US012331122B2

(12) United States Patent
Nioi et al.

(10) Patent No.: US 12,331,122 B2
(45) Date of Patent: Jun. 17, 2025

(54) ANTI-ASGR-1 MONOCLONAL INHIBITORY ANTIBODIES

(71) Applicant: Amgen Inc., Thousand Oaks, CA (US)

(72) Inventors: Paul Nioi, Wellesley, MA (US); Peter Coward, San Francisco, CA (US); Christopher Murawsky, Vancouver (CA); Derek E. Piper, Santa Clara, CA (US); Fernando Garces, San Mateo, CA (US); Brian Mingtung Chan, Port Coquitlam (CA)

(73) Assignee: Amgen Inc., Thousand Oaks, CA (US)

( * ) Notice: Subject to any disclaimer, the term of this patent is extended or adjusted under 35 U.S.C. 154(b) by 341 days.

(21) Appl. No.: 16/987,237

(22) Filed: Aug. 6, 2020

(65) Prior Publication Data
US 2021/0163601 A1 Jun. 3, 2021

Related U.S. Application Data

(60) Continuation of application No. 16/230,356, filed on Dec. 21, 2018, now Pat. No. 11,066,472, which is a division of application No. 15/279,162, filed on Sep. 28, 2016, now Pat. No. 10,358,497.

(60) Provisional application No. 62/319,740, filed on Apr. 7, 2016, provisional application No. 62/259,553, filed on Nov. 24, 2015, provisional application No. 62/234,546, filed on Sep. 29, 2015.

(51) Int. Cl.
| | |
|---|---|
| C07K 16/28 | (2006.01) |
| A61K 39/395 | (2006.01) |
| A61K 39/00 | (2006.01) |
| A61K 45/06 | (2006.01) |
| A61P 3/06 | (2006.01) |
| A61P 9/04 | (2006.01) |
| A61P 9/10 | (2006.01) |
| C07H 21/02 | (2006.01) |
| C07K 14/705 | (2006.01) |
| C12N 15/113 | (2010.01) |

(52) U.S. Cl.
CPC ...... *C07K 16/2851* (2013.01); *A61K 39/3955* (2013.01); *A61K 2039/505* (2013.01); *A61K 2039/507* (2013.01); *A61K 45/06* (2013.01); *A61P 3/06* (2018.01); *A61P 9/04* (2018.01); *A61P 9/10* (2018.01); *C07H 21/02* (2013.01); *C07K 14/705* (2013.01); *C07K 14/7056* (2013.01); *C07K 16/28* (2013.01); *C07K 2317/21* (2013.01); *C07K 2317/24* (2013.01); *C07K 2317/30* (2013.01); *C07K 2317/56* (2013.01); *C07K 2317/565* (2013.01); *C07K 2317/76* (2013.01); *C07K 2317/77* (2013.01); *C07K 2317/92* (2013.01); *C07K 2317/94* (2013.01); *C12N 15/1138* (2013.01)

(58) Field of Classification Search
CPC .. C07K 16/2851; C07K 16/28; A61K 39/395; A61K 39/3955
See application file for complete search history.

(56) References Cited

U.S. PATENT DOCUMENTS

| | | | |
|---|---|---|---|
| 3,720,760 A | 3/1973 | Wide et al. | |
| 4,179,337 A | 12/1979 | Davis et al. | |
| 4,301,144 A | 11/1981 | Iwashita et al. | |
| 4,331,647 A | 5/1982 | Goldenberg | |
| 4,496,689 A | 1/1985 | Mitra | |
| 4,518,584 A | 5/1985 | Mark et al. | |
| 4,522,811 A | 6/1985 | Eppstein et al. | |
| 4,640,835 A | 2/1987 | Shimizu et al. | |
| 4,670,417 A | 6/1987 | Iwasaki et al. | |
| 4,737,456 A | 4/1988 | Weng et al. | |
| 4,737,462 A | 4/1988 | Mark et al. | |
| 4,751,180 A | 6/1988 | Cousens et al. | |
| 4,791,192 A | 12/1988 | Nakagawa et al. | |
| 4,935,233 A | 6/1990 | Bell et al. | |
| 5,011,912 A | 4/1991 | Hopp et al. | |
| 5,208,020 A | 5/1993 | Chari et al. | |
| 5,223,409 A | 6/1993 | Ladner et al. | |
| 5,225,539 A | 7/1993 | Winter | |
| 5,416,064 A | 6/1995 | Chari et al. | |

(Continued)

FOREIGN PATENT DOCUMENTS

| | | |
|---|---|---|
| CN | 104418950 A | 3/2015 |
| EP | 404097 | 10/1991 |

(Continued)

OTHER PUBLICATIONS

Born, Sep. 2005, "Benefits and Application of Antibodies Against the H1 Carbohydrate Recognition Domain of the Human Hepatic Asialoglycoprotein Receptor", Dissertation, 324 pages as published.*

(Continued)

*Primary Examiner* — Zachary C Howard
(74) *Attorney, Agent, or Firm* — KNOBBE, MARTENS, OLSON & BEAR, LLP

(57) ABSTRACT

Antigen binding proteins that interact with ASGR, ASGR-1 and/or ASGR-2 are described as well as methods of making and using such antigen binding proteins. Methods of treating and preventing cardiovascular disease by administering a pharmaceutically effective amount of ASGR, ASGR-1 and/or ASGR-2 antigen binding proteins. Methods of treating and preventing cardiovascular disease by administering a pharmaceutically effective amount of interfering RNA compositions that reduce expression of ASGR, ASGR-1 and/or ASGR-2 are described.

17 Claims, 4127 Drawing Sheets
Specification includes a Sequence Listing.

(56) References Cited

U.S. PATENT DOCUMENTS

| | | |
|---|---|---|
| 5,457,035 A | 10/1995 | Baum et al. |
| 5,474,981 A | 12/1995 | Leder et al. |
| 5,475,092 A | 12/1995 | Chari et al. |
| 5,539,082 A | 7/1996 | Nielson et al. |
| 5,545,806 A | 8/1996 | Lonberg et al. |
| 5,569,825 A | 10/1996 | Lonberg et al. |
| 5,585,499 A | 12/1996 | Chari et al. |
| 5,624,821 A | 4/1997 | Winter et al. |
| 5,627,052 A | 5/1997 | Schrader |
| 5,693,762 A * | 12/1997 | Queen ............... C07K 16/2866 424/143.1 |
| 5,698,426 A | 12/1997 | Husebird |
| 5,714,331 A | 2/1998 | Buchardt et al. |
| 5,719,262 A | 2/1998 | Buchardt et al. |
| 5,814,318 A | 9/1998 | Lonberg et al. |
| 5,821,337 A | 10/1998 | Carter et al. |
| 5,859,205 A | 1/1999 | Adair et al. |
| 5,869,619 A | 2/1999 | Studnicka |
| 5,877,293 A | 3/1999 | Adair et al. |
| 5,877,397 A | 3/1999 | Lonberg et al. |
| 5,886,152 A | 3/1999 | Nakatani et al. |
| 5,898,031 A | 4/1999 | Crooke |
| 6,054,297 A | 4/2000 | Carter et al. |
| 6,107,094 A | 8/2000 | Crooke |
| 6,133,426 A | 10/2000 | Gonzalez et al. |
| 6,168,587 B1 | 1/2001 | Bellhouse et al. |
| 6,194,389 B1 | 2/2001 | Johnston et al. |
| 6,210,924 B1 | 4/2001 | Hu et al. |
| 6,277,375 B1 | 8/2001 | Ward |
| 6,340,701 B1 | 1/2002 | Chari et al. |
| 6,372,738 B2 | 4/2002 | Chari et al. |
| 6,395,272 B1 | 5/2002 | Deo et al. |
| 6,436,931 B1 | 8/2002 | Chari et al. |
| 6,471,996 B1 | 10/2002 | Sokoll et al. |
| 6,472,375 B1 | 10/2002 | Hoon et al. |
| 6,506,559 B1 | 1/2003 | Fire et al. |
| 6,573,099 B2 | 6/2003 | Graham |
| 6,602,684 B1 | 8/2003 | Umana et al. |
| 6,693,187 B1 | 2/2004 | Dellinger |
| 6,696,245 B2 | 2/2004 | Winter et al. |
| 6,703,199 B1 | 3/2004 | Koide |
| 6,846,634 B1 | 1/2005 | Tomlinson et al. |
| 6,881,557 B2 | 4/2005 | Foote |
| 7,029,872 B2 | 4/2006 | Gerngross |
| 7,056,704 B2 | 6/2006 | Tuschl et al. |
| 7,064,244 B2 | 6/2006 | Jakobovits et al. |
| 7,078,196 B2 | 7/2006 | Tuschl et al. |
| 7,563,459 B2 | 7/2009 | Phillips |
| 7,579,451 B2 | 8/2009 | Manoharan et al. |
| 7,695,963 B2 | 4/2010 | Agulnick et al. |
| 8,030,457 B2 | 10/2011 | Jackson et al. |
| 8,394,628 B2 | 3/2013 | Tuschl et al. |
| 8,502,014 B2 | 8/2013 | Grosveld |
| 8,507,455 B2 | 8/2013 | Manoharan et al. |
| 8,507,748 B2 | 8/2013 | Grosveld |
| 8,871,723 B2 | 10/2014 | Rubinstein et al. |
| 8,877,917 B2 | 11/2014 | Forst et al. |
| 9,006,292 B2 | 4/2015 | Raghavan |
| 9,181,551 B2 | 11/2015 | McSwiggen et al. |
| 10,358,497 B2 | 7/2019 | Nioi et al. |
| 11,066,472 B2 | 7/2021 | Nioi et al. |
| 2001/0036459 A1 | 11/2001 | Ravetch |
| 2003/0039958 A1 | 2/2003 | Holt et al. |
| 2003/0133939 A1 | 7/2003 | Ledbetter et al. |
| 2004/0009507 A1 | 1/2004 | Winter et al. |
| 2004/0038291 A2 | 2/2004 | Tomlinson et al. |
| 2004/0072290 A1 | 4/2004 | Umana et al. |
| 2004/0185045 A1 | 9/2004 | Koenig et al. |
| 2004/0202995 A1 | 10/2004 | De Wildt et al. |
| 2004/0261148 A1 | 12/2004 | Dickey et al. |
| 2005/0079605 A1 | 4/2005 | Umana et al. |
| 2005/0118643 A1 | 6/2005 | Burgess et al. |
| 2005/0202512 A1 | 9/2005 | Tomlinson et al. |
| 2005/0238646 A1 | 10/2005 | Ledbetter et al. |
| 2005/0272128 A1 | 12/2005 | Umana et al. |
| 2006/0039904 A1 | 2/2006 | Wu et al. |
| 2006/0040325 A1 | 2/2006 | Wu et al. |
| 2006/0067930 A1 | 3/2006 | Adams et al. |
| 2006/0257399 A1 | 11/2006 | Gerngross et al. |
| 2007/0031402 A1 | 2/2007 | Zhang et al. |
| 2007/0092521 A1 | 4/2007 | McPherson et al. |
| 2009/0028856 A1 | 1/2009 | Chen et al. |
| 2009/0169548 A1 | 7/2009 | Grosveld et al. |
| 2009/0274713 A1 | 11/2009 | Chari et al. |
| 2009/0285805 A1 | 11/2009 | Grosveld et al. |
| 2009/0307787 A1 | 12/2009 | Grosveld et al. |
| 2011/0092565 A1 | 4/2011 | Bumcrot et al. |
| 2011/0314563 A1 | 12/2011 | Craig et al. |
| 2012/0028596 A1 | 2/2012 | Yamada et al. |
| 2012/0151610 A1 | 6/2012 | Craig et al. |
| 2013/0024961 A1 | 1/2013 | Burlak et al. |
| 2015/0135344 A1 | 5/2015 | Tector, III et al. |
| 2015/0197746 A1 | 7/2015 | Rajeev et al. |
| 2015/0259689 A1 | 9/2015 | Kowalik et al. |
| 2016/0122761 A1 | 5/2016 | Prakash et al. |
| 2017/0088620 A1 | 3/2017 | Nioi et al. |
| 2019/0248902 A1 | 8/2019 | Nioi et al. |
| 2019/0309306 A1 | 10/2019 | Ollmann et al. |

FOREIGN PATENT DOCUMENTS

| | | |
|---|---|---|
| EP | 1144623 | 10/2001 |
| EP | 439095 | 12/2004 |
| JP | H04-356198 A | 12/1992 |
| KR | 10-2005-0024757 A | 3/2005 |
| WO | WO 87/05330 | 9/1987 |
| WO | WO 92/02551 | 2/1992 |
| WO | WO 93/10151 | 5/1993 |
| WO | WO 93/11161 | 6/1993 |
| WO | WO 93/21232 | 10/1993 |
| WO | WO 94/10308 | 5/1994 |
| WO | WO 97/34631 | 9/1997 |
| WO | WO 98/23289 | 6/1998 |
| WO | WO 98/24838 | 6/1998 |
| WO | WO 99/51642 | 10/1999 |
| WO | WO 99/58572 | 11/1999 |
| WO | WO 00/76310 | 12/2000 |
| WO | WO 01/79299 | 10/2001 |
| WO | WO 03/011878 | 2/2003 |
| WO | WO 2004/016750 | 2/2004 |
| WO | WO 2004/029207 | 4/2004 |
| WO | WO 2004/063351 | 7/2004 |
| WO | WO 2005/044859 | 5/2005 |
| WO | WO 2005/084390 | 9/2005 |
| WO | WO 2005/694879 | 10/2005 |
| WO | WO 2006/071280 | 7/2006 |
| WO | WO 2006/071856 | 7/2006 |
| WO | WO 2008/122886 | 10/2008 |
| WO | WO 2009/013620 | 1/2009 |
| WO | WO 2009/089004 | 7/2009 |
| WO | WO 2009/099728 | 8/2009 |
| WO | WO 2011/068798 A1 | 6/2011 |
| WO | WO 2014/023709 A1 | 2/2014 |
| WO | WO 2017/058944 A1 | 4/2017 |
| WO | WO 2018/039647 | 3/2018 |

OTHER PUBLICATIONS

NCBI Record for P07036, dated Feb. 23, 2022, 6 pages as printed, no author indicated; available on-line at www.ncbi.nlm.nih.gov/protein/P07036.*

Benjamini et al, 1991. Immunology: A Short Course, 2nd edition, p. 40 only.*

Ferrara et al (2015. mAbs. 7(1): 32-41).*

Adams et al., PHENIX: a comprehensive Python-based system for macromolecular structure solution, Acta crystallographica vol. 66, pp. 213-221 (2010).

Albert et al., The B-cell Epitope of the Monoclonal Anti-Factor VIII Antibody ESH8 Characterized by Peptide Array Analysis, Thromb Haemost vol. 99, pp. 634-637 (2008).

(56) References Cited

OTHER PUBLICATIONS

Alting-Mees et al., Monoclonal Antibody Expression Libraries: A Rapid Alternative to Hybridisms Strategies in Molecular Biology vol. 3, 1990).

Andrews et all Fragmentation of Immunoglobulin G, Current Protocols in Immunology, Unit 2.10A John Wiley & Sons (1997).

Aoki et al., Potential tumor-targeting peptide vector of histidylated oligolysine conjugated to a tumor-homing RGD motif, Cancer Gene Therapy vol. 8, pp. 783-787 (2001).

Aplin et al., Preparation, Properties, and Applications of Carbohydrate Conjugates of Proteins and Lipids, CRC Critical Reviews in Biochemistry, pp. 259-306, May 1981.

Arbones et al., Lymphocyte Homing and Leukocyte Rolling and Migration Are Impaired in L-Selectin-Deficient Mice, Immunity. vol. 1, pp. 247-260 (1994).

Ashkenazi et al., Protection Against Endotoxic Shock by a Tumor Necrosis Factor Receptor Immunoadhesin, Proceedings of the National Academy of Sciences USA, vol. 88, pp. 10535-10539, Dec. 1991.

Ashwell et al., "Carbohydrate-Specific Receptors of the Liver," Annual Review of Biochemistry, vol. 51, pp. 531-554. 1982.

Ausubel et al., Table of Contents of "Current Protocols in Molecular Biology," Book: Short Protocols in Molecular Biology, 2 ed., Greene Publishing Associates and John Wiley & Sons, 1992.

Babcock et al., A novel strategy for generating monoclonal antibodies from single, isolated lymphocytes producing antibodies of defined specificities, Proc. Natl. Acad. Sci. USA vol. 93, pp. 843-848 (1996).

Baines et al., Purification of Immunoglobulin G (IgG), Methods in Molecular Biology vol. 10, pp. 79-104, The Human Press Inc. (1992).

Baron et al., Co-regulation of two gene activities by tetracycline via a bidirectional promoter, Nucleic Acids Res. vol. 23, pp. 3605-3606 (1995).

Baum et al., "Molecular Characterization of Murine and Human OX40/OX40 Ligand Systems: Identification of a Human OX40 Ligand as the HTLV-1-Regulated Protein GP34," The EMBO Journal, vol. 13, No. 17, pp. 3992-4001, 1994.

Battye et al., iMOSFLM: a new graphical interface for diffraction-image processing with MOSFLM, Acta crystallographica vol. 67, pp. 271-281 (2011).

Bauer et al., A genetic enrichment for mutations constructed by oligodeoxynucleotide-directed mutagenesis Gene vol. 37, pp. 73 (1985).

Bebbington et al., The use of vectors based on gene amplification for the expression of cloned genes in mammalian cells, DNA Cloning, vol. 3. Academic Press (1987).

Bird et al., "Single-Chain Antigen-Binding Proteins," Science, vol. 242, pp. 423-426, 1988.

Bishop, Table of Contents of Guide to Huge Computers, ed., Academic Press, (1994).

Bowie et al., "A Method to Identify Protein Sequences That Fold Into a Known Three-Dimensional Structure," Science, vol. 253, pp. 164-170, Jul. 12, 1991.

Bloom et al., "Intrachain Disulfide Bond in the Core Hinge Region of Human IgG4," Protein Science, vol. 6, pp. 407-415, 1997.

Boerner et al., Production of antigen-specific human monoclonal antibodies from in vitro-primed human splenocytes Journal or Immunology vol. 147, pp. 86-95 (1991).

Born, R., Benefit and Application of Antibodies Against the HI Carbohydrate Recognition Domain of the Human Hepatic Asialoglycoprotein Receptor High Yield Recombinant Production of the HI Carbohydrate Recognition Domain And Production and Characterization of Murine Monoclonal and Chicken Polyclonal Antibodies, Thesis, (2005).

Branden et al., Table of Contents of "Introduction to Protein Structure," Garland Publishing, Inc., 6 pages, 1991.

Bruggemann et al., Production of human antibody repertoires in transgenic mice Current Opinions in Biotechnology vol. 8, pp. 455-458 (1997).

Burger et al., Human plasma R-type vitamin B12-binding proteins II. The role of transcobalamin I, transcobalamin III, and the normal granulocyte vitamin B12-binding protein in the plasma transport of vitamin B12, The Journal of Biological Chemistry vol. 250, pp. 7707-7713 (1975).

Burton et al., "Human Antibodies from Combinatorial Libraries," Advances in Immunology, vol. 57, pp. 191-280, 1994.

Byrn et al., "Biological Properties of a CD4 Immunoadhesion," Nature, vol. 344, pp. 667-670, Apr. 12, 1990.

Cao et al., "Characterization of a Single-Chain Variable Fragment (scFv) Antibody Directed Against the Human Asialoglycoprotein Receptor," Biotechnology and Applied Biochemistry, vol. 44, No. 2, pp. 65-72, 2006.

Carrillo, et al., "The Multiple Sequence Alignment Problem in Biology,"SIAM Journal on Applied Mathematics, vol. 48,, No. 5, pp. 1073-1082, Oct. 5, 1988.

CCP4, The CCP4 suite: programs for protein crystallography, Acta crystallographica vol. 50, pp. 760-763 (1994).

Chambers et al., Genome-wide association study identifies loci influencing concentrations of liver enzymes in plasma, Nature genetics vol. 43, pp. 1131-1138 (2011).

Chen et al., Immunoglobulin gene rearrangement in B-cell deficient mice generated by targeted deletion of the JH locus, International Immunology vol. 5, pp. 647-656 (1993).

Cheung et al., Epitope-Specific Antibody Response to the Surface Antigen of Duck Hepatitis 6 Virus in Infected Ducks Virology vol. 176, pp. 546-552 (1990).

Choi et al., Transgenic mice containing a human heavy chain immunoglobulin gene fragment cloned in a yeast artificial chromosome, Nature Genetics vol. 4, pp. 117-123 (1993).

Chothia, C et al., Canonical Structures for the Hypervariable Regions of Immunoglobulins, Journal of Molecular Biology vol. 196, pp. 901-917 (1987).

Chothia et al., Conformations of Immunoglobulin hypervariable regions, Nature vol. 342, pp. 878-883 (1989).

Chou et al., Prediction of the secondary structure of proteins from their amino acid sequence, Adv. Enzymol. Relat. Areas Mol. Biol. vol. 47, pp. 45-148 (1978).

Chou et al., Empirical predictions of protein conformation, Ann. Rev. Biochem. vol. 47, pp. 251-276.

Chou et al., Prediction of protein conformation, Biochemistry vol. 13(2), pp. 222-245 (1974).

Chou et al. Prediction of A-Turns, Biophys J. vol. 26, pp. 367-384 (1979).

Chou et al., Conformational Parameters for amino acids in helical b-sheet, and random coil regions calculated from proteins, Biochemistry vol. 113(2), pp. 211-222 (1974).

Clark, M., Antibody humanization: a case of the 'Emperor's new clothes'? Immunology Today vol. 21(8), pp. 397-402 (2000).

Coates et al., Epitope mapping by amide hydrogen/deuterium exchange coupled with immobilization of antibody, on-line proteolysis, liquid chromatography and mass spectrometry, Rapid Communication Mass Pectrometry vol. 23, pp. 639-647 (2009).

Cockett et al., High level of tissue inhibitor of metalloproteinases in Chinese hamster ovary cells using glutamine synthetase gene amplification, Bio/Technology vol. 8, pp. 2 (1990).

Colberre-Garapin et al., A New Dominant Hybrid Selective Marker for Higher Eukaryotic Cells J. Mol. Biol. vol. 150, pp. 1 (1981).

Cortez-Retamozo et al., Efficient Cancer Therapy with a Nanobody-Based Conjugate, Cancer Research vol. 64, pp. 2853-2857 (2004).

Courtenay-Luck, Genetic Manipulation of Monoclonal Antibodies, Monoclonal Antibodies: Production, Engineering and Clinical Application, Ritter et al. (eds.), pp. 166, Cambridge University Press (1995).

Craik, Use of oligonucleotides for site-specific mutagenesis, BioTechniques, 12-19 (1985).

Crameri et al., DNA shuffling of a family of genes from diverse species accelerates directed evolution, Nature vol. 391, pp. 288-291 (1998).

Creighton, Ed., Proteins, Structures, and Molecular Principles, W.H. Freeman and Company (1984).

Creighton, Proteins: Structure and Molecular Properties, W.H. Freeman & Co., pp. 79-86 (1983).

(56) References Cited

OTHER PUBLICATIONS

Crouse et al., Expression and Amplification of Engineered Mouse Dihydrofolate Reductase Minigenes, Mol. Cell. Biol. vol. 3, pp. 257 (1983).
Cunningham and Wells, High-resolution epitope mapping og HGH-receptor interactions by alanine-scanning mutagenesis, Science vol. 244, pp. 1081085 (1989).
D'Souza et al., Asialoglycoprotein receptor mediated hepatocyte targeting—Strategies and applications Journal of Control Release vol. 203, pp. 126-139 (2015).
Dall'Acqua et al., Antibody humanization by framework shuffling, Methods vol. 36(1), pp. 43-60 (2005).
Davis et al., Transgenic mice as a source of fully human antibodies for the treatment of cancer, Cancer Metastasis Rev. vol. 18, pp. 421-425 (1999).
Davis et al., Production of human antibodies from transgenic mice in Lo, ed. Antibody Engineering: Methods and Protocols, Humana Press, NJ, pp. 191-200 (2003).
Deleavey et al., Designing Chemically Modified Oligonucleotides for Targeted Gene Silencing Chemistry and Biology, vol. 19, pp. 937-954 (2012).
Devereux et al., A comprehensive set of sequence analysis programs for the VAX, Nucl. Acids Res. vol. 12(1), pp. 387 (1984).
Di Angelantonio et al., Major lipids, apolipoproteins, and risk of vascular disease, Jama vol. 302, pp. 1993-2000 (2009).
Do et al., Common variants associated with plasma triglycerides and risk for coronary artery disease. Nature genetics vol. 45, pp. 1345-1352 (2013).
Dracopoli et al. (eds), Table of Contents of Current Protocols in Human Genetics, John Wiley & Sons (1994).
Emsley et al., Features and development of Coot, Acta crystallographica vol. 66, pp. 486-501 (2010).
Evans, Scaling and assessment of data quality, Acta crystallographica vol. 62, pp. 72-82 (2006).
Fanslow et al., Structural characteristics of CD40 ligand that determine biological function, Semin. Immunol. vol. 6, pp. 267-278 (1994).
Fell et al., Genetic construction and characterization of a fusion protein consisting of a chimeric F(ab') with specificity for carcinomas and human IL-2., J. Immunol. vol. 146, pp. 2446-2452 (1991).
Fieser et al., Table of Contents of Fieser and Fieser's Reagents for Organic Synthesis, John Wiley and Sons (1994).
Fishwild et al., High-avidity human IgGk monoclonal antibodies from a novel strain of miniolocus transgenic mice Nature Biotechnology vol. 14, pp. 845-851 (1996).
Foecking et al., Powerful and versatile enhancer-promoter unit for mammalian expression vectors Gene vol. 45, pp. 101 (1986).
Fredericks et al., Identification of potent human anti-IL-1RI antagonist antibodies, Protein Engineering, Design, & Selection vol. 17, pp. 95-106 (2004).
Friedewald et al., Estimation of the concentration of low-density lipoprotein cholesterol in plasma, without use of the preparative ultracentrifuge. Clin. Chem. vol. 18, pp. 499-502 (1972).
Furger et al., Comparison of recombinant human haptocorrin expressed in human embryonic kidney cells and native haptocorrin PloS one vol. 7, e37421 (2012).
Gallo et al., The human immunoglobulin loci introduced into mice: V (D) and J gene segment usage similar to that of adult humans European Journal of Immunology vol. 30, pp. 534-540 (2000).
Gentz et al., Bioassay for trans-activation using purified human immunodeficiency virus tat-encoded protein: Trans-activation requires mRNA synthesis Proc. Natl. Acad. Sci. USA vol. 86, pp. 821-824 (1989).
Gerhardt et al. Structure of IL-17A in complex with a potent, fully human neutralizing antibody, Journal of Molecular Biology vol. 394, pp. 905-921 (2009).
Gibskov et al., Profile analysis: Detection of distantly related proteins. Proc. Nat. Acad. Sci. vol. 84(13), pp. 4355-4358 (1987).
Gillies et al., Antibody-targeted interleukin 2 stimulates T-cell killing of autologous tumor cells, Proc. Natl. Acad. Sci. vol. 89, pp. 1428-1432 (1992).
Glasky et al., Stability of Specific Immunoglobulin Secretion by EBV-Transformed Lymphoblastoid Cells and Human-Murine Heterohybridomas, Hybridoma vol. 8, pp. 377-389 (1989).
Gluzman et al., SV40-Transformed Simian Cells Support the Replication of Early SV40 Mutants, Cell vol. 23, pp. 175 (1981).
Goeddel, Gene Expression Technology: Methods in Enzymology vol. 185, Academic Press, (1990).
Gold et al., Aptamer-based multiplexed proteomic technology for biomarker discovery, PLoS One 5, e15004, doi:10.1371/journal.pone.0015004 (2010).
Green et al., Antigen-specific human monoclonal antibodies from mice engineered with human Ig heavy and light chain YACs Nat Genet. vol. 7, pp. 13-21 (1994).
Green et al., Regulation of B Cell Development by Variable Gene Complexity in Mice Reconstituted with Human Immunoglobulin Yeast Artificial Chromosomes, Journal of Experimental Medicine vol. 188, pp. 483-495 (1998).
Green, Antibody engineering via genetic engineering of the mouse: XenoMouse strains are a vehicle for the facile generation of therapeutic human monoclonal antibodies, Journal of Immunological Methods vol. 231, pp. 11-23 (1999).
Greene et al., Protection for the hydroxyl group, including 1, 2- and 1,3-diols, Protective Groups in Organic Synthesis, 2d. Ed., John Wiley and Sons (1991).
Gretarsdottir et al., Genome-wide association study identifies a sequence variant within the DAB2IP gene conferring susceptibility to abdominal aortic aneurysm, Nature genetics vol. 42, pp. 692 (2010).
Gretarsdottir et al., The gene encoding phosphodiesterase 4D confers risk of ischemic stroke, Nature genetics vol. 35, pp. 131-138 (2003).
Grewal, The Ashwell-Morell Receptor, Methods in Enzymology vol. 479, chapter 13, pp. 223-241 (2010).
Gribskov et al., Profile Analysis, Meth. Enzym. vol. 183, pp. 146-159 (1990).
Gribskov et al., Sequence analysis primer, eds., M Stockton Press, (1991).
Griffin, et al., Computer analysis of sequence data, part I, eds., Humana Press, (1994).
Gu et al. The asialoglycoprotein receptor suppresses the metastasis of hepatocellular carcinoma via LASS2-mediated inhibition of V-ATPase activity, Cancer Letters, vol. 379, pp. 107-116, (2016).
Gudbartssoon et al., Large Scale whole-genome sequencing of the Icelandic population, Nature Genetics vol. 47(5), pp. 435-444 (2015).
Haddad et al., Evidence for a third genetic locus causing familial hypercholesterolemia. A non-LDLR, non-APOB kindred, Journal of lipid research vol. 40, pp. 1113-1122 (1999).
Hamajima et al. Intranasal Administration of HIV-DNA vaccine formulated with a polymer, carboxymethycellulose, augments mucosal antibody production and cell-mediated immune response , Clin. Immunol. Immunopathol. vol. 88(2), pp. 205-210 (1998).
Harding et al., "Class Switching in Human Immunoglobulin Transgenic Mice," Annals of the New York Academy of Sciences, vol. 764, pp. 536-546, 1995.
Hardonk al., A Histochemical Study about the zonal distribution of galactose-biding protein in rat liver, Histochemistry vol. 69(3), pp. 289-297 (1980).
Harlow and Lane, Antibodies: A Laboratory Manual, Cold Spring Laboratory Press (1988 and 1990).
Harris, Processing of C-terminal lysine and arginine residues of proteins isolated from mammalian cell culture Journal of Chromatography vol. 705, pp. 129-134 (1995).
Haubner et al. Glycosylated RGD-Containing Peptides: Tracer for Tumor Targeting and Angiogenesis Imaging with Improved Biokinetics, Jour. Nucl. Med. vol. 42, pp. 326-336 (2001).
Hollenbaugh et al., Construction of Immunoglobulin Fusion Proteins, Current Protocols in Immunology, Suppl. 4, pp. 10.19.1-10.19.11. (1992).

(56) References Cited

OTHER PUBLICATIONS

Hollinger and Hudson, Engineered antibody fragments and the rise of single domains, Nature Biotechnology vol. 23(9), pp. 1126-1136 (2005).
Hollinger et al. "Diabodies": Small bivalent and bispecific antibody fragments, Proc. Natl. Acad. Sci. USA vol. 90, pp. 6444-6448 (1993).
Holm et al., Protein folds and families: sequence and structure alignments, Nucl. Acid. Res. vol. 27(1), pp. 244-247 (1999).
Honegger and Pluckthun, Yet another numbering scheme for immunoglobulin variable domains: An automatic modeling and analysis tool, Journal of Molecular Biology vol. 309(3), pp. 657-670 (2001).
Hoogenboom et al., Human antibodies from synthetic repertoires of germline VH Gene Segments Rearranged in vitro Journal of Molecular Biology vol. 227, pp. 381-388 (1992).
Hoogendoorn et al., Thyroid function and prevalence of anti-thyroperoxidase antibodies in a population with borderline sufficient iodine intake: influences of age and sex, Clinical chemistry vol. 52, pp. 104-111 (2006).
Hopp et al. A Short Polypeptide Marker Sequence useful for recombinant protein identification and purification, Bio/Technology vol. 6, pp. 1204 (1988).
Hoppe et al., A parallel three stranded o-helical bundle at the nucleation site of collagen triple-helix formation, FEBS Letters vol. 344, pp. 191 (1994).
Hudson et al., Sodium-coupled glycine uptake by Ehrlich ascites tumor cells results in an increase in cell volume and plasma membrane channel activities, Proc. Natl. Acad. Sci. USA vol. 85, pp. 5879-5883 (1988).
Hunt et al., Genetic localization to chromosome 1p32 of the third locus for familial hypercholesterolemia in a Utah kindred, Arterioscler Thromb Vasc Biol vol. 20, pp. 1089-1093 (2000).
Huse et al., Generation of a Large Combinatorial Library of the Immunoglobulin Repertoire in Phage Lambda, Science vol. 246, pp. 1275-1281 (1989).
Hwang et al., Use of human germline genes in a CDR homology-based approach to antibody humanization, Methods vol. 36(1), pp. 35-42 (2005).
International Preliminary Report on Patentability received in International Patent Application No. PCT/US2016/054222, dated Apr. 3, 2018.
International Search Report and Written Opinion received in International Patent Application No. PCT/US2016/054222, dated Mar. 10, 2017.
International Search Report and Written Opinion, mailed Feb. 5, 2018, received in International Patent Application No. PCT/US2017/048757.
Jakobovits et al., Analysis of homozygousmutant chimeric mice: Deletion of the immunoglobulin heavy-chain joining region blocks B-cell development and antibody production, Proc. Natl. Acad. Sci. USA vol. 90, pp. 2551-2555 (1993).
Jakobovits et al., Germ-line transmission and expression of a human-derived yeast artificial chromosome, Nature vol. 362, pp. 255-258 (1993).
Jakobovits, A., The long-awaited magic bullets: therapeutic human monoclonal antibodies from transgenic mice, Exp. Opin. Invest. Drugs vol. 7, pp. 607-614 (1998).
Jakobovits, A., Production and Selection of antigen-specific fully human monoclonal antibodies from mice engineered with human Ig loci, Advanced Drug Delivery Reviews vol. 31, pp. 33-42 (1998).
Jakobovits, A., Humanizing the mouse genome, Curr. Biol. vol. 4, pp. 761-763 (1994).
Janssens et al. Generation of heavy-chain-only antibodies in mice, PNAS vol. 103, pp. 15130-15135; Harbour Biologics, Rotterdam, Netherlands 2006.
Jia et al., A novel method of Multiplexed Competitive Antibody Binning for the characterization of monoclonal antibodies, Journal of immunological Methods vol. 288, pp. 91-98 (2004).
Jones, D., Progress in protein structure prediction, Current Opinions on Structural Biology vol. 7(3), pp. 377-387 (1997).
Jorgensen et al., Loss-of-function mutations in APOC3 and risk of ischemic vascular disease, The New England journal of medicine vol. 371, pp. 32-41 (2014).
Kabat, E.A. et al., Sequences of Proteins of Immunological Interest, NIH, Bethesda, MD (1987 and 1991).
Kabat E.A. et al., Sequences of Proteins of Immunological Interest, NIH, Bethesda, MD (1991).
Kang et al., Linkage of recognition and replication functions by assembling combinatorial antibody Fab libraries along phase surfaces, Proc Natl. Acad Sci. USA vol. 88, pp. 363-366 (1991).
Kellerman et al., Antibody discovery: the use of transgenic mice to generate human monoclonal antibodies for therapeutics, Current Opinion in Biotechnology vol. 13, pp. 593-597 (2002).
Kenneth et al., Monoclonal Antibodies, Hybridomas: A New Dimension in Biological Analyses, Plenum Press (1980).
Kohgo, Y., et al., Production and Characterization of Specific Asialoglycoprotein Receptor Antibodies, HYBRIDOMA, vol. 12, No. 5, pp. 591-598, (1993).
Kirkland et al., Analysis of the Fine Specificity and Cross-Reactivity of Monoclonal Anti-lipid A Antibodies, Journal of Immunology vol. 137, pp. 3614-3619 (1986).
Kohler, Immunoglobulin chain loss in hybridoma lines, Proc. Natl. Acad. Sci. USA vol. 77, pp. 2197 (1980).
Korndorfer et al., Crystallographic Analysis of an "Anticalin" with Tailored Specificity for Fluorescein Reveals High Structural Plasticity of the Lipocalin Loop Region, Proteins: Structure, Function, and Bioinformatics vol. 53(1), pp. 121-129 (2003).
Kortt et al. Dimeric and trimeric antibodies: high avidity scFvs for cancer targeting, Biomol. Eng. vol. 18, pp. 95-108 (2001).
Kortt et al., Single-chain Fv fragments of anti-neuraminidase antibody NC10 containing five-and ten-residue linkers form dimers and with zero-residue linker a trimer, Protein Engineering vol. 10, pp. 423 (1997).
Kostelny et al., Formation of a Bispecific Antibody by the Use of Leucine Zippers, Journal of Immunology vol. 148, pp. 1547-1553 (1992).
Kriegler, M., Table of Contents of Gene Transfer and Expression, A Laboratory Manual, Stockton Press (1990).
Kriangkum et al., Bispecific and bifunctional single chain recombinant antibodies, Biomol. Eng. vol. 18, pp. 31-40 (2001).
Lam et al., A new type of synthetic peptide library for identifying ligand-binding activity, Nature vol. 354, pp. 82-84 (1991).
Landschulz et al., The Leucine Zipper: A Hypothetical Structural Common to a New Class of DNA Binding Proteins, Science vol. 240, pp. 1759 (1988).
Lanitto et al., Chain Shuffling to Modify Properties of Recombinant Immunoglobulins, Methods in Molecular Biology vol. 178, pp. 303-316 (2002).
Larock, Comprehensive Organic Transformations, VCH Publishers (1989).
Larrick et al., Polymerase Chain Reaction Using Mixed Primers: Cloning of Human Monoclonal Antibody Variable Region Genes from Single Hybridoma Cells, Bio/Technology vol. 7, pp. 934 (1989).
Larrick et al., Methods: A Companion to Methods in Enzymology vol. 2, pp. 106 (1991).
Lefranc et al., IMGT unique numbering for immunoglobulin and T cell receptor constant domains and Ig superfamily C-like domains, Dev. Comp. Immunol. vol. 29, pp. 185-203 (2005).
Lesk, Computational molecular biology, A. M., ed., Oxford University Press, (1988).
Lim et al., A diversity of antibody epitopes can induce signaling through the erythropoietin receptor, Biochemistry vol. 49, pp. 3797-3804 (2010).
Liu et al., Chimeric mouse-human IgG1 antibody that can mediate lysis of cancer cells, Proc. Nat. Acad. Sci. USA vol. 84, pp. 3439 (1987).
Lonberg et al., Human Antibodies from Transgenic Mice, Internal Review of Immunology vol. 13, pp. 65-93 (1995).
Lonberg et al., Antigen-specific human antibodies from mice comprising four distinct genetic modifications, Nature vol. 368, pp. 856-859 (1994).

(56) References Cited

OTHER PUBLICATIONS

Lonberg, Transgenic Approaches to Human Monoclonal Antibodies in Handbook of Experimental Pharmacology vol. 113, pp. 49-101 (1994).
Low et al., Mimicking Somatic Hypermutation: Affinity Maturation of Antibodies Displayed on Bacteriophae Using a Bacterial Mutator Strain, Journal of Molecular Biology vol. 250, pp. 350-368 (1996).
Lowy et al., Isolation of Transforming DNA: Cloning the Hamster aprt Gene, Cell vol. 22, pp. 817 (1980).
Liu et al., A new splice variant of the major subunit of human asialogycoprotein receptor encodes a secreted form in hepatocytes PloS one, vol. 5, e12934 (2010).
Maniatis et al., Regulation of Inducible and Tissue-Specific Gene Expression, Science vol. 236, pp. 1237 (1987).
Manoharan, Oligonucleotide Conjugates in Antisense Technology, Antisense Drug Technology, ed. S. T. Crooke, Marcel Dekker, Inc. (2001).
Marks et al., By-passing Immunication: Building High Affinity Human Antibodies by Chain Shuffling, Bio/Technology vol. 10, pp. 779-783 (1992).
Massarelli et al., "Three-Dimensional Models of the Oligomeric Human Asialoglycoprotein Receptor (ASGP-R)", International Journal of Molecular Sciences, vol. 11, No. 10, pp. 3867-3884, 2010.
McCoy et al., Phaser crystallographic software, Journal of applied crystallography vol. 40, pp. 658-674 (2007).
McMahan et al., A novel IL-1 receptor, cloned from B cells by mammalian expression, is expressed in many cell types, EMBO J. vol. 10, pp. 2821 (1991).
Meier et al., Crystal structure of the carbohydrate recognition domain of the H1 subunit of the asialoglycoprotein receptor. Journal of molecular biology vol. 300, 857-865 (2000).
Mendez et al., Functional transplant of megabase human immunoglobulin loci recapitulates human antibody response in mice, Nat Gen. vol. 15, pp. 146-156 (1997).
Miller et al., Epitope binning of murine monoclonal antibodies by a multiplexed pairing assay, Journal of Immunological Methods vol. 365, pp. 118-125 (2011).
Moldenhauer et al., Identity of HML-1 Antigen on Intestinal Intraepithelial T Cells and B-ly7 Antigen on Hairy Cell Leukaemia, Scandinavian Journal of Immunology vol. 32, pp. 7-82 (1990).
Molecular Operating Environment (MOE), 08, Chemical Computing Group, Inc., (2013).
Morel et al., Monoclonal Antibodies to Bovine Serum Albumin: Affinity and Specificity Determinations, Molecular Immunology vol. 25, pp. 7-15 (1988).
Morell et al., The role of sialic acid in determining the survival of glycoproteins in the circulation, The Journal of biological chemistry vol. 246, pp. 1461-1467 (1971).
Morgan et al., Precise epitope mapping of malaria parasite inhibitory antibodies by TROSY NMR cross-saturation, Biochemistry vol. 44, pp. 518-523 (2005).
Moult, J., The current state of the art in protein structure prediction, Current Operations in Biotechnology vol. 7(4), pp. 422-427 (1996).
Mulligan et al., Selection for animal cells that express the *Escherichia coli* gene coding for xanthine-guanine phosphoribosyltransferase, Proc. Natl. Acad. Sci. USA vol. 78, pp. 2072 (1981).
Nanevicz et al., Mechanisms of Thrombin Receptor Agonist Specificity, Journal of Biological Chemistry vol. 270(37), pp. 21619-21625 (1995).
Naramura et al., Mechanisms of cellular cytotoxicity mediated by a recombinant antibody-IL2 fusion protein against human melanoma cells, Immunol. Lett. vol. 39, pp. 91-99 (1994).
Neuberger, Generating high-avidity human Mabs in mice, Nature Biotechnology vol. 14, pp. 826 (1996).
Nioi et al., Variant ASGR1 Associated with a Reduced Risk of Coronary Artery Disease, The New England journal of medicine vol. 374, pp. 2131-2141, doi:10.1056/NEJMoa1508419 (2016).
Nisonoff et al., Separation of Univalent Fragments from the Bivalent Rabbit Antibody Molecule by Reduction of Disulfide Bonds, Arch. Biochem. Biophys. vol. 89, pp. 230 (1960).
Nygren and Uhlen, Scaffolds for engineering novel binding sites in proteins, Current Opinion in Structural Biology vol. 7, pp. 463-469 (1997).
O'Hare et al., Transformation of mouse fibroblasts to methotrexate resistance by a recombinant plasmid expressing a prokaryotic dihydrofolate reductase, Proc. Natl. Acad. Sci. USA vol. 78, pp. 1527 (1981).
Olafsen et al., Characterization of engineered anti-p185-$^{HER-2}$ (scFv-$C_H3)_2$ antibody fragments (minibodies) for tumor targeting, Protein Eng Des Sel. vol. 17, pp. 315-323 (2004).
Olsen et al., N-terminal pro-brain natriuretic peptide, but not high sensitivity C-reactive protein, improves cardiovascular risk prediction in the general population, European heart journal vol. 28, pp. 1374-1381 (2007).
Padlan et al., Identification of specificity-determining residues in antibodies, FASEB J. vol. 9, pp. 133-139 (1995).
Paquette, ed., Encyclopedia of Reagents for Organic Synthesis, John Wiley and Sons (1995).
Paris et al. ASGR1 expressed by porcine enriched liver sinusoidal endothelial cells mediates human platelet phagocytosis in vitro, Xenotransplantation vol. 18, pp. 245-251, (2011).
Park et al., "Detection of Surface Asialoglycoprotein Receptor Expression in Hepatic and Extra-Hepatic Cells Using a Novel Monoclonal Aantibody," Biotechnology Letters, vol. 28. No. 14, pp. 1061-1069, 2006.
Patten et al., Applications of DNA shuffling to pharmaceuticals and vaccines, Current Opinions in Biotechnology vol. 8, pp. 724-733 (1997).
Paul, ed., Fundamental Immunology, 4$^{th}$ ed., Lippincott-Raven, Philadelphia (1999).
Paul, W., Fundamental Immunology Ch. 7, 2d ed., Raven Press, N.Y. (1989).
Poljak et al., Production and structure of diabodies, Structure vol. 2, pp. 1121-1123 (1994).
Porter, The Hydrolysis of Rabbit γ-Globulin and Antibodies with Crystalline Papain, Biochemistry Journal vol. 73, pp. 119 (1959).
Pouwels et al., Cloning Vectors: A Laboratory Manual, Elsevier (1985).
Powers et al., Expression of single-chain Fv-Fc fusions in Pichia pastoris, Journal of Immunological Methods vol. 251, pp. 123-135 (2001).
Proudfoot, Transcriptional interference and termination between duplicated α-globin gene constructs suggests a novel mechanism for gene regulation, Nature vol. 322, pp. 52 (1986).
Rajeev et al., Hepatocyte-Specific Delivery of siRNAs Conjugated to Novel Non-nucleosidic Trivalent N-Acetylgalactosamine Elicits Robust Gene Silencing in Vivo, ChemBiochem vol. 16(6), pp. 903-908 (2015).
Rasmussen et al., Isolation, characterization and recombinant protein expression in Veggie-CHO: A serum-free CHO host cell line, Cytotechnology vol. 28, pp. 31 (1998).
Rathanaswami et al., High-affinity binding measurements of antibodies to cell-surface-expressed antigens, Analytical Biochemistry vol. 373, pp. 52-60 (2008).
Riechmann et al., Reshaping human antibodies for therapy, Nature vol. 332, pp. 323 (1988).
Roggenbuck et al., Asialoglycoprotein receptor (ASGPR): a peculiar target of liver-specific autoimmunity, Autoimmune Highlights vol. 3, pp. 119-125 (2012).
Roque et al., Antibodies and Genetically Engineered Related Molecules: Production and Purification, Biotechnology Progress vol. 20, pp. 639-654 (2004).
Rotundo et al., Circulating Cellular Fibronectin May be a Natural Ligand for the Hepatic Asialoglycoprotein Receptor: Possible Pathway for Fibronectin Deposition and Turnover in the Rat Liver, Hepatology vol. 28, pp. 475-485 (1998).
Russel et al., Production of Protective Human Antipneumococcal Antibodies by Transgenic Mice with Human Immunoglobulin Loci, Infect Immun. vol. 68, pp. 1820-1826 (2000).
Sabrautzki et al., "New Mouse Models for Metabolic Bone Disease Generated by ENU Mutagenesis Genome-Wide ENU Mutagenesis," Mammalian Genome, vol. 23, pp. 416-430, 2012.

(56) References Cited

OTHER PUBLICATIONS

Saitou and Nei, The Neighbor-joining Method: A New Method for Reconstructing Phylogenetic Trees Molecular Biology and Evolution vol. 4, pp. 406-425 (1987).

Samani et al., Genomewide association analysis of coronary artery disease, The New England journal of medicine vol. 357, pp. 443-453 (2007).

Sambrook et al., Molecular Cloning: A Laboratory Manual, 2d ed., Cold Spring Harbor Laboratory Press. (1989).

Santerre et al., Expression of prokaryotic genes for hygromycin B and G418 resistance as dominant-selection markers in mouse L cells, Gene vol. 30, pp. 147 (1984).

Sastry et al., Cloning of the immunological repertoire in *Escherichia coli* for generation of monoclonal catalytic antibodies: Construction of a heavy chain variable region-specific cDNA library, Proc. Natl. Acad. Sci. USA vol. 86, pp. 5728-5732 (1989).

Schier et al., Isolation of Picomolar Affinity Anti-c-erbB-2 Single-chain Fv by Molecular Evolution of the Complementarity Determining Regions in the Center of the Antibody Binding Site, Journal of Molecular Biology vol. 263, pp. 551 (1996).

Scholtens et al., A histochemical study on the distribution of injected canine intestinal alkaline phosphatase in rat liver, Liver vol. 2(1), pp. 14-21 (1982).

Sclebusch et al., Production of a Single-Chain Fragment of the Murine Anti-Idiotypic Antibody ACA125 as Phage-Displayed and Soluble Antibody by Recombinant Phage Antibody Technique, Hybridoma vol. 16, pp. 47-52 (1997).

Sham et al., Statistical power and significance testing in large-scale genetic studies, Nature reviews, Genetics vol. 15, 335-346, doi:10.1038/nrg3706 (2014).

Shimada, M. A monoclonal antibody to rat asialoglycoprotein receptor that recognizes an epitope specific to its major subunit, Hepatology Research, vol. 26, No. 1, pp. 55-60, (2003).

Simeoni et al., Insight into the mechanism of the peptide-based gene delivery system MPG: implications for delivery of siRNA into mammalian cells, Nucl. Acids Res. vol. 31, pp. 2717-2724 (2003).

Sippl et al., Threading thrills and threats, Structure vol. 4(1), pp. 15-19 (1996).

Smith et al., Genetic Engineering: Principles and Methods, Plenum Press (1981).

Smith, Biocomputing: informatics and genome projects, ed., Academic Press, (1993).

Song et al., Epitope Mapping of Ibalizumab, a Humanized Anti-CD4 Monoclonal Antibody with Anti-HIV-1 Activity in Infected Patients, Journal of Virology vol. 84, pp. 6935-6942 (2010).

Songsivilai and Lachmann, Bispecific antibody: a tool for diagnosis and treatment of disease, Clinical Experimental Immunology vol. 79, pp. 315-321 (1990).

Stahli et al., Distinction of Epitopes by Monoclonal Antibodies, Methods in Enzymology vol. 9, pp. 242-253 (1983).

Stefanescu, R. et al., Epitope Structure of the Carbohydrate Recognition Domain of Asialoglycoprotein Receptor to a Monoclonal Antibody Revealed by High-Resolution Proteolytic Excision Mass Spectrometry, Journal of the American Society for Mass Spectrometry, vol. 22, No. 1, pp. 148-157, 2011.

Steinthorsdottir et al., Identification of low-frequency and rare sequence variants associated with elevated or reduced risk of type 2 diabetes. Nature genetics vol. 46, pp. 294-298 (2014).

Steirer et al., The asialoglycoprotein receptor regulates levels of plasma glycoproteins terminating with sialic acid alpha2,6-galactose., The Journal of Biological Chemistry vol. 284, pp. 3777-3783 (2009).

Stockert et al., IgA interaction with asialoglycoprotein receptor, PNAS vol. 79, pp. 6229-6231 (1982).

Stockert et al., Hepatic Binding Protein: The Protective Role of its Sialic Acid Residues, Science vol. 197, pp. 667-668 (1977).

Subbarao et al., pH-Dependent Bilayer Destabilization by an Amphipathic Peptide, Biochemistry vol. 26, pp. 2964-2972 (1987).

Szybalska & Szybalski, Genetics of Human Cell Lines, IV. DNA-Mediated Heritable Transformation of a Biochemical Trait, Proc. Natl. Acad. Sci. USA vol. 48, pp. 202 (1992).

Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, vol. 164, No. 3, pp. 1432-1441, 2000.

Taylor et al., Human immunoglobuline transgenes undergo rearrangement, somatic mutation and class switching in mice that lack endogenous IgM, International Immunology vol. 6, pp. 579-591 (1994).

Taylor et al., A transgenic mouse that expresses a diversity of human sequence heavy and light chain immunoglobulins, Nucleic Acid Research vol. 20, pp. 6287-6295 (1992).

Thompson et al. Clustal W: improving the sensitivity of progressive multiple sequence alignment through sequence weighting, position-specific gap penalties and weight matrix choice, Nucleic Acids Res. vol. 22, pp. 4673-4680 (1994).

Thompson et al., Affinity Maturation of a High-Affinity Human Monoclonal Antibody Against the Third Hypervariable Loop of Human Immunodeficiency Virus: Use of Phase Display to Improve Affinity and Broaden Strain Reactivity, Journal of Molecular Biology vol. 256, pp. 7-88 (1996).

Thornton et al., Prediction of progress at last, Nature vol. 354, pp. 105 (1991).

Timms KM, Wagner S, Samuels ME, et al. A mutation in PCSK9 causing autosomal-dominant hypercholesterolemia in a Utah pedigree. Human genetics vol. 114, pp. 349-353 (2004).

Tomizuka et al., Functional expression and germline transmission of a human chromosome fragment in chimaeric mice, Nature Genetics vol. 16, pp. 133-143 (1997).

Tomizuka et al., Double trans-chromosomic mice: Maintenance of two individual human chromosome fragments containing Ig heavy and κ loci and expression of fully human antibodies, Proceedings of the National Academy of Sciences USA vol. 97, pp. 722-727 (2000).

Tozawa et al., Asialoglycoprotein receptor deficiency in mice lacking the major receptor subunit, It's obligate requirement for the stable expression of oligomeric receptor, The Journal of Biological Chemistry vol. 276, pp. 12624-12628 (2001).

Trahtenherts et al., "An Internalizing Antibody Specific for the Human Asialoglycoprotein Receptor", Hybridoma, vol. 28, No. 4, pp. 225-233, Nov. 4, 2009.

Trufert et al., Synthesis, Purification and Characterization of Two Peptide-Oligonucleotide Conjugates as Potential Artificial Nucleases, Tetrahedron vol. 52, pp. 3005 (1996).

Tsuda et al., Inactivation of the Mouse HPR Locus by a 203-bp Retroposon Insertion and a 55-kb Gene-Targeted Deletion: Establishment of New HPRT-Deficient Mouse Embryonic Stem Cell Lines, Genomics vol. 42, pp. 413-421 (1997).

Tuaillon et al., Biased Utilization of $D_{HQ52}$ and $J_H4$ Gene Segments in a Human Ig Transgenic Minilocus is Independent of Antigenic Selection, Journal of Immunology vol. 152, pp. 2912-2920 (1994).

Tuaillon et al., Human immunoglobulin heavy-chain minilocus recombination in transgenic mice: Gene-segment use in $\mu$ and $\gamma$ transcripts, Proceedings of the National Academy of Sciences USA vol. 90, pp. 3720-3724 (1993).

Tuin et al., On the role and fate of LPS-dephosphorylating activity in the rat liver, American Journal of Physiology Gastrointestinal and Liver Physiology vol. 290, pp. 377-385 (2006).

Turk et al., Characterization of a novel pH-sensitive peptide that enhances drug release from folate-targeted liposomes at endosomal pHs, Biochem. Biophys. Acta, vol. 1559, pp. 56-68 (2002).

Urlaub et al., Isolation of Chinese hamster cell mutants deficient in dihydrofolate reductase activity, Proc. Natl. Acad. Sci. USA vol. 77, pp. 4216-4220 (1980).

Van Den Hamer et al., Physical and chemical studies on ceruloplasmin. IX. The role of galactosyl residues in the clearance of ceruloplasmin from the circulation, The Journal of biological chemistry vol. 245, pp. 4397-4402 (1970).

Varret et al., A third major locus for autosomal dominant hypercholesterolemia maps to 1p34.1-p32, American journal of human genetics vol. 64, pp. 1378-1387 (1999).

(56) References Cited

OTHER PUBLICATIONS

Vaughan et al., Human antibodies by design, Nature Biotechnology vol. 16, pp. 535-539 (1998).
Vogel et al., Peptide-Mediated Release of Folate-Targeted Liposome Contents from Endosomal Compartments, J. Am. Chem. Soc. vol. 118, pp. 1581-1586 (1996).
Von Heinje, Sequence analysis in molecular biology, Academic Press, (1987).
Voss et al., The role of enhancers in the regulation of cell-type-specific transcriptional control, Trends Biochem. Sci. vol. 11, pp. 287 (1986).
Walder et al., Oligodeoxynucleotide-directed mutagenesis using the yeast transformation system, Gene vol. 42, pp. 133 (1986).
Yang, et al. Kukoamine B promotes TLR4-independent lipopolysaccharide uptake in murine hepatocytes, Oncotarget, vol. 7, No. 36, pp. 57948-57510, (2016).
Yang et al. Antisense oligonucleotides targeted against asialoglycoprotein receptor 1 block human hepatitis B virus replication, Journal of Viral Hepatitis, vol. 13, pp. 158-165, (2006).
Zapata et al., Engineering linear F(ab')$_2$ fragments for efficient production in *Escherichia coli* and enhanced antiproliferative activity, Protein Eng. vol. 8, pp. 1057-1062 (1995).
Zeng et al., "A Specific Antibody to the Carbohydrate Recognition Domain of the Asialoglycoprotein Receptor RHL1 Subunit Does Not React with RHL2/3 But Blocks Ligand Binding," Biochemical And Biophysical Research Communications, vol. 249, No. 1, pp. 236-240, 1998.
Zhang et al., Humanization of an anti-human TNF-α antibody by variable region resurfacing with the aid of molecular modeling, Molecular Immunology vol. 42(12), pp. 1445-1451 (2005).
Zupnick et al., Mutational Analysis of the p53 Core Domain L1 Loop, Journal of Biological Chemistry vol. 281(29), pp. 20464-20473 (2006).
Office action dated Jun. 24, 2020 in European application No. 16781931.7.
Wittrup et al., "Knocking Down Disease: A Progress Report on siRNA Therapeutics", Nature Reviews Genetics, vol. 16, Sep. 2015, pp. 543-552.
EPO Communication under Rule 164(2)(a) EPC dated Dec. 6, 2019 in European Application No. 16 781 931.7.
Abin754108: "Asialoglycoprotein Receptor 1 antibody (ASGR1) (AA 250-290)" in: Asialoglycoprotein Receptor 1 antibody (ASGR1) (AA 250-290). This may be a reference to a website: https://www.antibodies-online.com/antibody/754108/anti-Asialoglycoprotein+Receptor+1+ASGR1+AA+250-290+antibody/; anitbodies-online.com; Product information for ABIN754108. It is not clear from the source of the reference (the ISR and EPO communication). No date of publication is immediately apparent in the document. It may be that this reference was cited in a Communication under Rule 164(2)(a) EPC ("Communication") issued by the European Patent Office with regard to European Application No. 16781931.7, which is a counterpart application of the instant U.S. Application. The Communication listed a date for a reference noting this "abin#" of "Jan. 1, 2014 (Jan. 1, 2014)"; however, no copy of this reference is available to the Applicant, and Applicant cannot verify the listed date or that this is actually the reference in question. The copy of the webpage provided herewith has a printed on date of Feb. 26, 2020.
Exhibits A-1/2 from Response to Office Action, filed Feb. 27, 2020 in U.S. Appl. No. 16/230,356.
File History of U.S. Appl. No. 15/279,162, filed Sep. 28, 2016.
Spiess et al., Sequence Of A Second Human Asialoglycoprotein Receptor: Conservation Of Two Receptor Genes During Evolution, Proceedings Of The National Academy Of Sciences Of The United States Of America, vol. 82, pp. 6465-6469, 1985.
Rudikoff et al., Single amino Acid substitution altering Antigen-binding Specificity, Proceedings of the National Academy of Sciences of the United States of America, vol. 79, pp. 1979-1983, 1982.
Notice of Allowability in U.S. Appl. No. 16/230,356, dated Jul. 28, 2020.
Notice of Allowance in U.S. Appl. No. 16/230,356, dated May 8, 2020.
Office Action in U.S. Appl. No. 16/230,356, dated Nov. 27, 2019.
File History of U.S. Appl. No. 16/230,356, filed Dec. 21, 2018.
Schwartz, A. L., et al., Antibody-Induced Receptor Loss, The Journal of Biological Chemistry, vol. 261, No. 32, Issue of Nov. 15, pp. 15225-15232, 1986.
European Office Action for EP Application No. 16781931.7 in 4 pages, dated Dec. 6, 2019.
European Office Action for EP Application No. 16781931.7 in 5 pages, dated Feb. 17, 2021.
Invitation to Pay Additional Fees and Partial Search Report for PCT Application No. PCT/US2016/054222 in 16 pages, dated Jan. 10, 2017.
Japanese Office Action for JP Application No. 2018-515951 with English translation in 12 pages, dated Oct. 27, 2020.
Japanese Office Action for JP Application No. 2018-515951 with English translation in 12 pages, dated Sep. 7, 2021.
Notice of Allowability for U.S. Appl. No. 16/230,356 in 3 pages, dated Dec. 15, 2020.
Re-examination Report for JP Application No. 2018-515951 with English translation in 7 pages, dated Mar. 29, 2022.
Fazio, S. et al., Debate: "How low should LDL cholesterol be lowered?" Viewpoint: "It doesn't need to be very low", Current Controlled Trials in Cardiovascular Medicine, Feb. 2001, vol. 2(1), pp. 8-11.
Office Action for AU Application No. 2016332900 in 7 pages, dated Sep. 15, 2022.
Office Action for AU Application No. 2016332900 in 5 pages, dated Feb. 8, 2023.
Office Action for Canadian Application No. CA 2,997,444 in 4 pages, dated Nov. 24, 2022.
Exhibits A-1/2, showing results of a Multiple Dose Study of Anti-ASGR1 Antibodies, and a Study to Assess the Safety and Tolerability of Anti-ASGR1 Antibody. No date is apparent in the Exhibits. The same Exhibits was first submitted to the USPTO in U.S. Appl. No. 15/279,162, filed Jun. 18, 2018.
Office Action for Japanese Application No. JP 2022-019964 with English translation in 8 pages, dated Jul. 4, 2023.
Office Action for Australian Application No. AU 2016332900 in 2 pages, dated Jun. 21, 2023.
Office Action for Japanese Application No. JP 2018-515951 with English translation in 4 pages, dated Jul. 11, 2023.
Office Action for Japanese Application No. JP 2022-019964 with English translation in 8 pages, dated Jan. 17, 2023.
Summons to Attend Oral Proceedings for EP Application No. 16781931.7 in 6 pages, dated Apr. 13, 2023.
Communication under Rule 71(3) EPC (Intention to Grant) for European Application No. EP 16781931.7 in 5 pages, dated Nov. 23, 2023.
Notice of Acceptance for Australian Application No. AU 2016332900 in 3 pages, dated Aug. 23, 2023.
Office Action for Japanese Application No. JP 2018-515951 with English translation in 17 pages, dated Dec. 19, 2023.
Office Action for Japanese Application No. JP 2022-019964 with English translation in 8 pages, dated Dec. 19, 2023.
Result of Consultation for European Application No. EP 16781931.7 in 3 pages, dated Oct. 17, 2023.
Result of Consultation for European Application No. EP 16781931.7 in 3 pages, dated Oct. 20, 2023.

\* cited by examiner

Figure 1A

ASGR1 Full Seq Multiple Sequence Alignment

Figure 1B

Human ASGR1 Sequence Alignment

ASGR2 Full Seq Multiple Sequence Alignment

Figure 2

Human ASGR1 vs Human ASGR2v2 Alignment

Figure 5
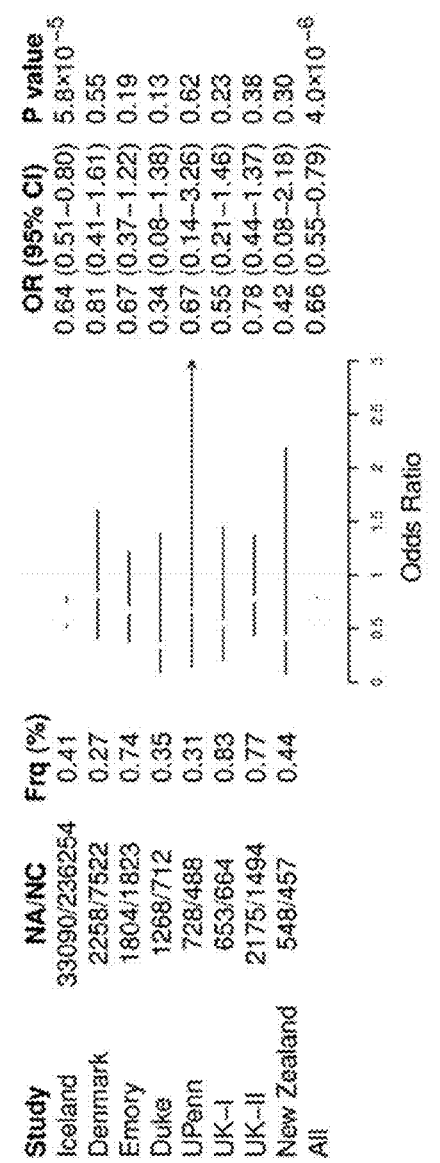
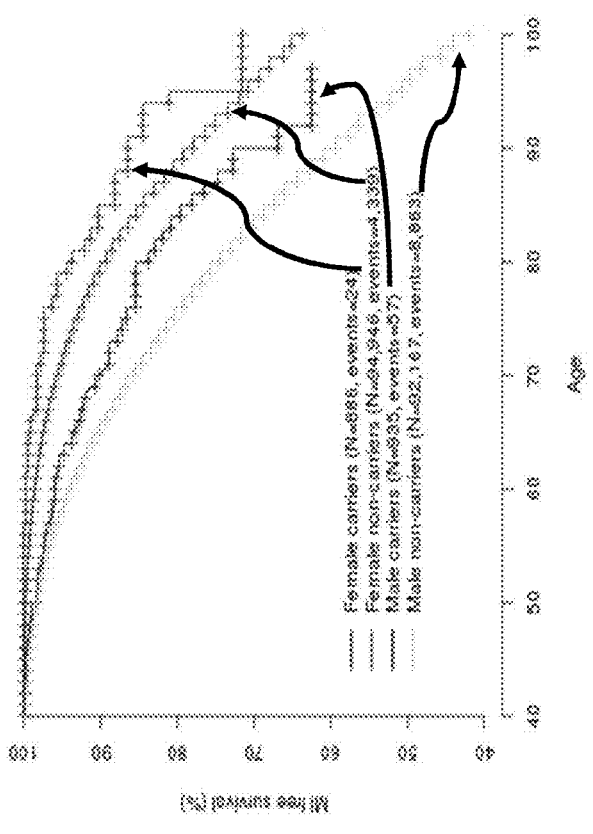
A.
B.

Figure 8
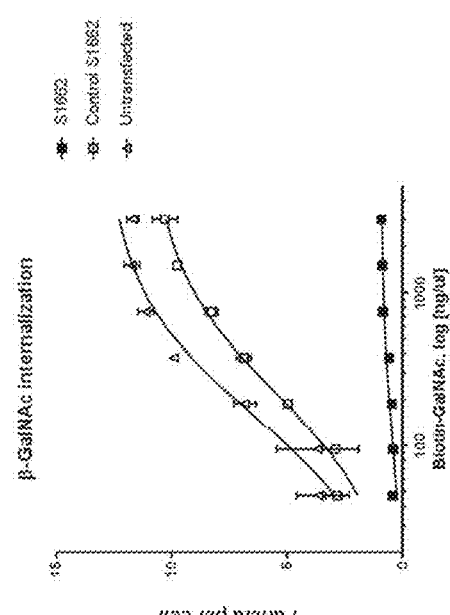
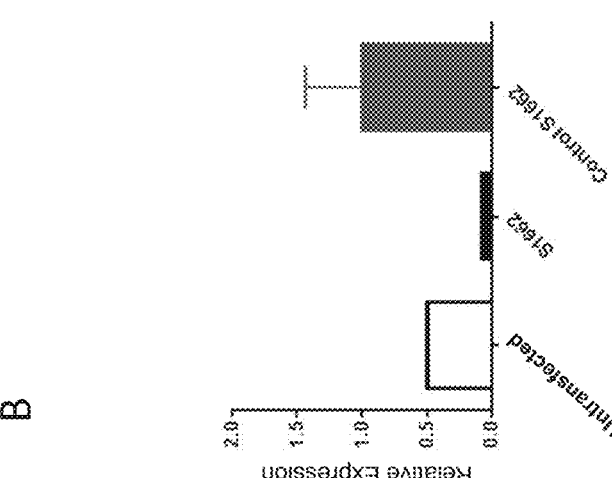
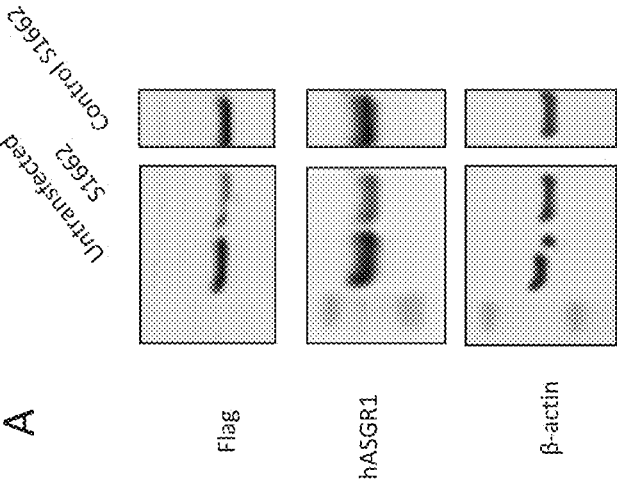

Figure 9
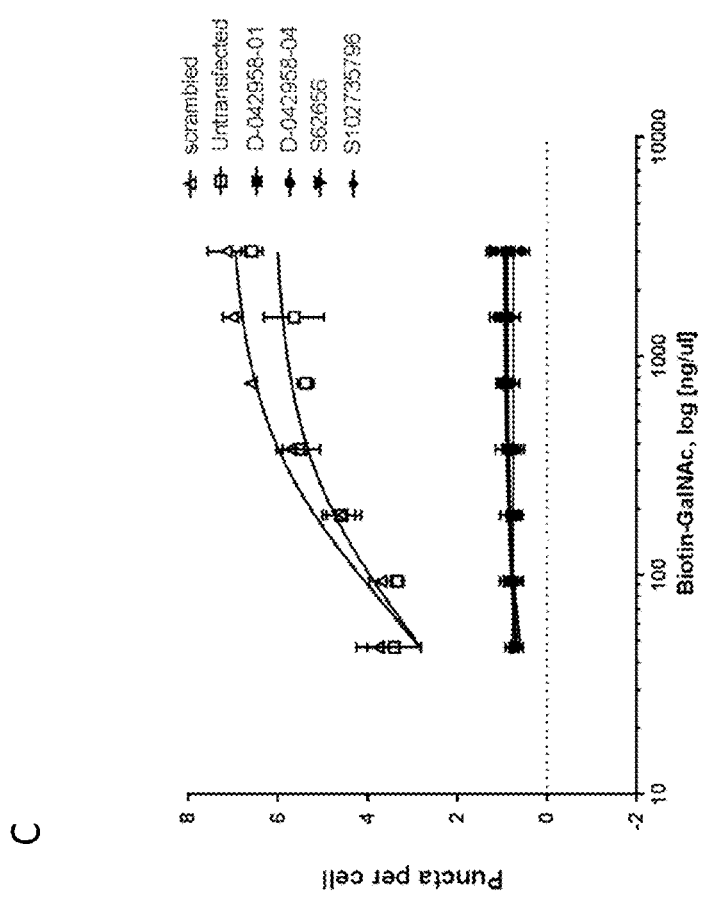
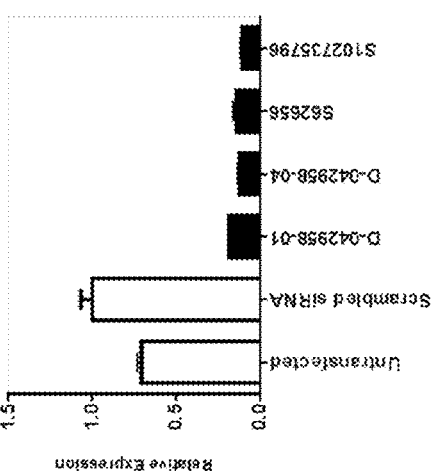
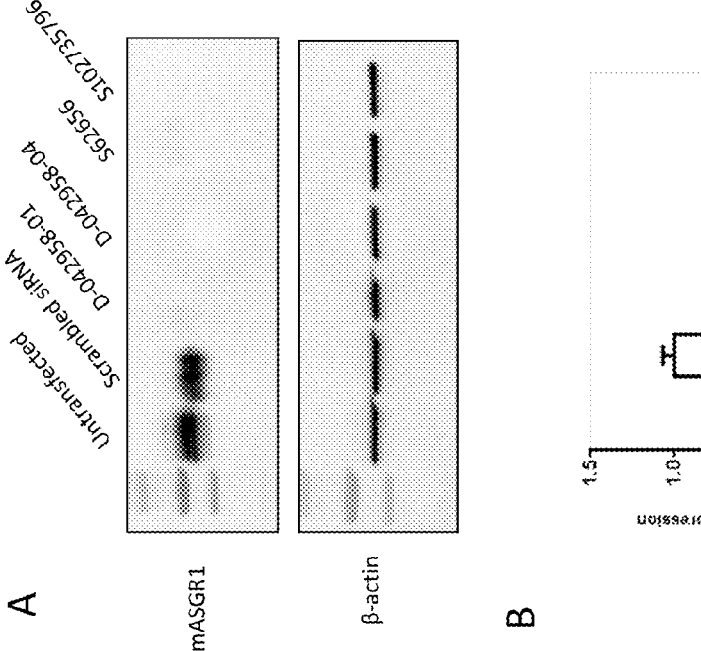

Figure 10
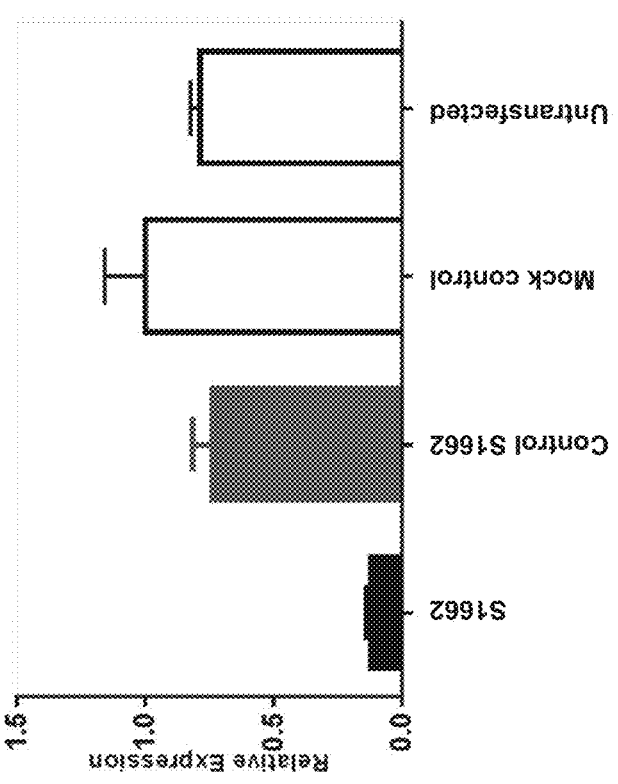
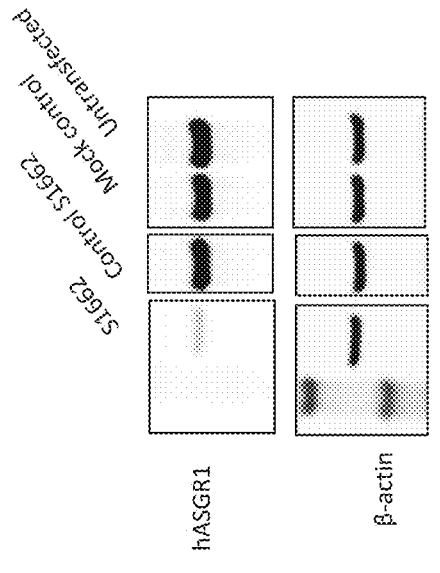

Figure 11
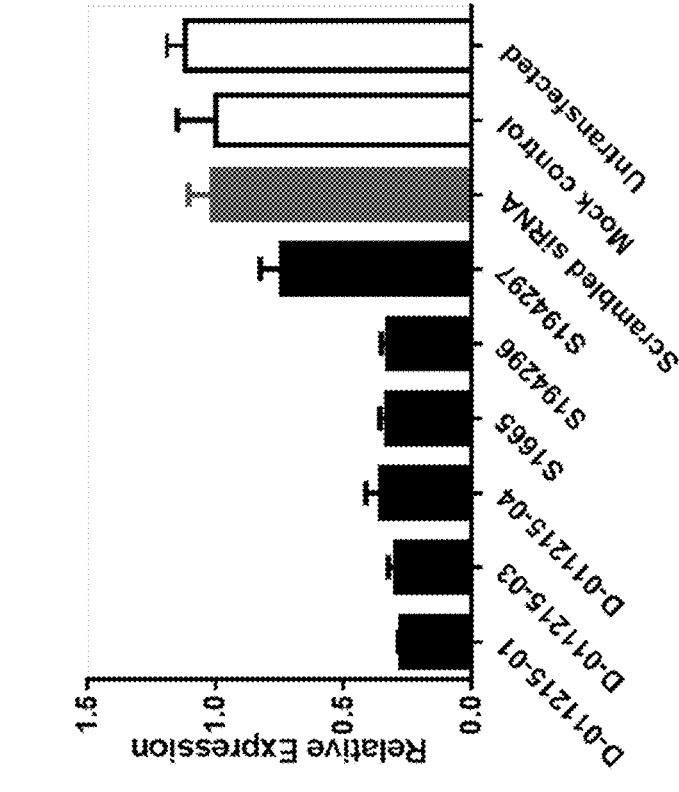
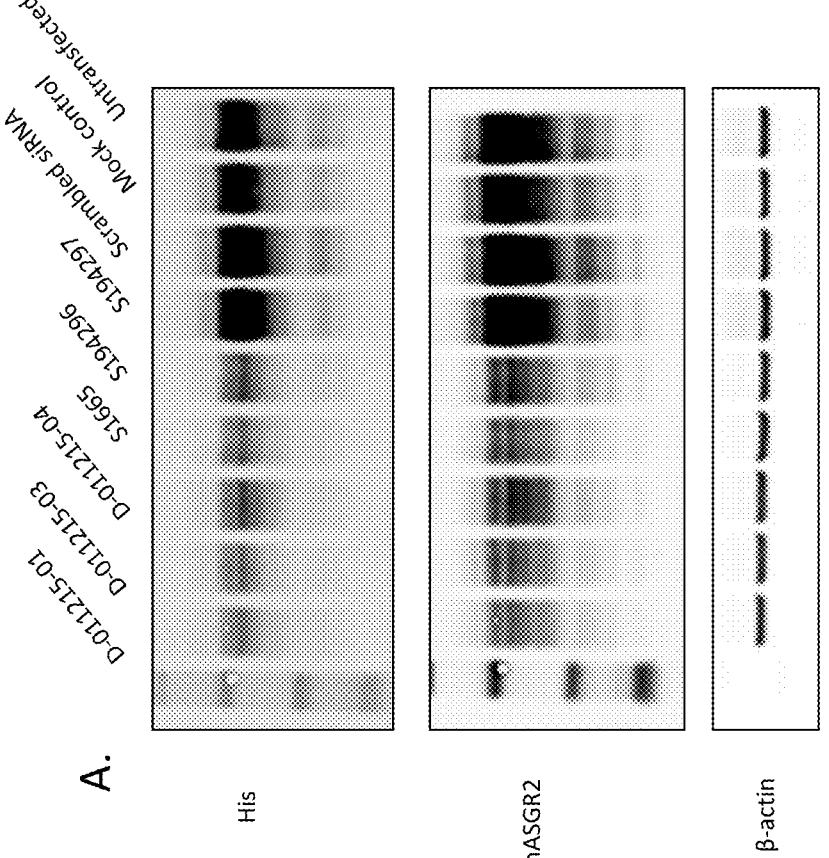

Figure 12
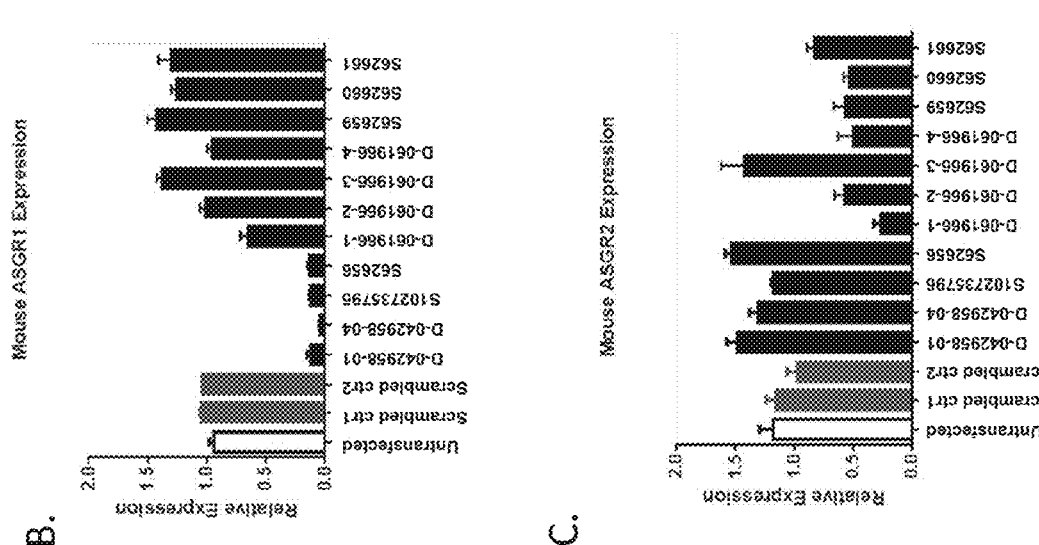
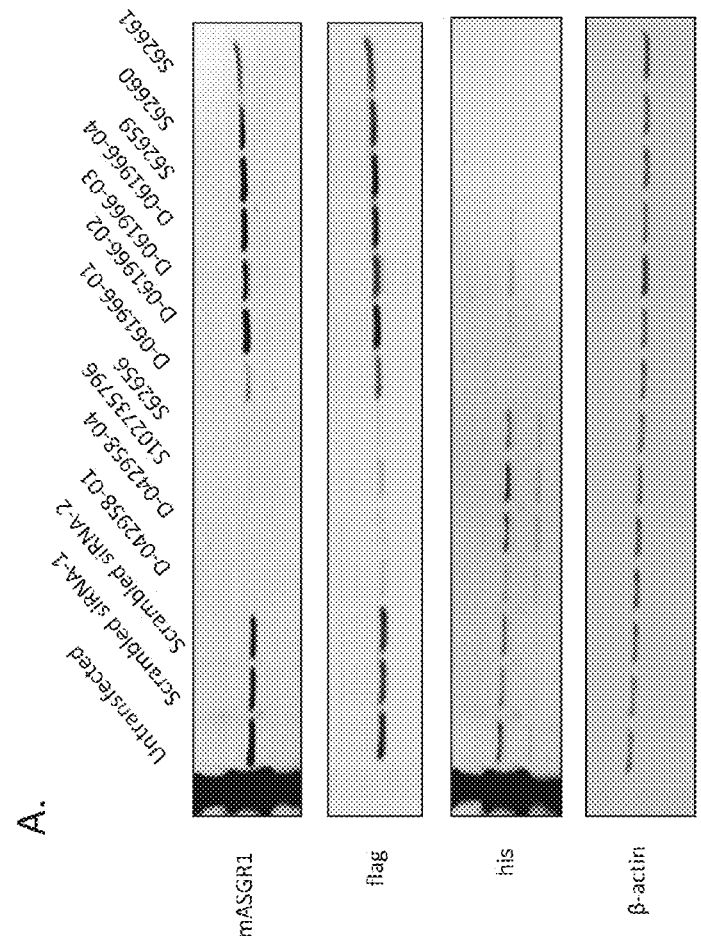

Figure 13
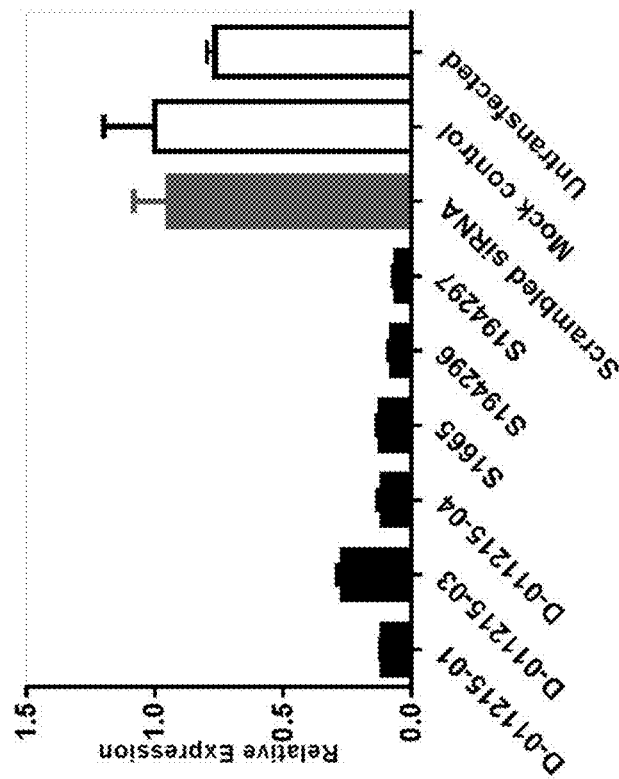
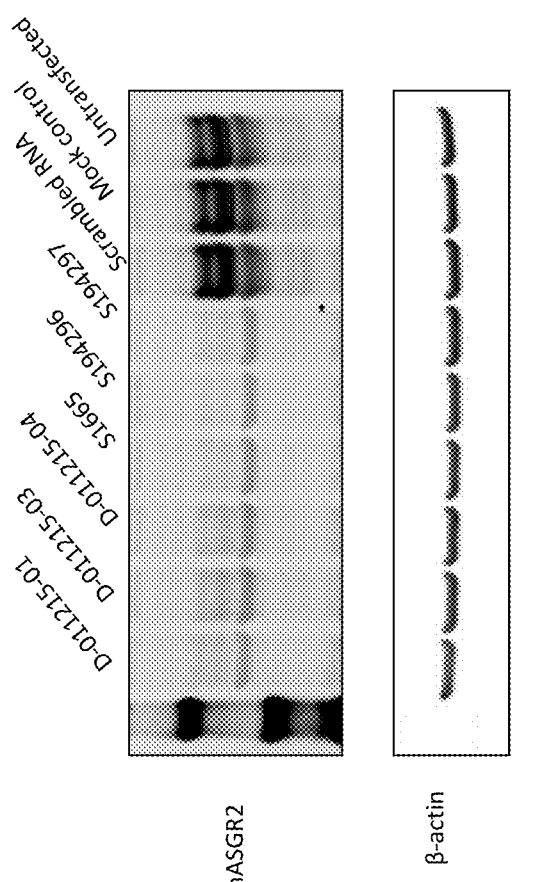

Figure 14
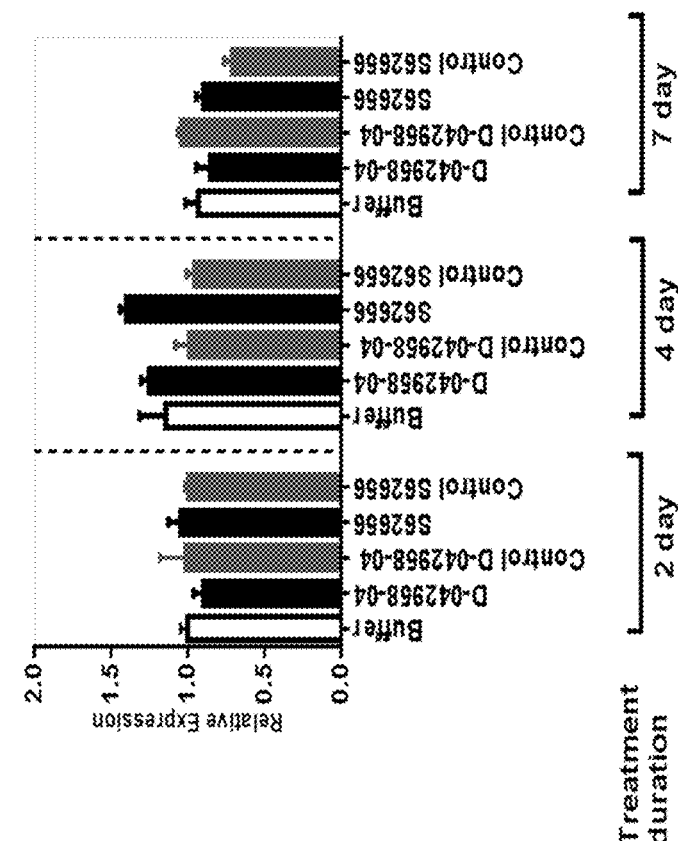
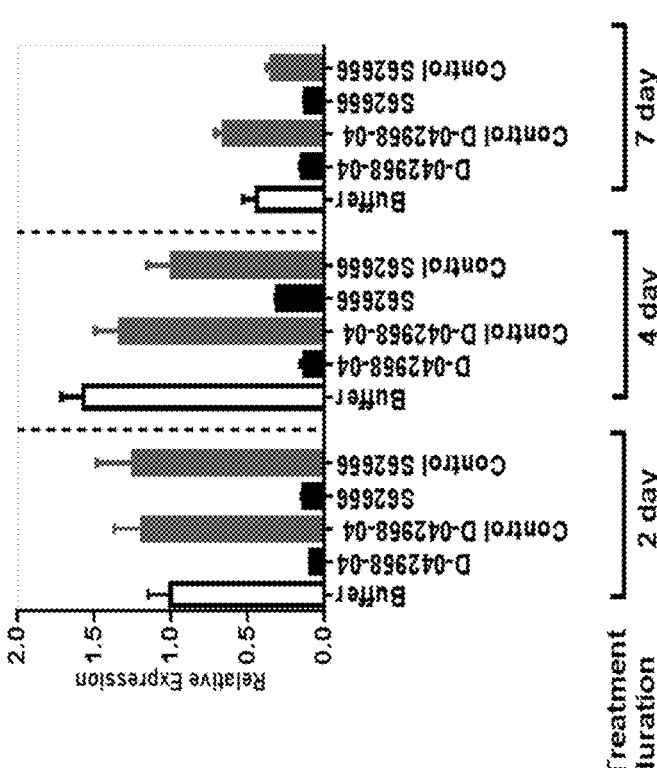

Figure 15
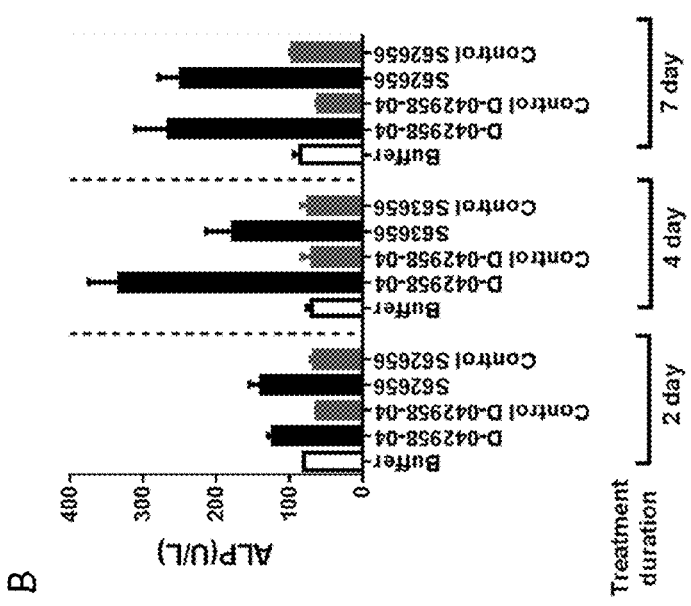
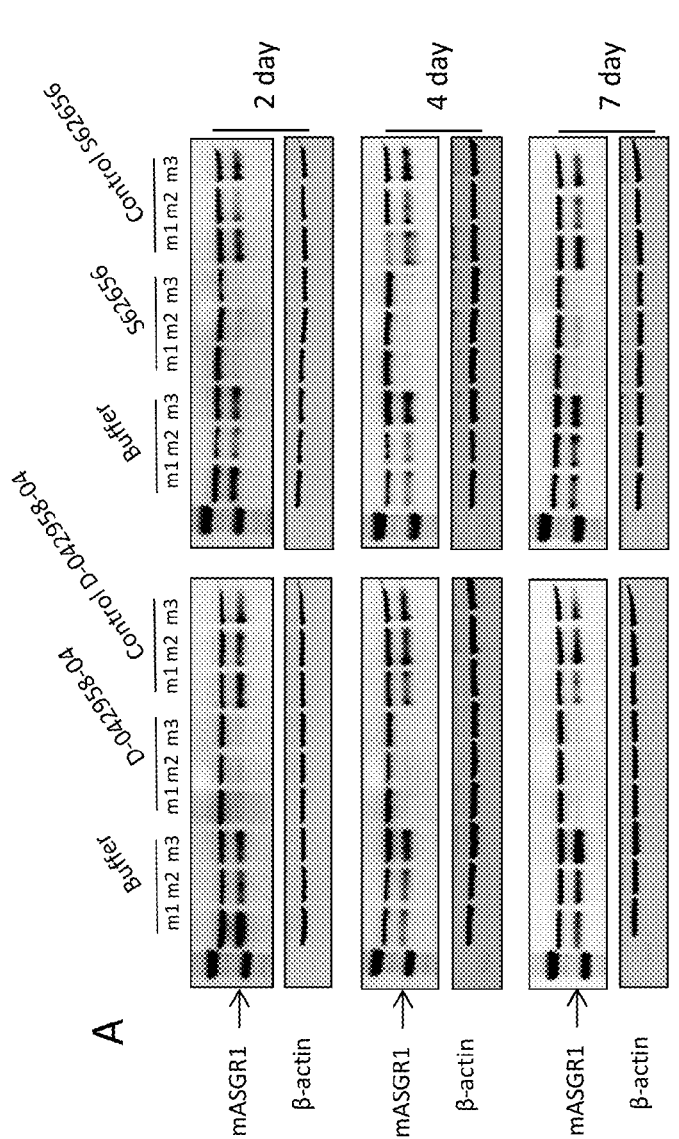

Figure 16
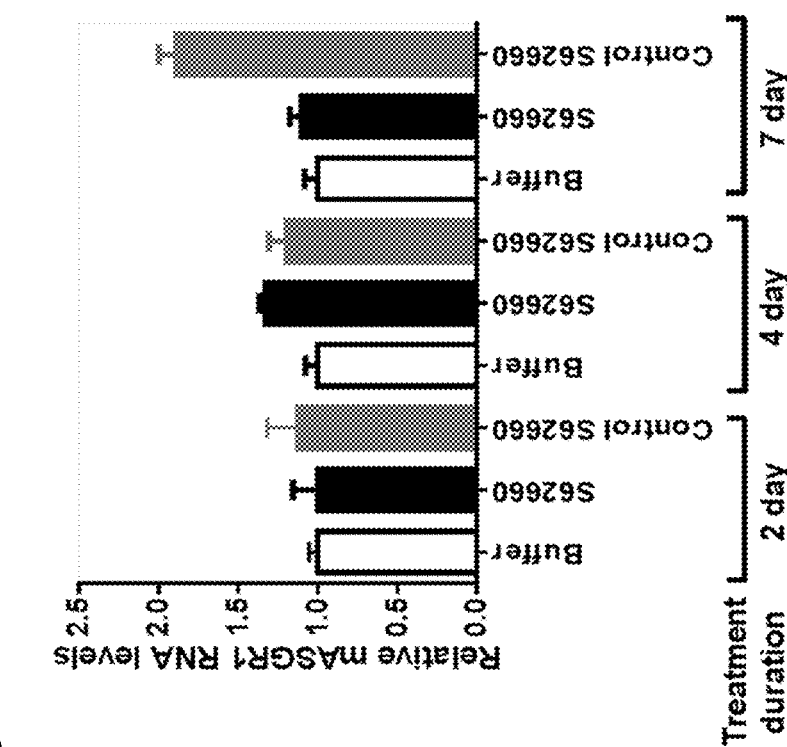
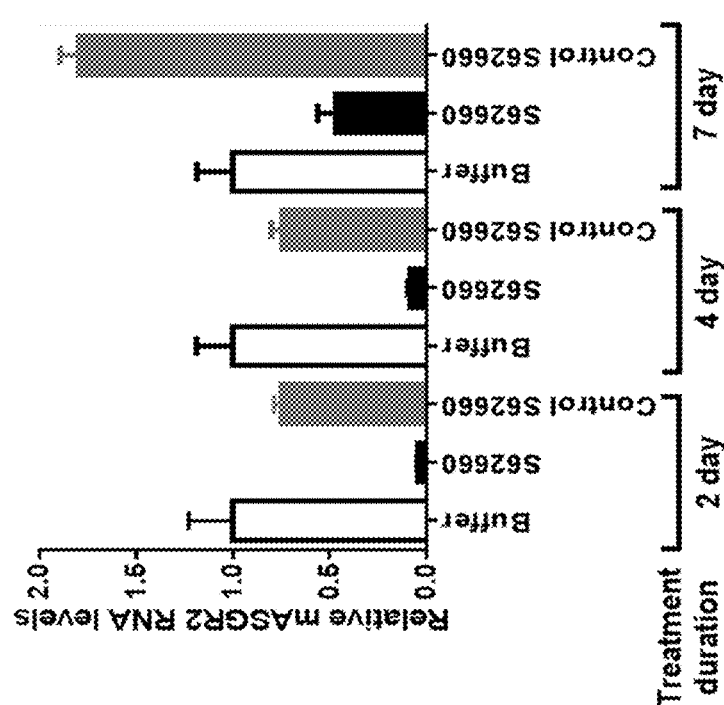

Figure 18
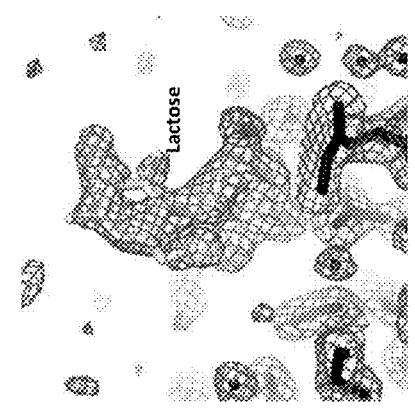
B
A
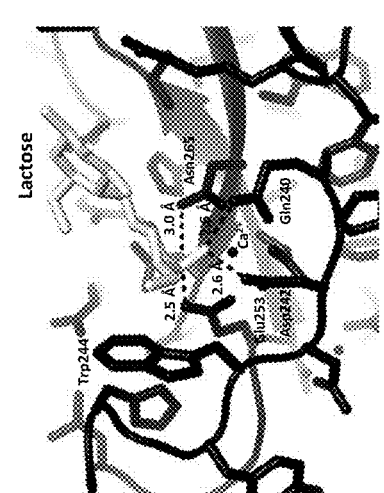
C

Figure 19
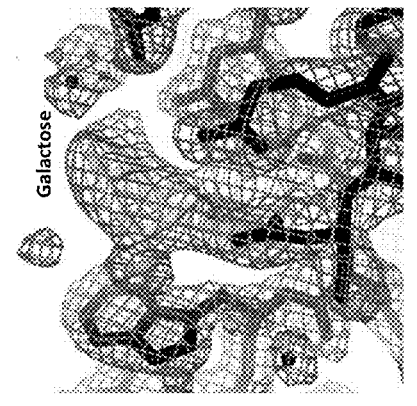
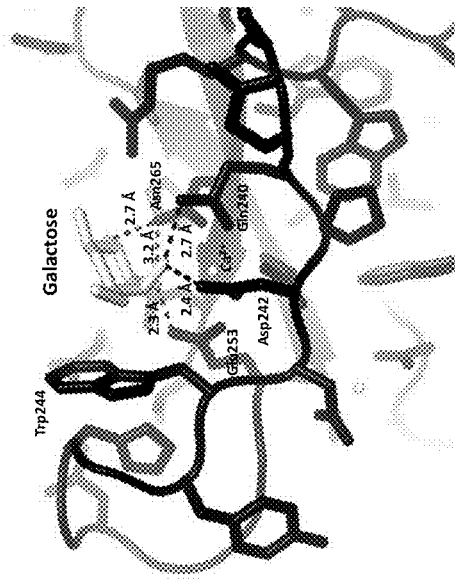

Figure 21
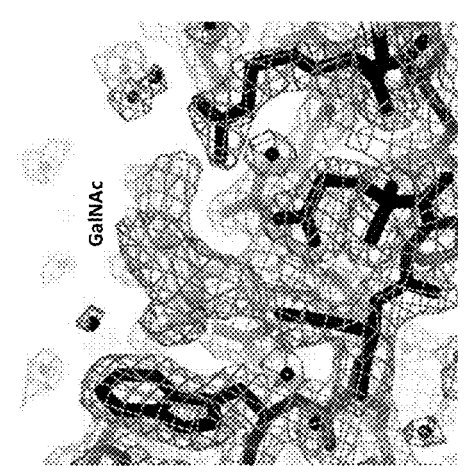
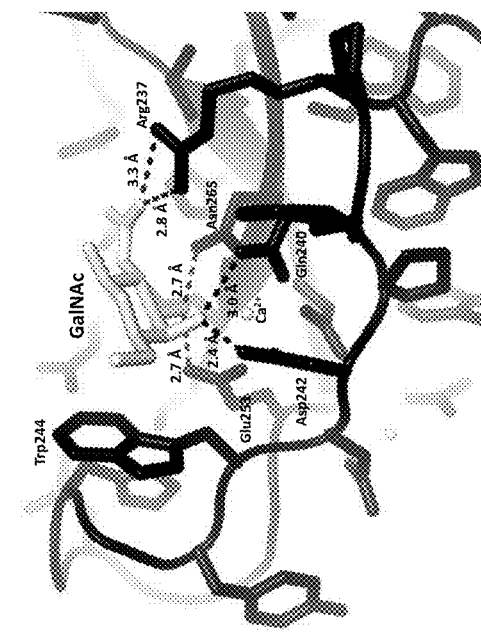
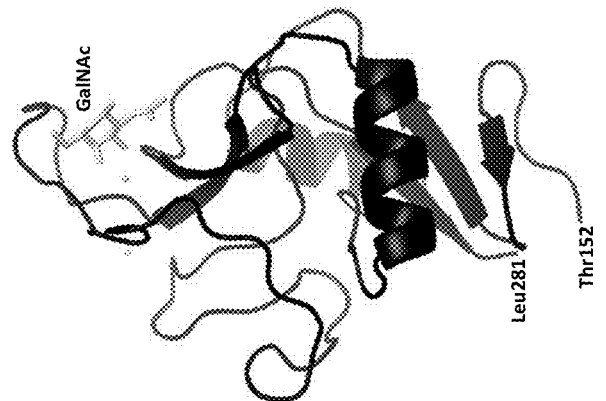

Figure 22
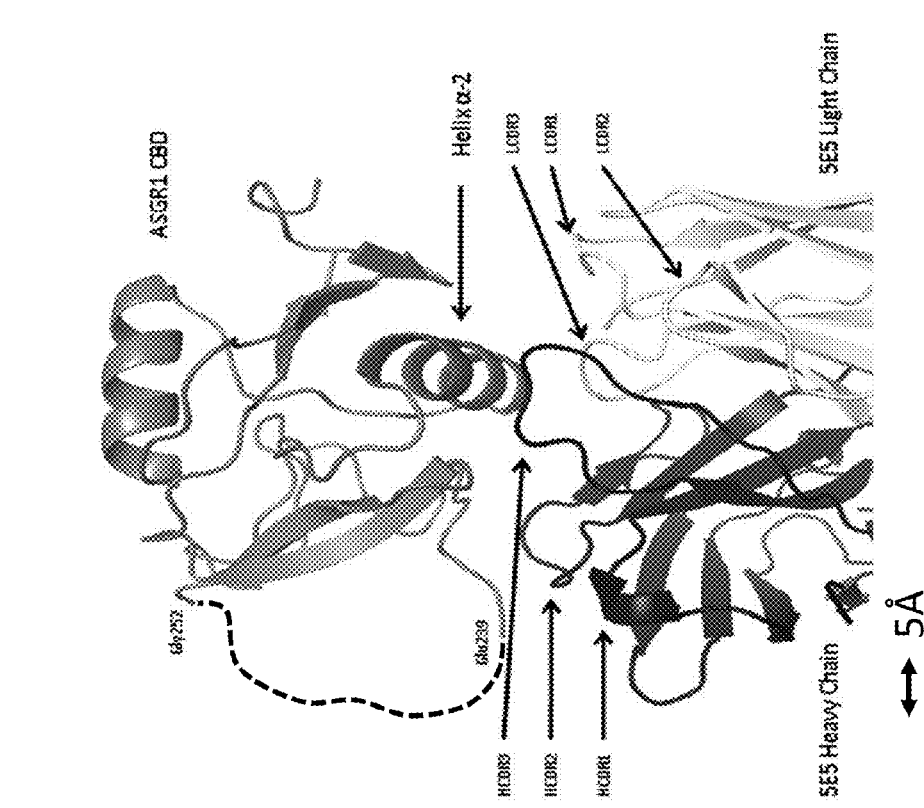
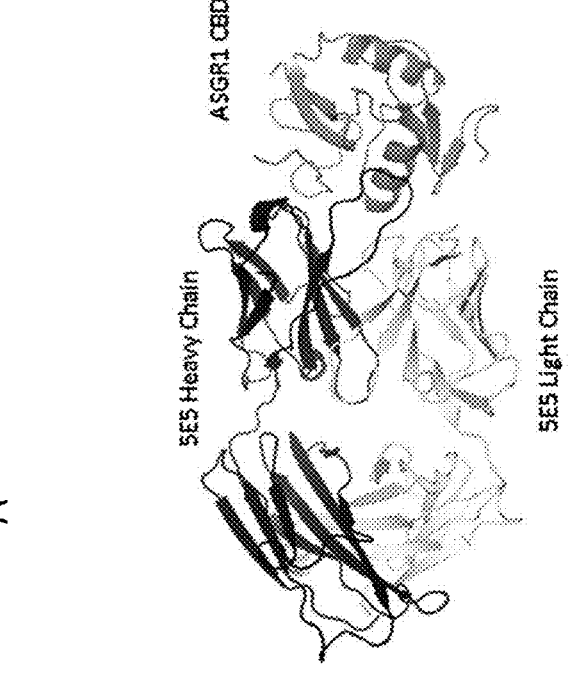

Figure 24
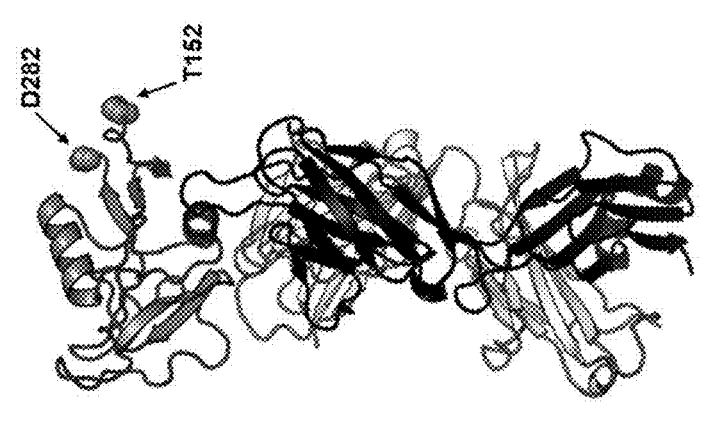
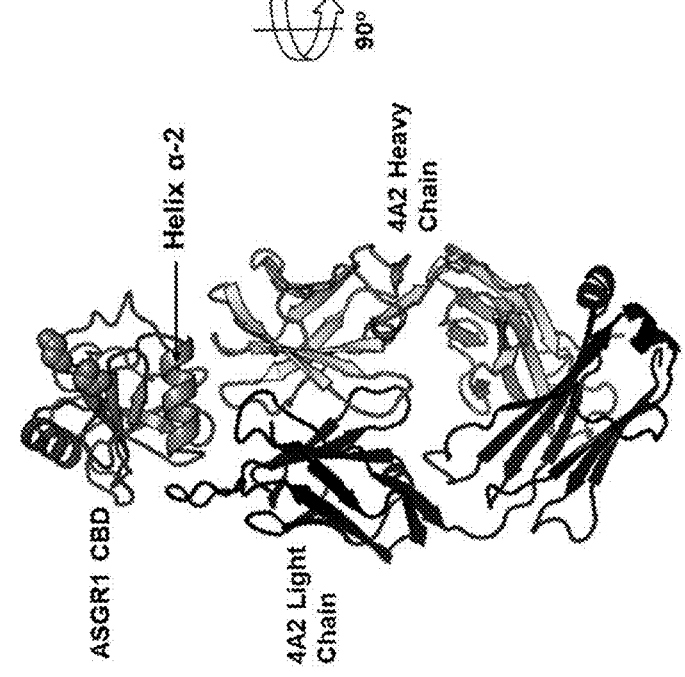

Figure 35
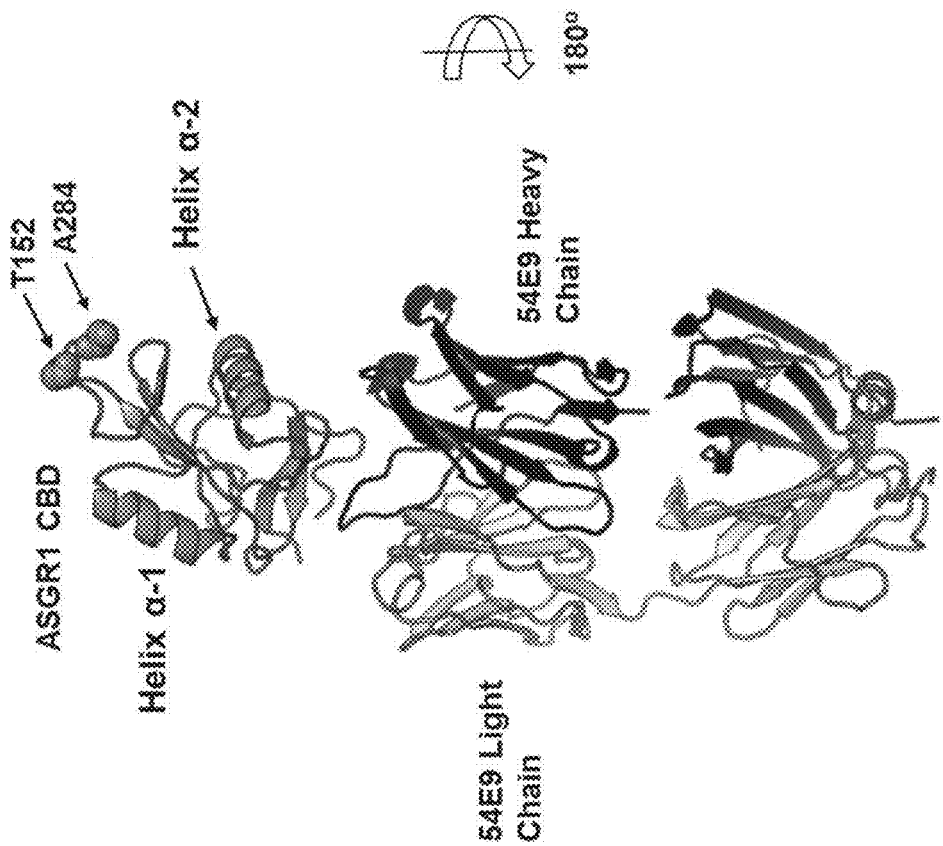

Figure 37
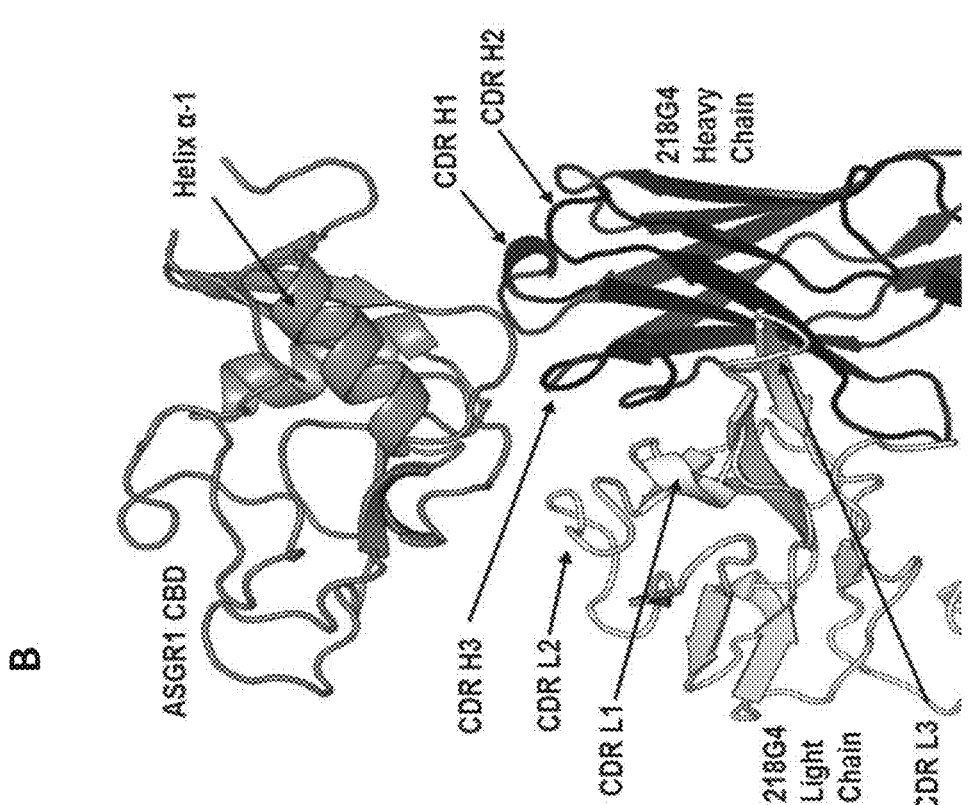
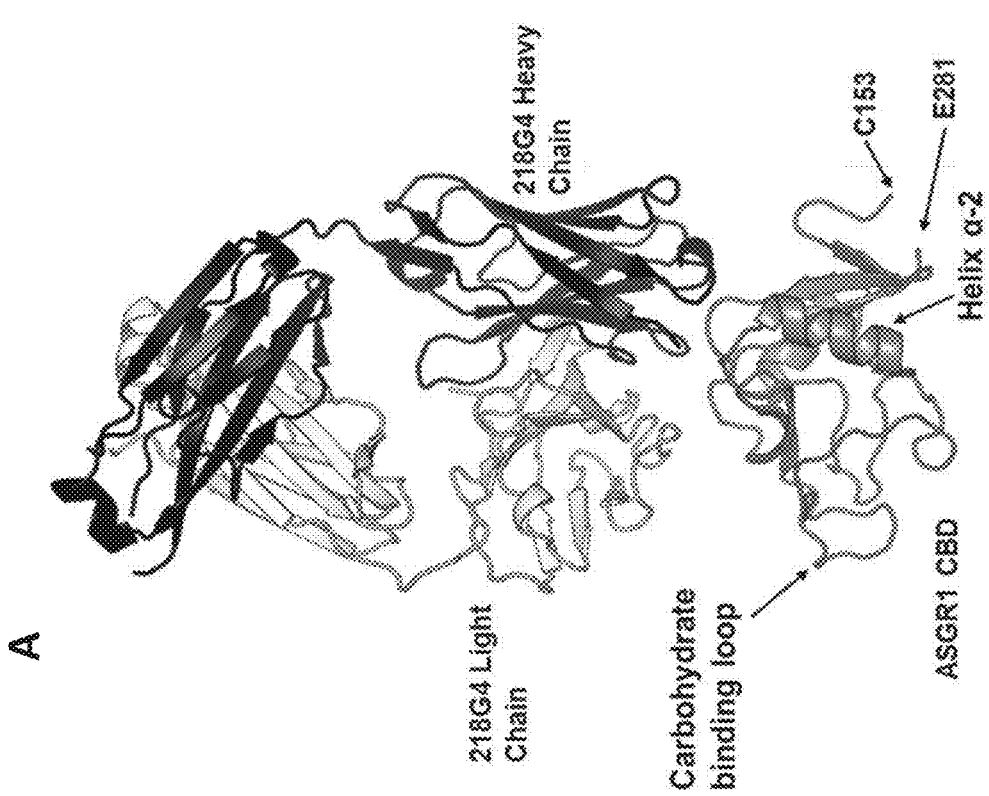

Binding of antibody 7F4 to parental and ASGR-expressing CHO-S cells

FIGURE 48

Table 1

Immunogens

| Name | Sequence Range | Tags | Amino Acid Sequence | Vector | SEQ ID NO: |
|---|---|---|---|---|---|
| muASGR1 | 1-284 | TCE | MTKDYQDFQHLDNDNDHHQLRRGPPPTPRLLQRLCSGSRLLLLSSSLSILLLVVVCVITSQNSQLREDLLALRQNFSNLTVSTEDQVKALSTQGSSVGRKMKLVESKLEKQQKDLTEDHSSLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTTDGRWNDDVCRRPYRWVCETKLDKAN | pTT5 | 1 |
| muAsgr2 | 1-301 | TCE | MEKDFCQDIQQLDSEENDHQLSGDEHGSHVQDPRIENPHWKGQPLSRPFPQRLCSTFRLSLLALAFNILLLVVICVVSSQSIQLQEEFRTLKETFSNFSSSTLMEFGALDTLGGSTNAILTSWLAQLEEKQQQLKADHSTLLFHLKHFPMDLRTLTCQLAYFQSNGTECCPVNWVEFGGSCYWFSRDGLTWAEADQYCQLENAHLLVINSREEQDFVVKHRSQFHIWIGLTDRDGSWKWVDGTDYRSNYRNWAFTQPDNWQGHEQGGGEDCAEILSDGHWNDNFCQQVNRWVCEKRRNITH | pTT5 | 2 |
| muASGR1(ECD) | 63-284 | TCE | SQLREDLLALRQNFSNLTVSTEDQVKALSTQGSSVGRKMKLVESKLEKQQKDLTEDHSSLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTTDGRWNDDVCRRPYRWVCETKLDKAN | pSLX235a | 3 |
| muASGR1(CBD) | 153-284 | TCE | CPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTTDGRWNDDVCRRPYRWVCETKLDKAN | pSLX235a | 4 |
| huASGR1 | 1-291 | TCE | MTKEYQDLQHLDNEESDHHQLRKGPPPPQPLLQRLCSGLCSGPRLLLLSLGLSLLLLVVVCVIGSSNSQLQEEERGLRETFSNFTASTEAQVKGLSTQGGNVGRKMKSLESQLEKQQKDLSEDHSSLLLHVKQFVSDLRSLSCQMAALQGNGSERTCCPVNWVEHERSCYWFSRSGKAWADADNYCRLEDAHLVVVTSWEEQKFVQHHIGPVNTWMGLHDQNGPWKWVDGTDYETGFKNWRPEQPDDWYGHGLGGGEDCAHFTDDGRWNDDVCQRPYRWVCETELDKASQEPPLL | pTT5 | 5 |
| huASGR2 | 1-287 | TCE | MAKDFQDIQQLSSEEENDHPFHQGPPPAQPLAQRLCSMVCFSLLALSFNILLLVVICVTGSQSAQLQAELRSLKEAFSNFSSSTLTEVGAISTHGGSVGDKITSLGAKLEKQQDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNWAVTQPDNWHGHELGGSEDCVEVQPDGRWNDDFCLQVYRWVCEKRRNATGEVA | pTT5 | 6 |
| huASGR1(ECD) | 64-291 | TCE | SQLQEELRGLRETFSNFTASTEAQVKGLSTQGGNVGRKMKSLESQLEKQQKDLSEDHSSLLLHVKQFVSDLRSLSCQMAALQGNGSERTCCPVNWVEHERSCYWFSRSGKAWADADNYCRLEDAHLVVVTSWEEQKFVQHHIGPVNTWMGLHDQNGPWKWVDGTDYETGFKNWRPEQPDDWYGHGLGGGEDCAHFTDDGRWNDDVCQRPYRWVCETELDKASQEPPLL | pSLX235a | 7 |
| huASGR1(CBD) | 154-291 | TCE | CPVNWVEHERSCYWFSRSGKAWADADNYCRLEDAHLVVVTSWEEQKFVQHHIGPVNTWMGLHDQNGPWKWVDGTDYETGFKNWRPEQPDDWYGHGLGGGEDCAHFTDDGRWNDDVCQRPYRWVCETELDKASQEPPLL | pSLX235a | 8 |

FIGURE 48
(Continued)

| Name | Sequence Range | Tags | Amino Acid Sequence | | |
|---|---|---|---|---|---|
| huASGR2(ECD) | 61-287 | TCE | QSAQLQAELRSLKEAFSNFSSSTLTEVQAISTHGGSVGDKITSLGAKLEKQQQDLKADHDALLFHLKHFPVQLRFV ACQMELLHSNGSQRTCCPVNWVEHQGSCYWFSHSGKAWAEAEKYCQLENAHLVVINSWEEQKFIVQHTNPFN TWIGLTDSDGSWKWVDGTDYRHNYKNWAVTQPDNWHGHELGGSEDCVEVQPDGRWNDDFCLQVYRWVCEK RRNATGEVA | pSLX235a | 9 |
| huASGR2(CBD) | 153-287 | TCE | CPVNWVEHQGSCYWFSHSGKAWAEAEKYCQLENAHLVVINSWEEQKFIVQHTNPFNTWIGLTDSDGSWKWVD GTDYRHNYKNWAVTQPDNWHGHELGGSEDCVEVQPDGRWNDDFCLQVYRWVCEKRRNATGEVA | pSLX235a | 10 |
| | | | Structural Work | | |
| Name | Sequence Range | Tags | Amino Acid Sequence | Vector | |
| M::huASGR1(154-281) | 154-281 | None | MCPVNWVEHERSCYWFSRSGKAWADADNYCRLEDAHLVVVTSWEEQKFVQHHIGPVNTWMGLHDQNGPWK WVDGTDYETGFKNWRPEQPDDWYGHGLGGGEDCAHFTDDGRWNDDVCQRPYRWVCETEL | pET21a | 11 |
| M::huASGR1(148-291) | 148-291 | None | MGSSERTCCPVNWVEHERSCYWFSRSGKAWADADNYCRLEDAHLVVVTSWEEQKFVQHHIGPVNTWMGLHDQ NGPWKWVDGTDYETGFKNWRPEQPDDWYGHGLGGGEDCAHFTDDGRWNDDVCQRPYRWVCETELDKASQ EPPLL | pET21a | 12 |
| MA::huASGR1(148-291) | 146-291 | None | MAGSERTCCPVNWVEHERSCYWFSRSGKAWADADNYCRLEDAHLVVVTSWEEQKFVQHHIGPVNTWMGLHD QNGPWKWVDGTDYETGFKNWRPEQPDDWYGHGLGGGEDCAHFTDDGRWNDDVCQRPYRWVCETELDKAS QEPPLL | pET21a | 13 |
| MA::huASGR1(154-281) | 154-281 | None | MACPVNWVEHERSCYWFSRSGKAWADADNYCRLEDAHLVVVTSWEEQKFVQHHIGPVNTWMGLHDQNGPW KWVDGTDYETGFKNWRPEQPDDWYGHGLGGGEDCAHFTDDGRWNDDVCQRPYRWVCETEL | pET21a | 14 |
| MA::huASGR1(60-153) | 60-153 | None | MAGSQNSQLQEELRGLRETFSNFTASTEAQVKGLSTQGGNVGRKMKSLESQLEKQQKDLSEDHSSLLLHVKQF VSDLRSLSCQMAALQGNGSSERTC | pET21a | 15 |
| MA::huASGR1(60-291) | 60-291 | None | MAGSQNSQLQEELRGLRETFSNFTASTEAQVKGLSTQGGNVGRKMKSLESQLEKQQKDLSEDHSSLLLHVKQF QHHIGPVNTWMGLHDQNGPWKWVDGTDYETGFKNWRPEQPDDWYGHGLGGGEDCAHFTDDGRWNDDVCQ RPYRWVCETELDKASQEPPLL | pET21a | 16 |
| MA::huASGR1(62-153) | 62-153 | None | MAQNSQLQEELRGLRETFSNFTASTEAQVKGLSTQGGNVGRKMKSLESQLEKQQKDLSEDHSSLLLHVKQF DLRSLSCQMAALQGNGSSERTC | pET21a | 17 |
| MA::huASGR1(58-153) | 58-153 | None | MAVIGSQNSQLQEELRGLRETFSNFTASTEAQVKGLSTQGGNVGRKMKSLESQLEKQQKDLSEDHSSLLLHVKQ FVSDLRSLSCQMAALQGNGSSERTC | pET21a | 18 |
| MA::huASGR1(58-143) | 58-143 | None | MAVIGSQNSQLQEELRGLRETFSNFTASTEAQVKGLSTQGGNVGRKMKSLESQLEKQQKDLSEDHSSLLLHVKQ FVSDLRSLSCQMAA | pET21a | 19 |
| MA::huASGR1(62-143) | 62-143 | None | MAQNSQLQEELRGLRETFSNFTASTEAQVKGLSTQGGNVGRKMKSLESQLEKQQKDLSEDHSSLLLHVKQFVS DLRSLSCQMAA | pET21a | 20 |
| MA::huASGR1(60-143) | 60-143 | None | MAGSQNSQLQEELRGLRETFSNFTASTEAQVKGLSTQGGNVGRKMKSLESQLEKQQKDLSEDHSSLLLHVKQF VSDLRSLSCQMAA | pET21a | 21 |

FIGURE 48
(Continued)

| | | | | |
|---|---|---|---|---|
| MA::huASGR1(60-282) | 60-282 | None | MAGSQNSQLQEELRGLRETFSNFTASTEAGVKGLSTQGGNVGRKMKSLESQLEKQKDLSEDHSSLLLHVKQF VSDLRSLSCQMAALQGNGSERTCCPVNWVEHERSCYWFSRSGKAWADADNYCRLEDAHLVVVTSWEEQKFV QHHIGPVNTWMGLHEQNGPWKWVDGTDYETGFKNWRPEQPDEWYGHGLGGGEDCAHFTEDDGRWNDDVCQ RPYRWVCETELD | pET21a | 22 |
| MA::huASGR1(62-291) | 62-291 | None | MAGNSQLQEELRGLRETFSNFTASTEAGVKGLSTQGGNVGRKMKSLESQLEKQKDLSEDHSSLLLHVKQFVS DLRSLSCQMAALQGNGSERTCCPVNWVEHERSCYWFSRSGKAWADADNYCRLEDAHLVVVTSWEEQKFVQH HIGPVNTWMGLHEQNGPWKWVDGTDYETGFKNWRPEQPDDWYGHGLGGGEDCAHFTEDDGRWNDDVCQRP YRWVCETELDKASQEPPLL | pET21a | 23 |
| MA::huASGR1(62-291) | 62-291 | None | MAGSQNSQLQEELRGLRETFSNFTASTEAGVKGLSTQGGNVGRKMKSLESQLEKQKDLSEDHSSLLLHVKQFV SDLRSLSCQMAALQGNGSERTCCPVNWVEHERSCYWFSRSGKAWADADNYCRLEDAHLVVVTSWEEQKFVQ HHIGPVNTWMGLHEQNGPWKWVDGTDYETGFKNWRPEQPDDWYGHGLGGGEDCAHFTEDDGRWNDDVCQR PYRWVCETELDKASQEPPLL | pET21a | 24 |
| MA::huASGR1(58-291) | 58-291 | None | MAVIGSQNSQLQEELRGLRETFSNFTASTEAQVKGLSTQGGNVGRKMKSLESQLEKQKQKDLSEDHSSLLLHVKQF VSDLRSLSCQMAALQGNGSERTCCPVNWVEHERSCYWFSRSGKAWADADNYCRLEDAHLVVVTSWEEQKF VQHHIGPVNTWMGLHDQNGPWKWVDGTDYETGFKNWRPEQPDDWYGHGLGGGEDCAHFTDDGRWNDDVC QRPYRWVCETELDKASQEPPLL | pET21a | 25 |
| MA::huASGR1(63-291) | 63-291 | None | MANSQLQEELRGLRETFSNFTASTEAQVKGLSTQGGNVGRKMKSLESQLEKQKDLSEDHSSLLLHVKQFVSDL RSLSCQMAALQGNGSERTCCPVNWVEHERSCYWFSRSGKAWADADNYCRLEDAHLVVVTSWEEQKFVQHH IGPVNTWMGLHDQNGPWKWVDGTDYETGFKNWRPEQPDDWYGHGLGGGEDCAHFTDDGRWNDDVCQRPYR WVCETELDKASQEPPLL | pET21a | 26 |
| MA::huASGR2(59-287) | 59-287 | None | MAGSQSAQLQAELRSLKEAFSNFSSSTLTEVQAISTHGGSVGDKITSLGAKLEKQQQDLKADHDALLFHLKHPV DLRFVACQMELLHSNGSQRTCCPVNWVEHQGSCYWFSHSGKAWAEAEKYCQLENAHLVVINSWEEQKFIVQH TNPFNTWIGLTDSDGSWKWVDGTDYRHNYKNWAVTQPDNWHGHELGGSSEDCVEVQPDGRWNDDFCLQVYR WVCEKRRNATGEVA | pET21a | 27 |
| MA::huASGR2(57-287) | 57-287 | None | MAVTGSQSAQLQAELRSLKEAFSNFSSSTLTEVQAISTHGGSVGDKITSLGAKLEKQQQDLKADHDALLFHLKHF PVDLRFVACQMELLHSNGSQRTCCPVNWVEHQGSCYWFSHSGKAWAEAEKYCQLENAHLVVINSWEEQKFIV QHTNPFNTWIGLTDSDGSWKWVDGTDYRHNYKNWAVTQPDNWHGHELGGSEDCVEVQPDGRWNDDFCLQV YRWVCEKRRNATGEVA | pET21a | 28 |
| MA::huASGR2(60-287) | 60-287 | None | MASQSAQLQAELRSLKEAFSNFSSSTLTEVQAISTHGGSVGDKITSLGAKLEKQQQDLKADHDALLFHLKHFPVDL RFVACQMELLHSNGSQRTCCPVNWVEHQGSCYWFSHSGKAWAEAEKYCQLENAHLVVINSWEEQKFIVQHTN PFNTWIGLTDSDGSWKWVDGTDYRHNYKNWAVTQPDNWHGHELGGSEDCVEVQPDGRWNDDFCLQVYRWV CEKRRNATGEVA | pET21a | 29 |
| MA::huASGR2(61-287) | 61-287 | None | MAQSAGLQAELRSLKEAFSNFSSSTLTEVQAISTHGGSVGDKITSLGAKLEKQQQDLKADHDALLFHLKHPVDL RFVACQMELLHSNGSQRTCCPVNWVEHQGSCYWFSHSGKAWAEAEKYCQLENAHLVVINSWEEQKFIVQHTN PFNTWIGLTDSDGSWKWVDGTDYRHNYKNWAVTQPDNWHGHELGGSEDCVEVQPDGRWNDDFCLQVYRWV CEKRRNATGEVA | pET21a | 30 |
| MA::huASGR2(62-287) | 62-287 | None | MASAQLQAELRSLKEAFSNFSSSTLTEVQAISTHGGSVGDKITSLGAKLEKQQQDLKADHDALLFHLKHPVDLRF VACQMELLHSNGSQRTCCPVNWVEHQGSCYWFSHSGKAWAEAEKYCQLENAHLVVINSWEEQKFIVQHTNPF NTWIGLTDSDGSWKWVDGTDYRHNYKNWAVTQPDNWHGHELGGSEDCVEVQPDGRWNDDFCLQVYRWVCE KRRNATGEVA | pET21a | 31 |

FIGURE 48
(Continued)

Complex Formation Assays

| Name | Sequence Range | Tags | Amino Acid Sequence | Vector | |
|---|---|---|---|---|---|
| huASGR1::GS::SNAP26f | 1-291 | SNAP26f | MTKEYQDLQHLDNEESDHHQLRKGPPPPQPLQRLCSGPRLLLLSLGLSLLLLVVVCVGSQNSQLQEELRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVVTSWEEQKFVQHHIGPVNTWMGLHDQNG PWKWVDGTDYETGFKNWRPEQPDDWYGHGLGGGEDCAHFTDDGRWNDDVCQRPYRWVCETELDKASQEP PLLGSSMDKDCEMKRTTLDSPLGKLELSGCEQGLHRIIFLGKGTSAADAVEVPAPAAVLGGPEPLMQATAWLNAYF HQPEAIEEFPVPALHHPVFQQESFTRQVLWKLLKVVKFGEVISYSHLAALAGNPAATAAVKTALSGNPVPILIPCHR VVQGDLDVGGYEGGLAVKEWLLAHEGHRLGKPGLG | pIRES_puro3.1 | 32 |
| huASGR1::GS::(G4S)3::SN AP26f | 1-291 | SNAP26f | MTKEYQDLQHLDNEESDHHQLRKGPPPPQPLQRLCSGPRLLLLSLGLSLLLLVVVCVGSQNSQLQEELRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGSGGGSGGGGSMDKDCEMKRTTLDSPLGKLELSGCEQGLHRIIFLGKGTSAADAVEVPAPAAVL GGPEPLMQATAWLNAYFHQPEAIEEFPVPALHHPVFQQESFTRQVLWKLLKVVKFGEVISYSHLAALAGNPAATA AVKTALSGNPVPILIPCHRVVQGDLDVGGYEGGLAVKEWLLAHEGHRLGKPGLG | pIRES_puro3.1, pJif1 | 33 |
| huASGR1::GS::CLIP | 1-291 | CLIP | MTKEYQDLQHLDNEESDHHQLRKGPPPPQPLQRLCSGPRLLLLSLGLSLLLLVVVCVGSQNSQLQEELRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVVTSWEEQKFVQHHIGPVNTWMGLHDQNG PWKWVDGTDYETGFKNWRPEQPDDWYGHGLGGGEDCAHFTDDGRWNDDVCQRPYRWVCETELDKASQEP PLLGSSMDKDCEMKRTTLDSPLGKLELSGCEQGLHRIIFLGKGTSAADAVEVPAPAAVLGGPEPLIQATAWLNAYF HQPEAIEEFPVPALHHPVFQQESFTRQVLWKLLKVVKFGEVISESHLAALVGNPAATAAVNTALDGNPVPILIPCH RVVQGDSDVGPYLGGLAVKEWLLAHEGHRLGKPGLG | pIRES_puro3.1, pJif1 | 34 |
| huASGR1::GS::(G4S)3::CL IP | 1-291 | CLIP | MTKEYQDLQHLDNEESDHHQLRKGPPPPQPLQRLCSGPRLLLLSLGLSLLLLVVVCVGSQNSQLQEELRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVVTSWEEQKFVQHHIGPVNTWMGLHDQNG PWKWVDGTDYETGFKNWRPEQPDDWYGHGLGGGSMDKDCEMKRTTLDSPLGKLELSGCEQGLHRIIFLGKGTSAADAVEVPAPAAVL GGPEPLIQATAWLLNAYFHQPEAIEEFPVPALHHPVFQQESFTRQVLWKLLKVVKFGEVISESHLAALVGNPAATAA VNTALDGNPVPILIPCHRVVQGDSDVGPYLGGLAVKEWLLAHEGHRLGKPGLG | pIRES_puro3.1, pJif1 | 35 |
| huASGR2::GS::SNAP26f | 1-287 | SNAP26f | MAKDFDIQIQGLSSEENDHPFHQGPPPAQPLAGRLCSMVCFSLLALSFNILLLVVICVTGSQSAGILQAELRSLKEAF SNFSSSTLTEVDAISTHSGSVEDKITSLSAKLEKQQGDLKADHDALLFHLKHFPVDLRFVACQMELLHSNGSQRT CCPVNWVEHQGSCYWFSHSGKAWAAEAEKYCQLENAHLVVINSWEEQKFVQHTNPFNTWIGLTDSDGSWKWV DGTDYRHNYKNWAVTQPDNWHGHELGGSEDCVEYQPDGRWNDDFCLGVYRWVCEKRRNATGEVAGSMDKD CEMKRTTLDSPLGKLELSGCQGLHRIIFLGKGTSAADAVEVPAPAAVLGGPEPLMQATAWLNAYFHQPEAIEEF PVPALIHPVFQQESFTRQVLWKLLKVVKFGEVISYSHLAALAGNPAATAAVKTALSGNPVPLIPCHRVVQGDLDV GGYEGGLAVKEWLLAHEGHRLGKPGLG | pIRES_puro3.1, pJif1 | 36 |

FIGURE 48
(Continued)

| Name | Range | Tag | Sequence | Vector | SEQ ID |
|---|---|---|---|---|---|
| huASGR2::GS::(G4S)3::SNAP26f | 1-287 | SNAP26f | MAKDFQDIQQLSSEENDHPFHQGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSMDKDCEMKRTTLDSPLGKLELSGCEQGLHRIIFLGKGTSAADAVEVPAPAAVLGGPEPLMQATAWLNAYFHQPEAIEEFPVPALHHPVFQQESFTRQVLWKLLKVVKFGEVISYSHLAALAGNPAATAAVKTALSGNPVPILIPCHRVVQGDLVGGYEGGLAVKEWLLAHEGHRLGKPGLG | pIRES_puro3.1 | 37 |
| huASGR2::GS::(G4S)3::CLIP | 1-287 | CLIP | MAKDFQDIQQLSSEENDHPFHQGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSMDKDCEMKRTTLDSPLGKLELSGCEQGLHRIIFLGKGTSAADAVEVPAPAAVLGGPEPLQATAWLNAYFHQPEAIEEFPVPALHHPVFQQESFTRQVLWKLLKVVKFGEVISESHLAALVGNPAATAAVNTALDGNPVPILIPCHRVVQGDSDVGPYLGGLAVKEWLLAHEGHRLGKPGLG | pIRES_puro3.1_pJiff1 | 38 |
| huASGR2::GS::(G4S)3::CLIP | 1-287 | CLIP | MAKDFQDIQQLSSEENDHPFHQGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSMDKDCEMKRTTLDSPLGKLELSGCEQGLHRIIFLGKGTSAADAVEVPAPAAVLGGPEPLQATAWLNAYFHQPEAIEEFPVPALHHPVFQQESFTRQVLWKLLKVVKFGEVISESHLAALVGNPAATAAVNTALDGNPVPILIPCHRVVQGDSDVGPYLGGLAVKEWLLAHEGHRLGKPGLG | pIRES_puro3.1 | 39 |
| huASGR2(v4)::GS::SNAP26f | 1-306 | SNAP26f | MAKDFQDIQQLSSEENDHPFHQGEGPGTRRLNPRRGNPFLKGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSGGGSGGGSGGGSMDKDCEMKRTTLDSPLGKLELSGCEQGLHRIIFLGKGTSAADAVEVPAPAAVLGGPEPLMQATAWLNAYFHQPEAIEEFPVPALHHPVFQQESFTRQVLWKLLKVVKFGEVISYSHLAALAGNPAATAAVKTALSGNPVPILIPCHRVVQGDLVGGYEGGLAVKEWLLAHEGHRLGKPGLG | pIRES_puro3.1 | 40 |
| huASGR2(v4)::GS::SNAP26f | 1-306 | SNAP26f | MAKDFQDIQQLSSEENDHPFHQGEGPGTRRLNPRRGNPFLKGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSMDKDCEMKRTTLDSPLGKLELSGCEQGLHRIIFLGKGTSAADAVEVPAPAAVLGGPEPLMQATAWLNAYFHQPEAIEEFPVPALHHPVFQQESFTRQVLWKLLKVVKFGEVISYSHLAALAGNPAATAAVKTALSGNPVPILIPCHRVVQGDLVGGYEGGLAVKEWLLAHEGHRLGKPGLG | pIRES_puro3.1_pJiff1 | 41 |
| huASGR2(v4)::GS::CLIP | 1-306 | CLIP | MAKDFQDIQQLSSEENDHPFHQGEGPGTRRLNPRRGNPFLKGPPPAQPLAGRLCSMVCFSLLALSFNILLLVVICVTGSQSAQLQAELRSLKEAFSNFSSSTLTEVQAISTHGGSVGDKITSLGAKLEKQQGDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNMAVTQPDNWHGHELGGSEDCVEVQPDGRWNDDFCLQVYRWVCEKRRNATGEVAGSMDKDCEMKRTTLDSPLGKLELSGCEQGLHRIIFLGKGTSAADAVEVPAPAAVLGGPEPLQATAWLNAYFHQPEAIEEFPVPALHHPVFQQESFTRQVLWKLLKVVKFGEVISESHLAALVGNPAATAAVNTALDGNPVPILIPCHRVVQGDSDVGPYLGGLAVKEWLLAHEGHRLGKPGLG | pIRES_puro3.1 | 42 |

FIGURE 48
(Continued)

| Name | Range | Tag | Sequence | Vector | SEQ ID |
|---|---|---|---|---|---|
| huASGR2(v4)::GS::(G4S)3::CLIP | 1-306 | CLIP | MAKDFQDIQLSSEEENDHPFHQGEGPGTRRLNPRRGNPFLKGPPPAQPLAQRLCSMVCFSLLALSFNILLLVVIC VTGSQSAQLQAELRSLKEAFSNFSSSTLTEVQAISTHQGSVGDKITSLGAKLEKQQQDLKADHDALLFHLKHFPVD LRFVACQMELLHSNGSQRTCCPVNWVEHQGSCYWFSHSGKAWAEAEKYCQLENAHLVVINSWEEQKFVQHT NPFNTWIGLTDSDGSWKWVDGTDYRHNYKNWAVTQPDNWHGHELGGSEDCVEVQPDGRWNDDFCLQVVRW VCEKRRNATGEVAGSGGGGSGGGGSGGGGSMDKDCEMKRTTLDSPLGKLELSGCEQGLHRIIFLGKGTSAADA VEVPAPAAVLGGPEPLIQATAWLNAYFHQPEAIEEFPVPAALHHPVFQGESFTRQVLWKLLKVVKFGEVSESHLAA LVGNPAATAAVNTALDGNPVPILIPCHRVVQGSDSDVGPYLGGLAVKEWLLAHEGHRLGKPGLG | pIRES_puro3.1 | 43 |

Mammalian Expression

| Name | Range | Tag | Sequence | Vector | SEQ ID |
|---|---|---|---|---|---|
| huASGR1 | 1-291 | None | MTKEYQDLQHLDNEESDHHQLRKGPPPPQPLLQRLCSGPRLLLSLGLSLLLLVVVCVIGSQNSQLQEEFLRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPYRWVCETELDKASQEP PLL | pTT5, pSLX235a, pJiF1 | 44 |
| huASGR1(Y273C) | 1-291 | None | MTKEYQDLQHLDNEESDHHQLRKGPPPPQPLLQRLCSGPRLLLSLGLSLLLLVVVCVIGSQNSQLQEEFLRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPCRWVCETELDKASQEP PLL | pTT5, pSLX235a, pJiF1 | 45 |
| huASGR1::Flag | 1-291 | Flag | MTKEYQDLQHLDNEESDHHQLRKGPPPPQPLLQRLCSGPRLLLSLGLSLLLLVVVCVIGSQNSQLQEEFLRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPYRWVCETELDKASQEP PLLDYKDDDDK | pTT5, pSLX235a | 46 |
| huASGR1(Y273C)::Flag | 1-291 | Flag | MTKEYQDLQHLDNEESDHHQLRKGPPPPQPLLQRLCSGPRLLLSLGLSLLLLVVVCVIGSQNSQLQEEFLRGLRE TFSNFTASTEAQVKGLSTQGGNVGRKMKSLESQLEKQQKDLSEDHSSLLLHVKQFVSDLRSLSCQMAALQGNG SERTCCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPCRWVCETELDKASQEP PLLDYKDDDDK | pTT5, pSLX235a | 47 |
| cyASGR1 | 1-291 | None | MTKEYQDLQHLDNEESDHHQLGKGPPPPQGSLLRRLCSGPRLLLSLGLSLLLLVVVCVIGSQNAQLQRELRGLRE TLSNFTASTEAQVKGLSTQGGNVEHERSCYWFSRSGKAWADADNYCRLEDAHLVVTSWEEQKFYQHHIGPVNTWMGLHDQNG SERACCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPYRWVCETELDKASQEP PLL | pTT5, pSLX235a | 48 |
| cyASGR1(Y273C) | 1-291 | None | MTKEYQDLQHLDNEESDHHQLGKGPPPPQGSLLRRLCSGPRLLLSLGLSLLLLVVVCVIGSQNAQLQRELRGLRE TLSNFTASTEAQVKGLSTQGGNVEHERSCYWFSRSGKAWADADNYCRLEDAHLVVTSWEEQKFYQHHIGPVNTWMGLHDQNG SERACCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPCRWVCETELDKASQEP PLL | pTT5, pSLX235a | 49 |
| cyASGR1::Flag | 1-291 | Flag | MTKEYQDLQHLDNEESDHHQLGKGPPPPQGSLLRRLCSGPRLLLSLGLSLLLLVVVCVIGSQNAQLQRELRGLRE TLSNFTASTEAQVKGLSTQGGNVEHERSCYWFSRSGKAWADADNYCRLEDAHLVVTSWEEQKFYQHHIGPVNTWMGLHDQNG SERACCPVNWVEHERSCYWFSRSGKAWADADNYCRLEDAHLVVTSWEEQKFYQHHIGPVNTWMGLHDQNG PWKWVDGTDYETGFKNWRPEQPDDWYGHGLGGGEDCAHFTDDGRWNDDVCQRPYRWVCETELDKASQEP PLLDYKDDDDK | pTT5, pSLX235a | 50 |

FIGURE 48
(Continued)

| Name | Range | Tag | Sequence | Vector | SEQ ID |
|---|---|---|---|---|---|
| cyASGR1(Y273C)::Flag | 1-291 | Flag | MTKEYQDLQHLDNEESDHHQLGKGPPPPQSLLRRLCSGPRLLLLSLGLSLILLVVVCVIGSQNAQLQRELRGLRETLSNFTASTEAQVKGLSTQGGNVGRKMKSLESQLEKQQKDLSEDHSSLLLHVKQFSDLRSLSCQMAALQGNGSERACCPVNWVEHERSCYWFSRSGKAWADADNYCRLEDAHLVVVTSWEEQKYQHHIGPVNTWMGLHDQNGPWKWVDGTDYETGFKNWRPEQPDDWYGHGLGGGEDCAHFTDDGRWNDDVCQRPCRWVCETELDKASQEPPLLDYKDDDDK | pTT5, pSLX235a | 51 |
| muASGR1 | 1-284 | None | MTKDYQDFQHLDNDNDHHQLRRGPPPTPRLLQRLCSGSRLLLLQRLCSGSRLLLLSSSLSILLLVVVCVITEDHSSLLLLHVKQLVSDVRSLSCQMAAFRGNGSERSNLTVSTEDQVKALSTQGSSVGRKMKLVESKLEKQQKDITEDHSSLLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTDGRWNDDVCRRPYRWVCETKLDKAN | pTT5, pJF1 | 52 |
| muASGR1(Y272C) | 1-284 | None | MTKDYQDFQHLDNDNDHHQLRRGPPPTPRLLQRLCSGSRLLLLQRLCSGSRLLLLSSSLSILLLVVVCVITEDHSSLLLLHVKQLVSDVRSLSCQMAAFRGNGSERSNLTVSTEDQVKALSTQGSSVGRKMKLVESKLEKQQKDITEDHSSLLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTDGRWNDDVCRRPCRWVCETKLDKAN | pTT5, pSLX235a, pJF1 | 53 |
| ratASGR1 | 1-284 | None | MTKDYQDFQHLDNENDHHQLQRGPPPAPRLLQRLCSGFRLRLFLLSLGLSLILLHVKQLVSDVREDLRVLRQNFSNFTVSTEDQVKALTQGERVGRKMKLVESGLEKHQEDLREDHSRLLLLHVKQLVSDVREDLRVLRQNFRICCPINWVEYEGSCYWFSSVKPWTEADKYCQLENAHLVVVTSWEEQRFVQQHMGPLNTWIGLTDGNGPWKWVDGTDYETGFKNWRPGQPDDWYGHGLGGGEDCAHFTTDGHWNDDVCRRPYRWVCETELGKAN | pTT5, pSLX235a | 54 |
| ratASGR1(Y272C) | 1-284 | None | MTKDYQDFQHLDNENDHHQLQRGPPPAPRLLQRLCSGFRLFLLSLGLSLILLHVKQLVSDVREDLRVLRQNFSNFTVSTEDQVKALTQGERVGRKMKLVESGLEKHQEDLREDHSRLLLLHVKQLVSDVREDLRVLRQNFRICCPINWVEYEGSCYWFSSVKPWTEADKYCQLENAHLVVVTSWEEQRFVQQHMGPLNTWIGLTDGNGPWKWVDGTDYETGFKNWRPGQPDDWYGHGLGGGEDCAHFTTDGHWNDDVCRRPCRWVCETELGKAN | pTT5, pSLX235a | 55 |
| muASGR1::Flag | 1-284 | Flag | MTKDYQDFQHLDNDNDHHQLRRGPPPTPRLLQRLCSGSRLLLLSSSLSILLLVVVCVITEDHSSLLLLHVKQLVSDVRSLSCQMAAFRGNGSERSNLTVSTEDQVKALSTQGSSVGRKMKLVESKLEKQQKDITEDHSSLLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTDGRWNDDVCRRPYRWVCETKLDKANDYKDDDDK | pTT5, pSLX235a | 56 |
| muASGR1(Y272C)::Flag | 1-284 | Flag | MTKDYQDFQHLDNDNDHHQLRRGPPPTPRLLQRLCSGSRLLLLSSSLSILLLVVVCVITEDHSSLLLLHVKQLVSDVRSLSCQMAAFRGNGSERSNLTVSTEDQVKALSTQGSSVGRKMKLVESKLEKQQKDITEDHSSLLLLHVKQLVSDVRSLSCQMAAFRGNGSERTCCPINWVEYEGSCYWFSSSVRPWTEADKYCQLENAHLVVVTSRDEQNFLQRHMGPLNTWIGLTDQNGPWKWVDGTDYETGFQNWRPEQPDNWYGHGLGGGEDCAHFTDGRWNDDVCRRPCRWVCETKLDKANDYKDDDDK | pTT5, pSLX235a | 57 |
| ratASGR1::Flag | 1-284 | Flag | MTKDYQDFQHLDNENDHHQLQRGPPPAPRLLQRLCSGFRLFLLSLGLSLILLHVKQLVSDVREDLRVLRQNFSNFTVSTEDQVKALTQGERVGRKMKLVESGLEKHQEDLREDHSRLLLLHVKQLVSDVREDLRVLRQNFRICCPINWVEYEGSCYWFSSVKPWTEADKYCQLENAHLVVVTSWEEQRFVQQHMGPLNTWIGLTDGNGPWKWVDGTDYETGFKNWRPGQPDDWYGHGLGGGEDCAHFTTDGHWNDDVCRRPYRWVCETELGKANDYKDDDDK | pTT5, pSLX235a | 58 |

FIGURE 48
(Continued)

| | | | | |
|---|---|---|---|---|
| ratASGR1(Y272C)::Flag | 1-284 | Flag | MTKDYQDFQHLDNENDHHQLQRGPPAPRLLQRLCSGFRLFLLSLGLSILLLVVVCVITSQNSQLREDLRVLRQNFSNFTVSTEDQVKALTTQGERVGRKMKLVESQLEKHQEDLREDHSRLLLHVKQLVSDVRSLSCQMAALRGNGSERICCPINWVEYEGSCYWFSSSVKPWTEADKYCQLENAHLVVTSWEEQRFVQQHMGPLNTWIGLTDQNGPWKWVDGTDYETGFKNWRPGQPDDWYGHGLGGGEDCAHFTTDGHWNDDVCRRPCRWVCETELGKANDYKDDDK | pTT5, pSLX235a | 59 |
| huASGR2 | 1-306 | None | MAKDFQDIQQLSSEENDHPFFHQGPPPAQPLAQRLCSMVCFSLLALSFNILLLVVICVTGSQSAGLQAELRSLKEAFSNFSSSTLTEVQAISTHGGSVGDKITSLGAKLEKQQQDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNWAVTQPDNWHGHELGGSEDCVEVQPDGRWNDFCLQVYRWVCEKRRNATGEVA | pTT5, pSLX235a, pJF1 | 60 |
| muASGR2 | 1-301 | None | MEKDFQDIQQLDSEEENDHQLSGDDEHGSHVQDPRIENPHWKGQPLSRPFPQRLCSTFRLSLLALAFNILLLVVICVVSSQSIQLQEEFRTLKEFSNFSSSTLMEFGALDTLGSSTNAILTSWLAQLEEKQQQLKADHSTLLFHLKHFPMDLRTLTCQLAYFQSNGTECCPVNWVEFGGSCYWFSRDGLTWAEADQYCQLENAHLLVINSREEQDFVVKHRSQFHIWIGLTDRDGSWKWVDGTDYRSNYRNWAFTQPDNWQGHEQGGGEDCAEILSDGHWNDFCGQVNRWVCEKRRNITH | pTT5, pJF1 | 61 |
| ratASGR2 | 1-301 | None | MEKDFQDIQQLDSEEENDHQLIGDEEQGSHVQNLRTENPRWGGQPPSRPFPQRLCSKFRLSLLALAFNILLLVVICVVSSQSMQLQKEFWTLKETLSNFSTTTLMEFKALDSHGGSRNDNLTSWETILEKKQKDIKADHSTLLFHLKHFPLDLRTLTCQLAFFLSNGTECCPVNWVEFGGSCYWFSRDGLTWAEADQYCQMENAHLLVINSREEQEFVVKHRGAFHIWIGLTDKDGSWKWVDGTEYRSNFKNWAFTQPDNWQGHEEGGSEDCAEILSDGLWNDFCGQVNRWACEKRDFTY | pTT5, pSLX235a | 62 |
| huASGR2::6xHis | 1-306 | 6xHis | MAKDFQDIQQLSSEENDHPFFHQGPPPAQPLAQRLCSMVCFSLLALSFNILLLVVICVTGSQSAGLQAELRSLKEAFSNFSSSTLTEVQAISTHGGSVGDKITSLGAKLEKQQQDLKADHDALLFHLKHFPVDLRFVACQMELLHSNGSQRTCCPVNWVEHQGSCYWFSHSGKAWAEAEKYCQLENAHLVVINSWEEQKFIVQHTNPFNTWIGLTDSDGSWKWVDGTDYRHNYKNWAVTQPDNWHGHELGGSEDCVEVQPDGRWNDFCLQVYRWVCEKRRNATGEVAHHHHHH | pTT5, pSLX235a | 63 |
| muASGR2::6xHis | 1-301 | 6xHis | MEKDFQDIQQLDSEEENDHQLSGDDEHGSHVQDPRIENPHWKGQPLSRPFPQRLCSTFRLSLLALAFNILLLVVICVVSSQSIQLQEEFRTLKEFSNFSSSTLMEFGALDTLGSSTNAILTSWLAQLEEKQQQLKADHSTLLFHLKHFPMDLRTLTCQLAYFQSNGTECCPVNWVEFGGSCYWFSRDGLTWAEADQYCQLENAHLLVINSREEQDFVVKHRSQFHIWIGLTDRDGSWKWVDGTDYRSNYRNWAFTQPDNWQGHEQGGGEDCAEILSDGHWNDFCGQVNRWVCEKRRNTHHHHHH | pTT5, pSLX235a | 64 |
| ratA::6xHis | 1-301 | 6xHis | MEKDFQDIQQLDSEEENDHQLIGDEEQGSHVQNLRTENPRWGGQPPSRPFPQRLCSKFRLSLLALAFNILLLVVICVVSSQSMQLQKEFWTLKETLSNFSTTTLMEFKALDSHGGSRNDNLTSWETILEKKQKDIKADHSTLLFHLKHFPLDLRTLTCQLAFFLSNGTECCPVNWVEFGGSCYWFSRDGLTWAEADQYCQMENAHLLVINSREEQEFVVKHRGAFHIWIGLTDKDGSWKWVDGTEYRSNFKNWAFTQPDNWQGHEEGGSEDCAEILSDGLWNDFCGQVNRWACEKRDFTYHHHHHH | pTT5, pSLX235a | 65 |
| dogASGR2::6xHis | 1-302 | 6xHis | MAKDFQDIQQLDSEDSDQQLGRGEGPGPRGHGPRREDRFCRRLPPHGPLLLQRLCSGYRLNLLVLGFNVLMLVAICVIGSQRAQLEEELRILKENFSHFSSGVLMELGVLLSDSGGASSQLTSLEAKLEKQGRDVKADHATLLHLKHFPSFDTWIGLTDSDGSWRWVDGTDYQQSYKNWAATQPDIWQGHEVGGGEDCAEVRANGRWNDFCKQVQRWVCEMRRNVFGHHHHHH | pTT5, pSLX235a | 66 |

FIGURE 48
(Continued)

| Name | Range | Tag | Sequence | Vector | # |
|---|---|---|---|---|---|
| dogASGR2 | 1-302 | None | MAKDFQDIQQLDSEDSDQQLGRGEGPGPRGSHGPRREDRFCRRLPPHQPLLLQRLCSGYRLNLLVLGFNVLMLV AICVIGSQRAQLEEELRILKENFSHFSSGVLMELGVLLSDGGASSQLTSLEAKLEKQQRDVKADHATLLLHLKHF PSDLRILTCQVAFFQSNGTDCCPVNWLEYEGSCYWFSRSGKTWEEAEKYCQLESAHLVVNSREEQKFILQHTN PFDTWIGLTDSDGSWRWVDGTEYQQSYKNWAATQPDDWQGHEVGGGEDCAEVRANGRWNDFCKQVQRW VCEMRRNVTG | pTT5, pSLX235a | 67 |
| cyASGR2 | 1-306 | None | MAKDFQDIQQLSSEEENDHPFHRGEGPGPRGLNLRRGNPSLKGPPPAQGPLAQRLCSMVRFSLLALSFNILLLVAIC VIGSQSAQLQAELWSLKEAFSNFSSSTLMEVHALGTHGGSVGDKITSLGDKLEKQGQDLKACHEDILLLHLKHFPV DLRFVACQMELLHSNGSQRTCCPVNWVEHQGSCYWFSRSGKAWAEAEKYCQLENSHLVVINSWEEQKFIVQH TNLFNTWIGLTDSDGSWKWVDGTEYRHNYKNWAVTQPDDWHGHELGGSEDCVEVRPDGRWNDFCLQVHR WVCEKRRNATGEAA | pTT5, pSLX235a | 68 |
| cyASGR2(L225P)::6xHis | 1-306 | 6xHis | MAKDFQDIQQLSSEEENDHPFHRGEGPGPRGLNLRRGNPSLKGPPPAQGPLAQRLCSMVRFSLLALSFNILLLVAIC VIGSQSAQLQAELWSLKEAFSNFSSSTLMEVHALGTHGGSVGDKITSLGDKLEKQQQDLKADHDILLLHLKHFPV DLRFVACQMELLHSNGSQRTCCPVNWVEHQGSCYWFSRSGKAWAEAEKYCQLENSHLVVINSWEEQKFIVQH TNPFNTWIGLTDSDGSWKWVDGTDYRHNYKNWAVTQPDDWHGHELGGSEDCVEVRPDGRWNDFCLQVHR WVCEKRRNATGEAAHHHHHH | pTT5, pSLX235a | 69 |
| pigASGR2 | 1-283 | 6xHis | MARDFQDIQGLDSEEENDHGLGRGTPLPQPLVLQRLCSKLRLSLLVLGFNVLMLVAVCVVGSQRTQLQMELQTLK ETFSNFSSSLLMEMLTLSTRGGSAGDKVTSLEAKMEKQQQDLKADHATLRLHLKHFPRDVRTLTCRLVFLQSNG TECCPVNWVDYEGSCYWFSRSGKAWAEAEKYCQLENAHLVVINSREEQKFIAQRTNPFQTWIGLTDSDGSWIK WVDGTDYGNGYKNWGALQPDDWQGHELGGSEDCVEIQGGRWNDFCQQVKRWVCEMKQNITMHHHHHH | pTT5, pSLX235a | 70 |
| cyASGR2(L225P) | 1-306 | None | MAKDFQDIQQLSSEEENDHPFHRGEGPGPRGLNLRRGNPSLKGPPPAQGPLAQRLCSMVRFSLLALSFNILLLVAIC VIGSQSAQLQAELWSLKEAFSNFSSSTLMEVHALGTHGGSVGDKITSLGDKLEKQQQDLKADHDILLLHLKHFPV DLRFVACQMELLHSNGSQRTCCPVNWVEHQGSCYWFSRSGKAWAEAEKYCQLENSHLVVINSWEEQKFIVQH TNPFNTWIGLTDSDGSWKWVDGTDYRHNYKNWAVTQPDDWHGHELGGSEDCVEVRPDGRWNDFCLQVHR WVCEKRRNATGEAA | pTT5, pSLX235a | 71 |
| pigASGR2 | 1-283 | None | MARDFQDIQGLDSEEENDHGLGRGTPLPQPLVLQRLCSKLRLSLLVLGFNVLMLVAVCVVGSQRTQLQMELQTLK ETFSNFSSSLLMEMLTLSTRGGSAGDKVTSLEAKMEKQQQDLKADHATLRLHLKHFPRDVRTLTCRLVFLQSNG TECCPVNWVDYEGSCYWFSRSGKAWAEAEKYCQLENAHLVVINSREEQKFIAQRTNPFQTWIGLTDSDGSWIK WVDGTDYGNGYKNWGALQPDDWQGHELGGSEDCVEIQGGRWNDFCQQVKRWVCEMKQNITM | pTT5, pSLX235a | 72 |
| dogASGR1 | 1-284 | None | MTNEYQDLQHLDNEDNDHHLRQVPPAPCQPLLRRLCSGPCLLLSVLLLVVVCVIGSQNSKLRGELQALRET FSNFTASTEVEVKALSSQGRKMKSLESQLEKQQKDLSEDHSDLLLHVKQFVSDLRSLSCQIAAHLHGNSTL TCCPVNWLEYEGSCYWFSRSGKSWPEADKYCQLESAHLVVNSREEQKFIQHHMGPVNTWMGLTDQSGPWK WVDGTDYETGFKNWRPEQPDDWYGHGLGGEDCVCQRPYRWVCEAARDPAT | pTT5, pSLX235a | 73 |
| pigASGR1 | 1-286 | None | MTKEYQDLQHLDNEENDQGHRKGPPPQPSLLRRLCSGPCLLLLSMGLSLLLHVSSSLLLHVVWSSWEEQKFIQHHVGPVNSWIGLTDQSGP RSLSCQMAVLQGNGS ERTCCPVNWVGYEGSCYWFSRSGKPWPEAAEKYCQLENAHLVVVGSWEEQKFIQHHVGPVNSWIGLTDQSGP WKWVDGTDYESGFKNWRPEQPDDWYGHGLGGEDCAHFTEDSGGWNDDICQRPYRWVCETQRDRDSGS | pTT5, pSLX235a | 74 |
| dogASGR1::Flag | 1-284 | Flag | MTNDYQDLQHLDNEDNDHHLRQVPPAPCQPLLRRLCSGPCLLLLSLGLSVLLLVVVCVIGSQNSKLRGELQALRET FSNFTASTEVEVKALSSQGRKMKSLESQLEHQQKDLSEDHSDLLLHVKQFVSDLRSLSCQIAAHLHGNSTL TCCPVNWLEYEGSCYWFSRSGKSWPEADKYCQLESAHLVVNSREEQKFIQHHMGPVNTWMGLTDQSGPWK WVDGTDYETGFKNWRPEQPDDWYGHGLGGEDCAHFTDDGRWNDDVCQRPYRWVCEAARDPATDYKDDD DK | pTT5, pSLX235a | 75 |

FIGURE 48
(Continued)

| | | | | | |
|---|---|---|---|---|---|
| pigASGR1::Flag | 1-286 | Flag | MTKEYQDLQHLDNEENDCQHRKGPPPQPSLLRRLCSGPCLLLISMGLSLLLLVVVCVIGSQNSKLQEELQALRET FSNLTASTDAKVKTLSMQGGNVGRKMKSLESQLEKGQQDLSEDHSSLLLHVKQFVSDLRSLSCQMAVLQGNGS ERTCCPVNWVGYEGSCYWFSRSGKPWPEAEKYCQLENAHLVVVGSWEEQKFIQHHVGPVNSWIGLTDQSGP WKWVDGTDYESGFKNWRPEQPDDWYGHGLGGGEDCAHFTEDGGWNDDICQRPYRWVCETQRDRDSGSDY KDDDDK | pTT5, pSLX235a. | 76 |
| huASGR1(deCODE) | 1-94. | None | MTKEYQDLQHLDNEESDHHQLRKGPPPPQPLLQRLCSGPRLLLLSLGLSLLLLVVVCVIGSQNSQLQEELRGLRE TFSNFTASTEAQEAMWEER | pJF1 | 77 |
| huASGR1(deCODE)::Myc | 1-94. | Myc | MTKEYQDLQHLDNEESDHHQLRKGPPPPQPLLQRLCSGPRLLLLSLGLSLLLLVVVCVIGSQNSQLQEELRGLRE TFSNFTASTEAQEAMWEERGGQKLISEEDL | pTT5 | 50759 |

FIGURE 49

Table 2A
Standard
IgG Antibody
VL CDRs

| iPS# | Ab | Type | CDR1 | CDR2 | CDR3 |
|---|---|---|---|---|---|
| iPS:451135 | 21-225_64A11 | NA | CGGGCAAGTCGGAGCGTTAGCAGATATTTAAAT SEQ ID NO:79 | GTTGCATCCGTTGCAAAGT SEQ ID NO:8091 | CAACAGAGTGACAGTTTCCTCTCACT SEQ ID NO:16103 |
| | | AA | RASRSVSRYLN SEQ ID NO:80 | VASRLQS SEQ ID NO:8092 | QQSDSFPLT SEQ ID NO:16104 |
| iPS:451141 | 21-225_164B11 | NA | AAGTCCAGCCAGAGTCTTTAAAGAGCTCCAACAATAAGAGCTACTTAGCT SEQ ID NO:81 | TGGGCATCTTCCCGGGAATCC SEQ ID NO:8093 | CAGCAATATTATAGTATTCCTCCCACT SEQ ID NO:16105 |
| | | AA | KSSQSLLKSSNNKSYLA SEQ ID NO:82 | WASSRES SEQ ID NO:8094 | QQYYSIPPT SEQ ID NO:16106 |
| iPS:451137 | 21-225_74A7 | NA | AAGTCCAGCCAGAGTGTTTATTCAGCTCCAACAATTATAACTACTTAGCT SEQ ID NO:83 | TGGGCATCTACCCGGGAATCC SEQ ID NO:8095 | CAGCAATATCATAGTTCTCCTCCGACG SEQ ID NO:16107 |
| | | AA | KSSQSVLFSSNNYNYLA SEQ ID NO:84 | WASTRES SEQ ID NO:8096 | QQYHSSPPT SEQ ID NO:16108 |
| iPS:451139 | 21-225_71A6 | NA | AAGTCTAGTCAGAGCCTCCTGCGTAGTGATGGAAAGACCCCTATTTGTAT SEQ ID NO:85 | GAAGTTCCAACGGTTCTCT SEQ ID NO:8097 | ATGCAAAGTAAACAGCTTCCTCTCACT SEQ ID NO:16109 |
| | | AA | KSSQSLLRSDGKTHLY SEQ ID NO:86 | EVSNRFS SEQ ID NO:8098 | MQSKQLPLT SEQ ID NO:16110 |

FIGURE 49
(Continued)

| | | | | | | |
|---|---|---|---|---|---|---|
| iPS:451143 | 21-225_66H11 | NA | CCGGGGAGTCAGGGCATTAG CAATTATTAGCT SEQ ID NO:87 | GGTGCATTCAATTTGCAC AGT SEQ ID NO:8099 | CAACAGTATAGTTGTTACCC ATTCACT SEQ ID NO:16111 | |
| | | AA | PASQGISNYLA SEQ ID NO:88 | GAFNLHS SEQ ID NO:8100 | QQYSCYPFT SEQ ID NO:16112 | |
| iPS:453445 | 21-225_148F10 | NA | TCTGGAGATAAATTGGGTAA TAAATATGTTTGT SEQ ID NO:89 | CAAGATAGCAAGCGGCC CTCA SEQ ID NO:8101 | CAGGCGTGGGACAGGAACAC TTATGTGGTG SEQ ID NO:16113 | |
| | | AA | SGDKLGNKYVC SEQ ID NO:90 | QDSKRPS SEQ ID NO:8102 | QAWDRNTYVV SEQ ID NO:16114 | |
| iPS:453447 | 21-225_65F10 | NA | CGGGGGGTCAGGGTCATTAG CACATGGTTAGCA SEQ ID NO:91 | GCTGCATCCAGTTTGCAA AGT SEQ ID NO:8103 | CAACAGGGTAACATTTTCCC ATTCACT SEQ ID NO:16115 | |
| | | AA | RGGQGISTWLA SEQ ID NO:92 | AASILQS SEQ ID NO:8104 | QQGNIFPFT SEQ ID NO:16116 | |
| iPS:453449 | 21-225_208A2 | NA | CGGACAAGTCAGGGCATTAG AAATGATTTAGGC SEQ ID NO:93 | CAAGATAGCAAGCGGCC CTCA SEQ ID NO:8105 | CTACAGTATAATAGTTACCC TCCCACC SEQ ID NO:16117 | |
| | | AA | RTSQGIRNDLG SEQ ID NO:94 | AASSLLS SEQ ID NO:8106 | LQYNSYPPT SEQ ID NO:16118 | |
| iPS:453451 | 21-225_52G11 | NA | CGGGCGAGTCAGGGTATTAG CAAAGTGGTTAGCC SEQ ID NO:95 | GCTGCATCCAGTTTGCAA AGT SEQ ID NO:8107 | CAACAGGCTAACAGTTCCC ATTCACT SEQ ID NO:16119 | |
| | | AA | RASQGISKWLA SEQ ID NO:96 | AASSLQS SEQ ID NO:8108 | QQANSFPFT SEQ ID NO:16120 | |
| iPS:453453 | 21-225_53F2 | NA | CGGGCGAGTCAGGGTATTAG CAAGTGGTTAGCC SEQ ID NO:97 | GCTGCATCCAGTTTGCAA AGT SEQ ID NO:8109 | CAACAGGCTAACAGTTCCC ATTCACT SEQ ID NO:16121 | |
| | | AA | RASQGISKWLA SEQ ID NO:98 | AASSLQS SEQ ID NO:8110 | QQANSFPFT SEQ ID NO:16122 | |

FIGURE 49
(Continued)

| | | | | | | |
|---|---|---|---|---|---|---|
| iPS:468810 | 21-225_74D5 | NA | AGGGCCAGTCAGAGTGTTAA CAGCAACTACTTAGCC | GGTGCATCCAGCAGGGC CACT | CAGCAGTATGAAAGCTCGCC GTGGACG | |
| | | | SEQ ID NO:99 | SEQ ID NO:8111 | SEQ ID NO:16123 | |
| | | AA | RASQSVNSNYLA | GASSRAT | QQYESSPWT | |
| | | | SEQ ID NO:100 | SEQ ID NO:8112 | SEQ ID NO:16124 | |
| iPS:468812 | 21-225_48H4 | NA | CGGGCAAGTCAGTCGAGACATTAG AAATGATTTAGGC | GCTGCATCCAGTTGCAA AGT | CTACAACATTATAGTTACC GCTCACT | |
| | | | SEQ ID NO:101 | SEQ ID NO:8113 | SEQ ID NO:16125 | |
| | | AA | RASRDIRNDLG | AASSLQS | LQHYSYPLT | |
| | | | SEQ ID NO:102 | SEQ ID NO:8114 | SEQ ID NO:16126 | |
| iPS:468816 | 21-225_52G8 | NA | AAGTCTAGTCAGAGCCTCCT GCATAGTGAAGGAAAGACC TATTTGTAT | GAAGTTTCCAAGCGGCT CTCT | ATGCAAAGTATGCAGTTCC GATTATC | |
| | | | SEQ ID NO:103 | SEQ ID NO:8115 | SEQ ID NO:16127 | |
| | | AA | KSSQSLLHSEGKTYLY | EVSKRLS | MQSMQLPII | |
| | | | SEQ ID NO:104 | SEQ ID NO:8116 | SEQ ID NO:16128 | |
| iPS:468814 | 21-225_223D11 | NA | CGGGCGAGTCAGGGCATTAG CAATTATTTAGCC | GCTGCATCCACTTTGCAA AGT | CAACAGTATAGTGGTTACC ATTCACT | |
| | | | SEQ ID NO:105 | SEQ ID NO:8117 | SEQ ID NO:16129 | |
| | | AA | RASQGISNYLA | AASTLQS | QQYSGYPFT | |
| | | | SEQ ID NO:106 | SEQ ID NO:8118 | SEQ ID NO:16130 | |
| iPS:468822 | 21-225_147E10 | NA | AAGTCTAGTCAGAGCCTCCT GCATGGTGATGGAAAGACCTTCT ATTTGTAT | GAAGTTTCCAACCGGTTC TCT | ATGCAAAGTATACAGGTTCC GTGGACG | |
| | | | SEQ ID NO:107 | SEQ ID NO:8119 | SEQ ID NO:16131 | |
| | | AA | KSSQRLLHGDGKTYLY | EVSNRFS | MQSIQVPWT | |
| | | | SEQ ID NO:108 | SEQ ID NO:8120 | SEQ ID NO:16132 | |
| iPS:468824 | 21-225_73G6 | NA | CGGGCAAGTCAGGGCATTAG AAATGATTTAGGC | GCTGCATCCAGTTGCAA AGT | CTACAGCATAATAGTTACC GCTCACT | |
| | | | SEQ ID NO:109 | SEQ ID NO:8121 | SEQ ID NO:16133 | |

FIGURE 49
(Continued)

| | | | | | | |
|---|---|---|---|---|---|---|
| iPS:468818 | | AA | RASQGIRNDLG SEQ ID NO:110 | AASSLQS SEQ ID NO:8122 | LQHNSYPLT SEQ ID NO:16134 | |
| | 21-225_190C8 | NA | CGGGCAAGTCAGGGCATTAG AAATGATTAGGC SEQ ID NO:111 | GCTGCATCCAGTTTGCAA AGT SEQ ID NO:8123 | CTACAGCATAATGATTACC GTTCACT SEQ ID NO:16135 | |
| iPS:468826 | | AA | RASQGIRNDLG SEQ ID NO:112 | AASSLQS SEQ ID NO:8124 | LQHNDYPFT SEQ ID NO:16136 | |
| | 21-225_201C5 | NA | CGGGCAAGTCAGGGCATTAG ACATGATTAGGC SEQ ID NO:113 | GCTGCATCCAGTTTGCAA AGT SEQ ID NO:8125 | CTACAGCATTATAGTTTCCCT CGGACG SEQ ID NO:16137 | |
| iPS:468828 | | AA | RASQGIRHDLG SEQ ID NO:114 | AASSLQS SEQ ID NO:8126 | LQHYSFPRT SEQ ID NO:16138 | |
| | 21-225_162A10 | NA | AGGGCCAGTCAGAGTGTTAA CAGCAACTTAGCC SEQ ID NO:115 | GGTGCATCCACCAGGGC CACT SEQ ID NO:8127 | CAGCAGTATAATGACTGGCC GTGCAGT SEQ ID NO:16139 | |
| iPS:468830 | | AA | RASQTVNSNLA SEQ ID NO:116 | GASTRAT SEQ ID NO:8128 | QQYNDWPCS SEQ ID NO:16140 | |
| | 21-225_191G11 | NA | AGGACCAGTCAGAGTGTTTG GATTAGCGTAGCC SEQ ID NO:117 | GGTGCAGCCACCAGGGC CACT SEQ ID NO:8129 | CAGCAGTATAATTACTGGCC GCTCACT SEQ ID NO:16141 | |
| iPS:468832 | | AA | RTSQSVWISVA SEQ ID NO:118 | GAATRAT SEQ ID NO:8130 | QQYNYWPLT SEQ ID NO:16142 | |
| | 21-225_76H10 | NA | CGGGCAAGTCAGGGCATTAG AAATTATTAGGC SEQ ID NO:119 | GGTGCATCCAGTTTGCA AAGT SEQ ID NO:8131 | CTACAGTATAATAGTTACC ATTCACT SEQ ID NO:16143 | |
| iPS:468834 | | AA | RASQDIRNYLG SEQ ID NO:120 | GASSLQS SEQ ID NO:8132 | LQYNSYPFT SEQ ID NO:16144 | |
| | 21-225_94G10 | NA | AGGGCCAGTCAGAGTGTTAA CAGCAACTACTTAGCC SEQ ID NO:121 | GGTGCATCCAGCAGGGC CACT SEQ ID NO:8133 | CAGCAGTATGAAAGCTCGCC GTGGACG SEQ ID NO:16145 | |

FIGURE 49
(Continued)

| | | | RASQSVNSNYLA | GASSRAT | QQYESSPWT |
|---|---|---|---|---|---|
| | | AA | SEQ ID NO:122 | SEQ ID NO:8134 | SEQ ID NO:16146 |
| iPS:468836 | 21-225_198E3 | NA | CGGGCAAGTCAGGGCATAA GAAAGATTAGGC SEQ ID NO:123 | GCTGCATCCAGTTTGCAA AGT SEQ ID NO:8135 | CTACAACATTATCGTTACCC TTTCACT SEQ ID NO:16147 |
| iPS:468838 | 21-225_80E12 | AA | RASQGIRKDLG SEQ ID NO:124 | AASSLQS SEQ ID NO:8136 | LQHYRYPFT SEQ ID NO:16148 |
| | | NA | AGGGCCAGTCAGAGCGTTAA CAGCAACTACTTAGCC SEQ ID NO:125 | GGTGCATCCAGCAGGGC CACT SEQ ID NO:8137 | CAGCAGTATGAAAGCTCGCC GTGGACG SEQ ID NO:16149 |
| iPS:468840 | 21-225_200H9 | AA | RASQSVNSNYLA SEQ ID NO:126 | GASSRAT SEQ ID NO:8138 | QQYESSPWT SEQ ID NO:16150 |
| | | NA | CGGGCAAGTCAGGGCATTAG AAATGATTAGGC SEQ ID NO:127 | GCTGCATCCAGTTTGCAA AGT SEQ ID NO:8139 | CTACAGCATAATAGTTACCC TCTCACT SEQ ID NO:16151 |
| iPS:468820 | 21-225_76E10 | AA | RASQGIRNDLG SEQ ID NO:128 | AASSLQS SEQ ID NO:8140 | LQHNSYPLT SEQ ID NO:16152 |
| | | NA | AGGGCCAGTCAGAGTGTTAA CAGCAACTACTTAGCC SEQ ID NO:129 | GGTGCATCCAGCAGGGC CACT SEQ ID NO:8141 | CAGCAGTATGAAAGCTCGCC GTGGACG SEQ ID NO:16153 |
| iPS:468842 | 21-225_50H4 | AA | RASQSVNSNYLA SEQ ID NO:130 | GASSRAT SEQ ID NO:8142 | QQYESSPWT SEQ ID NO:16154 |
| | | NA | CGGGCAAGTCAGGGCATTAG AAATGATTAGGC SEQ ID NO:131 | GCTGCATCCAGTTTGCAA AGT SEQ ID NO:8143 | CTACAACATTATAGTTACCC TCGGACG SEQ ID NO:16155 |
| iPS:468844 | 21-225_48E10 | AA | RASQGIRNDLG SEQ ID NO:132 | AASSLQS SEQ ID NO:8144 | LQHYSYPRT SEQ ID NO:16156 |
| | | NA | CGGGCAAGTCAGGGCATTAG AAGTGATTAGGC SEQ ID NO:133 | ACTGCATCCAGTTGCAA AGT SEQ ID NO:8145 | CTACAGTATAATAGTTACCC ATTCACT SEQ ID NO:16157 |

FIGURE 49
(Continued)

| | | | | | | |
|---|---|---|---|---|---|---|
| iPS:468846 | 21-225_53B10 | AA | RASQGIRSDLG<br>SEQ ID NO:134 | TASSLQS<br>SEQ ID NO:8146 | LQYNSYPFT<br>SEQ ID NO:16158 |
| | | NA | CGGGCAAGTCAGGACATTAG<br>AAATTATTTAGGC<br>SEQ ID NO:135 | GGTGCATCCAGTTGCA<br>AAGT<br>SEQ ID NO:8147 | CTACAGTATAATAGTTACCC<br>ATTCACT<br>SEQ ID NO:16159 |
| iPS:468848 | 21-225_54B1 | AA | RASQDIRNYLG<br>SEQ ID NO:136 | GASSLQS<br>SEQ ID NO:8148 | LQYNSYPFT<br>SEQ ID NO:16160 |
| | | NA | CGGGCAAGTCAGAACATTAG<br>CAGCTATTTAAAT<br>SEQ ID NO:137 | GCTGCATCCAGTTGCAT<br>AGT<br>SEQ ID NO:8149 | CAACAGAGTTACAGAACCCC<br>TCTGTGGACG<br>SEQ ID NO:16161 |
| iPS:468850 | 21-225_63F4 | AA | RASQNISSYLN<br>SEQ ID NO:138 | AASSLHS<br>SEQ ID NO:8150 | QQSYRTPLWT<br>SEQ ID NO:16162 |
| | | NA | AAGTCCAGCCAGAGTGTTT<br>ATCCAGCTCCAACAATAACA<br>ACTACTTAGCT<br>SEQ ID NO:139 | TGGGCATCTACCCGGGA<br>ATCC<br>SEQ ID NO:8151 | CAGCAATATTATACTACTCC<br>GTGCAGT<br>SEQ ID NO:16163 |
| iPS:468852 | 21-225_71F3 | AA | KSSQSVLSSSNNNNYLA<br>SEQ ID NO:140 | WASTRES<br>SEQ ID NO:8152 | QQYYTTPCS<br>SEQ ID NO:16164 |
| | | NA | AAGTCCAGCCAGAGTGTTT<br>ATCCAACTCCAACAATAACA<br>ACTACTTAGCT<br>SEQ ID NO:141 | TGGGCATCTACCCGGGA<br>ATCC<br>SEQ ID NO:8153 | CAGCAATATTATACTACTCC<br>GTGCAGT<br>SEQ ID NO:16165 |
| iPS:468854 | 21-225_72C4 | AA | KSSQSVLSNSNNNNYLA<br>SEQ ID NO:142 | WASTRES<br>SEQ ID NO:8154 | QQYYTTPCS<br>SEQ ID NO:16166 |
| | | NA | AGGTCTGGTCAAAGCCTCGT<br>ATACAGTGATGAAACACCT<br>ACTTGAAT<br>SEQ ID NO:143 | GAGGTTTCTAAGTGGGA<br>CTCT<br>SEQ ID NO:8155 | ATGCAAGGTACACACTGGCC<br>GCTCACT<br>SEQ ID NO:16167 |
| | | AA | RSGQSLVYSDGNTYLN<br>SEQ ID NO:144 | EVSKWDS<br>SEQ ID NO:8156 | MQGTHWPLT<br>SEQ ID NO:16168 |

FIGURE 49
(Continued)

| | | | | | |
|---|---|---|---|---|---|
| iPS:468856 | 21-225_77C9 | NA | AGGTCTAGTCAAAGCCTCGTTTACAGTGTTGGAAACACCTCCTTGAGT<br>SEQ ID NO:145 | AAGGTTTCTAACTGGGACTCT<br>SEQ ID NO:8157 | ATGCAAGGTACACACTGGCCATTCACT<br>SEQ ID NO:16169 |
| | | AA | RSSQSLVYSVGNTSLS<br>SEQ ID NO:146 | KVSNWDS<br>SEQ ID NO:8158 | MQGTHWPFT<br>SEQ ID NO:16170 |
| iPS:468858 | 21-225_148C9 | NA | CGGGCAAGTCGGGGCATTAGAGATGATTTAGGC<br>SEQ ID NO:147 | GCTGCATCCAGTTTGCAGAGT<br>SEQ ID NO:8159 | CTACACAGCATTATAAGTTATCCTCGGACG<br>SEQ ID NO:16171 |
| | | AA | RASRGIRDDLG<br>SEQ ID NO:148 | AASSLQS<br>SEQ ID NO:8160 | LQHYSYPRT<br>SEQ ID NO:16172 |
| iPS:468860 | 21-225_224E7 | NA | CGGGCAAGTCAGGGGCATTAGAAATGATTTAGGC<br>SEQ ID NO:149 | GCTGCATCCAGTTTGCAAAGT<br>SEQ ID NO:8161 | CTACAACATTATAAGTTACCCTCGGACG<br>SEQ ID NO:16173 |
| | | AA | RASQGIRNDLG<br>SEQ ID NO:150 | AASSLQS<br>SEQ ID NO:8162 | LQHYSYPRT<br>SEQ ID NO:16174 |
| iPS:468862 | 21-225_178H8 | NA | ACTGGAACCAGCAGTGACGTTGGTGGTTATAATTTTGTCTCC<br>SEQ ID NO:151 | GAGGTCAGTAATCGGCCCTCA<br>SEQ ID NO:8163 | AGCTCATATACAAGCAGCTACACTTGGGGTG<br>SEQ ID NO:16175 |
| | | AA | TGTSSDVGGYNFVS<br>SEQ ID NO:152 | EVSNRPS<br>SEQ ID NO:8164 | SSYTSSSYTWV<br>SEQ ID NO:16176 |
| iPS:468864 | 21-225_60D6 | NA | TCTGGAAGCAGCTCCAACATCGGAAGTAATACTGTAAAC<br>SEQ ID NO:153 | AGTAATAATCAGCGGCCCTCA<br>SEQ ID NO:8165 | GCAGCATGGGATGACAGCCTGAATGGTCCG<br>SEQ ID NO:16177 |
| | | AA | SGSSSNIGSNTVN<br>SEQ ID NO:154 | SNNQRPS<br>SEQ ID NO:8166 | AAWDDSLNGP<br>SEQ ID NO:16178 |
| iPS:468866 | | NA | ACTGGAGATGCAATGCCGAAAAAATATGCTTAT | GAGGACAGCAAGCGACCCTCC | AACTCAACAGACAGCAGTGGTAATCGGGTG |

FIGURE 49
(Continued)

| | | | | | | | |
|---|---|---|---|---|---|---|---|
| iPS:468868 | 21-225_190C1 | | SEQ ID NO:155 TGIDAMPKKYAY | AA | SEQ ID NO:8167 EDSKRPS | | SEQ ID NO:16179 NSTDSSGNRV |
| | | | SEQ ID NO:156 CGGGCAAGTCAGGGCATTAGAAATGATTAGGC | NA | SEQ ID NO:8168 GCTGCATCCAGTTTGCAAAGT | | SEQ ID NO:16180 CTACAGCATGATAGTTACCCTCTCACT |
| iPS:468870 | 21-225_74A1 | | SEQ ID NO:157 RASQGIRNDLG | AA | SEQ ID NO:8169 AASSLQS | | SEQ ID NO:16181 LQHDSYPLT |
| | 21-225_74A8 | | SEQ ID NO:158 AAGTCCAGCCAGAGTGTTTTGTACAGCTCCAACAGTCACAACTACTTAGCT | NA | SEQ ID NO:8170 TGGGCATCTACCCGGGAATCC | | SEQ ID NO:16182 CAGCAATATTATAGTACTCCGTGCAGT |
| | | | SEQ ID NO:159 KSSQSVLYSSNSHNYLA | AA | SEQ ID NO:8171 WASTRES | | SEQ ID NO:16183 QQYYSTPCS |
| iPS:472730 | 21-225_14B1_LC1 | | SEQ ID NO:160 CGGGCAAGTCAGGACATTAGAGATAATTAGGC | NA | SEQ ID NO:8172 ACTGCATACAGTTTGCAAAGT | | SEQ ID NO:16184 CTACAACATTATAATTACCCGCTCACT |
| | | | SEQ ID NO:161 RASQDIRDNLG | AA | SEQ ID NO:8173 TAYSLQS | | SEQ ID NO:16185 LQHYNYPLT |
| iPS:472731 | 21-225_14B1_LC2 | | SEQ ID NO:162 TCTGGAGATAAATTGGGGGATAAATATGCTTAC | NA | SEQ ID NO:8174 CAAGATAGGAAGCGCCCCTCA | | SEQ ID NO:16186 CAGGCGTGGGACAACAGCACTGTGGTG |
| | | | SEQ ID NO:163 SGDKLGDKYAY | AA | SEQ ID NO:8175 QDRKRPS | | SEQ ID NO:16187 QAWDNSTVV |
| iPS:472732 | 21-225_2B10_LC1 | | SEQ ID NO:164 AGGTCTAGTCAAAGCCTCGTATACAGTGATGGAAACACCTTCTTGAAT | NA | SEQ ID NO:8176 AAGGTTTCTAACTGGGACTCT | | SEQ ID NO:16188 ATACAAGTACCGCACTGGCCTTTCCCC |
| | | | SEQ ID NO:165 RSSQSLVYSDGNTFLN | AA | SEQ ID NO:8177 KVSNWDS | | SEQ ID NO:16189 IQGTHWPFP |
| | | | SEQ ID NO:166 | | SEQ ID NO:8178 | | SEQ ID NO:16190 |

FIGURE 49
(Continued)

| ID | Name | NA/AA | Seq 1 | Seq 2 | Seq 3 |
|---|---|---|---|---|---|
| iPS:472733 | 21-225_2B10_LC2 | NA | ACTGGAACCAGCAGTGACGT TGGTGGTTATAATTTGTCT CC SEQ ID NO:167 | GAGGTCAGTAATCGGCC CTCA SEQ ID NO:8179 | AGCTCATATACAAGCACCGG CACTGTGGTA SEQ ID NO:16191 |
| | | AA | TGTSSDVGGYNFVS SEQ ID NO:168 | EVSNRPS SEQ ID NO:8180 | SSYTSTGTVV SEQ ID NO:16192 |
| iPS:473253 | 21-225_7C3_LC1 | NA | CGGGCAAGTCAGGGCATTAG AAGTGATTTAGGC SEQ ID NO:169 | GCTGCATCCAGTTGCAA AGT SEQ ID NO:8181 | CTACAGCATAATAGTTACCT CCCCATCACC SEQ ID NO:16193 |
| | | AA | RASQGIRSDLG SEQ ID NO:170 | AASSLQS SEQ ID NO:8182 | LQHNSYLPIT SEQ ID NO:16194 |
| iPS:473254 | 21-225_7C3_LC2 | NA | CGGGCGAGTCAGGGTATTAG CAGCTGGTTAGCC SEQ ID NO:171 | GCTGCATCCAGGTTGCA AAGT SEQ ID NO:8183 | CAACAGGCTAACAGTTTCCC ATTCACT SEQ ID NO:16195 |
| | | AA | RASQGISSWLA SEQ ID NO:172 | AASRLQS SEQ ID NO:8184 | QQANSFPFT SEQ ID NO:16196 |
| iPS:473255 | 21-225_9F12_LC1 | NA | CGGGCGAGTCAGGGTATTAG CAGGTGGTTAGCC SEQ ID NO:173 | GCTGCATCCAGATTGCA AAGT SEQ ID NO:8185 | CAACAGGCTAACAGTTTCCC ATTCACT SEQ ID NO:16197 |
| | | AA | RASQGISRWLA SEQ ID NO:174 | AASRLQS SEQ ID NO:8186 | QQANSFPFT SEQ ID NO:16198 |
| iPS:473256 | 21-225_9F12_LC2 | NA | CGGGCAAGTCAGGGCATTAG AAATGATTTAGGC SEQ ID NO:175 | GCTGCATCCAGTTTGCAA AGT SEQ ID NO:8187 | CTACAGCATAATAGTTACCT CCCCATCACC SEQ ID NO:16199 |
| | | AA | RASQGIRNDLG SEQ ID NO:176 | AASSLQS SEQ ID NO:8188 | LQHNSYLPIT SEQ ID NO:16200 |
| iPS:472742 | 21-225_30D9_LC2 | NA | TCTGGAGATAAATTGGGGGA TAAATATGTTTAC SEQ ID NO:177 | CAAGATAGGAAGCGGCC CTCA SEQ ID NO:8189 | CAGGCGTGGGACAACAGCAC TGCGGTA SEQ ID NO:16201 |
| | | AA | SGDKLGDKYVY | QDRKRPS | QAWDNSTAV |

FIGURE 49
(Continued)

| | | | | | |
|---|---|---|---|---|---|
| iPS:472741 | 21-225_30D9_LC1 | NA | SEQ ID NO:178 AGGTCTAGTCAAAGCCTCGTATCCAGTGATGGAAACACCTTCTTGAAT | SEQ ID NO:8190 AAGGTTTCTAACTGGGACTCT | SEQ ID NO:16202 TTGCAAGGTACACACTGGCCTCTCACC |
| | | AA | SEQ ID NO:179 RSSQSLVSSDGNTFLN | SEQ ID NO:8191 KVSNWDS | SEQ ID NO:16203 LQGTHWPLT |
| iPS:472743 | 21-225_68G6 | NA | SEQ ID NO:180 TCTGGAGATAAATTGGGGGATAAATATACTTAC | SEQ ID NO:8192 CAAGATAGGAAGCGGCCCTCA | SEQ ID NO:16204 CAGGCGTGGGACAATAGTACTGCGGTA |
| | | AA | SEQ ID NO:181 SGDKLGDKYTY | SEQ ID NO:8193 QDRKRPS | SEQ ID NO:16205 QAWDNSTAV |
| iPS:472573 | 21-225_15G2 | NA | SEQ ID NO:182 ACTGGAACCAGCAGTGACGTTGGTGGTTATAACTATGTCTCC | SEQ ID NO:8194 GAGGTCAGTAATCGGCCCTCA | SEQ ID NO:16206 ACCTCATATACAAGCACCAGCACTGTGGTC |
| | | AA | SEQ ID NO:183 TGTSSDVGGYNYVS | SEQ ID NO:8195 EVSNRPS | SEQ ID NO:16207 TSYTSTSTVV |
| iPS:392583 | 21-225_10B10 | NA | SEQ ID NO:184 TCTGGAGATAAATTGGGGAATAAATATGCTTGG | SEQ ID NO:8196 CAAGATAGGAAGCGGCCCTCA | SEQ ID NO:16208 CAGGCGTGGACAACAGCACTGTGGTT |
| | | AA | SEQ ID NO:185 SGDKLGNKYAW | SEQ ID NO:8197 QDRKRPS | SEQ ID NO:16209 QAWDNSTVV |
| iPS:392585 | 21-225_14H11 | NA | SEQ ID NO:186 TCTGGAGATAAATTGGGGAAAAATATGTTTGC | SEQ ID NO:8198 CAAGATACCAAGCGGCCCTCA | SEQ ID NO:16210 CAGGCGTGGGACAGCAGCACTATA |
| | | AA | SEQ ID NO:187 SGDKLGEKYVC | SEQ ID NO:8199 QDTKRPS | SEQ ID NO:16211 QAWDSSTI |
| iPS:392587 | | NA | SEQ ID NO:188 TCTGGAGAGAAATTGGGGGATAAATATGTTTGT | SEQ ID NO:8200 CAAGATAGCAAGCGGCCCTCA | SEQ ID NO:16212 CAGGCGTGGAACAGCAGCAATGTGGTA |

FIGURE 49
(Continued)

| | | | | | | |
|---|---|---|---|---|---|---|
| iPS:392589 | 21-225_18G5 | AA | SEQ ID NO:189<br>SGEKLGDKYVC<br>SEQ ID NO:190 | SEQ ID NO:8201<br>QDSKRPS<br>SEQ ID NO:8202 | SEQ ID NO:16213<br>QAWNSSNVV<br>SEQ ID NO:16214 | |
| iPS:392593 | 21-225_27H2 | NA | TCTGGAGATAAATTGGGGGA<br>TAAATATGCTTCC<br>SEQ ID NO:191 | CAAGATGGCAAGCGGCC<br>CTCA<br>SEQ ID NO:8203 | CAGGCGTGGGACAGCAGCAC<br>TTATGTGGTA<br>SEQ ID NO:16215 | |
| | | AA | SGDKLGDKYAS<br>SEQ ID NO:192 | QDGKRPS<br>SEQ ID NO:8204 | QAWDSSTYVV<br>SEQ ID NO:16216 | |
| iPS:392596 | 21-225_3E10 | NA | GGGGGAAACAACATTGGAA<br>GTAAAGCTGTGCAC<br>SEQ ID NO:193 | AGCGATAGCAACCGGCC<br>CTCA<br>SEQ ID NO:8205 | CAGGTGTGGGACAGTAGTAG<br>TGATCATGTGGTA<br>SEQ ID NO:16217 | |
| | | AA | GGNNIGSKAVH<br>SEQ ID NO:194 | SDSNRPS<br>SEQ ID NO:8206 | QVWDSSSDHVV<br>SEQ ID NO:16218 | |
| iPS:392596 | 21-225_12D8 | NA | ACCCTAAGCAGTGAGCACAG<br>CACCTACCACCATCGAA<br>SEQ ID NO:195 | GTTAAGAGTGATGGCAG<br>CCACAGCAAGGGGGAC<br>SEQ ID NO:8207 | GGAGAGAGCCACACGATTGA<br>TGGCCAAGTCGGTGTGTA<br>SEQ ID NO:16219 | |
| | | AA | TILSSEHSTYTIE<br>SEQ ID NO:196 | VKSDGSHSKGD<br>SEQ ID NO:8208 | GESHTDGQVGVV<br>SEQ ID NO:16220 | |
| iPS:392598 | 21-225_18E10 | NA | TCTGGAGATAGATTGGGGGA<br>TAAATATGCTTGG<br>SEQ ID NO:197 | CAAGATCGCAAGCGGCC<br>CTCA<br>SEQ ID NO:8209 | CAGGCGTGGGACAGCAGCAC<br>AGTGGTA<br>SEQ ID NO:16221 | |
| | | AA | SGDRLGDKYAW<br>SEQ ID NO:198 | QDRKRPS<br>SEQ ID NO:8210 | QAWDSSTVV<br>SEQ ID NO:16222 | |
| iPS:392618 | 21-225_16F10 | NA | AAGTCTAGTCAGAGCCTCCT<br>GCATAGTGATGGAAAGACCCTCT<br>ATTTGAAT<br>SEQ ID NO:199 | GAAGTTTCCTACCGGTTC<br>SEQ ID NO:8211 | TTTCAAAGTATACAGCTTCC<br>GCTCACT<br>SEQ ID NO:16223 | |
| | | AA | KSSQSLLHSDGKTHLN<br>SEQ ID NO:200 | EVSYRFS<br>SEQ ID NO:8212 | FQSIQLPLT<br>SEQ ID NO:16224 | |

FIGURE 49
(Continued)

| | | | | | | |
|---|---|---|---|---|---|---|
| iPS:392620 | 21-225_17H5 | NA | CGGGCGAGTCAGGGCATTAG CAATTATTAGGC | GCTGCATCCAGTTTACAA AGT | CAACAGTATCATAGTTACCC ATTCACT | |
| | | | SEQ ID NO:201 | SEQ ID NO:8213 | SEQ ID NO:16225 | |
| | | AA | RASQGISNYLA | AASSLQS | QQYHSYPFT | |
| | | | SEQ ID NO:202 | SEQ ID NO:8214 | SEQ ID NO:16226 | |
| iPS:392622 | 21-225_17H8 | NA | CGGGCAAGTCAGGGCATTAG AAATGATTAGGC | GGTGCATCCAGTTTGCA AAGT | CTACAGCATAATAGTTACCC ACTCACT | |
| | | | SEQ ID NO:203 | SEQ ID NO:8215 | SEQ ID NO:16227 | |
| | | AA | RASQGIRNDLG | GASSLQS | LQHNSYPLT | |
| | | | SEQ ID NO:204 | SEQ ID NO:8216 | SEQ ID NO:16228 | |
| iPS:392624 | 21-225_17H12 | NA | CGGGCAAGTCAGGGCATTAG AAATGATTAGGC | GCTGCATCCAGTTTGCAA AGT | CTACAGCATTATAGTTATAT GTTCACT | |
| | | | SEQ ID NO:205 | SEQ ID NO:8217 | SEQ ID NO:16229 | |
| | | AA | RASQDIRNDLG | AASSLQS | LQHYSYMFT | |
| | | | SEQ ID NO:206 | SEQ ID NO:8218 | SEQ ID NO:16230 | |
| iPS:392626 | 21-225_18A5 | NA | CGGGCAAGTCAGGGCATTAG AAATGATTAGGC | GCTGCATCCAGTTTGCAA AGT | CTACAGCATAATAGTTACCC GTGGACG | |
| | | | SEQ ID NO:207 | SEQ ID NO:8219 | SEQ ID NO:16231 | |
| | | AA | RASQGIRNDLG | AASSLQS | LQHNSYPWT | |
| | | | SEQ ID NO:208 | SEQ ID NO:8220 | SEQ ID NO:16232 | |
| iPS:392628 | 21-225_20C2 | NA | CGGGCAAGTCAGGGCATTAG AAATGATTAGGC | GCTGCATCCAGTTTGCAA AGT | CTTCAACATGCTAGTTACCC GCTCACT | |
| | | | SEQ ID NO:209 | SEQ ID NO:8221 | SEQ ID NO:16233 | |
| | | AA | RASQGIRNDLG | AASSLQS | LQHASYPLT | |
| | | | SEQ ID NO:210 | SEQ ID NO:8222 | SEQ ID NO:16234 | |
| iPS:392630 | 21-225_20E5 | NA | CGGGCAAGTCAGGGCATTAG AAATGATTAGGC | GCTGCATCCAGTTTGCAA AGT | CTACAGCATAATAGTTACCC GCTCACT | |
| | | | SEQ ID NO:211 | SEQ ID NO:8223 | SEQ ID NO:16235 | |
| | | AA | RASQGIRNDLG | AASSLQS | LQHNSYPLT | |
| | | | SEQ ID NO:212 | SEQ ID NO:8224 | SEQ ID NO:16236 | |

FIGURE 49
(Continued)

| | | | | | |
|---|---|---|---|---|---|
| iPS:392632 | 21-225_16A11 | NA | CGGGCAAGTCAGGACATTAG AAATCATTAGGC SEQ ID NO:213 | GCTGCAATCCAGTTTGCAA AGT SEQ ID NO:8225 | CTACACAGTATAATAGTTATCC ATTCACT SEQ ID NO:16237 |
| | | AA | RASQDIRNHLG SEQ ID NO:214 | AASSLQS SEQ ID NO:8226 | LQYNSYPFT SEQ ID NO:16238 |
| iPS:392634 | 21-225_17H3 | NA | CGGGCAAGTCAGGGCATTAG AAGTGATTAGGC SEQ ID NO:215 | GCTGCATCCAGTTTGCAA AGT SEQ ID NO:8227 | CTACAGCAATATAGTTACCC TCGGACG SEQ ID NO:16239 |
| | | AA | RASQGIRSDLG SEQ ID NO:216 | AASSLQS SEQ ID NO:8228 | LQQYSYPRT SEQ ID NO:16240 |
| iPS:392636 | 21-225_17A6 | NA | CGGGCAAGTCAGACCATTAG CAACTATTAAAT SEQ ID NO:217 | GCTGCTTCCAGTTTGCAA AGT SEQ ID NO:8229 | CAACAGAGTCACACTTCCCC GCTCACT SEQ ID NO:16241 |
| | | AA | RASQTISNYLN SEQ ID NO:218 | AASSLQS SEQ ID NO:8230 | QQSHTSPLT SEQ ID NO:16242 |
| iPS:392638 | 21-225_17F9 | NA | CGGGCAAGTCAGGGCATTAG AAATGATTAGGC SEQ ID NO:219 | GCTGTATCCAGTTTGCAA AGT SEQ ID NO:8231 | CTACAACATAATACTTATCC GCTCACT SEQ ID NO:16243 |
| | | AA | RASQVIRNDLG SEQ ID NO:220 | AVSSLQS SEQ ID NO:8232 | LQHNTYPLT SEQ ID NO:16244 |
| iPS:392640 | 21-225_18A1 | NA | CGGGCAAGTCAGGGCATTAG AAATGATTAGGC SEQ ID NO:221 | GCTGCATCCAGTTTACAA AGT SEQ ID NO:8233 | CTACAGCATAATAGTTACCC GCTCACT SEQ ID NO:16245 |
| | | AA | RASQGIRNDLG SEQ ID NO:222 | AASSLQS SEQ ID NO:8234 | LQHNSYPLT SEQ ID NO:16246 |
| iPS:392642 | 21-225_18C6 | NA | CGGACAAGTCAGGGCATTAG AAATGATTAGGC SEQ ID NO:223 | GCTGCATCCAGTTTGCAA AGT SEQ ID NO:8235 | CTACAGCATAGTTCTTACCC GCTCACT SEQ ID NO:16247 |
| | | AA | RTSQGIRNDLG SEQ ID NO:224 | AASSLQS SEQ ID NO:8236 | LQHSSYPLT SEQ ID NO:16248 |

FIGURE 49
(Continued)

| | | | | | | |
|---|---|---|---|---|---|---|
| iPS:392644 | 21-225_19E1 | NA | CGGGCAAGTCAGGGCATTAG AAATGATTAGGC | GCTGCATCCAATTTACAA AGT | CTACAGCAGCATAATAGTTTCCC GCTCACT | |
| | | | SEQ ID NO:225 | SEQ ID NO:8237 | SEQ ID NO:16249 | |
| | | AA | RASQGIRNDLG | AASNLQS | LQHNSFPLT | |
| | | | SEQ ID NO:226 | SEQ ID NO:8238 | SEQ ID NO:16250 | |
| iPS:392646 | 21-225_20G2 | NA | CGGGCAAGTCAGGGCATTAG AAATGATTAGGC | GCTGCATCCAGTTTCCAA AGT | CTACAGCAGCATAATAGTTACCC GCTCACT | |
| | | | SEQ ID NO:227 | SEQ ID NO:8239 | SEQ ID NO:16251 | |
| | | AA | RASQGIRNDLG | AASSFQS | LQHNSYPLT | |
| | | | SEQ ID NO:228 | SEQ ID NO:8240 | SEQ ID NO:16252 | |
| iPS:392648 | 21-225_16D11 | NA | CGGGCGAGTCAGAGACCATTAG CAACTATTTAAAT | GCTGCATCCAGTTGCAA AGT | CAACAGAGTCACAGTTCCCG GCTCACT | |
| | | | SEQ ID NO:229 | SEQ ID NO:8241 | SEQ ID NO:16253 | |
| | | AA | RASQTISNYLN | AASSLQS | QQSHSSPLT | |
| | | | SEQ ID NO:230 | SEQ ID NO:8242 | SEQ ID NO:16254 | |
| iPS:392650 | 21-225_17A4 | NA | CGGGCGAGTCAGGGTATTGG CAACTGGTTAGCC | GCTGCATCCAGTTGCAA AGT | CAACAGGCTAACAGTTCCC TCGGACG | |
| | | | SEQ ID NO:231 | SEQ ID NO:8243 | SEQ ID NO:16255 | |
| | | AA | RASQGIGNWLA | AASSLQS | QQANSFPRT | |
| | | | SEQ ID NO:232 | SEQ ID NO:8244 | SEQ ID NO:16256 | |
| iPS:392652 | 21-225_17C6 | NA | CGGGCAAGTCAGAGACCATTAA TACTTATTTAAAT | GCTGCATCCAGTTGCAA AGT | CAACAGAGTTACAGAACCCC CTTTCACT | |
| | | | SEQ ID NO:233 | SEQ ID NO:8245 | SEQ ID NO:16257 | |
| | | AA | RASQSINTYLN | AASSLQS | QQSYRTPFFT | |
| | | | SEQ ID NO:234 | SEQ ID NO:8246 | SEQ ID NO:16258 | |
| iPS:392654 | 21-225_17A10 | NA | CGGGCAAGTCAGGGCATTAG AAATGATTAGGC | GCTGCATCCAGTTTACAA AGT | CTACAGCAGCATAATAGTTACCC GCTCACT | |
| | | | SEQ ID NO:235 | SEQ ID NO:8247 | SEQ ID NO:16259 | |
| | | AA | RASQGIRNDLG | AASSLQS | LQHNSYPLT | |
| | | | SEQ ID NO:236 | SEQ ID NO:8248 | SEQ ID NO:16260 | |

FIGURE 49
(Continued)

| | | | | | |
|---|---|---|---|---|---|
| iPS:392656 | 21-225_1F2 | NA | CGGGCAAGTCAGGGCATTAG AAATGATTAGGC SEQ ID NO:237 RASQGIRNDLG SEQ ID NO:238 | GCTGCATCCAGTGTGCA AAGT SEQ ID NO:8249 AASSVQS SEQ ID NO:8250 | CTACAGGCATAATAGTTACCC GCTCACT SEQ ID NO:16261 LQHNSYPLT SEQ ID NO:16262 |
| iPS:392658 | 21-225_18E8 | NA | CGGGCAAGTCAGGGCATTAG AAATGATTAGGC SEQ ID NO:239 RASQGIRNDLG SEQ ID NO:240 | GCTGCATCCAGTTTGCAA AGT SEQ ID NO:8251 AASSLQS SEQ ID NO:8252 | CTACAGGCATAATAGTTACCC GCTCACT SEQ ID NO:16263 LQHNSYPLT SEQ ID NO:16264 |
| iPS:392660 | 21-225_19B3 | NA | CGGGCAAGTCAGAGACATTAT CAACTATTTAAAT SEQ ID NO:241 RAGQNIHYLN SEQ ID NO:242 | GTTGCATCCAGTTTGCAA AGT SEQ ID NO:8253 VASSLQS SEQ ID NO:8254 | CAACAGAGTTACAGTACCCC TTTCACT SEQ ID NO:16265 QQSYSTPFT SEQ ID NO:16266 |
| iPS:392664 | 21-225_20F6 | NA | CGGGCAAGTCAGAGCATTAT CACCTATTTAAAT SEQ ID NO:243 RASQSHTYLN SEQ ID NO:244 | ACTGCATCCAGTTGCAA AGT SEQ ID NO:8255 TASSLQS SEQ ID NO:8256 | CAACAGACTTACAGTCCCCC GCTCACT SEQ ID NO:16267 QQTYSPPLT SEQ ID NO:16268 |
| iPS:392666 | 21-225_16F11 | NA | CGGGCAAGTCAGGGCATTAG AAATGATTAGGC SEQ ID NO:245 RASQGIRNDLG SEQ ID NO:246 | GCTGCATCCAGTGTACA AAGT SEQ ID NO:8257 AASSVQS SEQ ID NO:8258 | CTACAGGCATAATAGTTACCC GCTCACT SEQ ID NO:16269 LQHNSYPLT SEQ ID NO:16270 |
| iPS:392668 | 21-225_17B4 | NA | CGGGCAAGTCAGAACATTAG TAGTTATTTAAAT SEQ ID NO:247 RASQNISSYLN SEQ ID NO:248 | GGTGCATCCAGTTGCA AACT SEQ ID NO:8259 GASSLQT SEQ ID NO:8260 | CAACAGAGTTACAGAACCCC CTTTTCACT SEQ ID NO:16271 QQSYRTPFFT SEQ ID NO:16272 |

FIGURE 49
(Continued)

| | | | | | |
|---|---|---|---|---|---|
| iPS:392674 | 21-225_18C2 | NA | CGGGCAAGTCAGGGCATTAG AAATGATTAGGC<br>SEQ ID NO:249 | ACTGCATCCAGTTTGCAA AGT<br>SEQ ID NO:8261 | CTACAACATAATAGTTACCC GTGGACG<br>SEQ ID NO:16273 |
| | | AA | RASQGIRNDLG<br>SEQ ID NO:250 | TASSLQS<br>SEQ ID NO:8262 | LQHNSYPWT<br>SEQ ID NO:16274 |
| iPS:392676 | 21-225_19F3 | NA | CGGGCAAGTCAGGGCATAA GAAATGATTAGGC<br>SEQ ID NO:251 | GCTGTTTCCAGTTTGCAA AGT<br>SEQ ID NO:8263 | CTACAGCATGCCAGTTACC GCTCACT<br>SEQ ID NO:16275 |
| | | AA | RASQGIRNDLG<br>SEQ ID NO:252 | AVSSLQS<br>SEQ ID NO:8264 | LQHASYPLT<br>SEQ ID NO:16276 |
| iPS:392678 | 21-225_20F3 | NA | CGGGCAAGTCAGAGCATTAG TAGTTATTTATAT<br>SEQ ID NO:253 | GCTGCATCCAGTTTGCAA AGT<br>SEQ ID NO:8265 | CAACAGAGTTACAGTGCCC TCCATTCACT<br>SEQ ID NO:16277 |
| | | AA | RASQSISSYLY<br>SEQ ID NO:254 | AASSLQS<br>SEQ ID NO:8266 | QQSYSAPPFT<br>SEQ ID NO:16278 |
| iPS:392680 | 21-225_20A7 | NA | CGGGCAAGTCAGGGCATTAG AAATGATTAGGC<br>SEQ ID NO:255 | GCTGCATCCAGTTTGCAA AGT<br>SEQ ID NO:8267 | CTACAGCATAATAGTTACCC GCTCACT<br>SEQ ID NO:16279 |
| | | AA | RASQGIRNDLG<br>SEQ ID NO:256 | AASSLQS<br>SEQ ID NO:8268 | LQHNSYPLT<br>SEQ ID NO:16280 |
| iPS:392682 | 21-225_16A12 | NA | CGGGCAAGTCAGGGCATTAA CACTTATTTAGCC<br>SEQ ID NO:257 | GCTGCATCCAGTTTGCAA AGT<br>SEQ ID NO:8269 | CAACAGTATTATAGTTACCC GCTCACT<br>SEQ ID NO:16281 |
| | | AA | RASQAINTYLA<br>SEQ ID NO:258 | AASSLQS<br>SEQ ID NO:8270 | QQYYSYPLT<br>SEQ ID NO:16282 |
| iPS:392684 | 21-225_17F4 | NA | CGGGCAAGTCAGGGCATTAG AAATGATTAGGC<br>SEQ ID NO:259 | GCTGCATCCAGTTTGCAA AGT<br>SEQ ID NO:8271 | CTACAGCATAATAGTTACCC ATTCACT<br>SEQ ID NO:16283 |
| | | AA | RASQGIRNDLG<br>SEQ ID NO:260 | AASSLQS<br>SEQ ID NO:8272 | LQHNSYPFT<br>SEQ ID NO:16284 |

FIGURE 49
(Continued)

| iPS ID | Clone | Type | Col1 | Col2 | Col3 |
|---|---|---|---|---|---|
| iPS:392686 | 21-225_17C7 | NA | CGGGCAAGTCAGGGCATTAG AAATGATTAGGC SEQ ID NO:261 | GCTGCATCCAGTTTGCAA AGT SEQ ID NO:8273 | CTACAGCATAATAGTTACCC GTGGACG SEQ ID NO:16285 |
| | | AA | RASQGIRNDLG SEQ ID NO:262 | AASSLQS SEQ ID NO:8274 | LQHNSYPWT SEQ ID NO:16286 |
| iPS:392690 | 21-225_18F2 | NA | CGGGCAAGTCAGGGCATTAG AAATGATTAGGC SEQ ID NO:263 | GCTGCATCCAGTTTGCAA AGT SEQ ID NO:8275 | CTACAGCATAATAGTTACCC GTGGACG SEQ ID NO:16287 |
| | | AA | RASQGIRNDLG SEQ ID NO:264 | AASSLQS SEQ ID NO:8276 | LQHNSYPWT SEQ ID NO:16288 |
| iPS:392692 | 21-225_18G10 | NA | CGGGCGAGTCAGGACATTAT CTATTATTAAAT SEQ ID NO:265 | GTTGCATCCAGTTTGCAA AGT SEQ ID NO:8277 | TTACAGTATAATAGTTACCC ATTCACT SEQ ID NO:16289 |
| | | AA | RASQDISYYLA SEQ ID NO:266 | VASSLQS SEQ ID NO:8278 | LQYNSYPFT SEQ ID NO:16290 |
| iPS:392694 | 21-225_19A5 | NA | CGGGCAAGTCAGAACATTAT CAACTATTTAAAT SEQ ID NO:267 | GTTGCATCCAATTTACAA GGT SEQ ID NO:8279 | CAACAGAGTTACAGTACCC TTTCACT SEQ ID NO:16291 |
| | | AA | RASQNIINYLN SEQ ID NO:268 | VASNLQG SEQ ID NO:8280 | QQSYSTPFT SEQ ID NO:16292 |
| iPS:392696 | 21-225_20A4 | NA | CGGGCAAGTCAGAGACATTAG CAACTATTTAAAT SEQ ID NO:269 | GCTGCATCCAGTTTGCAC AGT SEQ ID NO:8281 | CAACAGAGTTACAGAACCC CTTATTCACT SEQ ID NO:16293 |
| | | AA | RASQSIINYLN SEQ ID NO:270 | AASSLHS SEQ ID NO:8282 | QQSYRTPLFT SEQ ID NO:16294 |
| iPS:392700 | 21-225_16E12 | NA | CGGGCAAGTCAGGGCATTAG AAATGATTAGGC SEQ ID NO:271 | GCTGCATCCAGTTACAA AGT SEQ ID NO:8283 | CTACAGCATAATAGTTACCC GCTCACT SEQ ID NO:16295 |
| | | AA | RASQGIRNDLG SEQ ID NO:272 | AASSLQS SEQ ID NO:8284 | LQHNSYPLT SEQ ID NO:16296 |

FIGURE 49
(Continued)

| | | | | | |
|---|---|---|---|---|---|
| iPS:392702 | 21-225_17F7 | NA | CGGGCAAGTCAGAGACCATTAG TAGTTTTTAAAT<br>SEQ ID NO:273<br>RASQTISSFLN<br>SEQ ID NO:274 | GCTGCTGCTTCCAGTTTGCAA AGT<br>SEQ ID NO:8285<br>AASSLQS<br>SEQ ID NO:8286 | CAACAGAGTTACAGAACCCC CTTTTTCACT<br>SEQ ID NO:16297<br>QQSYRTPFFT<br>SEQ ID NO:16298 |
| iPS:392704 | 21-225_17F11 | NA<br>AA | CGGGCAAGTCGGAGACCATTAA CAACTATTAAAT<br>SEQ ID NO:275<br>RASRTINNYLN<br>SEQ ID NO:276 | GCTACACATCCAGTTTACAA AGT<br>SEQ ID NO:8287<br>ATSSLQS<br>SEQ ID NO:8288 | CAACAGACTTACAGTACCCC CTTATTCGCT<br>SEQ ID NO:16299<br>QQTYSTPLFA<br>SEQ ID NO:16300 |
| iPS:392706 | 21-225_18A3 | NA<br>AA | CGGGCAAGTCAGGGCATTAG AAATGATTTAGGC<br>SEQ ID NO:277<br>RASQGIRNDLG<br>SEQ ID NO:278 | GTTGCATCCAGTTTGCAA AGT<br>SEQ ID NO:8289<br>VASSLQS<br>SEQ ID NO:8290 | CTACAGCATAGTAGTTACCC GCTCACT<br>SEQ ID NO:16301<br>LQHSSYPLT<br>SEQ ID NO:16302 |
| iPS:392708 | 21-225_18D11 | NA<br>AA | CGGGCGAGTCAGGGCATTAG CTATTATTTAGCC<br>SEQ ID NO:279<br>RASQGISYYLA<br>SEQ ID NO:280 | GTTGCATCCAGTTTGCAA AGT<br>SEQ ID NO:8291<br>VASSLQS<br>SEQ ID NO:8292 | CAACAGTATAATACTTACCC ATTCACT<br>SEQ ID NO:16303<br>QQYNTYPFT<br>SEQ ID NO:16304 |
| iPS:392710 | 21-225_19A10 | NA<br>AA | CGGGCAAGTCAGGGCATTAG AACTGATTTAGGC<br>SEQ ID NO:281<br>RASQGIRTDLG<br>SEQ ID NO:282 | ACTGCATCCAGTTTGCAA AGT<br>SEQ ID NO:8293<br>TASSLQS<br>SEQ ID NO:8294 | CTACAGCATAATGGTTACCC GTGGACG<br>SEQ ID NO:16305<br>LQHNGYPWT<br>SEQ ID NO:16306 |
| iPS:392714 | 21-225_16G12 | NA<br>AA | CGGGCGAGTCAGGACATTAG CAATTATTTAGCC<br>SEQ ID NO:283<br>RASQDISNYLA<br>SEQ ID NO:284 | GCTGCATCCAGTTTGCAA AGT<br>SEQ ID NO:8295<br>AASSLQS<br>SEQ ID NO:8296 | CAACAGTATCATAGTTCCC ATTCACT<br>SEQ ID NO:16307<br>QQYHSPFT<br>SEQ ID NO:16308 |

FIGURE 49
(Continued)

| | | | | | |
|---|---|---|---|---|---|
| iPS:392716 | 21-225_17B5 | NA | CGGGCAAGTCAGGGCATTAG AAATGATTTAGGC SEQ ID NO:285 | GCTGCATCCAATTTGCAA AGT SEQ ID NO:8297 | CTACAGCATAATAGTTACCC GCTCACT SEQ ID NO:16309 |
| | | AA | RASQGIRNDLG SEQ ID NO:286 | AASNLQS SEQ ID NO:8298 | LQHNSYPLT SEQ ID NO:16310 |
| iPS:392718 | 21-225_17B8 | NA | AGGTCTAGTCAGAGCCTCCT GCATAGTAATGGGAACAACT CTTTTGGAT SEQ ID NO:287 | TTGGGTTCTCATCGGGCC TCC SEQ ID NO:8299 | ATGCAAGTTCTACAAACTCC TCCCCTCACT SEQ ID NO:16311 |
| | | AA | RSSQSLLHSNGNNSLD SEQ ID NO:288 | LGSHRAS SEQ ID NO:8300 | MQVLQTPPLT SEQ ID NO:16312 |
| iPS:392720 | 21-225_17A12 | NA | CGGGCAAGTCAGAGCATTAG TAGTTATTTAAAT SEQ ID NO:289 | GCTGCATCCAGTTTGCAA AGT SEQ ID NO:8301 | CAACAGAGTTACAATACCCC CTTATTCACT SEQ ID NO:16313 |
| | | AA | RASQSISSYLN SEQ ID NO:290 | AASSLQS SEQ ID NO:8302 | QQSYNTPLFT SEQ ID NO:16314 |
| iPS:392722 | 21-225_18E12 | NA | CGGGCAAGTCAGAGCATTAA TAGTTATTTAAAT SEQ ID NO:291 | GCTGCATCCAGTTTACAA AGT SEQ ID NO:8303 | CAACAGAGTTACAGAACCCC CTTTTTCACT SEQ ID NO:16315 |
| | | AA | RASQSISSYLN SEQ ID NO:292 | AASSLQS SEQ ID NO:8304 | QQSYRTPFFT SEQ ID NO:16316 |
| iPS:392726 | 21-225_20B5 | NA | CGGGCAAGTCAGGGCATTAA CAATTATTTAGCC SEQ ID NO:293 | GCTGCATCCACTTTGCAA TCA SEQ ID NO:8305 | CAAAAGTATAACAGTGCCCC TCCGATCACC SEQ ID NO:16317 |
| | | AA | RASQGINNYLA SEQ ID NO:294 | AASTLQS SEQ ID NO:8306 | QKYNSAPPIT SEQ ID NO:16318 |
| iPS:392728 | 21-225_20F7 | NA | CGGGCGAGTCAGGGTATTAG CAGCTGGTTAGCC SEQ ID NO:295 | GCTGCATCCAGTTTGCAA AGT SEQ ID NO:8307 | CAACAGGCTAACAGTTTCC TCGGACG SEQ ID NO:16319 |
| | | AA | RASQGISSWLA | AASSLQS | QQANSFPRT |

FIGURE 49
(Continued)

| | | | | | | |
|---|---|---|---|---|---|---|
| iPS:392730 | 21-225_17A1 | NA | SEQ ID NO:296 CGGGCAAGTCAGAGAACATTAA CAATTATTTAAAT | SEQ ID NO:8308 ACTACATCTAGTTTACAA AGT | SEQ ID NO:16320 CAACAGAGTTACACTACCCC CACGTGGACG |
| | | | SEQ ID NO:297 RASQNINNYLN | SEQ ID NO:8309 TTSSLQS | SEQ ID NO:16321 QQSYTTPTWT |
| | | AA | | | |
| iPS:392732 | 21-225_17E5 | NA | SEQ ID NO:298 CGGGCAAGTCAGGGCATTAG AAATGATTTAGGC | SEQ ID NO:8310 ACTGCATCCAGTTTGCAA AGT | SEQ ID NO:16322 CTACAACATAATAGTTACCC GTTGACG |
| | | AA | SEQ ID NO:299 RASQGIRNDLG | SEQ ID NO:8311 TASSLQS | SEQ ID NO:16323 LQHNSYPLT |
| iPS:392734 | 21-225_17D8 | NA | SEQ ID NO:300 AGGGCCAGTCAGAGAGTGTTAG CAGCAACTTAGCC | SEQ ID NO:8312 GGTGCATCCACCAGGGC CAGT | SEQ ID NO:16324 CAGCAGTATAATAACTGGCC TCTGACG |
| | | AA | SEQ ID NO:301 RASQSVSSNLA | SEQ ID NO:8313 GASTRAS | SEQ ID NO:16325 QQYNNWPLT |
| iPS:392736 | 21-225_17B12 | NA | SEQ ID NO:302 CGGGCAAGTCAGAGAATATTAA CAACTATTTAAAT | SEQ ID NO:8314 ACTGCATCCAGTTTGCAA AGT | SEQ ID NO:16326 CAACAGACTTACACTACCCC CACGTGGACG |
| | | AA | SEQ ID NO:303 RASQNINNYLN | SEQ ID NO:8315 TASSLQS | SEQ ID NO:16327 QQTYTTPTWT |
| iPS:392738 | 21-225_18G4 | NA | SEQ ID NO:304 CGGGCAAGTCAGAGCATTAT CAGCTATTTAAAT | SEQ ID NO:8316 ACTGCATCCAGTTTGCAA ACT | SEQ ID NO:16328 CAACAGACTTACAGTCCCCC GCTCACT |
| | | AA | SEQ ID NO:305 RASQSIISYLN | SEQ ID NO:8317 TASSLQT | SEQ ID NO:16329 QQTYSPPLT |
| iPS:392740 | 21-225_18H12 | NA | SEQ ID NO:306 CGGGCAAGTCAGGGCATTAG AAATGATTTAGGC | SEQ ID NO:8318 ACTGCATCCAATTTGCAA AGT | SEQ ID NO:16330 CTACAACATAATAATTACCC GTGGACG |
| | | AA | SEQ ID NO:307 RASQGIRNDLG | SEQ ID NO:8319 TASNLQS | SEQ ID NO:16331 LQHNNYPWT |

FIGURE 49
(Continued)

| | | | | | | | |
|---|---|---|---|---|---|---|---|
| iPS:392742 | 21-225_20B2 | NA | SEQ ID NO:308 CGGGCAAGTCAGGACATTAG AAATGATTTAGGC | SEQ ID NO:8320 GCTGCATCCAGTTTGCAA AGT | SEQ ID NO:16332 CTACAGCATTATAATTACCC TCGGGCG |
| | | AA | SEQ ID NO:309 RASQDIRNDLG | SEQ ID NO:8321 AASSLQS | SEQ ID NO:16333 LQHYNYPRA |
| iPS:392744 | 21-225_20D5 | NA | SEQ ID NO:310 CGGGCAAGTCAGGGCATTAG AAATGATTTAGGC | SEQ ID NO:8322 GCTGCATCCAGTTTGCAA AGT | SEQ ID NO:16334 CTACAGCATAATAGTTACCC GTTCACT |
| | | AA | SEQ ID NO:311 RASQGIRNDLG | SEQ ID NO:8323 AASSLQS | SEQ ID NO:16335 LQHNSYPFT |
| iPS:392746 | 21-225_20H7 | NA | SEQ ID NO:312 CGGACGAGTCAGGGCATTAA CAATTATTTAGTC | SEQ ID NO:8324 GCTGCATCCAGTTTGCAA AGT | SEQ ID NO:16336 CAACAGTATTATAGTTACCC ATTCACT |
| | | AA | SEQ ID NO:313 RTSQGINNYLV | SEQ ID NO:8325 AASSLQS | SEQ ID NO:16337 QQYYSYPFT |
| iPS:392748 | 21-225_20A8 | NA | SEQ ID NO:314 CGGGCGAGTCAGGGCATTAA TAATTATTTAGTC | SEQ ID NO:8326 GCTGCATCCAGTTTGCTG AGT | SEQ ID NO:16338 CAACAGTATAATAGTTACCC GATCACC |
| | | AA | SEQ ID NO:315 RASQGINNYLV | SEQ ID NO:8327 AASSLLS | SEQ ID NO:16339 QQYNSYPIT |
| iPS:392750 | 21-225_20A10 | NA | SEQ ID NO:316 CGGGCAAGTCAGGGCATTAG AAATGATTTAGGC | SEQ ID NO:8328 GCTGCATCCAGTTTGCAA AGT | SEQ ID NO:16340 CTACAGCATAATAGATACCC GCTCACT |
| | | AA | SEQ ID NO:317 RASQGIRNDLG | SEQ ID NO:8329 AASSLQS | SEQ ID NO:16341 LQHNRYPLT |
| iPS:392754 | 21-225_21D3 | NA | SEQ ID NO:318 CGGGCAAGTCAGAGCATTAC TGGTTATTCAAAT | SEQ ID NO:8330 GCTACATACAGTTTGGA AAGT | SEQ ID NO:16342 CAACAGAGTTACAGTACCTC GATCACC |
| | | AA | SEQ ID NO:319 RASQSITGYSN | SEQ ID NO:8331 ATYSLES | SEQ ID NO:16343 QQSYSTSIT |

FIGURE 49
(Continued)

| | | | | | | | |
|---|---|---|---|---|---|---|---|
| iPS:392758 | 21-225_21G11 | NA | SEQ ID NO:320 CGGGCAAGTCAGGGCATTAG AAATGATTTAGGC | SEQ ID NO:8332 ACTGCATCCAGTTTGCAA AGT | SEQ ID NO:16344 CTACAACATAATAATTACCC GTGGACG |
| | | AA | SEQ ID NO:321 RASQGIRNDLG | SEQ ID NO:8333 TASSLQS | SEQ ID NO:16345 LQHNNYPWT |
| iPS:392760 | 21-225_22G3 | NA | SEQ ID NO:322 CGGGCAAGTCAGAGAGCATTAG TAATTATTTAAAT | SEQ ID NO:8334 GCTGCTTCCAGTTTGCAA AGT | SEQ ID NO:16346 CAACAGAGTTCAGAACCCC CTTTTTCACT |
| | | AA | SEQ ID NO:323 RASQSISNYLN | SEQ ID NO:8335 AASSLQS | SEQ ID NO:16347 QQSFRTPFFT |
| iPS:392762 | 21-225_22G5 | NA | SEQ ID NO:324 CGGGCAAGTCAGAGAACATTAG CAGCTATTTAAAT | SEQ ID NO:8336 GCTGCATCCAGTTTGCAA AAT | SEQ ID NO:16348 CAACAGAGTTACAGAACCCC CTTATTCACT |
| | | AA | SEQ ID NO:325 RASQNISSYLN | SEQ ID NO:8337 AASSLQN | SEQ ID NO:16349 QQSYRTPLFT |
| iPS:392764 | 21-225_22G10 | NA | SEQ ID NO:326 CGGGCAAGTCAGAGAGCATTTT CAGCTATTTAAAT | SEQ ID NO:8338 GCTGCATCCAGTTTACAA AGT | SEQ ID NO:16350 CAACAGAGTTCAGAACCCC CTTATTCACT |
| | | AA | SEQ ID NO:327 RASQSIFSYLN | SEQ ID NO:8339 AASSLQS | SEQ ID NO:16351 QQSFRTPLFT |
| iPS:392766 | 21-225_23H4 | NA | SEQ ID NO:328 CGGGCAAGTCAGAGAGCATTAG CAGGTATTTAAAT | SEQ ID NO:8340 TCTACATCCAGTTTGCAA AGT | SEQ ID NO:16352 CAACAGAGTTACAGTACCCC CACGTGGACG |
| | | AA | SEQ ID NO:329 RASQSISRYLN | SEQ ID NO:8341 STSSLQS | SEQ ID NO:16353 QQSYSTPTWT |
| iPS:392768 | 21-225_20B8 | NA | SEQ ID NO:330 AGGGCCAGTCAGAGTGTTAG CAGCAACTTAGCC | SEQ ID NO:8342 GGTGCATCCACCAGGGC CAGT | SEQ ID NO:16354 CAGCAGTATAATAACTGTCC TCTGACG |
| | | AA | SEQ ID NO:331 RASQSVSSNLA | SEQ ID NO:8343 GASTRAS | SEQ ID NO:16355 QQYNNCPLT |

FIGURE 49
(Continued)

| | | | | | | |
|---|---|---|---|---|---|---|
| iPS:392770 | 21-225_20C10 | NA | SEQ ID NO:332 CGGGCAAGTCACCACCATATTAG CAACTATTAAAT | SEQ ID NO:8344 ACTGCATCCAGTTTGCAA AGT | SEQ ID NO:16356 CAACAGAGTTACACTACCCC CACGTGGACG | |
| | | AA | SEQ ID NO:333 RASHHISNYLN | SEQ ID NO:8345 TASSLQS | SEQ ID NO:16357 QQSYTTPTWT | |
| iPS:392772 | 21-225_20E12 | NA | SEQ ID NO:334 CGGGCAAGTCAGGGCATTAG AAATGATTTAGGC | SEQ ID NO:8346 GCTGCATCCAGTTTGCAA AGT | SEQ ID NO:16358 CTACAGCATAATAGTTACCC GTTCACT | |
| | | AA | SEQ ID NO:335 RASQGIRNDLG | SEQ ID NO:8347 AASSLQS | SEQ ID NO:16359 LQHNSYPFT | |
| iPS:392774 | 21-225_21F3 | NA | SEQ ID NO:336 CGGGCAAGTCAGGGCATTAG AAATGATTTAGGC | SEQ ID NO:8348 GCTGCATCCAGTTTGCAA AGT | SEQ ID NO:16360 CTACAGCATAGTAGTTACCC CCTCACT | |
| | | AA | SEQ ID NO:337 RASQGIRNDLG | SEQ ID NO:8349 AASSLQS | SEQ ID NO:16361 LQHSSYPLT | |
| iPS:392776 | 21-225_21A12 | NA | SEQ ID NO:338 CGGGCGAGTCAAGGCATTAG CAAATATTTAGCC | SEQ ID NO:8350 GCTGCATCCAGTTTGCAA AGT | SEQ ID NO:16362 CAACAGTATAATAGTTACCC GTTCAGG | |
| | | AA | SEQ ID NO:339 RASQGISKYLA | SEQ ID NO:8351 AASSLQS | SEQ ID NO:16363 QQYNSYPFR | |
| iPS:392778 | 21-225_22B3 | NA | SEQ ID NO:340 CGGGCAAGTCAGGACATTAG AAATAATTTAGGC | SEQ ID NO:8352 CCTGCATCCAGTTTGCAA ACT | SEQ ID NO:16364 CTACAGGATAATAGTTACCC ATTCACT | |
| | | AA | SEQ ID NO:341 RASQDIRNNLG | SEQ ID NO:8353 PASSLQT | SEQ ID NO:16365 LQDNSYPFT | |
| iPS:392780 | 21-225_22B7 | NA | SEQ ID NO:342 CGGGCAAGTCAGGGCATTAG AAATGATTTAGGC | SEQ ID NO:8354 ACTGCATCCAGTTTGCAA AGT | SEQ ID NO:16366 CTACAGCATAATACTTACCC GCTCACT | |
| | | AA | SEQ ID NO:343 RASQGIRNDLG | SEQ ID NO:8355 TASSLQS | SEQ ID NO:16367 LQHNTYPLT | |

FIGURE 49
(Continued)

| | | | | | | |
|---|---|---|---|---|---|---|
| iPS:392782 | 21-225_22B12 | NA | SEQ ID NO:344 CGGGCGAGTCAGGGACATTAG CAATTATTTAGCC | SEQ ID NO:8356 GGTGCATCCAGTTTGCG GAGT | SEQ ID NO:16368 CAACAGTATCATAGTTACCC ATTCACT |
| | | AA | SEQ ID NO:345 RASQDISNYLA | SEQ ID NO:8357 GASSLRS | SEQ ID NO:16369 QQYHSYPFT |
| iPS:392784 | 21-225_23C7 | NA | SEQ ID NO:346 CGGGCGAGTCAGGGCATTGG CATTTATTTAGCC | SEQ ID NO:8358 GCTGCATCCAGTTTGCAA AGT | SEQ ID NO:16370 CAACAGTATAATAGTTACCC ATTCACT |
| | | AA | SEQ ID NO:347 RASQGIGIYLA | SEQ ID NO:8359 AASSLQS | SEQ ID NO:16371 QQYNSYPFT |
| iPS:392786 | 21-225_24E1 | NA | SEQ ID NO:348 AAGTCCAGCCAGAGTGTTT ATACACCTCCAACAATAACA ACTACTTAACT | SEQ ID NO:8360 TGGGCATCTACCCGGGA ATCC | SEQ ID NO:16372 CAGCAATTTTATAGTACTCC TCCGACG |
| | | AA | SEQ ID NO:349 KSSQSVLYTSNNNNYLT | SEQ ID NO:8361 WASTRES | SEQ ID NO:16373 QQFYSTPPT |
| iPS:392788 | 21-225_20C8 | NA | SEQ ID NO:350 CGGGCAAGTCAGGGCATTAG AAATGATTTAGGC | SEQ ID NO:8362 GCTGCATCCAGTTTGCAA AGT | SEQ ID NO:16374 CTACAAGATAATAGTTACCC GTTCACT |
| | | AA | SEQ ID NO:351 RASQGIRNDLG | SEQ ID NO:8363 AASSLQS | SEQ ID NO:16375 LQDNSYPFT |
| iPS:392790 | 21-225_20D10 | NA | SEQ ID NO:352 CGGGCAAGTCAGGGCATTAG AAATGATTTAGGC | SEQ ID NO:8364 GTTGCATACAGTTTGCAA AGT | SEQ ID NO:16376 ATACAGCAAAATAGTTACCC GTGGACG |
| | | AA | SEQ ID NO:353 RASQGIRNDLG | SEQ ID NO:8365 VAYSLQS | SEQ ID NO:16377 IQQNSYPWT |
| iPS:392792 | 21-225_20G12 | NA | SEQ ID NO:354 CGGGCGAGTCAGGGCATTAG CAATTATTTAGCC | SEQ ID NO:8366 ACTGCATCCACTTTGCAA TCA | SEQ ID NO:16378 CAAAAGTATAACAGTGCCCC TCCGATCACC |
| | | | SEQ ID NO:355 | SEQ ID NO:8367 | SEQ ID NO:16379 |

FIGURE 49
(Continued)

| | | AA | RASQGISNYLA | TASTLQS | QKYNSAPPIT |
|---|---|---|---|---|---|
| iPS:392794 | | | SEQ ID NO:356 | SEQ ID NO:8368 | SEQ ID NO:16380 |
| | 21-225_21H3 | NA | CGGGCAAGTCAGGGCATTAG AAATGATTAGGC | GCTGCGTCCAGTGTGCA AACT | CTACAGCATAATAGTTATCC GCTCACT |
| | | | SEQ ID NO:357 | SEQ ID NO:8369 | SEQ ID NO:16381 |
| iPS:392796 | | AA | RASQGIRNDLG | AASSVQF | LQHNSYPLT |
| | | | SEQ ID NO:358 | SEQ ID NO:8370 | SEQ ID NO:16382 |
| | 21-225_22A4 | NA | CGGGCAAGTCAGGGCATTAG AAATGATTAGGC | GCTGCATCCAGTTTGCAA AGT | CTTCAGCATAATAGTTACCC GTGGACG |
| | | | SEQ ID NO:359 | SEQ ID NO:8371 | SEQ ID NO:16383 |
| iPS:392798 | | AA | RASQGIRNDLG | AASSLQS | LQHNSYPWT |
| | | | SEQ ID NO:360 | SEQ ID NO:8372 | SEQ ID NO:16384 |
| | 21-225_22C7 | NA | CGGGCAAGTCAGAACATTAT CAGCTATTAAAT | ATTGCATCCAGTTTGCAG AGT | CAACAGACTTACAGTACCCC GCTCACT |
| | | | SEQ ID NO:361 | SEQ ID NO:8373 | SEQ ID NO:16385 |
| iPS:392800 | | AA | RASQNIISYLN | IASSLQS | QQTYSTPLT |
| | | | SEQ ID NO:362 | SEQ ID NO:8374 | SEQ ID NO:16386 |
| | 21-225_22D12 | NA | CGGGCAAGTCAGGGCATTAG AAATGATTAGGC | GCTGCATCCAGTTTGCAA AGT | CTACAGCATAGTACTTACCC TCTCACT |
| | | | SEQ ID NO:363 | SEQ ID NO:8375 | SEQ ID NO:16387 |
| iPS:392802 | | AA | RASQGIRNDLG | AASSLQS | LQHSTYPLT |
| | | | SEQ ID NO:364 | SEQ ID NO:8376 | SEQ ID NO:16388 |
| | 21-225_23E7 | NA | CGGGCGAGTCAGGGCATTAG CAATTATTAGCC | GCTGCATCCAGTTTGCAA AGT | CAACAGTTTTATAGTTACCC ATTCACT |
| | | | SEQ ID NO:365 | SEQ ID NO:8377 | SEQ ID NO:16389 |
| iPS:392806 | | AA | RASQGISNYLA | AASSLQS | QQFYSYPFT |
| | | | SEQ ID NO:366 | SEQ ID NO:8378 | SEQ ID NO:16390 |
| | 21-225_24H3 | NA | AGGGCCAGTCAGAGTGTTAG CAGCAACTTAGCC | TTTGCATCCATCAGGGCC ACT | CAGCAGTATAATAACTGGCC CATGTGCAGT |
| | | | SEQ ID NO:367 | SEQ ID NO:8379 | SEQ ID NO:16391 |

FIGURE 49
(Continued)

| ID | Clone | AA/NA | CDR1 | CDR2 | CDR3 |
|---|---|---|---|---|---|
| iPS:392808 | | AA | RASQSVSSNLA | FASIRAT | QQYNNWPMCS |
| | | NA | CGGGCAAGTCAGAGCATTAGCAGGTATTTAAAT SEQ ID NO:368 | GCTGCTTCCAGTTTGCAA AGT SEQ ID NO:8380 | CAACAGAGTTACAATACCCC CACGTGGACG SEQ ID NO:16392 |
| iPS:392810 | 21-225_20F8 | AA | RASQSISRYLN SEQ ID NO:369 | AASSLQS SEQ ID NO:8381 | QQSYNTPTWT SEQ ID NO:16393 |
| | | NA | CGGGCAAGTCAGGGCATTAG AAATGATTAGAC SEQ ID NO:370 | GCTGCATCCAGTTTGCAA AGT SEQ ID NO:8382 | CTACAGCATAATAGTTACCC GCTCACT SEQ ID NO:16394 |
| iPS:392812 | 21-225_20H12 | AA | RASQGIRNDLD SEQ ID NO:371 | AASSLQS SEQ ID NO:8383 | LQHNSYPLT SEQ ID NO:16395 |
| | | NA | CGGGCAAGTCAGAACATTGG TAGTTATTTAAAT SEQ ID NO:372 | GCTGCATCCAGTTTGCAA AGT SEQ ID NO:8384 | CAACAGAGTTACAGAACCCC CTTTTTCACT SEQ ID NO:16396 |
| iPS:392814 | 21-225_21F4 | AA | RASQNIGSYLN SEQ ID NO:373 | AASSLQS SEQ ID NO:8385 | QQSYRTPFFT SEQ ID NO:16397 |
| | | NA | AAGTCTAGTCAGAGCCTCCT GCATAGTGGTGGAAAGACCT ATTTATAT SEQ ID NO:374 | GAAGTTTCCAACCGGTTC TCT SEQ ID NO:8386 | ATGCAAACTTTACACCTTCC GTGGACG SEQ ID NO:16398 |
| iPS:392816 | 21-225_22A1 | AA | KSSQSLLHSGGKTYLY SEQ ID NO:375 | EVSNRFS SEQ ID NO:8387 | MQTLHLPWT SEQ ID NO:16399 |
| | | NA | CGGGCAAGTCAGAACATTAG TAGTTATTTAAAT SEQ ID NO:376 | GCTGCATCCAGTTTGCAA AGT SEQ ID NO:8388 | CAACAGAGTTACAATACCCC CTTATTCACT SEQ ID NO:16400 |
| iPS:392818 | 21-225_22E4 | AA | RASQNISSYLN SEQ ID NO:377 | AASSLQS SEQ ID NO:8389 | QQSYNTPLFT SEQ ID NO:16401 |
| | | NA | CGGACAAGTCAGAACAGTA ACAGTTATTTAAAT SEQ ID NO:378 | GCTGCATACAGTTTGGA AAGT SEQ ID NO:8390 | CAACAGACTTACGGTACCTC GATCACC SEQ ID NO:16402 |

FIGURE 49
(Continued)

| | | | | | | |
|---|---|---|---|---|---|---|
| iPS:392820 | 21-225_22D8 | AA | SEQ ID NO:379<br>RTSQNSNSYLN | SEQ ID NO:8391<br>AAYSLES | SEQ ID NO:16403<br>QQTYGTSIT | |
| iPS:392822 | 21-225_23D1 | NA | SEQ ID NO:380<br>CGGGCAAGTCAGGGCATCA<br>GAAATGATTTAGGC | SEQ ID NO:8392<br>GCTGCATCCAGTTACAA<br>AGT | SEQ ID NO:16404<br>CTACAGCATAGTAGTTACCC<br>TCTCACT | |
| | | AA | SEQ ID NO:381<br>RASQGIRNDLG | SEQ ID NO:8393<br>AASSLQS | SEQ ID NO:16405<br>LQHSSYPLT | |
| iPS:392824 | 21-225_23C8 | NA | SEQ ID NO:382<br>CGGGCAAGTCAGGGACATTAG<br>AAATGATTTAGGC | SEQ ID NO:8394<br>GGTGCATCCAGTGTGCA<br>AAGT | SEQ ID NO:16406<br>CTACAGCATAATAGTTACCC<br>GCTCACT | |
| | | AA | SEQ ID NO:383<br>RASQDIRNDLG | SEQ ID NO:8395<br>GASSVQS | SEQ ID NO:16407<br>LQHNSYPLT | |
| iPS:392826 | 21-225_24E5 | NA | SEQ ID NO:384<br>CGGGCAAGTCAGGGCATTAG<br>AAATGATTTAGGC | SEQ ID NO:8396<br>GCTGCATCCAGTTGCAA<br>AGT | SEQ ID NO:16408<br>CTACAGCATAGTAATTACCC<br>GCTCACT | |
| | | AA | SEQ ID NO:385<br>RASQGIRNDLG | SEQ ID NO:8397<br>AASSLQS | SEQ ID NO:16409<br>LQHSNYPLT | |
| iPS:392830 | 21-225_20B9 | NA | SEQ ID NO:386<br>CGGGCGAGTCAGGGCATTAG<br>CAATTATTTAGGC | SEQ ID NO:8398<br>GTTGCATCCAGTTGCAA<br>AGT | SEQ ID NO:16410<br>CAACAGTATAATACTTATCC<br>ATTCACT | |
| | | AA | SEQ ID NO:387<br>RASQGISNYLA | SEQ ID NO:8399<br>VASSLQS | SEQ ID NO:16411<br>QQYNTYPFT | |
| iPS:392832 | 21-225_21A5 | NA | SEQ ID NO:388<br>CGGGCAAGTCAGACCATTAG<br>CAGCCATTTAAAT | SEQ ID NO:8400<br>GCTGCATCCAGTTGCAA<br>AGT | SEQ ID NO:16412<br>CAACAGTATACAATATCC<br>ATTCACT | |
| | | AA | SEQ ID NO:389<br>RASQTISSHLN | SEQ ID NO:8401<br>AASSLQS | SEQ ID NO:16413<br>QQSYNISFT | |
| | | NA | SEQ ID NO:390<br>CGGGCAAGTCAGGGCATTAG<br>AAATGATTTAGGC | SEQ ID NO:8402<br>GCTGCATCCAGTTACAA<br>AGT | SEQ ID NO:16414<br>CTACAGCATAATAGTTACCC<br>GTGGACG | |

FIGURE 49
(Continued)

| | | | | | | | | |
|---|---|---|---|---|---|---|---|---|
| | 21-225_21H8 | AA | SEQ ID NO:391 RASQGIRNDLG | | SEQ ID NO:8403 AASSLQS | | SEQ ID NO:16415 LQHNSYPWT | |
| iPS:392834 | | NA | SEQ ID NO:392 CGGACAAGTCAGGGCATTAG AAATGATTTAGGC | | SEQ ID NO:8404 GCTGCATCCAGTTGCAA AGT | | SEQ ID NO:16416 CTACAGCATAGTACTTACCC GCTCACT | |
| | 21-225_22C1 | AA | SEQ ID NO:393 RTSQGIRNDLG | | SEQ ID NO:8405 AASSLQS | | SEQ ID NO:16417 LQHSTYPLT | |
| iPS:392836 | | NA | SEQ ID NO:394 CGGGCGAGTCAGGGCATTAG AGATGATTTAGGC | | SEQ ID NO:8406 GCTGCATCCAGTTGCAA AGT | | SEQ ID NO:16418 CTACACCACTATAGTTATCC TCGGACG | |
| | 21-225_22F4 | AA | SEQ ID NO:395 RASQVIRDDLG | | SEQ ID NO:8407 AASSLQS | | SEQ ID NO:16419 LHHYSYPRT | |
| iPS:392838 | | NA | SEQ ID NO:396 CGGACAAGTCAGGGCATTAG AAATGATTTAGGC | | SEQ ID NO:8408 GCTGCATCCAGTTGCAA AGT | | SEQ ID NO:16420 CTACAGCATAATAGTTACCC GCTCACT | |
| | 21-225_22G8 | AA | SEQ ID NO:397 RTSQGIRNDLG | | SEQ ID NO:8409 AASSLQS | | SEQ ID NO:16421 LQHNSYPLT | |
| iPS:392840 | | NA | SEQ ID NO:398 CGGGCGAGTCAGGGCATTAG CAATTATTTAGCC | | SEQ ID NO:8410 GCTGCATCCAGTTACAG AGT | | SEQ ID NO:16422 CAACAGTATAATAGTTACCC ATTCACT | |
| | 21-225_23G1 | AA | SEQ ID NO:399 RASQGISNYLA | | SEQ ID NO:8411 AASSLQS | | SEQ ID NO:16423 QQYNSYPFT | |
| iPS:392842 | | NA | SEQ ID NO:400 CGGGCGAGTCAGGGCATTAG AAATTATTTAGGC | | SEQ ID NO:8412 GCTGCATCCAGTTGCAA AGT | | SEQ ID NO:16424 CAACAGTATAATAGTTACCC TTTCACT | |
| | 21-225_23G8 | AA | SEQ ID NO:401 RASQGIRNYLA | | SEQ ID NO:8413 AASSLQS | | SEQ ID NO:16425 QQYNSYPFT | |
| iPS:392844 | | NA | SEQ ID NO:402 CGGGCAAGTCAGGGCATTAG AAATGATTTAGGC | | SEQ ID NO:8414 CCTGCATCCAGTTGCAA AGT | | SEQ ID NO:16426 CTACAGCATAATAGTTACCC GTGGACG | |

FIGURE 49
(Continued)

| | | | | | | | |
|---|---|---|---|---|---|---|---|
| iPS:392846 | 21-225_23E11 | AA | SEQ ID NO:403<br>RASQGIRNDLG | SEQ ID NO:8415<br>PASSLQS | SEQ ID NO:16427<br>LQHNSYPWT | | |
| | | NA | SEQ ID NO:404<br>CGGGCAAGTCAGGACATTAGAAATGATTTAGGC | SEQ ID NO:8416<br>GCTGCATCCAGTTTGCACAGT | SEQ ID NO:16428<br>CTACAGCATTATAGTTACCCTCGGACG | | |
| iPS:392848 | 21-225_24B6 | AA | SEQ ID NO:405<br>RASQDIRNDLG | SEQ ID NO:8417<br>AASSLHS | SEQ ID NO:16429<br>LQHYSYPRT | | |
| | | NA | SEQ ID NO:406<br>CGGGCGAGTCAGGGCATTAGCAATTATTTAGGCC | SEQ ID NO:8418<br>GCTGCATCCAGTTTGCAAAGT | SEQ ID NO:16430<br>CAACAGTATCATAGTTACCCGTGGACG | | |
| iPS:392850 | 21-225_20F9 | AA | SEQ ID NO:407<br>RASQGISNYLA | SEQ ID NO:8419<br>AASSLQS | SEQ ID NO:16431<br>QQYHSYPWT | | |
| | | NA | SEQ ID NO:408<br>CGGGCAAGTCAGGGCATTAGAAATAATTTAGGC | SEQ ID NO:8420<br>GCTGCATCCAGTTTGCAAAGT | SEQ ID NO:16432<br>CTACAGCATAATAGTTACCCGCTCACT | | |
| iPS:392852 | 21-225_20H10 | AA | SEQ ID NO:409<br>RASQSISSYLN | SEQ ID NO:8421<br>AASSLQS | SEQ ID NO:16433<br>LQHNSYPLT | | |
| | | NA | SEQ ID NO:410<br>CGGGCAAGTCAGAGTATTAGTAGTTATTTAAAT | SEQ ID NO:8422<br>GCTGCATCCAGTTTGCAAAGT | SEQ ID NO:16434<br>CAACAGTTACAGAACCCCTTTTTCACT | | |
| iPS:392854 | 21-225_21A2 | AA | SEQ ID NO:411<br>RASQSISSYLN | SEQ ID NO:8423<br>AASSLQS | SEQ ID NO:16435<br>QQSYRTPFFT | | |
| | | NA | SEQ ID NO:412<br>CGGGCAAGTCAGGGCATTAGAAATGATTTAGGC | SEQ ID NO:8424<br>GCTGCATCCAGTTTGCAAAGT | SEQ ID NO:16436<br>CTACAGCATAATAGTTACCCCCTCACT | | |
| iPS:392856 | 21-225_21E5 | AA | SEQ ID NO:413<br>RASQGIRNDLG | SEQ ID NO:8425<br>ATSSLQS | SEQ ID NO:16437<br>LQHNSYPLT | | |
| | | NA | SEQ ID NO:414<br>CGGGCGAGTCAGGGACATTAGCAATTATTTAGGCC | SEQ ID NO:8426<br>GCTGCATCCAGTTTGCAAAGT | SEQ ID NO:16438<br>CAACAGTATAATAGTTTCCCGCTCACT | | |

FIGURE 49
(Continued)

| | | | | | |
|---|---|---|---|---|---|
| iPS:392858 | 21-225_22A2 | | SEQ ID NO:415 RASQDISNYLA | SEQ ID NO:8427 AASSLQS | SEQ ID NO:16439 QQYNSFPLT |
| | | AA | SEQ ID NO:416 | SEQ ID NO:8428 | SEQ ID NO:16440 |
| iPS:392860 | 21-225_22H4 | NA | CGGGCAAGTCAGGGCATTAG AAATGATTAGGC | GCTGCATCCAGTGCA AGT | CTACAGCATAATAGTTACC GCTCACT |
| | | | SEQ ID NO:417 RASQGIRNDLG | SEQ ID NO:8429 AASSVQS | SEQ ID NO:16441 LQHNSYPLT |
| | | AA | SEQ ID NO:418 | SEQ ID NO:8430 | SEQ ID NO:16442 |
| iPS:392864 | 21-225_22H8 | NA | AAGTCTAGTCAGAGCCTCCT GCATAGTGATGGAAAGACCT TTTTGTAT | GAAGTTCCAACCGGTTC TCT | ATGCAAAGTATACAGCTTCC GCTCTCA |
| | | | SEQ ID NO:419 KSSQSLLHSDGKTFLY | SEQ ID NO:8431 EVSNRFS | SEQ ID NO:16443 MQSIQLPLS |
| | | AA | SEQ ID NO:420 | SEQ ID NO:8432 | SEQ ID NO:16444 |
| iPS:392864 | 21-225_23B9 | NA | AGGGCCAGTCAGAATGTTTA CAGCAGCTACTTAGCC | GGTGCATCCAGCAGGGC CAGT | CAGCAGTATGGTAGCTCACC TCGGACG |
| | | | SEQ ID NO:421 RASQNVYSSYLA | SEQ ID NO:8433 GASSRAS | SEQ ID NO:16445 QQYGSSPRT |
| | | AA | SEQ ID NO:422 | SEQ ID NO:8434 | SEQ ID NO:16446 |
| iPS:392866 | 21-225_23H11 | NA | CGGGCAAGTCAGGGCATTAG AAATGATTAGAC | GCTGCATCCAGTTGCAA AGT | CTACAGCATAATCGTTACC GCTCACT |
| | | | SEQ ID NO:423 RASQGIRNDLD | SEQ ID NO:8435 AASSLQS | SEQ ID NO:16447 LQHNRYPLT |
| | | AA | SEQ ID NO:424 | SEQ ID NO:8436 | SEQ ID NO:16448 |
| iPS:392868 | 21-225_24D6 | NA | CAGGCGAGTCAGGACATTAA CAACTATTTAAAT | GATGCATCCGATTTGGA AACA | CAACAGTATGAAAATCTCCC GATCACC |
| | | | SEQ ID NO:425 QASQDINNYLN | SEQ ID NO:8437 DASDLET | SEQ ID NO:16449 QQYENLPIT |
| | | AA | SEQ ID NO:426 | SEQ ID NO:8438 | SEQ ID NO:16450 |

FIGURE 49
(Continued)

| | | | | | |
|---|---|---|---|---|---|
| iPS:392870 | 21-225_20G9 | NA | CGGGCAAGTCAGGGCATTAG AAATGATTAGGC SEQ ID NO:427 | GCTGCATCCAGTTTGCAA AGT SEQ ID NO:8439 | CTACAGCATAGTACTTACCC TCTCACT SEQ ID NO:16451 |
| | | AA | RASQGIRNDLG SEQ ID NO:428 | AASSLQS SEQ ID NO:8440 | LQHSTYPLT SEQ ID NO:16452 |
| iPS:392872 | 21-225_20B11 | NA | CGGGCAAGTCAGGGCATTGG AAATGATTAGGC SEQ ID NO:429 | GCTGCATCCAGTTTGCAT AGT SEQ ID NO:8441 | CTACAGCATTATAGTTACCC TCGGACG SEQ ID NO:16453 |
| | | AA | RASQGIGNDLG SEQ ID NO:430 | AASSLHS SEQ ID NO:8442 | LQHYSYPRT SEQ ID NO:16454 |
| iPS:392874 | 21-225_21D2 | NA | CGGGCAAGTCAGAGCATTAG CGACTATTTAAAT SEQ ID NO:431 | GATACATCCAGTTTGCA AAGT SEQ ID NO:8443 | CAACAGACTTACAATATTCT TCCGGAGCGCAGT SEQ ID NO:16455 |
| | | AA | RASQSISDYLN SEQ ID NO:432 | DTSSLQS SEQ ID NO:8444 | QQTYNILPERS SEQ ID NO:16456 |
| iPS:392876 | 21-225_21F7 | NA | CGGGCAAGTCAGGGACATTAG AAATGATTAGGC SEQ ID NO:433 | GCTGCATCCAGTTTGCAA AGT SEQ ID NO:8445 | CTACAGCATAATAATTACCC GTGGACG SEQ ID NO:16457 |
| | | AA | RASQDIRNDLG SEQ ID NO:434 | AASNFQS SEQ ID NO:8446 | LQHNNYPWT SEQ ID NO:16458 |
| iPS:392878 | 21-225_22C5 | NA | CGGGCAAGTCAGAGACATTAG CAGCTATTTAAAT SEQ ID NO:435 | GCTGCATCCGTTTGCAA CAT SEQ ID NO:8447 | CAACAGAGTTACAGAACCCC CTTATTCACT SEQ ID NO:16459 |
| | | AA | RASQNISSYLN SEQ ID NO:436 | AASVLQH SEQ ID NO:8448 | QQSYRTPLFT SEQ ID NO:16460 |
| iPS:392880 | 21-225_22F9 | NA | CGGGCAAGTCAGGGCATTAG AAATGATTAGGC SEQ ID NO:437 | GCTGCATCCAGTTTACAA AGT SEQ ID NO:8449 | CTACAGCATAATAGTTACCC GCTCACT SEQ ID NO:16461 |
| | | AA | RASQGIRNDLG SEQ ID NO:438 | AASSLQS SEQ ID NO:8450 | LQHNSYPLT SEQ ID NO:16462 |

FIGURE 49
(Continued)

| | | | | | |
|---|---|---|---|---|---|
| iPS:392882 | 21-225_23A3 | NA | CGGGCAAGTCAGGGCATTAG AAATGATTAGGC SEQ ID NO:439 | GCTGCATCCAGTGTGCA AAGT SEQ ID NO:8451 | CTACAGGCATAATAGTTACC GCTCACT SEQ ID NO:16463 |
| | | AA | RASQGIRNDLG SEQ ID NO:440 | AASSVQS SEQ ID NO:8452 | LQHNSYPLT SEQ ID NO:16464 |
| iPS:392884 | 21-225_23A10 | NA | CGGGCAAGTCAGGGCATTAG AAATGATTAGGC SEQ ID NO:441 | GCTGCATCCAGTTGCAA AGT SEQ ID NO:8453 | CTGCAACATTATAGTTACC TCGGACG SEQ ID NO:16465 |
| | | AA | RASQGIRNDLG SEQ ID NO:442 | AASSLQS SEQ ID NO:8454 | LQHYSYPRT SEQ ID NO:16466 |
| iPS:392886 | 21-225_23A12 | NA | AAGTCCAGCCAGAGTGTTTT ATACAGCTCCAACAATAACA ATTATTTAGCT SEQ ID NO:443 | TGGACATCTACCCGGGA ATCC SEQ ID NO:8455 | CAGCAGTATTATGATACTCC TCCGACG SEQ ID NO:16467 |
| | | AA | KSSQSVLYSSNNNNYLA SEQ ID NO:444 | WTSTRES SEQ ID NO:8456 | QQYYDTPPT SEQ ID NO:16468 |
| iPS:392888 | 21-225_25A2 | NA | AAGTCTAGTCAGAGCCTCCT ACATAGTGAAGGAAAGACC TATTTGTAT SEQ ID NO:445 | GAAATTTCCAACCGGTTC TCT SEQ ID NO:8457 | ATGCAAAGTACACAGTTTCC GCTCACT SEQ ID NO:16469 |
| | | AA | KSSQSLLHSEGKTYLY SEQ ID NO:446 | EISNRFS SEQ ID NO:8458 | MQSTQFPLT SEQ ID NO:16470 |
| iPS:392890 | 21-225_20H9 | NA | CGGGCGAGTCAGGGCATTAG CAATTATTTAGCC SEQ ID NO:447 | GCTGCATCCAGTTGCAA AGT SEQ ID NO:8459 | CAACAGTATAATAGTTACC ATTCACT SEQ ID NO:16471 |
| | | AA | RASQGISNYLA SEQ ID NO:448 | AASSLQS SEQ ID NO:8460 | QQYNSYPFT SEQ ID NO:16472 |
| iPS:392892 | 21-225_20C11 | NA | CGGGCGAGTCAGGACATTAG CAATTATTTAGCC SEQ ID NO:449 | GCTGCATCCAGTTGCAA AGT SEQ ID NO:8461 | CAACAGTATCATAGTTTCC ATTCACT SEQ ID NO:16473 |

FIGURE 49
(Continued)

| | | | | | | | |
|---|---|---|---|---|---|---|---|
| iPS:392894 | 21-225_21G2 | AA | RASQDISNYLA SEQ ID NO:450 | | AASSLQS SEQ ID NO:8462 | | QQYHSFPFT SEQ ID NO:16474 |
| | | NA | CGGGCAAGTCAGGGCATTAG AAATGATTAGGC SEQ ID NO:451 | | ACTTCATCCAGTTTGCAA AGT SEQ ID NO:8463 | | CTACAACATAATAGTTACCC GTGGACG SEQ ID NO:16475 |
| iPS:392896 | 21-225_21G7 | AA | RASQGIRNDLG SEQ ID NO:452 | | TSSSLQS SEQ ID NO:8464 | | LQHNSYPWT SEQ ID NO:16476 |
| | | NA | CGGGCAAGTCAGGGCGTTAG AAATGATTAGGC SEQ ID NO:453 | | GCTGCATCCAGTTTGCAA AGT SEQ ID NO:8465 | | CTACAGCATAGTAGTTACCC GCTCACT SEQ ID NO:16477 |
| iPS:392898 | 21-225_21H10 | AA | RASQGVRNDLG SEQ ID NO:454 | | AASSLQS SEQ ID NO:8466 | | LQHSSYPLT SEQ ID NO:16478 |
| | | NA | AGGGCCAGTCAGAGTTTTAG CAGCAGCTACTTAGCC SEQ ID NO:455 | | GGTGCATCCAGCAGGGC CACT SEQ ID NO:8467 | | CAGCAGTATGGTAGCTCACG CAGT SEQ ID NO:16479 |
| iPS:392900 | 21-225_22F2 | AA | RASQSFSSSYLA SEQ ID NO:456 | | GASSRAT SEQ ID NO:8468 | | QQYGSSRS SEQ ID NO:16480 |
| | | NA | CGGGCAAGTCAGGGCATTAG AAATGATTAGGC SEQ ID NO:457 | | GCTGCATCCAGTTACAA AGT SEQ ID NO:8469 | | CTACAGCATAATAGTTACCC GCTCACT SEQ ID NO:16481 |
| iPS:392902 | 21-225_22D5 | AA | RASQGIRNDLG SEQ ID NO:458 | | AASSLQS SEQ ID NO:8470 | | LQHNSYPLT SEQ ID NO:16482 |
| | | NA | CGGGCAAGTCAGAACATTTT TAGTTATTAAAT SEQ ID NO:459 | | GCTGCATCCAGTTTGCAA AGT SEQ ID NO:8471 | | CAACAGAGTTACAGTACCCC CTTATTCACT SEQ ID NO:16483 |
| iPS:392904 | 21-225_22G9 | AA | RASQNIFSYLN SEQ ID NO:460 | | AASSLQS SEQ ID NO:8472 | | QQSYSTPLFT SEQ ID NO:16484 |
| | | NA | CGGGCAAGTCAGGGCATTAG AAATGATTAGGC SEQ ID NO:461 | | GCTGCTTCCAGTTTGCAA AGT SEQ ID NO:8473 | | CTACAGCATGCCAGTTACCC GCTCACT SEQ ID NO:16485 |

FIGURE 49
(Continued)

| | | | | | | | |
|---|---|---|---|---|---|---|---|
| iPS:392908 | | AA | RASQGIRNDLG SEQ ID NO:462 | | AASSLQS SEQ ID NO:8474 | | LQHASYPLT SEQ ID NO:16486 |
| | 21-225_23F12 | NA | CGGGCAAGTCAGGGCATTAG AAATGATTAGGC SEQ ID NO:463 | | GTTGCATCCAGTTTGCAA AGT SEQ ID NO:8475 | | CTACAGCATAATAGTTACC GTGGACG SEQ ID NO:16487 |
| iPS:392912 | | AA | RASQGIRNDLG SEQ ID NO:464 | | VASSLQS SEQ ID NO:8476 | | LQHNSYPWT SEQ ID NO:16488 |
| | 21-225_25A9 | NA | CGGGCAAGTCAGGGCATTAG AAATGATTAGGC SEQ ID NO:465 | | GCTGCATCCAGTTTGCAA AGT SEQ ID NO:8477 | | CTACAGCATAATAGTTACC ATTCACT SEQ ID NO:16489 |
| iPS:392914 | | AA | RASQGIRNDLG SEQ ID NO:466 | | AASSLQS SEQ ID NO:8478 | | LQHNSYPFT SEQ ID NO:16490 |
| | 21-225_25D12 | NA | CGGACAAGTCAGGGCATTAG AAATGATTAGGC SEQ ID NO:467 | | GCTGCATCCAGTTTGCAA ACA AGT SEQ ID NO:8479 | | CTACAGCATTATAGTTTCCCT CGGACG SEQ ID NO:16491 |
| iPS:392916 | | AA | RTSQGIRNDLG SEQ ID NO:468 | | AASSLQS SEQ ID NO:8480 | | LQHYSFPRT SEQ ID NO:16492 |
| | 21-225_27C5 | NA | CGGGCGAGTCAGGGTATTAG CAGCTGGTTAGCC SEQ ID NO:469 | | GGTGCATCCAGTTTGCA AAGT SEQ ID NO:8481 | | CAACAGTATGACAGTTTCCC TCGGACG SEQ ID NO:16493 |
| iPS:392918 | | AA | RASQGISSWLA SEQ ID NO:470 | | GASSLQS SEQ ID NO:8482 | | QQYDSFPRT SEQ ID NO:16494 |
| | 21-225_28F5 | NA | CGGGCAAGTCAGGGCATTAG AAATGATTAGGC SEQ ID NO:471 | | ACTGCATCCAGTTTGCAA AGT SEQ ID NO:8483 | | CTACAGCATAATATACTTACC GTGGACG SEQ ID NO:16495 |
| iPS:392920 | | AA | RASQGIRNDLG SEQ ID NO:472 | | TASSLQS SEQ ID NO:8484 | | LQHNTYPWT SEQ ID NO:16496 |
| | 21-225_29G4 | NA | CGGGCAAGTCAGGGCATTAG AAATGATTAGGC SEQ ID NO:473 | | GCTGCATCCAGTTTGCAA AGT SEQ ID NO:8485 | | CTACAGCATAATAGTTACC GCTCACT SEQ ID NO:16497 |

FIGURE 49
(Continued)

| | | | | | | | |
|---|---|---|---|---|---|---|---|
| iPS:392922 | 21-225_30G4 | AA | RASQGIRNDLG<br>SEQ ID NO:474 | | AASSLQS<br>SEQ ID NO:8486 | | LQHNSYPLT<br>SEQ ID NO:16498 |
| | | NA | CGGGCAACTCAGAACATTTT<br>CAGCTATTTAAAT<br>SEQ ID NO:475 | | ACTGCATCCAGTTTGCAA<br>GGT<br>SEQ ID NO:8487 | | CAACTCAGCTACAGTCCCC<br>GTACACT<br>SEQ ID NO:16499 |
| iPS:392924 | 21-225_32H2 | AA | RATQNIFSYLN<br>SEQ ID NO:476 | | TASSLQG<br>SEQ ID NO:8488 | | QLSYSPPYT<br>SEQ ID NO:16500 |
| | | NA | AGGTCTAGTCAGAGCCTCCT<br>CCATAGTGATGGAAGGACCT<br>ATTTGTAT<br>SEQ ID NO:477 | | GAACTTTCCAACCGGTTC<br>TCT<br>SEQ ID NO:8489 | | TTGCAAAGTATACAATATCC<br>CATCACC<br>SEQ ID NO:16501 |
| iPS:392928 | 21-225_25A4 | AA | RSSQSLLHSDGRTYLY<br>SEQ ID NO:478 | | ELSNRFS<br>SEQ ID NO:8490 | | LQSIQYPIT<br>SEQ ID NO:16502 |
| | | NA | AAGTCCAGCCAGAGTGTTTT<br>ATACAGCTCCCACAATAACA<br>ACTACTTAGCT<br>SEQ ID NO:479 | | TGGGCATCTACCCGGGA<br>ATCC<br>SEQ ID NO:8491 | | CAGCAGTATTATAGTACTCC<br>TCCGACG<br>SEQ ID NO:16503 |
| iPS:392930 | 21-225_25H9 | AA | KSSQSVLYSSHNNNYLA<br>SEQ ID NO:480 | | WASTRES<br>SEQ ID NO:8492 | | QQYYSTPPT<br>SEQ ID NO:16504 |
| | | NA | AAGTCTAGTCAGAGCCTCCT<br>GCATGGTGATGGAAAGACCT<br>ATTTGTTT<br>SEQ ID NO:481 | | GAAGTTTCCAATCGGTTC<br>TCT<br>SEQ ID NO:8493 | | ATGCAAAGTATACAGCTTCC<br>GTGGACG<br>SEQ ID NO:16505 |
| iPS:392934 | 21-225_27D5 | AA | KSSQSLLHGDGKTYLF<br>SEQ ID NO:482 | | EVSNRFS<br>SEQ ID NO:8494 | | MQSIQLPWT<br>SEQ ID NO:16506 |
| | | NA | CGGGCAAGTCAGGGCATTAG<br>AAATGATTTAGGC<br>SEQ ID NO:483 | | GCTGCATCCAGTTTGCAA<br>AGT<br>SEQ ID NO:8495 | | CTACAGCATAATAGTTACCC<br>ATTCACT<br>SEQ ID NO:16507 |
| | | AA | RASQGIRNDLG<br>SEQ ID NO:484 | | AASSLQS<br>SEQ ID NO:8496 | | LQHNSYPFT<br>SEQ ID NO:16508 |

FIGURE 49
(Continued)

| | | | | | |
|---|---|---|---|---|---|
| iPS:392936 | 21-225_28B6 | NA | CGGTCTAGTCAAAGCCTCGTATATAGTGATGGAGACACCTACTTGAAT SEQ ID NO:485 | AAGGTTTCTAACTGGGACTCT SEQ ID NO:8497 | ATGCATTGTACACACTGGCTCCTT SEQ ID NO:16509 |
| | | AA | RSSQSLVYSDGDTYLN SEQ ID NO:486 | KVSNWDS SEQ ID NO:8498 | MHCTHWLL SEQ ID NO:16510 |
| iPS:392938 | 21-225_29H4 | NA | AAGTCTAGTCAGAGCCTCCTGCATAGTGATGGAAAGACCTATTTGTAT SEQ ID NO:487 | GAGGTTTCCCACCGGTTCTCT SEQ ID NO:8499 | ATGCAAAGTATACAGCATCCGTTCACT SEQ ID NO:16511 |
| | | AA | KSSQSLLHSDGKTYLY SEQ ID NO:488 | EVSHRFS SEQ ID NO:8500 | MQSIQHPFT SEQ ID NO:16512 |
| iPS:392940 | 21-225_29D9 | NA | CGGGCAAGTCAGGGCATTAGAAATGATTTAGGC SEQ ID NO:489 | GCTGCATCCAGTTTGCAAAGT SEQ ID NO:8501 | CTACAGCATAATACTTACCCATTCACT SEQ ID NO:16513 |
| | | AA | RASQGIRNDLG SEQ ID NO:490 | AASSLQS SEQ ID NO:8502 | LQHNTYPFT SEQ ID NO:16514 |
| iPS:392942 | 21-225_30E9 | NA | CGGGCAAGTCAGGACATTAGAGATGATTTAGGC SEQ ID NO:491 | GGTGCATTCAGCTTGCAAAGT SEQ ID NO:8503 | CTACAGCATACTAGTTACCTCCTACT SEQ ID NO:16515 |
| | | AA | RASQDIRDDLG SEQ ID NO:492 | GAFSLQS SEQ ID NO:8504 | LQHTSYPPT SEQ ID NO:16516 |
| iPS:392944 | 21-225_31H5 | NA | CGGGCAAGTCAGGACATTAGAAGTGATTTAGGC SEQ ID NO:493 | GCTGCATCCAGTTTGCAAAGT SEQ ID NO:8505 | ATACAACATATTATTTACCCTCCTACT SEQ ID NO:16517 |
| | | AA | RASQDIRSDLG SEQ ID NO:494 | AASSLQS SEQ ID NO:8506 | IQHIIYPPT SEQ ID NO:16518 |
| iPS:392948 | 21-225_25G5 | NA | CGGGCAAGTCAGGACATTAGAAATGATTTAGGC SEQ ID NO:495 | GCTGCATCCAGTTTGCAAAGT SEQ ID NO:8507 | CTACAGCATAATAGTTACCCTTCACT SEQ ID NO:16519 |

FIGURE 49 (Continued)

| | | | | | | |
|---|---|---|---|---|---|---|
| iPS:392950 | 21-225_25C10 | AA | RASQDIRNDLG SEQ ID NO:496 | AASSLQS SEQ ID NO:8508 | LQHNSYPFT SEQ ID NO:16520 | |
| | | NA | CGGGCGAGTCAGGGCATTAG CAATTATTAGCC SEQ ID NO:497 | GCTGCATCCAGTTTGCAA AGT SEQ ID NO:8509 | CAACAGTATCATAGTTACCC ATTCACT SEQ ID NO:16521 | |
| iPS:392952 | 21-225_26G1 | AA | RASQGISNYLA SEQ ID NO:498 | AASSLQS SEQ ID NO:8510 | QQYHSYPFT SEQ ID NO:16522 | |
| | | NA | CGGGCGAGTCAGGACATTAG CAATTATTAGCC SEQ ID NO:499 | GCTGCATCCAGTTTGCGA AGT SEQ ID NO:8511 | CAACAGTATCATAGTTACCC ATTCACT SEQ ID NO:16523 | |
| iPS:392954 | 21-225_26A10 | AA | RASQDISNYLA SEQ ID NO:500 | AASSIRS SEQ ID NO:8512 | QQYHSYPFT SEQ ID NO:16524 | |
| | | NA | CGGGCAAGTCAGAGCATTAG CAGCTATTTAAAT SEQ ID NO:501 | GCTGCATCCAGTTGCA AAGT SEQ ID NO:8513 | CAACAGAGTTACAGTACCCC TACGTGGACG SEQ ID NO:16525 | |
| iPS:392956 | 21-225_27A11 | AA | RASQSISSYLN SEQ ID NO:502 | AASSLQS SEQ ID NO:8514 | QQSYSTPTWT SEQ ID NO:16526 | |
| | | NA | CGGGCGAGTCAGGGTATTAG TAGTTGGTTAGCC SEQ ID NO:503 | GGTGCATCCAGTTGCA AAGT SEQ ID NO:8515 | CAACAGTCTGACAGTTTCCC TCGGACG SEQ ID NO:16527 | |
| iPS:392958 | 21-225_28C7 | AA | RASQGISSWLA SEQ ID NO:504 | GASSLQS SEQ ID NO:8516 | QQSDSFPRT SEQ ID NO:16528 | |
| | | NA | CGGGCGAGTCAGGGCATTAG AAATGATTTAGGC SEQ ID NO:505 | ATTGCATCCAGTTGCAA AGT SEQ ID NO:8517 | CTACAGCATAATACTTACCC GTGGACG SEQ ID NO:16529 | |
| iPS:392960 | 21-225_29E6 | AA | RASQGIRNDLG SEQ ID NO:506 | IASSLQS SEQ ID NO:8518 | LQHNTYPWT SEQ ID NO:16530 | |
| | | NA | AAGTCCAGCCAGAGTGTTTT ATACAGCTCCACAATAACT ACTACTTAACT | TGGGCATCTTCCCGGGA ATCC | CAGCAGTATTATAGTACTCC TCCGACG | |

FIGURE 49
(Continued)

| | | | | | | |
|---|---|---|---|---|---|---|
| iPS:392962 | 21-225_29E6 | AA | SEQ ID NO:507 KSSQSVLYSSHNNYYLT | SEQ ID NO:8519 WASSRES | SEQ ID NO:16531 QQYYSTPPT | |
| | | NA | SEQ ID NO:508 CGGGCGAGTCAGGGCATTAG CAATTATTAGCC | SEQ ID NO:8520 GCTGCATCCAGTTGCAA ACT | SEQ ID NO:16532 CAACAGTATAATAGTTACCC ATTCACT | |
| iPS:392964 | 21-225_30A1 | AA | SEQ ID NO:509 RASQGISNYLA | SEQ ID NO:8521 AASSLQT | SEQ ID NO:16533 QQYNSYPFT | |
| | | NA | SEQ ID NO:510 CGGGCAAGTCAGGACATTAG AAGTGATTTAGGC | SEQ ID NO:8522 GCTGTATCCAGTTGCAA AGT | SEQ ID NO:16534 CTACAGCATACTATTACCC TCCTACT | |
| iPS:392966 | 21-225_31A8 | AA | SEQ ID NO:511 RASQDIRSDLG | SEQ ID NO:8523 AVSSLQS | SEQ ID NO:16535 LQHTIYPPT | |
| | | NA | SEQ ID NO:512 CGGGCGAGTCAGGCAGGCATTAG CAATTATTAGCC | SEQ ID NO:8524 GATACATCCAGTTGCA AAGT | SEQ ID NO:16536 CAACAGTATCATAGTTACCC GCTCACT | |
| iPS:392968 | 21-225_32G3 | AA | SEQ ID NO:513 RASQAISNYLA | SEQ ID NO:8525 DTSSLQS | SEQ ID NO:16537 QQYHSYPLT | |
| | | NA | SEQ ID NO:514 CGGGCAAGTCAGGGCATTAG AAATGATTTAGGC | SEQ ID NO:8526 CGTGCATCCAGTTGCAA AGT | SEQ ID NO:16538 CTACAGCATAATAGTTACCC ATTCACT | |
| iPS:392970 | 21-225_25B6 | AA | SEQ ID NO:515 RASQGIRNDLG | SEQ ID NO:8527 RASSLQS | SEQ ID NO:16539 LQHNSYPFT | |
| | | NA | SEQ ID NO:516 CGGGCAAGTCAGGGCATTAG AAGTGATTTAGGC | SEQ ID NO:8528 ACTGCATCCAGTTGCAA AGT | SEQ ID NO:16540 CTACAGCATAATCGTTACCC GTGGACG | |
| iPS:392972 | 21-225_26A2 | AA | SEQ ID NO:517 RASQGIRSDLG | SEQ ID NO:8529 TASSLQS | SEQ ID NO:16541 LQHNRYPWT | |
| iPS:392974 | | NA | SEQ ID NO:518 CGGGCAAGTCAGGGCCATTAG AAATGATTTAGGC | SEQ ID NO:8530 GCTGCATCCAGTTGCAA AGT | SEQ ID NO:16542 CTACAGCATTATAATTACCC TCGCAGT | |

FIGURE 49
(Continued)

| | | | | | | |
|---|---|---|---|---|---|---|
| iPS:392976 | 21-225_26A11 | AA | SEQ ID NO:519 RASQAIRNDLG | SEQ ID NO:8531 AASSLQS | SEQ ID NO:16543 LQHYNYPRS | |
| iPS:392978 | 21-225_27H12 | NA | SEQ ID NO:520 CGGGCGAGTCAGGGCATTAG CAATTATTAGCC | SEQ ID NO:8532 GGTGCATCCAGTTGCA AAGT | SEQ ID NO:16544 CAACAGTATTATAGTTACCC ATTCACT | |
| | | AA | SEQ ID NO:521 RASQGISNYLA | SEQ ID NO:8533 GASSLQS | SEQ ID NO:16545 QQYYSYPFT | |
| iPS:392980 | 21-225_28B8 | NA | SEQ ID NO:522 CGGGCAAGTCAGGGCATTAG AAATGATTTAGGC | SEQ ID NO:8534 GCTGCATCCAGTTGCAA AGT | SEQ ID NO:16546 CTACAGCATAATAGTTACCC ATTCACT | |
| | | AA | SEQ ID NO:523 RASQGIRNDLG | SEQ ID NO:8535 AASSLQS | SEQ ID NO:16547 LQHNSYPFT | |
| iPS:392982 | 21-225_29H6 | NA | SEQ ID NO:524 CGGGCAAGTCAGGGCATTAG AAATGATTTAGGC | SEQ ID NO:8536 GCTGCATCCAGTTGCAA AGT | SEQ ID NO:16548 CTACAGCATAATAGTTACCC GCTCACT | |
| | | AA | SEQ ID NO:525 RASQGIRNDLG | SEQ ID NO:8537 AASSLQS | SEQ ID NO:16549 LQHNSYPLT | |
| iPS:392984 | 21-225_30D1 | NA | SEQ ID NO:526 CGGGCAAGTCAGGACATTAG AAGTGATTTAGGC | SEQ ID NO:8538 GCTGCATCCAGTTGCAA AGT | SEQ ID NO:16550 CTACAGCATACTATTACCC TCCTACT | |
| | | AA | SEQ ID NO:527 RASQDIRSDLG | SEQ ID NO:8539 AASSLQS | SEQ ID NO:16551 LQHTIYPPT | |
| iPS:392986 | 21-225_30E11 | NA | SEQ ID NO:528 CGGGCAAGTCAGAGCATTAG CAACTATTTAAAT | SEQ ID NO:8540 GCTGCATCCAGTTGCAA AGT | SEQ ID NO:16552 CAACAGTATTACAGTACCCC ATTCACT | |
| | | AA | SEQ ID NO:529 RASQSISNYLN | SEQ ID NO:8541 AASSLQS | SEQ ID NO:16553 QQSYSTPFT | |
| | | NA | SEQ ID NO:530 CGGGCAAGTCAGGACATTAG AAGTGATTTAGGC | SEQ ID NO:8542 GGTGCATCCAGTTGCA AAGT | SEQ ID NO:16554 CTACAGCATATTATTACCCT CCTACT | |

FIGURE 49
(Continued)

| | | | | | | | |
|---|---|---|---|---|---|---|---|
| iPS:392988 | 21-225_31B8 | AA | SEQ ID NO:531 RASQDIRSDLG | SEQ ID NO:8543 GASSLQS | SEQ ID NO:16555 LQHIYPPT | | |
| iPS:392990 | 21-225_25E6 | NA | SEQ ID NO:532 CGGGCAAGTCAGGGCATTAGAAATGATTTAGGC | SEQ ID NO:8544 GCTGCATCCAGTTTGCAAAGT | SEQ ID NO:16556 CTACAGCATAATAGTTACCCGCTCACT | | |
| | | AA | SEQ ID NO:533 RASQGIRNDLG | SEQ ID NO:8545 AASSLQS | SEQ ID NO:16557 LQHNSYPLT | | |
| iPS:392990 | 21-225_25H10 | NA | SEQ ID NO:534 CGGGCAAGTCAGGGCATTAGAAATGATTTAGGC | SEQ ID NO:8546 GCTGCATCCAGTTTGCAAAGT | SEQ ID NO:16558 CTACAGCATAATAGTTACCCGCTCACT | | |
| | | AA | SEQ ID NO:535 RASRGIRNDLG | SEQ ID NO:8547 AAFSLQS | SEQ ID NO:16559 LQHNSYPLT | | |
| iPS:392992 | 21-225_26C4 | NA | SEQ ID NO:536 AAGTCCAGCCAGAGTGTTTTATACCGCTCCAACAATTACAACTACTTAGCT | SEQ ID NO:8548 TGGGCATCTACCCGGGAATCC | SEQ ID NO:16560 CAGCAATATTATAGTACTCCTCCGACG | | |
| | | AA | SEQ ID NO:537 KSSQSVLYRSNNYNYLA | SEQ ID NO:8549 WASTRES | SEQ ID NO:16561 QQYYSTPPT | | |
| iPS:392994 | 21-225_26G11 | NA | SEQ ID NO:538 AAGTCTAGTCAGACCCTCCTGCATGGTGAAGGAAAGACCTATTTGTAT | SEQ ID NO:8550 GAAGTTTCCAACCGGTTCTCT | SEQ ID NO:16562 ATGCAAAGTATAAAGCTTCCGCTCACT | | |
| | | AA | SEQ ID NO:539 KSSQTLLHGEGKTYLY | SEQ ID NO:8551 EVSNRFS | SEQ ID NO:16563 MQSIKLPLT | | |
| iPS:392996 | 21-225_28B1 | NA | SEQ ID NO:540 CGGGCGAGTCAGGCTATCAATGACTGGTTAGCC | SEQ ID NO:8552 GCTGCATCCAGTTTCCAAAGT | SEQ ID NO:16564 CAACAGGCTAGCAGTTTCCATTCACT | | |
| | | AA | SEQ ID NO:541 RASQAINDWLA | SEQ ID NO:8553 AASSFQS | SEQ ID NO:16565 QQASSFPFT | | |
| | | | SEQ ID NO:542 | SEQ ID NO:8554 | SEQ ID NO:16566 | | |

FIGURE 49
(Continued)

| | | | | | |
|---|---|---|---|---|---|
| iPS:392998 | 21-225_28A9 | NA | CGGGCAAGTCAGGGCATTAG AAATGATTAGGC SEQ ID NO:543 | GCTGCTGCTTCTAGTTTGCAA AAT SEQ ID NO:8555 | CTACAGGACATAATCGTTACCC ATTCACT SEQ ID NO:16567 |
| | | AA | RASQGIRNDLG SEQ ID NO:544 | AASSLQN SEQ ID NO:8556 | LQHNRYPFT SEQ ID NO:16568 |
| iPS:393000 | 21-225_29D7 | NA | CGGGCAAGTCAGGGCATTAG AAATGATTAGGC SEQ ID NO:545 | GCTGCATCCAGTTTACAA AGT SEQ ID NO:8557 | CTACAGCATAATAGTTACCC ATTCACT SEQ ID NO:16569 |
| | | AA | RASQGIRNDLG SEQ ID NO:546 | AASSLQS SEQ ID NO:8558 | LQHNSYPFT SEQ ID NO:16570 |
| iPS:393002 | 21-225_30G1 | NA | CGGCAAGTCAGAACATTTA CAGTCTATTAAAT SEQ ID NO:547 | GCTGCATCCAGTTTGCAT AGT SEQ ID NO:8559 | CAACAGAGTTACAGTACTCC GCTCACT SEQ ID NO:16571 |
| | | AA | RASQNIYSYLN SEQ ID NO:548 | AASSLHS SEQ ID NO:8560 | QQSYSTPLT SEQ ID NO:16572 |
| iPS:393004 | 21-225_30G11 | NA | CGGGCAAGTCAGGACATTAG AAGTGATTAGGC SEQ ID NO:549 | GCTGCATCCAGTTTGCAA AGT SEQ ID NO:8561 | CTACAGCATACTATTACCC TCCTACT SEQ ID NO:16573 |
| | | AA | RASQDIRSDLG SEQ ID NO:550 | AASSLQS SEQ ID NO:8562 | LQHTYPPT SEQ ID NO:16574 |
| iPS:393006 | 21-225_31G9 | NA | CGGGCAAGTCAGGGCATTAG AAATGATTAGGC SEQ ID NO:551 | CCTGCATCCAGTTTGCAA AGT SEQ ID NO:8563 | CTACAGGATAATAGTTACCC TTTCACT SEQ ID NO:16575 |
| | | AA | RASQGIRNDLG SEQ ID NO:552 | PASSLQS SEQ ID NO:8564 | LQDNSYPFT SEQ ID NO:16576 |
| iPS:393010 | 21-225_25E11 | NA | CGGGCGAGTCAGGGTATTAG CAACTGGTTAGCC SEQ ID NO:553 | ACTGCATCCAGTTTGCAA GGT SEQ ID NO:8565 | CAACAGGCTAACAGTTTCCC AATCACT SEQ ID NO:16577 |
| | | AA | RASQGISNWLA SEQ ID NO:554 | TASSLQG SEQ ID NO:8566 | QQANSFPIT SEQ ID NO:16578 |

FIGURE 49
(Continued)

| | | | | | | | |
|---|---|---|---|---|---|---|---|
| iPS:393012 | 21-225_26G7 | NA | AAGTCTAGTCAGAGCCTCCT GCATAGTGAGGGAAAGACC TATTTGTAT SEQ ID NO:555 | | GAAGTTCCCACCGGCTC TCT SEQ ID NO:8567 | | ATGCAAAGTATACAGTTCC GCTCACT SEQ ID NO:16579 |
| | | AA | KSSQSLLHSEGKTYLY SEQ ID NO:556 | | EVSHRLS SEQ ID NO:8568 | | MQSIQLPLT SEQ ID NO:16580 |
| iPS:393014 | 21-225_26D12 | NA | CGGGCGAGTCAGGGTATTAG TAGTTGGTTAGCC SEQ ID NO:557 | | GGTGCATCCAGTTGCA AAGT SEQ ID NO:8569 | | CAACAGTCTGACAGTTTCC TCGGACG SEQ ID NO:16581 |
| | | AA | RASQGISSWLA SEQ ID NO:558 | | GASSLQS SEQ ID NO:8570 | | QQSDSFPRT SEQ ID NO:16582 |
| iPS:393016 | 21-225_28F11 | NA | CGGGCGAGTCAGGGTATTAG CAACTGGTTAGCC SEQ ID NO:559 | | GCTGCATCCAATTGCAA AGT SEQ ID NO:8571 | | CAACAGGCTAACAGTCTCCC ATTCACT SEQ ID NO:16583 |
| | | AA | RASQGISNWLA SEQ ID NO:560 | | AASNLQS SEQ ID NO:8572 | | QQANSLPFT SEQ ID NO:16584 |
| iPS:393018 | 21-225_29B8 | NA | CGGGCAAGTCAGGGCATTAG AAATGATTTAGGC SEQ ID NO:561 | | GCTGCATCCAGTTGCAA AGT SEQ ID NO:8573 | | CTACAGCATAATAGTTACCC GCTCACT SEQ ID NO:16585 |
| | | AA | RASQGIRNDLG SEQ ID NO:562 | | AASSLQS SEQ ID NO:8574 | | LQHNSYPLT SEQ ID NO:16586 |
| iPS:393020 | 21-225_30E2 | NA | CAGGCGAGTCAGTACATTAG CAACTATTTAAAT SEQ ID NO:563 | | GATGGATCCAGTTTGGA AACA SEQ ID NO:8575 | | CAACAGTATGATAATCTCCC GATCACC SEQ ID NO:16587 |
| | | AA | QASQYISNYLN SEQ ID NO:564 | | DGSSLET SEQ ID NO:8576 | | QQYDNLPIT SEQ ID NO:16588 |
| iPS:393022 | 21-225_30H11 | NA | CGGGCAAGTCAGGGCATTAG AAATGATTTAGGC SEQ ID NO:565 | | CCTGCATCCAGTTGCAA AGT SEQ ID NO:8577 | | CTACAGGATAATAGTCATCC ATTCACT SEQ ID NO:16589 |
| | | AA | RASQGIRNDLG | | PASSLQS | | LQDNSHPFT |

FIGURE 49
(Continued)

| | | | | | | |
|---|---|---|---|---|---|---|
| iPS:393024 | 21-225_31H9 | NA | SEQ ID NO:566<br>CGGGCGAGTCAGGGTATTAC<br>CAGCTGGTTAACT | SEQ ID NO:8578<br>GATACATCCAGTTTGCA<br>AAGT | SEQ ID NO:16590<br>CAACAGGGTAACAGTTTCCC<br>ATTCACT |
| | | AA | SEQ ID NO:567<br>RASQGITSWLT | SEQ ID NO:8579<br>DTSSLQS | SEQ ID NO:16591<br>QQGNSFPFT |
| iPS:393026 | 21-225_32B6 | NA | SEQ ID NO:568<br>CGGGCAAGTCAGGGCATTAG<br>AAATGATTTAGGC | SEQ ID NO:8580<br>ATTGCATCCAGTTTGCAA<br>AGT | SEQ ID NO:16592<br>CTACAGCATAATAGTTACCC<br>GTGGACG |
| | | AA | SEQ ID NO:569<br>RASQGIRNDLG | SEQ ID NO:8581<br>IASSLQS | SEQ ID NO:16593<br>LQHNSYPWT |
| iPS:393028 | 21-225_25D7 | NA | SEQ ID NO:570<br>CGGGCGAGTCAGGATATTTT<br>CGACTGGTTAGCC | SEQ ID NO:8582<br>GCTGCATCCAGTTTGCAA<br>AGT | SEQ ID NO:16594<br>CAACAGGCTTACAGTTTCCC<br>GTGGACG |
| | | AA | SEQ ID NO:571<br>RASQDIFDWLA | SEQ ID NO:8583<br>AASSLQS | SEQ ID NO:16595<br>QQAYSFPWT |
| iPS:393030 | 21-225_25H11 | NA | SEQ ID NO:572<br>CGGGCAAGTCAGGGCATTAG<br>AACTGATTTAGGC | SEQ ID NO:8584<br>GCTGCATCCAGTTTACAA<br>AGT | SEQ ID NO:16596<br>CTACAGCATAATAGTTACCC<br>GCTCACT |
| | | AA | SEQ ID NO:573<br>RASQGIRTDLG | SEQ ID NO:8585<br>AASSLQS | SEQ ID NO:16597<br>LQHNSYPLT |
| iPS:393032 | 21-225_26F8 | NA | SEQ ID NO:574<br>AAGTCTAGTCAGAGCCTCCT<br>GCATGGTGATGGAAAGACCT<br>ATTTGTAT | SEQ ID NO:8586<br>GAAGTTTCCAACCGGTTC<br>TCT | SEQ ID NO:16598<br>ATGCAAAGTATACAGCTTCC<br>GTGGACG |
| | | AA | SEQ ID NO:575<br>KSSQSLLHGDGKTYLY | SEQ ID NO:8587<br>EVSNRFS | SEQ ID NO:16599<br>MQSIQLPWT |
| iPS:393034 | 21-225_27F2 | NA | SEQ ID NO:576<br>CGGGCAAGTCAGGGCATTAG<br>AAATGATTTAGGC | SEQ ID NO:8588<br>GTTGCATCCAGTTTGCAA<br>AGT | SEQ ID NO:16600<br>CTACAGCATAATAGTTACCC<br>GCTCACT |
| | | | SEQ ID NO:577 | SEQ ID NO:8589 | SEQ ID NO:16601 |

FIGURE 49
(Continued)

| | | | | | | |
|---|---|---|---|---|---|---|
| iPS:393036 | 21-225_28G3 | AA | RASQGIRNDLG<br>SEQ ID NO:578 | | VASSLQS<br>SEQ ID NO:8590 | | LQHNSYPLT<br>SEQ ID NO:16602 |
| | | NA | AAGTCTAGTCAGAGCCTCCT<br>ACATGGTGATGGAAAGACCT<br>ATTTGTAT<br>SEQ ID NO:579 | GAAGTTTCCAACCGGTTC<br>TCT<br>SEQ ID NO:8591 | ATGCAAGTATACAGATTCC<br>GTGGACG<br>SEQ ID NO:16603 |
| iPS:393038 | 21-225_29D8 | AA | KSSQSLLHGDGKTYLY<br>SEQ ID NO:580 | EVSNRFS<br>SEQ ID NO:8592 | MQSIQIPWT<br>SEQ ID NO:16604 |
| | | NA | CGGGCAAGTCAGGGCATTAG<br>AAATGATTTAGGC<br>SEQ ID NO:581 | ACTGCATCAGTTGCAA<br>AGT<br>SEQ ID NO:8593 | CTACAGCATAATAGTTACCC<br>ATTCACT<br>SEQ ID NO:16605 |
| iPS:393040 | 21-225_30E3 | AA | RASQGIRNDLG<br>SEQ ID NO:582 | TASSLQS<br>SEQ ID NO:8594 | LQHNSYPFT<br>SEQ ID NO:16606 |
| | | NA | CGGGCAAGTCAGGACATTAG<br>AGATGATTTAGGC<br>SEQ ID NO:583 | GCTGCATCAGTTGCA<br>AGT<br>SEQ ID NO:8595 | CTACAGCATACTAGTTACCC<br>TCCTACT<br>SEQ ID NO:16607 |
| iPS:393042 | 21-225_31F1 | AA | RASQDIRDDLG<br>SEQ ID NO:584 | AAFSLQS<br>SEQ ID NO:8596 | LQHTSYPPT<br>SEQ ID NO:16608 |
| | | NA | CGGGCAAGTCAGAGGATTA<br>GCAGCTATTTAAAT<br>SEQ ID NO:585 | GCTGCATCCAGTTCGCA<br>AAGT<br>SEQ ID NO:8597 | CAACAGAGTTACATTACCC<br>GCTCACT<br>SEQ ID NO:16609 |
| iPS:393044 | 21-225_25B8 | AA | RASQRISSYLN<br>SEQ ID NO:586 | AASSSQS<br>SEQ ID NO:8598 | QQSYITPLT<br>SEQ ID NO:16610 |
| | | NA | AGGGCCAGTCAGAGTGTTAG<br>AAGTAATTAGCC<br>SEQ ID NO:587 | GGTGCATCCACCAGGGC<br>CACT<br>SEQ ID NO:8599 | CAGCAGTATAATAATTGGCC<br>TCCGTGGCCG<br>SEQ ID NO:16611 |
| iPS:393046 | | AA | RASQSVRSNLA<br>SEQ ID NO:588 | GASTRAT<br>SEQ ID NO:8600 | QQYNNWPPWP<br>SEQ ID NO:16612 |
| | | NA | CGGGCAAGTCAGGCCATTAG<br>AGATGATTTAGGC | GCTGCATCCAGTTGCAA<br>AGT | CTACAGCATTATAATTACCC<br>TCGCAGT |

FIGURE 49
(Continued)

| | | | | | | |
|---|---|---|---|---|---|---|
| iPS:393048 | 21-225_25A12 | AA | SEQ ID NO:589<br>RASQAIRDDLG<br>SEQ ID NO:590 | SEQ ID NO:8601<br>AASSLQS<br>SEQ ID NO:8602 | SEQ ID NO:16613<br>LQHYNYPRS<br>SEQ ID NO:16614 | |
| iPS:393050 | 21-225_27C3 | NA | CGGGCAAGTCAGGGCATTAG<br>AAATGATTTAGGC<br>SEQ ID NO:591 | GCTGCATCCAGTTGCAA<br>AGT<br>SEQ ID NO:8603 | CTACAGCATAATCGTTACCC<br>GCTCACT<br>SEQ ID NO:16615 | |
| | | AA | RASQGIRNDLG<br>SEQ ID NO:592 | AASSLQS<br>SEQ ID NO:8604 | LQHNRYPLT<br>SEQ ID NO:16616 | |
| iPS:393050 | 21-225_28C5 | NA | AGGGCCAGTCAGAGAGTGTTAG<br>CAGCAACTTAGCC<br>SEQ ID NO:593 | GGTGCATCCACCAGGGC<br>CACT<br>SEQ ID NO:8605 | CAGCAGTATAATAATTGGCC<br>TCCGTGGCCG<br>SEQ ID NO:16617 | |
| | | AA | RASQSVSSNLA<br>SEQ ID NO:594 | GASTRAT<br>SEQ ID NO:8606 | QQYNNWPPWP<br>SEQ ID NO:16618 | |
| iPS:393054 | 21-225_29G8 | NA | CGGGCAAGTCAGGGCATTAG<br>AAATGATTTAGGC<br>SEQ ID NO:595 | GCTGCATCCAGTTGCAA<br>AGT<br>SEQ ID NO:8607 | CTACAGCATAATAGTTACCC<br>GCTCACT<br>SEQ ID NO:16619 | |
| | | AA | RASQGIRNDLG<br>SEQ ID NO:596 | AASSLQS<br>SEQ ID NO:8608 | LQHNSYPLT<br>SEQ ID NO:16620 | |
| iPS:393056 | 21-225_30F3 | NA | CGGGCAAGTCAGGGCATTAG<br>AAATGATTTAGGC<br>SEQ ID NO:597 | ACTGCATCCAGTTACAA<br>AGT<br>SEQ ID NO:8609 | CTACAGCATAATAGTTACCC<br>GTTCACT<br>SEQ ID NO:16621 | |
| | | AA | RASQGIRNDLG<br>SEQ ID NO:598 | TASSLQS<br>SEQ ID NO:8610 | LQHNSYPFT<br>SEQ ID NO:16622 | |
| iPS:393058 | 21-225_31H3 | NA | CGGGCAAGTCAGGACATTAG<br>AGATGATTTAGGC<br>SEQ ID NO:599 | GCTGCATCCAGTTGCAA<br>AGT<br>SEQ ID NO:8611 | CTACAGCATACTAGTTACCC<br>TCCTACT<br>SEQ ID NO:16623 | |
| | | AA | RASQDIRDDLG<br>SEQ ID NO:600 | AAFSLQS<br>SEQ ID NO:8612 | LQHTSYPPT<br>SEQ ID NO:16624 | |
| iPS:393060 | | NA | CGGGCAAGTCAGGACATTAG<br>AAGTGATTTAGGC | GCTGCATCCAGTTGCAA<br>AGT | CTGCAGCATACTATTACCC<br>TCCTACT | |

FIGURE 49
(Continued)

| | | | | | | |
|---|---|---|---|---|---|---|
| iPS:393062 | 21-225_32G12 | AA | SEQ ID NO:601<br>RASQDIRSDLG | SEQ ID NO:8613<br>AASSLQS | SEQ ID NO:16625<br>LQHTIYPPT |
| iPS:393064 | 21-225_33H3 | NA | SEQ ID NO:602<br>CAGGGCGAGTCAGGACATTTC<br>CAACTTTTTAAAT | SEQ ID NO:8614<br>GATGCATCCAATTGGTA<br>ACA | SEQ ID NO:16626<br>CAACAGTATGATAATCTCCC<br>GATCACC |
| | | AA | SEQ ID NO:603<br>QASQDISNFLN | SEQ ID NO:8615<br>DASNLVT | SEQ ID NO:16627<br>QQYDNLPIT |
| iPS:393066 | 21-225_33A9 | NA | SEQ ID NO:604<br>CGGGCAAGTCAGAGCATTAG<br>CAGGTATTTAAGT | SEQ ID NO:8616<br>GCTGCATCCAGTTTGCAA<br>AGT | SEQ ID NO:16628<br>CAACAGAGTTACAATATCCC<br>GATCACC |
| | | AA | SEQ ID NO:605<br>RASQSISRYLS | SEQ ID NO:8617<br>AASSLQS | SEQ ID NO:16629<br>QQSYNIPIT |
| iPS:393068 | 21-225_34D3 | NA | SEQ ID NO:606<br>CGGGCAAGTCAGAACACATTA<br>CAGCTATTTAAAT | SEQ ID NO:8618<br>GCTGCATCCAGTTTGCAT<br>AGT | SEQ ID NO:16630<br>CAACAGAGTTACAGTACTCC<br>GCTCACT |
| | | AA | SEQ ID NO:607<br>RASQNIYSYLN | SEQ ID NO:8619<br>AASSLHS | SEQ ID NO:16631<br>QQSYSTPLT |
| iPS:393070 | 21-225_34G9 | NA | SEQ ID NO:608<br>CGGGCAAGTCAGGACATTAG<br>AAGTGATTTAGGC | SEQ ID NO:8620<br>GCTGCATCCAGTTTGCAA<br>AGT | SEQ ID NO:16632<br>CTCCAGCATACTATTTACCCT<br>CCTACT |
| | | AA | SEQ ID NO:609<br>RASQDIRSDLG | SEQ ID NO:8621<br>AASSLQS | SEQ ID NO:16633<br>LQHTIYPPT |
| iPS:393072 | 21-225_36C5 | NA | SEQ ID NO:610<br>CGGGCAAGTCAGGACATTAGG<br>AAGTGATTTAGGC | SEQ ID NO:8622<br>GCTGCATCCAGTTTGCAA<br>AGT | SEQ ID NO:16634<br>CTCCATCATCCTATTTACCCT<br>CCTACT |
| | | AA | SEQ ID NO:611<br>RASQDIRSDLG | SEQ ID NO:8623<br>AASSLQS | SEQ ID NO:16635<br>LHHPIYPPT |
| iPS:393074 | | NA | SEQ ID NO:612<br>CGGACAAGTCAGGGCATTAG<br>AAATGATTTAGGC | SEQ ID NO:8624<br>ACTGCATCCAGTTTGCAA<br>AGT | SEQ ID NO:16636<br>CTACAGCATAATAGTTACCC<br>GCTCACT |

FIGURE 49
(Continued)

| | | | | | |
|---|---|---|---|---|---|
| iPS:393076 | 21-225_33B1 | AA | SEQ ID NO:613 RTSQGIRNDLG | SEQ ID NO:8625 TASSLQS | SEQ ID NO:16637 LQHNSYPLT |
| | | NA | SEQ ID NO:614 CGGGCAAGTCAGGACATTAG AAATGATGTAGGC | SEQ ID NO:8626 GCTGCATCCAGTTGCAA CGT | SEQ ID NO:16638 CTACAGCATTATAGTTACCC TCCTACT |
| iPS:393078 | 21-225_33A4 | AA | SEQ ID NO:615 RASQDIRNDVG | SEQ ID NO:8627 AASSLQR | SEQ ID NO:16639 LQHYSYPPT |
| | | NA | SEQ ID NO:616 TGGGCGAGTCAGGGCATTAA CAGTTATTTAGCC | SEQ ID NO:8628 GCTGCATCCAGTTGCAA GGT | SEQ ID NO:16640 CAACAGTTAATAGTTACCC TCTGACG |
| iPS:393080 | 21-225_33H11 | AA | SEQ ID NO:617 WASQGINSYLA | SEQ ID NO:8629 AASSLQG | SEQ ID NO:16641 QQFNSYPLT |
| | | NA | SEQ ID NO:618 CGGGCGAGTCAGGGTATTAG TAAGTGGTTAGCC | SEQ ID NO:8630 GCTGCATCCAGTTGCAA AGT | SEQ ID NO:16642 CAACAGGCTAACAGTTCCC TTTCACT |
| iPS:393082 | 21-225_34F3 | AA | SEQ ID NO:619 RASQGISKWLA | SEQ ID NO:8631 AASSLQS | SEQ ID NO:16643 QQANSFPFT |
| | | NA | SEQ ID NO:620 CGGGCAAGTCAGAACATTAG GAACTTTTAAAT | SEQ ID NO:8632 GGGTGCATCCACTTGCAA AGT | SEQ ID NO:16644 CAACAGACTTGCAGTACCCC GCTCACT |
| iPS:393084 | 21-225_34C11 | AA | SEQ ID NO:621 RASQNIRNFLN | SEQ ID NO:8633 GASTLQS | SEQ ID NO:16645 QQTCSTPLT |
| | | NA | SEQ ID NO:622 CGGGCGAGTCAGGGTATTAG CAAATGGTTAGCC | SEQ ID NO:8634 GCTGCATCCAGTTGCAG AGT | SEQ ID NO:16646 CAACAGGCTAACAGTTCCC ATTCACT |
| iPS:393086 | 21-225_35C6 | AA | SEQ ID NO:623 RASQGISKWLA | SEQ ID NO:8635 AASSLQS | SEQ ID NO:16647 QQANSFPFT |
| | | NA | SEQ ID NO:624 CGGGCGAGTCAGGGTATTAG CAGATGGTTAGCC | SEQ ID NO:8636 GCTGCATCCCGTTGCAA AGT | SEQ ID NO:16648 CAACAGGCTAACAGTTCCC TTTCACT |

FIGURE 49
(Continued)

| | | | | | | |
|---|---|---|---|---|---|---|
| iPS:393088 | 21-225_36H5 | AA | SEQ ID NO:625<br>RASQGISRWLA<br>SEQ ID NO:626 | | SEQ ID NO:8637<br>AASRLQS<br>SEQ ID NO:8638 | SEQ ID NO:16649<br>QQANSFPFT<br>SEQ ID NO:16650 |
| iPS:393090 | 21-225_33D1 | NA | AAGTCCATCCAGAGTGTTTT<br>ATACAGATCCAACAATAAGA<br>ACTACTTAACT<br>SEQ ID NO:627 | | TGGGCATCTACCGGGA<br>ATCC<br>SEQ ID NO:8639 | CAGCAATATTATAGTTCTCC<br>GTGCAGT<br>SEQ ID NO:16651 |
| | | AA | KSIQSVLYRSNNKNYLT<br>SEQ ID NO:628 | | WASTRES<br>SEQ ID NO:8640 | QQYYSSPCS<br>SEQ ID NO:16652 |
| iPS:393092 | 21-225_33A5 | NA | CGGGCAAGTCAGAGTCAGGGCATTAG<br>CAATTACTTAGCC<br>SEQ ID NO:629 | | GCTGCATCCAGTTGCAA<br>AGT<br>SEQ ID NO:8641 | CAACAGTATAATAGTTACCC<br>ATTCACT<br>SEQ ID NO:16653 |
| | | AA | RASQGISNYLA<br>SEQ ID NO:630 | | AASSLQS<br>SEQ ID NO:8642 | QQYNSYPFT<br>SEQ ID NO:16654 |
| iPS:393094 | 21-225_33C12 | NA | CGGGCAAGTCAGAGTCAGGGCATTAT<br>CAGCTATTTAAAT<br>SEQ ID NO:631 | | GTTGCATCCAGTTGCAA<br>GGT<br>SEQ ID NO:8643 | CAACAGAGTTACAGTACCCC<br>GTACACT<br>SEQ ID NO:16655 |
| | | AA | RASQSIISYLN<br>SEQ ID NO:632 | | VASSLQG<br>SEQ ID NO:8644 | QQSYSTPYT<br>SEQ ID NO:16656 |
| iPS:393094 | 21-225_34C4 | NA | CGGGCAAGTCAGGGCATTAG<br>AAATGATTAGGC<br>SEQ ID NO:633 | | ACTGCATCCAATTGCAA<br>AGT<br>SEQ ID NO:8645 | CTACAACATAGTTCTTACCC<br>CATCACC<br>SEQ ID NO:16657 |
| | | AA | RASQGIRNDLG<br>SEQ ID NO:634 | | TASNLQS<br>SEQ ID NO:8646 | LQHSSYPIT<br>SEQ ID NO:16658 |
| iPS:393096 | 21-225_34D11 | NA | CGGGCAAGTCAGGACATTAG<br>AAGTGATTTAGGC<br>SEQ ID NO:635 | | GCTGCATCCAGTTGCAA<br>AGT<br>SEQ ID NO:8647 | CTACAGCATACTATTTACCC<br>TCCTACT<br>SEQ ID NO:16659 |
| | | AA | RASQDIRSDLG<br>SEQ ID NO:636 | | AASSLQS<br>SEQ ID NO:8648 | LQHTYPPT<br>SEQ ID NO:16660 |

FIGURE 49
(Continued)

| | | NA | CGGGGCGAGTCAGGGTATTAG CCGGTGGTTAGCC SEQ ID NO:637 | GCTGCATCCAGGTTGCA AAGT SEQ ID NO:8649 | CAACAGGCTAACAGTTTCCC GTTCACT SEQ ID NO:16661 |
|---|---|---|---|---|---|
| iPS:393098 | 21-225_35G6 | AA | RASQGISRWLA SEQ ID NO:638 | AASRLQS SEQ ID NO:8650 | QQANSFPFT SEQ ID NO:16662 |
| iPS:393100 | 21-225_36B8 | NA | CGGGCAAGTCAGAGAGCATTAT CAGCTATTTAAAT SEQ ID NO:639 | GTTGCATCCAGTTTGCAA AGT SEQ ID NO:8651 | CAACAGAGTTACAGTACCCC GTACACT SEQ ID NO:16663 |
| | | AA | RASQSISYLN SEQ ID NO:640 | VASSLQS SEQ ID NO:8652 | QQSYSTPYT SEQ ID NO:16664 |
| iPS:393102 | 21-225_33F1 | NA | CGGACAAGTCAGGACATTAG AAGTGATTTAGGC SEQ ID NO:641 | GCTGCATCCAGTTTGCAA AGT SEQ ID NO:8653 | CTACAGCATACTATTTACCC TCCTACT SEQ ID NO:16665 |
| | | AA | RTSQDIRSDLG SEQ ID NO:642 | AASSLQS SEQ ID NO:8654 | LQHTYPPT SEQ ID NO:16666 |
| iPS:393104 | 21-225_33A7 | NA | CGGGCAAGTCAGGACATTAA AAGTGATTTAGGC SEQ ID NO:643 | GTTGCATCCAGTTTGCAA AGT SEQ ID NO:8655 | CTACAGCATACTATTTACCC TCCTACT SEQ ID NO:16667 |
| | | AA | RASQDIRSDLG SEQ ID NO:644 | VASSLQS SEQ ID NO:8656 | LQHTYPPT SEQ ID NO:16668 |
| iPS:393106 | 21-225_34A6 | NA | CGGACAAGTCAGGACATCA GAAATGATTTAGGC SEQ ID NO:645 | GCTGCATCCAGTTTGCAA AGT SEQ ID NO:8657 | CTACAGCATAATAGTTACCC TCCTACT SEQ ID NO:16669 |
| | | AA | RTSQDIRNDLG SEQ ID NO:646 | AASSLQS SEQ ID NO:8658 | LQHNSYPPT SEQ ID NO:16670 |
| iPS:393108 | 21-225_34G11 | NA | CGGGCAAGTCAGAACATTAA CAGGTATTTAAAT SEQ ID NO:647 | GGTGCATCCAGTTTGCA AAGT SEQ ID NO:8659 | CAACAGACTTACATTACCCC GCTCACT SEQ ID NO:16671 |
| | | AA | RASQNINRYLN SEQ ID NO:648 | GASSLQS SEQ ID NO:8660 | QQTYTPLT SEQ ID NO:16672 |

FIGURE 49
(Continued)

| | | | | | |
|---|---|---|---|---|---|
| iPS:393110 | 21-225_35B7 | NA | CGGGCAAGTCAGGACATTAG AAGTGATTAGGC<br>SEQ ID NO:649 | GCTGCATCCAGTTTGCAA AGT<br>SEQ ID NO:8661 | CTACAGGCATACTATTTACCC TCCTACT<br>SEQ ID NO:16673 |
| | | AA | RASQDIRSDLG<br>SEQ ID NO:650 | AASSLQS<br>SEQ ID NO:8662 | LQHTYPPT<br>SEQ ID NO:16674 |
| iPS:393112 | 21-225_33G1 | NA | CGGGCGAGTCAGGGTTATTAG CAGGTGGTTAGCC<br>SEQ ID NO:651 | GGTGCATACAGTCTGCA AAGT<br>SEQ ID NO:8663 | CAACAGGCTAACAGTTTCCC ATTCACT<br>SEQ ID NO:16675 |
| | | AA | RASQGISRWLA<br>SEQ ID NO:652 | GAYSLQS<br>SEQ ID NO:8664 | QQANSFPFT<br>SEQ ID NO:16676 |
| iPS:393114 | 21-225_33G12 | NA | CGGGCAAGTCAGAGCATTAG CAACTATTTAAAT<br>SEQ ID NO:653 | GCTGCATCCAGTTTGCAA AGT<br>SEQ ID NO:8665 | CAACAGAGTTACAGTACCCC ATTCACT<br>SEQ ID NO:16677 |
| | | AA | RASQSISNYLN<br>SEQ ID NO:654 | AASSLQS<br>SEQ ID NO:8666 | QQSYSPFT<br>SEQ ID NO:16678 |
| iPS:393116 | 21-225_34G7 | NA | CGGGCGAGTCAGGCTTATTAG CAAGTGGTTAGCC<br>SEQ ID NO:655 | GCTGCATCCAGTTTGCAA AGT<br>SEQ ID NO:8667 | CAACAGGCTAACAGTTTCCC ATTCACT<br>SEQ ID NO:16679 |
| | | AA | RASQLISKWLA<br>SEQ ID NO:656 | AASSLQS<br>SEQ ID NO:8668 | QQANSFPFT<br>SEQ ID NO:16680 |
| iPS:393118 | 21-225_34H11 | NA | CGGGCAAGTCAGGACATTAG AAATGATTAGGC<br>SEQ ID NO:657 | GCTACATCCAGTTTGCAA AGT<br>SEQ ID NO:8669 | CTACAGCATAATAGTTACCC TCCTACT<br>SEQ ID NO:16681 |
| | | AA | RASQDIRNDLG<br>SEQ ID NO:658 | ATSSLQS<br>SEQ ID NO:8670 | LQHNSYPPT<br>SEQ ID NO:16682 |
| iPS:393120 | 21-225_35H8 | NA | CGGGCGAGTCAGGCCATTAG TAATTATTTAGCC<br>SEQ ID NO:659 | GGTGCGTCCGGTTTGCA AAGT<br>SEQ ID NO:8671 | CAACAGTATAATAGTTACC ATTCACT<br>SEQ ID NO:16683 |
| | | AA | RASQAISNYLA<br>SEQ ID NO:660 | GASGLQS<br>SEQ ID NO:8672 | QQYNSYPFT<br>SEQ ID NO:16684 |

FIGURE 49
(Continued)

| iPS | | | | | | |
|---|---|---|---|---|---|---|
| iPS:393122 | 21-225_33B2 | NA | CGGGCAAGTCAGAGAGCATTAT CAGCTATTAAAT SEQ ID NO:661 | GTTGCATCCAGTTTGCAA AGT SEQ ID NO:8673 | CAACAGAGTTACAGTACCCC GTACACT SEQ ID NO:16685 | |
| | | AA | RASQSISYLN SEQ ID NO:662 | VASSLQS SEQ ID NO:8674 | QQSYSTPYT SEQ ID NO:16686 | |
| iPS:393124 | 21-225_33G7 | NA | CGGGCAAGTCAGGGCATTAG AAATGATTAGGC SEQ ID NO:663 | GCTGCATCCAGTTTGCAA AGT SEQ ID NO:8675 | CTACAGCATTATAGTTACCC TCCTACT SEQ ID NO:16687 | |
| | | AA | RASQGIRNDLG SEQ ID NO:664 | AASSLQS SEQ ID NO:8676 | LQHYSYPPT SEQ ID NO:16688 | |
| iPS:393126 | 21-225_35D1 | NA | CGGGCAAGTCAGGACATTAG AAGTGATTAGGC SEQ ID NO:665 | GCTGCATCCAGTTTGCAA AGT SEQ ID NO:8677 | CTACAGCATACTATTACCC TCCCACT SEQ ID NO:16689 | |
| | | AA | RASQDIRSDLG SEQ ID NO:666 | AASSLQS SEQ ID NO:8678 | LQHTYPPT SEQ ID NO:16690 | |
| iPS:393128 | 21-225_35F11 | NA | CGGGCAAGTCAGGACATTAG AAGTGATTAGGC SEQ ID NO:667 | GCTGCATCCAGTTTGCAA AGT SEQ ID NO:8679 | CTACAGCATACTGTTACCC TCCTACT SEQ ID NO:16691 | |
| | | AA | RASQDIRSDLG SEQ ID NO:668 | AASSLQS SEQ ID NO:8680 | LQHTVYPPT SEQ ID NO:16692 | |
| iPS:393130 | 21-225_33C2 | NA | CGGGCAAGTCAGGGCATTAG AAATGATTAGGC SEQ ID NO:669 | GCTGCACCCAGTTGCA AAGT SEQ ID NO:8681 | CTACAGCATAATAGTTACCC GTGGACG SEQ ID NO:16693 | |
| | | AA | RASQGIRNDLG SEQ ID NO:670 | AAPSLQS SEQ ID NO:8682 | LQHNSYPWT SEQ ID NO:16694 | |
| iPS:393132 | 21-225_33H7 | NA | CGGGCGAGTCAGGGTATTAG CCGGTGGTTAGCC SEQ ID NO:671 | GCTGCATCCAGGTTGCA AAGT SEQ ID NO:8683 | CAACAGGCTAACATTTCCC GTTCACT SEQ ID NO:16695 | |
| | | AA | RASQGISRWLA SEQ ID NO:672 | AASRLQS SEQ ID NO:8684 | QQANIFPFT SEQ ID NO:16696 | |

FIGURE 49
(Continued)

| | | | | |
|---|---|---|---|---|
| iPS:393134 | 21-225_34C2 | NA | CGGGCAAGTCAGAGAGAATTAT CAGCTATTTAAAT SEQ ID NO:673 | GTTGCATCCAGTTTGCAA AGT SEQ ID NO:8685 | CAACAGAGTTACAGTACCCC GTACACT SEQ ID NO:16697 |
| | | AA | RASQRIISYLN SEQ ID NO:674 | VASSLQS SEQ ID NO:8686 | QQSYSTPYT SEQ ID NO:16698 |
| iPS:393136 | 21-225_34D8 | NA | CGGGCAAGTCAGAGATCATTAT CAGCTATTTAAAT SEQ ID NO:675 | GTTGCATCCAGTTTGCAA AGT SEQ ID NO:8687 | CAACAGAGTTACAGTACCCC GTACACT SEQ ID NO:16699 |
| | | AA | RASQIISYLN SEQ ID NO:676 | VASSLQS SEQ ID NO:8688 | QQSYSTPYT SEQ ID NO:16700 |
| iPS:393138 | 21-225_35E3 | NA | CAGGCGAGTCAGGACATTTT CAACTATTTAAAT SEQ ID NO:677 | GATGCCTCCAATTTGGA AACA SEQ ID NO:8689 | CAACAGTATGATAATCTCCC GATCACC SEQ ID NO:16701 |
| | | AA | QASQDIFNYLN SEQ ID NO:678 | DASNLET SEQ ID NO:8690 | QQYDNLPIT SEQ ID NO:16702 |
| iPS:393140 | 21-225_35H12 | NA | CGGGCGAGTCAGGGTATTAG CAGATGGTTAGCC SEQ ID NO:679 | GCTGCATCCCGTTTGCAA AGT SEQ ID NO:8691 | CAACAGGCTAACAGTTTCCC ATTCACT SEQ ID NO:16703 |
| | | AA | RASQGISRWLA SEQ ID NO:680 | AASRLQS SEQ ID NO:8692 | QQANSFPFT SEQ ID NO:16704 |
| iPS:393142 | 21-225_33A3 | NA | CGGGCGAGTCAGGGCATTAA CAATTATTTAGCC SEQ ID NO:681 | GCTGCATCCAGTTTGCAA AGT SEQ ID NO:8693 | CAACAGTTTAATAGTTACCC TCCGACG SEQ ID NO:16705 |
| | | AA | RASQGINNYLA SEQ ID NO:682 | AASSLQS SEQ ID NO:8694 | QQFNSYPPT SEQ ID NO:16706 |
| iPS:393144 | 21-225_34D2 | NA | AAGTCTAGTCAGAGCCTCCT GCATAGTGATGGAAAGACCT ATTTGTAT SEQ ID NO:683 | GAAGTTTCCAACCGGTTC TCT SEQ ID NO:8695 | ATGCAAAGTAAACAGCTTCC TCCT SEQ ID NO:16707 |
| | | AA | KSSQSLLHSDGKTYLY | EVSNRFS | MQSKQLPP |

FIGURE 49
(Continued)

| | | | | | | |
|---|---|---|---|---|---|---|
| iPS:393146 | | | SEQ ID NO:684 CGGGCAAGTCAGGACATTAG AAGTGATTTAGGC | SEQ ID NO:8696 GCTGCATCCAGTTTGCAA AGT | SEQ ID NO:16708 CTACAGATACTATTTACCC TCCTACT |
| | 21-225_34G8 | NA | SEQ ID NO:685 RASQDIRSDLG | SEQ ID NO:8697 AASSLQS | SEQ ID NO:16709 LQHTIYPPT |
| | | AA | SEQ ID NO:686 | SEQ ID NO:8698 | SEQ ID NO:16710 |
| iPS:393148 | | NA | SEQ ID NO:687 CGGGCAAGTCAGAGCATTAG CAGCTATTTAAAT | SEQ ID NO:8699 GGTGCATCCAGTTTCCAA AGT | SEQ ID NO:16711 CACCAGAGTTACAATCTCCC GATCACC |
| | 21-225_35E5 | AA | SEQ ID NO:688 RASQSISSYLN | SEQ ID NO:8700 GASSFQS | SEQ ID NO:16712 HQSYNLPIT |
| iPS:393150 | | NA | SEQ ID NO:689 CGGACAAGTCAGGACATTAG AAATGATTTAGGC | SEQ ID NO:8701 GCTGCATCCAGTTTGCAA AGT | SEQ ID NO:16713 CTACACCACAATAGTTACCC TCCTAAG |
| | 21-225_36A5 | AA | SEQ ID NO:690 RTSQDIRNDLG | SEQ ID NO:8702 AASSLQS | SEQ ID NO:16714 LHHNSYPPK |
| iPS:393152 | | NA | SEQ ID NO:691 CGGGCGAGTCAGGGTATTAG CAGCTGGTTAGCC | SEQ ID NO:8703 GGTGCATCCAGTTTGCA AAGT | SEQ ID NO:16715 CAACAGTCTGACAGTTTCCC TCGGACG |
| | 21-225_25B3 | AA | SEQ ID NO:692 RASQGISSWLA | SEQ ID NO:8704 GASSLQS | SEQ ID NO:16716 QQSDSFPRT |
| iPS:393166 | | NA | SEQ ID NO:693 TCTGGAGATAAATTGGGGA TAAATATGCTTGC | SEQ ID NO:8705 CAAGATAGGAAGCGGCC CTCA | SEQ ID NO:16717 CAGGCGTGGGACAGCAGCTC TTATGTGGTA |
| | 21-225_27G6 | AA | SEQ ID NO:694 SGDKLGDKYAC | SEQ ID NO:8706 QDRKRPS | SEQ ID NO:16718 QAWDSSSYVV |
| iPS:393168 | | NA | SEQ ID NO:695 TCTGGAGATAAATTGGGGGA TAAATATGCTTAC | SEQ ID NO:8707 CAAGATAGTAAGCGGTC CTCA | SEQ ID NO:16719 CAGGCGTGGGACAACAGCAC TGTGGTA |
| | 21-225_32B11 | AA | SGDKLGDKYAY | QDSKRSS | QAWDNSTVV |

FIGURE 49
(Continued)

| | | | | | | |
|---|---|---|---|---|---|---|
| iPS:393172 | 21-225_3B12 | NA | SEQ ID NO:696 TCTGGAGATAAATTGGGGGA AAATATGCTTGC | SEQ ID NO:8708 CAAGATAGGAAGCGGCC CTCA | SEQ ID NO:16720 CAGGCGTGGGTCAACAACAC TATGATA | |
| | | AA | SEQ ID NO:697 SGDKLGEKYAC | SEQ ID NO:8709 QDRKRPS | SEQ ID NO:16721 QAWVNNTMI | |
| iPS:393174 | 21-225_15D8 | NA | SEQ ID NO:698 ACCCTAAGCAGTGAGCACAG CACCTACACCATCGAA | SEQ ID NO:8710 GTTAAGAGTGATGGCAG CCACAGCAAGGGGGAC | SEQ ID NO:16722 GGAGAGAGCCACACGATCGA TGGCCAAGTCGGTGTGGTA | |
| | | AA | SEQ ID NO:699 TILSSEHSTYTIE | SEQ ID NO:8711 VKSDGSHSKGD | SEQ ID NO:16723 GESHTIDGQVGVV | |
| iPS:393176 | 21-225_27E7 | NA | SEQ ID NO:700 TCTGGAGATAAATTGGGGAA TAAATATGCTTGC | SEQ ID NO:8712 CAAGATAGCAAGCGGCC CTTA | SEQ ID NO:16724 CAGGCGTGGGACAGTAGTAC TGTGGTA | |
| | | AA | SEQ ID NO:701 SGDKLGNKYAC | SEQ ID NO:8713 QDSKRPL | SEQ ID NO:16725 QAWDSSTVV | |
| iPS:393178 | 21-225_34D7 | NA | SEQ ID NO:702 TCTGGAGATAAATTGGGGGA GAAATATGCTTAC | SEQ ID NO:8714 CAAGATAGCAAGCGGCC CTCA | SEQ ID NO:16726 CAGGCGTGGGACAACACCAC TGTGGTA | |
| | | AA | SEQ ID NO:703 SGDKLGEKYAY | SEQ ID NO:8715 QDSKRPS | SEQ ID NO:16727 QAWDNTTVV | |
| iPS:393180 | 21-225_4G12 | NA | SEQ ID NO:704 TCTGGAACCAACTCCAACAT CGGAAGTTATACTGTAAAC | SEQ ID NO:8716 ATTAATAATCAGCGGCC CTCA | SEQ ID NO:16728 GCAGCATGGGATGACAGCCT GAATGGTCATGTGGTA | |
| | | AA | SEQ ID NO:705 SGTNSNIGSYTVN | SEQ ID NO:8717 INNQRPS | SEQ ID NO:16729 AAWDDSLNGHVV | |
| iPS:393182 | | NA | SEQ ID NO:706 TCTGGAGATAAATTGGGGGA TAAATATGCTTGC | SEQ ID NO:8718 CAAGATCGCAAGCGGCC CTCA | SEQ ID NO:16730 CAGGCGTGGGACAACAACAC TGTGATA | |

FIGURE 49
(Continued)

| | | | | | |
|---|---|---|---|---|---|
| iPS:393184 | 21-225_4B3 | AA | SEQ ID NO:707<br>SGDKLGDKYAC | SEQ ID NO:8719<br>QDRKRPS | SEQ ID NO:16731<br>QAWDNNTVI |
| | | NA | SEQ ID NO:708<br>TCTGGAGATAAATTGGGGGA<br>GAAATATGCTTGC | SEQ ID NO:8720<br>CAAGATAGGAAGCGGCC<br>CTCA | SEQ ID NO:16732<br>CAGGCGTGGGACAGCAGCAC<br>TGCGGTA |
| iPS:393186 | 21-225_15H11 | AA | SEQ ID NO:709<br>SGDKLGEKYAC | SEQ ID NO:8721<br>QDRKRPS | SEQ ID NO:16733<br>QAWDSSTAV |
| | | NA | SEQ ID NO:710<br>TCTGGAGATAAATTGGGGGA<br>TAAATATGCTTGC | SEQ ID NO:8722<br>CAAGATAGCAAGCGGCC<br>CTCA | SEQ ID NO:16734<br>CAGGCGTGGGTCAACAACAC<br>TGTA |
| iPS:393188 | 21-225_27B9 | AA | SEQ ID NO:711<br>SGYKLGDKYAC | SEQ ID NO:8723<br>QDSKRPS | SEQ ID NO:16735<br>QAWVNNTV |
| | | NA | SEQ ID NO:712<br>TCTGGAGATAAATTGGGGGA<br>GAAATATGTTTCC | SEQ ID NO:8724<br>CAAGATAGTAAGCGGCC<br>CTCA | SEQ ID NO:16736<br>CAGGCGTGGGACAGCAGCAC<br>TGTA |
| iPS:393192 | 21-225_34B9 | AA | SEQ ID NO:713<br>SGDKLGEKYVS | SEQ ID NO:8725<br>QDSKRPS | SEQ ID NO:16737<br>QAWDSSTV |
| | | NA | SEQ ID NO:714<br>TCTGGAGATAAATTGGGGGA<br>TAAATATGCTTGC | SEQ ID NO:8726<br>CAAGATCGCAAGCGGCC<br>CTCA | SEQ ID NO:16738<br>CAGGCGTGGGACAACAACAC<br>TGTGATA |
| iPS:393194 | 21-225_12B1 | AA | SEQ ID NO:715<br>SGDKLGDKYAC | SEQ ID NO:8727<br>QDRKRPS | SEQ ID NO:16739<br>QAWDNNTVI |
| | | NA | SEQ ID NO:716<br>TCTGGAGATAAATTGGGGGA<br>TAAATATGCTTGC | SEQ ID NO:8728<br>CAAGATAGCAAGCGGCC<br>CTCA | SEQ ID NO:16740<br>CAGGCGTGGGACAGCAGCAC<br>TGTGATA |
| iPS:393196 | 21-225_16D2 | AA | SEQ ID NO:717<br>SGDKLGDKYAC | SEQ ID NO:8729<br>QDSKRPS | SEQ ID NO:16741<br>QAWDSSTYVV |
| | | NA | SEQ ID NO:718<br>TCTGGAGATAAATTGGGGGA<br>AAAATATGCTTGC | SEQ ID NO:8730<br>CAAGATAGGAAGCGGCC<br>CTCA | SEQ ID NO:16742<br>CAGGCGTGGGTCAATAACAC<br>TATGATA |

FIGURE 49
(Continued)

| | | | | | | |
|---|---|---|---|---|---|---|
| iPS:393198 | 21-225_16G8 | AA | SEQ ID NO:719 SGDKLGEKYAC | | SEQ ID NO:8731 QDRKRPS | SEQ ID NO:16743 QAWVNNTMI |
| | | NA | SEQ ID NO:720 TCTGGAGATAAATTGGGGGA TAAATATGCTTGC | | SEQ ID NO:8732 CAAGATAGCAAGCGGCC CTCA | SEQ ID NO:16744 CAGGCGTGGGACAGTAGCAC TTATGTGGTA |
| iPS:393200 | 21-225_28A11 | AA | SEQ ID NO:721 SGDKLGDKYAC | | SEQ ID NO:8733 QDSKRPS | SEQ ID NO:16745 QAWDSSTYVV |
| | | NA | SEQ ID NO:722 TCTGGAGATAAATTGGGGGA AAAATATGCTTAC | | SEQ ID NO:8734 CAAGATAGGAAGCGGCC CTCA | SEQ ID NO:16746 CAGGCGTGGGACAACAGCAC TGCGGTA |
| iPS:393202 | 21-225_35E1 | AA | SEQ ID NO:723 SGDKLGEKYAY | | SEQ ID NO:8735 QDRKRPS | SEQ ID NO:16747 QAWDNSTAV |
| | | NA | SEQ ID NO:724 TCTGGAGATAAATTGGGGGA TAAATATGCTTGC | | SEQ ID NO:8736 CAAGATCGCAAGCGGCC CTCA | SEQ ID NO:16748 CAGGCGTGGGACAACAACAC TGTGATA |
| iPS:393204 | 21-225_6B4 | AA | SEQ ID NO:725 SGDKLGDKYAC | | SEQ ID NO:8737 QDRKRPS | SEQ ID NO:16749 QAWDNNTVI |
| | | NA | SEQ ID NO:726 GGGGGAAACAACATTGGAA GTAAAGCTGTGCAC | | SEQ ID NO:8738 AGCGATAGCAACCGGCC CTCA | SEQ ID NO:16750 CAGGTGTGGGACAGTAGTAG TGATCATGTGGTA |
| iPS:393206 | 21-225_8C12 | AA | SEQ ID NO:727 GGNNIGSKAVH | | SEQ ID NO:8739 SDSNRPS | SEQ ID NO:16751 QVWDSSSDHVV |
| | | NA | SEQ ID NO:728 TCTGGAGATAAATTGGGGGA TAAATATGCTTGC | | SEQ ID NO:8740 CAAGATAGCAAGCGGCC CTCA | SEQ ID NO:16752 CAGGCGTGGGGCAACAGCAC TGCTGTGGTA |
| iPS:393208 | 21-225_13F6 | AA | SEQ ID NO:729 SGDKLGDKYAC | | SEQ ID NO:8741 QDSKRPS | SEQ ID NO:16753 QAWGNSTAVV |
| | | NA | SEQ ID NO:730 GGGGGAAACAACATTGGAA GTAAAGTGTGCAC | | SEQ ID NO:8742 GATGATACCGACCGGCC CTCA | SEQ ID NO:16754 CAGGTGTGGGATAGTAGCAG TGATCATGTGGTA |

FIGURE 49
(Continued)

| | | | | | | |
|---|---|---|---|---|---|---|
| iPS:393210 | 21-225_16F3 | AA | SEQ ID NO:731 GGNNIGSKSVH | SEQ ID NO:8743 DDTDRPS | | SEQ ID NO:16755 QVWDSSSDHVV |
| iPS:393212 | 21-225_17D3 | NA | SEQ ID NO:732 TCTGGAGATAAATTGGGGA TAAATATGTTTAC | SEQ ID NO:8744 CAAGATAGGAAGCGGCC CTCA | | SEQ ID NO:16756 CAGGCGTGGGACAGCATCAC TGCAGTA |
| | | AA | SEQ ID NO:733 SGDKLGDKYVY | SEQ ID NO:8745 QDRKRPS | | SEQ ID NO:16757 QAWDSITAV |
| iPS:393214 | 21-225_30H6 | NA | SEQ ID NO:734 TCTGGAGATAAATTGGGTAA TAAATATGCTTGC | SEQ ID NO:8746 CAAGATAGCAAGCGGCC CTCA | | SEQ ID NO:16758 CAGGCGTGGGACAGCAGCAC TGTT |
| | | AA | SEQ ID NO:735 SGDKLGNKYAC | SEQ ID NO:8747 QDSKRPS | | SEQ ID NO:16759 QAWDSSTV |
| iPS:393218 | 21-225_33A1 | NA | SEQ ID NO:736 TCTGGAGATAAATTGGGGA TAAATTGTTTAT | SEQ ID NO:8748 CAAGATAGCAAGCGGCC CTCA | | SEQ ID NO:16760 CAGGCGTGGGACAGCACCAC CGTGGTA |
| | | AA | SEQ ID NO:737 SGDKLGDKFVY | SEQ ID NO:8749 QDSKRPS | | SEQ ID NO:16761 QAWDSTTVV |
| iPS:393222 | 21-225_14G3 | NA | SEQ ID NO:738 TCTGGAGATAAATTGGGGA TAAATATGCTTGC | SEQ ID NO:8750 CAAGATCGCAAGCGGCC CTCA | | SEQ ID NO:16762 CAGGCGTGGGGCAACAGCAC TGCTGTGGTA |
| | | AA | SEQ ID NO:739 SGDKLGDKYVC | SEQ ID NO:8751 QDRKRPS | | SEQ ID NO:16763 QAWGNSTAVV |
| iPS:393224 | 21-225_17F5 | NA | SEQ ID NO:740 TCTGGAGATAAATTGGGGA AAAATATGCTTGC | SEQ ID NO:8752 CAAGATAGAAAGCGCC CTCA | | SEQ ID NO:16764 CAGGCGTGGGACAGCAGCAC GGTA |
| | | AA | SEQ ID NO:741 SGDKLGEKYAC | SEQ ID NO:8753 QDRKRPS | | SEQ ID NO:16765 QAWDSSTV |
| | | NA | SEQ ID NO:742 TCTGGAGATAAATTGGGAAA TAAATATGCTTGC | SEQ ID NO:8754 CAAGATTCCAAGCGGCC CTCA | | SEQ ID NO:16766 CAGGCGTGGGACAGCAGCAC TGTA |

FIGURE 49
(Continued)

| | | | | | | |
|---|---|---|---|---|---|---|
| iPS:393226 | 21-225_31C2 | AA | SEQ ID NO:743<br>SGDKLGNKYAC | | SEQ ID NO:8755<br>QDSKRPS | | SEQ ID NO:16767<br>QAWDSSTV |
| | | NA | SEQ ID NO:744<br>TCTGGAGATAAATTGGGGGA<br>TAAATATGCTTAC | | SEQ ID NO:8756<br>CAAGATAGGAAGCGGCC<br>CTCA | | SEQ ID NO:16768<br>CAGGCGTGGACAACAGCAC<br>TGCGGTA |
| iPS:393230 | 21-225_33E6 | AA | SEQ ID NO:745<br>SGDKLGDKYAY | | SEQ ID NO:8757<br>QDRKRPS | | SEQ ID NO:16769<br>QAWDNSTAV |
| | | NA | SEQ ID NO:746<br>TCTGGAACCAACTCCAACAT<br>CGGAAGTTATACTGTAAAC | | SEQ ID NO:8758<br>ATTATAATCAGCGGCC<br>CTCA | | SEQ ID NO:16770<br>GCAGCATGGGATGACAGCCT<br>GAATGGTCATGTGGTA |
| iPS:393232 | 21-225_9G9 | AA | SEQ ID NO:747<br>SGTNSNIGSYTVN | | SEQ ID NO:8759<br>INNQRPS | | SEQ ID NO:16771<br>AAWDDSLNGHVV |
| | | NA | SEQ ID NO:748<br>ACTGGAGCCAGCAGTGACGT<br>TGGTGATTATAACTCTGTCT<br>CC | | SEQ ID NO:8760<br>GAGGTCAGTAATCGGCC<br>CTCA | | SEQ ID NO:16772<br>AGCTCATATACAAGCAGCAT<br>CACTGTGGTA |
| iPS:393234 | 21-225_17F12 | AA | SEQ ID NO:749<br>TGASSDVGDYNSVS | | SEQ ID NO:8761<br>EVSNRPS | | SEQ ID NO:16773<br>SSYTSSITVV |
| | | NA | SEQ ID NO:750<br>TCTGGAGATAAATTGGGGGA<br>TAAATATGTTTGC | | SEQ ID NO:8762<br>CAAGATAGCAAGCGGCC<br>CTCA | | SEQ ID NO:16774<br>CAGGCGTGGGTCAACAACAC<br>TGTA |
| iPS:393345 | 21-225_26C10 | AA | SEQ ID NO:751<br>SGDKLGDKYVC | | SEQ ID NO:8763<br>QDSKRPS | | SEQ ID NO:16775<br>QAWVNNTV |
| | | NA | SEQ ID NO:752<br>TCTGGAGATAAATTGGGGAA<br>TAAATATGCTTGG | | SEQ ID NO:8764<br>CAAGATAGGAAGCGGCC<br>CTCA | | SEQ ID NO:16776<br>CAGGCGTGGACAACAGCAC<br>TGTGGTT |
| iPS:393345 | 21-225_5G7 | AA | SEQ ID NO:753<br>SGDKLGNKYAW | | SEQ ID NO:8765<br>QDRKRPS | | SEQ ID NO:16777<br>QAWDNSTVV |
| | | | SEQ ID NO:754 | | SEQ ID NO:8766 | | SEQ ID NO:16778 |

FIGURE 49
(Continued)

| | | | | | |
|---|---|---|---|---|---|
| iPS:393368 | 21-225_29B18 | NA | AGGTCCAGCCAGAGTATTTT ACACAGCTCCAACAATTACA ACTACTTAGCT SEQ ID NO:755 | TGGGCATCTACCCGGGA ATCC SEQ ID NO:8767 | CAGCAATATTATTGTACTCC TCCGACG SEQ ID NO:16779 |
| | | AA | RSSQTLHSSNNYNYLA | WASTRES | QQYYCTPPT |
| | | | SEQ ID NO:756 | SEQ ID NO:8768 | SEQ ID NO:16780 |
| iPS:393565 | 21-225_34B11 | NA | TCTGGAGATAAATTGGGGGA TAAATATGCTTGC SEQ ID NO:757 | CAAGATATGAAGCGGCC CTCA SEQ ID NO:8769 | CAGGCGTGGGACAACAGCAC TGCGGTA SEQ ID NO:16781 |
| | | AA | SGDKLGDKYAC SEQ ID NO:758 | QDMKRPS SEQ ID NO:8770 | QAWDNSTAV SEQ ID NO:16782 |
| iPS:393802 | 21-225_3D12 | NA | AGGGCCAGTCAGAGTGTTAG CAGCAGCTACTTAGCC SEQ ID NO:759 | GGTACATCCAGCAGGGC CACT SEQ ID NO:8771 | CAGCAGTATGGTAGTTCACG CAGT SEQ ID NO:16783 |
| | | AA | RASQSVSSSYLA SEQ ID NO:760 | GTSSRAT SEQ ID NO:8772 | QQYGSSRS SEQ ID NO:16784 |
| iPS:393804 | 21-225_5H7 | NA | CGGGCAAGTCAGGGCATTAG AAATGATTTAGGC SEQ ID NO:761 | GTTACATCCAGTTTGCAA GGT SEQ ID NO:8773 | CTACAACATAATAGTTACCC GCTCACT SEQ ID NO:16785 |
| | | AA | RASQGIRNDLG SEQ ID NO:762 | VTSSLQG SEQ ID NO:8774 | LQHNSYPLT SEQ ID NO:16786 |
| iPS:393806 | 21-225_6A6 | NA | CGGGCAAGTCAGGGCATTAG AAATGATTTAGGC SEQ ID NO:763 | GCTGCATCCAGTTTGCAA AGT SEQ ID NO:8775 | CTACAGCATAGTAGTTACCC GCTCACT SEQ ID NO:16787 |
| | | AA | RASQGIRNDLG SEQ ID NO:764 | AASSLQS SEQ ID NO:8776 | LQHSSYPLT SEQ ID NO:16788 |
| iPS:393808 | 21-225_1A2 | NA | CGGGCAAGTCAGGGCATTAG AAATGATTTAGGC SEQ ID NO:765 | GCTGCATCCAGTTTGCAA AGT SEQ ID NO:8777 | CTACAGCATAATAGTCACCC TCTCACT SEQ ID NO:16789 |
| | | AA | RASQGIRNDLG | AASSLQS | LQHNSHPLT |

FIGURE 49
(Continued)

| | | | | | | |
|---|---|---|---|---|---|---|
| iPS:393810 | 21-225_5A4 | NA | SEQ ID NO:766 CGGGCGAGTCAGGGTATTAG CACCTGGTTAGCC | SEQ ID NO:8778 GATGCATCCAGTTTGCA AAGT | SEQ ID NO:16790 CAACAGGCTAACAGTTCCC GTGGACG | |
| | | AA | SEQ ID NO:767 RASQGISTWLA | SEQ ID NO:8779 DASSLQS | SEQ ID NO:16791 QQANSFPWT | |
| iPS:393812 | 21-225_6A11 | NA | SEQ ID NO:768 CGGGCAAGTCAGGGCATTAG AAATGATTTAGGC | SEQ ID NO:8780 GCTGCATCCAGTTTGCAA AGT | SEQ ID NO:16792 CTACAGCATAATAGTTACCC GTGGACG | |
| | | AA | SEQ ID NO:769 RASQGIRNDLG | SEQ ID NO:8781 AASSLQS | SEQ ID NO:16793 LQHNSYPWT | |
| iPS:393814 | 21-225_7F4 | NA | SEQ ID NO:770 CGGACAAGTCAGGGCATTAG AAATGATTTAGGC | SEQ ID NO:8782 GCTGCATCCAATTTGCAA AGT | SEQ ID NO:16794 CTACAGCATAGTGCTTACCC GCTCACT | |
| | | AA | SEQ ID NO:771 RTSQGIRNDLG | SEQ ID NO:8783 AASNLQS | SEQ ID NO:16795 LQHSAYPLT | |
| iPS:393816 | 21-225_6D4 | NA | SEQ ID NO:772 CGGGCAAGTCAGGGCATTAG AAATGATTTAGGC | SEQ ID NO:8784 GCTGCATCCAGTTTGCAA AGT | SEQ ID NO:16796 CTACAGCATAGTAGTTACCC GCTCACT | |
| | | AA | SEQ ID NO:773 RASQAIRNDLG | SEQ ID NO:8785 AASSLQS | SEQ ID NO:16797 LQHSSYPLT | |
| iPS:393818 | 21-225_6G12 | NA | SEQ ID NO:774 CGGGCAAGTCAGGGCATTAG AAATGATTTAGGC | SEQ ID NO:8786 GCTGCATCCACTTTGCAA AGT | SEQ ID NO:16798 CTACAGCATAATAGTTACCC GCTCACT | |
| | | AA | SEQ ID NO:775 RASQGIRNDLG | SEQ ID NO:8787 AASTLQS | SEQ ID NO:16799 LQHNSYPLT | |
| iPS:393820 | 21-225_8H7 | NA | SEQ ID NO:776 CGGGCAAGTCAGGGCATTAG AAATGATTTAGGC | SEQ ID NO:8788 GCTGCATCCAGTTTGCAA AGT | SEQ ID NO:16800 CTACAGCATAATAGTTACCC GTTCACT | |
| | | AA | SEQ ID NO:777 RASQGIRNDLG | SEQ ID NO:8789 AASSLQS | SEQ ID NO:16801 LQHNSYPFT | |

FIGURE 49
(Continued)

| iPS | Clone | | CDR1 | CDR2 | CDR3 |
|---|---|---|---|---|---|
| iPS:393822 | 21-225_15B11 | NA | SEQ ID NO:778 CGGGCAAGTCAGGGCATTAGAAATGATTTAGGC | SEQ ID NO:8790 GCTGCATCCAGTTTGCAAAGT | SEQ ID NO:16802 CTACAGCATAATAGTTACCCATTCACT |
| | | AA | SEQ ID NO:779 RASQGIRNDLG | SEQ ID NO:8791 AASSLQS | SEQ ID NO:16803 LQHNSYPFT |
| iPS:393824 | 21-225_10F12 | NA | SEQ ID NO:780 CGGGCAAGTCAGAACATTAGTAGTTATTTAAAT | SEQ ID NO:8792 GCTGCATCCAGTTTGCAAAGT | SEQ ID NO:16804 CAACAGAGTTACAATACCCCTTCTTCACT |
| | | AA | SEQ ID NO:781 RASQNISSYLN | SEQ ID NO:8793 AASSLQS | SEQ ID NO:16805 QQSYNTPFT |
| iPS:393826 | 21-225_10G5 | NA | SEQ ID NO:782 CGGGCAAGTCAGGGCATTAGAAATGATTTAGGC | SEQ ID NO:8794 GCTGCATCCAGTTTGCAAAGT | SEQ ID NO:16806 CTACAGCATAATAGTTACCCGCTCACT |
| | | AA | SEQ ID NO:783 RASQGIRNDLG | SEQ ID NO:8795 AASSLQS | SEQ ID NO:16807 LQHNSYPLT |
| iPS:393828 | 21-225_10H12 | NA | SEQ ID NO:784 CGGGCAAGTCAGGGCATTAGAAATGATTTAGGC | SEQ ID NO:8796 GGTGCATCCAGTTTGCAAAGT | SEQ ID NO:16808 CTACAGCATAATAGTTACCCGCTCACT |
| | | AA | SEQ ID NO:785 RASQGIRNDLG | SEQ ID NO:8797 GASSLQS | SEQ ID NO:16809 LQHNSYPLT |
| iPS:393830 | 21-225_12A1 | NA | SEQ ID NO:786 CGGGCAAGTCAGGGCATTAGAAATGATTTAGGC | SEQ ID NO:8798 GCTGCATCCAGTTTGCAAAGT | SEQ ID NO:16810 CTACAGCATAATAGTTACCCGCTCACT |
| | | AA | SEQ ID NO:787 RASQGIRNDLG | SEQ ID NO:8799 AASSLQS | SEQ ID NO:16811 LQHNSYPLT |
| iPS:393832 | 21-225_14B2 | NA | SEQ ID NO:788 CGGGCAAGTCAGGGCATTAGAAATGATTTAGGC | SEQ ID NO:8800 GTTACATCCAGTTTGCAAGGT | SEQ ID NO:16812 CTACAACATAATAGTTACCCGCTCACT |
| | | AA | SEQ ID NO:789 RASQGIRNDLG | SEQ ID NO:8801 VTSSLQG | SEQ ID NO:16813 LQHNSYPLT |

FIGURE 49 (Continued)

| | | | | | | | | |
|---|---|---|---|---|---|---|---|---|
| iPS:393836 | 21-225_15A2 | NA | SEQ ID NO:790 | CGGGCGAAGTCAGAGTCATTAG CAATTATTTAGCC | SEQ ID NO:8802 | GCTGCATCCAGTTTGCAA AGT | SEQ ID NO:16814 | CAACAGTATTATAGTTACCC ATTCACT |
| | | AA | SEQ ID NO:791 | RASQGISNYLA | SEQ ID NO:8803 | AASSLQS | SEQ ID NO:16815 | QQYYSYPFT |
| iPS:393838 | 21-225_6G2 | NA | SEQ ID NO:792 | CGGGCAAGTCAGGGCATTAG AAATGATTTAGGC | SEQ ID NO:8804 | GCTGCATCCAGTCTGCA AAGT | SEQ ID NO:16816 | ATACAGCATAATAGTTACCT GTGGACG |
| | | AA | SEQ ID NO:793 | RASQGIRNDLG | SEQ ID NO:8805 | AASSLQS | SEQ ID NO:16817 | IQHNSYLWT |
| iPS:393840 | 21-225_3F8 | NA | SEQ ID NO:794 | CGGGCAAGTCAGAGTATTCT CAGCTATTTAAAT | SEQ ID NO:8806 | ACTACATCCAGTTTGCAA AGT | SEQ ID NO:16818 | CAACAGACTTACAGTACCCC GCTCACT |
| | | AA | SEQ ID NO:795 | RASQSILSYLN | SEQ ID NO:8807 | TTSSLQS | SEQ ID NO:16819 | QQTYSTPLT |
| iPS:393844 | 21-225_3G7 | NA | SEQ ID NO:796 | CGGGCAAGTCAGAACATTA CAGGTATTTAAAT | SEQ ID NO:8808 | GCTGCATCCAGTTTCGCA AAGT | SEQ ID NO:16820 | CAACAGAGTTACAGTCCCCC TTTCACT |
| | | AA | SEQ ID NO:797 | RASQNIYRYLN | SEQ ID NO:8809 | AASSSQS | SEQ ID NO:16821 | QQSYSPPFT |
| iPS:393848 | 21-225_4H2 | NA | SEQ ID NO:798 | CGGGCAATTCAGAACATTA CAGCTATTTAAAT | SEQ ID NO:8810 | GCTGCATCCAGCTTGCA AAGT | SEQ ID NO:16822 | CAACAGAGTTACAGAACCCC CTTATTCACT |
| | | AA | SEQ ID NO:799 | RAIQNISSYLN | SEQ ID NO:8811 | AASSLQS | SEQ ID NO:16823 | QQSYRTPLFT |
| iPS:393852 | 21-225_12A10 | NA | SEQ ID NO:800 | CGGGCAAGTCAGAACATTA CAGCTATTTAAAT | SEQ ID NO:8812 | ACTGCATCCAGTTTGCAA AGT | SEQ ID NO:16824 | CAGCAGAGTTACAGTCCCCC TCTCACT |
| | | AA | SEQ ID NO:801 | RASQNIYSYLN | SEQ ID NO:8813 | TASSLQS | SEQ ID NO:16825 | QQSYSPPLT |

FIGURE 49
(Continued)

| | | | | | | |
|---|---|---|---|---|---|---|
| iPS:393854 | 21-225_7H11 | NA | SEQ ID NO:802<br>CTGGCAAGTCAGGGCATTAG<br>AAATGATTTAGGC | SEQ ID NO:8814<br>GTTGCATGTAGTTCCAA<br>AGT | SEQ ID NO:16826<br>CTACAACATAATCTTTACCC<br>GCTCACT |
| | | AA | SEQ ID NO:803<br>LASQGIRNDLG | SEQ ID NO:8815<br>VACSFQS | SEQ ID NO:16827<br>LQHNLYPLT |
| iPS:393856 | 21-225_14C2 | NA | SEQ ID NO:804<br>CGGGCAAGTCAGGGCATTAG<br>AAATGATTTAGAC | SEQ ID NO:8816<br>GCTGCATCCAGTTGCAA<br>AGT | SEQ ID NO:16828<br>GTACAGCATAATAGTTACCC<br>GCTCACT |
| | | AA | SEQ ID NO:805<br>RASQGIRNDLD | SEQ ID NO:8817<br>AASSLQS | SEQ ID NO:16829<br>VQHNSYPLT |
| iPS:393862 | 21-225_5G2 | NA | SEQ ID NO:806<br>CGGGCAAGTCAGAACATTAT<br>TAGTTATTTAAAT | SEQ ID NO:8818<br>GGTGCATCCAGTTGCA<br>AAGT | SEQ ID NO:16830<br>CAACAGAGTTACAGTACTCC<br>CTTATTCACT |
| | | AA | SEQ ID NO:807<br>RASQNIISYLN | SEQ ID NO:8819<br>GASSLQS | SEQ ID NO:16831<br>QQSYSTPLFT |
| iPS:393864 | 21-225_4C5 | NA | SEQ ID NO:808<br>CGGGCAAGTCGGGGCATCA<br>GAGGTGATTTAGGT | SEQ ID NO:8820<br>GCTGCATCCAATTGCAA<br>AGT | SEQ ID NO:16832<br>CTACAGCATTATAGTTACCC<br>TCGGACG |
| | | AA | SEQ ID NO:809<br>RASRGIRGDLG | SEQ ID NO:8821<br>AASNLQS | SEQ ID NO:16833<br>LQHYSYPRT |
| iPS:393866 | 21-225_14E3 | NA | SEQ ID NO:810<br>CGGGCAAGTCAGGGCATTAG<br>AAATGATTTAGGC | SEQ ID NO:8822<br>TCTGCATCCAGTTTGCAA<br>AGT | SEQ ID NO:16834<br>GTACAGCATTATAGTTACCC<br>GTTCACT |
| | | AA | SEQ ID NO:811<br>RASQGIRNDLG | SEQ ID NO:8823<br>SASSLQS | SEQ ID NO:16835<br>VQHYSYPFT |
| iPS:393868 | 21-225_9C11 | NA | SEQ ID NO:812<br>CGGGCAAGTCAGAACATTAG<br>AAATTATTTAAAT | SEQ ID NO:8824<br>GTTGCATCCAGTTTGCAA<br>AGT | SEQ ID NO:16836<br>CATCAGAGTAACAGTACTCC<br>TCTCACG |
| | | AA | SEQ ID NO:813<br>RASQNIRNYLN | SEQ ID NO:8825<br>VASSLQS | SEQ ID NO:16837<br>HQSNSTPLT |

FIGURE 49
(Continued)

| | | | | | | | |
|---|---|---|---|---|---|---|---|
| iPS:393870 | 21-225_7B1 | NA | SEQ ID NO:814 CGGGCGAAGTCAGGACATTAG CAATCATTTAGTC | SEQ ID NO:8826 GCTGCATCCAGTTTACAA AGT | SEQ ID NO:16838 CACCAGTATAATAGTTACCC CTTCACT |
| | | AA | SEQ ID NO:815 RASQDISNHLV | SEQ ID NO:8827 AASSLQS | SEQ ID NO:16839 HQYNSYPFT |
| iPS:393872 | 21-225_2A11 | NA | SEQ ID NO:816 CGGGCAAGTCAGGGCATTAG AAATGATTTAGGC | SEQ ID NO:8828 GCTGCATCCAGTTTGCAA AGT | SEQ ID NO:16840 CTACAGCATAATAGTTACCC GCTCACT |
| | | AA | SEQ ID NO:817 RASQGIRNDLG | SEQ ID NO:8829 AASSLQS | SEQ ID NO:16841 LQHNSYPLT |
| iPS:393874 | 21-225_4C8 | NA | SEQ ID NO:818 CGGGCAAGTCAGGGCATTAG AAATGATTTAGGC | SEQ ID NO:8830 GCTGCATCCAGTTTGCAA AGT | SEQ ID NO:16842 CTACAGCATAATAGTTACCC GCTCACT |
| | | AA | SEQ ID NO:819 RASQGIRNDLG | SEQ ID NO:8831 AASSLQS | SEQ ID NO:16843 LQHNSYPLT |
| iPS:393876 | 21-225_9A1 | NA | SEQ ID NO:820 CGGGCAAGTCAGGGCATTAG AAATGATTTAGGG | SEQ ID NO:8832 ACTGCATCCAGTTTGCAA AGT | SEQ ID NO:16844 ATACAGCATAATAGTTACCT GTGGACG |
| | | AA | SEQ ID NO:821 RASQGIRNDLG | SEQ ID NO:8833 TASSLQS | SEQ ID NO:16845 IQHNSYLWT |
| iPS:393878 | 21-225_7G12 | NA | SEQ ID NO:822 CGGGCAAGTCAGAATATTAA CAACTATTTAAAT | SEQ ID NO:8834 ACTGCATCCAGTTTGCAA AGT | SEQ ID NO:16846 CAACAGAGTTACACTACCCC CACGTGGACG |
| | | AA | SEQ ID NO:823 RASQNINNYLN | SEQ ID NO:8835 TASSLQS | SEQ ID NO:16847 QQSYTTPTWT |
| iPS:393880 | 21-225_15A1 | NA | SEQ ID NO:824 CGGGCAAGTCAGGGCATTAG AAATGATTTAGGC | SEQ ID NO:8836 GCTGCATCCAGTTTACAA AGT | SEQ ID NO:16848 CTACACAACAGTAGTTACC TGTTAAG |
| | | AA | SEQ ID NO:825 RASQGIRNDLG | SEQ ID NO:8837 AASSLQS | SEQ ID NO:16849 LHNSSYPVK |

FIGURE 49
(Continued)

| | | | | | |
|---|---|---|---|---|---|
| iPS:393882 | 21-225_15E3 | NA | SEQ ID NO:826 CGGGCAAGTCAGGGCATTAG AAATGATTTAGGC | SEQ ID NO:8838 GCTGCATCCAGTTTGCA AAGT | SEQ ID NO:16850 CTACAGCATCATAGTTACCC GCTCACT |
| | | AA | SEQ ID NO:827 RASQGIRNDLG | SEQ ID NO:8839 AASSSQS | SEQ ID NO:16851 LQHHSYPLT |
| iPS:393884 | 21-225_16F4 | NA | SEQ ID NO:828 CGGGCAAGTCAGGGCATTAG AAATGATTTAGGC | SEQ ID NO:8840 GTTGCATCCAGTTTGCAA AGT | SEQ ID NO:16852 ATACAGCATAATAGTTATCC GTTCACT |
| | | AA | SEQ ID NO:829 RASQGIRNDLG | SEQ ID NO:8841 VASSLQS | SEQ ID NO:16853 IQHNSYPFT |
| iPS:393886 | 21-225_2G9 | NA | SEQ ID NO:830 CGGGCAAGTCAGGGCATTAG AAATGATTTAGGT | SEQ ID NO:8842 GCTGCATCCAGTTTGCA AGT | SEQ ID NO:16854 TTACAGCATGAAAAGTTACCC TCTCACT |
| | | AA | SEQ ID NO:831 RASQGIRNDLG | SEQ ID NO:8843 AASSLQS | SEQ ID NO:16855 LQHESYPLT |
| iPS:393888 | 21-225_3E3 | NA | SEQ ID NO:832 CGGGCAAGTCAGAGAGCATTAG AAGTTATTTAAAT | SEQ ID NO:8844 GGTACATCCAGTTTGCA AAGT | SEQ ID NO:16856 CAACAGAGTTACAGTACCCC CTTGTTCACT |
| | | AA | SEQ ID NO:833 RASQSIRSYLN | SEQ ID NO:8845 GTSSLQS | SEQ ID NO:16857 QQSYSTPLFT |
| iPS:393890 | 21-225_4B1 | NA | SEQ ID NO:834 CGGGCAAGTCAGAGCATTACCATTAG AACCTATTTAAAC | SEQ ID NO:8846 GCTGCATCCAGTTTGCAA AGT | SEQ ID NO:16858 CAACAGAGTTACAATATCTC ATTCACT |
| | | AA | SEQ ID NO:835 RASHTIRTYLN | SEQ ID NO:8847 AASSLQS | SEQ ID NO:16859 QQSYNISFT |
| iPS:393892 | 21-225_6G7 | NA | SEQ ID NO:836 CAGGCGAGTCAGGACATTAG CAACTATTTAAAT | SEQ ID NO:8848 GATGCATCCACTTTGGA AACA | SEQ ID NO:16860 CAACAGTATGATAATGTCCC GATCACC |
| | | AA | SEQ ID NO:837 QASQDISNYLN | SEQ ID NO:8849 DASTLET | SEQ ID NO:16861 QQYDNVPIT |

FIGURE 49
(Continued)

| | | | | | | | |
|---|---|---|---|---|---|---|---|
| iPS:393894 | 21-225_5E11 | NA | SEQ ID NO:838<br>CGGGCGAGTCAGGGCATTAG<br>CAATTATTTAGCC | SEQ ID NO:8850<br>GCTGCATCCAGTGTGCA<br>GAGT | SEQ ID NO:16862<br>CACCAGTATCACAGTTACCC<br>ATTCACT | | |
| | | AA | SEQ ID NO:839<br>RASQGISNYLA | SEQ ID NO:8851<br>AASSVQS | SEQ ID NO:16863<br>HQYHSYPFT | | |
| iPS:393896 | 21-225_2A4 | NA | SEQ ID NO:840<br>CGGGCGAGTCAGGGCATTAG<br>CAATTATTTAGCC | SEQ ID NO:8852<br>ACTGCATCCAGTTTGCAA<br>AGT | SEQ ID NO:16864<br>CAACAGTATATAGTTACCC<br>ATTCACT | | |
| | | AA | SEQ ID NO:841<br>RASQGISNYLA | SEQ ID NO:8853<br>TASSLQS | SEQ ID NO:16865<br>QQYNSYPFT | | |
| iPS:393898 | 21-225_5F7 | NA | SEQ ID NO:842<br>CGGGCAAGTCAGAGACCATTAG<br>TAGTTATTTAAAT | SEQ ID NO:8854<br>GCTGCATCCAGTTTGCAA<br>AGT | SEQ ID NO:16866<br>CAACAGTTACAATACCCC<br>CTTATTCACT | | |
| | | AA | SEQ ID NO:843<br>RASQTISSYLN | SEQ ID NO:8855<br>AASSLQS | SEQ ID NO:16867<br>QQSYNTPLFT | | |
| iPS:393900 | 21-225_10E12 | NA | SEQ ID NO:844<br>CGGGCAAGTCAGAACATTTA<br>CAGTTATTTAAAT | SEQ ID NO:8856<br>GCTACATCCAGTTTGCAA<br>AGT | SEQ ID NO:16868<br>CAACAGAATTACAGTCCCC<br>TCTCACT | | |
| | | AA | SEQ ID NO:845<br>RASQNIYSYLN | SEQ ID NO:8857<br>ATSSLQS | SEQ ID NO:16869<br>QQNYSPPLT | | |
| iPS:393902 | 21-225_14E10 | NA | SEQ ID NO:846<br>CGGGCAAGTCAGGGCATTAG<br>AAATGATTTAGGC | SEQ ID NO:8858<br>GCTGCATCCAGTTACAA<br>AGT | SEQ ID NO:16870<br>CTGCAGCATTATAGTTACC<br>TCGGACG | | |
| | | AA | SEQ ID NO:847<br>RTSQGIRNDLG | SEQ ID NO:8859<br>AASSLQS | SEQ ID NO:16871<br>LQHYSYPRT | | |
| iPS:393904 | 21-225_8H11 | NA | SEQ ID NO:848<br>CGGGCAAGTCAGAACATTAT<br>CAGCTATTTAAAT | SEQ ID NO:8860<br>GTTACATCCAGTTTGCAC<br>AGT | SEQ ID NO:16872<br>CAACAGAGTTACAGTACCCCC<br>TTTCACT | | |
| | | AA | SEQ ID NO:849<br>RASQNIISYLN | SEQ ID NO:8861<br>VTSSLHS | SEQ ID NO:16873<br>QQSYSTPFT | | |

FIGURE 49
(Continued)

| | | | | | |
|---|---|---|---|---|---|
| iPS:393906 | | SEQ ID NO:850 AGGGCCAGTCAGGGACTGTTAG CAGCAACTTAGCC | SEQ ID NO:8862 GGTGCATCCACCAGGGC CACT | SEQ ID NO:16874 CAGCAGTATCACAGACTGGCC TCCGACG | |
| | 21-225_13D3 | NA | SEQ ID NO:851 RASQTVSSNLA | SEQ ID NO:8863 GASTRAT | SEQ ID NO:16875 QQYHDWPPT |
| | | AA | SEQ ID NO:852 | SEQ ID NO:8864 | SEQ ID NO:16876 |
| iPS:393908 | | NA | CGGGCAAGTCAGGACATTAG AAGTGATTTAGGC | GCTGCATCCAGTTGCAA AGT | CTACAGCAGTATTATAGTTACC TCGGACG |
| | 21-225_10E9 | | SEQ ID NO:853 RASQDIRSDLG | SEQ ID NO:8865 AASSLQS | SEQ ID NO:16877 LQHYSYPRT |
| | | AA | SEQ ID NO:854 | SEQ ID NO:8866 | SEQ ID NO:16878 |
| iPS:393910 | | NA | CAGGCGAATCAGGGACATTAC CAACTTTTAAAT | GATGCATCCAATTGGA AACA | CAACAGTATGATAATCTCCC GATCACC |
| | 21-225_15F10 | | SEQ ID NO:855 QANQDITNFLN | SEQ ID NO:8867 DASNLET | SEQ ID NO:16879 QQYDNLPIT |
| | | AA | SEQ ID NO:856 | SEQ ID NO:8868 | SEQ ID NO:16880 |
| iPS:393912 | | NA | CAGGCGAATCAGGGACATTAC CAACTTTTAAAT | GATGCATCCAATTGGA AACA | CAACAGTATGATAATCTCCC GATCACC |
| | 21-225_16F6 | | SEQ ID NO:857 QANQDITNFLN | SEQ ID NO:8869 DASNLET | SEQ ID NO:16881 QQYDNLPIT |
| | | AA | SEQ ID NO:858 | SEQ ID NO:8870 | SEQ ID NO:16882 |
| iPS:393914 | | NA | CGGGCGAGTCAGGGCATTAA CAATTATTAGCC | GCTGCATCCAGTGTGCA GAGT | CACCAGTATCACAGTTACC ATTCACT |
| | 21-225_16B8 | | SEQ ID NO:859 RASQGINNYLA | SEQ ID NO:8871 AASSVQS | SEQ ID NO:16883 HQYHSYPFT |
| | | AA | SEQ ID NO:860 | SEQ ID NO:8872 | SEQ ID NO:16884 |
| iPS:393916 | | NA | CGGGCAAGTCAGGGCATTAG AAATGATTTAGGC | GCTGCATCCAGTTTGCAC AGT | CTACAACAGTATTATAGTTCCCT CGGACG |
| | 21-225_2G4 | | SEQ ID NO:861 RASQGIRNDLG | SEQ ID NO:8873 AASSLHS | SEQ ID NO:16885 LQHYSFPRT |
| | | AA | | | |

FIGURE 49
(Continued)

| | | | | | | |
|---|---|---|---|---|---|---|
| iPS:393920 | | NA | SEQ ID NO:862 CGGGCAAGTCAGAACATTA CAGGTATTTAAAT | SEQ ID NO:8874 ACTGCATCCAGTTTACAA AGT | SEQ ID NO:16886 CAACAGAGTTACAGTCCCCC TCTCACT |
| | 21-225_1H12 | AA | SEQ ID NO:863 RASQNIYRYLN | SEQ ID NO:8875 TASSLQS | SEQ ID NO:16887 QQSYSPPLT |
| iPS:393922 | | NA | SEQ ID NO:864 CGGGCAAGTCAGGGCATTAG AAATGATTTAGGC | SEQ ID NO:8876 GCTGCATCCAGTTTACAA AGT | SEQ ID NO:16888 CTACAGCATAATAGTTACCC GCTCACT |
| | 21-225_2B2 | AA | SEQ ID NO:865 RASQGIRNDLG | SEQ ID NO:8877 AASSLQS | SEQ ID NO:16889 LQHNSYPLT |
| iPS:393926 | | NA | SEQ ID NO:866 CGGGCAAGTCAGAGACCATTAT CAGCTATTTAAAT | SEQ ID NO:8878 ACTGCATCCAGTTTGCAA AGT | SEQ ID NO:16890 CAACAGACTTACAGTACTCC GCTCACT |
| | 21-225_4G4 | AA | SEQ ID NO:867 RASQTIISYLN | SEQ ID NO:8879 TASSLQS | SEQ ID NO:16891 QQTYSTPLT |
| iPS:393928 | | NA | SEQ ID NO:868 CGGGCAAGTCAGGGCATTAG AAATGATTTAGGC | SEQ ID NO:8880 GCTGCATCCAGTTTGCAA AGT | SEQ ID NO:16892 TTACAGCATGATAATTACCC TCTCACT |
| | 21-225_4E10 | AA | SEQ ID NO:869 RASQGIRNDLG | SEQ ID NO:8881 AASSLQS | SEQ ID NO:16893 LQHDNYPLT |
| iPS:393930 | | NA | SEQ ID NO:870 CGGGCAAGTCAAAACATTAT CAGCTATTTAAAT | SEQ ID NO:8882 ACTGCATCCAGTTTGCAA AGT | SEQ ID NO:16894 CAACAGACTTACAGTACCCC GCTCACT |
| | 21-225_7E11 | AA | SEQ ID NO:871 RASQNIISYLN | SEQ ID NO:8883 TASSLQS | SEQ ID NO:16895 QQTYSTPLT |
| iPS:393932 | | NA | SEQ ID NO:872 CGGGCAAGTCAGAACATTA CAGGTATTTAAAT | SEQ ID NO:8884 ACTGCATCCAGTTTGCAA AGT | SEQ ID NO:16896 CAACAGAGTTACAGTCCCCC TCTCACT |
| | 21-225_10F5 | AA | SEQ ID NO:873 RASQNIYRYLN | SEQ ID NO:8885 TASSLQS | SEQ ID NO:16897 QQSYSPPLT |

FIGURE 49
(Continued)

| | | | | | | |
|---|---|---|---|---|---|---|
| iPS:393934 | 21-225_13E6 | NA | SEQ ID NO:874 CGGGCAAGTCAGGGCATTAG AAATGATTTAGGC | SEQ ID NO:8886 GCTGCATCCAGTTTGCAA AGT | SEQ ID NO:16898 GTACAGCATAATAGTTACCC GCTCACT |
| | | AA | SEQ ID NO:875 RASQGIRNDLG | SEQ ID NO:8887 AASSLQS | SEQ ID NO:16899 VQHNSYPLT |
| iPS:393936 | 21-225_14A11 | NA | SEQ ID NO:876 CGGGCAAGTCAGAGCATTAG CAGTTATTTAAAT | SEQ ID NO:8888 GCTGCATCCAGTTTGCAA AAT | SEQ ID NO:16900 CAACAGACTTACAGTAGCC TCCATTCACT |
| | | AA | SEQ ID NO:877 RASQSISSYLN | SEQ ID NO:8889 AASSLQN | SEQ ID NO:16901 QQTYSSPPFT |
| iPS:393940 | 21-225_16B2 | NA | SEQ ID NO:878 CGGGCAAGTCAGAGCATTAG CGGCTATTTAAAT | SEQ ID NO:8890 GCTGCATCCAGTTTGCAA AGT | SEQ ID NO:16902 CAACAGACTTACAATACCC TCCGGAGCGCAGT |
| | | AA | SEQ ID NO:879 RASQSISGYLN | SEQ ID NO:8891 AASSLQS | SEQ ID NO:16903 QQTYNTPPERS |
| iPS:393942 | 21-225_11E5 | NA | SEQ ID NO:880 AAGTCCAGCCAGAGTGTTT ATACAGCTCCAACAATAACA ACTACTTAACT | SEQ ID NO:8892 TGGGCATCTACCCGGGA ATCC | SEQ ID NO:16904 CAGCAATATTATAGTACTCC TCCGACG |
| | | AA | SEQ ID NO:881 KSSQSVLYSSNNNNYLT | SEQ ID NO:8893 WASTRES | SEQ ID NO:16905 QQYYSTPPT |
| iPS:393944 | 21-225_14D6 | NA | SEQ ID NO:882 CGGGCAAGTCAGGACATTAG AAATCATTTAGGC | SEQ ID NO:8894 GCTGCATCCAGTTTGCAA AGT | SEQ ID NO:16906 CTACAGTATAATAGTTACCC ATTCACT |
| | | AA | SEQ ID NO:883 RASQDIRNHLG | SEQ ID NO:8895 AASSLQS | SEQ ID NO:16907 LQYNSYPFT |
| iPS:393946 | 21-225_16A4 | NA | SEQ ID NO:884 CGGGCGAGTCAGGACATTAG TAATTATTTAGCC | SEQ ID NO:8896 GCTGCATCCAGTTTGCAA AGT | SEQ ID NO:16908 CAACAGTATCATAGTTACCC GTGGACG |
| | | | SEQ ID NO:885 | SEQ ID NO:8897 | SEQ ID NO:16909 |

FIGURE 49
(Continued)

| | | AA | | | | | |
|---|---|---|---|---|---|---|---|
| iPS:393948 | 21-225_16A5 | AA | RASQDISNYLA SEQ ID NO:886 | | AASSLQS SEQ ID NO:8898 | | QQYHSYPWT SEQ ID NO:16910 |
| | | NA | CGGGCAAGTCAGGGCATTAG AAATGATTAGGC SEQ ID NO:887 | | GCTGCATCCAGTTTGCAA AGT SEQ ID NO:8899 | | CTACAGCATAATAGTTACCC GTGGACG SEQ ID NO:16911 |
| iPS:393950 | 21-225_3H10 | AA | RASQGIRNDLG SEQ ID NO:888 | | AASSLQS SEQ ID NO:8900 | | LQHNSYPWT SEQ ID NO:16912 |
| | | NA | TCTGGAGATAAATTGGGGGA AAAATATGCTTGC SEQ ID NO:889 | | CAAGATAGGAAGCGGCC CTCA SEQ ID NO:8901 | | CAGGCGTGGGTCAACAACAC TATGATA SEQ ID NO:16913 |
| iPS:393952 | 21-225_1F1 | AA | SGDKLGEKYAC SEQ ID NO:890 | | QDRKRPS SEQ ID NO:8902 | | QAWVNNTMI SEQ ID NO:16914 |
| | | NA | CGGGCGAGTCAGGGCATTAA CAATTATTAGCC SEQ ID NO:891 | | GTTGCATCCAGTTTGCAA ACT SEQ ID NO:8903 | | CAACAGTATAATAGTTACCC TCTCACT SEQ ID NO:16915 |
| iPS:393954 | 21-225_4H6 | AA | RASQGINNYLA SEQ ID NO:892 | | VASSLQT SEQ ID NO:8904 | | QQYNSYPLT SEQ ID NO:16916 |
| | | NA | CGGGCGAGTCAGGGTATTAG CAGGTGGTTAGCC SEQ ID NO:893 | | GGTGCATCCAGTTTGCA AAGT SEQ ID NO:8905 | | CAACAGGCTAACAGTTCCC ATTCACT SEQ ID NO:16917 |
| iPS:393956 | 21-225_4D7 | AA | RASQGISRWLA SEQ ID NO:894 | | GASSLQS SEQ ID NO:8906 | | QQANSFPFT SEQ ID NO:16918 |
| | | NA | CGGGCAAGTCAGAGCATTAG CGACTATTAAAT SEQ ID NO:895 | | GATACAACCAGTTTGCA AAGT SEQ ID NO:8907 | | CAACAGACTTACAATACCC TCCGGAGCGCAGT SEQ ID NO:16919 |
| iPS:393958 | 21-225_5H2 | AA | RASQSISDYLN SEQ ID NO:896 | | DTTSLQS SEQ ID NO:8908 | | QQFYNTPPERS SEQ ID NO:16920 |
| | | NA | CGGGCAAGTCAGGGCATTAG AAATGATTAGGC SEQ ID NO:897 | | GCTGCATCCAGTTTGCAA AGT SEQ ID NO:8909 | | CTACAGCATAATAGTTACCC TCTCACT SEQ ID NO:16921 |

FIGURE 49
(Continued)

| | | | | | | |
|---|---|---|---|---|---|---|
| iPS:393960 | 21-225_7G2 | AA | RASQGIRNDLG SEQ ID NO:898 | | AASSLQS SEQ ID NO:8910 | | LQHNSYPLT SEQ ID NO:16922 |
| | | NA | CGGGCAAGTCAGGGCATTAG AAATGATTTAGGC SEQ ID NO:899 | ACTGCATCCAGTTTGCAA AGT SEQ ID NO:8911 | CTACAACATAATAGTTACCC GTGGACG SEQ ID NO:16923 |
| iPS:393962 | 21-225_7H7 | AA | RASQGIRNDLG SEQ ID NO:900 | TASSLQS SEQ ID NO:8912 | LQHNSYPWT SEQ ID NO:16924 |
| | | NA | CGGGCAAGTCAGGGCATTAG AAATGATTTAGGC SEQ ID NO:901 | GCTGCATCCAGTTTGCAA AGT SEQ ID NO:8913 | CTACAGCATAGTAGTTACCC GTTCACT SEQ ID NO:16925 |
| iPS:393964 | 21-225_6G1 | AA | RASQGIRNDLG SEQ ID NO:902 | AASSLQS SEQ ID NO:8914 | LQHSSYPFT SEQ ID NO:16926 |
| | | NA | CGGACAAGTCAGAACATTAT CAGCTATTTAAAT SEQ ID NO:903 | ACTGCATCCAATTTGCAA ACT SEQ ID NO:8915 | CAACAGCCTCACAGTCCCCC GCTCACT SEQ ID NO:16927 |
| iPS:393966 | 21-225_7F8 | AA | RTSQNIISYLN SEQ ID NO:904 | TASNLQT SEQ ID NO:8916 | QQPHSPPLT SEQ ID NO:16928 |
| | | NA | CGGGCAAGTCAGGGCATTGG AAATGATTTAGGC SEQ ID NO:905 | GCTGCATCCAGTTTGCAA AGT SEQ ID NO:8917 | CTACAACATTATACTTACCC TCGGACG SEQ ID NO:16929 |
| iPS:393968 | 21-225_5A5 | AA | RASQGIGNDLG SEQ ID NO:906 | AASSLQS SEQ ID NO:8918 | LQHYTYPRT SEQ ID NO:16930 |
| | | NA | CGGGCGAGTCAGGGCATTAG CAATTATTTAGGC SEQ ID NO:907 | GCTGCATCCAGTTTGCAA AGT SEQ ID NO:8919 | CAACAGTATAATAGTTACCC ATTCACT SEQ ID NO:16931 |
| iPS:393972 | 21-225_7C9 | AA | RASQGISNYLA SEQ ID NO:908 | AASSLQS SEQ ID NO:8920 | QQYNSYPFT SEQ ID NO:16932 |
| | | NA | CGGGCAAGTCAGGGCATTAG AAACGATTTAGGC SEQ ID NO:909 | GCTGCATCCAGTTTGCAA AGT SEQ ID NO:8921 | CTACAGTTTATAGTTACCCT CGGACG SEQ ID NO:16933 |

FIGURE 49
(Continued)

| | | | | | | |
|---|---|---|---|---|---|---|
| iPS:393974 | 21-225_7C4 | AA | RASQGIRNDLG SEQ ID NO:910 | AASSLQS SEQ ID NO:8922 | LQLYSYPRT SEQ ID NO:16934 |
| | | NA | CGGGCAAGTCAGGGCATTAG AAATGATTAGGC SEQ ID NO:911 | GCTGCATCCAGTTTGCAA AGT SEQ ID NO:8923 | CTACAGGATAATAGTTACCC GCTCACT SEQ ID NO:16935 |
| iPS:393976 | 21-225_7E9 | AA | RASQGIRNDLG SEQ ID NO:912 | AASSLQS SEQ ID NO:8924 | LQHNSYPLT SEQ ID NO:16936 |
| | | NA | CGGGCAAGTCAGGGCATTAG AAATGATTAGGC SEQ ID NO:913 | ACTGCATCCAGTTTGCAA AGT SEQ ID NO:8925 | CTACAGCATAATAGTTACCC GCTCACT SEQ ID NO:16937 |
| iPS:393978 | 21-225_4C12 | AA | RASQGIRNDLG SEQ ID NO:914 | TASSLQS SEQ ID NO:8926 | LQHNSYPLT SEQ ID NO:16938 |
| | | NA | CGGGCAAGTCAGGGCATTAG AAATGATTAGGC SEQ ID NO:915 | GCTGCATCCAGTTTGCAC AGT SEQ ID NO:8927 | CTACAACATTATAGTTTCCCT CGGACG SEQ ID NO:16939 |
| iPS:393980 | 21-225_6D3 | AA | RASQGIRNDLG SEQ ID NO:916 | AASSLHS SEQ ID NO:8928 | LQHYSFPRT SEQ ID NO:16940 |
| | | NA | CGGACAAGTCAGAGCATTAG TACTTATTAAAT SEQ ID NO:917 | GCTGCATCCAGTTTGCAA AGT SEQ ID NO:8929 | CAACAGAGTTACAGAACCCC CTTTTTCACT SEQ ID NO:16941 |
| iPS:393982 | 21-225_6C12 | AA | RTSQSISTYLN SEQ ID NO:918 | AASSLQS SEQ ID NO:8930 | QQSYRTPFFT SEQ ID NO:16942 |
| | | NA | CGGGCAAGTCAGGGCATTAG AAGTAATTAGGC SEQ ID NO:919 | GCTGCATCCAGTTTGGA AAGT SEQ ID NO:8931 | CTACAGGATAATAGTTATCC GTTCACT SEQ ID NO:16943 |
| iPS:393984 | 21-225_4F12 | AA | RASQGIRSNLG SEQ ID NO:920 | AASSLES SEQ ID NO:8932 | LQDNSYPFT SEQ ID NO:16944 |
| | | NA | CGGGCAAGTCAGGGCATTAG AAATGATTAGGC SEQ ID NO:921 | GCTGCATCCAGTTTGCAA AGT SEQ ID NO:8933 | CTACAGCATAATAGTTACGC GCTCACT SEQ ID NO:16945 |

FIGURE 49
(Continued)

| | | | | | | |
|---|---|---|---|---|---|---|
| iPS:393986 | 21-225_7G4 | AA | RASQGIRNDLG SEQ ID NO:922 | | AASSLQS SEQ ID NO:8934 | | LQHNSYALT SEQ ID NO:16946 |
| | | NA | CGGGCAAGTCAGGGCATTAG AAATGATTAGGC SEQ ID NO:923 | GCTGCATCCAGTTTGCAA AGT SEQ ID NO:8935 | CTACATCAATATAGTTACCC TCGGACG SEQ ID NO:16947 |
| iPS:393988 | 21-225_7F10 | AA | RASQGIRNDLG SEQ ID NO:924 | AASSLQS SEQ ID NO:8936 | LHQYSYPRT SEQ ID NO:16948 |
| | | NA | CGGGCGAGTCAGGACATTAG GAATTATTAGCC SEQ ID NO:925 | GTTGCATCCAGTTTGCAA AGT SEQ ID NO:8937 | CAACAGTATAATAGTTACCC TCTCACT SEQ ID NO:16949 |
| iPS:393990 | 21-225_11G7 | AA | RASQDIRNYLA SEQ ID NO:926 | VASSLQS SEQ ID NO:8938 | QQYNSYPLT SEQ ID NO:16950 |
| | | NA | CGGGCAAGTCAGGGCATTAG AAATGATTAGGC SEQ ID NO:927 | GCTGCATCCAGTTTGCAA AGT SEQ ID NO:8939 | CTACAGTATAATAGTTACCC TCTCACT SEQ ID NO:16951 |
| iPS:393992 | 21-225_14H8 | AA | RASQGIRNDLG SEQ ID NO:928 | AASSLQS SEQ ID NO:8940 | LQHSNYPLT SEQ ID NO:16952 |
| | | NA | CGGGCGAGTCAGGGCATTAG CTATTATTAGCC SEQ ID NO:929 | GTTGCATCCAGTTTGCAA AGT SEQ ID NO:8941 | CAACAGTATAATAGTTACCC ATTCACT SEQ ID NO:16953 |
| iPS:393994 | 21-225_8C9 | AA | RASQGISYYLA SEQ ID NO:930 | VASSLQS SEQ ID NO:8942 | QQYNSYPFT SEQ ID NO:16954 |
| | | NA | CGGGCAAGTCAGGGCATTAG AAATGATTAGAC SEQ ID NO:931 | GCTGCATCCAGTTTGCAA AGT SEQ ID NO:8943 | CTACAGCATATAGTTATCC GCTCACT SEQ ID NO:16955 |
| iPS:393996 | 21-225_15C11 | AA | RASQAIRNDLD SEQ ID NO:932 | AASSLQS SEQ ID NO:8944 | LQHNSYPLT SEQ ID NO:16956 |
| | | NA | CGGGCAAGTCAGGGCATTAG AAATGATTAGGC SEQ ID NO:933 | GCTGCATCCAGTTTGCAA AGT SEQ ID NO:8945 | CTACTGCATTATAGTTACCCT CGGACG SEQ ID NO:16957 |

FIGURE 49
(Continued)

| | | | | RASQGIRNDLG | | AASSLQS | | LLHYSYPRT | |
|---|---|---|---|---|---|---|---|---|---|
| | | | AA | SEQ ID NO:934 | | SEQ ID NO:8946 | | SEQ ID NO:16958 | |
| iPS:393998 | | 21-225_12B12 | NA | CGGGCAAGTCAGGGCATTAG AAATGATTAGGC | SEQ ID NO:935 | ACTGCATCCAGTTTGCAA AGT | SEQ ID NO:8947 | CTACAACATAATAGTTACCC GTGGACG | SEQ ID NO:16959 |
| iPS:394000 | | 21-225_11A2 | AA | RASQGIRNDLG | SEQ ID NO:936 | TASSLQS | SEQ ID NO:8948 | LQHNSYPWT | SEQ ID NO:16960 |
| | | | NA | CAGGCGAGTCAGGACATTAG CAACTATTAAAT | SEQ ID NO:937 | GATGCATCCAATTTGGA AACA | SEQ ID NO:8949 | CAACAGTATGATAATCTCCC GATCACC | SEQ ID NO:16961 |
| iPS:394002 | | 21-225_15G7 | AA | QASQDISNYLN | SEQ ID NO:938 | DASNLET | SEQ ID NO:8950 | QQYDNLPIT | SEQ ID NO:16962 |
| | | | NA | CGGGCAAGTCAGGGCATTAG AAATGATTAGGC | SEQ ID NO:939 | GCTGCATCCAGTTTGCAA AGT | SEQ ID NO:8951 | CTACAGCATAGTAATTACCC TCTCACT | SEQ ID NO:16963 |
| iPS:394004 | | 21-225_13A1 | AA | RASQGIRNDLG | SEQ ID NO:940 | AASSLQS | SEQ ID NO:8952 | LQHSNYPLT | SEQ ID NO:16964 |
| | | | NA | CAGGCGAGTCAGGACATTAA CAACTATTAAAT | SEQ ID NO:941 | GATGCATCCAATTTGGA AACA | SEQ ID NO:8953 | CAACAGTATGATGAAAATCTCCC GATCACT | SEQ ID NO:16965 |
| iPS:394006 | | 21-225_15C2 | AA | QASQDITNYLN | SEQ ID NO:942 | DGSNLET | SEQ ID NO:8954 | QQYENLPIT | SEQ ID NO:16966 |
| | | | NA | CAGGCGAGTCAGGACATTAC CAACTATTAAAT | SEQ ID NO:943 | GATGCATCCAATTTGGA AACA | SEQ ID NO:8955 | CAACAGTATGATAATCTCCC GATCACC | SEQ ID NO:16967 |
| iPS:394008 | | 21-225_15H8 | AA | QASQDITNYLN | SEQ ID NO:944 | DASNLET | SEQ ID NO:8956 | QQYDNLPIT | SEQ ID NO:16968 |
| | | | NA | CGGGCAAGTCAGGGCATTAG AAATGATTAGGC | SEQ ID NO:945 | GCTGCATCCAGTTTGCAA AGT | SEQ ID NO:8957 | CTACAGCATAATAGTTACCC GCTCACT | SEQ ID NO:16969 |

FIGURE 49
(Continued)

| | | | AA/NA | | | | | |
|---|---|---|---|---|---|---|---|---|
| iPS:394010 | 21-225_12G5 | | AA | RASQGIRNDLG SEQ ID NO:946 | | AASSLQS SEQ ID NO:8958 | | LQHNSYPLT SEQ ID NO:16970 |
| | | | NA | CGGGCGAGTCAGGGACATTAG CAATTATTAGCC SEQ ID NO:947 | | GCTGCATACACATTTTGCAA TCA SEQ ID NO:8959 | | CAAAAGTATGACAGTGCCCC ATTCACT SEQ ID NO:16971 |
| iPS:394012 | 21-225_15A3 | | AA | RASQDISNYLA SEQ ID NO:948 | | AAYILQS SEQ ID NO:8960 | | QKYDSAPFT SEQ ID NO:16972 |
| | | | NA | CGGGCAAGTCAGAGCATTAT CAGCTATTTAAAT SEQ ID NO:949 | | ACTGCATCCAGTTTGCAA AGT SEQ ID NO:8961 | | CAACAGACTTACAGTACCCC GCTCACT SEQ ID NO:16973 |
| iPS:394014 | 21-225_8G6 | | AA | RASQSISYLN SEQ ID NO:950 | | TASSLQS SEQ ID NO:8962 | | QQTYSTPLT SEQ ID NO:16974 |
| | | | NA | CGGGCAAGTCAGAGCATTAG TAGTTATTTAAAT SEQ ID NO:951 | | GCTGCATCCAGTTTGCAA AGT SEQ ID NO:8963 | | CAACAGAGTTACAGAACCCC CTTTTTCACT SEQ ID NO:16975 |
| iPS:394016 | 21-225_13D4 | | AA | RASQSIFSYLN SEQ ID NO:952 | | AASSLQS SEQ ID NO:8964 | | QQSYRTPFFT SEQ ID NO:16976 |
| | | | NA | CGGGCAAGTCAGAGCATTTT CAGCTACTTAAAT SEQ ID NO:953 | | ACTGCATCCAGTTTGCAA AAT SEQ ID NO:8965 | | CAACAGACTTACAGTCTTCC GCTCACT SEQ ID NO:16977 |
| iPS:394018 | 21-225_15B1 | | AA | RASQSIFSYLN SEQ ID NO:954 | | TASSLQN SEQ ID NO:8966 | | QQTYSLPLT SEQ ID NO:16978 |
| | | | NA | CGGGCGAGTCAGGGCATTAG CAATTATTAGCC SEQ ID NO:955 | | GCTGCATCCAGTTTGCAA AGT SEQ ID NO:8967 | | CAACAGTATCATAGTTACC ATTCACT SEQ ID NO:16979 |
| iPS:394020 | 21-225_15H10 | | AA | RASQGISNYLA SEQ ID NO:956 | | AASSLQS SEQ ID NO:8968 | | QQYHSYPFT SEQ ID NO:16980 |
| | | | NA | CGGGCAAGTCAGGGCATTAG AAATGATTTAGGC SEQ ID NO:957 | | GCTGCATCCAGTTTGCAA AGT SEQ ID NO:8969 | | CTACAGCATAATAGTTACCC GCTCACT SEQ ID NO:16981 |

FIGURE 49
(Continued)

| | | | | | | |
|---|---|---|---|---|---|---|
| iPS:394022 | 21-225_16H6 | AA | RASQGIRNDLG<br>SEQ ID NO:958 | CGGGCAAGTCAGGAACATTAG<br>CAGTATTAAAT<br>SEQ ID NO:959 | AASSLQS<br>SEQ ID NO:8970 | GCTGCATCCAGTTTGCAA<br>AGT<br>SEQ ID NO:8971 | LQHNSYPLT<br>SEQ ID NO:16982 | CAACAGAGTTACAGAACCCC<br>CTTATTCACT<br>SEQ ID NO:16983 |
| iPS:394024 | 21-225_16B7 | NA | RASQNISSYLN<br>SEQ ID NO:960 | | AASSLQS<br>SEQ ID NO:8972 | | QQSYRTPLFT<br>SEQ ID NO:16984 | |
| iPS:394026 | 21-225_16C7 | AA | RASQGIRNDLG<br>SEQ ID NO:961 | CGGGCAAGTCAGGGCATTAG<br>AAATGATTAGGC<br>SEQ ID NO:962 | AASSLQS<br>SEQ ID NO:8973 | GCTGCATCCAGTTTGCAA<br>AGT<br>SEQ ID NO:8974 | LQHNSYPLT<br>SEQ ID NO:16985 | CTACAGCATAATAGTTACC<br>GCTCACT<br>SEQ ID NO:16986 |
| iPS:394029 | 21-225_1B12 | NA | RASQGISNYLA<br>SEQ ID NO:963 | CGGGCGAGTCAGGGCATTAG<br>CAATTATTAGCC<br>SEQ ID NO:964 | AASSLQS<br>SEQ ID NO:8975 | GCTGCATCCAGTTTGCAA<br>AGT<br>SEQ ID NO:8976 | QQYNSYPFT<br>SEQ ID NO:16987 | CAACAGTATAATAGTTACC<br>ATTCACT<br>SEQ ID NO:16988 |
| iPS:394033 | 21-225_5F4 | AA | QASQDINNYLN<br>SEQ ID NO:965 | CAGGCGAGTCAGGACATTAA<br>CAACTATTAAAT<br>SEQ ID NO:966 | DASNLET<br>SEQ ID NO:8977 | GATGCATCCAATTGGA<br>AACA<br>SEQ ID NO:8978 | QQYENLPIT<br>SEQ ID NO:16989 | CAACAGTATGAAAATCTCCC<br>GATCACC<br>SEQ ID NO:16990 |
| iPS:394035 | 21-225_5G9 | NA | RASQGIRNHLG<br>SEQ ID NO:967 | CGGGCAAGTCAGGGCATTCG<br>AAATCATTAGGC<br>SEQ ID NO:968 | AASSLQS<br>SEQ ID NO:8979 | GCTGCCTCCAGTTTGCAA<br>AGT<br>SEQ ID NO:8980 | LQYNGYPFT<br>SEQ ID NO:16991 | CTACAGTATAATGGTTACC<br>ATTCACT<br>SEQ ID NO:16992 |
| | | AA | QASQDINNYLN<br>SEQ ID NO:969 | CAGGCGAGTCAGGGCATTAG<br>CAACTCTTTAAAT<br>SEQ ID NO:969 | DASNLET<br>SEQ ID NO:8981 | GATGCATCCAATTGGA<br>AACA<br>SEQ ID NO:8981 | | CAACAATATGATAATCTCCC<br>GCTCACT<br>SEQ ID NO:16993 |

FIGURE 49
(Continued)

| | | | | | | |
|---|---|---|---|---|---|---|
| iPS:394037 | 21-225_4F4 | AA | QASQGISNSLN SEQ ID NO:970 | DASNLET SEQ ID NO:8982 | QQYDNLPLT SEQ ID NO:16994 |
| | | NA | CGGGCAAGTCAGGGCATTAG AAATGATTAGGC SEQ ID NO:971 | GCTGCGTCCAGTGTGCA AACT SEQ ID NO:8983 | CTACAGCATAATAGTTACCC GCTCACT SEQ ID NO:16995 |
| iPS:394041 | 21-225_5E5 | AA | RASQGIRNDLG SEQ ID NO:972 | AASSVQT SEQ ID NO:8984 | LQHNSYPLT SEQ ID NO:16996 |
| | | NA | CGGGCAAGTCAGGGCATTAG AAATGATTAGGC SEQ ID NO:973 | GCTGCATCCAGTTGCAA AGT SEQ ID NO:8985 | CTACAGCATTATAGTTACCC TCGGACG SEQ ID NO:16997 |
| iPS:394043 | 21-225_3B1 | AA | RASQGIRNDLG SEQ ID NO:974 | AASSLQS SEQ ID NO:8986 | LQHYSYPRT SEQ ID NO:16998 |
| | | NA | CGGGCAAGTCAGAGTATTAA TAATTATTAAAT SEQ ID NO:975 | GCTACATCCAGTTGCAA AAT SEQ ID NO:8987 | CAACAGAGTTACAGTACCC CTTATTCACT SEQ ID NO:16999 |
| iPS:394045 | 21-225_4H4 | AA | RASQSINNYLN SEQ ID NO:976 | ATSSLQN SEQ ID NO:8988 | QQSYSTPLFT SEQ ID NO:17000 |
| | | NA | CGGGCAAGTCAGGGCATTAG AAATGATTAGGC SEQ ID NO:977 | GCTGCATCCAGTGTGCA AAGT SEQ ID NO:8989 | CTACAGCATAATAGTTACCC GCTCACT SEQ ID NO:17001 |
| iPS:394047 | 21-225_5E6 | AA | RASQGIRNDLG SEQ ID NO:978 | AASSVQS SEQ ID NO:8990 | LQHNSYPLT SEQ ID NO:17002 |
| | | NA | CAGGCGAGTCAGGACATTAA CAACTATTAAAT SEQ ID NO:979 | GATGCATCCAATTGGA AACA SEQ ID NO:8991 | CAACAGTATGATAATCTCCC GATCACC SEQ ID NO:17003 |
| iPS:394049 | 21-225_13H5 | AA | QASQDINNYLN SEQ ID NO:980 | DASNLET SEQ ID NO:8992 | QQYDNLPIT SEQ ID NO:17004 |
| | | NA | CGGGCAAGTCAGGGCATTAG AAATGATTAGGC SEQ ID NO:981 | GCTGCATCCAGTTGCAA ACT SEQ ID NO:8993 | CTACAGCATAATAGTTACCC TCTCACT SEQ ID NO:17005 |

FIGURE 49 (Continued)

| | | | | | | |
|---|---|---|---|---|---|---|
| iPS:394051 | 21-225_9E5 | AA | RASQGIRNDLG<br>SEQ ID NO:982 | AASSLQT<br>SEQ ID NO:8994 | LQHNSYPLT<br>SEQ ID NO:17006 |
| | | NA | CGGGCAAGTCAGAGCATTGCCAGTTATTAAAT<br>SEQ ID NO:983 | GGTGCATCCAGTTTGCAAGT<br>SEQ ID NO:8995 | CAACAGAGTTACAGTACCCCTTATTCAGT<br>SEQ ID NO:17007 |
| iPS:394053 | 21-225_11F10 | AA | RASQSIASYLN<br>SEQ ID NO:984 | GASSLQS<br>SEQ ID NO:8996 | QQSYSTPLFS<br>SEQ ID NO:17008 |
| | | NA | CGGGCAAGTCAGGGCATTAGAAATGATTTAGGC<br>SEQ ID NO:985 | GCTGCATCCAGTTTACAAAGT<br>SEQ ID NO:8997 | CTACAGCATAGTAGTTACCCTCTCACT<br>SEQ ID NO:17009 |
| iPS:394055 | 21-225_9C8 | AA | RASQGIRNDLG<br>SEQ ID NO:986 | AASSLQS<br>SEQ ID NO:8998 | LQHSSYPLT<br>SEQ ID NO:17010 |
| | | NA | CGGGGAGTCAGGGCATTAGCTATTATTAGCC<br>SEQ ID NO:987 | GTTGCATCCAGTTTGCAAAGT<br>SEQ ID NO:8999 | CAACAGTATGATAGTTACCCATTCACT<br>SEQ ID NO:17011 |
| iPS:394057 | 21-225_15H1 | AA | RASQGISYYLA<br>SEQ ID NO:988 | VASSLQS<br>SEQ ID NO:9000 | QQYDSYPFT<br>SEQ ID NO:17012 |
| | | NA | CGGGCAAGTCAGGGCATTAGAAATGATTTAGGC<br>SEQ ID NO:989 | ACTGCATCCAGTTTGCAAAGT<br>SEQ ID NO:9001 | CTACAGCATAGTAGTTACCCGCTCACT<br>SEQ ID NO:17013 |
| iPS:394059 | 21-225_9E8 | AA | RASQGIRNDLG<br>SEQ ID NO:990 | TASSLQS<br>SEQ ID NO:9002 | LQHSSYPLT<br>SEQ ID NO:17014 |
| | | NA | CGGGCAAGTCAGGGCATTAGAAATGATTTAGGC<br>SEQ ID NO:991 | GCTGCATCCAGTTTGCAAAGT<br>SEQ ID NO:9003 | CTACAGCATAATAGTTACCCGCTCACT<br>SEQ ID NO:17015 |
| iPS:394061 | 21-225_12D2 | AA | RASQGIRNDLG<br>SEQ ID NO:992 | AASSLQS<br>SEQ ID NO:9004 | LQHNSYPLT<br>SEQ ID NO:17016 |
| | | NA | AGGTCTAGTCAGAGCCTCCTCCATAGTAATGGATACAACTATTTGGAT | TTGGGTTCTAATCGGGCCTCC | ATGCAAGCTCTACAAACTCCTATCACC |

FIGURE 49
(Continued)

| | | | | | | |
|---|---|---|---|---|---|---|
| iPS:394063 | 21-225_12D2 | AA | SEQ ID NO:993<br>RSSQSLLHSNGYNYLD | SEQ ID NO:9005<br>LGSNRAS | SEQ ID NO:17017<br>MQALQTPIT |
| | | NA | SEQ ID NO:994<br>CGGGCAAGTCAGGGCATTAG<br>AAATGATTTAGGC | SEQ ID NO:9006<br>GCTGCGTCCAGTTTGCAA<br>AGT | SEQ ID NO:17018<br>CTACACCATAGTAATTACCC<br>TCTCACT |
| iPS:394065 | 21-225_16A1 | AA | SEQ ID NO:995<br>RASQGIRNDLG | SEQ ID NO:9007<br>AASSLQS | SEQ ID NO:17019<br>LHHSNYPLT |
| | | NA | SEQ ID NO:996<br>AAGTCCAACCAGAGAGTTT<br>ATCCAGTCCAACAATCACA<br>ACTACTTAGCT | SEQ ID NO:9008<br>TGGGCATCTACCGGGA<br>ATCC | SEQ ID NO:17020<br>CAGCAATATTTAGTACTCC<br>ATTCACT |
| iPS:394067 | 21-225_11E2 | AA | SEQ ID NO:997<br>KSNQRVLSSSNNHNYLA | SEQ ID NO:9009<br>WASTRES | SEQ ID NO:17021<br>QQYFSTPFT |
| | | NA | SEQ ID NO:998<br>CGGGCAAGTCAGGGCATTAG<br>AAATGATTTAGGC | SEQ ID NO:9010<br>GCTGCATCCAGTTTGCAA<br>AGT | SEQ ID NO:17022<br>CTACAGCATAATAGTTATCC<br>GTGGACG |
| iPS:394069 | 21-225_12F2 | AA | SEQ ID NO:999<br>RASQGIRNDLG | SEQ ID NO:9011<br>AASSLQS | SEQ ID NO:17023<br>LQHNSYPWT |
| | | NA | SEQ ID NO:1000<br>CGGGCAAGTCAGGGCATTAG<br>AGATATTTAGGC | SEQ ID NO:9012<br>GCTGCATCCAGTTTGCAA<br>AAT | SEQ ID NO:17024<br>CTACAGTATCATAGTTACCC<br>ATTCACT |
| iPS:394071 | 21-225_16H1 | AA | SEQ ID NO:1001<br>RASQGIRDILG | SEQ ID NO:9013<br>AASSLQN | SEQ ID NO:17025<br>LQYHSYPFT |
| | | NA | SEQ ID NO:1002<br>AGGTCTAGTCAGAGCCTCCT<br>GCATAGTAAGGGATACAACT<br>ATTTGGAT | SEQ ID NO:9014<br>TTGGGTTCTAATCGGGCC<br>TCC | SEQ ID NO:17026<br>ATGCAAGCTCTACAAACTCC<br>TCTCACC |
| | 21-225_10C7 | AA | SEQ ID NO:1003<br>RSSQSLLHSKGYNYLD | SEQ ID NO:9015<br>LGSNRAS | SEQ ID NO:17027<br>MQALQTPLT |
| | | | SEQ ID NO:1004 | SEQ ID NO:9016 | SEQ ID NO:17028 |

FIGURE 49
(Continued)

| | | | | | |
|---|---|---|---|---|---|
| iPS:394073 | 21-225_15C9 | NA | CGGGCAAGTCAGGGCATTAG AAATGATTAGGC SEQ ID NO:1005 | GCTGCATCCAGTTTGCAA AGT SEQ ID NO:9017 | CTACACAACATACTAGTTACCC GCTCACT SEQ ID NO:17029 |
| | | AA | RASQGIRNDLG SEQ ID NO:1006 | AASSLQS SEQ ID NO:9018 | LQHTSYPLT SEQ ID NO:17030 |
| iPS:394075 | 21-225_8D12 | NA | CGGGCAAGTCAGGGCATTAG AAATGATTAGGC SEQ ID NO:1007 | GCTGCATCCAGTTTGCAA AGT SEQ ID NO:9019 | CTACAGCATAGTAGTTACCC GCTCACT SEQ ID NO:17031 |
| | | AA | RASQGIRNDLG SEQ ID NO:1008 | AASSLQS SEQ ID NO:9020 | LQHSSYPLT SEQ ID NO:17032 |
| iPS:394077 | 21-225_8E12 | NA | CGGGCAAGTCAGGGCATTAG TAATTATTAAAT SEQ ID NO:1009 | GCTGCATCCAGTTTACAA AGT SEQ ID NO:9021 | CAACAGAGTTACAGAACCCC CTTTTCACT SEQ ID NO:17033 |
| | | AA | RASQSISNYLN SEQ ID NO:1010 | AASSVQS SEQ ID NO:9022 | QQSYRTPFFT SEQ ID NO:17034 |
| iPS:394079 | 21-225_11F5 | NA | CGGGCAAGTCAGGGCATTAG AAATGATTAGGC SEQ ID NO:1011 | GCTGCATCCAGTGTGCA AAGT SEQ ID NO:9023 | CTACAGCATAATAGTTACCC GCTCACT SEQ ID NO:17035 |
| | | AA | RASQGIRNDLG SEQ ID NO:1012 | AASSVQS SEQ ID NO:9024 | LQHNSYPLT SEQ ID NO:17036 |
| iPS:394081 | 21-225_16B3 | NA | CAGGCGAGTCAGGACATTAA CAACTATTAAAT SEQ ID NO:1013 | GATGCATCCAATTGGA AACA SEQ ID NO:9025 | CAACAGTTTGATAATCTCCC GATCACC SEQ ID NO:17037 |
| | | AA | QASQDINNYLN SEQ ID NO:1014 | DASNLET SEQ ID NO:9026 | QQFDNLPIT SEQ ID NO:17038 |
| iPS:394083 | 21-225_16E6 | NA | CGGGCAAGTCAGAGCATTAT CAGTATTTAAAT SEQ ID NO:1015 | ACTACATCCAGTTTGCAA AGT SEQ ID NO:9027 | CAGCAGACTTACAGTACCCC GCTCACT SEQ ID NO:17039 |
| | | AA | RASQSIISYLN SEQ ID NO:1016 | TTSSLQS SEQ ID NO:9028 | QQTYSTPLT SEQ ID NO:17040 |

FIGURE 49
(Continued)

| | | | | | | |
|---|---|---|---|---|---|---|
| iPS:394085 | 21-225_8B11 | NA | AAGTCCAGCCAGAATGTTTTATACAACTCCAACAATAACAACTACTTAGCT SEQ ID NO:1017 | TGGGCATCTACCCGGAAATCC SEQ ID NO:9029 | CAGCAATATTATACTACTCCGTGCAGT SEQ ID NO:17041 | |
| | | AA | KSSQNVLYNSNNNNYLA SEQ ID NO:1018 | WASTRKS SEQ ID NO:9030 | QQYYTTPCS SEQ ID NO:17042 | |
| iPS:394087 | 21-225_11A5 | NA | CGGGCAAGTCAGAACATTTAAGTTATTTAAAT SEQ ID NO:1019 | GCTGCATCCAGTTTGCAAAGT SEQ ID NO:9031 | CAACAGAGTTACAATACCCCCTTATTCACT SEQ ID NO:17043 | |
| | | AA | RASQNIYSYLN SEQ ID NO:1020 | AASSLQS SEQ ID NO:9032 | QQSYNTPLFT SEQ ID NO:17044 | |
| iPS:394089 | 21-225_12E6 | NA | CGGGCAAGTCAGGGCATTAGAAGTGATTTAGGC SEQ ID NO:1021 | GCTGCATCCAGTTTGCAAAGT SEQ ID NO:9033 | CTACAGCATAATAGTTACCCGTGGACG SEQ ID NO:17045 | |
| | | AA | RASQGIRSDLG SEQ ID NO:1022 | AASSLQS SEQ ID NO:9034 | LQHNSYPWT SEQ ID NO:17046 | |
| iPS:394091 | 21-225_13H3 | NA | CGGGCAAGTCAGGGCATTAGAAATGATTTAGGC SEQ ID NO:1023 | GCTGCATCCAGTTTGCAAAGT SEQ ID NO:9035 | CTACAGCATAATAGTTACCCGCTCACT SEQ ID NO:17047 | |
| | | AA | RASQGIRNDLG SEQ ID NO:1024 | AASSLQS SEQ ID NO:9036 | LQHNSYPLT SEQ ID NO:17048 | |
| iPS:394093 | 21-225_9D12 | NA | CGGGCAAGTCAGGGCATTAGAAATGATTTAGGC SEQ ID NO:1025 | GCTGCATCCAGTTTGCAAAGT SEQ ID NO:9037 | CTACAGCATAATAGTTACCCGTGGACG SEQ ID NO:17049 | |
| | | AA | RASQGIRNDLG SEQ ID NO:1026 | AASSLQS SEQ ID NO:9038 | LQHNSYPWT SEQ ID NO:17050 | |
| iPS:394095 | 21-225_16H4 | NA | CGGGCAAGTCAGGGCATTAGAAATGATTTAGGC SEQ ID NO:1027 | ACTGCATCCAGTTTGCAAAGT SEQ ID NO:9039 | CTACAGCATAATAGTTACCCGTGGACG SEQ ID NO:17051 | |
| | | AA | RASQGIRNDLG | TASSLQS | LQHNSYPWT | |

FIGURE 49
(Continued)

| | | | | | | |
|---|---|---|---|---|---|---|
| iPS:398097 | 21-225_16G7 | NA | SEQ ID NO:1028 CGGGCAAGTCAGGGCATTAG AAATGATTAGGC | SEQ ID NO:9040 GCTGCATCCAGTTTGCAA AGT | SEQ ID NO:17052 CTACAACATATAGTTACCC GTGGACG |
| | | AA | SEQ ID NO:1029 RASQGIRNDLG | SEQ ID NO:9041 AASSLQS | SEQ ID NO:17053 LQHNSYPWT |
| iPS:398470 | 21-225_14B7 | NA | SEQ ID NO:1030 TCTGGAGATAAAATTGGGGAA TAAATATGCTTAC | SEQ ID NO:9042 CAAGATAGAAAGCGGCC CTCA | SEQ ID NO:17054 CAGGCGTGGAACAACAGCAC TGTGGTA |
| | | AA | SEQ ID NO:1031 SGDKLGNKYAY | SEQ ID NO:9043 QDRKRPS | SEQ ID NO:17055 QAWNNSTVV |
| iPS:398472 | 21-225_16E4 | NA | SEQ ID NO:1032 TCTGGAGATAAAATTGGGGAA TAAATATGTTTAC | SEQ ID NO:9044 CAAGATAGCAAGCGGCC CTCA | SEQ ID NO:17056 CAGGCGTGGGACAGCAGCAC TGTGGTT |
| | | AA | SEQ ID NO:1033 SGDKLGDKYVY | SEQ ID NO:9045 QDSKRPS | SEQ ID NO:17057 QAWDSSTVV |
| iPS:398474 | 21-225_17B10 | NA | SEQ ID NO:1034 CGGTCAAGTCAGAGCATTAA CAGCTATTTAAAT | SEQ ID NO:9046 GCTGCATCCAGTTTGCAC CACGTGGACG | SEQ ID NO:17058 CAACAGGGTTACAATACCCC |
| | | AA | SEQ ID NO:1035 RSSQSINSYLN | SEQ ID NO:9047 AASSLHS | SEQ ID NO:17059 QQGYNTPTWT |
| iPS:398476 | 21-225_17C1 | NA | SEQ ID NO:1036 CGGGCAAGTCAGAACATTAA CGACTATTTAAAT | SEQ ID NO:9048 GCTGCATCCAATTTGCAA AGT | SEQ ID NO:17060 CAACAGACTTACAATACCCC TCCGGAGCGCAGT |
| | | AA | SEQ ID NO:1037 RASQNINDYLN | SEQ ID NO:9049 AASNLQS | SEQ ID NO:17061 QQTYNTPPERS |
| iPS:398478 | 21-225_17C10 | NA | SEQ ID NO:1038 CGGGCGAGTCAGGGCATTAG CAATTATTAGCC | SEQ ID NO:9050 GCTGCATCCACTTTGCAA TCA | SEQ ID NO:17062 CAAAAGTATAACAGTGCCCC TCCGCTCACC |
| | | AA | SEQ ID NO:1039 RASQGISNYLA | SEQ ID NO:9051 AASTLQS | SEQ ID NO:17063 QKYNSAPPLT |

FIGURE 49
(Continued)

| | | | | | | |
|---|---|---|---|---|---|---|
| iPS:398480 | 21-225_17G4 | NA | SEQ ID NO:1040 CGGACAAGTCAGAGAATATTAG CAACTATTTAAAT | SEQ ID NO:9052 GTTGCGTCCAGTTTCCA AGT | SEQ ID NO:17064 CAACAGAGTAACTTTTTCCC GCTCACT | |
| | | AA | SEQ ID NO:1041 RTSQNISNYLN | SEQ ID NO:9053 VASSFPS | SEQ ID NO:17065 QQSNFFPLT | |
| iPS:398482 | 21-225_17H6 | NA | SEQ ID NO:1042 CGGGCGAGTCGGGACATTAG CAATTATTTAGCC | SEQ ID NO:9054 ACTGCATCCAGTTTGCAA AGT | SEQ ID NO:17066 CAACAGTATCATAGTTACCC ATTCACT | |
| | | AA | SEQ ID NO:1043 RASRDISNYLA | SEQ ID NO:9055 TASSLQS | SEQ ID NO:17067 QQYHSYPFT | |
| iPS:398484 | 21-225_18D4 | NA | SEQ ID NO:1044 CGGGCAAGTCAGGGCATTAG AAATGATTTAGGC | SEQ ID NO:9056 GCTGCATCCAGTTTGGA AAGT | SEQ ID NO:17068 CTACACATCATAATAATTACCT CCCCATCACC | |
| | | AA | SEQ ID NO:1045 RASQGIRNDLG | SEQ ID NO:9057 AASSLES | SEQ ID NO:17069 LHHNNYLPIT | |
| iPS:398486 | 21-225_19A1 | NA | SEQ ID NO:1046 CGGGCAAGTCATACCATTAC CAGCTATTTAAAT | SEQ ID NO:9058 GCTACATCCAATCTCCAA AGT | SEQ ID NO:17070 CAACAGAGTTACAACTTCCC GCTCACT | |
| | | AA | SEQ ID NO:1047 RASHTITSYLN | SEQ ID NO:9059 ATSNLQS | SEQ ID NO:17071 QQSYNFPLT | |
| iPS:398488 | 21-225_19F6 | NA | SEQ ID NO:1048 TCTGGAGATAAATTGGGGA TAAATATGCTTGC | SEQ ID NO:9060 CAAGATAGCAAGCGGCC CTCA | SEQ ID NO:17072 CAGGCGTGGGACAACAACAC TGTGGTA | |
| | | AA | SEQ ID NO:1049 SGDKLGDKYAC | SEQ ID NO:9061 QDSKRPS | SEQ ID NO:17073 QAWDNNTVV | |
| iPS:398490 | 21-225_21D12 | NA | SEQ ID NO:1050 TCTGGAGATAAATTGGGGAA TAAATATGCTTAC | SEQ ID NO:9062 CAAGATAGAAAGAGGCC CTCA | SEQ ID NO:17074 CAGGCGTGGGACAACAGCAC TGTGGTA | |
| | | AA | SEQ ID NO:1051 SGDKLGNKYAY | SEQ ID NO:9063 QDRKRPS | SEQ ID NO:17075 QAWDNSTVV | |

FIGURE 49
(Continued)

| | | | | | | |
|---|---|---|---|---|---|---|
| iPS:398492 | 21-225_21F12 | NA | SEQ ID NO:1052 CGGGCGAGTCAGGGCATTAG GAATTTTTAGCC | SEQ ID NO:9064 GCTGCATCCAGTTTGCAA ACT | SEQ ID NO:1076 CAACAGTATAATAGTTTCCC ATTCACT |
| | | AA | SEQ ID NO:1053 RASQGIRNFLA | SEQ ID NO:9065 AASSLQT | SEQ ID NO:17077 QQYNSFPFT |
| iPS:398494 | 21-225_21H4 | NA | SEQ ID NO:1054 ACTGGAACCAGCAGTGACGT TGGTGGTTATAACTCTGTCT CC | SEQ ID NO:9066 GAGGTCAGTAATCGGCC CTCA | SEQ ID NO:17078 AGCTCATATACAAGGAGCAG CACTGTGGTA |
| | | AA | SEQ ID NO:1055 TGTSSDVGGYNSVS | SEQ ID NO:9067 EVSNRPS | SEQ ID NO:17079 SSYTRSSTVV |
| iPS:398496 | 21-225_22D2 | NA | SEQ ID NO:1056 AAGTCCAGCCAGAGTGTTTT ACACAGCTCCAACAATAACA ACTACTTAGCT | SEQ ID NO:9068 TGGGCATCTACCCGGAA ATCC | SEQ ID NO:17080 CAGCAATATTATAGTACTCC GTGCAGT |
| | | AA | SEQ ID NO:1057 KSSQSVLHSSNNNNYLA | SEQ ID NO:9069 WASTRKS | SEQ ID NO:17081 QQYYSTPCS |
| iPS:398498 | 21-225_22E6 | NA | SEQ ID NO:1058 TCTGGAGATAAATTGGGGGA GAAATATGCTTGC | SEQ ID NO:9070 CAAGATAGAAAGCGGCC CTCA | SEQ ID NO:17082 CAGGCGTGGGACAGCAGCAC TGCGGTA |
| | | AA | SEQ ID NO:1059 SGDKLGEKYAC | SEQ ID NO:9071 QDRKRPS | SEQ ID NO:17083 QAWDSSTAV |
| iPS:398500 | 21-225_23A11 | NA | SEQ ID NO:1060 CGGGCGAGTCAGGACATTAG CAATTATTTAGCC | SEQ ID NO:9072 GCTGCATCCACTTTGCAA AGT | SEQ ID NO:17084 CAACAGTATAATAGTTACCC ATTCACT |
| | | AA | SEQ ID NO:1061 RASQDISNYLA | SEQ ID NO:9073 AASTLQS | SEQ ID NO:17085 QQYNSYPFT |
| iPS:398502 | | NA | SEQ ID NO:1062 CGGGCGAGTCAGGGTATTAC CAAGTGGTTAGCC | SEQ ID NO:9074 GCTGCATCCAGTTTGCAA AGT | SEQ ID NO:17086 CAACAGGCTAACAGTTCCC ATTCACT |

FIGURE 49
(Continued)

| | | | | | | |
|---|---|---|---|---|---|---|
| iPS:398504 | 21-225_23B11 | | | | SEQ ID NO:1063 | SEQ ID NO:9075 | SEQ ID NO:17087 |
| | | AA | RASQGITKWLA | AASSLQS | QQANSFPFT |
| | | | SEQ ID NO:1064 | SEQ ID NO:9076 | SEQ ID NO:17088 |
| iPS:398506 | 21-225_23D7 | NA | TCTGGAGAAAAATTGGGGG ATAAATATGTTTGT | CAAGATAGCAAGCGGCC CTCA | CAGGCGTGGAACAGCAGCAA TGTGGTA |
| | | | SEQ ID NO:1065 | SEQ ID NO:9077 | SEQ ID NO:17089 |
| | | AA | SGEKLGDKYVC | QDSKRPS | QAWNSSNVV |
| | | | SEQ ID NO:1066 | SEQ ID NO:9078 | SEQ ID NO:17090 |
| iPS:398506 | 21-225_23G12 | NA | AAGTCCAGCCAGAGTATTT ATTCAGTCCAACAATAACA ACTACTTAGCT | TGGGCATCTACCCGGGA ATCC | CAGCAATATTCTAGTACTCC GTGGACG |
| | | | SEQ ID NO:1067 | SEQ ID NO:9079 | SEQ ID NO:17091 |
| | | AA | KSSQSILFSSNNNNYLA | WASTRES | QQYSSTPWT |
| | | | SEQ ID NO:1068 | SEQ ID NO:9080 | SEQ ID NO:17092 |
| iPS:398508 | 21-225_24B1 | NA | AGGTCTAGTCAAAGCCTCGT ATACAGTGATGGAAACACCT ACTTGAAT | AAGGTTTCTAACTGGGA CTCT | ATGCAAGGTGCACACTGGCC TCCGATCACC |
| | | | SEQ ID NO:1069 | SEQ ID NO:9081 | SEQ ID NO:17093 |
| | | AA | RSSQSLVYSDGNTYLN | KVSNWDS | MQGAHWPPIT |
| | | | SEQ ID NO:1070 | SEQ ID NO:9082 | SEQ ID NO:17094 |
| iPS:398510 | 21-225_25A3 | NA | AAGTCCAGCCAGAGTGTTT ATACAGTCCAACAATAAGA ACTACTTAGCT | TGGGCATCTACCCGGGA ATCC | CAGCAATATTATAGTACTCC GTGCAGT |
| | | | SEQ ID NO:1071 | SEQ ID NO:9083 | SEQ ID NO:17095 |
| | | AA | KSSQSVLYSSNNKNYLA | WASTRES | QQYYSTPCS |
| | | | SEQ ID NO:1072 | SEQ ID NO:9084 | SEQ ID NO:17096 |
| iPS:398512 | 21-225_25E12 | NA | AAGTCCAGCCAGAGTGTTT ATACCACTCCAACAATTACA ACTACTTAGCT | TGGGCATCTACCCGGGA GTCC | CAGCAATATTACAGTACTCC GTGCAGT |
| | | | SEQ ID NO:1073 | SEQ ID NO:9085 | SEQ ID NO:17097 |

FIGURE 49
(Continued)

| | | | | | | |
|---|---|---|---|---|---|---|
| iPS:398516 | 21-225_26A9 | AA | KSSQSVLYHSNNYNYLA<br>SEQ ID NO:1074 | | WASTRES<br>SEQ ID NO:9086 | QQYYSTPCS<br>SEQ ID NO:17098 |
| | | NA | AAGTCCAGCCAGAGTGTTTT<br>ATACAGCTCCAACAATAAGA<br>ACTACTTAGCT<br>SEQ ID NO:1075 | | TGGGCATCTACCCGGGA<br>ATCC<br>SEQ ID NO:9087 | CAGCAATATTATAGTAGTCC<br>GTGCAGT<br>SEQ ID NO:17099 |
| iPS:398520 | 21-225_31C4 | AA | KSSQVLYSSNKNYLA<br>SEQ ID NO:1076 | | WASTRES<br>SEQ ID NO:9088 | QQYYSSPCS<br>SEQ ID NO:17100 |
| | | NA | CGGGGGAGTCAGGGTATTAG<br>CAAATGGTTAGCC<br>SEQ ID NO:1077 | | GCTGCATCCAGTTGCAG<br>AGT<br>SEQ ID NO:9089 | CAACAGGCTAACAGTTTCC<br>ATTCACT<br>SEQ ID NO:17101 |
| | | AA | RASQGISKWLA<br>SEQ ID NO:1078 | | AASSLQS<br>SEQ ID NO:9090 | QQANSFPFT<br>SEQ ID NO:17102 |
| iPS:398522 | 21-225_32A1 | NA | AAGTCCAGCCAGAGTGTTTT<br>ATACAGCTCCAACAATACA<br>ACTACTTAGCT<br>SEQ ID NO:1079 | | TGGGCATCTACCCGGAA<br>ATCC<br>SEQ ID NO:9091 | CAACAATATTATACTTCTCC<br>GTGCAGT<br>SEQ ID NO:17103 |
| | | AA | KSSQSVLYSSNNYNYLA<br>SEQ ID NO:1080 | | WASTRKS<br>SEQ ID NO:9092 | QQYYTSPCS<br>SEQ ID NO:17104 |
| iPS:398524 | 21-225_32A5 | NA | AAGTCCAGCCAGAGTGTTTT<br>ACACAGCTCCAACAATAAGA<br>ACTACTTAGCT<br>SEQ ID NO:1081 | | TGGGCATCTACCCGGGA<br>ATCC<br>SEQ ID NO:9093 | CAGCAATATTATAGTTCTCC<br>GTGCAGT<br>SEQ ID NO:17105 |
| | | AA | KSSQSVLHSSNKNYLA<br>SEQ ID NO:1082 | | WASTRES<br>SEQ ID NO:9094 | QQYYSSPCS<br>SEQ ID NO:17106 |
| iPS:398526 | 21-225_32B3 | NA | CGGGCGAGTCAGGGCATTAG<br>CAATTATTTAGCC<br>SEQ ID NO:1083 | | GCTGCATCCAGTTACAA<br>AGT<br>SEQ ID NO:9095 | CAACAGTATAATAGTTATCC<br>ATTCACT<br>SEQ ID NO:17107 |
| | | AA | RASQGISNYLA<br>SEQ ID NO:1084 | | AASSLQS<br>SEQ ID NO:9096 | QQYNSYPFT<br>SEQ ID NO:17108 |

FIGURE 49
(Continued)

| | | | | | |
|---|---|---|---|---|---|
| iPS:398528 | 21-225_32G1 | NA | CGGGCAAGTCAGGAGACATGA GAAGTGATTTAGGC<br>SEQ ID NO:1085 | GCTGCATCCAGTTTGCAA AGT<br>SEQ ID NO:9097 | CTACAGGCATACTATTCCCCT CCTACT<br>SEQ ID NO:17109 |
| | | AA | RASQDMRSDLG<br>SEQ ID NO:1086 | AASSLQS<br>SEQ ID NO:9098 | LQHTISPPT<br>SEQ ID NO:17110 |
| iPS:398530 | 21-225_32G4 | NA | AGGTCAAGTCAAAGCCTCGT ATACAGTGATGGAAACACCT ACTTGAAT<br>SEQ ID NO:1087 | AAGGTTTCTAACTGGGA CTCT<br>SEQ ID NO:9099 | ATGCAAGGTATACACTGGCT CACT<br>SEQ ID NO:17111 |
| | | AA | RSSQSLVYSDGNTYLN<br>SEQ ID NO:1088 | KVSNWDS<br>SEQ ID NO:9100 | MQGIHWLT<br>SEQ ID NO:17112 |
| iPS:398532 | 21-225_33B7 | NA | CGGGCGAGTCAGGACATTAG CAATTATTTGGCC<br>SEQ ID NO:1089 | GCTGCATCTAGTTTGCAA AGT<br>SEQ ID NO:9101 | CAACAGTATCATAGTTACCC GCTCACC<br>SEQ ID NO:17113 |
| | | AA | RASQDISNYLA<br>SEQ ID NO:1090 | AASSLQS<br>SEQ ID NO:9102 | QQYHSYPLT<br>SEQ ID NO:17114 |
| iPS:398534 | 21-225_33B8 | NA | CGGGCAAGTCAGGACATTAG AAGTGATTTAGGC<br>SEQ ID NO:1091 | GCTGCATCCAGTTTGCAA AGT<br>SEQ ID NO:9103 | CTACAGCATACTATTACCC TCCTACT<br>SEQ ID NO:17115 |
| | | AA | RASQDIRSDLG<br>SEQ ID NO:1092 | AASSLQS<br>SEQ ID NO:9104 | LQHTIYPPT<br>SEQ ID NO:17116 |
| iPS:398536 | 21-225_33D12 | NA | CGGGCAAGTCAGAGAGCATTAG AAGCTATTTAAAT<br>SEQ ID NO:1093 | AGTGCATCCAGTTTGCA AAGT<br>SEQ ID NO:9105 | CAACAGAGTTACAGTATCC GATCACC<br>SEQ ID NO:17117 |
| | | AA | RASQSIRSYLN<br>SEQ ID NO:1094 | SASSLQS<br>SEQ ID NO:9106 | QQSYSIPIT<br>SEQ ID NO:17118 |
| iPS:398538 | 21-225_34H7 | NA | AAGTCCAGCCAGAGTGTTTT ATACAGCTCCAACAATTACA ACTACTTAGCT<br>SEQ ID NO:1095 | TGGGCATCTACCCGGAA ATCC<br>SEQ ID NO:9107 | CAGCAATATTATACTTCTCC GTGCAGT<br>SEQ ID NO:17119 |

FIGURE 49
(Continued)

| | | | | | |
|---|---|---|---|---|---|
| iPS:398540 | | AA | KSSQSVLYSSNNYNYLA | WASTRKS | QQYYTSPCS |
| | | | SEQ ID NO:1096 | SEQ ID NO:9108 | SEQ ID NO:17120 |
| | 21-225_35A6 | NA | CGGGCAAGTCAGGACATTAG AAGTGATTTAGGC | GCTACACATCCAGTTTGCAA AGT | CTACAGTATACTATTTACCC TCCTACT |
| | | | SEQ ID NO:1097 | SEQ ID NO:9109 | SEQ ID NO:17121 |
| iPS:398544 | | AA | RASQDIRSDLG | ATSSLQS | LQHTIYPPT |
| | | | SEQ ID NO:1098 | SEQ ID NO:9110 | SEQ ID NO:17122 |
| | 21-225_7C8 | NA | ACCCTAAGCAGTGAGCACAG CACCTACACCATGAA | GTTAAGAGTGATGGCAG CCACAGCAAGGGGGAC | GGAGAGAGCCACCGATTGA TGGCCAAGTCGGTGGTA |
| | | | SEQ ID NO:1099 | SEQ ID NO:9111 | SEQ ID NO:17123 |
| iPS:398546 | | AA | TLSSEHSTYTIE | VKSDGSHSKGD | GESHPIDGQVGVV |
| | | | SEQ ID NO:1100 | SEQ ID NO:9112 | SEQ ID NO:17124 |
| | 21-225_9H10 | NA | TCTGGAGATAAATTGGGGGA TAAATATGCTTGC | CAAGATAGCAAGCGCC CTCA | CAGGCGTGGACAGCAGCAC TTATGTGGTA |
| | | | SEQ ID NO:1101 | SEQ ID NO:9113 | SEQ ID NO:17125 |
| iPS:402219 | | AA | SGDKLGDKYAC | QDSKRPS | QAWDSSTYVV |
| | | | SEQ ID NO:1102 | SEQ ID NO:9114 | SEQ ID NO:17126 |
| | 21-225_1C12 | NA | CGGGCAAGTCAGGGCATTAG AAATGATTTAGGC | GCTGCATCCAGTTTGCAA AGT | CTACAACATAATAGTTACCC GCTCACT |
| | | | SEQ ID NO:1103 | SEQ ID NO:9115 | SEQ ID NO:17127 |
| iPS:402221 | | AA | RASQGIRNDLG | AASSLQS | LQHNSYPLT |
| | | | SEQ ID NO:1104 | SEQ ID NO:9116 | SEQ ID NO:17128 |
| | 21-225_2C12 | NA | CGGGCGAGTCAGGGCATTAG CAATTATTAGGC | GCTGCAACCAGTTTGCA AAGT | CAACAGTATTATAGTTACCC GATCACC |
| | | | SEQ ID NO:1105 | SEQ ID NO:9117 | SEQ ID NO:17129 |
| iPS:402223 | | AA | RASQGISNYLA | AATSLQS | QQYYSYPT |
| | | | SEQ ID NO:1106 | SEQ ID NO:9118 | SEQ ID NO:17130 |
| | | NA | CGGGCGAGTCAGGGTATTAG CAGATGGTTAGCC | GCTGCAATCCGTTTGCAA AGT | CAACAGGCTAACAGTTCCC ATTCACT |

FIGURE 49
(Continued)

| | | | | | | | |
|---|---|---|---|---|---|---|---|
| iPS:402225 | 21-225_30A11 | AA | SEQ ID NO:1107<br>RASQGISRWLA | SEQ ID NO:9119<br>AASRLQS | SEQ ID NO:17131<br>QQANSFPFT | | |
| iPS:402229 | 21-225_2B1 | NA | SEQ ID NO:1108<br>TCTGGAGATAAATTGGGGA<br>TAAATATGCTTGC | SEQ ID NO:9120<br>CAAGATCGCAAGCGGCC<br>CTCA | SEQ ID NO:17132<br>CAGGCGTGGGACAACAACAC<br>TGTGGTA | | |
| | | AA | SEQ ID NO:1109<br>SGDKLGDKYAC | SEQ ID NO:9121<br>QDRKRPS | SEQ ID NO:17133<br>QAWDNNTVV | | |
| iPS:402231 | 21-225_16H9 | NA | SEQ ID NO:1110<br>CGGGCAAGTCAGGGCATTAG<br>AAATTATTAGGC | SEQ ID NO:9122<br>GGTGCATCCAGTTGCA<br>AAGT | SEQ ID NO:17134<br>CTACAGTATCATAGTTATCT<br>ATTCACT | | |
| | | AA | SEQ ID NO:1111<br>RASQGIRNYLG | SEQ ID NO:9123<br>GASSLQS | SEQ ID NO:17135<br>LQYHSYLFT | | |
| iPS:402233 | 21-225_6D9 | NA | SEQ ID NO:1112<br>TCTGGAGATAAATTGGGGA<br>AAAATATGCTTGC | SEQ ID NO:9124<br>CAAGATAAGAAGCGGCC<br>CTCA | SEQ ID NO:17136<br>CAGGCGTGGGACAGCAGCAC<br>TGTA | | |
| | | AA | SEQ ID NO:1113<br>SGDKLGEKYAC | SEQ ID NO:9125<br>QDKKRPS | SEQ ID NO:17137<br>QAWDSSTV | | |
| iPS:402235 | 21-225_16D10 | NA | SEQ ID NO:1114<br>CGGGCGAGTCAGGACATAA<br>GTAATTATTAGCC | SEQ ID NO:9126<br>GCTACACCCAGTTGCA<br>GAGT | SEQ ID NO:17138<br>CAACAGTATAATAGTTACCC<br>GCTCACT | | |
| | | AA | SEQ ID NO:1115<br>RASQDISNYLA | SEQ ID NO:9127<br>ATPSLQS | SEQ ID NO:17139<br>QQYNSYPLT | | |
| iPS:402237 | 21-225_20F10 | NA | SEQ ID NO:1116<br>CGGGCGAGTCAGGGCATTGC<br>CAATTATTAGCC | SEQ ID NO:9128<br>GCTGCATCCAGTTGCAA<br>AGT | SEQ ID NO:17140<br>CAGCAATATATAGTTACCC<br>ATTCACT | | |
| | | AA | SEQ ID NO:1117<br>RASQGINNYLA | SEQ ID NO:9129<br>AASSLQS | SEQ ID NO:17141<br>QQYNSYPFT | | |
| | | NA | SEQ ID NO:1118<br>CGGGCGAGTCAGGGCATTGC<br>CAATTATTAGCC | SEQ ID NO:9130<br>GCTGCATCCAGTTGCAA<br>AGT | SEQ ID NO:17142<br>CAACAGTATCATAGTTACCC<br>GCTCACT | | |

FIGURE 49
(Continued)

| | | | | | |
|---|---|---|---|---|---|
| iPS:403868 | 21-225_23D11 | AA | SEQ ID NO:1119<br>RASQGIANYLA<br>SEQ ID NO:1120 | SEQ ID NO:9131<br>AASSLQS<br>SEQ ID NO:9132 | SEQ ID NO:17143<br>QQYHSYPLT<br>SEQ ID NO:17144 |
| iPS:403870 | 21-225_19D11 | NA | CGGGCAAGTCAGGGCATTAG<br>AAATGATTTAGGC<br>SEQ ID NO:1121 | GCTACATCCAGTTGCAA<br>AGT<br>SEQ ID NO:9133 | CTACAGTATTATAGTTACCC<br>GCTCACT<br>SEQ ID NO:17145 |
| | | AA | RASQGIRNDLG<br>SEQ ID NO:1122 | ATSSLQS<br>SEQ ID NO:9134 | LQYYSYPLT<br>SEQ ID NO:17146 |
| iPS:403872 | 21-225_23G4 | NA | CGGGCAAGTCAGAACATTTA<br>CAGCTATTTAAAT<br>SEQ ID NO:1123 | GCTGCATCCAGTTGCAA<br>AGT<br>SEQ ID NO:9135 | CAACAGAGTTACAATACCCC<br>TCCGGAGTGCAAT<br>SEQ ID NO:17147 |
| | | AA | RASQNIYSYLN<br>SEQ ID NO:1124 | AASSLQS<br>SEQ ID NO:9136 | QQSYNTPPECN<br>SEQ ID NO:17148 |
| iPS:403873 | 21-225_8F11 | NA | CGGGCAAGTCAGGGCATTAG<br>GAGTGATTTAGGC<br>SEQ ID NO:1125 | GATGCATCCAGTGTGCA<br>AAGT<br>SEQ ID NO:9137 | CTACAACATTATACTTACCC<br>GCTCACT<br>SEQ ID NO:17149 |
| | | AA | RASQGIRSDLG<br>SEQ ID NO:1126 | DASSVQS<br>SEQ ID NO:9138 | LQHYTYPLT<br>SEQ ID NO:17150 |
| iPS:404090 | 21-225_8D8 | NA | TCTGGAGATAAATTGGGGGA<br>GAAATATGCTTGC<br>SEQ ID NO:1127 | CAAGATAGGAAGCGGCC<br>CTCA<br>SEQ ID NO:9139 | CAGGGCGTGGGACAGCAGCAC<br>TGCGGTA<br>SEQ ID NO:17151 |
| | | AA | SGDKLGEKYAC<br>SEQ ID NO:1128 | QDRKRPS<br>SEQ ID NO:9140 | QAWDSSTAV<br>SEQ ID NO:17152 |
| iPS:412232 | 21-225_4A2 | NA | AAGTCCAGCCAGAGTATTTT<br>ACACAGTCCAACAATAACA<br>ACTACTTAGCT<br>SEQ ID NO:1129 | TGGGCATCTACCCGGGA<br>ATCC<br>SEQ ID NO:9141 | CAGCAATATTATATACTCC<br>AGTCACT<br>SEQ ID NO:17153 |
| | | AA | KSSQSILHSSNNNNYLA<br>SEQ ID NO:1130 | WASTRES<br>SEQ ID NO:9142 | QQYYNTPVT<br>SEQ ID NO:17154 |

FIGURE 49
(Continued)

| | | | | |
|---|---|---|---|---|
| iPS:422894 | 21-225_4A2.001 | NA | AAGTCCAGCCAGAGTATTT ACACAGCTCCAACAATAACA ACTACTTAGCT<br>SEQ ID NO:1131 | TGGGCATCTACCCGGGA ATCC<br>SEQ ID NO:9143 | CAGCAATATTATAATACTCC AGTCACT<br>SEQ ID NO:17155 |
| | | AA | KSSQSILHSSNNNYLA<br>SEQ ID NO:1132 | WASTRES<br>SEQ ID NO:9144 | QQYYNTPVT<br>SEQ ID NO:17156 |
| iPS:423018 | 21-225_31D12_LC2 | NA | TCTGGAGATAAATTGGGGGA TAAATATGCTTAC<br>SEQ ID NO:1133 | CAAGATAGGAAGCGGCC CTCA<br>SEQ ID NO:9145 | CAGGGGTGGGACAACAGCAC TGCGGTA<br>SEQ ID NO:17157 |
| | | AA | SGDKLGDKYAY<br>SEQ ID NO:1134 | QDRKRPS<br>SEQ ID NO:9146 | QAWDNSTAV<br>SEQ ID NO:17158 |
| iPS:423019 | 21-225_31D12_LC1 | NA | AGGTCAGTCAAAGCCTCAT ATACAGTGATGGAAACACCT TCTTGAAT<br>SEQ ID NO:1135 | AAGGTTCTAATTGGGA CTCT<br>SEQ ID NO:9147 | ATGCAAGGTACACACTGGCC TCTCACC<br>SEQ ID NO:17159 |
| | | AA | RSSQSLIYSDGNTFLN<br>SEQ ID NO:1136 | KVSNWDS<br>SEQ ID NO:9148 | MQGTHWPLT<br>SEQ ID NO:17160 |
| iPS:423314 | 21-225_12F11 | NA | AAGTCCAGCCAGAGTGTTTT ACACAGCTCCAACAATAACA ACTACTTAGCT<br>SEQ ID NO:1137 | TGGGCATCTACCCGGGA ATCC<br>SEQ ID NO:9149 | CAGCAATATTATGATACTCC ATTCACT<br>SEQ ID NO:17161 |
| | | AA | KSSQSVLHSSNNYNYLA<br>SEQ ID NO:1138 | WASTRES<br>SEQ ID NO:9150 | QQYYDTPFT<br>SEQ ID NO:17162 |
| iPS:424419 | 21-225_25A4.001 | NA | AAGTCCAGCCAGAGTGTTTT ATACAGTCCCACAATAACA ACTACTTAGCT<br>SEQ ID NO:1139 | TGGGCATCTACCCGGGA ATCC<br>SEQ ID NO:9151 | CAGCAGTATTATAGTACTCC TCCGACG<br>SEQ ID NO:17163 |
| | | AA | KSSQSVLYSSHNNNYLA<br>SEQ ID NO:1140 | WASTRES<br>SEQ ID NO:9152 | QQYYSTPPT<br>SEQ ID NO:17164 |

FIGURE 49
(Continued)

| | | | | | |
|---|---|---|---|---|---|
| iPS:424460 | 21-225_7E11.001 | NA | CGGGCAAGTCAAAACATTAT CAGCTATTTAAAT SEQ ID NO:1141 | ACTGCATCCAGTTTGCAA AGT SEQ ID NO:9153 | CAACAGACTTACAGTACCCC GCTCACT SEQ ID NO:17165 |
| | | AA | RASQNIISYLN SEQ ID NO:1142 | TASSLQS SEQ ID NO:9154 | QQTYSTPLT SEQ ID NO:17166 |
| iPS:426108 | 21-225_10G6 | NA | CGGGCGAGTCAGGGTATTAG CAAATGGTTAGCC SEQ ID NO:1143 | GCTGCATATAGTTTACAA AGT SEQ ID NO:9155 | CAACAGGCTAACAGTTTCCC ATTCACT SEQ ID NO:17167 |
| | | AA | RASQGISKWLA SEQ ID NO:1144 | AAYSLQS SEQ ID NO:9156 | QQANSFPFT SEQ ID NO:17168 |
| iPS:426110 | 21-225_12E9 | NA | CGGGCGAGTCAGGGTATTAG CAGCTGGTTAGCC SEQ ID NO:1145 | GCTGCATCCAGGTTGCA AAGT SEQ ID NO:9157 | CAACAGGCTAACAGTTTCCC ATTCACT SEQ ID NO:17169 |
| | | AA | RASQGISSWLA SEQ ID NO:1146 | AASRLQS SEQ ID NO:9158 | QQANSFPFT SEQ ID NO:17170 |
| iPS:426112 | 21-225_12F12 | NA | AAGTCCAGCCAGAGTGTTT ATTCAGCTCCAACAATAACC ACTACTTAGCA SEQ ID NO:1147 | TGGGCATCTACCCGGC ATCC SEQ ID NO:9159 | CAGCAATATATAGTAGTCC GTGGACG SEQ ID NO:17171 |
| | | AA | KSSQTVLFSSNNNHYLA SEQ ID NO:1148 | WASTRAS SEQ ID NO:9160 | QQYYSSPWT SEQ ID NO:17172 |
| iPS:426114 | 21-225_28H2 | NA | CGGGCAAGTCAGGGCATTAG AAATGATTTAGGC SEQ ID NO:1149 | GCTGCATCCAGTTTGCAA AGT SEQ ID NO:9161 | CTACAACATTATAGTTACCC TCGCAGT SEQ ID NO:17173 |
| | | AA | RASQGIRNDLG SEQ ID NO:1150 | AASSLQS SEQ ID NO:9162 | LQHYSYPRS SEQ ID NO:17174 |
| iPS:426116 | 21-225_29E2 | NA | CGGGCAAGTCAGGGCATTAG AAATGATTTAGGC SEQ ID NO:1151 | GCTGCATCCAGTTTGCAA AGT SEQ ID NO:9163 | TTACAGCATTATAATTACCC TCGCAGT SEQ ID NO:17175 |
| | | AA | RASQAIRNDLG | AASSLQS | LQHYNYPRS |

FIGURE 49
(Continued)

| | | | | | | |
|---|---|---|---|---|---|---|
| iPS:426118 | 21-225_7A10 | NA | CGGGCAAGTCAGAACATTA CAGCTATTTAAAT SEQ ID NO:1152 | SEQ ID NO:9164 TCTACATCCAGTTTGCAA AGT | SEQ ID NO:17176 CAACAGAGTTACAGTCCCC TCTCACT |
| | | | SEQ ID NO:1153 RASQNIYSYLN | SEQ ID NO:9165 STSSLQS | SEQ ID NO:17177 QQSYSPPLT |
| iPS:426124 | 21-225_32D6 | NA | CGGGCAAGTCAGAACATTA CAGCTATTTAAAT SEQ ID NO:1154 | SEQ ID NO:9166 GTTGCATCCGTTTGCAA AGT | SEQ ID NO:17178 CAACAGAGTTACAGTACCC GTACACT |
| | | AA | SEQ ID NO:1155 RASQNIISYLN | SEQ ID NO:9167 VASRLQS | SEQ ID NO:17179 QQSYSTPYT |
| iPS:426126 | 21-225_6G6 | NA | AAGTCCAGCCAGAGTGTTT ACACAACTCCAACAATTATA ACTATTTAGCT SEQ ID NO:1156 | SEQ ID NO:9168 TGGGCATCTACCCGGGA ATCC | SEQ ID NO:17180 CAGCAATATTATGATACTCC ATTCACT |
| | | AA | SEQ ID NO:1157 KSSQSVLHNSNNYNYLA | SEQ ID NO:9169 WASTRES | SEQ ID NO:17181 QQYYDTPFT |
| iPS:433895 | 21-225_43E1 | NA | CGGGCAAGTCAGGGCATTAG AAATGATTTAGGC SEQ ID NO:1158 | SEQ ID NO:9170 GCTGCATCCAGTTTGCAA AGT | SEQ ID NO:17182 CTACAGCATAATAGTTACCC ATTCACT |
| | | AA | SEQ ID NO:1159 RASQGIRNDLG | SEQ ID NO:9171 AASSLQS | SEQ ID NO:17183 LQHNSYPFT |
| iPS:433897 | 21-225_43C2 | NA | CGGGCAAGTCAGGGCATTAG CGACTGGTTAGCC SEQ ID NO:1160 | SEQ ID NO:9172 GCTGCATCCAGTTTGCAA AGT | SEQ ID NO:17184 CAACAGACTAACAGTTCCC GTGGACG |
| | | AA | SEQ ID NO:1161 RASQGISDWLA | SEQ ID NO:9173 AASSLQS | SEQ ID NO:17185 QQTNSFPWT |
| iPS:433899 | 21-225_43C3 | NA | CGGGCAAGTCAGGGCATTAG AAATGATTTAGGC SEQ ID NO:1162 | SEQ ID NO:9174 GCTGCATCCAGTTTGCAA AGT | SEQ ID NO:17186 CTACAGCATAATAGTTACCC TCTCACT |
| | | NA | SEQ ID NO:1163 | SEQ ID NO:9175 | SEQ ID NO:17187 |

FIGURE 49
(Continued)

| | | | | | | |
|---|---|---|---|---|---|---|
| iPS:433901 | | AA | RASQGIRNDLG SEQ ID NO:164 | AASSLQS SEQ ID NO:9176 | LQHNSYPLT SEQ ID NO:17188 | |
| | 21-225_43A4 | NA | CGGGCGAGTCAGGGCATTAA CAATTATTAGCC SEQ ID NO:1165 | GCTGCATCCAGTTTGCAA AGT SEQ ID NO:9177 | CAACAGTATTATAGTTACCC ATTCACT SEQ ID NO:17189 | |
| iPS:433903 | | AA | RASQGINNYLA SEQ ID NO:1166 | AASSLQS SEQ ID NO:9178 | QQYYSYPFT SEQ ID NO:17190 | |
| | 21-225_43H4 | NA | CGGGCGAGTCAGGGCATTAT CAACTGGTTAGCC SEQ ID NO:1167 | GCTGCATCCAGTTTGCAA AGT SEQ ID NO:9179 | CAACAGACTAACAGTTTCCC GTGGACG SEQ ID NO:17191 | |
| iPS:433905 | | AA | RASQGIINWLA SEQ ID NO:1168 | AASSLQS SEQ ID NO:9180 | QQTNSFPWT SEQ ID NO:17192 | |
| | 21-225_43E5 | NA | CGGGCAAGTCAGGGCATTAG AAATGATTAGGC SEQ ID NO:1169 | GGTGCATCCAATTTGCA AAGT SEQ ID NO:9181 | CTACAGCATACTAGTTTCCC ATTCACT SEQ ID NO:17193 | |
| iPS:433909 | | AA | RASQGIRNDLG SEQ ID NO:1170 | GASNLQS SEQ ID NO:9182 | LQHTSFPFT SEQ ID NO:17194 | |
| | 21-225_43D8 | NA | AAGTCCAGCAGCCAGAGTGTTT AATGACCTCCAACGATAAGA ACTACTTAACT SEQ ID NO:1171 | TGGGCTTCTACCCGGGA ATCC SEQ ID NO:9183 | CAGCAATATTATAGTACTCC TCCGACG SEQ ID NO:17195 | |
| iPS:433911 | | AA | KSSQSVLMTSNDKNYLT SEQ ID NO:1172 | WASTRES SEQ ID NO:9184 | QQYYSTPPT SEQ ID NO:17196 | |
| | 21-225_43E8 | NA | CGGGCGAGTCAGGGCATTAG CAACTGGTTAGCC SEQ ID NO:1173 | GCTGCATCCAGTTTGCAA AGT SEQ ID NO:9185 | CAACAGACTAACAGTTTCCC GTGGACG SEQ ID NO:17197 | |
| iPS:433913 | | AA | RASQGISNWLA SEQ ID NO:1174 | AASSLQS SEQ ID NO:9186 | QQTNSFPWT SEQ ID NO:17198 | |
| | | NA | CGGGCAAGTCAGGGCATTAG AAATGATTAGGC | GCTGCATCCAGTTTGCAA AGT | CTACAGCATAATAGTTTCCC ATTCACT | |

FIGURE 49
(Continued)

| | | | | | | |
|---|---|---|---|---|---|---|
| iPS:433915 | 21-225_43H8 | AA | SEQ ID NO:1175 RASQGIRNDLG SEQ ID NO:1176 | SEQ ID NO:9187 AASSLQS SEQ ID NO:9188 | SEQ ID NO:17199 LQHNSFPFT SEQ ID NO:17200 | |
| iPS:433917 | 21-225_43H9 | NA | CGGGCGAGTCAGGATATTAG CAGCTGGTTAGCC SEQ ID NO:1177 | GATGCATCCAGTTTGCA AAGT SEQ ID NO:9189 | CAACAGGCTAACAGTCTCC ATTCACT SEQ ID NO:17201 | |
| | | AA | RASQDISSWLA SEQ ID NO:1178 | DASSLQS SEQ ID NO:9190 | QQANSLPFT SEQ ID NO:17202 | |
| iPS:433917 | 21-225_43E11 | NA | AAGTCTAGTCAGAGCCTCCT GCACAGTGATGGAAGGACCT ATTTGTAT SEQ ID NO:1179 | GAAGTTTCCAACCGGTTC TCT SEQ ID NO:9191 | ATGCAAAGTATACAGCTTCC GTGGACG SEQ ID NO:17203 | |
| | | AA | KSSQSLLHSDGRTYLY SEQ ID NO:1180 | EVSNRFS SEQ ID NO:9192 | MQSIQLPWT SEQ ID NO:17204 | |
| iPS:433919 | 21-225_44B3 | NA | CGGGCAAGTCAGGGCATTAG AAATGATTAGGC SEQ ID NO:1181 | GCTGCATCCAGTTTGCAA AGT SEQ ID NO:9193 | CTACTGCATTATAATTACCT CGGACG SEQ ID NO:17205 | |
| | | AA | RASQGIRNDLG SEQ ID NO:1182 | AASSLQS SEQ ID NO:9194 | LLHYNYPRT SEQ ID NO:17206 | |
| iPS:433921 | 21-225_44C3 | NA | CGGGCAAGTCAGGGCATTAG AAATGATTAGGC SEQ ID NO:1183 | GCTGCATCCAGTTTGCAA AGT SEQ ID NO:9195 | CTACAGCATAGTAGTTACCC TCTCACT SEQ ID NO:17207 | |
| | | AA | RASQGIRNDLG SEQ ID NO:1184 | AASSLQS SEQ ID NO:9196 | LQHSSYPLT SEQ ID NO:17208 | |
| iPS:433923 | 21-225_44D3 | NA | CGGGCAAGTCAGGGCATTAG AGATGATTAGGC SEQ ID NO:1185 | GCTGCATCCAGTTTGCAA AGT SEQ ID NO:9197 | CTACAGCATTATAGTTACCC TCGGACG SEQ ID NO:17209 | |
| | | AA | RASQGIRDDLG SEQ ID NO:1186 | AASSLQS SEQ ID NO:9198 | LQHYSYPRT SEQ ID NO:17210 | |

FIGURE 49
(Continued)

| | | | | | |
|---|---|---|---|---|---|
| iPS:433925 | 21-225_44F3 | NA | CGGGGGAGTCAGGGTATTAG CGACTGGTTAGCC SEQ ID NO:1187 | GCTGCATCCAGTTTACAA AGT SEQ ID NO:9199 | CAACAGGCTAACAGTTTCCC ATTCACT SEQ ID NO:17211 |
| | | AA | RASQGISDWLA SEQ ID NO:1188 | AASSLQS SEQ ID NO:9200 | QQANSFPFT SEQ ID NO:17212 |
| iPS:433929 | 21-225_44D5 | NA | CGGGCAAGTCAGGACATTAG AAAGATTTAGGC SEQ ID NO:1189 | GCTGCATCCACTTTGGAA AGT SEQ ID NO:9201 | CTACAGCATTATAGTTTCCC GTGGACG SEQ ID NO:17213 |
| | | AA | RASQDIRKDLG SEQ ID NO:1190 | AASTLES SEQ ID NO:9202 | LQHYSFPWT SEQ ID NO:17214 |
| iPS:433931 | 21-225_44F6 | NA | AGGGCCAGTCAGAGTGTTAG TGGAAGCTACTTAGCC SEQ ID NO:1191 | GGTGCATCCAGCAGGGC CACT SEQ ID NO:9203 | CAGCAGTATGGTAGTTCACC GTGGACG SEQ ID NO:17215 |
| | | AA | RASQSVSGSYLA SEQ ID NO:1192 | GASSRAT SEQ ID NO:9204 | QQYGSSPWT SEQ ID NO:17216 |
| iPS:433933 | 21-225_44C8 | NA | CGGGCAAGTCAGGGCATTAG AAATGATTTAGGC SEQ ID NO:1193 | GCTGCATCCAATTGCAA AGT SEQ ID NO:9205 | CTACAGCATAATAGTTACCC ATTCACT SEQ ID NO:17217 |
| | | AA | RASQGIRNDLG SEQ ID NO:1194 | AASNLQS SEQ ID NO:9206 | LQHNSYPFT SEQ ID NO:17218 |
| iPS:433935 | 21-225_44F9 | NA | CGGGCAAGTCAGGGCATTAG AAATGATTTAGGC SEQ ID NO:1195 | GCTGCATCCAGTTTGCAA AGT SEQ ID NO:9207 | CTCCACCATTATAATTACCCT CGGACG SEQ ID NO:17219 |
| | | AA | RASQGIRNDLG SEQ ID NO:1196 | AASSLQS SEQ ID NO:9208 | LHHYNYPRT SEQ ID NO:17220 |
| iPS:433937 | 21-225_44B10 | NA | AAGTCTAGTCAGAGCCTCCT GCATAGTGAGGGAAGGACC TATTTGTAT SEQ ID NO:1197 | GAAATTTCCCACCGGTTC TCT SEQ ID NO:9209 | ATGCAAAGTATCCACCTTCC GTTCACT SEQ ID NO:17221 |
| | | AA | KSSQSLLHSEGRTYLY | EISHRFS | MQSIHLPFT |

FIGURE 49
(Continued)

| | | | | | | |
|---|---|---|---|---|---|---|
| iPS:433939 | 21-225_44C10 | NA | SEQ ID NO:1198 CGGGCAAGTCAGGGCATTAG AGATGATTTAGGC | SEQ ID NO:9210 GCTACATCCAGTTTGCAA AGT | SEQ ID NO:17222 CTACAGCATTATAGTTACCC TCGGACG |
| | | AA | SEQ ID NO:1199 RASQGIRDDLG | SEQ ID NO:9211 ATSSLQS | SEQ ID NO:17223 LQHYSYPRT |
| iPS:433941 | 21-225_44D10 | NA | SEQ ID NO:1200 CGGGCGAGTCAGGGCATTAG CGACTGGTTAGCC | SEQ ID NO:9212 GCTGCATCCAGTTTGCAA AGT | SEQ ID NO:17224 CAACAGACTAACAGTTTCCC GTGGACG |
| | | AA | SEQ ID NO:1201 RASQGISDWLA | SEQ ID NO:9213 AASSLQS | SEQ ID NO:17225 QQTNSFPWT |
| iPS:433943 | 21-225_44E10 | NA | SEQ ID NO:1202 AGGTCTAGTCAGAGCCTCCT GCATAGTAATGGATACAGCT ATTTGGAG | SEQ ID NO:9214 TTGGGTTCTAATCGGGCC TCC | SEQ ID NO:17226 ATGCAAACTCTACAAACTCC ATTCACT |
| | | AA | SEQ ID NO:1203 RSSQSLLHSNGYSYLE | SEQ ID NO:9215 LGSNRAS | SEQ ID NO:17227 MQTLQTPFT |
| iPS:433945 | 21-225_44C12 | NA | SEQ ID NO:1204 CGGGCGAGTCAGGGTATTAG CAACTGGTTAGCC | SEQ ID NO:9216 GCTGCATTCAGTTTGCAA AGT | SEQ ID NO:17228 CAACAGTCTAACAGTTTCCC GTGGACG |
| | | AA | SEQ ID NO:1205 RASQGISNWLA | SEQ ID NO:9217 AAFSLQS | SEQ ID NO:17229 QQSNSFPWT |
| iPS:433947 | 21-225_44E12 | NA | SEQ ID NO:1206 CGGACAAGTCAGGGCATTAG AAATGATTTAGGC | SEQ ID NO:9218 GCTGCATCCAGTTTGCAA AGT | SEQ ID NO:17230 CTACAACATAATAGTTACCC GCTCACT |
| | | AA | SEQ ID NO:1207 RTSQGIRNDLG | SEQ ID NO:9219 AASSLQS | SEQ ID NO:17231 LQHNSYPLT |
| iPS:433949 | 21-225_45H2 | NA | SEQ ID NO:1208 CGGGCAAGTCAGGGCATTAG AAATGATTTAGGC | SEQ ID NO:9220 GGTGCATCCAATTTGCA AAGT | SEQ ID NO:17232 CTACAGCATACTAGTTTCCC ATTCACT |
| | | | SEQ ID NO:1209 | SEQ ID NO:9221 | SEQ ID NO:17233 |

FIGURE 49
(Continued)

| | | | | | | |
|---|---|---|---|---|---|---|
| | | AA | RASQGIRNDLG | GASNLQS | LQHTSFPFT | |
| | | | SEQ ID NO:1210 | SEQ ID NO:9222 | SEQ ID NO:17234 | |
| iPS:433951 | 21-225_45B4 | NA | CGGGCAAGTCAGGGCATTAG AGATGATTAGGC | GCTGCATCCAGTTTGCAA AGT | CTACAGCATTATAGTTACCC TCGGACG | |
| | | | SEQ ID NO:1211 | SEQ ID NO:9223 | SEQ ID NO:17235 | |
| | | AA | RASQGIRDDLG | AASSLQS | LQHYSYPRT | |
| | | | SEQ ID NO:1212 | SEQ ID NO:9224 | SEQ ID NO:17236 | |
| iPS:433953 | 21-225_45H4 | NA | CGGGCGAGTCAGGGATATTAG CAGCTGGTTAGCC | GATGCATCCAGTTTGCA AAGT | CAACAGGCTAACAGTCTCCC TTTCACT | |
| | | | SEQ ID NO:1213 | SEQ ID NO:9225 | SEQ ID NO:17237 | |
| | | AA | RASQDISSWLA | DASSLQS | QQANSLPFT | |
| | | | SEQ ID NO:1214 | SEQ ID NO:9226 | SEQ ID NO:17238 | |
| iPS:433955 | 21-225_45B8 | NA | CGGGCAAGTCAGGGCATTAG AGATGATTAGGC | GCTGCATCCAGTTTGCAA AGT | CTACAGCATTATAATTACCC TCGGACG | |
| | | | SEQ ID NO:1215 | SEQ ID NO:9227 | SEQ ID NO:17239 | |
| | | AA | RASQDIRDDLG | AASSLQS | LQHYNYPRT | |
| | | | SEQ ID NO:1216 | SEQ ID NO:9228 | SEQ ID NO:17240 | |
| iPS:433957 | 21-225_45F8 | NA | CGGGCGAGTCAGGGATATTAG CGACTGGTTAGCC | GGTGCATCCAGTTTGCA AAGT | CAACAGACTAACAGTTTCCC GTGGACG | |
| | | | SEQ ID NO:1217 | SEQ ID NO:9229 | SEQ ID NO:17241 | |
| | | AA | RASQGISDWLA | GASSLQS | QQTNSFPWT | |
| | | | SEQ ID NO:1218 | SEQ ID NO:9230 | SEQ ID NO:17242 | |
| iPS:433959 | 21-225_45C9 | NA | CGGGCGAGTCAGGGATATTAG CGACTGGTTAGCT | GCTGCATCCAGTTTGGA AAGT | CAACAGGCTAACAGTTTCCC ATTCACT | |
| | | | SEQ ID NO:1219 | SEQ ID NO:9231 | SEQ ID NO:17243 | |
| | | AA | RASQDISDWLA | AASSLES | QQANSFPFT | |
| | | | SEQ ID NO:1220 | SEQ ID NO:9232 | SEQ ID NO:17244 | |
| iPS:433961 | 21-225_45D9 | NA | CGGGCGAGTCAGGGCATTAA CAATTATTTAGCC | GCTGCATCCAGTTTGCAA AGT | CAACACTATTATAGTTACCC ATTCACT | |
| | | | SEQ ID NO:1221 | SEQ ID NO:9233 | SEQ ID NO:17245 | |

FIGURE 49
(Continued)

| | | | | | | | |
|---|---|---|---|---|---|---|---|
| iPS:433963 | | AA | RASQGINNYLA SEQ ID NO:1222 | | AASSLQS SEQ ID NO:9234 | | QHYYSYPFT SEQ ID NO:17246 |
| | 21-225_46B1 | NA | CGGGCAAGTCAGGGCATTAG AAATGATTTAGGC SEQ ID NO:1223 | | GCTGCATCCAGTTTGCAA GGT SEQ ID NO:9235 | | CTACAGCATAATAGTTACC GCTCACT SEQ ID NO:17247 |
| iPS:433965 | | AA | RASQGIRNDLG SEQ ID NO:1224 | | AASSLQG SEQ ID NO:9236 | | LQHNSYPLT SEQ ID NO:17248 |
| | 21-225_46F2 | NA | AAGTCTAGTCAGAGCCTCCT GCATGGTGATGGAAAGACATTCT ATTTGTAT SEQ ID NO:1225 | | GAAGTTTCCAATCGGTTC TCT SEQ ID NO:9237 | | ATGCAAAGTATACAGTTTCC GTGGACG SEQ ID NO:17249 |
| iPS:433967 | | AA | KSSQSLLHGDGKTYLY SEQ ID NO:1226 | | EVSNRFS SEQ ID NO:9238 | | MQSIQLPWT SEQ ID NO:17250 |
| | 21-225_46C3 | NA | CGGGCAAGTCAGGGCATTAG AGATGATTTAGGC SEQ ID NO:1227 | | GCTGCATCCAGTTTGCAA AGT SEQ ID NO:9239 | | CTACAGCATTATAGTTACC TCGGACG SEQ ID NO:17251 |
| iPS:433969 | | AA | RASQGIRDDLG SEQ ID NO:1228 | | AASSLQS SEQ ID NO:9240 | | LQHYSYPRT SEQ ID NO:17252 |
| | 21-225_46F3 | NA | CGGGCAAGTCAGGGCATTAG AAAAGATTTAGGC SEQ ID NO:1229 | | GCTGCATCCAGTTTGCAA AGT SEQ ID NO:9241 | | CTACAGCATAATAGTTACC TCTCACT SEQ ID NO:17253 |
| iPS:433971 | | AA | RASQGIRKDLG SEQ ID NO:1230 | | AASSLQS SEQ ID NO:9242 | | LQHNSYPLT SEQ ID NO:17254 |
| | 21-225_46D4 | NA | CGGGCAAGTCAGGGACATTAG AAAAGATTTAGGC SEQ ID NO:1231 | | GCTGCATCCAGTTTGGA AAGT SEQ ID NO:9243 | | CTACAGCATTATAGTTTCC GTGGACG SEQ ID NO:17255 |
| iPS:433973 | | AA | RTSQDIRKDLG SEQ ID NO:1232 | | AASSLES SEQ ID NO:9244 | | LQHYSFPWT SEQ ID NO:17256 |
| | | NA | CGGGCGAGTCAGGGTATTAG CAACTGGTTAGCC | | GCTGCATCCAGTTTGCAA AGT | | CAACAGACTAACAGTTTCC GTGGACG |

FIGURE 49
(Continued)

| | | | | | | | |
|---|---|---|---|---|---|---|---|
| iPS:433975 | 21-225_46A6 | AA | SEQ ID NO:1233 RASQGISNWLA SEQ ID NO:1234 | SEQ ID NO:9245 AASSLQS SEQ ID NO:9246 | SEQ ID NO:17257 QQTNSFPWT SEQ ID NO:17258 |
| iPS:433977 | 21-225_46C6 | NA | CGGGCAAGTCAGGGCATTAG AAATGATTAGGC SEQ ID NO:1235 RASQGIRNDLG SEQ ID NO:1236 | GCTGCATCCAGTTTGCAA AGT SEQ ID NO:9247 AASSLQS SEQ ID NO:9248 | CTACAGCATAATAGTTACCC TCTCACT SEQ ID NO:17259 LQHNSYPLT SEQ ID NO:17260 |
| iPS:433979 | 21-225_46D8 | NA AA | CGGGCAAGTCAGGGCATTAG AAAGATTTAGGC SEQ ID NO:1237 RASQGIRKDLG SEQ ID NO:1238 | GCTGCATCCAGTTTGCAA AGT SEQ ID NO:9249 AASSLQS SEQ ID NO:9250 | CTACAGCATAATAGTTACCC TCTCACT SEQ ID NO:17261 LQHNSYPLT SEQ ID NO:17262 |
| | 21-225_46B9 | NA AA | AAGTCTAGTCAGAGCCTCCT GCATAGTGAGGGAAAGACC TATTTGTAT SEQ ID NO:1239 KSSQSLLHSEGKTYLY SEQ ID NO:1240 | GAAGTTTCTTACCGGTTC TCT SEQ ID NO:9251 EVSYRFS SEQ ID NO:9252 | ATGCACAGTATACAGTATCC GCTCACG SEQ ID NO:17263 MHSIQYPLT SEQ ID NO:17264 |
| iPS:433981 | 21-225_46E9 | NA AA | CGGGCAAGTCAGGGCATTAG AAATGATTAGGC SEQ ID NO:1241 RASQGIRNDLG SEQ ID NO:1242 | GCTGCATCCAGTTTGCAA AGT SEQ ID NO:9253 AASSLQS SEQ ID NO:9254 | CTTCAGCATACTAGTTTCCC ATTCACT SEQ ID NO:17265 LQHTSFPFT SEQ ID NO:17266 |
| iPS:433983 | 21-225_47A1 | NA AA | CGGGCAAGTCAGGACATTAG AAATGATTAGGC SEQ ID NO:1243 RASQDIRNDLG SEQ ID NO:1244 | GCTGCATTCAGTTTGCAA AGT SEQ ID NO:9255 AAFSLQS SEQ ID NO:9256 | CTGCAACATAATAGTTACCC GCTCACT SEQ ID NO:17267 LQHNSYPLT SEQ ID NO:17268 |

FIGURE 49
(Continued)

| | | | | | |
|---|---|---|---|---|---|
| iPS:433985 | 21-225_47C1 | NA | ACGTCTAGTCAGAGCCTCCT GCATAGTAGTGAAGGAAAGACC TATTTGTAT<br>SEQ ID NO:1245 | GAAGTTCCAACCGGTTC TCT<br>SEQ ID NO:9257 | ATGCAAAGTATACAGCTTCC GTGGACG<br>SEQ ID NO:17269 |
| | | AA | TSSQSLLHSEGKTYLY<br>SEQ ID NO:1246 | EVSNRFS<br>SEQ ID NO:9258 | MQSIQLPWT<br>SEQ ID NO:17270 |
| iPS:433987 | 21-225_47A5 | NA | CGGGCAAGTCAGGGCATTAG AAATGATTTAGGC<br>SEQ ID NO:1247 | GCTGCATCCAGTTTGCAA AGT<br>SEQ ID NO:9259 | CTACAGCATAATAGTTACC GCTCACT<br>SEQ ID NO:17271 |
| | | AA | RASQGIRNDLG<br>SEQ ID NO:1248 | AASSLQS<br>SEQ ID NO:9260 | LQHNSYPLT<br>SEQ ID NO:17272 |
| iPS:433989 | 21-225_47C7 | NA | AGGTCTAGTCAGAGCCTCCT GCATAGTAATGGATACAACT ATTTGGAA<br>SEQ ID NO:1249 | TTGGGTTTTAATCGGGCC TCC<br>SEQ ID NO:9261 | ATGCAAGTTCTACAAACTCC ATTCACT<br>SEQ ID NO:17273 |
| | | AA | RSSQSLLHSNGYNYLE<br>SEQ ID NO:1250 | LGFNRAS<br>SEQ ID NO:9262 | MQVLQTPFT<br>SEQ ID NO:17274 |
| iPS:433991 | 21-225_47E7 | NA | AAGTCTAGTCAGAGCCTCCT GCATAGTGATGAAGGACCTTCT ATTTGTAT<br>SEQ ID NO:1251 | GAAGTTCCAGCCGGTTC TCT<br>SEQ ID NO:9263 | ATGCAAAGTACACAACTTCC GTGGACG<br>SEQ ID NO:17275 |
| | | AA | KSSQSLLHSDGRTYLY<br>SEQ ID NO:1252 | EVSSRFS<br>SEQ ID NO:9264 | MQSTQLPWT<br>SEQ ID NO:17276 |
| iPS:433993 | 21-225_47G7 | NA | CGGGCGAAGTCAGGGTATTAG CAACTGGTTAGGC<br>SEQ ID NO:1253 | GCTGCCTCCAATTGCAA AGT<br>SEQ ID NO:9265 | CAACAGGTTAACAGTTTCCC GTGGACG<br>SEQ ID NO:17277 |
| | | AA | RASQGISNWLA<br>SEQ ID NO:1254 | AASNLQS<br>SEQ ID NO:9266 | QQVNSFPWT<br>SEQ ID NO:17278 |
| iPS:433995 | | NA | CGGACAAGTCAGGGCATTAG AAATGATTTAGGC | GCTGCATCCAGTTTGCAA AGT | CTACAACATACTAGTTTCCC ATTCACT |

FIGURE 49
(Continued)

| | | | | | | |
|---|---|---|---|---|---|---|
| iPS:433997 | 21-225_47H7 | AA | SEQ ID NO:1255 RTSQGIRNDLG | SEQ ID NO:9267 AASSLQS | SEQ ID NO:17279 LQHTSPFT | |
| | | NA | SEQ ID NO:1256 CGGACAAGTCAGGGCATTAG AAATGATTAGGC | SEQ ID NO:9268 AGAGCATCCAGTTGCA AAGT | SEQ ID NO:17280 CTACAGCATAATTTTACC GTGGACG | |
| iPS:433999 | 21-225_48C1 | AA | SEQ ID NO:1257 RTSQGIRNDLG | SEQ ID NO:9269 RASSLQS | SEQ ID NO:17281 LQHNFYPWT | |
| | | NA | SEQ ID NO:1258 CGGGCAAGTCAGAGCATTAG CAGCTATTTAATT | SEQ ID NO:9270 GCTGCATCCAGTTGCAA AGT | SEQ ID NO:17282 CAACAGAGTAACAGTATTCC ATTCACT | |
| iPS:434001 | 21-225_48D1 | AA | SEQ ID NO:1259 RASQSISSYLI | SEQ ID NO:9271 AASSLQS | SEQ ID NO:17283 QQSNSIPFT | |
| | | NA | SEQ ID NO:1260 CGGGCAAGTCGGGGCATTAG AGATGATTAGGC | SEQ ID NO:9272 GCTGCATCCAGTTGCAA AGT | SEQ ID NO:17284 CTACAGCAATATAGTTATCC TCGGACG | |
| iPS:434003 | 21-225_48F2 | AA | SEQ ID NO:1261 RASRGIRDDLG | SEQ ID NO:9273 AASSLQS | SEQ ID NO:17285 LQQYSYPRT | |
| | | NA | SEQ ID NO:1262 CGGGCAAGTCAGAGCATTAT CAGCTATTTAATT | SEQ ID NO:9274 GCTGCATCCAGTTGCAA AGT | SEQ ID NO:17286 CAACAGACTAACAGTATTCC ATTCACT | |
| iPS:434007 | 21-225_48C3 | AA | SEQ ID NO:1263 RASQSISYLI | SEQ ID NO:9275 AASSLQS | SEQ ID NO:17287 QQTNSIPFT | |
| | | NA | SEQ ID NO:1264 CGGGCGAAGTCAAAATATTAC CAGCTGGTTAGCC | SEQ ID NO:9276 AGTGCATCCAGTTGCA AAAT | SEQ ID NO:17288 CAACAGGCTAACAGTTTCCC GTGGACG | |
| iPS:434009 | 21-225_48D7 | AA | SEQ ID NO:1265 RASQNITSWLA | SEQ ID NO:9277 SASSLQN | SEQ ID NO:17289 QQANSFPWT | |
| | | NA | SEQ ID NO:1266 CGGGCAAGTCAGGGCATTAG AAATGATTAGGC | SEQ ID NO:9278 ATTGCATCCAGTTGCAA AGT | SEQ ID NO:17290 CTACAGCATAATCGTTACC GTGGACG | |

FIGURE 49
(Continued)

| | | | | | | | |
|---|---|---|---|---|---|---|---|
| iPS:434011 | 21-225_48A9 | AA | SEQ ID NO:1267<br>RASQGIRNDLG<br>SEQ ID NO:1268 | SEQ ID NO:9279<br>IASSLQS<br>SEQ ID NO:9280 | SEQ ID NO:17291<br>LQHNRYPWT<br>SEQ ID NO:17292 | |
| iPS:434013 | 21-225_48B10 | NA | CGGGCAAGTCAGAGAGCATTAG<br>GAAGTATTTAAAT<br>SEQ ID NO:1269 | GCTGCTTCCAGTTGCAA<br>AGT<br>SEQ ID NO:1270 | CAACAGACTTACAGTAACCC<br>ACTCACT<br>SEQ ID NO:17293 | |
| | | AA | RASQSIRKYLN<br>SEQ ID NO:1270 | AASSLQS<br>SEQ ID NO:9282 | QQTYSNPLT<br>SEQ ID NO:17294 | |
| iPS:434015 | 21-225_48D12 | NA | CGGGCAAGTCAGAGAGCATTAG<br>AAATGATTTAGGC<br>SEQ ID NO:1271 | GCTGCATCCACTTGCAA<br>AGT<br>SEQ ID NO:9283 | CTACAGCATAATAGTTACCC<br>GCTCACT<br>SEQ ID NO:17295 | |
| | | AA | RASQGIRNDLG<br>SEQ ID NO:1272 | AASTLQS<br>SEQ ID NO:9284 | LQHNSYPLT<br>SEQ ID NO:17296 | |
| iPS:434017 | 21-225_48F12 | NA | CGGGCAAGTCAGAGAGCATTAG<br>GAAGTATTTAAAT<br>SEQ ID NO:1273 | GCTGCTTCCAGTTGCAA<br>AGT<br>SEQ ID NO:9285 | CAACAGACTTACAGTAACCC<br>GCTCACT<br>SEQ ID NO:17297 | |
| | | AA | RASQSIRKYLN<br>SEQ ID NO:1274 | AASSLQS<br>SEQ ID NO:9286 | QQTYSNPLT<br>SEQ ID NO:17298 | |
| iPS:434019 | 21-225_48G12 | NA | CGGGCAAGTCAGAGAGCATTAG<br>GAAGTATTTAAAT<br>SEQ ID NO:1275 | GCTGCTTCCAGTTGCAA<br>AGT<br>SEQ ID NO:9287 | CAACAGACTTACAGTAACCC<br>GCTCACT<br>SEQ ID NO:17299 | |
| | | AA | RASQSIRKYLN<br>SEQ ID NO:1276 | AASSLQS<br>SEQ ID NO:9288 | QQTYSNPLT<br>SEQ ID NO:17300 | |
| iPS:434019 | 21-225_49A1 | NA | CGGGCAAGTCAGGGCATTAG<br>AAATGATTAGAC<br>SEQ ID NO:1277 | GCTGCATCCAGTTGCAA<br>AGT<br>SEQ ID NO:9289 | CTACAGCATAATAGTTACCC<br>GCTCACT<br>SEQ ID NO:17301 | |
| | | AA | RASQGIRNDLD<br>SEQ ID NO:1278 | AASSLQS<br>SEQ ID NO:9290 | LQHNSYPLT<br>SEQ ID NO:17302 | |

FIGURE 49 (Continued)

| | | | | | |
|---|---|---|---|---|---|
| iPS:434021 | 21-225_49C1 | NA | AAGTCTAGTCAGAGCCTCCT GCATAGGGAAGGAAAGACC TATTTGTAC SEQ ID NO:1279 | GAAGTTTCCCACCGGGTC TCT SEQ ID NO:9291 | ATGCAAAGTATACAGATTCC GATCACC SEQ ID NO:17303 |
| | | AA | KSSQSLLHREGKTYLY SEQ ID NO:1280 | EVSHRFS SEQ ID NO:9292 | MQSIQIPIT SEQ ID NO:17304 |
| iPS:434023 | 21-225_49F1 | NA | CGGGCGAGTCGGGATATTAA CGGCTGGTTAGCC SEQ ID NO:1281 | ACTGTCTCCAGTTTGCAA AGT SEQ ID NO:9293 | CAACAGTCTAACAGTTCCC ATTCACT SEQ ID NO:17305 |
| | | AA | RASRDINGWLA SEQ ID NO:1282 | TVSSLQS SEQ ID NO:9294 | QQSNSFPFT SEQ ID NO:17306 |
| iPS:434025 | 21-225_49G3 | NA | AAGTCTAGTCAGAGCCTCCT GCATAGTGAAGGAAAGACC TATTTGTAT SEQ ID NO:1283 | GAAGTTTCCAACCGGCT CTCT SEQ ID NO:9295 | ATGCAAAGTATGCAGCTTCC GATCACC SEQ ID NO:17307 |
| | | AA | KSSQSLLHSEGKTYLY SEQ ID NO:1284 | EVSNRLS SEQ ID NO:9296 | MQSMQLPIT SEQ ID NO:17308 |
| iPS:434027 | 21-225_49H5 | NA | CGGGCGAGTCAGGGTTTTAG CACCTGGTTAGCC SEQ ID NO:1285 | GCTGCATCCAGTTGCAA GAT SEQ ID NO:9297 | CAACAGACTAACAGTTCCC GTTCACT SEQ ID NO:17309 |
| | | AA | RASQGFSTWLA SEQ ID NO:1286 | AASSLQD SEQ ID NO:9298 | QQTNSFPFT SEQ ID NO:17310 |
| iPS:434029 | 21-225_49C6 | NA | CGGGCAAGTCAGGGCATTAG AAATGATTTAGGC SEQ ID NO:1287 | GCTGCATCCAGTTGCAA AGT SEQ ID NO:9299 | CTACAGCATAATAGTTACCC TCTCACT SEQ ID NO:17311 |
| | | AA | RASQGIRNDLG SEQ ID NO:1288 | AASSLQS SEQ ID NO:9300 | LQHNSYPLT SEQ ID NO:17312 |
| iPS:434031 | 21-225_49E7 | NA | AAGTCTAGTCAGATCTTCTT GCATAGTGAAGGAAAGACC TATTTGTAT | GAAGTTTCCAAGCGGCT CTCT | ATGCAAAGTATGCAGCTTCC GATTATC |

FIGURE 49
(Continued)

| | | | | | | |
|---|---|---|---|---|---|---|
| iPS:434033 | 21-225_49E7 | AA | SEQ ID NO:1289<br>KSSQIFLHSEGKTYLY<br>SEQ ID NO:1290 | SEQ ID NO:9301<br>EVSKRLS<br>SEQ ID NO:9302 | SEQ ID NO:17313<br>MQSMQLPH<br>SEQ ID NO:17314 | |
| | | NA | AAGTCTAATCAGAGCCTGT<br>GCATAATGAAGGAAAGACC<br>TATTTGTAT<br>SEQ ID NO:1291 | GAAGTTTCCAACCGGTTC<br>TCT<br>SEQ ID NO:9303 | ATGCAAAGTATACAGTATCC<br>GATCACC<br>SEQ ID NO:17315 | |
| iPS:434035 | 21-225_49F9 | AA | KSNQSLVHNEGKTYLY<br>SEQ ID NO:1292 | EVSNRFS<br>SEQ ID NO:9304 | MQSIQYPIT<br>SEQ ID NO:17316 | |
| iPS:434037 | 21-225_49F10 | NA | CGGGCGAGTCAGGGTATTAG<br>CAGGTGGTTAGCC<br>SEQ ID NO:1293 | GCTGCATCCACTTTGCAA<br>AGT<br>SEQ ID NO:9305 | CAACAGGCTAACAGTTTCCC<br>ATTCACT<br>SEQ ID NO:17317 | |
| | | AA | RASQGISRWLA<br>SEQ ID NO:1294 | AASTLQS<br>SEQ ID NO:9306 | QQANSFPFT<br>SEQ ID NO:17318 | |
| iPS:434039 | 21-225_49G12 | NA | CGGTCAAGTCAGAGCATTAG<br>TACCTATTAATG<br>SEQ ID NO:1295 | GCTGCATCCAGTTTGCAA<br>ATT<br>SEQ ID NO:9307 | CAACAGAGTTACAGTATCCC<br>ATTCACT<br>SEQ ID NO:17319 | |
| | | AA | RSSQSISTYLM<br>SEQ ID NO:1296 | AASSLQI<br>SEQ ID NO:9308 | QQSYSIPFT<br>SEQ ID NO:17320 | |
| iPS:434041 | 21-225_43B1 | NA | CGGGCAAGTCAGGGCATTAG<br>AAATGATTTAGGC<br>SEQ ID NO:1297 | GCTGCATCCAGTTGCAA<br>AGT<br>SEQ ID NO:9309 | CTACAGCATACTAGTTTCCC<br>ATTCACT<br>SEQ ID NO:17321 | |
| | | AA | RASQGIRNDLG<br>SEQ ID NO:1298 | AASSLQS<br>SEQ ID NO:9310 | LQHTSFPFT<br>SEQ ID NO:17322 | |
| iPS: | 21-225_50H8 | NA | CGGGCAAGTCAGAGCATTAG<br>CAGCTATTTAATT<br>SEQ ID NO:1299 | GCTGCATCCAGTCTGCA<br>AAGT<br>SEQ ID NO:9311 | CAACAGAGTAACAGTCTTCC<br>ATTCACT<br>SEQ ID NO:17323 | |
| | | AA | RASQSISSYLI<br>SEQ ID NO:1300 | AASSLQS<br>SEQ ID NO:9312 | QQSNSLPFT<br>SEQ ID NO:17324 | |

FIGURE 49
(Continued)

| | | | | | |
|---|---|---|---|---|---|
| iPS:434043 | 21-225_50G10 | NA | CGGGCAAGTCAGGGCATTAG AAATAATTAGGC SEQ ID NO:1301 | GCTGCATCCAGTTTGCAA AGT SEQ ID NO:9313 | CTACAGTATAATAGTTACCC GTTCACT SEQ ID NO:17325 |
| | | AA | RASQGIRNNLG SEQ ID NO:1302 | AASSLQS SEQ ID NO:9314 | LQYNSYPFT SEQ ID NO:17326 |
| iPS:434045 | 21-225_50H10 | NA | CGGGCAAGTCAGAGCATTA CAGCTATTTAATT SEQ ID NO:1303 | GCTGCATCCAGTTTGCAA AGT SEQ ID NO:9315 | CAACAGAGTAACAGTATTCC ATTCACT SEQ ID NO:17327 |
| | | AA | RASQSIYSYLI SEQ ID NO:1304 | AASSLQS SEQ ID NO:9316 | QQSNSIPFT SEQ ID NO:17328 |
| iPS:434047 | 21-225_50A12 | NA | CGGGCAAGTCAGGGCATTAG AAATGATTAGGC SEQ ID NO:1305 | ACTGCATCCAATTTACAA AGT SEQ ID NO:9317 | CTACAGCATAATAGTTACCC GTGGACG SEQ ID NO:17329 |
| | | AA | RASQGIRNDLG SEQ ID NO:1306 | TASNLQS SEQ ID NO:9318 | LQHNSYPWT SEQ ID NO:17330 |
| iPS:434049 | 21-225_50B12 | NA | CGGGCAAGTCAGAGCATTAG TAGTTATTTAAAT SEQ ID NO:1307 | GCTGCATCCAGTTTGCAA AGT SEQ ID NO:9319 | CAACAGAGTTACATTGCCCC ATTCACT SEQ ID NO:17331 |
| | | AA | RASQSISSYLN SEQ ID NO:1308 | AASSLQS SEQ ID NO:9320 | QQSYIAPFT SEQ ID NO:17332 |
| iPS:434053 | 21-225_51E1 | NA | AAGTCTAGTCAGAGCCTCCT GCATAGTGAGGGAAAGACC TATTTGTAT SEQ ID NO:1309 | GAAGTTTCCAACCGGTTC TCT SEQ ID NO:9321 | ATGCAAAGTATACAGCTTCC ATTCACT SEQ ID NO:17333 |
| | | AA | KSSQSLLHSEGKTYLY SEQ ID NO:1310 | EVSNRFS SEQ ID NO:9322 | MQSIQLPFT SEQ ID NO:17334 |
| iPS:434055 | 21-225_51B4 | NA | CAGGCGAGTCGGGACATTAC CTTCTATTTAAAT SEQ ID NO:1311 | GATGCATCCAATTTGGA AACA SEQ ID NO:9323 | CAACAGTATGATAATCTTCC ATTCACT SEQ ID NO:17335 |
| | | AA | QASRDITFYLN | DASNLET | QQYDNLPFT |

FIGURE 49
(Continued)

| | | | | | | | | |
|---|---|---|---|---|---|---|---|---|
| iPS:434057 | 21-225_51E4 | NA | SEQ ID NO:1312 | CGGGCAAGTCAGGGCAGGCATTAG AAATGATTTAGGC | SEQ ID NO:9324 | GCTGCATCCAGTTTGCAA AGT | SEQ ID NO:17336 | CTACAGCATAATAGTTACCC ATTCACT |
| | | AA | SEQ ID NO:1313 RASQGIRNDLG | | SEQ ID NO:9325 AASSLQS | | SEQ ID NO:17337 LQHNSYPFT | |
| iPS:434059 | 21-225_51C5 | NA | SEQ ID NO:1314 | CGGGCGAGTCAGGGCATTAG CAATTATTTAGCC | SEQ ID NO:9326 | GCTGCATCCAGTTTGCGA AGT | SEQ ID NO:17338 | CAACAGTATTATAGTTACCC ATTCACT |
| | | AA | SEQ ID NO:1315 RASQGISNYLA | | SEQ ID NO:9327 AASSLRS | | SEQ ID NO:17339 QQYYSYPFT | |
| iPS:434061 | 21-225_51C7 | NA | SEQ ID NO:1316 | CGGGCGAGTCAGGATGTTAA CAACTACTTAGCC | SEQ ID NO:9328 | GCTGCATCCAGTTTGCAA AAT | SEQ ID NO:17340 | CAACAAACTAACAGTTTCC ATTCACT |
| | | AA | SEQ ID NO:1317 RASQDVNNYLA | | SEQ ID NO:9329 AASSLQN | | SEQ ID NO:17341 QQTNSFPFT | |
| iPS:434063 | 21-225_51G7 | NA | SEQ ID NO:1318 | CGGGCGAGTCAGGATATTAA CAGTTGGTTAGCC | SEQ ID NO:9330 | GCTCCATCCAATTTGCAA AGT | SEQ ID NO:17342 | CAACAGGCTCACAGTTTCCC GTGGACG |
| | | AA | SEQ ID NO:1319 RASQDISSWLA | | SEQ ID NO:9331 APSNLQS | | SEQ ID NO:17343 QQAHSFPWT | |
| iPS:434065 | 21-225_50D4 | NA | SEQ ID NO:1320 | CGGGCGAGTCAGGGCATTAG CAGTGGTTAGCC | SEQ ID NO:9332 | GCTGCATCCACTTTGCAA AGT | SEQ ID NO:17344 | CAACAGGCTAACAGTTTCCC ATTCACT |
| | | AA | SEQ ID NO:1321 RASQGISRWLA | | SEQ ID NO:9333 AASTLQS | | SEQ ID NO:17345 QQANSFPFT | |
| iPS:434067 | 21-225_51H8 | NA | SEQ ID NO:1322 | CGGGCAAGTCAGGGCATTAG AAATGATTTGGGC | SEQ ID NO:9334 | GCTGCTTCCAGTTTGCAA AGT | SEQ ID NO:17346 | CTACAGCATAATAGTTACCC GTGGACG |
| | | AA | SEQ ID NO:1323 RASQGIRNDLG | | SEQ ID NO:9335 AASSLQS | | SEQ ID NO:17347 LQHNSYPWT | |

FIGURE 49
(Continued)

| | | | | | | |
|---|---|---|---|---|---|---|
| iPS:434069 | 21-225_51E9 | NA | SEQ ID NO:1324 CGGGCGAGTCAGGGTATTAG CAGTTGGTTAGCC | SEQ ID NO:9336 GTTGCATCCAGTTTGCAA AGT | SEQ ID NO:17348 CAACAGGCTAAAAGTTTCC ATTCACT |
| | | AA | SEQ ID NO:1325 RASQGISSWLA | SEQ ID NO:9337 VASSLQS | SEQ ID NO:17349 QQAKSFPFT |
| iPS:434071 | 21-225_51F9 | NA | SEQ ID NO:1326 CGGGCAAGTCAGGGCATTAG GACTGATTTAGGC | SEQ ID NO:9338 GCTGCATCCAGTTTGCAA CGT | SEQ ID NO:17350 CTACAGCATAATAGTTACCC ATTCACT |
| | | AA | SEQ ID NO:1327 RASQGIRTDLG | SEQ ID NO:9339 AASSLQR | SEQ ID NO:17351 LQHNSYPFT |
| iPS:434073 | 21-225_51H10 | NA | SEQ ID NO:1328 CGGGCAAGTCAGAGAGCATTAG TACCTATTTAATG | SEQ ID NO:9340 GCTGCATCCAGTTTGCAA AGT | SEQ ID NO:17352 CAACAGAGTTACAGTATCC ATTCACT |
| | | AA | SEQ ID NO:1329 RASQSISTYLM | SEQ ID NO:9341 AASSLQS | SEQ ID NO:17353 QQSYSIPFT |
| iPS:434075 | 21-225_51B11 | NA | SEQ ID NO:1330 CGGACAAGTCAGGGCATTAG AAATGATTTAGGC | SEQ ID NO:9342 GCTGCATCCAGTTTGCAA AGT | SEQ ID NO:17354 CTACAGCATAATAGTTACCC ATTCACT |
| | | AA | SEQ ID NO:1331 RTSQGIRNDLG | SEQ ID NO:9343 AASSLQS | SEQ ID NO:17355 LQHNSYPFT |
| iPS:434077 | 21-225_51F11 | NA | SEQ ID NO:1332 CGGGCAAGTCAGGGCATTAG AAATGATTTAGGC | SEQ ID NO:9344 GCTGCATCCAGTTTGCAA AGT | SEQ ID NO:17356 CTACAGCATAATAGTTACCC GTTCACT |
| | | AA | SEQ ID NO:1333 RASQGIRNDLG | SEQ ID NO:9345 AASSLQS | SEQ ID NO:17357 LQHNSYPFT |
| iPS:434079 | 21-225_52B1 | NA | SEQ ID NO:1334 CGGGCGAGTCAGGATATTCG CACCTGGTTAGCC | SEQ ID NO:9346 GCTGCATCCAGTTTGCAA AAT | SEQ ID NO:17358 CAACAGGCTAAAAGTTTCC ATTCACT |
| | | AA | SEQ ID NO:1335 RASQDIRTWLA | SEQ ID NO:9347 AASSLQN | SEQ ID NO:17359 QQAKSFPFT |

FIGURE 49
(Continued)

| | | | | | | |
|---|---|---|---|---|---|---|
| iPS:434081 | 21-225_52B2 | NA | SEQ ID NO:1336 CGGGCAAGTCAGGGCATTAG AAATGATTTAGGC | SEQ ID NO:9348 GCTGCATCCTCTTTTGCAA AGT | SEQ ID NO:17360 CTGCAGCATAATAGCTACCC TCTCACT | |
| | | AA | SEQ ID NO:1337 RASQGIRNDLG | SEQ ID NO:9349 AASFLQS | SEQ ID NO:17361 LQHNSYPLT | |
| iPS:434083 | 21-225_52H2 | NA | SEQ ID NO:1338 CGGGCGAGTCAGAGAATATTAC CAACTGGTTAGCC | SEQ ID NO:9350 ACTACATCCAGTTTGCAA AGT | SEQ ID NO:17362 CAACAGACTAACAGTTTCCC GTGGACG | |
| | | AA | SEQ ID NO:1339 RASQNITNWLA | SEQ ID NO:9351 TTSSLQS | SEQ ID NO:17363 QQTNSFPWT | |
| iPS:434085 | 21-225_52E3 | NA | SEQ ID NO:1340 CGGGCGAGTCAGGGCATTAG CAATTATTTAGCC | SEQ ID NO:9352 GCTGCATCCAGTTTACAA AGT | SEQ ID NO:17364 CAACAGTATAATAGTTTCCC TTTCACT | |
| | | AA | SEQ ID NO:1341 RASQGISNYLA | SEQ ID NO:9353 AASSLQS | SEQ ID NO:17365 QQYNSFPFT | |
| iPS:434087 | 21-225_52F6 | NA | SEQ ID NO:1342 CAGGCGAGTCAGGACACATTAG TAACTATTTACAT | SEQ ID NO:9354 GATGCATCCACTTTGGG AACA | SEQ ID NO:17366 CAACAGTGTGATAATCTCCC GCTCACT | |
| | | AA | SEQ ID NO:1343 QASQDISNYLH | SEQ ID NO:9355 DASTLGT | SEQ ID NO:17367 QQCDNLPLT | |
| iPS:434091 | 21-225_52B9 | NA | SEQ ID NO:1344 CGGGCAAGTCAGGGCATTAG AAATGATTTAGGC | SEQ ID NO:9356 GCTGCATCCAGTTTGCAA AGT | SEQ ID NO:17368 CTACAGCATAATAGTTACCC ATTCACT | |
| | | AA | SEQ ID NO:1345 RASQGIRNDLG | SEQ ID NO:9357 AASSLQS | SEQ ID NO:17369 LQHNSYPFT | |
| iPS:434093 | 21-225_52D10 | NA | SEQ ID NO:1346 AAGTCTAGTCAGTCAGAGCCTCCT GCATAGTGAAGGAAAGACC TATTTGTAT | SEQ ID NO:9358 GAAGTTTCCAACCGGGT CTCT | SEQ ID NO:17370 ATGCAAAGTATACAGTATCC GATCACC | |
| | | | SEQ ID NO:1347 | SEQ ID NO:9359 | SEQ ID NO:17371 | |

FIGURE 49
(Continued)

| | | | KSSQSLLHSEGKTYLY | EVSNRVS | MQSIQYPIT |
|---|---|---|---|---|---|
| | | AA | SEQ ID NO:1348 | SEQ ID NO:9360 | SEQ ID NO:17372 |
| iPS:434095 | 21-225_52F10 | NA | CGGGCGAGTCAGGGTATTAG TAATTATTAGGC SEQ ID NO:1349 | GCTGCATCTAGTTTGCAA AGT SEQ ID NO:9361 | CAACAGTATAATAGTTATCC TCCGACG SEQ ID NO:17373 |
| | | AA | RASQGISNYLG SEQ ID NO:1350 | AASSLQS SEQ ID NO:9362 | QQYNSYPPT SEQ ID NO:17374 |
| iPS:434097 | 21-225_52H10 | NA | CGGGCGAGTCAGGATATTAA CAGTTGGTTAGCC SEQ ID NO:1351 | GTTGCATCCAGTTTGCA AGT SEQ ID NO:9363 | CAACAGGCTAAAAGTTTCCC ATTCACT SEQ ID NO:17375 |
| | | AA | RASQDINSWLA SEQ ID NO:1352 | VASSLQS SEQ ID NO:9364 | QQAKSFPFT SEQ ID NO:17376 |
| iPS:434101 | 21-225_52H12 | NA | CGGGCAAGTCAGGGCATAA GAAATAATTAGGC SEQ ID NO:1353 | GGTGCATCCAGTTTGCA AAGT SEQ ID NO:9365 | CTACAGTATAATAGTTATCC ATTCACT SEQ ID NO:17377 |
| | | AA | RASQGIRNNLG SEQ ID NO:1354 | GASSLQS SEQ ID NO:9366 | LQYNSYPFT SEQ ID NO:17378 |
| iPS:434103 | 21-225_53G1 | NA | CGGGCAAGTCAGGGCATTAG AAATGATTAGGC SEQ ID NO:1355 | CCTGCATCCAGTTTACAA AGT SEQ ID NO:9367 | CTACAGGATAATAGTTACCC ATTCACT SEQ ID NO:17379 |
| | | AA | RASQGIRNDLG SEQ ID NO:1356 | PASSLQS SEQ ID NO:9368 | LQDNSYPPT SEQ ID NO:17380 |
| iPS:434105 | 21-225_53D2 | NA | CGGGCAAGTCAGGGCATTAG AAATGATTAGGC SEQ ID NO:1357 | GCTGCATCCAGTTTGCAA AGT SEQ ID NO:9369 | CTACAACATATAGATACCC GCTCACT SEQ ID NO:17381 |
| | | AA | RASQGIRNDLG SEQ ID NO:1358 | AASSLQS SEQ ID NO:9370 | LQHNRYPLT SEQ ID NO:17382 |
| iPS:434107 | 21-225_53E2 | NA | CGGGCAAGTCAGAGTTTTAG CCACTATTTAAAT SEQ ID NO:1359 | GCTGTATCCAGTTTGCAA AGT SEQ ID NO:9371 | CAACAGAGTTCAGTACCCC ATTCACT SEQ ID NO:17383 |

FIGURE 49
(Continued)

| | | | | | |
|---|---|---|---|---|---|
| iPS:434111 | 21-225_53H2 | AA | RASQSFSHYLN<br>SEQ ID NO:1360 | AVSSLQS<br>SEQ ID NO:9372 | QQSFSTPFT<br>SEQ ID NO:17384 |
| | | NA | CAGGCGAGTCAGGACATTAG<br>CAACTATTACAT<br>SEQ ID NO:1361 | GATGCATCCAATTGGA<br>AACA<br>SEQ ID NO:9373 | CATCAGTATGATAATCTCCC<br>GCTCACT<br>SEQ ID NO:17385 |
| iPS:434115 | 21-225_53E4 | AA | QASQDISNYLH<br>SEQ ID NO:1362 | DASNLET<br>SEQ ID NO:9374 | HQYDNLPLT<br>SEQ ID NO:17386 |
| | | NA | CGGGCGAGTCAGGTCAGTTCATTAG<br>CAATTATTAGCC<br>SEQ ID NO:1363 | GCTGCATCCAGTTGCAA<br>AGT<br>SEQ ID NO:9375 | CAACAGTATCATAGTTACC<br>ACTCACT<br>SEQ ID NO:17387 |
| iPS:434117 | 21-225_53C6 | AA | RASQVISNYLA<br>SEQ ID NO:1364 | AASSLQS<br>SEQ ID NO:9376 | QQYHSYPLT<br>SEQ ID NO:17388 |
| | | NA | CGGGCAAGTCAGTACAGTAG<br>CGACTATTAAAT<br>SEQ ID NO:1365 | GCTGCATCCAGTTGAA<br>AAGT<br>SEQ ID NO:9377 | CAACAGAGTTACAGTACCC<br>GTTCACC<br>SEQ ID NO:17389 |
| iPS:434119 | 21-225_53C6 | AA | RASQYSSDYLN<br>SEQ ID NO:1366 | AASSLKS<br>SEQ ID NO:9378 | QQSYSTPFT<br>SEQ ID NO:17390 |
| | | NA | CGGGCAAGTCAGGGCATTAG<br>AAATGATTAGGC<br>SEQ ID NO:1367 | GCTGCATCCAATTGCAA<br>AGT<br>SEQ ID NO:9379 | CTACAACATAATCGTTACC<br>GCTCACT<br>SEQ ID NO:17391 |
| iPS:434121 | 21-225_53E6 | AA | RASQGIRNDLG<br>SEQ ID NO:1368 | AASNLQS<br>SEQ ID NO:9380 | LQHNRYPLT<br>SEQ ID NO:17392 |
| | | NA | CAGGCGAGTCAAGACATTAC<br>CAACTATTAGAT<br>SEQ ID NO:1369 | GATGCATCCAATTGGG<br>AACA<br>SEQ ID NO:9381 | CAACAGTGTGATAATCTCCC<br>GCTCACT<br>SEQ ID NO:17393 |
| iPS:434123 | 21-225_53F6 | AA | QASQDITNYLD<br>SEQ ID NO:1370 | DASNLGT<br>SEQ ID NO:9382 | QQCDNLPLT<br>SEQ ID NO:17394 |
| | 21-225_53F7 | NA | CGGGCGAGTCAGGGTATTAG<br>CAGGTGGTTAGCC<br>SEQ ID NO:1371 | GCTGCATCCAGTTGCAA<br>AGT<br>SEQ ID NO:9383 | CAGCAGTAACAGTTTCCC<br>ATTCACT<br>SEQ ID NO:17395 |

FIGURE 49 (Continued)

| | | | | | | |
|---|---|---|---|---|---|---|
| iPS:434127 | 21-225_53H8 | AA | RASQGISRWLA SEQ ID NO:1372 | AASSLQS SEQ ID NO:9384 | QQANSFPFT SEQ ID NO:17396 |
| | | NA | AGGGCCAGTCAGAGTATTAC AAGCAGCTACTTAGCC SEQ ID NO:1373 | GGTGCGTCCGGCAGGGC CACT SEQ ID NO:9385 | CAGCAGTTTGAAAGCTCACC CATGTGCAGT SEQ ID NO:17397 |
| iPS:434129 | 21-225_53B12 | AA | RASQSITSSYLA SEQ ID NO:1374 | GASGRAT SEQ ID NO:9386 | QQFESSPMCS SEQ ID NO:17398 |
| | | NA | CGGGCAAGTCAGGGCATTAG AAATGATTTAGGC SEQ ID NO:1375 | GCTGCATCCAGTTGCAA AGT SEQ ID NO:9387 | CTACAGCATAATAGTTACCC ATTCACT SEQ ID NO:17399 |
| iPS:434131 | 21-225_54D3 | AA | RASQGIRNDLG SEQ ID NO:1376 | AASSLQS SEQ ID NO:9388 | LQHNSYPFT SEQ ID NO:17400 |
| | | NA | CGGGCAAGTCAGGGCATTAG AAATGATTTAGGC SEQ ID NO:1377 | GCTGCATCCAGTTGCAA AGT SEQ ID NO:9389 | CTACAACATAATAGTTACCC ATTCACT SEQ ID NO:17401 |
| iPS:434133 | 21-225_54G3 | AA | RASQGIRNDLG SEQ ID NO:1378 | AASSLQS SEQ ID NO:9390 | LQHNSYPFT SEQ ID NO:17402 |
| | | NA | CGGGCGAGTCAGGGTATTAG CAGCTGGTTAGGC SEQ ID NO:1379 | GATGCATCCAGTTGCA AAGT SEQ ID NO:9391 | CAACAGGCTAACAGTTTCC GTGGACG SEQ ID NO:17403 |
| iPS:434135 | 21-225_54H3 | AA | RASQGISSWLA SEQ ID NO:1380 | DASSLQS SEQ ID NO:9392 | QQANSFPWT SEQ ID NO:17404 |
| | | NA | CGGGCAAGTCAGGACATTAG AAATATTTAGGC SEQ ID NO:1381 | GCTGCATCCAATTGCAA AGT SEQ ID NO:9393 | CTACAGTATATAGTTACCC GTGGACG SEQ ID NO:17405 |
| iPS:434137 | 21-225_54D4 | AA | RASQDIRNILG SEQ ID NO:1382 | AASNLQS SEQ ID NO:9394 | LQYNSYPWT SEQ ID NO:17406 |
| | | NA | AAGTCTAGTCAGAGCCTCCT GCATAGTGAGGGAAAGACC TATTTGTAT | GAAGTTTCCAACCGGTTC TCT | ATGCAAGTATACAGTTTCC ATTCACT |

FIGURE 49
(Continued)

| | | | | | | | |
|---|---|---|---|---|---|---|---|
| iPS:434141 | 21-225_54D4 | AA | SEQ ID NO:1383<br>KSSQSLLHSEGKTYLY<br>SEQ ID NO:1384 | SEQ ID NO:9395<br>EVSNRFS<br>SEQ ID NO:9396 | SEQ ID NO:17407<br>MQSIQFPFT<br>SEQ ID NO:17408 |
| iPS:434143 | 21-225_54C6 | NA | CGGGCAAGTCAGGGCATTAG<br>AAATGATTAGGC<br>SEQ ID NO:1385 | GCTGCATCCAATTTGCAA<br>AGT<br>SEQ ID NO:9397 | CTACAGGCATAATGTTACC<br>GCTCACT<br>SEQ ID NO:17409 |
| | | AA | RASQGIRNDLG<br>SEQ ID NO:1386 | AASNLQS<br>SEQ ID NO:9398 | LQHNRYPLT<br>SEQ ID NO:17410 |
| iPS:434145 | 21-225_54G7 | NA | CGGGCAAGTCAGGGCATTAG<br>AAATGATTAGGC<br>SEQ ID NO:1387 | GCTGCATCCAGTTTGCAA<br>AGT<br>SEQ ID NO:9399 | CTACATCATATACTTACC<br>ATTCACT<br>SEQ ID NO:17411 |
| | | AA | RASQGIRNDLG<br>SEQ ID NO:1388 | AASSLQS<br>SEQ ID NO:9400 | LHHNTYPFT<br>SEQ ID NO:17412 |
| iPS:434147 | 21-225_55B1 | NA | CGGGCGAGTCAGGTTATTAG<br>CCGCTGGTTAGCC<br>SEQ ID NO:1389 | GCTGCATCCAGTTTGCAA<br>AGT<br>SEQ ID NO:9401 | CAACAGGCTAACAGTTTCC<br>ATTCACT<br>SEQ ID NO:17413 |
| | | AA | RASQVISRWLA<br>SEQ ID NO:1390 | AASSLQS<br>SEQ ID NO:9402 | QQANSFPFT<br>SEQ ID NO:17414 |
| iPS:434149 | 21-225_55E1 | NA | AGGGCCAGTCAGAGTGTTAG<br>CAGCGACTTAGCC<br>SEQ ID NO:1391 | GATGCATCCGCCAGGGC<br>CACT<br>SEQ ID NO:9403 | CAGCAGTATTATAACTGGCC<br>TCTCACT<br>SEQ ID NO:17415 |
| | | AA | RASQSVSSDLA<br>SEQ ID NO:1392 | DASARAT<br>SEQ ID NO:9404 | QQYYNWPLT<br>SEQ ID NO:17416 |
| iPS:434149 | 21-225_55H1 | NA | AAATCTAGTCAGAGCCTCCT<br>GCATAGTGAAGGAAAGACC<br>TATTTGTAT<br>SEQ ID NO:1393 | GAAGTTTCCCACCGGTTC<br>TCT<br>SEQ ID NO:9405 | ATGCAAAGTATACAGCTTCC<br>ATTCACT<br>SEQ ID NO:17417 |
| | | AA | KSSQSLLHSEGKTYLY<br>SEQ ID NO:1394 | EVSHRFS<br>SEQ ID NO:9406 | MQSIQLPFT<br>SEQ ID NO:17418 |

FIGURE 49
(Continued)

| | | | | | | |
|---|---|---|---|---|---|---|
| iPS:434151 | 21-225_55C2 | NA | AAGTCTAGTCAGAGCCTCGTGCATAGTGAAGGAAAGACCTATTTGTAT<br>SEQ ID NO:1395 | GAAGTTTCCAACCGGGTCTCT<br>SEQ ID NO:9407 | ATGCAAAGTATACTGTATCCGATCACC<br>SEQ ID NO:17419 |
| | | AA | KSSQSLVHSEGKTYLY<br>SEQ ID NO:1396 | EVSNRVS<br>SEQ ID NO:9408 | MQSILYPFT<br>SEQ ID NO:17420 |
| iPS:434155 | 21-225_55B3 | NA | CGGGCAAGTCAGGGCATTAGAAATGATTTAGGC<br>SEQ ID NO:1397 | GCTGCATCCAGTTTGCAAAGT<br>SEQ ID NO:9409 | CTACAACATAATAGTTACCATTCACT<br>SEQ ID NO:17421 |
| | | AA | RASQGIRNDLG<br>SEQ ID NO:1398 | AASSLQS<br>SEQ ID NO:9410 | LQHNSYPFT<br>SEQ ID NO:17422 |
| iPS:434157 | 21-225_55D4 | NA | CGGGCGAGTCAGGACATTAGCAATTATTTAAATC<br>SEQ ID NO:1399 | ACTGCATCCAGTTTGCAAAGT<br>SEQ ID NO:9411 | CAACAGTATCATAGTTTCCCTCTCACT<br>SEQ ID NO:17423 |
| | | AA | RASQDISNYLI<br>SEQ ID NO:1400 | TASSLQS<br>SEQ ID NO:9412 | QQYHSFPLT<br>SEQ ID NO:17424 |
| iPS:434159 | 21-225_55B8 | NA | CGGGCAAGTCAGGCCATTAGAAATGATTTAGGC<br>SEQ ID NO:1401 | GCTGCATTCAGGTTGCAAAGT<br>SEQ ID NO:9413 | CTACAGCATAATAGTTACCCTCTCACT<br>SEQ ID NO:17425 |
| | | AA | RASQAIRNDLG<br>SEQ ID NO:1402 | AAFRLQS<br>SEQ ID NO:9414 | LQHNSYPLT<br>SEQ ID NO:17426 |
| iPS:434161 | 21-225_55F9 | NA | AAGTCTAGTCAGAGCCTCCTGCATAGTGAAGGAAAGACCTATTTGTAT<br>SEQ ID NO:1403 | GAAGTTTCCAACCGGTTCTCT<br>SEQ ID NO:9415 | ATACAAAGTATACAACTTCCGATCACC<br>SEQ ID NO:17427 |
| | | AA | KSSQSLLHSEGKTYLY<br>SEQ ID NO:1404 | EVSNRFS<br>SEQ ID NO:9416 | IQSIQLPIT<br>SEQ ID NO:17428 |
| iPS:434163 | 21-225_50H1 | NA | CAGGCGAGTCAAGACATTAGCAACTATTTAGAT<br>SEQ ID NO:1405 | GATGCATCCAATTGGAAACA<br>SEQ ID NO:9417 | CAACAGTGTGATAATCCCCGCTCACT<br>SEQ ID NO:17429 |

FIGURE 49 (Continued)

| | | | | | | | |
|---|---|---|---|---|---|---|---|
| iPS:434165 | 21-225_50F2 | AA | QASQDISNYLD SEQ ID NO:1406 | | DASNLET SEQ ID NO:9418 | | QQCDNLPLT SEQ ID NO:17430 |
| | | NA | CGGGCAAGTCAGAGCATTCT CAGCTATTTGAAT SEQ ID NO:1407 | | GTTGCATCCAGTTCCAA AGT SEQ ID NO:9419 | | CAACAGAGTTACAGTCCCCC TCTCACT SEQ ID NO:17431 |
| iPS:434167 | 21-225_50F3 | AA | RASQSILSYLN SEQ ID NO:1408 | | VASSFQS SEQ ID NO:9420 | | QQSYSPPLT SEQ ID NO:17432 |
| | | NA | CGGGCGAGTCAGGATATTAG CAGCTGGTTGGCC SEQ ID NO:1409 | | GCTGCATCCAGTTTGCAA AAT SEQ ID NO:9421 | | CAACAGACTAACAGTTTCCC ATTCACT SEQ ID NO:17433 |
| iPS:434169 | 21-225_50C4 | AA | RASQDISSWLA SEQ ID NO:1410 | | AASSLQN SEQ ID NO:9422 | | QQTNSFPFT SEQ ID NO:17434 |
| | | NA | CGGGCAAGTCAGGGCATTAG AAATGATTTAGGC SEQ ID NO:1411 | | GCTGCATCCAGTTTGCAA AGT SEQ ID NO:9423 | | CTACAGCATAATGTTACC ATTCACT SEQ ID NO:17435 |
| iPS:434171 | 21-225_50G4 | AA | RASQGIRNDLG SEQ ID NO:1412 | | AASSLQS SEQ ID NO:9424 | | LQHNRYPFT SEQ ID NO:17436 |
| | | NA | CAGGCGAGTCAGGACATTAA CAACTTTTAAAT SEQ ID NO:1413 | | GATGCCTCCAATTTGGA AACA SEQ ID NO:9425 | | CAACAGTATGATAATCTGAT CACC SEQ ID NO:17437 |
| iPS:434175 | 21-225_55A11 | AA | QASQDITNFLN SEQ ID NO:1414 | | DASNLET SEQ ID NO:9426 | | QQYDNLIT SEQ ID NO:17438 |
| | | NA | CGGGCGAGTCAGGAGTCAGGACATTAA CATTTATTTAGCC SEQ ID NO:1415 | | GCTGCATCCAGTTTGCAA AGT SEQ ID NO:9427 | | CAACAGTATAATAGTTATCC TCTCACT SEQ ID NO:17439 |
| iPS:434177 | 21-225_56A1 | AA | RASQDINIYLA SEQ ID NO:1416 | | AASSLQS SEQ ID NO:9428 | | QQYNSYPLT SEQ ID NO:17440 |
| | | NA | AAGTCCAGCCAGAGTGTTTT ACATAGTTCCAACAATAAGA ACTACTTAGTT | | TGGGCATCTACCCGGGA ATCC | | CAGCAATATTATAGTACTCC TCCGACG |

FIGURE 49
(Continued)

| | | | | | | |
|---|---|---|---|---|---|---|
| iPS:434179 | 21-225_56A1 | AA | SEQ ID NO:1417 KSSQSVLHSSNKNYLV | SEQ ID NO:9429 WASTRES | SEQ ID NO:17441 QQYYSTPPT | |
| | | NA | SEQ ID NO:1418 CGGGCAAGTCAGGACATTAG AAATAATTTAGGC | SEQ ID NO:9430 GCTGCATCCAGTTTACAA AGT | SEQ ID NO:17442 CTACAGGATAATAGTCACCC GTTCACT | |
| iPS:434181 | 21-225_56F1 | AA | SEQ ID NO:1419 RASQDIRNLG | SEQ ID NO:9431 AASSLQS | SEQ ID NO:17443 LQDNSHPFT | |
| | | NA | SEQ ID NO:1420 CGGGCAAGTCAGAGTTTTAG CCACTATTTAAAT | SEQ ID NO:9432 GCTGTATCCAGTTTGCAA AGT | SEQ ID NO:17444 CAACAGAGTTACAGTACCC ATTCACT | |
| iPS:434187 | 21-225_56B2 | AA | SEQ ID NO:1421 RASQSFSHYLN | SEQ ID NO:9433 AVSSLQS | SEQ ID NO:17445 QQSYSTPFT | |
| | | NA | SEQ ID NO:1422 CGGGCAAGTCAGGACATTAG AAATCTTTAAAT | SEQ ID NO:9434 GCTGCATCCAGTTTGCAA AGT | SEQ ID NO:17446 CTACAGTATAATAGTTACCC ATTCACT | |
| iPS:434189 | 21-225_56A5 | AA | SEQ ID NO:1423 RASQDIRNLLG | SEQ ID NO:9435 AASSLQS | SEQ ID NO:17447 LQYNSYPFT | |
| | | NA | SEQ ID NO:1424 CGGGCGAGTCAGGGTATTAG GAAGTGGTTAGCC | SEQ ID NO:9436 GCTGCATCCAGTTGCAA AGT | SEQ ID NO:17448 CAACAGGCTAACAGTTCCC ATTCACT | |
| iPS:434191 | 21-225_56E5 | AA | SEQ ID NO:1425 RASQGIRKWLA | SEQ ID NO:9437 AASSLQS | SEQ ID NO:17449 QQANSFPFT | |
| | | NA | SEQ ID NO:1426 CGGGCAAGTCAGAGCATTT CAGATATTTAAAT | SEQ ID NO:9438 GCTGCATCCAGTTCCAA AGT | SEQ ID NO:17450 CAACAGACTTACAGTCCCCC TCTCACT | |
| iPS:434193 | 21-225_56B6 | AA | SEQ ID NO:1427 RASQSIFRYLN | SEQ ID NO:9439 AASSFQS | SEQ ID NO:17451 QQTYSPPLT | |
| | | NA | SEQ ID NO:1428 CGGGCGAGTCAGGGTATTAG CAGCTGGTTAGCC | SEQ ID NO:9440 GCTGCATCCAGATTGCA AAGT | SEQ ID NO:17452 CAACAGGCTAACAGTTCCC ATTCACT | |

FIGURE 49 (Continued)

| | | | | | | |
|---|---|---|---|---|---|---|
| iPS:434195 | 21-225_56C6 | | SEQ ID NO:1429 RASQGISSWLA | SEQ ID NO:1441 AASRLQS | SEQ ID NO:17453 QQANSFPFT | |
| | | AA | SEQ ID NO:1430 | SEQ ID NO:9442 | SEQ ID NO:17454 | |
| | | NA | CGGGTGAGTCAGGATATTAG CAAATGGTTAGCC | GTTGCATCCGGTTGCAA AGT | CAACAGGCTAACAGTTTCC ATTCACT | |
| iPS:434197 | 21-225_56F6 | | SEQ ID NO:1431 RVSQDISKWLA | SEQ ID NO:1443 VASGLQS | SEQ ID NO:17455 QQANSFPFT | |
| | | AA | SEQ ID NO:1432 | SEQ ID NO:9444 | SEQ ID NO:17456 | |
| | | NA | CGGGCAAGTCAGGGCATTAG AAATGATTTAGGC | ACTGCATCCAATTTACAA AGT | CTACAGCATAATAGTTATCC GTGGACG | |
| iPS:434199 | 21-225_56C7 | | SEQ ID NO:1433 RASQGIRNDLG | SEQ ID NO:1445 TASNLQS | SEQ ID NO:17457 LQHNSYPWT | |
| | | AA | SEQ ID NO:1434 | SEQ ID NO:9446 | SEQ ID NO:17458 | |
| | | NA | CGGGCAAGTCAGGGCATTAG AAATGATTTAGGC | GCTGCATCCAGTTGCAA AGT | CTACAGCATAATGTTACC TTTCACT | |
| iPS:434201 | 21-225_59F11 | | SEQ ID NO:1435 RASQGIRNDLG | SEQ ID NO:1447 AASSLQS | SEQ ID NO:17459 LQHNRYPFT | |
| | | AA | SEQ ID NO:1436 | SEQ ID NO:9448 | SEQ ID NO:17460 | |
| | | NA | AAGTCTAGTCAGAGCCTCCA GCATGGTGAAGGAAAGACC TATTTGTAT | GAAGTTTCCTATCGGTTT TCT | ATGCAAAGTACACAGCTTCC GCTCACC | |
| iPS:434201 | 21-225_59A12 | | SEQ ID NO:1437 KSSQSLQHGEGKTYLY | SEQ ID NO:1449 EVSYRFS | SEQ ID NO:17461 MQSTQLPLT | |
| | | AA | SEQ ID NO:1438 | SEQ ID NO:9450 | SEQ ID NO:17462 | |
| | | NA | CGGGCAAGTCAGGGCATTAG AAAAGATTAGGC | GCTGCATCCAGTTGCAA AGT | CTACAGCATAATAGTTACC GTGGACG | |
| iPS:434203 | 21-225_60E2 | | SEQ ID NO:1439 RASQGIRKDLG | SEQ ID NO:1451 AASSLQS | SEQ ID NO:17463 LQHNSYPWT | |
| | | AA | SEQ ID NO:1440 | SEQ ID NO:9452 | SEQ ID NO:17464 | |

FIGURE 49
(Continued)

| | | | | | |
|---|---|---|---|---|---|
| iPS:434205 | 21-225_60G2 | NA | AAGTCTAGTCAGAGCCTCCT GCATAGTGAAGGAAAGACC TATTTGTAT SEQ ID NO:1441 | GAAGTTTCCAACCGGAT CTCT SEQ ID NO:9453 | ATGCAAAGTATACAGCTTCC GCTCACT SEQ ID NO:17465 |
| | | AA | KSSQSLLHSEGKTYLY SEQ ID NO:1442 | EVSNRIS SEQ ID NO:9454 | MQSIQLPLT SEQ ID NO:17466 |
| iPS:434207 | 21-225_60A3 | NA | CGGGCAAGTCAGGGCATTAG AAATGATTTAGGC SEQ ID NO:1443 | GCTGCATTAGTTGCAA AGT SEQ ID NO:9455 | CTACAGCATAATAGTTACCC TTTCACT SEQ ID NO:17467 |
| | | AA | RASQGIRNDLG SEQ ID NO:1444 | AAFSLQS SEQ ID NO:9456 | LQHNSYPFT SEQ ID NO:17468 |
| iPS:434209 | 21-225_60C3 | NA | CGGGCAAGTCAGGGCATTAG AAATGATTTAGGC SEQ ID NO:1445 | TCTGCATCCAGTTACAA AGT SEQ ID NO:9457 | CTACAGCATAATAGTTACCC GTGGACG SEQ ID NO:17469 |
| | | AA | RASQGIRNDLG SEQ ID NO:1446 | SASSLQS SEQ ID NO:9458 | LQHNSYPWT SEQ ID NO:17470 |
| iPS:434211 | 21-225_60F3 | NA | AAGTCCAGCCAGAGTGTTT ATACAGCTCCAACAATAAGA ACTACTTAGCT SEQ ID NO:1447 | TGGGCATCTACCCGGGA ATCC SEQ ID NO:9459 | CAGCAATATTATAGTACTCC GTGCAGT SEQ ID NO:17471 |
| | | AA | KSSQSVLYSSNNKNYLA SEQ ID NO:1448 | WASTRES SEQ ID NO:9460 | QQYYSTPCS SEQ ID NO:17472 |
| iPS:434213 | 21-225_60A4 | NA | CGGGCGAGTCAGGGCATTAG CAATTACTTAGCC SEQ ID NO:1449 | GCTGCATCCAGTTGCAA AGT SEQ ID NO:9461 | CAACAATATAAAAGTCACCC ATTCACT SEQ ID NO:17473 |
| | | AA | RASQGISNYLA SEQ ID NO:1450 | AASSLQS SEQ ID NO:9462 | QQYKSHPFT SEQ ID NO:17474 |
| iPS:434215 | 21-225_60F7 | NA | CGGGCGAGTCAGGTCATTAA GAATTATTTAGTC SEQ ID NO:1451 | GCTGCGTCCAGTTGCAA AGT SEQ ID NO:9463 | CTACAGTTCATAGTTACC ATTCACT SEQ ID NO:17475 |

FIGURE 49
(Continued)

| | | | | | | | |
|---|---|---|---|---|---|---|---|
| iPS:434217 | | AA | RASQVIKNYLV | AASSLQS | LQFHSYPFT | | |
| | | | SEQ ID NO:1452 | SEQ ID NO:9464 | SEQ ID NO:17476 | | |
| iPS:434219 | 21-225_60E8 | NA | CGGGCAAGTCAGGGCATTAG AAATGATTTAGGC | GCTGCATCCAGTTTGCAA AGT | CTACAGCATAGTAGTTACCC GCTCACT | | |
| | | | SEQ ID NO:1453 | SEQ ID NO:9465 | SEQ ID NO:17477 | | |
| | | AA | RASQGIRNDLG | AASSLQS | LQHSSYPLT | | |
| | | | SEQ ID NO:1454 | SEQ ID NO:9466 | SEQ ID NO:17478 | | |
| iPS:434221 | 21-225_60E9 | NA | AGGGCCAGTCAGAGAGTTGTTAG CAGTTCCTTAGCC | GGTGCATCCACCAGGGC CACT | CAGCAGTATAATAACTGGCC ATTCACT | | |
| | | | SEQ ID NO:1455 | SEQ ID NO:9467 | SEQ ID NO:17479 | | |
| | | AA | RASQSVSSSLA | GASTRAT | QQYNNWPFT | | |
| | | | SEQ ID NO:1456 | SEQ ID NO:9468 | SEQ ID NO:17480 | | |
| iPS:434223 | 21-225_60A11 | NA | CGGGCGAGTCAGGTTATTAG CAACTGGTTAGCC | ACTGCATCCAGTTTGCAA AGT | CAACAGGCTAACAGTTTCCC GTGGACG | | |
| | | | SEQ ID NO:1457 | SEQ ID NO:9469 | SEQ ID NO:17481 | | |
| | | AA | RASQVISNWLA | TASSLQS | QQANSFPWT | | |
| | | | SEQ ID NO:1458 | SEQ ID NO:9470 | SEQ ID NO:17482 | | |
| iPS:434225 | 21-225_60C12 | NA | AAGTCTAGTCAGAGCCTCCT GCATAGTGAGGGAAAGACC TATTTGTAT | GAAGTTTCCAACCGGTTC TCT | ATGCAAAGTATAAAGTATCC GCTCACT | | |
| | | | SEQ ID NO:1459 | SEQ ID NO:9471 | SEQ ID NO:17483 | | |
| | | AA | KSSQSLLHSEGKTYLY | EVSNRFS | MQSIKYPLT | | |
| | | | SEQ ID NO:1460 | SEQ ID NO:9472 | SEQ ID NO:17484 | | |
| iPS:434227 | 21-225_60E12 | NA | CGGGCAAGTCAGAGCATTAG CAGCTATTTAAAT | GCTGCATCCAGTTTGCAA AGT | CAACAGAGTTACAATATTTC ATTCACT | | |
| | | | SEQ ID NO:1461 | SEQ ID NO:9473 | SEQ ID NO:17485 | | |
| | | AA | RASQSISSYLN | AASSLQS | QQSYNISFT | | |
| | | | SEQ ID NO:1462 | SEQ ID NO:9474 | SEQ ID NO:17486 | | |
| | | NA | CGGGCAAGTCAGAGCATTAG CAGCTATTTAAAT | GCTGCATCCAGTTTGCAA AGT | CAACAGAGTTACAATATTTC ATTCACT | | |

FIGURE 49
(Continued)

| | | | | | | |
|---|---|---|---|---|---|---|
| 21-225_61A1 | | | SEQ ID NO:1463 RASQSISSYLN | SEQ ID NO:9475 AASSLQS | SEQ ID NO:17487 QQSYNISFT | |
| iPS:434229 | | AA | SEQ ID NO:1464 CGGGCAAGTCAGGGCATTAGAAAAGATTTAGGC | SEQ ID NO:9476 GCTGCATCCAGTTTGCAAAGT | SEQ ID NO:17488 CTACAGCATAATAGTTACCCGTGGACG | |
| 21-225_61H1 | | NA | SEQ ID NO:1465 RASQGIRKDLG | SEQ ID NO:9477 AASSLQS | SEQ ID NO:17489 LQHNSYPWT | |
| iPS:434231 | | AA | SEQ ID NO:1466 CGGGCAAGTCAGGGCATTAGAGATGATTTAGGC | SEQ ID NO:9478 GCTGCATCCAGTTTGCAAAGT | SEQ ID NO:17490 CTACAGCATATAGTTACCCTCGCAGT | |
| 21-225_61F2 | | NA | SEQ ID NO:1467 RASQGIRDDLG | SEQ ID NO:9479 AASSLQS | SEQ ID NO:17491 LQHYSYPRS | |
| iPS:434233 | | AA | SEQ ID NO:1468 AAGTCTAGTCAGAGCCTCCTGCATAGTGAAGGAAAGACCTATTTGTAT | SEQ ID NO:9480 GAAGTTTCCAACCGGATCTCT | SEQ ID NO:17492 ATGCAAAGTATACAGCTTCCGCTCACT | |
| 21-225_61B3 | | NA | SEQ ID NO:1469 KSSQSLLHSEGKTYLY | SEQ ID NO:9481 EVSNRIS | SEQ ID NO:17493 MQSIQLPLT | |
| iPS:434235 | | AA | SEQ ID NO:1470 AAGTCCAGCCAGAGTGTTTTACACAGCTCCAACAATAACAATTACTTAGCT | SEQ ID NO:9482 TGGGCATCTATCCGGGAATCC | SEQ ID NO:17494 CAGCAATATTATAGTATTCCGTGCAGT | |
| 21-225_61E3 | | NA | SEQ ID NO:1471 KSSQSVLHSNNNNYLA | SEQ ID NO:9483 WASIRES | SEQ ID NO:17495 QQYYSIPCS | |
| iPS:434237 | | AA | SEQ ID NO:1472 AAGTCCAGCCAGAGTGTTTTATACAGTTCCAACAATAACAACTCCTTAACT | SEQ ID NO:9484 TGGGCATCTACCCGGGAATCC | SEQ ID NO:17496 CAGCAATATTATAGTACTCCGTCCGACG | |
| 21-225_61B5 | | NA | SEQ ID NO:1473 KSSQSVLYSSNNNNSLT | SEQ ID NO:9485 WASTRES | SEQ ID NO:17497 QQYYSTPPT | |

FIGURE 49
(Continued)

| | | | | | |
|---|---|---|---|---|---|
| iPS:434239 | 21-225_58F1 | NA | SEQ ID NO:1474<br>CGGGCAAGTCAGAGCATTAC<br>CAACTTTTTAAAT | SEQ ID NO:9486<br>GCTGCATCCAGTTTGCAA<br>AGT | SEQ ID NO:17498<br>CAACAGAGTTACAGTATCCC<br>GTGGACG |
| | | AA | SEQ ID NO:1475<br>RASQSITNFLN | SEQ ID NO:9487<br>AASSLQS | SEQ ID NO:17499<br>QQSYSIPWT |
| iPS:434241 | 21-225_61E6 | NA | SEQ ID NO:1476<br>CGGGCAAGTCAGGGCATTGG<br>AAATGATTTAGGC | SEQ ID NO:9488<br>GCTGCATCCAGTTTGCAA<br>AGT | SEQ ID NO:17500<br>CTACAACATAATAGTTTCCC<br>TCCGTGGACG |
| | | AA | SEQ ID NO:1477<br>RASQGIGNDLG | SEQ ID NO:9489<br>AASSLQS | SEQ ID NO:17501<br>LQHNSFPPWT |
| iPS:434243 | 21-225_62C1 | NA | SEQ ID NO:1478<br>AGGTCTAGTCAGAGCCTCCT<br>ACATAGTAATGGATACAACT<br>ATTTGGAT | SEQ ID NO:9490<br>TTGGTTTCTAATCGGGCC<br>TCC | SEQ ID NO:17502<br>CTGCAAGCTCTACAAACTCC<br>TCTCACC |
| | | AA | SEQ ID NO:1479<br>RSSQSLLHSNGYNYLD | SEQ ID NO:9491<br>LVSNRAS | SEQ ID NO:17503<br>LQALQTPLT |
| iPS:434245 | 21-225_62H1 | NA | SEQ ID NO:1480<br>CGGGCAAGTCAGAGAACATTTT<br>CAGCTATTTAAAT | SEQ ID NO:9492<br>GCTGTATTTAGTTTGCAA<br>AGT | SEQ ID NO:17504<br>CAACAGAGTTACAGTACCCC<br>ATTCACT |
| | | AA | SEQ ID NO:1481<br>RASQNIFSYLN | SEQ ID NO:9493<br>AVFSLQS | SEQ ID NO:17505<br>QQSYSTPFT |
| iPS:434247 | 21-225_62D2 | NA | SEQ ID NO:1482<br>CGGGCAAGTCAGAGCATTAT<br>CAGTTATTTAAAT | SEQ ID NO:9494<br>GCTACATCCAGTTTGCAA<br>AGT | SEQ ID NO:17506<br>CAACAGAGTTACAGTCCCCC<br>GCTCACT |
| | | AA | SEQ ID NO:1483<br>RASQSIISYLN | SEQ ID NO:9495<br>ATSSLQS | SEQ ID NO:17507<br>QQTYSPPLT |
| iPS:434249 | 21-225_62E2 | NA | SEQ ID NO:1484<br>CGGGCAAGTCAGGGCATTAG<br>AAATGATTTAGGC | SEQ ID NO:9496<br>GCTGCATCCGGTTTGCAA<br>AGT | SEQ ID NO:17508<br>CTACAGCATAGTAATTACCC<br>TCTCACT |
| | | | SEQ ID NO:1485 | SEQ ID NO:9497 | SEQ ID NO:17509 |

FIGURE 49
(Continued)

| | | | | | | | |
|---|---|---|---|---|---|---|---|
| iPS:434251 | | AA | RASQGIRNDLG | | AASRLQS | | LQHSNYPLT |
| | | | SEQ ID NO:1486 | | SEQ ID NO:9498 | | SEQ ID NO:17510 |
| | 21-225_62G3 | NA | CGGGCAAGTCAGGACATTAG AAATAATTAGGC | | ACTGCATCCAGTTTGCAA AGT | | CTACAGTATAATAGTTACCC ATTCACT |
| | | | SEQ ID NO:1487 | | SEQ ID NO:9499 | | SEQ ID NO:17511 |
| iPS:434253 | | AA | RASQDIRNNLG | | TASSLQS | | LQYNSYPFT |
| | | | SEQ ID NO:1488 | | SEQ ID NO:9500 | | SEQ ID NO:17512 |
| | 21-225_62E4 | NA | CGGGCAAGTCAGGGCATTAG AAATGATTAGGC | | GCTGCATTCAGTTTGCAA AGT | | CTACAGCATAATAGTTATCC GCTCACT |
| | | | SEQ ID NO:1489 | | SEQ ID NO:9501 | | SEQ ID NO:17513 |
| iPS:434255 | | AA | RASQGIRNDLG | | AAFSLQS | | LQHNSYPLT |
| | | | SEQ ID NO:1490 | | SEQ ID NO:9502 | | SEQ ID NO:17514 |
| | 21-225_62E6 | NA | AGGGCCAGTCAGAGTGTTAA CAGCAACTTAGCC | | GTTGCATCCACCAGGGC CACT | | CAGCAGTATAATGACTGGCC GTGTAGT |
| | | | SEQ ID NO:1491 | | SEQ ID NO:9503 | | SEQ ID NO:17515 |
| iPS:434257 | | AA | RASQSVNSNLA | | VASTRAT | | QQYNDWPCS |
| | | | SEQ ID NO:1492 | | SEQ ID NO:9504 | | SEQ ID NO:17516 |
| | 21-225_62F7 | NA | CGGGCAAGTCAGGGCCATTAG AAATGATTAGGC | | CCTGCATCCCGTTTGCAA AGT | | CTACAGTATAATAGTTACCC TCCGTGGACG |
| | | | SEQ ID NO:1493 | | SEQ ID NO:9505 | | SEQ ID NO:17517 |
| iPS:434259 | | AA | RASQAIRNDLG | | PASRLQS | | LQYNSYPPWT |
| | | | SEQ ID NO:1494 | | SEQ ID NO:9506 | | SEQ ID NO:17518 |
| | 21-225_62G7 | NA | CGGGCGAGTCAGGGCATTAG CAGCTGGTTAGCC | | GCTGCATCCAGTTTGCAA AGT | | CAACAGACTAACAGTTTCCC TCTCACT |
| | | | SEQ ID NO:1495 | | SEQ ID NO:9507 | | SEQ ID NO:17519 |
| iPS:434261 | | AA | RASQDISSWLA | | AASSLQS | | QQTNSFPLT |
| | | | SEQ ID NO:1496 | | SEQ ID NO:9508 | | SEQ ID NO:17520 |
| | 21-225_56F7 | NA | CGGGCGAGTCAGGGCATTAG CACTTATTAGCC | | GCTGCATCCAGTTTGCAA GGT | | CATCAGTATAATAGTTTCCC ATTTAAG |
| | | | SEQ ID NO:1497 | | SEQ ID NO:9509 | | SEQ ID NO:17521 |

FIGURE 49
(Continued)

| | | AA | RASQGISTYLA<br>SEQ ID NO:1498 | AASSLQG<br>SEQ ID NO:9510 | HQYNSFPFK<br>SEQ ID NO:17522 |
|---|---|---|---|---|---|
| iPS:434263 | 21-225_56H7 | NA | CGGGCAAGTCAGGACATTAG<br>AAATGATTTAGGC<br>SEQ ID NO:1499 | CCTGCATCCAGTTTGCTA<br>AGT<br>SEQ ID NO:9511 | CTACAGGATAATAGTTACCC<br>ATTCACT<br>SEQ ID NO:17523 |
| iPS:434265 | 21-225_57B2 | AA | RASQDIRNDLG<br>SEQ ID NO:1500 | PASSLLS<br>SEQ ID NO:9512 | LQDNSYPFT<br>SEQ ID NO:17524 |
| | | NA | CGGGCAAGTCAGGGCATTAG<br>AAATGCTTTAGGC<br>SEQ ID NO:1501 | GCTGCATCCAGTTTGCAA<br>AGT<br>SEQ ID NO:9513 | CTACAGCATAATAGTTACCC<br>ATTCACT<br>SEQ ID NO:17525 |
| iPS:434267 | 21-225_57F2 | AA | RASQGIRNALG<br>SEQ ID NO:1502 | AASSLQS<br>SEQ ID NO:9514 | LQHNSYPFT<br>SEQ ID NO:17526 |
| | | NA | CGGGCAAGTCAGAGCATTAG<br>CAGCTATTAAAT<br>SEQ ID NO:1503 | GCTGCATCCAGTTTGCAA<br>AGT<br>SEQ ID NO:9515 | CAACAGAGTTACAATATTTC<br>ATTCACT<br>SEQ ID NO:17527 |
| iPS:434269 | 21-225_57H3 | AA | RASQSISSYLN<br>SEQ ID NO:1504 | AASSLQS<br>SEQ ID NO:9516 | QQSYNISFT<br>SEQ ID NO:17528 |
| | | NA | AGGGCCAGTCAGAGTGTTAG<br>CAGCAGCTTAGCC<br>SEQ ID NO:1505 | GGTGCATCCACCAGGGC<br>CACT<br>SEQ ID NO:9517 | CAGCAGTATAATGACTGGCC<br>GTGCAGT<br>SEQ ID NO:17529 |
| iPS:434271 | 21-225_57A4 | AA | RASQSVSSSLA<br>SEQ ID NO:1506 | GASTRAT<br>SEQ ID NO:9518 | QQYNDWPCS<br>SEQ ID NO:17530 |
| | | NA | CGGGCAAGTCAGGGCATTAG<br>AAATGATTTAGGC<br>SEQ ID NO:1507 | GCTGCATCCAGTTTGCTA<br>AGT<br>SEQ ID NO:9519 | CTACAGCATAATAGTTACCC<br>ATTCACT<br>SEQ ID NO:17531 |
| iPS:434273 | 21-225_57E4 | AA | RASQGIRNDLG<br>SEQ ID NO:1508 | AASSLLS<br>SEQ ID NO:9520 | LQHNSYPFT<br>SEQ ID NO:17532 |
| | | NA | CGGGCGAGTCAGGATATTAG<br>CAACTGGTTAGCC<br>SEQ ID NO:1509 | GCTGCATCCAGTTTGCAA<br>AGT<br>SEQ ID NO:9521 | CAACAGGGTAACAGTTTCCC<br>ATTCACT<br>SEQ ID NO:17533 |

FIGURE 49 (Continued)

| | | | | | | |
|---|---|---|---|---|---|---|
| iPS:434275 | 21-225_57F4 | AA | RASQDISNWLA SEQ ID NO:1510 | AASSLQS SEQ ID NO:9522 | QQGNSFPFT SEQ ID NO:17534 |
| | | NA | CGGGCAAGTCAGGTCATTAG AAATGATTAGGC SEQ ID NO:1511 | GCTGCATCCAGTTTGCAA AGT SEQ ID NO:9523 | CTACAGTATGGTAGTTTCCC ATTCACT SEQ ID NO:17535 |
| iPS:434277 | 21-225_57A7 | AA | RASQVIRNDLG SEQ ID NO:1512 | AASSLQS SEQ ID NO:9524 | LQYGSFPFT SEQ ID NO:17536 |
| | | NA | CGGGGAGTCAGGGTATTAG CAGGTGGTTAGCC SEQ ID NO:1513 | GCTGCATCCAATTTGCAA AGT SEQ ID NO:9525 | CAACAGGCTAACAGTTTCCC ATTCACT SEQ ID NO:17537 |
| iPS:434279 | 21-225_57F7 | AA | RASQGISRWLA SEQ ID NO:1514 | AASNLQS SEQ ID NO:9526 | QQANSFPFT SEQ ID NO:17538 |
| | | NA | AGGGCCAGTCAGAGTGTTAG CAGGGACTTAGCC SEQ ID NO:1515 | GGTGCATCCACCAGGGC CACT SEQ ID NO:9527 | CAGCAGTATAGTAACTGGCC ATTCACT SEQ ID NO:17539 |
| iPS:434281 | 21-225_57B8 | AA | RASQSVSSDLA SEQ ID NO:1516 | GASTRAT SEQ ID NO:9528 | QQYSNWPFT SEQ ID NO:17540 |
| | | NA | CGGGCAAGTCAGGGCATTGG AAATGATTAGGC SEQ ID NO:1517 | GCTGCATCCAGTTTGCAA AGT SEQ ID NO:9529 | CTACAACATAATAGTTTCCC TCCGTGGACG SEQ ID NO:17541 |
| iPS:434283 | 21-225_57F8 | AA | RASQGIGNDLG SEQ ID NO:1518 | AASSLQS SEQ ID NO:9530 | LQHNSFPPWT SEQ ID NO:17542 |
| | | NA | CGGGGAGTCAGGGTATTAG CAACTGGTTAGCC SEQ ID NO:1519 | ACTGCATCCAGTTTGCAA AGT SEQ ID NO:9531 | CAACAGGCTAACAGTTTCCC GTGGACG SEQ ID NO:17543 |
| iPS:434285 | 21-225_57A11 | AA | RASQGISNWLA SEQ ID NO:1520 | TASSLQS SEQ ID NO:9532 | QQANSFPWT SEQ ID NO:17544 |
| | | NA | AAGTCCAGCCAAAGTGTTTT ACACAGCTCCAACAATTATA ACTACTTAGCT | TGGGCATCTACCCGGGC ATCC | CAGCAATATTATAGTACTCC GTGGACG |

FIGURE 49
(Continued)

| | | | | | | |
|---|---|---|---|---|---|---|
| iPS:434287 | 21-225_57A11 | AA | SEQ ID NO:1521 KSSQSVLHSSNNYNYLA | SEQ ID NO:9533 WASTRAS | SEQ ID NO:17545 QQYYSTPWT | |
| | | NA | SEQ ID NO:1522 AAGTCCAGCCAGAGTGTTTT ATTCAGCTCCAACAATTACA ATTACTTAGCT | SEQ ID NO:9534 TGGGCATCTACCCGGGA ATCC | SEQ ID NO:17546 CAGCAATATTATAGTAATCC GTGTAGT | |
| iPS:434289 | 21-225_57F12 | AA | SEQ ID NO:1523 KSSQSVLFSSNNYNYLA | SEQ ID NO:9535 WASTRES | SEQ ID NO:17547 QQYYSNPCS | |
| | | NA | SEQ ID NO:1524 AGGGCCAGTCAGTCAGAGTGTTAG CAGCGACTTAGCC | SEQ ID NO:9536 GCTGCATCTACCAGGGC CACT | SEQ ID NO:17548 CAGCAGTATGATAACTGGCC ATTCACT | |
| iPS:434291 | 21-225_57H12 | AA | SEQ ID NO:1525 RASQSVSSDLA | SEQ ID NO:9537 AASTRAT | SEQ ID NO:17549 QQYDNWPFT | |
| | | NA | SEQ ID NO:1526 AGGGCCAGTCAGTCAGAGTGTTAG CAGCGACTTAGCC | SEQ ID NO:9538 GCTGCATCTACCAGGGC CACT | SEQ ID NO:17550 CAGCAGTTTAATAACTGGCC ATTCACT | |
| iPS:434293 | 21-225_58A4 | AA | SEQ ID NO:1527 RASQSVSSDLA | SEQ ID NO:9539 AASTRAT | SEQ ID NO:17551 QQFNNWPFT | |
| | | NA | SEQ ID NO:1528 CGGGCAAGTCAGGGCATTAG AAATGATTAGGC | SEQ ID NO:9540 GCTGCATCCAGTTGCTA AGT | SEQ ID NO:17552 CTACAGCATAATAGTTACCC ATTCACT | |
| iPS:434295 | 21-225_58F5 | AA | SEQ ID NO:1529 RASQGIRNDLG | SEQ ID NO:9541 AASSLLS | SEQ ID NO:17553 LQHNSYPFT | |
| | | NA | SEQ ID NO:1530 AAGTCCGGCCAGAGTATTTT ATACAGCTCCAACAATAACA ACTACTTAGCT | SEQ ID NO:9542 TGGGCATCTACCCGGGA TTCC | SEQ ID NO:17554 CAGCAATATTATAGTACTCC TCCGACG | |
| iPS:434295 | 21-225_58B9 | AA | SEQ ID NO:1531 KSGQSILYSSNNNYLA | SEQ ID NO:9543 WASTRDS | SEQ ID NO:17555 QQYYSTPPT | |
| | | NA | SEQ ID NO:1532 | SEQ ID NO:9544 | SEQ ID NO:17556 | |

FIGURE 49
(Continued)

| | | | | | |
|---|---|---|---|---|---|
| iPS:434297 | 21-225_58A10 | NA | AGGGCCAGTCAGAGTGTTAG CAGCTCCTTAGCC SEQ ID NO:1533 | GGTGCATCCACCAGGGC CACT SEQ ID NO:9545 | CAGCAGTATAATAACTGGCC ATTCACT SEQ ID NO:17557 |
| | | AA | RASQSVSSSLA SEQ ID NO:1534 | GASTRAT SEQ ID NO:9546 | QQYNNWPFT SEQ ID NO:17558 |
| iPS:434299 | 21-225_58D11 | NA | CGGGCAAGTCAGGGCATTAG AAGTGATTAGAC SEQ ID NO:1535 | GCTGCATCCAGTTGCAA AGT SEQ ID NO:9547 | CTCCAGCATAATAATTTCCC ATTCACT SEQ ID NO:17559 |
| | | AA | RASQGIRSDLD SEQ ID NO:1536 | AASSLQS SEQ ID NO:9548 | LQHNNFPFT SEQ ID NO:17560 |
| iPS:434301 | 21-225_58F11 | NA | AGGGCCAGTCAGAGTGTTAG CAGCGACTTAGTC SEQ ID NO:1537 | GGTGTATCCACCAGGGC CACT SEQ ID NO:9549 | CAGCAGTATAATAACTGGCC ATTCACT SEQ ID NO:17561 |
| | | AA | RASQSVSSDLV SEQ ID NO:1538 | GVSTRAT SEQ ID NO:9550 | QQYNNWPFT SEQ ID NO:17562 |
| iPS:434303 | 21-225_58H11 | NA | AAGTCTAGTCAGAGCCTCCT GCATAGTGAGGGAAAGACC TATTTGTAT SEQ ID NO:1539 | GAAGTTTCCTATCGGTTT TCT SEQ ID NO:9551 | ATGCAAAGTATACAGCTTCC GCTCACT SEQ ID NO:17563 |
| | | AA | KSSQSLLHSEGKTYLY SEQ ID NO:1540 | EVSYRFS SEQ ID NO:9552 | MQSIQLPLT SEQ ID NO:17564 |
| iPS:434305 | 21-225_59E1 | NA | AAGTCCAGCCAGAGTGTTTT ATACAGCTCCAACAATAACA ACTACTTAGCT SEQ ID NO:1541 | TGGTCATCTACCCGGGA ATCC SEQ ID NO:9553 | CAGCAATATATTTTAGTATTCC GTGCAGT SEQ ID NO:17565 |
| | | AA | KSSQSVLYSSNNNNYLA SEQ ID NO:1542 | WSSTRES SEQ ID NO:9554 | QQYFSIPCS SEQ ID NO:17566 |
| iPS:434307 | 21-225_59B2 | NA | TGGGCCAGTCAGAGTGTTTA CAGCAGTTCTTAGCC SEQ ID NO:1543 | GGTGCATCCAGCAGGGC CACT SEQ ID NO:9555 | CAGCAATATGGTACCTCACC GTGGACG SEQ ID NO:17567 |

FIGURE 49
(Continued)

| | | | | | GASSRAT | | QQYGTSPWT |
|---|---|---|---|---|---|---|---|
| | | AA | WASQSVYSSFLA | | | | |
| | | | SEQ ID NO:1544 | | SEQ ID NO:9556 | | SEQ ID NO:17568 |
| iPS:434309 | 21-225_59B5 | NA | CGGGCAAGTCAGAGCATTAT CAGCTATTAAAT | GGTGCATCCAGTTTGCA GAGT | | CAACAGAGTTACAGTACCCC TATGTTCAGT | |
| | | | SEQ ID NO:1545 | | SEQ ID NO:9557 | | SEQ ID NO:17569 |
| | | AA | RASQSHSYLN | GASSLQS | | QQSYSTPMFS | |
| | | | SEQ ID NO:1546 | | SEQ ID NO:9558 | | SEQ ID NO:17570 |
| iPS:434311 | 21-225_59H5 | NA | AGGGCCAGTCAGAGTGTTAG CAGCATCTACTTAGCC | GGTGCATCCAGCAGGGC CACT | | CACCAGTATGGTAACTCACC ATTCACT | |
| | | | SEQ ID NO:1547 | | SEQ ID NO:9559 | | SEQ ID NO:17571 |
| | | AA | RASQSVSSIYLA | GASSRAT | | HQYGNSPFT | |
| | | | SEQ ID NO:1548 | | SEQ ID NO:9560 | | SEQ ID NO:17572 |
| iPS:434313 | 21-225_59E6 | NA | CGGGCAAGTCAGGGCATTAG AAATGATTAGGC | GCTGCATCCAGTTTGCAA AGT | | CTACAGCATAATAGTTACCC GCTCACT | |
| | | | SEQ ID NO:1549 | | SEQ ID NO:9561 | | SEQ ID NO:17573 |
| | | AA | RASQGIRNDLG | AASSLQS | | LQHNSYPLT | |
| | | | SEQ ID NO:1550 | | SEQ ID NO:9562 | | SEQ ID NO:17574 |
| iPS:434315 | 21-225_59G7 | NA | CGGGCAAGTCAGGGCATTAG AAATGATTAGGC | TCTGCATCCAGTTTACAA AGT | | CTACAGCATAATAGTTACCC GTGGACG | |
| | | | SEQ ID NO:1551 | | SEQ ID NO:9563 | | SEQ ID NO:17575 |
| | | AA | RASQGIRNDLG | SASSLQS | | LQHNSYPWT | |
| | | | SEQ ID NO:1552 | | SEQ ID NO:9564 | | SEQ ID NO:17576 |
| iPS:434317 | 21-225_59E8 | NA | CGGGCAAGTCAGAGCATTAG AAATGATTAGGC | GCTGCATCCAGTTTGCAA AGT | | CAACAGAGTTTCAGTAATTC GATACC | |
| | | | SEQ ID NO:1553 | | SEQ ID NO:9565 | | SEQ ID NO:17577 |
| | | AA | RASQSISSYLN | AASSLQS | | QQSFSNSIT | |
| | | | SEQ ID NO:1554 | | SEQ ID NO:9566 | | SEQ ID NO:17578 |
| iPS:434319 | 21-225_59B9 | NA | CGGGCAAGTCAGGACATTAG AAATGATTAGGC | GCTGCATCCAGTTTACAA AGT | | CTACAGCATAATAGTTACCC GTGGACG | |
| | | | SEQ ID NO:1555 | | SEQ ID NO:9567 | | SEQ ID NO:17579 |

FIGURE 49
(Continued)

| | | | | | | |
|---|---|---|---|---|---|---|
| iPS:434321 | 21-225_59F10 | AA | RASQDIRNDLG SEQ ID NO:1556 | AASSLQS SEQ ID NO:9568 | LQHNSYPWT SEQ ID NO:17580 |
| | | NA | AAGTCCAGCCAGACTGTTTTATACAGGTCCAACAATTACAACTACTTAGCT SEQ ID NO:1557 | TGGGCATCTACCCGGGAATCC SEQ ID NO:9569 | CAGCAATATTTTAGTACTCCTCCGACG SEQ ID NO:17581 |
| iPS:434323 | 21-225_62H8 | AA | KSSQTVLYRSNNYNYLA SEQ ID NO:1558 | WASTRES SEQ ID NO:9570 | QQYFSTPPT SEQ ID NO:17582 |
| | | NA | CGGGCAAGTCAGAGCATTTTCAGCTATTTAAAT SEQ ID NO:1559 | GCGTCATCCAGTTGCAAAGT SEQ ID NO:9571 | CAACAGAGTTACAGTACCCCATTCACT SEQ ID NO:17583 |
| iPS:434327 | 21-225_63G6 | AA | RASQSIFSYLN SEQ ID NO:1560 | ASSSLQS SEQ ID NO:9572 | QQSYSTPFT SEQ ID NO:17584 |
| | | NA | CGGGCAAGTCAGAGCATTTTCAGCTATTTAAAT SEQ ID NO:1561 | GATACATCCACTTGCAAACT SEQ ID NO:9573 | CAACAGAGTTACGGTATCCCATCACC SEQ ID NO:17585 |
| iPS:434331 | 21-225_63H8 | AA | RASQSIFSYLN SEQ ID NO:1562 | DTSTLQT SEQ ID NO:9574 | QQSYGIPFT SEQ ID NO:17586 |
| | | NA | CGGGCGAGTCAGGGCATTAGCAATTATTTAGCC SEQ ID NO:1563 | GCTGCATCCAGTTGCAAAGT SEQ ID NO:9575 | CAACAATATCATAGTACCCATTCACT SEQ ID NO:17587 |
| iPS:434333 | 21-225_63C9 | AA | RASQGISNYLA SEQ ID NO:1564 | AASSLQS SEQ ID NO:9576 | QQYHSYPFT SEQ ID NO:17588 |
| | | NA | CGGGCGAGTCAGGGTATTAGCAGCTGGTTAGCC SEQ ID NO:1565 | GCTGCATCCAGTTGCAAAGT SEQ ID NO:9577 | CAACAGATTAACAGTTCCTCTCACT SEQ ID NO:17589 |
| iPS:434335 | | AA | RASQGISSWLA SEQ ID NO:1566 | AASSLQS SEQ ID NO:9578 | QQINSFPLT SEQ ID NO:17590 |
| | | NA | CGGGCAAGTCAGAGCATTTCAGCTATTTACAT | GCTGCATCCAGTTTACAAAGT | CAACAGACTTACAGTCCCCCGCTCACT |

FIGURE 49
(Continued)

| | | | | | | |
|---|---|---|---|---|---|---|
| iPS:434337 | 21-225_63C10 | AA | SEQ ID NO:1567<br>RASQSIFSYLH<br>SEQ ID NO:1568 | | SEQ ID NO:9579<br>AASSLQS<br>SEQ ID NO:9580 | SEQ ID NO:17591<br>QQTYSPPLT<br>SEQ ID NO:17592 |
| iPS:434339 | 21-225_64E1 | NA | CGGGCAAGTCAGGGCATTAG<br>AAATGATTAGGC<br>SEQ ID NO:1569 | GCTGCATCCAGTTTGCAA<br>AGT<br>SEQ ID NO:9581 | | CTACAGCATTATAGTTACCC<br>GCTCACT<br>SEQ ID NO:17593 |
| | | AA | RASQGIRNDLG<br>SEQ ID NO:1570 | AASSLQS<br>SEQ ID NO:9582 | | LQHNSYPLT<br>SEQ ID NO:17594 |
| iPS:434341 | 21-225_64A4 | NA | CGGGCAAGTCAGGGCATTAG<br>AAATGATTAGGC<br>SEQ ID NO:1571 | GCTGCATCCAGTTTGCAA<br>AGT<br>SEQ ID NO:9583 | | CTACAGCATTATAGTTACCC<br>TCGGACG<br>SEQ ID NO:17595 |
| | | AA | RASQGIRNDLG<br>SEQ ID NO:1572 | AASSLQS<br>SEQ ID NO:9584 | | LQHYSYPRT<br>SEQ ID NO:17596 |
| iPS:434341 | 21-225_64F7 | NA | CGGGCAAGTCAGAACATTAA<br>GAAATATTTAAAT<br>SEQ ID NO:1573 | GGTGCATCCAGTTGCA<br>AAGT<br>SEQ ID NO:9585 | | CAACAGAGTTACAATATTTC<br>GTTCACT<br>SEQ ID NO:17597 |
| | | AA | RASQNIKKYLN<br>SEQ ID NO:1574 | GASSLQS<br>SEQ ID NO:9586 | | QQSYNISFT<br>SEQ ID NO:17598 |
| iPS:434343 | 21-225_64C8 | NA | CGGGCAAGTCAGGGCATTAG<br>AAATGATTAGGC<br>SEQ ID NO:1575 | GCTGCATCCAGTTTGCAA<br>AGT<br>SEQ ID NO:9587 | | CTACACCATTATAGTTACCC<br>TCGGACG<br>SEQ ID NO:17599 |
| | | AA | RASQGIRNDLG<br>SEQ ID NO:1576 | AASSLQS<br>SEQ ID NO:9588 | | LHHYSYPRT<br>SEQ ID NO:17600 |
| iPS:434345 | 21-225_64H9 | NA | AAGTCTAGTCAGAGCCTCCT<br>TCATGGTGATGGAAAGACCT<br>ATTTGTTT<br>SEQ ID NO:1577 | GAAGTTTCCAACCGGTT<br>GTGT<br>SEQ ID NO:9589 | | ATGCAAAGTATACAGGTTCC<br>GTGGACG<br>SEQ ID NO:17601 |
| | | AA | KSSQSLLHGDGKTYLF<br>SEQ ID NO:1578 | EVSNRLC<br>SEQ ID NO:9590 | | MQSIQVPWT<br>SEQ ID NO:17602 |

FIGURE 49
(Continued)

| | | | | | |
|---|---|---|---|---|---|
| iPS:434347 | 21-225_64H10 | NA | CGGGCGAGTCAGGGTATTAG CAGCTGGTTAGCC SEQ ID NO:1579 | GCTGCATCCAGTTTGCAA AGT SEQ ID NO:9591 | CAACAGATTAACAGTTTCCC TCTCACT SEQ ID NO:17603 |
| | | AA | RASQGISSWLA SEQ ID NO:1580 | AASSLQS SEQ ID NO:9592 | QQINSFPLT SEQ ID NO:17604 |
| iPS:434351 | 21-225_64A12 | NA | CGGGCAAGTCAGGGCATTAG AAATGATTAGGC SEQ ID NO:1581 | ACTGCATCCACTTTGCAA AGT SEQ ID NO:9593 | CTACAGCATAATGGTTACCC ATTCACT SEQ ID NO:17605 |
| | | AA | RASQGIRNDLG SEQ ID NO:1582 | TASTLQS SEQ ID NO:9594 | LQHNGYPFT SEQ ID NO:17606 |
| iPS:434353 | 21-225_64B12 | NA | CGGGCGAGTCAGGACATTAG CAATTATTAAAT SEQ ID NO:1583 | GATGCATCCATTTTGGAA ACA SEQ ID NO:9595 | CAACAGAGTGATAATCTCCC GTGCAGT SEQ ID NO:17607 |
| | | AA | RASQDISNYLN SEQ ID NO:1584 | DASILET SEQ ID NO:9596 | QQSDNLPCS SEQ ID NO:17608 |
| iPS:434355 | 21-225_64G12 | NA | CGGGCGAGTCAGGGTATTAG CACCTGGTTAGCC SEQ ID NO:1585 | GCTGCATCCAGTTTGCAA AGT SEQ ID NO:9597 | CAACAGGCTAACAGTTTCC ATTCACT SEQ ID NO:17609 |
| | | AA | RASQNITWLA SEQ ID NO:1586 | AASSLQS SEQ ID NO:9598 | QQANSFPFT SEQ ID NO:17610 |
| iPS:434357 | 21-225_65C1 | NA | CGGGCGAGTCAGGGTCATTAG CAGTTATTTACAT SEQ ID NO:1587 | AGTGCATCCAATTTGCA ATGT SEQ ID NO:9599 | CAACGGCCTTACAATGCCC GCTCACT SEQ ID NO:17611 |
| | | AA | RASQVISSYLH SEQ ID NO:1588 | SASNLQC SEQ ID NO:9600 | QRPYNAPLT SEQ ID NO:17612 |
| iPS:434359 | 21-225_65G3 | NA | CGGGCGAGTCAGGGTATTAG CAGCTGGTTAGCC SEQ ID NO:1589 | GCTGCATCCAGTTTGCAA AGT SEQ ID NO:9601 | CAACAGGTTAACAGTTTCCC TCTCACT SEQ ID NO:17613 |
| | | AA | RASQGISSWLA SEQ ID NO:1590 | AASSLQS SEQ ID NO:9602 | QQVNSFPLT SEQ ID NO:17614 |

FIGURE 49
(Continued)

| | | | | | |
|---|---|---|---|---|---|
| iPS:434361 | 21-225_65D5 | NA | CGGGCGAGTCAGGACATTAA CAATTATTAGCC SEQ ID NO:1591 | GCTGCATCCAGTTTGCAC AGT SEQ ID NO:9603 | CCACTGTATAAAGTTATCC ACTCACT SEQ ID NO:17615 |
| | | AA | RASQDINNYLA SEQ ID NO:1592 | AASSLHS SEQ ID NO:9604 | PLYKSYPLT SEQ ID NO:17616 |
| iPS:434363 | 21-225_65A6 | NA | AGGGCAGTCAGAGTGTTAA CAGCAACTTAGCC SEQ ID NO:1593 | GGTGCATCCACCAGGGC CACT SEQ ID NO:9605 | CAGCAGTATAATGACTGGCC GTGCAGT SEQ ID NO:17617 |
| | | AA | RASQSVNSNLA SEQ ID NO:1594 | GASTRAT SEQ ID NO:9606 | QQYNDWPCS SEQ ID NO:17618 |
| iPS:434367 | 21-225_65H11 | NA | CGGGCGAGTCAGGACATTAG CACTTATTAGCC SEQ ID NO:1595 | GCTGCATCCAGTTTGCAA AGT SEQ ID NO:9607 | CAACAGTATAATAGTTTCCC TCTCACT SEQ ID NO:17619 |
| | | AA | RASQDISTYLA SEQ ID NO:1596 | AASSLQS SEQ ID NO:9608 | QQYNSFPLT SEQ ID NO:17620 |
| iPS:434369 | 21-225_66B1 | NA | CGGGCGAGTCAGGGTATTAG CAGCTGGTTAGCC SEQ ID NO:1597 | GCTGCATCCAGTTTGCAA AGT SEQ ID NO:9609 | CAACAGACTAACAGTTTCCC TCTCACT SEQ ID NO:17621 |
| | | AA | RASQGISSWLA SEQ ID NO:1598 | AASSLQS SEQ ID NO:9610 | QQTNSFPLT SEQ ID NO:17622 |
| iPS:434373 | 21-225_66A7 | NA | CGGGCGAGTCAGGGTATTAG CAGCTGGTTAGCC SEQ ID NO:1599 | GCTGCATCCAGTTTGCAA AGT SEQ ID NO:9611 | CAACAGATTAATAGTTTCCC TCTCACT SEQ ID NO:17623 |
| | | AA | RASQGISSWLA SEQ ID NO:1600 | AASSLQS SEQ ID NO:9612 | QQINSFPLT SEQ ID NO:17624 |
| iPS:434375 | 21-225_66C7 | NA | CGGGCGAGTCAGGGCATTAG CAATTATTTACAT SEQ ID NO:1601 | TGTTGCATCCAATTACAA TGT SEQ ID NO:9613 | CAACAGCATAATAATTCCCC GCTCACT SEQ ID NO:17625 |
| | | AA | RASQGISNYLH SEQ ID NO:1602 | CASNLQC SEQ ID NO:9614 | QQHNNSPLT SEQ ID NO:17626 |

FIGURE 49
(Continued)

| | | | | | |
|---|---|---|---|---|---|
| iPS:434379 | 21-225_66A9 | NA | CGGGCAAGTCAGAGAACATTTT CAGCTATTAAAT SEQ ID NO:1603 RASQNIFSYLN SEQ ID NO:1604 | GCTGCATCCAGTTTACAA AGT SEQ ID NO:9615 AASSLQS SEQ ID NO:9616 | CAACAGACTTACAGTGTCCC TTTCACT SEQ ID NO:17627 QQTYSVPFT SEQ ID NO:17628 |
| iPS:434383 | 21-225_66F9 | AA | CGGGCAAGTCAGGACATTAG AAATGTTTAGGC SEQ ID NO:1605 RASQDIRNVLG SEQ ID NO:1606 | ACTGCATCCAGTTTACAA AGT SEQ ID NO:9617 TASSLQS SEQ ID NO:9618 | CTACAGTATAATAGTTACCC ATTCACT SEQ ID NO:17629 LQYNSYPFT SEQ ID NO:17630 |
| iPS:434385 | 21-225_66C10 | NA | CGGGCAAGTCAGGCCATTAG AAATGATTAGGC SEQ ID NO:1607 RASQAIRNDLG SEQ ID NO:1608 | CCTGCATCCAGTTTGCAA AGT SEQ ID NO:9619 PASSLQS SEQ ID NO:9620 | CTACAGTATAATAGTTACCC TCCGTGGACG SEQ ID NO:17631 LQYNSYPPWT SEQ ID NO:17632 |
| iPS:434387 | 21-225_66D11 | AA | CGGGCAAGTCAGGGCATTAG AAATGATTAGGT SEQ ID NO:1609 RASQGIRNDLG SEQ ID NO:1610 | GCTGCATCCAGTGTCAA AGT SEQ ID NO:9621 AASSCQS SEQ ID NO:9622 | ATAGTCATAATAGTTACCA TCGGACG SEQ ID NO:17633 IVHNSYPRT SEQ ID NO:17634 |
| iPS:434389 | 21-225_66F11 | NA | CGGGAGAGTCAGGGTATTAG CATCTGGTTAGCC SEQ ID NO:1611 RESQGISIWLA SEQ ID NO:1612 | GCTGCATCCAGTTGCAA AGT SEQ ID NO:9623 AASSLQS SEQ ID NO:9624 | CAACAGGCTAACAGTTCCC ATTCACT SEQ ID NO:17635 QQANSFPFT SEQ ID NO:17636 |
| iPS:434393 | 21-225_67C3 | AA | AGGGCCAGTCAGAGAGTGTTAA CAGCAACTTAGCC SEQ ID NO:1613 RASQSVNSNLA SEQ ID NO:1614 | ATTGCATCCACCAGGGC CACT SEQ ID NO:9625 IASTRAT SEQ ID NO:9626 | CAGCAGTATAATGACTGGCC GTGTAGT SEQ ID NO:17637 QQYNDWPCS SEQ ID NO:17638 |

FIGURE 49
(Continued)

| | | | | | | |
|---|---|---|---|---|---|---|
| iPS:434397 | 21-225_67H4 | NA | CGGGCGAGTCAGGGTATTAG CAGCTGGTTAGGC SEQ ID NO:1615 | GCTGCATCCAGTTTGCAA AGT SEQ ID NO:9627 | CAACAGATTAACAGTTTCCC TCTCACT SEQ ID NO:17639 |
| | | AA | RASQGISSWLA SEQ ID NO:1616 | AASSLQS SEQ ID NO:9628 | QQINSFPLT SEQ ID NO:17640 |
| iPS:434399 | 21-225_67B7 | NA | CGGGCAAGTCAGGGCATTAG AAATGATTAGGC SEQ ID NO:1617 | GCTGCATCCAGTTTGCAA AGT SEQ ID NO:9629 | CTACACCATAATAGTTACC ATTCAAA SEQ ID NO:17641 |
| | | AA | RASQGIRNDLG SEQ ID NO:1618 | AASSLQS SEQ ID NO:9630 | LHHNSYPFK SEQ ID NO:17642 |
| iPS:434405 | 21-225_68E6 | NA | CGGGCGAGTCAGGGCATTAG CTATTATTAGGC SEQ ID NO:1619 | GTTGCATCCAGTTTGCAA AGT SEQ ID NO:9631 | CAACAGTATGATAGTTACCC ATTCACT SEQ ID NO:17643 |
| | | AA | RASQGISYYLA SEQ ID NO:1620 | VASSLQS SEQ ID NO:9632 | QQYDSYPFT SEQ ID NO:17644 |
| iPS:434407 | 21-225_68G8 | NA | CGGGCAAGTCAGGGCATTAG AAATGATTAGGC SEQ ID NO:1621 | GCTGCATCCAGTGTGCA AAGT SEQ ID NO:9633 | CTACAGTATAATAGTTACC ATTCACT SEQ ID NO:17645 |
| | | AA | RASQGIRNNLG SEQ ID NO:1622 | AASSVQS SEQ ID NO:9634 | LQYNSYPFT SEQ ID NO:17646 |
| iPS:434411 | 21-225_68F11 | NA | CGGGCAAGTCAGGGCATTAG AAATGATTAGGC SEQ ID NO:1623 | GCTGCATCCAGTTTGCAA AGT SEQ ID NO:9635 | CTACAGCATAATAGTTACC GTTCACT SEQ ID NO:17647 |
| | | AA | RASQGIRNDLG SEQ ID NO:1624 | AASSLQS SEQ ID NO:9636 | LQHNSYPFT SEQ ID NO:17648 |
| iPS:434413 | 21-225_68D12 | NA | CGGGCAAGTCAGGGCATTAG AAATGATTAGGC SEQ ID NO:1625 | GCTGCATCCAGTTTGCAA AGT SEQ ID NO:9637 | CTACACGATAGTACTTACC GCTCACT SEQ ID NO:17649 |
| | | AA | RASQGIRNDLG SEQ ID NO:1626 | AASSLQS SEQ ID NO:9638 | LQHSTYPLT SEQ ID NO:17650 |

FIGURE 49
(Continued)

| | | | | | |
|---|---|---|---|---|---|
| iPS:434417 | 21-225_69C8 | NA | CGGGCAGGTCAGACCATTTA CAATTATTTAAAT SEQ ID NO:1627 | GTTGGCGTCCAGTTTGCAA AGT SEQ ID NO:9639 | CAACAGAGTTACAGTACCCC ATTCACT SEQ ID NO:17651 |
| | | AA | RAGQTIYNYLN SEQ ID NO:1628 | VASSLQS SEQ ID NO:9640 | QQSYSTPFT SEQ ID NO:17652 |
| iPS:434423 | 21-225_70D1 | NA | CGGGGAGTCAGGGTGTTAG CAGGTGGTTAGCC SEQ ID NO:1629 | GCTGCATCCAGTTTGCAA AGT SEQ ID NO:9641 | CAACAGGCTAACAGTTTCCC ATTCACT SEQ ID NO:17653 |
| | | AA | RASQGVSRWLA SEQ ID NO:1630 | AASSLQS SEQ ID NO:9642 | QQANSFPFT SEQ ID NO:17654 |
| iPS:434425 | 21-225_70A5 | NA | AGGGCCAGTCAGAGTGTTAA CAGCAACTTAGCC SEQ ID NO:1631 | ATTGCATCCACCAGGGC CACT SEQ ID NO:9643 | CAGCAGTATAATGACTGGCC GTGTAGT SEQ ID NO:17655 |
| | | AA | RASQSVNSNLA SEQ ID NO:1632 | IASTRAF SEQ ID NO:9644 | QQYNDWPCS SEQ ID NO:17656 |
| iPS:434427 | 21-225_70D6 | NA | CGGGGAGTCAGGGTATTAG CAAATGGTTAGCC SEQ ID NO:1633 | GCTGCATCCAGTTTGCAA AGT SEQ ID NO:9645 | CAACAGACTAACAGTTTCCC TCTCACT SEQ ID NO:17657 |
| | | AA | RASQGISKWLA SEQ ID NO:1634 | AASSLQS SEQ ID NO:9646 | QQTNSFPLT SEQ ID NO:17658 |
| iPS:434429 | 21-225_70H6 | NA | CGGACAAGTCAGAGCATTTT CAACTATTTAAAT SEQ ID NO:1635 | ACTGCATCCAGTTTGCAA AGT SEQ ID NO:9647 | CAACAGAGTTACAGTATCCC GCTCACT SEQ ID NO:17659 |
| | | AA | RTSQSIFNYLN SEQ ID NO:1636 | TASSLQS SEQ ID NO:9648 | QQSYSIPLT SEQ ID NO:17660 |
| iPS:434431 | 21-225_70E7 | NA | AAGTCCAGCAGTCAGAGTGTTT ATACAGCTCCAACAATAACA ACTACTTGGCT SEQ ID NO:1637 | TGGGCATCTACCCGGGA ATCC SEQ ID NO:9649 | CAGCAATATATAATATTCC TCCGACG SEQ ID NO:17661 |
| | | AA | KSSQSVLYSSNNNNYLA | WASTRES | QQYNIPPT |

FIGURE 49
(Continued)

| | | | | | |
|---|---|---|---|---|---|
| iPS:434433 | 21-225_70E8 | NA | SEQ ID NO:1638 CGGGCAAGTCAGGGCATTAG AAAGGATTTAGGC | SEQ ID NO:9650 GCTGCATCCAGTTTGCAA AGT | SEQ ID NO:17662 CTACAGCAGTAATCGTTACCC GCTCACT |
| | | AA | SEQ ID NO:1639 RASQGIRKDLG | SEQ ID NO:9651 AASSLQS | SEQ ID NO:17663 LQHNRYPLT |
| iPS:434435 | 21-225_70G9 | NA | SEQ ID NO:1640 CGGGCGAGTCAGGATATTAG CAGCTGGTTAGCC | SEQ ID NO:9652 GCTGCATCCAGTTTGCAA AGT | SEQ ID NO:17664 CAACAGACTAACAGTTTCCC TCTCACT |
| | | AA | SEQ ID NO:1641 RASQDISSWLA | SEQ ID NO:9653 AASSLQS | SEQ ID NO:17665 QQTNSFPLT |
| iPS:434437 | 21-225_70A12 | NA | SEQ ID NO:1642 CGGGCGAGTCAGGGTATTAG CAGCTGGTTAGCC | SEQ ID NO:9654 GCTGCATCCAGTTTGCAA AGT | SEQ ID NO:17666 CAACAGATTAACAGTTTCCC TCTCACT |
| | | AA | SEQ ID NO:1643 RASQGISSWLA | SEQ ID NO:9655 AASSLQS | SEQ ID NO:17667 QQINSFPLT |
| iPS:434439 | 21-225_70E12 | NA | SEQ ID NO:1644 CGGGCAAGTCAGGGCATTAA CAATAATTTAAAC | SEQ ID NO:9656 GCTGCATCCAGTTTGCAA AGT | SEQ ID NO:17668 CTACAGGAGTAATAGTTACCC GCTCACT |
| | | AA | SEQ ID NO:1645 RASQGINNNLN | SEQ ID NO:9657 AASSLQS | SEQ ID NO:17669 LQHNSYPLT |
| iPS:434441 | 21-225_71A2 | NA | SEQ ID NO:1646 CGTGCAAGTCAGGGCATTAG AAATGATTTAGGA | SEQ ID NO:9658 ATTGCATTCAGATTGCAA ATT | SEQ ID NO:17670 ATACACCATAATAGTTACCC GTGGACG |
| | | AA | SEQ ID NO:1647 RASQGIRNDLG | SEQ ID NO:9659 IAFRLQI | SEQ ID NO:17671 IHHNSYPWT |
| iPS:434443 | 21-225_71G3 | NA | SEQ ID NO:1648 AAGTCCAGCCAGAGTGTTTT ACACAGCTCCAACAATAACA ACTACTTAGAT | SEQ ID NO:9660 TGGGCATCTACCCGGGA ATTC | SEQ ID NO:17672 CAACAATATTATATTACTCC GTGCAGT |
| | | | SEQ ID NO:1649 | | SEQ ID NO:17673 |

FIGURE 49
(Continued)

| | | | | | | | | |
|---|---|---|---|---|---|---|---|---|
| iPS:434447 | | AA | KSSQSVLHSSNNNYLD | | WASTREF | | QQYYITPCS | |
| | | | SEQ ID NO:1650 | | SEQ ID NO:9662 | | SEQ ID NO:17674 | |
| | 21-225_71B6 | NA | CGGGCAAGTCAGGGCATTAG AAATGATTAGAT | | GCTGCATCCAGTTTGCAA AGT | | CTACAGCATAATAGTTACC ATTCACT | |
| | | | SEQ ID NO:1651 | | SEQ ID NO:9663 | | SEQ ID NO:17675 | |
| iPS:434449 | | AA | RASQGIRNDLD | | AASSLQS | | LQHNSYPFT | |
| | | | SEQ ID NO:1652 | | SEQ ID NO:9664 | | SEQ ID NO:17676 | |
| | 21-225_71H6 | NA | CGGGCAAGTCAGGGCATTAG AAATGTTTAGGC | | GCTGCATCCAGTTTGCAA AGT | | CTACAGTATAATAGTTACC ATTCACT | |
| | | | SEQ ID NO:1653 | | SEQ ID NO:9665 | | SEQ ID NO:17677 | |
| iPS:434451 | | AA | RASQGIRNVLG | | AASSLQS | | LQYNSYPFT | |
| | | | SEQ ID NO:1654 | | SEQ ID NO:9666 | | SEQ ID NO:17678 | |
| | 21-225_71B7 | NA | CGGGCGAGTCAGGGTATTAG CAGCTGGTTAGCC | | GCTGCATCCAGTTTGCAA GGT | | CAACAGACTAATACTTACC TCTCACT | |
| | | | SEQ ID NO:1655 | | SEQ ID NO:9667 | | SEQ ID NO:17679 | |
| iPS:434453 | | AA | RASQGISSWLA | | AASSLQG | | QQTNSFPLT | |
| | | | SEQ ID NO:1656 | | SEQ ID NO:9668 | | SEQ ID NO:17680 | |
| | 21-225_71B11 | NA | CGGGCAAGTCAGGGCATTAG AAATGATTAGAT | | GCTGCATCCAGTTTGCAA AGT | | CTACAGCATAATACTTACC ATTCACT | |
| | | | SEQ ID NO:1657 | | SEQ ID NO:9669 | | SEQ ID NO:17681 | |
| iPS:434455 | | AA | RASQGIRNDLD | | AASSLQS | | LQHNTYPFT | |
| | | | SEQ ID NO:1658 | | SEQ ID NO:9670 | | SEQ ID NO:17682 | |
| | 21-225_72F5 | NA | CGGGCAAGTCAGAACATTAG CAGTTATTAAAT | | GCTGCATCCAGTTTGCAA AGT | | CAACAGACTTACAGTACCC CACC | |
| | | | SEQ ID NO:1659 | | SEQ ID NO:9671 | | SEQ ID NO:17683 | |
| iPS:434457 | | AA | RASQNISSYLN | | AASSLQS | | QQFYSTPT | |
| | | | SEQ ID NO:1660 | | SEQ ID NO:9672 | | SEQ ID NO:17684 | |
| | 21-225_72G12 | NA | CGGGCGAGTCAGGGCATTAG CAGTTATTAAAT | | GGTGCTTCCAATTTGCAA TCT | | CAACAGAATTACAATGCCCC GCTCACT | |
| | | | SEQ ID NO:1661 | | SEQ ID NO:9673 | | SEQ ID NO:17685 | |

FIGURE 49
(Continued)

| | | | | | | |
|---|---|---|---|---|---|---|
| iPS:434459 | 21-225_71A7 | AA | RASQGISSYLN SEQ ID NO:1662 | CGGGCGAGTCAGGGTATTAG CAGCTGGTTAGCC SEQ ID NO:1663 | GASNLQS SEQ ID NO:9674 | GCTGCATCCAGTTTGCAA AGT SEQ ID NO:9675 | QQNYNAPLT SEQ ID NO:17686 | CAACAGGTTAACAGTTTCCC TCTCACT SEQ ID NO:17687 |
| iPS:434461 | 21-225_73A3 | AA | RASQGISSWLA SEQ ID NO:1664 | CGGGCGAGTCAGGGTATTAG CAACTGGTTAGCC SEQ ID NO:1665 | AASSLQS SEQ ID NO:9676 | GCTGCATCCAGTTTGCAA AGT SEQ ID NO:9677 | QQVNSFPLT SEQ ID NO:17688 | CAACAGGTTAACAGTTTCCC TCTCACT SEQ ID NO:17689 |
| iPS:434463 | 21-225_73A6 | AA | RASQGISNWLA SEQ ID NO:1666 | CGGGCAAGTCAGGGCATTAG AAATGATTAGGC SEQ ID NO:1667 | AASSLQS SEQ ID NO:9678 | GCTGCATCCAGTTTGCAA AGT SEQ ID NO:9679 | QQVNSFPLT SEQ ID NO:17690 | CTACAGCATAATAGTTACC ATTCACT SEQ ID NO:17691 |
| iPS:434467 | 21-225_73H8 | AA | RASQDIRNDLG SEQ ID NO:1668 | CGGGCAAGTCAGGACATCA GAAATGATTAGGC SEQ ID NO:1669 | AASNLQS SEQ ID NO:9680 | GCTGCATCCAGTTTGCAA AGT SEQ ID NO:9681 | LQHNSYPFT SEQ ID NO:17692 | ATACAGCATAATAGTTACC TCCGATCACC SEQ ID NO:17693 |
| iPS:434469 | 21-225_73C9 | AA | RASQGIRNDLG SEQ ID NO:1670 | CGGGCAAGTCAGGGCATTAG AAATGATTAGGC SEQ ID NO:1671 | AASSLQS SEQ ID NO:9682 | GCTGCATCCAGTTTGCAA AGT SEQ ID NO:9683 | IQHNSYPPIT SEQ ID NO:17694 | CTACAGCATATAGTTACC TCGGACG SEQ ID NO:17695 |
| iPS:434471 | 21-225_75G3 | AA | RASQGIRNDLG SEQ ID NO:1672 | AGGGCCCGTCAGAATGTTGA CAGCAGTACTTAGCC SEQ ID NO:1673 | GGTGCATCCAGCAGGGC CACT SEQ ID NO:9684 | | LQHYSYPRT SEQ ID NO:17696 | CAGCAGTATGAACGCTCACC GTGGACG SEQ ID NO:17697 |

FIGURE 49
(Continued)

| | | | | | | |
|---|---|---|---|---|---|---|
| iPS:434473 | | AA | RARQNVDSSYLA SEQ ID NO:1674 | GASSRAT SEQ ID NO:9686 | QQYERSPWT SEQ ID NO:17698 | |
| | 21-225_76D1 | NA | AGGGCCAGTCAGAATATTTA CAGCAACTACCTAGCC SEQ ID NO:1675 | GGTGCATCCAGCAGGGC CACT SEQ ID NO:9687 | CAGCAGTATGAAAGTTCACC GTGGACG SEQ ID NO:17699 | |
| iPS:434475 | | AA | RASQNIYSNYLA SEQ ID NO:1676 | GASSRAT SEQ ID NO:9688 | QQYESSPWT SEQ ID NO:17700 | |
| | 21-225_74F9 | NA | AAGTCCAGCCAGAGTGTTT ATACAGCTCCAACAATTACA ACTACTTAGCT SEQ ID NO:1677 | TGGGCATCTACCCGGGA ATCC SEQ ID NO:9689 | CAGCAATATTATAGTAGTCC TCCGACG SEQ ID NO:17701 | |
| iPS:434477 | | AA | KSSQSVLYSSNNYNYLA SEQ ID NO:1678 | WASTRES SEQ ID NO:9690 | QQYYSSPPT SEQ ID NO:17702 | |
| | 21-225_74A6 | NA | AAGTCCAGCCAGAGTGTTT ACACAGCTCCAACAATAACA ATTACTTAGCC SEQ ID NO:1679 | TGGGCATCAACCCGGGA ATCC SEQ ID NO:9691 | CAGCAATATTTTAGTACTCC GTGGACG SEQ ID NO:17703 | |
| iPS:434479 | | AA | KSSQSVLHSSNNNNYLA SEQ ID NO:1680 | WASTRES SEQ ID NO:9692 | QQYFSTPWT SEQ ID NO:17704 | |
| | 21-225_76H1 | NA | AGGGCCAGTCAGAGTGTTAG CAGCAGCTACTAGTC SEQ ID NO:1681 | GGTGCATCCACCAGGGC CACT SEQ ID NO:9693 | CAGCAGTATGGTTGCTCACC GCTCACT SEQ ID NO:17705 | |
| iPS:434481 | | AA | RASQSVSSSYLV SEQ ID NO:1682 | GASTRAT SEQ ID NO:9694 | QQYGCSPLT SEQ ID NO:17706 | |
| | 21-225_74B10 | NA | AAGTCCAGCCAGAGTGTTT ACACAGCTCCAACAATAAGA ACTACTTAACT SEQ ID NO:1683 | TGGGCATCTACTCGGGA ATCC SEQ ID NO:9695 | CAGCAATATTATAGTATTCC TCCGACG SEQ ID NO:17707 | |
| | | AA | KSSQSVLHSSNNKNYLT SEQ ID NO:1684 | WASTRES SEQ ID NO:9696 | QQYYSIPPT SEQ ID NO:17708 | |

FIGURE 49
(Continued)

| | | | | | |
|---|---|---|---|---|---|
| iPS:434483 | 21-225_74C12 | NA | AAGTCCAGCCAGAGTGTTT ATACAGCTCCAACAATGCGA ACTACTTAGCT SEQ ID NO:1685 | TGGGCATCTACCCGGGA ATCC SEQ ID NO:9697 | CAGCAATATTATAGTACTCC GTGCAGT SEQ ID NO:17709 |
| | | AA | KSSQSVLYSSNNANYLA SEQ ID NO:1686 | WASTRES SEQ ID NO:9698 | QQYYSTPCS SEQ ID NO:17710 |
| iPS:434485 | 21-225_76D2 | NA | AGGGCCAGTGTGAGTGTGT CAACAGCTTAGCC SEQ ID NO:1687 | GGTGCATCCACCAGGC CACT SEQ ID NO:9699 | CAGCAATATAATGACTGGCC GTGCAGT SEQ ID NO:17711 |
| | | AA | RASVSVVNSLA SEQ ID NO:1688 | GASTRAT SEQ ID NO:9700 | QQYNDWPCS SEQ ID NO:17712 |
| iPS:434487 | 21-225_76G2 | NA | AAGTCCAGCCAGAGTGTTT ACACAGCTCCAACAATTACA ACTACTTAGCT SEQ ID NO:1689 | TGGGCATCTACCCGGGA ATCC SEQ ID NO:9701 | CAGCAATATTATAGTTCTCC TCCGACG SEQ ID NO:17713 |
| | | AA | KSSQSVLHSSNNYNYLA SEQ ID NO:1690 | WASTRES SEQ ID NO:9702 | QQYYSSPPT SEQ ID NO:17714 |
| iPS:434489 | 21-225_74E4 | NA | CGGGCAAGTCAGGGCATTAG AAATGATTAGGC SEQ ID NO:1691 | GCTGCATCCACTTTGCAA AGT SEQ ID NO:9703 | CTACAGCATAGTAATTACC GCTCACT SEQ ID NO:17715 |
| | | AA | RASQGIRNDLG SEQ ID NO:1692 | AASTLQS SEQ ID NO:9704 | LQHSNYPLT SEQ ID NO:17716 |
| iPS:434493 | 21-225_76F3 | NA | AAGTCCAGCCAGAGTGTTTT ATTCAGCTCCAACAATATA ATTACTTAGCT SEQ ID NO:1693 | TGGGCATCTACCCGGGA ATCC SEQ ID NO:9705 | CAGCAATATCATAGTTCTCC TCTGACG SEQ ID NO:17717 |
| | | AA | KSSQSVLFSSNNYNYLA SEQ ID NO:1694 | WASTRES SEQ ID NO:9706 | QQYHSSPLT SEQ ID NO:17718 |
| iPS:434495 | | NA | AGGGCCAGTCAGAATATTA CAGCAGTTACTTAGCC | GGTGCATCCAGCAGGGC CACT | CAGCAGTATGAAAGCTCACC GTGGACC |

FIGURE 49
(Continued)

| | | | | | | |
|---|---|---|---|---|---|---|
| iPS:434497 | 21-225_74B2 | AA | SEQ ID NO:1695 RASQNIYSSYLA | SEQ ID NO:9707 GASSRAT | SEQ ID NO:17719 QQYESSPWT | |
| | | NA | SEQ ID NO:1696 AGGGCCAGTCAGAGTGTTTA CAGCAGCTACTTAGCC | SEQ ID NO:9708 GGTGCATCCAGCCGGGC CACT | SEQ ID NO:17720 CAGCAGTATGAATAACTCACC GTGGACG | |
| iPS:434501 | 21-225_76A4 | AA | SEQ ID NO:1697 RASQSVYSSYLA | SEQ ID NO:9709 GASSRAT | SEQ ID NO:17721 QHSDNSPWT | |
| | | NA | SEQ ID NO:1698 AGGGCCAGTCAGAGTGTTTA CAGCAGCTACTTAGCC | SEQ ID NO:9710 GGTGCATCCAGCCGGGC CACT | SEQ ID NO:17722 CAGCACTCTGATAACTCACC GTGGACG | |
| iPS:434503 | 21-225_76G4 | AA | SEQ ID NO:1699 RASQSVYSSYLA | SEQ ID NO:9711 GASSRAT | SEQ ID NO:17723 QHSDNSPWT | |
| | | NA | SEQ ID NO:1700 CGGGCAAGTCAGGGCATTAG AAATGATTTAGGC | SEQ ID NO:9712 GCTGCATCCAGTTGCAA AGT | SEQ ID NO:17724 CTTCAGCATAGTAATTACC GCTCACT | |
| iPS:434507 | 21-225_74D7 | AA | SEQ ID NO:1701 RASQGIRNDLG | SEQ ID NO:9713 AASSLQS | SEQ ID NO:17725 LQHSNYPLT | |
| | | NA | SEQ ID NO:1702 AGGGCCAGTCAGAGTGTTAA CAGCAACTACTTAGCC | SEQ ID NO:9714 GGTGCATTCAGCAGGGC CACT | SEQ ID NO:17726 CAGCAGTATGAAAGCTCACC GTGGACG | |
| iPS:434505 | 21-225_74C5 | AA | SEQ ID NO:1703 RASQSVNSNYLA | SEQ ID NO:9715 GAFSRAT | SEQ ID NO:17727 QQYESSPWT | |
| | | NA | SEQ ID NO:1704 AAGTCCAGCCAGAGTGTATT ACACAGCTCCAACAGTTACA ACTACTTAGCT | SEQ ID NO:9716 TGGACATCTACCCGGGA ATCC | SEQ ID NO:17728 CAGCAATATTATAGTAGTCC TCCGACG | |
| iPS:434509 | 21-225_76F5 | AA | SEQ ID NO:1705 KSSQSVLHSSNSYNYLA | SEQ ID NO:9717 WTSTRES | SEQ ID NO:17729 QQYYSSPPT | |
| | | | SEQ ID NO:1706 | SEQ ID NO:9718 | SEQ ID NO:17730 | |

FIGURE 49
(Continued)

| | | | | | | |
|---|---|---|---|---|---|---|
| iPS:434511 | 21-225_74B11 | NA | AAGTCCAGCCAGAGTATTTT ATACAACTCCAACAATAACA ACTACTTAGCT SEQ ID NO:1707 | TGGGCATCTACCCGGGA ATCC SEQ ID NO:9719 | CAGCAATATTATAGCACTCC TCCTACT SEQ ID NO:17731 |
| | | AA | KSSQSILYNSNNNNYLA SEQ ID NO:1708 | WASTRES SEQ ID NO:9720 | QQYYSTPPT SEQ ID NO:17732 |
| iPS:434513 | 21-225_76A6 | NA | AGGGCCAGTCAGAGTGTTAG CAGCAGCTACTTAGCC SEQ ID NO:1709 | GGTGCATCCACCAGGGC CACT SEQ ID NO:9721 | CAGCAGTATGGTAACTCACC GCTCACT SEQ ID NO:17733 |
| | | AA | RASQSVSSSYLA SEQ ID NO:1710 | GASTRAT SEQ ID NO:9722 | QQYGNSPLT SEQ ID NO:17734 |
| iPS:434515 | 21-225_74A5 | NA | AGGGCCAGTCAGAGTGTTAG CAGCAGCTACTTAGTC SEQ ID NO:1711 | GGTGCATCCACCAGGGC CACT SEQ ID NO:9723 | CAGCAGTATGGTTGCTCACC GCTCACT SEQ ID NO:17735 |
| | | AA | RASQSVSSSYLV SEQ ID NO:1712 | GASTRAT SEQ ID NO:9724 | QQYGCSPLT SEQ ID NO:17736 |
| iPS:434517 | 21-225_76A7 | NA | AGGGCCAGTCCGAGTGTGA CAGCAGCTACTTAGCC SEQ ID NO:1713 | GGTGCATCCAGCAGGGC CCCT SEQ ID NO:9725 | CAGCAGTATGAAAGTTCACC GTGGACG SEQ ID NO:17737 |
| | | AA | RASPSVDSSYLA SEQ ID NO:1714 | GASSRAP SEQ ID NO:9726 | QQYESSPWT SEQ ID NO:17738 |
| iPS:434519 | 21-225_74C7 | NA | AGGACCAGTCAGAGTGTTAG CAGCAGCTACTTAGCC SEQ ID NO:1715 | GGTGCATCCAGCAGGGC CACT SEQ ID NO:9727 | CAGCAGTATGAACGCTCACC GTGGACG SEQ ID NO:17739 |
| | | AA | RTSPNVDSSYLA SEQ ID NO:1716 | GASSRAT SEQ ID NO:9728 | QQYERSPWT SEQ ID NO:17740 |
| iPS:434523 | 21-225_75C3 | NA | AGGGCCAGTCAGAGTGTTAG CAGCAGGTACTTAGCC SEQ ID NO:1717 | GGTGCATCCAGCAGGGC CACT SEQ ID NO:9729 | CAGCATTATGATAGTCACC GTGGACG SEQ ID NO:17741 |
| | | AA | RASQSVSSRYLA | GASSRAT | QHYDSSPWT |

FIGURE 49
(Continued)

| | | | | | |
|---|---|---|---|---|---|
| iPS:434525 | 21-225_76E8 | NA | SEQ ID NO:1718 AAGTCCAGCCAGAGACTGTTTTACACAGTCCAACAATTATAACTACTTAGCT | SEQ ID NO:9730 TGGACATCTACCCGGGAATCC | SEQ ID NO:17742 CAGCAATATTTTAGTAGTCCTCTGACG |
| | | AA | SEQ ID NO:1719 KSSQTVLHSSNNYNYLA | SEQ ID NO:9731 WTSTRES | SEQ ID NO:17743 QQYFSSPLT |
| iPS:434529 | 21-225_76B9 | NA | SEQ ID NO:1720 AGGGCCAGTCAGAGTGTTAGCAGCAGCTACTTAGTC | SEQ ID NO:9732 GGTGCATCCACCAGGGCCACT | SEQ ID NO:17744 CAGCAGTATGGTTGCTCACCGCTCACT |
| | | AA | SEQ ID NO:1721 RASQSVSSSYLV | SEQ ID NO:9733 GASTRAT | SEQ ID NO:17745 QQYGCSPLT |
| iPS:434531 | 21-225_76C9 | NA | SEQ ID NO:1722 AGGGCCAGTCAGAGTGTTAGCAGTTACTTATCC | SEQ ID NO:9734 GGTGCATCCAGCAGGGCCACT | SEQ ID NO:17746 CAGCAGTATGGTAGGTCACGGACG |
| | | AA | SEQ ID NO:1723 RASQSVSSSYLS | SEQ ID NO:9735 GASSRAT | SEQ ID NO:17747 QQYGRSRT |
| iPS:434533 | 21-225_85F7 | NA | SEQ ID NO:1724 AGGGCCAGTCAGAATATTTACAGCAACACTTAGCC | SEQ ID NO:9736 GGTGCATCCAGCAGGGCCACT | SEQ ID NO:17748 CAGCAGTATGAAAAGCTCACCGTGGACC |
| | | AA | SEQ ID NO:1725 RASQNIYSNYLA | SEQ ID NO:9737 GASSRAT | SEQ ID NO:17749 QQYESSPWT |
| iPS:434535 | 21-225_74C8 | NA | SEQ ID NO:1726 CGGGCGAGTCAGGGCATTGGCAAGTATTTAGCC | SEQ ID NO:9738 ACTACATCCAATTACAAAGT | SEQ ID NO:17750 CAACAGTACAGTAATTACCGCTCACT |
| | | AA | SEQ ID NO:1727 RASQGIGKYLA | SEQ ID NO:9739 TTSNLQS | SEQ ID NO:17751 QQYSNYPLT |
| iPS:434537 | 21-225_74E11 | NA | SEQ ID NO:1728 AGGGCCAGTCTGAGTGTTGTCAACAGCTTAGCC | SEQ ID NO:9740 GGTGCATCCACCAGGGCCACT | SEQ ID NO:17752 CAGCAGTATAATGACTGGCCGTGCAGT |
| | | | SEQ ID NO:1729 | SEQ ID NO:9741 | SEQ ID NO:17753 |

FIGURE 49
(Continued)

| | | | | | | | |
|---|---|---|---|---|---|---|---|
| iPS:434539 | 21-225_74A2 | AA | RASLSVVNSLA | | GASTRAT | | QQYNDWPCS |
| | | | SEQ ID NO:1730 | | SEQ ID NO:9742 | | SEQ ID NO:17754 |
| | | NA | AGGTCTAGTCAGAGCCTCCT GCATAGTAATGGACACAACT ATTTGGAT | | TTGGGTTCTAATCGGGCC TCC | | ATGCAACCTCTACAAACTCC GTTCACT |
| | | | SEQ ID NO:1731 | | SEQ ID NO:9743 | | SEQ ID NO:17755 |
| iPS:434547 | 21-225_74H5 | AA | RSSQSLLHSNGHNYLD | | LGSNRAS | | MQPLQTPFT |
| | | | SEQ ID NO:1732 | | SEQ ID NO:9744 | | SEQ ID NO:17756 |
| | | NA | AGGGCCAGTCAGAGTGTTAA CAGCAACTACTTAGCC | | GGTGCATCCAGCAGGGC CACT | | CAGCAGTATGAAAGCTCGCC GTGGACG |
| | | | SEQ ID NO:1733 | | SEQ ID NO:9745 | | SEQ ID NO:17757 |
| iPS:434549 | 21-225_76E11 | AA | RASQSVNSNYLA | | GASSRAT | | QQYESSPWT |
| | | | SEQ ID NO:1734 | | SEQ ID NO:9746 | | SEQ ID NO:17758 |
| | | NA | AAGTCCCGCCAGAGTGTTT ACACAGTCCAACAATTACA ACTACTTAGCT | | TGGGCTTCTACCCGGA ATCC | | CAGCAATATTATAGTACTCC TCCGACG |
| | | | SEQ ID NO:1735 | | SEQ ID NO:9747 | | SEQ ID NO:17759 |
| iPS:434551 | 21-225_75C4 | AA | KSRQSVLHSSNNYNYLA | | WASTRES | | QQYSTPPT |
| | | | SEQ ID NO:1736 | | SEQ ID NO:9748 | | SEQ ID NO:17760 |
| | | NA | AAGTCCAGCCAGAGTATTTT ATACAGTCCAACAATAATA ACTACTTAGCT | | TGGGCATCTACCCGGGA ATCC | | CAGCAATATTATTATTACTCC TCCGACG |
| | | | SEQ ID NO:1737 | | SEQ ID NO:9749 | | SEQ ID NO:17761 |
| iPS:434559 | 21-225_74D11 | AA | KSSQSILYSSNNNNYLA | | WASTRES | | QQYYITPPT |
| | | | SEQ ID NO:1738 | | SEQ ID NO:9750 | | SEQ ID NO:17762 |
| | | NA | AGGGCCAGTCAGAGTGTTTA CAGCAGCTACTTAGCC | | GGTGCATCCAGCAGCGGGC CACT | | CAGCACTATGATAACTCACC GTGGACG |
| | | | SEQ ID NO:1739 | | SEQ ID NO:9751 | | SEQ ID NO:17763 |
| | | AA | RASQSVYSSYLA | | GASSRAT | | QHYDNSPWT |
| | | | SEQ ID NO:1740 | | SEQ ID NO:9752 | | SEQ ID NO:17764 |

FIGURE 49
(Continued)

| | | | | | |
|---|---|---|---|---|---|
| iPS:434561 | 21-225_77G1 | NA | AGGGCCAGTCAGAGTGTTTA CAGCAGCTACTTAGCC | GGTGCATCCAGCCGGGC CACT | CAGCACTATGATAACTCACC GTGGACG |
| | | | SEQ ID NO:1741 | SEQ ID NO:9753 | SEQ ID NO:17765 |
| | | AA | RASQSVYSSYLA | GASSRAT | QHYDNSPWT |
| | | | SEQ ID NO:1742 | SEQ ID NO:9754 | SEQ ID NO:17766 |
| iPS:434563 | 21-225_75D8 | NA | AGGTCTAGTCAGAGCCTCCT GCATAGTAGTGGATACAACT ATTTGGAT | TTGGGTTCTAATCGGGC TCC | ATGCAAGCTCTACACCCTCC TCTCACT |
| | | | SEQ ID NO:1743 | SEQ ID NO:9755 | SEQ ID NO:17767 |
| | | AA | RSSQSLLHSSGYNYLD | LGSNRAS | MQALHPPLT |
| | | | SEQ ID NO:1744 | SEQ ID NO:9756 | SEQ ID NO:17768 |
| iPS:434565 | 21-225_75B10 | NA | AGGGCCAGTCCGAGTGTTAA CAGCTACTTAGCC | GGTGCAACCAGCAGGGC CACT | CAGCAGTATGAAGACTCACC GTGGACG |
| | | | SEQ ID NO:1745 | SEQ ID NO:9757 | SEQ ID NO:17769 |
| | | AA | RASPSVNSYYLA | GATSRAT | QQYEDSPWT |
| | | | SEQ ID NO:1746 | SEQ ID NO:9758 | SEQ ID NO:17770 |
| iPS:434569 | 21-225_77H5 | NA | AGGGCCAGTCAGAGTGTTAG CAGCAGCTTAGCC | GGTGCATCCACCAGGGC CACT | CAGCAGTATAATGACTGGCC GTGCAGT |
| | | | SEQ ID NO:1747 | SEQ ID NO:9759 | SEQ ID NO:17771 |
| | | AA | RASQSVSSSLA | GASTRAT | QQYNDWPCS |
| | | | SEQ ID NO:1748 | SEQ ID NO:9760 | SEQ ID NO:17772 |
| iPS:434571 | 21-225_74D2 | NA | AGGGCCAGTCAGAGTGTTGA CAGCAACTACTTAGCC | GGTGCATCCAGCAGGGC CCCT | CAGCAGTATGAAAGCTCACC GTGGACG |
| | | | SEQ ID NO:1749 | SEQ ID NO:9761 | SEQ ID NO:17773 |
| | | AA | RASQSVDSNYLA | GASSRAP | QQYESSPWT |
| | | | SEQ ID NO:1750 | SEQ ID NO:9762 | SEQ ID NO:17774 |
| iPS:434573 | 21-225_77E6 | NA | CGGGCGAGTCAGGGCATTAG CAAGTATTTAGCC | GCTGCATCCAGTTTGCAA GGT | CAACAGTACAGTAATTACCC GCTCACT |
| | | | SEQ ID NO:1751 | SEQ ID NO:9763 | SEQ ID NO:17775 |
| | | AA | RASQGISKYLA | AASSLQG | QQYSNYPLT |

FIGURE 49
(Continued)

| | | | | | |
|---|---|---|---|---|---|
| iPS:434575 | | NA | SEQ ID NO:1752<br>AAGTCCAGCCAGAGACTGTTTT<br>ACACAGTCCAACAATTATA<br>ACTACTTAGCT | SEQ ID NO:9764<br>TGGACATCTACCCGGGA<br>ATCC | SEQ ID NO:17776<br>CAGCAATATTTTAGTAGTCC<br>TCCGACG |
| 21-225_77C7 | | AA | SEQ ID NO:1753<br>KSSQTVLHSSNNYNYLA | SEQ ID NO:9765<br>WTSTRES | SEQ ID NO:17777<br>QQYFSSPPT |
| iPS:434579 | | NA | SEQ ID NO:1754<br>AGGGCCAGTCAGAGTGTTTA<br>CAGCAGCTACTTAGCG | SEQ ID NO:9766<br>GGTGCATCCAGCCAGGGC<br>CACT | SEQ ID NO:17778<br>CAGCACTATGATAACTCACC<br>GTGGACG |
| 21-225_77F7 | | AA | SEQ ID NO:1755<br>RASQSVYSSYLA | SEQ ID NO:9767<br>GASSRAT | SEQ ID NO:17779<br>QHYDNSPWT |
| iPS:434581 | | NA | SEQ ID NO:1756<br>AGGGCCAGTCAGAGTGTTTA<br>CAGCAGCTACTTAGCC | SEQ ID NO:9768<br>GGTGCATCCAGCCAGGTC<br>CACT | SEQ ID NO:17780<br>CAGCACTATGATAACTCACC<br>GTGGACG |
| 21-225_74B12 | | AA | SEQ ID NO:1757<br>RASQSVYSSYLA | SEQ ID NO:9769<br>GASSRST | SEQ ID NO:17781<br>QHYDNSPWT |
| iPS:434583 | | NA | SEQ ID NO:1758<br>AGGGCCAGTCAGAGTGTTAG<br>CAGCAGCTACTTAGCG | SEQ ID NO:9770<br>GGTGCATCCACCAGGGC<br>CACT | SEQ ID NO:17782<br>CAGCAGTATGGTAACTCACC<br>GCTCACT |
| 21-225_74B6 | | AA | SEQ ID NO:1759<br>RASQSVSSSYLA | SEQ ID NO:9771<br>GASTRAT | SEQ ID NO:17783<br>QQYGNSPLT |
| iPS:434585 | | NA | SEQ ID NO:1760<br>AGGGCCAGTCAGAGTGTTAG<br>CAGCAGCTACTTAGCC | SEQ ID NO:9772<br>GGTGCATCCAGCAGGGC<br>CACT | SEQ ID NO:17784<br>CAGCATTATGATAGCTCACC<br>GTGGACG |
| 21-225_75A12 | | AA | SEQ ID NO:1761<br>RASQSVSSRYLA | SEQ ID NO:9773<br>GASSRAT | SEQ ID NO:17785<br>QHYDSSPWT |
| iPS:434587 | | NA | SEQ ID NO:1762<br>AGGGCCAGTCAGAGTGTTAG<br>CAGCAGCTACTTAGTC | SEQ ID NO:9774<br>GGTGCATCCACCAGGGC<br>CACT | SEQ ID NO:17786<br>CAGCAGTATGGTTGCTCACC<br>GCTCACT |
| 21-225_74G3 | | | SEQ ID NO:1763 | SEQ ID NO:9775 | SEQ ID NO:17787 |

FIGURE 49
(Continued)

| | | | | | | | |
|---|---|---|---|---|---|---|---|
| iPS:434595 | 21-225_77A10 | AA | RASQSVSSSYLV<br>SEQ ID NO:1764 | GASTRAT<br>SEQ ID NO:9776 | QQYGCSPLT<br>SEQ ID NO:17788 |
| | | NA | AGGGCCAGTCAGAGTGTTCACAGCAGGTACTTAGCC<br>SEQ ID NO:1765 | GGTGCATCCAGCAGGGCCACT<br>SEQ ID NO:9777 | CAGCATTATGATAGCTCACCGTGGACG<br>SEQ ID NO:17789 |
| | | AA | RASQSVHSRYLA<br>SEQ ID NO:1766 | GASSRAT<br>SEQ ID NO:9778 | QHYDSSPWT<br>SEQ ID NO:17790 |
| iPS:434597 | 21-225_77C10 | NA | AAGTCCAGCCAGAGTGTTTTATACACCTCCAACAATAACAACTACTTAGCT<br>SEQ ID NO:1767 | TGGGCATCTACCCGGGAATCC<br>SEQ ID NO:9779 | CAGCACTATTATAATACTCCGTGGAAG<br>SEQ ID NO:17791 |
| | | AA | KSSQSVLYTSNNNYLA<br>SEQ ID NO:1768 | WASTRES<br>SEQ ID NO:9780 | QHYNTPWK<br>SEQ ID NO:17792 |
| iPS:434603 | 21-225_77D11 | NA | AGGGCCAGTCAGAGTGTTAGCAGCAGTACTTAGTC<br>SEQ ID NO:1769 | GGTGCATCCACCAGGGCGCTCACT<br>SEQ ID NO:9781 | CAGCAGTATGGTTGCTCACCGCTCACT<br>SEQ ID NO:17793 |
| | | AA | RASQSVSSSYLV<br>SEQ ID NO:1770 | GASTRAT<br>SEQ ID NO:9782 | QQYGCSPLT<br>SEQ ID NO:17794 |
| iPS:434611 | 21-225_77C12 | NA | AGGGCCAGGCAGAGTGTTGACAGCAGTATTTAGCC<br>SEQ ID NO:1771 | GGTGCATCCAGCAGGGCCACT<br>SEQ ID NO:9783 | CAGCAGTATGAAAGCTCACCGTGGACG<br>SEQ ID NO:17795 |
| | | AA | RARQSVDSSYLA<br>SEQ ID NO:1772 | GASSRAT<br>SEQ ID NO:9784 | QQYESSPWT<br>SEQ ID NO:17796 |
| iPS:434613 | 21-225_77D12 | NA | AGGTCCAGCCAGAGTGTTTTATACAGCTCCAACAATTATAACTACTTAGCT<br>SEQ ID NO:1773 | TGGGCATCTACCCGGGATTCC<br>SEQ ID NO:9785 | CAGCAATATTATACTACTCCGTGCAGT<br>SEQ ID NO:17797 |
| | | AA | RSSQSVLYSSNNYNYLA<br>SEQ ID NO:1774 | WASTRDS<br>SEQ ID NO:9786 | QQYYTPCS<br>SEQ ID NO:17798 |

FIGURE 49
(Continued)

| | | | | | |
|---|---|---|---|---|---|
| iPS:434615 | 21-225_76C5 | NA | CGGGCGAGTCAGGTCATTAG CAAGTATTTAGCC SEQ ID NO:1775 | GCTGCATCCAGTTTGCAA AGT SEQ ID NO:9787 | CAACAGTACAGTAATTACC GCTCACT SEQ ID NO:17799 |
| | | AA | RASQVISKYLA SEQ ID NO:1776 | AASSLQS SEQ ID NO:9788 | QQYSNYPLT SEQ ID NO:17800 |
| iPS:434617 | 21-225_74B8 | NA | AAGTCCAGCCAGAGTGTTT ACACAGCTCAATAAAAGA ACTACTTAGCT SEQ ID NO:1777 | TGGGCATCTACCCGGGA ATCC SEQ ID NO:9789 | CAGCAATATTATAGGACTCC GTGGACG SEQ ID NO:17801 |
| | | AA | KSSQSVLHSSNKKNYLA SEQ ID NO:1778 | WASTRES SEQ ID NO:9790 | QQYYRTPWT SEQ ID NO:17802 |
| iPS:434619 | 21-225_78C1 | NA | AAGTCCAGCCAGAGTGTTT ATACACCTCCAACAATAACA ACTACTTAGCT SEQ ID NO:1779 | TGGGCATCTACCCGGGA ATCC SEQ ID NO:9791 | CAGCACTATTATAATACTCC GTGGAAG SEQ ID NO:17803 |
| | | AA | KSSQSVLYTSNNNNYLA SEQ ID NO:1780 | WASTRES SEQ ID NO:9792 | QHYYNTPWK SEQ ID NO:17804 |
| iPS:434621 | 21-225_74D1 | NA | AGGGCCAGTCAGAGTGTTGC CAGAAATTTAGCC SEQ ID NO:1781 | GGTGCATCCATCAGGGC CACT SEQ ID NO:9793 | CAGCAGTATAATAACTGGCC TCCGCTCACT SEQ ID NO:17805 |
| | | AA | RASQSVSRNLA SEQ ID NO:1782 | GASIRAT SEQ ID NO:9794 | QQYNWPPLT SEQ ID NO:17806 |
| iPS:434629 | 21-225_74C3 | NA | AGGGCCAGTCAGAGTGTTGC CAGCAGTTAGCC SEQ ID NO:1783 | GGTACATCCACCAGGGC CACT SEQ ID NO:9795 | CAGCAGTATAATGACTGGCC GTGCAGT SEQ ID NO:17807 |
| | | AA | RASQSVASSLA SEQ ID NO:1784 | GTSTRAT SEQ ID NO:9796 | QQYNDWPCS SEQ ID NO:17808 |
| iPS:434633 | 21-225_74G8 | NA | AGGGCCAGTCAGAGTTTAG CAGCGCCTACTTAGCC SEQ ID NO:1785 | GGTACTTCCAGCAGGGC CACT SEQ ID NO:9797 | CAACAGTATGGTAACTCAAG GACG SEQ ID NO:17809 |

FIGURE 49
(Continued)

| | | | | | | | |
|---|---|---|---|---|---|---|---|
| iPS:434635 | 21-225_78E6 | AA | RASQSFSSAYLA SEQ ID NO:1786 | | GTSSRAT SEQ ID NO:9798 | | QQYGNSRT SEQ ID NO:17810 |
| | | NA | AAGTCCAGCCAGAGTGTTTT GTACAGCTCCAACAGTCACA ACTACTTAGCT SEQ ID NO:1787 | | TGGGCATCTATCCGGGA ATCC SEQ ID NO:9799 | | CAGCAATATTATAGTACTCC GTGCAGT SEQ ID NO:17811 |
| iPS:434637 | 21-225_78E7 | AA | KSSQSVLYSSNSHNYLA SEQ ID NO:1788 | | WASIRES SEQ ID NO:9800 | | QQYYSTPCS SEQ ID NO:17812 |
| | | NA | AGGGCCAGTCAGAATGTTGA CAGCAACTACTACTTAGCC SEQ ID NO:1789 | | GGTGCATCCAGCAGGGC CACT SEQ ID NO:9801 | | CAGCAGTATGAAGGCTCACC GTGGACG SEQ ID NO:17813 |
| iPS:434639 | 21-225_74B7 | AA | RASQNVDSNYLA SEQ ID NO:1790 | | GASSRAT SEQ ID NO:9802 | | QQYERSPWT SEQ ID NO:17814 |
| | | NA | AAGTCCAGCCAGAGTGTTTT ACACAGCTCCAACAATTATA ACTACTTAGCT SEQ ID NO:1791 | | TGGACATCTACCCGGGA ATCC SEQ ID NO:9803 | | CAGCAATATTTTAGTAGTCC TCCGACG SEQ ID NO:17815 |
| iPS:434649 | 21-225_78E11 | AA | KSSQTVLHSSNNYNYLA SEQ ID NO:1792 | | WTSTRES SEQ ID NO:9804 | | QQYFSSPPT SEQ ID NO:17816 |
| | | NA | AAGTCCAGCCAGAGTGTTTT ATACAGCTCCAACAATTACA ACTACTTAGCT SEQ ID NO:1793 | | TGGGCATCTACCCGGGA ATCC SEQ ID NO:9805 | | CAGCAATATTATAGTAGTCC TCCGACG SEQ ID NO:17817 |
| iPS:434653 | 21-225_74B5 | AA | KSSQSVLYSFNNYNYLA SEQ ID NO:1794 | | WASTRES SEQ ID NO:9806 | | QQYYSSPPT SEQ ID NO:17818 |
| | | NA | AAGTCCAGCCAGAGTGTTT ATTCAGCTCCAACAATTATA ACTACTTAGCT SEQ ID NO:1795 | | TGGGCATCTACCCGGGA ATCC SEQ ID NO:9807 | | CAGCAATATTATAGTTCTCC TCCGACG SEQ ID NO:17819 |
| | | AA | KSSQSVLFSSNNYNYLA | | WASTRES | | QQYYSSPPT |

FIGURE 49
(Continued)

| | | | | | | |
|---|---|---|---|---|---|---|
| iPS:434655 | 21-225_78H12 | NA | SEQ ID NO:1796 AAGTCCAGCCAGAGTCTGTTT ACACAGTTCAACAATTATA ACTACTTAGCT | SEQ ID NO:9808 TGGACATCTACCCGGGA ATCC | SEQ ID NO:17820 CAGCAATATTTTAGTAGTCC TCCGACG | |
| | | AA | SEQ ID NO:1797 KSSQTVLHSFNNYNYLA | SEQ ID NO:9809 WTSTRES | SEQ ID NO:17821 QQYFSSPPT | |
| iPS:434657 | 21-225_79G1 | NA | SEQ ID NO:1798 AGGGCCAGTCAGAGTGTTTA CAGCAGCTACTTAGCC | SEQ ID NO:9810 GGTGCATCCAGCCGGTC CACT | SEQ ID NO:17822 CAGCACTATGATAACTCACC GTGGACG | |
| | | AA | SEQ ID NO:1799 RASQSVYSSYLA | SEQ ID NO:9811 GASSRST | SEQ ID NO:17823 QHYDNSPWT | |
| iPS:434663 | 21-225_79F3 | NA | SEQ ID NO:1800 AGGGCCAGTCAGAGTGTTTA CAGCAGCTACTTAGCC | SEQ ID NO:9812 GGTGCATCCAGCCGGTC CACT | SEQ ID NO:17824 CAGCACTATGATAACTCACC GTGGACG | |
| | | AA | SEQ ID NO:1801 RASQSVYSSYLA | SEQ ID NO:9813 GASSRST | SEQ ID NO:17825 QHYDNSPWT | |
| iPS:434665 | 21-225_74G4 | NA | SEQ ID NO:1802 AAGTCCAGCCAGAGTGTTTT ATACAGTTCCAACAATAATA ACTACTTAGCT | SEQ ID NO:9814 TGGGCATCTACCCGGGA ATCC | SEQ ID NO:17826 CAGCAATATTATAGTATTCC TCCGACG | |
| | | AA | SEQ ID NO:1803 KSSQSVLYSSNNNNYLA | SEQ ID NO:9815 WASTRES | SEQ ID NO:17827 QQYYSIPPT | |
| iPS:434669 | 21-225_79F4 | NA | SEQ ID NO:1804 CGGGGCAGTCAGGGCATTAG CAAGTATTTAGCC | SEQ ID NO:9816 GCTGCATCCAGTTTGCAA GGT | SEQ ID NO:17828 CAACAGTACAGTAATTACCC ACTCACT | |
| | | AA | SEQ ID NO:1805 RASQGISKYLA | SEQ ID NO:9817 AASSLQG | SEQ ID NO:17829 QQYSNYPLT | |
| iPS:434671 | | NA | SEQ ID NO:1806 AGGGCCAGTCAGAGATTTTAG CAGCAGCTACTTAGCC | SEQ ID NO:9818 GGTGCATCCAGCAGGGC CACT | SEQ ID NO:17830 CAGCAGTATGGTAGCTCACG GACG | |

FIGURE 49
(Continued)

| | | | | | | |
|---|---|---|---|---|---|---|
| iPS:434673 | 21-225_74F4 | AA | SEQ ID NO:1807<br>RASQIFSSSYLA | SEQ ID NO:9819<br>GASSRAT | SEQ ID NO:17831<br>QQYGSSRT | |
| iPS:434675 | 21-225_74E3 | NA | SEQ ID NO:1808<br>AGGGCCAGTCAGATCTGAGTGTTGT<br>CAACAGCTTAGCC | SEQ ID NO:9820<br>GGTGCATCCACCAGGGC<br>CACT | SEQ ID NO:17832<br>CAGCAGTATAATGACTGGCC<br>GTGCAGT | |
| | | AA | SEQ ID NO:1809<br>RASLSVVNSLA | SEQ ID NO:9821<br>GASTRAT | SEQ ID NO:17833<br>QQYNDWPCS | |
| iPS:434679 | 21-225_79G6 | NA | SEQ ID NO:1810<br>ATGTCCAGCAGCAGAGTGTTT<br>ACACAGCTTCAACAATAAGA<br>ACTACTTAACT | SEQ ID NO:9822<br>TGGGCATCTACTTGGA<br>ATCC | SEQ ID NO:17834<br>CAGCAATATTATAGTATTCC<br>TCCGACG | |
| | | AA | SEQ ID NO:1811<br>MSSQSVLHSFNNKNYLT | SEQ ID NO:9823<br>WASTWES | SEQ ID NO:17835<br>QQYYSIPPT | |
| iPS:434685 | 21-225_79G7 | NA | SEQ ID NO:1812<br>AAGTCCAGCCAGAGTGTTT<br>GTACAGCTCCAACAGTACA<br>ACTACTTAGCT | SEQ ID NO:9824<br>TGGGCATCTATCCGGGA<br>ATCC | SEQ ID NO:17836<br>CAGCAATATTATATTACTCC<br>GTGCAGT | |
| | | AA | SEQ ID NO:1813<br>KSSQSVLYSSNSHNYLA | SEQ ID NO:9825<br>WASIRES | SEQ ID NO:17837<br>QQYYSTPCS | |
| iPS:434685 | 21-225_79E9 | NA | SEQ ID NO:1814<br>AAGTCCAGCCAGAGTATTT<br>ATACAGCTCCAACAATAATA<br>ACTACTTAGCT | SEQ ID NO:9826<br>TGGGCATCTACCCGGA<br>ATCC | SEQ ID NO:17838<br>CAGCAATATTATATTACTCC<br>TCCGACG | |
| | | AA | SEQ ID NO:1815<br>KSSQSILYSSNNNNYLA | SEQ ID NO:9827<br>WASTRES | SEQ ID NO:17839<br>QQYYITPPT | |
| iPS:434687 | 21-225_75A5 | NA | SEQ ID NO:1816<br>AGGGCCAGTCAGAGTGTTA<br>CAGCAGCTACTTAGCC | SEQ ID NO:9828<br>GGTGCATCCAGCCGGGC<br>CACT | SEQ ID NO:17840<br>CAGCACTATGATAACTCACC<br>GTGGACG | |
| | | AA | SEQ ID NO:1817<br>RASQSVYSSYLA | SEQ ID NO:9829<br>GASSRAT | SEQ ID NO:17841<br>QHYDNSPWT | |

FIGURE 49
(Continued)

| | | | | | | |
|---|---|---|---|---|---|---|
| iPS:434689 | 21-225_79G10 | NA | SEQ ID NO:1818 AAGTCCAGCTCCAACAATTATAATTACTTAGCT | SEQ ID NO:9830 TGGGCATCTACCCGGAATCC | SEQ ID NO:17842 CAGCAATATCATAGTTCTCCTCTGACG |
| | | AA | SEQ ID NO:1819 KSSQSVLFSSNNYNYLA | SEQ ID NO:9831 WASTRES | SEQ ID NO:17843 QQYHSSPLT |
| iPS:434691 | 21-225_75G7 | NA | SEQ ID NO:1820 AGGGCCAGTCAGAGTGTTGACAGCAGTTATTTAGCC | SEQ ID NO:9832 GGTGCATCCAGCAGGGCCACT | SEQ ID NO:17844 CAGCAGTATGAAAGCTCACCGTGGACG |
| | | AA | SEQ ID NO:1821 RARQSVDSSYLA | SEQ ID NO:9833 GASSRAT | SEQ ID NO:17845 QQYESSPWT |
| iPS:434693 | 21-225_79F11 | NA | SEQ ID NO:1822 AGGGCCAGTCAGAGTGTTTACAGCAGCTACTTAGCC | SEQ ID NO:9834 GGTGCATCCAGCCGGGCCACT | SEQ ID NO:17846 CAGCACTCTGATAACTCACCGTGGACG |
| | | AA | SEQ ID NO:1823 RASQSVYSSYLA | SEQ ID NO:9835 GASSRAT | SEQ ID NO:17847 QHSDNSPWT |
| iPS:434697 | 21-225_79F12 | NA | SEQ ID NO:1824 AAGTCCAGCCAGAGTATTTTATACAGCTCCAACAATTACAACTACTTAGCT | SEQ ID NO:9836 TGGGCATCTACCCGGAATCC | SEQ ID NO:17848 CAGCAATATTATAGTACTCCGTGGACG |
| | | AA | SEQ ID NO:1825 KSSQSILYSSNNYNYLA | SEQ ID NO:9837 WASTRES | SEQ ID NO:17849 QQYYSTPWT |
| iPS:434699 | 21-225_79G12 | NA | SEQ ID NO:1826 AGGGCCAGTCAGAGTGTTTACAGCAGCTACTTAGCC | SEQ ID NO:9838 GGTGCATCCAGCCGGTCCACT | SEQ ID NO:17850 CAGCACTCTGATAACTCACCGTGGACG |
| | | AA | SEQ ID NO:1827 RASQSVYSSYLA | SEQ ID NO:9839 GASSRST | SEQ ID NO:17851 QHSDNSPWT |
| iPS:434701 | | NA | SEQ ID NO:1828 AGGGCCAGTCAGAGTGTTTACAGCAGCTACTTAGCC | SEQ ID NO:9840 GGTGCATCCAGCCGGTCCACT | SEQ ID NO:17852 CAGCACTCTGATAACTCACCGTGGACG |

FIGURE 49
(Continued)

| | | | | | | |
|---|---|---|---|---|---|---|
| iPS:434703 | 21-225_80A1 | NA | SEQ ID NO:1829 AGGGCCAGTCAGAGTGTTTA CAGCAGTCACTTAGCC | SEQ ID NO:9841 GGTGCATCCAGCCGGTC CACT | SEQ ID NO:17853 QHSDNSPWT | |
| | | AA | SEQ ID NO:1830 RASQSVYSSYLA | SEQ ID NO:9842 GASSRST | SEQ ID NO:17854 CAGCACTCTGATAACTCACC GTGGACG | |
| iPS:434705 | 21-225_80C1 | NA | SEQ ID NO:1831 AGGGCCAGTCAGAGTGTTAG CAGCAGTCACTTAGTC | SEQ ID NO:9843 GGTGCATCCAGCCGGGC CACT | SEQ ID NO:17855 QHSDNSPWT | |
| | | AA | SEQ ID NO:1832 RASQSVYSSYLA | SEQ ID NO:9844 GASSRST | SEQ ID NO:17856 CAGCAGTATGGTTGCTCACC GCTCACT | |
| iPS:434707 | 21-225_80A2 | NA | SEQ ID NO:1833 RASQSVSSSSYLV | SEQ ID NO:9845 GASTRAT | SEQ ID NO:17857 QQYGCSPLT | |
| | | AA | SEQ ID NO:1834 AAGTCCAGCCAGAGTGTTTT ATACACCTCCAACAATAACA ACTACTTAGCT | SEQ ID NO:9846 TGGGCATCTACCGGGA ATCC | SEQ ID NO:17858 CAGCACTACAATGAAACTCC AGGGAAG | |
| iPS:434709 | 21-225_80D3 | NA | SEQ ID NO:1835 KSSQSVLYTSNNNNYLA | SEQ ID NO:9847 WASTRES | SEQ ID NO:17859 QHYNETPGK | |
| | | AA | SEQ ID NO:1836 AGGGCCAGTCAGAGTGTTTA CAGCAGTCACTTAGCC | SEQ ID NO:9848 GGTGCATCCAGCCGGTC CACT | SEQ ID NO:17860 CAGCATTCTGATAACTCACC GTGGACG | |
| iPS:434711 | 21-225_80E3 | NA | SEQ ID NO:1837 RASQSVYSSYLA | SEQ ID NO:9849 GASSRST | SEQ ID NO:17861 QHSDNSPWT | |
| | | AA | SEQ ID NO:1838 AAGTCCAGCCAGAGTGTTTT ACACAGGTCCAACAATTACA ACTACTTAGCG | SEQ ID NO:9850 TGGGCATCTACCCGGGA ATCC | SEQ ID NO:17862 CAGCAATATTATAGTACTCC TCCGACG | |
| | 21-225_80H3 | NA | SEQ ID NO:1839 KSSQSVLHRSNNYNYLA | SEQ ID NO:9851 WASTRES | SEQ ID NO:17863 QQYYSTPPT | |
| | | AA | SEQ ID NO:1840 | SEQ ID NO:9852 | SEQ ID NO:17864 | |

FIGURE 49
(Continued)

| | | | | | |
|---|---|---|---|---|---|
| iPS:434715 | 21-225_80D5 | NA | AGGGCCAGTCAGAATATTTA CAGCAGCTACTTAGCC SEQ ID NO:1841 | GGTGCATCCAGCAGGGC CACT SEQ ID NO:9853 | CAGCAGTATGAAAGCTCACC GTGGACC SEQ ID NO:17865 |
| | | AA | RASQNIYSSYLA SEQ ID NO:1842 | GASSRAT SEQ ID NO:9854 | QQYESSPWT SEQ ID NO:17866 |
| iPS:434717 | 21-225_80A6 | NA | AGGGCCAGTCAGAGTGTTGA CAGCGGCTACTTAGCC SEQ ID NO:1843 | GGTGCATCCAGCAGGGC CCCT SEQ ID NO:9855 | CAGCAGTATGAAAGCTCACC GTGGACG SEQ ID NO:17867 |
| | | AA | RASQSVDSGYLA SEQ ID NO:1844 | GASSRAP SEQ ID NO:9856 | QQYESSPWT SEQ ID NO:17868 |
| iPS:434725 | 21-225_80H7 | NA | AGGGCCAGTCAGAGTATTAA CAGCAACTACTTAGCC SEQ ID NO:1845 | GGTGCATCCAGCAGGGC CACT SEQ ID NO:9857 | CAGCAGTATGAGAGCTCACC GTGGACG SEQ ID NO:17869 |
| | | AA | RASQSINSNYLA SEQ ID NO:1846 | GASSRAT SEQ ID NO:9858 | QQYESSPWT SEQ ID NO:17870 |
| iPS:434729 | 21-225_80B12 | NA | AAGTCCAGACAGAGTGTTT ATACAGTCCAACAATTACA ACTACTTAACT SEQ ID NO:1847 | TGGGCATCTACCCGGGA ATCC SEQ ID NO:9859 | CAGCAATATTATAGTTCTCC TCCTACT SEQ ID NO:17871 |
| | | AA | KSRQSVLYSSNNYNYLT SEQ ID NO:1848 | WASTRES SEQ ID NO:9860 | QQYYSSPPT SEQ ID NO:17872 |
| iPS:434731 | 21-225_80E9 | NA | AAGTCCAGCAGAGTGTTTT ATACACTCCAACAATAACA ACTACTTAGCT SEQ ID NO:1849 | TGGGCATCTACCCGGGA ATCC SEQ ID NO:9861 | CAGCAATATTATAATACTCC GTGGACG SEQ ID NO:17873 |
| | | AA | KSSQSVLYTSNNNNYLA SEQ ID NO:1850 | WASTRES SEQ ID NO:9862 | QQYYNTPWT SEQ ID NO:17874 |
| iPS:434735 | 21-225_80B10 | NA | AGGGCCAGTCAGAGTGTTGA CAGCAGCTACTTAGCC SEQ ID NO:1851 | GGTGCATCCAGCAGGGC CCCT SEQ ID NO:9863 | CAGCAGTATGAAAGCTCACC GTGGACG SEQ ID NO:17875 |

FIGURE 49
(Continued)

| | | | | | | |
|---|---|---|---|---|---|---|
| iPS:434737 | | AA | RASQSVDSSYLA SEQ ID NO:1852 | GASSRAP SEQ ID NO:9864 | QQYESSPWT SEQ ID NO:17876 | |
| | 21-225_74G6 | NA | CGGGGGAGTCAGGGCATTGG CAAGTATTTAGCC SEQ ID NO:1853 | ACTACATCCAGTTGCAA AGT SEQ ID NO:9865 | CAACAGTACAGTAATTACC GCTCACT SEQ ID NO:17877 | |
| iPS:434741 | | AA | RASQGIGKYLA SEQ ID NO:1854 | TTSSLQS SEQ ID NO:9866 | QQYSNYPLT SEQ ID NO:17878 | |
| | 21-225_80C11 | NA | CGGGGGAGTCAGGGCATTGG CAGGTATTTAGCC SEQ ID NO:1855 | ACTGCATCCAGTTGCAA AGT SEQ ID NO:9867 | CAACAGTACAGTAATTACC GCTCACT SEQ ID NO:17879 | |
| iPS:434743 | | AA | RASQGIGRYLA SEQ ID NO:1856 | TASSLQS SEQ ID NO:9868 | QQYSNYPLT SEQ ID NO:17880 | |
| | 21-225_74A4 | NA | AGGGCCAGTCAGAGTGTTTA CAGCAGCTACTTAGCC SEQ ID NO:1857 | GGTGCATCCAGCCGGTC CACT SEQ ID NO:9869 | CAGCACTCTGATAACTCACC GTGGACG SEQ ID NO:17881 | |
| iPS:434747 | | AA | RASQSVYSSYLA SEQ ID NO:1858 | GASSRST SEQ ID NO:9870 | QHSDNSPWT SEQ ID NO:17882 | |
| | 21-225_80C12 | NA | AGGGCCAGTCAGAGTGTTAG CAGCAGCTACTTAGCC SEQ ID NO:1859 | GGTGCATCCACCAGGGC CACT SEQ ID NO:9871 | CAGCAGTATGGTAACTCACC GCTCACT SEQ ID NO:17883 | |
| iPS:434751 | | AA | RASQSVSSSYLA SEQ ID NO:1860 | GASTRAT SEQ ID NO:9872 | QQYGNSPLT SEQ ID NO:17884 | |
| | 21-225_80H12 | NA | AGGGCCAGTCAGAGTGTTTA CAGCAGCTACTTAGCC SEQ ID NO:1861 | GGTGCATCCAGCCGGTC CACT SEQ ID NO:9873 | CAGCACTCTGATAACTCACC GTGGACG SEQ ID NO:17885 | |
| iPS:434759 | | AA | RASQSVYSSYLA SEQ ID NO:1862 | GASSRST SEQ ID NO:9874 | QHSDNSPWT SEQ ID NO:17886 | |
| | 21-225_81C5 | NA | AGGGCCAGTCAGAGTGTTTA CAGCAGCTACTTAGCC SEQ ID NO:1863 | GGTGCATCCAGCCGGTC CACT SEQ ID NO:9875 | CAGCATTCTGATAACTCACC GTGGACG SEQ ID NO:17887 | |

FIGURE 49
(Continued)

| | | | | | | | |
|---|---|---|---|---|---|---|---|
| iPS:434761 | 21-225_81E5 | AA | RASQSVYSSYLA SEQ ID NO:1864 | AAGTCCAGCCAGAGTGTTTT ATTCAGCTCCAACAATTATA ATTACTTAGCT SEQ ID NO:1865 | GASSRST SEQ ID NO:9876 | TGGGCATCTACCCGGGA ATCC SEQ ID NO:9877 | QHSDNSPWT SEQ ID NO:17888 CAGCAATATTATAGTTCTCC TCTGACG SEQ ID NO:17889 |
| iPS:434771 | 21-225_81F9 | NA | KSSQSVLFSSNNYNYLA SEQ ID NO:1866 | | WASTRES SEQ ID NO:9878 | | QQYYSSPLT SEQ ID NO:17890 |
| | | AA | KSSQSVLYTSNNNNYLA SEQ ID NO:1867 | AAGTCCAGCCAGAGTGTTTT ATACACCTCCAACAATAACA ACTACTTAGCT | TGGGCATCTACCCGGGA ATCC SEQ ID NO:9879 | | CAGCACTACAATGATACTCC AGGGAAG SEQ ID NO:17891 |
| iPS:434773 | 21-225_75D9 | NA | | | WASTRES SEQ ID NO:9880 | | QHYNDTPGK SEQ ID NO:17892 |
| | | AA | RASQSVSSSYLA SEQ ID NO:1869 | AGGGCCAGTCAGAGTGTTAG CAGCAGCTACTTAGCC SEQ ID NO:1868 | GGTGCATCCAGCAGGGC CACT SEQ ID NO:9881 | | CAGCAGTATGAAAGCTCACC GTGGACG SEQ ID NO:17893 |
| iPS:434777 | 21-225_81C11 | NA | RASQSVSSSYLA SEQ ID NO:1870 | | GASSRAT SEQ ID NO:9882 | | QQYESSPWT SEQ ID NO:17894 |
| | | AA | RASQSVYSSYLA SEQ ID NO:1871 | AGGGCCAGTCAGAGTGTTTA CAGCAGCTACTTAGCC | GGTGCATCCAGCCGGTC CACT SEQ ID NO:9883 | | CAGCATTCTGATAACTCACC GTGGACG SEQ ID NO:17895 |
| iPS:434793 | 21-225_82A5 | NA | RASQSVSSSYLA SEQ ID NO:1872 | | GASSRST SEQ ID NO:9884 | | QHSDNSPWT SEQ ID NO:17896 |
| | | AA | RASQSVSSSYLA SEQ ID NO:1874 | AGGGCCAGTCAGAGTGTTAG CAGCAGCTACTTAGCC SEQ ID NO:1873 | GGTGCATCCACCAGGGC CACT SEQ ID NO:9885 | | CAGCAGTATGGTAACTCACC GCTCACT SEQ ID NO:17897 |
| | | | | | GASTRAT SEQ ID NO:9886 | | QQYGNSPLT SEQ ID NO:17898 |

FIGURE 49
(Continued)

| | | | | | |
|---|---|---|---|---|---|
| iPS:434797 | 21-225_82G5 | NA | AGGGCCAGTGAGAGTGTTAG CAGCAGCTACTTAGTC SEQ ID NO:1875 | GGTGCATCCACCAGGGC CACT SEQ ID NO:9887 | CAGCAGTATGGTTGCTCACC GCTCACT SEQ ID NO:17899 |
| | | AA | RASESVSSSYLV SEQ ID NO:1876 | GASTRAT SEQ ID NO:9888 | QQYGCSPLT SEQ ID NO:17900 |
| iPS:434805 | 21-225_82D9 | NA | AGGGCCAGTGAGAGTGTTAG CAGCAGCTACTTAGTC SEQ ID NO:1877 | GGTGCATCCACCAGGGC CACT SEQ ID NO:9889 | CAGCAGTATGGTTGCTCACC GCTCACT SEQ ID NO:17901 |
| | | AA | RASESVSSSYLV SEQ ID NO:1878 | GASTRAT SEQ ID NO:9890 | QQYGCSPLT SEQ ID NO:17902 |
| iPS:434809 | 21-225_74F5 | NA | AGGGCCAGTCAGGAGTGTTTA CAGCAGCTACTTAGCC SEQ ID NO:1879 | GGTGCATCCAGCCGGTC CACT SEQ ID NO:9891 | CAGCACTCTGATAACTCACC GTGGACG SEQ ID NO:17903 |
| | | AA | RASQSVYSSYLA SEQ ID NO:1880 | GASSRST SEQ ID NO:9892 | QHSDNSPWT SEQ ID NO:17904 |
| iPS:434813 | 21-225_82C12 | NA | AGGGCCAGTGAGAGTGTTAG CAGCAGCTACTTAGGG SEQ ID NO:1881 | GGTGCATCCACCAGGGC CTCT SEQ ID NO:9893 | CAGCAGTATGGTAACTCACC GCTCACT SEQ ID NO:17905 |
| | | AA | RASQSVSSSYLA SEQ ID NO:1882 | GASTRAS SEQ ID NO:9894 | QQYGNSPLT SEQ ID NO:17906 |
| iPS:434815 | 21-225_74A11 | NA | CGGGCAAGTCAGGACATTAG AAATGATTAGGC SEQ ID NO:1883 | GCTGCATCCAGTTGCAA AGT SEQ ID NO:9895 | CTACAGCATAATGATTACCC ATTCACT SEQ ID NO:17907 |
| | | AA | RASQDIRNDLG SEQ ID NO:1884 | AASSLQS SEQ ID NO:9896 | LQHNDYPFT SEQ ID NO:17908 |
| iPS:434821 | 21-225_83G1 | NA | AGGGCCAAGTCAGAGTGTTTA CAGCAGCTACTTAGCC SEQ ID NO:1885 | GGTGCATCCAGCCGGTC CACG SEQ ID NO:9897 | CAGCACTCTGATAACTCACC GTGGACG SEQ ID NO:17909 |
| | | AA | RASQSVYSSYLA SEQ ID NO:1886 | GASSRST SEQ ID NO:9898 | QHSDNSPWT SEQ ID NO:17910 |

FIGURE 49
(Continued)

| | | | | | |
|---|---|---|---|---|---|
| iPS:434825 | 21-225_83C2 | NA | AGGGCCAGTCAGAGTGTTAG CAGCAGCTACTTAGTC SEQ ID NO:1887 | GGTGCATCCACCAGGGC CACT SEQ ID NO:9899 | CAGCAGTATGGTTGCTCACC GCTCACT SEQ ID NO:17911 |
| | | AA | RASQSVSSSYLV SEQ ID NO:1888 | GASTRAT SEQ ID NO:9900 | QQYGCSPLT SEQ ID NO:17912 |
| iPS:434827 | 21-225_83F3 | NA | AAGTCCAGCCAGAGTGTTT ATACACCTCCAACAATAACA ACTACTTAGCT SEQ ID NO:1889 | TGGGCATCTACCCGGGA ATCC SEQ ID NO:9901 | CAGCACTATAATGATACTCC ATGGAAG SEQ ID NO:17913 |
| | | AA | KSSQSVLYTSNNNNYLA SEQ ID NO:1890 | WASTRES SEQ ID NO:9902 | QHYNDTPWK SEQ ID NO:17914 |
| iPS:434829 | 21-225_83G3 | NA | AAGTCCAGCCAGAGTGTTT ATACACCTCCAACAATAACA ACTACTTAGCT SEQ ID NO:1891 | TGGGCATCTACCCGGGA ATCC SEQ ID NO:9903 | CAGCACTATTATAATACTCC GTGGACG SEQ ID NO:17915 |
| | | AA | KSSQSVLYTSNNNNYLA SEQ ID NO:1892 | WASTRES SEQ ID NO:9904 | QHYYNTPWT SEQ ID NO:17916 |
| iPS:434833 | 21-225_83C5 | NA | AGGGCCAGTGAGAGTGTTAG CAGCAGCTACTTAGTC SEQ ID NO:1893 | GGTGCATCCACCAGGGC CACT SEQ ID NO:9905 | CAGCAGTATGGTTGTTGCTCACC GCTCACT SEQ ID NO:17917 |
| | | AA | RASESVSSSYLV SEQ ID NO:1894 | GASTRAT SEQ ID NO:9906 | QQYGCSPLT SEQ ID NO:17918 |
| iPS:434835 | 21-225_83B6 | NA | AGGGCCAGTCAGAGTGTTGA CAGCAGCTACTTAGCC SEQ ID NO:1895 | GGTGCATCCAGCAGGAC CCCT SEQ ID NO:9907 | CAGCAGTATGAAAGCTCACC GTGGACG SEQ ID NO:17919 |
| | | AA | RASQSVDSGYLA SEQ ID NO:1896 | GASSRTP SEQ ID NO:9908 | QQYESSPWT SEQ ID NO:17920 |
| iPS:434839 | 21-225_83B7 | NA | AGGGCCAGTCAGAGTGTTTA CAGCAGCTACTTAGCG SEQ ID NO:1897 | GGTGCATCCAGCCGGTC CACT SEQ ID NO:9909 | CAGCACTCTGATAACTCACC GTGGACG SEQ ID NO:17921 |

FIGURE 49
(Continued)

| | | | | | | | |
|---|---|---|---|---|---|---|---|
| iPS:434841 | 21-225_83G7 | AA | RASQSVYSSYLA | | GASSRST | | QHSDNSPWT |
| | | | SEQ ID NO:1898 | | SEQ ID NO:9910 | | SEQ ID NO:17922 |
| | | NA | AAGTCCAGCCAGAGTGTTTT ACACAGTCCAACAATTATA ACTACTTAGCT | | TGGACATCTACCCGGGA ATCC | | CAGCAATATTTTAGTAGTCC TCTGACG |
| | | | SEQ ID NO:1899 | | SEQ ID NO:9911 | | SEQ ID NO:17923 |
| iPS:434849 | 21-225_83C10 | AA | KSSQTVLHSSNNYNYLA | | WTSTRES | | QQYFSSPLT |
| | | | SEQ ID NO:1900 | | SEQ ID NO:9912 | | SEQ ID NO:17924 |
| | | NA | AGGGCCAGTCCGAGTGTCA CAGCAACTACTTAGCC | | GGTGCATCCAGCAGGGC CACT | | CAGCAGTATGAAAGTTCACC GTGGACG |
| | | | SEQ ID NO:1901 | | SEQ ID NO:9913 | | SEQ ID NO:17925 |
| iPS:434851 | 21-225_75A6 | AA | RASPSVHSNYLA | | GASSRAT | | QQYESSPWT |
| | | | SEQ ID NO:1902 | | SEQ ID NO:9914 | | SEQ ID NO:17926 |
| | | NA | AAGTCCAGACAGAGTGTTTT ACACAGTCCAACAATTACA ACTACTTAGCT | | TGGGCATCTACCCGGGA ATCC | | CAGCAATATTATAGTACTCC TCCTACT |
| | | | SEQ ID NO:1903 | | SEQ ID NO:9915 | | SEQ ID NO:17927 |
| iPS:434863 | 21-225_84G7 | AA | KSRQSVLHSSNNYNYLA | | WASTRES | | QQYSTPPT |
| | | | SEQ ID NO:1904 | | SEQ ID NO:9916 | | SEQ ID NO:17928 |
| | | NA | AAGTCCAGCCAGAGTGTTTT ACACAGTCCAACAATTACA ACTACTTAGCT | | TGGACATCTACCCGGGA ATCC | | CAGCAATATTTTAGTAGTCC TCCGACG |
| | | | SEQ ID NO:1905 | | SEQ ID NO:9917 | | SEQ ID NO:17929 |
| iPS:434867 | 21-225_79A12 | AA | KSSQTVLHSSNNYNYLA | | WTSTRES | | QQYFSSPPT |
| | | | SEQ ID NO:1906 | | SEQ ID NO:9918 | | SEQ ID NO:17930 |
| | | NA | CGGGGCGAGTCAGGTCATTAG CAAGTATTTAGCC | | GCTGCATCCAGCAGTTGCAA AGT | | CAACAGTACAGTAATTACC GCTCACT |
| | | | SEQ ID NO:1907 | | SEQ ID NO:9919 | | SEQ ID NO:17931 |
| | | AA | RASQVISKYLA | | AASSLQS | | QQYSNYPLT |
| | | | SEQ ID NO:1908 | | SEQ ID NO:9920 | | SEQ ID NO:17932 |

FIGURE 49
(Continued)

| | | | | | |
|---|---|---|---|---|---|
| iPS:434869 | 21-225_84E12 | NA | AGGGCCAGTCAGAGTATTAA CAGCAACTACTTAGCC SEQ ID NO:1909 | GGTGCATCCAGCAGGGC CACT SEQ ID NO:9921 | CAGCAGTATGAGAGCTCACC GTGGACG SEQ ID NO:17933 |
| | | AA | RASQSINSNYLA SEQ ID NO:1910 | GASSRAT SEQ ID NO:9922 | QQYESSPWT SEQ ID NO:17934 |
| iPS:434871 | 21-225_85H11 | NA | AGGGCCAGTCAGAGGATGTTAT CACCTACTTAGCC SEQ ID NO:1911 | GGTGCATCCAGCACCAGGGC CACT SEQ ID NO:9923 | CAGGAGTATAATGACTGGCC GTGCAGT SEQ ID NO:17935 |
| | | AA | RASQDVITYLA SEQ ID NO:1912 | GASTRAT SEQ ID NO:9924 | QEYNDWPCS SEQ ID NO:17936 |
| iPS:434877 | 21-225_85B2 | NA | AAGTCCAGCCAGAGTGTTTT ACACAGCTCAATAAAAGA ACTACTTAGCT SEQ ID NO:1913 | TGGGCATCTACCCGGGA ATCC SEQ ID NO:9925 | CAGCAATATTATAGGACTCC GTGGACG SEQ ID NO:17937 |
| | | AA | KSSQSVLHSSNKKNYLA SEQ ID NO:1914 | WASTRES SEQ ID NO:9926 | QQYYRTPWT SEQ ID NO:17938 |
| iPS:434879 | 21-225_85A3 | NA | AGGGCCAGTCAGAGTGTTTA CAGCAGCTACTTAGCC SEQ ID NO:1915 | GGTGCATCCAGCCGGGC CAGT SEQ ID NO:9927 | CAGCACTATGATAACTCACC GTGGACG SEQ ID NO:17939 |
| | | AA | RASQSVYSSYLA SEQ ID NO:1916 | GASSRAS SEQ ID NO:9928 | QHYDNSPWT SEQ ID NO:17940 |
| iPS:434881 | 21-225_85B4 | NA | AGGGCCAGTCAGAGTGTTTA CAGCAGCTACTTAGCC SEQ ID NO:1917 | GGTGCATCCAGCCAGGGC CACT SEQ ID NO:9929 | CAGCACTATGATAACTCACC GTGGACG SEQ ID NO:17941 |
| | | AA | RASQSVYSSYLA SEQ ID NO:1918 | GASSRAT SEQ ID NO:9930 | QHYDNSPWT SEQ ID NO:17942 |
| iPS:434883 | 21-225_85B5 | NA | AGGTCCAGTCAGAGTGTTAG CAGCAGCTACTTAGTC SEQ ID NO:1919 | GGTGCATCCAGCACCAGGGC CACT SEQ ID NO:9931 | CAGCAGTATGGTTGCTCACC GCTCACT SEQ ID NO:17943 |
| | | AA | RSSQSVSSSYLV | GASTRAT | QQYGCSPLT |

FIGURE 49
(Continued)

| | | | | | | |
|---|---|---|---|---|---|---|
| iPS:434887 | 21-225_85D6 | NA | SEQ ID NO:1920 AGGGCCAGTCAGAGTGTTAG CAGCAGGTACTTAGCC | SEQ ID NO:9932 GGTGCATCCAGCAGGGC CACT | SEQ ID NO:17944 CAGCATTATGATAGCTCACC GTGGACG | |
| | | AA | SEQ ID NO:1921 RASQSVSSRYLA | SEQ ID NO:9933 GASSRAT | SEQ ID NO:17945 QHYDSSPWT | |
| iPS:434891 | 21-225_85G6 | NA | SEQ ID NO:1922 AGGGCCAGTCCAGAGTGTGA CAGCAGCTACTTAGCC | SEQ ID NO:9934 GGTGCAGCCAGCAGGGC CCCT | SEQ ID NO:17946 CAGCAGTATGAAAGTTCACC GTGGACG | |
| | | AA | SEQ ID NO:1923 RASPSVDSSYLA | SEQ ID NO:9935 GAASRAP | SEQ ID NO:17947 QQYESSPWT | |
| iPS:434895 | 21-225_74B7 | NA | SEQ ID NO:1924 AGGGCCAGTCAGAGAATATTA CAGCAGCTACTTAGCC | SEQ ID NO:9936 GGTGCATCCAGCAGGGC CACT | SEQ ID NO:17948 CAGCAGTATGAAAGTTCACC GTGGACC | |
| | | AA | SEQ ID NO:1925 RASQNIYSSYLA | SEQ ID NO:9937 GASSRAT | SEQ ID NO:17949 QQYESSPWT | |
| iPS:434899 | 21-225_85B9 | NA | SEQ ID NO:1926 AGGGCCAGTCAGAGTGTTAA CAGCAACTACTTAGCC | SEQ ID NO:9938 GGTGCATCCAGCAGGGC CACT | SEQ ID NO:17950 CAGCAGTATGAAAGTCGCC GTGGACG | |
| | | AA | SEQ ID NO:1927 RASQSVNSNYLA | SEQ ID NO:9939 GASSRAT | SEQ ID NO:17951 QQYESSPWT | |
| iPS:434901 | 21-225_85H9 | NA | SEQ ID NO:1928 AAGTCCAGCCAGAGTGTTTT ACACAGGTCCAACAATTACA ACTACTTAGCG | SEQ ID NO:9940 TGGGCATCTACCCGGGA ATCC | SEQ ID NO:17952 CAGCAATATTATAGTACTCC TCCGACG | |
| | | AA | SEQ ID NO:1929 KSSQSVLHRSNNYNYLA | SEQ ID NO:9941 WASTRES | SEQ ID NO:17953 QQYYSTPPT | |
| iPS:434907 | 21-225_85G10 | NA | SEQ ID NO:1930 AGGGCCAGTCAGAGTGTTTG GAGCGGTACTTAGCC | SEQ ID NO:9942 GGTGCATCTAGCAGGGC CACT | SEQ ID NO:17954 CAGCAGTATGAGAGTTCACC GTGGACG | |
| | | | SEQ ID NO:1931 | SEQ ID NO:9943 | SEQ ID NO:17955 | |

FIGURE 49
(Continued)

| | | | | | | |
|---|---|---|---|---|---|---|
| iPS:434909 | 21-225_85C11 | AA | RASQSVWSGYLA SEQ ID NO:1932 | GASSRAT SEQ ID NO:9944 | QQYESSPWT SEQ ID NO:17956 |
| | | NA | AAGTCCAGCAGAGTGTTT GTACAGTCCAACAGTCACA ACTTCTTAGCT SEQ ID NO:1933 | TGGGCATTTATCCGGGA ATCC SEQ ID NO:9945 | CAGCAATATTATAGTACTCC GTGCAGT SEQ ID NO:17957 |
| iPS:434911 | 21-225_85D11 | AA | KSSQSVLYSSNSHNFLA SEQ ID NO:1934 | WAFIRES SEQ ID NO:9946 | QQYYSTPCS SEQ ID NO:17958 |
| | | NA | AGGTCCAGTCAGAGTGTTAG CAGCAGTACTTAGTC SEQ ID NO:1935 | GGTGCATCCACCAGGGC CACT SEQ ID NO:9947 | CAGCAGTATGGTTGCTCACC GCTCACT SEQ ID NO:17959 |
| iPS:434913 | 21-225_86C1 | AA | RSSQSVSSSYLV SEQ ID NO:1936 | GASTRAT SEQ ID NO:9948 | QQYGCSPLT SEQ ID NO:17960 |
| | | NA | AGGGCCAGTCAGAGTGTTTA CAGCAGTACTTAGCC SEQ ID NO:1937 | GGTGCATCCAGCGGGC CACT SEQ ID NO:9949 | CAGCACTATGATAACTCACC GTGGACG SEQ ID NO:17961 |
| iPS:434921 | 21-225_86E4 | AA | RASQSVYSSYLA SEQ ID NO:1938 | GASSRAT SEQ ID NO:9950 | QHYDNSPWT SEQ ID NO:17962 |
| | | NA | AGGGCCAGTCAGAGTGTTTA CAGCAGTACTTAGCC SEQ ID NO:1939 | GGTGCATCCAGCCGGTC CACT SEQ ID NO:9951 | CAGCACTCTGATAACTCACC GTGGACG SEQ ID NO:17963 |
| | | AA | RASQSVYSSYLA SEQ ID NO:1940 | GASSRST SEQ ID NO:9952 | QHSDNSPWT SEQ ID NO:17964 |
| iPS:434935 | 21-225_86E9 | NA | AAGTCCAGCAGAGTGTTT GCACAGATCCAACAATTATA ATTACTTAGCT SEQ ID NO:1941 | TGGGCATCTACCGGGA ATCC SEQ ID NO:9953 | CAGCAATATCATAGTAGTCC ACTGACG SEQ ID NO:17965 |
| | | AA | KSSQSVLHRSNNYNYLA SEQ ID NO:1942 | WASTRES SEQ ID NO:9954 | QQYHSSPLT SEQ ID NO:17966 |

FIGURE 49
(Continued)

| | | | | | |
|---|---|---|---|---|---|
| iPS:434939 | 21-225_86C11 | NA | AGGGCCAGTCAGAGTGTTTAGCCAGCAGCTACTTAGCC<br>SEQ ID NO:1943 | GGTGCATCCAGCCGGTCCACT<br>SEQ ID NO:9955 | CAGCACTCTGATAACTCACCGTGGACG<br>SEQ ID NO:17967 |
| | | AA | RASQSVYSSYLA<br>SEQ ID NO:1944 | GASSRST<br>SEQ ID NO:9956 | QHSDNSPWT<br>SEQ ID NO:17968 |
| iPS:434943 | 21-225_87H1 | NA | AGGGCCAGTCAGAGTGTTGA<br>CAGCAACTACTTAGCC<br>SEQ ID NO:1945 | GGTGCATCTGCCAGGAC<br>CACT<br>SEQ ID NO:9957 | CAGCAGTATGAAAGCTCACC<br>GTGGACG<br>SEQ ID NO:17969 |
| | | AA | RASQSVDSNYLA<br>SEQ ID NO:1946 | GASARTT<br>SEQ ID NO:9958 | QQYESSPWT<br>SEQ ID NO:17970 |
| iPS:434945 | 21-225_87E5 | NA | AGGGCCAGTCAGAGTGTTTA<br>CAGCAGCTACTTAGCC<br>SEQ ID NO:1947 | GGTGCATCCAGCCGGTC<br>CACT<br>SEQ ID NO:9959 | CAGCATTCTGATAACTCACC<br>GTGGACG<br>SEQ ID NO:17971 |
| | | AA | RASQSVYSSYLA<br>SEQ ID NO:1948 | GASSRST<br>SEQ ID NO:9960 | QHSDNSPWT<br>SEQ ID NO:17972 |
| iPS:434947 | 21-225_87B7 | NA | CGGGCGAGTCAGGGCATTAG<br>CAATTATTAGCC<br>SEQ ID NO:1949 | GCTGCATCCAGTTGCAC<br>AGT<br>SEQ ID NO:9961 | CTACTCTATCTTACTTACCCG<br>CTCACC<br>SEQ ID NO:17973 |
| | | AA | RASQGISNYLA<br>SEQ ID NO:1950 | AASSLHS<br>SEQ ID NO:9962 | LLYLTYPLT<br>SEQ ID NO:17974 |
| iPS:434955 | 21-225_87C9 | NA | AGGGCCAGTCAGAGTGTTTA<br>CAGCAGCTACTTAGCC<br>SEQ ID NO:1951 | GGTGCATCCAGCCGGTC<br>CACT<br>SEQ ID NO:9963 | CAGCATTCTGATAACTCACC<br>GTGGACG<br>SEQ ID NO:17975 |
| | | AA | RASQSVYSSYLA<br>SEQ ID NO:1952 | GASSRST<br>SEQ ID NO:9964 | QHSDNSPWT<br>SEQ ID NO:17976 |
| iPS:434957 | 21-225_87A10 | NA | AGGGCCAGTCAGAGTGTTAG<br>CAGCAGCTACTTAGCC<br>SEQ ID NO:1953 | GGTGCATCCACCAGGGC<br>CTCT<br>SEQ ID NO:9965 | CAGCAGTATGGTAACTCACC<br>GCTCACT<br>SEQ ID NO:17977 |
| | | AA | RASQSVSSSYLA<br>SEQ ID NO:1954 | GASTRAS<br>SEQ ID NO:9966 | QQYGNSPLT<br>SEQ ID NO:17978 |

FIGURE 49
(Continued)

| | | | | | |
|---|---|---|---|---|---|
| iPS:434959 | 21-225_87E10 | NA | AAGTCCAGCCAGAGTGTTT ACACAGCTCCAACAATATGA ACTACTTAGCT SEQ ID NO:1955 | TGGGCATCTACCCGGAA ATCC SEQ ID NO:9967 | CAGCAATATTATAGTAGTCC GTGCAGT SEQ ID NO:17979 |
| | | AA | KSSQSVLHSSNNMNYLA SEQ ID NO:1956 | WASTRKS SEQ ID NO:9968 | QQYYSSPCS SEQ ID NO:17980 |
| iPS:434961 | 21-225_87A12 | NA | AGGGCCAGTCAGAGTGTTA CAGCAGCTACTTAGCC SEQ ID NO:1957 | GGTGCATCCAGCCGGTC CACT SEQ ID NO:9969 | CAGCACTCTGATAACTCACC GTGGACG SEQ ID NO:17981 |
| | | AA | RASQSVYSSYLA SEQ ID NO:1958 | GASSRST SEQ ID NO:9970 | QHSDNSPWT SEQ ID NO:17982 |
| iPS:434965 | 21-225_88A1 | NA | AAGTCCAGCCAGAGTGTTT ACACAGCTCCAACAATTACA ACTACTTAACT SEQ ID NO:1959 | TGGGCATCTACCCGGAA ATCC SEQ ID NO:9971 | CAGCAATATTATAGTTCTCC TCCGACG SEQ ID NO:17983 |
| | | AA | KSSQSVLHSSNNYNYLT SEQ ID NO:1960 | WASTRKS SEQ ID NO:9972 | QQYYSSPPT SEQ ID NO:17984 |
| iPS:434969 | 21-225_88H1 | NA | AGGGCCAGTCAGAGTGTTA CAGCAGCTACTTAGCC SEQ ID NO:1961 | GGTGCATCCAGCCGGTC CACG SEQ ID NO:9973 | CAGCATTCTGATAACTCACC GTGGACG SEQ ID NO:17985 |
| | | AA | RASQSVYSSYLA SEQ ID NO:1962 | GASSRST SEQ ID NO:9974 | QHSDNSPWT SEQ ID NO:17986 |
| iPS:434971 | 21-225_88G2 | NA | AAGTCCAGCCAGAGTGTTT ATACACCTCCAACAATAACA ACTACTTAGCT SEQ ID NO:1963 | TGGGCATCTACCCGGGA ATCC SEQ ID NO:9975 | CAGCAATATTATAATACTCC GTGGACG SEQ ID NO:17987 |
| | | AA | KSSQSVLYTSNNNNYLA SEQ ID NO:1964 | WASTRES SEQ ID NO:9976 | QQYYNTPWT SEQ ID NO:17988 |

FIGURE 49
(Continued)

| | | | | | |
|---|---|---|---|---|---|
| iPS:434973 | 21-225_88B4 | NA | AAGTCCAGCCAGAGTGTTTT ATACATCCAACAATAATA ATTACTTAGCT SEQ ID NO:1965 | TGGGCATCTACCCGGGA ATCC SEQ ID NO:9977 | CAGCAATATTATAGTACTCC TCCGACG SEQ ID NO:17989 |
| | | AA | KSSQSVLYISNNNNYLA SEQ ID NO:1966 | WASTRES SEQ ID NO:9978 | QQYYSTPPT SEQ ID NO:17990 |
| iPS:434977 | 21-225_88A5 | NA | CGGGCAAGTCAGGGCATTAG AAATGATTTAGGC SEQ ID NO:1967 | GCTGCATCCAGTTTGCAA AGT SEQ ID NO:9979 | CTACAGCATAATGATTACCC ATTCACT SEQ ID NO:17991 |
| | | AA | RASQGIRNDLG SEQ ID NO:1968 | AASSLQS SEQ ID NO:9980 | LQHNDYPFT SEQ ID NO:17992 |
| iPS:434981 | 21-225_88E7 | NA | AGGGCCAGTCAGAGTGTTTA CAGCAGCTACTTAGCC SEQ ID NO:1969 | GGTGCATCCAGCCGGTC CACT SEQ ID NO:9981 | CAGCACTCTGATAACTCACC GTGGACG SEQ ID NO:17993 |
| | | AA | RASQSVYSSYLA SEQ ID NO:1970 | GASSRST SEQ ID NO:9982 | QHSDNSPWT SEQ ID NO:17994 |
| iPS:434983 | 21-225_88F7 | NA | AGGGCCAGTCAGAGTGTTTA CAGCAGCTACTTAGCC SEQ ID NO:1971 | GGTGCATCCAGCCGGTC CACT SEQ ID NO:9983 | CAGCACTCTGATAACTCACC GTGGACG SEQ ID NO:17995 |
| | | AA | RASQSVYSSYLA SEQ ID NO:1972 | GASSRST SEQ ID NO:9984 | QHSDNSPWT SEQ ID NO:17996 |
| iPS:434995 | 21-225_88G9 | NA | AGGGCCAGTCAGAGTGTTTA CAGCAGCTACTTAGCC SEQ ID NO:1973 | GGTGCATCCAGCCGGTC CACT SEQ ID NO:9985 | CAGCACTCTGATAACTCACC GTGGACG SEQ ID NO:17997 |
| | | AA | RASQSVYSSYLA SEQ ID NO:1974 | GASSRST SEQ ID NO:9986 | QHSDNSPWT SEQ ID NO:17998 |
| iPS:434997 | 21-225_88C10 | NA | AAGTCCAGCCAGAGTGTTT ACACAGCTCCAACAATTGGA ATTACTTAGCT SEQ ID NO:1975 | TGGGCATTTACTCGGAA ATCC SEQ ID NO:9987 | CAGCAATATTATAGAGCTCC TCCGACG SEQ ID NO:17999 |

FIGURE 49
(Continued)

| | | | | | | |
|---|---|---|---|---|---|---|
| iPS:434999 | 21-225_75A8 | AA | KSSQSVLHSSNNWNYLA SEQ ID NO:1976 | WAFTRKS SEQ ID NO:9988 | QQYYRAPPT SEQ ID NO:18000 |
| | | NA | AGGGCCAGTCAGAGTGTTTA CAGCAGCTACTTAGCC SEQ ID NO:1977 | GGTTGCATCCAGCCGGGC CACT SEQ ID NO:9989 | CAGCACTCTGATAACTCACC GTGGACG SEQ ID NO:18001 |
| iPS:435009 | 21-225_89G4 | AA | RASQSVYSSYLA SEQ ID NO:1978 | GASSRAT SEQ ID NO:9990 | QHSDNSPWT SEQ ID NO:18002 |
| | | NA | AGGTCTAGTCAGAGCCTCCT GCATAGTAGTGGATACAACT ATTTGGAT SEQ ID NO:1979 | TTGGGTTCTAATCGGGGC TCC SEQ ID NO:9991 | ATGCAAGTCTACATATTCC TCTCACT SEQ ID NO:18003 |
| iPS:435013 | 21-225_89D5 | AA | RSSQSLLHSSGYNYLD SEQ ID NO:1980 | LGSNRAS SEQ ID NO:9992 | MQALHIPLT SEQ ID NO:18004 |
| | | NA | AGGGCCAGTCAGAGTGTTTA CAGCAGCTACTTAGCC SEQ ID NO:1981 | GGTTGCATCCAGCCGGTC CACT SEQ ID NO:9993 | CAGCACTATGATAACTCACC GTGGACG SEQ ID NO:18005 |
| iPS:435015 | 21-225_89H5 | AA | RASQSVYSSYLA SEQ ID NO:1982 | GASSRST SEQ ID NO:9994 | QHYDNSPWT SEQ ID NO:18006 |
| | | NA | AGGGCCAGTCAGAGTGTTAA CAGCAGCTACTTAGCC SEQ ID NO:1983 | GGTTGCATTCAGCAGGGC CACT SEQ ID NO:9995 | CAGCAGTATGAAAGCTCAGT GTGGACG SEQ ID NO:18007 |
| iPS:435025 | 21-225_89E10 | AA | RASQSVNSNYLA SEQ ID NO:1984 | GAFSRAT SEQ ID NO:9996 | QQYESSVVT SEQ ID NO:18008 |
| | | NA | AGGGCCAGTCAGAGTGTTTA CAGCAGCTACTTAGCC SEQ ID NO:1985 | GGTTGCATCCAGCCGGTC CACT SEQ ID NO:9997 | CAGCATTCTGATAACTCTCC GTGGACG SEQ ID NO:18009 |
| iPS:435029 | | AA | RASQSVYSSYLA SEQ ID NO:1986 | GASSRST SEQ ID NO:9998 | QHSDNSPWT SEQ ID NO:18010 |
| | | NA | AGGGCCAGTCAGAGTGTTGA CAGCAACTTCTTAGCC | GGTGCATCTGCCAGGAC CACT | CAGCAGTATGAAATCTCACC GTGGACG |

FIGURE 49
(Continued)

| | | | | | | |
|---|---|---|---|---|---|---|
| iPS:435039 | 21-225_89A11 | AA | SEQ ID NO:1987<br>RASQSVDSNFLA<br>SEQ ID NO:1988 | SEQ ID NO:9999<br>GASARTT<br>SEQ ID NO:10000 | SEQ ID NO:18011<br>QQYEISPWT<br>SEQ ID NO:18012 |
| iPS:435041 | 21-225_90G4 | NA | AGGGCCAGTCAGAGTGTTTA<br>CAGCAGCTACTTAGCC<br>SEQ ID NO:1989 | GGTGCATCCAGCCGTC<br>CACT<br>SEQ ID NO:10001 | CAGCACTCTGATAACTCACC<br>GTGGACG<br>SEQ ID NO:18013 |
| | | AA | RASQSVYSSYLA<br>SEQ ID NO:1990 | GASSRST<br>SEQ ID NO:10002 | QHSDNSPWT<br>SEQ ID NO:18014 |
| iPS:435043 | 21-225_90A5 | NA | AGGGCCAGTCAGAGTGTTTA<br>CAGCAGCTACTTAGCC<br>SEQ ID NO:1991 | GGTGCATCCAGCCGGGC<br>CACT<br>SEQ ID NO:10003 | CAGCACTATGATAACTCACC<br>GTGGACG<br>SEQ ID NO:18015 |
| | | AA | RASQSVYSSYLA<br>SEQ ID NO:1992 | GASSRAT<br>SEQ ID NO:10004 | QHYDNSPWT<br>SEQ ID NO:18016 |
| iPS:435044 | 21-225_90G5 | NA | AGGGCCAGTCAGAGTGTTTA<br>CAGCAGCTACTTAGCC<br>SEQ ID NO:1993 | GGTGCATCCAGCCGGGC<br>CACT<br>SEQ ID NO:10005 | CAGCACTATGATAACTCACC<br>GTGGACG<br>SEQ ID NO:18017 |
| | | AA | RASQSVYSSYLA<br>SEQ ID NO:1994 | GASSRAT<br>SEQ ID NO:10006 | QHYDNSPWT<br>SEQ ID NO:18018 |
| iPS:435045 | 21-225_90H5 | NA | CGGGCAAGTCAGGGCATTAG<br>AAATGATTAGGC<br>SEQ ID NO:1995 | ATTGCATCCAGTTGCAA<br>AGT<br>SEQ ID NO:10007 | CTACAGCATAATAGTTACCC<br>GATCACC<br>SEQ ID NO:18019 |
| | | AA | RASQGIRNDLG<br>SEQ ID NO:1996 | IASSLQS<br>SEQ ID NO:10008 | LQHNSYPIT<br>SEQ ID NO:18020 |
| iPS:435051 | 21-225_90D9 | NA | AAGTCCAGCCAGAGTGTTTT<br>ACACAGCTCCAACAATTATA<br>ACTACTTAGCT<br>SEQ ID NO:1997 | TGGACATCTACCCGGGA<br>ATCC<br>SEQ ID NO:10009 | CAGCAATATCTTAGTAGTCC<br>TCTGACG<br>SEQ ID NO:18021 |
| | | AA | KSSQTVLHSSNNYNYLA<br>SEQ ID NO:1998 | WTSTRES<br>SEQ ID NO:10010 | QQYLSSPLT<br>SEQ ID NO:18022 |

FIGURE 49
(Continued)

| | | | | | | |
|---|---|---|---|---|---|---|
| iPS:435053 | 21-225_75F9 | NA | AAGTCCAGCCAGAGTGTTT ACACAACTCCAACAATAATA ACTACTTGGCT SEQ ID NO:1999 | TGGGCATCTACGCGGGA GTCC SEQ ID NO:10011 | CAACAATATTATAGTAGTCC TCCGACG SEQ ID NO:18023 |
| | | AA | KSSQSVLHNSNNNYLA SEQ ID NO:2000 | WASTRES SEQ ID NO:10012 | QQYYSSPPT SEQ ID NO:18024 |
| iPS:435055 | 21-225_90F10 | NA | AGGGCCAGTCAGAGTGTTA CAGCAGCTACTTAGCC SEQ ID NO:2001 | GGTGCATCCAGCCGGTC CACT SEQ ID NO:10013 | CAGCACTATGATAACTCACC GTGGACG SEQ ID NO:18025 |
| | | AA | RASQSVYSSYLA SEQ ID NO:2002 | GASSRST SEQ ID NO:10014 | QHYDNSPWT SEQ ID NO:18026 |
| iPS:435059 | 21-225_90C11 | NA | AGGTATAGTTCAGAGAGCCTCGT GCATAGTAGTGGATACAACT ATTTGGAT SEQ ID NO:2003 | TTGGGTTCTAATCGGGCC TCC SEQ ID NO:10015 | ATGCAAGCTCTACACCCTCC TCTCACT SEQ ID NO:18027 |
| | | AA | RYSQSLVHSSGYNYLD SEQ ID NO:2004 | LGSNRAS SEQ ID NO:10016 | MQALHPPLT SEQ ID NO:18028 |
| iPS:435071 | 21-225_91F1 | NA | AAGTCCAGCCAGAGTGTTT ATACACCTCCAACAATAACA ACTACTTAGCT SEQ ID NO:2005 | TGGGCATCTACCCGGGA ATCC SEQ ID NO:10017 | CAGCACTATTATAATACTCC GTGGAAG SEQ ID NO:18029 |
| | | AA | KSSQSVLYTSNNNNYLA SEQ ID NO:2006 | WASTRES SEQ ID NO:10018 | QHYYNTPWK SEQ ID NO:18030 |
| iPS:435073 | 21-225_91B2 | NA | AGGGCCAGTCAGAGTGTTA CAGCAGCTACTTAGCC SEQ ID NO:2007 | GGTGCATCCAGCCGGTC CACT SEQ ID NO:10019 | CAGCACTATGATAACTCACC GTGGACG SEQ ID NO:18031 |
| | | AA | RASQSVYSSYLA SEQ ID NO:2008 | GASSRST SEQ ID NO:10020 | QHYDNSPWT SEQ ID NO:18032 |
| iPS:435075 | | NA | AGGGCCAGTCAGAGTGTTA CAGCAGCTACTTAGCC | GGTGCATCCAGCCGGTC CACT | CAGCACTATGATAACTCACC GTGGACG |

FIGURE 49
(Continued)

| | | | | | | |
|---|---|---|---|---|---|---|
| iPS:435077 | 21-225_91B3 | NA | SEQ ID NO:2009<br>AGGGCCAGTCAGAGTGTTTA<br>CAGCAGCTACTTAGCC | SEQ ID NO:2010<br>RASQSVYSSYLA | SEQ ID NO:10021<br>GGTGCATCCAGCCGGTC<br>CACT | SEQ ID NO:18033<br>QHYDNSPWT |
| | | AA | SEQ ID NO:2010<br>RASQSVYSSYLA | SEQ ID NO:2010<br>GASSRST | SEQ ID NO:10022<br>CAGCATTCTGATAACTCACC<br>GTGGACG | SEQ ID NO:18034<br>QHYDNSPWT |
| iPS:435079 | 21-225_91F3 | NA | SEQ ID NO:2011<br>AGGGCCAGTCAGAGTGTTTA<br>CAGCAGCTACTTAGCC | SEQ ID NO:10023<br>GGTGCATCCAGCCGGTC<br>CACT | SEQ ID NO:18035<br>QHSDNSPWT |
| | | AA | SEQ ID NO:2012<br>RASQSVYSSYLA | SEQ ID NO:10024<br>GASSRST | SEQ ID NO:18036<br>CAGCACTATGATAACTCACC<br>GTGGACG |
| iPS:435087 | 21-225_91B4 | NA | SEQ ID NO:2013<br>AGGGCCAGTCAGAGTGTTTA<br>CAGCAGCTACTTAGCC | SEQ ID NO:10025<br>GGTGCATCCAGCCGGTC<br>CACT | SEQ ID NO:18037<br>QHYDNSPWT |
| | | AA | SEQ ID NO:2014<br>RASQSVYSSYLA | SEQ ID NO:10026<br>GASSRST | SEQ ID NO:18038<br>CAGCAATATTATACTACTCC<br>GTGGACG |
| iPS:435089 | 21-225_91G8 | NA | SEQ ID NO:2015<br>AAGTCCAGCCAGAGTGTTT<br>ATACACCTCCAACAATAACA<br>ACTACTTAGCT | SEQ ID NO:10027<br>TGGGCATCTACCCGGGA<br>ATCC | SEQ ID NO:18039<br>QQYYTPWT |
| | | AA | SEQ ID NO:2016<br>KSSQSVLYTSNNNNYLA | SEQ ID NO:10028<br>WASTRES | SEQ ID NO:18040<br>CAGCACTCTGATAACTCACC<br>GTGGACG |
| iPS:435097 | 21-225_91E9 | NA | SEQ ID NO:2017<br>AGGGCCAGTCAGAGTGTTTA<br>CAGCAGCTACTTAGCG | SEQ ID NO:10029<br>GGTGCATCCAGCCGGGC<br>CACG | SEQ ID NO:18041<br>QHSDNSPWT |
| | | AA | SEQ ID NO:2018<br>RASQSVYSSYLA | SEQ ID NO:10030<br>GASSRAT | SEQ ID NO:18042<br>CAGCAGTATGAAAGTTCACC<br>GTGGACG |
| iPS:435097 | 21-225_92B1 | NA | SEQ ID NO:2019<br>AGGGCCAGTCAGAGTGTTGG<br>CAGCAACTACTTAGCC | SEQ ID NO:10031<br>GGTGCATCCAGCCAGGGC<br>CACT | SEQ ID NO:18043<br>QQYESSPWT |
| | | AA | SEQ ID NO:2020<br>RASQSVGSNYLA | SEQ ID NO:10032<br>GASSRAT | SEQ ID NO:18044 |

FIGURE 49 (Continued)

| | | | | | |
|---|---|---|---|---|---|
| iPS:435103 | 21-225_92B2 | NA | AGGTCTAGTCAGAGCCTCGT GCATAGTAGTGGATACAACT ATTTGGAT SEQ ID NO:2021 | TTGGGTTCTAATCGGGCC TCC SEQ ID NO:10033 | ATGCAAGCTCTACATATTCC TCTCACT SEQ ID NO:18045 |
| | | AA | RSSQSLVHSSGYNYLD SEQ ID NO:2022 | LGSNRAS SEQ ID NO:10034 | MQALHIPLT SEQ ID NO:18046 |
| iPS:435109 | 21-225_92H5 | NA | CGGGCCAGTCAGGATGTTAT CACCTACTTAGCC SEQ ID NO:2023 | GGTGCATCCACCAGGGC CACT SEQ ID NO:10035 | CAGGAGTATAATGACTGGCC GTGCAGT SEQ ID NO:18047 |
| | | AA | RASQDVITYLA SEQ ID NO:2024 | GASTRAT SEQ ID NO:10036 | QEYNDWPCS SEQ ID NO:18048 |
| iPS:435111 | 21-225_92D6 | NA | AGGGCCAGTCAGAGTGTTTA CAGCAGTACTTAGCC SEQ ID NO:2025 | GGTGCATCCAGCCGGTC CACT SEQ ID NO:10037 | CAGCATTATGATAACTCTCC GTGGACG SEQ ID NO:18049 |
| | | AA | RASQSVYSSYLA SEQ ID NO:2026 | GASSRST SEQ ID NO:10038 | QHYDNSPWT SEQ ID NO:18050 |
| iPS:435113 | 21-225_92E6 | NA | AAGTCCAGTCAGAATATTTT ATCCAGCTCCAACAATAAGA ACTACTAACT SEQ ID NO:2027 | TGGACATCTACCCGGGA ATCC SEQ ID NO:10039 | CAGCAATATATTTTAGTGTTCCT CCGACG SEQ ID NO:18051 |
| | | AA | KSSQNILSSSNNKNYLT SEQ ID NO:2028 | WTSTRES SEQ ID NO:10040 | QQYFSVPPT SEQ ID NO:18052 |
| iPS:435115 | 21-225_77C5 | NA | AGGGCCAGTCAGAGTGTTTA CAGCAGTACTTAGCC SEQ ID NO:2029 | GGTGCATCCAGCCGGTC CACT SEQ ID NO:10041 | CAGCACTATGATAACTCACC GTGGACG SEQ ID NO:18053 |
| | | AA | RASQSVYSSYLA SEQ ID NO:2030 | GASSRST SEQ ID NO:10042 | QHYDNSPWT SEQ ID NO:18054 |
| iPS:435167 | 21-225_92F12 | NA | AAGTCCAGCCAGAGTGTTTT ACACAGGTCCAACAATTACA ACTACTTAGCG | TGGGCATCTACCCGGGA ATCC | CAGCAATATTATAGTACTCC TCCGACG |

FIGURE 49
(Continued)

| | | | | | | |
|---|---|---|---|---|---|---|
| iPS:435171 | 21-225_92F12 | AA | SEQ ID NO:2031 KSSQSVLHRSNNYNYLA | SEQ ID NO:10043 WASTRES | SEQ ID NO:18055 QQYYSTPPT | |
| iPS:435177 | 21-225_93C2 | NA | SEQ ID NO:2032 AGGGCCAGTCAGAGTGTTA CAGCAGTACTTAGCC | SEQ ID NO:10044 GGTGCATCCAGCCGGGC CACT | SEQ ID NO:18056 CAGCACTATGATAACTCACC GTGGACG | |
| | | AA | SEQ ID NO:2033 RASQSVYSSYLA | SEQ ID NO:10045 GASSRAT | SEQ ID NO:18057 QHYDNSPWT | |
| iPS:435183 | 21-225_93E4 | NA | SEQ ID NO:2034 AGGGCCAGTCAGAGTGTTA CAGCAGTACTTAGCC | SEQ ID NO:10046 GGTGCATCCAGCCGGTC CACT | SEQ ID NO:18058 CAGCACTCTGATAACTCACC GTGGACG | |
| | | AA | SEQ ID NO:2035 RASQSVYSSYLA | SEQ ID NO:10047 GASSRST | SEQ ID NO:18059 QHSDNSPWT | |
| iPS:435189 | 21-225_93E9 | NA | SEQ ID NO:2036 AGGGCCAGTCAGAGTGTGA CAGCAGTACCTAGCC | SEQ ID NO:10048 GGTGCATCCAGCAGGGC CCCT | SEQ ID NO:18060 CAGCAGTATGAAAGCTCACC GTGGACG | |
| | | AA | SEQ ID NO:2037 RASQSVDSSYLA | SEQ ID NO:10049 GASSRAP | SEQ ID NO:18061 QQYESSPWT | |
| iPS:435195 | 21-225_94D3 | NA | SEQ ID NO:2038 AGGGCCAGTCAGAGTGTTAG CAGCAGTACTTAGCC | SEQ ID NO:10050 GGTGCATCCAGCAGGGC CACT | SEQ ID NO:18062 CAGCATTATGATAGCTCACC GTGGACG | |
| | | AA | SEQ ID NO:2039 RASQSVSSRYLA | SEQ ID NO:10051 GASSRAT | SEQ ID NO:18063 QHYDSSPWT | |
| iPS:435197 | 21-225_94F3 | NA | SEQ ID NO:2040 CGGGCAAGTCAGGCCATTAG AGATGATTAGGC | SEQ ID NO:10052 GCTGCATCCAGTTGCAA AGT | SEQ ID NO:18064 CTCCAGCATTATAGTTACCC TCGGACG | |
| | | AA | SEQ ID NO:2041 RASQAIRDDLG | SEQ ID NO:10053 AASSLQS | SEQ ID NO:18065 LQHYSYPRT | |
| | | | SEQ ID NO:2042 | SEQ ID NO:10054 | SEQ ID NO:18066 | |

FIGURE 49
(Continued)

| | | | | | |
|---|---|---|---|---|---|
| iPS:435203 | 21-225_75A7 | NA | AAGTCCAGCCAGAGACTGTTTT ACACAGCTCCAACAATTATA ACTACTTAGCT SEQ ID NO:2043 | TGGACATCTACCCGGGA ATCC SEQ ID NO:10055 | CAGCAATATTTTAGTAGTCC TCCGACG SEQ ID NO:18067 |
| | | AA | KSSQTVLHSSNNYNYLA SEQ ID NO:2044 | WTSTRES SEQ ID NO:10056 | QQYFSSPPT SEQ ID NO:18068 |
| iPS:435209 | 21-225_75A10 | NA | AAGTCCAGCCAGAGAGTGTTT ACACAACTCCAACAATTACA ACTACTTAACT SEQ ID NO:2045 | TGGGCATCTACCCGGAA ATCC SEQ ID NO:10057 | CAGCAATATTATAGTTCTCC TCCGACG SEQ ID NO:18069 |
| | | AA | KSSQVLHNSNNYNYLT SEQ ID NO:2046 | WASTRKS SEQ ID NO:10058 | QQYSSPPT SEQ ID NO:18070 |
| iPS:435211 | 21-225_94E11 | NA | AAGTCCAGCCAGAGAGTGTTT ATTCAGTCCAACAATTATA ATTACTTAGCT SEQ ID NO:2047 | TGGGCATCTACCCGGGA ATCC SEQ ID NO:10059 | CAGCAATATCATAGTCTCC TCTGACG SEQ ID NO:18071 |
| | | AA | KSSQSVLFSSNNYNYLA SEQ ID NO:2048 | WASTRES SEQ ID NO:10060 | QQYHSSPLT SEQ ID NO:18072 |
| iPS:435215 | 21-225_94E12 | NA | AAGTCCAGCCAGAGAGTGTTT ACACAGGTCCAACAATTACA ACTACTTAGCG SEQ ID NO:2049 | TGGGCATCTACCCGGGA ATCC SEQ ID NO:10061 | CAGCAATATTATAGTACTCC TCCGACG SEQ ID NO:18073 |
| | | AA | KSSQSVLHRSNNYNYLA SEQ ID NO:2050 | WASTRES SEQ ID NO:10062 | QQYSTPPT SEQ ID NO:18074 |
| iPS:435217 | 21-225_94F12 | NA | AGGGCCAGTCAGAGTGTTTA CAGCAGCTACTTAGCG SEQ ID NO:2051 | GGTGCATCCAGCGCGGTC CACT SEQ ID NO:10063 | CAGCATTATGATAACTCACC GTGGACG SEQ ID NO:18075 |
| | | AA | RASQSVYSSYLA SEQ ID NO:2052 | GASSRST SEQ ID NO:10064 | QHYDNSPWT SEQ ID NO:18076 |

FIGURE 49
(Continued)

| | | | | | |
|---|---|---|---|---|---|
| iPS:435219 | 21-225_95D2 | NA | AGGGCCAGTCAGAGTGTTTA CAGCAGCTACTTAGCC SEQ ID NO:2053 | GGTGCATCCAGCCGGGC CACT SEQ ID NO:10065 | CAGCACTATGATAACTCACC GTGGACG SEQ ID NO:18077 |
| | | AA | RASQSVYSSYLA SEQ ID NO:2054 | GASSRAT SEQ ID NO:10066 | QHYDNSPWT SEQ ID NO:18078 |
| iPS:435221 | 21-225_95G2 | NA | AGGGCCAGTCAGAGTGTGT CAACAGCTTAGCC SEQ ID NO:2055 | GGTGCATCCACCAGGGC CACT SEQ ID NO:10067 | CAGCAGTATAATGACTGGCC GTGCAGT SEQ ID NO:18079 |
| | | AA | RASMSVVNSLA SEQ ID NO:2056 | GASTRAT SEQ ID NO:10068 | QQYNDWPCS SEQ ID NO:18080 |
| iPS:435227 | 21-225_95G4 | NA | AAGTCCAGCAGAGTGTTTT ATTCAGATCCAACAATTATA ATTACTTAGCT SEQ ID NO:2057 | TGGGCATCTACCCGGGA ATCC SEQ ID NO:10069 | CAGCAATATCATAGTTCTCC TCTGACG SEQ ID NO:18081 |
| | | AA | KSSQSVLFRSNNYNYLA SEQ ID NO:2058 | WASTRES SEQ ID NO:10070 | QQYHSSPLT SEQ ID NO:18082 |
| iPS:435235 | 21-225_95F9 | NA | AGGGCCAGTCAGAGTGTTTA CAGCAGCTACTTAGCC SEQ ID NO:2059 | GGTGCATCCAGCCGGTC CACT SEQ ID NO:10071 | CAGCACTATGATAACTCACC GTGGACG SEQ ID NO:18083 |
| | | AA | RASQSVYSSYLA SEQ ID NO:2060 | GASSRST SEQ ID NO:10072 | QHYDNSPWT SEQ ID NO:18084 |
| iPS:435237 | 21-225_95G9 | NA | AGGGCCAGTCAGAGTGTTTA CAGCAGCTACTTAGCG SEQ ID NO:2061 | GGTGCATCCAGCCGGTC CACT SEQ ID NO:10073 | CAGCACTATGATAACTCACC GTGGACG SEQ ID NO:18085 |
| | | AA | RASQSVYSSYLA SEQ ID NO:2062 | GASSRST SEQ ID NO:10074 | QHYDNSPWT SEQ ID NO:18086 |
| iPS:435239 | 21-225_95H10 | NA | AGGGCCAGTCAGAGTGTTTA CAGCAGCTACTTAGCC SEQ ID NO:2063 | GGTGCATCCAGCCGGGC CACT SEQ ID NO:10075 | CAGCACTATGATAACTCTCC GTGGACG SEQ ID NO:18087 |
| | | AA | RASQSVYSSYLA | GASSRAT | QHYDNSPWT |

FIGURE 49
(Continued)

| | | | | | |
|---|---|---|---|---|---|
| iPS:435245 | 21-225_95E12 | NA | SEQ ID NO:2064 AAGTCCAGCCAGAGTGTTT ATACAGCTCCAACAATGCGA ACTACTTAGCT | SEQ ID NO:10076 TGGGCATCTACCGGGA ATCC | SEQ ID NO:18088 CAGCAATATTATAGTACTCC GTGCAGT |
| | | AA | SEQ ID NO:2065 KSSQSVLYSSNNANYLA | SEQ ID NO:10077 WASTRES | SEQ ID NO:18089 QQYYSTPCS |
| iPS:435247 | 21-225_96G1 | NA | SEQ ID NO:2066 AGGGCCAGTCAGTCAGAGCGTTAG CAGCAGCTACTTAGCT | SEQ ID NO:10078 GGTGCATCCACCAGGGC CTCT | SEQ ID NO:18090 CAGCAGTATGGTAACTCACC GCTCACT |
| | | AA | SEQ ID NO:2067 RASQSVSSSYLA | SEQ ID NO:10079 GASTRAS | SEQ ID NO:18091 QQYGNSPLT |
| iPS:435249 | 21-225_96E2 | NA | SEQ ID NO:2068 AAGTCCAGCCAGAGTGTTT ACACAGCTCTAATAAAAGA ACTACTTAGCT | SEQ ID NO:10080 TGGGCATCTACCTGGA ATCC | SEQ ID NO:18092 CAGCAATATTATAGGACTCC GTGGACG |
| | | AA | SEQ ID NO:2069 KSSQSVLHSSNKKNYLA | SEQ ID NO:10081 WASTWES | SEQ ID NO:18093 QQYYRTPWT |
| iPS:435251 | 21-225_96A3 | NA | SEQ ID NO:2070 CGGGCAAGTCAGGGCATTAG AAATGATTAGGC | SEQ ID NO:10082 GCTGCATCCACTTTGCAA AGT | SEQ ID NO:18094 CTACAGCATAGTAATTACCC GCTCACT |
| | | AA | SEQ ID NO:2071 RASQGIRNDLG | SEQ ID NO:10083 AASTLQS | SEQ ID NO:18095 LQHSNYPLT |
| iPS:435253 | 21-225_96A4 | NA | SEQ ID NO:2072 CGGGCAAGTCAGGACATTAG AAATGATTAGGC | SEQ ID NO:10084 GGTGTATCCAGTTGCAA AGT | SEQ ID NO:18096 CTACAGCATAATGATTACCC ATTCACT |
| | | AA | SEQ ID NO:2073 RASQDIRNDLG | SEQ ID NO:10085 GVSSLQS | SEQ ID NO:18097 LQHNDYPFT |
| | | | SEQ ID NO:2074 RASQDIRNDLG | SEQ ID NO:10086 | SEQ ID NO:18098 |

FIGURE 49
(Continued)

| | | | | | | |
|---|---|---|---|---|---|---|
| iPS:435255 | 21-225_96D5 | NA | AAGTCCAGCCAGAGTGTTT GCACAGTCCAACAATATA ATTACTTAGCT SEQ ID NO:2075 | TGGGCATCTACCCGGGA ATCC SEQ ID NO:10087 | CAGCAATATTATAGTAGTCC ACCGACG SEQ ID NO:18099 |
| | | AA | KSSQSVLHSSNNYNYLA SEQ ID NO:2076 | WASTRES SEQ ID NO:10088 | QQYYSSPPT SEQ ID NO:18100 |
| iPS:435257 | 21-225_96H5 | NA | AAGTCCAGCCAGAGTGTTT GTACAGTCCAACAGTCACA ACTACTTAGCT SEQ ID NO:2077 | TGGGCATCTATCCGGGA ATCC SEQ ID NO:10089 | CAGCAATATTATAGTACTCC GTGCAGT SEQ ID NO:18101 |
| | | AA | KSSQSVLYSSNSHNYLA SEQ ID NO:2078 | WASIRES SEQ ID NO:10090 | QQYSTPCS SEQ ID NO:18102 |
| iPS:435259 | 21-225_96C6 | NA | CGGGCGAGTCAGGGCATTAG CAATTATTAGCC SEQ ID NO:2079 | GCTGCTTCCAGTTGCAA AGT SEQ ID NO:10091 | CACCAGTATAATGATTACCC ATTCACT SEQ ID NO:18103 |
| | | AA | RASQGISNYLA SEQ ID NO:2080 | AASSLQS SEQ ID NO:10092 | HQYNDYPFT SEQ ID NO:18104 |
| iPS:435267 | 21-225_96D10 | NA | AAGTCCAGTCAGAATATTTT ATCCAGTCCAACAATAAGA ACTACTTAACT SEQ ID NO:2081 | TGGACATCTACCCGGGA ATCC SEQ ID NO:10093 | CAGCAATATTTAGTGTTCCT CCGACG SEQ ID NO:18105 |
| | | AA | KSSQNILSSSNNKNYLT SEQ ID NO:2082 | WTSTRES SEQ ID NO:10094 | QQYFSVPPT SEQ ID NO:18106 |
| iPS:435273 | 21-225_97A2 | NA | AGGGCCAGTCAGAGTGTTTA CAGCAGTCACTTAGCC SEQ ID NO:2083 | GGTGCATCCAGCCGGTC CACT SEQ ID NO:10095 | CAGCATTCTGATAACTCACC GTGGACG SEQ ID NO:18107 |
| | | AA | RASQSVYSSYLA SEQ ID NO:2084 | GASSRST SEQ ID NO:10096 | QHSDNSPWT SEQ ID NO:18108 |

FIGURE 49
(Continued)

| | | | | | |
|---|---|---|---|---|---|
| iPS:435279 | 21-225_97H4 | NA | AAGTCCAGCCAGAGTGTTTT ATACACCTCCAACAATAACA ACTACTTAGCT SEQ ID NO:2085 | TGGGCATCTACCCGGGA ATCC SEQ ID NO:10097 | CAGCACTACAATGATACTCC ATGGAAG SEQ ID NO:18109 |
| | | AA | KSSQSVLYTSNNNNYLA SEQ ID NO:2086 | WASTRES SEQ ID NO:10098 | QHYNDTPWK SEQ ID NO:18110 |
| iPS:435281 | 21-225_97E5 | NA | AGGGCCAGTCAGAGTGTTTA CAGCAGCTACTTAGCC SEQ ID NO:2087 | GGTGCATCCAGCCGGGC CACT SEQ ID NO:10099 | CAGCACTCTGATAACTCACC GTGGACG SEQ ID NO:18111 |
| | | AA | RASQSVYSSYLA SEQ ID NO:2088 | GASSRAT SEQ ID NO:10100 | QHSDNSPWT SEQ ID NO:18112 |
| iPS:435291 | 21-225_146E1 | NA | CGGGCGAGTCAGGGTATTAA CAACTGGTTAGTC SEQ ID NO:2089 | GCTGCATCCAGTTGCAA AGT SEQ ID NO:10101 | CAACAGGCTAACAGTTTCCC ATTCACT SEQ ID NO:18113 |
| | | AA | RASQGINNWLV SEQ ID NO:2090 | AASSLQS SEQ ID NO:10102 | QQANSFPFT SEQ ID NO:18114 |
| iPS:435293 | 21-225_146F1 | NA | CGGGCAAGTCAGGGCATTAG AAATGATTTAGGC SEQ ID NO:2091 | GCTGCATCCAGTTGCAA AGT SEQ ID NO:10103 | CTTCAGCATAGTACTTACCC GCTCACT SEQ ID NO:18115 |
| | | AA | RASQGIRNDLG SEQ ID NO:2092 | AASSLQS SEQ ID NO:10104 | LQHSTYPLT SEQ ID NO:18116 |
| iPS:435295 | 21-225_146H1 | NA | CGGGCAAGTCAGGGCATTAG CGACTATTTAAAT SEQ ID NO:2093 | ACTACATCCAGTTGCAA AGT SEQ ID NO:10105 | CAACAGAGTTACAGTACCCC CACT SEQ ID NO:18117 |
| | | AA | RASQSISDYLN SEQ ID NO:2094 | TTSSLQS SEQ ID NO:10106 | QQSYSTPT SEQ ID NO:18118 |
| iPS:435297 | 21-225_146B3 | NA | AAGTCTAGTCAGAGCCTCCT GCATGGTGATGGAAAGACCT ATTTGTAT SEQ ID NO:2095 | GAAGTTTCCAACGGTTC TCT SEQ ID NO:10107 | ATGCAAAGTATACAGCTTCC GTGGACG SEQ ID NO:18119 |

FIGURE 49
(Continued)

| | | | KSSQSLLHGDGKTYLY | EVSNRFS | MQSIQLPWT |
|---|---|---|---|---|---|
| iPS:435299 | | AA | SEQ ID NO:2096 | SEQ ID NO:10108 | SEQ ID NO:18120 |
| | 21-225_146D4 | NA | AAGTCCAGCCAGAGTGTTTTATACAGCTCCAACAACAACTACTTAGCT | TGGGCATCTACCCGGGAATCC | CAGCAATATTATAGTACTCCGTGCAGT |
| | | | SEQ ID NO:2097 | SEQ ID NO:10109 | SEQ ID NO:18121 |
| | | AA | KSSQSVLYSSNNNNYLA | WASTRES | QQYYSTPCS |
| | | | SEQ ID NO:2098 | SEQ ID NO:10110 | SEQ ID NO:18122 |
| iPS:435301 | 21-225_146G4 | NA | AGGGCCAGTCAGAGTCAGAGAATATTATCAGCAGCTATTTAGCC | GGTGTATCTAGTCGGGCCACT | CAACAATATGGTAGGTCACCATTCAAT |
| | | | SEQ ID NO:2099 | SEQ ID NO:10111 | SEQ ID NO:18123 |
| | | AA | RASQNIISSYLA | GVSSRAT | QQYGRSPFN |
| | | | SEQ ID NO:2100 | SEQ ID NO:10112 | SEQ ID NO:18124 |
| iPS:435303 | 21-225_146A6 | NA | CGGGCGAGTCAGGGTATTAGCAACTGGTTAGCC | GCTGCATCCAGTTGCAAGGT | CAACAGACTGACAGTTTCCATTCACT |
| | | | SEQ ID NO:2101 | SEQ ID NO:10113 | SEQ ID NO:18125 |
| | | AA | RASQGISNWLA | AASSLQG | QQTDSFPFT |
| | | | SEQ ID NO:2102 | SEQ ID NO:10114 | SEQ ID NO:18126 |
| iPS:435305 | 21-225_146C9 | NA | AAGTCCAGCCAGAGTGTTTTACACAGCTCCAACAACAATTATAATTACTTAGCT | TGGGCATCTACCCGGAATCC | CAGCAATATTATAGTACTCCGTGCAGT |
| | | | SEQ ID NO:2103 | SEQ ID NO:10115 | SEQ ID NO:18127 |
| | | AA | KSSQSVLHSSNNYNYLA | WASTRKS | QQYYSTPCS |
| | | | SEQ ID NO:2104 | SEQ ID NO:10116 | SEQ ID NO:18128 |
| iPS:435307 | 21-225_146E9 | NA | CGGGCAAGTCAGAGCATTAGCGACTATTTAAAT | ACTACATCCAGTTGCAAAGT | CAACAGAGTTACAGTACCCCCACT |
| | | | SEQ ID NO:2105 | SEQ ID NO:10117 | SEQ ID NO:18129 |
| | | AA | RASQSISDYLN | TTSSLQS | QQSYSTPT |
| | | | SEQ ID NO:2106 | SEQ ID NO:10118 | SEQ ID NO:18130 |

FIGURE 49
(Continued)

| | | | | | |
|---|---|---|---|---|---|
| iPS:435309 | 21-225_146F9 | NA | AAGTCCAGCCAGAATATTT ACACAGTCCAACAATAACA ACTACTTAGCT SEQ ID NO:2107 | TGGGCATCTACCCGGGA ATCC SEQ ID NO:10119 | CAGCAATATTATACTACTCC GTGCAGT SEQ ID NO:18131 |
| | | AA | KSSQNILHSSNNNNYLA SEQ ID NO:2108 | WASTRES SEQ ID NO:10120 | QQYYTTPCS SEQ ID NO:18132 |
| iPS:435311 | 21-225_146H9 | NA | CGGGCAAGTCAGGGCATTAG AAATGATTTAGGC SEQ ID NO:2109 | GCTGCATCCAGTTTGCAA AGT SEQ ID NO:10121 | CTACAGCAATAATAGTTACCC GCTCACT SEQ ID NO:18133 |
| | | AA | RASQGIRNDLG SEQ ID NO:2110 | AASSLQS SEQ ID NO:10122 | LQHNSYPLT SEQ ID NO:18134 |
| iPS:435313 | 21-225_146G11 | NA | CGGGCAAGTCAGGACATTAG AAATAATTTTGGC SEQ ID NO:2111 | GCTGCATCCAGTTTGCAA AGT SEQ ID NO:10123 | CTCCAACATGATAGTTACCC GCTCACT SEQ ID NO:18135 |
| | | AA | RASQDIRNNFG SEQ ID NO:2112 | AASSLQS SEQ ID NO:10124 | LQHDSYPLT SEQ ID NO:18136 |
| iPS:435315 | 21-225_147B2 | NA | AAGTCTAGTCAGAGCCTCCT GCATAGTGAAGGAAAGACC TATTGTAT SEQ ID NO:2113 | GAAGTTTCCCACCGGGT CTCT SEQ ID NO:10125 | ATGCAAAGTACACAGTTTCC TCCCACT SEQ ID NO:18137 |
| | | AA | KSSQSLLHSEGKTYLY SEQ ID NO:2114 | EVSHRVS SEQ ID NO:10126 | MQSTQFPPT SEQ ID NO:18138 |
| iPS:435317 | 21-225_147D2 | NA | AGGGCCAGTCAGAGTGTTGG CAGCAGTACTTAGCC SEQ ID NO:2115 | GGTGCATCCAGCAGGGC CACT SEQ ID NO:10127 | CAGCAGTATGGTAGCTTATT CACT SEQ ID NO:18139 |
| | | AA | RASQSVGSSYLA SEQ ID NO:2116 | GASSRAT SEQ ID NO:10128 | QQYGSLFT SEQ ID NO:18140 |
| iPS:435319 | 21-225_147E3 | NA | AGGGCCAGTCAGAGTGTTAT CAGTAGTACTTAGCC SEQ ID NO:2117 | GGTGCATCCAGCAGGGC CACT SEQ ID NO:10129 | CAACAATATGGTAGGTCACC ATTCAAT SEQ ID NO:18141 |

FIGURE 49
(Continued)

| | | | | | | |
|---|---|---|---|---|---|---|
| iPS:435321 | | AA | RASQSVISSYLA SEQ ID NO:2118 | GASSRAT SEQ ID NO:10130 | QQYGRSPFN SEQ ID NO:18142 |
| | 21-225_147E4 | NA | AAGTCCAGCCAGAGTGTTTT ACACAGCTCCAACAATTACA ACTACTTAGCT SEQ ID NO:2119 | TGGGCATCTACCCGGGA ATCC SEQ ID NO:10131 | CAGCAATATTATAGTACTCC ATCCACT SEQ ID NO:18143 |
| iPS:435323 | | AA | KSSQSVLHSSNNYNYLA SEQ ID NO:2120 | WASTRES SEQ ID NO:10132 | QQYYSTPST SEQ ID NO:18144 |
| | 21-225_147D5 | NA | AAGTCCAGCCAGAGTGTTTT ATACAGCTCCAACAATAACA ACTACTTAGCT SEQ ID NO:2121 | TGGGCATCTACCCGGGA ATCC SEQ ID NO:10133 | CACCAATATTATAGTACTCC GTGCAGT SEQ ID NO:18145 |
| iPS:435325 | | AA | KSSQSVLYSSNNNNYLA SEQ ID NO:2122 | WASTRES SEQ ID NO:10134 | HQYYSTPCS SEQ ID NO:18146 |
| | 21-225_147H5 | NA | CGGGCAAGTCGGGGCATTAG AGATGATTAGGC SEQ ID NO:2123 | GCTGCATCCAGTTTGCAG AGT SEQ ID NO:10135 | CTACACGCATTATAGTTATCC TCGGACG SEQ ID NO:18147 |
| iPS:435327 | | AA | RASRGIRDDLG SEQ ID NO:2124 | AASSLQS SEQ ID NO:10136 | LQHYSYPRT SEQ ID NO:18148 |
| | 21-225_147G6 | NA | AAGTCCAGCCAGAGTGTTTT ATACAGCTCCAACAGTAACA ACTACTTAGCT SEQ ID NO:2125 | TGGGCATCTGCCCGGGA ATCC SEQ ID NO:10137 | CAGCAATATTATACTACTCC TCCCACT SEQ ID NO:18149 |
| iPS:435329 | | AA | KSSQSVLYSSNSNNYLA SEQ ID NO:2126 | WASARES SEQ ID NO:10138 | QQYYTPPT SEQ ID NO:18150 |
| | 21-225_147A8 | NA | AAGACTAGTCAGAGCCTCCT GCATAGTGAAGGAAAGACC TATTTGTAT SEQ ID NO:2127 | GAAGTTCCAACCGGTTC TCT SEQ ID NO:10139 | ATGCAAAGTATACAGCTAAT CACC SEQ ID NO:18151 |
| | | AA | KTSQSLLHSEGKTYLY | EVSNRFS | MQSIQLIT |

FIGURE 49
(Continued)

| | | | | | | |
|---|---|---|---|---|---|---|
| iPS:435331 | 21-225_147G8 | NA | SEQ ID NO:2128 AGGGCCAGTCAGAGAATTT CAGCAACTACTTAGCC | SEQ ID NO:10140 GGTGCATCCAGCAGGGC CACT | SEQ ID NO:8152 CAGCAGTATGATAGCTCACC GTGGACG |
| | | AA | SEQ ID NO:2129 RASQRIFSNYLA | SEQ ID NO:10141 GASSRAT | SEQ ID NO:8153 QQYDSSPWT |
| iPS:435333 | 21-225_147E9 | NA | SEQ ID NO:2130 CGGGCGAGTCAGGACATTAA CAATTATTAGCC | SEQ ID NO:10142 GCTGCATCCAGTTTGCAA AGT | SEQ ID NO:8154 CAACAGTATAATAGTTACCC TCTCACT |
| | | AA | SEQ ID NO:2131 RASQDINNYLA | SEQ ID NO:10143 AASSLQS | SEQ ID NO:8155 QQYNSYPLT |
| iPS:435335 | 21-225_147D10 | NA | SEQ ID NO:2132 CGGGCGAGTCAGCAGAATATTAG CAACTGGTTAACC | SEQ ID NO:10144 GCTGCATCCAGTTTGCAA AGT | SEQ ID NO:8156 CAACAGACTGACAGTTTCCC ATTCACT |
| | | AA | SEQ ID NO:2133 RASQNISNWLT | SEQ ID NO:10145 AASSLQS | SEQ ID NO:8157 QQTDSFPFT |
| iPS:435339 | 21-225_147B12 | NA | SEQ ID NO:2134 CGGGCGAGTCAGGGTATTAG CAACTGGTTAGCC | SEQ ID NO:10146 GCTGCATCCAGTTTGCAA AGT | SEQ ID NO:8158 CAACAGACTGACAGTTTCCC ATTCACT |
| | | AA | SEQ ID NO:2135 RASQGISNWLA | SEQ ID NO:10147 AASSLQS | SEQ ID NO:8159 QQTDSFPFT |
| iPS:435341 | 21-225_148B2 | NA | SEQ ID NO:2136 AAGTCTAGTCAGAGCCTCCT GCATGGTGATGGAAAGACCT ATTTTTAT | SEQ ID NO:10148 GAAGTTTCCCACCGGTTC TCT | SEQ ID NO:8160 ATGCAAAGTATACAGATTCC GTGGACG |
| | | AA | SEQ ID NO:2137 KSSQSLLHGDGKTYFY | SEQ ID NO:10149 EVSHRFS | SEQ ID NO:8161 MQSIQIPWT |
| iPS:435343 | 21-225_148E2 | NA | SEQ ID NO:2138 CGGGCGAGTCAGGGTATTAG CAACTGGTTAGCC | SEQ ID NO:10150 GCTGCATCCAGTTTGCAA AGT | SEQ ID NO:8162 CAACAGACTGACAGTTTCCC ATTCACT |
| | | | SEQ ID NO:2139 | SEQ ID NO:10151 | SEQ ID NO:8163 |

FIGURE 49
(Continued)

| | | | | | | |
|---|---|---|---|---|---|---|
| iPS:435345 | 21-225_148G3 | AA | RASQGISNWLA SEQ ID NO:2140 | AASSLQS SEQ ID NO:10152 | QQTDSFPFT SEQ ID NO:18164 |
| | | NA | AAGTCCAGCCAACGTGTTTT ACACAGCTCCAACAATTATA ACTACTTAGCT SEQ ID NO:2141 | TGGGCATCTACCCGGGA TTCC SEQ ID NO:10153 | CAGCAATATTATAGTACTCC ATTCACT SEQ ID NO:18165 |
| iPS:435347 | 21-225_148C4 | AA | KSSQRVLHSSNNYNYLA SEQ ID NO:2142 | WASTRDS SEQ ID NO:10154 | QQYYSTPFT SEQ ID NO:18166 |
| | | NA | CGGGCAAGTCAGAGCATTAT CAACTATTTAAAT SEQ ID NO:2143 | ACTGCATCCAGTTTACAG AGT SEQ ID NO:10155 | CAACAGAGTTACAGTACCCC CACT SEQ ID NO:18167 |
| iPS:435349 | 21-225_148F5 | AA | RASQSIINYLN SEQ ID NO:2144 | TASSLQS SEQ ID NO:10156 | QQSYSTPT SEQ ID NO:18168 |
| | | NA | AAGTCTAGTCAGAGCCTCCT GCATAGTAGTGAAGGAAAGACC TATTTGTAT SEQ ID NO:2145 | GAAGTTTCCTACCGGGTC TCT SEQ ID NO:10157 | ATGCAAAGTATACAGCTTCC GCTCACT SEQ ID NO:18169 |
| iPS:435351 | 21-225_148B6 | AA | KSSQSLLHSEGKTYLY SEQ ID NO:2146 | EVSYRVS SEQ ID NO:10158 | MQSIQLPLT SEQ ID NO:18170 |
| | | NA | CGGGCGAGTCAGGGCATTAG CAAATATTAGCC SEQ ID NO:2147 | GCTGCATCCAGTTTGCAA AGT SEQ ID NO:10159 | CAACAGTATAATAGTTTCCC ATTCACT SEQ ID NO:18171 |
| iPS:435353 | 21-225_148F8 | AA | RASQGISKYLA SEQ ID NO:2148 | AASSLQS SEQ ID NO:10160 | QQYNSFPFT SEQ ID NO:18172 |
| | | NA | AAGTCCAGCCAGAGTGCTTT ACACAGCTCCAACAATTACA ACTACTTAGCT SEQ ID NO:2149 | TGGGCATCTACCCGGAA ATCC SEQ ID NO:10161 | CAGCAATATTATAGTATTCC TCCGACG SEQ ID NO:18173 |
| | | AA | KSSQSALHSSNNYNYLA SEQ ID NO:2150 | WASTRKS SEQ ID NO:10162 | QQYSIPPT SEQ ID NO:18174 |

FIGURE 49 (Continued)

| | | | | | |
|---|---|---|---|---|---|
| iPS:435355 | 21-225_148H9 | NA | CGGGCAAGTCAGAGCATTAG TAACTATTTAAAT SEQ ID NO:2151 | ATTGCATCCAGTTGCAA AGT SEQ ID NO:10163 | CAACAGAGTTACAGTACCCC CACT SEQ ID NO:18175 |
| | | AA | RASQSISNYLN SEQ ID NO:2152 | IASSLQS SEQ ID NO:10164 | QQSYSTPT SEQ ID NO:18176 |
| iPS:435357 | 21-225_148G10 | NA | AAGTCTAGTCAGAGCCTCCT GCATGGTGATGGAAAGACCT ATTTGTAT SEQ ID NO:2153 | GAAGTTTCCAACCGGTTC TCT SEQ ID NO:10165 | ATGCAAAGTATACAGCTTCC GTGGACG SEQ ID NO:18177 |
| | | AA | KSSQSLLHGDGKTYLY SEQ ID NO:2154 | EVSNRFS SEQ ID NO:10166 | MQSIQLPWT SEQ ID NO:18178 |
| iPS:435359 | 21-225_148H10 | NA | AAGTCTAGTCAGAGCCTCCT GCATAGTGAGGGAAAGACC TATTTGTAT SEQ ID NO:2155 | GAAGTTTCCTACCGGGTC TCT SEQ ID NO:10167 | ATGCAGAGTATACAGCTTCC GCTCACT SEQ ID NO:18179 |
| | | AA | KSSQSLLHSEGKTYLY SEQ ID NO:2156 | EVSYRVS SEQ ID NO:10168 | MQSIQLPLT SEQ ID NO:18180 |
| iPS:435361 | 21-225_148E11 | NA | CGGGCAAGTCAGGGCATTAG AAATGATTTAGGC SEQ ID NO:2157 | GCTGCATCCAGTTGCAA AGT SEQ ID NO:10169 | CTACAGCATCGTAATTACCC GCTCACT SEQ ID NO:18181 |
| | | AA | RASQGIRNDLG SEQ ID NO:2158 | AASSLQS SEQ ID NO:10170 | LQHRNYPLT SEQ ID NO:18182 |
| iPS:435363 | 21-225_148F12 | NA | CGGGCAAGTCAGGGCATTAG AAATGCCTTAGGC SEQ ID NO:2159 | GCTGCATCCAGTTGCAA AGT SEQ ID NO:10171 | CTACAGCATAATAGTTACCC TCTCATT SEQ ID NO:18183 |
| | | AA | RASQGIRNALG SEQ ID NO:2160 | AASSLQS SEQ ID NO:10172 | LQHNSYPLI SEQ ID NO:18184 |
| iPS:435365 | 21-225_149F1 | NA | AAGTCTAGTCAGAGCCTCCT GCATGGTGATGGAAAGACC ATTTTTAT | GAAGTTTCCCACCGGTTC TCT | ATGCAAAGTATACAGATTCC GTGGACG |

FIGURE 49
(Continued)

| | | | | | | |
|---|---|---|---|---|---|---|
| iPS:435367 | 21-225_149F1 | AA | SEQ ID NO:2161<br>KSSQSLLHGDGKTYFY | SEQ ID NO:10173<br>EVSHRFS | SEQ ID NO:18185<br>MQSIQIPWT | |
| | | NA | SEQ ID NO:2162<br>CGGGCAAGTCAGGGCATTAG<br>AAATGATTTAGGC | SEQ ID NO:10174<br>GCTGCATCCAATTGCAA<br>AGT | SEQ ID NO:18186<br>CTACAGCATAATAGTTACCC<br>GCTCACT | |
| iPS:435369 | 21-225_149G1 | AA | SEQ ID NO:2163<br>RASQGIRNDLG | SEQ ID NO:10175<br>AASNLQS | SEQ ID NO:18187<br>LQHNSYPLT | |
| | | NA | SEQ ID NO:2164<br>AAGTCCAGCCAGAGTGTTTT<br>ATACAGTCCCAACAATAACA<br>ACTACTTAGCT | SEQ ID NO:10176<br>TGGGCATCTACCCGGGA<br>ATCC | SEQ ID NO:18188<br>CAGCAATATTATAGTACTCC<br>GTGCAGT | |
| iPS:435371 | 21-225_149A2 | AA | SEQ ID NO:2165<br>KSSQSVLYSPNNNNYLA | SEQ ID NO:10177<br>WASTRES | SEQ ID NO:18189<br>QQYYSTPCS | |
| | | NA | SEQ ID NO:2166<br>CGGGCAAGTCAGAGCATTAG<br>CAGTTATTTAAAT | SEQ ID NO:10178<br>ACTGCATCCAGTTTGCAA<br>AGT | SEQ ID NO:18190<br>CAACAGAGTTACAGTATCC<br>CACT | |
| iPS:435373 | 21-225_149A3 | AA | SEQ ID NO:2167<br>RASQSISSYLN | SEQ ID NO:10179<br>TASSLQS | SEQ ID NO:18191<br>QQSYSIPT | |
| | | NA | SEQ ID NO:2168<br>AAGTCCAGCCAGAGACTGTTT<br>ACACAACTCCAATAATCACA<br>ATTACTTTGCT | SEQ ID NO:10180<br>TGGGCATCTACCCTGAG<br>ATCC | SEQ ID NO:18192<br>CAGCAATATTATAGTACTCC<br>TCCGACG | |
| iPS:435375 | 21-225_149E3 | AA | SEQ ID NO:2169<br>KSSQTVLHNSNHNYFA | SEQ ID NO:10181<br>WASTLRS | SEQ ID NO:18193<br>QQYYSTPPT | |
| | | NA | SEQ ID NO:2170<br>AAGTCCAGCCAGAGTGTTTT<br>ATCCAGCTCCAACGATAACA<br>ACTACTTAGCT | SEQ ID NO:10182<br>TGGTCATCTACCCGGGA<br>ATCC | SEQ ID NO:18194<br>CACCAATATTATAGTTATCC<br>TCCGACG | |
| | 21-225_149H4 | AA | SEQ ID NO:2171<br>KSSQSVLSSSNDNNYLA | SEQ ID NO:10183<br>WSSTRES | SEQ ID NO:18195<br>HQYYSYPPT | |

FIGURE 49
(Continued)

| | | | | | | |
|---|---|---|---|---|---|---|
| iPS:435377 | 21-225_149G5 | NA | SEQ ID NO:2172 CGGGCAAGTCAGGGCATTAG AAATGCCTTAGGC | SEQ ID NO:10184 GCTGCATCCAGTTTGCAA AGT | SEQ ID NO:18196 CTACAGCATAATAGTTACCC TCTCACT | |
| | | AA | SEQ ID NO:2173 RASQGIRNALG | SEQ ID NO:10185 AASSLQS | SEQ ID NO:18197 LQHNSYPLT | |
| iPS:435379 | 21-225_149B6 | NA | SEQ ID NO:2174 CGGGCGAGTCAGGGTATTAT CAGTTGGTTAGCC | SEQ ID NO:10186 GCTGCATCCAGTTTGCAA AGT | SEQ ID NO:18198 CAACAGGGTAACAGTTTCCC ATTCACT | |
| | | AA | SEQ ID NO:2175 RASQGIISWLA | SEQ ID NO:10187 AASSLQS | SEQ ID NO:18199 QQGNSFPFT | |
| iPS:435381 | 21-225_149C6 | NA | SEQ ID NO:2176 CGGGCGAGTCAGGGTATTAG CAACTGGTTAGCC | SEQ ID NO:10188 GCTGCATCCAGTTTGCAA GGT | SEQ ID NO:18200 CAACAGACTGACAGTTTCCC ATTCACT | |
| | | AA | SEQ ID NO:2177 RASQGISNWLA | SEQ ID NO:10189 AASSLQG | SEQ ID NO:18201 QQTDSFPFT | |
| iPS:435383 | 21-225_149D7 | NA | SEQ ID NO:2178 AGGGCCAGTCAGAGTATTAT CAGCAACTACTTAGCC | SEQ ID NO:10190 GGTGTATCTAGTAGGGC CACT | SEQ ID NO:18202 CAACAATATGGTCGGTCACC ATTCACT | |
| | | AA | SEQ ID NO:2179 RASQSIISNYLA | SEQ ID NO:10191 GVSSRAT | SEQ ID NO:18203 QQYGRSPFN | |
| iPS:435391 | 21-225_149F8 | NA | SEQ ID NO:2180 CGGGCGAGTCAGGGCATTAG CAACTGGTTAGCC | SEQ ID NO:10192 GCTGCATCCAGTTTGCAA AGT | SEQ ID NO:18204 CAACAGACTGACAGTTTCCC ATTCACT | |
| | | AA | SEQ ID NO:2181 RASQGISNWLA | SEQ ID NO:10193 AASSLQS | SEQ ID NO:18205 QQTDSFPFT | |
| iPS:435393 | 21-225_149D10 | NA | SEQ ID NO:2182 CGGGCAAGTCGGGGCATTAG AAATGATTTAGGC | SEQ ID NO:10194 GCTGCATCCAGTTTGCAG AGT | SEQ ID NO:18206 CTACAGCATTATAGTTATCC TCGGACG | |
| | | AA | SEQ ID NO:2183 RASRGIRNDLG | SEQ ID NO:10195 AASSLQS | SEQ ID NO:18207 LQHYSYPRT | |

FIGURE 49 (Continued)

| | | | | | |
|---|---|---|---|---|---|
| iPS:435395 | 21-225_149D11 | NA | SEQ ID NO:2184 CGGGCAAGTCAGAGAATATTAG CAACTGGTTAACC | SEQ ID NO:10196 GCTGCATCCAGTTTGCAA AGT | SEQ ID NO:18208 CAACAGACTGACAGTTCCC ATTCACT |
| | | AA | SEQ ID NO:2185 RASQNISNWLT | SEQ ID NO:10197 AASSLQS | SEQ ID NO:18209 QQTDSFPFT |
| iPS:435397 | 21-225_149F12 | NA | SEQ ID NO:2186 CGGGCAAGTCAGGGCATTAG AAATGATTTAGGC | SEQ ID NO:10198 GCTGCATCCAGTTTGCAA AGT | SEQ ID NO:18210 CTACAGCATAATAGTACC GCTCACT |
| | | AA | SEQ ID NO:2187 RASQGIRNDLG | SEQ ID NO:10199 AASNLQS | SEQ ID NO:18211 LQHNSYPLT |
| iPS:435399 | 21-225_150D2 | NA | SEQ ID NO:2188 AAGTCCAGCCAGAGTGTTTT ATACAGATCCAACAGTAAGA AATACTTAACT | SEQ ID NO:10200 TGGGCATCTACCCGGAA ATCC | SEQ ID NO:18212 CAGCAATATATTTAGTACTCC GTACAAT |
| | | AA | SEQ ID NO:2189 KSSQSVLYRSNSKKYLT | SEQ ID NO:10201 WASTRKS | SEQ ID NO:18213 QQYFSTPYN |
| iPS:435401 | 21-225_150E2 | NA | SEQ ID NO:2190 CGGGCAAGTCAGGGCATTGG AAATGATTTAGGC | SEQ ID NO:10202 GCTGCATCCAGTTTGCAA AGT | SEQ ID NO:18214 CTACAACATTATAGTTCCC GTACAGT |
| | | AA | SEQ ID NO:2191 RASQGIGNDLG | SEQ ID NO:10203 AASSLQS | SEQ ID NO:18215 LQHYSFPYS |
| iPS:435403 | 21-225_150C5 | NA | SEQ ID NO:2192 CGGGCAAGTCAGGGTATTAA CAACTGGTTAGCC | SEQ ID NO:10204 GCTGCATCCAGTTTGCAA GGT | SEQ ID NO:18216 CAACAGACTGACAGTTCCC ATTCACT |
| | | AA | SEQ ID NO:2193 RASQGINNWLA | SEQ ID NO:10205 AASSLQG | SEQ ID NO:18217 QQTDSFPFT |
| iPS:435405 | 21-225_150B7 | NA | SEQ ID NO:2194 AAGTCCAGCCAGAATGTTTT ATACAGTCCCACAATAACA ACTACTTAGCT | SEQ ID NO:10206 TGGGCATCTACCCGGAA ATCC | SEQ ID NO:18218 CAGCAATATATAGTACTCC ATTCACT |

FIGURE 49
(Continued)

| | | | | | | |
|---|---|---|---|---|---|---|
| iPS:435407 | 21-225_150B7 | AA | SEQ ID NO:2195<br>KSSQNVLYSSHNNNYLA | SEQ ID NO:10207<br>WASTRKS | SEQ ID NO:18219<br>QQYYSTPFT | |
| | | NA | SEQ ID NO:2196<br>CGGGCAAGTCAGGGCATTAG<br>AAATGATTTAGGC | SEQ ID NO:10208<br>GCTGCATCCAATTTGCAA<br>AGT | SEQ ID NO:18220<br>CTACAGCATAATAGTTACCC<br>GCTCACT | |
| iPS:435409 | 21-225_150E7 | AA | SEQ ID NO:2197<br>RASQGIRNDLG | SEQ ID NO:10209<br>AASNLQS | SEQ ID NO:18221<br>LQHNSYPLT | |
| | | NA | SEQ ID NO:2198<br>CGGGGAGTCAGGGCATTAG<br>CCATTATTTAGCC | SEQ ID NO:10210<br>GTTGCATCCAGTTTGCAA<br>AAT | SEQ ID NO:18222<br>CAACAGTATAATAATTACCC<br>GCTCACT | |
| iPS:435413 | 21-225_150G8 | AA | SEQ ID NO:2199<br>RASQGISHYLA | SEQ ID NO:10211<br>VASSLQN | SEQ ID NO:18223<br>QQYNNYPLT | |
| | | NA | SEQ ID NO:2200<br>AAGTCTAGTCAGAGCCTCGT<br>GCATGGTGGTGATGGAAAGACCT<br>ATTTGTAT | SEQ ID NO:10212<br>GAAGTTTCCAACCGGTTC<br>TCT | SEQ ID NO:18224<br>ATGCAAAGTATACAGCTTCC<br>GTGGACG | |
| iPS:435413 | 21-225_150B11 | AA | SEQ ID NO:2201<br>KSSQSLVHGDGKTYLY | SEQ ID NO:10213<br>EVSNRFS | SEQ ID NO:18225<br>MQSIQLPWT | |
| | | NA | SEQ ID NO:2202<br>CGGGCAAGTCAGAGCATTAG<br>CAGCTATTTAAAT | SEQ ID NO:10214<br>ACTGCATCCAGTTTGCAA<br>AGT | SEQ ID NO:18226<br>CAACAGAGTTACAGTATTTA<br>CACT | |
| iPS:435415 | 21-225_150C11 | AA | SEQ ID NO:2203<br>RASQSISSYLN | SEQ ID NO:10215<br>TASSLQS | SEQ ID NO:18227<br>QQSYSIYT | |
| | | NA | SEQ ID NO:2204<br>AAGTCTAGTCAGAGCCTCCT<br>GCATAGTGAGGGAAAGACC<br>TATTTGTAT | SEQ ID NO:10216<br>GAAGTTTCCTACCGGTTC<br>TCT | SEQ ID NO:18228<br>ATGCAAGGTATACAGCTTCC<br>GCTCACT | |
| iPS:435417 | 21-225_150D11 | AA | SEQ ID NO:2205<br>KSSQSLLHSEGKTYLY | SEQ ID NO:10217<br>EVSYRFS | SEQ ID NO:18229<br>MQGIQLPLT | |
| | | | SEQ ID NO:2206 | SEQ ID NO:10218 | SEQ ID NO:18230 | |

FIGURE 49
(Continued)

| | | | | | |
|---|---|---|---|---|---|
| iPS:435419 | 21-225_150C12 | NA | CGGGCAAGTCAGAGCATTAG CGACTATTAAAT SEQ ID NO:2207 | ACTACATCCAGTTGCAA AGT SEQ ID NO:10219 | CAACAGAGTTCAGTACCCC CACT SEQ ID NO:18231 |
| | | AA | RASQSISDYLN SEQ ID NO:2208 | TTSSLQS SEQ ID NO:10220 | QQSFSTPT SEQ ID NO:18232 |
| iPS:435421 | 21-225_151F1 | NA | AGGGCCAGTCAGAGTATTAA CATCAATATAGCC SEQ ID NO:2209 | GGTGCATCCACCAGGGC CACT SEQ ID NO:10221 | CAGCAGTATAATGACTGGCG TCCGTGGACG SEQ ID NO:18233 |
| | | AA | RASQSININIA SEQ ID NO:2210 | GASTRAT SEQ ID NO:10222 | QQYNDWPPWT SEQ ID NO:18234 |
| iPS:435423 | 21-225_151G5 | NA | AAGTCTAGTCAGGCGCTCCT GCATGGTGATGGAAAGACCT ATTTGTAT SEQ ID NO:2211 | GAAGTTCCAACCGGTTC TCT SEQ ID NO:10223 | ATGCAAAGTATACAGGTTCC GTGGACG SEQ ID NO:18235 |
| | | AA | KSSQRLLHGDGKTYLY SEQ ID NO:2212 | EVSNRFS SEQ ID NO:10224 | MQSIQVPWT SEQ ID NO:18236 |
| iPS:435425 | 21-225_151B12 | NA | CGGGCAAGTCAGAGCATTAG CAACTTTTAAAT SEQ ID NO:2213 | ACTGCATCCAGTTGGA AAGT SEQ ID NO:10225 | CAACAGAGTTACAGTACCCC CACT SEQ ID NO:18237 |
| | | AA | RASQSISNFLN SEQ ID NO:2214 | TASSLES SEQ ID NO:10226 | QQSYSTPT SEQ ID NO:18238 |
| iPS:435427 | 21-225_151C9 | NA | CGGGCCAGTCAGGGCATTAG CAAGTATTTAGCC SEQ ID NO:2215 | GATGCATCCAGGTTGCA AAGT SEQ ID NO:10227 | CATCAGTATAAACATTACCC GATCACC SEQ ID NO:18239 |
| | | AA | RASQGISKYLA SEQ ID NO:2216 | DASRLQS SEQ ID NO:10228 | HQYKHYPIT SEQ ID NO:18240 |
| iPS:435429 | 21-225_151A10 | NA | AAGTCTAGTCAGAGCCTCCT GCATGGTGATGGAAAGACCT ATTTGTAT SEQ ID NO:2217 | GAAGTTTCCCACCGGTTC TCT SEQ ID NO:10229 | ATGCAAAGTATACAGATTCC GTGGACG SEQ ID NO:18241 |

FIGURE 49
(Continued)

| | | | | | | |
|---|---|---|---|---|---|---|
| iPS:435431 | | AA | KSSQSLLHGDGKTYLY SEQ ID NO:2218 | EVSHRFS SEQ ID NO:10230 | MQSIQIPWT SEQ ID NO:18242 |
| | 21-225_152D2 | NA | CGGGCAAGTCAGAGCATTAG CGACTATTTAAAT SEQ ID NO:2219 | ACTACATCCAGTTTGCAA AGT SEQ ID NO:10231 | CAACAGAGTTACAGTACCCC CACT SEQ ID NO:18243 |
| iPS:435433 | | AA | RASQSISDYLN SEQ ID NO:2220 | TTSSLQS SEQ ID NO:10232 | QQSYSTPT SEQ ID NO:18244 |
| | 21-225_152E3 | NA | AAGTCCAGCCAGAGTGTTT ACACAGTCCAACAATTACA ACTACTTAGTT SEQ ID NO:2221 | TGGGCATCTACCCGGGA ATCC SEQ ID NO:10233 | CAGCAATATTACAGTACTCC ATTCACT SEQ ID NO:18245 |
| iPS:435435 | | AA | KSSQSVLHSSNNYNYLV SEQ ID NO:2222 | WASTRES SEQ ID NO:10234 | QQYYSTPFT SEQ ID NO:18246 |
| | 21-225_152H3 | NA | AAGTCCAGCCAGAGTGTTT GCACAGTCCAACAATTACA ACTACTTAACT SEQ ID NO:2223 | TGGGCATCTACCCGGAA ATCC SEQ ID NO:10235 | CAGCAATATTATAGTACTCC GTGCAGT SEQ ID NO:18247 |
| iPS:435437 | | AA | KSSQSVLHSSNNYNYLT SEQ ID NO:2224 | WASTRKS SEQ ID NO:10236 | QQYYSTPCS SEQ ID NO:18248 |
| | 21-225_152F4 | NA | AAGTCCAGCCAGAGTGTTT ATACAGTCCAACAATTACA ACTACTTAGCT SEQ ID NO:2225 | TGGGCATCTACCCGGAA ATCC SEQ ID NO:10237 | CAGCAATATTTTAATACTCC TCCCACT SEQ ID NO:18249 |
| iPS:435439 | | AA | KSSQSVLYSSNNYNYLA SEQ ID NO:2226 | WASTRKS SEQ ID NO:10238 | QQYFNTPPT SEQ ID NO:18250 |
| | 21-225_152G4 | NA | CGGGCAAGTCAGAGCATTAG CGACTATTTAAAT SEQ ID NO:2227 | ACTACATCCAGTTTGCAA AGT SEQ ID NO:10239 | CAACAGAGTTACAGTACCCC CACT SEQ ID NO:18251 |
| | | AA | RASQSISDYLN SEQ ID NO:2228 | TTSSLQS SEQ ID NO:10240 | QQSYSTPT SEQ ID NO:18252 |

FIGURE 49
(Continued)

| | | | | | |
|---|---|---|---|---|---|
| iPS:435441 | 21-225_152F6 | NA | AAGTCTAGTCAGAGCCTCCGGCATGGTGATGGAAAGACCTATTTGACT SEQ ID NO:2229 | GAAATTTCCAAGCGGTTCACT SEQ ID NO:10241 | ATGCAAAGTATACAGGTTCCGTGGACG SEQ ID NO:18253 |
| | | AA | KSSQSLRHGDGKTYLT SEQ ID NO:2230 | EISKRFT SEQ ID NO:10242 | MQSIQVPWT SEQ ID NO:18254 |
| iPS:435443 | 21-225_152E7 | NA | AGGGCCAGTCAGAGTGTTATCAGCAGCTACTTAGCC SEQ ID NO:2231 | GGTGTATCTAGTAGGGCCACT SEQ ID NO:10243 | CAACAATATGGTAGGTCACCATTCAAT SEQ ID NO:18255 |
| | | AA | RASQSVISSYLA SEQ ID NO:2232 | GVSSRAT SEQ ID NO:10244 | QQYGRSPFN SEQ ID NO:18256 |
| iPS:435445 | 21-225_152F7 | NA | CGGGCAAGTCAGGGCATTAGAAATGATTTAGGC SEQ ID NO:2233 | GCTACATCCAGTTTGCAAAGT SEQ ID NO:10245 | CTACAGCATTATAATTTCCCGTACAGT SEQ ID NO:18257 |
| | | AA | RASQGIRNDLG SEQ ID NO:2234 | ATSSLQS SEQ ID NO:10246 | LQHYNFPYS SEQ ID NO:18258 |
| iPS:435447 | 21-225_152H7 | NA | CGGGCGAGTCAGGATATTAGCAACTGGTTAGGC SEQ ID NO:2235 | GCTGCATCCAGTTTGCAAGGT SEQ ID NO:10247 | CAACAGACTGACAGTTTCCCATTCACT SEQ ID NO:18259 |
| | | AA | RASQDISNWLA SEQ ID NO:2236 | AASSLQG SEQ ID NO:10248 | QQTDSFPFT SEQ ID NO:18260 |
| iPS:435449 | 21-225_152H9 | NA | CGGGCAAGTCAGGGCATTAGAAATGATTTAGGC SEQ ID NO:2237 | GCTGCATCCAGTTTGCAAAGT SEQ ID NO:10249 | CTACAGCATAGTAATTACCCGCTCACT SEQ ID NO:18261 |
| | | AA | RASQGIRNDLG SEQ ID NO:2238 | AASSLQS SEQ ID NO:10250 | LQHSNYPLT SEQ ID NO:18262 |
| iPS:435451 | 21-225_152D10 | NA | AAGTCCAGCCAGAGTGTTTATACAGCTCCAACAATAAGAACTACTTAGCT SEQ ID NO:2239 | TGGGCATCTACCCGGGAATCC SEQ ID NO:10251 | CAGCAATATTATCGTAGTCCTAGT SEQ ID NO:18263 |

FIGURE 49
(Continued)

| | | | | | | |
|---|---|---|---|---|---|---|
| iPS:435453 | 21-225_152G10 | AA | KSSQSVLYSSNNKNYLA<br>SEQ ID NO:2240 | CGGGCGAGTCAGGGTATTAG<br>CAACTGGTTAGCC<br>SEQ ID NO:2241 | WASTRES<br>SEQ ID NO:10252 | QQYYRSPS<br>SEQ ID NO:18264 |
| | | NA | | | GCTGCATCCAGTTGCAA<br>AGT<br>SEQ ID NO:10253 | CAACAGACTGACAGTTCCC<br>ATTCACT<br>SEQ ID NO:18265 |
| iPS:435455 | 21-225_152B11 | AA | RASQGISNWLA<br>SEQ ID NO:2242 | | AASSLQS<br>SEQ ID NO:10254 | QQTDSFPFT<br>SEQ ID NO:18266 |
| | | NA | | CGGGCAAGTCAGAGCATTAG<br>CGACTATTTAAAT<br>SEQ ID NO:2243 | ACTACATCCAGTTGCAA<br>AGT<br>SEQ ID NO:10255 | CAACAGAGTTACAGTACCCC<br>CACT<br>SEQ ID NO:18267 |
| iPS:435457 | 21-225_152C11 | AA | RASQSISDYLN<br>SEQ ID NO:2244 | | TTSSLQS<br>SEQ ID NO:10256 | QQSYSTPT<br>SEQ ID NO:18268 |
| | | NA | | AAGTCTAGTCAGAGCCTCCT<br>GCATGGTGATGGAAAGACCT<br>ATTTATAT<br>SEQ ID NO:2245 | GAAGTTCCAACCGGTTC<br>TCT<br>SEQ ID NO:10257 | ATGCAAAGTATACAGATTCC<br>GTGGACG<br>SEQ ID NO:18269 |
| iPS:435459 | 21-225_152E12 | AA | KSSQSLLHGDGKTYLY<br>SEQ ID NO:2246 | | EVSNRFS<br>SEQ ID NO:10258 | MQSIQIPWT<br>SEQ ID NO:18270 |
| | | NA | | ACGTCCAGCCAGAGTATTT<br>ACACAGCTCCAATAATTACA<br>ACTACTTAGCT<br>SEQ ID NO:2247 | TGGGCATCTACCCGGGA<br>ATCC<br>SEQ ID NO:10259 | CAACAATATTATAGTGGTCC<br>GTGCAGT<br>SEQ ID NO:18271 |
| iPS:435461 | 21-225_153A1 | AA | TSSQSILHSSNNYNYLA<br>SEQ ID NO:2248 | | WASTRES<br>SEQ ID NO:10260 | QQYYSGPCS<br>SEQ ID NO:18272 |
| | | NA | | CGGGGAGTCAGGTCATTAG<br>CAATTATTATTAGCC<br>SEQ ID NO:2249 | GCTGCATCCAGTTGCGA<br>AGT<br>SEQ ID NO:10261 | CAACAGTATCATAGTTACCC<br>ATTCACT<br>SEQ ID NO:18273 |
| | | AA | RASQVISNYLA<br>SEQ ID NO:2250 | | AASSLRS<br>SEQ ID NO:10262 | QQYHSYPFT<br>SEQ ID NO:18274 |

FIGURE 49
(Continued)

| iPS: | Clone | Type | Seq 1 | Seq 2 | Seq 3 |
|---|---|---|---|---|---|
| iPS:435463 | 21-225_153D2 | NA | AAGTCTAGTCAGAGCCTCCGGCATGGTGATGGAAAGACCTATTTGACT SEQ ID NO:2251 | GAAGTTCCAAGCGGTTCACT SEQ ID NO:10263 | ATGCAAAGTATACAGGTTCCGTGGACG SEQ ID NO:18275 |
| | | AA | KSSQSLRHGDGKTYLT SEQ ID NO:2252 | EVSKRFT SEQ ID NO:10264 | MQSIQVPWT SEQ ID NO:18276 |
| iPS:435465 | 21-225_153A6 | NA | AGGGCCAGTCAGAGTGTTATCAGCAGCTACTTAGCC SEQ ID NO:2253 | GGTGTATCTAGTAGGGCCACT SEQ ID NO:10265 | CAACAATATGGTAGGTCACCATTCAAT SEQ ID NO:18277 |
| | | AA | RASQSVISSYLA SEQ ID NO:2254 | GVSSRAT SEQ ID NO:10266 | QQYGRSPFN SEQ ID NO:18278 |
| iPS:435467 | 21-225_153B9 | NA | AAGTCCAGCCAGAGTGTTTTATACAGCTCCAACAATAAGAACTACTTAGCT SEQ ID NO:2255 | TGGGCATCTACCCGGGAATTT SEQ ID NO:10267 | CAGCAATATAATCGTAGTCTTAGT SEQ ID NO:18279 |
| | | AA | KSSQSVLYSSNNKNYLA SEQ ID NO:2256 | WASTREF SEQ ID NO:10268 | QQYNRSLS SEQ ID NO:18280 |
| iPS:435469 | 21-225_153G9 | NA | AAGTCTAGTCAGAGCCTCCTGCATAGTGATGGAAAGACCTATTTGTAT SEQ ID NO:2257 | GAAGTTCCAAGCGGTTCTCT SEQ ID NO:10269 | ATGCAAAATATAAAGTATCCGCTCACT SEQ ID NO:18281 |
| | | AA | KSSQSLLHSDGKTYLY SEQ ID NO:2258 | EVSNRFS SEQ ID NO:10270 | MQNIKYPLT SEQ ID NO:18282 |
| iPS:435471 | 21-225_153F11 | NA | AAGTCCAGCCAGAGTGTTTTATACAGCTCCAACAATTACAAGTACTTAGCT SEQ ID NO:2259 | TGGGCATCTACCCGGAAATCC SEQ ID NO:10271 | CAGCAATATTATAGTACTCCGTGCAGT SEQ ID NO:18283 |
| | | AA | KSSQSVLYSSNNYKYLA SEQ ID NO:2260 | WASTRKS SEQ ID NO:10272 | QQYYSTPCS SEQ ID NO:18284 |

FIGURE 49
(Continued)

| | | | | | | |
|---|---|---|---|---|---|---|
| iPS:435475 | 21-225_154H6 | NA | AAGTCCAGCCAGAGTGTTT ACACAGTTCCAACAATTACA ACTATTTAGCT SEQ ID NO:2261 | TGGACATCTACCCGGAA ATCC SEQ ID NO:10273 | CAGCATTATTATAGTACTCC GTGCAGT SEQ ID NO:18285 |
| | | AA | KSSQSVLHSSNNYNYLA SEQ ID NO:2262 | WTSTRKS SEQ ID NO:10274 | QHYYSTPCS SEQ ID NO:18286 |
| iPS:435479 | 21-225_154E9 | NA | CGGGCGAGTCAGGATATTAG CAACTGGTTAGCC SEQ ID NO:2263 | GCTGCATCCAGTTTGCAA AGT SEQ ID NO:10275 | CAACAGGGTAACAGTTTCCC GCTCACT SEQ ID NO:18287 |
| | | AA | RASQDISNWLA SEQ ID NO:2264 | AASSLQS SEQ ID NO:10276 | QQGNSFPLT SEQ ID NO:18288 |
| iPS:435481 | 21-225_154A11 | NA | AGGTCAAGCCAGAGTGTTT ACACAGCTCCAACAATTATA ACTACTTAGCT SEQ ID NO:2265 | TGGGCATCTAAACGGGA TTCC SEQ ID NO:10277 | CAGCAATATTTTAGTTCTCCT CGGACG SEQ ID NO:18289 |
| | | AA | RSSQSVLHSSNNYNYLA SEQ ID NO:2266 | WASKRDS SEQ ID NO:10278 | QQYFSSPRT SEQ ID NO:18290 |
| iPS:435483 | 21-225_155A4 | NA | CGGGCGAGTCAGGGTATTAG CAACTGGTTAGCC SEQ ID NO:2267 | GCTGCATCCAGTTTGCAA GGT SEQ ID NO:10279 | CACCAGACTGACAGTTTCCC ATTCACT SEQ ID NO:18291 |
| | | AA | RASQGISNWLA SEQ ID NO:2268 | AASSLQG SEQ ID NO:10280 | HQTDSFPFT SEQ ID NO:18292 |
| iPS:435485 | 21-225_155B4 | NA | CGGGCGAGTCAGGATATTAG CAACTGGTTAGCC SEQ ID NO:2269 | GCTGCATCCAGTTTGCAA GGT SEQ ID NO:10281 | CACCAGACTGACAGTTTCCC ATTCACT SEQ ID NO:18293 |
| | | AA | RASQDISNWLA SEQ ID NO:2270 | AASSLQG SEQ ID NO:10282 | HQTDSFPFT SEQ ID NO:18294 |
| iPS:435487 | 21-225_155C4 | NA | CGGGCAAGTCAGAGCATTAG CAGCTATTTAAAT SEQ ID NO:2271 | ACTGCATCCAGTTTGCAA AGT SEQ ID NO:10283 | CAACAGAGTTACAGTACCC CACT SEQ ID NO:18295 |

FIGURE 49
(Continued)

| | | | | | | | | |
|---|---|---|---|---|---|---|---|---|
| iPS:435489 | 21-225_155A5 | AA | RASQSISSYLN | SEQ ID NO:2272 | TASSLQS | SEQ ID NO:10284 | QQSYSTPT | SEQ ID NO:18296 |
| | | NA | AAGTCTAGTCAGAGCCTCCTGCATGGTGATGGAAAGACCTATTTGTAT | SEQ ID NO:2273 | GAAGTTTCCAATCGGTTCTCT | SEQ ID NO:10285 | ATGCAAAGTATACAGGTTCCGTGGACG | SEQ ID NO:18297 |
| iPS:435491 | 21-225_155E5 | AA | KSSQSLLHGDGKTYLY | SEQ ID NO:2274 | EVSNRFS | SEQ ID NO:10286 | MQSIQVPWT | SEQ ID NO:18298 |
| | | NA | AAGTCCAGCCAGAGTGTTTTATCCAGCTCCAACAATAATAATTATTAGCT | SEQ ID NO:2275 | TGGGCATCTACCCGGAAATCC | SEQ ID NO:10287 | CAGCAATATTATAGTACTCCGTGCAGT | SEQ ID NO:18299 |
| iPS:435495 | 21-225_155B6 | AA | KSSQSVLSSSNNNNYLA | SEQ ID NO:2276 | WASTRKS | SEQ ID NO:10288 | QQYYSTPCS | SEQ ID NO:18300 |
| | | NA | AAGTCCAGCCAGAGTGTTTTACACAGCTCCAATAATTACAACTACTTAGCT | SEQ ID NO:2277 | TGGACATCTACCCGGAATCC | SEQ ID NO:10289 | CAACAATATTATAGTACTCCGTGCAGT | SEQ ID NO:18301 |
| iPS:435497 | 21-225_155H9 | AA | KSSQSVLHSSNNYNYLA | SEQ ID NO:2278 | WTSTRES | SEQ ID NO:10290 | QQYYSTPCS | SEQ ID NO:18302 |
| | | NA | AGGGCCAGTCAGAGTGTTAGTAGTAACTTAGCC | SEQ ID NO:2279 | GGTGCATCCACCAGGGCCACT | SEQ ID NO:10291 | CAGCAGTATGATGACTGGCCTCCGTGGACG | SEQ ID NO:18303 |
| iPS:435499 | 21-225_156G1 | AA | RASQSVSSNLA | SEQ ID NO:2280 | GASTRAT | SEQ ID NO:10292 | QQYDDWPPWT | SEQ ID NO:18304 |
| | | NA | CGGGCAAGTCAGGGCATTAGAAATGATTTAGGC | SEQ ID NO:2281 | GCTGCATCCAGTTGCAAAGT | SEQ ID NO:10293 | CTACAGCATAGTAATTACCCGCTCACT | SEQ ID NO:18305 |
| | | AA | RASQGIRNDLG | SEQ ID NO:2282 | AASSLQS | SEQ ID NO:10294 | LQHSNYPLT | SEQ ID NO:18306 |

FIGURE 49
(Continued)

| | | | | | |
|---|---|---|---|---|---|
| iPS:435501 | 21-225_156H1 | NA | AAGTCCAGCCAGAGTGTTTT ATACAGCTCCAACAATAACA ACTACTTAGCT<br>SEQ ID NO:2283 | TGGGCATCTACCCGGGA ATCC<br>SEQ ID NO:10295 | CACCAATATTATAGTACTCC GTGCAGT<br>SEQ ID NO:8307 |
| | | AA | KSSQSVLYSSNNNNYLA<br>SEQ ID NO:2284 | WASTRES<br>SEQ ID NO:10296 | HQYYSTPCS<br>SEQ ID NO:8308 |
| iPS:435503 | 21-225_156E4 | NA | CGGGCAAGTCAGAGAGCATTAG CAGCTATTTAAAT<br>SEQ ID NO:2285 | ACTGCATCCAGTTTGCAA AGT<br>SEQ ID NO:10297 | CAACAGAGTTACAGTGCCCC CACT<br>SEQ ID NO:8309 |
| | | AA | RASQSISSYLN<br>SEQ ID NO:2286 | TASSLQS<br>SEQ ID NO:10298 | QQSYSAPT<br>SEQ ID NO:8310 |
| iPS:435505 | 21-225_157C1 | NA | CGGGCGAGTCAGGGCATTAG CAATTATTTAGCC<br>SEQ ID NO:2287 | GCTGCATCCAGTTTGCTA AGT<br>SEQ ID NO:10299 | CAACAGTATAATAGTTTTCC ATTCACT<br>SEQ ID NO:8311 |
| | | AA | RASQGISNYLA<br>SEQ ID NO:2288 | AASSLS<br>SEQ ID NO:10300 | QQYNSFPFT<br>SEQ ID NO:8312 |
| iPS:435509 | 21-225_157H1 | NA | CGGGCGAGTCAGGACATTAG CAATTATTTAGTC<br>SEQ ID NO:2289 | GCTGCATCCAGTTTGCAA AGT<br>SEQ ID NO:10301 | CAACAATATCATAGTTACCC ATTCACT<br>SEQ ID NO:8313 |
| | | AA | RASQDISNYLV<br>SEQ ID NO:2290 | AASSLQS<br>SEQ ID NO:10302 | QQYHSYPFT<br>SEQ ID NO:8314 |
| iPS:435511 | 21-225_157C3 | NA | CGGGCAAGTCAGGGCATTAG AAATGATTTAGGC<br>SEQ ID NO:2291 | GCTGCATCCAGTTTGCAA AGT<br>SEQ ID NO:10303 | CTACAGCATAATAGTTACCC ATTCACT<br>SEQ ID NO:8315 |
| | | AA | RASQGIRNDLG<br>SEQ ID NO:2292 | AASSLQS<br>SEQ ID NO:10304 | LQHNSYPFT<br>SEQ ID NO:8316 |
| iPS:435513 | 21-225_157F3 | NA | CGGGCAAGTCAGAACATTAG CAGTTATTTAAAT<br>SEQ ID NO:2293 | ACTGCATCCAGTTTGCAA AGT<br>SEQ ID NO:10305 | CAACAGAGTTACAATACCCC CACGTGGACG<br>SEQ ID NO:8317 |
| | | AA | RASQNISSYLN | TASSLQS | QQSYNTPTWT |

FIGURE 49
(Continued)

| | | | | | | |
|---|---|---|---|---|---|---|
| iPS:435515 | 21-225_157E4 | NA | SEQ ID NO:2294 CGGGCGAGTCAGGGCATTAG CAATTATTTAGCC | SEQ ID NO:10306 GCTGCATCCAGTTTGCGA AGT | SEQ ID NO:18318 CAACAGTATCATAGTTATCC ATTCACT | |
| | | AA | SEQ ID NO:2295 RASQGISNYLA | SEQ ID NO:10307 AASSLRS | SEQ ID NO:18319 QQYHSYPFT | |
| iPS:435521 | 21-225_157H4 | NA | SEQ ID NO:2296 CGGGCAAGTCAGGGCATTAG AAATGATTTAGGC | SEQ ID NO:10308 CCTGCATCCAGTTTACAA ACT | SEQ ID NO:18320 CTACAGGATAATAGTTACCC ATTCACT | |
| | | AA | SEQ ID NO:2297 RASQGIRNDLG | SEQ ID NO:10309 PASSLQT | SEQ ID NO:18321 LQDNSYPFT | |
| iPS:435523 | 21-225_157G5 | NA | SEQ ID NO:2298 CGGGCGAGTCAGGGCATTAG CAATTATTTAGCC | SEQ ID NO:10310 GCTGCATCCAGTTTACAA AGT | SEQ ID NO:18322 CAACAGTATAATAGTTATCC ATTCACT | |
| | | AA | SEQ ID NO:2299 RASQGINNYLA | SEQ ID NO:10311 AASSLQS | SEQ ID NO:18323 QQYNSYPFT | |
| iPS:435525 | 21-225_157E7 | NA | SEQ ID NO:2300 CGGGCAAGTCAGAGCTTTAG CAGCTATTTAAAT | SEQ ID NO:10312 GCTGCATCCAGTTTGCAA AGT | SEQ ID NO:18324 CAAGAGAGTTATAGTATCCG CTTCGCC | |
| | | AA | SEQ ID NO:2301 RASQSFSSYLN | SEQ ID NO:10313 AASSLQS | SEQ ID NO:18325 QESYSIRFA | |
| iPS:435527 | 21-225_157G7 | NA | SEQ ID NO:2302 CGGGCAAGTCAGGGCATTAG AAATGATTTAGGC | SEQ ID NO:10314 GTTGCATCCAGTTTGCAA AGT | SEQ ID NO:18326 ATACAGGATAATAGTCACCC ATTCACT | |
| | | AA | SEQ ID NO:2303 RASQGIRNDLG | SEQ ID NO:10315 VASSLQS | SEQ ID NO:18327 IQDNSHPFT | |
| iPS:435529 | 21-225_157H7 | NA | SEQ ID NO:2304 CGGGCGAGTCAGGACATTAG CAATTTTTAGCC | SEQ ID NO:10316 ACTGCATCCAGTTTGCAA AGT | SEQ ID NO:18328 CAACAGTATCATAGTTACCC GATCACC | |
| | | AA | SEQ ID NO:2305 RASQDISNFLA | SEQ ID NO:10317 TASSLQS | SEQ ID NO:18329 QQYHSYPIT | |

FIGURE 49
(Continued)

| | | | | | | |
|---|---|---|---|---|---|---|
| iPS:435531 | 21-225_157G8 | NA | SEQ ID NO:2306 AAGTCTAGTCAGAGCCTCCTGCATGGTGATGGAAAGACCTATTTATAT | SEQ ID NO:10318 GAAATTTCCAAGCGGTTCTCT | SEQ ID NO:18330 ATGCAAAGTATACAGGTTCCGTGGACG |
| | | AA | SEQ ID NO:2307 KSSQSLLHGDGKTYLY | SEQ ID NO:10319 EISKRFS | SEQ ID NO:18331 MQSIQVPWT |
| iPS:435533 | 21-225_157H8 | NA | SEQ ID NO:2308 CGGGCAAGTCAGGGCATTAGAAATGATTTAGGC | SEQ ID NO:10320 GCTGCATCCAGTTTGCAAAGT | SEQ ID NO:18332 CTACAGCATAATAGTTACCATTCACT |
| | | AA | SEQ ID NO:2309 RASQGIRNDLG | SEQ ID NO:10321 AASSLQS | SEQ ID NO:18333 LQHNSYPFT |
| iPS:435535 | 21-225_157H10 | NA | SEQ ID NO:2310 CGGGCGAGTCAGGGCATTAGCAATTATTAGCC | SEQ ID NO:10322 ACTGCATCCAATTTGCAAAGT | SEQ ID NO:18334 CAACAGTATCATAGTTACCATTCACT |
| | | AA | SEQ ID NO:2311 RASQGITNYLA | SEQ ID NO:10323 TASNLQS | SEQ ID NO:18335 QQYHSYPFT |
| iPS:435537 | 21-225_157H12 | NA | SEQ ID NO:2312 CGGGCAAGTCAGGGCATTAGAAATGATTTGGC | SEQ ID NO:10324 GCTGCATCCAGTTTACAGAGT | SEQ ID NO:18336 CTACAGCATTATAGTTACCATTCACT |
| | | AA | SEQ ID NO:2313 RASQGIRNDFG | SEQ ID NO:10325 AASSLQS | SEQ ID NO:18337 LQHYSYPFT |
| iPS:435539 | 21-225_158G1 | NA | SEQ ID NO:2314 CGGGCAAGTCAGGGCATTAGAAATGATTTAGGC | SEQ ID NO:10326 ACTGCATCCAATTTGCAAAGT | SEQ ID NO:18338 CTACAGCATAATAGTTACCGTGGACG |
| | | AA | SEQ ID NO:2315 RASQGIRNDLG | SEQ ID NO:10327 TASNLQS | SEQ ID NO:18339 LQHNSYPWT |
| iPS:435543 | 21-225_158D4 | NA | SEQ ID NO:2316 CGGGCAAGTCAGGACATTAGAAAGGATTTAGGC | SEQ ID NO:10328 GCTGCATCCAGTTTGCAAAGT | SEQ ID NO:18340 CTACAGCATTATAGTTACCTCGGACG |
| | | | SEQ ID NO:2317 | SEQ ID NO:10329 | SEQ ID NO:18341 |

FIGURE 49 (Continued)

| | | | | | | |
|---|---|---|---|---|---|---|
| iPS:435545 | 21-225_158F4 | AA | RASQDIRKDLG SEQ ID NO:2318 | AASSLQS SEQ ID NO:10330 | LQHYSYPRT SEQ ID NO:18342 | |
| | | NA | CGGGCAAGTCAGGAACATTAG AAAGTATTTACAT SEQ ID NO:2319 | ACTGCATCCACTTTACAA AGT SEQ ID NO:10331 | CAACAGAGTTACAATATTTC ATTCACT SEQ ID NO:18343 | |
| iPS:435547 | 21-225_158F5 | AA | RASQNIRKYLH SEQ ID NO:2320 | TASTLQS SEQ ID NO:10332 | QQSYNISFT SEQ ID NO:18344 | |
| | | NA | CGGGCAAGTCAGGGCATTAG AAATGATTAGGC SEQ ID NO:2321 | GCTGCATCCAGTTTGCAA AGT SEQ ID NO:10333 | CTACAGGATAATAGTCACC ATTCACT SEQ ID NO:18345 | |
| iPS:435549 | 21-225_158H5 | AA | RASQGIRNDLG SEQ ID NO:2322 | AASSLQS SEQ ID NO:10334 | LQDNSHPFT SEQ ID NO:18346 | |
| | | NA | CGGGCAAGTCAGGGCATGA GAATTGATTTAGGG SEQ ID NO:2323 | CGTGCATCCAGTTGCAA AGT SEQ ID NO:10335 | GTACAGCATAATAGTTACC TCTCACT SEQ ID NO:18347 | |
| iPS:435551 | 21-225_158H6 | AA | RASQGMRIDLG SEQ ID NO:2324 | RASSLQS SEQ ID NO:10336 | VQHNSYPLT SEQ ID NO:18348 | |
| | | NA | CGGGCAAGTCAGGGACATTAG AAGTGATTTAGGC SEQ ID NO:2325 | ACTGCATCCAGTTGCAA AGT SEQ ID NO:10337 | CTACAGCATAATAGTTACC ATTCACT SEQ ID NO:18349 | |
| iPS:435553 | 21-225_158G8 | AA | RASQGIRSDLG SEQ ID NO:2326 | TASSLQS SEQ ID NO:10338 | LQHNSYPFT SEQ ID NO:18350 | |
| | | NA | CGGGCAAGTCAGGACATTAG AAATGATTTAGGC SEQ ID NO:2327 | ACTGCATCCAGTTGCAA AGT SEQ ID NO:10339 | CTACAGCATAATAGTTACC ATTCACT SEQ ID NO:18351 | |
| iPS:435557 | 21-225_158B12 | AA | RASQDIRNDLG SEQ ID NO:2328 | TASSLQS SEQ ID NO:10340 | LQHNSYPFT SEQ ID NO:18352 | |
| | | NA | AAGTCCAGCCAGAATGTTTT ACACAGCTCCAACAATAACA ACTACTTAACT | TGGGCATCTACCCGGGA ATCC | CAGCAATATTATAGTACTCC TCCGACG | |

FIGURE 49 (Continued)

| | | | | | |
|---|---|---|---|---|---|
| iPS:435559 | 21-225_158B12 | AA | SEQ ID NO:2329<br>KSSQNVLHSSNNNYLT | SEQ ID NO:2329<br>WASTRES | SEQ ID NO:18353<br>QQYYSTPPT |
| | | NA | SEQ ID NO:2330<br>CGGGCGAGTCAGGGCATTAA<br>CAATTATTAGCC | SEQ ID NO:10342<br>GCTGCATCCAGTTACAA<br>AGT | SEQ ID NO:18354<br>CAACAGTATCATAGTTACC<br>ATTCACT |
| iPS:435561 | 21-225_158H12 | AA | SEQ ID NO:2331<br>RASQGINNYLA | SEQ ID NO:10343<br>AASSLQS | SEQ ID NO:18355<br>QQYHSYPFT |
| | | NA | SEQ ID NO:2332<br>CGGGCAAGTCAGGCGTCAG<br>AAATGATTTAGGC | SEQ ID NO:10344<br>GATGCATCCAATTGCA<br>AAGT | SEQ ID NO:18356<br>CTACAGCATCATAGTTTCC<br>GATCACC |
| iPS:435563 | 21-225_159F1 | AA | SEQ ID NO:2333<br>RASQRVRNDLG | SEQ ID NO:10345<br>DASNLQS | SEQ ID NO:18357<br>LQHSFPIT |
| | | NA | SEQ ID NO:2334<br>CGGGCAAGTCAGAGCATTAG<br>CAAATATTTAAAT | SEQ ID NO:10346<br>GCTACATCCAATTGCAA<br>AGT | SEQ ID NO:18358<br>CAACAGAGTTACAGTCTCC<br>GGTCACT |
| iPS:435565 | 21-225_159H2 | AA | SEQ ID NO:2335<br>RASQSISKYLN | SEQ ID NO:10347<br>ATSNLQS | SEQ ID NO:18359<br>QQSYSLPVT |
| | | NA | SEQ ID NO:2336<br>CAGGCGAGTCAGGACATTAG<br>CGACTATTTAAAT | SEQ ID NO:10348<br>GATGCCTCCACTTTGGAA<br>ACA | SEQ ID NO:18360<br>CAACAATATGATAATCTCCC |
| iPS:435569 | 21-225_159C4 | AA | SEQ ID NO:2337<br>QASQDISDYLN | SEQ ID NO:10349<br>DASTLET | SEQ ID NO:18361<br>QQYDNLPIT |
| | | NA | SEQ ID NO:2338<br>CGGACAAGTCAGGACATTAG<br>AAATGATTTAGGC | SEQ ID NO:10350<br>GCTGCATCCAGTTGCAA<br>AGT | SEQ ID NO:18362<br>CTACAGCATAATAGTTATCC<br>GATCACC |
| iPS:435569 | 21-225_159C5 | AA | SEQ ID NO:2339<br>RTSQGIRNDLG | SEQ ID NO:10351<br>AASSLQS | SEQ ID NO:18363<br>LQHNSYPFT |
| | | NA | SEQ ID NO:2340<br>CGGGCAAGTCAGGACATTAG<br>AAAGGATTTAGG | SEQ ID NO:10352<br>GCTGCATCCAGTTGCAA<br>AGT | SEQ ID NO:18364<br>CTACAGCATCATAGTTATCC<br>TCGGACG |

FIGURE 49
(Continued)

| | | | | | | |
|---|---|---|---|---|---|---|
| | 21-225_159C8 | AA | SEQ ID NO:2341 RASQDIRKDLG | SEQ ID NO:10353 AASSLQS | SEQ ID NO:18365 LQHHSYPRT | |
| iPS:435573 | 21-225_159D8 | NA | SEQ ID NO:2342 CGGGCAAGTCGGGACATTGG AAATGATTAGGC | SEQ ID NO:10354 GCTGCATCCAGTTGCAA AGT | SEQ ID NO:18366 CTACAGCATTATAGTTACC TCGGACG | |
| iPS:435575 | 21-225_159H11 | AA | SEQ ID NO:2343 RASRDIGNDLG | SEQ ID NO:10355 AASSLQS | SEQ ID NO:18367 LQHYSYPRT | |
| | | NA | SEQ ID NO:2344 CGGGGAGTCAGGGCATTAG CAAATATTAGTC | SEQ ID NO:10356 GCTGCATCCAGTCTGCA AAGT | SEQ ID NO:18368 CAACAGTATAATAGTTACC ATTCACT | |
| iPS:435577 | 21-225_160B1 | AA | SEQ ID NO:2345 RASQGISKYLV | SEQ ID NO:10357 AASSLQS | SEQ ID NO:18369 QQYNSYPFT | |
| | | NA | SEQ ID NO:2346 AAGTCTAGTCAGAGCCTCCT GCATGGTGATGGGAAGACCT ATTTCTAT | SEQ ID NO:10358 GAAGTATCCAAGCGGTT CTCT | SEQ ID NO:18370 ATGCAAAGTATACAGATTCC GTGGACG | |
| iPS:435579 | 21-225_160G1 | AA | SEQ ID NO:2347 KSSQSLLHGDGKTYFY | SEQ ID NO:10359 EVSKRFS | SEQ ID NO:18371 MQSIQIPWT | |
| | | NA | SEQ ID NO:2348 CGGGGAGTCAGGACATTAA CAATTATTAGCC | SEQ ID NO:10360 GCTTCATCCAGTTGCAA AGT | SEQ ID NO:18372 CAACAATATCATAGTTACC ATTCACT | |
| iPS:435581 | 21-225_160H1 | AA | SEQ ID NO:2349 RASQDINNYLA | SEQ ID NO:10361 ASSSLQS | SEQ ID NO:18373 QQYHSYPFT | |
| | | NA | SEQ ID NO:2350 CGGGCAAGTCAGGACATTAG AAATGATTAGGC | SEQ ID NO:10362 GCTGCATCCAGTTGCAG AAT | SEQ ID NO:18374 CTACAGCATAATAGTTCCC GTGGACG | |
| | | AA | SEQ ID NO:2351 RASQDIRNDLG | SEQ ID NO:10363 AASSLQN | SEQ ID NO:18375 LQHNSFPWT | |
| | | | SEQ ID NO:2352 | SEQ ID NO:10364 | SEQ ID NO:18376 | |

FIGURE 49
(Continued)

| | | | | | |
|---|---|---|---|---|---|
| iPS:435583 | 21-225_160F2 | NA | CGGGCAAGTCAGGGCATTAG AAATGATTAGGC<br>SEQ ID NO:2353 | ACTGCATCCAATTTGCAA AGT<br>SEQ ID NO:10365 | CTACAGCATAATAGTTACCC GTGGACG<br>SEQ ID NO:18377 |
| | | AA | RASQGIRNDLG<br>SEQ ID NO:2354 | TASNLQS<br>SEQ ID NO:10366 | LQHNSYPWT<br>SEQ ID NO:18378 |
| iPS:435585 | 21-225_160G3 | NA | CGGGCGAGTCAGGACATTAA CAATTATTAGCC<br>SEQ ID NO:2355 | GCTTCATCCAGTTTGCAA AGT<br>SEQ ID NO:10367 | CAACAATATCATAGTTACCC ATTCACT<br>SEQ ID NO:18379 |
| | | AA | RASQDINNYLA<br>SEQ ID NO:2356 | ASSSLQS<br>SEQ ID NO:10368 | QQYHSYPFT<br>SEQ ID NO:18380 |
| iPS:435587 | 21-225_160H3 | NA | CGGGCAAGTCAGGGCATTAG AAATGATTAGGC<br>SEQ ID NO:2357 | GCTGCATCCAGTTTGCAA AGT<br>SEQ ID NO:10369 | CTACAGCATAGTAATTACCC GCTCACT<br>SEQ ID NO:18381 |
| | | AA | RASQGIRNDLG<br>SEQ ID NO:2358 | AASSLQS<br>SEQ ID NO:10370 | LQHSNYPLT<br>SEQ ID NO:18382 |
| iPS:435589 | 21-225_160A4 | NA | AAGTCCAGCAGGCCAGAGTGTTT ACACAGCTCCAACAATAATA ACTACTTAGCT<br>SEQ ID NO:2359 | TGGGCATCTACCCGGGA ATCC<br>SEQ ID NO:10371 | CAGCAATATTATAATAGTCC GTGCAGT<br>SEQ ID NO:18383 |
| | | AA | KSSQSVLHSSNNNNYLA<br>SEQ ID NO:2360 | WASTRES<br>SEQ ID NO:10372 | QQYYNSPCS<br>SEQ ID NO:18384 |
| iPS:435591 | 21-225_160C4 | NA | CGGGCAAGTCAGGACATTAG AAAGGATTAGGG<br>SEQ ID NO:2361 | GCTGCATCCAGTTTGCAA AGT<br>SEQ ID NO:10373 | CTACAGCATTATAGTTACCC TCGGACG<br>SEQ ID NO:18385 |
| | | AA | RASQDIRKDLG<br>SEQ ID NO:2362 | AASSLQS<br>SEQ ID NO:10374 | LQHSYPRT<br>SEQ ID NO:18386 |
| iPS:435593 | 21-225_160F4 | NA | CGGGCAAGTCAGGGCATTAG AAATGATTAGGC<br>SEQ ID NO:2363 | GTTGCATCCAGTTTGCAA AGT<br>SEQ ID NO:10375 | ATACAGGATAATAGTCACCC ATTCACT<br>SEQ ID NO:18387 |
| | | AA | RASQGIRNDLG | VASSLQS | IQDNSHPFT |

FIGURE 49
(Continued)

| | | | | | |
|---|---|---|---|---|---|
| iPS:435595 | 21-225_160H4 | NA | SEQ ID NO:2364 CGGGCGAGTCAGGACATTAG TAATTATTAGTC | SEQ ID NO:10376 GTTGCATCCAGTTTGCAA AGT | SEQ ID NO:18388 CAACAGTATAATAGTTACCC TCTCACT |
| | | AA | SEQ ID NO:2365 RASQDISNYLV | SEQ ID NO:10377 VASSLQS | SEQ ID NO:18389 QQYNSYPLT |
| iPS:435599 | 21-225_160B10 | NA | SEQ ID NO:2366 CGGGCAAGTCAGGGCATTAG AAATGATTTAGGC | SEQ ID NO:10378 GCTGCATCCAGTTTGCAA AGT | SEQ ID NO:18390 CTACAGCATAGTAGTTACCC GCTCACT |
| | | AA | SEQ ID NO:2367 RASQGIRNDLG | SEQ ID NO:10379 AASSLQS | SEQ ID NO:18391 LQHSSYPLT |
| iPS:435601 | 21-225_160G10 | NA | SEQ ID NO:2368 AAGTCTAGTCAGAGCCTCCT GCACGGTGATGGAAAGACCT ATTTGTAT | SEQ ID NO:10380 GAAGTTTCCAAAACGGTT CTCT | SEQ ID NO:18392 ATGCAAAGTATACAGCTTCC GTGGACG |
| | | AA | SEQ ID NO:2369 KSSQSLLHGDGKTYLY | SEQ ID NO:10381 EVSKRFS | SEQ ID NO:18393 MQSIQLPWT |
| iPS:435605 | 21-225_161A4 | NA | SEQ ID NO:2370 AGGTCCAGTCAGAGTGTTAA CAGCAACTTAGCC | SEQ ID NO:10382 GGTGCATCCATCAGGGC CACT | SEQ ID NO:18394 CAGCAGTATAATAACTGGTG GACG |
| | | AA | SEQ ID NO:2371 RSSQSVNSNLA | SEQ ID NO:10383 GASIRAT | SEQ ID NO:18395 QQYNNWWT |
| iPS:435607 | 21-225_161G4 | NA | SEQ ID NO:2372 CAGGGCGAGTCAGGACATTA CAATTATTTAAAT | SEQ ID NO:10384 GATGCATCCAATTTGGA AACA | SEQ ID NO:18396 CAACAGTATGATATTCTCCC GATCACC |
| | | AA | SEQ ID NO:2373 QASQDIYNYLN | SEQ ID NO:10385 DASNLET | SEQ ID NO:18397 QQYDILPIT |
| iPS:435609 | 21-225_161F7 | NA | SEQ ID NO:2374 CGGGCAAGTCAGGGCATTAG AAATGATTTGGGC | SEQ ID NO:10386 GCTGCATCCACTTTGCAA AGT | SEQ ID NO:18398 CTACTATATATTCGTTACCA TTCACT |
| | | | SEQ ID NO:2375 | SEQ ID NO:10387 | SEQ ID NO:18399 |

FIGURE 49 (Continued)

| | | | RASQGIRNDLG | AASTLQS | LLYIYRYPFT |
|---|---|---|---|---|---|
| iPS:435611 | | AA | SEQ ID NO:2376 | SEQ ID NO:10388 | SEQ ID NO:18400 |
| | 21-225_161F10 | NA | CAGGCGAGTCAGGGACATTTA CAACCATTAAGT | GATGCATCCAATTGGGA AACA | CAACAGTATGAAAATCTCCC GCTCACC |
| | | | SEQ ID NO:2377 | SEQ ID NO:10389 | SEQ ID NO:18401 |
| iPS:435613 | | AA | QASQDIYNHLS | DASNWET | QQYENLPLT |
| | | | SEQ ID NO:2378 | SEQ ID NO:10390 | SEQ ID NO:18402 |
| | 21-225_161D11 | NA | CGGGCAAGTCAGGCATTAG AAATGATTTGGGC | GCTGCATCCACCTTGCAA AGT | CTACAATATAATCGTTACC ATTCACT |
| | | | SEQ ID NO:2379 | SEQ ID NO:10391 | SEQ ID NO:18403 |
| iPS:435615 | | AA | RASQGIRNDLG | AASTLQS | LQYNRYPFT |
| | | | SEQ ID NO:2380 | SEQ ID NO:10392 | SEQ ID NO:18404 |
| | 21-225_161G12 | NA | CGGGCAAGTCAGGACATTAG AAAGGATTTAGGG | GCTGCATCCAGTTGCAA AGT | CTACAGCATCATAGTTATCC TCGGACG |
| | | | SEQ ID NO:2381 | SEQ ID NO:10393 | SEQ ID NO:18405 |
| iPS:435617 | | AA | RASQDIRKDLG | AASSLQS | LQHHSYPRT |
| | | | SEQ ID NO:2382 | SEQ ID NO:10394 | SEQ ID NO:18406 |
| | 21-225_162F2 | NA | CGGGCAAGTCAGGACATTAG AAATGATTTAGGC | GCTGCATCCAGTTGCAA AGT | ATACAGGATAATAGTCACC ATTCACT |
| | | | SEQ ID NO:2383 | SEQ ID NO:10395 | SEQ ID NO:18407 |
| iPS:435621 | | AA | RASQGIRNDLG | AASSLQS | IQDNSHPFT |
| | | | SEQ ID NO:2384 | SEQ ID NO:10396 | SEQ ID NO:18408 |
| | 21-225_162H3 | NA | CGGGCAAGTCAGGGCATTAG AAATGATTTAGGC | GCTGCATCCAGTTGCAA AGT | CTACAGGATAATAGTCACC ATTCACT |
| | | | SEQ ID NO:2385 | SEQ ID NO:10397 | SEQ ID NO:18409 |
| iPS:435623 | | AA | RASQGIRNDLG | AASSLQS | LQDNSHPFT |
| | | | SEQ ID NO:2386 | SEQ ID NO:10398 | SEQ ID NO:18410 |
| | 21-225_162D5 | NA | AAGTCCAACCATAGTGTTTT ATACAGGTCCAACAATAATC AATACTTAGCT | CGGACATCTATCCGGAA ATCC | CAGCAATATTATAGTACTCC TCCCACT |

FIGURE 49
(Continued)

| iPS | Clone | AA/NA | Sequence 1 | Sequence 2 | Sequence 3 |
|---|---|---|---|---|---|
| iPS:435627 | 21-225_162D5 | AA | SEQ ID NO:2387 KSNHSVLYRSNNNQYLA | SEQ ID NO:10399 RTSIRKS | SEQ ID NO:18411 QQYYSTPPT |
| | | NA | SEQ ID NO:2388 AAGTCCAGCAGTCCAACAATAACAACTACTTAACT | SEQ ID NO:10400 TGGCATCTACCCGGGAATCC | SEQ ID NO:18412 CAGCAATATTATAGTACTCCTCCGACG |
| iPS:435629 | 21-225_162F6 | AA | SEQ ID NO:2389 KSSQNVLHSSNNNNYLT | SEQ ID NO:10401 WASTRES | SEQ ID NO:18413 QQYYSTPPT |
| | | NA | SEQ ID NO:2390 AAGTCTACTACTCAGAGCCTCCTGCATGGTGATGGAAAGACCTATTTGTAT | SEQ ID NO:10402 GAAGTTTCCAAGCGGTTCTCT | SEQ ID NO:18414 AAGCAAAGTATACAGCTTCCGTGGACG |
| iPS:435631 | 21-225_162H6 | AA | SEQ ID NO:2391 KSTQSILHGDGKTYLY | SEQ ID NO:10403 EVSKRFS | SEQ ID NO:18415 KQSIQLPWT |
| | | NA | SEQ ID NO:2392 CGGGCGAGTCAGGACATTAGCAATTATTTAGGC | SEQ ID NO:10404 GCTGCATCCAGTTGCAAAGT | SEQ ID NO:18416 CAACAGTATAATAGTTACCCATTCACT |
| iPS:435635 | 21-225_163F1 | AA | SEQ ID NO:2393 RASQDISNYLA | SEQ ID NO:10405 AASSLQS | SEQ ID NO:18417 QQYNSYPFT |
| | | NA | SEQ ID NO:2394 CGGGCGAGTCAGGACATTAGCAATTATTTAGGC | SEQ ID NO:10406 CCTGCATCCAGTTGCAAAGT | SEQ ID NO:18418 CTACAGCATAATAGTCACCCATTCACT |
| iPS:435637 | 21-225_163E2 | AA | SEQ ID NO:2395 RASQDIRNDLG | SEQ ID NO:10407 PASSLQS | SEQ ID NO:18419 LQHNSHPFT |
| | | NA | SEQ ID NO:2396 CGGGCGAGTCAGGACATTAGCAATTATTTAGGC | SEQ ID NO:10408 GCTGCATCCAGTTGCAAAGT | SEQ ID NO:18420 CAACAGTATCATAGTTACCCGCTCACT |
| iPS:435639 | 21-225_163G6 | AA | SEQ ID NO:2397 RASQDISNYLV | SEQ ID NO:10409 AASSLLS | SEQ ID NO:18421 QQYHSYPLT |
| | | NA | SEQ ID NO:2398 RASQDISNYLV | SEQ ID NO:10410 GCTGCATCCAGTTGCTAAGT | SEQ ID NO:18422 |

FIGURE 49 (Continued)

| | | | | |
|---|---|---|---|---|
| iPS:435641 | 21-225_163F9 | NA | CGGGCAAGTCAGGACATTAG AGATGATTAGGC SEQ ID NO:2399 | CCTGCATCCAGTTGCAA AGT SEQ ID NO:10411 | CTACAGGATAATAGTTACCC ATTCACT SEQ ID NO:18423 |
| | | AA | RASQDIRDDLG SEQ ID NO:2400 | PASSLQS SEQ ID NO:10412 | LQDNSYPFT SEQ ID NO:18424 |
| iPS:435643 | 21-225_163G10 | NA | CGGGCAAGTCAGGACATTAG AAATAATTTAGGC SEQ ID NO:2401 | CCTGCATCCAGTTGCAA AGT SEQ ID NO:10413 | CTACAGGATTATAGTTACC ATTCACT SEQ ID NO:18425 |
| | | AA | RASQDIRNNLG SEQ ID NO:2402 | PASSLQS SEQ ID NO:10414 | LQDYSYPFT SEQ ID NO:18426 |
| iPS:435649 | 21-225_165H2 | NA | AAGTCCAGCAGTCAGAGTGTTT ACACAGCTCCAACAATAAGA ACTACTTAACT SEQ ID NO:2403 | TGGGCATCTACCCGAGA ATCC SEQ ID NO:10415 | CAGCAATCTTATAGTATTCC TCCCACT SEQ ID NO:18427 |
| | | AA | KSSQSVLHSSNNKNYLT SEQ ID NO:2404 | WASTRES SEQ ID NO:10416 | QQSYSIPPT SEQ ID NO:18428 |
| iPS:435653 | 21-225_166H12 | NA | CGGGCGAGTCAGGACATTAG CCATTATTAGCC SEQ ID NO:2405 | GCTGCATCCAGTTGCAA AGT SEQ ID NO:10417 | CAACAGTATAATAGTTTCCC GCTCACT SEQ ID NO:18429 |
| | | AA | RASQDISHYLA SEQ ID NO:2406 | AASSLQS SEQ ID NO:10418 | QQYNSFPLT SEQ ID NO:18430 |
| iPS:435655 | 21-225_167E2 | NA | AAGTCTAGTCAGAGCCTCCT GCACGGTGATGGGAAGACCT ATTTGTAT SEQ ID NO:2407 | GAAGTTTCCAAACGGTT CTCT SEQ ID NO:10419 | ATGCAAAGCATACAGCTTCC GTGGACG SEQ ID NO:18431 |
| | | AA | KSSQSLLHGDGKTYLY SEQ ID NO:2408 | EVSKRFS SEQ ID NO:10420 | MQSIQLPWT SEQ ID NO:18432 |
| iPS:435657 | 21-225_167H10 | NA | AAGTCTAGTCAGAGCCTCCT GCACGGTGATGGGAAGACCT ATTTGTAT | GAAGTTTCCAAACGGTT CTCT | ATGCAAAGCATACAGCTTCC GTGGACG |

FIGURE 49
(Continued)

| | | | | | | | |
|---|---|---|---|---|---|---|---|
| iPS:435659 | 21-225_167H10 | AA | SEQ ID NO:2409<br>KSSQSLLHGDGKTYLY | SEQ ID NO:10421<br>EVSKRFS | SEQ ID NO:18433<br>MQSIQLPWT | | |
| iPS:435663 | 21-225_167D12 | NA | SEQ ID NO:2410<br>CGGGGCGAGTCAGGGCATTAA<br>CAATTATTTAGGC | SEQ ID NO:10422<br>GCTGCATCCAGTTTGCAA<br>AGT | SEQ ID NO:18434<br>CAACAGTATAATAGTTATCC<br>ATTCACT | | |
| | | AA | SEQ ID NO:2411<br>RASQGINNYLA | SEQ ID NO:10423<br>AASSLQS | SEQ ID NO:18435<br>QQYNSYPFT | | |
| iPS:435665 | 21-225_169B1 | NA | SEQ ID NO:2412<br>CGGGCTAGTCAGGGCATTAG<br>AAATGATTTAGGC | SEQ ID NO:10424<br>GCTGAATCCAGTTTGCA<br>AAGT | SEQ ID NO:18436<br>CTACAGCATTATAGTTACCC<br>GCTCACT | | |
| | | AA | SEQ ID NO:2413<br>RASQGIRNDLG | SEQ ID NO:10425<br>AESSLQS | SEQ ID NO:18437<br>LQHYSYPLT | | |
| iPS:435667 | 21-225_169F2 | NA | SEQ ID NO:2414<br>AAGTCCAGCAGTCAGAGTGTTT<br>ATACATCTCCAACAATAAAA<br>ACTACTTAGCT | SEQ ID NO:10426<br>TGGGCATCTACCCGGGA<br>ATCC | SEQ ID NO:18438<br>CAGCAATATATGTGTGCTCC<br>CACC | | |
| | | AA | SEQ ID NO:2415<br>KSSQSVLYISNNKNYLA | SEQ ID NO:10427<br>WASTRES | SEQ ID NO:18439<br>QQYYRAPT | | |
| iPS:435669 | 21-225_169E3 | NA | SEQ ID NO:2416<br>AGGTCTAGTCAGAGCCTCCT<br>GCATAATAATGGATACAAGT<br>ATTTGGAT | SEQ ID NO:10428<br>TTGGGTTCTAATCGGGCC<br>TCC | SEQ ID NO:18440<br>ATGCAAGTTCTACAAACTCC<br>GTGGACG | | |
| | | AA | SEQ ID NO:2417<br>RSSQSLLHNNGYKYLD | SEQ ID NO:10429<br>LGSNRAS | SEQ ID NO:18441<br>MQVLQTPWT | | |
| iPS:435669 | 21-225_169F9 | NA | SEQ ID NO:2418<br>CGGGCAAGTCAGGGCATTAG<br>AAATGATTTAGGC | SEQ ID NO:10430<br>GCTGCATCCAGTTTGCAA<br>AGT | SEQ ID NO:18442<br>CTACAGCATTATAGTTACCC<br>GCTCACT | | |
| | | AA | SEQ ID NO:2419<br>RASQGIRNDLG | SEQ ID NO:10431<br>AASSLQS | SEQ ID NO:18443<br>LQHYSYPLT | | |
| | | | SEQ ID NO:2420 | SEQ ID NO:10432 | SEQ ID NO:18444 | | |

FIGURE 49
(Continued)

| | | | | | |
|---|---|---|---|---|---|
| iPS:435671 | 21-225_169H5 | NA | AAGTCCAGCCAGAGTGTTTT ATACATCTCCAACAATAAAA ACTACTTAGCT SEQ ID NO:2421 | TGGGCATCTACCCGGGA ATCC SEQ ID NO:10433 | CAGCAATATTATCGTGCTCC CACC SEQ ID NO:18445 |
| | | AA | KSSQSVLYISNNKNYLA SEQ ID NO:2422 | WASTRES SEQ ID NO:10434 | QQYYRAPT SEQ ID NO:18446 |
| iPS:435673 | 21-225_169E6 | NA | AGGTCTAGTCAGAGCCTCCT GCATAATAATGGATACAAGT ATTTGGAT SEQ ID NO:2423 | TTGGGTTCTAATCGGGCC TCC SEQ ID NO:10435 | ATGCAAGTTCTACAAACTCC GTGGACG SEQ ID NO:18447 |
| | | AA | RSSQSLLHNNGYKYLD SEQ ID NO:2424 | LGSNRAS SEQ ID NO:10436 | MQVLQTPWT SEQ ID NO:18448 |
| iPS:435675 | 21-225_169D7 | NA | CGGGCAAGTCAGGGCATTAG AAATGATTTAGGC SEQ ID NO:2425 | GCTGCATCCAGTTTGCAA AGT SEQ ID NO:10437 | CTACAGCATCATAGTTGCCC GTGGACG SEQ ID NO:18449 |
| | | AA | RASQGIRNDLG SEQ ID NO:2426 | AASSLQS SEQ ID NO:10438 | LQHHSCPWT SEQ ID NO:18450 |
| iPS:435677 | 21-225_169C10 | NA | CGGGCGAGTCAGGACATTAG CAATTATTTAGCC SEQ ID NO:2427 | TCTGCATCCAGTTTGCAA AGT SEQ ID NO:10439 | CAACAATCTGATAGTTACCC TCTCACT SEQ ID NO:18451 |
| | | AA | RASQDISNYLA SEQ ID NO:2428 | SASSLQS SEQ ID NO:10440 | QQSDSYPLT SEQ ID NO:18452 |
| iPS:435679 | 21-225_169D10 | NA | CGGGCGAGTCAGGGCATTAG CAATTATTTAGCC SEQ ID NO:2429 | GCTGCATCCAGTTTGCAA AGT SEQ ID NO:10441 | CAACAGTATCATAGTTACCC ATTCACT SEQ ID NO:18453 |
| | | AA | RASQDISNYLA SEQ ID NO:2430 | AASSLQS SEQ ID NO:10442 | QQYHSYPFT SEQ ID NO:18454 |
| iPS:435681 | 21-225_169D11 | NA | CGGGCAAGTCAGGGCATTAG AGATGATTTAGGC SEQ ID NO:2431 | GCTGCATCCAGTTTGCAA AGT SEQ ID NO:10443 | CTTCAGCATTATAGTTACCCT CGGACG SEQ ID NO:18455 |

FIGURE 49
(Continued)

| | | | | |
|---|---|---|---|---|
| iPS:435683 | AA | RASQGIRDDLG<br>SEQ ID NO:2432 | AASSLQS<br>SEQ ID NO:10444 | LQHYSYPRT<br>SEQ ID NO:18456 |
| | NA | AAGTCTAGTCAGAGCCTCCT<br>GCATGGTGATGGAAAGACCT<br>ATTTGTTT<br>SEQ ID NO:2433 | GAAGTTTCCAACCGGTTC<br>TCT<br>SEQ ID NO:10445 | ATGCAAAGTATTCAGCTTCC<br>GTGGACG<br>SEQ ID NO:18457 |
| iPS:435685 | AA | KSSQSLLHGDGKTYLF<br>SEQ ID NO:2434 | EVSNRFS<br>SEQ ID NO:10446 | MQSIQLPWT<br>SEQ ID NO:18458 |
| | NA | CGGGGGAGTCAGGGCATTAG<br>CAATTATTTAGGC<br>SEQ ID NO:2435 | GCTGCATCCAGTTTGCAA<br>AGT<br>SEQ ID NO:10447 | CAACAGTATCATAGTTACCC<br>ATTCACT<br>SEQ ID NO:18459 |
| iPS:435687 | AA | RASQGISNYLA<br>SEQ ID NO:2436 | AASSLQS<br>SEQ ID NO:10448 | QQYHSYPFT<br>SEQ ID NO:18460 |
| | NA | CGGGCAAGTCAGGGCATTAG<br>AAATGATTTAGGC<br>SEQ ID NO:2437 | GCTACACATCCAGTTTGCAA<br>AGT<br>SEQ ID NO:10449 | CTACAGCATAGTAGTAACCC<br>GTGGACG<br>SEQ ID NO:18461 |
| iPS:435689 | AA | RASQGIRNDLG<br>SEQ ID NO:2438 | ATSSLQS<br>SEQ ID NO:10450 | LQHSSNPWT<br>SEQ ID NO:18462 |
| | NA | CGGGCAAGTCGGGGCATTAG<br>AAATGATTTAGGC<br>SEQ ID NO:2439 | GCTGCATCCAGTTTGCAA<br>AGT<br>SEQ ID NO:10451 | CTACAGCATTATAGTTACCC<br>TCGGACG<br>SEQ ID NO:18463 |
| iPS:435693 | AA | RASRGIRNDLG<br>SEQ ID NO:2440 | AASSLQS<br>SEQ ID NO:10452 | LQHYSYPRT<br>SEQ ID NO:18464 |
| | NA | CGGGCAAGTCAGGGCATTAG<br>AAATGATTTAGGC<br>SEQ ID NO:2441 | GCTGCATCCAGTTTGCAA<br>AGT<br>SEQ ID NO:10453 | CTACAGCATTATAGTTACCC<br>GCTCACT<br>SEQ ID NO:18465 |
| iPS:435695 | AA | RASQGIRNDLG<br>SEQ ID NO:2442 | AASTLQS<br>SEQ ID NO:10454 | LQHYSYPLT<br>SEQ ID NO:18466 |
| | NA | CGGGCAAGTCAGGGCATTAG<br>AAATGATTTAGGC | GCTGCATCCAGTTTGCAA<br>AAT | CTACAGCATTATAGTTTCCC<br>GCTCACT |

FIGURE 49
(Continued)

| | | | | | | | |
|---|---|---|---|---|---|---|---|
| iPS:435697 | 21-225_170D5 | | SEQ ID NO:2443 RASQGIRNDLG | | SEQ ID NO:10455 AASSLQN | | SEQ ID NO:18467 LQHYSFPLT |
| | | AA | SEQ ID NO:2444 | | SEQ ID NO:10456 | | SEQ ID NO:18468 |
| iPS:435699 | 21-225_170G5 | NA | CGGGCAAGTCAGGGCATTAG AACTGATTAGGC | ACTGCATCCAGTTGCAA AGT | | CTACAGCATTATAGTTACCC GCTCACT | |
| | | | SEQ ID NO:2445 RASQGIRTDLG | | SEQ ID NO:10457 TASSLQS | | SEQ ID NO:18469 LQHYSYPLT |
| | | AA | SEQ ID NO:2446 | | SEQ ID NO:10458 | | SEQ ID NO:18470 |
| iPS:435701 | 21-225_170D6 | NA | CGGGGAGTCAGGACATTGG CAATTGTTAGCC | TCTGCGTCCAGTTGCAA AGT | | CAACAATCTGATAGTACTCC TCTCACT | |
| | | | SEQ ID NO:2447 RASQDIGNCLA | | SEQ ID NO:10459 SASSLQS | | SEQ ID NO:18471 QQSDSYPLT |
| | | AA | SEQ ID NO:2448 | | SEQ ID NO:10460 | | SEQ ID NO:18472 |
| iPS:435701 | 21-225_170F6 | NA | AAGTCCAGCCAGAGTGTTT ACACAGCTCCAACAATTACA ACTACTTAGCT | TGGGCATCTACCGGAA ATCC | | CAGCAATATATTATAGTACTCC GTGGACG | |
| | | | SEQ ID NO:2449 | | SEQ ID NO:10461 WASTRKS | | SEQ ID NO:18473 QQYYSTPWT |
| | | AA | SEQ ID NO:2450 KSSQSVLHSSNNYNYLA | | SEQ ID NO:10462 | | SEQ ID NO:18474 |
| iPS:435703 | 21-225_170D11 | NA | CGGGCAAGTCAGGGCATTAG AAATGATTAGGC | GCTGCATCCAGTTGCAA AAT | | CTACAGCATTATAGTTACCC GCTCACT | |
| | | | SEQ ID NO:2451 RASQGIRNDLG | | SEQ ID NO:10463 AASSLQN | | SEQ ID NO:18475 LQHYSFPLT |
| | | AA | SEQ ID NO:2452 | | SEQ ID NO:10464 | | SEQ ID NO:18476 |
| iPS:435705 | 21-225_171C3 | NA | CGGGCAAGTCAGGGCATTAG AACTGATTAGGC | ACTGCATCCAGTTGCAA AGT | | CTACAGCATTATAGTTACCC GCTCACT | |
| | | | SEQ ID NO:2453 RASQGIRTDLG | | SEQ ID NO:10465 TASSLQS | | SEQ ID NO:18477 LQHYSYPLT |
| | | AA | SEQ ID NO:2454 | | SEQ ID NO:10466 | | SEQ ID NO:18478 |

FIGURE 49
(Continued)

| | | | | | |
|---|---|---|---|---|---|
| iPS:435709 | 21-225_171A4 | NA | CGGGCAAGTCAGGGCATTAG AAATGATTTAGGC | ACTGCATCCAGTTTGCAA AGT | CTACAGGCATTATAGTTACCC GCTCACT |
| | | | SEQ ID NO:2455 | SEQ ID NO:10467 | SEQ ID NO:18479 |
| | | AA | RASQGIRNDLG | TASSLQS | LQHYSYPLT |
| | | | SEQ ID NO:2456 | SEQ ID NO:10468 | SEQ ID NO:18480 |
| iPS:435711 | 21-225_171G4 | NA | CGGGCGAGTCAGGGTGTTAA CGACTGGTTAGCC | GATGCATCCAAGTTGCA AAGT | CAACAGGCTAACAGTTTCCC GTGGACG |
| | | | SEQ ID NO:2457 | SEQ ID NO:10469 | SEQ ID NO:18481 |
| | | AA | RASQGVNDWLA | DASSLQS | QQANSFPWT |
| | | | SEQ ID NO:2458 | SEQ ID NO:10470 | SEQ ID NO:18482 |
| iPS:435713 | 21-225_171D7 | NA | AGGTCTAGTCAGAGCCTCCT GTATCATAATGGATACAACT ATTTGGAT | GTGGGTTCTAATCGGGC CTCC | ATGCAAACTCTACAAACTCC GCTCACT |
| | | | SEQ ID NO:2459 | SEQ ID NO:10471 | SEQ ID NO:18483 |
| | | AA | RSSQSLLYHNGYNYLD | VGSNRAS | MQTLQTPLT |
| | | | SEQ ID NO:2460 | SEQ ID NO:10472 | SEQ ID NO:18484 |
| iPS:435715 | 21-225_171A8 | NA | CGGGCGAGTCAGGGTATTAG CAACTGGTTAGCC | GCTGCATTCAGTTTGCAA GGT | CAACAGACTAACAGTTTCCC GTGGACG |
| | | | SEQ ID NO:2461 | SEQ ID NO:10473 | SEQ ID NO:18485 |
| | | AA | RASQGISNWLA | AAFSLQG | QQTNSFPWT |
| | | | SEQ ID NO:2462 | SEQ ID NO:10474 | SEQ ID NO:18486 |
| iPS:435717 | 21-225_171A9 | NA | CGGGCGAGTCAGGGCATTAG CACCTGGTTAGCC | GATGCATCCAGTTGCA AAGT | CTACAGACTAACAGTTTCCC GTGGACG |
| | | | SEQ ID NO:2463 | SEQ ID NO:10475 | SEQ ID NO:18487 |
| | | AA | RASQDITTWLA | DASSLQS | LQTNSFPWT |
| | | | SEQ ID NO:2464 | SEQ ID NO:10476 | SEQ ID NO:18488 |
| iPS:435719 | 21-225_171A11 | NA | CGGGCAAGTCAGGGCATTAG AAATAATTTAGGC | CCTGCATCCAGTTTGCAA AGT | CTACAGGATCATAGTTACC ATTCACT |
| | | | SEQ ID NO:2465 | SEQ ID NO:10477 | SEQ ID NO:18489 |
| | | AA | RASQGIRNNLG | PASSLQS | LQDHSYPFT |

FIGURE 49
(Continued)

| | | | | | | |
|---|---|---|---|---|---|---|
| iPS:435723 | 21-225_172B3 | NA | SEQ ID NO:2466 CGGGCTAGTCAGGGCATTAG AAATGATTAGGC | SEQ ID NO:10478 GCTGAATCCAGTTGCA AAGT | SEQ ID NO:18490 CTACAGCATTATAGTTACCC GCTCACT |
| | | AA | SEQ ID NO:2467 RASQGIRNDLG | SEQ ID NO:10479 AESSLQS | SEQ ID NO:18491 LQHYSYPLT |
| iPS:435723 | 21-225_172B7 | NA | SEQ ID NO:2468 AAGTCTAGTCAGAGCCTCCT GCATGGTGATGGAAAGACCT TCT ATTTCTAT | SEQ ID NO:10480 GAAGTTTCCCACCGGTTC | SEQ ID NO:18492 ATGCAAAGTATACAGTTTCC GTGGACG |
| | | AA | SEQ ID NO:2469 KSSQSLLHGDGKTYFY | SEQ ID NO:10481 EVSHRFS | SEQ ID NO:18493 MQSIQFPWT |
| iPS:435725 | 21-225_172G8 | NA | SEQ ID NO:2470 CGGGCAAGTCAGGGCGTTAG AAATGATTAGGC | SEQ ID NO:10482 GCTGCATCCAGTTGCAA AAT | SEQ ID NO:18494 CTACACCATTATAGTTTCCC GCTCACT |
| | | AA | SEQ ID NO:2471 RASQGVRNDLG | SEQ ID NO:10483 AASSLQN | SEQ ID NO:18495 LHHYSFPLT |
| iPS:435727 | 21-225_172E11 | NA | SEQ ID NO:2472 AAGTCCAGCAGAGTGTTT ACACAGCTCCAACATAACA ACTACTTAGCT | SEQ ID NO:10484 TGGGCATCTACTCGGGA ATCC | SEQ ID NO:18496 CAGCAATATTTACTACTACCC GTGCAGT |
| | | AA | SEQ ID NO:2473 KSSQSVLHSSNNNNYLA | SEQ ID NO:10485 WASTRES | SEQ ID NO:18497 QQYFTPCS |
| iPS:435729 | 21-225_173E7 | NA | SEQ ID NO:2474 CGTGCAAGTCAGAGACCATTAG CAACTATTTAAAT | SEQ ID NO:10486 GCTGCATCCAGTTGCAA ATT | SEQ ID NO:18498 CAACAGAGTTACAGAACCCC TCAGTGGACG |
| | | AA | SEQ ID NO:2475 RASQTISNYLN | SEQ ID NO:10487 AASSLQI | SEQ ID NO:18499 QQSYRTPQWT |
| | | | SEQ ID NO:2476 | SEQ ID NO:10488 | SEQ ID NO:18500 |

FIGURE 49
(Continued)

| | | | | |
|---|---|---|---|---|
| iPS:435731 | NA | AAGTCTAGTCAGAGCCTCCT GCATGGTGATGGAAAGACCT ATTTGTAT SEQ ID NO:2477 | GAAGTTCCAACCGGTTC TCT SEQ ID NO:10489 | ATGCAAAGTATACAGGTTCC GTGGACG SEQ ID NO:18501 |
| | | KSSQSLLHGDGKTYLY SEQ ID NO:2478 | EVSNRFS SEQ ID NO:10490 | MQSIQVPWT SEQ ID NO:18502 |
| 21-225_173A11 | AA |
| iPS:435733 | NA | AAGTCTAGTCAGAGCCTCCT GCATAGTGAGGGAAAGACC TACTTGTAT SEQ ID NO:2479 | GAAGTTCCCACCGGTTC TCT SEQ ID NO:10491 | ATGCAAAGTATACAGGTTCT CACT SEQ ID NO:18503 |
| | | KSSQSLLHSEGKTYLY SEQ ID NO:2480 | EVSHRFS SEQ ID NO:10492 | MQSIQLLT SEQ ID NO:18504 |
| 21-225_173C11 | AA |
| iPS:435735 | NA | CGGGCAAGTCAGGGCATTAG AAATGATTTAGGC SEQ ID NO:2481 | ACTACAGATCCAGTTTGCAA AGT SEQ ID NO:10493 | CTACAGCATTATAGTTTCCC GAACACT SEQ ID NO:18505 |
| | | RASQGIRNDLG SEQ ID NO:2482 | TTSSLQS SEQ ID NO:10494 | LQHYSFPNT SEQ ID NO:18506 |
| 21-225_173H12 | AA |
| iPS:435737 | NA | AAGTCCAGCCAGAGTGTATT ACACAGCTCCAACAATTACA ACTACTTAACT SEQ ID NO:2483 | TGGGCATCTACCGGGA ATCC SEQ ID NO:10495 | CAGCAATATTATCGTACTCC GTGGACG SEQ ID NO:18507 |
| | | KSSQSVLHSSNNYNYLT SEQ ID NO:2484 | WASTRES SEQ ID NO:10496 | QQYYRTPWT SEQ ID NO:18508 |
| 21-225_174G5 | AA |
| iPS:435739 | NA | CGGGGAGTCAGGGCATTAG CAACTGGTTAGCC SEQ ID NO:2485 | GCTGCATTCAGTTGCAA GGT SEQ ID NO:10497 | CAACAGACTAACAGTTTCCC GTGGACG SEQ ID NO:18509 |
| | | RASQGISNWLA SEQ ID NO:2486 | AAFSLQG SEQ ID NO:10498 | QQTNSFPWT SEQ ID NO:18510 |
| 21-225_174G7 | AA |
| iPS:435741 | NA | CGGGCAAGTCAGGGCATTAG AGATGATTTAGGC | GCTGCATCCAGTTGCAA AGT | CTTCAGCATCATAGTTACCC TCGGACG |

FIGURE 49
(Continued)

| | | | | | |
|---|---|---|---|---|---|
| iPS:435743 | 21-225_174G10 | AA | SEQ ID NO:2487<br>RASQGIRDDLG<br>SEQ ID NO:2488 | SEQ ID NO:10499<br>AASSLQS<br>SEQ ID NO:10500 | SEQ ID NO:18511<br>LQHHSYPRT<br>SEQ ID NO:18512 |
| iPS:435745 | 21-225_175G1 | NA | CGGGCAAGTCAGGGCATTAG<br>AACTGATTAGGC<br>SEQ ID NO:2489 | ACTGCATCCAGTTTGCAA<br>AGT<br>SEQ ID NO:10501 | CTACAGCATTATAGTTACCC<br>GCTCACT<br>SEQ ID NO:18513 |
| | | AA | RASQGIRDLG<br>SEQ ID NO:2490 | TASSLQS<br>SEQ ID NO:10502 | LQHYSYPLT<br>SEQ ID NO:18514 |
| iPS:435747 | 21-225_175G3 | NA | CGGGGAGTCAGGGACATTAG<br>CAATGATTAGGC<br>SEQ ID NO:2491 | TCTGCATCCAGTTTGCAA<br>AGT<br>SEQ ID NO:10503 | CAACAATCTGATAGTTACCC<br>TCTCACT<br>SEQ ID NO:18515 |
| | | AA | RASQDISNDLA<br>SEQ ID NO:2492 | SASSLQS<br>SEQ ID NO:10504 | QQSDSYPLT<br>SEQ ID NO:18516 |
| iPS:435749 | 21-225_175C4 | NA | CGGGCGAGTCAGGGCATTGG<br>GAATTATTAGGC<br>SEQ ID NO:2493 | GCTGCATCCGGTTTGCAA<br>AGT<br>SEQ ID NO:10505 | CAACAGTATTATAGTTACCC<br>ATTCACT<br>SEQ ID NO:18517 |
| | | AA | RASQGIGNYLA<br>SEQ ID NO:2494 | AASGLQS<br>SEQ ID NO:10506 | QQYYSYPFT<br>SEQ ID NO:18518 |
| iPS:435749 | 21-225_175C10 | NA | CGGGCGAGTCAGGGGTATTAC<br>CGACTGGTTAGGC<br>SEQ ID NO:2495 | GCTGCATCCAGTTTGCAA<br>AGT<br>SEQ ID NO:10507 | CAACAGACTAACAGTTCCC<br>GTGGACG<br>SEQ ID NO:18519 |
| | | AA | RASQGITDWLA<br>SEQ ID NO:2496 | AASSLQS<br>SEQ ID NO:10508 | QQTNSFPWT<br>SEQ ID NO:18520 |
| iPS:435751 | 21-225_175D10 | NA | AAGTCCAGCCAGAGTGTTT<br>ATACAGCTCCAACAATAACA<br>ACTACTTAGCT<br>SEQ ID NO:2497 | TGGACATCTACCCGGGA<br>ATCC<br>SEQ ID NO:10509 | CAGCAATATTATAGTACTCC<br>TCCGACG<br>SEQ ID NO:18521 |
| | | AA | KSSQSVLYSSNNNNYLA<br>SEQ ID NO:2498 | WTSTRES<br>SEQ ID NO:10510 | QQYYSTPPT<br>SEQ ID NO:18522 |

FIGURE 49
(Continued)

| | | | | |
|---|---|---|---|---|
| iPS:435753 | 21-225_175G10 | NA | CGGGCAAGTCAGAGACCATTGG CAACTATTTAAAT SEQ ID NO:2499 | GCTGCATCCAGTTTGCAC AGT SEQ ID NO:10511 | CAACAGAGTTACAGAACCCC TCAGTGGACG SEQ ID NO:18523 |
| | | AA | RASQTIGNYLN SEQ ID NO:2500 | AASSLHS SEQ ID NO:10512 | QQSYRTPQWT SEQ ID NO:18524 |
| iPS:435755 | 21-225_176H4 | NA | AAGTCTAGTCAGAGCCTCCT GCATGGTGATGGAAAGACCT TCT ATTTGTAT SEQ ID NO:2501 | GAAGTTTCCAACCGGTTC TCT SEQ ID NO:10513 | ATGCAAAGTATACAGATTCC GTGGACG SEQ ID NO:18525 |
| | | AA | KSSQSLLHGDGKTYLY SEQ ID NO:2502 | EVSNRFS SEQ ID NO:10514 | MQSIQIPWT SEQ ID NO:18526 |
| iPS:435759 | 21-225_176E6 | NA | AGGTCTAGTCAGAGCCTCCT GCATAATAATGGATACAAGT ATTGGAT SEQ ID NO:2503 | TTGGGTTCTAATCGGGCC TCC SEQ ID NO:10515 | ATGCAAGTTCTACAAACTCC GTGGACG SEQ ID NO:18527 |
| | | AA | RSSQSLLHNNGYKYLD SEQ ID NO:2504 | LGSNRAS SEQ ID NO:10516 | MQVLQTPWT SEQ ID NO:18528 |
| iPS:435761 | 21-225_176B11 | NA | CGGGCAAGTCAGGGCATTAG AAATGATTTAGGC SEQ ID NO:2505 | GCTGCATCCAGTTTGCAA AGT SEQ ID NO:10517 | CTACAGCATTATAGTTACCC GCTCACT SEQ ID NO:18529 |
| | | AA | RASQGIRNDLG SEQ ID NO:2506 | AASSLQS SEQ ID NO:10518 | LQHYSYPLT SEQ ID NO:18530 |
| iPS:435763 | 21-225_176H12 | NA | CGGGCAAGTCAGGGCATTAG AAATGATTTAGGC SEQ ID NO:2507 | GCTGCATCCAGTTTGCAA AGT SEQ ID NO:10519 | CTACAGCATAATAGTTACCC TCGCAGT SEQ ID NO:18531 |
| | | AA | RASQGIRNDLG SEQ ID NO:2508 | AASSLQS SEQ ID NO:10520 | LQHNSYPRS SEQ ID NO:18532 |
| iPS:435765 | 21-225_177D3 | NA | CGGGCGAGTCAGGGCATTAC CAATTATTTAGCC SEQ ID NO:2509 | GCTGCATCCAGTTTGCAA AGT SEQ ID NO:10521 | CAACAGTATAATAGTTACCC ATTCACT SEQ ID NO:18533 |

FIGURE 49
(Continued)

| | | | | | |
|---|---|---|---|---|---|
| iPS:435767 | 21-225_177B4 | AA | RASQGITNYLA SEQ ID NO:2510 | AASSLQS SEQ ID NO:10522 | QQYNSYPFT SEQ ID NO:18534 |
| | | NA | CGGGCAAGTCAGGGCATTAG AAATGATTTAGGC SEQ ID NO:2511 | GCTGCATCCAGTTTGCAA AGT SEQ ID NO:10523 | CTACAGCATTATAGTTTCCCT CGCAGT SEQ ID NO:18535 |
| iPS:435769 | 21-225_177B6 | AA | RASQGIRNDLG SEQ ID NO:2512 | AASSLQS SEQ ID NO:10524 | LQHYSFPRS SEQ ID NO:18536 |
| | | NA | CGGGCAAGTCAGGACATTAG CAATGATTTAGGC SEQ ID NO:2513 | GCTGCATCCAGTTTGCAA AGT SEQ ID NO:10525 | CTACAGCTTAATAGTTACCC ATTCACT SEQ ID NO:18537 |
| | | AA | RASQDISNDLG SEQ ID NO:2514 | AASSLQS SEQ ID NO:10526 | LQLNSYPFT SEQ ID NO:18538 |
| iPS:435771 | 21-225_177B11 | NA | AAGTCTAGTCAGGCGCCTCCT GCATGGTGATGGAAAGACCT ATTTGTAT SEQ ID NO:2515 | GAAGTTCCAACCGGTTC TCT SEQ ID NO:10527 | ATGCAAAGTATACAGATTCC GTGGACG SEQ ID NO:18539 |
| | | AA | KSSQRLLHGDGKTYLY SEQ ID NO:2516 | EVSNRFS SEQ ID NO:10528 | MQSIQIPWT SEQ ID NO:18540 |
| iPS:435773 | 21-225_177B12 | NA | AAGTCCAGCCAGAGTGTTT ACACAGCTCCAACAATAACA ACTACTTAACT SEQ ID NO:2517 | TGGGCATCTACCCGGGA ATCC SEQ ID NO:10529 | CAGCAATATTATAGTAGTCC TCCGACG SEQ ID NO:18541 |
| | | AA | KSSQSVLHSSNNNNYLT SEQ ID NO:2518 | WASTRES SEQ ID NO:10530 | QQYYSSPPT SEQ ID NO:18542 |
| iPS:435775 | 21-225_178A5 | NA | CGGGCGAGTCAGGGTATTAG CAACTGGTTAGCC SEQ ID NO:2519 | GCTGCTTCCAGTTTGCAA AGT SEQ ID NO:10531 | CAACAGGCTAACAGTTTACC GTGGACG SEQ ID NO:18543 |
| | | AA | RASQGISNWLA SEQ ID NO:2520 | AASSLQS SEQ ID NO:10532 | QQANSLPWT SEQ ID NO:18544 |

FIGURE 49
(Continued)

| | | | | | |
|---|---|---|---|---|---|
| iPS:435777 | 21-225_178F7 | NA | CGGGCGAGTCAGGATATTAC TGACTGGTTAGCC SEQ ID NO:2521 | GCTGCATCCAGTTTGCAG AGT SEQ ID NO:10533 | CAACAGGCTAACAGTTTACC GTGGACG SEQ ID NO:18545 |
| | | AA | RASQDIIDWLA SEQ ID NO:2522 | AASSLQS SEQ ID NO:10534 | QQANSLPWT SEQ ID NO:18546 |
| iPS:435779 | 21-225_178B10 | NA | CGGGCAAGTCAGGGCATTAG AAATGATTAGGC SEQ ID NO:2523 | GCTGCATCCAGTTTGCAA AAT SEQ ID NO:10535 | CTACACCATTATAGTTTCC GCTCACT SEQ ID NO:18547 |
| | | AA | RASQGIRNDLG SEQ ID NO:2524 | AASSLQN SEQ ID NO:10536 | LHHYSFPLT SEQ ID NO:18548 |
| iPS:435781 | 21-225_178C10 | NA | AAGTCTAGTCAGAGCCTCCT GCATAGTGGATGGGAAGACCT ATTTGTAT SEQ ID NO:2525 | GAAGTTTCCAACCGGTTT TCT SEQ ID NO:10537 | ATGCAAAGTATACAGGTTCC GTGGACG SEQ ID NO:18549 |
| | | AA | KSSQSLLHGDGKTYLY SEQ ID NO:2526 | EVSNRFS SEQ ID NO:10538 | MQSIQVPWT SEQ ID NO:18550 |
| iPS:435783 | 21-225_179G1 | NA | CGGGCGAGTCAGGATATTAG CGACTGGTTAGCC SEQ ID NO:2527 | GCTGCATCCAGTTTGCAA AGT SEQ ID NO:10539 | CAACAGGCTAACAGTTTACC GTGGACG SEQ ID NO:18551 |
| | | AA | RASQDISDWLA SEQ ID NO:2528 | AASSLQS SEQ ID NO:10540 | QQANSLPWT SEQ ID NO:18552 |
| iPS:435785 | 21-225_179C2 | NA | AAATCTAGTCAGAGCCTCCT GCATAGTGAGGGAAAGACC TACTTGTAT SEQ ID NO:2529 | GAGGTTTCCCACCGGTTC TCT SEQ ID NO:10541 | ATGCAAAGTATACAGGTTCT CACT SEQ ID NO:18553 |
| | | AA | KSSQSLLHSEGKTYLY SEQ ID NO:2530 | EVSHRFS SEQ ID NO:10542 | MQSIQVLT SEQ ID NO:18554 |
| iPS:435787 | 21-225_180A3 | NA | CGGGCGAGTCAGGATATTAC CAGCTGGTTAGCC SEQ ID NO:2531 | GCTGCATCCAGTTTGCAA AGT SEQ ID NO:10543 | CAACAGGCTAACAGTATCC ATTCACT SEQ ID NO:18555 |

FIGURE 49
(Continued)

| | | | | | | | |
|---|---|---|---|---|---|---|---|
| iPS:435789 | 21-225_180C4 | AA | RASQDITSWLA<br>SEQ ID NO:2532 | AASSLQS<br>SEQ ID NO:10544 | QQANSIPFT<br>SEQ ID NO:18556 |
| | | NA | AAGTCTAGTCAGAGACCTCCT<br>GCATGGTGATGGAAAGACCT<br>ATTTGTAT<br>SEQ ID NO:2533 | GCAACTTCCAACCGGTTC<br>CCT<br>SEQ ID NO:10545 | ATGCAAAGTATACAGGTTCC<br>GTGGACG<br>SEQ ID NO:18557 |
| iPS:435791 | 21-225_180H7 | AA | KSSQSLLHGDGKTYLY<br>SEQ ID NO:2534 | ATSNRFP<br>SEQ ID NO:10546 | MQSIQVPWT<br>SEQ ID NO:18558 |
| | | NA | CGGGCAAGTCAGGGCATTAG<br>AAATGATTTAGGC<br>SEQ ID NO:2535 | ACTGCATCCAGTTGCAA<br>AGT<br>SEQ ID NO:10547 | CTACAGCATAATAGTTACC<br>ATTCACT<br>SEQ ID NO:18559 |
| iPS:435793 | 21-225_180F8 | AA | RASQGIRNDLG<br>SEQ ID NO:2536 | TASSLQS<br>SEQ ID NO:10548 | LQHNSYPFT<br>SEQ ID NO:18560 |
| | | NA | CGGGCAAGTCAGAGACCATTCT<br>CAGCTATTTAAAT<br>SEQ ID NO:2537 | GGTGTATCCAGTTTACAA<br>AGT<br>SEQ ID NO:10549 | CAGCAGAGTTACAGGTACCC<br>ATTCACT<br>SEQ ID NO:18561 |
| iPS:435795 | 21-225_181C2 | AA | RASQTILSYLN<br>SEQ ID NO:2538 | GVSSLQS<br>SEQ ID NO:10550 | QQSYSTPFT<br>SEQ ID NO:18562 |
| | | NA | AAGTCTAGTCAGAGACCTCCT<br>GCATGGTGATGGAAAGACCT<br>ATTTGTAT<br>SEQ ID NO:2539 | GAAGTTTCCAACCGGTTC<br>TCT<br>SEQ ID NO:10551 | ATGCAAAGTATACAGGTTCC<br>CTGGACG<br>SEQ ID NO:18563 |
| iPS:435797 | 21-225_181G2 | AA | KSSQSLLHGDGKTYLY<br>SEQ ID NO:2540 | EVSNRFS<br>SEQ ID NO:10552 | MQSIQVPWT<br>SEQ ID NO:18564 |
| | | NA | CGGGGAGTCAGGGCATTAG<br>CAATTATTTAGCC<br>SEQ ID NO:2541 | GCTGCATCCAGTTGCAA<br>AGT<br>SEQ ID NO:10553 | CAACAGTATAATGGTTACC<br>ATTCACT<br>SEQ ID NO:18565 |
| | | AA | RASQGISNYLA<br>SEQ ID NO:2542 | AASSLQS<br>SEQ ID NO:10554 | QQYNGYPFT<br>SEQ ID NO:18566 |

FIGURE 49
(Continued)

| | | | | | |
|---|---|---|---|---|---|
| iPS:435799 | 21-225_181G3 | NA | CGGGCAAGTCACAGCAGCATTAG CAACTATTTAAAT SEQ ID NO:2543 | ACTACACATTGAATTTGCAA AGT SEQ ID NO:10555 | CAACAGAGTTACAGTTCTCC TCCGTGGACG SEQ ID NO:18567 |
| | | AA | RASHSISNYLN SEQ ID NO:2544 | TTLNLQS SEQ ID NO:10556 | QQSYSSPPWT SEQ ID NO:18568 |
| iPS:435801 | 21-225_181E5 | NA | AAGTCCAGCCAGAGTGTTT ACACAGTCCAACAATTACA ACTACTTAACT SEQ ID NO:2545 | TGGGCATCTACCCGGGA ATCC SEQ ID NO:10557 | CATCAGTATTTTATTACTCCG TGGACG SEQ ID NO:18569 |
| | | AA | KSSQSVLHSSNNYNYLT SEQ ID NO:2546 | WASTRES SEQ ID NO:10558 | HQYFITPWT SEQ ID NO:18570 |
| iPS:435805 | 21-225_181A8 | NA | CGGGCAAGTCAGGGCATTAG AAATGATTTAGGC SEQ ID NO:2547 | ACTGCATCCAGTTGCAA AGT SEQ ID NO:10559 | CTACAGCATAATAGTTACCC ATTCACT SEQ ID NO:18571 |
| | | AA | RASQGIRNDLG SEQ ID NO:2548 | TASSLQS SEQ ID NO:10560 | LQHNSYPFT SEQ ID NO:18572 |
| iPS:435807 | 21-225_181C10 | NA | AAGTCTAGTCAGAGCCTCCT GCATGGTGATGGAAAGACCT ATTTGTAT SEQ ID NO:2549 | GAAGTTTCCAATCGGTTC TCT SEQ ID NO:10561 | ATGCAAAGTATACAGATTCC CTGGACG SEQ ID NO:18573 |
| | | AA | KSSQSLLHGDGKTYLY SEQ ID NO:2550 | EVSNRFS SEQ ID NO:10562 | MQSIQIPWT SEQ ID NO:18574 |
| iPS:435809 | 21-225_182H5 | NA | CGGGCGAGTCAGGATATTAC CAGCTGGTTAGCC SEQ ID NO:2551 | GCTGCATCCAGTTACAA AGT SEQ ID NO:10563 | CAACAGGTTAACAGTTTCCC ATTCACT SEQ ID NO:18575 |
| | | AA | RASQDITSWLA SEQ ID NO:2552 | AASSLQS SEQ ID NO:10564 | QQVNSFPFT SEQ ID NO:18576 |
| iPS:435811 | 21-225_183H6 | NA | CAGGCGAGTCAGGACATTAG CAACTATTTAAAT SEQ ID NO:2553 | GATGCATCCAATTGGA AACA SEQ ID NO:10565 | CAACAGTATGATAATCTCCC TCTCACT SEQ ID NO:18577 |

FIGURE 49
(Continued)

| | | | | DASNLET | | QQYDNLPLT |
|---|---|---|---|---|---|---|
| iPS:435813 | | AA | QASQDISNYLN SEQ ID NO:2554 | SEQ ID NO:10566 | | SEQ ID NO:18578 |
| | 21-225_183A12 | NA | CGGGCAAGTCGGAACATCA GCAACTATTTAAAT SEQ ID NO:2555 | GTTGTATCCAGTTTGCAA AGT SEQ ID NO:10567 | | CAACAGAGTTACAGTTCCCC TCCGTGGACG SEQ ID NO:18579 |
| iPS:435815 | | AA | RASRNISNYLN SEQ ID NO:2556 | VVSSLQS SEQ ID NO:10568 | | QQSYSSPPWT SEQ ID NO:18580 |
| | 21-225_190G10 | NA | AGGGCCAGTCCGAGTGTTAG CAGCAGATTCTTAGCC SEQ ID NO:2557 | GGTGCATCCAGCAGGGC CACT SEQ ID NO:10569 | | CAGCAGTATGGTAGCTCACC TCCGTGGACG SEQ ID NO:18581 |
| iPS:435817 | | AA | RASPSVSSRFLA SEQ ID NO:2558 | GASSRAT SEQ ID NO:10570 | | QQYGSSPPWT SEQ ID NO:18582 |
| | 21-225_190B11 | NA | CGGGCCAGTCAGAGTATTGG TAGTAACTTACAC SEQ ID NO:2559 | TCTGCTTCCCAGTCCTTC TCA SEQ ID NO:10571 | | CAGCAGTAGTAGTTACC GTGGACG SEQ ID NO:18583 |
| iPS:435819 | | AA | RASQSIGSNLH SEQ ID NO:2560 | SASQSFS SEQ ID NO:10572 | | QQSSSLPWT SEQ ID NO:18584 |
| | 21-225_190C11 | NA | CGGACGAGTCAGGGCATTGG CAATTATTAGCC SEQ ID NO:2561 | AAAACATCCAGTTACA AAGT SEQ ID NO:10573 | | CAACAGTATATGACTTACCC GCTCACT SEQ ID NO:18585 |
| iPS:435821 | | AA | RTSQGIGNYLA SEQ ID NO:2562 | KTSSLQS SEQ ID NO:10574 | | QQYMTYPLT SEQ ID NO:18586 |
| | 21-225_190E11 | NA | AGGGCCAGTCAGAGTTTTCG CATCAACTTAGCC SEQ ID NO:2563 | GGTGCATCCACCAGGGC CACT SEQ ID NO:10575 | | CAGCAGTATAATAACTGGCC GCTCACT SEQ ID NO:18587 |
| iPS:435823 | | AA | RASQSFRINLA SEQ ID NO:2564 | GASTRAT SEQ ID NO:10576 | | QQYNNWPLT SEQ ID NO:18588 |
| | 21-225_190F11 | NA | CGGGCCAGTCAGAACATTGG TAGTAGCTTACAC SEQ ID NO:2565 | TATGCTTCCCAGTCCTTC TCA SEQ ID NO:10577 | | CATCAGAGTAGTAGTTTCCC TCGGACG SEQ ID NO:18589 |

FIGURE 49
(Continued)

| | | | | | | | |
|---|---|---|---|---|---|---|---|
| iPS:435825 | | AA | RASQNIGSSLH SEQ ID NO:2566 | | YASQSFS SEQ ID NO:10578 | | HQSSSFPRT SEQ ID NO:18590 |
| | 21-225_190G11 | NA | CGGACGAGTCAGGGCATTGG CAATTATTTAGCC SEQ ID NO:2567 | | AAAGCATCCAGTTTGCA AAGT SEQ ID NO:10579 | | CAACAGTATATGACTTACCC GCTCACT SEQ ID NO:18591 |
| iPS:435827 | | AA | RTSQGIGNYLA SEQ ID NO:2568 | | KASSLQS SEQ ID NO:10580 | | QQYMTYPLT SEQ ID NO:18592 |
| | 21-225_190H11 | NA | AAGTCTAGTCAGAGCCTCCT CCATAGTGATGGAAGGACCT ATTTGTAT SEQ ID NO:2569 | | GAGGTTTCCAACCGGTTC GCT SEQ ID NO:10581 | | ATGCAAAGTATACAGTTTCC CTGGACG SEQ ID NO:18593 |
| iPS:435829 | | AA | KSSQSLLHSDGRTYLY SEQ ID NO:2570 | | EVSNRFA SEQ ID NO:10582 | | MQSIQFPWT SEQ ID NO:18594 |
| | 21-225_190B12 | NA | CGGGCCAGTCAGAGTATTGG TAGTAGCTTACAC SEQ ID NO:2571 | | TATGCTTCCCAGTCCTTC TCA SEQ ID NO:10583 | | CATCAGACTAGAGAAGTTACC TCTCACT SEQ ID NO:18595 |
| iPS:435831 | | AA | RASQSIGSSLH SEQ ID NO:2572 | | YASQSFS SEQ ID NO:10584 | | HQTRSLPLT SEQ ID NO:18596 |
| | 21-225_190C12 | NA | CGGGCAAGTCAGGGCATTAG AAAAGATTTAGCC SEQ ID NO:2573 | | ACTGCATCCAGTTTGCAA AGT SEQ ID NO:10585 | | CTACAGCATAATAGTAGTTACCC GTGGACG SEQ ID NO:18597 |
| iPS:435833 | | AA | RASQGIRKDLG SEQ ID NO:2574 | | TASSLQS SEQ ID NO:10586 | | LQHNSYPWT SEQ ID NO:18598 |
| | 21-225_190D12 | NA | CGGGCGAGTCAGGGCATTAG CAATTATTTAGCC SEQ ID NO:2575 | | GTTGCATCCACTTTGCAA TCA SEQ ID NO:10587 | | CAAAAGTATAACAGTGCCCC ATTCACT SEQ ID NO:18599 |
| iPS:435835 | | AA | RASQGISNYLA SEQ ID NO:2576 | | VASTLQS SEQ ID NO:10588 | | QKYNSAPFT SEQ ID NO:18600 |
| | | NA | CGGGCGAGTCAGGGCATTGG CAAGTATTTAGCC | | GCTGCATCCAGTTTGCAA AGT | | CAACGATATGATACTTACCC ATTCACT |

FIGURE 49
(Continued)

| | | | | | | |
|---|---|---|---|---|---|---|
| iPS:435837 | 21-225_190F12 | AA | SEQ ID NO:2577<br>RASQGIGKYLA | SEQ ID NO:10589<br>AASSLQS | SEQ ID NO:18601<br>QRYDTYPFT | |
| | | NA | SEQ ID NO:2578<br>CGGAGGAGTCAGGGCATTGG<br>CAAGTATTTAGCC | SEQ ID NO:10590<br>AAAGCATCCAGTTGCA<br>AGGT | SEQ ID NO:18602<br>CAACAGTATATGACTTACCC<br>GCTCACT | |
| iPS:435839 | 21-225_198G3 | AA | SEQ ID NO:2579<br>RTSQGIGKYLA | SEQ ID NO:10591<br>KASSLQG | SEQ ID NO:18603<br>QQYMTYPLT | |
| | | NA | SEQ ID NO:2580<br>AGGTCTAGTCAGAGCCTCCT<br>GCATAGTGATGGAAAGACCT<br>ATTTGTTT | SEQ ID NO:10592<br>GAACTTCCAACCGGTTC<br>TCT | SEQ ID NO:18604<br>ATGCAAAGTTCCAGCTTCC<br>CTGGACG | |
| iPS:435841 | 21-225_191B1 | AA | SEQ ID NO:2581<br>RSSQSLLHSDGKTYLF | SEQ ID NO:10593<br>ELSNRFS | SEQ ID NO:18605<br>MQSFQLPWT | |
| | | NA | SEQ ID NO:2582<br>AGGTCCAGCCAGAGTGTTT<br>ACACAGCTCCAACAATTACA<br>ACTACTTAGCT | SEQ ID NO:10594<br>TGGGCATCTACCCGGGA<br>ATCC | SEQ ID NO:18606<br>CAACAATATTATAGTACTCC<br>TCCGACG | |
| iPS:435843 | 21-225_191D8 | AA | SEQ ID NO:2583<br>RSSQSVLHSSNNYNYLA | SEQ ID NO:10595<br>WASTRES | SEQ ID NO:18607<br>QQYYSTPPT | |
| | | NA | SEQ ID NO:2584<br>AGGGCCAGTCAGAGTATTAG<br>CCTCAACTTCTTAGCC | SEQ ID NO:10596<br>GGTGCATCCAGCAGGGC<br>CACT | SEQ ID NO:18608<br>CAGCAGTATGGTAGGTCACC<br>GTGGACG | |
| iPS:435845 | 21-225_191F1 | AA | SEQ ID NO:2585<br>RASQSISLNFLA | SEQ ID NO:10597<br>GASSRAT | SEQ ID NO:18609<br>QQYGRSPWT | |
| | | NA | SEQ ID NO:2586<br>CGGGCGAGTCAGGGCATTAG<br>CAATTATTTAGCC | SEQ ID NO:10598<br>GCTGCATCCAGTTGCAA<br>AGT | SEQ ID NO:18610<br>CAACATTATCTACTTACCCT<br>CTCACT | |
| | 21-225_191G1 | AA | SEQ ID NO:2587<br>RASQGISNYLA | SEQ ID NO:10599<br>AASSLQS | SEQ ID NO:18611<br>QHYLTYPLT | |
| | | | SEQ ID NO:2588 | SEQ ID NO:10600 | SEQ ID NO:18612 | |

FIGURE 49
(Continued)

| | | | | | |
|---|---|---|---|---|---|
| iPS:435847 | 21-225_191A3 | NA | AGGGCCAGTCAGAGTATTCGCAGCAGCTTCTTAGCC SEQ ID NO:2589 | GGTGCATCCAGCAGGGC CACT SEQ ID NO:10601 | CAGCAATATGGTAACTCACC GTGGGCG SEQ ID NO:18613 |
| | | AA | RASQSIRSSFLA SEQ ID NO:2590 | GASSRAT SEQ ID NO:10602 | QQYGNSPWA SEQ ID NO:18614 |
| iPS:435849 | 21-225_191C3 | NA | AGGGCCAGTCAGAGTATTCGCAGCAGCTTCTTAGCC SEQ ID NO:2591 | GGTGCATCCAGCAGGGC CACT SEQ ID NO:10603 | CAGCAGTATGGTAACTCACC GTGGGCG SEQ ID NO:18615 |
| | | AA | RASQSIRSSFLA SEQ ID NO:2592 | GASSRAT SEQ ID NO:10604 | QQYGNSPWA SEQ ID NO:18616 |
| iPS:435851 | 21-225_191D3 | NA | AGGGCCGGTCAAAGTATTAGAACCAACTTCTTAGCC SEQ ID NO:2593 | GGTGCATCCAGCAGGGC CACT SEQ ID NO:10605 | CAGCAGTATGGTAGCTCACC GTGGACG SEQ ID NO:18617 |
| | | AA | RAGQSIRTNFLA SEQ ID NO:2594 | GASSRAT SEQ ID NO:10606 | QQYGSSPWT SEQ ID NO:18618 |
| iPS:435853 | 21-225_191E3 | NA | AAGTCTAGTCAGAGCCTCCTCCATAGTGATGGAAGGACCTATTTGTAT SEQ ID NO:2595 | GAGGTTTCCAACCGGTTCGCT SEQ ID NO:10607 | ATGCAAAGTATACAACTTCCCTGGACG SEQ ID NO:18619 |
| | | AA | KSSQSLLHSDGRTYLY SEQ ID NO:2596 | EVSNRFA SEQ ID NO:10608 | MQSIQLPWT SEQ ID NO:18620 |
| iPS:435855 | 21-225_191G3 | NA | AAGTCCAGCCAGAGTGTTTTACACAGGTCCAACAGTTACAACTACTTAGCT SEQ ID NO:2597 | TGGGCATCTACCCGAAAATCC SEQ ID NO:10609 | CAGCAATATTATAGTAGTCCTCCCACT SEQ ID NO:18621 |
| | | AA | KSSQSVLHSSNSYNYLA SEQ ID NO:2598 | WASTRKS SEQ ID NO:10610 | QQYYSSPPT SEQ ID NO:18622 |
| iPS:435857 | 21-225_191A4 | NA | CGGGCAAGTCAGGGCATTAGAAAAGATTTAGGC SEQ ID NO:2599 | ACTGCATCCAGTTGCAAAAT SEQ ID NO:10611 | CTACAGCATAATAGTTACCGTGGACG SEQ ID NO:18623 |

FIGURE 49
(Continued)

| | | | RASQGIRKDLG | TASSLQN | LQHNSYPWT |
|---|---|---|---|---|---|
| iPS:435859 | | AA | RASQGIRKDLG<br>SEQ ID NO:2600 | TASSLQN<br>SEQ ID NO:10612 | LQHNSYPWT<br>SEQ ID NO:18624 |
| | 21-225_190E6 | NA | CGGACGAGTCAGGGCATTGG<br>CAATTATTAGCC<br>SEQ ID NO:2601 | AAAGCATCCAGTTTGCA<br>AAGT<br>SEQ ID NO:10613 | CAACAGTATATGACTTACCC<br>GCTCACT<br>SEQ ID NO:18625 |
| iPS:435861 | | AA | RTSQGIGNYLA<br>SEQ ID NO:2602 | KASSLQS<br>SEQ ID NO:10614 | QQYMTYPLT<br>SEQ ID NO:18626 |
| | 21-225_190A5 | NA | CGGGCGAGTCAGGGGATTG<br>GCAATCATTAGCC<br>SEQ ID NO:2603 | GCTGCATCCAGTTTGCAA<br>AGT<br>SEQ ID NO:10615 | CAACAGTATAGTAATTACCC<br>AGTCACT<br>SEQ ID NO:18627 |
| iPS:435863 | | AA | RASQGIGNHLA<br>SEQ ID NO:2604 | AASSLQS<br>SEQ ID NO:10616 | QQYSNYPVT<br>SEQ ID NO:18628 |
| | 21-225_191H4 | NA | CGGGCCAATCAGAGCATTGG<br>TAGTAGCTTACAC<br>SEQ ID NO:2605 | TATGCTTCCCAGTCCCTC<br>TCA<br>SEQ ID NO:10617 | CATCAGACTGGTAGGTTACC<br>TCTCACT<br>SEQ ID NO:18629 |
| iPS:435865 | | AA | RANQSIGSSLH<br>SEQ ID NO:2606 | YASQSLS<br>SEQ ID NO:10618 | HQTGRLPLT<br>SEQ ID NO:18630 |
| | 21-225_191A5 | NA | AGGGCCAGTCAGAGTGTTAG<br>CAGCAGGTTCTTAGCC<br>SEQ ID NO:2607 | GGTGCTTCCAACAGGGC<br>CACT<br>SEQ ID NO:10619 | CAGCAGTATGGTGGTTCACC<br>TCCGTGGACG<br>SEQ ID NO:18631 |
| iPS:435867 | | AA | RASQSVSSRFLA<br>SEQ ID NO:2608 | GASNRAT<br>SEQ ID NO:10620 | QQYGGSPPWT<br>SEQ ID NO:18632 |
| | 21-225_191E5 | NA | CGGGCCAGTCAGAGCATTGG<br>TAGTAGCTTACAC<br>SEQ ID NO:2609 | TATGCTTCCCAGTCCTTC<br>TCA<br>SEQ ID NO:10621 | CATCAGAGTAGTAGTTTCCC<br>TCGGACG<br>SEQ ID NO:18633 |
| iPS:435869 | | AA | RASQSIGSSLH<br>SEQ ID NO:2610 | YASQSFS<br>SEQ ID NO:10622 | HQSSSFPRT<br>SEQ ID NO:18634 |
| | 21-225_190B1 | NA | CGGGCGAGTCAGGGCATTAG<br>AAATTATTTAGCC<br>SEQ ID NO:2611 | GTTGCATCCAGTTTGGAA<br>AGT<br>SEQ ID NO:10623 | CAACAGTATCTTAATTACCC<br>AGTCACT<br>SEQ ID NO:18635 |

FIGURE 49
(Continued)

| | | | | RASQGIRNYLA | VASSLES | QQYLNYPVT |
|---|---|---|---|---|---|---|
| iPS:435871 | 21-225_191E6 | AA | | RASQGIRNYLA | VASSLES | QQYLNYPVT |
| | | | | SEQ ID NO:2612 | SEQ ID NO:10624 | SEQ ID NO:18636 |
| iPS:435873 | 21-225_191E6 | NA | | AAGTCTAGTCAGAGCCTCCT CCATAGTGATGGAAGGACCT ATTTGTAT | GAGGTTTCCAACCGGTTC GCT | ATGCAAAGTATACATTTTCC CTGGACG |
| | | | | SEQ ID NO:2613 | SEQ ID NO:10625 | SEQ ID NO:18637 |
| iPS:435873 | 21-225_190G4 | AA | | KSSQSLLHSDGRTYLY | EVSNRFA | MQSIHFPWT |
| | | | | SEQ ID NO:2614 | SEQ ID NO:10626 | SEQ ID NO:18638 |
| iPS:435875 | 21-225_190G4 | NA | | CGGGGGAGTCAGGACATTGG CAGATATTTAGCC | GCTGCATCCAGTTGCAA AGT | CAACAATATAGTACTTACCC GCTCACT |
| | | | | SEQ ID NO:2615 | SEQ ID NO:10627 | SEQ ID NO:18639 |
| iPS:435875 | 21-225_190B9 | AA | | RASQDIGRYLA | AASSLQS | QQYSTYPLT |
| | | | | SEQ ID NO:2616 | SEQ ID NO:10628 | SEQ ID NO:18640 |
| iPS:435877 | 21-225_190B9 | NA | | CGGGCGAGTCAGGGTATTAA CAACTGGTTAGCC | GGTGTTTCCAGTTGCAG AGT | CAACAGGCTAACAGTTCCC GTGGACG |
| | | | | SEQ ID NO:2617 | SEQ ID NO:10629 | SEQ ID NO:18641 |
| iPS:435877 | 21-225_184E7 | AA | | RASQGINNWLA | GVSSLQS | QQANSFPWT |
| | | | | SEQ ID NO:2618 | SEQ ID NO:10630 | SEQ ID NO:18642 |
| iPS:435879 | 21-225_184E7 | NA | | CGGGCGAGTCAGGGCATTAG CAATTATTTAGCC | GCTGCATCCAGTTGCAA AGT | CAACAGTATAATGGTTACCC ATTCACT |
| | | | | SEQ ID NO:2619 | SEQ ID NO:10631 | SEQ ID NO:18643 |
| iPS:435879 | 21-225_184H10 | AA | | RASQGISNYLA | AASSLQS | QQYNGYPFT |
| | | | | SEQ ID NO:2620 | SEQ ID NO:10632 | SEQ ID NO:18644 |
| iPS:435881 | 21-225_184H10 | NA | | CGGGCAAGTCAGGGCATTAG AAATGATTTAGGC | ATTGCATCCAGTTGCAA AGT | CTACACAGCATAATAGTTACCC ATTCACT |
| | | | | SEQ ID NO:2621 | SEQ ID NO:10633 | SEQ ID NO:18645 |
| iPS:435881 | | AA | | RASQGIRNDLG | IASSLQS | LQHNSYPFT |
| | | | | SEQ ID NO:2622 | SEQ ID NO:10634 | SEQ ID NO:18646 |
| | | NA | | CGGGCAAGTCAGGGCATTAG AAATGATTTAGGC | ATTGCATCCAGTTGCAA AGT | CTACACAGCATAATAGTTACCC ATTCACT |

FIGURE 49
(Continued)

| | | | | | | |
|---|---|---|---|---|---|---|
| iPS:435883 | 21-225_184D11 | AA | SEQ ID NO:2623 RASQGIRNDLG | SEQ ID NO:10635 IASSLQS | SEQ ID NO:18647 LQHNSYPFT | |
| | | NA | SEQ ID NO:2624 CGGGCGAGTCAGGGCATTAG CAATTATTAGCC | SEQ ID NO:10636 GTTGCATCCAGTTTGCAA AGT | SEQ ID NO:18648 CGACAATATCATAGTTACC ATTCACT | |
| iPS:435885 | 21-225_185A1 | AA | SEQ ID NO:2625 RASQGISNYLA | SEQ ID NO:10637 VASSLQS | SEQ ID NO:18649 RQYHSYPFT | |
| | | NA | SEQ ID NO:2626 CGGGCGAGTCAGGGCATTAG CAATTATTAGCC | SEQ ID NO:10638 GCTGCATCCAGTTTGCAA AGT | SEQ ID NO:18650 CAACAGTATAATGGTTACC ATTCACT | |
| iPS:435887 | 21-225_185E10 | AA | SEQ ID NO:2627 RASQGISNYLA | SEQ ID NO:10639 AASSLQS | SEQ ID NO:18651 QQYNGYPFT | |
| | | NA | SEQ ID NO:2628 AAGTCTAGTCAGAGCCTCCT GCATGGTGATGGAAAGACCT ATTTGTGT | SEQ ID NO:10640 GAAGTTTCCAAGCGGTT CTCT | SEQ ID NO:18652 ATGCAAAGTATACAGGTTCC CTGGACG | |
| iPS:435889 | 21-225_186F7 | AA | SEQ ID NO:2629 KSSQSLLHGDGKTYLC | SEQ ID NO:10641 EVSKRFS | SEQ ID NO:18653 MQSIQVPWT | |
| | | NA | SEQ ID NO:2630 CGGGCGAGTCAGGGCATTAG CAGCTGGTTAGCC | SEQ ID NO:10642 GCTGCATCCAGTTTACAA AGT | SEQ ID NO:18654 CAACAGGTTAACAGTTTCCC ATTCACT | |
| iPS:435891 | 21-225_186A11 | AA | SEQ ID NO:2631 RASQDITSWLA | SEQ ID NO:10643 AASSLQS | SEQ ID NO:18655 QQVNSFPFT | |
| | | NA | SEQ ID NO:2632 CGGGCGAGTCAGGGCATTAG CAATTATTAGCC | SEQ ID NO:10644 GCTGCTTCCAGTTTGCAA AGT | SEQ ID NO:18656 CAACAGTATAATAGTTATCC ATTCACT | |
| | 21-225_188H5 | AA | SEQ ID NO:2633 RASQGISNYLA | SEQ ID NO:10645 AASSLQS | SEQ ID NO:18657 QQYNSYPFT | |
| | | NA | SEQ ID NO:2634 | SEQ ID NO:10646 | SEQ ID NO:18658 | |

FIGURE 49
(Continued)

| | | | | | |
|---|---|---|---|---|---|
| iPS:435895 | 21-225_188E8 | NA | CGGGCGAATCAGGATATTTC CAGCTGGTTAGCC SEQ ID NO:2635 | GCTGCATCCAATTTGCAA AGT SEQ ID NO:10647 | CAGCAGGCTAACAGTTTCC GTGGACG SEQ ID NO:18659 |
| | | AA | RANQDISSWLA SEQ ID NO:2636 | AASNLQS SEQ ID NO:10648 | QQANSFPWT SEQ ID NO:18660 |
| iPS:435897 | 21-225_188B9 | NA | CGGGCGAGTCAGGGCATTAG CAATTATTAGCC SEQ ID NO:2637 | GCTGCATCCAGTTTGCAA AGT SEQ ID NO:10649 | CAACAGTATAATAGTTACC ATTCACT SEQ ID NO:18661 |
| | | AA | RASQGISNYLA SEQ ID NO:2638 | AASSLQS SEQ ID NO:10650 | QQYNSYPFT SEQ ID NO:18662 |
| iPS:435899 | 21-225_188G11 | NA | ATGTCTAGTCAGAGCCTCCT GCATGGTGATGGAAAGACCT ATTTATAT SEQ ID NO:2639 | GAAGTTTCCAACCGGTTC TCT SEQ ID NO:10651 | ATGCAAAGTATACAGATTCC TTGGACG SEQ ID NO:18663 |
| | | AA | MSSQSLLHGDGKTYLY SEQ ID NO:2640 | EVSNRFS SEQ ID NO:10652 | MQSIQIPWT SEQ ID NO:18664 |
| iPS:435901 | 21-225_189G2 | NA | AAGTCTAGTCAGAGCCTCCT GCATGGTGATGGAAAGACCT ATTTGTTT SEQ ID NO:2641 | GAAGTTTCCAACCGGTTC TCT SEQ ID NO:10653 | ATGCAAAGTATACAGATTCC GTGGACG SEQ ID NO:18665 |
| | | AA | KSSQSLLHGDGKTYLF SEQ ID NO:2642 | EVSNRFS SEQ ID NO:10654 | MQSIQIPWT SEQ ID NO:18666 |
| iPS:435903 | 21-225_190E2 | NA | AAGTCCAGCCAGAGTGTTTT ATTCAACTCCAACAATAAGA ACTACTTAGCT SEQ ID NO:2643 | TGGGCATCTACCCGGGA ATCC SEQ ID NO:10655 | CAGCAATATTGTAGTCTTCC ATTCACT SEQ ID NO:18667 |
| | | AA | KSSQSVLFNSNNKNYLA SEQ ID NO:2644 | WASTRES SEQ ID NO:10656 | QQYCSLPFT SEQ ID NO:18668 |
| iPS:435905 | | NA | AGGGCCAGTCAGAATATAA GGAGCAACTTCTTAGCC | GGTGCATCCAGCAGGGC CACT | CAGCAGTATGGTAACTCACC GTGGACG |

FIGURE 49
(Continued)

| | | | | | | |
|---|---|---|---|---|---|---|
| iPS:435907 | 21-225_190A3 | AA | SEQ ID NO:2645 RASQNIRSNFLA | SEQ ID NO:2646 | SEQ ID NO:10657 GASSRAT | SEQ ID NO:10658 | SEQ ID NO:18669 QQYGNSPWT | SEQ ID NO:18670 |
| iPS:435909 | 21-225_190G3 | NA | SEQ ID NO:2647 | CGGGCAAGTCAGGGCATTAG AAAAGATTTAGGC | SEQ ID NO:10659 AGT | ACTGCATCCAGTTGCAA | SEQ ID NO:18671 LQHNSYPWT | CTACAGGCATAATAGTTACCC GTGGACG |
| | | AA | SEQ ID NO:2648 RASQGIRKDLG | | SEQ ID NO:10660 TASSLQS | | SEQ ID NO:18672 | |
| iPS:435911 | 21-225_190H3 | NA | SEQ ID NO:2649 | CGGGGAGTCAGGGTCTTAA CAACTGGTTAGCC | SEQ ID NO:10661 AGT | GCTGTGTCCAGTTTGCAA | SEQ ID NO:18673 | CAACAGGCTAACAGTCTCCC GTGGACG |
| | | AA | SEQ ID NO:2650 RASQGLNNWLA | | SEQ ID NO:10662 AVSSLQS | | SEQ ID NO:18674 QQANSLPWT | |
| iPS:435913 | 21-225_190B4 | NA | SEQ ID NO:2651 | AGGGCCAGTCAGAGTATTCG CAGCAGCTTCTTAGCC | SEQ ID NO:10663 CACT | GGTGCATCCAGCAGGGC | SEQ ID NO:18675 | CAGCAGTATGGTAACTCACC GTGGGCG |
| | | AA | SEQ ID NO:2652 RASQSIRSSFLA | | SEQ ID NO:10664 GASSRAT | | SEQ ID NO:18676 QQYGNSPWA | |
| iPS:435915 | 21-225_190A7 | NA | SEQ ID NO:2653 | AGGGCCAGTCAGAGTGTTAG AAGCAACTTCTTAGCC | SEQ ID NO:10665 CACT | GGTGCATACCGCAGGGC | SEQ ID NO:18677 | CAGCAGTATGGTAACTCACC GTGGACG |
| | | AA | SEQ ID NO:2654 RASQSVRSNFLA | | SEQ ID NO:10666 GAYRRAT | | SEQ ID NO:18678 QQYGNSPWT | |
| iPS:435915 | 21-225_190H4 | NA | SEQ ID NO:2655 | AAGTCCAGCAGCAGAGTGTTT ACACAGTCCAACAATTACA ACTACTTAGCT | SEQ ID NO:10667 WASTRES | TGGGCATCTACCCGGGA ATCC | SEQ ID NO:18679 | CAGCAATATTATAGTATTCC TCCCACT |
| | | AA | SEQ ID NO:2656 KSSQSVLHSSNNYNYLA | | | | SEQ ID NO:18680 QQYYSIPPT | |

FIGURE 49 (Continued)

| | | | | | |
|---|---|---|---|---|---|
| iPS:435917 | 21-225_190D5 | NA | CGGGCCAAGTCAGAGTATTGG TAGTAACTTACAC SEQ ID NO:2657 | TCTGCTTCCCAGTCCTTC TCA SEQ ID NO:10669 | CAGCAGAGTAGTAGTTTACC GTGGACG SEQ ID NO:18681 |
| | | AA | RASQSIGSNLH SEQ ID NO:2658 | SASQSFS SEQ ID NO:10670 | QQSSSLPWT SEQ ID NO:18682 |
| iPS:435919 | 21-225_190H5 | NA | CGGGCAAGTCAGGGCATTAG AAAGATTTAGGC SEQ ID NO:2659 | ACTGCATCCAGTTGCAA AGT SEQ ID NO:10671 | CTACAGCATAATAATTACCG GTGGACG SEQ ID NO:18683 |
| | | AA | RASQGIRKDLG SEQ ID NO:2660 | TASSLQS SEQ ID NO:10672 | LQHNNYPWT SEQ ID NO:18684 |
| iPS:435921 | 21-225_190D6 | NA | CGGGCAAGTCAGGGCATTAG AAATGATTTAGGC SEQ ID NO:2661 | GCTGCATCCAGTTGCAA AGT SEQ ID NO:10673 | CTACAGCATTATAGTTTCCC ATTCACT SEQ ID NO:18685 |
| | | AA | RASQGIRNDLG SEQ ID NO:2662 | AASSLQS SEQ ID NO:10674 | LQHYSFPFT SEQ ID NO:18686 |
| iPS:435923 | 21-225_190H6 | NA | AAGTCCAGCCAGAGTGTTTT ATTCAACTCCAACAATAAGA ACTACTTAGCT SEQ ID NO:2663 | TGGGCATCTACCCGGGA ATCC SEQ ID NO:10675 | CAGCAATATTGTAGTCTTCC ATTCACT SEQ ID NO:18687 |
| | | AA | KSSQSVLFNSNKNYLA SEQ ID NO:2664 | WASTRES SEQ ID NO:10676 | QQYCSLPFT SEQ ID NO:18688 |
| iPS:435925 | 21-225_190D7 | NA | AAGTCCAGCCAGAGTGTTTT ATCCAGCTCCAACAATTACA ACTATTTAGTT SEQ ID NO:2665 | TGGGCATCTACCCGGAA ATCC SEQ ID NO:10677 | CAACAATATATCGTACTCC GTGGACG SEQ ID NO:18689 |
| | | AA | KSSQSVLSSSNNYNYLV SEQ ID NO:2666 | WASTRKS SEQ ID NO:10678 | QQYRTPWT SEQ ID NO:18690 |
| iPS:435927 | 21-225_190E7 | NA | AAGTCTAGTCAGAGCCTCCT CCATAGTGATGGAAGGACCT ATTTGTAT | GAGGTTTCCAACCGGTC TCT | ATGCAAAGTATACAGCTTCC CTGGACG |

FIGURE 49
(Continued)

| | | | | | | | | |
|---|---|---|---|---|---|---|---|---|
| iPS:435929 | 21-225_190E7 | AA | SEQ ID NO:2667 | KSSQSLLHSDGRTYLY | SEQ ID NO:10679 | EVSNRFS | SEQ ID NO:18691 | MQSIQLPWT |
| | | NA | SEQ ID NO:2668 CGGGCCAGTCAGAGCATTGGTAGTAGCTTACAC | SEQ ID NO:10680 TATGCTTCCCAGTCCTTCTCA | SEQ ID NO:18692 CATCAGAGTAGTAGTTTCCCTCGGACG | | | |
| iPS:435933 | 21-225_190D9 | AA | SEQ ID NO:2669 RASQSIGSSLH | SEQ ID NO:10681 YASQSFS | SEQ ID NO:18693 HQSSSFPRT | | |
| | | NA | SEQ ID NO:2670 CGGACGAGTCAGGGCATTGGCAATTATTTAGCC | SEQ ID NO:10682 AAAGCATCCAGTTTACAAAGT | SEQ ID NO:18694 CAACAGTATATGACTTACCACTCACT | | |
| iPS:435935 | 21-225_190F8 | AA | SEQ ID NO:2671 RTSQGIGNYLA | SEQ ID NO:10683 KASSLQS | SEQ ID NO:18695 QQYMFYPLT | | |
| | | NA | SEQ ID NO:2672 CGGGCCAGTCAGAGCATTGGTAGTAGCTTACAC | SEQ ID NO:10684 TATGCTTCCCAGTCCTTCTCA | SEQ ID NO:18696 CATCAGAGTAGTAGTTTCCCTCGGACG | | |
| iPS:435937 | 21-225_190H8 | AA | SEQ ID NO:2673 RASQSIGSSLH | SEQ ID NO:10685 YASQSFS | SEQ ID NO:18697 HQSSSFPRT | | |
| | | NA | SEQ ID NO:2674 CGGGCGAGTCAGGGCATTGGCAAGTATTTAGCC | SEQ ID NO:10686 GCTGCATCCAGTTGCAAAGT | SEQ ID NO:18698 CAACAGTATGATACTTACCATTCACT | | |
| iPS:435939 | 21-225_190H9 | AA | SEQ ID NO:2675 RASQGIGKYLA | SEQ ID NO:10687 AASSLQS | SEQ ID NO:18699 QRYDTYPFT | | |
| | | NA | SEQ ID NO:2676 AGGGCCGGTCAAAGTATTAGAACCGACTTCTTAGCC | SEQ ID NO:10688 GGTCCATCCAGCAGGGCCACT | SEQ ID NO:18700 CAGCAGTATGGTAGCTCACCGTGGACG | | |
| iPS:435941 | 21-225_191H7 | AA | SEQ ID NO:2677 RAGQSIRTDFLA | SEQ ID NO:10689 GPSSRAT | SEQ ID NO:18701 QQYGSSPWT | | |
| | | NA | SEQ ID NO:2678 AGGGCCCAGTCAGAGTTTAGCAGAAACTTAGCC | SEQ ID NO:10690 GGTGCATCCACTAGGGCCACT | SEQ ID NO:18702 CAGCAGTATAATAACTGGCCGCTCACT | | |

FIGURE 49
(Continued)

| | | | | | |
|---|---|---|---|---|---|
| iPS:435943 | 21-225_191E8 | AA | SEQ ID NO:2679<br>RPSQSFSRNLA<br>SEQ ID NO:2680 | SEQ ID NO:10691<br>GASTRAT<br>SEQ ID NO:10692 | SEQ ID NO:18703<br>QQYNNWPLT<br>SEQ ID NO:18704 |
| iPS:435945 | 21-225_191C9 | NA | CGGGCCAGTCAGAGTATTGG<br>TAGTAGTTTACAC<br>SEQ ID NO:2681 | TATGCTTCCCAGTCCTTC<br>TCA<br>SEQ ID NO:10693 | CATCAGACTAGAAGTTTACC<br>TCTCACT<br>SEQ ID NO:18705 |
| | | AA | RASQSIGSSLH<br>SEQ ID NO:2682 | YASQSFS<br>SEQ ID NO:10694 | HQTRSLPLT<br>SEQ ID NO:18706 |
| iPS:435947 | 21-225_191A10 | NA | CGGGCGAGTCAGGGCATTGG<br>CAAGTATTTAGCC<br>SEQ ID NO:2683 | GCTGCATCCAGTTTGCAA<br>AGT<br>SEQ ID NO:10695 | CAACAGTATAGTACTTACC<br>GCTCACT<br>SEQ ID NO:18707 |
| | | AA | RASQGIGKYLA<br>SEQ ID NO:2684 | AASSLQS<br>SEQ ID NO:10696 | QQYSTYPLT<br>SEQ ID NO:18708 |
| iPS:435949 | 21-225_191E10 | NA | CGGGCGAGTCAGGGCATTGG<br>CAAGTATTTAGCC<br>SEQ ID NO:2685 | GCTGCATCCAGTTTGCAA<br>AGT<br>SEQ ID NO:10697 | CAACAGTATAGTACTTACC<br>GCTCACT<br>SEQ ID NO:18709 |
| | | AA | RASQGIGKYLA<br>SEQ ID NO:2686 | AASSLQS<br>SEQ ID NO:10698 | QQYSTYPLT<br>SEQ ID NO:18710 |
| iPS:435953 | 21-225_191B12 | NA | AAGTCCAGCAGTCAGAGTGTTT<br>ATTCAACTCCAACAATAAGA<br>ACTACTTAGCT<br>SEQ ID NO:2687 | TGGGCCTCTACCCGGGA<br>ATCC<br>SEQ ID NO:10699 | CAGCAATATTCTAGTCTTCC<br>ATTCACT<br>SEQ ID NO:18711 |
| | | AA | KSSQSVLFNSNNKNYLA<br>SEQ ID NO:2688 | WASTRES<br>SEQ ID NO:10700 | QQYSSLPFT<br>SEQ ID NO:18712 |
| iPS:435957 | 21-225_191G12 | NA | CGGACGAGTCAGGGCATTGG<br>CAATTATTAGCC<br>SEQ ID NO:2689 | AAAGCATCCAGTTTGCA<br>AAGT<br>SEQ ID NO:10701 | CAACAGTATATCACTTACC<br>GCTCACT<br>SEQ ID NO:18713 |
| | | AA | RTSQGIGNYLA<br>SEQ ID NO:2690 | KASSLQS<br>SEQ ID NO:10702 | QQYITYPLT<br>SEQ ID NO:18714 |

FIGURE 49
(Continued)

| ID | | Seq 1 | Seq 2 | Seq 3 |
|---|---|---|---|---|
| iPS:435961 | NA | CGGGCGAATCAGGGCATTAA CAATTATTAGCC<br>SEQ ID NO:2691 | GCTGCATCCAGTTTGCAA AGT<br>SEQ ID NO:10703 | CAACAGTATAATAGTTACCC ATTCACT<br>SEQ ID NO:18715 |
| 21-225_192A2 | AA | RANQGINNYLA<br>SEQ ID NO:2692 | AASSLQS<br>SEQ ID NO:10704 | QQYNSYPFT<br>SEQ ID NO:18716 |
| iPS:435963 | NA | CGGGCGAGTCAGGGCATTAG CAATTATTAGCC<br>SEQ ID NO:2693 | GCTGCATCCAGTTTGCAA AGT<br>SEQ ID NO:10705 | CAACATTATGTTACTTACC GAACACT<br>SEQ ID NO:18717 |
| 21-225_192D2 | AA | RASQGISNYLA<br>SEQ ID NO:2694 | AASSLQS<br>SEQ ID NO:10706 | QHYVTYPNT<br>SEQ ID NO:18718 |
| iPS:435965 | NA | CGGGCGAGTCAGGGTATAA GTAGTTGGATAGCC<br>SEQ ID NO:2695 | GGTGCATCCAGTTTGCA AAGT<br>SEQ ID NO:10707 | CAACAGTCTAACAGTTTCCC ATTCACT<br>SEQ ID NO:18719 |
| 21-225_192H2 | AA | RASQGISSWIA<br>SEQ ID NO:2696 | GASSLQS<br>SEQ ID NO:10708 | QQSNSFPFT<br>SEQ ID NO:18720 |
| iPS:435967 | NA | AGGGCCAGTCAGAGTGTTCG CAGCAGTTCCTTGCC<br>SEQ ID NO:2697 | GGTGCATCTAGCAGGGC CACT<br>SEQ ID NO:10709 | CAGCAGTATGGTAACTCACC GTGGGCG<br>SEQ ID NO:18721 |
| 21-225_192B3 | AA | RASQSVRSSFLA<br>SEQ ID NO:2698 | GASSRAT<br>SEQ ID NO:10710 | QQYGNSPWA<br>SEQ ID NO:18722 |
| iPS:435971 | NA | CGGGCGAGTCAGGGCATTAG CAATTATTAGCC<br>SEQ ID NO:2699 | GCTGCATCCAGTTTGCAA AGT<br>SEQ ID NO:10711 | CTACATTATCTTACTTACCCT CTCACT<br>SEQ ID NO:18723 |
| 21-225_192D3 | AA | RASQGISNYLA<br>SEQ ID NO:2700 | AASSLQS<br>SEQ ID NO:10712 | LHYLTYPLT<br>SEQ ID NO:18724 |
| iPS:435973 | NA | AGGGCCAGTCAGAGTGTTAG CAGCAACTTCTTAGCC<br>SEQ ID NO:2701 | GGTGCATCCAGCAGGGC CACT<br>SEQ ID NO:10713 | CAGCAATATGGTATCTCACC GTGGACG<br>SEQ ID NO:18725 |
| 21-225_192H3 | AA | RASQSVSSNFLA<br>SEQ ID NO:2702 | GASSRAT<br>SEQ ID NO:10714 | QQYGISPWT<br>SEQ ID NO:18726 |

FIGURE 49
(Continued)

| | | | | | |
|---|---|---|---|---|---|
| iPS:435977 | 21-225_192E4 | NA | CGGGGCGAGTCAGGGCATTGG CAATTATTAGCC SEQ ID NO:2703 | GTTGTATCCAGTTTACAA AGT SEQ ID NO:10715 | CAACGGTATGATACTTACCC ATTCACT SEQ ID NO:18727 |
| | | AA | RASQGIGNYLA SEQ ID NO:2704 | VVSSLQS SEQ ID NO:10716 | QRYDTYPFT SEQ ID NO:18728 |
| iPS:435979 | 21-225_192H4 | NA | CGGGCGAGTCAGGACATTAG CAATTATTAGCC SEQ ID NO:2705 | GCTGCATCCAGTTTGCAA AGT SEQ ID NO:10717 | CTACATTATCTCAATTACCC GCTCACT SEQ ID NO:18729 |
| | | AA | RASQDISNYLA SEQ ID NO:2706 | AASSLQS SEQ ID NO:10718 | LHYLNYPLT SEQ ID NO:18730 |
| iPS:435983 | 21-225_192E5 | NA | CGGGCCAGTCAGAGCATTGG TAGGAGTTTACAC SEQ ID NO:2707 | TATGCTTCCAGTCATTC TCA SEQ ID NO:10719 | CATCAGAGTAGTCGTTTACC GCTCACT SEQ ID NO:18731 |
| | | AA | RASQSIGRSLH SEQ ID NO:2708 | YASQSFS SEQ ID NO:10720 | HQSSRLPLT SEQ ID NO:18732 |
| iPS:435985 | 21-225_192F6 | NA | CGGGCAAGTCAGGGCATTAG AAATGATTTAGGC SEQ ID NO:2709 | GCTGCATCCAGTTTGCAA AGT SEQ ID NO:10721 | CTACAGCATTATAGTTTCCC ATTCACT SEQ ID NO:18733 |
| | | AA | RASQGIRNDLG SEQ ID NO:2710 | AASSLQS SEQ ID NO:10722 | LQHYSFPFT SEQ ID NO:18734 |
| iPS:435987 | 21-225_192G6 | NA | CGGACGAGTCAGGGCATTGG CAATTATTAGCC SEQ ID NO:2711 | AAAGCATCCAGTTTGCA AAGT SEQ ID NO:10723 | CAACAGTATATGACTTACCC GCTCACT SEQ ID NO:18735 |
| | | AA | RTSQGIGNYLA SEQ ID NO:2712 | KASSLQS SEQ ID NO:10724 | QQYMTYPLT SEQ ID NO:18736 |
| iPS:435989 | 21-225_192F7 | NA | CGGGCAAGTCAGGGCATTAG AAAAGATTTAGGC SEQ ID NO:2713 | ACTGCATCCAGTTTGCAA AGT SEQ ID NO:10725 | CTACACGATACTAGTTACCC GTGGACG SEQ ID NO:18737 |
| | | AA | RASQGIRKDLG SEQ ID NO:2714 | TASSLQS SEQ ID NO:10726 | LQHTSYPWT SEQ ID NO:18738 |

FIGURE 49
(Continued)

| | | | | | |
|---|---|---|---|---|---|
| iPS:435993 | 21-225_192C8 | NA | CGGGCGAGTCAGGGCATTAG CAATTATTTAGCC SEQ ID NO:2715 RASQGISNYLA | GCTGCATCCAGTTTGCAA AGT SEQ ID NO:10727 AASSLQS | CAACATTATCTTACTTACCCT CTCACT SEQ ID NO:18739 QHYLTYPLT |
| | | AA | SEQ ID NO:2716 | SEQ ID NO:10728 | SEQ ID NO:18740 |
| iPS:435995 | 21-225_192F8 | NA | AGGGCCAGTCAGAGTATTAG CAGCAGTACTTAGCC SEQ ID NO:2717 RASQSISSSYLA | GGTGCATCCAGCAGGGC CACT SEQ ID NO:10729 GASSRAT | CAGCAGTATGAGAGTTCACC GTGGACG SEQ ID NO:18741 QQYESSPWT |
| | | AA | SEQ ID NO:2718 | SEQ ID NO:10730 | SEQ ID NO:18742 |
| iPS:435997 | 21-225_192G8 | NA | CGGACGAGTCAGGGCATTGG CAATTATTTAGCC SEQ ID NO:2719 RTSQGIGNYLA | AAAGCATCCAGTTTGCA AAGT SEQ ID NO:10731 KASSLQS | CAACAGTATATCACTTACCC GCTCACT SEQ ID NO:18743 QQYITYPLT |
| | | AA | SEQ ID NO:2720 | SEQ ID NO:10732 | SEQ ID NO:18744 |
| iPS:435999 | 21-225_192F9 | NA | AAGTCTAGTCAGAGCCTCCT CCATAGTGATGGAAGGACCT ATTTGTAT SEQ ID NO:2721 KSSQSLLHSDGRTYLY | GAGGTTTCCAACCGGTTC GCT SEQ ID NO:10733 EVSNRFA | ATGCAAAGTATACAGTTTCC CTGGACG SEQ ID NO:18745 MQSIQLPWT |
| | | AA | SEQ ID NO:2722 | SEQ ID NO:10734 | SEQ ID NO:18746 |
| iPS:436001 | 21-225_192C10 | NA | CGGGCGAGTCAGGGCATTGG CAAGTATTTAGCC SEQ ID NO:2723 RASQGIGKYLA | GCTGCATCCAGTTTGCAA AGT SEQ ID NO:10735 AASSLQS | CAACGATATGATACTTACCC ATTCACT SEQ ID NO:18747 QRYDTYPFT |
| | | AA | SEQ ID NO:2724 | SEQ ID NO:10736 | SEQ ID NO:18748 |
| iPS:436003 | 21-225_192G10 | NA | CGGGCAAGTCAGAGCATTAG CAACTATTTAAAT SEQ ID NO:2725 RASQSISNYLN | GCTGAATCCAGTTTACA AAGT SEQ ID NO:10737 AESSLQS | CAACAGAGTTACAGTTCCCC TCCGTGGACG SEQ ID NO:18749 QQSYSSPPWT |

FIGURE 49
(Continued)

| | | | | | | |
|---|---|---|---|---|---|---|
| iPS:436005 | 21-225_192H10 | NA | SEQ ID NO:2726 CGGGCGAGTCAGGGCATTGG CAAGTATTTAGCC | SEQ ID NO:10738 GCTGCATCCAGTTTGCAA AGT | SEQ ID NO:18750 CAACAGTATAGTACTTACCC GCTCACT |
| | | AA | SEQ ID NO:2727 RASQGIGKYLA | SEQ ID NO:10739 AASSLQS | SEQ ID NO:18751 QQYSTYPLT |
| iPS:436007 | 21-225_192G12 | NA | SEQ ID NO:2728 AGGGCCAGTCAGAGTGTCAG AAGCGACTTCTTAGCC | SEQ ID NO:10740 GGTGTATCCCGCAGGGC CACT | SEQ ID NO:18752 CAGCAGTATGGTAACTCACC GTGGACG |
| | | AA | SEQ ID NO:2729 RASQSVRSDFLA | SEQ ID NO:10741 GVSRRAT | SEQ ID NO:18753 QQYGNSPWT |
| iPS:436009 | 21-225_193A1 | NA | SEQ ID NO:2730 AGGGCCAGTCAGAGTGTTAG AAGCAACTTCTTAGCC | SEQ ID NO:10742 GGTGCATCCCGCAGGGC CACT | SEQ ID NO:18754 CAGCAGTATGGTAACTCACC GTGGACG |
| | | AA | SEQ ID NO:2731 RASQSVRSNFLA | SEQ ID NO:10743 GASRRAT | SEQ ID NO:18755 QQYGNSPWT |
| iPS:436011 | 21-225_193B1 | NA | SEQ ID NO:2732 AGGGCCAGTCAGAGTGTTAG AAGCAACTTCTTAGCC | SEQ ID NO:10744 GGTGCATCCCGCAGGGC CACT | SEQ ID NO:18756 CAGCAGTATGGTAACTCACC GTGGACG |
| | | AA | SEQ ID NO:2733 RASQSVRSNFLA | SEQ ID NO:10745 GASRRAT | SEQ ID NO:18757 QQYGNSPWT |
| iPS:436013 | 21-225_193F2 | NA | SEQ ID NO:2734 CGGGCCAGTCAGAGTATTAA CAACTGGTTAGCC | SEQ ID NO:10746 GGTGTTTCCAGTTTGCAA AGT | SEQ ID NO:18758 CAACAGGCTAACAGTTTCCC GTGGACG |
| | | AA | SEQ ID NO:2735 RASQGINNWLA | SEQ ID NO:10747 GVSSLQS | SEQ ID NO:18759 QQANSFPWT |
| iPS:436015 | 21-225_193D3 | NA | SEQ ID NO:2736 AGGGCCAGTCAGAGTATTCG CAGCAGTTCTTAGCC | SEQ ID NO:10748 GGTGCATCCAACAGGGC CACT | SEQ ID NO:18760 CAGCAGTATGGTAACTCACC GTGGGCG |
| | | AA | SEQ ID NO:2737 RASQSIRSSFLA | SEQ ID NO:10749 GASNRAT | SEQ ID NO:18761 QQYGNSPWA |

FIGURE 49
(Continued)

| | | | | | |
|---|---|---|---|---|---|
| iPS:436017 | 21-225_193F3 | NA | SEQ ID NO:2738<br>AGGGCCGGTCAAAGTATTAG<br>AACCGACTTCTTAGTC<br>SEQ ID NO:2739<br>RAGQSIRTDFLV | SEQ ID NO:10750<br>GGTGCATCCAGCAGGGC<br>CACT<br>SEQ ID NO:10751<br>GASSRAT | SEQ ID NO:18762<br>CAGCAGTATGGAAGCTCACC<br>GTGGACG<br>SEQ ID NO:18763<br>QQYGSSPWT |
| iPS:436019 | 21-225_193C4 | NA<br>AA | SEQ ID NO:2740<br>CGGCCGAGTCAGGGCATTAG<br>CATTTATTAGCC<br>SEQ ID NO:2741<br>RPSQGISIYLA | SEQ ID NO:10752<br>GCTGCATCCACCTTACAA<br>TCA<br>SEQ ID NO:10753<br>AASTLQS | SEQ ID NO:18764<br>CAAAAGTATAACAGTGCCCC<br>ATTCACT<br>SEQ ID NO:18765<br>QKYNSAPFT |
| iPS:436021 | 21-225_193G4 | NA<br>AA | SEQ ID NO:2742<br>AAGTCCAGCCAGAGTGTTT<br>ATACAGCTCCAACAATTATA<br>ACTACTTGACT<br>SEQ ID NO:2743<br>KSSQSVLYSSNNYNYLT | SEQ ID NO:10754<br>TGGGCATCTACCCGAAA<br>ATCC<br>SEQ ID NO:10755<br>WASTRKS | SEQ ID NO:18766<br>CAGCAATATATTATTACTCC<br>GTGGACG<br>SEQ ID NO:18767<br>QQYITPWT |
| iPS:436023 | 21-225_193A5 | NA<br>AA | SEQ ID NO:2744<br>CGGGCAAGTCAGGGCATTAG<br>AAATGATTTAGGG<br>SEQ ID NO:2745<br>RASQGIRNDLG | SEQ ID NO:10756<br>GCTGCATCCAGTTTGCAA<br>AGT<br>SEQ ID NO:10757<br>AASSLQS | SEQ ID NO:18768<br>CTACAGCATAATGATTTCCC<br>GTTCACT<br>SEQ ID NO:18769<br>LQHNDFPFT |
| iPS:436025 | 21-225_193B5 | NA<br>AA | SEQ ID NO:2746<br>CGGGCCAGTCAGAGCATTGG<br>TAGTAGCTTACAC<br>SEQ ID NO:2747<br>RASQSIGSSLH | SEQ ID NO:10758<br>TATGCTTCCCAGTCCTTC<br>TCA<br>SEQ ID NO:10759<br>YASQSFS | SEQ ID NO:18770<br>CATCAGAGTAGTCGTTTACC<br>ATTCACT<br>SEQ ID NO:18771<br>HQSSRLPFT |
| iPS:436027 | 21-225_193E6 | NA | SEQ ID NO:2748<br>AGGGCCAGTCAGAGTGTTAG<br>GAGCGGTTACTTAGCC<br>SEQ ID NO:2749 | SEQ ID NO:10760<br>GGTGCATCCAGCAGGGC<br>CACT<br>SEQ ID NO:10761 | SEQ ID NO:18772<br>CAGCAGTATGAGAGTTCACC<br>GTGGACG<br>SEQ ID NO:18773 |

FIGURE 49
(Continued)

| | | | | | | |
|---|---|---|---|---|---|---|
| iPS:436029 | | AA | RASQSVRSGYLA SEQ ID NO:2750 | GASSRAT SEQ ID NO:10762 | QQYESSPWT SEQ ID NO:18774 |
| iPS:436031 | 21-225_193H6 | NA | AGGGCCGGTCAAAGTATTAG AACCAACTTCTTAGCC SEQ ID NO:2751 | GGTGCATCCAGCAGGGC CACT SEQ ID NO:10763 | CAGCAGTATGGTAGCTCACC GTGGACG SEQ ID NO:18775 |
| iPS:436031 | | AA | RAGSQIRTNFLA SEQ ID NO:2752 | GASSRAT SEQ ID NO:10764 | QQYGSSPWT SEQ ID NO:18776 |
| iPS:436033 | 21-225_193C7 | NA | CGGGCGAGTCAGGGCATTGG CAAGTATTTAGCC SEQ ID NO:2753 | GCTGCATCCAGTTTGCAA AGT SEQ ID NO:10765 | CAACAGTATAGTACTTACC GCTCACT SEQ ID NO:18777 |
| iPS:436033 | | AA | RASQGIGKYLA SEQ ID NO:2754 | AASSLQS SEQ ID NO:10766 | QQYSTYPLT SEQ ID NO:18778 |
| iPS:436035 | 21-225_193E7 | NA | CGGGCAAGTCAGGGCATTAG AAATGATTAGGC SEQ ID NO:2755 | TCTGCATCCAGTTTGCAA AGG SEQ ID NO:10767 | CTACAGCATAAAAGGTACCC GCTCACT SEQ ID NO:18779 |
| iPS:436035 | | AA | RASQGIRNDLG SEQ ID NO:2756 | SASSLQR SEQ ID NO:10768 | LQHKRYPLT SEQ ID NO:18780 |
| iPS:436037 | 21-225_193C8 | NA | AGGGCCAGTCAGAGTATTCG CAGCAGCTTCTTAGCC SEQ ID NO:2757 | GGTGCATCCAGCAGGGC CACT SEQ ID NO:10769 | CAGCAATATGGTAACTCACC GTGGGCG SEQ ID NO:18781 |
| iPS:436037 | | AA | RASQSIRSSFLA SEQ ID NO:2758 | GASSRAT SEQ ID NO:10770 | QQYGNSPWA SEQ ID NO:18782 |
| iPS:436037 | 21-225_193D8 | NA | AGGGCCAGTCAGAGTATAA GGACCAACTTCTTAGCC SEQ ID NO:2759 | GGTGCATCCAGCAGGGC CACT SEQ ID NO:10771 | CAGCAGTATGGTAACTCACC GTGGACG SEQ ID NO:18783 |
| iPS:436037 | | AA | RASQSIRTNFLA SEQ ID NO:2760 | GASSRAT SEQ ID NO:10772 | QQYGNSPWT SEQ ID NO:18784 |
| iPS:436039 | 21-225_193F8 | NA | CGGGCGAGTCAGGGCGTTAG CAATCATTTAGCC SEQ ID NO:2761 | GCTGCATCCAGTTTGCAA AGT SEQ ID NO:10773 | CAACAGTATAATAGTTACCC ATTCACT SEQ ID NO:18785 |

FIGURE 49
(Continued)

| | | | | | | |
|---|---|---|---|---|---|---|
| iPS:436041 | 21-225_193G8 | AA | RASQGVSNHLA SEQ ID NO:2762 | AASSLQS SEQ ID NO:10774 | QQYNSYPFT SEQ ID NO:18786 | |
| | | NA | AGGGCCAGTCAGAGTGTTAG AACCAACTTCTTAGCC SEQ ID NO:2763 | GGTGCATCCCGCAGGGC CACT SEQ ID NO:10775 | CAGCAGTATGGTAACTCACC GTGGACG SEQ ID NO:18787 | |
| iPS:436043 | 21-225_193G9 | AA | RASQSVRTNFLA SEQ ID NO:2764 | GASRRAT SEQ ID NO:10776 | QQYGNSPWT SEQ ID NO:18788 | |
| | | NA | CGGGCCAGTCAGAGCATTGG TAGGAGTTACAC SEQ ID NO:2765 | TATGCTTCCCAGTCATTC TCA SEQ ID NO:10777 | CATCAGAGTAGTCGTTACC GCTCACT SEQ ID NO:18789 | |
| iPS:436045 | 21-225_193A10 | AA | RASQSIGRSLH SEQ ID NO:2766 | YASQSFS SEQ ID NO:10778 | HQSSRLPLT SEQ ID NO:18790 | |
| | | NA | CGGGCGAGTCAGGGCATTAG CAATTATTAGCC SEQ ID NO:2767 | GCTGCATCCAGTTTGCAA AGT SEQ ID NO:10779 | CAACATTATCTTACTTACCCT CTCACT SEQ ID NO:18791 | |
| iPS:436047 | 21-225_193B10 | AA | RASQGISNYLA SEQ ID NO:2768 | AASSLQS SEQ ID NO:10780 | QHYLTYPLT SEQ ID NO:18792 | |
| | | NA | AGGGCCAGTCCGAGTGTTAG CAGCAGCTACTTAGCC SEQ ID NO:2769 | GGTGCATCCAGGAGGGC CACT SEQ ID NO:10781 | CAGCAGTATGGTAGCTCACC TCCGTGGACG SEQ ID NO:18793 | |
| iPS:436049 | 21-225_193B12 | AA | RASPSVSSSYLA SEQ ID NO:2770 | GASRRAT SEQ ID NO:10782 | QQYGSSPWT SEQ ID NO:18794 | |
| | | NA | AGGGCCAGTCAGAGTATTCG CAGCAGCTTCTTAGCC SEQ ID NO:2771 | GATGCATCCAGCAGGGC CACT SEQ ID NO:10783 | CAGCAGTATGGTAACTCACC GTGGGCG SEQ ID NO:18795 | |
| iPS:436051 | 21-225_193G12 | AA | RASQSIRSSFLA SEQ ID NO:2772 | DASSRAT SEQ ID NO:10784 | QQYGNSPWA SEQ ID NO:18796 | |
| | | NA | AGGGCCAGTCAGAGTGTTAG CAGCAGCTTAGCC SEQ ID NO:2773 | GGTGCATCCACCAGGGC CACT SEQ ID NO:10785 | CAGCAGTATAATAACTGGCC GTGCAGT SEQ ID NO:18797 | |

FIGURE 49
(Continued)

| | | | | | | | |
|---|---|---|---|---|---|---|---|
| iPS:436054 | | AA | RASQSVSSSLA | | GASTRAT | | QQYNNWPCS |
| | | | SEQ ID NO:2774 | | SEQ ID NO:10786 | | SEQ ID NO:18798 |
| | 21-225_194C1 | NA | CGGGCGAGTCAGGGCATTAG CAATTATTAGCC | | GCTGCATCCAGTTGCAA AGT | | CTACATTATCTTACTTACCCT CTCACT |
| | | | SEQ ID NO:2775 | | SEQ ID NO:10787 | | SEQ ID NO:18799 |
| iPS:436056 | | AA | RASQGISNYLA | | AASSLQS | | LHYLTYPLT |
| | | | SEQ ID NO:2776 | | SEQ ID NO:10788 | | SEQ ID NO:18800 |
| | 21-225_194C3 | NA | CGGGCCAGTCAGAGTATTGG TAGTAACTTACAC | | TCTGCTTCCAGTCCTTC TCA | | CAGCAGAGTAGTAGTTTACC GTGGACG |
| | | | SEQ ID NO:2777 | | SEQ ID NO:10789 | | SEQ ID NO:18801 |
| iPS:436058 | | AA | RASQSIGSNLH | | SASQSFS | | QQSSSLPWT |
| | | | SEQ ID NO:2778 | | SEQ ID NO:10790 | | SEQ ID NO:18802 |
| | 21-225_194A4 | NA | AGGGCCAGTCGGGGGTGTTAG CAACATCTACTTAGCC | | GGTGCTTCCAACAGGGC CACT | | CAGCACAATGATTACTCAAT GTTCACT |
| | | | SEQ ID NO:2779 | | SEQ ID NO:10791 | | SEQ ID NO:18803 |
| iPS:436060 | | AA | RASRGVSNIYLA | | GASNRAT | | QHNDYSMFT |
| | | | SEQ ID NO:2780 | | SEQ ID NO:10792 | | SEQ ID NO:18804 |
| | 21-225_194F4 | NA | AAGTCTAGTCAGAGCCTCCT CCATAGTGATGGAAGGACCT ATTTGTAT | | GAGGTTTCCAACCGGTTC TCT | | ATGCAAAGTATACAGCTTCC CTGGACG |
| | | | SEQ ID NO:2781 | | SEQ ID NO:10793 | | SEQ ID NO:18805 |
| iPS:436062 | | AA | KSSQSLLHSDGRTYLY | | EVSNRFS | | MQSIQLPWT |
| | | | SEQ ID NO:2782 | | SEQ ID NO:10794 | | SEQ ID NO:18806 |
| | 21-225_194E5 | NA | AGGGCCGGTCAAAGTATTAG AACCAACTTCTTAGCC | | GGTGCATCCAGCAGGGC CACT | | CAGCAGTATGGTAGTTCACC GTGGACG |
| | | | SEQ ID NO:2783 | | SEQ ID NO:10795 | | SEQ ID NO:18807 |
| iPS:436064 | | AA | RAGQSIRTNFLA | | GASSRAT | | QQYGSSPWT |
| | | | SEQ ID NO:2784 | | SEQ ID NO:10796 | | SEQ ID NO:18808 |
| | | NA | AGGGCCAGTCAGAGTATTAG AAGCAACTTCTTAGCC | | GGTGCATCCAGCAGGGC CACT | | CAGCAGTATGGTAGTCACC GTGGACG |

FIGURE 49
(Continued)

| | | | | | | |
|---|---|---|---|---|---|---|
| iPS:436066 | 21-225_194E6 | AA | SEQ ID NO:2785 RASQSIRSNFLA | SEQ ID NO:10797 GASSRAT | SEQ ID NO:18809 QQYGSSPWT | |
| iPS:436068 | 21-225_194B7 | NA | SEQ ID NO:2786 CGGGCGAGTCAGGGCATTAG CAAATATTTAGCC | SEQ ID NO:10798 GGTGCATCCAGGTTGCA AAGT | SEQ ID NO:18810 CAACATTATCTTAATTACCCT CTCACC | |
| | | AA | SEQ ID NO:2787 RASQGISKYLA | SEQ ID NO:10799 GASRLQS | SEQ ID NO:18811 QHYLNYPLT | |
| iPS:436072 | 21-225_194F7 | NA | SEQ ID NO:2788 CGGGCGAGTCAGGGTATTAA CAGGTGGTTAGCC | SEQ ID NO:10800 GCTGCATCCAGTTTGCAA AGT | SEQ ID NO:18812 CAACAGGCTAACAGTTTCCC GTGGACG | |
| | | AA | SEQ ID NO:2789 RASQGISRWLA | SEQ ID NO:10801 AASSLQS | SEQ ID NO:18813 QQANSFPWT | |
| iPS:436074 | 21-225_194C10 | NA | SEQ ID NO:2790 AGGGCCAGTCCGAGTGTTAA CAGCGGCTACTTAGCC | SEQ ID NO:10802 GGTGCATCCAGCAGGGC CACT | SEQ ID NO:18814 CAGCAGTATGAAAAGCTCACC GTGGACG | |
| | | AA | SEQ ID NO:2791 RASPSVNSGYLA | SEQ ID NO:10803 GASSRAT | SEQ ID NO:18815 QQYESSPWT | |
| iPS:436076 | 21-225_194F10 | NA | SEQ ID NO:2792 CGGGCAAGTCAGGGCATTAG AAATGATTTAGGC | SEQ ID NO:10804 GCTGCATCCAGTTTACAA AGT | SEQ ID NO:18816 CTACAGCATTATAGTTTCC ATTCACT | |
| | | AA | SEQ ID NO:2793 RASQGIRNDLG | SEQ ID NO:10805 AASSLQS | SEQ ID NO:18817 LQHYSFPFT | |
| iPS:436078 | 21-225_194H11 | NA | SEQ ID NO:2794 CGGGCGAGTCAGGGCATTAG CAATTATTTAGCC | SEQ ID NO:10806 GCTGCATCCAGTTTACAA AGT | SEQ ID NO:18818 CAACATTATCTTACTTACCCT CTCACC | |
| | | AA | SEQ ID NO:2795 RASQGISNYLA | SEQ ID NO:10807 AASSLQS | SEQ ID NO:18819 QHYLTYPLT | |
| | | NA | SEQ ID NO:2796 CGGGCGAGTCAGGGCATTGG CAAGTATTTAGCA | SEQ ID NO:10808 GCTGCATCCAGTTTGCAA AGT | SEQ ID NO:18820 CAACGATGATACTTACCC ATTCACT | |

FIGURE 49
(Continued)

| | | | | | | |
|---|---|---|---|---|---|---|
| iPS:436080 | 21-225_194H12 | AA | SEQ ID NO:2797<br>RASQGIGKYLA | SEQ ID NO:10809<br>AASSLQS | SEQ ID NO:18821<br>QRYDTYPFT | |
| iPS:436082 | 21-225_195B1 | NA | SEQ ID NO:2798<br>AGGGCCAGTCGAGTGTTAA<br>CAGTAACTACTTAGCC | SEQ ID NO:10810<br>GGTGCATCCAACAGGGC<br>CACT | SEQ ID NO:18822<br>CAGCAGTATGAAAGCTCACC<br>GTGGACG | |
| | | AA | SEQ ID NO:2799<br>RASPSVNSNYLA | SEQ ID NO:10811<br>GASNRAT | SEQ ID NO:18823<br>QQYESSPWT | |
| iPS:436084 | 21-225_195D9 | NA | SEQ ID NO:2800<br>CGGGCGAGTCAGGGTATTAG<br>CAGGTGGTTAGCC | SEQ ID NO:10812<br>GCTGCATCCAGTTTGCTA<br>GGT | SEQ ID NO:18824<br>CAACGGGCTAACAGTTTCC<br>GTGCAGT | |
| | | AA | SEQ ID NO:2801<br>RASQGISRWLA | SEQ ID NO:10813<br>AASSLLG | SEQ ID NO:18825<br>QRANSFPCS | |
| iPS:436086 | 21-225_195F2 | NA | SEQ ID NO:2802<br>CGGGCCAGTCAGAGCAGTTGG<br>TAGTAGCTTACAC | SEQ ID NO:10814<br>TATGCTTCCCAGTCCTTC<br>TCA | SEQ ID NO:18826<br>CATCAGAGTAGAACTTACC<br>GCTCACT | |
| | | AA | SEQ ID NO:2803<br>RASQSIGSSLH | SEQ ID NO:10815<br>YASQSFS | SEQ ID NO:18827<br>HQSRTLPLT | |
| iPS:436088 | 21-225_191G10 | NA | SEQ ID NO:2804<br>CGGACGAGTCAGGGCATTGG<br>CAAGTATTTAGCC | SEQ ID NO:10816<br>AAAGTATCCAGTTTGCA<br>AAGT | SEQ ID NO:18828<br>CAACAGTATATGACTTACC<br>GCTCACT | |
| | | AA | SEQ ID NO:2805<br>RTSQGIGKYLA | SEQ ID NO:10817<br>KVSSLQS | SEQ ID NO:18829<br>QQYMTYPLT | |
| iPS:436088 | 21-225_195C8 | NA | SEQ ID NO:2806<br>AGGGCCAGTCAGAGTATTCG<br>CAGCAGTTCTTAGCC | SEQ ID NO:10818<br>GGTGCATTAGTAGGGC<br>CACT | SEQ ID NO:18830<br>CAGCAGTATGGTAACTCACC<br>GTGGGCG | |
| | | AA | SEQ ID NO:2807<br>RASQSIRSSFLA | SEQ ID NO:10819<br>GAFSRAT | SEQ ID NO:18831<br>QQYGNSPWA | |
| iPS:436090 | | NA | SEQ ID NO:2808<br>CGGGCGAGTCAGGGCATTAG<br>CAATTATTTAGCC | SEQ ID NO:10820<br>GCTGCATCCAGTTTGCAA<br>AGT | SEQ ID NO:18832<br>CAACATTATCTTACTTACCCT<br>CTCACT | |

FIGURE 49
(Continued)

| | | | | | | |
|---|---|---|---|---|---|---|
| iPS:436092 | 21-225_195A9 | AA | SEQ ID NO:2809<br>RASQGISNYLA<br>SEQ ID NO:2810 | SEQ ID NO:2809<br>AASSLQS<br>SEQ ID NO:10822 | SEQ ID NO:18833<br>QHYLTYPLT<br>SEQ ID NO:18834 |
| iPS:436094 | 21-225_195B9 | NA | CGGGCAAGTCAGGGCATAA<br>GAAAAGATTAGGC<br>SEQ ID NO:2811 | GCTGCATCCGATTTGCAA<br>AGT<br>SEQ ID NO:10823 | CTACAGCATTATCGTTACC<br>ATTCACT<br>SEQ ID NO:18835 |
| | | AA | RASQGIRKDLG<br>SEQ ID NO:2812 | AASDLQS<br>SEQ ID NO:10824 | LQHYRYPFT<br>SEQ ID NO:18836 |
| iPS:436096 | 21-225_195B10 | NA | CGGGCCAGTCAGAGCATTGG<br>TAGTAGCTTACAC<br>SEQ ID NO:2813 | TATGCTTCCCAGTCCTTC<br>TCA<br>SEQ ID NO:10825 | CATCAGAGTGGTCGTTACC<br>GCTCACT<br>SEQ ID NO:18837 |
| | | AA | RASQSIGSSLH<br>SEQ ID NO:2814 | YASQSFS<br>SEQ ID NO:10826 | HQSGRLPLT<br>SEQ ID NO:18838 |
| iPS:436098 | 21-225_195E10 | NA | CGGGCCAGTCAGAGCATTGG<br>TAGTAGCTTACAC<br>SEQ ID NO:2815 | TATGCTTCCCAGTCCTTC<br>TCA<br>SEQ ID NO:10827 | CATCAGAGTAGTCGTTACC<br>ATTCACT<br>SEQ ID NO:18839 |
| | | AA | RASQSIGSSLH<br>SEQ ID NO:2816 | YASQSFS<br>SEQ ID NO:10828 | HQSSRLPFT<br>SEQ ID NO:18840 |
| iPS:436100 | 21-225_195G11 | NA | AAGTCCAGCCAGAGTGTTT<br>ATTCAACTCCAACAATAAGA<br>ACTACTTAGCT<br>SEQ ID NO:2817 | TGGGCATCTACCCTGGA<br>ATCT<br>SEQ ID NO:10829 | CAGCAATATTGTAGTTTTCC<br>ATTCACT<br>SEQ ID NO:18841 |
| | | AA | KSSQSVLFNSNKNYLA<br>SEQ ID NO:2818 | WASTLES<br>SEQ ID NO:10830 | QQYCSFPFT<br>SEQ ID NO:18842 |
| iPS:436100 | 21-225_195G12 | NA | CGGGCGAGTCAGGGTATTAA<br>CAACTGGTTAGCC<br>SEQ ID NO:2819 | GGTGTTTCCAGTTTGCAG<br>AGT<br>SEQ ID NO:10831 | CAACAGGCTAACAGTTTCCC<br>GTGGACG<br>SEQ ID NO:18843 |
| | | AA | RASQGINNWLA<br>SEQ ID NO:2820 | GVSSLQS<br>SEQ ID NO:10832 | QQANSFPWT<br>SEQ ID NO:18844 |

FIGURE 49
(Continued)

| | | | | |
|---|---|---|---|---|
| iPS:436102 | 21-225_196B1 | NA | AAGTCCAGCCAGAGTATTTT ATTCAGCTCCAACAATAAGA GGTACTTAGCT SEQ ID NO:2821 | TGGGCATCTATCCGGGA ATCC SEQ ID NO:10833 | CAGCAATATTCTAGTCTTCC ATTCACT SEQ ID NO:18845 |
| | | AA | KSSQSILFSSNNKRYLA SEQ ID NO:2822 | WASIRES SEQ ID NO:10834 | QQYSSLPFT SEQ ID NO:18846 |
| iPS:436104 | 21-225_196C1 | NA | AAGTCCAGCCAGAGTGTTT ATTCAACTCCAACAATAAGA ACTACTTAGCT SEQ ID NO:2823 | TGGGCATCTACCCTGGA ATCT SEQ ID NO:10835 | CAGCAATATTGTAGTTTTCC ATTCACT SEQ ID NO:18847 |
| | | AA | KSSQSVLFNSNNKNYLA SEQ ID NO:2824 | WASTLES SEQ ID NO:10836 | QQYCSFPFT SEQ ID NO:18848 |
| iPS:436106 | 21-225_196F2 | NA | CGGGCGAGTCAGGGTATTAG CAGCTGGTTAGCC SEQ ID NO:2825 | GCTGCATCCAGTTTGCAA AGT SEQ ID NO:10837 | CAACAGACTAACAGTGTCCC ATTCACT SEQ ID NO:18849 |
| | | AA | RASGQGISSWLA SEQ ID NO:2826 | AASSLQS SEQ ID NO:10838 | QQTNSVPFT SEQ ID NO:18850 |
| iPS:436110 | 21-225_196F4 | NA | CGGGCAAGTCAGGCCATTCA CAGCTATTAAAT SEQ ID NO:2827 | ACTGCATCCAGTTTGCAA GGT SEQ ID NO:10839 | CAACAGAGCTACGGTTCCCC TCTCACT SEQ ID NO:18851 |
| | | AA | RASQRIHSYLN SEQ ID NO:2828 | TASSLQG SEQ ID NO:10840 | QQSYGSPLT SEQ ID NO:18852 |
| iPS:436112 | 21-225_196C7 | NA | CGGGCGAATCAGGCCATTAG CAATTATTAGCC SEQ ID NO:2829 | GCTGCATCCAGTTTGCAA AGT SEQ ID NO:10841 | CAACATTATCTCACTTACCCT CTCACT SEQ ID NO:18853 |
| | | AA | RANQAISNYLA SEQ ID NO:2830 | AASSLQS SEQ ID NO:10842 | QHYLTYPLT SEQ ID NO:18854 |
| iPS:436114 | 21-225_196G8 | NA | AAGTCCAGCCAGAGTGTTTT ACACAGCTCCAACAATAACA ACTACTTAGCT | TGGGCATCTACCCGGGA ATCC | CAGCAATATTATAATACTCC TCCGACA |

FIGURE 49
(Continued)

| | | | | | | |
|---|---|---|---|---|---|---|
| iPS:436116 | 21-225_196G8 | AA | SEQ ID NO:2831 KSSQSVLHSSNNNNYLA | SEQ ID NO:2832 WASTRES | SEQ ID NO:10843 | SEQ ID NO:18855 QQYYNTPPT |
| iPS:436118 | 21-225_196B9 | NA | SEQ ID NO:2833 CGGGCGAGTCAGGGTATTAG CAACTGCTTAGCC | SEQ ID NO:10844 GCTGCATCCAGTTGCAA AGT | SEQ ID NO:18856 CAACAGGGTGACACAGTTCCC TCCGACG |
| | | AA | SEQ ID NO:2834 RASQGISNCLA | SEQ ID NO:10845 AASSLQS | SEQ ID NO:18857 QQGDSFPPT |
| iPS:436120 | 21-225_196A10 | NA | SEQ ID NO:2835 CGGGCGAGTCAGGGTATTAG CAGGTGGTTAGCC | SEQ ID NO:10846 GCTGCATCCAGTTGCTA GGT | SEQ ID NO:18858 CAACGGGATAACACAGTTACC GTGCAGT |
| | | AA | SEQ ID NO:2836 RASQGISRWLA | SEQ ID NO:10847 AASSLLG | SEQ ID NO:18859 QRDNSLPCS |
| iPS:436122 | 21-225_196C10 | NA | SEQ ID NO:2837 CGGGCAAGTCAGGGCATTAG AAATGATTTAGGC | SEQ ID NO:10848 GCTGCATCCAGTTGCAA AGT | SEQ ID NO:18860 CTACAATATAATAGTTACCC TCTCACT |
| | | AA | SEQ ID NO:2838 RASQGIRNDLG | SEQ ID NO:10849 AASSLQS | SEQ ID NO:18861 LQYNSYPLT |
| iPS:436132 | 21-225_196C10 | NA | SEQ ID NO:2839 AGGGCCAGTCAGAGTGTTAG CAACAGCTTCTTAGCC | SEQ ID NO:10850 GGTGCATCCAGCAGGGC CACT | SEQ ID NO:18862 CAGCAGTATGGTAGCTCACC TCCGTGGACG |
| | | AA | SEQ ID NO:2840 RASPSVSNSFLA | SEQ ID NO:10851 GASSRAT | SEQ ID NO:18863 QQYGSSPPWT |
| iPS:436132 | 21-225_196C12 | NA | SEQ ID NO:2841 CGGGCAAGTCAGGGCATTAG AAATGATCTAGGC | SEQ ID NO:10852 GCTGCATCCAGTTGCAA AGT | SEQ ID NO:18864 CTACACAGCATAATGATTCCC GTTCACT |
| | | AA | SEQ ID NO:2842 RASQGIRNDLG | SEQ ID NO:10853 AASSLQS | SEQ ID NO:18865 LQHNDFPFT |
| iPS:436134 | | NA | AGGGCCAGTCAGAGTGTTAG AAGCAACTTCTTAGCC | SEQ ID NO:10854 GGTGCATACCGCAGGGC CACT | SEQ ID NO:18866 CAGCAGTATGGTAACTCACC GTGGACG |

FIGURE 49
(Continued)

| | | | | | | |
|---|---|---|---|---|---|---|
| iPS:436138 | 21-225_196H12 | AA | SEQ ID NO:2843<br>RASQSVRSNFLA | SEQ ID NO:10855<br>GAYRRAT | SEQ ID NO:18867<br>QQYGNSPWT | |
| iPS:436140 | 21-225_197F2 | NA | SEQ ID NO:2844<br>CGGACGAGTCAGGGCATTGG<br>CAATTATTAGCC | SEQ ID NO:10856<br>AAAACATCCAGTTTGCA<br>AAGT | SEQ ID NO:18868<br>CAACAATATATCACTACTACCC<br>GCTCACT | |
| | | AA | SEQ ID NO:2845<br>RTSQGIGNYLA | SEQ ID NO:10857<br>KTSSLQS | SEQ ID NO:18869<br>QQYITYPLT | |
| iPS:436146 | 21-225_197G3 | NA | SEQ ID NO:2846<br>CGGGGAGTCAGGGCATTGG<br>CAATCATTAGCC | SEQ ID NO:10858<br>GCTGCATCCAGTTTGCAA<br>AGT | SEQ ID NO:18870<br>CAACAGTATAGTAATTACCC<br>GGTCACT | |
| | | AA | SEQ ID NO:2847<br>RASQGIGNHLA | SEQ ID NO:10859<br>AASSLQS | SEQ ID NO:18871<br>QQYSNYPVT | |
| iPS:436146 | 21-225_197F4 | NA | SEQ ID NO:2848<br>AGGGCCAGTCAGAGTATTCG<br>CAGCAGTTCTTAGCC | SEQ ID NO:10860<br>GGTGCATCCAGCAGGGC<br>CACT | SEQ ID NO:18872<br>CAGCAGTATGGAAAACTCACG<br>GTGGGCG | |
| | | AA | SEQ ID NO:2849<br>RASQSIRSSFLA | SEQ ID NO:10861<br>GASSRAT | SEQ ID NO:18873<br>QQYGNSPWA | |
| iPS:436150 | 21-225_197H4 | NA | SEQ ID NO:2850<br>AGGTCCAGCCAGAGTGTTT<br>ACACAGTTCAACAATTACA<br>ACTACTTAGCT | SEQ ID NO:10862<br>TGGGCATCTACCCGGGA<br>ATCC | SEQ ID NO:18874<br>CAACAATATTATAGTACTCC<br>TCCGACG | |
| | | AA | SEQ ID NO:2851<br>RSSQSVLHSFNNYNYLA | SEQ ID NO:10863<br>WASTRES | SEQ ID NO:18875<br>QQYSTPPT | |
| iPS:436152 | 21-225_197B6 | NA | SEQ ID NO:2852<br>CGGGCGAGTCAGGGCATTGG<br>CAAATATTAGCC | SEQ ID NO:10864<br>GGTGCATCCAGTTTGCA<br>AAGT | SEQ ID NO:18876<br>CAACAATATAGTACTTACCC<br>GCTCACT | |
| | | AA | SEQ ID NO:2853<br>RASQGIGKYLA | SEQ ID NO:10865<br>GASSLQS | SEQ ID NO:18877<br>QQYSTYPLT | |
| | | | SEQ ID NO:2854 | SEQ ID NO:10866 | SEQ ID NO:18878 | |

FIGURE 49
(Continued)

| | | | | | |
|---|---|---|---|---|---|
| iPS:436154 | 21-225_197C6 | NA | AGGTCCAGCCAGAGTGTTT ACACAGCTCCAACAATACA ACTACTTAGCT SEQ ID NO:2855 | TGGGCATCTACCCGGGA ATCC SEQ ID NO:10867 | CAACAATATTATAGTACTCC TCCGACG SEQ ID NO:18879 |
| | | AA | RSSQSVLHSSNNYNYLA SEQ ID NO:2856 | WASTRES SEQ ID NO:10868 | QQYYSTPPT SEQ ID NO:18880 |
| iPS:436156 | 21-225_197C8 | NA | AAGTCCAGCCAGAGTGTTT ACACAGTTCCAACAATAAGA ACTACTTAGCT SEQ ID NO:2857 | TGGGCATCTACCCGGGA ATCC SEQ ID NO:10869 | CAGCAGTCTTATACTATTCC ATTCACT SEQ ID NO:18881 |
| | | AA | KSSQSVLHSSNNKNYLA SEQ ID NO:2858 | WASTRES SEQ ID NO:10870 | QQSYTIPFT SEQ ID NO:18882 |
| iPS:436158 | 21-225_197G8 | NA | AAGTCTAGTCAGAACCTCCT GCATAGTGATGAAAGACCT TCT ATTTGTAT SEQ ID NO:2859 | GAAGTTTCCAACCGGTTC TCT SEQ ID NO:10871 | ATGCAAAGTATACAGTTCC CTGGACG SEQ ID NO:18883 |
| | | AA | KSSQNLLHSDGKTYLY SEQ ID NO:2860 | EVSNRFS SEQ ID NO:10872 | MQSIQLPWT SEQ ID NO:18884 |
| iPS:436160 | 21-225_197C9 | NA | CGGGGCGAGTCAGGGTATTAG CAACTGGTTAGGC SEQ ID NO:2861 | GCTGCATCCAGTTTGCAA AGT SEQ ID NO:10873 | CAACAGGCTAACAGTTCCC GTGGACG SEQ ID NO:18885 |
| | | AA | RASQGISNWLA SEQ ID NO:2862 | AASSLQS SEQ ID NO:10874 | QQANSFPWT SEQ ID NO:18886 |
| iPS:436164 | 21-225_197G10 | NA | CGGGCAAGTCAGGGCATTAG AAATGATTTAGGC SEQ ID NO:2863 | GGTGCATCCAGTTTACA AAGT SEQ ID NO:10875 | CTACAGCATTATAGGTACCC ATTCACT SEQ ID NO:18887 |
| | | AA | RASQGIRNDLG SEQ ID NO:2864 | GASSLQS SEQ ID NO:10876 | LQHYRYPFT SEQ ID NO:18888 |
| iPS:436167 | | NA | CGGGCGGAGTCAGGGCATTAA CAAGTATTTATCC | GCTGCATCCAGTGTGCA AAGT | CAACGATATGACACTTACCC ATTCACT |

FIGURE 49
(Continued)

| | | | | | | |
|---|---|---|---|---|---|---|
| iPS:436173 | 21-225_197E11 | AA | SEQ ID NO:2865 RASQGINKYLS | SEQ ID NO:10877 AASSVQS | SEQ ID NO:18889 QRYDTYPFT | |
| iPS:436177 | 21-225_197G12 | NA | SEQ ID NO:2866 CGGAGGAGTCAGGGCATTGG CAATTATTTAGCC | SEQ ID NO:10878 AAAACATCCAGTTGCA AAGT | SEQ ID NO:18890 CAACAATATATGACTTACCC GCTCACT | |
| | | AA | SEQ ID NO:2867 RTSQGIGNYLA | SEQ ID NO:10879 KTSSLQS | SEQ ID NO:18891 QQYMTYPLT | |
| iPS:436179 | 21-225_198B1 | NA | SEQ ID NO:2868 AGGGCCGGTCAAAGTATTAG AACCAACTTCTTAGCC | SEQ ID NO:10880 GGTGCATCCAGCAGGGC CACT | SEQ ID NO:18892 CAGCAGTATGGTAGCTCACC GTGGACG | |
| | | AA | SEQ ID NO:2869 RAGQSIRTNFLA | SEQ ID NO:10881 GASSRAT | SEQ ID NO:18893 QQYGSSPWT | |
| iPS:436181 | 21-225_198E1 | NA | SEQ ID NO:2870 AGGGCCAGTCAGAGTATAA GGAGCAACTTCTTAGCC | SEQ ID NO:10882 GGTGCATTCAGTAGGGC CACT | SEQ ID NO:18894 CAGCAGTATGGTAATTCACC GTGGACG | |
| | | AA | SEQ ID NO:2871 RASQSIRSNFLA | SEQ ID NO:10883 GAFSRAT | SEQ ID NO:18895 QQYGNSPWT | |
| iPS:436189 | 21-225_198C2 | NA | SEQ ID NO:2872 AGGGCCAGTCAGAGTGTTAG AAGCAGTACTTAGCC | SEQ ID NO:10884 GGTGCATTCAGTAGGGC CAGT | SEQ ID NO:18896 CAGCAGTATGGTAACTCACC GTGGACG | |
| | | AA | SEQ ID NO:2873 RASQSVRSSYLA | SEQ ID NO:10885 GAFSRAS | SEQ ID NO:18897 QQYGNSPWT | |
| iPS:436189 | 21-225_198B6 | NA | SEQ ID NO:2874 CGGGCGAGTCAGGGCATTGG CAATTATTTAGCC | SEQ ID NO:10886 GCTGCATCCAGTTGCAA AGT | SEQ ID NO:18898 CAACAATATAGTACTTACCC GCTCACT | |
| | | AA | SEQ ID NO:2875 RASQGIGNYLA | SEQ ID NO:10887 AASSLQS | SEQ ID NO:18899 QQYSTYPLT | |
| iPS:436191 | | NA | SEQ ID NO:2876 CGGGCAAGTCAGGGCATAA GAAAAGATTTAGGC | SEQ ID NO:10888 GCTGCATCCAGTTGCAA AGT | SEQ ID NO:18900 CTACAACATTATCGTTACCC TTTCACT | |

FIGURE 49
(Continued)

| | | | | | |
|---|---|---|---|---|---|
| iPS:436193 | 21-225_198B9 | AA | SEQ ID NO:2877<br>RASQGIRKDLG<br>SEQ ID NO:2878 | SEQ ID NO:10889<br>AASSLQS<br>SEQ ID NO:10890 | SEQ ID NO:18901<br>LQHYRYPFT<br>SEQ ID NO:18902 |
| | 21-225_198A10 | NA | AAGTCTAGTCAGAGAGCCTCCT<br>CTATAGTGATGGAAGGACCTTCT | GAGGTTCCAACCGGTTC | ATGCAAAGTATACAGCTTCC<br>CTGGACG |
| | | AA | SEQ ID NO:2879<br>KSSQSLLYSDGRTYLY<br>SEQ ID NO:2880 | SEQ ID NO:10891<br>EVSNRFS<br>SEQ ID NO:10892 | SEQ ID NO:18903<br>MQSIQLPWT<br>SEQ ID NO:18904 |
| iPS:436195 | 21-225_198G10 | NA | AGGGCCAGTCAGAGTATTCG<br>CAGCAGCTTCTTAGCC | GGTGCATCCAGCAGGGC<br>CACT | CAGCAGTATGGTAACTCACC<br>GTGGGCG |
| | | AA | SEQ ID NO:2881<br>RASQSIRSSFLA<br>SEQ ID NO:2882 | SEQ ID NO:10893<br>GASSRAT<br>SEQ ID NO:10894 | SEQ ID NO:18905<br>QQYGNSPWA<br>SEQ ID NO:18906 |
| iPS:436197 | 21-225_199C2 | NA | AGGGCCAGTCAGAGTATTCG<br>CAGCAGCTTCTTAGCC | GGTGCATCCAGCAGGGC<br>CACT | CAGCAGTATGGTAACTCACC<br>GTGGGCG |
| | | AA | SEQ ID NO:2883<br>RASQSIRSSFLA<br>SEQ ID NO:2884 | SEQ ID NO:10895<br>GASSRAT<br>SEQ ID NO:10896 | SEQ ID NO:18907<br>QQYGNSPWA<br>SEQ ID NO:18908 |
| iPS:436199 | 21-225_199E3 | NA | CGGGCAAGTCAGGGCATTAG<br>AAATGATTTAGGC | TCTGCATCCAGTTGCAA<br>AGG | CTACAGCATAAAAGGTACCC<br>GCTCACT |
| | | AA | SEQ ID NO:2885<br>RASQGIRNDLG<br>SEQ ID NO:2886 | SEQ ID NO:10897<br>SASSLQR<br>SEQ ID NO:10898 | SEQ ID NO:18909<br>LQHKRYPLT<br>SEQ ID NO:18910 |
| iPS:436201 | 21-225_199C5 | NA | CGGGGAGTCAGGGCATTAG<br>CAAGTATTTAGGC | GCTGCATCCAGTTGCAA<br>AGT | CAACAGTATCTTACTTACCC<br>GCTCACT |
| | | AA | SEQ ID NO:2887<br>RASQGISKYLA<br>SEQ ID NO:2888 | SEQ ID NO:10899<br>AASSLQS<br>SEQ ID NO:10900 | SEQ ID NO:18911<br>QQYLTYPLT<br>SEQ ID NO:18912 |

FIGURE 49
(Continued)

| | | | | | |
|---|---|---|---|---|---|
| iPS:436203 | 21-225_199A6 | NA | AGGCCCAGTCAGAGTTTTAG CAGAAACTTAGCC SEQ ID NO:2889 | GGTGCATCCACTAGGGC CACT SEQ ID NO:10901 | CAGCAGTATAATAACTGGCC GCTCACT SEQ ID NO:18913 |
| | | AA | RPSQSFSRNLA SEQ ID NO:2890 | GASTRAT SEQ ID NO:10902 | QQYNNWPLT SEQ ID NO:18914 |
| iPS:436205 | 21-225_199A7 | NA | CGGGCAAGTCAGGGCATAA GAAAAGATTTAGGC SEQ ID NO:2891 | GCTGCATCCAGTTTGCAA AGT SEQ ID NO:10903 | CTACAACATTATCGTTACCC TTTCACT SEQ ID NO:18915 |
| | | AA | RASQGIRKDLG SEQ ID NO:2892 | AASSLQS SEQ ID NO:10904 | LQHYRYPFT SEQ ID NO:18916 |
| iPS:436207 | 21-225_199C7 | NA | AGGGCCAGTCAGAGTATAA GGACCAACTTCTTAGCC SEQ ID NO:2893 | GGTGCATCCAGCAGGGC CACT SEQ ID NO:10905 | CAGCAGTATGGTAACTCACC GTGGACG SEQ ID NO:18917 |
| | | AA | RASQSIRTNFLA SEQ ID NO:2894 | GASSRAT SEQ ID NO:10906 | QQYGNSPWT SEQ ID NO:18918 |
| iPS:436210 | 21-225_199G11 | NA | AGGGCCAGTCAGAGTGTTAG AAGCAGTACTTAGCC SEQ ID NO:2895 | GGTGCATTCAGCAGGGC CACT SEQ ID NO:10907 | CAGCAGTATGGTAACTCACC GTGGACG SEQ ID NO:18919 |
| | | AA | RASQSVRSSYLA SEQ ID NO:2896 | GAFSRAT SEQ ID NO:10908 | QQYGNSPWT SEQ ID NO:18920 |
| iPS:436212 | 21-225_200G1 | NA | CGGGCAAGTCAGAGCATTAG CAGTCTATTTAAAT SEQ ID NO:2897 | GCTGAGTCCAGTTACA AAGT SEQ ID NO:10909 | CAACAGAGTTACAGTTCCCC TCCGTGGACG SEQ ID NO:18921 |
| | | AA | RASQSISSYIN SEQ ID NO:2898 | AESSLQS SEQ ID NO:10910 | QQSYSSPPWT SEQ ID NO:18922 |
| iPS:436214 | 21-225_200F6 | NA | CGGGCAAGTCAGGACATTAG AAATGATTTAGGC SEQ ID NO:2899 | GCTGCATCCAGTTTGCAA AGT SEQ ID NO:10911 | CTACACAGGCATTATCGTTACC ATTCACT SEQ ID NO:18923 |
| | | AA | RASQDIRNDLG SEQ ID NO:2900 | AASSLQS SEQ ID NO:10912 | LQHYRYPFT SEQ ID NO:18924 |

FIGURE 49
(Continued)

| | | | | | |
|---|---|---|---|---|---|
| iPS:436216 | 21-225_200B7 | NA | CGGGCCAGTCAGAGAACATTGG TAATACCTTGCAC<br>SEQ ID NO:2901<br>RASQNIGNTLH<br>SEQ ID NO:2902 | TATGCTTCCCAGTCCTTC TCA<br>SEQ ID NO:10913<br>Y ASQSFS<br>SEQ ID NO:10914 | CATCAGAGTGGTAGTTTACC TCAGACG<br>SEQ ID NO:18925<br>HQSGSLPQT<br>SEQ ID NO:18926 |
| iPS:436218 | 21-225_200G7 | NA | AAGTCCAGCCAGAGTGTTT ACACAGTCCAACAATAACA ACTACTTAGCT<br>SEQ ID NO:2903<br>KSSQSVLHSSNNNNYLA<br>SEQ ID NO:2904 | TGGGCATCTACCCGGGA ATCC<br>SEQ ID NO:10915<br>WASTRES<br>SEQ ID NO:10916 | CAGCAATATTATAATACTCC TCCGACA<br>SEQ ID NO:18927<br>QQYYNTPPT<br>SEQ ID NO:18928 |
| iPS:436220 | 21-225_200F8 | NA | CGGGCCAGTCAGAGTATTGG TAGTAACTTACAC<br>SEQ ID NO:2905<br>RASQSIGSNLH<br>SEQ ID NO:2906 | TCTGCTTCCCAGTCCTTC TCA<br>SEQ ID NO:10917<br>SASQSFS<br>SEQ ID NO:10918 | CAGCAGAGTAGTAGTTTACC GTGGACG<br>SEQ ID NO:18929<br>QQSSSLPWT<br>SEQ ID NO:18930 |
| iPS:436222 | 21-225_200C9 | NA | CGGGCAACTCAGGGCATTAG AAAAGATTTAGGC<br>SEQ ID NO:2907<br>RATQGIRKDLG<br>SEQ ID NO:2908 | ACTGCATCCAGTTTGCAA AGT<br>SEQ ID NO:10919<br>TASSLQS<br>SEQ ID NO:10920 | CTACAGCATAATAGTTACC GTGGACG<br>SEQ ID NO:18931<br>LQHNSYPWT<br>SEQ ID NO:18932 |
| iPS:436226 | 21-225_200F10 | NA | AGGGCCAGTCAGAGAATATTCG CAGCAGCTTCTTAGCC<br>SEQ ID NO:2909<br>RASQNIRSSFLA<br>SEQ ID NO:2910 | GGTGCATCCAGCAGGGC CACT<br>SEQ ID NO:10921<br>GASSRAT<br>SEQ ID NO:10922 | CAGCAGTATGGTAACTCACC GTGGGCG<br>SEQ ID NO:18933<br>QQYGNSPWA<br>SEQ ID NO:18934 |
| iPS:436228 | 21-225_200F12 | NA | CGGGCAAGTCAGGGCATTAG AAATGATTTAGGC<br>SEQ ID NO:2911<br>RASQGIRNDLG<br>SEQ ID NO:2912 | TCTGCATCCAGTTTGCAT ACT<br>SEQ ID NO:10923<br>SASSLHT<br>SEQ ID NO:10924 | CTACAGCATAAGAGTTACC GCTCACT<br>SEQ ID NO:18935<br>LQHKSYPLT<br>SEQ ID NO:18936 |

FIGURE 49
(Continued)

| | | | | | | |
|---|---|---|---|---|---|---|
| iPS:436230 | 21-225_201A1 | NA | SEQ ID NO:2912 CGGGCAAGTCAGGGCATTAG GAATGATTTAGGC | SEQ ID NO:10924 TCTGCATCCATTTTACAA AGG | SEQ ID NO:18936 CTACAGCATAAAAGTTACC TCTCACT | |
| | | AA | SEQ ID NO:2913 RASQGIRNDLG | SEQ ID NO:10925 SASILQR | SEQ ID NO:18937 LQHKSYPLT | |
| iPS:436232 | 21-225_201E1 | NA | SEQ ID NO:2914 AGGGCCAGTCCGAGTATTAA CAGCGGCTTCTTAGCC | SEQ ID NO:10926 GGTGCATCCAGCAGGGC CACT | SEQ ID NO:18938 CACCAGTATGAGACCTCACC GTGGACG | |
| | | AA | SEQ ID NO:2915 RASPSINSGFLA | SEQ ID NO:10927 GASSRAT | SEQ ID NO:18939 HQYETSPWT | |
| iPS:436234 | 21-225_51E3 | NA | SEQ ID NO:2916 TCTGGAAGCAACTCCAACAT CGGAAGTAATATTGTAACC | SEQ ID NO:10928 AGTAATGATCAGCGGCC CTCA | SEQ ID NO:18940 ACAGCATGGATGACAGCCT GAATGGTTGGGTG | |
| | | AA | SEQ ID NO:2917 SGSNSNIGSNIVT | SEQ ID NO:10929 SNDQRPS | SEQ ID NO:18941 TAWDIDSLNGWV | |
| iPS:436236 | 21-225_201F7 | NA | SEQ ID NO:2918 AGGGCCAGTCAGAATATTAA AACAACTTAGCC | SEQ ID NO:10930 GGTGCATCCACCAGGGC CACT | SEQ ID NO:18942 CAGCAGTTTTATAACTGGCT GTGCAGT | |
| | | AA | SEQ ID NO:2919 RASQNIKNLA | SEQ ID NO:10931 GASTRAT | SEQ ID NO:18943 QQFYNWLCS | |
| iPS:436238 | 21-225_201B2 | NA | SEQ ID NO:2920 AGGGCCAGTCAGAGTGTTAG CAGCAACTACTTAGCC | SEQ ID NO:10932 GGTGCATCCAGCAGGGC CACT | SEQ ID NO:18944 CAGCAGTATGAAAACTCACC GTGGACG | |
| | | AA | SEQ ID NO:2921 RASQSVSSNYLA | SEQ ID NO:10933 GASSRAT | SEQ ID NO:18945 QQYENSPWT | |
| iPS:436240 | 21-225_201E8 | NA | SEQ ID NO:2922 CGGGCCAGTCAGAACATTGG TCGTAGTTTACAC | SEQ ID NO:10934 TATGCTTCCCAGTCCTTC TCA | SEQ ID NO:18946 CATCAGAGTCGAAGTTTACC GCTCACT | |
| | | | SEQ ID NO:2923 | SEQ ID NO:10935 | SEQ ID NO:18947 | |

FIGURE 49
(Continued)

| | | | | | | | |
|---|---|---|---|---|---|---|---|
| iPS:436242 | | AA | RASQNIGRSLH SEQ ID NO:2924 | YASQSFS SEQ ID NO:10936 | HQSRSLPLT SEQ ID NO:18948 | | |
| iPS:436244 | 21-225_201A10 | NA | CGGGCAAGTCAGGGCATTAG AAATGATTTAGGC SEQ ID NO:2925 | TCTACATCCAGTTTGCAT TCT SEQ ID NO:10937 | CTACAGCATAATAGTTACCC GCTCACT SEQ ID NO:18949 | | |
| | | AA | RASQGIRNDLG SEQ ID NO:2926 | STSSLHS SEQ ID NO:10938 | LQHNSYPLT SEQ ID NO:18950 | | |
| iPS:436246 | 21-225_201H10 | NA | CGGGCAAGTCACAACATTAA CAGCTATTTAAAT SEQ ID NO:2927 | GCTGCATCCAGTTTGCAA AGT SEQ ID NO:10939 | CAACAGAGTTACAGTTTCCC GCTCACT SEQ ID NO:18951 | | |
| | | AA | RASHNINSYLN SEQ ID NO:2928 | AASSLQS SEQ ID NO:10940 | QQSYSFPLT SEQ ID NO:18952 | | |
| iPS:436248 | 21-225_201G6 | NA | AGGTCTAGTCAGAGCCTCCT CCATAATAATAGATACAACC ATTTGGAT SEQ ID NO:2929 | TTGGGTTCTAATCGGGCC TCC SEQ ID NO:10941 | ATGCAAGCTCTACAAACTCC CACT SEQ ID NO:18953 | | |
| | | AA | RSSQSLLHNNRYNHLD SEQ ID NO:2930 | LGSNRAS SEQ ID NO:10942 | MQALQPFT SEQ ID NO:18954 | | |
| iPS:436250 | 21-225_202A3 | NA | CGGGCAAGTCAGGGCATTAG AAATGATTTAGGC SEQ ID NO:2931 | GCTGCATCCAGTTGCA AAGT SEQ ID NO:10943 | CTACAGCATATGACTACCC ATTCACT SEQ ID NO:18955 | | |
| | | AA | RASQGIRNDLG SEQ ID NO:2932 | AASRLQS SEQ ID NO:10944 | LQHHDYPFT SEQ ID NO:18956 | | |
| iPS:436252 | 21-225_201A4 | NA | AGGTCCAAGTCAGAATATTAA AAGCAACTTAGCC SEQ ID NO:2933 | GGTGCATCCACCAGGGC CACT SEQ ID NO:10945 | CAGCAGTTTATAAACTGGCT GTGCAGT SEQ ID NO:18957 | | |
| | | AA | RSSQNIKSNLA SEQ ID NO:2934 | GASTRAT SEQ ID NO:10946 | QQFYNWLCS SEQ ID NO:18958 | | |
| | | NA | AGGGCCAGTCAGAGAATTA ACAACAACTTAGCC | GGTGCATCCACCAGGGC CACT | CAGCAGTATTATAACTGGCT GTGCAGT | | |

FIGURE 49
(Continued)

| | | | | | | |
|---|---|---|---|---|---|---|
| | | 21-225_202A8 | AA | SEQ ID NO:2935<br>RASQRINNNLA<br>SEQ ID NO:2936 | SEQ ID NO:10947<br>GASTRAT<br>SEQ ID NO:10948 | SEQ ID NO:18959<br>QQYYNWLCS<br>SEQ ID NO:18960 |
| iPS:436254 | | 21-225_202C12 | NA | AGGTCTAGTCAGAGCCTCCT<br>GCATAATAATACAACC<br>ATTTGGAT<br>SEQ ID NO:2937 | TTGGGTTCTAATCGGGCC<br>TCC<br>SEQ ID NO:10949 | ATGCAAGCTCTACAAACTCC<br>CACT<br>SEQ ID NO:18961 |
| iPS:436256 | | 21-225_202D9 | AA | RSSQSLLHNNKYNHLD<br>SEQ ID NO:2938 | LGSNRAS<br>SEQ ID NO:10950 | MQALQTPT<br>SEQ ID NO:18962 |
| | | | NA | AGGGCCAGTCAGAGTGTTAA<br>CAGCGGCTACTTAGCC<br>SEQ ID NO:2939 | GGTGCATCCAGCAGGGC<br>CACT<br>SEQ ID NO:10951 | CAACAATATGAGACCTCACC<br>GTGGACG<br>SEQ ID NO:18963 |
| iPS:436258 | | 21-225_202F12 | AA | RASQSVNSGYLA<br>SEQ ID NO:2940 | GASSRAT<br>SEQ ID NO:10952 | QQYETSPWT<br>SEQ ID NO:18964 |
| | | | NA | AGGGCCAGTCAGAGTGTTCT<br>GAACAACTTAGCC<br>SEQ ID NO:2941 | GGTGCATCCACTAGGGC<br>CACT<br>SEQ ID NO:10953 | CAGCAGTATGATAACTGGCC<br>TCCGTGCAGT<br>SEQ ID NO:18965 |
| iPS:436260 | | 21-225_203H1 | AA | RASQSVLNNLA<br>SEQ ID NO:2942 | GASTRAT<br>SEQ ID NO:10954 | QQYDNWPPCS<br>SEQ ID NO:18966 |
| | | | NA | CGGGCGAGTCAGGGCATTGG<br>CAATTATTTAGCC<br>SEQ ID NO:2943 | GTTGCATCCAGGTTGCA<br>AAGT<br>SEQ ID NO:10955 | CAACGGTATCATACTTACCC<br>GCTCACT<br>SEQ ID NO:18967 |
| iPS:436262 | | 21-225_203E3 | AA | RASQGIGNYLA<br>SEQ ID NO:2944 | VASRLQS<br>SEQ ID NO:10956 | QRYHTYPLT<br>SEQ ID NO:18968 |
| | | | NA | CGGGCAAGTCACAACATTAA<br>CAGCTATTTAAAT<br>SEQ ID NO:2945 | GCTGCATCCAGTTGCAA<br>AGT<br>SEQ ID NO:10957 | CAACAGAGTTACAGTTTCCC<br>GCTCACT<br>SEQ ID NO:18969 |
| | | | AA | RASHNINSYLN<br>SEQ ID NO:2946 | AASSLQS<br>SEQ ID NO:10958 | QQSYSFPLT<br>SEQ ID NO:18970 |

FIGURE 49
(Continued)

| | | | | |
|---|---|---|---|---|
| iPS:436264 | 21-225_203F7 | NA | CGGGCAAGTCAGGGCATTAG ACATGATTAGGC<br>SEQ ID NO:2947 | GCTGCATCCAGTTTGCAA AGT<br>SEQ ID NO:10959 | CTACAGCATTATAGTTTCCCT CGGACG<br>SEQ ID NO:18971 |
| | | AA | RASQGIRHDLG<br>SEQ ID NO:2948 | AASSLQS<br>SEQ ID NO:10960 | LQHYSFPRT<br>SEQ ID NO:18972 |
| iPS:436268 | 21-225_203B9 | NA | CGGGCAAGTCAGGGCATTAG AAATGATTAGGC<br>SEQ ID NO:2949 | AGGGCATCCAGTGTGCA AAAT<br>SEQ ID NO:10961 | CTACAGCATAATAGTTACCC ATTCACT<br>SEQ ID NO:18973 |
| | | AA | RASQGIRNDLG<br>SEQ ID NO:2950 | RASSVQN<br>SEQ ID NO:10962 | LQHNSYPFT<br>SEQ ID NO:18974 |
| iPS:436270 | 21-225_203F10 | NA | AAGTCCAGCCAGAGTGTTTT TTCCACTCGAACAATAAGA ACTACTTAGCT<br>SEQ ID NO:2951 | TGGGCATCTACCCGGGA ATCC<br>SEQ ID NO:10963 | CAACAATATTTTAGTCTTCC ATTCACT<br>SEQ ID NO:18975 |
| | | AA | KSSQSVFFHSNNKNYLA<br>SEQ ID NO:2952 | WASTRES<br>SEQ ID NO:10964 | QQYFSLPFT<br>SEQ ID NO:18976 |
| iPS:436272 | 21-225_201F5 | NA | AAGTCCAGCCAGAGTGTTTT ATACAGTTCCAACAATAAGA ACTACTTAGTT<br>SEQ ID NO:2953 | TGGGCATCTACCCGGGA ATCC<br>SEQ ID NO:10965 | CAGCAATATTATAGTACTCC TCCGACG<br>SEQ ID NO:18977 |
| | | AA | KSSQSVLYSSNNKNYLV<br>SEQ ID NO:2954 | WASTRES<br>SEQ ID NO:10966 | QQYYSTPPT<br>SEQ ID NO:18978 |
| iPS:436274 | 21-225_204H3 | NA | CGGGCAAGTCAGGGCATTAG AAATGATTAGGC<br>SEQ ID NO:2955 | GCTGCAGCCAGTTGCA AGT<br>SEQ ID NO:10967 | CTACAGCATTATAGTTACCC TCGGACG<br>SEQ ID NO:18979 |
| | | AA | RASQGIRNDLG<br>SEQ ID NO:2956 | AAASLQG<br>SEQ ID NO:10968 | LQHYSYPRT<br>SEQ ID NO:18980 |
| iPS:436276 | 21-225_204H4 | NA | CGGGCAAGTCACAACATTAA CAGCTATTTAAAT<br>SEQ ID NO:2957 | GCTGCATCCAGTTGCAA AGT<br>SEQ ID NO:10969 | CAACAGAGTTACAGTTTCCC GCTCACT<br>SEQ ID NO:18981 |

FIGURE 49
(Continued)

| | | | | | | |
|---|---|---|---|---|---|---|
| iPS:436278 | 21-225_201F2 | AA | RASHNINSYLN<br>SEQ ID NO:2958 | AGGGCCAGTCAGGAATATTAA<br>AAGCAACTTAGCC<br>SEQ ID NO:2959 | AASSLQS<br>SEQ ID NO:10970 | QQSYSFPLT<br>SEQ ID NO:18982 |
| | | NA | | | GGTGCATCCACCAGGGC<br>CACT<br>SEQ ID NO:10971 | CAGCAGTTTTATAACTGGCT<br>GTGCAGT<br>SEQ ID NO:18983 |
| iPS:436280 | 21-225_204D6 | AA | RASQNIKSNLA<br>SEQ ID NO:2960 | | GASTRAT<br>SEQ ID NO:10972 | QQFYNWLCS<br>SEQ ID NO:18984 |
| | | NA | CGGGCAAGTCGGAGCGTTCA<br>CACCTATTTAAAT<br>SEQ ID NO:2961 | | GGTGCATCCAGTTTGCA<br>ACGT<br>SEQ ID NO:10973 | CAACAGAGTTACAGTTCCCC<br>GCTCACT<br>SEQ ID NO:18985 |
| iPS:436282 | 21-225_204G6 | AA | RASRSVHTYLN<br>SEQ ID NO:2962 | | GASSLQR<br>SEQ ID NO:10974 | QQSYSSPLT<br>SEQ ID NO:18986 |
| | | NA | CGGACGAGTCAGGGCATTGG<br>CAATTATTAGCC<br>SEQ ID NO:2963 | | GCTGCATCCAGTTTGCAA<br>AGT<br>SEQ ID NO:10975 | CAACACTATCTTAGTTACCC<br>TCTCACT<br>SEQ ID NO:18987 |
| iPS:436284 | 21-225_204G8 | AA | RTSQGIGNYLA<br>SEQ ID NO:2964 | | AASSLQS<br>SEQ ID NO:10976 | QHYLSYPLT<br>SEQ ID NO:18988 |
| | | NA | CGGGCGAGTCAGGGCATAA<br>GTAATCATTAGCC<br>SEQ ID NO:2965 | | GCTGCATCCAGTTTGCAA<br>AGT<br>SEQ ID NO:10977 | CAACAGTATAGTAATTACCC<br>GGTCACT<br>SEQ ID NO:18989 |
| iPS:436286 | 21-225_204H8 | AA | RASQGISNHLA<br>SEQ ID NO:2966 | | AASSLQS<br>SEQ ID NO:10978 | QQYSNYPVT<br>SEQ ID NO:18990 |
| | | NA | CGGGCAAGTCAGGGCATTAG<br>AAATGATTAGCC<br>SEQ ID NO:2967 | | TCTGCATCCAGTTTGCAA<br>AGT<br>SEQ ID NO:10979 | CTACAACATAATAGTTACCC<br>TCTCACT<br>SEQ ID NO:18991 |
| | | AA | RASQGIRNDLG<br>SEQ ID NO:2968 | | SASSLQS<br>SEQ ID NO:10980 | LQHNSYPLT<br>SEQ ID NO:18992 |
| iPS:436290 | 21-225_205G3 | NA | AGGGCCAGTCAGGGAATGTTAG<br>TTACAGTACTTAGCC<br>SEQ ID NO:2969 | | GGTGCATCCAGGAGGGC<br>CACT<br>SEQ ID NO:10981 | CAGCAGTATGGTAGCTCACC<br>GTGCAGT<br>SEQ ID NO:18993 |

FIGURE 49
(Continued)

| | | | | | | | |
|---|---|---|---|---|---|---|---|
| iPS:436292 | | AA | RASQNVSYSYLA SEQ ID NO:2970 | | GASRRAT SEQ ID NO:10982 | | QQYGSSPCS SEQ ID NO:18994 |
| | 21-225_205H3 | NA | CGGGCGAGTCAGGCCATTAG TAATCATTAGCC SEQ ID NO:2971 | | GCTGCATCCAGTTTGCAA AGT SEQ ID NO:10983 | | CAACAATATAGTAATTACC ACTCACT SEQ ID NO:18995 |
| iPS:436294 | | AA | RASQAISNHLA SEQ ID NO:2972 | | AASSLQS SEQ ID NO:10984 | | QQYSNYPLT SEQ ID NO:18996 |
| | 21-225_205G4 | NA | AGGGCCAGTCAGAATATTAA AAGCAACTTAGCC SEQ ID NO:2973 | | GGTGCATCCACCAGGGC CACT SEQ ID NO:10985 | | CAGCAGTTTTATAACTGGCT GTGCAGT SEQ ID NO:18997 |
| iPS:436296 | | AA | RASQNIKSNLA SEQ ID NO:2974 | | GASTRAT SEQ ID NO:10986 | | QQFYNWLCS SEQ ID NO:18998 |
| | 21-225_205F5 | NA | CGGGCGAGTCAGGGCATTGG CAATTATTAGCC SEQ ID NO:2975 | | GGTGTCTCCAGTTTGCAA AGT SEQ ID NO:10987 | | CAACAATATAGTAATTACC TCTCACT SEQ ID NO:18999 |
| iPS:436302 | | AA | RASQGIGNYLA SEQ ID NO:2976 | | GVSSLQS SEQ ID NO:10988 | | QQYSNYPLT SEQ ID NO:19000 |
| | 21-225_205G7 | NA | AGGGCCAGTCAGAGTGTTTT CAGCAACTACTTAGCC SEQ ID NO:2977 | | GGTGCATCCAGCAGGGC CGCT SEQ ID NO:10989 | | CAGCAGTATGAAAGTTCACC GTGGACG SEQ ID NO:19001 |
| iPS:436304 | | AA | RASQSVFSNYLA SEQ ID NO:2978 | | GASSRAA SEQ ID NO:10990 | | QQYESSPWT SEQ ID NO:19002 |
| | 21-225_201F3 | NA | AGGTCTAGTCAGAGAGCTCCT GCATAATAATAGATACAACC ATTTGGAT SEQ ID NO:2979 | | TTGGGTTCTAATCGGGCC TCC SEQ ID NO:10991 | | ATGCAAGCTCTACAAACTCC CACT SEQ ID NO:19003 |
| iPS:436306 | | AA | RSSQSLLHNNRYNHLD SEQ ID NO:2980 | | LGSNRAS SEQ ID NO:10992 | | MQALQTPT SEQ ID NO:19004 |
| | | NA | AGGGCCAGTCAGAGTGTTAA TAGCTACTTAGCC SEQ ID NO:2981 | | GGTGCATCCACCAGGGC CACT | | CAAGAGTATAATGACTGGCC GTGCAGT |

FIGURE 49
(Continued)

| iPS | Clone | Type | SEQ ID | CDR-L1 | SEQ ID | CDR-L2 | SEQ ID | CDR-L3 |
|---|---|---|---|---|---|---|---|---|
| iPS:436308 | 21-225_201H4 | AA | SEQ ID NO:2981 | RASQSVNSYLA | SEQ ID NO:10993 | GASTRAT | SEQ ID NO:19005 | QEYNDWPCS |
| | | NA | SEQ ID NO:2982 | CGGGCAAGTCAGGGCATTAGAAATGATTTAGGC | SEQ ID NO:10994 | TCTGCATCCTTTTGCAAAGA | SEQ ID NO:19006 | CTACAGCATAATAGTTACCGCTCACT |
| iPS:436310 | 21-225_205H8 | AA | SEQ ID NO:2983 | RASQGIRNDLG | SEQ ID NO:10995 | SASFLQR | SEQ ID NO:19007 | LQHNSYPLT |
| | | NA | SEQ ID NO:2984 | AGGGCCAGTCAGAGTATTAACAGCAACTACTTAGCC | SEQ ID NO:10996 | GGTGCATCCAGCAGGCCACT | SEQ ID NO:19008 | CAGCAGTATGAAAACTCACCGTGGACG |
| iPS:436312 | 21-225_202D11 | AA | SEQ ID NO:2985 | RASQSINSNYLA | SEQ ID NO:10997 | GASSRAT | SEQ ID NO:19009 | QQYENSPWT |
| | | NA | SEQ ID NO:2986 | CGGGCAAGTCACAACATTAACAGCTATTTAAAT | SEQ ID NO:10998 | GCTGCATCCAGTTGCAAAGT | SEQ ID NO:19010 | CAACAGAGTTACAGTTTCCCGCTCACT |
| iPS:436314 | 21-225_206A4 | AA | SEQ ID NO:2987 | RASHNINSYLN | SEQ ID NO:10999 | AASSLQS | SEQ ID NO:19011 | QQSYSFPLT |
| | | NA | SEQ ID NO:2988 | CGGGCCAGTCAGAGCATTGGTCGTAGCTTACAC | SEQ ID NO:11000 | TATGCTTCCCAGTCCTTCTCA | SEQ ID NO:19012 | CATCAGAGTAGAAGTTACCGCTCACT |
| iPS:436316 | 21-225_206G4 | AA | SEQ ID NO:2989 | RASQSIGRSLH | SEQ ID NO:11001 | YASQSFS | SEQ ID NO:19013 | HQSRSLPLT |
| | 21-225_206A5 | NA | SEQ ID NO:2990 | CGGGCAAGTCACAACATTAACAGCTATTTAAAT | SEQ ID NO:11002 | GCTGCATCCAGTTGCAAAGT | SEQ ID NO:19014 | CAACAGAGTTACAGTTTCCCGCTCACT |
| | | AA | SEQ ID NO:2991 | RASHNINSYLN | SEQ ID NO:11003 | AASSLQS | SEQ ID NO:19015 | QQSYSFPLT |
| iPS:436324 | | NA | SEQ ID NO:2992 | CGGGCCAGTCAGGGCATTAGAAATTATTTAGCC | SEQ ID NO:11004 | GCTGCATCCAGTTTGCAAAGT | SEQ ID NO:19016 | CAACAGTACACAGTAATTACCTCTCACT |

FIGURE 49
(Continued)

| | | | | | | |
|---|---|---|---|---|---|---|
| iPS:436328 | 21-225_207G6 | AA | SEQ ID NO:2993<br>RASQGIRNYLA<br>SEQ ID NO:2994 | SEQ ID NO:11005<br>AASSLQS<br>SEQ ID NO:11006 | | SEQ ID NO:19017<br>QQYSNYPLT<br>SEQ ID NO:19018 |
| iPS:436332 | 21-225_207F12 | NA | CGGGCAAGTCAGGGCATTAG<br>AAATGATTTAGGC<br>SEQ ID NO:2995 | GCTGCATCCAGTTGCAA<br>AGT<br>SEQ ID NO:11007 | CTACAGCATAATAGTTACCC<br>TCTCACC<br>SEQ ID NO:19019 |
| | | AA | RASQGIRNDLG<br>SEQ ID NO:2996 | AASSLQS<br>SEQ ID NO:11008 | LQHNSYPLT<br>SEQ ID NO:19020 |
| iPS:436334 | 21-225_208B2 | NA | CGGGCAAGTCAGGGCATTAG<br>ACATGATTTAGGC<br>SEQ ID NO:2997 | GCTGCATCCAGTTGCAA<br>AGT<br>SEQ ID NO:11009 | CTACAGCATTATAGTTACCC<br>TCGGACG<br>SEQ ID NO:19021 |
| | | AA | RASQGIRHDLG<br>SEQ ID NO:2998 | AASSLQS<br>SEQ ID NO:11010 | LQHYSYPRT<br>SEQ ID NO:19022 |
| iPS:436336 | 21-225_208G3 | NA | AGGGTCTAGTCAGAGCCTCCT<br>GCATAATAATAAATACAACC<br>ATTTGGAT<br>SEQ ID NO:2999 | TTGGGTTCTAATCGGGCC<br>TCC<br>SEQ ID NO:11011 | ATGCAAGCTCTACAAACTCC<br>CACT<br>SEQ ID NO:19023 |
| | | AA | RSSQSLLHNNKYNHLD<br>SEQ ID NO:3000 | LGSNRAS<br>SEQ ID NO:11012 | MQALQTPT<br>SEQ ID NO:19024 |
| iPS:436338 | 21-225_208B5 | NA | AGGGCCAGTCAGAGTGTTAG<br>CAGCAACTACTTAGCC<br>SEQ ID NO:3001 | GGTGCATCCAGCAGGGC<br>CACT<br>SEQ ID NO:11013 | CAGCACTACGAAAACTCACC<br>GTGGACG<br>SEQ ID NO:19025 |
| | | AA | RASQSVSSNYLA<br>SEQ ID NO:3002 | GASSRAT<br>SEQ ID NO:11014 | QHYENSPWT<br>SEQ ID NO:19026 |
| iPS:436338 | 21-225_208E8 | NA | CGGGCAAGTCACAACATTAA<br>CAGCTATTTAAAT<br>SEQ ID NO:3003 | GCTGCATCCAGTTGCAA<br>AGT<br>SEQ ID NO:11015 | CAACAGAGTTACAGTTTCCC<br>GCTCACT<br>SEQ ID NO:19027 |
| | | AA | RASHNINSYLN<br>SEQ ID NO:3004 | AASSLQS<br>SEQ ID NO:11016 | QQSYSFPLT<br>SEQ ID NO:19028 |

FIGURE 49
(Continued)

| | | | | | | |
|---|---|---|---|---|---|---|
| iPS:436340 | 21-225_208A9 | NA | AGGGCCAGTCAGAGTGTTAG CAACAACTACTTAGCC SEQ ID NO:3005 | GGTGCATCCAGCAGGGC CACT SEQ ID NO:11017 | CAGCACTATCATAGCTCACC GTGGACG SEQ ID NO:19029 |
| | | AA | RASQSVSNNYLA SEQ ID NO:3006 | GASSRAT SEQ ID NO:11018 | QHYHSSPWT SEQ ID NO:19030 |
| iPS:436344 | 21-225_208B11 | NA | CGGGCAAGTCACAACATTAA CAGCTATTAAAT SEQ ID NO:3007 | GCTGCATCCAGTTGCAA AGT SEQ ID NO:11019 | CAACAGAGTTACAGTTTCCC GCTCACT SEQ ID NO:19031 |
| | | AA | RASHNINSYLN SEQ ID NO:3008 | AASSLQS SEQ ID NO:11020 | QQSYSFPLT SEQ ID NO:19032 |
| iPS:436350 | 21-225_210E4 | NA | CGGGCAAGTCAGGGCATTAG AAATGATTAGGC SEQ ID NO:3009 | GCTGCATCCAGTTGCAA AGT SEQ ID NO:11021 | CTACAGCATAATAGTTACCC ATTCACT SEQ ID NO:19033 |
| | | AA | RASQGIRNDLG SEQ ID NO:3010 | AASSLQS SEQ ID NO:11022 | LQHNSYPFT SEQ ID NO:19034 |
| iPS:436352 | 21-225_210G5 | NA | CGGGCAAGTCAGGGCATTAG ACATGATTAGGC SEQ ID NO:3011 | GCTGCATCCAGTTGCAA AGT SEQ ID NO:11023 | CTACACCATTATAGTTACCC TCGGACG SEQ ID NO:19035 |
| | | AA | RASQGIRHDLG SEQ ID NO:3012 | AASSLQS SEQ ID NO:11024 | LHHYSYPRT SEQ ID NO:19036 |
| iPS:436354 | 21-225_210G10 | NA | CGGACAAGTCAGGGCATTAA AAGCAACTTAGGC SEQ ID NO:3013 | GCTGCATCCAGTTGTTT AGT SEQ ID NO:11025 | CTACAGTATAATAGTTACCC TCCCACC SEQ ID NO:19037 |
| | | AA | RTSQGIRNDLG SEQ ID NO:3014 | AASSLFS SEQ ID NO:11026 | LQYNSYPPT SEQ ID NO:19038 |
| iPS:436356 | 21-225_210H10 | NA | AGGGCCAGTCAGAGTGTTAA AAGCAACTTAGCC SEQ ID NO:3015 | GGTGCATCCACCAGGGC CACT SEQ ID NO:11027 | CAGCAGTATTATAACTGGCT GTGCAGT SEQ ID NO:19039 |
| | | AA | RASQSVKSNLA SEQ ID NO:3016 | GASTRAT SEQ ID NO:11028 | QQYYNWLCS SEQ ID NO:19040 |

FIGURE 49
(Continued)

| | | | | | |
|---|---|---|---|---|---|
| iPS:436358 | 21-225_210D11 | NA | CGGGCAAGTCACAACATTAA CAGCTATTAAAT SEQ ID NO:3017 | GCTGCATCCAGTTTGCAA AGT SEQ ID NO:11029 | CAACAGAGTTACAGTTTCCC GCTCACT SEQ ID NO:19041 |
| | | AA | RASHNINSYLN SEQ ID NO:3018 | AASSLQS SEQ ID NO:11030 | QQSYSFPLT SEQ ID NO:19042 |
| iPS:436360 | 21-225_210H11 | NA | CGGGCGAGTCAGGGTATTAG CATCTGGTTAGCC SEQ ID NO:3019 | GCTGCATCCAGTTTGCAA AGT SEQ ID NO:11031 | CAACAGGCTAAAAGTTTCCC ATTCACT SEQ ID NO:19043 |
| | | AA | RASQGISIWLA SEQ ID NO:3020 | AASSLQS SEQ ID NO:11032 | QQAKSFPFT SEQ ID NO:19044 |
| iPS:436362 | 21-225_210C12 | NA | AGGTCTAGTCAGAGCCTCCT GCATTATAAATGGACACAACT TTTTGGAT SEQ ID NO:3021 | TTGGTTTCTAATCGGGCC TCC SEQ ID NO:11033 | ATGCAAGCTCTACAAACTCC CATGTGCAGT SEQ ID NO:19045 |
| | | AA | RSSQSLLHYNGHNFLD SEQ ID NO:3022 | LVSNRAS SEQ ID NO:11034 | MQALQTPMCS SEQ ID NO:19046 |
| iPS:436364 | 21-225_211A11 | NA | CGGGCGAGTCAGGGCATTGG CAATTATTTAGCC SEQ ID NO:3023 | GATGCATCCAGTTTGGA AAGT SEQ ID NO:11035 | CAACACTATATGACTTACC GCTCACT SEQ ID NO:19047 |
| | | AA | RASQGIGNYLA SEQ ID NO:3024 | DASSLES SEQ ID NO:11036 | QHYMTYPLT SEQ ID NO:19048 |
| iPS:436366 | 21-225_211A3 | NA | CGGGCGAGTCAGGCCATTGG GAAACATTTAGCC SEQ ID NO:3025 | GCTGCATCCAGATTGCA AAGT SEQ ID NO:11037 | CAACAGTATAGTAATTATCC GCTCACT SEQ ID NO:19049 |
| | | AA | RASQAIGKHLA SEQ ID NO:3026 | AASRLQS SEQ ID NO:11038 | QQYSNYPLT SEQ ID NO:19050 |
| iPS:436368 | 21-225_211G3 | NA | AGGGCCAGTCAGAGTGTTAG CAGCAGCTTCTTAGCC SEQ ID NO:3027 | GGTGCATCCAGCAGGGC CACT SEQ ID NO:11039 | CAGCAGTATGTTAGCTCACC GCTCACT SEQ ID NO:19051 |
| | | AA | RASQSVSSFLA | GASSRAT | QQYVSSPLT |

FIGURE 49
(Continued)

| | | | | | |
|---|---|---|---|---|---|
| iPS:436370 | 21-225_211A6 | NA | SEQ ID NO:3028<br>CGGGCGAGTCAGGGCATTGG<br>CAAGTATTTAGCC | SEQ ID NO:11040<br>GCTGCATCCAGTTTGCTA<br>AGT | SEQ ID NO:19052<br>CAAAAGTATGATACTTACCC<br>ATTCACT |
| | | AA | SEQ ID NO:3029<br>RASQGIGKYLA | SEQ ID NO:11041<br>AASSLLS | SEQ ID NO:19053<br>QKYDTYPFT |
| iPS:436372 | 21-225_211A8 | NA | SEQ ID NO:3030<br>CGGGCGAGTCAGGGCATTAG<br>CAGATATTTAGCC | SEQ ID NO:11042<br>GCTGCATCCAGTTTGCAA<br>AGT | SEQ ID NO:19054<br>CTACGGTATGATACTTACCC<br>TCTCATT |
| | | AA | SEQ ID NO:3031<br>RASQGISRYLA | SEQ ID NO:11043<br>AASSLQS | SEQ ID NO:19055<br>LRYDTYPLI |
| iPS:436374 | 21-225_211C10 | NA | SEQ ID NO:3032<br>AGGTCTAGTCAGAGCCTCCT<br>CCATAGTAATGGATACAACT<br>ATTTGGAT | SEQ ID NO:11044<br>TTGGGTTCTAATCGGGCC<br>TCC | SEQ ID NO:19056<br>ATGCAAGCTCTACTAACTCC<br>CGTGTGCAGT |
| | | AA | SEQ ID NO:3033<br>RSSQSLLHSNGYNYLD | SEQ ID NO:11045<br>LGSNRAS | SEQ ID NO:19057<br>MQALLTPVCS |
| iPS:436376 | 21-225_212E6 | NA | SEQ ID NO:3034<br>CGGGCGAGTCAGGGCATTAG<br>CAATCATTAGCC | SEQ ID NO:11046<br>GCTGCATCCAGTTTGCAA<br>AGT | SEQ ID NO:19058<br>CAACAGTATGTTACCTACCC<br>TCTCACT |
| | | AA | SEQ ID NO:3035<br>RASQGISNHLA | SEQ ID NO:11047<br>AASSLQS | SEQ ID NO:19059<br>QQYVIYPLT |
| iPS:436378 | 21-225_212D7 | NA | SEQ ID NO:3036<br>CGGGCGAGTCAGGGCATTAG<br>CAATCATTAGCC | SEQ ID NO:11048<br>GCTGCATCCAGTTTGCAA<br>AGT | SEQ ID NO:19060<br>CAGCAGTATAGTAATTACCC<br>TCTCACT |
| | | AA | SEQ ID NO:3037<br>RASQGISNHLA | SEQ ID NO:11049<br>AASSLQS | SEQ ID NO:19061<br>QQYSNYPLT |
| iPS:436380 | 21-225_212H9 | NA | SEQ ID NO:3038<br>CGGGCGAGTCAGGGCATTAG<br>CAGTTATTTAGCC | SEQ ID NO:11050<br>GCTGCATCCAGTTTGCAA<br>AGT | SEQ ID NO:19062<br>CTACGGTATGATACTTACCC<br>TCTCACT |
| | | | SEQ ID NO:3039 | SEQ ID NO:11051 | SEQ ID NO:19063 |

FIGURE 49
(Continued)

| | | | | | | |
|---|---|---|---|---|---|---|
| | | RASQGISSYLA | | AASSLQS | | LRYDTYPLT |
| | AA | SEQ ID NO:3040 | | SEQ ID NO:11052 | | SEQ ID NO:19064 |
| iPS:436382 | NA | AGGGCCAGTCAGAGTGTTGC CAGCAGCTTAGCC | | GGTACATCCACCAGGGC CACT | | CAGCAGTATAATGACTGGCC GTGCAGT |
| 21-225_212C10 | | SEQ ID NO:3041 | | SEQ ID NO:11053 | | SEQ ID NO:19065 |
| | AA | RASQSVASSLA | | GTSTRAT | | QQYNDWPCS |
| iPS:436384 | | SEQ ID NO:3042 | | SEQ ID NO:11054 | | SEQ ID NO:19066 |
| 21-225_212F10 | NA | CGGGCGAGTCAGGGCATTAG CAATTATTAGAC | | TCTGCATCCAATTTGCAA AGT | | CAACACTATAGTAATTACC GCTCACT |
| | | SEQ ID NO:3043 | | SEQ ID NO:11055 | | SEQ ID NO:19067 |
| iPS:436386 | AA | RASQGISNYLD | | SASNLQS | | QHYSNYPLT |
| | | SEQ ID NO:3044 | | SEQ ID NO:11056 | | SEQ ID NO:19068 |
| 21-225_212B11 | NA | CGGGCAAGTCAGGGCATTAG AAATGATTAGGC | | GCTGCATCCAGTTTGCAA AGT | | CTACTGCATTATAGTTACCCT CGGACG |
| | | SEQ ID NO:3045 | | SEQ ID NO:11057 | | SEQ ID NO:19069 |
| iPS:436388 | AA | RASQGIRNDLG | | AASSLQS | | LLHYSYPRT |
| | | SEQ ID NO:3046 | | SEQ ID NO:11058 | | SEQ ID NO:19070 |
| 21-225_212H11 | NA | CGGGCGAGTCAGGGCATTGG GAAACATTAGCC | | GCTGCATCCAGATTGCA AAGT | | CAACACTATAGTAATTACC GCTCACT |
| | | SEQ ID NO:3047 | | SEQ ID NO:11059 | | SEQ ID NO:19071 |
| iPS:436390 | AA | RASQAIGKHLA | | AASRLQS | | QHYSNYPLT |
| | | SEQ ID NO:3048 | | SEQ ID NO:11060 | | SEQ ID NO:19072 |
| 21-225_213D2 | NA | CGGGCGAGTCAGGGCATTAG CAATCATTAGCC | | GCTGCATCCAGTTTGCAA AGT | | CACCAGTATAGTAATTACC TCTCACT |
| | | SEQ ID NO:3049 | | SEQ ID NO:11061 | | SEQ ID NO:19073 |
| iPS:436392 | AA | RASQGISNHLA | | AASSLQS | | HQYSNYPLT |
| | | SEQ ID NO:3050 | | SEQ ID NO:11062 | | SEQ ID NO:19074 |
| 21-225_213B3 | NA | CGGGCGAGTCAGGGCATTGG CAAGTATTAGCC | | GCTGCATCCAGTGTGCTA AGT | | CAAAAGTATGATACTTACC ATTCACT |
| | | SEQ ID NO:3051 | | SEQ ID NO:11063 | | SEQ ID NO:19075 |

FIGURE 49
(Continued)

| | | | | | | | |
|---|---|---|---|---|---|---|---|
| | | | RASQGIGKYLA | AASSVLS | | QKYDTYPFT | |
| iPS:436394 | | AA | SEQ ID NO:3052 | SEQ ID NO:11064 | | SEQ ID NO:19076 | |
| | 21-225_213C4 | NA | CGGGCGAGTCAGGCCATTAGGAATTATTAGCC | GCTGCATCCAGTTTGCAAAGT | | CAACAGTATAGTAATTACCCTCTCACT | |
| | | | SEQ ID NO:3053 | SEQ ID NO:11065 | | SEQ ID NO:19077 | |
| | | | RASQAIRNYLA | AASSLQS | | QQYSNYPLT | |
| iPS:436396 | | AA | SEQ ID NO:3054 | SEQ ID NO:11066 | | SEQ ID NO:19078 | |
| | 21-225_213E5 | NA | CGGGCGAGTCAGGCCATTGGGAAACATTTAGCC | GCTGCATCCAGATTGCAAAGT | | CAACACTATAGTAATTACCCGCTCACT | |
| | | | SEQ ID NO:3055 | SEQ ID NO:11067 | | SEQ ID NO:19079 | |
| | | | RASQAIGKHLA | AASRLQS | | QHYSNYPLT | |
| iPS:436398 | | AA | SEQ ID NO:3056 | SEQ ID NO:11068 | | SEQ ID NO:19080 | |
| | 21-225_213B8 | NA | CGGGCGAGTCAGGCCATTAGCAATCATTAGCC | GCTGCATCCAGTTTGCAAAGT | | CAACAGTATAGTAATTACCCTCTCACT | |
| | | | SEQ ID NO:3057 | SEQ ID NO:11069 | | SEQ ID NO:19081 | |
| | | | RASQGISNHLA | AASSLQS | | QQYSNYPLT | |
| | | AA | SEQ ID NO:3058 | SEQ ID NO:11070 | | SEQ ID NO:19082 | |
| | 21-225_213H7 | NA | AAGTCCAGCCAGAATGTTTTAGACATCTCCAACAATAAGAATTCCTTAGGT | TGGGCATCTACCCGGGAATCC | | CAGCAATATTATAACATTCCTCCGACG | |
| iPS:436400 | | | SEQ ID NO:3059 | SEQ ID NO:11071 | | SEQ ID NO:19083 | |
| | | | KSSQNVLDISNNKNSLG | WASTRES | | QQYYNIPPT | |
| | | AA | SEQ ID NO:3060 | SEQ ID NO:11072 | | SEQ ID NO:19084 | |
| | 21-225_213H12 | NA | AAGTCCAGCCAGAATGTTTTAAAGACCTCCAACAATAGGAACTACTTAGCT | TGGGCATCTACCCGGGAATCC | | CACCAATATTATAGTATTCCGTGGACC | |
| iPS:436402 | | | SEQ ID NO:3061 | SEQ ID NO:11073 | | SEQ ID NO:19085 | |
| | | | KSSQNVLKTSNNRNYLA | WASTRES | | HQYYSIPWT | |
| | | AA | SEQ ID NO:3062 | SEQ ID NO:11074 | | SEQ ID NO:19086 | |

FIGURE 49
(Continued)

| | | | | | |
|---|---|---|---|---|---|
| iPS:436404 | 21-225_214C3 | NA | CGGGCGAGTCAGGGCATTGG CAATTATTAGCC SEQ ID NO:3063 | GCTGCATCCAGTTTGCAA AGT SEQ ID NO:11075 | CAACAATATATGACTTACCC AATCACT SEQ ID NO:19087 |
| | | AA | RASQGIGNYLA SEQ ID NO:3064 | AASSLQS SEQ ID NO:11076 | QQYMTYPIT SEQ ID NO:19088 |
| iPS:436406 | 21-225_214E4 | NA | CGGGCGAGTCAGGGCATTAG CAATTATTAGCC SEQ ID NO:3065 | GCTGCATCCAGTTTGCAA AGT SEQ ID NO:11077 | CAACAGTATCTTACTTACCC ATTCACT SEQ ID NO:19089 |
| | | AA | RASQGISNYLA SEQ ID NO:3066 | AASSLQS SEQ ID NO:11078 | QQYLTYPFT SEQ ID NO:19090 |
| iPS:436408 | 21-225_214H8 | NA | CGGGCCAGTCAGAGCATTGG TGTTAGTTTACAC SEQ ID NO:3067 | TATGCTTCCCAGTCCTTC TCA SEQ ID NO:11079 | CATCAGAGTCGTAGTTTACC ATTCACT SEQ ID NO:19091 |
| | | AA | RASQSIGVSLH SEQ ID NO:3068 | YASQSFS SEQ ID NO:11080 | HQSRSLPFT SEQ ID NO:19092 |
| iPS:436410 | 21-225_212E10 | NA | CGGGCGAGTCAGGGCATTAG CAATCATTAGCC SEQ ID NO:3069 | GCTGCATCCAGTTTGCAA AGT SEQ ID NO:11081 | CAACAGTATAGTAATTACCC TCTCACT SEQ ID NO:19093 |
| | | AA | RASQGISNHLA SEQ ID NO:3070 | AASSLQS SEQ ID NO:11082 | QQYSNYPLT SEQ ID NO:19094 |
| iPS:436412 | 21-225_214H9 | NA | CGGGCAAGTCAGGGCATTAG AAATGATTTAGGC SEQ ID NO:3071 | GCTGCATCCAGTTTGCAA AGT SEQ ID NO:11083 | CTACAGCATTATAGTTACCC TCGGACG SEQ ID NO:19095 |
| | | AA | RASQGIRNDLG SEQ ID NO:3072 | AASSLQS SEQ ID NO:11084 | LQHYSYPRT SEQ ID NO:19096 |
| iPS:436414 | 21-225_214G10 | NA | CGGGCAAGTCAGGGCATTAG AAATGATTTAGGC SEQ ID NO:3073 | GCTGCATCCAGTTTGCAA AGT SEQ ID NO:11085 | CTACTGCATAATAGTTACCC TCGGACG SEQ ID NO:19097 |
| | | AA | RASQGIRNDLG SEQ ID NO:3074 | AASSLQS SEQ ID NO:11086 | LLHNSYPRT SEQ ID NO:19098 |

FIGURE 49
(Continued)

| | | | | | |
|---|---|---|---|---|---|
| iPS:436416 | 21-225_214G12 | NA | CGGGCAAGTCAGGGCATTAG AAATGATTTAGGC SEQ ID NO:3075 | GCTGCATCCAGTTTGCAA AGT SEQ ID NO:11087 | GTAATGCATTATAGTTACC TCGGACG SEQ ID NO:19099 |
| | | AA | RASQGIRNDLG SEQ ID NO:3076 | AASSLQS SEQ ID NO:11088 | VMHYSYPRT SEQ ID NO:19100 |
| iPS:436418 | 21-225_215E3 | NA | CGGGCAAGTCAGGGCATTAG AAATGATTTAGGC SEQ ID NO:3077 | GCTGCATCCAGTTTGCAA AGT SEQ ID NO:11089 | GTAATGCATAATAGTTACC TCGGACG SEQ ID NO:19101 |
| | | AA | RASQGIRNDLG SEQ ID NO:3078 | AASSLQS SEQ ID NO:11090 | VMHNSYPRT SEQ ID NO:19102 |
| iPS:436420 | 21-225_215B5 | NA | CGGGCGAGTCAGGGCATTAG CAATCATTTAGCC SEQ ID NO:3079 | GCTGCATCCAGTTTGCAA AGT SEQ ID NO:11091 | CAGCAGTATATTAATTACCC TCTCACT SEQ ID NO:19103 |
| | | AA | RASQGISNHLA SEQ ID NO:3080 | AASSLQS SEQ ID NO:11092 | QQYINYPLT SEQ ID NO:19104 |
| iPS:436422 | 21-225_215D6 | NA | CGGGCGAGTCAGGGCATTAG CAATCATTTAGCC SEQ ID NO:3081 | GCTGCATCCAGTTTGCAT AGT SEQ ID NO:11093 | CAACAGTATGTTACTTACCC TCTCACT SEQ ID NO:19105 |
| | | AA | RASQGISNHLA SEQ ID NO:3082 | AASSLHS SEQ ID NO:11094 | QQYVTYPLT SEQ ID NO:19106 |
| iPS:436424 | 21-225_215H6 | NA | CGGGCCAGTCAGAGCATCGG TGTTAGTTACAC SEQ ID NO:3083 | TATGCTTCCCAGTCCCTC TCA SEQ ID NO:11095 | CATCAGAGTCGCAGTTACC ATTCACT SEQ ID NO:19107 |
| | | AA | RASQSIGVSLH SEQ ID NO:3084 | YASQSLS SEQ ID NO:11096 | HQSRSLPFT SEQ ID NO:19108 |
| iPS:436426 | 21-225_215C7 | NA | AGGGCCAGTCAGAGAGGATTAC CACCAACTTCTTAGCT SEQ ID NO:3085 | GGTGCATCCAGCAGGGC CACT SEQ ID NO:11097 | CAGCAGTATGTTAGTTCATT GCTCACT SEQ ID NO:19109 |
| | | AA | RASQRITTNFLA SEQ ID NO:3086 | GASSRAT SEQ ID NO:11098 | QQYVSSLLT SEQ ID NO:19110 |

FIGURE 49
(Continued)

| | | | | | |
|---|---|---|---|---|---|
| iPS:436428 | 21-225_215E11 | NA | CGGGCAAGTCAGGGCATTAG AAATGATTTAGGC SEQ ID NO:3087 | GCTGCATCCAGTTTGCAA AGT SEQ ID NO:11099 | GTAATGCATTATAGTTACC TCGGACG SEQ ID NO:19111 |
| | | AA | RASQGIRNDLG SEQ ID NO:3088 | AASSLQS SEQ ID NO:11100 | VMHYSYPRT SEQ ID NO:19112 |
| iPS:436430 | 21-225_215A12 | NA | CGGAGAGTCAGGAGACATTGG CAATTATTAGCC SEQ ID NO:3089 | GCTGCATCCAGTTTACAG AGT SEQ ID NO:11101 | CAACAGTATGTTACTTACC GCTCACT SEQ ID NO:19113 |
| | | AA | RTSQDIGNYLA SEQ ID NO:3090 | AASSLQS SEQ ID NO:11102 | QQYVTYPLT SEQ ID NO:19114 |
| iPS:436432 | 21-225_215H12 | NA | AGGGCCAGTCAGAGTGTTAG CAGCAGTTCTTAGCT SEQ ID NO:3091 | GGTGCATCCAGCAGGGC CATT SEQ ID NO:11103 | CAGCAGTATGTTAGCTCAC GCTCACT SEQ ID NO:19115 |
| | | AA | RASQSVSSSFLA SEQ ID NO:3092 | GASSRAI SEQ ID NO:11104 | QQYVSSPLT SEQ ID NO:19116 |
| iPS:436434 | 21-225_216B10 | NA | AGGGCCAGTCAGAGTGTTAA CAACAACTTAGCC SEQ ID NO:3093 | GGTGCATCCACCAGGGC CACT SEQ ID NO:11105 | CAGCAGTATAATGACTGGC GTGCAGT SEQ ID NO:19117 |
| | | AA | RASQSVNNNLA SEQ ID NO:3094 | GASTRAT SEQ ID NO:11106 | QQYNDWPCS SEQ ID NO:19118 |
| iPS:436436 | 21-225_216F10 | NA | AGGGCCAGTCAGAGTGTTAG CAGCAGTTCTTAGCC SEQ ID NO:3095 | GGTACATCCACCAGGGC CACT SEQ ID NO:11107 | CAACAGTATGATAGGTCAC ATTCACT SEQ ID NO:19119 |
| | | AA | RASQSVSSSFLA SEQ ID NO:3096 | GTSTRAT SEQ ID NO:11108 | QQYDRSPFT SEQ ID NO:19120 |
| iPS:436438 | 21-225_216E8 | NA | CGGGCAAGTCAGGGCATTAG AAATGATTTAGGC SEQ ID NO:3097 | GCTGCATCCAGTTTGCAA AGT SEQ ID NO:11109 | CTAATGCATTATAGTTACC TCGGACG SEQ ID NO:19121 |
| | | AA | RASQGIRNDLG SEQ ID NO:3098 | AASSLQS SEQ ID NO:11110 | LMHYSYPRT SEQ ID NO:19122 |

FIGURE 49
(Continued)

| | | | | | |
|---|---|---|---|---|---|
| iPS:436446 | 21-225_216H12 | NA | CGGGCAAGTCAGGGCATTAG AAATGATTTAGGC SEQ ID NO:3099 | GGTGCATCCAGTTTGCA AAGT SEQ ID NO:11111 | GTAATGCATAATAGTTACCC TCGGACG SEQ ID NO:19123 |
| | | AA | RASQGIRNDLG SEQ ID NO:3100 | GASSLQS SEQ ID NO:11112 | VMHNSYPRT SEQ ID NO:19124 |
| iPS:436448 | 21-225_217A3 | NA | CGGGCCAGTCAGAGCATTGG TAGTAGTTACAC SEQ ID NO:3101 | TATGCTTCCCAGTCCTTC TCA SEQ ID NO:11113 | CATCAGAGTAGAAGTTACC GTGACG SEQ ID NO:19125 |
| | | AA | RASQSIGSSLH SEQ ID NO:3102 | YASQSFS SEQ ID NO:11114 | HQSRSLPWT SEQ ID NO:19126 |
| iPS:436450 | 21-225_217E5 | NA | CGGGCAAGTCAGGGCATTAG AAATGATTTAGGC SEQ ID NO:3103 | GCTGCATCCAGTTGCAA AGT SEQ ID NO:11115 | GTAATGCATAATAGTTACCC TCGGACG SEQ ID NO:19127 |
| | | AA | RASQGIRNDLG SEQ ID NO:3104 | AASSLQS SEQ ID NO:11116 | VMHNSYPRT SEQ ID NO:19128 |
| iPS:436452 | 21-225_217G5 | NA | CGGGGCGAGTCAGGGCATTGG CAATTATTTAGCC SEQ ID NO:3105 | GCTGCATCCAGTTTGCAA AGT SEQ ID NO:11117 | CAACACAGTATGTTAATACCC TCTCACT SEQ ID NO:19129 |
| | | AA | RASQGIGNYLA SEQ ID NO:3106 | AASSLQS SEQ ID NO:11118 | QQYVNYPLT SEQ ID NO:19130 |
| iPS:436454 | 21-225_217B10 | NA | CGGGCGAGTCAGGCCATTGG GAAACATTTAGCC SEQ ID NO:3107 | GCTGCATCCAGTTTGCA AGT SEQ ID NO:11119 | CAACACACCAGTAAATCTCC AGTGCAG SEQ ID NO:19131 |
| | | AA | RASQAIGKHLA SEQ ID NO:3108 | AASRLQS SEQ ID NO:11120 | QHTSKSPVQ SEQ ID NO:19132 |
| iPS:436456 | 21-225_217G10 | NA | CGGGCAAGTCAGGGCATTAG AAATGATTTAGGC SEQ ID NO:3109 | GCTGCATCCAGTTTGCAA AGT SEQ ID NO:11121 | GTAATGCATAATAGTTACCC TCGGACG SEQ ID NO:19133 |
| | | AA | RASQGIRNDLG SEQ ID NO:3110 | AASSLQS SEQ ID NO:11122 | VMHNSYPRT SEQ ID NO:19134 |

FIGURE 49
(Continued)

| | | | | | |
|---|---|---|---|---|---|
| iPS:436458 | 21-225_217H12 | NA | CGGGCAAGTCAGGGCATTAG AAATGATTAGGC SEQ ID NO:3111 RASQGIRNDLG SEQ ID NO:3112 | GCTGCATCCAGTTTGCAA AGT SEQ ID NO:11123 AASSLQS SEQ ID NO:11124 | CTAATGCATTATAGTTACC TCGGACG SEQ ID NO:19135 LMHYSYPRT SEQ ID NO:19136 |
| | | AA | | | |
| iPS:436462 | 21-225_218C4 | NA | CGGGCAAGTCAGGGCATTAG AAATGATTAGGC SEQ ID NO:3113 RASQGIRNDLG SEQ ID NO:3114 | GCTGCATCCAGTTTGCAA AGT SEQ ID NO:11125 AASSLQS SEQ ID NO:11126 | GTAATGCATTATAGTTACC TCGGACG SEQ ID NO:19137 VMHYSYPRT SEQ ID NO:19138 |
| | | AA | | | |
| iPS:436464 | 21-225_219H1 | NA | CGGGCGAGTCAGGGTATTAG CAATTATTTAGAC SEQ ID NO:3115 RASQGISNYLD SEQ ID NO:3116 | TCTGCATCCAATTTGCAA AGT SEQ ID NO:11127 SASNLQS SEQ ID NO:11128 | CAACACTATAGTAATTACC GCTCACT SEQ ID NO:19139 QHYSNYPLT SEQ ID NO:19140 |
| | | AA | | | |
| iPS:436472 | 21-225_220E1 | NA | AGGGCGAGTCAGAGTATTAG CCGCAGCCACTTAGTC SEQ ID NO:3117 RASQSISRSHLV SEQ ID NO:3118 | GTTACATCCAGCAGGGC CACT SEQ ID NO:11129 VTSSRAT SEQ ID NO:11130 | CAGCAGTATGGTAGCTCACC GTGGACG SEQ ID NO:19141 QQYGSSPWT SEQ ID NO:19142 |
| | | AA | | | |
| iPS:436480 | 21-225_220F8 | NA | CGGGCAAGTCAGGGCATTAG AAATGATTAGGC SEQ ID NO:3119 RASQGIRNDLG SEQ ID NO:3120 | GGTGCATCCAGTTGCA AAGT SEQ ID NO:11131 GASSLQS SEQ ID NO:11132 | GTAATGCATAATAGTTACC TCGGACG SEQ ID NO:19143 VMHNSYPRT SEQ ID NO:19144 |
| | | AA | | | |
| iPS:436488 | 21-225_221A6 | NA | CGGGCGAGTCAGGGTATTAG CAGCTGGTTAGCC SEQ ID NO:3121 RASQGISSWLA SEQ ID NO:3122 | ACTGCATCCAATTTGCAA AGT SEQ ID NO:11133 TASNLQS SEQ ID NO:11134 | CAACAGGCTAACAGTTCCC ATTCACT SEQ ID NO:19145 QQANSFPFT SEQ ID NO:19146 |
| | | AA | | | |

FIGURE 49
(Continued)

| | | | | | |
|---|---|---|---|---|---|
| iPS:436490 | 21-225_221F6 | NA | CGGGGCGAGTCAGGGCATTAG CAATTATTAGCC SEQ ID NO:3123 | GCTGCATCCAATTTACAA AGT SEQ ID NO:11135 | CAACAGTATATGACTTACCC GCTCACT SEQ ID NO:19147 |
| | | AA | RASQGISNYLA SEQ ID NO:3124 | AASNLQS SEQ ID NO:11136 | QQYMTYPLT SEQ ID NO:19148 |
| iPS:436494 | 21-225_221F12 | NA | CGGGCGAGTCAGGGTATTAG CAGCTGGTTAGCC SEQ ID NO:3125 | ACTGCATCCAATTTGCAA AGT SEQ ID NO:11137 | CAACAGGCTAACAGTTTCCC ATTCACT SEQ ID NO:19149 |
| | | AA | RASQGISSWLA SEQ ID NO:3126 | TASNLQS SEQ ID NO:11138 | QQANSFPFT SEQ ID NO:19150 |
| iPS:436496 | 21-225_222E1 | NA | CGGGCGAGTCAGGGTATTAG CAGCTGGTTAGCC SEQ ID NO:3127 | ACTGCATCCAATTTGCAA AGT SEQ ID NO:11139 | CAACAGGCTAACAGTTTCCC ATTCACT SEQ ID NO:19151 |
| | | AA | RASQGISSWLA SEQ ID NO:3128 | TASNLQS SEQ ID NO:11140 | QQANSFPFT SEQ ID NO:19152 |
| iPS:436500 | 21-225_222H3 | NA | AAGTCCAGCAGGTCAGAGTGTTT GAAAAGTTCCAACCATAGGA ACTACTTAGCT SEQ ID NO:3129 | TGGGCATCTACCCGGGA AACC SEQ ID NO:11141 | CAGCAATATTCTCTCTATTCCG TGGACG SEQ ID NO:19153 |
| | | AA | KSSQSVLKSSNHRNYLA SEQ ID NO:3130 | WASTRET SEQ ID NO:11142 | QQYSSIPWT SEQ ID NO:19154 |
| iPS:436502 | 21-225_222A11 | NA | CGGGCGAGTCAGGGCATTAG CAATTATTTGGCC SEQ ID NO:3131 | GCTGCATCCAGTTTGCAA AGT SEQ ID NO:11143 | CTATATTATCTTAATTATCCG CTCACT SEQ ID NO:19155 |
| | | AA | RASQGISNYLA SEQ ID NO:3132 | AASSLQS SEQ ID NO:11144 | LYYLNYPLT SEQ ID NO:19156 |
| iPS:436504 | 21-225_222H4 | NA | CGGGCAAGTCAGAACATTAG TAATTATGTTAAT SEQ ID NO:3133 | ACTGCATCGAGTTTGCA AAGT SEQ ID NO:11145 | CAGCAGTATTACTTTACCCC ATTCACT SEQ ID NO:19157 |
| | | AA | RASQNISNYVN | TASSLQS | QQYFTPFT |

FIGURE 49
(Continued)

| | | | | | |
|---|---|---|---|---|---|
| iPS:436506 | 21-225_222C7 | NA | SEQ ID NO:3134 AGGGCCAGTCAGAGTGTTA CAGCAACTACTTAGCC | SEQ ID NO:11146 GGTGCATCAAGCAGGGC CACT | SEQ ID NO:19158 CAGCAGTATGAAGACTCACC GTGGACG |
| | | AA | SEQ ID NO:3135 RASQSVYSNYLA | SEQ ID NO:11147 GASSRAT | SEQ ID NO:19159 QQYEDSPWT |
| iPS:436508 | 21-225_222F7 | NA | SEQ ID NO:3136 CGGGGCGAGTCAGGGTATTAG CAGCTGGTTAGCC | SEQ ID NO:11148 ACTGCATCCAATTGCAA AGT | SEQ ID NO:19160 CAACAGGCTAACAGTTCC ATTCACT |
| | | AA | SEQ ID NO:3137 RASQGISSWLA | SEQ ID NO:11149 TASNLQS | SEQ ID NO:19161 QQANSFPFT |
| iPS:436510 | 21-225_222H8 | NA | SEQ ID NO:3138 CGGGCAAGTCAGAGACATTAG TAATTATGTTAAT | SEQ ID NO:11150 ATTGCATCGAGTTGCAA AGT | SEQ ID NO:19162 CAGCAGTATTACTTACCCC ATTCACT |
| | | AA | SEQ ID NO:3139 RASQNISNYVN | SEQ ID NO:11151 IASSLQS | SEQ ID NO:19163 QQYFTPFT |
| iPS:436514 | 21-225_222D10 | NA | SEQ ID NO:3140 CGGGCGAGTCAGGGCATTAG CAATTATTTGGCC | SEQ ID NO:11152 GCTGCATCCAGTTGCAA AGT | SEQ ID NO:19164 CTACATTATCTTAATTACCCG CTCACT |
| | | AA | SEQ ID NO:3141 RASQGISNYLA | SEQ ID NO:11153 AASSLQS | SEQ ID NO:19165 LHYLNYPLT |
| iPS:436516 | 21-225_222C12 | NA | SEQ ID NO:3142 CGGGTGAGTCAGGGTATTAG CAGCTGGTTAGCC | SEQ ID NO:11154 ACTGCATCCAATTGCAA AGT | SEQ ID NO:19166 CAACAGGATAACAGTTCC ATTCACT |
| | | AA | SEQ ID NO:3143 RVSQGISSWLA | SEQ ID NO:11155 TASNLQS | SEQ ID NO:19167 QQDNSFPFT |
| iPS:436520 | 21-225_223G10 | NA | SEQ ID NO:3144 AAGTCCAGCCAGAGTATTTT ACTCAGTCCAACAATAAGA ACTACTTAGCT | SEQ ID NO:11156 TGGGCATCTACCCGGGA ATCC | SEQ ID NO:19168 CTGCAATATTTTAGTACTCC GTGGACG |
| | | | SEQ ID NO:3145 | SEQ ID NO:11157 | SEQ ID NO:19169 |

FIGURE 49
(Continued)

| | | | | | | |
|---|---|---|---|---|---|---|
| iPS:436522 | | AA | KSSQSILLSSNNKNYLA SEQ ID NO:3146 | WASTRES SEQ ID NO:11158 | LQYFSTPWT SEQ ID NO:19170 |
| | 21-225_223H10 | NA | CGGGCAAGTCAGGGCATTAG TAATTATTTGGCC SEQ ID NO:3147 | GCTGCATCCAATTTGCAA AGT SEQ ID NO:11159 | CTACATTATCTTAATTACCCA CTCACT SEQ ID NO:19171 |
| iPS:436526 | | AA | RASQGISNYLA SEQ ID NO:3148 | AASNLQS SEQ ID NO:11160 | LHYLNYPLT SEQ ID NO:19172 |
| | 21-225_224A1 | NA | CGGGCAAGTCAGGGCATTGA AAATGATTAGGC SEQ ID NO:3149 | GCTGCATCCAGTTTGCAA AGT SEQ ID NO:11161 | CTACAGCATAATAGTTACCC GCTCACT SEQ ID NO:19173 |
| iPS:436528 | | AA | RASQGIENDLG SEQ ID NO:3150 | AASSLQS SEQ ID NO:11162 | LQHNSYPLT SEQ ID NO:19174 |
| | 21-225_224B1 | NA | CGGGCAAGTCAGGGCATTAG TAATGATTAGGC SEQ ID NO:3151 | GCTGCATCCAGTTTGCAA AGT SEQ ID NO:11163 | CTACAGCATAATAGTTACCC TCCTACT SEQ ID NO:19175 |
| iPS:436534 | | AA | RASQGISNDLG SEQ ID NO:3152 | AASSLQS SEQ ID NO:11164 | LQHNSYPPT SEQ ID NO:19176 |
| | 21-225_224F1 | NA | CGGGCAAGTCAGGGCATTAG AGATGATTAGGC SEQ ID NO:3153 | GCTGCATCCAGTTTGCAA AGT SEQ ID NO:11165 | CTACAGCATTATAGTTACCC TCGGACG SEQ ID NO:19177 |
| iPS:436536 | | AA | RASQGIRDDLG SEQ ID NO:3154 | AASSLQS SEQ ID NO:11166 | LQHYSYPRT SEQ ID NO:19178 |
| | 21-225_224G1 | NA | AAGTCTGGTCAGAGCCTCCT GCATAGTGATGGAAAGACCT TTTTGTCT SEQ ID NO:3155 | GAAATTTCCAACCGGTTC TCT SEQ ID NO:11167 | ATGCAAAGTACACAGTTCC TCGGACG SEQ ID NO:19179 |
| iPS:436538 | | AA | KSGQSLLHSDGKTFLS SEQ ID NO:3156 | EISNRFS SEQ ID NO:11168 | MQSTQLPRT SEQ ID NO:19180 |
| | | NA | CGGGCAAGTCAGGACATTAG AAATGATTAGGC | GCTACATCCAGTTTGCAA AGT | CTACAGCATAATAGTTACCC GCTCACT |

FIGURE 49
(Continued)

| | | | | | | |
|---|---|---|---|---|---|---|
| iPS:436540 | 21-225_224C3 | AA | SEQ ID NO:3157<br>RASQDIRNDLG | SEQ ID NO:11169<br>ATSSLQS | SEQ ID NO:19181<br>LQHNSYPLT | |
| iPS:436544 | 21-225_224F3 | NA | SEQ ID NO:3158<br>CGGGCAAGTCAGGGCATTAG<br>AAATGATTTAGGC | SEQ ID NO:11170<br>GCTGCATCCAGTTTGCAA<br>AGT | SEQ ID NO:19182<br>CTTCAGCATTATAATTACCCT<br>CGGGCG | |
| | | AA | SEQ ID NO:3159<br>RASQGIRNDLG | SEQ ID NO:11171<br>AASSLQS | SEQ ID NO:19183<br>LQHYNYPRA | |
| iPS:436544 | 21-225_224H5 | NA | SEQ ID NO:3160<br>AAGTCCAGCCAGAGTGTTT<br>ATACAGCTCCAACAATTTCA<br>ACTACTTAACT | SEQ ID NO:11172<br>TGGGCATCTACCGGGA<br>ATCC | SEQ ID NO:19184<br>CAGCAATATTATAGTACTCC<br>TCCGACG | |
| | | AA | SEQ ID NO:3161<br>KSSQSVLYSSNNFNYLT | SEQ ID NO:11173<br>WASTRES | SEQ ID NO:19185<br>QQYYSTPPT | |
| iPS:436546 | 21-225_224D6 | NA | SEQ ID NO:3162<br>CGGGCGAGTCAGGGTATTAG<br>CAGCTGGTTAGCC | SEQ ID NO:11174<br>GCTGCATCCAGTTTGCAA<br>AGT | SEQ ID NO:19186<br>CAACAGGCTAACAGTTTCCC<br>GTGGACG | |
| | | AA | SEQ ID NO:3163<br>RASQGISSWLA | SEQ ID NO:11175<br>AASSLQS | SEQ ID NO:19187<br>QQANSFPWT | |
| iPS:436548 | 21-225_224A7 | NA | SEQ ID NO:3164<br>AAGTCTAGTCAGAGCCTCCT<br>GCATAGTGATGGAAAGACCT<br>TTTGTAT | SEQ ID NO:11176<br>GAAATTTCCAACCGGTTC<br>TCT | SEQ ID NO:19188<br>ATGCAAAGTACACAGTTCC<br>TCCGACG | |
| | | AA | SEQ ID NO:3165<br>KSSQSLLHSDGKTFLY | SEQ ID NO:11177<br>EISNRFS | SEQ ID NO:19189<br>MQSTQLPRT | |
| iPS:436550 | 21-225_224D8 | NA | SEQ ID NO:3166<br>AAGTCCAGCCAGAGTGTTT<br>ATACAGCTCCAACAATAAGA<br>ACTACTTAGCT | SEQ ID NO:11178<br>TGGTCGTCTACCCGGAA<br>ATCC | SEQ ID NO:19190<br>CAGCAATATTTAGTACTCC<br>TCCGACG | |
| | | AA | SEQ ID NO:3167<br>KSSQSVLYSSNNKNYLA | SEQ ID NO:11179<br>WSSTRKS | SEQ ID NO:19191<br>QQYFSTPPT | |

FIGURE 49
(Continued)

| | | | | | | | |
|---|---|---|---|---|---|---|---|
| iPS:436554 | 21-225_224C10 | NA | SEQ ID NO:3168 AAGTCCAGCCAGAGTGTTT ATACAATTCCAACAATAAGA ACTACTTAGCT | SEQ ID NO:11180 TGGGCATCTACCCGGGA GTCC | SEQ ID NO:19192 CAACAATATATATTAATCC GTGCAGT |
| | | AA | SEQ ID NO:3169 KSSQSVLYNSNKNYLA | SEQ ID NO:11181 WASTRES | SEQ ID NO:19193 QQYYINPCS |
| iPS:436556 | 21-225_224D10 | NA | SEQ ID NO:3170 CGGGCAAGTCAGGGCATTAG AAATGATTAGGC | SEQ ID NO:11182 GCTGCATCCAGTTTACAA AGT | SEQ ID NO:19194 CTACAACATAATAGTTACC GCTCACT |
| | | AA | SEQ ID NO:3171 RASQGIRNDLG | SEQ ID NO:11183 AASSLQS | SEQ ID NO:19195 LQHNSYPLT |
| iPS:436558 | 21-225_224C11 | NA | SEQ ID NO:3172 AAGTCTAGTCAGAGCCTCCT GCATAGTGATGAAGAAGACCTTCT TTTTGTAT | SEQ ID NO:11184 GAAATTTCCAACGGTTC TCT | SEQ ID NO:19196 ATGCAAAGTACACAGCTTCC TCGGACG |
| | | AA | SEQ ID NO:3173 KSSQSLLHSDGKTFLY | SEQ ID NO:11185 EISNRFS | SEQ ID NO:19197 MQSTQLPRT |
| iPS:436560 | 21-225_224F11 | NA | SEQ ID NO:3174 AAGTCCAGCCAGAGTGTTT ATCCAGTCCAACAATCACA ACTACTTAGCT | SEQ ID NO:11186 TGGGCATCTACCCGGGA ATCC | SEQ ID NO:19198 CAGCAATATATACTACTCC GTGCAGT |
| | | AA | SEQ ID NO:3175 KSSQSVLSSSNNHNYLA | SEQ ID NO:11187 WASTRES | SEQ ID NO:19199 QQYYTTPCS |
| iPS:436562 | 21-225_224H11 | NA | SEQ ID NO:3176 AAGTCTAGTCAGAGCCTCCT GCATAGTGATGAAGAAGACCTTCT TTTTGTAT | SEQ ID NO:11188 GAAATTTCCAACGGTTC TCT | SEQ ID NO:19200 ATGCAAAGTACACAGCTTCC TCGGACG |
| | | AA | SEQ ID NO:3177 KSSQSLLHSDGKTFLY | SEQ ID NO:11189 EISNRFS | SEQ ID NO:19201 MQSTQLPRT |
| | | | SEQ ID NO:3178 | SEQ ID NO:11190 | SEQ ID NO:19202 |

FIGURE 49
(Continued)

| | | | | |
|---|---|---|---|---|
| iPS:436564 | 21-225_225A1 | NA | CGGGCAAGTCAGGGCATTAG AGATGATTAGGC SEQ ID NO:3179 | GCTGCATCCAGTTTGCAA AGT SEQ ID NO:11191 | CTGCAGCATTATAGTTACCC TCGGACG SEQ ID NO:19203 |
| | | AA | RASQGIRDDLG SEQ ID NO:3180 | AASSLQS SEQ ID NO:11192 | LQHYSYPRT SEQ ID NO:19204 |
| iPS:436568 | 21-225_225B3 | NA | AGGGCCAGTCAGTCAGAATCTTAG CAGCAGCTACTTAGGC SEQ ID NO:3181 | GATACATCCAGCAGGGC CACT SEQ ID NO:11193 | CAGGAGTATGGTAGCTCACT CATGTGCAGT SEQ ID NO:19205 |
| | | AA | RASQNLSSSYLG SEQ ID NO:3182 | DTSSRAT SEQ ID NO:11194 | QEYGSSLMCS SEQ ID NO:19206 |
| iPS:436570 | 21-225_225F4 | NA | AAGTCCAGCCAGAGTGTTTT ATATAGCTCCAACAATAAGA ACTACTTAGCT SEQ ID NO:3183 | TGGGCATCTACCCGGGA ATCC SEQ ID NO:11195 | CACCAATATCATAATTCTCC TCCCACT SEQ ID NO:19207 |
| | | AA | KSSQSVLYSSNNKNYLA SEQ ID NO:3184 | WASTRES SEQ ID NO:11196 | HQYHNSPPT SEQ ID NO:19208 |
| iPS:436572 | 21-225_225G4 | NA | AAGTCTAGTCAGAGCCTCCT GCATAGTGATGGAAAGACCT TTTGTAT SEQ ID NO:3185 | GAAATTTCCAACCGGTTC TCT SEQ ID NO:11197 | ATGCAAAGTACACAGCTTCC TCGGACG SEQ ID NO:19209 |
| | | AA | KSSQSLLHSDGKTFLY SEQ ID NO:3186 | EISNRFS SEQ ID NO:11198 | MQSTQLPRT SEQ ID NO:19210 |
| iPS:436574 | 21-225_225F5 | NA | AAGTCCAGCCAGAATGTTTT ATACAACTCCAACAATAACA ACTACTTAGCT SEQ ID NO:3187 | TGGGCATCTACCGGGA ATCC SEQ ID NO:11199 | CAGCAATATTATAGTTCTCC TCCGACG SEQ ID NO:19211 |
| | | AA | KSSQNVLYNSNNNNYLA SEQ ID NO:3188 | WASTRES SEQ ID NO:11200 | QQYYSSPPT SEQ ID NO:19212 |
| iPS:436576 | | NA | CGGGCAAGTCAGGGCATGA GAAAAGATTTAGGC | GCTGCAACCAGTTTGCA AAGT | CTACAGCATAATAGTTATCC ATTCACT |

FIGURE 49
(Continued)

| | | | | | | |
|---|---|---|---|---|---|---|
| iPS:436578 | 21-225_225B6 | AA | SEQ ID NO:3189<br>RASQGMRKDLG | SEQ ID NO:11201<br>AATSLQS | SEQ ID NO:19213<br>LQHNSYPFT | |
| | | NA | SEQ ID NO:3190<br>CGGGCAAGTCAGGGCATTAG<br>AAATGATTTAGGC | SEQ ID NO:11202<br>GCTGCATCCAGTTTACAA<br>AGT | SEQ ID NO:19214<br>CTTCAGCATAATACTTACCC<br>ATTCACT | |
| iPS:436580 | 21-225_225D6 | AA | SEQ ID NO:3191<br>RASQGIRNDLG | SEQ ID NO:11203<br>AASSLQS | SEQ ID NO:19215<br>LQHNTYPFT | |
| | | NA | SEQ ID NO:3192<br>AGGGCCAGTCAGAGTGTTTA<br>CAGCAGTACTAGGCC | SEQ ID NO:11204<br>GGTGCATCCAGCAGGGC<br>CACT | SEQ ID NO:19216<br>CAGCAGTATGGTACCTCACC<br>TCGGACG | |
| iPS:436582 | 21-225_225E7 | AA | SEQ ID NO:3193<br>RASQSVYSSYLA | SEQ ID NO:11205<br>GASSRAT | SEQ ID NO:19217<br>QQYGTSPRT | |
| | | NA | SEQ ID NO:3194<br>CGGGCAAGTCAGGGCATTAG<br>AAATGATTTAGGC | SEQ ID NO:11206<br>GCTGCATCCAGTTGCTA<br>GGT | SEQ ID NO:19218<br>CTACAACATAATAGTTACCC<br>ATTCACT | |
| iPS:436584 | 21-225_225F8 | AA | SEQ ID NO:3195<br>RASQGIRNDLG | SEQ ID NO:11207<br>AASSLLG | SEQ ID NO:19219<br>LQHNSYPFT | |
| | | NA | SEQ ID NO:3196<br>AAGTCCAGCCAGAGTGTTTT<br>ATACAGCTCCAACAATAACA<br>ACTACTTAGCT | SEQ ID NO:11208<br>TGGGCATCTACCCGGGA<br>ATCC | SEQ ID NO:19220<br>CAACACTCCAAGAGTATTCC<br>TGGTAAG | |
| iPS:436586 | 21-225_225B9 | AA | SEQ ID NO:3197<br>KSSQSVLYSSNNNNYLA | SEQ ID NO:11209<br>WASTRES | SEQ ID NO:19221<br>QHSKSIPGK | |
| | | NA | SEQ ID NO:3198<br>AAGTCCAGCCAGAGTGTTTT<br>ATACAGCTCCAACAATTACA<br>ACTACTTAGCT | SEQ ID NO:11210<br>TGGGCTTCTACCCGGGA<br>ATCC | SEQ ID NO:19222<br>CAGCAATATTATACTACTCC<br>TCCGACG | |
| | 21-225_225F11 | AA | SEQ ID NO:3199<br>KSSQSVLYSSNNYNYLA | SEQ ID NO:11211<br>WASTRES | SEQ ID NO:19223<br>QQYYTTPPT | |
| | | | SEQ ID NO:3200 | SEQ ID NO:11212 | SEQ ID NO:19224 | |

FIGURE 49
(Continued)

| | | | | | |
|---|---|---|---|---|---|
| iPS:436588 | 21-225_225F12 | NA | AAGTCCAGCCAGAGTGTTTATACAGCTCCAACAATCAGAACTACTTAGCT SEQ ID NO:3201 | TGGACATCTACCCGGGAATCC SEQ ID NO:11213 | CAGCAATATATTACTCCGTGCAGT SEQ ID NO:19225 |
| | | AA | KSSQSVLYSSNNQNYLA SEQ ID NO:3202 | WTSTRES SEQ ID NO:11214 | QQYYITPCS SEQ ID NO:19226 |
| iPS:436590 | 21-225_225H12 | NA | AAGTCCAGCCAGAGTGTTTATACAACTCCAACAATAACAACTACTTAGCT SEQ ID NO:3203 | TGGGCATCTACCCGGGAATCC SEQ ID NO:11215 | CAGCAATATATTACTCCGTGCAGT SEQ ID NO:19227 |
| | | AA | KSSQSVLYNSNNNYLA SEQ ID NO:3204 | WASTRES SEQ ID NO:11216 | QQYYITPCS SEQ ID NO:19228 |
| iPS:436592 | 21-225_226B1 | NA | AAGTCTAGTCAGAGCCTCCTGCATGGTGATGGAAAGACCTTATTTGTAT SEQ ID NO:3205 | GAAGTTTCCATCCGGTTCTCT SEQ ID NO:11217 | ATGCAAAGTATACAGATTCCGTGGACG SEQ ID NO:19229 |
| | | AA | KSSQSLLHGDGKTYLY SEQ ID NO:3206 | EVSIRFS SEQ ID NO:11218 | MQSIQIPWT SEQ ID NO:19230 |
| iPS:436594 | 21-225_226A5 | NA | AAGTCTAGTCAGAGCCTCCTACATGGTGATGGAAAGACCTTATTTGTAT SEQ ID NO:3207 | GAAGTTTCCAACCGGTTCTCT SEQ ID NO:11219 | ATGCAAAGTATACAGATTCCGTGGACG SEQ ID NO:19231 |
| | | AA | KSSQSLLHGDGKTYLY SEQ ID NO:3208 | EVSNRFS SEQ ID NO:11220 | MQSIQIPWT SEQ ID NO:19232 |
| iPS:436596 | 21-225_226C6 | NA | CGGGCAAGTCAGGGCATTAGAAATGATTTAGGC SEQ ID NO:3209 | GCTGCATCCAGTTTGCAAAGT SEQ ID NO:11221 | CTACAGCATTATAATTACCCTCGGGCG SEQ ID NO:19233 |
| | | AA | RASQGIRNDLG SEQ ID NO:3210 | AASSLQS SEQ ID NO:11222 | LQHYNYPRA SEQ ID NO:19234 |

FIGURE 49
(Continued)

| | | | | | |
|---|---|---|---|---|---|
| iPS:436598 | 21-225_226D6 | NA | AAGTCCAGCCAGAGTATTT ATACATCTCCAACAATAAGA ACTACTTAGCT SEQ ID NO:3211 | TGGGCATCTACCCGGGA ATCC SEQ ID NO:11223 | CAGCAATATTATAGTTCTCC GTGCAGT SEQ ID NO:19235 |
| | | AA | RSSQSILYISNNKNYLA SEQ ID NO:3212 | WASTRES SEQ ID NO:11224 | QQYYSSPCS SEQ ID NO:19236 |
| iPS:436600 | 21-225_226F6 | NA | AAGTCCAGCCAGAGTATTT ATACAGCTCCAACAATTACA ACTACTTAGCT SEQ ID NO:3213 | TGGGCTTCTACCCGGGA ATCC SEQ ID NO:11225 | CAGCAATATTATACTACTCC TCCGACG SEQ ID NO:19237 |
| | | AA | KSSQSILYSSNNYNYLA SEQ ID NO:3214 | WASTRES SEQ ID NO:11226 | QQYYTPPT SEQ ID NO:19238 |
| iPS:436602 | 21-225_226E7 | NA | AAGTCTAGTCAGAGCCTCCT GCATGGTGATGGAAAGACCT ATTTGTAT SEQ ID NO:3215 | GAAGTTCCAACCGGTTC TCT SEQ ID NO:11227 | ATGCAAAGTATACAGGTTCC GTGGACG SEQ ID NO:19239 |
| | | AA | KSSQSLLHGDGKTYLY SEQ ID NO:3216 | EVSNRFS SEQ ID NO:11228 | MQSIQVPWT SEQ ID NO:19240 |
| iPS:436604 | 21-225_226F7 | NA | CGGGCAAGTCAGGGCATTGG GAATGATTTAGGC SEQ ID NO:3217 | GCTGCCTCCAGTTTGCAA AGT SEQ ID NO:11229 | CTACATCATTATAGTTACCT CGGACG SEQ ID NO:19241 |
| | | AA | RASQGIGNDLG SEQ ID NO:3218 | AASSLQS SEQ ID NO:11230 | LHHYSYPRT SEQ ID NO:19242 |
| iPS:436606 | 21-225_226G8 | NA | AAGTCTAGTCAGAGCCTCCT GCATAGTGATGGAAAGACCT TTTTGTAT SEQ ID NO:3219 | GAAATTTCCAACCGGTTC TCT SEQ ID NO:11231 | ATGCAAAGTACACAGCTTCC TCGGACG SEQ ID NO:19243 |
| | | AA | KSSQSLLHSDGKTFLY SEQ ID NO:3220 | EISNRFS SEQ ID NO:11232 | MQSTQLPRT SEQ ID NO:19244 |

FIGURE 49
(Continued)

| iPS:436608 | 21-225_226A9 | NA | CGGGCAAGTCAGGGCATTAG AAATGATTTAGGC | GCTGCATCCAGTTGCAA AGT | CTACAGCATAATAGTTACCC ATTCACT |
|---|---|---|---|---|---|
| | | | SEQ ID NO:3221 | SEQ ID NO:11233 | SEQ ID NO:19245 |
| | | AA | RASQGIRNDLG | AASSLQS | LQHNSYPFT |
| | | | SEQ ID NO:3222 | SEQ ID NO:11234 | SEQ ID NO:19246 |
| iPS:436610 | 21-225_226F9 | NA | AAGTCTAGTCAGAGCCTCCT GCATAGTGATGGAAAGACCTTCT TTTTGTAT | GAAATTTCCAACCGGTTC TCT | ATGCAAAGTACACAGCTTCC TCGGACG |
| | | | SEQ ID NO:3223 | SEQ ID NO:11235 | SEQ ID NO:19247 |
| | | AA | KSSQSLLHSDGKTFLY | EISNRFS | MQSTQLPRT |
| | | | SEQ ID NO:3224 | SEQ ID NO:11236 | SEQ ID NO:19248 |
| iPS:436612 | 21-225_226H9 | NA | AAGTCTAGTCAGAGCCTCCT GCATAGTGATGGAAAGACCTTCT TTTTGTAT | GAAGTTTCCAACCGGTTC TCT | ATGCAAAGTACACAGCTTCC TCGGACG |
| | | | SEQ ID NO:3225 | SEQ ID NO:11237 | SEQ ID NO:19249 |
| | | AA | KSSQSLLHSDGKTFLY | EVSNRFS | MQSTQLPRT |
| | | | SEQ ID NO:3226 | SEQ ID NO:11238 | SEQ ID NO:19250 |
| iPS:436614 | 21-225_226F10 | NA | AAGTCTAGTCAGAGCCTCCT GCATAGTGATGGAAAGACCTTCT TTTTGTAT | GAAATTTCCAACCGGTTC TCT | ATGCAAAGTACACAGCTTCC TCGGACG |
| | | | SEQ ID NO:3227 | SEQ ID NO:11239 | SEQ ID NO:19251 |
| | | AA | KSSQSLLHSDGKTFLY | EISNRFS | MQSTQLPRT |
| | | | SEQ ID NO:3228 | SEQ ID NO:11240 | SEQ ID NO:19252 |
| iPS:436616 | 21-225_226D11 | NA | AAGTCCAGCCAGAATGTTTT ACACAGCTCCAACAGTAATA ACTACTTAGTT | TGGGCATCTACCCGGGA ATCC | CAGCAATATTATAAAACTCC GTGGACG |
| | | | SEQ ID NO:3229 | SEQ ID NO:11241 | SEQ ID NO:19253 |
| | | AA | KSSQNVLHSSNSNNYLV | WASTRES | QQYYKTPWT |
| | | | SEQ ID NO:3230 | SEQ ID NO:11242 | SEQ ID NO:19254 |

FIGURE 49
(Continued)

| | | | | | |
|---|---|---|---|---|---|
| iPS:436618 | 21-225_226E11 | NA | AAGTCTAGTCAGAGCCTCCTGCATAGTGATGGAAAGACCTTTTTGTAT SEQ ID NO:3231 | GAAATTTCCAACCGGTTCTCT SEQ ID NO:11243 | ATGCAAAGTACACAGCTTCCTCGGACG SEQ ID NO:19255 |
| | | AA | KSSQSLLHSDGKTFLY SEQ ID NO:3232 | EISNRFS SEQ ID NO:11244 | MQSTQLPRT SEQ ID NO:19256 |
| iPS:436620 | 21-225_226H11 | NA | CGGACAAGTCAGGGCATTAGAAATGATTTAGGC SEQ ID NO:3233 | GCTGCATCCAGTTTGCAAAGT SEQ ID NO:11245 | CTACAGCATTATAGTTACCTCGGACG SEQ ID NO:19257 |
| | | AA | RTSQGIRNDLG SEQ ID NO:3234 | AASSLQS SEQ ID NO:11246 | LQHYSYPRT SEQ ID NO:19258 |
| iPS:436622 | 21-225_226A12 | NA | AAGTCCAGCCAGAATGTTTTATACAGTTCCAACAATAACAACTACTAGCT SEQ ID NO:3235 | TGGGCATCTACCCGGAAATCC SEQ ID NO:11247 | CAGCAATAATTATAGTAGTCCTCCGACG SEQ ID NO:19259 |
| | | AA | KSSQNVLYSSNNNNYLA SEQ ID NO:3236 | WASTRKS SEQ ID NO:11248 | QQYYSSPPT SEQ ID NO:19260 |
| iPS:436624 | 21-225_226H12 | NA | AAGTCTAGTCAGAGCCTCCTGCATAGTGATGGAAAGACCTTTTTGTAT SEQ ID NO:3237 | GAAATTTCCAACCGGTTCTCT SEQ ID NO:11249 | ATGCAAAGTACACAGCTTCCTCGGACG SEQ ID NO:19261 |
| | | AA | KSSQSLLHSDGKTFLY SEQ ID NO:3238 | EISNRFS SEQ ID NO:11250 | MQSTQLPRT SEQ ID NO:19262 |
| iPS:436626 | 21-225_227C1 | NA | AAGTCTAGTCAGAGCCTCCTGCATAGTGATGGAAAGACCTTTTTGTAT SEQ ID NO:3239 | GAAATTTCCAACCGGTTCTCT SEQ ID NO:11251 | ATGCAAAGTACACAGCTTCCTCGGACG SEQ ID NO:19263 |
| | | AA | KSSQSLLHSDGKTFLY SEQ ID NO:3240 | EISNRFS SEQ ID NO:11252 | MQSTQLPRT SEQ ID NO:19264 |

FIGURE 49
(Continued)

| | | | | | |
|---|---|---|---|---|---|
| iPS:436628 | 21-225_227F2 | NA | AAGTCTAGTCAGAGCCTCCT GCATAGTGATGGAAAGACCT TTTTGTAT SEQ ID NO:3241 | GAAATTTCCAACCGGTTC TCT SEQ ID NO:11253 | ATGCAAAGTACACAGCTTCC TCGGACG SEQ ID NO:19265 |
| | | AA | KSSQSLLHSDGKTFLY SEQ ID NO:3242 | EISNRFS SEQ ID NO:11254 | MQSTQLPRT SEQ ID NO:19266 |
| iPS:436630 | 21-225_227G3 | NA | CGGGCAAGTCAGGGCATTAG AAATGATTTAGGC SEQ ID NO:3243 | GCTGCATCCAGTTTGCAA AGT SEQ ID NO:11255 | CTACACCATAATAGTTACCC ATTCACT SEQ ID NO:19267 |
| | | AA | RASQGIRNDLG SEQ ID NO:3244 | AASSLQS SEQ ID NO:11256 | LHHNSYPFT SEQ ID NO:19268 |
| iPS:436632 | 21-225_227E4 | NA | CGGGCGAGTCAGGGTATTAT CAACTGGTTAGCC SEQ ID NO:3245 | GCTGCATCCAGTTTGCAA AGT SEQ ID NO:11257 | CAACAGGCTAACAGTTCCC GTGGACG SEQ ID NO:19269 |
| | | AA | RASQGIINWLA SEQ ID NO:3246 | AASSLQS SEQ ID NO:11258 | QQANSFPWT SEQ ID NO:19270 |
| iPS:436634 | 21-225_227H5 | NA | CGGGCAAGTCAGGACATTAG AAATGATTTAGGC SEQ ID NO:3247 | GCTGCATCCAGTTTGCAA AGT SEQ ID NO:11259 | CTACAGCATAATAGTTACCC ATTCACT SEQ ID NO:19271 |
| | | AA | RASQDIRNDLG SEQ ID NO:3248 | AASSLQS SEQ ID NO:11260 | LQHNSYPFT SEQ ID NO:19272 |
| iPS:436636 | 21-225_227E6 | NA | AAGTCCAGCCAGAGTGTTTT ATACAGCTCCAACGATAAGA ACTACTTAGCT SEQ ID NO:3249 | TGGGCATCTACCCGGGA ATCC SEQ ID NO:11261 | CAGCAATATTATAGTTACTCC GTGCAGT SEQ ID NO:19273 |
| | | AA | KSSQSVLYSSNDKNYLA SEQ ID NO:3250 | WASTRES SEQ ID NO:11262 | QQYYITPCS SEQ ID NO:19274 |
| iPS:436638 | 21_225_227C7 | NA | AGGTCCAGCCAGATTGTTTT ATCCGACTCCAACAATAACA ACTACTTAGCT | TGGGCATCTACCCGGGA ATCC | CAGCAATATTATAGTTCTCC TCCGACG |

FIGURE 49
(Continued)

| | | | | | | |
|---|---|---|---|---|---|---|
| iPS:4366640 | 21-225_227C7 | AA | SEQ ID NO:3251<br>RSSQIVLSDSNNNNYLA<br>SEQ ID NO:3252 | SEQ ID NO:11263<br>WASTRES<br>SEQ ID NO:11264 | SEQ ID NO:19275<br>QQYYSSPPT<br>SEQ ID NO:19276 | |
| iPS:4366640 | 21-225_227A8 | NA | AAGTCTAGTCAGAGCCTCCT<br>GCATAGTGATGGAAAGACCT<br>TTTTGTAT<br>SEQ ID NO:3253 | GAAATTTCCAACCGGTTC<br>TCT<br>SEQ ID NO:11265 | ATGCAAAGTACACAGCTTCC<br>TCGGACG<br>SEQ ID NO:19277 | |
| iPS:4366644 | 21-225_227A8 | AA | KSSQSLLHSDGKTFLY<br>SEQ ID NO:3254 | EISNRFS<br>SEQ ID NO:11266 | MQSTQLPRT<br>SEQ ID NO:19278 | |
| iPS:4366644 | 21-225_227G9 | NA | AAGTCCAGCCAGAGTGTTT<br>ACACAGCTCCAACAATAACA<br>ACTACTTAGCT<br>SEQ ID NO:3255 | TGGGGATCTACCCGGGA<br>ATCC<br>SEQ ID NO:11267 | CAGCAATATTATAGTGCTCC<br>GTACAGT<br>SEQ ID NO:19279 | |
| iPS:4366646 | 21-225_227G9 | AA | KSSQSVLHSSNNNNYLA<br>SEQ ID NO:3256 | WGSTRES<br>SEQ ID NO:11268 | QQYYSAPYS<br>SEQ ID NO:19280 | |
| iPS:4366646 | 21-225_227D11 | NA | AAGTCCAGCCAGAGTGTTT<br>ACACAGTTCCAACAATAATA<br>ACTACTTAGCT<br>SEQ ID NO:3257 | TGGGCATCTACCCGGGA<br>ATCC<br>SEQ ID NO:11269 | CAGCAATATTATAATACTCC<br>GTGCAGT<br>SEQ ID NO:19281 | |
| iPS:4366648 | 21-225_227D11 | AA | KSSQSVLHSSNNNNYLA<br>SEQ ID NO:3258 | WASTRES<br>SEQ ID NO:11270 | QQYYNTPCS<br>SEQ ID NO:19282 | |
| iPS:4366648 | 21-225_227F11 | NA | TGGTCTAGTCAGAGCCTCCT<br>GCATAGTAATGGATACAACT<br>ATTTGGAT<br>SEQ ID NO:3259 | TTGGGTTCTAATCGGGCC<br>TCC<br>SEQ ID NO:11271 | ATGCAAGCTCTACAAACTCC<br>TCTCACC<br>SEQ ID NO:19283 | |
| iPS:4366650 | 21-225_227F11 | AA | WSSQSLLHSNGYNYLD<br>SEQ ID NO:3260 | LGSNRAS<br>SEQ ID NO:11272 | MQALQTPLT<br>SEQ ID NO:19284 | |
| iPS:4366650 | 21-225_227C12 | NA | CGGGCAAGTCAGGGCATTAG<br>AAATGATTTAGGC<br>SEQ ID NO:3261 | GCTGCATCCAGTTTGCAA<br>AGT<br>SEQ ID NO:11273 | CTACAGCATAATAGTTACCC<br>ATTCACT<br>SEQ ID NO:19285 | |

FIGURE 49
(Continued)

| | | AA | RASQGIRNDLG | AASSLQS | LQHNSYPFT |
|---|---|---|---|---|---|
| iPS:436652 | | | SEQ ID NO:3262 | SEQ ID NO:11274 | SEQ ID NO:19286 |
| | 21-225_146B11 | NA | TCTGGAGATAAATTGGGGGA TAAATATGCTTCC | CAAGATAGCAAGCGGCC CTCA | CAGGCGTGGGACAGCAGCAC TGTGGTA |
| | | | SEQ ID NO:3263 | SEQ ID NO:11275 | SEQ ID NO:19287 |
| | | AA | SGDKLGDKYAS | QDSKRPS | QAWDSSTVV |
| iPS:436654 | | | SEQ ID NO:3264 | SEQ ID NO:11276 | SEQ ID NO:19288 |
| | 21-225_146C11 | NA | TCTGGAGATAAATTGGGGGA TAAATATGCTTCC | CAAGATAGCAAGCGGCC CTCA | CAGGCGTGGGACAGCAGCAC TGTGGTA |
| | | | SEQ ID NO:3265 | SEQ ID NO:11277 | SEQ ID NO:19289 |
| | | AA | SGDKLGDKYAS | QDSKRPS | QAWDSSTVV |
| iPS:436658 | | | SEQ ID NO:3266 | SEQ ID NO:11278 | SEQ ID NO:19290 |
| | 21-225_146A2 | NA | TCTGGAGATAAATTGGGGGA TAAATATGCTTCC | CAAGATAGCAAGCGGCC CTCA | CAGGCGTGGGACAGCAGCAC TGTGGTA |
| | | | SEQ ID NO:3267 | SEQ ID NO:11279 | SEQ ID NO:19291 |
| | | AA | SGDKLGDKYAS | QDSKRPS | QAWDSSTVV |
| iPS:436660 | | | SEQ ID NO:3268 | SEQ ID NO:11280 | SEQ ID NO:19292 |
| | 21-225_146D8 | NA | TCTGGAAGCAGCTCCTACAT CGGAAGTAATACTGTAGAC | AGTAATAATCAGCGGCC CTCA | GCAGCATGGGATGACAGCCT TAATGGCGTGGTA |
| | | | SEQ ID NO:3269 | SEQ ID NO:11281 | SEQ ID NO:19293 |
| | | AA | SGSSSYIGSNTVD | SNNQRPS | AAWDDSLNGVV |
| iPS:436662 | | | SEQ ID NO:3270 | SEQ ID NO:11282 | SEQ ID NO:19294 |
| | 21-225_147D7 | NA | TCTGGAGATAAATTGGGGGA TAAATTGCTTGC | CAAGATAGGAAGCGGCC CTCA | CAGGCGTGGGACACAGGAACAC CGCTGTC |
| | | | SEQ ID NO:3271 | SEQ ID NO:11283 | SEQ ID NO:19295 |
| | | AA | SGDKLGDKFAC | QDRKRPS | QAWDRNTAV |
| iPS:436664 | | | SEQ ID NO:3272 | SEQ ID NO:11284 | SEQ ID NO:19296 |
| | | NA | TCTGGAGATAAATTGGGGGA TAAATATGCTTCC | CAAGATAGCAAGCCCC CTCA | CAGGCGTGGGACAGCAGCAC TGTGGTA |

FIGURE 49
(Continued)

| | | | | | | |
|---|---|---|---|---|---|---|
| iPS:4366666 | 21-225_147E7 | AA | SEQ ID NO:3273 SGDKLGDKYAS | SEQ ID NO:11285 QDSKRPS | SEQ ID NO:19297 QAWDSSTVV | |
| iPS:4366668 | 21-225_147B8 | NA | SEQ ID NO:3274 TCTGGAGATAAATTGGGGGA TAAATATGTTTGC | SEQ ID NO:11286 CAAGATAGGAAGCGGCC CTCA | SEQ ID NO:19298 CAGGCGTGGGCAGTAACAC TGCTGTGGTA | |
| | | AA | SEQ ID NO:3275 SGDKLGDKYVC | SEQ ID NO:11287 QDSKRPS | SEQ ID NO:19299 QAWGSNTAVV | |
| iPS:4366670 | 21-225_147B9 | NA | SEQ ID NO:3276 TCTGGAGATAAATTGGGGGA TAAATATGTTTCC | SEQ ID NO:11288 CAAGATAGGAAGCGGCC CTCA | SEQ ID NO:19300 CTGGCGTGGGACAGCAGCAC TTTTGTGGTA | |
| | | AA | SEQ ID NO:3277 SGDKLGDKYVS | SEQ ID NO:11289 QDRKRPS | SEQ ID NO:19301 LAWDSSTFVV | |
| iPS:4366672 | 21-225_147D9 | NA | SEQ ID NO:3278 TCTGGAGATAAATTGGGTAA TAAATATGTTTGC | SEQ ID NO:11290 CAAGATAGCAAGCGGCC CTCA | SEQ ID NO:19302 CAGGCGTGGGACAGGAACAC TTATGTGGTG | |
| | | AA | SEQ ID NO:3279 SGDKLGNKYVC | SEQ ID NO:11291 QDSKRPS | SEQ ID NO:19303 QAWDRNTYVV | |
| iPS:4366674 | 21-225_147F9 | NA | SEQ ID NO:3280 TCTGGAGATAAATTGGGGGA TAAATATGCTTGC | SEQ ID NO:11292 CAAGATAGCAAGCGGCC CTCA | SEQ ID NO:19304 CAGGCGTGGCACAGCAGCAC TGTGGTA | |
| | | AA | SEQ ID NO:3281 SGDELGNKYAC | SEQ ID NO:11293 QDSKRPS | SEQ ID NO:19305 QAWHSSTVV | |
| iPS:4366676 | 21-225_147G9 | NA | SEQ ID NO:3282 TCTGGAGATGAATGGGGGA TAAATATGCTTGC | SEQ ID NO:11294 CAAGATAGCAAGCGGCC CTCA | SEQ ID NO:19306 CAGGCGTGGCACAGCAGTAC TGTGGTA | |
| | | AA | SEQ ID NO:3283 SGDKLGDKYAC | SEQ ID NO:11295 QDRKRPS | SEQ ID NO:19307 QAWHSSTVV | |
| | | NA | SEQ ID NO:3284 TCTGGAGATAAATGGGGGA TAAATATGCTTCC | SEQ ID NO:11296 CAAGATAGCAAGCGGCC CTCA | SEQ ID NO:19308 CAGGCGTGGGACAGCAGCAC TGTGGTA | |

FIGURE 49
(Continued)

| | | | | | | |
|---|---|---|---|---|---|---|
| iPS:4366678 | 21-225_147E11 | AA | SEQ ID NO:3285 SGDKLGDKYAS | SEQ ID NO:11297 QDSKRPS | SEQ ID NO:19309 QAWDSSTVV |
| iPS:4366680 | 21-225_147B12 | NA | SEQ ID NO:3286 TCTGGAGATAAATTGGGGA TAAATATGCTTCC | SEQ ID NO:11298 CAAGATAGCAAGCGGCC CTCA | SEQ ID NO:19310 CAGGCGTGGACAGCAGCAC TGTGGTA |
| | | AA | SEQ ID NO:3287 SGDKLGDKYAS | SEQ ID NO:11299 QDSKRPS | SEQ ID NO:19311 QAWDSSTVV |
| | 21-225_147H12 | NA | SEQ ID NO:3288 TCTGGAAGCAGCTCCAACAT CGGAAGTTATGCTGTAAAC | SEQ ID NO:11300 AGTAATAATCACGGGCC CTCA | SEQ ID NO:19312 GAAGCATGGATGACAGCCT GAATGGTCCGGTA |
| | | AA | SEQ ID NO:3289 SGSSSNIGSYAVN | SEQ ID NO:11301 SNNHRPS | SEQ ID NO:19313 EAWDIDSLNGPV |
| iPS:4366682 | 21-225_146A8 | NA | SEQ ID NO:3290 TCTGGAAGCAGCTCCAACAT CGGAAGTAATTCTATAAAC | SEQ ID NO:11302 AGTAATGATCAGGGGCC CTCA | SEQ ID NO:19314 GCAGCATGGATGACAGCCT GAACGGCGTGGTA |
| | | AA | SEQ ID NO:3291 SGSSSNIGSNSIN | SEQ ID NO:11303 SNDQRPS | SEQ ID NO:19315 AAWDDSLNGVV |
| iPS:4366684 | 21-225_146B6 | NA | SEQ ID NO:3292 TCTGGAAGCAGCTCCAACAT CGGAAGTAATGCTGTAAAC | SEQ ID NO:11304 AGTAATAATCAGGGGCC CTCA | SEQ ID NO:19316 GCAGCATGGATGACAGCCT GAATGGCGTGGTA |
| | | AA | SEQ ID NO:3293 SGSSSNIGSNAVN | SEQ ID NO:11305 SNNQRPS | SEQ ID NO:19317 AAWDDSLNGVV |
| iPS:4366686 | 21-225_148G6 | NA | SEQ ID NO:3294 TCTGGAGATAAATTGGGGA TAAATATGCTTCC | SEQ ID NO:11306 CAAGATAGCAAGCGGCC CTCA | SEQ ID NO:19318 CAGGCGTGGACAGCAGCAC TGTGGTA |
| | | AA | SEQ ID NO:3295 SGDKLGDKYAS | SEQ ID NO:11307 QDSKRPS | SEQ ID NO:19319 QAWDSSTVV |

FIGURE 49
(Continued)

| | | | | | |
|---|---|---|---|---|---|
| iPS:436688 | 21-225_148C8 | NA | SEQ ID NO:3296<br>TCTGGAGATAAATTGGGGGA<br>TAAATATGTTTCC<br>SEQ ID NO:3297 | SEQ ID NO:11308<br>CAAGATAGGAAGCGGCC<br>CTCA<br>SEQ ID NO:11309 | SEQ ID NO:19320<br>CTGGCGTGGGACAGCAGCAC<br>TTTTGTGGTA<br>SEQ ID NO:19321 |
| | | AA | SGDKLGDKYVS<br>SEQ ID NO:3298 | QDRKRPS<br>SEQ ID NO:11310 | LAWDSSTFVV<br>SEQ ID NO:19322 |
| iPS:436690 | 21-225_148A9 | NA | TCTGGAGATAAATTGGGGGA<br>TAAATATGTTTGC<br>SEQ ID NO:3299 | CAAGATAGCAAGCGGCC<br>CTCA<br>SEQ ID NO:11311 | CAGGCGTGGCACAGCAGCAC<br>TGTGGTA<br>SEQ ID NO:19323 |
| | | AA | SGDKLGNKYVC<br>SEQ ID NO:3300 | QDSKRPS<br>SEQ ID NO:11312 | QAWHSSTVV<br>SEQ ID NO:19324 |
| iPS:436694 | 21-225_148G11 | NA | TCTGGAGATAAATTGGGGGA<br>TAAATTGCTTCC<br>SEQ ID NO:3301 | CAAGATAGCAAGCGGCC<br>CTCA<br>SEQ ID NO:11313 | CAGGCGTGGGACAGCAGCAC<br>TGTGGTA<br>SEQ ID NO:19325 |
| | | AA | SGDKLGDKFAS<br>SEQ ID NO:3302 | QDSKRPS<br>SEQ ID NO:11314 | QAWDSSTVV<br>SEQ ID NO:19326 |
| iPS:436696 | 21-225_149A1 | NA | TCTGGAAGCAGCTCCAACAT<br>CGGAAGTAATGCTGTAAAC<br>SEQ ID NO:3303 | AGTAATAATCAGGGCC<br>CTCA<br>SEQ ID NO:11315 | GCAGCATGGGATGACAGCCT<br>GAATGGCGTGGTA<br>SEQ ID NO:19327 |
| | | AA | SGSSSNIGSNAVN<br>SEQ ID NO:3304 | SNNQRPS<br>SEQ ID NO:11316 | AAWDDSLNGVV<br>SEQ ID NO:19328 |
| iPS:436698 | 21-225_149B5 | NA | TCTGGATATAAATTGGGGTA<br>TAAATATGTTTGC<br>SEQ ID NO:3305 | CAAAATAACCAGCGGCC<br>CTCA<br>SEQ ID NO:11317 | CAGGCGTGGGACAGCAGCAC<br>TGTGGTA<br>SEQ ID NO:19329 |
| | | AA | SGYKLGYKYVC<br>SEQ ID NO:3306 | QNNQRPS<br>SEQ ID NO:11318 | QAWDSSTVV<br>SEQ ID NO:19330 |
| iPS:436700 | 21-225_149C7 | NA | TCTGGAAATAAATTGGGGGA<br>TAAATATGCTTCC<br>SEQ ID NO:3307 | CAAGATAGCAAGCGGCC<br>CTCA<br>SEQ ID NO:11319 | CAGGCGTGGGACAGCAGCAC<br>TGTGGTA<br>SEQ ID NO:19331 |

FIGURE 49
(Continued)

| | | | | | QDSKRPS | | QAWDSSTVV |
|---|---|---|---|---|---|---|---|
| iPS:436702 | | AA | SGNKLGDKYAS | | QDSKRPS | | QAWDSSTVV |
| | | | SEQ ID NO:3308 | | SEQ ID NO:11320 | | SEQ ID NO:19332 |
| | 21-225_149E8 | NA | ACCTTACGCAGTGGCATCAC TGTTACTACCTATAGGATAT AC | | TACACATCAGACTCAGA TAAACCAGGGCTCT | | ATGATTTGGCACAGCAGGCGC TTGGGTG |
| | | | SEQ ID NO:3309 | | SEQ ID NO:11321 | | SEQ ID NO:19333 |
| | | AA | TLRSGITVTTYRIY | | YTSDSDKHQGS | | MIWHSSAWV |
| | | | SEQ ID NO:3310 | | SEQ ID NO:11322 | | SEQ ID NO:19334 |
| iPS:436704 | | NA | TCTGGAGATAAATTGGGGA TAAATATGCTTCC | | CAAGATAACAAGCGGCC CTCA | | CAGGCGTGGGACAGCAGCAC TGTGGTA |
| | 21-225_149C10 | | SEQ ID NO:3311 | | SEQ ID NO:11323 | | SEQ ID NO:19335 |
| | | AA | SGDKLGDKYAS | | QDSRRPS | | QAWDSSTVV |
| | | | SEQ ID NO:3312 | | SEQ ID NO:11324 | | SEQ ID NO:19336 |
| iPS:436706 | | NA | TCTGGAGATAAATTGGGGA TAAATATGTTTCC | | CAAGATAGCAGGCGGCC CTCA | | CTGGCGTGGGACAGCAGCAC TTTTGTGGTC |
| | 21-225_149A11 | | SEQ ID NO:3313 | | SEQ ID NO:11325 | | SEQ ID NO:19337 |
| | | AA | SGDKLGNKYVS | | QDSRRPS | | LAWDSSTFVV |
| | | | SEQ ID NO:3314 | | SEQ ID NO:11326 | | SEQ ID NO:19338 |
| iPS:436708 | | NA | TCTGGAGATGAATTGGGGA TAAATATGCTTGC | | CAAGATAACAAGCGGCC CTCA | | CAGGCGTGGCACACAGCAGCAC TGTGGTA |
| | 21-225_150D3 | | SEQ ID NO:3315 | | SEQ ID NO:11327 | | SEQ ID NO:19339 |
| | | AA | SGDELGNKYAC | | QDNKRPS | | QAWHSSTVV |
| | | | SEQ ID NO:3316 | | SEQ ID NO:11328 | | SEQ ID NO:19340 |
| iPS:436710 | | NA | TCTGGAGATAAATTGGGGA TAAATATGCTTCC | | CAAGATAGCAAGCGGCC CTCA | | CAGGCGTGGGACAGCAGCAC TGTGGTA |
| | 21-225_150F6 | | SEQ ID NO:3317 | | SEQ ID NO:11329 | | SEQ ID NO:19341 |
| | | AA | SGDKLGDKYAS | | QDSKRPS | | QAWDSSTVV |
| | | | SEQ ID NO:3318 | | SEQ ID NO:11330 | | SEQ ID NO:19342 |

FIGURE 49
(Continued)

| | | | | | |
|---|---|---|---|---|---|
| iPS:436712 | 21-225_150F9 | NA | TCTGGAAGCAGCTCCAACAT CGGAAGTAATGCTGTAAAC SEQ ID NO:3319 | AGTAATAGTCAGCGGCC CTCA SEQ ID NO:11331 | GCAGCATGGGATGACAGCCT GAATGGCGTGGTA SEQ ID NO:19343 |
| | | AA | SGSSSNIGSNAVN SEQ ID NO:3320 | SNSQRPS SEQ ID NO:11332 | AAWDDSLNGVV SEQ ID NO:19344 |
| iPS:436714 | 21-225_150H11 | NA | TCTGGAGATAAATTGGGGGA TAAATATGCTTCC SEQ ID NO:3321 | CAAGATAGCAAGCGGCC CTCA SEQ ID NO:11333 | CAGGCGTGGACAGCAGCAC TGTGGTA SEQ ID NO:19345 |
| | | AA | SGDKLGDKYAS SEQ ID NO:3322 | QDSKRPS SEQ ID NO:11334 | QAWDSSTVV SEQ ID NO:19346 |
| iPS:436716 | 21-225_151F3 | NA | TCTGGAGATAAATTGGGGGA TAAATATGTTTGC SEQ ID NO:3323 | CAAGATCGCAAGCGGCC CTCA SEQ ID NO:11335 | CAGGCGTGGACAGCAGCAC TGTGGTA SEQ ID NO:19347 |
| | | AA | SGDKLGDKYVC SEQ ID NO:3324 | QDRKRPS SEQ ID NO:11336 | QAWHSSTVV SEQ ID NO:19348 |
| iPS:436718 | 21-225_151H5 | NA | TCTGGAGATAAATTGGGGGA TAAATATGCTTCC SEQ ID NO:3325 | CAAGATAGCAAGCGGCC CTCA SEQ ID NO:11337 | CAGGCGTGGACAGCAGCAC TGTGGTA SEQ ID NO:19349 |
| | | AA | SGDKLGDKYAS SEQ ID NO:3326 | QDSKRPS SEQ ID NO:11338 | QAWDSSTVV SEQ ID NO:19350 |
| iPS:436720 | 21-225_151H6 | NA | TCTGGAGATAAATTGGGGGA TAAATATGCTTGC SEQ ID NO:3327 | CAAGATACCAAGCGGCC CTCA SEQ ID NO:11339 | CAGGCGTGGACAGCAGCAC TTATGTC SEQ ID NO:19351 |
| | | AA | SGDKLGDKYAC SEQ ID NO:3328 | QDTKRPS SEQ ID NO:11340 | QAWDSTYV SEQ ID NO:19352 |
| iPS:436722 | 21-225_151H7 | NA | TCTGGAGATAAATTGGGGGA TAAATATGCTTCC SEQ ID NO:3329 | CAAGATAGCAAGCGGCC CTCA SEQ ID NO:11341 | CAGGCGTGGACAGCAGCAC TGTGGTA SEQ ID NO:19353 |
| | | AA | SGDKLGDKYAS | QDSKRPS | QAWDSSTVV |

FIGURE 49
(Continued)

| | | | | | | | |
|---|---|---|---|---|---|---|---|
| iPS:436724 | 21-225_151B9 | NA | SEQ ID NO:3330<br>TCTGGAGATAAATTGGGGGA<br>TAAATATGCTTCC | SEQ ID NO:11342<br>CAAGATAGCAAGCGGCC<br>CTCA | SEQ ID NO:19354<br>CAGGCGTGGGACAGCAGCAC<br>TGTGGTA |
| | | AA | SEQ ID NO:3331<br>SGDNLGDKYAS | SEQ ID NO:11343<br>QDSKRPS | SEQ ID NO:19355<br>QAWDSSTVV |
| iPS:436726 | 21-225_152G5 | NA | SEQ ID NO:3332<br>SEQ ID NO:3333<br>TCTGGAGATAAATTGGGGGA<br>TAAATATGCTTGC | SEQ ID NO:11344<br>CAAGATTCCAAGCGGCC<br>CTCA | SEQ ID NO:19356<br>CAGGCGTGGGACAGCAGCAC<br>TTATGTC |
| | | AA | SEQ ID NO:3334<br>SGDKLGDKYAC | SEQ ID NO:11345<br>QDSKRPS | SEQ ID NO:19357<br>QAWDSSTYV |
| iPS:436728 | 21-225_152G6 | NA | SEQ ID NO:3335<br>TCTGGAGATAAATTGGGGGA<br>TAAATATGCTTCC | SEQ ID NO:11346<br>CAAGATAGCAAGCGGCC<br>CTCA | SEQ ID NO:19358<br>CAGGCGTGGGACAACAGCAC<br>TGTGGTA |
| | | AA | SEQ ID NO:3336<br>SGDKLGDKYAS | SEQ ID NO:11347<br>QDSKRPS | SEQ ID NO:19359<br>QAWDNSTVV |
| iPS:436730 | 21-225_152D7 | NA | SEQ ID NO:3337<br>TCTGGAGATAAATTGGGGGA<br>TAAATATGCTTCC | SEQ ID NO:11348<br>CAAGATAGCAAGCGGCC<br>CTCA | SEQ ID NO:19360<br>CAGGCGTGGGACAGCAGCAC<br>TGTGGTA |
| | | AA | SEQ ID NO:3338<br>SGDKLGDKYAS | SEQ ID NO:11349<br>QDSKRPS | SEQ ID NO:19361<br>QAWDSSTVV |
| iPS:436732 | 21-225_152B12 | NA | SEQ ID NO:3339<br>TCTGGCGATAAATTGGGGAAA<br>TAAATATGCTTGC | SEQ ID NO:11350<br>CAAGATACCAAGCGGCC<br>CTCA | SEQ ID NO:19362<br>CAGGCGTGGGACAGCAGCAC<br>TTATGTC |
| | | AA | SEQ ID NO:3340<br>SGDKLGNKYAC | SEQ ID NO:11351<br>QDTKRPS | SEQ ID NO:19363<br>QAWDSSTYV |
| iPS:436734 | 21-225_153A8 | NA | SEQ ID NO:3341<br>TCTGGAGATAAATTGGGGGA<br>TAAATATGCTTGC | SEQ ID NO:11352<br>CAAGATACCAAGCGGCC<br>CTCA | SEQ ID NO:19364<br>CAGGCGTGGGACAGCAGCAC<br>TTATGTC |
| | | AA | SEQ ID NO:3341<br>SGDKLGDKYAC | SEQ ID NO:11353<br>QDTKRPS | SEQ ID NO:19365<br>QAWDSSTYV |

FIGURE 49
(Continued)

| | | | | | | |
|---|---|---|---|---|---|---|
| iPS:436736 | 21-225_153E8 | NA | SEQ ID NO:3342 TCTGGAGAAGTAAATTGGGTAA TAAATATGTTTGC | SEQ ID NO:11354 CAAGATAACAAGCGGCC CTCA | SEQ ID NO:19366 CAGGCGTGGGACAGCAGCAC TTATGTGATA |
| | | AA | SEQ ID NO:3343 SGSKLGNKYVC | SEQ ID NO:11355 QDNKRPS | SEQ ID NO:19367 QAWDSSTYVI |
| iPS:436738 | 21-225_153D9 | NA | SEQ ID NO:3344 TCTGGAGATAAATTGGGGGA TAAATATGCTTGC | SEQ ID NO:11356 CAAGATAGGAAGCGGCC CTCA | SEQ ID NO:19368 CAGGCGTGGCACAGCAGTAC TGTGGTA |
| | | AA | SEQ ID NO:3345 SGDKLGDKYAC | SEQ ID NO:11357 QDRKRPS | SEQ ID NO:19369 QAWHSSTVV |
| iPS:436740 | 21-225_154C3 | NA | SEQ ID NO:3346 TCTGGAGATAAATTGGGGGA TAAATATGTTTGC | SEQ ID NO:11358 CAAGATAGGAAGCGGCC CTCA | SEQ ID NO:19370 CAGGCGTGGCACAGCAGCAC TGTGGTA |
| | | AA | SEQ ID NO:3347 SGDKLGDKYVC | SEQ ID NO:11359 QDRKRPS | SEQ ID NO:19371 QAWHSSTVV |
| iPS:436742 | 21-225_154C4 | NA | SEQ ID NO:3348 TCTGGAGATAAATTGGGGGA TAAATATGCTTCC | SEQ ID NO:11360 CAAGATAGCAAGCGGCC CTCA | SEQ ID NO:19372 CAGGCGTGGGACAGCAGCAC TGTGGTA |
| | | AA | SEQ ID NO:3349 SGDKLGDKYAS | SEQ ID NO:11361 QDSKRPS | SEQ ID NO:19373 QAWDSSTVV |
| iPS:436744 | 21-225_154F4 | NA | SEQ ID NO:3350 TCTGGAGATAAATTGGGGGA TAAATATGTTTGT | SEQ ID NO:11362 AAAGATAGTAAGCGGCC CTCA | SEQ ID NO:19374 CAGGCGTGGGACAACAGTAC TTTAGTA |
| | | AA | SEQ ID NO:3351 SGDKLGNKYVC | SEQ ID NO:11363 KDSKRPS | SEQ ID NO:19375 QAWDNSTLV |
| iPS:436746 | 21-225_154E10 | NA | SEQ ID NO:3352 TCTGGAGATAAATTGGGGGA TAAATATGCTTCC | SEQ ID NO:11364 CAAGATAGCAAGCGGCC CTCA | SEQ ID NO:19376 CAGGCGTGGGACAACAGCAC TGTGGTA |
| | | AA | SEQ ID NO:3353 SGDKLGDKYAS | SEQ ID NO:11365 QDSKRPS | SEQ ID NO:19377 QAWDNSTVV |

FIGURE 49
(Continued)

| | | | | | | |
|---|---|---|---|---|---|---|
| iPS:436748 | 21-225_154D11 | NA | SEQ ID NO:3354 TCTGGAGATAAATTGGGGGA TAAATATGCTTGC | SEQ ID NO:11366 CAAGATAAGAAGCGCC CTCA | SEQ ID NO:19378 CAGGCGTGGCACAGCAGTAT TGTGGTA | |
| | | AA | SEQ ID NO:3355 SGDKLGDKYAC | SEQ ID NO:11367 QDKKRPS | SEQ ID NO:19379 QAWHSSIVV | |
| iPS:436750 | 21-225_154G12 | NA | SEQ ID NO:3356 TCTGGAAGCAGCTCCAACAT CGGAAATAATGCTGTAAGC | SEQ ID NO:11368 AGTAATGATCACCGGCC CTCA | SEQ ID NO:19380 GCAGCATGGGATGACAGCCT GAAGGGTCCGGTA | |
| | | AA | SEQ ID NO:3357 SGSSSNIGNNAVS | SEQ ID NO:11369 SNDHRPS | SEQ ID NO:19381 AAWDDSLKGPV | |
| iPS:436752 | 21-225_155H1 | NA | SEQ ID NO:3358 ACTGGGAGCAGCTCCAATAT CGGGGCAGGTTATGATGTAC AC | SEQ ID NO:11370 GGTAACAGCAATCGGCC CTCA | SEQ ID NO:19382 CAGTCCTATGACAGCAGCCT GAGTGGTCCTGTGATA | |
| | | AA | SEQ ID NO:3359 TGSSSNIGAGYDVH | SEQ ID NO:11371 GNSNRPS | SEQ ID NO:19383 QSYDSSLSGPVI | |
| iPS:436754 | 21-225_155G3 | NA | SEQ ID NO:3360 TCTGGAGATAAAGTTGGGGGA TAAATATGTTTGC | SEQ ID NO:11372 CAAGATAGTAAGCGGCC CTCA | SEQ ID NO:19384 CAGGCGTGGGACAATAGTAT TTATGTC | |
| | | AA | SEQ ID NO:3361 SGDKLGDKYVC | SEQ ID NO:11373 QDSKRPS | SEQ ID NO:19385 QAWDNSIYV | |
| iPS:436756 | 21-225_146A10 | NA | SEQ ID NO:3362 TCTGGAGATAAATTGGGGGA TAAATATGTTTGC | SEQ ID NO:11374 CAAGATAGAAAGCGGCC CTCA | SEQ ID NO:19386 CAGGCGTGGGACAGCAGCAC TGTGGTG | |
| | | AA | SEQ ID NO:3363 SGDKLGDKYVC | SEQ ID NO:11375 QDRKRPS | SEQ ID NO:19387 QAWDSSTVV | |
| iPS:436758 | | NA | SEQ ID NO:3364 TCTGGAGATAAATTGGGGGA TAAATATGTTTCC | SEQ ID NO:11376 CAAGATAGCAAGCGGCC CTCA | SEQ ID NO:19388 CAGGCGTGGGACAGCAGCAC TGTGGTA | |

FIGURE 49
(Continued)

| | | | | | | |
|---|---|---|---|---|---|---|
| iPS:436760 | 21-225_155C10 | NA | SEQ ID NO:3365<br>SGDKLGDKYVS<br>SEQ ID NO:3366 | SEQ ID NO:11377<br>QDSKRPS<br>SEQ ID NO:11378 | SEQ ID NO:19389<br>QAWDSSTVV<br>SEQ ID NO:19390 |
| | | AA | TCTGGAGATAAATTGGGGGA<br>TAAATATGTTTCC | CAAGATAGGAAGCGGCC<br>CTCA | CTGGCGTGGACAGCAGCAC<br>TTTGTGGTA |
| iPS:436762 | 21-225_155E10 | NA | SEQ ID NO:3367<br>SGDKLGDKYVS<br>SEQ ID NO:3368 | SEQ ID NO:11379<br>QDRKRPS<br>SEQ ID NO:11380 | SEQ ID NO:19391<br>LAWDSSTFVV<br>SEQ ID NO:19392 |
| | | AA | TCTGGAAGCAGCTCCAACAT<br>CGGAAGTAATACTGTAAAT | AGTAGTAATCAGCGGCC<br>CTCA | GCAGCATGGGATGACAGCCT<br>GAATGGCGTGGTA |
| iPS:436764 | 21-225_156H2 | NA | SEQ ID NO:3369<br>SGSSSNIGSNTVN<br>SEQ ID NO:3370 | SEQ ID NO:11381<br>SSNQRPS<br>SEQ ID NO:11382 | SEQ ID NO:19393<br>AAWDDSLNGVV<br>SEQ ID NO:19394 |
| | | AA | TCTGGAGATAAATTGGGGGA<br>TAAATATGTTTGC | CAAGATAGTAAGCGGCC<br>CTCA | CAGGCGTGGGACAACAGCAG<br>CTTTGTGCTA |
| iPS:436766 | 21-225_158E9 | NA | SEQ ID NO:3371<br>SGDKLGDKYVC<br>SEQ ID NO:3372 | SEQ ID NO:11383<br>QDSKRPS<br>SEQ ID NO:11384 | SEQ ID NO:19395<br>QAWDNSSFVL<br>SEQ ID NO:19396 |
| | | AA | TCTGGAGATAAATTGGGGGA<br>TAAATATGTTTGC | CAAGATCGCAAGCGGCC<br>CTCA | CAGGCGTGGGCAACAGCAG<br>CTTGTGTGTA |
| iPS:436768 | 21-225_158D10 | NA | SEQ ID NO:3373<br>SGDKLGDKYVC<br>SEQ ID NO:3374 | SEQ ID NO:11385<br>QDRKRPS<br>SEQ ID NO:11386 | SEQ ID NO:19397<br>QAWGNSSFVV<br>SEQ ID NO:19398 |
| | | AA | TCTGGAGATAAATTGGGGGA<br>TAAATATGTTTGC | CAAGATAGGAAGCGGCC<br>CTCA | CAGGCGTGGGCAACAGCAG<br>CTTTGTGGTA |
| | 21-225_159H8 | NA | SEQ ID NO:3375<br>SGDKLGDKYVC<br>SEQ ID NO:3376 | SEQ ID NO:11387<br>QDRKRPS<br>SEQ ID NO:11388 | SEQ ID NO:19399<br>QAWGNSSFVV<br>SEQ ID NO:19400 |

FIGURE 49
(Continued)

| | | | | | |
|---|---|---|---|---|---|
| iPS:436770 | 21-225_160B12 | NA | TCTGGAGATAAATTGGGGA TAAATATGTTTGC SEQ ID NO:3377 | CAAGATAGCAAGCGGCC CTCA SEQ ID NO:11389 | CAGGGCGTGGGCAACAGCAG CTTTGTGGTA SEQ ID NO:19401 |
| | | AA | SGDKLGDKYVC SEQ ID NO:3378 | QDSKRPS SEQ ID NO:11390 | QAWGNSSFVV SEQ ID NO:19402 |
| iPS:436772 | 21-225_161H3 | NA | TCTGGAGATAGATTGGGGA TAAATATGTTTGC SEQ ID NO:3379 | CAAGATAACAAGCGGCC CTCA SEQ ID NO:11391 | CAGGCGTGGGTCAACAACAC TGCAGTGGTT SEQ ID NO:19403 |
| | | AA | SGDRLGDKYVC SEQ ID NO:3380 | QDNKRPS SEQ ID NO:11392 | QAWVNNTAVV SEQ ID NO:19404 |
| iPS:436774 | 21-225_161F10 | NA | TCTGGAGATAAATTGGGGA TAAATATGTTTGC SEQ ID NO:3381 | CAAGATAGCAAGCGGCC CTCA SEQ ID NO:11393 | CAGACGTGGGACAACAGTAG TTTTGCGGTT SEQ ID NO:19405 |
| | | AA | SGDKLGDKYVC SEQ ID NO:3382 | QDSKRPS SEQ ID NO:11394 | QTWDNSSFAL SEQ ID NO:19406 |
| iPS:436776 | 21-225_161F12 | NA | TCTGGAGATAAATTGGGTGA TAAATATGCTTGC SEQ ID NO:3383 | CAAGATACCAAGCGGCC CTCA SEQ ID NO:11395 | CAGGCGTGGGACAGCACCAC TCTGGTT SEQ ID NO:19407 |
| | | AA | SGDKLGDKYAC SEQ ID NO:3384 | QDTKRPS SEQ ID NO:11396 | QAWDSTTLV SEQ ID NO:19408 |
| iPS:436780 | 21-225_165H3 | NA | TCTGGAGATAAATTGGGTGA TAAATATGCTTGC SEQ ID NO:3385 | CAAGATAGCAAGCGGCC CTCA SEQ ID NO:11397 | CAGGCGTGGGACAGCACCAC TCTGGTT SEQ ID NO:19409 |
| | | AA | SGDKLGDKYAC SEQ ID NO:3386 | QDSKRPS SEQ ID NO:11398 | QAWDSTTLV SEQ ID NO:19410 |
| iPS:436782 | 21-225_166G11 | NA | TCTGGAGATAAATTGGGGA TAAATATGTTCAC SEQ ID NO:3387 | CAAGATAGCAAGCGGCC CTCA SEQ ID NO:11399 | CAGGCGTGGGACAACAGCAC TGCGGTA SEQ ID NO:19411 |
| | | AA | SGDKLGDKYVH SEQ ID NO:3388 | QDSKRPS SEQ ID NO:11400 | QAWDNSTAV SEQ ID NO:19412 |

FIGURE 49
(Continued)

| | | | | | |
|---|---|---|---|---|---|
| iPS:436784 | 21-225_169C1 | NA | TCTGGAGAGATAAATTGGGGGA TAAATATGTTTGT | AAAGATATCAAGCGGCC CTCA | CAGGGCGTGGGACACCAACAC TGTGATA |
| | | | SEQ ID NO:3389 | SEQ ID NO:11401 | SEQ ID NO:19413 |
| | | AA | SGDKLGDKYVC | KDIKRPS | QAWDTNTVI |
| | | | SEQ ID NO:3390 | SEQ ID NO:11402 | SEQ ID NO:19414 |
| iPS:436786 | 21-225_169A6 | NA | TCTGGAGAGATAAATTGGGGGA TAAATATGTTTGT | CAGGATTACAAGCGGCC CTCA | CAGGGCGTGGGACACCAACAC TGTGCTT |
| | | | SEQ ID NO:3391 | SEQ ID NO:11403 | SEQ ID NO:19415 |
| | | AA | SGDKLGDKYVC | QDYKRPS | QAWDTNTVL |
| | | | SEQ ID NO:3392 | SEQ ID NO:11404 | SEQ ID NO:19416 |
| iPS:436788 | 21-225_169B7 | NA | TCTGGAGAGATAAATTGGGGGG AAAATATGCTTCC | CAAGATAGGAAGCGGCC CTCA | CAGGGCGTGGGACAAGAACAC TGTGGTA |
| | | | SEQ ID NO:3393 | SEQ ID NO:11405 | SEQ ID NO:19417 |
| | | AA | SGDKLGDKYAS | QDRKRPS | QAWDKNTVV |
| | | | SEQ ID NO:3394 | SEQ ID NO:11406 | SEQ ID NO:19418 |
| iPS:436790 | 21-225_169G11 | NA | TCTGGAGAGATAAATTGGGGGA TAAATATGCTTGC | CAAGATAGTAAGCGGCC CTCA | CAGGGCGTGGGACAACAGCAC TGCGGTA |
| | | | SEQ ID NO:3395 | SEQ ID NO:11407 | SEQ ID NO:19419 |
| | | AA | SGDKLGDKYAC | QDSKRPS | QAWDNSTAV |
| | | | SEQ ID NO:3396 | SEQ ID NO:11408 | SEQ ID NO:19420 |
| iPS:436792 | 21-225_169D12 | NA | ACCCGCAGCAGTGGCAGCAT TACCGGCAACTATGTGCAG | GAGGATAAAAAAGACC CTCT | CAGTCTTATTATAGCGGCAA TTGGGTG |
| | | | SEQ ID NO:3397 | SEQ ID NO:11409 | SEQ ID NO:19421 |
| | | AA | TRSSGSITGNYVQ | EDKKRPS | QSYYSGNWV |
| | | | SEQ ID NO:3398 | SEQ ID NO:11410 | SEQ ID NO:19422 |
| iPS:436794 | 21-225_170F1 | NA | TCTGGAGAGATAAATTGGGGGA TAAATATTCTTGC | CAAGATAGTAAGCGGCC CTCA | CAGGGCGTGGGACAGCAACAC TGCGGTA |
| | | | SEQ ID NO:3399 | SEQ ID NO:11411 | SEQ ID NO:19423 |
| | | AA | SGDKLGDKYSC | QDSKRPS | QAWDSNTAV |

FIGURE 49
(Continued)

| | | | | | | |
|---|---|---|---|---|---|---|
| iPS:436796 | 21-225_170A5 | NA | SEQ ID NO:3400 TCTGGAGATAAATTGGGGGA TAAATATGCTTGT | SEQ ID NO:11412 CAAGATTACAAGCGGCC CTCA | SEQ ID NO:19424 CAGGCGTGGGACAACAGCAC TATGGTA |
| | | AA | SEQ ID NO:3401 SGDKLGDKYAC | SEQ ID NO:11413 QDYKRPS | SEQ ID NO:19425 QAWDNSTMV |
| iPS:436798 | 21-225_171F5 | NA | SEQ ID NO:3402 TCTGGAGATAAATTGGGGGG AAAATATGCTTCC | SEQ ID NO:11414 CAAGATAGGAAGCGGCC CTCA | SEQ ID NO:19426 CAGGCGTGGGACAAGAACAC TGTGGTA |
| | | AA | SEQ ID NO:3403 SGDKLGGKYAS | SEQ ID NO:11415 QDRKRPS | SEQ ID NO:19427 QAWDKNTVV |
| iPS:436800 | 21-225_171D12 | NA | SEQ ID NO:3404 CAAGGAGACAGCCTCAGAA GCTATTATGCAAGC | SEQ ID NO:11416 GCTAAAAACAACCGGCC CTCA | SEQ ID NO:19428 AACTCCCGGGACAGCAGTGG CAGCCATGTGGTA |
| | | AA | SEQ ID NO:3405 QGDSLRSYYAS | SEQ ID NO:11417 AKNNRPS | SEQ ID NO:19429 NSRDSSGSHVV |
| iPS:436802 | 21-225_171E12 | NA | SEQ ID NO:3406 TCTGGAGATAAATTGGGGGA TAAATATGCTTGC | SEQ ID NO:11418 CAAGATCGCAAGCGGCC CTCA | SEQ ID NO:19430 CAGGCGTGGGACATCAGCAC TTATGTGGTA |
| | | AA | SEQ ID NO:3407 SGDKLGDKYAC | SEQ ID NO:11419 QDRKRPS | SEQ ID NO:19431 QAWDISTYVV |
| iPS:436804 | 21-225_172C3 | NA | SEQ ID NO:3408 CAAGGAGACAGCCTCAGAA ACTATTATGTAAGC | SEQ ID NO:11420 ACTAAAAACAGCCGGCC CTCA | SEQ ID NO:19432 AACTCCCGGGACAGCAGTGG CAACCATGTGGTA |
| | | AA | SEQ ID NO:3409 QGDSLRNYYVS | SEQ ID NO:11421 TKNSRPS | SEQ ID NO:19433 NSRDSSGNHVV |
| iPS:436806 | 21-225_172B12 | NA | SEQ ID NO:3410 CAAGGAGACAGCCTCAGAA ACTATTATGCAAGC | SEQ ID NO:11422 ACTAAAAACAGCCGGCC CTCA | SEQ ID NO:19434 AACTCCCGGGACAGCAGTGG CAACCATGTGGTA |
| | | AA | SEQ ID NO:3411 QGDSLRNYYAS | SEQ ID NO:11423 TKNSRPS | SEQ ID NO:19435 NSRDSSGNHVV |

FIGURE 49
(Continued)

| | | | | | | |
|---|---|---|---|---|---|---|
| iPS:436808 | 21-225_173F8 | NA | SEQ ID NO:3412<br>TCTGGAAATAAATTGGGGAA<br>TAAATATGTTTGC | SEQ ID NO:11424<br>CAAGATAGCAGGCGGCC<br>CTCA | SEQ ID NO:19436<br>CAGGCGTGGGACAGCTTCAC<br>TGTGGTA |
| | | AA | SEQ ID NO:3413<br>SGNKLGNKYVC | SEQ ID NO:11425<br>QDSRRPS | SEQ ID NO:19437<br>QAWDSFTVV |
| iPS:436810 | 21-225_175F4 | NA | SEQ ID NO:3414<br>ACTGGAACCAGCAGTGATGT<br>TGGACGTTTTAACCTTGTCT<br>CC | SEQ ID NO:11426<br>GAGGTCAGTAAGCGGCC<br>CTCA | SEQ ID NO:19438<br>TGCTCATATGCAGGTAGTAG<br>CACCTATGTGGTA |
| | | AA | SEQ ID NO:3415<br>TGTSSDVGRFNLVS | SEQ ID NO:11427<br>EVSKRPS | SEQ ID NO:19439<br>CSYAGSSTYVV |
| iPS:436812 | 21-225_175C6 | NA | SEQ ID NO:3416<br>TCTGGAGATAAATTGGGGGA<br>TAAATATGCTTGT | SEQ ID NO:11428<br>CAAGATTACAAGCGGCC<br>CTCA | SEQ ID NO:19440<br>CAGGCGTGGGACAACAGCAC<br>TATGGTA |
| | | AA | SEQ ID NO:3417<br>SGDKLGDKYAC | SEQ ID NO:11429<br>QDYKRPS | SEQ ID NO:19441<br>QAWDNSTMV |
| iPS:436814 | 21-225_178H10 | NA | SEQ ID NO:3418<br>ACTGGAACCAGCAGTGATGT<br>TGGACGTTTTAACCTTGTCT<br>CC | SEQ ID NO:11430<br>GAAGTCAGTAAGCGGCC<br>CTCA | SEQ ID NO:19442<br>TGCTCATATGCAGGTAGTAG<br>CACCTTTGTAGTA |
| | | AA | SEQ ID NO:3419<br>TGTSSDVGRFNLVS | SEQ ID NO:11431<br>EVSKRPS | SEQ ID NO:19443<br>CSYAGSSTFVV |
| iPS:436816 | 21-225_179H5 | NA | SEQ ID NO:3420<br>CAAGGAGACAGTCTCAGAA<br>ACTATTATGCAAGC | SEQ ID NO:11432<br>GGTAAAACAACCGGCC<br>CTCA | SEQ ID NO:19444<br>AACTCCCGGGACAGCAGTGG<br>TAACCATTGGGTG |
| | | AA | SEQ ID NO:3421<br>QGDSLRNYYAS | SEQ ID NO:11433<br>GKNNRPS | SEQ ID NO:19445<br>NSRDSSGNHWV |
| iPS:436818 | | NA | SEQ ID NO:3422<br>TCTGGAGATAAATTGGGGGA<br>TAAATATGTTTGC | SEQ ID NO:11434<br>CAGGATAGTAAGCGGCC<br>CTCA | SEQ ID NO:19446<br>CAGGCGTGGGACAGCAACAC<br>TGCAGTGGTA |

FIGURE 49
(Continued)

| | | | | | | |
|---|---|---|---|---|---|---|
| iPS:436820 | 21-225_179C7 | AA | SEQ ID NO:3423<br>SGDKLGDKYVC<br>SEQ ID NO:3424 | SEQ ID NO:11435<br>QDSKRPS<br>SEQ ID NO:11436 | SEQ ID NO:19447<br>QAWDSNTAVV<br>SEQ ID NO:19448 |
| iPS:436822 | 21-225_179D10 | NA | ACTGGGAGCAGCTCCAACTT<br>CGGGACAGATTATGATGTAC<br>AC | GGTCACAGCAACCGGCC<br>CTCA | CAGTCCTATGATAGAAGCCT<br>GAATGTGGTC |
| | | AA | SEQ ID NO:3425<br>TGSSSNFGTDYDVH<br>SEQ ID NO:3426 | SEQ ID NO:11437<br>GHSNRPS<br>SEQ ID NO:11438 | SEQ ID NO:19449<br>QSYDRSLNVV<br>SEQ ID NO:19450 |
| iPS:436824 | 21-225_180D4 | NA | TCTGGAGATAGATTGGGGGA<br>TAAATATGCTTGC | GAAGATAGGAAGCGGCC<br>CTCA | CAGGGGTGGGACAGTAGGAA<br>AGTGGTA |
| | | AA | SEQ ID NO:3427<br>SGDRLGDKYAC<br>SEQ ID NO:3428 | SEQ ID NO:11439<br>EDRKRPS<br>SEQ ID NO:11440 | SEQ ID NO:19451<br>QAWDSRKVV<br>SEQ ID NO:19452 |
| iPS:436826 | 21-225_180C5 | NA | TCTGGAGATAAATTGGGGGA<br>AAAATATGCTTGC | CAAGATAGAAAGCGGCC<br>CTCA | CAGGGGTGGGACAGCAGCAC<br>TGCGGTA |
| | | AA | SEQ ID NO:3429<br>SGDKLGEKYAC<br>SEQ ID NO:3430 | SEQ ID NO:11441<br>QDRKRPS<br>SEQ ID NO:11442 | SEQ ID NO:19453<br>QAWDSSTAV<br>SEQ ID NO:19454 |
| iPS:436826 | 21-225_180G5 | NA | TCTGGAGATAAATTGGGGGA<br>TAAATATGTTAGC | CAAGATAGCAAGCGGCC<br>CTCA | CAGGCGTGGGACATCACCAC<br>TGCGGTA |
| | | AA | SEQ ID NO:3431<br>SGDKLGDKYVS<br>SEQ ID NO:3432 | SEQ ID NO:11443<br>QDSKRPS<br>SEQ ID NO:11444 | SEQ ID NO:19455<br>QAWDITTAV<br>SEQ ID NO:19456 |
| iPS:436828 | 21-225_181H1 | NA | TCTGGAGATAAATTGGGGGA<br>TAAATATGCTTGC | GAAGATAGGAAGCGGCC<br>CTCA | CAGGGGTGGGACAGCAGGA<br>AAGTGGTA |
| | | AA | SEQ ID NO:3433<br>SGDKLGDKYAC<br>SEQ ID NO:3434 | SEQ ID NO:11445<br>EDRKRPS<br>SEQ ID NO:11446 | SEQ ID NO:19457<br>QAWDSRKVV<br>SEQ ID NO:19458 |

FIGURE 49
(Continued)

| | | | | | | |
|---|---|---|---|---|---|---|
| iPS:436830 | 21-225_51F4 | NA | TCTGGAAGCAGCTCCAACAT CGGAAGTAATATTGTGACC | SEQ ID NO:3435 | AGTAATGATCAGCGGCC CTCA | SEQ ID NO:11447 | ACAGCATGGGATGACAGCCT GAATGGTTGGGTG | SEQ ID NO:19459 |
| | | AA | SGSSSNIGSNIVT | SEQ ID NO:3436 | SNDQRPS | SEQ ID NO:11448 | TAWDDSLNGWV | SEQ ID NO:19460 |
| iPS:436832 | 21-225_51D8 | NA | ACTGGGAGCAGCTCCAACAT CGGGGCAGGTTTTGAAGTAC AC | SEQ ID NO:3437 | GGTAACAGCAATCGCC CTCA | SEQ ID NO:11449 | CAGTCCTATGACAGCAGCCT GAGTGGTTATGTC | SEQ ID NO:19461 |
| | | AA | TGSSSNIGAGFEVH | SEQ ID NO:3438 | GNSNRPS | SEQ ID NO:11450 | QSYDSSLSGYV | SEQ ID NO:19462 |
| iPS:436834 | 21-225_52F1 | NA | TCTGGAAGCAGCTCCAACAT CGGAAGTAATATTGTGACC | SEQ ID NO:3439 | AGTAATGATCAGCGGCC CTCA | SEQ ID NO:11451 | GCAGCATGGGATGACAGCCT GAATGGTTGGGTG | SEQ ID NO:19463 |
| | | AA | SGSSSNIGSNIVT | SEQ ID NO:3440 | SNDQRPS | SEQ ID NO:11452 | AAWDDSLNGWV | SEQ ID NO:19464 |
| iPS:436836 | 21-225_52H3 | NA | TCTGGAGATAAATTGGGGGA TAAATATGTTTCC | SEQ ID NO:3441 | CAAGATAGAAAGCGGCC CTCA | SEQ ID NO:11453 | CAGGCGTGGGACAACAGCAC TGTGGTA | SEQ ID NO:19465 |
| | | AA | SGDKLGDKYVS | SEQ ID NO:3442 | QDRKRPS | SEQ ID NO:11454 | QAWDNSTVV | SEQ ID NO:19466 |
| iPS:436838 | 21-225_52H4 | NA | ACTGGAACCAGCAGTGACGT TGGTGGTTATAACTATGTCT CC | SEQ ID NO:3443 | GAGGTCAGTAATCGGCC CTCA | SEQ ID NO:11455 | AACTCATATACAAGCAACAT CACTTGGGTG | SEQ ID NO:19467 |
| | | AA | TGTSSDVGGYNYVS | SEQ ID NO:3444 | EVSNRPS | SEQ ID NO:11456 | NSYTSNITWV | SEQ ID NO:19468 |

FIGURE 49
(Continued)

| | | | | | |
|---|---|---|---|---|---|
| iPS:436840 | 21-225_53E9 | NA | TCTGGAACTAAATTGGGGA TAAATATGTTTGC SEQ ID NO:3445 | CAAGATACAATGCGGCC CTCA SEQ ID NO:11457 | CAGACGTGGGACAGCAGCAC TGCGGTT SEQ ID NO:19469 |
| | | AA | SGTKLGDKYVC SEQ ID NO:3446 | QDTMRPS SEQ ID NO:11458 | QTWDSSTAV SEQ ID NO:19470 |
| iPS:436842 | 21-225_54E9 | NA | TCTGGAAGCAACTCCAACAT CGGAAATAATATTGTCACC SEQ ID NO:3447 | GTTAATGATCAGCGGCC CTCA SEQ ID NO:11459 | GCAGTATGGGATGACAGCCT GAATGGTTGGGTG SEQ ID NO:19471 |
| | | AA | SGSNSNIGNNIVT SEQ ID NO:3448 | VNDQRPS SEQ ID NO:11460 | AAWDDSLNGWV SEQ ID NO:19472 |
| iPS:436844 | 21-225_56G1 | NA | TCTGGAAGCAGCTCCAACAT CGGAAGTCATATTGTTACC SEQ ID NO:3449 | AGTAATGATCAGCGGCC CTCA SEQ ID NO:11461 | GCAGTATGGGATGACAGCCT GATTGGTTGGGTG SEQ ID NO:19473 |
| | | AA | SGSSSNIGSHIVT SEQ ID NO:3450 | SNDQRPS SEQ ID NO:11462 | AVWDDSLIGWV SEQ ID NO:19474 |
| iPS:436846 | 21-225_56E3 | NA | TCTGGAAGCAGCTCCAACAT CGGAAGTAATATTGTTACC SEQ ID NO:3451 | AGTAATAATCAGCGGCC CTCA SEQ ID NO:11463 | GCAGCATGGGATGACAGCCT GAATGGTTGGGTG SEQ ID NO:19475 |
| | | AA | SGSSSNIGSNIVT SEQ ID NO:3452 | SNNQRPS SEQ ID NO:11464 | AAWDDSLNGWV SEQ ID NO:19476 |
| iPS:436848 | 21-225_57F1 | NA | TCTGGAGATAAACTGGGGGA AAAATATGCTTGC SEQ ID NO:3453 | CAAGATAGGAAGCGGCC CTCA SEQ ID NO:11465 | CAGGCGTGGGACAGCAGCAC TGTGGTA SEQ ID NO:19477 |
| | | AA | SGDKLGEKYAC SEQ ID NO:3454 | QDRKRPS SEQ ID NO:11466 | QAWDSSTVV SEQ ID NO:19478 |
| iPS:436850 | | NA | TCTGGAGAGAAATTGGGGG AAAAATTTGCTTGC | CAAGATAGCAAGCGGCC CTCA | CAGGCGTGGGACAGCAGCAC TGTGGTA |

FIGURE 49
(Continued)

| | | | | | | |
|---|---|---|---|---|---|---|
| iPS:436852 | 21-225_57D9 | AA | SEQ ID NO:3455 SGEKLGEKFAC | SEQ ID NO:11467 QDSKRPS | SEQ ID NO:19479 QAWDSSTVV | |
| | | NA | SEQ ID NO:3456 TCTGGAGATAAAACTGGGGGA AAATATGCTTGC | SEQ ID NO:11468 CAAGATAGGAAGCGGCC CTCA | SEQ ID NO:19480 CAGGCGTGGACAGCAGCAC TGTGGTA | |
| iPS:436854 | 21-225_57H11 | AA | SEQ ID NO:3457 SGDKLGEKYAC | SEQ ID NO:11469 QDRKRPS | SEQ ID NO:19481 QAWDSSTVV | |
| | | NA | SEQ ID NO:3458 TCTGGAGATAAAATTGGGGAA TAAATATGCTTGC | SEQ ID NO:11470 CAAGATAGGAAGCGGCC CTCA | SEQ ID NO:19482 CAGGCGTGGACAGCAGCAC TGCA | |
| iPS:436856 | 21-225_58C1 | AA | SEQ ID NO:3459 SGDKLGNKYAC | SEQ ID NO:11471 QDRKRPS | SEQ ID NO:19483 QAWDSSTA | |
| | | NA | SEQ ID NO:3460 TCTGGAAGCAGCTCCAACAT TGGGAATAATTATGTATCC | SEQ ID NO:11472 GACAATAATAAGGACC CTCA | SEQ ID NO:19484 GGAACATGGGATATCAGTCT GAGTGTTGGGGTA | |
| iPS:436858 | 21-225_58C5 | AA | SEQ ID NO:3461 SGSSSNIGNNYVS | SEQ ID NO:11473 DNNKRPS | SEQ ID NO:19485 GTWDISLSVGV | |
| | | NA | SEQ ID NO:3462 TCTGGAGATAAAATTGGGGA TAAATATACTTGC | SEQ ID NO:11474 CAAGATAACAAGCGGCC CTCA | SEQ ID NO:19486 CAGGCGTGGAACAACTACAC TGTGGTA | |
| iPS:436860 | 21-225_58E7 | AA | SEQ ID NO:3463 SGDKLGDKYTC | SEQ ID NO:11475 QDNKRPS | SEQ ID NO:19487 QAWNNYTVV | |
| | | NA | SEQ ID NO:3464 TCTGGAGATAAAATTGGGGA TAAATATGCTTGC | SEQ ID NO:11476 CAAGATAGGAAGCGGCC CTCA | SEQ ID NO:19488 CAGGCGTGGACAGCAGCAC TGTGGTA | |
| iPS:436860 | 21-225_58F7 | AA | SEQ ID NO:3465 SGDKLGDKYAC | SEQ ID NO:11477 QDRKRPS | SEQ ID NO:19489 QAWDSSTVV | |
| | | | SEQ ID NO:3466 | SEQ ID NO:11478 | SEQ ID NO:19490 | |

FIGURE 49
(Continued)

| | | | | | |
|---|---|---|---|---|---|
| iPS:436862 | 21-225_58F8 | NA | TCTGGAGATAAATTGGGAAA TAAATATGCTTGC SEQ ID NO:3467 | CAAGATAGCAAGCGGCC CTCA SEQ ID NO:11479 | CAGGGCGTGGACAACAGCAC TGTGGTA SEQ ID NO:19491 |
| | | AA | SGDKLGNKYAC SEQ ID NO:3468 | QDSKRPS SEQ ID NO:11480 | QAWDSSTVV SEQ ID NO:19492 |
| iPS:436864 | 21-225_58G11 | NA | TCTGGAGATAAATTGGGGGA TAAATATGCTTCC SEQ ID NO:3469 | CAAGATAACAAGCGGCC CTCA SEQ ID NO:11481 | CAGGCGTGGAACAACAACAC TGTAATG SEQ ID NO:19493 |
| | | AA | SGDKLGDKYAS SEQ ID NO:3470 | QDNKRPS SEQ ID NO:11482 | QAWNNNTVM SEQ ID NO:19494 |
| iPS:436866 | 21-225_59F2 | NA | TCTGGAGATAAATTGGGGGA TAAATATGCTTCT SEQ ID NO:3471 | CAAGATAACAAGCGGCC CTCA SEQ ID NO:11483 | CAGGCGTGGGACAACAGCAC TGTGGTC SEQ ID NO:19495 |
| | | AA | SGDKLGDKYAS SEQ ID NO:3472 | QDNKRPS SEQ ID NO:11484 | QAWDNNTVV SEQ ID NO:19496 |
| iPS:436868 | 21-225_59B11 | NA | TCTGGAGATAAATTGGGGGA TAAATATGCTTGC SEQ ID NO:3473 | CAAGATAGCAAGCGGCC CTCA SEQ ID NO:11485 | CAGGCGTGGGACACAGCAC TTATGTGGTA SEQ ID NO:19497 |
| | | AA | SGDKLGDKYAC SEQ ID NO:3474 | QDSKRPS SEQ ID NO:11486 | QAWDSSTYVV SEQ ID NO:19498 |
| iPS:436870 | 21-225_60B1 | NA | TCTGGAGATAAACTGGGGGA AAAATATGCTTGC SEQ ID NO:3475 | CAAGATAGGAAGCGGCC CTCA SEQ ID NO:11487 | CAGGCGTGGGACAACAGCAC TGTGGTA SEQ ID NO:19499 |
| | | AA | SGDKLGEKYAC SEQ ID NO:3476 | QDRKRPS SEQ ID NO:11488 | QAWDSSTVV SEQ ID NO:19500 |
| iPS:436872 | 21-225_60D2 | NA | TCTGGAAATAAATTGGGGGA TAAATATGCTTCT SEQ ID NO:3477 | CAAGATAACAAGCGGCC CTCA SEQ ID NO:11489 | CAGGCGTGGACAACAACAC TGTGGTC SEQ ID NO:19501 |
| | | AA | SGNKLGDKYAS SEQ ID NO:3478 | QDNKRPS SEQ ID NO:11490 | QAWDNNTVV SEQ ID NO:19502 |

FIGURE 49
(Continued)

| | | | | | |
|---|---|---|---|---|---|
| iPS:436874 | 21-225_60A12 | NA | TCTGGAGATAAATTGGGGAA TAAATATGCTTGC SEQ ID NO:3479 | CAAGATAGGAAGCGGCC CTCA SEQ ID NO:11491 | CAGGGCGTGGGACAGCAGCAC TGCT SEQ ID NO:19503 |
| | | AA | SGDKLGNKYAC SEQ ID NO:3480 | QDRKRPS SEQ ID NO:11492 | QAWDSSTA SEQ ID NO:19504 |
| iPS:436876 | 21-225_61F5 | NA | TCTGGAGATAAATTGGGGGA AAAATATGCTTGC SEQ ID NO:3481 | CAAGATAGCAAGCGGCC CTCA SEQ ID NO:11493 | CAGGGCGTGGGACAGCAGCAC TGTGGTT SEQ ID NO:19505 |
| | | AA | SGDKLGEKYAC SEQ ID NO:3482 | QDSKRPS SEQ ID NO:11494 | QAWDSSTVV SEQ ID NO:19506 |
| iPS:436878 | 21-225_62E3 | NA | TCTGGAGATAAATTGGGGAA TAAATATGCTTGC SEQ ID NO:3483 | CAAGATAGGAAGCGGCC CTCA SEQ ID NO:11495 | CAGGGCGTGGGACAGCAGCAC TGCGGTA SEQ ID NO:19507 |
| | | AA | SGDKLGNKYAC SEQ ID NO:3484 | QDRKRPS SEQ ID NO:11496 | QAWDSSTAV SEQ ID NO:19508 |
| iPS:436880 | 21-225_62E8 | NA | TCTGGAGATAGATTGGGGAA TAAATATGCTTCC SEQ ID NO:3485 | CAGGATAGGAAGCGGCC CTCA SEQ ID NO:11497 | CAGGGCGTGGGACAGCAGCAC TGCGGTA SEQ ID NO:19509 |
| | | AA | SGDRLGNKYAS SEQ ID NO:3486 | QDRKRPS SEQ ID NO:11498 | QAWDSSTAV SEQ ID NO:19510 |
| iPS:436882 | 21-225_62D10 | NA | TCTGGAGATAAATTGGGGAA TAAATATGCTTGC SEQ ID NO:3487 | CAAGATAGGAAGCGGCC CTCA SEQ ID NO:11499 | CAGGGCGTGGGACAGCAGCAC TGCGGTA SEQ ID NO:19511 |
| | | AA | SGDKLGNKYAC SEQ ID NO:3488 | QDRKRPS SEQ ID NO:11500 | QAWDSSTAV SEQ ID NO:19512 |
| iPS:436884 | 21-225_62A12 | NA | TCTGGAGATAAATTGGGGAA TAAATATGCTTGC SEQ ID NO:3489 | CAAGATAGGAAGCGGCC CTCA SEQ ID NO:11501 | CAGGGCGTGGGACAGCAGCAC TGCGGTA SEQ ID NO:19513 |
| | | AA | SGDKLGNKYAC SEQ ID NO:3490 | QDRKRPS SEQ ID NO:11502 | QAWDSSTAV SEQ ID NO:19514 |

FIGURE 49
(Continued)

| | | | | | |
|---|---|---|---|---|---|
| iPS:436886 | 21-225_62B12 | NA | TCTGGAGAGATAAATTGGGGAA TAAATATACTTGC SEQ ID NO:3491 | CAAGATAGGAAGCGGCC CTCA SEQ ID NO:11503 | CAGGGCGTGGACAGCAGCAC TGCGGTA SEQ ID NO:19515 |
| | | AA | SGDKLGNKYTC SEQ ID NO:3492 | QDRKRPS SEQ ID NO:11504 | QAWDSSTAV SEQ ID NO:19516 |
| iPS:436888 | 21-225_63G7 | NA | ACCCGCAGCAATGGCAGCAT TGTCAGCAACTATGTGCAG SEQ ID NO:3493 | GAGGATAGCCGAAGACC CTCT SEQ ID NO:11505 | CAGTCTTATGATGGCATCAA TGTGGTA SEQ ID NO:19517 |
| | | AA | TRSNGSIVSNYVQ SEQ ID NO:3494 | EDSRRPS SEQ ID NO:11506 | QSYDGINVV SEQ ID NO:19518 |
| iPS:436890 | 21-225_63A10 | NA | ACCCGCAGCAATGGCAGCAT TGTCAGCAACTATGTGCAG SEQ ID NO:3495 | GAGGATAAAAGAAGACC CTCA SEQ ID NO:11507 | CAGTCTTATGATAGCATCAA TGTGGTA SEQ ID NO:19519 |
| | | AA | TRSNGSIVSNYVQ SEQ ID NO:3496 | EDKRRPS SEQ ID NO:11508 | QSYDSINVV SEQ ID NO:19520 |
| iPS:436892 | 21-225_65E9 | NA | TCTGGAGAGATAAATTGGGGAA TAAATATGATTAC SEQ ID NO:3497 | CAAGATAGAAGCGGCC CTCA SEQ ID NO:11509 | CAGGGCGTGGACAACAGCAC TGTGGTA SEQ ID NO:19521 |
| | | AA | SGDKLGNKYDY SEQ ID NO:3498 | QDRKRPS SEQ ID NO:11510 | QAWDNSTVV SEQ ID NO:19522 |
| iPS:436894 | 21-225_66G9 | NA | TCTGGAGAGATAAATTGGGGAA TAAATATGCTTGC SEQ ID NO:3499 | CAAGATAGGAAGCGGCC CTCA SEQ ID NO:11511 | CAGGGCGTGGGACATCAACAC TGCGGTA SEQ ID NO:19523 |
| | | AA | SGDKLGNKYAC SEQ ID NO:3500 | QDRKRPS SEQ ID NO:11512 | QAWDINTAV SEQ ID NO:19524 |
| iPS:436896 | 21-225_67F10 | NA | TCTGGAGAGATAAATTGGGGTA TAAATATGCTTGG SEQ ID NO:3501 | GAAGATAGGAAGCGGCC CTCA SEQ ID NO:11513 | CAGGGCGTGGACAACAGCAC TGTGGTA SEQ ID NO:19525 |

FIGURE 49
(Continued)

| | | | SGDKLGYKYAW | | EDRKRPS | | QAWDNSTVV | |
|---|---|---|---|---|---|---|---|---|
| | | AA | SEQ ID NO:3501 | | SEQ ID NO:11513 | | SEQ ID NO:19526 | |
| iPS:436898 | 21-225_68D8 | NA | TCTGGAGATAAATTGGGGGA TAAATATGCTTGC | SEQ ID NO:3502 | CAAGATAGCAAGCGGCC CTCA | SEQ ID NO:11514 | CAGGCGTGGACAACAGCAC TGTGGTA | SEQ ID NO:19527 |
| | | AA | SGDKLGDKYAC | SEQ ID NO:3503 | QDSKRPS | SEQ ID NO:11515 | QAWDNSTVV | SEQ ID NO:19528 |
| iPS:436900 | 21-225_69B9 | NA | TCTGGAGATAAATTGGGGGA TAAATATGATTAC | SEQ ID NO:3504 | CAAGATAGAAAGCGGCC CTCA | SEQ ID NO:11516 | CAGGCGTGGACAACAGCAC TGTGGTA | SEQ ID NO:19529 |
| | | AA | SGDKLGNKYDY | SEQ ID NO:3505 | QDRKRPS | SEQ ID NO:11517 | QAWDNSTVV | SEQ ID NO:19530 |
| iPS:436902 | 21-225_69B11 | NA | TCTGGAGATAAATTGGGGGA TAAATATGCTTGG | SEQ ID NO:3506 | GAAGATAGGAAGCGGCC CTCA | SEQ ID NO:11518 | CAGGCGTGGACAACAGCAC TGTGGTA | SEQ ID NO:19531 |
| | | AA | SGDKLGDKYAW | SEQ ID NO:3507 | EDRKRPS | SEQ ID NO:11519 | QAWDNSTVV | SEQ ID NO:19532 |
| iPS:436904 | 21-225_71D4 | NA | TCTGGAGATAAATTGGGGGA TAAATATGCTTAC | SEQ ID NO:3508 | CAAGATAGGAAGCGGCC CTCA | SEQ ID NO:11520 | CAGGCGTGGTCAACAGCAC TGTGGTA | SEQ ID NO:19533 |
| | | AA | SGDKLGDKYAY | SEQ ID NO:3509 | QDSKRPS | SEQ ID NO:11521 | QAWVNSTVV | SEQ ID NO:19534 |
| iPS:436906 | 21-225_72B4 | NA | TCTGGAGATAAATTGGGGGA TAAATATGCTTGG | SEQ ID NO:3510 | GAAGATAGGAAGCGGCC CTCA | SEQ ID NO:11522 | CAGGCGTGGACAACAGCAC TGTGGTA | SEQ ID NO:19535 |
| | | AA | SGDKLGDKYAW | SEQ ID NO:3511 | EDRKRPS | SEQ ID NO:11523 | QAWDNSTVV | SEQ ID NO:19536 |
| iPS:436908 | 21-225_72D5 | NA | TCTGGAGATAAATTGGGGGA TAAATATGCTTGC | SEQ ID NO:3512 | CAAGATAGGAAGCGGCC CTCA | SEQ ID NO:11524 | CAGGCGTGGACAGCAGCAC TGCGGTA | SEQ ID NO:19537 |
| | | | | SEQ ID NO:3513 | | SEQ ID NO:11525 | | |

FIGURE 49
(Continued)

| | | AA/NA | | | | | | |
|---|---|---|---|---|---|---|---|---|
| iPS:436910 | 21-225_73G1 | AA | SGDKLGNKYAC | SEQ ID NO:3514 | QDRKRPS | SEQ ID NO:11526 | QAWDSSTAV | SEQ ID NO:19538 |
| | | NA | GGCTTGAGCTCTGGCTCAGTCTCTACTAGTTACTACCCCAGC | SEQ ID NO:3515 | AACACAAACACTCGCTCTTCT | SEQ ID NO:11527 | GTTCTATATGGGTAGTGCCATTTGGGTG | SEQ ID NO:19539 |
| iPS:436912 | 21-225_73C4 | AA | GLSSGSVSTSYYPS | SEQ ID NO:3516 | NTNTRSS | SEQ ID NO:11528 | VLYMGSAIWV | SEQ ID NO:19540 |
| | | NA | TCTGGAGATAAATTGGGGAATAAATATGCTTGC | SEQ ID NO:3517 | CAAGATATGAAGCGGCCCTCA | SEQ ID NO:11529 | CAGGGCGTGGGACAGCAGCACTGCGGTA | SEQ ID NO:19541 |
| | | AA | SGDKLGNKYAC | SEQ ID NO:3518 | QDMKRPS | SEQ ID NO:11530 | QAWDSSTAV | SEQ ID NO:19542 |
| iPS:436914 | 21-225_76B4 | NA | TCTGGAGATAGATTGGGGACTAAATTGCTTGC | SEQ ID NO:3519 | CAAGATAACAGGCGGCCCTCA | SEQ ID NO:11531 | CAGGGCGTGGGACAGCAGCACTGTA | SEQ ID NO:19543 |
| | | AA | SGDRLGTKFAC | SEQ ID NO:3520 | QDSKRPS | SEQ ID NO:11532 | QAWDSSTV | SEQ ID NO:19544 |
| iPS:436916 | 21-225_74A9 | NA | TCTGGAGATAAATTGGGTAATAAATATGTTTGT | SEQ ID NO:3521 | CAAGATAACAGGCGGCCCTCA | SEQ ID NO:11533 | CAGGGCGTGGGACAGCAGTCCTGTGATA | SEQ ID NO:19545 |
| | | AA | SGDKLGNKYVC | SEQ ID NO:3522 | QDNRRPS | SEQ ID NO:11534 | QAWDSSPVI | SEQ ID NO:19546 |
| iPS:436918 | 21-225_77A2 | NA | TCTGGAGATAGATTGGGGGATAAATATGCTTGC | SEQ ID NO:3523 | CAAGATAGGAAGCGGCCCTCA | SEQ ID NO:11535 | CAGGGCGTGGGACAGCAGTACTGCGGTA | SEQ ID NO:19547 |
| | | AA | SGDRLGDKYAC | SEQ ID NO:3524 | QDRKRPS | SEQ ID NO:11536 | QAWDSSTAV | SEQ ID NO:19548 |

FIGURE 49
(Continued)

| | | | | | | |
|---|---|---|---|---|---|---|
| iPS:436920 | 21-225_74E5 | NA | GCTTCCAGCACTGAAACAGT CACCAGTGGTTCTTATCCGA AC | AGTACAAGCAACAAACA CTCC | CTGCTCTACTATGGTGGTGC TCAACTGGTA | |
| | | | SEQ ID NO:3525 | SEQ ID NO:11537 | SEQ ID NO:19549 | |
| | | AA | ASSTETVTSGSYPN | STSNKHS | LLYYGGAQLV | |
| | | | SEQ ID NO:3526 | SEQ ID NO:11538 | SEQ ID NO:19550 | |
| iPS:436922 | 21-225_78E9 | NA | TCAGGAGATAAATTGGGGA ATAAATATGTTTCC | CAAGATAACAGGCGGCC GTCA | CAGGCGTGGGACAGCAGCCC TGTGATA | |
| | | | SEQ ID NO:3527 | SEQ ID NO:11539 | SEQ ID NO:19551 | |
| | | AA | SGDKLGNKYVS | QDNRRPS | QAWDSSPVI | |
| | | | SEQ ID NO:3528 | SEQ ID NO:11540 | SEQ ID NO:19552 | |
| iPS:436924 | 21-225_74B3 | NA | TCTGGAGATAAATTGGGGGA TAAATATGCTTGC | CAAGATAGCAAGCGGCC CTCA | CAGGCGTGGGACAGCAGCCAC TGTGGTA | |
| | | | SEQ ID NO:3529 | SEQ ID NO:11541 | SEQ ID NO:19553 | |
| | | AA | SGDKLGDKYAC | QDSKRPS | QAWDSTTVV | |
| | | | SEQ ID NO:3530 | SEQ ID NO:11542 | SEQ ID NO:19554 | |
| iPS:436926 | 21-225_78D10 | NA | GCTTCCAGCACTGGAGCAGT CACCAGTGGTTACTTTCCAA AC | AGTACAGACAACAAACA CTCC | CTCCTCTACTATGGTGGTGCT CAGCTGATG | |
| | | | SEQ ID NO:3531 | SEQ ID NO:11543 | SEQ ID NO:19555 | |
| | | AA | ASSTGAVTSGYFPN | STDNKHS | LLYYGGAQLM | |
| | | | SEQ ID NO:3532 | SEQ ID NO:11544 | SEQ ID NO:19556 | |
| iPS:436928 | 21-225_79E7 | NA | TCAGGAGATAAATTGGGGA ATAAATATGTTTCC | CAAGATAACAGGCGGCC CTCA | CAGGCGTGGGACAGCAGCCC TGTGATA | |
| | | | SEQ ID NO:3533 | SEQ ID NO:11545 | SEQ ID NO:19557 | |
| | | AA | SGDKLGNKYVS | QDNRRPS | QAWDSSPVI | |
| | | | SEQ ID NO:3534 | SEQ ID NO:11546 | SEQ ID NO:19558 | |
| iPS:436932 | 21-225_92A4 | NA | TCTGGAGATAAATTGGGGAA TAAATATGTTTGC | CAAGATAACAGGCGGCC CTCA | CAGGCGTGGGACAGCAGCCC TGTGATA | |
| | | | SEQ ID NO:3535 | SEQ ID NO:11547 | SEQ ID NO:19559 | |

FIGURE 49
(Continued)

| | | AA/NA | | | | | | | |
|---|---|---|---|---|---|---|---|---|---|
| iPS:436934 | 21-225_96B5 | AA | SGDKLGNKYVC | SEQ ID NO:3536 | | | QDNRRPS | SEQ ID NO:11548 | | | QAWDSSPVI | SEQ ID NO:19560 |
| | | NA | TCTGGAGATAAATTGGGGAC TAAATTTGCTTGC | SEQ ID NO:3537 | CAAGATAGCAAGCGGCC CTCA | SEQ ID NO:11549 | CAGGCGTGGACAGCAGCAC TGTA | SEQ ID NO:19561 |
| iPS:436936 | 21-225_97E6 | AA | SGDRLGTKFAC | SEQ ID NO:3538 | | | QDSKRPS | SEQ ID NO:11550 | | | QAWDSSTV | SEQ ID NO:19562 |
| | | NA | TCTGGAGATAAATTGGGGAA TAAATATGTTCC | SEQ ID NO:3539 | CAAGATAACAGGCGGCC GTCA | SEQ ID NO:11551 | CAGGCGTGGACAGCACCCC TGTGATA | SEQ ID NO:19563 |
| iPS:436938 | 21-225_146A3 | AA | SGDKLGNKYVS | SEQ ID NO:3540 | | | QDNRRPS | SEQ ID NO:11552 | | | QAWDSTPVI | SEQ ID NO:19564 |
| | | NA | TCTGGAGATAAATTGGGGAA TAGATATGCTTGC | SEQ ID NO:3541 | CAAGATAGCAAGCGGCC CTCA | SEQ ID NO:11553 | CAGGCGTGGACAGCAGCAC TGTGGTA | SEQ ID NO:19565 |
| iPS:436940 | 21-225_146B8 | AA | SGNKLGNRYAC | SEQ ID NO:3542 | | | QDSKRPS | SEQ ID NO:11554 | | | QAWDSSTVV | SEQ ID NO:19566 |
| | | NA | TCTGGAGATAAATTGGGGAA TAAATATGTTGC | SEQ ID NO:3543 | CAAGATAGGAAGCGGCC CTCA | SEQ ID NO:11555 | CAGGCGTGGCACAGCAGCAC TGTGGTA | SEQ ID NO:19567 |
| iPS:436942 | 21-225_146H8 | AA | SGDKLGDKYAC | SEQ ID NO:3544 | | | QDRKRPS | SEQ ID NO:11556 | | | QAWHSSTVV | SEQ ID NO:19568 |
| | | NA | TCTGGAGATAAATTGGGGAA TAAATATGCTTGC | SEQ ID NO:3545 | CAAGATAAGAAGCGGCC CTCA | SEQ ID NO:11557 | CAGGCGTGGACATCAGAAC TGTGGTA | SEQ ID NO:19569 |
| iPS:436944 | 21-225_182D12 | AA | SGDKLGDKYAC | SEQ ID NO:3546 | | | QDKKRPS | SEQ ID NO:11558 | | | QAWDIRTVV | SEQ ID NO:19570 |
| | | NA | TCTGGAGATAAATTGGGGAA GAAATATGCTTGC | SEQ ID NO:3547 | CAAGATAGAAAGCGGCC CTCA | SEQ ID NO:11559 | CAGGCGTGGACAGTAGAAC TGCGGTA | SEQ ID NO:19571 |

FIGURE 49
(Continued)

| ID | Sub-ID | Type | Sequence | SEQ ID | Sequence | SEQ ID | Sequence | SEQ ID |
|---|---|---|---|---|---|---|---|---|
| iPS:436946 | 21-225_183F4 | AA | SGDKLGEKYAC | SEQ ID NO:3548 | QDRKRPS | SEQ ID NO:11560 | QAWDSRTAV | SEQ ID NO:19572 |
| | | NA | TCTGGAGATAAATTGGGGGATAAATATGCTTGT | SEQ ID NO:3549 | CAAGATAAGAAACGGCCCTCA | SEQ ID NO:11561 | CAGGCGTGGGACAACAGCACTGCTGTGGTA | SEQ ID NO:19573 |
| iPS:436948 | 21-225_183F5 | AA | SGDKLGDKYAC | SEQ ID NO:3550 | QDKKRPS | SEQ ID NO:11562 | QAWDNSTAVV | SEQ ID NO:19574 |
| | | NA | GGCTTGAGCTCTGGCTCAGTCTCTACTACTTCTACCCCAGC | SEQ ID NO:3551 | AACACAAACACTCGCTCTTCT | SEQ ID NO:11563 | GTGCTTTATATGGGTAGTGGCATTTGGGTG | SEQ ID NO:19575 |
| iPS:436950 | 21-225_184G4 | AA | GLSSGSVSTFYPS | SEQ ID NO:3552 | NTNTRSS | SEQ ID NO:11564 | VLYMGSGIWV | SEQ ID NO:19576 |
| | | NA | TCTGGAGATAAATTGGGGGATAAATATGCTTGC | SEQ ID NO:3553 | GAAGATAGGAAGCGGCCCTCA | SEQ ID NO:11565 | CAGGCGTGGGACAGCCGCACTGTGTA | SEQ ID NO:19577 |
| iPS:436952 | 21-225_185D2 | AA | SGDKLGDKFAC | SEQ ID NO:3554 | EDRKRPS | SEQ ID NO:11566 | QAWDSRTVV | SEQ ID NO:19578 |
| | | NA | TCTGGAGATAAATTGGGGGATAAATATGCTTGC | SEQ ID NO:3555 | GAAGATAGGAAGCGGCCCTCA | SEQ ID NO:11567 | CAGGCGTGGGACAGCAGGAAAGTGGTA | SEQ ID NO:19579 |
| iPS:436954 | 21-225_185G7 | AA | SGDKLGDKYAC | SEQ ID NO:3556 | EDRKRPS | SEQ ID NO:11568 | QAWDSRKVV | SEQ ID NO:19580 |
| | | NA | TCTGGAGATAAATTGGGGGATAAATATGCTTGC | SEQ ID NO:3557 | CAAGATCGCAAGCGGCCCTCA | SEQ ID NO:11569 | CAGGCGTGGGACAGCAGCACGGTA | SEQ ID NO:19581 |
| iPS:436956 | | AA | SGDKLGHKFVC | SEQ ID NO:3558 | QDRKRPS | SEQ ID NO:11570 | QAWDSSTV | SEQ ID NO:19582 |
| | | NA | TCTGGAGATAAATGGGGGAAAAATATGCTTGC | | CAAGATAGAAAGCGGCCCTCA | | CAGGCGTGGGACAGCAGCACTGCGGTA | |

FIGURE 49
(Continued)

| | | | | SEQ ID NO:3559 | | SEQ ID NO:11571 | | SEQ ID NO:19583 |
|---|---|---|---|---|---|---|---|---|
| iPS:436958 | 21-225_186H6 | | AA | SGDKMGEKYAC | | QDRKRPS | | QAWDSSTAV |
| | | | | SEQ ID NO:3560 | | SEQ ID NO:11572 | | SEQ ID NO:19584 |
| iPS:436960 | 21-225_190D1 | | NA | GCTTCCAGCACTGGAGCAGTCACCAGTGGTTCCTATCCAAAC | | AGTACAAGTAACAAACACTCC | | CTGCTCTACTATGGTGGTGCTCAGGTGGCA |
| | | | | SEQ ID NO:3561 | | SEQ ID NO:11573 | | SEQ ID NO:19585 |
| | | | AA | ASSTGAVTSGSYPN | | STSNKHS | | LLYYGGAQVA |
| | | | | SEQ ID NO:3562 | | SEQ ID NO:11574 | | SEQ ID NO:19586 |
| iPS:436962 | 21-225_198D2 | | NA | TCTGGAAGCAGCTCCAACATTGGGAGTAATTATGTTTCC | | GACAATAATAAGCGACCCTCA | | GGAACATGGGATAGCAGACTGAATGTGGGGTA |
| | | | | SEQ ID NO:3563 | | SEQ ID NO:11575 | | SEQ ID NO:19587 |
| | | | AA | SGSSSNIGSNYVS | | DNNKRPS | | GTWDSRLNVGV |
| | | | | SEQ ID NO:3564 | | SEQ ID NO:11576 | | SEQ ID NO:19588 |
| iPS:436963 | 21-225_190H1 | | NA | TCTGGAGATAAATTGGGGATAGATTGCTTAC | | CAAGATAGCAAGCAAGCGGCCCTCA | | AAGGCGTGGGACAGCAGCACTGTGTA |
| | | | | SEQ ID NO:3565 | | SEQ ID NO:11577 | | SEQ ID NO:19589 |
| | | | AA | SGDKLGDRFAY | | QDSKRPS | | KAWDSSTVV |
| | | | | SEQ ID NO:3566 | | SEQ ID NO:11578 | | SEQ ID NO:19590 |
| iPS:436964 | 21-225_190B3 | | NA | CAAGGAGACAAAACTCAGAACCTATTATGCAAGC | | GGAAAAAACAACCGGCCCTCA | | AACTCCCGGGACACAGCAGTGGTAACCATCTTGTACTA |
| | | | | SEQ ID NO:3567 | | SEQ ID NO:11579 | | SEQ ID NO:19591 |
| | | | AA | QGDKLRTYYAS | | GKNNRPS | | NSRDSSGNHLVL |
| | | | | SEQ ID NO:3568 | | SEQ ID NO:11580 | | SEQ ID NO:19592 |
| iPS:436966 | 21-225_190C3 | | NA | TCTGGAAGCAGCTCCAACATTGGAAATAATTATGTATCC | | GACAGTAATAAGCGACCCTCA | | GGAACATGGGATAGCAGCCTGAGTACTGTGTA |
| | | | | SEQ ID NO:3569 | | SEQ ID NO:11581 | | SEQ ID NO:19593 |
| | | | AA | SGSSSNIGNNYVS | | DSNKRPS | | GTWDSSLSTVV |
| | | | | SEQ ID NO:3570 | | SEQ ID NO:11582 | | SEQ ID NO:19594 |

FIGURE 49
(Continued)

| | | | | | |
|---|---|---|---|---|---|
| iPS:436968 | 21-225_190B10 | NA | TCTGGAAGCAGCTCCAACAT TGGGAATAATTATGTATCC SEQ ID NO:3571 | GACAATAATAAGCGACC CTCA SEQ ID NO:11583 | GGAACATGGGATAGCAGCCT GAGTGCTGGGGTT SEQ ID NO:19595 |
| | | AA | SGSSSNIGNNYVS SEQ ID NO:3572 | DNNKRPS SEQ ID NO:11584 | GTWDSSLSAGV SEQ ID NO:19596 |
| iPS:436970 | 21-225_190B8 | NA | CAAGGAGACACCCTCAGACC CTATTATGTAAGC SEQ ID NO:3573 | GGTAAAAACAACCGGCC CTCA SEQ ID NO:11585 | AACTCCCGGGACAGCAGTGG TAACCATCTGTGGTA SEQ ID NO:19597 |
| | | AA | QGDTLRPYYVS SEQ ID NO:3574 | GKNNRPS SEQ ID NO:11586 | NSRDSSGNHLVV SEQ ID NO:19598 |
| iPS:436972 | 21-225_190C7 | NA | TCTGGAGGCAGCTCCAACAT TGGGAATAATTATGTATCC SEQ ID NO:3575 | GACAATAATAAGCGACC CTCA SEQ ID NO:11587 | GGAACATGGGATCGCACCCT GAGTGATTGGGTA SEQ ID NO:19599 |
| | | AA | SGGSSNIGNNYVS SEQ ID NO:3576 | DNNKRPS SEQ ID NO:11588 | GTWDRTLSDWV SEQ ID NO:19600 |
| iPS:436974 | 21-225_190H7 | NA | TCTGGAAGCAGCTCCAACAT TGGGAGTAATTATGTTTCC SEQ ID NO:3577 | GACAATAATAAGCGACC CTCA SEQ ID NO:11589 | GGAACATGGGATGGCAGACT GAATGTTGGGGTA SEQ ID NO:19601 |
| | | AA | SGSSSNIGSNYVS SEQ ID NO:3578 | DNNKRPS SEQ ID NO:11590 | GTWDGRLNVGV SEQ ID NO:19602 |
| iPS:436976 | 21-225_190D8 | NA | TCTGGAAGCAGCTCCAACAT TGGGAATTCATTATGTCTCC SEQ ID NO:3579 | GACAGTAGTAAGCGACC CTCA SEQ ID NO:11591 | GGAACATGGGATAGTAGTCT GAGTACTGTGGTA SEQ ID NO:19603 |
| | | AA | SGSSSNIGNHYVS SEQ ID NO:3580 | DSSKRPS SEQ ID NO:11592 | GTWDSSLSTVV SEQ ID NO:19604 |
| iPS:436978 | 21-225_190G9 | NA | TCTGGAGATAAATTGGGGGA TAGATTGCTTAC SEQ ID NO:3581 | CAAGATAACAAGCGGCC CTCA SEQ ID NO:11593 | CAGGCGTGGACAGCAGCAC TGTGGTA SEQ ID NO:19605 |

FIGURE 49
(Continued)

| | | | | | | |
|---|---|---|---|---|---|---|
| iPS:436980 | 21-225_190C10 | AA | SGDKLGDRFAY | QDNKRPS | QAWDSSTVV | |
| | | | SEQ ID NO:3582 | SEQ ID NO:11594 | SEQ ID NO:19606 | |
| | | NA | CAAGGAGACAGCCTCAGAC CCTATTATGCAAGC | GGTAAAAACAACCGGCC CTCA | AACTCCCGGGACAGCAGTGG TAACCATCTGTGGTA | |
| | | | SEQ ID NO:3583 | SEQ ID NO:11595 | SEQ ID NO:19607 | |
| iPS:436982 | 21-225_190D10 | AA | QGDSLRPYYAS | GKNNRPS | NSRDSSGNHLVV | |
| | | | SEQ ID NO:3584 | SEQ ID NO:11596 | SEQ ID NO:19608 | |
| | | NA | TCTGGAAGCAGCTCCAACAT TGGGAGTAATTATGTTTCC | GACAATAATAAGCGACC CTCA | GGAACATGGGATAGCAGACT GAATGTTGGGGTA | |
| | | | SEQ ID NO:3585 | SEQ ID NO:11597 | SEQ ID NO:19609 | |
| iPS:436984 | 21-225_190F10 | AA | SGSSSNIGSNYVS | DNNKRPS | GTWDSRLNVGV | |
| | | | SEQ ID NO:3586 | SEQ ID NO:11598 | SEQ ID NO:19610 | |
| | | NA | GTTTTTAGCACTGGAGCAGT CACCAGTGGTTCCTTCCAA AC | AGTACAAGCAACAAACA CTCC | CTGCTCTACTGTGGTGGTGC TCAGCTGGTG | |
| | | | SEQ ID NO:3587 | SEQ ID NO:11599 | SEQ ID NO:19611 | |
| iPS:436986 | 21-225_191A1 | AA | VFSTGAVTSGSFPN | STSNKHS | LLYCGGAQLV | |
| | | | SEQ ID NO:3588 | SEQ ID NO:11600 | SEQ ID NO:19612 | |
| | | NA | TCTGGAAGCAGCTCCAACCT TGGAAATAATTTTGTATCC | GACAATTATAAGCGACC CTCA | GGAACATGGGATAGCAGCCT GAATACTGGGGTA | |
| | | | SEQ ID NO:3589 | SEQ ID NO:11601 | SEQ ID NO:19613 | |
| iPS:436988 | 21-225_191A2 | AA | SGSSSNLGNNFVS | DNYKRPS | GTWDSSLNTGV | |
| | | | SEQ ID NO:3590 | SEQ ID NO:11602 | SEQ ID NO:19614 | |
| | | NA | GTTCTTAGCACTGGAGCAGT CACCAGTGGTTCCTTCCAA AC | AGTACAAGCAACAAACA CTCC | ATGCTCTACTGTGGTGGTGC TCAGCTGGTG | |
| | | | SEQ ID NO:3591 | SEQ ID NO:11603 | SEQ ID NO:19615 | |
| | | AA | VLSTGAVTSGSFPN | STSNKHS | MLYCGGAQLV | |
| | | | SEQ ID NO:3592 | SEQ ID NO:11604 | SEQ ID NO:19616 | |

FIGURE 49
(Continued)

| | | | | |
|---|---|---|---|---|
| iPS:436992 | 21-225_191B8 | NA | CAAGGAGACACCCTCAGACCCTATTATGCAAGT SEQ ID NO:3593 | GGTAAAAACAACCGGCCCTCA SEQ ID NO:11605 | AACTCCCGGGACAGCAGTGGTAACCATCTGTGGTA SEQ ID NO:19617 |
| | | AA | QGDTLRPYYAS SEQ ID NO:3594 | GKNNRPS SEQ ID NO:11606 | NSRDSSGNHLVV SEQ ID NO:19618 |
| iPS:436994 | 21-225_191A9 | NA | CAAGGAGACAGCCTCAGACCCTATTATGCAAGC SEQ ID NO:3595 | GGTAAAAACAACCGGCCCTCA SEQ ID NO:11607 | AACTCCCGGGACAGCAGTGTGGTAACCATCTGTGGTA SEQ ID NO:19619 |
| | | AA | QGDSLRPYYAS SEQ ID NO:3596 | GKNNRPS SEQ ID NO:11608 | NSRDSCGNHLVV SEQ ID NO:19620 |
| iPS:436996 | 21-225_191B9 | NA | TCTGGAAGCAGCTCCAACATCGGGAATAATTATGTATCC SEQ ID NO:3597 | GACAATAAAAAGCGACCCTCA SEQ ID NO:11609 | GGAACATGGATAGCAGCCTGAGTGTTTGTGTC SEQ ID NO:19621 |
| | | AA | SGSSSNIGNNYVS SEQ ID NO:3598 | DNKKRPS SEQ ID NO:11610 | GTWDSSLSVCV SEQ ID NO:19622 |
| iPS:437000 | 21-225_191G9 | NA | ACCTTACGCAGTGGCATCAATGTTGGTACCTACAGGATATAC SEQ ID NO:3599 | TACAAATCAGACTCAGATAAGCAGCAGGGCTCT SEQ ID NO:11611 | ATGATTTGGCACAGCAGCGCTGTGGTA SEQ ID NO:19623 |
| | | AA | TLRSGINVGTYRIY SEQ ID NO:3600 | YKSDSDKQQGS SEQ ID NO:11612 | MIWHSSAVV SEQ ID NO:19624 |
| iPS:437002 | 21-225_191H9 | NA | GCTTCCAGCACTGGAGCAGTCACCAGTGCTTACTATCCAAAC SEQ ID NO:3601 | AGTACAAACAACAAACACTCC SEQ ID NO:11613 | CTGATCTTCTATGGTGGTGTACATGTGATA SEQ ID NO:19625 |
| | | AA | ASSTGAVTSAYYPN SEQ ID NO:3602 | STNNKHS SEQ ID NO:11614 | LIFYGGVHVI SEQ ID NO:19626 |

FIGURE 49
(Continued)

| | | | | | |
|---|---|---|---|---|---|
| iPS:437006 | 21-225_192G2 | NA | TCTGGAAGCAGCTCCAACAT TGGGAATAATTATGTATCC SEQ ID NO:3603 | GACAATAATAAGCGACC CTCA SEQ ID NO:1615 | GGAACATGGGATAGCAGCCT GAGTGCTGGGGTA SEQ ID NO:19627 |
| | | AA | SGSSSNIGNNYVS SEQ ID NO:3604 | DNNKRPS SEQ ID NO:1616 | GTWDSSLSAGV SEQ ID NO:19628 |
| iPS:437008 | 21-225_192E3 | NA | GCTTTCAGCACTGGATCAGT CACCAGTGGTTCCTATCCAA AC SEQ ID NO:3605 | AGTACAAACAACAAACA CTCC SEQ ID NO:1617 | CTGCTATACTATGGTGGTGC TCAGCTGGTG SEQ ID NO:19629 |
| | | AA | AFSTGSVTSGSYPN SEQ ID NO:3606 | STNNKHS SEQ ID NO:1618 | LLYYGGAQLV SEQ ID NO:19630 |
| iPS:437010 | 21-225_192G3 | NA | TCTGGAAGCAGCTCCAACAT CGGAAGTAATACTGTAAAC SEQ ID NO:3607 | GGTAATAAGCAGCGGCC CTCA SEQ ID NO:1619 | GCAGCGTGGGATGACAGCCT GAATGGTTGGGTG SEQ ID NO:19631 |
| | | AA | SGSSSNIGSNTVN SEQ ID NO:3608 | GNKQRPS SEQ ID NO:1620 | AAWDDSLNGWV SEQ ID NO:19632 |
| iPS:437012 | 21-225_192G7 | NA | GCTTCCAGCACTGGAGCAGT CACCAGTGGTAACTATCCAC AG SEQ ID NO:3609 | AGTACAACCAACAGACA TTCC SEQ ID NO:1621 | CTGTTCTACTATGGTGGTGCT CAGGTGATA SEQ ID NO:19633 |
| | | AA | ASSTGAVTSGNYPQ SEQ ID NO:3610 | STTNRHS SEQ ID NO:1622 | LFYYGGAQVI SEQ ID NO:19634 |
| iPS:437014 | 21-225_192H8 | NA | GCTTTCAGCACTGGAACAGT CACCAGTGGTTTCTATCCAA AC SEQ ID NO:3611 | AATACAAGCAACAGACA CTCC SEQ ID NO:1623 | CTGCTGTACTATGGTGGTGC TCAGCTGATG SEQ ID NO:19635 |
| | | AA | AFSTGTVTSGFYPN SEQ ID NO:3612 | NTSNRHS SEQ ID NO:1624 | LLYYGGAQLM SEQ ID NO:19636 |

FIGURE 49
(Continued)

| | | | | | |
|---|---|---|---|---|---|
| iPS:437016 | 21-225_193A6 | NA | CAAGGAGACAGCCTCAGAAGCTATTATGCAAAC | GCTAAGAACAACCGCCCTCA | AATTCCCGGGACAGCAGTGGTAACCATCTGGTA |
| | | | SEQ ID NO:3613 | SEQ ID NO:11625 | SEQ ID NO:19637 |
| | | AA | QGDSLRSYYAN | AKNNRPS | NSRDSSGNHLV |
| | | | SEQ ID NO:3614 | SEQ ID NO:11626 | SEQ ID NO:19638 |
| iPS:437018 | 21-225_193H5 | NA | TCTGGAGATAAATTGGGGGATAGATTTGCTTGC | CAAGATAGCAAGCGGCCCTCA | CAGGCGTGGGACAGCAGCACTGCGGTA |
| | | | SEQ ID NO:3615 | SEQ ID NO:11627 | SEQ ID NO:19639 |
| | | AA | SGDKLGDRFAC | QDSKRPS | QAWDSSTAV |
| | | | SEQ ID NO:3616 | SEQ ID NO:11628 | SEQ ID NO:19640 |
| iPS:437020 | 21-225_193F11 | NA | TTCGGAGGCAGCTCCAACATTGGGAATAATTATGTATCC | GACAATAATAAGCGACCCTCA | GGAACATGGGATCGCACCATGAGTGATTGGGTA |
| | | | SEQ ID NO:3617 | SEQ ID NO:11629 | SEQ ID NO:19641 |
| | | AA | FGGSSNIGNNYVS | DNNKRPS | GTWDRTMSDWV |
| | | | SEQ ID NO:3618 | SEQ ID NO:11630 | SEQ ID NO:19642 |
| iPS:437022 | 21-225_194G5 | NA | GCTTCCAGCACTGGAGCAGTCACCAGTGGTAACTATCCAAC | AGTACAAGCAACAAACACTCC | CTGATCTACTATGGTGGTGCTCAGCTGATG |
| | | | SEQ ID NO:3619 | SEQ ID NO:11631 | SEQ ID NO:19643 |
| | | AA | ASSTGAVTSGNYPN | STSNKHS | LIYYGGAQLM |
| | | | SEQ ID NO:3620 | SEQ ID NO:11632 | SEQ ID NO:19644 |
| iPS:437024 | 21-225_194F11 | NA | TCTGGAAGCAGCTCCAACATTGGGAATAATTATGTATCC | GACAATAATAAGCGACCCTCA | GGAACATGGGATAGCAGCCTGAGTGCTGGGGTT |
| | | | SEQ ID NO:3621 | SEQ ID NO:11633 | SEQ ID NO:19645 |
| | | AA | SGSSSNIGNNYVS | DNNKRPS | GTWDSSLSAGV |
| | | | SEQ ID NO:3622 | SEQ ID NO:11634 | SEQ ID NO:19646 |

FIGURE 49
(Continued)

| | | | | | |
|---|---|---|---|---|---|
| iPS:437026 | 21-225_194D12 | NA | GCTTCCAGCACTGGAGCAGTCACCAGTGGTTCCTTCCAAGC<br>SEQ ID NO:3623 | AGTACAAGCAACAGACACTCC<br>SEQ ID NO:11635 | CTGATCTACTATGGTGGTGCTCAGCTGGCA<br>SEQ ID NO:19647 |
| | | AA | ASSTGAVTSGSFPS<br>SEQ ID NO:3624 | STSNRHS<br>SEQ ID NO:11636 | LIYYGGAQLA<br>SEQ ID NO:19648 |
| iPS:437028 | 21-225_194G12 | NA | TCTGGAAGCAGCTCCAACATTGGGAATAATTATGTATCC<br>SEQ ID NO:3625 | GACAATAATAAGCGACCCTCA<br>SEQ ID NO:11637 | GGAACATGGGATAGCAGCCTGAGTGTTGGGGTA<br>SEQ ID NO:19649 |
| | | AA | SGSSSNIGNNYVS<br>SEQ ID NO:3626 | DNNKRPS<br>SEQ ID NO:11638 | GTWDSSLSVGV<br>SEQ ID NO:19650 |
| iPS:437030 | 21-225_195E3 | NA | TCTGGAGATAAATTGGGGTATAGATCTGTTTGC<br>SEQ ID NO:3627 | GAAGATAGCAAGCGACCCTCA<br>SEQ ID NO:11639 | CAGGCGTGGGACAGTGTCACTGTGGTA<br>SEQ ID NO:19651 |
| | | AA | SGDKLGYRSVC<br>SEQ ID NO:3628 | EDSKRPS<br>SEQ ID NO:11640 | QAWDSVTVV<br>SEQ ID NO:19652 |
| iPS:437032 | 21-225_195H6 | NA | TCTGGAAGCAGCTCCAACATCGGAAGTCATACTGTAAAC<br>SEQ ID NO:3629 | AATAATTATCAGCGGCCCTCA<br>SEQ ID NO:11641 | GCAACATGGGATGACAGCCTGAGTGTTTGGGTG<br>SEQ ID NO:19653 |
| | | AA | SGSSSNIGSHTVN<br>SEQ ID NO:3630 | NNYQRPS<br>SEQ ID NO:11642 | ATWDDSLSVWV<br>SEQ ID NO:19654 |
| iPS:437034 | 21-225_195E9 | NA | TCAGGAGATAAATTGGGGAATAAATATGCTTAC<br>SEQ ID NO:3631 | CAAGATAGGAAGCGGCCCTCA<br>SEQ ID NO:11643 | CAGGCGTGGGACAGAGGAATTGTGGTA<br>SEQ ID NO:19655 |
| | | AA | SGDKLGNKYAY<br>SEQ ID NO:3632 | QDRKRPS<br>SEQ ID NO:11644 | QAWDRGIVV<br>SEQ ID NO:19656 |

FIGURE 49
(Continued)

| | | | | | |
|---|---|---|---|---|---|
| iPS:437036 | 21-225_195H9 | NA | TCTGGAGGCAGCTCCAACAT TGGGAATAATTATGTATCC | GACAATAATAAGCGACC CTCA | GGAACATGGGATCGCACCAT GAGTGATTGGGTA |
| | | | SEQ ID NO:3633 | SEQ ID NO:11645 | SEQ ID NO:19657 |
| | | AA | SGGSSNIGNNYVS | DNNKRPS | GTWDRTMSDWV |
| | | | SEQ ID NO:3634 | SEQ ID NO:11646 | SEQ ID NO:19658 |
| iPS:437040 | 21-225_196E7 | NA | GCTTCCAGCACTGGAGCAGT CACCAGTGCTTACTACCAA AC | AGTACAAACAACAAACA CTCC | CTGATTTCTATGGTGGTGTA CATGTGATA |
| | | | SEQ ID NO:3635 | SEQ ID NO:11647 | SEQ ID NO:19659 |
| | | AA | ASSTGAVTSAYYPN | STNNKHS | LIFYGGVHVI |
| | | | SEQ ID NO:3636 | SEQ ID NO:11648 | SEQ ID NO:19660 |
| iPS:437042 | 21-225_197E8 | NA | TCTGGAAGCAGCTCCAACAT TGGGAATAAATATGTATCC | GACAATAATAAGCGACC CTCA | GGAATATGGGATCGCAGTCT GAGTGTTATGGTG |
| | | | SEQ ID NO:3637 | SEQ ID NO:11649 | SEQ ID NO:19661 |
| | | AA | SGSSSNIGNKYVS | DNNKRPS | GIWDRSLSVMV |
| | | | SEQ ID NO:3638 | SEQ ID NO:11650 | SEQ ID NO:19662 |
| iPS:437044 | 21-225_197F9 | NA | TCTGGAAGCAGCTCCAACAT CGGAAGTAATACTGTAAAC | AGTAATAATCAGCGGCC CTCA | GCAGCATGGAGATGACAGTAT GAATGGTCCGGTG |
| | | | SEQ ID NO:3639 | SEQ ID NO:11651 | SEQ ID NO:19663 |
| | | AA | SGSSSNIGSNTVN | SNNQRPS | AAWDDSMNGPV |
| | | | SEQ ID NO:3640 | SEQ ID NO:11652 | SEQ ID NO:19664 |
| iPS:437048 | 21-225_197B11 | NA | GCTTTCAGCACTGGATCAGT CACCAGTGGTTCCTATCCAA AC | AGTACAAACAACAAACA CTCC | CTGCTCTACTATGGTGGTGC TCAGCTGGTG |
| | | | SEQ ID NO:3641 | SEQ ID NO:11653 | SEQ ID NO:19665 |
| | | AA | AFSTGSVTSGSYPN | STNNKHS | LLYYGGAQLV |
| | | | SEQ ID NO:3642 | SEQ ID NO:11654 | SEQ ID NO:19666 |

FIGURE 49
(Continued)

| | | | | | |
|---|---|---|---|---|---|
| iPS:437050 | 21-225_197C11 | NA | GCTTCCAGCACTGGAGCAGTCACCAGTGCTTACTATCCAAAC<br>SEQ ID NO:3643 | AGTACAAGCAACAAACACTCC<br>SEQ ID NO:11655 | CTGATCTTCTATGGTGGTGTACATGTGATA<br>SEQ ID NO:19667 |
| | | AA | ASSTGAVTSAYYPN<br>SEQ ID NO:3644 | STSNKHS<br>SEQ ID NO:11656 | LIFYGGVHVI<br>SEQ ID NO:19668 |
| iPS:437054 | 21-225_194G3 | NA | TCTGGAAGCAGCTCCAACATCGGGAATAATTATATATCC<br>SEQ ID NO:3645 | GACAATAAAAAGCGACCCTCA<br>SEQ ID NO:11657 | GGAACATGGGATAGCAGCCTGAGTGTTTGTGTC<br>SEQ ID NO:19669 |
| | | AA | SGSSSNIGNNYIS<br>SEQ ID NO:3646 | DNKKRPS<br>SEQ ID NO:11658 | GTWDSSLSVCV<br>SEQ ID NO:19670 |
| iPS:437056 | 21-225_198B8 | NA | GTTCTTAGCACTGGAGCAGTCACCAGTGGTTCCTTCCAAAC<br>SEQ ID NO:3647 | AGTACAAGCAACAAACATTCC<br>SEQ ID NO:11659 | ATGCTTTACAGTGGTGGAGCTCAGATGGTG<br>SEQ ID NO:19671 |
| | | AA | VLSTGAVTSGSFPN<br>SEQ ID NO:3648 | STSNKHS<br>SEQ ID NO:11660 | MLYSGGAQMV<br>SEQ ID NO:19672 |
| iPS:437058 | 21-225_199F3 | NA | TCTGGAAGCAGCTCCAACATTGGGAATAATTATGTATCC<br>SEQ ID NO:3649 | GACAATAATAAGCGCCCTCA<br>SEQ ID NO:11661 | GGAACATGGGATAGCAGCCTGAGTGCTTGTGTC<br>SEQ ID NO:19673 |
| | | AA | SGSSSNIGNNYVS<br>SEQ ID NO:3650 | DNNKRPS<br>SEQ ID NO:11662 | GTWDSSLSACV<br>SEQ ID NO:19674 |
| iPS:437060 | 21-225_198C3 | NA | TCTGGAAGCAGCTCCAACATCGGAAGTAAATACTGTAAAC<br>SEQ ID NO:3651 | AGTAATAATCAGGGCCCTCA<br>SEQ ID NO:11663 | GCAGCATGGGATGACAGCCTGAATGGTCCGGTG<br>SEQ ID NO:19675 |
| | | AA | SGSSSNIGSNTVN<br>SEQ ID NO:3652 | SNNQRPS<br>SEQ ID NO:11664 | AAWDDSLNGPV<br>SEQ ID NO:19676 |

FIGURE 49
(Continued)

| | | | | | |
|---|---|---|---|---|---|
| iPS:437062 | 21-225_200H11 | NA | GCTTCCAACACTGGAGCAGTCACCAGTGGTTCCTATCCAAC | CATACAAACAACAAACACTCC | CTGATCTACTATGGTGGTGCTCAGCTGGTG |
| | | | SEQ ID NO:3653 | SEQ ID NO:11665 | SEQ ID NO:19677 |
| | | AA | ASNIGAVTSGSYPN | HTNNKHS | LIYYGGAQLV |
| | | | SEQ ID NO:3654 | SEQ ID NO:11666 | SEQ ID NO:19678 |
| iPS:437064 | 21-225_200G8 | NA | TCTGGAAGCAGCTCCAACCTTGGAAATAATTTTGTATCC | GACAATTATAAGCGACCCTCA | GGAACTTGGGATAGCAGCCTGAATACTGGGGTA |
| | | | SEQ ID NO:3655 | SEQ ID NO:11667 | SEQ ID NO:19679 |
| | | AA | SGSSSNLGNNFVS | DNYKRPS | GTWDSSLNTGV |
| | | | SEQ ID NO:3656 | SEQ ID NO:11668 | SEQ ID NO:19680 |
| iPS:437066 | 21-225_200G9 | NA | GCTTCCAACACTGGAGCAGTCACCAGTGGTTCCTATCCAAT | CATACAGACAACAAACACTCC | CTGATCTACTATGGTGGTGCTCAGCTGGTG |
| | | | SEQ ID NO:3657 | SEQ ID NO:11669 | SEQ ID NO:19681 |
| | | AA | ASNIGAVTSGSYPN | HTDNKHS | LIYYGGAQLV |
| | | | SEQ ID NO:3658 | SEQ ID NO:11670 | SEQ ID NO:19682 |
| iPS:437068 | 21-225_200A11 | NA | GCTTCCAGCACTGGAGCAGTCACCAGTGGTTACTATCCAAC | AGTACAAACAACAAACACTCC | CTGCTCTATTATGGTGGTGCTCACCTGGCA |
| | | | SEQ ID NO:3659 | SEQ ID NO:11671 | SEQ ID NO:19683 |
| | | AA | ASSTGAVTSGYYPN | STNNKHS | LLYYGGAHLA |
| | | | SEQ ID NO:3660 | SEQ ID NO:11672 | SEQ ID NO:19684 |
| iPS:437070 | 21-225_201G11 | NA | TCTGGAGATAAATTGGGGGATAGATTTGCTTGC | CAAGATAGCAGCGGCCCTCA | CAGGGTGGGACAGCAGCACTGTGGTA |
| | | | SEQ ID NO:3661 | SEQ ID NO:11673 | SEQ ID NO:19685 |
| | | AA | SGDKLGDRFAC | QDSKRPS | QAWDSSTVV |
| | | | SEQ ID NO:3662 | SEQ ID NO:11674 | SEQ ID NO:19686 |

FIGURE 49
(Continued)

| | | | | | | |
|---|---|---|---|---|---|---|
| iPS:437074 | 21-225_203B2 | NA | GGGGGAAACAACATTGGAA GAAAAAATGTGCAC SEQ ID NO:3663 | AGGGATAGGGACCGGCC CTCT SEQ ID NO:11675 | CAGGTGTGGGACAGCGGCAC TGCGGTA SEQ ID NO:19687 |
| | | AA | GGNNIGRKNVH SEQ ID NO:3664 | RDSDRPS SEQ ID NO:11676 | QVWDSGTAV SEQ ID NO:19688 |
| iPS:437076 | 21-225_203G6 | NA | TCTGGAGATAAATTGGGGA TAGATTTGCTTGC SEQ ID NO:3665 | CAAGATAACAAGCGGCC CTCA SEQ ID NO:11677 | CAGGCGTGGGACAGCAGCAC TGTGGTA SEQ ID NO:19689 |
| | | AA | SGDKLGDRFAC SEQ ID NO:3666 | QDNKRPS SEQ ID NO:11678 | QAWDSSTVV SEQ ID NO:19690 |
| iPS:437082 | 21-225_205E12 | NA | GGGGGAAACAACATTGGAA GAAAAAATGTGCAC SEQ ID NO:3667 | AGGGATAGGGACCGGCC CTCT SEQ ID NO:11679 | CAGGTGTGGGACAGCGGCAC TGCGGTA SEQ ID NO:19691 |
| | | AA | GGNNIGRKNVH SEQ ID NO:3668 | RDSDRPS SEQ ID NO:11680 | QVWDSGTAV SEQ ID NO:19692 |
| iPS:437084 | 21-225_206B5 | NA | GGGGGAAACAACATTGGAA GAAAAAATGTGCAC SEQ ID NO:3669 | AGGGATAGTACCGATC TTCT SEQ ID NO:11681 | CAGGATTGGGACAGCAGCAC TGTGGTG SEQ ID NO:19693 |
| | | AA | GGNNIGRKNVH SEQ ID NO:3670 | RDSYRSS SEQ ID NO:11682 | QDWDSSTVV SEQ ID NO:19694 |
| iPS:437086 | 21-225_209A8 | NA | TCTGGAAGCAGCTCCAACAT TGGGAGTAATTTTTTATCC SEQ ID NO:3671 | GACAATAATAAGCGACC CTCA SEQ ID NO:11683 | GGAACATGGATAGCAGCCT GAGTGCTGGGGTA SEQ ID NO:19695 |
| | | AA | SGSSSNIGSNFLS SEQ ID NO:3672 | DNNKRPS SEQ ID NO:11684 | GTWDSSLSAGV SEQ ID NO:19696 |
| iPS:437088 | 21-225_209H10 | NA | GGGGGAAACAACATTGGAA GAAAAAATGTGCAC SEQ ID NO:3673 | AGGGATAGTACCGGTC TTCT SEQ ID NO:11685 | CAGGATTGGGACAGCAGCAC TGTGGTG SEQ ID NO:19697 |
| | | AA | GGNNIGRKNVH SEQ ID NO:3674 | RDSYRSS SEQ ID NO:11686 | QDWDSSTVV SEQ ID NO:19698 |

FIGURE 49
(Continued)

| | | | | | |
|---|---|---|---|---|---|
| iPS:437090 | 21-225_210F11 | NA | GCTTTCAGCACTGGAGCAGTCACCAGTGGTAATTATCCAAAC<br>SEQ ID NO:3675 | AGTACAAGCAACAAACACTCC<br>SEQ ID NO:11687 | CTGCTCTACTACTATGGTGGTGCTCAGCTGGTG<br>SEQ ID NO:19699 |
| | | AA | AFSTGAVTSGNYPN<br>SEQ ID NO:3676 | STSNKHS<br>SEQ ID NO:11688 | LLYYGGAQLV<br>SEQ ID NO:19700 |
| iPS:437092 | 21-225_210B12 | NA | ACTGGAACCAGCAGTGACGTTGGTGGTTATAACTATGTCTCC<br>SEQ ID NO:3677 | GAGGTCAGTAATCGGCCCTCA<br>SEQ ID NO:11689 | AGCTCATATACCAGCAGCCGCACTCTGGTA<br>SEQ ID NO:19701 |
| | | AA | TGTSSDVGGYNYVS<br>SEQ ID NO:3678 | EVSNRPS<br>SEQ ID NO:11690 | SSYTSSRTLV<br>SEQ ID NO:19702 |
| iPS:437094 | 21-225_210D12 | NA | ACTGGAACCAGCAGTGACGTTGGTGGTTATAACTATGTCTCC<br>SEQ ID NO:3679 | GAGGTCAGTAATCGGCCCTCA<br>SEQ ID NO:11691 | AACTCATATACAAGCAGCATCACTTGGGTG<br>SEQ ID NO:19703 |
| | | AA | TGTSSDVGGYNYVS<br>SEQ ID NO:3680 | EVSNRPS<br>SEQ ID NO:11692 | NSYTSSITWV<br>SEQ ID NO:19704 |
| iPS:437096 | 21-225_210E12 | NA | ACTGGAACCAGCAGTGACGTTGGTGGTTATAACTATGTCTCC<br>SEQ ID NO:3681 | GAGGTCAGTAATCGGCCCTCA<br>SEQ ID NO:11693 | GGCTCATATGTAAAAGGCATCACTTGGGTG<br>SEQ ID NO:19705 |
| | | AA | TGTSSDVGGYNYVS<br>SEQ ID NO:3682 | EVSNRPS<br>SEQ ID NO:11694 | GSYVKGITWV<br>SEQ ID NO:19706 |
| iPS:437098 | 21-225_211C1 | NA | ACTGGAACCAGCAGTGACGTTGGTAGTTATAACTATGTCTCC<br>SEQ ID NO:3683 | GAGGTCAGTAATCGGCCCTCA<br>SEQ ID NO:11695 | AACTCATATACAAGCAGCATCACTTGGGTG<br>SEQ ID NO:19707 |
| | | AA | TGTSSDVGSYNYVS<br>SEQ ID NO:3684 | EVSNRPS<br>SEQ ID NO:11696 | NSYTSSITWV<br>SEQ ID NO:19708 |

FIGURE 49
(Continued)

| | | | | | |
|---|---|---|---|---|---|
| iPS:437100 | 21-225_211H2 | NA | GGGGGAAACAACATTGGAC GTAGAAATGTGCAC SEQ ID NO:3685 | AGAGATCGGACCCGCC CTCT SEQ ID NO:11697 | CAGGTGTGGGACAGCAGTAC TGCGGTG SEQ ID NO:19709 |
| | | AA | GGNNIGRRNVH SEQ ID NO:3686 | RDRDRPS SEQ ID NO:11698 | QVWDSSTAV SEQ ID NO:19710 |
| iPS:437102 | 21-225_211E5 | NA | TCTGGAGATGCATTGCCAAA GCAATATGCTTAT SEQ ID NO:3687 | AAAGACAGTGCGAGGCC CTCA SEQ ID NO:11699 | CAATTAGTGTACAGCAGTGA TACTTATGTC SEQ ID NO:19711 |
| | | AA | SGDALPKQYAY SEQ ID NO:3688 | KDSARPS SEQ ID NO:11700 | QLVYSSDTYV SEQ ID NO:19712 |
| iPS:437104 | 21-225_211G5 | NA | ACTGGAACCAGCAGTGACGT TGGTGGTTATAACTATGTCT CC SEQ ID NO:3689 | GAGGTCAGTAATCGGCC CTCA SEQ ID NO:11701 | AACTCATATACAAGAAGCAT CACTTGGGTG SEQ ID NO:19713 |
| | | AA | TGTSSDVGGYNYVS SEQ ID NO:3690 | EVSNRPS SEQ ID NO:11702 | NSYTRSITWV SEQ ID NO:19714 |
| iPS:437106 | 21-225_211H7 | NA | GCTTTCAGCACTGGAGCAGT CACCAGTGGTAACTATCCAA GT SEQ ID NO:3691 | AGTACAAGCAACAACAGACA CTCC SEQ ID NO:11703 | CTGCTCTACTATGGTGGTGC TCAGCTGGTG SEQ ID NO:19715 |
| | | AA | AFSTGAVTSGNYPS SEQ ID NO:3692 | STSNRHS SEQ ID NO:11704 | LLYYGGAQLV SEQ ID NO:19716 |
| iPS:437108 | 21-225_211C9 | NA | GGTTCCAGCACTGGATCAGT CACCAGTGGTTACTTTCCAA AC SEQ ID NO:3693 | AGTACAAACAACAAGCA CTCC SEQ ID NO:11705 | CTGCTCTACTATGTGGTGC TCAGCTGGCA SEQ ID NO:19717 |
| | | AA | GSSTGSVTSGYFPN SEQ ID NO:3694 | STNNKHS SEQ ID NO:11706 | LLYYGGAQLA SEQ ID NO:19718 |

FIGURE 49
(Continued)

| | | | | | |
|---|---|---|---|---|---|
| iPS:437110 | 21-225_211E9 | NA | GCTTCCAGCACTGGAGCAGTCACCAGTGGTAACTATCCAAAC<br>SEQ ID NO:3695 | AGTACAATCAACAAACACTCC<br>SEQ ID NO:11707 | CTGCTCTACTATGGTGGTGCTCAGCTGGCA<br>SEQ ID NO:19719 |
| | | AA | ASSTGAVTSGNYPN<br>SEQ ID NO:3696 | STINKHS<br>SEQ ID NO:11708 | LLYYGGAQLA<br>SEQ ID NO:19720 |
| iPS:437112 | 21-225_212C2 | NA | ACTGGAACCAGCAGTGACGTTGGTGGTTATAACTATGTCTCC<br>SEQ ID NO:3697 | GAGGTCAGTAATCGGCCCTCA<br>SEQ ID NO:11709 | AGCTCATATACACGCAGCATCACTTGGGTG<br>SEQ ID NO:19721 |
| | | AA | TGTSSDVGGYNYVS<br>SEQ ID NO:3698 | EVSNRPS<br>SEQ ID NO:11710 | SSYTRSITWV<br>SEQ ID NO:19722 |
| iPS:437114 | 21-225_212A4 | NA | ACTGGAACCAGCAGTGACGTTGGTGGTTATAACTATGTCTCC<br>SEQ ID NO:3699 | GAGGTCAGTAATCGGCCCTCA<br>SEQ ID NO:11711 | GGCTCATATGTAAAAGGCATCACTTGGGTG<br>SEQ ID NO:19723 |
| | | AA | TGTSSDVGGYNYVS<br>SEQ ID NO:3700 | EVSNRPS<br>SEQ ID NO:11712 | GSYVKGITWV<br>SEQ ID NO:19724 |
| iPS:437116 | 21-225_212F6 | NA | ACTGGAACCAGCAGTGACGTTGGTGGTTATAACTATGTCTCC<br>SEQ ID NO:3701 | GAGGTCAGTAATCGGCCCTCA<br>SEQ ID NO:11713 | AACTCATATACAAGCAGCATCACTTGGGTG<br>SEQ ID NO:19725 |
| | | AA | TGTSSDVGGYNYVS<br>SEQ ID NO:3702 | EVSNRPS<br>SEQ ID NO:11714 | NSYTSSITWV<br>SEQ ID NO:19726 |
| iPS:437118 | 21-225_212G7 | NA | ACTGGAACCAGCAGTGACGTTGGTGGTTATATTATGTCTCC<br>SEQ ID NO:3703 | GAGGTCAGTAATCGGCCCTCA<br>SEQ ID NO:11715 | AACTCATATACAAGCAGCATCACTTGGGTG<br>SEQ ID NO:19727 |
| | | AA | TGTSSDVGGYNYVS<br>SEQ ID NO:3704 | EVSNRPS<br>SEQ ID NO:11716 | NSYTSSITWV<br>SEQ ID NO:19728 |

FIGURE 49
(Continued)

| | | | | | | |
|---|---|---|---|---|---|---|
| iPS:437120 | 21-225_212A9 | NA | GCTTCCAGCACTGGAGCAGT CACCAGTGGTTACTATCCAA AC SEQ ID NO:3705 | AGTACAAACAACAAACA CTCC SEQ ID NO:11717 | CTGCTCTACTATGGTGGTGC TCAGGTGGGA SEQ ID NO:19729 |
| | | AA | ASSTGAVTSGYYPN SEQ ID NO:3706 | STNNKHS SEQ ID NO:11718 | LLYYGGAQVG SEQ ID NO:19730 |
| iPS:437124 | 21-225_212H12 | NA | GCTTCCAGCACTGGAGCAGT CACCAGTGGTTACTATCCAA AC SEQ ID NO:3707 | AGTACAAGCAACAAACA CTCC SEQ ID NO:11719 | CTGCTCTACTATGGTGGTGC TCATGTGGTA SEQ ID NO:19731 |
| | | AA | ASSTGAVTSGYYPN SEQ ID NO:3708 | STSNKHS SEQ ID NO:11720 | LLYYGGAHVV SEQ ID NO:19732 |
| iPS:437128 | 21-225_213G3 | NA | ACTGGAACCAGCAGTGACGT TGGTGGTTATAACTATGTCT CC SEQ ID NO:3709 | GAGGTCAGGAATCGGCC CTCA SEQ ID NO:11721 | AACTCATATACACGCAGCAT CACTTGGGTG SEQ ID NO:19733 |
| | | AA | TGTSSDVGGYNYVS SEQ ID NO:3710 | EVRNRPS SEQ ID NO:11722 | NSYTRSITWV SEQ ID NO:19734 |
| iPS:437130 | 21-225_213D5 | NA | ACTGGAACCAGCAGTGACGT TGGTGGTTATAACTATGTCT CC SEQ ID NO:3711 | GAGGTCCGTAATCGGCC CTCA SEQ ID NO:11723 | TGCTCATATATACAAGAAGAAT CACTTGGGTG SEQ ID NO:19735 |
| | | AA | TGTSSDVGGYNYVS SEQ ID NO:3712 | EVRNRPS SEQ ID NO:11724 | CSYTRRITWV SEQ ID NO:19736 |
| iPS:437132 | 21-225_213F5 | NA | GGTTCCAGCACTGGATCAGT CACCAGTGGTTACTTTCCAA AC SEQ ID NO:3713 | AGTACAAACAACAAGCA CTCC SEQ ID NO:11725 | CTGCTCTACTTTGGTGGTGCT CAGCTGCA SEQ ID NO:19737 |
| | | AA | GSSTGSVTSGYFPN SEQ ID NO:3714 | STNNKHS SEQ ID NO:11726 | LLYFGGAQLA SEQ ID NO:19738 |

FIGURE 49
(Continued)

| | | | | | |
|---|---|---|---|---|---|
| iPS:437134 | 21-225_213A7 | NA | ACTGGAACCAGCAGTGACGT TGGTGGTTATAACTATGTCT CC | GAGGTCAGGAATCGGCC CTCA | AGCTCATATACCAGCAGCCG CACTCTGGTA |
| | | | SEQ ID NO:3715 | SEQ ID NO:11727 | SEQ ID NO:19739 |
| | | AA | TGTSSDVGGYNYVS | EVRNRPS | SSYTSSRTLV |
| | | | SEQ ID NO:3716 | SEQ ID NO:11728 | SEQ ID NO:19740 |
| iPS:437136 | 21-225_214H3 | NA | GCTTCCAGCACTGGAGCAGT CACCAGTGGTTACTATCCAA AC | AGTACAAGCAACAAACA CTCC | CTGCTCTACTATGGTGGTGC TCATGTGGTA |
| | | | SEQ ID NO:3717 | SEQ ID NO:11729 | SEQ ID NO:19741 |
| | | AA | ASSTGAVTSGYYPN | STSNKHS | LLYYGGAHVV |
| | | | SEQ ID NO:3718 | SEQ ID NO:11730 | SEQ ID NO:19742 |
| iPS:437138 | 21-225_214D8 | NA | TCTGGAAGCAGCTCCAACAT TGGGAATAATTATGTATCC | GACAATAATAAGGACC CTCA | GGAGCATGGGATAGCAGCCT GAGTGTCTGTGGTA |
| | | | SEQ ID NO:3719 | SEQ ID NO:11731 | SEQ ID NO:19743 |
| | | AA | SGSSSNIGNNYVS | DNNKRPS | GAWDSSLSAVV |
| | | | SEQ ID NO:3720 | SEQ ID NO:11732 | SEQ ID NO:19744 |
| iPS:437140 | 21-225_214E12 | NA | GCTTCCAGCACTGGAGCAGT CACCAGTGGCTACTATCCAA AC | AGTACAAGCAATAAACA CTCC | CTGCTCTACTGTGATGGTGC CCAGCTGGTG |
| | | | SEQ ID NO:3721 | SEQ ID NO:11733 | SEQ ID NO:19745 |
| | | AA | ASSTGAVTSGYYPN | STSNKHS | LLYCDGAQLV |
| | | | SEQ ID NO:3722 | SEQ ID NO:11734 | SEQ ID NO:19746 |
| iPS:437142 | 21-225_215A3 | NA | GCTTCCAGCACTGAAGCCGT CACCAGTGGTAACTATCCAA GC | AGTACAAGCAACAAACA CTCC | CTGCTCTACTATGGTGGCGC TCAGCTGGCA |
| | | | SEQ ID NO:3723 | SEQ ID NO:11735 | SEQ ID NO:19747 |
| | | AA | ASSTEAVTSGNYPS | STSNKHS | LLYYGGAQLA |
| | | | SEQ ID NO:3724 | SEQ ID NO:11736 | SEQ ID NO:19748 |

FIGURE 49
(Continued)

| | | | | | |
|---|---|---|---|---|---|
| iPS:437144 | 21-225_215B3 | NA | TCTGGAGATAAATTGGGGA TAAATTTGCTTGC SEQ ID NO:3725 | CAAGATAGCAAGCGGCC CTCA SEQ ID NO:11737 | CAGGGGTGGGACAGCAGCAC TGTGGTA SEQ ID NO:19749 |
| | | AA | SGDKLGDKFAC SEQ ID NO:3726 | QDSKRPS SEQ ID NO:11738 | QAWDSSTVV SEQ ID NO:19750 |
| iPS:437146 | 21-225_215D3 | NA | ACTGGAACCAGCAGTGACAT TGGTGGTTATAACTATGTCT CC SEQ ID NO:3727 | GAGGTCAGTAATCGGCC CTCA SEQ ID NO:11739 | AACTCATATAAAAGGGGCAG CACTTGGGTG SEQ ID NO:19751 |
| | | AA | TGTSSDIGGYNYVS SEQ ID NO:3728 | EVSNRPS SEQ ID NO:11740 | NSYKRGSTWV SEQ ID NO:19752 |
| iPS:437148 | 21-225_215H3 | NA | GCTTCCAGCACTGGAGCAGT CACCAGTGGTTACTATCCAA AC SEQ ID NO:3729 | AGTACAAACAACAAACA CTCC SEQ ID NO:11741 | CTGCTCTACTATGGTGGTGC TCAGGTGGGA SEQ ID NO:19753 |
| | | AA | ASSTGAVTSGYYPN SEQ ID NO:3730 | STNNKHS SEQ ID NO:11742 | LLYYGGAQVG SEQ ID NO:19754 |
| iPS:437150 | 21-225_216A3 | NA | ACTGGAACCAGCAGTGACGT TGGTGGTTATAATTATGTCT CC SEQ ID NO:3731 | GAGGTCAGTAATCGGCC CTCA SEQ ID NO:11743 | AACTCATATACAAGCAGCAT CACTTGGGTG SEQ ID NO:19755 |
| | | AA | TGTSSDVGGYNYVS SEQ ID NO:3732 | EVSNRPS SEQ ID NO:11744 | NSYTSSITWV SEQ ID NO:19756 |
| iPS:437154 | 21-225_216A7 | NA | GCTTCCAGCACTGGAGCAGT CACCAGTGGTTACTATCCAA AC SEQ ID NO:3733 | AGTACAAACAACAAACA CTCC SEQ ID NO:11745 | CTGCTCTACTATGGTGGTGC TCAGGTGGGA SEQ ID NO:19757 |
| | | AA | ASSTGAVTSGYYPN SEQ ID NO:3734 | STNNKHS SEQ ID NO:11746 | LLYYGGAQVG SEQ ID NO:19758 |

FIGURE 49
(Continued)

| | | | | | |
|---|---|---|---|---|---|
| iPS:437158 | 21-225_216H11 | NA | GCTTCCAGCACTGGAGCAGT CACCAGTGGCTACTATCCAA AC | AGTACAAGCAATAAACA CTCC | CTGCTCTACTGTGATGGTGC TCAGCTGGTG |
| | | | SEQ ID NO:3735 | SEQ ID NO:11747 | SEQ ID NO:19759 |
| | | AA | ASSTGAVTSGYYPN | STSNKHS | LLYCDGAQLV |
| | | | SEQ ID NO:3736 | SEQ ID NO:11748 | SEQ ID NO:19760 |
| iPS:437160 | 21-225_216B12 | NA | GGGGGAGACAACATTAGAA GAAGAAATGTGCAC | AGGGATAGCAACCGGCC CTCT | CAGGTGTGGGACAGCAGCAC TGGGGTG |
| | | | SEQ ID NO:3737 | SEQ ID NO:11749 | SEQ ID NO:19761 |
| | | AA | GGDNIRRRNVH | RDSNRPS | QVWDSSTGV |
| | | | SEQ ID NO:3738 | SEQ ID NO:11750 | SEQ ID NO:19762 |
| iPS:437162 | 21-225_217B2 | NA | ACTGGAACCAGCAGTGACGT TGGTGGTTATAACTATGTCT CC | GAGGTCAGTAATCGGCC CTCA | GGCTCATATGTAAAAGGCAT CACTTGGGTG |
| | | | SEQ ID NO:3739 | SEQ ID NO:11751 | SEQ ID NO:19763 |
| | | AA | TGTSSDVGGYNYVS | EVSNRPS | GSYVKGITWV |
| | | | SEQ ID NO:3740 | SEQ ID NO:11752 | SEQ ID NO:19764 |
| iPS:437164 | 21-225_217C6 | NA | TCTGGAGATGCATTGCCAAA GCAATATGCTTAT | AAAGACAGTGAGAGGCC CTCA | CAATTAATAGTCAGCAGTGA TACTTATGTC |
| | | | SEQ ID NO:3741 | SEQ ID NO:11753 | SEQ ID NO:19765 |
| | | AA | SGDALPKQYAY | KDSERPS | QLIVSSDTYV |
| | | | SEQ ID NO:3742 | SEQ ID NO:11754 | SEQ ID NO:19766 |
| iPS:437166 | 21-225_217G11 | NA | TCTGGAGATGCATTGCCAAA ACAATATGCTTAT | AAAGACAGTGAGAGGCC CTCA | CAATTAGTGTACAGCAGTGA TACTTATGTC |
| | | | SEQ ID NO:3743 | SEQ ID NO:11755 | SEQ ID NO:19767 |
| | | AA | SGDALPKQYAY | KDSERPS | QLVYSSDTYV |
| | | | SEQ ID NO:3744 | SEQ ID NO:11756 | SEQ ID NO:19768 |
| iPS:437168 | 21-225_218G4 | NA | TCTGGAAGCAGCTCAACAT TGGGAATAATTATGTATCC | GACAGTAATAAGCGACC CTCA | GGAACATGGGATAGCAGCCT GAATACTGTGGTA |

FIGURE 49
(Continued)

| | | | | | | |
|---|---|---|---|---|---|---|
| iPS:437170 | 21-225_218G4 | AA | SEQ ID NO:3745 SGSSSNIGNYVS | SEQ ID NO:11757 DSNKRPS | SEQ ID NO:19769 GTWDSSLNTVV | |
| iPS:437172 | 21-225_218E5 | NA | SEQ ID NO:3746 TCTAGAGATGTATTGCCGAA GCAATATGCTTAT | SEQ ID NO:11758 AAAGACAGTGAGAGGCC CTCA | SEQ ID NO:19770 CAATTAGTTGTCAGCAGTGA TACTTATGTC | |
| | | AA | SEQ ID NO:3747 SRDVLPKQYAY | SEQ ID NO:11759 KDSERPS | SEQ ID NO:19771 QLVVSSDTYV | |
| iPS:437172 | 21-225_219A7 | NA | SEQ ID NO:3748 ACTGGAACCAGCAGTGACGT TGGTGGTTATAATTATGTCT CC | SEQ ID NO:11760 GAGGTCAGGAAATCGGCC CTCA | SEQ ID NO:19772 TGCTCATATACAAGGAGCAT CACTTGGGTG | |
| | | AA | SEQ ID NO:3749 TGTSSDVGGYNYVS | SEQ ID NO:11761 EVRNRPS | SEQ ID NO:19773 CSYTRSITWV | |
| iPS:437182 | 21-225_221H2 | NA | SEQ ID NO:3750 ACTGGAACCAGCAGTGACGT TGGTGGTTATAACTATGTCT CC | SEQ ID NO:11762 GAGGTCAGGAATCGGCC CTCA | SEQ ID NO:19774 AACTCATATACACGCAGCAT CACTTGGGTG | |
| | | AA | SEQ ID NO:3751 TGTSSDVGGYNYVS | SEQ ID NO:11763 EVRNRPS | SEQ ID NO:19775 NSYTRSITWV | |
| iPS:437184 | 21-225_221G4 | NA | SEQ ID NO:3752 ACTGGAACCAGCAGTGACGT TGGTGGTTATAACTATGTCT CC | SEQ ID NO:11764 GAGGTCAGGAATCGGCC CTCA | SEQ ID NO:19776 AACTCATATACACGCAGCAT CACTTGGGTG | |
| | | AA | SEQ ID NO:3753 TGTSSDVGGYNYVS | SEQ ID NO:11765 EVRNRPS | SEQ ID NO:19777 NSYTRSITWV | |
| iPS:437186 | 21-225_224H2 | NA | SEQ ID NO:3754 TCTGGAGATAATTTGGGGGT TAAATATACTTAC | SEQ ID NO:11766 CAAGATAGCAAGCGGCC CTCA | SEQ ID NO:19778 CAGGCGTGGACAGCAGCAC TGTGGTA | |
| | | AA | SEQ ID NO:3755 SGDNLGVKYTY | SEQ ID NO:11767 QDSKRPS | SEQ ID NO:19779 QAWDSSTVV | |

FIGURE 49
(Continued)

| iPS: | | | | | |
|---|---|---|---|---|---|
| iPS:437188 | 21-225_224B11 | NA | SEQ ID NO:3756 ACTGGGAGCAGCTCCAACAT CGGGGCAGGTTATGATGTAC AC | SEQ ID NO:11768 GGTAACAGCAGCAATCGGCC CTCA | SEQ ID NO:19780 CAGTCCTATGACAACAGCCT GAGTGGTGTG |
| | | AA | SEQ ID NO:3757 TGSSSNIGAGYDVH | SEQ ID NO:11769 GNSNRPS | SEQ ID NO:19781 QSYDNSLSGV |
| iPS:437190 | 21-225_225A9 | NA | SEQ ID NO:3758 TCTGGAGATAAATTGGGGAA TAAATATGCTGC | SEQ ID NO:11770 CAAGATAGCAAGCGGCC CTCA | SEQ ID NO:19782 CAGGCGTGGGACAGCAACAC TGCATGTGTC |
| | | AA | SEQ ID NO:3759 SGDKLGNKYAC | SEQ ID NO:11771 QDSKRPS | SEQ ID NO:19783 QAWDSNTACV |
| iPS:437192 | 21-225_225E9 | NA | SEQ ID NO:3760 TCTGGAGATAATTTGGGGAA TAGATATGCTGC | SEQ ID NO:11772 CAAGATCGCAAGCGGCC CTCA | SEQ ID NO:19784 CAGGCGTGGGACAGCAGAAC TGCTGTGGTA |
| | | AA | SEQ ID NO:3761 SGDNLGNRYAC | SEQ ID NO:11773 QDRKRPS | SEQ ID NO:19785 QAWDSRTAVV |
| iPS:437194 | 21-225_226B2 | NA | SEQ ID NO:3762 TCTGGAGATACATTGGGGGG TAAATATGCTGG | SEQ ID NO:11774 CAAGATCGCAAGCGGCC CTCA | SEQ ID NO:19786 CAGGCGTGGGACAACGGCGC TGCGGTT |
| | | AA | SEQ ID NO:3763 SGDTLGGKYAW | SEQ ID NO:11775 QDRKRPS | SEQ ID NO:19787 QAWDNGAAV |
| iPS:437196 | 21-225_226B7 | NA | SEQ ID NO:3764 TCTGGAGATGCATTGCCAAG GCATTATGTTTAT | SEQ ID NO:11776 AAAGACAGTGAGAGGCC CTCA | SEQ ID NO:19788 CAATCAGCAGACAGCAGTGG TACTTATGTC |
| | | AA | SEQ ID NO:3765 SGDALPRHYVY | SEQ ID NO:11777 KDSERPS | SEQ ID NO:19789 QSADSSGTYV |
| iPS:437198 | 21_225_226F8 | NA | SEQ ID NO:3766 ACTGGGAGCAGCTCCAACAT CGGGGCAGGTTATGATGTAC AC | SEQ ID NO:11778 GGTAACAGCAATCGGCC CTCA | SEQ ID NO:19790 CAGTCCTATGACAACAGCCT GAGTGGTGTG |

FIGURE 49
(Continued)

| | | | | | | |
|---|---|---|---|---|---|---|
| iPS:437200 | 21-225_226F8 | AA | SEQ ID NO:3767 TGSSSNIGAGYDVH | SEQ ID NO:11779 GNSNRPS | SEQ ID NO:19791 QSYDNSLSGV | |
| iPS:437202 | 21-225_226A10 | NA | SEQ ID NO:3768 TCTGGAGATACATTGGGGGG TAAATATGCTTGG | SEQ ID NO:11780 CAAGATCGCAAGCGGCC CTCA | SEQ ID NO:19792 CAGGCGTGGACAACGGCGC TGCGGTT | |
| | | AA | SEQ ID NO:3769 SGDTLGGKYAW | SEQ ID NO:11781 QDRKRPS | SEQ ID NO:19793 QAWDNGAAV | |
| iPS:437204 | 21-225_227D3 | NA | SEQ ID NO:3770 ACTGGGAGCAGCTCCAACAT CGGGGCAGGTTATGATGTAC AC | SEQ ID NO:11782 GGTAACAGCAATCGGCC CTCA | SEQ ID NO:19794 CAGTCCTATGACAACAGCCT GAGTGGTGTG | |
| | | AA | SEQ ID NO:3771 TGSSSNIGAGYDVH | SEQ ID NO:11783 GNSNRPS | SEQ ID NO:19795 QSYDNSLSGV | |
| iPS:437206 | 21-225_227E5 | NA | SEQ ID NO:3772 TCTGGAGATAAATTGGGGGA AAAATATGCTTGC | SEQ ID NO:11784 CAAGATAGGAAGCGGCC CTCA | SEQ ID NO:19796 CAGGCGTGGGTCAACAACAC TATGATA | |
| | | AA | SEQ ID NO:3773 SGDKLGEKYAC | SEQ ID NO:11785 QDRKRPS | SEQ ID NO:19797 QAWVNNTMI | |
| iPS:437208 | 21-225_227C10 | NA | SEQ ID NO:3774 ACTGGGAGCAGCTCCAACAT CGGGGCAGGTTATGATGTAC AC | SEQ ID NO:11786 GGTAACAGCAATCGGCC CTCA | SEQ ID NO:19798 CAGTCCTATGACAACAACCT GAGTGGTGTG | |
| | | AA | SEQ ID NO:3775 TGSSSNIGAGYDVH | SEQ ID NO:11787 GNSNRPS | SEQ ID NO:19799 QSYDNNLSGV | |
| iPS:437210 | 21-225_227E12 | NA | SEQ ID NO:3776 TCTGGAGATAAATTGGGGGA TAAATATGTTTGT | SEQ ID NO:11788 CAAGATAGCAAGCGGCC CTCA | SEQ ID NO:19800 CAGGCGTGGAACAGCAGCAA TGTGGTA | |
| | | AA | SEQ ID NO:3777 SGDKLGDKYVC | SEQ ID NO:11789 QDSKRPS | SEQ ID NO:19801 QAWNSSNVV | |
| | | | SEQ ID NO:3778 | SEQ ID NO:11790 | SEQ ID NO:19802 | |

FIGURE 49
(Continued)

| | | | | | |
|---|---|---|---|---|---|
| iPS:437214 | 21-225_48B12 | NA | TCTGGAGATGCATTGCCAAA AAATATGCTTAT SEQ ID NO:3779 | GAGGACAGCAAAACGACC CTCC SEQ ID NO:11791 | AACTCAACAGACAGCAGTGG TAATCATGTGGTA SEQ ID NO:19803 |
| | | AA | SGDALPKYAY SEQ ID NO:3780 | EDSKRPS SEQ ID NO:11792 | NSTDSSGNHVV SEQ ID NO:19804 |
| iPS:437216 | 21-225_51D5 | NA | CGGGCAGTCAGGGCATTAA CAATTATTAGCC SEQ ID NO:3781 | GCTGCATCCAGTTTGCGA AGT SEQ ID NO:11793 | CAACAGTATTATAGTTACCC ATTCACT SEQ ID NO:19805 |
| | | AA | RASQGINNYLA SEQ ID NO:3782 | AASSLRS SEQ ID NO:11794 | QQYYSYPFT SEQ ID NO:19806 |
| iPS:437220 | 21-225_55H6 | NA | CGGGCAAGTCAGGGCATTAG AAACGATTTAGCC SEQ ID NO:3783 | GGTGCATCCAGTTTGCA AAGT SEQ ID NO:11795 | CTACAGGTGATAGTTACCC GTTCACT SEQ ID NO:19807 |
| | | AA | RASQGIRNDLG SEQ ID NO:3784 | GASSLQS SEQ ID NO:11796 | LQRDSYPFT SEQ ID NO:19808 |
| iPS:437224 | 21-225_56H1 | NA | CGGGCGAGTCAGGGCATTAG CCATTATTTAGCC SEQ ID NO:3785 | GCTGCATCCGGTTTGCAA AGT SEQ ID NO:11797 | CAACAATATCAGAATTACCC CTTCACT SEQ ID NO:19809 |
| | | AA | RASQGISHYLA SEQ ID NO:3786 | AASGLQS SEQ ID NO:11798 | QQYQNYPFT SEQ ID NO:19810 |
| iPS:437226 | 21-225_57C2 | NA | AGGTCTAGTCAAAGCCTCGT ATACAGTGATGGAAACACCT ACTTGAAT SEQ ID NO:3787 | GAGGTTTCTAACTGGGA CTCT SEQ ID NO:11799 | GTGCAAGGTACACACTGGCC TCGGACG SEQ ID NO:19811 |
| | | AA | RSSQSLVYSDGNTYLN SEQ ID NO:3788 | EVSNWDS SEQ ID NO:11800 | VQGTHWPRT SEQ ID NO:19812 |
| iPS:437228 | 21-225_60C11 | NA | AGGGCCAGTCAGAGTGTTAG CAACGACTTAGCC SEQ ID NO:3789 | GGTGCATCCACCAGGGC CACT SEQ ID NO:11801 | CAGCAGTATAGTAACTGGCC ATTCACT SEQ ID NO:19813 |
| | | AA | RASQSVSNDLA | GASTRAT | QQYSNWPFT |

FIGURE 49
(Continued)

| iPS | clone | type | | | |
|---|---|---|---|---|---|
| iPS:437230 | 21-225_62H10 | NA | SEQ ID NO:3790 CGGGCAAGTCAGAGCATTAC CAGCTATTTAAAT | SEQ ID NO:11802 ACTGCATCCAGTTGCAA AGT | SEQ ID NO:19814 CAACAGAGTCACAGTTCCC ATTCACT |
| | | AA | SEQ ID NO:3791 RASQSITSYLN | SEQ ID NO:11803 TASSLQS | SEQ ID NO:19815 QQSHSFPFT |
| iPS:437232 | 21-225_63E1 | NA | SEQ ID NO:3792 CGTGCGAGTCAGGGTATTAG CAGCTACTTAGCC | SEQ ID NO:11804 GCTGCATCCAGTTGCAA AGT | SEQ ID NO:19816 CAACAGGCTAACAGTTTCCC GCTCACT |
| | | AA | SEQ ID NO:3793 RASQGISSYLA | SEQ ID NO:11805 AASSLQS | SEQ ID NO:19817 QQANSFPLT |
| iPS:437234 | 21-225_64E2 | NA | SEQ ID NO:3794 CGGGCGAGTCAGGGTATTAG CAGGTGGTTAGCC | SEQ ID NO:11806 GCTGCATCCAGTTGCAA AGT | SEQ ID NO:19818 CAACAGGCTAACAGTTTCCC ATTCACT |
| | | AA | SEQ ID NO:3795 RASQGISRWLA | SEQ ID NO:11807 AASSLQS | SEQ ID NO:19819 QQANSFPFT |
| iPS:437248 | 21-225_97H3 | NA | SEQ ID NO:3796 AGGTCTAGTCAGAGCCTCCT GCATAGTAATGGAACACAACT TGGAT | SEQ ID NO:11808 TTGGGTTCTAATCGGGCC TCC | SEQ ID NO:19820 ATGCAACCTCTACAAACTCC GTTCACT |
| | | AA | SEQ ID NO:3797 RSSQSLLHSNGHNYLD | SEQ ID NO:11809 LGSNRAS | SEQ ID NO:19821 MQPLQTPFT |
| iPS:437250 | 21-225_148C6 | NA | SEQ ID NO:3798 AGGTCTAGTCAAAGCCTCGT ATACAGTGATGGAAACACCT ACTGAAT | SEQ ID NO:11810 AAGGTTCTAACTGGGA CTCT | SEQ ID NO:19822 ATGCAAGGTACACACTGGTC GCTCACT |
| | | AA | SEQ ID NO:3799 RSSQSLVYSDGNTYLN | SEQ ID NO:11811 KVSNWDS | SEQ ID NO:19823 MQGTHWSLT |
| | | | SEQ ID NO:3800 | SEQ ID NO:11812 | SEQ ID NO:19824 |

FIGURE 49
(Continued)

| | | | | | |
|---|---|---|---|---|---|
| iPS:437252 | 21-225_148H11 | NA | AGGTCTAGTCAAAGCCTCGTATACAGTGATGGAAACACCTACTTGAAT<br>SEQ ID NO:3801 | AAGGTTTCTAACTGGGACTCT<br>SEQ ID NO:11813 | ATGCAAGGTACACACTGGTTGCTCACT<br>SEQ ID NO:19825 |
| | | AA | RSSQSLVYSDGNTYLN<br>SEQ ID NO:3802 | KVSNWDS<br>SEQ ID NO:11814 | MQGTHWLLT<br>SEQ ID NO:19826 |
| iPS:437254 | 21-225_149F2 | NA | AGGTCTAGTCAAAGCCTCGTATACAGTGATGGAAACACCTCCTTGAAT<br>SEQ ID NO:3803 | AAGGTTTCTAACTGGGACTCT<br>SEQ ID NO:11815 | ATGCAAGGTACACACTGGCCTCCCACT<br>SEQ ID NO:19827 |
| | | AA | RSSQSLVYSDGNTSLN<br>SEQ ID NO:3804 | KVSNWDS<br>SEQ ID NO:11816 | MQGTHWPPT<br>SEQ ID NO:19828 |
| iPS:437256 | 21-225_150F11 | NA | AGGTCTAGTCAAAGCCTCGTATACAGTGATGGAAACACCTCCTTGAAT<br>SEQ ID NO:3805 | AAGGTTTCTAACTGGGACTAT<br>SEQ ID NO:11817 | ATGCAAGGTACACACTGGCCTCCCACT<br>SEQ ID NO:19829 |
| | | AA | RSSQSLVYSDGNTSLN<br>SEQ ID NO:3806 | KVSNWDY<br>SEQ ID NO:11818 | MQGTHWPPT<br>SEQ ID NO:19830 |
| iPS:437258 | 21-225_153F9 | NA | CGGGCGAGTCAGGGCATTAGCAATTATTTAGCC<br>SEQ ID NO:3807 | GCTGCATCCAGTTGCAAAGT<br>SEQ ID NO:11819 | CAACAGTATAATAGTTACCCGCTCAGT<br>SEQ ID NO:19831 |
| | | AA | RASQGISNYLA<br>SEQ ID NO:3808 | AASSLQS<br>SEQ ID NO:11820 | QQYNSYPLS<br>SEQ ID NO:19832 |
| iPS:437260 | 21-225_170D1 | NA | CGGGCGAGTCAGGACATTAGCAATTATTTAGCC<br>SEQ ID NO:3809 | GCTGCATCCAGTTGCAAAGT<br>SEQ ID NO:11821 | CAACAGTGATAGTTTCCCTCTCACT<br>SEQ ID NO:19833 |
| | | AA | RASQDISNYLA<br>SEQ ID NO:3810 | AASSLQS<br>SEQ ID NO:11822 | QQCDSFPLT<br>SEQ ID NO:19834 |
| iPS:437262 | | NA | CGGGCAAGTCAGGGCATTAGGAAATGATTTAGGC | GTTGCATCCGGTTTGCAAAGT | CTACAGCACAATAGTTACCCTCCGTGGACG |

FIGURE 49
(Continued)

| | | | | | | | |
|---|---|---|---|---|---|---|---|
| iPS:437264 | 21-225_170E4 | AA | SEQ ID NO:3811 RASQGIRNDLG | SEQ ID NO:3812 | SEQ ID NO:11823 VASGLQS | SEQ ID NO:11824 | SEQ ID NO:19835 LQHNSYPPWT | SEQ ID NO:19836 |
| iPS:437266 | 21-225_171H12 | NA | CGGGCGAGTCAGGACATTAG CAATTATTAGCC | SEQ ID NO:3813 | TCTGCATCCAGTTGCAA AGT | SEQ ID NO:11825 | CAACAATCTGATAGTTACCC TCTCACT | SEQ ID NO:19837 |
| | | AA | RASQDISNYLA | SEQ ID NO:3814 | SASSLQS | SEQ ID NO:11826 | QQSDSYPLT | SEQ ID NO:19838 |
| iPS:437268 | 21-225_177A5 | NA | CGGGCGAGTCAGGACATTAG CAATTATTAGCC | SEQ ID NO:3815 | TCTGCATCCAGTTGCAA AGT | SEQ ID NO:11827 | CAACAATCTGATAGTTACCC TCTCACT | SEQ ID NO:19839 |
| | | AA | RASQDISNYLA | SEQ ID NO:3816 | SASSLQS | SEQ ID NO:11828 | QQSDSYPLT | SEQ ID NO:19840 |
| iPS:437270 | 21-225_177D2 | NA | AGGTCTAGTCAAAGCCTCGT ATACAGTGATGGAAACACCT ACTTGAAT | SEQ ID NO:3817 | AAGGTTTCTAACTGGGA CTCT | SEQ ID NO:11829 | ATGCAAGGTACACACTGGCC TCTCACT | SEQ ID NO:19841 |
| | | AA | RSSQSLVYSDGNTYLN | SEQ ID NO:3818 | KVSNWDS | SEQ ID NO:11830 | MQGTHWPLT | SEQ ID NO:19842 |
| iPS:437272 | 21-225_178H4 | NA | CGGGCGAGTCAGGACATTAG CAATTATTAGCC | SEQ ID NO:3819 | TCTGCATCCAGTTGCAA AGT | SEQ ID NO:11831 | CAACAATCTAATAGTTACCC TCTCACT | SEQ ID NO:19843 |
| | | AA | RASQDISNYLA | SEQ ID NO:3820 | SASSLQS | SEQ ID NO:11832 | QQSNSYPLT | SEQ ID NO:19844 |
| iPS:437274 | 21-225_196D4 | NA | CGGGCGAGTCAGGACATTAG CAATTATTAGCC | SEQ ID NO:3821 | GCTGCATCCAGTTGCAA AGT | SEQ ID NO:11833 | CAACATTATCTTAATTACCCT CTCACC | SEQ ID NO:19845 |
| | | AA | RASQGISNYLA | SEQ ID NO:3822 | AASSLQS | SEQ ID NO:11834 | QHYLNYPLT | SEQ ID NO:19846 |

FIGURE 49
(Continued)

| | | | | | |
|---|---|---|---|---|---|
| iPS:437280 | 21-225_203C10 | NA | CGGGCAAGTCAGGACATTAG AAATGATTAGGC SEQ ID NO:3823 | AGAGCATCCAGTTTGCA AGT SEQ ID NO:11835 | CTACAGCATAATAGTTACCC GTGGACG SEQ ID NO:19847 |
| | | AA | RASQDIRNDLG SEQ ID NO:3824 | RASSLQS SEQ ID NO:11836 | LQHNSYPWT SEQ ID NO:19848 |
| iPS:437282 | 21-225_207C9 | NA | CGGGCAAGTCAGAGGGTTTAG TAACTATTTAAAT SEQ ID NO:3825 | ACTGCATCCAGTTTGCAA AGT SEQ ID NO:11837 | CAACAGAGTTACAGTATTCC GCTCACT SEQ ID NO:19849 |
| | | AA | RASQRFSNYLN SEQ ID NO:3826 | TASSLQS SEQ ID NO:11838 | QQSYSIPLT SEQ ID NO:19850 |
| iPS:437286 | 21-225_208F1 | NA | CGGGCAAGTCAGGGCATTAG ACATGATTTAGGC SEQ ID NO:3827 | GCTGCATCCAGTTTGCAA AGT SEQ ID NO:11839 | CTACAGCATTATAGTTTCCT CGGACG SEQ ID NO:19851 |
| | | AA | RASQGIRHDLG SEQ ID NO:3828 | AASSLQS SEQ ID NO:11840 | LQHYSFPRT SEQ ID NO:19852 |
| iPS:437290 | 21-225_210G6 | NA | CGGGCAAGTCAGGGCATTAG ACATGATTTAGGC SEQ ID NO:3829 | GCTGCATCCAGTTCGCA AAGT SEQ ID NO:11841 | GTACAGCATTATAGTTTCCC TCGGACG SEQ ID NO:19853 |
| | | AA | RASQGIRHDLG SEQ ID NO:3830 | AASSSQS SEQ ID NO:11842 | VQHYSFPRT SEQ ID NO:19854 |
| iPS:437294 | 21-225_216D5 | NA | AGGTCTAGTCAAAGCCTCGT ATACAGTGATGGAAACACCT ACTTGAAT SEQ ID NO:3831 | AAGGTTTCTAACTGGGA CTCT SEQ ID NO:11843 | ATGCAAGGTGCACACTGGTT CACC SEQ ID NO:19855 |
| | | AA | RSSQSLVYSDGNTYLN SEQ ID NO:3832 | KVSNWDS SEQ ID NO:11844 | MQGAHWFT SEQ ID NO:19856 |
| iPS:437302 | 21-225_225B11 | NA | CAGGCGAGTCAGGACATTTT CAACTATTTAAAT SEQ ID NO:3833 | GATGCATCCACTTTGGA AACA SEQ ID NO:11845 | CAACAGTATGATAATCTCCC GATCACC SEQ ID NO:19857 |
| | | AA | QASQDIFNYLN | DASTLET | QQYDNLPIT |

FIGURE 49
(Continued)

| | | | | | | |
|---|---|---|---|---|---|---|
| iPS:437320 | 21-225_75A1 | NA | SEQ ID NO:3834 AGGTCTAGTCAGAGCCTCCTGCATAGTAATGGACACAACTTATTTGGAT | SEQ ID NO:11846 TTGGGTTCTAATCGGGCCTCC | SEQ ID NO:19858 ATGCAACCTCTACAAACTCCGTTCACT |
| | | AA | SEQ ID NO:3835 RSSQSLLHSNGHNYLD | SEQ ID NO:11847 LGSNRAS | SEQ ID NO:19859 MQPLQTPFT |
| iPS:437322 | 21-225_75B1 | NA | SEQ ID NO:3836 AGGGCCAGTCAGAGTGTTAGCAGCAGCTACTTAGTC | SEQ ID NO:11848 GGTGCATCCACCAGGGCCACT | SEQ ID NO:19860 CAGCAGTATGGTTGCTCACCGCTCACT |
| | | AA | SEQ ID NO:3837 RASQSVSSSYLV | SEQ ID NO:11849 GASTRAT | SEQ ID NO:19861 QQYGCSPLT |
| iPS:437324 | 21-225_75C2 | NA | SEQ ID NO:3838 AGGGCCAGTCAGAGTGTTTACAGCAGCTACTTAGCC | SEQ ID NO:11850 GGTGCATCCAGCCGGGCCACT | SEQ ID NO:19862 CAGCACTATGATAACTCACCGTGGACG |
| | | AA | SEQ ID NO:3839 RASQSVYSSYLA | SEQ ID NO:11851 GASSRAT | SEQ ID NO:19863 QHYDNSPWT |
| iPS:437326 | 21-225_75C10 | NA | SEQ ID NO:3840 CGGGCGAGTCAGGGCATTAGCATCTGGTTAGCC | SEQ ID NO:11852 GCTGCATCCAGTTTGCAAAGT | SEQ ID NO:19864 CAACAGGCTAAAAGTTTCCCGCTCACT |
| | | AA | SEQ ID NO:3841 RASQGISIWLA | SEQ ID NO:11853 AASSLQS | SEQ ID NO:19865 QQAKSFPLT |
| iPS:437328 | 21-225_75D3 | NA | SEQ ID NO:3842 AGGGCCAGTCAGAGTGTTTACAGCAGCTACTTAGCC | SEQ ID NO:11854 GGTGCATCCAGCCGGTCCACT | SEQ ID NO:19866 CAGCACTATGATAACTCACCGTGGACG |
| | | AA | SEQ ID NO:3843 RASQSVYSSYLA | SEQ ID NO:11855 GASSRST | SEQ ID NO:19867 QHYDNSPWT |
| iPS:437332 | 21-225_75F3 | NA | SEQ ID NO:3844 AGGGCCAGTCAGAGTGTTTACAGCAGCTACTTAGCC | SEQ ID NO:11856 GGTGCATCCAGCCGGGCCACT | SEQ ID NO:19868 CAGCACTATGATAACTCACCGTGGACG |
| | | | SEQ ID NO:3845 | SEQ ID NO:11857 | SEQ ID NO:19869 |

FIGURE 49
(Continued)

| | | | | | | |
|---|---|---|---|---|---|---|
| iPS:437334 | 21-225_75F11 | AA | RASQSVYSSYLA SEQ ID NO:3846 | GASSRAT SEQ ID NO:11858 | QHYDNSPWT SEQ ID NO:19870 |
| | | NA | AGGGCCAGTCAGAGTGTTAG CAGAAATTTAGCC SEQ ID NO:3847 | GGTGCATCCATCAGGGC CACT SEQ ID NO:11859 | CAGCAGTATAATAACTGGCC TCCGCTCACT SEQ ID NO:19871 |
| iPS:437340 | 21-225_75G9 | AA | RASQSVSRNLA SEQ ID NO:3848 | GASIRAT SEQ ID NO:11860 | QQYNNWPPLT SEQ ID NO:19872 |
| | | NA | AGGGCCAGTCCGAGTGTTGA CAGCAGCTACTTAGCC SEQ ID NO:3849 | GGTGCATCCAGCAGGGC CCCT SEQ ID NO:11861 | CAGCAGTATGAAAGTTCACC GTGGACG SEQ ID NO:19873 |
| iPS:437344 | 21-225_75G12 | AA | RASPSVDSSYLA SEQ ID NO:3850 | GASSRAP SEQ ID NO:11862 | QQYESSPWT SEQ ID NO:19874 |
| | | NA | AGGGCCAGTCAGAGTGTTTA CAGCAGCTACTTAGCC SEQ ID NO:3851 | GGTGCATCCAGCAGCCGGGC CACT SEQ ID NO:11863 | CAGCACTATGATAACTCACC GTGGACG SEQ ID NO:19875 |
| iPS:437346 | 21-225_75H7 | AA | RASQSVYSSYLA SEQ ID NO:3852 | GASSRAT SEQ ID NO:11864 | QHYDNSPWT SEQ ID NO:19876 |
| | | NA | CGGGCAAGTCAGGGCATAA GAAATGATTTAGCC SEQ ID NO:3853 | GATGCATCCAGTTTGCA AAGT SEQ ID NO:11865 | ATACAGCATAGTAATTACC GCTCACT SEQ ID NO:19877 |
| iPS:437350 | 21-225_74A3 | AA | RASQGIRNDLG SEQ ID NO:3854 | DASSLQS SEQ ID NO:11866 | IQHSNYPLT SEQ ID NO:19878 |
| | | NA | AGGGCCAGTCAGAGTGTTTA CAGCAGCTACTTAGCC SEQ ID NO:3855 | GGTGCATCCAGCGCGGTC CACT SEQ ID NO:11867 | CAGCACTCTGATAACTCACC GTGGACG SEQ ID NO:19879 |
| iPS:437356 | 21_225_74B1 | AA | RASQSVYSSYLA SEQ ID NO:3856 | GASSRST SEQ ID NO:11868 | QHSDNSPWT SEQ ID NO:19880 |
| | | NA | AAGTCCAGCCAGAGTGTTTT ACACAGGTCCAACAATTACA ACTACTTAGCG | TGGGCATCTACCCGGGA ATCC | CAGCAATATTATAGTACTCC TCCGACG |

FIGURE 49
(Continued)

| | | | | | | |
|---|---|---|---|---|---|---|
| iPS:437361 | 21-225_74B1 | AA | SEQ ID NO:3857 KSSQSVLHRSNNYNYLA | SEQ ID NO:11869 WASTRES | SEQ ID NO:19881 QQYYSTPPT | |
| | | NA | SEQ ID NO:3858 AAGTCCAGCCAGAGTATTTT ACACAGTCCAACAATTACA ATTACTTAGCT | SEQ ID NO:11870 TGGGCATCTACCCGGGA ATCC | SEQ ID NO:19882 CAGCAATATTATAGTACTCC GTGGACG | |
| iPS:437363 | 21-225_74C1 | AA | SEQ ID NO:3859 KSSQSILHSSNNYNYLA | SEQ ID NO:11871 WASTRES | SEQ ID NO:19883 QQYYSTPWT | |
| | | NA | SEQ ID NO:3860 AAGTCCAGCCAGAGTGTTTT ATACAGTCCAACAATGCGA ACTACTTAGCT | SEQ ID NO:11872 TGGGCATCTACCCGGGA ATCC | SEQ ID NO:19884 CAGCAATATTATAGTACTCC GTGCAGT | |
| iPS:437369 | 21-225_74C10 | AA | SEQ ID NO:3861 KSSQSVLYSSNNANYLA | SEQ ID NO:11873 WASTRES | SEQ ID NO:19885 QQYYSTPCS | |
| | | NA | SEQ ID NO:3862 AGGGCCAGTCAGAGTGTTTA CAGCAGCTACTTAGCC | SEQ ID NO:11874 GGTGCATCCAGCGGGC CACT | SEQ ID NO:19886 CAGCATTATGATAACTCACC GTGGACG | |
| iPS:437371 | 21-225_74D6 | AA | SEQ ID NO:3863 RASQSVYSSYLA | SEQ ID NO:11875 GASSRAT | SEQ ID NO:19887 QHYDNSPWT | |
| | | NA | SEQ ID NO:3864 AGGTCTAGTCAGAGCCTCGT GCATAGTAGTGGATACAACT ATTTGGAT | SEQ ID NO:11876 TTGGGTTCTAATCGGACC TCC | SEQ ID NO:19888 ATGCAAGCTCTACACCCTCC TCTCACT | |
| iPS:437377 | 21-225_74D8 | AA | SEQ ID NO:3865 RSSQSLVHSSGYNYLD | SEQ ID NO:11877 LGSNRAS | SEQ ID NO:19889 MQALHPPLT | |
| | | NA | SEQ ID NO:3866 AGGGCCAGTCAGAGTGTTAG CAGCAGCTACTTAGTC | SEQ ID NO:11878 GGTGCATCCACCAGGGC CACT | SEQ ID NO:19890 CAGCAGTATGGTTGCTCACC GCTCACT | |
| | 21-225_74G9 | AA | SEQ ID NO:3867 RASQSVSSSYLV | SEQ ID NO:11879 GASTRAT | SEQ ID NO:19891 QQYGCSPLT | |

FIGURE 49 (Continued)

| | | | | | |
|---|---|---|---|---|---|
| iPS:437379 | 21-225_74H2 | NA | SEQ ID NO:3868 AAGTCCAGCCAGAGTGTTT ACACAGCTCCAACAATAAGA ACTACTTAACT | SEQ ID NO:11880 TGGGCATCTACTCGGGA ATCC | SEQ ID NO:19892 CAGCAATATTATAGTATTCC TCCGACG |
| | | AA | SEQ ID NO:3869 KSSQSVLHSSNKNYLT | SEQ ID NO:11881 WASTRES | SEQ ID NO:19893 QQYYSIPPT |
| iPS:437383 | 21-225_74H8 | NA | SEQ ID NO:3870 AGGGCCAGTCAGAGTTTTAG CAGCAGCTACTTAGCC | SEQ ID NO:11882 GGTGCATCCAGCAGGGC CACT | SEQ ID NO:19894 CAGCAGTATGGTAGCTCAAG GACG |
| | | AA | SEQ ID NO:3871 RASQSFSSSYLA | SEQ ID NO:11883 GASSRAT | SEQ ID NO:19895 QQYGSSRT |
| iPS:438664 | 21-225_216G1 | NA | SEQ ID NO:3872 CGGGCGAGTCAGGGCATTAG CAGTTATTAGCC | SEQ ID NO:11884 GCTGCATCCAGTCAGTTGCAA AGT | SEQ ID NO:19896 CTACGGTATGATACTTACCC TCTCACT |
| | | AA | SEQ ID NO:3873 RASQGISSYLA | SEQ ID NO:11885 AASSLQS | SEQ ID NO:19897 LRYDTYPLT |
| iPS:441468 | 21-225_25A4.001.001 | NA | SEQ ID NO:3874 AAGTCCAGCCAGAGTGTTT ATACAGCTCCCACAATAACA ACTACTTAGCT | SEQ ID NO:11886 TGGGCATCTACCCGGGA ATCC | SEQ ID NO:19898 CAGCAGTATTATAGTACTCC TCCGACG |
| | | AA | SEQ ID NO:3875 KSSQSVLYSSHNNNYLA | SEQ ID NO:11887 WASTRES | SEQ ID NO:19899 QQYYSTPPT |
| iPS:441475 | 21-225_25A4.001.002 | NA | SEQ ID NO:3876 AAGTCCAGCCAGAGTGTTT ATACAGCTCCCACAATAACA ACTACTTAGCT | SEQ ID NO:11888 TGGGCATCTACCCGGGA ATCC | SEQ ID NO:19900 CAGCAGTATTATAGTACTCC TCCGACG |
| | | AA | SEQ ID NO:3877 KSSQSVLYSSHNNNYLA | SEQ ID NO:11889 WASTRES | SEQ ID NO:19901 QQYYSTPPT |
| | | | SEQ ID NO:3878 | SEQ ID NO:11890 | SEQ ID NO:19902 |

FIGURE 49
(Continued)

| | | | | | | |
|---|---|---|---|---|---|---|
| iPS:441482 | 21-225_25A4.001.003 | NA | AAGTCCAGCCAGAGTGTTTT ATACAGTCCCACAATAACA ACTACTTAGCT<br>SEQ ID NO:3879 | TGGGCATCTACCCGGGA ATCC<br>SEQ ID NO:11891 | CAGCAGTATTATAGTACTCC TCCGACG<br>SEQ ID NO:19903 |
| | | AA | KSSQSVLYSSHNNNYLA<br>SEQ ID NO:3880 | WASTRES<br>SEQ ID NO:11892 | QQYYSTPPT<br>SEQ ID NO:19904 |
| iPS:441489 | 21-225_25A4.001.004 | NA | AAGTCCAGCCAGAGTGTTTT ATACAGTCCCACAATAACA ACTACTTAGCT<br>SEQ ID NO:3881 | TGGGCATCTACCCGGGA ATCC<br>SEQ ID NO:11893 | CAGCAGTATTATAGTACTCC TCCGACG<br>SEQ ID NO:19905 |
| | | AA | KSSQSVLYSSHNNNYLA<br>SEQ ID NO:3882 | WASTRES<br>SEQ ID NO:11894 | QQYYSTPPT<br>SEQ ID NO:19906 |
| iPS:441496 | 21-225_25A4.001.005 | NA | AAGTCCAGCCAGAGTGTTTT ATACAGTCCCACAATAACA ACTACTTAGCT<br>SEQ ID NO:3883 | TGGGCATCTACCCGGGA ATCC<br>SEQ ID NO:11895 | CAGCAGTATTATAGTACTCC TCCGACG<br>SEQ ID NO:19907 |
| | | AA | KSSQSVLYSSHNNNYLA<br>SEQ ID NO:3884 | WASTRES<br>SEQ ID NO:11896 | QQYYSTPPT<br>SEQ ID NO:19908 |
| iPS:441505 | 21-225_25A4.001.006 | NA | AAGTCCAGCCAGAGTGTTTT ATACAGTCCCACAATAACA ACTACTTAGCT<br>SEQ ID NO:3885 | TGGGCATCTACCCGGGA ATCC<br>SEQ ID NO:11897 | CAGCAGTATTATAGTACTCC TCCGACG<br>SEQ ID NO:19909 |
| | | AA | KSSQSVLYSSHNNNYLA<br>SEQ ID NO:3886 | WASTRES<br>SEQ ID NO:11898 | QQYYSTPPT<br>SEQ ID NO:19910 |
| iPS:441512 | 21-225_25A4.001.007 | NA | AAGTCCAGCCAGAGTGTTTT ATACAGTCCCACAATAACA ACTACTTAGCT<br>SEQ ID NO:3887 | TGGGCATCTACCCGGGA ATCC<br>SEQ ID NO:11899 | CAGCAGTATTATAGTACTCC TCCGACG<br>SEQ ID NO:19911 |
| | | AA | KSSQSVLYSSHNNNYLA<br>SEQ ID NO:3888 | WASTRES<br>SEQ ID NO:11900 | QQYYSTPPT<br>SEQ ID NO:19912 |

FIGURE 49
(Continued)

| iPS: | | | | | | |
|---|---|---|---|---|---|---|
| iPS:441519 | 21-225_25A4.001.008 | NA | AAGTCCAGCCAGAGTGTTTT ATACAGTCCCACAATAACA ACTACTTAGCT SEQ ID NO:3889 | TGGGCATCTACCCGGGA ATCC SEQ ID NO:11901 | CAGCAGTATTATAGTACTCC TCCGACG SEQ ID NO:19913 |
| | | AA | KSSQSVLYSSHNNNYLA SEQ ID NO:3890 | WASTRES SEQ ID NO:11902 | QQYYSTPPT SEQ ID NO:19914 |
| iPS:441554 | 21-225_25A4.001.013 | NA | AAGTCCAGCCAGAGTGTTTT ATACAGTCCCACAATAACA ACTACTTAGCT SEQ ID NO:3891 | TGGGCATCTACCCGGGA ATCC SEQ ID NO:11903 | CAGCAGTATTATAGTACTCC TCCGACG SEQ ID NO:19915 |
| | | AA | KSSQSVLYSSHNNNYLA SEQ ID NO:3892 | WASTRES SEQ ID NO:11904 | QQYYSTPPT SEQ ID NO:19916 |
| iPS:441595 | 21-225_25A4.001.019 | NA | AAGTCCAGCCAGAGTGTTTT ATACAGTCCCACAATAACA ACTACTTAGCT SEQ ID NO:3893 | TGGGCATCTACCCGGGA ATCC SEQ ID NO:11905 | CAGCAGTATTATAGTACTCC TCCGACG SEQ ID NO:19917 |
| | | AA | KSSQSVLYSSHNNNYLA SEQ ID NO:3894 | WASTRES SEQ ID NO:11906 | QQYYSTPPT SEQ ID NO:19918 |
| iPS:441604 | 21-225_25A4.001.020 | NA | AAGTCCAGCCAGAGTGTTTT ATACAGTCCCACAATAACA ACTACTTAGCT SEQ ID NO:3895 | TGGGCATCTACCCGGGA ATCC SEQ ID NO:11907 | CAGCAGTATTATAGTACTCC TCCGACG SEQ ID NO:19919 |
| | | AA | KSSQSVLYSSHNNNYLA SEQ ID NO:3896 | WASTRES SEQ ID NO:11908 | QQYYSTPPT SEQ ID NO:19920 |
| iPS:441613 | 21-225_25A4.001.021 | NA | AAGTCCAGCCAGAGTGTTTT ATACAGTCCCACAATAACA ACTACTTAGCT SEQ ID NO:3897 | TGGGCATCTACCCGGGA ATCC SEQ ID NO:11909 | CAGCAGTATTATAGTACTCC TCCGACG SEQ ID NO:19921 |
| | | AA | KSSQSVLYSSHNNNYLA SEQ ID NO:3898 | WASTRES SEQ ID NO:11910 | QQYYSTPPT SEQ ID NO:19922 |

FIGURE 49
(Continued)

| | | | | | |
|---|---|---|---|---|---|
| iPS:441841 | 21-225_4A2.001.001 | NA | AAGTCCAGCCAGAGTATTTT ACACAGCTCCAACAATAACA ACTACTTAGCT SEQ ID NO:3899 | TGGGCATCTACCCGGGA ATCC SEQ ID NO:11911 | CAGCAATATTATAGTACTCC AGTCACT SEQ ID NO:19923 |
| | | AA | KSSQSILHSSNNNYLA SEQ ID NO:3900 | WASTRES SEQ ID NO:11912 | QQYYSTPVT SEQ ID NO:19924 |
| iPS:441847 | 21-225_4A2.001.002 | NA | AAGTCCAGCCAGAGTATTTT ACACAGCTCCAACAATAACA ACTACTTAGCT SEQ ID NO:3901 | TGGGCATCTACCCGGGA ATCC SEQ ID NO:11913 | CAGCAATATTATAATGCTCC AGTCACT SEQ ID NO:19925 |
| | | AA | KSSQSILHSSNNNYLA SEQ ID NO:3902 | WASTRES SEQ ID NO:11914 | QQYYNAPVT SEQ ID NO:19926 |
| iPS:441853 | 21-225_4A2.001.003 | NA | AAGTCCAGCCAGAGTATTTT ACACAGCTCCAACAATAACA ACTACTTAGCT SEQ ID NO:3903 | TGGGCATCTACCCGGGA ATCC SEQ ID NO:11915 | CAGCAATATTATCAAACTCC AGTCACT SEQ ID NO:19927 |
| | | AA | KSSQSILHSSNNNYLA SEQ ID NO:3904 | WASTRES SEQ ID NO:11916 | QQYYQTPVT SEQ ID NO:19928 |
| iPS:441859 | 21-225_4A2.001.004 | NA | AAGTCCAGCCAGAGTATTTT ACACAGCTCCAACAATAACA ACTACTTAGCT SEQ ID NO:3905 | TGGGCATCTACCCGGGA ATCC SEQ ID NO:11917 | CAGCAATATTATAATACTCC AGTCACT SEQ ID NO:19929 |
| | | AA | KSSQSILHSSNNNYLA SEQ ID NO:3906 | WASTRES SEQ ID NO:11918 | QQYYNTPVT SEQ ID NO:19930 |
| iPS:441866 | 21-225_4A2.001.005 | NA | AAGTCCAGCCAGAGTATTTT ACACAGCTCCAACAATAACA ACTACTTAGCT SEQ ID NO:3907 | TGGGCATCTACCCGGGA ATCC SEQ ID NO:11919 | CAGCAATATTATAATACTCC AGTCACT SEQ ID NO:19931 |
| | | AA | KSSQSILHSSNNNYLA SEQ ID NO:3908 | WASTRES SEQ ID NO:11920 | QQYYNTPVT SEQ ID NO:19932 |

FIGURE 49
(Continued)

| | | | | | |
|---|---|---|---|---|---|
| iPS:441873 | 21-225_4A2.001.006 | NA | AAGTCCAGCCAGAGTATTTT ACACAGCTCCAACAATAACA ACTACTTAGCT SEQ ID NO:3909 | TGGGCATCTACCCGGGA ATCC SEQ ID NO:11921 | CAGCAATATTATAATACTCC AGTCACT SEQ ID NO:19933 |
| | | AA | KSSQSILHSSNNNNYLA SEQ ID NO:3910 | WASTRES SEQ ID NO:11922 | QQYYNTPVT SEQ ID NO:19934 |
| iPS:441880 | 21-225_4A2.001.007 | NA | AAGTCCAGCCAGAGTATTTT ACACAGCTCCAACAATAACA ACTACTTAGCT SEQ ID NO:3911 | TGGGCATCTACCCGGGA ATCC SEQ ID NO:11923 | CAGCAATATTATAGTACTCC AGTCACT SEQ ID NO:19935 |
| | | AA | KSSQSILHSSNNNNYLA SEQ ID NO:3912 | WASTRES SEQ ID NO:11924 | QQYYSTPVT SEQ ID NO:19936 |
| iPS:441884 | 21-225_4A2.001.008 | NA | AAGTCCAGCCAGAGTATTTT ACACAGCTCCAACAATAACA ACTACTTAGCT SEQ ID NO:3913 | TGGGCATCTACCCGGGA ATCC SEQ ID NO:11925 | CAGCAATATTATAGTACTCC AGTCACT SEQ ID NO:19937 |
| | | AA | KSSQSILHSSNNNNYLA SEQ ID NO:3914 | WASTRES SEQ ID NO:11926 | QQYYSTPVT SEQ ID NO:19938 |
| iPS:441888 | 21-225_4A2.001.009 | NA | AAGTCCAGCCAGAGTATTTT ACACAGCTCCAACAATAACA ACTACTTAGCT SEQ ID NO:3915 | TGGGCATCTACCCGGGA ATCC SEQ ID NO:11927 | CAGCAATATTATAAATGCTCC AGTCACT SEQ ID NO:19939 |
| | | AA | KSSQSILHSSNNNNYLA SEQ ID NO:3916 | WASTRES SEQ ID NO:11928 | QQYYNAPVT SEQ ID NO:19940 |
| iPS:441892 | 21-225_4A2.001.010 | NA | AAGTCCAGCCAGAGTATTTT ACACAGCTCCAACAATAACA ACTACTTAGCT SEQ ID NO:3917 | TGGGCATCTACCCGGGA ATCC SEQ ID NO:11929 | CAGCAATATTATCAAACTCC AGTCACT SEQ ID NO:19941 |
| | | AA | KSSQSILHSSNNNNYLA SEQ ID NO:3918 | WASTRES SEQ ID NO:11930 | QQYYQTPVT SEQ ID NO:19942 |

FIGURE 49
(Continued)

| | | | | | |
|---|---|---|---|---|---|
| iPS:441896 | 21-225_4A2.001.011 | NA | AAGTCCAGCCAGAGTATTTTACACAGCTCCAACAATAACAACTACTTAGCT SEQ ID NO:3919 | TGGGCATCTACCCGGGAATCC SEQ ID NO:11931 | CAGCAATATTATCAAACTCCAGTCACT SEQ ID NO:19943 |
| | | AA | KSSQSILHSSNNNNYLA SEQ ID NO:3920 | WASTRES SEQ ID NO:11932 | QQYYQTPVT SEQ ID NO:19944 |
| iPS:441900 | 21-225_4A2.001.012 | NA | AAGTCCAGCCAGAGTATTTTACACAGCTCCAACAATAACAACTACTTAGCT SEQ ID NO:3921 | TGGGCATCTACCCGGGAATCC SEQ ID NO:11933 | CAGCAATATTATCAAACTCCAGTCACT SEQ ID NO:19945 |
| | | AA | KSSQSILHSSNNNNYLA SEQ ID NO:3922 | WASTRES SEQ ID NO:11934 | QQYYQTPVT SEQ ID NO:19946 |
| iPS:441955 | 21-225_4A2.001.022 | NA | AAGTCCAGCCAGAGTATTTTACACAGCTCCAACAATAACAACTACTTAGCT SEQ ID NO:3923 | TGGGCATCTACCCGGGAATCC SEQ ID NO:11935 | CAGCAATATTATAGTACTCCAGTCACT SEQ ID NO:19947 |
| | | AA | KSSQSILHSSNNNNYLA SEQ ID NO:3924 | WASTRES SEQ ID NO:11936 | QQYYSTPVT SEQ ID NO:19948 |
| iPS:441962 | 21-225_4A2.001.023 | NA | AAGTCCAGCCAGAGTATTTTACACAGCTCCAACAATAACAACTACTTAGCT SEQ ID NO:3925 | TGGGCATCTACCCGGGAATCC SEQ ID NO:11937 | CAGCAATATTATAGTACTCCAGTCACT SEQ ID NO:19949 |
| | | AA | KSSQSILHSSNNNNYLA SEQ ID NO:3926 | WASTRES SEQ ID NO:11938 | QQYYSTPVT SEQ ID NO:19950 |
| iPS:441971 | 21-225_4A2.001.024 | NA | AAGTCCAGCCAGAGTATTTTACACAGCTCCAACAATAACAACTACTTAGCT SEQ ID NO:3927 | TGGGCATCTACCCGGGAATCC SEQ ID NO:11939 | CAGCAATATTATAGTACTCCAGTCACT SEQ ID NO:19951 |
| | | AA | KSSQSILHSSNNNNYLA SEQ ID NO:3928 | WASTRES SEQ ID NO:11940 | QQYYSTPVT SEQ ID NO:19952 |

FIGURE 49
(Continued)

| | | | | | |
|---|---|---|---|---|---|
| iPS:441999 | 21-225_4A2.001.028 | NA | AAGTCCAGCCAGAGTATTTT ACACAGCTCCAACAATAACA ACTACTTAGCT SEQ ID NO:3929 | TGGGCATCTACCCGGGA ATCC SEQ ID NO:11941 | CAGCAATATTATAGTACTCC AGTCACT SEQ ID NO:19953 |
| | | AA | KSSQSILHSSNNNNYLA SEQ ID NO:3930 | WASTRES SEQ ID NO:11942 | QQYYSTPVT SEQ ID NO:19954 |
| iPS:442006 | 21-225_4A2.001.029 | NA | AAGTCCAGCCAGAGTATTTT ACACAGCTCCAACAATAACA ACTACTTAGCT SEQ ID NO:3931 | TGGGCATCTACCCGGGA ATCC SEQ ID NO:11943 | CAGCAATATTATAGTACTCC AGTCACT SEQ ID NO:19955 |
| | | AA | KSSQSILHSSNNNNYLA SEQ ID NO:3932 | WASTRES SEQ ID NO:11944 | QQYYSTPVT SEQ ID NO:19956 |
| iPS:442020 | 21-225_4A2.001.031 | NA | AAGTCCAGCCAGAGTATTTT ACACAGCTCCAACAATAACA ACTACTTAGCT SEQ ID NO:3933 | TGGGCATCTACCCGGGA ATCC SEQ ID NO:11945 | CAGCAATATTATAATACTCC AGTCACT SEQ ID NO:19957 |
| | | AA | KSSQSILHSSNNNNYLA SEQ ID NO:3934 | WASTRES SEQ ID NO:11946 | QQYYNTPVT SEQ ID NO:19958 |
| iPS:442050 | 21-225_4H6.004 | NA | CGGGCGAGTCAGGGTATTAG CAGGTGGTTAGCC SEQ ID NO:3935 | GGTGCATCCAGTTGCA AAGT SEQ ID NO:11947 | CAACAGGCTAACAGTTCCC ATTCACT SEQ ID NO:19959 |
| | | AA | RASQGISRWLA SEQ ID NO:3936 | GASSLQS SEQ ID NO:11948 | QQANSFPFT SEQ ID NO:19960 |
| iPS:442059 | 21-225_4H6.005 | NA | CGGGCGAGTCAGGGTATTAG CAGGTGGTTAGCC SEQ ID NO:3937 | GGTGCATCCAGTTGCA AAGT SEQ ID NO:11949 | CAACAGGCTAACAGTTCCC ATTCACT SEQ ID NO:19961 |
| | | AA | RASQGISRWLA SEQ ID NO:3938 | GASSLQS SEQ ID NO:11950 | QQANSFPFT SEQ ID NO:19962 |
| iPS:442065 | | NA | CGGGCGAGTCAGGGTATTAG CAGGTGGTTAGCC | GGTGCATCCAGTTGCA AAGT | CAACAGGCTAACAGTTCCC ATTCACT |

FIGURE 49
(Continued)

| | | | | | | |
|---|---|---|---|---|---|---|
| iPS:442071 | 21-225_4H6.006 | AA | SEQ ID NO:3939<br>RASQGISRWLA<br>SEQ ID NO:3940 | SEQ ID NO:11951<br>GASSLQS<br>SEQ ID NO:11952 | SEQ ID NO:19963<br>QQANSFPFT<br>SEQ ID NO:19964 | |
| iPS:442078 | 21-225_4H6.007 | NA | CGGGCGAGTCAGGGTATTAG<br>CAGGTGGTTAGCC<br>SEQ ID NO:3941 | GGTGCATCCAGTTTGCA<br>AAGT<br>SEQ ID NO:11953 | CAACAGGCTAACAGTTTCCC<br>ATTCACT<br>SEQ ID NO:19965 | |
| | | AA | RASQGISRWLA<br>SEQ ID NO:3942 | GASSLQS<br>SEQ ID NO:11954 | QQANSFPFT<br>SEQ ID NO:19966 | |
| iPS:442085 | 21-225_4H6.008 | NA | CGGGCGAGTCAGGGTATTAG<br>CAGGTGGTTAGCC<br>SEQ ID NO:3943 | GGTGCATCCAGTTTGCA<br>AAGT<br>SEQ ID NO:11955 | CAACAGGCTAACAGTTTCCC<br>ATTCACT<br>SEQ ID NO:19967 | |
| | | AA | RASQGISRWLA<br>SEQ ID NO:3944 | GASSLQS<br>SEQ ID NO:11956 | QQANSFPFT<br>SEQ ID NO:19968 | |
| iPS:442089 | 21-225_4H6.009 | NA | CGGGCGAGTCAGGGTATTAG<br>CAGGTGGTTAGCC<br>SEQ ID NO:3945 | GGTGCATCCAGTTTGCA<br>AAGT<br>SEQ ID NO:11957 | CAACAGGCTAACAGTTTCCC<br>ATTCACT<br>SEQ ID NO:19969 | |
| | | AA | RASQGISRWLA<br>SEQ ID NO:3946 | GASSLQS<br>SEQ ID NO:11958 | QQANSFPFT<br>SEQ ID NO:19970 | |
| iPS:442093 | 21-225_4H6.010 | NA | CGGGCGAGTCAGGGTATTAG<br>CAGGTGGTTAGCC<br>SEQ ID NO:3947 | GGTGCATCCAGTTTGCA<br>AAGT<br>SEQ ID NO:11959 | CAACAGGCTAACAGTTTCCC<br>ATTCACT<br>SEQ ID NO:19971 | |
| | | AA | RASQGISRWLA<br>SEQ ID NO:3948 | GASSLQS<br>SEQ ID NO:11960 | QQANSFPFT<br>SEQ ID NO:19972 | |
| iPS:442115 | 21-225_4H6.011 | NA | CGGGCGAGTCAGGGTATTAG<br>CAGGTGGTTAGCC<br>SEQ ID NO:3949 | GGTGCATCCAGTTTGCA<br>AAGT<br>SEQ ID NO:11961 | CAACAGGCTAACAGTTTCCC<br>ATTCACT<br>SEQ ID NO:19973 | |
| | | AA | RASQGISRWLA<br>SEQ ID NO:3950 | GASSLQS<br>SEQ ID NO:11962 | QQANSFPFT<br>SEQ ID NO:19974 | |
| | | NA | CGGGCAAGTCAGGGCATTAG<br>AAATGATTTAGGC | GCTGCATCCAGTTTGCAA<br>AGT | CTACAGGCATTATAGTTACCC<br>TCGGACG | |

FIGURE 49
(Continued)

| | | | | | | |
|---|---|---|---|---|---|---|
| iPS:442122 | 21-225_5E5.003 | AA | SEQ ID NO:3951<br>RASQGIRNDLG | SEQ ID NO:11963<br>AASSLQS | SEQ ID NO:19975<br>LQHYSYPRT |
| | | NA | SEQ ID NO:3952<br>CGGGCAAGTCAGGGCATTAG<br>AAATGATTTAGGC | SEQ ID NO:11964<br>GCTGCATCCAGTTGCAA<br>AGT | SEQ ID NO:19976<br>CTACAGCATTATAGTTACCC<br>TCGGACG |
| iPS:442129 | 21-225_5E5.004 | AA | SEQ ID NO:3953<br>RASQGIRNDLG | SEQ ID NO:11965<br>AASSLQS | SEQ ID NO:19977<br>LQHYSYPRT |
| | | NA | SEQ ID NO:3954<br>CGGGCAAGTCAGGGCATTAG<br>AAATGATTTAGGC | SEQ ID NO:11966<br>GCTGCATCCAGTTGCAA<br>AGT | SEQ ID NO:19978<br>CTACAGCATTATAGTTACCC<br>TCGGACG |
| iPS:442136 | 21-225_5E5.005 | AA | SEQ ID NO:3955<br>RASQGIRNDLG | SEQ ID NO:11967<br>AASSLQS | SEQ ID NO:19979<br>LQHYSYPRT |
| | | NA | SEQ ID NO:3956<br>CGGGCAAGTCAGGGCATTAG<br>AAATGATTTAGGC | SEQ ID NO:11968<br>GCTGCATCCAGTTGCAA<br>AGT | SEQ ID NO:19980<br>CTACAGCATTATAGTTACCC<br>TCGGACG |
| iPS:442171 | 21-225_5E5.006 | AA | SEQ ID NO:3957<br>RASQGIRNDLG | SEQ ID NO:11969<br>AASSLQS | SEQ ID NO:19981<br>LQHYSYPRT |
| | | NA | SEQ ID NO:3958<br>CGGGCAAGTCAGGGCATTAG<br>AAATGATTTAGGC | SEQ ID NO:11970<br>GCTGCATCCAGTTGCAA<br>AGT | SEQ ID NO:19982<br>CTACAGCATTATAGTTACCC<br>TCGGACG |
| iPS:442178 | 21-225_5E5.011 | AA | SEQ ID NO:3959<br>RASQGIRNDLG | SEQ ID NO:11971<br>AASSLQS | SEQ ID NO:19983<br>LQHYSYPRT |
| | | NA | SEQ ID NO:3960<br>CGGGCAAGTCAGGGCATTAG<br>AAATGATTTAGGC | SEQ ID NO:11972<br>GCTGCATCCAGTTGCAA<br>AGT | SEQ ID NO:19984<br>CTACAGCATTATAGTTACCC<br>TCGGACG |
| iPS:442199 | 21-225_5E5.012 | AA | SEQ ID NO:3961<br>RASQGIRNDLG | SEQ ID NO:11973<br>AASSLQS | SEQ ID NO:19985<br>LQHYSYPRT |
| | | NA | SEQ ID NO:3962<br>CGGGCAAGTCAGGGCATTAG<br>AAATGATTTAGGC | SEQ ID NO:11974<br>GCTGCATCCAGTTGCAA<br>AGT | SEQ ID NO:19986<br>CTACAGCATTATAGTTACCC<br>TCGGACG |

FIGURE 49
(Continued)

| | | | | | | |
|---|---|---|---|---|---|---|
| iPS:442206 | 21-225_5E5.015 | AA | SEQ ID NO:3963<br>RASQGIRNDLG<br>SEQ ID NO:3964 | SEQ ID NO:11975<br>AASSLQS<br>SEQ ID NO:11976 | SEQ ID NO:19987<br>LQHYSYPRT<br>SEQ ID NO:19988 |
| | | NA | CGGGCAAGTCAGGGCATTAG<br>AAATGATTTAGGC<br>SEQ ID NO:3965 | GCTGCATCCAGTTGCAA<br>AGT<br>SEQ ID NO:11977 | CTACAGCATTATAGTTACCC<br>TCGGACG<br>SEQ ID NO:19989 |
| iPS:442213 | 21-225_5E5.016 | AA | RASQGIRNDLG<br>SEQ ID NO:3966 | AASSLQS<br>SEQ ID NO:11978 | LQHYSYPRT<br>SEQ ID NO:19990 |
| | | NA | CGGGCAAGTCAGGGCATTAG<br>AAATGATTTAGGC<br>SEQ ID NO:3967 | GCTGCATCCAGTTGCAA<br>AGT<br>SEQ ID NO:11979 | CTACAGCATTATAGTTACCC<br>TCGGACG<br>SEQ ID NO:19991 |
| iPS:442220 | 21-225_5E5.017 | AA | RASQGIRNDLG<br>SEQ ID NO:3968 | AASSLQS<br>SEQ ID NO:11980 | LQHYSYPRT<br>SEQ ID NO:19992 |
| | | NA | CGGGCAAGTCAGGGCATTAG<br>AAATGATTTAGGC<br>SEQ ID NO:3969 | GCTGCATCCAGTTGCAA<br>AGT<br>SEQ ID NO:11981 | CTACAGCATTATAGTTACCC<br>TCGGACG<br>SEQ ID NO:19993 |
| iPS:442227 | 21-225_5E5.018 | AA | RASQGIRNDLG<br>SEQ ID NO:3970 | AASSLQS<br>SEQ ID NO:11982 | LQHYSYPRT<br>SEQ ID NO:19994 |
| | | NA | CGGGCAAGTCAGGGCATTAG<br>AAATGATTTAGGC<br>SEQ ID NO:3971 | GCTGCATCCAGTTGCAA<br>AGT<br>SEQ ID NO:11983 | CTACAGCATTATAGTTACCC<br>TCGGACG<br>SEQ ID NO:19995 |
| iPS:442255 | 21-225_5E5.019 | AA | RASQGIRNDLG<br>SEQ ID NO:3972 | AASSLQS<br>SEQ ID NO:11984 | LQHYSYPRT<br>SEQ ID NO:19996 |
| | | NA | CGGGCAAGTCAGGGCATTAG<br>AAATGATTTAGGC<br>SEQ ID NO:3973 | GCTGCATCCAGTTGCAA<br>AGT<br>SEQ ID NO:11985 | CTACAGCATTATAGTTACCC<br>TCGGACG<br>SEQ ID NO:19997 |
| iPS:442262 | 21-225_5E5.023 | AA | RASQGIRNDLG<br>SEQ ID NO:3974 | AASSLQS<br>SEQ ID NO:11986 | LQHYSYPRT<br>SEQ ID NO:19998 |
| | | NA | CGGGCAAGTCAGGGCATTAG<br>AAATGATTTAGGC | GCTGCATCCAGTTGCAA<br>AGT | CTACAGCATTATAGTTACCC<br>TCGGACG |

FIGURE 49
(Continued)

| | | | | | | | |
|---|---|---|---|---|---|---|---|
| iPS:442269 | 21-225_5E5.024 | AA | SEQ ID NO:3975<br>RASQGIRNDLG | SEQ ID NO:11987<br>AASSLQS | SEQ ID NO:19999<br>LQHYSYPRT | | |
| | | NA | SEQ ID NO:3976<br>CGGGCAAGTCAGGGCATTAG<br>AAATGATTTAGGC | SEQ ID NO:11988<br>GCTGCATCCAGTTGCAA<br>AGT | SEQ ID NO:20000<br>CTACAGCATTATAGTTACCC<br>TCGGACG | | |
| iPS:442311 | 21-225_5E5.025 | AA | SEQ ID NO:3977<br>RASQGIRNDLG | SEQ ID NO:11989<br>AASSLQS | SEQ ID NO:20001<br>LQHYSYPRT | | |
| | | NA | SEQ ID NO:3978<br>CGGGCAAGTCAAAACATTAT<br>CAGCTATTTAAAT | SEQ ID NO:11990<br>ACTGCATCCAGTTGCAA<br>AGT | SEQ ID NO:20002<br>CAACAGACTTACAGTACCCC<br>GCTCACT | | |
| iPS:442317 | 21-225_7E11.001.001 | AA | SEQ ID NO:3979<br>RASQNIISYLN | SEQ ID NO:11991<br>TASSLQS | SEQ ID NO:20003<br>QQTYSTPLT | | |
| | | NA | SEQ ID NO:3980<br>CGGGCAAGTCAAAACATTAT<br>CAGCTATTTAAAT | SEQ ID NO:11992<br>ACTGCATCCAGTTGCAA<br>AGT | SEQ ID NO:20004<br>CAACAGACTTACAGTACCCC<br>GCTCACT | | |
| iPS:442323 | 21-225_7E11.001.002 | AA | SEQ ID NO:3981<br>RASQNIISYLN | SEQ ID NO:11993<br>TASSLQS | SEQ ID NO:20005<br>QQTYSTPLT | | |
| | | NA | SEQ ID NO:3982<br>CGGGCAAGTCAAAACATTAT<br>CAGCTATTTAAAT | SEQ ID NO:11994<br>ACTGCATCCAGTTGCAA<br>AGT | SEQ ID NO:20006<br>CAACAGACTTACAGTACCCC<br>GCTCACT | | |
| iPS:442330 | 21-225_7E11.001.003 | AA | SEQ ID NO:3983<br>RASQNIISYLN | SEQ ID NO:11995<br>TASSLQS | SEQ ID NO:20007<br>QQTYSTPLT | | |
| | | NA | SEQ ID NO:3984<br>CGGGCAAGTCAAAACATTAT<br>CAGCTATTTAAAT | SEQ ID NO:11996<br>ACTGCATCCAGTTGCAA<br>AGT | SEQ ID NO:20008<br>CAACAGACTTACAGTACCCC<br>GCTCACT | | |
| iPS:442337 | 21-225_7E11.001.004 | AA | SEQ ID NO:3985<br>RASQNIISYLN | SEQ ID NO:11997<br>TASSLQS | SEQ ID NO:20009<br>QQTYSTPLT | | |
| | | NA | SEQ ID NO:3986<br>CGGGCAAGTCAAAACATTAT<br>CAGCTATTTAAAT | SEQ ID NO:11998<br>ACTGCATCCAGTTGCAA<br>AGT | SEQ ID NO:20010<br>CAACAGACTTACAGTACCCC<br>GCTCACT | | |

FIGURE 49
(Continued)

| | | | | | |
|---|---|---|---|---|---|
| 21-225_7E11.001.005 | | SEQ ID NO:3987 | SEQ ID NO:11999 | SEQ ID NO:20011 | |
| | AA | RASQNIISYLN | TASSLQS | QQTYSTPLT | |
| iPS:442344 | NA | SEQ ID NO:3988 | SEQ ID NO:12000 | SEQ ID NO:20012 | CAACAGACTTACAGTACCCC GCTCACT |
| | | CGGGCAAGTCAAAACATTAT CAGCTATTTAAAT | ACTGCATCCAGTTGCAA AGT | | |
| 21-225_7E11.001.006 | | SEQ ID NO:3989 | SEQ ID NO:12001 | SEQ ID NO:20013 | |
| | AA | RASQNIISYLN | TASSLQS | QQTYSTPLT | |
| iPS:442351 | NA | SEQ ID NO:3990 | SEQ ID NO:12002 | SEQ ID NO:20014 | CAACAGACTTACAGTACCCC GCTCACT |
| | | CGGGCAAGTCAAAACATTAT CAGCTATTTAAAT | ACTGCATCCAGTTGCAA AGT | | |
| 21-225_7E11.001.007 | | SEQ ID NO:3991 | SEQ ID NO:12003 | SEQ ID NO:20015 | |
| | AA | RASQNIISYLN | TASSLQS | QQTYSTPLT | |
| iPS:442358 | NA | SEQ ID NO:3992 | SEQ ID NO:12004 | SEQ ID NO:20016 | CAACAGACTTACAGTACCCC GCTCACT |
| | | CGGGCAAGTCAAAACATTAT CAGCTATTTAAAT | ACTGCATCCAGTTGCAA AGT | | |
| 21-225_7E11.001.008 | | SEQ ID NO:3993 | SEQ ID NO:12005 | SEQ ID NO:20017 | |
| | AA | RASQNIISYLN | TASSLQS | QQTYSTPLT | |
| iPS:442365 | NA | SEQ ID NO:3994 | SEQ ID NO:12006 | SEQ ID NO:20018 | CAACAGACTTACAGTACCCC GCTCACT |
| | | CGGGCAAGTCAAAACATTAT CAGCTATTTAAAT | ACTGCATCCAGTTGCAA AGT | | |
| 21-225_7E11.001.009 | | SEQ ID NO:3995 | SEQ ID NO:12007 | SEQ ID NO:20019 | |
| | AA | RASQNIISYLN | TASSLQS | QQTYSTPLT | |
| iPS:442372 | NA | SEQ ID NO:3996 | SEQ ID NO:12008 | SEQ ID NO:20020 | CAACAGACTTACAGTACCCC GCTCACT |
| | | CGGGCAAGTCAAAACATTAT CAGCTATTTAAAT | ACTGCATCCAGTTGCAA AGT | | |
| 21-225_7E11.001.010 | | SEQ ID NO:3997 | SEQ ID NO:12009 | SEQ ID NO:20021 | |
| | AA | RASQNIISYLN | TASSLQS | QQTYSTPLT | |
| iPS:442379 | NA | SEQ ID NO:3998 | SEQ ID NO:12010 | SEQ ID NO:20022 | CAACAGACTTACAGTACCCC GCTCACT |
| | | CGGGCAAGTCAAAACATTAT CAGCTATTTAAAT | ACTGCATCCAGTTGCAA AGT | | |

FIGURE 49
(Continued)

| | | | | | | |
|---|---|---|---|---|---|---|
| | 21-225_7E11.001.011 | | SEQ ID NO:3999 | SEQ ID NO:12011 | | SEQ ID NO:20023 |
| | | AA | RASQNIISYLN | TASSLQS | | QQTYSTPLT |
| iPS:442386 | 21-225_7E11.001.012 | NA | SEQ ID NO:4000 CGGGCAAGTCAAAACATTAT CAGCTATTTAAAT | SEQ ID NO:12012 ACTGCATCCAGTTGCAA AGT | SEQ ID NO:20024 CAACAGACTTACAGTACCCC GCTCACT |
| | | | SEQ ID NO:4001 | SEQ ID NO:12013 | | SEQ ID NO:20025 |
| | | AA | RASQNIISYLN | TASSLQS | | QQTYSTPLT |
| iPS:442390 | 21-225_7E11.001.013 | NA | SEQ ID NO:4002 CGGGCAAGTCAAAACATTAT CAGCTATTTAAAT | SEQ ID NO:12014 ACTGCATCCAGTTGCAA AGT | SEQ ID NO:20026 CAACAGACTTACAGTACCCC GCTCACT |
| | | | SEQ ID NO:4003 | SEQ ID NO:12015 | | SEQ ID NO:20027 |
| | | AA | RASQNIISYLN | TASSLQS | | QQTYSTPLT |
| iPS:442394 | 21-225_7E11.001.014 | NA | SEQ ID NO:4004 CGGGCAAGTCAAAACATTAT CAGCTATTTAAAT | SEQ ID NO:12016 ACTGCATCCAGTTGCAA AGT | SEQ ID NO:20028 CAACAGACTTACAGTACCCC GCTCACT |
| | | | SEQ ID NO:4005 | SEQ ID NO:12017 | | SEQ ID NO:20029 |
| | | AA | RASQNIISYLN | TASSLQS | | QQTYSTPLT |
| iPS:442398 | 21-225_7E11.001.015 | NA | SEQ ID NO:4006 CGGGCAAGTCAAAACATTAT CAGCTATTTAAAT | SEQ ID NO:12018 ACTGCATCCAGTTGCAA AGT | SEQ ID NO:20030 CAACAGACTTACAGTACCCC GCTCACT |
| | | | SEQ ID NO:4007 | SEQ ID NO:12019 | | SEQ ID NO:20031 |
| | | AA | RASQNIISYLN | TASSLQS | | QQTYSTPLT |
| iPS:442402 | 21-225_7E11.001.016 | NA | SEQ ID NO:4008 CGGGCAAGTCAAAACATTAT CAGCTATTTAAAT | SEQ ID NO:12020 ACTGCATCCAGTTGCAA AGT | SEQ ID NO:20032 CAACAGACTTACAGTACCCC GCTCACT |
| | | | SEQ ID NO:4009 | SEQ ID NO:12021 | | SEQ ID NO:20033 |
| | | AA | RASQNIISYLN | TASSLQS | | QQTYSTPLT |
| iPS:442406 | | NA | SEQ ID NO:4010 CGGGCAAGTCAAAACATTAT CAGCTATTTAAAT | SEQ ID NO:12022 ACTGCATCCAGTTGCAA AGT | SEQ ID NO:20034 CAACAGACTTACAGTACCCC GCTCACT |

FIGURE 49
(Continued)

| | | | | | | | | |
|---|---|---|---|---|---|---|---|---|
| iPS:442410 | 21-225_7E11.001.017 | AA | SEQ ID NO:4011 | RASQNIISYLN | SEQ ID NO:12023 | TASSLQS | SEQ ID NO:20035 | QQTYSTPLT |
| | | NA | SEQ ID NO:4012 | CGGGCAAGTCAAAACATTAT CAGCTATTTAAAT | SEQ ID NO:12024 | ACTGCATCCAGTTGCAA AGT | SEQ ID NO:20036 | CAACAGACTTACAGTACCCC GCTCACT |
| iPS:442417 | 21-225_7E11.001.018 | AA | SEQ ID NO:4013 | RASQNIISYLN | SEQ ID NO:12025 | TASSLQS | SEQ ID NO:20037 | QQTYSTPLT |
| | | NA | SEQ ID NO:4014 | CGGGCAAGTCAAAACATTAT CAGCTATTTAAAT | SEQ ID NO:12026 | ACTGCATCCAGTTGCAA AGT | SEQ ID NO:20038 | CAACAGACTTACAGTACCCC GCTCACT |
| iPS:442431 | 21-225_7E11.001.019 | AA | SEQ ID NO:4015 | RASQNIISYLN | SEQ ID NO:12027 | TASSLQS | SEQ ID NO:20039 | QQTYSTPLT |
| | | NA | SEQ ID NO:4016 | CGGGCAAGTCAAAACATTAT CAGCTATTTAAAT | SEQ ID NO:12028 | ACTGCATCCAGTTGCAA AGT | SEQ ID NO:20040 | CAACAGACTTACAGTACCCC GCTCACT |
| iPS:442438 | 21-225_7E11.001.021 | AA | SEQ ID NO:4017 | RASQNIISYLN | SEQ ID NO:12029 | TASSLQS | SEQ ID NO:20041 | QQTYSTPLT |
| | | NA | SEQ ID NO:4018 | CGGGCAAGTCAAAACATTAT CAGCTATTTAAAT | SEQ ID NO:12030 | ACTGCATCCAGTTGCAA AGT | SEQ ID NO:20042 | CAACAGACTTACAGTACCCC GCTCACT |
| | 21-225_7E11.001.022 | AA | SEQ ID NO:4019 | RASQNIISYLN | SEQ ID NO:12031 | TASSLQS | SEQ ID NO:20043 | QQTYSTPLT |
| | | NA | SEQ ID NO:4020 | CGGGCAAGTCAAAACATTAT CAGCTATTTAAAT | SEQ ID NO:12032 | ACTGCATCCAGTTGCAA AGT | SEQ ID NO:20044 | CAACAGACTTACAGTACCCC GCTCACT |
| iPS:442568 | 21-225_149D8 | AA | SEQ ID NO:4021 | RASQSVISSYLA | SEQ ID NO:12033 | GVSSWAT | SEQ ID NO:20045 | QQYGRSPFN ATTCAAT |
| | | NA | SEQ ID NO:4022 | AGGGCCAGTCAGAGTGTGAT CAGCAGCTACTTAGCC | SEQ ID NO:12034 | GGTGTATCTAGTTGGGCC ACT | SEQ ID NO:20046 | CAACAATATGGTAGGTCACC |

FIGURE 49
(Continued)

| iPS: | | | | |
|---|---|---|---|---|
| iPS:443003 | 21-225_43F11_LC2 | NA | ACTGGGAGCAGCTCCAACAT CGGGGCAGGTTATGATGTAC AC | GGTAACAGCAATCGGCC CTCA | CAGTCCTATGACAACAGCCT GAGTGGTTGGTA |
| | | | SEQ ID NO:4023 | SEQ ID NO:12035 | SEQ ID NO:20047 |
| | | AA | TGSSSNIGAGYDVH | GNSNRPS | QSYDNSLSGSV |
| | | | SEQ ID NO:4024 | SEQ ID NO:12036 | SEQ ID NO:20048 |
| iPS:443005 | 21-225_43F11_LC1 | NA | AGGTCTAGTCAAAGCCTCGT ATACAGTGATGGAAACACCT ACTTGAAT | AAGGTTCTAACTGGGA CTCT | ATGCAAGGTACACACTGGCC GCTCACT |
| | | | SEQ ID NO:4025 | SEQ ID NO:12037 | SEQ ID NO:20049 |
| | | AA | RSSQSLVYSDGNTYLN | KVSNWDS | MQGTHWPLT |
| | | | SEQ ID NO:4026 | SEQ ID NO:12038 | SEQ ID NO:20050 |
| iPS:443006 | 21-225_25A4.001.029 | NA | AAGTCCAGCAGAGTGTTT ATACAGTCCCACAATAACA ACTACTTAGCT | TGGGCATCTACCCGGGA ATCC | CAGCAGTATTATAGTACTCC TCCGACG |
| | | | SEQ ID NO:4027 | SEQ ID NO:12039 | SEQ ID NO:20051 |
| | | AA | KSSQSVLYSSHNNNYLA | WASTRES | QQYYSTPPT |
| | | | SEQ ID NO:4028 | SEQ ID NO:12040 | SEQ ID NO:20052 |
| iPS:443016 | 21-225_4H6.014 | NA | CGGGCAGAGTCAGGGTATTAG CAGGTGGTAGCC | GGTGCATCCAGTTGCA AAGT | CAACAGGCTAACAGTTTCCC ATTCACT |
| | | | SEQ ID NO:4029 | SEQ ID NO:12041 | SEQ ID NO:20053 |
| | | AA | RASQGISRWLA | GASSLQS | QQANSFPFT |
| | | | SEQ ID NO:4030 | SEQ ID NO:12042 | SEQ ID NO:20054 |
| iPS:443027 | 21-225_7E11.001.023 | NA | CGGGCAAGTCAAAACATTAT CAGCTATTTAAAT | ACTGCATCCAGTTGCAA AGT | CAACAGACTTACAGTACCCC GCTCACT |
| | | | SEQ ID NO:4031 | SEQ ID NO:12043 | SEQ ID NO:20055 |
| | | AA | RASQNIISYLN | TASSLQS | QQTYSTPLT |
| | | | SEQ ID NO:4032 | SEQ ID NO:12044 | SEQ ID NO:20056 |

FIGURE 49
(Continued)

| | | | | | | | |
|---|---|---|---|---|---|---|---|
| iPS:446086 | 21-225_94D8 | NA | AAGTCCAGACAGAGTGTTTT ATACAGTCCAACAATTACA ACTACTTAACT SEQ ID NO:4033 | TGGGCATCTACCCGGGA ATCC SEQ ID NO:12045 | CAGCAATATTATAGTTCTCC TCCTACT SEQ ID NO:20057 |
| | | AA | KSRQSVLYSSNNYNYLT SEQ ID NO:4034 | WASTRES SEQ ID NO:12046 | QQYYSSPPT SEQ ID NO:20058 |
| iPS:446094 | 21-225_77E1 | NA | AAGTCCAGCCAGACTGTCT ACACAGTCCAACAATTATA ACTACTTAGCT SEQ ID NO:4035 | TGGACATCTACCCGGGA ATCC SEQ ID NO:12047 | CACCAATATCTTAGTAGTCC TCTGACG SEQ ID NO:20059 |
| | | AA | KSSQTVLHSSNNYNYLA SEQ ID NO:4036 | WTSTRES SEQ ID NO:12048 | HQYLSSPLT SEQ ID NO:20060 |
| iPS:448904 | 21-225_65C12 | NA | AGGGCCAGTCAGAGTGTTAG CATCAACTTAGCC SEQ ID NO:4037 | GGTGCATCCACCAGGGC CACT SEQ ID NO:12049 | CAGCAGTATAATACCTGGCC TCTCACT SEQ ID NO:20061 |
| | | AA | RASQSVSINLA SEQ ID NO:4038 | GASTRAT SEQ ID NO:12050 | QQYNTWPLT SEQ ID NO:20062 |
| iPS:448906 | 21-225_72G9 | NA | CGGGCAAGTCAGAGCATTAC CAGCTATTTAAAT SEQ ID NO:4039 | ACTGCATCCAGTTTGCAA AGT SEQ ID NO:12051 | CAACAGAGTCACAGTTTCCC ATTCACT SEQ ID NO:20063 |
| | | AA | RASQSITSYLN SEQ ID NO:4040 | TASSLQS SEQ ID NO:12052 | QQSHSFPFT SEQ ID NO:20064 |
| iPS:448908 | 21-225_50G9 | NA | TCTGGAGATAAATTGGGGGA TAAATATGCTGC SEQ ID NO:4041 | CAAGATAGCAAGCGGCC CTCA SEQ ID NO:12053 | CAGGGCGCGGAACAGCCGCAG AGGGGTA SEQ ID NO:20065 |
| | | AA | SGDKLGDKYAC SEQ ID NO:4042 | QDSKRPS SEQ ID NO:12054 | QARNSRRGV SEQ ID NO:20066 |
| iPS:451102 | 21-225_45F6 | NA | TCTGGAGATAAATTGGGGGA TAAATATGCTTCC SEQ ID NO:4043 | CAAGATAGTAAGCGGCC CTCA SEQ ID NO:12055 | CAGGCGTGGACAACAGAAC TATGGTA SEQ ID NO:20067 |

FIGURE 49
(Continued)

| iPS ID | Clone | | Sequence 1 | Sequence 2 | Sequence 3 |
|---|---|---|---|---|---|
| iPS:451104 | 21-225_49C5 | AA | SGDKLGDKYAS<br>SEQ ID NO:4044 | QDSKRPS<br>SEQ ID NO:12056 | QAWDNRTMV<br>SEQ ID NO:20068 |
| | | NA | TCTGGAAGCAGCTCCAACAT<br>CGGAAGTAATATTGTGACC<br>SEQ ID NO:4045 | AGTAATGATCAGCGGCC<br>CTCA<br>SEQ ID NO:12057 | ACAGCATGGGATGACAGCCT<br>GAATGGTTGGGTG<br>SEQ ID NO:20069 |
| iPS:451106 | 21-225_49D10 | AA | SGSSSNIGSNIVT<br>SEQ ID NO:4046 | SNDQRPS<br>SEQ ID NO:12058 | TAWDDSLNGWV<br>SEQ ID NO:20070 |
| | | NA | TCTGGAAGCAACTCCAACAT<br>CGGAAGTAATATTGTAACC<br>SEQ ID NO:4047 | AGTAATGATCAGCGGCC<br>CTCA<br>SEQ ID NO:12059 | GCAGCATGGGATGACAGCCT<br>GAATGGTTGGGTG<br>SEQ ID NO:20071 |
| iPS:451108 | 21-225_53E8 | AA | SGSNSNIGSNIVT<br>SEQ ID NO:4048 | SNDQRPS<br>SEQ ID NO:12060 | AAWDDSLNGWV<br>SEQ ID NO:20072 |
| | | NA | TCTGGAAGCTGCTCCAACAT<br>CGGAAGTAATATTGTGACC<br>SEQ ID NO:4049 | AGTAATGATCAGCGGCC<br>CTCA<br>SEQ ID NO:12061 | ACAGCATGGGATGACAGCCT<br>GAATGATTGGGTG<br>SEQ ID NO:20073 |
| iPS:451110 | 21-225_74C9 | AA | SGSCSNIGSNIVT<br>SEQ ID NO:4050 | SNDQRPS<br>SEQ ID NO:12062 | TAWDDSLNDWV<br>SEQ ID NO:20074 |
| | | NA | TCAGGAGATAAATCGGGGA<br>ATAAATATGTTTCC<br>SEQ ID NO:4051 | CAAGATAACAGGCGGCC<br>GTCA<br>SEQ ID NO:12063 | CAGGCGTGGGACAGCACCC<br>TGTGATA<br>SEQ ID NO:20075 |
| iPS:451112 | 21-225_53D10 | AA | SGDKSGNKYVS<br>SEQ ID NO:4052 | QDNRRPS<br>SEQ ID NO:12064 | QAWDSTPVI<br>SEQ ID NO:20076 |
| | | NA | TCTGGAGATAAATGGGGAA<br>TAAATATGCTTGC<br>SEQ ID NO:4053 | CAAGATCGCAAGCGGCC<br>CTCA<br>SEQ ID NO:12065 | CAGGCGTGGGACAGCAGCAC<br>TGTGGTA<br>SEQ ID NO:20077 |
| | | AA | SGDKLGNKYAC<br>SEQ ID NO:4054 | QDRKRPS<br>SEQ ID NO:12066 | QAWDSSTVV<br>SEQ ID NO:20078 |

FIGURE 49
(Continued)

| | | | | |
|---|---|---|---|---|
| iPS:451114 | 21-225_159A3 | NA | CGGGCAAGTCAGGACATTAG AAAGGATTAGGC SEQ ID NO:4055 | GCTGCATCCAGTTGCAA AGT SEQ ID NO:12067 | CTACAGGCATCATAGTTATCC TCGGACG SEQ ID NO:20079 |
| | | AA | RASQDIRKDLG SEQ ID NO:4056 | AASSLQS SEQ ID NO:12068 | LQHHSYPRT SEQ ID NO:20080 |
| iPS:451116 | 21-225_164A4 | NA | AAGTCCAGCCAGAGTGTTT ATACAGCTCCAACAATAAGA ACTACTTAACT SEQ ID NO:4057 | TGGGCATCTACCCGGA ATCC SEQ ID NO:12069 | CAGCAATATTTTAGTACTCC GTGGACG SEQ ID NO:20081 |
| | | AA | KSSQSVLYSSNNKNYLT SEQ ID NO:4058 | WASTRES SEQ ID NO:12070 | QQYFSTPWT SEQ ID NO:20082 |
| iPS:451118 | 21-225_191C8 | NA | AGGGCCAGTCAGAGTGTTCG CAGTAACTTAGCC SEQ ID NO:4059 | GGTGCATCCAGCCACCAGGC CACT SEQ ID NO:12071 | CAGCAGTCTTTTACCTGGCT CCGGACG SEQ ID NO:20083 |
| | | AA | RASQSVRSNLA SEQ ID NO:4060 | GASTRAT SEQ ID NO:12072 | QQSFTWLRT SEQ ID NO:20084 |
| iPS:451120 | 21-225_197D3 | NA | CGGGCGAGTCAGGGCATTAG AAATTATTTAGCC SEQ ID NO:4061 | GCTGCATCCAGTTGCAA AGT SEQ ID NO:12073 | CAACATTATCTTACTTACCC GCTCACT SEQ ID NO:20085 |
| | | AA | RASQGIRNYLA SEQ ID NO:4062 | AASSLQS SEQ ID NO:12074 | QHYLTYPLT SEQ ID NO:20086 |
| iPS:451122 | 21-225_200A1 | NA | AGGGCCAGTCAGAGTGTTAA CAGCAACTATTTAGCC SEQ ID NO:4063 | GGGGCATCCAGCAGGC CACT SEQ ID NO:12075 | CAGCAGTATGAGATCTCACC GTGGACG SEQ ID NO:20087 |
| | | AA | RASQSVNSNYLA SEQ ID NO:4064 | GASSRAT SEQ ID NO:12076 | QQYEISPWT SEQ ID NO:20088 |
| iPS:451124 | 21-225_74F6 | NA | AAGTCCAGTCAGAATATTT ATCCAGCTCCAACAATAAGA ACTACTTAACT SEQ ID NO:4065 | TGGACATCTACCCGGGA ATCC SEQ ID NO:12077 | CAGCAATATTTTAGTGTTCCT CTGACG SEQ ID NO:20089 |

FIGURE 49
(Continued)

| | | | | | | |
|---|---|---|---|---|---|---|
| iPS:451127 | 21-225_164A7 | AA | KSSQNILSSSNNKNYLT<br>SEQ ID NO:4066 | WTSTRES<br>SEQ ID NO:12078 | QQYFSVPLT<br>SEQ ID NO:20090 |
| | | NA | AAGTCCAGCCAGAGTGTTTT<br>ACACAGCTCCAACAATAACA<br>ACTACTTAGCT<br>SEQ ID NO:4067 | TGGACATCTACCCGGGA<br>ATCC<br>SEQ ID NO:12079 | CAGCAATATTATAGTATTCC<br>TCTGACG<br>SEQ ID NO:20091 |
| iPS:451129 | 21-225_94D2 | AA | KSSQSVLHSSNNNNYLA<br>SEQ ID NO:4068 | WTSTRES<br>SEQ ID NO:12080 | QQYYSIPLT<br>SEQ ID NO:20092 |
| | | NA | AAGTCCAGCCAGAGTGTTTT<br>ACACAGCTCCAACAATAAGA<br>ACTACTTAGCT<br>SEQ ID NO:4069 | TGGGCATCTACTCGGGA<br>ATCC<br>SEQ ID NO:12081 | CAGCAATATCATAGTATTCC<br>TCCGACG<br>SEQ ID NO:20093 |
| iPS:451131 | 21-225_160A7 | AA | KSSQSVLHSSNNKNYLT<br>SEQ ID NO:4070 | WASTRES<br>SEQ ID NO:12082 | QQYHSIPPT<br>SEQ ID NO:20094 |
| | | NA | AAGTCCAGCCAGAGTGTTTT<br>ATCCAACTCCCAACAATAACA<br>ACTACTTAGCT<br>SEQ ID NO:4071 | TGGGCATCTACCCGGGA<br>ATCC<br>SEQ ID NO:12083 | CAGCAATATTATAGTACTCC<br>GTGCAGT<br>SEQ ID NO:20095 |
| iPS:451133 | 21-225_95H4 | AA | KSSQSVLSNSHNNNYLA<br>SEQ ID NO:4072 | WASTRES<br>SEQ ID NO:12084 | QQYYSTPCS<br>SEQ ID NO:20096 |
| | | NA | AAGTCCAGCCAGAGTGTTTT<br>ATTCAGCTCCAACAATTATA<br>ATTACTTAGCT<br>SEQ ID NO:4073 | TGGGCATCTACCCGGGA<br>ATCC<br>SEQ ID NO:12085 | CAGCAATATCATAGTTCTCC<br>TCTGACG<br>SEQ ID NO:20097 |
| | | AA | KSSQSVLFSSNNYNYLA<br>SEQ ID NO:4074 | WASTRES<br>SEQ ID NO:12086 | QQYHSSPLT<br>SEQ ID NO:20098 |
| iPS:437240 | 21-225_84H12 | NA | CGGGCAAGTCAGGGCATTAG<br>AAATGATTTAGGC<br>SEQ ID NO:4075 | GCTGCATCCAGTTTGCAA<br>AGT<br>SEQ ID NO:12087 | TTACAGCATAATGATTACCC<br>ATTCACT<br>SEQ ID NO:20099 |
| | | AA | RASQGIRNDLG | AASSLQS | LQHNDYPFT |

FIGURE 49
(Continued)

| | | | | | |
|---|---|---|---|---|---|
| iPS:434577 | | NA | SEQ ID NO:4076 CGGGCAAGTCAGGGCATTAG AAATGATTTAGGC | SEQ ID NO:12088 GCTGCATCCAGTTTGCAA AGT | SEQ ID NO:20100 CTACAGCATAATGATTACC ATTCACT |
| | 21-225_75C11 | | SEQ ID NO:4077 RASQGIRNDLG | SEQ ID NO:12089 AASSLQS | SEQ ID NO:20101 LQHNDYPFT |
| | | AA | SEQ ID NO:4078 | SEQ ID NO:12090 | SEQ ID NO:20102 |
| iPS:435477 | | NA | SEQ ID NO:4079 CGGGCGAGTCAGTTTATTAG CAGCTGGTTAGCC | SEQ ID NO:12091 ACTGCATCCAGTTTGCAA AGT | SEQ ID NO:20103 CAACAGGCTAACAGTTCCC GTGGACG |
| | 21-225_154E8 | | SEQ ID NO:4080 RASQFISSWLA | SEQ ID NO:12092 TASSLQS | SEQ ID NO:20104 QQANSFPWT |
| | | AA | SEQ ID NO:4081 | SEQ ID NO:12093 | SEQ ID NO:20105 |
| iPS:434553 | | NA | SEQ ID NO:4082 CGGGCAAGTCAGGGCATTAG AAATGATTTAGGC | SEQ ID NO:12094 GCTGCATCCAGTTTGCA AAGT | SEQ ID NO:20106 CTACAGCATAATGATTACC ATTCACT |
| | 21-225_76H12 | | SEQ ID NO:4083 RASQGIRNDLG | SEQ ID NO:12095 AASRLQS | SEQ ID NO:20107 LQHNDYPFT |
| | | AA | SEQ ID NO:4084 | SEQ ID NO:12096 | SEQ ID NO:20108 |
| iPS:434927 | | NA | SEQ ID NO:4085 CGGGCAAGTCAGGGCATTAG AAATGATTTAGGC | SEQ ID NO:12097 GCTGCATCCAGTTTGCAA AGT | SEQ ID NO:20109 CAACAGGCTAACAGTTTCCC GTGGACG |
| | 21-225_86E5 | | SEQ ID NO:4086 RASQGIRNDLG | SEQ ID NO:12098 AASSLQS | SEQ ID NO:20110 QQANSFPWT |
| | | AA | RASQFISSWLA | AASSLQS | LQHNDYPFT |
| iPS:435385 | 21-225_149G7 | | | | |

Table 2B

FIGURE 49
(Continued)

Standard
IgG Antibody
VH CDRs

| IPS# | Ab | Type | CDR1 | | CDR2 | | CDR3 | |
|---|---|---|---|---|---|---|---|---|
| iPS:451135 | 21-225_64A11 | NA | AACTATGGCATGCAC | SEQ ID NO:4087 | GTTATATCATATGTTGGAAGTAATAAATACTATGCAGACTCCGTGAAGGGC | SEQ ID NO:12099 | AGAGGAGCAGTGGCTCGTAGCTACGGTATGGACGTC | SEQ ID NO:20111 |
| | | AA | NYGMH | SEQ ID NO:4088 | VISYVGSNKYYADSVKG | SEQ ID NO:12100 | RGAVAPYYGMDV | SEQ ID NO:20112 |
| iPS:451141 | 21-225_164B11 | NA | AATTATGATATCAAC | SEQ ID NO:4089 | TGGATGACCCCTAACAGTGGTAACACAGGCTATGCACAGAAGTTCCAGGGC | SEQ ID NO:12101 | AGCAGTGGCTGGTACATGTTTGACTAC | SEQ ID NO:20113 |
| | | AA | NYDIN | SEQ ID NO:4090 | WMTPNSGNTGYAQKFQG | SEQ ID NO:12102 | SSGWYMFDY | SEQ ID NO:20114 |
| iPS:451137 | 21-225_74A7 | NA | AATTATGATATCAAC | SEQ ID NO:4091 | TGGATGAACCCTAACAGTGGTAACACAGGCTATGCACAGAAGTTCCAGGGC | SEQ ID NO:12103 | TCCAGTGGCTGGAACTGGTTCGACCCC | SEQ ID NO:20115 |
| | | AA | NYDIN | SEQ ID NO:4092 | WMNPNSGNTGYAQKFQG | SEQ ID NO:12104 | SSGWNWFDP | SEQ ID NO:20116 |
| iPS:451139 | 21-225_71A6 | NA | AACTATGGCATGCAC | SEQ ID NO:4093 | GTTATATCATATGATGGAAGTAATGAATACTATGCAGACTCCGTGAAGGGC | SEQ ID NO:12105 | GATCACAGATATGGGGTTCGGGGAGGCTTTGACTAC | SEQ ID NO:20117 |
| | | AA | NYGMH | | VISYDGSNEYYADSVKG | | DHRYGVRGGFDY | |

FIGURE 49
(Continued)

| | | | | | | |
|---|---|---|---|---|---|---|
| iPS:451143 | 21-225_66H11 | NA | SEQ ID NO:4094 ACCTATGGTATCAGC | SEQ ID NO:12106 TGGATCAGCGCTTACAATGTAACACAAACTATGCACAGAAGCTCCAGGGC | SEQ ID NO:20118 GGGGAAGCAGTGGCTGCTTCGACCCC |
| | | AA | SEQ ID NO:4095 TYGIS | SEQ ID NO:12107 WISAYNGNTNYAQKLQG | SEQ ID NO:20119 GEAVAVFDP |
| iPS:453445 | 21-225_148E10 | NA | SEQ ID NO:4096 AGCTATGGCATGCAC | SEQ ID NO:12108 GTTATATGGTTTGATGGCAGTAATAAATACTATGTAGACTCCGTGAAGGAC | SEQ ID NO:20120 GATCGGGTGGAGGGTTCGGGGACTCCTACTACTACGGTATGGACGTC |
| | | AA | SEQ ID NO:4097 SYGMH | SEQ ID NO:12109 VIWFDGSNKYYVDSVKD | SEQ ID NO:20121 DRVEGGIPYYYYGMDV |
| iPS:453447 | 21-225_65F10 | NA | SEQ ID NO:4098 GGCTACCATATGCAC | SEQ ID NO:12110 TGGATCAACCCTAACAATGGTGGCACAAGCTATGCACAGAAGTTTCAGGAC | SEQ ID NO:20122 GATAGTAGGTCGTCCTGGGACTAC |
| | | AA | SEQ ID NO:4099 GYHMH | SEQ ID NO:12111 WINPNNGGTSYAQKFQD | SEQ ID NO:20123 DSRSSWDY |
| iPS:453449 | 21-225_208A2 | NA | SEQ ID NO:4100 AGTTACTACTGGAGC | SEQ ID NO:12112 CGTATCTATACCAGTGGGAGCACCGACTACAACCCCTCCCTCAAGAGT | SEQ ID NO:20124 GGGTTCGGTGACTGGGACTAC |
| | | AA | SEQ ID NO:4101 SYYWS | SEQ ID NO:12113 RIYTSGSTDYNPSLKS | SEQ ID NO:20125 GFGDWDY |
| | | | SEQ ID NO:4102 | SEQ ID NO:12114 | SEQ ID NO:20126 |

FIGURE 49
(Continued)

| | | | | | |
|---|---|---|---|---|---|
| iPS:453451 | 21-225_52G11 | NA | GGCTACTATTTGCAC | TGGATCAACCCTAATAG AAATGGCACAAACTATG CACAGAAGTTTCAGGGC | GACGGTACCAGCAGCTTTGA CTAC |
| | | | SEQ ID NO:4103 | SEQ ID NO:12115 | SEQ ID NO:20127 |
| | | AA | GYYLH | WINPNRNGTNYAQKFQG | DGTSSFDY |
| | | | SEQ ID NO:4104 | SEQ ID NO:12116 | SEQ ID NO:20128 |
| iPS:453453 | 21-225_53F2 | NA | GGCTACTATTTGCAC | TGGATCAACCCTAATAG AAATGGCACAAACTATG CACAGAAGTTTCAGGGC | GACGGTACCAGTAGCTTTGA CTAC |
| | | | SEQ ID NO:4105 | SEQ ID NO:12117 | SEQ ID NO:20129 |
| | | AA | GYYLH | WINPNRNGTNYAQNFQG | DGTSSFDY |
| | | | SEQ ID NO:4106 | SEQ ID NO:12118 | SEQ ID NO:20130 |
| iPS:468810 | 21-225_74D5 | NA | GGTTGCTACTGGAGC | GAAATCAATTATAGTGG AAGGACCAACTTCAACC CGTCCCTCAAGAGT | GACTACGGCGGTATGGACGT C |
| | | | SEQ ID NO:4107 | SEQ ID NO:12119 | SEQ ID NO:20131 |
| | | AA | GCYWS | EINYSGRTNFNPSLKS | DYGGMDV |
| | | | SEQ ID NO:4108 | SEQ ID NO:12120 | SEQ ID NO:20132 |
| iPS:468812 | 21-225_48H4 | NA | GACTCTCTCATGCAC | GTTATATGGTATGATGG AAGTAATAAATACTATA CAGACTCCGTTAAGGGC | GAAAACTATAGCAGTGGCTG GTACGGGTACGGTATGGACG TC |
| | | | SEQ ID NO:4109 | SEQ ID NO:12121 | SEQ ID NO:20133 |
| | | AA | DSLMH | VIWYDGSNKYYTDSVKG | ENYSSGWYGYGMDV |
| | | | SEQ ID NO:4110 | SEQ ID NO:12122 | SEQ ID NO:20134 |

FIGURE 49
(Continued)

| | | | | | |
|---|---|---|---|---|---|
| iPS:468816 | 21-225_52G8 | NA | AGCTATGGCATGCAC | GTTATATGGTATGATGG AAGTAATAAATACTATG CAGACTCCGTGAAGGGC | AGGTATAGCAGCAGCTGGTC GGGCGGTATGGACGTC |
| | | | SEQ ID NO:4111 | SEQ ID NO:12123 | SEQ ID NO:20135 |
| | | AA | SYGMH | VIWYDGSNKYYADSVKG | RYSSSWSGGMDV |
| | | | SEQ ID NO:4112 | SEQ ID NO:12124 | SEQ ID NO:20136 |
| iPS:468814 | 21-225_223D11 | NA | AACTATGGCATGGAC | GTTATATGGTATGATGG AAGTAATGACTACTATG CAGACTCCGTGAAGGGC | GATCGGGGGATCGGTACAA CGATATGGACGTC |
| | | | SEQ ID NO:4113 | SEQ ID NO:12125 | SEQ ID NO:20137 |
| | | AA | NYGMD | VIWYDGSNDYYADSVKG | DRGIGYNDMDV |
| | | | SEQ ID NO:4114 | SEQ ID NO:12126 | SEQ ID NO:20138 |
| iPS:468822 | 21-225_147E10 | NA | AACTATGGCTTACAC | ATTATATGGTATGATGG AAGTAATAAATACTATG CAGACTCCGTGAAGGGC | GATCATTACGATTTTTGGAG TGGTCACTTTGACTAC |
| | | | SEQ ID NO:4115 | SEQ ID NO:12127 | SEQ ID NO:20139 |
| | | AA | NYGLH | IIWYDGSNKYYADSVKG | DHYDFWSGHFDY |
| | | | SEQ ID NO:4116 | SEQ ID NO:12128 | SEQ ID NO:20140 |
| iPS:468824 | 21-225_73G6 | NA | AGCTATGGCATGCAC | GTTATATGGTATGATGTA AGTAATAAATACTATGG AGAACTCCGTGAAGGGC | GAAGTGGGGATGACTTCTGA CTAC |
| | | | SEQ ID NO:4117 | SEQ ID NO:12129 | SEQ ID NO:20141 |
| | | AA | SYGMH | VIWYDVSNKYYGDSVKG | EVGMTSDY |
| | | | SEQ ID NO:4118 | SEQ ID NO:12130 | SEQ ID NO:20142 |

FIGURE 49
(Continued)

| | | | | | |
|---|---|---|---|---|---|
| iPS:468818 | 21-225_190C8 | NA | AGTTATGATATCAAC | TGGATGAACCCTAAAAG GGGTAACACAGGCTATG CACAGAAGTTCCAGGGC | GGAGACCCGTATAACTGGAA CTCCTACGCTATGGACGTC |
| | | | SEQ ID NO:4119 | SEQ ID NO:12131 | SEQ ID NO:20143 |
| | | AA | SYDIN | WMNPKRGNTGYAQKFQG | GDPYNWNSYAMDV |
| | | | SEQ ID NO:4120 | SEQ ID NO:12132 | SEQ ID NO:20144 |
| iPS:468826 | 21-225_201C5 | NA | GACTATGTCATGCAC | GTTATATGGTATGATGG AAGTAATAAATACTATG TAGACTCCGTGAAGGGC | GAACGGTATAGCAGTGGCTT GTACGACTACGGTATGGACG TC |
| | | | SEQ ID NO:4121 | SEQ ID NO:12133 | SEQ ID NO:20145 |
| | | AA | DYVMH | VIWYDGSNKYYVDSVKG | ERYSSGLYDYGMDV |
| | | | SEQ ID NO:4122 | SEQ ID NO:12134 | SEQ ID NO:20146 |
| iPS:468828 | 21-225_162A10 | NA | AGCTGTGGCATGCAC | GCTATATGGTATGATGG AAGCAATAAATACTATG CAGACTCCGTGAAGGGC | GACAAAATATAATGGGAGA TACTTGGTTTGACTTC |
| | | | SEQ ID NO:4123 | SEQ ID NO:12135 | SEQ ID NO:20147 |
| | | AA | SCGMH | AIWYDGSNKYYADSVKG | DKNIMGDTWFDF |
| | | | SEQ ID NO:4124 | SEQ ID NO:12136 | SEQ ID NO:20148 |
| iPS:468830 | 21-225_191G11 | NA | GGCTACTATATGCAC | TGGATCAACCCTAATAG TGGTGGCACAAACTTTG CACAGAAGTTTCAGGGC | GGAAAGAACTATGGCTCCTA CTTTGACTAC |
| | | | SEQ ID NO:4125 | SEQ ID NO:12137 | SEQ ID NO:20149 |
| | | AA | GYYMH | WINPNSGGTNFAQKFQG | GKNYGSYFDY |
| | | | SEQ ID NO:4126 | SEQ ID NO:12138 | SEQ ID NO:20150 |

FIGURE 49
(Continued)

| | | NA/AA | | | |
|---|---|---|---|---|---|
| iPS:468832 | 21-225_76H10 | NA | GGTTGCTACTGGAGC | GAAATCAATTATAGTGGAAGGACCAACTTCAACCCGTCCCTCAAGAGT | GACTACGGCGCGGTATGGACGTC |
| | | | SEQ ID NO:4127 | SEQ ID NO:12139 | SEQ ID NO:20151 |
| | | AA | GCYWS | EINYSGRTNFNPSLKS | DYGGMDV |
| | | | SEQ ID NO:4128 | SEQ ID NO:12140 | SEQ ID NO:20152 |
| iPS:468834 | 21-225_94G10 | NA | GGTTGCTACTGGAGC | GAAATCAATTATAGTGGAAGGACCAACTTCAACCCGTCCCTCAAGAGT | GACTACGGCGGTATGGACGTC |
| | | | SEQ ID NO:4129 | SEQ ID NO:12141 | SEQ ID NO:20153 |
| | | AA | GCYWS | EINYSGRTNFNPSLKS | DYGGMDV |
| | | | SEQ ID NO:4130 | SEQ ID NO:12142 | SEQ ID NO:20154 |
| iPS:468836 | 21-225_198E3 | NA | AGCTATGGCATGCAC | GTTATATCATATGATGGAGGTTATAAAACTATGCAGACTCCGTGAAGGGC | GGTACCCACGGGTACTACTACGGTGTGGACGTC |
| | | | SEQ ID NO:4131 | SEQ ID NO:12143 | SEQ ID NO:20155 |
| | | AA | SYGMH | VISYDGGYKNYADSVKG | GTHGYYYGVDV |
| | | | SEQ ID NO:4132 | SEQ ID NO:12144 | SEQ ID NO:20156 |
| iPS:468838 | 21-225_80E12 | NA | GGTTGCTACTGGAGC | GAAATCAATTATAGTGGAAGGACCAACTTCAACCCGTCCCTCAAGAGT | GACTACGGCGCGGTATGGACGTC |
| | | | SEQ ID NO:4133 | SEQ ID NO:12145 | SEQ ID NO:20157 |
| | | AA | GCYWS | EINYSGRTNFNPSLKS | DYGGMDV |
| | | | SEQ ID NO:4134 | SEQ ID NO:12146 | SEQ ID NO:20158 |
| iPS:468840 | 21-225_200H9 | NA | AGTGGTGGTGACTACTGGAGC | TACATCTATTACAGTGGGAGCACCTACTACAACCCGTCCCTCAAGAGT | ATGGACTACAGTAACTACTACTACGGTATGGACGTC |
| | | | SEQ ID NO:4135 | SEQ ID NO:12147 | SEQ ID NO:20159 |
| | | AA | SGGDYWS | YIYYSGSTYYNPSLKS | MDYSNYYYGMDV |
| | | | SEQ ID NO:4136 | SEQ ID NO:12148 | SEQ ID NO:20160 |

FIGURE 49
(Continued)

| | | | | | |
|---|---|---|---|---|---|
| iPS:468820 | 21-225_76E10 | NA | GGTTCCTACTGGAGC | GAAATCAATTATAGTGG AAGGACCAACTTCAACC CGTCCCTCAAGAGT | GACTACGGGCGGTATGGACGT C |
| | | | SEQ ID NO:4137 | SEQ ID NO:12149 | SEQ ID NO:20161 |
| | | AA | GSYWS | EINYSGRTNFNPSLKS | DYGGMDV |
| | | | SEQ ID NO:4138 | SEQ ID NO:12150 | SEQ ID NO:20162 |
| iPS:468842 | 21-225_50H4 | NA | AGCTATGTCATGCAC | GCTATATGGTATGATGG AAGTAATAAATACTATG CAGACTCCGTGAAGGGC | GAGTTGTATAGCAGCAACTG GTACGACTACGGTATGGACG TC |
| | | | SEQ ID NO:4139 | SEQ ID NO:12151 | SEQ ID NO:20163 |
| | | AA | SYVMH | AIWYDGSNKYYADSVKG | ELYSSNWYDYGMDV |
| | | | SEQ ID NO:4140 | SEQ ID NO:12152 | SEQ ID NO:20164 |
| iPS:468844 | 21-225_48E10 | NA | AGCTATAACATGAAC | TCCATTAGTGGTAGTAGT AGTTACATATACTACGC AGACTCAGTGAAGGGC | AGCCTCGACCTC |
| | | | SEQ ID NO:4141 | SEQ ID NO:12153 | SEQ ID NO:20165 |
| | | AA | SYNMN | SISGSSSYIYYADSVKG | SLDL |
| | | | SEQ ID NO:4142 | SEQ ID NO:12154 | SEQ ID NO:20166 |
| iPS:468846 | 21-225_53B10 | NA | AGCTATAGCATGAAC | TCCATTAGTGGTAGTAGC AGTTACATATACTACGTA GACTCAGTGAAGGGC | GTCAACTCTTTTGACTCC |
| | | | SEQ ID NO:4143 | SEQ ID NO:12155 | SEQ ID NO:20167 |
| | | AA | SYSMN | SISGSSSYIYYVDSVKG | VNSFDS |
| | | | SEQ ID NO:4144 | SEQ ID NO:12156 | SEQ ID NO:20168 |
| iPS:468848 | 21-225_54B1 | NA | AGCTATGCCATGAGC | GTTCTTAGTGGTAGTGGT GGTAGCACATTCTACGC AGACTCCGTGAAGGGC | AGAGGCCGTGAATATAGTGG CTACGATTACTTTGACTAC |
| | | | SEQ ID NO:4145 | SEQ ID NO:12157 | SEQ ID NO:20169 |

FIGURE 49
(Continued)

| | | | | SYAMS | VLSGSGGSTFYADSVKG | RGREYSGYDYFDY |
|---|---|---|---|---|---|---|
| iPS:468850 | | | AA | SEQ ID NO:4146 | SEQ ID NO:12158 | SEQ ID NO:20170 |
| | 21-225_63F4 | | NA | AATTATGATGTCAAC | TGGATGCACCCTAACAGTGGTAACACAGGCTATGCACAGAAGTTCCGGGGC | AGCAGTGGCTGGTACGTTTTTGACTAC |
| | | | | SEQ ID NO:4147 | SEQ ID NO:12159 | SEQ ID NO:20171 |
| | | | AA | NYDVN | WMHPNSGNTGYAQKFRG | SSGWYVFDY |
| iPS:468852 | | | | SEQ ID NO:4148 | SEQ ID NO:12160 | SEQ ID NO:20172 |
| | 21-225_71F3 | | NA | AATTATGATGTCAAC | TGGATGCACCCTAACAGTGGTAACACAGGCTATGCACAGAAGTTCCAGGGC | AGCAGTGGCTGGTACGTTTTTGACTCC |
| | | | | SEQ ID NO:4149 | SEQ ID NO:12161 | SEQ ID NO:20173 |
| | | | AA | NYDVN | WMHPNSGNIGYAQKFQG | SSGWYVFDS |
| iPS:468854 | | | | SEQ ID NO:4150 | SEQ ID NO:12162 | SEQ ID NO:20174 |
| | 21-225_72C4 | | NA | AATTATGATGTCAAC | TGGATGCACCCTAACAGTGGTAACACAGGCTATGCACAGAAGTTCCAGGGC | AGCAGTGGCTGGTACGTTTTTGACTAC |
| | | | | SEQ ID NO:4151 | SEQ ID NO:12163 | SEQ ID NO:20175 |
| | | | AA | NYDIN | WMHPNSGNTGYAQKFQG | SSGWYLFDY |
| iPS:468856 | | | | SEQ ID NO:4152 | SEQ ID NO:12164 | SEQ ID NO:20176 |
| | 21-225_77C9 | | NA | AGGAGTAGTTACTACTGGGGC | AGTATCTATTATAGTGGGAGCGCTACTCCAACCCGTCCCTCAAGAGT | CTTGACTCTAACTGGGGTCTTGACTAC |
| | | | | SEQ ID NO:4153 | SEQ ID NO:12165 | SEQ ID NO:20177 |
| | | | AA | RSSYYWG | SIYYSGSAYSNPSLKS | LDSNWGLDY |
| | | | | SEQ ID NO:4154 | SEQ ID NO:12166 | SEQ ID NO:20178 |

FIGURE 49
(Continued)

| | | | | | |
|---|---|---|---|---|---|
| iPS:468858 | 21-225_148C9 | NA | GACTATGGCATGCAC | GTTATATGGTATGATGG AAGTAATAAGTACTATG CAGACTCCGTGAAGGGC | GAGAGGTATAGCAGTGGCTG GTACGACTACGGTTGGACG TC |
| | | | SEQ ID NO:4155 | SEQ ID NO:12167 | SEQ ID NO:20179 |
| | | AA | DYGMH | VIWYDGSNKYYADSVKG | ERYSSGWYDYGLDV |
| | | | SEQ ID NO:4156 | SEQ ID NO:12168 | SEQ ID NO:20180 |
| iPS:468860 | 21-225_224E7 | NA | AGCTATGTCATGCAC | GTTATATGGTATGATGG AAGTAATAAATACTATG CAGACTCCGTGAAGGGC | GAACAGTATAGCAGCAGCTG GTACGACTTCGGTCTGGACG TC |
| | | | SEQ ID NO:4157 | SEQ ID NO:12169 | SEQ ID NO:20181 |
| | | AA | SYVMH | VIWYDGSNKYYADSVKG | EQYSSWYDFGLDV |
| | | | SEQ ID NO:4158 | SEQ ID NO:12170 | SEQ ID NO:20182 |
| iPS:468862 | 21-225_178H8 | NA | GACTATTATATGCAC | TGGATCAACCCTAACAG AGGTGGCACAAACTATG CTCAGAAGTTCAGGGC | GAGGAGGATCGCAGTGGCTG GTACTACTACTACGGTATGG ACGTC |
| | | | SEQ ID NO:4159 | SEQ ID NO:12171 | SEQ ID NO:20183 |
| | | AA | DYYMH | WINPNRGGTNYAQKFQG | EEDRSGWYYYYGMDV |
| | | | SEQ ID NO:4160 | SEQ ID NO:12172 | SEQ ID NO:20184 |
| iPS:468864 | 21-225_60D6 | NA | ACTAGTGGAGTGGGTGTGG C | CTCATTATTGGAAAGAT GATGAGGCTACAGCCC ATCTCTGAAGAGC | GCAGTGGCTGTCTCCTTGA CTAC |
| | | | SEQ ID NO:4161 | SEQ ID NO:12173 | SEQ ID NO:20185 |
| | | AA | TSGVGVG | LIYWKDDERYSPSLKS | AVAVSFDY |
| | | | SEQ ID NO:4162 | SEQ ID NO:12174 | SEQ ID NO:20186 |
| iPS:468866 | 21_225_190C1 | NA | GGCTACTATATGCAC | TGGATCAACCCTTACAGT GGTGGCACAAACTATGC ACAGAAGTTTCAGGGC | GATAGAGCAGTGGCTGGAAA CTACTTCTACTACGGTATGG ACGTC |

FIGURE 49
(Continued)

| | | | | | | | |
|---|---|---|---|---|---|---|---|
| iPS:468868 | 21-225_190C1 | AA | SEQ ID NO:4163<br>GYYMH | | SEQ ID NO:12175<br>WINPYSGGTNYAQKFQG | | SEQ ID NO:20187<br>DRAVAGNYFYYGMDV |
| | | NA | SEQ ID NO:4164 | | SEQ ID NO:12176 | | SEQ ID NO:20188 |
| | | | GGTAGTAGTTACTACTGGGG<br>C | | AATATCTATTATAGTGGG<br>AGCACCTACCAACCC<br>GTCCCTCAAGAGT | | CATGATTACTTTGGTCCCTT<br>GACTTC |
| iPS:468870 | 21-225_74A1 | AA | SEQ ID NO:4165<br>GSSYYWG | | SEQ ID NO:12177<br>NIYYSGSTYHNPSLKS | | SEQ ID NO:20189<br>HDLLWSLDF |
| | | NA | SEQ ID NO:4166 | | SEQ ID NO:12178 | | SEQ ID NO:20190 |
| | | | AATTATGATATCAAC | | TGGATGCACCTAACAG<br>TGGTAACACAGGCTATG<br>CACAGAAGTTCCAGGGC | | AGTAGTGGCTGGTACAAATT<br>TGACTAC |
| iPS:472730 | 21-225_74A8 | AA | SEQ ID NO:4167<br>NYDIN | | SEQ ID NO:12179<br>WMHPNSGNTGYAQKFQG | | SEQ ID NO:20191<br>SSGWYKFDY |
| | | NA | SEQ ID NO:4168<br>AGCTATACCATGAAC | | SEQ ID NO:12180<br>TCCATAAGTGGTAGTAG<br>TAGTTACTTATACTACCC<br>AGACTCAGTGAAGGGC | | SEQ ID NO:20192<br>GATAGAGGCAGCAGC |
| iPS:472731 | 21-225_14B1_LC1 | AA | SEQ ID NO:4169<br>SYTMN | | SEQ ID NO:12181<br>SISGSSSYLYYPDSVKG | | SEQ ID NO:20193<br>DRGSS |
| | | NA | SEQ ID NO:4170<br>AGCTATACCATGAAC | | SEQ ID NO:12182<br>TCCATAAGTGGTAGTAG<br>TAGTTACTTATACTACCC<br>AGACTCAGTGAAGGGC | | SEQ ID NO:20194<br>GATAGAGGCAGCAGC |
| | 21-225_14B1_LC2 | AA | SEQ ID NO:4171<br>SYTMN | | SEQ ID NO:12183<br>SISGSSSYLYYPDSVKG | | SEQ ID NO:20195<br>DRGSS |
| | | | SEQ ID NO:4172 | | SEQ ID NO:12184 | | SEQ ID NO:20196 |

FIGURE 49
(Continued)

| iPS: | Name | NA/AA | CDR1 | CDR2 | CDR3 |
|---|---|---|---|---|---|
| iPS:472732 | 21-225_2B10_LC1 | NA | AGCTATGTCATGCAC SEQ ID NO:4173 | GTTATATGGTATGATGG AAGTAATAAATACTATG CAGACTCCGTGAAGGTC SEQ ID NO:12185 | GAGAGATATACCAGTGGCTG GTATGACTACGGTATGGACG TC SEQ ID NO:20197 |
| | | AA | SYVMH SEQ ID NO:4174 | VIWYDGSNKYYADSVKV SEQ ID NO:12186 | ERYTSGWYDYGMDV SEQ ID NO:20198 |
| iPS:472733 | 21-225_2B10_LC2 | NA | AGCTATGTCATGCAC SEQ ID NO:4175 | GTTATATGGTATGATGG AAGTAATAAATACTATG CAGACTCCGTGAAGGTC SEQ ID NO:12187 | GAGAGATATACCAGTGGCTG GTATGACTACGGTATGGACG TC SEQ ID NO:20199 |
| | | AA | SYVMH SEQ ID NO:4176 | VIWYDGSNKYYADSVKV SEQ ID NO:12188 | ERYTSGWYDYGMDV SEQ ID NO:20200 |
| iPS:473253 | 21-225_7C3_LC1 | NA | GACTACTATTTGCAC SEQ ID NO:4177 | TGGATCCACCCTAACAG TGGTGGCACAAACTATG CACAGAAGTTTCAGGGC SEQ ID NO:12189 | GATGGTACCAGCTCGTTTGA CTAC SEQ ID NO:20201 |
| | | AA | DYYLH SEQ ID NO:4178 | WIHPNSGGTNYAQKFQG SEQ ID NO:12190 | DGTSSFDY SEQ ID NO:20202 |
| iPS:473254 | 21-225_7C3_LC2 | NA | GACTACTATTTGCAC SEQ ID NO:4179 | TGGATCCACCCTAACAG TGGTGGCACAAACTATG CACAGAAGTTTCAGGGC SEQ ID NO:12191 | GATGGTACCAGCTCGTTTGA CTAC SEQ ID NO:20203 |
| | | AA | DYYLH SEQ ID NO:4180 | WIHPNSGGTNYAQKFQG SEQ ID NO:12192 | DGTSSFDY SEQ ID NO:20204 |

FIGURE 49
(Continued)

| iPS: | | | | | |
|---|---|---|---|---|---|
| iPS:473255 | 21-225_9F12_LC1 | NA | GACTACTATTTGCAC  SEQ ID NO:4181 | TGGATCCACCCTAACAG TGGTGGCACAAGTTTG CACAGAAGTTTCAGGGC  SEQ ID NO:12193 | GATGGTACCAGCTCGTTTGA CTAC  SEQ ID NO:20205 |
| | | AA | DYYLH  SEQ ID NO:4182 | WIHPNSGGTNFAQKFQG  SEQ ID NO:12194 | DGTSSFDY  SEQ ID NO:20206 |
| iPS:473256 | 21-225_9F12_LC2 | NA | GACTACTATTTGCAC  SEQ ID NO:4183 | TGGATCCACCCTAACAG TGGTGGCACAAACTTTG CACAGAAGTTTCAGGGC  SEQ ID NO:12195 | GATGGTACCAGCTCGTTTGA CTAC  SEQ ID NO:20207 |
| | | AA | DYYLH  SEQ ID NO:4184 | WIHPNSGGTNFAQKFQG  SEQ ID NO:12196 | DGTSSFDY  SEQ ID NO:20208 |
| iPS:472742 | 21-225_30D9_LC2 | NA | GGCTACTATCTGCAC  SEQ ID NO:4185 | TGGATCAACCCTAACAG TGGTGGCACAAACTATG CACAGAAGTTTCAGGGC  SEQ ID NO:12197 | GTGTATTACTATGGTTCGGG GAGTTATTATAACGAGTTTG ACAAC  SEQ ID NO:20209 |
| | | AA | GYYLH  SEQ ID NO:4186 | WINPNSGGTNYAQKFQG  SEQ ID NO:12198 | VYYYGSGSYYNEFDN  SEQ ID NO:20210 |
| iPS:472741 | 21-225_30D9_LC1 | NA | GGCTACTATCTGCAC  SEQ ID NO:4187 | TGGATCAACCCTAACAG TGGTGGCACAAACTATG CACAGAAGTTTCAGGGC  SEQ ID NO:12199 | GTGTATTACTATGGTTCGGG GAGTTATTATAACGAGTTTG ACAAC  SEQ ID NO:20211 |
| | | AA | GYYLH  SEQ ID NO:4188 | WINPNSGGTNYAQKFQG  SEQ ID NO:12200 | VYYYGSGSYYNEFDN  SEQ ID NO:20212 |
| iPS:472743 | 21-225_68G6 | NA | GGGTACTATATGCAC  SEQ ID NO:4189 | TCGATCTACCGTAACAGT GGTGGCACAAATTATGC ACAGAAGTTTCAGGGC  SEQ ID NO:12201 | GCCTTTTACTATGGTTCGGG GACTATTATAACGAATTTG ACTAC  SEQ ID NO:20213 |
| | | AA | GYYMH  SEQ ID NO:4190 | SIYRNSGGTNYAQKFQG  SEQ ID NO:12202 | AFYYGSGTYYNEFDY  SEQ ID NO:20214 |

FIGURE 49
(Continued)

| | | | | |
|---|---|---|---|---|
| iPS:392573 | 21-225_15G2 | NA | ACTAGTGGAGTGGGTGTGG C<br>SEQ ID NO:4191<br>TSGVGVG<br>SEQ ID NO:4192 | CTCATTTATTGGAATGAT GATAAGGCGCTACAGCCC ATCTCTGAAGAGC<br>SEQ ID NO:12203<br>LIYWNDDKRYSPSLKS<br>SEQ ID NO:12204 | ACCGGTGTCAGCTGCTGCTA TTTTCACTAT<br>SEQ ID NO:20215<br>TGVSCCYFHY<br>SEQ ID NO:20216 |
| iPS:392583 | 21-225_10B10 | NA | ACTGGTGGAGTGGGTGTGG C<br>SEQ ID NO:4193<br>TGGVGVG<br>SEQ ID NO:4194 | TTCATTTATTGGAGTGAT GATAAGCGCTACAGCCC ATCTCTGAAGAGC<br>SEQ ID NO:12205<br>FIYWSDDKRYSPSLKS<br>SEQ ID NO:12206 | ATAGCAGCAGTTGCCTTTGA CTAC<br>SEQ ID NO:20217<br>IAAVAFDY<br>SEQ ID NO:20218 |
| iPS:392585 | 21-225_14H11 | NA | GGCCACTATATGTGC<br>SEQ ID NO:4195<br>GHYMC<br>SEQ ID NO:4196 | TGGATCAACCCTAATAG TGGTGGCACAAACTATG CACAGAAGTTTCAGGGC<br>SEQ ID NO:12207<br>WINPNSGGTNYAQKFQG<br>SEQ ID NO:12208 | GGATATTGTAGTAGTTCCAG CTGCTATTGCAACCGGGTT ATTACGGTATGGACGTC<br>SEQ ID NO:20219<br>GYCSSSSCYLQPGYYGMDV<br>SEQ ID NO:20220 |
| iPS:392587 | 21-225_18G5 | NA | ACTAGTGGAGTGGGTGTGG C<br>SEQ ID NO:4197<br>TSGVGVG<br>SEQ ID NO:4198 | CTCATTTATTGGAATGAT GATAAGGTCTACAGCCC ATCTCTGAAGAGC<br>SEQ ID NO:12209<br>LIYWNDKVYSPSLKS<br>SEQ ID NO:12210 | AGGGGACAGCAGCTGCCCT CGACTAC<br>SEQ ID NO:20221<br>RGQQLALDY<br>SEQ ID NO:20222 |
| iPS:392589 | 21-225_27H2 | NA | GGCTATGGCATGCAC<br>SEQ ID NO:4199 | GTTATATGGTATGATGG AAGTAATAAATACTATG CAGACTCCGTGAAGGGC<br>SEQ ID NO:12211 | GATAGGGTATATTGTAGTAG TACCAGCTGCTCCCCTTACT ACTACTACGGTATGGAC GTC<br>SEQ ID NO:20223 |

FIGURE 49
(Continued)

| | | | | GYGMH | VIWYDGSNKYYADSVKG | DRVYCSSTSCSPYYYYGMDV |
|---|---|---|---|---|---|---|
| | | | AA | SEQ ID NO:4200 | SEQ ID NO:12212 | SEQ ID NO:20224 |
| iPS:392593 | 21-225_3E10 | | NA | ACTGGTGGAGTGGGTGTGGGC | CTCATTTATTGGAATGATGATAAGGCGCCACAGCCCATCTCTGAAGAGC | CTTATAGAAGTGGCCTTTGACTAT |
| | | | AA | TGGVGVG | LIYWNDDKRHSPSLKS | LIEVAFDY |
| iPS:392596 | 21-225_12D8 | | | SEQ ID NO:4201 | SEQ ID NO:12213 | SEQ ID NO:20225 |
| | | | NA | AGCTATGTCATGAGC | ACTATTAGTGTTGGTGGTGGTAGCACATACTACGCAGACTCCGTGAAGGGC | TGGGGACGTGGATACAGCTATGAATACTACGGTATGGACGTC |
| | | | AA | SYVMS | SEQ ID NO:12214 | SEQ ID NO:20226 |
| iPS:392598 | 21-225_18E10 | | | SEQ ID NO:4202 | TISVGGSTYYADSVKG | WGRGYSYEYYYGMDV |
| | | | NA | GGCTACTACTATATGCAC | SEQ ID NO:12215 | SEQ ID NO:20227 |
| | | | AA | SEQ ID NO:4203 | TGGATCAACCTAACAGTGGTGCACAAACTATGCACAGAAGTTTCAGGGC | TCGTACTACTATGGTTCGGGGAGTTATTATAACGAGTTTGACTAC |
| iPS:392618 | 21-225_16F10 | | | GYYMH | SEQ ID NO:12216 | SEQ ID NO:20228 |
| | | | NA | SEQ ID NO:4204 | WINPNSGGTNYAQKFQG | SYYYGSGSYYNEFDY |
| | | | AA | GACTATGGCATGCAC | SEQ ID NO:12217 | SEQ ID NO:20229 |
| | | | | SEQ ID NO:4205 | GTCATATGGTATGATGGAAATAATAAATACTATGTAGACTCCGTGAAGGGC | GAGCTTGCCTGGTACGAGGACTAC |
| | | | | GYGMH | SEQ ID NO:12218 | SEQ ID NO:20230 |
| | | | | SEQ ID NO:4206 | SEQ ID NO:12219 | SEQ ID NO:20231 |
| | | | | DYGMH | VIWYDGNNKYYVDSVKG | ELAWYEDY |
| | | | | SEQ ID NO:4207 | SEQ ID NO:12220 | SEQ ID NO:20232 |
| | | | | SEQ ID NO:4208 | | |

FIGURE 49
(Continued)

| | | | | |
|---|---|---|---|---|
| iPS:392620 | 21-225_17H5 | NA | AGCTATAGCATGAAC | TCCATTAGTAGTAGTAGTACTTACATATACTACGCAGACTCAGTGAAGGGC | GTGGCTTCATTTGACTAC |
| | | | SEQ ID NO:4209 | SEQ ID NO:12221 | SEQ ID NO:20233 |
| | | AA | SYSMN | SISSSSTYIYYADSVKG | VASFDY |
| | | | SEQ ID NO:4210 | SEQ ID NO:12222 | SEQ ID NO:20234 |
| iPS:392622 | 21-225_17H8 | NA | AGAAGTAGTTACTACTGGGGC | AATATCTATTATGGTGGGAACACCTACTACAACCCGTCCCTCAAGAGT | CATGGAAAAGACTGGGCTTGACTAC |
| | | | SEQ ID NO:4211 | SEQ ID NO:12223 | SEQ ID NO:20235 |
| | | AA | RSSYYWG | NIYYGGNTYYNPSLKS | HGKDWGLDY |
| | | | SEQ ID NO:4212 | SEQ ID NO:12224 | SEQ ID NO:20236 |
| iPS:392624 | 21-225_17H12 | NA | AGCTATACCATGAAC | TCCATTAGTGGTAGTAGTAGTTACATATACTACGCAGACTCAGTGAAGGGC | GATCGAGGCTCCATC |
| | | | SEQ ID NO:4213 | SEQ ID NO:12225 | SEQ ID NO:20237 |
| | | AA | SYTMN | SISGSSSYIYYADSVKG | DRGSI |
| | | | SEQ ID NO:4214 | SEQ ID NO:12226 | SEQ ID NO:20238 |
| iPS:392626 | 21-225_18A5 | NA | GACTATGGCATGCAC | GTTATATGGTTTGATGGAAGTAATAAATACTATGCAGACTCCGTGAAGGGC | GATCTGGCTGGCTGGACGGAAGAGTAC |
| | | | SEQ ID NO:4215 | SEQ ID NO:12227 | SEQ ID NO:20239 |
| | | AA | DYGMH | VIWFDGSNKYYADSVKG | DLGWTFEY |
| | | | SEQ ID NO:4216 | SEQ ID NO:12228 | SEQ ID NO:20240 |
| iPS:392628 | 21-225_20C2 | NA | AGAAGTAGTTACTACTGGGGC | AATATCTATTATAGTGGGACTGCCTACTGTAATTCGTCCCTCAAGAGT | CATAGTAGCAGCTGGTCCCTTGACAAC |
| | | | SEQ ID NO:4217 | SEQ ID NO:12229 | SEQ ID NO:20241 |
| | | AA | RSSYYWG | NIYYSGTAYCNSSLKS | HSSSWSLDN |

FIGURE 49
(Continued)

| | | | | | | | | |
|---|---|---|---|---|---|---|---|---|
| iPS:392630 | 21-225_20E5 | NA | SEQ ID NO:4218 | GACTATGGCATGCAC | SEQ ID NO:12230 | GTTATTTGGTATGAAGA AATAATCAATACTATG CAGACTCCGTGAAGGGC | SEQ ID NO:20242 | GAACTGGGGGTTCCGGTCTGA CTAC |
| | | AA | SEQ ID NO:4219 | DYGMH | SEQ ID NO:12231 | VIWYEENNQYYADSVKG | SEQ ID NO:20243 | ELGFRSDY |
| iPS:392632 | 21-225_16A11 | NA | SEQ ID NO:4220 | AGCTATAGCATGAAC | SEQ ID NO:12232 | TCCATTAGTGGTAGTAGT AGTCTCATATACTACGCA GACTCAGTGAAGGGC | SEQ ID NO:20244 | GTAGCAGCCTTTGACTAC |
| | | AA | SEQ ID NO:4221 | SYSMN | SEQ ID NO:12233 | SISGSSSLIYYADSVKG | SEQ ID NO:20245 | VAAFDY |
| iPS:392634 | 21-225_17H3 | NA | SEQ ID NO:4222 | AACTGTGTCATGCAC | SEQ ID NO:12234 | GTTATATGGTATGATGG AAGTAATAAATACTATG CAGACTCCGTGAAGGGC | SEQ ID NO:20246 | GAAAAGTATAGCAGCAGCTG GTACGACTACGGTATGGACG TC |
| | | AA | SEQ ID NO:4223 | NCVMH | SEQ ID NO:12235 | VIWYDGSNKYYADSVKG | SEQ ID NO:20247 | EKYSSSWYDYGMDV |
| iPS:392636 | 21-225_17A6 | NA | SEQ ID NO:4224 | CGCAACACTGCTGCTTGGAG C | SEQ ID NO:12236 | AGGACATATACAGGTC CAAGTGGTATAATGATT ATGCAGTATCTGTGAAA AGT | SEQ ID NO:20248 | GTAAGCAGTGGCTGGTCCA TCACTACTACTACGGTA TGGACGTC |
| | | AA | SEQ ID NO:4225 | RNTAAWS | SEQ ID NO:12237 | RTYYRSKWYNDYAVSVK S | SEQ ID NO:20249 | VSSGWSHHYYYYGMDV |

FIGURE 49
(Continued)

| | | | | | | |
|---|---|---|---|---|---|---|
| iPS:392638 | 21-225_17F9 | NA | SEQ ID NO:4226 AGAAGTAGTTACTATTGGGGC | SEQ ID NO:12238 AATATCTATTATAGTGGGAGCACCTACAATCCGTCCCTCAAGAGT | SEQ ID NO:20250 CATGGAAAAGACTGGGGCCTTGACTAC | |
| | | AA | SEQ ID NO:4227 RSSYYWG | SEQ ID NO:12239 NIYYSGSTYYNPSLKS | SEQ ID NO:20251 HGKDWGLDY | |
| iPS:392640 | 21-225_18A1 | NA | SEQ ID NO:4228 AGCTATGGCATGCAT | SEQ ID NO:12240 GTTATATATGGTATGAGGAAATATAAATATTATGTAGACTCCGTGAAGGGC | SEQ ID NO:20252 GAGCTAGGCTTCCAGTCTGACTAC | |
| | | AA | SEQ ID NO:4229 SYGMH | SEQ ID NO:12241 VIWYEENNKYYVDSVKG | SEQ ID NO:20253 ELGFQSDY | |
| iPS:392642 | 21-225_18C6 | NA | SEQ ID NO:4230 AGGAGTAGTTATTATTACTGGGGC | SEQ ID NO:12242 AATATCTATTATAGTGGGTACACCTACTACAACCCGTCCCTCAAGAGT | SEQ ID NO:20254 CATAGTAGCAGTTGGTCCCTTGACGAC | |
| | | AA | SEQ ID NO:4231 RSSYYWG | SEQ ID NO:12243 NIYYSGYTYYNPSLKS | SEQ ID NO:20255 HSSSWSLDD | |
| iPS:392644 | 21-225_19E1 | NA | SEQ ID NO:4232 AACTATGGCATGCAC | SEQ ID NO:12244 GTTATTTGGTATGAAGAAATAATCAATACTATGCAGACTCCGTGAAGGGC | SEQ ID NO:20256 GAACTGGGGGTTCCGGTCTGACTAC | |
| | | AA | SEQ ID NO:4233 NYGMH | SEQ ID NO:12245 VIWYEENNQYYADSVKG | SEQ ID NO:20257 ELGFRSDY | |
| | | | SEQ ID NO:4234 | SEQ ID NO:12246 | SEQ ID NO:20258 | |

FIGURE 49
(Continued)

| | | | | |
|---|---|---|---|---|
| iPS:392646 | 21-225_20G2 | NA | AGGGATGACATGCAC | GTTATATGGTTTGATGGAAGTATAAATACTATGCAGACTCCGTGAAGGGC | GATCTGATAGCAGCAGCTGGTACGGTTGACTAC |
| | | | SEQ ID NO:4235 | SEQ ID NO:12247 | SEQ ID NO:20259 |
| | | AA | SDDMH | VIWFDGSNKYYADSVKG | DLIAAAGFVDY |
| | | | SEQ ID NO:4236 | SEQ ID NO:12248 | SEQ ID NO:20260 |
| iPS:392648 | 21-225_16D11 | NA | CGCAACACTGCTGCTTGGAGC | AGGACATACTACAGGTCCAAGTGGTATAATGATTATGCAGTATCTGTGAAAAGT | GTAAACAGTGGCTGGTCCATCACTACTACTACGGTATGGACGTC |
| | | | SEQ ID NO:4237 | SEQ ID NO:12249 | SEQ ID NO:20261 |
| | | AA | RNTAAWS | RTYYRSKWYNDYAVSVKS | VNSGWSHHYYYGMDV |
| | | | SEQ ID NO:4238 | SEQ ID NO:12250 | SEQ ID NO:20262 |
| iPS:392650 | 21-225_17A4 | NA | GACTACTACATGAGC | CACATTAGTAGTAGTGGTAGTACCATATATTACGCAGACTCTGTGAAGGGC | TATCGGAATAACCGGGATACTTCGATCTC |
| | | | SEQ ID NO:4239 | SEQ ID NO:12251 | SEQ ID NO:20263 |
| | | AA | DYYMS | HISSSGSTIYYADSVKG | YRNNRGYFDL |
| | | | SEQ ID NO:4240 | SEQ ID NO:12252 | SEQ ID NO:20264 |
| iPS:392652 | 21-225_17C6 | NA | AGCTATGCCATGAAC | GTTATTAGTGGTGGTGGTGGTAACACATTCTACGCAGACTCCGTGAAGGGC | CGTTGGCAGTGGCTGGCTCGGAGGCTTTTGATATC |
| | | | SEQ ID NO:4241 | SEQ ID NO:12253 | SEQ ID NO:20265 |
| | | AA | SYAMN | VISGRGGNTFYADSVKG | RLAVAGSEAFDI |
| | | | SEQ ID NO:4242 | SEQ ID NO:12254 | SEQ ID NO:20266 |

FIGURE 49
(Continued)

| iPS:392654 | 21-225_17A10 | NA | AACTATGGCATGCAC | GTTATTTGGTATGAAGAAATAATCAATACTATGCAGACTCCGTGAAGGGC | GAACTGGGGGTTCCGGTCTGACTAC |
|---|---|---|---|---|---|
| | | | SEQ ID NO:4243 | SEQ ID NO:12255 | SEQ ID NO:20267 |
| | | AA | NYGMH | VIWYEENNQYYADSVKG | ELGFRSDY |
| | | | SEQ ID NO:4244 | SEQ ID NO:12256 | SEQ ID NO:20268 |
| iPS:392656 | 21-225_1F2 | NA | AGGAGTAGTTACTACTGGGGC | AATATTTATTATAGTGGGAGCGGCCTACACAACCCGTCCCTCAAGGGT | CATGGAAAAGACTGGGGCCTTGACTAC |
| | | | SEQ ID NO:4245 | SEQ ID NO:12257 | SEQ ID NO:20269 |
| | | AA | RSSYYWG | NIYYSGSAYNNPSLKG | HGKDWGLDY |
| | | | SEQ ID NO:4246 | SEQ ID NO:12258 | SEQ ID NO:20270 |
| iPS:392658 | 21-225_18E8 | NA | AACTATGGCATGCAC | GTTATTTGGTATGAAGAAATAATCAATACTATGCAGACTCCGTGAAGGGC | GAACTGGGGGTTCCGGTCTGACTAC |
| | | | SEQ ID NO:4247 | SEQ ID NO:12259 | SEQ ID NO:20271 |
| | | AA | NYGMH | VIWYEENNQYYADSVKG | ELGFRSDY |
| | | | SEQ ID NO:4248 | SEQ ID NO:12260 | SEQ ID NO:20272 |
| iPS:392660 | 21-225_19B3 | NA | AGTTATGACATGCAC | GTTATATGGTATGACGGAAGTGATAAATACTATGCAGACTCCGTGAAGGGC | GATCGGGCCTATAGCAGCTCGTCTGACTAC |
| | | | SEQ ID NO:4249 | SEQ ID NO:12261 | SEQ ID NO:20273 |
| | | AA | SYDMH | VIWYDGSDKYYADSVKG | DRAYSSSSDY |
| | | | SEQ ID NO:4250 | SEQ ID NO:12262 | SEQ ID NO:20274 |

FIGURE 49
(Continued)

| iPS:392664 | 21-225_20F6 | NA | AGCTATGGCATGCAC SEQ ID NO:4251 | GTTATATGGCATGATGG AAGTAATAAATACTATG CAGACTCCGTGAAGGGC SEQ ID NO:12263 | GATCTGAGTATGGGCGGAAT GGACGTC SEQ ID NO:20275 |
|---|---|---|---|---|---|
| | | AA | SYGMH SEQ ID NO:4252 | VIWHDGSNKYYADSVKG SEQ ID NO:12264 | DLSMGGMDV SEQ ID NO:20276 |
| iPS:392666 | 21-225_16F11 | NA | AGCTATGGCATGCAC SEQ ID NO:4253 | GTTATATGGTATGGAGGA AAATAATAAATACTATG TAGACTCCGTGAAGGGC SEQ ID NO:12265 | GAACTAGGCTTCCAGTCTGA CTAC SEQ ID NO:20277 |
| | | AA | SYGMH SEQ ID NO:4254 | VIWYEENNKYYVDSVKG SEQ ID NO:12266 | ELGFQSDY SEQ ID NO:20278 |
| iPS:392668 | 21-225_17B4 | NA | AGCTATGCCATGAAC SEQ ID NO:4255 | GTTATTAGTGGCCGTGGT GGTAACACATTCTACGC AGACTCCGTGAAGGGC SEQ ID NO:12267 | CGTTGGCAGTGGCTGGCTC GGAGGCTTTTGATATC SEQ ID NO:20279 |
| | | AA | SYAMN SEQ ID NO:4256 | VISGRGGNTFYADSVKG SEQ ID NO:12268 | RLAVAGSEAFDI SEQ ID NO:20280 |
| iPS:392674 | 21-225_18C2 | NA | GACTATGGCATGCAC SEQ ID NO:4257 | GTTATATGGTATGATGTA ACTAATAAATACTATGC AGACTCCGTGAAGGGC SEQ ID NO:12269 | GAGCTTGGCTGGTACGAGGA CTAC SEQ ID NO:20281 |
| | | AA | DYGMH SEQ ID NO:4258 | VIWYDVTNKYYADSVKG SEQ ID NO:12270 | ELGWYEDY SEQ ID NO:20282 |

FIGURE 49
(Continued)

| | | | | | |
|---|---|---|---|---|---|
| iPS:392676 | 21-225_19F3 | NA | GGTAGTAGTTACTACTGGGG C | AATATCTATTATATAGTGGG AGCACCTACTACAACCC GTCCTTCAAGAGT | CATTCCAGTAGTAGCTGGTCCCT TGACTAC |
| | | | SEQ ID NO:4259 | SEQ ID NO:12271 | SEQ ID NO:20283 |
| | | AA | GSSYYWG | NIYYSGSTYYNPSFKS | HSSSWSLDY |
| | | | SEQ ID NO:4260 | SEQ ID NO:12272 | SEQ ID NO:20284 |
| iPS:392678 | 21-225_20F3 | NA | AGCTATGCCATGAAC | GTTATTAGTGGTAGTGGT GGTAGCACATACTACGC AGACTCCGTGAAGGGC | AGGATAGCAGCAGCTGGTAC GGAGTACTTCGATCTC |
| | | | SEQ ID NO:4261 | SEQ ID NO:12273 | SEQ ID NO:20285 |
| | | AA | SYAMN | VISGSGGSTYYADSVKG | RIAAAGTEYFDL |
| | | | SEQ ID NO:4262 | SEQ ID NO:12274 | SEQ ID NO:20286 |
| iPS:392680 | 21-225_20A7 | NA | AACTATGGCATGCAC | GTTATTTGGTATGAAGA AATAATCAATACTATG CAGACTCCGTGAAGGGC | GAACTGGGGTTCCGGTCTGA CTAC |
| | | | SEQ ID NO:4263 | SEQ ID NO:12275 | SEQ ID NO:20287 |
| | | AA | NYGMH | VIWYEENNQYYADSVKG | ELGPRSDY |
| | | | SEQ ID NO:4264 | SEQ ID NO:12276 | SEQ ID NO:20288 |
| iPS:392682 | 21-225_16A12 | NA | AGCTATAGAATGAAC | TCCATTAGTGGTAGTAGT ACTGACATATACGC AGACTCAGTGAAGGGC | AGGGACTTC |
| | | | SEQ ID NO:4265 | SEQ ID NO:12277 | SEQ ID NO:20289 |
| | | AA | SYRMN | SISGSSTDIYYADSVKG | RDF |
| | | | SEQ ID NO:4266 | SEQ ID NO:12278 | SEQ ID NO:20290 |
| iPS:392684 | 21_225_17F4 | NA | AACTATGGCATGAAC | GTTATATGGTATGATGG AATAATAAACACTATG CAGACTCCGTGAAGGGC | AGTGGGAGCTACTTCTTTGA CTAC |

FIGURE 49
(Continued)

| | | | | | |
|---|---|---|---|---|---|
| iPS:392686 | 21-225_17F4 | AA | SEQ ID NO:4267<br>NYGMN | SEQ ID NO:12279<br>VIWYDGNNKHYADSVKG | SEQ ID NO:20291<br>SGSYFFDY |
| | | NA | SEQ ID NO:4268<br>GACTATGGCATGCAC | SEQ ID NO:12280<br>GTTATATGGTTTGATGGA<br>AGTAATAAATACTATGC<br>AGACTCCGTGAAGGGC | SEQ ID NO:20292<br>GATCTTGGCTGGACGGAAGA<br>ATAC |
| iPS:392690 | 21-225_17C7 | AA | SEQ ID NO:4269<br>DYGMH | SEQ ID NO:12281<br>VIWFDGSNKYYADSVKG | SEQ ID NO:20293<br>DLGWTEEY |
| | | NA | SEQ ID NO:4270<br>GACTATGGCATGCAC | SEQ ID NO:12282<br>GTTATATGGTTTGATGGAAGA<br>AGTAATAAATACTATGT<br>AGACTCCGTGAAGGGC | SEQ ID NO:20294<br>GATCTTGGCTGGACGGAAGA<br>GTAC |
| iPS:392692 | 21-225_18F2 | AA | SEQ ID NO:4271<br>DYGMH | SEQ ID NO:12283<br>VIWFDGSNKYYVDSVKG | SEQ ID NO:20295<br>DLGWTEEY |
| | | NA | SEQ ID NO:4272<br>ACCTATAGCATGAAC | SEQ ID NO:12284<br>TACATTAGTAGGAGTAG<br>TAGTACCATAGACTACG<br>CAGACTCTGTGAAGGGC | SEQ ID NO:20296<br>GGAGGTGGGAGCCCTTTGA<br>CTAC |
| iPS:392694 | 21-225_18G10 | AA | SEQ ID NO:4273<br>TYSMN | SEQ ID NO:12285<br>YISRSSTIDYADSVKG | SEQ ID NO:20297<br>GGGSPFDY |
| | | NA | SEQ ID NO:4274<br>AGCTATAGCCATGCAC | SEQ ID NO:12286<br>GTTATATGGTTTGATGGA<br>AGTGATAAATACTATGC<br>AGACTCCGTGAAGGGC | SEQ ID NO:20298<br>GATCGGGCCTATAGTAGCTC<br>GTCTGACTAC |
| | 21-225_19A5 | AA | SEQ ID NO:4275<br>SYAMH | SEQ ID NO:12287<br>VIWFDGSDKYYADSVKG | SEQ ID NO:20299<br>DRAYSSSSDY |
| | | NA | SEQ ID NO:4276 | SEQ ID NO:12288 | SEQ ID NO:20300 |

FIGURE 49
(Continued)

| | | | | |
|---|---|---|---|---|
| iPS:392696 | 21-225_20A4 | NA | AGCTATGCCATGACC | GTTATAAGTGGTAGTGGTGGTTACACATACAACGCGGACTCCGTGAAGGGC | CGTATAGCAGTAGTGGCTGGCTCGGAGGCTTTTGATATC |
| | | | SEQ ID NO:4277 | SEQ ID NO:12289 | SEQ ID NO:20301 |
| | | AA | SYAMT | VISGSGGTYNADSVKG | RIAVAGSEAFDI |
| | | | SEQ ID NO:4278 | SEQ ID NO:12290 | SEQ ID NO:20302 |
| iPS:392700 | 21-225_16E12 | NA | AACTATGGCATGCAC | GTTATATGGTATGAGGGAAGTAATAAATATTATGTAGACTCCGTGAGGGGC | GAGCTAGGCTTCCAGTCTGATCAC |
| | | | SEQ ID NO:4279 | SEQ ID NO:12291 | SEQ ID NO:20303 |
| | | AA | NYGMH | VIWYEGSNKYYVDSVRG | ELGFQSDH |
| | | | SEQ ID NO:4280 | SEQ ID NO:12292 | SEQ ID NO:20304 |
| iPS:392702 | 21-225_17F7 | NA | AGCTATGCCATGAAC | ATTATTAGTGGTCGTGGTGGTAACACATTCTACGCAGACTCCGTGAAGGGC | CGTTTGGCAGTGGCTGGCTCGGAGGCTTTTGATATC |
| | | | SEQ ID NO:4281 | SEQ ID NO:12293 | SEQ ID NO:20305 |
| | | AA | SYAMN | IISGRGGNTFYADSVKG | RLAVAGSEAFDI |
| | | | SEQ ID NO:4282 | SEQ ID NO:12294 | SEQ ID NO:20306 |
| iPS:392704 | 21-225_17F13 | NA | AGCTATGCCATGAGC | GTTATTAGTGGTAGAGGTGGTAACACATACTCCGCAGACTCCGTGAAGGGC | CGTTTAGCAGTGGCTGGCTCGGAGGCTTTTTCATATC |
| | | | SEQ ID NO:4283 | SEQ ID NO:12295 | SEQ ID NO:20307 |
| | | AA | SYAMS | VISGRGGNTYSADSVKG | RLAVAGSEAFHI |
| | | | SEQ ID NO:4284 | SEQ ID NO:12296 | SEQ ID NO:20308 |
| iPS:392706 | 21-225_18A3 | NA | AGAAGTAGTTATTACTGGGC | AATATCTATTATATAGTGGGTATACCTACTACACTCCGTCCCTCAAGAGT | CATAGCACCAGCTGGTCCCTTGACTAC |
| | | | SEQ ID NO:4285 | SEQ ID NO:12297 | SEQ ID NO:20309 |
| | | AA | RSSYYWG | NIYYSGYTYTPSLKS | HSTSWSLDY |
| | | | SEQ ID NO:4286 | SEQ ID NO:12298 | SEQ ID NO:20310 |

FIGURE 49
(Continued)

| iPS: | Clone | Type | Seq1 | Seq2 | Seq3 |
|---|---|---|---|---|---|
| iPS:392708 | 21-225_18D11 | NA | AGCTATAGCATGAAC<br>SEQ ID NO:4287 | TACATTAGTAGTAGTAGT<br>GGTACCATATACTGC<br>AGACTCTGTGAAGGGC<br>SEQ ID NO:12299 | GGAGGTGGGAGCCCTTTGA<br>CTAC<br>SEQ ID NO:20311 |
| | | AA | SYSMN<br>SEQ ID NO:4288 | YISSSSGTIYYADSVKG<br>SEQ ID NO:12300 | GGGSPFDY<br>SEQ ID NO:20312 |
| iPS:392710 | 21-225_19A10 | NA | AGCTATGGCATGCAC<br>SEQ ID NO:4289 | GTTATATGGTATGATGA<br>AAGTAATAAATACTATG<br>CAGACTCCGTGAAGGGC<br>SEQ ID NO:12301 | GAGCTGCCTGGTACGAGGA<br>CTCC<br>SEQ ID NO:20313 |
| | | AA | SYGMH<br>SEQ ID NO:4290 | VIWYDESNKYYADSVKG<br>SEQ ID NO:12302 | ELAWYEDS<br>SEQ ID NO:20314 |
| iPS:392714 | 21-225_16G12 | NA | AGCTATGCCATGACC<br>SEQ ID NO:4291 | ACTATTAGTGGTCGTGGT<br>GGTCACACATACTACG<br>AGACTCCGTGAGGGC<br>SEQ ID NO:12303 | CAGGACTGC<br>SEQ ID NO:20315 |
| | | AA | SYAMT<br>SEQ ID NO:4292 | TISGRGGHTYYADSVRG<br>SEQ ID NO:12304 | QDC<br>SEQ ID NO:20316 |
| iPS:392716 | 21-225_17B5 | NA | GACTATGGCATGCAC<br>SEQ ID NO:4293 | GTTATATGGTATGATGA<br>AAGTAATAAACACTATA<br>TAGACTCCGTGAAGGGC<br>SEQ ID NO:12305 | GAACTGGGGTTCCGGTTTGA<br>CTAC<br>SEQ ID NO:20317 |
| | | AA | DYGMH<br>SEQ ID NO:4294 | VIWYDESNKHYIDSVKG<br>SEQ ID NO:12306 | ELGFRFDY<br>SEQ ID NO:20318 |
| iPS:392718 | | NA | AGCTATGCTATCAAC | TGGATGAACCCTAACAC<br>TGGTAACACAGGCTATG<br>CACAGAAGTTCCAGGGC | AAGGCTGGGTTTGACTAC |

FIGURE 49
(Continued)

| | | | | | |
|---|---|---|---|---|---|
| iPS:392720 | 21-225_17B8 | AA | SEQ ID NO:4295 SYAIN | SEQ ID NO:12307 WMNPNTGNTGYAQKFQG | SEQ ID NO:20319 KAGFDY |
| iPS:392722 | 21-225_17A12 | NA | SEQ ID NO:4296 AGCTATGCCATGAGC | SEQ ID NO:12308 ATTATTAGTGGTCGTGGG GGAAACGCATTCTACGC AGACTCCGTGAAGGGC | SEQ ID NO:20320 CGTATAGCAGTGGCTGGCTC GGAGGCTTTTGATATC |
| | | AA | SEQ ID NO:4297 SYAMS | SEQ ID NO:12309 IISGRGGNAFYADSVKG | SEQ ID NO:20321 RIAVAGSEAFDI |
| iPS:392726 | 21-225_18E12 | NA | SEQ ID NO:4298 AGCTATGCCATGAGC | SEQ ID NO:12310 ATTATTAGTGGTCGTGGT GGTAACACATTCTACGC AGACTCCGTGAAGGGC | SEQ ID NO:20322 CGTCTGGCCAGTGGCTGGCTC GGAGGCTTTTGATATC |
| | | AA | SEQ ID NO:4299 SYAMS | SEQ ID NO:12311 IISGRGGNTFYADSVKG | SEQ ID NO:20323 RLAVAGSEAFDI |
| iPS:392728 | 21-225_20B5 | NA | SEQ ID NO:4300 AGCTATAGCATGAAC | SEQ ID NO:12312 TCCATTAGTGGGAGTAG TAGTTACATATACTAGC AGACTCAGTGAAGGGC | SEQ ID NO:20324 GATCGTGGGAGCTAC |
| | | AA | SEQ ID NO:4301 SYSMN | SEQ ID NO:12313 SISGSSSYIYYADSVKG | SEQ ID NO:20325 DRGSY |
| | 21-225_20F7 | NA | SEQ ID NO:4302 GACTATTACATGAGC | SEQ ID NO:12314 CACATTAGTAGTAGTGG TAGTACCATATACTACGC AGACTCTGTGAAGGGC | SEQ ID NO:20326 TATCGGAATAACCGGGGGTA CTTCGATCTC |
| | | AA | SEQ ID NO:4303 DYYMS | SEQ ID NO:12315 HISSSGSTYYADSVKG | SEQ ID NO:20327 YRNNRGYFDL |
| | | | SEQ ID NO:4304 | SEQ ID NO:12316 | SEQ ID NO:20328 |

FIGURE 49
(Continued)

| | | | | | |
|---|---|---|---|---|---|
| iPS:392730 | 21-225_17A1 | NA | AGCTATGGCCATGAAC | GTTATTAGTAGTGGTAGTGGT AGTAACACATACTACGC AGACTCCGTGAAGGGC | AGATATACCAGTGACTGGCA TGATGCTTTTGATATC |
| | | | SEQ ID NO:4305 | SEQ ID NO:12317 | SEQ ID NO:20329 |
| | | AA | SYAMN | VISGSGSNTYYADSVKG | RYTSDWHDAFDI |
| | | | SEQ ID NO:4306 | SEQ ID NO:12318 | SEQ ID NO:20330 |
| iPS:392732 | 21-225_17E5 | NA | GACTATGGCATGCAC | CTTATATGGTATGATGTA ACTAATAAATACTATGG AGACTCCGTGAAGGGC | GAGCTTGGCTGGTACGAGGA CTAC |
| | | | SEQ ID NO:4307 | SEQ ID NO:12319 | SEQ ID NO:20331 |
| | | AA | DYGMH | LIWYDVTNKYYGDSVKG | ELGWYEDY |
| | | | SEQ ID NO:4308 | SEQ ID NO:12320 | SEQ ID NO:20332 |
| iPS:392734 | 21-225_17D8 | NA | AGCTATGGCTTGAAC | TCCATTAGTGGTAGTGGT AGTCACATATCCTACGC GGACTCAGTGAAGGGC | GATCGGGGCAGTGGC |
| | | | SEQ ID NO:4309 | SEQ ID NO:12321 | SEQ ID NO:20333 |
| | | AA | SYGLN | SISGSGSHISYADSVKG | DRGSG |
| | | | SEQ ID NO:4310 | SEQ ID NO:12322 | SEQ ID NO:20334 |
| iPS:392736 | 21-225_17B12 | NA | AGCTATGCCATGAAC | GTTATTAGTGGTAGTGGT GGTAGCACATACTACGC AGACTCCGTGAAGGGC | AGGTATACCAGTGACTGGCA TGATGCTTTTGATATC |
| | | | SEQ ID NO:4311 | SEQ ID NO:12323 | SEQ ID NO:20335 |
| | | AA | SYAMN | VISGSGGSTYYADSVKG | RYTSDWHDAFDI |
| | | | SEQ ID NO:4312 | SEQ ID NO:12324 | SEQ ID NO:20336 |
| iPS:392738 | 21-225_18G4 | NA | AGCTATGGCATGCAC | ATTATATGGTATGATGG AAGTAATAAATACTATG CAGACTCCGTGAAGGGC | GATCTGAGTATGGGCGGTAT GGACGTC |

FIGURE 49
(Continued)

| | | | | | |
|---|---|---|---|---|---|
| iPS:392740 | 21-225_18H12 | AA | SEQ ID NO:4313 SYGMH | SEQ ID NO:12325 HWYDGSNKYYADSVKG | SEQ ID NO:20337 DLSMGGMDV |
| | | NA | SEQ ID NO:4314 GACTATGGCATGCAC | SEQ ID NO:12326 GTTATATGGTATGATGTAACTAATAAATACTATGCAGACTCCGTGAAGGGC | SEQ ID NO:20338 GAGGTTGGCTGGTACGAGGACTAC |
| iPS:392742 | 21-225_20B2 | AA | SEQ ID NO:4315 DYGMH | SEQ ID NO:12327 VIWYDVTNKYYADSVKG | SEQ ID NO:20339 EVGWYEDY |
| | | NA | SEQ ID NO:4316 AATTATGTCATTCAC | SEQ ID NO:12328 GTTATATGGTATGATGGAAGTAATAAATACTATGCAGACTCCGTGAAGGGC | SEQ ID NO:20340 GAGAAGTATAGCAGCAGCTGGTACGACTACGGTATGGACGTC |
| iPS:392744 | 21-225_20D5 | AA | SEQ ID NO:4317 NYVIH | SEQ ID NO:12329 VIWYDGSNKYYADSVKG | SEQ ID NO:20341 EKYSSSWYDYGMDV |
| | | NA | SEQ ID NO:4318 AGCTATGGCATGCAC | SEQ ID NO:12330 GTTATTTGGTATGAAGAAATAATCAATACTATGCAGACTCCGTGAAGGGC | SEQ ID NO:20342 GAACTGGGGTTCCGGTCTGACTAC |
| iPS:392746 | 21-225_20H7 | AA | SEQ ID NO:4319 SYGMH | SEQ ID NO:12331 VIWYEENNQYYADSVKG | SEQ ID NO:20343 ELGFRSDY |
| | | NA | SEQ ID NO:4320 AGCTATAGCATGAAC | SEQ ID NO:12332 TCCATTAGTGGTAGTAGTAGTTTCATATACTACGCAGACTCAGTGAAGGGC | SEQ ID NO:20344 GTAGCAGCTCTTGACTAC |

FIGURE 49
(Continued)

| | | | | | | |
|---|---|---|---|---|---|---|
| iPS:392748 | 21-225_20H7 | AA | SEQ ID NO:4321<br>SYSMN | SEQ ID NO:12333<br>SISGSSSFIYYADSVKG | SEQ ID NO:20345<br>VAALDY | |
| | | NA | SEQ ID NO:4322<br>AGCTATAGCGTGAAC | SEQ ID NO:12334<br>TCCATTAGTAGTAGTAGTAGT<br>AGTTCCTATACTACGCA<br>GACTCAGTGAAGGGC | SEQ ID NO:20346<br>AACTGGGACTAC | |
| iPS:392750 | 21-225_20A8 | AA | SEQ ID NO:4323<br>SYSVN | SEQ ID NO:12335<br>SISSSSFLYYADSVKG | SEQ ID NO:20347<br>NWDY | |
| | | NA | SEQ ID NO:4324<br>AGCGATGACATGCAC | SEQ ID NO:12336<br>GTTATATGGTTTGATGGA<br>AGTAATAAATACTATGC<br>AGACTCCGTGAAGGGC | SEQ ID NO:20348<br>GATCTAATAGCAGCAGCTGG<br>TACGGTTGACTAC | |
| iPS:392750 | 21-225_20A10 | AA | SEQ ID NO:4325<br>SDDMH | SEQ ID NO:12337<br>VIWFDGSNKYYADSVKG | SEQ ID NO:20349<br>DLIAAAGTVDY | |
| | | NA | SEQ ID NO:4326<br>AGCTATGGCATGCAC | SEQ ID NO:12338<br>GTTATATCATATGATGGA<br>AGTAATAAATACTATGC<br>AGACTCCGTGAAGGGC | SEQ ID NO:20350<br>GGGGTATGGTTCGGGGACCT<br>C | |
| iPS:392754 | 21-225_21D3 | AA | SEQ ID NO:4327<br>SYGMH | SEQ ID NO:12339<br>VISYDGSNKYYADSVKG | SEQ ID NO:20351<br>GVWFGDL | |
| | | NA | SEQ ID NO:4328<br>GACTATGGCATGCAC | SEQ ID NO:12340<br>GTTATATGGTATGATGTA<br>ACTAATGAATACTATGC<br>AGACTCCGTGAAGGGC | SEQ ID NO:20352<br>GAGCTTGGCTGGTACGAGGA<br>CTAC | |
| iPS:392758 | 21-225_21G11 | AA | SEQ ID NO:4329<br>DYGMH | SEQ ID NO:12341<br>VIWYDVTNEYYADSVKG | SEQ ID NO:20353<br>ELGWYEDY | |
| | | | SEQ ID NO:4330 | SEQ ID NO:12342 | SEQ ID NO:20354 | |

FIGURE 49
(Continued)

| | | NA | AGCTATGCCATGAAC | ATTATTAGTGGTGGTCGTGGT GTTAACACATTCTACGCA GACTCCGTGAAGGGC | CGTTTGGCAGTGGCTGGCTC GGAGGCTTTTGATATC |
|---|---|---|---|---|---|
| iPS:392760 | 21-225_22G3 | | SEQ ID NO:4331 | SEQ ID NO:12343 | SEQ ID NO:20355 |
| | | AA | SYAMN | IISGRGVNTFYADSVKG | RLAVAGSEAFDI |
| | | | SEQ ID NO:4332 | SEQ ID NO:12344 | SEQ ID NO:20356 |
| iPS:392762 | 21-225_22G5 | NA | AGCTATGCCATGAAC | GTTATTAGTCGTAGTGGT GGTTACACATACTACGC GGACTCCGTGAAGGGC | CGTTTAGCAGTGGCTGGCTC GGAGGCTTTTGATATC |
| | | | SEQ ID NO:4333 | SEQ ID NO:12345 | SEQ ID NO:20357 |
| | | AA | SYAMN | VISRSGGYTYYADSVKG | RLAVAGSEAFDI |
| | | | SEQ ID NO:4334 | SEQ ID NO:12346 | SEQ ID NO:20358 |
| iPS:392764 | 21-225_22G10 | NA | AGCTATGCCATGAAC | GTTATTAGTGGTGGTCGTGGT GGTAACACATTCTACGC AGACTCCGTGAAGGGC | CGTATGGCAGTGGCTGGCTC GGAGGCTTTTGATATC |
| | | | SEQ ID NO:4335 | SEQ ID NO:12347 | SEQ ID NO:20359 |
| | | AA | SYAMN | VISGSGGNTFYADSVKG | RMAVAGSEAFDI |
| | | | SEQ ID NO:4336 | SEQ ID NO:12348 | SEQ ID NO:20360 |
| iPS:392766 | 21-225_23H4 | NA | AGCTATGCCATGAAC | GTTATTAGTGGTAGTGGT GGTACCACATACTTCGC AGACTCCGTGAAGGGC | AGAAATAGCAGTGGCTGGCA TGATGTTTTTGATATC |
| | | | SEQ ID NO:4337 | SEQ ID NO:12349 | SEQ ID NO:20361 |
| | | AA | SYAMN | VISGSGGTTYFADSVKG | RNSSGWHDVFDI |
| | | | SEQ ID NO:4338 | SEQ ID NO:12350 | SEQ ID NO:20362 |
| iPS:392768 | 21-225_20B8 | NA | AGTTATAGCATGAAC | TCCATCAGTGGCAGTGG TAGTCACATATACTACGC GGACTCAGTGAAGGGC | GATCGGGGCAGTGGC |
| | | | SEQ ID NO:4339 | SEQ ID NO:12351 | SEQ ID NO:20363 |
| | | AA | SYSMN | SISGSGSHIYYADSVKG | DRGSG |
| | | | SEQ ID NO:4340 | SEQ ID NO:12352 | SEQ ID NO:20364 |

FIGURE 49
(Continued)

| iPS: | | | | | | |
|---|---|---|---|---|---|---|
| iPS:392770 | 21-225_20C10 | NA | AGCTATGCCATGAAC | GTTATTAGTAGTGGTAGTGGT GGTACCACATACTACGC AGACTCCGTGAAGGGC | AGGTATACCAGTGACTGGCA TGATGCTTTTGATATC | |
| | | AA | SEQ ID NO:4341 SYAMN | SEQ ID NO:12353 VISGSGGTTYYADSVKG | SEQ ID NO:20365 RYTSDWHDAFDI | |
| iPS:392772 | 21-225_20E12 | NA | SEQ ID NO:4342 AGCTATGGCATGCAC | SEQ ID NO:12354 GTTATGTGGTATGATGA AAGTAATAAACACTATG CAGACTCCGTGAAGGGC | SEQ ID NO:20366 GAACTGGGGTTCCGGTTTGA CTAC | |
| | | AA | SEQ ID NO:4343 SYGMH | SEQ ID NO:12355 VMWYDESNKHYADSVKG | SEQ ID NO:20367 ELGFRFDY | |
| iPS:392774 | 21-225_21F3 | NA | SEQ ID NO:4344 AGAAGTAGTTACTACTGGG C | SEQ ID NO:12356 AGCATCTATTATAGTGG GAGCACCTACTACAACC CGTCCCTCAAGAGT | SEQ ID NO:20368 CTTAGCAGCAGCTGGGACTT CCAGCAC | |
| | | AA | SEQ ID NO:4345 RSSYYWG | SEQ ID NO:12357 SIYYSGSTYYNPSLKS | SEQ ID NO:20369 LSSSWDFQH | |
| iPS:392776 | 21-225_21A12 | NA | SEQ ID NO:4346 AGCTATAGCATGAAC | SEQ ID NO:12358 TCCATTAGTGGTAGTAGT AGTTACATATACTACGC AGACTCAGTGAAGGGC | SEQ ID NO:20370 GCGGCTGGCTTGACTAC | |
| | | AA | SEQ ID NO:4347 SYSMN | SEQ ID NO:12359 SISGSSSYIYYADSVKG | SEQ ID NO:20371 AAGFDY | |
| iPS:392778 | 21-225_22H3 | NA | SEQ ID NO:4348 AGCTATAGCATGAAC | SEQ ID NO:12360 TCCATTAGTAGTAGTAGT AGTTACATATACTACGC AGACTCAGTGAAGGGC | SEQ ID NO:20372 GATAGGGGCAGCCTC | |
| | | | SEQ ID NO:4349 | SEQ ID NO:12361 | SEQ ID NO:20373 | |

FIGURE 49
(Continued)

| | | | | | | |
|---|---|---|---|---|---|---|
| iPS:392780 | 21-225_22B7 | AA | SYSMN<br>SEQ ID NO:4350 | SISSSSSYIYYADSVKG<br>SEQ ID NO:12362 | DRGSL<br>SEQ ID NO:20374 |
| | | NA | AGCTATGGCATGAAC | GTTATTTGGTATGAAGA<br>AAATAATCAATACTATG<br>CAGACTCCGTGAAGGGC | GAAGTGGGGTTCCGGTCTGA<br>CTAC |
| | | | SEQ ID NO:4351 | SEQ ID NO:12363 | SEQ ID NO:20375 |
| iPS:392782 | 21-225_22B12 | AA | SYGMH | VIWYEENNQYYADSVKG | EVGFRSDY |
| | | | SEQ ID NO:4352 | SEQ ID NO:12364 | SEQ ID NO:20376 |
| | | NA | AGCTATAGCATGAAC | TCCATTAGTAGTAGTAGT<br>AGTTACACATACTACGC<br>AGACTCCGTGAAGGGC | GTAGCAGCCCTTGACTCC |
| | | | SEQ ID NO:4353 | SEQ ID NO:12365 | SEQ ID NO:20377 |
| iPS:392784 | 21-225_23C7 | AA | SYSMN | SISGSSSYTYYADSVKG | VAALDS |
| | | | SEQ ID NO:4354 | SEQ ID NO:12366 | SEQ ID NO:20378 |
| | | NA | AGCTATGTTATGAGC | GCTATGAGTGGTAGTGG<br>TGGTAGCACATATTATGT<br>AGACTCCGTGAAGGGC | ACTGGGGTCTTTGACTAC |
| | | | SEQ ID NO:4355 | SEQ ID NO:12367 | SEQ ID NO:20379 |
| iPS:392786 | 21-225_24E1 | AA | SYVMS | AMSGSGGSTYYVDSVKG | TGVFDY |
| | | | SEQ ID NO:4356 | SEQ ID NO:12368 | SEQ ID NO:20380 |
| | | NA | AATTATGATATCAAC | TGGATGCACCTAACAG<br>TGGTAACACAGGCTATG<br>CACAGAGGTTCCAGGGC | AGCAGTGGCTGGGAGGTCTT<br>TGACTAC |
| | | | SEQ ID NO:4357 | SEQ ID NO:12369 | SEQ ID NO:20381 |
| | | AA | NYDIN | WMHPNSGNTGYAQRFQG | SSGWEVFDY |
| | | | SEQ ID NO:4358 | SEQ ID NO:12370 | SEQ ID NO:20382 |

FIGURE 49
(Continued)

| | | | | |
|---|---|---|---|---|
| iPS:392788 | 21-225_20C8 | NA | AGCTATAGCATGAAC | TCCATTAGTGGCAGTAGTACGC | GACAGAGGCAGTCTC |
| | | | | AGTTACATATACTACGC | |
| | | | | AGACTCAGTGAAGGCC | |
| | | | SEQ ID NO:4359 | SEQ ID NO:12371 | SEQ ID NO:20383 |
| | | AA | SYSMN | SISGSSSYIYYADSVKA | DRGSL |
| | | | SEQ ID NO:4360 | SEQ ID NO:12372 | SEQ ID NO:20384 |
| iPS:392790 | 21-225_20D10 | NA | GACTATGGCATGCAC | GTTATATGGTTTGATGGAAGTAATAAATACTATGT | GATCTTGGCTGGACGGAAGAGTAC |
| | | | | AGACTCCGTGAAGGGC | |
| | | | SEQ ID NO:4361 | SEQ ID NO:12373 | SEQ ID NO:20385 |
| | | AA | DYGMH | VIWFDGSNKYYVDSVKG | DLGWTEEY |
| | | | SEQ ID NO:4362 | SEQ ID NO:12374 | SEQ ID NO:20386 |
| iPS:392792 | 21-225_20G12 | NA | AGCTATAGCATGAAC | TCCATTAGCGGTAGTGTGCA | GATCGTGGGAGTAC |
| | | | | AGTTACATCTACTACGCA | |
| | | | | GACTCACTGAAGGGC | |
| | | | SEQ ID NO:4363 | SEQ ID NO:12375 | SEQ ID NO:20387 |
| | | AA | SYSMN | SISGSSSYIYYADSLKG | DRGSY |
| | | | SEQ ID NO:4364 | SEQ ID NO:12376 | SEQ ID NO:20388 |
| iPS:392794 | 21-225_21H3 | NA | AGGAGTAGTTACTGGGGC | AATATTTATTATAGTGGGAGCACCTACGACAACCCGTCCCTCAAGAGT | CATGGAAAAGACTGGGCCTTGACTAC |
| | | | SEQ ID NO:4365 | SEQ ID NO:12377 | SEQ ID NO:20389 |
| | | AA | RSSYYWG | NIYYSGSTYDNPSLKS | HGKDWGLDY |
| | | | SEQ ID NO:4366 | SEQ ID NO:12378 | SEQ ID NO:20390 |
| iPS:392796 | 21-225_22A4 | NA | GACTATGGCATACAC | GTTATATGGTTTGATGGAAGTAATAAATACTATGCAGACTCCGTGAAGGGC | GATCTTGGCTGGACGGAAGAGTAC |
| | | | SEQ ID NO:4367 | SEQ ID NO:12379 | SEQ ID NO:20391 |

FIGURE 49
(Continued)

| | | AA | DYGIH | VIWFDGSNKYYADSVKG | DLGWTEEY |
|---|---|---|---|---|---|
| iPS:392798 | | | SEQ ID NO:4368 | SEQ ID NO:12380 | SEQ ID NO:20392 |
| | 21-225_22C7 | NA | AGCTATGGCATGCAC | GTTATATGGCATGATGG AAGTAATAAATACTATG CAGACTCCGTGAAGGGC | GATCTGAGTATGGGCGGTAT GGACGTC |
| | | | SEQ ID NO:4369 | SEQ ID NO:12381 | SEQ ID NO:20393 |
| | | AA | SYGMH | VIWHDGSNKYYADSVKG | DLSMGGMDV |
| | | | SEQ ID NO:4370 | SEQ ID NO:12382 | SEQ ID NO:20394 |
| iPS:392800 | 21-225_22D12 | NA | AGGAGTAGTTACTACTGGGG C | AATATCTATTATAGTGGG ACCACCTCCTACAACCC GTCCCTCAAGAGT | CTCAGCAGCAGCTGGTCCGT TGACTAC |
| | | | SEQ ID NO:4371 | SEQ ID NO:12383 | SEQ ID NO:20395 |
| | | AA | RSSYYWG | NIYYSGTSYNPSLKS | LSSSWSVDY |
| | | | SEQ ID NO:4372 | SEQ ID NO:12384 | SEQ ID NO:20396 |
| iPS:392802 | 21-225_23E7 | NA | AGCTATGCCATGAAC | GCTATTAGTGGTAGTGGT GGTTTCACATACTACGCA GACTCCGTGAAGGGC | ACCAGTGGCTTTGACTAC |
| | | | SEQ ID NO:4373 | SEQ ID NO:12385 | SEQ ID NO:20397 |
| | | AA | SYAMN | AISGSGGFTYYADSVKG | TSGFDY |
| | | | SEQ ID NO:4374 | SEQ ID NO:12386 | SEQ ID NO:20398 |
| iPS:392806 | 21-225_24H3 | NA | AGCTATGGCATGCAC | GTTATATGGTATGATGG AAGTAATAAATACTATG CAGACTCCGTGAAGGGC | GTAGCAGTGGCAGGCGGTAT GGACGTC |
| | | | SEQ ID NO:4375 | SEQ ID NO:12387 | SEQ ID NO:20399 |
| | | AA | SYGMH | VIWYDGSNKYYADSVKG | VAVAGGMDV |
| | | | SEQ ID NO:4376 | SEQ ID NO:12388 | SEQ ID NO:20400 |

FIGURE 49
(Continued)

| | | | | | |
|---|---|---|---|---|---|
| iPS:392808 | 21-225_20F8 | NA | AGCTATGCCATGAGC<br>SEQ ID NO:4377 | GTTATTAGTGGTAGTGGT<br>GGTAGCACATATTACGC<br>AGACTCCGTGAAGGGC<br>SEQ ID NO:12389 | AGGTATAACAGTGGCTGGCA<br>TGATGTTTTTGATATC<br>SEQ ID NO:20401 |
| | | AA | SYAMS<br>SEQ ID NO:4378 | VISGSGGSTYYADSVKG<br>SEQ ID NO:12390 | RYNSGWHDVFDI<br>SEQ ID NO:20402 |
| iPS:392810 | 21-225_20H12 | NA | AACTATGGCATGCAC<br>SEQ ID NO:4379 | GTTATATGGTATGATGA<br>AATAATAAATACTATG<br>TAGACTCCGTGAAGGGC<br>SEQ ID NO:12391 | GAGTTGGGGTTCCGGTCTGA<br>CTAC<br>SEQ ID NO:20403 |
| | | AA | NYGMH<br>SEQ ID NO:4380 | VIWYDENNKYYVDSVKG<br>SEQ ID NO:12392 | ELGFRSDY<br>SEQ ID NO:20404 |
| iPS:392812 | 21-225_21F4 | NA | AGCTATGCCATGAAC<br>SEQ ID NO:4381 | GTTATTAGTGGTCGTGGT<br>GGTAACACATTCTACGC<br>AGACTCCGTGAAGGGC<br>SEQ ID NO:12393 | CGTTTGGCAGTGGCTGGCTC<br>GGAGGCTTGTGATATC<br>SEQ ID NO:20405 |
| | | AA | SYAMN<br>SEQ ID NO:4382 | VISGRGGNTFYADSVKG<br>SEQ ID NO:12394 | RLAVAGSEACDI<br>SEQ ID NO:20406 |
| iPS:392814 | 21-225_22A1 | NA | AGCTATGCCATGCAC<br>SEQ ID NO:4383 | GTTATGTGGTATGATGG<br>AAGTAATAAATATTATG<br>CAGACTCCGTGAAGGGC<br>SEQ ID NO:12395 | GATGGGGGATTTTTGGAGTG<br>GTTAGACTAC<br>SEQ ID NO:20407 |
| | | AA | SYGMH<br>SEQ ID NO:4384 | VMWYDGSNKYYADSVK<br>G<br>SEQ ID NO:12396 | DGGFLEWLDY<br>SEQ ID NO:20408 |
| iPS:392816 | 21-225_22E4 | NA | AGCTATGCCATGAGC | ATTATTAGTGGTCGTGGT<br>ACTAACACATTCTACGC<br>AGACTCCGTGAAGGGC | CGTATAGCAGTGGCTGGCTC<br>GGAGGCTTTTGATATC |

FIGURE 49
(Continued)

| | | | | | | | |
|---|---|---|---|---|---|---|---|
| iPS:392818 | 21-225_22E4 | AA | SEQ ID NO:4385 SYAMS | SEQ ID NO:12397 IISGRGTNTFYADSVKG | SEQ ID NO:20409 RIAVAGSEAFDI | | |
| | | NA | SEQ ID NO:4386 AGCTATGGCATGCAC | SEQ ID NO:12398 ATTATATCATATGATGGAAGTAATAAATACTATGCAGACTCCGTGAAGGGC | SEQ ID NO:20410 GGGGTTTGTTTGGGGACTT C | | |
| iPS:392820 | 21-225_22D8 | AA | SEQ ID NO:4387 SYGMH | SEQ ID NO:12399 IISYDGSNKYYADSVKG | SEQ ID NO:20411 GVWFGDF | | |
| | | NA | SEQ ID NO:4388 AGAAGTAGTAGTAGTACTACTGGGG C | SEQ ID NO:12400 AGTATCTATTATAGTGGGAGCGCCCAGTACAACCCGTCCCTCAAGAGT | SEQ ID NO:20412 CTGAGCAGCAGCTGGTCTTTGACTAC | | |
| iPS:392822 | 21-225_23D1 | AA | SEQ ID NO:4389 RSSYYWG | SEQ ID NO:12401 SIYYSGSAQYNPSLKS | SEQ ID NO:20413 LSSSWSFDY | | |
| | | NA | SEQ ID NO:4390 AGGAGTAGTTACTACTGGGG C | SEQ ID NO:12402 AATATTTATTATAGTGGGACCACTTACAACAACCCGTCCCTCAAGAGT | SEQ ID NO:20414 CATGGAAAAGACTGGGGCCTTGACTAC | | |
| iPS:392823 | 21-225_23C8 | AA | SEQ ID NO:4391 RSSYYWG | SEQ ID NO:12403 NIYYSGTTYNNPSLKS | SEQ ID NO:20415 HGKDWGLDY | | |
| | | NA | SEQ ID NO:4392 AGGAGTAGTTACTACTGGGG C | SEQ ID NO:12404 AGTATCTATTATAGTGTGGGAGCGCCAACTACAACCCGTCCCTCAAGAGT | SEQ ID NO:20416 CTCAGCAGCAGCTGGTCCATTGACAAC | | |
| iPS:392824 | 21-225_24E5 | AA | SEQ ID NO:4393 RSSYYWG | SEQ ID NO:12405 SIYYSGSANYNPSLKS | SEQ ID NO:20417 LSSSWSIDN | | |
| | | NA | SEQ ID NO:4394 | SEQ ID NO:12406 | SEQ ID NO:20418 | | |

FIGURE 49
(Continued)

| | | | | |
|---|---|---|---|---|
| iPS:392826 | 21-225_20B9 | NA | AGCTATAGCATGAAC | TACATTAGTAGTAGTAGT AGTACCATATACTATGC AGACTCTGTGAAGGGC | TCACTATGGTCCCCCTTTGAC TAC |
| | | | SEQ ID NO:4395 | SEQ ID NO:12407 | SEQ ID NO:20419 |
| | | AA | SYSMN | YISSSSSTIYYADSVKG | SLWSPFDY |
| | | | SEQ ID NO:4396 | SEQ ID NO:12408 | SEQ ID NO:20420 |
| iPS:392830 | 21-225_21A5 | NA | AGTTACTTCTGGAGC | CGTATCTATACCAGTGG GATCACCAACTACAACC CCTCCCTCAAGAGT | GGCCCGACTTCGGGGTGGTT CGACCCC |
| | | | SEQ ID NO:4397 | SEQ ID NO:12409 | SEQ ID NO:20421 |
| | | AA | SYFWS | RIYTSGITNYNPSLKS | GPTSGWFDP |
| | | | SEQ ID NO:4398 | SEQ ID NO:12410 | SEQ ID NO:20422 |
| iPS:392832 | 21-225_21H8 | NA | GACTATGGCATGCAC | GTTATATGGTTTGATGGA AGTAATAAATACTATGC AGACTCCGTGAAGGGC | GATCTTGGCTGGACGGAAGA GTAC |
| | | | SEQ ID NO:4399 | SEQ ID NO:12411 | SEQ ID NO:20423 |
| | | AA | DYGMH | VIWFDGSNKYYADSVKG | DLGWTEEY |
| | | | SEQ ID NO:4400 | SEQ ID NO:12412 | SEQ ID NO:20424 |
| iPS:392834 | 21-225_22C1 | NA | AGGAGTAGTTACTACTGGGG C | AATATCTATTATAGTGGG GCCACCTATTATAATTCG TCCCTCAAGAGT | CATAGCGGCAGCTGGTCCCT TGACTAC |
| | | | SEQ ID NO:4401 | SEQ ID NO:12413 | SEQ ID NO:20425 |
| | | AA | RSSYYWG | NIYYSGATYNSSLKS | HSGSWSLDY |
| | | | SEQ ID NO:4402 | SEQ ID NO:12414 | SEQ ID NO:20426 |
| iPS:392836 | 21-225_22F4 | NA | GACTATGGCATGCAC | GTTATATGGTATGATGG AAGTAATAAATACTATG TAGACTCCGTGAAGGGC | GAAAAGTATAGCAGCAGCTG GTACGACTACGGTATGGACG TC |
| | | | SEQ ID NO:4403 | SEQ ID NO:12415 | SEQ ID NO:20427 |

FIGURE 49
(Continued)

| | | | | DYGMH | | VIWYDGSNKYYVDSVKG | EKYSSSWYDYGMDV |
|---|---|---|---|---|---|---|---|
| iPS:392838 | 21-225_22G8 | | AA | SEQ ID NO:4404 | | SEQ ID NO:12416 | SEQ ID NO:20428 |
| | | | NA | AGGAGTAGTTACTACTGGGGC | | AATATCTATTATAGTGGGAGCACCTACTACAACCCGTCCGTCAAGAGT | CATGGAAAAGACTGGGGCCTTGACTAC |
| | | | AA | SEQ ID NO:4405 RSSYYWG | | SEQ ID NO:12417 NIYYSGSTYYNPSVKS | SEQ ID NO:20429 HGKDWGLDY |
| iPS:392840 | 21-225_23G1 | | NA | SEQ ID NO:4406 AGCTATGCCATGAGC | | SEQ ID NO:12418 GTTATTAGTGGTAGTGGTGGTACCACATATAACACAGACTCCGTGAAGGGC | SEQ ID NO:20430 AGCTCCTTGTTTGACTAC |
| | | | AA | SEQ ID NO:4407 SYAMS | | SEQ ID NO:12419 VISGSGGTTYNTDSVKG | SEQ ID NO:20431 SSLFDY |
| iPS:392842 | 21-225_23G8 | | NA | SEQ ID NO:4408 AGCTATGCCATGAGC | | SEQ ID NO:12420 GCTATTAGTGGTAGTGGTAGTGGTAGCACATACTAGCAGACTCCGTGAAGGGC | SEQ ID NO:20432 AGCAGTGGCTGGTTCGCC |
| | | | AA | SEQ ID NO:4409 SYAMS | | SEQ ID NO:12421 AISGSGGSTYYADSVKG | SEQ ID NO:20433 SSGWFA |
| iPS:392844 | 21-225_23E11 | | NA | SEQ ID NO:4410 TCCTATACCATGAAC | | SEQ ID NO:12422 TCCATTAGTGGTAGTAGTAGTTACATATGGTATGTAGACTCAGTGAAGGGC | SEQ ID NO:20434 GATCGGGGCCAGTCTC |
| | | | AA | SEQ ID NO:4411 SYTMN | | SEQ ID NO:12423 SISGSSSYIWYVDSVKG | SEQ ID NO:20435 DRGSL |
| | | | | SEQ ID NO:4412 | | SEQ ID NO:12424 | SEQ ID NO:20436 |

FIGURE 49
(Continued)

| | | | | |
|---|---|---|---|---|
| iPS:392846 | 21-225_24B6 | NA | AACTATGTCATGCAC | GTTATATGGTATGATGG AAGTAATAAATACTATG CAGACTCCGTGAAGGGC | GAGGAATATAGTAGTGGCTG GTACGACTACGGTATGGACG TC |
| | | | SEQ ID NO:4413 | SEQ ID NO:12425 | SEQ ID NO:20437 |
| | | AA | NYVMH | VIWYDGSNKYYADSVKG | EEYSSGWYDYGMDV |
| | | | SEQ ID NO:4414 | SEQ ID NO:12426 | SEQ ID NO:20438 |
| iPS:392848 | 21-225_20F9 | NA | AGCTATAGCATGAAC | TCCATTAGTAGTAGTAGT AGTTACATACATACGC AGACTCAGTGAAGGGC | GATCGTGGGAGCTGC |
| | | | SEQ ID NO:4415 | SEQ ID NO:12427 | SEQ ID NO:20439 |
| | | AA | SYSMN | SISSSSSYIYYADSVKG | DRGSC |
| | | | SEQ ID NO:4416 | SEQ ID NO:12428 | SEQ ID NO:20440 |
| iPS:392850 | 21-225_20H10 | NA | ACCTATAGCATGAAC | TCCATTAGTAGTAGTAGT AGTTACATATACTACGC AGACTCAGTGAAGGGC | GATCGTGTGGGAGCCTC |
| | | | SEQ ID NO:4417 | SEQ ID NO:12429 | SEQ ID NO:20441 |
| | | AA | TYSMN | SISSSSSYIYYADSVKG | DRGSL |
| | | | SEQ ID NO:4418 | SEQ ID NO:12430 | SEQ ID NO:20442 |
| iPS:392852 | 21-225_21A2 | NA | AGCTATGCCATGAAC | ATTATTAGTGGTCGTGGT GGTAACACATTCTACGC AGACTCCGTGAAGGGC | CGTTGGCAGTGGCTGGCTC GGAGGCTTTTGATATC |
| | | | SEQ ID NO:4419 | SEQ ID NO:12431 | SEQ ID NO:20443 |
| | | AA | SYAMN | IISGRGGNTFYADSVKG | RLAVAGSEAFDI |
| | | | SEQ ID NO:4420 | SEQ ID NO:12432 | SEQ ID NO:20444 |
| iPS:392854 | 21_225_21E5 | NA | GACTATGGCATGCAC | GTTATATGGTATGATGA AAGTAATAAATACTATG CAGACTCCGTGAAGGGC | GAACTGGGGTTCCGGTCTGA CTAT |

FIGURE 49
(Continued)

| | | | | | |
|---|---|---|---|---|---|
| iPS:392856 | 21-225_21E5 | AA | SEQ ID NO:4421<br>DYGMH | SEQ ID NO:12433<br>VIWYDESNKYYADSVKG | SEQ ID NO:20445<br>ELGFRSDY |
| | | NA | SEQ ID NO:4422<br>AGCTATGCCATGAGC | SEQ ID NO:12434<br>GGTATTAGTGGTAGTGG<br>AGGTAACACACCCTACG<br>CAGACTCCGTGAAGGGC | SEQ ID NO:20446<br>GTAGTGGGAGCTGTCCAC |
| iPS:392858 | 21-225_22A2 | AA | SEQ ID NO:4423<br>SYAMS | SEQ ID NO:12435<br>GISGSGGNTPYADSVKG | SEQ ID NO:20447<br>VVGAVH |
| | | NA | SEQ ID NO:4424<br>AGGAGTAGTTACTACTGGGG<br>C | SEQ ID NO:12436<br>AATATTATTATAGTGGG<br>AGCACCTACCACAACCC<br>GTCTCTCAAGAGT | SEQ ID NO:20448<br>CATGGAAAAGACTGGGGCCT<br>TGACTAC |
| iPS:392860 | 21-225_22H4 | AA | SEQ ID NO:4425<br>RSSYYWG | SEQ ID NO:12437<br>NIYYSGSTYHNPSLKS | SEQ ID NO:20449<br>HGKDWGLDY |
| | | NA | SEQ ID NO:4426<br>AGCTATGGCATGCAC | SEQ ID NO:12438<br>GTTATCTGGTATGATGGA<br>AATAATAAATACTATGC<br>AGACTCCGTGAAGGGC | SEQ ID NO:20450<br>GAGCTTGCCTGGTACGAAGA<br>CTAC |
| | 21-225_22H8 | AA | SEQ ID NO:4427<br>SYGMH | SEQ ID NO:12439<br>VIWYDGNNKYYADSVKG | SEQ ID NO:20451<br>ELAWYEDY |
| iPS:392864 | 21-225_23B9 | NA | SEQ ID NO:4428<br>AGTGGTGGTTACTACTGGAG<br>C | SEQ ID NO:12440<br>TACATCTATTACAGTGGG<br>AGCACCTACTACAACCC<br>GTCCCTCAAGAGT | SEQ ID NO:20452<br>GAGGACGGTGCCTTCGGCTA<br>CTACGGTATGGACGTC |
| | | AA | SEQ ID NO:4429<br>SGGYYWS | SEQ ID NO:12441<br>YIYYSGSTYYNPSLKS | SEQ ID NO:20453<br>EDGAFGYYGMDV |

FIGURE 49
(Continued)

| iPS | Clone | NA/AA | CDR1 | CDR2 | CDR3 |
|---|---|---|---|---|---|
| iPS:392866 | 21-225_23H11 | NA | SEQ ID NO:4430 AGCTATGGCATGCAC | SEQ ID NO:12442 GTTATATGGTATGATGAAATAATAAATACTATGTAGACTCCGTGAAGGGC | SEQ ID NO:20454 GAATTGGGGTTCCGGTCTGACTAC |
| | | AA | SEQ ID NO:4431 SYGMH | SEQ ID NO:12443 VIWYDENNKYYVDSVKG | SEQ ID NO:20455 ELGFRSDY |
| iPS:392868 | 21-225_24D6 | NA | SEQ ID NO:4432 AGCTATGGCATGCAC | SEQ ID NO:12444 ATTATATCATATGCTGAAGTAATAAATCCTATGCAGACTCCGTGAAGGGC | SEQ ID NO:20456 CGGGATACAGCTATGGCGGGTACGGTATGGACGTC |
| | | AA | SEQ ID NO:4433 SYGMH | SEQ ID NO:12445 IISYAGSNKSYADSVKG | SEQ ID NO:20457 RGYSYGGYGMDV |
| iPS:392870 | 21-225_20G9 | NA | SEQ ID NO:4434 AGGAGTAGTTACTACTGGGGC | SEQ ID NO:12446 AGTATCTATTATATAGTGGGAGCGCCCTCTTACAACCCGTCCCTCAAGAGT | SEQ ID NO:20458 CTGAGCAGCAGCTGGTCTTTTGACTAC |
| | | AA | SEQ ID NO:4435 RSSYYWG | SEQ ID NO:12447 SIYYSGSASYNPSLKS | SEQ ID NO:20459 LSSSWSFDY |
| iPS:392872 | 21-225_20B11 | NA | SEQ ID NO:4436 AGCTATGTCATGCAC | SEQ ID NO:12448 GTTATAGTGGTATGATGGAAGTAATAAATACTATGCAGACTCCGTGAAGGTC | SEQ ID NO:20460 GAGAGATATACCAGTGGCTGGTATGACTACGGTATGGACGTC |
| | | AA | SEQ ID NO:4437 SYVMH | SEQ ID NO:12449 VIWYDGSNKYYADSVKV | SEQ ID NO:20461 ERYTSGWYDYGMDV |
| | | | SEQ ID NO:4438 | SEQ ID NO:12450 | SEQ ID NO:20462 |

FIGURE 49
(Continued)

| | | | | |
|---|---|---|---|---|
| iPS:392874 | 21-225_21D2 | NA | AACTATGCCATGAGC | GTTCTTAGTGTGTAGTGGT GGTAGCACATTCTACGC AGACTCCGTGAAGGGC | TATTGTAGTAGTAGTGCCAGGTG CCCTTATGATGCCTTTGATAT C |
| | | | SEQ ID NO:4439 | SEQ ID NO:12451 | SEQ ID NO:20463 |
| | | AA | NYAMS | VLSGSGGSTFYADSVKG | YCSSARCPYDAFDI |
| | | | SEQ ID NO:4440 | SEQ ID NO:12452 | SEQ ID NO:20464 |
| iPS:392876 | 21-225_21F7 | NA | GACTATGGCATGCAC | GTTATATGGTTTGATGGA AATAATAAATACTATGT AGACTCCGTGAAGGGC | GATCTTGGCTGGACCGGAAGA GTAC |
| | | | SEQ ID NO:4441 | SEQ ID NO:12453 | SEQ ID NO:20465 |
| | | AA | DYGMH | VIWFDGNNKYYVDSVKG | DLGWTEEY |
| | | | SEQ ID NO:4442 | SEQ ID NO:12454 | SEQ ID NO:20466 |
| iPS:392878 | 21-225_22C5 | NA | AGCTATGCCATGAGC | ATTATTAGTGGTAGTGGT GGTTACACATACTACGC GGACTCCGTGAAGGGC | CGTATAGCAGTGGTGGCTC GGAGGCTTTTGATATC |
| | | | SEQ ID NO:4443 | SEQ ID NO:12455 | SEQ ID NO:20467 |
| | | AA | SYAMS | IISGSGGYTYYADSVKG | RIAVAGSEAFDI |
| | | | SEQ ID NO:4444 | SEQ ID NO:12456 | SEQ ID NO:20468 |
| iPS:392880 | 21-225_22F9 | NA | AGCTATGGCATGCAC | GTTATATGGTATGAGGA AATAATAAAGACTATG TAGACTCCGTGAAGGGC | GAGTTAGGCTTCCAGTCTGA CTAC |
| | | | SEQ ID NO:4445 | SEQ ID NO:12457 | SEQ ID NO:20469 |
| | | AA | SYGMH | VIWYEENNKDYVDSVKG | ELGFQSDY |
| | | | SEQ ID NO:4446 | SEQ ID NO:12458 | SEQ ID NO:20470 |

FIGURE 49
(Continued)

| | | | | |
|---|---|---|---|---|
| iPS:392882 | 21-225_23A3 | NA | AGGAGTAGTTACTACTGGGG C<br>SEQ ID NO:4447 | AATATTATTATAGTGGG AGCACCTACAACAACCC GTCCCTCAAGAGT<br>SEQ ID NO:12459 | CATGGAAAAGACTGGGCCT TGACTTC<br>SEQ ID NO:20471 |
| | | AA | RSSYYWG<br>SEQ ID NO:4448 | NIYYSGSTYNNPSLKS<br>SEQ ID NO:12460 | HGKDWGLDF<br>SEQ ID NO:20472 |
| iPS:392884 | 21-225_23A10 | NA | AGCTATGGCATGCAC<br>SEQ ID NO:4449 | GTTATATGGTATGATGG AAGTAATAAATACTATG CAGACTCCGTGAAGGGC<br>SEQ ID NO:12461 | GAAAGGTATAGCAGTGGCTG GCACGACTACGGTATGGACG TC<br>SEQ ID NO:20473 |
| | | AA | SYGMH<br>SEQ ID NO:4450 | VIWYDGSNKYYADSVKG<br>SEQ ID NO:12462 | ERYSSGWHDYGMDV<br>SEQ ID NO:20474 |
| iPS:392886 | 21-225_23A12 | NA | AATTATGATATCAAC<br>SEQ ID NO:4451 | TGGATGCACCCTAACAG TGGTAACACAGGCTATG CACAGAAGTTCCAGGGC<br>SEQ ID NO:12463 | AGCAGTGGCTGGTACTACTT TGACTAC<br>SEQ ID NO:20475 |
| | | AA | NYDIN<br>SEQ ID NO:4452 | WMHPNSGNTGYAQKFQG<br>SEQ ID NO:12464 | SSGWYYFDY<br>SEQ ID NO:20476 |
| iPS:392888 | 21-225_25A2 | NA | AGCTATGGCATGCAC<br>SEQ ID NO:4453 | GTTATATGGTATGATGG AAGTAATAAATACTATG CAGACTCCGTGAAGGGC<br>SEQ ID NO:12465 | AGGTATAGCAGCAGTGGTC AGGGGGTATGGACGTC<br>SEQ ID NO:20477 |
| | | AA | SYGMH<br>SEQ ID NO:4454 | VIWYDGSNKYYADSVKG<br>SEQ ID NO:12466 | RYSSSWSGGMDV<br>SEQ ID NO:20478 |

FIGURE 49
(Continued)

| iPS ID | Clone | | Seq 1 | Seq 2 | Seq 3 |
|---|---|---|---|---|---|
| iPS:392890 | 21-225_20H9 | NA | AGCTATGCCATGAGC | GCTATTAGTGGTAGTGGT GGTTACACATACTACGC AGACTCCGTGAAGGGC | GGGGGGTCCCTCTTCTAC |
| | | | SEQ ID NO:4455 | SEQ ID NO:12467 | SEQ ID NO:20479 |
| | | AA | SYAMS | AISGSGGYTYYADSVKG | GGSLFY |
| | | | SEQ ID NO:4456 | SEQ ID NO:12468 | SEQ ID NO:20480 |
| iPS:392892 | 21-225_20C11 | NA | AGCTATGCCATGAGC | ACTATTAGTGGTCGTGGT GGTCACACATACTACGC AGACTCCGTGAAGGGC | CAGGACTGC |
| | | | SEQ ID NO:4457 | SEQ ID NO:12469 | SEQ ID NO:20481 |
| | | AA | SYAMS | TISGRGGHTYYADSVKG | QDC |
| | | | SEQ ID NO:4458 | SEQ ID NO:12470 | SEQ ID NO:20482 |
| iPS:392894 | 21-225_21G2 | NA | GACTATGGCATGCAC | GTTATATGGTATGATGTA ACTAATAAATACTATGC AGACTCCGTGAAGGGC | GAGCTTGGCTGGTACGAGGA CTAC |
| | | | SEQ ID NO:4459 | SEQ ID NO:12471 | SEQ ID NO:20483 |
| | | AA | DYGMH | VIWYDVTNKYYADSVKG | ELGWYEDY |
| | | | SEQ ID NO:4460 | SEQ ID NO:12472 | SEQ ID NO:20484 |
| iPS:392896 | 21-225_21G7 | NA | AGAAGTAGTTACTACTGGGG C | AATATCTATTATAGTGGG TATAGTTACTACAATCCG TCCCTCAAGAGT | CATAGCACCAGCTGGTCCCT TGACTAC |
| | | | SEQ ID NO:4461 | SEQ ID NO:12473 | SEQ ID NO:20485 |
| | | AA | RSSYYWG | NIYYSGYSYNPSLKS | HSTSWSLDY |
| | | | SEQ ID NO:4462 | SEQ ID NO:12474 | SEQ ID NO:20486 |
| iPS:392898 | 21-225_21H10 | NA | AACGCCCTGGATGAAC | CGTATTAAAAGCAAAAC TGATGGTGGGACAACAG ACTACGCTGCACCCGTG AAAGGC | GAAGGCTGGAACACGGACTA C |

FIGURE 49
(Continued)

| | | | | | | |
|---|---|---|---|---|---|---|
| iPS:392980 | 21-225_21H10 | AA | SEQ ID NO:4463 NAWMN | SEQ ID NO:12475 RIKSKTDGGTTDYAAPVKG | SEQ ID NO:20487 EGWNTDY | |
| | | NA | SEQ ID NO:4464 GACTATGGCATGAGC | SEQ ID NO:12476 GTTATATGGTATGAGGGAAGTAATAAATACTATGTAGACTCCGTGAGGGC | SEQ ID NO:20488 GAGCTAGGCTTCCAGTCTGACTAC | |
| iPS:392982 | 21-225_22F2 | AA | SEQ ID NO:4465 DYGMH | SEQ ID NO:12477 VIWYEGSNKYYVDSVRG | SEQ ID NO:20489 ELGFQSDY | |
| | | NA | SEQ ID NO:4466 AGCTATGCCATGAGC | SEQ ID NO:12478 GTTATTAGTGGTCGTGGTGGTAACACATTCTACGCAGACTCCGTGAAGGGC | SEQ ID NO:20490 CGTATAGCAGTGGCTGGCTCGGAGGCTTTTGATATC | |
| iPS:392984 | 21-225_22D5 | AA | SEQ ID NO:4467 SYAMS | SEQ ID NO:12479 VISGRGGNTFYADSVKG | SEQ ID NO:20491 RIAVAGSEAFDI | |
| | | NA | SEQ ID NO:4468 GGTAGTAATATTACTACTGGGGC | SEQ ID NO:12480 AATATCTATTATAGTGGGAGCACCTACTACAACCCGTCCCTCAAGAGT | SEQ ID NO:20492 CATAGCAGTAGCTGGTCCCTGACTAC | |
| iPS:392986 | 21-225_22G9 | AA | SEQ ID NO:4469 GSNYYWG | SEQ ID NO:12481 NIYYSGSTYYNPSLKS | SEQ ID NO:20493 HSSSWSLDY | |
| | | NA | SEQ ID NO:4470 AGCTATGGCATGCAC | SEQ ID NO:12482 GTTATATGGTATGATGAAACTAATAAATACTATGCAGACTCCGTGAAGGGC | SEQ ID NO:20494 GAGCTTGCCTGGTACGAGGACTAC | |
| iPS:392988 | 21-225_23F12 | AA | SEQ ID NO:4471 SYGMH | SEQ ID NO:12483 VIWYDETNKYYADSVKG | SEQ ID NO:20495 ELAWYEDY | |

FIGURE 49
(Continued)

| | | | | | | | |
|---|---|---|---|---|---|---|---|
| iPS:392912 | 21-225_25A9 | NA | SEQ ID NO:4472 AGCTATGGCATGCAC | SEQ ID NO:12484 GTTATATGGTATGATGTAACTAATAAATACTATACAGGCTCCGTGAAGGGC | SEQ ID NO:20496 GAAATTGGCTGGTTAGATGACTAC |
| | | AA | SEQ ID NO:4473 SYGMH | SEQ ID NO:12485 VIWYDVTNKYYTGSVKG | SEQ ID NO:20497 EIGWLDDY |
| iPS:392914 | 21-225_25D12 | NA | SEQ ID NO:4474 AGCGATGGCATGAAC | SEQ ID NO:12486 GTTATATGGTATGATGGAAGTAATAAATACTATGCAGACTCCGTGAAGGGC | SEQ ID NO:20498 GAGAGGTATAGCAGCAGCTGGTACGACTACGGTATGGACGTC |
| | | AA | SEQ ID NO:4475 SDGMH | SEQ ID NO:12487 VIWYDGSNKYYADSVKG | SEQ ID NO:20499 ERYSSSWYDYGMDV |
| iPS:392916 | 21-225_27C5 | NA | SEQ ID NO:4476 AGCTATAGCATGAAC | SEQ ID NO:12488 TCCACTAGTAGTAGTGATAGTTATATACTACGCAGACTCAGTGAAGGGC | SEQ ID NO:20500 GTGGCGTCCTTTGACTGC |
| | | AA | SEQ ID NO:4477 SYSMN | SEQ ID NO:12489 STSSSDSYIYYADSVKG | SEQ ID NO:20501 VASFDC |
| iPS:392918 | 21-225_28F5 | NA | SEQ ID NO:4478 AGCTATGGCATGCAC | SEQ ID NO:12490 GTTATATGGTATGATGAAAATAATAAATACTATGCAGACTCCGTGAAGGGC | SEQ ID NO:20502 GAATTAGGCTGGTTACGACGACTAC |
| | | AA | SEQ ID NO:4479 SYGMH | SEQ ID NO:12491 VIWYDENNKYYADSVKG | SEQ ID NO:20503 ELGWYDDY |

FIGURE 49
(Continued)

| | | | | | | |
|---|---|---|---|---|---|---|
| iPS:392920 | 21-225_29G4 | NA | SEQ ID NO:4480 GACTATGGCATACAC | SEQ ID NO:12492 GTTATATGGTATGATGA AAGTAATAAATACTATG CAGACTCCATGAAGGGC | SEQ ID NO:20504 GAACTGGGAATGACGGGTGA CTAC |
| | | AA | SEQ ID NO:4481 DYGIH | SEQ ID NO:12493 VIWYDESNKYYADSMKG | SEQ ID NO:20505 ELGMTGDY |
| iPS:392922 | 21-225_30G4 | NA | SEQ ID NO:4482 AGCTATGGCATGCAC | SEQ ID NO:12494 GTTATATGGTATGATGG AACTGATAAATACTATG TAGACTCCGTGAAGGGC | SEQ ID NO:20506 GAAAATAGCAGCTCGTACTA CTTTGACTAC |
| | | AA | SEQ ID NO:4483 SYGMH | SEQ ID NO:12495 VIWYDGIDKYYVDSVKG | SEQ ID NO:20507 ENSSSYYFDY |
| iPS:392924 | 21-225_32H2 | NA | SEQ ID NO:4484 AGCTATGCCATGCAC | SEQ ID NO:12496 GTTATATGGTATGATGG AAGTAATAAATACTATG CAGACTCCGTGAAGGGC | SEQ ID NO:20508 AGATATAGCAGCAGCTGGAC GGGGGTATGGACGTC |
| | | AA | SEQ ID NO:4485 SYGMH | SEQ ID NO:12497 VIWYDGSNKYYADSVKG | SEQ ID NO:20509 RYSSSWTGGMDV |
| iPS:392928 | 21-225_25A4 | NA | SEQ ID NO:4486 AATTATGATATTAAT | SEQ ID NO:12498 TGGATGTACCTAACAG TGGTAACACAGGCTATG CACAGAAATTCCAGGGC | SEQ ID NO:20510 AGCAGTGGCTGGTACTACTT TGACTAC |
| | | | SEQ ID NO:4487 | SEQ ID NO:12499 | SEQ ID NO:20511 |

FIGURE 49
(Continued)

| | | | | WMYPNSGNTGYAQKFQG | SSGWYYFDY |
|---|---|---|---|---|---|
| | | AA | NYDIN | SEQ ID NO:12500 | SEQ ID NO:20512 |
| iPS:392930 | 21-225_25H9 | NA | AACTATGGCATGCAC | ATTATATGGTATGATGG AAGTATAAATACTATG CAGACTCCGTGAAGGGC | GAGGGATACGATTTTTGGAG TGGCTTCTTTGACTCC |
| | | | | SEQ ID NO:12501 | SEQ ID NO:20513 |
| | | AA | NYGMH | IIWYDGSYKYYADSVKG | EGYDFWSGFFDS |
| | | | SEQ ID NO:4490 | SEQ ID NO:12502 | SEQ ID NO:20514 |
| iPS:392934 | 21-225_27D5 | NA | AGCTATGGCATGCAC | GTTATATGGTATGATGA AAGTAATAAATACTATG GAGACTCCGTGAAGGGC | GAACTGGGGTTCCTCTCTGA CTAC |
| | | | SEQ ID NO:4491 | SEQ ID NO:12503 | SEQ ID NO:20515 |
| | | AA | SYGMH | VIWYDESNKYYGDSVKG | ELGFLSDY |
| | | | SEQ ID NO:4492 | SEQ ID NO:12504 | SEQ ID NO:20516 |
| iPS:392936 | 21-225_28B6 | NA | AATTATGATATTAAT | TGGATGCACCCTGACAG TGGTAACACAGGCTATG CACAGAAGTTCCAGGGC | AGCAGTGGCTGGTACTACTT TGACTAC |
| | | | SEQ ID NO:4493 | SEQ ID NO:12505 | SEQ ID NO:20517 |
| | | AA | NYDIN | WMHPDSGNTGYAQKFQG | SSGWYYFDY |
| | | | SEQ ID NO:4494 | SEQ ID NO:12506 | SEQ ID NO:20518 |
| iPS:392938 | 21-225_29H4 | NA | AGCTATGGCATACAC | GTTATATGGTATGATGG AAGTAATAAATACTATG CAGACTCCGTGAAGGGC | AGGTATAGCAGCAGCTGGTC AGGGGGTATGGACGTC |
| | | | SEQ ID NO:4495 | SEQ ID NO:12507 | SEQ ID NO:20519 |

FIGURE 49
(Continued)

| | | | | | | |
|---|---|---|---|---|---|---|
| iPS:392940 | 21-225_29D9 | AA | SYGIH | | VIWYDGSNKYYADSVKG | RYSSSWSGGMDV |
| | | | SEQ ID NO:4496 | | SEQ ID NO:12508 | SEQ ID NO:20520 |
| | | NA | GACTATGGCATTCAC | | GTTATATGGTATGATGAAGTAATAACTACTATGCAGACTCCGTGAAGGC | GAAATTGGCTGGTAGATGACTAC |
| | | | SEQ ID NO:4497 | | SEQ ID NO:12509 | SEQ ID NO:20521 |
| iPS:392942 | 21-225_30E9 | AA | DYGIH | | VIWYDESNNYYADSVKG | EIGWLDDY |
| | | | SEQ ID NO:4498 | | SEQ ID NO:12510 | SEQ ID NO:20522 |
| | | NA | AGCTGTGCCATGAGC | | GCTATTAGTGGTCGTGGTGGTAGCACATTCTACGCAGACTCCGTGAAGGGC | GGGGAGCTACTAGAGGACTACTACTACTACGGTATGGACGTC |
| | | | SEQ ID NO:4499 | | SEQ ID NO:12511 | SEQ ID NO:20523 |
| iPS:392944 | 21-225_31H5 | AA | SCAMN | | AISGRGGSTFYADSVKG | GELLEDYYYGMDV |
| | | | SEQ ID NO:4500 | | SEQ ID NO:12512 | SEQ ID NO:20524 |
| | | NA | AGCTATGCCATGAGC | | GCTATTAGTGGTCGTGGTGGTGAAGCATATTCCACGCAGACTCCGTGAAGGGC | GGGGAGCTACTAGAGGACTACTACTTCTACGGTATGGACGTC |
| | | | SEQ ID NO:4501 | | SEQ ID NO:12513 | SEQ ID NO:20525 |
| iPS:392948 | 21-225_25G5 | AA | SYAMS | | AISGRGGSIFHADSVKG | GELLEDYYFYGMDV |
| | | | SEQ ID NO:4502 | | SEQ ID NO:12514 | SEQ ID NO:20526 |
| | | NA | GACTATGGCATACAC | | GTTATTGGTATGATGAAATAATAAATATTATGCAGACTCCGTGAAGGC | GAAATTGGCTGGTAGATGACTAC |
| | | | SEQ ID NO:4503 | | SEQ ID NO:12515 | SEQ ID NO:20527 |
| | | AA | DYGIH | | VIWYDGNNKYYADSVKG | EIGWLDDY |
| | | | SEQ ID NO:4504 | | SEQ ID NO:12516 | SEQ ID NO:20528 |

FIGURE 49
(Continued)

| | | | | | |
|---|---|---|---|---|---|
| iPS:392950 | 21-225_25C10 | NA | AGCTATAGGATGAAC | TCCATTAGTAGTAGTAGT AGTACCATATACTACGC AGACTCTGTGAAGGGC | ACGGCTGGTTTTGACTAC |
| | | | SEQ ID NO:4505 | SEQ ID NO:12517 | SEQ ID NO:20529 |
| | | AA | SYRMN | SISSSSTIYYADSVKG | TAGFDY |
| | | | SEQ ID NO:4506 | SEQ ID NO:12518 | SEQ ID NO:20530 |
| iPS:392952 | 21-225_26G1 | NA | AGCTATGGCATGAAC | TCCATTAGTGGTAGTAGT AGTTACATATACTACGC GGACTCAGTGAAGGGC | CTGACTACCTTTGACTTC |
| | | | SEQ ID NO:4507 | SEQ ID NO:12519 | SEQ ID NO:20531 |
| | | AA | SYGMN | SISGSSSYIYYADSVKG | LTTFDF |
| | | | SEQ ID NO:4508 | SEQ ID NO:12520 | SEQ ID NO:20532 |
| iPS:392954 | 21-225_26A10 | NA | AGCTATGCCATGAGC | GTTATTAGTGGTAGTGGT GTTAACACATTCTACGCA GACTCCGTGAAGGGC | AAGATAGCAGTGGCTGGTAC TCACTACTTTGACTAC |
| | | | SEQ ID NO:4509 | SEQ ID NO:12521 | SEQ ID NO:20533 |
| | | AA | SYAMS | VISGSGVNTFYADSVKG | KIAVAGTHYFDY |
| | | | SEQ ID NO:4510 | SEQ ID NO:12522 | SEQ ID NO:20534 |
| iPS:392956 | 21-225_27A11 | NA | AGCTATGGCATGCAC | GTTATATGGTATGATGG AAGTAATAAATACTATG CAGACTCCGTGAAGGGC | GATTCCTCCCCTACGGTAT GGACGTC |
| | | | SEQ ID NO:4511 | SEQ ID NO:12523 | SEQ ID NO:20535 |
| | | AA | SYGMH | VIWYDGSNKYYADSVKG | DSSPYGMDV |
| | | | SEQ ID NO:4512 | SEQ ID NO:12524 | SEQ ID NO:20536 |
| iPS:392958 | 21_225_28C7 | NA | AGCTATGGCATGCAC | GTTATATGGTATGATGA AAGTAATAAATACTATG CAGACTCCGTGAAGGGC | GAATTAGGCTGGTACGACGA CTAC |

FIGURE 49
(Continued)

| | | | | | | | |
|---|---|---|---|---|---|---|---|
| iPS:392960 | 21-225_28C7 | AA | SEQ ID NO:4513<br>SYGMH | SEQ ID NO:12525<br>VIWYDESNKYYADSVKG | SEQ ID NO:20537<br>ELGWYDDY |
| | | NA | SEQ ID NO:4514<br>AATTATATGATATTAAT | SEQ ID NO:12526<br>TGGATGCACCTAACAG<br>TGGTAACACAGGCTATG<br>CACAGAAATTCCAGGGC | SEQ ID NO:20538<br>AGCAGTGGCTGGTACTACTT<br>TGACTAC |
| iPS:392962 | 21-225_29E6 | AA | SEQ ID NO:4515<br>NYDIN | SEQ ID NO:12527<br>WMHPNSGNTGYAQKFQG | SEQ ID NO:20539<br>SSGWYYFDY |
| | | NA | SEQ ID NO:4516<br>AGCTATGTCATGAAC | SEQ ID NO:12528<br>GCTATTAGTGGTAGTGGT<br>GGTAGCACATACTACGC<br>AGACTCCGTGAAGGGC | SEQ ID NO:20540<br>ACTGGGGTCTTTGACTAC |
| iPS:392964 | 21-225_30A1 | AA | SEQ ID NO:4517<br>SYVMN | SEQ ID NO:12529<br>AISGSGGSTYYADSVKG | SEQ ID NO:20541<br>TGVFDY |
| | | NA | SEQ ID NO:4518<br>AGCTATGCCATGAGC | SEQ ID NO:12530<br>GCTATTAGTGGTGGTGGT<br>GGTAGCACATTCCACGC<br>AGACTCCGTGAAGGGC | SEQ ID NO:20542<br>GGGGAGCTACTAGAGGACTA<br>CTACTTCTACGGTATGGACG<br>TC |
| iPS:392964 | 21-225_31A8 | AA | SEQ ID NO:4519<br>SYAMS | SEQ ID NO:12531<br>AISGRGGSTFHADSVKG | SEQ ID NO:20543<br>GELLEDYYFYGMDV |
| | | NA | SEQ ID NO:4520<br>AGCTATAGCATGAAC | SEQ ID NO:12532<br>TCCATTAGTGGTAGTAGT<br>AGTTACATATACTACGC<br>AGACTCAGTGAAGGGC | SEQ ID NO:20544<br>GGCAATATAGCAAGGGACTA<br>C |
| iPS:392966 | 21-225_32G3 | AA | SEQ ID NO:4521<br>SYSMN | SEQ ID NO:12533<br>SISGSSSYIYYADSVKG | SEQ ID NO:20545<br>GNIARDY |
| | | | SEQ ID NO:4522 | SEQ ID NO:12534 | SEQ ID NO:20546 |

FIGURE 49
(Continued)

| | | | | | |
|---|---|---|---|---|---|
| iPS:392968 | 21-225_25B6 | NA | AACTATGGCATGCAC | GTTATATGGTATGAGGAAGTAATAAATACTATACAGAGTCCGTGAAGGGC | GAACTGGGGTTCCTCTCTGACTAC |
| | | | SEQ ID NO:4523 | SEQ ID NO:12535 | SEQ ID NO:20547 |
| | | AA | NYGMH | VIWYEESNKYYTESVKG | ELGFLSDY |
| | | | SEQ ID NO:4524 | SEQ ID NO:12536 | SEQ ID NO:20548 |
| iPS:392972 | 21-225_26A2 | NA | AGCTATGGCATGCAC | GTTATATGGTATGAAGGAAGTAATAAATACTATGTAGACTCCGTGAAGGGC | GAATTAGGCTGTGGTACGACGACTAC |
| | | | SEQ ID NO:4525 | SEQ ID NO:12537 | SEQ ID NO:20549 |
| | | AA | SYGMH | VIWYEGSNKYYVDSVKG | ELGWYDDY |
| | | | SEQ ID NO:4526 | SEQ ID NO:12538 | SEQ ID NO:20550 |
| iPS:392974 | 21-225_26A11 | NA | AACTGTGTCATGCAC | GTTATATGGTATGATGGAAGTAATAATACTATGCAGACTCCGTGAAGGGC | GAGGAGTATAGCAGTGGCTGGTACGACTACGGTATGGACGTC |
| | | | SEQ ID NO:4527 | SEQ ID NO:12539 | SEQ ID NO:20551 |
| | | AA | NCVMH | VIWYDGSNKYYADSVKG | EEYSSGWYDYGMDV |
| | | | SEQ ID NO:4528 | SEQ ID NO:12540 | SEQ ID NO:20552 |
| iPS:392976 | 21-225_27H12 | NA | AGCTATAGCCTGAAC | TCCATTAGTGGTAGTAGTAGTAACATATACACAGACTCAGTGAAGGGC | GTGGCGTCCTTTGACTAC |
| | | | SEQ ID NO:4529 | SEQ ID NO:12541 | SEQ ID NO:20553 |
| | | AA | SYSLN | SISGSSNYYTDSVKG | VASFDY |
| | | | SEQ ID NO:4530 | SEQ ID NO:12542 | SEQ ID NO:20554 |

FIGURE 49
(Continued)

| | | | | | |
|---|---|---|---|---|---|
| iPS:392978 | 21-225_28B8 | NA | GACTATGGCATGCAC | GTTATATGGTATGATGCA AATAATAAATACTATGC AGACTCCGTGAAGGGC | GAAATTGGCTGCTTGGTTAGATGA CTAC |
| | | | SEQ ID NO:4531 | SEQ ID NO:12543 | SEQ ID NO:20555 |
| | | AA | DYGMH | VIWYDANNKYYADSVKG | EIGWLDDY |
| | | | SEQ ID NO:4532 | SEQ ID NO:12544 | SEQ ID NO:20556 |
| iPS:392980 | 21-225_29H6 | NA | GACTATGGCATGCAC | GTTATATGGTATAATGA AATAATAAATACTATG CAGACTCCGTGAAGGGC | GAACTGGGGATGACGGGTGA CTCC |
| | | | SEQ ID NO:4533 | SEQ ID NO:12545 | SEQ ID NO:20557 |
| | | AA | DYGMH | VIWYNENNKYYADSVKG | ELGMTGDS |
| | | | SEQ ID NO:4534 | SEQ ID NO:12546 | SEQ ID NO:20558 |
| iPS:392982 | 21-225_30D1 | NA | AGCTATGCCATGAGC | GCTATTAGTGGTGGTCGTGGT GGTAGCACATTCCACGC AGACTCCGTGAAGGGC | GGGGAGCTACTAGAGGACTA CTACTTCTACGGTTTGGACG TC |
| | | | SEQ ID NO:4535 | SEQ ID NO:12547 | SEQ ID NO:20559 |
| | | AA | SYAMS | AISGRGGSTFHADSVKG | GELLEDYYFYGLDV |
| | | | SEQ ID NO:4536 | SEQ ID NO:12548 | SEQ ID NO:20560 |
| iPS:392984 | 21-225_30E11 | NA | ATCTATGCCATGAGC | GTTATTAGTGGTAGTGGT GGTAGCTCATTCTACGCA GACTCCGTGAAGGGC | GATCGGGTGAAAGCTCATGA TGGTTTTGATATC |
| | | | SEQ ID NO:4537 | SEQ ID NO:12549 | SEQ ID NO:20561 |
| | | AA | IYAMS | VISGSGGSSFYADSVKG | DRVKAHDGFDI |
| | | | SEQ ID NO:4538 | SEQ ID NO:12550 | SEQ ID NO:20562 |

FIGURE 49
(Continued)

| | | | | | |
|---|---|---|---|---|---|
| iPS:392986 | 21-225_31B8 | NA | AGCTATGGCCATGAGC<br>SEQ ID NO:4539 | GCTATTAGTGGTCGTGGT<br>GGTAGCACATTCCACGC<br>AGACTCCGTGAAGGGC<br>SEQ ID NO:12551 | GGGGAGTACTAGAGGACTA<br>CTACTTCTACGGTATGGACG<br>TC<br>SEQ ID NO:20563 |
| | | AA | SYAMS<br>SEQ ID NO:4540 | AISGRGGSTFHADSVKG<br>SEQ ID NO:12552 | GELLEDYYFYGMDV<br>SEQ ID NO:20564 |
| iPS:392988 | 21-225_25E6 | NA | GACTATGGCATGCAC<br>SEQ ID NO:4541 | GTTATATGGTATGATGA<br>AATAATAAATACTATG<br>CAGACTCCGTGAAGGGC<br>SEQ ID NO:12553 | GAACTGGGGATGACGGGTGA<br>CTCC<br>SEQ ID NO:20565 |
| | | AA | DYGMH<br>SEQ ID NO:4542 | VIWYDENNKYYADSVKG<br>SEQ ID NO:12554 | ELGMTGDS<br>SEQ ID NO:20566 |
| iPS:392990 | 21-225_25H10 | NA | GACTATGGCATGCAC<br>SEQ ID NO:4543 | GTTATATGGTATGATGA<br>AAGTAATAAATACTATG<br>CAGACTCCATGAAGGGC<br>SEQ ID NO:12555 | GAACTGGGGATGACGGGTGA<br>CTAC<br>SEQ ID NO:20567 |
| | | AA | DYGMH<br>SEQ ID NO:4544 | VIWYDESNKYYADSMKG<br>SEQ ID NO:12556 | ELGMTGDY<br>SEQ ID NO:20568 |
| iPS:392992 | 21-225_26C4 | NA | AATTATGATATCAAC<br>SEQ ID NO:4545 | TGGATGAACCCTAACAG<br>TGGTAACACAGGCTATG<br>CACAGAGATTCCAGGGC<br>SEQ ID NO:12557 | AGCAGTGGCTGGTACTACTT<br>TGACTAC<br>SEQ ID NO:20569 |
| | | AA | NYDIN<br>SEQ ID NO:4546 | WMNPNSGNTGYAQRFQG<br>SEQ ID NO:12558 | SSGWYYFDY<br>SEQ ID NO:20570 |

FIGURE 49
(Continued)

| | | | | | |
|---|---|---|---|---|---|
| iPS:392994 | 21-225_26G11 | NA | | GTTATATGGTATGATGG AAGTAATAAATACTATG CAGACTCCGTGAAGGGC | AGGTATAGCAACAGCTGGTC AGGGGTATGGACGTC |
| | | | SEQ ID NO:4547 | SEQ ID NO:12559 | SEQ ID NO:20571 |
| | | AA | SYGMH | VIWYDGSNKYYADSVKG | RYSNSWSGGMDV |
| | | | SEQ ID NO:4548 | SEQ ID NO:12560 | SEQ ID NO:20572 |
| iPS:392996 | 21-225_28B1 | NA | AGCTATGCCATGAGC | GCTATTAGTGGTAGTGG AGTAACACATTCTACG CAGACTCCGTGAAGGGC | TTGGGGCGTATAGCAGTGAC TGGTCCTTACTTTGACTAC |
| | | | SEQ ID NO:4549 | SEQ ID NO:12561 | SEQ ID NO:20573 |
| | | AA | SYAMS | AISGSGGNTFYADSVKG | LGRIAVTGPYFDY |
| | | | SEQ ID NO:4550 | SEQ ID NO:12562 | SEQ ID NO:20574 |
| iPS:392998 | 21-225_28A9 | NA | AGCTATGGCATACAC | GTTATATGGTTTGATGGA AGTAATAAATACTATGC AGACTCCGTGAAGGGC | GAAATTGGCTGGTTAGATGA CTAC |
| | | | SEQ ID NO:4551 | SEQ ID NO:12563 | SEQ ID NO:20575 |
| | | AA | SYGIH | VIWFDGSNKYYADSVKG | EIGWLDDY |
| | | | SEQ ID NO:4552 | SEQ ID NO:12564 | SEQ ID NO:20576 |
| iPS:393000 | 21-225_29D7 | NA | AGCTATGGCATGCAC | GTTATATGGTATGATGA AAGTAATAAATACTATG GAGACTCCGTGAAGGGC | GAACTGGGGGTTCCTCTCTGA CTAC |
| | | | SEQ ID NO:4553 | SEQ ID NO:12565 | SEQ ID NO:20577 |
| | | AA | SYGMH | VIWYDESNKYYGDSVKG | ELGFLSDY |
| | | | SEQ ID NO:4554 | SEQ ID NO:12566 | SEQ ID NO:20578 |

FIGURE 49
(Continued)

| | | | | | |
|---|---|---|---|---|---|
| iPS:393002 | 21-225_30G1 | NA | TACTATGGCATGCAC | GTTATATGGCATGGATGG AAGTAATAAATACTATG TAGACTCCGTGAAGGGC | GAAAATAGCAGTTCGTACTA CTTTGACTAC |
| | | | SEQ ID NO:4555 | SEQ ID NO:12567 | SEQ ID NO:20579 |
| | | AA | YYGMH | VIWHDGSNKYYVDSVKG | ENSSSYYFDY |
| | | | SEQ ID NO:4556 | SEQ ID NO:12568 | SEQ ID NO:20580 |
| iPS:393004 | 21-225_30G11 | NA | AGCTATGCCATGAGC | GCTATTAGTGGTGGTGGT GGTAGCACATTCAACGC AGACTCCGTGAAGGGC | GGGGAGCTACTAGAGGACTA CTACTTCTACGGTATGGACG TC |
| | | | SEQ ID NO:4557 | SEQ ID NO:12569 | SEQ ID NO:20581 |
| | | AA | SYAMS | AISGRGGSTFNADSVKG | GELLEDYYFYGMDV |
| | | | SEQ ID NO:4558 | SEQ ID NO:12570 | SEQ ID NO:20582 |
| iPS:393006 | 21-225_31G9 | NA | AGCTATAGCATGAAC | TCAATTAGTAGTAGTAGT AGTTACATATACTACGC AGACTCAGTGAAGGGC | GATCGAGGCAGCAGC |
| | | | SEQ ID NO:4559 | SEQ ID NO:12571 | SEQ ID NO:20583 |
| | | AA | SYSMN | SISSSSYTYYADSVKG | DRGSS |
| | | | SEQ ID NO:4560 | SEQ ID NO:12572 | SEQ ID NO:20584 |
| iPS:393010 | 21-225_25E11 | NA | AGCTATGCCATGAGC | GTTATTAGTGGTGGTGGT GGTAGCACATACTACGC AGACTCCGTGAAGGGC | CGTGGATATAGTGGCTACGA GGACCTCCTCTACTTTGACT GC |
| | | | SEQ ID NO:4561 | SEQ ID NO:12573 | SEQ ID NO:20585 |
| | | AA | SYAMS | VISGGGGSTYYADSVKG | RGYSGYEDLLYFDC |
| | | | SEQ ID NO:4562 | SEQ ID NO:12574 | SEQ ID NO:20586 |
| iPS:393012 | 21-225_26G7 | NA | AGCTATGGCATGCAC | GTTATATGGTATGATGG AAGTAATAAATATTATG CAGACTCCGTGAAGGGC | AGGTATAGCAGCAGCTGGTC AGGGGTATGGACGTC |
| | | | SEQ ID NO:4563 | SEQ ID NO:12575 | SEQ ID NO:20587 |

FIGURE 49
(Continued)

| | | | | | |
|---|---|---|---|---|---|
| | | AA | SYGMH | VIWYDGSNKYYADSVKG | RYSSSWSGGMDV |
| iPS:393014 | 21-225_26D12 | NA | SEQ ID NO:4564 AGTTATGGCATGCAC | SEQ ID NO:12576 GTTATATGGTAGTGGT AAGTAATAATACTATG CAGACTCCGTGAAGGC | SEQ ID NO:20588 GATCCTCCCCCTACGGTAT GGACGTC |
| | | AA | SEQ ID NO:4565 SYGMH | SEQ ID NO:12577 VIWYDGSNEYYADSVKG | SEQ ID NO:20589 DSSPYGMDV |
| iPS:393016 | 21-225_28F11 | NA | SEQ ID NO:4566 AGCTATGCCATGAGC | SEQ ID NO:12578 GTTACTAGTGGTAGTGGT GGTACCACATTCTACGC AGACTCCGTGAAGGGC | SEQ ID NO:20590 CGGACCCAGTTTGATGATTT TGATATC |
| | | AA | SEQ ID NO:4567 SYAMS | SEQ ID NO:12579 VTSGSGGTTFYADSVKG | SEQ ID NO:20591 RTQFDDFDI |
| iPS:393018 | 21-225_29B8 | NA | SEQ ID NO:4568 GACTATGGCATGCAC | SEQ ID NO:12580 GTTATATGGTATGATGA AAATAATAAATACTATG CAGACTCCGTGAAGGGC | SEQ ID NO:20592 GAACTGGGGATGACGGGTGA CTCC |
| | | AA | SEQ ID NO:4569 DYGMH | SEQ ID NO:12581 VIWYDENNKYYADSVKG | SEQ ID NO:20593 ELGMTGDS |
| iPS:393020 | 21-225_30E2 | NA | SEQ ID NO:4570 AGCTATGCCATGCAC | SEQ ID NO:12582 GTTATATCATATGGTGGA AGTAATAAATTCTATGC AGTCTCCGTGAAGGGC | SEQ ID NO:20594 AGGGGGTATAGCAGTGGAGG CTACGGTATGGACGTC |
| | | AA | SEQ ID NO:4571 SYGMH | SEQ ID NO:12583 VISYGGSNKFYAVSVKG | SEQ ID NO:20595 RGYSSGGYGMDV |
| | | | SEQ ID NO:4572 | SEQ ID NO:12584 | SEQ ID NO:20596 |

FIGURE 49
(Continued)

| | | | | |
|---|---|---|---|---|
| iPS:393022 | 21-225_30H11 | NA | AGCTATAGCATGAAC SEQ ID NO:4573 | TCCATTAGTAGTGGTAGTAGT AGTTACATATACTACGC AGACTCAGTGAAGGGC SEQ ID NO:12585 | GATAGGGGGAGCCTC SEQ ID NO:20597 |
| | | AA | SYSMN SEQ ID NO:4574 | SISGSSSYIYYADSVKG SEQ ID NO:12586 | DRGSL SEQ ID NO:20598 |
| iPS:393024 | 21-225_31H9 | NA | AGCTGTGCCATGAAC SEQ ID NO:4575 | GCTATTAGTGGTAGTGGT GGTAGCTCATTCTACGCA GACTCCGTGAAGGGC SEQ ID NO:12587 | CGGACTCCCTATGATGTCTTT GATATC SEQ ID NO:20599 |
| | | AA | SCAMN SEQ ID NO:4576 | AISGSGGSSFYADSVKG SEQ ID NO:12588 | RTPYDVFDI SEQ ID NO:20600 |
| iPS:393026 | 21-225_32B6 | NA | GACTATGGCATGCAC SEQ ID NO:4577 | GTTATATGGTATGATGA AATACTAATACTATG CAGACTCCGTGAAGGGC SEQ ID NO:12589 | GAGTGGGGGGACTAC SEQ ID NO:20601 |
| | | AA | DYGMH SEQ ID NO:4578 | VIWYDENTKYYADSVKG SEQ ID NO:12590 | EWGDY SEQ ID NO:20602 |
| iPS:393028 | 21-225_25D7 | NA | AGCTATGCCATGAGC SEQ ID NO:4579 | GCTATTAGTGGTAGAGG TGGTACCACATTCTACGC AGACTCCGTGAAGGGC SEQ ID NO:12591 | GACGGGTACGGTGGTAACTC CTTCTTTGACTAC SEQ ID NO:20603 |
| | | AA | SYAMS SEQ ID NO:4580 | AISGRGGTTFYADSVKG SEQ ID NO:12592 | DGYGGNSFFDY SEQ ID NO:20604 |
| iPS:393030 | 21-225_25H11 | NA | GACTATGGCATGCAC | GTTATATGGTATGATGA AATAATGAATACTATG CAGACTCCGTGAAGGGC | GAACTGGGGATGACGGGTGA CTCC |

FIGURE 49
(Continued)

| | | | | | | |
|---|---|---|---|---|---|---|
| iPS:393032 | 21-225_25H11 | AA | SEQ ID NO:4581<br>DYGMH | SEQ ID NO:12593<br>VIWYDENNEYYADSVKG | SEQ ID NO:20605<br>ELGMTGDS | |
| | | NA | SEQ ID NO:4582<br>GGCTATGGCATGCAC | SEQ ID NO:12594<br>ATTATATGGTATGATGG AAGTAATAAATACTATG CAGACTCCGTGAAGGGC | SEQ ID NO:20606<br>GAGAGGTACGATTTTTGGAG TGGTTGTATGGACGTC | |
| iPS:393034 | 21-225_26F8 | AA | SEQ ID NO:4583<br>GYGMH | SEQ ID NO:12595<br>IIWYDGSNKYYADSVKG | SEQ ID NO:20607<br>ERYDFWSGCMDV | |
| | | NA | SEQ ID NO:4584<br>GACTATGGCATGCAC | SEQ ID NO:12596<br>GTTATATGGTATGATGA AATAATAAATACTATG TAGACTCCGTGAGGGGC | SEQ ID NO:20608<br>GAACTGGGGATGACGGGTGA CTCC | |
| iPS:393034 | 21-225_27F2 | AA | SEQ ID NO:4585<br>DYGMH | SEQ ID NO:12597<br>VIWYDENNKYYVDSVRG | SEQ ID NO:20609<br>ELGMTGDS | |
| | | NA | SEQ ID NO:4586<br>ACCTATGGCATGCAC | SEQ ID NO:12598<br>GTTATATGGTATGATGG AAGTAATAAATACTATG CAGACTCCGTGAAGGGC | SEQ ID NO:20610<br>GATCGATACGATTTTTGGAG TGGTTATTTTGACTAC | |
| iPS:393036 | 21-225_28G3 | AA | SEQ ID NO:4587<br>TYGMH | SEQ ID NO:12599<br>VIWYDGSNKYYADSVKG | SEQ ID NO:20611<br>DRYDFWSGYFDY | |
| | | | SEQ ID NO:4588 | SEQ ID NO:12600 | SEQ ID NO:20612 | |

FIGURE 49
(Continued)

| | | | | |
|---|---|---|---|---|
| iPS:393038 | 21-225_29D8 | NA | GACTATGGCATACAC | GTTATATGGTTTGATGGAACTAATAAATACTATGCAGACTCCGTGAAGGGC | GAAATTGGCTGGTTAGATGACTAC |
| | | | SEQ ID NO:4589 | SEQ ID NO:12601 | SEQ ID NO:20613 |
| | | AA | DYGIH | VIWFDGTNKYYADSVKG | EIGWLDDY |
| | | | SEQ ID NO:4590 | SEQ ID NO:12602 | SEQ ID NO:20614 |
| iPS:393040 | 21-225_30E3 | NA | AGCTATGCCATGAAC | GCTATTAGTGGTCGTGGTGGTAGCACATTCTACGCAGACTCCGAGAAGGGC | GGGGAGCTATTAGAGGACTACTACTACTACGGAATGGACGTC |
| | | | SEQ ID NO:4591 | SEQ ID NO:12603 | SEQ ID NO:20615 |
| | | AA | SYAMN | AISGRGGSTFYADSEKG | GELLEDYYYGMDV |
| | | | SEQ ID NO:4592 | SEQ ID NO:12604 | SEQ ID NO:20616 |
| iPS:393042 | 21-225_31F1 | NA | GACTACTATATGCAC | TGGATCAACCCTAACAGTGGTGGCACAAACTATGCACAGAAGTTTCAGGGC | GATAGTAGCAATTTCAGCAACTGGTACGATTACTACGGTATGGACGTC |
| | | | SEQ ID NO:4593 | SEQ ID NO:12605 | SEQ ID NO:20617 |
| | | AA | DYYMH | WINPNSGGTNYAQKFQG | DSSNFSNWYDYYGMDV |
| | | | SEQ ID NO:4594 | SEQ ID NO:12606 | SEQ ID NO:20618 |
| iPS:393044 | 21-225_25B8 | NA | AGCTATGGTATCAGC | TGGATCAGGGCTTACAATGGTAACACAACCTATGCACAGAAGCTCCGGGGC | ACCGCTGCTGGGTATAGCAGCAGCTGGTTTGACTAC |
| | | | SEQ ID NO:4595 | SEQ ID NO:12607 | SEQ ID NO:20619 |
| | | AA | SYGIS | WISAYNGNTTYAQKLRG | TAAGYSSSWFDY |
| | | | SEQ ID NO:4596 | SEQ ID NO:12608 | SEQ ID NO:20620 |

FIGURE 49
(Continued)

| | | | | | |
|---|---|---|---|---|---|
| iPS:393046 | 21-225_25A12 | NA | | AACTGTGTCATGCAC | | GTTATATGGTATGATGG AAGTAATAAATACTATG CAGACTCCGTGAAGGGC | | GAGGAGTATAGCAGTGGCTG GTACGACTACGGTATGGACG TC |
| | | | | SEQ ID NO:4597 | | SEQ ID NO:12609 | | SEQ ID NO:20621 |
| | | AA | | NCVMH | | VIWYDGSNKYYADSVKG | | EEYSSGWYDYGMDV |
| | | | | SEQ ID NO:4598 | | SEQ ID NO:12610 | | SEQ ID NO:20622 |
| iPS:393048 | 21-225_27C3 | NA | | GACTATGGCATGCAC | | GTTATATGGTATGATGA AATAATAAATCCTATG CAGACTCCGTGAAGGGC | | GAACTGGGGATGACGGGTGA CTCC |
| | | | | SEQ ID NO:4599 | | SEQ ID NO:12611 | | SEQ ID NO:20623 |
| | | AA | | DYGMH | | VIWYDENKSYADSVKG | | ELGMTGDS |
| | | | | SEQ ID NO:4600 | | SEQ ID NO:12612 | | SEQ ID NO:20624 |
| iPS:393050 | 21-225_28C5 | NA | | AGCTATGGTATCAGC | | TGGATCAGCGCTTACAA TGGTAACAACCTATG CACAGAAGCTCCGGGGC | | ACCGCTGCTGGGTATAGCAG CAGCTGGTTTGACTAC |
| | | | | SEQ ID NO:4601 | | SEQ ID NO:12613 | | SEQ ID NO:20625 |
| | | AA | | SYGIS | | WISAYNGNTTYAQKLRG | | TAAGYSSSWFDY |
| | | | | SEQ ID NO:4602 | | SEQ ID NO:12614 | | SEQ ID NO:20626 |
| iPS:393054 | 21-225_29G8 | NA | | GACTATGGCATGCAC | | GTTATATGGTATGATGA AACTAATAAATACTATG CAGACTCCGTGAAGGGC | | GAACTGGGGATGACGAGTGA CTAC |
| | | | | SEQ ID NO:4603 | | SEQ ID NO:12615 | | SEQ ID NO:20627 |
| | | AA | | DYGMH | | VIWYDETNKYYADSVKG | | ELGMTSDY |
| | | | | SEQ ID NO:4604 | | SEQ ID NO:12616 | | SEQ ID NO:20628 |

FIGURE 49
(Continued)

| | | NA/AA | | | |
|---|---|---|---|---|---|
| iPS:393056 | 21-225_30F3 | NA | AGCTATGGCATGCAC | GTTATATGGTATGATGTA AGTAATAAATACTATGC AGACTCCGTGAAGGGC | GAAATGGGCTGGTACGATGA CTAC |
| | | | SEQ ID NO:4605 | SEQ ID NO:12617 | SEQ ID NO:20629 |
| | | AA | SYGMH | VIWYDVSNKYYADSVKG | EMGWYDY |
| | | | SEQ ID NO:4606 | SEQ ID NO:12618 | SEQ ID NO:20630 |
| iPS:393058 | 21-225_31H3 | NA | AGCTATGCCATGAAC | GCTATTAGTGGTCGTGGT GGTAACACATTCTACGC AGACTCCGTGAAGGGC | GGGGAGTACTAGAGGACTA CTACTACTACGGAATGGACG TC |
| | | | SEQ ID NO:4607 | SEQ ID NO:12619 | SEQ ID NO:20631 |
| | | AA | SYAMN | AISGRGGNTFYADSVKG | GELLEDYYYYGMDV |
| | | | SEQ ID NO:4608 | SEQ ID NO:12620 | SEQ ID NO:20632 |
| iPS:393060 | 21-225_32G12 | NA | AGCTATGGCCATGAGC | TCTATTAGTGGTCGTGGT GGTAGCACATTCCACGC AGACTCCGTGAAGGGC | GGGGAGTACTAGAGGACTA CTACTTCTACGGTATGGACG TC |
| | | | SEQ ID NO:4609 | SEQ ID NO:12621 | SEQ ID NO:20633 |
| | | AA | SYAMS | SISGRGGSTFHADSVKG | GELLEDYFYGMDV |
| | | | SEQ ID NO:4610 | SEQ ID NO:12622 | SEQ ID NO:20634 |
| iPS:393062 | 21-225_33H3 | NA | AGCTATGGCATGCAC | ATTATATCATATGGTGGA AGTAATAACTTCTATGCA GACTCCGTGAAGGGC | AGGGGTATAGCAGTGGAGG CTACGGTATGGACGTC |
| | | | SEQ ID NO:4611 | SEQ ID NO:12623 | SEQ ID NO:20635 |
| | | AA | SYGMH | IISYGGSNNFYADSVKG | RGYSSGGYGMDV |
| | | | SEQ ID NO:4612 | SEQ ID NO:12624 | SEQ ID NO:20636 |
| iPS:393064 | 21-225_33A9 | NA | AGTTATGATATCAAC | TGGATGAACCCTAACAG TGGTAACACAGGCTATG CACAGAAGTTCCAGGGC | AAGAAGGCTAACGACTAC |
| | | | SEQ ID NO:4613 | SEQ ID NO:12625 | SEQ ID NO:20637 |

FIGURE 49
(Continued)

| | | AA/NA | | | | | |
|---|---|---|---|---|---|---|---|
| iPS:393066 | 21-225_34D3 | AA | SYDIN | | WMNPNSGNTGYAQKFQG | | KKANDY |
| | | NA | SEQ ID NO:4614 TACTATGGCATGCAC | | SEQ ID NO:12626 GTTATATGGCATGATGG AAGTAATAAATACTATG TAGACTCCGTGAAGGGC | | SEQ ID NO:20638 GAAAATAGCAGTTCGTTCTA CTTTGACTAC |
| iPS:393068 | 21-225_34G9 | AA | YYGMH | | SEQ ID NO:12627 VIWHDGSNKYYVDSVKG | | SEQ ID NO:20639 ENSSSFYFDY |
| | | NA | SEQ ID NO:4616 AGCTATGCCATGAGC | | SEQ ID NO:12628 GCTATTAGTGGTCGTGGT GGTAGCACATTCCACGC AGACTCCGTGAAGGGC | | SEQ ID NO:20640 GGGGAGCTACTAGAGGACTA CTACTTCTACGGTATGGACG TC |
| iPS:393072 | 21-225_36C5 | AA | SYAMS | | SEQ ID NO:12629 AISGRGGSTFHADSVKG | | SEQ ID NO:20641 GELLEDYYFYGMDV |
| | | NA | SEQ ID NO:4618 AGCTATGCCATGAAC | | SEQ ID NO:12630 GCTATTAGTGGTCGTGGT GGTAGCACATTCCACGC AGACTCCGTGAAGGGC | | SEQ ID NO:20642 GGGGAGCTATTAGAGGACTA CTACTTCTACGGTATGGACG TC |
| iPS:393074 | 21-225_33B1 | AA | SYAMN | | SEQ ID NO:12631 AISGRGGSTFHADSVKG | | SEQ ID NO:20643 GELLEDYYFYGMDV |
| | | NA | SEQ ID NO:4620 GACTATGGCATGCAC | | SEQ ID NO:12632 GTTATATGGTATGATAG AAATAATAAATACTATG CAGACTCCGTGAAGGGC | | SEQ ID NO:20644 GAAATGGGCTGGTACGATGA CTAC |
| | | AA | DYGMH | | SEQ ID NO:12633 VIWYDRNNKYYADSVKG | | SEQ ID NO:20645 EMGWYDDY |

FIGURE 49
(Continued)

| | | | | | | |
|---|---|---|---|---|---|---|
| iPS:393076 | 21-225_33A4 | NA | SEQ ID NO:4622 AGCTATGCCATGAAC | SEQ ID NO:12634 GCTATTAGTGTCGTGGT GGTAGCACATTCTACGC AGACTCCGTGAAGGGC | SEQ ID NO:20646 GGGGAACTACTAGAGAGACTA CTCCTACTACGGTATCGACG TC |
| | | AA | SEQ ID NO:4623 SYAMN | SEQ ID NO:12635 AISRRGGSTFYADSVKG | SEQ ID NO:20647 GELLEDYSYYGIDV |
| iPS:393078 | 21-225_33H11 | NA | SEQ ID NO:4624 AGCTATAGCATGAAC | SEQ ID NO:12636 TCCATTAGTGGTAGTAGT AGTTACATATACTACGC AGACTCAGTGAAGGGC | SEQ ID NO:20648 ACAAACGGTATGGACGTC |
| | | AA | SEQ ID NO:4625 SYSMN | SEQ ID NO:12637 SISGSSSYIYYADSVKG | SEQ ID NO:20649 TNGMDV |
| iPS:393080 | 21-225_34F3 | NA | SEQ ID NO:4626 GGCTACCATATATGCAC | SEQ ID NO:12638 TGGATCAACCTAACAG TGGTGGCACAAACTATG CACAGAAGTTTCAGGGC | SEQ ID NO:20650 GACGGTACCAGCTCCTTTGA CTAC |
| | | AA | SEQ ID NO:4627 GYHMH | SEQ ID NO:12639 WINPNSGGTNYAQKFQG | SEQ ID NO:20651 DGTSSFDY |
| iPS:393082 | 21-225_34C11 | NA | SEQ ID NO:4628 AGTTATACCATGAGC | SEQ ID NO:12640 TCCATTAGTGGTAGTAGT AATTACATATACTACGC AGACTCAGTGAAGGGC | SEQ ID NO:20652 TTAACTGGTTTTGACTAC |
| | | AA | SEQ ID NO:4629 SYTMS | SEQ ID NO:12641 SISGSSNYIYYADSVKG | SEQ ID NO:20653 LTGFDY |
| iPS:393084 | 21-225_35C6 | NA | SEQ ID NO:4630 GGCGATTATATGCAC | SEQ ID NO:12642 TGGATCAGCCCTAAAAA TGGTGGCACAAACTATG CACAGAAGTTTCAGGGC | SEQ ID NO:20654 GATGGAACTGGGTCCTTTGA CTAC |
| | | | SEQ ID NO:4631 | SEQ ID NO:12643 | SEQ ID NO:20655 |

FIGURE 49
(Continued)

| | | | | | | |
|---|---|---|---|---|---|---|
| iPS:393086 | 21-225_36H5 | AA | GDYMH | | WISPKNGGTNYAQKFQG | DGTGSFDY |
| | | | SEQ ID NO:4632 | | SEQ ID NO:12644 | SEQ ID NO:20656 |
| | | NA | GACTATCATATGCAC | | TGGATCAACCCTAATAG GGGTGGCACAAACTATG CACAGAAGTTCAGGAC | GATGGAACTGGGTCCTTTGA CTAC |
| | | | SEQ ID NO:4633 | | SEQ ID NO:12645 | SEQ ID NO:20657 |
| | | AA | DYHMH | | WINPNRGGTNYAQKFQD | DGTGSFDY |
| | | | SEQ ID NO:4634 | | SEQ ID NO:12646 | SEQ ID NO:20658 |
| iPS:393088 | 21-225_33D1 | NA | AATTATGACATTAAC | | TGGATGCACCCTAACAG TGGTAACACAGGCTTTG CACAGAAGTTCCGGGGC | AGCAGTGGCTGGTACTTTTT TGACTAC |
| | | | SEQ ID NO:4635 | | SEQ ID NO:12647 | SEQ ID NO:20659 |
| | | AA | NYDIN | | WMHPNSGNTGFAQKFRG | SSGWYFFDY |
| | | | SEQ ID NO:4636 | | SEQ ID NO:12648 | SEQ ID NO:20660 |
| iPS:393090 | 21-225_33A5 | NA | AGCTATGTCATAAAC | | GCTATTAGTGGTAGTGGT GTTAGCACATACTACGC AGACTCCGTGAAGGGC | ACTTCCCTCTTTGACTAC |
| | | | SEQ ID NO:4637 | | SEQ ID NO:12649 | SEQ ID NO:20661 |
| | | AA | SYVIN | | AISGSGVSTYYADSVKG | TSLFDY |
| | | | SEQ ID NO:4638 | | SEQ ID NO:12650 | SEQ ID NO:20662 |
| iPS:393092 | 21-225_33C12 | NA | CACTATGGCATGCAC | | GTTATATGGTATGATGG AAGTAATAAATACTATG CAGACTCCGTGAAGGGC | GAAAATAGCAGCTCGTACTA CTTTGACTAC |
| | | | SEQ ID NO:4639 | | SEQ ID NO:12651 | SEQ ID NO:20663 |
| | | AA | HYGMH | | VIWYDGSNKYYADSVKG | ENSSSYYFDY |
| | | | SEQ ID NO:4640 | | SEQ ID NO:12652 | SEQ ID NO:20664 |

FIGURE 49
(Continued)

| | | | | | |
|---|---|---|---|---|---|
| iPS:393094 | 21-225_34C4 | NA | AGAAGTAGTTACTACTGGGGC | AGTATCTATTATAGTGGGAGCACCGCCTACAATCCGTCCCTCAAGAGT | CTGAGCAGCAGCTGGTCTTTTGACTAC |
| | | | SEQ ID NO:4641 | SEQ ID NO:12653 | SEQ ID NO:20665 |
| | | AA | RSSYYWG | SIYYSGSTAYNPSLKS | LSSSWSFDY |
| | | | SEQ ID NO:4642 | SEQ ID NO:12654 | SEQ ID NO:20666 |
| iPS:393096 | 21-225_34D11 | NA | AGCTATGCCATGAAC | GCTATTAGTGGTCGTGGTGGTAGCACATTCCACGCAGACTCCGTGAAGGGC | GGGGAGTAGTGAGAGAGGACTACTACTTCTACGGTATGGACGTC |
| | | | SEQ ID NO:4643 | SEQ ID NO:12655 | SEQ ID NO:20667 |
| | | AA | SYAMN | AISGRGGSTFHADSVKG | GELVEDYYFYGMDV |
| | | | SEQ ID NO:4644 | SEQ ID NO:12656 | SEQ ID NO:20668 |
| iPS:393098 | 21-225_35G6 | NA | GACTACCATATACAC | TGGATCAACCCTAACAATGGTGGCACACACTATGCACAGGAGTTTCAGGGC | GATGGAACTGGGTCCTTTGACTAC |
| | | | SEQ ID NO:4645 | SEQ ID NO:12657 | SEQ ID NO:20669 |
| | | AA | DYHIH | WINPNNGGTHYAQEFQG | DGTGSFDY |
| | | | SEQ ID NO:4646 | SEQ ID NO:12658 | SEQ ID NO:20670 |
| iPS:393100 | 21-225_36B8 | NA | AACTATGGCATGCAC | GTTATATATGGCATGATGGAAGTAATAAATACTATGGAGACTCCGTGAAGGGC | GAAAATAGCAGCTCGTACTACTTTGACTAC |
| | | | SEQ ID NO:4647 | SEQ ID NO:12659 | SEQ ID NO:20671 |
| | | AA | NYGMH | VIWHDGSNKYYGDSVKG | ENSSSYYFDY |
| | | | SEQ ID NO:4648 | SEQ ID NO:12660 | SEQ ID NO:20672 |
| iPS:393102 | 21_225_33F1 | NA | AGCTATGCCATGAGC | TCTATTAGTGGTCGTGGTGGTAGCACATTCCACGCAGACTCCGTGAAGGGC | GGGGAGTACTTCTACGGTATGGACGTCTAGAGGACTACTACTTCTACGGTATGGACGTC |

FIGURE 49
(Continued)

| | | | | | |
|---|---|---|---|---|---|
| iPS:393104 | 21-225_33F1 | AA | SEQ ID NO:4649<br>SYAMS | SEQ ID NO:12661<br>SISGRGGSTFHADSVKG | SEQ ID NO:20673<br>GELLEDYYFYGMDV |
| | | NA | SEQ ID NO:4650<br>AGCTGTGCCATGAGC | SEQ ID NO:12662<br>GCTATTAGTGGTCGTGGT<br>GGTAGCACATTCCACGC<br>AGACTCCGTGAAGGGC | SEQ ID NO:20674<br>GGGGAACTACTAGAGGACTA<br>CTACTTCTACGGTATGGACG<br>TC |
| iPS:393106 | 21-225_33A7 | AA | SEQ ID NO:4651<br>SCAMS | SEQ ID NO:12663<br>AISGRGGSTFHADSVKG | SEQ ID NO:20675<br>GELLEDYYFYGMDV |
| | | NA | SEQ ID NO:4652<br>AACTATGCCATGAAC | SEQ ID NO:12664<br>GCTATTAGTCGTCGTGTGGT<br>GGTAGCACATTCTACG<br>AGACTCCGTGAAGGGC | SEQ ID NO:20676<br>GGGGAGCTACTAGAGGACTA<br>CTACTACTTCGCTATGGACG<br>TC |
| iPS:393108 | 21-225_34A6 | AA | SEQ ID NO:4653<br>NYAMN | SEQ ID NO:12665<br>AISRRGGSTFYADSVKG | SEQ ID NO:20677<br>GELLEDYYFAMDV |
| | | NA | SEQ ID NO:4654<br>GGCTACTATATGCAC | SEQ ID NO:12666<br>TGGATCAACCCTAACAG<br>TGGTGGCACAAACTATG<br>CACAGAAGTTTCAGGGC | SEQ ID NO:20678<br>GATATTAGTAATTTCAGCAG<br>CTGGTACGATTACTACGCTA<br>TGGACGTC |
| iPS:393110 | 21-225_34G11 | AA | SEQ ID NO:4655<br>GYYMH | SEQ ID NO:12667<br>WINPNSGGTNYAQKFQG | SEQ ID NO:20679<br>DISNFSSWYDYYAMDV |
| | | NA | SEQ ID NO:4656<br>AGCTATGCCATGAGC | SEQ ID NO:12668<br>GCTATTAGTGGTCGTGGT<br>GGTAGCACATTCCACGC<br>AGACTCCGTGAAGGGC | SEQ ID NO:20680<br>GGGGAGCTACTAGAGGACTA<br>CTACTTCTACGGTATGGACG<br>TC |
| iPS:393112 | 21-225_35B7 | AA | SEQ ID NO:4657<br>SYAMS | SEQ ID NO:12669<br>AISGRGGSTFHADSVKG | SEQ ID NO:20681<br>GELLEDYYFYGMDV |
| | 21_225_33G1 | NA | SEQ ID NO:4658<br>GGCTACTATATGCAC | SEQ ID NO:12670<br>TGGATCAGCCCTAACAA<br>TGGTGGCACAAACTATG<br>CACAGAAGTTTCAGGGC | SEQ ID NO:20682<br>GATGGAACTGGGTCCTTTGA<br>CTAC |

FIGURE 49
(Continued)

| | | | | | | |
|---|---|---|---|---|---|---|
| iPS:393114 | 21-225_33G1 | AA | SEQ ID NO:4659<br>GYYMH | SEQ ID NO:12671<br>WISPNNGGTNYAQKFQG | SEQ ID NO:4671<br>DGTGSFDY | |
| | | NA | SEQ ID NO:4660<br>AGCTATGCCATGAGC | SEQ ID NO:12672<br>GTTATTAGTGGTAGTGGT<br>GGTAGCTCATTCTACGCA<br>GACTCCGTGAAGGGC | SEQ ID NO:20684<br>GATCGGGTGAGAGCTCATGA<br>TGGTTTGATATC | |
| iPS:393116 | 21-225_33G12 | AA | SEQ ID NO:4661<br>SYAMS | SEQ ID NO:12673<br>VISGSGGSSFYADSVKG | SEQ ID NO:20685<br>DRVRAHDGFDI | |
| | | NA | SEQ ID NO:4662<br>GACTACCATATTCAC | SEQ ID NO:12674<br>TGGATCAACCCTAACAA<br>TGGTGGCACACACTATG<br>CACAGAAGTTTCAGGGC | SEQ ID NO:20686<br>GATGGAACTGGGTCCTTTGA<br>CTAC | |
| iPS:393118 | 21-225_34G7 | AA | SEQ ID NO:4663<br>DYHIH | SEQ ID NO:12675<br>WINPNNGGTHYAQKFQG | SEQ ID NO:20687<br>DGTGSFDY | |
| | | NA | SEQ ID NO:4664<br>AGCTATGCCATGAAC | SEQ ID NO:12676<br>GCTATTAGTGGTGGTGGT<br>GGTAGCACATTCTACGC<br>AGACTCCGTGAAGGGC | SEQ ID NO:20688<br>GGGGAGCTACTAGAGGACTA<br>CTACTACTACGGTATGGACG<br>TC | |
| iPS:393120 | 21-225_34H11 | AA | SEQ ID NO:4665<br>SYAMN | SEQ ID NO:12677<br>AISQRGGSTFYADSVKG | SEQ ID NO:20689<br>GELLEDYYYGMDV | |
| | | NA | SEQ ID NO:4666<br>AGTTATAGCATGAAC | SEQ ID NO:12678<br>TCCATTAGTGGTACTGGT<br>AGTTTCATATACTACGCA<br>GACTCAGTGAAGGGC | SEQ ID NO:20690<br>GTCTCTGGCTTTGACTAC | |
| | 21-225_35H8 | AA | SEQ ID NO:4667<br>SYSMN | SEQ ID NO:12679<br>SISGTGSFIYYADSVKG | SEQ ID NO:20691<br>VSGFDY | |
| | | NA | SEQ ID NO:4668 | SEQ ID NO:12680 | SEQ ID NO:20692 | |

FIGURE 49
(Continued)

| | | | | | |
|---|---|---|---|---|---|
| iPS:393122 | 21-225_33B2 | NA | AACTATGGCATGCAC SEQ ID NO:4669 | GTTATATGGCATGATGG AAGTAATAAATACTATG CAGACTCCGTGAAGGGC SEQ ID NO:12681 | GAAAATAGCAGCTCGTACTA CTTTGACTAC SEQ ID NO:20693 |
| | | AA | NYGMH SEQ ID NO:4670 | VIWHDGSNKYYADSVKG SEQ ID NO:12682 | ENSSSYYFDY SEQ ID NO:20694 |
| iPS:393124 | 21-225_33G7 | NA | AACTATGCCATGAGC SEQ ID NO:4671 | GCTATTAGTGCTGTCGTGGT GGTAGCACATTCTACGC AGACTCCGTGAAGGGC SEQ ID NO:12683 | GGGGAGTTACTAGAGGACTA CTCCTACTACGGTATGGACG TC SEQ ID NO:20695 |
| | | AA | NYAMS SEQ ID NO:4672 | AISRGGSTFYADSVKG SEQ ID NO:12684 | GELLEDYSYYGMDV SEQ ID NO:20696 |
| iPS:393126 | 21-225_35D1 | NA | AGCTATGCCATGAGC SEQ ID NO:4673 | GCTATTAGTGGTCGTGGT GGTAGCACATTCCACGC AGACTCCGTGAAGGGC SEQ ID NO:12685 | GGGGAGTTACTAGAGGACTA CTACTTCTACGGTATGGACG TC SEQ ID NO:20697 |
| | | AA | SYAMS SEQ ID NO:4674 | AISRGGSTFHADSVKG SEQ ID NO:12686 | GELLEDYYFYGMDV SEQ ID NO:20698 |
| iPS:393128 | 21-225_35F11 | NA | AGCTATGCCATGAGC SEQ ID NO:4675 | GCTATTAGTGGTCGTGGT GGTAGCACATTCCACGC AGACTCCATGAAGGGC SEQ ID NO:12687 | GGGGAGTTACTAGAGGACTA CTACTTCTACGGTATGGACG TC SEQ ID NO:20699 |
| | | AA | SYAMS SEQ ID NO:4676 | AISRGGSTFHADSMKG SEQ ID NO:12688 | GELLEDYYFYGMDV SEQ ID NO:20700 |
| iPS:393130 | 21-225_33C2 | NA | AGCTATACCATGAAC SEQ ID NO:4677 | TCCATTAGTGGTAGTAGT AGTTACATATACTACGC GGACTCAGTGAAGGGC SEQ ID NO:12689 | GATCGGGGGGGGACC SEQ ID NO:20701 |

FIGURE 49
(Continued)

| | | AA | SYTMN | | SISGSSSYIYYADSVKG | | DRGGT | |
|---|---|---|---|---|---|---|---|---|
| iPS:393132 | | | SEQ ID NO:4678 | | SEQ ID NO:12690 | | SEQ ID NO:20702 | |
| | 21-225_33H7 | NA | GACTACCATATACAC | | TGGATCAACCCTAACAATGGTGGCACACTATGCACAGGAGTTCAGGGC | | GATGGAACTGGGTCCTTTGACTAC | |
| | | | SEQ ID NO:4679 | | SEQ ID NO:12691 | | SEQ ID NO:20703 | |
| | | AA | DYHIH | | WINPNNGGTHYAQEFQG | | DGTGSFDY | |
| | | | SEQ ID NO:4680 | | SEQ ID NO:12692 | | SEQ ID NO:20704 | |
| iPS:393134 | | NA | AACTATGTCATGCAC | | CTTATATATGGTATGATGGAAGTAATAAATACTATGCAGACTCCGTGAAGGGC | | GAAAATAGCAGCTCGTACTACTTTGACTAC | |
| | 21-225_34C2 | | SEQ ID NO:4681 | | SEQ ID NO:12693 | | SEQ ID NO:20705 | |
| | | AA | NYVMH | | LIWYDGSNKYYADSVKG | | ENSSSYYFDY | |
| | | | SEQ ID NO:4682 | | SEQ ID NO:12694 | | SEQ ID NO:20706 | |
| iPS:393136 | | NA | AACTATGGCATGCAC | | GTTATATGGTATGATGGAAGTAATAAATACTATGCAGACTCCGTGAAGGGC | | GAAAATAGCAGCTCGTACTACTTTGACTAC | |
| | 21-225_34D8 | | SEQ ID NO:4683 | | SEQ ID NO:12695 | | SEQ ID NO:20707 | |
| | | AA | NYGMH | | VIWYDGSNKYYADSVKG | | ENSSSYYFDY | |
| | | | SEQ ID NO:4684 | | SEQ ID NO:12696 | | SEQ ID NO:20708 | |
| iPS:393138 | | NA | AGCTATGGCATGCAC | | GTTATATCATATGGTGTGGAAGTAATAAATACTATGCAGACTCCGTGAAGGGC | | AGGGGTATAGCAGTGGAGGCTACGGTATGGACGTC | |
| | 21-225_35E3 | | SEQ ID NO:4685 | | SEQ ID NO:12697 | | SEQ ID NO:20709 | |

FIGURE 49
(Continued)

| | | | | | | |
|---|---|---|---|---|---|---|
| iPS:393140 | 21-225_35H12 | AA | SYGMH<br>SEQ ID NO:4686 | | VISYGGSNKYYADSVKG<br>SEQ ID NO:12698 | RGYSSGGYGMDV<br>SEQ ID NO:20710 |
| | | NA | GACTACTATATACAC<br>SEQ ID NO:4687 | | TGGATCAACCCTAATAG<br>GGGTGGCACAAACTATG<br>CACAGAAGTTCAGGGC<br>SEQ ID NO:12699 | GATGGAACTGGGTCCTTTGA<br>CTAC<br>SEQ ID NO:20711 |
| iPS:393142 | 21-225_33A3 | AA | DYYIH<br>SEQ ID NO:4688 | | WINPNRGGTNYAQKFQG<br>SEQ ID NO:12700 | DGTGSFDY<br>SEQ ID NO:20712 |
| | | NA | AGCTATGGCATGAAC<br>SEQ ID NO:4689 | | TCCATTAGTGGTAGTAGT<br>ACTTACATATACTACGCA<br>GACTCAGTGAAGGGC<br>SEQ ID NO:12701 | ACAAACGGTATGGACGTC<br>SEQ ID NO:20713 |
| iPS:393144 | 21-225_34D2 | AA | SYGMN<br>SEQ ID NO:4690 | | SISGSSTYIYYADSVKG<br>SEQ ID NO:12702 | TNGMDV<br>SEQ ID NO:20714 |
| | | NA | AATTATGACATTAAC<br>SEQ ID NO:4691 | | TGGCTGCACCCTAACAG<br>TGGTACCACAGGCTTTGC<br>ACAGAAGTTCCGGGGC<br>SEQ ID NO:12703 | AGCAGTGGCTGGTACTTTTT<br>TGACTAC<br>SEQ ID NO:20715 |
| iPS:393146 | 21-225_34G8 | AA | NYDIN<br>SEQ ID NO:4692 | | WLHPNSGTTGFAQKFRG<br>SEQ ID NO:12704 | SSGWYFFDY<br>SEQ ID NO:20716 |
| | | NA | AGCTATGCCATGAGC<br>SEQ ID NO:4693 | | GCTATTAGTGGTGGTCGTGGT<br>GGTAGCACATTCCACGC<br>AGACTCCGTGAAGGGC<br>SEQ ID NO:12705 | GGGGAGCTACTAGAGGACTA<br>CTACTTCTACGGTATGGACG<br>TC<br>SEQ ID NO:20717 |
| iPS:393148 | 21-225_35E5 | AA | SYAMS<br>SEQ ID NO:4694 | | AISGRGGSTFHADSVKG<br>SEQ ID NO:12706 | GELLEDYYFYGMDV<br>SEQ ID NO:20718 |
| | | NA | AGTTATGATATCAAC<br>SEQ ID NO:4695 | | TGGATGAACCCTAACAG<br>TGGTAACACAGGCTATG<br>CACAGAAGTTCCAGGGC<br>SEQ ID NO:12707 | AAGAAGTCTAACGACTAC<br>SEQ ID NO:20719 |

FIGURE 49
(Continued)

| | | | | | | |
|---|---|---|---|---|---|---|
| iPS:393150 | 21-225_36A5 | AA | SYDIN | | WMNPNSGNTGYAQKFQG | KKSNDY |
| | | | SEQ ID NO:4696 | | SEQ ID NO:12708 | SEQ ID NO:20720 |
| | | NA | AACTATGCCATGAAC | | GCTATTAGTGCGTCGTGGT GGTAACACATTCTACGG AGACTCCGTGAAGGGC | GGGGAGCTACTAGAGGACTA CTACTACTACGCTATGGACG TC |
| | | | SEQ ID NO:4697 | | SEQ ID NO:12709 | SEQ ID NO:20721 |
| | | AA | NYAMN | | AISRGGNTFYADSVKG | GELLEDYYYYAMDV |
| | | | SEQ ID NO:4698 | | SEQ ID NO:12710 | SEQ ID NO:20722 |
| iPS:393152 | 21-225_25B3 | NA | AGCTATGGCATGCAC | | GTTATATGGTATGATGG AAGTAATAAATATTATG CAGACTCCGTGAAGGGC | GATTCCTCCCCCTACGGTAT GGACGTC |
| | | | SEQ ID NO:4699 | | SEQ ID NO:12711 | SEQ ID NO:20723 |
| | | AA | SYGMH | | VIWYDGSNKYYADSVKG | DSSPYGMDV |
| | | | SEQ ID NO:4700 | | SEQ ID NO:12712 | SEQ ID NO:20724 |
| iPS:393166 | 21-225_27G6 | NA | GGCTATGGCATGCAC | | ATTATATGGTATGATGG AAGTAAAAATACAATG CAGACTCCGTGAAGGGC | GATAGGTATATTGTAGTAG TACCAGCTGCTCCCTTACT ACTACTACTACGGTATGGAC GTC |
| | | | SEQ ID NO:4701 | | SEQ ID NO:12713 | SEQ ID NO:20725 |
| | | AA | GYGMH | | IIWYDGSKKYNADSVKG | DRVYCSSTSCSPYYYYYGMD V |
| | | | SEQ ID NO:4702 | | SEQ ID NO:12714 | SEQ ID NO:20726 |
| iPS:393168 | 21-225_32B11 | NA | GGCTACTATATGCAC | | TGGATCAACCCTAACAG TGATGGCACTAACTATG CACAGAAGTTTCAGGGC | GGGTTTTACTATGGTTCGGG GAGTATTATAACGACCTCG ACCCC |
| | | | SEQ ID NO:4703 | | SEQ ID NO:12715 | SEQ ID NO:20727 |
| | | AA | GYYMH | | WINPNSDGTNYAQKFQG | GFYYGSGSYYNDLDP |
| | | | SEQ ID NO:4704 | | SEQ ID NO:12716 | SEQ ID NO:20728 |

FIGURE 49
(Continued)

| | | | | |
|---|---|---|---|---|
| iPS:393172 | 21-225_3B12 | NA | TACTATGGCATGCAC | GTTATATCATATGATGGAAGTAATAAATACTATGAGACTCCGTGAAGGGC | GATCGGGAGGGGGGGCTATGGAGTCCCGATGCTTTTGATATC |
| | | | SEQ ID NO:4705 | SEQ ID NO:12717 | SEQ ID NO:20729 |
| | | AA | YYGMH | VISYDGSNKYYADSVKG | DRRGGYGVPDAFDI |
| | | | SEQ ID NO:4706 | SEQ ID NO:12718 | SEQ ID NO:20730 |
| iPS:393174 | 21-225_15D8 | NA | GGCTATGGCATGCAC | GTTATATCATATGATGGAAGTAATAAATACTATGAGACTCCGTGAAGGGC | GATCGGGTCTATTGTAGTAGTACCAGCTGCGTCCCTTACTACGACTACGGTATGGACGTC |
| | | | SEQ ID NO:4707 | SEQ ID NO:12719 | SEQ ID NO:20731 |
| | | AA | GYGMH | VISYDGSNKYYADSVKG | DRVYCSSTSCVPYYDYYGMDV |
| | | | SEQ ID NO:4708 | SEQ ID NO:12720 | SEQ ID NO:20732 |
| iPS:393176 | 21-225_27E7 | NA | AGTATGGCATGCAC | GTTATATGGTATGATGGAAGTAATAAATACTATGCAGACTCCGTGAAGGGC | GAGGATTCCTATTGTAGTAGTACCAGCTGCCCTTACTACTACTACTACGGTATGGACGTC |
| | | | SEQ ID NO:4709 | SEQ ID NO:12721 | SEQ ID NO:20733 |
| | | AA | SYGMH | VIWYDGSNKYYADSVKG | EDSYCSSTSCPYYYYYGMDV |
| | | | SEQ ID NO:4710 | SEQ ID NO:12722 | SEQ ID NO:20734 |
| iPS:393178 | 21-225_34D7 | NA | GGCTACTATATGCAC | TGGATCAACCCTAACAGTGGTGGCACAAACTATGCACAGAAGTTTCAGGGC | GGGTATTACTATGGTTCGGGGAGTTATTATAACGACCTCGACCCC |
| | | | SEQ ID NO:4711 | SEQ ID NO:12723 | SEQ ID NO:20735 |
| | | AA | GYYMH | WINPNSGGTNYAQKFQG | GYYYGSGSYYNDLDP |
| | | | SEQ ID NO:4712 | SEQ ID NO:12724 | SEQ ID NO:20736 |

FIGURE 49
(Continued)

| | | | | | | |
|---|---|---|---|---|---|---|
| iPS:393180 | 21-225_4G12 | NA | AGCTATGCCATGAGC | ACTCTTAGTGGTCGTGGT GGTAGCACATACGC AGACTCCGTGAAGGGC | TGGGGACGTGGATACAGCTA TGAGTACTACGGTATGG ACGTC |
| | | | SEQ ID NO:4713 | SEQ ID NO:12725 | SEQ ID NO:20737 |
| | | AA | SYAMS | TLSGRGGSTYYADSVKG | WGRGYSYEYYYGMDV |
| | | | SEQ ID NO:4714 | SEQ ID NO:12726 | SEQ ID NO:20738 |
| iPS:393182 | 21-225_4B3 | NA | GGCTACTATATGCAC | TGGATCAACCCTAACAG TGGTGGCACAAACTCTG CACAGAAGTTCAGGGC | TCCTATTACTATGGTTCGGG GAGTTATTATAACGAGTTTG ACTAC |
| | | | SEQ ID NO:4715 | SEQ ID NO:12727 | SEQ ID NO:20739 |
| | | AA | GYYMH | WINPNSGGTNSAQKFQG | SYYYGSGSYYNEFDY |
| | | | SEQ ID NO:4716 | SEQ ID NO:12728 | SEQ ID NO:20740 |
| iPS:393184 | 21-225_15H11 | NA | ACTGGTGGGAGTGGGTGTGG C | CTCATTTATTGGCAATGAT GATAAGCGCTACAGTCC ATCTCTGAGGAGC | ATAGTAGCAGTTGCCTTTGA CTAC |
| | | | SEQ ID NO:4717 | SEQ ID NO:12729 | SEQ ID NO:20741 |
| | | AA | TGGVGVG | LIYWHDDKRYSPSLRS | IVAVAFDY |
| | | | SEQ ID NO:4718 | SEQ ID NO:12730 | SEQ ID NO:20742 |
| iPS:393186 | 21-225_27D9 | NA | GGCTACTATATGCAC | TGGATCAACCCTAACAG TGGTGGCACAAAGTATG CACAGAAGTTCAGGGC | GAGAGGTGTAGTACTACCAG TTGCTATTTAGGAATTACGG GCTACTACGGTATGGACGTC |
| | | | SEQ ID NO:4719 | SEQ ID NO:12731 | SEQ ID NO:20743 |
| | | AA | GYYMH | WINPNSGGTKYAQKFQG | ERCSTTSCYLGITGYYGMDV |
| | | | SEQ ID NO:4720 | SEQ ID NO:12732 | SEQ ID NO:20744 |
| iPS:393188 | 21-225_34B9 | NA | ACTAGTGGGAGTGGGTGTGG C | CTCATTTATTGGAATGAT GATAAGCGCTACAGCCC ATCTCTGAAGAGC | TTAATAGCAGTGACTTTGA CTCC |
| | | | SEQ ID NO:4721 | SEQ ID NO:12733 | SEQ ID NO:20745 |
| | | AA | TSGVGVG | LIYWNDDKRYSPSLKS | LIAVTPDS |

FIGURE 49
(Continued)

| | | | | | |
|---|---|---|---|---|---|
| iPS:393192 | 21-225_12B1 | NA | SEQ ID NO:4722 AGCTATGGCATGCAC | SEQ ID NO:12734 GTTATATGGAATGATGG AAGTAATAAATACTATG CAGACTCCGTGAAGGGC | SEQ ID NO:20746 GATCGGGTAGCAGCAGCTGG TACCCCTACTACTACTACG GTATGGACGTC |
| | | AA | SEQ ID NO:4723 SYGMH | SEQ ID NO:12735 VIWNDGSNKYYADSVKG | SEQ ID NO:20747 DRVAAAGTPYYYYGMDV |
| iPS:393194 | 21-225_16D2 | NA | SEQ ID NO:4724 AACGCCTGGATGAAC | SEQ ID NO:12736 CGTATTAAAAGCAAAAC TGATGGTGGGACAACAG ACTACGCTGCACCCGTG AAAGGC | SEQ ID NO:20748 GATACGGGTCCTATAGCAGC TCGTCTCGCTTACTACTACTA CTACGCTATGGACGTC |
| | | AA | SEQ ID NO:4725 NAWMN | SEQ ID NO:12737 RIKSKTDGGTTDYAAPVK G | SEQ ID NO:20749 DTGPIAARLAYYYYYAMDV |
| iPS:393196 | 21-225_16G8 | NA | SEQ ID NO:4726 AGCTATGCCATGAGC | SEQ ID NO:12738 GGTATTAGTGGTAGTGG TGGTAGCACATACTACG CAGACTCCGTGAAGGGC | SEQ ID NO:20750 GAATATTGTGGTGGTGACTG CTATTCCCCTTACTACTACTA CTACGGTATGGACGTC |
| | | AA | SEQ ID NO:4727 SYAMS | SEQ ID NO:12739 GISGSGGSTYYADSVKG | SEQ ID NO:20751 EYCGGDCYSPYYYYYGMDV |
| iPS:393198 | 21-225_28A11 | NA | SEQ ID NO:4728 GGCTATGGCCTGCAC | SEQ ID NO:12740 CTTATATGGTATGATGGA AATAATACATACTATG AGACTCCGTGAAGGGC | SEQ ID NO:20752 GATAGGGTATATTGTAGTAG TACCAGCTGCTCCCCTACT ACTACTACTACGGTATGGAC GTC |
| | | | SEQ ID NO:4729 | SEQ ID NO:12741 | SEQ ID NO:20753 |

FIGURE 49
(Continued)

| | | | | | | | |
|---|---|---|---|---|---|---|---|
| iPS:393200 | 21-225_35E1 | AA | GYGLH | | LIWYDGNNTYYADSVKG | | DRVYCSSTSCSPYYYYGMDV |
| | | NA | GGCTACTATATGCAC | SEQ ID NO:4730 | TGGATCAACCTAAAAG TGGTGGCACAAATATG CACAGAAGTTCAGGGC | SEQ ID NO:12742 | GTGTATTACCATGGTTCGGG GAGTTATTATAACGAGTTTG ATTAT | SEQ ID NO:20754 |
| iPS:393202 | 21-225_6B4 | AA | GYYMH | SEQ ID NO:4731 | WINPKSGGTNYAQKFQG | SEQ ID NO:12743 | VYYHGSGSYYNEFDY | SEQ ID NO:20755 |
| | | NA | AGCTATGGCATGAGC | SEQ ID NO:4732 | GCTATTAGTGGTAGTGGT AGTAGCACATACTACGC AGACTCCGTGAAGGGC | SEQ ID NO:12744 | GAATATTGTGGTGGTGACTG CTATTCCCTTACTACTACTA CTACGGTATGGACGTC | SEQ ID NO:20756 |
| iPS:393204 | 21-225_8C12 | AA | SYAMS | SEQ ID NO:4733 | AISGSGSSTYYADSVKG | SEQ ID NO:12745 | EYCGGDCYSPYYYYGMDV | SEQ ID NO:20757 |
| | | NA | AGCTATGGCATGCAC | SEQ ID NO:4734 | CTTATATGGTATGATGGA AGTAATAAATACTATGC AGACTCCGTGAAGGGC | SEQ ID NO:12746 | GATCGGGTATCTTTGTAGTAG TTCCAGCTGCTATCCTTACTA CTACTACTACGGTATGGACG TC | SEQ ID NO:20758 |
| iPS:393206 | 21-225_13F6 | AA | SYGMH | SEQ ID NO:4735 | LIWYDGSNKYYADSVKG | SEQ ID NO:12747 | DRVSCSSSSCYPYYYYGMDV | SEQ ID NO:20759 |
| | | NA | GGCTACTATATGCAC | SEQ ID NO:4736 | TGGATCAACCTAACAG TGGTGGCAAACTATG CACAGAAGTTCAGGGC | SEQ ID NO:12748 | TCGTTTACTATGGTTCGGG GACTTATTATAACGAGTTTG ACTAC | SEQ ID NO:20760 |
| | | AA | GYYMH | SEQ ID NO:4737 | WINPNSGGANYAQKFQG | SEQ ID NO:12749 | SFYYGSGTYYNEFDY | SEQ ID NO:20761 |

FIGURE 49 (Continued)

| | | | | | |
|---|---|---|---|---|---|
| iPS:393208 | 21-225_16F3 | NA | SEQ ID NO:4738<br>GGGCACTATATGCAC | SEQ ID NO:12750<br>TGGATCAACCCTAACAG<br>TGGTGGCACAAACTATG<br>CACAGAAGTTTCAGGGC | SEQ ID NO:20762<br>TCGTATTACTATGGTTCGGG<br>GACTTATTATAACGAGTTTG<br>ACTAC |
| | | AA | SEQ ID NO:4739<br>GHYMH | SEQ ID NO:12751<br>WINPNSGGTNYAQKFQG | SEQ ID NO:20763<br>SYYYGSGTYYNEFDY |
| iPS:393210 | 21-225_17D3 | NA | SEQ ID NO:4740<br>GGCTACTATATGCAC | SEQ ID NO:12752<br>TGGATCAACCCTAACAG<br>TGGTGGCACAAACTATG<br>CACAGAAGTTTCAGGGC | SEQ ID NO:20764<br>GCGAATTACTATGGTTCGGG<br>GAGTTATTATAACGACTTTG<br>ACTAC |
| | | AA | SEQ ID NO:4741<br>GYYMH | SEQ ID NO:12753<br>WINPNSGGTNYAQKFQG | SEQ ID NO:20765<br>ANYYGSGSYYNDFDY |
| iPS:393212 | 21-225_30H6 | NA | SEQ ID NO:4742<br>ACTGGTGGAGTGGGTGTGGG<br>C | SEQ ID NO:12754<br>CTCATTATTGGCATGAT<br>GATAAGCGCTACAGTCC<br>CTCTCTGAAGAGC | SEQ ID NO:20766<br>TTAATAGCAGTGGCTTTTGA<br>CTAT |
| | | AA | SEQ ID NO:4743<br>TGGVGVG | SEQ ID NO:12755<br>LIYWHDDKRYSPSLKS | SEQ ID NO:20767<br>LIAVAFDY |
| iPS:393214 | 21-225_33A1 | NA | SEQ ID NO:4744<br>GGCTACTATATGCAC | SEQ ID NO:12756<br>TGGATCAACCCTAACAA<br>TGGTGGCACACACTATG<br>CACAGAAGTTTCAGGGC | SEQ ID NO:20768<br>GGATATTATTATGCTTCGGG<br>GAGTTATTATAACGACCTCG<br>ACCCC |
| | | AA | SEQ ID NO:4745<br>GYYMH | SEQ ID NO:12757<br>WINPNNGGTHYAQKFQG | SEQ ID NO:20769<br>GYYYASGSYYNDLDP |
| iPS:393218 | 21-225_14G3 | NA | SEQ ID NO:4746<br>GGCTACTATATGTAC | SEQ ID NO:12758<br>TGGATCAACCCTAACAG<br>TGGTGGCACAAACTATG<br>CACAGAAGTTTCAGGGC | SEQ ID NO:20770<br>TCGTATTTTTATGGTTCGGGG<br>AGTTATTATAACGAGTTTGA<br>CTAC |

FIGURE 49
(Continued)

| | | | | | | |
|---|---|---|---|---|---|---|
| iPS:393222 | 21-225_14G3 | AA | SEQ ID NO:4747<br>GYYMY | SEQ ID NO:12759<br>WINPNSGGTNYAQKFQG | SEQ ID NO:20771<br>SYFYGSGSYYNEFDY | |
| | | NA | SEQ ID NO:4748<br>ACTAGTGGAGTGGGTGTGGGC | SEQ ID NO:12760<br>CTCATTTATTGGGATGATGATAAGCGCTACAGCCCATCTCTGAAGAGC | SEQ ID NO:20772<br>ATTATAGCAGTGGCTTTTGACTAC | |
| iPS:393224 | 21-225_17F5 | AA | SEQ ID NO:4749<br>TSGVGVG | SEQ ID NO:12761<br>LIYWDDDKRYSPSLKS | SEQ ID NO:20773<br>HAVAFDY | |
| | | NA | SEQ ID NO:4750<br>ACTGGTGGAGTGGGTGTGGGC | SEQ ID NO:12762<br>CTCATTTATTGGAATGATGATGAGGCTACAGCCCATCTCTGAAGAGC | SEQ ID NO:20774<br>TTAATAGCAGTTCCTTTGACTAC | |
| iPS:393226 | 21-225_31C2 | AA | SEQ ID NO:4751<br>TGGVGVG | SEQ ID NO:12763<br>LIYWNDDERYSPSLKS | SEQ ID NO:20775<br>LIAVSFDY | |
| | | NA | SEQ ID NO:4752<br>GGCTACTATATGCAC | SEQ ID NO:12764<br>TGGATCAACCCTAACCTAACAGTGGTGGCACAAACTATGCACAGAAGTTTCAGGGC | SEQ ID NO:20776<br>GTGTATTACTATGGTTCGGGGAGTTATTATAACGAGTTTGACTAC | |
| iPS:393230 | 21-225_33E6 | AA | SEQ ID NO:4753<br>GYYMH | SEQ ID NO:12765<br>WINPNSGGTNYAQKFQG | SEQ ID NO:20777<br>VYYYGSGSYYNEFDY | |
| | | NA | SEQ ID NO:4754<br>GGCTACTATATACAC | SEQ ID NO:12766<br>TGGATCAACCCTAACAGTGGTGGCACAGACTATGCACAGAAGTTTCAGGGC | SEQ ID NO:20778<br>TCGTATTACTATGGTTCGGGGACTTATTATAACGAGTTTGACTAC | |
| iPS:393232 | 21-225_9G9 | AA | SEQ ID NO:4755<br>GYYIH | SEQ ID NO:12767<br>WINPNSGGTDYAQKFQG | SEQ ID NO:20779<br>SYYYGSGTYYNEFDY | |
| | 21_225_17F12 | NA | SEQ ID NO:4756<br>AGCTATGCCATGAGC | SEQ ID NO:12768<br>GCTATTAGTGGTGGTGGTAGCACATACTACGCAGACTCCGTGAAGGGC | SEQ ID NO:20780<br>TGGGGACGTGGATACAACTATGAGTACTACTACGGTATGGACGTC | |

FIGURE 49
(Continued)

| | | | | | | |
|---|---|---|---|---|---|---|
| iPS:393234 | 21-225_17F12 | AA | SEQ ID NO:4757<br>SYAMS | SEQ ID NO:12769<br>AISGGGGSTYYADSVKG | SEQ ID NO:20781<br>WGRGYNYEYYYGMDV | |
| iPS:393345 | 21-225_26C10 | NA | SEQ ID NO:4758<br>GGCTACTATGCAC | SEQ ID NO:12770<br>TGGATCAACCCTAACAG<br>TGGTGGCACAAACTATG<br>CACAGAAGTTTCAGGGC | SEQ ID NO:20782<br>GAGAGGTGTAGTACTACCAG<br>CTGCTATTTAGGAATTACGG<br>GCTACTACGGTATGGACGTC | |
| | | AA | SEQ ID NO:4759<br>GYYVH | SEQ ID NO:12771<br>WINPNSGGTNYAQKFQG | SEQ ID NO:20783<br>ERCSTTSCYLGITGYYGMDV | |
| iPS:393368 | 21-225_5G7 | NA | SEQ ID NO:4760<br>AGCTATGCCATGAGC | SEQ ID NO:12772<br>GCTATTAGTGGTAGTGGT<br>GGTAGCACATACTACGC<br>AGACTCCGTGAAGGGC | SEQ ID NO:20784<br>GAATATTGTGGTGGTGACTG<br>CTATTCCCCTACTACTACTA<br>CTACGGTATGGACGTC | |
| | | AA | SEQ ID NO:4761<br>SYAMS | SEQ ID NO:12773<br>AISGSGGSTYYADSVKG | SEQ ID NO:20785<br>EYCGGDCYSPYYYYYGMDV | |
| iPS:393565 | 21-225_29H8 | NA | SEQ ID NO:4762<br>AATTATGATATCAAC | SEQ ID NO:12774<br>TGGATGAACCCTAACAG<br>TGGTAACACAGGCTATG<br>CACAGAGAGTTCCAGGGC | SEQ ID NO:20786<br>AGCAGTGGCTGGTACTACTT<br>TGACTAC | |
| | | AA | SEQ ID NO:4763<br>NYDIN | SEQ ID NO:12775<br>WMNPNSGNTGYAQRFQG | SEQ ID NO:20787<br>SSGWYYFDY | |
| | 21-225_34B11 | NA | SEQ ID NO:4764<br>GGCTACTATATGCAC | SEQ ID NO:12776<br>TGGATCAACCCTAACAG<br>TGGTGGCACAAACTATG<br>CACAGAAGTTTCAGGGC | SEQ ID NO:20788<br>GTGTATTTCTATGGTTCGGG<br>GAGTTATTATAACGAGTTTG<br>ACTAC | |
| | | AA | SEQ ID NO:4765<br>GYYMH | SEQ ID NO:12777<br>WINPNSGGTNYAQKFQG | SEQ ID NO:20789<br>VYFYGSGSYYNEFDY | |
| | | | SEQ ID NO:4766 | SEQ ID NO:12778 | SEQ ID NO:20790 | |

FIGURE 49
(Continued)

| | | | | | |
|---|---|---|---|---|---|
| iPS:393802 | 21-225_3D12 | NA | ACCGCTGGATGAAC | CGGATTAAAACAAAATTGATGGTGGGACAACAGACTACGTTGCACCCGTGAAAGGC | GAAGGCTGGAACACGGACTAC |
| | | | SEQ ID NO:4767 | SEQ ID NO:12779 | SEQ ID NO:20791 |
| | | AA | TAWMN | RIKNKIDGGTDYVAPVKG | EGWNTDY |
| | | | SEQ ID NO:4768 | SEQ ID NO:12780 | SEQ ID NO:20792 |
| iPS:393804 | 21-225_5H7 | NA | AGAAGTAGTTATTACTGGGGC | AATATCTATTATAGTGGGACCACCTACTACAACCCGTCCCTCAAGAGT | CATGGAAAAGACTGGGGCCTTGACTAC |
| | | | SEQ ID NO:4769 | SEQ ID NO:12781 | SEQ ID NO:20793 |
| | | AA | RSSYYWG | NIYYSGTTYYNPSLKS | HGKDWGLDY |
| | | | SEQ ID NO:4770 | SEQ ID NO:12782 | SEQ ID NO:20794 |
| iPS:393806 | 21-225_6A6 | NA | AGAAGTAGTTACTACTGGGGC | AATATCTATTATAGTGGGATCCCTACTACAACCCGTCCCTCAAGAGT | CACAGCAGCAGCTGGTCTCT |
| | | | SEQ ID NO:4771 | SEQ ID NO:12783 | SEQ ID NO:20795 |
| | | AA | RSSYYWG | NIYYSGIPYYNPSLKS | HSSSWSLDY |
| | | | SEQ ID NO:4772 | SEQ ID NO:12784 | SEQ ID NO:20796 |
| iPS:393808 | 21-225_1A2 | NA | AGCTATACCATGAAC | TCCATTAGTGGTAGTGGTAGTTACATATACTACGCAGACTCAGTGAAGGGC | GGGAGCAGCTCGTCCGGGTTTGACTAC |
| | | | SEQ ID NO:4773 | SEQ ID NO:12785 | SEQ ID NO:20797 |
| | | AA | SYTMN | SISGSGSYIYYADSVKG | GSSSSGFDY |
| | | | SEQ ID NO:4774 | SEQ ID NO:12786 | SEQ ID NO:20798 |
| iPS:393810 | 21-225_5A4 | NA | AGCTCTGCCATGAGC | GCTATTAGTGGTGGTCGTGGTGGTAACACATTCTACACAGACTCCGTGAAGGGC | CTGGGGAAAGACTACTACTACTACGGTATGGACGTC |
| | | | SEQ ID NO:4775 | SEQ ID NO:12787 | SEQ ID NO:20799 |

FIGURE 49
(Continued)

| | | | | | | | |
|---|---|---|---|---|---|---|---|
| iPS:393812 | 21-225_6A11 | AA | SSAMS | | AISGRGGNTFYTDSVKG | | LGKDYYYGMDV |
| | | | SEQ ID NO:4776 | | SEQ ID NO:12788 | | SEQ ID NO:20800 |
| | | NA | GACTATGGCATGCAC | | GTTATATGGTTTGATGGA AGTAATAAATACTATGC AGACTCCGTGAAGGGC | | GATCTTGGCTGGACGGAAGA GTAC |
| | | | SEQ ID NO:4777 | | SEQ ID NO:12789 | | SEQ ID NO:20801 |
| | | AA | DYGMH | | VIWFDGSNKYYADSVKG | | DLGWTEEY |
| | | | SEQ ID NO:4778 | | SEQ ID NO:12790 | | SEQ ID NO:20802 |
| iPS:393814 | 21-225_7F4 | NA | AGGAGTAGTTACTACTGGGG C | | AATATCTATTATAGTGGG GCCACTACTACAACCC GTCCCTCAAGAGT | | CATAGCGGGCAGCAGCTGGTCCCT TGACTAC |
| | | | SEQ ID NO:4779 | | SEQ ID NO:12791 | | SEQ ID NO:20803 |
| | | AA | RSSYYWG | | NIYYSGATYYNPSLKS | | HSGSWSLDY |
| | | | SEQ ID NO:4780 | | SEQ ID NO:12792 | | SEQ ID NO:20804 |
| iPS:393816 | 21-225_6D4 | NA | AGAAGTAGTTCCTACTGGGG C | | AATATCTATTATAGTGGG AGCGCCTACTACATTCCG TCCCTCAAGAGT | | CACAGCAGCAGCTGGTCTCT TGACTGC |
| | | | SEQ ID NO:4781 | | SEQ ID NO:12793 | | SEQ ID NO:20805 |
| | | AA | RSSSYWG | | NIYYSGSAYYIPSLKS | | HSSSWSLDC |
| | | | SEQ ID NO:4782 | | SEQ ID NO:12794 | | SEQ ID NO:20806 |
| iPS:393818 | 21-225_6G12 | NA | AGCTATGGCATGCAC | | GTTATTGGTATGATGATAGA AGTAATAACTACTATGC AGACTCCGTGAAGGGC | | GAACTGGGGTTCCGGTCTGA CTAC |
| | | | SEQ ID NO:4783 | | SEQ ID NO:12795 | | SEQ ID NO:20807 |
| | | AA | SYGMH | | VIWYDRSNNYYADSVKG | | ELGFRSDY |
| | | | SEQ ID NO:4784 | | SEQ ID NO:12796 | | SEQ ID NO:20808 |

FIGURE 49
(Continued)

| | | | | | |
|---|---|---|---|---|---|
| iPS:393820 | 21-225_8H7 | NA | GACTTTGGCATGCAC | GTTATTTGGTATGAAGAAAATAATCAATACTATGCAGACTCCGTGAAGGGC | GAGCTGGGGGTTCCGGTCTGACTAC |
| | | | SEQ ID NO:4785 | SEQ ID NO:12797 | SEQ ID NO:20809 |
| | | AA | DFGMH | VIWYEENNQYYADSVKG | ELGFRSDY |
| | | | SEQ ID NO:4786 | SEQ ID NO:12798 | SEQ ID NO:20810 |
| iPS:393822 | 21-225_15B11 | NA | AACTATGGCATGCAC | GTTATATGGTATGAGAAAGTAATAATACTATCAGACTCCGTGAAGGGC | GAAGTGGGGGATTCACTGAGGACTAC |
| | | | SEQ ID NO:4787 | SEQ ID NO:12799 | SEQ ID NO:20811 |
| | | AA | NYGMH | VIWYEESNKYYTDSVKG | EVGFTEDY |
| | | | SEQ ID NO:4788 | SEQ ID NO:12800 | SEQ ID NO:20812 |
| iPS:393824 | 21-225_10F12 | NA | AGCTATGCCATGAGC | ATTATTAGTGGTGGTCGTGGTGGTAACACATTCTACGCAGACTCCGTGAAGGGC | CGTGTAGCAGTGGCTGGCTCGGAGGCTTTTGCTATC |
| | | | SEQ ID NO:4789 | SEQ ID NO:12801 | SEQ ID NO:20813 |
| | | AA | SYAMS | IISGRGGNTFYADSVKG | RVAVAGSEAFAI |
| | | | SEQ ID NO:4790 | SEQ ID NO:12802 | SEQ ID NO:20814 |
| iPS:393826 | 21-225_10G5 | NA | AACTATGGCATGCAC | GTTATTTGGTATGAAGAAAATAATCAATACTATGCAGACTCCGTGAAGGGC | GAACTGGGGGTTCCGGTCTGACTAC |
| | | | SEQ ID NO:4791 | SEQ ID NO:12803 | SEQ ID NO:20815 |
| | | AA | NYGMH | VIWYEENNQYYADSVKG | ELGFRSDY |
| | | | SEQ ID NO:4792 | SEQ ID NO:12804 | SEQ ID NO:20816 |

FIGURE 49
(Continued)

| | | | | | |
|---|---|---|---|---|---|
| iPS:393828 | 21-225_10H12 | NA | GACTATGGCATGCAC | GTTATTGGTATGAAGAC AATAATCAATACTATGC AGACTCCGTGAAGGGC | GAACTGGGGTTCCGGTCTGA CTAC |
| | | | SEQ ID NO:4793 | SEQ ID NO:12805 | SEQ ID NO:20817 |
| | | AA | DYGMH | VIWYEDNNQYYADSVKG | ELGFRSDY |
| | | | SEQ ID NO:4794 | SEQ ID NO:12806 | SEQ ID NO:20818 |
| iPS:393830 | 21-225_12A1 | NA | AGTTATGGCATGCAC | GTTATTGGTATGAAGA AATAATCAATACTATG CAGACTCCGTGAAGGGC | GAACTGGGGTTCCGGTCTGA CTAC |
| | | | SEQ ID NO:4795 | SEQ ID NO:12807 | SEQ ID NO:20819 |
| | | AA | SYGMH | VIWYEENNQYYADSVKG | ELGFRSDY |
| | | | SEQ ID NO:4796 | SEQ ID NO:12808 | SEQ ID NO:20820 |
| iPS:393832 | 21-225_14B2 | NA | AGAAGTAGTTATTACTGGG T | AATATCTATTATAGTGG ACCACCTACTACAACCC GTCCCTCAAGAGT | CATGGAAAAGACTGGGGCCT TGACTAC |
| | | | SEQ ID NO:4797 | SEQ ID NO:12809 | SEQ ID NO:20821 |
| | | AA | RSSYYWG | NIYYSGTTYYNPSLKS | HGKDWGLDY |
| | | | SEQ ID NO:4798 | SEQ ID NO:12810 | SEQ ID NO:20822 |
| iPS:393836 | 21-225_15A2 | NA | AGCTATACCATGAAC | TCCATTAGTGGTAGTGGT AGTTACATATACTACGC AGACTCAGTGAAGGGC | GTGGCTTCATTGACTAC |
| | | | SEQ ID NO:4799 | SEQ ID NO:12811 | SEQ ID NO:20823 |
| | | AA | SYTMN | SISGSGSYIYYADSVKG | VASFDY |
| | | | SEQ ID NO:4800 | SEQ ID NO:12812 | SEQ ID NO:20824 |

FIGURE 49
(Continued)

| | | | | |
|---|---|---|---|---|
| iPS:393838 | 21-225_6G2 | NA | GACTATGGCATACAC | GTCATTGGTTTGATGGA AGTAATAAATACTATGC AGACTCCGTGAAGGGC | GATCTTGGCTGGACGGAAGA GTAC |
| | | | SEQ ID NO:4801 | SEQ ID NO:12813 | SEQ ID NO:20825 |
| | | AA | DYGIH | VIWFDGSNKYYADSVKG | DLGWTEEY |
| | | | SEQ ID NO:4802 | SEQ ID NO:12814 | SEQ ID NO:20826 |
| iPS:393840 | 21-225_3F8 | NA | AGCTATGGCATGCAC | GTTATATGGCATGATGG AAGTAATAAATACTATG CAGACTCCGTGAAGGGC | GATCTGAGTATGGGCGGTAT GGACGTC |
| | | | SEQ ID NO:4803 | SEQ ID NO:12815 | SEQ ID NO:20827 |
| | | AA | SYGMH | VIWHDGSNKYYADSVKG | DLSMGGMDV |
| | | | SEQ ID NO:4804 | SEQ ID NO:12816 | SEQ ID NO:20828 |
| iPS:393844 | 21-225_3G7 | NA | AACTATGGCATGCAC | GTCATATGGCATGATGG AAGTAATAAATACTATG TAGACTCCGTGAAGGGC | GATGAGAGGCTGGGGGATTTT TGACTAC |
| | | | SEQ ID NO:4805 | SEQ ID NO:12817 | SEQ ID NO:20829 |
| | | AA | NYGMH | VIWHDGSNKYYVDSVKG | DERLGFDY |
| | | | SEQ ID NO:4806 | SEQ ID NO:12818 | SEQ ID NO:20830 |
| iPS:393848 | 21-225_4H2 | NA | GGCTATGCCATGAAC | GTTATTAGTCGTAGTGGT GGTTACACATACTACGC GGACTCCGTGAAGGGC | CGTTTAGCAGTCAGTGGCTGGCTC GGAGGCTTTTGATATC |
| | | | SEQ ID NO:4807 | SEQ ID NO:12819 | SEQ ID NO:20831 |
| | | AA | GYAMN | VISRSGGYTYYADSVKG | RLAVAGSEAFDI |
| | | | SEQ ID NO:4808 | SEQ ID NO:12820 | SEQ ID NO:20832 |

FIGURE 49
(Continued)

| iPS:393852 | 21-225_12A10 | NA | AGCTATGGCATGCAC<br><br>SEQ ID NO:4809 | GTTATATGGCATGATGA<br>AAGTAATAAATACTATA<br>CAGACTCCGTGAAGGGC<br><br>SEQ ID NO:12821 | GACGAGAGGCTGGGGATTTT<br>TGACTAC<br><br>SEQ ID NO:20833 |
| --- | --- | --- | --- | --- | --- |
| | | AA | SYGMH<br>SEQ ID NO:4810 | VIWHDESNKYYTDSVKG<br>SEQ ID NO:12822 | DERLGIFDY<br>SEQ ID NO:20834 |
| iPS:393854 | 21-225_7H11 | NA | GACTATGGCATGCAC<br><br>SEQ ID NO:4811 | GTTATATGGTATGATGA<br>AAATAATAAATACTATG<br>CAGACTCCGTGAAGGGC<br><br>SEQ ID NO:12823 | GAACTGGGGTTCCGGTCTGA<br>CTAC<br><br>SEQ ID NO:20835 |
| | | AA | DYGMH<br>SEQ ID NO:4812 | VIWYDENNKYYADSVKG<br>SEQ ID NO:12824 | ELGFRSDY<br>SEQ ID NO:20836 |
| iPS:393856 | 21-225_14C2 | NA | GACTATGGCATGCAC<br><br>SEQ ID NO:4813 | GTTATATGGTATGACGA<br>AAGTAATAAATACTATG<br>AAGACTCCGTGAAGGGC<br><br>SEQ ID NO:12825 | GAAGTGGGATTCCGGTCTGA<br>CTAC<br><br>SEQ ID NO:20837 |
| | | AA | DYGMH<br>SEQ ID NO:4814 | VIWYDESNKYYEDSVKG<br>SEQ ID NO:12826 | EVGFRSDY<br>SEQ ID NO:20838 |
| iPS:393862 | 21-225_5G2 | NA | AGCTATGCCATGAGC<br><br>SEQ ID NO:4815 | GTTATTAGTGGTCGTGGT<br>GTTAACACATTCTACGCA<br>GACTCCGTGAAGGGC<br><br>SEQ ID NO:12827 | CGTATAGCAGTGGCTGGCTC<br>GGAGGCTTTGATATC<br><br>SEQ ID NO:20839 |
| | | AA | SYAMS<br>SEQ ID NO:4816 | VISGRGVNTFYADSVKG<br>SEQ ID NO:12828 | RIAVAGSEAFDI<br>SEQ ID NO:20840 |

FIGURE 49
(Continued)

| | | | | | |
|---|---|---|---|---|---|
| iPS:393864 | 21-225_4C5 | NA | AGCTATGTCCTGCAC | GTTATATGGTATGATGG AAGTAATAAATACTATG CAGACTCCGTGAAGGGC | GAAAAGTATACCAGCAGCTG GTACGACTACGGTATGGACG TC |
| | | | SEQ ID NO:4817 | SEQ ID NO:12829 | SEQ ID NO:20841 |
| | | AA | SYVLH | VIWYDGSNKYYADSVKG | EKYTSSWYDYGMDV |
| | | | SEQ ID NO:4818 | SEQ ID NO:12830 | SEQ ID NO:20842 |
| iPS:393866 | 21-225_14E3 | NA | GACTTGGCATGCAC | GTTATTGGTATGAAGAA AATAATCAATACTATG CAGACTCCGTGAAGGGC | GAGCTGGGGTTCCGGTCTGA CTAC |
| | | | SEQ ID NO:4819 | SEQ ID NO:12831 | SEQ ID NO:20843 |
| | | AA | DFGMH | VIWYEENNQYYADSVKG | ELGFRSDY |
| | | | SEQ ID NO:4820 | SEQ ID NO:12832 | SEQ ID NO:20844 |
| iPS:393868 | 21-225_9C11 | NA | AGCTATGGCATGCAC | GTTATATGGCATGATGA AACTAATAAATACTATG CAGATTCCGTGAAGGGC | GACGAGAGGCTGGGGATTTT TGACTAC |
| | | | SEQ ID NO:4821 | SEQ ID NO:12833 | SEQ ID NO:20845 |
| | | AA | SYGMH | VIWHDETNKYYADSVKG | DERLGIFDY |
| | | | SEQ ID NO:4822 | SEQ ID NO:12834 | SEQ ID NO:20846 |
| iPS:393870 | 21-225_7B1 | NA | AGCTATGACATGAGC | ACTATTAGTGGTAGTGGT GGTATCACATACGC AGACTCCGTGAAGGGC | GATCGGGGCAGGGTC |
| | | | SEQ ID NO:4823 | SEQ ID NO:12835 | SEQ ID NO:20847 |
| | | AA | SYDMS | TISGSGGITYYADSVKG | DRGSV |
| | | | SEQ ID NO:4824 | SEQ ID NO:12836 | SEQ ID NO:20848 |

FIGURE 49
(Continued)

| | | | | |
|---|---|---|---|---|
| iPS:393872 | 21-225_2A11 | NA | AGGAGTAGTTACTACTGGGGC | AATATCTATTATAGTGGGAGCACCTACTACAACCCGTCCGTCAAGAGT | CATGGAAAAGACTGGGGCCTTGAAGAC |
| | | | SEQ ID NO:4825 | SEQ ID NO:12837 | SEQ ID NO:20849 |
| | | AA | RSSYYWG | NIYYSGSTYYNPSVKS | HGKDWGLED |
| | | | SEQ ID NO:4826 | SEQ ID NO:12838 | SEQ ID NO:20850 |
| iPS:393874 | 21-225_4C8 | NA | AACTATGGCATGAAC | GTTATTGTATGAAGAAATAATCAATACTATGCAGACTCCGTGAAGGGC | GAAATGGGGTTCCTGTCTGACTAC |
| | | | SEQ ID NO:4827 | SEQ ID NO:12839 | SEQ ID NO:20851 |
| | | AA | NYGMH | VIWYEENNQYYADSVKG | EMGFLSDY |
| | | | SEQ ID NO:4828 | SEQ ID NO:12840 | SEQ ID NO:20852 |
| iPS:393876 | 21-225_9A1 | NA | GACTATGGCATGCAC | GTTATATGGTTTGATGGAAGTAGCACATACTATGCAGACTCCGTGAAGGGC | GATCTTGGCTGGACGGAAGAGTAC |
| | | | SEQ ID NO:4829 | SEQ ID NO:12841 | SEQ ID NO:20853 |
| | | AA | DYGMH | VIWFDGSNKYYADSVKG | DLGWTEEY |
| | | | SEQ ID NO:4830 | SEQ ID NO:12842 | SEQ ID NO:20854 |
| iPS:393878 | 21-225_7G12 | NA | AGCTATGCCATGAAC | GTTATTAGTGGTAGTGGTGGTAGCACATACTACGCAGACTCCGTGAAGGGC | AGGTATACCAGTGACTGGCATGATGCTTTTGATATC |
| | | | SEQ ID NO:4831 | SEQ ID NO:12843 | SEQ ID NO:20855 |
| | | AA | SYAMN | VISGSGGSTYYADSVKG | RYTSDWHDAFDI |
| | | | SEQ ID NO:4832 | SEQ ID NO:12844 | SEQ ID NO:20856 |
| iPS:393880 | 21_225_15A1 | NA | AGAAGTAGTTACTACTGGGGC | AGTATCTATTATAGTGGGAGCGCCAGTACAACCCGTCCCTCAAGAGT | CTGAGCAGCAGCTGGTCTTT |

FIGURE 49
(Continued)

| | | | | | | | |
|---|---|---|---|---|---|---|---|
| iPS:393882 | 21-225_15A1 | AA | SEQ ID NO:4833<br>RSSYYWG | | SEQ ID NO:12845<br>SIYYSGSAQYNPSLKS | | SEQ ID NO:20857<br>LSSSWSFDY |
| | | NA | SEQ ID NO:4834<br>AGCTATGGCATGCAC | | SEQ ID NO:12846<br>GTTATATGGTATGAGGA<br>AATAATAAACACTATG<br>CAGACTCCGTGAAGGGC | | SEQ ID NO:20858<br>GAGCTGGGGGTTCCTCTCTGA<br>CTAC |
| iPS:393884 | 21-225_15E3 | AA | SEQ ID NO:4835<br>SYGMH | | SEQ ID NO:12847<br>VIWYEENNKHYADSVKG | | SEQ ID NO:20859<br>ELGFLSDY |
| | | NA | SEQ ID NO:4836<br>AACTATGGCATGCAC | | SEQ ID NO:12848<br>GTTATATGGTATGAAGGA<br>AAGTAATCAATACTATG<br>GAGACTCCGTGAAGGGC | | SEQ ID NO:20860<br>GAGCTGGGGTTCCTCTCTGA<br>CTAC |
| iPS:393886 | 21-225_16F4 | AA | SEQ ID NO:4837<br>NYGMH | | SEQ ID NO:12849<br>VIWYEGSNQYYGDSVKG | | SEQ ID NO:20861<br>ELGFLSDY |
| | | NA | SEQ ID NO:4838<br>CCTAATTACTACTGGGGC | | SEQ ID NO:12850<br>AGTATCTATTATAGTGGA<br>AGCACCTCCTACAACCC<br>GTCCCTCAACAGT | | SEQ ID NO:20862<br>CTAAGCAGCAGCAACTGGGACTT<br>TGACAAC |
| iPS:393888 | 21-225_2G9 | AA | SEQ ID NO:4839<br>PNYYWG | | SEQ ID NO:12851<br>SIYYSGSTSYNPSLNS | | SEQ ID NO:20863<br>LSSNWDFDN |
| | | NA | SEQ ID NO:4840<br>AGCTATGTCATGAGC | | SEQ ID NO:12852<br>ATTATTAGTGGTCGTGGT<br>GGTAACACATTCTACGC<br>AGACTCCGTGAAGGGC | | SEQ ID NO:20864<br>CGTTTAGCAGTCAGTGGCTGGCTC<br>GGAGGCTTTTGATATC |
| iPS:393890 | 21-225_3E3 | AA | SEQ ID NO:4841<br>SYVMS | | SEQ ID NO:12853<br>IISGRGGNTFYADSVKG | | SEQ ID NO:20865<br>RLAVAGSEAFDI |
| | | NA | SEQ ID NO:4842 | | SEQ ID NO:12854 | | SEQ ID NO:20866 |

FIGURE 49
(Continued)

| | | | | | | |
|---|---|---|---|---|---|---|
| iPS:393890 | 21-225_4B1 | NA | AGTTACTCCTGGAGC | | CGTATCTATACCAGTGG GAGCACCAACTACATCC CCTCCCTCAAGAGT | | GATTTGAAGAGCAGTGGCTG CCTTTCTTTGACTAC |
| | | | SEQ ID NO:4843 | | SEQ ID NO:12855 | | SEQ ID NO:20867 |
| | | AA | SYSWS | | RIYTSGSTNYIPSLKS | | DLKSSGCLFFDY |
| | | | SEQ ID NO:4844 | | SEQ ID NO:12856 | | SEQ ID NO:20868 |
| iPS:393892 | 21-225_6G7 | NA | AGCTATGGCATGCAC | | ATTATATCATATGTTGGA AAGAATAATATTATGC AGACTCCGTGAAGGGC | | CGGGGAAACAGTATGGCGG GTACGGTATGGACGTC |
| | | | SEQ ID NO:4845 | | SEQ ID NO:12857 | | SEQ ID NO:20869 |
| | | AA | SYGMH | | IISYVGKNKYYADSVKG | | RGNSYGGYGMDV |
| | | | SEQ ID NO:4846 | | SEQ ID NO:12858 | | SEQ ID NO:20870 |
| iPS:393894 | 21-225_5E11 | NA | AGCTATAGCATGAAC | | TCCATTAGTGGTAGTAGT ACTTACATATACGCA GACTCAGTGAAGGGC | | GTGGCTTCATTTGACTAC |
| | | | SEQ ID NO:4847 | | SEQ ID NO:12859 | | SEQ ID NO:20871 |
| | | AA | SYSMN | | SISGSSTYIYYADSVKG | | VASFDY |
| | | | SEQ ID NO:4848 | | SEQ ID NO:12860 | | SEQ ID NO:20872 |
| iPS:393896 | 21-225_2A4 | NA | AGCTATAGCATGAAC | | TCCATTAGTGGTAGTAGT ACTTACATATACGCA GACTCAGTGAAGGGC | | GTGGCTTCATTTGACTAC |
| | | | SEQ ID NO:4849 | | SEQ ID NO:12861 | | SEQ ID NO:20873 |
| | | AA | SYSMN | | SISGSSTYIYYADSVKG | | VASFDY |
| | | | SEQ ID NO:4850 | | SEQ ID NO:12862 | | SEQ ID NO:20874 |
| iPS:393898 | 21-225_5F7 | NA | AGCTATGCCATGAGC | | ATTATTAGTGGTCGTGGT GGTAACACATTCTACGC AGACTCCGTGAAGGGC | | CGTATAGCAGTGGCTGGCTC GGAGGCTTTTGCTATC |
| | | | SEQ ID NO:4851 | | SEQ ID NO:12863 | | SEQ ID NO:20875 |
| | | AA | SYAMS | | IISGRGGNTFYADSVKG | | RIAVAGSEAFAI |

FIGURE 49
(Continued)

| | | | | | |
|---|---|---|---|---|---|
| iPS:393900 | 21-225_10E12 | NA | SEQ ID NO:4852 AACTATGGCATGCAC | SEQ ID NO:12864 GTTATATGGCATGATGG AAGTAATAAATACTATG TAGACTCCGTGAAGGGC | SEQ ID NO:20876 GATGAGAGGCTGGGATTTT TGACTAC |
| | | AA | SEQ ID NO:4853 NYGMH | SEQ ID NO:12865 VIWHDGSNKYYVDSVKG | SEQ ID NO:20877 DERLGIFDY |
| iPS:393902 | 21-225_14E10 | NA | SEQ ID NO:4854 GACTATGGCATGCAC | SEQ ID NO:12866 GTTATATGGTATGATGG AAGTAATAAATACTATG CAGACTCCGTGAAGGGC | SEQ ID NO:20878 GAGAAGTATAGCAGCAGCTG GTACGACTACGGTATGGACG TC |
| | | AA | SEQ ID NO:4855 DYGMH | SEQ ID NO:12867 VIWYDGSNKYYADSVKG | SEQ ID NO:20879 EKYSSSWYDYGMDV |
| iPS:393904 | 21-225_8H11 | NA | SEQ ID NO:4856 ACCTATAACATGCAC | SEQ ID NO:12868 GTTATATGGTATGATGG AAGTGATAGATACTCTG CAGACTCCGTGAAGGGC | SEQ ID NO:20880 GATCGGGCCTATAGCAGCTC GTCTGACTTC |
| | | AA | SEQ ID NO:4857 TYNMH | SEQ ID NO:12869 VIWYDGSDRYSADSVKG | SEQ ID NO:20881 DRAYSSSSDF |
| | | | SEQ ID NO:4858 | SEQ ID NO:12870 | SEQ ID NO:20882 |
| iPS:393906 | 21-225_13D3 | NA | AGTTATATACCATGAAC | TCCATTAGTGGTAGTAGT AGTTACATATACTACG GGACTCAGTGAAGGGC | GATCGGGGCAGTGGC |
| | | AA | SEQ ID NO:4859 SYTMN | SEQ ID NO:12871 SISGSSSYIYYADSVKG | SEQ ID NO:20883 DRGSG |
| | | | SEQ ID NO:4860 | SEQ ID NO:12872 | SEQ ID NO:20884 |

FIGURE 49
(Continued)

| | | | | |
|---|---|---|---|---|
| iPS:393908 | 21-225_10E9 | NA | AACTATGTCATACAC | GTTATATGGTATGATGG AAGTAATAAATACTATG CAGACTCCGTGAAGGGC | GAAAAGTATAGCAGCAGCTG GTACGACTACGGTATGGACG TC |
| | | | SEQ ID NO:4861 | SEQ ID NO:12873 | SEQ ID NO:20885 |
| | | AA | NYVIH | VIWYDGSNKYYADSVKG | EKYSSSWYDYGMDV |
| | | | SEQ ID NO:4862 | SEQ ID NO:12874 | SEQ ID NO:20886 |
| iPS:393910 | 21-225_15F10 | NA | AGCTATGGCATGCAC | GTTATATCATATGGTGGA AGTAATAATTACTATGC AGACTCCGTGAAGGGC | CGGGGATACAGCTATGGCGG GTACGGTATGGACGTC |
| | | | SEQ ID NO:4863 | SEQ ID NO:12875 | SEQ ID NO:20887 |
| | | AA | SYGMH | VISYGGSNNYYADSVKG | RGYSYGGYGMDV |
| | | | SEQ ID NO:4864 | SEQ ID NO:12876 | SEQ ID NO:20888 |
| iPS:393912 | 21-225_16F6 | NA | AACTATGGCATGAAC | GTTATATGGTATGATGG AAGTAATCAATACTATG GAGACTCCGTGAAGGGC | GAGCTGGGGTTCCTCTCTGA TTAC |
| | | | SEQ ID NO:4865 | SEQ ID NO:12877 | SEQ ID NO:20889 |
| | | AA | NYGMH | VIWYEGSNQYYGDSVKG | ELGFLSDY |
| | | | SEQ ID NO:4866 | SEQ ID NO:12878 | SEQ ID NO:20890 |
| iPS:393914 | 21-225_16B8 | NA | AGCTATAGCATGAAC | TCCATTAGTGGTAGTAGT ACTTACATATACTACGCA GACTCAGTGAAGGGC | GTGGCTTCATTGACTAC |
| | | | SEQ ID NO:4867 | SEQ ID NO:12879 | SEQ ID NO:20891 |
| | | AA | SYSMN | SISGSSTYIYYADSVKG | VASFDY |
| | | | SEQ ID NO:4868 | SEQ ID NO:12880 | SEQ ID NO:20892 |
| iPS:393916 | 21_225_2G4 | NA | AGCTATGTCATGCAC | GTTATATGGTATGATGG AAGTAATAAATACTATG CAGACTCCGTGAAGGGC | GAGAAGTATAGCAGCAGCTG GTACGACTACGGTATGGACG TC |

FIGURE 49
(Continued)

| | | | | | | | |
|---|---|---|---|---|---|---|---|
| iPS:393920 | 21-225_2G4 | AA | SEQ ID NO:4869 SYVMH | | SEQ ID NO:12881 VIWYDGSNKYYADSVKG | | SEQ ID NO:20893 EKYSSSWYDYGMDV |
| | | NA | SEQ ID NO:4870 AGCTATGGCATGCAC | | SEQ ID NO:12882 ATTATATGGCATGATGG AAGTAATAAATACTATG TAGACTCCGTGAAGGGC | | SEQ ID NO:20894 GATGAGAGGCTCGGGATTTT TGACTAC |
| iPS:393922 | 21-225_1H12 | AA | SEQ ID NO:4871 SYGMH | | SEQ ID NO:12883 IIWHDGSNKYYVDSVKG | | SEQ ID NO:20895 DERLGIFDY |
| | | NA | SEQ ID NO:4872 AGCTATGGCATGCAC | | SEQ ID NO:12884 GTTATATGGTATGAGGA AATAATAAATACTATG TAGACTCCGTGAAGGGC | | SEQ ID NO:20896 GAACTAGGCTTCCAGTCTGA CTAC |
| iPS:393924 | 21-225_2B2 | AA | SEQ ID NO:4873 SYGMH | | SEQ ID NO:12885 VIWYEENNKYYVDSVKG | | SEQ ID NO:20897 ELGFQSDY |
| | | NA | SEQ ID NO:4874 AGCTATGGCATGCAC | | SEQ ID NO:12886 GTTATATGGCATGATGG AAGTAATAAATACTATG CAGACTCCGTGAAGGGC | | SEQ ID NO:20898 GATCTGAGAATGGGCGGTAT GGACGTC |
| iPS:393926 | 21-225_4G4 | AA | SEQ ID NO:4875 SYGMH | | SEQ ID NO:12887 VIWHDGSNKYYADSVKG | | SEQ ID NO:20899 DLRMGGMDV |
| | | NA | SEQ ID NO:4876 CGTAGTAGTTACTACTGGGG C | | SEQ ID NO:12888 AGTGTCTATTATAGTGGG GCCACCTCCTACAACCC GTCCCTCAAGAGT | | SEQ ID NO:20900 CTAAGCAGCAACTGGGACTT TGACTAC |
| iPS:393928 | 21-225_4E10 | NA | | | | | |

FIGURE 49
(Continued)

| | | | | | | | |
|---|---|---|---|---|---|---|---|
| iPS:393930 | 21-225_4E10 | AA | SEQ ID NO:4877<br>RSSYYWG | SEQ ID NO:4878<br>AGCTTTGGCATGCAC | SEQ ID NO:12889<br>SVYYSGATSYNPSLKS | SEQ ID NO:12890<br>ATTATATGGCATGATGG<br>AAGTAATAAATACTATG<br>CAGACTCCGTGAAGGGC | SEQ ID NO:20901<br>LSSNWDFDY | SEQ ID NO:20902<br>GATCTGAGTGATGGGCGGTAT<br>GGACGTC |
| iPS:393932 | 21-225_7E11 | AA<br>NA | SEQ ID NO:4879<br>SFGMH<br>SEQ ID NO:4880<br>AGCTATGGCATGCAC | | SEQ ID NO:12891<br>IIWHDGSNKYYADSVKG<br>SEQ ID NO:12892 | SEQ ID NO:20903<br>DLSMGGMDV<br>SEQ ID NO:20904 | | |
| iPS:393932 | 21-225_10F5 | AA<br>NA | SEQ ID NO:4881<br>SYGMH<br>SEQ ID NO:4882<br>AACTATGGCATGCAC | | SEQ ID NO:12893<br>IIWHDGSNKYYVDSVKG<br>SEQ ID NO:12894 | ATTATATGGCATGATGG<br>AAGTAATAAATATTATG<br>TAGACTCCGTGAAGGGC | SEQ ID NO:20905<br>DERLGIFDY<br>SEQ ID NO:20906 | GATGAGAGGCTGGGGATTTT<br>TGACTAC |
| iPS:393934 | 21-225_13E6 | AA<br>NA | SEQ ID NO:4883<br>NYGMH<br>SEQ ID NO:4884<br>AGCTATGCCATGAAC | | SEQ ID NO:12895<br>VIWYDENNKYYIDSVKG<br>SEQ ID NO:12896 | GTTATTAGTGGTAGAGG<br>AATAATAAATATTATA<br>TAGACTCCGTGAAGGGC | SEQ ID NO:20907<br>ELGFRSDY<br>SEQ ID NO:20908 | GAATTGGGGTTCCGGTCTGA<br>CTAC |
| iPS:393936 | 21-225_14A11 | AA | SEQ ID NO:4885<br>SYAMN<br>SEQ ID NO:4886 | | SEQ ID NO:12897<br>VISGRGGSTYYADSVKG<br>SEQ ID NO:12898 | GTTATTAGTGGTAGAGG<br>TGGTAGTACATACTACG<br>CAGACTCCGTGAAGGGC | SEQ ID NO:20909<br>RIAAGMEYFDL<br>SEQ ID NO:20910 | AGGATAGCAGCTGGTATGGA<br>GTACTTCGATCTC |

FIGURE 49
(Continued)

| | | | | |
|---|---|---|---|---|
| iPS:393940 | 21-225_16B2 | NA | AGCTATGCCATGACC | GTTATTAGTAGTGGTAGTGGT GGTAGCACATTCTACGC AGACTCCGTGAAGGGC | TATTGTAGTAGTAGTACCAGGTG CCCTTATGATGCCTTTGATAT C |
| | | | SEQ ID NO:4887 | SEQ ID NO:12899 | SEQ ID NO:20911 |
| | | AA | SYAMT | VISGSGGSTFYADSVKG | YCSSTRCPYDAFDI |
| | | | SEQ ID NO:4888 | SEQ ID NO:12900 | SEQ ID NO:20912 |
| iPS:393942 | 21-225_11E5 | NA | AATTATGATATCAAC | TGGATGCACCTAACAG TGGTGCCACCGGCTATG CACAGAGGTTCCAGGGC | AGCAGTGGCTGGGAGGTCTT TGACTAC |
| | | | SEQ ID NO:4889 | SEQ ID NO:12901 | SEQ ID NO:20913 |
| | | AA | NYDIN | WMHPNSGATGYAQRFQG | SSGWEVFDY |
| | | | SEQ ID NO:4890 | SEQ ID NO:12902 | SEQ ID NO:20914 |
| iPS:393944 | 21-225_14D6 | NA | AGTTATACCATGAAC | TCCATTAGTGGTAGTGGT AGTTACATATACTACGC AGACTCAGTGAAGGGC | GTAGCAGCCTTTGACTCC |
| | | | SEQ ID NO:4891 | SEQ ID NO:12903 | SEQ ID NO:20915 |
| | | AA | SYTMN | SISGSGSYIYYADSVKG | VAAFDS |
| | | | SEQ ID NO:4892 | SEQ ID NO:12904 | SEQ ID NO:20916 |
| iPS:393946 | 21-225_16A4 | NA | AGCTATAGCATGAAC | TCCATTAGTGGTAGTAGT ACTACAAATACTACGC AGACTCAGTGAAGGGC | GATCGTGGGGAGCTAC |
| | | | SEQ ID NO:4893 | SEQ ID NO:12905 | SEQ ID NO:20917 |
| | | AA | SYSMN | SISGSSTYKYYADSVKG | DRGSY |
| | | | SEQ ID NO:4894 | SEQ ID NO:12906 | SEQ ID NO:20918 |
| iPS:393948 | 21-225_16A5 | NA | GACTATGGCATGCAC | GTTATATGGTTTGATGGA AGTAATAAATACTATGT AGACTCCGTGAAGGGC | GATCTTGGCTGGACGGAAGA GTAC |
| | | | SEQ ID NO:4895 | SEQ ID NO:12907 | SEQ ID NO:20919 |

FIGURE 49
(Continued)

| | | | | | | | |
|---|---|---|---|---|---|---|---|
| iPS:393950 | 21-225_3H10 | AA | DYGMH | | VIWFDGSNKYYVDSVKG | | DLGWTEEY |
| | | | SEQ ID NO:4896 | | SEQ ID NO:12908 | | SEQ ID NO:20920 |
| | | NA | AGCTATGTCATGCAC | | GTTATATGGTATGATGG AAGTAATAAATACTATG CAGACTCCGTGAAGGGC | | GAGAGATATAGCAGTGGCTG GTATGACTACGGTTTGGACG TC |
| | | | SEQ ID NO:4897 | | SEQ ID NO:12909 | | SEQ ID NO:20921 |
| iPS:393952 | 21-225_1F1 | AA | SYVMH | | VIWYDGSNKYYADSVKG | | ERYSSGWYDYGLDV |
| | | | SEQ ID NO:4898 | | SEQ ID NO:12910 | | SEQ ID NO:20922 |
| | | NA | AGCTATAACATGAAC | | TCCATTAGTAGTAGTAGT AGTTACATATACTACGC AGACTCAGTGAAGGGC | | GTTAACCTCTTTGACTAC |
| | | | SEQ ID NO:4899 | | SEQ ID NO:12911 | | SEQ ID NO:20923 |
| iPS:393954 | 21-225_4H6 | AA | SYNMN | | SISSSSYIYYADSVKG | | VNLFDY |
| | | | SEQ ID NO:4900 | | SEQ ID NO:12912 | | SEQ ID NO:20924 |
| | | NA | GACTACTATTTGCAC | | TGGATCCACCCTAACAG TGGTGGCACAAACTATG CACAGAAGTTTCAGGGC | | GATGGTACCAGCTCGTTTGA CTAC |
| | | | SEQ ID NO:4901 | | SEQ ID NO:12913 | | SEQ ID NO:20925 |
| iPS:393956 | 21-225_4D7 | AA | DYYLH | | WIHPNSGGTNYAQKFQG | | DGTSSFDY |
| | | | SEQ ID NO:4902 | | SEQ ID NO:12914 | | SEQ ID NO:20926 |
| | | NA | AGCTATGCCATGAGC | | GTTCTTAGTGGTAGTGGT GGTAGCACATTCTACGC AGACTCCGTGAAGGGC | | TATTGTAGTAGTGCCAGGTG CCCTTATGATGCCTTTGATAT C |
| | | | SEQ ID NO:4903 | | SEQ ID NO:12915 | | SEQ ID NO:20927 |
| | | AA | SYAMS | | VLSGSGGSTFYADSVKG | | YCSSARCPYDAFDI |
| | | | SEQ ID NO:4904 | | SEQ ID NO:12916 | | SEQ ID NO:20928 |

FIGURE 49
(Continued)

| | | | | |
|---|---|---|---|---|
| iPS:393958 | 21-225_5H2 | NA | AGCTATACCATGAAC | TCCATTAGTGGTAGTAGT AGTTACATATACTACGC AGACTCAGTGAAGGGC | GGGAGCAGCTCGTCGGCTT TGACTAC |
| | | | SEQ ID NO:4905 | SEQ ID NO:12917 | SEQ ID NO:20929 |
| | | AA | SYTMN | SISGSSYIYYADSVKG | GSSSSGFDY |
| | | | SEQ ID NO:4906 | SEQ ID NO:12918 | SEQ ID NO:20930 |
| iPS:393960 | 21-225_7G2 | NA | GACTATGGCATGCAC | GTTATATGGTATGATGTA ACTAATAAATACTATGC AGACTCCGTGAAGGGC | GAACTTGGCTGGTACGAGGA CTAC |
| | | | SEQ ID NO:4907 | SEQ ID NO:12919 | SEQ ID NO:20931 |
| | | AA | DYGMH | VIWYDVTNKYYADSVKG | ELGWYEDY |
| | | | SEQ ID NO:4908 | SEQ ID NO:12920 | SEQ ID NO:20932 |
| iPS:393962 | 21-225_7H7 | NA | AGAAGTAGTTACTACTGGGG C | AATATCTATTATAGTGGG AGCACCTACTACATCCC GTCCCTCAAGAGT | CACAGTACCAGCTGGTCTCT TGACCAC |
| | | | SEQ ID NO:4909 | SEQ ID NO:12921 | SEQ ID NO:20933 |
| | | AA | RSSYYWG | NIYYSGSTYYIPSLKS | HSTSWSLDH |
| | | | SEQ ID NO:4910 | SEQ ID NO:12922 | SEQ ID NO:20934 |
| iPS:393964 | 21-225_6G1 | NA | AGCTATGGCATGCAC | ATTATATGGTATGATGG AAGTAATAAATACTATG CAGACTCCGTGAAGGGC | GATCTGAGTATGGGCGGTAT GGACGTC |
| | | | SEQ ID NO:4911 | SEQ ID NO:12923 | SEQ ID NO:20935 |
| | | AA | SYGMH | IIWYDGSNKYYADSVKG | DLSMGGMDV |
| | | | SEQ ID NO:4912 | SEQ ID NO:12924 | SEQ ID NO:20936 |

FIGURE 49
(Continued)

| | | NA | AGCTGTGTCATGCAC | GTTATATGGTATGATGGAAGTAATAAATACTATGCAGACTCCGTGAAGGGC | GAAAGGTATACCAGTGGCTGGCACGACTACGGTATGGACGTC |
|---|---|---|---|---|---|
| iPS:393966 | 21-225_7F8 | | SEQ ID NO:4913 | SEQ ID NO:12925 | SEQ ID NO:20937 |
| | | AA | SCVMH | VIWYDGSNKYYADSVKG | ERYTSGWHDYGMDV |
| | | | SEQ ID NO:4914 | SEQ ID NO:12926 | SEQ ID NO:20938 |
| | | NA | AGCTATGCCATGAAC | GCTATTAGTGGTAGTGGTGGTTACACATACTACGCAGACTCCGTGAAGGGC | GGGGGGTCCCTCTCTAC |
| iPS:393968 | 21-225_5A5 | | SEQ ID NO:4915 | SEQ ID NO:12927 | SEQ ID NO:20939 |
| | | AA | SYAMN | AISGSGGYTYYADSVKG | GGSLFY |
| | | | SEQ ID NO:4916 | SEQ ID NO:12928 | SEQ ID NO:20940 |
| | | NA | AACTATGTCATGCAC | GTTATATGGTATGATGGAAGTAATAAATACTATGCAGACTCCGTGAAGGGC | GAGAAGTATAGCAGCAGCTGGTACGACTACGGTATGGACGTC |
| iPS:393972 | 21-225_7C9 | | SEQ ID NO:4917 | SEQ ID NO:12929 | SEQ ID NO:20941 |
| | | AA | NYVMH | VIWYDGSNKYYADSVKG | EKYSSSWYDYGMDV |
| | | | SEQ ID NO:4918 | SEQ ID NO:12930 | SEQ ID NO:20942 |
| | | NA | AACTATGGCATGCAC | GTTATTGGTATGAAGAAATAATCAATACTATGCAGACTCCGTGAAGGGC | GAACTGGGGTTCCGGTCTGACTAC |
| iPS:393974 | 21-225_7C4 | | SEQ ID NO:4919 | SEQ ID NO:12931 | SEQ ID NO:20943 |
| | | AA | NYGMH | VIWYEENNQYYADSVKG | ELGFRSDY |
| | | | SEQ ID NO:4920 | SEQ ID NO:12932 | SEQ ID NO:20944 |

FIGURE 49
(Continued)

| | | | | | |
|---|---|---|---|---|---|
| iPS:393976 | 21-225_7E9 | NA | GACTATGGCATGCAC SEQ ID NO:4921 | GTTATATGGTATGATGA AATAATAAATACTATG TAGACTCCGTGAAGGGC SEQ ID NO:12933 | GAATTGGGGTTCCGGTCTGA CTAC SEQ ID NO:20945 |
| | | AA | DYGMH SEQ ID NO:4922 | VIWYDENNKYYVDSVKG SEQ ID NO:12934 | ELGFRSDY SEQ ID NO:20946 |
| iPS:393978 | 21-225_4C12 | NA | AGCTATGTCATGCAC SEQ ID NO:4923 | GTTATATGGTATGATGG AAGTAATAAATACTATG CAGACTCCGTGAAGGGC SEQ ID NO:12935 | GAGAAGTATAGCAGCAGCTG GTACGACTACGGTATGGACG TC SEQ ID NO:20947 |
| | | AA | SYVMH SEQ ID NO:4924 | VIWYDGSNKYYADSVKG SEQ ID NO:12936 | EKYSSSWYDYGMDV SEQ ID NO:20948 |
| iPS:393980 | 21-225_6D3 | NA | AGCTATGCCATGAAC SEQ ID NO:4925 | GTTATTAGTGGTCGTGGT GGTAACACATTCTACGC AGACTCCGTGAAGGGC SEQ ID NO:12937 | CGTTTGGCAGTGGCTGGCTC GGAGGCTTTGATATC SEQ ID NO:20949 |
| | | AA | SYAMN SEQ ID NO:4926 | VISGRGGNTFYADSVKG SEQ ID NO:12938 | RLAVAGSEAFDI SEQ ID NO:20950 |
| iPS:393982 | 21-225_6C12 | NA | AGCTATATAGCATGAAC SEQ ID NO:4927 | TCCATTAGTAGTAGTAGT AGTTACATATACTACGC AGACTCAGTGAAGGGC SEQ ID NO:12939 | GATCGTGTGGGAGCCTC SEQ ID NO:20951 |
| | | AA | SYSMN SEQ ID NO:4928 | SISSSSYIYYADSVKG SEQ ID NO:12940 | DRGSL SEQ ID NO:20952 |

FIGURE 49
(Continued)

| | | | | |
|---|---|---|---|---|
| iPS:393984 | 21-225_4F12 | NA | AGCTATGGCATGCAC | GTTATATGGTATGATGTTACTAATAAAAGTATGCAGACTCCGTGAAGGGC | GAAAAGGGGGGGTCTATTTGACTAC |
| | | | SEQ ID NO:4929 | SEQ ID NO:12941 | SEQ ID NO:20953 |
| | | AA | SYGMH | VIWYDVTNKKYADSVKG | EKGGLFDY |
| | | | SEQ ID NO:4930 | SEQ ID NO:12942 | SEQ ID NO:20954 |
| iPS:393986 | 21-225_7G4 | NA | AACTATGTCATGCAC | GTTATATGGTATGATGGAAGTAATAAATACTATGCAGACTCCGTGAAGGGC | GAGAAGTATAGCAGCAACTGGTACGACTACGGTATGGACGTC |
| | | | SEQ ID NO:4931 | SEQ ID NO:12943 | SEQ ID NO:20955 |
| | | AA | NYVMH | VIWYDGSNKYYADSVKG | EKYSSNWYDYGMDV |
| | | | SEQ ID NO:4932 | SEQ ID NO:12944 | SEQ ID NO:20956 |
| iPS:393988 | 21-225_7F10 | NA | AGCTATAGCATGAAC | TCCATTAGTAGTAGTAGTAGTTACATATACTACGCAGACTCAGTGAAGGGC | GCTAACCTCTTTGACTAC |
| | | | SEQ ID NO:4933 | SEQ ID NO:12945 | SEQ ID NO:20957 |
| | | AA | SYSMN | SISSSSSYIYYADSVKG | ANLFDY |
| | | | SEQ ID NO:4934 | SEQ ID NO:12946 | SEQ ID NO:20958 |
| iPS:393990 | 21-225_11G7 | NA | AGGAGTACTTACTACTGGGGC | AGTATCTATTATAGTGGGAGCACCTCCTACAGCCCGTCCCTCAAGAGT | CTGAACAGCAGCTGGTCTTTGACTAC |
| | | | SEQ ID NO:4935 | SEQ ID NO:12947 | SEQ ID NO:20959 |
| | | AA | RSTYYWG | SIYYSGSTSYSPSLKS | LNSSWSFDY |
| | | | SEQ ID NO:4936 | SEQ ID NO:12948 | SEQ ID NO:20960 |

FIGURE 49
(Continued)

| | | | | | |
|---|---|---|---|---|---|
| iPS:393992 | 21-225_14H8 | NA | AGCAATAGGCATGAAC | TACATTAGTAGTAGTAGT AGTACCATATACAGC AGACTCTGTGAAGGGC | GGAGGTGGGGAGCCCTTTGA CTAC |
| | | | SEQ ID NO:4937 | SEQ ID NO:12949 | SEQ ID NO:20961 |
| | | AA | SNSMN | YISSSSSTIYYADSVKG | GGGSPFDY |
| | | | SEQ ID NO:4938 | SEQ ID NO:12950 | SEQ ID NO:20962 |
| iPS:393994 | 21-225_8C9 | NA | AGCTATGGCATGCAC | GTTATATGGTATGATGA AATAATAAATACTATG TAGACTCCGTGAAGGGC | GAATTGGGGGTTCCGGTCTGA CTAC |
| | | | SEQ ID NO:4939 | SEQ ID NO:12951 | SEQ ID NO:20963 |
| | | AA | SYGMH | VIWYDENNKYYVDSVKG | ELGFRSDY |
| | | | SEQ ID NO:4940 | SEQ ID NO:12952 | SEQ ID NO:20964 |
| iPS:393996 | 21-225_15C11 | NA | GACTATGTCATGCAC | GTTATATGGTATGATGG AAGTAATAAATACTATG CAGACTCCGTGAAGGGC TC | GAGAAGTATAGCAGCAGCTG GTACGACTACGGGTTGGACG |
| | | | SEQ ID NO:4941 | SEQ ID NO:12953 | SEQ ID NO:20965 |
| | | AA | DYVMH | VIWYDGSNKYYADSVKG | EKYSSSWYDYGLDV |
| | | | SEQ ID NO:4942 | SEQ ID NO:12954 | SEQ ID NO:20966 |
| iPS:393998 | 21-225_12B12 | NA | GACTATGGCATGCAC | GTTATATGGTATGATGTA ACTAATAAATACTATGC AGACTCCGTGAAGGGC | GAGCTTGGCTGGTACGAGGA CTAC |
| | | | SEQ ID NO:4943 | SEQ ID NO:12955 | SEQ ID NO:20967 |
| | | AA | DYGMH | VIWYDVTNKYYADSVKG | ELGWYEDY |
| | | | SEQ ID NO:4944 | SEQ ID NO:12956 | SEQ ID NO:20968 |

FIGURE 49
(Continued)

| | | | | | |
|---|---|---|---|---|---|
| iPS:394000 | 21-225_11A2 | NA | AGCTATGGCATGCAC SEQ ID NO:4945 | GTTATATCATATGGTGGA AGTAATAAAGACTCTGC AGACTCCGTGAAGGGC SEQ ID NO:12957 | CGGGGATACAGCTATGGCGG GTACGGTATGGACGTC SEQ ID NO:20969 |
| | | AA | SYGMH SEQ ID NO:4946 | VISYGGSNKDSADSVKG SEQ ID NO:12958 | RGYSYGGYGMDV SEQ ID NO:20970 |
| iPS:394002 | 21-225_15G7 | NA | AGGAGTAGTTCCTACTGGGG C SEQ ID NO:4947 | AGTATCTATTATAGTGGG TACACCTATTACACCCCG TCCCTCAAGAGT SEQ ID NO:12959 | CTGAGCAGCAGTTGGTCTTT TGACTTC SEQ ID NO:20971 |
| | | AA | RSSSYWG SEQ ID NO:4948 | SIYYSGYTYTPSLKS SEQ ID NO:12960 | LSSSWSFDF SEQ ID NO:20972 |
| iPS:394004 | 21-225_13A1 | NA | AGCTATGGCATGCAC SEQ ID NO:4949 | GTTATATCATATGGTGG AACTAATAATCACTATG CAGACTCCGTGAAGGGC SEQ ID NO:12961 | CGGGGATACAGCTATGGCGG GTACGGTATGGACGTC SEQ ID NO:20973 |
| | | AA | SYGMH SEQ ID NO:4950 | VISYAGTNQYYADSVKG SEQ ID NO:12962 | RGYSYGGYGMDV SEQ ID NO:20974 |
| iPS:394006 | 21-225_15C2 | NA | AGCTATGGCATGCAC SEQ ID NO:4951 | ATAATATCATATGGTGG AGTAATAATCACTATG CAGACTCCGTGAAGGGC SEQ ID NO:12963 | CGGGGATACAGCTATGGCGG GTACGGTATGGACGTC SEQ ID NO:20975 |
| | | AA | SYGMH SEQ ID NO:4952 | IISYGGRNNHYADSVKG SEQ ID NO:12964 | RGYSYGGYGMDV SEQ ID NO:20976 |
| iPS:394008 | 21-225_15H8 | NA | AGCTATGTCATGAAAC SEQ ID NO:4953 | TCCATTAGTGGTAGTAGT ACTTACATATACTGCGCA GACTCAATCAAGGGC SEQ ID NO:12965 | GATCGAGGCTCCATC SEQ ID NO:20977 |

FIGURE 49
(Continued)

| | | AA | SYVMN | | SISGSSTYIYCADSIKG | | DRGSI | |
|---|---|---|---|---|---|---|---|---|
| iPS:394010 | | NA | AACTATGGCATCTAC | | GTTATATCATATGATGGA AGTAATAAATACTATGC AGACTCCGTGAAGGGC | SEQ ID NO:12966 | GATCGGGGAGCAGTGGCTGC TTACTACTACTACGGTATAG ACGTC | SEQ ID NO:20978 |
| | 21-225_12G5 | | SEQ ID NO:4955 | | SEQ ID NO:12967 | | SEQ ID NO:20979 | |
| | | AA | NYGIY | | VISYDGSNKYYADSVKG | | DRGAVAAYYYYGIDV | |
| | | NA | SEQ ID NO:4956 | | SEQ ID NO:12968 | | SEQ ID NO:20980 | |
| iPS:394012 | | | AGCTATGGCATTCAC | | GTTATATGGCATGATGG AAGTAATAAATACTATG CAGACTCCGTGAAGGGC | SEQ ID NO:12969 | GATCTGAGTATGGCGGTAT GGACGTC | SEQ ID NO:20981 |
| | 21-225_15A3 | | SEQ ID NO:4957 | | | | | |
| | | AA | SYGIH | | VIWHDGSNKYYADSVKG | | DLSMGGMDV | |
| | | NA | SEQ ID NO:4958 | | SEQ ID NO:12970 | | SEQ ID NO:20982 | |
| iPS:394014 | | | AGCTATGTCATGAAC | | GTTATTAGTGGTCGTGGT GGTAACACATTCTACGC AGACTCCGTGAAGGGC | SEQ ID NO:12971 | CGTTTGGCAGTGGCTGGCTC GGAGGCTTTTGATATC | SEQ ID NO:20983 |
| | 21-225_8G6 | | SEQ ID NO:4959 | | | | | |
| | | AA | SYVMN | | VISGRGGNTFYADSVKG | | RLAVAGSEAFDI | |
| | | NA | SEQ ID NO:4960 | | SEQ ID NO:12972 | | SEQ ID NO:20984 | |
| iPS:394016 | | | AGCTATGGCATGCAC | | GTTATATGGCATGATGG AAGTAATAAATACTATG CAGACTCCGTGAAGGGC | SEQ ID NO:12973 | GATCTGAGTATGGCGGTAT GGACGTC | SEQ ID NO:20985 |
| | 21-225_13D4 | | SEQ ID NO:4961 | | | | | |
| | | AA | SYGMH | | VIWHDGSNKYYADSVKG | | DLSMGGMDV | |

FIGURE 49
(Continued)

| | | | | SEQ ID NO:4962 AGTATGTCATGAGC | SEQ ID NO:12974 GGTATTAGTGGTAGTGG TGGTAGCACAAACAACG CAGACTCCGTGAAGGGC | SEQ ID NO:20986 AGCTCCTTGTTGACTAC |
|---|---|---|---|---|---|---|
| iPS:394018 | 21-225_15B1 | NA | | | | |
| | | AA | | SEQ ID NO:4963 SYVMS | SEQ ID NO:12975 GISGSGGSTNNADSVKG | SEQ ID NO:20987 SSLFDY |
| iPS:394020 | 21-225_15H10 | NA | | SEQ ID NO:4964 AACTATGGCATGCAC | SEQ ID NO:12976 GTTATATGGTATGATGA AGTAATAAATACTATG AAGACTCCGTGAAGGGC | SEQ ID NO:20988 GAAGTGGGGTTTCTTTCTGA CTAC |
| | | AA | | SEQ ID NO:4965 NYGMH | SEQ ID NO:12977 VIWYDESNKYYEDSVKG | SEQ ID NO:20989 EVGFLSDY |
| iPS:394022 | 21-225_16H6 | NA | | SEQ ID NO:4966 AGCTATGGCATGAAC | SEQ ID NO:12978 GTTATTAGTGTGTAGTGGT GGTTACACATACTACGC GGAGGCTTTTGATATC | SEQ ID NO:20990 CGTTAGCAGTGGCTGGCTC |
| | | AA | | SEQ ID NO:4967 SYAMN | SEQ ID NO:12979 VISRSGGYTYYADSVKG | SEQ ID NO:20991 RLAVAGSEAFDI |
| iPS:394024 | 21-225_16B7 | NA | | SEQ ID NO:4968 AGCTATGGCATGCAC | SEQ ID NO:12980 GTTATATGGTATGATGA AAGTAATAAATACTATG CAGACTCCGTGAAGGGC | SEQ ID NO:20992 GAACTGGGGTTTCTCTCTGA CTAC |
| | | AA | | SEQ ID NO:4969 SYGMH | SEQ ID NO:12981 VIWYDESNKYYADSVKG | SEQ ID NO:20993 ELGFLSDY |
| | | | | SEQ ID NO:4970 | SEQ ID NO:12982 | SEQ ID NO:20994 |

FIGURE 49
(Continued)

| | | | | | |
|---|---|---|---|---|---|
| iPS:394026 | 21-225_16C7 | NA | AGCTATGTCATGACC SEQ ID NO:4971 | ACTATTAGTAGTGGTAGTGGT GGTTGGACATATTATGC AGACTCCGTGAAGGGC SEQ ID NO:12983 | AGCTCCTCTTGTTTGACTAT SEQ ID NO:20995 |
| | | AA | SYVMT SEQ ID NO:4972 | TISGSGGWTYYADSVKG SEQ ID NO:12984 | SSLFDY SEQ ID NO:20996 |
| iPS:394029 | 21-225_1B12 | NA | AGCTATGGCATGCAC SEQ ID NO:4973 | ATTATATCATATGCTGGA AGTAATAAATCCTATGC AGACTCCGTGAAGGGC SEQ ID NO:12985 | CGGGGATACAGCTATGGCGG GTACGGTATGGACGTC SEQ ID NO:20997 |
| | | AA | SYGMH SEQ ID NO:4974 | IISYAGSNKSYADSVKG SEQ ID NO:12986 | RGYSYGGYGMDV SEQ ID NO:20998 |
| iPS:394033 | 21-225_5F4 | NA | AGCTATAGCATGAAC SEQ ID NO:4975 | TCCATTAGTGGTAGTAGT AGTTACATATACTACGC AGACTCCGTGAAGGGC SEQ ID NO:12987 | GTTAACAACTTTGACTAC SEQ ID NO:20999 |
| | | AA | SYSMN SEQ ID NO:4976 | SISGSSSYIYYADSVKG SEQ ID NO:12988 | VNNFDY SEQ ID NO:21000 |
| iPS:394035 | 21-225_5G9 | NA | AATTATGGCATGCAC SEQ ID NO:4977 | ATTATATCATATGCTGGA AGTAATAAATACTATGC AGACTCCGTGAAGGGC SEQ ID NO:12989 | CGTATAACAGCTCGTCTCTA CTACGGTATGGACGTC SEQ ID NO:21001 |
| | | AA | NYGMH SEQ ID NO:4978 | IISYAGSNKYYADSVKG SEQ ID NO:12990 | RITARLYYGMDV SEQ ID NO:21002 |
| iPS:394037 | 21-225_4F4 | NA | AGGAGTAGTTACTACTGGGG C SEQ ID NO:4979 | AATATTTATTATAGTGGG AGCACCTACGACAACCC GTCCCTCAAGAGT SEQ ID NO:12991 | CATGAAAAGACTGGGGCCT TGACTAC SEQ ID NO:21003 |
| | | AA | RSSYYWG | NIYYSGSTYDNPSLKS | HGKDWGLDY |

FIGURE 49
(Continued)

| | | | | | |
|---|---|---|---|---|---|
| iPS:394041 | 21-225_5E5 | NA | SEQ ID NO:4980 AACTATGTCATGCAC | SEQ ID NO:12992 GTTATATGGTATGATGG AAGTAATAAATACTATG CAGACTCCGTGAAGGGC | SEQ ID NO:21004 GAGGTATATAGCAGTGGCTG GTACGACTACGGTATGGACG TC |
| | | AA | SEQ ID NO:4981 NYVMH | SEQ ID NO:12993 VIWYDGSNKYYADSVKG | SEQ ID NO:21005 EVYSSGWYDYGMDV |
| iPS:394043 | 21-225_3B1 | NA | SEQ ID NO:4982 AGCTATGCCATGAAC | SEQ ID NO:12994 GTTATTAGTGGTCGTGGT ATTAACACATTCTACGCA GACTCCGTGAAGGGC | SEQ ID NO:21006 CGTTTAGCAGTGGCTGGCTC GGAGGCTTTGATATC |
| | | AA | SEQ ID NO:4983 SYAMN | SEQ ID NO:12995 VISGRGINTFYADSVKG | SEQ ID NO:21007 RLAVAGSFAFDI |
| iPS:394045 | 21-225_4H4 | NA | SEQ ID NO:4984 AGGAGTAGTTACTACTGGGG C | SEQ ID NO:12996 AATATTATTATAGTGGG AACACCTACAACAACCC GTCCCTCAAGAGT | SEQ ID NO:21008 CATGGAAAAGACTGGGGCCT TGACTAC |
| | | AA | SEQ ID NO:4985 RSSYYWG | SEQ ID NO:12997 NIYYSGNTYNNPSLKS | SEQ ID NO:21009 HGKDWGLDY |
| iPS:394047 | 21-225_5E6 | NA | SEQ ID NO:4986 AGCTATGGCATGCAC | SEQ ID NO:12998 ATTATATCATATGTTGGA AATAATAAATACTATGC AGACTCCGTGAAGGGC | SEQ ID NO:21010 CGGGGATACAGCTATGGCGG GTACGGTATGGACGTC |
| | | AA | SEQ ID NO:4987 SYGMH | SEQ ID NO:12999 IISYVGNNKYYADSVKG | SEQ ID NO:21011 RGYSYGGYGMDV |
| | | | SEQ ID NO:4988 | SEQ ID NO:13000 | SEQ ID NO:21012 |

FIGURE 49
(Continued)

| | | NA | AGAAGTAGTTACTACTGGGG C | AGTATCTATTATATAGTGGG AGCACCTACTACAACCC GTCCCTCAAGAGT | CTTAGCAGCAGCAGCTGGGACTT CCAGCAC |
|---|---|---|---|---|---|
| iPS:394049 | 21-225_13H5 | | SEQ ID NO:4989 | SEQ ID NO:13001 | SEQ ID NO:21013 |
| | | AA | RSSYYWG | SIYYSGSTYYNPSLKS | LSSSWDFQH |
| | | | SEQ ID NO:4990 | SEQ ID NO:13002 | SEQ ID NO:21014 |
| iPS:394051 | 21-225_9E5 | NA | AACTATGCCATGAAC | GCTATTAGTGGTGGTGGT GGTAACACATTCTACGC AGACTCCGTGAAGGGC | CGTATAGCAGTGGCTGGCTC GGAGGCTTTTGCTATC |
| | | | SEQ ID NO:4991 | SEQ ID NO:13003 | SEQ ID NO:21015 |
| | | AA | NYAMN | AISGGGNTFYADSVKG | RIAVAGSEAFAI |
| | | | SEQ ID NO:4992 | SEQ ID NO:13004 | SEQ ID NO:21016 |
| iPS:394053 | 21-225_11F10 | NA | AGAAGTAGTTACTACTGGGG C | AGTATTATTATATAGTGGG AGCGCCAGTACAACCC GTCCCTCAAGAGT | CTGAGCAGCAGCAGCTGGTCTTT TGACTAC |
| | | | SEQ ID NO:4993 | SEQ ID NO:13005 | SEQ ID NO:21017 |
| | | AA | RSSYYWG | SIYYSGSAQYNPSLKS | LSSSWSFDY |
| | | | SEQ ID NO:4994 | SEQ ID NO:13006 | SEQ ID NO:21018 |
| iPS:394055 | 21-225_9C8 | NA | AGCCAGAGCATGAAC | TACATTAGTATTAGTAGT ACCATATACTATGCAGA CTCTGTGAAGGGC | GGAGGTGGGAGCCCTTTGA CTCC |
| | | | SEQ ID NO:4995 | SEQ ID NO:13007 | SEQ ID NO:21019 |
| | | AA | SQSMN | YISISSTIYYADSVKG | GGGSPFDS |
| | | | SEQ ID NO:4996 | SEQ ID NO:13008 | SEQ ID NO:21020 |
| iPS:394057 | 21-225_15H1 | NA | AGAAGTAGTTACTACTGGGG C | AATATCTATTATATAGTGGG TATCCCTACTACAATCCG TCCCTCAAGAGT | CATAGCACCAGCTGGTCCCT TGACTAC |
| | | | SEQ ID NO:4997 | SEQ ID NO:13009 | SEQ ID NO:21021 |
| | | AA | RSSYYWG | NIYYSGYPYYNPSLKS | HSTSWSLDY |
| | | | SEQ ID NO:4998 | SEQ ID NO:13010 | SEQ ID NO:21022 |

FIGURE 49
(Continued)

| | | | | | |
|---|---|---|---|---|---|
| iPS:394059 | 21-225_9E8 | NA | AGCTATGGCATGCAC | GTTATTGGTATGAAGAAATAATCAATACTATGCAGACTCCGTGAAGGGC | GAACTGGGGTTCCGGTCTGACTAC |
| | | | SEQ ID NO:4999 | SEQ ID NO:13011 | SEQ ID NO:21023 |
| | | AA | SYGMH | VIWYEENNQYYADSVKG | ELGFRSDY |
| | | | SEQ ID NO:5000 | SEQ ID NO:13012 | SEQ ID NO:21024 |
| iPS:394061 | 21-225_12D2 | NA | AGCTATAGCATGAAC | TCCATTAGTAGTAGTAGTAGTACATATACGCAGACTCAGTGAAGGGC | TTAGGGGACTAC |
| | | | SEQ ID NO:5001 | SEQ ID NO:13013 | SEQ ID NO:21025 |
| | | AA | SYSMN | SISSSSYIYYADSVKG | LGDY |
| | | | SEQ ID NO:5002 | SEQ ID NO:13014 | SEQ ID NO:21026 |
| iPS:394063 | 21-225_16A1 | NA | AGGAGTAGTTACTACTGGGGC | AGTATCTATTATAGTGGGAGCGCTATCACAACCCGTCCCTCAAGAGT | CTGAGCAGCAGCTGGTCCTTTGACTAC |
| | | | SEQ ID NO:5003 | SEQ ID NO:13015 | SEQ ID NO:21027 |
| | | AA | RSSYYWG | SIYYSGSAYHNPSLKS | LSSSWSFDY |
| | | | SEQ ID NO:5004 | SEQ ID NO:13016 | SEQ ID NO:21028 |
| iPS:394065 | 21-225_11E2 | NA | AATTATGATATCAAC | TGGATGAACACTAACAGTGGTAACACAGGCTATGCACAGAAGTTCCAGGGC | AGTCATGGCTGGTTCCTCTTTGACTAC |
| | | | SEQ ID NO:5005 | SEQ ID NO:13017 | SEQ ID NO:21029 |
| | | AA | NYDIN | WMNTNSGNTGYAQKFQG | SHGWFLFDY |
| | | | SEQ ID NO:5006 | SEQ ID NO:13018 | SEQ ID NO:21030 |

FIGURE 49
(Continued)

| | | | | | |
|---|---|---|---|---|---|
| iPS:394067 | 21-225_12F2 | NA | GACTATGGCATGCAC | GTTATATGGTTGATGA AATAATAAATACTATGT AGATTCCGTGAAGGGC | GAGCTTGCTGGTCCGAGGA CTAC |
| | | | SEQ ID NO:5007 | SEQ ID NO:13019 | SEQ ID NO:21031 |
| | | AA | DYGMH | VIWFDGNNKYYVDSVKG | ELAWSEDY |
| | | | SEQ ID NO:5008 | SEQ ID NO:13020 | SEQ ID NO:21032 |
| iPS:394069 | 21-225_16H1 | NA | AGCTATAGCATGAAC | TCCATTAGTGGTAGTAGT ACTTACATATACTACGCA GACTCAGTGAAGGGC | GTAGCAGCCTTGACTAC |
| | | | SEQ ID NO:5009 | SEQ ID NO:13021 | SEQ ID NO:21033 |
| | | AA | SYSMN | SISGSSTYTYYADSVKG | VAAFDY |
| | | | SEQ ID NO:5010 | SEQ ID NO:13022 | SEQ ID NO:21034 |
| iPS:394071 | 21-225_10C7 | NA | AGCTATAGCATGAAC | TCCATTAGTAGTAGTAAT AATTACATATACTACGC AGACTCAGTGAAGGGC | TTAGGGGTCTAC |
| | | | SEQ ID NO:5011 | SEQ ID NO:13023 | SEQ ID NO:21035 |
| | | AA | SYSMN | SISSSNNYTYYADSVKG | LGVY |
| | | | SEQ ID NO:5012 | SEQ ID NO:13024 | SEQ ID NO:21036 |
| iPS:394073 | 21-225_15C9 | NA | AGAAGTAGTTACTACTGGGG C | AATATCTATTATAGTGGG AGCACCTACAACAACCC GTCCCTCAAGAGT | CAGGGCAGTGGCTGGGAGGT TGACTAC |
| | | | SEQ ID NO:5013 | SEQ ID NO:13025 | SEQ ID NO:21037 |
| | | AA | RSSYYWG | NIYYSGSTYNNPSLKS | QGSGWEVDY |
| | | | SEQ ID NO:5014 | SEQ ID NO:13026 | SEQ ID NO:21038 |
| iPS:394075 | 21-225_8D12 | NA | AGAAGTAGTTACTACTGGGG C | AATATCTATTATAGTGGG TATCCCTACTACAATCCG TCCCTCAAGAGT | CATAGCACCAGCTGGTCCCT |
| | | | SEQ ID NO:5015 | SEQ ID NO:13027 | SEQ ID NO:21039 |

FIGURE 49
(Continued)

| | | | | | | |
|---|---|---|---|---|---|---|
| iPS:394077 | 21-225_8E12 | AA | RSSYYWG | | NIYYSGYPYYNPSLKS | HSTSWSLDY |
| | | | SEQ ID NO:5016 | | SEQ ID NO:13028 | SEQ ID NO:21040 |
| | | NA | AGCTATGGCCATGAGC | | ATTATTAGTGGTCGTGGT GTAACACATTCTACGC AGACTCCGTGAAGGGC | CGTATGGCAGTGGCTGGCTC GGAGGCTTTTGATATC |
| | | | SEQ ID NO:5017 | | SEQ ID NO:13029 | SEQ ID NO:21041 |
| | | AA | SYAMS | | IISGRGGNTFYADSVKG | RMAVAGSEAFDI |
| | | | SEQ ID NO:5018 | | SEQ ID NO:13030 | SEQ ID NO:21042 |
| iPS:394079 | 21-225_11F5 | NA | AGGAGTAGTTACTACTGGGG C | | AATATTATTATAGTGGG AGCACCTACACCAACCC GTCCCTCAAGAGT | CATGGAAAAAGACTGGGGCCT TGACAAC |
| | | | SEQ ID NO:5019 | | SEQ ID NO:13031 | SEQ ID NO:21043 |
| | | AA | RSSYYWG | | NIYYSGSTYTNPSLKS | HGKDWGLDN |
| | | | SEQ ID NO:5020 | | SEQ ID NO:13032 | SEQ ID NO:21044 |
| iPS:394081 | 21-225_16B3 | NA | AGCTATGGCATGCAC | | GTTATATCATATGCTGGA ATTAATAAATCCTATGCA GACTCCGTGAAGGGC | CGGGGATACAGTCTATGGCGG GTATGGTATGGACGTC |
| | | | SEQ ID NO:5021 | | SEQ ID NO:13033 | SEQ ID NO:21045 |
| | | AA | SYGMH | | VISYAGINKSYADSVKG | RGYSYGGYGMDV |
| | | | SEQ ID NO:5022 | | SEQ ID NO:13034 | SEQ ID NO:21046 |
| iPS:394083 | 21-225_16E6 | NA | AGCTATGGCATGCAC | | GTTATATGGCATGATGG AAGTAATAAATACTATG TAGACTCCGTGAAGGGC | GATCTGAGTATGGGCGGTAT GGACGTC |
| | | | SEQ ID NO:5023 | | SEQ ID NO:13035 | SEQ ID NO:21047 |
| | | AA | SYGMH | | VIWHDGSNKYYVDSVKG | DLSMGGMDV |
| | | | SEQ ID NO:5024 | | SEQ ID NO:13036 | SEQ ID NO:21048 |

FIGURE 49
(Continued)

| | | | | |
|---|---|---|---|---|
| iPS:394085 | 21-225_8B11 | NA | AATTATGATATCAAC | TGGATGCACCCTAACAG TGTAACACAGGCTATG CACAGAAGTTCCAGGGC | AGCAGTGGCTGGTACTTCTT TGACTAC |
| | | | SEQ ID NO:5025 | SEQ ID NO:13037 | SEQ ID NO:21049 |
| | | AA | NYDIN | WMHPNSGNTGYAQKFQG | SSGWYFFDY |
| | | | SEQ ID NO:5026 | SEQ ID NO:13038 | SEQ ID NO:21050 |
| iPS:394087 | 21-225_11A5 | NA | AGCTATGCCATGAGC | GTTATTAGTGGTCGTGGT GTTAACACATTCTACGCA GACTCCGTGAAGGGC | CGTATCGCCAGTGGCTGGCTC GGAGGCTTTGATATC |
| | | | SEQ ID NO:5027 | SEQ ID NO:13039 | SEQ ID NO:21051 |
| | | AA | SYAMS | VISGRGVNTFYADSVKG | RIAVAGSEAFDI |
| | | | SEQ ID NO:5028 | SEQ ID NO:13040 | SEQ ID NO:21052 |
| iPS:394089 | 21-225_12E6 | NA | GACTATGGCATGCAC | GTTATATGGTATGATGA AAGTAATAAATACTATG CAGACTCCGTGAAGGGC | GAGCTTGCTGGTACGAGGA CTAC |
| | | | SEQ ID NO:5029 | SEQ ID NO:13041 | SEQ ID NO:21053 |
| | | AA | DYGMH | VIWYDESNKYYADSVKG | ELAWYEDY |
| | | | SEQ ID NO:5030 | SEQ ID NO:13042 | SEQ ID NO:21054 |
| iPS:394091 | 21-225_13H3 | NA | AGCTATGGCATGCAC | GTTATTGGTATGAGGA AAGTAATAAATACTATG TAGACTCCGTGAGGGGC | GAACTAGGCTTCCAGTCTGA CTTC |
| | | | SEQ ID NO:5031 | SEQ ID NO:13043 | SEQ ID NO:21055 |
| | | AA | SYGMH | VIWYEESNKYYVDSVRG | ELGFQSDF |
| | | | SEQ ID NO:5032 | SEQ ID NO:13044 | SEQ ID NO:21056 |

FIGURE 49
(Continued)

| | | | | | |
|---|---|---|---|---|---|
| iPS:394093 | 21-225_9D12 | NA | GACTATGGCATGCAC | GTTATATGGTATGATGG AAATAATAATTACTATG CAGACTCCGTGAAGGGC | GAGCTTGCCTGGTACGAGGA CTTC |
| | | | SEQ ID NO:5033 | SEQ ID NO:13045 | SEQ ID NO:21057 |
| | | AA | DYGMH | VIWYDGNNYYADSVKG | ELAWYEDF |
| | | | SEQ ID NO:5034 | SEQ ID NO:13046 | SEQ ID NO:21058 |
| iPS:394095 | 21-225_16H4 | NA | AACTATGGCATGCAC | GTTATATGGTATGATGTA AGTAATAAATACTATGC AGACTCCGTGAAGGGC | GAAATGGGCTGGACCGATGA CTGC |
| | | | SEQ ID NO:5035 | SEQ ID NO:13047 | SEQ ID NO:21059 |
| | | AA | NYGMH | VIWYDVSNKYYADSVKG | EMGWTDDC |
| | | | SEQ ID NO:5036 | SEQ ID NO:13048 | SEQ ID NO:21060 |
| iPS:394097 | 21-225_16G7 | NA | GACTATGGCATGCAC | GTTATTGGTATGATGAA AATAATGAATACTATGC AGACTCCGTGAAGGGC | GAGCTTGCCTGGTACGAGGA CTAC |
| | | | SEQ ID NO:5037 | SEQ ID NO:13049 | SEQ ID NO:21061 |
| | | AA | DYGMH | VIWYDENNEYYADSVKG | ELAWYEDY |
| | | | SEQ ID NO:5038 | SEQ ID NO:13050 | SEQ ID NO:21062 |
| iPS:398470 | 21-225_14B7 | NA | GGCTACTATATGCAC | TGGATCAACCCTAACAG TGGTGGCACAAACTATG TACAGAAGTTTCAGGGC | TCGTTTTCTATGGTTCGGGG AGTTATTATAACGAATTTGA CTAC |
| | | | SEQ ID NO:5039 | SEQ ID NO:13051 | SEQ ID NO:21063 |
| | | AA | GYYMH | WINPNSGGTNYVQKFQG | SFFYGSGSYYNEFDY |
| | | | SEQ ID NO:5040 | SEQ ID NO:13052 | SEQ ID NO:21064 |

FIGURE 49
(Continued)

| | | | | |
|---|---|---|---|---|
| iPS:398472 | 21-225_16E4 | NA | AGCTATGTCATGAGC | ACTATTAGTAGTGGTGGT GGTACCACATACTACGC AGACTCCGTGAAGGGC | TGGGGACGTGGCAACAGCTA TGAGTACTACGGTATGG ACGTC |
| | | | SEQ ID NO:5041 | SEQ ID NO:13053 | SEQ ID NO:21065 |
| | | AA | SYVMS | TISVGGGTTYYADSVKG | WGRGNSYEYYYGMDV |
| | | | SEQ ID NO:5042 | SEQ ID NO:13054 | SEQ ID NO:21066 |
| iPS:398474 | 21-225_17B10 | NA | AGCTATGCCATGAGC | GTTATTAGTGGTAGTGGT GGTAACACATACTTCGC AGACTCCGTGAAGGGC | AGGGGTATACCAGAGAGGCTGA TGCTTTTGATATC |
| | | | SEQ ID NO:5043 | SEQ ID NO:13055 | SEQ ID NO:21067 |
| | | AA | SYAMS | VISGSGGNTYFADSVKG | RGIPEADAFDI |
| | | | SEQ ID NO:5044 | SEQ ID NO:13056 | SEQ ID NO:21068 |
| iPS:398476 | 21-225_17C1 | NA | AGCTATGCCATGAGC | GTTATTAGTGGTAGTGGT GGTACCACATTCTACGC AGACTCCGTGAAGGGC | TATTGTAGTAGTACCAGGTG TCCTTATGATGCCTTTGATAT C |
| | | | SEQ ID NO:5045 | SEQ ID NO:13057 | SEQ ID NO:21069 |
| | | AA | SYAMS | VISGSGGTTFYADSVKG | YCSSTRCPYDAFDI |
| | | | SEQ ID NO:5046 | SEQ ID NO:13058 | SEQ ID NO:21070 |
| iPS:398478 | 21-225_17C10 | NA | AGCTATAGCATGAAC | TCCATTAGTGGTAGTAGT AGTTACATGTACTACGC AGACTCAGTGAAGGGC | GATCGTGGGAGCTCC |
| | | | SEQ ID NO:5047 | SEQ ID NO:13059 | SEQ ID NO:21071 |
| | | AA | SISMN | SISGSSSYMYYADSVKG | DRGSS |
| | | | SEQ ID NO:5048 | SEQ ID NO:13060 | SEQ ID NO:21072 |
| iPS:398480 | 21-225_17G4 | NA | GACTATTATATGCAC | TGGATCAACCCTAACAG TGGTGGCACAAACTATG AACAGAAGTTTCAGGGC | GGATACAGCTATGGGTACAA CTGGTTCGACCCC |
| | | | SEQ ID NO:5049 | SEQ ID NO:13061 | SEQ ID NO:21073 |
| | | AA | DYYMH | WINPNSGGTNYEQKFQG | GYSYGYNWFDP |
| | | | SEQ ID NO:5050 | SEQ ID NO:13062 | SEQ ID NO:21074 |

FIGURE 49
(Continued)

| | | | AGCTATAGCATGAAC | TCCATTAGTAGTGGTAGTAGT AGTTACATATACTACGC AGACTCAGTGAAGGGC | GTGGGCTTCATTTGACTAC |
|---|---|---|---|---|---|
| iPS:398482 | 21-225_17H6 | NA | | | |
| | | AA | SEQ ID NO:5051 SYSMN | SEQ ID NO:13063 SISGSSSYIYYADSVKG | SEQ ID NO:21075 VASFDY |
| | | | SEQ ID NO:5052 | SEQ ID NO:13064 | SEQ ID NO:21076 |
| iPS:398484 | 21-225_18D4 | NA | GGCTACTATTGCAC | TGGATCAACCTAACAG TAATGGCACAATCTCTGC ACAGAAGTTTCAGGGC | GATGGTACCAGCTCGCTTGA CTAC |
| | | AA | SEQ ID NO:5053 GYYLH | SEQ ID NO:13065 WINPNSNGTISAQKFQG | SEQ ID NO:21077 DGTSSLDY |
| | | | SEQ ID NO:5054 | SEQ ID NO:13066 | SEQ ID NO:21078 |
| iPS:398486 | 21-225_19A1 | NA | GGCTACTATATGCAC | TGGATCAATCCTAACAG TGGTGGCACAAACTATG CACAGAAGTTTCAGGGC | GGATACAGCTATGGGTACAA CTGGTTCGACCCC |
| | | AA | SEQ ID NO:5055 GYYMH | SEQ ID NO:13067 WINPNSGGTNYAQKFQG | SEQ ID NO:21079 GYSYGYNWFDP |
| | | | SEQ ID NO:5056 | SEQ ID NO:13068 | SEQ ID NO:21080 |
| iPS:398488 | 21-225_19F6 | NA | AACGCCTGGATGAAC | CGTATTAAAAGCAAAAC TGATGGTGGGACAACAG ACTACGCTGCACCCGTG AAAGGC | GATACGGGTCCTATAGCAGC TCGTCTCGCTTACTACTACTA TTACGCTATGGACGTC |
| | | AA | SEQ ID NO:5057 NAWMN | SEQ ID NO:13069 RIKSKTDGGTTDYAAPVK G | SEQ ID NO:21081 DTGPIAARLAYYYYAMDV |
| | | | SEQ ID NO:5058 | SEQ ID NO:13070 | SEQ ID NO:21082 |
| iPS:398490 | 21-225_21D12 | NA | GACTACTATATTCAC | TGGATCAACCTAACAG TGGTGGGACAAACAATG CACAGAAGTTTCAGGGC | TCGTATTACTATGGTTCGGG GACTTATTATAACGAATTTG ACTAC |
| | | | SEQ ID NO:5059 | SEQ ID NO:13071 | SEQ ID NO:21083 |

FIGURE 49
(Continued)

| | | | | | WINPNSGGTNNAQKFQG | SYYYGSGTYYNEFDY |
|---|---|---|---|---|---|---|
| | | | DYYIH | | SEQ ID NO:13072 | SEQ ID NO:21084 |
| iPS:398494 | | AA | SEQ ID NO:5060 | | | |
| | 21-225_21H4 | NA | AGCTATGCCATGAGC | GCTCTTAGTGGTGGTCGTGGT GGTAGCACATACTACGC AGACTCCGTGAAGGGC | TGGGGACGTGGATACAGCTA TGAGTACTACTACGGTATGG ACGTC | |
| | | | SEQ ID NO:5061 | SEQ ID NO:13073 | SEQ ID NO:21085 | |
| | | AA | SYAMS | ALSGRGGSTYYADSVKG | WGRGYSYEYYYGMDV | |
| | | | SEQ ID NO:5062 | SEQ ID NO:13074 | SEQ ID NO:21086 | |
| iPS:398496 | | NA | AATTATGATATCAAC | TGGATGCACCCTGACAG TGGTAACACAGGCTATG CACAGAAGTTCCAGGGC | AGTAGTGGCTGGTACTACTT TGACTAC | |
| | 21-225_22D2 | | SEQ ID NO:5063 | SEQ ID NO:13075 | SEQ ID NO:21087 | |
| | | AA | NYDIN | WMHPDSGNIGYAQKFQG | SSGWYYFDY | |
| | | | SEQ ID NO:5064 | SEQ ID NO:13076 | SEQ ID NO:21088 | |
| iPS:398498 | | NA | ACTGGTGGTGGAGTGGGTGTGGG C | CTCATTTATTGGAATGAT GATAAGCGCTACAGCCC ATCTCTGAAGAGC | ACTATAGCAGTTCGTGGCTT TGACTAC | |
| | 21-225_22E6 | | SEQ ID NO:5065 | SEQ ID NO:13077 | SEQ ID NO:21089 | |
| | | AA | TGGVGVG | LIYWNDDKRYSPSLKS | TIAVRGFDY | |
| | | | SEQ ID NO:5066 | SEQ ID NO:13078 | SEQ ID NO:21090 | |
| iPS:398500 | | NA | AGTTATAGCATGAAC | TCCATTAGTGGTAGTAGT ACTTACATATACTACGCA GACTCAGTGAAGGGC | GTGGCTTCATTTGACTAC | |
| | 21-225_23A11 | | SEQ ID NO:5067 | SEQ ID NO:13079 | SEQ ID NO:21091 | |
| | | AA | SYSMN | SISGSSTYIYYADSVKG | VASFDY | |
| | | | SEQ ID NO:5068 | SEQ ID NO:13080 | SEQ ID NO:21092 | |

FIGURE 49
(Continued)

| | | | | | |
|---|---|---|---|---|---|
| iPS:398502 | 21-225_23B11 | NA | GGCTACTATCTGCAC | TGGATCAACCCTAACAATAATGGCACAAACTATGCACAGAAGTTTCAGGGC | GATGGTACCAGCTCGTTTGACTAC |
| | | | SEQ ID NO:5069 | SEQ ID NO:13081 | SEQ ID NO:21093 |
| | | AA | GYYLH | WINPNNNGTNYAQKFQG | DGTSSFDY |
| | | | SEQ ID NO:5070 | SEQ ID NO:13082 | SEQ ID NO:21094 |
| iPS:398504 | 21-225_23D7 | NA | ACTAGTGGAGTGGGTGTGGGC | CTCATTTATTGGAATAATGATAAGGTCTACAGCCCATCTCTGAAGAGC | AGGGGACAGCAGCTGGCCCTCGACTAC |
| | | | SEQ ID NO:5071 | SEQ ID NO:13083 | SEQ ID NO:21095 |
| | | AA | TSGVGVG | LIYWNNDKVYSPSLKS | RGQQLALDY |
| | | | SEQ ID NO:5072 | SEQ ID NO:13084 | SEQ ID NO:21096 |
| iPS:398506 | 21-225_23G12 | NA | AATTATGATATCAAC | TGGATGTACCCTAACAGTGGTAACACGGGCTATGCACAGAAGTTCCAGGGC | AGCGGTGGCTGGTACTACTTTGACTAC |
| | | | SEQ ID NO:5073 | SEQ ID NO:13085 | SEQ ID NO:21097 |
| | | AA | NYDIN | WMYPNSGNTGYAQKFQG | SGGWYYFDY |
| | | | SEQ ID NO:5074 | SEQ ID NO:13086 | SEQ ID NO:21098 |
| iPS:398508 | 21-225_24B1 | NA | AGCTATGCCATGAGC | GCTATTAGTGGTCGTGGTGGTAGCACATACTACGCAGACTCCGTGAAGGGC | TGGGGACGTGGATACAGCTATGAGTACTACTACGGTATGGACGTC |
| | | | SEQ ID NO:5075 | SEQ ID NO:13087 | SEQ ID NO:21099 |
| | | AA | SYAMS | AISGRGGSTYYADSVKG | WGRGYSYEYYYGMDV |
| | | | SEQ ID NO:5076 | SEQ ID NO:13088 | SEQ ID NO:21100 |
| iPS:398510 | | NA | AATTATGATATCAAC | TGGATGCACCCTAACAGTGGTAACACAGGCTATGCACAGAAGTTCCAGGGC | AGCAGTGGCTGGTATTGGTTCGACCCC |

FIGURE 49
(Continued)

| | | | | | | |
|---|---|---|---|---|---|---|
| iPS:398512 | 21-225_25A3 | | AA | SEQ ID NO:5077 NYDIN | SEQ ID NO:13089 WMHPNSGNTGYAQKFQG | SEQ ID NO:21101 SSGWYWFDP |
| | | | NA | SEQ ID NO:5078 AATTATGATATCAAC | SEQ ID NO:13090 TGGATGAACCCTAACAG TGGTAACACAGGCTATG CACAGAAGTTCCAGGGC | SEQ ID NO:21102 AGCAATGGCTGGTACTACTT TGACTAC |
| iPS:398516 | 21-225_25E12 | | AA | SEQ ID NO:5079 NYDIN | SEQ ID NO:13091 WMNPNSGNTGYAQKFQG | SEQ ID NO:21103 SNGWYYFDY |
| | | | NA | SEQ ID NO:5080 AATTATGATATCAAC | SEQ ID NO:13092 TGGATGCACCTAACAG TGGTAACACAGGCTGTG CACAGAAGTTCCAGGGC | SEQ ID NO:21104 AGCAGTGGCTGGTACTGGTT CGACCCC |
| iPS:398520 | 21-225_26A9 | | AA | SEQ ID NO:5081 NYDIN | SEQ ID NO:13093 WMHPNSGNTGCAQKFQG | SEQ ID NO:21105 SSGWYWFDP |
| | 21-225_31C4 | | NA | SEQ ID NO:5082 GGCGATTATATGCAC | SEQ ID NO:13094 TGGATCAGCCCTAAAAA TGGTGGCACAAACTATG CACAGAAGTTTCAGGGC | SEQ ID NO:21106 GATGGAACTGGGTCCTTTGA CTAC |
| | | | AA | SEQ ID NO:5083 GDYMH | SEQ ID NO:13095 WISPKNGGTNYAQKFQG | SEQ ID NO:21107 DGTGSFDY |
| iPS:398522 | 21-225_32A1 | | NA | SEQ ID NO:5084 AACTATGATATTAAC | SEQ ID NO:13096 TGGATGAACCCTAACAG TGGTAACACAGGCTATG CACAGAAGTTCCAGGGC | SEQ ID NO:21108 AGCAGTGGCTGGTACTTTT TGACTAC |
| | | | | SEQ ID NO:5085 | SEQ ID NO:13097 | SEQ ID NO:21109 |

FIGURE 49
(Continued)

| | | | | | |
|---|---|---|---|---|---|
| iPS:398524 | | AA | NYDIN | WMNPNSGNTGYAQKFQG | SSGWYFFDY |
| | | | SEQ ID NO:5086 | SEQ ID NO:13098 | SEQ ID NO:21110 |
| | 21-225_32A5 | NA | AATTATGACATCAAC | TGGATGAACCCTAACAGTGGTAACACAGGCTTTGCACAGAAGTTCCGGGGC | AGCAGTGGCTGGTACTTTTTTGACTAC |
| | | | SEQ ID NO:5087 | SEQ ID NO:13099 | SEQ ID NO:21111 |
| iPS:398526 | | AA | NYDIN | WMHPNSGNTGFAQKFRG | SSGWYFFDY |
| | | | SEQ ID NO:5088 | SEQ ID NO:13100 | SEQ ID NO:21112 |
| | 21-225_32B3 | NA | AGCTATAGCATGAAC | TCCATTAGTGGTAGTAGTACTTACATATACGCAGACTCCGTGAAGGGC | GTGGCTGGCTTTGACTAC |
| | | | SEQ ID NO:5089 | SEQ ID NO:13101 | SEQ ID NO:21113 |
| | | AA | SYSMN | SISGSSTYIYYADSVKG | VAGFDY |
| | | | SEQ ID NO:5090 | SEQ ID NO:13102 | SEQ ID NO:21114 |
| iPS:398528 | 21-225_32G1 | NA | AGCTATGCCATGAGC | GCTATTAGTGGTCGTGGTGGTAGCACATTCCACGCAGACTCCGTGAAGGGC | GGGGAGCTACTAGAGGACTACTACTTCTACGGTATGGACGTC |
| | | | SEQ ID NO:5091 | SEQ ID NO:13103 | SEQ ID NO:21115 |
| | | AA | SYAMS | AISGRGGSTFHADSVKG | GELLEDYYFYGMDV |
| | | | SEQ ID NO:5092 | SEQ ID NO:13104 | SEQ ID NO:21116 |
| iPS:398530 | 21-225_32G4 | NA | AGTTATGATATCAAC | TGGATGAACCCTAACAGTGGTAACACAGGCTATGCACAGAAGTTCCAGGGC | AAGAAGGCTAACGACTAC |
| | | | SEQ ID NO:5093 | SEQ ID NO:13105 | SEQ ID NO:21117 |
| | | AA | SYDIN | WMNPNSGNTGYAQKFQG | KKANDY |
| | | | SEQ ID NO:5094 | SEQ ID NO:13106 | SEQ ID NO:21118 |

FIGURE 49
(Continued)

| | | NA | AGCTATAACATGAAC | | TCCATTAGTAGTGGTAGTAGT AGTTACATATACGC AGACTCAGTGAAGGGC | TTAAATGGTTTTGACTAC |
|---|---|---|---|---|---|---|
| iPS:398532 | 21-225_33B7 | | SEQ ID NO:5095 | | SEQ ID NO:13107 | SEQ ID NO:21119 |
| | | AA | SYNMN | | SISGSSSYIYYADSVKG | LNGFDY |
| | | | SEQ ID NO:5096 | | SEQ ID NO:13108 | SEQ ID NO:21120 |
| iPS:398534 | 21-225_33B8 | NA | AGCTATGCCATGAGC | | GCTATTAGTGGTCGTGGT GGTAGCACATTCCACGC AGACTCCGTGAAGGGC | GGGGAGCTACTAGAGGACTA CTACTTCTACGGTATGGACG TC |
| | | | SEQ ID NO:5097 | | SEQ ID NO:13109 | SEQ ID NO:21121 |
| | | AA | SYAMS | | AISGRGGSTFHADSVKG | GELLEDYYFYGMDV |
| | | | SEQ ID NO:5098 | | SEQ ID NO:13110 | SEQ ID NO:21122 |
| iPS:398536 | 21-225_33D12 | NA | AGTTATGATATCAGC | | TGGATGAACCCTAACAG TGGTAACACAGGCTATG CACAGAAGTTCCAGGGC | AAGAGGGCTAACGACTAC |
| | | | SEQ ID NO:5099 | | SEQ ID NO:13111 | SEQ ID NO:21123 |
| | | AA | SYDIS | | WMNPNSGNTGYAQKFQG | KRANDY |
| | | | SEQ ID NO:5100 | | SEQ ID NO:13112 | SEQ ID NO:21124 |
| iPS:398538 | 21-225_34H7 | NA | AACTATGATATTAAC | | TGGATGAACCCTAACAG TGGTAACACAGGCTATG CACAGAAGTTCCAGGGC | AGCAGTGGCTGGTACTTTTT TGACTAC |
| | | | SEQ ID NO:5101 | | SEQ ID NO:13113 | SEQ ID NO:21125 |
| | | AA | NYDIN | | WMNPNSGNTGYAQKFQG | SSGWYFFDY |
| | | | SEQ ID NO:5102 | | SEQ ID NO:13114 | SEQ ID NO:21126 |
| iPS:398540 | 21-225_35A6 | NA | AGCTATGCCATGAGC | | ACTATTAGTGGTCGTGGT GGTAGCACATTCCACGC AGACTCCGTGAAGGGC | GGGGAGCTACTAGAGGACTA CTACTTCTACGGTATGGACG TC |
| | | | SEQ ID NO:5103 | | SEQ ID NO:13115 | SEQ ID NO:21127 |

FIGURE 49
(Continued)

| | | AA/NA | | | | | |
|---|---|---|---|---|---|---|---|
| iPS:398544 | 21-225_7C8 | AA | SYAMS | | TISGRGGSTFHADSVKG | | GELLEDYYFYGMDV |
| | | | SEQ ID NO:5104 | | SEQ ID NO:13116 | | SEQ ID NO:21128 |
| | | NA | AACGCCCGGATGAAC | | CGTATTAAAAGCAAAAC TGATGGTGGGACAACAG ACTACGCTGCACCCGTG AAAGGC | | GATACGGGTCCTATAGCAGC TCGTCTCGCTTACTACTACTA CTACGCTATGGACGTC |
| | | | SEQ ID NO:5105 | | SEQ ID NO:13117 | | SEQ ID NO:21129 |
| iPS:398546 | 21-225_9H10 | AA | NARMN | | RIKSKTDGGTTDYAAPVK G | | DTGPIAARLAYYYYYAMDV |
| | | | SEQ ID NO:5106 | | SEQ ID NO:13118 | | SEQ ID NO:21130 |
| | | NA | ACTAGTGGAGTGGGTGTGG C | | CTCATTATTGGAGTGAT GATAAGCGCTACAGCCC ATCTCTGAAGAGC | | ACCGGTCTAGCTGCTGCTA TTTTGACTAC |
| | | | SEQ ID NO:5107 | | SEQ ID NO:13119 | | SEQ ID NO:21131 |
| | | AA | TSGVGVG | | LIYWSDDKRYSPSLKS | | TGSSCCYFDY |
| | | | SEQ ID NO:5108 | | SEQ ID NO:13120 | | SEQ ID NO:21132 |
| iPS:402219 | 21-225_1C12 | NA | AACTATGGCATGCAC | | GTTATATGGTATGATGA AAATAATAATACTATG TAGACTCCGTGAAGGGC | | GAATTGGGGTTCCGGTCTGA CTAC |
| | | | SEQ ID NO:5109 | | SEQ ID NO:13121 | | SEQ ID NO:21133 |
| | | AA | NYGMH | | VIWYDENNKYYVDSVKG | | ELGFRSDY |
| | | | SEQ ID NO:5110 | | SEQ ID NO:13122 | | SEQ ID NO:21134 |
| iPS:402221 | 21-225_2C12 | NA | AGCTATAGCATGAAC | | TCCATTAGTGGTAGTAGT AGTTACATGTACTACGC AGACTCAGTGAAGGGC | | GTGAATCTCTTTGACTAC |
| | | | SEQ ID NO:5111 | | SEQ ID NO:13123 | | SEQ ID NO:21135 |
| | | AA | SYSMN | | SISGSSSYMYYADSVKG | | VNLFDY |
| | | | SEQ ID NO:5112 | | SEQ ID NO:13124 | | SEQ ID NO:21136 |

FIGURE 49
(Continued)

| iPS:402223 | 21-225_30A11 | NA | GACTATCATATGCAC SEQ ID NO:5113 | TGGATCAACCCTAATAG GGGTGGCACAAACTATG CACAGAAGTTTCAGGAC SEQ ID NO:13125 | GATGGAACTGGGTCCTTTGA CTAC SEQ ID NO:21137 |
|---|---|---|---|---|---|
| | | AA | DYHMH SEQ ID NO:5114 | WINPNRGGTNYAQKFQD SEQ ID NO:13126 | DGTGSFDY SEQ ID NO:21138 |
| iPS:402225 | 21-225_2B1 | NA | AGCTATAGCATGAAC SEQ ID NO:5115 | TCCATTAGTAGTAGTAGT AGTTACATATACTACGC AGACTCAGTGAAGGGC SEQ ID NO:13127 | CTGGGGAACTAC SEQ ID NO:21139 |
| | | AA | SYSMN SEQ ID NO:5116 | SISSSSSYIYYADSVKG SEQ ID NO:13128 | LGNY SEQ ID NO:21140 |
| iPS:402229 | 21-225_16H9 | NA | AGCTATAGCATGAAC SEQ ID NO:5117 | TCCATTAGTGGTAGTAGT AGTTACATATACTACGC AGACTCAGTGAAGGGC SEQ ID NO:13129 | GTCAACGTGTATGGACGTC SEQ ID NO:21141 |
| | | AA | SYSMN SEQ ID NO:5118 | SISGSSSYIYYADSVKG SEQ ID NO:13130 | VNGMDV SEQ ID NO:21142 |
| iPS:402231 | 21-225_6D9 | NA | AACGCCTGGATGAAC SEQ ID NO:5119 | CGTATTAAAAGCAAAAC TGATGGTGGGACAACAG ACTACGCTGCACCCGTG AAAGGC SEQ ID NO:13131 | GATACGGGTCCTATAGCAGC TCGTCTCGCTTACTACTACTA CTACGCTATGGACGTC SEQ ID NO:21143 |
| | | AA | NAWMN SEQ ID NO:5120 | RIKSKTDGGTTDYAAPVK G SEQ ID NO:13132 | DTGPIAARLAYYYYAMDV SEQ ID NO:21144 |
| iPS:402233 | 21-225_16D10 | NA | ACCTATAACTTGAAC | TCCATTAGTGGTGGTGCC GGTCACATATATTACTCA GACTCAGTGAAGGGC | ACTAATGGGTTTGACTTC |

FIGURE 49
(Continued)

| iPS | Clone | Type | CDR1 / SEQ ID | CDR2 / SEQ ID | CDR3 / SEQ ID |
|---|---|---|---|---|---|
| iPS:402235 | 21-225_16D10 | AA | SEQ ID NO:5121<br>TYNLN | SEQ ID NO:13133<br>SISGGAGHIYYSDSVKG | SEQ ID NO:21145<br>TNGFDF |
| | | NA | SEQ ID NO:5122<br>AGCTATAGCCATGAAC | SEQ ID NO:13134<br>TCCATTAGTACTAGTACTTTCATATATACGCAGATTCAGTGAAGGGC | SEQ ID NO:21146<br>AAGGCTGGGCTTGATATC |
| iPS:402237 | 21-225_20F10 | AA | SEQ ID NO:5123<br>SYSMN | SEQ ID NO:13135<br>SISTSTFIYYADSVKG | SEQ ID NO:21147<br>KAGLDI |
| | | NA | SEQ ID NO:5124<br>AGCTATAAACATAAAC | SEQ ID NO:13136<br>TCCATTAGTGGTAATAGTGGTTACATATACTACGCAGACTCAGTGAAGGGC | SEQ ID NO:21148<br>ACTAACCTCTTTGACTAC |
| iPS:402237 | 21-225_23D11 | AA | SEQ ID NO:5125<br>SYNIN | SEQ ID NO:13137<br>SISGNSGYIYYADSVKG | SEQ ID NO:21149<br>TNLFDY |
| | | NA | SEQ ID NO:5126<br>AGAAGTAGTTATTACTGGGC | SEQ ID NO:13138<br>AGTATCTATTATAGTGGGAGCGCCAACTACTACACCCGTCCCTCAAGAGT | SEQ ID NO:21150<br>CTGGACAGGGGCTGGTCCTTTGACTAC |
| iPS:403868 | 21-225_19D11 | AA | SEQ ID NO:5127<br>RSSYYWG | SEQ ID NO:13139<br>SIYYSGSANYNPSLKS | SEQ ID NO:21151<br>LDRGWSFDY |
| | | NA | SEQ ID NO:5128<br>AGCTATGCCATGAGC | SEQ ID NO:13140<br>GGTAGCACATACTACGCAGACTCCGTGAAGGGC | SEQ ID NO:21152<br>AGGGGGATAGTGGGAGCTACTGAGGCTTTTGATATC |
| iPS:403870 | 21-225_23G4 | AA | SEQ ID NO:5129<br>SYAMS | SEQ ID NO:13141<br>VISGRGGSTYYADSVKG | SEQ ID NO:21153<br>RGIVGATEAFDI |
| | | NA | SEQ ID NO:5130<br>AGGACTAGTTACTACTGGGGC | SEQ ID NO:13142<br>AATATTTATTATAGTGGGAGCGCCTACACAACCCGTCCCTCAAGAGT | SEQ ID NO:21154<br>CATGGACAAGACTGGGCCTTGACTAC |
| iPS:403872 | 21-225_8F11 | NA | | | |

FIGURE 49
(Continued)

| ID | Name | AA/NA | CDR1 | CDR2 | CDR3 |
|---|---|---|---|---|---|
| iPS:404090 | 21-225_8F11 | AA | SEQ ID NO:5131 RTSYYWG | SEQ ID NO:13143 NIYYSGSAYNNPSLKS | SEQ ID NO:21155 HGQDWGLDY |
|  |  | NA | SEQ ID NO:5132 AGCTATAGCATGAAC | SEQ ID NO:13144 TCCATTAGTAGTAGTAGT AGTACATATACGC AGACTCAGTGAAGGGC | SEQ ID NO:21156 CTGGGTAACTAC |
| iPS:412232 | 21-225_8D8 | AA | SEQ ID NO:5133 SYSMN | SEQ ID NO:13145 SISSSSSYIYYADSVKG | SEQ ID NO:21157 LGNY |
|  |  | NA | SEQ ID NO:5134 | SEQ ID NO:13146 TGGATGCACCCTAACAG TGGTAACACAGGCTATG CACAGAAGTTCCAGGGC | SEQ ID NO:21158 AGCAGTGGCTGGTACTACTT TGACTAC |
| iPS:422894 | 21-225_4A2 | AA | SEQ ID NO:5135 NYDIN | SEQ ID NO:13147 WMHPNSGNTGYAQKFQG | SEQ ID NO:21159 SSGWYYFDY |
|  |  | NA | SEQ ID NO:5136 AATTATGATATCAAC | SEQ ID NO:13148 TGGATGCACCCTAACAG TGGTAACACAGGCTATG CACAGAAGTTCCAGGGC | SEQ ID NO:21160 AGCAGTGGCTGGTACTACTT TGACTAC |
|  | 21-225_4A2.001 | AA | SEQ ID NO:5137 NYDIN | SEQ ID NO:13149 WMHPNSGNTGYAQKFQG | SEQ ID NO:21161 SSGWYYFDY |
|  |  | NA | SEQ ID NO:5138 AATTATGATATCAAC | SEQ ID NO:13150 TGGATCAACCCTAACAG TGGTGGCACAAACTATG TACAGAAGTTTCAGGGC | SEQ ID NO:21162 GTGTATTACTATGGTTCGGG GAGTTATTATAACGAGTTTG ACTAC |
| iPS:423018 | 21-225_31D12_LC2 | AA | SEQ ID NO:5139 GYYMH | SEQ ID NO:13151 WINPNSGGTNYVQKFQG | SEQ ID NO:21163 VYYYGSGSYYNEFDY |
|  |  | NA | SEQ ID NO:5140 GGCTACTATATGCAC | SEQ ID NO:13152 | SEQ ID NO:21164 |

FIGURE 49
(Continued)

| | | | | |
|---|---|---|---|---|
| iPS:423019 | 21-225_31D12_LC1 | NA | GGCTACTACTATATGCAC | TGGATCAACCCTAACAG TGGTGGCACAAACTATG TACAGAAGTTCAGGGC | GTGTATTACTATGGTTCGGG GAGTTATTATAACGAGTTTG ACTAC |
| | | | SEQ ID NO:5141 | SEQ ID NO:13153 | SEQ ID NO:21165 |
| | | AA | GYYMH | WINPNSGGTNYVQKFQG | VYYYGSGSYYNEFDY |
| | | | SEQ ID NO:5142 | SEQ ID NO:13154 | SEQ ID NO:21166 |
| iPS:423314 | 21-225_12F11 | NA | AATTATGATATATCAAC | TGGATGCACCCTAACAG TGGTAACACAGGCTATG CAAAGAAGTTCCAGGGC | AGCAGTGGCTGGTACTACTT TGACTAC |
| | | | SEQ ID NO:5143 | SEQ ID NO:13155 | SEQ ID NO:21167 |
| | | AA | NYDIN | WMHPNSGNTGYAKKFQG | SSGWYYFDY |
| | | | SEQ ID NO:5144 | SEQ ID NO:13156 | SEQ ID NO:21168 |
| iPS:424419 | 21-225_25A4.001 | NA | AATTATGATATATTAAT | TGGATGTACCCTAACAG TGGTAACACAGGCTATG CACAGAAATTCCAGGGC | AGCAGTGGCTGGTACTACTT TGACTAC |
| | | | SEQ ID NO:5145 | SEQ ID NO:13157 | SEQ ID NO:21169 |
| | | AA | NYDIN | WMYPNSGNTGYAQKFQG | SSGWYYFDY |
| | | | SEQ ID NO:5146 | SEQ ID NO:13158 | SEQ ID NO:21170 |
| iPS:424460 | 21-225_7E11.001 | NA | AGCTTTGGCATGCAC | ATTATCTGGCATGATGG AAGTAATAAATACTATG CAGACTCCGTGAAGGGC | GATCTGAGTATGGGCGGTAT GGACGTC |
| | | | SEQ ID NO:5147 | SEQ ID NO:13159 | SEQ ID NO:21171 |
| | | AA | SFGMH | IIWHDGSNKYYADSVKG | DLSMGGMDV |
| | | | SEQ ID NO:5148 | SEQ ID NO:13160 | SEQ ID NO:21172 |

FIGURE 49
(Continued)

| | | | | GCCTACCATATGCAC | TGGATCAACCCTAACAA<br>TAATGGCACAAACTATG<br>CACAGAAGTTTCAGGGC | GATGTTACCAGCTCGTTTGA<br>CTAT |
|---|---|---|---|---|---|---|
| iPS:426108 | 21-225_10G6 | | NA | SEQ ID NO:5149 | SEQ ID NO:13161 | SEQ ID NO:21173 |
| | | | AA | AYHMH | WINPNNGTNYAQKFQG | DVTSSFDY |
| | | | NA | SEQ ID NO:5150<br>GACTACTATTTGCAC | SEQ ID NO:13162<br>TGGGTCCACCTAACAG<br>TGGTGGCACAAACTTTG<br>CACAGAAGTTTCAGGAC | SEQ ID NO:21174<br>GATGGTACCAGCTCGTTTGA<br>CTAC |
| iPS:426110 | 21-225_12E9 | | AA | SEQ ID NO:5151<br>DYYLH | SEQ ID NO:13163<br>WVHPNSGGTNFAQKFQD | SEQ ID NO:21175<br>DGTSSFDY |
| | | | NA | SEQ ID NO:5152<br>AATTATGATATCAAC | SEQ ID NO:13164<br>TGGATGTACCCTAACAG<br>TGGTAACACGGGCTATG<br>CACAGAAGTTCCAGGGC | SEQ ID NO:21176<br>AGCAGTGGCTGGTACTACTT<br>TGACTTC |
| iPS:426112 | 21-225_12F12 | | AA | SEQ ID NO:5153<br>NYDIN | SEQ ID NO:13165<br>WMYPNSGNTGYAQKFQG | SEQ ID NO:21177<br>SSGWYYFDF |
| | | | NA | SEQ ID NO:5154<br>AACTATGTCATGCAC | SEQ ID NO:13166<br>GTTATATGGTATGATGG<br>AAGTAATAAGTACTATG<br>CAGACTCCGTGAAGGGC | SEQ ID NO:21178<br>GAGGAGTATAGCAGTGGCTG<br>GTACGACTACGGTATGGACG<br>TC |
| iPS:426114 | 21-225_28H2 | | AA | SEQ ID NO:5155<br>NYVMH | SEQ ID NO:13167<br>VIWYDGSNKYADSVKG | SEQ ID NO:21179<br>EEYSSGWYDYGMDV |
| | | | | SEQ ID NO:5156 | SEQ ID NO:13168 | SEQ ID NO:21180 |

FIGURE 49
(Continued)

| | | | | | | |
|---|---|---|---|---|---|---|
| iPS:426116 | 21-225_29E2 | NA | AACTGTGTCATGCAC | | GTTATATGGTATGATGG AAGTAATAAATACTATG CAGACTCCGTGAAGGGC | | GAGGAGTATAGCAGTGGCTG GTACGACTACGGTATGGACG TC |
| | | | SEQ ID NO:5157 | | SEQ ID NO:13169 | | SEQ ID NO:21181 |
| | | AA | NCVMH | | VIWYDGSNKYYADSVKG | | EEYSSGWYDYGMDV |
| | | | SEQ ID NO:5158 | | SEQ ID NO:13170 | | SEQ ID NO:21182 |
| iPS:426118 | 21-225_7A10 | NA | AGCTATGGCATGCAC | | GTTATATGGTATGATGG AAGTAATAAATACTATG CAGACTCCGTGAAGGGC | | GATGAGAGGCTGGGGATTTT TGACTAC |
| | | | SEQ ID NO:5159 | | SEQ ID NO:13171 | | SEQ ID NO:21183 |
| | | AA | SYGMH | | VIWYDGSNKYYADSVKG | | DERLGIFDY |
| | | | SEQ ID NO:5160 | | SEQ ID NO:13172 | | SEQ ID NO:21184 |
| iPS:426124 | 21-225_32D6 | NA | AGCTATGGCATGCAC | | GTTATATGGCATGATGG AAGTAATGCATACTATG CAGACTCCGTGAAGGGC | | GAAAATAGCAGCTCGTACTA CTTTGACTAC |
| | | | SEQ ID NO:5161 | | SEQ ID NO:13173 | | SEQ ID NO:21185 |
| | | AA | SYGMH | | VIWHDGSNAYYADSVKG | | ENSSSYYFDY |
| | | | SEQ ID NO:5162 | | SEQ ID NO:13174 | | SEQ ID NO:21186 |
| iPS:426126 | 21-225_6G6 | NA | AATTATGATATCAAC | | TGGATGCACCCTAACAG TGGTAACACAGGCTATG CAAAGAAGTTCCAGGGC | | AGCAGTGGCTGGTACTACTT TGACTAC |
| | | | SEQ ID NO:5163 | | SEQ ID NO:13175 | | SEQ ID NO:21187 |
| | | AA | NYDIN | | WMHPNSGNTGYAKKFQG | | SSGWYYFDY |

FIGURE 49
(Continued)

| | | | | | |
|---|---|---|---|---|---|
| iPS:433895 | 21-225_43E1 | NA | SEQ ID NO:5164<br>AGCTATAGCATGAAC | SEQ ID NO:13176<br>GCCATTAGTGGTAATAG<br>TACTTACATATACTACGC<br>AGACTCGTTGAAGGGC | SEQ ID NO:21188<br>GATCGGGGCAGTGAA |
| | | AA | SEQ ID NO:5165<br>SYSMN | SEQ ID NO:13177<br>AISGNSTYIYYADSLKG | SEQ ID NO:21189<br>DRGSE |
| iPS:433897 | 21-225_43C2 | NA | SEQ ID NO:5166<br>AGCTATGCCATGAGC | SEQ ID NO:13178<br>GCTATTAGTGGTCGTGGT<br>GTTAACACATTCGACGC<br>AGACTCCGTGAAGGGC | SEQ ID NO:21190<br>GAAAGGAGTGGGAGCTATTT<br>TGACTAC |
| | | AA | SEQ ID NO:5167<br>SYAMS | SEQ ID NO:13179<br>AISGRGVNTFDADSVKG | SEQ ID NO:21191<br>ERSGSYFDY |
| iPS:433899 | 21-225_43C3 | NA | SEQ ID NO:5168<br>AGCTATGGCATACAC | SEQ ID NO:13180<br>GTTATATGGTATGATGA<br>AAATAATAAATACTATG<br>CAGACTCCGTGAAGGGC | SEQ ID NO:21192<br>GAGCTAGGATTTTCCAATGA<br>CTAC |
| | | AA | SEQ ID NO:5169<br>SYGIH | SEQ ID NO:13181<br>VIWYDENNKYYADSVKG | SEQ ID NO:21193<br>ELGFSNDY |
| iPS:433901 | 21-225_43A4 | NA | SEQ ID NO:5170<br>AGCTATACCATGAAC | SEQ ID NO:13182<br>TCCATTAGTGGAAGTAG<br>TACTTACATATACTACGC<br>AGACTCAGTGAAGGGC | SEQ ID NO:21194<br>GTGACCTCTTTTGACTAC |
| | | AA | SEQ ID NO:5171<br>SYTMN | SEQ ID NO:13183<br>SISGSSTYIYYADSVKG | SEQ ID NO:21195<br>VTSFDY |
| iPS:433903 | 21_225_43H4 | NA | SEQ ID NO:5172<br>AGCTATGCCATGAGC | SEQ ID NO:13184<br>GCTATTAGTGGTCGTGGT<br>ATTAACACATTCGACGC<br>AGACTCCGTGAAGGGC | SEQ ID NO:21196<br>GAAAGGAGTGGGAGCTATTT<br>TGACTAC |

FIGURE 49
(Continued)

| | | | | | |
|---|---|---|---|---|---|
| iPS:433905 | 21-225_43H4 | AA | SEQ ID NO:5173<br>SYAMS | SEQ ID NO:13185<br>AISGRGINTFDADSVKG | SEQ ID NO:21197<br>ERSGSYFDY |
| | | NA | SEQ ID NO:5174<br>GACTACACATGAGC | SEQ ID NO:13186<br>TACATTAGTAGTAGTGGT<br>ATTACCAAATACTACGC<br>AGACTCTATGAAGGGC | SEQ ID NO:21198<br>GATACAATCTAC |
| iPS:433909 | 21-225_43E5 | AA | SEQ ID NO:5175<br>DYYMI | SEQ ID NO:13187<br>YISSSGITKYYADSMKG | SEQ ID NO:21199<br>DTIY |
| | | NA | SEQ ID NO:5176<br>AATTATGATATCAAC | SEQ ID NO:13188<br>TGGATGCACCTAACAG<br>TGGTAACACAGGCTATG<br>CACAGAAGTTCCAGGGC | SEQ ID NO:21200<br>AGCAGTGGCTGGACCCTCTT<br>TGACTAC |
| iPS:433911 | 21-225_43D8 | AA | SEQ ID NO:5177<br>NYDIN | SEQ ID NO:13189<br>WMHPNSGNTGYAQKFQG | SEQ ID NO:21201<br>SSGWTLFDY |
| | | NA | SEQ ID NO:5178<br>AGCTATGCCATGAGC | SEQ ID NO:13190<br>GCTATTAGTGGTCGTGGT<br>ATTAACACATTCGACGC<br>AGACTCCGTGAAGGGC | SEQ ID NO:21202<br>GAAAGGAGTGGGAGCTATTT<br>TGACTAC |
| iPS:433911 | 21-225_43E8 | AA | SEQ ID NO:5179<br>SYAMS | SEQ ID NO:13191<br>AISGRGINTFDADSVKG | SEQ ID NO:21203<br>ERSGSYFDY |
| | | NA | SEQ ID NO:5180<br>GACTACACATGAAC | SEQ ID NO:13192<br>TACATTAGTAGTAGTGGT<br>AGAACCATATTCTACGC<br>AGACTCTTTGAAGGGC | SEQ ID NO:21204<br>GATACAATCTAC |
| iPS:433913 | 21-225_43H8 | AA | SEQ ID NO:5181<br>DYYMN | SEQ ID NO:13193<br>YISSSGRTHFYADSLKG | SEQ ID NO:21205<br>DTIY |
| | | | SEQ ID NO:5182 | SEQ ID NO:13194 | SEQ ID NO:21206 |

FIGURE 49
(Continued)

| | | | | |
|---|---|---|---|---|
| iPS:433915 | 21-225_43H9 | NA | AGCTATGCCATGAGT<br>SEQ ID NO:5183 | GCTATTAGTGGTAGTGGT<br>AGTAACACATTCTACGC<br>AGACTCCGTGAAGGGC<br>SEQ ID NO:13195 | CGAACGCCCTCTGATGTTTT<br>GATATC<br>SEQ ID NO:21207 |
| | | AA | SYAMS<br>SEQ ID NO:5184 | AISGSGSNTFYADSVKG<br>SEQ ID NO:13196 | RTPSDVFDI<br>SEQ ID NO:21208 |
| iPS:433917 | 21-225_43E11 | NA | GACTATGGCATGCAC<br>SEQ ID NO:5185 | GTTATATGGTATGATGG<br>AAGTAATAAATACTATG<br>CAGACTCCGTGAAGGGC<br>SEQ ID NO:13197 | CGGTATGTCAGAAGCTGGT<br>GGGAGGTATGGACGTC<br>SEQ ID NO:21209 |
| | | AA | DYGMH<br>SEQ ID NO:5186 | VIWYDGSNKYYADSVKG<br>SEQ ID NO:13198 | RYVRSWVGGMDV<br>SEQ ID NO:21210 |
| iPS:433919 | 21-225_44B3 | NA | GACTATGGCATGCAC<br>SEQ ID NO:5187 | GTTATATGGTATGATGG<br>AAGTAATAAATACTATG<br>CAGACTCCGTGAAGGGC<br>SEQ ID NO:13199 | GAGAGGTATAGCAGTGGCTG<br>GTACGACTACGGTATGGACG<br>TC<br>SEQ ID NO:21211 |
| | | AA | DYGMH<br>SEQ ID NO:5188 | VIWYDGSNKYYADSVKG<br>SEQ ID NO:13200 | ERYSSGWYDYGMDV<br>SEQ ID NO:21212 |
| iPS:433921 | 21-225_44C3 | NA | AGCTATGGCATGCAC<br>SEQ ID NO:5189 | GTTATATGGTTTGAAGG<br>AAGTAATAAATACTATG<br>CAGATTCCGTGAAGGGC<br>SEQ ID NO:13201 | GAACTAGGATTTTCCACCGA<br>CTAC<br>SEQ ID NO:21213 |
| | | AA | SYGMH<br>SEQ ID NO:5190 | VIWFEGSNKYYADSVKG<br>SEQ ID NO:13202 | ELGFSTDY<br>SEQ ID NO:21214 |

FIGURE 49
(Continued)

| | | | | | |
|---|---|---|---|---|---|
| iPS:433923 | 21-225_44D3 | NA | AGCTATGTCATCATGCAC SEQ ID NO:5191 | GTTATATGGTATGATGG AAGTAATAAATACTATG CTGACTCCGTGAAGGGC SEQ ID NO:13203 | GAAAGGTATAGCAGTGGCTT GTACGACTACGGTATGGACG TC SEQ ID NO:21215 |
| | | AA | SYVMH SEQ ID NO:5192 | VIWYDGSNKYYADSVKG SEQ ID NO:13204 | ERYSSGLYDYGMDV SEQ ID NO:21216 |
| iPS:433925 | 21-225_44F3 | NA | AGCTATGCCATGAGC SEQ ID NO:5193 | ATTCTCAGTGGTGGTGGT AAGACCACATACTACGC AGACTCCGTGAAGGGC SEQ ID NO:13205 | CGAACGCCCTCTGATGCTTT TGATATC SEQ ID NO:21217 |
| | | AA | SYAMS SEQ ID NO:5194 | ILSGGGKTTYADSVKG SEQ ID NO:13206 | RTPSDAFDI SEQ ID NO:21218 |
| iPS:433929 | 21-225_44D5 | NA | AGCTATGTCATGCAC SEQ ID NO:5195 | GTTATATGGTATGATGG AAGTAATAAATACTATG CAGACTCCGTGAAGGGC SEQ ID NO:13207 | GTCCGTATAGCAGCAGCTG GTACGACTACGGTATGGACG TC SEQ ID NO:21219 |
| | | AA | SYVMH SEQ ID NO:5196 | VIWYDGSNKYYADSVKG SEQ ID NO:13208 | VPYSSSWYDYGMDV SEQ ID NO:21220 |
| iPS:433931 | 21-225_44F6 | NA | AGTTACTACTGGAGC SEQ ID NO:5197 | TATATCTATTACAGTGGA AACACCAACTACAACCC CTCCCTCAAGAGT SEQ ID NO:13209 | GGGGTGGCTATAAAGAACTA C SEQ ID NO:21221 |
| | | AA | SYYWS SEQ ID NO:5198 | YIYYSGNTNYNPSLKS SEQ ID NO:13210 | GVAIKNY SEQ ID NO:21222 |

FIGURE 49
(Continued)

| | | | | | |
|---|---|---|---|---|---|
| iPS:433933 | 21-225_44C8 | NA | AACTATGGCATGCAC | GTTATATGGTATGAAGG AAGTAATAAATACTATG CAGACTCCGTGAAGGGC | GAACTGGGGTTCCTCTCTGA CTAC |
| | | | SEQ ID NO:5199 | SEQ ID NO:13211 | SEQ ID NO:21223 |
| | | AA | NYGMH | VIWYEGSNKYYADSVKG | ELGFLSDY |
| | | | SEQ ID NO:5200 | SEQ ID NO:13212 | SEQ ID NO:21224 |
| iPS:433935 | 21-225_44F9 | NA | AGCTATGTCATGCAC | GTTATATGGTATGATGG AAGTAATAAATACTATG CAGACTCCGTGAAGGGC | GAACCATATAGCAGCAGCTG GTACGACTACGGTATGGACG TC |
| | | | SEQ ID NO:5201 | SEQ ID NO:13213 | SEQ ID NO:21225 |
| | | AA | SYVMH | VIWYDGSNKYYADSVKG | EPYSSSWYDYGMDV |
| | | | SEQ ID NO:5202 | SEQ ID NO:13214 | SEQ ID NO:21226 |
| iPS:433937 | 21-225_44B10 | NA | AGCTATGGCATGCAC | GTTATATGGTATGATGG AAGTAATAAATACTATG CAGACTCCGTGAAGGGC | CGGTATAGCAGCAGCTGGGT GGGGGTATGGACGTC |
| | | | SEQ ID NO:5203 | SEQ ID NO:13215 | SEQ ID NO:21227 |
| | | AA | SYGMH | VIWYDGSNKYYADSVKG | RYSSSWVGGMDV |
| | | | SEQ ID NO:5204 | SEQ ID NO:13216 | SEQ ID NO:21228 |
| iPS:433939 | 21-225_44C10 | NA | GACTGTGTCATGCAC | GTTATATGGTATGATGG AAGTAATAAATACTATG CTGACTCCGTGAAGGGC | GAAAGGTATAGCAGCAGTGGCTT GTACGACTACGGTATGGACG TC |
| | | | SEQ ID NO:5205 | SEQ ID NO:13217 | SEQ ID NO:21229 |

FIGURE 49
(Continued)

| | | | | | |
|---|---|---|---|---|---|
| iPS:433941 | 21-225_44D10 | AA | DCVMH<br>SEQ ID NO:5206 | VIWYDGSNKYYADSVKG<br>SEQ ID NO:13218 | ERYSSGLYDYGMDV<br>SEQ ID NO:21230 |
| | | NA | AGCTATGCCATGAGC<br>SEQ ID NO:5207 | GCTATTAGTGGTGGTGTGGT GTAACACATTCGACGC AGACTCCGTGAAGGGC<br>SEQ ID NO:13219 | GAAAGGAGTGGGAGCTATTT TGACTAC<br>SEQ ID NO:21231 |
| iPS:433943 | 21-225_44E10 | AA | SYAMS<br>SEQ ID NO:5208 | AISGRGVNTFDADSVKG<br>SEQ ID NO:13220 | ERSGSYFDY<br>SEQ ID NO:21232 |
| | | NA | AGCTATGCCATGAAC<br>SEQ ID NO:5209 | GGTGTTGTTGGTAGTGGT GGTAGAACATATACGC AGACTCCGTGAAGGGC<br>SEQ ID NO:13221 | GATCGGGGGCAGTGGCTCCT AGGCGGTATGGACGTC<br>SEQ ID NO:21233 |
| iPS:433945 | 21-225_44C12 | AA | SYSVN<br>SEQ ID NO:5210 | GVVGSGGRTYYADSVKG<br>SEQ ID NO:13222 | DRGQWLLGGMDV<br>SEQ ID NO:21234 |
| | | NA | AGCTATAGCGTGAAC<br>SEQ ID NO:5211 | TACATTAGTAGTAGTAGT AGTACCATATACTACGC AGACTCTGTGAAGGGC<br>SEQ ID NO:13223 | AGTGGATACAGCTATGCTTA CTACTACTACGGTATGG ACGTC<br>SEQ ID NO:21235 |
| | 21-225_44E12 | AA | SYSVN<br>SEQ ID NO:5212 | YISSSSTIYYADSVKG<br>SEQ ID NO:13224 | SGYSYAYYYYGMDV<br>SEQ ID NO:21236 |
| iPS:433947 | | NA | AGCGATGACACGCAC<br>SEQ ID NO:5213 | GTTATATGGTTTGATGAA TATAATAATACTATGC AGACTCCGTGAAGGGC<br>SEQ ID NO:13225 | GATCTAATAGCAGCAGCTGG GACGGGAGACTAC<br>SEQ ID NO:21237 |
| | | AA | SDDTH<br>SEQ ID NO:5214 | VIWFDEYNKYYADSVKG<br>SEQ ID NO:13226 | DLIAAGTGDY<br>SEQ ID NO:21238 |

FIGURE 49
(Continued)

| | | | | | | | |
|---|---|---|---|---|---|---|---|
| iPS:433949 | 21-225_45H2 | NA | GACTACTACATGAAC | | TACATTAGTAGTAGTGGT ATTACCAAATACTACG AGACTCTGTGAAGGGC | | GATACAATCTAC |
| | | | SEQ ID NO:5215 | | SEQ ID NO:13227 | | SEQ ID NO:21239 |
| | | AA | DYYMN | | YISSSGITKYYADSVKG | | DTIY |
| | | | SEQ ID NO:5216 | | SEQ ID NO:13228 | | SEQ ID NO:21240 |
| iPS:433951 | 21-225_45B4 | NA | GACTGTGTCATGCAC | | GTTATATGGTATGATGG AAGTAATAAATACTATG CTGACTCCGTGAAGGGC | | GAAAGGTATAGCAGTGGCTT GTACGACTACGGTATGGACG TC |
| | | | SEQ ID NO:5217 | | SEQ ID NO:13229 | | SEQ ID NO:21241 |
| | | AA | DCVMH | | VIWYDGSNKYYADSVKG | | ERYSSGLYDYGMDV |
| | | | SEQ ID NO:5218 | | SEQ ID NO:13230 | | SEQ ID NO:21242 |
| iPS:433953 | 21-225_45H4 | NA | AGCTATGCCATGAGT | | GCTATTAGTGGTAGTGGT AGTAACACATTCTACGC AGACTCCGTGAAGGGC | | CGAACGCCCTCTGATGTTTTT GATATC |
| | | | SEQ ID NO:5219 | | SEQ ID NO:13231 | | SEQ ID NO:21243 |
| | | AA | SYAMS | | AISGSGSNTFYADSVKG | | RTPSDVFDI |
| | | | SEQ ID NO:5220 | | SEQ ID NO:13232 | | SEQ ID NO:21244 |
| iPS:433955 | 21-225_45B8 | NA | GACTGTGTCATGCAC | | GTTATATGGTATGATGG AAGTAATAAATACTATG CTGACTCCGTGAAGGGC | | GAAAGGTATAGCAGTGGCTT GTACGACTACGGTATGGACG TC |
| | | | SEQ ID NO:5221 | | SEQ ID NO:13233 | | SEQ ID NO:21245 |
| | | AA | DCVMH | | VIWYDGSNKYYADSVKG | | ERYSSGLYDYGMDV |
| | | | SEQ ID NO:5222 | | SEQ ID NO:13234 | | SEQ ID NO:21246 |

FIGURE 49
(Continued)

| | | | | |
|---|---|---|---|---|
| iPS:433957 | 21-225_45F8 | NA | AGCTATGCCATGAGC | GCTATTAGTAGTGGTGGTGGTGGT GTTAACACATTCGACGC AGACTCCGTGAAGGGC | GAAAGGAGTGGGAGCTATTT TGACTAC |
| | | | SEQ ID NO:5223 | SEQ ID NO:13235 | SEQ ID NO:21247 |
| | | AA | SYAMS | AISGRGVNTFDADSVKG | ERSGSYFDY |
| | | | SEQ ID NO:5224 | SEQ ID NO:13236 | SEQ ID NO:21248 |
| iPS:433959 | 21-225_45C9 | NA | AGCTATGCCATGAGC | GTTATTAGTGGTGGTGGTGGT GGTACCACATACTACGC AGACTCCGTGAAGGGC | CGAACGCCCTCTGATGCTTT TGATATC |
| | | | SEQ ID NO:5225 | SEQ ID NO:13237 | SEQ ID NO:21249 |
| | | AA | SYAMS | VISGRGGTYYADSVKG | RTPSDAFDI |
| | | | SEQ ID NO:5226 | SEQ ID NO:13238 | SEQ ID NO:21250 |
| iPS:433961 | 21-225_45D9 | NA | AGCTATACCATGAAC | TCCATTAGTGGAAGTAG TACTTACATATACTACGC AGACTCCGTGAAGGGC | GTGACCTCTTTTGACTAC |
| | | | SEQ ID NO:5227 | SEQ ID NO:13239 | SEQ ID NO:21251 |
| | | AA | SYTMN | SISGSSTYIYYADSVKG | VTSFDY |
| | | | SEQ ID NO:5228 | SEQ ID NO:13240 | SEQ ID NO:21252 |
| iPS:433963 | 21-225_46B1 | NA | AGCGATGACTCGCAC | GTTATATGGTTTGATGAA TATACTAAATACTATGCA GACTCCGTGAAGGGC | GATCTAATAGCAGCAACTGG GACGGGAGACTAC |
| | | | SEQ ID NO:5229 | SEQ ID NO:13241 | SEQ ID NO:21253 |
| | | AA | SDDSH | VIWFDEYTKYYADSVKG | DLIAAIGTGDY |
| | | | SEQ ID NO:5230 | SEQ ID NO:13242 | SEQ ID NO:21254 |
| iPS:433965 | 21-225_46F2 | NA | AGCTATGGCATGCAC | ATTATATGGTATGATGG AAGTAATAAATACTATG TAGACTCCGTGAAGGGC | GATCGATACGATTTTTGGAG TGGTTACTTGACTAC |
| | | | SEQ ID NO:5231 | SEQ ID NO:13243 | SEQ ID NO:21255 |
| | | AA | SYGMH | IIWYDGSNKYYVDSVKG | DRYDFWSGYFDY |

FIGURE 49
(Continued)

| | | | | | | |
|---|---|---|---|---|---|---|
| iPS:433967 | 21-225_46C3 | NA | SEQ ID NO:5232 AGCTATGTCATGCAC | SEQ ID NO:13244 GTTATATGGTATGGATGG AAGTAATAAATACTATG CTGACTCCGTGAAGGGC | SEQ ID NO:21256 GAAAGGTATAGCAGTGGCTT GTACGACTACGGTATGGACG TC |
| | | AA | SEQ ID NO:5233 SYVMH | SEQ ID NO:13245 VIWYDGSNKYYADSVKG | SEQ ID NO:21257 ERYSSGLYDYGMDV |
| iPS:433969 | 21-225_46F3 | NA | SEQ ID NO:5234 GATTATGGCATGCAC | SEQ ID NO:13246 GTTATATGGTTTGAAGG AAGTAATAAATACTATG CAGATTCCGTGAAGGGC | SEQ ID NO:21258 GAACTAGGATTTTCCAATGA CTAC |
| | | AA | SEQ ID NO:5235 DYGMH | SEQ ID NO:13247 VIWFEGSNKYYADSVKG | SEQ ID NO:21259 ELGFSNDY |
| iPS:433971 | 21-225_46D4 | NA | SEQ ID NO:5236 AGCTATGTCATGCAC | SEQ ID NO:13248 GTTATATGGTATGATGG AAGTAATAAATACTATG CAGACTCCGTGAAGGGC | SEQ ID NO:21260 GTCCCGTATAGCAGCAGTTG GTACGACTACGGTATGGACG TC |
| | | AA | SEQ ID NO:5237 SYVMH | SEQ ID NO:13249 VIWYDGSNKYYADSVKG | SEQ ID NO:21261 VPYSSSWYDYGMDV |
| iPS:433973 | 21-225_46A6 | NA | SEQ ID NO:5238 AGCTATGCCATGAGC | SEQ ID NO:13250 GCTATTAGTGGTCGTGGT ATTAACACATTCGACGC AGACTCCGTGAAGGGC | SEQ ID NO:21262 GAAAGGAGTGGGAGCTATTT TGACTAC |
| | | AA | SEQ ID NO:5239 SYAMS | SEQ ID NO:13251 AISGRGINTFDADSVKG | SEQ ID NO:21263 ERSGSYFDY |
| | | | SEQ ID NO:5240 | | SEQ ID NO:21264 |

FIGURE 49
(Continued)

| | | | | | |
|---|---|---|---|---|---|
| iPS:433975 | 21-225_46C6 | NA | AGCTATGGCATACAC | GTTATATGGTATGATGAAATAATAAATACTATGCAGACTCCGTGAAGGGC | GAGCTAGGAGATTTCCAATGACTAC |
| | | | SEQ ID NO:5241 | SEQ ID NO:13253 | SEQ ID NO:21265 |
| | | AA | SYGIH | VIWYDENNKYYADSVKG | ELGFSNDY |
| | | | SEQ ID NO:5242 | SEQ ID NO:13254 | SEQ ID NO:21266 |
| iPS:433977 | 21-225_46D8 | NA | GATTATGGCATACAC | GTTATATGGTTTGAAGGAAGTAATAAATACTATGCAGATTCCGTGAAGGGC | GAACTAGGAGATTTCCAATGACTAC |
| | | | SEQ ID NO:5243 | SEQ ID NO:13255 | SEQ ID NO:21267 |
| | | AA | DYGIH | VIWYFEGSNKYYADSVKG | ELGFSNDY |
| | | | SEQ ID NO:5244 | SEQ ID NO:13256 | SEQ ID NO:21268 |
| iPS:433979 | 21-225_46B9 | NA | AGCTATGGCATGCAC | GTTATATGGTATGATGATAAGAAATAAATACTATGCAGACTCCGTGAAGGGC | CGGTATAGCAGCAGCTGGATGGGAGGTATGGACGTC |
| | | | SEQ ID NO:5245 | SEQ ID NO:13257 | SEQ ID NO:21269 |
| | | AA | SYGMH | VIWYDGRNKYYADSVKG | RYSSSWMGGMDV |
| | | | SEQ ID NO:5246 | SEQ ID NO:13258 | SEQ ID NO:21270 |
| iPS:433981 | 21-225_46E9 | NA | GACTACTACATGAAC | TACATTAATAGTAATGGTTTTACCATATACTGCAGACTCTGTGAAGGGC | GATACAATCTAC |
| | | | SEQ ID NO:5247 | SEQ ID NO:13259 | SEQ ID NO:21271 |
| | | AA | DYYMN | YINSNGFTIYYADSVKG | DTIY |
| | | | SEQ ID NO:5248 | SEQ ID NO:13260 | SEQ ID NO:21272 |

FIGURE 49 (Continued)

| | | | | |
|---|---|---|---|---|
| iPS:433983 | 21-225_47A1 | NA | GACTATGGCATGCAC | GTTATATGGTATGATGACTATAATAAAAAGTATGCAGACTCCGTGAAGGGC | GAACTGGGGATGCTCTTTGACTAC |
| | | | SEQ ID NO:5249 | SEQ ID NO:13261 | SEQ ID NO:21273 |
| | | AA | DYGMH | VIWYDDYNKKYADSVKG | ELGMLFDY |
| | | | SEQ ID NO:5250 | SEQ ID NO:13262 | SEQ ID NO:21274 |
| iPS:433985 | 21-225_47C1 | NA | GACTATGGCATGCAC | GTTATATGGTATGATGGAAGTAATAAATACTATGCAGACTCCGTGAAGGGC | CGGTATAGCCGCAGCTGGGTGGGAGGTATGGACGTC |
| | | | SEQ ID NO:5251 | SEQ ID NO:13263 | SEQ ID NO:21275 |
| | | AA | DYGMH | VIWYDGSNKYYADSVKG | RYSRSWVGGMDV |
| | | | SEQ ID NO:5252 | SEQ ID NO:13264 | SEQ ID NO:21276 |
| iPS:433987 | 21-225_47A5 | NA | GACGATGACACACAC | GTTATATGGTTTGATGGAAGTAATAAATACTATGCAGACTCCGTGAAGGGC | GATCTTATAGCAGCAGCTGGTACAGTTGACTAC |
| | | | SEQ ID NO:5253 | SEQ ID NO:13265 | SEQ ID NO:21277 |
| | | AA | DDDTH | VIWFDGSNKYYADSVKG | DLIAAAGTVDY |
| | | | SEQ ID NO:5254 | SEQ ID NO:13266 | SEQ ID NO:21278 |
| iPS:433989 | 21-225_47C7 | NA | AACTATGCCATGAGC | GGTATTAGTGGTAGTGGTAGTCGCACATACTACGCAGACTCCGTGAAGGGC | GATCGGGGGCAGTGGCTCATAGGCGGTATGGACGTC |
| | | | SEQ ID NO:5255 | SEQ ID NO:13267 | SEQ ID NO:21279 |
| | | AA | NYAMS | GISGSGSRTYYADSVKG | DRGQWLIGGMDV |
| | | | SEQ ID NO:5256 | SEQ ID NO:13268 | SEQ ID NO:21280 |

FIGURE 49
(Continued)

| iPS:433991 | 21-225_47E7 | NA | ATCTATGGCATGCAC | GTTATATGGTATGATGGAAGTAATAAATACTATGCAGACTCCGTGAAGGGC | CGGTATAGCAGAAGCTGGGTGGGAGGTATGGACGTC |
|---|---|---|---|---|---|
| | | | SEQ ID NO:5257 | SEQ ID NO:13269 | SEQ ID NO:21281 |
| | | AA | IYGMH | VIWYDGSNKYYADSVKG | RYSRSWVGGMDV |
| | | | SEQ ID NO:5258 | SEQ ID NO:13270 | SEQ ID NO:21282 |
| iPS:433993 | 21-225_47G7 | NA | AGCTATGCCATGAGT | GCTATTAGTGGTGTCGTGGTGGTAACACATTCTACGCAGAGTCCGTGAGGGC | ATTATCGGGAGCAGTGGGCCTTTGACTAC |
| | | | SEQ ID NO:5259 | SEQ ID NO:13271 | SEQ ID NO:21283 |
| | | AA | SYAMS | AISGRGGNTFYAESVRG | HREQWAFDY |
| | | | SEQ ID NO:5260 | SEQ ID NO:13272 | SEQ ID NO:21284 |
| iPS:433995 | 21-225_47H7 | NA | GACTACTACATGATC | TACATTAATAGTAATGGTTTTACCAAATACTACGCAGACTCTGTGAAGGGC | GATACAGTCTAC |
| | | | SEQ ID NO:5261 | SEQ ID NO:13273 | SEQ ID NO:21285 |
| | | AA | DYYMI | YINSNGFTKYYADSVKG | DTVY |
| | | | SEQ ID NO:5262 | SEQ ID NO:13274 | SEQ ID NO:21286 |
| iPS:433997 | 21-225_48C1 | NA | AGCTATGGCATGCAC | GTTGTATGGTATGATGAAATTAATAAAAAGTATGCAGACTCCGTGAAGGGC | GAATTAGGGTGGGAGGCTGACTAC |
| | | | SEQ ID NO:5263 | SEQ ID NO:13275 | SEQ ID NO:21287 |
| | | AA | SYGMH | VVWYDEINKKYADSVKG | ELGWEADY |
| | | | SEQ ID NO:5264 | SEQ ID NO:13276 | SEQ ID NO:21288 |

FIGURE 49
(Continued)

| | | | | | |
|---|---|---|---|---|---|
| iPS:433999 | 21-225_48D1 | NA | AGTTATGCCATGAGC | GTTATTAGTAGTGGTCGTGGT GGTAGCACATTCTACGC AGACTCCGTGAAGGGC | CGTATAGCAGTGGCTGGAA TGAGGCTTTTGATATC |
| | | | SEQ ID NO:5265 | SEQ ID NO:13277 | SEQ ID NO:21289 |
| | | AA | SYAMS | VISGRGGSTFYADSVKG | RIAVAGNEAFDI |
| | | | SEQ ID NO:5266 | SEQ ID NO:13278 | SEQ ID NO:21290 |
| iPS:434001 | 21-225_48F2 | NA | AACTATGTCATGCAC | GTTATATGGTATAGAGG AAGTAATAAATACTATG CAGACTCCGTGAAGGGC | GAGAGGTATAGCAGCAGCTG GTACGACTACGGTCTGGACG TC |
| | | | SEQ ID NO:5267 | SEQ ID NO:13279 | SEQ ID NO:21291 |
| | | AA | NYVMH | VIWYDGSNKYYADSVKG | ERYSSSWYDYGLDV |
| | | | SEQ ID NO:5268 | SEQ ID NO:13280 | SEQ ID NO:21292 |
| iPS:434003 | 21-225_48C3 | NA | AGTTATGCCATGAGC | GTTATTAGTAGTGGTCGTGGT GGTAGCACATTCTACGC AGACTCCGTGAAGGGC | CGTATAGCAGTGGCTGGAA TGAGGCTTTTGATATC |
| | | | SEQ ID NO:5269 | SEQ ID NO:13281 | SEQ ID NO:21293 |
| | | AA | SYAMS | VISGRGGSTFYADSVKG | RIAVAGNEAFDI |
| | | | SEQ ID NO:5270 | SEQ ID NO:13282 | SEQ ID NO:21294 |
| iPS:434007 | 21-225_48D7 | NA | AACTCTGCCATGAAC | GCTATTAGTGGTATGAGGA GGTACCACATTCTACGC AGACTCCGTGAAGGGC | TGTGGGCGGGAGCAGTGGCT TGACTAC |
| | | | SEQ ID NO:5271 | SEQ ID NO:13283 | SEQ ID NO:21295 |
| | | AA | NSAMN | AISGSGGTTFYADSVKG | CGREQWLDY |
| | | | SEQ ID NO:5272 | SEQ ID NO:13284 | SEQ ID NO:21296 |
| iPS:434009 | 21_225_48A9 | NA | AGCTATGGCATGCAC | GTTATATGGTATGAGGA AATAAGAAATACTATG CAGACTCCGTGAAGGGC | GAACTTGCCTGGTACGAGGA CTAC |

FIGURE 49
(Continued)

| | | | | | | | |
|---|---|---|---|---|---|---|---|
| iPS:434011 | 21-225_48A9 | AA | SEQ ID NO:5273 SYGMH | | SEQ ID NO:13285 VIWYEENKKYYADSVKG | | SEQ ID NO:21297 ELAWYEDY |
| iPS:434013 | 21-225_48B10 | NA | SEQ ID NO:5274 GACTACTTCATGACC | | SEQ ID NO:13286 TACATTAGTAGTGCTGGT GGTGCCATATACTACGC AGACTCTGTGAAGGGC | | SEQ ID NO:21298 GCAGTGGCTGCCCCTGGTGT TTTTGATATC |
| | | AA | SEQ ID NO:5275 DYFMT | | SEQ ID NO:13287 YISSAGGAIYYADSVKG | | SEQ ID NO:21299 AVAAPGVFDI |
| iPS:434015 | 21-225_48D12 | NA | SEQ ID NO:5276 GACTATGGCATGCAC | | SEQ ID NO:13288 GTTATATGGTATGATGTA AGTAATAAATACTATGT AGACTCCGTGAAGGGC | | SEQ ID NO:21300 GAACTGGGGATGAGATCTGA CTAC |
| | | AA | SEQ ID NO:5277 DYGMH | | SEQ ID NO:13289 VIWYDVSNKYYVDSVKG | | SEQ ID NO:21301 ELGMRSDY |
| iPS:434015 | 21-225_48F12 | NA | SEQ ID NO:5278 GACTACTTCATGACC | | SEQ ID NO:13290 TACATTAGTAGTGCTGGT GGTGCCATATACTACGC AGACTCTGTGAAGGGC | | SEQ ID NO:21302 GCAGTGGCTGCCCCTGGTGC TTTTGATATC |
| | | AA | SEQ ID NO:5279 DYFMT | | SEQ ID NO:13291 YISSAGGAIYYADSVKG | | SEQ ID NO:21303 AVAAPGAFDI |
| iPS:434017 | 21-225_48G12 | NA | SEQ ID NO:5280 GACTACTTCATGACC | | SEQ ID NO:13292 TACATTAGTAGTGCTGGT GGTGCCATATACTACGC AGACTCTGTGAAGGGC | | SEQ ID NO:21304 GCAGTGGCTGCCCCTGGTGC TTTTGATATC |
| | | AA | SEQ ID NO:5281 DYFMT | | SEQ ID NO:13293 YISSAGGAIYYADSVKG | | SEQ ID NO:21305 AVAAPGAFDI |
| | | | SEQ ID NO:5282 | | SEQ ID NO:13294 | | SEQ ID NO:21306 |

FIGURE 49
(Continued)

| | | | | | |
|---|---|---|---|---|---|
| iPS:434019 | 21-225_49A1 | NA | GACTATGGCATGCAC SEQ ID NO:5283 | GTTATATGGTATGATGA AGATAAATATTATG TAGACTCCGTGAAGGGC SEQ ID NO:13295 | GAACTGGGGGTTCCTCTCTGA CTAC SEQ ID NO:21307 |
| | | AA | DYGMH SEQ ID NO:5284 | VIWYDEDNKYYVDSVKG SEQ ID NO:13296 | ELGFLSDY SEQ ID NO:21308 |
| iPS:434021 | 21-225_49C1 | NA | AGCTATGGCATGCAC SEQ ID NO:5285 | GTTATATGGTATGATGG AAGTAATAAATACTATG CAGACTCCGTGAAGGGC SEQ ID NO:13297 | AGGTATAGCAGCAGCTGGTC GGGCGGTATGGACGTC SEQ ID NO:21309 |
| | | AA | SYGMH SEQ ID NO:5286 | VIWYDGSNKYYADSVKG SEQ ID NO:13298 | RYSSSWSGGMDV SEQ ID NO:21310 |
| iPS:434023 | 21-225_49F1 | NA | AGCTATGGCATGAGC SEQ ID NO:5287 | GTTATTAGTGGTAGTGGT GGTAGCACATTCTACGC AGACTCCGTGAAGGGC SEQ ID NO:13299 | GCTATAGCAGCAGCGGCTGGTGC CCACTATTTTGACTAC SEQ ID NO:21311 |
| | | AA | SYAMS SEQ ID NO:5288 | VISGSGGSTFYADSVKG SEQ ID NO:13300 | AIAAAGAHYFDY SEQ ID NO:21312 |
| iPS:434025 | 21-225_49G3 | NA | AGTTATGGCATGCAC SEQ ID NO:5289 | GTTATATGGTATGATGG AAGTAATAAATACTATG CAGACTCCGTGAAGGGC SEQ ID NO:13301 | AGGTATAGCAGCAGCTGGTC GGGCGGAATGGACGTC SEQ ID NO:21313 |
| | | AA | SYGMH SEQ ID NO:5290 | VIWYDGSNKYYADSVKG SEQ ID NO:13302 | RYSSSWSGGMDV SEQ ID NO:21314 |

FIGURE 49
(Continued)

| iPS: | | | | | |
|---|---|---|---|---|---|
| iPS:434027 | 21-225_49H5 | NA | AGCTATGGCATGACC | GCTATTAGTGTGGTAGTGGT GGTAACTCATTCTACGCA GACTCCGTGAAGGGC | GCAAGGGCAGTGGCTGGGTC ACACTGGTTCGACCCC |
| | | | SEQ ID NO:5291 | SEQ ID NO:13303 | SEQ ID NO:21315 |
| | | AA | SYAMT | AISGSGGNSFYADSVKG | ARAVAGSHWFDP |
| | | | SEQ ID NO:5292 | SEQ ID NO:13304 | SEQ ID NO:21316 |
| iPS:434029 | 21-225_49C6 | NA | AACTATGGCATGCAC | GTTATATGGTTTGATGGTA AGTAATAAAAGTATGT AGACTCCGTGAAGGGC | GATCTGGGGATGATCGAGGA CTAC |
| | | | SEQ ID NO:5293 | SEQ ID NO:13305 | SEQ ID NO:21317 |
| | | AA | NYGMH | VIWFDVSNKKYVDSVKG | DLGMIEDY |
| | | | SEQ ID NO:5294 | SEQ ID NO:13306 | SEQ ID NO:21318 |
| iPS:434031 | 21-225_49E7 | NA | AGCTATGGCATGCAC | GTTATATGGTATGATGG AAGTAATAAATACTATGC CAGACTCCGTGAAGGGC | AGGTATAGCAGCAGCTGGTC GGGCGGTATGGACGTC |
| | | | SEQ ID NO:5295 | SEQ ID NO:13307 | SEQ ID NO:21319 |
| | | AA | SYGMH | VIWYDGSNKYYADSVKG | RYSSSWSGGMDV |
| | | | SEQ ID NO:5296 | SEQ ID NO:13308 | SEQ ID NO:21320 |
| iPS:434033 | 21-225_49F9 | NA | AGTTATGGCATGCAC | CTTATATGGTATGATGGA AGGAATAAATACTATGC AGACTCCGTGAAGGGC | AGGTATAGCAGCAGCTGGTC GGGCGGTATGGACGTC |
| | | | SEQ ID NO:5297 | SEQ ID NO:13309 | SEQ ID NO:21321 |
| | | AA | SYGMH | LIWYDGRNKYYADSVKG | RYSSSWSGGMDV |
| | | | SEQ ID NO:5298 | SEQ ID NO:13310 | SEQ ID NO:21322 |

FIGURE 49
(Continued)

| | | | | | |
|---|---|---|---|---|---|
| iPS:434035 | 21-225_49F10 | NA | GGCTACCATATGCAC | TGGATCAACCTAATAACAATGCCACAAACTATGCTCAGAACTTTCAGGGC | GACGGTACCAGCAGCTTTGACTTC |
| | | | SEQ ID NO:5299 | SEQ ID NO:13311 | SEQ ID NO:21323 |
| | | AA | GYHMH | WINPNNNATNYAQNFQG | DGTSSFDF |
| | | | SEQ ID NO:5300 | SEQ ID NO:13312 | SEQ ID NO:21324 |
| iPS:434037 | 21-225_49G12 | NA | AGCTATGCCATGAGC | GTTATTAGTGGTAGTGGTGGTACCACATTCTACGCAGACTCCGTGAAGGGC | CGTATAGCAGTGGCTGGGAATGATGCTTTTGATATC |
| | | | SEQ ID NO:5301 | SEQ ID NO:13313 | SEQ ID NO:21325 |
| | | AA | SYAMS | VISGSGGTTFYADSVKG | RIAVAGNDAFDI |
| | | | SEQ ID NO:5302 | SEQ ID NO:13314 | SEQ ID NO:21326 |
| iPS:434039 | 21-225_43B1 | NA | GACTACTACATGAAC | TACATTAATAGTAATGGTTTTACCATATACTACGCAGACTCTGTGAAGGGC | GATACAATCTAC |
| | | | SEQ ID NO:5303 | SEQ ID NO:13315 | SEQ ID NO:21327 |
| | | AA | DYYMN | YINSNGFTIYYADSVKG | DTIY |
| | | | SEQ ID NO:5304 | SEQ ID NO:13316 | SEQ ID NO:21328 |
| iPS:434041 | 21-225_50H8 | NA | AGTTATGCCATGAGC | GTTATTAGTGGTCGTGGTGGTACCACATTCTACGCAGACTCCGTGAAGGGC | CGTATAGCAGTGGCTGGGAATGAGGCTTTTGATATC |
| | | | SEQ ID NO:5305 | SEQ ID NO:13317 | SEQ ID NO:21329 |
| | | AA | SYAMS | VISGRGGTTFYADSVKG | RIAVAGNEAFDI |
| | | | SEQ ID NO:5306 | SEQ ID NO:13318 | SEQ ID NO:21330 |
| iPS:434043 | 21-225_50G10 | NA | AGCTATAGCATGAAC | TCCATTAGTGGTGGTAGTAGTAGTTACATATACTACGCAGACTCAGTGAAGGGC | GTAGCAACTTTTGACTAC |
| | | | SEQ ID NO:5307 | SEQ ID NO:13319 | SEQ ID NO:21331 |

FIGURE 49
(Continued)

| | | | | | | |
|---|---|---|---|---|---|---|
| iPS:434045 | 21-225_50H10 | AA | SYSMN<br>SEQ ID NO:5308 | SISGSSSYIYYADSVKG<br>SEQ ID NO:13320 | VATFDY<br>SEQ ID NO:21332 | |
| | | NA | AGTTATGCCCATGAGC<br>SEQ ID NO:5309 | GTTATTAGTGGTCGTGGT<br>GGTAGCACATTCTACGC<br>AGACTCCGTGAAGGGC<br>SEQ ID NO:13321 | CGTATAGCAGTGGCTGGGAA<br>TGAGGCTTTTGATATC<br>SEQ ID NO:21333 | |
| iPS:434047 | 21-225_50A12 | AA | SYAMS<br>SEQ ID NO:5310 | VISGRGGSTFYADSVKG<br>SEQ ID NO:13322 | RIAVAGNEAFDI<br>SEQ ID NO:21334 | |
| | | NA | GGCCACTATATAAAC<br>SEQ ID NO:5311 | TGGGTCAACCTAACAG<br>TGGTGGCACAAACTCTG<br>CACAGAAGTTTCAGGGC<br>SEQ ID NO:13323 | GGAGGGCAGCTCGGCGGGTT<br>TAACTACTACTACTACGGTA<br>TGGACGTG<br>SEQ ID NO:21335 | |
| iPS:434049 | 21-225_50B12 | AA | GHYIN<br>SEQ ID NO:5312 | WVNPNSGGTNSAQKFQG<br>SEQ ID NO:13324 | GGQLGGFNYYYYGMDV<br>SEQ ID NO:21336 | |
| | | NA | AGCCATAGCATGAAC<br>SEQ ID NO:5313 | TCCATCAGTAGTAGTAGT<br>AATTACATATACTACGC<br>AGACTCAGTGAAGGGC<br>SEQ ID NO:13325 | GATCGGAGCATAGTAGTGGC<br>TGGTCCCTGGGACTACTACG<br>GTATGGACGTC<br>SEQ ID NO:21337 | |
| iPS:434053 | 21-225_51E1 | AA | SHSMN<br>SEQ ID NO:5314 | SISSSNYIYYADSVKG<br>SEQ ID NO:13326 | DRSIVVAGPWDYYGMDV<br>SEQ ID NO:21338 | |
| | | NA | AGCTATGGCATGCAC<br>SEQ ID NO:5315 | GTTATATGGTATGATGG<br>AAGTAGTAAATACTATG<br>CAGACTCCGTGAAGGGC<br>SEQ ID NO:13327 | AGGTATAGCAGCAGTGGTC<br>GGGCGGTATGGACGTC<br>SEQ ID NO:21339 | |
| iPS:434055 | 21_225_51B4 | AA | SYGMH<br>SEQ ID NO:5316 | VIWYDGSSKYYADSVKG<br>SEQ ID NO:13328 | RYSSSWSGGMDV<br>SEQ ID NO:21340 | |
| | | NA | AGCTATGTCATGAGC | GCTATTAGTGGTCGTGGT<br>AGTAACACATTCTACAC<br>AGACTCCGTGAAGGGC | GGGATAACTGGATCACACGG<br>TGCTTTTGATATC | |

FIGURE 49
(Continued)

| | | | | | | |
|---|---|---|---|---|---|---|
| iPS:434057 | 21-225_51B4 | AA | SEQ ID NO:5317<br>SYVMS | SEQ ID NO:13329<br>AISGRGSNTFYTDSVKG | SEQ ID NO:21341<br>GITGSHGAFDI | |
| | | NA | SEQ ID NO:5318<br>AGCTATGGCATGCAC | SEQ ID NO:13330<br>GTTATATGGTATGATGA<br>AAGTAATAAATACTATG<br>CAGACTCCGTGAAGGGC | SEQ ID NO:21342<br>GAACTGGGGATTTCTCTGA<br>CTAC | |
| iPS:434059 | 21-225_51E4 | AA | SEQ ID NO:5319<br>SYGMH | SEQ ID NO:13331<br>VIWYDESNKYYADSVKG | SEQ ID NO:21343<br>ELGFLSDY | |
| | | NA | SEQ ID NO:5320<br>AGCTATGTCATGAGC | SEQ ID NO:13332<br>ACTATGAGTGGTAGTGG<br>TGGTCGCACATACTACG<br>CAGACTCCGTGAAGGGC | SEQ ID NO:21344<br>GTGACTGCTCTTTGACTAC | |
| iPS:434061 | 21-225_51C5 | AA | SEQ ID NO:5321<br>SYVMS | SEQ ID NO:13333<br>TMSGSGGRTYYADSVNG | SEQ ID NO:21345<br>VTAFDY | |
| | | NA | SEQ ID NO:5322<br>AACTATGCCATGACC | SEQ ID NO:13334<br>GTTATTAGTGCTAGTGGT<br>GGTAACTCATTCTACGCA<br>GACTCCGTGAAGGGC | SEQ ID NO:21346<br>GCAAGGGCAGTGGCTGGGTC<br>ACACTGGTTGACCCC | |
| iPS:434063 | 21-225_51C7 | AA | SEQ ID NO:5323<br>NYAMT | SEQ ID NO:13335<br>VISASGGNSFYADSVKG | SEQ ID NO:21347<br>ARAVAGSHWFDP | |
| | | NA | SEQ ID NO:5324<br>AGCTATAGCATGAAC | SEQ ID NO:13336<br>TCCATTAGTAGTAGTAGT<br>AGTTACATATACTACG<br>AGACTCAGTGAAGGGC | SEQ ID NO:21348<br>GCTCGCCTTGACTAC | |
| | 21-225_51G7 | AA | SEQ ID NO:5325<br>SYSMN | SEQ ID NO:13337<br>SISSSSSYIYYADSVKG | SEQ ID NO:21349<br>ARLDY | |
| | | | SEQ ID NO:5326 | SEQ ID NO:13338 | SEQ ID NO:21350 | |

FIGURE 49
(Continued)

| | | | | | |
|---|---|---|---|---|---|
| iPS:434065 | 21-225_50D4 | NA | GGCTACCATATGCAC SEQ ID NO:5327 | TGGATCAACCCTAATAATAATGCCACAAACTATGCTCAGAGCTTTCAGGGC SEQ ID NO:13339 | GACGGTACCAGCAGCTTTGACTTC SEQ ID NO:21351 |
| | | AA | GYHMH SEQ ID NO:5328 | WINPNNNATNYAQSFQG SEQ ID NO:13340 | DGTSSFDF SEQ ID NO:21352 |
| iPS:434067 | 21-225_51H8 | NA | GGCCACTATATGAAC SEQ ID NO:5329 | TGGGTCAACCCTAACAGTGGTGGCTCAAACTCTGCACAGCAGTTTCAGGGC SEQ ID NO:13341 | GGAGGGCAGCTCGGCGGCTTTAACTTCTACTACGGTATGGACGTC SEQ ID NO:21353 |
| | | AA | GHYMN SEQ ID NO:5330 | WVNPNSGGSNSAQQFQG SEQ ID NO:13342 | GGQLGGFNFYYYGMDV SEQ ID NO:21354 |
| iPS:434069 | 21-225_51E9 | NA | GGCTACCATATACAC SEQ ID NO:5331 | TGGATCAACCCTAACACTAATGGCACACAGTATGCACACAGAAGTTTCAGGGC SEQ ID NO:13343 | GATGGCACCTCGTCCTTTGACTAC SEQ ID NO:21355 |
| | | AA | GYHIH SEQ ID NO:5332 | WINPNTNGTQYAQKFQG SEQ ID NO:13344 | DGTSSFDY SEQ ID NO:21356 |
| iPS:434071 | 21-225_51F9 | NA | GACTATGGCATGCAC SEQ ID NO:5333 | GTTATATGGTTGATGGAAATAATAAATACTATGCAGACTCCGTGAAGGGC SEQ ID NO:13345 | GAGCTGGATTCTCTCTGACTAC SEQ ID NO:21357 |
| | | AA | DYGMH SEQ ID NO:5334 | VIWFDGNNKYYADSVKG SEQ ID NO:13346 | ELGFLSDY SEQ ID NO:21358 |
| iPS:434073 | 21-225_51H10 | NA | AGCTATGCCATGAGC SEQ ID NO:5335 | GTTATTAGTGGTAGTGGTGGTACCACATTCTACGCAGACTCCGTGAAGGGC SEQ ID NO:13347 | CGTATAGCAGTGGCTGGGAATGATGCTTTTGATATC SEQ ID NO:21359 |

FIGURE 49
(Continued)

| | | AA | SYAMS | | VISGSGGTTFYADSVKG | | RIAVAGNDAFDI | |
|---|---|---|---|---|---|---|---|---|
| iPS:434075 | | | SEQ ID NO:5336 | | SEQ ID NO:13348 | | SEQ ID NO:21360 | |
| | 21-225_51B11 | NA | GACTATGGCATGCAC | | GTTATATGGTTGGTGGA AATAATAAATACTATG AGACTCCGTGAAGGC | | GAGCTGGGATTTCTCTGA CTAC | |
| | | | SEQ ID NO:5337 | | SEQ ID NO:13349 | | SEQ ID NO:21361 | |
| | | AA | DYGMH | | VIWFGGNNKYYGDSVKG | | ELGFLSDY | |
| iPS:434077 | | | SEQ ID NO:5338 | | SEQ ID NO:13350 | | SEQ ID NO:21362 | |
| | 21-225_51F11 | NA | AACTTGGCATGCAC | | GTTATATGGTATGAGGA AGTAATAAATACTATG CAGACTCCGTGAAGGGC | | GAACTGGGGTTCCTCTGA CTTC | |
| | | | SEQ ID NO:5339 | | SEQ ID NO:13351 | | SEQ ID NO:21363 | |
| | | AA | NFGMH | | VIWYEESNKYYADSVKG | | ELGFLSDF | |
| iPS:434079 | | | SEQ ID NO:5340 | | SEQ ID NO:13352 | | SEQ ID NO:21364 | |
| | 21-225_52B1 | NA | GGCTATCATATGCAG | | TGGATCAACCTAACAG TGGTGCCACAACTATG CACAGAACTTTCAGGGC | | GATGGCAACCTCGTCCTTTGA CTAC | |
| | | | SEQ ID NO:5341 | | SEQ ID NO:13353 | | SEQ ID NO:21365 | |
| | | AA | GYHMQ | | WINPNSGATNYAQNFQG | | DGTSSFDY | |
| iPS:434081 | | | SEQ ID NO:5342 | | SEQ ID NO:13354 | | SEQ ID NO:21366 | |
| | 21-225_52B2 | NA | AACTATGGCATGCAC | | GTTACATGGTTGATGGA AGTAATCAACGCTATGC AGACTCCGTGAAGGGC | | GATCTGGGGATGATGAGGA CTTC | |
| | | | SEQ ID NO:5343 | | SEQ ID NO:13355 | | SEQ ID NO:21367 | |
| | | AA | NYGMH | | VTWFDGSNQRYADSVKG | | DLGMIEDF | |
| | | | SEQ ID NO:5344 | | SEQ ID NO:13356 | | SEQ ID NO:21368 | |

FIGURE 49
(Continued)

| | | | | |
|---|---|---|---|---|
| iPS:434083 | 21-225_52H2 | NA | AGAAATGCCATGAGC SEQ ID NO:5345 | GCTATTAGTGGTCGTGGT GGTAATACATTCTACGC AGACTCCGTGAAGGGC SEQ ID NO:13357 | AATGGGCGAGAGCAGTGGCT TGACTAC SEQ ID NO:21369 |
| | | AA | RNAMS SEQ ID NO:5346 | AISGRGGNTFY ADSVKG SEQ ID NO:13358 | NGREQWLDY SEQ ID NO:21370 |
| iPS:434085 | 21-225_52E3 | NA | AGCTATAAAATGAAC SEQ ID NO:5347 | TCCATTAGTAGTGGTAAT AGTTCCATATACTACGCA GACTCAGTGAAGGGC SEQ ID NO:13359 | GTTAGCAGTAATGACTAC SEQ ID NO:21371 |
| | | AA | SYKMN SEQ ID NO:5348 | SISSGNSSIYY ADSVKG SEQ ID NO:13360 | VSSNDY SEQ ID NO:21372 |
| iPS:434087 | 21-225_52F6 | NA | AGCTATGGCATGCAC SEQ ID NO:5349 | ATTATATCATATGGAGG AAGTAATAAATACTATG CAGACTCCGTGAAGGGC SEQ ID NO:13361 | AGGTCAGCAGCTCGGCCGGG CTACGGTATGGACGTC SEQ ID NO:21373 |
| | | AA | SYGMH SEQ ID NO:5350 | IISYGGSNKYY ADSVKG SEQ ID NO:13362 | RSAARPGYGMDV SEQ ID NO:21374 |
| iPS:434091 | 21-225_52B9 | NA | GACTATGGCATGCAC SEQ ID NO:5351 | GTTATATGGTTTGATGGA AATAATAAATACTATGC AGACTCCGTGAAGGGC SEQ ID NO:13363 | GAGCTGGGATTTCTCTCGA CTAC SEQ ID NO:21375 |
| | | AA | DYGMH SEQ ID NO:5352 | VIWFDGNNKYY ADSVKG SEQ ID NO:13364 | ELGFLSDY SEQ ID NO:21376 |

FIGURE 49
(Continued)

| | | | | |
|---|---|---|---|---|
| iPS:434093 | 21-225_52D10 | NA | AGTTATGGCATGCAC | CTTATATGGTATGATGGAAGTAATAATACCATGCAGACTCCGTGAAGGGC | AGGTATAGCAGCAGCTGGTCGGGCGGGTATGGACGTC |
| | | | SEQ ID NO:5353 | SEQ ID NO:13365 | SEQ ID NO:21377 |
| | | AA | SYGMH | LIWYDGSNKYHADSVKG | RYSSSWSGGMDV |
| | | | SEQ ID NO:5354 | SEQ ID NO:13366 | SEQ ID NO:21378 |
| iPS:434095 | 21-225_52F10 | NA | TTCTATGGCATGCAC | GTTATATGGGACGATGGAAGTAATAAATACTATGCAGACTCCGTGAAGGGC | GATTCTCTGTATAGCAGCAGCTGGTTGTTTGACTAC |
| | | | SEQ ID NO:5355 | SEQ ID NO:13367 | SEQ ID NO:21379 |
| | | AA | FYGMH | VIWDDGSNKYYADSVKG | DSLYSSSWLFDY |
| | | | SEQ ID NO:5356 | SEQ ID NO:13368 | SEQ ID NO:21380 |
| iPS:434097 | 21-225_52H10 | NA | GGCTACCATATGCAG | TGGATCAACCCTAACAATGGTGGCACACAGTATGCACAGAAGTTTCAGGGC | GATGGCACCTCGTCCTTTGACTAC |
| | | | SEQ ID NO:5357 | SEQ ID NO:13369 | SEQ ID NO:21381 |
| | | AA | GYHMQ | WINPNNGGTQYAQKFQG | DGTSSFDY |
| | | | SEQ ID NO:5358 | SEQ ID NO:13370 | SEQ ID NO:21382 |
| iPS:434101 | 21-225_53H12 | NA | AGCTATAGCATGAAC | TCCATTAGTGGTAGTAGTACTTACATATACGCAGACTCAGTGAAGGGC | GTCAACTCCTTTGACTAC |
| | | | SEQ ID NO:5359 | SEQ ID NO:13371 | SEQ ID NO:21383 |
| | | AA | SYSMN | SISGSSTYIYYADSVKG | VNSFDY |
| | | | SEQ ID NO:5360 | SEQ ID NO:13372 | SEQ ID NO:21384 |

FIGURE 49
(Continued)

| | | | | | |
|---|---|---|---|---|---|
| iPS:434103 | 21-225_53G1 | NA | AGCTATAGCATGAAC | TCCATTAGTAGTAGTAGTAGT AGTACATATACTGC AGACTCAGTGAAGGGC | GATCGGGGCAGCAGCACC |
| | | | SEQ ID NO:5361 | SEQ ID NO:13373 | SEQ ID NO:21385 |
| | | AA | SYSMN | SISGSSSYIYYADSVKG | DRGST |
| | | | SEQ ID NO:5362 | SEQ ID NO:13374 | SEQ ID NO:21386 |
| iPS:434105 | 21-225_53D2 | NA | AACTATGGCATGCAC | GTTGTATGGGATGATGG AAGTAATAAATACTATG CAGACTCCGTGAAGGGC | GGCCTTGGCTTTACGGGAGA CTAC |
| | | | SEQ ID NO:5363 | SEQ ID NO:13375 | SEQ ID NO:21387 |
| | | AA | NYGMH | VVWDGSNKYYADSVKG | GLGFTGDY |
| | | | SEQ ID NO:5364 | SEQ ID NO:13376 | SEQ ID NO:21388 |
| iPS:434107 | 21-225_53E2 | NA | AGCTATGCCATGAGC | GCTATTAGTGGTAGTGGT GGTAACACATTCTACGC AGACTCCGTGAAGGGC | AAGGTCGTGGATACAGCCAT GGCTCTTGACTAC |
| | | | SEQ ID NO:5365 | SEQ ID NO:13377 | SEQ ID NO:21389 |
| | | AA | SYAMS | AISGSGGNTFYADSVKG | KVVDTAMALDY |
| | | | SEQ ID NO:5366 | SEQ ID NO:13378 | SEQ ID NO:21390 |
| iPS:434111 | 21-225_53H2 | NA | AGCTATGGCATGCAC | GTTATATCATATGGTGGA AGTAATAAATACCATGC AGACTCCGTGAAGGGC | CGGGGAGCAGCTCGTCTGG CTACGGTATGGACGTC |
| | | | SEQ ID NO:5367 | SEQ ID NO:13379 | SEQ ID NO:21391 |
| | | AA | SYGMH | VISYGGSNKYHADSVKG | RGAARPGYGMDV |
| | | | SEQ ID NO:5368 | SEQ ID NO:13380 | SEQ ID NO:21392 |
| iPS:434115 | 21-225_53E4 | NA | AGCTATGTCATGAGC | GGTATTAGTGGTAGTGG TGGTCGCACATACTACG CAGACTCCGTGAAGGGC | GTGGCCCTTTTTGACTAC |

FIGURE 49
(Continued)

| | | | | | | | | | |
|---|---|---|---|---|---|---|---|---|---|
| iPS:434117 | 21-225_53E4 | AA | SEQ ID NO:5369 | SYVMS | SEQ ID NO:13381 | GISGSGGRTYYADSVKG | SEQ ID NO:21393 | VALFDY | |
| | | NA | SEQ ID NO:5370 | AGCTATGGCATGAAC | SEQ ID NO:13382 | GCTATTAGTGGTAGTGGT GGTGCCACATACTACGC AGACTCCGTGAAGGGC | SEQ ID NO:21394 | CCTCTAGTGGGAGCCCATGA TGCTTTTGAAATC | |
| iPS:434119 | 21-225_53C6 | AA | SEQ ID NO:5371 | SYAMN | SEQ ID NO:13383 | AISGSGGATYYADSVKG | SEQ ID NO:21395 | PLVGAHDAFEI | |
| | | NA | SEQ ID NO:5372 | GACTATGGCATCCAC | SEQ ID NO:13384 | GTTATATGGTATGATGA AAGTAATAAATACTATG GAGACTCCGTGAAGGGC | SEQ ID NO:21396 | GAACTGGGGATGACGTCTGA CTAC | |
| iPS:434121 | 21-225_53E6 | AA | SEQ ID NO:5373 | DYGIH | SEQ ID NO:13385 | VIWYDESNKYYGDSVKG | SEQ ID NO:21397 | ELGMTSDY | |
| | | NA | SEQ ID NO:5374 | AGCTATGGCATGCAC | SEQ ID NO:13386 | GTTATATCATATGGTGGA AGTAATAATACGATGC AGACTCCGTGAAGGGC | SEQ ID NO:21398 | CGACGGGCAGCTCGTCCAGG GTACGGTATGGACGTC | |
| iPS:434123 | 21-225_53F6 | AA | SEQ ID NO:5375 | SYGMH | SEQ ID NO:13387 | VISYGGSNKYDADSVKG | SEQ ID NO:21399 | RRAARPGYGMDV | |
| | | NA | SEQ ID NO:5376 | GGCTACCATATGCAC | SEQ ID NO:13388 | TGGATCAACCTAACAA TAACGGCACAAACTATG CACAGAAGTTTCAGGGC | SEQ ID NO:21400 | GACGGTACCAGCAGCTTTGA CTAC | |
| | 21-225_53F7 | | SEQ ID NO:5377 | | SEQ ID NO:13389 | | SEQ ID NO:21401 | | |

FIGURE 49
(Continued)

| | | | | | | | |
|---|---|---|---|---|---|---|---|
| iPS:434127 | 21-225_53H8 | AA | GYHMH | | WINPNNGTNYAQKFQG | | DGTSSPDY |
| | | | SEQ ID NO:5378 | | SEQ ID NO:13390 | | SEQ ID NO:21402 |
| | | NA | AGCTATGGCATGCAC | | GTTATATGGTATGGATGG AAGTAATAAATACTATG CAGACTCCGTGAAGGGC | | GCCCGTATTGGGTACTTTGA CTCC |
| | | | SEQ ID NO:5379 | | SEQ ID NO:13391 | | SEQ ID NO:21403 |
| iPS:434129 | 21-225_53B12 | AA | SYGMH | | VIWYDGSNKYYADSVKG | | ARIGYFDS |
| | | | SEQ ID NO:5380 | | SEQ ID NO:13392 | | SEQ ID NO:21404 |
| | | NA | AACTTTGGCATGCAC | | GTTGTATGGTATGGATGG AAATAATAGATACTATG CAGACTCCGTGAAGGGC | | GAACTGGGATTCTCTCTGA CTTC |
| | | | SEQ ID NO:5381 | | SEQ ID NO:13393 | | SEQ ID NO:21405 |
| iPS:434131 | 21-225_54D3 | AA | NFGMH | | VVWYDGNNRYYADSVKG | | ELGFLSDF |
| | | | SEQ ID NO:5382 | | SEQ ID NO:13394 | | SEQ ID NO:21406 |
| | | NA | AACTATGGCATGCAC | | GTTACATGGTTTGATGGA AATAACTACTATGC AGACTCCGTGAAGGGC | | GAACTGGGGTTCCTTCTGA TTAT |
| | | | SEQ ID NO:5383 | | SEQ ID NO:13395 | | SEQ ID NO:21407 |
| iPS:434133 | 21_225_54G3 | AA | NYGMH | | VTWFDGNNNYYADSVKG | | ELGFLSDY |
| | | | SEQ ID NO:5384 | | SEQ ID NO:13396 | | SEQ ID NO:21408 |
| | | NA | ACCTATGCCATGAGT | | GCTATTAGTGGTAGTGGT GTTAACACATTCTACGCA GACTCCGTGAAGGGC | | CTGGGGAAGGACTACTACTA CTACGGTATGGACGTC |

FIGURE 49
(Continued)

| | | | | | | |
|---|---|---|---|---|---|---|
| iPS:434135 | 21-225_54G3 | AA | SEQ ID NO:5385 TYAMS | SEQ ID NO:13397 AISGSGVNFYADSVKG | SEQ ID NO:21409 LGKDYYYGMDV | |
| | | NA | SEQ ID NO:5386 AGCTATAGCATGATC | SEQ ID NO:13398 TCCATTAGTGGTACTAGT AGTTACATATACGC AGACTCAGTGAAGGGC | SEQ ID NO:21410 ATGACTACAGTAATT | |
| iPS:434137 | 21-225_54H3 | AA | SEQ ID NO:5387 SYSMI | SEQ ID NO:13399 SISGTSSYIYYADSVKG | SEQ ID NO:21411 MTTVI | |
| | | NA | SEQ ID NO:5388 AGCTATAGCATGCAC | SEQ ID NO:13400 GTTATATGGTATGATGG AAGTAATAAATACTATG CAGACTCCGTGAAGGGC | SEQ ID NO:21412 AGGTATAGCAGCAGCTGGTC GGGCGGTATGGACGTC | |
| | 21-225_54D4 | AA | SEQ ID NO:5389 SYGMH | SEQ ID NO:13401 VIWYDGSNKYYADSVKG | SEQ ID NO:21413 RYSSSWSGGMDV | |
| | | NA | SEQ ID NO:5390 GACTATGGCATCCAC | SEQ ID NO:13402 GTTATATGGTATGATGA AAATAATAAATACTATG CAGACTCCGTGAAGGGC | SEQ ID NO:21414 GAACTGGGGATGACGTCTGA CTAC | |
| iPS:434141 | 21-225_54C6 | AA | SEQ ID NO:5391 DYGIH | SEQ ID NO:13403 VIWYDENNKYYADSVKG | SEQ ID NO:21415 ELGMTSDY | |
| | | NA | SEQ ID NO:5392 AACTATGGCATGCAC | SEQ ID NO:13404 GTTATATGGTATGAGGA AAGTAATAAATACTATG GAGACTCCGTGAAGGGC | SEQ ID NO:21416 GAATTGGGGTTCCTCTCTGA CTAC | |
| iPS:434143 | 21-225_54G7 | | SEQ ID NO:5393 | SEQ ID NO:13405 | SEQ ID NO:21417 | |

FIGURE 49
(Continued)

| | | | | | | | |
|---|---|---|---|---|---|---|---|
| iPS:434145 | 21-225_55B1 | AA | NYGMH | VIWYEESNKYYGDSVKG | ELGFLSDY | | |
| | | | SEQ ID NO:5394 | SEQ ID NO:13406 | SEQ ID NO:21418 | | |
| | | NA | GGCTACTATTTCCAC | TGGATCCACCTAACAATAATGCCACAAACTATGCACAGAAGTTCAGGGC | GATGGCAGATCGTCCTTTGACTAC | | |
| | | | SEQ ID NO:5395 | SEQ ID NO:13407 | SEQ ID NO:21419 | | |
| iPS:434147 | 21-225_55E1 | AA | GYYFH | WIHPNNNATNYAQKFQG | DGRSSFDY | | |
| | | | SEQ ID NO:5396 | SEQ ID NO:13408 | SEQ ID NO:21420 | | |
| | | NA | AGCTATGCCATGAGC | GCTATTAGTAGTGGTCGTGGTAGTAGCACATTCTACGCAGACTCCGTGAAGGGC | GATCACGGTATAGTGGGAACTATTTACTTGACTAC | | |
| | | | SEQ ID NO:5397 | SEQ ID NO:13409 | SEQ ID NO:21421 | | |
| iPS:434149 | 21-225_55H1 | AA | SYAMS | AISGRGSSTFYADSVKG | DHGIVGTIYFDY | | |
| | | | SEQ ID NO:5398 | SEQ ID NO:13410 | SEQ ID NO:21422 | | |
| | | NA | AGCTATGGCATGCAC | GTTATATGGTATGATGGAAGTAATAAATACTATGCAGACTCCGTGAAGGGC | AGGTATAGCAGCAGCTGGTCGGGCGGGTATGGACGTC | | |
| | | | SEQ ID NO:5399 | SEQ ID NO:13411 | SEQ ID NO:21423 | | |
| iPS:434151 | 21-225_55C2 | AA | SYGMH | VIWYDGSNKYYADSVKG | RYSSSWSGGMDV | | |
| | | | SEQ ID NO:5400 | SEQ ID NO:13412 | SEQ ID NO:21424 | | |
| | | NA | AGTTATGGCATGCAC | CTTATATGGTATGATGGAAGTAATAAATACCATGCAGACTCCGTGAAGGGC | AGGTATAGCAGCAGCTGGTCGGGGGTATGGACGTC | | |
| | | | SEQ ID NO:5401 | SEQ ID NO:13413 | SEQ ID NO:21425 | | |
| | | AA | SYGMH | LIWYDGSNKYHADSVKG | RYSSSWSGGMDV | | |

FIGURE 49
(Continued)

| | | | | | | | |
|---|---|---|---|---|---|---|---|
| iPS:434155 | 21-225_55B3 | NA | SEQ ID NO:5402 AGCTATGGCATGCAC | SEQ ID NO:13414 GTTATATGGTTTGATGGAAATAATAAATACTATGAAGACTCCGTGAAGGGC | SEQ ID NO:21426 GAACTGGGATTTCTCTCTGACTAC |
| | | AA | SEQ ID NO:5403 SYGMH | SEQ ID NO:13415 VIWFDGNNKYYEDSVKG | SEQ ID NO:21427 ELGFLSDY |
| iPS:434157 | 21-225_55D4 | NA | SEQ ID NO:5404 AGTTATATGGGATGAAC | SEQ ID NO:13416 TCCATTAGTAGTAGTAGTAATCACATAGACTACGCAGACTCAGTGAAGGGC | SEQ ID NO:21428 GGGACTGACTAC |
| | | AA | SEQ ID NO:5405 SYRMN | SEQ ID NO:13417 SISSSSNHIDYADSVKG | SEQ ID NO:21429 GTDY |
| iPS:434159 | 21-225_55B8 | NA | SEQ ID NO:5406 GACTATGGCATGCAC | SEQ ID NO:13418 GTTATATGGTATGATGAAAATAATAAATACTATGCAGACTCCGTGAAGGGC | SEQ ID NO:21430 GAATGGTTTGACTAC |
| | | AA | SEQ ID NO:5407 DYGMH | SEQ ID NO:13419 VIWYDENNKYYADSVKG | SEQ ID NO:21431 EWFDY |
| iPS:434161 | 21-225_55F9 | NA | SEQ ID NO:5408 AGCTATGGCATGCAC | SEQ ID NO:13420 GTTATATGGTATGATGGAAATGGCAAATATTATGCAGACTCCGTGAAGGGC | SEQ ID NO:21432 AGGTATAGCAGCAGCTGGTCGGGCGGTATGGGACGTC |
| | | AA | SEQ ID NO:5409 SYGMH | SEQ ID NO:13421 VIWYDGNGKYYADSVKG | SEQ ID NO:21433 RYSSSWSGGMDV |
| | | | SEQ ID NO:5410 | SEQ ID NO:13422 | SEQ ID NO:21434 |

FIGURE 49
(Continued)

| | | | | |
|---|---|---|---|---|
| iPS:434163 | 21-225_50H1 | NA | AGCTATGGCATGCAC | ATTATATCATATGGTGGAAGTAATAAATACGATGCAGACTCCGTGAAGGGC | CGACGGGCAGCTCGTCCAGGGTACGGTATGGACGTC |
| | | | SEQ ID NO:5411 | SEQ ID NO:13423 | SEQ ID NO:21435 |
| | | AA | SYGMH | IISYGGSNKYDADSVKG | RRAARPGYGMDV |
| | | | SEQ ID NO:5412 | SEQ ID NO:13424 | SEQ ID NO:21436 |
| iPS:434165 | 21-225_50F2 | NA | AGCTATGGCATGCAC | GTTATATGGCATGATGGAAGTAATAAATACTATGCAGACTCCGTGAAGGGC | GACGAGCAGCTCGGACCTTTGACTAC |
| | | | SEQ ID NO:5413 | SEQ ID NO:13425 | SEQ ID NO:21437 |
| | | AA | SYGMH | VIWHDGSNKYYADSVKG | DEQLGTFDY |
| | | | SEQ ID NO:5414 | SEQ ID NO:13426 | SEQ ID NO:21438 |
| iPS:434167 | 21-225_50F3 | NA | ACCTATGCCATGACC | GCTATCAGTGGTAGTGGTGTTAACTCATTCTACGCAGACTCCGTGAAGGGC | GCAAGGGCAGTGGCTGGGTCACACTGGTTCGACCCC |
| | | | SEQ ID NO:5415 | SEQ ID NO:13427 | SEQ ID NO:21439 |
| | | AA | TYAMT | AISGSGVNSFYADSVKG | ARAVAGSHWFDP |
| | | | SEQ ID NO:5416 | SEQ ID NO:13428 | SEQ ID NO:21440 |
| iPS:434169 | 21-225_50C4 | NA | GACTATGGCATGCAC | GTTATATGGTATGAAGAAACTAATAAATACTATGCAGACTCCGTGAAGGGC | GAAGTGGGGTTCCTGAATGACTAC |
| | | | SEQ ID NO:5417 | SEQ ID NO:13429 | SEQ ID NO:21441 |
| | | AA | DYGMH | VIWYEETNKYYADSVKG | EVGFLNDY |
| | | | SEQ ID NO:5418 | SEQ ID NO:13430 | SEQ ID NO:21442 |

FIGURE 49
(Continued)

| | | | | | | |
|---|---|---|---|---|---|---|
| iPS:434171 | 21-225_50G4 | NA | AGTTACTATATACAC | | GTAATCAACCCTAGTAATGGTAGAACAAGCTACGCACAGAAGTTCCAGGGC | | GATCGAGGAGATGGTTACTACTTCTACTACGGTATGGACGTC |
| | | | SEQ ID NO:5419 | | SEQ ID NO:13431 | | SEQ ID NO:21443 |
| | | AA | SYYIH | | VINPSNGRTSYAQKFQG | | DRGDGYYFYYGMDV |
| | | | SEQ ID NO:5420 | | SEQ ID NO:13432 | | SEQ ID NO:21444 |
| iPS:434175 | 21-225_55A11 | NA | AGCTATGGCATGCAC | | GTTATATCATATGTTGGAAGTACTAAATACTATGCAGACTCCGTGAGGGC | | GGGAGAGGTCGATATAGTGACTACGGTCATGATGCTTTTGATATC |
| | | | SEQ ID NO:5421 | | SEQ ID NO:13433 | | SEQ ID NO:21445 |
| | | AA | SYGMH | | VISYVGSTKYYADSVRG | | GRGRYSDYGHDAFDI |
| | | | SEQ ID NO:5422 | | SEQ ID NO:13434 | | SEQ ID NO:21446 |
| iPS:434177 | 21-225_56A1 | NA | AATTATGATATCAAC | | TGGATGCACCCTAACAGTGGTAACACAGGCTATGCACAGAAGTTCCAGGGC | | AGCAGTGGCTGGTACGTTTTTGACTAC |
| | | | SEQ ID NO:5423 | | SEQ ID NO:13435 | | SEQ ID NO:21447 |
| | | AA | NYDIN | | WMHPNSGNTGYAQKFQG | | SSGWYVFDY |
| | | | SEQ ID NO:5424 | | SEQ ID NO:13436 | | SEQ ID NO:21448 |
| iPS:434179 | 21-225_56F1 | NA | AGCTATAGCATGAAC | | TCCATTAGTAGTAGTAGTAGTACTTACATATACGGAGACTCAGTGAAGGGC | | GATCGGGGCCAGCAGC |
| | | | SEQ ID NO:5425 | | SEQ ID NO:13437 | | SEQ ID NO:21449 |
| | | AA | SYSMN | | SISSSSTYIYYGDSVKG | | DRGSS |
| | | | SEQ ID NO:5426 | | SEQ ID NO:13438 | | SEQ ID NO:21450 |
| iPS:434181 | 21-225_56B2 | NA | AGCTATGCCATGAGC | | GCTATTAGTGGTAGTGGTAACACATTCTACGCAGACTCCGTGAAGGGC | | AAGGTCGTGGATACAGCCATGGCTCTTGACTAC |
| | | | SEQ ID NO:5427 | | SEQ ID NO:13439 | | SEQ ID NO:21451 |
| | | AA | SYAMS | | AISGSGGNTFYADSVKG | | KVVDTAMALDY |

FIGURE 49
(Continued)

| | | | | | |
|---|---|---|---|---|---|
| iPS:434187 | 21-225_56A5 | NA | SEQ ID NO:5428 AGCTATAGCATGAAC | SEQ ID NO:13440 TCCATTAGTGGTAGTAGTAGTTACATATACTACGCAGACTCAGTGAAGGC | SEQ ID NO:21452 GTGGCTACTTTTGACTAC |
| | | AA | SEQ ID NO:5429 SYSMN | SEQ ID NO:13441 SISGSSSYIYYADSVKG | SEQ ID NO:21453 VATFDY |
| iPS:434189 | 21-225_56E5 | NA | SEQ ID NO:5430 GGCTACCATATGCAC | SEQ ID NO:13442 TGGATCAACCCTAACAATAATGCCACAAACTATGCACAGAAGTTTCAGGGC | SEQ ID NO:21454 GATGGCACCTCGTCTTTGACTAC |
| | | AA | SEQ ID NO:5431 GYHMH | SEQ ID NO:13443 WINPNNNATNYAQKFQG | SEQ ID NO:21455 DGTSSFDY |
| iPS:434191 | 21-225_56B6 | NA | SEQ ID NO:5432 AGCTATGGCATGCAC | SEQ ID NO:13444 GTTATATGGCATGATGGAAGTAATAAATATTATGTAGACTCCGTGAAGGGC | SEQ ID NO:21456 GACGAGCAGCTCGGGACCTTTGACTAC |
| | | AA | SEQ ID NO:5433 SYGMH | SEQ ID NO:13445 VIWHDGSNKYYVDSVKG | SEQ ID NO:21457 DEQLGTFDY |
| iPS:434193 | 21-225_56C6 | NA | SEQ ID NO:5434 GACTACCATATGCAC | SEQ ID NO:13446 TGGATCAACCCTAACAGAGGTGGCACAAATTATGTACAGAAGTTTCAGGGT | SEQ ID NO:21458 GATGGCACCTCGTCTTTGACTAT |
| | | AA | SEQ ID NO:5435 DYHMH | SEQ ID NO:13447 WINPNRGGTNYVQKFQG | SEQ ID NO:21459 DGTSSFDY |
| | | | SEQ ID NO:5436 | SEQ ID NO:13448 | SEQ ID NO:21460 |

FIGURE 49
(Continued)

| | | | | GACTACTATATGCAC | TGGATCAACCCTAACAG<br>TGGTGGCACAAACTATG<br>CACAGAGGTTTCAGGGC | GAGGGAGCAACTCGTCCGAC<br>GGGTTTTGACTAC |
|---|---|---|---|---|---|---|
| iPS:434195 | 21-225_56F6 | NA | | SEQ ID NO:5437 | SEQ ID NO:13449 | SEQ ID NO:21461 |
| | | AA | | DYYMH | WINPNSGGTNYAQRFQG | EGATRPFGFDY |
| | | NA | | SEQ ID NO:5438<br>GGCCACTATATAAAC | SEQ ID NO:13450<br>TGGGTCAACCCTAACAG<br>TGGTGGCACAAACTCTG<br>CACAGAAGTTTCAGGGC | SEQ ID NO:21462<br>GGAGGGCAGCTCGGCGGGTT<br>TAACTACTACTACTACGGTA<br>TGGACGTC |
| iPS:434197 | 21-225_56C7 | AA | | SEQ ID NO:5439<br>GHYIN | SEQ ID NO:13451<br>WVNPNSGGTNSAQKFQG | SEQ ID NO:21463<br>GGQLGGFNYYYYGMDV |
| | | NA | | SEQ ID NO:5440<br>AACTATGGCATGCAC | SEQ ID NO:13452<br>GTTATATGGTATGATGA<br>AAGTAATAAACACTATG<br>CAGACTCCGTGAAGGGC | SEQ ID NO:21464<br>GAACTGGGGGATGAACGGAG<br>ACTAC |
| iPS:434199 | 21-225_59F11 | AA | | SEQ ID NO:5441<br>NYGMH | SEQ ID NO:13453<br>VIWYDESNKHYADSVKG | SEQ ID NO:21465<br>ELGMNGDY |
| | | NA | | SEQ ID NO:5442<br>AGCTATGGCATGCAC | SEQ ID NO:13454<br>GTTATATGGTATGATGG<br>AAGTAATAAATACTATG<br>CAGACTCCGTGAAGGGC | SEQ ID NO:21466<br>CGGTATAGCAGCAGCTGGGA<br>CGGGGGTATGGACGTC |
| iPS:434201 | 21-225_59A12 | AA | | SEQ ID NO:5443<br>SYGMH | SEQ ID NO:13455<br>VIWYDGSNKYADSVKG | SEQ ID NO:21467<br>RYSSSWDGGMDV |
| | | | | SEQ ID NO:5444 | SEQ ID NO:13456 | SEQ ID NO:21468 |

FIGURE 49
(Continued)

| | | | | | |
|---|---|---|---|---|---|
| iPS:434203 | 21-225_60E2 | NA | GACTATGGCATGCAC | ATTATATGGTATGATGA AATAATAAATACTATG CAGACTCCGTGAAGGGC | GATGTTCTGGACCCTTTTGA CTAC |
| | | | SEQ ID NO:5445 | SEQ ID NO:13457 | SEQ ID NO:21469 |
| | | AA | DYGMH | IIWYDENNKYYADSVKG | DVLDPFDY |
| | | | SEQ ID NO:5446 | SEQ ID NO:13458 | SEQ ID NO:21470 |
| iPS:434205 | 21-225_60G2 | NA | AGTTATGGCATGCAC | GTTATATGGTATGATGG AAGTAATAAATACTATG CAGACTCCGTGAAGGGC | AGGTATAGCAGAAGCTGGAC GGGAGGCATGGACGTC |
| | | | SEQ ID NO:5447 | SEQ ID NO:13459 | SEQ ID NO:21471 |
| | | AA | SYGMH | VIWYDGSNKYYADSVKG | RYSRSWTGGMDV |
| | | | SEQ ID NO:5448 | SEQ ID NO:13460 | SEQ ID NO:21472 |
| iPS:434207 | 21-225_60A3 | NA | AGTTATGGCATGCAC | GTTATATGGTATGAAGA AAGTAATAAATACTATG CAGACTCCGTGAAGGGC | GAACTGGGGATGACCGGAGA CTAC |
| | | | SEQ ID NO:5449 | SEQ ID NO:13461 | SEQ ID NO:21473 |
| | | AA | SYGMH | VIWYEESNKYYADSVKG | ELGMTGDY |
| | | | SEQ ID NO:5450 | SEQ ID NO:13462 | SEQ ID NO:21474 |
| iPS:434209 | 21-225_60C3 | NA | GGCCACTATATACAC | TGGATCAACCCTAACAG CGGTGGCACAAACTATG TACAGAAATTTCAGGGC | GGGGGCCTACTGGGAGTAC CAACTACTATTATTACGGTA TGGACGTC |
| | | | SEQ ID NO:5451 | SEQ ID NO:13463 | SEQ ID NO:21475 |
| | | AA | GHYIH | WINPNSGGTNYVQKFQG | GGLLGATNYYYYGMDV |
| | | | SEQ ID NO:5452 | SEQ ID NO:13464 | SEQ ID NO:21476 |

FIGURE 49
(Continued)

| | | | | | |
|---|---|---|---|---|---|
| iPS:434211 | 21-225_60F3 | NA | AATTATGATATCAAC SEQ ID NO:5453 | TGGATGCACCCTAACAG TGGTAACACAGGCTATG CACAGAAGTTCCAGGGC SEQ ID NO:13465 | AGCAGTGGCTGGTACTTCTT TGACTAC SEQ ID NO:21477 |
| | | AA | NYDIN SEQ ID NO:5454 | WMHPNSGNTGYAQKFQG SEQ ID NO:13466 | SSGWYFFDY SEQ ID NO:21478 |
| iPS:434213 | 21-225_60A4 | NA | AGCTATGTCATGAGC SEQ ID NO:5455 | TCTATTAGTGGTAGTGGT GGTGGACAAACTACGC AGACTCCGTGAAGGGC SEQ ID NO:13467 | CTAACTGGATTTGACTAT SEQ ID NO:21479 |
| | | AA | SYVMS SEQ ID NO:5456 | SISGSGGWTNYADSVKG SEQ ID NO:13468 | LTGFDY SEQ ID NO:21480 |
| iPS:434215 | 21-225_60F7 | NA | AGCTATGTCATGAGC SEQ ID NO:5457 | GGTATTAGTGGTAGTGG TAATAGAACATACTACG CAGACTCCGTGAAGGGC SEQ ID NO:13469 | TTGGGGATTGAC SEQ ID NO:21481 |
| | | AA | SYVMS SEQ ID NO:5458 | GISGSGNRTYYADSVKG SEQ ID NO:13470 | LGID SEQ ID NO:21482 |
| iPS:434217 | 21-225_60E8 | NA | AGGAGTAGTTACTACTGGGG C SEQ ID NO:5459 | AGTATCTATTATAGTGGG AGGGCCTCCTACAACCC GTCCCTCAAGAGT SEQ ID NO:13471 | CTGGACAGTGGCTGGTCGTT TGACTAC SEQ ID NO:21483 |
| | | AA | RSSYYWG SEQ ID NO:5460 | SIYYSGSASYNPSLKS SEQ ID NO:13472 | LDSGWSFDY SEQ ID NO:21484 |
| iPS:434219 | 21-225_60E9 | NA | AGCTATGCCATGAGC SEQ ID NO:5461 | GCTATTAGTGGTAGTGGT GGTAACACATTCTACGC AGACTCCGTGAAGGGC SEQ ID NO:13473 | TTTTTCGTATAGTGGGAGC CGGGTACTTTGACTAC SEQ ID NO:21485 |

FIGURE 49
(Continued)

| | | | | | | |
|---|---|---|---|---|---|---|
| iPS:434221 | 21-225_60A11 | AA | SYAMS | | AISGSGGNTFYADSVKG | FFGIVGAGYFDY |
| | | | SEQ ID NO:5462 | | SEQ ID NO:13474 | SEQ ID NO:21486 |
| | | NA | AACTATGCCATGACC | | GCTATTAGTGGTAGTGGT GGTAACACATTCTACGC AGACTCCGTGACGGGC | CTGGGGAAGGACTACCACTA CTACGGTATGGACGTC |
| | | | SEQ ID NO:5463 | | SEQ ID NO:13475 | SEQ ID NO:21487 |
| iPS:434223 | 21-225_60C12 | AA | NYAMT | | AISGSGGNTFYADSVTG | LGKDYHYYGMDV |
| | | | SEQ ID NO:5464 | | SEQ ID NO:13476 | SEQ ID NO:21488 |
| | | NA | AGCTATGGCATGCAC | | GTTATATGGTATGATGG AAGTAATAAATACTATG TAGACTCCGTGAAGGGC | AGGTATAGCAGAAGCTGGAC GGGAGGTATGGACGTC |
| | | | SEQ ID NO:5465 | | SEQ ID NO:13477 | SEQ ID NO:21489 |
| iPS:434225 | 21-225_60E12 | AA | SYGMH | | VIWYDGSNKYYVDSVKG | RYSRSWTGGMDV |
| | | | SEQ ID NO:5466 | | SEQ ID NO:13478 | SEQ ID NO:21490 |
| | | NA | AGTTACTTCTGGAGC | | CGCATCTATACCAGGGG GAGCACCAACTACAACC CCTCCCTCAAGAGT | GAGGGAAAAACTGGGGGGG TTTCTTACTTTGACTAC |
| | | | SEQ ID NO:5467 | | SEQ ID NO:13479 | SEQ ID NO:21491 |
| iPS:434227 | 21-225_61A1 | AA | SYFWS | | RIYTRGSTNYNPSLKS | EGKTGGVSYFDY |
| | | | SEQ ID NO:5468 | | SEQ ID NO:13480 | SEQ ID NO:21492 |
| | | NA | AGTCACTTCTGGAGC | | CGCATCTATATCAGGGG GAGCACCAACTACAACC CCTCCCTCAAGAGT | GAGGGAAAAACTGGGGGGG TTTCTTACTTTGACTAC |
| | | | SEQ ID NO:5469 | | SEQ ID NO:13481 | SEQ ID NO:21493 |
| | | AA | SHFWS | | RIYIRGSTNYNPSLKS | EGKTGGVSYFDY |
| | | | SEQ ID NO:5470 | | SEQ ID NO:13482 | SEQ ID NO:21494 |

FIGURE 49
(Continued)

| | | | | | | |
|---|---|---|---|---|---|---|
| iPS:434229 | 21-225_61H1 | NA | GACTATGGCATGCAC SEQ ID NO:5471 | ATTATATGGTATGATGA AGTAATAAATACTATG CAGACTCCGTGAAGGGC SEQ ID NO:13483 | GATGTTCTGGACCCTTTTGA CTAC SEQ ID NO:21495 |
| | | AA | DYGMH SEQ ID NO:5472 | IIWYDESNKYYADSVKG SEQ ID NO:13484 | DVLDPFDY SEQ ID NO:21496 |
| iPS:434231 | 21-225_61F2 | NA | AGCTATGGCATGCAC SEQ ID NO:5473 | GTTATATGGTATGATGG AATAATAAATACTATG CAGACTCCGTGAAGGGC SEQ ID NO:13485 | GAGAGGTATAGCAGTGGCTG GTACGACTACGGTATGGACG TC SEQ ID NO:21497 |
| | | AA | SYGMH SEQ ID NO:5474 | VIWYDGSNKYYADSVKG SEQ ID NO:13486 | ERYSSGWYDYGMDV SEQ ID NO:21498 |
| iPS:434233 | 21-225_61B3 | NA | AGCTATGGCATGCAC SEQ ID NO:5475 | GTTATATGGTATGATGG AATAATAAATACTATG CAGACTCCGTGAAGGGC SEQ ID NO:13487 | AGGTATAGCAGAAGCTGGGC GGGAGGCATGGACGTC SEQ ID NO:21499 |
| | | AA | SYGMH SEQ ID NO:5476 | VIWYDGSNKYYADSVKG SEQ ID NO:13488 | RYSRSWAGGMDV SEQ ID NO:21500 |
| iPS:434235 | 21-225_61E3 | NA | AATTATATGATATCAAC SEQ ID NO:5477 | TGGATGACCCCTAACAG TGGTAACACAGGCTATG CACAGAAGTTCCAGGGC SEQ ID NO:13489 | AGCAGTGGCTGGTACCGCTT TGACTAC SEQ ID NO:21501 |
| | | AA | NYDIN SEQ ID NO:5478 | WMTPNSGNTGYAQKFQG SEQ ID NO:13490 | SSGWYRFDY SEQ ID NO:21502 |

FIGURE 49
(Continued)

| | | | | | |
|---|---|---|---|---|---|
| iPS:434237 | 21-225_61B5 | NA | AATTATGATATCAAC<br>SEQ ID NO:5479 | TGGATGCACCCTAACAG<br>TGGTAGCACAGGCTATG<br>CACAGAAGTTCCAGGGC<br>SEQ ID NO:13491 | AGCAGTGGCTGGTACTACTT<br>TGACTAC<br>SEQ ID NO:21503 |
| | | AA | NYDIN<br>SEQ ID NO:5480 | WMHPNSGSTGYAQKFQG<br>SEQ ID NO:13492 | SSGWYYFDY<br>SEQ ID NO:21504 |
| iPS:434239 | 21-225_58F1 | NA | AGCTATGCCATGAGT<br>SEQ ID NO:5481 | GCTATTAGTACTGGTGGT<br>GGTAACACATACTACGC<br>AGACTCCGTGAAGGGC<br>SEQ ID NO:13493 | CGGGGGGTCTACGGTGACTT<br>TGATGCTTTTGATATC<br>SEQ ID NO:21505 |
| | | AA | SYAMS<br>SEQ ID NO:5482 | AISTGGNTYYADSVKG<br>SEQ ID NO:13494 | RGVYGDFDAFDI<br>SEQ ID NO:21506 |
| iPS:434241 | 21-225_61E6 | NA | AGCTATGCCATGAGC<br>SEQ ID NO:5483 | GCTACTAGTGGTAGTGG<br>TGTTAACACATTCTACGC<br>AGACTCCGTGAAGGGC<br>SEQ ID NO:13495 | TTGGAACTGGGGATCTTTGA<br>CTAC<br>SEQ ID NO:21507 |
| | | AA | SYAMS<br>SEQ ID NO:5484 | ATSGSGVNTFYADSVKG<br>SEQ ID NO:13496 | LELGIFDY<br>SEQ ID NO:21508 |
| iPS:434243 | 21-225_62C1 | NA | AGCTATAGCATGAAC<br>SEQ ID NO:5485 | TCCATTAGTAGTAGTAGT<br>AGTTACATATACTACGC<br>AGACTCAGTGAAGGGC<br>SEQ ID NO:13497 | TTTGGAGTGGAC<br>SEQ ID NO:21509 |
| | | AA | SYSMN<br>SEQ ID NO:5486 | SISSSSSYIYYADSVKG<br>SEQ ID NO:13498 | FGVD<br>SEQ ID NO:21510 |
| iPS:434245 | 21-225_62H1 | NA | AGCTATGGCATGCAC<br>SEQ ID NO:5487 | ATTATATGGTATGATGG<br>AAGTAATAAATACTATG<br>CAGACTCCGTGAAGGGC<br>SEQ ID NO:13499 | GAAGACCCGGTACCAGCTG<br>CTCTGACTAC<br>SEQ ID NO:21511 |

FIGURE 49
(Continued)

| | | | | | | |
|---|---|---|---|---|---|---|
| iPS:434247 | 21-225_62D2 | AA | SYGMH | | IIWYDGSNKYYADSVKG | EDPRTSCSDY |
| | | | SEQ ID NO:5488 | | SEQ ID NO:13500 | SEQ ID NO:21512 |
| | | NA | AGCTATGGCATGCAC | | GTTATATGGTATGATGG AAGTAATAAATACTCTG CAGACTCCGTGAAGGGC | GATAATGGTAACTGGAACTA CCTTGACTAC |
| | | | SEQ ID NO:5489 | | SEQ ID NO:13501 | SEQ ID NO:21513 |
| iPS:434249 | 21-225_62E2 | AA | SYGMH | | VIWYDGSNKYSADSVKG | DNGNWNYLDY |
| | | | SEQ ID NO:5490 | | SEQ ID NO:13502 | SEQ ID NO:21514 |
| | | NA | AGAAGTAGTTACTACTGGGG C | | AGCATCTATTATAGTGG GATCGCCTCCTATAATCC GTCCCTCAAGAGT | CTGAGCAGTGGCTGGTCCTT TGACTAC |
| | | | SEQ ID NO:5491 | | SEQ ID NO:13503 | SEQ ID NO:21515 |
| iPS:434251 | 21-225_62G3 | AA | RSSYYWG | | SIYYSGIASYNPSLKS | LSSGWSFDY |
| | | | SEQ ID NO:5492 | | SEQ ID NO:13504 | SEQ ID NO:21516 |
| | | NA | AGCTATAGCATGAAC | | TCCATTAGTAGTAGTAGT AGTTACATATACGC AGACTCAGTGAAGGGC | GTTAACTCTTTTGACTCC |
| | | | SEQ ID NO:5493 | | SEQ ID NO:13505 | SEQ ID NO:21517 |
| iPS:434253 | 21-225_62E4 | AA | SYSMN | | SISSSSSYIYYADSVKG | VNSFDS |
| | | | SEQ ID NO:5494 | | SEQ ID NO:13506 | SEQ ID NO:21518 |
| | | NA | GACTATGGCATGCAC | | GTTATATGGTATGATGG AAGTAATAAATACTATG CAGACTCCGTGAAGGGC | GAGCTTGGGTTCAGCAGTGA CTAC |
| | | | SEQ ID NO:5495 | | SEQ ID NO:13507 | SEQ ID NO:21519 |
| | | AA | DYGMH | | VIWYDRSNKYYADSVKG | ELGFSSDY |
| | | | SEQ ID NO:5496 | | SEQ ID NO:13508 | SEQ ID NO:21520 |

FIGURE 49
(Continued)

| | | | | |
|---|---|---|---|---|
| iPS:434255 | 21-225_62E6 | NA | TCCTATGGCATGCAC | GCTATATGGTATGATGG AAGTAATAAATACTATG GAGACTCCGTGAAGGGC | GATCAGGGCATAGTGGGAGC TACTTGGTTTGACTAC |
| | | | SEQ ID NO:5497 | SEQ ID NO:13509 | SEQ ID NO:21521 |
| | | AA | SYGMH | AIWYDGSNKYYGDSVKG | DQGIVGATWFDY |
| | | | SEQ ID NO:5498 | SEQ ID NO:13510 | SEQ ID NO:21522 |
| iPS:434257 | 21-225_62F7 | NA | AGCTATGTTATGAGC | GGTATTAGTGGTAGTGG TGCTAAACATACTATG CAGACTCCGTGAAGGGC | CTGGGGATAGACTACTACTA CGGTATGGACGTC |
| | | | SEQ ID NO:5499 | SEQ ID NO:13511 | SEQ ID NO:21523 |
| | | AA | SYVMS | GISGSGAKTYYADSVKG | LGIDYYYGMDV |
| | | | SEQ ID NO:5500 | SEQ ID NO:13512 | SEQ ID NO:21524 |
| iPS:434259 | 21-225_62G7 | NA | GGCTACTATATGCAC | TGGATCAAACCTAAAAG TGGTGGCACAAACCAAG CACAGAAGTTTCAGGGC | GCTCCGGGTATAGCAGCAGC TGGTACATGGGGATACTTTG ACTAC |
| | | | SEQ ID NO:5501 | SEQ ID NO:13513 | SEQ ID NO:21525 |
| | | AA | GYYMH | WIKPKSGGTNQAQKFQG | APGIAAAGTWGYFDY |
| | | | SEQ ID NO:5502 | SEQ ID NO:13514 | SEQ ID NO:21526 |
| iPS:434261 | 21-225_56F7 | NA | AGCTATGTCTTAAAC | GCTATGAGTGGTAGTGG TGGTAGAACATACTACG CAGACTCCGTGAAGGGC | ACTACGCACTTTGACTAC |
| | | | SEQ ID NO:5503 | SEQ ID NO:13515 | SEQ ID NO:21527 |
| | | AA | SYVLN | AMSGSGGRTYYADSVKG | TTHFDY |
| | | | SEQ ID NO:5504 | SEQ ID NO:13516 | SEQ ID NO:21528 |
| iPS:434263 | 21_225_56H7 | NA | AGCTATAGCATGAAC | TCCATTAGTAGTAGTAGT ACTTACATATACTACGG AGACTCAGTGAAGGGC | GATCGGGGCAGCAGC |

FIGURE 49
(Continued)

| | | | | | | |
|---|---|---|---|---|---|---|
| iPS:434265 | 21-225_56H7 | AA | SEQ ID NO:5505 SYSMN | SEQ ID NO:13517 SISSSSTYIYGDSVKG | SEQ ID NO:21529 DRGSS | |
| | | NA | SEQ ID NO:5506 AGCTATAGCATGAAC | SEQ ID NO:13518 TCCATTAGTGGTAGTAGT AGTTACATAAACTACAC AGACTCAGTGAAGGGC | SEQ ID NO:21530 GTGGCTGGCTTTGACTAC | |
| iPS:434267 | 21-225_57B2 | AA | SEQ ID NO:5507 SYSMN | SEQ ID NO:13519 SISGSSSYINYTDSVKG | SEQ ID NO:21531 VAGFDY | |
| | | NA | SEQ ID NO:5508 AGTTACTACTGGAGC | SEQ ID NO:13520 CGCATCTATACCAGGGG GAGCACCAACTACAACC CCTCCCTCAAGAGT | SEQ ID NO:21532 GAGGGAAAAACTGGGGGGG TTTCTTACTTTGACTAC | |
| iPS:434269 | 21-225_57F2 | AA | SEQ ID NO:5509 SYYWS | SEQ ID NO:13521 RIYTRGSTNYNPSLKS | SEQ ID NO:21533 EGKTGGVSYFDY | |
| | | NA | SEQ ID NO:5510 AGCTATGGCATGCAC | SEQ ID NO:13522 GCTATATGGTATGATGG AAGTAATAAATACTATG CAGACTCCGTGAAGGGC | SEQ ID NO:21534 GATTATGGTATAGTGGGAGC TACATATTTGACTAC | |
| iPS:434269 | 21-225_57H3 | AA | SEQ ID NO:5511 SYGMH | SEQ ID NO:13523 AIWYDGSNKYYADSVKG | SEQ ID NO:21535 DYGIVGATYFDY | |
| | | NA | SEQ ID NO:5512 GACTATGGCATGCAC | SEQ ID NO:13524 GTTATATGGTATGCTGGA AGTAATAAATACTATGT AGACTCCGTGAAGGGC | SEQ ID NO:21536 GAACTGGGGATGAGGTCTGA CTAC | |
| iPS:434271 | 21-225_57A4 | AA | SEQ ID NO:5513 DYGMH | SEQ ID NO:13525 VIWYAGSNKYYVDSVKG | SEQ ID NO:21537 ELGMRSDY | |

FIGURE 49
(Continued)

| | | | | | |
|---|---|---|---|---|---|
| iPS:434273 | 21-225_57E4 | NA | SEQ ID NO:5514 AGCTATGCCATGAGC | SEQ ID NO:13526 GTTATTAGTGGTAGTGGT GGTAGTACATTCTACGC AGACTCCGTGAAGGGC | SEQ ID NO:21538 AGGGACTGGAACGACGTTTT TGACTAC |
| | | AA | SEQ ID NO:5515 SYAMS | SEQ ID NO:13527 VISGSGGSTFYADSVKG | SEQ ID NO:21539 RDWNDVFDY |
| iPS:434275 | 21-225_57F4 | NA | SEQ ID NO:5516 GACTACTACATGAAC | SEQ ID NO:13528 TACATTAGTAGTAGTGGT AGTACCATATACTACGC AGACTCTGTGAAGGGC | SEQ ID NO:21540 GATATGATTACG |
| | | AA | SEQ ID NO:5517 DYYMN | SEQ ID NO:13529 YISSSGSTIYYADSVKG | SEQ ID NO:21541 DMIT |
| iPS:434277 | 21-225_57A7 | NA | SEQ ID NO:5518 GGCTACCATATACAC | SEQ ID NO:13530 TGGATCAACCTAACAA TAATGGCACAAACTATG CACAGAAGTTCAGGGC | SEQ ID NO:21542 GATGGGAGAAGTGGTTTTGA CTAC |
| | | AA | SEQ ID NO:5519 GYHIH | SEQ ID NO:13531 WINPNNNGTNYAQKFQG | SEQ ID NO:21543 DGRSGFDY |
| iPS:434279 | 21-225_57F7 | NA | SEQ ID NO:5520 AGCTATGCCATGAGC | SEQ ID NO:13532 GCTATTAGTGGTAGTGGT GGTAACACATTCTACGC AGACTCCGTGAAGGGC | SEQ ID NO:21544 TTTTTCGGTGTAGTGGAGT CGGGTGCTTTGACTAC |
| | | AA | SEQ ID NO:5521 SYAMS | SEQ ID NO:13533 AISGSGGNTFYADSVKG | SEQ ID NO:21545 FFGVVGVGCFDY |
| iPS:434281 | 21-225_57B8 | NA | SEQ ID NO:5522 AGCTATGCCATGAGC | SEQ ID NO:13534 GCTATTAGTGGTAGTGGT GGTAACACATTCTACGC AGACTCCGTGAAGGGC | SEQ ID NO:21546 TTGGAACTGGGGATCTTTGA CTAC |

FIGURE 49
(Continued)

| | | | | | | |
|---|---|---|---|---|---|---|
| iPS:434283 | 21-225_57B8 | AA | SEQ ID NO:5523<br>SYAMS | SEQ ID NO:13535<br>AISGSGGNTFYADSVKG | SEQ ID NO:21547<br>LELGIFDY | |
| | | NA | SEQ ID NO:5524<br>AACTATGCCATGAGC | SEQ ID NO:13536<br>GCTAGCAGTGGTAGTGG TGGTAACACATTCTACGC AGACTCCGTGACGGGC | SEQ ID NO:21548<br>CTGGGGAAGGACTACCACTA CTACGGTATGGACGTC | |
| iPS:434285 | 21-225_57F8 | AA | SEQ ID NO:5525<br>NYAMS | SEQ ID NO:13537<br>ASSGSGGNTFYADSVTG | SEQ ID NO:21549<br>LGKDYHYYGMDV | |
| | | NA | SEQ ID NO:5526<br>AATTATGATATCAAC | SEQ ID NO:13538<br>TGGATGAACCCTAACAG TGTTAACACAGGCTATG CACAGAAGTTCCAGGGC | SEQ ID NO:21550<br>AGCAGTGGCTGGAACTGGTT CGACCCC | |
| iPS:434287 | 21-225_57A11 | AA | SEQ ID NO:5527<br>NYDIN | SEQ ID NO:13539<br>WMNPNSVNTGYAQKFQG | SEQ ID NO:21551<br>SSGWNWFDP | |
| | | NA | SEQ ID NO:5528<br>AATTATGATATCAAC | SEQ ID NO:13540<br>TGGATGAACCCTAACAA TGGTAACACAGGCTATG CACAGAAGTTCCAGGGC | SEQ ID NO:21552<br>AGCAGTGGCTGGTGTACCGGTT CGACCCC | |
| iPS:434289 | 21-225_57F12 | AA | SEQ ID NO:5529<br>NYDIN | SEQ ID NO:13541<br>WMNPNSGNTGYAQKFQG | SEQ ID NO:21553<br>SSGWYRFDP | |
| | | NA | SEQ ID NO:5530<br>AGCTACGCCATGAGC | SEQ ID NO:13542<br>GCTATTAGTGGTAGTGGT GGTAACACATTCTACGG AGACTCCGTGAAGGGC | SEQ ID NO:21554<br>TTTTTCGGTATAGTGGGTGC CGGGTACTTGACTAC | |
| | 21-225_57H12 | AA | SEQ ID NO:5531<br>SYAMS | SEQ ID NO:13543<br>AISGSGGNTFYGDSVKG | SEQ ID NO:21555<br>FFGIVGAGYFDY | |
| | | NA | SEQ ID NO:5532 | SEQ ID NO:13544 | SEQ ID NO:21556 | |

FIGURE 49
(Continued)

| | | | | | |
|---|---|---|---|---|---|
| iPS:434291 | 21-225_58A4 | NA | AGCTACGCCATGAGC | GCTATTAGTGGTAGTGGT GGTAACACATTCTACGG AGACTCCGTGAAGGGC | TTTTTCGGTATAGTGGGAGC CGGGTCTTCTTTGACTCC |
| | | | SEQ ID NO:5533 | SEQ ID NO:13545 | SEQ ID NO:21557 |
| | | AA | SYAMS | AISGSGGNTFYGDSVKG | FFGIVGAGFFDS |
| | | | SEQ ID NO:5534 | SEQ ID NO:13546 | SEQ ID NO:21558 |
| iPS:434293 | 21-225_58F5 | NA | GACTATGGCATGCAC | GTTATATATGGTATGCTGGA AGTAATAAATACCATGT AGACTCCGTGAAGGGC | GAACTGGGGATGAGGTCTGA CTAC |
| | | | SEQ ID NO:5535 | SEQ ID NO:13547 | SEQ ID NO:21559 |
| | | AA | DYGMH | VIWYAGSNKYHVDSVKG | ELGMRSDY |
| | | | SEQ ID NO:5536 | SEQ ID NO:13548 | SEQ ID NO:21560 |
| iPS:434295 | 21-225_58B9 | NA | AATTATGATATCAAC | TGGATGAACCCTAACAG TGGTAGCACAGGCTATG CACAGAAGTTCCAGGGC | AGCAGTGGCTGGTACTACTT TGACTAC |
| | | | SEQ ID NO:5537 | SEQ ID NO:13549 | SEQ ID NO:21561 |
| | | AA | NYDIN | WMNPNSGSTGYAQKFQG | SSGWYYFDY |
| | | | SEQ ID NO:5538 | SEQ ID NO:13550 | SEQ ID NO:21562 |
| iPS:434297 | 21-225_58A10 | NA | AGCTATGCCATGAGC | GCTATTAGTGGTAGTGGT GGTAACACATTCTACGC AGACTCCGTGAAGGGC | TTTTTCGGTATAGTGGGAGC CGGGTACTTTGACTAC |
| | | | SEQ ID NO:5539 | SEQ ID NO:13551 | SEQ ID NO:21563 |
| | | AA | SYAMS | AISGSGGNTFYADSVKG | FFGIVGAGYFDY |
| | | | SEQ ID NO:5540 | SEQ ID NO:13552 | SEQ ID NO:21564 |

FIGURE 49
(Continued)

| | | | | | |
|---|---|---|---|---|---|
| iPS:434299 | 21-225_58D11 | NA | GACTATGACATACAC SEQ ID NO:5541 | GTTATATGGTATGATGG AAGTAAAAATATTATG CAGACTCCGTGAAGGGC SEQ ID NO:13553 | GATCGGGTCACTTTTGACTA C SEQ ID NO:21565 |
| | | AA | DYDIH SEQ ID NO:5542 | VIWYDGSKKYYADSVKG SEQ ID NO:13554 | DRVTFDY SEQ ID NO:21566 |
| iPS:434301 | 21-225_58F11 | NA | AGCTATGCCATGAGC SEQ ID NO:5543 | GCTATTAGTGGTAGTGGT GGTAACACATTCTACGC AGACTCCGTGAAGGGC SEQ ID NO:13555 | TTTTTCGGTATGGTGGGAGC CGGATTCTTTGACTAC SEQ ID NO:21567 |
| | | AA | SYAMS SEQ ID NO:5544 | AISGSGGNTFYADSVKG SEQ ID NO:13556 | FFGMVGAGFFDY SEQ ID NO:21568 |
| iPS:434303 | 21-225_58H11 | NA | AGCTATGGCATGCAC SEQ ID NO:5545 | GTTATATGGTATGATGG AAGTAATAATACCATG CAGACTCCGTGAAGGGC SEQ ID NO:13557 | CGGTATAGCAGCAGCTGGGA CGGGGGTATGGACGTC SEQ ID NO:21569 |
| | | AA | SYGMH SEQ ID NO:5546 | VIWYDGSNKYHADSVKG SEQ ID NO:13558 | RYSSSWDGGMDV SEQ ID NO:21570 |
| iPS:434305 | 21-225_59E1 | NA | AATTATGATATCAAC SEQ ID NO:5547 | TGGATGACTCCTAACAG TGGTAACACAGGCTATG CACAGAAGTTCCAGGGC SEQ ID NO:13559 | AGCAGTGGCTGGTACTTCTT TGACTAC SEQ ID NO:21571 |
| | | AA | NYDIN SEQ ID NO:5548 | WMTPNSGNTGYAQKFQG SEQ ID NO:13560 | SSGWYFFDY SEQ ID NO:21572 |

FIGURE 49
(Continued)

| | | NA | GGCTACTATATACAC | | TGGATCAACCCTAACAGTGGTGGCACAAACTATGCACAGAAGTTTCAGGGC | | GATCCGGGGCCCCTTTGACTAC |
|---|---|---|---|---|---|---|---|
| iPS:434307 | 21-225_59B2 | | SEQ ID NO:5549 | | SEQ ID NO:13561 | | SEQ ID NO:21573 |
| | | AA | GYYIH | | WINPNSGGTNYAQKFQG | | DPGPFDY |
| | | | SEQ ID NO:5550 | | SEQ ID NO:13562 | | SEQ ID NO:21574 |
| iPS:434309 | 21-225_59B5 | NA | AGCTATGCCATGAAC | | GCTATTAGTGGTAGTGGTGGTAACACATTCTACGCAGACTCCGTGAAGGGC | | AGGGGGGTCTACGGTGACTACGAGGCTTTTGATATC |
| | | | SEQ ID NO:5551 | | SEQ ID NO:13563 | | SEQ ID NO:21575 |
| | | AA | SYAMN | | AISGSGGNTFYADSVKG | | RGVYGDYEAFDI |
| | | | SEQ ID NO:5552 | | SEQ ID NO:13564 | | SEQ ID NO:21576 |
| iPS:434311 | 21-225_59H5 | NA | AGCTATGGCATGCAC | | GTTATATGGTATGATGGAAGTAATAAATACTATGCAGACTCCGTGAAGGGC | | GAGAGGGTATAGCAGTGGGGTACTACGGTATGGACGTC |
| | | | SEQ ID NO:5553 | | SEQ ID NO:13565 | | SEQ ID NO:21577 |
| | | AA | SYGMH | | VIWYDGSNKYYADSVKG | | ERGIAVGYYGMDV |
| | | | SEQ ID NO:5554 | | SEQ ID NO:13566 | | SEQ ID NO:21578 |
| iPS:434313 | 21-225_59E6 | NA | AGAAGTAGTTACTACTGGGGC | | AATATCTATTATAGTGGGAGCACCTACTACAACCCGTCCCTCAAGAGT | | CATAGCAGCAGCTGGTCCCTTGACTAC |
| | | | SEQ ID NO:5555 | | SEQ ID NO:13567 | | SEQ ID NO:21579 |
| | | AA | RSSYYWG | | NIYYSGSTYYNPSLKS | | HSSSWSLDY |
| | | | SEQ ID NO:5556 | | SEQ ID NO:13568 | | SEQ ID NO:21580 |
| iPS:434315 | 21-225_59G7 | NA | GGCCACTATATACAC | | TGGATCAACCGAACAGTGGTGGCACAAACTATGTACAGAAATTTCAGGGC | | GGGGGCCTACTGGGAGCTACCAACTACTACTACGGTATGGACGTC |

FIGURE 49
(Continued)

| | | | | | | | |
|---|---|---|---|---|---|---|---|
| iPS:434317 | 21-225_59E8 | AA | SEQ ID NO:5557<br>GHYIH | SEQ ID NO:13569<br>WINPNSGGTNYVQKFQG | SEQ ID NO:21581<br>GGLLGATNYYYYGMDV | | |
| | | NA | SEQ ID NO:5558<br>AGCTATAGCATGAAT | SEQ ID NO:13570<br>TACATTAGTAGTAGTAGT<br>GGGACCATATACTACGC<br>AGACTCTGTGAAGGGC | SEQ ID NO:21582<br>GAATGGGGAATGGCAGTGGC<br>TGGCCCGTTTGACTAC | | |
| iPS:434319 | 21-225_59B9 | AA | SEQ ID NO:5559<br>SYSMN | SEQ ID NO:13571<br>YISSSSGTIYYADSVKG | SEQ ID NO:21583<br>EWGMAVAGPFDY | | |
| | | NA | SEQ ID NO:5560<br>GGCAATTATATACAC | SEQ ID NO:13572<br>TGGATCAACCCTAACAG<br>TGGTGGCACAAACTATG<br>TACAGAAGTTCCAGGGC | SEQ ID NO:21584<br>GGGGGCCTACTGGGAGCTAC<br>CTACTACTACTACGGTA<br>TGGACGTC | | |
| iPS:434321 | 21-225_59F10 | AA | SEQ ID NO:5561<br>GNYIH | SEQ ID NO:13573<br>WINPNSGGTNYVQKFQG | SEQ ID NO:21585<br>GGLLGATYYYYGMDV | | |
| | | NA | SEQ ID NO:5562<br>AATTATGATATCAAC | SEQ ID NO:13574<br>TGGATGAACCCTAACAG<br>TGGTAACACAGGCTATG<br>CACAGAAGTTCCAGGGC | SEQ ID NO:21586<br>AGCAGTGGCTGGTACTACTT<br>TGACTAC | | |
| iPS:434323 | 21-225_62H8 | AA | SEQ ID NO:5563<br>NYDIN | SEQ ID NO:13575<br>WMNPNSGNTGYAQKFQG | SEQ ID NO:21587<br>SSGWYYFDY | | |
| | | NA | SEQ ID NO:5564<br>ACCTATGGCATGCAC | SEQ ID NO:13576<br>GTTATATGGCATGGATGG<br>AAGTGATAAATATTATG<br>TAGACTCCGTGAAGGGC | SEQ ID NO:21588<br>GAAGACCCGCGCTACCAGCTG<br>CTCTGACTAC | | |
| | | AA | SEQ ID NO:5565<br>TYGMH | SEQ ID NO:13577<br>VIWHDGSDKYYVDSVKG | SEQ ID NO:21589<br>EDPRTSCSDY | | |
| | | | SEQ ID NO:5566 | SEQ ID NO:13578 | SEQ ID NO:21590 | | |

FIGURE 49
(Continued)

| | | | | | |
|---|---|---|---|---|---|
| iPS:434327 | 21-225_63G6 | NA | AGCTATGGCATGCAC | GTTATATGGTATGATGG AAGTAATAAATACTATG CAGACTCCGTGAAGGGC | GATAGCCTCTCGGGTATAGC AGCAGCTTTGACTAC |
| | | | SEQ ID NO:5567 | SEQ ID NO:13579 | SEQ ID NO:21591 |
| | | AA | SYGMH | VIWYDGSNKYYADSVKG | DSLSGIAAAFDY |
| | | | SEQ ID NO:5568 | SEQ ID NO:13580 | SEQ ID NO:21592 |
| iPS:434331 | 21-225_63H8 | NA | AGCTATAACATGAAC | TCCATTAGTGGTAGTAGC ACTTACATGAACTACAC AGACTCAGTGAAGGGC | CTACGTAATTTTGACTAC |
| | | | SEQ ID NO:5569 | SEQ ID NO:13581 | SEQ ID NO:21593 |
| | | AA | SYNMN | SISGSSTYMNYTDSVKG | LRNFDY |
| | | | SEQ ID NO:5570 | SEQ ID NO:13582 | SEQ ID NO:21594 |
| iPS:434333 | 21-225_63C9 | NA | GGCTACTATATGCAC | TGGATCAACCCTAACAG TGGTGGCACAAACTTTG CACAGAAGTTTCAGGGC | GCTCCGGGTGTAGCAGCAGC TGGTTCATGGGGATACTTTG ACTAC |
| | | | SEQ ID NO:5571 | SEQ ID NO:13583 | SEQ ID NO:21595 |
| | | AA | GYYMH | WINPNSGGTNFAQKFQG | APGVAAAGSWGYFDY |
| | | | SEQ ID NO:5572 | SEQ ID NO:13584 | SEQ ID NO:21596 |
| iPS:434335 | 21-225_63C10 | NA | AGCTATGGCATGCAC | GTCATATGGTATGATGG AAGTAATAAATACTATG CAGACTCCGTGAAGGGC | GATGATCCCAGATCCTCGGC CGGGGACTAC |
| | | | SEQ ID NO:5573 | SEQ ID NO:13585 | SEQ ID NO:21597 |
| | | AA | SYGMH | VIWYDGSNKYYADSVKG | DDPRSSAGDY |
| | | | SEQ ID NO:5574 | SEQ ID NO:13586 | SEQ ID NO:21598 |

FIGURE 49
(Continued)

| | | | | | |
|---|---|---|---|---|---|
| iPS:434337 | 21-225_64E1 | NA | AGCTATGGCATGCAC | GTTATATGGTTTGATGAA ACTAATAAATACTATGG AGACTCCGTGAAGGGC | GAGCTTGGGTTCAGCAGTGA CTAT |
| | | | SEQ ID NO:5575 | SEQ ID NO:13587 | SEQ ID NO:21599 |
| | | AA | SYGMH | VIWFDETNKYYGDSVKG | ELGFSSDY |
| | | | SEQ ID NO:5576 | SEQ ID NO:13588 | SEQ ID NO:21600 |
| iPS:434339 | 21-225_64A4 | NA | GATTATGTCATGCAC | GTCATATGGTATGATGG AAGTAATAAATACTATG CAGACTCCGTGAAGGGC | GAAAGGTATAGCAGCAGCTG GTACGACTACGGTATGGACG TC |
| | | | SEQ ID NO:5577 | SEQ ID NO:13589 | SEQ ID NO:21601 |
| | | AA | DYVMH | VIWYDGSNKYYADSVKG | ERYSSSWYDYGMDV |
| | | | SEQ ID NO:5578 | SEQ ID NO:13590 | SEQ ID NO:21602 |
| iPS:434341 | 21-225_64F7 | NA | AGTTACTTCTGGAGC | CGTATCTATACCAGTGG GATCTCCAACTACACAATCC TACCTCCCTCAAGAGT | TTTAGCAGTGGCTTTTTGAC TAC |
| | | | SEQ ID NO:5579 | SEQ ID NO:13591 | SEQ ID NO:21603 |
| | | AA | SYFWS | RIYTSGISNYNPSLKS | FSSGFFDY |
| | | | SEQ ID NO:5580 | SEQ ID NO:13592 | SEQ ID NO:21604 |
| iPS:434343 | 21-225_64C8 | NA | GACTATGTCATGCAC | GTTATATGGTATGATGG AAGTAATAAATACTATG CAGACTCCATGAAGGGC | GAACGGTATAGCAGTGGCTG GTACGACTACGGTATGGACG TC |
| | | | SEQ ID NO:5581 | SEQ ID NO:13593 | SEQ ID NO:21605 |
| | | AA | DYVMH | VIWYDGSNKYYADSMKG | ERYSSGWYDYGMDV |
| | | | SEQ ID NO:5582 | SEQ ID NO:13594 | SEQ ID NO:21606 |

FIGURE 49
(Continued)

| iPS:434345 | 21-225_64H9 | NA | ACCTATGGCATGCAC SEQ ID NO:5583 | ATTATATGGTATGATGG AAGTAATAAATACTATG CAGACTCCGTGAAGGGC SEQ ID NO:13595 | GATACATACGATTTTTGGAG TGGTTATTGGGCTAC SEQ ID NO:21607 |
| --- | --- | --- | --- | --- | --- |
| | | AA | TYGMH SEQ ID NO:5584 | IIWYDGSNKYYADSVKG SEQ ID NO:13596 | DTYDFWSGYLGY SEQ ID NO:21608 |
| iPS:434347 | 21-225_64H10 | NA | GGCTACTATATGCAC SEQ ID NO:5585 | TGGATCAAACCAAACAG TGGTGGCACAAACCAAG CACAGAAGTTTCAGGGC SEQ ID NO:13597 | GCTCCGGGTACTGCAGCAAC TGGTACATGGGGATACTTTG ACTAC SEQ ID NO:21609 |
| | | AA | GYYMH SEQ ID NO:5586 | WIKPNSGGTNQAQKFQG SEQ ID NO:13598 | APGTAATGTWGYFDY SEQ ID NO:21610 |
| iPS:434351 | 21-225_64A12 | NA | AGCTATGGCATGCAC SEQ ID NO:5587 | GTTATATGGTATGATGA AAGTAATAAATACTATG TAGACTCCGTGAAGGGC SEQ ID NO:13599 | GAACTCGGGTTCCTCTCTGA CCAC SEQ ID NO:21611 |
| | | AA | SYGMH SEQ ID NO:5588 | VIWYDESNKYYVDSVKG SEQ ID NO:13600 | ELGFLSDH SEQ ID NO:21612 |
| iPS:434353 | 21-225_64B12 | NA | AGAAGTAGTTACTACTGGGG C SEQ ID NO:5589 | AGTATCTATTACAGTGG GAGCACCTCCTACAACC CGTCCCTCAAGAGT SEQ ID NO:13601 | CTGGACAGTGGCTGGTCCTT TGACTAC SEQ ID NO:21613 |
| | | AA | RSSYYWG SEQ ID NO:5590 | SIYYSGSTSYNPSLKS SEQ ID NO:13602 | LDSGWSFDY SEQ ID NO:21614 |

FIGURE 49
(Continued)

| iPS ID | Clone | Type | CDR1 | CDR2 | CDR3 |
|---|---|---|---|---|---|
| iPS:434355 | 21-225_64G12 | NA | AGTAATGCCATGAGC (SEQ ID NO:5591) | GTTATTAGTGGTAGTGGTGGTAGCACATACTACGCAGACTCCGTGAAGGGC (SEQ ID NO:13603) | AGGAACTACGACGATGCTTTTGATATC (SEQ ID NO:21615) |
| | | AA | SNAMS (SEQ ID NO:5592) | VISGSGGSTYYADSVKG (SEQ ID NO:13604) | RNYDDAFDI (SEQ ID NO:21616) |
| iPS:434357 | 21-225_65C1 | NA | GACTATGGCATGCAC (SEQ ID NO:5593) | GTGTATGGTTGAGGGAAGTAATAAACACTATACAGACTCCGTGAAGGGC (SEQ ID NO:13605) | GAACTTGGGTTCAGCAGTGACTAC (SEQ ID NO:21617) |
| | | AA | DYGMH (SEQ ID NO:5594) | VIWFEGSNKHYTDSVKG (SEQ ID NO:13606) | ELGFSSDY (SEQ ID NO:21618) |
| iPS:434359 | 21-225_65G3 | NA | GGCTACTATATACAC (SEQ ID NO:5595) | TGGATCAACCCTAACAGTGGTGGCACAACTCTGCACAGAAGTTTCAGGGC (SEQ ID NO:13607) | GCTCCGGGTAAAGCAGCAGCTGGTACATGGGGATACTTTGACTAC (SEQ ID NO:21619) |
| | | AA | GYYIH (SEQ ID NO:5596) | WINPNSGGTNSAQKFQG (SEQ ID NO:13608) | APGKAAAGTWGYFDY (SEQ ID NO:21620) |
| iPS:434361 | 21-225_65D5 | NA | AGCTATGGTATCAGT (SEQ ID NO:5597) | TGGATCAGCGCTTACAGTGGTAACACAAACTATGCACAGAAGCTCCAGGGC (SEQ ID NO:13609) | GGGGAAGCAGTGGCTGTCTTCGACCCC (SEQ ID NO:21621) |
| | | AA | SYGIS (SEQ ID NO:5598) | WISAYSGNTNYAQKLQG (SEQ ID NO:13610) | GEAVAVFDP (SEQ ID NO:21622) |
| iPS:434363 | 21_225_65A6 | NA | AACTATGGCATGCAC | GTTATATGGTATGATGGAAGTAATAAATACTATGGAGACTCCGTGAAGGGC | GATCAGGGCATAGTGGGAGCTACTTGGTTTGACTAC |

FIGURE 49
(Continued)

| | | | SEQ ID NO:5599 | SEQ ID NO:13611 | SEQ ID NO:21623 |
| --- | --- | --- | --- | --- | --- |
| iPS:434367 | 21-225_65A6 | AA | NYGMH | VIWYDGSNKYYGDSVKG | DQGIVGAFWFDY |
| | | NA | SEQ ID NO:5600 AGCTATAGGATGAAC | SEQ ID NO:13612 TCCATTAGTAGTAGTAAT AGTTCCATATACTACGCA GACTCAGTGAAGGGC | SEQ ID NO:21624 ACAAGTGGGAGC |
| iPS:434369 | 21-225_65H11 | AA | SEQ ID NO:5601 SYRMN | SEQ ID NO:13613 SISSSNSSIYYADSVKG | SEQ ID NO:21625 TSGS |
| | | NA | SEQ ID NO:5602 GGCTACTATATGCAC | SEQ ID NO:13614 TGGATCAACCCTAACAG TGGTGGCACAAACAATG CACAGAAGTTTCAGGGC | SEQ ID NO:21626 GCTCCGGGTACAGCAGCAGC TGGTACATGGGGATACTTTG ACTAC |
| iPS:434371 | 21-225_66B1 | AA | SEQ ID NO:5603 GYYMH | SEQ ID NO:13615 WINPNSGGTNNAQKFQG | SEQ ID NO:21627 APGTAAAGTWGYFDY |
| | | NA | SEQ ID NO:5604 GGCTACTATATGCAC | SEQ ID NO:13616 TGGATCAACCAAACAAG TGGTGGCACAAACCAAG CACAGAAGTTCCAGGGC | SEQ ID NO:21628 GCTCCGGGCACAGTAGCAGC TGGTACATGGGGATACTTTG ACTAT |
| iPS:434373 | 21-225_66A7 | AA | SEQ ID NO:5605 GYYMH | SEQ ID NO:13617 WIKPNSGGTNQAQKFQG | SEQ ID NO:21629 APGTVAAGTWGYFDY |
| | | NA | SEQ ID NO:5606 GACTATGGCATGCAC | SEQ ID NO:13618 GTTATATGGTTTGAGGG AAGTCATAAATACTATA CAGACTCCGTGAAGGGC | SEQ ID NO:21630 GAACTTGGGTTCAGCAGTGA CTAC |
| iPS:434375 | 21-225_66C7 | AA | SEQ ID NO:5607 DYGMH | SEQ ID NO:13619 VIWFEGSHKYYTDSVKG | SEQ ID NO:21631 ELGFSSDY |
| | | | SEQ ID NO:5608 | SEQ ID NO:13620 | SEQ ID NO:21632 |

FIGURE 49
(Continued)

| | | | | | |
|---|---|---|---|---|---|
| iPS:434379 | 21-225_66A9 | NA | AGCTATGGCATGCAC | GTTATATGGCATGATGG AAGTGATAAATACTATG CAGACTCCGTGAAGGGC | GAAGACCCGCGTACCAGTTG TTCTGACTAC |
| | | | SEQ ID NO:5609 | SEQ ID NO:13621 | SEQ ID NO:21633 |
| | | AA | SYGMH | VIWHDGSDKYYADSVKG | EDPRTSCSDY |
| | | | SEQ ID NO:5610 | SEQ ID NO:13622 | SEQ ID NO:21634 |
| iPS:434383 | 21-225_66F9 | NA | AGCTATAGCATGAAC | TCCATTAGTGGTACTAGT AGTTACATATACTACGC AGACTCAGTGAAGGGC | ACCAATGCTTTTGATATC |
| | | | SEQ ID NO:5611 | SEQ ID NO:13623 | SEQ ID NO:21635 |
| | | AA | SYSMN | SISGTSSYIYYADSVKG | TNAFDI |
| | | | SEQ ID NO:5612 | SEQ ID NO:13624 | SEQ ID NO:21636 |
| iPS:434385 | 21-225_66C10 | NA | AGCTATGTTATGAGC | GGTATTAGTGGTAGTGG TGCTAGAACATACTACG CAGACTCCGTGAAGGGC | CTGGGGATAGACTACTACTA CGGTATGGACGTC |
| | | | SEQ ID NO:5613 | SEQ ID NO:13625 | SEQ ID NO:21637 |
| | | AA | SYVMS | GISGSGARTYYADSVKG | LGIDYYYGMDV |
| | | | SEQ ID NO:5614 | SEQ ID NO:13626 | SEQ ID NO:21638 |
| iPS:434387 | 21-225_66D11 | NA | AGCTATATGGCATGCAC | GTTATATGGTATGATGG AAGTAATAAATACTATG CAGACTCCGTGAAGGGC | GAGATGTATAGCAGCAACTG GTACGACTACGGTTTGGACG TC |
| | | | SEQ ID NO:5615 | SEQ ID NO:13627 | SEQ ID NO:21639 |
| | | AA | SYGMH | VIWYDGSNKYYADSVKG | EMYSSNWYDYGLDV |
| | | | SEQ ID NO:5616 | SEQ ID NO:13628 | SEQ ID NO:21640 |

FIGURE 49
(Continued)

| | | | | | |
|---|---|---|---|---|---|
| iPS:434389 | 21-225_66F11 | NA | GGCTACCATATGCAC | TGGATCAACCCTAACAATGGTGGCACACACTATGCACAGAAGTTTCAGGAC | GATAGTAGAAGTTCGTGGACTAC |
| | | | SEQ ID NO:5617 | SEQ ID NO:13629 | SEQ ID NO:21641 |
| | | AA | GYHMH | WINPNNGGTHYAQKFQD | DSRSSWDY |
| | | | SEQ ID NO:5618 | SEQ ID NO:13630 | SEQ ID NO:21642 |
| iPS:434393 | 21-225_67C3 | NA | AGTTATGGCATGCAC | GCTATATGGTATGATGGAAGTAATAAATATTATGGAGACTCCGTGAAGGGC | GATCAGGGCATAGTGGGAGCTACTTGTTTGACTAC |
| | | | SEQ ID NO:5619 | SEQ ID NO:13631 | SEQ ID NO:21643 |
| | | AA | SYGMH | AIWYDGSNKYYGDSVKG | DQGIVGATWFDY |
| | | | SEQ ID NO:5620 | SEQ ID NO:13632 | SEQ ID NO:21644 |
| iPS:434397 | 21-225_67H4 | NA | GGCTACTATATGCAC | TGGATCAAACCAACAACAGTGGTGGCACAAACCAAGCACAGAAGTTTCAGGGC | GCTCCGGGTACTGCAGCAACTGGTACATGGGGATACTTTG ACTAC |
| | | | SEQ ID NO:5621 | SEQ ID NO:13633 | SEQ ID NO:21645 |
| | | AA | GYYMH | WIKPNSGGTNQAQKFQG | APGTAAFGTWGYFDY |
| | | | SEQ ID NO:5622 | SEQ ID NO:13634 | SEQ ID NO:21646 |
| iPS:434399 | 21-225_67B7 | NA | AACTATGGCATGCAC | GTTATATTATATGAATGGAAGTAAGAAATACTATGCAGACTCCGTGAAGGGC | AGTATCCCGGAATTTGACTAT |
| | | | SEQ ID NO:5623 | SEQ ID NO:13635 | SEQ ID NO:21647 |
| | | AA | NYGMH | VILYDGSKKYYADSVKG | SIPEFDY |
| | | | SEQ ID NO:5624 | SEQ ID NO:13636 | SEQ ID NO:21648 |

FIGURE 49
(Continued)

| | | NA | AGCTTTGGCATGAAC | TACATTAGTAGAAGTAG TAGTCACATATACGC AGACTCAGTGAAGGGC | TCTAGTGGGAGCCCTTGA CTAC |
|---|---|---|---|---|---|
| iPS:434405 | 21-225_68E6 | | SEQ ID NO:5625 | SEQ ID NO:13637 | SEQ ID NO:21649 |
| | | AA | SFGMN | YISRSSSHIYYADSVKG | SSGSPFDY |
| | | | SEQ ID NO:5626 | SEQ ID NO:13638 | SEQ ID NO:21650 |
| iPS:434407 | 21-225_68G8 | NA | AGCTATAGCATGAAC | TCCATTAGTGGTAGTAGT AGTTACATATATTACGCA GACTCAGTGATGGGC | GTCAACAGCTTTGACTCC |
| | | | SEQ ID NO:5627 | SEQ ID NO:13639 | SEQ ID NO:21651 |
| | | AA | SYSMN | SISGSSYIYYADSVMG | VNSFDS |
| | | | SEQ ID NO:5628 | SEQ ID NO:13640 | SEQ ID NO:21652 |
| iPS:434411 | 21-225_68F11 | NA | GACTATGGCATGCAC | GTTATATGGTATGATGTA AGTAATAAATACTATGC AGACTCCGTGAAGGGC | GAACTGGGGATGACCTCTGA CTGC |
| | | | SEQ ID NO:5629 | SEQ ID NO:13641 | SEQ ID NO:21653 |
| | | AA | DYGMH | VIWYDVSNKYYADSVKG | ELGMTSDC |
| | | | SEQ ID NO:5630 | SEQ ID NO:13642 | SEQ ID NO:21654 |
| iPS:434413 | 21-225_68D12 | NA | AGAAGTAGTTACTACTGGGG C | AATATCTATTATAGTGGG AGCACCTATTACATCCCG TCCCTCAAGAGT | CATAGCACCAGCTGGTCCAT TGACTAC |
| | | | SEQ ID NO:5631 | SEQ ID NO:13643 | SEQ ID NO:21655 |
| | | AA | RSSYYWG | NIYYSGSTYYIPSLKS | HSTSWSIDY |
| | | | SEQ ID NO:5632 | SEQ ID NO:13644 | SEQ ID NO:21656 |
| iPS:434417 | 21-225_69C8 | NA | AACTATGCCATGCAC | GTTATATGGTATGATGG AAGTGATAAATACTATG CAGACTCCGTGAAGGGC | GATATCCCTAGCAACTCGGC GGGGGACTAC |
| | | | SEQ ID NO:5633 | SEQ ID NO:13645 | SEQ ID NO:21657 |

FIGURE 49
(Continued)

| | | | | | | | |
|---|---|---|---|---|---|---|---|
| iPS:434423 | 21-225_70D1 | AA | NYAMH | | VIWYDGSDKYYADSVKG | | DIPSNSAGDY |
| | | NA | GGCTACCATATGCAC | SEQ ID NO:5634 | TGGATCAACCCTAACAG TAATGCCACAAACTATAT CACAGAAGTTTCAGGGC | SEQ ID NO:13646 | GATAGCATATCGTCGTGGGA CTAC | SEQ ID NO:21658 |
| | | AA | GYHMH | SEQ ID NO:5635 | WINPNSNATNYAQKFQG | SEQ ID NO:13647 | DSISSWDY | SEQ ID NO:21659 |
| iPS:434425 | 21-225_70A5 | NA | AGCTATGGCATGCAC | SEQ ID NO:5636 | GTTATATATGGTATGATGG AAGTAATAAATACTATG CAGACTCCGTGAAGGGC | SEQ ID NO:13648 | GATCAGGGCATAGTGGGAGC TACTTGGTTTGACTAC | SEQ ID NO:21660 |
| | | AA | SYGMH | SEQ ID NO:5637 | VIWYDGSNKYYADSVKG | SEQ ID NO:13649 | DQGIVGATWFDY | SEQ ID NO:21661 |
| iPS:434427 | 21-225_70D6 | NA | GGCTACTATATGCAC | SEQ ID NO:5638 | TGGATCAACCCTAACAG TGGTGGCACAAACTCTG CACAGAAGTTTCAGGGC | SEQ ID NO:13650 | GCTCCGGGTAAAGCAGCAGC TGGTACATGGGGATTCTTTG ACTAC | SEQ ID NO:21662 |
| | | AA | GYYMH | SEQ ID NO:5639 | WINPKSGGTNSAQKFQG | SEQ ID NO:13651 | APGKAAAGTWGFFDY | SEQ ID NO:21663 |
| iPS:434429 | 21-225_70H6 | NA | AGTTATGGCATGCAC | SEQ ID NO:5640 | GTTATATGGCATGATGG AAGTAATAAATACTATG CAGACTCCGTGAAGGGC | SEQ ID NO:13652 | GATGATCCCAGATCCTCGGC CGGGGACTAC | SEQ ID NO:21664 |
| | | AA | SYGMH | SEQ ID NO:5641 | VIWHDGSNKYYADSVKG | SEQ ID NO:13653 | DDPRSSAGDY | SEQ ID NO:21665 |

FIGURE 49
(Continued)

| | | | | | |
|---|---|---|---|---|---|
| iPS:434431 | 21-225_70E7 | NA | SEQ ID NO:5642<br>AATTATGATATCAAC | SEQ ID NO:13654<br>TGGATGCACCCTAACAG<br>TGGTAACACAGGCTATG<br>CACAGAAGTTCCAGGGC | SEQ ID NO:21666<br>AGCAGTGGCTGGTACGTCTT<br>TGACTAC |
| | | AA | SEQ ID NO:5643<br>NYDIN | SEQ ID NO:13655<br>WMHPNSGNTGYAQKFQG | SEQ ID NO:21667<br>SSGWYVFDY |
| iPS:434433 | 21-225_70E8 | NA | SEQ ID NO:5644<br>AGCTATGGCATGCTC | SEQ ID NO:13656<br>ATTATATGGTATGATGA<br>AAGTAATAAATACTATG<br>CAGACTCCGTGAAGGGC | SEQ ID NO:21668<br>GACCTACTGGACCCACGGGA<br>CTAC |
| | | AA | SEQ ID NO:5645<br>SYGML | SEQ ID NO:13657<br>IIWYDESNKYYADSVKG | SEQ ID NO:21669<br>DLLDPRDY |
| iPS:434435 | 21-225_70C9 | NA | SEQ ID NO:5646<br>GGCTACTATATGCAC | SEQ ID NO:13658<br>TGGATCAAACCTAACAG<br>TGGTGGCACAAACCAAG<br>CACAGAAGTTTCAGGGC | SEQ ID NO:21670<br>GCTCCGGGTATAGCAGCAGC<br>TGGTACATGGGGATACTTTG<br>ACTAC |
| | | AA | SEQ ID NO:5647<br>GYYMH | SEQ ID NO:13659<br>WIKPNSGGTNQAQKFQG | SEQ ID NO:21671<br>APGIAAAGTWGYFDY |
| iPS:434437 | 21-225_70A12 | NA | SEQ ID NO:5648<br>GGCTACTATATGCAC | SEQ ID NO:13660<br>TGGATCAAACCAAACCAAG<br>TGGTGGCACAAACCAAG<br>CACAGAAGTTTCAGGGC | SEQ ID NO:21672<br>GCTCCGGGTACTGCAGCAAC<br>TGGTACATGGGGATACTTTG<br>ACTAC |
| | | AA | SEQ ID NO:5649<br>GYYMH | SEQ ID NO:13661<br>WIKPNSGGTNQAQKFQG | SEQ ID NO:21673<br>APGTAATGTWGYFDY |
| | | | SEQ ID NO:5650 | SEQ ID NO:13662 | SEQ ID NO:21674 |

FIGURE 49
(Continued)

| | | | | | |
|---|---|---|---|---|---|
| iPS:434439 | 21-225_70E12 | NA | AGCTATAGCATGAAC | TCCATTAGTAGTGGTAATAGT ACTTACATATACTACACA GACTCAGTGAAGGGC | GTGGCCGCCTTTGACTGC |
| | | | SEQ ID NO:5651 | SEQ ID NO:13663 | SEQ ID NO:21675 |
| | | AA | SYSMN | SISGNSTYIYYTDSVKG | VAAFDC |
| | | | SEQ ID NO:5652 | SEQ ID NO:13664 | SEQ ID NO:21676 |
| iPS:434441 | 21-225_71A2 | NA | GACTATGGCATGCAC | GTGATATGGTATGATGA AAGTAATAAATACTATG CAGACTCCGTGAAGGGC | GAATTGGGGTGGCAGGATGA TTAC |
| | | | SEQ ID NO:5653 | SEQ ID NO:13665 | SEQ ID NO:21677 |
| | | AA | DYGMH | VIWYDESNKYYADSVKG | ELGWQDDY |
| | | | SEQ ID NO:5654 | SEQ ID NO:13666 | SEQ ID NO:21678 |
| iPS:434443 | 21-225_71G3 | NA | AATTATGATATCAAC | TGGATGCACCCTAACAG TGGTAGCACAGGCTATG CACAGAAGTTCCAGGGC | AGCAGTGGCTGGTACTACTT TGACTAC |
| | | | SEQ ID NO:5655 | SEQ ID NO:13667 | SEQ ID NO:21679 |
| | | AA | NYDIN | WMHPNSGSTGYAQKFQG | SSGWYYFDY |
| | | | SEQ ID NO:5656 | SEQ ID NO:13668 | SEQ ID NO:21680 |
| iPS:434447 | 21-225_71B6 | NA | AACTATGGCATGCAC | GTTATTTGGTATGATAGA ACAAATAAATACTATGC AGACTCCGTGAAGGGC | GAACTGGGGATGTTGTCTGA CTAC |
| | | | SEQ ID NO:5657 | SEQ ID NO:13669 | SEQ ID NO:21681 |
| | | AA | NYGMH | VIWYDRTNKYYADSVKG | ELGMLSDY |
| | | | SEQ ID NO:5658 | SEQ ID NO:13670 | SEQ ID NO:21682 |

FIGURE 49
(Continued)

| | | | | | |
|---|---|---|---|---|---|
| iPS:434449 | 21-225_71H6 | NA | AGCTATAGCATGAAC | TCCATTAGTGGTACTAGTAGTTACATATACTACGCAGACTCAGTGAAGGGC | ACCAATGCTTTTGATATC |
| | | | SEQ ID NO:5659 | SEQ ID NO:13671 | SEQ ID NO:21683 |
| | | AA | SYSMN | SISGTSSYIYYADSVKG | TNAFDI |
| | | | SEQ ID NO:5660 | SEQ ID NO:13672 | SEQ ID NO:21684 |
| iPS:434451 | 21-225_71B7 | NA | GGCTACTATATGCAC | TGGATCAACCCTAACAGTGGTGGCACAAACTCTGCACAGAAGTTTCAGGGC | GCTCCGGGTAAAGCAGCAGCTGGTACATGGGGATTCTTTGACTAC |
| | | | SEQ ID NO:5661 | SEQ ID NO:13673 | SEQ ID NO:21685 |
| | | AA | GYYMH | WINPNSGGTNSAQKFQG | APGKAAAGTWGFFDY |
| | | | SEQ ID NO:5662 | SEQ ID NO:13674 | SEQ ID NO:21686 |
| iPS:434453 | 21-225_71B11 | NA | GACTATGGCATGCAC | GTTATATGGTATGATAGAAATAATACTATGGAGACTCCGTGAAGGGC | GAACTGGGGATGTTGTCTGACTAC |
| | | | SEQ ID NO:5663 | SEQ ID NO:13675 | SEQ ID NO:21687 |
| | | AA | DYGMH | VIWYDRNNKYYGDSVKG | ELGMLSDY |
| | | | SEQ ID NO:5664 | SEQ ID NO:13676 | SEQ ID NO:21688 |
| iPS:434455 | 21-225_72F5 | NA | AGCTATGCCATGATC | ACTATTAGTGGTAGTGGTGGTTACACATACTCCGCAGACTCCGTGAAGGGC | CGTATAGCAGTGACTGGGACGGAATGGTACGACCCC |
| | | | SEQ ID NO:5665 | SEQ ID NO:13677 | SEQ ID NO:21689 |
| | | AA | SYAMI | TISGSGGYTYSADSVKG | RIAVTGTEWYDP |
| | | | SEQ ID NO:5666 | SEQ ID NO:13678 | SEQ ID NO:21690 |
| iPS:434457 | 21-225_72G12 | NA | AGCTATGGCATGCAC | GTTATATGGTTTGATGAAAGTAATAAATACTATGCAGACTCCGTGAAGGGC | GAGCTTGGTTTCAGCAGTGACTAC |

FIGURE 49
(Continued)

| | | | | | | | |
|---|---|---|---|---|---|---|---|
| iPS:434459 | 21-225_71A7 | AA | SEQ ID NO:5667<br>SYGMH | SEQ ID NO:13679<br>VIWFDESNKYYADSVKG | SEQ ID NO:21691<br>ELGFSSDY |
| | | NA | SEQ ID NO:5668<br>GGCTACTATATGCAC | SEQ ID NO:13680<br>TGGATCAACCCTAAAAG<br>TGGTGGCACAAATTATG<br>TACAGAAGTTTCAGGGC | SEQ ID NO:21692<br>GCTCCGGGTACAGCACCAGC<br>TGGGTCATGGGGATACTTTG<br>ACTAC |
| iPS:434461 | 21-225_73A3 | AA | SEQ ID NO:5669<br>GYYMH | SEQ ID NO:13681<br>WINPKSGGTNYVQKFQG | SEQ ID NO:21693<br>APGTAPAGSWGYFDY |
| | | NA | SEQ ID NO:5670<br>GGCTACTATATGCAC | SEQ ID NO:13682<br>TGGATCAACCCTAAAAG<br>TGGTGGCACGAATCATG<br>TCCAGAAGTTTCAGGGC | SEQ ID NO:21694<br>GCTCCGGGTACAGCAGCAGC<br>TGGGTCATGGGGATGCTTTG<br>ACTAC |
| iPS:434463 | 21-225_73A6 | AA | SEQ ID NO:5671<br>GYYMH | SEQ ID NO:13683<br>WINPKSGGTNHVQKFQG | SEQ ID NO:21695<br>APGTAAAGSWGCFDY |
| | | NA | SEQ ID NO:5672<br>TACTATGGCATGGAGC | SEQ ID NO:13684<br>GTTATATTATATGATGGA<br>AGTAAGAAATACTATGC<br>AGCCTCCGTGAAGGGC | SEQ ID NO:21696<br>AGTATCCCGGACTTTGACTA<br>C |
| iPS:434467 | 21-225_73H8 | AA | SEQ ID NO:5673<br>YYGMH | SEQ ID NO:13685<br>VILYDGSKKYYAASVKG | SEQ ID NO:21697<br>SIPDFDY |
| | | NA | SEQ ID NO:5674<br>AGCAATGCCATGAGC | SEQ ID NO:13686<br>GACATTAGTCGTAGTGG<br>TGGTACCACATTCTACGC<br>AGACTCCGTGAAGGGC | SEQ ID NO:21698<br>TGGGATAGCAGCAGCTGGTA<br>CGACGTGACTCCCTTGACT<br>AC |
| | | AA | SEQ ID NO:5675<br>SNAMS | SEQ ID NO:13687<br>DISRSGGTFYADSVKG | SEQ ID NO:21699<br>WDSSSWYDVTPFDY |
| | | | SEQ ID NO:5676 | SEQ ID NO:13688 | SEQ ID NO:21700 |

FIGURE 49
(Continued)

| | | NA/AA | | | |
|---|---|---|---|---|---|
| iPS:434469 | 21-225_73C9 | NA | AATTATGTCATGCAC SEQ ID NO:5677 | GTTATATGGTATGATGG AAGTAATAAATACTATG CAGACTCCGTGAAGGGC SEQ ID NO:13689 | GAAAGGTATAGCAGCAGCTG GTTCGACTACGGTATGGACG TC SEQ ID NO:21701 |
| | | AA | NYVMH | VIWYDGSNKYYADSVKG SEQ ID NO:13690 | ERYSSSWFDYGMDV SEQ ID NO:21702 |
| iPS:434471 | 21-225_75G3 | NA | GGTTCCTACTGGAGC SEQ ID NO:5679 | GAAATCAATCTTAGTGG AAGTACCAACTACAACC CGTCCCTCAAGAGT SEQ ID NO:13691 | GACTACGGTGGCCTTGACTA C SEQ ID NO:21703 |
| | | AA | GSYWS SEQ ID NO:5680 | EINLSGSTNYNPSLKS SEQ ID NO:13692 | DYGGLDY SEQ ID NO:21704 |
| iPS:434473 | 21-225_76D1 | NA | GGTTGCTACTGGAGC SEQ ID NO:5681 | GAAATCAATCATAGTGG AAGAACCAACTACAACC CGTCCCTCAAGAGT SEQ ID NO:13693 | GACTACGGCGGGTATGGACGT C SEQ ID NO:21705 |
| | | AA | GCYWS SEQ ID NO:5682 | EINHSGRTNYNPSLKS SEQ ID NO:13694 | DYGGMDV SEQ ID NO:21706 |
| iPS:434475 | 21-225_74F9 | NA | AATTATGATATCAAC SEQ ID NO:5683 | TGGATGAACCCTAACAG TGGTAACACAGGCTGTG CACAGAAGTTCCAGGGC SEQ ID NO:13695 | AGCAGTGGCTGGAACTTCTT TGACTAC SEQ ID NO:21707 |
| | | AA | NYDIN | WMNPNSGNTGCAQKFQG SEQ ID NO:13696 | SSGWNFFDY SEQ ID NO:21708 |
| iPS:434477 | | NA | AATTATGATATCAAC | TGGATGCACCTAACAG TGGTAACAGGCTATG CACAGAAGTTCCGGGC | AGCAGTGGCTGGTACTACTT TGACTAC |

FIGURE 49
(Continued)

| | | | | | | |
|---|---|---|---|---|---|---|
| iPS:434479 | 21-225_74A6 | AA | SEQ ID NO:5685<br>NYDIN | SEQ ID NO:13697<br>WMHPNSGNTGYAQKFRG | SEQ ID NO:21709<br>SSGWYYFDY | |
| | | NA | SEQ ID NO:5686<br>AATTATGATATCAAC | SEQ ID NO:13698<br>TGGATGCACCCTAACAG<br>TGGTAACACAGGCTATG<br>CACAGAAGTTCCAGGGC | SEQ ID NO:21710<br>AGTAGTGGCTGGTACTGGTT<br>CGACCCC | |
| iPS:434481 | 21-225_76H1 | AA | SEQ ID NO:5687<br>NYDIN | SEQ ID NO:13699<br>WMHPNSGNTGYAQKFQG | SEQ ID NO:21711<br>SSGWYWFDP | |
| | | NA | SEQ ID NO:5688<br>AATTATGATATCAAC | SEQ ID NO:13700<br>TGGATGCACCCTAACAG<br>TGGTAACACAGGCTTTG<br>CACAGAAGTTCCAGGGC | SEQ ID NO:21712<br>TCCAGTGGCTGGTACTGGTT<br>CGACCCC | |
| iPS:434483 | 21-225_74B10 | AA | SEQ ID NO:5689<br>NYDIN | SEQ ID NO:13701<br>WMHPNSGNTGFAQKFQG | SEQ ID NO:21713<br>SSGWYWFDP | |
| | | NA | SEQ ID NO:5690<br>AATTATGATATCAAC | SEQ ID NO:13702<br>TGGATGAACCCTAACAG<br>TGGTAACACAGGCTATG<br>CACAGAAGTTCCAGGGC | SEQ ID NO:21714<br>AGCAGTGGCTGGTACTGGTT<br>CGACCCC | |
| iPS:434485 | 21-225_74C12 | AA | SEQ ID NO:5691<br>NYDIN | SEQ ID NO:13703<br>WMNPNSGNTGYAQKFQG | SEQ ID NO:21715<br>SSGWYWFDP | |
| | 21-225_76D2 | NA | SEQ ID NO:5692<br>AGCTATGGCATGCAC | SEQ ID NO:13704<br>GTTATTGGTATGATGGA<br>AGTAATAAATACTATGC<br>AGACTCCGTGAAGGGC | SEQ ID NO:21716<br>GATGCAATATAGTGGAGC<br>TACTTACTTGAGTCC | |
| | | | SEQ ID NO:5693 | SEQ ID NO:13705 | SEQ ID NO:21717 | |

FIGURE 49
(Continued)

| | | | | VIWYDGSNKYYADSVKG | DRNIVGATYFES |
|---|---|---|---|---|---|
| | | AA | SYGMH | SEQ ID NO:13706 | SEQ ID NO:21718 |
| iPS:434487 | 21-225_76G2 | NA | AATTATGATATCAAC | TGGATGAACCCTAACAG TGGTAACACAGGCTATG CACAGAAGTTCCAGGGC | AGCAGTGGCTGGTACATGTT TGACTAC |
| | | | | SEQ ID NO:13707 | SEQ ID NO:21719 |
| | | AA | NYDIN | WMNPNSGNTGYAQKFQG | SSGWYMFDY |
| | | | SEQ ID NO:5696 | SEQ ID NO:13708 | SEQ ID NO:21720 |
| iPS:434489 | 21-225_74E4 | NA | AGTAGTAATTACTACTGGGG C | AGTATCTATTATAGTGGA TACACCTCCTACAACCCG TCCCTCAAGAGT | CTTGACTCTAACTGGGGTCT TGACTAC |
| | | | SEQ ID NO:5697 | SEQ ID NO:13709 | SEQ ID NO:21721 |
| | | AA | SSNYYWG | SIYYSGYTSYNPSLKS | LDSNWGLDY |
| | | | SEQ ID NO:5698 | SEQ ID NO:13710 | SEQ ID NO:21722 |
| iPS:434493 | 21-225_76F3 | NA | AATTATGATATCAAC | TGGATGAACCCTAACAG TGGTAACACAGGCTATG CACAGAAGTTCCAGGGC | TCCAGTGGCTGGTGAACTGGTT CGACCCC |
| | | | | SEQ ID NO:13711 | SEQ ID NO:21723 |
| | | AA | NYDIN | WMNPNSGNTGYAQKFQG | SSGWNWFDP |
| | | | SEQ ID NO:5700 | SEQ ID NO:13712 | SEQ ID NO:21724 |
| iPS:434495 | 21-225_74B2 | NA | GGTCCCTACTGGAGC | GAAATCAATCATAGTGG AAGCACCAACTACAACC CGTCCCCTCACGAGT | GACTACGGGGGTTTGGACGT C |
| | | | SEQ ID NO:5701 | SEQ ID NO:13713 | SEQ ID NO:21725 |
| | | AA | GPYWS | EINHSGSTNYNPSLTS | DYGGLDV |
| | | | SEQ ID NO:5702 | SEQ ID NO:13714 | SEQ ID NO:21726 |

FIGURE 49
(Continued)

| | | | | |
|---|---|---|---|---|
| iPS:434497 | 21-225_76A4 | NA | GGTTGCTACTGGAGC | GAAATCAATCATAGTGGAAGCACCAACTACAACCCGTCCCTCAAGAGT | GACTACGGCGGTATGGACGTC |
| | | | SEQ ID NO:5703 | SEQ ID NO:13715 | SEQ ID NO:21727 |
| | | AA | GCYWS | EINHSGSTNYNPSLKS | DYGGMDV |
| | | | SEQ ID NO:5704 | SEQ ID NO:13716 | SEQ ID NO:21728 |
| iPS:434501 | 21-225_76G4 | NA | GGTTGCTACTGGAGC | GAAATCAATCATAGTGGAAGCACCAACTACAACCACGTCCCTCAAGAGT | GACTACGGCGGTATGGACGTC |
| | | | SEQ ID NO:5705 | SEQ ID NO:13717 | SEQ ID NO:21729 |
| | | AA | GCYWS | EINHSGSTNYNPSLKS | DYGGMDV |
| | | | SEQ ID NO:5706 | SEQ ID NO:13718 | SEQ ID NO:21730 |
| iPS:434503 | 21-225_74D7 | NA | AGAAGTAGTTACTACTGGGGC | GGTATCTATTATAGTGGGAGCACCTCCTACAACCCGTCCCTCAAGAGT | CTGCGACCTAACTGGGACTTTGACTAC |
| | | | SEQ ID NO:5707 | SEQ ID NO:13719 | SEQ ID NO:21731 |
| | | AA | RSSYYWG | GIYYSGSTSYNPSLKS | LRPNWDFDY |
| | | | SEQ ID NO:5708 | SEQ ID NO:13720 | SEQ ID NO:21732 |
| iPS:434507 | 21-225_74C5 | NA | GGTTGCTACTGGAGC | GAAATCAATCATAGTGGATGCACCAACTTCAACCCGTCCCTCAAGAGT | GACTACGGCGGTATGGACGTC |
| | | | SEQ ID NO:5709 | SEQ ID NO:13721 | SEQ ID NO:21733 |
| | | AA | GCYWS | EINHSGCTNFNPSLKS | DYGGMDV |
| | | | SEQ ID NO:5710 | SEQ ID NO:13722 | SEQ ID NO:21734 |
| iPS:434509 | 21-225_76F5 | NA | AATTATGATATCAAC | TGGATGAACCCTAACAGTGGTAACACAGGCTATGCACAGAAGTTCCAGGGC | AGCAGTGGCTGGTACTGGTTCGACCCC |
| | | | SEQ ID NO:5711 | SEQ ID NO:13723 | SEQ ID NO:21735 |
| | | AA | NYDIN | WMNPNSGNTGYAQKFQG | SSGWYWFDP |

FIGURE 49
(Continued)

| | | | | | | |
|---|---|---|---|---|---|---|
| iPS:434511 | 21-225_74B11 | NA | SEQ ID NO:5712 AATTATGATATCAAC | SEQ ID NO:13724 TGGATGCACCCTAACAGTGGTAACACAGGCTATGCACAGAAGTTCCAGGGC | SEQ ID NO:21736 AGCAGTGGCTGGTACTACTTTGACTAC | |
| | | AA | SEQ ID NO:5713 NYDIN | SEQ ID NO:13725 WMHPNSGNTGYAQKFQG | SEQ ID NO:21737 SSGWYYFDY | |
| iPS:434513 | 21-225_76A6 | NA | SEQ ID NO:5714 AATTATGATATCAAC | SEQ ID NO:13726 TGGATGCACCCTAACAATGGTAACACAGGCTATGCACAGAAGTTCCAGGGC | SEQ ID NO:21738 AGCAGTGGCTGGTACTGGTTCGACCCC | |
| | | AA | SEQ ID NO:5715 NYDIN | SEQ ID NO:13727 WMHPNNGNTGYAQKFQG | SEQ ID NO:21739 SSGWYWFDP | |
| iPS:434515 | 21-225_74A5 | NA | SEQ ID NO:5716 AATTATGATATCAAC | SEQ ID NO:13728 TGGATGCACCCTAACAGTGGTAACACAGGCTATGCACAGAAGTTCCAGGGC | SEQ ID NO:21740 AGTAGTGGCTGGTACTGGTTCGACCCC | |
| | | AA | SEQ ID NO:5717 NYDIN | SEQ ID NO:13729 WMHPNSGNTGYAQKFQG | SEQ ID NO:21741 SSGWYWFDP | |
| iPS:434517 | 21-225_76A7 | NA | SEQ ID NO:5718 GGTTGCTACTGGAGC | SEQ ID NO:13730 GAAATCAATCATATGTGGAAGGACCAACTACAACCCGTCCCTCAAGAGT | SEQ ID NO:21742 GACTACGGTGGGCTTGACTAC | |
| | | AA | SEQ ID NO:5719 GCYWS | SEQ ID NO:13731 EINHSGRTNYNPSLKS | SEQ ID NO:21743 DYGGLDY | |
| | | | SEQ ID NO:5720 | SEQ ID NO:13732 | SEQ ID NO:21744 | |

FIGURE 49
(Continued)

| | | | | | |
|---|---|---|---|---|---|
| iPS:434519 | 21-225_74C7 | NA | GGTTCCTACTGGAGC | GAAATCAATCTTAGTGG AAGCACCAACTACAACC CGTCCCTCAAGAGT | GACTACGGTGGCCTTGACTA C |
| | | | SEQ ID NO:5721 | SEQ ID NO:13733 | SEQ ID NO:21745 |
| | | AA | GSYWS | EINLSGSTNYNPSLKS | DYGGLDY |
| | | | SEQ ID NO:5722 | SEQ ID NO:13734 | SEQ ID NO:21746 |
| iPS:434523 | 21-225_75C3 | NA | GGTTGCTACTGGAGC | GAAATCAATTATAGTGG AAGAACCAACTACAACC CGTCCCTCAAGAGT | GACTACGGCGGTATGGACGT C |
| | | | SEQ ID NO:5723 | SEQ ID NO:13735 | SEQ ID NO:21747 |
| | | AA | GCYWS | EINYSGRTNYNPSLKS | DYGGMDV |
| | | | SEQ ID NO:5724 | SEQ ID NO:13736 | SEQ ID NO:21748 |
| iPS:434525 | 21-225_76E8 | NA | AATTATGATATCAAC | TGGATGAACCCTAACAG TGGTAACACAGGCTATG CACAGAAGTTCCAGGGC | TCCAGTGGCTGGCACTGGTT CGACCCC |
| | | | SEQ ID NO:5725 | SEQ ID NO:13737 | SEQ ID NO:21749 |
| | | AA | NYDIN | WMNPNSGNTGYAQKFQG | SSGWHWFDP |
| | | | SEQ ID NO:5726 | SEQ ID NO:13738 | SEQ ID NO:21750 |
| iPS:434529 | 21-225_76B9 | NA | AATTATGATATCAAC | TGGATGCACCCTAACAG TGGTAACACAGGCTATG CACAGAAGTTCCAGGGC | AGTAGTGGCTGGTACTGGTT CGACCCC |
| | | | SEQ ID NO:5727 | SEQ ID NO:13739 | SEQ ID NO:21751 |
| | | AA | NYDIN | WMHPNSGNTGYAQKFQG | SSGWYWFDP |
| | | | SEQ ID NO:5728 | SEQ ID NO:13740 | SEQ ID NO:21752 |
| iPS:434531 | 21_225_76C9 | NA | AACGCCCTGGATGAAC | CGTATTAAAAACAAAGC TGATGGTGGGACAACAG ACTTCGCTGCACCCGTGA AAGGC | GTGGGACCTACTACGGACTA C |

FIGURE 49
(Continued)

| | | | | | | |
|---|---|---|---|---|---|---|
| iPS:434533 | 21-225_76C9 | AA | SEQ ID NO:5729 NAWMN | SEQ ID NO:13741 RIKNKADGGTTDFAAPVK G | SEQ ID NO:21753 VGPTTDY |
| | | NA | SEQ ID NO:5730 GGTCCCTACTGGAGC | SEQ ID NO:13742 GAAATCAATCATAGTGG AAGCACCACTACAACC CGTCCCTCAAGAGT | SEQ ID NO:21754 GACTACGGGGGTTTGGACGT C |
| iPS:434535 | 21-225_85F7 | AA | SEQ ID NO:5731 GPYWS | SEQ ID NO:13743 EINHSGSTNYNPSLKS | SEQ ID NO:21755 DYGGLDV |
| | | NA | SEQ ID NO:5732 AGCTATGGCATGCAC | SEQ ID NO:13744 GTTATATGGTATGGATGG AAGTAATAAAACTATG CAGACTCCGTGAAGGGC | SEQ ID NO:21756 GATGGCAGCTATGGTTATGA CGGCCTTGACTAC |
| iPS:434537 | 21-225_74C8 | AA | SEQ ID NO:5733 SYGMH | SEQ ID NO:13745 VIWYDGSNKYYADSVKG | SEQ ID NO:21757 DGSYGYDGLDY |
| | | NA | SEQ ID NO:5734 AGCTATGGCATGCAC | SEQ ID NO:13746 GTTATTGGTATGATGGA AGTAATAAATACTATGC AGACTCCGTGAAGGGC | SEQ ID NO:21758 GATCGCAATATAGTGGAGC TACTTACTTTGAGTCC |
| iPS:434539 | 21-225_74E11 | AA | SEQ ID NO:5735 SYGMH | SEQ ID NO:13747 VIWYDGSNKYYADSVKG | SEQ ID NO:21759 DRNIVGATYFES |
| | | NA | SEQ ID NO:5736 GATTACTACTGGAGC | SEQ ID NO:13748 GAAATCAATCATAGTGG AGACACCAACTACAACC CGTCCCTCAAGAGT | SEQ ID NO:21760 GAGTTCCATATAGTGGAAG CTACCTCTACTACTGGTA TGGACGTC |
| | 21-225_74A2 | | SEQ ID NO:5737 | SEQ ID NO:13749 | SEQ ID NO:21761 |

FIGURE 49
(Continued)

| | | | AA | DYYWS | | EINHSGDTNYNPSLKS | | EFPYSGSYLYYYGMDV | |
|---|---|---|---|---|---|---|---|---|---|
| iPS:434547 | | | | SEQ ID NO:5738 | | SEQ ID NO:13750 | | SEQ ID NO:21762 | |
| | 21-225_74H5 | | NA | GGTTGCTACTGGAGC | | GAAATCAATCATAGTGG AAGGACCAACTTCAACC CGTCCCTCAAGAGT | | GACTACGGCGGGTATGGACGT C | |
| | | | | SEQ ID NO:5739 | | SEQ ID NO:13751 | | SEQ ID NO:21763 | |
| | | | AA | GCYWS | | EINHSGRTNFNPSLKS | | DYGGMDV | |
| iPS:434549 | | | | SEQ ID NO:5740 | | SEQ ID NO:13752 | | SEQ ID NO:21764 | |
| | 21-225_76E11 | | NA | AATTATGATATCAAC | | TGGATGAACCCTAACAG TGGTAACACAGGCTATG CACAGAAGTTCCAGGGC | | AGCAGTGGCTGGTACTACTT TGACTAC | |
| | | | | SEQ ID NO:5741 | | SEQ ID NO:13753 | | SEQ ID NO:21765 | |
| | | | AA | NYDIN | | WMNPNSGNTGYAQKFQG | | SSGWYYFDY | |
| iPS:434551 | | | | SEQ ID NO:5742 | | SEQ ID NO:13754 | | SEQ ID NO:21766 | |
| | 21-225_75C4 | | NA | AATTATGATATCAAC | | TGGATGCATCCTAACAG TGGTAACACAGGCTATG CACAGAAGTTCCAGGGC | | AGCAGTGGCTGGTACTACTT TGACTAC | |
| | | | | SEQ ID NO:5743 | | SEQ ID NO:13755 | | SEQ ID NO:21767 | |
| | | | AA | NYDIN | | WMHPNSGNTGYAQKFQG | | SSGWYYFDY | |
| iPS:434559 | | | | SEQ ID NO:5744 | | SEQ ID NO:13756 | | SEQ ID NO:21768 | |
| | 21-225_74D11 | | NA | GGTTGCTACTGGAGC | | GAAATCAATCATAGTGG AAGCACCAACTACAACC CGTCCCTCAAGAGT | | GACTACGGCGGGTATGGACGT C | |
| | | | | SEQ ID NO:5745 | | SEQ ID NO:13757 | | SEQ ID NO:21769 | |
| | | | AA | GCYWS | | EINHSGSTNYNPSLKS | | DYGGMDV | |
| | | | | SEQ ID NO:5746 | | SEQ ID NO:13758 | | SEQ ID NO:21770 | |

FIGURE 49
(Continued)

| | | | | | |
|---|---|---|---|---|---|
| iPS:434561 | 21-225_77G1 | NA | GGTTGCTACTGGAGC SEQ ID NO:5747 | GAAATCAATCATAGTGG AAGCACCAACTACAACC CGTCCCTCAAGAGT SEQ ID NO:13759 | GACTACGGGCGGTATGGACGT C SEQ ID NO:21771 |
| | | AA | GCYWS SEQ ID NO:5748 | EINHSGSTNYNPSLKS SEQ ID NO:13760 | DYGGMDV SEQ ID NO:21772 |
| iPS:434563 | 21-225_75D8 | NA | AACTACGACATGCAC SEQ ID NO:5749 | GCTATTGGTACTGCTGGT GACACATACTATCCAGG CTCCGTGAAGGGC SEQ ID NO:13761 | GTTCTTGACTACGGTGACTC CTTGGGCTACTACTACTACG GTATGGACGTC SEQ ID NO:21773 |
| | | AA | NYDMH SEQ ID NO:5750 | AIGTAGDTYYPGSVKG SEQ ID NO:13762 | VLDYGDSLGYYYYGMDV SEQ ID NO:21774 |
| iPS:434565 | 21-225_75B10 | NA | GGTTACTACTGGAGC SEQ ID NO:5751 | GAAATCAATCACAGTGG AAGCACCAACTACAACC CGTCCCTCAAGAGT SEQ ID NO:13763 | GACTACGGTGGTTGGACGT C SEQ ID NO:21775 |
| | | AA | GYYWS SEQ ID NO:5752 | EINHSGSTNYNPSLKS SEQ ID NO:13764 | DYGGLDV SEQ ID NO:21776 |
| iPS:434569 | 21-225_77H5 | NA | AATTATGGCATGCAC SEQ ID NO:5753 | GTTATATGGTATGATGG AAGAAATAAATACTATG CAGACTCCGTGAAGGGC SEQ ID NO:13765 | GATCGGAGTATATTGGGAGC TACTTCTTTGACTAC SEQ ID NO:21777 |
| | | AA | NYGMH SEQ ID NO:5754 | VIWYDGRNKYYADSVKG SEQ ID NO:13766 | DRSILGATFFDY SEQ ID NO:21778 |
| iPS:434571 | 21-225_74D2 | NA | GGTTGCTACTGGAGC SEQ ID NO:5755 | GAAATCAATCATAGTGG AAGGACCAACTACAACC CGTCCCTCAAGAGT SEQ ID NO:13767 | GACTACGGTGGGCTTGACTA C SEQ ID NO:21779 |

FIGURE 49
(Continued)

| | | | | GCYWS | | EINHSGRTNYNPSLKS | | DYGGLDY | |
|---|---|---|---|---|---|---|---|---|---|
| iPS:434573 | | AA | | SEQ ID NO:5756 | | SEQ ID NO:13767 | | SEQ ID NO:21780 | |
| | 21-225_77E6 | NA | | AGTTATGGCATGCAC | | GTTATATGGTATGATGG AAGTAATCAAAACTATG CAGACTCCGTGAAGGGC | | GATGGCAGCTATGGTTACGA CGGCCTTGACTAC | |
| | | | | SEQ ID NO:5757 | | SEQ ID NO:13768 | | SEQ ID NO:21781 | |
| iPS:434575 | | AA | | SYGMH | | VIWYDGSNQNYADSVKG | | DGSYGYDGLDY | |
| | | | | SEQ ID NO:5758 | | SEQ ID NO:13769 | | SEQ ID NO:21782 | |
| | 21-225_77C7 | NA | | AATTATGATATCAAC | | TGGATGAACCCTAACAG TGGTAACACAGGCTATG CACAGAAGTTCCAGGGC | | TCCAGTGGCTGGCACTGGTT CGACCCC | |
| | | | | SEQ ID NO:5759 | | SEQ ID NO:13770 | | SEQ ID NO:21783 | |
| iPS:434579 | | AA | | NYDIN | | WMNPNSGNTGYAQKFQG | | SSGWHWFDP | |
| | | | | SEQ ID NO:5760 | | SEQ ID NO:13771 | | SEQ ID NO:21784 | |
| | 21-225_77F7 | NA | | GGTTGCTACTGGAGC | | GAAATCAATCATAGTGG AAGCACCAACTACAACC CGTCCCTCAAGAGT | | GACTACGGCGGGTATGGACGT C | |
| | | | | SEQ ID NO:5761 | | SEQ ID NO:13772 | | SEQ ID NO:21785 | |
| iPS:434581 | | AA | | GCYWS | | EINHSGSTNYNPSLKS | | DYGGMDV | |
| | | | | SEQ ID NO:5762 | | SEQ ID NO:13773 | | SEQ ID NO:21786 | |
| | 21-225_74B12 | NA | | GGTTGCTACTGGAGC | | GAAATCAATCATAGTGG AAGCACCAACTACAACC CGTCCCTCAAGAGT | | GACTACGGCGGGTATGGACGT C | |
| | | | | SEQ ID NO:5763 | | SEQ ID NO:13774 | | SEQ ID NO:21787 | |
| | | AA | | GCYWS | | EINHSGSTNYNPSLKS | | DYGGMDV | |
| | | | | SEQ ID NO:5764 | | SEQ ID NO:13776 | | SEQ ID NO:21788 | |

FIGURE 49
(Continued)

| | | | | | |
|---|---|---|---|---|---|
| iPS:434583 | 21-225_74B6 | NA | AATTATGATATCAAC | TGGATGCACCCTAACAA TGGTAACACAGGCTATG CACAGAAGTTCCAGGGC | AGCAGTGGCTGGTACTGGTT CGACCCC |
| | | | SEQ ID NO:5765 | SEQ ID NO:13777 | SEQ ID NO:21789 |
| | | AA | NYDIN | WMHPNSGNTGYAQKFQG | SSGWYWFDP |
| | | | SEQ ID NO:5766 | SEQ ID NO:13778 | SEQ ID NO:21790 |
| iPS:434585 | 21-225_75A12 | NA | GGTTGCTACTGGAGC | GAAATCAATTATAGTGG AAGAACCAACTACAACC CGTCCCTCAAGAGT | GACTACGGCGGTATGGACGT C |
| | | | SEQ ID NO:5767 | SEQ ID NO:13779 | SEQ ID NO:21791 |
| | | AA | GCYWS | EINYSGRTNYNPSLKS | DYGGMDV |
| | | | SEQ ID NO:5768 | SEQ ID NO:13780 | SEQ ID NO:21792 |
| iPS:434587 | 21-225_74G3 | NA | AATTATGATATCAAC | TGGATGCACCCTAACAG TGGTAACACAGGCTATG CACAGAAGTTCCAGGGC | AGTAGTGGCTGGTACTGGTT CGACCCC |
| | | | SEQ ID NO:5769 | SEQ ID NO:13781 | SEQ ID NO:21793 |
| | | AA | NYDIN | WMHPNSGNTGYAQKFQG | SSGWYWFDP |
| | | | SEQ ID NO:5770 | SEQ ID NO:13782 | SEQ ID NO:21794 |
| iPS:434595 | 21-225_77A10 | NA | GGTTGCTACTGGAGC | GAAATCAATTATAGTGG AAGAACCAACTACAACC CGTCCCTCAAGAGT | GACTACGGCGGTATGGACGT C |
| | | | SEQ ID NO:5771 | SEQ ID NO:13783 | SEQ ID NO:21795 |
| | | AA | GCYWS | EINYSGRTNYNPSLKS | DYGGMDV |
| | | | SEQ ID NO:5772 | SEQ ID NO:13784 | SEQ ID NO:21796 |
| iPS:434597 | 21-225_77C10 | NA | AATTATGATATCAAC | TGGATGCACCCTAACAG TGGTAACACAGGCTATG CACAGAAGTTCCAGGGC | AGCAGTGGCTGGTACTGGTT CGACCCC |
| | | | SEQ ID NO:5773 | SEQ ID NO:13785 | SEQ ID NO:21797 |

FIGURE 49
(Continued)

| | | AA | NYDIN | SEQ ID NO:5774 | WMHPNSGNTGYAQKFQG | SEQ ID NO:13786 | SSGWYWFDP | SEQ ID NO:21798 |
|---|---|---|---|---|---|---|---|---|
| iPS:434603 | 21-225_77D11 | NA | AATTATGATATCAAC | SEQ ID NO:5775 | TGGATGCACCCTAACAGTGGTAACACAGGCTATGCACAGAAGTTCCAGGGC | SEQ ID NO:13787 | AGTAGTGGCTGGTACTGGTTCGACCCC | SEQ ID NO:21799 |
| | | AA | NYDIN | SEQ ID NO:5776 | WMHPNSGNTGYAQKFQG | SEQ ID NO:13788 | SSGWYWFDP | SEQ ID NO:21800 |
| iPS:434611 | 21-225_77C12 | NA | GGTTCCTACTGGAGC | SEQ ID NO:5777 | GAAATCAATTATAGGGGAAGCACCAACTACAACCCGTCCCTCAAGAGT | SEQ ID NO:13789 | GACTACGGGCGGTATGGACGTC | SEQ ID NO:21801 |
| | | AA | GSYWS | SEQ ID NO:5778 | EINYRGSTNYNPSLKS | SEQ ID NO:13790 | DYGGMDV | SEQ ID NO:21802 |
| iPS:434613 | 21-225_77D12 | NA | AATTATGATATCAAC | SEQ ID NO:5779 | TGGATGAACCCTAACAGTGGTAACACAGGCTATGCACAGAAGTTCCAGGGC | SEQ ID NO:13791 | AGCAGTGGCTGGTACTGGTTCGACCCC | SEQ ID NO:21803 |
| | | AA | NYDIN | SEQ ID NO:5780 | WMNPNSGNTGYAQKFQG | SEQ ID NO:13792 | SSGWYWFDP | SEQ ID NO:21804 |
| iPS:434615 | 21-225_76C5 | NA | AGCTATGGCATGCAC | SEQ ID NO:5781 | GTTATATGGTATGATGGAAGTAATAAAAACTATGCAGACTCCGTGAAGGGC | SEQ ID NO:13793 | GATGGCAGCTATGGTTACGACGGCCTTGACTAC | SEQ ID NO:21805 |
| | | AA | SYGMH | | VIWYDGSNKNYADSVKG | | DGSYGYDGLDY | |

FIGURE 49
(Continued)

| | | | | | | |
|---|---|---|---|---|---|---|
| iPS:434617 | 21-225_74B8 | NA | SEQ ID NO:5782<br>AATTATGATATCAAC | SEQ ID NO:13794<br>TGGATGCACCCTAACAG<br>TGGTAACACAGGCTATG<br>CACAGAAGTTCCAGGGC | SEQ ID NO:21806<br>TCCAGTGGCTGGTACTGGTT<br>CGACCCC |
| | | AA | SEQ ID NO:5783<br>NYDIN | SEQ ID NO:13795<br>WMHPNSGNTGYAQKFQG | SEQ ID NO:21807<br>SSGWYWFDP |
| iPS:434619 | 21-225_78C1 | NA | SEQ ID NO:5784<br>AATTATGATATCAAC | SEQ ID NO:13796<br>TGGATGCACCCTAACAG<br>TGGTAACACAGGCTATG<br>CACAGAAGTTCCAGGGC | SEQ ID NO:21808<br>AGCAGTGGCTGGTACTGGTT<br>CGACCCC |
| | | AA | SEQ ID NO:5785<br>NYDIN | SEQ ID NO:13797<br>WMHPNSGNTGYAQKFQG | SEQ ID NO:21809<br>SSGWYWFDP |
| iPS:434621 | 21-225_74D1 | NA | SEQ ID NO:5786<br>AGCTATGGCATGCAC | SEQ ID NO:13798<br>GTTATATGGTATGATGGA<br>AGTAATAAATACCATG<br>CAGACTCCGTGAAGGGC | SEQ ID NO:21810<br>GATGAGGGGTTCGGGAGTT<br>CGACTACTACAACTACGGTA<br>TGGACGTC |
| | | AA | SEQ ID NO:5787<br>SYGMH | SEQ ID NO:13799<br>VIWYDGSNKYHADSVKG | SEQ ID NO:21811<br>DEGFGEFDYYNYGMDV |
| iPS:434629 | 21-225_74C3 | NA | SEQ ID NO:5788<br>AGCTTTGGCATGCAC | SEQ ID NO:13800<br>GCTATTTGGTATGATGGA<br>AGTAATAAATACTGTGC<br>AGACTCCGTGAAGGGC | SEQ ID NO:21812<br>GATCGGAGTATACTGGAGC<br>TGCTTTCTTTGACTAC |
| | | AA | SEQ ID NO:5789<br>SFGMH | SEQ ID NO:13801<br>AIWYDGSNKYCADSVKG | SEQ ID NO:21813<br>DRSILGAAFFDY |
| | | | SEQ ID NO:5790 | SEQ ID NO:13802 | SEQ ID NO:21814 |

FIGURE 49
(Continued)

| | | | | | | |
|---|---|---|---|---|---|---|
| iPS:434633 | 21-225_74G8 | NA | AACGCCTGGATGAAC | SEQ ID NO:5791 | CGTATTAAAAACAAAGCTGATGGTGGGACAACAGACTACGCTGCACCCGTGAAAGGC | SEQ ID NO:13803 | GTGGGAGCTACTACGGACTAC | SEQ ID NO:21815 |
| | | AA | NAWMN | SEQ ID NO:5792 | RIKNKADGGTTDYAAPVKG | SEQ ID NO:13804 | VGATTDY | SEQ ID NO:21816 |
| iPS:434635 | 21-225_78E6 | NA | AATTATGATATCAAC | SEQ ID NO:5793 | TGGATGCACCCTAACAGTGGTAACACAGGCTATGCACAGAAGTTCCAGGGC | SEQ ID NO:13805 | AGTAGTGGCTGGTACAAATTTGACTAC | SEQ ID NO:21817 |
| | | AA | NYDIN | SEQ ID NO:5794 | WMHPNSGNTGYAQKFQG | SEQ ID NO:13806 | SSGWYKFDY | SEQ ID NO:21818 |
| iPS:434637 | 21-225_78E7 | NA | GGTTCCTACTGGAGC | SEQ ID NO:5795 | GAAATCAATCTTAGTGGAAGCACCAACTACAACCCGTCCCTCAAGAGT | SEQ ID NO:13807 | GACTACGGTGGCCTTGACTAC | SEQ ID NO:21819 |
| | | AA | GSYWS | SEQ ID NO:5796 | EINLSGSTNYNPSLKS | SEQ ID NO:13808 | DYGGLDY | SEQ ID NO:21820 |
| iPS:434639 | 21-225_74B7 | NA | AATTATGATATCAAC | SEQ ID NO:5797 | TGGATGAACCCTAACAGTGGTAACACAGGCTATGCACAGAAGTTCCAGGGC | SEQ ID NO:13809 | TCCAGTGGCTGGCACTGGTTCGACCCC | SEQ ID NO:21821 |
| | | AA | NYDIN | SEQ ID NO:5798 | WMNPNSGNTGYAQKFQG | SEQ ID NO:13810 | SSGWHWFDP | SEQ ID NO:21822 |

FIGURE 49
(Continued)

| | | | | | |
|---|---|---|---|---|---|
| iPS:434649 | 21-225_78E11 | NA | AATTATGATATCAAC | TGGATGAACCCTAACAG TGGTAACACAGGCTGTG CACAGAAGTTCCAGGGC | AGCAGTGGCTGGAACTTCTT TGACTAC |
| | | | SEQ ID NO:5799 | SEQ ID NO:13811 | SEQ ID NO:21823 |
| | | AA | NYDIN | WMNPNSGNTGCAQKFQG | SSGWNFFDY |
| | | | SEQ ID NO:5800 | SEQ ID NO:13812 | SEQ ID NO:21824 |
| iPS:434653 | 21-225_74B5 | NA | AATTATGATATCAAC | TGGATGAACCCTAACAG TGGTAACACAGGCTATG CACAGAAGTTCCAGGGC | TCCAGTGGCTGGAACTGGTT CGACCCC |
| | | | SEQ ID NO:5801 | SEQ ID NO:13813 | SEQ ID NO:21825 |
| | | AA | NYDIN | WMNPNSGNTGYAQKFQG | SSGWNWFDP |
| | | | SEQ ID NO:5802 | SEQ ID NO:13814 | SEQ ID NO:21826 |
| iPS:434655 | 21-225_78H12 | NA | AATTATGATATCAAC | TGGATGAACCCTAACAG TGGTAACACAGGCTATG CACAGAAGTTCCAGGGC | TCCAGTGGCTGGCACTGGTT CGACCCC |
| | | | SEQ ID NO:5803 | SEQ ID NO:13815 | SEQ ID NO:21827 |
| | | AA | NYDIN | WMNPNSGNTGYAQKFQG | SSGWHWFDP |
| | | | SEQ ID NO:5804 | SEQ ID NO:13816 | SEQ ID NO:21828 |
| iPS:434657 | 21-225_79G1 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5805 | SEQ ID NO:13817 | SEQ ID NO:21829 |
| | | AA | GCYWS | EINHSGSTNYNPSLKS | DYGGMDV |
| | | | SEQ ID NO:5806 | SEQ ID NO:13818 | SEQ ID NO:21830 |
| iPS:434663 | 21_225_79F3 | NA | GGTTGCTACTGGAGC | GAAATCAATCATAGTGG AAGCACCAACTACAACC CGTCCCTCAAGAGT | GACTACGGGGGTATGGACGT C |

FIGURE 49
(Continued)

| | | | | | | |
|---|---|---|---|---|---|---|
| iPS:434665 | 21-225_79F3 | AA | SEQ ID NO:5807<br>GCYWS | SEQ ID NO:13819<br>EINHSGSTNYNPSLKS | SEQ ID NO:21831<br>DYGGMDV |
| | | NA | SEQ ID NO:5808<br>AATTATGATGTCAAC | SEQ ID NO:13820<br>TGGATGCACCTAACAG<br>TGGTAACACAGGCTATG<br>CACAGAAGTTCCAGGGC | SEQ ID NO:21832<br>AGCAGTGGCTGGTACCATTT<br>TGACTAC |
| iPS:434669 | 21-225_74G4 | AA | SEQ ID NO:5809<br>NYDVN | SEQ ID NO:13821<br>WMHPNSGNTGYAQKFQG | SEQ ID NO:21833<br>SSGWYHFDY |
| | | NA | SEQ ID NO:5810<br>AACTATGGCATGCAC | SEQ ID NO:13822<br>GTTATATGGTATGGATGG<br>AAGTAATCAAAACTATG<br>CAGACTCCGTGAAGGGC | SEQ ID NO:21834<br>GATGGCAGCTATGGTTATGA<br>CGGCCTTGACTAC |
| iPS:434671 | 21-225_79F4 | AA | SEQ ID NO:5811<br>NYGMH | SEQ ID NO:13823<br>VIWYDGSNQNYADSVKG | SEQ ID NO:21835<br>DGSYGYDGLDY |
| | | NA | SEQ ID NO:5812<br>AACGCCTGGATGAAC | SEQ ID NO:13824<br>CGAATTAAAAACAAAAT<br>TGATGGTGGGACAACAG<br>ACTACGCTGCACCCGTG<br>AAAGGC | SEQ ID NO:21836<br>GTGGGAGCTACTACGGACTA<br>C |
| iPS:434673 | 21-225_74F4 | AA | SEQ ID NO:5813<br>NAWMN | SEQ ID NO:13825<br>RIKNKIDGGTTDYAAPVK<br>G | SEQ ID NO:21837<br>VGAFTDY |
| | 21_225_74E3 | NA | SEQ ID NO:5814<br>AGCTATGGCATGCAC | SEQ ID NO:13826<br>GTTATTTGGTATGATGGA<br>AGTAATAAATACTATGC<br>AGACTCCGTGAAGGGC | SEQ ID NO:21838<br>GATCGCAATATAGTGGGAGC<br>TACTTACTTGAGTCC |

FIGURE 49
(Continued)

| | | | | | |
|---|---|---|---|---|---|
| iPS:434675 | 21-225_74E3 | AA | SEQ ID NO:5815 SYGMH | SEQ ID NO:13827 VIWYDGSNKYYADSVKG | SEQ ID NO:21839 DRNIVGATYFES |
| | | NA | SEQ ID NO:5816 AATTATGATATCAAC | SEQ ID NO:13828 TGGATGCACCCTAACAG TGGTAACACAGGCTTTG CACAGAAGTTCCAGGGC | SEQ ID NO:21840 TCCAGTGGCTGGTACTGGTT CGACCCC |
| iPS:434679 | 21-225_79G6 | AA | SEQ ID NO:5817 NYDIN | SEQ ID NO:13829 WMHPNSGNTGFAQKFQG | SEQ ID NO:21841 SSGWYWFDP |
| | | NA | SEQ ID NO:5818 AATTATGATATCAAC | SEQ ID NO:13830 TGGATGCACCCTAACAG TGGTAACACAGGCTATG CACAGAAGTTCCAGGGC | SEQ ID NO:21842 AGTAGTGGCTGGTACAAATT TGACTAC |
| iPS:434685 | 21-225_79G7 | AA | SEQ ID NO:5819 NYDIN | SEQ ID NO:13831 WMHPNSGNTGYAQKFQG | SEQ ID NO:21843 SSGWYKFDY |
| | | NA | SEQ ID NO:5820 AATTATGATATCAAC | SEQ ID NO:13832 TGGATGCATCCTAACAG TGGTAACACAGGCTATG CACAGAAGTTCCAGGGC | SEQ ID NO:21844 AGCAGTGGCTGGTACTACTT TGACTAC |
| iPS:434685 | 21-225_79E9 | AA | SEQ ID NO:5821 NYDIN | SEQ ID NO:13833 WMHPNSGNTGYAQKFQG | SEQ ID NO:21845 SSGWYYFDY |
| | | NA | SEQ ID NO:5822 GGTTGCTACTGGAGC | SEQ ID NO:13834 GAAATCAATCATAGTGG AAGCACCAACTACAACC CGTCCCTCAAGAGT | SEQ ID NO:21846 GACTACGGCGGTATGGACGT C |
| iPS:434687 | 21-225_75A5 | AA | SEQ ID NO:5823 GCYWS | SEQ ID NO:13835 EINHSGSTNYNPSLKS | SEQ ID NO:21847 DYGGMDV |

FIGURE 49 (Continued)

| | | | | | |
|---|---|---|---|---|---|
| iPS:434689 | 21-225_79G10 | NA | SEQ ID NO:5824 AATTATGATATCAAC | SEQ ID NO:13836 TGGATGAACCCTAACAG TGGTAACACAGGCTATG CACAGAAGTTCCAGGGC | SEQ ID NO:21848 TCCAGTGGCTGGAACTGGTT CGACCCC |
| | | AA | SEQ ID NO:5825 NYDIN | SEQ ID NO:13837 WMNPNSGNTGYAQKFQG | SEQ ID NO:21849 SSGWNWFDP |
| iPS:434691 | 21-225_75G7 | NA | SEQ ID NO:5826 GGTTCCTACTGGAGC | SEQ ID NO:13838 GAAATCAATTATAGGGG AAGCACCAACTACAACC CGTCCCTCAAGAGT | SEQ ID NO:21850 GACTACGGCGGTATGGACGT C |
| | | AA | SEQ ID NO:5827 GSYWS | SEQ ID NO:13839 EINYRGSTNYNPSLKS | SEQ ID NO:21851 DYGGMDV |
| iPS:434693 | 21-225_79F11 | NA | SEQ ID NO:5828 GGTTGCTACTGGAGC | SEQ ID NO:13840 GAAATCAATCATAGTGG AAGCACCAACTACAACC CGTCCCTCAAGAGT | SEQ ID NO:21852 GACTACGGCGGTATGGACGT C |
| | | AA | SEQ ID NO:5829 GCYWS | SEQ ID NO:13841 EINHSGSTNYNPSLKS | SEQ ID NO:21853 DYGGMDV |
| iPS:434697 | 21-225_79F12 | NA | SEQ ID NO:5830 AATTATGATATCAAC | SEQ ID NO:13842 TGGATGAACCCTAACAG TGGTAACACAGGCTATG CACAGAAGTTCCAGGGC | SEQ ID NO:21854 AGCAGTGGCTGGTACTTCTT TGACTAC |
| | | AA | SEQ ID NO:5831 NYDIN | SEQ ID NO:13843 WMNPNSGNTGYAQKFQG | SEQ ID NO:21855 SSGWYFFDY |
| iPS:434699 | 21-225_79G12 | NA | SEQ ID NO:5832 GGTTGCTACTGGAGC | SEQ ID NO:13844 GAAATCAATCATAGTGG AAGCACCAACTACAACC CGTCCCTCAAGAGT | SEQ ID NO:21856 GACTACGGCGGTATGGACGT C |

FIGURE 49
(Continued)

| | | | | | | |
|---|---|---|---|---|---|---|
| iPS:434701 | 21-225_79G12 | AA | SEQ ID NO:5833 GCYWS | SEQ ID NO:13845 EINHSGSTNYNPSLKS | SEQ ID NO:21857 DYGGMDV | |
| | | NA | SEQ ID NO:5834 GGTTGCTACTGGAGC | SEQ ID NO:13846 GAAATCAATCATAGTGG AAGCACCAACTACAACC CGTCCCTCAAGAGT | SEQ ID NO:21858 GACTACGGCGGGTATGGACGT C | |
| iPS:434703 | 21-225_80A1 | AA | SEQ ID NO:5835 GCYWS | SEQ ID NO:13847 EINHSGSTNYNPSLKS | SEQ ID NO:21859 DYGGMDV | |
| | | NA | SEQ ID NO:5836 GGTTGCTACTGGAGC | SEQ ID NO:13848 GAAATCAATCATAGTGG AAGCACCAACTACAACC CGTCCCTCAAGAGT | SEQ ID NO:21860 GACTACGGCGGGTATGGACGT C | |
| iPS:434705 | 21-225_80C1 | AA | SEQ ID NO:5837 GCYWS | SEQ ID NO:13849 EINHSGSTNYNPSLKS | SEQ ID NO:21861 DYGGMDV | |
| | | NA | SEQ ID NO:5838 AATTATGATATCAAC | SEQ ID NO:13850 TGGATGCACCTAACAG TGGTAACACAGGCTATG CACAGAAGTTCCAGGGC | SEQ ID NO:21862 AGTAGTGGCTGGTACTGGTT CGACCCC | |
| iPS:434707 | 21-225_80A2 | AA | SEQ ID NO:5839 NYDIN | SEQ ID NO:13851 WMHPNSGNTGYAQKFQG | SEQ ID NO:21863 SSGWYWFDP | |
| | | NA | SEQ ID NO:5840 AATTATGATATCAAC | SEQ ID NO:13852 TGGATGCACCTAACAG TGGTAACACAGGCTATG CACAGAAGTTCCAGGGC | SEQ ID NO:21864 AGCAGTGGCTGGTACTGGTT CGACCCC | |
| iPS:434709 | 21-225_80D3 | AA | SEQ ID NO:5841 NYDIN | SEQ ID NO:13853 WMHPNSGNTGYAQKFQG | SEQ ID NO:21865 SSGWYWFDP | |
| | | | SEQ ID NO:5842 | SEQ ID NO:13854 | SEQ ID NO:21866 | |

FIGURE 49
(Continued)

| iPS:434709 | 21-225_80E3 | NA | GGTTGCTACTGGAGC | GAAATCAATCATAGTGG AAGCACCAACAACTACAACC CGTCCCTCAAGAGT | GACTACGGGCGGGTATGGACGT C |
| --- | --- | --- | --- | --- | --- |
| | | | SEQ ID NO:5843 | SEQ ID NO:13855 | SEQ ID NO:21867 |
| | | AA | GCYWS | EINHSGSTNYNPSLKS | DYGGMDV |
| | | | SEQ ID NO:5844 | SEQ ID NO:13856 | SEQ ID NO:21868 |
| iPS:434713 | 21-225_80H3 | NA | AATTATGATATCAAC | TGGATGAACCCTAACAG TGGTAACACAGGCTATG CACAGAAGTTCCAGGGC | ACCAGTGGCTGGAACTTCTT TGACTAC |
| | | | SEQ ID NO:5845 | SEQ ID NO:13857 | SEQ ID NO:21869 |
| | | AA | NYDIN | WMNPNSGNTGYAQKFQG | TSGWNFFDY |
| | | | SEQ ID NO:5846 | SEQ ID NO:13858 | SEQ ID NO:21870 |
| iPS:434715 | 21-225_80D5 | NA | GGTCCCTACTGGAGC | GAAATCAATCATAGTGG AAGCACCAACAACTACAACC CGTCCCTCAAGAGT | GACTACGGGGGGTTGGACGT C |
| | | | SEQ ID NO:5847 | SEQ ID NO:13859 | SEQ ID NO:21871 |
| | | AA | GPYWS | EINHSGSTNYNPSLKS | DYGGLDV |
| | | | SEQ ID NO:5848 | SEQ ID NO:13860 | SEQ ID NO:21872 |
| iPS:434717 | 21-225_80A6 | NA | GGTTGCTACTGGAGC | GAAATCAATCATAGTGG AAGGACCAACAACTACAACC CGTCCCTCAAGAGT | GACTACGGTGGGCTTGACTA C |
| | | | SEQ ID NO:5849 | SEQ ID NO:13861 | SEQ ID NO:21873 |
| | | AA | GCYWS | EINHSGRTNYNPSLKS | DYGGLDY |
| | | | SEQ ID NO:5850 | SEQ ID NO:13862 | SEQ ID NO:21874 |
| iPS:434725 | 21-225_80H7 | NA | GGTTCCTACTGGAGC | GAAATCAATCAAAGTGG ACGCACCAACTACAACC CGTCCCTCAAGAGT | GACTACGGGGGTATAGACGT C |
| | | | SEQ ID NO:5851 | SEQ ID NO:13863 | SEQ ID NO:21875 |
| | | AA | GSYWS | EINQSGRTNYNPSLKS | DYGGIDV |

FIGURE 49
(Continued)

| | | | | | |
|---|---|---|---|---|---|
| iPS:434729 | 21-225_80B12 | NA | SEQ ID NO:5852 AATTATGATATCAAC | SEQ ID NO:13864 TGGATGAACCCTAACAG TGGTAACACAGGCTATG CACAGAAGTTCCAGGTC | SEQ ID NO:21876 AGCAGTGGCTGGTACATCTT TGACTAC |
| | | AA | SEQ ID NO:5853 NYDIN | SEQ ID NO:13865 WMNPNSGNTGYAQKFQV | SEQ ID NO:21877 SSGWYIFDY |
| iPS:434731 | 21-225_80E9 | NA | SEQ ID NO:5854 AATTATGATATCAAC | SEQ ID NO:13866 TGGATGCACCTAACAG TGGTAACACAGGCTATG CACAGAAGTTCCAGGGC | SEQ ID NO:21878 AGCAGTGGCTGGTACTGGTT CGACCCC |
| | | AA | SEQ ID NO:5855 NYDIN | SEQ ID NO:13867 WMHPNSGNTGYAQKFQG | SEQ ID NO:21879 SSGWYWFDP |
| iPS:434735 | 21-225_80B10 | NA | SEQ ID NO:5856 GGTGCTACTGGAGC | SEQ ID NO:13868 GAAATCAATCATAGTGG AAGCACCAACTACAACC CGTCCCTCAAGAGT | SEQ ID NO:21880 GACTACGGGTGGGCTTGACTA C |
| | | AA | SEQ ID NO:5857 GCYWS | SEQ ID NO:13869 EINHSGSTNYNPSLKS | SEQ ID NO:21881 DYGGLDY |
| iPS:434737 | 21-225_74G6 | NA | SEQ ID NO:5858 AGCTATGGCATGCAC | SEQ ID NO:13870 GTTATATGGTATGATGG AAGTAATAAAAACTATG CAGACTCCGTGAAGGGC | SEQ ID NO:21882 GATGGCAGTATGGTTATGA CGGCCTGACTAC |
| | | AA | SEQ ID NO:5859 SYGMH | SEQ ID NO:13871 VIWYDGSNKNYADSVKG | SEQ ID NO:21883 DGSYGYDGLDY |
| | | | SEQ ID NO:5860 | SEQ ID NO:13872 | SEQ ID NO:21884 |

FIGURE 49
(Continued)

| | | | | | |
|---|---|---|---|---|---|
| iPS:434741 | 21-225_80C11 | NA | AGCTATGGCATGCAC | GTTATATGGTATGATGG AAGTAATAAAACTATG CAGACTCCGTGAAGGGC | GATGGCAGCTATGGGTATGA CGGCCTTGACTAC |
| | | | SEQ ID NO:5861 | SEQ ID NO:13873 | SEQ ID NO:21885 |
| | | AA | SYGMH | VIWYDGSNKNYADSVKG | DGSYGYDGLDY |
| | | | SEQ ID NO:5862 | SEQ ID NO:13874 | SEQ ID NO:21886 |
| iPS:434743 | 21-225_74A4 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5863 | SEQ ID NO:13875 | SEQ ID NO:21887 |
| | | AA | GCYWS | EINHSGSTNYNPSLKS | DYGGMDV |
| | | | SEQ ID NO:5864 | SEQ ID NO:13876 | SEQ ID NO:21888 |
| iPS:434747 | 21-225_80C12 | NA | AATTATGATATCAAC | TGGATGCACCCTAACAA TGGTAACACAGGCTATG CACAGAAGTTCCAGGGC | AGCAGTGGCTGGTACTGGTT CGACCCC |
| | | | SEQ ID NO:5865 | SEQ ID NO:13877 | SEQ ID NO:21889 |
| | | AA | NYDIN | WMHPNNGNTGYAQKFQG | SSGWYWFDP |
| | | | SEQ ID NO:5866 | SEQ ID NO:13878 | SEQ ID NO:21890 |
| iPS:434751 | 21-225_80H12 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5867 | SEQ ID NO:13879 | SEQ ID NO:21891 |
| | | AA | GCYWS | EINHSGSTNYNPSLKS | DYGGMDV |
| | | | SEQ ID NO:5868 | SEQ ID NO:13880 | SEQ ID NO:21892 |
| iPS:434759 | 21_225_81C5 | NA | GGTTGCTACTGGAGC | GAAATCAATCATAGTGG AAGCACCAACTACAACC CGTCCCTCAAGAGT | GACTACGGCGGTATGGACGT C |

FIGURE 49
(Continued)

| | | | | | | | |
|---|---|---|---|---|---|---|---|
| iPS:434761 | (illegible) | AA | SEQ ID NO:5869<br>GCYWS | SEQ ID NO:13881<br>EINHSGSTNYNPSLKS | SEQ ID NO:21893<br>DYGGMDV |
| | | NA | SEQ ID NO:5870<br>AATTATGATATCAAC | SEQ ID NO:13882<br>TGGATGAACCCTAACAG<br>TGGTAACACAGGCTATG<br>CACAGAAGTTCCAGGGC | SEQ ID NO:21894<br>TCCAGTGGCTGGAACTGGTT<br>CGACCCC |
| iPS:434771 | 21-225_81E5 | AA | SEQ ID NO:5871<br>NYDIN | SEQ ID NO:13883<br>WMNPNSGNTGYAQKFQG | SEQ ID NO:21895<br>SSGWNWFDP |
| | | NA | SEQ ID NO:5872<br>AATTATGATATCAAC | SEQ ID NO:13884<br>TGGATGCACCCTAACAG<br>TGGTAACACAGGCTATG<br>CACAGAAGTTCCAGGGC | SEQ ID NO:21896<br>AGCAGTGGCTGGTACTGGTT<br>CGACCCC |
| iPS:434773 | 21-225_81F9 | AA | SEQ ID NO:5873<br>NYDIN | SEQ ID NO:13885<br>WMHPNSGNTGYAQKFQG | SEQ ID NO:21897<br>SSGWYWFDP |
| | | NA | SEQ ID NO:5874<br>GGTCCCTACTGGAGC | SEQ ID NO:13886<br>GAAATCAATTATAGGGG<br>AAGCACCAACTACAACC<br>CGTCCCTCAAGAGT | SEQ ID NO:21898<br>GACTACGGCGGTATGGACGT<br>C |
| iPS:434775 | 21-225_75D9 | AA | SEQ ID NO:5875<br>GPYWS | SEQ ID NO:13887<br>EINYRGSTNYNPSLKS | SEQ ID NO:21899<br>DYGGMDV |
| | | NA | SEQ ID NO:5876<br>GGTTGCTACTGGAGC | SEQ ID NO:13888<br>GAAATCAATCATAGTGG<br>AAGCACCAACTACAACC<br>CGTCCCTCAAGAGT | SEQ ID NO:21900<br>GACTACGGCGGTATGGACGT<br>C |
| iPS:434777 | 21-225_81C11 | AA | SEQ ID NO:5877<br>GCYWS | SEQ ID NO:13889<br>EINHSGSTNYNPSLKS | SEQ ID NO:21901<br>DYGGMDV |
| | | | SEQ ID NO:5878 | SEQ ID NO:13890 | SEQ ID NO:21902 |

FIGURE 49
(Continued)

| | | | | | |
|---|---|---|---|---|---|
| iPS:434793 | 21-225_82A5 | NA | AATTATGATATCAAC | TGGATGCACCCTAACAA TGGTAACACAGGCTATG CACAGAAGTTCCAGGGC | AGCAGTGGCTGGTACTGGTT CGACCCC |
| | | | SEQ ID NO:5879 | SEQ ID NO:13891 | SEQ ID NO:21903 |
| | | AA | NYDIN | WMHPNGNTGYAQKFQG | SSGWYWFDP |
| | | | SEQ ID NO:5880 | SEQ ID NO:13892 | SEQ ID NO:21904 |
| iPS:434797 | 21-225_82G5 | NA | AATTATGATATCAAC | TGGATGCACCCTAACAG TGGTAACACAGGCTATG CACAGAAGTTCCAGGGC | AGTAGTGGCTGGTACTGGTT CGACCCC |
| | | | SEQ ID NO:5881 | SEQ ID NO:13893 | SEQ ID NO:21905 |
| | | AA | NYDIN | WMHPNSGNTGYAQKFQG | SSGWYWFDP |
| | | | SEQ ID NO:5882 | SEQ ID NO:13894 | SEQ ID NO:21906 |
| iPS:434805 | 21-225_82D9 | NA | AATTATGATATCAAC | TGGATGCACCCTAACAG TGGTAACACAGGCTATG CACAGAAGTTCCAGGGC | AGTAGTGGCTGGTACTGGTT CGACCCC |
| | | | SEQ ID NO:5883 | SEQ ID NO:13895 | SEQ ID NO:21907 |
| | | AA | NYDIN | WMHPNSGNTGYAQKFQG | SSGWYWFDP |
| | | | SEQ ID NO:5884 | SEQ ID NO:13896 | SEQ ID NO:21908 |
| iPS:434809 | 21-225_74F5 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5885 | SEQ ID NO:13897 | SEQ ID NO:21909 |
| | | AA | GCYWS | EINHSGSTNYNPSLKS | DYGGMDV |
| | | | SEQ ID NO:5886 | SEQ ID NO:13898 | SEQ ID NO:21910 |
| iPS:434813 | | NA | AATTATGATATCAAC | TGGATGCACCCTAACAA TGGTAACACAGGCTATG CACAGAAGTTCCAGGGC | AGCAGTGGCTGGTACTGGTT CGACCCC |

FIGURE 49
(Continued)

| | | | | | | |
|---|---|---|---|---|---|---|
| iPS:434815 | 21-225_82C12 | AA | SEQ ID NO:5887 NYDIN | SEQ ID NO:13899 WMHPNSGNTGYAQKFQG | SEQ ID NO:21911 SSGWYWFDP |
| | | NA | SEQ ID NO:5888 AGTTATGATATCAAC | SEQ ID NO:13900 TGGATGAACCCTAACAG TGGTAACACAGGCTATG CACAGAAGTTCCAGGGC | SEQ ID NO:21912 GGCTTTTACGATACTTGACT GGTTCCGGCTACTACTACGT TATGGACGTC |
| iPS:434821 | 21-225_74A11 | AA | SEQ ID NO:5889 SYDIN | SEQ ID NO:13901 WMNPNSGNTGYAQKFQG | SEQ ID NO:21913 GFYDILTGSGYYYVMDV |
| | | NA | SEQ ID NO:5890 GGTTGCTACTGGAGC | SEQ ID NO:13902 GAAATCAATCATAGTGG AAGCACCAACTACAACC CGTCCCTCAAGAGT | SEQ ID NO:21914 GACTACGGCGGTATGGACGT C |
| iPS:434823 | 21-225_83G1 | AA | SEQ ID NO:5891 GCYWS | SEQ ID NO:13903 EINHSGSTNYNPSLKS | SEQ ID NO:21915 DYGGMDV |
| | | NA | SEQ ID NO:5892 AATTATGATATCAAC | SEQ ID NO:13904 TGGATGCACCCTAACAG TGGTAACACAGGCTATG CACAGAAGTTCCAGGGC | SEQ ID NO:21916 AGTAGTGGCTGGTACTGGTT CGACCCC |
| iPS:434825 | 21-225_83C2 | AA | SEQ ID NO:5893 NYDIN | SEQ ID NO:13905 WMHPNSGNTGYAQKFQG | SEQ ID NO:21917 SSGWYWFDP |
| | | NA | SEQ ID NO:5894 AATTATGATATCAAC | SEQ ID NO:13906 TGGATGCACCCTAACAG TGGTAACACAGGCTATG CACAGAAGTTCCAGGGC | SEQ ID NO:21918 AGCAGTGGCTGGTACTGGTT CGACCCC |
| iPS:434827 | 21-225_83F3 | AA | SEQ ID NO:5895 NYDIN | SEQ ID NO:13907 WMHPNSGNTGYAQKFQG | SEQ ID NO:21919 SSGWYWFDP |

FIGURE 49
(Continued)

| | | | | | | |
|---|---|---|---|---|---|---|
| iPS:434829 | | NA | SEQ ID NO:5896 AATTATGATATCAAC | SEQ ID NO:13908 TGGATGCACCCTAACAG TGGTAACACAGGCTATG CACAGAAGTTCCAGGGC | SEQ ID NO:21920 AGCAGTGGCTGGTACTGGTT CGACCCC |
| | 21-225_83G3 | AA | SEQ ID NO:5897 NYDIN | SEQ ID NO:13909 WMHPNSGNTGYAQKFQG | SEQ ID NO:21921 SSGWYWFDP |
| iPS:434833 | | NA | SEQ ID NO:5898 AATTATGATATCAAC | SEQ ID NO:13910 TGGATGCACCCTAACAG TGGTAACACAGGCTATG CACAGAAGTTCCAGGGC | SEQ ID NO:21922 AGTAGTGGCTGGTACTGGTT CGACCCC |
| | 21-225_83C5 | AA | SEQ ID NO:5899 NYDIN | SEQ ID NO:13911 WMHPNSGNTGYAQKFQG | SEQ ID NO:21923 SSGWYWFDP |
| iPS:434835 | | NA | SEQ ID NO:5900 GGTTGCTACTGGAGC | SEQ ID NO:13912 GAAATCAATCATAGTGG AAGGACCAACTACAACC CCTCCCTCAAGAGT | SEQ ID NO:21924 GACTACGGTGGGCTTGACTA C |
| | 21-225_83B6 | AA | SEQ ID NO:5901 GCYWS | SEQ ID NO:13913 EINHSGRTNYNPSLKS | SEQ ID NO:21925 DYGGLDY |
| iPS:434839 | | NA | SEQ ID NO:5902 GGTTGCTACTGGAGC | SEQ ID NO:13914 GAAATCAATCATAGTGG AAGCACCAACTACAACC CGTCCCTCAAGAGT | SEQ ID NO:21926 GACTACGGCGGTATGGACGT C |
| | 21-225_83B7 | AA | SEQ ID NO:5903 GCYWS | SEQ ID NO:13915 EINHSGSTNYNPSLKS | SEQ ID NO:21927 DYGGMDV |
| iPS:434841 | | NA | SEQ ID NO:5904 AATTATGATATCAAC | SEQ ID NO:13916 TGGATGAACCCTAACAG TGGTAACACAGGCTATG CACAGAAGTTCCAGGGC | SEQ ID NO:21928 TCCAGTGGCTGGCACTGGTT CGACCCC |

FIGURE 49
(Continued)

| | | | | | | |
|---|---|---|---|---|---|---|
| iPS:434849 | 21-225_83G7 | AA | SEQ ID NO:5905<br>NYDIN | SEQ ID NO:13917<br>WMNPNSGNTGYAQKFQG | SEQ ID NO:21929<br>SSGWHWFDP | |
| | | NA | SEQ ID NO:5906<br>GGTTACTACTGGAGC | SEQ ID NO:13918<br>GAAATCAATCATAGTGG<br>AAGCACCAACTTCAACC<br>CGTCCCTCAAGAGT | SEQ ID NO:21930<br>GACTACGGTGGCTTGACTA<br>C | |
| iPS:434851 | 21-225_83C10 | AA | SEQ ID NO:5907<br>GYYWS | SEQ ID NO:13919<br>EINHSGSTNFNPSLKS | SEQ ID NO:21931<br>DYGGLDY | |
| | | NA | SEQ ID NO:5908<br>AATTATGATATCAAC | SEQ ID NO:13920<br>TGGATGAACCCTAACAG<br>TGGTAACACAGGCTATG<br>CACAGAAGTTCCAGGGC | SEQ ID NO:21932<br>AGCAGTGGCTGGTACATCTT<br>TGACTAC | |
| iPS:434863 | 21-225_75A6 | AA | SEQ ID NO:5909<br>NYDIN | SEQ ID NO:13921<br>WMNPNSGNTGYAQKFQG | SEQ ID NO:21933<br>SSGWYIFDY | |
| | | NA | SEQ ID NO:5910<br>AATTATGATATCAAC | SEQ ID NO:13922<br>TGGATGAACCCTAACAG<br>TGGTAACACAGGCTATG<br>CACAGAAGTTCCAGGGC | SEQ ID NO:21934<br>TCCAGTGGCTGGCACTGGTT<br>CGACCCC | |
| iPS:434865 | 21-225_84G7 | AA | SEQ ID NO:5911<br>NYDIN | SEQ ID NO:13923<br>WMNPNSGNTGYAQKFQD | SEQ ID NO:21935<br>SSGWHWFDP | |
| | | NA | SEQ ID NO:5912<br>AGCTATGGCATGCAC | SEQ ID NO:13924<br>GTTATATGGTATGATGG<br>AAGTAATAAAAACTATG<br>CAGACTCCGTGAAGGGC | SEQ ID NO:21936<br>GATGGCAGCTATGGTTACGA<br>CGGCCTTGACTAC | |
| iPS:434867 | 21-225_79A12 | | SEQ ID NO:5913 | SEQ ID NO:13925 | SEQ ID NO:21937 | |

FIGURE 49
(Continued)

| | | | | | | | |
|---|---|---|---|---|---|---|---|
| iPS:434869 | 21-225_84E12 | AA | SYGMH | | VIWYDGSNKNYADSVKG | | DGSYGYDGLDY | |
| | | NA | GGTTCCTACTGGAGC | SEQ ID NO:5914 | GAAATCAATCAAAGTGG ACGCACCAACTACAACC CGTCCCTCAAGAGT | SEQ ID NO:13926 | GACTACGGGGGTATAGACGT C | SEQ ID NO:21938 |
| | | | | SEQ ID NO:5915 | | SEQ ID NO:13927 | | SEQ ID NO:21939 |
| iPS:434871 | 21-225_85H1 | AA | GSYWS | | EINQSGRTNYNPSLKS | | DYGGIDV | |
| | | | | SEQ ID NO:5916 | | SEQ ID NO:13928 | | SEQ ID NO:21940 |
| | | NA | AGCTATGGCATACAAC | | GTTATATATGGTATGATGG AAGTAATAAATACTATG CAGACTCCGTGAAGGGC | | GATCCCTTTATAGTGGGAGC TACTTACTTTGACTAC | |
| | | | | SEQ ID NO:5917 | | SEQ ID NO:13929 | | SEQ ID NO:21941 |
| iPS:434877 | 21-225_85H2 | AA | SYGIH | | VIWYDGSNKYYADSVKG | | DPFIVGATYFDY | |
| | | | | SEQ ID NO:5918 | | SEQ ID NO:13930 | | SEQ ID NO:21942 |
| | | NA | AATTATGATATCAAC | | TGGATGCACCTAATAG TGGTAACACAGGCTATG CACAGAAGTTCCAGGGC | | TCCAGTGGCTGGTACTGGTT CGACCCC | |
| | | | | SEQ ID NO:5919 | | SEQ ID NO:13931 | | SEQ ID NO:21943 |
| iPS:434879 | 21-225_85A3 | AA | NYDIN | | WMHPNSGNTGYAQKFQG | | SSGWYWFDP | |
| | | | | SEQ ID NO:5920 | | SEQ ID NO:13932 | | SEQ ID NO:21944 |
| | | NA | GGTTGCTACTGGAGC | | GAAATCAATCATATGG AAGCACCAACTACAACC CGTCCCTCAAGAGT | | GACTACGGCGGGTATGGACGT C | |
| | | | | SEQ ID NO:5921 | | SEQ ID NO:13933 | | SEQ ID NO:21945 |
| | | AA | GCYWS | | EINHSGSTNYNPSLKS | | DYGGMDV | |
| | | | | SEQ ID NO:5922 | | SEQ ID NO:13934 | | SEQ ID NO:21946 |

FIGURE 49
(Continued)

| | | NA/AA | | | |
|---|---|---|---|---|---|
| iPS:434881 | 21-225_85B4 | NA | GGTTGCTACTGGAGC | GAAATCAATCATATAGTGG AAGCACCAACTACAACC CGTCCCTCAAGAGT | GACTACGGGCGGTATGGACGT C |
| | | AA | SEQ ID NO:5923 GCYWS | SEQ ID NO:13935 EINHSGSTNYNPSLKS | SEQ ID NO:21947 DYGGMDV |
| iPS:434883 | 21-225_85B5 | NA | SEQ ID NO:5924 AATTATGATATCAAC | SEQ ID NO:13936 TGGATGCACCCTAACAG TGGTAACACAGGCTATG CACAGAAGTTCCAGGGC | SEQ ID NO:21948 AGTAGTGGCTGGTACTGGTT CGACCCC |
| | | AA | SEQ ID NO:5925 NYDIN | SEQ ID NO:13937 WMHPNSGNTGYAQKFQG | SEQ ID NO:21949 SSGWYWFDP |
| iPS:434887 | 21-225_85D6 | NA | SEQ ID NO:5926 GGTTGCTACTGGAGC | SEQ ID NO:13938 GAAATCAATTATAGTGG AAGAACCACTACAACC CGTCCCTCAAGAGT | SEQ ID NO:21950 GACTACGGCGGTATGGACGT C |
| | | AA | SEQ ID NO:5927 GCYWS | SEQ ID NO:13939 EINYSGRTNYNPSLKS | SEQ ID NO:21951 DYGGMDV |
| iPS:434891 | 21-225_85G6 | NA | SEQ ID NO:5928 GATTGCTACTGGAGC | SEQ ID NO:13940 GAAATCAATCATATAGTGG AAGGACCAACTACAACC CGTCCCTCAAGAGT | SEQ ID NO:21952 GACTACGGTGGGCTTGACTA C |
| | | AA | SEQ ID NO:5929 DCYWS | SEQ ID NO:13941 EINHSGRTNYNPSLKS | SEQ ID NO:21953 DYGGLDY |
| iPS:434895 | 21-225_74H7 | NA | SEQ ID NO:5930 GGTCCCTACTGGAGC | SEQ ID NO:13942 GAAATCAATCATATAGTGG AAGCACCAACTACAACC CGTCCCTCAAGAGT | SEQ ID NO:21954 GACTACGGGGGTTGGACGT C |
| | | AA | SEQ ID NO:5931 GPYWS | SEQ ID NO:13943 EINHSGSTNYNPSLKS | SEQ ID NO:21955 DYGGLDV |

FIGURE 49
(Continued)

| | | | SEQ ID NO:5932 GGTTGCTACTGGAGC | SEQ ID NO:13944 GAAATCAATCATAGTGG AAGGACCAACTTCAACC CGTCCCTCAAGAGT | SEQ ID NO:21956 GACTACGGCGGTATGGACGT C |
|---|---|---|---|---|---|
| iPS:434899 | 21-225_85B9 | NA | | | |
| | | AA | SEQ ID NO:5933 GCYWS | SEQ ID NO:13945 EINHSGRTNFNPSLKS | SEQ ID NO:21957 DYGGMDV |
| | | NA | SEQ ID NO:5934 AATTATGATATCAAC | SEQ ID NO:13946 TGGATGAACCCTAACAG TGGTAACACAGGCTATG CACAGAAGTTCCAGGGC | SEQ ID NO:21958 ACCAGTGGCTGGAACTTCTT TGACTAC |
| iPS:434901 | 21-225_85H9 | AA | SEQ ID NO:5935 NYDIN | SEQ ID NO:13947 WMNPNSGNTGYAQKFQG | SEQ ID NO:21959 TSGWNFFDY |
| | | NA | SEQ ID NO:5936 GGTTGTTACTGGAGC | SEQ ID NO:13948 GAAATCAATCATAGTGG AATCACCAACTACAACC CGTCCCTCAAGAGT | SEQ ID NO:21960 GACTACGGTGGTTTGGACGT C |
| iPS:434907 | 21-225_85G10 | AA | SEQ ID NO:5937 GCYWS | SEQ ID NO:13949 EINHSGITNYNPSLKS | SEQ ID NO:21961 DYGGLDV |
| | | NA | SEQ ID NO:5938 AATTATGATATCAAC | SEQ ID NO:13950 TGGATGCACCTAACAG TGGTAACACAGGCTATG CACAGAAGTTCCAGGGC | SEQ ID NO:21962 AGTAGTGGCTGGTACAAATT TGACTAC |
| iPS:434909 | 21-225_85C11 | AA | SEQ ID NO:5939 NYDIN | SEQ ID NO:13951 WMIHPNSGNTGYAQKFQG | SEQ ID NO:21963 SSGWYKFDY |
| iPS:434911 | | NA | SEQ ID NO:5940 AATTATGATATCAAC | SEQ ID NO:13952 TGGATGCACCTAACAG TGGTAACACAGGCTATG CACAGAAGTTCCAGGGC | SEQ ID NO:21964 AGTAGTGGCTGGTACTGGTT CGACCCC |

FIGURE 49
(Continued)

| | | | | | | | | |
|---|---|---|---|---|---|---|---|---|
| iPS:434913 | 21-225_85D11 | AA | | NYDIN | SEQ ID NO:5941 | WMHPNSGNTGYAQKFQG | SEQ ID NO:13953 | SSGWYWFDP | SEQ ID NO:21965 |
| | | NA | | GGTTGCTACTGGAGC | SEQ ID NO:5942 | GAAATCAATCATAGTGGAAGCACCAACTACAACCCGTCCCTCAAGAGT | SEQ ID NO:13954 | GACTACGGGCGGGTATGGACGTC | SEQ ID NO:21966 |
| iPS:434921 | 21-225_86C1 | AA | | GCYWS | SEQ ID NO:5943 | EINHSGSTNYNPSLKS | SEQ ID NO:13955 | DYGGMDV | SEQ ID NO:21967 |
| | | NA | | GGTTGCTACTGGAGC | SEQ ID NO:5944 | GAAATCAATCATAGTGGAAGCACCAACTACAACCCGTCCCTCAAGAGT | SEQ ID NO:13956 | GACTACGGGCGGGTATGGACGTC | SEQ ID NO:21968 |
| iPS:434935 | 21-225_86E4 | AA | | GCYWS | SEQ ID NO:5945 | EINHSGSTNYNPSLKS | SEQ ID NO:13957 | DYGGMDV | SEQ ID NO:21969 |
| | | NA | | AATTATGATATCAAC | SEQ ID NO:5946 | TGGATGAACCCTAACAGTGGTAACACAGGCTATGCACAGAAGTTCCAGGGC | SEQ ID NO:13958 | TCCAGTGGCTGGTCCTGGTTCGACCCC | SEQ ID NO:21970 |
| iPS:434937 | 21-225_86E9 | AA | | NYDIN | SEQ ID NO:5947 | WMNPNSGNTGYAQKFQG | SEQ ID NO:13959 | SSGWSWFDP | SEQ ID NO:21971 |
| | | NA | | GGTTGCTACTGGAGC | SEQ ID NO:5948 | GAAATCAATCATAGTGGAAGCACCAACTACAACCCGTCCCTCAAGAGT | SEQ ID NO:13960 | GACTACGGGCGGGTATGGACGTC | SEQ ID NO:21972 |
| iPS:434939 | 21-225_86C11 | AA | | GCYWS | SEQ ID NO:5949 | EINHSGSTNYNPSLKS | SEQ ID NO:13961 | DYGGMDV | SEQ ID NO:21973 |
| | | | | | SEQ ID NO:5950 | | SEQ ID NO:13962 | | SEQ ID NO:21974 |

FIGURE 49
(Continued)

| | | | | | | |
|---|---|---|---|---|---|---|
| iPS:434943 | 21-225_87H1 | NA | GGTTACTACTGGAGC | | GAAATCAATCATAGTGG ACGCACCAACTACAACC CGTCCCTCAAGAGT | | GACTACGGTGGTTTGGACGT C |
| | | | SEQ ID NO:5951 | | SEQ ID NO:13963 | | SEQ ID NO:21975 |
| | | AA | GYYWS | | EINHSGRTNYNPSLKS | | DYGGLDV |
| | | | SEQ ID NO:5952 | | SEQ ID NO:13964 | | SEQ ID NO:21976 |
| iPS:434945 | 21-225_87E5 | NA | GGTTGCTACTGGAGC | | GAAATCAATCATAGTGG AAGCACCAACTACAACC CGTCCCTCAAGAGT | | GACTACGGCGGTATGGACGT C |
| | | | SEQ ID NO:5953 | | SEQ ID NO:13965 | | SEQ ID NO:21977 |
| | | AA | GCYWS | | EINHSGSTNYNPSLKS | | DYGGMDV |
| | | | SEQ ID NO:5954 | | SEQ ID NO:13966 | | SEQ ID NO:21978 |
| iPS:434947 | 21-225_87B7 | NA | AGCTATGGCATGCAC | | GTTATATGGTATGATGG AAGTAATAAAAACTATG CAGACTCCGTGAAGGGC | | GATTTTGGAGTGGGCTACTA CGGTATGGACGTC |
| | | | SEQ ID NO:5955 | | SEQ ID NO:13967 | | SEQ ID NO:21979 |
| | | AA | SYGMH | | VIWYDGSNKNYADSVKG | | DFGVGYYGMDV |
| | | | SEQ ID NO:5956 | | SEQ ID NO:13968 | | SEQ ID NO:21980 |
| iPS:434955 | 21-225_87C9 | NA | GGTTGCTACTGGAGC | | GAAATCAATCATAGTGG AAGCACCAACTACAACC CGTCCCTCAAGAGT | | GACTACGGCGGTATGGACGT C |
| | | | SEQ ID NO:5957 | | SEQ ID NO:13969 | | SEQ ID NO:21981 |
| | | AA | GCYWS | | EINHSGSTNYNPSLKS | | DYGGMDV |
| | | | SEQ ID NO:5958 | | SEQ ID NO:13970 | | SEQ ID NO:21982 |
| iPS:434957 | 21-225_87A10 | NA | AATTATGATATCAAC | | TGGATGCACCCTAACAA TGGTAACACAGGCTATG CACAGAAGTTCCAGGGC | | AGCAGTGGCTGGTACTGGTT CGACCCC |
| | | | SEQ ID NO:5959 | | SEQ ID NO:13971 | | SEQ ID NO:21983 |

FIGURE 49
(Continued)

| | | | | | |
|---|---|---|---|---|---|
| iPS:434959 | 21-225_87E10 | AA | NYDIN | WMHPNNGNTGYAQKFQG | SSGWYWFDP |
| | | | SEQ ID NO:5960 | SEQ ID NO:13972 | SEQ ID NO:21984 |
| | | NA | AATTATGATATCAAC | TGGATGAACCCTAACAGTGGTAACACAGGCTATGCACAGAAGTTCCAGGGC | AGCAGTGGCTGGTACTTCTTTGACTAC |
| | | | SEQ ID NO:5961 | SEQ ID NO:13973 | SEQ ID NO:21985 |
| iPS:434961 | 21-225_87A12 | AA | NYDIN | WMNPNSGNTGYAQKFQG | SSGWYFFDY |
| | | | SEQ ID NO:5962 | SEQ ID NO:13974 | SEQ ID NO:21986 |
| | | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:5963 | SEQ ID NO:13975 | SEQ ID NO:21987 |
| | | AA | GCYWS | EINHSGSTNYNPSLKS | DYGGMDV |
| | | | SEQ ID NO:5964 | SEQ ID NO:13976 | SEQ ID NO:21988 |
| iPS:434965 | 21-225_88A1 | NA | AATTATGATATCAAC | TGGATGAACCCTAACAGTGGTAACACAGGCTATGCACAGAAGTTCCAGGGC | AGCAGTGGCTGGTACTACTTTGACTAC |
| | | | SEQ ID NO:5965 | SEQ ID NO:13977 | SEQ ID NO:21989 |
| | | AA | NYDIN | WMNPNSGNTGYAQKFQG | SSGWYFFDY |
| | | | SEQ ID NO:5966 | SEQ ID NO:13978 | SEQ ID NO:21990 |
| iPS:434969 | 21-225_88H1 | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:5967 | SEQ ID NO:13979 | SEQ ID NO:21991 |
| | | AA | GCYWS | EINHSGSTNYNPSLKS | DYGGMDV |
| | | | SEQ ID NO:5968 | SEQ ID NO:13980 | SEQ ID NO:21992 |

FIGURE 49
(Continued)

| iPS:434971 | 21-225_88G2 | NA | AATTATGATATCAAC | TGGATGCACCCTAACAG TGGTAACACAGGCTATG CACAGAAGTTCCAGGGC | AGCAGTGGCTGGTACTGGTT CGACCCC |
| --- | --- | --- | --- | --- | --- |
| | | | SEQ ID NO:5969 | SEQ ID NO:13981 | SEQ ID NO:21993 |
| | | AA | NYDIN | WMHPNSGNTGYAQKFQG | SSGWYWFDP |
| | | | SEQ ID NO:5970 | SEQ ID NO:13982 | SEQ ID NO:21994 |
| iPS:434973 | 21-225_88B4 | NA | AATTATGATATCAAC | TGGATGAACCCTAACAG TGGTGACACAGGCTATG CACAGAAGTTCCAGGGC | AGCAGTGGCTGGTACTACTT TGACTAC |
| | | | SEQ ID NO:5971 | SEQ ID NO:13983 | SEQ ID NO:21995 |
| | | AA | NYDIN | WMNPNSGDTGYAQKFQG | SSGWYYFDY |
| | | | SEQ ID NO:5972 | SEQ ID NO:13984 | SEQ ID NO:21996 |
| iPS:434977 | 21-225_88A5 | NA | AGTTATGATATCAAC | TGGATGAACCCTAACAG TGGTAACACAGGCTATG CACAGAAGTTCCAGGGC | GGGTTTTACGATTTTTTGACT GGTTATTCCCCACTACTA CTACTACGATATGGACGTC |
| | | | SEQ ID NO:5973 | SEQ ID NO:13985 | SEQ ID NO:21997 |
| | | AA | SYDIN | WMNPNSGNTGYAQKFQG | GFYDFLTGYSPTYYYYDMDV |
| | | | SEQ ID NO:5974 | SEQ ID NO:13986 | SEQ ID NO:21998 |
| iPS:434981 | 21-225_88E7 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:5975 | SEQ ID NO:13987 | SEQ ID NO:21999 |
| | | AA | GCYWS | EINHSGSTNYNPSLKS | DYGGMDV |
| | | | SEQ ID NO:5976 | SEQ ID NO:13988 | SEQ ID NO:22000 |

FIGURE 49
(Continued)

| | | | | | |
|---|---|---|---|---|---|
| iPS:434983 | 21-225_88F7 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5977 | SEQ ID NO:13989 | SEQ ID NO:22001 |
| | | AA | GCYWS | EINHSGSTNYNPSLKS | DYGGMDV |
| | | | SEQ ID NO:5978 | SEQ ID NO:13990 | SEQ ID NO:22002 |
| iPS:434995 | 21-225_88G9 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5979 | SEQ ID NO:13991 | SEQ ID NO:22003 |
| | | AA | GCYWS | EINHSGSTNYNPSLKS | DYGGMDV |
| | | | SEQ ID NO:5980 | SEQ ID NO:13992 | SEQ ID NO:22004 |
| iPS:434997 | 21-225_88C10 | NA | AATTATGATATCAAC | TGGATGACCCCTAACAG TGGTAACACAGGCTATG CACAGAAGTTCCAGGGC | AGCAGTGGCTGGTACTACTT TGACTCC |
| | | | SEQ ID NO:5981 | SEQ ID NO:13993 | SEQ ID NO:22005 |
| | | AA | NYDIN | WMTPNSGNTGYAQKFQG | SSGWYYFDS |
| | | | SEQ ID NO:5982 | SEQ ID NO:13994 | SEQ ID NO:22006 |
| iPS:434999 | 21-225_75A8 | NA | GGTTGCTACTGGAGC | GAAATCAATCATAGTGG AAGCACCAACTACAACC CGTCCCTCAAGAGT | GACTACGGCGGTATGGACGT C |
| | | | SEQ ID NO:5983 | SEQ ID NO:13995 | SEQ ID NO:22007 |
| | | AA | GCYWS | EINHSGSTNYNPSLKS | DYGGMDV |
| | | | SEQ ID NO:5984 | SEQ ID NO:13996 | SEQ ID NO:22008 |
| iPS:435009 | 21-225_89G4 | NA | AGCTACGACATGCAC | GCTATTGGTACTGCTGGT GACACATACTATCCAGG CTCCGTGAAGGGC | GCTCTTGACTACGGTGACTC CTTGGGCTACTACTACGGTA TGGACGTC |
| | | | SEQ ID NO:5985 | SEQ ID NO:13997 | SEQ ID NO:22009 |
| | | AA | SYDMH | AIGTAGDTYYPGSVKG | ALDYGDSLGYYYYGMDV |

FIGURE 49
(Continued)

| | | | | | | | |
|---|---|---|---|---|---|---|---|
| iPS:435013 | 21-225_89D5 | NA | SEQ ID NO:5986 GGTTGCTACTGGAGC | SEQ ID NO:13998 GAAATCAATCATATGG AAGCACCAACTACAACC CGTCCCTCAAGAGT | SEQ ID NO:22010 GACTACGGCGGTATGGACGT C |
| | | AA | SEQ ID NO:5987 GCYWS | SEQ ID NO:13999 EINHSGSTNYNPSLKS | SEQ ID NO:22011 DYGGMDV |
| iPS:435015 | 21-225_89H5 | NA | SEQ ID NO:5988 GGTTGCTACTGGAGC | SEQ ID NO:14000 GAAATCAATTATAGTGG AAGCACCAACTTCAACC CGTCCCTCAAGAGT | SEQ ID NO:22012 GACTACGGCGGGTATGGACGT C |
| | | AA | SEQ ID NO:5989 GCYWS | SEQ ID NO:14001 EINYSGSTNFNPSLKS | SEQ ID NO:22013 DYGGMDV |
| iPS:435025 | 21-225_89E10 | NA | SEQ ID NO:5990 GGTTGCTACTGGAGC | SEQ ID NO:14002 GAAATCAATCATATGTGG AAGCACCAACTACAACC CGTCCCTCAAGAGT | SEQ ID NO:22014 GACTACGGCGGTATGGACGT C |
| | | AA | SEQ ID NO:5991 GCYWS | SEQ ID NO:14003 EINHSGSTNYNPSLKS | SEQ ID NO:22015 DYGGMDV |
| iPS:435029 | 21-225_89A11 | NA | SEQ ID NO:5992 GGTTACTACTGGAGC | SEQ ID NO:14004 GAAATCAATCATATGTGG ACGCACCAGTCAACC CGTCCCTCAAGAGT | SEQ ID NO:22016 GACTACGGTGGTTTGGACGT C |
| | | AA | SEQ ID NO:5993 GYYWS | SEQ ID NO:14005 EINHSGRTSYNPSLKS | SEQ ID NO:22017 DYGGLDV |
| iPS:435039 | 21-225_90G4 | NA | SEQ ID NO:5994 GGTTGCTACTGGAGC | SEQ ID NO:14006 GAAATCAATCATATGG AAGCACCAACTACAACC CGTCCCTCAAGAGT | SEQ ID NO:22018 GACTACGGCGGTATGGACGT C |
| | | AA | SEQ ID NO:5995 GCYWS | SEQ ID NO:14007 EINHSGSTNYNPSLKS | SEQ ID NO:22019 DYGGMDV |

FIGURE 49
(Continued)

| ID | Clone | | | | | |
|---|---|---|---|---|---|---|
| iPS:435041 | 21-225_90A5 | NA | SEQ ID NO:5996<br>GGTTGCTACTGGAGC | SEQ ID NO:14008<br>GAAATCAATCATAGTGG<br>AAGCACCAACTACAACC<br>CGTCCCTCAAGAGT | SEQ ID NO:22020<br>GACTACGGCGGTATGGACGT<br>C |
| | | AA | SEQ ID NO:5997<br>GCYWS | SEQ ID NO:14009<br>EINHSGSTNYNPSLKS | SEQ ID NO:22021<br>DYGGMDV |
| iPS:435043 | 21-225_90G5 | NA | SEQ ID NO:5998<br>GGTTGCTACTGGAGC | SEQ ID NO:14010<br>GAAATCAATCATAGTGG<br>AAGCACCAACTACAACC<br>CGTCCCTCAAGAGT | SEQ ID NO:22022<br>GACTACGGCGGTATGGACGT<br>C |
| | | AA | SEQ ID NO:5999<br>GCYWS | SEQ ID NO:14011<br>EINHSGSTNYNPSLKS | SEQ ID NO:22023<br>DYGGMDV |
| iPS:435045 | 21-225_90H5 | NA | SEQ ID NO:6000<br>GACTATGGGCATGCAC | SEQ ID NO:14012<br>GTTATATGGTATGAAGG<br>AAGTAATACATACTATG<br>CAGACTCCGTGAAGGGC | SEQ ID NO:22024<br>GAGATGGGGTGGTTAGATGA<br>CTAC |
| | | AA | SEQ ID NO:6001<br>DYGMH | SEQ ID NO:14013<br>VIWYEGSNTYYADSVKG | SEQ ID NO:22025<br>EMGWLDDY |
| iPS:435051 | 21-225_90D9 | NA | SEQ ID NO:6002<br>AATTATGATATCAAC | SEQ ID NO:14014<br>TGGATGAACCCTAACAG<br>TGGTAACACAGGCTATG<br>CACAGAAGTTCCAGGGC | SEQ ID NO:22026<br>TCCAGTGGCTGGCACTGGTT<br>CGACCCC |
| | | AA | SEQ ID NO:6003<br>NYDIN | SEQ ID NO:14015<br>WMNPNSGNTGYAQKFQG | SEQ ID NO:22027<br>SSGWHWFDP |
| iPS:435053 | 21-225_75F9 | NA | SEQ ID NO:6004<br>AATTATGATATCAAC | SEQ ID NO:14016<br>TGGATGCACCCTAACAG<br>TGGTAACACAGGCTATG<br>CACAGAAGTTCCAGGGC | SEQ ID NO:22028<br>AGCAGTGGCTGGTACATCTT<br>TGACTAC |
| | | | SEQ ID NO:6005 | SEQ ID NO:14017 | SEQ ID NO:22029 |

FIGURE 49
(Continued)

| | | | | | | | | |
|---|---|---|---|---|---|---|---|---|
| iPS:435055 | 21-225_90F10 | AA | NYDIN | SEQ ID NO:6006 | WMHPNSGNTGYAQKFQG | SEQ ID NO:14018 | SSGWYIFDY | SEQ ID NO:22030 |
| | | NA | GGTTGCTACTGGAGC | SEQ ID NO:6007 | GAAATCAATCATAGTGG AAGCACCAACTACAACC CGTCCCTCAAGAGT | SEQ ID NO:14019 | GACTACGGCGGGTATGGACGT C | SEQ ID NO:22031 |
| | | AA | GCYWS | SEQ ID NO:6008 | EINHSGSTNYNPSLKS | SEQ ID NO:14020 | DYGGMDV | SEQ ID NO:22032 |
| iPS:435059 | 21-225_90C11 | NA | AACTACGACATGCAC | SEQ ID NO:6009 | GCTATTGGTACTGCTGGT GACACATATCCAGG CTCCGTGAAGGGC | SEQ ID NO:14021 | GTTCTTGACTACGGTGACTC CTGGGCTACTACTACG GTATGGACGTC | SEQ ID NO:22033 |
| | | AA | NYDMH | SEQ ID NO:6010 | AIGTAGDTYYPGSVKG | SEQ ID NO:14022 | VLDYGDSLGYYYYGMDV | SEQ ID NO:22034 |
| iPS:435071 | 21-225_91F1 | NA | AATTATGATATCAAC | SEQ ID NO:6011 | TGGATGCACCCTAACAG TGGTAACACAGGCTATG CACAGAAGTTCCAGGGC | SEQ ID NO:14023 | AGCAGTGGCTGGTACTGGTT CGACCCC | SEQ ID NO:22035 |
| | | AA | NYDIN | SEQ ID NO:6012 | WMHPNSGNTGYAQKFQG | SEQ ID NO:14024 | SSGWYWFDP | SEQ ID NO:22036 |
| iPS:435073 | 21-225_91B2 | NA | GGTTGCTACTGGAGC | SEQ ID NO:6013 | GAAATCAATCATAGTGG AAGCACCAACTACAACC CGTCCCTCAAGAGT | SEQ ID NO:14025 | GACTACGGCGGGTATGGACGT C | SEQ ID NO:22037 |
| | | AA | GCYWS | SEQ ID NO:6014 | EINHSGSTNYNPSLKS | SEQ ID NO:14026 | DYGGMDV | SEQ ID NO:22038 |

FIGURE 49
(Continued)

| | | | | | |
|---|---|---|---|---|---|
| iPS:435075 | 21-225_91B3 | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:6015 | SEQ ID NO:14027 | SEQ ID NO:22039 |
| | | AA | GCYWS | EINHSGSTNYNPSLKS | DYGGMDV |
| | | | SEQ ID NO:6016 | SEQ ID NO:14028 | SEQ ID NO:22040 |
| iPS:435077 | 21-225_91F3 | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:6017 | SEQ ID NO:14029 | SEQ ID NO:22041 |
| | | AA | GCYWS | EINHSGSTNYNPSLKS | DYGGMDV |
| | | | SEQ ID NO:6018 | SEQ ID NO:14030 | SEQ ID NO:22042 |
| iPS:435079 | 21-225_91B4 | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:6019 | SEQ ID NO:14031 | SEQ ID NO:22043 |
| | | AA | GCYWS | EINHSGSTNYNPSLKS | DYGGMDV |
| | | | SEQ ID NO:6020 | SEQ ID NO:14032 | SEQ ID NO:22044 |
| iPS:435087 | 21-225_91G8 | NA | AATTATGATATCAAC | TGGATGCACCCTAACAGTGGTAACACAGGCTATGCACAGAAGTTCCAGGGC | AGCAGTGGCTGGTACTGGTTCGACCCC |
| | | | SEQ ID NO:6021 | SEQ ID NO:14033 | SEQ ID NO:22045 |
| | | AA | NYDIN | WMHPNSGNTGYAQKFQG | SSGWYWFDP |
| | | | SEQ ID NO:6022 | SEQ ID NO:14034 | SEQ ID NO:22046 |
| iPS:435089 | 21-225_91E9 | NA | GGTTGCTACTGGAGC | GAAATCAATCATAGTGGAAGCACCAACTACAACCCGTCCCTCAAGAGT | GACTACGGCGGGTATGGACGTC |
| | | | SEQ ID NO:6023 | SEQ ID NO:14035 | SEQ ID NO:22047 |
| | | AA | GCYWS | EINHSGSTNYNPSLKS | DYGGMDV |

FIGURE 49
(Continued)

| | | | | | | |
|---|---|---|---|---|---|---|
| iPS:435097 | 21-225_92B1 | NA | SEQ ID NO:6024 GGTTGCTACTGGAGC | SEQ ID NO:14036 GAAATCAATTATAGGGG AAGCACCAACTACAACC CGTCCCTCAAGAGT | SEQ ID NO:22048 GACTACGGCGGTTGGACGT C | |
| | | AA | SEQ ID NO:6025 GSYWS | SEQ ID NO:14037 EINYRGSTNYNPSLKS | SEQ ID NO:22049 DYGGLDV | |
| iPS:435103 | 21-225_92B2 | NA | SEQ ID NO:6026 AACTACGACATGCAC | SEQ ID NO:14038 GCTATTGGTACTGCTGGT GACACATACTATCCAGG CTCCGTGAAGGGC | SEQ ID NO:22050 GCTCTTGACTACGGTGACTC CTTGGGCTACTACTACGG GTATGGACGTC | |
| | | AA | SEQ ID NO:6027 NYDMH | SEQ ID NO:14039 AIGTAGDTYYPGSVKG | SEQ ID NO:22051 ALDYGDSLGYYYYGMDV | |
| iPS:435109 | 21-225_92H5 | NA | SEQ ID NO:6028 AGCTATGGCATGCAC | SEQ ID NO:14040 GTTATATGGTATGATGG AAGTAATAAATACTATG CAGACTCCGTGAAGGGC | SEQ ID NO:22052 GATCCCTTTATAGTGGGAGC TACTTACTTTGACTAC | |
| | | AA | SEQ ID NO:6029 SYGMH | SEQ ID NO:14041 VIWYDGSNKYYADSVKG | SEQ ID NO:22053 DPFIVGATYFDY | |
| iPS:435111 | 21-225_92D6 | NA | SEQ ID NO:6030 GGTTGCTACTGGAGC | SEQ ID NO:14042 GAAATCAATTATAGTGG AAGCACCAACTACAACC CGTCCCTCAAGAGT | SEQ ID NO:22054 GACTACGGCGGTATGGACGT C | |
| | | AA | SEQ ID NO:6031 GCYWS | SEQ ID NO:14043 EINHSGSTNYNPSLKS | SEQ ID NO:22055 DYGGMDV | |
| iPS:435113 | | NA | SEQ ID NO:6032 AATTATGATATCAAC | SEQ ID NO:14044 TGGATGCACCCTAACAG TGGTAACACAGGCTATG CACAGAAGTTCCAGGGC | SEQ ID NO:22056 AGCAGTGGCTGGTACTTTTT TGACTAC | |

FIGURE 49
(Continued)

| | | | | | | SEQ ID NO:22057 |
|---|---|---|---|---|---|---|
| iPS:435115 | 21-225_92E6 | AA | SEQ ID NO:6033 NYDIN | SEQ ID NO:14045 WMHPNSGNTGYAQKFQG | SSGWYFFDY |
| | | NA | SEQ ID NO:6034 GGTTGCTACTGGAGC | SEQ ID NO:14046 GAAATCAATCATAGTGG AAGCACCAACTACAACC CGTCCCTCAAGAGT | SEQ ID NO:22058 GACTACGGCGGGTATGGACGTC |
| iPS:435167 | 21-225_77C5 | AA | SEQ ID NO:6035 GCYWS | SEQ ID NO:14047 EINHSGSTNYNPSLKS | SEQ ID NO:22059 DYGGMDV |
| | | NA | SEQ ID NO:6036 AATTATGATATCAAC | SEQ ID NO:14048 TGGATGAACCCTAACAG TGGTAACACAGGCTATG CACAGAAGTTCCAGGGC | SEQ ID NO:22060 ACCAGTGGCGGGGAAGTTCTT CGACTAC |
| | 21-225_92F12 | AA | SEQ ID NO:6037 NYDIN | SEQ ID NO:14049 WMNPNSGNTGYAQKFQG | SEQ ID NO:22061 TSGGKFFDY |
| iPS:435171 | 21-225_93C2 | NA | SEQ ID NO:6038 GGTTGCTACTGGAGC | SEQ ID NO:14050 GAAATCAATCATAGTGG AAGCACCAACTACAACC CGTCCCTCAAGAGT | SEQ ID NO:22062 GACTACGGCGGGTATGGACGTC |
| | | AA | SEQ ID NO:6039 GCYWS | SEQ ID NO:14051 EINHSGSTNYNPSLKS | SEQ ID NO:22063 DYGGMDV |
| iPS:435177 | 21-225_93E4 | NA | SEQ ID NO:6040 GGTTGCTACTGGAGC | SEQ ID NO:14052 GAAATCAATCATAGTGG AAGCACCAACTACAACC CGTCCCTCAAGAGT | SEQ ID NO:22064 DYGGMDV |
| | | AA | SEQ ID NO:6041 GCYWS | SEQ ID NO:14053 EINHSGSTNYNPSLKS | SEQ ID NO:22065 GACTACGGCGGGTATGGACGTC |
| | | | SEQ ID NO:6042 | SEQ ID NO:14054 | SEQ ID NO:22066 DYGGMDV |

FIGURE 49
(Continued)

| | | NA | GGTTGCTACTGGAGC | GAAATCAATCATAGTGGAAGGACCAACTACAACCCGTCCCTCAAGAGT | GACTACGGTGTGGGCTTGACTAC |
|---|---|---|---|---|---|
| iPS:435183 | 21-225_93E9 | | SEQ ID NO:6043 | SEQ ID NO:14055 | SEQ ID NO:22067 |
| | | AA | GCYWS | EINHSGRTNYNPSLKS | DYGGLDY |
| | | | SEQ ID NO:6044 | SEQ ID NO:14056 | SEQ ID NO:22068 |
| | | NA | GGTTGCTACTGGAGC | GAAATCAATTATAGTGGAAGAACCAACTACAACCCGTCCCTCAAGAGT | GACTACGGCGGGTATGGACGTC |
| iPS:435195 | 21-225_94D3 | | SEQ ID NO:6045 | SEQ ID NO:14057 | SEQ ID NO:22069 |
| | | AA | GCYWS | EINYSGRTNYNPSLKS | DYGGMDV |
| | | | SEQ ID NO:6046 | SEQ ID NO:14058 | SEQ ID NO:22070 |
| | | NA | AACGATATCATGCAC | GTTATATGGTATGGATGAAGTAATAAATACTATGCAGACTCCGTGAAGGGC | GAAAAATATAGCAGTGGCTGGTACGACTACGGTATGGACGTC |
| iPS:435197 | 21-225_94F3 | | SEQ ID NO:6047 | SEQ ID NO:14059 | SEQ ID NO:22071 |
| | | AA | NDIMH | VIWYDGSNKYYADSVKG | EKYSSGWYDYGMDV |
| | | | SEQ ID NO:6048 | SEQ ID NO:14060 | SEQ ID NO:22072 |
| | | NA | AATTATGATATCAAC | TGGATGAACCCTAACAGTGGTAACACAGGCTATGCACAGAAGTTCCAGGAC | TCCAGTGGCTGGCACTGGTTCGACCCC |
| iPS:435203 | 21-225_75A7 | | SEQ ID NO:6049 | SEQ ID NO:14061 | SEQ ID NO:22073 |
| | | AA | NYDIN | WMNPNSGNTGYAQKFQD | SSGWHWFDP |
| | | | SEQ ID NO:6050 | SEQ ID NO:14062 | SEQ ID NO:22074 |

FIGURE 49 (Continued)

| iPS: | | | | | |
|---|---|---|---|---|---|
| iPS:435209 | 21-225_75A10 | NA | AATTATGATATCAAC | TGGATGAACCCTAACAG TGGTAACACAGGCTATG CACAGAAGTTCCAGGGC | AGCAGTGGCTGGTACTACTT TGACTAC |
| | | | SEQ ID NO:6051 | SEQ ID NO:14063 | SEQ ID NO:22075 |
| | | AA | NYDIN | WMNPNSGNTGYAQKFQG | SSGWYYFDY |
| | | | SEQ ID NO:6052 | SEQ ID NO:14064 | SEQ ID NO:22076 |
| iPS:435211 | 21-225_94E11 | NA | AATTATGATATCAAC | TGGATGAACCCTAACAG TGGTAACACAGGCTATG CACAGAAGTTCCAGGGC | TCCAGTGGCTGGAAGTGGTT CGACCCC |
| | | | SEQ ID NO:6053 | SEQ ID NO:14065 | SEQ ID NO:22077 |
| | | AA | NYDIN | WMNPNSGNTGYAQKFQG | SSGWKWFDP |
| | | | SEQ ID NO:6054 | SEQ ID NO:14066 | SEQ ID NO:22078 |
| iPS:435215 | 21-225_94E12 | NA | AATTATGATATCAAC | TGGATGAACCCTAACAG TGGTAACACAGGCTATG CACAGAAGTTCCAGGGC | ACCAGTGGCTGGAAGTTCTT TGACTAC |
| | | | SEQ ID NO:6055 | SEQ ID NO:14067 | SEQ ID NO:22079 |
| | | AA | NYDIN | WMNPNSGNTGYAQKFQG | TSGWKFFDY |
| | | | SEQ ID NO:6056 | SEQ ID NO:14068 | SEQ ID NO:22080 |
| iPS:435217 | 21-225_94F12 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:6057 | SEQ ID NO:14069 | SEQ ID NO:22081 |
| | | AA | GCYWS | EINHSGSTNYNPSLKS | DYGGMDV |
| | | | SEQ ID NO:6058 | SEQ ID NO:14070 | SEQ ID NO:22082 |
| iPS:435219 | 21-225_95D2 | NA | GGTTGCTACTGGAGC | GAAATCAATCATAGTGG AAGCACCAACTACAACC CGTCCCTCAAGAGT | GACTACGGCGGGTATGGACGT C |

FIGURE 49
(Continued)

| | | | | | |
|---|---|---|---|---|---|
| iPS:435221 | 21-225_95D2 | AA | SEQ ID NO:6059<br>GCYWS | SEQ ID NO:14071<br>EINHSGSTNYNPSLKS | SEQ ID NO:22083<br>DYGGMDV |
| | | NA | SEQ ID NO:6060<br>AGCTATGGCATGCAC | SEQ ID NO:14072<br>GTTATTGGTATGATGGA<br>AGTAATAAATACTATGC<br>AGACTCCGTGAAGGGC | SEQ ID NO:22084<br>GATCGCAATATAGTGGAGC<br>TACTTACTTTGAGTCC |
| iPS:435227 | 21-225_95G2 | AA | SEQ ID NO:6061<br>SYGMH | SEQ ID NO:14073<br>VIWYDGSNKYYADSVKG | SEQ ID NO:22085<br>DRNIVGATYFES |
| | | NA | SEQ ID NO:6062<br>AATTATGATATCAAC | SEQ ID NO:14074<br>TGGATGAACCCTAACAG<br>TGGTAACAGGCTATG<br>CACAGAAGTTCCAGGGC | SEQ ID NO:22086<br>TCCAGTGGCTGGAACTGGT<br>CGACCCC |
| iPS:435235 | 21-225_95G4 | AA | SEQ ID NO:6063<br>NYDIN | SEQ ID NO:14075<br>WMNPNSGNTGYAQKFQG | SEQ ID NO:22087<br>SSGWNWFDP |
| | | NA | SEQ ID NO:6064<br>GGTTGCTACTGGAGC | SEQ ID NO:14076<br>GAAATCAATCATAGTGG<br>AAGCACCAACTACAACC<br>CGTCCCTCAAGAGT | SEQ ID NO:22088<br>GACTACGGCGGTATGGACGT<br>C |
| iPS:435237 | 21-225_95F9 | AA | SEQ ID NO:6065<br>GCYWS | SEQ ID NO:14077<br>EINHSGSTNYNPSLKS | SEQ ID NO:22089<br>DYGGMDV |
| | | NA | SEQ ID NO:6066<br>GGTTGCTACTGGAGC | SEQ ID NO:14078<br>GAAATCAATCATAGTGG<br>AAGCACCAACTACAACC<br>CGTCCCTCAAGAGT | SEQ ID NO:22090<br>GACTACGGCGGTATGGACGT<br>C |
| | 21-225_95G9 | AA | SEQ ID NO:6067<br>GCYWS | SEQ ID NO:14079<br>EINHSGSTNYNPSLKS | SEQ ID NO:22091<br>DYGGMDV |
| | | NA | SEQ ID NO:6068 | SEQ ID NO:14080 | SEQ ID NO:22092 |

FIGURE 49 (Continued)

| | | | | | |
|---|---|---|---|---|---|
| iPS:435239 | 21-225_95H10 | NA | GGTTGCTACTGGAGC SEQ ID NO:6069 | GAAATCAATCATAGTGG AAGCACCAACTACAACC CGTCCCTCAAGAGT SEQ ID NO:14081 | GACTACGGGCGGTATGGACGT C SEQ ID NO:22093 |
| | | AA | GCYWS SEQ ID NO:6070 | EINHSGSTNYNPSLKS SEQ ID NO:14082 | DYGGMDV SEQ ID NO:22094 |
| iPS:435245 | 21-225_95E12 | NA | AATTATGATATCAAC SEQ ID NO:6071 | TGGATGAACCCTAACAG TGGTAACACAGGCTATG CACAGAAGTTCCAGGGC SEQ ID NO:14083 | AGCAGTGGCTGGTACTGGTT CGACCCC SEQ ID NO:22095 |
| | | AA | NYDIN SEQ ID NO:6072 | WMHPNSGNTGYAQKFQG SEQ ID NO:14084 | SSGWYWFDP SEQ ID NO:22096 |
| iPS:435247 | 21-225_96G1 | NA | AATTATGATATCAAC SEQ ID NO:6073 | TGGATGCACCCTAACAA TGGTAACACAGGCTATG CACAGAAGTTCCAGGGC SEQ ID NO:14085 | AGCAGTGGCTGGTACTGGTT CGACCCC SEQ ID NO:22097 |
| | | AA | NYDIN SEQ ID NO:6074 | WMHPNSGNTGYAQKFQG SEQ ID NO:14086 | SSGWYWFDP SEQ ID NO:22098 |
| iPS:435249 | 21-225_96E2 | NA | AATTATGATATCAAC SEQ ID NO:6075 | TGGATGCACCCTAATAG TGGTAACACAGGCTATG CACAGAAGTTCCAGGGC SEQ ID NO:14087 | TCCAGTGGCTGGTACTGGTT CGACCCC SEQ ID NO:22099 |
| | | AA | NYDIN SEQ ID NO:6076 | WMHPNSGNTGYAQKFQG SEQ ID NO:14088 | SSGWYWFDP SEQ ID NO:22100 |
| iPS:435251 | 21-225_96A3 | NA | AGTAGTAATTACTACTGGGG C | AGTATCTATTATAGTGGA TACACCTCCTACAACCCG TCCCTCAAGAGT | CTTGACTCTAACTGGGGTCT |

FIGURE 49
(Continued)

| | | | | | | | | | |
|---|---|---|---|---|---|---|---|---|---|
| iPS:435253 | 21-225_96A3 | AA | SEQ ID NO:6077 | SSNYYWG | SEQ ID NO:14089 | SIYYSGYTSYNPSLKS | SEQ ID NO:22101 | LDSNWGLDY | |
| | | NA | SEQ ID NO:6078 | AGTTATTATGATATCAAC | SEQ ID NO:14090 | TGGATGAACCCTAACAGTGGTAACACAGGCTATGCACAGAAGTTCCAGGGC | SEQ ID NO:22102 | GGCTTTTACGATACTTTGACTGGTTCCGGCTACTACTACGTTATGGACGTC | |
| iPS:435255 | 21-225_96A4 | AA | SEQ ID NO:6079 | SYDIN | SEQ ID NO:14091 | WMNPNSGNTGYAQKFQG | SEQ ID NO:22103 | GFYDTLTGSGYYYVMDV | |
| | | NA | SEQ ID NO:6080 | AATTATGATATCAAC | SEQ ID NO:14092 | TGGATGAACCCTAACAGTGGTAACACAGGCTATGCACAGAAGTTCCAGGGC | SEQ ID NO:22104 | TCCAGTGGCTGGTCCTGGTTCGACCCC | |
| iPS:435257 | 21-225_96D5 | AA | SEQ ID NO:6081 | NYDIN | SEQ ID NO:14093 | WMNPNSGNTGYAQKFQG | SEQ ID NO:22105 | SSGWSWFDP | |
| | | NA | SEQ ID NO:6082 | AATTATGATATCAAC | SEQ ID NO:14094 | TGGATGCACCCTAACAGTGGTAACACAGGCTATGCACAGAAGTTCCAGGGC | SEQ ID NO:22106 | AGTAGTGGCTGGTCCTGGTACAAATTTGACTAC | |
| iPS:435257 | 21-225_96H5 | AA | SEQ ID NO:6083 | NYDIN | SEQ ID NO:14095 | WMHPNSGNTGYAQKFQG | SEQ ID NO:22107 | SSGWYKFDY | |
| | | NA | SEQ ID NO:6084 | AGTTATGATATCAAC | SEQ ID NO:14096 | TGGATGAACCCTAACAGTCGTAACACAGGCTATGCACAGAAGTTCCAGGGC | SEQ ID NO:22108 | GGCGGCTAGCGATGTTTTGCCTGGGAATAACTACTACTACGATATGGACGTC | |
| iPS:435259 | 21-225_96C6 | AA | SEQ ID NO:6085 | SYDIN | SEQ ID NO:14097 | WMNPNSRNTGYAQKFQG | SEQ ID NO:22109 | GGYDVLPGNNYYYDMDV | |

FIGURE 49
(Continued)

| | | | SEQ ID NO:6086 | | SEQ ID NO:14098 | | SEQ ID NO:22110 |
|---|---|---|---|---|---|---|---|
| iPS:435267 | 21-225_96D10 | NA | AATTATGATATCAAC | | TGGATGCACCCTAACAG TGGTAACACAGGCTATG CACAGAAGTTCCAGGGC | | AGCAGTGGCTGGTACTTTT TGACTAC |
| | | AA | SEQ ID NO:6087 NYDIN | | SEQ ID NO:14099 WMHPNSGNTGYAQKFQG | | SEQ ID NO:22111 SSGWYFFDY |
| iPS:435273 | 21-225_97A2 | NA | SEQ ID NO:6088 GGTTGCTACTGGAGC | | SEQ ID NO:14100 GAAATCAATCATAGTGG AAGCACCAACTACAACC CGTCCCTCAAGAGT | | SEQ ID NO:22112 GACTACGGCGGGTATGGACGT C |
| | | AA | SEQ ID NO:6089 GCYWS | | SEQ ID NO:14101 EINHSGSTNYNPSLKS | | SEQ ID NO:22113 DYGGMDV |
| iPS:435279 | 21-225_97H4 | NA | SEQ ID NO:6090 AATTATGATATCAAC | | SEQ ID NO:14102 TGGATGCACCCTAACAG TGGTAACACAGGCTATG CACAGAAGTTCCAGGGC | | SEQ ID NO:22114 AGCAGTGGCTGGTACTGGTT CGACCCC |
| | | AA | SEQ ID NO:6091 NYDIN | | SEQ ID NO:14103 WMHPNSGNTGYAQKFQG | | SEQ ID NO:22115 SSGWYWFDP |
| iPS:435281 | 21-225_97E5 | NA | SEQ ID NO:6092 GGTTGCTACTGGAGC | | SEQ ID NO:14104 GAAATCAATCATAGTGG AAGCACCAACTACAACC CGTCCCTCAAGAGT | | SEQ ID NO:22116 GACTACGGCGGGTATGGACGT C |
| | | AA | SEQ ID NO:6093 GCYWS | | SEQ ID NO:14105 EINHSGSTNYNPSLKS | | SEQ ID NO:22117 DYGGMDV |
| | | | SEQ ID NO:6094 | | SEQ ID NO:14106 | | SEQ ID NO:22118 |

FIGURE 49
(Continued)

| | | | | |
|---|---|---|---|---|
| iPS:435291 | 21-225_146E1 | NA | AGCTATGGCATGCAC | ATTATATGGTATGATGG AAGTAATAAATACTATG CAGACTCCGTGAAGGGC | GATCGTTAGTGGGAGCTAC CGCTGATGCTTTGATATC |
| | | | SEQ ID NO:6095 | SEQ ID NO:14107 | SEQ ID NO:22119 |
| | | AA | SYGMH | IIWYDGSNKYYADSVKG | DRLVGATADAFDI |
| | | | SEQ ID NO:6096 | SEQ ID NO:14108 | SEQ ID NO:22120 |
| iPS:435293 | 21-225_146F1 | NA | AGAAGTAGTTACTACTGGGG C | AGTATATATTATAGTGG GAGTACCTCCTACAACC CGTCCCTCAAGAGT | CTTGATCTCCTGTGTGGAGTTTT GACTAC |
| | | | SEQ ID NO:6097 | SEQ ID NO:14109 | SEQ ID NO:22121 |
| | | AA | RSSYYWG | SIYYSGSTSYNPSLKS | LDLLWSFDY |
| | | | SEQ ID NO:6098 | SEQ ID NO:14110 | SEQ ID NO:22122 |
| iPS:435295 | 21-225_146H1 | NA | AGCTATGCCATGAGC | GCTATTAGTGGTGTCGTGGT GGTAACACATTCTACGC AGACTCCGTGAAGGGC | CGGGTGACGGACTACGGTGG TAACGACTGGTTCGACCCC |
| | | | SEQ ID NO:6099 | SEQ ID NO:14111 | SEQ ID NO:22123 |
| | | AA | SYAMS | AISGRGGNTFYADSVKG | RVTDYGGNDWFDP |
| | | | SEQ ID NO:6100 | SEQ ID NO:14112 | SEQ ID NO:22124 |
| iPS:435297 | 21-225_146B3 | NA | AGCTATGGCATGCAC | GTTATATGGTATGATGG AAGTTATAAATACTATG CAGACTCCGTGAAGGGC | ATGGGTATAGAAGTGGCTGT GGACTACTACTACGGTATGG ACGTC |
| | | | SEQ ID NO:6101 | SEQ ID NO:14113 | SEQ ID NO:22125 |
| | | AA | SYGMH | VIWYDGSYKYYADSVKG | MGIEVAVDYYYGMDV |
| | | | SEQ ID NO:6102 | SEQ ID NO:14114 | SEQ ID NO:22126 |
| iPS:435299 | 21-225_146D4 | NA | AATTATGATATCAAC | TGGGTGCACCCTAACAG TGGTAACACAGGCTATG CACAGAAGTTCCAGGGC | AGCAGTGGCTGGTACTACTT TGACTAC |
| | | | SEQ ID NO:6103 | SEQ ID NO:14115 | SEQ ID NO:22127 |

FIGURE 49
(Continued)

| | | | | WVHPNSGNTGYAQKFQG | SSGWYYFDY |
|---|---|---|---|---|---|
| iPS:435301 | 21-225_146G4 | AA | NYDIN | | |
| | | | SEQ ID NO:6104 | SEQ ID NO:14116 | SEQ ID NO:22128 |
| | | NA | AACAGTGGTTACTACTGGAG C | TACAGTATTACAGTGG GAGCACCTACTACAACC CGTCCCTCAAGAGT | GGGAAATATAACTGGAACCA TGCTTTTGATATC |
| | | | SEQ ID NO:6105 | SEQ ID NO:14117 | SEQ ID NO:22129 |
| iPS:435303 | 21-225_146A6 | AA | NSGYYWS | YSYYSGSTYYNPSLKS | GKYNWNHAFDI |
| | | | SEQ ID NO:6106 | SEQ ID NO:14118 | SEQ ID NO:22130 |
| | | NA | AGCTATGCCATGAAC | GCTATTAGTGGTAGTGGT GGTAACACATTCTACGC AGACTCCGTGAAGGGC | AAGGATAATGATTACGTTTG GGGGAGTCCTTACTTTGACT AC |
| | | | SEQ ID NO:6107 | SEQ ID NO:14119 | SEQ ID NO:22131 |
| iPS:435305 | 21-225_146C9 | AA | SYAMS | AISGSGGNTFYADSVKG | KDNDYVWGSPYFDY |
| | | | SEQ ID NO:6108 | SEQ ID NO:14120 | SEQ ID NO:22132 |
| | | NA | AATTATGATATCAAC | TGGATGCACCTAACAG TGGTAACACAGGCTATG CACAGAAGTTCCAGGGC | AGCAGTGGCTGGTACTCCTT TGACTAC |
| | | | SEQ ID NO:6109 | SEQ ID NO:14121 | SEQ ID NO:22133 |
| iPS:435307 | 21-225_146E9 | AA | NYDIN | WMHPNSGNTGYAQKFQG | SSGWYSFDY |
| | | | SEQ ID NO:6110 | SEQ ID NO:14122 | SEQ ID NO:22134 |
| | | NA | AGCTATGCCATGAGC | GCTATTAGTGGTGGTCGTGGT GGTAACACATTCTACGC AGACTCCGTGAAGGGC | CGGGTGACGGACTACGGTGG TAACGACTGGTTCGACCCC |
| | | | SEQ ID NO:6111 | SEQ ID NO:14123 | SEQ ID NO:22135 |
| | | AA | SYAMS | AISGRGGNTFYADSVKG | RVIDYGGNDWFDP |
| | | | SEQ ID NO:6112 | SEQ ID NO:14124 | SEQ ID NO:22136 |

FIGURE 49
(Continued)

| | | | | | |
|---|---|---|---|---|---|
| iPS:435309 | 21-225_146F9 | NA | AATTATGATATCAAC | TGGATGCACCCTAACAGTGGTAACACAGGCTATGCACAGAAGTTCCAGGGC | AGCAGTGGCTGGTACTTTTTTGACTAC |
| | | | SEQ ID NO:6113 | SEQ ID NO:14125 | SEQ ID NO:22137 |
| | | AA | NYDIN | WMHPNSGNTGYAQKFQG | SSGWYFFDY |
| | | | SEQ ID NO:6114 | SEQ ID NO:14126 | SEQ ID NO:22138 |
| iPS:435311 | 21-225_146H9 | NA | AGCTATGGCATGCAC | GTGATATGGTTTGATGAAAGTAATAAACACTATGGAGACTCCGTGAAGGGC | GAATTGGGATTTCTCTCTGACTAT |
| | | | SEQ ID NO:6115 | SEQ ID NO:14127 | SEQ ID NO:22139 |
| | | AA | SYGMH | VIWFDESNKHYGDSVKG | ELGFLSDY |
| | | | SEQ ID NO:6116 | SEQ ID NO:14128 | SEQ ID NO:22140 |
| iPS:435313 | 21-225_146G11 | NA | AGCTATAGCATGAAC | TCCATTAGTGGTAGTGGTAGCTACACATACTACGCAGACTCAGTGAAGGGC | GGTAGCAGCTCGTCCGGGTTTGACTAC |
| | | | SEQ ID NO:6117 | SEQ ID NO:14129 | SEQ ID NO:22141 |
| | | AA | SYSMN | SISGSGSYTYYADSVKG | GSSSSGFDY |
| | | | SEQ ID NO:6118 | SEQ ID NO:14130 | SEQ ID NO:22142 |
| iPS:435315 | 21-225_147B2 | NA | AGCTATGGCATGCAC | GTTATATGGTATGATGGAAGTAATAAATACTATGCAGACTCCGTGAAGGGC | AGGTATAGCAGCAGCTGGTCGGGGGTATGGACGTC |
| | | | SEQ ID NO:6119 | SEQ ID NO:14131 | SEQ ID NO:22143 |
| | | AA | SYGMH | VIWYDGSNKYYADSVKG | RYSSSWSGGMDV |
| | | | SEQ ID NO:6120 | SEQ ID NO:14132 | SEQ ID NO:22144 |

FIGURE 49
(Continued)

| | | | | |
|---|---|---|---|---|
| iPS:435317 | 21-225_147D2 | NA | AGTGGTGATTACTACTGGAA C SEQ ID NO:6121 | TTCATCTATTACACTGGG AGCACTACTACAACCC GTCCCTCAAGAGT SEQ ID NO:14133 | GGGGGAGCTTACTACTCCTA CTACGGTATGGACGTC SEQ ID NO:22145 |
| | | AA | SGDYYWN SEQ ID NO:6122 | FIYYTGSTYYNPSLKS SEQ ID NO:14134 | GGAYYSYYGMDV SEQ ID NO:22146 |
| iPS:435319 | 21-225_147E3 | NA | AATAGTGGTTACTACTATAG C SEQ ID NO:6123 | TACATCTATTACAGGTGGG GGCACCTACTACAACCC GTCCCTCAAGAGT SEQ ID NO:14135 | GGGGGATATAACTGGAACCA TGCTTTTGATTTC SEQ ID NO:22147 |
| | | AA | NSGYYYS SEQ ID NO:6124 | YIYYSGGTYYNPSLKS SEQ ID NO:14136 | GGYNWNHAFDF SEQ ID NO:22148 |
| iPS:435321 | 21-225_147E4 | NA | AATTATATGATATCAAC SEQ ID NO:6125 | TGGATGAACCTAACAG TGGTAACACAGGCTATG CACAGAAGTTCCAGGGC SEQ ID NO:14137 | AGCAGTGGCTGGTACTTTT TGACTAC SEQ ID NO:22149 |
| | | AA | NYDIN SEQ ID NO:6126 | WMNPNSGNTGYAQKFQG SEQ ID NO:14138 | SSGWYFDY SEQ ID NO:22150 |
| iPS:435323 | 21-225_147D5 | NA | AATTATATGATATCAAC SEQ ID NO:6127 | TGGGTGCACCTAACAG TGGTAACACAGGCTATG CACAGAAGTTCCAGGGC SEQ ID NO:14139 | AGCAGTGGCTGGTACTACTT TGACTAC SEQ ID NO:22151 |
| | | AA | NYDIN SEQ ID NO:6128 | WVHPNSGNTGYAQKFQG SEQ ID NO:14140 | SSGWYFDY SEQ ID NO:22152 |
| iPS:435325 | 21-225_147H5 | NA | GACTATGGCATGCAC SEQ ID NO:6129 | GTTATATGGTATGATGG AAGTAATAAGTACTATG CAGACTCCGTGAAGGGC SEQ ID NO:14141 | GAGAGGTATAGCAGTGGCTG GTACGACTACGGTTTGGACG TC SEQ ID NO:22153 |

FIGURE 49 (Continued)

| | | AA/NA | CDR1 | CDR2 | CDR3 |
|---|---|---|---|---|---|
| iPS:435327 | 21-225_147G6 | AA | DYGMH | VIWYDGSNKYYADSVKG | ERYSSGWYDYGLDV |
| | | NA | SEQ ID NO:6130<br>AATTATGATATCAAC | SEQ ID NO:14142<br>TGGATGCACCCAACAGTGGTAACACAGGCTATGCACAGAAGTTCCAGGGC | SEQ ID NO:22154<br>AGCAGTGGCTGGTACTGGTTCGACCCC |
| iPS:435329 | 21-225_147A8 | AA | NYDIN<br>SEQ ID NO:6131 | WMHPNSGNTGYAQKFQG<br>SEQ ID NO:14143 | SSGWYWFDP<br>SEQ ID NO:22155 |
| | | NA | SEQ ID NO:6132<br>AGCTATGGCATGCAC | SEQ ID NO:14144<br>GTTATATGGTATGATGGAAGTAATAAATACTATGCAGACTCCGTGAAGGGC | SEQ ID NO:22156<br>AGGTATAGCAGCAGCTGGACGGGGGTATGGACGTC |
| iPS:435331 | 21-225_147G8 | AA | SYGMH<br>SEQ ID NO:6133 | VIWYDGSNKYYADSVKG<br>SEQ ID NO:14145 | RYSSSWTGGMDV<br>SEQ ID NO:22157 |
| | | NA | SEQ ID NO:6134<br>GCTTACTACTGGAGC | SEQ ID NO:14146<br>GAAATCAATCATAGTGGAAGTACCAACTACAAACCGTCCCTCAAGAGT | SEQ ID NO:22158<br>GACTACGGTGTTTTTGACTAC |
| iPS:435333 | 21-225_147E9 | AA | AYYWS<br>SEQ ID NO:6135 | EINHSGSTNYKPSLKS<br>SEQ ID NO:14147 | DYGVFDY<br>SEQ ID NO:22159 |
| | | NA | SEQ ID NO:6136<br>AGCTATAGCATGAAC | SEQ ID NO:14148<br>TCCATTAGTGGTAGAAACACTACCATATACTATGCAGACTCTGTGAAGGGC | SEQ ID NO:22160<br>GATCGGGGGCAGTTGC |
| | | AA | SYSMN<br>SEQ ID NO:6137 | SISGRNTTIYYADSVKG<br>SEQ ID NO:14149 | DRGSC<br>SEQ ID NO:22161 |
| | | | SEQ ID NO:6138 | SEQ ID NO:14150 | SEQ ID NO:22162 |

FIGURE 49
(Continued)

| | | | | |
|---|---|---|---|---|
| iPS:435335 | 21-225_147D10 | NA | AGCTATGCCATGAGC | GCTATTAGTGTGGTCGTGGT GGTAACACATTCTACGC AGACTCCGTGAAGGGC | AAGGATTATGATTACGTTTG GGGGAGTCCTTACTTTGACT AC |
| | | | SEQ ID NO:6139 | SEQ ID NO:14151 | SEQ ID NO:22163 |
| | | AA | SYAMS | AISGRGGNTFYADSVKG | KDYDYVWGSPYFDY |
| | | | SEQ ID NO:6140 | SEQ ID NO:14152 | SEQ ID NO:22164 |
| iPS:435339 | 21-225_147D12 | NA | AGCTATGCCATGAGC | GCTATTAGTGTGGTCGTGGT GGTAACACATTCTACGC AGACTCCGTGAAGGGC | AAGGATTATGATTACGTTTG GGGGAGTCCTTACTTTGACT AC |
| | | | SEQ ID NO:6141 | SEQ ID NO:14153 | SEQ ID NO:22165 |
| | | AA | SYGMH | AISGRGGNTFYADSVKG | KDYDYVWGSPYFDY |
| | | | SEQ ID NO:6142 | SEQ ID NO:14154 | SEQ ID NO:22166 |
| iPS:435341 | 21-225_148B2 | NA | AGCTATGCCATGCAC | ATTATCTGGTATGATGGA AGTTATAAATACTATGC AGACTCCGTGAAGGGC | GATCATTTCGATTTTTGGAGT GGTCACTTTGACTAC |
| | | | SEQ ID NO:6143 | SEQ ID NO:14155 | SEQ ID NO:22167 |
| | | AA | SYGMH | IIWYDGSYKYYADSVKG | DHFDFWSGHFDY |
| | | | SEQ ID NO:6144 | SEQ ID NO:14156 | SEQ ID NO:22168 |
| iPS:435343 | 21-225_148E2 | NA | AGCTATGCCATGAGC | GCTATTAGTGTGGTCGTGGT GGTAACACATTCTACGC AGACTCCGTGAAGGGC | AAGGATTATGATTACGTTTG GGGGAGTCCTTACTTTGACT AC |
| | | | SEQ ID NO:6145 | SEQ ID NO:14157 | SEQ ID NO:22169 |
| | | AA | SYAMS | AISGRGGNTFYADSVKG | KDYDYVWGSPYFDY |
| | | | SEQ ID NO:6146 | SEQ ID NO:14158 | SEQ ID NO:22170 |
| iPS:435345 | 21-225_148G3 | NA | AATTATGATATCAAC | TGGATGCACCCTAACAG TGGTAACACAGGCTATG CACAGAACTTCCAGGGC | AGCAGTGGCTGGTACTTTTT TGACTAC |
| | | | SEQ ID NO:6147 | SEQ ID NO:14159 | SEQ ID NO:22171 |
| | | AA | NYDIN | WMHPNSGNTGYAQNFQG | SSGWYFFDY |

FIGURE 49
(Continued)

| | | | | | | |
|---|---|---|---|---|---|---|
| iPS:435347 | 21-225_148C4 | NA | SEQ ID NO:6148 AGCTATGCCATGAAC | SEQ ID NO:14160 GCTATTAGTGGTAGTGGT GGTAACACATTCTACGC AGACTCCGTGAAGGGC | SEQ ID NO:22172 CGGGTGACGGACTACGGTGG TAACGACTGGTTCGACCCC | |
| | | AA | SEQ ID NO:6149 SYAMN | SEQ ID NO:14161 AISGSGGNTFYADSVKG | SEQ ID NO:22173 RVTDYGGNDWFDP | |
| iPS:435349 | 21-225_148F5 | NA | SEQ ID NO:6150 AGCTATGGCATGCAC | SEQ ID NO:14162 GTTATATGGTATGATGG AAGTAATAAATACTATG CAGACTCCGTGAAGGGC | SEQ ID NO:22174 AGGTATAGCAGCAGCTGGTC GGGGGGTATGGACGTC | |
| | | AA | SEQ ID NO:6151 SYGMH | SEQ ID NO:14163 VIWYDGSNKYYADSVKG | SEQ ID NO:22175 RYSSSWSGGMDV | |
| iPS:435351 | 21-225_148B6 | NA | SEQ ID NO:6152 GGCTACTATATGCAC | SEQ ID NO:14164 TGGATCCACCTAACAA TGGTGGCACAAACTATG CACAGACGTTTCAGGGC | SEQ ID NO:22176 GATCCTGTAGTAGTACCAGC TGCCCCCTTTGACTAC | |
| | | AA | SEQ ID NO:6153 GYYMH | SEQ ID NO:14165 WIHPNNGGTNYAQTFQG | SEQ ID NO:22177 DPVVPAAPFDY | |
| iPS:435353 | 21-225_148F8 | NA | SEQ ID NO:6154 AATTATGATATCAAC | SEQ ID NO:14166 TGGATGAACCCTAACAG TGGTAACACAGGCTATG CACAGAAGTTCCAGGGC | SEQ ID NO:22178 AGCAGTGGCTGGTACTACTT TGACTAC | |
| | | AA | SEQ ID NO:6155 NYDIN | SEQ ID NO:14167 WMNPNSGNTGYAQKFQG | SEQ ID NO:22179 SSGWYYFDY | |
| | | | SEQ ID NO:6156 | SEQ ID NO:14168 | SEQ ID NO:22180 | |

FIGURE 49 (Continued)

| | | | | | |
|---|---|---|---|---|---|
| iPS:435355 | 21-225_148H9 | NA | AGCTATGCCATGAGC | GCTATTAGTGGTCGTGTGGT GGTAACACATTCTACGC AGACTCCGTGAAGGGC | CGGGTGACGGACTACGGTGG TAACGACTGGTTCGACCCC |
| | | | SEQ ID NO:6157 | SEQ ID NO:14169 | SEQ ID NO:22181 |
| | | AA | SYAMS | AISGRGGNTFYADSVKG | RVTDYGGNDWFDP |
| | | | SEQ ID NO:6158 | SEQ ID NO:14170 | SEQ ID NO:22182 |
| iPS:435357 | 21-225_148G10 | NA | AGCTATGGCATGCAC | ATTATATGGTATGATGG AAGTAATAAATACTATG CAGACTCCGTGAAGGGC | GATCGTTACGATTTTGAG TGGTCACTTTGACTAC |
| | | | SEQ ID NO:6159 | SEQ ID NO:14171 | SEQ ID NO:22183 |
| | | AA | SYGMH | IIWYDGSNKYYADSVKG | DRYDFWSGHFDY |
| | | | SEQ ID NO:6160 | SEQ ID NO:14172 | SEQ ID NO:22184 |
| iPS:435359 | 21-225_148H10 | NA | AGCTATGGCATGCAC | GTTATATGGTATGATGG AAGTAATAAATACTATG GAGACTCCGTGAAGGGC | AGGTATAGCAGCAGCTGGTC GGGGGTATGGACGTC |
| | | | SEQ ID NO:6161 | SEQ ID NO:14173 | SEQ ID NO:22185 |
| | | AA | SYGMH | VIWYDGSNKYYGDSVKG | RYSSSWSGGMDV |
| | | | SEQ ID NO:6162 | SEQ ID NO:14174 | SEQ ID NO:22186 |
| iPS:435361 | 21-225_148E11 | NA | AGAAGTAGTTACTACTGGGG C | AGTATCTATTATACAGTGGG AGCACCTCCTACAACCC GTCCCTCAAGAGT | CTTGATCCCCAGTGGAGTTT TGACTAC |
| | | | SEQ ID NO:6163 | SEQ ID NO:14175 | SEQ ID NO:22187 |
| | | AA | RSSYYWG | SIYYSGSTSYNPSLKS | LDPQWSFDY |
| | | | SEQ ID NO:6164 | SEQ ID NO:14176 | SEQ ID NO:22188 |
| iPS:435363 | 21-225_148F12 | NA | AATGGTGGTTACTACTGGAA C | TACATCTATTACAGTGGG AGCACTACTACAACCC GTCCCTCAAGAGT | TACAGTAGTACTAGGACTACTA CTACGGTATGGACGTC |

FIGURE 49
(Continued)

| | | | | | | |
|---|---|---|---|---|---|---|
| iPS:435365 | 21-225_148F12 | AA | SEQ ID NO:6165<br>NGGYYWN | SEQ ID NO:14177<br>YIYYSGSTYYNPSLKS | SEQ ID NO:22189<br>YSTYDYYYGMDV |
| | | NA | SEQ ID NO:6166<br>AGCTATGGCATGCAC | SEQ ID NO:14178<br>ATTATCTGGTATGATGGA<br>AGTATAAATACTATGC<br>AGACTCCGTGAAGGGC | SEQ ID NO:22190<br>GATCATTTGATTTTTGGAGT<br>GGTCACTTGACTAC |
| iPS:435367 | 21-225_149F1 | AA | SEQ ID NO:6167<br>SYGMH | SEQ ID NO:14179<br>IIWYDGSYKYYADSVKG | SEQ ID NO:22191<br>DHFDFWSGHFDY |
| | | NA | SEQ ID NO:6168<br>GACTATGGCATGCAC | SEQ ID NO:14180<br>GTTATATGGTATGAAGG<br>AAGTAATAAATACTATG<br>CAGACTCCGTGAAGGGC | SEQ ID NO:22192<br>GAAATAGGATTCAGTGAGGA<br>CTAC |
| iPS:435369 | 21-225_149G1 | AA | SEQ ID NO:6169<br>DYGMH | SEQ ID NO:14181<br>VIWYEGSNKYYADSVKG | SEQ ID NO:22193<br>EIGFSEDY |
| | | NA | SEQ ID NO:6170<br>AATTATGATATCAAC | SEQ ID NO:14182<br>TGGGTGCACCTAACAG<br>TGGTAACACAGGCTATG<br>CAGACACATTCCAGGGC | SEQ ID NO:22194<br>AGCAGTGGCTGGTACTACTT<br>TGACTAC |
| iPS:435371 | 21-225_149A2 | AA | SEQ ID NO:6171<br>NYDIN | SEQ ID NO:14183<br>WVHPNSGNTGYAQKFQG | SEQ ID NO:22195<br>SSGWYYFDY |
| | | NA | SEQ ID NO:6172<br>AACTATGCCATGACC | SEQ ID NO:14184<br>GCTATTAGTAGTGGTGGT<br>GGTAACACATTCTACGC<br>AGACTCCGTGAAGGGC | SEQ ID NO:22196<br>CGGGTGACGGACGACTACGGTGG<br>TAACGACTGGTTCGACCCC |
| iPS:435371 | 21-225_149A3 | AA | SEQ ID NO:6173<br>NYAMT | SEQ ID NO:14185<br>AISGRGGNTFYADSVKG | SEQ ID NO:22197<br>RVTDYGGNDWFDP |
| | | | SEQ ID NO:6174 | SEQ ID NO:14186 | SEQ ID NO:22198 |

FIGURE 49 (Continued)

| | | | | | |
|---|---|---|---|---|---|
| iPS:435373 | 21-225_149E3 | NA | AATTATGATATCAAC<br>SEQ ID NO:6175 | TGGATGCACCCTAACAG<br>TGGTAACACAGGCTATG<br>CACAGAAGTTCCAGGGC<br>SEQ ID NO:14187 | AGCAGTGGCTGGTACTGGTT<br>TGACTAC<br>SEQ ID NO:22199 |
| | | AA | NYDIN<br>SEQ ID NO:6176 | WMHPNSGNTGYAQKFQG<br>SEQ ID NO:14188 | SSGWYWFDY<br>SEQ ID NO:22200 |
| iPS:435375 | 21-225_149H4 | NA | AATTATGATATCAAC<br>SEQ ID NO:6177 | TGGATGCACCCTAACAG<br>TGGTAACACAGACTATG<br>CACAGAAGTTCCAGGGC<br>SEQ ID NO:14189 | AGCAGTGGCTGGTACTACTT<br>TGACTAC<br>SEQ ID NO:22201 |
| | | AA | NYDIN<br>SEQ ID NO:6178 | WMHPNSGNTDYAQKFQG<br>SEQ ID NO:14190 | SSGWYYFDY<br>SEQ ID NO:22202 |
| iPS:435377 | 21-225_149G5 | NA | AATGGTGGTTACTACTGGAA<br>C<br>SEQ ID NO:6179 | TACATCTATTACAGTGGG<br>AGCACCTACTACAACCC<br>GTCCCTCAAGAGT<br>SEQ ID NO:14191 | TACAGTACTACGACTACTA<br>CTACGGTATGGACGTC<br>SEQ ID NO:22203 |
| | | AA | NGGYYWN<br>SEQ ID NO:6180 | YIYYSGSTYYNPSLKS<br>SEQ ID NO:14192 | YSTYDYYYGMDV<br>SEQ ID NO:22204 |
| iPS:435379 | 21-225_149B6 | NA | AGCTATGCCATGAGC<br>SEQ ID NO:6181 | GTTATTAGTGGTAGTGGT<br>GGTAGCACATTCTACGC<br>AGACTCCGTGAAGGGC<br>SEQ ID NO:14193 | CGAACTCCGGAAGATGTTT<br>TGATATC<br>SEQ ID NO:22205 |
| | | AA | SYAMS<br>SEQ ID NO:6182 | VISGSGGSTFYADSVKG<br>SEQ ID NO:14194 | RTPEDVFDI<br>SEQ ID NO:22206 |
| iPS:435381 | 21-225_149C6 | NA | AGCTATGCCATGAGC<br>SEQ ID NO:6183 | GCTATTAGTGGTAGTGGT<br>GGTAACACATTCTACGC<br>AGACTCCGTGAAGGGC<br>SEQ ID NO:14195 | AAGGATTATGATTACGTTTG<br>GGGGAGTCCTTACTTTGACT<br>AC<br>SEQ ID NO:22207 |

FIGURE 49
(Continued)

| | | | | SYAMS | AISGSGGNTFYADSVKG | KDYDYVWGSPYFDY |
|---|---|---|---|---|---|---|
| iPS:435383 | | | AA | SEQ ID NO:6184 | SEQ ID NO:14196 | SEQ ID NO:22208 |
| | 21-225_149D7 | | NA | AACAGTGGTTACTACTGGAG C | TACAGCTATTACAGTGG GAGCACCTACTACAACC CGTCCCTCAAGAGT | GGGGGATATAACTGGAACCA TGCTTTGATATC |
| | | | | SEQ ID NO:6185 | SEQ ID NO:14197 | SEQ ID NO:22209 |
| | | | AA | NSGYYWS | YSYYSGSTYYNPSLKS | GGYNWNHAFDI |
| | | | | SEQ ID NO:6186 | SEQ ID NO:14198 | SEQ ID NO:22210 |
| iPS:435391 | 21-225_149F8 | | NA | AGCTATGCCATGAGC | GCTATTAGTGGTCGTGGT GGTAACACATTCTACGC AGACTCCGTGAAGGGC | AAGGATTATGATTACGTTTG GGGGAGTCCTTACTTTGACT AC |
| | | | | SEQ ID NO:6187 | SEQ ID NO:14199 | SEQ ID NO:22211 |
| | | | AA | SYAMS | AISGRGGNTFYADSVKG | KDYDYVWGSPYFDY |
| | | | | SEQ ID NO:6188 | SEQ ID NO:14200 | SEQ ID NO:22212 |
| iPS:435393 | 21-225_149D10 | | NA | GACTATGGCATGCAC | GTTATATGGTATGATGG AAGTAATAAGTACTATG CAGACTCCGTGAAGGGC TC | GAGAGGTATAGCAGTGGCTG GTACGACTACGGTATGGACG |
| | | | | SEQ ID NO:6189 | SEQ ID NO:14201 | SEQ ID NO:22213 |
| | | | AA | DYGMH | VIWYDGSNKYYADSVKG | ERYSSGWYDYGMDV |
| | | | | SEQ ID NO:6190 | SEQ ID NO:14202 | SEQ ID NO:22214 |
| iPS:435395 | 21-225_149D11 | | NA | AGCTATGCCATGAGC | GCTATTAGTGGTCGTGGT GGTAACACATTCTACGC AGACTCCGTGAAGGGC | AAGGATTATGATTACGTTTG GGGGAGTCCTTACTTTGACT AC |
| | | | | SEQ ID NO:6191 | SEQ ID NO:14203 | SEQ ID NO:22215 |
| | | | AA | SYAMS | AISGRGGNTFYADSVKG | KDYDYVWGSPYFDY |
| | | | | SEQ ID NO:6192 | SEQ ID NO:14204 | SEQ ID NO:22216 |

FIGURE 49
(Continued)

| | | | | |
|---|---|---|---|---|
| iPS:435397 | 21-225_149F12 | NA | GACTATGGCATGCAC | GTTATATGGTATGAAGA AATAATAAATACTATG CAGACTCCGTGAAGGC | GAAATAGGGTTCAGTGAAGGA CTAC |
| | | | SEQ ID NO:6193 | SEQ ID NO:14205 | SEQ ID NO:22217 |
| | | AA | DYGMH | VIWYEENNKYYADSVKG | EIGFSEDY |
| | | | SEQ ID NO:6194 | SEQ ID NO:14206 | SEQ ID NO:22218 |
| iPS:435399 | 21-225_150D2 | NA | AATTATGATATCAAC | TGGATGCACCTAACAG TGGTAACACAGGCTATG CACAGAAGTTCCAGGGC | AGCAGTGGCTGTACTACTT TGACTAC |
| | | | SEQ ID NO:6195 | SEQ ID NO:14207 | SEQ ID NO:22219 |
| | | AA | NYDIN | WMHPNSGNTGYAQKFQG | SSGWYYFDY |
| | | | SEQ ID NO:6196 | SEQ ID NO:14208 | SEQ ID NO:22220 |
| iPS:435401 | 21-225_150E2 | NA | AGCTATGTCATGCAC | GTTATATGGTATGATGG AAGTAATAAATACTATG CAGACTCCGTGAAGGGC | GAGGAGTATAGCAGCAGCTG GTACGGGTACGGTATGGACG TC |
| | | | SEQ ID NO:6197 | SEQ ID NO:14209 | SEQ ID NO:22221 |
| | | AA | SYVMH | VIWYDGSNKYYADSVKG | EEYSSSWYGYGMDV |
| | | | SEQ ID NO:6198 | SEQ ID NO:14210 | SEQ ID NO:22222 |
| iPS:435403 | 21-225_150C5 | NA | AGCTATGCCATGAGC | GCTATTAGTGGTAGTGGT GGTAACACATTCTACGC AGACTCCGTGAAGGGC | AAGGATTATGATTACGTTTG GGGGAGTCCTACTTTGACT AC |
| | | | SEQ ID NO:6199 | SEQ ID NO:14211 | SEQ ID NO:22223 |
| | | AA | SYAMS | AISGSGGNTFYADSVKG | KDYDYVWGSPYFDY |
| | | | SEQ ID NO:6200 | SEQ ID NO:14212 | SEQ ID NO:22224 |

FIGURE 49
(Continued)

| | | | | |
|---|---|---|---|---|
| iPS:435405 | 21-225_150B7 | NA | AATTATGATATCAAC | TGGATGCACCCTAACAG TGGTAACACAGGCTATG CACAGAAGTTCCAGGGC | AGCAGTGGCTGGTACTTTTT TGACTAC |
| | | | SEQ ID NO:6201 | SEQ ID NO:14213 | SEQ ID NO:22225 |
| | | AA | NYDIN | WMHPNSGNTGYAQKFQG | SSGWYFFDY |
| | | | SEQ ID NO:6202 | SEQ ID NO:14214 | SEQ ID NO:22226 |
| iPS:435407 | 21-225_150E7 | NA | GACTATGGCATGCAC | GTTATATGGTATGAAGA AATAATAAATACTATG CAGACTCCGTGAAGGGC | GAAATAGGGTTCAGTGAGGA CTAC |
| | | | SEQ ID NO:6203 | SEQ ID NO:14215 | SEQ ID NO:22227 |
| | | AA | DYGMH | VIWYEENNKYYADSVKG | EIGFSEDY |
| | | | SEQ ID NO:6204 | SEQ ID NO:14216 | SEQ ID NO:22228 |
| iPS:435409 | 21-225_150G8 | NA | ACCTATAGCATGACT | TACATTAGTAGGAGTAG TAGTACCATATACTACGC AGACTCTGTGAAGGGC | TCGGCATTTAGCCCTTTGAT CTAC |
| | | | SEQ ID NO:6205 | SEQ ID NO:14217 | SEQ ID NO:22229 |
| | | AA | TYSMT | YISRSSSTIYYADSVKG | SAFSPFDY |
| | | | SEQ ID NO:6206 | SEQ ID NO:14218 | SEQ ID NO:22230 |
| iPS:435413 | 21-225_150B11 | NA | AGCTATGGCATGCAC | ATTATATGGTATGATGG AAGTAATAAATACTATG CAGACTCCGTGAAGGGC | GATCGTTACGATTTTGGAG TGGTCACTTTGACTAC |
| | | | SEQ ID NO:6207 | SEQ ID NO:14219 | SEQ ID NO:22231 |
| | | AA | SYGMH | IIWYDGSNKYYADSVKG | DRYDFWSGHFDY |
| | | | SEQ ID NO:6208 | SEQ ID NO:14220 | SEQ ID NO:22232 |

FIGURE 49
(Continued)

| iPS:435415 | 21-225_150C11 | NA | AGCTATGGCATGAAC SEQ ID NO:6209 | GCTATTAGTAGTGGTAGTGGT GGTAACACATTCTACGC AGACTCCGTGAAGGGC SEQ ID NO:14221 | CGGGTGACGGACTACGGTGG TAACGACTGGTTCGACCCC SEQ ID NO:22233 |
| --- | --- | --- | --- | --- | --- |
|  |  | AA | SYAMN SEQ ID NO:6210 | AISGSGGNTFYADSVKG SEQ ID NO:14222 | RVTDYGGNDWFDP SEQ ID NO:22234 |
| iPS:435417 | 21-225_150D11 | NA | AGCTATGGCATGCAC SEQ ID NO:6211 | GTTATATTCTATGATGGA AGTAATAAACACTATGC AGACTCCGTGAAGGGC SEQ ID NO:14223 | AGGTTTAGCAGCAGCTGGTC GGGGGTATGGACGTC SEQ ID NO:22235 |
|  |  | AA | SYGMH SEQ ID NO:6212 | VIFYDGSNKHYADSVKG SEQ ID NO:14224 | RFSSSWSGGMDV SEQ ID NO:22236 |
| iPS:435419 | 21-225_150C12 | NA | AGCTATGGCATGAGC SEQ ID NO:6213 | GCTATTAGTGGTGTCGTGGT GGTAACACATTCTACGC AGACTCCGTGAAGGGC SEQ ID NO:14225 | CGGGTGACGGACTACGGTGG TAACGACTGGTTCGACCCC SEQ ID NO:22237 |
|  |  | AA | SYAMS SEQ ID NO:6214 | AISGRGGNTFYADSVKG SEQ ID NO:14226 | RVTDYGGNDWFDP SEQ ID NO:22238 |
| iPS:435421 | 21-225_151F1 | NA | AGCTTTAGCATGAAC SEQ ID NO:6215 | TCCATTAGTAGTAGTAGT TATTACATATACGCA GACTCAGTGAAGGGC SEQ ID NO:14227 | GATACACCACTGGTTTAC SEQ ID NO:22239 |
|  |  | AA | SFSMN SEQ ID NO:6216 | SISSSSYIYYADSVKG SEQ ID NO:14228 | DTPLVY SEQ ID NO:22240 |
| iPS:435423 | 21-225_151G5 | NA | AGCTATGGCATGCAC SEQ ID NO:6217 | ATTATATGGTATGATGG AAGTAATAAATACTATG CAGACTCCGTGAAGGGC SEQ ID NO:14229 | GATCGATACGATTTTGGAG TGGTCACTTTGACTAC SEQ ID NO:22241 |

FIGURE 49
(Continued)

| | | | | | |
|---|---|---|---|---|---|
| iPS:435425 | 21-225_151B12 | AA | SYGMH<br>SEQ ID NO:6218 | IIWYDGSNKYYADSVKG<br>SEQ ID NO:14230 | DRYDFWSGHFDY<br>SEQ ID NO:22242 |
| | | NA | AGCTATGCCATGAAC<br>SEQ ID NO:6219 | GCTATTAGTGGTAGTGGT<br>AAAAACACATTCTACGC<br>AGACTCCGTGAAGGGC<br>SEQ ID NO:14231 | CGGGTGACGGACTACGGTGG<br>TAACGACTGGTTCGACCCC<br>SEQ ID NO:22243 |
| iPS:435427 | 21-225_151C9 | AA | SYAMN<br>SEQ ID NO:6220 | AISGSGKNTFYADSVKG<br>SEQ ID NO:14232 | RVTDYGGNDWFDP<br>SEQ ID NO:22244 |
| | | NA | AGCTATGGCATGCAC<br>SEQ ID NO:6221 | GTTATATCATATGGATGGA<br>AGTAATAAATACTATGC<br>AGACTCCGTGAAGGGC<br>SEQ ID NO:14233 | GGGGTATTACTATGGTTCGG<br>GGAGCTAGAAGATGACTGGT<br>TCGACCCC<br>SEQ ID NO:22245 |
| iPS:435429 | 21-225_151A10 | AA | SYGMH<br>SEQ ID NO:6222 | VISYDGSNKYYADSVKG<br>SEQ ID NO:14234 | GVLLWFGELEDDWFDP<br>SEQ ID NO:22246 |
| | | NA | AACTATGGCATGCAC<br>SEQ ID NO:6223 | ATTATATATGGTATGATGG<br>AAGTAATAAATACTATG<br>CAGACTCCGTGAAGGGC<br>SEQ ID NO:14235 | GATCATTAGATTTTTGGAG<br>TGGTCACTTTGACTAC<br>SEQ ID NO:22247 |
| iPS:435431 | 21-225_152D2 | AA | NYGMH<br>SEQ ID NO:6224 | IIWYDGSNKYYADSVKG<br>SEQ ID NO:14236 | DHYDFWSGHFDY<br>SEQ ID NO:22248 |
| | | NA | AGCTATGCCATGAGC<br>SEQ ID NO:6225 | GCTATTAGTGGTCGTGGT<br>GGTAACACATTCTACGC<br>AGACTCCGTGAAGGGC<br>SEQ ID NO:14237 | CGGGTGACGGACTACGGTGG<br>TAACGACTGGTTCGACCCC<br>SEQ ID NO:22249 |
| | | AA | SYAMS<br>SEQ ID NO:6226 | AISGRGNTFYADSVKG<br>SEQ ID NO:14238 | RVTDYGGNDWFDP<br>SEQ ID NO:22250 |

FIGURE 49 (Continued)

| | | | | | |
|---|---|---|---|---|---|
| iPS:435433 | 21-225_152E3 | NA | AATTATGATATCAAC | TGGATGCACCCTAACAGTGGTAACACAGGCTATGCACAGAAGTTCCAGGGC | AGCAGTGGCTGGTACTTTTTTGACTAC |
| | | | SEQ ID NO:6227 | SEQ ID NO:14239 | SEQ ID NO:22251 |
| | | AA | NYDIN | WMHPNSGNTGYAQKFQG | SSGWYFFDY |
| | | | SEQ ID NO:6228 | SEQ ID NO:14240 | SEQ ID NO:22252 |
| iPS:435435 | 21-225_152H3 | NA | AATTATGATATCAAC | TGGATGCACCCTAACAGTGGTAACACAGGCTATGCACAGAAGTTCCAGGGC | AGCAGTGGCTGGTACTGGTTTGACTAC |
| | | | SEQ ID NO:6229 | SEQ ID NO:14241 | SEQ ID NO:22253 |
| | | AA | NYDIN | WMHPNSGNTGYAQKFQG | SSGWYWFDY |
| | | | SEQ ID NO:6230 | SEQ ID NO:14242 | SEQ ID NO:22254 |
| iPS:435437 | 21-225_152F4 | NA | AATTATGATATCAAC | TGGATGCACCCTAACAGTGGTAACACAGGCTATGCACAGAAGTTCCAGGGC | AGCAGTGGCTGGTACTGGTTCGACCCC |
| | | | SEQ ID NO:6231 | SEQ ID NO:14243 | SEQ ID NO:22255 |
| | | AA | NYDIN | WMHPNSGNTGYAQKFQG | SSGWYWFDP |
| | | | SEQ ID NO:6232 | SEQ ID NO:14244 | SEQ ID NO:22256 |
| iPS:435439 | 21-225_152G4 | NA | AGCTATGGCCATGAGC | GCTATTAGTGGTGGTGGTGGTAACACATTCTACGCAGACTCCGTGAAGGGC | CGGGTGACGGACTACGGTGGTAACGACTGGTTCGACCCC |
| | | | SEQ ID NO:6233 | SEQ ID NO:14245 | SEQ ID NO:22257 |
| | | AA | SYAMS | AISGRGGNTFYADSVKG | RVTDYGGNDWFDP |
| | | | SEQ ID NO:6234 | SEQ ID NO:14246 | SEQ ID NO:22258 |
| iPS:435441 | 21-225_152F6 | NA | AGCTATGGCATGCAC | ATTATATGGTATGATGGAAGTTATAAATACTATGCAGACTCCGTGAAGGGC | GAGGGGTACGATTTTGGAGTGGTTACCTTGGCTAC |

FIGURE 49
(Continued)

| | | | | | | |
|---|---|---|---|---|---|---|
| iPS:435443 | 21-225_152F6 | AA | SEQ ID NO:6235<br>SYGMH | SEQ ID NO:14247<br>IIWYDGSYKYYADSVKG | SEQ ID NO:22259<br>EGYDFWSGYLGY | |
| | | NA | SEQ ID NO:6236<br>AACAGTGGTTACTACTGGAG<br>C | SEQ ID NO:14248<br>TACAGTTATTACAGTGG<br>GAGCACCTACTACAACC<br>CGTCCCTCAAGAGT | SEQ ID NO:22260<br>GGGGGATATAACTGGAACCA<br>TGCTTTTGATATC | |
| iPS:435445 | 21-225_152E7 | AA | SEQ ID NO:6237<br>NSGYYWS | SEQ ID NO:14249<br>YSYYYSGSTYYNPSLKS | SEQ ID NO:22261<br>GGYNWNHAFDI | |
| | | NA | SEQ ID NO:6238<br>AGCTATATCATGCAC | SEQ ID NO:14250<br>GTTATATGGTATGATGG<br>AAGTAATAAATACTATG<br>CAGACTCCGTGAAGGGC | SEQ ID NO:22262<br>GAGGAGTATAGCAGCAGCTG<br>GTACGGGTACGGTATGGACG<br>TC | |
| iPS:435447 | 21-225_152F7 | AA | SEQ ID NO:6239<br>SYIMH | SEQ ID NO:14251<br>VIWYDGSNKYYADSVKG | SEQ ID NO:22263<br>EEYSSSWYGYGMDV | |
| | | NA | SEQ ID NO:6240<br>AGCTATGCCATGAAC | SEQ ID NO:14252<br>GCTATTAGTGGTAGTGGT<br>GGTAACACATTCTACGC<br>AGACTCCGTGAAGGGC | SEQ ID NO:22264<br>AAGGATAATGATTACGTTTG<br>GGGGAGTCCTTACTTTGACT<br>AC | |
| iPS:435447 | 21-225_152H7 | AA | SEQ ID NO:6241<br>SYAMN | SEQ ID NO:14253<br>AISGSGGNTFYADSVKG | SEQ ID NO:22265<br>KDNDYVWGSPYFDY | |
| | | NA | SEQ ID NO:6242 | SEQ ID NO:14254 | SEQ ID NO:22266 | |
| iPS:435449 | 21-225_152H9 | NA | SEQ ID NO:6243<br>AGAAGTAGTTACTACTGGGG<br>C | SEQ ID NO:14255<br>AGTATCTATTATAGTGGG<br>AGCGCCTCCTACAACCC<br>GTCCCTCAAGAGT | SEQ ID NO:22267<br>CTTGATCTCCAGTGGAGTTTT<br>GACTTC | |
| | | AA | SEQ ID NO:6244<br>RSSYYWG | SEQ ID NO:14256<br>SIYYSGSASYNPSLKS | SEQ ID NO:22268<br>LDLQWSFDF | |

FIGURE 49
(Continued)

| | | | | |
|---|---|---|---|---|
| iPS:435451 | 21-225_152D10 | NA | AATTACTACTGGAGC SEQ ID NO:6245 | CGTATCGATACCAGTGG GATCACCAACTACAAC CCTCCCTCAAGAGT SEQ ID NO:14257 | GAGGGGGGGATTGGGAGCTAC CTTCTTTGACTAC SEQ ID NO:22269 |
| | | AA | NYYWS SEQ ID NO:6246 | RIDTSGITNYNPSLKS SEQ ID NO:14258 | EGGLGATFFDY SEQ ID NO:22270 |
| iPS:435453 | 21-225_152D10 | NA | AGCTATGCCATGAGC SEQ ID NO:6247 | GCTATTAGTGGTCGTGGT GGTAACACATTCTACGC AGACTCCGTGAAGGGC SEQ ID NO:14259 | AAGGATTATGATTACGTTTG GGGGAGTCCTTACTTTGACT AC SEQ ID NO:22271 |
| | | AA | SYAMS SEQ ID NO:6248 | AISGRGGNTFYADSVKG SEQ ID NO:14260 | KDYDYVWGSPYFDY SEQ ID NO:22272 |
| iPS:435455 | 21-225_152G10 | NA | AGCTATGCCATGAAC SEQ ID NO:6249 | GCTATTAGTGGTCGTGGT GGTAACACATTCTACGC AGACTCCGTGAAGGGC SEQ ID NO:14261 | CGGGTGACGGACTACGGTGG TAACGACTGGTTCGACCCC SEQ ID NO:22273 |
| | | AA | SYAMN SEQ ID NO:6250 | AISGRGGNTFYADSVKG SEQ ID NO:14262 | RVTDYGGNDWFDP SEQ ID NO:22274 |
| iPS:435457 | 21-225_152C11 | NA | AACTATGGCATGCAC SEQ ID NO:6251 | ATTATATGGTATGATGG AAGTAATAAATACTATG CAGACTCCGTGAAGGGC SEQ ID NO:14263 | GAGGCTTACGATTTTTGGAG TGGTTATTTTGACTAC SEQ ID NO:22275 |
| | | AA | NYGMH SEQ ID NO:6252 | IIWYDGSNKYYADSVKG SEQ ID NO:14264 | EAYDFWSGYFDY SEQ ID NO:22276 |
| iPS:435459 | 21-225_152E12 | NA | AATTATGATATCAAC SEQ ID NO:6253 | TGGATGAACCCTAACAG TGGTAACACAGGCTATG CACAGAAGTTCCAGGGC SEQ ID NO:14265 | AGCAGTGGCTGTACTACTT TGACTAC SEQ ID NO:22277 |

FIGURE 49
(Continued)

| | | | | | | |
|---|---|---|---|---|---|---|
| iPS:435461 | 21-225_153A1 | AA | NYDIN | | WMNPNSGNTGYAQKFQG | SSGWYYFDY |
| | | | SEQ ID NO:6254 | | SEQ ID NO:14266 | SEQ ID NO:22278 |
| | | NA | AGCTATGTCATGAGT | | GCTATTAGTGGAAGTGG TGATAGAACATACTACG CAGACTCCGTGAAGGGC | ACGGCGACTAAGGACTAC |
| | | | SEQ ID NO:6255 | | SEQ ID NO:14267 | SEQ ID NO:22279 |
| | | AA | SYVMS | | AISGSGDRTYYADSVKG | TATKDY |
| | | | SEQ ID NO:6256 | | SEQ ID NO:14268 | SEQ ID NO:22280 |
| iPS:435463 | 21-225_153D2 | NA | AGCTATGGCATGCAC | | ATTATATGGTATGATGG AAGTTATAAATACTATG CAGACTCCGTGAAGGGC | GAGGGGTACGATTTTTGGAG TGGTTACCTTGGCTAC |
| | | | SEQ ID NO:6257 | | SEQ ID NO:14269 | SEQ ID NO:22281 |
| | | AA | SYGMH | | IIWYDGSYKYYADSVKG | EGYDFWSGYLGY |
| | | | SEQ ID NO:6258 | | SEQ ID NO:14270 | SEQ ID NO:22282 |
| iPS:435465 | 21-225_153A6 | NA | AACAGTGGTTACTACTGGAGC | | TACAGCTATTACAGTGG GAGCACCTACTACAACC CGTCCCTCAAGAGT | GGGGGATATAACTGGAACCA TGCTTTTGATATC |
| | | | SEQ ID NO:6259 | | SEQ ID NO:14271 | SEQ ID NO:22283 |
| | | AA | NSGYYWS | | YSYYSGSTYYNPSLKS | GGYNWNHAFDI |
| | | | SEQ ID NO:6260 | | SEQ ID NO:14272 | SEQ ID NO:22284 |
| iPS:435467 | 21-225_153B9 | NA | AGTTACTACTGGAGC | | CGTATCGATACCAGTGG GATCACCAACTACAACC CCTCCCTCAAGAGT | GAGGGGGGAGTGGGAGCTA CGTACTTTGACTAC |
| | | | SEQ ID NO:6261 | | SEQ ID NO:14273 | SEQ ID NO:22285 |
| | | AA | SYYWS | | RIDTSGITNYNPSLKS | EGGVGATYFDY |
| | | | SEQ ID NO:6262 | | SEQ ID NO:14274 | SEQ ID NO:22286 |

FIGURE 49
(Continued)

| | | NA | AGCTATGGCATGCAC | CTTATATTCTATGATGGA AGTAATAAATACTATGC AGACTCCGTGAAGGGC | CGCTATAGCCGCAGCTGGGC CGGGGGTATGGACGTC |
|---|---|---|---|---|---|
| iPS:435469 | 21-225_153G9 | | SEQ ID NO:6263 | SEQ ID NO:14275 | SEQ ID NO:22287 |
| | | AA | SYGMH | LIFYDGSNKYYADSVKG | RYSRSWAGGMDV |
| | | NA | SEQ ID NO:6264 | SEQ ID NO:14276 | SEQ ID NO:22288 |
| | | NA | AATTATGATATCAAC | TGGATGCACCCTAACAG TGGTAACACAGGCTATG CACAGAAGTTCCAGGGC | AGCAGTGGCTGGTACTTCTT TGACAAC |
| iPS:435471 | 21-225_153F11 | | SEQ ID NO:6265 | SEQ ID NO:14277 | SEQ ID NO:22289 |
| | | AA | NYDIN | WMHPNSGNTGYAQKFQG | SSGWYFFDN |
| | | NA | SEQ ID NO:6266 | SEQ ID NO:14278 | SEQ ID NO:22290 |
| | | NA | AATTATGATATCAAC | TGGATGAACCCTAACAG TGGTAACACAGGCTATG CACAGAAGTTCCAGGGC | AGCAGTGGCTGGTACACATCTT TGACTAC |
| iPS:435475 | 21-225_154H6 | | SEQ ID NO:6267 | SEQ ID NO:14279 | SEQ ID NO:22291 |
| | | AA | NYDIN | WMNPNSGNTGYAQKFQG | SSGWYIFDY |
| | | NA | SEQ ID NO:6268 | SEQ ID NO:14280 | SEQ ID NO:22292 |
| | | NA | AGCTATGCCATGAGC | GCTATTAGTGGTCGTGGT GGTAACACATTCTACGC AGACTCCGTGAAGGGC | AGGGGATTTCGATTTTTGGA GTGGTTGGGGGGCTTTGACT AC |
| iPS:435479 | 21-225_154E9 | | SEQ ID NO:6269 | SEQ ID NO:14281 | SEQ ID NO:22293 |
| | | AA | SYAMS | AISGRGGNTFYADSVKG | RGFRFLEWLGGFDY |
| | | NA | SEQ ID NO:6270 | SEQ ID NO:14282 | SEQ ID NO:22294 |
| iPS:435481 | | NA | AATTATGATATCAAC | TGGATGAACCCTAACAG TGGTAACACAGGCTATG CACAGAAGTTCCAGGGC | AGCAGTGGCTGGTACTACTT CGACTAC |

FIGURE 49
(Continued)

| | | | | | | |
|---|---|---|---|---|---|---|
| iPS:435483 | 21-225_154A11 | AA | SEQ ID NO:6271<br>NYDIN | SEQ ID NO:14283<br>WMNPNSGNTGYAQKFQG | SEQ ID NO:22295<br>SSGWYFDY |
| | | NA | SEQ ID NO:6272<br>AGCTATGCCATGAGC | SEQ ID NO:14284<br>GCTATTAGTGGTAGTGGT<br>GGTAACACATTCTACGC<br>AGACTCCGTGAAGGGC | SEQ ID NO:22296<br>AAGGATTATGATTACGTTTG<br>GGGGAGTCCTTACTTTGACT<br>AC |
| iPS:435485 | 21-225_155A4 | AA | SEQ ID NO:6273<br>SYAMS | SEQ ID NO:14285<br>AISGSGGNTFYADSVKG | SEQ ID NO:22297<br>KDYDYVWGSPYFDY |
| | | NA | SEQ ID NO:6274<br>AGCTATGCCATGAGC | SEQ ID NO:14286<br>GCTATTAGTGGTAGTGGT<br>GGTAACACATTCTACGC<br>AGACTCCGTGAAGGGC | SEQ ID NO:22298<br>AAGGATTATGATTACGTTTG<br>GGGGAGTCCTTACTTTGACT<br>AC |
| iPS:435487 | 21-225_155B4 | AA | SEQ ID NO:6275<br>SYAMS | SEQ ID NO:14287<br>AISGSGGNTFYADSVKG | SEQ ID NO:22299<br>KDYDYVWGSPYFDY |
| | | NA | SEQ ID NO:6276<br>AGCTATGCCATGAGC | SEQ ID NO:14288<br>GCTATTAGTGGTGGTCGTGGT<br>GGTAACACATTCTACGC<br>AGACTCCGTGAAGGGC | SEQ ID NO:22300<br>CGGGTGACGGACTACGGTGG<br>TAACGACTGGTTCGACCCC |
| iPS:435489 | 21-225_155C4 | AA | SEQ ID NO:6277<br>SYAMS | SEQ ID NO:14289<br>AISGRGGNTFYADSVKG | SEQ ID NO:22301<br>RVTDYGGNDWFDP |
| | | NA | SEQ ID NO:6278<br>AGCTATGCCATGCAC | SEQ ID NO:14290<br>ATTATATGGTATGATGG<br>AAGTAGTAAATACTATG<br>CAGACTCCGTGAAGGGC | SEQ ID NO:22302<br>GATCGATACGATTTTGGAG<br>TGGTCACTTTGACTAC |
| | 21-225_155A5 | AA | SEQ ID NO:6279<br>SYGMH | SEQ ID NO:14291<br>HWYDGSSKYYADSVKG | SEQ ID NO:22303<br>DRYDFWSGHFDY |
| | | | SEQ ID NO:6280 | SEQ ID NO:14292 | SEQ ID NO:22304 |

FIGURE 49
(Continued)

| | | | | |
|---|---|---|---|---|
| iPS:435491 | 21-225_155E5 | NA | AATTATGATATCAAC SEQ ID NO:6281 | TGGATGCACCCTAACAG TGGTAGTACAGGCTATG CACAGAGGTTCCAGGGC SEQ ID NO:14293 | AGCAGTGGCTGGTACTATTT TGACTAC SEQ ID NO:22305 |
| | | AA | NYDIN SEQ ID NO:6282 | WMHPNSGSTGYAQRFQG SEQ ID NO:14294 | SSGWYYFDY SEQ ID NO:22306 |
| iPS:435495 | 21-225_155B6 | NA | AATTATGATATCAAC SEQ ID NO:6283 | TGGATGAACCCTAACAG TGGTAACACAGGCTATG CACAGAAGTTCCAGGGC SEQ ID NO:14295 | AGCAGTGGCTGGTACTACTT TGACTAC SEQ ID NO:22307 |
| | | AA | NYDIN SEQ ID NO:6284 | WMNPNSGNTGYAQKFQG SEQ ID NO:14296 | SSGWYYFDY SEQ ID NO:22308 |
| iPS:435497 | 21-225_155H9 | NA | AGCTATGCCATGAAC SEQ ID NO:6285 | ACTATTAGTGGTAGAGG TCTTGGCACATACTACG AGACTCCGTGAAGGGC SEQ ID NO:14297 | GACCATGACTACGGTGACTA CAATATCTACTTTGACTAC SEQ ID NO:22309 |
| | | AA | SYAMN SEQ ID NO:6286 | TISGRGLGTYYADSVKG SEQ ID NO:14298 | DHDYGDYNYFDY SEQ ID NO:22310 |
| iPS:435499 | 21-225_156G1 | NA | AGAAGTAGTTACTACTGGGG C SEQ ID NO:6287 | AGTATCTATTATAGTGGG AGCGCCTCCTACAACCC GTCCCTCAAGAGT SEQ ID NO:14299 | CTTGATCTCCAGTGGAGTTTT GACTTC SEQ ID NO:22311 |
| | | AA | RSSYYWG SEQ ID NO:6288 | SIYYSGSASYNPSLKS SEQ ID NO:14300 | LDLQWSFDF SEQ ID NO:22312 |
| iPS:435501 | 21-225_156H1 | NA | AATTATGATATCAAC SEQ ID NO:6289 | TGGGTGCACCCTAACAG TGGTAACACAGGCTATG CACAGAAGTTCCAGGGC SEQ ID NO:14301 | AGCAGTGGCTGGTACTACTT TGACTAC SEQ ID NO:22313 |

FIGURE 49
(Continued)

| | | | | | |
|---|---|---|---|---|---|
| iPS:435503 | 21-225_156F4 | AA | NYDIN | WVHPNSGNTGYAQKFQG | SSGWYYFDY |
| | | | SEQ ID NO:6290 | SEQ ID NO:14302 | SEQ ID NO:22314 |
| | | NA | AGCTATGCCATGAGC | GCTATTAGTGGTCGTGGT GGTAACACATTCTACGC AGACTCCGTGAAGGGC | CGGGTGACGGACTACGGTGG TAACGACTGGTTCGACCCC |
| | | | SEQ ID NO:6291 | SEQ ID NO:14303 | SEQ ID NO:22315 |
| iPS:435505 | 21-225_157C1 | AA | SYAMS | AISGRGGNTFYADSVKG | RVTDYGGNDWFDP |
| | | | SEQ ID NO:6292 | SEQ ID NO:14304 | SEQ ID NO:22316 |
| | | NA | AGCTATAGAATGAAC | TCCATGAGTAATAGTAG TAGTTCCATATACTACGC AGACTCAGTGAAGGGC | CAGGCAGCCCAGGACTAC |
| | | | SEQ ID NO:6293 | SEQ ID NO:14305 | SEQ ID NO:22317 |
| iPS:435509 | 21-225_157H1 | AA | SYRMN | SMSNSSSSIYYADSVKG | QAAQDY |
| | | | SEQ ID NO:6294 | SEQ ID NO:14306 | SEQ ID NO:22318 |
| | | NA | AGTTATAGGATGAAC | GATATTAGTGGTAGTGG TGGTACCACATACTACG CAGACTCCGTGAAGGGC | ACCTACCTC |
| | | | SEQ ID NO:6295 | SEQ ID NO:14307 | SEQ ID NO:22319 |
| iPS:435511 | 21-225_157C3 | AA | SYAMR | DISGSGGTTYYADSVKG | TYL |
| | | | SEQ ID NO:6296 | SEQ ID NO:14308 | SEQ ID NO:22320 |
| | | NA | ACCTATGGCATGCAC | GTTATATGGTATGATGTA AATAATAAATACTATGC AGACTCCGTGAAGGGC | GAGCTGGGGGTTCCTCTCTGA CTAT |
| | | | SEQ ID NO:6297 | SEQ ID NO:14309 | SEQ ID NO:22321 |
| | | AA | TYGMH | VIWYDVNNKYYADSVKG | ELGFLSDY |
| | | | SEQ ID NO:6298 | SEQ ID NO:14310 | SEQ ID NO:22322 |

FIGURE 49
(Continued)

| | | | | | |
|---|---|---|---|---|---|
| iPS:435513 | 21-225_157F3 | NA | ACCTATGCCATGAGC | GTTATTAGTGGTAGTGGT GGTAGCACATACTACGC AGACTCCGTGAAGGGC | AGGAGCAGTGGCTGGTACGA GGATGCTCTTGATATC |
| | | | SEQ ID NO:6299 | SEQ ID NO:14311 | SEQ ID NO:22323 |
| | | AA | TYAMS | VISGSGGSTYYADSVKG | RSSGWYEDALDI |
| | | | SEQ ID NO:6300 | SEQ ID NO:14312 | SEQ ID NO:22324 |
| iPS:435515 | 21-225_157E4 | NA | AGCTATACCATGAAC | TCCATTAGTGGTAGTAGT AGTTACATATACTACGC AGACTCAGTGAAGGGC | GTAGCTACCTTTGACTAC |
| | | | SEQ ID NO:6301 | SEQ ID NO:14313 | SEQ ID NO:22325 |
| | | AA | SYTMN | SISGSSSYIYYADSVKG | VATFDY |
| | | | SEQ ID NO:6302 | SEQ ID NO:14314 | SEQ ID NO:22326 |
| iPS:435521 | 21-225_157H4 | NA | AGTTATAGCATGAAC | TCCATTAGTAGTAGTAGT ACTACATATACTACGCA GACTCAGTGAAGGGC | GATAGAGGGTCCATC |
| | | | SEQ ID NO:6303 | SEQ ID NO:14315 | SEQ ID NO:22327 |
| | | AA | SYSMN | SISSSSTYIYYADSVKG | DRGSI |
| | | | SEQ ID NO:6304 | SEQ ID NO:14316 | SEQ ID NO:22328 |
| iPS:435523 | 21-225_157G5 | NA | AGCTATGTCATGAGC | GCTATGAGTGGTAGTGG TGGTAGAACATACTACG CAGACTCCGTGAAGGGC | TATACCTGGAACGGCTAC |
| | | | SEQ ID NO:6305 | SEQ ID NO:14317 | SEQ ID NO:22329 |
| | | AA | SYVMS | AMSGSGGRTYYADSVKG | YTWNGY |
| | | | SEQ ID NO:6306 | SEQ ID NO:14318 | SEQ ID NO:22330 |
| iPS:435525 | 21-225_157E7 | NA | AGTGGTAGTTACTACTGGGG C | AGTATCTACTATAGTGG GAGCACTACTACAATC CGTCCCTCAAGAGT | CATAAAGTGGCTGGTCCCTT TGACTAC |
| | | | SEQ ID NO:6307 | SEQ ID NO:14319 | SEQ ID NO:22331 |
| | | AA | SGSYYWG | SIYYSGSTYNPSLKS | HKVAGPFDY |
| | | | SEQ ID NO:6308 | SEQ ID NO:14320 | SEQ ID NO:22332 |

FIGURE 49
(Continued)

| iPS:435527 | 21-225_157G7 | NA | AGTTATAGCATGAAC | TCCATTAGTAGTGGTAGTAGT ACGTACATATACTGC AGACTCAGTGAAGGGC | GATCGGGGCAGCAGC |
|---|---|---|---|---|---|
| | | | SEQ ID NO:6309 | SEQ ID NO:14321 | SEQ ID NO:22333 |
| | | AA | SYSMN | SISGSSTYIYYADSVKG | DRGSS |
| | | | SEQ ID NO:6310 | SEQ ID NO:14322 | SEQ ID NO:22334 |
| iPS:435529 | 21-225_157H7 | NA | AGCTATAGCATGAAC | TGCATTAGTGGTAGTAGT AGTTACATATATTATGCA GACTCAGTGAAGGGC | GATCGAGGGGGCTAT |
| | | | SEQ ID NO:6311 | SEQ ID NO:14323 | SEQ ID NO:22335 |
| | | AA | SYSMN | CISGSSSYIYYADSVKG | DRGGY |
| | | | SEQ ID NO:6312 | SEQ ID NO:14324 | SEQ ID NO:22336 |
| iPS:435531 | 21-225_157G8 | NA | AATTATGGCATGCAC | ATTATATGGTATGATGG AAGTTATAAATACTATG CAGACTCCGTGAAGGGC | GAGGGATACGATTTTTGGAG TGGTTCTTTGACTCC |
| | | | SEQ ID NO:6313 | SEQ ID NO:14325 | SEQ ID NO:22337 |
| | | AA | NYGMH | IIWYDGSYKYYADSVKG | EGYDFWSGFFDS |
| | | | SEQ ID NO:6314 | SEQ ID NO:14326 | SEQ ID NO:22338 |
| iPS:435533 | 21-225_157H8 | NA | AGCTATGGCATGCAC | GTTATATGGTATGATGTA AATAATAAATACTATGC AGACTCCGTGAAGGGC | GAGCTGGGGTTCCTCTCTGA CTAC |
| | | | SEQ ID NO:6315 | SEQ ID NO:14327 | SEQ ID NO:22339 |
| | | AA | SYGMH | VIWYDVNNKYYADSVKG | ELGFLSDY |
| | | | SEQ ID NO:6316 | SEQ ID NO:14328 | SEQ ID NO:22340 |
| iPS:435535 | 21-225_157H10 | NA | AGCTATACCATGAAC | TCCATTAGTGGTAGCAGT AGTTACATAAACTACGC AGACTCAGTGAAGGGC | GTGGCTCACTTTGACTAC |
| | | | SEQ ID NO:6317 | SEQ ID NO:14329 | SEQ ID NO:22341 |

FIGURE 49
(Continued)

| | | | | | | |
|---|---|---|---|---|---|---|
| iPS:435537 | 21-225_157H12 | AA | SYTMN<br>SEQ ID NO:6318 | SISGSSYINYADSVKG<br>SEQ ID NO:14330 | VAHFDY<br>SEQ ID NO:22342 | |
| | | NA | AGTTATAGCATGAAC<br>SEQ ID NO:6319 | TCCATTAGTGGTAGTGGT<br>AGTTACATAAACTACGC<br>AGACTCAGTGAAGGGC<br>SEQ ID NO:14331 | TCCAAGTTTGACTCC<br>SEQ ID NO:22343 | |
| iPS:435539 | 21-225_158G1 | AA | SYSMN<br>SEQ ID NO:6320 | SISGSGSYINYADSVKG<br>SEQ ID NO:14332 | SKFDS<br>SEQ ID NO:22344 | |
| | | NA | AGTTATGGCATGAAC<br>SEQ ID NO:6321 | TCCATTAGTGGTAGTGGT<br>AGTTACATATACTACGC<br>AGACTCAGTGAAGGGC<br>SEQ ID NO:14333 | AGCAGTGGCTGGTCT<br>SEQ ID NO:22345 | |
| iPS:435543 | 21-225_158D4 | AA | SYGMN<br>SEQ ID NO:6322 | SISGSGSYIYYADSVKG<br>SEQ ID NO:14334 | SSGWS<br>SEQ ID NO:22346 | |
| | | NA | GACTATGTCATGCAC<br>SEQ ID NO:6323 | GTTATATGGTATGATGG<br>AAGTAATAAATACTATG<br>CAGACTCCGTGAAGGGC<br>SEQ ID NO:14335 | GAACCGTATACTAGTGGCTG<br>GTACGACTACGGTATGGACG<br>TC<br>SEQ ID NO:22347 | |
| | | AA | DYVMH<br>SEQ ID NO:6324 | VIWYDGSNKYYADSVKG<br>SEQ ID NO:14336 | EPYTSGWYDYGMDV<br>SEQ ID NO:22348 | |
| iPS:435545 | 21-225_158F4 | NA | AGTCACTTCTGGAGC<br>SEQ ID NO:6325 | CGTATCTATACCAGTGG<br>GACCACCAACTACACCC<br>CCTCCCTCAAGAGT<br>SEQ ID NO:14337 | TTGAGCAGTGGCTGGTTTGA<br>CTAC<br>SEQ ID NO:22349 | |
| | | AA | SHFWS<br>SEQ ID NO:6326 | RIYTSGTTNYTPSLKS<br>SEQ ID NO:14338 | LSSGWFDY<br>SEQ ID NO:22350 | |

FIGURE 49
(Continued)

| | | | | | | |
|---|---|---|---|---|---|---|
| iPS:435547 | 21-225_158F5 | NA | AGTTATAGCATGAAC | | TCCATTAGTAGTGGTAGTAGT ACGTACATATACTGC AGACTCAGTGAAGGGC | GATCGGGGCAGCAGC |
| | | | SEQ ID NO:6327 | | SEQ ID NO:14339 | SEQ ID NO:22351 |
| | | AA | SYSMN | | SISGSSTYIYYADSVKG | DRGSS |
| | | | SEQ ID NO:6328 | | SEQ ID NO:14340 | SEQ ID NO:22352 |
| iPS:435549 | 21-225_158H5 | NA | AGCTATAGCATGAAC | | TCCATCAGTGGTAGTAGT ACTTACATATACTACGCA GACTCAGTGAAGGGC | GATCGGGGCAGCAGC |
| | | | SEQ ID NO:6329 | | SEQ ID NO:14341 | SEQ ID NO:22353 |
| | | AA | SYSMN | | SISGSSTYIYYADSVKG | DRGSS |
| | | | SEQ ID NO:6330 | | SEQ ID NO:14342 | SEQ ID NO:22354 |
| iPS:435551 | 21-225_158H6 | NA | AGCTATGGCATGCAC | | GTTATATGGTATGATGTA ACTAATAAATACTATGC AGACTCCGTGAAGGGC | GAACTGGGATGGGCGGAGG ACTAC |
| | | | SEQ ID NO:6331 | | SEQ ID NO:14343 | SEQ ID NO:22355 |
| | | AA | SYGMH | | VIWYDVTNKYYADSVKG | ELGWAEDY |
| | | | SEQ ID NO:6332 | | SEQ ID NO:14344 | SEQ ID NO:22356 |
| iPS:435553 | 21-225_158G8 | NA | AGCTATACCATGAAC | | TTGATTAGTGGCAGTAGT AGTTACATATACTACGC AGACTCAGTGAAGGGC | GATCGAGGCAGCCTC |
| | | | SEQ ID NO:6333 | | SEQ ID NO:14345 | SEQ ID NO:22357 |
| | | AA | SYTMN | | LISGSSYIYYADSVKG | DRGSL |
| | | | SEQ ID NO:6334 | | SEQ ID NO:14346 | SEQ ID NO:22358 |
| iPS:435557 | 21-225_158B12 | NA | AATTATGATATCAAC | | TGGATGCACCCTAACAG TGGTAACACAGGCTATG CACAGAAGTTCCAGGGC | AGCAGTGGCTGGTACCGCTT TGACTAC |
| | | | SEQ ID NO:6335 | | SEQ ID NO:14347 | SEQ ID NO:22359 |

FIGURE 49
(Continued)

| | | | | WMHPNSGNTGYAQKFQG | SSGWYRFDY |
|---|---|---|---|---|---|
| | | AA | NYDIN | SEQ ID NO:14348 | SEQ ID NO:22360 |
| iPS:435559 | 21-225_158H12 | NA | AGCTATGTCATGAGC | GCTATTAGTGGTAGTGGT GGTAGGACAGACTACGC AGACTCCGTAAAGGGC | GGGGGCTGGAACCACGAC |
| | | | | SEQ ID NO:14349 | SEQ ID NO:22361 |
| | | AA | SYVMS | AISGSGGRTDYADSVKG | GGWNHD |
| | | | SEQ ID NO:6338 | SEQ ID NO:14350 | SEQ ID NO:22362 |
| iPS:435561 | 21-225_159F1 | NA | AGCTATAGAATGAAC | TCCATAAGTGGTAGTGG TAATTACATAGACTACG CAGACTCAGTGAAGGGC | GGTTGGGACGTC |
| | | | SEQ ID NO:6339 | SEQ ID NO:14351 | SEQ ID NO:22363 |
| | | AA | SYRMN | SISGSGNYIDYADSVKG | GWDV |
| | | | SEQ ID NO:6340 | SEQ ID NO:14352 | SEQ ID NO:22364 |
| iPS:435563 | 21-225_159H2 | NA | AGTTATGATATCAAC | TGGATGAACCCTAACAG TGGTAACACAGGCTATG TACAGAAGTTCCAGGGC | AAGAAAACTGGGACTAC |
| | | | SEQ ID NO:6341 | SEQ ID NO:14353 | SEQ ID NO:22365 |
| | | AA | SYDIN | WMNPNSGNTGYVQKFQG | KKTGDY |
| | | | SEQ ID NO:6342 | SEQ ID NO:14354 | SEQ ID NO:22366 |
| iPS:435565 | 21-225_159C4 | NA | AACTATGGCATGCAC | GTTATATCATATTCTGGA AACAATAAATACTATGC AGACTCCGTGAAGGGC | CGGAGCAGCTCGTGGGGGGG CTACGGTATGGACGTC |
| | | | SEQ ID NO:6343 | SEQ ID NO:14355 | SEQ ID NO:22367 |
| | | AA | NYGMH | VISYSGNNKYYADSVKG | RSSSWGGYGMDV |
| | | | SEQ ID NO:6344 | SEQ ID NO:14356 | SEQ ID NO:22368 |

FIGURE 49
(Continued)

| | | | | | | |
|---|---|---|---|---|---|---|
| iPS:435569 | 21-225_159C5 | NA | AGCTATGGCATACAC | GTTGTATGGTATGATGTA AATAATAAATACTATGC AGACTCCGTGAAGGGC | GAGCTGGGGTTCCTCTCTGA CTAC | |
| | | | SEQ ID NO:6345 | SEQ ID NO:14357 | SEQ ID NO:22369 | |
| | | AA | SYGIH | VVWYDVNNKYYADSVK G | ELGFLSDY | |
| | | | SEQ ID NO:6346 | SEQ ID NO:14358 | SEQ ID NO:22370 | |
| iPS:435571 | 21-225_159C8 | NA | GACTATGTCATGCAG | GTTATATGGTATGATGG AAGTAATAAATACTATG CAGACTCCGTGAAGGGC | GAACCGTATAATAGTGGCTG GTACGACTACGGTATGGACG TC | |
| | | | SEQ ID NO:6347 | SEQ ID NO:14359 | SEQ ID NO:22371 | |
| | | AA | DYVMQ | VIWYDGSNKYYADSVKG | EPYNSGWYDYGMDV | |
| | | | SEQ ID NO:6348 | SEQ ID NO:14360 | SEQ ID NO:22372 | |
| iPS:435573 | 21-225_159D8 | NA | AACTATGTCATGCAC | GTTATATGGTATGATGG AAGTAATAAATACTATG CAGACTCCGTGAAGGGC | GAACCGTATAGTAGTGGCTG GTACGACTACGGTATGGACG TC | |
| | | | SEQ ID NO:6349 | SEQ ID NO:14361 | SEQ ID NO:22373 | |
| | | AA | NYVMH | VIWYDGSNKYYADSVKG | EPYSSGWYDYGMDV | |
| | | | SEQ ID NO:6350 | SEQ ID NO:14362 | SEQ ID NO:22374 | |
| iPS:435575 | 21-225_159H11 | NA | AGCTATACCATGAAC | TCCATTAGTAGTAGTAGT AGTTACATATACTACGC AGACTCAGTGAAGGGC | GTGAGCTGGGGCTGACTGC | |
| | | | SEQ ID NO:6351 | SEQ ID NO:14363 | SEQ ID NO:22375 | |
| | | AA | SYTMN | SISGSSSYIYYADSVKG | VSWADC | |
| | | | SEQ ID NO:6352 | SEQ ID NO:14364 | SEQ ID NO:22376 | |

FIGURE 49
(Continued)

| | | | | | |
|---|---|---|---|---|---|
| iPS:435577 | 21-225_160B1 | NA | AGCTATGGCATGCAC SEQ ID NO:6353 | GTTATATGGTATGATGG AAGTTATAAATACTATG CAGACTCCGTGAAGGGC SEQ ID NO:14365 | GAGGCCTACGATTTTTGGAG TGGTTATTATGACTAC SEQ ID NO:22377 |
| | | AA | SYGMH SEQ ID NO:6354 | VIWYDGSYKYYADSVKG SEQ ID NO:14366 | EAYDFWSGYYDY SEQ ID NO:22378 |
| iPS:435579 | 21-225_160G1 | NA | AGCTATGTCATGAGC SEQ ID NO:6355 | GCTATGAGTGGTAGTGG TGGTCACATACTACG CAGACTCCGTGAAGGGC SEQ ID NO:14367 | CATGGATACAGC SEQ ID NO:22379 |
| | | AA | SYVMS SEQ ID NO:6356 | AMSGSGGHTYY ADSVKG SEQ ID NO:14368 | HGYS SEQ ID NO:22380 |
| iPS:435581 | 21-225_160H1 | NA | AGCTATCGCATGAAC SEQ ID NO:6357 | TCCATTAGTAGTAGTACT GGTTACATGTACTACG AGACTCAGTGAAGGGC SEQ ID NO:14369 | GATAAAGATTAC SEQ ID NO:22381 |
| | | AA | SYRMN SEQ ID NO:6358 | SISSSTGYMYYADSVKG SEQ ID NO:14370 | DKDY SEQ ID NO:22382 |
| iPS:435583 | 21-225_160F2 | NA | AGTTATGGCATGAAC SEQ ID NO:6359 | TCCATTAGTGGTAGTGGT AGTTACATATACTACG AGACTCCGTGAAGGGC SEQ ID NO:14371 | AGCAGTGGCTGGTCT SEQ ID NO:22383 |
| | | AA | SYGMN SEQ ID NO:6360 | SISGSGSYIYYADSVKG SEQ ID NO:14372 | SSGWS SEQ ID NO:22384 |
| iPS:435585 | 21-225_160G3 | NA | AGCTATGTCATGAGC SEQ ID NO:6361 | GCTATGAGTGGTAGTGG TGGTCACATACCGTACG CAGACTCCGTGAAGGGC SEQ ID NO:14373 | CATGGATACAGC SEQ ID NO:22385 |

FIGURE 49
(Continued)

| | | | | | | | |
|---|---|---|---|---|---|---|---|
| iPS:435587 | 21-225_160H3 | AA | SYVMS | SEQ ID NO:6362 | AMSGSGGHTYYADSVKG | SEQ ID NO:14374 | HGYS | SEQ ID NO:22386 |
| | | NA | AGAAGTAGTTACTACTGGGGC | SEQ ID NO:6363 | AGTATCTATTATAGTGGGAGTACCTCCTACAACCCGTCTCTCGAGAGT | SEQ ID NO:14375 | CTCTCTCAACGGTGGGACTTTGACTAC | SEQ ID NO:22387 |
| | | AA | RSSYYWG | SEQ ID NO:6364 | SIYYSGSTSYNPSLES | SEQ ID NO:14376 | LSQRWDFDY | SEQ ID NO:22388 |
| iPS:435589 | 21-225_160A4 | NA | AATTATGATATCAAC | SEQ ID NO:6365 | TGGATGCACCTAACAGTGGTAACACAGGCTATCCACAGAAGTTCCAGGGC | SEQ ID NO:14377 | AGCAGCGGCTGGTACATTTTGACTAC | SEQ ID NO:22389 |
| | | AA | NYDIN | SEQ ID NO:6366 | WMHPNSGNTGYPQKFQG | SEQ ID NO:14378 | SSGWYIFDY | SEQ ID NO:22390 |
| iPS:435591 | 21-225_160C4 | NA | GACTATGTCATGCAG | SEQ ID NO:6367 | GTTATATGGTAGTGATGGAAGTAATAAATACTATGCAGACTCCGTGAAGGGC | SEQ ID NO:14379 | GAACCGTATAATAGTGGCTGGTACGACTACGGTATGGACGTC | SEQ ID NO:22391 |
| | | AA | DYVMQ | SEQ ID NO:6368 | VIWYDGSNKYYADSVKG | SEQ ID NO:14380 | EPYNSGWYDYGMDV | SEQ ID NO:22392 |
| iPS:435593 | 21-225_160F4 | NA | AGTTATATAGCATGAAC | SEQ ID NO:6369 | TCCATTAGTAGTGGTAGTAGTACATATACGCAGACTCAGTGAAGGGC | SEQ ID NO:14381 | GATCGGGGCAGCAGC | SEQ ID NO:22393 |
| | | AA | SYSMN | SEQ ID NO:6370 | SISGSSTYIYYADSVKG | SEQ ID NO:14382 | DRGSS | SEQ ID NO:22394 |

FIGURE 49
(Continued)

| | | | | | |
|---|---|---|---|---|---|
| iPS:435595 | 21-225_160H4 | NA | AGCTATAGGATGAAC | TCCATTAGTAGTGGTAGTAGT AGTTACATAGACTACGC AGACTCAGTGAAGGGC | AAGAGTTGGTTTGACTAC |
| | | | SEQ ID NO:6371 | SEQ ID NO:14383 | SEQ ID NO:22395 |
| | | AA | SYRMN | SISGSSSYIDYADSVKG | KSWFDY |
| | | | SEQ ID NO:6372 | SEQ ID NO:14384 | SEQ ID NO:22396 |
| iPS:435599 | 21-225_160B10 | NA | AGAAGTAGCTACTACTGGGG C | AATATCTATTATAGTGGG AGCGCTACCACATTCC GTCCCTCAAGAGT | CATGACCCAAACTGGGGAGT TGACTAC |
| | | | SEQ ID NO:6373 | SEQ ID NO:14385 | SEQ ID NO:22397 |
| | | AA | RSSYYWG | NIYYSGSAYHIPSLKS | HDPNWGVDY |
| | | | SEQ ID NO:6374 | SEQ ID NO:14386 | SEQ ID NO:22398 |
| iPS:435601 | 21-225_160G10 | NA | AGCTTTGGCATGCAC | GTCATATGGTATGATGG AAGTTATAAATACTATG CAGACTCCGTGAAGGGC | GTTGGTATAGAAGTGGCTGG TGACTACTACTTCGGTATGG AAGTC |
| | | | SEQ ID NO:6375 | SEQ ID NO:14387 | SEQ ID NO:22399 |
| | | AA | SFGMH | VIWYDGSYKYYADSVKG | VGIEVAGDYYFGMEV |
| | | | SEQ ID NO:6376 | SEQ ID NO:14388 | SEQ ID NO:22400 |
| iPS:435605 | 21-225_161A4 | NA | AGCAACTACTACGAGC | GTTATTTATACCGGTGGT AGCACATACAACGCAGA CTCCGTGAAGGGC | AATTGGGGAATGGCTGGCCC CTTTGACTAC |
| | | | SEQ ID NO:6377 | SEQ ID NO:14389 | SEQ ID NO:22401 |
| | | AA | SNYMS | VIYTGGSTYNADSVKG | NWGMAGPFDY |
| | | | SEQ ID NO:6378 | SEQ ID NO:14390 | SEQ ID NO:22402 |
| iPS:435607 | 21-225_161G4 | NA | AGCTATGGCATGCAC | GTTATATCATATGGTGGA AGTAATAAATACCATGC AGACTCCGTGAAGGGC | CGGAGCAGCTCGTCGGGGGG CTACGGTATGGACGTC |
| | | | SEQ ID NO:6379 | SEQ ID NO:14391 | SEQ ID NO:22403 |

FIGURE 49
(Continued)

| | | | | | | |
|---|---|---|---|---|---|---|
| iPS:435609 | 21-225_161F7 | AA | SYGMH<br>SEQ ID NO:6380 | VISYGGSNKYHADSVKG<br>SEQ ID NO:14392 | RSSSSGGYGMDV<br>SEQ ID NO:22404 |
| | | NA | GACTTTGGCTTGCAC<br>SEQ ID NO:6381 | GTTATATGGTTTGATGGA<br>AGTAATAAATACTATGC<br>AGACTCCGTGAAGGGC<br>SEQ ID NO:14393 | GAGATTGGCTGGCTCTCTGA<br>CTAC<br>SEQ ID NO:22405 |
| iPS:435611 | 21-225_161F10 | AA | DFGLH<br>SEQ ID NO:6382 | VIWFDGSNKYYADSVKG<br>SEQ ID NO:14394 | EIGWLSDY<br>SEQ ID NO:22406 |
| | | NA | AGCTATGGCATGCAC<br>SEQ ID NO:6383 | ATTATATCATATTCTGA<br>AGAAATGATTTCTATGC<br>AGACTCCGTGAAGGGC<br>SEQ ID NO:14395 | CGTATAGCAGCAGTGGTCA<br>CTACGGTATGGACGTC<br>SEQ ID NO:22407 |
| iPS:435613 | 21-225_161D11 | AA | SYGMH<br>SEQ ID NO:6384 | IISYSGRNDFYADSVKG<br>SEQ ID NO:14396 | RIAAAGHYGMDV<br>SEQ ID NO:22408 |
| | | NA | GACTTTGGCTTGCAC<br>SEQ ID NO:6385 | GTTATATGGTTTGATGGA<br>AGTAATAAATACTATGC<br>AGACTCCGTGAAGGGC<br>SEQ ID NO:14397 | GAGATTGGCTGGCTCTCTGA<br>CTAC<br>SEQ ID NO:22409 |
| iPS:435615 | 21-225_161G12 | AA | DFGLH<br>SEQ ID NO:6386 | VIWFDGSNKYYADSVKG<br>SEQ ID NO:14398 | EIGWLSDY<br>SEQ ID NO:22410 |
| | | NA | GACTATGTCATGCAG<br>SEQ ID NO:6387 | GTTATATGGTATGATGG<br>AAGTAATAAATACTATG<br>CAGACTCCGTGAAGGGC<br>SEQ ID NO:14399 | GAACCGTATAATAGTGGCTG<br>GTACGACTACGGTATGGACG<br>TC<br>SEQ ID NO:22411 |
| | | AA | DYVMQ<br>SEQ ID NO:6388 | VIWYDGSNKYYADSVKG<br>SEQ ID NO:14400 | EPYNSGWYDYGMDV<br>SEQ ID NO:22412 |

FIGURE 49 (Continued)

| | | | | |
|---|---|---|---|---|
| iPS:435617 | 21-225_162F2 | NA | AGTTATAGCATGAAC<br>SEQ ID NO:6389 | TCCATTAGTGGTAGTAGT<br>ACGTACACATATACGC<br>AGACTCAGTGAAGGC<br>SEQ ID NO:14401 | GATCGGGGCAGCAGC<br>SEQ ID NO:22413 |
| | | AA | SYSMN<br>SEQ ID NO:6390 | SISGSSTYIYYADSVKG<br>SEQ ID NO:14402 | DRGSS<br>SEQ ID NO:22414 |
| iPS:435621 | 21-225_162H3 | NA | AGTTATAGCATGAAC<br>SEQ ID NO:6391 | TCCATTAGTGGTAGTAGT<br>ACGTACACATATACGC<br>AGACTCAGTGAAGGC<br>SEQ ID NO:14403 | GATCGGGGCAGCAGC<br>SEQ ID NO:22415 |
| | | AA | SYSMN<br>SEQ ID NO:6392 | SISGSSTYIYYADSVKG<br>SEQ ID NO:14404 | DRGSS<br>SEQ ID NO:22416 |
| iPS:435623 | 21-225_162D5 | NA | AATTATGATATCAAC<br>SEQ ID NO:6393 | TGGATGCACCTAACAG<br>TGGTAACACAGGCTATG<br>CACAGAAGTTCCAGGGC<br>SEQ ID NO:14405 | AGCAGTGGCTGGTACTTCTT<br>TGACTAC<br>SEQ ID NO:22417 |
| | | AA | NYDIN<br>SEQ ID NO:6394 | WMHPNSGNTGYAQKFQG<br>SEQ ID NO:14406 | SSGWYFFDY<br>SEQ ID NO:22418 |
| iPS:435627 | 21-225_162F6 | NA | AATTATGATATCAAC<br>SEQ ID NO:6395 | TGGATGCACCTAACAG<br>TGGTAACACAGGCTATG<br>CACAGAAGTTCCAGGGC<br>SEQ ID NO:14407 | AGCAGTGGCTGGTACCGCTT<br>TGACTAC<br>SEQ ID NO:22419 |
| | | AA | NYDIN<br>SEQ ID NO:6396 | WMHPNSGNTGYAQKFQG<br>SEQ ID NO:14408 | SSGWYRFDY<br>SEQ ID NO:22420 |
| iPS:435629 | 21-225_162H6 | NA | AACTATGGCATGCAC | GTTTATATGGTATGATGG<br>AAGTAATAAATACTATG<br>CAGACTCCGTGAAGGGC | AAAGGTATAGCAGCAGTTGG<br>AGACTACTACGGTATGG<br>ACGTC |

FIGURE 49
(Continued)

| | | | | | | |
|---|---|---|---|---|---|---|
| iPS:435635 | 21-225_162H6 | AA | SEQ ID NO:6397<br>NYGMH | SEQ ID NO:14409<br>VIWYDGSNKYYADSVKG | SEQ ID NO:22421<br>KGIAAVGDYYGMDV |
| | | NA | SEQ ID NO:6398<br>AGCTATAGCATGAAC | SEQ ID NO:14410<br>TCCATTAGTAGTGGTAGTGGT<br>AGTTACATATACTACGC<br>AGACTCAGTGAAGGGC | SEQ ID NO:22422<br>TATAGCAGCTCGCACTAT |
| iPS:435637 | 21-225_163F1 | AA | SEQ ID NO:6399<br>SYSMN | SEQ ID NO:14411<br>SISGSGSYIYYADSVKG | SEQ ID NO:22423<br>YSSSHY |
| | | NA | SEQ ID NO:6400<br>AGTTATAGCATGAAC | SEQ ID NO:14412<br>TCCACTAGTGGGAGTTCT<br>ACTTACATATACTACGCA<br>GACTCAGTGAAGGGC | SEQ ID NO:22424<br>GATCGAGGCAGCCTC |
| iPS:435639 | 21-225_163E2 | AA | SEQ ID NO:6401<br>SYSMN | SEQ ID NO:14413<br>STSGSSTYIYYADSVKG | SEQ ID NO:22425<br>DRGSL |
| | | NA | SEQ ID NO:6402<br>AGTTATAGCATGAGC | SEQ ID NO:14414<br>TCCATTAGTGGTAGTAGT<br>GCTTACATATACTACGCA<br>GACTCAGTGAAGGGC | SEQ ID NO:22426<br>TTGAGCGGTATGGACGTC |
| iPS:435641 | 21-225_163G6 | AA | SEQ ID NO:6403<br>SYSMS | SEQ ID NO:14415<br>SISGSSAYIYYADSVKG | SEQ ID NO:22427<br>LSGMDV |
| | | NA | SEQ ID NO:6404<br>AGCTATAGCATGAAC | SEQ ID NO:14416<br>TCCATTAGTGGTAGTAGT<br>ACTTACATATACTACGCA<br>GACTCAGTGAAGGGC | SEQ ID NO:22428<br>GATCGAGGCAGCCTC |
| iPS:435641 | 21-225_163F9 | AA | SEQ ID NO:6405<br>SYSMN | SEQ ID NO:14417<br>SISGSSTYIYYADSVKG | SEQ ID NO:22429<br>DRGSL |
| | | NA | SEQ ID NO:6406 | SEQ ID NO:14418 | SEQ ID NO:22430 |

FIGURE 49
(Continued)

| | | NA | AGCTATAGCATGAAC | TCCATTAGTGGTAGTAGT ACTTACATATACGCA GACTCAGTGAAGGGC | GCCCGTATGGACGTC |
|---|---|---|---|---|---|
| iPS:435643 | 21-225_163G10 | | SEQ ID NO:6407 | SEQ ID NO:14419 | SEQ ID NO:22431 |
| | | AA | SYSMN | SISGSSTYIYYADSVKG | ARMDV |
| | | | SEQ ID NO:6408 | SEQ ID NO:14420 | SEQ ID NO:22432 |
| iPS:435649 | 21-225_165H2 | NA | CATTATGATATCAAC | TGGATGCACCCTAACAG TCATAAGACAGGCTATG CACAGAAGTTCCAGGGC | AGCAGTGGCTGGTACATGT TGACTAC |
| | | | SEQ ID NO:6409 | SEQ ID NO:14421 | SEQ ID NO:22433 |
| | | AA | HYDIN | WMHPNSHKTGYAQKFQG | SSGWYMFDY |
| | | | SEQ ID NO:6410 | SEQ ID NO:14422 | SEQ ID NO:22434 |
| iPS:435653 | 21-225_166H12 | NA | AGCTATAGCATGAGC | TCCATTAGTGGGAGTAG TAGTTACAGTTACTACGC AGACTCAGTGAAGGGC | CTAACTGGCTTTGACTAC |
| | | | SEQ ID NO:6411 | SEQ ID NO:14423 | SEQ ID NO:22435 |
| | | AA | SYSMS | SISGSSSYSYYADSVKG | LTGFDY |
| | | | SEQ ID NO:6412 | SEQ ID NO:14424 | SEQ ID NO:22436 |
| iPS:435655 | 21-225_167E2 | NA | AGCTTTGGCATGCAC | GTCATATGGTATGGATGG AACTTATAAATACTATGC AGACTCCGTGAAGGGC | GTTGGTATTGAAGTGGCTGG TGACTACTACTACGGTATGG AAGTC |
| | | | SEQ ID NO:6413 | SEQ ID NO:14425 | SEQ ID NO:22437 |
| | | AA | SFGMH | VIWYDGTYKYYADSVKG | VGIEVAGDYYYGMEV |
| | | | SEQ ID NO:6414 | SEQ ID NO:14426 | SEQ ID NO:22438 |
| iPS:435657 | 21-225_167H10 | NA | AGCTTTGGCATGCAC | GTCATATGGTATGGATGG AAGTTATAAGTACCATG CAGACTCCGTGAAGGGC | GTTGGTATAGAAGTGGCTGG TGACTACTACTACGGTATGG AAGTC |
| | | | SEQ ID NO:6415 | SEQ ID NO:14427 | SEQ ID NO:22439 |

FIGURE 49
(Continued)

| | | | | | VIWYDGSYKYHADSVKG | VGIEVAGDYYYGMEV |
|---|---|---|---|---|---|---|
| iPS:435659 | 21-225_167D12 | AA | SFGMH | | | |
| | | | SEQ ID NO:6416 | | SEQ ID NO:14428 | SEQ ID NO:22440 |
| | | NA | AGCTATGGTCATGAGC | | GCTATGAGTGGTAGTGG TGGTAGAACATACTACG CAGACTCCGTGAAGGGC | TATACCTGGAACGGCTAC |
| | | | SEQ ID NO:6417 | | SEQ ID NO:14429 | SEQ ID NO:22441 |
| iPS:435663 | 21-225_169B1 | AA | SYVMS | | AMSGSGGRTYYADSVKG | YTWNGY |
| | | | SEQ ID NO:6418 | | SEQ ID NO:14430 | SEQ ID NO:22442 |
| | | NA | AGCTATGGCATGCAC | | GTTATATGGTATGATGG AAGTAATAAATACTATG CAGACTCCGTGAGGGGC | GATCCCTTACGTGGATACAA TGACCCGGTTATGGACTAC |
| | | | SEQ ID NO:6419 | | SEQ ID NO:14431 | SEQ ID NO:22443 |
| | | AA | SYGMH | | VIWYDGSNKYYADSVRG | DPLRGYNDPVMDY |
| | | | SEQ ID NO:6420 | | SEQ ID NO:14432 | SEQ ID NO:22444 |
| iPS:435665 | 21-225_169F2 | NA | AGTTACTACTGGAGT | | CGTATCGATACCAGTGG GATCACCAACTACAACC CCTCCCTCAAGAGT | GAGGGAGGAGTGGGAGCTA CCTACTTTGACTAC |
| | | | SEQ ID NO:6421 | | SEQ ID NO:14433 | SEQ ID NO:22445 |
| | | AA | SYYWS | | RIDTSGITNYNPSLKS | EGGVGATYFDY |
| | | | SEQ ID NO:6422 | | SEQ ID NO:14434 | SEQ ID NO:22446 |
| iPS:435667 | 21-225_169E3 | NA | GGCCATAGCATGAAC | | TACATTAGCCTTAGTGGT AGTACCATAAAGTACGC AGACTCTGTGAAGGGC | AGGGGGATTACTGTGGTTCG GAATGAGGACGGTTGGACG TC |
| | | | SEQ ID NO:6423 | | SEQ ID NO:14435 | SEQ ID NO:22447 |
| | | AA | GHSMN | | YISLSGSTIKYADSVKG | RGITVRNEDGLDV |
| | | | SEQ ID NO:6424 | | SEQ ID NO:14436 | SEQ ID NO:22448 |

FIGURE 49
(Continued)

| | | | | | |
|---|---|---|---|---|---|
| iPS:435669 | 21-225_169F9 | NA | ACCTATGGCATGCAC | ATTATATGGTATGATGG AACTAATAAATACTATG CAGACTCCGTGAAGGGC | GATCCCTTACGTGGATACAA TGACCCGGTTATGGACTAC |
| | | | SEQ ID NO:6425 | SEQ ID NO:14437 | SEQ ID NO:22449 |
| | | AA | TYGMH | IIWYDGTNKYYADSVKG | DPLRGYNDPVMDY |
| | | | SEQ ID NO:6426 | SEQ ID NO:14438 | SEQ ID NO:22450 |
| iPS:435671 | 21-225_169H5 | NA | AGTTACTACTGGAGT | CGTATCGATACCAGTGG GATACCAACTACAACC CCTCCCTCAAGAGT | GAGGGAGGAGTGGGAGCTA CCTACTTTGACTAC |
| | | | SEQ ID NO:6427 | SEQ ID NO:14439 | SEQ ID NO:22451 |
| | | AA | SYYWS | RIDTSGITNYNPSLKS | EGGVGATYFDY |
| | | | SEQ ID NO:6428 | SEQ ID NO:14440 | SEQ ID NO:22452 |
| iPS:435673 | 21-225_169E6 | NA | GGCCATAGCATGAAC | TACATTAGCATTAGTAGT AGTACCATAAAGTACGC AGACTCTGTGAAGGGC | AGGGGGATTACTGTGGTTCG GAATGAGGACGGTTTGGACG TC |
| | | | SEQ ID NO:6429 | SEQ ID NO:14441 | SEQ ID NO:22453 |
| | | AA | GHSMN | YISISSSTIKYADSVKG | RGITVVRNEDGLDV |
| | | | SEQ ID NO:6430 | SEQ ID NO:14442 | SEQ ID NO:22454 |
| iPS:435675 | 21-225_169D7 | NA | AGTTACTACTGGACC | CGTATCTATACCAGTGG GAGCACCAACTACAACC CCTCCCTCAAGAGT | GTCGGGAGGTACTACTACGG TATGGACGTC |
| | | | SEQ ID NO:6431 | SEQ ID NO:14443 | SEQ ID NO:22455 |
| | | AA | SYYWT | RIYTSGSTNYNPSLKS | VGRYYYGMDV |
| | | | SEQ ID NO:6432 | SEQ ID NO:14444 | SEQ ID NO:22456 |
| iPS:435677 | 21-225_169C10 | NA | GGCTACTTTATGCAC | TGGATCAAGCCTAAGAG TGGTGGCACAAACTCTG CACAGAGGTTTCAGGGC | GGGGGGACTACGGTGGCTAC GTGGGGGTCTTTGACTAC |
| | | | SEQ ID NO:6433 | SEQ ID NO:14445 | SEQ ID NO:22457 |
| | | AA | GYFMH | WIKPKSGGTNSAQRFQG | GGTVATWGVFDY |

FIGURE 49 (Continued)

| | | | | | |
|---|---|---|---|---|---|
| iPS:435679 | 21-225_169D10 | NA | SEQ ID NO:6434<br>AGCTATGTCATGAGT | SEQ ID NO:14446<br>GCTATTAGTGGTAGTGGT<br>AGTAGAATATACGC<br>GGACTCCGTGAAGGC | SEQ ID NO:22458<br>GTGGCTTTCTTTGACTAT |
| | | AA | SEQ ID NO:6435<br>SYVMS | SEQ ID NO:14447<br>AISGSGSRIYYADSVKG | SEQ ID NO:22459<br>VAFFDY |
| iPS:435681 | 21-225_169D11 | NA | SEQ ID NO:6436<br>GACTATGTCATGCAC | SEQ ID NO:14448<br>GTTATATGGTATGATGG<br>AAGTAATAAATACTATG<br>CAGACTCCGTGAAGGGC<br>TC | SEQ ID NO:22460<br>GAAAGGTATAGCAGTGGCTG<br>GTACGACTACGGTATGGACG<br>TC |
| | | AA | SEQ ID NO:6437<br>DYVMH | SEQ ID NO:14449<br>VIWYDGSNKYYADSVKG | SEQ ID NO:22461<br>ERYSSGWYDYGMDV |
| iPS:435683 | 21-225_170A1 | NA | SEQ ID NO:6438<br>AGCTATGGCATGCAC | SEQ ID NO:14450<br>ATTATATGGTATGATGG<br>AAGTTATAAATACTATG<br>CAGATTCCGTGAAGGGC | SEQ ID NO:22462<br>GATGCCCAGGATTTTTGGAG<br>TGGTTACTTTGACTCC |
| | | AA | SEQ ID NO:6439<br>SYGMH | SEQ ID NO:14451<br>IIWYDGSYKYYADSVKG | SEQ ID NO:22463<br>DAHDFWSGYFDS |
| iPS:435685 | 21-225_170E1 | NA | SEQ ID NO:6440<br>AGCTATGTCATGAGT | SEQ ID NO:14452<br>GCTATTAGTGGTAGTGGT<br>AATAGAATATACGC<br>AGACTCCGTGAAGGC | SEQ ID NO:22464<br>GTGGCTTTCTTTGACTAT |
| | | AA | SEQ ID NO:6441<br>SYVMS | SEQ ID NO:14453<br>AISGSGNRIYYADSVKG | SEQ ID NO:22465<br>VAFFDY |
| iPS:435687 | 21-225_170H1 | NA | SEQ ID NO:6442<br>AGTTATTACTGGAGC | SEQ ID NO:14454<br>CGTATCTATACCAGTGG<br>GAGCACCAACTACAACC<br>CCTCCCTCAAGAGT | SEQ ID NO:22466<br>GTCGGGAGGTACTACTATGG<br>TATGGACGTC |

FIGURE 49
(Continued)

| | | | | | | | |
|---|---|---|---|---|---|---|---|
| iPS:435689 | 21-225_170H1 | AA | SEQ ID NO:6443<br>SYYWS | SEQ ID NO:14455<br>RIYTSGSTNYNPSLKS | SEQ ID NO:22467<br>VGRYYYGMDV | | |
| | | NA | SEQ ID NO:6444<br>GACTATGTCATGCAC | SEQ ID NO:14456<br>GTTATATGGTATGATGG<br>AAGTAATAAATACTATG<br>AAGACTCCGTGAAGGGC | SEQ ID NO:22468<br>GAGACGTATAGCAGCAGCTG<br>GTACGACTACGGTTATGGACG<br>TC | | |
| iPS:435693 | 21-225_170F3 | AA | SEQ ID NO:6445<br>DYVMH | SEQ ID NO:14457<br>VIWYDGSNKYYEDSVKG | SEQ ID NO:22469<br>ETYSSSWYDYGMDV | | |
| | | NA | SEQ ID NO:6446<br>ACCTATGGCATGCAC | SEQ ID NO:14458<br>ATTATATGGTATGATGG<br>AACTAATAAATACTATG<br>CAGACTCCGTGAAGGGC | SEQ ID NO:22470<br>GATCCCTTACGTGGATACAA<br>TGACCCGGTTATGGACTAC | | |
| iPS:435695 | 21-225_170G4 | AA | SEQ ID NO:6447<br>TYGMH | SEQ ID NO:14459<br>IIWYDGTNKYYADSVKG | SEQ ID NO:22471<br>DPLRGYNDPVMDY | | |
| | | NA | SEQ ID NO:6448<br>AGCTATGGCATGCAC | SEQ ID NO:14460<br>ATTATATGGTATGATGG<br>AACTAATAAATACTATG<br>CAGACTCCGTGAAGGGC | SEQ ID NO:22472<br>GATCCCTTACGTGGATACAA<br>TGACCCGGTTATGGACTAC | | |
| iPS:435697 | 21-225_170D5 | AA | SEQ ID NO:6449<br>SYGMH | SEQ ID NO:14461<br>IIWYDGTNKYYADSVKG | SEQ ID NO:22473<br>DPLRGYNDPVMDY | | |
| | | NA | SEQ ID NO:6450<br>ACCTATGGCATGCAC | SEQ ID NO:14462<br>ATTATATGGTATGATGG<br>GACTAATAAATACTATG<br>CAGACTCCGTGAAGGGC | SEQ ID NO:22474<br>GATCCCTTACGTGGATACAA<br>TGACCCGGTTATGGACTAC | | |
| | 21-225_170G5 | AA | SEQ ID NO:6451<br>TYGMH | SEQ ID NO:14463<br>IIWYDGTNKYYADSVKG | SEQ ID NO:22475<br>DPLRGYNDPVMDY | | |

FIGURE 49
(Continued)

| | | | | SEQ ID NO:6452 | SEQ ID NO:14464 | SEQ ID NO:22476 |
| --- | --- | --- | --- | --- | --- | --- |
| iPS:435699 | 21-225_170D6 | | NA | GGCTACTTTATACAC | TGGATCAAGCCTAACAG TGGTGGCACAAACTCTG CACAGAGGTTTCAGGGC | GGGGGACTACGGTGGCTAC GTGGGGGGTCTTTGACTAC |
| | | | | SEQ ID NO:6453 | SEQ ID NO:14465 | SEQ ID NO:22477 |
| | | | AA | GYFIH | WIKPNSGGTNSAQRFQG | GGTTVATWGVFDY |
| | | | | SEQ ID NO:6454 | SEQ ID NO:14466 | SEQ ID NO:22478 |
| iPS:435701 | 21-225_170F6 | | NA | AATTATGATATCAAC | TGGATGAACCCTAACAG TGGTAACACAGGCTATG CACAGAAGTTCCAGGAC | AGCAGTGGCTGGTACTGGTT CGACCCC |
| | | | | SEQ ID NO:6455 | SEQ ID NO:14467 | SEQ ID NO:22479 |
| | | | AA | NYDIN | WMNPNSGNTGYAQKFQD | SSGWYWFDP |
| | | | | SEQ ID NO:6456 | SEQ ID NO:14468 | SEQ ID NO:22480 |
| iPS:435703 | 21-225_170D11 | | NA | AGCTATGGCATGCAC | ATTATATGGTATGATGG AACTAATAAATACTATG CAGACTCCGTGAAGGGC | GATCCCTTACGTGGATACAA TGACCCGGTTATGGACTAC |
| | | | | SEQ ID NO:6457 | SEQ ID NO:14469 | SEQ ID NO:22481 |
| | | | AA | SYGMH | IIWYDGTNKYYADSVKG | DPLRGYNDPVMDY |
| | | | | SEQ ID NO:6458 | SEQ ID NO:14470 | SEQ ID NO:22482 |
| iPS:435705 | 21-225_171C3 | | NA | ACCTATGGCATGCAC | ATTATATGGTATGATGG GACTAATAAATACTATG CAGACTCCGTGAAGGGC | GATCCCTTACGTGGATACAA TGACCCGGTTATGGACTAC |
| | | | | SEQ ID NO:6459 | SEQ ID NO:14471 | SEQ ID NO:22483 |
| | | | AA | TYGMH | IIWYDGTNKYYADSVKG | DPLRGYNDPVMDY |
| | | | | SEQ ID NO:6460 | SEQ ID NO:14472 | SEQ ID NO:22484 |

FIGURE 49
(Continued)

| | | | | |
|---|---|---|---|---|
| iPS:435709 | 21-225_171A4 | NA | ACCTATGGCATGCAC | ATTATATGGTATGATGG AAGTAATAAATACTATG CAGACTCCGTGAAGGGC | GATCCCTTACGTGGATACAA TGACCCGGTTATGGACTAC |
| | | | SEQ ID NO:6461 | SEQ ID NO:14473 | SEQ ID NO:22485 |
| | | AA | TYGMH | IIWYDGSNKYYADSVKG | DPLRGYNDPVMDY |
| | | | SEQ ID NO:6462 | SEQ ID NO:14474 | SEQ ID NO:22486 |
| iPS:435711 | 21-225_171G4 | NA | AGCTGTGCCATGACC | GCTATTAGTGGTGGTCGTGGT GGTACCACGTTCTACGC AGACTCCGTGAGGGC | GATCTTATTGGGGGAGCTAC TTACTTTGACTAC |
| | | | SEQ ID NO:6463 | SEQ ID NO:14475 | SEQ ID NO:22487 |
| | | AA | SCAMT | AISGRGGTTFYADSVRG | DLIGGATYFDY |
| | | | SEQ ID NO:6464 | SEQ ID NO:14476 | SEQ ID NO:22488 |
| iPS:435713 | 21-225_171D7 | NA | AGCTATGGCATGCAC | GTTATATCATATGACGG AAACAATAGACACTATG CAGACTCCGTGCAGGGC | GATCGTCACCGTTGGACTA CTACGGTTTGGACGTC |
| | | | SEQ ID NO:6465 | SEQ ID NO:14477 | SEQ ID NO:22489 |
| | | AA | SYGMH | VISYDGNNRHYADSVQG | DRHRLDYYALDV |
| | | | SEQ ID NO:6466 | SEQ ID NO:14478 | SEQ ID NO:22490 |
| iPS:435715 | 21-225_171A8 | NA | AGCTCTGCCATGAGC | GTTATTAGTGGTAGTGGT GGTAGCACATTCTACAC AGACTCCGTGAAGGGC | TCGAATAGCAGTGGCTGGTT TGACTAC |
| | | | SEQ ID NO:6467 | SEQ ID NO:14479 | SEQ ID NO:22491 |
| | | AA | SSAMS | VISGSGGSTFYTDSVKG | SNSSGWFDY |
| | | | SEQ ID NO:6468 | SEQ ID NO:14480 | SEQ ID NO:22492 |
| iPS:435717 | 21-225_171A9 | NA | AGCTATGCCATGACT | GCTATTAGTGGTAGTGGT GGTAACACATTCAACGC AGACTCCGTGAAGGGC | CTGGGGATCGACTACTACTA CTACGGTATGGACGTC |
| | | | SEQ ID NO:6469 | SEQ ID NO:14481 | SEQ ID NO:22493 |

FIGURE 49
(Continued)

| | | | | | | |
|---|---|---|---|---|---|---|
| iPS:435719 | 21-225_171A11 | AA | SYAMT<br>SEQ ID NO:6470 | | AISGSGGNTFNADSVKG<br>SEQ ID NO:14482 | LGIDYYYGMDV<br>SEQ ID NO:22494 |
| | | NA | AGCTATAGCATGAAC<br>SEQ ID NO:6471 | TCCATTAGTGGTAGTAGT<br>AGTTACATATACTACGC<br>AGACTCAGTGAAGGGC<br>SEQ ID NO:14483 | | GATAGGGGCAGCTCC<br>SEQ ID NO:22495 |
| iPS:435721 | 21-225_172B3 | AA | SYSMN<br>SEQ ID NO:6472 | | SISGSSSYIYYADSVKG<br>SEQ ID NO:14484 | DRGSS<br>SEQ ID NO:22496 |
| | | NA | ACCTATGGCATGCAC<br>SEQ ID NO:6473 | GTTATATGGTATGATGG<br>AAGTAATAAATACTATG<br>CAGACTCCGTGAAGGGC<br>SEQ ID NO:14485 | | GATCCCTTACGTGGATACAA<br>TGACCCGGTTATGGGACTAC<br>SEQ ID NO:22497 |
| iPS:435723 | 21-225_172B7 | AA | TYGMH<br>SEQ ID NO:6474 | | VIWYDGSNKYYADSVKG<br>SEQ ID NO:14486 | DPLRGYNDPVMDY<br>SEQ ID NO:22498 |
| | | NA | AACTATGGCATGCAC<br>SEQ ID NO:6475 | ATTATATGGTATGATGG<br>AAGTAATAAATACTATG<br>TAGACTCCGTGAAGGGC<br>SEQ ID NO:14487 | | GAGGCGTACGATTTTTGGAG<br>TGGTTATTGGGACTAC<br>SEQ ID NO:22499 |
| iPS:435725 | 21-225_172G8 | AA | NYGMH<br>SEQ ID NO:6476 | | IIWYDGSNKYYVDSVKG<br>SEQ ID NO:14488 | EAYDFWSGYWDY<br>SEQ ID NO:22500 |
| | | NA | ACCTATGGCATGCAC<br>SEQ ID NO:6477 | ATTATATGGTATGATGG<br>AACTAATAAATACTATG<br>CAGACTCCGTGAAGGGC<br>SEQ ID NO:14489 | | GATCCCTTACGTGGATACAA<br>TGACCCGGTTATGGGACTAC<br>SEQ ID NO:22501 |
| | | AA | TYGMH<br>SEQ ID NO:6478 | | IIWYDGTNKYYADSVKG<br>SEQ ID NO:14490 | DPLRGYNDPVMDY<br>SEQ ID NO:22502 |

FIGURE 49
(Continued)

| | | | | | |
|---|---|---|---|---|---|
| iPS:435727 | 21-225_172E11 | NA | AATTATGATATCAAC SEQ ID NO:6479 | TGGATGCACCCTAACAG TGGTAACACAGGCTATG CACAGAAGTTCCAGGGC SEQ ID NO:14491 | AGCAGTGGCTGGTACCGGTT TGACTAC SEQ ID NO:22503 |
| | | AA | NYDIN | WMHPNSGNTGYAQKFQG | SSGWYRFDY SEQ ID NO:22504 |
| iPS:435729 | 21-225_173E7 | NA | AGCTATGCCATGAGC SEQ ID NO:6480 | TTTATTAGTGGTAGTGGT GGTAACACATTCTACGC AGACTCCGTGAAGGGC SEQ ID NO:14492 | AGGGATACCTACAACGGTTG GGATGCTTTTGATATC SEQ ID NO:22505 |
| | | AA | SYAMS SEQ ID NO:6481 | FISGSGGNTFYADSVKG SEQ ID NO:14493 | RDTYNGWDAFDI SEQ ID NO:22506 |
| iPS:435731 | 21-225_173A11 | NA | AGCTATGGCATGCAC SEQ ID NO:6482 | ATTATATGGTATGATGG AAGTAATAAATACTATG CAGACTCCGTGAAGGGC SEQ ID NO:14494 | GAGGCTACGATTTTTGGAG TGGTTTCTTTGACTCC SEQ ID NO:22507 |
| | | AA | SYGMH SEQ ID NO:6483 | IIWYDGSNKYYADSVKG SEQ ID NO:14495 | EAYDFWSGFFDS SEQ ID NO:22508 |
| iPS:435733 | 21-225_173C11 | NA | AGCTATGGCATACAC SEQ ID NO:6484 | CTTATATTTTATGATGGA AGTAATAAATACTATGC AGACTCCGTGAAGGGC SEQ ID NO:14496 | CGGTATAGCAGCAGCTGGTC CGGTGGTATGGACGTC SEQ ID NO:22509 |
| | | AA | SYGIH SEQ ID NO:6485 | LIFYDGSNKYYADSVKG SEQ ID NO:14497 | RYSSSWSGGMDV SEQ ID NO:22510 |
| | | | SEQ ID NO:6486 | SEQ ID NO:14498 | |

FIGURE 49
(Continued)

| | | | | | |
|---|---|---|---|---|---|
| iPS:435735 | 21-225_173H12 | NA | AGCTATGGCATGCAC | ATTATATGGTATGATGG AACTAAACAAATACTATG CAGACTCCGTGAAGGGC | GATCCCTTACGTGGATACAA TGACCCGGTTATGGACTAC |
| | | | SEQ ID NO:6487 | SEQ ID NO:14499 | SEQ ID NO:22511 |
| | | AA | SYGMH | IIWYDGTNKYYADSVKG | DPLRGYNDPVMDY |
| | | | SEQ ID NO:6488 | SEQ ID NO:14500 | SEQ ID NO:22512 |
| iPS:435737 | 21-225_174G5 | NA | AATTATGATATCAAC | TGGATGCACCCTAACAG TGGTAACACAGGCTATG CACAGAAGTTCCAGGGC | AGCAGTGGCTGGTACTGGTT CGACCCC |
| | | | SEQ ID NO:6489 | SEQ ID NO:14501 | SEQ ID NO:22513 |
| | | AA | NYDIN | WMHPNSGNTGYAQKFQG | SSGWYWFDP |
| | | | SEQ ID NO:6490 | SEQ ID NO:14502 | SEQ ID NO:22514 |
| iPS:435739 | 21-225_174G7 | NA | AGCTCTGCCATGAGC | GTTATTAGTGGTAGTGGT GGTAGCACATTCTACAC AGACTCCGTGAAGGGC | TCGAATAGCAGTGGCTGGTT TGACTAC |
| | | | SEQ ID NO:6491 | SEQ ID NO:14503 | SEQ ID NO:22515 |
| | | AA | SSAMS | VISGSGGSTFYTDSVKG | SNSSGWFDY |
| | | | SEQ ID NO:6492 | SEQ ID NO:14504 | SEQ ID NO:22516 |
| iPS:435741 | 21-225_174G10 | NA | GACTATGTCATGCAC | GTTATATGGTATGATGG AAGTAATAAATACTATG CAGACTCCGTGAAGGGC | GAAAGGTATAGCAGTGGCTG GTACGACTACGGTATGGACG TC |
| | | | SEQ ID NO:6493 | SEQ ID NO:14505 | SEQ ID NO:22517 |
| | | AA | DYVMH | VIWYDGSNKYYADSVKG | ERYSSGWYDYGMDV |
| | | | SEQ ID NO:6494 | SEQ ID NO:14506 | SEQ ID NO:22518 |

FIGURE 49
(Continued)

| | | | | |
|---|---|---|---|---|
| iPS:435743 | 21-225_175G1 | NA | ACCTATGGCATGCAC | GTTATATGGTATGATGG AAGTAATAAATACTATG CAGACTCCGTGAAGGGC | GATCCCTTACGTGGATACAA TGACCCGGTTATGGACTAC |
| | | AA | SEQ ID NO:6495 TYGMH | SEQ ID NO:14507 VIWYDGSNKYYADSVKG | SEQ ID NO:22519 DPLRGYNDPVMDY |
| iPS:435745 | 21-225_175G3 | NA | SEQ ID NO:6496 GGCTACTTTATGCAC | SEQ ID NO:14508 TGGATCAAGCCTAAAAG TGGTGGCACAAACTGTG CACAGAGGTTCAGGGC | SEQ ID NO:22520 GGGGGACTACGGTGACTAC GTGGGGGTCTTTGACTAC |
| | | AA | SEQ ID NO:6497 GYFMH | SEQ ID NO:14509 WIKPKSGGTNCAQRFQG | SEQ ID NO:22521 GGTTVTFWGVFDY |
| iPS:435747 | 21-225_175C4 | NA | SEQ ID NO:6498 AGCTATGTCATGAGC | SEQ ID NO:14510 GCTATTAGTGGTAGTGGT GATAGAACATACTACGC AGACTCCGTGAAGGGC | SEQ ID NO:22522 ACAGCGGGCTTTGACTAC |
| | | AA | SEQ ID NO:6499 SYVMS | SEQ ID NO:14511 AISGSGDRTYYADSVKG | SEQ ID NO:22523 TAGFDY |
| iPS:435749 | 21-225_175C10 | NA | SEQ ID NO:6500 AGCTATGCCATGAGC | SEQ ID NO:14512 TCTATTAGTGGTCGTGGT GGTAGCACGTTCTACGC AGACTCCGTGAAGGGC | SEQ ID NO:22524 TCGAATAGCAGTGGCTGGTT TGACTAC |
| | | AA | SEQ ID NO:6501 SYAMS | SEQ ID NO:14513 SISGRGGSTFYADSVKG | SEQ ID NO:22525 SNSSGWFDY |
| iPS:435751 | | NA | SEQ ID NO:6502 AATTATGATCTCAAC | SEQ ID NO:14514 TGGATGCACCCTAACAG TGGTAACACAGGCTATG CACAGAAGTTCCAGGGC | SEQ ID NO:22526 AGCAGTGGCTGGTACTACTT TGACTAC |

FIGURE 49
(Continued)

| | | | SEQ ID NO:6503 | SEQ ID NO:14515 | SEQ ID NO:22527 |
|---|---|---|---|---|---|
| | 21-225_175D10 | AA | NYDLN | WMHPNSGNTGYAQKFQG | SSGWYYFDY |
| iPS:435753 | | NA | SEQ ID NO:6504 AGCTATGCCATGAGC | SEQ ID NO:14516 ATTATTAGTGGTAGTGGT GGTAACACATACTACGC AGACTCCGTGAAGGGC | SEQ ID NO:22528 AGGGATACCTGGAACGGTTG GGATGCTTTTGATATC |
| | 21-225_175G10 | AA | SEQ ID NO:6505 SYAMS | SEQ ID NO:14517 IISGSGGNTYYADSVKG | SEQ ID NO:22529 RDTWNGWDAFDI |
| iPS:435755 | | NA | SEQ ID NO:6506 AGCTATGGCATGCAC | SEQ ID NO:14518 ATTATATGGTATGATGG AAGTTATAAATACTATG CAGACTCCGTGAAGGGC | SEQ ID NO:22530 GATGCCACGATTTTTGGAG TGGTTACTTGCCTAC |
| | 21-225_176H4 | AA | SEQ ID NO:6507 SYGMH | SEQ ID NO:14519 IIWYDGSYKYYADSVKG | SEQ ID NO:22531 DAHDFWSGYFAY |
| iPS:435759 | | NA | SEQ ID NO:6508 GGCCATAGTATGAAC | SEQ ID NO:14520 TACATTAGCATTAGTGGT AGTACCATAAAGTACGC AGACTCTGTGAAGGGC | SEQ ID NO:22532 AGGGGGATTACTGTGGTTCG GAATGAGGACGGTTGGACG TC |
| | 21-225_176E6 | AA | SEQ ID NO:6509 GHSMN | SEQ ID NO:14521 YTSISGSTIKYADSVKG | SEQ ID NO:22533 RGITVVRNEDGLDV |
| iPS:435761 | | NA | SEQ ID NO:6510 ACCTATGGCATGCAC | SEQ ID NO:14522 ATTATATGGTATGATGG AACTAATAAATACTATG CAGACTCCGTGAAGGGC | SEQ ID NO:22534 GATCCCTTAGTAGTGGATACAA TGACCCGGTTTTGGACTAC |
| | 21-225_176B11 | AA | SEQ ID NO:6511 TYGMH | SEQ ID NO:14523 IIWYDGTNKYYADSVKG | SEQ ID NO:22535 DPLRGYNDPVLDY |
| | | | SEQ ID NO:6512 | SEQ ID NO:14524 | SEQ ID NO:22536 |

FIGURE 49
(Continued)

| | | | | |
|---|---|---|---|---|
| iPS:435763 | 21-225_176H12 | NA | GACTATGTCATGCAC | GTTATATGGTATGATGG AAGTAATAAATACTATG CCGACTCCGTGAAGGGC | GAAAAGTATAGCAGCAACTG GTACGACTACGGTATGGACG TC |
| | | | SEQ ID NO:6513 | SEQ ID NO:14525 | SEQ ID NO:22537 |
| | | AA | DYVMH | VIWYDGSNKYYADSVKG | EKYSSNWYDYGMDV |
| | | | SEQ ID NO:6514 | SEQ ID NO:14526 | SEQ ID NO:22538 |
| iPS:435765 | 21-225_177D3 | NA | AGCTATGTCATGAAC | GGTATGAGCGGTAGTGG TGGTAGAACATACTACG CAGACTCCGTGAAGGAC | GTGACTTTCTTTGACTAT |
| | | | SEQ ID NO:6515 | SEQ ID NO:14527 | SEQ ID NO:22539 |
| | | AA | SYVMN | GMSGSGGRTYYADSVKD | VTFFDY |
| | | | SEQ ID NO:6516 | SEQ ID NO:14528 | SEQ ID NO:22540 |
| iPS:435767 | 21-225_177B4 | NA | GATTATGTCATGCAC | GTTATATGGTATGATGG AAGTAATAAATACTATG CAGACTCCGTGAAGGGC | GAAAAGTATAGCAGCAGCTG GTACGACTACGGTTTGGACG TC |
| | | | SEQ ID NO:6517 | SEQ ID NO:14529 | SEQ ID NO:22541 |
| | | AA | DYVMH | VIWYDGSNKYYADSVKG | EKYSSSWYDYGLDV |
| | | | SEQ ID NO:6518 | SEQ ID NO:14530 | SEQ ID NO:22542 |
| iPS:435769 | 21-225_177B6 | NA | AGTTATGCCATGAGC | GTTATTAGTAGTGGTAGTGGT AGTAACACATACTACGT AGACTCCGTGAAGGGC | GGTTACTATGATAGTAGTGG TTATTACTACCCTTTTGACTT C |
| | | | SEQ ID NO:6519 | SEQ ID NO:14531 | SEQ ID NO:22543 |
| | | AA | SYAMS | VISGSGSNTYYVDSVKG | GYYDSSGYYPFDF |
| | | | SEQ ID NO:6520 | SEQ ID NO:14532 | SEQ ID NO:22544 |

FIGURE 49
(Continued)

| | | | | |
|---|---|---|---|---|
| iPS:435771 | 21-225_177B11 | NA | AGCTATGGCATGCAC | ATTATATGGTATGATGG AAGTTATAAATACTATA CAGACTCCGTGAAGGGC | GAGACTTACGATTTTTGGAG TGGTTATTTGTCTTC |
| | | | SEQ ID NO:6521 | SEQ ID NO:14533 | SEQ ID NO:22545 |
| | | AA | SYGMH | IIWYDGSYKYYTDSVKG | ETYDFWSGYFVF |
| | | | SEQ ID NO:6522 | SEQ ID NO:14534 | SEQ ID NO:22546 |
| iPS:435773 | 21-225_177B12 | NA | AATTATATGATATCAAC | TGGATGCACCCTAACAG TGGTAACACAGGCTATG CACAGAAGTTCCAGGGC | AGCAGTGGCTGGTACTACTT TGACTTC |
| | | | SEQ ID NO:6523 | SEQ ID NO:14535 | SEQ ID NO:22547 |
| | | AA | NYDIN | WMHPNSGNTGYAQKFQG | SSGWYYFDF |
| | | | SEQ ID NO:6524 | SEQ ID NO:14536 | SEQ ID NO:22548 |
| iPS:435775 | 21-225_178A5 | NA | AGCTATGCCATGACC | GTTATTAGTGGTAGTGGT GGTAATACATTCTACGC AGACTCCGTGAAGGGC | CGGGAGGTGACTACTTTGA CTAC |
| | | | SEQ ID NO:6525 | SEQ ID NO:14537 | SEQ ID NO:22549 |
| | | AA | SYAMT | VISGSGGNTFYADSVKG | RDGDYFDY |
| | | | SEQ ID NO:6526 | SEQ ID NO:14538 | SEQ ID NO:22550 |
| iPS:435777 | 21-225_178F7 | NA | AGCTATGCCATGACC | GTTATTAGTGGTAGTGGT GGTAACACATTCTACGC AGACTCCGTGAAGGGC | CGGTACGGTGACTACTTTGA CTAC |
| | | | SEQ ID NO:6527 | SEQ ID NO:14539 | SEQ ID NO:22551 |
| | | AA | SYAMT | VISGSGGNTFYADSVKG | RYGDYFDY |
| | | | SEQ ID NO:6528 | SEQ ID NO:14540 | SEQ ID NO:22552 |
| iPS:435779 | 21-225_178B10 | NA | ACCTATGGCATGCAC | ATTATATGGTATGATGG AACTAATAAATACTATG CAGACTCCGTGAAGGGC | GATCCCTTACGTGGATACAA TGACCCGGTTATGGACTAC |
| | | | SEQ ID NO:6529 | SEQ ID NO:14541 | SEQ ID NO:22553 |

FIGURE 49
(Continued)

| | | | | | | |
|---|---|---|---|---|---|---|
| iPS:435781 | 21-225_178G10 | AA | TYGMH<br>SEQ ID NO:6530 | IIWYDGTNKYYADSVKG<br>SEQ ID NO:14542 | DPLRGYNDPVMDY<br>SEQ ID NO:22554 | |
| | | NA | ACCTATGGCCATGAAC<br>SEQ ID NO:6531 | GTTATATGGTATGATGG<br>AAGTAATAAATACTACG<br>CAGACTCCGTGAAGGGC<br>SEQ ID NO:14543 | GAACGGTACGATTTTGGAG<br>TGGTCATTTGACTAC<br>SEQ ID NO:22555 | |
| iPS:435783 | 21-225_179G1 | AA | TYGMH<br>SEQ ID NO:6532 | VIWYDGSNKYYADSVKG<br>SEQ ID NO:14544 | ERYDFWSGHFDY<br>SEQ ID NO:22556 | |
| | | NA | AGCTATGGCCATGACC<br>SEQ ID NO:6533 | GTTATTAGTGGTTTTGGT<br>GGTAACACATTCTACGC<br>AGACTCCGTGAAGGGC<br>SEQ ID NO:14545 | CGGTACGGTGACTACTTTGA<br>CTAC<br>SEQ ID NO:22557 | |
| iPS:435785 | 21-225_179C2 | AA | SYAMT<br>SEQ ID NO:6534 | VISGFGGNTFYADSVKG<br>SEQ ID NO:14546 | RYGDYFDY<br>SEQ ID NO:22558 | |
| | | NA | AGCTATGGCCATGCAC<br>SEQ ID NO:6535 | CTTATATTTTATGATGGA<br>AGTAATAAATACTATGC<br>AGACTCCGTGAAGGGC<br>SEQ ID NO:14547 | CGGTATAGCGGCAGCTGGTC<br>CGGTGGTATGGACGTC<br>SEQ ID NO:22559 | |
| iPS:435787 | 21-225_180A3 | AA | SYGMH<br>SEQ ID NO:6536 | LIFYDGSNKYYADSVKG<br>SEQ ID NO:14548 | RYSGSWSGGMDV<br>SEQ ID NO:22560 | |
| | | NA | AGCTTTGCCATGAAC<br>SEQ ID NO:6537 | GTTATTAGCGGGTCGCGGT<br>GGTAACACATTCTACGC<br>AGACTCCGTGAAGGGC<br>SEQ ID NO:14549 | CGGACTGGGGATGATGTTTT<br>TGATGTC<br>SEQ ID NO:22561 | |
| | | AA | SFAMN<br>SEQ ID NO:6538 | VISGRGGNTFYADSVKG<br>SEQ ID NO:14550 | RTGDDVFDV<br>SEQ ID NO:22562 | |

FIGURE 49
(Continued)

| iPS | | | | | |
|---|---|---|---|---|---|
| iPS:435789 | 21-225_180C4 | NA | GCCTATGGCATGCAC SEQ ID NO:6539 | ATTATTGGTATGATGGA AGTTATAAATACTATGC AGACTCCGTGAAGGGC SEQ ID NO:14551 | ACCGGTGTGGATCCCTGGGA CTACTACAACGGAATGGACG TC SEQ ID NO:22563 |
| | | AA | AYGMH SEQ ID NO:6540 | IIWYDGSYKYYADSVKG SEQ ID NO:14552 | TGVDPWDYYNGMDV SEQ ID NO:22564 |
| iPS:435791 | 21-225_180H7 | NA | GACTATGGCATGCAC SEQ ID NO:6541 | GTTATATGGTATGATGA AAATAATAAACACTATG CAGACTCCGCGAAGGGC SEQ ID NO:14553 | GAGGTTGGCTGGTCCGATGA CTAC SEQ ID NO:22565 |
| | | AA | DYGMH SEQ ID NO:6542 | VIWYDENNKHYADSAKG SEQ ID NO:14554 | EVGWSDDY SEQ ID NO:22566 |
| iPS:435793 | 21-225_180F8 | NA | AGCTATGGCATGCAC SEQ ID NO:6543 | GTTATATGGTATGATGG AAGTGATAAATACTATG AAGACTCCGTGAAGGGC SEQ ID NO:14555 | GATCATCCCGGGTGGAGCTA CGGAGACTAC SEQ ID NO:22567 |
| | | AA | SYGMH SEQ ID NO:6544 | VIWYDGSDKYYEDSVKG SEQ ID NO:14556 | DHPRWSYGDY SEQ ID NO:22568 |
| iPS:435795 | 21-225_181C2 | NA | AGCTATGGCATGCAC SEQ ID NO:6545 | ATTATATGGTATGATGG AAGTTATAAATACTATG CAGACTCCGTGAAGGGC SEQ ID NO:14557 | GATCATTAGGATTTTGGAG TGGGCACTTTGACTTC SEQ ID NO:22569 |
| | | AA | SYGMH SEQ ID NO:6546 | IIWYDGSYKYYADSVKG SEQ ID NO:14558 | DHYDFWSGHFDF SEQ ID NO:22570 |

FIGURE 49
(Continued)

| | | | | |
|---|---|---|---|---|
| iPS:435797 | 21-225_181G2 | NA | AGCTACAATATGCAC | TGGATCAACCCTAACAATGGTGGCTCAAACTATACACAGAAGTTTCAGGGC | AAGTTTGGGGAC |
| | | | SEQ ID NO:6547 | SEQ ID NO:14559 | SEQ ID NO:22571 |
| | | AA | SYNMH | WINPNNGGSNYTQKFQG | KFGD |
| | | | SEQ ID NO:6548 | SEQ ID NO:14560 | SEQ ID NO:22572 |
| iPS:435799 | 21-225_181G3 | NA | AGCTATGCCATGAGT | GTTATTAGTGGTAGTGGTGGTAACACATTCTACGGAGACTCCGTGAAGGGC | CGGGAGACCTACGACTGGGGATCCGATGCTTTTGATATC |
| | | | SEQ ID NO:6549 | SEQ ID NO:14561 | SEQ ID NO:22573 |
| | | AA | SYAMS | VISGSGGNTFYGDSVKG | RETYDWGSDAFDI |
| | | | SEQ ID NO:6550 | SEQ ID NO:14562 | SEQ ID NO:22574 |
| iPS:435801 | 21-225_181E5 | NA | AATTATGATATCAAC | TGGATGAACCCTAACAGTGGTAACACAGGCTATGCACAGAAGTTCCAGGGC | AGTAGTGGCTGGTACATCTTTGACTAC |
| | | | SEQ ID NO:6551 | SEQ ID NO:14563 | SEQ ID NO:22575 |
| | | AA | NYDIN | WMNPNSGNTGYAQKFQG | SSGWYIFDY |
| | | | SEQ ID NO:6552 | SEQ ID NO:14564 | SEQ ID NO:22576 |
| iPS:435805 | 21-225_181A8 | NA | GACTATGGCATGCAC | GTTATATGGTATGATGAAATAATAAACACTATGCAGACTCCGCGAAGGGC | GAGGTTGGCTGGTCCGATGACTAC |
| | | | SEQ ID NO:6553 | SEQ ID NO:14565 | SEQ ID NO:22577 |
| | | AA | DYGMH | VIWYDENNKHYADSAKG | EVGWSDDY |
| | | | SEQ ID NO:6554 | SEQ ID NO:14566 | SEQ ID NO:22578 |

FIGURE 49
(Continued)

| | | NA | AGCTATGGCATGCAC | ATTATATGGTATGATGG AAGTTATAAATACTATG CAGACTCCGTGAAGGGC | GATCATTACGATTTTTGGAG TGGGCACTTTGACTAC |
|---|---|---|---|---|---|
| iPS:435807 | 21-225_181C10 | | SEQ ID NO:6555 | SEQ ID NO:14567 | SEQ ID NO:22579 |
| | | AA | SYGMH | IIWYDGSYKYYADSVKG | DHYDFWSGHFDY |
| | | | SEQ ID NO:6556 | SEQ ID NO:14568 | SEQ ID NO:22580 |
| iPS:435809 | 21-225_182H5 | NA | AGCTATGCCATGAGT | GTTATTAGTGGTAGAGG TGGTACCACATTCTACGC AGACTCCGTGAAGGGC | CGGACTGGGGATGATGTTTT TGATATC |
| | | | SEQ ID NO:6557 | SEQ ID NO:14569 | SEQ ID NO:22581 |
| | | AA | SYAMS | VISGRGGTTFYADSVKG | RTGDDVFDI |
| | | | SEQ ID NO:6558 | SEQ ID NO:14570 | SEQ ID NO:22582 |
| iPS:435811 | 21-225_183H6 | NA | AGCTATGGCATGCAC | ATTATACATCATATGCTGGA AGTACTAAATTCTATGCA GACTCCGTGAAGGGC | AGGCCCCGCCAGTGGCTGGT AGAGGGCTACGGTATGGACG TC |
| | | | SEQ ID NO:6559 | SEQ ID NO:14571 | SEQ ID NO:22583 |
| | | AA | SYGMH | IISYAGSTKFYADSVKG | RPPQWLVEGYGMDV |
| | | | SEQ ID NO:6560 | SEQ ID NO:14572 | SEQ ID NO:22584 |
| iPS:435813 | 21-225_183A12 | NA | AGCTATGGCATGCAC | GTTATATCATCTGCTGGA AGTAATAAATACTATGC AGACTCCGTGAAGGGC | AGGTATAGCAGTGGCTGGGA CTGGTTCGACCCC |
| | | | SEQ ID NO:6561 | SEQ ID NO:14573 | SEQ ID NO:22585 |
| | | AA | SYGMH | VISSAGSNKYYADSVKG | RYSSGWDWFDP |
| | | | SEQ ID NO:6562 | SEQ ID NO:14574 | SEQ ID NO:22586 |
| iPS:435815 | 21-225_190G10 | NA | GACTATAGCATGAAC | TCTATTAGTAGTGGTAGT GGTTACATACACTACGC AGACTCAGTGAAGGGC | GCAACTATGGCCCCTTGACTA C |
| | | | SEQ ID NO:6563 | SEQ ID NO:14575 | SEQ ID NO:22587 |
| | | AA | DYSMN | SISSGSGYIHYADSVKG | ATMALDY |

FIGURE 49
(Continued)

| | | | | | |
|---|---|---|---|---|---|
| iPS:435817 | 21-225_190B11 | NA | SEQ ID NO:6564 AATTACTACTGGAGC | SEQ ID NO:14576 CGTATCTATACCAGTGG GAGCACCAACTACAACC CCTCCCTCAAGAGT | SEQ ID NO:22588 GATCGGGGATACTATGGCTA CTACGGTATGGACGTC |
| | | AA | SEQ ID NO:6565 NYYWS | SEQ ID NO:14577 RIYTSGSTNYNPSLKS | SEQ ID NO:22589 DRGYGYYGMDV |
| iPS:435819 | 21-225_190C11 | NA | SEQ ID NO:6566 AGCTATGGCATGCAC | SEQ ID NO:14578 GTTATATGGTATGATGG AAGTAATAAAAACTATG CAGACTCCGTGAAGGGC | SEQ ID NO:22590 GATCAGGGCGTGGGCTACGA CGGTTTGGACGTC |
| | | AA | SEQ ID NO:6567 SYGMH | SEQ ID NO:14579 VIWYDGSNKNYADSVKG | SEQ ID NO:22591 DQGVGYDGLDV |
| iPS:435821 | 21-225_190E11 | NA | SEQ ID NO:6568 AACTATGGCATGCAC | SEQ ID NO:14580 ATTATATGGTTTGATGGA AGTAATAAATACTATGC AGACTCCGTGAAGGGC | SEQ ID NO:22592 GCCCAGGGGGTCTACTACTA CGTTATGGACGTC |
| | | AA | SEQ ID NO:6569 NYGMH | SEQ ID NO:14581 IIWFDGSNKYYADSVKG | SEQ ID NO:22593 AQGVYYYVMDV |
| iPS:435823 | 21-225_190F11 | NA | SEQ ID NO:6570 AGCTATGCCATGAAC | SEQ ID NO:14582 ACTATTAGTGGTACTGGT CGTAGGACATACTACGC AGACTCCGTGAAGGGC | SEQ ID NO:22594 GAGGAGGATTACTATGATAG TAGTGGCCCGGGGGTTCGACC CC |
| | | AA | SEQ ID NO:6571 SYAMN | SEQ ID NO:14583 TISGTGRRTYYADSVKG | SEQ ID NO:22595 EEDYDSSGPGFDP |
| | | | SEQ ID NO:6572 | SEQ ID NO:14584 | SEQ ID NO:22596 |

FIGURE 49
(Continued)

| | | | | | |
|---|---|---|---|---|---|
| iPS:435825 | 21-225_190G11 | NA | ATTTATGGCATGCAC<br>SEQ ID NO:6573 | GTTATATATGGTATGATGG<br>AAGTAATAAAAACTATG<br>CAGACTCCGTGAAGGGC<br>SEQ ID NO:14585 | GATCAGGGCGTGGGCTACGA<br>CGGTTTGGACGTC<br>SEQ ID NO:22597 |
| | | AA | IYGMH<br>SEQ ID NO:6574 | VIWYDGSNKNYADSVKG<br>SEQ ID NO:14586 | DQGVGYDGLDV<br>SEQ ID NO:22598 |
| iPS:435827 | 21-225_190H11 | NA | AGCTACCACTGGAGC<br>SEQ ID NO:6575 | CTTATCTATACCAGTAGG<br>AGCACCATTATACAACCC<br>CTCCCTCAAGAGT<br>SEQ ID NO:14587 | CTCCGGTATAACTGAACTT<br>CCCTTACTTTGACTAC<br>SEQ ID NO:22599 |
| | | AA | SYHWS<br>SEQ ID NO:6576 | LIYTSRSTIYNPSLKS<br>SEQ ID NO:14588 | LRYNWNFPYFDY<br>SEQ ID NO:22600 |
| iPS:435829 | 21-225_190B12 | NA | AGTGGTGGTTACTACTGGAA<br>C<br>SEQ ID NO:6577 | TATATCTATTACAGTGGG<br>AGCACCTACTACAACCC<br>GTCCCTCAAGAGT<br>SEQ ID NO:14589 | TCCGGTATAATTGGACGC<br>CGGGGTCGACCCC<br>SEQ ID NO:22601 |
| | | AA | SGGYYWN<br>SEQ ID NO:6578 | YIYYSGSTYYNPSLKS<br>SEQ ID NO:14590 | SGYNWDAGVDP<br>SEQ ID NO:22602 |
| iPS:435831 | 21-225_190C12 | NA | AGCTATGGCATGCAC<br>SEQ ID NO:6579 | GTTATATCATATGGTAATGGT<br>GGTTATAAAAACTATGT<br>AGACTCCGTGAAGGGC<br>SEQ ID NO:14591 | GGTACCACCACGGGTACTACTA<br>CGGTGTGGACGTC<br>SEQ ID NO:22603 |
| | | AA | SYGMH<br>SEQ ID NO:6580 | VISYDGGYKNYVDSVKG<br>SEQ ID NO:14592 | GTHGYYYGVDV<br>SEQ ID NO:22604 |
| iPS:435833 | 21-225_190D12 | NA | AGCTATGCCATGAGC<br>SEQ ID NO:6581 | GCTATTATTGGTAATGGT<br>GGTAGGACATACTACGC<br>AGACTCCGTGAAGGGC<br>SEQ ID NO:14593 | GATATGGTAGATACAGCTA<br>TGGTTTCTTTGACTAC<br>SEQ ID NO:22605 |

FIGURE 49
(Continued)

| | | | SYAMS | AIIGNGGRTYYADSVKG | DMGRYSYGFFDY |
|---|---|---|---|---|---|
| | | AA | SEQ ID NO:6582 | SEQ ID NO:14594 | SEQ ID NO:22606 |
| iPS:435835 | 21-225_190F12 | NA | AACTATGGCATGCAC | GTTATATGGTTTGATGGA AGTAATGACTACTATGC AGACTCCGTGAAGGGC | GATAGAAGCGTCGGCTACGA CGGTTTAGATGTC |
| | | | SEQ ID NO:6583 | SEQ ID NO:14595 | SEQ ID NO:22607 |
| | | AA | NYGMH | VIWFDGSNDYYADSVKG | DRSVGYDGLDV |
| | | | SEQ ID NO:6584 | SEQ ID NO:14596 | SEQ ID NO:22608 |
| iPS:435837 | 21-225_198G3 | NA | ACCTATGGCATGCAC | GTTATATGGTATGATGG AACTAATAAAAACTATG CAGACTCCGTGAAGGGC | GATCAGGGCGTGGGCTACGA CGGTTTGGACGTC |
| | | | SEQ ID NO:6585 | SEQ ID NO:14597 | SEQ ID NO:22609 |
| | | AA | TYGMH | VIWYDGTNKNYADSVKG | DQGVGYDGLDV |
| | | | SEQ ID NO:6586 | SEQ ID NO:14598 | SEQ ID NO:22610 |
| iPS:435839 | 21-225_191B1 | NA | AGTTATCACTGGAGC | CATATCTATACCAGTGG GAGCACCAAGTACAACC CCTCCCTCAAGAGT | CTCCGGTATAACTGGAACTT CCCTTTCTTTGACTAT |
| | | | SEQ ID NO:6587 | SEQ ID NO:14599 | SEQ ID NO:22611 |
| | | AA | SYHWS | HIYTSGSTKYNPSLKS | LRYNWNPFFDY |
| | | | SEQ ID NO:6588 | SEQ ID NO:14600 | SEQ ID NO:22612 |
| iPS:435841 | 21-225_191D8 | NA | AATTATGATATCAAC | TGGATGCACCCTAACAG TGGTAACACAGGCTATG CACAGAAGTTCCAGGGC | AGCAGTGGCTGTACTACTT TGACTAC |
| | | | SEQ ID NO:6589 | SEQ ID NO:14601 | SEQ ID NO:22613 |
| | | AA | NYDIN | WMHPNSGNTGYAQKFQG | SSGWYYFDY |
| | | | SEQ ID NO:6590 | SEQ ID NO:14602 | SEQ ID NO:22614 |

FIGURE 49
(Continued)

| | | | | | |
|---|---|---|---|---|---|
| iPS:435843 | 21-225_191F1 | NA | AGTGGTGGTTACTACTGGAA C | TACATCTTTTACAGTGGG AGCACCTACTACAACCC GTCCCTCAAGAGT | GGGGATTACGATGGTTCGGG GAGTTATCACTACTATTACG GTATGGACGTC |
| | | | SEQ ID NO:6591 | SEQ ID NO:14603 | SEQ ID NO:22615 |
| | | AA | SGGYYWN | YIFYSGSTYYNPSLKS | GDYDGSGSYHYYYGMDV |
| | | | SEQ ID NO:6592 | SEQ ID NO:14604 | SEQ ID NO:22616 |
| iPS:435845 | 21-225_191G1 | NA | AGCTATGGCATGCAC | GTTATATGGTATGATGG AAGTAATGAACACTATG CAGACTCCGTGAAGGGC | GATAGGGGGGGTGGGTTACTA CGGTTTGGACGTC |
| | | | SEQ ID NO:6593 | SEQ ID NO:14605 | SEQ ID NO:22617 |
| | | AA | SYGMH | VIWYDGSNEHYADSVKG | DRGVGYYGLDV |
| | | | SEQ ID NO:6594 | SEQ ID NO:14606 | SEQ ID NO:22618 |
| iPS:435847 | 21-225_191A3 | NA | AGTGGTGATTACTACTGGAA C | TACATCTTTTACAGTGGG AGCACCTACTACAACCC GTCCCTCAAGAGT | GGGGATTACGATGGTTCGGG GAGTTATCACTACTACTACG GTATGGACGTC |
| | | | SEQ ID NO:6595 | SEQ ID NO:14607 | SEQ ID NO:22619 |
| | | AA | SGDYYWN | YIFYSGSTYYNPSLKS | GDYDGSGSYHYYYGMDV |
| | | | SEQ ID NO:6596 | SEQ ID NO:14608 | SEQ ID NO:22620 |
| iPS:435849 | 21-225_191C3 | NA | AGTGGTGATTACTACTGGAA C | TACATCTTTTACAGTGGG AGCACCTACTACAACCC GTCCCTCAAGAGT | GGGGATTACGATGGTTCGGG GAGTTATCACTTCTACTACG GTATGGACGTC |
| | | | SEQ ID NO:6597 | SEQ ID NO:14609 | SEQ ID NO:22621 |
| | | AA | SGDYYWN | YIFYSGSTYYNPSLKS | GDYDGSGSYHFYYGMDV |
| | | | SEQ ID NO:6598 | SEQ ID NO:14610 | SEQ ID NO:22622 |
| iPS:435851 | 21-225_191D3 | NA | AGTGGTGATTACTACTGGAA C | TACATCTTTTACAGTGGG AGCACCTACTACAACCC GTCCCTCAAGAGT | GGGGATTACGATGGTTCGGG GAGTTATCACTACTATTACG GTATGGACGTC |
| | | | SEQ ID NO:6599 | SEQ ID NO:14611 | SEQ ID NO:22623 |

FIGURE 49
(Continued)

| | | | | | | | |
|---|---|---|---|---|---|---|---|
| iPS:435853 | 21-225_191E3 | AA | SGDYYWN | | YIFYSGSTYYNPSLKS | | GDYDGSGSYHYYYGMDV |
| | | | SEQ ID NO:6600 | | SEQ ID NO:14612 | | SEQ ID NO:22624 |
| | | NA | AGCTACCACTGGAGC | | CTTATCTATACCAGTAGG AGCACCAATTACAACCC CTCCCTCAAGAGT | | CTCCGGTATAACTGGAACTT CCCTTACTTGACTAC |
| | | | SEQ ID NO:6601 | | SEQ ID NO:14613 | | SEQ ID NO:22625 |
| | | AA | SYHWS | | LIYTSRSTNYNPSLKS | | LRYNWNFPYFDY |
| | | | SEQ ID NO:6602 | | SEQ ID NO:14614 | | SEQ ID NO:22626 |
| iPS:435855 | 21-225_191G3 | NA | AATTATGATATCAAC | | CGGATGAACCTAACAG TGGTAACACAGGCTATG CACAGAAGTTCCAGGGC | | AGCAGTGGCTGGTACATCTT TGACTAC |
| | | | SEQ ID NO:6603 | | SEQ ID NO:14615 | | SEQ ID NO:22627 |
| | | AA | NYDIN | | RMNPNSGNTGYAQKFQG | | SSGWYIFDY |
| | | | SEQ ID NO:6604 | | SEQ ID NO:14616 | | SEQ ID NO:22628 |
| iPS:435857 | 21-225_191A4 | NA | AGCTATGGCATGCAC | | GTTATATCATATGATGA GGTTATAAAAACTATGC AGACTCCGTGAAGGGC | | GGTACCCACGGTACTACTA CGGTGTGGACGTC |
| | | | SEQ ID NO:6605 | | SEQ ID NO:14617 | | SEQ ID NO:22629 |
| | | AA | SYGMH | | VISYDGGYKNYADSVKG | | GTHGYYYGVDV |
| | | | SEQ ID NO:6606 | | SEQ ID NO:14618 | | SEQ ID NO:22630 |
| iPS:435859 | 21-225_190E6 | NA | AGCTATGGCATGCAC | | GTTATATGGTATGATGG AAGTAATAAAAACTATG CAGACTCCGTGAAGGGC | | GATCAGGGCGTGGGCTACGA CGGTTTGGACGTC |
| | | | SEQ ID NO:6607 | | SEQ ID NO:14619 | | SEQ ID NO:22631 |
| | | AA | SYGMH | | VIWYDGSNKNYADSVKG | | DQGVGYDGLDV |
| | | | SEQ ID NO:6608 | | SEQ ID NO:14620 | | SEQ ID NO:22632 |

FIGURE 49 (Continued)

| | | | | |
|---|---|---|---|---|
| iPS:435861 | 21-225_190A5 | NA | AGTTATGGCATGCAC SEQ ID NO:6609 | GTTATATGGTATGATGG AAGTAATAAAACTATG CAGACTCCGTGAAGGGC SEQ ID NO:14621 | GATTTCTCTGTAGGGTACGA CGGTATGGACGTC SEQ ID NO:22633 |
| | | AA | SYGMH SEQ ID NO:6610 | VIWYDGSNKNYADSVKG SEQ ID NO:14622 | DFSVGYDGMDV SEQ ID NO:22634 |
| iPS:435863 | 21-225_191H4 | NA | AGTGGTGGTTACTACTGGAAC SEQ ID NO:6611 | TACATCTTTACAGTGGG AGCACCTACTACAACCC GTCCCTCAGGAGT SEQ ID NO:14623 | TCCGGGTATAACTGGGACAA CGGGGTCGACCCC SEQ ID NO:22635 |
| | | AA | SGGYYWN SEQ ID NO:6612 | YIFYSGSTYYNPSLRS SEQ ID NO:14624 | SGYNWDNGVDP SEQ ID NO:22636 |
| iPS:435865 | 21-225_191A5 | NA | GACTATAGCATGAAC SEQ ID NO:6613 | TCCATTAGTAGTAGTAGT GGTTACATATATTATGCAC GACTCAGTGAAGGGC SEQ ID NO:14625 | GCTACTATGGCCCTTGACTA C SEQ ID NO:22637 |
| | | AA | DYSMN SEQ ID NO:6614 | SISSSGYIYYADSVKG SEQ ID NO:14626 | ATMALDY SEQ ID NO:22638 |
| iPS:435867 | 21-225_191E5 | NA | AGCTATATGGCCATGAAC SEQ ID NO:6615 | ACTATTAGTGGTACTGGT CGTAGGACATACTAGC AGACTCCGTGAAGGGC SEQ ID NO:14627 | GAGGAGGATTACTATGATAG TAGTGGCCCGGGGTTCGACC CC SEQ ID NO:22639 |
| | | AA | SYAMN SEQ ID NO:6616 | TISGTGRRTYYADSVKG SEQ ID NO:14628 | EEDYYDSSGPGFDP SEQ ID NO:22640 |
| iPS:435869 | 21-225_190B1 | NA | AGCTATATGGCATGCAC | GTTATATGGTATGATGG AAGTAATAAACATTATG CAGACTCCGTGAAGGGC | GATAGAACAGTGGGATACTC CGGTATGGACGTC |

FIGURE 49
(Continued)

| | | | | | | |
|---|---|---|---|---|---|---|
| iPS:435871 | 21-225_190B1 | AA | SEQ ID NO:6617<br>SYGMH | SEQ ID NO:14629<br>VIWYDGSNKHYADSVKG | SEQ ID NO:22641<br>DRTVGYSGMDV |
| | | NA | SEQ ID NO:6618<br>AGCTACCACTGGAGC | SEQ ID NO:14630<br>CTTATCTATACCAGTAGG<br>AGCACCAATTACAACCC<br>CTCCCTCAAGAGT | SEQ ID NO:22642<br>CTCCGGTATAACTGGAACTT<br>CCCTTACTTGACTTC |
| iPS:435873 | 21-225_191E6 | AA | SEQ ID NO:6619<br>SYHWS | SEQ ID NO:14631<br>LIYTSRSTNYNPSLKS | SEQ ID NO:22643<br>LRYNWNFPYFDF |
| | | NA | SEQ ID NO:6620<br>AGCTATGGCATGCAC | SEQ ID NO:14632<br>GTTATATGGTATGATGG<br>AAGTAATAAAACTACG<br>CAGACTCCGTGAAGGGC | SEQ ID NO:22644<br>GATCAGGGCGTGGGCTACGA<br>CGGTTTGGACGTC |
| iPS:435875 | 21-225_190G4 | AA | SEQ ID NO:6621<br>SYGMH | SEQ ID NO:14633<br>VIWYDGSNKNYADSVKG | SEQ ID NO:22645<br>DQGVGYDGLDV |
| | | NA | SEQ ID NO:6622<br>ACCTATGCCATGAGT | SEQ ID NO:14634<br>GCTATTAGTGGTAGTGGT<br>GGTAACACACACTACGC<br>AGACTCCGTGAAGGGC | SEQ ID NO:22646<br>GATGGATTCGGTGGGAGCTC<br>CTACTTTGACTAC |
| iPS:435877 | 21-225_190B9 | AA | SEQ ID NO:6623<br>TYAMS | SEQ ID NO:14635<br>AISRSGGNTHYADSVKG | SEQ ID NO:22647<br>DCFGGSSYFDY |
| | | NA | SEQ ID NO:6624<br>AGCTACAATATGCAC | SEQ ID NO:14636<br>TGGATCAACCCTAACAA<br>TGGTGGCTCAAACTATA<br>CACAGAAGTTTCAGGGC | SEQ ID NO:22648<br>AAGTTTGGGGAC |
| | 21-225_184E7 | AA | SEQ ID NO:6625<br>SYNMH | SEQ ID NO:14637<br>WINPNNGGSNYTQKFQG | SEQ ID NO:22649<br>KFGD |

FIGURE 49
(Continued)

| | | | | | | |
|---|---|---|---|---|---|---|
| iPS:435879 | 21-225_184H10 | NA | SEQ ID NO:6626 GACTATGGCATGCAC | SEQ ID NO:14638 GTTATTTGGTATGATGAA ACTAATAAACACTATGG AGACTCCGTGAAGGGC | SEQ ID NO:22650 GAGGTTGGCTGGCACGATGA CTAT |
| | | AA | SEQ ID NO:6627 DYGMH | SEQ ID NO:14639 VIWYDETNKHYGDSVKG | SEQ ID NO:22651 EVGWHDDY |
| iPS:435881 | 21-225_184D11 | NA | SEQ ID NO:6628 GACTATGGCATGCAC | SEQ ID NO:14640 GTTATTTGGTATGATGAA ACTAATAAACACTATGG AGACTCCGTGAAGGGC | SEQ ID NO:22652 GAGGTTGGCTGGCACGATGA CTAT |
| | | AA | SEQ ID NO:6629 DYGMH | SEQ ID NO:14641 VIWYDETNKHYGDSVKG | SEQ ID NO:22653 EVGWHDDY |
| iPS:435883 | 21-225_185A1 | NA | SEQ ID NO:6630 AGCTATAGCATGAAC | SEQ ID NO:14642 TCCATTAGCAGTAGTGGT AGTTACATATATTACGGA GACTCAGTGAAGGGC | SEQ ID NO:22654 AGCAACCTTTTTGACTGC |
| | | AA | SEQ ID NO:6631 SYSMN | SEQ ID NO:14643 SISSSGSYIYYADSVKG | SEQ ID NO:22655 SNLFDC |
| iPS:435885 | 21-225_185E10 | NA | SEQ ID NO:6632 AGCTACAATATGCAC | SEQ ID NO:14644 TGGATCAACCCTAACAA TGGTGGCTCAAACTATA CACAGAAGTTTCAGGGC | SEQ ID NO:22656 AAGTTTGGGGAC |
| | | AA | SEQ ID NO:6633 SYNMH | SEQ ID NO:14645 WINPNNGGSNYTQKFQG | SEQ ID NO:22657 KFGD |
| | | | SEQ ID NO:6634 | SEQ ID NO:14646 | SEQ ID NO:22658 |

FIGURE 49
(Continued)

| | | | | | |
|---|---|---|---|---|---|
| iPS:435887 | 21-225_186F7 | NA | ACCTATGGCATGCAC | ATTATATGGTATGATGG AAGTTATAAATATATGC AGACTCCGTGAAGGGC | GATCATTACGATTTTGGGAG TGGGCACTTTGACTAC |
| | | | SEQ ID NO:6635 | SEQ ID NO:14647 | SEQ ID NO:22659 |
| | | AA | TYGMH | IIWYDGSYKYYADSVKG | DHYDFWSGHFDY |
| | | | SEQ ID NO:6636 | SEQ ID NO:14648 | SEQ ID NO:22660 |
| iPS:435889 | 21-225_186A11 | NA | AGCTATGCCATGAGT | GTTATTAGTGGTAGAGG TGGTACCACATTCTACGC AGACTCCGTGAAGGGC | CGGACTGGGGATGATGTTT TGATATC |
| | | | SEQ ID NO:6637 | SEQ ID NO:14649 | SEQ ID NO:22661 |
| | | AA | SYAMS | VISGRGGTFYADSVKG | RTGDDVFDI |
| | | | SEQ ID NO:6638 | SEQ ID NO:14650 | SEQ ID NO:22662 |
| iPS:435891 | 21-225_188H5 | NA | AGCTACAATATGCAC | TGGATCAACCCTAACAG TGGTGGCTCAAACTATA CACAGAAGTTTCAGGGC | AAGTTTGGGGAC |
| | | | SEQ ID NO:6639 | SEQ ID NO:14651 | SEQ ID NO:22663 |
| | | AA | SYNMH | WINPNSGGSNYTQKFQG | KFGD |
| | | | SEQ ID NO:6640 | SEQ ID NO:14652 | SEQ ID NO:22664 |
| iPS:435895 | 21-225_188E8 | NA | AGCTCTGCCATGAAC | GTTATTAGTGGTAGTGGT GGTTACACATACTACGC AGACTCCGTGAAGGGC | AGGAACACCGATGATGCTTT TGATATC |
| | | | SEQ ID NO:6641 | SEQ ID NO:14653 | SEQ ID NO:22665 |
| | | AA | SSAMN | VISGSGGYTYYADSVKG | RNTDDAFDI |
| | | | SEQ ID NO:6642 | SEQ ID NO:14654 | SEQ ID NO:22666 |
| iPS:435897 | 21-225_188B9 | NA | AGCTACAATATGCAC | TGGATCAACCCTAACAG TGGTGGCTCAAACTATA CACAGAAGTTTCAGGGC | AAGTTTGGGGAC |
| | | | SEQ ID NO:6643 | SEQ ID NO:14655 | SEQ ID NO:22667 |
| | | AA | SYNMH | WINPNSGGSNYTQKFQG | KFGD |
| | | | SEQ ID NO:6644 | SEQ ID NO:14656 | SEQ ID NO:22668 |

FIGURE 49
(Continued)

| | | | | |
|---|---|---|---|---|
| iPS:435899 | 21-225_188G11 | NA | AGTTATGGCATGCAC | ATTATATGGTATGATGG AAGTTATAAATACTATG CAGACTCCGTGAAGGGC | GAGAGATACGATTTTTGGAG TGGTCATTTTGACTAC |
| | | | SEQ ID NO:6645 | SEQ ID NO:14657 | SEQ ID NO:22669 |
| | | AA | SYGMH | IIWYDGSYKYYADSVKG | ERYDFWSGHFDY |
| | | | SEQ ID NO:6646 | SEQ ID NO:14658 | SEQ ID NO:22670 |
| iPS:435901 | 21-225_189G2 | NA | AACTATGGCATGCAC | ATTATATGGTATGATGG AAGTTATAAATACTATG CAGACTCCGTGAAGGGC | GATCGATTCGATTTTGGAG TGGTTATTCCGACTAC |
| | | | SEQ ID NO:6647 | SEQ ID NO:14659 | SEQ ID NO:22671 |
| | | AA | NYGMH | IIWYDGSYKYYADSVKG | DRFDFWSGYSDY |
| | | | SEQ ID NO:6648 | SEQ ID NO:14660 | SEQ ID NO:22672 |
| iPS:435903 | 21-225_190E2 | NA | GACTACTACATGAGC | TACATTAGTAGTAGTGGT ACTACCGTATTCTACGCA GACTCTGTGAAGGGC | GAATGGGTGGGAGCCGACTA C |
| | | | SEQ ID NO:6649 | SEQ ID NO:14661 | SEQ ID NO:22673 |
| | | AA | DYYMS | YISSSGTTVFYADSVKG | EWVGADY |
| | | | SEQ ID NO:6650 | SEQ ID NO:14662 | SEQ ID NO:22674 |
| iPS:435905 | 21-225_190A3 | NA | AGTGGTGGTTACTACTGGAA C | TTCATCTTTATAGTGGG AGCACCTACTACAACC GTCCCTCAAGAGT | GGGGATTACGATGGTTCGG GAGTTATCACTACTATTACG GTAFGGACGTC |
| | | | SEQ ID NO:6651 | SEQ ID NO:14663 | SEQ ID NO:22675 |
| | | AA | SGGYYWN | FIFYSGSTYYNPSLKS | GDYDGSGSYHYYYGMDV |
| | | | SEQ ID NO:6652 | SEQ ID NO:14664 | SEQ ID NO:22676 |
| iPS:435907 | 21-225_190G3 | NA | AGCTATGGCATGCAC | GTTATATCATATGATGGA GGTTATAAAAACTATGT AGACTCCGTGAAGGGC | GGTACCCACGGGTACTACTA CGGTGTGGACGTC |
| | | | SEQ ID NO:6653 | SEQ ID NO:14665 | SEQ ID NO:22677 |
| | | AA | SYGMH | VISYDGGYKNYVDSVKG | GTHGYYYGVDV |
| | | | SEQ ID NO:6654 | SEQ ID NO:14666 | SEQ ID NO:22678 |

FIGURE 49
(Continued)

| | | | | | |
|---|---|---|---|---|---|
| iPS:435909 | 21-225_190H3 | NA | AGCTATGCCATGAGC | GCTATTAGTGGTGTCGTGGT GGTAACACATACTACG AGACTCCGTGAAGGGC | GATGGATTCGTCGTGGGAGCTC CTATTTGACTAC |
| | | | SEQ ID NO:6655 | SEQ ID NO:14667 | SEQ ID NO:22679 |
| | | AA | SYAMS | AISGRGGNTYYADSVKG | DGFGGSSYFDY |
| | | | SEQ ID NO:6656 | SEQ ID NO:14668 | SEQ ID NO:22680 |
| iPS:435911 | 21-225_190B4 | NA | AGTGGTGATTACTACTGGAGC | TACATCTTTACAGTGGG AGCACCTACTACAACCC GTCCCTCAAGAGT | GGGGATTACGATGGTTCGGG GAGTTATCACTACTACTACG GTATGGACGTC |
| | | | SEQ ID NO:6657 | SEQ ID NO:14669 | SEQ ID NO:22681 |
| | | AA | SGDYYWN | YIFYSGSTYYNPSLKS | GDYDGSGSYHYYYGMDV |
| | | | SEQ ID NO:6658 | SEQ ID NO:14670 | SEQ ID NO:22682 |
| iPS:435913 | 21-225_190A7 | NA | AGTGGTGTTTACTACTGGAGC | AACATCTATTACAGTGG GAGCACCTACAACAACC CGTCCCTCAAGAGT | GGGGATTACGATGGTTCGGG GAGTTATCACTACTACTACG GTTTGGACGTC |
| | | | SEQ ID NO:6659 | SEQ ID NO:14671 | SEQ ID NO:22683 |
| | | AA | SGVYYWS | NIYYSGSTYNNPSLKS | GDYDGSGSYHYYYGLDV |
| | | | SEQ ID NO:6660 | SEQ ID NO:14672 | SEQ ID NO:22684 |
| iPS:435915 | 21-225_190H4 | NA | AATTATGATATCAAC | TGGATGAACCCTAACAG TGGTAACACAGGCTATG CACAGAAGTTCCAGGGC | AGCAGTGGCTGGTACATCTT TGACTAC |
| | | | SEQ ID NO:6661 | SEQ ID NO:14673 | SEQ ID NO:22685 |
| | | AA | NYDIN | WMNPNSGNTGYAQKFQG | SSGWYIFDY |
| | | | SEQ ID NO:6662 | SEQ ID NO:14674 | SEQ ID NO:22686 |
| iPS:435917 | 21-225_190D5 | NA | AATTACTACTGGAGC | CGTATCTATGCCAGTGG GAGCACCAACTACAACC CCTCCCTCAAGAGT | GATCGGGGATACTATGGCTA CTACGGTATGGACGTC |
| | | | SEQ ID NO:6663 | SEQ ID NO:14675 | SEQ ID NO:22687 |
| | | AA | NYYWS | RIYASGSTNYNPSLKS | DRGYYGYYGMDV |

FIGURE 49
(Continued)

| | | | | SEQ ID NO:6664 AGCTATGGCATGCAC | SEQ ID NO:14676 GTTATATCATATGATGGA GGTTATAAAAACTATGC AGACTCCGTGAAGGGC | SEQ ID NO:22688 GGTACCCACGGGTACTACTA CGGTGTGGACGTC |
|---|---|---|---|---|---|---|
| iPS:435919 | 21-225_190H5 | NA | | | | |
| | | AA | | SEQ ID NO:6665 SYGMH | SEQ ID NO:14677 VISYDGGYKNYADSVKG | SEQ ID NO:22689 GTHGYYYGVDV |
| | | | | SEQ ID NO:6666 | SEQ ID NO:14678 | SEQ ID NO:22690 |
| iPS:435921 | 21-225_190D6 | NA | | AGCTTTATCATGCAC | GTTATATGGTATGATGG AAGTAATAAATACTATG CAGACTCCGTGAAGGGC | GAGGAGTATAGCAGTGGCTG GTTCGGGTACGGTATGGACG TC |
| | | AA | | SEQ ID NO:6667 SFIMH | SEQ ID NO:14679 VIWYDGSNKYYADSVKG | SEQ ID NO:22691 EEYSSGWFGYGMDV |
| iPS:435923 | 21-225_190H6 | NA | | SEQ ID NO:6668 GACTACTACATGAGC | SEQ ID NO:14680 TACATTAGTAGTAGTGGT ACTACCGTATTCTACGCA C GACTCTGTGAAGGGC | SEQ ID NO:22692 GAATGGGTGGGAGCCGACTA C |
| | | AA | | SEQ ID NO:6669 DYYMS | SEQ ID NO:14681 YISSSGTTVFYADSVKG | SEQ ID NO:22693 EWVGADY |
| iPS:435925 | 21-225_190D7 | NA | | SEQ ID NO:6670 AATTATGATATCAAC | SEQ ID NO:14682 TGGATGAACCCTAATAG TGGTAATACAGGCTATG CACAGAAGTTCCAGGGC | SEQ ID NO:22694 AGCAGTGGCTGGTACTTCTT TGACTAC |
| | | AA | | SEQ ID NO:6671 NYDIN | SEQ ID NO:14683 WMNPNSGNTGYAQKFQG | SEQ ID NO:22695 SSGWYFFDY |
| | | | | SEQ ID NO:6672 | | SEQ ID NO:22696 |

FIGURE 49
(Continued)

| | | | | | |
|---|---|---|---|---|---|
| iPS:435927 | 21-225_190E7 | NA | AGTTACCACTGGAGT | CATATCTATACCAGTAG GAGCACCAACTACAACC CCTCCCTCAAGAGT | CTCCGGTATAACTGGAACTT CCCTTACTTGACTAC |
| | | | SEQ ID NO:6673 | SEQ ID NO:14685 | SEQ ID NO:22697 |
| | | AA | SYHWS | HIYTSRSTNYNPSLKS | LRYNWNFPYFDY |
| | | | SEQ ID NO:6674 | SEQ ID NO:14686 | SEQ ID NO:22698 |
| iPS:435929 | 21-225_190D9 | NA | AGCTATGCCATGAGT | ACTATTAGTGGTACTGGT CGTAGGACATACTACGC AGACTCCGTGAAGGGC | GAGGAGGATTACTATGATAG TAGTGGCCCGGGGTTCGACC CC |
| | | | SEQ ID NO:6675 | SEQ ID NO:14687 | SEQ ID NO:22699 |
| | | AA | SYAMS | TISGTGRRTYYADSVKG | EEDYYDSSGPGFDP |
| | | | SEQ ID NO:6676 | SEQ ID NO:14688 | SEQ ID NO:22700 |
| iPS:435933 | 21-225_190F8 | NA | ACTTATGGCATGCAC | GTTATATGGTATGATGG AAGTAATAAAAACTATG CAGACTCCGTGAAGGGC | GATCAGGGCGTGGGCTACGA CGGTTGGACGTC |
| | | | SEQ ID NO:6677 | SEQ ID NO:14689 | SEQ ID NO:22701 |
| | | AA | TYGMH | VIWYDGSNKNYADSVKG | DQGVGYDGLDV |
| | | | SEQ ID NO:6678 | SEQ ID NO:14690 | SEQ ID NO:22702 |
| iPS:435935 | 21-225_190H8 | NA | AGCTATGCCATGAGC | ACTATTAGTGGTACTGGT CGTAGGACATATTACGC AGACTCCGTGAAGGGC | GAGGAGGATTACTATGATAG TAGTGGCCCGGGGTTCGACC CC |
| | | | SEQ ID NO:6679 | SEQ ID NO:14691 | SEQ ID NO:22703 |
| | | AA | SYAMS | TISGTGRRTYYADSVKG | EEDYYDSSGPGFDP |
| | | | SEQ ID NO:6680 | SEQ ID NO:14692 | SEQ ID NO:22704 |
| iPS:435937 | 21-225_190H9 | NA | AACTATGGCATGCAC | GTTATATGGTTTGATGGA AGTAATGACTACTATGC AGACTCCGTGAAGGGC | GATAGAAGGTCGGCTACGA CGGTTTAGATGTC |
| | | | SEQ ID NO:6681 | SEQ ID NO:14693 | SEQ ID NO:22705 |

FIGURE 49
(Continued)

| | | AA | NYGMH | VIWFDGSNDYYADSVKG | DRSVGYDGLDV |
|---|---|---|---|---|---|
| iPS:435939 | 21-225_191H7 | | SEQ ID NO:6682 | SEQ ID NO:14694 | SEQ ID NO:22706 |
| | | NA | AGTGGTGGTTGATTACTACTGGAAC | TACATCTTTTACAGTGGGAGCACCTACTACAACCCGTCCCTCAAGAGT | GGGGATTACGATGGTTCGGGAGTTATCACTACTATTACGGTATGGACGTC |
| | | | SEQ ID NO:6683 | SEQ ID NO:14695 | SEQ ID NO:22707 |
| | | AA | SGDYYWN | YIFYSGSTYYNPSLKS | GDYDGSGSYHYYGMDV |
| iPS:435941 | 21-225_191E8 | | SEQ ID NO:6684 | SEQ ID NO:14696 | SEQ ID NO:22708 |
| | | NA | AACTATGGCATGCAC | ATTATATGGTTTGATGGAAGTAATCAATACTATGCCGACTCCGTGAAGGGC | GCCCACGGGGTCTACTACTACGCCATGGACGTC |
| | | | SEQ ID NO:6685 | SEQ ID NO:14697 | SEQ ID NO:22709 |
| | | AA | NYGMH | HWFDGSNQYYADSVKG | AHGVYYYAMDV |
| iPS:435943 | 21-225_191C9 | | SEQ ID NO:6686 | SEQ ID NO:14698 | SEQ ID NO:22710 |
| | | NA | AGTGGTGGTTACTACTGGAAC | TATATCTATTACAGTGGGAGCACCTACTACAACCCGTCCCTCAAGAGT | TCCGGGTATAATTGGGACGCCGGGGTCGACCCC |
| | | | SEQ ID NO:6687 | SEQ ID NO:14699 | SEQ ID NO:22711 |
| | | AA | SGGYYWN | YIYYSGSTYYNPSLKS | SGYNWDAGVDP |
| iPS:435945 | 21-225_191A10 | | SEQ ID NO:6688 | SEQ ID NO:14700 | SEQ ID NO:22712 |
| | | NA | AGCTATGGCATGCAC | GTTTATATGGTATGATGGAAGTAATAAAAACTACGCAGACTCCGTGAAGGGC | GATCAGGGGCGTGGGCTACGACGGTTTGGACGTC |
| | | | SEQ ID NO:6689 | SEQ ID NO:14701 | SEQ ID NO:22713 |
| | | AA | SYGMH | VIWYDGSNKNYADSVKG | DQGVGYDGLDV |
| | | | SEQ ID NO:6690 | SEQ ID NO:14702 | SEQ ID NO:22714 |

FIGURE 49
(Continued)

| | | | | | |
|---|---|---|---|---|---|
| iPS:435947 | 21-225_191E10 | NA | AGCTATGGCATGCAC | GTTATATGGTATGATGGAAGTAATAAAACTACGCAGACTCCGTGAAGGGC | GATCAGGGGCGTGGGCTACGACGGTTTGGACGTC |
| | | | SEQ ID NO:6691 | SEQ ID NO:14703 | SEQ ID NO:22715 |
| | | AA | SYGMH | VIWYDGSNKNYADSVKG | DQGVGYDGLDV |
| | | | SEQ ID NO:6692 | SEQ ID NO:14704 | SEQ ID NO:22716 |
| iPS:435953 | 21-225_191B12 | NA | GACTACTACATGAGC | TACATTAGTAGTAGTGGTACTACCGTATTCTACGCACGACTCTGTGAAGGGC | GAATGGGTGGGAGCCGACTAC |
| | | | SEQ ID NO:6693 | SEQ ID NO:14705 | SEQ ID NO:22717 |
| | | AA | DYYMS | YISSSGTTVFYADSVKG | EWVGADY |
| | | | SEQ ID NO:6694 | SEQ ID NO:14706 | SEQ ID NO:22718 |
| iPS:435957 | 21-225_191G12 | NA | AGCTATGGCATGCAC | GTTATATGGTATGATGGAAGTAATAAAACTATGCAGACTCCGTGAAGGGC | GATCAGGGGCGTGGGCTACGACGGTTTGGACGTC |
| | | | SEQ ID NO:6695 | SEQ ID NO:14707 | SEQ ID NO:22719 |
| | | AA | SYGMH | VIWYDGSNKNYADSVKG | DQGVGYDGLDV |
| | | | SEQ ID NO:6696 | SEQ ID NO:14708 | SEQ ID NO:22720 |
| iPS:435961 | 21-225_192A2 | NA | AGCTATGGCATGCAC | GTTATATGGTATGATGGAAGTTATAAATACTATGCAGACTCCGTGAAGGGC | GAGGATTCCCCTTATAGTGGCTACGCCTTGGACTACTTCTACGGTATGGACGTC |
| | | | SEQ ID NO:6697 | SEQ ID NO:14709 | SEQ ID NO:22721 |
| | | AA | SYGMH | VIWYDGSYKYYADSVKG | EDSPYSGYALDYFYGMDV |
| | | | SEQ ID NO:6698 | SEQ ID NO:14710 | SEQ ID NO:22722 |

FIGURE 49
(Continued)

| | | | | | |
|---|---|---|---|---|---|
| iPS:435963 | 21-225_192D2 | NA | AGCTATGGCATGCAC | GTTATATGGTATGATGG AAGTAATAAAACTATG CAGACTCCGTGAAGGGC | GATCGTGGGGTTGGCTACTA CGGTATGGACGTC |
| | | | SEQ ID NO:6699 | SEQ ID NO:14711 | SEQ ID NO:22723 |
| | | AA | SYGMH | VIWYDGSNKNYADSVKG | DRGVGYYGMDV |
| | | | SEQ ID NO:6700 | SEQ ID NO:14712 | SEQ ID NO:22724 |
| iPS:435965 | 21-225_192H2 | NA | AGCTCTGCCATGAGC | GCCATTAGTGGTAGTGG TGGTAACACATTCTACGC AGACTCCGTGAAGGGC | CTCATAGCAGTAGTGGGTC CCACTACTTTGACTAC |
| | | | SEQ ID NO:6701 | SEQ ID NO:14713 | SEQ ID NO:22725 |
| | | AA | SSAMS | AISGSGGNTFYADSVKG | LIAVVGSHYFDY |
| | | | SEQ ID NO:6702 | SEQ ID NO:14714 | SEQ ID NO:22726 |
| iPS:435967 | 21-225_192B3 | NA | AGTGGTGATTACTACTGGAA C | TTCATCTTTACAGTGGG AGCACCTACTACAACCC GTCCCTCAAGAGT | GGGGATTACGATGGTTCGG GAGTTATCACCACTACTACG GTATGGACGTC |
| | | | SEQ ID NO:6703 | SEQ ID NO:14715 | SEQ ID NO:22727 |
| | | AA | SGDYYWN | FIFYSGSTYYNPSLKS | GDYDGSGSYHHYYGMDV |
| | | | SEQ ID NO:6704 | SEQ ID NO:14716 | SEQ ID NO:22728 |
| iPS:435971 | 21-225_192D3 | NA | AGCTATGGCATGCAC | GTTATATGGTATGATGG AAGTAATGAACACTATG CAGACTCCGTGAAGGGC | GATAGGGGGGGTGGGTTACTA CGGTTTGGACGTC |
| | | | SEQ ID NO:6705 | SEQ ID NO:14717 | SEQ ID NO:22729 |
| | | AA | SYGMH | VIWYDGSNEHYADSVKG | DRGVGYYGLDV |
| | | | SEQ ID NO:6706 | SEQ ID NO:14718 | SEQ ID NO:22730 |

FIGURE 49
(Continued)

| iPS:435973 | 21-225_192H3 | NA | AGTGTTAGTTACTACTGGAGC | AACCTCTATTACAGTGGGAGCACTACAACCCGTCCCTCAGGAGT | GGGGATTACGATGGTTCGGGGAGTTATCACTACTACCACGGTATGGACGTC |
|---|---|---|---|---|---|
| | | | SEQ ID NO:6707 | SEQ ID NO:14719 | SEQ ID NO:22731 |
| | | AA | SVSYYWS | NLYYSGSTYYNPSLRS | GDYDGSGSYHYYHGMDV |
| | | | SEQ ID NO:6708 | SEQ ID NO:14720 | SEQ ID NO:22732 |
| iPS:435977 | 21-225_192E4 | NA | AGTTATGGCATGCAC | GTTATATGGTATGATGGAAGTAACAAAAACTATGTAGACTCCGTGAGGGGC | GATAGAAGGCGTCGGCTACGACGGTATGGACGTC |
| | | | SEQ ID NO:6709 | SEQ ID NO:14721 | SEQ ID NO:22733 |
| | | AA | SYGMH | VIWYDGSNKNYVDSVRG | DRSVGYDGMDV |
| | | | SEQ ID NO:6710 | SEQ ID NO:14722 | SEQ ID NO:22734 |
| iPS:435979 | 21-225_192H4 | NA | AGCTATGGCATGCAC | GTTATATGGTATGATGGAAGCAATAAAACTATGCAGACTCCGTGAAGGGC | GATCAAGGTGTGGGGTACTACGGTATGGACGTC |
| | | | SEQ ID NO:6711 | SEQ ID NO:14723 | SEQ ID NO:22735 |
| | | AA | SYGMH | VIWYDGSNKNYADSVKG | DQGVGYYGMDV |
| | | | SEQ ID NO:6712 | SEQ ID NO:14724 | SEQ ID NO:22736 |
| iPS:435983 | 21-225_192E5 | NA | AATGGTGGATACTACTGGAGC | TACATCTTTTACAGCGGGAGCACTACAACCCGTCCCTCAAGAGT | GCGGGATATAACTGGGACAACGGGTTTGACTAC |
| | | | SEQ ID NO:6713 | SEQ ID NO:14725 | SEQ ID NO:22737 |
| | | AA | NGGYYWS | YIFYSGSTYYNPSLKS | AGYNWDNGFDY |
| | | | SEQ ID NO:6714 | SEQ ID NO:14726 | SEQ ID NO:22738 |

FIGURE 49
(Continued)

| iPS:435985 | 21-225_192F6 | NA | AGCTTTATCATGCAC SEQ ID NO:6715 | GTTATATGGTATGATGG AAGTAATAAATACTATG TAGACTCCGTGAAGGGC SEQ ID NO:14727 | GAGGAGTATAGTAGCGGCTG GTTCGGGTACGGTATGGACG TC SEQ ID NO:22739 |
|---|---|---|---|---|---|
| | | AA | SFIMH | VIWYDGSNKYYVDSVKG SEQ ID NO:14728 | EEYSSGWFGYGMDV SEQ ID NO:22740 |
| iPS:435987 | 21-225_192G6 | NA | AGCTATGGCATGCAC SEQ ID NO:6716 | GTTTATGTATGATGATGGA ACTAATAAAAACTATGC AGACTCCGTGAAGGGC SEQ ID NO:14729 | GATCAGGGCGTGGGCTACGA CGGTTTGGACGTC SEQ ID NO:22741 |
| | | AA | SYGMH SEQ ID NO:6717 | VLWYDGTNKNYADSVKG SEQ ID NO:14730 | DQGVGYDGLDV SEQ ID NO:22742 |
| iPS:435989 | 21-225_192F7 | NA | AGCTATGGCATGCAC SEQ ID NO:6718 | GTTATATCATATGATGGA GGTTATAAAAACTATGC AGACTCCGTGAAGGGC SEQ ID NO:14731 | GGTACCCACGGGTACTACTA CGGTGTGGACGTC SEQ ID NO:22743 |
| | | AA | SYGMH SEQ ID NO:6719 | VISYDGGYKNYADSVKG SEQ ID NO:14732 | GTHGYYYGVDV SEQ ID NO:22744 |
| iPS:435993 | 21-225_192C8 | NA | AGCTATGGCATGCAC SEQ ID NO:6720 | GTTATATGGTATGATGG AAGTAATGAACACTATG CAGACTCCGTGAAGGGC SEQ ID NO:14733 | GATAGGGAGTGGGTTACTA CGGTATGGACGTC SEQ ID NO:22745 |
| | | AA | SYGMH SEQ ID NO:6721 | VIWYDGSNEHYADSVKG SEQ ID NO:14734 | DRGVGYYGMDV SEQ ID NO:22746 |
| | | | SEQ ID NO:6722 | | |

FIGURE 49
(Continued)

| | | | | |
|---|---|---|---|---|
| iPS:435995 | 21-225_192F8 | NA | GGTTGCTACTGGAGC | GAAATCAATCAAAGTGG AAGGTCAACTACAACC CGTCCCTCAAGAGT | GACTACGGTGTCTTTGACTA C |
| | | | SEQ ID NO:6723 | SEQ ID NO:14735 | SEQ ID NO:22747 |
| | | AA | GCYWS | EINQSGRSNYNPSLKS | DYGVFDY |
| | | | SEQ ID NO:6724 | SEQ ID NO:14736 | SEQ ID NO:22748 |
| iPS:435997 | 21-225_192G8 | NA | AGCTATGGCATGCAC | GTTATATGGTAFGATGG AAGTAATAAAAACTATG CAGACTCCGTGAAGGGC | GATCAGGGCGTGGGCTACGA CGGTTTGGACGTC |
| | | | SEQ ID NO:6725 | SEQ ID NO:14737 | SEQ ID NO:22749 |
| | | AA | SYGMH | VIWYDGSNKNYADSVKG | DQGVGYDGLDV |
| | | | SEQ ID NO:6726 | SEQ ID NO:14738 | SEQ ID NO:22750 |
| iPS:435999 | 21-225_192F9 | NA | AGCTACCACTGGAGC | CTTATCTATACTAGTAGG AGCACCAATTACAACCC CTCCCTCAAGAGT | CTCCGGTATAACTGGAACTT CCCTTACTTGACTAC |
| | | | SEQ ID NO:6727 | SEQ ID NO:14739 | SEQ ID NO:22751 |
| | | AA | SYHWS | LIYTSRSTNYNPSLKS | LRYNWNFPYFDY |
| | | | SEQ ID NO:6728 | SEQ ID NO:14740 | SEQ ID NO:22752 |
| iPS:436001 | 21-225_192C10 | NA | AACTATGGCATGCAC | GTTATATGGTTTGATGGA AGTAATGACTACTATGC AGACTCCGTGAAGGGC | GATAGAAGCGTCGGCTACGA CGGTTTAGATGTC |
| | | | SEQ ID NO:6729 | SEQ ID NO:14741 | SEQ ID NO:22753 |
| | | AA | NYGMH | VIWFDGSNDYYADSVKG | DRSVGYDGLDV |
| | | | SEQ ID NO:6730 | SEQ ID NO:14742 | SEQ ID NO:22754 |
| iPS:436003 | 21-225_192G10 | NA | AGCTATGCCATGAGC | GCTATTAGTGGTAGTAGA CGGTAGTACATTCTACGC AGACTCCGTGAAGGGC | CGTTTAGCACTGGATGGCTA TGATGCTTTTGATATC |
| | | | SEQ ID NO:6731 | SEQ ID NO:14743 | SEQ ID NO:22755 |

FIGURE 49
(Continued)

| | | AA | SYAMS | | AISGRGGSTFYADSVKG | | RLALDGYDAFDI | |
|---|---|---|---|---|---|---|---|---|
| iPS:436005 | | | SEQ ID NO:6732 | | SEQ ID NO:14744 | | SEQ ID NO:22756 | |
| | 21-225_192H10 | NA | AGCTATGGCATGCAC | | GTTATATGGTATGATGG AAGTAATAAAAACTACG CAGACTCCGTGAAGGGC | | GATCAGGGCGGTGGCTACGA CGGTTTGGACGTC | |
| | | | SEQ ID NO:6733 | | SEQ ID NO:14745 | | SEQ ID NO:22757 | |
| | | AA | SYGMH | | VIWYDGSNKNYADSVKG | | DQGVGYDGLDV | |
| iPS:436007 | | | SEQ ID NO:6734 | | SEQ ID NO:14746 | | SEQ ID NO:22758 | |
| | 21-225_192G12 | NA | AGTGGTGTTTACCACTGGAG C | | AACATCCATTACAGCGG GAGCACCTACAACAACC CGTCCCTCAAGAGT | | GGGGATTACGATGGTTCGGG GAGTTATCACTACTACTACG GTATGGACGTC | |
| | | | SEQ ID NO:6735 | | SEQ ID NO:14747 | | SEQ ID NO:22759 | |
| | | AA | SGVYHWS | | NIHYSGSTYNNPSLKS | | GDYDGSGSYHYYYGMDV | |
| iPS:436009 | | | SEQ ID NO:6736 | | SEQ ID NO:14748 | | SEQ ID NO:22760 | |
| | 21-225_193A1 | NA | AGTGGTGTTTACTACTGGAG C | | AACATCTATTACAGTGG GAGCACCTACAACAACC CGTCCCTCAAGAGT | | GGGGATTACGATGGTTCGGG GAGTTATCACTACTACTACG GTATGGACGTC | |
| | | | SEQ ID NO:6737 | | SEQ ID NO:14749 | | SEQ ID NO:22761 | |
| | | AA | SGVYYWS | | NIYYSGSTYNNPSLKS | | GDYDGSGSYHYYYGMDV | |
| iPS:436011 | | | SEQ ID NO:6738 | | SEQ ID NO:14750 | | SEQ ID NO:22762 | |
| | 21-225_193B1 | NA | AGTGGTGTTTACTACTGGAG C | | AACATCTATTACAGTGG GAGCACCTACAACAACC CGTCCCTCAAGAGT | | GGGGATTACGATGGTTCGGG GAGTTATCACTACTACTACG GTATGGACGTC | |
| | | | SEQ ID NO:6739 | | SEQ ID NO:14751 | | SEQ ID NO:22763 | |
| | | AA | SGVYYWS | | NIYYSGSTYNNPSLKS | | GDYDGSGSYHYYYGMDV | |
| | | | SEQ ID NO:6740 | | SEQ ID NO:14752 | | SEQ ID NO:22764 | |

FIGURE 49
(Continued)

| | | | | | |
|---|---|---|---|---|---|
| iPS:436013 | 21-225_193F2 | NA | ACCTTTGCCATGAGT | GCTATTAGTCGTAGTGGT GGTAACACACACTACGC AGACTCCGTGAAGGGC | GATGGATTCGTGGAGCTC CTACTTTGACTAC |
| | | | SEQ ID NO:6741 | SEQ ID NO:14753 | SEQ ID NO:22765 |
| | | AA | TFAMS | AISRSGGNTHYADSVKG | DGFGGSSYFDY |
| | | | SEQ ID NO:6742 | SEQ ID NO:14754 | SEQ ID NO:22766 |
| iPS:436015 | 21-225_193D3 | NA | AGTGGTGATTACTACTGGAAC | TACATCTTTACAGTGGG AGCACCTACTACAACCC GTCCCTCAAGAGT | GGGGATTACGATGGTTCGGG GAGTTATCACTTCTACTACG GTATGGACGTC |
| | | | SEQ ID NO:6743 | SEQ ID NO:14755 | SEQ ID NO:22767 |
| | | AA | SGDYYWN | YIFYSGSTYYNPSLKS | GDYDGSGSYHFYYGMDV |
| | | | SEQ ID NO:6744 | SEQ ID NO:14756 | SEQ ID NO:22768 |
| iPS:436017 | 21-225_193F3 | NA | AGTGGTGATTACTACTGGAAC | TACATCTTTACAGTGGG AGCACCTACTACAACCC GTCCCTCAAGAGT | GGGGATTACGATGGTTCGGG GAGTTATCACTACTATTACG GTATGGACGTC |
| | | | SEQ ID NO:6745 | SEQ ID NO:14757 | SEQ ID NO:22769 |
| | | AA | SGDYYWN | YIFYSGSTYYNPSLKS | GDYDGSGSYHYYYGMDV |
| | | | SEQ ID NO:6746 | SEQ ID NO:14758 | SEQ ID NO:22770 |
| iPS:436019 | 21-225_193C4 | NA | AGCTATGCCATGAAC | GCTATTATTGGTAATGGT GGTAGAACATATACGGC AGACTCCGTGAAGGGC | GATCTGGGTAGATACAGCTA TGGTTTCTTTGACTAC |
| | | | SEQ ID NO:6747 | SEQ ID NO:14759 | SEQ ID NO:22771 |
| | | AA | SYAMN | AIIGNGGRTYYADSVKG | DLGRYSYGFFDY |
| | | | SEQ ID NO:6748 | SEQ ID NO:14760 | SEQ ID NO:22772 |
| iPS:436021 | 21-225_193G4 | NA | AATTATATGATATCAAC | TGGATGAACCCTAACAG TGGTAACACAGGCTATG CACAGAAGTTCCAGGGC | AGCAGTGGCTGGTACTTCTT TGACTAC |
| | | | SEQ ID NO:6749 | SEQ ID NO:14761 | SEQ ID NO:22773 |
| | | AA | NYDIN | WMNPNSGNTGYAQKFQG | SSGWYFFDY |

FIGURE 49
(Continued)

| | | | | | | |
|---|---|---|---|---|---|---|
| iPS:436023 | 21-225_193A5 | NA | SEQ ID NO:6750 AGTTATGATATCAAC | SEQ ID NO:14762 TGGATGAACCCTAAAAG GGTAACACAGGCTATG CACAGAAGTTCCAGGGC | SEQ ID NO:22774 GGAGACCCGTATAACTGGAA CTCCTACGCTATGGACGTC |
| | | AA | SEQ ID NO:6751 SYDIN | SEQ ID NO:14763 WMNPKRGNTGYAQKFQG | SEQ ID NO:22775 GDPYNWNSYAMDV |
| iPS:436025 | 21-225_193B5 | NA | SEQ ID NO:6752 AGTGGTGGTTACTACTGGAG C | SEQ ID NO:14764 TACATCTATTACAGTGGG AGCACCTACTACAACCC AGCACCTACAAGAGT | SEQ ID NO:22776 GGAGAGTATAACTGGAACCA CGGTATGGACGTC |
| | | AA | SEQ ID NO:6753 SGGYYWS | SEQ ID NO:14765 YIYYSGSTYYNPSLKS | SEQ ID NO:22777 GEYNWNHGMDV |
| | | | SEQ ID NO:6754 | SEQ ID NO:14766 | SEQ ID NO:22778 |
| iPS:436027 | 21-225_193E6 | NA | SEQ ID NO:6755 GGTCCCTACTGGAGT | SEQ ID NO:14767 GAATCCAATCATAGTGG ACGCACCAACTACAACC CGTCCCTCAAGAGT | SEQ ID NO:22779 GACTACGGTGGTTTGGACTA C |
| | | AA | SEQ ID NO:6756 GPYWS | SEQ ID NO:14768 ESNHSGRTNYNPSLKS | SEQ ID NO:22780 DYGGLDY |
| iPS:436029 | 21-225_193H6 | NA | SEQ ID NO:6757 AGTGGTGATTACTACTGGAA C | SEQ ID NO:14769 TACATCTTTTACAGTGGG AGCACCTACTACAACCC GTCCCTCAAGAGT | SEQ ID NO:22781 GGGGATTACGATGGTTCGGG GAGTTATCACTACTATTACG GTATGGACGTC |
| | | AA | SEQ ID NO:6758 SGDYYWN | SEQ ID NO:14770 YIFYSGSTYYNPSLKS | SEQ ID NO:22782 GDYDGSGSYHYYYGMDV |

FIGURE 49
(Continued)

| | | NA | AGCTATGGCATGCAC | GTTATATGGTATGATGG AAGTAATAAAAACTACG CAGACTCCGTGAAGGGC | GATCAGGGCGTGGCTACGA CGGCTTGGACGTC |
|---|---|---|---|---|---|
| iPS:436031 | 21-225_193C7 | | SEQ ID NO:6759 | SEQ ID NO:14771 | SEQ ID NO:22783 |
| | | AA | SYGMH | VIWYDGSNKNYADSVKG | DQGVGYDGLDV |
| | | | SEQ ID NO:6760 | SEQ ID NO:14772 | SEQ ID NO:22784 |
| | | NA | GGTTACTTCTGGACC | GAAATCAATAATCATAGTGG AAGCACCAACTACACC CGTCCCTCAAGAGT | GACTACGGTGCTGACTAC |
| iPS:436033 | 21-225_193E7 | | SEQ ID NO:6761 | SEQ ID NO:14773 | SEQ ID NO:22785 |
| | | AA | GYFWT | EINHSGSTNYNPSLKS | DYGADY |
| | | | SEQ ID NO:6762 | SEQ ID NO:14774 | SEQ ID NO:22786 |
| | | NA | AGTGGTGATTACTGGAA C | TACATCTTTACAGTGGG AGCACCTACTACAACCC GTCCCTCAAGAGT | GGGGATTACGATGGTTCGGG GAGTTATCACTACTACTACG GTATGGACGTC |
| iPS:436035 | 21-225_193G8 | | SEQ ID NO:6763 | SEQ ID NO:14775 | SEQ ID NO:22787 |
| | | AA | SGDYYWN | YIFYSGSTYYNPSLKS | GDYDGSGSYHYYYGMDV |
| | | | SEQ ID NO:6764 | SEQ ID NO:14776 | SEQ ID NO:22788 |
| | | NA | AGTGGTGGTTACTGGAA C | TTCATCTTTACAGTGGG AGCACCTACTACAACCC GTCCCTCAAGAGT | GGGGATTACGATGGTTCGGG GAGTTATCACTACTACTATACG GTATGGACGTC |
| iPS:436037 | 21-225_193D8 | | SEQ ID NO:6765 | SEQ ID NO:14777 | SEQ ID NO:22789 |
| | | AA | SGGYYWN | FIFYSGSTYYNPSLKS | GDYDGSGSYHYYYGMDV |
| | | | SEQ ID NO:6766 | SEQ ID NO:14778 | SEQ ID NO:22790 |
| | | NA | ATCTATGGCATGGAC | GTTATATGGTATGATGG AAGTTATAAATACTATG CAGACTCCGTGAAGGGC | GAGGATTCCCCTTATAGTGG CTACGGCTTGGACTACTACT ACGGTATGGACGTC |
| iPS:436039 | 21-225_193F8 | | SEQ ID NO:6767 | SEQ ID NO:14779 | SEQ ID NO:22791 |

FIGURE 49 (Continued)

| | | | | | | | | |
|---|---|---|---|---|---|---|---|---|
| iPS:436041 | 21-225_193G8 | AA | IYGMD | SEQ ID NO:6768 | VIWYDGSYKYYADSVKG | SEQ ID NO:14780 | EDSPYSGYGLDYYYGMDV | SEQ ID NO:22792 |
| | | NA | AGTGTGTTTACTACTGGAG C | SEQ ID NO:6769 | AACATCTATTACAGTGG GAGCACCTACAACAACC CGTCCCTCAAGAGT | SEQ ID NO:14781 | GGGGATTACGATGGTTCGGG GAGTTATCACTTCTACTACG GTTTGGACGTC | SEQ ID NO:22793 |
| iPS:436043 | 21-225_193G9 | AA | SGVYYWS | SEQ ID NO:6770 | NIYYSGSTYNNPSLKS | SEQ ID NO:14782 | GDYDGSGSYHFYYGLDV | SEQ ID NO:22794 |
| | | NA | AATGGTGGATACTACTGGAG C | SEQ ID NO:6771 | TACATCTTTTACAGCGGG AGCACCTACAACCC GTCCCTCAAGAGT | SEQ ID NO:14783 | GCGGGATATAACTGGGACAA CGGGTTTGACTAC | SEQ ID NO:22795 |
| iPS:436045 | 21-225_193A10 | AA | NGGYYWS | SEQ ID NO:6772 | YIFYSGSTYYNPSLKS | SEQ ID NO:14784 | AGYNWDNGFDY | SEQ ID NO:22796 |
| | | NA | AGCTATGGCATGCAC | SEQ ID NO:6773 | GTTATATGGTATGATGG AAGTAATGAACACTATG CAGACTCCGTGAAGGGC | SEQ ID NO:14785 | GATAGGGGGGTGGGTTACTA CGGTTTGGACGTC | SEQ ID NO:22797 |
| iPS:436047 | 21-225_193B10 | AA | SYGMH | SEQ ID NO:6774 | VIWYDGSNEHYADSVKG | SEQ ID NO:14786 | DRGVGYYGLDV | SEQ ID NO:22798 |
| | | NA | GACTATAGCATGAAC | SEQ ID NO:6775 | TCCATTAGTAGTGCTGGT GGTTACATATACTACGC AGACTCACTGAAGGGC | SEQ ID NO:14787 | GCAACTATGGCCCTTGACTA C | SEQ ID NO:22799 |
| | | AA | DYSMN | SEQ ID NO:6776 | SISSAGGYIYYADSLKG | SEQ ID NO:14788 | ATMALDY | SEQ ID NO:22800 |

FIGURE 49
(Continued)

| | | | | | |
|---|---|---|---|---|---|
| iPS:436049 | 21-225_193B12 | NA | AGTGCTGATTACTACTGGAAC | TACATCTTTTACAGTGGGAGCACCTACTACAACCCGTCCCCTCAAGAGT | GGGGATTACGATGGTTCGGGAGTTATCACTTCTACTACGGTATGGACGTC |
| | | | SEQ ID NO:6777 | SEQ ID NO:14789 | SEQ ID NO:22801 |
| | | AA | SADYYWN | YIFYSGSTYYNPSLKS | GDYDGSGSYHFYYGMDV |
| | | | SEQ ID NO:6778 | SEQ ID NO:14790 | SEQ ID NO:22802 |
| iPS:436051 | 21-225_193G12 | NA | AGCTATGCCATGCAC | GTTATATGGTATGATGGAACTAATAAATACTATGGAGACTCCGTGAAGGGC | GATTTCACTATAAACTGGAGCTACATATTTTGACTAC |
| | | | SEQ ID NO:6779 | SEQ ID NO:14791 | SEQ ID NO:22803 |
| | | AA | SYAMH | VIWYDGTNKYYGDSVKG | DFTITGATYFDY |
| | | | SEQ ID NO:6780 | SEQ ID NO:14792 | SEQ ID NO:22804 |
| iPS:436054 | 21-225_194C1 | NA | AGCTATGGCATGCAC | GTTATATGGTATGATGGAAGTAATGAACACTATGCAGACTCCGTGAAGGGC | AATAGGGGGGTGGGTTACTACGGTTTGGACGTC |
| | | | SEQ ID NO:6781 | SEQ ID NO:14793 | SEQ ID NO:22805 |
| | | AA | SYGMH | VIWYDGSNEHYADSVKG | NRGVGYYGLDV |
| | | | SEQ ID NO:6782 | SEQ ID NO:14794 | SEQ ID NO:22806 |
| iPS:436056 | 21-225_194C3 | NA | AATTACTACTGGAGC | CGTATCTATGCCAGTGGGAGCACCAACTACAACCCCTCCCTCAAGAGT | GATCGGGGATACTATGGCTACTACGGTATGGACGTC |
| | | | SEQ ID NO:6783 | SEQ ID NO:14795 | SEQ ID NO:22807 |
| | | AA | NYYWS | RIYASGSTNYNPSLKS | DRGYYGYYGMDV |
| | | | SEQ ID NO:6784 | SEQ ID NO:14796 | SEQ ID NO:22808 |

FIGURE 49
(Continued)

| | | NA/AA | | | |
|---|---|---|---|---|---|
| iPS:436058 | 21-225_194A4 | NA | GTCTACTATTTGAAC | TGGATCAACCCTAACAGTGGTGGCACAAACTATGCACAGAAGTTTCAGGGC | GGCTACGATATTTGACTGGT |
| | | | SEQ ID NO:6785 | SEQ ID NO:14797 | SEQ ID NO:22809 |
| | | AA | VYYLN | WINPNSGGTNYAQKFQG | GYDILFG |
| | | | SEQ ID NO:6786 | SEQ ID NO:14798 | SEQ ID NO:22810 |
| iPS:436060 | 21-225_194F4 | NA | AGTTACCACTGGAGC | CTTATCTATACCAGTAGGAGCACCAACTACACAACCCCTCCCTCAAGAGT | CTCCGGTATAACTGGAACTTCCCTTACTTTGACTAC |
| | | | SEQ ID NO:6787 | SEQ ID NO:14799 | SEQ ID NO:22811 |
| | | AA | SYHWS | LIYTSRSTNYNPSLKS | LRYNWNFPYFDY |
| | | | SEQ ID NO:6788 | SEQ ID NO:14800 | SEQ ID NO:22812 |
| iPS:436062 | 21-225_194E5 | NA | AGTGGTGATTACTACTGGAAC | TACATCTTTTACAGTGGGAGCACCTACTACAACCCGTCCCTCAAGAGT | GGGGATTACGATGGTTCGGGGAGTTATCACTACTATTACGGTATGGACGTC |
| | | | SEQ ID NO:6789 | SEQ ID NO:14801 | SEQ ID NO:22813 |
| | | AA | SGDYYWN | YIFYSGSTYYNPSLKS | GDYDGSGSYHYYYGMDV |
| | | | SEQ ID NO:6790 | SEQ ID NO:14802 | SEQ ID NO:22814 |
| iPS:436064 | 21-225_194E6 | NA | AGTGGTGATTACTACTGGAAC | TTCATCTTTTACAGTGGGAGCACCTACTACAACCCGTCCCTCAAGAGT | GGGGATTACGATGGTTCGGGGAGTTATCACTACTATTACGGTATGGACGTC |
| | | | SEQ ID NO:6791 | SEQ ID NO:14803 | SEQ ID NO:22815 |
| | | AA | SGDYYWN | FIFYSGSTYYNPSLKS | GDYDGSGSYHYYYGMDV |
| | | | SEQ ID NO:6792 | SEQ ID NO:14804 | SEQ ID NO:22816 |
| iPS:436066 | 21-225_194B7 | NA | AGTATGGCATGCAC | GTTATATGGTATGATGGAAGTAATAAAAACTATGCAGACTCCGTGAAGGGC | GATCGGTCTAAGGGGTTACGACGGTATGGACGTC |
| | | | SEQ ID NO:6793 | SEQ ID NO:14805 | SEQ ID NO:22817 |

FIGURE 49
(Continued)

| | | AA | SYGMH | | VIWYDGSNKNYADSVKG | | DRSKGYDGMDV | |
|---|---|---|---|---|---|---|---|---|
| iPS:436068 | | | | SEQ ID NO:6794 | | SEQ ID NO:14806 | | SEQ ID NO:22818 |
| | 21-225_194F7 | NA | GACTACTACATACAC | | TGGATCAACCTAACAA TGGTGGCACAAACTATG CACAGAAATTTCAGGGC | | GAACCCTTGGTTACTATGG TTCGGGGAGTTATGGGCCT ACGGTATGGACGTC | |
| iPS:436072 | | AA | DYYIH | SEQ ID NO:6795 | WINPNNGGTNYAQKFQG | SEQ ID NO:14807 | EPLGYYGSGSYGAYGMDV | SEQ ID NO:22819 |
| | 21-225_194C10 | NA | TATTACTACTGGAGC | SEQ ID NO:6796 | GAAATCAATCATAGTGG AAGCACCAACTACAACC CGTCCCTCAAGAGT | SEQ ID NO:14808 | GACTACGGTGCTTTTGATAT C | SEQ ID NO:22820 |
| iPS:436074 | | AA | YYYWS | SEQ ID NO:6797 | EINHSGSTNYNPSLKS | SEQ ID NO:14809 | DYGAFDI | SEQ ID NO:22821 |
| | 21-225_194F10 | NA | AGCTTTATCATGCAC | SEQ ID NO:6798 | GTTATATGGTATGATGG AAGTAATAAATACTATG CAGACTCCGTGAAGGGC | SEQ ID NO:14810 | GAGGAGTATAGCAGTGGCTG GTTCGGGTACGGTATGGACG TC | SEQ ID NO:22822 |
| iPS:436076 | | AA | SFIMH | SEQ ID NO:6799 | VIWYDGSNKYYADSVKG | SEQ ID NO:14811 | EEYSSGWFGYGMDV | SEQ ID NO:22823 |
| | 21-225_194H11 | NA | AGCTATGGCATGCAC | SEQ ID NO:6800 | GTTATATGGTATGATGG AAGTAATGAACACTATG CAGACTCCGTGAAGGGC | SEQ ID NO:14812 | GATAGGGGGGTGGGTTATTA CGGTTTGGACGTC | SEQ ID NO:22824 |
| | | | | SEQ ID NO:6801 | | SEQ ID NO:14813 | | SEQ ID NO:22825 |

FIGURE 49
(Continued)

| | | | AA | SYGMH | VIWYDGSNEHYADSVKG | DRGVGYYGLDV |
|---|---|---|---|---|---|---|
| iPS:436078 | 21-225_194H12 | | | SEQ ID NO:6802 | SEQ ID NO:14814 | SEQ ID NO:22826 |
| | | | NA | AACTATGGCATGCAC | GTTATATGGTTTGATGGAAGTAATGACTACTATGCAGACTCCGTGAAGGGC | GATAGAAGCGTCGGCTACGACGGTTTAGATGTC |
| | | | | SEQ ID NO:6803 | SEQ ID NO:14815 | SEQ ID NO:22827 |
| iPS:436080 | 21-225_195B1 | | AA | NYGMH | VIWFDGSNDYYADSVKG | DRSVGYDGLDV |
| | | | | SEQ ID NO:6804 | SEQ ID NO:14816 | SEQ ID NO:22828 |
| | | | NA | TATTACTTCTGGAGC | GAAATCAATCATAGTGGACGCACCAACTACAACCCGTCCCTCAAGAGT | GACTACGGTGCTTTTGATATC |
| | | | | SEQ ID NO:6805 | SEQ ID NO:14817 | SEQ ID NO:22829 |
| iPS:436082 | 21-225_195D9 | | AA | YYFWS | EINHSGRTNYNPSLKS | DYGAFDI |
| | | | | SEQ ID NO:6806 | SEQ ID NO:14818 | SEQ ID NO:22830 |
| | | | NA | CACTATGTCATGCAC | GTTATTGGTATGATGGAACTAATAAATACTATGCAGACTCCGTGAAGGGC | GATTGGTTCGGGGAGGGAACTACTACGGTATGGACGTC |
| | | | | SEQ ID NO:6807 | SEQ ID NO:14819 | SEQ ID NO:22831 |
| iPS:436084 | 21-225_195F2 | | AA | HYVMH | VIWYDGTNKYYADSVKG | DWFGEGNYYGMDV |
| | | | | SEQ ID NO:6808 | SEQ ID NO:14820 | SEQ ID NO:22832 |
| | | | NA | AGCGGTGGTTACTACTGGAGC | TACAGCTATTACAGTGGGAGCACCAACTATAACCCGTCCCTCAAGAGT | GGGGGTATAACTGGAACAACGGGTTTGACTAC |
| | | | | SEQ ID NO:6809 | SEQ ID NO:14821 | SEQ ID NO:22833 |
| | | | AA | SGGYYWS | YSYYSGSTNYNPSLKS | GGYNWNNGFDY |
| | | | | SEQ ID NO:6810 | SEQ ID NO:14822 | SEQ ID NO:22834 |

FIGURE 49
(Continued)

| | | | | |
|---|---|---|---|---|
| iPS:436086 | 21-225_191G10 | NA | AGCTATGGCATGCAC | GTTATATGGTATGATGG AAGTAATAAAAACTATG CAGACTCCGTGAAGGGC | GATCAGGGCGTGGGCTACGA CGGTTTGGACGTC |
| | | | SEQ ID NO:6811 | SEQ ID NO:14823 | SEQ ID NO:22835 |
| | | AA | SYGMH | VIWYDGSNKNYADSVKG | DQGVGYDGLDV |
| | | | SEQ ID NO:6812 | SEQ ID NO:14824 | SEQ ID NO:22836 |
| iPS:436088 | 21-225_195C8 | NA | AGTGGTGATTACTACTGGAA C | TACATCTTTACAGTGGG AGCACCTACTACAACCC GTCCCTCAAGAGT | GGGGATTACGATGGTTCGGG GAGTTATCACTTCTACTACG GTATGGACGTC |
| | | | SEQ ID NO:6813 | SEQ ID NO:14825 | SEQ ID NO:22837 |
| | | AA | SGDYYWN | YIFYSGSTYYNPSLKS | GDYDGSGSYHFYYGMDV |
| | | | SEQ ID NO:6814 | SEQ ID NO:14826 | SEQ ID NO:22838 |
| iPS:436090 | 21-225_195A9 | NA | AGCTATGGCATGCAC | GTTATATGGTATGATGG AAGTAATGAACACTATG CAGACTCCGTGAAGGGC | GATAGGGGGGGTGGGTTACTA CGGTTTGGACGTC |
| | | | SEQ ID NO:6815 | SEQ ID NO:14827 | SEQ ID NO:22839 |
| | | AA | SYGMH | VIWYDGSNEHYADSVKG | DRGVGYYYGLDV |
| | | | SEQ ID NO:6816 | SEQ ID NO:14828 | SEQ ID NO:22840 |
| iPS:436092 | 21-225_195B9 | NA | AGCTATGGCATGCAC | GTTATATGGTATGATGG AAGTAATAAATACTATG CAGACTCCGTGAAGGGC | GAATGGCTACAATTCAGGTA CTACTACGGTATGGACGTC |
| | | | SEQ ID NO:6817 | SEQ ID NO:14829 | SEQ ID NO:22841 |
| | | AA | SYGMH | VIWYDGSNKYYADSVKG | EWLQFRYYGMDV |
| | | | SEQ ID NO:6818 | SEQ ID NO:14830 | SEQ ID NO:22842 |

FIGURE 49
(Continued)

| | | | | | |
|---|---|---|---|---|---|
| iPS:436094 | 21-225_195B10 | NA | AATAGTGGTTACTACTGGAG C SEQ ID NO:6819 | TACATGTGTATTACAGTGG GAGCACCTACTACAACC CGTCCCTCAAGAGT SEQ ID NO:14831 | GGGGGGTATAACTGGAACAA TGGGTTTGACTGT SEQ ID NO:22843 |
| | | AA | NSGYYWS SEQ ID NO:6820 | YMYYSGSTYYNPSLKS SEQ ID NO:14832 | GGYNWNGFDC SEQ ID NO:22844 |
| iPS:436096 | 21-225_195E10 | NA | AGTGGTGGTTACTACTGGAG C SEQ ID NO:6821 | TACATCTATTACAGTGGG AGCACCTACTACAACCC GTCCCTCAAGAGT SEQ ID NO:14833 | GGGGGGTATAACTGGAACCA CGGTATGGACGTC SEQ ID NO:22845 |
| | | AA | SGGYYWS SEQ ID NO:6822 | YIYYSGSTYYNPSLKS SEQ ID NO:14834 | GGYNWNHGMDV SEQ ID NO:22846 |
| iPS:436098 | 21-225_195G11 | NA | GACTACTACATGAGC SEQ ID NO:6823 | TACATTAGTAGTAGTGGT ACTACCGTATTCTACGCA GACTCTGTGAAGGGC SEQ ID NO:14835 | GAATGGGTGGGAGCCGACTA C SEQ ID NO:22847 |
| | | AA | DYYMS SEQ ID NO:6824 | YISSSGTTVFYADSVKG SEQ ID NO:14836 | EWVGADY SEQ ID NO:22848 |
| iPS:436100 | 21-225_195G12 | NA | ACCTATGCCATGAGT SEQ ID NO:6825 | GCTATTAGTCGTAGTGGT GGTAACACACTACGC AGACTCCGTGAAGGGC SEQ ID NO:14837 | GATGGATTCGGTGGGAGCTC CTACTTTGACTAC SEQ ID NO:22849 |
| | | AA | TYAMS SEQ ID NO:6826 | AISRSGGNTHYADSVKG SEQ ID NO:14838 | DGFGGSSYFDY SEQ ID NO:22850 |
| iPS:436102 | 21-225_196B1 | NA | GACTACTACATGAGC SEQ ID NO:6827 | TACATTAGTAGTAGTGGT ATTACCATGTACTACGCA C GACTCTGTGAAGGGC SEQ ID NO:14839 | GAATGGGTGGGAGCCGACTA C SEQ ID NO:22851 |
| | | AA | DYYMS SEQ ID NO:6828 | YISSSGITMYYADSVKG SEQ ID NO:14840 | EWVGADY SEQ ID NO:22852 |

FIGURE 49
(Continued)

| | | | | GACTACTACATGAGC | | TACATTAGTAGTAGTGGT ACTACGTATTCTACGCAC GACTCTGTGAAGGGC | GAATGGGTGGGAGCCGACTA C |
|---|---|---|---|---|---|---|---|
| iPS:436104 | 21-225_196C1 | NA | | | | | |
| | | AA | | DYYMS | SEQ ID NO:6829 | YISSSGTTVFYADSVKG SEQ ID NO:14841 | EWVGADY SEQ ID NO:22853 |
| iPS:436106 | 21-225_196F2 | NA | | AGCTTTGGCATGCAC | SEQ ID NO:6830 | GTTATATTAAATGATGG AAGTAATAAAAGTGTG CAGACTCCGTGAAGGGC | GGACAGCAGTGGCTGGTAAA CGGTGTGGACGTC SEQ ID NO:22854 |
| | | AA | | SFGMH | SEQ ID NO:6831 | VILNDGSNKKCADSVKG SEQ ID NO:14843 | GQQWLVNGVDV SEQ ID NO:22855 |
| iPS:436110 | 21-225_196F4 | NA | | AGCTGTGCCATGACC | SEQ ID NO:6832 | GCTATTAGTGGTAGTGGT GGTAGCACATACTACGC AGACTCCGTGAAGGGC | GTGGGGGTTGACTGGCTC CTACTACTACTACGGTATGG ACGTC SEQ ID NO:22857 |
| | | AA | | SCAMT | SEQ ID NO:6833 | AISGSGGSTYYADSVKG SEQ ID NO:14845 | VGGLTGSYYYYGMDV SEQ ID NO:22857 |
| iPS:436112 | 21-225_196C7 | NA | | AGCTATGGCATGCAC | SEQ ID NO:6834 | GTTATATGGTATGATGG AAGTAATGAACACTATG CAGACTCCGTGAAGGGC | GATAGGGGGGTGGGTTACTA CGGTTTGGACGTC SEQ ID NO:22859 |
| | | AA | | SYGMH | SEQ ID NO:6835 | VIWYDGSNEHYADSVKG SEQ ID NO:14847 | DRGVGYYGLDV SEQ ID NO:22859 |
| iPS:436114 | | NA | | AATTATGATATCAAC | SEQ ID NO:6836 | TGGATGCACTTAACAG TGGTAACACAGGCTATG CACCGAAGTTCCAGGGC | AGCGGTGGCTGGTACGTGTT CGACCCC SEQ ID NO:22860 |

FIGURE 49
(Continued)

| | | | | | | |
|---|---|---|---|---|---|---|
| iPS:436116 | 21-225_196G8 | AA | SEQ ID NO:6837 NYDIN | SEQ ID NO:14849 WMHLNSGNTGYAPKFQG | SEQ ID NO:22861 SGGWYVFDP | |
| | | NA | SEQ ID NO:6838 GGCTACTATATGCAC | SEQ ID NO:14850 TGGATCAACCCTAACAG TGGTGGCACAAACTTTG CACAGAAGTTTCGGGGC | SEQ ID NO:22862 GGGGGGGTTCGGGGAGTTCC CAACTACTACGTTATGG ACGTC | |
| iPS:436118 | 21-225_196B9 | AA | SEQ ID NO:6839 GYYMH | SEQ ID NO:14851 WINPNSGGTNFAQKFRG | SEQ ID NO:22863 GGVRGVPNYYVMDV | |
| | | NA | SEQ ID NO:6840 CACTATGTCATGCAC | SEQ ID NO:14852 GTTATTGGTTATGATGGA ACTAATAAATACTATGC AGACTCCGTGAAGGGC | SEQ ID NO:22864 GATTGGTTCGGGGAGGGGAA CTACTACGGTATGGACGTC | |
| iPS:436120 | 21-225_196A10 | AA | SEQ ID NO:6841 HYVMH | SEQ ID NO:14853 VIWYDGTNKYYADSVKG | SEQ ID NO:22865 DWFGEGNYYGMDV | |
| | | NA | SEQ ID NO:6842 AGTGGTGGTGACTACTGGAG C | SEQ ID NO:14854 TTCATCTATTACAGTGGG AGCACCTACTACAATCC GTCCCTCAAGAGT | SEQ ID NO:22866 ATGGACTACAGTAACTACTA CTACGGTATGGACGTC | |
| iPS:436122 | 21-225_196C10 | AA | SEQ ID NO:6843 SGGDYWS | SEQ ID NO:14855 FIYYSGSTYYNPSLKS | SEQ ID NO:22867 MDYSNYYYGMDV | |
| | | NA | SEQ ID NO:6844 GACTATAGCATGAAC | SEQ ID NO:14856 TCTATTAGTAGTGGTAGT GGTTACATACACTACGC AGACTCAGTGAAGGGC | SEQ ID NO:22868 GCAACTATGGCCCTTGACTA C | |
| iPS:436122 | 21-225_196G10 | AA | SEQ ID NO:6845 DYSMN | SEQ ID NO:14857 SISSGSGYTHYADSVKG | SEQ ID NO:22869 ATMALDY | |
| | | | SEQ ID NO:6846 | SEQ ID NO:14858 | SEQ ID NO:22870 | |

FIGURE 49
(Continued)

| | | | | | |
|---|---|---|---|---|---|
| iPS:436132 | 21-225_196C12 | NA | AGTTATGATATCAAC | TGGATGAACCCTAAAAG GGGTAACACAGGCTATG CACAGAAGTTCCAGGGC | GGAGACCCGTATAACTGGAA CTCCTACGCTATGGACGTC |
| | | | SEQ ID NO:6847 | SEQ ID NO:14859 | SEQ ID NO:22871 |
| | | AA | SYDIN | WMNPKRGNTGYAQKFQG | GDPYNWNSYAMDV |
| | | | SEQ ID NO:6848 | SEQ ID NO:14860 | SEQ ID NO:22872 |
| iPS:436134 | 21-225_196H12 | NA | AGTGGTGTTACTACTGGAG C | AACATCTATTACAGTGG GAGCACCTACAACAAC CGTCCCTCAAGAGT | GGGGATTACGATGGTTCGGG GAGTTATCACTACTACTACG GTTTGGACGTC |
| | | | SEQ ID NO:6849 | SEQ ID NO:14861 | SEQ ID NO:22873 |
| | | AA | SGVYYWS | NIYYSGSTYNNPSLKS | GDYDGSGSYHYYYGLDV |
| | | | SEQ ID NO:6850 | SEQ ID NO:14862 | SEQ ID NO:22874 |
| iPS:436138 | 21-225_197F2 | NA | AGCTATGGCATGCAC | GTTATATGGTATGATGG AAGTAATAAAAACTATG CAGACTCCGTGAAGGGC | GATCAGGGCGTGGGCTACGA CGGTTTGGACGTC |
| | | | SEQ ID NO:6851 | SEQ ID NO:14863 | SEQ ID NO:22875 |
| | | AA | SYGMH | VIWYDGSNKNYADSVKG | DQGVGYDGLDV |
| | | | SEQ ID NO:6852 | SEQ ID NO:14864 | SEQ ID NO:22876 |
| iPS:436140 | 21-225_197G3 | NA | AGCCATGGCATGCAC | GTTATATGGTATGATGG AAGTAATAAAAACTATG CAGACTCCGTGAAGGGC | GATCCCTCTGTAGGGTACGA CGGTATGGACGTC |
| | | | SEQ ID NO:6853 | SEQ ID NO:14865 | SEQ ID NO:22877 |
| | | AA | SHGMH | VIWYDGSNKNYADSVKG | DPSVGYDGMDV |
| | | | SEQ ID NO:6854 | SEQ ID NO:14866 | SEQ ID NO:22878 |

FIGURE 49
(Continued)

| | | | | | | |
|---|---|---|---|---|---|---|
| iPS:436146 | 21-225_197F4 | NA | AGTGGTGATTACTACTGGAA C | TACATCTTTTACAGTGGG AGCACTACTACAACCC GTCCCTCAAGAGT | GGGGATTACGATGGTTCGGG GAGTTATCACTACTACTACG GTTTGGACGTC |
| | | AA | SEQ ID NO:6855 SGDYYWN | SEQ ID NO:14867 YIFYSGSTYYNPSLKS | SEQ ID NO:22879 GDYDGSGSYHYYYGLDV |
| iPS:436150 | 21-225_197H4 | NA | SEQ ID NO:6856 AATTATGATATCAAC | SEQ ID NO:14868 TGGATGCACCCTAACAG TGGTAACACAGGCTATG CACAGAAGTTCCAGGGC | SEQ ID NO:22880 AGCAGTGGCTGGTACTACTT TGACTAC |
| | | AA | SEQ ID NO:6857 NYDIN | SEQ ID NO:14869 WMHPNSGNTGYAQKFQG | SEQ ID NO:22881 SSGWYYFDY |
| iPS:436152 | 21-225_197B6 | NA | SEQ ID NO:6858 AGCTATGGCATGCAC | SEQ ID NO:14870 GTTATATGGTATGATGG AAGTAATAAAAACTACG CAGACTCCGTGAAGGGC | SEQ ID NO:22882 GATCAGGGCGGTGGGCTACGA CGGTTTGGACGTC |
| | | AA | SEQ ID NO:6859 SYGMH | SEQ ID NO:14871 VIWYDGSNKNYADSVKG | SEQ ID NO:22883 DQGVGYDGLDV |
| iPS:436154 | 21-225_197C6 | NA | SEQ ID NO:6860 AATTATGATATCAAC | SEQ ID NO:14872 TGGATGCACCCTAACAG TGGTAACACAGGCTATG CACAGAAGTTCCAGGGC | SEQ ID NO:22884 AGCAGTGGCTGGTACTACTT TGACTAC |
| | | AA | SEQ ID NO:6861 NYDIN | SEQ ID NO:14873 WMHPNSGNTGYAQKFQG | SEQ ID NO:22885 SSGWYYFDY |
| | | | SEQ ID NO:6862 | SEQ ID NO:14874 | SEQ ID NO:22886 |

FIGURE 49
(Continued)

| | | NA | AGCTCTGCCATGACC | GCTATCATTGGTAATGGT GGTAGAGCATACTACGC AGACTCCGTGAAGGGC | GATCGGGGATATAGCAGGAT AGCAGTGGCTGGTACCTTTG ACTAC |
|---|---|---|---|---|---|
| iPS:436156 | 21-225_197C8 | | SEQ ID NO:6863 | SEQ ID NO:14875 | SEQ ID NO:22887 |
| | | AA | SSAMT | AIIGNGGRAYYADSVKG | DRGYSRIAVAGTFDY |
| | | | SEQ ID NO:6864 | SEQ ID NO:14876 | SEQ ID NO:22888 |
| iPS:436158 | 21-225_197G8 | NA | GCTTACTCCTGGAGC | CGTCTCTCTCCTGGTGG AGCACCAACTTCAACCC CTCCCTCAAGAGT | CTCCGGTATAACTGGAACTT CCCTTACTTTGACTAC |
| | | | SEQ ID NO:6865 | SEQ ID NO:14877 | SEQ ID NO:22889 |
| | | AA | AYSWS | RLSPGGSTNFNPSLKS | LRYNWNFPYFDY |
| | | | SEQ ID NO:6866 | SEQ ID NO:14878 | SEQ ID NO:22890 |
| iPS:436160 | 21-225_197C9 | NA | AGCTATGCCATGAGC | GTTATTAGTGGTAGAGG TGGTAACACATACTACG CAGACTCCGTGAAGGGC | GGCATAGCAGTGGCTGGCTC GCACTACTTTGACTAC |
| | | | SEQ ID NO:6867 | SEQ ID NO:14879 | SEQ ID NO:22891 |
| | | AA | SYAMS | VISGRGGNTYYADSVKG | GIAVAGSHYFDY |
| | | | SEQ ID NO:6868 | SEQ ID NO:14880 | SEQ ID NO:22892 |
| iPS:436164 | 21-225_197G10 | NA | AGCTATGGCATGCAC | GTTACATGGTATGATGG AAGTAATAAATACTATG CAGACTCCGTGAAGGGC | GAATGGCTACAATTAGGTA CTACTACGGTATAGACGTC |
| | | | SEQ ID NO:6869 | SEQ ID NO:14881 | SEQ ID NO:22893 |
| | | AA | SYGMH | VTWYDGSNKYYADSVKG | EWLQFRYYYGIDV |
| | | | SEQ ID NO:6870 | SEQ ID NO:14882 | SEQ ID NO:22894 |
| iPS:436167 | 21-225_197E11 | NA | AACTATGGCATGCAC | GTTATATGGTTTGATGGA AGTAATGACTACTATGC AGACTCCGTGAAGGGC | GATAGAAGGTCGGCTACGA CGGTTTAGATGTC |
| | | | SEQ ID NO:6871 | SEQ ID NO:14883 | SEQ ID NO:22895 |

FIGURE 49
(Continued)

| | | | | | | |
|---|---|---|---|---|---|---|
| iPS:436173 | 21-225_197G12 | AA | NYGMH | | VIWFDGSNDYYADSVKG | DRSVGYDGLDV |
| | | | SEQ ID NO:6872 | | SEQ ID NO:14884 | SEQ ID NO:22896 |
| | | NA | AGCTATGGCATGCAC | | GTTATATGGTATGATGG AAGTAATAAAAACTATG CAGACTCCGTGAAGGGC | GATCAGGGCGTGGCTACGA CGGTTTGGACGTC |
| | | | SEQ ID NO:6873 | | SEQ ID NO:14885 | SEQ ID NO:22897 |
| iPS:436177 | 21-225_198B1 | AA | SYGMH | | VIWYDGSNKNYADSVKG | DQGVGYDGLDV |
| | | | SEQ ID NO:6874 | | SEQ ID NO:14886 | SEQ ID NO:22898 |
| | | NA | AGTGGTGGTTACTACTGGAAC | | TACATCTTCCACAGTGGG AGCACCTACTACAACCC GTCCCTCAAGAGT | GGGGATTACGATGGTTCGGG GAGTTATCACTACTATTACG GTATGGACGTC |
| | | | SEQ ID NO:6875 | | SEQ ID NO:14887 | SEQ ID NO:22899 |
| iPS:436179 | 21-225_198E1 | AA | SGDYYWN | | YIFHSGSTYYNPSLKS | GDYDGSGSYHYYYGMDV |
| | | | SEQ ID NO:6876 | | SEQ ID NO:14888 | SEQ ID NO:22900 |
| | | NA | AGTGGTGGTTACTACTGGAG | | TTCATCTTTTACAGTGGG AGCACCTACTACAACCC GTCCCTCAAGAGT | GGGGATTACGATGGTTCGGG GAGTTATCACTACTATTACG GTATGGACGTC |
| | | | SEQ ID NO:6877 | | SEQ ID NO:14889 | SEQ ID NO:22901 |
| iPS:436181 | 21-225_198C2 | AA | SGGYYWN | | FIFYSGSTYYNPSLKS | GDYDGSGSYHYYYGMDV |
| | | | SEQ ID NO:6878 | | SEQ ID NO:14890 | SEQ ID NO:22902 |
| | | NA | AGTGGTGGTTACTATGGTTCGGG | | AACATCTATTACAGTGG GAGCACCTACTACAAC CGTCCCTCAAGAGT | GGGGATTACTATGGTTCGGG GAGTTATCACAACTACTACG GTTTGGACGTC |
| | | | SEQ ID NO:6879 | | SEQ ID NO:14891 | SEQ ID NO:22903 |
| | | AA | SGGYYWS | | NIYYSGSTYYNPSLKS | GDYYGSGSYHNYYGLDV |
| | | | SEQ ID NO:6880 | | SEQ ID NO:14892 | SEQ ID NO:22904 |

FIGURE 49 (Continued)

| iPS: | | | | | |
|---|---|---|---|---|---|
| iPS:436189 | 21-225_198B6 | NA | AGTTATGGCATGCAC SEQ ID NO:6881 | GTTATATGGTATGATGG AAGTAATAAACACTATG CAGACTCCGTGAAGGGC SEQ ID NO:14893 | GATCAGGGCGTGGGCTACTA CGGTATGGACGTC SEQ ID NO:22905 |
| | | AA | SYGMH SEQ ID NO:6882 | VIWYDGSNKHYADSVKG SEQ ID NO:14894 | DQGVGYYGMDV SEQ ID NO:22906 |
| iPS:436191 | 21-225_198B9 | NA | AACTATGGCATGCAC SEQ ID NO:6883 | ATTATATGGTTTGATGGA AGTAATAAATACTATGT AGACTCCGTGAAGGGC SEQ ID NO:14895 | GAATGGCTACAATTCAGGTA CTACTACGGTATGGACGTC SEQ ID NO:22907 |
| | | AA | NYGMH SEQ ID NO:6884 | IIWFDGSNKYYVDSVKG SEQ ID NO:14896 | EWLQFRYYYGMDV SEQ ID NO:22908 |
| iPS:436193 | 21-225_198A10 | NA | AGTTACCACTGGAGT SEQ ID NO:6885 | CATATCTATACCAGTAG GAGCACCAACTACAACC CCTCCCTCAAGAGT SEQ ID NO:14897 | CTCCGGTATAACTGGAACTT CCCTTACTTTGACTAC SEQ ID NO:22909 |
| | | AA | SYHWS SEQ ID NO:6886 | HIYTSRSTNYNPSLKS SEQ ID NO:14898 | LRYNWNFPYFDY SEQ ID NO:22910 |
| iPS:436195 | 21-225_198G10 | NA | AGTGGTGATTACTACTGGAA C SEQ ID NO:6887 | TACATCTTTTACAGTGGG AGCACCTACTACAACCC GTCCCTCAAGAGT SEQ ID NO:14899 | GGGGATTACGATGGTTCGGG GAGTTATCACTTCTACTACG GTATGGACGTC SEQ ID NO:22911 |
| | | AA | SGDYYWN SEQ ID NO:6888 | YIFYSGSTYYNPSLKS SEQ ID NO:14900 | GDYDGSGSYHFYYGMDV SEQ ID NO:22912 |
| iPS:436197 | 21-225_199C2 | NA | AGTGGTGATTACTACTGGAA C | TACATCTTTTACAGTGGG AGCACCTACTACAACCC GTCCCTCAAGAGT | GGGGATTACGATGGTTCGGG GAGTATCACTACTACTACG GTATGGACGTC |

FIGURE 49
(Continued)

| | | | | | |
|---|---|---|---|---|---|
| iPS:436199 | 21-225_199C2 | AA | SEQ ID NO:6889<br>SGDYYWN | SEQ ID NO:14901<br>YIFYSGSTYYNPSLKS | SEQ ID NO:22913<br>GDYDGSGSYHYYYGMDV |
| | | NA | SEQ ID NO:6890<br>GGTTACTTCTGGAAC | SEQ ID NO:14902<br>GAAATCAATCATATGG<br>AAGCACCAACTACAACC<br>CGTCCCTCAAGAGT | SEQ ID NO:22914<br>GACTACGGTGCTGACTAC |
| iPS:436201 | 21-225_199E3 | AA | SEQ ID NO:6891<br>GYFWT | SEQ ID NO:14903<br>EINHSGSTNYNPSLKS | SEQ ID NO:22915<br>DYGADY |
| | | NA | SEQ ID NO:6892<br>AGCTATGGCATGCAC | SEQ ID NO:14904<br>GTTATATGGTATGATGG<br>AAGTAATAAAAACTATG<br>CAGACTCCGTGAAGGGC | SEQ ID NO:22916<br>GATCAGGGGCGTGGGCTACTA<br>CGGTATGGACGTC |
| iPS:436203 | 21-225_199C5 | AA | SEQ ID NO:6893<br>SYGMH | SEQ ID NO:14905<br>VIWYDGSNKNYADSVKG | SEQ ID NO:22917<br>DQGVGYYYGMDV |
| | | NA | SEQ ID NO:6894<br>AACTATGGCATGCAC | SEQ ID NO:14906<br>ATTATATGGTTTGATGGA<br>AGTAATCAATACTATGC<br>CGACTCCGTGAAGGGC | SEQ ID NO:22918<br>GCCCACGGGGTCTACTACTA<br>CGCTATGGACGTC |
| iPS:436205 | 21-225_199A6 | AA | SEQ ID NO:6895<br>NYGMH | SEQ ID NO:14907<br>IIWFDGSNQYYADSVKG | SEQ ID NO:22919<br>AHGVYYYAMDV |
| | | NA | SEQ ID NO:6896<br>AACTATGGCATGCAC | SEQ ID NO:14908<br>ATTATATGGTTTGATGGA<br>AGTAATAAATACTATGC<br>AGACTCCGTGAAGGGC | SEQ ID NO:22920<br>GAATGGCTACAATTCAGGTA<br>CTACTACGGTATGGACGTC |
| iPS:436205 | 21-225_199A7 | AA | SEQ ID NO:6897<br>IIWFDGSNKYYADSVKG | SEQ ID NO:14909<br>IIWFDGSNKYYADSVKG | SEQ ID NO:22921<br>EWLQFRYYYGMDV |
| | | | SEQ ID NO:6898<br>NYGMH | SEQ ID NO:14910 | SEQ ID NO:22922 |

FIGURE 49
(Continued)

| | | | | |
|---|---|---|---|---|
| iPS:436207 | 21-225_199C7 | NA | AGTGGTGGTTACTACTGGAAC<br>SEQ ID NO:6899 | TTCATCTTTTACAGTGGGAGCACTACTACAACCCGTCCCTCAAGAGT<br>SEQ ID NO:14911 | GGGGATTACGATGGTTCGGGGAGTTATCACTACTATTACGGTATGGACGTC<br>SEQ ID NO:22923 |
| | | AA | SGGYYWN<br>SEQ ID NO:6900 | FIFYSGSTYYNPSLKS<br>SEQ ID NO:14912 | GDYDGSGSYHYYYGMDV<br>SEQ ID NO:22924 |
| iPS:436210 | 21-225_199G11 | NA | AGTGGTGGTTACTACTGGAGC<br>SEQ ID NO:6901 | AACATCTATTACAGTGGGAGCACCTACTACAACCCGTCCCTCAAGAGT<br>SEQ ID NO:14913 | GGGGATTACTATGGTTCGGGGAGTTATCACAACTACTACGGTTTGGACGTC<br>SEQ ID NO:22925 |
| | | AA | SGGYYWS<br>SEQ ID NO:6902 | NIYYSGSTYYNPSLKS<br>SEQ ID NO:14914 | GDYYGSGSYHNYYGLDV<br>SEQ ID NO:22926 |
| iPS:436212 | 21-225_200G1 | NA | AGCTATGCCATGAGC<br>SEQ ID NO:6903 | GCTATTAGTGGTAGAGGCGGTAATACATTCTACGCAGACTCCGTGAGGGGC<br>SEQ ID NO:14915 | CGTATAGCAGTGGATGGCTATGATGCTTTTGATGTC<br>SEQ ID NO:22927 |
| | | AA | SYAMS<br>SEQ ID NO:6904 | AISGRGGNTFYADSVRG<br>SEQ ID NO:14916 | RIAVDGYDAFDV<br>SEQ ID NO:22928 |
| iPS:436214 | 21-225_200F6 | NA | AGTTATGGCATGCAC<br>SEQ ID NO:6905 | GTTATATGGTATGATGGAAGTAATAAATACTATGCAGACTCCGTGAAGGGC<br>SEQ ID NO:14917 | GAATGGCTACAATTAGGTATTACTACGGTATGGACGTC<br>SEQ ID NO:22929 |
| | | AA | SYGMH<br>SEQ ID NO:6906 | VIWYDGSNKYYADSVKG<br>SEQ ID NO:14918 | EWLQFRYYYGMDV<br>SEQ ID NO:22930 |
| iPS:436216 | 21-225_200B7 | NA | AGTGGTGGTTACTACTGGAGC<br>SEQ ID NO:6907 | TACATCTTTTACAGTGGGAGCACCAACTACTACAACCCGTCCCTCAGGAGT<br>SEQ ID NO:14919 | GCCGGGTATAACTGGAACAACGGTATGGACGTC<br>SEQ ID NO:22931 |

FIGURE 49
(Continued)

| | | | | | | |
|---|---|---|---|---|---|---|
| iPS:436218 | 21-225_200G7 | AA | SGGYYWS | YIFYSGSTNYNPSLRS | AGYNWNNGMDV | |
| | | | SEQ ID NO:6908 | SEQ ID NO:14920 | SEQ ID NO:22932 | |
| | | NA | AATTATGATATCAAC | TGGATGCACCTTAACAGTGGTAACACAGGCTATGCACCGAAGTTCCAGGGC | AGCGGTGGCTGGTACGTGTTCGACCCC | |
| | | | SEQ ID NO:6909 | SEQ ID NO:14921 | SEQ ID NO:22933 | |
| | | AA | NYDIN | WMHLNSGNTGYAPKFQG | SGGWYVFDP | |
| | | | SEQ ID NO:6910 | SEQ ID NO:14922 | SEQ ID NO:22934 | |
| iPS:436220 | 21-225_200F8 | NA | AATTACTACTGGAGC | CGTATCTATACCAGTGGGAGCACCAACTACAACCCCTCCCTCAAGAGT | GATCGGGGATACTATGGCTACTACGGTATGGACGTC | |
| | | | SEQ ID NO:6911 | SEQ ID NO:14923 | SEQ ID NO:22935 | |
| | | AA | NYYWS | RIYTSGSTNYNPSLKS | DRGYGYYGMDV | |
| | | | SEQ ID NO:6912 | SEQ ID NO:14924 | SEQ ID NO:22936 | |
| iPS:436222 | 21-225_200C9 | NA | AGCTATGGCATGCAC | GTTATATCATATGATGGAGGTTATAAAACTATATAGACTCCGTGAAGGGC | GGTACCACCAGGGTACTACTACGGTGTGGACGTC | |
| | | | SEQ ID NO:6913 | SEQ ID NO:14925 | SEQ ID NO:22937 | |
| | | AA | SYGMH | VISYDGGYKNYIDSVKG | GTHGYYYGVDV | |
| | | | SEQ ID NO:6914 | SEQ ID NO:14926 | SEQ ID NO:22938 | |
| iPS:436226 | 21-225_200F10 | NA | AGTGGTGATTACTACTGGAAC | TACATCTTTACAGTGGGAGCACCACTACAACCCGTCCCTCAAGAGT | GGGGATTACGATGGTTCGGGAGTTATCACTACTACGGTATGGACGTC | |
| | | | SEQ ID NO:6915 | SEQ ID NO:14927 | SEQ ID NO:22939 | |
| | | AA | SGDYYWN | YIFYSGSTYYNPSLKS | GDYDGSGSYHYYYGMDV | |
| | | | SEQ ID NO:6916 | SEQ ID NO:14928 | SEQ ID NO:22940 | |

FIGURE 49
(Continued)

| | | | | | |
|---|---|---|---|---|---|
| iPS:436228 | 21-225_200F12 | NA | GGTTACTTCTGGACC | GAAATCAGTCATAGTGG AAGCACCAACTACAACC CGTCCCTCAAGAGT | GACTACGGGGCGGACTAC |
| | | | SEQ ID NO:6917 | SEQ ID NO:14929 | SEQ ID NO:22941 |
| | | AA | GYFWT | EISHSGSTNYNPSLKS | DYGADY |
| | | | SEQ ID NO:6918 | SEQ ID NO:14930 | SEQ ID NO:22942 |
| iPS:436230 | 21-225_201A1 | NA | GGTTACTTCTGGACC | GAAATCAGTCATAGTGG ACGCACCAACTACAACC CGTCCCTCAAGAGT | GACTACGGGGCGGACTAC |
| | | | SEQ ID NO:6919 | SEQ ID NO:14931 | SEQ ID NO:22943 |
| | | AA | GYFWT | EISHSGRTNYNPSLKS | DYGADY |
| | | | SEQ ID NO:6920 | SEQ ID NO:14932 | SEQ ID NO:22944 |
| iPS:436232 | 21-225_201E1 | NA | CCTTACTACTGGAGC | GAAGTCAATCATAGTGG AAGCACCAACTACAACC CGTCCCTCAAGAGT | GACTACGGGGGGTTTAGACTAC |
| | | | SEQ ID NO:6921 | SEQ ID NO:14933 | SEQ ID NO:22945 |
| | | AA | PYYWS | EVNHSGSTNYNPSLKS | DYGGLDY |
| | | | SEQ ID NO:6922 | SEQ ID NO:14934 | SEQ ID NO:22946 |
| iPS:436234 | 21-225_51E3 | NA | AGCTATGGTATCAGC | TGGATCAGCGCTTATAAT GGTAACACAAAGAATGC ACAGAGGTTCCAGGC | CACGATTTTGGAGTGGTTA TTATAAGGTATGGACGTC |
| | | | SEQ ID NO:6923 | SEQ ID NO:14935 | SEQ ID NO:22947 |
| | | AA | SYGIS | WISAYNGNTKNAQRFQG | HDFWSGYYKGMDV |
| | | | SEQ ID NO:6924 | SEQ ID NO:14936 | SEQ ID NO:22948 |
| iPS:436236 | 21-225_201F7 | NA | AGCAACAGTGCTGCTTGGAA C | AGGACATACTACAGGTC CAAGTGGTATAATTATTA TGAAGTATCTGTGAGAA GT | GATCAACGGTACTACGGTAT GGACGTC |
| | | | SEQ ID NO:6925 | SEQ ID NO:14937 | SEQ ID NO:22949 |

FIGURE 49 (Continued)

| | | | | RTYYRSKWYNYYEVSVRS | DQRYYGMDV |
|---|---|---|---|---|---|
| iPS:436238 | 21-225_201B2 | AA | SNSAAWN | | |
| | | | SEQ ID NO:6926 | SEQ ID NO:14938 | SEQ ID NO:22950 |
| | | NA | GTTACTACTGGACC | GAAATCAATCATAGTGG AAGCACCAACTACAACC CGTCCCTCAAGAGT | GACTATGGTGTCTTTGATTA C |
| | | | SEQ ID NO:6927 | SEQ ID NO:14939 | SEQ ID NO:22951 |
| | | AA | VYYWT | EINHSGSTNYNPSLKS | DYGVFDY |
| iPS:436240 | 21-225_201E8 | | SEQ ID NO:6928 | SEQ ID NO:14940 | SEQ ID NO:22952 |
| | | NA | GGCTACTATATGCAC | TGGATCGACCCTAACAG TGGTGGCACAAACTATC CACAGAAGTTTCAGGGC | GATCAAGGTATAACTGGAA CTCTTTTGACTAC |
| | | | SEQ ID NO:6929 | SEQ ID NO:14941 | SEQ ID NO:22953 |
| | | AA | GYYMH | WIDPNSGGTNYPQKFQG | DQGYNWSFDY |
| iPS:436242 | 21-225_201A10 | | SEQ ID NO:6930 | SEQ ID NO:14942 | SEQ ID NO:22954 |
| | | NA | GGTTACTTCTGGACC | GAAATCAGTCATAGTGG AAGCACCAACTACAACC CGTCCCTCAAGAGT | GACTACGGGGCGGGACTAC |
| | | | SEQ ID NO:6931 | SEQ ID NO:14943 | SEQ ID NO:22955 |
| | | AA | GYFWT | EISHSGSTNYNPSLKS | DYGADY |
| iPS:436244 | 21-225_201H10 | | SEQ ID NO:6932 | SEQ ID NO:14944 | SEQ ID NO:22956 |
| | | NA | GGCTACTATATCCAC | TGGATCAACCCTAATAG TGGTGGCACAAACTATG CACAGAAGTTTCAGGGC | GGATACAGCTATGGTTACAA CTGGTTCGACCCC |
| | | | SEQ ID NO:6933 | SEQ ID NO:14945 | SEQ ID NO:22957 |
| | | AA | GYYIH | WINPNSGGTNYAQKFQG | GYSYGYNWFDP |
| iPS:436246 | 21-225_201G6 | | SEQ ID NO:6934 | SEQ ID NO:14946 | SEQ ID NO:22958 |
| | | NA | AGCTATGCCATGAGC | ACTATTAGTGGTAGTGGT GTTAGAACATACTACGC AGACTCCGTGAAGGGC | GGGGGAGCTAGGAGCAGTG GCTGGTTCCACTTGACTAC |

FIGURE 49
(Continued)

| | | | | | | |
|---|---|---|---|---|---|---|
| iPS:436248 | 21-225_201G6 | AA | SEQ ID NO:6935 SYAMS | SEQ ID NO:14947 TISGSGVRTYYADSVKG | SEQ ID NO:22959 GGARSSGWFHFDY | |
| | | NA | SEQ ID NO:6936 AGTTATGATATCAAC | SEQ ID NO:14948 TGGATGAACCCTAAGAG AGGTAACACAGGCTATG CACAGAAGTTCCAGGGC | SEQ ID NO:22960 GGAAGGTATAGCAGGAGG ATTACTACTACTATTATGAT ATGGACGTC | |
| iPS:436250 | 21-225_202A3 | AA | SEQ ID NO:6937 SYDIN | SEQ ID NO:14949 WMNPKRGNTGYAQKFQG | SEQ ID NO:22961 GRYSREDYYYYDMDV | |
| | | NA | SEQ ID NO:6938 AGCAACAGTGCTGCTGGAA C | SEQ ID NO:14950 AGGACATACTACAGGTC CAAGTGGTATAATTATTA TGAAGTATCTGTGAAAA GT | SEQ ID NO:22962 GATCAACGGTACTACCGTAT GGACGTC | |
| iPS:436252 | 21-225_201A4 | AA | SEQ ID NO:6939 SNSAAWN | SEQ ID NO:14951 RTYYRSKWYNYYEVSVK S | SEQ ID NO:22963 DQRYYGMDV | |
| | | NA | SEQ ID NO:6940 AGCAACAGTGCTGCTGGAA C | SEQ ID NO:14952 AGGACATACTACAGGTC CAAGTGGTATAATGAGT ATGCAGATATCTGTGAGA AGT | SEQ ID NO:22964 GATCAACGGTACTACCGTAT GGACGTC | |
| iPS:436254 | 21-225_202A8 | AA | SEQ ID NO:6941 SNSAAWN | SEQ ID NO:14953 RTYYRSKWYNEYAVSVRS | SEQ ID NO:22965 DQRYYGMDV | |
| | | NA | SEQ ID NO:6942 AGCTATGCCATGAGC | SEQ ID NO:14954 ACTATTAGTGGTAGTGGT GTTAGAACATACTACGC AGACTCCGTGAAGGGC | SEQ ID NO:22966 GGGGGAGCTAGGAGCAGTG GCTGGTTCCACTTTGACTAC | |
| | 21-225_202C12 | | SEQ ID NO:6943 | SEQ ID NO:14955 | SEQ ID NO:22967 | |

FIGURE 49 (Continued)

| | | | | | | | |
|---|---|---|---|---|---|---|---|
| iPS:436256 | 21-225_202D9 | AA | SYAMS | SEQ ID NO:6944 | TISGSGVRTYYADSVKG | SEQ ID NO:14956 | GGARSSGWFHFDY | SEQ ID NO:22968 |
| | | NA | CCTTACTACTGGAGC | SEQ ID NO:6945 | GAAATCAATCATAGTGG AAGCACCAACTACAATC CGTCCCTCAAGAGT | SEQ ID NO:14957 | GACTACGGGGGTTTAGACTA C | SEQ ID NO:22969 |
| iPS:436258 | 21-225_202F12 | AA | PYYWS | SEQ ID NO:6946 | EINHSGSTNYNPSLKS | SEQ ID NO:14958 | DYGGLDY | SEQ ID NO:22970 |
| | | NA | TACTATGGCATGCAC | SEQ ID NO:6947 | ATTATATGGTATGATGG AAGTAATAAATTCTATG CAGACTCCGTGAAGGGC | SEQ ID NO:14959 | AATATAGCAGCAGCTGCCCC TTACTTTGACTAC | SEQ ID NO:22971 |
| iPS:436260 | 21-225_203H1 | AA | YYGMH | SEQ ID NO:6948 | HWYDGSNKFYADSVKG | SEQ ID NO:14960 | NIAAAPYFDY | SEQ ID NO:22972 |
| | | NA | AGCTATGGCATGCAC | SEQ ID NO:6949 | GTTATATGGTATGATGG AAGTAATAAAAACTATG CAGACTCCGTGAAGGGC | SEQ ID NO:14961 | GATAGAACAGTTGGCTACAA CGGTATGGACGTC | SEQ ID NO:22973 |
| iPS:436262 | 21-225_203E3 | AA | SYGMH | SEQ ID NO:6950 | VIWYDGSNKNYADSVKG | SEQ ID NO:14962 | DRTVGYNGMDV | SEQ ID NO:22974 |
| | | NA | GGCTACTATATCCAC | SEQ ID NO:6951 | TGGATCAACCCTAATAG TGGTGGCACAAACTATG CACAGAAGTTTCAGGGC | SEQ ID NO:14963 | GGATACAGCTATGGTTACAA CTGGTTCGACCCC | SEQ ID NO:22975 |
| | | AA | GYYIH | SEQ ID NO:6952 | WINPNSGGTNYAQKFQG | SEQ ID NO:14964 | GYSYGYNWFDP | SEQ ID NO:22976 |

FIGURE 49
(Continued)

| | | | | |
|---|---|---|---|---|
| iPS:436264 | 21-225_203F7 | NA | GACTATGTCATGCAC<br>SEQ ID NO:6953 | GTATATGGTATGATGG<br>AAGTAATAAATACTATG<br>TAGACTCCGTGAAGGGC<br>SEQ ID NO:14965 | GAACGGTATAGCAGTGGCTT<br>GTACGACTACGGTATGGACG<br>TC<br>SEQ ID NO:22977 |
| | | AA | DYVMH<br>SEQ ID NO:6954 | VIWYDGSNKYYVDSVKG<br>SEQ ID NO:14966 | ERYSSGLYDYGMDV<br>SEQ ID NO:22978 |
| iPS:436268 | 21-225_203B9 | NA | AGTTTTGGCATGCAC<br>SEQ ID NO:6955 | GTTATATGGTATGATGTA<br>AATAATAAATACTATGC<br>AGACTCCGTGAAGGGC<br>SEQ ID NO:14967 | GAACTGGGGTTCCTCTCTGA<br>CTAC<br>SEQ ID NO:22979 |
| | | AA | SFGMH<br>SEQ ID NO:6956 | VIWYDVNKYYADSVKG<br>SEQ ID NO:14968 | ELGFLSDY<br>SEQ ID NO:22980 |
| iPS:436270 | 21-225_203F10 | NA | GACTACTACATGAGC<br>SEQ ID NO:6957 | TACATTAGTAGTGGTAGTGGT<br>ACTACCACATACTACGC<br>AGACTCTGTGAAGGGC<br>SEQ ID NO:14969 | GATAGGGGGGGGTTTGGACGT<br>C<br>SEQ ID NO:22981 |
| | | AA | DYYMS<br>SEQ ID NO:6958 | YISGSGTTYYADSVKG<br>SEQ ID NO:14970 | DRGGLDV<br>SEQ ID NO:22982 |
| iPS:436272 | 21-225_201F5 | NA | AATTATGATATCAAC<br>SEQ ID NO:6959 | TGGATGCACCTAACAG<br>TGGTAACACAGGCTATG<br>CACAGAAGTTCCAGGGC<br>SEQ ID NO:14971 | AGCAGTGGCTGGTACTACTT<br>TGACTAC<br>SEQ ID NO:22983 |
| | | AA | NYDIN<br>SEQ ID NO:6960 | WMHPNSGNTGYAQKFQG<br>SEQ ID NO:14972 | SSGWYYFDY<br>SEQ ID NO:22984 |

FIGURE 49
(Continued)

| | | | | | |
|---|---|---|---|---|---|
| iPS:436274 | 21-225_204H3 | NA | AGCTATGTCATGCAC<br>SEQ ID NO:6961 | GTTATATGGTATGATGG<br>AAGTAATAAATATAATG<br>CAGACTCCGTGAAGGGC<br>SEQ ID NO:14973 | GAACCGTATAGCAGCAGCTG<br>GTACGACTACGGTATGGACG<br>TC<br>SEQ ID NO:22985 |
| | | AA | SYVMH<br>SEQ ID NO:6962 | VIWYDGSNKYNADSVKG<br>SEQ ID NO:14974 | EPYSSSWYDYGMDV<br>SEQ ID NO:22986 |
| iPS:436276 | 21-225_204H4 | NA | GGCTACTACTATATCCAC<br>SEQ ID NO:6963 | TGGATCAACCCTAATAG<br>TGGTGGCACAAACTATG<br>CACAGAAGTTTCAGGGC<br>SEQ ID NO:14975 | GGATACAGCTATGGTTACAA<br>CTGGTTCGACCCC<br>SEQ ID NO:22987 |
| | | AA | GYYIH<br>SEQ ID NO:6964 | WINPNSGGTNYAQKFQG<br>SEQ ID NO:14976 | GYSYGYNWFDP<br>SEQ ID NO:22988 |
| iPS:436278 | 21-225_201F2 | NA | AGCAACAGTGCTGCTTGGAA<br>C<br>SEQ ID NO:6965 | AGGACATACTACACGTC<br>CAAGTGGTATAATTATTA<br>TGAAGTATCTGTGAGAA<br>GT<br>SEQ ID NO:14977 | GATCAACGGTACTACGGTAT<br>GGACGTC<br>SEQ ID NO:22989 |
| | | AA | SNSAAWN<br>SEQ ID NO:6966 | RTYYRSKWYNYYEVSVRSS<br>DQRYYGMDV<br>SEQ ID NO:14978 | SEQ ID NO:22990 |
| iPS:436280 | 21-225_204D6 | NA | ACCTATGCCATGAGC<br>SEQ ID NO:6967 | GCTATTAGTAGTGGTAGTGGT<br>GGTAGCACATATTACGC<br>AGACTCCGTGAAGGGC<br>SEQ ID NO:14979 | GGGATAAGTGGTGGAACCGGCTC<br>CTACTACTACGGTGTGG<br>ACGTC<br>SEQ ID NO:22991 |
| | | AA | TYAMS<br>SEQ ID NO:6968 | AISGSGGSTYYADSVKG<br>SEQ ID NO:14980 | GISGIGSYYYYGVDV<br>SEQ ID NO:22992 |

FIGURE 49
(Continued)

| iPS: | | | | | |
|---|---|---|---|---|---|
| iPS:436282 | 21-225_204G6 | NA | AGCTATGGCATGCAC | GTTATATGGTATGATGG AAGTAATAAAAACTATG CAGACTCCGTGAAGGGC | GATCGAGGTGTCGGCTACGA CGGTATGGACGTC |
| | | | SEQ ID NO:6969 | SEQ ID NO:14981 | SEQ ID NO:22993 |
| | | AA | SYGMH | VIWYDGSNKNYADSVKG | DRGVGYDGMDV |
| | | | SEQ ID NO:6970 | SEQ ID NO:14982 | SEQ ID NO:22994 |
| iPS:436284 | 21-225_204G8 | NA | AGCTATGGCATGCAC | GTTATATGGTATGATGGT AGCAATGAAAATTATGT AGCCTCCGTGAAGGGC | GATCTGGGGATAGGGTATTA CGGTATGGACGTC |
| | | | SEQ ID NO:6971 | SEQ ID NO:14983 | SEQ ID NO:22995 |
| | | AA | SYGMH | VIWYDGSNENYVASVKG | DLGIGYYGMDV |
| | | | SEQ ID NO:6972 | SEQ ID NO:14984 | SEQ ID NO:22996 |
| iPS:436286 | 21-225_204H8 | NA | GGTTACTTCTGGACC | GAAATCAGTCATAGTGG AAGCACCAGTTACAACC CGTCCCTCAAGAGT | GACTACGGGGCCGACTAC |
| | | | SEQ ID NO:6973 | SEQ ID NO:14985 | SEQ ID NO:22997 |
| | | AA | GYFWT | EISHSGSTSYNPSLKS | DYGADY |
| | | | SEQ ID NO:6974 | SEQ ID NO:14986 | SEQ ID NO:22998 |
| iPS:436290 | 21-225_205G3 | NA | GGTCACTACTGGAGC | GAAAGTATCATTTTGGA AACACCAACTACAACCC GTCCCTCAAGAGT | GTGGGGCAGTGGCTGGCTTT TGATATC |
| | | | SEQ ID NO:6975 | SEQ ID NO:14987 | SEQ ID NO:22999 |
| | | AA | GHYWS | EMYHFGNTNYNPSLKS | VGQWLAFDI |
| | | | SEQ ID NO:6976 | SEQ ID NO:14988 | SEQ ID NO:23000 |

FIGURE 49
(Continued)

| | | | | |
|---|---|---|---|---|
| iPS:436292 | 21-225_205H3 | NA | AGCTATGGCATGCAC | GTTATATGGTATGATGG AAGTAATAAATACTATG CAGACTCCGTGAAGGGC | GATAGATCAGTTGGCTACGA CGGTACGGGACGTC |
| | | | SEQ ID NO:6977 | SEQ ID NO:14989 | SEQ ID NO:23001 |
| | | AA | SYGMH | VIWYDGSNKYYADSVKG | DRSVGYDGTDV |
| | | | SEQ ID NO:6978 | SEQ ID NO:14990 | SEQ ID NO:23002 |
| iPS:436294 | 21-225_205G4 | NA | AGCAACAGTGCTGCTTGGAAC | AGGACATATTACAGGTC CAAGTGGTATAATTATTA TGAAGTATCTGTGAGAA GT | GATCAACGGTACTACGGTAT GGACGTC |
| | | | SEQ ID NO:6979 | SEQ ID NO:14991 | SEQ ID NO:23003 |
| | | AA | SNSAAWN | RTYYRSKWYNYYEVSVRS | DQRYYGMDV |
| | | | SEQ ID NO:6980 | SEQ ID NO:14992 | SEQ ID NO:23004 |
| iPS:436296 | 21-225_205F5 | NA | AGATATGGCATGCAC | GTTATATGGTATGATGG AAGTAATGAGAATTAIG TAGACTCCGTGAAGGGC | GATATGGGGATAGGGTATTA TGGTATGGACGTC |
| | | | SEQ ID NO:6981 | SEQ ID NO:14993 | SEQ ID NO:23005 |
| | | AA | RYGMH | VIWYDGSNENYVDSVKG | DMGIGYYGMDV |
| | | | SEQ ID NO:6982 | SEQ ID NO:14994 | SEQ ID NO:23006 |
| iPS:436302 | 21-225_205G7 | NA | GTTTATTACTGGAGC | GAAAGCAATCAGAGTGG ACGCACCACTACAACC CGTCCCTCAAGAGT | GACTACGGTGTCTTTGACTA C |
| | | | SEQ ID NO:6983 | SEQ ID NO:14995 | SEQ ID NO:23007 |
| | | AA | VYYWS | ESNQSGRTTYNPSLKS | DYGVFDY |
| | | | SEQ ID NO:6984 | SEQ ID NO:14996 | SEQ ID NO:23008 |

FIGURE 49
(Continued)

| | | | | | |
|---|---|---|---|---|---|
| iPS:436304 | 21-225_201F3 | NA | AGCTATGCCATGAGC | ACTATTAGTAGTGGTAGTGGT GTTAGAACATACGC AGACTCCGTGAAGGGC | GGGGGAGCTAGGAGCAGTG GCTGGTTCCACTTTGACTAC |
| | | | SEQ ID NO:6985 | SEQ ID NO:14997 | SEQ ID NO:23009 |
| | | AA | SYAMS | TISGSGVRTYYADSVKG | GGARSSGWFHFDY |
| | | | SEQ ID NO:6986 | SEQ ID NO:14998 | SEQ ID NO:23010 |
| iPS:436306 | 21-225_201H4 | NA | AGCTATGCCATGCAC | GCTATATGGTATGAGAGG AAGTAATAAATACAATG CAGACTCCGTGAAGGGC | GATGTGGGTACAGTGGGAGC TACCTACTTTGACTGC |
| | | | SEQ ID NO:6987 | SEQ ID NO:14999 | SEQ ID NO:23011 |
| | | AA | SYAMH | AIWYDGSNKYNADSVKG | DVGTVGATYFDC |
| | | | SEQ ID NO:6988 | SEQ ID NO:15000 | SEQ ID NO:23012 |
| iPS:436308 | 21-225_205H8 | NA | GGTTACTTCTGGAGC | GAAATCAGTCATAGTGG ACGCACCAACTACAACC CGTCCCTCAAGAGC | GACTACGGGGCGGACTAC |
| | | | SEQ ID NO:6989 | SEQ ID NO:15001 | SEQ ID NO:23013 |
| | | AA | GYFWS | EISHSGRTNYNPSLKS | DYGADY |
| | | | SEQ ID NO:6990 | SEQ ID NO:15002 | SEQ ID NO:23014 |
| iPS:436310 | 21-225_202D11 | NA | GGTCCCTACTGGAGC | GAAATCAATCATAGTGG AAGCACCAACTACAACC CGTCCCTCAAGAGT | GACTACGGTGTCCTTGACTA C |
| | | | SEQ ID NO:6991 | SEQ ID NO:15003 | SEQ ID NO:23015 |
| | | AA | GPYWS | EINHSGTNYNPSLKS | DYGVLDY |
| | | | SEQ ID NO:6992 | SEQ ID NO:15004 | SEQ ID NO:23016 |
| iPS:436312 | 21-225_206A4 | NA | GGCTACTATATCCAC | TGGATCAACCTAATAG TGGTGGCACAAACTATG CACAGAAGTTTCAGGGC | GGATACAGCTATGGTTACAA CTGGTTCGACCCC |
| | | | SEQ ID NO:6993 | SEQ ID NO:15005 | SEQ ID NO:23017 |

FIGURE 49
(Continued)

| | | | | | | | |
|---|---|---|---|---|---|---|---|
| iPS:436314 | 21-225_206G4 | AA | GYYIH | | WINPNSGGTNYAQKFQG | | GYSYGYNWFDP |
| | | | SEQ ID NO:6994 | | SEQ ID NO:15006 | | SEQ ID NO:23018 |
| | | NA | GGCTACTATATACAC | | TGGATCAACCCTAATAG TGGTGGCACAAACTATG CACAGAAGTTCAGGGC | | GATCAAGGGTATAACTGGAA CTCTTTTGACTAC |
| | | | SEQ ID NO:6995 | | SEQ ID NO:15007 | | SEQ ID NO:23019 |
| iPS:436316 | 21-225_206A5 | AA | GYYIH | | WIDPNSGGTNYAQKFQG | | DQGYNWNSFDY |
| | | | SEQ ID NO:6996 | | SEQ ID NO:15008 | | SEQ ID NO:23020 |
| | | NA | GGCTACTATATCCAC | | TGGATCAACCCTAATAG TGGTGGCACAAACTATG CACAGAAGTTCAGGGC | | GGATACAGCTATGGTTACAA CTGGTTCGACCCC |
| | | | SEQ ID NO:6997 | | SEQ ID NO:15009 | | SEQ ID NO:23021 |
| | | AA | GYYIH | | WINPNSGGTNYAQKFQG | | GYSYGYNWFDP |
| | | | SEQ ID NO:6998 | | SEQ ID NO:15010 | | SEQ ID NO:23022 |
| iPS:436324 | 21-225_207G6 | NA | AGCTATGGCATGCAC | | GTTATATGGTATGATGG AAGTAATAAAACTATG CAGAGTCCGTGAAGGGC | | GATGCGGGTATTGGATACTA CGGTATAGACGTC |
| | | | SEQ ID NO:6999 | | SEQ ID NO:15011 | | SEQ ID NO:23023 |
| | | AA | SYGMH | | VIWYDGSNKNYAESVKG | | DAGIGYYGIDV |
| | | | SEQ ID NO:7000 | | SEQ ID NO:15012 | | SEQ ID NO:23024 |
| iPS:436328 | 21-225_207F12 | NA | AACTATGGCATGCAC | | GTTATATGGTATGATGG AAATAATAAATACTATG GTGACTCCGTGAAGGGC | | GAACTGGGGTTCCTCTTTGA CTAC |
| | | | SEQ ID NO:7001 | | SEQ ID NO:15013 | | SEQ ID NO:23025 |
| | | AA | NYGMH | | VIWYDRNNKYYGDSVKG | | ELGFLFDY |
| | | | SEQ ID NO:7002 | | SEQ ID NO:15014 | | SEQ ID NO:23026 |

FIGURE 49
(Continued)

| | | | | |
|---|---|---|---|---|
| iPS:436332 | 21-225_208B2 | NA | GACTGTGTCATGCAC SEQ ID NO:7003 | GTTATATGGTATGATGG AAGTAATAAATACTATG TAGACTCCGTGAAGGGC SEQ ID NO:15015 | GAACGGTATAGCAGTGGCTT GTACGACTACGGTTGGACG TC SEQ ID NO:23027 |
| | | AA | DCVMH | VIWYDGSNKYYVDSVKG | ERYSSGLYDYGLDV |
| iPS:436334 | 21-225_208G3 | NA | AGCTATGCCATGAGC SEQ ID NO:7004 | ACTATTAGTGGTAGTGGT GTTAGAACATACTACGC AGACTCCGTGAAGGGC SEQ ID NO:15016 | GGGGAGCTAGGAGCAGTG GCTGGTTCCACTTTGACTAC SEQ ID NO:23028 |
| | | AA | SYAMS SEQ ID NO:7005 | TISGSGVRTYYADSVKG SEQ ID NO:15017 | GGARSSGWFHFDY SEQ ID NO:23029 |
| iPS:436336 | 21-225_208B5 | NA | GTTTACTACTGGACC SEQ ID NO:7006 | GAAATCAATCATAGTGG AAGCACCAACTACAACC CGTCCCTCAAGAGT SEQ ID NO:15018 | GACTATGGTGTCTTTGATTA C SEQ ID NO:23030 |
| | | AA | VYYWT SEQ ID NO:7007 | EINHSGSTNYNPSLKS SEQ ID NO:15019 | DYGVFDY SEQ ID NO:23031 |
| iPS:436338 | 21-225_208E8 | NA | GGCTACTATATCCAC SEQ ID NO:7008 | TGGATCAACCCTAATAG TGGTGGCACAAACTATG CACAGAAGTTTCAGGGC SEQ ID NO:15020 | GGATACAGCTATGTTACAA CTGGTTCGACCCC SEQ ID NO:23032 |
| | | AA | GYYIH SEQ ID NO:7009 | WINPNSGGTNYAQKFQG SEQ ID NO:15021 | GYSYGYNWFDP SEQ ID NO:23033 |
| iPS:436340 | 21-225_208A9 | NA | GTTTCCTACTGGAGC SEQ ID NO:7010 | GAAATCAATCATAGTGG ACGGCCAACTACAACC CGTCCCTCAAGAGT SEQ ID NO:15022 | GACTACGGTGTCCTTGACTA C SEQ ID NO:23034 |
| | | | SEQ ID NO:7011 | SEQ ID NO:15023 | SEQ ID NO:23035 |

FIGURE 49
(Continued)

| | | AA/NA | | | | | | |
|---|---|---|---|---|---|---|---|---|
| iPS:436344 | 21-225_208B11 | AA | VSYWS | SEQ ID NO:7012 | EINHSGRANYNPSLKS | SEQ ID NO:15024 | DYGVLDY | SEQ ID NO:23036 |
| | | NA | GGCTACTACTATATCCAC | SEQ ID NO:7013 | TGGATCAACCCTAATAGTGGTGGCACAAACTATGCACAGAAGTTCAGGGC | SEQ ID NO:15025 | GGATACAGCTATGGTTACAACTGGTTCGACCCC | SEQ ID NO:23037 |
| iPS:436350 | 21-225_210E4 | AA | GYYIH | SEQ ID NO:7014 | WINPNSGGTNYAQKFQG | SEQ ID NO:15026 | GYSYGYNWFDP | SEQ ID NO:23038 |
| | | NA | AACTATGGCATGCAC | SEQ ID NO:7015 | GTTATATGGTATGATGAAATAATAAATACTATGTAGACTCCGTGAAGGGC | SEQ ID NO:15027 | GAGACGGGTTTCTGAGGGACTAC | SEQ ID NO:23039 |
| iPS:436352 | 21-225_210G5 | AA | NYGMH | SEQ ID NO:7016 | VIWYDENNKYYVDSVKG | SEQ ID NO:15028 | ETGFLSDY | SEQ ID NO:23040 |
| | | NA | GACTGTGTCATGCAC | SEQ ID NO:7017 | GTTATATGGTATGATGGAAGTAATAAATACTATGTAGACTCCGTGAAGGGC | SEQ ID NO:15029 | GAACGGTATAGCAGTGGCTTGTACGACTACGGGTTTGGACGTC | SEQ ID NO:23041 |
| iPS:436354 | 21-225_210G10 | AA | DCVMH | SEQ ID NO:7018 | VIWYDGSNKYYVDSVKG | SEQ ID NO:15030 | ERYSSGLYDYGLDV | SEQ ID NO:23042 |
| | | NA | AGTTACTACTGGAGC | SEQ ID NO:7019 | CGTATCTATACCAGTGGGAGCACCGACTACAACCCCTCCCTCAAGAGT | SEQ ID NO:15031 | GGGTTCGGTGACTGGGACTAC | SEQ ID NO:23043 |
| | | AA | SYYWS | SEQ ID NO:7020 | RIYTSGSTDYNPSLKS | SEQ ID NO:15032 | GFGDWDY | SEQ ID NO:23044 |

FIGURE 49
(Continued)

| iPS: | clone | | | | |
|---|---|---|---|---|---|
| iPS:436356 | 21-225_210H10 | NA | AGCAACAGTGCTGCTTGGAAC<br>SEQ ID NO:7021<br>SNSAAWN | AGGACATACTACAGGTCCAAGTGGTATAATTATTATCCAGTATCTGTGAGAAGT<br>SEQ ID NO:15033<br>RTYYRSKWYNYYPVSVRS | GATCAACGGTACTACGGTATGGACGTC<br>SEQ ID NO:23045<br>DQRYYGMDV |
| | | AA | | | SEQ ID NO:23046 |
| iPS:436358 | 21-225_210D11 | NA | GGCTACTACTATATCCAC<br>SEQ ID NO:7023<br>GYYIH | TGGATCAACCCTAATAGTGGTGGCACAAACTATGCACAGAAGTTTCAGGGC<br>SEQ ID NO:15035<br>WINPNSGGTNYAQKFQG | GGATACAGCTATGGTTACAACTGGTTCGACCCC<br>SEQ ID NO:23047<br>GYSYGYNWFDP |
| | | AA | | | SEQ ID NO:23048 |
| iPS:436360 | 21-225_210H11 | NA | AGCCATGGCATGCAC<br>SEQ ID NO:7025<br>SHGMH | GTTACATGGTATGATGGAAGTGATAAATACTATGCAGACTCCGTGAAGGGC<br>SEQ ID NO:15037<br>VTWYDGSDKYYADSVKG | GACCCGGCTAGTGGGAGCTACTACCGATGCTTTGATATC<br>SEQ ID NO:23049<br>DRLVGATTDAFDI |
| | | AA | | | SEQ ID NO:23050 |
| iPS:436362 | 21-225_210C12 | NA | AACAATGGTATCAGC<br>SEQ ID NO:7027<br>NNGIS | TGGATCAACGCTTACAATGGTCACAAACTATGCACAGAAGTTCCAGGGC<br>SEQ ID NO:15039<br>WINAYNGHTNYAQKFQG | GATCCTACGGTGACCCACTACTATTACTACGGTATGGACG TC<br>SEQ ID NO:23051<br>DPTVTHYYYYGMDV |
| | | AA | SEQ ID NO:7028 | SEQ ID NO:15040 | SEQ ID NO:23052 |

FIGURE 49
(Continued)

| | | | | | |
|---|---|---|---|---|---|
| iPS:436364 | 21-225_211A11 | NA | AGCTATGGCATGCAC | GTTCTTTGGTTTGATGGA AGTAATAGAAACTATGC AGACTCCGTGAAGGGC | GATCGGGGAGTGGGCTACTA CGGTACGGACGTC |
| | | | SEQ ID NO:7029 | SEQ ID NO:15041 | SEQ ID NO:23053 |
| | | AA | SYGMH | VLWFDGSNRNYADSVKG | DRGVGYYGTDV |
| | | | SEQ ID NO:7030 | SEQ ID NO:15042 | SEQ ID NO:23054 |
| iPS:436366 | 21-225_211A3 | NA | AGTTATGGCATGCAC | GTTATATGGTATGATGG AAGTAATAAAAACTATG AAGACTCCGTGAAGGGC | GATGGGAGTTATGGTTACGA CGGTATGGACGTC |
| | | | SEQ ID NO:7031 | SEQ ID NO:15043 | SEQ ID NO:23055 |
| | | AA | SYGMH | VIWYDGSNKNYEDSVKG | DGSYGYDGMDV |
| | | | SEQ ID NO:7032 | SEQ ID NO:15044 | SEQ ID NO:23056 |
| iPS:436368 | 21-225_211G3 | NA | AACTATGGCATGCAC | GTTATATGGCATGATGG AAGTAATAAATACTATG CAGACTCCGTGAAGGGC | TTAGACTACAGTAACTACGG GTGGTTCGACCCC |
| | | | SEQ ID NO:7033 | SEQ ID NO:15045 | SEQ ID NO:23057 |
| | | AA | NYGMH | VIWHDGSNKYYADSVKG | LDYSNYGWFDP |
| | | | SEQ ID NO:7034 | SEQ ID NO:15046 | SEQ ID NO:23058 |
| iPS:436370 | 21-225_211A6 | NA | AGCTATGGCATGCAC | GTTATATGGTATGATGG AAGTAATAAAAACTATG CAGACTCCGTGAAGGGC | GATAGGACGGTGGGCTATGA TGGTTTTGATATC |
| | | | SEQ ID NO:7035 | SEQ ID NO:15047 | SEQ ID NO:23059 |
| | | AA | SYGMH | VIWYDGSNKNYADSVKG | DRIVGYDGFDI |

FIGURE 49
(Continued)

| | | | | | | | |
|---|---|---|---|---|---|---|---|
| iPS:436372 | 21-225_211A8 | NA | SEQ ID NO:7036<br>AGCTATGGCATGCAC | SEQ ID NO:15048<br>GTTATATGGTATGATGG<br>AAGTAATGAACACTATG<br>CAGACTCCGTGAAGGC | SEQ ID NO:23060<br>GACCACGGTGTCGGGTACTA<br>CGGTATGGACGTC |
| | | AA | SEQ ID NO:7037<br>SYGMH | SEQ ID NO:15049<br>VIWYDGSNEHYADSVKG | SEQ ID NO:23061<br>DHGVGYYGMDV |
| iPS:436374 | 21-225_211C10 | NA | SEQ ID NO:7038<br>AGGCATGGTATCAGG | SEQ ID NO:15050<br>TGGATCAGCGCTTACAA<br>TGGTCTCACAAACTATGC<br>ACAGAAGTTCCAGGGC | SEQ ID NO:23062<br>GATCCTACGGTGACCCACTA<br>CTACTACTACGGTATGGACG<br>TC |
| | | AA | SEQ ID NO:7039<br>RHGIS | SEQ ID NO:15051<br>WISAYNGLTNYAQKFQG | SEQ ID NO:23063<br>DPTVTHYYYYGMDV |
| iPS:436376 | 21-225_212E6 | NA | SEQ ID NO:7040<br>AGCTATGGCATGCAC | SEQ ID NO:15052<br>GTTATATGGTATGATGG<br>AAGTAATAAAACTATG<br>TAGACTCCGTGAAGGC | SEQ ID NO:23064<br>GACTACGGTGTCGGGTACTA<br>CGGTACGGACGTC |
| | | AA | SEQ ID NO:7041<br>SYGMH | SEQ ID NO:15053<br>VIWYDGSNKNYVDSVKG | SEQ ID NO:23065<br>DYGVGYYGTDV |
| iPS:436378 | 21-225_212D7 | NA | SEQ ID NO:7042<br>AGCTATGGCATGCAC | SEQ ID NO:15054<br>GTTATATGGTATGATGG<br>AAGTAATAAAATTATG<br>CAGACTCCGTGAAGGC | SEQ ID NO:23066<br>GACTACGGTGTCGGGTACTA<br>CGGTACGGACGTC |
| | | AA | SEQ ID NO:7043<br>SYGMH | SEQ ID NO:15055<br>VIWYDGSNKNYADSVKG | SEQ ID NO:23067<br>DYGVGYYGTDV |

FIGURE 49
(Continued)

| | | | | | |
|---|---|---|---|---|---|
| iPS:436380 | 21-225_212H9 | NA | SEQ ID NO:7044 AGCTATGGCATGCAC | SEQ ID NO:15056 GTTATATGGTATGATGG AAGTAATGAACACTATG CAGACTCCGTGAAGGGC | SEQ ID NO:23068 GACCACGGTGTCGGGTACTA CGGTATGGACGTC |
| | | AA | SEQ ID NO:7045 SYGMH | SEQ ID NO:15057 VIWYDGSNEHYADSVKG | SEQ ID NO:23069 DHGVGYYGMDV |
| iPS:436382 | 21-225_212C10 | NA | SEQ ID NO:7046 AGCTATGGCATGCAC | SEQ ID NO:15058 GCTATATGGTATGATGG AAGTCATAAATACTATA CAGATTCCGTGAAGGGC | SEQ ID NO:23070 GATCGGAGTATAGTGGGAGC TACCTACTTTGACTAC |
| | | AA | SEQ ID NO:7047 SYGMH | SEQ ID NO:15059 AIWYDGSHKYYTDSVKG | SEQ ID NO:23071 DRSIVGATYFDY |
| iPS:436384 | 21-225_212F10 | NA | SEQ ID NO:7048 AGATATGGCATGCAC | SEQ ID NO:15060 GTTATATGGTATGATGG AAGTAATAAACACTATG CAGACTCCGTGAAGGGC | SEQ ID NO:23072 GATCGGGGAGTGGGCTACAA CGGTATGGACGTC |
| | | AA | SEQ ID NO:7049 RYGMH | SEQ ID NO:15061 VIWYDGSNKHYADSVKG | SEQ ID NO:23073 DRGVGYNGMDV |
| iPS:436386 | 21-225_212B11 | NA | SEQ ID NO:7050 GACTATGTCATGCAC | SEQ ID NO:15062 GTTATATGGTATGATGG AAGTAATAAATATTATG CAGACTCCGTGAAGGGC | SEQ ID NO:23074 GAACGTTATAGCAGTGGCTG GTACGACTACGGTATGGACG TC |
| | | | SEQ ID NO:7051 | SEQ ID NO:15063 | SEQ ID NO:23075 |

FIGURE 49
(Continued)

| | | AA | DYVMH | | VIWYDGSNKYYADSVKG | | ERYSSGWYDYGMDV | |
|---|---|---|---|---|---|---|---|---|
| iPS:436388 | | NA | AGTTATGGCATGCAC | SEQ ID NO:7052 | GTTATATGGTGATGG AAGTAATAAAAACTATG AAGACTCCGTGAAGGGC | SEQ ID NO:15064 | GATGGGAGTTATGGTTACGA CGGTATGGACGTC | SEQ ID NO:23076 |
| | 21-225_212H11 | AA | SYGMH | SEQ ID NO:7053 | VIWYDGSNKNYEDSVKG | SEQ ID NO:15065 | DGSYGYDGMDV | SEQ ID NO:23077 |
| iPS:436390 | | NA | AGCTATGGCATGCAC | SEQ ID NO:7054 | GTTATATGGTATGATGG AAGTAATAAAAATTATG CAGACTCCGTGAAGGGC | SEQ ID NO:15066 | GACTACGGTGTCGGGTACTA CGGTACGGACGTC | SEQ ID NO:23078 |
| | 21-225_213D2 | AA | SYGMH | SEQ ID NO:7055 | VIWYDGSNKNYADSVKG | SEQ ID NO:15067 | DYGVGYYYGTDV | SEQ ID NO:23079 |
| iPS:436392 | | NA | AGCTATGGCATGCAC | SEQ ID NO:7056 | GTTATATGGTATGATGG AAGTAATAAAAACTATG CAGACTCCGTGAAGGGC | SEQ ID NO:15068 | GATAGGACGGTGGGCTATGA TGGTTTTGATATC | SEQ ID NO:23080 |
| | 21-225_213B3 | AA | SYGMH | SEQ ID NO:7057 | VIWYDGSNKNYADSVKG | SEQ ID NO:15069 | DRTVGYDGFDI | SEQ ID NO:23081 |
| | | NA | AGCTATGGCATGCAC | SEQ ID NO:7058 | | SEQ ID NO:15070 | | SEQ ID NO:23082 |

FIGURE 49
(Continued)

| | | NA | AGCTATGGCATGCAC | GTTATATGGTATGATGG AAGTAATAAACACTATG CAGACTCCGTGAAGGGC | GACTACGGTGTCGGGTACGA CGGTATGGACGTC |
|---|---|---|---|---|---|
| iPS:436394 | 21-225_213C4 | | SEQ ID NO:7059 | SEQ ID NO:15071 | SEQ ID NO:23083 |
| | | AA | SYGMH | VIWYDGSNKHYADSVKG | DYGVGYDGMDV |
| | | | SEQ ID NO:7060 | SEQ ID NO:15072 | SEQ ID NO:23084 |
| | | NA | AGTTATGGCATGCAC | GTTATATGGTATGATGG AAGTAATAAAACACTATG AAGACTCCGTGAAGGGC | GATGGGAGTTATGGTTACGA CGGTATGGACGTC |
| iPS:436396 | 21-225_213E5 | | SEQ ID NO:7061 | SEQ ID NO:15073 | SEQ ID NO:23085 |
| | | AA | SYGMH | VIWYDGSNKHYEDSVKG | DGSYGYDGMDV |
| | | | SEQ ID NO:7062 | SEQ ID NO:15074 | SEQ ID NO:23086 |
| | | NA | AGCTATGGCATGCAC | GTTATATGGTATGATGG AAGTAATAAACACTATG CAGACTCCGTGAAGGGC | GACTACGGTGTCGGGTACTA CGGTACGGACGTC |
| iPS:436398 | 21-225_213B8 | | SEQ ID NO:7063 | SEQ ID NO:15075 | SEQ ID NO:23087 |
| | | AA | SYGMH | VIWYDGSNKHYADSVKG | DYGVGYYGTDV |
| | | | SEQ ID NO:7064 | SEQ ID NO:15076 | SEQ ID NO:23088 |
| | | NA | GGCTACCATATGCAC | TGGATCAATCCTAAGAG TGATGGCACAAACTATG CACAGAAGTTTCAGGGC | GAAAAGCCTGGGAGCTACTA CAAATAC |
| iPS:436400 | 21-225_213H7 | | SEQ ID NO:7065 | SEQ ID NO:15077 | SEQ ID NO:23089 |
| | | AA | GYHMH | WINPKSDGTNYAQKFQG | EKPGSYYKY |
| | | | SEQ ID NO:7066 | SEQ ID NO:15078 | SEQ ID NO:23090 |

FIGURE 49
(Continued)

| iPS: | | NA/AA | | | |
|---|---|---|---|---|---|
| iPS:436402 | 21-225_213H12 | NA | AGCTATGGTATCAAC | TGGATCAGGGTTCACAA TGGTAACACAGACTATG CACAGAAGTTCCAGGGC | GACTACTACTACGGTATGGA CGTC |
| | | | SEQ ID NO:7067 | SEQ ID NO:15079 | SEQ ID NO:23091 |
| | | AA | SYGIN | WISVHNGNTDYAQKFQG | DYYYGMDV |
| | | | SEQ ID NO:7068 | SEQ ID NO:15080 | SEQ ID NO:23092 |
| iPS:436404 | 21-225_214C3 | NA | AGCTATGGCATGCAC | GTTATATGGTATGATGG AAGTAATAAAAACTATG GAGACTCCGTGAAGGGC | GATCGGGGAGTGGGCTACGA CGGAATGGACGTC |
| | | | SEQ ID NO:7069 | SEQ ID NO:15081 | SEQ ID NO:23093 |
| | | AA | SYGMH | VIWYDGSNKNYGDSVKG | DRGVGYDGMDV |
| | | | SEQ ID NO:7070 | SEQ ID NO:15082 | SEQ ID NO:23094 |
| iPS:436406 | 21-225_214E4 | NA | AGCTATGGCATGCAC | GTTATATGGTATGATGG AAGTAATGAAAACTATG CAGACTCCGTGAAGGGC | GATAGGACGGTGGGCTATGA TGGTTGTGATATC |
| | | | SEQ ID NO:7071 | SEQ ID NO:15083 | SEQ ID NO:23095 |
| | | AA | SYGMH | VIWYDGSNENYADSVKG | DRTVGYDGCDI |
| | | | SEQ ID NO:7072 | SEQ ID NO:15084 | SEQ ID NO:23096 |
| iPS:436408 | 21-225_214H8 | NA | GGCCACTATATACAC | TGGATCAACTCTAACAG TGGTGGCACAAACTATG CACAGAAGTTTCAGGGC | GACGGGAGATACAGCTATGG TTACGACTGGTTCGACCCC |
| | | | SEQ ID NO:7073 | SEQ ID NO:15085 | SEQ ID NO:23097 |
| | | AA | GHYIH | WINSNSGGTNYAQKFQG | DGRYSYGYDWFDP |
| | | | SEQ ID NO:7074 | SEQ ID NO:15086 | SEQ ID NO:23098 |

FIGURE 49
(Continued)

| | | | | | |
|---|---|---|---|---|---|
| iPS:436410 | 21-225_212E10 | NA | AGCTATGGCATGCAC SEQ ID NO:7075 | GTTATATGGTATGATGG AAGTAATAAATACTATG CAGACTCCGTGAAGGGC SEQ ID NO:15087 | GACTACGGTGTCGGGTACTA CGGTACGGACGTC SEQ ID NO:23099 |
| | | AA | SYGMH SEQ ID NO:7076 | VIWYDGSNKYYADSVKG SEQ ID NO:15088 | DYGVGYYGTDV SEQ ID NO:23100 |
| iPS:436412 | 21-225_214H9 | NA | AGCTATGTCATGCAC SEQ ID NO:7077 | GTTATATGGTATGATGG AAGTAATAAATACTATG CAGACTCCGTGAAGGGC SEQ ID NO:15089 | GAGAGGTATACCAGCAGCTG GTACGACTACGGTATGGACG TC SEQ ID NO:23101 |
| | | AA | SYVMH SEQ ID NO:7078 | VIWYDGSNKYYADSVKG SEQ ID NO:15090 | ERYTSSWYDYGMDV SEQ ID NO:23102 |
| iPS:436414 | 21-225_214G10 | NA | GACTATGTCATGCAC SEQ ID NO:7079 | GTTATATGGTATGATGG AAGTAATAAATATTATG CAGACTCCGTGAAGGGC SEQ ID NO:15091 | GAACGTTATAGCAGTGGCTG GTACGACTACGGTATGGACG TC SEQ ID NO:23103 |
| | | AA | DYVMH SEQ ID NO:7080 | VIWYDGSNKYYADSVKG SEQ ID NO:15092 | ERYSSGWYDYGMDV SEQ ID NO:23104 |
| iPS:436416 | 21-225_214G12 | NA | GACTATGTCATGCAC SEQ ID NO:7081 | GTTATATGGTATGATGG AAGTAATAAATATTATG CAGACTCCGTGAAGGGC SEQ ID NO:15093 | GAACGTTATAGCAGTGGCTG GTACGACTACGGTATGGACG TC SEQ ID NO:23105 |
| | | AA | DYVMH SEQ ID NO:7082 | VIWYDGSNKYYADSVKG SEQ ID NO:15094 | ERYSSGWYDYGMDV SEQ ID NO:23106 |

FIGURE 49
(Continued)

| | | | | | |
|---|---|---|---|---|---|
| iPS:436418 | 21-225_215E3 | NA | GACTATGTCATACAC | GTTATATGGTATGATGG AAGTAATAAATATTATG CAGACTCCGTGAAGGGC | GAACGTTATAGCAGTGGCTG GTACGACTACGGTATGGACG TC |
| | | | SEQ ID NO:7083 | SEQ ID NO:15095 | SEQ ID NO:23107 |
| | | AA | DYVIH | VIWYDGSNKYYADSVKG | ERYSSGWYDYGMDV |
| | | | SEQ ID NO:7084 | SEQ ID NO:15096 | SEQ ID NO:23108 |
| iPS:436420 | 21-225_215B5 | NA | AGCTATGGCATGCAC | GTTATATGGTATGATGG AAGTAATAAAATTATG CAGACTCCGTGAAGGGC | GACTACGGTGTCGGGTACTA CGGTACGGACGTC |
| | | | SEQ ID NO:7085 | SEQ ID NO:15097 | SEQ ID NO:23109 |
| | | AA | SYGMH | VIWYDGSNKNYADSVKG | DYGVGYYGTDV |
| | | | SEQ ID NO:7086 | SEQ ID NO:15098 | SEQ ID NO:23110 |
| iPS:436422 | 21-225_215D6 | NA | AGCTATGGCATGCAC | GTTATATGGTATGATGG AAGTAATAAAACTATG CAGATTCCGTGAAGGGC | GACTGCGGTGTCGGATACTA CGGTACGGACGTC |
| | | | SEQ ID NO:7087 | SEQ ID NO:15099 | SEQ ID NO:23111 |
| | | AA | SYGMH | VIWYDGSNKNYADSVKG | DCGVGYYGTDV |
| | | | SEQ ID NO:7088 | SEQ ID NO:15100 | SEQ ID NO:23112 |
| iPS:436424 | 21-225_215H6 | NA | GGCCACTATATACAC | TGGATCAACTCTAACAG TGGTGGCACAAATTATG CAGAGAAGTTTCAGGGC | GACGGGAGATACAGCTATGG TCACGACTGGTTCGACCCC |
| | | | SEQ ID NO:7089 | SEQ ID NO:15101 | SEQ ID NO:23113 |
| | | AA | GHYTH | WINSNSGGTNYAEKFQG | DGRYSYGHDWFDP |
| | | | SEQ ID NO:7090 | SEQ ID NO:15102 | SEQ ID NO:23114 |

FIGURE 49
(Continued)

| | | | | | | |
|---|---|---|---|---|---|---|
| iPS:436426 | 21-225_215C7 | NA | TACTATGGCATGCAC | | GTTATATGGCATGATGG AAGTAATAAATACTATG CAGACTCCGTGAAGGGC | | TTAGACTACAGTAATTACGG GTGGTTCGACCCC |
| | | AA | SEQ ID NO:7091 YYGMH | SEQ ID NO:15103 VIWYDGSNKYYADSVKG | SEQ ID NO:23115 LDYSNYGWFDP |
| iPS:436428 | 21-225_215E11 | NA | SEQ ID NO:7092 GACTATGTCATGCAC | SEQ ID NO:15104 GTTATATGGTATGATGG AAGTAATAAATATTATG CAGACTCCGTGAAGGGC | SEQ ID NO:23116 GAACGTTATAGCAGTGGCTG GTACGACTACGGTATGGACG TC |
| | | AA | SEQ ID NO:7093 DYVMH | SEQ ID NO:15105 VIWYDGSNKYYADSVKG | SEQ ID NO:23117 ERYSSGWYDYGMDV |
| iPS:436430 | 21-225_215A12 | NA | SEQ ID NO:7094 AGCTATGGCATGCAC | SEQ ID NO:15106 GTTATATGGTATGATGG AAGTAATGAACACTATG CAGACTCCGTGAAGGGC | SEQ ID NO:23118 GATCGGGGAGTGGGCTACTA CGGTATGGACGTC |
| | | AA | SEQ ID NO:7095 SYGMH | SEQ ID NO:15107 VIWYDGSNEHYADSVKG | SEQ ID NO:23119 DRGVGYYGMDV |
| iPS:436432 | 21-225_215H12 | NA | SEQ ID NO:7096 AACTATGGCATGCAC | SEQ ID NO:15108 GTTATATGGCATGATGG AAGTAATAAATACTATG CAGACTCCGTGAAGGGC | SEQ ID NO:23120 TTAGACTACAGTAACTACGG GTGGTTCGACCCC |
| | | AA | SEQ ID NO:7097 NYGMH | SEQ ID NO:15109 VIWHDGSNKYYADSVKG | SEQ ID NO:23121 LDYSNYGWFDP |

FIGURE 49
(Continued)

| | | | | | | |
|---|---|---|---|---|---|---|
| iPS:436434 | 21-225_216B10 | NA | SEQ ID NO:7098 AGCTATGGCATGCAC | SEQ ID NO:15110 GCTATATGGTATGATGG AAGTAATAAATACTATG CAGACTCCGTGAAGGGC | SEQ ID NO:23122 GATCCAACATAGTGGGAGC TACTTGGTTTGACTAC | |
| | | AA | SEQ ID NO:7099 SYGMH | SEQ ID NO:15111 AIWYDGSNKYYADSVKG | SEQ ID NO:23123 DPNIVGATWFDY | |
| iPS:436436 | 21-225_216F10 | NA | SEQ ID NO:7100 AGCTATAGCATGAAC | SEQ ID NO:15112 TACATTACTGGTAGTAGT AGTACCATATACTACG AGACTCTGTGAAGGGC | SEQ ID NO:23124 TCGGGTTTAGCAGTGGAGGA CTAC | |
| | | AA | SEQ ID NO:7101 SYSMN | SEQ ID NO:15113 YITGSSSTIYYADSVKG | SEQ ID NO:23125 SGLAVEDY | |
| iPS:436438 | 21-225_216E8 | NA | SEQ ID NO:7102 GACTATGTCATGCAC | SEQ ID NO:15114 GTTATATGGTATGATGG AAGTAATAAATATTATG CAGACTCCGTGAAGGGC | SEQ ID NO:23126 GAACGTTATAGCAGTGGCTG GTACGACTACGGTATGGACG TC | |
| | | AA | SEQ ID NO:7103 DYVMH | SEQ ID NO:15115 VIWYDGSNKYYADSVKG | SEQ ID NO:23127 ERYSSGWYDYGMDV | |
| iPS:436440 | 21-225_216H12 | NA | SEQ ID NO:7104 GACTATGTCATGCAC | SEQ ID NO:15116 GTTATATGGTATGATGG AAGTAATAAATATTATG CAGACTCCGTGAAGGGC | SEQ ID NO:23128 GAACGTTATAGCAGTGGCTG GTACGACTACGGTATGGACG TC | |
| | | AA | SEQ ID NO:7105 DYVMH | SEQ ID NO:15117 VIWYDGSNKYYADSVKG | SEQ ID NO:23129 ERYSSGWYDYGMDV | |
| | | | SEQ ID NO:7106 | SEQ ID NO:15118 | SEQ ID NO:23130 | |

FIGURE 49
(Continued)

| | | | | | |
|---|---|---|---|---|---|
| iPS:436448 | 21-225_217A3 | NA | AGCTATAATATGAAC | TACATTAGTAGTAGTCGT AATATCATATATTACGCA GACTCTGTGAAGGGC | GATGGCTCTTATAGCAGTGG CTGGTACGGGGTTTTGACT AC |
| | | AA | SEQ ID NO:7107 SYNMN | SEQ ID NO:15119 YISSSRNIIYYADSVKG | SEQ ID NO:23131 DGSYSSGWYWGFDY |
| iPS:436450 | 21-225_217E5 | NA | SEQ ID NO:7108 GACTATGTCATGCAC | SEQ ID NO:15120 GTTATATGGTATGATGG AAGTAATAAATATTATG CAGACTCCGTGAAGGGC | SEQ ID NO:23132 GAACGTTATAGCAGTGGCTG GTACGACTACGGTATGGACG TC |
| | | AA | SEQ ID NO:7109 DYVMH | SEQ ID NO:15121 VIWYDGSNKYYADSVKG | SEQ ID NO:23133 ERYSSGWYDYGMDV |
| iPS:436452 | 21-225_217G5 | NA | AGCAATGGCATGCAC | GTTATATGGTATGAGG AAGTAATAAAACTATG CGGTCTGGACGTC | GACTACGGTGTCGGGTACTA CGGTCTGGACGTC |
| | | AA | SEQ ID NO:7110 SNGMH | SEQ ID NO:15122 | SEQ ID NO:23134 |
| | | | SEQ ID NO:7111 | SEQ ID NO:15123 VIWYDGSNKNYADSVKG | SEQ ID NO:23135 DYGVGYYGLDV |
| iPS:436454 | 21-225_217B10 | NA | AGTTATATGGCATGCAC | GTTATATGGTATGATGG AAGTAATAAAACTATG AAGACTCCGTGAAGGGC | GATGGGAGTTATGGTTACGA CGGTATGGACGTC |
| | | AA | SEQ ID NO:7112 SYGMH | SEQ ID NO:15124 | SEQ ID NO:23136 |
| | | | SEQ ID NO:7113 | SEQ ID NO:15125 VIWYDGSNKNYEDSVKG | SEQ ID NO:23137 DGSYGYDGMDV |
| | | | SEQ ID NO:7114 | SEQ ID NO:15126 | SEQ ID NO:23138 |

FIGURE 49
(Continued)

| | | | | | |
|---|---|---|---|---|---|
| iPS:436456 | 21-225_217G10 | NA | GACTATGTCATGCAC SEQ ID NO:7115 | GTTATATGGTATGATGG AAGTAATAAATATTATG CAGACTCCGTGAAGGGC SEQ ID NO:15127 | GAACGTTATAGCAGTGGCTG GTACGACTACGGTATGGACG TC SEQ ID NO:23139 |
| | | AA | DYVMH SEQ ID NO:7116 | VIWYDGSNKYYADSVKG SEQ ID NO:15128 | ERYSSGWYDYGMDV SEQ ID NO:23140 |
| iPS:436458 | 21-225_217H12 | NA | GACTATGTCATGCAC SEQ ID NO:7117 | GTTATATGGTATGATGG AAGTAATAAATATTATG CAGACTCCGTGAAGGGC SEQ ID NO:15129 | GAACGTTATAGCAGTGGCTG GTACGACTACGGTATGGACG TC SEQ ID NO:23141 |
| | | AA | DYVMH SEQ ID NO:7118 | VIWYDGSNKYYADSVKG SEQ ID NO:15130 | ERYSSGWYDYGMDV SEQ ID NO:23142 |
| iPS:436462 | 21-225_218C4 | NA | GACTATGTCATGCAC SEQ ID NO:7119 | GTTATATGGTATGATGG AAGTAATAAATATTATG CAGACTCCGTGAAGGGC SEQ ID NO:15131 | GAACGTTATAGCAGTGGCTG GTACGACTACGGTATGGACG TC SEQ ID NO:23143 |
| | | AA | DYVMH SEQ ID NO:7120 | VIWYDGSNKYYADSVKG SEQ ID NO:15132 | ERYSSGWYDYGMDV SEQ ID NO:23144 |
| iPS:436464 | 21-225_219H1 | NA | AGATATGGCATGCAC SEQ ID NO:7121 | GTTATATGGTATGATGG AAGTAATAAACACTATG CAGACTCCGTGAAGGGC SEQ ID NO:15133 | GATCGGGGAGTGGCTACAA CGGTATGGACGTC SEQ ID NO:23145 |
| | | AA | RYGMH SEQ ID NO:7122 | VIWYDGSNKHYADSVKG SEQ ID NO:15134 | DRGVGYNGMDV SEQ ID NO:23146 |

FIGURE 49 (Continued)

| | | | | | |
|---|---|---|---|---|---|
| iPS:436472 | 21-225_220E1 | NA | ACTTACTACTGGAGC | TATATCTATTACAGTGGG ACCACCAACTACAACCC CTCCCTCAAGAGT | GACCAGCAGTGGCTGGTACG TGGGAGGGACAACTACTACT ACGGTATGGACGTC |
| | | | SEQ ID NO:7123 | SEQ ID NO:15135 | SEQ ID NO:23147 |
| | | AA | TYYWS | YIYYSGTTNYNPSLKS | DQQWLVRGRDNYYYGMDV |
| | | | SEQ ID NO:7124 | SEQ ID NO:15136 | SEQ ID NO:23148 |
| iPS:436480 | 21-225_220F8 | NA | GACTATGTCATGCAC | GTTATATGGTATGATGG AAGTAATAAATATTATG CAGACTCCGTGAAGGGC | GAACGTTATAGCAGTGGCTG GTACGACTACGGTATGGACG TC |
| | | | SEQ ID NO:7125 | SEQ ID NO:15137 | SEQ ID NO:23149 |
| | | AA | DYVMH | VIWYDGSNKYYADSVKG | ERYSSGWYDYGMDV |
| | | | SEQ ID NO:7126 | SEQ ID NO:15138 | SEQ ID NO:23150 |
| iPS:436488 | 21-225_221A6 | NA | GGCTACTATATGCAC | TGGATCCACCCTAACAG TGGTGGCACAAACTATG CACAGAAATTTCAGGGC | GATGGGACCAGCTCGTTTGA CTAC |
| | | | SEQ ID NO:7127 | SEQ ID NO:15139 | SEQ ID NO:23151 |
| | | AA | GYYMH | WIHPNSGGTNYAQKFQG | DGTSSFDY |
| | | | SEQ ID NO:7128 | SEQ ID NO:15140 | SEQ ID NO:23152 |
| iPS:436490 | 21-225_221F6 | NA | AGCAATGGCATGCAC | GTTATATGGTACGATGG AAGTAATGAAAACTATG CAGACTCCGTGAAGGGC | GATCGGACAGTGGGCTACAA CGGTATGGACGTC |
| | | | SEQ ID NO:7129 | SEQ ID NO:15141 | SEQ ID NO:23153 |
| | | AA | SNGMH | VIWYDGSNENYADSVKG | DRTVGYNGMDV |
| | | | SEQ ID NO:7130 | SEQ ID NO:15142 | SEQ ID NO:23154 |
| iPS:436496 | 21-225_222E1 | NA | GGCTACTATATGCAC | TGGATCCACCCTAACAG TGGTGGCACAAACTATG CACAGAAATTTCAGGGC | GATGGGACCAGCTCGTTTGA CTAC |

FIGURE 49
(Continued)

| | | | | | |
|---|---|---|---|---|---|
| iPS:436500 | 21-225_222E1 | AA | SEQ ID NO:7131<br>GYYMH | SEQ ID NO:15143<br>WIHPNSGGTNYAQKFQG | SEQ ID NO:23155<br>DGTSSFDY |
| | | NA | SEQ ID NO:7132<br>AGCTATGGTATCAAC | SEQ ID NO:15144<br>TGGATCAGCGTTTACAAT<br>GGTAACACAAACTATGC<br>ACAGAAGCTCCAGGGC | SEQ ID NO:23156<br>GACTACTACGGTTTTGA<br>CGTC |
| iPS:436502 | 21-225_222H3 | AA | SEQ ID NO:7133<br>SYGIN | SEQ ID NO:15145<br>WISVYNGNTNYAQKLQG | SEQ ID NO:23157<br>DYYYGFDV |
| | | NA | SEQ ID NO:7134<br>AGCTATGGCATGCAC | SEQ ID NO:15146<br>GTTATATGGTATGATGG<br>AAGTAATAAAAACTATG<br>CAGACTCCGTGAAGGGC | SEQ ID NO:23158<br>GATCGGGATGTCGGGTACAA<br>CGGTATGGACGTC |
| iPS:436504 | 21-225_222A11 | AA | SEQ ID NO:7135<br>SYGMH | SEQ ID NO:15147<br>VIWYDGSNKNYADSVKG | SEQ ID NO:23159<br>DRDVGYNGMDV |
| | | NA | SEQ ID NO:7136<br>AACTTTGCCATGAGT | SEQ ID NO:15148<br>AGTATTGTTGGTAGTGGT<br>GGTGCACGTACTACGC<br>AGACTCCGTGAAGGGC | SEQ ID NO:23160<br>GACCCTTATCGTGTAGCAGT<br>GGCTGGGGCCTTTGACTAC |
| | 21-225_222H4 | AA | SEQ ID NO:7137<br>NFAMS | SEQ ID NO:15149<br>SIVGSGGRTYYADSVKG | SEQ ID NO:23161<br>DPYRVAVAGAFDY |
| iPS:436506 | | NA | SEQ ID NO:7138<br>GGTCGCTACTGGAGC | SEQ ID NO:15150<br>GAAATAATCATATGG<br>AAGGGCCAACTACAACC<br>CGTCCCTCAAGAGT | SEQ ID NO:23162<br>GACTACGGCGCCCTTGATTT<br>C |
| | 21-225_222C7 | AA | SEQ ID NO:7139<br>GRYWS | SEQ ID NO:15151<br>EINHSGSANYNPSLKS | SEQ ID NO:23163<br>DYGALDF |

FIGURE 49
(Continued)

| | | | | | |
|---|---|---|---|---|---|
| iPS:436508 | 21-225_222F7 | NA | SEQ ID NO:7140<br>GGCTACTATATGCAC | SEQ ID NO:15152<br>TGGATCCACCCTAACAG<br>TGGTGGCACAAACTATG<br>CACAGAAATTTCAGGGC | SEQ ID NO:23164<br>GATGGGACCAGCTCGTTTGA<br>CTAC |
| | | AA | SEQ ID NO:7141<br>GYYMH | SEQ ID NO:15153<br>WIHPNSGGTNYAQKFQG | SEQ ID NO:23165<br>DGTSSFDY |
| iPS:436510 | 21-225_222H8 | NA | SEQ ID NO:7142<br>AACTTTGCCATGAGT | SEQ ID NO:15154<br>AGTATTGTTGGTAGTGGT<br>GGTCGCACGTACTACGC<br>AGACTCCGTGAAGGGC | SEQ ID NO:23166<br>GACCCTTATCGTGTAGCAGT<br>GGCTGGGGCCTTTGACTAC |
| | | AA | SEQ ID NO:7143<br>NFAMS | SEQ ID NO:15155<br>SIVGSGGRTYYADSVKG | SEQ ID NO:23167<br>DPYRVAVAGAFDY |
| iPS:436514 | 21-225_222D10 | NA | SEQ ID NO:7144<br>AGTATGGCATGCAC | SEQ ID NO:15156<br>GTTATATGGTATGATGG<br>AAGTAATAAAAACTATG<br>CAGACTCCGTGAAGGGC | SEQ ID NO:23168<br>GATCGGGATGTCGGGTACAA<br>CGGTATGGACGTC |
| | | AA | SEQ ID NO:7145<br>SYGMH | SEQ ID NO:15157<br>VIWYDGSNKNYADSVKG | SEQ ID NO:23169<br>DRDVGYNGMDV |
| iPS:436516 | 21-225_222C12 | NA | SEQ ID NO:7146<br>GGCTACTATATGCAC | SEQ ID NO:15158<br>TGGATCCACCCTAACAG<br>TGGTGGCACAAACTATG<br>CACAGAAATTTCAGGGC | SEQ ID NO:23170<br>GATGGGACCAGCTCGTTTGA<br>CTAC |
| | | AA | SEQ ID NO:7147<br>GYYMH | SEQ ID NO:15159<br>WIHPNSGGTNYAQKFQG | SEQ ID NO:23171<br>DGTSSFDY |
| | | | SEQ ID NO:7148 | SEQ ID NO:15160 | SEQ ID NO:23172 |

FIGURE 49
(Continued)

| iPS | | | | |
|---|---|---|---|---|
| iPS:436520 | 21-225_223G10 | NA | AGCTATGGTATCAAC | TGGATCAGGGTTTACAGTGGTAACACAAACTATGCACAGAAGTCCAGGGC | GACTACTACTACGGTATGGACGTC |
| | | | SEQ ID NO:7149 | SEQ ID NO:15161 | SEQ ID NO:23173 |
| | | AA | SYGIN | WISVYSGNTNYAQKLQG | DYYYGMDV |
| | | | SEQ ID NO:7150 | SEQ ID NO:15162 | SEQ ID NO:23174 |
| iPS:436522 | 21-225_223H10 | NA | AGCTATGGCATGCAC | GTTATATGGTATGATGGAAGTAATAAAAACTATGCAGACTCCGTGAAGGGC | GATCGGGATGTCGGGTACAACGGTATGGACGTC |
| | | | SEQ ID NO:7151 | SEQ ID NO:15163 | SEQ ID NO:23175 |
| | | AA | SYGMH | VIWYDGSNKNYADSVKG | DRDVGYNGMDV |
| | | | SEQ ID NO:7152 | SEQ ID NO:15164 | SEQ ID NO:23176 |
| iPS:436526 | 21-225_224A1 | NA | AGCTATGCCATGAGC | GCTATTAGTGGCAGAGGCGGCAGCACATACTACGCAGACGCCGTGAAGGGC | GGCTCCTAGGATAGTAGTGGTTATTACCACTACTTAGACCAC |
| | | | SEQ ID NO:7153 | SEQ ID NO:15165 | SEQ ID NO:23177 |
| | | AA | SYAMS | AISGRGGSTYYADAVKG | GSYDSSGYYHYLDH |
| | | | SEQ ID NO:7154 | SEQ ID NO:15166 | SEQ ID NO:23178 |
| iPS:436528 | 21-225_224B1 | NA | AGCTATGCCATGAGC | GCTATTAGTGGTAGTGGTGGTAACACATACTACGCAGACTCCGTGAAGGGC | GAGGGGGCTACTACTATTACTACGGTGTGGACGTC |
| | | | SEQ ID NO:7155 | SEQ ID NO:15167 | SEQ ID NO:23179 |
| | | AA | SYAMS | AISGSGGNTYADSVKG | EGGYYYYYGVDV |
| | | | SEQ ID NO:7156 | SEQ ID NO:15168 | SEQ ID NO:23180 |

FIGURE 49
(Continued)

| | | | | |
|---|---|---|---|---|
| iPS:436534 | 21-225_224F1 | NA | AGCTATATCATGCAC | GTTATATGGTATGATGG AAGTAATAAATACTATG CAGACTCCGTGAAGGGC | GAGAGGTATAGCAGCAGCAACTG GTACGACTACGGTATGGACG TC |
| | | | SEQ ID NO:7157 | SEQ ID NO:15169 | SEQ ID NO:23181 |
| | | AA | SYIMH | VIWYDGSNKYYADSVKG | ERYSSNWYDYGMDV |
| | | | SEQ ID NO:7158 | SEQ ID NO:15170 | SEQ ID NO:23182 |
| iPS:436536 | 21-225_224G1 | NA | GGCTACTATATACAC | TGGATCAACCCTACAGT GGTGACACAAACTATGC ACAGAAGTTCAGGGC | GATTGGGGTGGCTACAGTTC TTACTACTACGGTATGGACG TC |
| | | | SEQ ID NO:7159 | SEQ ID NO:15171 | SEQ ID NO:23183 |
| | | AA | GYYIH | WINPYSGDTNYAQKFQG | DWGGYSSYYGMDV |
| | | | SEQ ID NO:7160 | SEQ ID NO:15172 | SEQ ID NO:23184 |
| iPS:436538 | 21-225_224C3 | NA | AGAAGTAGTTACTACTGGGG C | AATATCTATTATAGTGGG AGCACTACTACAACCC GTCCCTCAAGAGT | CAGGGTCGGGACTGGGGTGT TGACTAC |
| | | | SEQ ID NO:7161 | SEQ ID NO:15173 | SEQ ID NO:23185 |
| | | AA | RSSYYWG | NIYYSGSTYYNPSLKS | QGRDWGVDY |
| | | | SEQ ID NO:7162 | SEQ ID NO:15174 | SEQ ID NO:23186 |
| iPS:436540 | 21-225_224F3 | NA | AGCTATGGCATGCAC | GTTATATGGTATGATGG AAGTAATAAATACTATG CAGACTCCGTGAAGGGC | GAGAGGTATAGCAGCAGCAGCTG GTACGACTACGGTATGGACG TC |
| | | | SEQ ID NO:7163 | SEQ ID NO:15175 | SEQ ID NO:23187 |
| | | AA | SYGMH | VIWYDGSNKYYADSVKG | ERYSSSWYDYGMDV |
| | | | SEQ ID NO:7164 | SEQ ID NO:15176 | SEQ ID NO:23188 |

FIGURE 49
(Continued)

| | | | | | |
|---|---|---|---|---|---|
| iPS:436544 | 21-225_224H5 | NA | AATTATGATATCAAC | TGGATGAACCCTAACAG TGGTAACACAGGCTATG CACAGAAGTTCCAGGGC | TCCAGTGGCTGGAACTGGTT CGACCCC |
| | | | SEQ ID NO:7165 | SEQ ID NO:15177 | SEQ ID NO:23189 |
| | | AA | NYDIN | WMNPNSGNTGYAQKFQG | SSGWNWFDP |
| | | | SEQ ID NO:7166 | SEQ ID NO:15178 | SEQ ID NO:23190 |
| iPS:436546 | 21-225_224D6 | NA | AGCGATGCCATGAGC | GCTATTAGTGGTAGTGGT GATAACACATTCTACGC AGACTCCGTGAAGGGC | GTCTATAGTGCCTACGATTC TCACTGGTTCGACCCC |
| | | | SEQ ID NO:7167 | SEQ ID NO:15179 | SEQ ID NO:23191 |
| | | AA | SDAMS | AISGSGDNTFYADSVKG | VYSAYDSHWFDP |
| | | | SEQ ID NO:7168 | SEQ ID NO:15180 | SEQ ID NO:23192 |
| iPS:436548 | 21-225_224A7 | NA | GGCTACTATATACAC | TGGATCAACCCTACAGT GGTAACACAAACTATGC ACAGAAGTTCCAGGGC | GATTGGGGTGGCTACAGTTC TTACTACTACGGTATGGACG TC |
| | | | SEQ ID NO:7169 | SEQ ID NO:15181 | SEQ ID NO:23193 |
| | | AA | GYYIH | WINPYSGDTNYAQKFQG | DWGGYSSYYYGMDV |
| | | | SEQ ID NO:7170 | SEQ ID NO:15182 | SEQ ID NO:23194 |
| iPS:436550 | 21-225_224D8 | NA | AATTATGATATCAAC | TGGTTGTACCCTAACAGT GGTAACACAGGCTATGC ACAGAAGTTCCAGGGC | AGCAGTGGCTGGTACTACTT TGACTAC |
| | | | SEQ ID NO:7171 | SEQ ID NO:15183 | SEQ ID NO:23195 |
| | | AA | NYDIN | WLYPNSGNTGYAQKFQG | SSGWYYFDY |
| | | | SEQ ID NO:7172 | SEQ ID NO:15184 | SEQ ID NO:23196 |
| iPS:436554 | 21-225_224C10 | NA | AATTATGATATCAAC | TGGATGCACCCTAACAG TGGTAACACAGGCTATG CACAGAAGTTCCAGGGC | AGCAGTGGCTGGTACAAGTT TGACTAC |
| | | | SEQ ID NO:7173 | SEQ ID NO:15185 | SEQ ID NO:23197 |

FIGURE 49
(Continued)

| | | AA | NYDIN | WMHPNSGNTGYAQKFQG | SSGWYKFDY |
|---|---|---|---|---|---|
| iPS:436556 | 21-225_224D10 | | SEQ ID NO:7174 | SEQ ID NO:15186 | SEQ ID NO:23198 |
| | | NA | AGCTATGGCATGCAC | GTTATATGGTATGAGGG AAGTAATAAATACTATG TAGACTCCGTGAGGGC | GAGCTAGGCTTCCAGTCTGA CTAC |
| | | | SEQ ID NO:7175 | SEQ ID NO:15187 | SEQ ID NO:23199 |
| | | AA | SYGMH | VIWYEGSNKYYVDSVRG | ELGFQSDY |
| iPS:436558 | 21-225_224C11 | | SEQ ID NO:7176 | SEQ ID NO:15188 | SEQ ID NO:23200 |
| | | NA | GGCTACTATATACAC | TGGATCAACCCTACAGT GGTGACACAAACTATGC ACAGAAGTTTCAGGGC | GATTGGGGTGGCTACAGTC TTACTACTTCGGTATGGACG TC |
| | | | SEQ ID NO:7177 | SEQ ID NO:15189 | SEQ ID NO:23201 |
| | | AA | GYYIH | WINPYSGDTNYAQKFQG | DWGGYSSYYFGMDV |
| iPS:436560 | 21-225_224F11 | | SEQ ID NO:7178 | SEQ ID NO:15190 | SEQ ID NO:23202 |
| | | NA | AATTATATGATATCAAC | TGGATGAACCCTAACAG TGGTAACACAGGCTATG CACAGAAGTTCCAGGGC | AGCAGTGGCTGCTGTACAAGTT TGACTAC |
| | | | SEQ ID NO:7179 | SEQ ID NO:15191 | SEQ ID NO:23203 |
| | | AA | NYDIN | WMNPNSGNTGYAQKFQG | SSGWYKFDY |
| iPS:436562 | 21-225_224H11 | | SEQ ID NO:7180 | SEQ ID NO:15192 | SEQ ID NO:23204 |
| | | NA | GGCTACTATATACAC | TGGATCAACCCTACAGT GGTGACACAAACTATGC ACAGAAGTTTCAGGGC | GATTGGGGTGGCTACAGTC TTACTACTACTTCGGTATGGACG TC |
| | | | SEQ ID NO:7181 | SEQ ID NO:15193 | SEQ ID NO:23205 |
| | | AA | GYYIH | WINPYSGDTNYAQKFQG | DWGGYSYYYGMDV |
| | | | SEQ ID NO:7182 | SEQ ID NO:15194 | SEQ ID NO:23206 |

FIGURE 49
(Continued)

| | | | | | |
|---|---|---|---|---|---|
| iPS:436564 | 21-225_225A1 | NA | GACTATGTCATCCAC | GTTATATGGTATGATGG AAGTAATAAATACTATG CAGACTCCGTGAAGGGC | GAGAGGTATAGCAGTGGCTG GTACGACTACGGTATGGACG TC |
| | | | SEQ ID NO:7183 | SEQ ID NO:15195 | SEQ ID NO:23207 |
| | | AA | DYVIH | VIWYDGSNKYYADSVKG | ERYSSGWYDYGMDV |
| | | | SEQ ID NO:7184 | SEQ ID NO:15196 | SEQ ID NO:23208 |
| iPS:436568 | 21-225_225B3 | NA | AGCTACTACTATGCAC | ATAATCAACCCTAGTGG TGGTAGCACAAGCTACG CACAGAAGTTCCAGGGC | GATTAGCAGCTCGTCTTA CTACTACTACTTCGGTATGG ACGTC |
| | | | SEQ ID NO:7185 | SEQ ID NO:15197 | SEQ ID NO:23209 |
| | | AA | SYYMH | IINPSGGSTSYAQKFQG | DLAARSYYYFGMDV |
| | | | SEQ ID NO:7186 | SEQ ID NO:15198 | SEQ ID NO:23210 |
| iPS:436570 | 21-225_225F4 | NA | AATTATGATATCAAC | TGGATGCACCCTAACAG TGGTAGCACAGGCTATG CACAGAAGTTCCAGGGC | AGCAGTGGCTGGTACTGGTT CGACCCC |
| | | | SEQ ID NO:7187 | SEQ ID NO:15199 | SEQ ID NO:23211 |
| | | AA | NYDIN | WMHPNSGSTGYAQKFQG | SSGWYWFDP |
| | | | SEQ ID NO:7188 | SEQ ID NO:15200 | SEQ ID NO:23212 |
| iPS:436572 | 21-225_225G4 | NA | GGCTACTATATACAC | TGGATCAACCCTACAGT GGTGACACAAACTATGC ACAGAAGTTCAGGGC | GATTGGGGTGGCTACAGTTC TTACTACTACGGTATGGACG TC |
| | | | SEQ ID NO:7189 | SEQ ID NO:15201 | SEQ ID NO:23213 |
| | | AA | GYYIH | WINPYSGDTNYAQKFQG | DWGGYSSYYYGMDV |
| | | | SEQ ID NO:7190 | SEQ ID NO:15202 | SEQ ID NO:23214 |
| iPS:436574 | | NA | AATTATGATATCAAC | TGGATGCATCCTAACAG TGGTAACACAGGCTTTG CACAGAAGTTCCAGGGC | AGCAGTGGCTGGTACCGCTT TGACTAC |

FIGURE 49 (Continued)

| | | | SEQ ID NO:7191 NYDIN | SEQ ID NO:15203 WMHPNSGNTGFAQKFQG | SEQ ID NO:23215 SSSGWYRFDY |
|---|---|---|---|---|---|
| iPS:436576 | 21-225_225F5 | AA | | | |
| | | NA | SEQ ID NO:7192 GACTATGGCATGCAC | SEQ ID NO:15204 GTTATATGGTATGATGA AAATAATAAATACTATG CAGACTCCGTGAAGGGC | SEQ ID NO:23216 GAAGTGGGATTCACTGAGGA CTAC |
| iPS:436578 | 21-225_225B6 | AA | SEQ ID NO:7193 DYGMH | SEQ ID NO:15205 VIWYDENNKYYADSVKG | SEQ ID NO:23217 EVGFTEDY |
| | | NA | SEQ ID NO:7194 AACTATGGCATGCAC | SEQ ID NO:15206 GTTATATGGTATGATGA AAATAATAAATACTATG CAGACTCCGTGAAGGGC | SEQ ID NO:23218 GAAGTGGGATTCACTGAGGA CTAC |
| iPS:436580 | 21-225_225D6 | AA | SEQ ID NO:7195 NYGMH | SEQ ID NO:15207 VIWYDENNKYYADSVKG | SEQ ID NO:23219 EVGFTEDY |
| | | NA | SEQ ID NO:7196 AGTGGTCATTACTACTGGAG C | SEQ ID NO:15208 TTCATCTATTACACTGGG AGCACTACTACAACCC GTCCCTCAAGAGT | SEQ ID NO:23220 GAGGCCGGTGACTACGGCTA CTACGGTATGGACGTC |
| iPS:436582 | 21-225_225E7 | AA | SEQ ID NO:7197 SGHYYWS | SEQ ID NO:15209 FIYYTGSTYNPSLKS | SEQ ID NO:23221 EAGDYGYYGMDV |
| | 21-225_225F8 | NA | SEQ ID NO:7198 AGCTATGGCATGCAC | SEQ ID NO:15210 GTTATATGGTATGATGA AAATAATAAATACTATG TAGACTCCGTGAAGGGC | SEQ ID NO:23222 GAAGTGGGATTACTGAGGA CTAC |

FIGURE 49
(Continued)

| | | | | | | |
|---|---|---|---|---|---|---|
| iPS:436584 | 21-225_225F8 | AA | SEQ ID NO:7199<br>SYGMH | SEQ ID NO:15211<br>VIWYDENNKYYVDSVKG | SEQ ID NO:23223<br>EVGFTEDY | |
| | | NA | SEQ ID NO:7200<br>AATTATGATATCAAC | SEQ ID NO:15212<br>TGGATGCACCCTAACAG<br>TGGTAACACAGGCTATG<br>CACAGAAGTTCCGGGGC | SEQ ID NO:23224<br>AGCAGTGGCTGGTACCGGCTTT<br>TGACTAC | |
| iPS:436586 | 21-225_225B9 | AA | SEQ ID NO:7201<br>NYDIN | SEQ ID NO:15213<br>WMHPNSGNTGYAQKFRG | SEQ ID NO:23225<br>SSGWTLFDY | |
| | | NA | SEQ ID NO:7202<br>AATTATGATATCAAC | SEQ ID NO:15214<br>TGGATGCACCCTAACAG<br>TGGTAACACAGGCTATG<br>CACAGAAGTTCCAGGGC | SEQ ID NO:23226<br>AGCAGTGGCTGGTACCGGCTTT<br>TGACTAC | |
| iPS:436588 | 21-225_225F11 | AA | SEQ ID NO:7203<br>NYDIN | SEQ ID NO:15215<br>WMHPNSGNTGYAQKFQG | SEQ ID NO:23227<br>SSGWYRFDY | |
| | | NA | SEQ ID NO:7204<br>CATTATGATATCAAC | SEQ ID NO:15216<br>TGGATGCACCCAAACAG<br>TGGTAACACAGGCTATG<br>CACAGAAGTTCCAGGGC | SEQ ID NO:23228<br>AGCAGTGGCTGGTACAAGTT<br>TGACTAC | |
| iPS:436590 | 21-225_225F12 | AA | SEQ ID NO:7205<br>HYDIN | SEQ ID NO:15217<br>WMHPNSGNTGYAQKFQG | SEQ ID NO:23229<br>SSGWYKFDY | |
| | | NA | SEQ ID NO:7206<br>AATTATGATATCAAC | SEQ ID NO:15218<br>TGGATGCACCCTAACAG<br>TGGTAACACAGGCTATG<br>CACAGAAGTTCCAGGGC | SEQ ID NO:23230<br>AGCAGTGGCTGGTACAAGTT<br>TGACTAC | |
| | 21-225_225H12 | | SEQ ID NO:7207 | SEQ ID NO:15219 | SEQ ID NO:23231 | |

FIGURE 49
(Continued)

| ID | SubID | AA/NA | CDR1 | SEQ ID | CDR2 | SEQ ID | CDR3 | SEQ ID |
|---|---|---|---|---|---|---|---|---|
| iPS:436592 | 21-225_226B1 | AA | NYDIN | | WMHPNSGNTGYAQKFQG | | SSGWYKFDY | |
| | | NA | ACCTATGGCATGCAC | SEQ ID NO:7208 | ATTATATGGTATGATGG AGGTTATAAATACTATG CAGACTCCGTGAAGGC | SEQ ID NO:15220 | GATCACTACGATTTTGGAG TGGTTATCTTACCCAC | SEQ ID NO:23232 |
| iPS:436594 | 21-225_226A5 | AA | TYGMH | SEQ ID NO:7209 | IIWYDGGYKYYADSVKG | SEQ ID NO:15221 | DHYDFWSGYLTH | SEQ ID NO:23233 |
| | | NA | AACTATGGCATGCAC | SEQ ID NO:7210 | ATTATATGGTATGATGG AACTATAAATACTATA CAGACTCCGTGAAGGGC | SEQ ID NO:15222 | GAGGGTCACGATTTTGGAG TGGCTTTTTTGTTAC | SEQ ID NO:23234 |
| iPS:436596 | 21-225_226C6 | AA | NYGMH | SEQ ID NO:7211 | IIWYDGTNKYYTDSVKG | SEQ ID NO:15223 | EGHDFWSGFFCY | SEQ ID NO:23235 |
| | | NA | GACTATGGCATGCAC | SEQ ID NO:7212 | GTTATATGGTATGATGG AAGTAATAAATACTATG CAGACTCCGTGAAGGGC | SEQ ID NO:15224 | GAGAGGTATAGCAGCAGCTG GTACGACTACGGTATGGACG TC | SEQ ID NO:23236 |
| iPS:436598 | 21-225_226B6 | AA | DYGMH | SEQ ID NO:7213 | VIWYDGSNKYYADSVKG | SEQ ID NO:15225 | ERYSSSWYDYGMDV | SEQ ID NO:23237 |
| | | NA | AATTATGATATCAAC | SEQ ID NO:7214 | TGGATGCACCCTAACAG TGGTAACACAGGCTATG CACAGAAGTTCCAGGGC | SEQ ID NO:15226 | AGCAGTGGCTGGTACAAGTT TGACTAC | SEQ ID NO:23238 |
| | | AA | NYDIN | SEQ ID NO:7215 | WMHPNSGNTGYAQKFQG | SEQ ID NO:15227 | SSGWYKFDY | SEQ ID NO:23239 |

FIGURE 49
(Continued)

| | | | | |
|---|---|---|---|---|
| iPS:436600 | 21-225_226F6 | NA | SEQ ID NO:7216<br>AATTATGATATCAAC | SEQ ID NO:15228<br>TGGATGCACCCTAACAG<br>TGGTAACACAGGCTATG<br>CACAGAAGTTCCAGGGC | SEQ ID NO:23240<br>AGCAGTGGCTGGTACCGCTT<br>TGACTAC |
| | | AA | SEQ ID NO:7217<br>NYDIN | SEQ ID NO:15229<br>WMHPNSGNTGYAQKFQG | SEQ ID NO:23241<br>SSGWYRFDY |
| iPS:436602 | 21-225_226E7 | NA | SEQ ID NO:7218<br>ACCTATGGCATGCAC | SEQ ID NO:15230<br>ATTATATGGTATGATGG<br>AAGTAATAAATACTATG<br>CAGACTCCGTGAAGGGC | SEQ ID NO:23242<br>GAGAATTACGATTTTGGAG<br>TGGTTATTATGGCTAC |
| | | AA | SEQ ID NO:7219<br>TYGMH | SEQ ID NO:15231<br>IIWYDGSNKYYADSVKG | SEQ ID NO:23243<br>ENYDFWSGYYGY |
| iPS:436604 | 21-225_226F7 | NA | SEQ ID NO:7220<br>AGCTATGGCATGCAC | SEQ ID NO:15232<br>ATTATATGGTATGATGG<br>AAGTAATAAATACTATG<br>CAGACTCCGTGAAGGGC | SEQ ID NO:23244<br>GAGAGGTATAACAGCGGCTG<br>GTACGACTACGGTTTGGACG<br>TC |
| | | AA | SEQ ID NO:7221<br>SYGMH | SEQ ID NO:15233<br>IIWYDGSNKYYADSVKG | SEQ ID NO:23245<br>ERYNSGWYDYGLDV |
| iPS:436606 | 21-225_226G8 | NA | SEQ ID NO:7222<br>GGCTACTATATACAC | SEQ ID NO:15234<br>TGGATCAACCCTTACAGT<br>GGTGACACAAAGTATGC<br>ACAGAAGTTTCAGGGC | SEQ ID NO:23246<br>GATTGGGGTGGCTACAGTTC<br>TTACTACTACGGTATGGACG<br>TC |
| | | AA | SEQ ID NO:7223<br>GYYIH | SEQ ID NO:15235<br>WINPYSGDTKYAQKFQG | SEQ ID NO:23247<br>DWGGYSSYYYGMDV |
| | | | SEQ ID NO:7224 | SEQ ID NO:15236 | SEQ ID NO:23248 |

FIGURE 49
(Continued)

| | | | | |
|---|---|---|---|---|
| iPS:436608 | 21-225_226A9 | NA | AACTATGGCATGCAC<br><br>SEQ ID NO:7225 | GTTATATGGTATGAGGA<br>AAGTAATAAATACTATA<br>CAGACTCCGTGAAGGC<br><br>SEQ ID NO:15237 | GAAGTGGGATTCACTGAGGA<br>CTAC<br><br>SEQ ID NO:23249 |
| | | AA | NYGMH<br>SEQ ID NO:7226 | VIWYEESNKYYTDSVKG<br>SEQ ID NO:15238 | EVGFTEDY<br>SEQ ID NO:23250 |
| iPS:436610 | 21-225_226F9 | NA | GGCTACTATATACAC<br><br>SEQ ID NO:7227 | TGGATCAACCCTTACAGT<br>GGTGACACAAAGTATGC<br>ACAGAAGTTTCAGGGC<br><br>SEQ ID NO:15239 | GATTGGGGTGGCTACAGTTC<br>TTACTACTACGGTATGGACG<br>TC<br><br>SEQ ID NO:23251 |
| | | AA | GYYIH<br>SEQ ID NO:7228 | WINPYSGDTKYAQKFQG<br>SEQ ID NO:15240 | DWGGYSSYYYGMDV<br>SEQ ID NO:23252 |
| iPS:436612 | 21-225_226H9 | NA | GGCTACTATATACAC<br><br>SEQ ID NO:7229 | TGGATCAACCCTTACAGT<br>GGTGACACAAACTCTGC<br>ACAGAAGTTTCAGGGC<br><br>SEQ ID NO:15241 | GATTGGGGTGGCTACAGTTC<br>TTACTACTACGGTATGGACG<br>TC<br><br>SEQ ID NO:23253 |
| | | AA | GYYIH<br>SEQ ID NO:7230 | WINPYSGDTNSAQKFQG<br>SEQ ID NO:15242 | DWGGYSSYYYGMDV<br>SEQ ID NO:23254 |
| iPS:436614 | 21-225_226F10 | NA | GGCTACTATATACAC<br><br>SEQ ID NO:7231 | TGGATCAACCCATACAG<br>TGGTGACAAAACTATG<br>CACAGAAGTTTCAGGGC<br><br>SEQ ID NO:15243 | GATTGGGGTGGCTACAGTTC<br>TTACTACTACGGTATGGACG<br>TC<br><br>SEQ ID NO:23255 |
| | | AA | GYYIH<br>SEQ ID NO:7232 | WINPYSGDTNYAQKFQG<br>SEQ ID NO:15244 | DWGGYSSYYYGMDV<br>SEQ ID NO:23256 |
| iPS:436616 | 21-225_226D11 | NA | AATTATGATATCAAC<br><br>SEQ ID NO:7233 | TGGATGCACCCTAACAG<br>TGGTAACACAGGCTATG<br>CACAGAAGTTCCAGGGC<br><br>SEQ ID NO:15245 | AGCAGTGGCTGTACTACTT<br>TGACTAC<br><br>SEQ ID NO:23257 |

FIGURE 49
(Continued)

| | | | | WMHPNSGNTGYAQKFQG | SSGWYYFDY |
|---|---|---|---|---|---|
| | | AA | NYDIN | | |
| iPS:436618 | 21-225_226E11 | NA | SEQ ID NO:7234 GGCTACTATATACAC | SEQ ID NO:15246 TGGATCAACCCTTACAGT GGTGACACAAACTATGC ACAGAAGTTTCAGGGC | SEQ ID NO:23258 GATGGGGTGGCTACAGTTC TTACTACTACGGTATGGACG TC |
| | | AA | GYYIH | SEQ ID NO:15247 WINPYSGDTNYAQKFQG | SEQ ID NO:23259 DWGGYSSYYYGMDV |
| iPS:436620 | 21-225_226H11 | NA | SEQ ID NO:7236 AACTGTGGCATGCAC | SEQ ID NO:15248 GTTATATATGGTATGATGG AAGTAATAAATACTATG CAGACTCCGTGAAGGGC | SEQ ID NO:23260 GAGCTGTATAGCAGCAGCTG GTACGACTACGGTTTGGACG TC |
| | | AA | NCGMH | SEQ ID NO:15249 VIWYDGSNKYYADSVKG | SEQ ID NO:23261 ELYSSSWYDYGLDV |
| iPS:436622 | 21-225_226A12 | NA | SEQ ID NO:7238 AATTATGATATCAAC | SEQ ID NO:15250 TGGATGCACCCTAACAG TGGTAACACAGGCTATG CACAGAAGTTCCAGGGC | SEQ ID NO:23262 AGCAGTGGCTGGTACTACTT TGACTAC |
| | | AA | NYDIN | SEQ ID NO:15251 WMHPNSGNTGYAQKFQG | SEQ ID NO:23263 SSGWYYFDY |
| iPS:436624 | 21-225_226H12 | NA | SEQ ID NO:7240 GGCTACTATATACAC | SEQ ID NO:15252 TGGATCAACCCTTACAGT GGTGACACAAACTATGC ACAGAAGTTTCAGGGC | SEQ ID NO:23264 GATGGGGTGGCTACAGTTC TTACTACTACGGTATGGACG TC |
| | | AA | GYYIH | SEQ ID NO:15253 WINPYSGDTNYAQKFQG | SEQ ID NO:23265 DWGGYSSYYYGMDV |
| | | | SEQ ID NO:7242 | SEQ ID NO:15254 | SEQ ID NO:23266 |

FIGURE 49
(Continued)

| | | | | |
|---|---|---|---|---|
| iPS:436626 | 21-225_227C1 | NA | GGCTACTATATACAC<br>SEQ ID NO:7243 | TGGATCAACCCTTACAGT<br>GGTGGCACAAACTATGC<br>ACAGAAGTTTCAGGGC<br>SEQ ID NO:15255 | GATTGGGGTGGCTACAGTTC<br>TTACTACTACGGTATGGACG<br>TC<br>SEQ ID NO:23267 |
| | | AA | GYYTH<br>SEQ ID NO:7244 | WINPYSGGTNYAQKFQG<br>SEQ ID NO:15256 | DWGGYSYYYGMDV<br>SEQ ID NO:23268 |
| iPS:436628 | 21-225_227F2 | NA | GGCTACTATATACAC<br>SEQ ID NO:7245 | TGGATCAACCCTTACAGT<br>GGTGACACAAAGTATGC<br>ACAGAAGTTTCAGGGC<br>SEQ ID NO:15257 | GATTGGGGTGGCTACAGTTC<br>TTACTACTACGGTATGGACG<br>TC<br>SEQ ID NO:23269 |
| | | AA | GYYIH<br>SEQ ID NO:7246 | WINPYSGDTKYAQKFQG<br>SEQ ID NO:15258 | DWGGYSYYYGMDV<br>SEQ ID NO:23270 |
| iPS:436630 | 21-225_227G3 | NA | AGCTATGGCATGCAC<br>SEQ ID NO:7247 | GTTATATGGTATGTTGGA<br>AGTAATCAATACTATGC<br>AGACTCCGTGAAGGGC<br>SEQ ID NO:15259 | GAAGTGGGATTCACTGAGGA<br>CTAC<br>SEQ ID NO:23271 |
| | | AA | SYGMH<br>SEQ ID NO:7248 | VIWYVGSNQYYADSVKG<br>SEQ ID NO:15260 | EVGFTEDY<br>SEQ ID NO:23272 |
| iPS:436632 | 21-225_227E4 | NA | ACTTTTGCCATGACC<br>SEQ ID NO:7249 | GTTATTAGTGGTAGAGG<br>TGGTAGCTCATTCTACGC<br>AGACTCCGTGAAGGGC<br>SEQ ID NO:15261 | GATCAACTATGGTTTGACTA<br>C<br>SEQ ID NO:23273 |
| | | AA | TFAMT<br>SEQ ID NO:7250 | VISGRGGSSFYADSVKG<br>SEQ ID NO:15262 | DQLWFDY<br>SEQ ID NO:23274 |
| iPS:436634 | 21-225_227H5 | NA | AACTATGGCATGCAC<br>SEQ ID NO:7251 | GTTATATGGTATGAAGA<br>AGTAATAAATACTATG<br>CAGACTCCGTGAAGGGC<br>SEQ ID NO:15263 | GAAGTGGGATTCACTGAGGA<br>CTAC<br>SEQ ID NO:23275 |

FIGURE 49
(Continued)

| | | | | | | | |
|---|---|---|---|---|---|---|---|
| iPS:436636 | 21-225_227E6 | AA | NYGMH | | VIWYFESNKYYADSVKG | | EVGFFTEDY |
| | | | SEQ ID NO:7252 | | SEQ ID NO:15264 | | SEQ ID NO:23276 |
| | | NA | AATTATGATATCAAC | | TGGATGCACCCTAACAG TGGTAACACAGGCTATG CACAGAAGTTCCAGGGC | | AGCAGTGGCTGGTACAAGTT TGACTAC |
| | | | SEQ ID NO:7253 | | SEQ ID NO:15265 | | SEQ ID NO:23277 |
| iPS:436638 | 21-225_227C7 | AA | NYDIN | | WMHPNSGNTGYAQKFQG | | SSGWYKFDY |
| | | | SEQ ID NO:7254 | | SEQ ID NO:15266 | | SEQ ID NO:23278 |
| | | NA | AATTATGATATCAAC | | TGGATGCATCCTAACAG TGGTAACACAGGCTATG CACAGAAGTTCCAGGGC | | AGCAGTGGCTGGTACCGGTT TGACTAC |
| | | | SEQ ID NO:7255 | | SEQ ID NO:15267 | | SEQ ID NO:23279 |
| iPS:436640 | 21-225_227A8 | AA | NYDIN | | WMHPNSGNTGYAQKFQG | | SSGWYRFDY |
| | | | SEQ ID NO:7256 | | SEQ ID NO:15268 | | SEQ ID NO:23280 |
| | | NA | GGCTACTATATACAC | | TGGATCAACCCTTACAGT GGTGACACAAACTATGC ACAGAAGTTTCAGGGC | | GATTGGGGTGGCTACAGTTC TTACTACTACGGTATGGACG TC |
| | | | SEQ ID NO:7257 | | SEQ ID NO:15269 | | SEQ ID NO:23281 |
| iPS:436644 | 21-225_227G9 | AA | GYYIH | | WINPYSGDTNYAQKFQG | | DWGGYSSYYYGMDV |
| | | | SEQ ID NO:7258 | | SEQ ID NO:15270 | | SEQ ID NO:23282 |
| | | NA | AATTATGATATCAAC | | TGGATGTACCCTAACAG TGGTAACACAGGCTATG CACAGAAGTTCCAGGGC | | AGCAGTGGCTGGTACTGGTT CGACCCC |
| | | | SEQ ID NO:7259 | | SEQ ID NO:15271 | | SEQ ID NO:23283 |
| | | AA | NYDIN | | WMYPNSGNTGYAQKFQG | | SSGWYWFDP |
| | | | SEQ ID NO:7260 | | SEQ ID NO:15272 | | SEQ ID NO:23284 |

FIGURE 49
(Continued)

| | | | | | | |
|---|---|---|---|---|---|---|
| iPS:436646 | 21-225_227D11 | NA | AATTATGATATCAAC | | TGGATGCACCCTAACAG TGGTAACACAGGCTATG CACAGAAGTTCCAGGGC | | AGCAGTGGCTGGTACTACTT TGACTAC |
| | | AA | SEQ ID NO:7261 NYDIN | | SEQ ID NO:15273 WMHPNSGNTGYAQKFQG | | SEQ ID NO:23285 SSGWYYFDY |
| iPS:436648 | 21-225_227F11 | NA | ACCTATAGCATGAAC | | SEQ ID NO:15274 TCCATTAGTAGTAGTATT AATTACATGTACTACGC AGACTCAGTGAAGGGC | | SEQ ID NO:23286 TTAGGGGTCTAC |
| | | AA | SEQ ID NO:7263 TYSMN | | SEQ ID NO:15275 SISSSINYMYYADSVKG | | SEQ ID NO:23287 LGVY |
| iPS:436650 | 21-225_227C12 | NA | AACTATGGCATGCAC | | SEQ ID NO:15276 GTTATATGTAGTATATGGA AGTAATCAATACTACGC GGACTCCGTGAAGGGC | | SEQ ID NO:23288 GAAGTGGGATTCACTGAGGA CTAC |
| | | AA | SEQ ID NO:7265 NYGMH | | SEQ ID NO:15277 VIWYIGSNQYYADSVKG | | SEQ ID NO:23289 EVGFTEDY |
| iPS:436652 | 21-225_146B11 | NA | AGCTATGCCATGAGC | | SEQ ID NO:15278 GTTATTAGTGGTGGTGGT AGTAGCACATACTACGC AGACTCCGTGAAGGGC | | SEQ ID NO:23290 TGGCGAGGTAACCCCACTGA CTACGGTATGGACGTC |
| | | AA | SEQ ID NO:7267 SYAMS | | SEQ ID NO:15279 VISGGGSSTYYADSVKG | | SEQ ID NO:23291 WRGNPTDYGMDV |
| iPS:436654 | 21-225_146C11 | NA | AGCTATGCCATGAGC | | SEQ ID NO:15280 GTTATTAGTGGTGGTGGT AGTAGCACATACTACGC AGACTCCGTGAAGGGC | | SEQ ID NO:23292 TGGCGAGGTAACCCCACTGA CTACGGTATGGACGTC |
| | | AA | SEQ ID NO:7269 SYAMS | | SEQ ID NO:15281 VISGGGSSTYYADSVKG | | SEQ ID NO:23293 WRGNPTDYGMDV |

FIGURE 49
(Continued)

| | | | | | | |
|---|---|---|---|---|---|---|
| iPS:436658 | 21-225_146A2 | NA | SEQ ID NO:7270<br>AGCTATGCCATGAGC | SEQ ID NO:15282<br>GTTATTAGTGGTGGTGGT<br>AGTAGCACATACTACGC<br>AGACTCCGTGAAGGGC | SEQ ID NO:23294<br>TGGCGAGGTAACCCCACTGA<br>CTACGGTATGGACGTC | |
| | | AA | SEQ ID NO:7271<br>SYAMS | SEQ ID NO:15283<br>VISGGGSSTYYADSVKG | SEQ ID NO:23295<br>WRGNPTDYGMDV | |
| iPS:436660 | 21-225_146D8 | NA | SEQ ID NO:7272<br>AACTATAACATGAAC | SEQ ID NO:15284<br>TACATTAGTAGAAGTAG<br>TAATACCAAATACTATGT<br>AGACTCTGTGAAGGGC | SEQ ID NO:23296<br>GATAGGAGTGGGAGCTACGG<br>GTACTTCTACTACTACGGTTT<br>GGACGTC | |
| | | AA | SEQ ID NO:7273<br>NYNMN | SEQ ID NO:15285<br>YISRSSNTKYYVDSVKG | SEQ ID NO:23297<br>DRSGSYGYFYYYGLDV | |
| iPS:436662 | 21-225_147D7 | NA | SEQ ID NO:7274<br>AGTTATGATATCAAC | SEQ ID NO:15286<br>TGGATGAACCCTAACAG<br>TGGTAACACAGGCTATG<br>CACAGAAGTTCCAGGGC | SEQ ID NO:23298<br>GCGGATATTGTATTAGTACC<br>AGCTGCTATCCCTTATAATT<br>ACTACTTCGCTATGGACGTC | |
| | | AA | SEQ ID NO:7275<br>SYDIN | SEQ ID NO:15287<br>WMNPNSGNTGYAQKFQG | SEQ ID NO:23299<br>ADIVLVPAAIPYNYYFAMDV | |
| iPS:436664 | 21-225_147E7 | NA | SEQ ID NO:7276<br>AGCTATGCCATGAGC | SEQ ID NO:15288<br>GTTATTAGTGGTGGTGGT<br>AGTAGCACATACTACGC<br>AGACTCCGTGAAGGGC | SEQ ID NO:23300<br>TGGCGAGGTAACCCCACTGA<br>CTACGGTATGGACGTC | |
| | | AA | SEQ ID NO:7277<br>SYAMS | SEQ ID NO:15289<br>VISGGGSSTYYADSVKG | SEQ ID NO:23301<br>WRGNPTDYGMDV | |
| iPS:436666 | 21-225_147B8 | NA | SEQ ID NO:7278<br>GACTACTATTTGCAC | SEQ ID NO:15290<br>TGGATCAACCCTAACAG<br>TGGTGACACAAACTATG<br>CACAGAAGTTCAGGGC | SEQ ID NO:23302<br>GATCGGGACTCTGGTTCGGG<br>GAGTTACCCTACTACTACT<br>ACTACGGTATGGACGTC | |
| | | | SEQ ID NO:7279 | SEQ ID NO:15291 | SEQ ID NO:23303 | |

FIGURE 49
(Continued)

| | | | | | | |
|---|---|---|---|---|---|---|
| iPS:436668 | 21-225_147B9 | AA | DYYLH | | WINPNSGDTNYAQKFQG | DRDSGSGSYPYYYGMDV |
| | | | SEQ ID NO:7280 | | SEQ ID NO:15292 | SEQ ID NO:23304 |
| | | NA | AGCTATGGCATGCAC | | GTTATATGGTATGATGG AAGTAATAAATACTATG CAGACTCCGTGAAGGGC | GATCGTGACTACGGTGACCC CCCTACTACTACTACTACG GTATGGACGTC |
| | | | SEQ ID NO:7281 | | SEQ ID NO:15293 | SEQ ID NO:23305 |
| iPS:436670 | 21-225_147D9 | AA | SYGMH | | VIWYDGSNKYYADSVKG | DRDYGDPYYYYGMDV |
| | | | SEQ ID NO:7282 | | SEQ ID NO:15294 | SEQ ID NO:23306 |
| | | NA | AGCTATGGCATGCAC | | GATATATGGTTGATGGC AGTAATAAATACTATGT AGACTCCGTGAAGGAC | GATCGGGTGGAGGGTTCGGG GACTCCCTACTACTACTACG GTATGGACGTC |
| | | | SEQ ID NO:7283 | | SEQ ID NO:15295 | SEQ ID NO:23307 |
| iPS:436672 | 21-225_147F9 | AA | SYGMH | | DIWFDGSNKYYVDSVKD | DRVEGSGTPYYYYGMDV |
| | | | SEQ ID NO:7284 | | SEQ ID NO:15296 | SEQ ID NO:23308 |
| | | NA | ACCTATGGCATGCAC | | GTTATATGGTATGGTGG AAGTGATAAAGACTATG CAGACTCCGTGAAGGGC | GATCGGGATTATTGTAGTGG TGGTACTTGTCCTACTACTA CTACTACGGTATGGACGTC |
| | | | SEQ ID NO:7285 | | SEQ ID NO:15297 | SEQ ID NO:23309 |
| iPS:436674 | 21-225_147G9 | AA | TYGMH | | VIWYGGSDKDYADSVKG | DRDYCSGGTCPYYYYGMDV |
| | | | SEQ ID NO:7286 | | SEQ ID NO:15298 | SEQ ID NO:23310 |
| | | NA | ACCTATGGCATGCAC | | GTTATATGGTATGGTGG AAGTGATAAAGACTATG CAGACTCCGTGAAGGGC | GATCGGGATTATTGTAGTGG TGGTAGCTGCCCTTACTACT ACTACTACGGTATGGACGTC |
| | | | SEQ ID NO:7287 | | SEQ ID NO:15299 | SEQ ID NO:23311 |

FIGURE 49
(Continued)

| | | AA | TYGMH | | VIWYGGSDKDYADSVKG | | DRDYCSGGSCPYYYYGMDV | |
|---|---|---|---|---|---|---|---|---|
| iPS:436676 | | | SEQ ID NO:7288 | | SEQ ID NO:15300 | | SEQ ID NO:23312 | |
| | 21-225_147E11 | NA | AACTATGTCATGAGC | | GTTATTAGTGGTGGTGGT AGTAGTACATACTACGC AGACTCCGTGAAGGGC | | TGGCGAGGTAACCCCACTGA CTACGGTATGGACGTC | |
| | | | SEQ ID NO:7289 | | SEQ ID NO:15301 | | SEQ ID NO:23313 | |
| | | AA | NYVMS | | VISGGGSSTYYADSVKG | | WRGNPTDYGMDV | |
| iPS:436678 | | | SEQ ID NO:7290 | | SEQ ID NO:15302 | | SEQ ID NO:23314 | |
| | 21-225_147B12 | NA | AGCTATGCCATGAGC | | GTTATTAGTGGTGGTGGT AGTAGCACATACTACGC AGACTCCGTGAAGGGC | | TGGCGAGGTAACCCCACTGA CTACGGTATGGACGTC | |
| | | | SEQ ID NO:7291 | | SEQ ID NO:15303 | | SEQ ID NO:23315 | |
| | | AA | SYAMS | | VISGGGSSTYYADSVKG | | WRGNPTDYGMDV | |
| iPS:436680 | | | SEQ ID NO:7292 | | SEQ ID NO:15304 | | SEQ ID NO:23316 | |
| | 21-225_147H12 | NA | AGTGGTTATTACCACTGGAGC | | TACATCTATTACAGTGGG AGCACCTACTACAACCC GTCCCTCAAGAGT | | GATTGGGGTGGCTACGATTC GAGTGGCTGTTCGACCCC | |
| | | | SEQ ID NO:7293 | | SEQ ID NO:15305 | | SEQ ID NO:23317 | |
| | | AA | SGYYHWS | | YIYYSGSTYYNPSLKS | | DWGGYDSSGWFDP | |
| iPS:436682 | | | SEQ ID NO:7294 | | SEQ ID NO:15306 | | SEQ ID NO:23318 | |
| | 21-225_146A8 | NA | AACTATAACATGAAC | | TACATTAGTAGAAGTAG TAATACCAAATACTACG CAGACTCTGTGAGGGGC | | GATAGGAGTGGGAGCTACGG GTACTTCTACTACTACGGTTT GGACGTC | |
| | | | SEQ ID NO:7295 | | SEQ ID NO:15307 | | SEQ ID NO:23319 | |
| | | AA | NYNMN | | YISRSSNTKYYADSVRG | | DRSGSGYFYYYGLDV | |
| | | | SEQ ID NO:7296 | | SEQ ID NO:15308 | | SEQ ID NO:23320 | |

FIGURE 49
(Continued)

| | | | | | |
|---|---|---|---|---|---|
| iPS:436684 | 21-225_146B6 | NA | AGCTATAACATGAAC | TACATTAGTAGAAGTAG TAATACCAAAACACTACG CAGACTCTGTGAAGGGC | GATAGGAGTGGGAGCTACGG GTACTTCTACTACTACGGTTT GGACGTC |
| | | | SEQ ID NO:7297 | SEQ ID NO:15309 | SEQ ID NO:23321 |
| | | AA | SYNMN | YISRSSNTKHYADSVKG | DRSGSYGFYYYGLDV |
| | | | SEQ ID NO:7298 | SEQ ID NO:15310 | SEQ ID NO:23322 |
| iPS:436686 | 21-225_148G6 | NA | AGCTATGCCATGAGC | GTTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7299 | SEQ ID NO:15311 | SEQ ID NO:23323 |
| | | AA | SYAMS | VISGGGSTYYADSVKG | WRGNPTDYGMDV |
| | | | SEQ ID NO:7300 | SEQ ID NO:15312 | SEQ ID NO:23324 |
| iPS:436688 | 21-225_148C8 | NA | AGCTATGGCATGCAC | GTTATATGGTATGATGG AAGTAATAAATACTATG CAGACTCCGTGAAGGGC | GATCGTGACTAGGTGACC CCCTACTACTACTACTACG GTATGGACGTC |
| | | | SEQ ID NO:7301 | SEQ ID NO:15313 | SEQ ID NO:23325 |
| | | AA | SYGMH | VIWYDGSNKYYADSVKG | DRDYGDPPYYYYGMDV |
| | | | SEQ ID NO:7302 | SEQ ID NO:15314 | SEQ ID NO:23326 |
| iPS:436690 | 21-225_148A9 | NA | ACCTATGGCATGCAC | GTTATATGGTATGGTGG AAGTGATAAAGACTATG CAGACTCCGTGAAGGGC | GATCGGGATTATTGTAGTGG TGGTACTTGTCCTTACTACTA CTACTACGGTATGGACGTC |
| | | | SEQ ID NO:7303 | SEQ ID NO:15315 | SEQ ID NO:23327 |
| | | AA | TYGMH | VIWYGGSDKDYADSVKG | DRDYCSGGTCPYYYYGMDV |
| | | | SEQ ID NO:7304 | SEQ ID NO:15316 | SEQ ID NO:23328 |

FIGURE 49
(Continued)

| | | | | | | |
|---|---|---|---|---|---|---|
| iPS:436694 | 21-225_148G11 | NA | AGCTATCCCATGAGC SEQ ID NO:7305 | GTTATTAGTGGTGGTGGT AGTAGTGCATACTACGC AGACTCCGTGAAGGGC SEQ ID NO:15317 | TGGCGAGGTAACCCCACTGA CTACGGTATGGACGTC SEQ ID NO:23329 | |
| | | AA | SYPMS SEQ ID NO:7306 | VISGGGSSAYYADSVKG SEQ ID NO:15318 | WRGNPTDYGMDV SEQ ID NO:23330 | |
| iPS:436696 | 21-225_149A1 | NA | AGCTATAACATGAAC SEQ ID NO:7307 | TACATTAGTAGAAGTAG TAATACCAAACACTACG CAGACTCTGTGAAGGGC SEQ ID NO:15319 | GATAGGAGTGGGAGCTACGG GTACTTCTACTACTACGGTTT GGACGTC SEQ ID NO:23331 | |
| | | AA | SYNMN SEQ ID NO:7308 | YISRSSNTKHYADSVKG SEQ ID NO:15320 | DRSGSYGYFYYYGLDV SEQ ID NO:23332 | |
| iPS:436698 | 21-225_149B5 | NA | GGCTATGGCATGAAC SEQ ID NO:7309 | AACATAAAGCAAGATGG AAGTGAGAAATACTATG TGGACTCTGTGAAGGGC SEQ ID NO:15321 | GGGATGTATAGCAGTGGCTG GTACGTCTTTGACTAC SEQ ID NO:23333 | |
| | | AA | GYWMN SEQ ID NO:7310 | NIKQDGSEKYYVDSVKG SEQ ID NO:15322 | GMYSSGWYVFDY SEQ ID NO:23334 | |
| iPS:436700 | 21-225_149C7 | NA | AGCTATGCCATGAGC SEQ ID NO:7311 | GTTATTAGTGGTGGTGGT AGTAGCACATACTACGC AGACTCCGTGAAGGGC SEQ ID NO:15323 | TGGCGAGGTAACCCCACTGA CTACGGTATGGACGTC SEQ ID NO:23335 | |
| | | AA | SYAMS SEQ ID NO:7312 | VISGGGSSTYYADSVKG SEQ ID NO:15324 | WRGNPTDYGMDV SEQ ID NO:23336 | |
| iPS:436702 | 21-225_149E8 | NA | AGTTATAGCATGAAC SEQ ID NO:7313 | GCCATTAGTAGTAGTACTGGT AGTTACATATATTACGCA GACTCAGTGAAGGGC SEQ ID NO:15325 | ACGGCAGTGGCTGTGGTACTGG GTGGTTGACCCC SEQ ID NO:23337 | |

FIGURE 49
(Continued)

| | | | | | | | |
|---|---|---|---|---|---|---|---|
| iPS:436704 | 21-225_149C10 | AA | SYSMN<br>SEQ ID NO:7314 | | AISSTGSVIYYADSVKG<br>SEQ ID NO:15326 | | TAVAGTGWFDP<br>SEQ ID NO:23338 |
| | | NA | AGCCACGCCATGAGC<br>SEQ ID NO:7315 | | GTTATAAGTGGAGGTGG<br>TAGTAGCACATATTACG<br>CAGACTCCGTGAAGGGC<br>SEQ ID NO:15327 | | TGGCGAGGTAACCCCACTGA<br>CTACGGTATGGACGTC<br>SEQ ID NO:23339 |
| iPS:436706 | 21-225_149A11 | AA | SHAMS<br>SEQ ID NO:7316 | | VISGGGSSTYYADSVKG<br>SEQ ID NO:15328 | | WRGNPTDYGMDV<br>SEQ ID NO:23340 |
| | | NA | AGCTATGGCATGCAC<br>SEQ ID NO:7317 | | GTTATATGGTATGATGG<br>AAGTAATAAATACTATG<br>CAGACTCCGTGAAGGGC<br>SEQ ID NO:15329 | | GATCGTGACTACGGTGACC<br>CCCCTACTACTACTACTACG<br>GTATGGACGTC<br>SEQ ID NO:23341 |
| iPS:436708 | 21-225_150D3 | AA | SYGMH<br>SEQ ID NO:7318 | | VIWYDGSNKYYADSVKG<br>SEQ ID NO:15330 | | DRDYGDPPYYYYGMDV<br>SEQ ID NO:23342 |
| | | NA | ACCTATGGCATGCAC<br>SEQ ID NO:7319 | | GTTATATGGTATGGTGG<br>AAGTAATAAAGACTATG<br>CAGACTCCGTGAAGGGC<br>SEQ ID NO:15331 | | GATCGGGATTATTGTAGTGG<br>TGGTACCTGCCCTTACTACT<br>ACTACTACGGTATGGACGTC<br>SEQ ID NO:23343 |
| iPS:436710 | 21-225_150F6 | AA | TYGMH<br>SEQ ID NO:7320 | | VIWYGGSNKDYADSVKG<br>SEQ ID NO:15332 | | DRDYCSGGTCPYYYYGMDV<br>SEQ ID NO:23344 |
| | | NA | AGCTATGGCATGAGC<br>SEQ ID NO:7321 | | GTTATTAGTGGTGGTGGT<br>AGTAGCACATACTACGC<br>AGACTCCGTGAAGGGC<br>SEQ ID NO:15333 | | TGGCGAGGTAACCCCACTGA<br>CTACGGTATGGACGTC<br>SEQ ID NO:23345 |
| | | AA | SYAMS<br>SEQ ID NO:7322 | | VISGGGSSTYYADSVKG<br>SEQ ID NO:15334 | | WRGNPTDYGMDV<br>SEQ ID NO:23346 |

FIGURE 49
(Continued)

| | | | | | |
|---|---|---|---|---|---|
| iPS:436712 | 21-225_150F9 | NA | AGCTATAACATGAAC | TACATTAGTAGTAGAAGTAG TAATACCAAACACTACG CAGACTCTGTGAAGGGC | GATAGGAGTGGGAGCTACGG GTACTTCTACTACTACGGTTT GGACGTC |
| | | | SEQ ID NO:7323 | SEQ ID NO:15335 | SEQ ID NO:23347 |
| | | AA | SYNMN | YISRSSNTKHYADSVKG | DRSGSYGYFYYYGLDV |
| | | | SEQ ID NO:7324 | SEQ ID NO:15336 | SEQ ID NO:23348 |
| iPS:436714 | 21-225_150H11 | NA | ACCTATGCCATGAGC | ATTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7325 | SEQ ID NO:15337 | SEQ ID NO:23349 |
| | | AA | TYAMS | IISGGGSSTYYADSVKG | WRGNPTDYGMDV |
| | | | SEQ ID NO:7326 | SEQ ID NO:15338 | SEQ ID NO:23350 |
| iPS:436716 | 21-225_151F3 | NA | ACCTATGCCATGCAC | GTTATATGGTATGGTGG AAGTAATACAGACTATG CAGACTCCGTGAAGGGC | GATCGGGATTATTGTAGTGG TACTAGCTGCCCTTACTACT ACTACTACGGTATGGACGTC |
| | | | SEQ ID NO:7327 | SEQ ID NO:15339 | SEQ ID NO:23351 |
| | | AA | TYGMH | VIWYGGSNTDYADSVKG | DRDYCSGTSCPYYYYYGMDV |
| | | | SEQ ID NO:7328 | SEQ ID NO:15340 | SEQ ID NO:23352 |
| iPS:436718 | 21-225_151H5 | NA | AGCTATGCCATGAGC | GTTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7329 | SEQ ID NO:15341 | SEQ ID NO:23353 |
| | | AA | SYAMS | VISGGGSSTYYADSVKG | WRGNPTDYGMDV |
| | | | SEQ ID NO:7330 | SEQ ID NO:15342 | SEQ ID NO:23354 |

FIGURE 49
(Continued)

| | | | | | |
|---|---|---|---|---|---|
| iPS:436720 | 21-225_151H6 | NA | GACTATGGCATGCAC | CTTATATGGTATGATGGA AGTAATAAATACTATGC AGACTCCGTGAAGGGC | GATGACCGATCTGTAGTAG AACCAGCTGCCTTACTACT ACTACTACGGTTTGGACGTC |
| | | | SEQ ID NO:7331 | SEQ ID NO:15343 | SEQ ID NO:23355 |
| | | AA | DYGMH | LIWYDGSNKYYADSVKG | DDRSCSRTSCPYYYYGLDV |
| | | | SEQ ID NO:7332 | SEQ ID NO:15344 | SEQ ID NO:23356 |
| iPS:436722 | 21-225_151H7 | NA | AGCTATGCCATGAGC | GTTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7333 | SEQ ID NO:15345 | SEQ ID NO:23357 |
| | | AA | SYAMS | VISGGGSSTYYADSVKG | WRGNPTDYGMDV |
| | | | SEQ ID NO:7334 | SEQ ID NO:15346 | SEQ ID NO:23358 |
| iPS:436724 | 21-225_151B9 | NA | AGCTATGCCATGAGC | GTTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7335 | SEQ ID NO:15347 | SEQ ID NO:23359 |
| | | AA | SYAMS | VISGGGSSTYYADSVKG | WRGNPTDYGMDV |
| | | | SEQ ID NO:7336 | SEQ ID NO:15348 | SEQ ID NO:23360 |
| iPS:436726 | 21-225_152G5 | NA | GACTATGGCATGCAC | CTTATATGGTATGATGGA AGTAATAAATACTATGC AGACTCCGTGAAGGGC | GATGACCGATCTGTAGTAG AACCAGCTGCCTTACTACT ACTACTACGGTTTGGACGTC |
| | | | SEQ ID NO:7337 | SEQ ID NO:15349 | SEQ ID NO:23361 |
| | | AA | DYGMH | LIWYDGSNKYYADSVKG | DDRSCSRTSCPYYYYGLDV |
| | | | SEQ ID NO:7338 | SEQ ID NO:15350 | SEQ ID NO:23362 |

FIGURE 49
(Continued)

| | | | | |
|---|---|---|---|---|
| iPS:436728 | 21-225_152G6 | NA | AGCTATGGCCATGAGC<br>SEQ ID NO:7339 | GTTATTAGTGGTGGTGGT<br>AGTAGCACATACTACGC<br>AGACTCCGTGAAGGGC<br>SEQ ID NO:15351 | TGGCGAGGTAACCCCACTGA<br>CTACGGTATGGACGTC<br>SEQ ID NO:23363 |
| | | AA | SYAMS<br>SEQ ID NO:7340 | VISGGGSTYYADSVKG<br>SEQ ID NO:15352 | WRGNPTDYGMDV<br>SEQ ID NO:23364 |
| iPS:436730 | 21-225_152D7 | NA | AGCTATGGCCATGAGC<br>SEQ ID NO:7341 | GTTATTAGTGGTGGTGGT<br>AGTAGCACATACTACGC<br>AGACTCCGTGAAGGGC<br>SEQ ID NO:15353 | TGGCGAGGTAACCCCACTGA<br>CTCCGGTATGGACGTC<br>SEQ ID NO:23365 |
| | | AA | SYAMS<br>SEQ ID NO:7342 | VISGGGSTYYADSVKG<br>SEQ ID NO:15354 | WRGNPTDSGMDV<br>SEQ ID NO:23366 |
| iPS:436732 | 21-225_152B12 | NA | GACTATGGCATGCAC<br>SEQ ID NO:7343 | GTTATATGGTATGATGG<br>AAGTAATAAATACTATG<br>CAGACTCCGTGAAGGGC<br>SEQ ID NO:15355 | GATGACCGATCTGTAGTAG<br>TACCAGCTGCCCTTACTACT<br>ACTACTACGGTTTGGACGTC<br>SEQ ID NO:23367 |
| | | AA | DYGMH<br>SEQ ID NO:7344 | VIWYDGSNKYYADSVKG<br>SEQ ID NO:15356 | DDRSCSSFSCPYYYYGLDV<br>SEQ ID NO:23368 |
| iPS:436734 | 21-225_153A8 | NA | GACTATGGCATGCAC<br>SEQ ID NO:7345 | CTTATATGGTATGATGGA<br>AGTAATAAATACTATGC<br>AGACTCCGTGAAGGGC<br>SEQ ID NO:15357 | GATGACCGATCTGTAGTAG<br>AACCAGCTGCCCTTACTACT<br>ACTACTACGGTTTGGACGTC<br>SEQ ID NO:23369 |
| | | AA | DYGMH<br>SEQ ID NO:7346 | LIWYDGSNKYYADSVKG<br>SEQ ID NO:15358 | DDRSCSRTSCPYYYYGLDV<br>SEQ ID NO:23370 |

FIGURE 49
(Continued)

| iPS:436736 | 21-225_153E8 | NA | AACTATGGCATGCAC | | GTTATATGGTTTGATGGC AGTAATAAATACTATGTT GACTCCGTGAAGGAC | GATCGGGTGGAGGGTTCGGG GACTCCTACTACTACG GTATGGACGTC |
| --- | --- | --- | --- | --- | --- | --- |
| | | | SEQ ID NO:7347 | | SEQ ID NO:15359 | SEQ ID NO:23371 |
| | | AA | NYGMH | | VIWFDGSNKYYVDSVKD | DRVEGSGTPYYYGMDV |
| | | | SEQ ID NO:7348 | | SEQ ID NO:15360 | SEQ ID NO:23372 |
| iPS:436738 | 21-225_153D9 | NA | ACCTATGCCATGCAC | | GTTATATGGTATGGTGG AAGTAATAAAGACTATG CAGACTCCGTGAAGGGC | GATCGGGATTATTGTAGTGG TGGTAGCTGTCCTTACTACT ACTACTACGGTATGGACGTC |
| | | | SEQ ID NO:7349 | | SEQ ID NO:15361 | SEQ ID NO:23373 |
| | | AA | TYGMH | | VIWYGGSNKDYADSVKG | DRDYCSGGSCPYYYYGMDV |
| | | | SEQ ID NO:7350 | | SEQ ID NO:15362 | SEQ ID NO:23374 |
| iPS:436740 | 21-225_154C3 | NA | ACCTATGCCATGCAC | | GTTGTATGGTATGGTGG AAATAATAAAGACTATG CAGACTCCGTGAAGGGC | GATCGGGATTATTGTAGTGG TGGTAGCTGCCCTTACTACT ACTACTACGGTATGGACGTC |
| | | | SEQ ID NO:7351 | | SEQ ID NO:15363 | SEQ ID NO:23375 |
| | | AA | TYGMH | | VVWYGGNNKDYADSVK G | DRDYCSGGSCPYYYYGMDV |
| | | | SEQ ID NO:7352 | | SEQ ID NO:15364 | SEQ ID NO:23376 |
| iPS:436742 | 21-225_154C4 | NA | AGCTATGCCATGAGC | | GTTATTAGTGGTGGTGGT AGTAGCACATACTACGC AGACTCCGTGAAGGGC | TGGCGAGGTAACCCCACTGA CTACGGTATGGACGTC |
| | | | SEQ ID NO:7353 | | SEQ ID NO:15365 | SEQ ID NO:23377 |
| | | AA | SYAMS | | VISGGGSTYYADSVKG | WRGNPTDYGMDV |
| | | | SEQ ID NO:7354 | | SEQ ID NO:15366 | SEQ ID NO:23378 |

FIGURE 49
(Continued)

| | | | | | |
|---|---|---|---|---|---|
| iPS:436744 | 21-225_154F4 | NA | AGCTATGGCATGCAC | GTTATATGGTATGATGG AAGTAATAAATACTATG CAGACTCCGTGAAGGGC | GAGGATTCCTATTGTAGTGG TACCAGCTGCCCTACTACT ACTACTACGGTATGGACGTC |
| | | | SEQ ID NO:7355 | SEQ ID NO:15367 | SEQ ID NO:23379 |
| | | AA | SYGMH | VIWYDGSNKYYADSVKG | EDSYCSGTSCPYYYYYGMDV |
| | | | SEQ ID NO:7356 | SEQ ID NO:15368 | SEQ ID NO:23380 |
| iPS:436746 | 21-225_154E10 | NA | AGCTATGCCATGAGC | GTTATTAGTGGTGGTGGT AGTAGCACATACTACGC AGACTCCGTGAAGGGC | TGGCGAGGTAACCCCACTGA CTACGGTATGGACGTC |
| | | | SEQ ID NO:7357 | SEQ ID NO:15369 | SEQ ID NO:23381 |
| | | AA | SYAMS | VISGGGSSTYYADSVKG | WRGNPTDYGMDV |
| | | | SEQ ID NO:7358 | SEQ ID NO:15370 | SEQ ID NO:23382 |
| iPS:436748 | 21-225_154D11 | NA | ACCTATGGCATGCAC | GTTATATGGTATGGTGG AAGTAATAAAGACTATG CAGACTCTGTGAAGGGC | GATCGGGATTATTGTAGTGG TGGTAGTGCCCCTTACTACT ACTACTACGGTATGGACGTC |
| | | | SEQ ID NO:7359 | SEQ ID NO:15371 | SEQ ID NO:23383 |
| | | AA | TYGMH | VIWYGGSNKDYADSVKG | DRDYCSGGSCPYYYYYGMDV |
| | | | SEQ ID NO:7360 | SEQ ID NO:15372 | SEQ ID NO:23384 |
| iPS:436750 | 21-225_154G12 | NA | AGTGGTTATTACTACTGGAG C | TACATCTATTATAGTGGG AGCACCTACTACAACCC GTCCCTCAAGAGT | GATTGGGGTGGCTACGATTC GAGTGGCTGGTTCGACCCC |
| | | | SEQ ID NO:7361 | SEQ ID NO:15373 | SEQ ID NO:23385 |
| | | AA | SGYYYWS | YIYYSGSTYYNPSLKS | DWGGYDSSGWFDP |
| | | | SEQ ID NO:7362 | SEQ ID NO:15374 | SEQ ID NO:23386 |

FIGURE 49
(Continued)

| | | | | |
|---|---|---|---|---|
| iPS:436752 | 21-225_155H1 | NA | AGCTACTGGATCGGC | CTCATCTATCCTGGTGCC TCTGATACCAGATACAG CCCGTCCTTCCAAGGC | CAGGCCATAGCAAGTCGAGG GAGGTACTACTACTACGGTA TGGACGTC |
| | | | SEQ ID NO:7363 | SEQ ID NO:15375 | SEQ ID NO:23387 |
| | | AA | SYWIG | LIYPGASDTRYSPSFQG | QAIASRGRYYYYGMDV |
| | | | SEQ ID NO:7364 | SEQ ID NO:15376 | SEQ ID NO:23388 |
| iPS:436754 | 21-225_155G3 | NA | AGCTATGGCATGCAC | GTTATATCATATGATGGA AGTAATAAATACTATGC AGACTCCGTGAAGGGC | GATACGGAGAGATGGCTACC ATACTCCTACGGTATGGACG TC |
| | | | SEQ ID NO:7365 | SEQ ID NO:15377 | SEQ ID NO:23389 |
| | | AA | SYGMH | VISYDGSNKYYADSVKG | DTERWLPYSYGMDV |
| | | | SEQ ID NO:7366 | SEQ ID NO:15378 | SEQ ID NO:23390 |
| iPS:436756 | 21-225_146A10 | NA | GGCTATGGCATGCAC | CTTATACGGTATGATGG AAGCGATAAAAACTATG CAGACTCCGTGAAGGGC | GATCGGGTTTTTTGTAGTAG TACCAGCTGCCTCTCTTACTA CTACTACTACGGTATGGACG TC |
| | | | SEQ ID NO:7367 | SEQ ID NO:15379 | SEQ ID NO:23391 |
| | | AA | GYGMH | LIRYDGSDKNYADSVKG | DRVFCSSTSCLSYYYYGMDV |
| | | | SEQ ID NO:7368 | SEQ ID NO:15380 | SEQ ID NO:23392 |
| iPS:436758 | 21-225_155C10 | NA | AGCTATGCCATGAGC | GTTATTAGTGGTGGTGGT AGTAGCACATACTACGC AGACTCCGTGAAGGGC | TGGCGAGGTAACCCACTGA CTACGGTATGGACGTC |
| | | | SEQ ID NO:7369 | SEQ ID NO:15381 | SEQ ID NO:23393 |
| | | AA | SYAMS | VISGGGSSTYYADSVKG | WRGNPTDYGMDV |
| | | | SEQ ID NO:7370 | SEQ ID NO:15382 | SEQ ID NO:23394 |

FIGURE 49
(Continued)

| | | | | |
|---|---|---|---|---|
| iPS:436760 | 21-225_155E10 | NA | AGCTATGGCATGCAC SEQ ID NO:7371 | GTTATATGGTATGATGG AAGTAATAAATACTATG CAGACTCCGTGAAGGGC SEQ ID NO:15383 | GATCGTGACTACGGTGACCC CCCTACTACTACTACG GTATGGACGTC SEQ ID NO:23395 |
| | | AA | SYGMH SEQ ID NO:7372 | VIWYDGSNKYYADSVKG SEQ ID NO:15384 | DRDYGDPPYYYYGMDV SEQ ID NO:23396 |
| iPS:436762 | 21-225_156H2 | NA | AACTATAACATGAAC SEQ ID NO:7373 | TACATTAGTAGAAGTAG TAATACCAAATACTACG CAGACTCTGTGAAGGGC SEQ ID NO:15385 | GATAGGAGTGGGAGCTACGG GTACTTCTACTACTACGGTA TGGACGTC SEQ ID NO:23397 |
| | | AA | NYNMN SEQ ID NO:7374 | YISRSSNTKYYADSVKG SEQ ID NO:15386 | DRSGSYGYFYYYGMDV SEQ ID NO:23398 |
| iPS:436764 | 21-225_158E9 | NA | AGCTATGGCATGCAC SEQ ID NO:7375 | GTTATATGGTATGATGG AAGTAATAAATACTATG CAGACTCCGTGAAGGGC SEQ ID NO:15387 | GATCGGGTTTTTGTAGTGG TACCAGCTGCCCTTACTACT ACTACTACGGTATGGACGTC SEQ ID NO:23399 |
| | | AA | SYGMH SEQ ID NO:7376 | VIWYDGSSKYYADSVKG SEQ ID NO:15388 | DRVFCSGTSCPYYYYGMDV SEQ ID NO:23400 |
| iPS:436766 | 21-225_158D10 | NA | AGCTATGGCATGCAC SEQ ID NO:7377 | GTTATATGGTATGATGG AAGTAATAAATACTATG CAGACTCCGTGAAGGGC SEQ ID NO:15389 | GATCGGGTTCTTGTAGTAG TACCAGCTGCCCTTACTACT ACTACTACGGTATGGACGTC SEQ ID NO:23401 |
| | | AA | SYGMH | VIWYDGSNKYYADSVKG | DRVSCSSTSCPYYYYGMDV |

FIGURE 49
(Continued)

| | | | SEQ ID NO:7378 | | SEQ ID NO:15390 | | SEQ ID NO:23402 |
|---|---|---|---|---|---|---|---|
| iPS:436768 | | NA | ACCTATGGCATGCAC | | GTTATATGGTATGATGG AAGTAATAAATACTATG CAGACTCCGTGAAGGGC | | GATCGGGTTTCTTGTAGTAG TACCAGCTGCCCTTACTACT ACTACTACGGTATGGACGTC |
| | 21-225_159H8 | | SEQ ID NO:7379 | | SEQ ID NO:15391 | | SEQ ID NO:23403 |
| | | AA | TYGMH | | VIWYDGSNKYYADSVKG | | DRVSCSSTSCPYYYYYGMDV |
| iPS:436770 | | NA | SEQ ID NO:7380 AGCTATGGCATGCAC | | SEQ ID NO:15392 GTTATATGGTATGATGG AAGTAATAAATACTATG CAGACTCCGTGAAGGGC | | SEQ ID NO:23404 GATCGGGTTTCTTGTAGTAG TACCAGCTGCCCTTACTACT ACTACTACGGTATGGACGTC |
| | 21-225_160B12 | | SEQ ID NO:7381 | | SEQ ID NO:15393 | | SEQ ID NO:23405 |
| | | AA | SYGMH | | VIWYDGSNKYYADSVKG | | DRVSCSSTSCPYYYYYGMDV |
| iPS:436772 | | NA | SEQ ID NO:7382 AGCTATGGCATGCAC | | SEQ ID NO:15394 GTTATATGGTATGATGG AAGTAATAAATACTATG CAGACTCCGTGAAGGGC | | SEQ ID NO:23406 GTCGGGTATAGCGGTGGCTG GTACATCTTTGACTAC |
| | 21-225_161H3 | | SEQ ID NO:7383 | | SEQ ID NO:15395 | | SEQ ID NO:23407 |
| | | AA | SYGMH | | VIWYDGSNKYYADSVKG | | VGYSGGWYIFDY |
| iPS:436774 | | NA | SEQ ID NO:7384 AGCTATGGCATGCAC | | SEQ ID NO:15396 GTTATATGGTATGATGG AAGTAATAAATACTATG TAGACTCCGTGAAGGGC | | SEQ ID NO:23408 GATCGGGTTTTTGTAGTAG TACCAGCTGCCCTTACTACT ACTACTACGGTATGGACGTC |
| | 21-225_161E10 | | SEQ ID NO:7385 | | SEQ ID NO:15397 | | SEQ ID NO:23409 |

FIGURE 49
(Continued)

| | | | | SYGMH | SEQ ID NO:7386 | VIWYDGSNKYYVDSVKG | SEQ ID NO:15398 | DRVFCSGTSCPYYYYGMDV | SEQ ID NO:23410 |
|---|---|---|---|---|---|---|---|---|---|
| iPS:436776 | 21-225_161F12 | | AA | | | | | | |
| | | NA | | AGTGGTGGTTACTACTGGAGC | SEQ ID NO:7387 | TACATCTATTACAGTGGGAGCCCCTACTACAACCCGTCCCTCAAGAGT | SEQ ID NO:15399 | TCGAATTGTAGTAGTGCCAACTGCTATACGGTGGGGTTCTACTACTACGGTTTGGACGTC | SEQ ID NO:23411 |
| iPS:436780 | 21-225_165H3 | | AA | SGGYYWS | SEQ ID NO:7388 | YIYYSGSPYYNPSLKS | SEQ ID NO:15400 | SNCSSANCYTVGFYYYGLDV | SEQ ID NO:23412 |
| | | NA | | AGTGGTGGTTACTACTGGAGC | SEQ ID NO:7389 | TACATCTATTACAGTGGGAGCCCCTACTACAATCCGTCCCTCAAGAGT | SEQ ID NO:15401 | TCGAATTGTAGTAGTGCCAACTGCTATACGGTGGGGTTCTACTACTACGGTATGGACGTC | SEQ ID NO:23413 |
| iPS:436782 | 21-225_166G11 | | AA | SGGYYWS | SEQ ID NO:7390 | YIYYSGSPYYNPSLKS | SEQ ID NO:15402 | SNCSSANCYTVGFYYYGMDV | SEQ ID NO:23414 |
| | | NA | | GGCTATGGCATGCAC | SEQ ID NO:7391 | GTTATATGGTATGATGGAAGTAATAAATACTATGCAGACTCCGTGAAGGGC | SEQ ID NO:15403 | GATGATAGATATTGTAGTAGTCCCACCTGCCATCCTTACTACTACTACGGTCTGGACGTC | SEQ ID NO:23415 |
| | | | AA | GYGMH | SEQ ID NO:7392 | VIWYDGSNKYYADSVKG | SEQ ID NO:15404 | DDRYCSSPTCHPYYYYGLDV | SEQ ID NO:23416 |

FIGURE 49
(Continued)

| | | NA/AA | | | |
|---|---|---|---|---|---|
| iPS:436784 | 21-225_169C1 | NA | AGCAATGGCATGCAC SEQ ID NO:7393 | GTTATATGGTATGATGG AAGTAATAAATACTATG CAGACTCCGTGAAGGGC SEQ ID NO:15405 | GATCAGTACAACCGGAACGA CGGACCACCAGCTTACTACT ACTACTACGGTTTGGACGTC SEQ ID NO:23417 |
| | | AA | SNGMH SEQ ID NO:7394 | VIWYDGSNKYYADSVKG SEQ ID NO:15406 | DQYNRNDGPPAYYYYYGLDV SEQ ID NO:23418 |
| iPS:436786 | 21-225_169A6 | NA | AGCAATGGCATGCAC SEQ ID NO:7395 | GTTATATGGTATGATGG AAGTAATAAATACTATG CAGACTCCGTGAAGGGC SEQ ID NO:15407 | GATCAGTACAACCGGAACGA CGGACCACCAGCTTACTACT ACTACTACGGTATGGACGTC SEQ ID NO:23419 |
| | | AA | SNGMH SEQ ID NO:7396 | VIWYDGSNKYYADSVKG SEQ ID NO:15408 | DQYNRNDGPPAYYYYYGMD V SEQ ID NO:23420 |
| iPS:436788 | 21-225_169B7 | NA | AGCTATAGCTTGAAC SEQ ID NO:7397 | TACATTGGTAGTAGTGG CAGTATCATATTCTACGC AGACTCGTGAAGGGC SEQ ID NO:15409 | GGGGATACAGCTGGGGTTAC CTATTACTACGGTATGGACG TC SEQ ID NO:23421 |
| | | AA | SYSLN SEQ ID NO:7398 | YIGSSGSIIFYADSVKG SEQ ID NO:15410 | GDTAGVTYYYGMDV SEQ ID NO:23422 |
| iPS:436790 | 21-225_169G11 | NA | AGCTATGGCATGCAC SEQ ID NO:7399 | ATTATATGGTATGATGG AAGTAATAAATACTATG CAGACTCCGTGAAGGGC SEQ ID NO:15411 | GAGGGGGCTACGTATTACCA TGGTTCGGGGAGTATTATATC CGGCTACTAACTACGGTATG GACGTC SEQ ID NO:23423 |
| | | AA | SYGMH SEQ ID NO:7400 | IIWYDGSNKYYADSVKG SEQ ID NO:15412 | EGATYHGSGSYYPATNYGM DV SEQ ID NO:23424 |

FIGURE 49
(Continued)

| | | | | | |
|---|---|---|---|---|---|
| iPS:436792 | 21-225_169D12 | NA | AGCTATGGCATGCAC | GTTATATGGTATGATGGAAGTAATAAATATTATGCAGACTCCGTGAAGGGC | CCCCCTTTACGATATGGGACTCTACTACGATATGGACGTC |
| | | | SEQ ID NO:7401 | SEQ ID NO:15413 | SEQ ID NO:23425 |
| | | AA | SYGMH | VIWYDGSNKYYADSVKG | PLYDMGLYDMDV |
| | | | SEQ ID NO:7402 | SEQ ID NO:15414 | SEQ ID NO:23426 |
| iPS:436794 | 21-225_170F1 | NA | GGCTATGGCATGAAC | ATTATATGGTATGATGGAAATAATAAATACTATGCAGACTCCGTGAAGGGC | GATCGGGTTTATTGTAGTAGTACCAGCTGCCATCCCTATTACTACTACGCTATGGACGTC |
| | | | SEQ ID NO:7403 | SEQ ID NO:15415 | SEQ ID NO:23427 |
| | | AA | GYGMN | IIWYDGNNKYYADSVKG | DRVYCSSTSCHPYYYYYAMDV |
| | | | SEQ ID NO:7404 | SEQ ID NO:15416 | SEQ ID NO:23428 |
| iPS:436796 | 21-225_170A5 | NA | AACTGTGGCATGCAC | ATTATATGGTATGATGGAAGTAATAAATACTATGCAGACTCCGTGAAGGGC | GATCAGTACAACAGGAACGACGGACCACCAGCTTACTACTACTACTACGGTTTGGACGTC |
| | | | SEQ ID NO:7405 | SEQ ID NO:15417 | SEQ ID NO:23429 |
| | | AA | NCGMH | IIWYDGSNKYYADSVKG | DQYNRNDGPPAYYYYYGLDV |
| | | | SEQ ID NO:7406 | SEQ ID NO:15418 | SEQ ID NO:23430 |
| iPS:436798 | 21-225_171F5 | NA | AGCTATAGCTTGAAC | TACATTGGTAGTAGTGGCAGTATCATATTCTACGCAGACTCTGTGAAGGGC | GGGGATACAGCTGGGGTTACCTATTACTACGGTATGGACGTC |
| | | | SEQ ID NO:7407 | SEQ ID NO:15419 | SEQ ID NO:23431 |
| | | AA | SYSLN | YIGSSGSIIFYADSVKG | GDTAGVTYYYGMDV |
| | | | SEQ ID NO:7408 | SEQ ID NO:15420 | SEQ ID NO:23432 |

FIGURE 49
(Continued)

| | | | | | |
|---|---|---|---|---|---|
| iPS:436800 | 21-225_171D12 | NA | AGTTACTATATGTAT | ATAATCAACCCTAGTGGTGGTAGCACAAACTACGCACAGAAGTTCCAGGGC | GGTTGGGAGTTAAACTAC |
| | | | SEQ ID NO:7409 | SEQ ID NO:15421 | SEQ ID NO:23433 |
| | | AA | SYYMY | IINPSGGSTNYAQKFQG | GWELNY |
| | | | SEQ ID NO:7410 | SEQ ID NO:15422 | SEQ ID NO:23434 |
| iPS:436802 | 21-225_171E12 | NA | AGTTATGGCATGCAC | GTTATATGGAATGATGGAGGTAATAAATATAATGGAGACTCCGTGAAGGGC | GACCGTACGTATTACTCTGGTTCGGGGAGCCCCCCTACTACTACTACGGTATGGACGTC |
| | | | SEQ ID NO:7411 | SEQ ID NO:15423 | SEQ ID NO:23435 |
| | | AA | SYGMH | VIWNDGGNKYNGDSVKG | DRTYYSGSGSPPYYYYGMDV |
| | | | SEQ ID NO:7412 | SEQ ID NO:15424 | SEQ ID NO:23436 |
| iPS:436804 | 21-225_172C3 | NA | AGTTACTATATGTAT | ACAATCAACCCTAGTGGTGGTAGCACAGACTACGCACAGAAGTTCCAGGGC | GGCTGGGAGTTAAACTAC |
| | | | SEQ ID NO:7413 | SEQ ID NO:15425 | SEQ ID NO:23437 |
| | | AA | SYYMY | TINPSGGSTNYAQKFQG | GWELNY |
| | | | SEQ ID NO:7414 | SEQ ID NO:15426 | SEQ ID NO:23438 |
| iPS:436806 | 21-225_172B12 | NA | AGTTACTATATGTAT | ACAATCAACCCTAGTGGTGGTAGCACAGACTACGCACAGAAGTTCCAGGGC | GGCTGGGAATTAAACTAC |
| | | | SEQ ID NO:7415 | SEQ ID NO:15427 | SEQ ID NO:23439 |
| | | AA | SYYMY | TINPSGGSTDYAQKFQG | GWELNY |
| | | | SEQ ID NO:7416 | SEQ ID NO:15428 | SEQ ID NO:23440 |
| iPS:436808 | 21-225_173F8 | NA | AGCTATGGCATGCAC | GTTATATCATATGATGGAAGTCCTAAATACTGTGCAGACTCCGTGAAGGGC | GATGAAAGGCAGTGGCTGCCGGCCCCTACGGTATGGACGTC |
| | | | SEQ ID NO:7417 | SEQ ID NO:15429 | SEQ ID NO:23441 |

FIGURE 49
(Continued)

| | | AA | SYGMH | VISYDGSPKYCADSVKG | DERQWLPAPYGMDV |
|---|---|---|---|---|---|
| iPS:436810 | 21-225_175F4 | | SEQ ID NO:7418 | SEQ ID NO:15430 | SEQ ID NO:23442 |
| | | NA | AGCAACAGTGTGCTGCTTGGAAC | AGGACATACTACAGGTCCAAGTGGTATAATGCTTATCCAGTATCTATGAAAGT | GATAAGGCAGCTGGGAGGAATGACTTCTACTACGGTATGGACGTC |
| | | | SEQ ID NO:7419 | SEQ ID NO:15431 | SEQ ID NO:23443 |
| iPS:436812 | 21-225_175C6 | AA | SNSAAWN | RTYYRSKWYNAYPVSMES | DKAAGRNDFYYGMDV |
| | | | SEQ ID NO:7420 | SEQ ID NO:15432 | SEQ ID NO:23444 |
| | | NA | AACTGTGGCATGCAC | ATTATATGGTATGATGGAAGTAATAAATACTATGCAGACTCCGTGAAGGGC | GATCAGTACAACAGGAACGACGGACCACCAGCTACTACTACTACTACGGTTTGGACGTC |
| | | | SEQ ID NO:7421 | SEQ ID NO:15433 | SEQ ID NO:23445 |
| iPS:436814 | 21-225_178H10 | AA | NCGMH | IIWYDGSNKYYADSVKG | DQYNRNDGPPAYYYYYGLDV |
| | | | SEQ ID NO:7422 | SEQ ID NO:15434 | SEQ ID NO:23446 |
| | | NA | AGCAACAGTGTGCTGCTTGGAAC | AGGACATACTACAGGTCCAAGTGGTATAATGCTTATCCAGTATCTATGAAAGT | GATAAGGCAGCTGGGAGGAATGACTTCTACTACTACGGTATGGACGTC |
| | | | SEQ ID NO:7423 | SEQ ID NO:15435 | SEQ ID NO:23447 |
| iPS:436816 | 21-225_179H5 | AA | SNSAAWN | RTYYRSKWYSAYPVSMES | DKAAGRNDFYYGMDV |
| | | | SEQ ID NO:7424 | SEQ ID NO:15436 | SEQ ID NO:23448 |
| | | NA | AGCTATGGCATGCAC | GTTATATGGTATGATGGAAGTAATGAATACTATGCAGACTCCGTGAAGGGC | GATATCCGGAACTACTACTACGGTTTGGACGTC |
| | | | SEQ ID NO:7425 | SEQ ID NO:15437 | SEQ ID NO:23449 |

FIGURE 49
(Continued)

| | | | | SYGMH | VIWYDGSNEYYADSVKG | DIRNYYYGLDV |
|---|---|---|---|---|---|---|
| iPS:436818 | 21-225_179C7 | | AA | SEQ ID NO:7426 | SEQ ID NO:15438 | SEQ ID NO:23450 |
| | | | NA | AACTCTGGCATGCAC | ATTATATATTGATGGAAGTTATAAATACAATGCAGACTCCGTGAAGGGC | GACCGTCATTACGATTCCACGTTCCTACTATTACTATTACGGTATGGACGTC |
| | | | | | | SEQ ID NO:23451 |
| | | | AA | NSGMH | IIYYDGSYKYNADSVKG | DRHYDFHVPYYYYGMDV |
| iPS:436820 | 21-225_179D10 | | | SEQ ID NO:7428 | SEQ ID NO:15440 | SEQ ID NO:23452 |
| | | | NA | AGCTATAGCATGAAC | TACATTAGTAGTAGTGGAAGTACCACATACGCAGACTCTGTGCAGGC | GATAGTAGGAAGGGGTTCTACTACGGTCTGGACGTC |
| | | | | | SEQ ID NO:15441 | SEQ ID NO:23453 |
| | | | AA | SYSMN | YISSSGSTTYYADSVQG | DSRKGFYYGLDV |
| iPS:436822 | 21-225_180D4 | | | SEQ ID NO:7430 | SEQ ID NO:15442 | SEQ ID NO:23454 |
| | | | NA | AACTTTGGCATGCAC | ATTATATGGTATGATGGAAGTGATAAATACTATGCAGACTCCGTGAAGGGC | GGGGGGCCCCGTTCTCTACGGTGACTATGTACTTGACTAC |
| | | | | | | SEQ ID NO:23455 |
| | | | AA | NFGMH | IIWYDGSDKYYADSVKG | GGPPFSTVTMYFDY |
| iPS:436824 | 21-225_180C5 | | | SEQ ID NO:7432 | SEQ ID NO:15444 | SEQ ID NO:23456 |
| | | | NA | ACTAGTGGAGTGGGTGTGGGC | TTCATTTCTTGGAATGATGATAAGCGCTACAGCCCATCTCTGAAGAGC | AAAGCAGCAGCTGTTGCTTTTGATATC |
| | | | | | SEQ ID NO:15445 | SEQ ID NO:23457 |
| | | | AA | TSGVGVG | FISWNDDKRYSPSLKS | KAAAVAFDI |
| | | | | SEQ ID NO:7434 | SEQ ID NO:15446 | SEQ ID NO:23458 |

FIGURE 49
(Continued)

| | | NA/AA | | | | | |
|---|---|---|---|---|---|---|---|
| iPS:436826 | 21-225_180G5 | NA | AGTTATGATATCAAC | | TGGATGAACCCTAACAGTGGTAACACAGGCTATGCACAGAAGTTCCAGGGC | | GGGTTTTATTACTACTATGGTTCGGGGAGTCATGTCCCTACCACTACTACGGTTTGGACGTC |
| | | AA | SEQ ID NO:7435<br>SYDIN | | SEQ ID NO:15447<br>WMNPNSGNTGYAQKFQG | | SEQ ID NO:23459<br>GFYYYGSGSHVPYHYYYGLDV |
| iPS:436828 | 21-225_181H1 | NA | AACTATGGCATGCAC | | ATTATATGGTATGATGGAAGTGATAAATACTATGCAGACTCCGTGAAGGGC | | GGGGGCCCCCGTTTCTACGGTGACTATGTACTTCGACTAC |
| | | AA | SEQ ID NO:7436<br>NYGMH | | SEQ ID NO:15448<br>IIWYDGSDKYYADSVKG | | SEQ ID NO:23460<br>GGPPFSTVTMYFDY |
| | | | SEQ ID NO:7437 | | SEQ ID NO:15449 | | SEQ ID NO:23461 |
| iPS:436830 | 21-225_51F4 | NA | AGCTATGGTATCAGC | | TGGATCAGCGCTTATAATGGTAACACAAAGTATGCACAGAAGCTCCAGGGC | | CACGATTTTGGAGTGGTTATTATAAGGGTATGGACGTC |
| | | AA | SEQ ID NO:7438<br>SYGIS | | SEQ ID NO:15450<br>WISAYNGNTKYAQKLQG | | SEQ ID NO:23462<br>HDFWSGYYKGMDV |
| | | | SEQ ID NO:7439 | | SEQ ID NO:15451 | | SEQ ID NO:23463 |
| iPS:436832 | 21-225_51D8 | NA | AGTAACAGTGCTGCTTGGAAC | | AGGACATACTACAGGTCCAAGTGGTATAATGATTATGCAGTATCTGTGAAAAGT | | GACCGCTATAACTGGAACTACCCCTACTGGTACTTCGATCTC |
| | | AA | SEQ ID NO:7440<br>SNSAAWN | | SEQ ID NO:15452<br>RTYYRSKWYNDYAVSVKS | | SEQ ID NO:23464<br>DRYNWNYPYWYFDL |
| | | | SEQ ID NO:7441 | | SEQ ID NO:15453 | | SEQ ID NO:23465 |
| | | | SEQ ID NO:7442 | | SEQ ID NO:15454 | | SEQ ID NO:23466 |

FIGURE 49
(Continued)

| | | | | |
|---|---|---|---|---|
| iPS:436834 | 21-225_52F1 | NA | AGCTATGGTGTCAGC SEQ ID NO:7443 | TGGATCAGCGGCTTATAAT GGTAACAGAAAGTATGC ACAGAAGCTCCAGGGC SEQ ID NO:15455 | CACGATTTTGGAGTGGTTA TTATAAGGGTATGGACGTC SEQ ID NO:23467 |
| | | AA | SYGVS SEQ ID NO:7444 | WISAYNGNRKYAQKLQG SEQ ID NO:15456 | HDFWSGYYKGMDV SEQ ID NO:23468 |
| iPS:436836 | 21-225_52H1 | NA | GGCTATGGCATGCAC SEQ ID NO:7445 | GTTATATGGTATGATGG AAGTAATAAATACTATG CAGACTCCGTGAAGGGC SEQ ID NO:15457 | GATGGGTCTATTGTAGTAG TTCCAGCTGCTCATATTACTA CTACTACTACGGTATGGACG TC SEQ ID NO:23469 |
| | | AA | GYGMH SEQ ID NO:7446 | VIWYDGSNKYYADSVKG SEQ ID NO:15458 | DRVYCSSSSCSYYYYGMD V SEQ ID NO:23470 |
| iPS:436838 | 21-225_52H4 | NA | CACTTTGGCATGCAC SEQ ID NO:7447 | GTTATTTGGTATGATGATGGA AGTAATAAATACTATGC AGACTCCGTGAAGGGC SEQ ID NO:15459 | GGGGACTGGAACTACGAGGG TTTTGACTAC SEQ ID NO:23471 |
| | | AA | HFGMH SEQ ID NO:7448 | VIWYDGSNKYYADSVKG SEQ ID NO:15460 | GDWNYEGFDY SEQ ID NO:23472 |
| iPS:436840 | 21-225_53E9 | NA | GGCTACTATATGCAC SEQ ID NO:7449 | TGGATCATCCCTAACAGT GGTGACACAAACTATGC ACAGAAGTTTCAGGGC SEQ ID NO:15461 | GATGGGTATAGCAGTGGCTG GTTCAACTGGTTCGACCCC SEQ ID NO:23473 |
| | | AA | GYYMH SEQ ID NO:7450 | WIIPNSGDTNYAQKFQG SEQ ID NO:15462 | DGYSSGWFNWFDP SEQ ID NO:23474 |

FIGURE 49
(Continued)

| iPS: | | | | | | |
|---|---|---|---|---|---|---|
| iPS:436842 | 21-225_54E9 | NA | AGCTATGGTATCAGC | TGGATTAGTGCTTATAATGGTAACACAAAGAATGCACAGAAGTCCAGGGC | CACGATTTTTGGAGTGGTTATTATAAGGGTATGGACGTC | |
| | | | SEQ ID NO:7451 | SEQ ID NO:15463 | SEQ ID NO:23475 | |
| | | AA | SYGIS | WISAYNGNTKNAQKLQG | HDFWSGYYKGMDV | |
| | | | SEQ ID NO:7452 | SEQ ID NO:15464 | SEQ ID NO:23476 | |
| iPS:436844 | 21-225_56G1 | NA | AGCTATGGTATCAGC | TGGATCAGCGCTTATAATGGTAACACAAAGTATGCACAGAAGTTCCAGGGC | CACGATTTTTGGAGTGGTTATTATAAGGGTATGGACGTC | |
| | | | SEQ ID NO:7453 | SEQ ID NO:15465 | SEQ ID NO:23477 | |
| | | AA | SYGIS | WISAYNGNTKYAQKFQG | HDFWSGYYKGMDV | |
| | | | SEQ ID NO:7454 | SEQ ID NO:15466 | SEQ ID NO:23478 | |
| iPS:436846 | 21-225_56E3 | NA | AGCTATGGTTTCAGC | TGGATCAGCGCTTATAATGGTAACACAAAGGAAGCACAGAAGTTCCAGGGC | CACGATTTTTGGAGTGGTTATTATAAGGGTATGGACGTC | |
| | | | SEQ ID NO:7455 | SEQ ID NO:15467 | SEQ ID NO:23479 | |
| | | AA | SYGFS | WISAYNGNTKEAQKFQG | HDFWSGYYKGMDV | |
| | | | SEQ ID NO:7456 | SEQ ID NO:15468 | SEQ ID NO:23480 | |
| iPS:436848 | 21-225_57F1 | NA | ACTAGTGGAGTGGGTGTGGGC | CTCATTTATTGGCATGAAGATAAGCGCTACAGCCCATCTCTGAAGAGC | GTCACAGGTATAGCAGCTCCCTAC | |
| | | | SEQ ID NO:7457 | SEQ ID NO:15469 | SEQ ID NO:23481 | |
| | | AA | TSGVGVG | LIYWHEDKRYSPSLKS | VTGIAAPY | |
| | | | SEQ ID NO:7458 | SEQ ID NO:15470 | SEQ ID NO:23482 | |

FIGURE 49
(Continued)

| | | | | | | |
|---|---|---|---|---|---|---|
| iPS:436850 | 21-225_57D9 | NA | ACTAGTGGAGTGGGTGTGGGC | | CTCATTTATTGGAATGAT GATAAGCGCTACAGTCC ATCTCTGAAGAGC | GCAGTGGCTGTGTCCTTTGA CTAC |
| | | | SEQ ID NO:7459 | | SEQ ID NO:15471 | SEQ ID NO:23483 |
| | | AA | TSGVGVG | | LIYWNDDKRYSPSLKS | AVAVSFDY |
| | | | SEQ ID NO:7460 | | SEQ ID NO:15472 | SEQ ID NO:23484 |
| iPS:436852 | 21-225_57H11 | NA | ACTAGTGGAGTGGGTGTGGGC | | CTCATTTATTGGCATGAA GATAGGCGCTACAGCCC ATCTCTGAAGAGC | GTCACAGGTATAGCAGCTCC CTAC |
| | | | SEQ ID NO:7461 | | SEQ ID NO:15473 | SEQ ID NO:23485 |
| | | AA | TSGVGVG | | LIYWHEDRRYSPSLKS | VTGIAAPY |
| | | | SEQ ID NO:7462 | | SEQ ID NO:15474 | SEQ ID NO:23486 |
| iPS:436854 | 21-225_58C1 | NA | ACTAGTGGAGTGGGTGTGGGC | | CTCATTTATTGGATGAT GATAAGCGCTACAGCCC ATCTCTGAAGAGC | CTTATAGCAGTGGCCTTTGA CTCC |
| | | | SEQ ID NO:7463 | | SEQ ID NO:15475 | SEQ ID NO:23487 |
| | | AA | TSGVGVG | | LIYWDDDKRYSPSLKS | LIAVAFDS |
| | | | SEQ ID NO:7464 | | SEQ ID NO:15476 | SEQ ID NO:23488 |
| iPS:436856 | 21-225_58C5 | NA | AGCTATAGCATGAAC | | TCCATTAGTAGTAGTAGT TATTACTTATACTACGCA GACTCAGTGAAGGGC | ACCTATAGCAGTGGGAGTTTTGA CTAC |
| | | | SEQ ID NO:7465 | | SEQ ID NO:15477 | SEQ ID NO:23489 |
| | | AA | SYSMN | | SISSSSYYLYYADSVKG | TYSGSFDY |
| | | | SEQ ID NO:7466 | | SEQ ID NO:15478 | SEQ ID NO:23490 |
| iPS:436858 | 21-225_58E7 | NA | TTCTATGGCATGCAC | | GTTACATCATATGATGG AAGTGATAAATACTATG CAGACTCCGTGAAGGGC | DATGACTATGGTTCGGGGAG TCCCTATACTACGGTATGG ACGTC |
| | | | SEQ ID NO:7467 | | SEQ ID NO:15479 | SEQ ID NO:23491 |
| | | AA | FYGMH | | VTSYDGSDKYYADSVKG | DDYGSGSPLYYGMDV |

FIGURE 49
(Continued)

| | | | | | |
|---|---|---|---|---|---|
| iPS:436860 | 21-225_58F7 | NA | SEQ ID NO:7468 AGCTTTTGGATGAGC | SEQ ID NO:15480 CACATAAGCAAGATGG AAGTGAGAAATACTATG TGGACTCTGTGAAGGGC | SEQ ID NO:23492 GGGGACCTCCATACAGTC GGGCTACTACTACGGTATGG ACGTC |
| | | AA | SEQ ID NO:7469 SFWMS | SEQ ID NO:15481 HIKQDGSEKYYVDSVKG | SEQ ID NO:23493 GDLPYSSGYYYGMDV |
| iPS:436862 | 21-225_58F8 | NA | SEQ ID NO:7470 AGCTATGGCATGCAC | SEQ ID NO:15482 GTTATATCATATGATGGA AGTAATAAATACTATGC AGACTCCGTGAAGGGC | SEQ ID NO:23494 GATGAGGGACGTGGATATGG TGGCTACGAGAGGGATATT ACTACTACTACGGTATG GACGTC |
| | | AA | SEQ ID NO:7471 SYGMH | SEQ ID NO:15483 VISYDGSNKYYADSVKG | SEQ ID NO:23495 DEGRGYGGYERGYYYYYG MDV |
| iPS:436864 | 21-225_58G11 | NA | SEQ ID NO:7472 AGCTATAGCATGAAC | SEQ ID NO:15484 TACATTAGTACTAGTAGT AGTACCATATTCTACGCA GACTCTGTGAAGGGC | SEQ ID NO:23496 GGGGATACAGCTATGGTCCT CTACTACTACGGTATGGACG TC |
| | | AA | SEQ ID NO:7473 SYSMN | SEQ ID NO:15485 YISTSSSTIFYADSVKG | SEQ ID NO:23497 GDTAMVLYYYGMDV |
| iPS:436866 | 21-225_59F2 | NA | SEQ ID NO:7474 AGCTATAGCATGAAC | SEQ ID NO:15486 TACATTAGTGGGAGTAG TAATATCATATACTACAC AGACTCTGTGAAGGGC | SEQ ID NO:23498 GCGGATACACCTATGGTCCT TTACTTCTACGGTATGGACG TC |
| | | AA | SEQ ID NO:7475 SYSMN | SEQ ID NO:15487 YISGSSNIYYTDSVKG | SEQ ID NO:23499 ADTPMVLYFYGMDV |
| | | | SEQ ID NO:7476 | SEQ ID NO:15488 | SEQ ID NO:23500 |

FIGURE 49
(Continued)

| | | | | | |
|---|---|---|---|---|---|
| iPS:436868 | 21-225_59B11 | NA | AGTTATGGGCGTGCAC SEQ ID NO:7477 | GCTATATGGTATGATGG AAGTAATAAATACTATG CAGACTCCGTGAAGGGC SEQ ID NO:15489 | GATAGGGACTATTGTAGTAG TTCCAGCTGCCTTACTACTA CTACTACGGTATGGACGTC SEQ ID NO:23501 |
| | | AA | SYGVH SEQ ID NO:7478 | AIWYDGSNKYYADSVKG SEQ ID NO:15490 | DRDYCSSSSCPYYYYYGMDV SEQ ID NO:23502 |
| iPS:436870 | 21-225_60B1 | NA | ACTAGTGGAGTGGGTGTGG C SEQ ID NO:7479 | CTCATTTATTGGCATGAA GATAAGCGCTACAGCCC ATCTCTGAAGAGC SEQ ID NO:15491 | GTCACATATATAGCAGCTCC CTAC SEQ ID NO:23503 |
| | | AA | TSGVGVG SEQ ID NO:7480 | LIYWHEDKRYSPSLKS SEQ ID NO:15492 | VTYIAAPY SEQ ID NO:23504 |
| iPS:436872 | 21-225_60D2 | NA | AGCTATAGCATGAAC SEQ ID NO:7481 | TACATTAGTGAGAGTAG TAATATCATATACTACAC AGACTCTGTGAAGGGC SEQ ID NO:15493 | GCGGATACACCTATGGTCCT TTACTTCTACGGTATGGACG TC SEQ ID NO:23505 |
| | | AA | SYSMN SEQ ID NO:7482 | YISESSNIYYTDSVKG SEQ ID NO:15494 | ADTPMVLYFYGMDV SEQ ID NO:23506 |
| iPS:436874 | 21-225_60A12 | NA | ACTAGTGGAGTGGGTGTGG C SEQ ID NO:7483 | CTCATTTATTGGGATGAT GATAAGCGCTACAGCCC ATCTCTGAAGAGC SEQ ID NO:15495 | CTTATAGCAGTGGCCTTTGA CTCC SEQ ID NO:23507 |
| | | AA | TSGVGVG SEQ ID NO:7484 | LIYWDDDKRYSPSLKS SEQ ID NO:15496 | LIAVAFDS SEQ ID NO:23508 |
| iPS:436876 | 21-225_61F5 | NA | ACTAGTGGGTTGGGTGTGG C SEQ ID NO:7485 | CTCATTTATTCACATGAA GATAAGCGCTACAGCCC ATCTCTGAAGAGC SEQ ID NO:15497 | GTCACAGGTATAGCAGCTCC CTAC SEQ ID NO:23509 |

FIGURE 49
(Continued)

| | | AA | TSGLGVG | | LIYSHEDKRYSPSLKS | | VTGIAAPY | |
|---|---|---|---|---|---|---|---|---|
| | | | SEQ ID NO:7486 | | SEQ ID NO:15498 | | SEQ ID NO:23510 | |
| iPS:436878 | 21-225_62E3 | NA | ACTAGTGGAGTGGGTGTGGG C | SEQ ID NO:7487 | CTCATTAATTGGAATGAT GATAAGCGCTACAGCCC ATCTCTGAAGAGC | SEQ ID NO:15499 | AAAGCTACCTGGGTGGCTTT TGATATC | SEQ ID NO:23511 |
| | | AA | TSGVGVG | SEQ ID NO:7488 | LINWNDDKRYSPSLKS | SEQ ID NO:15500 | KATWVAFDI | SEQ ID NO:23512 |
| iPS:436880 | 21-225_62E8 | NA | ACTAGTGGAGTGGGTGTGGG C | SEQ ID NO:7489 | CTCATTAATTGGAATGAT GATAAGCGCTACAGCCC ATCTCTGAAGAGC | SEQ ID NO:15501 | AAAGCTACCTGGGTGGCTTT TGATATC | SEQ ID NO:23513 |
| | | AA | TSGVGVG | SEQ ID NO:7490 | LINWNDDKRYSPSLKS | SEQ ID NO:15502 | KATWVAFDI | SEQ ID NO:23514 |
| iPS:436882 | 21-225_62D10 | NA | ACTAGTGGAGTGGGTGTGGG C | SEQ ID NO:7491 | CTCATTAATTGGAATGAT GATAAGCGCTACAGCCC ATCTCTGAAGAGC | SEQ ID NO:15503 | AAAGCTACCTGGGTGGCTTT TGATATC | SEQ ID NO:23515 |
| | | AA | TSGVGVG | SEQ ID NO:7492 | LINWNDDKRYSPSLKS | SEQ ID NO:15504 | KATWVAFDI | SEQ ID NO:23516 |
| iPS:436884 | 21-225_62A12 | NA | ACTAGTGGAGTGGGTGTGGG C | SEQ ID NO:7493 | CTCATTAATTGGAATGAT GATAAACGCTACAGCCC ATCTCTGAAGAGC | SEQ ID NO:15505 | AAAACTACCTGGGTGGCTTT TGATATC | SEQ ID NO:23517 |
| | | AA | TSGVGVG | SEQ ID NO:7494 | LINWNDDKRYSPSLKS | SEQ ID NO:15506 | KTTWVAFDI | SEQ ID NO:23518 |
| iPS:436886 | 21-225_62B12 | NA | ACTAGTGGAGTGGGTGTGGG C | SEQ ID NO:7495 | CTCATTAATTGGAATGAT GATAAGCGCTACAGCCC GTCTCTGAAGAGC | SEQ ID NO:15507 | AAAGCTACCTGGGTGGCTTT TGATATC | SEQ ID NO:23519 |

FIGURE 49
(Continued)

| | | AA/NA | | | | | |
|---|---|---|---|---|---|---|---|
| iPS:436888 | 21-225_63G7 | AA | TSGVGVG | SEQ ID NO:7496 | LINWNDDKRYSPSLKS | SEQ ID NO:15508 | KATWVAFDI | SEQ ID NO:23520 |
| | | NA | AGCTATAGCATGAAC | SEQ ID NO:7497 | TACATTAGTAGTAGTACTAGTACCATATACTACGCAGCCCTCTGTGAAGGGC | SEQ ID NO:15509 | GATCACCGTTACTATGATAGTAGTGGTTATTACTCTGATGCTTTTGATATC | SEQ ID NO:23521 |
| iPS:436890 | 21-225_63A10 | AA | SYSMN | SEQ ID NO:7498 | YISSSTSTIYYAASVKG | SEQ ID NO:15510 | DHRYYDSSGYYSDAFDI | SEQ ID NO:23522 |
| | | NA | AGCTATAGCATGAAC | SEQ ID NO:7499 | TACATTAGTAGTAGTACTAGTACCATATACTACGCAGCCCTCTGTGAAGGGC | SEQ ID NO:15511 | GATCACCGTTACTATGATAGTAGTGGTTATTACTCTGATGCTTTTGATATC | SEQ ID NO:23523 |
| iPS:436892 | 21-225_65E9 | AA | SYSMN | SEQ ID NO:7500 | YISSSTSTIYYAASVKG | SEQ ID NO:15512 | DHRYYDSSGYYSDAFDI | SEQ ID NO:23524 |
| | | NA | GGCTACTATATGCAC | SEQ ID NO:7501 | TGGATCAACCCTAACAGTGGTGGCACAAATTATGCACAGAAGTTTCAGGGC | SEQ ID NO:15513 | GCGTATTATTATGGTTCGGGGAGTTATTATAATGAATTTGATATG | SEQ ID NO:23525 |
| iPS:436894 | 21-225_66G9 | AA | GYYMH | SEQ ID NO:7502 | WINPNSGGTNYAQKFQG | SEQ ID NO:15514 | AYYYGSGSYYNEFDM | SEQ ID NO:23526 |
| | | NA | ACTAGTGGAGTGGGTGTGGGC | SEQ ID NO:7503 | CTCATTAATTGGAATGATGATAAGCGCTTCAGCCCATCTCTGAAGAGC | SEQ ID NO:15515 | AAAGCTACCTGGGTGGCTTTTGATATC | SEQ ID NO:23527 |
| | | AA | TSGVGVG | SEQ ID NO:7504 | LINWNDDKRFSPSLKS | SEQ ID NO:15516 | KATWVAFDI | SEQ ID NO:23528 |
| iPS:436896 | 21-225_67F10 | NA | GGCTACTATATGCAC | SEQ ID NO:7505 | TGGATCAACCCTAACAGTGGTGGCACAAACTATGGACAGAAGTTTCAGGGC | SEQ ID NO:15517 | ACGTATTTCTATGGTTCGGGGAGTTATTATAACGGCTTTGACTAC | SEQ ID NO:23529 |

FIGURE 49
(Continued)

| | | | | | | | |
|---|---|---|---|---|---|---|---|
| iPS:436898 | 21-225_68D8 | AA | GYYMH | | WINPNSGGTNYGQKFQG | | TYFYGSGSYYNGFDY |
| | | | SEQ ID NO:7506 | | SEQ ID NO:15518 | | SEQ ID NO:23530 |
| | | NA | AGCAACAGTGCTGCTTGGAAC | | AGGACATACTACAGGTCCGAGTGCTATAATGATTATGCAGTATCTGTGCAGAGT | | GATAGAGGGCATAGAGGGTTCTACGGTATGGACGTC |
| | | | SEQ ID NO:7507 | | SEQ ID NO:15519 | | SEQ ID NO:23531 |
| | | AA | SNSAAWN | | RTYYRSECYNDYAVSVQS | | DRGHRGFYGMDV |
| iPS:436900 | 21-225_69B9 | | SEQ ID NO:7508 | | SEQ ID NO:15520 | | SEQ ID NO:23532 |
| | | NA | GGCTACCATATGCAC | | TGGATCAACCCTAACAGTGGTGGCACAAATTATGCACAGAAGTTTCAGGGC | | GCGTATTATTATGGTTCGGGGAGTTATTATAATGAATCTGATATG |
| | | | SEQ ID NO:7509 | | SEQ ID NO:15521 | | SEQ ID NO:23533 |
| | | AA | GYHMH | | WINPNSGGTNYAQKFQG | | AYYYGSGSYYNESDM |
| iPS:436902 | 21-225_69B11 | | SEQ ID NO:7510 | | SEQ ID NO:15522 | | SEQ ID NO:23534 |
| | | NA | GGCTACTATATGCAC | | TGGATCAACCCTAACAGTGGTGGCACAAACTATGGACAGAAGTTTCAGGAC | | ACGTATTACTATGGGTCGGGGAGTTATTATAACGGCTTTGACTAC |
| | | | SEQ ID NO:7511 | | SEQ ID NO:15523 | | SEQ ID NO:23535 |
| | | AA | GYYMH | | WINPNSGGTNYGQKFQD | | TYYYGGSGSYYNGFDY |
| iPS:436904 | 21-225_71D4 | | SEQ ID NO:7512 | | SEQ ID NO:15524 | | SEQ ID NO:23536 |
| | | NA | GGCTACTGTATGCAC | | TGGATCAACCCTAACAGTGGTGGCACAAACTATGCACAGAAGTTTCAGGTC | | GCGTATTACTATGGTTCGGGGACTTATCATAACGAATTTG ACTAC |
| | | | SEQ ID NO:7513 | | SEQ ID NO:15525 | | SEQ ID NO:23537 |
| | | AA | GYCMH | | WINPNSGGTNYAQKFQV | | AYYYGSGTYHNEFDY |
| | | | SEQ ID NO:7514 | | SEQ ID NO:15526 | | SEQ ID NO:23538 |

FIGURE 49
(Continued)

| | | | | |
|---|---|---|---|---|
| iPS:436906 | 21-225_72B4 | NA | GGCTACTACTATATGCAC<br>SEQ ID NO:7515 | TGGATCAACCCTAACAG<br>TGGTGGCACAAACTATG<br>GACAGAAGTTTCAGGGC<br>SEQ ID NO:15527 | ACGTATTACTATGGTTCGGG<br>GAGTTATTATAACGGCTTTG<br>ACTAC<br>SEQ ID NO:23539 |
| | | AA | GYYMH<br>SEQ ID NO:7516 | WINPNSGGTNYGQKFQG<br>SEQ ID NO:15528 | TYYYGSGSYYNGFDY<br>SEQ ID NO:23540 |
| iPS:436908 | 21-225_72D5 | NA | ACTAGTGGAGTGGGTGTGG<br>C<br>SEQ ID NO:7517 | CTCATTAATTGGAATGAT<br>GATAAGCGCTACAGCCC<br>ATCTCTGAAGAGC<br>SEQ ID NO:15529 | AAAGCTACCTGGGTGGCTTT<br>TGATATC<br>SEQ ID NO:23541 |
| | | AA | TSGVGVG<br>SEQ ID NO:7518 | LINWNDDKRYSPSLKS<br>SEQ ID NO:15530 | KATWVAFDI<br>SEQ ID NO:23542 |
| iPS:436910 | 21-225_73G1 | NA | TACTATGGCATGCAC<br>SEQ ID NO:7519 | GTTACAACATATGATGG<br>AAGTAATAAATACTATG<br>CAGACTCCGTGAAGGGC<br>SEQ ID NO:15531 | GAGACTGGAACCTGGGCTTT<br>TGATATC<br>SEQ ID NO:23543 |
| | | AA | YYGMH<br>SEQ ID NO:7520 | VTTYDGSNKYYADSVKG<br>SEQ ID NO:15532 | ETGTWAFDI<br>SEQ ID NO:23544 |
| iPS:436912 | 21-225_73C4 | NA | ACTAGTGGAGTGGGTGTGG<br>C<br>SEQ ID NO:7521 | CTCATTAATTGGAATGAT<br>GATAAGCGCTACAGCCC<br>ATCTCTGAAGAGC<br>SEQ ID NO:15533 | AAAACTACCTGGGTGGCTTT<br>TGATATC<br>SEQ ID NO:23545 |
| | | AA | TSGVGVG<br>SEQ ID NO:7522 | LINWNDDKRYSPSLKS<br>SEQ ID NO:15534 | KTTWVAFDI<br>SEQ ID NO:23546 |
| iPS:436914 | 21-225_76B4 | NA | ACTGGTGGAGTGGGTGTGG<br>C<br>SEQ ID NO:7523 | CTCATTATTGGGATGAT<br>GATAAGCGCTACAGCCC<br>ATCTCTGAAGAGC<br>SEQ ID NO:15535 | CTTATAGCAGTGGCCTTTGA<br>CTAC<br>SEQ ID NO:23547 |

FIGURE 49
(Continued)

| | | AA | TGGVGVG | LIYWDDKRYSPSLKS | LIAVAFDY |
|---|---|---|---|---|---|
| iPS:436916 | 21-225_74A9 | NA | AGCTATGGCATGCAC SEQ ID NO:7524 | GTTATATGGTATGATGG AATAATAAATCCTATG CAGACTCCGTGAAGGGC SEQ ID NO:15535 | GATCGAGATTATTGTAGTGG TACCAGCTGCCCTTATTA CTACTACGGTATGGACGTC SEQ ID NO:23548 |
| | | AA | SYGMH SEQ ID NO:7525 | VIWYDGNNKSYADSVKG SEQ ID NO:15537 | DRDYCSGTSCPYYYYYGMDV SEQ ID NO:23549 |
| iPS:436918 | 21-225_77A2 | NA | ACTAGTGGAGTGGGTGTGG C SEQ ID NO:7526 | TTCATTTATTGGGATGAT GATAAGCGCTACAGCCC ATCTCTGAAGAGC SEQ ID NO:15538 | CTTATAGCAGTGGCCTTTGA CTAC SEQ ID NO:23550 |
| | | AA | TSGVGVG SEQ ID NO:7527 | FIYWDDKRYSPSLKS SEQ ID NO:15539 | LIAVAFDY SEQ ID NO:23551 |
| iPS:436920 | 21-225_74E5 | NA | AGTGGTGGTTACTACTGGAG C SEQ ID NO:7528 | TACATCTATTACAGTGGG AGCACCTACTACAACCC GTCCCTCAGGAGT SEQ ID NO:15540 | GATTCACCAGTGGCTGGTAC TGACTAC SEQ ID NO:23552 |
| | | AA | SGGYYWS SEQ ID NO:7529 | YIYYSGSTYYNPSLRS SEQ ID NO:15541 | DSPVAGTDY SEQ ID NO:23553 |
| iPS:436922 | 21-225_78E9 | NA | AGCTATGGCATGCAC SEQ ID NO:7530 | GTTATATGGTATGATGG AATAATAAATCCTATG CAGACTCCGTGAAGGGC SEQ ID NO:15542 | GATCGAGATTATTGTAGTGG TACCAGCTGCCCTTATTA CTACTACGGTATGGACGTC SEQ ID NO:23554 |
| | | AA | SYGMH SEQ ID NO:7531 | VIWYDGNNKSYADSVKG SEQ ID NO:15543 | DRDYCSSTSCPYYYYGMDV SEQ ID NO:23555 |
| | | NA | SEQ ID NO:7532 | SEQ ID NO:15544 | SEQ ID NO:23556 |

FIGURE 49
(Continued)

| iPS:436924 | 21-225_74B3 | NA | CGATATGGCATGCAC | GTTTTTGGTATGATGGA AGTAATAAAGACTATGC AGACTCCGTGAAGGGC | GATCGAGATTATTGTAGTAG TACCAGCTGCCCTTACTACT ACTACTACGGTATGGACGTC |
|---|---|---|---|---|---|
| | | | SEQ ID NO:7533 | SEQ ID NO:15545 | SEQ ID NO:23557 |
| | | AA | RYGMH | VFWYDGSNKDYADSVKG | DRDYCSSTSCPYYYYGMDV |
| | | | SEQ ID NO:7534 | SEQ ID NO:15546 | SEQ ID NO:23558 |
| iPS:436926 | 21-225_78D10 | NA | AGTGGTGGTTACTACTGGAG C | TACATCTATTACACATTGGG AGTGTTTACTACAACCCG TCCCTCAAGAGT | GATGCCCCGACTTCGGTAT GGACGTC |
| | | | SEQ ID NO:7535 | SEQ ID NO:15547 | SEQ ID NO:23559 |
| | | AA | SGGYYWS | YIYYIGSVYYNPSLKS | DAPDFGMDV |
| | | | SEQ ID NO:7536 | SEQ ID NO:15548 | SEQ ID NO:23560 |
| iPS:436928 | 21-225_79E7 | NA | AGCTATGGCATGCAC | GTTATATGGTATGATGG AAATAATAAATCCTATG CAGACTCCGTGAAGGGC | GATCGAGATTATTGTAGTAG TACCAGCTGCCCTTATTATTA CTACTACGGTATGGACGTC |
| | | | SEQ ID NO:7537 | SEQ ID NO:15549 | SEQ ID NO:23561 |
| | | AA | SYGMH | VIWYDGNNKSYADSVKG | DRDYCSSTSCPYYYYGMDV |
| | | | SEQ ID NO:7538 | SEQ ID NO:15550 | SEQ ID NO:23562 |
| iPS:436932 | 21-225_92A4 | NA | AGCTATGGCATGCAC | GTTATATGGTATGATGG AAATAATAAATCCTATG CAGACTCCGTGAAGGGC | GATCGAGATTATTGTAGTAG TACCAGCTGCCCTTATTATTA CTACTACGGTATGGACGTC |
| | | | SEQ ID NO:7539 | SEQ ID NO:15551 | SEQ ID NO:23563 |
| | | AA | SYGMH | VIWYDGNNKSYADSVKG | DRDYCSSTSCPYYYYGMDV |
| | | | SEQ ID NO:7540 | SEQ ID NO:15552 | SEQ ID NO:23564 |

FIGURE 49
(Continued)

| | | | | |
|---|---|---|---|---|
| iPS:436934 | 21-225_96B5 | NA | ACTGGTGGAGTGGGTGTGGG C<br>SEQ ID NO:7541 | CTCATTTATTGGGATGAT GATAAGCGCTACAGCCC ATCTCTGAAGAGC<br>SEQ ID NO:15553 | CTTATAGCAGTGGCCTGTGA CTAC<br>SEQ ID NO:23565 |
| | | AA | TGGVGVG<br>SEQ ID NO:7542 | LIYWDDDKRYSPSLKS<br>SEQ ID NO:15554 | LIAVACDY<br>SEQ ID NO:23566 |
| iPS:436936 | 21-225_97E6 | NA | AGCTATGGCATGAGC<br>SEQ ID NO:7543 | GTTATATGGTATGATGG AAATAATAAATCCTATG CAGACTCCGTGAAGGGC<br>SEQ ID NO:15555 | GATCGAGATTATTGTAGTAG TACCAGTGCCCTTATTATTA CTACTACGGTATGGACGTC<br>SEQ ID NO:23567 |
| | | AA | SYGMH<br>SEQ ID NO:7544 | VIWYDGNNKSYADSVKG<br>SEQ ID NO:15556 | DRDYCSSTSCPYYYYYGMDV<br>SEQ ID NO:23568 |
| iPS:436938 | 21-225_146A3 | NA | AGCTATGGCATGAGC<br>SEQ ID NO:7545 | GTTATTAGTGGTGGTGGT ACTACCACATACTACGC AGACTCCGTGAAGGGC<br>SEQ ID NO:15557 | TGGCGAGGTAACCCACTGA CTACGGTATGGACGTC<br>SEQ ID NO:23569 |
| | | AA | SYAMS<br>SEQ ID NO:7546 | VISGGGTTTYYADSVKG<br>SEQ ID NO:15558 | WRGNPTDYGMDV<br>SEQ ID NO:23570 |
| iPS:436940 | 21-225_146B8 | NA | ACCTATGGCATGCAC<br>SEQ ID NO:7547 | GTTGTATGGTATGGTGG AAATGATAAAGACTTTG CAGACTCCGTGACGGGC<br>SEQ ID NO:15559 | GATCGGGATTATTATTGTAGTGG TGGTAGCTGCCCTTACTACT ACTACTACGGTATGGACGTC<br>SEQ ID NO:23571 |
| | | AA | TYGMH<br>SEQ ID NO:7548 | VVWYGGNDKFADSVTG<br>SEQ ID NO:15560 | DRDYCSGGSCPYYYYYGMDV<br>SEQ ID NO:23572 |

FIGURE 49
(Continued)

| | | | | | |
|---|---|---|---|---|---|
| iPS:436942 | 21-225_146H8 | NA | AGTTATGATATCAAT SEQ ID NO:7549 | TGGATGAACCCTAACAG TGGTAACACAGGCTATG CACAGAAGTTCCAGGGC SEQ ID NO:15561 | GGAGATTATTACTATGATAG TAGTGGTCACCAGCCTACT ACTACTACGTATGGAC GTC SEQ ID NO:23573 |
| | | AA | SYDIN SEQ ID NO:7550 | WMNPNSGNTGYAQKFQG SEQ ID NO:15562 | GDYYYDSSGHQPYYYYGMD V SEQ ID NO:23574 |
| iPS:436944 | 21-225_182D12 | NA | ACTACTGGAGTGGGTGTGG C SEQ ID NO:7551 | ATCCTTTTTTGGAATGAT GATGAGCGCTACAGCCC ATCTCTGAAGAGC SEQ ID NO:15563 | AAATGCAGCTCGTCTACTT TGACTAC SEQ ID NO:23575 |
| | | AA | TTGVGVG SEQ ID NO:7552 | ILFWNDDERYSPSLKS SEQ ID NO:15564 | KSQLVYFDY SEQ ID NO:23576 |
| iPS:436946 | 21-225_183F4 | NA | AGTTATGGCATGCAC SEQ ID NO:7553 | GTTATATGGTATGATGG AAGTAATAAATACTATG CAGACTCCGTGAAGGGC SEQ ID NO:15565 | GAAAGGACGTATTGTAGTGG TACCACCTGCCCTACTACT ACTACTACGGTCTGGGGGTC SEQ ID NO:23577 |
| | | AA | SYGMH SEQ ID NO:7554 | VIWYDGSNKYYADSVKG SEQ ID NO:15566 | ERTYCSGTTCPYYYYYGLGV SEQ ID NO:23578 |
| iPS:436948 | 21-225_183F5 | NA | AGTTATGGCATGCTC SEQ ID NO:7555 | GTTATATGGTATGATGG AAGTGGTAAATACTATG CAGACTCCGTGAAGGGC SEQ ID NO:15567 | GAGAATTTTTGGAGTGGTGA CTAC SEQ ID NO:23579 |
| | | AA | SYGML SEQ ID NO:7556 | VIWYDGSGKYYADSVKG SEQ ID NO:15568 | ENFWSGDY SEQ ID NO:23580 |

FIGURE 49
(Continued)

| | | NA/AA | | | | |
|---|---|---|---|---|---|---|
| iPS:436950 | 21-225_184G4 | NA | AGCTATGGCATGCAC | | ATTATATGGTATGATGGAAGTAATAAATACTATGCAGACTCCGTGAAGGGC | GGGGGGCCCCGTTCTCTACGGTGACTATGTACTTGACTAC |
| | | | SEQ ID NO:7557 | | SEQ ID NO:15569 | SEQ ID NO:23581 |
| | | AA | SYGMH | | IIWYDGSNKYYADSVKG | GGPPFSTVTMYFDY |
| | | | SEQ ID NO:7558 | | SEQ ID NO:15570 | SEQ ID NO:23582 |
| iPS:436952 | 21-225_185D2 | NA | AACTATGGCATGCAC | | ATTATATGGTATGATGGAAGTGATAAATACTATGCAGACTCCGTGAAGGGC | GGGGGGCCCCGTTCTCTACGGTGACTATGTACTTGACTAC |
| | | | SEQ ID NO:7559 | | SEQ ID NO:15571 | SEQ ID NO:23583 |
| | | AA | NYGMH | | IIWYDGSDKYYADSVKG | GGPPFSTVTMYFDY |
| | | | SEQ ID NO:7560 | | SEQ ID NO:15572 | SEQ ID NO:23584 |
| iPS:436954 | 21-225_185G7 | NA | ACTGGTGGAGTGGGTGTGGGC | | CTCATTTATTGGAATGATGATGAGCGCTACAGCCCATCTCTGAAGAGC | ATTATAGCAGTGGCCTTCCAGCAT |
| | | | SEQ ID NO:7561 | | SEQ ID NO:15573 | SEQ ID NO:23585 |
| | | AA | TGGVGVG | | LIYWNDDERYSPSLKS | IIAVAFQH |
| | | | SEQ ID NO:7562 | | SEQ ID NO:15574 | SEQ ID NO:23586 |
| iPS:436956 | 21-225_186H6 | NA | ACTAGTGGTGGTTACTACTGGAGC | | TTCATTTCTTGGAATGATGATAAGGCTACACCCATCTCTGAAGAGC | AAAGCAGCAGCTGTTGCTTTTGATATC |
| | | | SEQ ID NO:7563 | | SEQ ID NO:15575 | SEQ ID NO:23587 |
| | | AA | TSGVGVG | | FISWNDDKRYSPSLKS | KAAAVAFDI |
| | | | SEQ ID NO:7564 | | SEQ ID NO:15576 | SEQ ID NO:23588 |
| iPS:436958 | 21-225_190D1 | NA | AGTGGTGGTTACTACTGGAGC | | TACATCTATTACAGTGGGAGCACCTACTACAACCCGTCCCTCAAGAGT | GATTCCCCACTACGAGGCTTGACTAC |
| | | | SEQ ID NO:7565 | | SEQ ID NO:15577 | SEQ ID NO:23589 |
| | | AA | SGGYYWS | | YIYYSGSTYYNPSLKS | DSPLRGFDY |

FIGURE 49
(Continued)

| | | | | | | | | |
|---|---|---|---|---|---|---|---|---|
| iPS:436960 | 21-225_198B2 | NA | SEQ ID NO:7566 | AGCTATGGCATGCAT | SEQ ID NO:15578 | GTTATAATATATGGATGG AAGTTATAAGTACTATG CAGACTCCGTGAAGGGC | SEQ ID NO:23590 | ACGTATAGCGGGGGTATGGA CGTC |
| | | AA | SEQ ID NO:7567 | SYGMH | SEQ ID NO:15579 | VIIYDGSYKYYADSVKG | SEQ ID NO:23591 | TYSGGMDV |
| iPS:436962 | 21-225_190H1 | NA | SEQ ID NO:7568 | AGGAAAAGTGCTACTTGGAAC | SEQ ID NO:15580 | AAGACATACTACAGGTC CAAGTGGTATAATGATT ATGCAGTATCTGTGAAA AGT | SEQ ID NO:23592 | GATCCGGGTGGCCTCTTTGA CTAC |
| | | AA | SEQ ID NO:7569 | RKSATWN | SEQ ID NO:15581 | KTYYRSKWYNDYAVSVK S | SEQ ID NO:23593 | DPGGLFDY |
| iPS:436964 | 21-225_190B3 | NA | SEQ ID NO:7570 | AACTATGGCATACAC | SEQ ID NO:15582 | GTTATATGGTTGATGGA GATAATAAATACTATGC AGACTCCGTGAAGGGC | SEQ ID NO:23594 | GATAACTGGAACTACGGCGA TCACTACTACTTCGGTAT GGACGTC |
| | | AA | SEQ ID NO:7571 | NYGIH | SEQ ID NO:15583 | VIWFDGDNKYYADSVKG | SEQ ID NO:23595 | DNWNYGDHYYFGMDV |
| iPS:436966 | 21-225_190C3 | NA | SEQ ID NO:7572 | AGCTATGGCATGCAC | SEQ ID NO:15584 | GTTATATGGTATGATGG AAGTAATAAATACTATG CAGACTCCGTGAAGGGC | SEQ ID NO:23596 | TGGTACTACTACTACTACGG TATGGACGTC |
| | | AA | SEQ ID NO:7573 | SYGMH | SEQ ID NO:15585 | VIWYDGSNKYYADSVKG | SEQ ID NO:23597 | WYYYYYGMDV |

FIGURE 49
(Continued)

| | | | | | | |
|---|---|---|---|---|---|---|
| iPS:436968 | 21-225_190B10 | NA | SEQ ID NO:7574<br>AGCTATGGCATGCAC | SEQ ID NO:15586<br>GTTATATGGAATGATGG<br>AAGTAAAAATACCATG<br>TAGACTCCGTGAAGGGC | SEQ ID NO:23598<br>GATCTGGATAAGAGGAACTT<br>TCCTTATTACTACTACTACGG<br>TATGGACGTC |
| | | AA | SEQ ID NO:7575<br>SYGMH | SEQ ID NO:15587<br>VIWNDGSKKYHVDSVKG | SEQ ID NO:23599<br>DLDKRNFPYYYYYGMDV |
| iPS:436970 | 21-225_190B8 | NA | SEQ ID NO:7576<br>AGCTATGGCATGCAC | SEQ ID NO:15588<br>GTTATATGGTTTGATGGA<br>AGTATAATAATACTATAC<br>AGACTCCGTGAAGGGC | SEQ ID NO:23600<br>GATAACTGGAACTACGGCGA<br>TTACTACTACTACTACGTA<br>TGGACGTC |
| | | AA | SEQ ID NO:7577<br>SYGMH | SEQ ID NO:15589<br>VIWFDGSNKYYTDSVKG | SEQ ID NO:23601<br>DNWNYGDYYYYYGMDV |
| iPS:436972 | 21-225_190C7 | NA | SEQ ID NO:7578<br>GGCTACTATATGCAC | SEQ ID NO:15590<br>TGGATCAACCCTAACAG<br>TGGTGGCACAAACTATG<br>CACAGAAGTTTCAGGGC | SEQ ID NO:23602<br>GATAGAGCAGTGGCTGGAAA<br>CTACTTCTACTACGGTATGG<br>ACGTC |
| | | AA | SEQ ID NO:7579<br>GYYMH | SEQ ID NO:15591<br>WINPNSGGTNYAQKFQG | SEQ ID NO:23603<br>DRAVAGNYFYYGMDV |
| iPS:436974 | 21-225_190H7 | NA | SEQ ID NO:7580<br>AGCTATGGCATGCAT | SEQ ID NO:15592<br>GTTATATATATGATGG<br>AAGTTATAAGTACTATG<br>CAGACTCCGTGAAGGGC | SEQ ID NO:23604<br>ACGTATAGCGGGGGGTATGGA<br>CGTC |
| | | AA | SEQ ID NO:7581<br>SYGMH | SEQ ID NO:15593<br>VIIYDGSYKYYADSVKG | SEQ ID NO:23605<br>TYSGGMDV |
| | | | SEQ ID NO:7582 | SEQ ID NO:15594 | SEQ ID NO:23606 |

FIGURE 49
(Continued)

| | | | | | |
|---|---|---|---|---|---|
| iPS:436976 | 21-225_190B8 | NA | AGCTATGGCCTGCAC | GTTATATGGTATGATGG AAGTAATAAATACTATG CAGACTCCGTGAAGGGC | TGGTACTACTACTACTACGG TATGGACGTC |
| | | | SEQ ID NO:7583 | SEQ ID NO:15595 | SEQ ID NO:23607 |
| | | AA | SYGLH | VIWYDGSNKYYADSVKG | WYYYYYGMDV |
| | | | SEQ ID NO:7584 | SEQ ID NO:15596 | SEQ ID NO:23608 |
| iPS:436978 | 21-225_190C9 | NA | AGGAAAAGTGCTACTGGAA C | AGGACATACAGGTC CAAGTGGTATAATGATT ATGCAGTATCTGTGAAA AGT | GATCCGGGTGGCCTCTTTGA CTAC |
| | | | SEQ ID NO:7585 | SEQ ID NO:15597 | SEQ ID NO:23609 |
| | | AA | RKSATWN | RTYYRSKWYNDYAVSVK S | DPGGLFDY |
| | | | SEQ ID NO:7586 | SEQ ID NO:15598 | SEQ ID NO:23610 |
| iPS:436980 | 21-225_190C10 | NA | AACTATGGCATGCAC | GTTATATGGTTTGGTGGA GATAATAAATACTATGC AGACTCCGTGAGGGGC | GATAACTGGAACTACGGCGA TCACTACTACTATTACGGAA TGGACGTC |
| | | | SEQ ID NO:7587 | SEQ ID NO:15599 | SEQ ID NO:23611 |
| | | AA | NYGMH | VIWFGGDNKYYADSVRG | DNWNYGDHYYYYGMDV |
| | | | SEQ ID NO:7588 | SEQ ID NO:15600 | SEQ ID NO:23612 |
| iPS:436982 | 21-225_190D10 | NA | AGCTATGGCATGCAT | GTTATATAATATATGATGG AAGTTATAAGTACTATG CAGACTCCGTGAAGGGC | ACGTATAGCGGGGGTATGGA CGTC |
| | | | SEQ ID NO:7589 | SEQ ID NO:15601 | SEQ ID NO:23613 |
| | | AA | SYGMH | VIIYDGSYKYYADSVKG | TYSGGMDV |
| | | | SEQ ID NO:7590 | SEQ ID NO:15602 | SEQ ID NO:23614 |

FIGURE 49
(Continued)

| | | | | | |
|---|---|---|---|---|---|
| iPS:436984 | 21-225_190F10 | NA | AGTGGTGGTGTGACTACTGGAGC SEQ ID NO:7591 | TACATCTATTATACAGTGGGATCACCTACTACAATCCGTCCCTCAAGAGT SEQ ID NO:15603 | GATAGCAGCTCGGGGGTATGGACGTC SEQ ID NO:23615 |
| | | AA | SGGDYWS SEQ ID NO:7592 | YIYYSGITYNPSLKS SEQ ID NO:15604 | DSSSRGMDV SEQ ID NO:23616 |
| iPS:436986 | 21-225_191A1 | NA | AGTTACTACTGGATC SEQ ID NO:7593 | TATATCTATTACAGTGGGAGTACTAAGTACAACCCCTCCCTCAAGAGT SEQ ID NO:15605 | AAGGGAGTGGGAACCATCACTTTGACTAC SEQ ID NO:23617 |
| | | AA | SYYWI SEQ ID NO:7594 | YIYYSGSTKYNPSLKS SEQ ID NO:15606 | KGVGTIHFDY SEQ ID NO:23618 |
| iPS:436988 | 21-225_191A2 | NA | AGTGGTGGTGTGACTACTGGAGC SEQ ID NO:7595 | TACATCTATTATACAGTGGGATCACCTACTACAATCCGTCCCTCAAGAGT SEQ ID NO:15607 | GATAGCAGCTCGGGGGTATGGACGTC SEQ ID NO:23619 |
| | | AA | SGGDYWS SEQ ID NO:7596 | YIYYSGITYNPSLKS SEQ ID NO:15608 | DSSSRGMDV SEQ ID NO:23620 |
| iPS:436992 | 21-225_191B8 | NA | AGCTATGGCATGCAC SEQ ID NO:7597 | GTTATATGGTTTGATGGAAGTAATAAATACTATGCAGACTCCGTGAAGGGC SEQ ID NO:15609 | GATAACTGGAACTACGGCGATCAACTACTACTATTACGGTATGGACGTC SEQ ID NO:23621 |
| | | AA | SYGMH SEQ ID NO:7598 | VIWFDGSNKYYADSVKG SEQ ID NO:15610 | DNWNYGDHYYYGMDV SEQ ID NO:23622 |
| iPS:436994 | 21-225_191A9 | NA | AATTATGGCATGCAC SEQ ID NO:7599 | GTTATATGGTTTGGTGGAGATAATAAATACTATGCAGACTCCGTGAAGGGC SEQ ID NO:15611 | GATAACTGGAACTACGGCGATCAACTACTACTATTACGGTATGGACGTC SEQ ID NO:23623 |

FIGURE 49
(Continued)

| | | | | | |
|---|---|---|---|---|---|
| iPS:436996 | 21-225_191B9 | AA | NYGMH | VIWFGGDNKYYADSVKG | DNWNYGDHYYYYGMDV |
| | | NA | TTCCATGGCATGCAC<br>SEQ ID NO:7600 | GTTATATGGTTATGATGG<br>AAGTAAAAATACTATG<br>CAGACTCCGTGAAGGGC<br>SEQ ID NO:15612 | GAAGGTATAGCAGTGGCTT<br>TTACAGGGGGTTGACAAC<br>SEQ ID NO:23624 |
| iPS:437000 | 21-225_191G9 | AA | FHGMH<br>SEQ ID NO:7601 | VIWYDGSKKYYADSVKG<br>SEQ ID NO:15613 | EGYSSGFYRGFDN<br>SEQ ID NO:23625 |
| | | NA | ACCTATGGCATGCAC<br>SEQ ID NO:7602 | CTTATATGGTTTGATGGA<br>AGTAATAAATACTATGC<br>AGACTCCGTGAAGGGC<br>SEQ ID NO:15614 | GATCGGGTGGGAGGTACTAG<br>TCCTCCTACTACTACTACTA<br>CGGTATGGACGTC<br>SEQ ID NO:23626 |
| iPS:437002 | 21-225_191H9 | AA | TYGMH<br>SEQ ID NO:7603 | LIWFDGSNKYYADSVKG<br>SEQ ID NO:15615 | DRVGGTSPPYYYYYGMDV<br>SEQ ID NO:23627 |
| | | NA | GGCTACAATATGCAC<br>SEQ ID NO:7604 | TGGATCAACCCTAATAG<br>TGGTGGCACAAACTATG<br>CACACAAGTTTCAGGGC<br>SEQ ID NO:15616 | GATTTCTATGATAGTGGTGG<br>AGAAGGGTGGTTCGACCCC<br>SEQ ID NO:23628 |
| iPS:437006 | 21-225_192G2 | AA | GYNMH<br>SEQ ID NO:7605 | WINPNSGGTNYAHKFQG<br>SEQ ID NO:15617 | DFYDSGGEGWFDP<br>SEQ ID NO:23629 |
| | | NA | AGCTATGGCATGCAC<br>SEQ ID NO:7606 | GTTATATGGAATGATGG<br>AAGTAATAAATACTATG<br>CAGACTCCGTGAAGGGC<br>SEQ ID NO:15618 | GATCTGGATAAGAGGAACTT<br>TCCTTATTACTACTACTACGG<br>TATGGACGTC<br>SEQ ID NO:23630 |
| | | | SEQ ID NO:7607 | SEQ ID NO:15619 | SEQ ID NO:23631 |

FIGURE 49 (Continued)

| | | | SYGMH | VIWNDGSNKYYADSVKG | DLDKRNFPYYYYGMDV |
|---|---|---|---|---|---|
| iPS:437008 | 21-225_192E3 | AA | SEQ ID NO:7608 | SEQ ID NO:15620 | SEQ ID NO:23632 |
| | | NA | AGTGGTGGTTACTACTGGAGC | TACATCTATTACACTGGGAGCACCTACTACAACCCGTCCCTCAAGAGT | GACGATCCCCTCTACGGAATGGACGTC |
| | | | SEQ ID NO:7609 | SEQ ID NO:15621 | SEQ ID NO:23633 |
| iPS:437010 | 21-225_192G3 | AA | SGGYYWS | YIYYTGSTYNPSLKS | DDPLYGMDV |
| | | NA | SEQ ID NO:7610 | SEQ ID NO:15622 | SEQ ID NO:23634 |
| | | | AATTACTACTGGAGC | CGGATCTATTCCAGTGGGAGCACCAACTACAACCCCTCCCTCAAGAGT | GGGTGGGAGCTAAACTAC |
| iPS:437012 | 21-225_192G7 | AA | SEQ ID NO:7611 | SEQ ID NO:15623 | SEQ ID NO:23635 |
| | | NA | NYYWS | RIYSSGSTNYNPSLKS | GWFLNY |
| | | | SEQ ID NO:7612 | SEQ ID NO:15624 | SEQ ID NO:23636 |
| | | | AGTGGTGGTTACTACTGGAGC | TACATCTATTACAGAGGGAGTACCTACTACAATCCGTCCCTCAAGAGT | GACTCCCCGGTGACAGGATTTGACTAT |
| iPS:437014 | 21-225_192H8 | AA | SEQ ID NO:7613 | SEQ ID NO:15625 | SEQ ID NO:23637 |
| | | NA | SGGYYWS | YIYYTGSTYNPSLKS | DSPVTGFDY |
| | | | SEQ ID NO:7614 | SEQ ID NO:15626 | SEQ ID NO:23638 |
| | | | AGTGGTGGTGGACTACTGGAG | TACATCTATTACAGTGGGCCCACCTACTACAACCCGTCCCTCAAGAGT | GATAGCTCCCTCTACGGTATGGACGTC |
| iPS:437016 | 21-225_193A6 | AA | SEQ ID NO:7615 | SEQ ID NO:15627 | SEQ ID NO:23639 |
| | | NA | SGGDYWS | YIYYSGPTYYNPSLKS | DSSLYGMDV |
| | | | SEQ ID NO:7616 | SEQ ID NO:15628 | SEQ ID NO:23640 |
| | | | AGTTACTACTGGAGC | TATATCTATTACAGTGGGAGCACCAACTACAACCCCTCCCTCAAGAGT | GGATGGGAGCTAAACTAC |

FIGURE 49 (Continued)

| | | | | | |
|---|---|---|---|---|---|
| iPS:437018 | 21-225_193A6 | AA | SEQ ID NO:7617<br>SYYWS | SEQ ID NO:15629<br>YIYYSGSTNYNPSLKS | SEQ ID NO:23641<br>GWELNY |
| | | NA | SEQ ID NO:7618<br>AACGCCTACATGACC | SEQ ID NO:15630<br>CGTATTAAAAGCAAAAC<br>TGATGGTGGGACAACAG<br>ACTACGCTGCACCCGTG<br>AAAGGC | SEQ ID NO:23642<br>GATCCCGGGTGGTATCTTTGA<br>CTAC |
| iPS:437020 | 21-225_193H5 | AA | SEQ ID NO:7619<br>NAYMT | SEQ ID NO:15631<br>RIKSKTDGGTTDYAAPVK<br>G | SEQ ID NO:23643<br>DPGGIFDY |
| | | NA | SEQ ID NO:7620<br>GGCTACTATATGCAC | SEQ ID NO:15632<br>TGGATCAACCCTTACAGT<br>GGTGGCACAAACTATGC<br>ACAGAAGTTTCAGGGC | SEQ ID NO:23644<br>GATAGAGCAGTGGCTGGAAA<br>CTACTTCTACTACGGTATGG<br>ACGTC |
| iPS:437022 | 21-225_193F11 | AA | SEQ ID NO:7621<br>GYYMH | SEQ ID NO:15633<br>WINPYSGGTNYAQKFQG | SEQ ID NO:23645<br>DRAVAGNYFYYGMDV |
| | | NA | SEQ ID NO:7622<br>AGTGGTGGTGGTGACTACTGGAG<br>C | SEQ ID NO:15634<br>TACATCTATTACAGTGGG<br>AGCACCTACTACAACCC<br>GTCTCTCAAGAGT | SEQ ID NO:23646<br>GATCACTCCCTCTACGGTAT<br>GGACGTC |
| iPS:437024 | 21-225_194G5 | AA | SEQ ID NO:7623<br>SGGDYWS | SEQ ID NO:15635<br>YIYYSGSTYYNPSLKS | SEQ ID NO:23647<br>DHSLYGMDV |
| | | NA | SEQ ID NO:7624<br>AGCTATGGCATGCAC | SEQ ID NO:15636<br>GTTATATGGAATGATGG<br>AAGTAAAAAATACCATG<br>TAGACTCCGTGAAGGGC | SEQ ID NO:23648<br>GATCTGGATAAGAGGAACTT<br>TCCTTATTACTACTACGG<br>TATGGACGTC |
| iPS:437026 | 21-225_194F11 | AA | SEQ ID NO:7625<br>SYGMH | SEQ ID NO:15637<br>VIWNDGSKKYHVDSVKG | SEQ ID NO:23649<br>DLDKRNFPYYYYGMDV |

FIGURE 49 (Continued)

| | | | | |
|---|---|---|---|---|
| iPS:437026 | 21-225_194D12 | NA | SEQ ID NO:7626 AGTGGTGGTGACTACTGGAGC | SEQ ID NO:15638 TACATCTATTACAGTGGGAGTACCTACTACAACCCGTCCCTCAAGAGT | SEQ ID NO:23650 GATGGGGTCGGCACGGTATGGACGTC |
| | | AA | SEQ ID NO:7627 SGGDYWS | SEQ ID NO:15639 YIYYSGSTYYNPSLKS | SEQ ID NO:23651 DGARHGMDV |
| iPS:437028 | 21-225_194G12 | NA | SEQ ID NO:7628 AGCTATGGCATGCAC | SEQ ID NO:15640 GTTATATGGAATGATGGAAGTAATAAATACTATGCAGACTCCGTGAAGGGC | SEQ ID NO:23652 GATCTGGATAAGAGGAACTTTCCTTATTACTACTACGGTATGGACGTC |
| | | AA | SEQ ID NO:7629 SYGMH | SEQ ID NO:15641 VIWNDGSNKYYADSVKG | SEQ ID NO:23653 DLDKRNFPYYYYGMDV |
| iPS:437030 | 21-225_195E3 | NA | SEQ ID NO:7630 GACTACTACATGAGC | SEQ ID NO:15642 TATATTACTAGTAGTGGTAATACCATATACTACGCAGACTCTGTGAAGGGC | SEQ ID NO:23654 GATAGTCGATATTTTGACTGGTTTGACTAC |
| | | AA | SEQ ID NO:7631 DYYMS | SEQ ID NO:15643 YITSSGNTIYYADSVKG | SEQ ID NO:23655 DSRYFDWFDY |
| iPS:437032 | 21-225_195H6 | NA | SEQ ID NO:7632 AATTACTACTGGAGC | SEQ ID NO:15644 CGTATCTATAGCAGTGGGAGCACCAACTACAACCCCTCCCTCAAGAGT | SEQ ID NO:23656 GGGTGGGAGCTAAACAAC |
| | | AA | SEQ ID NO:7633 NYYWS | SEQ ID NO:15645 RIYSSGNTNYNPSLKS | SEQ ID NO:23657 GWELNN |
| iPS:437034 | 21-225_195E9 | NA | SEQ ID NO:7634 GGCTACTATATGCAC | SEQ ID NO:15646 TGGATCAACCCTAACAGTGGTGCCACAAACTATGCACAGAAGTTTCAGGGC | SEQ ID NO:23658 GCCTATTACTATGGTTCGGGACTTATTATAAGGAGTTCGACTAC |

FIGURE 49 (Continued)

| | | | | | |
|---|---|---|---|---|---|
| iPS:437036 | 21-225_195E9 | AA | SEQ ID NO:7635<br>GYYMH | SEQ ID NO:15647<br>WINPNSGATNYAQKFQG | SEQ ID NO:23659<br>AYYYGSGTYNEFDY |
| | | NA | SEQ ID NO:7636<br>GGCTACTATATGCAC | SEQ ID NO:15648<br>TGGATCAACCCTACAGTGGTGGCACAAACTATGCACAGAAGTTTCAGGAC | SEQ ID NO:23660<br>GATAGAGCAGTGGCTGGAAACTACTTCTACTACGGTATGGACGTC |
| iPS:437040 | 21-225_195H9 | AA | SEQ ID NO:7637<br>GYYMH | SEQ ID NO:15649<br>WINPYSGGTNYAQKFQD | SEQ ID NO:23661<br>DRAVAGNYFYYGMDV |
| | | NA | SEQ ID NO:7638<br>GGCTACAATATGCAC | SEQ ID NO:15650<br>TGGATCAACCCTAATAGTGGTGGCACAAACTATGCACACAAGTTTCAGGGC | SEQ ID NO:23662<br>GATTACTATGATACTAGTGGAGAAGGGTGGTTCGACCCC |
| iPS:437042 | 21-225_196E7 | AA | SEQ ID NO:7639<br>GYNMH | SEQ ID NO:15651<br>WINPNSGTNYAHKFQG | SEQ ID NO:23663<br>DYYDTSGEGWFDP |
| | | NA | SEQ ID NO:7640<br>GGCTACTATATACAC | SEQ ID NO:15652<br>TGGATCAACCCTAACAGTGGTGGCACAAACTATGCACAGAGGTTTCAGGGC | SEQ ID NO:23664<br>GAGATAGCAGTGGCTGGAAACTACTTCTACTACGGTATGGCGTC |
| iPS:437044 | 21-225_197E8 | AA | SEQ ID NO:7641<br>GYYIH | SEQ ID NO:15653<br>WINPNSGGTNYAQRFQG | SEQ ID NO:23665<br>EIAVAGNYFYYGMGV |
| | | NA | SEQ ID NO:7642<br>ATTTACTACTGGAGC | SEQ ID NO:15654<br>TATGTCTATTACACTGGGAGCACCACTACAACCCCTCCCTCAAGAGT | SEQ ID NO:23666<br>GAAAGGGGAGTAGCCACAGATGGGGGACTACTACGGAATGGACGTC |
| | 21-225_197F9 | AA | SEQ ID NO:7643<br>IYYWS | SEQ ID NO:15655<br>YVYYSGSTTYNPSLKS | SEQ ID NO:23667<br>ERGSSHRWGDYYGMDV |
| iPS:437048 | 21-225_197B11 | NA | SEQ ID NO:7644<br>AGTGGTGGTTACTACTGGAGC | SEQ ID NO:15656<br>TACATCTATTACACTGGGAGCACCACTACAACCCGTCCCTCAAGAGT | SEQ ID NO:23668<br>GACGATCCCTCTACGGAATGGACGTC |

FIGURE 49
(Continued)

| | | | | | | |
|---|---|---|---|---|---|---|
| iPS:437050 | 21-225_197B11 | AA | SGGYYWS | SEQ ID NO:7645 | YIYYTGSTYYNPSLKS | SEQ ID NO:15657 | DDPLYGMDV | SEQ ID NO:23669 |
| | | NA | GGCTACAATATGCAC | SEQ ID NO:7646 | TGGATCAACCCTAATAGTGGTGGCACAAACTATGCACACAAGTTTCAGGGC | SEQ ID NO:15658 | GATTACTATGATAGTAGTGGAGAAGGGTGGTTCGACCCC | SEQ ID NO:23670 |
| iPS:437054 | 21-225_197C11 | AA | GYNMH | SEQ ID NO:7647 | WINPNSGGTNYAHKFQG | SEQ ID NO:15659 | DYYDSSGEGWFDP | SEQ ID NO:23671 |
| | | NA | TTCCATGGCATGCAC | SEQ ID NO:7648 | GTTATATGGTATGATGGAAGTAAAAATACTATGCAGACTCCGTGAAGGGC | SEQ ID NO:15660 | GAAGGGTTTAGCAGTGGCTTTTACAGGGGTTTGACAAC | SEQ ID NO:23672 |
| | 21-225_194G3 | AA | FHGMH | SEQ ID NO:7649 | VIWYDGSKKYYADSVKG | SEQ ID NO:15661 | EGFSSGFYRGFDN | SEQ ID NO:23673 |
| | | NA | AGTGGTGGTGACTACTGGAGC | SEQ ID NO:7650 | TACATCTATTACAGTGGGATCACTACCAATCCGTCCCTCAAGAGT | SEQ ID NO:15662 | GATAGCAGCTCGCGGGGTATGGACGTC | SEQ ID NO:23674 |
| iPS:437056 | 21-225_198B8 | AA | SGGDYWS | SEQ ID NO:7651 | YIYYSGITYYNPSLKS | SEQ ID NO:15663 | DSSSRGMDV | SEQ ID NO:23675 |
| | | NA | TTCTATGGCATGCAC | SEQ ID NO:7652 | GTTATTTGGTATGATGGAAGTAGTAAATACTATGCAGACTCCGTGAAGGGC | SEQ ID NO:15664 | GAAGGGTATAGCAGTGGCTTTTACAGGGGATTTGCCAAC | SEQ ID NO:23676 |
| iPS:437058 | 21-225_199F3 | AA | FYGMH | SEQ ID NO:7653 | VIWYDGSSKYYADSVKG | SEQ ID NO:15665 | EGYSSGFYRGFAN | SEQ ID NO:23677 |
| | | NA | | SEQ ID NO:7654 | | SEQ ID NO:15666 | | SEQ ID NO:23678 |

FIGURE 49
(Continued)

| | | | | |
|---|---|---|---|---|
| iPS:437060 | 21-225_199C3 | NA | ATTTACTACTGGAGC | TATATCTATTACAGTGGG AGCACCACCTACAACCC CTCCCTCAAGAGT | GAAAGGGGGAGTAGCCACA GATGGGGGGACTACTACGGA ATGGACGTC |
| | | | SEQ ID NO:7655 | SEQ ID NO:15667 | SEQ ID NO:23679 |
| | | AA | IYYWS | YIYYSGSTYYNPSLKS | ERGSSHRWGDYYGMDV |
| | | | SEQ ID NO:7656 | SEQ ID NO:15668 | SEQ ID NO:23680 |
| iPS:437062 | 21-225_200H1 | NA | AGTGGTGGTGACTATTGGAG C | TACATCTATTATAGTGGG AGCACCTACAACCC GTCCCTCAAGAGA | GATGGAGCAGCTCTGGGTAT GGACGTC |
| | | | SEQ ID NO:7657 | SEQ ID NO:15669 | SEQ ID NO:23681 |
| | | AA | SGGDYWS | YIYYSGSTYYNPSLKS | DGAALGMDV |
| | | | SEQ ID NO:7658 | SEQ ID NO:15670 | SEQ ID NO:23682 |
| iPS:437064 | 21-225_200G8 | NA | AGTTACTACTGGAGC | TATATCTATTACAGTGGG AGTACTAAGTACAACCC CTCCCTCAAGAGT | AAGGGAGTGGGAACCATCCA CTTTGACTAC |
| | | | SEQ ID NO:7659 | SEQ ID NO:15671 | SEQ ID NO:23683 |
| | | AA | SYYWS | YIYYSGSTKYNPSLKS | KGVGTIHFDY |
| | | | SEQ ID NO:7660 | SEQ ID NO:15672 | SEQ ID NO:23684 |
| iPS:437066 | 21-225_200G9 | NA | AGTGGTGGTGACTACTGGAG C | TACATCTATTACAGTGGG AGCACCACTACAACC GTCCCTCAAGAGT | GATGGAGCAGCTCTGGGTAT GGACGTC |
| | | | SEQ ID NO:7661 | SEQ ID NO:15673 | SEQ ID NO:23685 |
| | | AA | SGGDYWS | YIYYSGSTYYNPSLKS | DGAALGMDV |
| | | | SEQ ID NO:7662 | SEQ ID NO:15674 | SEQ ID NO:23686 |
| iPS:437068 | 21-225_200A11 | NA | AGTGGTGGTGACTACTGGAG C | TACATCTATTACAGAGG GAGCACCACTACAACC CGTCCCTCAAGAGT | GATGCAGCAGCCCACGGCAT GGACGTC |
| | | | SEQ ID NO:7663 | SEQ ID NO:15675 | SEQ ID NO:23687 |
| | | AA | SGGDYWS | YIYYRGSTYYNPSLKS | DAAAHGMDV |
| | | | SEQ ID NO:7664 | SEQ ID NO:15676 | SEQ ID NO:23688 |

FIGURE 49
(Continued)

| | | | | | | | |
|---|---|---|---|---|---|---|---|
| iPS:437070 | 21-225_201G11 | NA | CGCATCAATCCTACTTGGAA C | AGGACATACTACAGGTC CAAGTGTATCATGTTTA TGCAGTATCTGTGAAAA GT | GATCCTGGGGGGCTCTTTGA CTAC | | |
| | | | SEQ ID NO:7665 | SEQ ID NO:15677 | SEQ ID NO:23689 | | |
| | | AA | RINPTWN | RTYYRSKWYHVYAVSVK S | DPGGLFDY | | |
| | | | SEQ ID NO:7666 | SEQ ID NO:15678 | SEQ ID NO:23690 | | |
| iPS:437074 | 21-225_203B2 | NA | AACTATGGCATGCAC | ATTATATGGTTTGATGGA AGTAATGAATACTATGC AGACTCCGTGAAGGGC | GAAAGTGGGAGCTATGCTCT TTATATC | | |
| | | | SEQ ID NO:7667 | SEQ ID NO:15679 | SEQ ID NO:23691 | | |
| | | AA | NYGMH | IIWFDGSNEYYADSVKG | ESGSYALYI | | |
| | | | SEQ ID NO:7668 | SEQ ID NO:15680 | SEQ ID NO:23692 | | |
| iPS:437076 | 21-225_203G6 | NA | CGCACCAATCCTACTTGGAA C | AGGACATACTACAGGTC CAAGTGTATCATGTTTA TGCACTATCTGTGAAAA GT | GATCCTGGGGGGCCTCTTTGA CTAC | | |
| | | | SEQ ID NO:7669 | SEQ ID NO:15681 | SEQ ID NO:23693 | | |
| | | AA | RTNPTWN | RTYYRSKWYHVYALSVK S | DPGGLFDY | | |
| | | | SEQ ID NO:7670 | SEQ ID NO:15682 | SEQ ID NO:23694 | | |
| iPS:437082 | 21-225_205E12 | NA | AACTATGGCATGCAC | ATTATATGGTTTGATGGA AGTAATGAATACTATGC AGACTCCGTGAAGGGC | GAAAGTGGGAGCTATGCTCT TTATATC | | |
| | | | SEQ ID NO:7671 | SEQ ID NO:15683 | SEQ ID NO:23695 | | |
| | | AA | NYGMH | IIWFDGSNEYYADSVKG | ESGSYALYI | | |
| | | | SEQ ID NO:7672 | SEQ ID NO:15684 | SEQ ID NO:23696 | | |

FIGURE 49
(Continued)

| | | | | |
|---|---|---|---|---|
| iPS:437084 | 21-225_206B5 | NA | AGCTATGGCATGCAC | GTTATATGGTATGATGG AAGTAATAAATACTATG CAGACTCCGTGAAGGGC | GAGGGTGGGAGCTACCACCT TGACTAC |
| | | | SEQ ID NO:7673 | SEQ ID NO:15685 | SEQ ID NO:23697 |
| | | AA | SYGMH | VIWYDGSNKYYADSVKG | EGGSYHLDY |
| | | | SEQ ID NO:7674 | SEQ ID NO:15686 | SEQ ID NO:23698 |
| iPS:437086 | 21-225_209A8 | NA | AGTTATAGCATGAAC | TACATTAGTAGTAGTAGT AGTATCAAAAAGTACGC AGACTCTGTGAAGGGC | GATGATGGGAGCTACTACTT TGACTAC |
| | | | SEQ ID NO:7675 | SEQ ID NO:15687 | SEQ ID NO:23699 |
| | | AA | SYSMN | YISSSSSIKKYADSVKG | DDGSYYFDY |
| | | | SEQ ID NO:7676 | SEQ ID NO:15688 | SEQ ID NO:23700 |
| iPS:437088 | 21-225_209H10 | NA | AGCTATGGCATGCAC | GTTATATGGTATGATGG AAGTAATAAATACTATG CAGACTCCGTGAAGGGC | GAGGGTGGGAGCTACCACCT TGACTAC |
| | | | SEQ ID NO:7677 | SEQ ID NO:15689 | SEQ ID NO:23701 |
| | | AA | SYGMH | VIWYDGSNKYYADSVKG | EGGSYHLDY |
| | | | SEQ ID NO:7678 | SEQ ID NO:15690 | SEQ ID NO:23702 |
| iPS:437090 | 21-225_210F11 | NA | AGTGGTGGTTCCTACTGGAG C | TACATCTATTACATTGGG ACCACTACTACAACCC GTCCCTCAAGAGT | GATGAGCCATTGACCGGTAT GGACGTC |
| | | | SEQ ID NO:7679 | SEQ ID NO:15691 | SEQ ID NO:23703 |
| | | AA | SGGSYWS | YIYYIGTTYNPSLKS | DEPLTGMDV |
| | | | SEQ ID NO:7680 | SEQ ID NO:15692 | SEQ ID NO:23704 |

FIGURE 49
(Continued)

| | | | | | | |
|---|---|---|---|---|---|---|
| iPS:437092 | 21-225_210B12 | NA | GACTACTATATGAAC | TGGATCAACCCTAACAGTGGTGGCACAAACTATGCACAGAAGTTTCAGGGC | GGGTATGACTCGTTCGCCCC | |
| | | | SEQ ID NO:7681 | SEQ ID NO:15693 | SEQ ID NO:23705 | |
| | | AA | DYYMN | WINPNSGGTNYAQKFQG | GYDSFAP | |
| | | | SEQ ID NO:7682 | SEQ ID NO:15694 | SEQ ID NO:23706 | |
| iPS:437094 | 21-225_210D12 | NA | CACTATGGCATGCAC | GTTATATGGTATGATGGAAGTAATAAATACTATGCAGACTCCGTGAAGGGC | GGGGACTGGAACCCCGAGGGTTTGGACGTC | |
| | | | SEQ ID NO:7683 | SEQ ID NO:15695 | SEQ ID NO:23707 | |
| | | AA | HYGMH | VIWYDGSNKYYADSVKG | GDWNPEGLDV | |
| | | | SEQ ID NO:7684 | SEQ ID NO:15696 | SEQ ID NO:23708 | |
| iPS:437096 | 21-225_210E12 | NA | AACTATGGCATGCAC | GTTATATGGTATGATGGAAGTAATAAATACTATGCAGACTCCGTGAAGGGC | GGGGACTGGAACCCCGAGGGTATGGACGTC | |
| | | | SEQ ID NO:7685 | SEQ ID NO:15697 | SEQ ID NO:23709 | |
| | | AA | NYGMH | VIWYDGSNKYYADSVKG | GDWNPEGMDV | |
| | | | SEQ ID NO:7686 | SEQ ID NO:15698 | SEQ ID NO:23710 | |
| iPS:437098 | 21-225_211C1 | NA | CACTATGGCATGCAC | GTTATATGGTATGATGGAAGTAATAAATACTATGCAGACTCCGTGAAGGGC | GGGGACTGGAACCCCGAGGGTTTGGACGTC | |
| | | | SEQ ID NO:7687 | SEQ ID NO:15699 | SEQ ID NO:23711 | |
| | | AA | HYGMH | VIWYDGSNKYYADSVKG | GDWNPEGLDV | |
| | | | SEQ ID NO:7688 | SEQ ID NO:15700 | SEQ ID NO:23712 | |

FIGURE 49
(Continued)

| | | NA | AGCTATGCCATGCAC | GTTATATGGTATGATGG AAGTAATAAATACTATG CAGACTCCGTGAAGGGC | GATCCTGGGAGCTACGGGTT CGACCCC |
|---|---|---|---|---|---|
| iPS:437100 | 21-225_211H2 | | SEQ ID NO:7689 | SEQ ID NO:15701 | SEQ ID NO:23713 |
| | | AA | SYAMH | VIWYDGSNKYYADSVKG | DPGSYGFDP |
| | | NA | AACTATGGCATGCAC | ATTATATGGTTTGATGGA AGTGATCAATACTATGC AGACTCCGTGAAGGGC | GGCCTCTCTGTCTACTACTAC GGTATGGGCGTC |
| iPS:437102 | 21-225_211E5 | | SEQ ID NO:7690 | SEQ ID NO:15702 | SEQ ID NO:23714 |
| | | | SEQ ID NO:7691 | SEQ ID NO:15703 | SEQ ID NO:23715 |
| | | AA | NYGMH | HWFDGSDQYYADSVKG | GLSVYYYGMGV |
| | | | SEQ ID NO:7692 | SEQ ID NO:15704 | SEQ ID NO:23716 |
| iPS:437104 | 21-225_211G5 | NA | CACTATGGCATGCAC | GTTATATGGTATGATGG AAGTAATAAATACTATG CAGACTCCGTGAAGGGC | GGGGACTGGAACCCGAGGG TTTGGACGTC |
| | | | SEQ ID NO:7693 | SEQ ID NO:15705 | SEQ ID NO:23717 |
| | | AA | HYGMH | VIWYDGSNKYYADSVKG | GDWNPEGLDV |
| | | | SEQ ID NO:7694 | SEQ ID NO:15706 | SEQ ID NO:23718 |
| iPS:437106 | 21-225_211H7 | NA | AGTGGTGGTTACTACTGGAG C | TACATCTATTACGTTGGG AGCACTACTACAACCC GTCCCTCAAGAGT | GATGGGCCATTGAGGCGGTAT GGACGTC |
| | | | SEQ ID NO:7695 | SEQ ID NO:15707 | SEQ ID NO:23719 |
| | | AA | SGGYYWS | YIYYVGSTYNPSLKS | DGPLSGMDV |
| | | | SEQ ID NO:7696 | SEQ ID NO:15708 | SEQ ID NO:23720 |

FIGURE 49
(Continued)

| | | | | | |
|---|---|---|---|---|---|
| iPS:437108 | 21-225_211C9 | NA | AGTGGTGGTGACTACTGGAG C | TACATCTATTATAGTGG AGCAACTACTACAACCC GTCCCTCAAGAGT | GATTCAGCAGTGTACAATAT GGACGTC |
| | | | SEQ ID NO:7697 | SEQ ID NO:15709 | SEQ ID NO:23721 |
| | | AA | SGGDYWS | YIYYSGSTYYNPSLKS | DSAVYNMDV |
| | | | SEQ ID NO:7698 | SEQ ID NO:15710 | SEQ ID NO:23722 |
| iPS:437110 | 21-225_211E9 | NA | AGTGGTGGTGACTACTGGAG C | TACATCTATTACACTGGG AGCAACTACTACAACCC GTCCCTCAAGAGT | GATTCAGCAGTGTACGGTAT GGACGTC |
| | | | SEQ ID NO:7699 | SEQ ID NO:15711 | SEQ ID NO:23723 |
| | | AA | SGGDYWS | YIYYTGSNYYNPSLKS | DSAVYGMDV |
| | | | SEQ ID NO:7700 | SEQ ID NO:15712 | SEQ ID NO:23724 |
| iPS:437112 | 21-225_212C2 | NA | CACTATGGCATGCAC | GTTATATGGTATGATGG AAGTAATAAATACTATG CAGACTCCGTGAAGGGC | GGGGACTGGAACCCCGAGGG TATGGACGTC |
| | | | SEQ ID NO:7701 | SEQ ID NO:15713 | SEQ ID NO:23725 |
| | | AA | HYGMH | VIWYDGSNKYYADSVKG | GDWNPEGMDV |
| | | | SEQ ID NO:7702 | SEQ ID NO:15714 | SEQ ID NO:23726 |
| iPS:437114 | 21-225_212A4 | NA | AACTATGGCATGCAC | GTTATATGGTATGATGG AAGTAATAAATACTATG CAGACTCCGTGAAGGGC | GGGGACTGGAACCCCGAGGG TATGGACGTC |
| | | | SEQ ID NO:7703 | SEQ ID NO:15715 | SEQ ID NO:23727 |
| | | AA | NYGMH | VIWYDGSNKYYADSVKG | GDWNPEGMDV |
| | | | SEQ ID NO:7704 | SEQ ID NO:15716 | SEQ ID NO:23728 |

FIGURE 49
(Continued)

| ID | Clone | Type | CDR1 | CDR2 | CDR3 |
|---|---|---|---|---|---|
| iPS:437116 | 21-225_212F6 | NA | CACTATGGCATGCAC SEQ ID NO:7705 | GTTATATGGTATGATGGAAGTAATAAATACTATGCGGACTCCGTGAAGGGC SEQ ID NO:15717 | GGGGACTGGAACCCCGAGGGTTTGGACGTC SEQ ID NO:23729 |
| | | AA | HYGMH SEQ ID NO:7706 | VIWYDGSNKYYADSVKG SEQ ID NO:15718 | GDWNPEGLDV SEQ ID NO:23730 |
| iPS:437118 | 21-225_212G7 | NA | CACTATGGCATGCAC SEQ ID NO:7707 | GTTATATGGTATGATGGAAGTAATAAATACTATGCAGACTCCGTGAAGGGC SEQ ID NO:15719 | GGAGACTGGAACCCCGAGGGTTTGGACGTC SEQ ID NO:23731 |
| | | AA | HYGMH SEQ ID NO:7708 | VIWYDGSNKYCADSVKG SEQ ID NO:15720 | GDWNPEGLDV SEQ ID NO:23732 |
| iPS:437120 | 21-225_212A9 | NA | AGTGGTGGTGACTACTGGAGC SEQ ID NO:7709 | TATATGTATTACAGTGGGAGCACCTACTACAACCCGTCCCTCAAGAGT SEQ ID NO:15721 | GATTCAGCAGTGTACGGTATGGACGTC SEQ ID NO:23733 |
| | | AA | SGGDYWS SEQ ID NO:7710 | YMYYSGSTYYNPSLKS SEQ ID NO:15722 | DSAVYGMDV SEQ ID NO:23734 |
| iPS:437124 | 21-225_212H12 | NA | AGTGGTGGTGACTACTGGAGT SEQ ID NO:7711 | TACATCTATTACAGTGGGAGCACCTACTACAACCCGTCCCTCAAGAGT SEQ ID NO:15723 | GATAGCAGCTCTACGGTATGGACGTC SEQ ID NO:23735 |
| | | AA | SGGDYWS SEQ ID NO:7712 | YIYYSGSTYYNPSLKS SEQ ID NO:15724 | DSSSYGMDV SEQ ID NO:23736 |

FIGURE 49
(Continued)

| | | | | | |
|---|---|---|---|---|---|
| iPS:437128 | 21-225_213G3 | NA | CACTATGGCATGCAC | GTTATATGGTAGTGATGG AAGTAATAAATACTATG CAGACTCCGTGAAGGGC | GGGGACTGGGAACCCCGAGGG TATGGACGTC |
| | | | SEQ ID NO:7713 | SEQ ID NO:15725 | SEQ ID NO:23737 |
| | | AA | HYGMH | VIWYDGSNKYYADSVKG | GDWNPEGMDV |
| | | | SEQ ID NO:7714 | SEQ ID NO:15726 | SEQ ID NO:23738 |
| iPS:437130 | 21-225_213D5 | NA | CACTATGGCATGCAC | GTTATATGGTAGTGATGG AAGTAATAAATACTATG CAGACTCCGTGAAGGGC | GGGGACTGGGAACCCCGAGGG TATGGACGTC |
| | | | SEQ ID NO:7715 | SEQ ID NO:15727 | SEQ ID NO:23739 |
| | | AA | HYGMH | VIWYDGSNKYYADSVKG | GDWNPEGMDV |
| | | | SEQ ID NO:7716 | SEQ ID NO:15728 | SEQ ID NO:23740 |
| iPS:437132 | 21-225_213F5 | NA | AGTGGTGGTGACTACTGGAG C | TACATCTATTATAGTGGG AGCACTACTACAACCC GTCCCTCAAGAGT | GATTCAGCAGTGTACAATAT GGACGTC |
| | | | SEQ ID NO:7717 | SEQ ID NO:15729 | SEQ ID NO:23741 |
| | | AA | SGGDYWS | YIYYSGSTYYNPSLKS | DSAVYNMDV |
| | | | SEQ ID NO:7718 | SEQ ID NO:15730 | SEQ ID NO:23742 |
| iPS:437134 | 21-225_213A7 | NA | GACTACTATATGAAC | TGGATCAACCCTAAGAA TGGTGGCACAAACTATG CACAGAAGTTTCAGGGC | GGGTATGATTCGTTCGCCCC C |
| | | | SEQ ID NO:7719 | SEQ ID NO:15731 | SEQ ID NO:23743 |
| | | AA | DYYMN | WINPKNGGTNYAQKFQG | GYDSFAP |
| | | | SEQ ID NO:7720 | SEQ ID NO:15732 | SEQ ID NO:23744 |

FIGURE 49
(Continued)

| | | | | |
|---|---|---|---|---|
| iPS:437136 | 21-225_214H3 | NA | AGTGGTGGTGACTACTGGAGT SEQ ID NO:7721 | TACATCTATTACAGTGGG AGCACCTACACAACCC GTCCCTCAAGAGT SEQ ID NO:15733 | GATAGCAGCTCCTACGGTAT GGACGTC SEQ ID NO:23745 |
| | | AA | SGGDYWS SEQ ID NO:7722 | YIYYSGSTYYNPSLKS SEQ ID NO:15734 | DSSSYGMDV SEQ ID NO:23746 |
| iPS:437138 | 21-225_214D8 | NA | ACTGCTTTTACTACTGGAG C SEQ ID NO:7723 | TACATCTATTACAGTGGG AGCACCTACACAACCC GTCCCTCAAGAGT SEQ ID NO:15735 | GCAAGGGATATCACTACACAG TATCTTTGACTAC SEQ ID NO:23747 |
| | | AA | TAFYYWS SEQ ID NO:7724 | YIYYSGSTYYNPSLKS SEQ ID NO:15736 | ARGYHYSIFDY SEQ ID NO:23748 |
| iPS:437140 | 21-225_214E12 | NA | AGTGGTGGTGATTACTGGAG C SEQ ID NO:7725 | TACATCTATTACAGTGGG CCCACCTACACAACCC GTCCCTCAAGAGT SEQ ID NO:15737 | GATGGGCTGCGGAGGGTAT GGACGTC SEQ ID NO:23749 |
| | | AA | SGGDYWS SEQ ID NO:7726 | YIYYSGPTYYNPSLKS SEQ ID NO:15738 | DGAAEGMDV SEQ ID NO:23750 |
| iPS:437142 | 21-225_215A3 | NA | AGTGGTGGTGACTACTGGAG C SEQ ID NO:7727 | TACATCTATTACACTGGG AGCAACTACACAACCC GTCCCTCAAGAGT SEQ ID NO:15739 | GATTCAGCAGTGTACGGTAT GGACGTC SEQ ID NO:23751 |
| | | AA | SGGDYWS SEQ ID NO:7728 | YIYYTGSNYYNPSLKS SEQ ID NO:15740 | DSAVYGMDV SEQ ID NO:23752 |
| iPS:437144 | 21-225_215B3 | NA | AACGCCTGGATGCAC SEQ ID NO:7729 | CGTATTAAAAGCAAAAC TAATGGTGGGACAACAG ACTACGCTGCACCCGTG AAAGGC SEQ ID NO:15741 | GATCCGGGGGGGATCTTTGA CTAC SEQ ID NO:23753 |

FIGURE 49
(Continued)

| | | | | | | |
|---|---|---|---|---|---|---|
| iPS:437146 | 21-225_215D3 | AA | NAWMH | | RIKSKTNGGTTDYAAPVK G | DPGGIFDY |
| | | | SEQ ID NO:7730 | | SEQ ID NO:15742 | SEQ ID NO:23754 |
| | | NA | CACTATGGCATGCAC | | GTTATATGGTATGATGG AAGTAATAAGTACTATG CAGACTCCGTGAAGGGC | GGGGACTGGAACCCCGAGGG TATGGACGTC |
| | | | SEQ ID NO:7731 | | SEQ ID NO:15743 | SEQ ID NO:23755 |
| iPS:437148 | 21-225_215H3 | AA | HYGMH | | VIWYDGSNEYYADSVKG | GDWNPEGMDV |
| | | | SEQ ID NO:7732 | | SEQ ID NO:15744 | SEQ ID NO:23756 |
| | | NA | AGTGGTGGTGACTACTGGAG C | | TATATGTATTACAGTGGG AGCACTACTACAACCC GTCCCTCAAGAGT | GATTCAGCAGTGTACGGTAT GGACGTC |
| | | | SEQ ID NO:7733 | | SEQ ID NO:15745 | SEQ ID NO:23757 |
| iPS:437150 | 21-225_216A3 | AA | SGGDYWS | | YMYYSGSTYYNPSLKS | DSAVYGMDV |
| | | | SEQ ID NO:7734 | | SEQ ID NO:15746 | SEQ ID NO:23758 |
| | | NA | CACTATGGCATGCAC | | GTTATATGGTATGATGG AAGTAATAAATACTATG CAGACTCCGTGAAGGGC | GGGGACTGGAACCCCGAGGG TTTGGACGTC |
| | | | SEQ ID NO:7735 | | SEQ ID NO:15747 | SEQ ID NO:23759 |
| iPS:437154 | 21-225_216A7 | AA | HYGMH | | VIWYDGSNKYYADSVKG | GDWNPEGLDV |
| | | | SEQ ID NO:7736 | | SEQ ID NO:15748 | SEQ ID NO:23760 |
| | | NA | AGTGGTGGTGACTACTGGAG C | | TATATGTATTACAGTGGG AGCACTACTACAACCC GTCCCTCAAGAGT | GATTCAGCAGTGTACGGTAT GGACGTC |
| | | | SEQ ID NO:7737 | | SEQ ID NO:15749 | SEQ ID NO:23761 |
| | | AA | SGGDYWS | | YMYYSGSTYYNPSLKS | DSAVYGMDV |
| | | | SEQ ID NO:7738 | | SEQ ID NO:15750 | SEQ ID NO:23762 |

FIGURE 49
(Continued)

| | | | | | |
|---|---|---|---|---|---|
| iPS:437158 | 21-225_216H11 | NA | AGTGGTGGTGATTACTGGAGC | TACATCTATTACAGTGGGCCCACCTACTACAACCCGTCCCTCAAGAGT | GATGGGGCTGCGGAGGGTTTGGACGTC |
| | | | SEQ ID NO:7739 | SEQ ID NO:15751 | SEQ ID NO:23763 |
| | | AA | SGGDYWS | YIYYSGPTYYNPSLKS | DGAAEGLDV |
| | | | SEQ ID NO:7740 | SEQ ID NO:15752 | SEQ ID NO:23764 |
| iPS:437160 | 21-225_216B12 | NA | AGCTATGCCATGCAC | GTTATATGGTATGATGGAAGTAATAAATACTATGCAGACTCCGTGAAGGGC | GATCGGGACTGGGATACTTCTTTGACTAC |
| | | | SEQ ID NO:7741 | SEQ ID NO:15753 | SEQ ID NO:23765 |
| | | AA | SYAMH | VIWYDGSNKYYADSVKG | DLGLGYFFDY |
| | | | SEQ ID NO:7742 | SEQ ID NO:15754 | SEQ ID NO:23766 |
| iPS:437162 | 21-225_217B2 | NA | AACTATGGCATGCAC | GTTATATGGTATGATGGAAGTAATAAATACTATGCAGACTCCGTGAAGGGC | GGGGACTGGAACCCCGAGGGTATGGACGTC |
| | | | SEQ ID NO:7743 | SEQ ID NO:15755 | SEQ ID NO:23767 |
| | | AA | NYGMH | VIWYDGSNKYYADSVKG | GDWNPEGMDV |
| | | | SEQ ID NO:7744 | SEQ ID NO:15756 | SEQ ID NO:23768 |
| iPS:437164 | 21-225_217C6 | NA | AACTATGGCATGCAC | ATTATATGGTTTGATGAAGTGATGAATACTATGCAGAGACTCCGTGAAGGGC | GGCCTATCTGTCTACTACTACGGTATGGACGTC |
| | | | SEQ ID NO:7745 | SEQ ID NO:15757 | SEQ ID NO:23769 |
| | | AA | NYGMH | IIWFDGSDEYYADSVKG | GLSVYYYGMDV |
| | | | SEQ ID NO:7746 | SEQ ID NO:15758 | SEQ ID NO:23770 |

FIGURE 49
(Continued)

| | | | | |
|---|---|---|---|---|
| iPS:437166 | 21-225_217G11 | NA | AACTATGGCATGCAC | ATTATATGGTTTGATGGA AGTGATCAGTACTATGC AGACTCCGTGAAGGGC | GGCCTCTCTGTCTACTACTAC GGTATGGACGTC |
| | | | SEQ ID NO:7747 | SEQ ID NO:15759 | SEQ ID NO:23771 |
| | | AA | NYGMH | IIWFDGSDQYYADSVKG | GLSVYYYGMDV |
| | | | SEQ ID NO:7748 | SEQ ID NO:15760 | SEQ ID NO:23772 |
| iPS:437168 | 21-225_218G4 | NA | AGTATATGGCTTGCAC | GTTATATGGTATGATGG AAGTAATAAATACTATG CAGACTCCGTGAAGGGC | TGGTACTACTATTACTACTAC GGTATGGACGTC |
| | | | SEQ ID NO:7749 | SEQ ID NO:15761 | SEQ ID NO:23773 |
| | | AA | SYGLH | VIWYDGSNKYYADSVKG | WYYYYYGMDV |
| | | | SEQ ID NO:7750 | SEQ ID NO:15762 | SEQ ID NO:23774 |
| iPS:437170 | 21-225_218E5 | NA | AACTATGGCATGCAC | ATTATATGGTTTGATGGA AGTGATGAATACTATGC AGACTCCGTGAAGGGC | GGCCTATCTGTCTACTACTA CGGTATGGACGTC |
| | | | SEQ ID NO:7751 | SEQ ID NO:15763 | SEQ ID NO:23775 |
| | | AA | NYGMH | IIWFDGSDEYYADSVKG | GLSVYYYGMDV |
| | | | SEQ ID NO:7752 | SEQ ID NO:15764 | SEQ ID NO:23776 |
| iPS:437172 | 21-225_219A7 | NA | CACTATGGCATGCAC | GTCATATGGTATGATGG AAGTAATAAATACTATG CAGACTCCGTGAAGGGC | GGGGACTGGAACCCCGAGGG TATGGACGTC |
| | | | SEQ ID NO:7753 | SEQ ID NO:15765 | SEQ ID NO:23777 |
| | | AA | HYGMH | VIWYDGSNKYYADSVKG | GDWNPEGMDV |
| | | | SEQ ID NO:7754 | SEQ ID NO:15766 | SEQ ID NO:23778 |

FIGURE 49
(Continued)

| | | NA | CACTATGGCATGCAC | GTTATATGGTATGATGG AAGTAATAAATACTATG CAGACTCCGTGAAGGGC | GGGGACTGGAACCCCGAGGG TATGGACGTC |
|---|---|---|---|---|---|
| iPS:437182 | 21-225_221H2 | | SEQ ID NO:7755 | SEQ ID NO:15767 | SEQ ID NO:23779 |
| | | AA | HYGMH | VIWYDGSNKYYADSVKG | GDWNPEGMDV |
| | | | SEQ ID NO:7756 | SEQ ID NO:15768 | SEQ ID NO:23780 |
| | | NA | CACTATGGCATGCAC | GTTATATGGTATGATGG AAGTAATAAATACTATG CAGACTCCGTGAAGGGC | GGGGACTGGAACCCCGAGGG TATGGACGTC |
| iPS:437184 | 21-225_221G4 | | SEQ ID NO:7757 | SEQ ID NO:15769 | SEQ ID NO:23781 |
| | | AA | HYGMH | VIWYDGSNKYYADSVKG | GDWNPEGMDV |
| | | | SEQ ID NO:7758 | SEQ ID NO:15770 | SEQ ID NO:23782 |
| | | NA | AGCAACAGTGCTGCTTGGAA C | AGGACATACTACACAGTC CAAGTGGTATAATGATT ATGCAGTATCTGTGAAA AGT | GAGGGGGGCTAGGATATTG TAGTAGTACCAGTGCTATG GAGGCTGGTTCGACCCC |
| iPS:437186 | 21-225_224H2 | | SEQ ID NO:7759 | SEQ ID NO:15771 | SEQ ID NO:23783 |
| | | AA | SNSAAWN | RTYYRSKWYNDYAVSVK S | EGGLGYCSSTSCYGGWFDP |
| | | | SEQ ID NO:7760 | SEQ ID NO:15772 | SEQ ID NO:23784 |
| | | NA | GGCTACTATATACAC | TGGATCAACCTAAAAA TGGTGGCACAAACTATG CACAGAAGTTTCAGGGC | GGAGGGTTTGATTACTTCTA CTACTACGCTATGGACGTC |
| iPS:437188 | 21-225_224B11 | | SEQ ID NO:7761 | SEQ ID NO:15773 | SEQ ID NO:23785 |

FIGURE 49
(Continued)

| | | | | | | |
|---|---|---|---|---|---|---|
| iPS:437190 | 21-225_225A9 | AA | GYYIH | | WINPKNGGTNYAQKFQG | GAFDYFYYYAMDV |
| | | | SEQ ID NO:7762 | | SEQ ID NO:15774 | SEQ ID NO:23786 |
| | | NA | ACCTATGGCATGCAC | | GTTATATGGTATGATGG AAGTAATAAATACTATG CAGACTCCGTGAAGGGC | GATAACCACTATTGTAGTAG TACCAGCTGCTCCCCATACT ACTACTACTTCGGTATGGAC GTC |
| | | | SEQ ID NO:7763 | | SEQ ID NO:15775 | SEQ ID NO:23787 |
| iPS:437192 | 21-225_225E9 | AA | TYGMH | | VIWYDGSNKYYADSVKG | DNHYCSSTSCSPYYYFGMDV |
| | | | SEQ ID NO:7764 | | SEQ ID NO:15776 | SEQ ID NO:23788 |
| | | NA | AGCTATGGCATGCAC | | GTTATGTGGTATGATGG AGGTAATAAAGACTATG CAGACTCCGTGAAGGGC | GATCGGGAATATTGTACTAG TACCAGCTGCCCTTACTACT ACTACTACGGTATGGACGTC |
| | | | SEQ ID NO:7765 | | SEQ ID NO:15777 | SEQ ID NO:23789 |
| iPS:437194 | 21-225_226B2 | AA | SYGMH | | VMWYDGGNKDYADSVKG | DREYCTSTSCPYYYYYGMDV |
| | | | SEQ ID NO:7766 | | SEQ ID NO:15778 | SEQ ID NO:23790 |
| | | NA | GGCTACTTTATGCAC | | TGGATCAACCCTAACAG TGGTGACACAAACTATG CACAGAAGTTTCAGGGC | GGGACTTACTATGGTTCGGG GAGTTATTTAACGAACTTG ACTCC |
| | | | SEQ ID NO:7767 | | SEQ ID NO:15779 | SEQ ID NO:23791 |
| iPS:437196 | 21-225_226B7 | AA | GYFMH | | WINPNSGDTNYAQKFQG | GTYYGSGSYFNELDS |
| | | | SEQ ID NO:7768 | | SEQ ID NO:15780 | SEQ ID NO:23792 |
| | | NA | GGCTACTACTATGCAC | | TGGATCAACCCTAACAG TGGAGGCACAAACTATG CACAGAAGTTTCAGGAC | GGATATTACTATGGTTCGGG GAGTTATTATAACTGGTTCG ACTCC |
| | | | SEQ ID NO:7769 | | SEQ ID NO:15781 | SEQ ID NO:23793 |
| | | AA | GYYMH | | WINPNSGGTNYAQKFQD | GYYYGSGSYYNWFDS |

FIGURE 49
(Continued)

| | | | | | |
|---|---|---|---|---|---|
| iPS:437198 | 21-225_226F8 | NA | SEQ ID NO:7770<br>GGCTACTATATACAC | SEQ ID NO:15782<br>TGGATCAACCCTAACAG<br>TGGTGGCACAAACTATG<br>CACGGAAGTTTCAGGGC | SEQ ID NO:23794<br>GGAGGCGTTTGATTACTACTA<br>CTACTACGCTTTGGACGTC |
| | | AA | SEQ ID NO:7771<br>GYYIH | SEQ ID NO:15783<br>WINPNSGGTNYARKFQG | SEQ ID NO:23795<br>GAFDYYYYALDV |
| iPS:437200 | 21-225_226A10 | NA | SEQ ID NO:7772<br>GGCTACTTTATGCAC | SEQ ID NO:15784<br>TGGATCAACCCTAACAG<br>TGGTGACAAACTATG<br>CACAGAAGTTTCAGGGC | SEQ ID NO:23796<br>GGGACTTACTATGGTTCGG<br>GAGTTATTTAACGAACTTG<br>ACTCC |
| | | AA | SEQ ID NO:7773<br>GYFMH | SEQ ID NO:15785<br>WINPNSGDTNYAQKFQG | SEQ ID NO:23797<br>GTYYGSGSYFNELDS |
| iPS:437202 | 21-225_227B3 | NA | SEQ ID NO:7774<br>GGCTACTATATGCAC | SEQ ID NO:15786<br>TGGATCAACCCTAAGAG<br>TGGTGGCACAAACTTTG<br>CACAGAAGTTTCAGGGC | SEQ ID NO:23798<br>GGAGGCGTTTGATTACTTCTA<br>CTACTACGGTATGGACGTC |
| | | AA | SEQ ID NO:7775<br>GYYMH | SEQ ID NO:15787<br>WINPKSGGTNFAQKFQG | SEQ ID NO:23799<br>GAFDYFYYYGMDV |
| iPS:437204 | 21-225_227E5 | NA | SEQ ID NO:7776<br>AGCTATGCCATGAGC | SEQ ID NO:15788<br>GCTATTAGTGGTAGTGGT<br>GGTAGCACATACTACGC<br>AGACTCCGTGAAGGGC | SEQ ID NO:23800<br>GAATATTGTGGTGGTGACTG<br>CTATTCCCCTACTACTA<br>CTACGGTATGGACGTC |
| | | AA | SEQ ID NO:7777<br>SYAMS | SEQ ID NO:15789<br>AISGSGGSTYYADSVKG | SEQ ID NO:23801<br>EYCGGDCYSPYYYYYGMDV |
| iPS:437208 | 21-225_227C10 | NA | SEQ ID NO:7778<br>GGCTACTATATGCAC | SEQ ID NO:15790<br>TGGATCAACCCTAAGAG<br>TGGTGGCACAAACTATG<br>CACAGAAGTTTCAGGGC | SEQ ID NO:23802<br>GGAGGCGTTTGATTACTTCTA<br>CTACTACGGTATGGACGTC |
| | | | SEQ ID NO:7779 | SEQ ID NO:15791 | SEQ ID NO:23803 |

FIGURE 49
(Continued)

| | | | | | WINPKSGGTNYAQKPQG | GAFDYFYYGMDV |
|---|---|---|---|---|---|---|
| | | | | GYYMH | SEQ ID NO:15792 | SEQ ID NO:23804 |
| iPS:437210 | 21-225_227E12 | NA | | ACTAGTGGAGTGGGTGTGGGC | CTCATTTATTGGAATGATGATAAGGTCTACAGCCCATCTCTGAAGAGC | AGGGGACAGCAGCTGGCCCTCGACTAC |
| | | AA | | SEQ ID NO:7781 | SEQ ID NO:15793 | SEQ ID NO:23805 |
| | | | | TSGVGVG | LIYWNDDKVYSPSLKS | RGQQLALDY |
| | | | | SEQ ID NO:7782 | SEQ ID NO:15794 | SEQ ID NO:23806 |
| iPS:437214 | 21-225_48B12 | NA | | AGCTATGCCATGAAC | GCTATTAGTGGTGGTCGTGGTGGTAACACATTCTACGCAGACTCCGTGAAGGGC | AGAGAGACGTATAACTGGAACTACGAAGGGTTTGACTAC |
| | | AA | | SEQ ID NO:7783 | SEQ ID NO:15795 | SEQ ID NO:23807 |
| | | | | SYAMN | AISGRGGNTFYADSVKG | RETYNWNYEGFDY |
| | | | | SEQ ID NO:7784 | SEQ ID NO:15796 | SEQ ID NO:23808 |
| iPS:437216 | 21-225_51D5 | NA | | AGCTATAGCATGAGC | ACTATGAGTGGTAGTGGTGGTCGCACATACTACGCAGACTCCGTGAACGGC | GTGACTGCTTTTGACTAC |
| | | AA | | SEQ ID NO:7785 | SEQ ID NO:15797 | SEQ ID NO:23809 |
| | | | | SYVMS | TMSGSGGRTYYADSVNG | VTAFDY |
| | | | | SEQ ID NO:7786 | SEQ ID NO:15798 | SEQ ID NO:23810 |
| iPS:437220 | 21-225_55H6 | NA | | AGCTATAGCATGAAC | TCCATTAGTGGTAGTAGTACTTACACATATACTACGCAGACTCAGTGAAGGGC | ACTGGGGTCTTTGACTAC |
| | | AA | | SEQ ID NO:7787 | SEQ ID NO:15799 | SEQ ID NO:23811 |
| | | | | SYSMN | SISGSSTYIYYADSVKG | TGVFDY |
| | | | | SEQ ID NO:7788 | SEQ ID NO:15800 | SEQ ID NO:23812 |
| iPS:437224 | 21-225_56H1 | NA | | AACTATAGAATGAAC | TCCATTAGTGGTAGTAGTACTGACATATACTACGAGACTCAGTGAAGGGC | GTGGCCTCCTTTGACTAC |
| | | | | SEQ ID NO:7789 | SEQ ID NO:15801 | SEQ ID NO:23813 |

FIGURE 49 (Continued)

| | | AA/NA | | | | | |
|---|---|---|---|---|---|---|---|
| iPS:437226 | 21-225_57C2 | AA | NYRMN | SISGSSTIDIYYADSVKG | VASFDY | | |
| | | | SEQ ID NO:7790 | SEQ ID NO:15802 | SEQ ID NO:23814 | | |
| | | NA | AGCTTTGGCATGAAC | TCTATTAGTAGTAGTACT GGTTACATATACAACGC AGACTCAGTGAAGGGC | ACCTATAGTGGGAGCCTGGA CGTC | | |
| | | | SEQ ID NO:7791 | SEQ ID NO:15803 | SEQ ID NO:23815 | | |
| iPS:437228 | 21-225_60C11 | AA | SFGMN | SISSSTGYIYNADSVKG | TYSGSLDV | | |
| | | | SEQ ID NO:7792 | SEQ ID NO:15804 | SEQ ID NO:23816 | | |
| | | NA | AGCTATGCCATGAGC | GCTATTAGTGGTAGTGGT GGTAACACATTCTACGC AGACTCCGTGAAGGGC | TTTTTCGGTGTAGTGGGAGT CGGGTGCTTGACTAC | | |
| | | | SEQ ID NO:7793 | SEQ ID NO:15805 | SEQ ID NO:23817 | | |
| iPS:437230 | 21-225_62H10 | AA | SYAMS | AISGSGGNTFYADSVKG | FFGVGVGCFDY | | |
| | | | SEQ ID NO:7794 | SEQ ID NO:15806 | SEQ ID NO:23818 | | |
| | | NA | AGCTATAGCATGAAC | TCCATTAGTAGTAGTAGT AGTTACATATACTACGC AGACTCAGTGAAGGGC | GGGGGTTCGAGGGGGTTCGA CCCC | | |
| | | | SEQ ID NO:7795 | SEQ ID NO:15807 | SEQ ID NO:23819 | | |
| iPS:437232 | 21-225_63E1 | AA | SYSMN | SISSSSYIYYADSVKG | GGSRGFDP | | |
| | | | SEQ ID NO:7796 | SEQ ID NO:15808 | SEQ ID NO:23820 | | |
| | | NA | ACTTCTGCCATGAGC | GCTATTAGTGGTAGTGGT GCTAACACATTCTACGC AGACTCCGTGAAGGGC | GTTATAGCAGTGGCTGGAGG GCACTTTTCGACCCC | | |
| | | | SEQ ID NO:7797 | SEQ ID NO:15809 | SEQ ID NO:23821 | | |
| iPS:437234 | 21-225_64E2 | AA | TSAMS | AISGSGANTFYADSVKG | VIAVAGGHFFDP | | |
| | | | SEQ ID NO:7798 | SEQ ID NO:15810 | SEQ ID NO:23822 | | |
| | | NA | GGCTACTATATGCAC | TGGATCAACCCTAACAA TAATGGCACAAACTATG CACAGAAGTTTCAGGGC | GATGGGAGCAGTGGCTTTGA CTAC | | |

FIGURE 49
(Continued)

| | | | | SEQ ID NO:7799<br>GYYMH | SEQ ID NO:15811<br>WINPNNGITNYAQKFQG | SEQ ID NO:23823<br>DGSSGFDY |
|---|---|---|---|---|---|---|
| iPS:437248 | 21-225_64E2 | AA | | SEQ ID NO:7800<br>GATTACTACTGGAGC | SEQ ID NO:15812<br>GAAATCAATCATAGTGG<br>AGACACCAACTACAACC<br>CGTCCCTCAAGAGT | SEQ ID NO:23824<br>GAGTTCCATATAGTGGAAG<br>CTACCTCTACTACTACGGTA<br>TGGACGTC |
| iPS:437250 | 21-225_97H3 | NA | | SEQ ID NO:7801<br>DYYWS | SEQ ID NO:15813<br>EINHSGDTNYNPSLKS | SEQ ID NO:23825<br>EFPYSGSYLYYYGMDV |
| | | AA | | SEQ ID NO:7802<br>AGCTATGCCATGAGC | SEQ ID NO:15814<br>GTTATTAGTGGTGGTGGT<br>AGTAGTACATACTACGC<br>AGACTCCGTGAAGGGC | SEQ ID NO:23826<br>TGGCGAGGTAACCCCACTGA<br>CTACGGTATGGACGTC |
| iPS:437252 | 21-225_148C6 | NA | | SEQ ID NO:7803<br>SYAMS | SEQ ID NO:15815<br>VISGGGSSTYYADSVKG | SEQ ID NO:23827<br>WRGNPTDYGMDV |
| | | AA | | SEQ ID NO:7804<br>AGCTATGCCATGAGC | SEQ ID NO:15816<br>GTTATTAGTGGTGGTGGT<br>AGTAGCACATACTACGC<br>AGACTCCGTGAAGGGC | SEQ ID NO:23828<br>TGGCGAGGTAACCCCACTGA<br>CTACGGTATGGACGTC |
| iPS:437254 | 21-225_148H11 | NA | | SEQ ID NO:7805<br>SYAMS | SEQ ID NO:15817<br>VISGGGSSTYYADSVKG | SEQ ID NO:23829<br>WRGNPTDYGMDV |
| | | AA | | SEQ ID NO:7806<br>CGCTATGCCATGCAC | SEQ ID NO:15818<br>TTTATATGGTATGATGGA<br>AGTGAGAACTACTATGC<br>AGACTCCGTGAAGGGC | SEQ ID NO:23830<br>GATCGGGTGGAGGGTTCGGG<br>GACTCCCTACTACTACTACG<br>GTATGGACGTC |
| | 21-225_149F2 | | | SEQ ID NO:7807<br>RYGMH | SEQ ID NO:15819<br>FIWYDGSENYYADSVKG | SEQ ID NO:23831<br>DRVEGSGTPYYYGMDV |
| | | AA | | SEQ ID NO:7808 | SEQ ID NO:15820 | SEQ ID NO:23832 |

FIGURE 49 (Continued)

| | | | | |
|---|---|---|---|---|
| iPS:437256 | 21-225_150F11 | NA | CGCTATGGCATGCAC SEQ ID NO:7809 | TTTATATGGTATGATGGA AGTGAGAACTACTATGC AGACTCCGTGAAGGGC SEQ ID NO:15821 | GATCGGGTGGAGGGTTCGGG GACTCCTACTACTACG GTATGGACGTC SEQ ID NO:23833 |
| | | AA | RYGMH SEQ ID NO:7810 | FIWYDGSENYYADSVKG SEQ ID NO:15822 | DRVEGSGTPYYYYGMDV SEQ ID NO:23834 |
| iPS:437258 | 21-225_153F9 | NA | ACCTATGGCATGCAC SEQ ID NO:7811 | GTTATATGGTATGGTGG AAGTGATACAGACTATG CAGACTCCGTGAGGGGC SEQ ID NO:15823 | GATCGGGATTATTGTAGTGG TGGTAACTGCCCTTACTACT ACTACTACGGTATGGACGTC SEQ ID NO:23835 |
| | | AA | TYGMH SEQ ID NO:7812 | VIWYGGSDTDYADSVRG SEQ ID NO:15824 | DRDYCSGGNCPYYYYGMDV SEQ ID NO:23836 |
| iPS:437260 | 21-225_170D1 | NA | GGCTACTTTATGCAC SEQ ID NO:7813 | TGGATCAAGCCTAAAAG CGGTGGCACAAACTGTG CACAGAAGTTTCAGGGC SEQ ID NO:15825 | GGGGGGCTACGGTGACTAC GTGGGGGTCTTTGACTAC SEQ ID NO:23837 |
| | | AA | GYFMH SEQ ID NO:7814 | WIKPKSGGTNCAQKFQG SEQ ID NO:15826 | GGATVTWGVFDY SEQ ID NO:23838 |
| iPS:437262 | 21-225_170E4 | NA | AGCTATAGCATGAAC SEQ ID NO:7815 | TACATTAGCAGTAGTGG TAGTACCAAATACTACG CAGACTCTGTGGAGGGC SEQ ID NO:15827 | GATAGTAGGAAGGGGTTCTA CTACGGTCTGGACGTC SEQ ID NO:23839 |
| | | AA | SYSMN SEQ ID NO:7816 | YISSSGSTKYYADSVEG SEQ ID NO:15828 | DSRKGFYYGLDV SEQ ID NO:23840 |
| iPS:437264 | 21-225_171H12 | NA | GGCTACTTTATGCAC | TGGATCAAGCCTAAGAG TGGTGGCACAAACTCTG CACAGAGTTTCAGGGC | GGGGGACTACGGTGGCTAC GTGGGGGGTCTTTGACTAC |

FIGURE 49
(Continued)

| | | | | | | | |
|---|---|---|---|---|---|---|---|
| iPS:437266 | 21-225_171H12 | AA | GYFMH | SEQ ID NO:7817 | WIKPKSGGTNSAQRFQG | SEQ ID NO:15829 | GGTTVATWGVFDY | SEQ ID NO:23841 |
| | | NA | GGCTACTTTATGCAC | SEQ ID NO:7818 | TGGATCAAGCCTAAGAG TGGTGGCACAAACTCTG CACAGAGTTTCAGGGC | SEQ ID NO:15830 | GGGGGACTACGGTGGCTAC GTGGGGGGTCTTTGACTAC | SEQ ID NO:23842 |
| iPS:437268 | 21-225_177A5 | AA | GYFMH | SEQ ID NO:7819 | WIKPKSGGTNSAQRFQG | SEQ ID NO:15831 | GGTTVATWGVFDY | SEQ ID NO:23843 |
| | | NA | AGCTATGGCATGGAC | SEQ ID NO:7820 | ATTATATGGTTTGATGGA AGTAATAAATACTATGC AGACTCCGTGAAGGGC | SEQ ID NO:15832 | GCATATTGTGGTGGTGACTG CTATTTCCCCATCTCCATTA CTACGGTATGGACGTC | SEQ ID NO:23844 |
| iPS:437270 | 21-225_177D2 | AA | SYGMD | SEQ ID NO:7821 | IIWFDGSNKYYADSVKG | SEQ ID NO:15833 | AYCGGDCYFPHLHYYGMDV | SEQ ID NO:23845 |
| | | NA | GGCTACTTTATGCAC | SEQ ID NO:7822 | TGGATCAAGCCTAAAAG TGGTGGCACAAACTGTG CACAGAAGTTTCAGGGC | SEQ ID NO:15834 | GGGGGACTACGGTGGACTAC GTGGGGGGTCTTTGACTAC | SEQ ID NO:23846 |
| iPS:437272 | 21-225_178H4 | AA | GYFMH | SEQ ID NO:7823 | WIKPKSGGTNCAQKFQG | SEQ ID NO:15835 | GGTTVITWGVFDY | SEQ ID NO:23847 |
| | | NA | AGCTATGGCATGGAC | SEQ ID NO:7824 | GTTATATGGTATGATGG AAGTAATAGAAACTATG CAGACTCCGTGAAGGGC | SEQ ID NO:15836 | GATCGGTCTAAGGGTTACGA CGGTATGGACGTC | SEQ ID NO:23848 |
| iPS:437274 | 21-225_196D4 | | | SEQ ID NO:7825 | | SEQ ID NO:15837 | | SEQ ID NO:23849 |

FIGURE 49
(Continued)

| | | | | | | |
|---|---|---|---|---|---|---|
| | | AA | SYGMH | | VIWYDGSNRNYADSVKG | DRSKGYDGMDV |
| iPS:437280 | | NA | GACTATGGCATGCAC | | GTTATATGGTAGTAATAGAAATAATAATATA CAGACTCCGTGAAGGGC | GAAGTGGGTTGGCTTGATGA CTAC |
| | 21-225_203C10 | | SEQ ID NO:7826 | | SEQ ID NO:15838 | SEQ ID NO:23850 |
| | | | SEQ ID NO:7827 | | SEQ ID NO:15839 | SEQ ID NO:23851 |
| iPS:437282 | | AA | DYGMH | | VIWYDGGNTHYTDSVKG | EVGWLDDY |
| | 21-225_207C9 | NA | AGCTATGCCATGAGC | | GCTATTAGTGGTAGTGGT GGTAGCACATACTACGC AGACTCCGTGAAGGGC | CTACTACTACAACGGTATGG ACGTC |
| | | | SEQ ID NO:7828 | | SEQ ID NO:15840 | SEQ ID NO:23852 |
| | | | SEQ ID NO:7829 | | SEQ ID NO:15841 | SEQ ID NO:23853 |
| iPS:437286 | | AA | SYAMS | | AISGSGGSTYYADSVKG | AGGTTGSYYYNGMDV |
| | 21-225_208F1 | NA | GACTATGTCATGCAC | | GTTATATGGTATGATGG AAGTAATAAATACTATG TAGACTCCGTGAAGGGC | GAACGGTATAGCAGTGGCTT GTACGACTACGGTATGGACG TC |
| | | | SEQ ID NO:7830 | | SEQ ID NO:15842 | SEQ ID NO:23854 |
| | | | SEQ ID NO:7831 | | SEQ ID NO:15843 | SEQ ID NO:23855 |
| iPS:437290 | | AA | DYVMH | | VIWYDGSNKYYVDSVKG | ERYSSGLYDYGMDV |
| | 21-225_210G6 | NA | GACTATGTCATGCAC | | GTTATATGGTATGATGG AAGTAATAAATACTATG TAGACTCCGTGAAGGGC | GAACGGTATAGCAGTGGCTT GTACGACTACGGTATGGACG TC |
| | | | SEQ ID NO:7832 | | SEQ ID NO:15844 | SEQ ID NO:23856 |
| | | | SEQ ID NO:7833 | | SEQ ID NO:15845 | SEQ ID NO:23857 |

FIGURE 49
(Continued)

| | | | DYVMH | VIWYDGSNKYYVDSVKG | ERYSSGLYDYGMDV |
|---|---|---|---|---|---|
| | | AA | SEQ ID NO:7834 | SEQ ID NO:15846 | SEQ ID NO:23858 |
| iPS:437294 | 21-225_216D5 | NA | AGTGGTGGTTACTACTGGAGC | TACATCTATTACAGTGGGAGCACCTACTACAACCCGTCCCTCAAGAGT | GATTCCCCTGACAGGGGGGTTTGACTAC |
| | | AA | SGGYYWS | YIYYSGSTYYNPSLKS | DSPDRGFDY |
| | | | SEQ ID NO:7835 | SEQ ID NO:15847 | SEQ ID NO:23859 |
| iPS:437302 | 21-225_225B11 | NA | AGCTATGGCATGCAC | ATTATATCATATAGTGGAAGTAATAAATACTATGCAGACTCCGTGAAGGGC | CGGGGATACAGCTATGGCGGGTACGGTATGGACGTC |
| | | | SEQ ID NO:7836 | SEQ ID NO:15848 | SEQ ID NO:23860 |
| | | AA | SYGMH | IISYSGSNKYYADSVKG | RGYSYGGYGMDV |
| | | | SEQ ID NO:7837 | SEQ ID NO:15849 | SEQ ID NO:23861 |
| iPS:437320 | 21-225_75A1 | NA | GATTACTACTGGAGC | GAAATCAATCATAGTGGAGACACCAACTACAACCCGTCCCTCAAGAGT | GAGTTCCATATAGTGGAAGCTACCTCTACTACGGTATGGACGTC |
| | | | SEQ ID NO:7838 | SEQ ID NO:15850 | SEQ ID NO:23862 |
| | | AA | DYYWS | EINHSGDTNYNPSLKS | EFPYSGSYLYYYGMDV |
| | | | SEQ ID NO:7839 | SEQ ID NO:15851 | SEQ ID NO:23863 |
| iPS:437322 | 21-225_75B1 | NA | AATTATGATATCAAC | TGGATGCACCCTAACAGTGGTAACACAGGCTATGCACAGAAGTTCCAGGGC | AGTAGTGGCTGGTACTGGTTCGACCCC |
| | | | SEQ ID NO:7840 | SEQ ID NO:15852 | SEQ ID NO:23864 |
| | | AA | NYDIN | WMHPNSGNTGYAQKFQG | SSGWYWFDP |
| | | | SEQ ID NO:7841 | SEQ ID NO:15853 | SEQ ID NO:23865 |
| | | | SEQ ID NO:7842 | SEQ ID NO:15854 | SEQ ID NO:23866 |

FIGURE 49
(Continued)

| | | | | | |
|---|---|---|---|---|---|
| iPS:437324 | 21-225_75C2 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:7843 | SEQ ID NO:15855 | SEQ ID NO:23867 |
| | | AA | GCYWS | EINHSGSTNYNPSLKS | DYGGMDV |
| | | | SEQ ID NO:7844 | SEQ ID NO:15856 | SEQ ID NO:23868 |
| iPS:437326 | 21-225_75C10 | NA | AGTTATGGCATGCAT | GTTATATGGTATGATGG AAGTGATAAATACTATG CAGACTCCGTGAAGGGC | GATCGGTTAGTGGGAGCTAC GGTTGATGCTTTTGATATC |
| | | | SEQ ID NO:7845 | SEQ ID NO:15857 | SEQ ID NO:23869 |
| | | AA | SYGMH | VIWYDGSDKYYADSVKG | DRLVGATVDAFDI |
| | | | SEQ ID NO:7846 | SEQ ID NO:15858 | SEQ ID NO:23870 |
| iPS:437328 | 21-225_75D3 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:7847 | SEQ ID NO:15859 | SEQ ID NO:23871 |
| | | AA | GCYWS | EINHSGSTNYNPSLKS | DYGGMDV |
| | | | SEQ ID NO:7848 | SEQ ID NO:15860 | SEQ ID NO:23872 |
| iPS:437332 | 21-225_75F3 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:7849 | SEQ ID NO:15861 | SEQ ID NO:23873 |
| | | AA | GCYWS | EINHSGSTNYNPSLKS | DYGGMDV |
| | | | SEQ ID NO:7850 | SEQ ID NO:15862 | SEQ ID NO:23874 |
| iPS:437334 | 21-225_75F11 | NA | ACTGGTGGAGTGGGTGTGG C | CTCATTATTGGGATGAT GATAAGCGCTACAGCCC ATCTCTGAAGAGC | CTTATAGCAGTGGCCTTTGA CTAC |
| | | | SEQ ID NO:7851 | SEQ ID NO:15863 | SEQ ID NO:23875 |
| | | AA | TGGVGVG | LIYWDDDKRYSPSLKS | LIAVAFDY |

FIGURE 49
(Continued)

| | | | | | | | |
|---|---|---|---|---|---|---|---|
| iPS:437340 | 21-225_75G9 | NA | SEQ ID NO:7852 GGTTGCTACTGGAGC | SEQ ID NO:15864 GAAATCAATCATAGTGG AAGGACCAACTACAACC CGTTCCCTCAAGAGT | SEQ ID NO:23876 GACTACGGTGGGCTTGACTA C |
| | | AA | SEQ ID NO:7853 GCYWS | SEQ ID NO:15865 EINHSGRTNYNPSLKS | SEQ ID NO:23877 DYGGLDY |
| iPS:437344 | 21-225_75G12 | NA | SEQ ID NO:7854 GGTTGCTACTGGAGC | SEQ ID NO:15866 GAAATCAATCATAGTGG AAGCACCAACTACAACC CGTTCCCTCAAGAGT | SEQ ID NO:23878 GACTACGGGCGGTATGGACGT C |
| | | AA | SEQ ID NO:7855 GCYWS | SEQ ID NO:15867 EINHSGSTNYNPSLKS | SEQ ID NO:23879 DYGGMDV |
| iPS:437346 | 21-225_75H7 | NA | SEQ ID NO:7856 AGGAGTAGTTACTACTGGGG C | SEQ ID NO:15868 AGTATCTATTATAGTGGG AGCGCTACTCCAACCC GTCCCTCAAGAGT | SEQ ID NO:23880 CTTGACTCTAACTGGGGTCT TGACTAC |
| | | AA | SEQ ID NO:7857 RSSYYWG | SEQ ID NO:15869 SIYYSGSAYSNPSLKS | SEQ ID NO:23881 LDSNWGLDY |
| iPS:437350 | 21-225_74A3 | NA | SEQ ID NO:7858 GGTTGCTACTGGAGC | SEQ ID NO:15870 GAAATCAATCATAGTGG AAGCACCAACTACAACC CGTTCCCTCAAGAGT | SEQ ID NO:23882 GACTACGGGCGGTATGGACGT C |
| | | AA | SEQ ID NO:7859 GCYWS | SEQ ID NO:15871 EINHSGSTNYNPSLKS | SEQ ID NO:23883 DYGGMDV |
| iPS:437356 | 21-225_74B1 | NA | SEQ ID NO:7860 AATTATGATATCAAC | SEQ ID NO:15872 TGGATGAACCCTAACAG TGGTAACACAGGCTATG CACAGAAGTTCCAGGGC | SEQ ID NO:23884 ACCAGTGGCTGGAACTTCTT TGACTAC |
| | | | SEQ ID NO:7861 | SEQ ID NO:15873 | SEQ ID NO:23885 |

FIGURE 49
(Continued)

| | | | | WMNPNSGNTGYAQKFQG | TSGWNFFDY |
|---|---|---|---|---|---|
| iPS:437361 | | AA | NYDIN | SEQ ID NO:15874 | SEQ ID NO:23886 |
| | 21-225_74C1 | NA | AATTATGATATCAAC | TGGATGAACCCTGACAG TGGTAACACAGGCTTTG CACAGAAGTTCCAGGGC | TCCAGTGGCTGGTACTGGTT CGACCCC |
| | | | | SEQ ID NO:15875 | SEQ ID NO:23887 |
| | | AA | NYDIN | WMNPDSGNTGFAQKFQG | SSGWYWFDP |
| iPS:437363 | | | SEQ ID NO:7864 | SEQ ID NO:15876 | SEQ ID NO:23888 |
| | 21-225_74C10 | NA | AATTATGATATCAAC | TGGATGAACCCTAACAG TGGTAACATAGGCTATG CACAGAAGTTCCAGGGC | AGCAGTGGCTGGTACTGGTT CGACCCC |
| | | | SEQ ID NO:7865 | SEQ ID NO:15877 | SEQ ID NO:23889 |
| | | AA | NYDIN | WMNPNSGNIGYAQKFQG | SSGWYWFDP |
| iPS:437369 | | | SEQ ID NO:7866 | SEQ ID NO:15878 | SEQ ID NO:23890 |
| | 21-225_74D6 | NA | GGTTGCTACTGGAGC | GAAATCAATCATAGTGG AAGCACCAACTACAACC CGTCCCTCAAGAGT | GACTACGGCGGGTATGGACGT C |
| | | | SEQ ID NO:7867 | SEQ ID NO:15879 | SEQ ID NO:23891 |
| | | AA | GCYWS | EINHSGSTNYNPSLKS | DYGGMDV |
| iPS:437371 | | | SEQ ID NO:7868 | SEQ ID NO:15880 | SEQ ID NO:23892 |
| | 21-225_74D8 | NA | AACTACGACATGCAC | GCTATTGGTACTGCTGGT GACACATATATCCAGG CTCCGTGAAGGGC | GTTCTTGACTACGGTGACTC CTGGGCTACTACTACACG GTATGGACGTC |
| | | | SEQ ID NO:7869 | SEQ ID NO:15881 | SEQ ID NO:23893 |
| | | AA | NYDMH | AIGTAGDTYYPGSVKG | VLDYGDSLGYYYYGMDV |
| | | | SEQ ID NO:7870 | SEQ ID NO:15882 | SEQ ID NO:23894 |

FIGURE 49
(Continued)

| | | | ACTGGTGGAGTGGGTGTGG C | CTCATTTATTGGGATGAT GATAAGGCGTACAGCCC ATCTCTGAAGAGC | CTTATAGCAGTGGCCTTTGA CTAC |
|---|---|---|---|---|---|
| iPS:437377 | 21-225_74G9 | NA | SEQ ID NO:7871 | SEQ ID NO:15883 | SEQ ID NO:23895 |
| | | AA | TGGVGVG | LIYWDDDKRYSPSLKS | LIAVAFDY |
| | | NA | SEQ ID NO:7872 AATTATGATATCAAC | SEQ ID NO:15884 TGGATGCACCCTAACAG TGGTAACACAGGCTTTG CACAGAAGTTCCAGGGC | SEQ ID NO:23896 TCCAGTGGCTGGTACTGGTT CGACCCC |
| iPS:437379 | 21-225_74H2 | | SEQ ID NO:7873 | SEQ ID NO:15885 | SEQ ID NO:23897 |
| | | AA | NYDIN | WMHPNSGNTGFAQKFQG | SSGWYWFDP |
| | | NA | SEQ ID NO:7874 AACGCCTGGATGAAC | SEQ ID NO:15886 CGTATTAAAAGCAAAAC TGATGGTGGGACAACAG ACTACGCTGCACCCGTG AAAGGC | SEQ ID NO:23898 GTGGGAGTACTACGGACTA C |
| iPS:437383 | 21-225_74H8 | | SEQ ID NO:7875 | SEQ ID NO:15887 | SEQ ID NO:23899 |
| | | AA | NAWMN | RIKSKTDGGTTDYAAPVK G | VGATTDY |
| | | NA | SEQ ID NO:7876 AACTATGGCATGCAC | SEQ ID NO:15888 GTTATATGGTATGATGG AAGTAATAAATACTATG CAGACTCCGTGAAGGGC | SEQ ID NO:23900 GGGGACTGGAACCCCGAGGG TATGGACGTC |
| iPS:438664 | 21-225_216G1 | | SEQ ID NO:7877 | SEQ ID NO:15889 | SEQ ID NO:23901 |
| | | AA | NYGMH | VIWYDGSNKYADSVKG | GDWNPEGMDV |
| | | | SEQ ID NO:7878 | SEQ ID NO:15890 | SEQ ID NO:23902 |

FIGURE 49
(Continued)

| | | | | |
|---|---|---|---|---|
| iPS:441468 | 21-225_25A4.001.001 | NA | AATTATGATATTAAT SEQ ID NO:7879 | TGGATGTACCCTAACAG TGGTAGCACAGGCTATG CACAGAAATTCCAGGGC SEQ ID NO:15891 | AGCAGTGGCTGGTACTACTT TGACTAC SEQ ID NO:23903 |
| | | AA | NYDIN SEQ ID NO:7880 | WMYPNSGSTGYAQKFQG SEQ ID NO:15892 | SSGWYYFDY SEQ ID NO:23904 |
| iPS:441475 | 21-225_25A4.001.002 | NA | AATTATGATATTAAT SEQ ID NO:7881 | TGGATGTACCCTAACAG TGGTAACGCAGGCTATG CACAGAAATTCCAGGGC SEQ ID NO:15893 | AGCAGTGGCTGGTACTACTT TGACTAC SEQ ID NO:23905 |
| | | AA | NYDIN SEQ ID NO:7882 | WMYPNSGNAGYAQKFQG SEQ ID NO:15894 | SSGWYYFDY SEQ ID NO:23906 |
| iPS:441482 | 21-225_25A4.001.003 | NA | AATTATGATATTAAT SEQ ID NO:7883 | TGGATGTACCCTAACAG TGGTAACGTAGGCTATG CACAGAAATTCCAGGGC SEQ ID NO:15895 | AGCAGTGGCTGGTACTACTT TGACTAC SEQ ID NO:23907 |
| | | AA | NYDIN SEQ ID NO:7884 | WMYPNSGNVGYAQKFQG SEQ ID NO:15896 | SSGWYYFDY SEQ ID NO:23908 |
| iPS:441489 | 21-225_25A4.001.004 | NA | AATTATGATATTAAT SEQ ID NO:7885 | TGGATGTACCCTAACAG TGGTCAAACAGGCTATG CACAGAAATTCCAGGGC SEQ ID NO:15897 | AGCAGTGGCTGGTACTACTT TGACTAC SEQ ID NO:23909 |

FIGURE 49
(Continued)

| | | AA | NYDIN | | WMYPNSGQTGYAQKFQG | SSGWYYFDY |
|---|---|---|---|---|---|---|
| iPS:441496 | | | SEQ ID NO:7886 | | SEQ ID NO:15898 | SEQ ID NO:23910 |
| | 21-225_25A4.001.005 | NA | AATTATGATATTAAT | | TGGATGTACCCTAACAGTGGTAGCACAGGCTATGCACAGAAATTCCAGGGC | AGCAGTGGCTGGTACTACTTTGACTAC |
| | | | SEQ ID NO:7887 | | SEQ ID NO:15899 | SEQ ID NO:23911 |
| | | AA | NYDIN | | WMYPNSGSTGYAQKFQG | SSGWYYFDY |
| iPS:441505 | | | SEQ ID NO:7888 | | SEQ ID NO:15900 | SEQ ID NO:23912 |
| | 21-225_25A4.001.006 | NA | AATTATGATATTAAT | | TGGATGTACCCTAACAGTGGTAACGCAGGCTATGCACAGAAATTCCAGGGC | AGCAGTGGCTGGTACTACTTTGACTAC |
| | | | SEQ ID NO:7889 | | SEQ ID NO:15901 | SEQ ID NO:23913 |
| | | AA | NYDIN | | WMYPNSGNAGYAQKFQG | SSGWYYFDY |
| iPS:441512 | | | SEQ ID NO:7890 | | SEQ ID NO:15902 | SEQ ID NO:23914 |
| | 21-225_25A4.001.007 | NA | AATTATGATATTAAT | | TGGATGTACCCTAACAGTGGTAACGTAGGCTATGCACAGAAATTCCAGGGC | AGCAGTGGCTGGTACTACTTTGACTAC |
| | | | SEQ ID NO:7891 | | SEQ ID NO:15903 | SEQ ID NO:23915 |
| | | AA | NYDIN | | WMYPNSGNVGYAQKFQG | SSGWYYFDY |
| | | | SEQ ID NO:7892 | | SEQ ID NO:15904 | SEQ ID NO:23916 |

FIGURE 49
(Continued)

| iPS: | code | | | | |
|---|---|---|---|---|---|
| iPS:441519 | 21-225_25A4.001.008 | NA | AATTATGATATTAAT SEQ ID NO:7893 | TGGATGTACCCTAACAG TGGTCAAACAGGCTATG CACAGAAATTCCAGGGC SEQ ID NO:15905 | AGCAGTGGCTGGTACTACTT TGACTAC SEQ ID NO:23917 |
| | | AA | NYDIN SEQ ID NO:7894 | WMYPNSGQTGYAQKFQG SEQ ID NO:15906 | SSGWYYFDY SEQ ID NO:23918 |
| iPS:441554 | 21-225_25A4.001.013 | NA | AATTATGATATTAAT SEQ ID NO:7895 | TGGATGTACCCTAACAG TGGTAGCACAGGCTATG CACAGAAATTCCAGGGC SEQ ID NO:15907 | AGCAGTGGCTGGTACTACTT TGACTAC SEQ ID NO:23919 |
| | | AA | NYDIN SEQ ID NO:7896 | WMYPNSGSTGYAQKFQG SEQ ID NO:15908 | SSGWYYFDY SEQ ID NO:23920 |
| iPS:441595 | 21-225_25A4.001.019 | NA | AATTATGATATTAAT SEQ ID NO:7897 | TGGATGTACCCTAACAG TGGTAGCACAGGCTATG CACAGAAATTCCAGGGC SEQ ID NO:15909 | AGCAGTGGCTGGTACTACTT TGACTAC SEQ ID NO:23921 |
| | | AA | NYDIN SEQ ID NO:7898 | WMYPNSGSTGYAQKFQG SEQ ID NO:15910 | SSGWYYFDY SEQ ID NO:23922 |
| iPS:441604 | 21-225_25A4.001.020 | NA | AATTATGATATTAAT SEQ ID NO:7899 | TGGATGTACCCTAACAG TGGTCAAACAGGCTATG CACAGAAATTCCAGGGC SEQ ID NO:15911 | AGCAGTGGCTGGTACTACTT TGACTAC SEQ ID NO:23923 |

FIGURE 49
(Continued)

| | | AA | NYDIN | WMYPNSGQTGYAQKFQG | SSGWYYFDY |
|---|---|---|---|---|---|
| | | | SEQ ID NO:7900 | SEQ ID NO:15912 | SEQ ID NO:23924 |
| iPS:441613 | 21-225_25A4.001.021 | NA | AATTATGATATTAAT | TGGATGTACCCTAACAG TGGTAACGCAGGCTATG CACAGAAATTCCAGGGC | AGCAGTGGCTGGTACTACTT TGACTAC |
| | | | SEQ ID NO:7901 | SEQ ID NO:15913 | SEQ ID NO:23925 |
| | | AA | NYDIN | WMYPNSGNAGYAQKFQG | SSGWYYFDY |
| | | | SEQ ID NO:7902 | SEQ ID NO:15914 | SEQ ID NO:23926 |
| iPS:441841 | 21-225_4A2.001.001 | NA | AATTATGATATTCAAC | TGGATGCACCCTAACAG TGGTAACACAGGCTATG CACAGAAGTTCCAGGGC | AGCAGTGGCTGGTACTACTT TGACTAC |
| | | | SEQ ID NO:7903 | SEQ ID NO:15915 | SEQ ID NO:23927 |
| | | AA | NYDIN | WMHPNSGNTGYAQKFQG | SSGWYYFDY |
| | | | SEQ ID NO:7904 | SEQ ID NO:15916 | SEQ ID NO:23928 |
| iPS:441847 | 21-225_4A2.001.002 | NA | AATTATGATATTCAAC | TGGATGCACCCTAACAG TGGTAACACAGGCTATG CACAGAAGTTCCAGGGC | AGCAGTGGCTGGTACTACTT TGACTAC |
| | | | SEQ ID NO:7905 | SEQ ID NO:15917 | SEQ ID NO:23929 |
| | | AA | NYDIN | WMHPNSGNTGYAQKFQG | SSGWYYFDY |
| | | | SEQ ID NO:7906 | SEQ ID NO:15918 | SEQ ID NO:23930 |
| iPS:441853 | 21-225_4A2.001.003 | NA | AATTATGATATTCAAC | TGGATGCACCCTAACAG TGGTAACACAGGCTATG CACAGAAGTTCCAGGGC | AGCAGTGGCTGGTACTACTT TGACTAC |
| | | | SEQ ID NO:7907 | SEQ ID NO:15919 | SEQ ID NO:23931 |

FIGURE 49
(Continued)

| | | | | | |
|---|---|---|---|---|---|
| iPS:441859 | 21-225_4A2.001.004 | AA | NYDIN | WMHPNSGNTGYAQKFQG | SSGWYYFDY |
| | | NA | AATTATGATATCAAC SEQ ID NO:7908 | TGGATGCACCCTAACAG TGGTAACCGGCTATG CACAGAAGTTCCAGGGC SEQ ID NO:15920 | AGCAGTGGCTGGTACTACTT TGACTAC SEQ ID NO:23932 |
| iPS:441866 | 21-225_4A2.001.005 | AA | NYDIN SEQ ID NO:7909 | WMHPNSGNAGYAQKFQG SEQ ID NO:15921 | SSGWYYFDY SEQ ID NO:23933 |
| | | NA | AATTATGATATCAAC SEQ ID NO:7910 | TGGATGCACCCTAACAG TGGTAGCACAGGCTATG CACAGAAGTTCCAGGGC SEQ ID NO:15922 | AGCAGTGGCTGGTACTACTT TGACTAC SEQ ID NO:23934 |
| iPS:441873 | 21-225_4A2.001.006 | AA | NYDIN SEQ ID NO:7911 | WMHPNSGSTGYAQKFQG SEQ ID NO:15923 | SSGWYYFDY SEQ ID NO:23935 |
| | | NA | AATTATGATATCAAC SEQ ID NO:7912 | TGGATGCACCCTAACAG TGGTCAAACAGGCTATG CACAGAAGTTCCAGGGC SEQ ID NO:15924 | AGCAGTGGCTGGTACTACTT TGACTAC SEQ ID NO:23936 |
| iPS:441880 | 21-225_4A2.001.007 | AA | NYDIN SEQ ID NO:7913 | WMHPNSGQTGYAQKFQG SEQ ID NO:15925 | SSGWYYFDY SEQ ID NO:23937 |
| | | NA | AATTATGATATCAAC SEQ ID NO:7914 | TGGATGCACCCTAACAG TGGTCAAACAGGCTATG CACAGAAGTTCCAGGGC SEQ ID NO:15926 | AGCAGTGGCTGGTACTACTT TGACTAC SEQ ID NO:23938 |
| | | AA | NYDIN SEQ ID NO:7915 | WMHPNSGQTGYAQKFQG SEQ ID NO:15927 | SSGWYYFDY SEQ ID NO:23939 |

FIGURE 49
(Continued)

| iPS | | | | | | |
|---|---|---|---|---|---|---|
| iPS:441884 | 21-225_4A2.001.008 | NA | SEQ ID NO:7916 AATTATGATATCAAC | SEQ ID NO:15928 TGGATGCACCCTAACAG TGGTAACGCAGGCTATG CACAGAAGTTCCAGGGC | SEQ ID NO:23940 AGCAGTGGCTGGTACTACTT TGACTAC |
| | | AA | SEQ ID NO:7917 NYDIN | SEQ ID NO:15929 WMHPNSGNAGYAQKFQG | SEQ ID NO:23941 SSGWYYFDY |
| iPS:441888 | 21-225_4A2.001.009 | NA | SEQ ID NO:7918 AATTATGATATCAAC | SEQ ID NO:15930 TGGATGCACCCTAACAG TGGTCAAACAGGCTATG CACAGAAGTTCCAGGGC | SEQ ID NO:23942 AGCAGTGGCTGGTACTACTT TGACTAC |
| | | AA | SEQ ID NO:7919 NYDIN | SEQ ID NO:15931 WMHPNSGQTGYAQKFQG | SEQ ID NO:23943 SSGWYYFDY |
| iPS:441892 | 21-225_4A2.001.010 | NA | SEQ ID NO:7920 AATTATGATATCAAC | SEQ ID NO:15932 TGGATGCACCCTAACAG TGGTAACGCAGGCTATG CACAGAAGTTCCAGGGC | SEQ ID NO:23944 AGCAGTGGCTGGTACTACTT TGACTAC |
| | | AA | SEQ ID NO:7921 NYDIN | SEQ ID NO:15933 WMHPNSGNAGYAQKFQG | SEQ ID NO:23945 SSGWYYFDY |
| iPS:441896 | 21-225_4A2.001.011 | NA | SEQ ID NO:7922 AATTATGATATCAAC | SEQ ID NO:15934 TGGATGCACCCTAACAG TGGTCAAACAGGCTATG CACAGAAGTTCCAGGGC | SEQ ID NO:23946 AGCAGTGGCTGGTACTACTT TGACTAC |
| | | AA | SEQ ID NO:7923 NYDIN | SEQ ID NO:15935 WMHPNSGQTGYAQKFQG | SEQ ID NO:23947 SSGWYYFDY |
| | | | SEQ ID NO:7924 | SEQ ID NO:15936 | SEQ ID NO:23948 |

FIGURE 49
(Continued)

| iPS: | | | | | |
|---|---|---|---|---|---|
| iPS:441900 | 21-225_4A2.001.012 | NA | AATTATGATATCAAC | TGGATGCACCCTAACAG TGGTAGCACAGGCTATG CACAGAAGTTCCAGGGC | AGCAGTGGCTGGTACTACTT TGACTAC |
| | | | SEQ ID NO:7925 | SEQ ID NO:15937 | SEQ ID NO:23949 |
| | | AA | NYDIN | WMHPNSGSTGYAQKFQG | SSGWYYFDY |
| | | | SEQ ID NO:7926 | SEQ ID NO:15938 | SEQ ID NO:23950 |
| iPS:441955 | 21-225_4A2.001.022 | NA | AATTATGATATCAAC | TGGATGCACCCTAACAG TGGTAACACAGGCTATG CACAGAAGTTCCAGGGC | AGCAGTGGCTGGTACTACTT TGACTAC |
| | | | SEQ ID NO:7927 | SEQ ID NO:15939 | SEQ ID NO:23951 |
| | | AA | NYDIN | WMHPNSGNTGYAQKFQG | SSGWYYFDY |
| | | | SEQ ID NO:7928 | SEQ ID NO:15940 | SEQ ID NO:23952 |
| iPS:441962 | 21-225_4A2.001.023 | NA | AATTATGATATCAAC | TGGATGCACCCTAACAG TGGTAACACAGGCTATG CACAGAAGTTCCAGGGC | AGCAGTGGCTGGTACTACTT TGACTAC |
| | | | SEQ ID NO:7929 | SEQ ID NO:15941 | SEQ ID NO:23953 |
| | | AA | NYDIN | WMHPNSGNTGYAQKFQG | SSGWYYFDY |
| | | | SEQ ID NO:7930 | SEQ ID NO:15942 | SEQ ID NO:23954 |
| iPS:441971 | 21-225_4A2.001.024 | NA | AATTATGATATCAAC | TGGATGCACCCTAACAG TGGTCAAACAGGCTATG CACAGAAGTTCCAGGGC | AGCAGTGGCTGGTACTACTT TGACTAC |
| | | | SEQ ID NO:7931 | SEQ ID NO:15943 | SEQ ID NO:23955 |
| | | AA | NYDIN | WMHPNSGQTGYAQKFQG | SSGWYYFDY |
| | | | SEQ ID NO:7932 | SEQ ID NO:15944 | SEQ ID NO:23956 |

FIGURE 49 (Continued)

| iPS | | | | | | |
|---|---|---|---|---|---|---|
| iPS:441999 | 21-225_4A2.001.028 | NA | AATTATGATATCAAC | TGGATGCACCCTAACAG TGGTCAAACAGGCTATG CACAGAAGTTCCAGGGC | AGCAGTGGCTGGTACTACTT TGACTAC | |
| | | | SEQ ID NO:7933 | SEQ ID NO:15945 | SEQ ID NO:23957 | |
| | | AA | NYDIN | WMHPNSGQTGYAQKFQG | SSGWYYFDY | |
| | | | SEQ ID NO:7934 | SEQ ID NO:15946 | SEQ ID NO:23958 | |
| iPS:442006 | 21-225_4A2.001.029 | NA | AATTATGATATCAAC | TGGATGCACCCTAACAG TGGTAGCACAGGCTATG CACAGAAGTTCCAGGGC | AGCAGTGGCTGGTACTACTT TGACTAC | |
| | | | SEQ ID NO:7935 | SEQ ID NO:15947 | SEQ ID NO:23959 | |
| | | AA | NYDIN | WMHPNSGSTGYAQKFQG | SSGWYYFDY | |
| | | | SEQ ID NO:7936 | SEQ ID NO:15948 | SEQ ID NO:23960 | |
| iPS:442020 | 21-225_4A2.001.031 | NA | AATTATGATATCAAC | TGGATGCACCCTAACAG TGGTAACGAAGGCTATG CACAGAAGTTCCAGGGC | AGCAGTGGCTGGTACTACTT TGACTAC | |
| | | | SEQ ID NO:7937 | SEQ ID NO:15949 | SEQ ID NO:23961 | |
| | | AA | NYDIN | WMHPNSGNEGYAQKFQG | SSGWYYFDY | |
| | | | SEQ ID NO:7938 | SEQ ID NO:15950 | SEQ ID NO:23962 | |
| iPS:442050 | 21-225_4H6.004 | NA | GACTACTATTTGCAC | TGGATCCACCCTAACAG TGGTGGCACAAACTATG CACAGAAGTTTCAGGGC | GATGGTACCAGCTCGTTTGA CTAC | |
| | | | SEQ ID NO:7939 | SEQ ID NO:15951 | SEQ ID NO:23963 | |
| | | AA | DYYLH | WIHPNSGGTNYAQKFQG | DGTSSFDY | |
| | | | SEQ ID NO:7940 | SEQ ID NO:15952 | SEQ ID NO:23964 | |
| iPS:442059 | 21-225_4H6.005 | NA | GACTACTATTTGCAC | TGGATCCACCCTAACAG TGGTGGCACAAACTATG CACAGAAGTTTCAGGGC | GATGGTACCAGCTCGTTTGA CTAC | |

FIGURE 49 (Continued)

| | | | | | | |
|---|---|---|---|---|---|---|
| iPS:442065 | 21-225_4H6.005 | AA | SEQ ID NO:7941<br>DYYLH | SEQ ID NO:15953<br>WIHPNSGGTNY AQKFQG | SEQ ID NO:23965<br>DGTSSFDY | |
| | | NA | SEQ ID NO:7942<br>GACTACTATTTGCAC | SEQ ID NO:15954<br>TGGATCCACCTAACAG TGGTGGCACAAACTATG CACAGAAGTTTCAGGGC | SEQ ID NO:23966<br>GATGGTACCAGCTCGTTTGA CTAC | |
| iPS:442071 | 21-225_4H6.006 | AA | SEQ ID NO:7943<br>DYYLH | SEQ ID NO:15955<br>WIHPNSGGTNY AQKFQG | SEQ ID NO:23967<br>DGTSSFDY | |
| | | NA | SEQ ID NO:7944<br>GACTACTATTTGCAC | SEQ ID NO:15956<br>TGGATCCACCTAACAG TGGTGGCACAAACTATG CACAGAAGTTTCAGGGC | SEQ ID NO:23968<br>GATGCTACCAGCTCGTTTGA CTAC | |
| iPS:442078 | 21-225_4H6.007 | AA | SEQ ID NO:7945<br>DYYLH | SEQ ID NO:15957<br>WIHPNSGGTNY AQKFQG | SEQ ID NO:23969<br>DATSSFDY | |
| | | NA | SEQ ID NO:7946<br>GACTACTATTTGCAC | SEQ ID NO:15958<br>TGGATCCACCTAACAG TGGTGGCACAAACTATG CACAGAAGTTTCAGGGC | SEQ ID NO:23970<br>AGTGGTACCAGCTCGTTTGA CTAC | |
| iPS:442085 | 21-225_4H6.008 | AA | SEQ ID NO:7947<br>DYYLH | SEQ ID NO:15959<br>WIHPNSGGTNY AQKFQG | SEQ ID NO:23971<br>SGTSSFDY | |
| | | NA | SEQ ID NO:7948<br>GACTACTATTTGCAC | SEQ ID NO:15960<br>TGGATCCACCTAACAG TGGTGGCACAAACTATG CACAGAAGTTTCAGGGC | SEQ ID NO:23972<br>AGTGGTACCAGCTCGTTTGA CTAC | |
| iPS:442089 | 21-225_4H6.009 | AA | SEQ ID NO:7949<br>DYYLH | SEQ ID NO:15961<br>WIHPNSGGTNY AQKFQG | SEQ ID NO:23973<br>SGTSSFDY | |
| | 21-225_4H6.010 | NA | SEQ ID NO:7950<br>GACTACTATTTGCAC | SEQ ID NO:15962<br>TGGATCCACCTAACAG TGGTGGCACAAACTATG CACAGAAGTTTCAGGGC | SEQ ID NO:23974<br>GATGCTACCAGCTCGTTTGA CTAC | |

FIGURE 49
(Continued)

| | | | | | | | |
|---|---|---|---|---|---|---|---|
| iPS:442093 | 21-225_4H6.010 | AA | SEQ ID NO:7951<br>DYYLH | SEQ ID NO:7952<br>GACTACTATTTGCAC | SEQ ID NO:15963<br>WIHPNSGGTNYAQKFQG | SEQ ID NO:15964<br>TGGATCCACCTAACAGTGGTGGCACAAACTATGCACAGAAGTTTCAGGGC | SEQ ID NO:23975<br>DATSSFDY | SEQ ID NO:23976<br>GATGCTACCAGCTCGTTTGACTAC |
| iPS:442115 | 21-225_4H6.011 | AA<br>NA | SEQ ID NO:7953<br>DYYLH<br>SEQ ID NO:7954<br>AACTATGTCATGCAC | | SEQ ID NO:15965<br>WIHPNSGGTNYAQKFQG<br>SEQ ID NO:15966<br>GTTATCTGGTATGATGCAAGTAATAAATACTATGCAGACTCCGTGAAGGGC | | SEQ ID NO:23977<br>DATSSFDY<br>SEQ ID NO:23978<br>GAGGTATATAGCAGTGGCTGGTACGACTACGGTATGGACGTC | |
| iPS:442122 | 21-225_5E5.003 | AA<br>NA | SEQ ID NO:7955<br>NYVMH<br>SEQ ID NO:7956<br>AACTATGTCATGCAC | | SEQ ID NO:15967<br>VIWYDASNKYYADSVKG<br>SEQ ID NO:15968<br>GTTATCTGGTATGATGCAAGTAATAAATACTATGCAGAATCCGTGAAGGGC | | SEQ ID NO:23979<br>EVYSSGWYDYGMDV<br>SEQ ID NO:23980<br>GAGGTATATAGCAGTGGCTGGTACGACTACGGTATGGACGTC | |
| iPS:442129 | 21-225_5E5.004 | AA<br>NA | SEQ ID NO:7957<br>NYVMH<br>SEQ ID NO:7958<br>AACTATGTCATGCAC | | SEQ ID NO:15969<br>VIWYDGSNKYYAESVKG<br>SEQ ID NO:15970<br>GTTATCTGGTATGATGGAAGTAATAAATACTATGCAGGCTCCGTGAAGGGC | | SEQ ID NO:23981<br>EVYSSGWYDYGMDV<br>SEQ ID NO:23982<br>GAGGTATATAGCAGTGGCTGGTACGACTACGGTATGGACGTC | |
| | 21-225_5E5.005 | | SEQ ID NO:7959 | | SEQ ID NO:15971 | | SEQ ID NO:23983 | |

FIGURE 49
(Continued)

| | | | | | | |
|---|---|---|---|---|---|---|
| iPS:442136 | 21-225_5E5.006 | AA | NYVMH | VIWYDGSNKYYAGSVKG | EVYSSGWYDYGMDV | |
| | | | SEQ ID NO:7960 | SEQ ID NO:15972 | SEQ ID NO:23984 | |
| | | NA | AACTATGTCATGCAC | GTTATCTGGTATGATGGAAGTAATAAATACTATGCAGACGCCGTGAAGGGC | GAGGTATATAGCAGTGGCTGGTACGACTACGGTATGGACGTC | |
| | | | SEQ ID NO:7961 | SEQ ID NO:15973 | SEQ ID NO:23985 | |
| iPS:442171 | 21-225_5E5.011 | AA | NYVMH | VIWYDGSNKYYADAVKG | EVYSSGWYDYGMDV | |
| | | | SEQ ID NO:7962 | SEQ ID NO:15974 | SEQ ID NO:23986 | |
| | | NA | AACTATGTCATGCAC | GTTATCTGGTATGATGCAAGTAATAAATACTATGCAGAATCCGTGAAGGGC | GAGGTATATAGCAGTGGCTGGTACGACTACGGTATGGACGTC | |
| | | | SEQ ID NO:7963 | SEQ ID NO:15975 | SEQ ID NO:23987 | |
| iPS:442178 | 21-225_5E5.012 | AA | NYVMH | VIWYDASNKYYAESVKG | EVYSSGWYDYGMDV | |
| | | | SEQ ID NO:7964 | SEQ ID NO:15976 | SEQ ID NO:23988 | |
| | | NA | AACTATGTCATGCAC | GTTATCTGGTATGATGCAAGTAATAAATACTATGCAGAGACGCCGTGAAGGGC | GAGGTATATAGCAGTGGCTGGTACGACTACGGTATGGACGTC | |
| | | | SEQ ID NO:7965 | SEQ ID NO:15977 | SEQ ID NO:23989 | |
| | | AA | NYVMH | VIWYDASNKYYADAVKG | EVYSSGWYDYGMDV | |
| | | | SEQ ID NO:7966 | SEQ ID NO:15978 | SEQ ID NO:23990 | |

FIGURE 49
(Continued)

| | | | | | |
|---|---|---|---|---|---|
| iPS:442199 | 21-225_5E5.015 | NA | AACTATGTCATGCAC SEQ ID NO:7967 | GTTATCTGGTATGATGCA AGTAATAAATACTATGC AGACTCCGTGAAGGGC SEQ ID NO:15979 | GAGGTATATAGCAGTGGCTA TTACGACTACGGTATGGACG TC SEQ ID NO:23991 |
| | | AA | NYVMH SEQ ID NO:7968 | VIWYDASNKYYADSVKG SEQ ID NO:15980 | EVYSSGYYDYGMDV SEQ ID NO:23992 |
| iPS:442206 | 21-225_5E5.016 | NA | AACTATGTCATGCAC SEQ ID NO:7969 | GTTATCTGGTATGATGCA AGTAATAAATACTATGC AGACTCCGTGAAGGGC SEQ ID NO:15981 | GAGGTATATAGCAGTGGCTT CTACGACTACGGTATGGACG TC SEQ ID NO:23993 |
| | | AA | NYVMH SEQ ID NO:7970 | VIWYDASNKYYADSVKG SEQ ID NO:15982 | EVYSSGFYDYGMDV SEQ ID NO:23994 |
| iPS:442213 | 21-225_5E5.017 | NA | AACTATGTCATGCAC SEQ ID NO:7971 | GTTATCTGGTATGATGGA AGTAATAAATACTATGC AGAATCCGTGAAGGGC SEQ ID NO:15983 | GAGGTATATAGCAGTGGCTA TTACGACTACGGTATGGACG TC SEQ ID NO:23995 |
| | | AA | NYVMH SEQ ID NO:7972 | VIWYDGSNKYYAESVKG SEQ ID NO:15984 | EVYSSGYYDYGMDV SEQ ID NO:23996 |
| iPS:442220 | 21-225_5E5.018 | NA | AACTATGTCATGCAC SEQ ID NO:7973 | GTTATCTGGTATGATGGA AGTAATAAATACTATGC AGACTCCGTGAAGGGC SEQ ID NO:15985 | GAGGTATATAGCAGTGGCTA TTACGACTACGGTATGGACG TC SEQ ID NO:23997 |

FIGURE 49
(Continued)

| | | | AA | NYVMH | | VIWYDGSNKYYADSVKG | | EVYSSGYYDYGMDV |
|---|---|---|---|---|---|---|---|---|
| iPS:442227 | | | | SEQ ID NO:7974 | | SEQ ID NO:15986 | | SEQ ID NO:23998 |
| | 21-225_5E5.019 | | NA | AACTATGTCATGCAC | | GTTATCTGGTATGATGGA AGTAATAAATACTATGC AGACTCCGTGAAGGGC | | GAGGTATATAGCAGTGGCTT CTACGACTACGGTATGGACG TC |
| | | | | SEQ ID NO:7975 | | SEQ ID NO:15987 | | SEQ ID NO:23999 |
| | | | AA | NYVMH | | VIWYDGSNKYYADSVKG | | EVYSSGFYDYGMDV |
| iPS:442255 | | | | SEQ ID NO:7976 | | SEQ ID NO:15988 | | SEQ ID NO:24000 |
| | 21-225_5E5.023 | | NA | AACTATGTCATGCAC | | GTTATCTGGTATGATGCA AGTAATAAATACTATGC AGAATCCGTGAAGGGC | | GAGGTATATAGCAGTGGCTA TTACGACTACGGTATGGACG TC |
| | | | | SEQ ID NO:7977 | | SEQ ID NO:15989 | | SEQ ID NO:24001 |
| | | | AA | NYVMH | | VIWYDASNKYYAESVKG | | EVYSSGYYDYGMDV |
| iPS:442262 | | | | SEQ ID NO:7978 | | SEQ ID NO:15990 | | SEQ ID NO:24002 |
| | 21-225_5E5.024 | | NA | AACTATGTCATGCAC | | GTTATCTGGTATGATGCA AGTAATAAATACTATGC AGACGCCGTGAAGGGC | | GAGGTATATAGCAGTGGCTA TTACGACTACGGTATGGACG TC |
| | | | | SEQ ID NO:7979 | | SEQ ID NO:15991 | | SEQ ID NO:24003 |
| | | | AA | NYVMH | | VIWYDASNKYYADAVKG | | EVYSSGYYDYGMDV |
| | | | | SEQ ID NO:7980 | | SEQ ID NO:15992 | | SEQ ID NO:24004 |

FIGURE 49
(Continued)

| | | | | GTTATCTGGTATGATGGA AGTAATAAATACTATGC AGAATCCGTGAAGGGC | GAGGTATATAGCAGTGGCTG GTACGACTACGGTATGGACG TC |
|---|---|---|---|---|---|
| iPS:442269 | 21-225_5E5.025 | NA | AACTATGTCATGCAC | | |
| | | | SEQ ID NO:7981 NYVMH | SEQ ID NO:15993 VIWYDGSNKYYAESVKG | SEQ ID NO:24005 EVYSSGWYDYGMDV |
| | | AA | SEQ ID NO:7982 AGCTTTGGCATGCAC | SEQ ID NO:15994 ATTATCTGGCATGATGG AAGTAATAAATACTATG CAGACTCCGTGAAGGGC | SEQ ID NO:24006 GATCTGAGTATGGGCGGTAT GGACGTC |
| iPS:442311 | 21-225_7E11.001.001 | | SEQ ID NO:7983 SFGMH | SEQ ID NO:15995 IIWHDGSNKYYADSVKG | SEQ ID NO:24007 DLSMGGMDV |
| | | NA | SEQ ID NO:7984 AGCTTTGGCATGCAC | SEQ ID NO:15996 ATTATCTGGCATGATGG AAGTAATAAATACTATG CAGACTCCGTGAAGGGC | SEQ ID NO:24008 GATCTGAGTATGGGCGGTAT GGACGTC |
| iPS:442317 | 21-225_7E11.001.002 | AA | SEQ ID NO:7985 SFGMH | SEQ ID NO:15997 IIWHDGSNKYYADSVKG | SEQ ID NO:24009 DLSMGGMDV |
| | | | SEQ ID NO:7986 AGCTTTGGCATGCAC | SEQ ID NO:15998 ATTATCTGGCATAGTGG AAGTAATAAATACTATG CAGACTCCGTGAAGGGC | SEQ ID NO:24010 GATCTGAGTATGGGCGGTAT GGACGTC |
| iPS:442323 | 21-225_7E11.001.003 | NA | SEQ ID NO:7987 SFGMH | SEQ ID NO:15999 IIWHSGSNKYYADSVKG | SEQ ID NO:24011 DLSMGGMDV |
| | | AA | SEQ ID NO:7988 | SEQ ID NO:16000 | SEQ ID NO:24012 |

FIGURE 49
(Continued)

| iPS:442330 | 21-225_7E11.001.004 | NA | AGCTTTGGCATGCAC | ATTATCTGGCATGAAGG AAGTAATAAATACTATG CAGACTCCGTGAAGGGC | GATCTGAGTATGGGCGGTAT GGACGTC |
|---|---|---|---|---|---|
| | | | SEQ ID NO:7989 | SEQ ID NO:16001 | SEQ ID NO:24013 |
| | | AA | SFGMH | HWHEGSNKYYADSVKG | DLSMGGMDV |
| | | | SEQ ID NO:7990 | SEQ ID NO:16002 | SEQ ID NO:24014 |
| iPS:442337 | 21-225_7E11.001.005 | NA | AGCTTTGGCATGCAC | ATTATCTGGCATGATGCA AGTAATAAATACTATG AGACTCCGTGAAGGGC | GATCTGAGTATGGGCGGTAT GGACGTC |
| | | | SEQ ID NO:7991 | SEQ ID NO:16003 | SEQ ID NO:24015 |
| | | AA | SFGMH | HWHDASNKYYADSVKG | DLSMGGMDV |
| | | | SEQ ID NO:7992 | SEQ ID NO:16004 | SEQ ID NO:24016 |
| iPS:442344 | 21-225_7E11.001.006 | NA | AGCTTTGGCATGCAC | ATTATCTGGCATGATGG AAGTAATAAATACTATG CAGAATCCGTGAAGGGC | GATCTGAGTATGGGCGGTAT GGACGTC |
| | | | SEQ ID NO:7993 | SEQ ID NO:16005 | SEQ ID NO:24017 |
| | | AA | SFGMH | HWHDGSNKYYAESVKG | DLSMGGMDV |
| | | | SEQ ID NO:7994 | SEQ ID NO:16006 | SEQ ID NO:24018 |
| iPS:442351 | 21-225_7E11.001.007 | NA | AGCTTTGGCATGCAC | ATTATCTGGCATGATGG AAGTAATAAATACTATG CAGACGCCGTGAAGGGC | GATCTGAGTATGGGCGGTAT GGACGTC |
| | | | SEQ ID NO:7995 | SEQ ID NO:16007 | SEQ ID NO:24019 |
| | | AA | SFGMH | HWHDGSNKYYADAVKG | DLSMGGMDV |
| | | | SEQ ID NO:7996 | SEQ ID NO:16008 | SEQ ID NO:24020 |

FIGURE 49
(Continued)

| iPS:442358 | 21-225_7E11.001.008 | NA | AGCTTTGGCATGCAC | ATTATCTGGCATGAAGG AAGTAATAAATACTATG CAGACGCCGTGAAGGGC | GATCTGAGTATGGGCGGTAT GGACGTC |
|---|---|---|---|---|---|
| | | | SEQ ID NO:7997 | SEQ ID NO:16009 | SEQ ID NO:24021 |
| | | AA | SFGMH | IIWHEGSNKYYADAVKG | DLSMGGMDV |
| | | | SEQ ID NO:7998 | SEQ ID NO:16010 | SEQ ID NO:24022 |
| iPS:442365 | 21-225_7E11.001.009 | NA | AGCTTTGGCATGCAC | ATTATCTGGCATGAAGG AAGTAATAAATACTATG CAGAATCCGTGAAGGGC | GATCTGAGTATGGGCGGTAT GGACGTC |
| | | | SEQ ID NO:7999 | SEQ ID NO:16011 | SEQ ID NO:24023 |
| | | AA | SFGMH | IIWHEGSNKYYAESVKG | DLSMGGMDV |
| | | | SEQ ID NO:8000 | SEQ ID NO:16012 | SEQ ID NO:24024 |
| iPS:442372 | 21-225_7E11.001.010 | NA | AGCTTTGGCATGCAC | ATTATCTGGCATAGTGG AAGTAATAAATACTATG CAGACGCCGTGAAGGGC | GATCTGAGTATGGGCGGTAT GGACGTC |
| | | | SEQ ID NO:8001 | SEQ ID NO:16013 | SEQ ID NO:24025 |
| | | AA | SFGMH | IIWHSGSNKYYAESVKG | DLSMGGMDV |
| | | | SEQ ID NO:8002 | SEQ ID NO:16014 | SEQ ID NO:24026 |
| iPS:442379 | 21-225_7E11.001.011 | NA | AGCTTTGGCATGCAC | ATTATCTGGCATAGTGG AAGTAATAAATACTATG CAGACGCCGTGAAGGGC | GATCTGAGTATGGGCGGTAT GGACGTC |
| | | | SEQ ID NO:8003 | SEQ ID NO:16015 | SEQ ID NO:24027 |
| | | AA | SFGMH | IIWHSGSNKYYADAVKG | DLSMGGMDV |
| | | | SEQ ID NO:8004 | SEQ ID NO:16016 | SEQ ID NO:24028 |

FIGURE 49
(Continued)

| | | | | | | | |
|---|---|---|---|---|---|---|---|
| iPS:442386 | 21-225_7E11.001.012 | NA | AGCTTTGGCATGCAC | | ATTATCTGGCATAGTGG AAGTAATAAATACTATG CAGACTCCGTGAAGGGC | | GATCTGAGTATGGGCGGTAT GGACGTC |
| | | | SEQ ID NO:8005 SFGMH | | SEQ ID NO:16017 IIWHSGSNKYYADSVKG | | SEQ ID NO:24029 DLSMGGMDV |
| | | AA | SEQ ID NO:8006 | | SEQ ID NO:16018 | | SEQ ID NO:24030 |
| iPS:442390 | 21-225_7E11.001.013 | NA | AGCTTTGGCATGCAC | | ATTATCTGGCATGATGG AAGTAATAAATACTATG CAGAATCCGTGAAGGGC | | GATCTGAGTATGGGCGGTAT GGACGTC |
| | | | SEQ ID NO:8007 SFGMH | | SEQ ID NO:16019 IIWHDGSNKYYAESVKG | | SEQ ID NO:24031 DLSMGGMDV |
| | | AA | SEQ ID NO:8008 | | SEQ ID NO:16020 | | SEQ ID NO:24032 |
| iPS:442394 | 21-225_7E11.001.014 | NA | AGCTTTGGCATGCAC | | ATTATCTGGCATAGTGG AAGTAATAAATACTATG CAGAATCCGTGAAGGGC | | GATCTGAGTATGGGCGGTAT GGACGTC |
| | | | SEQ ID NO:8009 SFGMH | | SEQ ID NO:16021 IIWHSGSNKYYAESVKG | | SEQ ID NO:24033 DLSMGGMDV |
| | | AA | SEQ ID NO:8010 | | SEQ ID NO:16022 | | SEQ ID NO:24034 |
| iPS:442398 | 21-225_7E11.001.015 | NA | AGCTTTGGCATGCAC | | ATTATCTGGCATAGTGG AAGTAATAAATACTATG CAGACTCCGTGAAGGGC | | GATCTGAGTATGGGCGGTAT GGACGTC |
| | | | SEQ ID NO:8011 SFGMH | | SEQ ID NO:16023 IIWHSGSNKYYADSVKG | | SEQ ID NO:24035 DLSMGGMDV |
| | | AA | SEQ ID NO:8012 | | SEQ ID NO:16024 | | SEQ ID NO:24036 |

FIGURE 49
(Continued)

| | | | | | |
|---|---|---|---|---|---|
| iPS:442402 | 21-225_7E11.001.016 | NA | AGCTTTGGCATGCAC | ATTATCTGGCATAGTGG AAGTAATAAATACTATG CAGAATCCGTGAAGGGC | GATCTGAGTATGGGCGGTAT GGACGTC |
| | | | SEQ ID NO:8013 | SEQ ID NO:16025 | SEQ ID NO:24037 |
| | | AA | SFGMH | IIWHSGSNKYYAESVKG | DLSMGGMDV |
| | | | SEQ ID NO:8014 | SEQ ID NO:16026 | SEQ ID NO:24038 |
| iPS:442406 | 21-225_7E11.001.017 | NA | AGCTTTGGCATGCAC | ATTATCTGGCATGAAGG AAGTAATAAATACTATG AGACGCCGTGAAGGGC | GATCTGAGTATGGGCGGTAT GGACGTC |
| | | | SEQ ID NO:8015 | SEQ ID NO:16027 | SEQ ID NO:24039 |
| | | AA | SFGMH | IIWHEGSNKYYADAVKG | DLSMGGMDV |
| | | | SEQ ID NO:8016 | SEQ ID NO:16028 | SEQ ID NO:24040 |
| iPS:442410 | 21-225_7E11.001.018 | NA | AGCTTTGGCATGCAC | ATTATCTGGCATGATGCA AGTAATAAATACTATGC AGAATCCGTGAAGGGC | GATCTGAGTATGGGCGGTAT GGACGTC |
| | | | SEQ ID NO:8017 | SEQ ID NO:16029 | SEQ ID NO:24041 |
| | | AA | SFGMH | IIWHDASNKYYAESVKG | DLSMGGMDV |
| | | | SEQ ID NO:8018 | SEQ ID NO:16030 | SEQ ID NO:24042 |
| iPS:442417 | 21-225_7E11.001.019 | NA | AGCTTTGGCATGCAC | ATTATCTGGCATGATGG AAGTAATAAATACTATG CAGAATCCGTGAAGGGC | GATCTGAGTATGGGCGGTAT GGACGTC |
| | | | SEQ ID NO:8019 | SEQ ID NO:16031 | SEQ ID NO:24043 |
| | | AA | SFGMH | IIWHDGSNKYYAESVKG | DLSMGGMDV |
| | | | SEQ ID NO:8020 | SEQ ID NO:16032 | SEQ ID NO:24044 |

FIGURE 49
(Continued)

| | | | | | |
|---|---|---|---|---|---|
| iPS:442431 | 21-225_7E11.001.021 | NA | AGCTTTGGCATGCAC SEQ ID NO:8021 | ATTATCTGGCATAGTGG AAGTAATAAATACTATG CAGAATCCGTGAAGGGC SEQ ID NO:16033 | GATCTGAGTATGGGCGGTAT GGACGTC SEQ ID NO:24045 |
| | | AA | SFGMH SEQ ID NO:8022 | IIWHSGSNKYYAESVKG SEQ ID NO:16034 | DLSMGGMDV SEQ ID NO:24046 |
| iPS:442438 | 21-225_7E11.001.022 | NA | AGCTTTGGCATGCAC SEQ ID NO:8023 | ATTATCTGGCATGAAGG AAGTAATAAATACTATG CAGAATCCGTGAAGGGC SEQ ID NO:16035 | GATCTGAGTATGGGCGGTAT GGACGTC SEQ ID NO:24047 |
| | | AA | SFGMH SEQ ID NO:8024 | IIWHEGSNKYYAESVKG SEQ ID NO:16036 | DLSMGGMDV SEQ ID NO:24048 |
| iPS:442568 | 21-225_149D8 | NA | AACAGTGGTTACTACTGGAG C SEQ ID NO:8025 | TACAGCTATTACAGTGG GAGCACCTACTACAACC CGTCCCTCAAGAGT SEQ ID NO:16037 | GGGGGATATAACTGGAACCA TGCTTTTGATATC SEQ ID NO:24049 |
| | | AA | NSGYYWS SEQ ID NO:8026 | YSYYSGSTYYNPSLKS SEQ ID NO:16038 | GGYNWNHAFDI SEQ ID NO:24050 |
| iPS:443803 | 21-225_43F11_LC2 | NA | GGCTACTATATACAC SEQ ID NO:8027 | TGGATCAACCCTAACAG TGGTGGCACAAACTATG CACAGAAGTTTCAGGGC SEQ ID NO:16039 | GGAGGGAATTACTTCTACAA CCACGTTATGGACGTC SEQ ID NO:24051 |
| | | AA | GYYIH SEQ ID NO:8028 | WINPNSGGTNYAQKFQG SEQ ID NO:16040 | GGNYFYNHVMDV SEQ ID NO:24052 |
| iPS:443805 | 21-225_43F11_LC1 | NA | GGCTACTATATACAC SEQ ID NO:8029 | TGGATCAACCCTAACAG TGGTGGCACAAACTATG CACAGAAGTTTCAGGGC SEQ ID NO:16041 | GGAGGGAATTACTTCTACAA CCACGTTATGGACGTC SEQ ID NO:24053 |

FIGURE 49
(Continued)

| | | | | | | | | |
|---|---|---|---|---|---|---|---|---|
| iPS:443006 | 21-225_25A4.001.029 | AA | GYYIH | SEQ ID NO:8030 | WINPNSGGTNYAQKFQG | SEQ ID NO:16042 | GGNYFYNHVMDV | SEQ ID NO:24054 |
| | | NA | AATTATGATATTAAT | SEQ ID NO:8031 | TGGATGTACCCTAACAGTGGTCAAACAGGCTATGCACAGAAATTCCAGGGC | SEQ ID NO:16043 | AGCAGTGGCTGGTACTACTTTGACTAC | SEQ ID NO:24055 |
| iPS:443016 | 21-225_4H6.014 | AA | NYDIN | SEQ ID NO:8032 | WMYPNSGQTGYAQKFQG | SEQ ID NO:16044 | SSGWYYFDY | SEQ ID NO:24056 |
| | | NA | GACTACTATTTGCAC | SEQ ID NO:8033 | TGGATCCACCTAACAGTGGTGGCACAAACTATGCACAGAAGTTTCAGGGC | SEQ ID NO:16045 | GATGCTACCAGCTCGTTTGACTAC | SEQ ID NO:24057 |
| iPS:443027 | 21-225_7E11.001.023 | AA | DYYLH | SEQ ID NO:8034 | WIHPNSGGTNYAQKFQG | SEQ ID NO:16046 | DATSSFDY | SEQ ID NO:24058 |
| | | NA | AGCTTTGGCATGCAC | SEQ ID NO:8035 | ATTATCTGGCATGATGCAAGTAATAAATACTATGCAGACGCCGTGAAGGGC | SEQ ID NO:16047 | GATCTGAGTATGGGCGGTATGGACGTC | SEQ ID NO:24059 |
| iPS:446086 | 21-225_94D8 | AA | SFGMH | SEQ ID NO:8036 | IIWHDASNKYYADAVKG | SEQ ID NO:16048 | DLSMGGMDV | SEQ ID NO:24060 |
| | | NA | AATTATGATATCAAC | SEQ ID NO:8037 | TGGATGAACCCTAACAGTGGTAACACAGGCTATGCACAGAAGTTCCAGGTC | SEQ ID NO:16049 | AGCAGTGGCTGGTACATCTTTGACTAC | SEQ ID NO:24061 |
| | | AA | NYDIN | | WMNPNSGNTGYAQKFQV | | SSGWYIFDY | |

FIGURE 49 (Continued)

| | | | | |
|---|---|---|---|---|
| iPS:446094 | 21-225_77E1 | NA | SEQ ID NO:8038<br>AATTATGATATCAAC | SEQ ID NO:16050<br>TGGATGAACCCTAACAG<br>TGGTAACACAGGCTATG<br>CACAGAAGTTCCAGGGC | SEQ ID NO:24062<br>TCCAGTGGCTGGCACTGGTT<br>CGACCCC |
| | | AA | SEQ ID NO:8039<br>NYDIN | SEQ ID NO:16051<br>WMNPNSGNTGYAQKFQG | SEQ ID NO:24063<br>SSGWHWFDP |
| iPS:448904 | 21-225_65C12 | NA | SEQ ID NO:8040<br>AGCTTTAGCTTGAAC | SEQ ID NO:16052<br>TCCATTAGTAGTAGTAGT<br>AGTTACATATACTACGC<br>AGACTCAGTGAAGGGC | SEQ ID NO:24064<br>GATGCGTATAGCCACTAC |
| | | AA | SEQ ID NO:8041<br>SFSLN | SEQ ID NO:16053<br>SISSSSYIYYADSVKG | SEQ ID NO:24065<br>DAYSHY |
| iPS:448906 | 21-225_72G9 | NA | SEQ ID NO:8042<br>AGTTATAGCATGAAC | SEQ ID NO:16054<br>TCCATTAGTGGTAGTAGT<br>AGTTACATATACTACGC<br>AGACTCAGTGAAGGGC | SEQ ID NO:24066<br>GGGGGTTCGAGGGGGGTTCGA<br>CCCC |
| | | AA | SEQ ID NO:8043<br>SYSMN | SEQ ID NO:16055<br>SISGSSSYIYYADSVKG | SEQ ID NO:24067<br>GGSRGFDP |
| iPS:448908 | 21-225_50G9 | NA | SEQ ID NO:8044<br>AGCTATGGCATGCAC | SEQ ID NO:16056<br>GTTATATCACAAGATGG<br>AATTATTAGATACTATGC<br>AGACTCCGTGAAGGGC | SEQ ID NO:24068<br>GATGTGAAGCAGTGGCTGGT<br>ACGGACCTACGGTATGGACG<br>TC |
| | | AA | SEQ ID NO:8045<br>SYGMH | SEQ ID NO:16057<br>VISQDGIIRYYADSVKG | SEQ ID NO:24069<br>DVKQWLVRTYGMDV |
| iPS:451102 | 21-225_45F6 | NA | SEQ ID NO:8046<br>TACTATGGCTTGCAC | SEQ ID NO:16058<br>GTTATATCATATGATGGA<br>AGTAATAAATATTATGC<br>AGACTCCGTGAAGGGC | SEQ ID NO:24070<br>GAGGATGCGATATTGTAGTGG<br>TACCAGCTGCCCTACTACT<br>ACTACTACGGTATGGACGTC |

FIGURE 49
(Continued)

| | | | SEQ ID NO:8047 | SEQ ID NO:16059 | SEQ ID NO:24071 |
| --- | --- | --- | --- | --- | --- |
| iPS:451104 | 21-225_45F6 | AA | YYGLH | VISYDGSNKYYADSVKG | EDRYCSGTSCPYYYYGMDV |
| | | NA | SEQ ID NO:8048 AGCTATGGTATCAGC | SEQ ID NO:16060 TGGATCAGCGCTTATAAT GGTAACACAAAGTATGC ACAGAAGCTCCAGGGC | SEQ ID NO:24072 CACGATTTTTGGAGTGGTTA TTATAAGGGTATGGACGTC |
| iPS:451106 | 21-225_49C5 | AA | SEQ ID NO:8049 SYGIS | SEQ ID NO:16061 WISAYNGNTKYAQKLQG | SEQ ID NO:24073 HDFWSGYYKGMDV |
| | 21-225_49D10 | NA | SEQ ID NO:8050 AGCTATGGTATCAGC | SEQ ID NO:16062 TGGATCAGCGCTTATAAT GGTAACACAAAGAATGC ACAGAAGCTCCAGGGC | SEQ ID NO:24074 CACGATTTTTGGAGTGGTTA TTATAAGGGTATGGACGTC |
| | | AA | SEQ ID NO:8051 SYGIS | SEQ ID NO:16063 WISAYNGNTKNAQKLQG | SEQ ID NO:24075 HDFWSGYYKGMDV |
| iPS:451108 | 21-225_53E8 | NA | SEQ ID NO:8052 AGCTATGGTATCAGC | SEQ ID NO:16064 TGGATCAGCGCTTATAAT GGTAACACAAAGTTGC ACAGAAGCTCCAGGGC | SEQ ID NO:24076 CACGATTTTTGGAGTGGTTA TTATAAGGGTATGGACGTC |
| | | AA | SEQ ID NO:8053 SYGIS | SEQ ID NO:16065 WISAYNGNTKFAQKLQG | SEQ ID NO:24077 HDFWSGYYKGMDV |
| | | | SEQ ID NO:8054 | SEQ ID NO:16066 | SEQ ID NO:24078 |

FIGURE 49
(Continued)

| | | | | | |
|---|---|---|---|---|---|
| iPS:451110 | 21-225_74C9 | NA | AGCTATGGCATGCAC | GTTATATGGTATGATGG AATAATAAATCCTATG CAGACTCCGTGAAGGGC | GATCGAGATTATTGTAGTAG TACCAGCTGCCCTATTATTA CTACTACGGTATGGACGTC |
| | | | SEQ ID NO:8055 | SEQ ID NO:16067 | SEQ ID NO:24079 |
| | | AA | SYGMH | VIWYDGNNKSYADSVKG | DRDYCSSTSCPYYYYGMDV |
| | | | SEQ ID NO:8056 | SEQ ID NO:16068 | SEQ ID NO:24080 |
| iPS:451112 | 21-225_53D10 | NA | GGCTACTATATACAC | TGGATCAACCCTAACAG TGGTGGCACAAACTATG CACAGAAGTTTCAGGGC | GAAAACGAAAGTCTAGCAAC TCGTCCTTTCTACGACTACTA CGGTATGGACGTC |
| | | | SEQ ID NO:8057 | SEQ ID NO:16069 | SEQ ID NO:24081 |
| | | AA | GYYIH | WINPNSGGTNYAQKFQG | ENESLATRPFYDYYGMDV |
| | | | SEQ ID NO:8058 | SEQ ID NO:16070 | SEQ ID NO:24082 |
| iPS:451114 | 21-225_159A3 | NA | GACTATGTCATGCAG | GTTATATGGTATGATGG AAGTAATAAATACTATG CAGACTCCGTGAAGGGC | GAACCGTATAATAGTGGCTG GTACGACTACGGTATGGACG TC |
| | | | SEQ ID NO:8059 | SEQ ID NO:16071 | SEQ ID NO:24083 |
| | | AA | DYVMQ | VIWYDGSNKYYADSVKG | EPYNSGWYDYGMDV |
| | | | SEQ ID NO:8060 | SEQ ID NO:16072 | SEQ ID NO:24084 |
| iPS:451116 | 21-225_164A4 | NA | AATTATGATATCAAC | TGGATGCACCTAACAG TGGTAACACAGGCTATG CACAGAAGTTCCAGGGC | AGCAGTGGCTGGTACTTCTT TGACTAC |
| | | | SEQ ID NO:8061 | SEQ ID NO:16073 | SEQ ID NO:24085 |
| | | AA | NYDIN | WMHPNSGNTGYAQKFQG | SSGWYFFDY |
| | | | SEQ ID NO:8062 | SEQ ID NO:16074 | SEQ ID NO:24086 |

FIGURE 49
(Continued)

| | | | | | |
|---|---|---|---|---|---|
| iPS:451118 | 21-225_191C8 | NA | AGTGGTGGTTACTACTGGAG C | TATATCTATTATACAGTGGG ACCACCATTACAACCC TCCCTCAAGAGT | GACACGTTTGCTTTGATGG TTGTGGTTATTCTTTGACTC C |
| | | | SEQ ID NO:8063 | SEQ ID NO:16075 | SEQ ID NO:24087 |
| | | AA | SGGYYWS | YIYYSGTTIYNPSLKS | DTFCFDGCGYFFDS |
| | | | SEQ ID NO:8064 | SEQ ID NO:16076 | SEQ ID NO:24088 |
| iPS:451120 | 21-225_197D3 | NA | AGCCATGGCATGCAC | GTTATATGTAATGAACACTATG CAGACTCCGTGAAGGGC | GATCAAGGTGTGGGGTACTA CGGTATGGACGTC |
| | | | SEQ ID NO:8065 | SEQ ID NO:16077 | SEQ ID NO:24089 |
| | | AA | SHGMH | VIWYDGSNEHYADSVKG | DQGVGYYGMDV |
| | | | SEQ ID NO:8066 | SEQ ID NO:16078 | SEQ ID NO:24090 |
| iPS:451122 | 21-225_200A1 | NA | GTTTACTATTGGAGC | GAAATCAATCATAGTGG AAGCACCAACTACAACC CGTCCCTCAAGAGT | GACTACGGTGTCTTTGACTA C |
| | | | SEQ ID NO:8067 | SEQ ID NO:16079 | SEQ ID NO:24091 |
| | | AA | VYYWS | EINHSGSTNYNPSLKS | DYGVFDY |
| | | | SEQ ID NO:8068 | SEQ ID NO:16080 | SEQ ID NO:24092 |
| iPS:451124 | 21-225_74F6 | NA | AATTATGATATCAAC | TGGATGCACCCTAACAG TGGTAACACAGGCTATG CACAGAAGTTCCAGGGC | AGCAGTGGCTGGTACTTTTT TGACTAC |
| | | | SEQ ID NO:8069 | SEQ ID NO:16081 | SEQ ID NO:24093 |
| | | AA | NYDIN | WMHPNSGNTGYAQKFQG | SSGWYFFDY |
| | | | SEQ ID NO:8070 | SEQ ID NO:16082 | SEQ ID NO:24094 |
| iPS:451127 | | NA | AATTATGATGTCAAC | TGGATGCACCCTAACAG TGGTAACACAGGCTATG CACAGAAGTTCCAGGGC | AGCAGTGGCTGGTACCTCTT T |

FIGURE 49
(Continued)

| | | | | | | SEQ ID NO:16083 WMHPNSGNTGYAQKFQG | SEQ ID NO:24095 SSGWYLFDY |
|---|---|---|---|---|---|---|---|
| iPS:451129 | 21-225_164A7 | AA | SEQ ID NO:8071 NYDVN | | | | |
| | | NA | SEQ ID NO:8072 AATTATGATATCAAC | | | SEQ ID NO:16084 TGGATGCACCCTAACAG TGGTAACACAGGCTTTG CACAGAAGTTCCAGGGC | SEQ ID NO:24096 TCCAGTGGCTGGTACTGGTT CGACCCC |
| iPS:451131 | 21-225_94D2 | AA | SEQ ID NO:8073 NYDIN | | | SEQ ID NO:16085 WMHPHSGNTGFAQKFQG | SEQ ID NO:24097 SSGWYWFDP |
| | | NA | SEQ ID NO:8074 AATTATGATATCAAC | | | SEQ ID NO:16086 TGGATGCACCCTCACAG TGGTAACACAGGCTATG CACAGAAGTTCCAGGGC | SEQ ID NO:24098 AGCAGTGGCTGGTACTACTT TGACTAC |
| iPS:451133 | 21-225_160A7 | AA | SEQ ID NO:8075 NYDIN | | | SEQ ID NO:16087 WMHPSGNTGFAQKFQG | SEQ ID NO:24099 SSGWYYFDY |
| | | NA | SEQ ID NO:8076 AATTATGATATCAAC | | | SEQ ID NO:16088 TGGATGAACCCTAACAG TGGTAACACAGGCTATG CACAGAAGTTCCAGGGC | SEQ ID NO:24100 TCCAGTGGCTGGAACTGGTT CGACCCC |
| iPS:451133 | 21-225_95H4 | AA | SEQ ID NO:8077 NYDIN | | | SEQ ID NO:16089 WMNPNSGNTGYAQKFQG | SEQ ID NO:24101 SSGWNWFDP |
| | | NA | SEQ ID NO:8078 AGTTATGATATCAAC | | | SEQ ID NO:16090 TGGCTGAACCCTCACAG TGGTAACACAGGCTATG CACAGAAGTTCCAGGGC | SEQ ID NO:24102 GGGTTTACGATATTTGACT GGTTATTCCCCACCTACTA CTACTACGATATGGACGTC |
| iPS:437240 | 21-225_84H12 | | SEQ ID NO:8079 | | | SEQ ID NO:16091 | SEQ ID NO:24103 |

FIGURE 49
(Continued)

| | | AA | SYDIN | WLNPHSGNTGYAQKFQG | GFYDILTGYSPTYYYYDMDV |
|---|---|---|---|---|---|
| iPS:434577 | 21-225_75C11 | | SEQ ID NO:8080 | SEQ ID NO:16092 | SEQ ID NO:24104 |
| | | NA | AGTTATGATATCAAC | TGGCTGAACCCTCACAGTGGTAACACAGGCTATGCACAGAAGTTCCAGGGC | GGGTTTACGATATTTGACTGGTTATTCCCCACTACTACTACTACGATATGGACGTC |
| iPS:435477 | 21-225_154E8 | AA | SYDIN | WLNPHSGNTGYAQKFQG | GFYDILTGYSPTYYYYDMDV |
| | | | SEQ ID NO:8081 | SEQ ID NO:16093 | SEQ ID NO:24105 |
| | | NA | AGTTATGCCATGAGC | GCTATTAGTGGTAGTGGTGGTAACACATTCTACGCAGACTCCGTGAAGGGC | CACGGTATAGCAGTGGCTGGTACTGGGGCTCACTACTTTGACTAC |
| | | | SEQ ID NO:8082 | SEQ ID NO:16094 | SEQ ID NO:24106 |
| | | AA | SYAMS | AISGSGGNTFYADSVKG | HGIAVAGTGAHYFDY |
| | | | SEQ ID NO:8083 | SEQ ID NO:16095 | SEQ ID NO:24107 |
| iPS:434553 | 21-225_76H12 | NA | AGTTATGATATCAAC | TGGCTGAACCCTCACAGTGGTAACACAGGCTATGCACAGAAGTTCCAGGGC | GGGTTTACGATATTTGACTGGTTATTCCCCACTACTACTACTACGATATGGACGTC |
| | | | SEQ ID NO:8084 | SEQ ID NO:16096 | SEQ ID NO:24108 |
| | | AA | SYDIN | WLNPHSGNTGYAQKFQG | GFYDILTGYSPTYYYYDMDV |
| iPS:434927 | 21-225_86E5 | | SEQ ID NO:8085 | SEQ ID NO:16097 | SEQ ID NO:24109 |
| | | NA | AGTTATGATATCAAC | TGGATGAACCCTAACAGTGGTAACACAGGCTATGCACAGAAGTTCCAGGGC | GGGTTTACGATATTTGACTGGTTATTCCCCACTACTACTACTACGATATGGACGTC |
| | | | SEQ ID NO:8086 | SEQ ID NO:16098 | SEQ ID NO:24110 |
| | | | SEQ ID NO:8087 | SEQ ID NO:16099 | SEQ ID NO:24111 |

FIGURE 49
(Continued)

| | | AA | SYDIN | | WMNPNSGNTGYAQKFQG | GFYDILTGYSPTYYYDMDV |
|---|---|---|---|---|---|---|
| | | | SEQ ID NO:8088 | | SEQ ID NO:16100 | SEQ ID NO:24112 |
| iPS:435385 | 21-225_149G7 | NA | AGCTATGCCATGAGC | | GCTATTAGTGGTAGTGGT GGTAACACATTCTACGC AGACTCCGTGAAGGGC | CACGGTATAGCAGTGGCTGG TACTGGGGCTCACTACTTTG ACTAC |
| | | | SEQ ID NO:8089 | | SEQ ID NO:16101 | SEQ ID NO:24113 |
| | | AA | SYAMS | | AISGSGGNTFYADSVKG | HGIAVAGTGAHYFDY |
| | | | SEQ ID NO:8090 | | SEQ ID NO:16102 | SEQ ID NO:24114 |

FIGURE 50

Table 3
Standard IgG Antibody Variable Region Sequences

| IPS# | Ab | Type | LC V-region | HC V-region |
|---|---|---|---|---|
| iPS:451135 | 21-225_64A11 | NA | GACATCCAGATGACCCAGTCTCCATTCTCCT GTCTGCATCTGTAGGCGACAGAGTCACCATCA CTTGCCGGGCAAGTCGGAGCGTTAGCAGATAT TTAAATTGGTATCAGCAGAAACTGGGAAAGC CCTTAAGCTCTTGATATCTGTGCATCCCGTTT GCAAAGTGGGGTCCCATCGAGGTTCAGTGGCA GTGGATCTGGGACAGATTTCACTCTCACCATC AGCAGTCTGCAACAGTGAAGATTTTGCAACTTA CTTCTGTCAACAGAGTGACAGTTTCCCTCTCAC TTTCGGCGGAGGGACCAAGGTGGAGATCAAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGCT GGAGTGGGTGGCAGTTATATCATATGTTGAAGT AATAAATACTATGCAGACTCCGTGAAGGGCCGA TTCACCATCTCCAGAGACAATTCCAAGAACACGC TGTATCTGCAAATGAACACCCTGAGAGCTGAGG ACACGGCTGTGTATTACTGTGCGAGAGAGGAG CAGTGGCTCCGTACTACGGTATGGACGTCTGGGG CCAAGGGACCACGGTCACCGTCTCCTCA |
| | | | SEQ ID NO: 24115 | SEQ ID NO: 28121 |
| | | AA | DIQMTQSPFSLSASVGDRVTITCRASRSVSRYLN WYQQTLGKALKLLISVASRLQSGVPSRFSGSGSG TDFTLTISSVQREDFATYFCQQSDSFPLTFGGGTK VEIK | QVQLVESGGGVVQPGRSLRLSCAASGFTFSNYGM HWVRQAPGKGLEWVAVISYVGSNKYYADSVKGR FTISRDNSKNTLYLQMNTLRAEDTAVYYCARRGAV APYYGMDVWGQGTTVTVSS |
| | | | SEQ ID NO: 24116 | SEQ ID NO: 28122 |

FIGURE 50
(Continued)

| | | | |
|---|---|---|---|
| iPS:451141 | 21-225_164B11 | NA | GACATCGTGATGACCCAGTCTCCAGACTCCCTGGCTGTGTCTCTGGGCGAGAGGGCCACCATCAACTGCAAGTCCAGCCAGAGTCTTTAAAGAGCTCCAACAATAAGAGCTACTTAGCTTCGTACCAGCAGAAGCCAGGACAGTTCCCGGGAATCCGGGTCTTTACTGGCATCTCCCGGGAATCCGGGGTCCCTGACCGATTCAGTGGCAGCGGGTCTGGGACAGATTTCACTCTCACCATCAGCAGCCTGCAGGCTGAAGATGTGGCACTTTATTACTGTCAGCAATATTATAGTATTCCTCCCACTTTCGGCCATGGGACCAATGTGGATATCACG<br/><br/>SEQ ID NO: 24117 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGACCCTAACAGTGGTAACACAGGCTATGCACAGAAGTTCCAGGCAGAGTCACCATGACCAGGAACACTTCCATGAGCACCGCCTACATGGAGCTGAGCAGCCTGAGATCTGAGGACTCGGCCGTGTATTACTGTTCCTATAGCAGTGGCTGGTACATGTTTGACTACTGGGGCCAGGGAACCCTGGTCACCGTCTCCTCA<br/><br/>SEQ ID NO: 28123 |
| | | AA | DIVMTQSPDSLAVSLGERATINCKSSQSLLKSSNNKSYLASYQQKPGQLPKLLIYWASSRESGVPDRFSGSGSGTDFLTISSLQAEDVALYYCQQYYSIPPTFGHGTNVDIT<br/><br/>SEQ ID NO: 24118 | QVQLVQSGAEVKKPGASVKVSCKASGYTFTNYDINWVRQATGQGLEWMGWMTPNSGNTGYAQKFQGRVTMTRNTSMSTAYMELSSLRSEDSAVYYCSYSSGWYMFDYWGQGTLVTVSS<br/><br/>SEQ ID NO: 28124 |
| iPS:451137 | 21-225_74A7 | NA | GACATCGTTATGACCCAGTCTCCAGACTCCCTGGCTGTGTCTCTGGGCGAGAGGGCCACCATCAACTGCAAGTCCAGCCAGAGTGTTTATTCAGCTCCAACAATTATAACTACTTAGCTTGGTACCAGCAGAGACCAGGACAGCCTCCTAACCTGCTCATTTACTGGGCATCTACCCGGGAGAGTGGGGTCCCTGACCGATTCAGTGGCAGCGGGTCTGGGACAGATTTCACTCTCACCATCAGCAGCCTGCAGGCTGCTGATGTGGCAGTTTATTACTGTCAGCAATATCATAGTTCTCCTCCGACGTTCGGCCAAGGGACCACGGTGCAAATCAAA<br/><br/>SEQ ID NO: 24119 | CAGGTGCAGTTGGTGCAGTCTGGGGCTGAGGTGAAGAAGCCTGGGGCCTCAGTGAAGGTCTCTGCAAGGCTTCTGGATACACCTTCACCAATTATGATATCAACTGGGTGCGACAGGCCACTGGACAAGGGCTTGAGTGGATGGGATGAACCCTAACAGGTAACACAGGCTATGCACAGAAGTTCCAGGGCAGAGTCACCATGACCAGGAACACCTCCACAAGCACAGCCCACATGGAGCTGAGCAGCCTGAGATCTGAGGACACGGCCGTGTATTACTGTGCGGTCTCCAGTGGCACGGCCGGTTCGACCCCTGGGGCCAGGGAACCCTGGTCACCGTCTCCTCA<br/><br/>SEQ ID NO: 28125 |

FIGURE 50
(Continued)

| | | | |
|---|---|---|---|
| iPS:451139 | 21-225_71A6 | AA | DIVMTQSPDSLAVSLGERATINCKSSQSVLFSSN NYNYLAWYQQRPGQPPNLLIYWASTRESGVPD RFSGSGSGTDFTLTISSLQAADVAVYYCQQYHSS PPTFGQGTTVQIK<br>SEQ ID NO: 24120 | QVQLVQSGAEVKKPGASVKVSCKASGYTFTNYDIN WVRQATGQGLEWMGWMNPNSGNTGYAQKFQGR VTMTRNTSTSTAHMELSSLRSEDTAVYYCAVSSGW NWFDPWGQGTLVTVSS<br>SEQ ID NO: 28126 |
| | | NA | GATATTGTGATGACCCAGACTCCACTCTCTCTC TCTGTCACACCTGGACAGCCGGCCTCCATCTC CTGCAAGTCTAGTCAGAGCCTCTGCGTAGTG ATGGAAAGACCCATTTGTATTGGTACCTGCAG AAGCCAGGCCAGCCTCCACAGCTCTAATCTA TGAAGTTTCCAACGGTTCTCTGGAGTGTCAG ATAGGTTCAGTGCAGGGTCAGGGACAGA TTTCACACTGAAAATCAGCCGGGTGGAGGCTG AGGATGTTGGGGTTTATTACTGCATGCAAAGT AAACAGCTTCCTCTCACTTTCGGCGGAGGGAC CAAGGTGGAGTTCAAA<br>SEQ ID NO: 24121 | CAGGTGCAACTGGTGGAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGGCT GGAGTGGGTGGCAGTTATATCATATGATGGAAGT AATGAATACTATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGCGAGAGATCACAG ATATGGGGTTCGGGGAGGCTTTGACTACTGGGGC CAGGGAACCCTGGTCACCGTCTCCTCA<br>SEQ ID NO: 28127 |
| | | AA | DIVMTQTPLSLSVTPGQPASISCKSSQSLLRSDGK THLYWYLQKPGQPPQLLIYEVSNRFSGVSDRFSG SGSGTDFTLKISRVEAEDVGVYYCMQSKQLPLT FGGGTKVEFK<br>SEQ ID NO: 24122 | QVQLVESGGGVVQPGRSLRLSCAASGFTFSNYGM HWVRQAPGKGLEWVAVISYDGSNEYYADSVKGRF TISRDNSKNTLYLQMNSLRAEDTAVYYCARDHRY GVRGGFDYWGQGTLVTSS<br>SEQ ID NO: 28128 |

FIGURE 50
(Continued)

| | | | | |
|---|---|---|---|---|
| iPS:451143 | 21-225_66H11 | NA | GACATCCAGATGACCCAGTTTCCATCCTCACT GTTTGCATTTGTAGGAGACAGAGTCACCATCA CTTGTCCGGCAGTCAGGGCATTAGCAATTAT TTAGCTTGGTTTCAGCAGAAACCAGGAAAGC CCCTAAGTCCCTATTTATGTGCATTCAATTT GCACAGTGGGGTCCCATCAAAGTTCAGCGGCA GTGGATTTGGGACAGATTTCACTCTCACCATC AACAGCCTGCAGCCAACAGTATGTTGTTACCCATTCAC TTTCGGCCATGGGACCAAAGTGGATATCAAA | CAGGTTCAGCTGGTCAGTCTGGAGCTGAGGTGA AGAAGCCTGGGGCCTCAGTGAAGGTCTCCTGCA AGGCTTCTGGTTACACCTTTGCCACCTATGTAT CAGCTGGGTGCGACAGGCCCCTGGACAGGGCT TGAGTGGATGGGATGGATCAGCGTTACAATGGT AACACAAACTATGCACAGAAGTCCAGGGCAGA GTCACCATGACCACAGACACATCCACGAGCACA GCCTACATGGAGCTGAGGAGCCTGAGATCGAC GACACGGCCGTGTATTACTGTGCGAGAGGGAA GCAGTGGCGTCGTCTTCGACCCCTGGGGCCAGGGAA CCCTGGTCACCGTCTCCTCA |
| | | | SEQ ID NO: 24123 | SEQ ID NO: 28129 |
| | | AA | DIQMTQFPSSLFAFVGDRVTITCPASQGISNYLA WFQQKPGKAPKSLIYGAFNLHSGVPSKFSGSGF GTDFTLTINSLQPEDFANYYCQQYSCYPFTFGHG TKVDIK | QVQLVQSGAEVKKPGASVKVSCKASGYTFATYGIS WVRQAPGQGLEWMGWISAYNGNTNYAQKLQGR VTMTDTSTSTAYMELRSLRSDDTAVYYCARGEA VAVFDPWGQGTLVTVSS |
| | | | SEQ ID NO: 24124 | SEQ ID NO: 28130 |
| iPS:453445 | 21-225_148E10 | NA | TCCTATGAGCTGACTCAGCCACCTCAGTGTC CGTGTCCCCAGGACAGACAGCCAGCATCACCT GCTCTGGAGATAAATTGGGTAATAAATATGTT TGTTGGTATCAGCAGAGGCCAGGCCATGCTGC TGTGCTGATCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGATGAGGCTGACTATT TCTGTCAGGCGTGGGACACAGAACACTTATGTG GTGTTCGGCGGAGGGACCAAGCTGACCGTCCT A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTGGCAT GCACTGGGTCCGCCAGGCTCCAGGCAAGGGCT GGAGTGGGTGGCAGTTATATAGACTCCGTGGAAGTGCAGT AATAAATACTATGTAGACTCCGTGAAGGACCGAT TCACCATCTCCAGAGACAATTCCAAGAACACGCT GTATCTGCAAATGAACAGCCTGAGAGCCGAGGA CACGGCTGTTATTACTGTGCGAGAGATCGGGTG GAGGGTTCGGGGACTCCTACTACTACTACGGTA TGGACGTCTGGGGCCAAGGGACCACGGTCACCG TCTCCTCA |
| | | | SEQ ID NO: 24125 | SEQ ID NO: 28131 |

FIGURE 50
(Continued)

| | | | |
|---|---|---|---|
| iPS:453447 | 21-225_65F10 | AA | SYELTQPPSVSVSPGQTASITCSGDKLGNKYVCW YQQRPGHAAVLIIYQDSKRPSGIPERFSGSNSGNT ATLTISGTQAMDEADYFCQAWDRNTYVFGGG TKLTVL<br>SEQ ID NO: 24126 | QVQLVESGGGVVQPGRSLRLSCAASGFTFSSYGMH WVRQAPGKGLEWVAVIWFDGSNKYYVDSVKDRF TISRDNSKNTLYLQMNSLRAEDTAVYYCARDRVEG SGTPYYYYGMDVWGQGTTVTSS<br>SEQ ID NO: 28132 |
| | | NA | GACATCCAGATGACCCAGTCTCCATCTTCCGT GTCTGCATCTGTAGGAGACAGAGTCACCATCA CTTGTCGGGGGGGTCAGGTATTAGCACATGG TTAGCATGGTATCAGCAGAAACCAGGGAAAG CCCCTAAGCTCCTGATCTATGCTGCATCCATTT TGCAAAGTGGGGTCCCATCAAGGTTCAGAGGC AGGGGATCTGGGACAGATTTCACTCTCACCAT CAGCAGCCTGCAGCCTGAAGATTTTGCAACTT ATTATTGTCAACAGGGTAACATTTTCCCATTCA CTTTCGGCCGAGGGACCAAAGTGGATATCAAA<br>SEQ ID NO: 24127 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACCATA TGCACTGGGTGCGACAGGCCCCTGGACAAGGGC TTGAGTGGATGGGATGGATCAACCCTAACAATGG TGGCACAAGCTATGCACAGAAGTTTCAGGACAG GGTCACAATGACCAGGGACACGTCCATCAGCAC AGCCTACATGGAGCTGAGCAGGCTGAGATCTGA CGACACGGCCGTGTACTACTGTGCGAGAGATAGT AGGTCGTCCTGGGACTACTGGGGCCAGGGAACC CTGGTCACCGTCTCCTCA<br>SEQ ID NO: 28133 |
| | | AA | DIQMTQSPSSVSASVGDRVTITCRGGQGISTWLA WYQQKPGKAPKLLIYAASILQSGVPSRFRGRGS GTDFTLTISSLQPEDFATYYCQQGNIFPFTFGRGT KVDIK<br>SEQ ID NO: 24128 | QVQLVQSGAEVKKPGASVKVSCKASGYTFTGYHM HWVRQAPGQGLEWMGWINPNNGGTSYAQKFQDR VNMTRDTSISTAYMELSRLRSDDTAVYYCARDSRS SWDYWGQGTLVTVSS<br>SEQ ID NO: 28134 |

FIGURE 50
(Continued)

| | | | |
|---|---|---|---|
| iPS:453449 | 21-225_208A2 | NA | GACATCCAGATGACCCAGTCTCCATCCTCCCT GTCTGCATCTGTAGGAGACAGAGTCACCATCA CTTGCCGGACAAGTCAGGGCATTAGAAATGAT TTAGGCTGGTATCAGCAGCAACCAGGGAAA CCCCTAAGCGCCTGATCTATGCTGCATCCAGT TTGCTTAGTGGGGTCCCATCAAGGTTCAGCGG CAGTAGATCTGGGACAGATTTCACTCTCACAA TCAGCAGCCTGCAGCCTGAAGATTTTGCAACT TATTACTGTCTACAGTATAATAGTTACCCTCCC ACCTTCGGCCAAGGGACACGACTGGAGATTAA A<br><br>SEQ ID NO: 24129 | CAGGTGCAGCTGCAGGAGTCGGGCCCAGGACTG GTGAAGCCTTCGGAGACCCTGTCCTCAACTGCA CTGTCTCTGGTGGCTCCATCAGGAGTTACTACTG GAGCTGGATCCGGCAGCCCGCCGGGAAGGGACT GGAGTGGATTGGGCGTATCTATACCAGTGGGAGC ACCGACTACAACCCCTCCCTCAAGAGTCGAATCA CCATGTCAGTAGACACGTCCAAGAACCAGTTCTC TTTGAAGCTGAGCTCTGTGACCGCCGCGGACACG GCCGTGTATTACTGTGCGAGAGAGGTTCGGTGACT GGGACTACTGGGGCCAGGGAACCCTGGTCACCG TCTCCTCA<br><br>SEQ ID NO: 28135 |
| | | AA | DIQMTQSPSSLSASVGDRVTITCRTSQGIRNDLG WYQQKPGKTPKRLIYAASSLSGVPSRFSGSRSG TDFTLTISSLQPEDFATYYCLQYNSYPPTFGQGT RLEIK<br><br>SEQ ID NO: 24130 | QVQLQESGPGLVKPSETLSLNCTVSGGSIRSYYWS WIRQPAGKGLEWIGRIYTSGSTDYNPSLKSRITMSV DTSKNQFSLKLSSVTAADTAVYYCARGFGDWDYW GQGTLVTVSS<br><br>SEQ ID NO: 28136 |
| iPS:453451 | 21-225_52G11 | NA | GACATCCAGATGACCCAGTCTCCATCTTCCGT GTCTGCATCTGTAGGAGACAGAGTCACCATCA CTTGTCGGGCGAGTCAGGGTATTAGCAAATGG TTAGCCTGGTATCAGCAGAGAACCAGGGAAAG CCCCTAAGCTCCCTGATCTCTATGCTGCATCCAGTT TGCAAAGTGGGGTCCCATCAAGATTCAGCGCC AGTGGATCTGGGACAGGATTTCACTCTCACCAT CAGCAGTTTGCAGCCTGAAGATTTTGCAACTT ACTATTGTCAACAGGCTAACAGTTTCCCATTC ACTTTCGGCCCTGGGACCAAAGTGGATGTCAA A<br><br>SEQ ID NO: 24131 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATT TGCACTGGGTGCGACAGGCCCCTGGACAAGGGC TTGAGTGGATGGGATGGATCAACCTAATAGAA ATGGCACAAACTATGCACAGGGACACGTCCATCACA GGGTCACCATGACCAGGGACACAGTTCAGGGCA CAGCCTTCATGGAGCTGAGCAGGCTGAGATCGA CGACACGCCGTGTATTACTGTGCGGAGAGACGGT ACCAGCAGTTTGACTACTGGGGCCAGGGAACC CTGGTCACCGTCTCCTCA<br><br>SEQ ID NO: 28137 |

FIGURE 50
(Continued)

| | | | |
|---|---|---|---|
| iPS:453453 | | AA | DIQMTQSPSSVSASVGDRVTITCRASQGISKWLA WYQQKPGKAPKLLLYAASSLQSGVPSRFSASGS GTDFTLTISSLQPEDFATYYCQQANSFPFTFGPGT KVDVK<br>SEQ ID NO: 24132 | QVQLVQSGAEVKKPGASVKVSCKASGYTFTGYYL HWVRQAPGQGLEWMGWINPNRNGTNYAQKFQGR VTMTRDTSISTAFMELSRLRSDDTAVYYCARDGTS SFDYWGQGTLVTVSS<br>SEQ ID NO: 28138 |
| | 21-225_53F2 | NA | GACATCCAGATGACCCAGTCTCCATCTTCCGT GTCTGCATCTGTAGGAGACAGAGTCACCATCA CTTGTCGGGCGAGTCAGGGTATTAGCAAGTGG TTAGCCTGGTATCAGCAGAAACCAGGGAAAG CCCCTAAGCTCCTCTATGCTGCATCCAGTT TGCAAAGTGGGGTCCCATCAAAATTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATGTCAA A<br>SEQ ID NO: 24133 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATT TGCACTGGGTGCGACAGGCCCCTGGACAAGGC TTGAGTGGATGGGATGGATCAACCCTAACAGAA ATGGCACAAACTATGCACAGGACACAGAA GGGTCACCATGACCAGGGACACGTCCATCAGCA CAGCCTACATGGAGCTGAGCAGACTGAAATCTG ACGACACGGCCGTGTATTACTGTGCGAGAGACG GTACCAGTAGCTTTGACTACTGGGGCCAGGGAAC CCTGGTCACCGTCTCCTCA<br>SEQ ID NO: 28139 |
| | | AA | DIQMTQSPSSVSASVGDRVTITCRASQGISKWLA WYQQKPGKAPNLLLYAASSLQSGVPSKFSGSGS GTDFTLTISSLQPEDFATYYCQQANSFPFTFGPGT KVDVK<br>SEQ ID NO: 24134 | QVQLVQSGAEVKKPGASVKVSCKASGYTFTGYYL HWVRQAPGQGLEWMGWINPNRNGTNYAQNFQGR VTMTRDTSISTAYMELSRLKSDDTAVYYCARDGTS SFDYWGQGTLVTVSS<br>SEQ ID NO: 28140 |

FIGURE 50
(Continued)

| | | | |
|---|---|---|---|
| iPS:468810 | 21-225_74D5 | NA | GAAATTGTGTTGACGCAGTCTCCAGGCACCCTGTCTTTGTCTCCAGGGGAGAGAGCCACCCTCCTGCAGGGCCAGTCAGAGTGTTAACAGCAACTACTTAGCCTGGTACCGGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCATTCTCATCATCAGCAGACTGGAGCCTGAGGATTTTGCAGTGTATTACTGTCAGCAGTATGAAAGCTCGCCGTGGACGTTCGGCCAAGGGACCAAGGTGGAAATCAAA SEQ ID NO: 24135 |
| | | AA | EIVLTQSPGTLSLSPGERATLSCRASQSVNSNYLAWYRQKPGQAPRLLIYGASSRATGIPDRFSGSGSGTDFTLTISRLEPEDFAVYYCQQYESSPWTFGQGTKVEIK SEQ ID NO: 24136 |
| | | NA | CAGGTGCAGCTACAACAGTGGGGCGCAGGACTGTTGAAGCCTTCGGAGACCCTGTCCCTCACTTGCGCTGTCAATGGTGGGCCCTTCAGCGGTTGCTACTGGAGCTGGATCCGCCAGCCCCCAGGGAAGGGGCTGGAGTGGATTGGGGAAATCAATTATAGTGGAAGGACCAACTTCAACCCGTCCCTCAAGAGTCGAGTCACCATATCAGTTGACACGTCCAAGAACCAGTTCTCCCTGAAGCTGAGCTCTGTGACCGCCGCGGACACGGCTGTGTATTACTGTGCGAGAGACTACGGCGGTATGGACGTCTGGGGCCAAGGGACCACGGTCACCGTCTCCTCA SEQ ID NO: 28141 |
| | | AA | QVQLQQWGAGLLKPSETLSLTCAVNGGPFSGCYWSWIRQPPGKGLEWIGEINYSGRTNFNPSLKSRVTISVDTSKNQFSLKLSSVTAADTAVYYCARDYGGMDVWGQGTTVTVSS SEQ ID NO: 28142 |
| iPS:468812 | 21-225_48H4 | NA | GACATCCAGATGACCCAGTTTCCATCCTCCCTGTCTGCATCTGTAGGAGACAGAGTCACCATCACTTGCCGGGCAAGTCAGAGCATTAGAAATGATCTTGCCTGGTATCAGCAGAAACCAGGGAAAGCCCCTAAGCGCCTGATCTATGCTGCCAGTTTGCAAAGTGGGGTCCCATCAAGGTTCAGCGGCAGTGGATCTGGGACAGAATTCACTCTCACAACAGCAGCCTGCAGCCTGAAGATTTTGCAACTTATTACTGTCTACAACATTATAGTTACCCGCTCACTTTCGGCGGAGGGACCAAGGTGGAGATCAAA SEQ ID NO: 24137 |
| | | NA | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTCTCATGCACTGGGTCCGCCAGGCTCCAGGCAAGGGGCTGGAGTGGGTGGCAGTTATATATGGTATGATGAAGTAATAAATACTATACAGACTCCGTTAAGGGCCGATTCACCATCTCCAGAGACAATGCCAAGAACACGCTGTATCTGCAAATGAACAGCCTGAGAGCCGAGGACACGGCTGTGTATTACTGTGCGAGAAAACTATAGCAGTGGCTGGTACGGGTACGGTATGGACGTCTGGGGCCAAGGGACCACGGTCACCGTCTCCTCA SEQ ID NO: 28143 |

FIGURE 50
(Continued)

| | | | |
|---|---|---|---|
| iPS:468816 | 21-225_52G8 | AA | DIQMTQFPSSLSASVGDRVTITCRASRDIRNDLG WYQQKPGKAPKRLIYAASSLQSGVPSRFSGSGS GTEFTLTISSLQPEDFATYYCLQHYSYPLTFGGG TKVEIK |
| | | | SEQ ID NO: 24138 |
| | | | QVQLVESGGGVVQPGRSLRLSCAASGFTFSDSLMH WVRQAPGKGLEWVAVIWYDGSNKYYTDSVKGRF TISRDNSKNTLYLQMNSLRAEDTAVYYCARENYSS GWYGYGMDVWGQGTTVTVSS |
| | | | SEQ ID NO: 28144 |
| | | NA | GATATTGTGATGACCCAGACTCCACTCTCTCT GTCCGTCACCCCTGGACAGCCGGCCTCCATGT CCTGCAAGTCTAGTCAGAGCCTCCTGCATAGT GAAGGAAAGACCTATTTGTATTGGTACCTGCA GAAGACAGGCCAGCTCCACACCTCCTGATCT ATGAAGTTTCCAAGCGGTTCTCTGGCCGTGCA GATAGGTTCAGTGGCAGCGGGTCAGGGACAG ATTTCACACTGAAAATCAGCCGGATGGAGGCT GAGGATGTTGGGGTTTATTACTGCATGCAAAG TATGCAGCTTCCGATTATCTTCGGCCAGGGGA CACGACTGGAGATTAAA |
| | | | SEQ ID NO: 24139 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTCTGTATTACTGTGCGAGAAGGTATAG CAGCAGCTGGTGTCGGGCGGTATGGACGTCTGGGG CCAAGGGACCACGGTCACCGTCTCCTCA |
| | | | SEQ ID NO: 28145 |
| | | AA | DIVMTQTPLSLSVTPGQPASMSCKSSQSLLHSEG KTYLYWYLQKTGQPPHLLIYEVSKRLSGVPDRF SGSGSGTDFTLKISRMEAEDVGVYYCMQSMQLP IIFGQGTRLEIK |
| | | | SEQ ID NO: 24140 |
| | | | QVQLVESGGGVVQPGRSLRLSCAASGFTFSSYGMH WVRQAPGKGLEWVAVIWYDGSNKYYADSVKGRF TISRDNSKNTLYLQMNSLRAEDTALYYCARRYSSS WSGGMDVWGQGTTVTVSS |
| | | | SEQ ID NO: 28146 |

FIGURE 50
(Continued)

| | | | |
|---|---|---|---|
| iPS:468814 | 21-225_223D11 | NA | GACATCCAGATGACCCAGTCTCCCTCCTCACT GTCTGCATCTGTAGGAGACAGAGTCACCATCA CTTGTGGGCGAGTCAGGGATTAGCAGTATTAT TTAGCCTGGTTTCAGCAGAAACCAGGAAAGC CCCTAAGTCCCTGATCTATGCTGCATCCACTTT GCAAAGTGGGGTCCCATCAAAGTTCAGCGGCA GTAGATCTGGGACAGATTTAATCTCACCATC AGCAACCTGCAGCCTGAAGATTTTGCAACTTA TTACTGCCAACAGTATAGTGGTTACCATTCA CTTTCGGCCCTGGGACCAAAGTGGATACCAAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAACTATGGCAT GGACTGGGTCCGCCAGGCTCCAGGCAAGGGCT GGAGTGGGTGGCAGTTATATGGTATGAAGT AATGACTACTATGCAGACTCCGTGAAGGGCCGAT TCACCATCTCCAGAGACAACAATTCCAAGAACACGCT GTTTCTGCAAATGAACAGCCTGAGAGCCGAGA CACGGCTGTGTATTACTGTGCGAGAGATCGGGGG ATCGGGTACAACGATATGGACGTCTGGGGCCAA GGGACCACGGTCACCGTCTCCTCA |
| | | | SEQ ID NO: 24141 | SEQ ID NO: 28147 |
| | | AA | DIQMTQSPSSLSASVGDRVTITCRASQGISNYLA WFQQKPGKAPKSLIYAASTLQSGVPSKFSGSRSG TDFNLTISNLQPEDFATYYCQQYSGYPFTFGPGT KVDTK | QVQLVESGGGVVQPGRSLRLSCAASGFTFSNYGM DWVRQAPGKGLEWVAVIWYDGSNDYYADSVKGR FTISRDNSKNTLFLQMNSLRAEDTAVYYCARDRGI GYNDMDVWGQGTTVTVSS |
| | | | SEQ ID NO: 24142 | SEQ ID NO: 28148 |
| iPS:468822 | 21-225_147E10 | NA | GCTATTGTGATGACCCAGACTCCACTCTCTCTG TCCGTCACCCCTGGACAGCCGGCCTCCATCTC CTGCAAGTCTAGTCAGGGCCTCCTGCATGGTG ATGGAAAGACCTATTTGTATTGGTACCTGCAG AAGCCAGGCCAGCCTCCACACCTCCTGATCTC TGAAGTTTCCAACCGGTTCTCTGGAGTGCCAG ATAGGTTCAGTGGCAGCGGGTCAGGGACAGA TTTCACACTGAAAATCAGCCGGGTGGAGGCTG AGGATGTTGGGGTTTATTACTGCATGCAAAGT ATACAGGTTCCGTGACGTTCGGCCAAGGGAC CAAGGTGGAAATCAAA | CAGGTGCAGCTGGTGGAGTCTGGGGGAGGCGTG GTCCAGCCTGGGAAGTCCCTGAGACTCTCCTGTG CTGCCTCTGGATTCACCTTCAGTAACTATGGCTT ACACTGGGTCCGCCAGGCTCCAGGCAAGGGGCT GGAGTGGGTGGCAATTATATGGTATGATGAAGT AATAAATACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGATCATTA CGATTTTTGGAGTGGTCACTTTGACTACTGGGGC CAGGGAACCCTGGTCACCGTCTCCTCA |
| | | | SEQ ID NO: 24143 | SEQ ID NO: 28149 |

FIGURE 50
(Continued)

| | | | |
|---|---|---|---|
| | | AA | AIVMTQTPLSLSVTPGQPASISCKSSQRLLHGDG KTYLYWYLQKPGQPPHLLISEVSNRFSGVPDRFS GSGSGTDFTLKISRVEAEDVGVYCMQSIQVPW TFGQGTKVEIK<br>SEQ ID NO: 24144 | QVQLVESGGGVVQPGKSLRLSCAASGFTFSNYGLH WVRQAPGKGLEWVAIIWYDGSNKYYADSVKGRFT ISRDNSKNTLYLQMNSLRAEDTAVYYCARDHYDF WSGHFDYWGQGTLVTVSS<br>SEQ ID NO: 28150 |
| iPS:468824 | 21-225_73G6 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCGTCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24145 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGAAGTGGG GATGACTTCTGACTACTGGGGCCAGGGAACCCTG GTCACCGTCTCCTCA<br>SEQ ID NO: 28151 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24146 | QVQLVESGGGVVQPGRSLRLSCAASGFTFSSYGMH WVRQAPGKGLEWVAVIWYDVSNKYYGDSVKGRF TISRDNSKNTLYLQMNSLRAEDTAVYYCAREVGM TSDYWGQGTLVTVSS<br>SEQ ID NO: 28152 |

FIGURE 50
(Continued)

| | | | | |
|---|---|---|---|---|
| iPS:468818 | 21-225_190C8 | NA | GACATCCAGATGACCCAGTCTCCATCCTCCT GTCTGCATCTGTAGGAGACAGAGTCACCATCA CTTGCCGGGCAAGTCAGGACAGTCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACTT ATTACTGTCTACAGCATAATGATTACCCGTTC ACTTTCGGCGGAGGGACCAAGGTGGAGATCA AA | CAGGTGCAGCTGGTGCAGTCTGGGGCTGAGGTG AAGAAGCCTGGGGCCTCAGTGAAGGTCTCCTGC AAGGCTTCTGGATACACCTTCATCAGTTATGATA TCAACTGGGTGCGACAGGCCACTGGACAAGGGC TTGAGTGGATGGGATGGATGAACCCTAAAAGG GTAACACAGGCTATGCACAGAAGTTCCAGGGCA GAGTCACCATGACCAGGGACACCTCCATAAGCA CAGCCTACATGGAGCTGAGCAGCCTGAGATCTG AGGACACGGCCGTTTATTACTGTGCGAGAGGAG ACCCGTATAAACTGGAACTCCTACGCTATGGACGT CTGGGGCCAAGGGACCACGGTCACCGTCTCCTCA |
| | | | SEQ ID NO: 24147 | SEQ ID NO: 28153 |
| | | AA | DIQMTQSPSSLSASVGDRVTITCRASQGIRNDLG WYQQKPGKAPKRLIYAASSLQSGVPSRFSGSGS GTEFTLTISSLQPEDFETYYCLQHNDYPFTFGGG TKVEIK | QVQLVQSGAEVKKPGASVKVSCKASGYTFISYDIN WVRQATGQGLEWMGWMNPKRGNTGYAQKFQGR VTMTRDTSISTAYMELSSLRSEDTAVYYCARGDPY NWNSYAMDVWGQGATVTVSS |
| | | | SEQ ID NO: 24148 | SEQ ID NO: 28154 |
| iPS:468826 | 21-225_201C5 | NA | GACATCCAGATGACCCAGTCTCCATCCTCCCT GTCTGCATCTGTAGGAGACAGAGTCACCATCA CTTGCCGGGCAAGTCAGGACAGTCATTAGACATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACACAGCATTATAGTTCCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGCT GGAGTGGGTGGCAGTTATATGACTCCGTGAAGGGCCGAT AATAAATACTATGTAGACTCCGTGAAGGGCCGAT TCACCATCTCCAGAGACAATTCCAGGAACACGCT GTATCTGCAAATGAACAGCCTGAGAGCCGAGGA CACGGCTGTGTATTACTGTGCGAGAGAACGGTAT AGCAGTGGCTTGTACGACTACGGTATGGACGTCT GGGGCCAAGGGACCACGGTCACCGTCTCCTCA |
| | | | SEQ ID NO: 24149 | SEQ ID NO: 28155 |

FIGURE 50
(Continued)

| | | | |
|---|---|---|---|
| iPS:468828 | 21-225_162A10 | AA | DIQMTQSPSSLSASVGDRVTITCRASQGIRHDLG WYQQKPGKAPKRLIYAASSLQSGVPSRFSGSGS GTEFTLTISSLQPEDFATYYCLQHYSFPRTFGQGT KVEIK<br>SEQ ID NO: 24150 | QVQLVESGGGVVQPGRSLRLSCAASGFTFSDYVM HWVRQAPGKGLEWVAVIWYDGSNKYYVDSVKGR FTISRDNSRNTLYLQMNSLRAEDTAVYYCARERYS SGLYDYGMDVWGQGTTVTVSS<br>SEQ ID NO: 28156 |
| | | NA | GAAATAGTGATGACGCAGTCTCCAGCCACCCT GTCTGTGTCTCCAGGGGAAAGAGCCACCCTCT CCTGCAGGGCCAGTCAGAGTCTGTTAACAGCAAC TTAGCCTGGTACCAGCAGAAATCTGGCCAGGC TCCCAGGCTCCTCATCTTTGGTGCATCCACCAG GGCCACTGTTATCCCAGCCAGGATCAATGGCA GTGGGTCTGGGACAGAGTTCACTCTCACCATC AGCAGCCTGCGGTCTGAAGATTTTGCAGTTTA TTTCTGTCAGCAGTATAATGACTGGCCGTGCA GTTTTGGCCAGGGGACCAAGCTGGAGATCAAA<br>SEQ ID NO: 24151 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTAGTGTGCAT GCACTGGGTCCGCCAGGCTCCAGGCAAGGGGCT GGAATGGGTGGCAGTATATGGTATGATGGAAG CAATAAATACTACTCCAGAGACTCCGTGAAGGGCCG ATTCACCATCTCCAGAGACAATTCCAAGAACACG CTGTTTCTGCAAATGAACAGCCTGAGAGCCGAGG ACACGGCTGTGTATTACTGTGCGAGAGACAAAA ATATAATGGAGATACTTGGTTTGACTTCTGGGG CCAGGGAACCCTGGTCACCGTCTCCTCA<br>SEQ ID NO: 28157 |
| | | AA | EIVMTQSPATLSVSPGERATLSCRASQTVNSNLA WYQQKSGQAPRLLIFGASTRATVIPARINGSGSG TEFTLTISSLRSEDFAVYFCQQYNDWPCSFGQGT KLEIK<br>SEQ ID NO: 24152 | QVQLVESGGGVVQPGRSLRLSCAASGFTFSSCGMH WVRQAPGKGLEWVAAIWYDGSNKYYADSVKGRF TISRDNSKNTLFLQMNSLRAEDTAVYYCARDKNIM GDTWFDFWGQGTLVTVSS<br>SEQ ID NO: 28158 |

FIGURE 50
(Continued)

| | | | |
|---|---|---|---|
| iPS:468830 | 21-225_191G11 | NA | GAAATAGTGATGACGCAGTCCCAGCCACCCT GTCTGTGTCTCCAGGGGAAAGAGCCAACCTCT CCTGCAGGACCAGTCAGAGTGTTTGGATTAGC GTAGCCTGGTACCACCAGAAACCTGGCCAGGC TCCCAGGCTCCTCATCTATGGTGCAGCCACCA GGGCCACTGGTATCCCAGCCAGGTTTAGTGGC AGTGGGTCTGGGACAGAGTTCACTCTCACCAT CAGCAGCCTGCAGTCTGAAGATTTTGCAGTTT ATTACTGTCAGCAGTATAATTACTGGCCGCTC ACTTTCGGCGGAGGGACCAAGGTGGAGATCA AA SEQ ID NO: 24153 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCTGGACAAGGAC TTGAGTGGATGGGATGGATCAACCTAATAGTGG TGGCACAAACTTTGCACAGAAGTTTCAGGGCAG GGTCACCTTGACCAGGGACACGTCCATCAACACA GCCTACATGGAGCTGAGCTGGCTGCGATCGACG ACACGGCCGTATATTACTGTGCGCGTGGGAAGA ACTATGGCTCCTACTTGACTACTGGGGCCAGGG AACCCTGGTCACCGTCCTCG SEQ ID NO: 28159 |
| | | AA | EIVMTQSPATLSVSPGERANLSCRTSQSVWISVA WYHQKPGQAPRLLIYGAATRATGIPARFSGSGS GTEFTLTISSLQSEDFAVYYCQQYNYWPLTFGG GTKVEIK SEQ ID NO: 24154 | QVQLVQSGAEVKKPGASVKVSCKASGYTFTGYYM HWVRQAPGQGLEWMGWINPNSGGTNFAQKFQGR VTLTRDTSINTAYMELSWLRSDDTAVYYCARGKN YGSYFDYWGQGTLVTVSS SEQ ID NO: 28160 |
| iPS:468832 | 21-225_76H10 | NA | GACATCCAGATGACCCAGTCTCCATCCTCCCT GTCTGCCTCTGCAGGAGACAGAGTCACCATCA CTTGCCGGGCAAGTCAGGACATTAGAAATTAT TTAGGCTGGTATCAGCAGAAACCAGGGAAAG CCCCTAAGCGACTGATCTATGGTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TTTTACTGTCTACAGTATAATAGTTACCCATTC ACTTTCGGCCCTGGGACCAAAGTGGATATCAA A SEQ ID NO: 24155 | CAGGTGCAGCTACAACAGTGGGGCGCAGGACTG TTGAAGCCTTCGGAGACCCTGTCCCTCACTTGCG CTGTCAATGGTGGGCCCTTCAGCGGTTGCTACTG GAGCTGGATCCGCCAGCCCCAGGGAAGGGGCT GGAGTGGATTGGGGAAATCAATTATAGTGGAAG GACCAACTTCAACCCGTCCCTCAAGAGTCGAGTC ACCATATCAGTTGACAGGTCCAAGAACCAGTTCT CCCTGAAGCTGAGCTCTGTGCGAGAGACTACGGCGGT GGCTGTGTATTACTGTGCGGGCCAAGGACTACGGCGGT ATGGACGTCTGGGGCCAAGGGACCACGGTCACC GTCTCCTCA SEQ ID NO: 28161 |

FIGURE 50
(Continued)

| | | | DIQMTQSPSSLSASAGDRVTITCRASQDIRNYLG WYQQKPGKAPKRLIYGASSLQSGVPSRFSGSGS GTEFTLTISSLQPEDFATFYCLQYNSYPFTFGPGT KVDIK | QVQLQQWGAGLLKPSETLSLTCAVNGGPFSGCYW SWIRQPPGKGLEWIGEINYSGRTNFNPSLKSRVTISV DTSKNQFSLKLSSVTAADTAVYYCARDYGGMDV WGQGTTVTVSS |
|---|---|---|---|---|
| | | AA | SEQ ID NO: 24156 | SEQ ID NO: 28162 |
| iPS:468834 | 21-225_94G10 | NA | GAAATTGTGTTGACGCAGTCTCCAGGCACCCT GTCTTTGTCTCCAGGGGAGAGAGCCACCCTCT CCTGCAGGGCCAGTCAGAGTGTTAACAGCAAC TACTTAGCCTGGTACCGGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCATTCTCAT CATCAGCAGACTGGAGCCTGAGGATTTTGCAG TGTATTACTGTCAGCAGTATGAAAGCTCGCCG TGGACGTTCGGCCAAGGGACCAAGGTGGAAA TCAAA | CAGGTGCAGTCACAACAGTGGGGCGCAGGACTG TTGAAGCCTTCGGAGAGACCCTGTCCCTCACTGCG CTGTCAATGTGTGGCCCTTCAGCGGTTGCTACTG GAGCGGGATCCGCCAGCCCCCAGGGAAGGGGCG GGAGTGGATTGGGGAAATCAATTATAGTGGAAG GACCAACTTCAACCCGTCCCTCAAGAGTCGAGTC ACCATATCAGTTGACAGTCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA |
| | | | SEQ ID NO: 24157 | SEQ ID NO: 28163 |
| | | AA | EIVLTQSPGTLSLSPGERATLSCRASQSVSNSYLA WYRQKPGQAPRLLIYGASSRATGIPDRFSGSGSG TDFILISRLEPEDFAVYYCQQYESSPWTFGQGTK VEIK | QVQLQQWGAGLLKPSETLSLTCAVNGGPFSGCYW SGIRQPPGKGREWIGEINYSGRTNFNPSLKSRVTISV DTSKNQFSLKLSSVTAADTAVYYCARDYGGMDV WGQGTTVTVSS |
| | | | SEQ ID NO: 24158 | SEQ ID NO: 28164 |

FIGURE 50
(Continued)

| | | | | | | |
|---|---|---|---|---|---|---|
| iPS:468836 | 21-225_198E3 | NA | GACATCCAGATGACCCAGTCTCCATCCTCCT GTCTGCATCTGTAGGAGACAGAGTCACCATCA CTTGCCGGGCAAGTCAGGGCATAAGAAAAGA TTTAGGCTGGTATCAGCAGAAACCAGGGAAA GCCCCTAAGCGCCTGATCTATGCTGCATCCAG TTTGCAAAGTGGGGTCCCATCAAGGTTCAGC GCAGTGGATCGGGACAGAATTCACTCTCACA ATCAGCAGCCTGCAGCCTGAAGATTTTGCAAC TTATGTCTGTCTACAACATTATCGTTACCCTTT CACTTTCGGCCCTGGGACCAAAGTGGATTTCA AA | SEQ ID NO: 24159 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCATATGATGGAGGT TATAAAACTATGCAGACTCCGTGAAGGGCCGA TTCACCATCTCCAGAGACAATTCCAAGAACACGC TGTATCTGCAAATGAATAGCCTGAGAGCTGAGGA CACGGCTGTGTATTACTGTGCGAGAGGTACCCAC GGGTACTACTACGGTGTGGACGTCTGGGGCCAA GGGACCACGGTCACCGTCTCCTCA | SEQ ID NO: 28165 |
| | | AA | DIQMTQSPSSLSASVGDRVTITCRASQGIRKDLG WYQQKPGKAPKRLIYAASSLQSGVPSRFSGSGS GTEFTLTISSLQPEDFATYVCLQHYRYPFTFGPGT KVDFK | SEQ ID NO: 24160 | QVQLVESGGGVVQPGRSLRLSCAASGFTFSSYGMH WVRQAPGKGLEWVAVISYDGGYKNYADSVKGRF TISRDNSKNTLYLQMNSLRAEDTAVYYCARGTHG YYYGVDVWGQGTTVTVSS | SEQ ID NO: 28166 |
| iPS:468838 | 21-225_80E12 | NA | GAAATTGTGTTGACGCAGTGTCCAGGCACCCT GTCTTTGTCTCCAGGGGAGAGAGCCACCGTCT CCTGCAGGGCCAGTCAGAGCGTTAACAGCAAC TACTTAGCCTGGTACCGGCAGAAACCTGACCA GGCTCCCAGGCTCCTCATCTATGGTGCATCCA GCAGGGCCACTGGCATCCCAGACAGGTTCAGT GGCAGTGGGTCTGGGACAGCCTGAGCATTCTCTCAT CATCAGCAGACTGGAGCCTGAGGATTTTGCAG TGTATTACTGTCAGCAGTATGAAAGCTCGCCG TGGACGTTCGGCCAAGGGACCAAGGTGGAAA TCAAA | SEQ ID NO: 24161 | CAGGTGCAGCTACAACAGTGGGGCGCAGGACTG TTGAAGCCTTCGGAGACCCTGTCCCTCACTTGCG CTGTCAATGGTGGGCCCTTCAGCGGTTGCTACTG GAGCTGGATCCGCCAGCCCCAGGGAAGGGCT GGAGTGGATTGGGAAATCAATTATAGTGGAAG GACCAACTTCAACCCGTCCCTCAAGAGTCGAGTC ACCATATCAGTTGACACGTCCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA | SEQ ID NO: 28167 |

FIGURE 50
(Continued)

| | | | |
|---|---|---|---|
| iPS:468840 | 21-225_200H9 | AA | EIVLTQCPGTLSLSPGERATVSCRASQSVNSNYL AWYRQKPDQAPRLLIYGASSRATGIPDRFSGSGS GTDFILISRLEPEDFAVYYCQQYESSPWTFGQGT KVEIK<br>SEQ ID NO: 24162 | QVQLQQWGAGLLKPSETLSLTCAVNGGPFSGCYW SWIRQPPGKGLEWIGEINYSGRTNFNPSLKSRVTISV DTSKNQFSLKLSSVTAADTAVYYCARDYGGMDV WGQGTTVTVSS<br>SEQ ID NO: 28168 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGATCCCATCCAAGGTTCAGCGG CAGTGGATCTGGGACAGAGAATTCACTCTCACAA TCAGCAGCCTGCAGCCTGAAGATTTTGCAACT TATTACTGTCTACAGATCATAATAGTTACCCTCTC ACTTTCGGCGGAGGGACCAAGGTGGAGATCA AA<br>SEQ ID NO: 24163 | CAGGTGCAGCTGCAGGAGTCGGGCCAGGACTG GTGAAGCCTTCACAGACCCTGTCCCTCACCTGCA TTGTCTCTGGTGGCTCCATGAGGAGTGGTGGTGA CTACTGGAGCTGGATCCGCCAGCACCCAGGGAA GGGCCTGGAGTGGTTGGGTACATCTATTACAGT GGGAGCACCTACTACAACCCGTCCCTCAAGAGTC GAGTTACCTTATCAGTAGACACGTCTAAGAACCA GTTCTCCCTGAAGCTGAGCTCTGTGACTGCCGCG GACACGGCCGTGTATTACTGTGCGAGAATGGACT ACAGTAACTACTACTACGGTATGGACGTCTGGGG CCAAGGGACCTCGGTCACCGTCTCCTCA<br>SEQ ID NO: 28169 |
| | | AA | DIQMTQSPSSLSASVGDRVTITCRASQGIRNDLG WYQQKPGKAPKRLIYAASSLQSGIPSRFSGSGSG TEFTLTISSLQPEDFATYYCLQHNSYPLTFGGGT KVEIK<br>SEQ ID NO: 24164 | QVQLQESGPGLVKPSQTLSLTCIVSGGSMRSGGDY WSWIRQHPGKGLEWFGYIYYSGSTYYNPSLKSRVT LSVDTSKNQFSLKLSSVTAADTAVYYCARMDYSN YYYGMDVWGQGTSVTVSS<br>SEQ ID NO: 28170 |

FIGURE 50
(Continued)

| | | | |
|---|---|---|---|
| iPS:468820 | 21-225_76E10 | NA | GAAATTGTGTTGACGCAGTCTCCAGGCACCCT GTCTTTGTCTCCAGGGGAGAGAGCACCCTCT CCTGCAGGGCCAGTCAGTCAGAGTGTTAACAGCAAC TACTTAGCCTGGTACCGGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCATTCTCAT CATCAGCAGACTGGAGCCTGAGGATTTTGCAG TGTATTACTGTCAGCAGTATGAAAGCTCGCCG TGGACGTTCGGCCAAGGGACCAAGGTGGAAA TCAAA SEQ ID NO: 24165 | CAGGTGCAGCTCCAACAGTGGGCGCAGGACTG TTGAAGCCTTCGGAGACCCTGTCCCTCACTTGCG CTGTCAATGGTGGGCCCTTCAGCGGTTCCTACTG GAGCTGGATCCGCCAGCCCCCAGGGAAGGGGCT GGAGTGGATTGGGGAAATCAATTATAGTGGAAG GACCAACTTCAACCCGTCCCTCAAGAGTCGAGTC ACCATATCAGTTGACACGTCCAAGAACCAGTTCT CCCTGAAGCTGAGCTCTGTGACCGCCGGACAC GGCTGTGTATTACTGTGCGAGAGACTACGGCGGT ATGGACGTCTGGGGCCAAGGGACCACGGTCACC GTCTCCTCA SEQ ID NO: 28171 |
| | | AA | EIVLTQSPGTLSLSPGERATLSCRASQSVNSNYLA WYRQKPGQAPRLLIYGASSRATGIPDRFSGSGSG TDFTLTISRLEPEDFAVYYCQQYESSPWTFGQGTK VEIK SEQ ID NO: 24166 | QVQLQQWGAGLLKPSETLSLTCAVNGGPFSGSYW SWIRQPPGKGLEWIGEINYSGRTNFNPSLKSRVTISV DTSKNQFSLKLSSVTAADTAVYYCARDYGGMDV WGQGTTVTVSS SEQ ID NO: 28172 |
| iPS:468842 | 21-225_50H4 | NA | GACATCCAGATGACCCAGTCTCCATCCTCCCT GTCTGCATCTGTTGGAGACAGAGTCACCATCA CTTGCCGGGCAAGTCAGGGCATTAGAAATGAT TTAGGCTGGTATCAGCAGAAACCAGGGAAGG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTACAGCCTGAAGATTTTGCAACT TATTACTGTCTACAACATTATAGTTACCCTCGG ACGTTCGGCCAAGGGACCAAGGTGGAAATCA AA SEQ ID NO: 24167 | CAGGTGCAGCTGGTGGAGTCTGGGGGAGGCGTG GTCCAGCCTGGGGAGGTCCCTGAGACTCTCCTG CAGCGTCTGGATTCACCTTCAGTAGCTATGTCAT GCACTGGGTCCGCCAGGCTCCAGGCAAGGGGCT GGAGTGGGTGGCAGCTATATGGTATGATGGAAG TAATAAATACTATGCAGACTCCGTGAAGGGCCG ATTCACCATCTCCAGAGACAATTCCAAGAACACG CTGGATCTGCAAATGAACAGCTGAGAGCCGAG GACACGGCTGTGTATTACTGTGCGAGAGAGTTGT ATAGCAGCAACTGGTACGACTACGGTATGGACG TCTGGGGCCAAGGGACCACGGTCACCGTCTCCTC A SEQ ID NO: 28173 |

FIGURE 50
(Continued)

| | | | |
|---|---|---|---|
| | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEIK<br><br>SEQ ID NO: 24168 | QVQLVESGGGVVQPGRSLRLSCAASGFTFSSYVMH WVRQAPGKGLEWVAAIWYDGSNKYYADSVKGRF TISRDNSKNTLDLQMNSLRAEDTAVYYCARELYSS NWYDYGMDVWGQGTTVTVSS<br><br>SEQ ID NO: 28174 |
| iPS:468844 | NA | GACATCCAGATGACCCAGTCTCCATCCTCCCT GTCTGCATCTGTAGGAGACAGAGTCACCATCA CTTGCCGGGCAAGTCAGGGCATTAGAAGTGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGGAATTCACTCTCACAA TCAGCAGCCTGCAGCCTGAAGATTTTGCAACT TATTACTGTCTACAGATATATAGTTACCCATTC ACTTTCGGCCCTGGGACCAAAGTGGATATCAA A<br><br>SEQ ID NO: 24169 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAACAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAAGCCTCGAC CTCTGGGGCCAGGGAACCCTGGTCACCGTCTCCT CA<br><br>SEQ ID NO: 28175 |
| 21-225_48E10 | AA | DIQMTQSPSSLSASVGDRVTITCRASQGIRSDLG WYQQKPGKAPKRLIYTASSLQSGVPSRFSGSGSG TEFTLTISSLQPEDFATYYCLQYNSYPFTFGPGTK VDIK<br><br>SEQ ID NO: 24170 | EVQLVESGGGLVKPGGSLRLSCAASGFTFSSYNMN WVRQAPGKGLEWVSSISGSSSYIYYADSVKGRFTIS RDNAKNSLYLQMNSLRAEDTAVYYCARSLDLWG QGTLVTVSS<br><br>SEQ ID NO: 28176 |

FIGURE 50
(Continued)

| | | | |
|---|---|---|---|
| iPS:468846 | 21-225_53B10 | NA | GACATCCAGATGACCCAGTCTCCATCCTCCCT GTCTGCCTCTGCAGGAGACAGAGTCACCATCA CTTGCCGGGCAAGTCAGGACAGATTAGAAATTAT TTAGGCTGGTATCAGCAGAAACCAGGGAAAG CCCCTAAGCGCCTGATCTATGTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TTTTACTGTCTACAGTATAATAGTTACCCATTC ACTTTCGGCCCTGGGACCAAGTGGATATCAA A<br/>SEQ ID NO: 24171 | GAGGTGCAGTTGGTGGAGTCTGGGGGAGGCTTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGCAGT TACATATACTAGTAGACTCAGTGAAGGCCGAT TCACCATCTCCAGAGACAACGCCAAGAACTCACT GTATCTGCAAATGAACAGCCTGAGAGCCGAGA CACGGCTGTGTATTACTGTGCGAGAGTCAACTCT TTTGACTCCTGGGGCCAGGGAACCCTGGTCACCG TCTCCTCA<br/>SEQ ID NO: 28177 |
| | | AA | DIQMTQSPSSLSASAGDRVTITCRASQDIRNYLG WYQQKPGKAPKRLIYGASSLQSGVPSRFSGSGS GTEFTLTISSLQPEDFATFYCLQYNSYPFTFGPGT KVDIK<br/>SEQ ID NO: 24172 | EVQLVESGGGLVKPGGSLRLSCAASGFTFSSYSMN WVRQAPGKGLEWVSSISGSSSYIYVDSVKGRFTIS RDNAKNSLYLQMNSLRAEDTAVYYCARVNSFDSW GQGTLVTVSS<br/>SEQ ID NO: 28178 |
| iPS:468848 | 21-225_54B1 | NA | GACATCCAGATGACCCAGTCTCCATCCTCCCT GTCTGCTTCTATTGGAGACAGAGTCACCATCA CTTGCCGGGCAAGTCAGAACATTAGCAGCTAT TTAAATTGGTATCAGCAGAAACCAGGGAAGG CCCCCAAGTCTCTGATCTATGCTGCATCCAGT TGCATAGTGGGGTCCCACCAAGGTTCACTCTCACCAT AGTGGATCTGGGACAGTTCACTCTCACCAT CAGCAGTCTGCAACTGAAGATTTTGCAATTT ACTACTGTCAACAGAGTTACAGAACCCCTCTG TGGACGTTCGGCCAAGGGACCAAGGTGGAAA TCAAA<br/>SEQ ID NO: 24173 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTCTTAGTGGTAGTGGTGGT AGCACATTCTACGCAGACTCCGTGAAGGGCCGGT TCACCATCTCCAGAGACAATTCCAAGAACACGCT GTATCTGCAAATGAGCAGCCTGAGAGCCGAGGA CACGGCCGTATATTACTGTGCCGAAGAGGCCGT GAATATAGTGGCTACGATTACTTTGACTACTGGG GCCAGGGAACCCTGGTCACCGTCTCCTCA<br/>SEQ ID NO: 28179 |

FIGURE 50
(Continued)

| | | | |
|---|---|---|---|
| iPS:468850 | 21-225_63F4 | AA | DIQMTQSPSSLSASIGDRVTITCRASQNISSYLNW YQQKPGKAPKFLIYAASSLHSGVPPRFSGSGSGT DFTLTISSLQPEDFAIYYCQQSYRTPLWTFGQGT KVEIK<br>SEQ ID NO: 24174 | EVQLLESGGGLVQPGGSLRLSCAASGFTFSSYAMS WVRQAPGKGLEWVSVLSGSGGSTFYADSVKGRFTI SRENSKNTLYLQMSSLRAEDTAVYYCARRGREYS GYDYFDYWGQGTLVTVSS<br>SEQ ID NO: 28180 |
| | | NA | GACATCGTGATGACCCAATCTCCAGACTCCCT GGCTGTGTCTCTGGGCGAGAGGGCCACCATCA ACTGCAAGTCCAGCCAGAGTGTTTTATCCAGC TCCAACAATAACAACTACTTAGCTTGGTACCA GCAGAAACCAGGACAGCCTCCTAAGCTGCTCA TTTACTGGGCATCTACCCGGGAATCCGGGATC CCTGACCGATTCAGTGGCAGCGGGTCTGGGAC AGGTTTCACTCTCACCATCAGCAGCCTGCAGG CTGAGGATGTGGCAGTTTATTACTGTCAGCAA TATTATACTACTCCGTGCAGTTTTGGCCAGGG GACCAAGCTGGAGATCAAT<br>SEQ ID NO: 24175 | CAGGTGCAGCTGGTGCAATCTGGGGCTGAGGTG AAGAAGCCTGGGGCCTCAGTGAAGGTCTCCTGC AAGGCTTCTGGATACACCTTCACCAATTATGATG TCAACTGGGTGCGACAGGCCACTGGACAAGGC TTGAGTGGATGGGATGCACCCTAACAGTGG TAACACAGGCTATGCACAGAAGTTCCGGGGCAG AGTCACCATGACCAGGAACACCTCCCTAAGCAC AGTCTACATGGAGCTGAGCAGCCTGCGATCTGAG GACACGGCCGTGTATTACTGTGCCTATAGCAGTG GCTGGTACGTTTTGACTACTGGGGCCAGGGAAC CCTGGTCACCGTCCTCA<br>SEQ ID NO: 28181 |
| | | AA | DIVMTQSPDSLAVSLGERATINCKSSQSVLSSSN NNNYLAWYQQKPGQPPKLLIYWASTRESGIPDR FSGSGSGTGFTLTISSLQAEDVAVYYCQQYYTTP CSFGQGTKLEIN<br>SEQ ID NO: 24176 | QVQLVQSGAEVKKPGASVKVSCKASGYTFNYDV NWVRQATGQGLEWMGWMHPNSGNTGYAQKFRG RVTMTRNTSLSTVYMELSSLRSEDTAVYYCAYSSG WYVFDYWGQGTLVTVSS<br>SEQ ID NO: 28182 |

FIGURE 50
(Continued)

| | | | | |
|---|---|---|---|---|
| iPS:468852 | 21-225_71F3 | NA | GACATCGTGATGACCCAATCTCCAGACTCCCT GGCTGTGTCTCTGGCGGCAGAGGCCACCATCA ACTGCAAGTCCAGCCAGAGTGTTTTATCCAAC TCCAACAATAACAACTACTTAGCTTGGTACCA GCAGAAACCAGGACAGCCTCCTAAGCTGCTCA TTTACTGGGCATCTACCCGGGAATCCGGGATC CCTGACCGATTCAGTGGCAGCGGGTCTGGGAC AGATTTCACTCTCACCATCAACAGCCTGCAGG CTGAAGATGTGGCAGTTTATTACTGTCAGCAA TATTATACTACTCCGTGCAGTTTGGCCAGGG GACCAAGCTGGAGATCAAA<br><br>SEQ ID NO: 24177 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATG TCAACTGGGTGCGACAGGCCACTGGACAAGGGC TTGAGTGGATGGGATGGATGCACCTAACAGTGG TAACACAGGCTATGCACAGAAGTTCAGGGCAG AGTCACCATGACCAGGAACACCTCCATAAGCAC AGCCTACATGGAGCTGAGCAGCCTGCGATCTGA GGACACGGCCGTGTATTACTGTGCCTATAGCAGT GGCTGGTACGTTTTGACTTCCTGGGGCCAGGGAA CCCTGGTCACCGTCTCCTCA<br><br>SEQ ID NO: 28183 |
| | | AA | DIVMTQSPDSLAVSLGARATINCKSSQSVLSNSN NNNYLAWYQQKPGQPPKLLIYWASTRESGIPDR FSGSGSGTDFTLTINSLQAEDVAVYYCQQYYTTP CSFGQGTKLEIK<br><br>SEQ ID NO: 24178 | QVQLVQSGAEVKKPGASVKVSCKASGYTFTNYDV NWVRQATGQGLEWMGWMHPNSGNTGYAQKFQG RVTMTRNTSISTAYMELSSLRSEDTAVYYCAYSSG WYVFDSWGQGTLVTVSS<br><br>SEQ ID NO: 28184 |
| iPS:468854 | 21-225_72C4 | NA | GATGTTGTAATGACTCAGTCTCCGCTCTCCCTG CCCGTCACCCTTGGACAGCCGGCCTCCATCTC CTGCAGGTCTGTCAAGCCTCGTACACAGTG ATGGAAACACCTACTTGAATTGGTTCAGCAG AGGCCAGGCCAATCTCCAAGGCGCCTAATTA TGAGGTTTCTAAGTGGGACTCTGGGGTCCCAG ACAGATTCAGTGGCAGTGGGTCAGGCACTGAT TTCACACTGAAAATCAGCAGGGTGGAGGCTGA GGATGTTGGGGTCTTTTACTGCATGCAAGGTA CACACTGGCCGCCTCACTTTCGGCGGAGGGACC AAGGTGGAGATCAAA<br><br>SEQ ID NO: 24179 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCACTGGACAAGGGC TTGAGTGGATGGGATGGATGCACAGAAGTTCAGGGCAG TAACACAGGCTATGCACAGAAGTTCAGGGCAG AGTCACCATGACCAGGAACACCTCCATAAGCAC AGCCTACATGAACAGCTGAACAGCCTGAGATCTGA GGACACGCCCGTGTATTACTGTGCATAGCAGT GGCTGGTACCTCTTTGACTACTGGGGCCAGGGAA CCCTGGTCACCGTCTCCTCA<br><br>SEQ ID NO: 28185 |

FIGURE 50
(Continued)

| | | | |
|---|---|---|---|
| | | AA | DVVMTQSPLSLPVTLGQPASISCRSGQSLVYSDG NTYLNWFQQRPGQSPRRLIYEVSKWDSGVPDRF SGSGSGTNFTLKISRVEAEDVGVFYCMQGTHWP LTFGGGTKVEIK<br>SEQ ID NO: 24180 | QVQLVQSGAEVKKPGASVKVSCKASGYTFTNYDIN WVRQVTGQGLEWMGWMHPNSGNTGYAQKFQGR VTMTRNTSISTAYMELNSLRSEDTAVYYCSHSSGW YLFDYWGQGTLVTVSS<br>SEQ ID NO: 28186 |
| iPS:468856 | 21-225_77C9 | NA | GATGTTGTGATGACTCAGTCTCCACTCTCCCTG CCCGTCACCCTTGGACAGCCGGCCTCCATCTC CTGCAGGTCTAGTCAAAGCCTCGTTTACAGTG TTGGAAACACCTCCTTGAGTTGGTTTCAGCAG AGGCCAGGCCAATCTCCAAGGCGCCTAATTTA TAAGGTTTCTAACTGGGACTCTGGGGTCCCA ACAGATTCAGCGGCCAGTGGGTCAGGCACTGAT TTCACACTGAAAATCAGCAGGGTGGAGGCTGA GGATGTTGGGGTTTATTACCGCATGCAAGGTA CACACTGGCCATTCACTTTCGGCCCTGGGACC AAAGTGGATATCAAA<br>SEQ ID NO: 24181 | CAGCTGCAGCTGCAGGAGTCGGGCCAGGACTG GTGACGCCTTCGAGGAGACCCTGTCCTCACCTGCA CTGTCTCTGGCGGCTCCATCAGCAGGAGTAGTTA CTACTGGGGCTGGATCCGCCAGCCCCAGGGAA GGGGCTGAGTGGATTGGAGTATCTATTATAGT GGGAGCGCCTACTCCAACCCGTCCTCAAGAGTC GAGTCACCATATCCGTAGACACGTCCAAGAACC AGTTCTCCCTGAAGCTGAGCTCTGTGACCGCCGC GGACACGGCTCTGTTTTACTGTGCGAGACTTGAC TCTAACTGGGGTCTTGACTACTGGGGCCAGGAA CCCTGGTCACCGTCTCCTCA<br>SEQ ID NO: 28187 |
| | | AA | DVVMTQSPLSLPVTLGQPASISCRSSQSLVYSVG NTSLSWFQQRPGQSPRRLIYKVSNWDSGVPDRF SGSGSGTDFTLKISRVEAEDVGVYYRMQGTHWP FTFGPGTKVDIK<br>SEQ ID NO: 24182 | QLQLQESGPGLVTPSETLSLTCTVSGGSISRSSYYW GWIRQPPGKGLEWIGSIYYSGSAYSNPSLKSRVTIS VDTSKNQFSLKLSSVTAADTALFYCARLDSNWGLD YWGQGTLVTVSS<br>SEQ ID NO: 28188 |

FIGURE 50
(Continued)

| | | | | |
|---|---|---|---|---|
| iPS:468858 | 21-225_148C9 | NA | GACATCCAGATGACCCAGTCTCCATCCTCCCT GTCTGCATCTGTAGGAGACAGAGTCACCATCA CTTGCCGGGCAAGTCTGGGGCATTAGAGATGAT TTAGGCTGGTATCAGCAGAAACCAGGGAAAG CCCCTAAGCGCCTGATCTATGCTGCATCCAGT TTGCAGAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATTATAGTTATCCTCGG ACGTTCGGCCAAGGGACCAAGGTGGAAATCA AA | CAGGTGCAGCTGGTGGAGTCTGGGGGAGGCGTG GCCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGGAAGT AATAAGTACTATGCAGACTCCGTGAAGGGCCGA CTCACCATCTCCAGAGACAATTCCAAGAACACGC TGTATCTGCAAATGAACAGCCTGAGAGCCGAGG ACACGGCTGTGTATTACTGTGCGAGAGAGAGGTA TAGCAGTGGCTGGTACGACTACGGTTTGGACGTC TGGGGCCAAGGGACCACGGTCACCGTCTCCTCA |
| | | | SEQ ID NO: 24183 | SEQ ID NO: 28189 |
| | | AA | DIQMTQSPSSLSASVGDRVTITCRASRGIRDDLG WYQQKPGKAPKRLIYAASSLQSGVPSRFSGSGS GTEFTLTISSLQPEDFATYYCLQHYSYPRTFGQG TKVEIK | QVQLVESGGGVAQPGRSLRLSCAASGFTFSDYGM HWVRQAPGKGLEWVAVIWYDGSNKYYADSVKGR LTISRDNSKNTLYLQMNSLRAEDTAVYYCARERYS SGWYDYGLDVWGQGTTVTVSS |
| | | | SEQ ID NO: 24184 | SEQ ID NO: 28190 |
| iPS:468860 | 21-225_224E7 | NA | GACATCCAGATGACCCAGTCTCCTTCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTACGCGCCTGATCTATGCTGCATCCAGT TGCAAAGTGGGGTCCCATCGAGGTTCAGCGGC AGTGGATCTGGGACAGATCACTCTCACAAT CAGCAGCCTGCAGCCTGAAGATTTTGCAACTT ATTACTGTCTACAACATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGCCTCTCCTGTG CAGCGTCTGGATTCACCTTCAGTAGCTATGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAACAGTA TAGCAGCAGCTGGTACGACTTCGGTCTGACGTC TGGGGCCAAGGGACCACGGTCACCGTCTCCTCA |
| | | | SEQ ID NO: 24185 | SEQ ID NO: 28191 |

FIGURE 50
(Continued)

| | | | |
|---|---|---|---|
| iPS:468862 | 21-225_178H8 | AA | DIQMTQSPSSLSASVGDRVTITCRASQGIRNDLGWYQQKPGKAPTRLIYAASSLQSGVPSRFSGSGSGTEFTLTISSLQPEDFATYYCLQHYSYPRTFGQGTKVEIK<br>SEQ ID NO: 24186 |
| | | | QVQLVESGGGVVQPGRSLSLSCAASGFTFSSYVMHWVRQAPGKGLEWVAVIWYDGSNKYYADSVKGRFTISRDNSKNTLYLQMNSLRAEDTAVYYCAREQYSSSWYDFGLDVWGQGTTVTVSS<br>SEQ ID NO: 28192 |
| | | NA | CAGTCTGCCCTGACTCAGTCTGCCTCCGTGTCGGGGTCTCCTGGACAGTCGATCACCATCTCCTGCACTGGAACCAGCAGTGACGTTGGTGGTTATAATTTTGTCTCCTGGTACCAACAGCACCCAGGCAAAGTCCCCAAATTCATGATTTATGAGGTCAGTAATCGGCCCTCAAGGGGTTCCTAATCGTTTTCTGGCTCCAAGTCTGGCAACACGGCCTCCCTGACCATCTCTGGCCTCCAGGCTGAGGACGAGGCTGATTATTACTGCAGTCATATACAAGCAGTACACTTGGGTGTTCGGCGGAGGGACCAAACTGACCGTCCTA<br>SEQ ID NO: 24187 |
| | | | CAGGTGCAGCTGGTGCAGTCTGGGGCTGAGGTGAGGACGCCTGGGGCCTCAGTGAAGGTCTCCTGCAAGGCTTCTGGATACACCTTCACCGACTATTATGCACTGGGTGCGACAGGCCCCTGGACAAGGGCTTGAGTGGATGGGATGGATCAACCCTAACAGAGGTGGCACAAACTATGCTCAGAAGTTTCAGGGCAGGGTCACCATGACCAGGGACACGTCCATCAGCACAGCCTACATGGAGCTGAGCAGGCTGAGATCTGACGACACGGCCGTGTATTACTGTGCGAGAGGAGGATCGCAGTGGCTGGTACTACTACGGTATGGACGTCTGGGGCCAAGGGACCACGGTCACCGTCTCCTCA<br>SEQ ID NO: 28193 |
| | | AA | QSALTQSASVSGSPGQSITISCTGTSSDVGGYNFVSWYQQHPGKVPKFMIYEVSNRPSGVPNRFSGSKSGNTASLTISGLQAEDEADYYCSSYTSSYTWVFGGGTKLTVL<br>SEQ ID NO: 24188 |
| | | | QVQLVQSGAEVRTPGASVKVSCKASGYTFTDYYMHWVRQAPGQGLEWMGWINPNRGGTNYAQKFQGRVTMTRDTSISTAYMELSRLRSDDTAVYYCAREEDRSGWYYYGMDVWGQGTTVTVSS<br>SEQ ID NO: 28194 |

FIGURE 50
(Continued)

| | | | |
|---|---|---|---|
| iPS:468864 | 21-225_60D6 | NA | CAGTCTGTGCTGACTCAGCCACCCTCAGCGTC TGGGACCCCGGGCAGAGGGTCACCATCTCT GTTCTGGAAGCAGCTCCAACATCGAAGTAAT ACTGTAAACTGGTACCAGCAGCTCCCAGGAAC GGCCCCAAACTCCTCATCTATAGTAATAATC AGCGGCCCTCAGGGGTCCCTGACCGATTCTCT AGCGGCTCCAAGTCTGGCACCTCAGCTCCCTGGC CATCAGTGGGCTCCAGTCTGAGGATGACAGCTG ATTATTACTGTGCAGCATGGGATGACAGCTG AATGGTCCGGTCGGCGGAGGGACCAAGCTGA CCGTCCTA | CAGATCACCTTGAAGGAGTCTGGTCCTACGCTGG TGAAACCACACAGACCCTCACGTCACCTGCAC CTTCTCTGGGTTCTCACTCAGCACTAGTGGAGTG GGTGTGGGCTGGATCCGTCAGCCCCCAGAAAG GCCCTGGAGTGGCTTGCACTCATTTATTGGAAAG ATGATGAGCGTACAGCCCATCTGAAGAGCA GGCTCACCATCACCAAGGACACTTCCAAAACC AGTGGTCCTTACAATGACCAACATGACCCTGT GGACACAGCCACATATTACTGTGCACATGCAGTG GCTGTCTCCTTGACTACTGGGGCCAGGGAACCC TGGTCACCGTCCTCA |
| | | | SEQ ID NO: 24189 | SEQ ID NO: 28195 |
| | | AA | QSVLTQPPSASGTPGQRVTISCSGSSSNIGSNTVN WYQQLPGTAPKLLIYSNNQRPSGVPDRFSGSKS GTSASLAISGLQSEDEADYYCAAWDDSLNGPVG GGTKLTVL | QITLKESGPTLVKPTQTLTLTCTFSGFSLSTSGVGVG WIRQPPGKALEWLALIYWKDDERYSPSLKSRLTITK DTSKNQVLTMTNMDPVDTATYYCAHAVAVSFD YWGQGTLVTVSS |
| | | | SEQ ID NO: 24190 | SEQ ID NO: 28196 |
| iPS:468866 | 21-225_190C1 | NA | TCCTATGAGCTGACACAGCCACCCTCGGTGTC AGTGTCCCCAGGACAAAACGGCCAGGATCACCT GCACTGGAGATGCAATGCCGAAAAATATGCT TATTGGGACCAGCAGAAGTCAGGCCAGGGAC TGTGCTGGTCATCTGAGGACAGCAAGGCGAC CCTCCGGGATCCCTGAGAGATTCTCTGGCTCC AGCTCAGGGACAATGGCCCCTTGACTATCAG TGGGGCCCAGGTGGAGGATGAAACTGACTAC GACTGTAACTCAACAGACAGCAGTGGTAATCG GGTGTTCGGCGGAGGGACCAAGCTGACCGTCC TA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGAC TTGAGTGGATGGGATGGATCAACCCTTACAGTGG TGCACAAACTATGCACAGAAGTTTCAGGGCAG GGTCACCATGACCAGGGACACGTCCATCAGCAC AGCCTACATGGAACTGAGCAGGCTGAGATCTGA CGACACGGCCGTGTATTACTGTGCGAGAGATAG AGCAGTGGCTGGAAACTACTTCTACTACGGTATG GACGTCTGGGGCCAAGGGACCACGGTCACCGTC TCCTCA |
| | | | SEQ ID NO: 24191 | SEQ ID NO: 28197 |

FIGURE 50
(Continued)

| | | | |
|---|---|---|---|
| | | AA | SYELTQPPSVSVSPGQTARITCTGDAMPKKYAY WDQQKSGQAPVLVISEDSKRPSGIPERFSGSSSG TMAPLTISGAQVEDETDYDCNSTDSSGNRVFGG GTKLTVL<br>SEQ ID NO: 24192 | QVQLVQSGAEVKKPGASVKVSCKASGYTFTGYYM HWVRQAPGQGLEWMGWINPYSGGTNYAQKFQGR VTMTRDTSISTAYMELSRLRSDDTAVYYCARDRAV AGNYFYGMDVWGQGTTVTVSS<br>SEQ ID NO: 28198 |
| iPS:468868 | 21-225_74A1 | NA | GACATCCAGATGACCCAGTCTCCATCCTCCCT GTCGGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTACGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATGATAGTTACCCTCTC ACTTTCGGCGGAGGGACCAAGGTGGAGATCA AA<br>SEQ ID NO: 24193 | CAACTGCAGCTGCAGGAGTCGGGCCCGGACTG GTGAAGCCTTCGGAGACCCTGTCCCTCACCTGCA CTGTCTCTGGTGGCTCCATCAGCGGTAGTAGTTA CTACTGGGGCTGGATCCGCCAGCCCCGGGAA GGGCTGGAGTGGATTGGGAATATCTATTATAGT GGGAGCACCTACCACAACCCGTCCCTCAAGAGTC GAGTCACCATATCCGTGGACACGTCCAAGAACC AGTTCTCCCTGAAGCTGACCTCTGTGACCGCCGC AGACACGGCTGTGTTTACTGTGCGAGACATGAT TACTTTGGTCCCTTGACTCTGACTCTGGGCCAGGAA TTCTGGTCACCGTCTCCTCA<br>SEQ ID NO: 28199 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHDSYPLTFGGG AKVEIK<br>SEQ ID NO: 24194 | QLQLQESGPGLVKPSETLSLTCTVSGGSISGSSYYW GWIRQPPGKGLEWIGNIYSGSTYHNPSLKSRVTIS VDTSKNQFSLKLTSVTAADTAVFYCARHDLLWSLD FWGQGILVTVSS<br>SEQ ID NO: 28200 |

FIGURE 50
(Continued)

| | | | | |
|---|---|---|---|---|
| iPS:468870 | 21-225_74A8 | NA | GACATCGTGATGACCCAGTCTCCAGACTCCCTGGCTGTGTCTCTGGGCGAGAGGGCCACCATCAACTGCAAGTCCAGCCAGAGTGTTTTGTACAGCTCCAACAGTCACAACTACTTAGCTTGGTACCAGCAGAAACCAGGACAGCCTCCTAAACTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTCCGTGCAGTTTTGGCCAGGGGACCAAGCTGGAGATCAAA | |
| | | | | SEQ ID NO: 24195 |
| | | AA | DIVMTQSPDSLAVSLGERATINCKSSQSVLYSSNSHNYLAWYQQKPGQPPKLLIYWASTRESGVPDRFSGSGSGTDFTLTISSLQAEDVAVYYCQQYYSTPCSFGQGTKLEIK | QVQLVQSGAEVKKPGASVKVSCKASGYTFTNYDINWVRQASGQQLEWMGWMHPNSGNTGYAQKFQGRVTMTRNTSISTAYMELSSLRSEDSAVYYCAYSSGWYKFDYWSQGTLVTVSS |
| | | | SEQ ID NO: 24196 | SEQ ID NO: 28202 |
| iPS:472730 | 21-225_14B1_LC1 | NA | GACATCCAGATGACCCAGTCTCCATCCTACCTGTCTGCATCTGTAGGAGACAGAGTCACCATCACTTGCCGGGCAAGTCAGGACATTAGAGATAATTTAGGCTGGTATCAGCAGAAACCAGGGAAAGCCCCTAAACGCCTGATCTATCTGCATACAGTTTGCAAAGTGGGGTCCCATCAAGGTTCAGCGGCAGTGGATCTGGGACAGATTCACTCTCACAATCAGCAGCCTGCAGCCTGAGGATTTTGCAACTTATTACTGTCTACAACATTATAATTACCCGCTCACTTTCGGCGGAGGGACCAAGGTGGAGATCA | GAGGTGCAGCTGGTGGAGTCTGGGGGAGGCCTGGTCAAGCCTGGGGGGTCCCTGAGACTCTCCTGTGCAGCCTCTGGATTCACCTTCAGTAGCTATACCATGAACTGGGTCCGCCAGGCTCCAGGGAAGGGGCTGGAGTGGGTCTCATCCATAAGTGGTAGTAGTTCAACCATCCAGAGACAACAGCCAAGAACTCTGTATCTGCAAATGAACAGCCTGAGAGCCGAGGACACGGCTGTGTATTACTGTGCGAGAGATAGAGGCAGCAGCTGGGGCCAGGAACCCTGGTCACCGTCTCCTCA |
| | | | SEQ ID NO: 24197 | SEQ ID NO: 28203 |

FIGURE 50
(Continued)

| | | | |
|---|---|---|---|
| | | AA | DIQMTQSPSYLSASVGDRVTITCRASQDIRDNLG WYQQKPGKAPKRLIYTAYSLQSGVPSRFSGSGS GTEFTLTISSLQPEDFATYYCLQHYNYPLTFGGG TKVEIK<br><br>SEQ ID NO: 24198 | EVQLVESGGGLVKPGGSLRLSCAASGFTFSSYTMN WVRQAPGKGLEWVSSISGSSSYLYYPDSVKGRFTIS RDNAKNSLYLQMNSLRAEDTAVYYCARDRGSSW GQGTLVTVSS<br><br>SEQ ID NO: 28204 |
| iPS:472731 | 21-225_14B1_LC2 | NA | TCCTTTGAGCTGACTCAGCCACCTCAGTGTCC GTGTCCCCAGGACAGACAGCCAGCATCACCTG CTCTGGAGATAAATTGGGGGATAAATATGCTT ACTGGTATCAGCAGAAGCCAGGCCAGTCCCCT GTGTTGGTCATCTATCAAGATAGGAAGCGCC CTCAGGGATCCCTGAGCGATTCTCTGGCTCA ACTCTGGGAACACAGCCACTCTGACCATCAGC GGGACCCAGGCTATGGATGAGGCTGACTATTA CTGTCAGGCGTGGGACAACAGCACTGTGGTGT TCGGCGGAGGGACCAAGCTGACCGTCCTA<br><br>SEQ ID NO: 24199 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATACCAT GAACTGGGTCCGCCAGGCTCCAGGGAAGGGGCT GGAGTGGGTCTCATCCATAAGTGGTAGTAGTAGT TACTTATATACTACCCAGAGACTCAGTGAAGGGCCGAT TCACCATCTCCAGAGACAACGCCAAGAACTCTCT GTATCTGCAAATGAACAGCCTGAGAGCCGAGGA CACGGCTGTGTATTACTGTGCAGAGATAGAGGC AGCAGCTGGGGCCAGGGAACCCTGGTCACCGTC TCCTCA<br><br>SEQ ID NO: 28205 |
| | | AA | SFELTQPPSVSVSPGQTASITCSGDKLGDKYAYW YQQKPGQSPVLVIYQDRKRPSGIPERFSGSNSGN TATLTISGTQAMDEADYYCQAWDNSTVFGGG TKLTVL<br><br>SEQ ID NO: 24200 | EVQLVESGGGLVKPGGSLRLSCAASGFTFSSYTMN WVRQAPGKGLEWVSSISGSSSYLYYPDSVKGRFTIS RDNAKNSLYLQMNSLRAEDTAVYYCARDRGSSW GQGTLVTVSS<br><br>SEQ ID NO: 28206 |

FIGURE 50
(Continued)

| | | | | |
|---|---|---|---|---|
| iPS:472732 | 21-225_2B10_LC1 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTTCTTGAATTGGTTTCAGCAG AGGCCAGGCCAATCTCCAAGGCGCCTAATTTA TAAGGTTTCTAACTGGGACTCTGGGGTCCCAG ACAGATTCAGCGGCAGTGGGTCAGGCACTGGT TTCACACTGAAAATCAGCAGGGTGGAGGCTGA GGATGTTGGGGTTTATTACTGCATACAAGGTA CGCACTGGCCTTTCCCCTTCGGCCAAGGGACA CGACTGGAGATTAAA<br>SEQ ID NO: 24201 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGGCT GGAGTGGGTGGCGGTTATATGGTATGATGGAAGT AATAAATACTATGCAGACTCCGTGAAGGTCCGAT TCACCGTCTCCAGAGACAATTCCAAGAACACGCT GTCTCTGCAAATGAACAGCCTGAGAGCCGAGGA CACGGCTGTGTATTACTGTGCGAGAGAGATAT ACCAGTGGCTGGTATGACTACGGTATGGACGTCT GGGGCCAAGGGACCACGGTCACCGTCTCCTCA<br>SEQ ID NO: 28207 |
| | | AA | DVVMTQSPLSLPVTLGQPASISCRSSQSLVYSDG NTFLNWFQQRPGQSPRRLIYKVSNWDSGVPDRF SGSGSGTGFTLKISRVEAEDVGVYYCIQGTHWPF PFGQGTRLEIK<br>SEQ ID NO: 24202 | QVQLVESGGGVVQPGRSLRLSCAASGFTFSSYVMH WVRQAPGKGLEWVAVIWYDGSNKYYADSVKVRF TVSRDNSKNTLSLQMNSLRAEDTAVYYCARERYTS GWYDYGMDVWGQGTTVTVSS<br>SEQ ID NO: 28208 |
| iPS:472733 | 21-225_2B10_LC2 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ATTTTGTCTCCTGGTACCAACAGCACCCAGAC AAAGCCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAGTCATCATATACAAGCACCGG CACTGTGGTAATCGGCGGAGGGACCAAACTG ACCGTCCTA<br>SEQ ID NO: 24203 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGGCT GGAGTGGGTGGCGGTTATATGGTATGATGGAAGT AATAAATACTATGCAGACTCCGTGAAGGTCCGAT TCACCGTCTCCAGAGACAATTCCAAGAACACGCT GTCTCTGCAAATGAACAGCCTGAGAGCCGAGGA CACGGCTGTGTATTACTGTGCGAGAGAGATAT ACCAGTGGCTGGTATGACTACGGTATGGACGTCT GGGGCCAAGGGACCACGGTCACCGTCTCCTCA<br>SEQ ID NO: 28209 |

FIGURE 50
(Continued)

| | | | AA | QSALTQPASVSGSPGQSITISCTGTSSDVGGYNFV SWYQQHPDKAPKLMIYEVSNRPSGVSNRFSGSK SGNTASLTISGLQAEDEADYYCSSYTSTGTVVIG GGTKLTVL<br><br>SEQ ID NO: 24204 | QVQLVESGGGVVQPGRSLRLSCAASGFTFSSYVMH WVRQAPGKGLEWVAVIWYDGSNKYYADSVKVRF TVSRDNSKNTLSLQMNSLRAEDTAVYYCARERYTS GWYDYGMDVWGQGTTVTVSS<br><br>SEQ ID NO: 28210 |
|---|---|---|---|---|---|
| iPS:473253 | 21-225_7C3_LC1 | | NA | GACATCCAGATGACCCAGTCTCCATCCTCCCT GTCTGCATCTGTAGGAGACAGAGTCACCATCA CTTGCCGGGCAAGTCAGGGCATTAGAAGTGAT TTAGGCTGGTATCAGCAGAATCCAGTCAAAGC CCCTAAGCGCCTGATCTATGCTGCATCCAGTTT GCAAAGTGGGGTCCCATCGAGGTTCAGCGGCA GTGGATCTGGGACAGAATTCACTCTCACAGTC AGCAGCCTGCAGCCTGAAGATTTTGCATTTTA TTACTGTCTACAGCATAATAGTTACCTCCCCAT CACCTTCGGCCAAGGGACACGACTGGAAATTA AA<br><br>SEQ ID NO: 24205 | CAGGTGCAGCTGGTACAGTCTGGGGCTGAGGTG AAGAAGCCTGGGGCCTCAGTGAAGGTCTCCTGC AAGGCTTCTGGATACACCTTCAACGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCTGTCTGTGCGAGATGGTA GACACGGCCGTGTATTCCTGTGCGAGAGATGGTA CCAGCTCGTTTGACTACTGGGGCCAGGGAACCCT GGTCACCGTCTCCTCA<br><br>SEQ ID NO: 28211 |
| | | | AA | DIQMTQSPSSLSASVGDRVTITCRASQGIRSDLG WYQQNPVKAPKRLIYAASSLQSGVPSRFSGSGS GTEFTLTVSSLQPEDFAFYYCLQHNSYLPITFGQ GTRLEIK<br><br>SEQ ID NO: 24206 | QVQLVQSGAEVKKPGASVKVSCKASGYTFNDYYL HWVRQAPGQGLEWMGWIHPNSGGTNYAQKFQGR VTMTRDTSISTAYMELSSLRSDDTAVYSCARDGTSS FDYWGQGTLVTVSS<br><br>SEQ ID NO: 28212 |

FIGURE 50
(Continued)

| | | | |
|---|---|---|---|
| iPS:473254 | 21-225_7C3_LC2 | NA | GACATCCAGATGACCCAGTCTCCATCTTCCGT GTCTGCATCTGTAGGAGACAGAGTCACCATCA CTTGTCGGGCGAGTCAGGTATTAGCAGCTGG TTAGCCTGGTATCAGCAGAAACAAGGGAAAG CCCCTAAGCTCCTGATCTTTGCTGCATCCAGT TGCAAAGTGGGGCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A<br><br>SEQ ID NO: 24207 | CAGGTGCAGCTGGTACAGTCTGGGGCTGAGGTG AAGAAGCCTGGGGCCTCAGTGAAGGTCTCCTGC AAGGCTTCTGGATACACCTTCAACGACTACTATT TGCACTGGGTGCGACAGGCCCCTGGACAAGGTCT TGAGTGGATGGGATGGATCCACAGAAGTTTCACCTAACAGTGGT GGCACAAACTATGCACAGAAGTTTCAGGGCAGG GTCACCATGACCAGGGACACGTCCATCAGCACA GCCTACATGGAGCTGAGCAGCCTGAGATCTGAC GACACGGCCGTGTATTCCTGTGCGAGAGATGGTA CCAGTCGTTTGACTACTGGGGCCAGGGAACCCT GGTCACCGTCTCCTCA<br><br>SEQ ID NO: 28213 |
| | 21-225_7C3_LC2 | AA | DIQMTQSPSSVSASLGDRVTITCRASQGISSWLA WYQQKPGKAPKLLIFAASSRLQSGAPSRFSGSGS GTDFTLTISSLQPEDFATYYCQQANSFPFTFGPGT KVDIK<br><br>SEQ ID NO: 24208 | QVQLVQSGAEVKKPGASVKVSCKASGYTFNDYYL HWVRQAPGQGLEWMGWIHPNSGGTNYAQKFQGR VTMTRDTSISTAYMELSSLRSDDTAVYSCARDGTSS FDYWGQGTLVTVSS<br><br>SEQ ID NO: 28214 |
| iPS:473255 | 21-225_9F12_LC1 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCTGCATCCAGA TTGCAAAGTGGGGTCCCATCAAGGTTCAGCGG CAGTGGATCTGGGACAGATTTCACTCTCACCA TCAGCGGCCTGCTGCCTGAAGATTTTGCAATT TATTATTGTCAACAGGCTAACAGTTTCCCATTC ACTTTCGGCCCTGGGACCAAAGTGGATTTCAA A<br><br>SEQ ID NO: 24209 | CAGGTGCAGCTGGTACAGTCTGGGGCTGAGGTG AAGAAGCCTGGGGCCTCAGTGAAGGTCTCCTGC AAGGCTTCTGGATACACCTTCGCCGACTACTATT TGCACTGGGTGCGACAGGCCCCTGGACAAGGTCT TGAGTGGATGGGATGGATCCACAGACCTAACAGTGGT GGCACAAACTTTGCACAGAAGTTTCAGGGCAGG GTCACCATGACCAGGGACACGTCCATCAGCACA GCCTACCTGGAACTGAGCAGTCTGAGAGATGACG ACACGGCCCTCTATTACTGTGCGAGAGATGGTAC CAGTCGTTTGACTACTGGGGCCAGGGAACCCTG GTCACCGTCTCCTCA<br><br>SEQ ID NO: 28215 |

FIGURE 50
(Continued)

| | | | | |
|---|---|---|---|---|
| | | AA | DIQMTQSPSSVSASVGDRVTITCRASQGISRWLA WYQQKPGKAPKLLIYAASRLQSGVPSRFSGSGS GTDFTLTISGLLPEDFAIYYCQQANSFPFTFGPGT KVDFK<br><br>SEQ ID NO: 24210 | QVQLVQSGAEVKKPGASVKVSCKASGYTFADYYL HWVRQAPGQGLEWMGWIHPNSGGTNFAQKFQGR VTMTRDTSISTAYLELSSLRSDDTAFYYCARDGTSS FDYWGQGTLVTSS<br><br>SEQ ID NO: 28216 |
| iPS:473256 | 21-225_9F12_LC2 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGTCAAAGC CCCTAAGCGCCTTATCTATGCTGCATCCAGTTT GCAAAGTGGGGGTCCCATCAAGGTTCAGCGGCA GTGGATCTGGGACAGAATTCACTCTCACAATC AGCAGCCTGCAGCCTGAAGATTTGCAACTTA TTACTGTCTACAGCATAATAGTTACCTCCCCAT CACCTTCGGCCAAGGACACAGACTGGAGATTA AA<br><br>SEQ ID NO: 24211 | CAGGTGCAGCTGGTACAGTCTGGGGCTGAGGTG AAGAAGCCTGGGGCCTCAGTGAAGGTCTCCTGC AAGGCTTCTGGATACACCTTCGCCGACTACTATT TGCACTGGGTGCGACAGGCCCCTGGACAAGGTCT TGAGTGGATGGGATGGATCCACCTAACAGTGGT GGCACAAACTTTGCACAGAAGTTTCAGGGCAGG GTCACCATGACCAGGGACACGTCCATCAGCACA GCCTACCTGGAACTGAGCAGTCTGAGATCGACG ACACGGCCTTCTATTACTGTGCGAGAGATGGTAC CAGTCGTTTGACTACTGGGGCCAGGGAACCCTG GTCACCGTCTCCTCA<br><br>SEQ ID NO: 28217 |
| | | AA | DIQMTQSPSSLSASVGDRVTITCRASQGIRNDLG WYQQKPVKAPKRLIYAASSLQSGVPSRFSGSGS GTEFTLTISSLQPEDFATYYCLQHNSYLPITFGQG TRLEIK<br><br>SEQ ID NO: 24212 | QVQLVQSGAEVKKPGASVKVSCKASGYTFADYYL HWVRQAPGQGLEWMGWIHPNSGGTNFAQKFQGR VTMTRDTSISTAYLELSSLRSDDTAFYYCARDGTSS FDYWGQGTLVTVSS<br><br>SEQ ID NO: 28218 |

FIGURE 50
(Continued)

| | | | | |
|---|---|---|---|---|
| iPS:472742 | 21-225_30D9_LC2 | NA | TCCTATGAGCTGACTCAGCCACCCTCAGTGTCCGTGTCCCCAGGACAGACAGCCAGCATCACCTGCTCTGGAGATAAATTGGGGGATAAATATGTTTACTGGTTTCAGCAGAAGCCAGGCCAGTCCCCTGTGCTAGTCATCTATCAAGATAGGAAGCGGCCCTCAGGGATCCCTGAGCGATTCTCTGGCTCCAACTCTGGGAACACAGCCACTCTGACCATCAGCGGGACGCAGGCTCTGGATGAGGCTGACTATTACTGTCAGGCGTGGGACAACAGCACTGCGGTATTCGGCGGAGGGACCAAGCTGACCGTCCTA SEQ ID NO: 24213 | CAGGTGAAACTGGTGCAGTCTGGGGCTGAGGTGGAGAAGCCTGGGGCCTCAGTGAAGGTCTCCTGCAAGGCTTCAGGATACACCTTCACCGGCTACTATCTGCACTGGGTGCGACAGGCCCCTGGACAAGGGCTTGAGTGGATGGGATGGATCAACCCTAACAGTGGTGCACAAACTATGCACAGAAGTTTCAGGGCAGGGTCACCATGACCAGGGACACGTCCATCAGCACAGCCTACATGGAGCTGAGCAGGCTGAGATCTGACACGGCCGTGTATTACTGTGCGAGAGTGTATTACTATGTTCGGGGAGTTATTATAACGAGTTGACAACTGGGGCCAGGGAACCCTGGTCACCGTCTCCTCA SEQ ID NO: 28219 |
| | | AA | QVKLVQSGAEVEKPGASVKVSCKASGYTFTGYYLHWVRQAPGQGLEWMGWINPNSGTNYAQKFQGRVTMTRDTSISTAYMELSRLRSDDTAVYYCARVYYYGSGSYYNEFDNWGQGTLVTVSS SEQ ID NO: 28220 | |
| iPS:472741 | 21-225_30D9_LC1 | NA | GATGTCGTGATGACTCAGTCTCCACTCTCCCTGCCCGTCACCCTTGGACAGCCGGCCTCCATCTCCTGCAGGTCTAGTCAAAGCCTCGTACTCCAGTGATGGAAACACCTTCTTGAATTGGTTTCAGCAGAGGCCAGGCCAATCTCAAGGCGCCTAATTTAAGGTTTCTAACTGGGACTCTGGGGTCCCAGACAGATTCAGCGGCAGTGGGTCAGGCACTGATTTCACACTGAAAATCAGCAGGGTTGAGGCTGAGGATGTTGGGGTTTATTACTGTCTGCAAGGTACACACTGGCCTCTCACCTTCGGCCAAGGGACACGACTGGAGATTAAA SEQ ID NO: 24215 | CAGGTGAAACTGGTGCAGTCTGGGGCTGAGGTGGAGAAGCCTGGGGCCTCAGTGAAGGTCTCCTGCAAGGCTTCAGGATACACCTTCACCGGCTACTATCTGCACTGGGTGCGACAGGCCCCTGGACAAGGGCTTGAGTGGATGGGATGGATCAACCCTAACAGTGGTGCACAAACTATGCACAGAAGTTTCAGGGCAGGGTCACCATGACCAGGGACACGTCCATCAGCACAGCCTACATGGAGCTGAGCAGGCTGAGATCTGACACGGCCGTGTATTACTGTGCGAGAGTGTATTACTATGTTCGGGGAGTTATTATAACGAGTTGACAACTGGGGCCAGGGAACCCTGGTCACCGTCTCCTCA SEQ ID NO: 28221 |

FIGURE 50
(Continued)

| | | | |
|---|---|---|---|
| iPS:472743 | 21-225_68G6 | AA | DVVMTQSPLSLPVTLGQPASISCRSSQSLVSSDG NTFLNWFQQRPGQSPRRLIYKVSNWDSGVPDRF SGSGSGTDFTLKISRLEAEDVGVYYCLQGTHWP LTFGQGTRLEIK<br>SEQ ID NO: 24216 | QVKLVQSGAEVEKPGASVKVSCKASGYTFTGYYL HWVRQAPGQGLEWMGWINPNSGGTNYAQKFQGR VTMTRDTSISTAYMELSRLRSDDTAVYYCARVYYY GSGSYYNEFDNWGQGTLVTVSS<br>SEQ ID NO: 28222 |
| | | NA | TCCTATGAGGTGACTCAGCCACCCTCAGTGTC CGTGTCCCCAGGACAGAGACAGCCAGCATCACCT GCTCTGGAGATAAATTGGGGGATAAATATACT TACTGGTATCAGCAGAAGGCAGGCCAGTCCCC TTTCCTGGTCATCTATCAAGATAGGAAGCGGC CCTCAGGGATCCCTGACCGATTCTCTGGCTCC AACTCTGGGAACACAGCCACTCTGACCATCAG CGGGACCCAGGCTATGGAGACAATAGTACTGCGGTA ACTGTCAGGCGTGGGACCAAGCTGACCGTCCTA<br>SEQ ID NO: 24217 | CAGGTGCAGTTGGTGCAGTTTGGGGGTGAGGTGA AGAAGCCTGGGTCCTCAGTGAAGGTNTCCTGCAA GGCTTCAGGATACACCTTCACCGGGTTACTATATG CACTGGGTGCGACAGGCCCCTGGACAAGGGCTT GAGTGGATGGGATCGATCTACCGTAACAGTGGTG GCACAAATTATGCACAGAAGTTTCAGGGCAGGG TCACCATGACCAGGGACAAGTCCATCAGCACCG CCTACATGGAGAAGAGCAGGATCAGATCTGATG ACACGGCCGTGTATTACTGTGCGAGAGCCTTTA CTATGGTTCGGGGACTTATTATAACGAATTTGAC TACTGGGGCCAGGGAACCCTGGTCACCGTCTCCT CA<br>SEQ ID NO: 28223 |
| | | AA | SYEVTQPPSVSVSPGQTASITCSGDKLGDKYTY WYQQKAGQSPFLVIYQDRKRPSGIPDRFSGSNSG NTATLTISGTQAMDAADFYCQAWDNSTAVFGG GTKLTVL<br>SEQ ID NO: 24218 | QVQLVQFGGEVKKPGSSVKVSCKASGYTFTGYYM HWVRQAPGQGLEWMGSIYRNSGGTNYAQKFQGR VTMTRDKSISTAYMEKSRIRSDDTAVYYCARAFYY GSGTYYNEFDYWGQGTLVTVSS<br>SEQ ID NO: 28224 |

FIGURE 50
(Continued)

| | | | |
|---|---|---|---|
| iPS:392573 | 21-225_15G2 | NA | CAGTCTGCCCTGACTCAGCCTGCCTCCGTGTCT GGGTCTCCTGGACAGTCGGATCACCATCTCCTG CACTGGAACCAGCAGTGACGTTGGTGGTATA ACTATGTCTCCTGGTACCAACAGCACCAGGC AAAGCCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCACCTCATATACAAGCACCAG CACTGTGGTCTTCGGCGGAGGGACCAAGCTGA CCGTCCTA<br><br>SEQ ID NO: 24219 | CAGATCACCTTGAAGGAGTCTGGTCCTACGCTGG TGAAACCACACAGACCCTCACGCTGACCTGCAC CTTCTCTGGATTCTCACTCAGCACTAGTGGAGTG GGTGTGGGCTGGATCCGTCAGCCCCCAGGAAAG GCCCTGGAGTGGCTTGCACTCATTTATTGGAATG ATGATAAGCGCTACAGCCCATCTCTGAAGAGCA GGCTCACCATCTCCAAGGACACCTCCAAAAACC AGTTGGTCCTTACAATGACCAACATGGACCCTGT GGACACAGCCACATATTACTGTGCAGACACGGT GTCAGCTGCTGCTATTTCACTATTGGGGCCAGG GAACCCTGGTCACCGTCTCCTCA<br><br>SEQ ID NO: 28225 |
| | | AA | QSALTQPASVSGSPGQSITISCTGTSSDVGGYNY VSWYQQHPGKAPKLMIYEVSNRPSGVSNRFSGS KSGNTASLTISGLQAEDEADYYCTSYTSTSTVVF GGGTKLTVL<br><br>SEQ ID NO: 24220 | QITLKESGPTLVKPTQTLTLTCTFSGFSLSTSGVGVG WIRQPPGKALEWLALIYWNDDKRYSPSLKSRLTIT KDTSKNQVVLTMTNMDPVDTATYYCADTGVSCC YFHYWGQGTLVTVSS<br><br>SEQ ID NO: 28226 |
| iPS:392583 | 21-225_10B10 | NA | TCCTATGAGCTGACTCAGCCACCCTCAGTGTC CGTGTCCCAGGACAGACAGCAGCATCACCT GCTCTGGAGATAAATTGGGAATAAATATGCT TGGTGTATCAGCAGAAGCCAGGCCAGTCCCC TGTGCTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAACAGCACTGTGGTT TTCGGCGGAGGGACCAAACTGACCGTCCTA<br><br>SEQ ID NO: 24221 | CAGATCACCTTGAAGGAGTCTGGTCCTACGCTGG TGAAACCACACAGACCCTCACGCTGACCTGCAC CTTCTCTGGGTTCTCACTCAGCACTAGTGGAGTG GGTGTGGGCTGGATCCGTCAGCCCCCAGGAAAG GCCCTGGAGTGGCTTGTATTCATTTATTGGAGTG ATGATAAGCGCTACAGCCCATCTCTGAAGAGCA GGCTCTCCATCACCAAGGACACCTCCAAAAACCA GGTGGTCCTTACAATGACCAACATGGACCCTGTG GACACAGCCACATATTACTGTGCACGTATAGCAG CAGTTGCCTTTGACTACTGGGGCCAGGAGAACCCT GGTCACCGTCTCCTCA<br><br>SEQ ID NO: 28227 |

FIGURE 50
(Continued)

| | | | |
|---|---|---|---|
| iPS:392585 | 21-225_14H11 | AA | SYELTQPPSVSVSPGQTASITCSGDKLGNKYAW WYQQKPGQSPVLVIYQDRKRPSGIPERFSGSNSG NTATLTISGTQAMDEADYYCQAWDNSTVVFGG GTKLTVL<br>SEQ ID NO: 24222 | QITLKESGPTLVKPTQTLTLTCTFSGFSLSTGGVGVG WIRQPPGKALEWLVFIYWSDDKRYSPSLKSRLSITK DTSKNQVVLTMTNMDPVDTATYYCARIAAVAFDY WGQGTLVTVSS<br>SEQ ID NO: 28228 |
| | | NA | ACCTATGAGCTGACTCAGCCATCCTCAGTGTC CGTGTCCCCAGGACAGACAGCCAGCATCACCT GCTCTGGAGATAAATTGGGGAAAATATGTT TGCTGGTATCAGCAGAAGCCAGGCCAGTCCCC TGTGCTGGTCATATATCAGGATCTCTGGCTCC CCTCAGGGATCCCTGAGCGATTCTCTGGCTCC AACTCTGGGAACACAGCCACTCTGACCATCAG CGGAACCCAGGCTATGGAGGCTGACTATT ACTGTCAGGCGTGGGACAGCAGCACTATATTC GGCGGAGGGACCAAGCTGACCGTCCTA<br>SEQ ID NO: 24223 | CAGGTGCAGCTGGTGCAGTCTGGGGCTGAGGTG AAGAAGCCTGGGGCCTCAGTGAAGGTCTCCTGCC AGGGTTCTGGATACACCTTCACCGGCCACTATAT GTGCTGGGTGCGACAGGCCCCTGGACAAGGGCT TGAGTGGATGGGATGGATCAACCTAATAGTGGT GGCACAAACTATGCACAGGACACGTTCAGGGCAGG GTCACCATGACCAGGGACACGTCCATCAGCACA GCCTACATGGAGCTGAGCAGGCTGAGATCTGAC GACACGGCCGTGTATTACTGTGCGGCTGATATT GTAGTAGTTCCAGCTGCTATTTGCAACCGGGTTA TACGGTATGGACGTCTGGGGCCAAGGGACCAC GGTCACCGTCTCCTCA<br>SEQ ID NO: 28229 |
| | | AA | TYELTQPSSVSVSPGQTASITCSGDKLGEKYVCW YQQKPGQSPVLVIYQDTKRPSGIPERFSGSNSGN TATLTISGTQAMDEADYYCQAWDSSTIFGGGTK LTVL<br>SEQ ID NO: 24224 | QVQLVQSGAEVKKPGASVKVSCQGSGYTFGHYM CWVRQAPGQGLEWMGWINPNSGGTNYAQKFQGR VTMTRDTSISTAYMELSRLRSDDTAVYYCAAGYCS SSSCYLQPGYYGMDVWGQGTTVTVSS<br>SEQ ID NO: 28230 |

FIGURE 50
(Continued)

| | | | | |
|---|---|---|---|---|
| iPS:392587 | 21-225_18G5 | NA | TCCTATGAGCTGACTCAGCCACCCTCAGTGTCCGTGTCCCCAGGACAGACAGCCAGCATCACCTGCTCTGGAGAGAAATTGGGGGATAAATATGTTTGTTGGTATCAGCAGAAGCCAGGCCAGTCCCCTGTGCTGGTCATCTATCAAGATAGCAAGCGGCCCTCAGGGATCCCTGAGCGATTCTCTGGCTCCAACTCTGGGAACAGCACTGGATGAGGCTGACTATTCGGGACCCAGGCTGTGAACAGCAGCAATGTGGTAACTGTCAGGGCGTGGGGACCAAGCTGACCGTCCTATTCGGCGGAGGGACCAAGCTGACCGTCCTA | CAGATCACCTTGAAGGAGTCTGGTCCTACGCTGG TGAAACCCACACAGACCCTCACGCTGACCTGCAC CTTCTCTGGGTTCTCACTCAGCACTAGTGGAGTG GGTGTGGGCTGATCCGTCAGCCCCCAGGAAAG GCCCTGGAGTGCCTTCACTCATTTATTGGAATG ATGATAAGGTCTACAGCCCATCTCTGAAGAGCAG GCTCACCATCACCAAGTACACCCTCAAAACCAG GTGGTCCTTACAATGACCAACATGACCCTGTGG ACACAGCCACATATTACTGTGCACACAGGGAC AGCAGCTGGCCCTGACTACTGGGGCCAGGGAA CCCTGGTCACCGTCTCCTCA |
| | | | SEQ ID NO: 24225 | SEQ ID NO: 28231 |
| | | AA | SYELTQPPSVSVSPGQTASITCSGEKLGDKYVCW YQQKPGQSPVLVIYQDSKRPSGIPERFSGSNSGN TATLTISGTQAMDEADYYCQAWNSSNVFGGG TKLTVL | QITLKESGPTLVKPTQTLTLTCTFSGFSLSTSGVVG WIRQPPGKALECLSLIYWNDDKVYSPSLKSRLTITK YTSKNQVVLTMTNMDPVDTATYYCAHRGQQLAL DYWGQGTLVTVSS |
| | | | SEQ ID NO: 24226 | SEQ ID NO: 28232 |
| iPS:392589 | 21-225_27H2 | NA | TCCTATGAGCTGACTCAGCCACCCTCAGTGTCCGTATCCCCAGGACAGACAGCCAGCATCACCTGCTCTGGAGATAAATTGGGGGATAAATATGCTTCCTGGTATCAGCAGAAGCCAGGCCAGTCCCCTGTTTTGGTCATCTATCAAGATGGCAAGCGGCCCTCAGGGATCCCTGAGCGATTCTCTGGCTCCAACTCTGGGAACACAGGCTATGATGAGGCTGACTATTCAGGGACCCAGGCTGTGGACAGCAGCACTTATGTGACTGTCAGGCGGTGGGACAGCAGCAAGCTGACCGTCCTAGTATTCGGCGGAGGGACCAAGCTGACCGTCCTA | CAGGTGCAGTTGGTGGAGTCTGGGGGAGGCGTG GTCCAGCCTGGAGGGTCCCTGAGACTCTCCTGTG CAGCGTCTGGATTCACCTTCAGTGGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTTTCTGCAAATGAACAGCCTGAGAGCCGAGG ACACGGCTGTGTATTACTGTGCGAGAGATAGGGT ATATTGTAGTAGTACCAGCTGCTCCCCTTACTAC TACTACTACGGTATGGACGTCTGGGGCCAAGGG ACCACGGTCACCGTCTCCTCA |

FIGURE 50
(Continued)

| | | | SEQ ID NO: 24227 | SEQ ID NO: 28233 |
|---|---|---|---|---|
| | | AA | SYELTQPPSVSVSPGQTASITCSGDKLGDKYASW YQQKPGQSPVLVIYQDKRPSGIPERFSGSNSGN TATLTLSGTQAMDEADYYCQAWDSSTYVFGG GTKLTVL | QVQLVESGGGVVQPGRSLRLSCAASGFTFSGYGM HWVRQAPGKGLEWVAVIWYDGSNKYADSVKGR FTISRDNSKNTLFLQMNSLRAEDTAVYYCARDRVY CSSTSCSPYYYYGMDVWGQGTTVTVSS |
| | | | SEQ ID NO: 24228 | SEQ ID NO: 28234 |
| iPS:392593 | 21-225_3E10 | NA | TCCTATGAGCTGACTCAGCCACACTCAGTGTC AGTGGCCACAGCACAGATGGCCAGGATCACCT GTGGGGAAACAACATTGGAAGTAAAGCTGT GCACTGGTACCAGCAAAAGCCAGGACAGGAC CCTGTGCTGGTCATCTATAGCGATAGCAACCG GCCCTCAGGGATCCCTGAGCGATTCTCTGGCT CCAACCCAGGGAACACCGCCACCCTAACCATC AGCAGGATCGAGGCTGGGGATGCAGTAGTGAT ATTACTGTCAGGTGTGGGCGGAGGAGGACCAAGCTGAC CATGTGGTATTCGGCGGAGGGACCAAGCTGAC CGTCCTA | CAGATCACCTTGAAGGAGTCTGGTCCTACGCTGG TGAAACCCACACAGACCCTCACGCTGACCTGCAC CTTCTCTGGGTTCTCACTCAATACTGGTGGAGTG GGTGTGGCGTGGATCCGTCAGCCCCCAGGAAAG GCCCTGGAGTGGCTTGCACTCATTTATTGGAATG ATGATAAGCGCCACAGCCATCTGAAGAGCA GGCTCACCATCACCAAAGACACCTCCAAAAACC AGTTGGTCCTTACAATGACCACATGGCCCCTGT GGACACAGCCACATATTACTGTGCACACCTTATA GAAGTGGCCTTTGACTATTGGGGCCAGGGAACCC TGGTCACCGTCTCCTCA |
| | | | SEQ ID NO: 24229 | SEQ ID NO: 28235 |
| | | AA | SYELTQPHSVSVATAQMARITCGGNNIGSKAVH WYQQKPGQDPVLVIYSDSNRPSGIPERFSGSNPG NTATLTISRIEAGDEADYYCQVWDSSSDHVFG GGTKLTVL | QITLKESGPTLVKPTQTLTLTCTFSGFSLNTGGVGV GWIRQPPGKALEWLALIYWNDDKRHSPSLKSRLTI TKDTSKNQVVLTMTHMAPVDTATYCAHLIEVAF DYWGQGTLVTVSS |
| | | | SEQ ID NO: 24230 | SEQ ID NO: 28236 |

FIGURE 50
(Continued)

| | | | |
|---|---|---|---|
| iPS:392596 | 21-225_12D8 | NA | CTGCCTCTGTGCTGACTCAGCCCCGTCTGCATCT GCCTTGCTGGGAGCCTGATCAAGCTCACCTG CACCCTAAGCAGTGAGCACAGCACTACACCA TCGAATGGTATCAACAGAGACCAGGAGGTC CCCCAGTATATATAAGGTTAAGAGTGATG GCAGCCACAGCAAGGGGACGGGATCCCGA TCGCTTCATGGGCTCCAGTTCTGGGCTGACC GCTACCTCACCTTCTCCAACCTCCAGTCTGACG ATGAGGATGAGTATCACTGTGGAGAGAGCCA CACGATTGATGCCAAGTCGGTGTGTATTCG GCGGAGGGACCAAGCTGACCGTCCTA SEQ ID NO: 24231 | GAGGTGCAGTTGTTGAATCTGGGGAGGCTGG TACAGCCTGGGGGGTCCCTGAGACTCTCCTGTGC AGCCTCTGGATTCACCTTTAGCAGCTATGTCATG AGCTGGGTCCGCCAGGCTCCAGGGAAGGGCTG GAGTGGGTCTCAACTATTAGTGTTGGTGGTGTA GCACATACTACGCAGACTCCGTGAAGGGCCGGTT CACCATCTCCAGAGACAATTCCAAGACCACGCTG TATCTGCAAATGAACAGCCTGAGAGCCGAGGAC ACGGCCGTATATTACTGTGCGAAATGGGGACGTG GATACAGCTATGAATACTACTACGGTATGGACGT CTGGGGCCAAGGGACCACGGTCACCGTCTCCTCA SEQ ID NO: 28237 |
| | | AA | LPVLTQPPSASALLGASIKLTCTLSSEHSTYTIEW YQQRPGRSPQYIMKVKSDGSHSKGDGIPDRFMG SSSGADRYLTFSNLQSDDEDEYHCGESHTIDGQV GVVFGGGTKLTVL SEQ ID NO: 24232 | EVQLLESGGGLVQPGGSLRLSCAASGFTFSSYVMS WVRQAPGKGLEWVSTISVGGGSTYYADSVKGRFTI SRDNSKTTLYLQMNSLRAEDTAVYYCAKWGRGYS YEYYYGMDVWGQGTTVTVSS SEQ ID NO: 28238 |
| iPS:392598 | 21-225_18E10 | NA | TCCTATGAACTGACGCAGCCACCCTCAGTGTC CGTGTCCCCAGGACAGACAGCCAGCATCACCT GCTCTGGAGATAGATTGGGGGATAAATATGCT TGGTGGTATCAGCAGAAGCCAGGCCAGTCCCC TGTGCTGGTCATATATCAAGATCGCAAGCGGC CCTCAGGGATCCCTGAGCGATTCTCTGGCTCC AATTCAGGGAACACACACTCTGACCATCAG CGGGACCCAGGCTATGGATGAGGCTGACTATT ACTGTCAGGCGTGGGACAGCAGCACAGTGGT ATTCGGCGGAGGGACCAAGCTGACCGTCCTA SEQ ID NO: 24233 | CAGGTGCAGCTGGTGCAGTCTGGGGCTGAGGTG AAGAAGCCTGGGGCCTCAGTGAAGGTCTCCTGC AAGGCTTCTGGATACACCTTCACGGGCTACTATA TGCACTGGGTGCGACAGGCCCCTGGACAAGGGC TTGAGTGGATGGGGTGGATCAACCCTAACAGTGG TGGCACAAACTATGCACAGAAGTTTCAGGGCAG GGTCACCATGACCAGGGACTCGTCCATCAACACA GCCTACATGGAGCTGAGCAGGCTGAGATCTGAC GACACGGCCGTGTATTACTGTGCGAGGTCGTACT ACTATGGTTCGGGGAGTTATTATAACGAGTTTGA CTACTGGGGCCAGGGAACCCTGGTCACCGTCTCC TCA SEQ ID NO: 28239 |

FIGURE 50
(Continued)

| | | | |
|---|---|---|---|
| iPS:392618 | 21-225_16F10 | AA | SYELTQPPSVSVSPGQTASITCSGDRLGDKYAW WYQQKPGQSPVLVIYQDRKRPSGIPERFSGSNSG NTATLTISGTQAMDEADYYCQAWDSSTVVFGG GTKLTVL<br>SEQ ID NO: 24234 | QVQLVQSGAEVKKPGASVKVSCKASGYTFTGYYM HWVRQAPGQGLEWMGWINPNSGGTNYAQKFQGR VTMTRDSSINTAYMELSRLRSDDTAVYYCARSYYY GSGSYYNEFDYWGQGTLVTVSS<br>SEQ ID NO: 28240 |
| | | NA | GATATTGTGATGACCCAGACTCCACTCTCTCT GTCCGTCATTCCTGACAGCCGGCCTCCATCT CCTGCAAGTCTAGTCAGAGCCTCCTGCATAGT GATGGAAAGACCCATTTGAATTGGTACCTGCA GAAGCCAGGCCAGCCTCCACAGCTCCTGATCT ATGAAGTTTCCTACCGGTTCTCTGGAGTGCCA GATAGGTTCAGTGGCAGTGGGTCAGGGACAG TTTTCACACTGGAGATCAGCGGGGTGGAGGCT GCGGATGTTGGGGTTTATTACTGCTTTCAAAG TATACAGCTTCCGCTCACTTTCGGCGGAGGGA CCAAGGTGGAGATCAAA<br>SEQ ID NO: 24235 | CAGGTGCAGCTGGTGGAGTCTGGGGGAGGCGTG GTCCAGCCTGGGAGGTCCCTGAGACTCTCCTGTG CAGCGTCTGGATTCACCTTCACTGACTATGGCAT GCACTGGGTCCGCCAGGCTCCAGGCAAGGGCT GGAGTGGGTGGCAGTCATATGGTATGATGAAA TAATAAATACTATGTAGACTCCGTGAAGGGCCGA TTCACCATCTCAAGAGACAACAATTCCAAGAATACGC TGTATCTGCAAATGAACAGCCTGAGAGCCGAGG ACACGGCTGTGTATTACTGTGCGAGAGAGCTTGC CTGGTACGAGGACTACTGGGGCCAGGGAACCCT GGTCACCGTCTCCTCA<br>SEQ ID NO: 28241 |
| | | AA | DIVMTQTPLSLSVIPGQPASISCKSSQSLLHSDGK THLNWYLQKPGQPPQLLIYEVSYRFSGVPDRFSG SGSGTVFTLEISRVEAADVGVYYCFQSIQLPLTF GGGTKVEIK<br>SEQ ID NO: 24236 | QVQLVESGGGVVQPGRSLRLSCAASGFTFSDYGM HWVRQAPGKGLEWVAVIWYDGNNKYYVDSVKG RFTISRDNSKNTLYLQMNSLRAEDTAVYYCARELA WYEDYWGQGTLVTVSS<br>SEQ ID NO: 28242 |

FIGURE 50
(Continued)

| | | | |
|---|---|---|---|
| iPS:392620 | 21-225_17H5 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCAATGCTGCATCCAGTT ACAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATCATAGTTACCCATTCA CTTTCGGCCCTGGGACCAAAGTGGATATCAAA<br/>SEQ ID NO: 24237 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCATTAGTAGTAGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGTGGCTTCA TTTGACTACTGGGGCCAGGGAACCCTGGTCACCG TCTCCTCA<br/>SEQ ID NO: 28243 |
| | | AA | DIQMTQSPSSLSASVGDRVTITCRASQGISNYLA WFQQKPGKAPKSLINAASSLQSGVPSKFSGSGSG TDFTLTISSLQPEDFATYYCQQYHSYPFTFGPGT KVDIK<br/>SEQ ID NO: 24238 | EVQLVESGGGLVKPGGSLRLSCAASGFTFSSYSMN WVRQAPGKGLEWVSSISSSSTYIYYADSVKGRFTIS RDNAKNSLYLQMNSLRAEDTAVYYCARVASFDY WGQGTLVTVSS<br/>SEQ ID NO: 28244 |
| iPS:392622 | 21-225_17H8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGGTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTACAACT TATTACTGTCTACAGCATAATAGTTACCCACTC ACTTTCGGCGGAGGGACCAAGGTGGAGATCA AA<br/>SEQ ID NO: 24239 | CAGCTGCAGCTGCAGGAGTCGGGCCCAGGACTG GTGAAGCCTTCGGAGACCCTGTCCTCACCTGCA CTGTCTCTGGTGGCTCATCAGTAGAAGTAGTTA CTACTGGGGCTGGATCCGCCAGCCCCCAGGGAG GGGGCTGGAGTGGATTGGGAATATCTATTATGGT GGGAACACTACTACAACCGTCCCTCAAGAGTC GAGTCACCATATCCGTAGACACGTCCAAGAACC AGTTCTCCCTGAAGCTGAGCTCTGTGACCGCCGC AGACACGGCTGTGTATTACTGTGCGAGACATGGA AAAGACTGGGCCTTGACTACTGGGGCCAGGGA ACCCTGGTCACCGTCTCCTCA<br/>SEQ ID NO: 28245 |

FIGURE 50
(Continued)

| | | AA | DIQMTQSPSSLSASVGDRVTITCRASQGIRNDLG WYQQKPGKAPKRLIYGASSLQSGVPSRFSGSGS GTEFTLTISSLQPEDFTTYCLQHNSYPLTFGGGT KVEIK SEQ ID NO: 24240 | QLQLQESGPGLVKPSETLSLTCTVSGGSISRSSYYW GWIRQPPGRGLEWIGNIYYGGNTYNPSLKSRVTIS VDTSKNQFSLKLSSVTAADTAVYYCARHGKDWGL DYWGQGTLVTVSS SEQ ID NO: 28246 |
|---|---|---|---|---|
| iPS:392624 | 21-225_17H12 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAAGCAGGAAAG CCCCTAAGCGCCTGATCAATGCTGCATCCAGT TTGCAAAGTGGGGTCCCATCCAAGGTTCAGCGG CATTGGCTCTGGGACAGAATTCACTCTCACAA TCACCGGCCTGCAGCCTGAAGATTTTGCAACT TATTACTGTCTACAGCATTATAGTTATATGTTC ACTTTCGGCGGAGGGACCAAGGTGGAGATCA AA SEQ ID NO: 24241 | GAGGTGCAACTGGTGGAGTCTGGGGGAGGCCTG GTCAAGCCTGGGGGGTCCCTGAGACTCTCCTGTG CAGCCTCTGGATTCACCTTCAGTAGCTATACCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATTTGCAAATGAACAGCCTGAGAGCCGAGGA CACGGCTGTATATTACTGTGCGAGAGATCGAGGC TCCATCTGGGGCCAAGGGACAATGGTCACCGTCT CTTCA SEQ ID NO: 28247 |
| | | AA | DIQMTQSPSSLSASVGDRVTITCRASQDIRNDLG WYQQKAGKAPKRLINAASSLQSGVPSRFSGIGS GTEFTLTITGLQPEDFATYYCLQHYSYMFTFGGG TKVEIK SEQ ID NO: 24242 | EVQLVESGGGLVKPGGSLRLSCAASGFTFSSYTMN WVRQAPGKGLEWVSSISGSSSYIYYADSVKGRFTIS RDNAKNSLYLQMNSLRAEDTAVYYCARDRGSIWG QGTMVTVSS SEQ ID NO: 28248 |

FIGURE 50
(Continued)

| | | | |
|---|---|---|---|
| iPS:392626 | 21-225_18A5 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAATAGTTACCCGTGGACGTTCGGCCAAGGGACCAAGGTGGAAATCAAA<br><br>SEQ ID NO: 24243 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKVEIK<br><br>SEQ ID NO: 24244 | CAGGTGCAGTTGGTGGAGTCTGGGGGAGGCGTGGTCCAGCCTGGGAGGTCCCTGAGACTCTCCTATACAGCGTCTGGATTCACCTTCAGTGACTATGGCATGCACTGGGTCCGCCAGGCTCCAGGCAAGGGGCTGGAGTGGGTGGCAGTTATATGGTTTGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCTTGGCTGGACGGAAGAGTACTGGGGCCAGGGAACCCTGGTCACCGTCTCCTCA<br><br>SEQ ID NO: 28249 |
| | | | QVQLVESGGGVVQPGRSLRLSYTASGFTFSDYGMHWVRQAPGKGLEWVAVIWFDGSNKYYADSVKGRFTISRDNSKNTLYLQMNSLRAEDTAVYYCARDLGWTEEYWGQGTLVTVSS<br><br>SEQ ID NO: 28250 |
| iPS:392628 | 21-225_20C2 | NA | GACATCCAGATGACCCAGTCTCCATCCTCCCTGTCTGCATCTGTACAAGACAGAGTCACCATCACTTGCCGGGCAAGTCAGGGCATTAGAAATGATTTAGGCTGGTATCAGCAGAAACCAGGGAAAGCCCCTAAGCGCCTGATCTTTGCTGCATCCAGTTTGCAAAGTGGGGTCCCGTCAAGGTTCAGCGGCAGTGGATCTGGGACAGAATTCACTCTCACAATCAGCAGCCTGCAGCCTGAAGATGTCTAGTTACCCGCTCAATTACTGTCTCAACATGCTAGTTACCCGCTCACTTTTCGGCGGAGGGACCAAGGTGGAGATCGAA<br><br>SEQ ID NO: 24245 | CAGCTGCAGCTGCAGGAGTCGGGCCCAGGACTGGTGAAGCCTTCGGAGACCCTGTCCTCACCTGCACTGTCTCTGGTGGCTCCATCAGCAGAAGTAGTTACTACTGGGGCTGGATCCGCCAGCCCCCAGGGAAGGGGCTGGAGTGGATTGGGAATATCTATTATAGTGGGAGCTACCTGTAATTCGTCCCTCAAGAGTCGAGTCATTATATCCGTAGACACGTCCAAGAACCAGTTCTCCCTGAAGCTGAGCTGTGTGACCGCCACAGACACGGCTGTGTATTACTGTGCGAGACATAGTAGCAGCTGGTTCCTTGACAACTGGGGCCAGGGAACCCTGGTCACCGTCTCCTCA<br><br>SEQ ID NO: 28251 |

FIGURE 50
(Continued)

| | | | |
|---|---|---|---|
| iPS:392630 | | AA | DIQMTQSPSSLSASVGDRVTITCRASQGIRNDLG WYQQKPGKAPKRLIFAASSLQSGVPSRFSGSGSG TEFTLTISSLQPEDFATYYCLQHASYPLTFGGGT KVEIE<br>SEQ ID NO: 24246 | QLQLQESGPGLVKPSETLSLTCTVSGGSISRSSYYW GWIRQPPGKGLEWIGNIYYSGTAYCNSSLKSRVIIS VDTSKNQFSLKLSSVTATDTAVYYCARHSSSWSLD NWGQGTLVTVSS<br>SEQ ID NO: 28252 |
| | 21-225_20E5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGACAGAATTCACTCTCACAA TCAGCAGCCTGCAGCCTGAAGATTTTGCAACT TATTACTGTCTACAGCATATAGTTACCCGCTC ACTTTCGGCGGAGGGACCAAGGTGGAGATCA AA<br>SEQ ID NO: 24247 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATTTGGTATGAAGAAAAT AATCAATACTATGCAGACTCCGTGAAGGGCCGAT TCACCATCTCCAGAGACAATCCAAGAACACGCT GTATCTGCAAATGAACAGCCTGAGAGCCGAGA CACGGCTGTGTATTACTGTGCGAGAGAACTGGGG TTCCGGTCTGACTACTGGGGCCAGGGAACCCTGG TCACCGTCTCCTCA<br>SEQ ID NO: 28253 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24248 | QVQLVESGGGVVQPGRSLRLSCAASGFTFSDYGM HWVRQAPGKGLEWVAVIWYEENNQYYADSVKGR FTISRDNSKNTLYLQMNSLRAEDTAVYYCARELGF RSDYWGQGTLVTVSS<br>SEQ ID NO: 28254 |

FIGURE 50
(Continued)

| | | | |
|---|---|---|---|
| iPS:392632 | 21-225_16A11 | NA | GACATCCAGATGACCCAGTCTCCATCCTCCT GTCTGCATCTGTGGAGACAGTCACCATCT CTTGCCGGGCAAGTCAGGACATTAGAAATCAT TTAGGCTGGTATCAGCGTAACCAGGGAAAGC CCCTAAGCGCCTGATCTATGCTGCATCCAGTT GCAAAGTGGGGTCCCATCAAGGTTCAGCGGCA GTGGATCTGGGACAGACTTCACTCTCACAATC AGCAGCCTGCAGCCTGAAGACTTTGCAACTTA TTACTGTCTACAGTATATAAGTTATCCATTCAC TTTCGGCCCTGGGACCAAAGTGGACATCAAA<br><br>SEQ ID NO: 24249 | GAGGTGCAGCTGGTGGAGTCTGGGGAGGCCTG GTCAAGCCTGGGGGGGTCCCTGAGACTCTCCTG CAGCCCTGGATTCACCTTCAGTAGCTATAGCAT GAACTGGGTCCGCCAGGCTCCAGGGAAGGGGCT GGAGTGGGTCTCATCCATTAGTAGTGGTAGTAGT CTCATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGTAGCAGCC TTTGACTACTGGGGCCAGGGAACCCTGGTCACCG TCTCCTCA<br><br>SEQ ID NO: 28255 |
| | | AA | DIQMTQSPSSLSASVGDSVTISCRASQDIRNHLG WYQRNPGKAPKRLIYAASSLQSGVPSRFSGSGS GTEFTLTISSLQPEDFATYYCLQYNSYPFTFGPGT KVDIK<br><br>SEQ ID NO: 24250 | EVQLVESGGGLVKPGGSLRLSCAASGFTFSSYSMN WVRQAPGKGLEWVSSISGSSSLIYYADSVKGRFTIS RDNAKNSLYLQMNSLRAEDTAVYYCARVAAFDY WGQGTLVTVSS<br><br>SEQ ID NO: 28256 |
| iPS:392634 | 21-225_17H3 | NA | GACATCCAGATGACCCAGTCTCCATCCTCCCT GTCTGCATCTGTAGGAGACAGAGTCACCTTCA CTTGCCGGGCAAGTCAGGGCATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATCGGGACACTCACAA TCAGCAGCCTGCAGCCTGAAGATTTTGCAACT TATTACTGTCTACAGCAATATAGTTACCCTCG GACGTTCGGCCAAGGGACCAAGGTGGAAATC AAA<br><br>SEQ ID NO: 24251 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTAACTGTCAT GCACTGGGTCCGCCAGGCTCCAGGCAAGGGGCT GGAGTGGGTGGCAGTTATATGGTATGATGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGAAAAGTA TAGCAGCAGCTGGTACGACTACGGTATGGACGTC TGGGGCCAAGGGACCACGGTCACCGTCTCCTCA<br><br>SEQ ID NO: 28257 |

FIGURE 50
(Continued)

| | | | | |
|---|---|---|---|---|
| iPS:392636 | 21-225_17A6 | AA | DIQMTQSPSSLSASVGDRVTFTCRASQGIRSDLG WYQQKPGKAPKRLIYAASSLQSGVPSRFSGSGS GTEFTLTISSLQPEDFATYYCLQQYSYPRTFGQG TKVEIK<br><br>SEQ ID NO: 24252 | QVQLVESGGGVVQPGRSLRLSCAASGFTFSNCVMH WVRQAPGKGLEWVAVIWYDGSNKYYADSVKGRF TISRDNSKNTLYLQMNSLRAEDTAVYYCAREKYSS SWYDYGMDVWGQGTTVTVSS<br><br>SEQ ID NO: 28258 |
| | | NA | GACATCCAGATGACCCAGTCTCCATCCTCCCT GTCTGCATCTGTGGAGACAGAGTCACCATCA CTTGCCGGGCAAGTCAGAGCATTAGCAACTAT TTAAATTGGTATCATCAGAAACCAGGGAAAGC CCCTAAGCTCCTGATCTATGCTGCTTCCAGTTT GCAAAGTGGGGTCCCATCAAGGTTCAGTGGCA GTGGATCTGGGACAGATTTCACTCTCACCATC AGCAGTCTGCAACTGAAGATTTTGCAACTTA CTACTGTCAACAGAGTACACTTCCCCGCTCA CTTTCGGCGGAGGGACCAAGGTGGAGATCAA A<br><br>SEQ ID NO: 24253 | CAGGTACAGCTGCAGCAGTCAGGTCCAGGACTG GTGAAGCCCTCGCAGACCCTCTCACTCACCTGTG CCATCTCCGGGGACAGTGTCTCTGCAACACTGC TGCTTGGAGCTGGATCAGGCAGTCCCCATCGAGA GGCCTTGAGTGGCTGGGAAGGACATACTACAGG TCCAAGTGGTATAATGATTATGCAGTATCTGTGA AAAGTCGAGTAACCATCAACCAGACACATCCA AGAACCAGTTCTCCCTGCAGCTGAACTCTGTGAC TCCCGAGGACACGGCTGTGTATTACTGTGCAAGA GTAAGCAGTGGCTGGTCCCATCACTACTACTACT ACGGTATGGACGTCTGGGGCCAAGGGACCACGG TCACCGTCTCCTCA<br><br>SEQ ID NO: 28259 |
| | | AA | DIQMTQSPSSLSASVGDRVTITCRASQTISNYLN WYHQKPGKAPKLLIYAASSLQSGVPSRFSGSGS GTDFTLTISSLQPEDFATYYCQQSHTSPLTFGGGT KVEIK<br><br>SEQ ID NO: 24254 | QVQLQQSGPGLVKPSQTLSLTCAISGDSVSRNTAA WSWIRQSPSRGLEWLGRTYYRSKWYNDYAVSVKS RVTINPDTSKNQFSLQLNSVTPEDTAVYYCARVSSG WSHHYYYGMDVWGQGTTVTVSS<br><br>SEQ ID NO: 28260 |

FIGURE 50
(Continued)

| | | | |
|---|---|---|---|
| iPS:392638 | 21-225_17F9 | NA | GACATCCAGATGACCCAGTCTCCATCCTCCT GTCTGCATCTGTAGGAGACAGAGTCACCATCA CTTGCCGGGCAAGTCAGTCAGAGACAGTAAATGAT TTAGGCTGGTATCAGCAGAAACCAGGGAAAG CCCCTAAGCGCCTGATCTATGCTGTATCCAGT TGCAAAGTGGGGTCCCATCAAGGTTCAGCGGC AGTGGATCTGGGACAGAATTCACTCTCACAAT CAACAGCCTGCAGCCTGAAGATTTTGCAACTT ATTACTGTCTACAACATAATACTTATCCGCTCA CTTTCGGCGGAGGGACCAAGGTGGAGTTCAAA | CAGCTGCAGCTGCAGGAGAGTCGGGCCCAGGACTG GTGAAGCCTTCGGAGAGACCCTGTCCCTCACTGCA CTGTCTCTGGGGCTCCATCAGCAGAAGTAGTTA CTATTGGGGCTGGATCCGCCAGCCCCCAGGGAA GGGCCTGGAGTGGATTGGGAATATCTATTATAGT GGGAGCACCTACTACAATCCGTCCCTCAAGAGTC GAGTCACCATATCGTAGACTCGTCCAAGAACCA GTTCTCCCTGAACCTGAACTCTGTGACCGCCGCA GACACGGCTGTGTATTCCTGTGCGAGACATGAA AAGACTGGGGCCTGACTACTGGGGCCAGGGAA CCCTGGTCACCGTCTCCTCA |
| | | | SEQ ID NO: 24255 | SEQ ID NO: 28261 |
| | | AA | DIQMTQSPSSLSASVGDRVTITCRASQVIRNDLG WYQQKPGKAPKRLIYAVSSLQSGVPSRFSGSGS GTEFTLTINSLQPEDFATYCLQHNTYPLTFGGG TKVEFK | QLQLQESGPGLVKPSETLSLTCTVSGGSISRSSYYW GWIRQPPGKGLEWIGNIYYSGSTYYNPSLKSRVTIS VDSSKNQFSLNLNSVTAADTAVYSCARHGKDWGL DYWGQGTLVTVSS |
| | | | SEQ ID NO: 24256 | SEQ ID NO: 28262 |
| iPS:392640 | 21-225_18A1 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGATCTGGGACAGCCTGAAGATTTTGCAACT TCAGCAGCCTGAAGATTTTGCAACT TATTACTGTCTACAGCATAATAGTTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCTGAGACTCTCCTGTG CAGTGTCTGGATTCACCTTCAGTAGCTATGGCAT GCATTGGGTCCGCCAGGCTCCAGGCAAGGGCT GGAGTGGGTGGCAGTTATATGGTATGAGGAAAA TAATAAATATATTCCAGAGACACAAATTCCAGAGGCCGA TTCACCATCTCCAGAGACAATGAACAGCCTGAGAGCGC TGTATCTGCAAATGAACAGCCTGAGAGCCGAGG ACACGGCTGTGTATTACTGTGTGAGAGAGTAGG CTTCCAGTCTGACTACTGGGGCCAGGGAACCCCG GTCACCGTCTCCTCA |
| | | | SEQ ID NO: 24257 | SEQ ID NO: 28263 |

FIGURE 50
(Continued)

| | | | |
|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK | QVQLVESGGGVVQPGRSLRLSCAVSGFTFSSYGMH WVRQAPGKGLEWVAVIWYEENNKYVDSVKGRF TISRDNSKSTLYLQMNSLRAEDTAVYYCVRELGFQ SDYWGQGTPVTVSS |
| | | | SEQ ID NO: 24258 | SEQ ID NO: 28264 |
| iPS:392642 | 21-225_18C6 | NA | GACATCCAGATGACCCAGTCTCCATCCTCCCT GTCTGCATCTGTAGGAGACAGAGTCACCATCA CTTGCCGGACAAGTCAGGGCATTAGAAATGAT TTAGGCTGGTATCAGCAGAAACCGGGGAAAG CCCCTAAGCGCCTGATCTATGCTGCATCCAGT TTGCAAAGTGGGGTCCCGTCAAGGTTCAGCGG CAGTGGATCTGGGACAGAATTCACTCTCACAA TCAGCAGCCTGCAGCCTGAAGATTTTGCAACT TATTACTGTCTACAGCATAGTTCTTACCCGCTC ACTTTCGGCGGAGGGACCAAGGTGGAGATCA AA | CAGCTGCAGCTGCAGGAGTCGGGCCAGGACTG GTGAAGCCTTCGGAGACCCTGTCCCTCACCTGCA CTGTCTCTGGTGGCTCCATCAGTAGGAGTAGTTA TTACTGGGGCTGGATCCGCCAGCCCCCAGGGAA GGGGCTGGAGTGGATTGGGAATATCTATTATAGT GGGTACACCTACTACAACCCGTCCTCAAGAGTC GAGTCATCATATCCGTAGACACGTCCAAGAACCA GTTCTCCCTGAAGCTGAGCTCTGTGACCGCCGCA GACACGGCTCTGTATTACTGTGCGAGACATAGTA GCAGTTGGTCCCTGGACGACTGGGGCCAGGGAA CCCTGGTCACCGTCTCCTCT |
| | | | SEQ ID NO: 24259 | SEQ ID NO: 28265 |
| | | AA | DIQMTQSPSSLSASVGDRVTITCRTSQGIRNDLG WYQQKPGKAPKRLIYAASSLQSGVPSRFSGSGS GTEFTLTISSLQPEDFATYYCLQHSSYPLTFGGGT KVEIK | QLQLQESGPGLVKPSETLSLTCTVSGGSISRSSYYW GWIRQPPGKGLEWIGNIYSGYTYNPSLKSRVIIS VDTSKNQFSLKLSSVTAADTALYYCARHSSSWSLD DWGQGTLVTVSS |
| | | | SEQ ID NO: 24260 | SEQ ID NO: 28266 |

FIGURE 50
(Continued)

| | | | |
|---|---|---|---|
| iPS:392644 | 21-225_19E1 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAAT TTACAAAGTGGGGTCCCATCAAGGTTCAGCGG CAGTGGATCTGGGACAGAATTCACTCTCACAA TTCCAAAGTGCAGCCTGCAGCCTGAAGATTTTGCAACT TATTACTGTCTACAGCATAATAGTTTCCCGCTC ACTTTCGGCGGAGGGACCAAGGTGGAGATCA AA<br>SEQ ID NO: 24261 | CAGGTGCAGCTGTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCCGGCAAGGGGCT GGAGTGGGTGGCAGTTATTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG TTCCGGTCTGACTACTGGGGCCAGGGAACCCTGG TCACCGTCTCCTCA<br>SEQ ID NO: 28267 |
| | | AA | DIQMTQSPSSLSASVGDRVTITCRASQGIRNDLG WYQQKPGKAPKRLIYAASNLQSGVPSRFSGSGS GTEFTLTISSLQPEDFATYYCLQHNSFPLTFGGGT KVEIK<br>SEQ ID NO: 24262 | QVQLVESGGGVVQPGRSLRLSCAASGFTFSNYGM HWVRQAPGKGLEWVAVIWYEENNQYYADSVKGR FTISRDNSKNTLYLQMNSLRAEDTAVYYCARELGF RSDYWGQGTLVTVSS<br>SEQ ID NO: 28268 |
| iPS:392646 | 21-225_20G2 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTCCAAAGTGGGGTCCCATCAAGGTTCAGCGG CAGTGGATCTGGGACAGAATTCACTCTCACAA TCAGCAGCCTGCAGCCTGAAGATTTTGCAAGT TATTACTGTCTACAGCATAATAGTACCCGCTC ACTTTCGGCGGAGGGACCAAGGTGGAGATCA AA<br>SEQ ID NO: 24263 | CAGGTGCAGCTGTGGTGGAGTCTGGGGGAGGCGTG GTCCAGCCTGGGAGGTCCCTGAGACTCTCCTGTG CAGCGTCTGGATTCACCTTCAGTAGCGATGACAT GCACTGGGTCCGCCAGGAACCAGGCAAGGGGCT GGAGTGGGTGGCAGTTATATGGTTTGATGGAAGT AATAAATACTATGCAGACTCCGTGAAGGGCCGA TTCATCATGTCCAAGAGACAATTCCAAGAACACCC TGTATCTGCAAATGAACAGCCTGAGAGCCGGGG ACACGGCTGTGTATTACTGTGCGAGAGATCGAT AGCAGCAGCTGGTACGGTTGACTACTGGGGCCA GGGAACCCTGGTCACCGTCTCCTCA<br>SEQ ID NO: 28269 |

FIGURE 50
(Continued)

| | | | |
|---|---|---|---|
| iPS:392648 | | AA | DIQMTQSPSSLSASVGDRVTITCRASQGIRNDLG WYQQKPGKAPKRLIYAASSFQSGVPSRFSGSGS GTEFTLTISSLQPEDFASYYCLQHNSYPLTFGGGT KVEIK<br>SEQ ID NO: 24264 | QVQLVESGGGVVQPGRSLRLSCAASGFTLSSDDMH WVRQEPGKGLEWVAVIWFDGSNKYYADSVKGRFI MSRDNSKNTLYLQMNSLRAGDTAVYYCARDLIAA AGTVDYWGQGTLVTVSS<br>SEQ ID NO: 28270 |
| | 21-225_16D11 | NA | GACATCCAGATGACCCAGTCTCCATCCTCCCT GTCTGCATCTGTGGAGACAGAGTCACCATCA CTTGCCGGGCAAGTCAGAGCATTAGCAACTAT TTAAATTGGTATCATCAGAAACCAGGGAAAGC CCCTAAGCTCCTGATCTATGCTGCATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTACTGTCAACAGAGTCACAGTTCCCCGCTCA CTTTCGGCGGAGGGACCAAGGTGGAGATCAA A<br>SEQ ID NO: 24265 | CAGGTACAGCTGCAGCAGTCAGGTCCAGGACTG GTGAAGCCCTCGCAGACCCTCTCACTCACCTGTG CCATCTCCGGGGACAGTGTCTCTGCAACACTGC TGCTTGGAGCTGGATCAGGCAGTCCCCATGGAGA GGCCTTGAGTGGCTGGGAAGGACATACTACAGG TCCAAGTGGTATAATGATTATGCAGTATCTGTGA AAAGTCGAATAACCATCAACCAGACACATCCA AGAACCAGTTCTCCCTGCAGCTGAACTCTGTGAC TCCCGAGGACACGGCTGTGTATTACTGTGCAAGA GTAAACAGTGGCTGGTCCCATCACTACTACTACT ACGGTATGGACGTCTGGGGCCAAGGGACCACGG TCACCGTCTCCTCA<br>SEQ ID NO: 28271 |
| | | AA | DIQMTQSPSSLSASVGDRVTITCRASQTISNYLN WYHQKPGKAPKLLIYAASSLQSGVPSRFSGSGS GTDFTLTISSLQPEDFATYYCQQSHSSPLTFGGGT KVEIK<br>SEQ ID NO: 24266 | QVQLQQSGPGLVKPSQTLSLTCAISGDSVSRNTAA WSWIRQSPSRGLEWLGRTYYRSKWYNDYAVSVKS RITINPDTSKNQFSLQLNSVTPEDTAVYYCARVNSG WSHHYYYGMDVWGQGTTVTVSS<br>SEQ ID NO: 28272 |

FIGURE 50
(Continued)

| | | | | | |
|---|---|---|---|---|---|
| iPS:392650 | 21-225_17A4 | NA | GACATCCAGATGACCCAGTCTCCATCTTCCGT GTCTGCATCTGTAGGAGACAGAGTCACCATCA CTTGTCGGGCGAGTCAGGGTATTGGCAACTGG TTAGCCTGGTATCAGCAGAAACCAGGGAAAG CCCCTAAACTCCTGATCTTTGCTGCATCCAGTT TGCAAAGTGGGGTCCCATCACGGTTCAGCGGC AGTGGATCTGGGACAGATTTCACTCTCACCAT CAGCAGCCTGCAGCCTGAAGATTTTGTAACTT ACTATTGTCAACAGGCTAACAGTTTCCCTCGG ACGTTCGGCCAAGGGACCAAGGTGGAAATCA AA | CAGGTGCAGCTGGTGGAGTCTGGGGGAGGCTTG GTCAAGCCTGGAGGGTCCCTGAGACTCTCCTGTG CAGCCCTCTGATTCACCTTCAGTGACTACTACAT GAGCTGGATCCGCCAGGCTCCAGGGAAGGGGCT GGAGTGGGTTTCACACATTAGTAGTAGTGGTAGT ACCATATATTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGATATCGGAAT AACCGGGGATACTTCGATCTCTGGGGCCGTGGCA CCCTGGTCACTGTCTCTTCA |
| | | | SEQ ID NO: 24267 | SEQ ID NO: 28273 |
| | | AA | DIQMTQSPSSVSASVGDRVTITCRASQGIGNWLA WYQQKPGKAPKLLIFAASSLQSGVPSRFSGSGSG TDFTLTISSLQPEDFVTYYCQQANSFPRTFGQGT KVEIK | QVQLVESGGGLVKPGGSLRLSCAASGFTFSDYYMS WIRQAPGKGLEWVSHISSSGSTIYYADSVKGRFTIS RDNAKNSLYLQMNSLRAEDTAVYYCARYRNNRG YFDLWGRGTLVTVSS |
| | | | SEQ ID NO: 24268 | SEQ ID NO: 28274 |
| iPS:392652 | 21-225_17C6 | NA | GACATCCAGATGACCCAGTCTCCATCTCCCT GTCTGCATCTGTAGGAGACAGAGTCACCATCA CTTGCCGGGCAAGTCAGAGCATTAATACTTAT TTAAATTGGTATCAGCAGAAAAACCAGGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTTCTGTCAACAGAGTTACAGAACCCCCTTT TCACTTTCGGCCCTGGGACCAAAGTGGATAT CAAA | GAGGTGCAGCTGTTGGAGTCTGGGGGAGGCTTG GTACAGCCTGGGGGGTCCCTGAGACTCTCCTGTG CAGCCTCTGAATTCACCTTTAGCAGCTATGCCAT GAACTGGGTCCGCCAGGCTCCAGGGAAGGGGCT GGAGTGGGTCTCAGTTATTAGTGGTCGTGGTGGT AACACATTCTACGCAGACTCCGTGAAGGGCCGGT TCACCATCTCCAGAGACAATTCCAAGAACACGCT CTTTCTGCAAATGAACAGCCTGAGAGCCGAGGA CACGGCCGTATATTATTGTGCGCTCCCGTTTGCA GTGGCTGGCTCGGAGGCGTTTGATATCTGGGGCC AAGGGACAATGGTCACCGTCTCTTCA |
| | | | SEQ ID NO: 24269 | SEQ ID NO: 28275 |

FIGURE 50
(Continued)

| | | | |
|---|---|---|---|
| iPS:392654 | 21-225_17A10 | AA | DIQMTQSPSSLSASVGDRVTITCRASQSINTYLN WYQQKPGKAPKLLIYAASSLQSGVPSRFSGSGS GTDFTLTISSLQPEDFATYFCQQSYRTPFFTFGPG TKVDIK<br>SEQ ID NO: 24270 | EVQLLESGGGLVQPGGSLRLSCAASEFTFSSYAMN WVRQAPGKGLEWVSVISGRGNTFYADSVKGRFTI SRDNSKNTLFLQMNSLRAEDTAVYYCASRLAVAG SEAFDIWGQGTMVTVSS<br>SEQ ID NO: 28276 |
| | | NA | GACATCCAGATGACCCAGTCTCCATCCTCCCT GTCTGCATCTGTAGGAGACAGAGTCACCATCA CTTGCCGGGCAAGTCAGAGCATTAGAAATGAT TTAGGCTGGTATCAGCAGAAACCAGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24271 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGCCAAGGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG TTCCGGTCTGACTACTGGGGCCAGGGAACCCTGG TCACCGTCTCCTCA<br>SEQ ID NO: 28277 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24272 | QVQLVESGGGVVQPGRSLRLSCAASGFTFSNYGM HWVRQAPAKGLEWVAVIWYEENNQYYADSVKGR FTISRDNSKNTLYLQMNSLRAEDTAVYYCARELGF RSDYWGQGTLVTVSS<br>SEQ ID NO: 28278 |

FIGURE 50
(Continued)

| | | | |
|---|---|---|---|
| iPS:392656 | 21-225_1F2 | NA | GACATCCAGATGACCCAGTCTCCATCCTCCT GTCTGCATCTGTAGGAGACAGAGTCACCATCA CTTGCCGGGCAAGTCAGGGACATTAGGCATT AGAAATGAT TTAGGCTGGTATCAGCAGAAACCAGGGAAAG CCCCTAAGCTCCTGATCTATGCTGCATCCAGT GTGCAAAGTGGGGTCCCATCAAGGTTCAGCGG CAGTGGATCTGGGACAGAATTCACTCTCACAA TCAGCAGCCTGCAGCCTGAAGATTTTGCAATT TATTACTGTCTACAGCATAATAGTTACCCGCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCACTTGCA CTGTCTCTGGTGGCTCCATCAGTAGGAGTAGTTA CTACTGGGGCTGGATCCGCCAGCCCCCAGGGAA GGGGCTGGAGTGGATTGGGAATATTTATTATAGT GGGAGCGCTACAACAACCGTCCCTCAAGGGT CGAGTCACCATATCGTAGACACGTCAAGAACC AGTTCTCCCTGAAGCTGAACTCTGTGACCGCCGC AGACACGGCTGTGTATTACTGTGTGGAGACATGGA AAAGACTGGGGCCTTGACTACTGGGGCCAGGGA ACCCTGGTCACCGTCCTCA |
| | | AA | SEQ ID NO: 24273 | SEQ ID NO: 28279 |
| | | | DIQMTQSPSSLSASVGDRVTITCRASQGIRNDLG WYQQKPGKAPKRLIYAASSVQSGVPSRFSGSGS GTEFTLTISSLQPEDFAIYYCLQHNSYPLTFGGGT KVEIK | QLQLQESGPGLVKPSETLSLTCTVSGGSISRSSYYW GWIRQPPGKGLEWIGNIYYSGSAYNNPSLKGRVTIS VDTSKNQFSLKLNSVTAADTAVYYCGRHGKDWGL DYWGQGTLVTVSS |
| | | | SEQ ID NO: 24274 | SEQ ID NO: 28280 |
| iPS:392658 | 21-225_18E8 | NA | GACATCCAGATGACCCAGTCTCCATCCTCCCT GTCTGCATCTGTAGGAGACAGAGTCACCATCA CTTGCCGGGCAAGTCAGGGACATTAGGCATT AGAAATGAT TTAGGCTGGTATCAGCAGAAACCAGGGAAAG CCCCTAAGCTCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA | CAGGTGCAGTTGGTGCAGTCTGGGGGAGGCGTG GTCCAGCCTGGGAGGTCCCTGAGACTCTCCTGTG CAGCCGTCTGATTCACCTTCAGTAACTATGGCAT GCACTGGGTCCGCCAGGCTCCAGGCAAGGGCT GGAGTGGGTGGCAGTTATTTGGTATGAAGAAAAT AATCAATACTATGCAGACTCCGTGAAGGGCCGAT TCACCGTCTCCAGAGACAATTCCAAGAACACGCT GTTTCTGCAAATGAACAGCCTGAGAGCCGAGGA CACGGCTGTGTATTACTGTGCGAGAGAACTGGG TTCCGGTCTGACTACTGGGGCCAGGGAACCCTGG TCACCGTCCCTCA |
| | | | SEQ ID NO: 24275 | SEQ ID NO: 28281 |

FIGURE 50
(Continued)

| | | | |
|---|---|---|---|
| iPS:392660 | | AA | DIQMTQAPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24276 | QVQLVESGGGVVQPGRSLRLSCAASGFTFSNYGM HWVRQAPGKGLEWVAVIWYEENNQYYADSVKGR FTVSRDNSKNTLFLQMNSLRAEDTAVYYCARELGF RSDYWGQGTLVTVSS<br>SEQ ID NO: 28282 |
| | 21-225_19B3 | NA | GACATCCAGATGACCCAGTCTCCATCCTCCCT GTCTGCTTCTGTGGGAGACAGAATCACCATCA CTTGCCGGCAGGTCAGAGTCAGAACATTATCAACTAT TAAATTGGTATCAGCAGAAACCAGGGAAAG CCCCTAACCTCGTGATATATGTTGCATCCAGTT TGCAAAGTGGGGTCCCATCAAGGTTCAATGGC AGTGGATCTGGGACAGATTTCACTCTCACCAT CAGCAGTCTGCAACCTGAAGATTTTGCAACTT ACTACTGTCAACAGAGTTACAGTACCCCTTTC ACTTTCGGCCCTGGGACCAAAGTGGATATCAA A<br>SEQ ID NO: 24277 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGACAT GCACTGGGTCCGCCAGGCTCCAGGCAAGGGGCT GGAGTGGGTGGCAGTTATATGTATGACGGAAG TGATAAATACTATGCAGACTCCGTGAAGGGCCG ATTCACCATCTCCAGAGACAACAGCTCCAAGAACACG CTCTTTCTGCAAATGAACAGCTGTGCGAGAGATCGGGC ACACGGCTGTGTATTACTGTGCGAGAGAGATCGGGC CTATAGCAGCTCGTCTGACTACTGGGGCCAGGA ACCCGTCACCGTCTCCTCA<br>SEQ ID NO: 28283 |
| | | AA | DIQMTQSPSSLSASVGDRITITCRAGQNIINYLNW YQQKPGKAPNLLIYVASSLQSGVPSRFNGSGSGT DFTLTISSLQPEDFATYYCQQSYSTPFTFGPGTKV DIK<br>SEQ ID NO: 24278 | QVQLVESGGGVVQPGRSLRLSCAASGFTFSSYDMH WVRQAPGKGLEWVAVIWYDGSDKYYADSVKGRF TISRDNSKNTLFLQMNSLRAEDTAVYYCARDRAYS SSSDYWGQGTLVTVSS<br>SEQ ID NO: 28284 |

FIGURE 50
(Continued)

| | | NA | GACATCCAGATGACCCAGTCTCCATCCTCCT GTCTGCATCTGTAGGAGACAGAGTCACCATCA CTTGCCGGGCAAGTCAGAGCATTATCACCTAT TTAAATGGTATCAGCAGAAACCAGGGAAAG CCCCTAAGGTCCTGATCCATACTGCATCCAGT TTGCAAAGTGGGGTCCCATCAAGGTTCAGTGG CAGTGGATCTGGGACAGATTTCACTCTCACCA TCAGCAGTCTGCAACCTGAAGATTTTGCAACT TACTACTGTCAACAGAGCTTACAGTCCCCGCT CACTTTCGGCGGAGGGACCAAGGTGGAGATC AAA | CAGGTGCAGCTGGTGGAGTCTGGGGGAGGCGTG GTCCAGCCTGGGAGGTCCCTGAGACTCTCCTGTG TAGCCGTCTGGATTCACCTTCAGTAGCTATGGCAT GCACTGGGTCCGCCAGGCTCCAGGCAAGGGGCT GGAGTGGGGGCAGTTATATGCAGACTCCGTGAAG TAATAAATACTATCCAGAGACAATGCCAAGAACAC ATTCACCATCTCGAAATGAACAGCTGAGAGCCGA GCTGTATCTGCAAATGAACAGCTGTGCGAGATCTG GGACACGGCTGTGTATTACTGTGCGAGAGATCTG AGTATGGGCGGAATGGACGTCTGGGGCCAAGGG ACCACGGTCACCGTCTCCTCA |
| iPS:392664 | 21-225_20F6 | | SEQ ID NO: 24279 | SEQ ID NO: 28285 |
| | | AA | DIQMTQSPSSLSASVGDRVTITCRASQSIITYLNW YQQKPGKAPKVLIHTASSLQSGVPSRFSGSGSGT DFTLTISSLQPEDFATYYCQQTYSPPLTFGGGTK VEIK | QVQLVESGGGVVQPGRSLRLSCVASGFTFSSYGMH WVRQAPGKGLEWGAVIWHDGSNKYYADSVKGRF TISRDNAKNTLYLQMNSLRAEDTAVYYCARDLSM GGMDVWGQGTTVTVSS |
| | | | SEQ ID NO: 24280 | SEQ ID NO: 28286 |
| iPS:392666 | 21-225_16F11 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGGCCCTGATCTATGCTGCATCCAGT GTACAAAGTGGGGTCCCATCAAGGTTCAGCGG CAGTGGATCTGGGACAGATTTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA | CAGGTGCAGATGGTGGAGTCTGGGGGAGGCGTG GTCCAGCCTGGGAGGTCCCTGAGACTCTCTGTG AAGCGTCTGGATTCACCTTCAGTAGCTATGGCAT GCACTGGGTCCGCCAGGCTCCAGGCAAGGGGCT GGAGTGGGTGGCAGTTATATGGTATGAGGAAAA TTCACCATCTCCAGAGACAATTCCAAGAGCACGC TGTATCTGCAAATGAATAGCCTGAGAGCCGAGG ACACGGCTGTGTATTACTGTGTGAGAGAACTAGG CTTCCAGTCTGACTACTGGGGCCAGGGAACCCCG GTCACCGTCTCCTCA |
| | | | SEQ ID NO: 24281 | SEQ ID NO: 28287 |

FIGURE 50
(Continued)

| | | | | |
|---|---|---|---|---|
| | | AA | DIQMTQSPSSLSASVGDRVTITCRASQGIRNDLG WYQQKPGKAPKRLIYAASSVQSGVPSRFSGSGS GTEFTLTISSLQPEDFATYYCLQHNSYPLTFGGG TKVEIK <br><br> SEQ ID NO: 24282 | QVQMVESGGGVVQPGRSLRLSCEASGFTFSSYGM HWVRQAPGKGLEWVAVIWYEENNKYYVDSVKGR FTISRDNSKSTLYLQMNSLRAEDTAVYYCVRELGF QSDYWGQGTPVTVSS <br><br> SEQ ID NO: 28288 |
| iPS:392668 | 21-225_17B4 | NA | GACATCCAGATGACCCAGTCTCCATCCTCCCT GTCTGCATCTGTAGGCGACAGAGTCACCATCA CTTGCCGGGCAAGTCAGAACATTAGTAGTTAT TTAAATTGGTATCAGCAGAAACCAGGGAAAG CCCCTAAGCTCCTGATCTTTGGTGTGCATCCAGTT TGCAAACTGGGGTCCCATCAAGGTTCAGTGGC AGTGGATCTGGGACAGATTTCACTCTCACCAT CAACAGTCTGCAACCTGAAGATTTTGCAACTT ACTTCTGTCAACAGAGTTACAGAACCCCCTTT TTCACTTTCGGCCCTGGGACCAAAGTGGATAT CAAA <br><br> SEQ ID NO: 24283 | GAGGTGCAGCTGTTGGAGTCTGGGGGAGGCTTG GTACAGCCTGGGGGGTCCCTGAGACTCTCCTGTG CAGCCTCTGAATTTACCTTTAGCAGCTATGCCAT GAACTGGGTCCGCCAGGCTCCAGGGAAGGGGCT GGAGTGGGTCTCAGTTATTAGTGGCCGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGTCCCGTTTGGCA GTGGCTGGCTCGGAGGCTTTGATATCTGGGGCC AAGGGACAATGGTCACCGTCTCTTCA <br><br> SEQ ID NO: 28289 |
| | | AA | DIQMTQSPSSLSASVGDRVTITCRASQNISSYLN WYQQKPGKAPKLLIFGASSLQTGVPSRFSGSGSG TDFTLTINSLQPEDFATYFCQQSYRTPFFTFGPGT KVDIK <br><br> SEQ ID NO: 24284 | EVQLLESGGGLVQPGGSLRLSCAASEFTFSSYAMN WVRQAPGKGLEWVSVISGRGGNTFYADSVKGRFTI SRDNSKNTLYLQMNSLRAEDTAVYYCASRLAVAG SEAFDIWGQGTMVTVSS <br><br> SEQ ID NO: 28290 |

FIGURE 50
(Continued)

| | | | | |
|---|---|---|---|---|
| iPS:392674 | 21-225_18C2 | NA | GACATCCAGATGACCCAGTCTCCATCCTCCCTGTCTGCGTCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATTTGGGACAGAATTCACTCTCACAATCAGCAGCCTGCAGCCTGAAGATTTTGCAACTTATTACTGTCTACAACATAATAGTTACCCGTGGACGTTCGGCCAAGGGACCAAGGTGGAGATCAAAA | CAGGTGCAACTGGTGGAGTCTGGGGGAGGCGTGGTCCAGCCTGGGAGGTCCCTGAGACTCTCCTGTAGCGTCTGGATTCACCTTCAGTGACTATGGCATGCACTGGGTCCGCCAGGCTCCAGGCAAGGGGCTGGAGTGGATGGCAGTTATATGGTATGATGTAACTAATAAATACTATGCAGACTCCGTGAAGGGCCGATTCACCATCTCCAGAGACAATTCCAAGAACACGCTGTATCTGCAAATGAACAGCCTGAGCCGCGAGGACACGGCTGTTTATTACTGTGCGAGAGAGCTTGGCTGGTACGAGGACTACTGGGGCCAGGGAACCCTGGTCACCGTCTCCTCA |
| | | | SEQ ID NO: 24285 | SEQ ID NO: 28291 |
| | | AA | DIQMTQSPSSLSASVGDRVTITCRASQGIRNDLGWYQQKPGKAPKRLIYTASSLQSGVPSRFSGSGFGTEFTLTISSLQPEDFATYCYCLQHNSYPWTFGLGTKVVIK | QVQLVESGGGVVQPGRSLRLSCVASGFTFSDYGMHWVRQAPGKGLEWMAVIWYDVTNKYYADSVKGRFTISRDNSKNTLYLQMNSLSAEDTAVYYCARELGWYEDYWGQGTLVTVSS |
| | | | SEQ ID NO: 24286 | SEQ ID NO: 28292 |
| iPS:392676 | 21-225_19F3 | NA | GACATCCAGATGACCCAGTCTCCATCCTCCCTGTCTGCATCTGTACGAGACAGAGTCACCATCACTTGCCGGGCAAGTCAGGGCATAAGAAATGATTTAGGCTGGTATCAGCAGAAACCAGGGAAAGCCCCTAAGCGCCTGATCTATGCTGTTTCCAGTTGCAAAGTGGGGTCCCATCAAGGTTCAGCGGCTGCAGAGTCTGGGACAGCACTACAACCGAGCCACCATATCCGTAGACACGTCCAAGAACCAGCAGGATCTGGGACAGCCTGAAGATTTTGCAACTTATTACTGTCTACAGCATGCCAGTTACCCGCTCACTTTCGGCGGAGGGACCAAGGTGGAGATCAAAA | CAGGTGCAGCTGCAGGAGTCGGGCCCAGGACTGGTGAAGCCTTCCGGGTGGGCCCTGTCCCTCACCTGCACTGTCTCCGGTGGCCATCAGCGGTAGTTACTACTGGGGCTGGATCCGCCAGCCCCCAGGGAAGGGAGCACCTACAACCCGTCCTTCAAGAGTCGAGTCACCATATCCGTAGACACGTCAAGAACCAGTTCTCCCTGAAGCTGAGCTCTGTGACCGCGAGACACGGCTGTCTATTACTGTGCGAGACATTCCAGTAGCTGGTCCCTTGACTACTGGGGCCAGGGAACCCCTGGTCACCGTCTCCTCT |
| | | | SEQ ID NO: 24287 | SEQ ID NO: 28293 |

FIGURE 50
(Continued)

| | | | | |
|---|---|---|---|---|
| | | AA | DIQMTQSPSSLSASVRDRVTITCRASQGIRNDLG WYQQKPGKAPKRLIYAVSSLQSGVPSRFSGSGS GTEFTLTISSLQPEDFATYYCLQHASYPLTFGGG TKVEIK<br>SEQ ID NO: 24288 | QVQLQESGPGLVKPSETLSLTCTVSGGAISGSSYYW GWIRQPPGKQLEWIGNIYYSGSTYNPSFKSRVTIS VDTSKNQFSLKLSSVTAEDTAVYYCARHSSSWSLD YWGQGTLVTVSS<br>SEQ ID NO: 28294 |
| iPS:392678 | 21-225_20F3 | NA | GACATCCAGATGACCCAGTCTCCATCCTCCCT GTCTGCATCTGTAGGAGACAGAGTCACCATCA CTTGCCGGGCAAGTCAGAGCATTAGTAGTTAT TTATATTGGTATCAGCAGAAACCAGGGAAAGC CCCTAAGCTCCTGATCTATGCTGCATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTACTGTCAACAGAGTTACAGTGCCCCTCCAT TCACTTTCGGCCCTGGGACCAAAGTGGATATC AAA<br>SEQ ID NO: 24289 | GAGGTGCAGCTGTTGGAGTCTGGGGGAGGCTTG GTACAGCCGGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGTTATTAGTGGTAGTGGTGGT AGCACATACTACGCAGACTCCGTGAAGGGCCGG TTCACCATCTCCAGAGACACAATTCCAAGAACACGC TGTATCTGCAAATGAACAGCCTGAGAGCCGAGG ACACGGCCGTATATTACTGTGCGAAAGGATAG CAGCAGCTGGTACGGAGTACTTCGATCTCTGGGG CCGTGGCACCCTGGTCACTGTCTCCTCA<br>SEQ ID NO: 28295 |
| | | AA | DIQMTQSPSSLSASVGDRVTITCRASQSISSYLYW YQQKPGKAPKLLIYAASSLQSGVPSRFSGSGSGT DFTLTISSLQPEDFATYYCQQSYSAPPFTFGPGTK VDIK<br>SEQ ID NO: 24290 | EVQLLESGGGLVQPGGSLRLSCAASGFTFSSYAMN WVRQAPGKGLEWVSVISGSGGSTYYADSVKGRFTI SRDNSKNTLYLQMNSLRAEDTAVYYCAKRIAAAG TEYFDLWGRGTLVTVSS<br>SEQ ID NO: 28296 |

FIGURE 50
(Continued)

| | | | |
|---|---|---|---|---|
| iPS:392680 | 21-225_20A7 | NA | GACATCCAGATGACCCAGTCTCCATCCTCCT GTCTGCATCTGTAGGAGACAGAGTCACCATCA CTTGCCGGGCAAGTCAGGCATTAGAAATGAT TTAGGCTGGTATCAGCAAAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24291 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAACTATGGCAT GCACTGGGTCCGCCAGGCTCCAGGCAAGGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTATTTATTACTGTGCGAGAGAACTGGGG TTCCGGTCTGACTACTGGGGCCAGGGAACCCTGG TCACCGTCTCCTCA<br>SEQ ID NO: 28297 |
| | | AA | DIQMTQSPSSLSASVGDRVTITCRASQGIRNDLG WYQQKPGKAPKRLIYAASSLQSGVPSRFSGSGS GTEFSLTISSLQPEDFATYYCLQHNSYPLTFGGGT KVEIK<br>SEQ ID NO: 24292 | QVQLVESGGGVVQPGRSLRLSCAASGFTFSNYGM HWVRQAPGKGLEWVAVIWYEENNQYYADSVKGR FTISRDNSKNTLYLQMNSLRAEDTAIYYCARELGFR SDYWGQGTLVTVSS<br>SEQ ID NO: 28298 |
| iPS:392682 | 21-225_16A12 | NA | GACATCCAGATGACCCAGTCTCCATCCTCACT GTCTGCATCTGTAGGAGACAGAGTCACCATCA CTTGTCGGGCGAGTCAGGCATTAGCAGTGCATTAT TTAGCCTGGTTTCAGCAGAAACCAGGGAAAGC CCCTAAGTCCCTGATTTCTGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTTGCAACTTA TTACTGCCAACAGTATTATAGTTATCCGCTCAC TTTCGGCGGAGGGACCAAGGTGGAGATCAAA<br>SEQ ID NO: 24293 | GAGGTGCAGCTGGTGGAGTCTGGGGGAGGCCTG GTCAAGCCTGGGGGGTCCCTGAGACTCTCCGTGT CAGCCTCTGGATTCACCTTCAGTAGTAGTAGAAT GAACTGGGTTCCGCAGGCTCCAGGGAAGGGGCT GGAGTGGGTCTCATCCATTAGTAGTGTAGTAGTACT GACATATACTACGCAGACTCAGTGAAGGGCCGA TTCACCATCTCCAGAGACAACGCCGAGAACTCAC TGTATCTGCAAATGAACAGCCTGAGAGCCGAGG ACACGGCTGTGTATTACTGTGCGAGAAGGGACTT CTGGGGCCAGGGAACCCTGGTCACCGTCTCCTCA<br>SEQ ID NO: 28299 |

FIGURE 50
(Continued)

| | | AA | DIQMTQSPSSLSASVGDRVTITCRASQAINTYLA WFQQKPGKAPKSLSAASSLQSGVPSKFSGSGSG TEFTLTISSLQPEDFATYYCQQYYSYPLTFGGGT KVEIK<br>SEQ ID NO: 24294 | EVQLVESGGGLVKPGGSLRLSCAASGFTFSSYRMN WFRQAPGKGLEWVSSISGSSTDIYYADSVKGRFTIS RDNAENSLYLQMNSLRAEDTAVYYCARRDFWGQ GTLVTVSS<br>SEQ ID NO: 28300 |
|---|---|---|---|---|
| iPS:392684 | 21-225_17F4 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br>SEQ ID NO: 24295 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GAACTGGGTCCGCCAGGCTCCAGGCAAGGGGCT GGAGTGGGTGGCAGTTATATGGTATGATGGAAAT AATAAACACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGTAGTGGGAG CTACTTCTTTGACTACTGGGGCCAGGGAACCCTG GTCACCGTCTCCTCA<br>SEQ ID NO: 28301 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br>SEQ ID NO: 24296 | QVQLVESGGGVVQPGRSLRLSCAASGFTFSNYGM NWVRQAPGKGLEWVAVIWYDGNNKHYADSVKG RFTISRDNSKNTLYLQMNSLRAEDTAVYYCASSGS YFFDYWGQGTLVTVSS<br>SEQ ID NO: 28302 |

FIGURE 50
(Continued)

| | | | |
|---|---|---|---|
| iPS:392686 | 21-225_17C7 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGATTCAGCGG CAGTGGATCTGGGACAGATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br>SEQ ID NO: 24297 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGCAGACTCCGTGAAGGGCCGA AATAAATACTATGCAGACTCCGTGAAGGGCCGA TTCACCATCTCCAGAGACAATTCCAAGAACACGC TGTATCTGCAAATGAACAGCCTGAGAGCCGAGG GCACGGCTGTGTATTACTGTGCGAGAGATCTTGG CTGGACGGAAGAATACTGGGGCCAGGGAACCCT GGTCACCGTCTCCTCA<br>SEQ ID NO: 28303 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPWTFGQG TKVEIK<br>SEQ ID NO: 24298 | QVQLVESGGGVVQPGKSLRLSCAASGFTFSDYGM HWVRQAPGKGLEWVAVIWFDGSNKYYADSVKGR FTISRDNSKNTLYLQMNSLRAEGTAVYYCARDLG WTEEYWGQGTLVTVSS<br>SEQ ID NO: 28304 |
| iPS:392690 | 21-225_18F2 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br>SEQ ID NO: 24299 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTTTGATGAAGT AATAAATACTATGCAGACTCCGTGAAGGGCCGAT TCACCATCTCCAGAGACAATTCCAAGAACACGCT GTATCTGCAAATGAACAGCCTGAGAGTCGAGGA CACGGCTGTGTATTACTGTGCGAGAGATCTTGGC TGGACGGAAGAGTACTGGGGCCAGGGAACCCTG GTCACCGTCTCCTCA<br>SEQ ID NO: 28305 |

FIGURE 50
(Continued)

| | | | |
|---|---|---|---|
| iPS:392692 | 21-225_18G10 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPWTFGQG TKVEIK SEQ ID NO: 24300 | QVQLVESGGGVVQPGRSLRLSCAASGFTFSDYGM HWVRQAPGKGLEWVAVIWFDGSNKYYVDSVKGR FTISRDNSKNTLYLQMNSLRVEDTAVYYCARDLG WTEEYWGQGTLVTVSS SEQ ID NO: 28306 |
| | | NA | GACATCCAGATGACCCAGTCTCCATCCTCACT GTCTGCATCTGTAGGAGACAGAGTCACCATCA CTTGTCGGGCGAGTCAGGACATTAGCTATTAT TTAGCCTGGTTTCAGCAGAAACCAGGGAAAGC CCCTAAGTCCCTGATTTATGTTGCATCCAGTTT GCAAAGTGGGGTCCCATCAAAGTTCGGCGGCA GTGGATTTGGGACAGATTTCACTCTCACCATC AGCAGCCTGCAGCCTGAAGATTTTGCAACTTA TTACTGTCTTACAGTATAATAGTTACCCATTCAC TTTCGGCCCTGGGACCAAAGTGGATATCAAA SEQ ID NO: 24301 | GAGGTGCAGCTGGTGGAGTCTGGGGGAGGCTTG GTACAGCCTGGGGGGTCCCTGAGACTCTCTGTG CAGCCTCTGGAATCACCTTCAGTACTACTAGCAT GAACTGGGTCCGCCAGGCTCCAGGGAAGGGGCT GGAGTGGGTTTCATACATTAGTAGGAGTAGTAGT ACCATAGACTACGCAGACTCTGTGAAGGGCCGA TTCACCATCTCCAGAGACAATGCCAAGAACTCAC TGTATCTGCAAATGAACAGCCTGAGAGACGAGG ACACGGCTGTGTATTACTGTGCGAGAGGAGGTGG GAGCCCTTTTGACTACTGGGGCCAGGGAACCCTG GTCACCGTCTCCTCA SEQ ID NO: 28307 |
| | | AA | DIQMTQSPSSLSASVGDRVTITCRASQDISYYLA WFQQKPGKAPKSLIYVASSLQSGVPSKFGGSGF GTDFFTLTISSLQPEDFATYYCLQYNSYPFTFGPGT KVDIK SEQ ID NO: 24302 | EVQLVESGGGLVQPGGSLRLLCAASGITFSTYSMN WVRQAPGKGLEWVSYISRSSSTIDYADSVKGRFTIS RDNAKNSLYLQMNSLRDEDTAVYYCARGGGSPFD YWGQGTLVTVSS SEQ ID NO: 28308 |

FIGURE 50
(Continued)

| | | | | |
|---|---|---|---|---|
| iPS:392694 | 21-225_19A5 | NA | GACATCCAGATGACCCAGTCTCCATCCTCCCT GTCTGCACCTGTGTAGGAGACAGAGTCTCCATCA CTTGCCGGGCAAGTCAGAACAGATTATCAACTAT TTAAATTGGTATCAGCAGAAACCAGGAAAG CCCCTAAGCTCCTGATAGATGTGCATCCAAT TTACAAGGTGGGGTCCCATCAAGGTTCACTCTCACCA CAGTGGATCTGGGACAGATTTCACTCTCACCA TCAGCAGTCTGCAACCTGAGAGTTACAGATTTTGCAACT TACTACTGTCAACAGAGTTACAGAACCCCTTT CACTTTTCGGCCCCTGGGACCCAAAGTGGATATCA AA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGCCAT GCACTGGGTCCGCCAGGCTCCAGGCAAGGGCT GGAGTGGGTGGCAGTTATATGGTTTGATGAAGT GATAAATACTATGCAGACTCCGTGAAGGGCCGA TTCACCATCTCCAGAGACAATTCCAAGAACACGC TGTATCTACAAATGAACAGCCTGAGAGCCGAGG ACACGGCTGTGTATTACTGTGCGAGAGATCGGGC CTATAGTAGCTCGTCTGACTACTGGGGCCAGGGA ACCCTGGTCACCGTCTCCTCA |
| | | | SEQ ID NO: 24303 | SEQ ID NO: 28309 |
| | | AA | DIQMTQSPSSLSAPVGDRVSITCRASQNIINYLN WYQQKPGKAPKLLIDVASNLQGVPSRFSGSGS GTDFTLTISSLQPEDFATYCQQSYSTPFTFGPGT KVDIK | QVQLVESGGGVVQPGRSLRLSCAASGFTFSSYAMH WVRQAPGKGLEWVAVIWFDGSDKYYADSVKGRF TISRDNSKNTLYLQMNSLRAEDTAVYYCARDRAYS SSSDYWGQGTLVTVSS |
| | | | SEQ ID NO: 24304 | SEQ ID NO: 28310 |
| iPS:392696 | 21-225_20A4 | NA | GACATCCAGATGACCCAGTCTCCATCCTCCCT GTCTGCATCTGTAGGAGACAGAGTCACCATCA CTTGCCGGGCAAGTCAGAGCATTATCAACTAT TTAAATTGGTATCAGCAGAGACCAGGGAAATC CCCTAAGCTCCTGATCTATGCTGCATCCAGTTT GCACAGTGGGGTCCCATCAAGGTTCAGTGGCA GAGGATCTGGGACAGATTTCACTCTCACCATC AGTAGTCTGCAACCTGAAGATTTTGCAACTTA CTTCTGTCAACAGAGTTACAGAACCCCCTTAT TCACTTTCGGCCCTGGGACCAAAGTAGATTTC AAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GACCTGGGTCCGCCAGGCTCCAGGATGGGCT GGAGTGGGTCTCAGTTATAAGTGTAGTGGTGGT TACACATACAACGGGGACTCCGTGAAGGGCCGG TTCACCATCTCCAGAGACAATTCCAAGAACACGC TGTATCTGCAAATGAACAGCCTGAGAGTCGAGG ACACGGCCGTATATTACTGTGCGTCCGTATAGC AGTGGCTGGTCGGAGGCTTTGATATCTGGGGC CAAGGGACAATGGTCACCGTCTCTTCA |
| | | | SEQ ID NO: 24305 | SEQ ID NO: 28311 |

FIGURE 50
(Continued)

| | | | |
|---|---|---|---|
| iPS:392700 | 21-225_16E12 | AA | DIQMTQSPASLSASVGDRVTITCRASQSIINYLN WYQQRPGKSPKLLIYAASSLHSGVPSRFSGRGSG TDFTLTISSLQPEDFATYFCQQSYRTPLFTFGPGT KVDFK<br>SEQ ID NO: 24306 | EVQLLESGGGLVQPGGSLRLSCAASGFTFSSYAMT WVRQGPGMGLEWVSVISGSGYTNADSVKGRFT ISRDNSKNTLYLQMNSLRVEDTAVYYCASRIAVAG SEAFDIWGQGFMVTVSS<br>SEQ ID NO: 28312 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTACAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24307 | CAGGTGCAGCTGGTGGAGTCTGGGGGAGGCCTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGTAGACTCCGTGAGGGGCCGA TAATAAATATTATGTAGACTCCGTGAGGGGCCGA TTCACCATCTCCAGAGACAATTCCAAGAGCACGC TGTATCTGCAAATGAACAGCCTGAGAGCCGAGG ACACGGCTGTGTATTACTGTGTGAGAGAGCTAGG CTTCCAGTCTGATCACTGGGGCCAGGGAACCCCG GTCACCGTCTCCTCA<br>SEQ ID NO: 28313 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24308 | QVQLVESGGGLVQPGRSLRLSCAASGFTFSNYGMH WVRQAPGKGLEWVAVIWYEGSNKYYVDSVRGRF TISRDNSKSTLYLQMNSLRAEDTAVYYCVRELGFQ SDHWGQGTPVTVSS<br>SEQ ID NO: 28314 |

FIGURE 50
(Continued)

| | | | | |
|---|---|---|---|---|
| iPS:392702 | 21-225_17F7 | NA | GACATCCAGATGACCCAGTCTCCATCCTCCCT GTCTGCATCTGTTGGAGACAGAGTCACCATCA CTTGCCGGGCAAGTCAGAGACCATTAGTAGTTTT TTAAATTGGTATCAGCAGAAACCAGGGAAAG CCCCTAAACTCCTGATCTATGCTGCTTCCAGTT TGCAAAGTGGGGTCCCGTCAAGGTTCAGTGGC AGTGGATCTGGGACAGATTTCACTCTCACCAT CAGCGGTCTGCAACCTGAAGATTTTGCAACTT ACTTCTGTCAACAGAGTTACAGAACCCCTTT TTCACTTTCGGCCCTGGGACCAAAGTGGATAT CAAA SEQ ID NO: 24309 | GAGGTGCAGCTGTTGGAGTCTGGGGGAGGCTTG GTACAGCCTGGGGGGTCCCTGAGACTCTCCTGTG CAGCCCTCTGAATTCACCTTTAGCAGCTATGCCAT GAACTGGGTCCGCCAGGCTCCAGGGAAGGGGCT GGAGTGGGTCTCAATTATTAGTGGTCGTGGTGGT AACACATTCTACGCAGACTCCGTGAAGGGCCGGT TCACCATCTCCAGAGACAACAGCCTGAGAGCCGAGGA GTATCTGCAAATGAACAGCCTGAGAGCCGAGGA CACGGCCGTATATTACTGTGCGTCCCGTTTGGCA GTGGCTGGCTCGGAGGCTTTTGATATCTGGGGCC AAGGGACAATGGTCACCGTCTCTTCA SEQ ID NO: 28315 |
| | | AA | DIQMTQSPSSLSASVGDRVTITCRASQTISSFLNW YQQKPGKAPKLLIYAASSLQSGVPSRFSGSGSGT DFTLTISGLQPEDFATYFCQQSYRTPFFTFGPGTK VDIK SEQ ID NO: 24310 | EVQLLESGGGLVQPGGSLRLSCAASEFTFSSYAMN WVRQAPGKGLEWVSIISGRGGNTFYADSVKGRFTI SRDNSKNTLYLQMNSLRAEDTAVYYCASRLAVAG SEAFDIWGQGTMVTVSS SEQ ID NO: 28316 |
| iPS:392704 | 21-225_17F11 | NA | GACATCCAGATGACCCAGTCTCCATCCTCCCT GTCTGCATCTATAGGAGACAGAGTCACCATCA CTTGCCGGGCAAGTCGGACCATTAACAACTAT TTAAATTGGTATCAGCAGAAACCAGGGAAAG CCCCTAAACTCCTGATCTTTGCTACATCCAGTT TACAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCCTTA TTCGCTTTCGGCCCTGGGACCAAAGTGGATAT CAAA SEQ ID NO: 24311 | GAGGGCGCAGCTGTTGGAGTCTGGGGGAGGCTTG GAACAGCCTGGGGGGTCCCTGAGACTCTCCTGTG CAGCCCTCTGAATTCACCTTTAGCAGCTATGCCAT GAGCTGGGTCCGCCAGGCTCCAGGGAAGGGGCT GGAGTGGGTCTCAGTTATTAGTGGTAGAGGTGGT AACACATACTCCCGAGACTCCGTGAAGGGCCGG TTCACCATCTCCAGAGACAATTCCAAGAACACGC TATATCTACAAATGAACAGCCTGAGAGCCGAGG ACACGGCCGTATATTACTGTGCGTCGTCCCGTTTAGC AGTGGCTGGCTCGGAGGCTTTCATATCTGGGGC CAAGGGACAATGGTCACCGTCTCTTCA SEQ ID NO: 28317 |

FIGURE 50
(Continued)

| | | | | |
|---|---|---|---|---|
| iPS:392706 | 21-225_18A3 | AA | DIQMTQSPSSLSASIGDRVSITCRASRTINNYLNW YQQKPGKAPKLLIFATSSLQSGVPSRFSGSGSGT DFTLTISSLQPEDFATYYCQQTYSTPLFAFGPGTK VDIK<br>SEQ ID NO: 24312 | EAQLLESGGGLEQPGGSLRLSCAASGFTFSSYAMS WVRQAPGKGLEWVSVISGRGNTYSADSVKGRFTI SRDNSKNTLYLQMNSLRAEDTAVYYCASRLAVAG SEAFHIWGQGTMVTVSS<br>SEQ ID NO: 28318 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGTTGCATCCAGTT TGCAAAGTGGGGTCCCATCAAGGTTCAACGGC AGTGGATCTGGGACAGAATTCACTCTCACAAT CAGCAGCCTGCAGCCTGAAGATATTTGCAACTT ATTACTGTCTACAGCATAGTAGTTACCCGCTC ACTTTCGGCGGAGGGACCAAGGTGGAGATCA AA<br>SEQ ID NO: 24313 | CAGCTCGAGTCTGCAGGAGTCGGGGCCAGGACTG GTGAAGTTTTCGGAGACCCTGTCCCTCACCTGCA CTGTCTCTGGTGGCTCCATCAGCAGAAGTAGTTA TTACTGGGGCTGGATCCGCCAGCCCCCAGGGAA GGGGCTGGAGTGGATAGGGAATATCTATTATAGT GGGTATACCTACTACTACCTCCGTCCCTCCAAGAGTC GAGTCACCATATCCGTAGACACGTCCAAGAACC AGTTCTCCCTGAAGCTGAGCTCTGTGACCGCCGC AGACACGGCTGTGTATTACTGTGCGAGACATAGC ACCAGCTGGTCCCTGACTACTGGGGCCAGGGAA CCCTGGTCACCGTCTCCTCA<br>SEQ ID NO: 28319 |
| | | AA | DIQMTQSPSSLSASVGDRVTITCRASQGIRNDLG WYQQKPGKAPKRLIYVASSLQSGVPSRFNGSGS GTEFTLTISSLQPEDFATYYCLQHSSYPLTFGGGT KVEIK<br>SEQ ID NO: 24314 | QLQLQESGPGLVKFSETLSLTCTVSGGSISRSSYYW GWIRQPPGKGLEWIGNIYYSGYTYTPSLKSRVTIS VDTSKNQFSLKLSSVTAADTAVYYCARHSTSWSLD YWGQGTLVTVSS<br>SEQ ID NO: 28320 |

FIGURE 50
(Continued)

| | | | | |
|---|---|---|---|---|
| iPS:392708 | 21-225_18D11 | NA | GACATCCAGATGACCCAGTCTCCATCCTCCACT GTTTGCATTTGTAGGAGACAGAGTCACCATCA CTTGTCGGGCGAGTCAGGGCATTAGTTATTAT TTAGCCTGGTTTCAGCAGAAACCAGGGAAAGC CCCTAAGTCCCTGATTTATGTTGCATCCAGTTT GCAAAGTGGGGTCCCATCAAAGTTCAGCGGCA GTGGATTTGGGACAGATTTCACTCTCACCATC AGCAGCCTGCAGCCTGAAGATTTTGCAACTTA TTACTGCCAACAGTATAATACTTACCCATTCA CTTTCGGCCCTGGGACCACAGTGGATATCAAG <br>SEQ ID NO: 24315 | GAGGTGCAGCTGGTGGAGTCTGGGGGAGGCTTG GTACAGCCTGGGGGGTCCCTGAGACTCTCCTGTG CAGCCTCTGGATTCACCTTCAGAAGCTATAGCAT GAACTGGGTCCGCCAGGCTCCAGGGAAGGGGCT GGAGTGGCTTTCATACATTAGTAGTAGTAGTGGT ACCATATACTACGCAGACTCTGTGAAGGGCCGAT TCACCATCTCCAGAGACAACGCCAGGAACTCACT GAATCTGCAAATGAACAGCCTGAGAGACGAGGA CACGGCTGTGTATTACTGTGCGAGAGAGGAGGTGGG AGCCCTTTTGACTACTGGGGCCAGGGAATCCTGG TCACCGTCTCCTCA <br>SEQ ID NO: 28321 |
| | | AA | DIQMTQSPSSLFAFVGDRVTITCRASQGISYYLA WFQQKPGKAPKSLIYVASSLQSGVPSKFSGSGFG TDFTLTISSLQPEDFATYYCQQYNTYPFTFGPGT VDIK <br>SEQ ID NO: 24316 | EVQLVESGGGLVQPGGSLRLSCAASGFTFRSYSMN WVRQAPGKGLEWLSYISSSSGTIYYADSVKGRFTIS RDNARNSLNLQMNSLRDEDTAVYYCARGGGSPFD YWGQGILVTVSS <br>SEQ ID NO: 28322 |
| iPS:392710 | 21-225_19A10 | NA | GACATCCAGATGACCCAGTCTCCATCCTCCCT GTCTGCATCTGTAGGAGACAGAGTCACCATCA CTTGCCGGGCAAGTCAGGGCATTAGAAACTGAT TTAGGCTGGTATCAGCAGAGACCAGGGAAAG CCCCTAAGCGCCTGATCTATACTGCATCCAGT TTGCAAAGTGGGGTCCCATCAAGGTTCAGCGG CAGTGGATCTGGGACAGATTCACTCTCACAA TCAGCAGGCTGCAGCCTGAAGATTTTGCAACT TATTACTGTCTACAGCATAATATGGTTACCCGTG GACGTTCGGCCAAGGGACCAAGGTGAAATC AAA <br>SEQ ID NO: 24317 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGCAGACTCCGTGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGAGTTGC CTGTACGAGGACTCCTGGGGCCAGGGAACCCT GGTCACCGTCTCCTCA <br>SEQ ID NO: 28323 |

FIGURE 50
(Continued)

| | | | | |
|---|---|---|---|---|
| | | AA | DIQMTQSPSSLSASVGDRVTITCRASQGIRTDLG WYQQRPGKAPKRLIYTASSLQSGVPSRFSGSGSG TEFTLTISRLQPEDFATYYCLQHNGYPWTFGQGT KVEIK<br><br>SEQ ID NO: 24318 | QVQLVESGGGVVQPGRSLRLSCAASGFTFSSYGMH WVRQAPGKGLEWVAVIWYDESNKYYADSVKGRF TISRDNSKNTLYLQMNSLRAEDTAVYYCARELAW YEDSWGQGTLVTVSS<br><br>SEQ ID NO: 28324 |
| iPS:392714 | 21-225_16G12 | NA | GACATCCAGATGACCCAGTCTCCATCCTCACT GTCTGCATCTGTTGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGAGGC AGTGGATCTGGGACAGATTTCACTCTCACCAT CAGCAACCTGCAGCCTGAAGATTTTGCATCTT ATTACTGCCAACAGTATCATAGTTTCCCATTCA CTTTCGGCCCTGGGACCAAAGTGGATATCAAA<br><br>SEQ ID NO: 24319 | GAGGTGCAACTGTTGGAGTCGGGGGAGGCTTG GTACAGCCTGGGGGGTCCCTGAGACTCTCCTGTG CAGCCTCTGGATTCTCCTTTAGTAGCTATGCCAT GACCTGGGTCCGCCAGGCTCCAGGGAAGGGCT GGAGTGGGTCTCAACTATTAGTGGTCGTGGTGGT CACACATACTACGCAGACTCCGTGAGGGCCGG TTCGCCATCTCCAGAGACAATTCCAAGAACACGC TGTATCTGCAAATGAACAGCCTGAGAGCCGAGG ACACGGCCGTATATTACTGTGCGAAACAGGACTG CTGGGGCCAGGGAACCCTGGTCACCGTCTCCTCA<br><br>SEQ ID NO: 28325 |
| | | AA | DIQMTQSPSSLSASVGDRVTITCRASQDISNYLA WFQQKPGKAPKSLIYAASSLQSGVPSKFRGSGSG TDFTLTISNLQPEDFASYYCQQYHSFPFTFGPGTK VDIK<br><br>SEQ ID NO: 24320 | EVQLLESGGGLVQPGGSLRLSCAASGFSFSSYAMT WVRQAPGKGLEWVSTISGRGGHTYADSVRGRFA ISRDSSKNTLYLQMNSLRAEDTAVYYCAKQDCWG QGTLVTVSS<br><br>SEQ ID NO: 28326 |

FIGURE 50
(Continued)

| | | | |
|---|---|---|---|
| iPS:392716 | 21-225_17B5 | NA | GACATCCAGATGACCCAGTCTCCATCCCTGTCTGCATCTGTAGGAGACAGAGTCACCATCACTTGCCGGGCAAGTCAGGGCATTAGAAATGATTTAGGCCTGGTATCAGCAGAAACCAGGGAAAGCCCCTAAGCGCCTGATCTATGCTGCATCCAATTTGCAAAGTGGGGTCCCATCAAGGTTCAGCGGCAGTGGATCTGGGACAGAATTCAGTTCACAATCAGCAGCCTGCAGCCTGAAGATTTTGCAACTTATTACTGTCTACAGCATAATAGTTACCCGCTCACTTTCGGCGGAGGGACCAAGGTGGAGATCAAAA SEQ ID NO: 24321 | CAGGTGCAGTTGGTGGAGTCTGGGGGAGGCGTGGTCCAGCCTGGGAGGTCCCTGAGACTCTCCTGTCAGCCGTCTGGATTCACCTTCAGTGACTATGGCATGCACTGGGTCCGCCAGGCTCCAGGCAAGGGGCTGGAGTGGGTGGCAGTTATATGGTATGATGAAAGTAATAAACACTATATAGACTCCGTGAAGGGCCGATTCACCATCTCCAGAGACACAATTCCAAGAACACGCTGTATCTGCAAATGAACAGCCTGAGAGCCGAGGACACGGCTGTGTATTATTGCGTGAGAGAACTGGGGTTCCGGTTTGACTACTGGGGCCAGGGAACCCTGGTCACCGTCTCCTCA SEQ ID NO: 28327 |
| | | AA | DIQMTQSPSSLSASVGDRVTITCRASQGIRNDLGWYQQKPGKAPKRLIYAASNLQSGVPSRFSGSGSGTEFSFTISSLQPEDFATYYCLQHNSYPLTFGGGTKVEIK SEQ ID NO: 24322 | QVQLVESGGGVVQPGRSLRLSCAASGFTFSDYGMHWVRQAPGKGLEWVAVIWYDESNKHYIDSVKGRFTISRDNSKNTLYLQMNSLRAEDTAVYYCVRELGFRFDYWGQGTLVTVSS SEQ ID NO: 28328 |
| iPS:392718 | 21-225_17B8 | NA | GATATTGTGATGACTCAGTCTCCACTCTCCCTGCCCGTCACCCCTGGAGAGCCGGCCTCCATCTCCTGTAGGTCTAGTCAGAGCCTCCTGCATAGTAATGGGAACAACTCTTTGGATTGGTACCTGCAGAAGCCAGGCCAGTCTCCACAGCTCCTGATCTATTTTGGGGTTCTCATCGGGCCTCCGGGGTCCCTGACAGGTTCAGTGACAGTGGATCAGGCACAGATTTTACACTGAAAATCAGCAGAGTGGAGGCTGAAGATGTTGGGGTTTATTACTGCATGCAAGGTCTACAAACTCCTCCCCTCACTTTCGGCGGAGGGACCAAGGTGGAGATCAAA SEQ ID NO: 24323 | CAGGTGCAGCTGGTGCAGTCTGGGGCTGAGGTGAAGAAGCCTGGGGCCTCAGTGAAGGTCTCCTGCAAGGCGTCTGGATACACCTTCACCAGCTATGCTATCAACTGGGTGCGACAGGCCACTGGACAAGGGCTTGAGTGGATGGGATGGATGAACCTAACACTGGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACGGCCGTATATTTCTGTACGAGAAAGGCTGGGTTTGACTACTGGGGCCAGGGAACCCTGGTCACCGTCTCCTCA SEQ ID NO: 28329 |

FIGURE 50
(Continued)

| | | | |
|---|---|---|---|
| | | AA | DIVMTQSPLSLPVTPGEPASISCRSSQSLLHSNGN NSLDWYLQKPGQSPQLLIYLGSHRASGVPDRFS DSGSGTDFTLKISRVEAEDVGVYYCMQVLQTPP LTFGGGTKVEIK<br>SEQ ID NO: 24324 | QVQLVQSGAEVKKPGASVKVSCKASGYTFTSYAIN WVRQATGQGLEWMGWMNPNTGNTGYAQKFQGR VTMTRNTSISTAYMELSSLRSEDTAVYFCTRKAGF DYWGQGTLVTVSS<br>SEQ ID NO: 28330 |
| iPS:392720 | 21-225_17A12 | NA | GACATCCAGATGACCCAGTCTCCATCCTCCCT GTCTGCATCTGTAGGAGACAGAGTCACCATCA CTTGCCGGGCAAGTCAGAGCATTAGTAGTTAT TTAAATTGGTATCACCAGAAACCAGGAAAGC CCCTAAGCTCCTGATCTATGCTGCATCCAGTTT GCAAAGTGGGGTCCCATCAAGGTTCAGTGGCA GTGGATCTGGGACAGATTTCACTCTCACCATC AGCAATCTGCAACCTGAAGATTTTGCAACTTA CTACTGTCAACAGAGTTACAATACCCCCTTAT TCACTTTCGGCCCTGGGACCAAAGTGGATATC AAA<br>SEQ ID NO: 24325 | GAGGTGCAGCTGTTGGAGTCTGGGGGAGGCTTG ATACAGCCTGGGGGGTCCCTGAGACTCTCCTGTG CAGCCTCTGAATTCACCTTCAGCAGCTATGCCAT GAGCTGGGTCCGCCAGGATCCAGGGAAGGGGCT GGAGTGGGTCTCAATTATTAGTGGTCGTGGGGA AACGCATTCTACGCAGACTCCGTGAAGGGCCGGT TCACCATCTCCAGAGACAATTCCAAGAACACGCT GTATCTGCAAATGAACAGCTGAGAGCCGAGGA CACGGCCGTATATTACTGTGCGTCCCGTATAGCA GTGGCTGGCTCGGAGGCTTTTGATATCTGGGGCC AAGGGACAATGGTCACCGTCTCTCTCA<br>SEQ ID NO: 28331 |
| | | AA | DIQMTQSPSSLSASVGDRVTITCRASQSISSYLNW YHQKPGKAPKLLIYAASSLQSGVPSRFSGSGSGT DFTLTISNLQPEDFATYYCQQSYNTPLFTFGPGT KVDIK<br>SEQ ID NO: 24326 | EVQLLESGGGLIQPGGSLRLSCAASEFTFSSYAMSW VRQDPGKGLEWVSIISGRGGNAFYADSVKGRFTISR DNSKNTLYLQMNSLRAEDTAVYYCASRIAVAGSE AFDIWGQGTMVTVSS<br>SEQ ID NO: 28332 |

FIGURE 50
(Continued)

| | | | | |
|---|---|---|---|---|
| iPS:392722 | 21-225_18E12 | NA | GACATCCAGATGACCCAGTCTCCATCCTCCCT GTCTGCATCTGTAGGAGACAGAGTCACCATCA CTTGCCGGGCAAGTCAGAGCATTAGTAGTTAT TTAAATTGGTATCAGCAGAAACCAGGGAAAG CCCCTACGCTCCTGATCTATGCTGCATCCAGTT TACAAAGTGGGGTCCCATCAAGGTTCAGTGGC AGTGGATCTGGGACAGATTTCACTCTCACCAT CAACAGTCTGCAACAGAGAGTTACAGAACCCCTTT ACTTCTGTCAACAGAGTTACAGAACCCCTTT TTCACTTTCGGCCCTGGGACCAAAGTGGATAT CAAA | GAGGTGCAGCTGTTGGAGTCTGGGGGAGGCTTG GTACAGCCTGGGGGGTCCCTGAGACTCTCCTGTG CAGCCTCTGAATTCACCTTTAGCAGCTATGCCAT GAGCTGGGTCCGCCAGGCTCCAGGGACGGGCT GGAGTGGGTCTCAATTATTAGTGGTCGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGTCCCGTCTGGCA GTGGCTGGCTCGGAGGCTTTGATATCTGGGGCC AAGGGACGATGGTCACCGTCTCTTCA |
| | | | SEQ ID NO: 24327 | SEQ ID NO: 28333 |
| | | AA | DIQMTQSPSSLSASVGDRVTITCRASQSISSYLNW YQQKPGKAPTLLIYAASSLQSGVPSRFSGSGSGT DFTLTINSLQPEDFATYFCQQSYRTPFFTGPGTK VDIK | EVQLLESGGGLVQPGGSLRLSCAASEFTFSSYAMS WVRQAPGTGLEWVSIISGRGGNTFYADSVKGRFTI SRDNSKNTLYLQMNSLRAEDTAVYYCASRLAVAG SEAFDIWGQGTMVTVSS |
| | | | SEQ ID NO: 24328 | SEQ ID NO: 28334 |
| iPS:392726 | 21-225_20B5 | NA | GACATCCAGATGACCCAGTCTCCATCCTCCCT GTCTGCATCTGTAGGAGACAGAGTCACCATCA CTTGCCGGGCGAGTCAGGGCATTAACAATTAT TTAGCCTGGTATCAGCAGAAACCAGGGAAAAT TCCTAAGCTCCTGATCTATGCTGCATCCACTTT GCAATCAGGGGTCCCCTCCGTTCAGTGGCA GTGGATCTGGGACAGATTTCACTCTCACCATC AGCAGCCTGCAAAGTATAACAGTGCCCCTCCGA TTGCTGTCAAAAGTATAACAGTGCCCCTCCGA TCACCTTCGGCCAAGGGACACGACTGGAGATT AAA | GAGGTGCAGCTGTGGTGGAGGCCGGGAGGCCTG GTCAAGCCTGGGGGGGTCCCTGAGACTCTCCTGTG CAGCCTCTGGATTCACCTTCACCAGCTATAGCAT GAACTGGGTCCGCCAGGCTCCAGGGAAGGGCT GGAGTGGGTCTCATCCATTAGTGGGAGTAGTAGT TACATATACTACCAGAGACTCAGTGAAGGCCGAT TCACCATCTCCAGAGACAATCGCCAAGAACTCACT GTATCTGCAAATGAACAGCCTGAGAGCCGAGGA CACGGCTGTGTATTACTGTGCGAGAGATCGTGGG AGTACTGGGGCCAGGGTACCCTGGTCACCGTCT CCTCA |
| | | | SEQ ID NO: 24329 | SEQ ID NO: 28335 |

FIGURE 50
(Continued)

| | | | |
|---|---|---|---|
| | | AA | DIQMTQSPSSLSASVGDRVTITCRASQGINNYLA WYQQKPGKIPKLLIYAASTLQSGVPSRFSGSGSG TDFTLTISSLQPEDVATYCCQKYNSAPPITFGQGT RLEIK<br>SEQ ID NO: 24330 | EVQLVEAGGGLVKPGGSLRLSCAASGFTFTSYSMN WVRQAPGKGLEWVSSISGSSSYIYYADSVKGRFTIS RDNAKNSLYLQMNSLRAEDTAVYYCARDRGSYW GQGTLVTVSS<br>SEQ ID NO: 28336 |
| iPS:392728 | 21-225_20F7 | NA | GACATCCAGATGACCCAGTCTCCATCTTCCGT GTCTGCATCTGTAGGAGACGGAGTCACCATCA CTTGTCGGGCGAGTCAGGGTATTAGCAGCTGG TTAGCCTGGTATCAGCAGAAACCAGGGAAAG CCCCTAAACTCTTGATTTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCTCGG ACGTTCGGCCAAGGGACCAAGGTGGAAATCA AA<br>SEQ ID NO: 24331 | CAGGTGCAGCTGGTGGAGTCTGGGGGAGGCTTG GTCAAGCCTGGAGGGTCCCTGAGACTCTCCTGTG CAGCCTCTGGATTCACCTTCACTAGCTATTACAT GAGCTGGATCCGCCAGGCTCCAGGGAAGGGGCT GGAGTGGGTTCACATTAGTAGTAGTGGTAGT ACCATATACTACGCAGACTCTGTGAAGGGCCGAT TCACCATCTCCAGGGACAACGGCGAGAACTCACT GTATCTGCAAATGAACAGCCTGAGAGCCGAGGA CACGGCCGTGTATTACTGTGCGAGATATCGAAT AACCGGGGGTACTTCGATCTCTGGGGCCGTGGCT CCCTGGTCACTGTCTCCTCA<br>SEQ ID NO: 28337 |
| | | AA | DIQMTQSPSSVSASVGDGVTITCRASQGISSWLA WYQQKPGKAPKLLIYAASSLQSGVPSRFSGSGS GTDFTLTISSLQPEDFATYCCQQANSFPRTFGQG TKVEIK<br>SEQ ID NO: 24332 | QVQLVESGGGLVKPGGSLRLSCAASGFTFSDYYMS WIRQAPGKGLEWVSHISSSGSTIYYADSVKGRFTIS RDNGENSLYLQMNSLRAEDTAVYYCARYRNNRG YFDLWGRGSLVTVSS<br>SEQ ID NO: 28338 |

FIGURE 50
(Continued)

| | | | |
|---|---|---|---|
| iPS:392730 | 21-225_17A1 | NA | GACATCCAGATGACCCAGTCTCCATCCTCCT GTCTGCATCTGTAGGAGACAGAGTCACCATCA CCTGCCGGGCAAGTCAGAACATTAACAATTAT TTAAATTGGTATCAGCAGCAGAAACCAGGAAAG GCCCTAAGGTCCTGATCTTTACTACATCTAGTT TACAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACACTACCCCCACG TGGACGTTCGGCCAAGGGACCAAGGTGGAAA TCAAA SEQ ID NO: 24333 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGTTATTAGTGGTAGTGGTAGT AACACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAAAGATATAC CAGTGACTGGCATGATGCTTTTGATATCTGGGGC CAAGGGACAATGGTCACCGTCTCTTCA SEQ ID NO: 28339 |
| | | AA | DIQMTQSPSSLSASVGDRVTITCRASQNINNYLN WYQQKPGKAPKVLIFTTSSLQSGVPSRFSGSGSG TDFTLTISSLQPEDFATYYCQQSYTTPTWTFGQG TKVEIK SEQ ID NO: 24334 | EVQLLESGGGLVQPGGSLRLSCAASGFTFSSYAMN WVRQAPGKGLEWVSVISGSGSNTYYADSVKGRFTI SRDNSKNTLYLQMNSLRAEDTAVYYCAKRYTSDW HDAFDIWGQGTMVTVSS SEQ ID NO: 28340 |
| iPS:392732 | 21-225_17E5 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGCAGAAACCAGGAAAG CCCCTAAGGCCCTGATCTATACTGCATCCAGT TTGCAAAGTGGGGTCCCATCAAGGTTCAGCGG CAGTGGATCTGGGACAGACCTCACTCTCACAA TCAGCAGCCTGCAGCCTGAAGATTTTGCAACT TATTACTGTCTACAACATAATAGTTACCCGTTG ACGTTCGGCCAAGGGACCAAGGTGGTCATCAA A SEQ ID NO: 24335 | CAGGTGCAACTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCACTTATATGGACTCCGTGAAGG GCCGAAATAAATACTATGGACTCCGTGAAGGGCCGA TTCACCATCTCCAGAGACAATTCCAAGAACAGC TGTATCTGCAACTGAACAGCCTGAGAGCCGAGG ACACGGCTGTGTATTACTGTGCGAGAGAGCTTGG CTGGTACGAGGACTACTGGGGCCAGGGAACCCT GGTCACCGTCTCCTCA SEQ ID NO: 28341 |

FIGURE 50
(Continued)

| | | | |
|---|---|---|---|
| iPS:392734 | | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNSYPLTFGPGTK VVIK<br>SEQ ID NO: 24336 | QVQLVESGGGVVQPGRSLRLSCAASGFTFSDYGM HWVRQAPGKGLEWVALIWYDVTNKYYGDSVKGR FTISRDNSQNTLYLQLNSLRAEDTAVYYCARELGW YEDYWGQGTLVTVSS<br>SEQ ID NO: 28342 |
| | 21-225_17D8 | NA | GAAATAGTGATGACGCAGTCTCCATCCACCCT GTCTGTGTCTCCAGGGGAAAGAGCCACCCTCT CCTGCAGGGCCAGTCAGAGTGTTAGCAGCAAC CAGCCCTGGTCTGATTCACCTTCAGTAGCTATGCTT TTAGCCTGGTTCCAGCAGAAACCTGGCCAGGC GAACCTGGGTCCGCCAGGCTCCAGGGAAGGGCT TCCCAGGCTCCTCATCAATGGTGCATCCACCA GGAGTGGGTCTCATCCATTAGTGGTAGTGGTAGT GGGCCAGTGGTATCCCAGCCAGGTTCAGTGGC CACATATCCTACGCGGACTCAGTGAAGGGCCGAT AGTGGGTCTGGGACAGAGTTCACTCTCACCAT TCACCATCTCCAGAGACAACGCCAAGAACTCACT CAGCAGCCTGCAGTCTGAAGATTATAATAACTGGCCTCTG GTATCTGCAACTGAACAGCCTGAGAGCCGAGGA ATTACTGTCAGCAGTATAATAACTGGCCTCTG CACGGCTGTGTATTACTGTGCGAGAGATCGGGGC ACGTTCGGCCAAGGGACCAAGGTGGAAATCA AGTGGCTGGGGCCAGGGAACCCTGGTCACCGTCT AA CCTCA<br>SEQ ID NO: 24337 | SEQ ID NO: 28343 |
| | | AA | EIVMTQSPSTLSVSPGERATLSCRASQSVSSNLA WFQQKPGQAPRLLINGASTRASGIPARFSGSGSG TEFTLTISSLQSEDFAVYYCQQYNNWPLTFGQGT KVEIK<br>SEQ ID NO: 24338 | EVQLVESGGGLVKPGGSLRLSCAASGFTFSSYGLN WVRQAPGKGLEWVSSISGSGSHISYADSVKGRFTIS RDNAKNSLYLQLNSLRAEDTAVYYCARDRGSGWG QGTLVTVSS<br>SEQ ID NO: 28344 |

FIGURE 50
(Continued)

| | | | | |
|---|---|---|---|---|
| iPS:392736 | 21-225_17B12 | NA | GACATCCAGATGACCCAGTCTCCATCCTCCCT GTCTGCATCTGTAGGAGACAGAGTCTCCATCA CTTGCCGGGCAAGTCAGAATATTAACAACTAT TTAAATTGGTATCAGCAGAAACCAGGGAAAG GCCCTAAGGTCCTGATCCTTACTGCATCCAGTT TGCAAAGTGGGGGTCCCATCAAGGTTCAGTGGC AGTGGATCTGGGACAGATTTCACTCTCACCAT CAGCAGTCTACAACCTGAAGATTTTGCAACTT ACTACTGTCAACAGACTTACACTCCCCACG TGGACGTTCGGCCAAGGGACCAAGGTGAAA TCAAA<br><br>SEQ ID NO: 24339 | GAGGTGCAGCTGTTGGAGTCTGGGGGAGGCTTG GTACAGCCTGGGGGGTCCCTGAGACTCTCCTGTG TAGCCCTCTGGATTCACCTTTAGCAGCAGTATGCCAT GAACTGGGTCCGCCAGGCTCCAGGGAAGGGGCT GGAGTGGGTCTCAGTTATTAGTGGTAGTGGTGGT AGCACATACTACGCAGACTCCGTGAAGGGCCGG TTCACCATCTCCAGAGACAATTCCAAGAACACGC TGTATCTGCAAATGAACACCCTGAGAGCCGAGG ACACGGCCGTATATTACTGTGCGAAAGGTATAC CAGTGACTGGCATGATGCTTTTGATATCTGGGGC CAAGGGACAATGGTCACCGTCTCTTCA<br><br>SEQ ID NO: 28345 |
| | | AA | DIQMTQSPSSLSASVGDRVSITCRASQNINNYLN WYQQKPGKVLILTASSLQSGVPSRFSGSGSG TDFTLTISSLQPEDFATYYCQQTYTPTWTFGQG TKVEIK<br><br>SEQ ID NO: 24340 | EVQLLESGGGLVQPGGSLRLSCVASGFTFSSYAMN WVRQAPGKGLEWVSVISGSGSTYYADSVKGRFTI SRDNSKNTLYLQMNTLRAEDTAVYYCAKRYTSDW HDAFDIWGQGTMVTVSS<br><br>SEQ ID NO: 28346 |
| iPS:392738 | 21-225_18G4 | NA | GACATCCACATGACCCAGTCTCCATCCTCCCT GTCTGCATCTGTAGGAGACAGAGTCACCATCA CTTGCCGGGCAAGTCAGAGCATTATCAGCTAT TTAAATTGGTATCAGCAGAAACCAGGGAAAG CCCCTAAGGTCCTGATCTATACTGCATCCAGTT TGCAAACTGGGGTCCCATCAGGGTTCAGTGGC AGTGGATCTGGGACAGATTTCACTCTCACCAT CAGCAGTCTGCAACAGACTTACAGTCCCCCGCTC ACTTTCGGCGGTGGGACCAAGGTGGAGATCAA A<br><br>SEQ ID NO: 24341 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCTGAG TATGGGCGGTATGGACGTCTGGGGCCAAGGGAC CACGGTCACCGTCTCCTCA<br><br>SEQ ID NO: 28347 |

FIGURE 50
(Continued)

| | | | |
|---|---|---|---|
| iPS:392740 | 21-225_18H12 | AA | DIHMTQSPSSLSASVGDRVTITCRASQSIISYLNW YQQKPGKAPKVLIYTASSLQTGVPSGFSGSGSGT DFTLTISSLQPEDFATYYCQQTYSPPLTFGGGTK VEIK<br>SEQ ID NO: 24342 | QVQLVESGGGVVQPGRSLRLSCAASGFTFSSYGMH WVRQAPGKGLEWVAIIWYDGSNKYYADSVKGRFT ISRDNSKNTLYLQMNSLRAEDTAVYYCARDLSMG GMDVWGQGTTVTVSS<br>SEQ ID NO: 28348 |
| | | NA | GACATCCAGATGACCCAGTCTCCATCCTCCCT GTCTGCGTCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATACTGCATCCAAT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAACATAATAATTACCCGTG GACGTTCGGCCCTAGGGACCAAGGTGGTCATCA AA<br>SEQ ID NO: 24343 | CAGGTGCAACTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGATGGCAGTTATATGGTATGATGGTAACT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTTTATTACTGTGCGAGAGAGGTTGG CTGGTACGAGGACTACTGGGGCCAGGGAACCCT GGTCACCGTCTCCTCA<br>SEQ ID NO: 28349 |
| | | AA | DIQMTQSPSSLSASVGDRVTITCRASQGIRNDLG WYQQKPGKAPKRLIYTASNLQSGVPSRFSGSGS GTEFTLTISSLQPEDFATYYCLQHNNYPWTFGLG TKVVIK<br>SEQ ID NO: 24344 | QVQLVESGGGVVQPGRSLRLSCAASGFTFSDYGM HWVRQAPGKGLEWMAVIWYDVTNKYYADSVKG RFTISRDNSKNTLYLQMNSLRAEDTAVYYCAREVG WYEDYWGQGTLVTVSS<br>SEQ ID NO: 28350 |

FIGURE 50
(Continued)

| | | | |
|---|---|---|---|
| iPS:392742 | 21-225_20B2 | NA | GACATCCAGATGACCCAGTCTCCATCCTCCT<br>GTCTGCCTCTGTAGGAGACAGAGTCAATATCA<br>CTTGCCGGGCAAGTCAGGACATTAGAAATGAT<br>TTAGGCTGGTATCAGCAGCAGAAACCAGGAAAG<br>CCCCTAAGCGCCTGATCTATGCTGCATCCAGT<br>TTGCAAAGTGGGGTCCCATCAAGGTTCAGCGG<br>CAGTGGATCTGGGACAGATTCACTCTCACGA<br>TCAGCAGCCTGCAGCCTGAAGATTTTGCAACT<br>TATTACTGTCTACAGCATTATAATTACCCTCGG<br>GCGTTCGGCCAAGGGACCAAGGTGGATATCA<br>AA | CAGGTGCAACTGGTGGAGTCTGGGGGAGGCGTG<br>GTCCAGCCTGGGAGGTCCCTGAGACTCTCCTGTG<br>CAGCGTCTGATTCACCTTCAGTAATTATGTCATT<br>CACTGGGTCCGCCAGGCTCCAGGCAAGGGACTG<br>GAGTGGGTGGCAGTTATATGCAGACTCCGTGAAGTA<br>ATAAATACTATGCAGACTCCGTGAAGGGCCGTT<br>CACCATCTCCAGAGACAATTCCAAGAACACGCTG<br>TATCTGCAAATGAACAGCCTGAGAGCCGAGGAC<br>ACGGCTGTGTATTCCTGTGCGAGAGAAGTATA<br>GCAGCAGCTGGTACGACTACGGTATGGACGTCTG<br>GGGCCAAGGGACCACGGTCACCGTCTCCTCA |
| | | AA | SEQ ID NO: 24345 | SEQ ID NO: 28351 |
| | | | DIQMTQSPSSLSASVGDRVNITCRASQDIRNDLG<br>WYQQKPGKAPKRLIYAASSLQSGVPSRFSGSGS<br>GTEFTLTISSLQPEDFATYYCLQHYNYPRAFGQG<br>TKVDIK | QVQLVESGGGVVQPGRSLRLSCAASGFTFSNYVIH<br>WVRQAPGKGLEWVAVIWYDGSNKYYADSVKGRF<br>TISRDNSKNTLYLQMNSLRAEDTAVYSCAREKYSS<br>SWYDYGMDVWGQGTTVTVSS |
| | | | SEQ ID NO: 24346 | SEQ ID NO: 28352 |
| iPS:392744 | 21-225_20D5 | NA | GACATCCAGATGACCCAGTCTCCATCCTCCT<br>GTCTGCATCTGTAGGAGACAGAGTCACCATCA<br>CTTGCCGGGCAAGTCAGGGCATTAGAAATGAT<br>TTAGGCTGGTATCAGCAGCAGAAACCAGGAAAG<br>CCCCTAAGCGCCTGATCTATGCTGCATCCAGT<br>TTGCAAAGTGGGGTCCCATCAAGGTTCAGCGG<br>CAGTGGATCTGGGACAGATTCACTCTCACAA<br>TCAGCAGCCTGCAGCCTGAAGATTTTGCAACT<br>TATTACTGTCTACAGCATAATAGTTACCCGTTC<br>ACTTTCGGCGGAGGGACCAAGGTGGAGATCA<br>AA | CAGGTGCAGCTGGTGGAGTCTGGGGGAGGCGTG<br>GTCCAGCCTGGGAGGTCCCTGAGACTCTCCTGTG<br>CAGCGTCTGATTCACCTTCAGTAGTAGCTATGGCAT<br>GCACTGGGTCCGCCAGGCTCCAGGCAAGGGGCT<br>GGAGTGGGTGGCAGTTATTTGGTATGAAGAAAAT<br>AATCAATACTATGCAGACTCCGTGAAGGGCCGAT<br>TCACCATCTCCAGAGACAATTCCAAGAACACGCT<br>GTATCTGCAAATGAACAGCCTGAGAGCCGACGA<br>CACGGCTGTGTATTACTGTGCGAGAGAACTGGGG<br>TTCCGGTCTGACTACTGGGGCCAGGGAACCCTGG<br>TCACCGTCTCCTCA |
| | | | SEQ ID NO: 24347 | SEQ ID NO: 28353 |

FIGURE 50
(Continued)

| | | | |
|---|---|---|---|
| iPS:392746 | 21-225_20H7 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGGGT KVEIK<br>SEQ ID NO: 24348 | QVQLVESGGGVVQPGRSLRLSCAASGFTFSSYGMH WVRQAPGKGLEWVAVIWYEENNQYYADSVKGRF TISRDNSKNTLYLQMNSLRADDTAVYYCARELGFR SDYWGQGTLVTVSS<br>SEQ ID NO: 28354 |
| | | NA | GACATCCAGATGACCCAGTCTCCATCCTCACT GTCTGCATCTGTAGGAGACAGAGTCACCATCA CTTGTCGGACGAGTCAGGGCATTAACAATTAT TTAGTCTGGTTTCAGCAGAAACCAGGGAAAGC CCCTAAGCGCCTGATCTATGCTGCATCCAGTT GCAAAGTGGGGTCCCATCAAAGTTCAGCGGCA GTGGATCTGGGACAGAGCCTGAAGATTTTGCAACTA TTACTGCCAACAGTATTATAGTTACCCATTCAC TTTCGGCCCTGGGACCAAAATGATTTCAAA<br>SEQ ID NO: 24349 | GAGGTGCACCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TTCATATACTACCAGAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGTAGCAGCT CTTGACTACTGGGGCCAGGGAACCCTGGTCACCG TCTCCTCA<br>SEQ ID NO: 28355 |
| | | AA | DIQMTQSPSSLSASVGDRVTITCRTSQGINNYLV WFQQKPGKAPKRLIYAASSLQSGVPSKFSGSGSG TDFTLTISSLQPEDFATYYCQQYYSYPFTFGPGT KMDFK<br>SEQ ID NO: 24350 | EVHLVESGGGLVKPGGSLRLSCAASGFTFSSYSMN WVRQAPGKGLEWVSSISGSSSFIYADSVKGRFTIS RDNAKNSLYLQMNSLRAEDTAVYYCARVAALDY WGQGTLVTVSS<br>SEQ ID NO: 28356 |

FIGURE 50
(Continued)

| | | | |
|---|---|---|---|
| iPS:392748 | 21-225_20A8 | NA | GACATCCAGATGACCCAGTCTCCATCCTCACT GTCTGCATCTGTAGGAGACAGAGTCACCATCA CTTGTCGGGCGAGTCAGGGCATTAATAATTAT TTAGTCTGGTTTCAGCAGAAACCAGGGAAAGC CCCTAAGTCCCTGATCTATGCTGCATCCAGTT GCTGAGTGGGGTCCCATCAAAGTTCAGGGGCA GTGGATCGGGACAGATTTCACTCTCACCATC AGCAGCCTGCAGCCTGAAGATTTTGCAACTTA TTACTGCCAACAGTATAATAGTTACCCGATCA CCTTCGGCCAAGGGACACGACTGGAGATTAAA<br>SEQ ID NO: 24351 | GAGGTGCAGCTGGTGGAGTCTGGGGGAGGCCTG GTCAAGCCTGGGGGGTCCCTAAGACTCTCCTGTG CAGCCTCTGGATTCACCTTCAGTAGTATAGCGT GAACTGGGTCCGCCGGGCTCCAGGGAAGGGGCT GGAGTGGGTCTCATCCATTAGTAGTAGTAGTAGT TCCTATACTACGCAGACTCAGTGAAGGGCCGAT TCACCATCTCCAGAGACAACGCCAAGAACTCAGT GTATCTGCAAATGAACAGCCTGAGAGCCGAGA CACGGCTGTATATTACTGTGCGAGAAACTGGGAC TACTGGGGCCAGGGAACCCTGGTCACCGTCTCCT CA<br>SEQ ID NO: 28357 |
| | | AA | DIQMTQSPSSLSASVGDRVTITCRASQGINNYLV WFQQKPGKAPKSLIYAASSLLSGVPSKFSGSGSG TDFTLTISSLQPEDFATYYCQQYNSYPITFGQGTR LEIK<br>SEQ ID NO: 24352 | EVQLVESGGGLVKPGGSLRLSCAASGFTFSSYSVN WVRRAPGKGLEWVSSISSSSFLYYADSVKGRFTIS RDNAKNSVYLQMNSLRAEDTAVYYCARNWDYW GQGTLVTVSS<br>SEQ ID NO: 28358 |
| iPS:392750 | 21-225_20A10 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACAAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACCA TCAGCAGCCTGCAGCCTGAAGATTTTGCAACT TATTACTGTCTACAGCATAATAGATACCCGCT CACTTTCGGCGGAGGGACCAAGGTGGAGATC AAA<br>SEQ ID NO: 24353 | CAGGTGCAGCTGGTGGAGTCTGGGGGAGGCGTG GTCCAGCCTGGGAGGTCCCTGAGACTCTCCTGTG CAGCGTCTGGATTCACCTCACCAGTAGCGATGACAT GCACTGGGTCCGCCAGGCTCCAGGCAAGGGGCT GGAGTGGGTGGCAGTTATATGGTTTGATGGAAGT AATAAATACTATGCAGACTCCGTGAAGGGCCGA TTCATCATCTCCAGAGACACAATTCCAAGAACACGC TGTATCTGCAAATGAACAGCCTGAGAGCCGAGG ACACGGCTATGTATTACTGTGCGAGAGATCTAAT AGCAGCAGCTGGTACGGTTGACTACTGGGGCCA GGGAACCCTGGTCACCGTCTCCTCA<br>SEQ ID NO: 28359 |

FIGURE 50
(Continued)

| | | AA | DIQMTQSPSSLSASVGDRVTITCRASQGIRNDLG WYQQKQGKAPKRLIYAASSLQSGVPSRFSGSGS GTEFTLTISSLQPEDFATYYCLQHNRYPLTFGGG TKVEIK SEQ ID NO: 24354 | QVQLVESGGGVVQPGRSLRLSCAASGFTLSSDDMH WVRQAPGKGLEWVAVIWFDGSNKYYADSVKGRFI ISRDNSKNTLYLQMNSLRAEDTAMYYCARDLIAAA GTVDYWGQGTLVTVSS SEQ ID NO: 28360 |
|---|---|---|---|---|
| iPS:392754 | 21-225_21D3 | NA | GACATCCAGATGACCCAGTCTCCATCCTCCCT GTCTGCATCTGTAGGAGACAGAGTCACCATCA CTTGCCGGGCAAGTCAGAGACATTACTGGTTAT TCAAATTGGTATCAGCAGAAGCCAGGAAAA CCCCTAAACTCCTGATCTTTGCTACATACAGTT TGGAAAGTGGGGTCCCATCAAGGTTCAGTGGC AGTGGATTTGGGACAACTTCACTCTCACCAT CACCAGTCTGCAACCTGAAGATTTTGCAACTT ACTACTGTCAACAGAGTTACAGTACCTCGATC ACCTTCGGCCAAGGGACACGACTGGAGATTAA A SEQ ID NO: 24355 | CAGGTGCAGCTGGTGGTGGAGTCTGGGGAGGCGTG GTCCAGCCTGGGAGGTCCCTGAGACTCTCCTGTG TTGCCTCTGGATTCACCTTCAGTAGCTAGCTATGGCAT GCACTGGGTCCGCCAGGCTCCAGGCAAGGGGCT GGAGTGGGTGACAGTTATATCATATGATGGAAGT AATAAATACTATGCAGACTCCGTGAAGGGCCGA TTCACCATCTCAGAGACAATTCCAAGAACACGC TGTATCTGCAAATGAACAGCCTGAGAGCTGAGG ACACGGCTGTGTATTACTGTGCGAGAGGGGTATG GTTCGGGGACCTCTGGGGCCAGGGAACCCTGGTC ACCGTCTCCTCA SEQ ID NO: 28361 |
| | | AA | DIQMTQSPSSLSASVGDRVTITCRASQSITGYSN WYQQKPGKTPKLLIFATYSLESGVPSRFSGSGFG TNFTLTITSLQPEDFATYYCQQSYSTSITFGQGTR LEIK SEQ ID NO: 24356 | QVQLVESGGGVVQPGRSLRLSCVASGFTFSSYGMH WVRQAPGKGLEWVTVISYDGSNKYYADSVKGRFT ISRDNSKNTLYLQMNSLRAEDTAVYYCARGVWFG DLWGQGTLVTVSS SEQ ID NO: 28362 |

FIGURE 50
(Continued)

| | | | |
|---|---|---|---|
| iPS:392758 | 21-225_21G11 | NA | GACATCCAGATGACCCAGTCTCCATCCTCCCTGTCTGCGTCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATACTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAACATAATAATTACCCGTGGACGTTCGGCCAAGGGACCAAGGTGGTCATCAAA SEQ ID NO: 24357 | CAGGTGCAACTGGTGGAGTCTGGGGGAGGCGTGGTCCAGCCTGGGAGGTCCCTGAGACTCTCCTGTGCAGCGTCTGGATTCACCTTCAGTGACTATGGCATGCACTGGGTCCGCCAGGCTCCAGGCAAGGGGCTGGAGTGGATGGCAGTTATATGGTATGATGTAACTAATGAATACTATGCAGACTCCGTGAAGGGCCGATTCACCATCTCCAGAGACAATTCCAAGAACACGCTGTATCTGCAAATGAACAGCCTGAGAGAGCTTGGACACGGCTGTTTATTACTGTGCGAGAGAGAGCTTGGCTGGTACGAGGACTACTGGGGCCAGGGAACCCTGGTCACCGTCTCCTCA SEQ ID NO: 28363 |
| | | AA | DIQMTQSPSSLSASVGDRVTITCRASQGIRNDLGWYQQKPGKAPKRLIYTASSLQSGVPSRFSGSGSGTEFTLTISSLQPEDFATYYCLQHNNYPWTFGLGTKVVIK SEQ ID NO: 24358 | QVQLVESGGGVVQPGRSLRLSCAASGFTFSDYGMHWVRQAPGKGLEWMAVIWYDVTNEYYADSVKGRFTISRDNSKNTLYLQMNSLRAEDTAVYYCARELGWYEDYWGQGTLVTVSS SEQ ID NO: 28364 |
| iPS:392760 | 21-225_22G3 | NA | GACATCCAGATGACCCAGTCTCCATCCTCCCTGTCTGCATCTGTAGGAGACAGAGTCACCATCACTTGCCGGGCAAGTCAGAGCATTAGTAATTATTTAAATTGGTATCAGCAGAAACCAGGGAAAGCCCCTAAGCTCCTGATCTTTGCTGTTCCAGTTTGCAAAGTGGGGTCCCATCAAGGTTCAGTGGCAGTGGATCTGGGACAGATTTCACTCTCACCATCAGCGGTCTACAACCTGAAGATTTTGCAACTTACTTCTGTCAACAGAGTTTCAGAACCCCTTTTCACTTTCGGCGGCCCTGGGACCAAAGTGGATATCAAA SEQ ID NO: 24359 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGTATGCCATGAACTGGGTCCGCCAGGCTCCAGGGAAGGGGCTGGAGTGGGTCTCAATTATTAGTGGTCGTGGTGTTAACACATTCTACGCAGACTCCGTGAAGGGCCGGTTCACCATCTCCAGAGACAATGCCAAGAACTCCCTGTATCTGCAAATGAACAGCCTGAGAGCCGAGGACACGGCCGTATATTACTGTGCGAGAGGGGAGGCTGGCTCGGAGGCTTTTGATATCTGGGGCCAAGGGACAATGGTCACCGTCTCTTCA SEQ ID NO: 28365 |

FIGURE 50
(Continued)

| | | | | |
|---|---|---|---|---|
| | | | AA | DIQMTQSPSSLSASVGDRVTITCRASQSISNYLN WYQQKPGKAPKLLIFAASSLQSGVPSRFSGSGSG TDFTLTISGLQPEDFATYFCQQSFRTPFFTFGPGT KVDIK<br><br>SEQ ID NO: 24360 | EVQLLESGGGLVQPGGSLRLSCAASEFTFSSYAMN WVRQAPGKGLEWVSIISGRGVNTFYADSVKGRFTI SRDNSKNTLYLQMNSLRAEDTAVYYCASRLAVAG SEAFDIWGQGTMVTVSS<br><br>SEQ ID NO: 28366 |
| iPS:392762 | 21-225_22G5 | | NA | GACATCCAGATGACCCAGTCTCCATCCTCCCT GTCTGCATCTGTAGGAGACAGAGTCACCATCA CTTGCCGGGCAAGTCAGACAATTAGCAGCTAT TTAAATTGGTATCAGCAGAAACAAGGAAAG CCCCTAAGCTCCTGATCTATGCTGCATCCAGT TGCAAAATGGGGTCCCATCAAGGTTCAGTGGC AGAGGATCTGGGACAGATTTCACTCTCACCAT CAGTAGTCTGCAACCTGAAGATTTTGCAACTT ACTACTGTCAACAGAGTTACAGAACCCCTTA TTCACTTTCGGCCCTGGGACCAAGGTTGATTTC AAA<br><br>SEQ ID NO: 24361 | GAGGTGCAGCTGTTGGAGTCTGGGGGAGGCTTG GTACAGCCTGGGGGGTCCCTGAGACTCTCCTGT GCAGCCTCTGGATTCACCTTTAGCAGCTATGCCAT GAACTGGGTCCGCCAGGCTCCAGGGATGGGGCT GGAGTGGGTCTCAGTTATTAGTCGTAGTGGTGGT TACACATACTACGCGACTCCGTGAAGGGCCGGT TCACCATCTCCAGAGACAATTCCAAGAACACGCT GTATCTGCAAATGAACAGCCTGAGAGCCGAGGA CACGGCCGTCTATTACTGTGCGTCCCGTTTAGCA GTGGCTGGCTCGGAGGCTTTTGATATCTGGGGCC AAGGGACACTGGTCACCGTCTCTCA<br><br>SEQ ID NO: 28367 |
| | | | AA | DIQMTQSPSSLSASVGDRVTITCRASQNISSYLN WYQQKQGKAPKLLIYAASSLQNGVPSRFSGRGS GTDFTLTISSLQPEDFATYYCQQSYRTPLFTFGPG TKVDFK<br><br>SEQ ID NO: 24362 | EVQLLESGGGLVQPGGSLRLSCAASGFTFSSYAMN WVRQAPGMGLEWVSVISRSGGYTYYADSVKGRFT ISRDNSKNTLYLQMNSLRAEDTAVYYCASRLAVAG SEAFDIWGQGTLVTVSS<br><br>SEQ ID NO: 28368 |

FIGURE 50
(Continued)

| | | | | |
|---|---|---|---|---|
| iPS:392764 | 21-225_22G10 | NA | GACATCCAGATGACCCAGTCTCCATCCTCCT GTCTGCATCTGTAGGAGACAGAGTCACCATCA CTTGCCGGGCAAGTCAGAGCATTTTCAGCTAT TTAAATTGGTATCAGCAGAAACCAGGGAAAG CCCCTAAACTCCTGATCTATGCTGCATCCAGTT TACAAAGTGGGGTCCCATCAAGGTTCAGTGGC AGTGGATCTGGGACAGATTTCACTCTCACCAT CAGCAGTCTCCAACCTGAAGATTTTGCAACTT ACTTCTGTCAACAGAGTTTCAGAACCCCTTA TTCACTTTCGGCCCTGGGACCAAGGTGGATTT CAAA | GAGGTGCAGCTGTTGGAGTCTGGGGGAGACTTG GTACAGCCTGGGGGGTCCCTGAGACTCTCCTGTA CAGCCCTCTGATTCACCTTTAGCAGCTATGCCAT GAACTGGGTCCGCCAGGCTCCAGGGAAGGGGCT GGAGTGGGTCTCAGTTATTAGTGGTAGTGGTGGT AACACATTCTACGCAGACTCCGTGAAGGGCCGAT TCACCATCTCCAGAGACAATTCCAAGAACACGCT GTTTCTGCACATGAACAGCCTGAGAGCCGAGGA CACGGCCGTTTATTACTGTGCGTCCGTATGGCA GTGGCTGCTCGGAGGCTTTTGATATCTGGGGCC AAGGGACAATGGTCACCGTCTCTTCA |
| | | | SEQ ID NO: 24363 | SEQ ID NO: 28369 |
| | | AA | DIQMTQSPSSLSASVGDRVTITCRASQSIFSYLNW YQQKPGKAPKLLIYAASSLQSGVPSRFSGSGSGT DFTLTISSLQPEDFATYFCQQSFRTPLFTFGPGTK VDFK | EVQLLESGGDLVQPGGSLRLSCTASGFTFSSYAMN WVRQAPGKGLEWVSVISGSGGNTFYADSVKGRFTI SRDNSKNTLFLHMNSLRAEDTAVYYCASRMAVAG SEAFDIWGQGTMVTVSS |
| | | | SEQ ID NO: 24364 | SEQ ID NO: 28370 |
| iPS:392766 | 21-225_23H4 | NA | GACATCCAGATGACCCAGTCTCCATCCTCCCT GTCTGCATCTGTAGGAGACAGAGTCACCATCA CTTGCCGGGCAAGTCAGAGCATTAGCAGTAT TTAAATTGGTATCAGCAGAAACCAGGGAGAG CCCCTAAACTCCTGATCTGTTCTACATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ATTACTGTCAACAGAGTTACAGTACCCCCACG TGGACGTTCGGCCAAGGGACCAAGGTGGAAA TCAGA | GAGGTGCAGCTGTTGGAGTCTGGGGGAGGCTTG GTACAGCCTGGGGGGTCCCTGAGACTCTCCTGTG CAGCCTCTGATTCACCTTTAGCAGCTATGCCAT GAACTGGGTCCGCCAGGCTCCAGGGAAGGGGCT GGAGTGGGTCTCAGTTATTAGTGGTAGTGGTGGT ACCACATACTTCCGAGACTCCGTGAAGGGCCGGT TCACCATCTCCAAAGAAAATGAACAGCCTGAGAGAAACACGCT GTATCTGCAAATGAACAGCCTGAGAGCCGAGGA CAGTGGCTGGCATGATGTTTTGATATCTGGGGC CAAGGGACAAAGGTCACCGTCTCTCA |
| | | | SEQ ID NO: 24365 | SEQ ID NO: 28371 |

FIGURE 50
(Continued)

| | | | |
|---|---|---|---|
| | | AA | DIQMTQSPSSLSASVGDRVTITCRASQSISRYLN WYQQKPGRAPKLLICSTSSLQSGVPSRFSGSGSG TDFTLTISSLQPEDFATYYCQQSYSYTPTWTFGQG TKVEIR<br><br>SEQ ID NO: 24366 | EVQLLESGGGLVQPGGSLRLSCAASGFTFSSYAMN WVRQAPGKGLEWVSVISGSGGTTYYFADSVKGRFTI SRDNSKNTLYLQMNSLRAEDTAVYYCAKRNSSGW HDVFDIWGQGTKVTVSS<br><br>SEQ ID NO: 28372 |
| iPS:392768 | 21-225_20B8 | NA | GAAATAGTGATGACGCAGTCTCCATCCACCCT GTCTGTGTCTCCAGGGGAAAGAGTCACCCTCT CTTGCAGGGCCAGTCAGAGTGTTAGCAGCAAC TTAGCCTGGTTTCAGCAGAAACCTGGCCAGGC TCCCAGGCTCCTCATCAATGGTGCATCCACCA GGGCCAGTGGTATCCCAGCCAGGTTCAGTGGC AGTGGGTCTGGGACAGAGTTCACTCTCACCAT CAGCAGCCTGCAGTCTGAAGATTTTGCAGTT ATTACTGTCAGCAGTCAGTATAATAACTGTCCTCTG ACGTTCGGCCAAGGGACCAAGGTGGAAATCA AA<br><br>SEQ ID NO: 24367 | GAGGTGCAGCTGGTGGAGTCTGGGGGAGGCTG GTCAAGCCTGGGGGGGTCCCTGAGACTCTCCTGTG CAGCCCTCTGGATTCACCTTCAGTAGTTATAGCAT GAACTGGGTCCGCCAGGCTCCAGGGAAGGGGCT GGAGTGGGTCTCATCCATCAGTGGCAGTGGTAGT CACATATACTACGCGGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGATCGGGG CAGTGGCTGGGGCCAGGGAACCCTGGTCACCGT CTCCTCA<br><br>SEQ ID NO: 28373 |
| | | AA | EIVMTQSPSTLSVSPGERVTLSCRASQSVSSNLA WFQQKPGQAPRLLINGASTRASGIPARFSGSGSG TEFTLTISSLQSEDFAVYYCQQYNNCPLTFGQGT KVEIK<br><br>SEQ ID NO: 24368 | EVQLVESGGGLVKPGGSLRLSCAASGFTFSSYSMN WVRQAPGKGLEWVSSISGSGSHIYYADSVKGRFTIS RDNAKNSLYLQMNSLRAEDTAVYYCARDRGSGW GQGTLVTVSS<br><br>SEQ ID NO: 28374 |

FIGURE 50
(Continued)

| | | | |
|---|---|---|---|
| iPS:392770 | 21-225_20C10 | NA | GACATCCACATGACCCAGTCTCCATCCTCCT GTCTGCATCTGTGGAGACAAAGTCTCCATCA CTTGCCGGGCAAGTCACCATTAGCAACTAT TTAAATTGGTATCAGCAGAAACCAGGAAAG GCCCTAAGGTCCTGATCCTTACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACACTACCCCCACG TGGACGTTCGGCCAAGGGACCAAGGTGGAAA TCAAA <br><br> SEQ ID NO: 24369 | GAGGTGCAGCTGTTGGAGTCTGGGGGAGGCTTG GTACAGCCTGGGGGGTCCCTGAGACTCTCCTGTG CAGCCTCTGGATTCACTTTAGCAGCTATGCCAT GAACTGGGTCCGCCAGGCTCCAGGGAAGGGCT GGAGTGGGTCTCAGTTATTAGTGGTAGTGGTGGT ACCACATACTACGCAGACTCCGTGAAGGGCCGG TTCACCATCTCCAGAGACAATTCCAAGAACACGC TGTATCTGCAAATGAACACCCTGAGAGCCGAGG ACACGGCCGTATATTACTGTGCGAAAAGTATAC CAGTGACTGCATGAFGCTTTTGATATCTGGGGC CAAGGGACAATGGTCACCGTCTCTCA <br><br> SEQ ID NO: 28375 |
| | | AA | DIHMTQSPSSLSASVGDKVSITCRASHHISNYLN WYQQKPGKGPKVLILTASSLQSGVPSRFSGSGSG TDFTLTISSLQPEDFATYYCQQSYTTPTWTFGQG TKVEIK <br><br> SEQ ID NO: 24370 | EVQLLESGGGLVQPGGSLRLSCAASGFTFSSYAMN WVRQAPGKGLEWVSVISGSGGTTYYADSVKGRFTI SRDNSKNTLYLQMNTLRAEDTAVYYCAKRYTSDW HDAFDIWGQGTMVTVSS <br><br> SEQ ID NO: 28376 |
| iPS:392772 | 21-225_20E12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTTTGCTGCATCCAGTT TACAAAGTGGGGTCCCATCAAGGTTCAGCGGC AGTGGATCTGGGACAGCCTGCAGCCTGAAGATTCACTCTCACAAT CAGCAGCCTGCAGCCTGAAGATTTTGCAACTT ATTACTGTCTACAGCATAATAGTTACCCGTTC ACTTTCGGCGGAGGGACCAAGGTGGAGATCA AA <br><br> SEQ ID NO: 24371 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGGCT GGAGTGGGTGGCAGTTATGTGGTATGATGAAAGT AATAAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GTTCCGGTTTGACTACTGGGGCCAGGGAACCCTG GTCACCGTCTCTCA <br><br> SEQ ID NO: 28377 |

FIGURE 50
(Continued)

| | | | | |
|---|---|---|---|---|
| iPS:392774 | | AA | DIQMTQSPSSLSASVGDRVTITCRASQGIRNDLG WYQQKPGKAPKRLIFAASSLQSGVPSRFSGSGSG TEFTLTISSLQPEDFATYYCLQHNSYPFTFGGGTK VEIK | QVQLVESGGGVVQPGRSLRLSCAASGFTFSSYGMH WVRQAPGKGLEWVAVMWYDESNKHYADSVKGR FTISRDNSRNTLYLQMNSLRAEDTAVYYCARELGF RFDYWGQGTLVTVSS |
| | | | SEQ ID NO: 24372 | SEQ ID NO: 28378 |
| | | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTTCATTCTCACAA TCAGCAGCCTGCAGCCTGAAGATTTTGCAACT TATTACTGTCTACAGCATAGTAGTTACCCCTC ACTTTCGGCGGAGGGACCAAGGTGGAGATCA AA | CAGCTGCAGCTGCAGGAGTCGGGCCCAGGACTG GTGAAGCCTGCGGAGACCCTGTCCCTCACCTGCA CTGTCTCTGGTGGCTCCATCAGCAGAAGTAGTTA CTACTGGGGCTGGATCCGCCAGCCCCCAGGGAA GGTGCTGGAGTGGATTGGGAGCATCTATTATAGT GGGAGCACCTACTACAACCCGTCCCTCAAGAGTC GAGTCACCATATCCGTCGACACGTCCAAGAACCA GTTCTCCCTGAAGCTGAGCTCTGTGACCGCCGCA GACACGGCTGAGTATTACTGTGCGAGCCTTAGCA GCAGCTGGGACTTCCAGCACTGGGGCCAGGGCA CCCTGGTCACCGTCTCCTCA |
| | | | SEQ ID NO: 24373 | SEQ ID NO: 28379 |
| 21-225_21F3 | | AA | DIQMTQSPSSLSASVGDRVTITCRASQGIRNDLG WYQQKPGKAPKRLIYAASSLQSGVPSRFSGSGS GTDFILTISSLQPEDFATYYCLQHSSYPLTFGGGT KVEIK | QLQLQESGPGLVKPAETLSLTCTVSGGSISRSSYYW GWIRQPPGKVLEWIGSIYYSGSTYNPSLKSRVTIS VDTSKNQFSLKLSSVTAADTAEYYCASLSSSWDFQ HWGQGTLVTVSS |
| | | | SEQ ID NO: 24374 | SEQ ID NO: 28380 |

FIGURE 50
(Continued)

| | | | | |
|---|---|---|---|---|
| iPS:392776 | 21-225_21A12 | NA | GACATCCAGATGACCCAGTCTCCATCCTCACT GTCTGCATCTGTGGGAGAGTCAAGGACAGAGTCACCATCA CTTGCCGGGCAGTCAAGGCATTAGCAGCAAATAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATAATAGTTACCCGTTCA GGTTTGGCCAGGGGACCAAGCTGGAGATCAA A<br><br>SEQ ID NO: 24375 | GAGGTGCAGCTGGTGGAGTCTGGGGGAGGCTG GTCAAGCCTGGGGGGTCCCTGAGACTCTCCTGTG CAGCCTCTGGATTCACCTTCAATAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTCTGTATTACTGTGCGAGAGCGGGCTGGC TTTGACTACTGGGGCCAGGGAACCCTGGTCACCG TCTCCTCA<br><br>SEQ ID NO: 28381 |
| | | AA | DIQMTQSPSSLSASVGDRVTITCRASQGISKYLA WFQQKPGKAPKSLIYAASSLQSGVPSKFSGSGSG TDFTLTISSLQPEDFATYYCQQYNSYPFRFGQGT KLEIK<br><br>SEQ ID NO: 24376 | EVQLVESGGGLVKPGGSLRLSCAASGFTFNSYSMN WVRQAPGKGLEWVSSISGSSSYIYYADSVKGRFTIS RDNAKNSLYLQMNSLRAEDTALYYCARAAGFDY WGQGTLVTVSS<br><br>SEQ ID NO: 28382 |
| iPS:392778 | 21-225_22H3 | NA | GACATCCAGATGACCCAGTCTCCATCCTCCCT GTCTGCATCTGTAGGAGACAGAGTCACCATCA CTTGCCGGGCAAGTCAGAGCATTAGAAATAAT TTAGGCTGGTATCAGCAGAAACCAGGGAAAG CCCCTAAGCGCCTGATCTATCCTGCATCCAGT TGCAAACTGGGGTCCCATCAAGGTTCAGCGGC AGTGGATCTGGGACAGAATTCACTCTCACAAT CAGCAGCCTGCAGCCTGAAGATTTTGCAACTT ATTTCTGTCTACAGGATAATAGTTACCATTCA CTTTCGGCCCTGGGACCAAAGTGGATATCAAA<br><br>SEQ ID NO: 24377 | GCGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTCTGTGTTTACTGTGCGAGAGATAGGGGC AGCCCTCGGGGCCAGGGAACCCTGGTCACCGTCT CCTCT<br><br>SEQ ID NO: 28383 |

FIGURE 50
(Continued)

| | | | |
|---|---|---|---|
| iPS:392780 | 21-225_22B7 | AA | DIQMTQSPSSLSASVGDRVTITCRASQDIRNNLG WYQQKPGKAPKRLIYPASSLQTGVPSRFSGSGSG TEFTLTISSLQPEDFATYFCLQDNSYPFTFGPGTK VDIK<br>SEQ ID NO: 24378 | AVQLVESGGGLVKPGGSLRLSCAASGFTFSSYSMN WVRQAPGKGLEWVSSISSSSYIYYADSVKGRFTIS RDNAKNSLYLQMNSLRAEDTAVFYCARDRGSLWG QGTLVTVSS<br>SEQ ID NO: 28384 |
| | | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGAAAG CCCCTAAACGCCTGATCTATTACTGCATCCAGT TTGCAAAGTGGGGTCCCATCAAGGTTCAGCGG CAGTGGTTCTGGGACAGAATTCACTCTCACAA TCAGCAGCCTGCAGCCTGAAGATTTTGCAACT TATTACTGTCTACAGCATAATAGTTACCCGTC ACTTTCGGCCCTGGGACCAAGGTGGAGATCA AA<br>SEQ ID NO: 24379 | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAGCTATGGCAT GCACTGGGTCCGCCAGGCTCCAGGCAAGGGGCT GGAGTGGGTGGCAGTTATTGGTATGAAGAAAAT AATCAATACTATGCAGACTCCGTGAAGGGCCGAT TCACCATCTCAAGAGACAATTCCAAGAACACGCT GTATCTGCAAATGAACAGCCTGAGAGCCGAGGA CACGGCTGTGTTATTACTGTGCAGAGAAGTGGGG TTCCGGTCGACTACTGGGGCCAGGGAACCCTGG TCACCGTCTCCTCA<br>SEQ ID NO: 28385 |
| | | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNTYPLTFGGGT KVEIK<br>SEQ ID NO: 24380 | QVQLVESGGGVVQPGRSLRLSCAASGFTFSSYGMH WVRQAPGKGLEWVAVIWYEENNQYYADSVKGRF TISRDNSKNTLYLQMNSLRAEDTAVYYCAREVGFR SDYWGQGTLVTVSS<br>SEQ ID NO: 28386 |

FIGURE 50
(Continued)

| | | | |
|---|---|---|---|
| iPS:392782 | 21-225_22B12 | NA | GACATCCAGATGACCCAGTCTCCATCCTCACT GTCTGCGTCTGTAGGAGACAGAGTCACCATCA CTTGTCGGGCGAGTCAGGACATTAGCAATTAT TTAGCCTGGTTTCAGGAGAAACCAGGGAAAGC CCATAAGTCCCTGATCTATGGTGCATCCAGTTT GCGGAGTGGGGTCCCATCAAAGTTCAGCGGCA GTGGATCTGGGACAGATTTCAATCTCACCATC AGCAGCCTGCAGCCTGAAGATCTTGCAACTTA TTACTGCCAACAGTATCATAGTTACCCATTCA CTTTCGGCCCTGGGACCAAAGTGGATTTCAAA SEQ ID NO: 24381 | GAGGTGCAGCTGGTGGAGTCTGGGGGAGGCTG GTCAAGCCTGGGGGGTCCCTGAGACTCTCCTGTG CAGCCTCTGGATTCACCTTCAGCAGCAGTATAGCAT GAACTGGGTCCGCCAGGCTCCAGGGAAGGGGCT GGAGTGGGTCTCATCCATTAGTGGTAGTAGTAGT TACACATACTACGCAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGTAGCAGC CCTTGACTCCTGGGGCCAGGGAACCCTGGTCACC GTCTCCTCA SEQ ID NO: 28387 |
| | | AA | DIQMTQSPSSLSASVGDRVTIICRASQDISNYLA WFQEKPGKAHKSLIYGASSLRSGVPSKFSGSGSG TDFNLTISSLQPEDLATYYCQQYHSYPFTFGPGT KVDFK SEQ ID NO: 24382 | EVQLVESGGGLVKPGGSLRLSCAASGFTFSSYSMN WVRQAPGKGLEWVSSISGSSSYTYADSVKGRFTI SRDNAKNSLYLQMNSLRAEDTAVYYCARVAALDS WGQGTLVTVSS SEQ ID NO: 28388 |
| iPS:392784 | 21-225_23C7 | NA | GACATCCAGATGACCCAGTCTCCATCCTCACT GTCTGCATCTGTAGGAGACAGAGTCACCATCA CTTGCCGGGCGAGTCAGGGCATTGGCATTTAT TTAGCCTGGTATCAGCAGAAACCAGGGAAAGC CCCTAAGTCCCTGATCTCTGCTGCATCCAGTTT GCAAAGTGGGGTCCCATCAAGGTTCAGCGGCA GTGGATCTGGGACAGAGTTCACTCTCACCATC AGCAGCCTGCAGCCTGAAGATTTGCAACTTA TTACTGCCAACAGTATAATAGTTACCCATTCA CTTTCGGCCCTGGGACCAAAGTGGATATCAAA SEQ ID NO: 24383 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGTTAT GAGCTGGGTCCGCCAGGCTCCAGGGAAGGGGCT GGAGTGGGTCTCAGTTATGAGTGGTAGTGGTGGT AGCACATATTATGTAGACTCCGTGAAGGGCCGGT TCACCATCTCCAGAGACAATTCCAAGAACACGCT GTATCTGCAAATGAACAGCCTGAGAGCCGAGGA CACGGCCGTATATTATTGTGCGGAACTGGGGTC TTTGACTACTGGGGCCAGGGAACCCTGGTCATCG TCTCCTCA SEQ ID NO: 28389 |

FIGURE 50
(Continued)

| | | | |
|---|---|---|---|
| | | AA | DIQMTQSPSSLSASVGDRVTITCRASQGIGIYLA WFQQKPGKAPKSLISAASSLQSGVPSKFSGSGSG TEFTLTISSLQPEDFATYYCQQYNSYPFTFGPGTK VDIK | EVQLLESGGGLVQPGGSLRLSCAASGFTFSSYVMS WVRQAPGKGLEWVSAMSGSGGSTYYVDSVKGRF TISRDNSKNTLYLQMNSLRAEDTAVYYCARTGVFD YWGQGTLVIVSS |
| | | | SEQ ID NO: 24384 | SEQ ID NO: 28390 |
| iPS:392786 | 21-225_24E1 | NA | GACATCGTGATGACCCAGTCTCCAGACTCCCT GGCTGTGTCTCTGGGCGAGAGGGCCACCATCA ACTGCAAGTCCAGCCAGAGTGTTTATACACC TCCAACAATAACAACTACTTAACTTGGTACCA GCAGAAACCTGGACAGCGTCCTAACCTGCTCA TTTACTGGGCATCTCACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TTTTATAGTACTCCTCCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAGTGG TAACACAGGCTATGCACAGAGGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGACAAGCAGT GGCTGGGAGGTCTTTGACTACTGGGGCCAGGGA ACCCTGGTCACCGTCTCCTCA |
| | | | SEQ ID NO: 24385 | SEQ ID NO: 28391 |
| | | AA | DIVMTQSPDSLAVSLGERATINCKSSQSVLYTSN NNNYLTWYQQKPGQRPNLLIYWASTRESGVPD RFSGSGSGTDFTLTISSLQAEDVAVYYCQQFYST PPTFGQGTKVEIK | QVQLVQSGAEVKKPGASVKVSCKASGYTFTNYDIN WVRQATGQGLEWMGWMHPNSGNTGYAQRFQGR VTMTRNTSISTAYMELSSLRSEDTAVYYCATSSGW EVFDYWGQGTLVTVSS |
| | | | SEQ ID NO: 24386 | SEQ ID NO: 28392 |

FIGURE 50
(Continued)

| | | | |
|---|---|---|---|
| iPS:392788 | 21-225_20C8 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGAAGAAACCAGGGAAAG CCCCTAAGCGCCTGATCAATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATATTGCAACT TATTACTGTCTACAAGATAATAGTTACCCGTTC ACTTTCGGCGGAGGGACCAAGGTGGAGATCA CA<br><br>SEQ ID NO: 24387 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGTAGTTACAT GAACTGGGTCCGCCAGGCTCCAGGGAAGGGCCT GGAGTGGGTCTCATCCATTAGTGGCAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGACAGAGG CAGTCTCTGGGGCCAGGGAACCCTGGTCACCGTC TCCTCA<br><br>SEQ ID NO: 28393 |
| | | AA | DIQMTQSPSSLSASVGDRVTITCRASQGIRNDLG WYQKKPGKAPKRLINAASSLQSGVPSRFSGSGS GTEFTLTISSLQPEDFATYYCLQDNSYPFTFGGGT KVEIT<br><br>SEQ ID NO: 24388 | EVQLVESGGGLVKPGGSLRLSCAASGFTFSSYSMN WVRQAPGKGLEWVSSISGSSSYIYYADSVKARFTIS RDNAKNSLYLQMNSLRAEDTAVYYCARDRGSLW GQGTLVTVSS<br><br>SEQ ID NO: 28394 |
| iPS:392790 | 21-225_20D10 | NA | GACATCCAGATGACCCAGTCTCCATCCTCCCT GTCTGCATTTGTAGGAGACAGAGTCACCATCA CTTGCCGGGCAAGTCAGGGCATTAGAAATGAT TTAGGCTGGTATCAGCAGAAACCAGGGAAAG CCCGTAAGCGCCTGATCTATGTTGCATACAGT TTGCAAAGTGGGGTCCCATCAAGGTTCAGCGG CAGTGGATATGGGACAGCTTGCATATATGGGAAG TCAGCAGCTTGCAGCCTGAAGATTTTGCAACT TATTACTGTCTACAGCAACAAAATAGTTACCCGTG GACGTTCGGCCAAGGGACCAAGGTGGAAATC AAA<br><br>SEQ ID NO: 24389 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGGAAGT AATAAATACTATGTAGACTCCGTGAAGGGCCGAT TCACCATCTCCAGAGACGATTCCAAGAACACTCT GTATCTGCAAATGAACAGCCTGAGAGCCGAGGA CACGGCTGTGTATTACTGCGCGGAGAGATCTTGCC TGGACGGAAGAGTACTGGGGCCAGGGAACCCTG GTCACCGTCTCCTCA<br><br>SEQ ID NO: 28395 |

FIGURE 50
(Continued)

| | | | |
|---|---|---|---|
| | | AA | DIQMTQSPSSLSAFVGDRVTITCRASQGIRNDLG WYQQKPGKARKRLIYVAYSLQSGVPSRFSGSGY GTEFTLTISSLQPEDFATYYCIQQNSYPWTFGQG TKVEIK<br>SEQ ID NO: 24390 | QVQLVESGGGVVQPGRSLRLSCAASGFTFSDYGM HWVRQAPGKGLEWVAVIWFDGSNKYYVDSVKGR FTISRDDSKNTLYLQMNSLRAEDTAVYYCARDLG WTEEYWGQGTLVTVSS<br>SEQ ID NO: 28396 |
| iPS:392792 | 21-225_20G12 | NA | GACATCCAGATGACCCAGTCTCCATCCTCCCT GTCTGCATCTGTAGGAGACAGAGTCACCATCA CTTGCCGGGCGAGTCAGGGCATTAGCAATTAT TTAGCCTGGTATCAGCAGAAACCAGGGAAAGT TCCTAAGGTCTTGATCTATTATGCATCCACTTT GCAATCAGGGGTCCCCATCTCGGTTCAGTGGCA GTGGATCTGGGACAGATTTCACTCTCACCGTC AGCAGCCTGCAGCCTGAAGATATAACAGTGCCCCTCGA TTACTGTCAAAGTATAACAGTGCCCCTCGA TCACCTTCGGCCAAGGGACACGACTGGAGATT AAA<br>SEQ ID NO: 24391 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGCGGTAGTAGTAGT TACATCTACTACGCAGACTCACTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGTGGG AGCTACTGGGGCCAGGGAACCCTGGTCACCGTCT CCTCA<br>SEQ ID NO: 28397 |
| | | AA | DIQMTQSPSSLSASVGDRVTITCRASQGISNYLA WYQQKPGKVPKVLIYTASTLQSGVPSRFSGSGS GTDFTLTVSSLQPEDVATYYCQKYNSAPPITFGQ GTRLEIK<br>SEQ ID NO: 24392 | EVQLVESGGGLVKPGGSLRLSCAASGFTFSSYSMN WVRQAPGKGLEWVSSISGSSSYIYYADSLKGRFTIS RDNAKNSLYLQMNSLRAEDTAVYYCARDRGSYW GQGTLVTVSS<br>SEQ ID NO: 28398 |

FIGURE 50
(Continued)

| | | | |
|---|---|---|---|
| iPS:392794 | 21-225_21H3 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCGTCCAGT GTGCAAACTGGGGTCCCATCAAGGTTCAGCGG CAGTGGATCTGGGACAGAATTCACTCTCACAA TCAGCAGCCTGCAGGCTGAAGATTTTGCAATT TATTACTGTCTACAGCATAATAGTTATCCGTC ACTTTCGGCGGAGGGACCAAGGTGGAGATCA AA SEQ ID NO: 24393 | CAGCTGCAGCTGCAGGAGTCGGGCCCAGGACTG GTGAAGCCTTCGGAGACCCTGTCCCTCACCTGCA CTGTCTCTGGTGGCTCCATCAGTAGGAGTAGTTA CTACTGGGGCTGGATCCGCCAGCCCCCAGGGAA GGGAGCACCTACGACAACCCGTCCCTCAAGAGT CGAGTCACCATATCGTAGACACGTCCAAGAACC AGTTCTCCCTGAAGCTGAGCTCTGTGACCGCCGC GGACACGGCTGTTTATTACTGTGTGGAGACATGA AAAGACTGGGGCCTTGACTACTGGGGCCAGGGA ACCCTGGTCACCGTCCTCA SEQ ID NO: 28399 |
| | | AA | DIQMTQSPSSLSASVGDRVTITCRASQGIRNDLG WYQQKPGKAPKRLIYAASSVQTGVPSRFSGSGS GTEFTLTISSLQAEDLAIYYCLQHNSYPLTFGGGT KVEIK SEQ ID NO: 24394 | QLQLQESGPGLVKPSETLSLTCTVSGGSISRSSYYW GWIRQPPGKGLEWIGNIYYSGSTYDNPSLKSRVTIS VDTSKNQFSLKLSSVTAADTAVYYCGRHGKDWGL DYWGQGTLVTVSS SEQ ID NO: 28400 |
| iPS:392796 | 21-225_22A4 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGACCTCACTCTCACAA TCAGCAGCCTGCAGCCTGAAGATTTTGCAACT TATTACTGTCTTCAGCATAATAGTTACCCGTGG ACGTTCGGCCAAGGGACCAAGGTGGAAATCA AA SEQ ID NO: 24395 | CAGGTGCAGCTGGTGGAGTCTGGGGGAGGCGTG GTCCAGCCTGGGAGGTCCCTGAGACTCTCCTGTG CAGCCTCTGGATTCACCTTCAGTGACTATGGCAT ACACTGGGTCCGCCAGGCTCCAGGCAAGGGGCT GGAGTGGGTGGCAGTTATATGGTTTGATGGAAGT AATAAATACTATGCAGACTCCGTGAAGGGCCGA ATCACCATCTCTAGAGACAATTCCAAGAACACGC TGTATCTGCAAATGAACAGCCTGAGAGCCGAGG ACACGGCTGTGTATTACTGTGCGAGAGATCTTGG CTGGACGGAAAGAGTACTGGGGCCAGGGAACCCT GGTCACCGTCTCCTCA SEQ ID NO: 28401 |

FIGURE 50
(Continued)

| | | | |
|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPWTFGQG TKVEIK | QVQLVESGGGVVQPGRSLRLSCAASGFTFSDYGIH WVRQAPGKGLEWVAVIWFDGSNKYYADSVKGRIT ISRDNSKNTLYLQMNSLRAEDTAVYYCARDLGWT EEYWGQGTLVTVSS |
| | | | SEQ ID NO: 24396 | SEQ ID NO: 28402 |
| iPS:392798 | 21-225_22C7 | NA | GACATCCAGATGACCCAGTCTCCATCCTCCCT GTCTGCATCTGTAGGAGACAGAGTCACCATCA CTTGCCGGGCAAGTCAGAACATTATCAGTTAT TTAAATTGGTATCAGCAGAAACCAGAGAAAG CCCCTAAACTCCTGATCCATATTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGACTTACAGTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGGGCAGTTATATGGCATGATGAAG TAATAAATACTATGCAGACTCCGTGAAGGGCCG ATTCACCATCTCCAGAGACAATGCCAAGAACAC GCTGTATCTGCAAATGAACAGCTGAGAGCCGA GGACACGGCTGTGTATTACTGTGCGAGAGATCTG AGTATGGGCGGTATGGACGTCTGGGGCCAAGGG ACCACGGTCACCGTCTCCTCA |
| | | | SEQ ID NO: 24397 | SEQ ID NO: 28403 |
| | | AA | DIQMTQSPSSLSASVGDRVTITCRASQNIISYLNW YQQKPEKAPKLLIHIASSLQSGVPSRFSGSGSGTD FTLTISSLQPEDFATYYCQQTYSTPLTFGGGTKV EIK | QVQLVESGGGVVQPGRSLRLSCAASGFTFSSYGMH WVRQAPGKGLEWGAVIWHDGSNKYYADSVKGRF TISRDNAKNTLYLQMNSLRAEDTAVYYCARDLSM GGMDVWGQGTTVTVSS |
| | | | SEQ ID NO: 24398 | SEQ ID NO: 28404 |

FIGURE 50
(Continued)

| | | | |
|---|---|---|---|
| iPS:392800 | 21-225_22D12 | NA | GACATCCAGATGACCCAGTCTCCATCCTCCT GTCTGCATCTGTAGGAGACAGAGTCACCATCA CTTGTCGGGCAAGTCAGGGCATTAGAAATGAT TTAGGCTGGTATCAGCAGAAACCAGGGAAAG CCCCTAAGCGCCTGATCTATGCTGCATCCAGT TTGCAGAGTGGGGTCCCATCTAGGTTCAGCGG CAGTGGATCTGGGACAGATTTCACTCTCACAA TCAGCAGCCTGCAGCCTGAAGATTTTGCAACT TATTACTGTCTACAGCATAGTACTTACCCTCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCACTTGCA CTGTCTCTGGTGGCTCCATCAGCAGGAGTAGTTA CTACTGGGGCTGGATCCGCCAGCCCCCAGGGAA GGGGCTGGAGTGGATTGGAAATATCTATTATAGT GGGACCACCTCCTACAACCCGTCCCTCAAGAGTC GAGTCACCATATCGTTGACACGTCCAGGAACCA GTTCTCCCTGAAGCTGAGCTGTGTGCAGACTCAGA GACACGGCTGTGTTTACTGTGCGAGACTCAGCA GCAGCTGTGTCCGTTGACTACTGGGGCCAGGGAA CCCTGGTCACCGTCTCCTCA |
| | | | SEQ ID NO: 24399 | SEQ ID NO: 28405 |
| | | AA | DIQMTQSPSSLSASVGDRVTITCRASQGIRNDLG WYQQKPGKAPKRLIYAASSLQSGVPSRFSGSGS GTDFTLTISSLQPEDFATYYCLQHSTYPLTFGGG TKVEIK | QLQLQESGPGLVKPSETLSLTCTVSGGSISRSSYYW GWIRQPPGKGLEWIGNIYYSGTTSYNPSLKSRVTIS VDTSRNQFSLKLSSVTAADTAVFYCARLSSSWSVD YWGQGTLVTVSS |
| | | | SEQ ID NO: 24400 | SEQ ID NO: 28406 |
| iPS:392802 | 21-225_23E7 | NA | GACATCCAGATGACCCAGTCTCCATCCTCACT GTCTGCATCTGTAGGAGACAGAGTCACCATCA CTTGTCGGGCGAGTCAGGGCATTAGCAATGAT TTAGCCTGGTTTCAGCAGATACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTATAGTTAC TTACTGCTGCCAACAGTTTTATAGTTACCCATTCAC TTTCGGCCCTGGGACCAAAGTGGATATCAAT | GAGGTGCAGCTGTTGGAGTCTGGGGGAGGCTTG GTACAGCCTGGGGGGTCCCTGAGACTCTCCTGTA CAGCCTCTGGATTCACCTTTAGCAGCTATGCCAT GAACTGGGTCCGCCAGGCTCCAGGGAAGGGGCT GGAGTGGGTCTCAGCTATTAGTGGTAGTGGTGGT TCACATACTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGCGTACCAGTGGC TTTGACTACTGGGGCCAGGGAACCCTGGTCACCG TCTCCTCA |
| | | | SEQ ID NO: 24401 | SEQ ID NO: 28407 |

FIGURE 50
(Continued)

| | | | |
|---|---|---|---|
| iPS:392806 | 21-225_24H3 | AA | DIQMTQSPSSLSASVGDRVTITCRASQGISNYLA WFQQIPGKAPKSLIYAASSLQSGVPSKFSGSGSG TDFTLTISSLQPEDFATYYCQQFYSYPFTFGPGTK VDIN<br>SEQ ID NO: 24402 | EVQLLESGGGLVQPGGSLRLSCTASGFTFSSYAMN WVRQAPGKGLEWVSAISGSGGFTYYADSVKGRFTI SRDNSRNTLYLQMNSLRAEDTAVYYCARTSGFDY WGQGTLVTVSS<br>SEQ ID NO: 28408 |
| | | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCAAC TTAGCCTGGTACCAGCAGAAACCTGGCCAGGC TCCCAGGCTCCTCATCTATTTTGCATCCATCAG GGCCACTGGTATCCCAGCCAGGTTCAGTGGCA GTGGGTCTGGGACAGAGTTCACTCTCACCATC AGCAGCCTGCAGTCTGAAGATTTTGCAGTTTA TTACTGTCAGCAGTATAATAACTGGCCCATGT GCAGTTTTGGCCAGGGGACCAAGCTGGAGATC AAA<br>SEQ ID NO: 24403 | CAGGTGCAGCTGGTGGAGTCTGGGGGAGGCGTG GTCCAGCCTGGGAGGTCCCTGAGACTCTCCTGTG GAGCGTCTGGATTCACCTTCAGTAGCTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCAGAGACAATTCCAAGAACACGC TGTATCTGCAAATGAACAGCCTGAGAGCCGAGG ACACGGCTGTGTATTACTGTGCGAGAGTAGCAGT GGCAGGCGGTATGGACGTCTGGGGCCAAGGGAC CACGGTCACCGTCTCCTCA<br>SEQ ID NO: 28409 |
| | | AA | EIVMTQSPATLSVSPGERATLSCRASQSVSSNLA WYQQKPGQAPRLLIYFASIRATGIPARFSGSGSG TEFTLTISSLQSEDFAVYYCQQYNNWPMCSFGQ GTKLEIK<br>SEQ ID NO: 24404 | QVQLVESGGGVVQPGRSLRLSCGASGFTFSSYGMH WVRQAPGKGLEWVAVIWYDGSNKYYADSVKGRF TISRDNSKNTLYLQMNSLRAEDTAVYYCARVAVA GGMDVWGQGTTVTVSS<br>SEQ ID NO: 28410 |

FIGURE 50
(Continued)

| | | | |
|---|---|---|---|
| iPS:392808 | 21-225_20F8 | NA | GACATCCAGATGACCCAGTCTCCATCCTCCT GTCTGCATCTGTAGGAGACAGAGTCACCATCA CTTGCCGGGCAAGTCAGAGCATTAGCAGGTAT TTAAATTGGTATCAGCAGCAGAAACCAGGGAAAG CCCCTGAGCTCCTGATCTATGCTGCTTCCAGTT TGCAAAGTGGGGTCCCATCAAGGTTCAGTGGC AGTGGATCTGGGACAGATTTCATTCTCACCAT CAGCAGTCTACAACCTGAAGATTTTGCAACTT ACTACTGTCAACAGAGTTACAATACCCCCACG TGGACGTTCGGCCAAGGGACCAAGGTGGAAA TCAAA <br><br> SEQ ID NO: 24405 | GAGGTGCAGCTGTTGGAGTCTGGGGGAGGCTTG GTACAGCCTGGGGGGTCCCTGAGACTCTCCTGTG CAGCCTCTGGATTCACCTTTAGAAGCTATGCCAT GAGCTGGATCCGCCAGGCTCCAGGGAAGGGGCT GGAGTGGTCTTCAGTTATTAGTGGTAGTGGTGGT AGCACATATTACGCAGACTCCGTGAAGGGCCGG TTCACCATCTCCAGAGACAATTCCAAGAACACGC TGTATCTGCAAATGAGCAGCCTGAGAGCCGAAG ACACGGCCGTATATTACTGTGCGAAAAGGTATAA CAGTGGCTGCATGATGTTTTGATATCTGGGGC CAAGGGACAATGGTCACCGTCTCTTCA <br><br> SEQ ID NO: 28411 |
| | | AA | DIQMTQSPSSLSASVGDRVTITCRASQSISRYLN WYQQKPGKAPELLIYAASSLQSGVPSRFSGSGSG TDFTLTISSLQPEDFATYYCQQSYNTPTWTFGQG TKVEIK <br><br> SEQ ID NO: 24406 | EVQLLESGGGLVQPGGSLRLSCAASGFTFRSYAMS WIRQAPGRGLEWSSVISGSGGSTYYADSVKGRFTIS RDNSKNTLYLQMSSLRAEDTAVYYCAKRYNSGW HDVFDIWGQGTMVTVSS <br><br> SEQ ID NO: 28412 |
| iPS:392810 | 21-225_20H12 | NA | GACATCCAGATGACCCAGTCTCCATCCTCCT GTCTGCTTCTGTAGGAGACAGAGTCACCATCA CTTGCCGGGCAAGTCAGGGCATTAGAAACGAT TTAGACTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA <br><br> SEQ ID NO: 24407 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAACTACTGGCAT GCACTGGGTCCGCCAGGCTCCAGGCAAGGGGCT GGAGTGGGTGGCAGTTATATGACTCCGTGATGAAAAT AATAAATACTATGTAGACAACTCCAAGAGCGCT GTATCTGCAAATGAACAGCCTGAGAGCCGAGGA CACGGCTGTGTATTACTGTGCGAGAGAGTTGGGG TTCCGGTCTGACTACTGGGGCCAGGGAACCCTGG TCACCGTCCTCA <br><br> SEQ ID NO: 28413 |

FIGURE 50
(Continued)

| | | | | |
|---|---|---|---|---|
| iPS:392812 | 21-225_21F4 | AA | DIQMTQSPSSLSASVGDRVTITCRASQGIRNDLD WYQQKPGKAPKRLIYAASSLQSGVPSRFSGSGS GTEFTLTISSLQPEDFATYYCLQHNSYPLTFGGG TKVEIK<br><br>SEQ ID NO: 24408 | QVQLVESGGGVVQPGRSLRLSCAASGFTFSNYGM HWVRQAPGKGLEWVAVIWYDENNKYYVDSVKGR FTISRDNSKNTLYLQMNSLRAEDTAVYYCARELGF RSDYWGQGTLVTVSS<br><br>SEQ ID NO: 28414 |
| | | NA | GACATCCAGATGACCCAGTCTCCATCCTCCCT GTCTGCATCTGTAGGAGACAGAGTCACCATCA CTTGCCGGGCAAGTCAGAACATTGGTAGTTAT TTAAATTGGTATCAGCAGAAACCAGGGAAAG CCCCTAAGCTCCTGATCTTTGCTGCATCCAGTT TGCAAAGTGGGTCCCATCAAGGTTCAGTGGC AGTGGATCTGGGACAGATTTCACTCTCACCAT CAGCAGTCTGCAACCTGAAGATTTTGCAACTT TCTTCTGTCAACAGAGTTACAGAACCCCTTTT TCACTTTCGGCCCTGGGACCAAAGTGGATTTC AAA<br><br>SEQ ID NO: 24409 | GAGGTGCAGCTGTTGGAGTCTGGGGGAGGCTTG GTACAGCCTGGGGGGTCCCTGAGACTCTCCTGTG CAGCCTCTGAATTCACCTTTAGCAGCTATGCCAT GAACTGGGTCCGCCAGGCTCCAGGGAAGGGGCT GGAGTGGGTCTCAGTTATTAGTGGTCGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGTCCCGTTTGGCA GTGGCTGGCTCGGAGGCTTGTGATATCTGGGGCC AAGGGACAATGGTCACCGTCTCTCA<br><br>SEQ ID NO: 28415 |
| | | AA | DIQMTQSPSSLSASVGDRVTITCRASQNIGSYLN WYQQKPGKAPKLLIFAASSLQSGVPSRFSGSGSG TDFTLTISSLQPEDFATFFCQQSYRTPFFTFGPGT KVDFK<br><br>SEQ ID NO: 24410 | EVQLLESGGGLVQPGGSLRLSCAASEFTFSSYAMN WVRQAPGKGLEWVSVISGRGGNTFYADSVKGRFTI SRDNSKNTLYLQMNSLRAEDTAVYYCASRLAVAG SEACDIWGQGTMVTVSS<br><br>SEQ ID NO: 28416 |

FIGURE 50
(Continued)

| | | | | |
|---|---|---|---|---|
| iPS:392814 | 21-225_22A1 | NA | GATATTGTGATGACCCAGACTCCACTCTCT GTCCGTCACCCCTGACAGCGGCCTCCATCT CCTGCAAGTCTAGTGCAGAGCTCCTGCATAGT GGTGAAAGAACTACTATTTATATTGGTACCTGCA GAAGCCAGGCCAGCCTCCACAGCTCCTGATCT ATGAAGTTTCCAACCGGTTCTCTGGACTGCCA GATAGGTTCAGTGCAGCGGGTCAGGGACAG ATTTCACACTGAAAATCAGCGGGTGGAGGCT GCGGATGTTGGGGTTTATTACTGCATGCAAAC TTTACACCTTCCGTGGACGTTCGGCCAAGGGA CCAAGGTGGAAATCAAA SEQ ID NO: 24411 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATGTGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATGGGGA TTTTTGGAGTGGTTAGACTACTGGGGCCAGGGAA CCCTGGTCACCGTCTCCTCA SEQ ID NO: 28417 |
| | | AA | DIVMTQTPLSLSVTPGQPASISCKSSQSLLHSGGK TYLYWYLQKPGQPPQLLIYEVSNRFSGLPDRFSG SGSGTDFTLKISRVEAADVGVYYCMQTLHLPWT FGQGTKVEIK SEQ ID NO: 24412 | QVQLVESGGGVVQPGRSLRLSCAASGFTFSSYGMH WVRQAPGKGLEWVAVMWYDGSNKYYADSVKGR FTISRDNSKNTLYLQMNSLRAEDTAVYYCARDGGF LEWLDYWGQGTLVTVSS SEQ ID NO: 28418 |
| iPS:392816 | 21-225_22E4 | NA | GACATCCAGATGACCCAGTCTCCATCCTCCCT GTCTGCATCTGTAGGAGACAGAGTCACCATCA CTTGCCGGGCAAGTCAGAACATTAGTAGTTAT TTAAATTGGTATCAGCAGAAACCAGGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACATACCCCCTA TTCACTTTCGGCCCTGGGACCAAAGTGGATAT CAAA SEQ ID NO: 24413 | GAGGTGCAGCTGTTGGAGTCTGGGGGAGGCTTG GTGCAGCCTGGGGGGTCCCTGAGACTCTCCTGTG CAGCCTCTGGAATTCACCTTTAGCAGTTATGCCAT GAGCTGGGTCCGCCAGGCTCCAGGGAAGGGGCT GGAGTGGGTCTCAATTATTAGTAGTGGTCGTGGTACT AACACATTCTACGCAGACTCCGTGAAGGGCCGGT TCACCATCTCCAGAGTCAATTCCAAGAACACGCT GTATCTGCAAATGAACAGCCTGAGAGCCGAGGA CACGGCCGTATATTACTGTGCGTCCCGTATAGCA GTGGCTGGCTCGGAGGCTTTTGATATCTGGGGCC AAGGGACAATGGTCACCGTCTCTTCA SEQ ID NO: 28419 |

FIGURE 50
(Continued)

| | | | |
|---|---|---|---|
| iPS:392818 | 21-225_22D8 | AA | DIQMTQSPSSLSASVGDRVTITCRASQNISSYLN WYQQKPGKAPKLLIYAASSLQSGVPSRFSGSGS GTDFTLTISSLQPEDFATYYCQQSYNTPLFTFGPG TKVDIK<br>SEQ ID NO: 24414 | EVQLLESGGGLVQPGGSLRLSCAASEFTFSSYAMS WVRQAPGKGLEWVSIISGRGTNTFYADSVKGRFTI SRVNSKNTLYLQMNSLRAEDTAVYYCASRIAVAGS EAFDIWGQGTMVTVSS<br>SEQ ID NO: 28420 |
| | | NA | GACATCCAGATGACCCAGTCTCCATCCTCCCT GTCTGCATCTGTAGGAGACAGAGTCACCATCA CTTGCCGGACAAGTCAGAACAGTAACAGTTAT TTAAATTGGTATCAGCAGAAACCAGGGAAAG CCCCTAAGCTCCTGATCTTTGCTGCATACAGTT TGGAAAGTGGGGTCCCATCAAGGTTCAGTGGC AATAGATCTGGGACAGATTCACTCTCACCAT CAGCAGTCTGCAACCTGAAGATTTTGCAACTT ACTACTGTCAACAGAGTTACGGTACCTCGATC ACCTTCGGCCAAGGGACACGACTGGAGATTAA A<br>SEQ ID NO: 24415 | CAGGTGCAGCTGGTGGAGTCTGGGGGAGGCGTG GTCCAGCCTGGGAGGTCCCTGAGACTCTCCTGTG TAGCCTCTGGATTCACCTTCAGGAGCTATGGCAT GCACTGGGTCCGCCAGGCTCCAGGCAAGGGGCT GGAGTGGGTGACAATTATATCATATGGAAGT AATAAATACTATGCAGACTCCGTGAAGGGCCGA TTCACCATCTCCAGAGACAATTCCAAGAACACGC TGTATCTGCAAATGAACAGCCTGAGAGCTGAGG ACACGGCTGTATATTTCTGTGCGAGAGGGTTTG GTTCGGGGACTTCTGGGGCCAGGGAACCCTGGTC ACCGTCTCCTCA<br>SEQ ID NO: 28421 |
| | | AA | DIQMTQSPSSLSASVGDRVTITCRTSQNSNSYLN WYQQKPGKAPKLQIFAAYSLESGVPSRFSGNRS GTEFTLTISSLQPEDFATYYCQQTYGTSIFGQGT RLEIK<br>SEQ ID NO: 24416 | QVQLVESGGGVVQPGRSLRLSCVASGFTFRSYGMH WVRQAPGKGLEWVTIISYDGSNKYYADSVKGRFTI SRDNSKNTLYLQMNSLRAEDTAVYFCARGVWFGD FWGQGTLVTVSS<br>SEQ ID NO: 28422 |

FIGURE 50
(Continued)

| | | | | | |
|---|---|---|---|---|---|
| iPS:392820 | 21-225_23D1 | NA | GACATCCAGATGACCCAGTCTCCATCCTCCCT GTCTGCATCTGTAGGAGACAGAGTCACCATCA CTTGCCGGGCAAGTCAGGGCATCAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGTTCTGGGACAGAATTCACTCTCACAG TCAGCAGCCTGCAGCCTGAAGATTTTGCAACT TATTACTGTCTACAGCATAGTAGTTACCCTCTC ACTTTCGGCGGAGGGACCAAGGTGGAGATCA AA<br><br>SEQ ID NO: 24417 | DIQMTQSPSSLSASVGDRVTITCRASQGIRNDLG WYQQKPGKAPKRLIYAASSLQSGVPSRFSGSGS GTEFTLTVSSLQPEDFATYYCLQHSSYPLTFGGG TKVEIK<br><br>SEQ ID NO: 24418 | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTA CTACTGGGGCTGGATCCGCCAGCCCCAGGGAA GGGACTGGAGTGGATTGGGAGTATCTATTATAGT GGGAGCGCCCAGTACAACCCGTCCCTCAAGAGT CGAGTCACCATATCCGTCGACACGTCCAAGAACC AGTTCTCCCTGACGCTGAGCTCTGTGACCGCGC AGACACGGCTTTATATTACTGTGCGAGACTGAGC AGCAGCTGGTCTTTTGACTACTGGGGCCAGGGAA CCCTGGTCACCGTCCTCA<br><br>SEQ ID NO: 28423 | QLQLQESGPGLVKPSETLSLTCTVSGGSISRSSYYW GWIRQPPGKGLEWIGSIYYSGSAQYNPSLKSRVTIS VDTSKNQFSLTLSSVTAADTALYYCARLSSSWSFD YWGQGTLVTVSS<br><br>SEQ ID NO: 28424 |
| iPS:392822 | 21-225_23C8 | NA | GACATCCAGATGACCCAGTCTCCATCCTCCCG GTCTGCATCTGTAGGGGACAGAGTCACCATCA CTTGCCGGGCAAGTCAGGACAGTCATTAGAAATGAT TTAGGCTGGTATCAGCAGAAACCAGGGAGAG CCCCTAAGCGCCTGATCAGCAGAAGTGTCCAGT GTGCAAAGTGGGGTCCCATCAAGGTTCAGCGG CAGTGGATCTGGGACAGAATTCACTCTCACAA TCAGCAGCCTGCAGCCTGAAGATTTTGTAATT TATTACTGTCTACAGCATAATAGTTACCCGCTC ACTTTCGGCGGAGGGACCAAGGTGGAGATCA AA<br><br>SEQ ID NO: 24419 | | CAGTTGCAACTGCAGGAGTCGGGCCCAGGACTG GTGAAGCCTTCGGAGACCCTGTCCCTCACCTGCA CTGTCTCTGGTGGCTCCATCAGTAGGAGTAGTTA CTACTGGGGCTGGATCCGCCAGCCCCAGGGAA GGGGCTGGAGTGGATTGGGAATATTATTATAGT GGGACCACTTACAACACCGTCCTCAAGAGTC GAGTCACCATATCCGTAGACACGTCCAAGAACC ACTTCTCCCTGAAGCTGAGCTCTGTGACCGCGC AGACACGGCTGTGTATTACTGTGGGAGACATGGA AAAGACTGGGGCTTGACTACTGGGGCCAGGGA ACCCTGGTCACCGTCCTCA<br><br>SEQ ID NO: 28425 |

FIGURE 50
(Continued)

| | | | |
|---|---|---|---|
| iPS:392824 | 21-225_24E5 | AA | DIQMTQSPSSRSASVGDRVTITCRASQDIRNDLGWYQQKPGRAPKRLINGASSVQSGVPSRFSGSGSGTEFTLTISSLQPEDFVIYYCLQHNSYPLTFGGGTKVEIK<br>SEQ ID NO: 24420 | QLQLQESGPGLVKPSETLSLTCTVSGGSISRSSYYWGWIRQPPGKGLEWIGNIYSGTTYNNPSLKSRVTISVDTSKNHFSLKLSSVTAADTAVYYCGRHGKDWGLDYWGQGTLVTVSS<br>SEQ ID NO: 28426 |
| | | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAGTAATACCCGTCACTTTCGGCGGAGGGACCAAGGTGGAGATCAAAA<br>SEQ ID NO: 24421 | CAGCTGCAGCTGCAGGAGTCGGGCCCAGGACTGGTGAAGCCCTCGGAGACCCTGTCCCTCACCTGCACTGTCTCTGGTGGCTCCATCAGCAGGAGTAGTTACTACTGGGGCTGGATCCGCCAGCCCCCAGGGAAGGGGCTGGAGTGGATTGGGAGTATCTATTATAGTGGGAGCGCCAACTACAACCCGTCCCTCAAGAGTCGAGTCACCATATCCGTAGACACGTCCAAGAACCAGTTCTCCCTGAAGCTGAGCTCTGTGACCGCCGCAGACACGGCTGTGTATTACTGTGCGAGACTCAGCAGCAGTCGGTCCATTGACAACTGGGGCCAGGGAACCCTGGTCACCGTCTCCTCA<br>SEQ ID NO: 28427 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHSNYPLTFGGGTKVEIK<br>SEQ ID NO: 24422 | QLQLQESGPGLVKPSETLSLTCTVSGGAISRSSYYWGWIRQPPGKGLEWIGSIYSGSANYNPSLKSRVTISVDTSKNQFSLKLSSVTAADTAVYYCARLSSSWSIDNWGQGTLVTVSS<br>SEQ ID NO: 28428 |

FIGURE 50
(Continued)

| | | | | |
|---|---|---|---|---|
| iPS:392826 | 21-225_20B9 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGTTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATAATACTTATCCATTCAC TTTCGGCCCTGGGACCAAAGTGGATATCAAA SEQ ID NO: 24423 | GAGGTGCAGCTGGTGGAGTCTGGGGGAGGCTTG GTACAGCCTGGGGGGTCCCTGAGACTCTCCTGTG CAGCCTCTGGATTCACCTTCAGTAGTAGTATAT GAACTGGGTCCGCCAGGCTCCAGGGAAGGGGCT GGAGTGGGTTTCATACATTAGTAGTAGTAGTAGT ACCATATACTATGCAGACTCTGTGAAGGGCCGAT TCACCATCTCCAGAGACAATGCCAAGAACTCACT GTACCTGCAAATGAACAGCCTGAGAGACGAGA CACGGCTGTGTATTACTGTGCGAGGTCACTATGG TCCCCCTTTGACTACTGGGGCCAGGGAACCCTGG TCACCGTCTCCTCA SEQ ID NO: 28429 |
| | | AA | DIQMTQSPSSLSASVGDRVTITCRASQGISNYLA WFQQKPGKAPKSLIYVASSLQSGVPSKFSGSGSG TDFTLTISSLQPEDFATYYCQQYNTYPFTFGPGT KVDIK SEQ ID NO: 24424 | EVQLVESGGGLVQPGGSLRLSCAASGFTFSSYSMN WVRQAPGKGLEWVSYISSSSSTIYYADSVKGRFTIS RDNAKNSLYLQMNSLRDEDTAVYYCARSLWSPFD YWGQGTLVTVSS SEQ ID NO: 28430 |
| iPS:392830 | 21-225_21A5 | NA | GACATCCAGATGACCCAGTCTCCATCCTCCCT GTGTGCATCTGTAGGAGACAGAGTCACCATCA CTTGCCGGGCAAGTCAGGACGTCAGCCAT GAAACCAGGGAAAG TTAAATTGGTATCAGCAGAAACCAGGGAAAG CCCCTAAACTCCTGATCTATGCTGCATCCAGTT TGCAAAGTGGGGTCCCATCACGGTTCAGTGGC AGTGGATCTGGGACAGATTTCACTCTCACCAT CAGCAGTGTGCAACAGAGTTACAATCTCATTC ACTTTCGGCCCTGGGACCAAAGTGGATATCAA A SEQ ID NO: 24425 | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTTCTGG AGCTGGATCCGGCAGCCCGCCGGGAAGGGACTG GAGTGGATTGGGCGTATCTATACCAGTGGGATCA CCAACTACAACCCCTCCCTCAAGAGTCGAGTCAC CATGTCAGTAGACACGTCCAAGAACCAGTTCTCC CTGAAACTGAGTTCTGTGACCGCCGCGGACACGG CCATATATTACTGTGCGAGAGGCCCGACTTCGGG GTGGTTCGACCCCTGGGGCCAGGGAACCCTGGTC ACCGTCTCCTCA SEQ ID NO: 28431 |

FIGURE 50
(Continued)

| | | | |
|---|---|---|---|
| iPS:392832 | 21-225_21H8 | AA | DIQMTQSPSSLLCASVGDRVTITCRASQTISSHLN WYQRKPGKAPKLLIYAASSLQSGVPSRFSGSGSG TDFTLTISSVQPEDFATYYCQQSYNISFTFGPGTK VDIK<br>SEQ ID NO: 24426 | QVQLQESGPGLVKPSETLSLTCTVSGGSISSYFWSW IRQPAGKGLEWIGRIYTSGITNYNPSLKSRVTMSVD TSKNQFSLKLSSVTAADTAIYYCARGPTSGWFDPW GQGTLVTVSS<br>SEQ ID NO: 28432 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCCAAGGTTCAGAGG CAGTGGATCTGGGACAGAATTCACTCTCACAA TCAGCAGCCTGCAGCCTGAAGATATAGTTACCCGTG TATTACTGTCTACAGCATAATAGTTTCACCCGTG GACGTTCGGCCAAGGGACCAAGGTGGAAATC AAA<br>SEQ ID NO: 24427 | CAGGTGCAGCTGGTGGAGTCTGGGGGAGGCGTG GTCCAGTCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTTTGATGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGATCTTGG CTGGACGGAAGAGTACTGGGGCCAGGGAACCCT GGTCACCGTCTCCTCA<br>SEQ ID NO: 28433 |
| | | AA | DIQMTQSPSSLSASVGDRVTITCRASQGIRNDLG WYQQKPGKAPKRLIYAASSLQSGVPSRFRGSGS GTEFTLTISSLQPEDFATYYCLQHNSYPWTFGQG TKVEIK<br>SEQ ID NO: 24428 | QVQLVESGGGVVQSGRSLRLSCAASGFTFSDYGM HWVRQAPGKGLEWVAVIWFDGSNKYADSVKGR FTISRDNSKNTLYLQMNSLRAEDTAVYYCARDLG WTEEYWGQGTLVTVSS<br>SEQ ID NO: 28434 |

FIGURE 50
(Continued)

| | | | | SEQ ID NO |
|---|---|---|---|---|
| iPS:392834 | 21-225_22C1 | NA | GACATCCAGATGACCCAGTCTCCATCCTCCT GTCTGCATCTGTAGGAGACAGAGTCACCATCA CTTGCCGGACAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAGTACTTACCCGCTC ACTTTCGGCGGAGGGACCAAGGTGGAGATCA AA | CAACTGCAGCTGCAGGAGTCGGGCCCAGGACTG GTGAAGCCTTCGGAGACCCTGTCCTCACCTGTA CTGTTTCTGGTGGCTCCATCAACAGAGTAGTTA CTACTGGGGCTGGATCCGCCAGCCCCCAGGAA GGGGCTGGAGTGGATTGGGAATATCTATTATAGT GGGGCCACCTATTATAATTGTCCCTCAAGAGTC GAGTCACCATCTCCGTAGACACGTCCACGAACCA GTTCTCCCTGAAGCTGAGCTCTGTGACCGCCGCA GACACGGCTGTGTATTACTGTGCGAGACATAGCG GCAGCTGGTCCCTTGACTACTGGGGCCAGGGAAC CCTGGTCACCGTCTCCTCA |
| | | AA | DIQMTQSPSSLSASVGDRVTITCRTSQGIRNDLG WYQQKPGKAPKRLIYAASSLQSGVPSRFSGSGS GTEFTLTISSLQPEDFATYYCLQHSTYPLTFGGGT KVEIK | QLQLQESGPGLVKPSETLSLTCTVSGGSINRSSYYW GWIRQPPGKGLEWIGNIYYSGATYYNSSLKSRVTIS VDTSTNQFSLKLSSVTAADTAVYYCARHSGWSLD YWGQGTLVTVSS |
| | | | SEQ ID NO: 24429 | SEQ ID NO: 28435 |
| iPS:392836 | 21-225_22F4 | NA | GACATCCAGATGACCCAGTCTCCATCCTCCCT GTCTGCTTCTGTTGGAGACAGAGTCACCATCA CTTGCCGGGCAAGTCAGTCAGTTAGAGATGAT TTAGGCTGGTATCAGCAGAAACCAGGGAAAG CCCCTAAGCGCCTGATCTATGCTGCATCCAGT TTGCAAAGTGGGGTCCCATCGAGGTTCAGCGG CAGTAGATCTGGGACAGAATTCACTCTCACAA TCAGCAGCCTGCAGCCTGAAGATTTTGCAACT TATTACTGTCTACACCACTATAGTATCTCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGCGACTATGGCAT GCACTGGGTCCGCCAGGCTCCAGGCAAGGGGCT GGAGTGGGTGGCAGTTATATGTAGACTCCGTGAAGTGGAAGT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAAAGTAT AGCAGCAGTGGTACGACTACGGTATGGACGTCT GGGGCCAAGGGACCACGGTCACCGTCTCCTCA |
| | | AA | | |
| | | | SEQ ID NO: 24430 | SEQ ID NO: 28436 |
| | | | SEQ ID NO: 24431 | SEQ ID NO: 28437 |

FIGURE 50
(Continued)

| | | | |
|---|---|---|---|
| | | AA | DIQMTQSPSSLSASVGDRVTITCRASQVIRDDLG WYQQKPGKAPKRLIYAASSLQSGVPSRFSGSRS GTDFTLTISSLQPEDFATYYCLHHYSYPRTFGQG TKVEIK | QVQLVESGGGVVQPGRSLRLSCAASGFTFSDYGM HWVRQAPGKGLEWVAVIWYDGSNKYYVDSVKGR FTISRDNSKNTLYLQMNSLRAEDTAVYYCAREKYS SSWYDYGMDVWGQGTTVTVSS |
| | | | SEQ ID NO: 24432 | SEQ ID NO: 28438 |
| iPS:392838 | 21-225_22G8 | NA | GACATCCAGATGATCCAGTCTCCATCCTCCCT GTTCGCATCTGTAGGAGACAGAGTCACCATCA CTTGCCGGACAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAAATTCAGCGG CAGTGGATCTGGGACAGATTCACTCTCTCAA TCAGCAGCCTGCAGCTGAAGATTTTGCAACT TATTACTGTCTACAGCATAATAGTTACCCGCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCACCTGCA CTGTCTCTGGTGGCTCCATCAACAGGAGTAGTTA CTACTGGGGCTGGATCCGCCAGCCCCCAGGGAA GGGGCTGGACTGGATTGGGAATATCTATTATAGT GGGAGCACCTACTACAACCCGTCCGTCAAGAGTC GATTCACCATATCCGTAGACACGTCCAAGAACCA GTTCTCCCTGAAGCTGAGCTCTGTGACCGCCGCA GACACGGCTGTGTATTACTGTGCGAGACATGGAA AAGACTGGGGCCTTGACTACTGGGGCCAGGGAA CCCTGGTCACCGTCTCCTCA |
| | | | SEQ ID NO: 24433 | SEQ ID NO: 28439 |
| | | AA | DIQMIQSPSSLFASVGDRVTITCRTSQGIRNDLG WYQQKPGKAPKRLIYAASSLQSGVPSKFSGSGS GTEFTLSISSLQPEDFATYYCLQHNSYPLTFGGGT KVEIK | QLQLQESGPGLVKPSETLSLTCTVSGGSINRSSYYW GWIRQPPGKGLDWIGNIYYSGSTYYNPSVKSRFTIS VDTSKNQFSLKLSSVTAADTAVYYCARHGKDWGL DYWGQGTLVTVSS |
| | | | SEQ ID NO: 24434 | SEQ ID NO: 28440 |

FIGURE 50
(Continued)

| | | | |
|---|---|---|---|
| iPS:392840 | 21-225_23G1 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTCTGTGCTGCATCCAGTTT ACAGAGTGGGGTCCCATCACAGTTCAGCGGCA GTGGATTTGGACAGATTTCACTCTCACCATC AGCAGCCTGCAGCCTGAGGATATTTGCAACTTA TTACTGCCAACAGTATAATAGTTACCCATTCA CTTTCGGCCCTGGGACCAAAGTGGATATCAAA<br><br>SEQ ID NO: 24435 | GAGGTGCAACTGTTGGAGTCTGGGGGAGGCTTG GTACAGCCTGGGGGGTCCCTGAGACTCTCCTGTG CAGCCTCTGGATTCACCTTTAGCAGTTATGCCAT GAGCTGGGTCCGCCAGGCTCCAGGGAGGGGGCT GGAGTGGGTCTCAGTTATTAGTGGTAGTGGTGGT ACCACATAACACAGACTCCGTGAAGGGCCGG TTCACCATCTCCAGAGACAATCCAAGAACACGC TATATCTGCAAATGAACAGCCTGAGAGCCGAGG ACACGGCCGTATATTACTGTGCCCGCAGCTCTT GTTTGACTACTGGGGCCAGGGAACCCTGGTCACC GTCTCCTCA<br><br>SEQ ID NO: 28441 |
| | | AA | DIQMTQSPSSLSASVGDRVTITCRASQGISNYLA WFQQKPGKAPKSLISAASSLQSGVPSQFSGSGFG TDFTLTISSLQPEDFATYYCQQYNSYPFTFGPGT KVDIK<br><br>SEQ ID NO: 24436 | EVQLLESGGGLVQPGGSLRLSCAASGFTFSSYAMS WVRQAPGRGLEWVSVSGGTTYNTDSVKGRFTI SRDNSKNTLYLQMNSLRAEDTAVYYCARSSLFDY WGQGTLVTVSS<br><br>SEQ ID NO: 28442 |
| iPS:392842 | 21-225_23G8 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAACTTCAGCGGCA GTGGATCTGGACAGCTCACTCTCACCATC AGTAGCCTGCAACAGTATAATAGTTACCCTTCAC TATCGGCCCTGGGACCAAAGTGGATATCAAA<br><br>SEQ ID NO: 24437 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTTATGCCAT GAGCTGGGTCCGCCAGGCTCCAGGGAAGGGGGCT GGAGTGGGTCTCAGTTATTAGTGGTAGTGGTGGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGGTTAGCAGTGG CTGGTTCGCCTGGCCAGGGAACCCTGGTCACC GTCTCCTCA<br><br>SEQ ID NO: 28443 |

FIGURE 50
(Continued)

| | | | |
|---|---|---|---|
| iPS:392844 | | AA | DIQMTQSPSSLSASVGDRVTITCRASQGIRNYLA WFQQKPGKAPKSLIYAASSLQSGVPSNFSGSGSG TDFTLTISSLQPEDFATYYCQQYNSYPFTIGPGTK VDIK<br>SEQ ID NO: 24438 | EVQLLESGGGLVQPGGSLRLSCAASGFTFSSYAMS WVRQAPGKGLEWVSAISGSGGSTYYADSVKGRFTI SRDNSKNTLYLQMNSLRAEDTAVYYCAVSSGWFA WGQGTLVTVSS<br>SEQ ID NO: 28444 |
| | 21-225_23E11 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTTTCAGCAGAAACCAGGAAAG CCCCTAAGCGCCTGATCTATCCTGCATCCAGT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAGTTACCCGTGG ACGTTCGGCCAAGGGACCAAGGTGGAAATCA AA<br>SEQ ID NO: 24439 | GAGGTGCAACTGGTGGAGTCTGGGGGAGGCCTG GTCAAGCCTGGGGGGTCCCTGAGACTCTCCTGTG CAGCCTCTGGATTCACCTTCAGTTCCTATACCAT GAACTGGGTCCGCCAGGCTCCAGGGAAGGGGCT GGAGTGGGTCTCATCCATTAGTGGTAGTAGTAGT TACATATGGTATGTAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGGGGC AGTCTCTGGGGCCAGGGAACCCTGGTCACCGTCT CCTCA<br>SEQ ID NO: 28445 |
| | | AA | DIQMTQSPSSLSASVGDRITITCRASQGIRNDLG WYQQKPGKAPKRLIYPASSLQSGVPSRFSGSGSG TEFTLTISSLQPEDFATYYCLQHNSYPWTFGQGT KVEIK<br>SEQ ID NO: 24440 | EVQLVESGGGLVKPGGSLRLSCAASGFTFSSYTMN WVRQAPGKGLEWVSSISGSSSYIWYVDSVKGRFTI SRDNAKNSLYLQMNSLRAEDTAVYYCARDRGSLW GQGTLVTVSS<br>SEQ ID NO: 28446 |

FIGURE 50
(Continued)

| | | | | |
|---|---|---|---|---|
| iPS:392846 | 21-225_24B6 | NA | GACATCCAGATGACCCAGTCTCCATCCTCCT GTCTGCATCTGTGGAGACAGAGTCACCATCA CTTGCCGGGCAAGTCAGGACATTAGAAATGAT TTAGGCTGGTATCAGCAGAAGCCAGGGAAAG CCCCTAAGCGCCTGATCTATGCTGCATCCAGT TTGCACAGTGGGGTCCCATCAAGGTTCAGCGG CAGTGGATCTGGGACAGAATTCACTCTCACAA TCAGCAGCCTGCAGACTGAAGATTTTGCAACT TATTACTGTCTACAGCATTATAGTTACCCTCGG ACGTTCGGCCAAGGGACCAAGGTGGAAGTCA AG | CAGGTGCAGCTGGTGGAGTCTGGGGGAGGCGTG GTCCAGCCTGGGAGGTCCCCGAGACTCTCCTGTG CAGCGTCTGGATTCATCTTCAGTAACTATGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGAATA TAGTAGTGGCTGGTACGACTACGGTATGGACGTC TGGGGCCAAGGGACCACGGTCACCGTCTCCTCA |
| | | | SEQ ID NO: 24441 | SEQ ID NO: 28447 |
| | | AA | DIQMTQSPSSLSASVGDRVTITCRASQDIRNDLG WYQQKPGKAPKRLIYAASSLHSGVPSRFSGSGS GTEFTLTISSLQTEDFATYYCLQHYSYPRTFGQG TKVEVK | QVQLVESGGGVVQPGRSPRLSCAASGFIFSNYVMH WVRQAPGKGLEWVAVIWYDGSNKYYADSVKGRF TISRDNSKNTLYLQMNSLRAEDTAVYYCAREEYSS GWYDYGMDVWGQGTTVTVSS |
| | | | SEQ ID NO: 24442 | SEQ ID NO: 28448 |
| iPS:392848 | 21-225_20F9 | NA | GACATCCAGATGACCCAGTCTCCATCCTCACT GTCTGCATCTGTAGGAGACAGAATCACCATCA CTTGTCGGGCGAGTCAGGGCATTAGCAATTAT TTAGCCTGGTTTCAGCAGAAACCAGGGAAAGC CCCTAAGTCCCTGATCTCTGCTGCATCCAGTTT GCAAAGTGGGGTCCCTTCAAAGTTCAGCGGCA GTGGATCCGGGACAGATTTCACTCTCACCATC AGCAGCCTGCAGCCTGAAGATTTTGCAACTTA TTGCTGCCAAACAGTATCATAGTTACCCGTGA CGTTCGGCCAAGGGACCAAGGTGGAAATCAA A | GAAGTGCAGCTGGTGGAATCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGTAGT TACATATACTACCGAGACAGTCAGTGAAGGCCGAT TCACCATCTCCAGAGACAATGCCAAGAACTCACT GTATCTGCAAATGAACAGCCTGAGAGCCGAGGA CACGGCTGTGTATTATTGTGCGAGAGATCGTGGG AGCTGTGGGGCCAGGGAACCCTGGTCACCATCT CCTCA |
| | | | SEQ ID NO: 24443 | SEQ ID NO: 28449 |

FIGURE 50
(Continued)

| | | | |
|---|---|---|---|
| iPS:392850 | 21-225_20H10 | AA | DIQMTQSPSSLSASVGDRITITCRASQGISNYLAWFQQKPGKAPKSLISAASSLQSGVPSKFSGSGSGTDFTLTISSLQPEDFATYCCQQYHSYPWTFGQGTKVEIK<br>SEQ ID NO: 24444 | EVQLVESGGGLVKPGGSLRLSCAASGFTFSSYSMNWVRQAPGKGLEWVSSISSSSYIYADSVKGRFTISRDNAKNSLYLQMNSLRAEDTAVYYCARDRGSCWGQGTLVTISS<br>SEQ ID NO: 28450 |
| | | NA | GGCATCCAGATGACCCAGTCTCCATCCTCCCTGTCTGCATCTGTAGGAGACAGAGTCACCATCACTTGCCGGGCAAGTCAGGGCATTAAAAATAATTTAGGCTGGTATCAGCAGAAACCAGGGAAAGGCCCTAAGTGCCTGATCTATGCTGCATCCAGTTTGCAAAGTGGGGTCCCATCCAAGGTTCAGCGGCAGTGGATCTGGGACAGAATTCACTCTCACAATCAGCAGCCTGCAGCCTGAAGATTTTGCAACTTATTACTGTCTACAGCATAATAGTTACCCGCTCACTTTCGGCGGAGGGACCAAGGTGGAGATCAAA<br>SEQ ID NO: 24445 | GAGGTGCAGCTGGTGGAGTCTGGGGGAGGCCTGGTCAAGCCTGGGGGGTCCCTGAGACTCTCCTGTGCAGCCTCTGGATTCACCTTCAGTAGCTACTATAGCATGAACTGGGTCCGCCAGGCTCCAGGGAAGGGCTGGAGTGGGTCTCATCATTAGTAGTAGTAGTTACATATACTACGCAGACTCAGTGAAGGGCCGATTCACCATCTCCAGAGACAACGCCAAGAACTCACTGTATCTGCAAATGAACAGCCTGAGAGCCGAGGACACGGCTATTTATTACTGTGCGAGAGATCGTGGGAGCCTCGGGGCCAGGGAACCCTGGTCACCGTCTCCTCA<br>SEQ ID NO: 28451 |
| | | AA | GIQMTQSPSSLSASVGDRVTITCRASQGIKNNLGWYQQKPGKGPKCLIYAASSLQSGVPSRFSGSGSGTEFTLTISSLQPEDFATYYCLQHNSYPLTFGGGTKVEIK<br>SEQ ID NO: 24446 | EVQLVESGGGLVKPGGSLRLSCAASGFTFSTYSMNWVRQAPGKGLEWVSSISSSSYIYADSVKGRFTISRDNAKNSLYLQMNSLRAEDTAIYYCARDRGSLWGQGTLVTVSS<br>SEQ ID NO: 28452 |

FIGURE 50
(Continued)

| | | | |
|---|---|---|---|
| iPS:392852 | 21-225_21A2 | NA | GACATCCAGATGACCCAGTCTCCATCCTCCT GTCTGCATCTGTAGGAGACAGAGTCACCATCA CTTGCCGGGCAAGTCAGAGTATTAGTAGTTAT TTAAATGGTATCAGCAGAAACCAGGGAAAG CCCCTAAGCTCCTGATCTATGCTGCATCCAGTT TGCAAAGTGGGGTCCCATCAAGGTTCAGTGGC AGTGGATCTGGGACAGACTTCACTCTCACCAT CAGTAGTCTGCAACCTGAAGATTTTGCAACTT ACTTCTGTCAACAGAGTTACAGAACCCCTTT TTCACTTTCGGCCCTGGGACCAAAGTGGATAT CAAA<br><br>SEQ ID NO: 24447 | GAGGTGCAGCTGTTGGAGTCTGGGGGAGGCTTG GTACAGCCTGGGGGGTCCCTGAGACTCTCCTGTG CAGCCTCTAATTCACCTTTAGCAGCTATGCCAT GAACTGGGTCCGCCAGGCTCCAGGGAAGGGGCT GGAGTGGATCTCAATTATTAGTGGTCGTGGTGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGTCCCGTTTGGCA GTGGCTGGCTCGGAGGCTTTGATATCTGGGGCC AAGGGACAATGGTCACCGTCTCTCA<br><br>SEQ ID NO: 28453 |
| | | AA | DIQMTQSPSSLSASVGDRVTITCRASQSISSYLNW YQQKPGKAPKLLIYAASSLQSGVPSRFSGSGSGT DFTLTISSLQPEDFATYFCQQSYRTPFFTFGPGTK VDIK<br><br>SEQ ID NO: 24448 | EVQLLESGGGLVQPGGSLRLSCAASKFTFSSYAMN WVRQAPGKGLEWISIISGRGGNTFYADSVKGRFTIS RDNSKNTLYLQMNSLRAEDTAVYYCASRLAVAGS EAFDIWGQGTMVTVSS<br><br>SEQ ID NO: 28454 |
| iPS:392854 | 21-225_21E5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCTCCTGATCTATGCTACATCCAGT TTGCAAAGTGGGGTCCCATCAAGGTTCAGCGG CAGTGGATCTGGGACAGACCTGCAGCCTGCAGCCTCACAA TCAGCAGCCTGCAGCCTGAAGATTTTGCAACT TATTACTGTCTACAGCATAATAGTTACCCCCTC ACTTTCGGCGGAGGGACCAAGGTGGAGATCA AA<br><br>SEQ ID NO: 24449 | CAGGTGCAGCTGGTGGTGGAGTCTGGGGGAGGCGTG GTCCAGCCTGGGAGGTCCCTGAGACTCTCCTGTT CAGCGTCTGGATTCACCTTCAGTGACTGACATGGCAT GCACTGGGTCCGCCAGGCTCCAGGCAAGGGGCT GGAGTGGGGTGGCAGTTATATGTGATGAAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTACGAGAGAACTGGG GTTCCGGTCTGACTATTGGGGCCAGGGAACCCTG GTCACCGTCTCCTCA<br><br>SEQ ID NO: 28455 |

FIGURE 50
(Continued)

| | | | |
|---|---|---|---|
| iPS:392856 | 21-225_22A2 | AA | DIQMTQSPSSLSASVGDRVTITCRASQGIRNDLG WYQQKPGKAPKRLIYATSSLQSGVPSRFSGSGSG TEFTLTISSLQPEDFATYYCLQHNSYPLTFGGGT KVEIK SEQ ID NO: 24450 | QVQLVESGGGVVQPGRSLRLSCSASGFTFSDYGMH WVRQAPGKGLEWVAVIWYDESNKYYADSVKGRF TISRDNSKNTLYLQMNSLRAEDTAMYYCTRELGFR SDYWGQGTLVTVSS SEQ ID NO: 28456 |
| | | NA | GACATCCAGATGACCCAGTCTCCATCCTCACT GTCTGCATCTGTCGGAGACAGAGTCACCATCA CTTGTCGGGCGAGTCAGGACATTAGCAATTAT TTAGCCTGGTTCAGCAGAAACCAGGGAAAG CCCCTAAGTCCCTGATCTACGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAAGTT ATTACTGCCAACAGTATAATAGTTTCCCGCTC ACTTTCGGCGGAGGGACCAAGGTGGAGATCA AA SEQ ID NO: 24451 | GAGGTGCAGCTGTTGGAGTCTGGGGGAGGCTTG GTCCAACCTGGGGGGTCCCTGAGACTCTCCTGTG CAGCCTCTGGATTCACCTTTAGCGACTATGGCCAT GAGCTGGGTCCGCCAGGCTCCAGGGAAGGGGCT GGAGTGGGTCTCAGGTATTAGTGGTAGTGGAGGT AACACACCTACGCAGCAGACTCCGTGAAGGGCCGG TTCACCATCTCCAGAGACAATTCCAAGAACACGC TGTATCTGCAAATGAACAGCCTGAGAGCCGAAG ACACGGCCGTATATTACTGTGCGAAAGTAGTGGG AGCTGTCCACTGGGGCCGGGGAACCCTGGTCACC GTCTCCTCA SEQ ID NO: 28457 |
| | | AA | DIQMTQSPSSLSASVGDRVTITCRASQDISNYLA WVQQKPGKAPKSLIYAASSLQSGVPSKFSGSGS GTDFTLTISSLQPEDFASYYCQQYNSFPLTFGGG TKVEIK SEQ ID NO: 24452 | EVQLLESGGGLVQPGGSLRLSCAASGFTFSSYAMS WVRQAPGKGLEWVSGISGSGGNTPYADSVKGRFTI SRDISKNTLYLQMNSLRAEDTAVYYCAKVVGAVH WGRGTLVTVSS SEQ ID NO: 28458 |

FIGURE 50
(Continued)

| | | | |
|---|---|---|---|
| iPS:392858 | 21-225_22H4 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT GTGCAAAGTGGGGTCCCATCAAGGTTCAGCGG CAGTGGATCTGGGACAGAATTCACTCTCACAA TCAGCAGCCTGCAGCCTGAAGATTTTGCACTT TATTACTGTCTACAGCATAATAGTTACCCGCTC ACTTTCGGCGGAGGGACCAAGGTGGAGATCA AA |
| | | | SEQ ID NO: 24453 |
| | | AA | DIQMTQSPSSLSASVGDRVTITCRASQGIRNDLG WYQQKPGKAPKRLIYAASSVQSGVPSRFSGSGS GTEFTLTISSLQPEDFALYYCLQHNSYPLTFGGG TKVEIK |
| | | | SEQ ID NO: 24454 |
| | | NA | CAGGTGCAGCTGGTGGAGTCTGGGGGAGGCGTG GTCCAGCCTGGGAGGTCCTGAGACTCTCCTGTG CTGTCTCTGGATTCACCTTCAGTAGTTATTATA TGCACTGGGGCTGGATCCGCCAGCCCCAGGGAA GGGCTGGAGTGGATTGGAATATTATTATAGT GGGAGCACCTACCACAACCCGTCTCTCAAGAGTC GAGTCACCATATCGTAGACACGTCCATGAACCA GTTCTCCCTGAAGTTGACCTCTGTGACCGCCGCA GACACGGCTGTGTATTTCTGTGGGAGACATGAA AAGACTGGGGCCTTGACTACTGGGGCCAGGGAA CCCTGGTCACCGTCTCCTCA |
| | | | SEQ ID NO: 28459 |
| | | AA | QLQLQESGPGLVKPSETLSLTCTVSGGSISRSSYYW GWIRQPPGKGLEWIGNIYYSGSTYHNPSLKSRVTIS VDTSMNQFSLKLTSVTAADTAVFCGRHGKDWGL DYWGQGTLVTVSS |
| | | | SEQ ID NO: 28460 |
| iPS:392860 | 21-225_22H8 | NA | GATATTGTGATGACCCAGACTCCACTCTCTCT GTCCGTCACCCTGGACAGCCGGCCTCCATCT CCTGCAAGTCTAGTCAGAGCCTCCTGCATAGT GATGGAAAGAACCTTTTGTATTGGTACCTGCA GAAGCCAGGCCATCCTCCACAGTCCTGATCT ATGAAGTTTCCAACCGGTTCTCTGGAGTGCCA GATAGGTTCAGTGGCAGCGGGTCAGGGACAG ATTTCACACTGAAAATCAGCCGGGTGGAGGCT GAGGATGTTGGAATTTATTACTGCATGCAAAG TATACAGCTTCCGCTCTCATTCGGCGGAGGGA CCAAGGTGGAGATCAAC |
| | | | SEQ ID NO: 24455 |
| | | NA | CAGGTGCAGCTGGTGGTGGAGTCTGGGGGAGGCGTG GTCCAGCCTGGGAGGTCCTGAGACTCTCCTGTG CAGCCTCTGGATTCACCTTCAGTAGTTACTATGCCAT GCACTGGGTCCGCCAGGCTCCAGGCAAGGGGCT GGAGTGGGTGGCAGTTATCTGGTATGATGGAAAT AATAAATACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGAGCTTGC CTGGTACGAAGACTACTGGGGCCAGGGAACCCT GGTCACCGTCTCCTCA |
| | | | SEQ ID NO: 28461 |

FIGURE 50
(Continued)

| | | | |
|---|---|---|---|
| | | AA | DIVMTQTPLSLSVTPGQPASISCKSSQSLLHSDGK TFLYWYLQKPGHPPQLLIYEVSNRFSGVPDRFSG SGSGTDFTLKISRVEAEDVGIYYCMQSIQLPLSFG GGTKVEIN<br><br>SEQ ID NO: 24456 | QVQLVESGGGVVQPGRSLRLSCAASGFTFSSYGMH WVRQAPGKGLEWVAVIWYDGNNKYYADSVKGRF TISRDNSKNTLYLQMNSLRAEDTAVYYCARELAW YEDYWGQGTLVTVSS<br><br>SEQ ID NO: 28462 |
| iPS:392864 | 21-225_23B9 | NA | GAAATTGTGTTGACGCAGTCTCCAGGCACCCT GTCTTTGTCTCCAGGAGAAAGAGCCACCCTCT CCTGCAGGGCCAGTCAGTCAGAATGTTACAGCAGC TACTTAGCCTGGTACCAGCAGAAACCTGGCCA GACTCCCAGGCTCCTCATCTATGGTGCATCA GCAGGGCCAGTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAGCTCACCT CGGACGTTCGGCCAAGGGACCAAGGTGGAAA TCAAA<br><br>SEQ ID NO: 24457 | CAGGTGCAGCTGCAGGCGTCGGGCCAGGACTG GTGAAGCCTTCACAGACCCTGTCCCTCACCTGCA CTGTCTCTGATGGCTCCATCAGCAGTGGTGTTA CTACTGGAGCTGGATCCGCCAGCACCCAGGAA GGGCCTGGAGTGGATTGGGTACATCTATTACAGT GGGAGCACCTACTACAACCCGTCCCTCAAGAGTC GAGTTACCATATCAGTAGACAGTCTAAGAACCA GTTCTCCCTGAAGCTGAGTTCTGTGACTGCCGCG GACACGGCCGTATATTACTGTGCGAGAGAGGAC GGTGCCTTCGGCTACTACGGTATGGACGTCTGGG GCCAAGGGACCACGGTCACCGTCTCCTCA<br><br>SEQ ID NO: 28463 |
| | | AA | EIVLTQSPGTLSLSPGERATLSCRASQNVYSSYLA WYQQKPGQTPRLLIYGASSRASGIPDRFSGSGSG TDFTLTISRLEPEDFAVYYCQQYGSSPRTFGQGT KVEIK<br><br>SEQ ID NO: 24458 | QVQLQASGPGLVKPSQTLSLTCTVSDGSISSGYY WSWIRQHPGKGLEWIGYIYYSGSTYYNPSLKSRVTI SVDTSKNQFSLKLSSVTAADTAVYYCAREDGAFGY YGMDVWGQGTTVTVSS<br><br>SEQ ID NO: 28464 |

FIGURE 50
(Continued)

| | | | |
|---|---|---|---|
| iPS:392866 | 21-225_23H11 | NA | GACATCCAGATGACCCAGTCTCCATCCTCCCT GTCTGCATCTGTAGGAGACAGAGTCACCATCA CTTGCCGGGCAAGTCAGGACAGTCAGGCATT AGAAATGATTTAGACTGGTATCAGCAGAAACCAGGGAAAG CCCCTAAGGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATCGTTACCCGCTC ACTTTCGGCGGAGGGACCAAGGTGGAGATCA AA<br>SEQ ID NO: 24459 | CAGGAGCAGCTGGTGGAGTCTGGGGGAGGCGTG GTCCAGCCTGGGAGGTCCCTGAGACTCTCCTGTG CAGCCGTCTGGATTCACCTTCAGTAGCTATGGCAT GCACTGGGTCCGCCAGGCTCCAGGCAAGGGGCT GGAGTGGGTGGCAGTTATATGGTATGATGAAAAT AATAAATACTATGTAGACTCCGTGAAGGGCCGAT TCACCATCTCCAGAGACAACTCCAAGAACACGCT GTATCTGCAAATGAACAGCCTGAGAGCCGAGGA CACGGCTGTGTATTACTGTGCGAGAGAATTGGGG TTCCGGTCGACTACTGGGGCCAGGGAACCCTGG TCACCGTCTCCTCA<br>SEQ ID NO: 28465 |
| | | AA | DIQMTQSPSSLSASVGDRVTITCRASQGIRNDLD WYQQKPGKAPKRLIYAASSLQSGVPSRFSGSGS GTEFTLTISSLQPEDFATYYCLQHNRYPLTFGGG TKVEIK<br>SEQ ID NO: 24460 | QEQLVESGGGVVQPGRSLRLSCAASGFTFSSYGMH WVRQAPGKGLEWVAVIWYDENNKYYVDSVKGRF TISRDNSKNTLYLQMNSLRAEDTAVYYCARELGFR SDYWGQGTLVTVSS<br>SEQ ID NO: 28466 |
| iPS:392868 | 21-225_24D6 | NA | GACATCCAGATGACCCAGTCTCCATCCTCCCT GTCTGCATCTGTAGGAGACAGAGTCACCATCA CTTGCCAGGCGAGTCAGGACATTAACAACTAT TTAAAATTGGTATCAGCAGAAACCAGGGAAAG CCCCTTAAGCTCTTGATATACGATGCATCCGATT TGGAAACAGGGGTCCCATCAAGGTTCAGTGGA AGTGGATCTGGGACAGATCCTGAAGATATTGCAATAT CAGCAGTCTGCAACAGTATGAAAATCTCCGATC ACCTTCGGCCAAGGGACACGACTGGAGATTAA A<br>SEQ ID NO: 24461 | CAGGTGCAACTGGTAGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGTTCCAGGCAAGGGGCT GGAGTGGGTGGCAATTATATCATATGCTGGAAGT AATAAATCCTATGCAGACTCCGTGAAGGGCCGAT TCACCATCTCCAGAGACAACATTCCAAGAACACGCT GTATCTGCAAATGAACAGCCTGAGAGCTGAGGA CACGGCTGTGTATTACTGTGTGAGACGGGGATAC AGCTATGGCGGGTACGTATGGACGTCTGGGGC CAAGGGGCCACGGTCACCGTCTCCTCA<br>SEQ ID NO: 28467 |

FIGURE 50
(Continued)

| | | | | |
|---|---|---|---|---|
| | | AA | DIQMTQSPSSLSASVGDRVTITCQASQDINNYLNWYQQKPGKALKLLIYDASDLETGVPSRFSGSGSGTDFTFTISSLQPEDIAIYYCQQYENLPITFGQGTRLEIK<br><br>SEQ ID NO: 24462 | QVQLVESGGGVVQPGRSLRLSCAASGFTFSSYGMHWVRQVPGKGLEWVAIISYAGSNKSYADSVKGRFTISRDNSKNTLYLQMNSLRAEDTAVYYCVRRGYSYGGYGMDVWGQGATVTVSS<br><br>SEQ ID NO: 28468 |
| iPS:392870 | 21-225_20G9 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAGTACTTACCCTCTCACTTTCGGCGGAGGGACCAAGGTGGAGATCAAAA<br><br>SEQ ID NO: 24463 | CAGCTGCAGCTGCAGGAGTCGGGCCCAGGACTGGTGAAGCCTTCGGAGACCCTGTCCCTCACCTGCACTGTCTCTGGTGGCTCCATCAGCAGGAGTAGTTACTACTGGGGCTGGATCCGCCAGCCCCCAGGGAAGGGACTGGAGTGGATTGGGAGTATCTATTATAGTGGGAGCGCCTCTTACAACCGGTCCTCCAAGAGTCAGTCACCATATCCGTAGACACGTCCAGGAACCAGTTCTCCCTGAAGCTGAGCTCTGTGACCGCCGCAGACACGGCTGCGTATTACTGTGCGAGACTGAGCAGCAGCTGGTCTTTTGACTACTGGGGCCAGGGAACCCTGGTCACCGTCTCCTCA<br><br>SEQ ID NO: 28469 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHSTYPLTFGGGTKVEIK<br><br>SEQ ID NO: 24464 | QLQLQESGPGLVKPSETLSLTCTVSGGSISRSSYYWGWIRQPPGKGLEWIGSIYYSGSASYNPSLKSRVTISVDTSRNQFSLKLSSVTAADTAAYYCARLSSSWSFDYWGQGTLVTVSS<br><br>SEQ ID NO: 28470 |

FIGURE 50
(Continued)

| | | | | |
|---|---|---|---|---|
| iPS:392872 | 21-225_20B11 | NA | GACATCCAGATGACCCAGTCTCCATCCTCCT GTCTGCATCTGTAGGAGACAGAGTCACCATCA CTTGCCGGGCAAGTCAGGGCATTGGAAATGAT TTAGGCTGGTATCAGCAGAAACCAGAGAAAG CCCCTAAGCGCCTGATCTATGCTGCATCCAGT TTGCATAGTGGGGTCCCATCCAGGTTCAGCGG CAGTGGCTCTGGGACAGAATTCACTCTCACAA TCAGCAGCCTGCAGCCTGAAGATTTTGCAACT TATTACTGTCTACAGCATTATAGTTACCCTCGG ACGTTTGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGTCAT GCACTGGGTCCGCCAGGCTCCAGGCAAGGGCT GGAGTGGGTGGCAGTTATATGGTATGATGGAAGT AATAAATACTATGCAGAGACTCCGTGAAGGTCCGAT TCACCGTCTCCAGAGACACAATTCCAAGAACACGCT GTCTCTGCAAATGAACAGCCTGAGAGCCGAGGA CACGGCTGTGTATTACTGTGCGAGAGAGATAT ACCAGTGGCTGGTATGACTACGGTATGGACGTCT GGGGCCAAGGGACCACGGTCACCGTCTCCTCA |
| | | | SEQ ID NO: 24465 | SEQ ID NO: 28471 |
| | | AA | DIQMTQSPSSLSASVGDRVTITCRASQGIGNDLG WYQQKPEKAPKRLIYAASSLHSGVPSRFSGSGSG TEFTLTISSLQPEDFATYYCLQHYSYPRTFGQGT KVEIK | QVQLVESGGGVVQPGRSLRLSCAASGFTFSSYVMH WVRQAPGKGLEWVAVIWYDGSNKYYADSVKVRF TVSRDNSKNTLSLQMNSLRAEDTAVYYCARERYTS GWYDYGMDVWGQGTTVTVSS |
| | | | SEQ ID NO: 24466 | SEQ ID NO: 28472 |
| iPS:392874 | 21-225_21D2 | NA | GACATCCAGATGACCCAGTCTCCATCCTCCCT GTTTGCATCTGTAGGAGACAGAGTCACCATCA CTTGCCGGGCAAGTCAGAGCATTAGCGACTAT TTAAATTGGTATCAGCAGAAACCAGGGAGAG CCCCTAAACTCCTGATCTATGATACATCCAGTT TGCAAAGTGGGGTCCCATCAAGGTTCAGTGGC AGTGGATCTGGGACAGATTTCACTCTCACCAT CAACAGTCTGCAACAGACTACATATTCTTCCG ACTACTGTCAACAGAGTTACAATATTCTTCCG GAGGCCAGTTTTGGCCGGGGGACCAAGCTGG AGATCAAA | GAGGTGAAGCTGTTGGAGTCTGGGGGAGGCTTG GTACAGCCGGGGGGGTCCCTGAGACTCTCCTGTG CAGCCTCTGGATTCACCTTTAACAACTATGCCAT GAGCTGGGTCCGCCAGGCTCCAGGGAAGGGGCT GGAGTGGGTCTCAGTTCTTAGTGGTAGTGGTGGT AGCACATTCTACGCAGACTCCGTGAAGGGCCGGT TCACCATCTCCAGAGACAATTCCAAGAACACGCT GTATCTGCAAATGAGCAGCCTGAGAGCCGGGGA CACGGCCGTATATTCTGTGCCCGATATTGTAGT AGTGCCAGGTGCCCTTATGATGCCTTTGATATCT GGGGCCAAGGGACAATGGTCACCGTCTCCTCA |
| | | | SEQ ID NO: 24467 | SEQ ID NO: 28473 |

FIGURE 50
(Continued)

| | | | | |
|---|---|---|---|---|
| iPS:392876 | | AA | DIQMTQSPSSLFASVGDRVTITCRASQSISDYLN WYQQKPGRAPKLLIYDTSSLQSGVPSRFSGSGSG TDFTLTINSLQPEDFATYYCQQTYNILPERSFGRG TKLEIK<br>SEQ ID NO: 24468 | EVKLLESGGGLVQPGGSLRLSCAASGFTFNNYAMS WVRQAPGKGLEWVSVLSGSGGSTFYADSVKGRFTI SRDNSKNTLYLQMSSLRAGDTAVYFCARYCSSARC PYDAFDIWGQGTMVTVSS<br>SEQ ID NO: 28474 |
| | | NA | GACATCCAGATGACCCAGTCTCCATCCTCCCT GTCTGCATCTGTAGGAGACAGAGTCACCATCA CTTGCCGGGCAAGTCAGGACAGATTAGAAATGAT TAGGCTGGTATCAGCAGAAACCAGGGAAAG CCCCTAAGCGCCTGATCTATGCTGCATCCAAT TTTCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAATTACCCGTG GACGTTCGGCCAAGGGACCAAGGTGGAAATC AAA<br>SEQ ID NO: 24469 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGTAGACTCCGTGAAGGGCCGAT AATAAATACTATGTAGACTCCGTGAAGGGCCGAT TCACCATCTCAGAGACAATTCCAAGAACACGCT GTATCTGCAAATGAACAGCCTGAGAGCCGAGGA CACGGCTGTGTATTACTGTGCGAGAGATCTTGGC TGGACGGAAGAGTACTGGGGCCAGGGAACCCTG GTCACCGTCTCCTCA<br>SEQ ID NO: 28475 |
| 21-225_21F7 | | AA | DIQMTQSPSSLSASVGDRVTITCRASQDIRNDLG WYQQKPGKAPKRLIYAASNFQSGVPSRFSGSGS GTEFTLTISSLQPEDFATYYCLQHNNYPWTFGQG TKVEIK<br>SEQ ID NO: 24470 | QVQLVESGGGVVQPGRSLRLSCAASGFTFSDYGM HWVRQAPGKGLEWVAVIWFDGNNKYYVDSVKGR FTISRDNSKNTLYLQMNSLRAEDTAVYYCARDLG WTEEYWGQGTLVTVSS<br>SEQ ID NO: 28476 |

FIGURE 50
(Continued)

| | | | | |
|---|---|---|---|---|
| iPS:392878 | 21-225_22C5 | NA | GACATCCAGATGACCCAGTCTCCAGCCTCCCT GTCTGCGTCTGTGTTGGAGACAGAGTCACCATCA CTTGCCGGGCAAGTCAGAACATTAGCAGCTAT TTAAATGGTATCAGCAGAAACCAGGGAAGG CCCCTAAACTCCTGATCTATGCTGCATCCGTTT TGCAACATGGGATCCCATCAAGGTTCAGTGGC AGGGGATCTGGGACAGATTTCACTCTCATCAT CAGTAGTCTGCAACCTGAAGATTTTGCAACTT ACTACTGTCAACAGAGTTACAGAACCCCTTA TTCACTTTCGGCCCTGGGACCAAAGTAGATTT CAAA<br><br>SEQ ID NO: 24471 | GAGGTGCAGCTGTTGGAGTCTGGGGGAGGCTTG GTACAGGTTGGGGGGTCCCTGAGACTCTCCTGTG CAGCCTCTGGATTCACTTTAGCAGCTATGCCAT GAGCTGGGTCCGCCAGGCTCCAGGGATGGGGCT GGAGTGGGTCTCAATTATTAGTGGTAGTGGTGT TACACATACTACGCGGACTCCGTGAAGGGCCGAT TCACCATCTCCAGAGACAATTCCAAGAACACGCT GTATCTGCAAATGAACAGCCTGAGAGCCGAGGA CACGGCCGTATATTATTGTGCGTCCCGTATAGCA GTGGCTGGCTCGGAGGCTTTTGATATCTGGGGCC AAGGGACAATGGTCACCGTCTCTCA<br><br>SEQ ID NO: 28477 |
| | | AA | DIQMTQSPASLSASVGDRVTITCRASQNISSYLN WYQQKPGKAPKLLIYAASVLQHGIPSRFSGRGS GTDFTLTISSLQPEDFATYYCQQSYRTPLFTFGPG TKVDFK<br><br>SEQ ID NO: 24472 | EVQLLESGGGLVQVGGSLRLSCAASGFTFSSYAMS WVRQAPGMGLEWVSIISGSGGYTYYADSVKGRFTI SRDNSKNTLYLQMNSLRAEDTAVYYCASRIAVAGS EAFDIWGQGTMVTVSS<br><br>SEQ ID NO: 28478 |
| iPS:392880 | 21-225_22F9 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGGCCCTGATCTATGCTGCATCCAGT TTACAAAGTGGGGTCCCATCAAGGTTCAGCGG CAGTGGATCTGGGACAGGATTTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br><br>SEQ ID NO: 24473 | CAGGTGCAGATGGTGGAGTCTGGGGGAGGCGTG GTCCAGCCTGGGAGGTCCCTGAGACTCTCCTGTG CAGCGTCTGGATTCACCTTCAGTAGTAGCTATGCAT GCACTGGGTCCGCCAGGCTCCAGGCAAGGGGCT GGAGTGGGTGGCAGTTATATGTAGACTCCGTGAAGGGCCG TAATAAAGACTATGTAGACTCCGTGAAGGGCCG ATTCACCATCTCCAGAGACAATTCCAAGAGCACG CTGTATCTGCAAATGAATAGTCTGAGAGCCGAGG ACACGGCTGTGTATTACTGTGTGAGAGATTAGG CTTCCAGTCTGACTACTGGGGCCAGGGAACCCCG GTCACCGTCTCCTCA<br><br>SEQ ID NO: 28479 |

FIGURE 50
(Continued)

| | | | | |
|---|---|---|---|---|
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPLTFGGGTKVEIK | QVQMVESGGGVVQPGRSRLRLSCAASGFTFSSYGMHWVRQAPGKGLEWVAVIWYEENNKDYVDSVKGRFTISRDNSKSTLYLQMNSLRAEDTAVYYCVRELGFQSDYWGQGTPVTVSS |
| | | | SEQ ID NO: 24474 | SEQ ID NO: 28480 |
| iPS:392882 | 21-225_23A3 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTGTGCAAAGTGGGGTCCCATCAAGGTTCAGCGGCAGTGGATCTGGGACAGAATTCACTCTCACAATCAGCAGCCTGCAGCCTGAAGATATTGCAATTTATTTCTGTCTACAGCATAATAGTTACCCGCTCACTTTCGGCGGAGGGACCAAGGTGGAGATCAAA | CAGCTGCAGCTGCAGGAGTCGGGCCCAGGACTGGTGAAGCCTTCGGAGACCCTGTCCCTCACCTGCACTGTCTCTGGTGGCTCCATCAGTAGAGTAGTTACTACTGGGGCTGGATCCGCCAGCCCCCAGGGCAGGGGGCTGGAGTGGATTGGAATATTTATTATAGTGGGAGCACCTACAACAACCCGTCCTCCAAGAGTCGAGTCTCCATATCCGTTGACACGTCCAAGAACCAGTTCTCCCTGAACCTGAGCTCTGTGACCGCCGCAGACACGGCTGTGTATTACTGTGGGAGACATGGAAAAGACTGGGGCCTTGACTTCTGGGGCCAGGGAACCCTGGTCACCGTCTCCTCA |
| | | | SEQ ID NO: 24475 | SEQ ID NO: 28481 |
| | | AA | DIQMTQSPSSLSASVGDRVTITCRASQGIRNDLGWYQQKPGKAPKRLIYAASSVQSGVPSRFSGSGSGTEFTLTISSLQPEDFAIYFCLQHNSYPLTFGGGTKVEIK | QLQLQESGPGLVKPSETLSLTCTVSGGSISRSSYYWGWIRQPPGQGLEWIGNIYYSGSTYNNPSLKSRVSISVDTSKNQFSLNLSSVTAADTAVYYCGRHGKDWGLDFWGQGTLVTVSS |
| | | | SEQ ID NO: 24476 | SEQ ID NO: 28482 |

FIGURE 50
(Continued)

| | | | | |
|---|---|---|---|---|
| iPS:392884 | 21-225_23A10 | NA | GACATCTGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATCGTGCATCCAGT TTGCAAAGTGGGGTCCCATCAAGGTTCAGCGG CAGTGGATCTGGGACAGAATTCACTCTCACAA TCGGCAGCCTGCAGCCTGAAGATTTGCAACT TATTACTGTCTGCAACATTATAGTTACCCTCGG ACGTTCGGCCTAGGGACCAAGGTGGAAATCA AA | CAGGTGCAGTTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAAGGTA TAGCAGTGGCTGGCACGACTACGGTATGGACGTC TGGGGCCAAGGGACCACGGTCACCGTCTCCTCA |
| | | | SEQ ID NO: 24477 | SEQ ID NO: 28483 |
| | | AA | DIQMTQSPSSLSASVGDRVTITCRASQGIRNDLG WYQQKPGKAPKRLIYAASSLQSGVPSRFSGSGS GTEFTLTIGSLQPEDFATYYCLQHYSYPRTFGLG TKVEIK | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARERYSS GWHDYGMDVWGQGTTVTVSS |
| | | | SEQ ID NO: 24478 | SEQ ID NO: 28484 |
| iPS:392886 | 21-225_23A12 | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATAACAATTATTTAGCTTGGTACCA GCAGAAACCAGGACAGCCTCCTAAGCTGCTCA TTTACTGGGACATCTACCCGGGAATCCGGGGTC CCTGACCGATTCAGTGGCAGCGGGTCTGGGAC AGATTTCACTCTCACCATCAGCAGCCTGCAGG CTGAAGATGTGGCCGTTTATTACTGTCAGCAG TATTATGATACTCCTCCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACCCCTTCACCAATTATGATA TCAACTGGGTGCGACAGGCCACTGGACAAGGGC TTGAGTGGATGGGATGGATGCACCTAACAGTGG TAACACAGGCTATGCACAGAAGTTCCAGGGCAG AGTCACCATGACCAGGAACACCTCCATAAACAC AGCCTACATGGAACTGAGCAGCCTGAGATCTGA GGACACGGCCGTGTATTACTGTGCGCGGTAGCAGT GGCTGGTACTACTTTGACTACTGGGGCCAGGGAA CCCTGGTCACCGTCTCCTCA |
| | | | SEQ ID NO: 24479 | SEQ ID NO: 28485 |

FIGURE 50
(Continued)

| | | | |
|---|---|---|---|
| iPS:392888 | 21-225_25A2 | AA | DIVMTQSPDSLAVSLGERATINCKSSQSVLYSSN NNNYLAWYQQKPGQPPKLLIYWTSTRESGVPDR FSGSGSGTDFTLTISSLQAEDVAVYYCQQYYDTP PTFGQGTKVEIK<br>SEQ ID NO: 24480 | QVQLVQSGAEVKKPGASVKVSCKASGYPFTNYDIN WVRQATGQGLEWMGWMHPNSGNTGYAQKFQGR VTMTRNTSINTAYMELSSLRSEDTAVYYCAGSSGW YYFDYWGQGTLVTVSS<br>SEQ ID NO: 28486 |
| | | NA | GATATTGTGATGAACCAGACTCCACTCTCTCT GTCCGTCACCCCTGGACAGCCGGCCTCCATCT CCTGCAAGTCTAGTCAGAGCCTCCTACATAGT GAAGGAAAGACCTATTTGTATTGGTATCTGCA GAAGCCAGGCCAGCCTCCACAACTCCTGATCT ATGAAATTTCCAACGGTTCTCTGGAGTGCCA GCTAGGTTAAGTGGCAGCGGGTCAGGGACAG ATTTCACACTGAAAATCAGCGGGTGGAGGCT GAGGATGTTGGGGTTTATTACTGCATGCAAAG TACACAGTTTCCGCTCACTTTCGGCGGAGGGA CCAAGGTGGAGATCAAA<br>SEQ ID NO: 24481 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAGTAGTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCAGGGGTATGGACGTCTGGGG CCAAGGGACCACGGTCACCGTCTCCTCA<br>SEQ ID NO: 28487 |
| | | AA | DIVMNQTPLSLSVTPGQPASISCKSSQSLLHSEGK TYLYWYLQKPGQPPQLLIYEISNRFSGVPARLSG SGSGTDFTLKISRVEAEDVGVYYCMQSTQFPLTF GGGTKVEIK<br>SEQ ID NO: 24482 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTVSS<br>SEQ ID NO: 28488 |

FIGURE 50
(Continued)

| | | | |
|---|---|---|---|
| iPS:392890 | 21-225_20H9 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCGTCCCTGATCTCTGTGCATCCAGTTT GCAAAGTGGGGTCCCATCAAAGTTCAGGGCA GTGGATCTGGGACAGATTCACTCTCACCATC AGCAGCCTGCAGCCTGAAGATTTTGCAACTTA TTACTGCCAACAGTATAATAGTTACCCATTCA CTTTCGGCCCTGGGACCAAAGTGGATATCAAA <br><br> SEQ ID NO: 24483 | GAGGTGCAGCTGTTGGAGTCGGGGGAGGCTTG GTACAGCCTGGGGGGTCCCTGAGACTCTCCTGTG CAGCCTCCGGATTCACCTTTAGCAGCTATGCCAT GAGCTGGGTCCGCCAGGCTCCAGGGAAGGGGCT GGAGTGGGTCTCAGCTATTAGTGGTAGTGGTGGT TACACATACTACGCAGACTCCGTGAAGGGCCGGT TCACCATCTCCAGAGACAATTCCGAGAACACGCT GTATCTGCAAATGAGCAGCCTGAGAGCCGAGGA CACGGCCGTTTATTACTGTGCGAAAGGGGGGTCC CTCTTCTACTGGGGCCAGGGAACCCTGGTCACCG TCTCCTCA <br><br> SEQ ID NO: 28489 |
| | | AA | DIQMTQSPSSLSASVGDRVTITCRASQGISNYLA WFQQKPGKAPKSLISAASSLQSGVPSKFSGSGSG TDFTLTISSLQPEDFATYYCQQYNSYPFTFGPGT KVDIK <br><br> SEQ ID NO: 24484 | EVQLLESGGGLVQPGGSLRLSCAASGFTFSSYAMS WVRQAPGKGLEWVSAISGSGGYTYYADSVKGRFT ISRDNSENTLYLQMSSLRAEDTAVYYCAKGGSLFY WGQGTLVTVSS <br><br> SEQ ID NO: 28490 |
| iPS:392892 | 21-225_20C11 | NA | GACATCCAGATGACCCAGTCTCCATCCTCACT GTCTGCATCTGTTGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTATGCTGCATCCAGTTT GCAAAGTGGGGTCCCATCATGCAAAGTTCAGTGG AGTGGATCTGGGACAGCTTCACTCTCACCAT CAGCAGCCTGCAGCCTGAAGATTTTGCAACTT ATTACTGCCAACAGTATCATAGTTTCCCATTCA CTTTCGGCCCTGGGACCAAAGTGGATGTCAAA <br><br> SEQ ID NO: 24485 | GAGGTGCAGCTGTTGGAGTCGGGGGAGGCTTG GTACAGCCTGGGGGGTCCCTGAGACTCTCCTGTG CAGCCTCTGGATTCTCCTTTAGTAGCTATGCCAT GAGCTGGGTCCGCCAGGCTCCAGGGAAGGGGCT GGAGTGGGTCTCAACTATTAGTGGTCGTGGTGGT CACACATACTACGCAGACTCCGTGAAGGGCCGG TTCGCCATCTCCAGAGACAGTTCCAAGAACACGC TGTATCTGCAAATGCGTATATTACTGTGCGAAACAGC ACACGGCCGTATATTACTGTGCGAAACAGGACTG CTGGGGCCAGGGAACCCTGGTCACCGTCTCCTCA <br><br> SEQ ID NO: 28491 |

FIGURE 50
(Continued)

| | | | |
|---|---|---|---|
| iPS:392894 | 21-225_21G2 | AA | DIQMTQSPSSLSASVGDRVTITCRASQDISNYLA WFQQKPGKAPKSLIYAASSLQSGVPSKFRGSGSG TDFTLTISSLQPEDFATYYCQQYHSFPFTFGPGTK VDVK<br>SEQ ID NO: 24486 | EVQLLESGGGLVQPGGSLRLSCAASGFSFSSYAMS WVRQAPGKGLEWVSTISGRGGHTYYADSVKGRFA ISRDSSKNTLYLQMNSLRAEDTAVYYCAKQDCWG QGTLVTVSS<br>SEQ ID NO: 28492 |
| | | NA | GACATCCAGATGACCCAGTCTCCATCCTCCCT GTCTGCGTCTGTAGGAGACAGAGTCACCATCA CTTGCCGCGGGCAAGTCAGGGACATTAGAAATGAT TTAGGCTGGTATCAGCAGAAACCAGGAAAG CCCCTAAGCGCCTGATCTATACTTCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAACATATAGTTACCCGTGG ACGTTCGGCCTAGGGACCAAGGTGGTCATCAA A<br>SEQ ID NO: 24487 | CAGGTGCAACTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGATGGCAGTTATATGGTATGATGTAACT AATAAATACTATGCAGACTCCGTGAAGGGCCGA TTCACCATCTCCAGAGACAATTCCAAGAACACGC TGTATCTGGAAATGAACAGCCTGAGAGCCGAGG ACACGGCTGTTTATTACTGTGCGAGAGAGCTTGG CTGGTACGAGGACTACTGGGGCCAGGGAACCCT GGTCACCGTCTCCTCA<br>SEQ ID NO: 28493 |
| | | AA | DIQMTQSPSSLSASVGDRVTITCRASQGIRNDLG WYQQKPGKAPKRLIYTSSSLQSGVPSRFSGSGSG TEFTLTISSLQPEDFATYYCLQHNSYPWTFGLGT KVVIK<br>SEQ ID NO: 24488 | QVQLVESGGGVVQPGRSLRLSCAASGFTFSDYGM HWVRQAPGKGLEWMAVIWYDVTNKYYADSVKG RFTISRDNSKNTLYLEMNSLRAEDTAVYYCARELG WYEDYWGQGTLVTVSS<br>SEQ ID NO: 28494 |

FIGURE 50
(Continued)

| | | | | |
|---|---|---|---|---|
| iPS:392896 | 21-225_21G7 | NA | GACATCCAGATGACCCAGTCTCCATCCTCCT GTCTGCATCTGTAGGAGACAGAGTCACCATCA CTTGCCGGGCAAGTCAGGGCGTTAGAAATGAT TTAGGCTGGTATCAGCAGAAACCAGGGAAAG CCCCTCAGCGCCTGATCTATGCTGCATCCAGTT TGCAAAGTGGGGGTCCCATCAAGGTTCAAGGC AGTGGATCTGGGACAGAATTCACTCTCACAAT CAGCAGCCTGCAGCCTGAAGATTTTGCAACTT ATTACTGTCTACAGCATAGTAGTTACCCGCTC ACTTTCGGCGGAGGGACCAAGGTGGAGATCA AA | CAGCTGCAGCTGCAGGAGTCGGGCCCAGGACTG GTGAAGTTTTGGAGACCCTGTCCCTCACCTGCA CTGTCTCTGGTGGCTCCATCAGCAGAAGTAGTTA CTACTGGGGCTGGATCCGCCAGCCCCCAGGAA GGGGCAGGAGTGGATAGGGAATATCTATTATAG TGGGTATAGTTACTACAATCCGTCCCTCAAGAGT CGAGTCACCATATCGTAGACACGTCCAAGAACC AGTTCCCTGAAGCTGAGCTCTGTGACCGCGC AGACACGGCTGTGTATTACTGTGCGAGACATAGC ACCAGCTGGTCCCTTGACTACTGGGGCCAGGGAA CCCTGGTCACCGTCCTCA |
| | | | SEQ ID NO: 24489 | SEQ ID NO: 28495 |
| | | AA | DIQMTQSPSSLSASVGDRVTITCRASQGVRNDLG WYQQKPGKAPQRLIYAASSLQSGVPSRFNGSGS GTEFTLTISSLQPEDFATYYCLQHSSYPLTFGGGT KVEIK | QLQLQESGPGLVKFSETLSLTCTVSGGSISRSSYYW GWIRQPPGKGQEWIGNIYYSGYSYNPSLKSRVTIS VDTSKNQFSLKLSSVTAADTAVYYCARHSTWSLD YWGQGTLVTVSS |
| | | | SEQ ID NO: 24490 | SEQ ID NO: 28496 |
| iPS:392898 | 21-225_21H10 | NA | GAAATTGTGTTGACGCAGTCTCCAGGCACCCT GTCTTTGTCTCCAGGGGAAAGAGCCACCCTCT CCTGCAGGGCCAGTCAGAGTTTTAGCAGC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAGCTCACGC AGTTTTGGCCAGGGGACCAAGCTGGAGATCAA A | GAGGTGCAGCTGGTGGAGTCTGGGGGAGGCTTG GTAAAGCCTGGGGGGTCCCTTAGACTCTCCTGTG CAGCCTCTGGATTCACTTTCAGTAACGCCTGAT GAACTGGGTCCGCCAGGCTCCAGGGAAGGGCT GGAGTGGGTTGGCCGTATTAAAAGCAAAACTGA TGGTGGGACAACAGACTACGCTGCACCCGTGAA AGGCAGATTCACCATCTCAAGAGATGATTCAAA AAACACCGTATCTGCAAATGAACAGCCTGA AACCGAGGACACAGCCGTGTATTACTGTACCACA GAAGGCTGGAACACGGACTACTGGGGCCAGGGA ACCCTGGTCACCGTCTCCTCA |
| | | | SEQ ID NO: 24491 | SEQ ID NO: 28497 |

FIGURE 50
(Continued)

| | | AA | EIVLTQSPGTLSLSPGERATLSCRASQSFSSSYLA WYQQKPGQAPRLLIYGASSRATGIPDRFSGSGSG TDFTLTISRLEPEDFAVYYCQQYGSSRSFGQGTK LEIK<br>SEQ ID NO: 24492 | EVQLVESGGGLVKPGGSLRLSCAASGFTFSNAWM NWVRQAPGKGLEWVGRIKSKTDGGTTDYAAPVK GRFTISRDDSKNTLYLQMNSLKTEDTAVYYCTTEG WNTDYWGQGTLVTVSS<br>SEQ ID NO: 28498 |
|---|---|---|---|---|
| iPS:392900 | 21-225_22F2 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGAAAG CCCCTAAGCGCCTGATCTATGCTGCATCCAGT TTACAAAGTGGGGTCCCATCAAGGTTCAGCGG CAGTGGATCTGGGACAGGATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24493 | CAGGTGCAGTTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGAGGGAAG TAATAAATACTATGTAGACTCCGTGAGGGGCCGA TTCACCATCTCCAGAGACAATTCCAAGAACACGC TGTATCTGCAAATGAACAGCCTGAGAGCCGAGG ACACGGCTGTTTATTACTGTGTGAGAGAGCTAGG CTTCCAGTCTGACTACTGGGGCCAGGGAACCCCG GTCACCGTCTCCTCA<br>SEQ ID NO: 28499 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24494 | QVQLVESGGGVVQPGRSLRLSCAASGFTFSDYGM HWVRQAPGKGLEWVAVIWYEGSNKYYVDSVRGR FTISRDNSKSTLYLQMNSLRAEDTAVYYCVRELGF QSDYWGQGTPVTVSS<br>SEQ ID NO: 28500 |

FIGURE 50
(Continued)

| | | | |
|---|---|---|---|
| iPS:392902 | 21-225_22D5 | NA | GACATCCAGATGACCCAGTCTCCATCCTCCT GTCTGCATCTGTAGGAGACAGAGTCACCATCA CTTGCCGGGCAAGTCAGAACAGTTTTAGTTAT TTAAATTGGTATCATCAGAAACCAGGGAAAGC CCCTAAGCTCCTGATCTATGCTGCATCCAGTT TGCAAAGTGGGGGTCCCATCAAGGTTCAGTGGCA GTGGATCTGGGACAGATTTCACTCTCACCATC AGCAGTCTACAACCTGAAGATTTTGCAACTTA CTACTGTCAACAGAGTTACAGTACCCCTTAT TCACTTTCGGCCCTGGGACCAAAGTGGATATC AAA |
| | | | SEQ ID NO: 24495 |
| | | AA | DIQMTQSPSSLSASVGDRVTITCRASQNIFSYLN WYHQKPGKAPKLLIYAASSLQSGVPSRFSGSGS GTDFTLTISSLQPEDFATYCQQSYSTPLFTFGPG TKVDIK |
| | | | SEQ ID NO: 24496 |
| | | | GAGGTGCAGCTGTTGGAGTCTGGGGAGGCTTG GTACAGCCTGGGGGGGTCCCTGAGACTCTCCTGTG CAGCCTCTGAATTCACCTTTAGCAGCTATGCCAT GAGCTGGGTCCGCCAGGCTCCAGGGAAGGGCT GGAGTGGGTCTCAGTTATTAGTGGTCGTGGTGGT AACACATTCTACGCAGACTCCGTGAAGGGCCGGT TCACCATCTCCAGAGACAATGAACAGCCTGAGAGCCGAGGA GTATCTGCAAATGAACAGCCTGAGAGCCGAGGA CACGGCCGTATATTACTGTGCGTCCCGTATAGCA GTGGCTGGCTCGGAGGCTTTTGATATCTGGGGCC AAGGGACAATGGTCACCGTCTCTTCA |
| | | | SEQ ID NO: 28501 |
| | | | EVQLLESGGGLVQPGGSLRLSCAASEFTFSSYAMS WVRQAPGKGLEWVSVISGRGGNTFYADSVKGRFTI SRDNSKNTLYLQMNSLRAEDTAVYYCASRIAVAGS EAFDIWGQGTMVTVSS |
| | | | SEQ ID NO: 28502 |
| iPS:392904 | 21-225_22G9 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAAG CCCCTAAGCGCCTGATCTATGCTGCTTCCAGTT TGCAAAGTGGGGTCCCATCAAGGTTCAGCGGC AGTGGATCTGGGACAGAGTTCACTCTCACAAT CAGCAGCCTGCAGCCTGAAGATTTTGCAACTT ATTACTGTCTACAGCATAATAGTTACCCGCTC ACTTTCGGCGGAGGGACCAAGGTGGAGATCA AA |
| | | | SEQ ID NO: 24497 |
| | | | CAGCTGCAGCTGCAGGAGTCGGGCCCAGGACTG GTGAAGCCTTCGGAGACCCTGTCCCTCACCTGCA CTGTCTCCGGTGGCGCCATCAGCGGTAGTAATTA CTACTGGGGCTGGATCCGCCAGCCCCCAGGGAA GGGACTGGAGTGGATTGGAAATATCTATTATAGT GGGAGCACCTACTACAACCCGTCCCTCAAGAGTC GAGTCACCATATCCGTAGACACGTCCAAGAACC AGTTCTCCCTGAAGCTGACGACGACATAGC AGACACGGCTGTGTATTACTGTGCGAGACATAGC AGTAGTGGTCCCTTGACTACTGGGGCCAGGGAA CCCTGGTCACCGTCTCCTCA |
| | | | SEQ ID NO: 28503 |

FIGURE 50
(Continued)

| | | | | |
|---|---|---|---|---|
| iPS:392908 | 21-225_23F12 | AA | DIQMTQSPSSLSASVGDRVTITCRASQGIRNDLGWYQQKPGKAPKRLIYAASSLQSGVPSRFSGSGSGTEFTLTISSLQPEDFATYYCLQHASYPLTFGGGTKVEIK<br><br>SEQ ID NO: 24498 | QLQLQESGPGLVKPSETLSLTCTVSGGAISGSNYYWGWIRQPPGKELEWIGNIYYSGSTYYNPSLKSRVTISVDTSKNQFSLKLRSVTAEDTAVYYCARHSSSWSLDYWGQGTLVTVSS<br><br>SEQ ID NO: 28504 |
| | | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGAAAGCCCCTAAGCGCCTGATCTATGTTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAAGTTATTACTGTCTACAGCATATAGTTACCCGTGGACGTTCGGCCAAGGGACCAAGGTGGAAATCAAA<br><br>SEQ ID NO: 24499 | CAGGTGCAGCTGGTGGAGTCTGGGGGAGGCGTGGTCCAGCCTGGGAGGTCCCTGAGACTCTCCTGTGTAGCGTCTGGATTCACCTTCAGTAGCTATGCATGCACTGGGTCCGCCAGGCTCCAGGCAAGGGGCTGGAGTGGGTGGCAGTTATATGGTATGATGAAACTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTATTTATTACTGTGCGAGAGAGCTTGCCTGGTACGAGGACTACTGGGGCCAGGGGATCCCTGGTCACCGTCTCCTCA<br><br>SEQ ID NO: 28505 |
| | | AA | DIQMTQSPSSLSASVGDRVTITCRASQGIRNDLGWYQQKPGKAPKRLIYVASSLQSGVPSRFSGSGSGTEFTLTISSLQPEDFASYYCLQHNSYPWTFGQGTKVEIK<br><br>SEQ ID NO: 24500 | QVQLVESGGGVVQPGRSLRLSCVASGFTFSSYGMHWVRQAPGKGLEWVAVIWYDETNKYYADSVKGRFTISRDNSKNTLYLQMNSLRAEDTAIYYCARELAWYEDYWGQGSLVTVSS<br><br>SEQ ID NO: 28506 |

FIGURE 50
(Continued)

| | | | |
|---|---|---|---|
| iPS:392912 | 21-225_25A9 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGTGGCAGTGGATCTGGGACAGATTCACTCTCACAATCAGCAGCCTGCAGCCTGAAGATTTTGCAACTTATTACTGTCTACAGCATAATAGTTACCCATTCACTTTCGGCCCTGGGACCAAAGTGGATATCAA A |  CAGGTGCAGCTGGTGGAGTCTGGGGGAGGCGTGGTCCAGCCTGGGAGGTCCCTGAGACTCTCCTGTGCAGCCGTCTGGATTCACCTTCAGTAGCTATGGCATGCACTGGGTCCGCCAGGCTCCAGGCAAGGGGCTGGAGTGGGTGGCAGTTATATGGTATGATGTAACTAATAAATACTATACAGGCTCCGTGAAGGGCCGATTCACCATCTCCAGAGACAATTCCAAGAACACGCTGTATCTGCAAATGAACAGCCTGAGAGCCGAGGACACGGCTGTATATTACTGTGCGAGAGAAATTGGCTGGTTAGATGACTACTGGGGCCAGGGAACCCTGGTCACCGTCTCCTCA |
| | | | SEQ ID NO: 24501 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPFTFGPGTKVDIK | QVQLVESGGGVVQPGRSLRLSCAASGFTFSSYGMHWVRQAPGKGLEWVAVIWYDVTNKYYTGSVKGRFTISRDNSKNTLYLQMNSLRAEDTAVYYCAREIGWLDDYWGQGTLVTVSS |
| | | | SEQ ID NO: 24502 | SEQ ID NO: 28508 |
| iPS:392914 | 21-225_25D12 | NA | GACATCCAGATGACCCAGTCTCCATCCTCCCTGTCTGCATCTGTAGGAGACAGAGTCACCATCACTTGCCGGGACAAGTCAGGGCATTAGAAATGATTTAGGCTGGTATCAGCAGAAAACCAGGGAAAGCCCCTAAGCGCCTGATCTATGCTGCATCCAGTTTACAAAGTGGGGTCCCATCAAGGTTCAGCGGCAGTGGATCTGGGACAGATTCACTCTCACAATCAGCAGCCTGCAGCCTGAAGATTTTGCAACTTATTACTGTCTACAGCATTATAGTTTCCCTCGGACGTTCGGCCAAGGGACCAAGGTGGAAATCA AA | CAGGTGCAGCTGGTGGAGTCTGGGGGAGGCGTGGTCCAGCCTGGGAGGTCCCTGAGACTCTCCTGTGCAGCCGTCTGGATTCACCTTCAGTAGCGATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGGTATAGCAGCAGCTGGTACGACTACGGTATGGACGTCTGGGGCCAAGGGACCACGGTCACCGTCTCCTCA |
| | | | SEQ ID NO: 24503 | SEQ ID NO: 28509 |

FIGURE 50
(Continued)

| | | | |
|---|---|---|---|
| | | AA | DIQMTQSPSSLSASVGDRVTITCRTSQGIRNDLG WYQQKPGKAPKRLIYAASSLQSGVPSRFSGSGS GTEFTLTISSLQPEDFATYYCLQHYSFPRTFGQGT KVEIK<br><br>SEQ ID NO: 24504 | QVQLVESGGGVVQPGRSLRLSCAASGFTFSSDGMH WVRQAPGKGLEWVAVIWYDGSNKYYADSVKGRF TISRDNSKNTLYLQMNSLRAEDTAVYYCARERYSS SWYDYGMDVWGQGTTVTVSS<br><br>SEQ ID NO: 28510 |
| iPS:392916 | 21-225_27C5 | NA | GACATCCAGATGACCCAGTCTCCCTCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGTTCCTGATCTATGCTGCATCCAGTT TGCAAAGTGGGGTCCCATCAAGGTTCAGCGCC AGTGGATCTGGGACAGAGTTCACTCTCACCAT CAGCAGCCTGCAGCCTGAAGATTTTGCAACTT ACTGTTGTCAACAGTATGACAGTTCCCTCGG ACGTTCGGCCAAGGGACCAAGGTGGAAATCA AA<br><br>SEQ ID NO: 24505 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCACTAGTAGTAGTGATAGT TATATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGTGGCGTCC TTTGACTGCTGGGGCCAGGGAACCCTGGTCACCG TCTCCTCA<br><br>SEQ ID NO: 28511 |
| | | AA | DIQMTQSPSSVSASVGDRVTITCRASQGISSWLA WYQQKPGKAPKFLIYGASSLQSGVPSRFSASGSG TEFTLTISSLQPEDFATYCCQQYDSFPRTFGQGTK VEIK<br><br>SEQ ID NO: 24506 | EVQLVESGGGLVKPGGSLRLSCAASGFTFSSYSMN WVRQAPGKGLEWVSSTSSSDSYIYYADSVKGRFTI SRDNAKNSLYLQMNSLRAEDTAVYYCARVASFDC WGQGTLVTVSS<br><br>SEQ ID NO: 28512 |

FIGURE 50
(Continued)

| | | | |
|---|---|---|---|
| iPS:392918 | 21-225_28F5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATACTTACCCGTG GACGTTCGGCCAAGGGACCAAGGTGGAAGTC AAA<br><br>SEQ ID NO: 24507 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTATGGCAT GCACTGGGTCCGCCAGGCTCCAGGCAAGGGGCT GGAGTGGGTGGCAGTTATATGCAGACTCCGTGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAATTAGG CTGTACGACGACTACTGGGGCCAGGGAACCCT GGTCACCGTCTCCTCA<br><br>SEQ ID NO: 28513 |
| | | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNTYPWTFGQGT KVEVK<br><br>SEQ ID NO: 24508 | QVQLVESGGGVVQPGRSLRLSCAASGFTFSSYGMH WVRQAPGKGLEWVAVIWYDENNKYYADSVKGRF TISRDNSKNTLYLQMNSLRAEDTAVYYCARELGW YDDYWGQGTLVTVSS<br><br>SEQ ID NO: 28514 |
| iPS:392920 | 21-225_29G4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA CA<br><br>SEQ ID NO: 24509 | CAGGTGCAGCTGGTGGAGTCTGGGGGAGGCGTG GTCCAGCCTGGGAGGTCCCTGAGACTCTCACCTGTG CAGCGTCTGGATTCACCTTCAGTGACTATGGCAT ACACTGGGTCCGCCAGGCTCCAGGCAAGGGCT GGAGTGGGTGGCAGTTATATGCAGACTCATGAAAGT AATAAATACTATGCAGACTCCATGAAGGGCCGA TTCACCATCTGCAAATGAACAGCCTGAGAGCCGAGG ACACGGCTGTGTATTACTGTGCGAGAGAACTGGG AATGACGGGTGACTACTGGGGCCAGGGAACCCT GGTCACCGTCTCCTCA<br><br>SEQ ID NO: 28515 |

FIGURE 50
(Continued)

| | | | |
|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIT<br>SEQ ID NO: 24510 | QVQLVESGGGVVQPGRSLRLTCAASGFTFSDYGIH WVRQAPGKGLEWVAVIWYDESNKYYADSMKGRF TISRDNSKNTLYLQMNSLRAEDTAVYYCARELGMT GDYWGQGTLVTVSS<br>SEQ ID NO: 28516 |
| iPS:392922 | 21-225_30G4 | NA | GACATCCAGATGACCCAGTCTCCACCCTCCCT GTCTACATCTGTAGGAGACAGAGTCACCATCA CTTGCCGGGCAACTCAGAACATTTCAGTCTAT TTAAATTGGCATCAGCAGAAACCAGGGAAAG CCCCTAAGCTCCTGATCCATATGCATCCAGTT TGCAAGTGGTGGGTCCCATCAAGGTTCAGTGGC AGTGGATCTGGGACAGATTTCACTCTCACCAT CATCAGTATGCAACCTGAAGATTTTCCACTT ACTACTGTCAACTCAGTACAGTCCCCCGTAC ACTTTTGGCGGAGGGACCAAGGTGGAGATCA AA<br>SEQ ID NO: 24511 | CAGGTGCAGTTGGTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCCGGGGGCT GGAATGGGTGGCAGTTATATGTATGATGGAACT GATAAATACTATGTAGACTCCGTGAAGGGCCGAT TCACCATCTCCAGAGACAATTCCAAGAACACGCT GTATCTGCAAATGAACAGCCTGAGAGCCGAGGA CTCGGCTGTGTATTACTGTGCGAGAGAAAATAGC AGCTCGTACTACTTTGACTACTGGGGCCAGGAA CCCTGGTCACCGTCTCCTCA<br>SEQ ID NO: 28517 |
| | | AA | DIQMTQSPPSLSTSVGDRVTITCRATQNIFSYLN WHQQKPGKAPKLLIHTASSLQGGVPSRFSGSGS GTDFTLTIISMQPEDFSTYYCQLSYSPPYTFGGGT KVEIK<br>SEQ ID NO: 24512 | QVQLVESGGGVVQPGRSLRLSCAASGFTFSSYGMH WVRQAPGRGLEWVAVIWYDGTDKYYVDSVKGRF TISRDNSKNTLYLQMNSLRAEDSAVYYCARENSSS YYFDYWGQGTLVTVSS<br>SEQ ID NO: 28518 |

FIGURE 50
(Continued)

| | | | | |
|---|---|---|---|---|
| iPS:392924 | 21-225_32H2 | NA | GATATTGTGATGACCCAGACTCCACTCTCT GTCCGTCACCCCTGACAGCGGCCTCCATCT CCTGCAGGTCTAGTCAGAGCCTCCTCCATAGT GATGGAAGGACCTATTTGTATTGGTACCTGCA GAAGCCAGGCCAGCCTCCACAGCTCCTGATCT ATGAACTTTCCAACCGGTTCTGAGTGCCA GATAGGTTCAGTGGCAGCGGGTCAGGACAG ATTTCACACTGAAAATCAGCGGGTGGAGGCT GAGGATGTTGGGATTTATTCCTGCTTGCAAAG TATACAATATCCCATCACCTTCGGCCAAGGGA CACGACTGGAGATTAAA SEQ ID NO: 24513 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAATACTATGCAGAGACTCCGTGAAGGCCGA TTCACCATCTCCAGAGACAATTCCAAGAACACGC TGAATCTGCAAATGAACAGCCTGAGAGCCGAGG ACACGGGTGTGTATTACTGTGCGAGAGATATAG CAGCAGCTGGACGGGGGGTATGGACGTCTGGGG CCAAGGGACCACGGTCACCGTCTCCTCA SEQ ID NO: 28519 |
| | | AA | DIVMTQTPLSLSVTPGQPASISCRSSQSLLHSDGR TYLYWYLQKPGQPPQLLIYELSNRFSGVPDRFSG SGSGTDFTLKISRVEAEDVGIYSCLQSIQYPITFG QGTRLEIK SEQ ID NO: 24514 | QVQLVESGGGVVQPGRSLRLSCAASGFTFSSYGMH WVRQAPGKGLEWVAVIWYDGSNKYYADSVKGRF TISRDNSKNTLNLQMNSLRAEDTGVYYCARRYSSS WTGGMDVWGQGTTVTVSS SEQ ID NO: 28520 |
| iPS:392928 | 21-225_25A4 | NA | GACATCGTGATGACCCAGTTTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGGAATCCGGGGTC CCTGACCGATTCAGTGGCAGCGGGTCTGGGAC AGAATTCACTCTCACCATCAGCAGCCTGGAGG CTGAAGATGTGGCAGTTATTATTACTGTCAGCAG TATTATAGTACTCCTCGACGTTCGGCCAAGG GACCAAGGTGAAATCAAA SEQ ID NO: 24515 | CAGGTGCTCCTGGTGCAGTCTGGGGCTGAGGTGA AGAAGCCTGGGGCCTCAGTGAAGGTCTCCTGCA AGGCTTCTGGATACACCTTCACCAATTATGATAT TAATTGGGTGCGACAGGCCACTGGACAAGGGCT TGAGTGGATGGGATGGATGTACACAGAAATTCCAGGGCAGA AACACAGGCTATGCACAGGAACACCTCCATAAGCACA GTCACCATGACCAGGGACACGTCGAGATCTGAG GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTCTCCTCA SEQ ID NO: 28521 |

FIGURE 50
(Continued)

| | | | |
|---|---|---|---|
| iPS:392930 | 21-225_25H9 | AA | DIVMTQFPDSLAVSLGERATIKCKSSQSVLYSSH NNNYLAWYQQKPGQPPKLLLYWASTRESGVPD RFSGSGSGTEFTLTISSLEAEDVAVYYCQQYYST PPTFGQGTKVEIK<br>SEQ ID NO: 24516 | QVLLVQSGAEVKRPGASVKVSCKASGYTFTNYDIN WVRQATGQGLEWMGWMYPNSGNTGYAQKFQGR VTMTRNTSISTAYMELSSLRSEDTAVYYCASSSGW YYFDYWGQGTLVTVSS<br>SEQ ID NO: 28522 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GATGGAAAGACCTATTTGTTTTGGTACCTGCA GAAGCCAGGCCAGCCTCCACAGCTCCTGATCT ATGAAGTTTCCAATCGGTTCTCTGGAGTGCCA GATAGGTTCAGTGGCAGCGGGTCAGGGACAG ATTTCACACTGAAAATCAGCGGGTGGAGGCT GAGGATGTTGGGGTTTATTACTGCATGCAAAG TATACAGCTTCCGTGGACGTTCGGCCAAGGGA CCAAGGTGGAAATCAAA<br>SEQ ID NO: 24517 | CAGGTGCAGCTGGTGGAGTCTGGGGGAGGCGTG GTCCAGCCTGGGAGGTCCCTGAGACTCTCCTGTG CAGCGTCTGGATTCCCCTTCAATAACTATGGCAT GCACTGGGTCCGCCAGGCTCCAGGCAAGGGCT GGAGTGGGTGTCAATTATATGGTATGATGAAGT TATAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAGGATAC GATTTTTGAGTGGCTTCTTTGACTCTCTGGGCC AGGGAACCCTGGTCACCGTCTCCTCA<br>SEQ ID NO: 28523 |
| | | AA | DIVMTQTPLSLSVTPGQPASISCKSSQSLLHGDG KTYLFWYLQKPGQPPQLLIYEVSNRFSGVPDRFS GSGSGTDFTLKISRVEAEDVGVYYCMQSIQLPW TFGQGTKVEIK<br>SEQ ID NO: 24518 | QVQLVESGGGVVQPGRSLRLSCAASGFPFNNYGM HWVRQAPGKGLEWVSIIWYDGSYKYYADSVKGRF TISRDNSKNTLYLQMNSLRAEDTAVYYCAREGYDF WSGFFDSWGQGTLVTVSS<br>SEQ ID NO: 28524 |

FIGURE 50
(Continued)

| | | | |
|---|---|---|---|
| iPS:392934 | 21-225_27D5 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAACAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A SEQ ID NO: 24519 | CAGGTGCAACTGGTGGAGTCTGGGGGAGGCGTG GTCCAGCCTGGGAGGTCCCTGAGACTCTCCTGT GCAGCCGTCTGGATTCACCTTCAGTAGCTATGGCAT GCACTGGGTCCGCCAGGCTCCAGGCAAGGGCT GGAGTGGGTGGCAGTTATATGGTATGATGAAAGT AATAAATACTATGGAGACTCCGTGAAGGGCCGA TTCACCATCTCCAGAGACAATTCCAAGAATATGC TGTATCTGCAAATGAACAGCCTGAGAGCCGAGG ACACGGCTCTGTATTACTGTGCGAGAGAACTGGG GTTCCTCTGACTACTGGGGCCAGGGAACCCTG GTCACCGTCTCCTCA SEQ ID NO: 28525 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK SEQ ID NO: 24520 | QVQLVESGGGVVQPGRSLRLSCAASGFTFSSYGMH WVRQAPGKGLEWVAVIWYDESNKYYGDSVKGRF TISRDNSKNMLYLQMNSLRGEDTALYYCARELGFL SDYWGQGTLVTVSS SEQ ID NO: 28526 |
| iPS:392936 | 21-225_28B6 | NA | GATGTTGTGATGACTCAGTCTCCACTCTCCCTG CCCGTCACCCTTGGACAGCCGGCCTCCATCTC CTGCCGGTCTAGTCAAAGCCTGTATAGTG ATGGAGACACCAACTTGAATTGGTTTCAGCAG AGGCCAGGCCAATCTCCAAGGCGCCAAATTTA TAAGGTTTCTAACTGGGACTCTGGGGTCCCAG ACAGATTCAGCGGCAGTGGGTCAGGCACTGAT TTCACACTGAAACATCAGCAGGGTGGAGGCTGA GGATGTTGGGATTTATTTCTGCATGCATTGTAC ACACTGGCTCCTTTTCGGCCCTGGGACCAAAG TGGATATCAAA SEQ ID NO: 24521 | CAGGTGCTCCTGGTGCAGTCTGGGGCTGAGGTGA AGAGGCCTGGGGCCTCAGTGAAGGTCTCCTGCA AGGCTTCTGGATACACCTTCACCAATTATGATAT TAATTGGGTGCGACAGGCCACTGGACAAGGTCTT GAGTGGATGGGATGGATGCACCCTGACAGTGGT AACACAGGCTATGCACAGAAGTTCCAGGGCAGA GTCACCATGACCAGGAACACCTCCATAAGCACG GCCTACATGGAGCTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTCTCCTCA SEQ ID NO: 28527 |

FIGURE 50
(Continued)

| | | | |
|---|---|---|---|
| iPS:392938 | 21-225_29H4 | AA | DVVMTQSPLSLPVTLGQPASISCRSSQSLVYSDG DTYLNWFQQRPGQSPRRQIYKVSNWDSGVPDRF SGSGSGTDFTLNISRVEAEDVGIYFCMHCTHWLL FGPGTKVDIK<br>SEQ ID NO: 24522 | QVLLVQSGAEVKRPGASVKVSCKASGYTFTNYDIN WVRQATGQGLEWMGWMHPDSGNTGYAQKFQGR VTMTRNTSISTAYMELSSLRSEDTAVYYCASSSGW YYFDYWGQGTLVTVSS<br>SEQ ID NO: 28528 |
| | | NA | GATATTGTGATGACCCAGACTCCACTCTCTCT GTCCGTCACCCCTGGACAGCCGGCCTCCTTCT CCTGCAAGTCTAGTCAGAGCCTCCTGCATAGT GATGGAAAGACCTATTTGTATTGGTACCTGCA GAAGCCAGGCCAGTCCACAGCTCCTGGACTGCCA TTGAGGTTTCCCACCGGTTCTCTGGACTGCCA GATAGGTTCAGTGGCAGCGGGTCAGGGACAG ATTTCACACTGAAAATCAGCGGGGTGGAGCT GAGGATGTTGGGGTTTATTACTGCATGCAAAG TATACAGCATCCGTTCACTTTCGGCGGAGGGA CCAGGGTGGAGATCAAA<br>SEQ ID NO: 24523 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT ACACTGGGTCCGCCAGGCTCCAGGCAAGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCAGGGGTATGGACGTCTGGGG CCAAGGGACCACGGTCACCGTCTCCTCA<br>SEQ ID NO: 28529 |
| | | AA | DIVMTQTPLSLSVTPGQPASFSCKSSQSLLHSDG KTYLYWYLQKPGQPPQLLIFEVSHRFSGLPDRFS GSGSGTDFTLKISRVEAEDVGVYYCMQSIQHPFT FGGGTRVEIK<br>SEQ ID NO: 24524 | QVQLVESGGGVVQPGRSLRLSCAASGFTFSSYGIH WVRQAPGKGLEWVAVIWYDGSNKYYADSVKGRF TISRDNSKNTLYLQMNSLRAEDTAVYYCARRYSSS WSGGMDVWGQGTTVTVSS<br>SEQ ID NO: 28530 |

FIGURE 50
(Continued)

| | | | |
|---|---|---|---|
| iPS:392940 | 21-225_29D9 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTTTCAGCAGAAACCGGGGAAAGC CCCTAAGCGCCTGATCTATGCTGCATCCAGTT GCAAAGTGGGGTCCCATCAAGGTTCAGCGGCA GTGGATCTGGGACAGAGAATTCACTCTCACAATC AGCAGCCTGCAGCCTGAAGATATACTTACCCATTCAC TTACTGTCTACAGCATAATACTTACCCATTCAC TTTCGGCCCTGGGACCAAAGTGGATTTCAAA<br>SEQ ID NO: 24525 | CAGGTGCAGCTGGTGGTGGAGTCTGGGGGAGGCGTG GTCCAGCCTGGGAGGTCCCTGAAACTCTCCTGT CAGCGTCTGGATTCACCTTCAGTGACTATGGCAT TCACTGGGTCCGCCAGGCTCCAGGCAAGGGCT GGAGTGGGTGGCAGTTATATGGTATGATGAAAGT AATAACTATTACGAGACTCCGTGAAGGGCCGAT TCACCATCTCCAGAGACAATTCCAAGAACACGCT GTATCTGCAAATGAACAGCCTGAGAGCCGAGA CACGGCTGTGTACTACTGTGCGAGAGAAATTGGC TGGTTAGATGACTACTGGGGGCCAGGGAACCCAG GTCACCGTCTCCTCA<br>SEQ ID NO: 28531 |
| | | AA | DIQMTQSPSSLSASVGDRVTITCRASQGIRNDLG WFQQKPGKAPKRLIYAASSLQSGVPSRFSGSGSG TEFTLTISSLQPEDFATYYCLQHNTYPFTFGPGTK VDFK<br>SEQ ID NO: 24526 | QVQLVESGGGVVQPGRSLKLSCSASGFTFSDYGIH WVRQAPGKGLEWVAVIWYDESNNYYADSVKGRF TISRDNSKNTLYLQMNSLRAEDTAVYYCAREIGWL DDYWGQGTQVTVSS<br>SEQ ID NO: 28532 |
| iPS:392942 | 21-225_30E9 | NA | GACATCCAGATGACCCAGTCTCCATCCTCCCT GTCTGCATCTGTAGGAGACAGAGTCACCATCA CTTGCCGGGCAAGTCAGGACATTAGAGATGAT TTAGGCTGGTATCAGCAGAAACCAGGGAAAG CCCCTAGGCGCCTGATCTATGGTGCATTCAGC TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAGTAGTACCCTCCT ACTTTCGCGCGAGGGACCAAGGTGGAGATCA AA<br>SEQ ID NO: 24527 | GAGGTGCAGGTGTTGGAGTCTGGGGGAGGCTTG GTACAGCCTGGGGGGTCCCTGAGACTCTCCTGTG CAGCCTCTGGATTCACCTTTAGCAGCTGTGCCAT GAACTGGGTCCGCCAGGCTCCAGGGAAGGGGCT GGAGTGGGTCTCCGTCATTAGTGGTGGTGGTGGT AGCACATTCTACGCAGACTCCGTGAAGGGCCGGT TCACCATCTCCAGAGACAATTCCAAGAACACGCT GTATCTGCAAATGAACAGCCTGAGAGCCGAGA CACGGCCGTATATTACTGTGCGAAAGGGAGCT ACTAGAGGACTACTACTACTACGGAATGACGTC TGGGGCCAAGGGACCACGGTCACCGTCTCCTCA<br>SEQ ID NO: 28533 |

FIGURE 50
(Continued)

| | | | | |
|---|---|---|---|---|
| | | AA | DIQMTQSPSSLSASVGDRVTITCRASQDIRDDLG WYQQKPGKAPRRLIYGAFSLQSGVPSRFSGSGS GTEFTLTISSLQPEDFATYYCLQHTSYPPTFGGGT KVEIK | EVQVLESGGGLVQPGGSLRLSCAASGFTFSSCAMN WVRQAPGKGLEWVSAISGRGGSTFYADSVKGRFTI SRDNSKNTLYLQMNSLRAEDTAVYYCAKGELLED YYYYGMDVWGQGTTVTVSS |
| | | | SEQ ID NO: 24528 | SEQ ID NO: 28534 |
| iPS:392944 | 21-225_31H5 | NA | GACATCCAGATGACCCAGTCTCCATCCTCCCT GTCTGCATCTGTAGGAGACAGATTCACCATCT CTTTCCGGCAAGTCAGGACATTAGAAGTGAT TTAGGCTGGTATCAGCAGAAACCAGGAAAG CCCATAAGGCGCATCATCTATGCTGCATCCAGT TTGCAAAGTGGGGTCCCATCAAGGTTCAGCGT CAGTGGATCTGGGACAGATTCACTTTCACAA TCAGCAGCATGCAGCCTGACGATTTTCAAAT TATTACTGTATACAACATATTATTACCCTCCT ACTTTCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCCGCTATTAGTGGTCGTGGTGGA AGCATATTCCACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGTGAAAGGGGAGCTA CTAGAGGACTACTACTTCTACGGTATGGACGTCT GGGGCCAAGGGACCACGGTCACCGTCTCCTCA |
| | | | SEQ ID NO: 24529 | SEQ ID NO: 28535 |
| | | AA | DIQMTQSPSSLSASVGDRFTISFRASQDIRSDLGW YQQKPGKAHKRIIYAASSLQSGVPSRFSVSGSGT EFTFTISSMQPDDFSNYYCIQHIIYPPTFGGGTKV EIK | EVQLLESGGGLVQPGGSLRLSCAASGFTFSSYAMS WVRQAPGKGLEWVSAISGRGGSIFHADSVKGRFTI SRDNSKNTLYLQMNSLRAEDTAVYCVKGELLED YYFYGMDVWGQGTTVTVSS |
| | | | SEQ ID NO: 24530 | SEQ ID NO: 28536 |

FIGURE 50
(Continued)

| | | | |
|---|---|---|---|
| iPS:392948 | 21-225_25G5 | NA | GACATCCAGATGACCCAGTCTCCATCCTCACTGTCTGCATCTGTTGGAGACAGAGTCACCATCACTTGCCGGGCAAGTCAGAGACATTAGAAATGATTTAGGCTGGTATCAGCAGAAACCAGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAGTCAGCAGCCTGCAGCCTGAAGATTTTGCAACTTATTACTGTCTACAGCATAATAGTTACCCCTTCACTTTCGGCCCTGGGACCAAAGTGGATATCAAA<br><br>SEQ ID NO: 24531 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGGCATACACTGGGTCCGCCAGGCTCCAGGCAAGGGGCTGGAGTGGGTGGCAGTTATTTGGTATGATGGAAATAATAAATATTATGCAGACTCCGTGAAGGGCCGATTCACCATCTCCAGAGACAATGAACAACTGAGAGCCGAGGATACGGCTGTGTATTACTGTGCGAGAGAAATTGGCTGGTTAGATGACTACTGGGGCCAGGGAACCCTGGTCACCGTCTCCTCA<br><br>SEQ ID NO: 28537 |
| | | AA | DIQMTQSPSSLSASVGDRVTITCRASQDIRNDLGWYQQKPGKAPKRLIYAASSLQSGVPSRFSGSGSGTEFTLTVSSLQPEDFATYYCLQHNSYPFTFGPGTKVDIK<br><br>SEQ ID NO: 24532 | QVQLVESGGGVVQPGRSLRLSCAASGFTFSDYGIHWVRQAPGKGLEWVAVIWYDGNNKYYADSVKGRFTISRDNSKNTLYLQMNLRAEDTAVYYCAREIGWLDDYWGQGTLVTVSS<br><br>SEQ ID NO: 28538 |
| iPS:392950 | 21-225_25C10 | NA | GACATCCAGATGACCCAGTCTCCATCCTCACTGTCTGCATCTGTAGGAGACAGAGTCACCATCACTTGTCGGGCGAGTCAGGGCATTAGCAGCGCATTAGCCTGGTTTCAGCAGAAACCAGGGAAAGCCCCTAAGTCCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGTCAACAGTATCATAGTTACCATTCACTTTCGGCCCTGGGACCAAAGTGGATATCAAA<br><br>SEQ ID NO: 24533 | GAGGTGCAGTTGGTGGAGTCTGGGGGAGGCTTGGTACAGCCTGGGGGGTCCCTGAGACTCTCCTGTGCAGCCTCTGGATTCACCTTCAGTAGCTATAGGATGAACTGGGTCCGCCAGGCTCCAGGGAAGGGGCTGGAGTGGGTTTCATCCATTAGTAGTAGTAGTACCATATACTACGCAGACTCTGTGAAGGGCCGATTCACCATCTCCAGAGACAACGCCAAGAACTCACTGTATCTGCAAATGAACAGCTGAGAGACGGCTGTTCACCGGCTGTGTATTACTGTGCGAGAACCGGCTGGTTTGACTACTGGGGCCAGGGAACCCTGGTCACCGTCTCCTCA<br><br>SEQ ID NO: 28539 |

FIGURE 50
(Continued)

| | | | | |
|---|---|---|---|---|
| iPS:392952 | 21-225_26G1 | AA | DIQMTQSPSSLSASVGDRVTITCRASQGISNYLA WFQQKPGKAPKSLIYAASSLQSGFPSKFSGSGSG TDFTLTISSLQPEDFATYYCQQYHSYPFTFGPGT KVDIK<br><br>SEQ ID NO: 24534 | EVQLVESGGGLVQPGGSLRLSCAASGFTFSSYRMN WFQQAPGKGLEWVSSISSSSTIYYADSVKGRFTIS RDNAKNSLYLQMNSLRDEDTAVYYCARTAGFDY WGQGTLVTVSS<br><br>SEQ ID NO: 28540 |
| | | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTATGCTGCATCCAGTTT GCGAAGTGGGGTCCCATCAAACTTCAGCGGCA GTGGATCTGGGACAGATTTCACTCTCACCATC AGCAGCCTGCAGCCTGAAGATTTTGCAACTTA TTACTGCCAACAGTATCATAGTTACCCATTCA CTTTCGGCCCTGGGACCAAAGTGGATATCAAA<br><br>SEQ ID NO: 24535 | GAGGTGCAGCTGGTGGTGGAGTCTGGGGGAGGCCTG GTCAAGCCTGGGGGTCCCTGAGACTCTCCTGTG CAGCCCTCTGGATTCACCTTCAGTAGCTATGCAT GAACTGGGTCCGCCAGGCTCCAGGGAAGGGGCT GGAGTGGGTCTCATCCATTAGTGGTAGTAGTAGT TACATATACTACGCGGACTCAGTGAAGGCCGAT TCACCATCTCCAGAGACAACGCCAAGAACTCACT GTATCTGCAAATGAACAGCCTGAGAGCCGAGGA CACGGCTGTGTATTACTGTGCGAGACTGACTACC TTTGACTTCTGGGGCCAGGGAACCCTGGTCACCG TCTCCTCA<br><br>SEQ ID NO: 28541 |
| | | AA | DIQMTQSPSSLSASVGDRVTITCRASQDISNYLA WFQQKPGKAPKSLIYAASSLRSGVPSNFSGSGSG TDFTLTISSLQPENFATYYCQQYHSYPFTFGPGT KVDIK<br><br>SEQ ID NO: 24536 | EVQLVESGGGLVKPGGSLRLSCAASGFTFSSYGMN WVRQAPGKGLEWVSSISGSSSYIYYADSVKGRFTIS RDNAKNSLYLQMNSLRAEDTAVYYCARLTFDFW GQGTLVTVSS<br><br>SEQ ID NO: 28542 |

FIGURE 50
(Continued)

| | | | |
|---|---|---|---|
| iPS:392954 | 21-225_26A10 | NA | GACATCCAGATGACCCAGTCTCCATCCTCCT GTCTGCATCTGTAGGAGACAGAATCACCATCA CTTGCCGGGCAAGTCAGAGCATTAGCAGCTAT TTAAATTGGTATCAGCAGAAACCAGGGAAAG CCCCTAAGGTCCTGATCTATGCTGCATCCAGC TTGCAAAGTGGGGTCCCATCAAGATTCAGTGG CAGTGGATCTGGGACAGATTTCACTCTCACCA TCAGCAGTCTGCAACCTGAAGATTTTGCAACT TACTACTGTCAACAGAGTTACAGTACCCCTAC GTGGACGTTCGGCCAAGGGACCAAGGTGGAA ATCAAA <br><br> SEQ ID NO: 24537 | GAGGTGCAGCTGCTGGAGTCTGGGGGAGGCTTG GTACAGCCTGGGGGGTCCCTGAGACTCTCCTGTG CAGCCCTCTGATTCACCTTTAGCAGCTATGCCAT GAGCTGGGTCCGCCAGGCTCCAGGGAAGGGTCT GGAGTGGGTCTCAGTTATTAGTGGTAGTGGTGTT AACACATTCTACGCAGACTCCGTGAAGGGCCGGT TCACCATCTCCAGAGACAATTCCAAGAACACGCT GTATCTGCTAATGAACAGCCTGAGAGCCGAGGA CACGGCCGTATATTACTGTGCGAAAAGATAGC AGTGGCTGGTACTCACTACTTTGACTACTGGGGC CAGGGAACCCTGGTCACCGTCTCCTCA <br><br>SEQ ID NO: 28543 |
| | | AA | DIQMTQSPSSLSASVGDRITITCRASQSISSYLNW YQQKPGKAPKVLIYAASSLQSGVPSRFSGSGSGT DFTLTISSLQPEDFATYYCQQSYSTPTWTFGQGT KVEIK <br><br> SEQ ID NO: 24538 | EVQLLESGGGLVQPGGSLRLSCAASGFTFSSYAMS WVRQAPGKGLEWVSVISGSGVNTFYADSVKGRFTI SRDNSKNTLYLLMNSLRAEDTAVYYCAKKIAVAG THYFDYWGQGTLVTVSS <br><br>SEQ ID NO: 28544 |
| iPS:392956 | 21-225_27A11 | NA | GACATCCAGATGACCCAGTCTCCCTCTTCCGT GTCTGCATCTGTCGTAGGAGACAGAGTCACCATCA CTTGTCGGGCGAGTCAGGGTATTAGTAGTTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGCC AGTGGATCTGGGACAGATTTCACTCTCACCAT CAGCAGCCTGCAGCCTGAAGATTTTGCAACTT ACTGTTGTCAACAGTGTGACAGTTTCCCTCGG ACGTTCGGCCAAGGGACCAAGGTGGAAATCA AA <br><br>SEQ ID NO: 24539 | CAGGTGCAGCTGGTGGAGTCTGGGGGAGGCGTG GTCCAGCCTGGGGAGGTCCCTGAGACTCTCCTGTG CAGCGTCTGGATTCACCTTCAGCAGTATGCAT GCACTGGGTCCGCCAGGCTCCAGGCAAGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TATATCTACAAATGAACAGCCTGAGAGCCGAGG ACACGGCTGTGTATCACTGTGCGAGAGATTCCTC CCCTACGGTATGGACGTCTGGGGCCAAGGGAC CACGGTCACCGTCTCCTCA <br><br>SEQ ID NO: 28545 |

FIGURE 50
(Continued)

| | | AA | DIQMTQSPSSVSASVGDRVTITCRASQGISSWLA WYQQKPGKAPKLLIYGASSLQSGVPSRFSASGS GTDFTLTISSLQPEDFATYCCQQSDSFPRTFGQGT KVEIK<br><br>SEQ ID NO: 24540 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYHCARDSSPY GMDVWGQGTTVTSS<br><br>SEQ ID NO: 28546 |
|---|---|---|---|---|
| iPS:392958 | 21-225_28C7 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATACTTACCCGTGG ACGTTCGGCCAAGGGACCAAGGTGGAAATCA AA<br><br>SEQ ID NO: 24541 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTATGGATGAAAGT AATAAATACTATGCAGACTCCGTGAAGGGCCGA TTCACCATCTCAGAGACAATTCCAAGAACACGC TGTATCTGCAAATGAACAGCCTGAGAGCCGAGG ACACGGCTGTGTATTACTGTGCGAGAGAATTAGG CTGGTACGACGACTACTGGGGCCAGGGAACCCT GGTCACCGTCTCCTCT<br><br>SEQ ID NO: 28547 |
| | | AA | DIQMTQSPSSLSASVGDRVTITCRASQGIRNDLG WYQQKPGKAPKRLIYIASSLQSGVPSRFSGSGSG TEFTLTISSLQPEDFATYYCLQHNTYPWTFGQGT KVEIK<br><br>SEQ ID NO: 24542 | QVQLVESGGGVVQPGRSLRLSCAASGFTFSSYGMH WVRQAPGKGLEWVAVIWYDESNKYYADSVKGRF TISRDNSKNTLYLQMNSLRAEDTAVYYCARELGW YDDYWGQGTLVTVSS<br><br>SEQ ID NO: 28548 |

FIGURE 50
(Continued)

| | | | |
|---|---|---|---|
| iPS:392960 | 21-225_29E6 | NA | GACATCGTGATGACCCAGTTTCCAGACTCCCT GGCTGTGTCTCTGGGCGAGAGGGCCACCATCA ACTGTAAGTCCAGCCAGAGTGTTTTATACAGC TCCCACAATAACTACTACTTAACTGGTACCA GCAGAAACCAGGACAGCCTCATAAGTTGCTCC TTTACTGGGCATCTTCCCGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCTCGACGTTCGGCCAAGG GACCAAGGTGGAAATCAAA<br><br>SEQ ID NO: 24543 | CAGGTGCTCCTGGTGCAGTCTGGGGCTGAGGTGA AGAGGCCTGGGGCCTGGGTCTCAGTGAAGGTCTCCTGCA AGGCTTCTGGATACACCTTCACCAATTATGATAT TAATTGGGTGCGACAGGCCACTGGACAAGGCT TGAGTGGATGGGATGGATGCACCTAACAGTGGT AACACAGGCTATGCACAGAAATTCCAGGGCAGA GTCACCATGACCAGGAACACCTCCATAAGCACA GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTCCTCA<br><br>SEQ ID NO: 28549 |
| | | AA | DIVMTQFPDSLAVSLGERATINCKSSQSVLYSSH NNYYLTWYQQKPGQPHKLLIYWASSRESGVPD RFSGSGSGTEFTLTISSLQAEDVAVYYCQQYYST PPTFGQGTKVEIK<br><br>SEQ ID NO: 24544 | QVLLVQSGAEVKRPGASVKVSCKASGYTFTNYDIN WVRQATGQGLEWMGWMHPNSGNTGYAQKFQGR VTMTRNTSISTAYMELSSLRSEDTAVYYCASSSGW YYFDYWGQGTLVTVSS<br><br>SEQ ID NO: 28550 |
| iPS:392962 | 21-225_30A1 | NA | GACATCCAGATGACCCAGTCTCCATCCTCACT GTCTGCATCTGTAGGAGACAGAGTCACCATCA CTTGTCGGGCAGTCAGGGCATTAGCAATTAT TTAGCCTGGTTTCAGCAGAAACCAGGGAAAGC CCCTAAGTCCCTGATCTCTGCTGCATCCAGTTT GCAAACTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGAGTATATAGTTACCATTCA CTTTCGGCCCTGGGACCAAAGTGGATATCAAA<br><br>SEQ ID NO: 24545 | GAGGTGCAGCTGTTGGAGTCTGGGGGAGGCCTG GTACAGCCGGGGGGGTCCCTGAGACTCTCCTGTG CAGCCTCTGGATTCACCTTTAGCAGCTATGTCAT GAACTGGGTCCGCCAGGCTCCAGGGAAGGGGCT GGAGTGGGTCTCAGTCTATTAGTGGTAGTGGTGGT AGCACATACTACGCAGACTCCGTGAAGGGCCGG TTCACCATCTCCAGAAACACAATTCCAAGAACACGC TGTATCTGCAAATGAACAGCCTGAGAGCCGAGG ACACGGCCGTATATTACTGTGCGCGAACTGGGGT CTTTGACTACTGGGGCCAGGGAACCCTGGTCACC GTCTCCTCA<br><br>SEQ ID NO: 28551 |

FIGURE 50
(Continued)

| | | | | |
|---|---|---|---|---|
| | | AA | DIQMTQSPSSLSASVGDRVTITCRASQGISNYLA WFQQKPGKAPKSLISAASSLQTGVPSKFSGSGSG TDFTLTISSLQPEDFATYYCQQYNSYPFTFGPGT KVDIK<br><br>SEQ ID NO: 24546 | EVQLLESGGGLVQPGGSLRLSCAASGFTFSSYVMN WVRQAPGKGLEWVSAISGSGGSTYYADSVKGRFTI SRNNSKNTLYLQMNSLRAEDTAVYYCARTGVFDY WGQGTLVTVSS<br><br>SEQ ID NO: 28552 |
| iPS:392964 | 21-225_31A8 | NA | GACATCCAGATGACCCAGTCTCCATCCTCCCT GTCTGCATCTGTAGGAGACAGAGTCACCATCA CTTGCCGGGCAAGTCAGGACATTAGAAGTGAT CTTAGGCTGGTATCAGCAGAAACCAGGGAAAG CCCCTAAGCGCCTGATCTATGCTGTATCCAGTT TGCAAAGTGGGGTCCCATCAAGGTTCAGCGGC AGTGGCTCTGGGACAGAATTCACTCTCACAAT CAGCAGCCTGCAGCCTGAAGATTTTGCCACTT ATTACTGTCTACAGCATACTATTTACCCTCCTA CTTTCGGCGGAGGGACCAAGGTGGAGATCAA A<br><br>SEQ ID NO: 24547 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGACGAGG ACACGGCCGTATATTACTGTGTGAAAGGGGAGCT ACTAGAGGACTACTACTTCTACGTATGGACGTC TGGGGCCAAGGGACCACGGTCACCGTCTCCTCA<br><br>SEQ ID NO: 28553 |
| | | AA | DIQMTQSPSSLSASVGDRVTITCRASQDIRSDLG WYQQKPGKAPKRLIYAVSSLQSGVPSRFSGSGS GTEFTLTISSLQPEDFATYYCLQHTIYPPTFGGGT KVEIK<br><br>SEQ ID NO: 24548 | EVQLLESGGGLVQPGGSLRLSCAASGFTFSSYAMS WVRQAPGKGLEWVSAISGRGGSTFHADSVKGRFTI SRDNSKNTLYLQMNSLRDEDTAVYYCVKGELLED YFYGMDVWGQGTTVTVSS<br><br>SEQ ID NO: 28554 |

FIGURE 50
(Continued)

| | | | |
|---|---|---|---|
| iPS:392966 | 21-225_32G3 | NA | GACATCCAGATGACCCAGTCTCCATCCTCACT GTCTGCATCTGTCGGAGACAGAGTCACCATCA CTTGTCGGGCGAGTCAGGCATTAGCAATTAT TTAGCCTGGTTTCAGCAGAAACCAGGGAAAGC CCCTAAGTCCCTGATCTATGATACATCCAGTTT GCAAAGTGGGGTCCCATCAAAATTCAGCGGCA GTGGGTCTGGGACAGATTTCACTCTCACCATC AGCACCCTACAGCCTGAAGATTTTGCAACTTA TTACTGCCAACAGTATCATAGTTACCCGCTCA CTTTCGGCGGAGGGACCAAGGTGGAGATCAA G SEQ ID NO: 24549 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGATCAGTGAAGGCCGAT TCACCATCTCCAGAGACAACGCCAAGAACTCACT GTATCTGCAAATCAACAGCCTGAGAGCCGAGA CACGGCTGTGTATTACTGTGCGAGAGGCAATATA GCAAGGGACTACTGGGGCCAGGGAACCCTGGTC ACCGTCTCCTCA SEQ ID NO: 28555 |
| | | AA | DIQMTQSPTSLSASVGDRVTITCRASQAISNYLA WFQQKPGKAPKSLIYDTSSLQSGVPSKFSGSGSG TDFTLTISTLQPEDFATYYCQQYHSYPLTFGGGT KVEIK SEQ ID NO: 24550 | EVQLVESGGGLVKPGGSLRLSCAASGFTFSSYSMN WVRQAPGKGLEWVSSISGSSSYIYADSVKGRFTIS RDNAKNSLYLQINSLRAEDTAVYYCARGNIARDY WGQGTLVTVSS SEQ ID NO: 28556 |
| iPS:392968 | 21-225_25B6 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAAG CCCCTAAGCGCCTGATCTATCGTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A SEQ ID NO: 24551 | CAGGTGCAGCTGGTGGAGTCTGGGGGAGGCGTG GTCCAGCCTGGGAGGTCCCTGAGAGTCTCCTGTA CAGCGTCTGGATTCACCTCAGAAACTATGGCAT GCACTGGGTCCGCCAGGCTCCAGGCAAGGGGCT GGAGTGGGTGGCAGTTATATGGTATGAGGAAAG TAATAAATACTATACAGAGTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAACTGG GGTTCCTCTCTCGACTACTGGGGCCAGGGAACCCT GGTCACCGTCTCCTCA SEQ ID NO: 28557 |

FIGURE 50
(Continued)

| | | | |
|---|---|---|---|
| | | AA | DIQMTQSPSSLSASVGDRVTITCRASQGIRNDLG WYQQKPGKAPKRLIYRASSLQSGVPSRFSGSGS GTEFTLTISSLQPEDFATYYCLQHNSYPFTFGPGT KVDIK<br>SEQ ID NO: 24552 | QVQLVESGGGVVQPGRSLRVSCTASGFTLRNYGM HWVRQAPGKGLEWVAVIWYEESNKYYTESVKGR FTISRDNSKNTLYLQMNSLRAEDTAVYYCARELGF LSDYWGQGTLVTVSS<br>SEQ ID NO: 28558 |
| iPS:392972 | 21-225_26A2 | NA | GACATCCAGATGACCCAGTCTCCATCCTCCCT GTCTGCATCTGTAGGAGACAGAGTCACCATCA CTTGCCGGGCAAGTCAGGGCATTAGAAGTGAT TTAGGCTGGTATCAGCAGAAACCAGGGAAAG CCCCTAAGCGCCTGATCTATAGAGGCATCCAGT TTGCAGAGTGGGGGTCCCATCAAGATTCAGCGG CAGTGGATCTGGGACAGAATTCACTCTCACAT TCAGCAGCCTGCAGCCTGAAGATTTTGCAACG TATTACTGTCTACAGCATAATCGTTACCCGTG GACGTTCGGCCAAGGGACCAAGGTGGAAATC AAA<br>SEQ ID NO: 24553 | CAGGTGCAGCTGGTGGAGTCTGGGGGAGGCGTG GTCCAGCCTGGGAGGTCCCTGAGACTCTCCGTG CAGCGTCTGGATTCACCTTCAGTAGCTATGGCAT GCACTGGGTCCGCCAGGCTCCAGGCAAGGGCT GGAGTGGGTGGCAGTTATATGACTCCGTGAAGGGCCGA TAATAAATACTATGTAGAGACTCCGTGAAGGGCCGA TTCACCATCTCAGAGACAATTCACAAGAACACGC TGTATCTGCAAATGAACAGCCTGAGAGCCGAGG ACACGGCTGTGTATTACTGTGCGAGAGAATTAGG CTGGTACGACGACTACTGGGGCCAGGGAACCCT GGTCACCGTCTCCTCA<br>SEQ ID NO: 28559 |
| | | AA | DIQMTQSPSSLSASVGDRVTITCRASQGIRSDLG WYQQKPGKAPKRLIYTASSLQSGVPSRFSGSGSG TEFTLTFSSLQPEDFATYYCLQHNRYPWTFGQGT KVEIK<br>SEQ ID NO: 24554 | QVQLVESGGGVVQPGRSLRLSCAASGFTFSSYGMH WVRQAPGKGLEWVAVIWYEGSNKYYVDSVKGRF TISRDNSKNTLYLQMNSLRAEDTAVYYCARELGW YDDYWGQGTLVTVSS<br>SEQ ID NO: 28560 |

FIGURE 50
(Continued)

| | | | |
|---|---|---|---|
| iPS:392974 | 21-225_26A11 | NA | GACATCCAGATGACCCAGTCTCCAATTTCCT GTCTGCATCTGTAGGAGACAGAGTCACCATCA CTTGCCGGGCAAGTCAGGCCATTAGAAATGAT TTAGGCTGGTATCAGCAGAGACCAGGAAAG CCCCTAAGCGCCTGATCTATGCTGCATCCAGT TTGCAAAGTGGGGTCCCATCAAGGTTCAGCGG CAGTGGATCTGGGACAGAATTATTCTCACAA TCAGCAGCCTGCAGCCTGAAGATTTTGCAACT TATTACTGTCTACAGCATTATAATTACCCTGC AGTTTTGGCCAGGGGACCAAGCTGGAGATCAG A |  |
| | | | SEQ ID NO: 24555 | SEQ ID NO: 28561 |
| | | AA | DIQMTQSPISLSASVGDRVTITCRASQAIRNDLG WYQQRPGKAPKRLIYAASSLQSGVPSRFSGSGS GTEFILTISSLQPEDFATYYCLQHYNYPRSFGQGT KLEIR | QVQLVESGGGVVQPGRSLRLSCAASGFTFSNCVMH WVRQAPGKGLEWVAVIWYDGSNKYYADSVKGRF TISRDNSKNTLYLQMNSLRAEDTAVYYCAREEYSS GWYDYGMDVWGQGTTVTVSS |
| | | | SEQ ID NO: 24556 | SEQ ID NO: 28562 |
| iPS:392976 | 21-225_27H12 | NA | GACATCCAGATGACCCAGTCTCCATCCTCACT GTCTGCATCTGTAGGAGACAGAGTCACCATCA CTTGTCGGGCGAGTCAGGGATCAGCAATTAT TTAGCCTGGTTTCAGCAGAAACCAGGGAAAGC CCCTAAGTCCCTGATCAATGGTGCATCCAGT TGCAAAGTGGGGTCCCATCAAGTTCAGCGGC AGTGGATCTGGGACAGATTTCACTCTCACCAT CAGCAGCCTGCAGCCTGAAGATTTTGCAACTT ATTACTGCCAACAGTATTATAGTTACCCATTC ACTTTCGGCCCTGGGACCAAAGTGAATATCAA T | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCCT GAACTGGGTCCGCCAGGCTCCAGGGAAGGGGCT GGAGTGGGTCTCATCATTAGTGGTAGTAGTAGT AACATATACTACCAGATCAGTGAAGGGCGA TTCACCATCTCCAGAGACAACGCCAAGAACTCAC TGTTTCTGCAAATGAACAGCTGAGAGCCGAGG ACACGGCTGTGTATTACTGTGCGAGAGTGGCGTC CTTTGACTACTGGGGCCAGGGAACCCTGGTCACC GTCTCCTCA |
| | | | SEQ ID NO: 24557 | SEQ ID NO: 28563 |

FIGURE 50
(Continued)

| | | | |
|---|---|---|---|
| | | AA | DIQMTQSPSSLSASVGDRVTITCRASQGISNYLA WFQQKPGKAPKSLNGASSLQSGVPSKFSGSGSG TDFTLTISSLQPEDFATYYCQQYSYPFTFGPGT KVNIN<br><br>SEQ ID NO: 24558 | EVQLVESGGGLVKPGGSLRLSCAASGFTFSSYSLN WVRQAPGKGLEWVSSISGSSSNIYYTDSVKGRFTIS RDNAKNSLFLQMNSLRAEDTAVYYCARVASFDYW GQGTLVTVSS<br><br>SEQ ID NO: 28564 |
| iPS:392978 | 21-225_28B8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTTTCAGCACAAACCAGGAAAG CCCCTAAGCGCCTGATCTATGCTGCATCCAGT TTGCAAAGTGGGGTCCCATCAAGGTTCAGCGG CAGTGGATCTGGGACAGGATTCACTCTCACAA TCAGCAGCCTGCAGCCTGAAGATTTTGCAACT TATTACTGTCTACAGCATATAAGTTACCCATTC ACTTTCGGCCCTGGGACCAAAGTGGATATCAA T<br><br>SEQ ID NO: 24559 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTGACTGGCAT GCACTGGGTCCGCCAGGCTCCAGGCAAGGGCT GGAGTGGGTGACAGTTATATGTATGATGCAAAT AATAAATACTATGCAGACTCCGTGAAGGGCCGA TTCACCATCTCAGAGACAATTCAAAACACGG TGTATCTGCAAATGAACAGCCTGAGAGCCGAGG ACACGGCTGTGTATTACTGTGCGAGAGAAATTGG CTGGTTAGATGACTACTGGGGCCAGGGAACCCTG GTCACCGTCTCCTCA<br><br>SEQ ID NO: 28565 |
| | | AA | DIQMTQSPSSLSASVGDRVTITCRASQGIRNDLG WYQHKPGKAPKRLIYAASSLQSGVPSRFSGSGS GTEFTLTISSLQPEDFATYYCLQHNSYPFTFGPGT KVDIN<br><br>SEQ ID NO: 24560 | QVQLVESGGGVVQPGRSLRLSCAASGFTFSDYGM HWVRQAPKGLEWVTVIWYDANNKYYADSVKGR FTISRDNFKNTVYLQMNSLRAEDTAVYYCAREIGW LDDYWGQGTLVTVSS<br><br>SEQ ID NO: 28566 |

FIGURE 50
(Continued)

| | | | |
|---|---|---|---|
| iPS:392980 | 21-225_29H6 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAATCAGGGAAAA CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGTCTGCAGCCTGAAGATTTTGCAACC TATTACTGTCTACAGCATAATAGTTACCCGCTC ACTTTCGGCGGAGGGACCAAGGTGGAGATCA AA SEQ ID NO: 24561 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGACAGTTATATGGTATAATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GATGACGGGTGACTCCTGGGGCCAGGGAACCCT GGTCACCGTCTCCTCA SEQ ID NO: 28567 |
| | | AA | DIQMTQSPSSLSASVGDRVTITCRASQGIRNDLG WYQQKSGKTPKRLIYAASSLQSGVPSRFSGSGSG TEFTLTISSLQPEDFATYYCLQHNSYPLTFGGGT KVEIK SEQ ID NO: 24562 | QVQLVESGGGVVQPGRSLRLSCAASGFTFSDYGM HWVRQAPGKGLEWVTVIWYNENNKYYADSVKGR FTISRDNSKNTLYLQMNSLRAEDTAVYYCARELGM TGDSWGQGTLVTVSS SEQ ID NO: 28568 |
| iPS:392982 | 21-225_30D1 | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAACAGAAACCAGGGAAAG CCCCTGAGCGCCTGATCTATGCTGCATCCAGT TTGCAAAGTGGGGTCCCATCAAGGTTCAGCGG CAGTGGATCTGGGACAGCCTGAAGATTTTACAACT TCAGCAGCCTGCAGCCTGAAGATATTTACCCTCCT ACTTTCGGCGGAGGGACCAAGGTGGAGATCA AA SEQ ID NO: 24563 | GAGGTGCAGGTGTTGGAGTCTGGGGGAGGCTTG GTACAGCCTGGGGGGTCCCTGAGACTCTCCTGTG CAGCCTCTGGATTCACCTTTAGCAGTCATGCCAT GAGCTGGGTCCGCCAGGCTCCAGGGAAGGGGCT GGAGTGGGTCTCCGTCATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATTACTGTGTGAAAGGGGAGCT ACTAGAGGACTACTACTTCTACGGTTTGACGTC TGGGGCCAAGGGACCACGGTCACCGTCTCCTCA SEQ ID NO: 28569 |

FIGURE 50
(Continued)

| | | | |
|---|---|---|---|
| iPS:392984 | 21-225_30E11 | AA | DIQMTQSPSSLSASVGDRVTITCRASQDIRSDLG WYQQKPGKAPERLIYAASSLQSGVPSRFSGSGSG TEFTLTISSLQPEDFTTYYCLQHTIYPPTFGGGTK VEIK<br>SEQ ID NO: 24564 | EVQVLESGGGLVQPGGSLRLSCAASGFTFSSYAMS WVRQAPGKGLEWSAISGRGGSTFHADSVKGRFTI SRDNSKNTLYLQMNSLRAEDTAVYYCVKGELLED YYFYGLDVWGQGTTVTVSS<br>SEQ ID NO: 28570 |
| | | NA | GACATCCAGATGACCCAGTCTCCATCCTCCCT GTCTGCATCTGTAGGAGACAGAGTCACCATCA CTTGCCGGGCAAGTCAGAGCATTAGCAACTAT TTAAATTGGTATCAACAGCAAACAGGGAAAG CCCCTAAGTTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCATTC ACTTTCGGCCCTGGGACCAAAGTGGATATCAA A<br>SEQ ID NO: 24565 | GAGGTGCAGCTGTTGGAGTCTGGGGGAGACATG GTCCAGCCTGGGGGGTCCCTGAGACTCTCCTGTG CAGCCTCCGGATTCACCTTTAGCAGCTATGCCAT GAGCTGGGTCCGCCAGGCTCCAGGGAAGGGGCT GGAGTGGGTCTCAGTTATTAGTGGTAGTGGTGGT AGTCATTCTACGCAGACTCCGTGAAGGGCCGGT TCACCATCTCCAGAGACAATTCCAAGAACACGCT GTATCTGCAAATGAACAGCTGAGAGCCGAGGA CACGGCCGTATATTACTGTGTACGAAAGATCGGGTG AAAGCTCATGATGGTTTTGATATCTGGGGCCAAG GGACAATGGTCACCGTCTCCTCA<br>SEQ ID NO: 28571 |
| | | AA | DIQMTQSPSSLSASVGDRVTITCRASQSISNYLN WYQQQTGKAPKFLIYAASSLQSGVPSRFSGSGS GTDFTLTISSLQPEDFATYYCQQSYSTPFTFGPGT KVDIK<br>SEQ ID NO: 24566 | EVQLLESGGDMVQPGGSLRLSCAASGFTFSIYAMS WVRQAPGKGLEWVSVISGSGGSSFYADSVKGRFTI SRDNSKNTLYLQMNSLRAEDTAVYYCTKDRVKAH DGFDIWGQGTMVTVSS<br>SEQ ID NO: 28572 |

FIGURE 50
(Continued)

| | | | |
|---|---|---|---|
| iPS:392986 | 21-225_31B8 | NA | GACATCCAGATGATCCAGTCTCCATCCTCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGGTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATATTATTACCCTCCT ACTTTCGGCGGAGGGACCAAGGTGGAGATCA AA<br><br>SEQ ID NO: 24567 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTGGTGGTGT AGCACATTCCACGCAGACTCCGTGAAGGGCCGG TTCACCATCTCCAGAGACAATTCCAAGAACACGC TGTATCTACAACTGAACAGCCTGAGAGCCGATGA CACGGCCGTATATTACTGTGTGAAAGGGAGCTA CTAGAGGACTACTTCTACGGTATGGACGTCT GGGGCCAAGGGACCACGGTCACCGTCTCCTCA<br><br>SEQ ID NO: 28573 |
| | | AA | DIQMIQSPSSLSASVGDRVTITCRASQDIRSDLGW YQQKPGKAPKRLIYGASSLQSGVPSRFSGSGSGT EFTLTISSLQPEDFATYYCLQHIIYPPTFGGGTKV EIK<br><br>SEQ ID NO: 24568 | EVQLLESGGGLVQPGGSLRLSCAASGFTFSSYAMS WVRQAPGKGLEWVSAISGRGGSTFHADSVKGRFTI SRDNSKNTLYLQLNSLRADDTAVYYCVKGELLED YYFYGMDVWGQGTTVTVSS<br><br>SEQ ID NO: 28574 |
| iPS:392988 | 21-225_25E6 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCCGCGG CAGTGGATCTGGGACAGATTTCACTCTCACAA TCAACAGTCTGCAGCCTGAAGATTTTGCAACC TATTACTGTCTACAGCATAATAGTTACCCGCTC ACTTTCGGCGGAGGGACCAAGGTGGAGATCA AA<br><br>SEQ ID NO: 24569 | CAGGTGCAGCTGGTGGAGTCTGGGGGAGGCGTG GTCCAGCCTGGGAGGTCCCTGAGACTCTCCTGTG CAGCGTCTGGATTCAGTTCACCTTCAGTGACTATGGCAT GCACTGGGTCCGCCAGGCTCCAGGCAAGGGGCT GGAGTGGGTGGCAGTTATATGCTCCGTGAAGGGCCGA AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTCTGTATTACTGTGCGACAGAACTGGG GATGACGGTGACTCCTGGGGCCAGGGAACCCT GGTCACCGTCTCCTCA<br><br>SEQ ID NO: 28575 |

FIGURE 50
(Continued)

| | | | | |
|---|---|---|---|---|
| iPS:392990 | 21-225_25H10 | AA | DIQMTQSPSSLSASVGDRVTITCRASQGIRNDLG WYQRKPGKAPKRLIYAASSLQSGVPSRFRGSGS GTEFTLTINSLQPEDFATYYCLQHNSYPLTFGGG TKVEIK<br>SEQ ID NO: 24570 | QVQLVESGGGVVQPGRSLRLSCAASGFTFSDYGM HWVRQAPGKGLEWVAVIWYDENNKYYADSVKGR FTISRDNSKNTLYLQMNSLRAEDTALYYCATELGM TGDSWGQGTLVTSS<br>SEQ ID NO: 28576 |
| | | NA | GACATCCAGATGACCCAGTCTCCATCCTCCCT GTCTGCATCTGTAGGAGACAGAGTCACCATCA CTTGCCGGGCAAGTCGGGCATTAGAAATGAT TTAGGCTGGTATCAGCAGAAACCAGGAAAG CCCCTAAGCGCCTGATCTATGCTGCATTCAGT TGCAAAGTGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAGTTACCCGCTC ACTTTCGGCGGAGGGACCAAGGTGGAGATCA AA<br>SEQ ID NO: 24571 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGAAAGT AATAAATACTATGCAGACTCCATGAAGGGCCGA TTCACCATCTCAGAGACAATTCCAAGAACACGC TGTATCTGCAAATGAACAGCCTGAGAGCCGAGG ACACGGCTGTGTATTACTGTGCGAGAGAACTGGG GATGACGGGTGACTACTGGGGCCAGGGAACCCT GGTCACCGTCTCCTCA<br>SEQ ID NO: 28577 | |
| | | AA | DIQMTQSPSSLSASVGDRVTITCRASRGIRNDLG WYQQKPGKAPKRLIYAAFSLQSGVPSRFSGSGS GTEFTLTISSLQPEDFATYYCLQHNSYPLTFGGG TKVEIK<br>SEQ ID NO: 24572 | QVQLVESGGGVVQPGRSLRLSCAASGFTFSDYGM HWVRQAPGKGLEWVAVIWYDESNKYYADSMKGR FTISRDNSKNTLYLQMNSLRAEDTAVYYCARELGM TGDYWGQGTLVTVSS<br>SEQ ID NO: 28578 |

FIGURE 50
(Continued)

| | | | | |
|---|---|---|---|---|
| iPS:392992 | 21-225_26C4 | NA | GACATCGTGATGACCCAGTCTCCAGACTCCCT GGCTGTGTCTCTGGGCGAGAGGGCCACCATCA ACTGCAAGTCCAGCCAGAGTGTTTTATACCGC TCCAACAATTACAACTACTTAGCTTGGTACCA GCACAAACCAGGACAGCCTCCTAAGCTGCTCA TTTACTGGGCATCTACCCGGGAATCGGGGTC CCTGACCGCTTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCCTCGACGTTCGGCCAAGG GACCAAGGTGGAATTCAAA SEQ ID NO: 24573 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCTGTGACAAGGGC TTGAGTGGATGGGATGGATGAACCTAACAGTG GTAACACAGGCTATGCACAGAGATTCCAGGCA GAGTCACCATGACCAGGAACACCTCCATAACA CAGCCTACATGGAGCTGAGCAGCCTGAGATCTG AGGACACGGCCGTATATTACTGTGCGAGTAGCA GTGGCTGGTACTACTTTGACTACTGGGGCCAGGG AACCCTGGTCACCGTCTCCTCA SEQ ID NO: 28579 |
| | | AA | DIVMTQSPDSLAVSLGERATINCKSSQSVLYRSN NYNYLAWYQHKPGQPPKLLIYWASTRESGVPD RFSGSGSGTDFTLTISSLQAEDVAVYYCQQYYST PPTFGQGTKVEFK SEQ ID NO: 24574 | QVQLVQSGAEVKKPGASVKVSCKASGYTFTNYDIN WVRQASGQGLEWMGWMNPNSGNTGYAQRFQGR VTMTRNTSINTAYMELSSLRSEDTAVYYCASSSGW YYFDYWGQGTLVTVSS SEQ ID NO: 28580 |
| iPS:392994 | 21-225_26G11 | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GAAGGAAAGACCTATTTGTATTGGTACCTGCA GAAGCCAGGCCAGCCTCCACACCTCCTGATCT ATGAAGTTTCCAACCGGTTCTCTGGAGTGCCA GATAGGTTCAGTGGCAGCGGGTCAGGGACAG ATTTCACACTGAAAATCAGCGGGGTGCAGGCT GAGGATGTTGGGATTTATTACTGCATGCAAAG TATAAAGCTTCCGCTCACTTTCGGCGGAGGGA CCAAGGTGGAGATCAAA SEQ ID NO: 24575 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAACAGCTGGTCAGGGGTATGACGTCTGGGG CCAAGGGACCACGGTCACCGTCTCCTCA SEQ ID NO: 28581 |

FIGURE 50
(Continued)

| | | | |
|---|---|---|---|
| iPS:392996 | | AA | DIVMTQTPLSLSVTPGQPASISCKSSQTLLHGEGK TYLYWYLQKPGQPPHLLIYEVSNRFSGVPDRFSG SGSGTDFTLKISRVEAEDVGIYYCMQSIKLPLTFG GGTKVEIK<br>SEQ ID NO: 24576 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSNS WSGGMDVWGQGTTVTSS<br>SEQ ID NO: 28582 |
| | 21-225_28B1 | NA | GACATCCAGATGACCCAGTCTCCATCTTCCGT GTCTGCATCTGTAGGAGACAGAGTCACCATCA CTTGTCGGGCGAGTCAGGCTATCAATGACTGG TTAGCCTGGTATCAGCAGAAACCAGGGAAAG CCCCTAAGCTCCTGATCTATGCTGCATCCAGTT TCCAAAGTGGGGTCCCATCCAAGGTTCAGCGGC AGTGGATCTGGGACAGATTTCACTCTCACCAT CACCAGCCTGCAGCCTGAAGATTTTGCAACTT ACTATTGTCAACAGGCTAGCAGTTTCCCATTC ACTTTCGGCCCTGGGACCAAAGTGGATATCAA A<br>SEQ ID NO: 24577 | GAGGTGCAGCTGTTGGAGTCTGGGGGAGGCTTG GTACAGCCTGGGGGGTCCCTGAGATTGTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGAGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGAAATTGGGGCGT ATAGCAGTGACTGGTCCTTACTTTGACTACTGGG GCCAGGGAACCCTGGTCACCGTCTCCTCA<br>SEQ ID NO: 28583 |
| | | AA | DIQMTQSPSSVSASVGDRVTITCRASQAINDWLA WYQQKPGKAPKLLIYAASSFQSGVPSRFSGSGSG TDFTLTITSLQPEDFATYYCQQASSFPFTFGPGTK VDIK<br>SEQ ID NO: 24578 | EVQLLESGGGLVQPGGSLRLSCAASGFTFSSYAMS WVRQAPGKGLEWVSAISGSGGNTFYADSVKGRFTI SRDNSKNTLYLQMNSLRAEDTAVYYCAKLGRIAV TGPYFDYWGQGTLVTVSS<br>SEQ ID NO: 28584 |

FIGURE 50
(Continued)

| | | | | |
|---|---|---|---|---|
| iPS:392998 | 21-225_28A9 | NA | GACATCCAGATGACCCAGTCTCCATCCTCCCT GTCTGCATCTGTAGGAGACAGAGTCACCATCA CTTGCCGGGCAAGTCAGGACAGTCATTAGAAATGAT TTAGGCTGGTATCAGCAGAAACCAGGGAAAG CCCCTAAGCGCCTGATCTATGCTGCTTCTAGTT TGCAAAATGGAGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATAATCGTTACCATTCA CTTTCGGCCCTGGGACCAAGTGGATATCAA SEQ ID NO: 24579 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTATGGCAT ACACTGGGTCCGCCAGGCTCCAGGCAAGGGGCT GGAGTGGGTGGCAGTTATATGCAGACTCCGTGAAGGGCCGA AATAAATACTATGCAGACTCCGTGAAGGGCCGA TTCACCATCTCCAGAGACAATTCCAAGAACACGC TGTTTCTGCAAATGAACAGCCTGAGAGTCGAGGA CACGGCTGTGTATTACTGTGCGAGAGAAATTGGC TGGTTAGATGACTACTGGGGCCAGGGAACCCTG GTCACCGTCTCCTCA SEQ ID NO: 28585 |
| | | AA | DIQMTQSPSSLSASVGDRVTITCRASQGIRNDLG WYQQKPGKAPKRLIYAASSLQNGVPSRFSGSGS GTEFTLTISSLQPEDFATYYCLQHNRYPFTFGPGT KVDIK SEQ ID NO: 24580 | QVQLVESGGGVVQPGRSLRLSCAASGFTFSSYGIH WVRQAPGKGLEWVAVIWFDGSNKYYADSVKGRF TISRDNSKNTLFLQMNSLRVEDTAVYYCAREIGWL DDYWGQGTLVTVSS SEQ ID NO: 28586 |
| iPS:393000 | 21-225_29D7 | NA | GACATCCAGATGACCCAGTCTCCATCCTCCCT GTCTGCATCTGTAGGAGACAGAGTCACCATCA CTTGCCGGGCAAGTCAGGACAGTCATTAGAAATGAT TTAGGCTGGTATCAACAGAAACCAGGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCATTC ACTTTCGGCCCTGGGACCAAAGTGGATATCAA A SEQ ID NO: 24581 | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGAAAGT AATAAATACTATGCAGACTCCGTGAAGGGCCGA TTCACCATCTGCAAATGAACAGCCTGAGAGACACGC TGTATCTGCAAATGAACAGCCTGAGAGGAGG ACACGGCTCTGTATTACTGTGCGAGAGAACTGGG GTTCCTCTCTGACTACTGGGGCCAGGGAACCCTG GTCACCGTCTCCTCA SEQ ID NO: 28587 |

FIGURE 50
(Continued)

| | | | | |
|---|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK | QVQLVESGGGVVQPGRSLRLSCAASGFTFSSYGMH WVRQAPGKGLEWVAVIWYDESNKYYGDSVKGRF TISRDNSKNTLYLQMNSLRGEDTALYYCARELGFL SDYWGQGTLVTVSS |
| | | | SEQ ID NO: 24582 | SEQ ID NO: 28588 |
| iPS:393002 | 21-225_30G1 | NA | GACATCCAGATGACCCAGTCTCCATCCTCCCT GTCTGCATCTGTAGGAGACAGAGTCACCATCA CTTGCCGGGCAAGTCAGAACATTTACAGTAT TTAAATTGGTATCAGCAGAAACCAGGGAAAG ACCCTAAGCTCCTGATCTATGCTGCATCCAGT TGCATAGTGTGGGGTCCCGTCACGGTTCAGTGGC AGTGGTTCTGGGACAGATTTCACTCTCACCAT CAGCAGTCTGCAACCTGAAGATTTTGCAACTT ACTACTGTCAACAGAGTTACAGTACTCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGACTCCGTGAAGGGCCGA TAATAAATACTATGTAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAATAG CAGTTCGTACTACTTTGACTACTGGGGCCAGGGA ACCCTGGTCACCGTCTCCTCA |
| | | | SEQ ID NO: 24583 | SEQ ID NO: 28589 |
| | | AA | DIQMTQSPSSLSASVGDRVTITCRASQNIYSYLN WYQQKPGKDPKLLIYAASSLHSGVPSRFSGSGS GTDFTLTISSLQPEDFATYYCQQSYSTPLTFGGGT KVEIK | QVQLVESGGGVVQPGRSLRLSCAASGFTFSYYGM HWVRQAPGKGLEWVAVIWHDGSNKYYVDSVKGR FTISRDNSKNTLYLQMNSLRAEDTAVYYCARENSS SYYFDYWGQGTLVTVSS |
| | | | SEQ ID NO: 24584 | SEQ ID NO: 28590 |

FIGURE 50
(Continued)

| | | | |
|---|---|---|---|
| iPS:393004 | 21-225_30G11 | NA | GACATCCAGATGACCCAGTCTCCATCCTCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCGGCAGCCTGCAGCCTGAAGATTTTGCAACT TATTTCTGTCTACAGCATACTATTTACCCTCCT ACTTTCGGCGGAGGGACCAAGGTGGAGATCA AA <br><br>SEQ ID NO: 24585 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTCGTGGTGGT AGCACATTCAACGCAGACTCCGTGAAGGGCCGG TTCACCATCTCCAGAGACAATTCCAAGACCACGC TGTATCTGCAAATGAACAGCCTGAGAGCCGAGG ACACGGCCGTATATTACTGTGTGAAAGGGAGCT ACTAGAGGACTACTACTTCTACGGTATGGACGTC TGGGGCCAAGGGACCACGGTCACCGTCTCCTCA <br><br>SEQ ID NO: 28591 |
| | | AA | DIQMTQSPSSLSASVGDRVTITCRASQDIRSDLG WYQQKPGKAPKRLIYAASSLQSGVPSRFSGSGS GTEFTLTIGSLQPEDFATYFCLQHTIYPPTFGGGT KVEIK <br><br>SEQ ID NO: 24586 | EVQLLESGGGLVQPGGSLRLSCAASGFTFSSYAMS WVRQAPGKGLEWVSAISGRGGSTFNADSVKGRFTI SRDNSKTTLYLQMNSLRAEDTAVYYCVKGELLED YYFYGMDVWGQGTTVTVSS <br><br>SEQ ID NO: 28592 |
| iPS:393006 | 21-225_31G9 | NA | GACATCCAGATGACCCAGTCTCCATCCTCCCT GTCTGCATCTATAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATCCTGCATCCAGT TGCAAAGTGGGGTCCCATCAAGGTTCAGCGGC AGTGGATCTGGGACAGAGTTCACTCTCACAAT CAGCAGCCTGCAGCCTGAAGATTTTGCAACTT ATTACTGTCTACAGGATAATAGTTACCCTTTCA CTTTCGGCCCTGGGACCAAAGTGGATATCAAA <br><br>SEQ ID NO: 24587 | GAGGTGCAGCTGTGGTGGAGTCTGGGGGAGGCCTG GTCAAGCCTGGGGGGTCCCTGAGACTCTCCTGTG CAGCCTCTGGATTCACCTTCAGTAGCTAGCTATAGCAT GAACTGGGTCCGCCAGGCTCCAGGGAAGGGGCT GGAGTGGGTCTCATCAATTAGTAGTAGTAGTAGT TACATATACTACCAGAGACTCAGTGAAGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGAGGC AGCAGCTGGGGCCAGGGAACCCTGGTCACCGTC TCCTCA <br><br>SEQ ID NO: 28593 |

FIGURE 50
(Continued)

| | | | | |
|---|---|---|---|---|
| | | AA | DIQMTQSPSSLSASIGDRVTITCRASQGIRNDLG WYQQKPGKAPKRLIYPASSLQSGVPSRFSGSGSG TEFTLTISSLQPEDFATYYCLQDNSYPFTFGPGTK VDIK<br><br>SEQ ID NO: 24588 | EVQLVESGGGLVKPGGSLRLSCAASGFTFSSYSMN WVRQAPGKGLEWVSSISSSSYIYYADSVKGRFTIS RDNAKNSLYLQMNSLRAEDTAVYYCARDRGSSW GQGTLVTVSS<br><br>SEQ ID NO: 28594 |
| iPS:393010 | 21-225_25E11 | NA | GACATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTATACTGCATCCAGTT TGCAAGGTGGGGTCCCATCAAGGTTCAGCGGC AGTGGATCTGGGACAGATTTCACTATCAGCAT CAGCAGCCTGCAGCCTGAAGATTTTGCAACTT ACTATTGTCAACAGGCTAACAGTTTCCCAATC ACTTTCGGCCCTGGGACCAAAGTGGATATCAA A<br><br>SEQ ID NO: 24589 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTGGTGGTGGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAACGTGGATA TAGTGGCTACGAGGACCTCCTCTACTTTGACTGC TGGGGCCAGGGAACCCTGGTCACCGTCTCCTCA<br><br>SEQ ID NO: 28595 |
| | | AA | DIQMTQSPSSVSASVGDRVTITCRASQGISNWLA WYQQKPGKAPKLLIYTASSLQGGVPSRFSGSGS GTDFTISISSLQPEDFATYYCQQANSFPITFGPGT KVDIK<br><br>SEQ ID NO: 24590 | EVQLLESGGGLVQPGGSLRLSCAASGFTFSSYAMS WVRQAPGKGLEWVSVISGGGGSTYYADSVKGRFT ISRDNSKNTLYLQMNSLRAEDTAVYYCAKRGYSG YEDLLYFDCWGQGTLVTVSS<br><br>SEQ ID NO: 28596 |

FIGURE 50
(Continued)

| | | | | |
|---|---|---|---|---|
| iPS:393012 | 21-225_26G7 | NA | GATATCTTGATGACCCAGACTCCACTCTCTG TCCGTCACCCCTGGAGAGCAGCCGGCTCCATCTC CTGCAAGTCTAGTCAGAGCCTCCTGCATAGTG AGGGAAAGACCTATTTGTATGGTACCTGCAG AAGCCAGGCCAGCCTCCACAGTTCCTGATCTA TGAAGTTCCACCGGCTCTCTGGAGTGCCAG ATAGGTTCAGTGGCAGCGGGTCAGGGACAGA TTTCACACTGAAAATCAGCCGGTTGAGGCTG AGGATGTTGGGGTTTATTACTGCATGCAAAGT ATACAGCTTCCGCTCACTTTCGGCGGAGGGAC CAAGGTGGAGATCAAA SEQ ID NO: 24591 | CAGGTGCAGCTGGTGGAGTCTGGGGGAGGCGTG GTCCAGCCTGGGAGGTCCCTGAGACTGTCCTGTG CAGCCTCTGGATTCACCTTCAGTAGCTATGGCAT GCACTGGGTCCGCCAGGCTCCAGGCAAGGGCT GGAGTGGGTGGCAGTTATATGCAGACTCCGTGAAGGGCCGAT AATAAATATTATGCAGACTCCGTGAAGGGCCGAT TCACCATCTCCAGAGACACAATTCCAATAACACGCT GTATCTGCAAATGAACAGCCTGAGAGCCGAGGA CACGGCTGTGTATTACTGTGCGAGAAGGTATAGC AGCAGCTGGTCAGGGGGTATGGACGTCTGGGGC CAAGGGACCACGGTCACCGTCTCCTCA SEQ ID NO: 28597 |
| | | AA | DILMTQTPLSLSVTPGQPASISCKSSQSLLHSEGK TYLYWYLQKPGQPPQFLIYEVSHRLSGVPDRFSG SGSGTDFTLKISRVEAEDVGVYYCMQSIQLPLTF GGGTKVEIK SEQ ID NO: 24592 | QVQLVESGGGVVQPGRSLRLSCAASGFTFSSYGMH WVRQAPGKGLEWVAVIWYDGSNKYYADSVKGRF TISRDNSNNTLYLQMNSLRAEDTAVYYCARRYSSS WSGGMDVWGQGTTVTVSS SEQ ID NO: 28598 |
| iPS:393014 | 21-225_26D12 | NA | GACATCCAGATGACCCAGTCTCCCCTCTCCGT GTCTGCATCTGTAGGAGACAGAGTCACCATCA CTTGTCGGGCGAGTCAGGGTATTAGTAGTTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGCC AGTGGATCTGGGACAGATTTCACTCTCACCAT CAGCAGCCTGCAGCCTGAAGATTTTGCAACTT ACTGTTGTCAACAGTCTGACAGTTCCCTCGG ACGTTCGGCCAAGGGACCAAGGTGGAAATCA AA SEQ ID NO: 24593 | CAGGTGCAGCTGGTGGAGTCTGGGGGAGGCGTG GTCCAGCCTGGGAGGTCCCTGAGACTCTCCTGTG CAGCCTCTGGATTCACCTTCAGCAGTTATGGCAT GCACTGGGTCCGCCAGGCTCCAGGCAAGGGCT GGAGTGGGTGGCAGTTATATGGATATGGATGAAGT AATGAATACTATGCAGACTCCGTGAAGGGCCGA TTCACCATCTCCAGAGACAATTCCAAGAACACGC TATATCTACAAATGAACAGCCTGAGAGCCGCGG ACACGGCTGTGTATTACTGTGCGAGAGATTCCTC CCCTACGGTATGGACGTCTGGGGCCAAGGGAC CACGGTCACCGTCTCCTCA SEQ ID NO: 28599 |

FIGURE 50
(Continued)

| | | AA | DIQMTQSPSSVSASVGDRVTITCRASQGISSWLA WYQQKPGKAPKLLIYGASSLQSGVPSRFSASGS GTDFTLTISSLQPEDFATYCCQQSDSFPRTFGQGT KVEIK<br><br>SEQ ID NO: 24594 | QVQLVESGGGVVQPGRSLRLSCAASGFTFSSYGMH WVRQAPGKGLEWVAVIWYDGSNEYYADSVKGRF TISRDNSKNTLYLQMNSLRAADTAVYYCARDSSPY GMDVWGQGTTVTSS<br><br>SEQ ID NO: 28600 |
|---|---|---|---|---|
| iPS:393016 | 21-225_28F11 | NA | GACATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTCTGCTGCATCCAATT TGCAAAGTGGGTCCCATCAAGGTTCAGAGGC AGTGGATCTGGGACAGATTTCACTCTCACCAT CACCAGCCTGCAGCCTGAAGATTTTGCAACTT ACTGTTGTCAACAGGCTAACAGTCTCCCATTC ACTTTCGGCCCTGGGACCAAAGTGGATATCAA A<br><br>SEQ ID NO: 24595 | GAGGTGCAGCTGTTGGAGTCTGGGGGAGGCTTG GTACAGCCGGGGGGGTCCCTGAGACTCTCCTGTG CAGCCTCTGGATTCATCTTTAGCAGCTATGCCAT GAGCTGGGTCCGCCAGGCTCCAGGGAAGGGGCT GGAGTGGGTCTCAGTTACTACTAGTGGTGGTGGT ACCACATTCTACGCAGACTCCGTGAAGGGCCGGT TCACCATCTCCAGAGACAATCCAAGAACACGCT TTATCTGCAAATGAACAGCTGAGAGCCGAGGA CACGGCCGTTTATTACTGTGCGAAACGGACCCAG TTTGATGATTTTGATATCTGGGGCCAAGGGACAA TGGTCACCGTCTCTTCA<br><br>SEQ ID NO: 28601 |
| | | AA | DIQMTQSPSSVSASVGDRVTITCRASQGISNWLA WYQQKPGKAPKLLISAASNLQSGVPSRFRGSGS GTDFTLTITSLQPEDFATYCCQQANSLPFTFGPGT KVDIK<br><br>SEQ ID NO: 24596 | EVQLLESGGGLVQPGGSLRLSCAASGFIFSSYAMS WVRQAPGKGLEWVSVTSGSGGTFYADSVKGRFT ISRDNSKNTLYLQMNSLRAEDTAVYYCAKRTQFDD FDIWGQGTMVTVSS<br><br>SEQ ID NO: 28602 |

FIGURE 50
(Continued)

| | | | |
|---|---|---|---|
| iPS:393018 | 21-225_29B8 | NA | GACATCCAGATGACCCAGTCTCCATCCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTAGATCTGGGACAGAATTCACTCTCACAA TCAGCAGTCTGCAGCCTGAAGATTTTGCAACC TATTACTGTCTACAGCATAATAGTTACCCGCTC ACTTTCGGCGGAGGGACCAAGGTGGAGATCA AA SEQ ID NO: 24597 | CAGGTGCAGCTGGTGGAGTCTGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGGTATGATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GATGACGGGTGACTCCTGGGGCCAGGGAACCCT GGTCACCGTCTCCTCA SEQ ID NO: 28603 |
| | | AA | DIQMTQSPSSLSASVGDRVTITCRASQGIRNDLG WYQQKPGKAPKRLIYAASSLQSGVPSRFSGSRS GTEFTLTISSLQPEDFATYYCLQHNSYPLTFGGG TKVEIK SEQ ID NO: 24598 | QVQLVESGGGVVQPGRSLRLSCAASGFTFSDYGM HWVRQAPGKGLEWVAVIWYDENNKYADSVKGR FTISRDNSKNTLYLQMNSLRAEDTAVYYCARELGM TGDSWGQGTLVTVSS SEQ ID NO: 28604 |
| iPS:393020 | 21-225_30E2 | NA | GACATCCAGATGACCCAGTCTCCACATTCCCT GTCTGCATCTGTAGGAGACAGAGTCACCATCA CTTGCCAGGCGAGTCAGTACATTAGCAACTAT TTAAATTGGTATCAGCAGCAGAAATCAGGAAAGC CCCTAAGCTCCTGATCTACGATGATCCAGTT TGGAAACAGGGGTCCCATCAAGGTTCAGTGGA AGTGGATCTGGGACAGATTTACTTCACCAT CAGCAGCCTGCAGCCTGAAGATCTTGCAACAT ATTACTGTCAACAGTATGATAATCTCCGATC ACCTTCGGCCAAGGGACACGACTGGAGATTAA A SEQ ID NO: 24599 | CAGGTGCAGCTGGTGGAGTCTGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATCATATGGTGGAAGT AATAAATTCTATGCAGTCTCCGTGAAGGGCCGAT TCAACATCTCCAGAGACAATTCCAAGAACACGCT GTATCTGCAAATGAACAGCCTGAGAGCTGAGGA CACGGCTGTGTATTACTGTGTGAGAAGGGGTAT AGCAGTGGAGCTACGGTATGGACGTCTGGGGC CAAGGGACCACGGTCACCGTCTCCTCA SEQ ID NO: 28605 |

FIGURE 50
(Continued)

| | | | |
|---|---|---|---|
| iPS:393022 | 21-225_30H11 | AA | DIQMTQSPHSLSASVGDRVTITCQASQYISNYLN WYQQKSGKAPKLLIYDGSSLETGVPSRFSGSGSG TDFTFTISSLQPEDLATYYCQQYDNLPITFGQGTR LEIK<br><br>SEQ ID NO: 24600 | QVQLVESGGGVVQPGRSLRLSCAASGFTFSSYGMH WVRQAPGKGLEWVAVISYGGSNKFYAVSVKGRFN ISRDNSKNTLYLQMNSLRAEDTAVYYCVRRGYSSG GYGMDVWGQGTTVTVSS<br><br>SEQ ID NO: 28606 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCCTCTATGATGGCAGT TGCAAAGTGGGGTCCCCATCAAGGTTCAGCGGC AGTGGATCTGGGACAGAATTCACTCTCACAAT CAGCAGCCTGCAGCCTGAAGATAATAGTCATCCATTC ATTACTGTCTACAGATATAATGGATATCAC ACTTTCGGCCCTGGGACCAAAGTGGATATCAC A<br><br>SEQ ID NO: 24601 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCAGAGACAAACGCCAAGAACTCACT GTATCTGCAAATGAACAGCCTGAGAGCCGAGGA CACGGCTGTGTATTACTGTGCGAGAGATAGGGGG AGCCTCTGGGGCCAGGGAACCCTGGTCACCGTCT CCTCA<br><br>SEQ ID NO: 28607 |
| | | AA | DIQMTQSPSSLSASVGDRVTITCRASQGIRNDLG WYQQKPGKAPKRLVYPASSLQSGVPSRFSGSGS GTEFTLTISSLQPEDFATYYCLQDNSHPFTFGPGT KVDIT<br><br>SEQ ID NO: 24602 | EVQLVESGGGLVKPGGSLRLSCAASGFTFSSYSMN WVRQAPGKGLEWVSSISGSSSYIYYADSVKGRFTIS RDNAKNSLYLQMNSLRAEDTAVYYCARDRGSLW GQGTLVTVSS<br><br>SEQ ID NO: 28608 |

FIGURE 50
(Continued)

| | | | |
|---|---|---|---|
| iPS:393024 | 21-225_31H9 | NA | GACATCCAGATGACCCAGTCTCCATCTTCCGT GTCTGCATCTGTAGGAGACAGAGTCACCATCA CTTGTCGGGCGAGTCAGGGTATTACCAGCTGG TTAACTTGGTATCAGCAGAAACCAGGGAAAGC CCCTAAACTCCTGATCTATGATACATCCAGTT GCAAAGTGGGGTCCCATCAAGGTTCAGCGGCA GTGGATCTGGGACAGATTCATTTCACCATC AGCAGCCTGCAGCCTGAAGATTTTGCCACTTA TTATTGTCAACAGGGTAACAGTTTCCCATTCA CTTTCGGCCCTGGGACCAAAGTGGATATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTGTGCCAT GAACTGGGTCCGCCAGGCTCCAGGGAAGGGGCT GGAGTGGGTCTCAGCTATTAGTGGTAGTGGTGGT AGCTCATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGAAACGGACTCC TATGAGTGTCTTGATATCTGGGGCCAAGGACAA TGGTCACCGTCTCTTCA SEQ ID NO: 28609 |
| | | | SEQ ID NO: 24603 | |
| | | AA | DIQMTQSPSSVSASVGDRVTITCRASQGITSWLT WYQQKPGKAPKLLIYDTSSLQSGVPSRFSGSGSG TDFIFTISSLQPEDFATYYCQQGNSFPFTFGQGTK VDIK SEQ ID NO: 24604 | EVQLLESGGGLVQPGGSLRLSCAASGFTFSSCAMN WVRQAPGKGLEWVSAISGSGGSSFYADSVKGRFTI SRDNSKNTLYLQMNSLRAEDTAVYYCAKRTPYDV FDIWGQGTMVTVSS SEQ ID NO: 28610 |
| iPS:393026 | 21-225_32B6 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATATTGCATCCAGTT TGCAAAGTGGGGTCCCATCAAGGTTCAGCGGC AGTGGATCTGGGACAGACCTTCACTCTCACAAT CAGCAGCCTGCAGCCTGAAGATTTTGCAACTT ATTACTGTCTACAGCATATAATAGTTACCCGTGG ACGTTCGGCCAAGGGACCAAGGTGGAAATCA AA SEQ ID NO: 24605 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGACACAAGGGCT GGAGTGGGTGGCAGTTATATGCAGACTCCGTGAAGGGCCGAT ACTAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAGTGGGGG GACTACTGGGGCCAGGGAACCCTGGTCACCGTCT CCTCA SEQ ID NO: 28611 |

FIGURE 50
(Continued)

| | | | |
|---|---|---|---|
| | | AA | DIQMTQSPSSLSASVGDRVTITCRASQGIRNDLGWYQQKPGKAPKRLIYIASSLQSGVPSRFSGSGSGTEFTLTISSLQPEDFATYYCLQHNSYPWTFGQGTKVEIK<br>SEQ ID NO: 24606 | QVQLVESGGGVVQPGRSLRLSCAASGFTFSDYGMHWVRQAPDKGLEWVAVIWYDENTKYYADSVKGRFTISRDNSKNTLYLQMNSLRAEDTAVYYCAREWGDYWGQGTLVTVSS<br>SEQ ID NO: 28612 |
| iPS:393028 | 21-225_25D7 | NA | GACATCCAGATGACCCAGTCTCCATCTTCCGTGTCTGCATCTGTAGGAGACAGAGTCACCTTCACTTGTCGGGCGAGTCAGGATATTTTCGACTGGTTAGCCTGGTATCAGCAGAAACCCGGACAGCCCCTAAGCTCCTGATCTATGCTGCATCCAGTTTGCAAAGTGGGGTCCCATCAAGGTTCAGCGGCAGTGGATCTGGGACAAATTTCACTCTCACCGTCAGCGGCCTGCAGCCTGAAGATTTTGCTACTTACTATTGTCAACAGGCTTACAGTTTCCCGTGGACGTTCGGCCAAGGGACCAAAGTGGAAATCAAA<br>SEQ ID NO: 24607 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGACTCCAGGGAAGGGGCTGGAGTGGGTCTCAGCTATTAGTGGTGGTGGAGGTGGTACCACATTCTACGCAGACTCCGTGAAGGGCCGGTTCACCATCTCCAGAGACACAATTCCAAGAACACGCTGTATCTGCAAATGAACAGCCTGAGAGCCGAGGACACGGCCGTATATTACTGTGCGAAAGACGGGTACGGTGGTAACTCCTTCTTTGACTACTGGGGCCAGGGAACCCTGGTCACCGTCTCCTCA<br>SEQ ID NO: 28613 |
| | | AA | DIQMTQSPSSVSASVGDRVTFTCRASQDIFDWLAWYQQKPGTAPKLLIYAASSLQSGVPSRFSGSGSGTNFTLTVSGLQPEDFATYYCQQAYSFPWTFGQGTKVEIK<br>SEQ ID NO: 24608 | EVQLLESGGGLVQPGGSLRLSCAASGFTFSSYAMSWVRQTPGQGLEWVSAISGRGGTTFYADSVKGRFTISRDNSKNTLYLQMNSLRAEDTAVYYCAKDGYGGNSFFDYWGQGTLVTVSS<br>SEQ ID NO: 28614 |

FIGURE 50
(Continued)

| | | | |
|---|---|---|---|
| iPS:393030 | 21-225_25H11 | NA | GACATCCAGATGACCCAGTCTCCATCCTCCT GTCTGCGTCTGTAGGAGACAGAGTCACCATCA CTTGCCGGGCAAGTCAGGGACAGATCACCATCA TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGTAGTCTGCAGCCTGAAGATTTTGCAACC TATTACTGTCTACAGCATAATAGTTACCCGCTC ACTTTCGGCGGAGGGACCAAGGTGGAGATCA AA SEQ ID NO: 24609 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGAAAAT AATGAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GATGACGGGTGACTCCTGGGGCCAGGGAACCCT GGTCACCGTCTCCTCA SEQ ID NO: 28615 |
| | | AA | DIQMTQSPSSLSASVGDRVTITCRASQGIRTDLG WYQQKPGKAPKRLIYAASSLQSGVPSRFSGSGS GTEFTLTISSLQPEDFATYYCLQHNSYPLTFGGG TKVEIK SEQ ID NO: 24610 | QVQLVESGGGVVQPGRSLRLSCAASGFTFSDYGM HWVRQAPGKGLEWVAVIWYDENNEYYADSVKGR FTISRDNSKNTLYLQMNSLRAEDTAVYYCARELGM TGDSWGQGTLVTVSS SEQ ID NO: 28616 |
| iPS:393032 | 21-225_26F8 | NA | GATATTGTGATGACCCAGACTCCACTCTCT GTCCGTCACCCTGGACAGCCGGCCTCCATCT CCTGCAAGTCTAGTCAGAGCCTCCTGCATGGT GATGGAAAGACCTATTTGTATTGGTACCTGCA GAAGCCAGGCCAGCCTCCACAGCTCCTGATCT ATGAAGTTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGGTTTATTACTGCATGCAAAG TATACAGCTTCCGTGACGTTCGGCCAGGGGA CCAAGGTGGAAATCAAA SEQ ID NO: 24611 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGGCTATGGCAT GCACTGGGTCCGCCAGGCTCCAGGCAAGGGGCT GGAGTGGGTGGCAATTATATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGTA CGATTTTTGGAGTGGTTGTATGGACGTCTCGGCGC CAAGGGACCACGGTCACCGTCTCCTCA SEQ ID NO: 28617 |

FIGURE 50
(Continued)

| | | | |
|---|---|---|---|
| iPS:393034 | 21-225_27F2 | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGVYYCMQSIQLPW TFGQGTKVEIK SEQ ID NO: 24612 | QVQLVESGGGVVQPGRSLRLSCAASGFTFSGYGM HWVRQAPGKGLEWVAIIWYDGSNKYYADSVKGR FTISRDNSKNTLYLQMNSLRAEDTAVYYCARERYD FWSGCMDVWGQGTTVTVSS SEQ ID NO: 28618 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGTTGCATCCAGTT TGCAAAGTGGGGTCCCATCAAGGTTCAGCGGC AGTGGATCTGGGACAGATTCACTCTCACAAT CAGCAGTCTGCAGCCTGAAGATTTTGCAACCT ATTACTGTCTACAGCATATAAGTTACCCGCTC ACTTTCGGCGGAGGGACCAAGGTGGAGATCA AA | CAGGAGCAGTCTGGTGGAGTCTGGGGGAGGCGTG GTCCAGCCTGGGAGGTCCCTGAGACTCTCCTGTG CAGCGTCTGGATTCATCTTCAGTGACTTCGACTATGGCAT GCACTGGGTCCGCCAGGCTCCAGGCAAGGGCT GGAGTGGGTGGCAGTTATATGTAGACTCCGTGAGGGGCCGAT AATAAATACTATGTAGACTCCGTGAGGGGCCGAT TCACCATCTCCAGAGACAATTCCAAGAACACGCT GTATCTGCAAATGAACAGCTGAGAGCCGAGGAG CACGGCTGTGTATTACTGTGCGAGAGAACTGGGG ATGACGGGTGACTCCTGGGGCCAGGGAACCCTG GTCACCGTCTCCTCA SEQ ID NO: 28619 |
| | | AA | DIQMTQSPSSLSASVGDRVTITCRASQGIRNDLG WYQQKPGKAPKRLIYVASSLQSGVPSRFSGSGS GTEFTLTISSLQPEDFATYYCLQHNSYPLTFGGG TKVEIK SEQ ID NO: 24614 | QEQLVESGGGVVQPGRSLRLSCAASGFIFSDYGMH WVRQAPGKGLEWVAVIWYDENNKYYVDSVRGRF TISRDNSKNTLYLQMNSLRAEDTAVYYCARELGMT GDSWGQGTLVTVSS SEQ ID NO: 28620 |

FIGURE 50
(Continued)

| | | | |
|---|---|---|---|
| iPS:393036 | 21-225_28G3 | NA | GAAATTGTGATGACCCAGACTCCACTCTCT GTCCTCACCCTGAGCAGCCGGCCTCCATCT CCTGCAAGTCTAGTCAGAGCCTCCTACATGGT GATGGAAAGACCTATTTGTATTGGTACCTGCA GAAGCCAGGCCAGCTCCACAGCTCCTGATCT ATGAAGTTTCCAACCGGTTCTCTGGAGTGCCA GAAAGGTTCAGTGGTGTAGCGGGTCAGGGACAG ATTTCACACTGAAAATCAGCGGTTATTACTGCAAAG GAGGATGTTGGGGTTTATTACTGTATGCAAAG TATACAGATTCCGTGGACGTTCGGCCAAGGGA CCAAGGTGGAAATCAAA<br><br>SEQ ID NO: 24615 | CAGGTGCAGCTGGTGGAGTCTGGGGGAGGCGTG GTCCAGCCTGGGAGGTCCCTGAGACTCTCCTGTG CAGCGTCTGGATTCATCTTCAGTACCTATGGCAT GCACTGGGTCCGCCAGGCTCCAGGCAAGGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCTGAGAGCCGAGG ACACGGCTGTGTATTACTGTGCGAGAGATCGATA CGATTTTGGAGTGGTTATTTGACTACTGGGGC CAGGGAACCCTGGTCACCGTCCTCA<br><br>SEQ ID NO: 28621 |
| | | AA | EIVMTQTPLSLSVTPGQPASISCKSSQSLLHGDGK TYLYWYLQKPGQPPQLLIYEVSNRFSGVPERFSG SGSGTDFTLKISRVEAEDVGVYYCMQSIQIPWTF GQGTKVEIK<br><br>SEQ ID NO: 24616 | QVQLVESGGGVVQPGRSLRLSCAASGFIFSTYGMH WVRQAPGKGLEWVAVIWYDGSNKYYADSVKGRF TISRDNSKNTLYLQMNSLRAEDTAVYYCARDRYDF WSGYFDYWGQGTLVTVSS<br><br>SEQ ID NO: 28622 |
| iPS:393038 | 21-225_29D8 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGGCCCTGATCTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br><br>SEQ ID NO: 24617 | CAGGTGCAGCTGGTGGAGTCTGGGGGAGGCGTG GTCCAGCCTGGGAGGTCCCTGAGACTCTCCTGTG CAGCGTCTGATTCACCTTCAGGGACTATGGCAT ACACTGGGTCCGCCAGGCTCCAGGCAAGGGGCT GGAGTGGGTGGCAGTTATATGGTTGATGGAACT AATAAATACTATGCAGACTCCGTGAAGGGCCGA TTCACCATCTCCAGAGACAATTCCAAGAACACGC TGTATCTGCAAATGAACAGCTGAGAGCCGAAG ACACGGCTGTGTATTACTGTGGGAGAGAAATTGG CTGGTTAGATGACTACTGGGGCCAGGGAACCCTG GTCACCGTCCTCA<br><br>SEQ ID NO: 28623 |

FIGURE 50
(Continued)

| | | | |
|---|---|---|---|
| iPS:393040 | | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNSYPFTFGPGTK VDIK<br>SEQ ID NO: 24618 | QVQLVESGGGVVQPGRSLRLSCAASGFTFRDYGIH WVRQAPGKGLEWVAVIWFDGTNKYYADSVKGRF TISRDNSKNTLYLQMNSLRAEDTAVYYCGREIGWL DDYWGQGTLVTVSS<br>SEQ ID NO: 28624 |
| | 21-225_30E3 | NA | GACATCCAGATGACCCAGTCTCCATCCTCCCT GTCTGCATCTGTAGGAGACAGAGTCACCATCA CTTGCCGGGCAAGTCAGGACATTAGAGATGAT TTAGGCTGGTATCAGCAGAAACCAGGAAAG CCCCTAGGCGCCCTGATCTATGCTGCATTCAGC TTGCAAAGTGGGGTCCCATCCAAGGTTCAGCGG CAGTGGATCTGGGACAGATTCACTCTCACAA TCAGCAGCCTGCAGCCTGAAGATTTTGCAACT TATTACTGTCTACAGCATACTAGTTACCCTCCT ACTTTCGGCGGAGGGACCAAGGTGGAGATCA AA<br>SEQ ID NO: 24619 | GAGGTGCAGGTGTTGGAGTCTGGGGGAGGCTTG GTACAGCCTGGGGGGTCCCTGAGACTCTCCTGTG CAGCCTCTGGATTCACCTTTAGCAGTTATGCCAT GAACTGGGTCCGCCAGGCTCCAGGGAAGGGGCT GGAGTGGGTCTCCGCTATTAGTGGTGGTGGT AGCACATTCTACGCAGACTCCGAGAAGGGCCGG TTCACCATCTCCAGAGACAATTCCAAGAACACGC TGTATCTGCAAATGAACAGCCTGAGAGCCGAGG ACACGGCCCTATATTACTGTGCGAAAGGGAGCT ATTAGAGGACTACTACTACTACGGAATGGACGTC TGGGGCCAAGGGACCACGGTCACCGTCTCCTCA<br>SEQ ID NO: 28625 |
| | | AA | DIQMTQSPSSLSASVGDRVTITCRASQDIRDDLG WYQQKPGKAPRRLIYAAFSLQSGVPSRFSGSGS GTEFTLTISSLQPEDFATYYCLQHTSYPPTFGGGT KVEIK<br>SEQ ID NO: 24620 | EVQVLESGGGLVQPGGSLRLSCAASGFTFSSYAMN WVRQAPGKGLEWVSAISGRGGSTFYADSEKGRFTI SRDNSKNTLYLQMNSLRAEDTALYYCAKGELLED YYYYGMDVWGQGTTVTVSS<br>SEQ ID NO: 28626 |

FIGURE 50
(Continued)

| | | | |
|---|---|---|---|
| iPS:393042 | 21-225_31F1 | NA | GACATCCAGATGACCCAGTCTCCATCCCCT GTCTGCATCTGTAGGAGACAGAGTCACCATCA CTTGCCGGGCAAGTCAGAGGATTAGCAGCTAT TTAAATTGGTATCAGCAGAAACCAGGGAAAG CCCCTAAGCTCCTGATCTTTGCTGCATCCAGTT CGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACATTACCCCGCTC ACTTTCGGCGGAGGGACCAAGGTGGAGATCA GA<br><br>SEQ ID NO: 24621 | CAGGTGCAGCTGGTGCAGTCTGGGGCTGAGGTG AAGAAGCCTGGGGCCTCAGTGAAGGTCTCCTGC AAGGCTTCTGGATACACCTTCACCGACTACTATA TGCACTGGGTGCGACAGGCCCCTGGACAGGGGC TTGAGTGGATGGGATGGATCAACCCTAACAGTGG TGGCACAAACTATGCACAGAAGTTTCAGGGCAG GGTCACCATGACCAGGGACACGTCCATTATGACA GCCTATATGGAGCTGAGCAGGCTGAGATCTGAC GACACGGCCGTGTATTACTGTGCGAGAGATAGTA GCAATTTCAGCAACTGGTACGATTACTACGGTAT GGACGTCTGGGGCCAAGGGACCACGGTCACCGT CTCCTCA<br><br>SEQ ID NO: 28627 |
| | | AA | DIQMTQSPSSLSASVGDRVTITCRASQRISSYLN WYQQKPGKAPKLLIFAASSSQSGVPSRFSGSGSG TDFTLTISSLQPEDFATYYCQQSYITPLTFGGGTT VEIR<br><br>SEQ ID NO: 24622 | QVQLVQSGAEVKKPGASVKVSCKASGYTFTDYYM HWVRQAPGQGLEWMGWINPNSGGTNYAQKFQGR VTMTRDTSIMTAYMELSRLRSDDTAVYYCARDSSN FSNWYDYYGMDVWGQGTTVTVSS<br><br>SEQ ID NO: 28628 |
| iPS:393044 | 21-225_25B8 | NA | GAAATAGTGATGACGCAGTCTCCAGCCACCCT GTCTGTGTCTCCAGGGGAAAGAGCCACCCTCT CCTGCAGGGCCAGTCAGAGTGTTAGAAGTAAT TTAGCCTGGTACCAGCAGAAACCTGGCCAGGC TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCAGCCTGCAGTCTGAAGATTTTGCACTTT ATTACTGTCAGCAGTATAATAATTGGCCTCCG TGGCCGTTCGGCCAAGGGACCAAGGTGGAAA TCAAA<br><br>SEQ ID NO: 24623 | CAGGTTCAGTTGGTGCAGTCTGGAGCTGAGGTGA AGAAGCCTGGGGCCTCAGTGAAGGTCTCCTGCA AGGCTTCTGGTTACACCTTCACCAGCTATGTAT CAGCTGGGTGCGACAGGCCCCTGGACAAGGGCT TGAGTGGATGGGATGGATCAGCGCTTACAATGGT AACACAACCTATGCACAGAAGCTCCGGGGCAGA GTCACCATGACCACAGACACATCCACGAGCACA GCCTACATGGAGCTGAGGAGCTGAGATCTGACG ACACGGCCGTGTATTACTGTGCGAGAACCGCTGC TGGGTATAGCAGCAGCTGGTTTGACTACTGGGGC CAGGGAACCCTGGTCACCGTCTCCTCA<br><br>SEQ ID NO: 28629 |

FIGURE 50
(Continued)

| | | | |
|---|---|---|---|
| | | AA | EIVMTQSPATLSVSPGERATLSCRASQSVRSNLAWYQQKPGQAPRLLIYGASTRATGIPARFSGSGSGTEFTLTISSLQSEDFALYYCQQYNNWPPWPFGQGTKVEIK<br>SEQ ID NO: 24624 | QVQLVQSGAEVKKPGASVKVSCKASGYTFTSYGISWVRQAPGQGLEWMGWISAYNGNTTYAQKLRGRVTMTDTSTSTAYMDLRSLRSDDTAVYYCARTAAGYSSSWFDYWGQGTLVTVSS<br>SEQ ID NO: 28630 |
| iPS:393046 | 21-225_25A12 | NA | GACATCCAGATGACCCAGTCTCCATCCTCCCTGTCTGCATCTGTAGGAGACAGAGTCACCGTCACTTGCCGGGCAAGTCAGGCCATTAGAGATGATCAGCGTCTGGATTCACCTTCAGTAACTGTGTCATGCACTGGGTCCGCCAGGCTCCAGGCAAGGGCTTTAGGCTGGTATCAGCAGAGACCAGGAAAGGGAGTGGGTGGCAGTTATATGTATGGAAGTCCCCTAAGCGCCTGATCTATGCTGCATCCAGTAATAAATACTATGCAGACTCCGTGAAGGGCCGATTGCAAAGTGGGGTCCCATCCAAGGTTCAGCGGTTCACCATCTCCAGAGACAATTCCAAGAACACGCCAGTGGATCTGGGACAGTCTGAAGATTTATTCTCACAATGTATCTGCAAATGAACAGCCTGAGAGCCGAGGTCAGCAGCCTGCAGCCTGAAGATTTTGCAACTACACGGCTGTGTATTACTGTGCGAGAGAGAGTATATTACTGTCTACAGCATTATAATTACCCTCGCTAGCAGTGGCTGGTACGACTACGGTATGGACGTCAGTTTTGGCCAGGGGACCAAGCTGGAGATCAATGGGGCCAAGGGACCACATGGTCACCGTCTCCTCAA<br>SEQ ID NO: 24625 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAACTGTGTCATGCACTGGGTCCGCCAGGCTCCAGGCAAGGGGCTGGAGTGGGTGGCAGTTATATGTATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGTATAGCAGTGGCTGGTACGACTACGGTATGGACGTCTGGGGCCAAGGGACCACATGGTCACCGTCTCCTCA<br>SEQ ID NO: 28631 |
| | | AA | DIQMTQSPSSLSASVGDRVTVTCRASQAIRDDLGWYQQRPGKAPKRLIYAASSLQSGVPSRFSGSGSGTEFILTISSLQPEDFATYYCLQHYNYPRSFGQGTKLEIK<br>SEQ ID NO: 24626 | QVQLVESGGGVVQPGRSLRLSCAASGFTFSNCVMHWVRQAPGKGLEWVAVIWYDGSNKYYADSVKGRFTISRDNSKNTLYLQMNSLRAEDTAVYYCAREEYSSGWYDYGMDVWGQGTMVTVSS<br>SEQ ID NO: 28632 |

FIGURE 50
(Continued)

| | | | |
|---|---|---|---|
| iPS:393048 | 21-225_27C3 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGTCTGCAGCCTGAAGATTTTGCAACC TATTACTGTCTACAGCATAATCGTTACCCGCTC ACTTTCGGCGGAGGGACCAAGGTGGAGATCA AA SEQ ID NO: 24627 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGAAAAT AATAAATCTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG ATGACGGGTGACTCCTGGGGCCAGGGAACCCTG GTCACCGTCTCCTCA SEQ ID NO: 28633 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNRYPLTFGGG TKVEIK SEQ ID NO: 24628 | QVQLVESGGGVVQPGRSLRLSCAASGFTFSDYGM HWVRQAPGKGLEWVAVIWYDENNKSYADSVKGR FTISRDNSKNTLYLQMNSLRAEDTAVYYCARELGM TGDSWGQGTLVTVSS SEQ ID NO: 28634 |
| iPS:393050 | 21-225_28C5 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCAAC TTAGCCTGGTACCATCAGAAACCTGGCCAGGC TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCAGCCTGCAGTCTGAAGATATAATTGGCCTCCG ATTACTGTCAGCAGTATAATAATTGGCCTCCG TGGCCCGTTCGGCCAAGGGACCAAGGTGGAAA TCAAA SEQ ID NO: 24629 | CAGGTTCAGTTGGTGCAGTCTGGGAGCTGAGGTGA AGAAGCCTGGGGCCTCAGTGAAGGTCTCCTGCA AGGCTTCTGATTACACCTTCACCAGCTATGGTAT CAGCTGGGTGCGACAGGCCCCTGGACAAGGCT TGAGTGGATGGGATGGATCAGCGTTACAATGGT AACACAACCTATGCACAGAAGCTCCGGGCAGA GTCACCATGACCACAGACACATCCACGAGCACA GCCTACATGGATCTGAGGAGCCTGAGATCTGACG ACACGGCCGTGTATTACTGTGCGAGAACCGCTGC TGGGTATAGCAGCAGCAGCTGGTTTGACTACTGGGGC CAGGGAACCCTGGTCACCGTCTCCTCA SEQ ID NO: 28635 |

FIGURE 50
(Continued)

| | | | |
|---|---|---|---|
| iPS:393054 | | AA | EIVMTQSPATLSVSPGERATLSCRASQVSSNLA WYHQKPGQAPRLLIYGASTRATGIPARFSGSGSG TEFTLTISSLQSEDFALYYCQQYNNWPWPFGQ GTKVEIK<br>SEQ ID NO: 24630 | QVQLVQSGAEVKKPGASVKVSCKASDYTFTSYGIS WVRQAPGQGLEWMGWISAYNGNTTYAQKLRGRV TMTDTSTSTAYMDLRSLRSDDTAVYYCARTAAG YSSSSWFDYWGQGTLVTVSS<br>SEQ ID NO: 28636 |
| | 21-225_29G8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCTGAAACCAGGAAAGC CCCTAAGCGCCTGATCTATGCTGCATCCAGTTT GCAAAGTGGGGTCCCATCAAGGTTCAGCGGCA GTGGATCTGGGACAGAATTCACTCTCACAATC AGCAGCCTGCAGCCTGAAGATTTGCAACTTA TAACTGTCTACAGCATAATAGTTATCCGCTCA CTTTCGGCGGAGGGACCAAGGTGGAGATCAA A<br>SEQ ID NO: 24631 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGAAACT AATAAATACTATGCAGACTCCGTGAAGGGCCGA TTCACCATCTCAGAGACAATTCCAAGAACACGC TGTATCTGCAAATGAACAGCCTGAGAGCCGAGG ACACGGCTGTGTATTACTGTGCGAGAGAACTGGG GATGACGAGTGACTACTGGGGCCAGGGAACCCT GGTCACCGTCTCCTCA<br>SEQ ID NO: 28637 |
| | | AA | DIQMTQSPSSLSASVGDRVTITCRASQGIRNDLG WYQLKPGKAPKRLIYAASSLQSGVPSRFSGSGSG TEFTLTISSLQPEDFATYNCLQHNSYPLTFGGGT KVEIK<br>SEQ ID NO: 24632 | QVQLVESGGGVVQPGRSLRLSCAASGFTFSDYGM HWVRQAPGKGLEWVAVIWYDETNKYYADSVKGR FTISRDNSKNTLYLQMNSLRAEDTAVYYCARELGM TSDYWGQGTLVTVSS<br>SEQ ID NO: 28638 |

FIGURE 50
(Continued)

| | | | | |
|---|---|---|---|---|
| iPS:393056 | 21-225_30F3 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGATCTGGGACAGATTTCACTCTCACAA TCAGCAGCCTGCAGCCTGAAGATTTTGCAAGT TATTACTGTCTACAGCATAATAGTTACCCGTTC ACTTTCGGCGGAGGGACCAAGGTGGAGATCA AA SEQ ID NO: 24633 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGTAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAATGGG CTGGTACGATGACTACTGGGGCCAGGGAACCCT GGTCACCGTCTCCTCA SEQ ID NO: 28639 |
| | | AA | DIQMTQSPSSLSASVGDRVTITCRASQGIRNDLG WYQQKPGKAPKRLIYTASSLQSGVPSRFSGSGSG TDFTLTISSLQPEDFASYYCLQHNSYPFTFGGGT KVEIK SEQ ID NO: 24634 | QVQLVESGGGVVQPGRSLRLSCAASGFTFSSYGMH WVRQAPGKGLEWVAVIWYDVSNKYYADSVKGRF TISRDNSKNTLYLQMNSLRAEDTAVYYCAREMGW YDDYWGQGTLVTVSS SEQ ID NO: 28640 |
| iPS:393058 | 21-225_31H3 | NA | GACATCCAGATGACACAGTCTCCATCCTCCCT GTCTGCATCTGTAGGAGACAGAGTCACCATCA CTTGCCGGGCAAGTCAGGACATTAGAGATGAT TTAGGCTGGTATCAGCAGAAACCAGGGAAAG CCCCTAGGCGCCTGATCTATGCTGCATTCAGC TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAGTTACCCTCCT ACTTTCGGCGGAGGGACCAAGGTGGAGATCA AA SEQ ID NO: 24635 | GAGGTGCAGGTGTTGGAGTCTGGGGGAGGCTTG GTACAGCCTGGGGGGTCCCTGAGACTCTCCTGTG CAGCCTCTGGATTCACCTTTAGCAGCAGTATGCCAT GAACTGGGTCCGCCAGGCTCCAGGGAAGGGGCT GGAGTGGGTCTCCGTATTAGTGGTCGTGGTGGT AACACATTCTACGCAGACTCCGTGAAGGGCCGGT TCACCATCTCCAGAGACAATGAACAGCCTGAGGA GTATCTGCAAATGAACAGCCTGAGAGCCGAGGA CACGGCCGTATATTACTGTGCGAAGGGGAGTTA CTAGAGAGACTACTACTACTACGGAATGGACGTCT GGGGCCAAGGGACCACGGTCACCGTCTCCTCA SEQ ID NO: 28641 |

FIGURE 50
(Continued)

| | | | | |
|---|---|---|---|---|
| | | AA | DIQMTQSPSSLSASVGDRVTITCRASQDIRDDLG WYQQKPGKAPRRLIYAAFSLQSGVPSRFSGSGS GTEFTLTISSLQPEDFATYYCLQHTSYPPTFGGGT KVEIK | EVQVLESGGGLVQPGGSLRLSCAASGFTFSSYAMN WVRQAPGKGLEWVSAISGRGNTFYADSVKGRFTI SRDNSKNTLYLQMNSLRAEDTAVYYCAKGELLED YYYYGMDVWGQGTTVTVSS |
| | | | SEQ ID NO: 24636 | SEQ ID NO: 28642 |
| iPS:393060 | 21-225_32G12 | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAGCAGAAACCAGGAAAAG CCCCTAAGCGCCTGATCTATGCTGCATCCAGT TTGCAAAGTGGGGTCCCATCAAGGTTCAGCGG CAGTGGATCTGGGACAGATCACTCTCACAA TCAGCAGCCTACAGCCTGAAGATTTTGCAACT TATTACTGTCTGCAGCATACTATTTACCCTCCT ACTTTCGGCGGAGGGACCAAGGTGGAGATCA AA | GAGGTGCAGCTGTTGGAGTCTGGGGGAGGCTTGC TACAGCCTGGGGGGTCCCTGAGACTCTCCTGTGC AGCCTCTGGATTCACCTTTAATAGCTATGCCATG AGCTGGGTCCGCCAGGCTCCAGGAAGGGGCTG GAGTGGGTCTCCTCATTAGTGGTGTGTGGTA GCACATTCCACGCAGACTCCGTGAAGGGCCGGTT CACCATCTCCAGAGACAATTCCAGGAACACGCTG TATCTGCAAATGAACAGCCTGAGAGCCGAGGAC ACGGCCGTATATTACTGTGTGAAAGGGGAGCTAC TAGAGGACTACTACTTCTACGGTATGGACGTCTG GGGCCAAGGGACCACGGTCACCGTCTCCTCA |
| | | | SEQ ID NO: 24637 | SEQ ID NO: 28643 |
| | | AA | DIQMTQSPSSLSASVGDRVTITCRASQDIRSDLG WYQQRPGKAPKRLIYAASSLQSGVPSRFSGSGS GTEFTLTISSLQPEDFATYYCLQHTIYPPTFGGGT KVEIK | EVQLLESGGGLLQPGGSLRLSCAASGFTFNSYAMS WVRQAPGKGLEWVSSISGRGGSTFHADSVKGRFTI SRDNSRNTLYLQMNSLRAEDTAVYYCVKGELLED YYFYGMDVWGQGTTVTVSS |
| | | | SEQ ID NO: 24638 | SEQ ID NO: 28644 |

FIGURE 50
(Continued)

| | | | |
|---|---|---|---|
| iPS:393062 | 21-225_33H3 | NA | GACATCCAGATGACCCAGTCTCCATCCTCCCT GTCTGCATCTGTTGGAGACAGAGTCACCATCA CTTGCCAGGCGAGTCAGGACATTTCCAACTTT TTAAAATTGGTTTCGCAGAAACCAGGAAAAGC CCCTAACTCCCTGATCTACGATGCATCCAATTT GGTAACAGGGGTCCCATCAAGGTTCAGTGGAC GTGGATCTGGGACAGATTTACTTTCACCATC AGCAGCCTGCAGCCTGAAGATTTTGCAACATA TTACTGTCAACAGTATGATAATCTCCCGATCA CCTTCGGCCAAGGGACACGGCTGGAGATTAAA | CAGGTGCAGCTGGTGGTGGAGTCTGGGGAGGCGTG GTCCAGCCTGGGAGGTCCCTGAGACTCTCCTGTG CAGCCTCTGGATTCACCTTCAGTAGCTATGGCAT GCACTGGGTCCGCCGGGCTCCAGGCAAGGGGCT GGAGTGGGTGGCAATTATATCATATGGTGAAGT AATAACTTCTATGCAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGCGAGAAGGGGTAT AGCAGTGGAGGCTACGGTATGGACGTCTGGGGC CAAGGGACCACGGTCACCGTCTCCTCA |
| | | | SEQ ID NO: 24639 | SEQ ID NO: 28645 |
| | | AA | DIQMTQSPSSLSASVGDRVTITCQASQDISNFLN WFRQKPGKAPNSLIYDASNLVTGVPSRFSGRGS GTDFTFTISSLQPEDFATYYCQQYDNLPITFGQGT RLEIK | QVQLVESGGGVVQPGRSLRLSCAASGFTFSSYGMH WVRRAPGKGLEWVAIISYGGSNNFYADSVKGRFTI SRDNSKNTLYLQMNSLRAEDTAVYYCARRGYSSG GYGMDVWGQGTTVTVSS |
| | | | SEQ ID NO: 24640 | SEQ ID NO: 28646 |
| iPS:393064 | 21-225_33A9 | NA | GACATCCAGATGACCCAGTCTCCATCCTCCCT GTCTGCATCTGTAGGAGACAGAGTCACCATCA CTTGCCCGGGCAAGTCAGAGCATTAGCAGGTAT TTAAGTTGGTATCAGCAGAAACCAGGGAGAG CCCCTAACCTCCAGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAATATCCCGATC ACCTTCGGCCAAGGGACACGACTGGAGATTAA A | CAGGTGCAGCTGGTGCAGTCTGGGGCTGAGGTG AAGAAGCCTGGGGCCTCAGTGAAGGTCTCCTGTA AGGCTTCTGGATACACCTTCACCAGTTATGATAT CAACTGGGTGCGACAGGCCACTGGTCAAGGCT TGAGTGGATGGGATGGATGAACCTAACAGTGG TAACACAGGCTATGCACAGAAGTTCCAGGGCAG AGTCACCATGACCAGGAACACCTCCATAAGCAC AGCCTACATGGAGCTGAGCAGCCTGGGATCTGA GGACACGGCCGTGTATTACTGTGCGAGAAAGAA GGCTAACGACTACTGGGGCCAGGGAACCCTGGT CACCGTCTCCTCA |
| | | | SEQ ID NO: 24641 | SEQ ID NO: 28647 |

FIGURE 50
(Continued)

| | | | |
|---|---|---|---|
| | | AA | DIQMTQSPSSLSASVGDRVTITCRASQSISRYLSW YQQKPGRAPNLQIYAASSLQSGVPSRFSGSGSGT DFTLTISSLQPEDFATYYCQQSYNIPITFGQGTRL EIK | QVQLVQSGAEVKKPGASVKVSCKASGYTFTSYDIN WVRQATGQGLEWMGWMNPNSGNTGYAQKFQGR VTMTRNTSISTAYMELSSLGSEDTAVYYCARKKAN DYWGQGTLVTVSS |
| | | | SEQ ID NO: 24642 | SEQ ID NO: 28648 |
| iPS:393066 | 21-225_34D3 | NA | GACATCCAGATGACCCAGTCTCCATCCTCCCT GTCTGCATCTGTTGGAGACAGAGTCACCATCA CTTGCCGGGCAAGTCAGAACATTTACAGCTAT TTAAATTGGTATCAGCAGAAACCAGGGAAAG ACCCTAAACTCCTGATCTATGCTGCATCCAGTT TGCATAGTGGGGTCCCGTCACGGTTCAGTGGC AGTGGTTCTGGGACAGATTTCACTCTCACCAT CAGCAGTCTGCAACCTGAAGATTTTGCAACTT TCTACTGTCAACAGAGTTACAGTACTCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTTACTATGGCAT GCACTGGGTCCGCCAGGCTCCAGGCAAGGGCT GGAGTGGGTGGCAGTTATATGCATGATGAAAG TAATAAATACTATGTAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAATAG CAGTTCGTTCTACTTTGACTACTGGGGCCAGGA ACCCTGGTCACCGTCTCCTCA |
| | | | SEQ ID NO: 24643 | SEQ ID NO: 28649 |
| | | AA | DIQMTQSPSSLSASVGDRVTITCRASQNIYSYLN WYQQKPGKDPKLLIYAASSLHSGVPSRFSGSGS GTDFTLTISSLQPEDFATFYCQQSYSTPLTFGGGT KVEIK | QVQLVESGGGVVQPGRSLRLSCAASGFTFSYYGM HWVRQAPGKGLEWVAVIWHDGSNKYYVDSVKGR FTISRDNSKNTLYLQMNSLRAEDTAVYYCARENSS SFYFDYWGQGTLVTVSS |
| | | | SEQ ID NO: 24644 | SEQ ID NO: 28650 |

FIGURE 50
(Continued)

| | | | | |
|---|---|---|---|---|
| iPS:393068 | 21-225_34G9 | NA | GACATCCAGATGACCCAGTCTCCATCCTCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCACGTG CAGTGGCTCTGGGACAGAATTCACTCTCACAA TCAGCAGCCTGCAGCCTGAAGCTTTTGCAATT TATTACTGTCTCCAGCATACTATTTACCCTCCT ACTTTCGGCGGAGGGACCAAGGTGGAGATCAA A | GAGGTGCAGCTGGTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCCGCTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAAGGGAGCT ACTAGAGGACTACTACTTCTACGGTATGACGTC TGGGGCCAAGGGACCACGGTCACCGTCTCCTCA |
| | | | SEQ ID NO: 24645 | SEQ ID NO: 28651 |
| | | AA | DIQMTQSPSSLSASVGDRVTITCRASQDIRSDLG WYQQKPGKAPKRLIYAASSLQSGVPSRFTGSGS GTEFTLTISSLQPEAFAIYYCLQHTIYPPTFGGGT KVWIK | EVQLVESGGGLVQPGGSLRLSCAASGFTFSSYAMS WVRQAPGKGLEWVSAISGRGGSTFHADSVKGRFTI SRDNSKNTLYLQMNSLRAEDTAVYYCVKGELLED YYFYGMDVWGQGTTVTVSS |
| | | | SEQ ID NO: 24646 | SEQ ID NO: 28652 |
| iPS:393072 | 21-225_36C5 | NA | GACATCCAGATGACCCAGTCTCCATCCTCCT GTCTGCATCTGTAGGAGACAGAGTCACCATCA CTTGCCGGGCAAGTCAGGACAGTCACCATCA TTAGGCTGGTATCAGCAGAAACCAGGGAAAG CCCCTAAGCGCCTGATCTATGCTGCATCCAGT TTGCAAAGTGGGGTCCCATCAAGGTTCACCGG CAGTGGATCTGGGACAGAATTCACTCTCACAA TCAGCAGCGTGCAGCCTGAAGATTTTGCAACT TATTACTGTCTCTCCATCATCCTATTTACCCTCT ACTTTCGGCGGAGGGACCAAGGTGTGGATCAA A | GAGGTGCAGCTGGTGGAGTCTGGGGGAGGCTTG GTACAGCCTGGGGGGTCCCTGAGACTCTCCTGTG CAGCCCTCTGGATTCACCTTTAGCAGCTATGCCAT GAACTGGGTCCGCCAGGCTCCAGGGAAGGGGCT GGAGTGGGTCTCCGCTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAAGGGAGCT ATTAGAGGACTACTACTTCTACGGTATGGACGTC TGGGGCCAAGGGACCACGGTCACCGTCTCCTCA |
| | | | SEQ ID NO: 24647 | SEQ ID NO: 28653 |

FIGURE 50
(Continued)

| | | AA | DIQMTQSPSSLSASVGDRVTITCRASQDIRSDLG WYQQKPGKAPKRLIYAASSLQSGVPSRFTGSGS GTEFTLTISSVQPEDFATYYCLHHPIYPPTFGGGT KVWIK SEQ ID NO: 24648 | EVQLVESGGGLVQPGGSLRLSCAASGFTFSSYAMN WVRQAPGKGLEWVSAISGRGGSTHADSVKGRFTI SRDNSKNTLYLQMNSLRAEDTAVYYCVKGELLED YYFYGMDVWGQGTTVTVSS SEQ ID NO: 28654 |
|---|---|---|---|---|
| iPS:393074 | 21-225_33B1 | NA | GACATCCAGATGACCCAGTCTCCATCCTCCCT GTCTGCATCTGTAGGAGACAGAGTCACCATCA CTTGCCGGACAAGTCAGGGACAGAGTCATTAGAAATGAT TTAGGCTGGTTTCAGCAGAAACCAGGAAAGC GCACTAAGCGCCTGATCTATACTGCATCCAGTTT CCCTAAGCGCCTGATCTATACTGCATCCAGTTT GCAAAGTGGGGTCCCATCAAGGTTCAGCGGCA GTGGATCTGGGACAGAATTCACTCTCACAATT AGCAGCCTGCAGCCTGAAGATTTGCAACTTA TTACTGTCTACAGCATAATAGTTACCCGCTCA CTTTCGGCGGAGGGACCAAGGTGGAGGTCAA A SEQ ID NO: 24649 | CAGGTGCAGCTGGTGGTGGAGTCTGGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGCCAAGGGGCT GGAGTGGGTGGCAGTTATATGCAGACTCCGTGAAGGGCCGA AATAAATACTATGCAGACTCCGTGAAGGGCCGA TTCACCATCTCAGAGAGACAATCCAAGAACACGC TGTATCTGCAAATGAACAGCCTGAGAGCCGAGG ACACGGCTGTATATTACTGTGCGAGAGAATGGG CTGGTACGATGACTACTGGGGCCAGGGAACCCT GGTCACCGTCTCCTCA SEQ ID NO: 28655 |
| | | AA | DIQMTQSPSSLSASVGDRVTITCRTSQGIRNDLG WFQQKPGKAPKRLIYTASSLQSGVPSRFSGSGSG TEFTLTISSLQPEDFATYYCLQHNSYPLTFGGGT KVEVK SEQ ID NO: 24650 | QVQLVESGGGVVQPGRSLRLSCAASGFTFSDYGM HWVRQAPAKGLEWVAVIWYDRNNKYYADSVKG RFTISRDNSKNTLYLQMNSLRAEDTAVYYCAREMG WYDDYWGQGTLVTVSS SEQ ID NO: 28656 |

FIGURE 50
(Continued)

| | | | |
|---|---|---|---|
| iPS:393076 | 21-225_33A4 | NA | GACATCCAGATGACCCAGTCTCCATCCTCCT<br>GTCTGCATCTGTAGGAGACAGAGTCACCATCA<br>CTTGCCGGGCAAGTCAGGACATTAGAAATGAT<br>GTAGGCTGGTATCAGCAGCAGAAACCAGGAAAG<br>CCCCTGAGCGCCTGATCTATGCTGCATCCAGT<br>TTGCAACGTGGGGTCCCATCAAGGTTCAGCGG<br>CAGTGGATCTGGGACAGATTCACTCTCACAA<br>TCAGCAGCCTGCAGCCTGAAGATTTTGCAAGA<br>TATTACTGTCTACAGCATTATAGTTACCCTCCT<br>ACTTTCGGCGGAGGGACCAAGGTGGAGATCA<br>AA<br><br>SEQ ID NO: 24651 | GAGGTGCAGTTGTTGGAGTCTGGGGGAGGCTTGG<br>TACAGTCTGGGGGGTCCCTGAGACTCTCCTGTGA<br>AGCCTCAGGATTCATCTTTAGCAGCTATGCCATG<br>AACTGGGTCCGCCAGGTTCCAGGGAAGGGGCTG<br>GAGTGGGTCTCAGCTATTAGTCGTCGTGGTGTA<br>GCACATTCTACGCAGACTCCGTGAAGGGCCGGTT<br>CACCATTTCCAGAGACAATTCCAAGAACACGCTG<br>TATCTGCAAATGAACAGCCTGAGAGCCGAGGAC<br>ACGGCCGTATATTTCTGTGCGAAAGGGGAACTAC<br>TAGAGGACTACTCCTACTACGGTATGCGAGCTG<br>GGGCCAGGGGACCACGGTCACCGTCTCCTCA<br><br>SEQ ID NO: 28657 |
| | | AA | DIQMTQSPSSLSASVGDRVTITCRASQDIRNDVG<br>WYQQKPGKAPERLIYAASSLQRGVPSRFSGSGS<br>GTEFTLTISSLQPEDFARYYCLQHYSYPPTFGGG<br>TKVEIK<br><br>SEQ ID NO: 24652 | EVQLLESGGGLVQSGGSLRLSCEASGFIFSSYAMN<br>WVRQVPGKLEWVSAISRRGGSTFYADSVKGRFTI<br>SRDNSKNTLYLQMNSLRAEDTAVYFCAKGELLED<br>YSYYGIDVWGQGTTVTVSS<br><br>SEQ ID NO: 28658 |
| iPS:393078 | 21-225_33H11 | NA | GACATCCAGATGACCCAGTCTCCATCCTCACT<br>GTCTGCATTTGTAGGAGACAGAGTCACCATCA<br>CTTGTGTTGGGCGAGTCAGGGCATTAACAGTTAT<br>TTAGCCTGGTTTCAGCAGAGACCAGGGAAAGC<br>CCATAAGTCCTGATCTATGCTGCATCCAGTTT<br>GCAAGGTGGGGTCCCATCAAAGTTCAGCGGCA<br>GTGGATCTGGGACAGATTTCATTCTCACCATC<br>AGCAGCCTGCAGCCTGAAGATTTTGCAACTTA<br>TTACTGCCAACAGTTTAATAGTTACCCTCTGAC<br>GTTCGGCCAAGGGACCAAGGTGGAAATCAAA<br><br>SEQ ID NO: 24653 | GAGGTGCAGCTGGTGGAGTCTGGGGGAGGCCTG<br>GTCAAGCCTGGGGGGTCCCTGAGACTCTCCTGTG<br>CAGCCTCTGGATTCACCTTCAGTAGCTATAGCAT<br>GAACTGGGTCCGCCAGGCTCCAGGGAAGGGGCT<br>GGAGTGGGTCTCATCCATTAGTAGTGGTAGTAGT<br>TACATATACTACCAGAGACTCAGTGAAGGGCCGAT<br>TCACCATCTCCAGAGACAACGCCAAGAACTCACT<br>GTATCTGCAAATGAGCAGCCTGAGAGCCGAGGA<br>CACGGCTGTGTACTACTGTGCGAGAACAACGGT<br>ATGGACGTCTGGGGCCAAGGGACCACGGTTACC<br>GTCTCCTCA<br><br>SEQ ID NO: 28659 |

FIGURE 50
(Continued)

| | | | |
|---|---|---|---|
| iPS:393080 | 21-225_34F3 | AA | DIQMTQSPSSLSAFVGDRVTITCWASQGINSYLA WFQQRPGKAHKSLIYAASSLQGGVPSKFSGSGS GTDFILTISSLQREDFATYYCQQFNSYPLTFGQGT KVEIK<br>SEQ ID NO: 24654 | EVQLVESGGGLVKPGGSLRLSCAASGFTFSSYSMN WVRQAPGKGLEWVSSISGSSSYIYYADSVKGRFTIS RDNAKNSLYLQMSSLRAEDTAVYYCARTNGMDV WGQGTTVTVSS<br>SEQ ID NO: 28660 |
| | | NA | GACATCCAGATGACCCAGTCTCCGTCTTCCGT GTCTGCAACTGTAGGAGACAGAGTCACCAGCA CTTGTGCGGGCGAGTCAGGTATTAGTAAGTGG TTAGCCTGGTATCAGCAGAAGCCAGGGAAAG CCCCTAAACTCCTGATCTATGCTGCATCCAGT TGCAAAGTGGGGTCCCATCAAGGTTCAGCGGC AGTGGATCTGGGACAGATTTCACTCTCACCAT CAGCAGCCTGCAGCCTGAAGACTCTGCAACTT ACTATTGTCAACAGGCTAACAGTTTCCCTTTCA CTTTCGGCCCTGGGACCAAAGTGGATATCAAA<br>SEQ ID NO: 24655 | CAGGTGCAGCTGGTGCAGTCTGGGGCTGAGGTG AAGAAGCCTGGGGCCTCAGTGAAGGTCCTGC AAGGCTTCTGATACACCTTCACCGGCTACCATA TGCACTGGGTGCGACAGGCCCCTGGACAAGGC TTGACTGGATGGGATGGATCAACCTAACAGTGG TGGCACAAACTATGCACAGAAGTTTCAGGCAG GGTCACCATGACCAGGGACACGTCCATCAGCAC AGCCTATATGGAGCTGAGCAGGCTGAGATCTGA CGACACGGCCGTGTATTACTGTGCGAGAGACGGT ACCAGTCCTTTGACTACTGGGGCCAGGGAACCC TGGTCACCGTCTCCTCA<br>SEQ ID NO: 28661 |
| | | AA | DIQMTQSPSSVSATVGDRVTSTCRASQGISKWLA WYQQKPGKAPKLLIYAASSLQSGVPSRFSGSGS GTDFTLTISSLQPEDSATYYCQQANSFPFTFGPGT KVDIK<br>SEQ ID NO: 24656 | QVQLVQSGAEVKKPGASVKVSCKASGYTFTGYHM HWVRQAPGQGLDWMGWINPNSGGTNYAQKFQGR VTMTRDTSISTAYMELSRLRSDDTAVYYCARDGTS SFDYWGQGTLVTVSS<br>SEQ ID NO: 28662 |

FIGURE 50
(Continued)

| | | | |
|---|---|---|---|
| iPS:393082 | 21-225_34C11 | NA | GACATCCAGATGACCCAGTCTCCATCTTCCTGTCTGCATCTGTAGGAGACAGAGTCACCATCACTTGCCGGGCAAGTCAGAGCATTAGCAGCAATTTAAATTGGTATCAGCAGAAACCTGAGAAAGACCCTAAGCTCCAGATCTATGGTGCATCCACTTTGCAAAGTGGGGTCCCATCAAGGTTCAGTGGCAGTGGATTTGGGACAGATTTCACTCTCACCATCAGTAGTCTGCAACCTGAAGATTTTGCAACTACTACTGTCAACAGACTTGCAGTACCCCGCTCACTTTCGGCGGAGGGACCAAGGTGGAGATCAAA SEQ ID NO: 24657 | GAGGTGCAGCTGGTGGAGTCTGGGGGAGGCTGGTCAAGCCTGGGGGGTCCCTGAGACTCTCCTGTGCAGCCTCTGGATTCACCTTCAGTAGTTATACCATGAGCTGGGTCCGCCAGGCTCCAGGGAAGGGCTGGAGTGGGTCTCATCCATTAGTGGTAGTAGTAATTACATATACTACGCAGACTCAGTGAAGGGCCGATTCACCATCTCCAGAGACAACGCCAAGAACTCACTGTATCTGCAAATGAACAGCCTGAGAGCCGAGGACACGGCTGTGTATTACTGTGCGAGATTAACTGGTTTTGACTACTGGGGCCAGGGAACCCTGGTCACCGTCTCCTCA SEQ ID NO: 28663 |
| | | AA | DIQMTQFPSSLSTSVGDRVTSTCRASQNIRNFLNWYQQKPEKDPKLQIYGASTLQSGVPSRFSGSGFGTDFTLTISSLQPKDFATYYCQQTCSTPLTFGGGTKVEIK SEQ ID NO: 24658 | EVQLVESGGGLVKPGGSLRLSCAASGFTFSSYTMSWVRQAPGKGLEWVSSISGSSNYIYADSVKGRFTISRDNAKNSLYLQMNSLRAEDTAVYYCARLTGFDYWGQGTLVTVSS SEQ ID NO: 28664 |
| iPS:393084 | 21-225_35C6 | NA | GACATCCAGATGACCCAGTCTCCATCTTCCGTGTCTGCATCTGTAGGAGACAGAGTCACCATCACTTGTGTCGGGCGAGTCAGGGTATTAGCAACAGGGAAAGTTAGCCTGGTATCAGCAGAGAAACCAGGGAAAGCCCCTAAACCCCTGATCTATGCTGCATCCAGTTTGCAGAGTGGGGTCCCAACAAGTTTCACTCTCACCATCAGCAGCCTGCAGCCTGAAGATTTTGCAATTTACTATTGTCAACAGGCTAACAGTTTCCCATTCACTTTCGGCCCTGGGACCAAAGTGGATATCAAA SEQ ID NO: 24659 | CAGGTGCAGTTGGTGCAGTCTGGGACTGAGGTGAAGAAGCCTGGGGCCTCAGTGAAGGTCTCTGCAAGGCTTCTGGATACACCTTCACCGGCGATTATATGCACTGGGTGCGACAGGCCCCTGGACAAGGGCTTGAGTGGATGGGATGGATCAGCCTAAAAATGGTGGCACAAACTATGCACAGAAGTTTCAGGCAGGGTCACCATGACCAGGGACACGTCCATCAGCAGCCTACATGGAGCTGAACAGGCTGAGATCTGACGAACACGGCCGTGTATTACTGTGCGGGAGATGGAACTGGGTCCTTTGACTACTGGGGCCAGGGAACCCTGGTCACCGTCTCCTCA SEQ ID NO: 28665 |

FIGURE 50
(Continued)

| | | | |
|---|---|---|---|
| iPS:393086 | 21-225_36H5 | AA | DIQMTQSPSSVSASVGDRVTITCRASQGISKWLA WYQQKPGKAPKPLIYAASSLQSGVPTRFSGSGS GTDFTLTISSLQPEDFAIYYCQQANSFPFTFGPGT KVDIK<br>SEQ ID NO: 24660 | QVQLVQSGTEVKKPGASVKVSCKASGYTFTGDYM HWVRQAPGQGLEWMGWISPKNGGTNYAQKFQGR VTMTRDTSISTAYMELNRLRSDDTAVYYCARDGT GSFDYWGQGTLVTVSS<br>SEQ ID NO: 28666 |
| | | NA | GACATCCAGATGACCCAGTCTCCATCTTCCGT GTCTGCATCTGTAGGAGACAGAGTCACCATCA CTTGTCGGGCGAGTCAGGGTATTAGCAGATGG TTAGCCTGGTATCAGCAGAAACCAGGGAAAG CCCCTGAACTCCTGATCTATGCTGCATCCCGTT TGCAAAGTGGGATCCCATCCAGGTTCAGCGGC AGTGGATCTGGGACAGACCTTCACTCTCACCAT CAGCAGCCTGCAGCCTGAAGATTTTGCAACTT ACTATTGTCAACAGGCTAACAGTTTCCCTTTCA CTTTCGGCCCTGGGACCAAAGTGGATATCAAA<br>SEQ ID NO: 24661 | CAGGTGCAGCTGGTGCAGTCTGGGGCTGAGGTG AAGAAGCCTGGGGCCTCAATGAAGGTCTCCTGC AAGGCTTCTGGATACACCTTCACCGACTATCATA TGCACTGGGTGCGACAGGCCCCTGGACAAGGGC TTGAGTGGATGGGATGGATCAACCTAATAGGG GTGGCACAAACTATGCACAGAAGTTTCAGGACA GGGTCACCATGACCAGGGACACGTCCATCAGCA CAGCCTACATGGAACTGAACTGAGCAGGCTGAGATCTG ACGACACGGCCGTGTATTTCTGTGCGAGAGATGG AACTGGGTCCTTTGACTACTGGGGCCAGGGAACC CTGGTCACCGTCTCCTCA<br>SEQ ID NO: 28667 |
| | | AA | DIQMTQSPSSVSASVGDRVTITCRASQGISRWLA WYQQKPGKAPELLIYAASRLQSGIPSRFSGSGSG TDFTLTISSLQPEDFATYYCQQANSFPFTFGPGTK VDIK<br>SEQ ID NO: 24662 | QVQLVQSGAEVKKPGASMKVSCKASGYTFTDYHM HWVRQAPGQGLEWMGWINPNRGGINYAQKFQDR VTMTRDTSISTAYMELSRLRSDDTAVYFCARDGTG SFDYWGQGTLVTVSS<br>SEQ ID NO: 28668 |

FIGURE 50
(Continued)

| | | | |
|---|---|---|---|
| iPS:393088 | 21-225_33D1 | NA | GACATCGTGATGACCCAGTCTCCAGACTCCCT GTCTGTGTCTCTTGGGCGAGAGGGCCACCATCA ACTGCAAGTCCATCCAGAGTGTTTATACAGA TCCAACAATAAGAACCTACTTAACTGGTATCA GCAGAAACCAGGACAGCCTCGTAAACTGTTCA TTTATTGGGCATCTACCCGGGAATCCGGGGTC CTTGACCGATTCAGTGGCAGCGGGTGTGGGAC AGATTTCACTCTCACCATCATCAGCCTGCAGG CTGAAGATGTGGCACTTTATTACTGTCAGCAA TATTATAGTTCTCCGTGCAGTTTTGGCCAGGG GACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGACA TTAACTGGGTGCGACAGGCCACTGGACAAGGGC TTGAGTGGATGGGATGGATGCACCTAACAGTGG TAACACAGGCTTTGCACAGAAGTTCCGGGCAG AGTCACCATGACCAGAAACACCTCCATAAGCAC AGCCTACATGGAACTGAGCAGCCTGAGATCTGA GGACACGGCCGTGTATTACTGTGCGAGCAGCAGT GGCTGGTACTTTTTGACTACTGGGGCCAGGGAA CCCTGGTCACCGTCTCCTCA |
| | | | SEQ ID NO: 24663 | SEQ ID NO: 28669 |
| | | AA | DIVMTQSPDSLSVSLGERATINCKSIQSVLYRSNN KNYLTWYQQKPGQPRKLFIYWASTRESGVLDRF SGSGCGTDFTLTIISLQAEDVALYYCQQYYSSPC SFGQGTKLEIK | QVQLVQSGAEVKKPGASVKVSCKASGYTFTNYDIN WVRQATGQGLEWMGWMHPNSGNTGFAQKFRGR VTMTRNTSISTAYMELSSLRSEDTAVYYCASSSGW YFFDYWGQGTLVTVSS |
| | | | SEQ ID NO: 24664 | SEQ ID NO: 28670 |
| iPS:393090 | 21-225_33A5 | NA | GACATCCAGATGACCCAGTCTCCATCCTCACT GTCTGCATCTGTAGGAGACAGAGTCACCATCA CTTGTCGGGCAGTCAGGGCATTAGCAATTAC TTAGCCTGGTTTCAGCAGAAACCAGGGAAAGC CCCTAAGTCCCTGATCTCTGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATATAGTTACCCATTCA CTTTCGGCCCTGGGACCAACGTGGATATCAAA | GAGGTGCAGCTGTGTTAGAGTCTGGGGGAGGCTTG GTACAGCCTGGGGGGTCCCTGAGACTCTCCTGTG CAGCCTCTGGATTCACCTTTAGCAGCTATGTCAT AAACTGGGTCCGCCAGGCTCCAGGGAAGGGCT GGAGTGGGTCTCAGCTATTAGTGGTAGTGGTGTT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAGAACTTCCCT CTTTGACTACTGGGGCCAGGGAACCCTGGTCACC GTCTCCTCA |
| | | | SEQ ID NO: 24665 | SEQ ID NO: 28671 |

FIGURE 50
(Continued)

| | | | |
|---|---|---|---|
| | | AA | DIQMTQSPSSLSASVGDRVTITCRASQGISNYLA WFQQKPGKAPKSLISAASSLQSGVPSKFSGSGSG TDFTLTISSLQPEDFATYYCQQYNSYPFTFGPGT NVDIK<br>SEQ ID NO: 24666 | EVQLLESGGGLVQPGGSLRLSCAASGFTFSSYVINW VRQAPGKGLEWVSAISGSGVSTYYADSVKGRFTIS RDNSKNTLYLQMNSLRAEDTAVYYCARTSLFDYW GQGTLVTVSS<br>SEQ ID NO: 28672 |
| iPS:393092 | 21-225_33C12 | NA | GACATCCAGATGACCCAGTCTCCATCCTCCCT GTCTACATCTGTAGGAGACAGAGTCACCATCA CTTGCCGGGCAAGTCAGAGACATTATCAGTAT TTAAATTGGTATCAGCAGAAACCAGGGAAAG CCCCTAAACTCCTGATCTATGTTGCATCCAGTT TGCAAGGTGGGGTCCCATCCAAGGTTCAATGGC AGTGGATCTGGGACAGATTTCACTCTCACCAT CAGCAGTCTGCAACCTGAAGATTTTGCAACTT ACTACTGTCAACAGAGTTACAGTACCCCGTAC ACTTTCGGCGGGGGGACCAAGGTGGAGATCA AA<br>SEQ ID NO: 24667 | CAGGTGCAGTTGGTGGAATCTGGGGGAGGCGTG GTCCAGCCTGGGAGGTCCCTGAGACTCTCCTGTG CAGCGTCTGATTCACCTTCAGTCAGTCACTATGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAAATAG CAGCTCGTACTACTTTGACTACTGGGGCCAGGGA ACCCTGGTCACCGTCTCCTCA<br>SEQ ID NO: 28673 |
| | | AA | DIQMTQSPSSLSTSVGDRVTITCRASQSIISYLNW YQQKPGKAPKLLIYVASSLQGGVPSRFNGSGSG TDFTLTISSLQPEDFATYYCQQSYSTPYTFGGGT KVEIK<br>SEQ ID NO: 24668 | QVQLVESGGGVVQPGRSLRLSCAASGFTFSHYGM HWVRQAPGKGLEWVAVIWYDGSNKYADSVKGR FTISRDNSKNTLYLQMNSLRAEDTAVYYCARENSS SYYFDYWGQGTLVTVSS<br>SEQ ID NO: 28674 |

FIGURE 50
(Continued)

| | | | | |
|---|---|---|---|---|
| iPS:393094 | 21-225_34C4 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAACAGAAACCAGGGAAAG CCCCTAAGCGCCTGATCTATACTGCATCCAAT TTGCAAAGTGGGGTCCCATCAAGGTTCAGCGG CAGTGGATCTGGGACAGAATTCACTCTCACAA TCAGCAGCCTGCAGCTGAAGATTTGCAACT TATTACTGTCTACAACATAGTTCTTACCCCATC ACCTTTCGGCCAAGGGACACGACTGGAGATTAA A | CAGCTGCAGCTGCAGGAGTCGGGCCCAGGACTG GTGAAGCCTTCGGAGACCCTGTCCTCACCTGCA CTGTCTCTGGTGGCTCCATCAGTAGAAGTAGTTA CTACTGGGGCTGGATCCGCCAGTCCCAGGAA GGGGCTGGAGTGGATTGGGAGTATCTATTATAGT GGGAGCACCGCCTACAATCCGTCCCTCAAGAGTC GAGTCACCATATCCGTAGACACGTCCAAGAACC AGTTCTCCCTGAAGCTGAGCTCCGTGACCGCC AGACACGGCTGTGTATTACTGTGCGAGACTGAGC AGCAGCTGGTCTTTTGACTACTGGGGCCAGGGAA CCCTGGTCACCGTCCTCA |
| | | | SEQ ID NO: 24669 | SEQ ID NO: 28675 |
| | | AA | DIQMTQSPSSLSASVGDRVTITCRASQGIRNDLG WYQQKPGKAPKRLIYTASNLQSGVPSRFSGSGS GTEFTLTISSLQPEDFATYYCLQHSSYPITFGQGT RLEIK | QLQLQESGPGLVKPSETLSLTCTVSGGSISRSSYYW GWIRQSPGKGLEWIGSIYYSGSTAYNPSLKSRVTIS VDTSKNQVSLKLSSVTAADTAVYYCARLSSSWSFD YWGQGTLVTVSS |
| | | | SEQ ID NO: 24670 | SEQ ID NO: 28676 |
| iPS:393096 | 21-225_34D11 | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCTAAGCGCCTGATCTATGCTGCATCCAGT TTGCAAAGTGGGGTCCCATCAAGGTTCAGCGG CAGTGGATCTGGGACAGAATTCACTCTCACAG TCATCAGCCTGCAGCTGAAGATTTTGCAACT TATTACTGTCTACAGCATACTATTTACCCTCCT ACTTTCGGCGGAGGGACCAAGGTGGGGATCA AA | GAGGTGCAGCTGTCGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCCGCTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAGGGGAGTT AGTAGAGGACTACTACTTCTACGGTATGGACGTC TGGGGCCAAGGGACCACGGTCACCGTCTCCTCA |
| | | | SEQ ID NO: 24671 | SEQ ID NO: 28677 |

FIGURE 50
(Continued)

| | | | |
|---|---|---|---|
| | | AA | DIQMTQSPSSLSASVGDRVTITCRASQDIRSDLG WYQQKPGKAPKRLIYAASSLQSGVPSRFSGSGS GTEFTLTVISLQPEDFATYYCLQHTIYPPTFGGGT KVGIK<br><br>SEQ ID NO: 24672 | EVQLSESGGGLVQPGGSLRLSCAASGFTFSSYAMN WVRQAPGKGLEWVSAISGRGGSTHADSVKGRFTI SRDNSKNTLYLQMNSLRAEDTAVYYCVKGELVED YYFYGMDVWGQGTTVTVSS<br><br>SEQ ID NO: 28678 |
| iPS:393098 | 21-225_35G6 | NA | GACATCCAGATGACCCAGTCTCCATCTTCCGT GTCTGCATCTGTAGGCGACAGACTCACCATCA CTTGTCGGGCGAGTCAGGGTATTAGCCGGTGG TTAGCCTGGTATCAGCAGAAAGTGGGGAAAGT CCCCAAACTCCTGATCTATGCTGCATCCAGGT TGCAAAGTGGGGTCCCATCAAGGTTCAGCGGC AGTGGATCTGGGACAGCTTTCACTCTCACCAT CGGCAGCCTGCAGCCTGAAGATTTTGCAACTT ACTATTGTCAACAGGCTAACAGTTTCCCGTTC ACTTTCGGCCCTGGGACCAAAGTGGATCTCAA A<br><br>SEQ ID NO: 24673 | CAGGTGCAGCTGGTGCAGTCTGGGGCTGACGTG AAGAAGCCTGGGGCTCAGTGAAGGTCTCCTGC AAGGCTTCTGGATACACCTTCACCGACTACCATA TACACTGGGTGCGACAGGCCCCTGGACAAGGGC TTGAGTGGATGGGATGGATCAACCCTAACAATGG TGGCACACACTATGCACAGGAGTTTCAGGGCAG GGTCACCATGACCAGGGACACAGTCCATCAGCAC AGCCTACATGGAGCTGAGTAGCCTGAGATCTGAC GACACGGCCGTGTATTACTGTGCGAGAGATGGA ACTGGGTCCTTTGACTACTGGGGCCAGGGAACCC TGGTCACCGTCTCCTCA<br><br>SEQ ID NO: 28679 |
| | | AA | DIQMTQSPSSVSASVGDRLTITCRASQGISRWLA WYQQKPGKVPKLLIYAASRLQSGVPSRFSGSGS GTAFTLTIGSLQPEDFATYYCQQANSFPFTFGPG TKVDLK<br><br>SEQ ID NO: 24674 | QVQLVQSGADVKKPGASVKVSCKASGYTFTDYHI HWVRQAPGQGLEWMGWINPNNGGTHYAQEFQGR VTMTRDTSISTAYMELSSLRSDDTAVYYCARDGTG SFDYWGQGTLVTVSS<br><br>SEQ ID NO: 28680 |

FIGURE 50
(Continued)

| | | | | |
|---|---|---|---|---|
| iPS:393100 | 21-225_36B8 | NA | GACATCCAGATGACCCAGTCTCCATCCTCCCT GTCTACTTCTGTAGGAGACAGAGTCACCATCA CTTGCCGGGCAAGTCAGAGACATTATCAGCTAT TTAAATTGGTATCAGCAGAAACCAGGGAAAG CCCCTAAACTCCTGATCTATGTTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCGACTT ACTACTGTCAACAGAGTTACAGTACCCGTAC ACTTTCGGCGGAGGGACCAAGATGGAGATCA AA | CAGGTGCAGTTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAGTTATATGGCATGATGAAG TAATAAATACTATGGAGACTCCGTGAAGGGCCG ATTCACCATCTCCAGAGACAATTCCAAGAACACA CTGTATCTGCAAATGAACAGCCTGAGAGCCGAG GACACGGCTGTGTATTACTGTGCGAGAGAAATA GCAGCTCGTACTACTTTGACTACTGGGGCCAGGG AACCCTGGTCACCGTCTCCTCA |
| | | | SEQ ID NO: 24675 | SEQ ID NO: 28681 |
| | | AA | DIQMTQSPSSLSTSVGDRVTITCRASQSIISYLNW YQQKPGKAPKLLIYVASSLQSGVPSRFSGSGSGT DFTLTISSLQPEDFATYYCQQSYSTPYTFGGGTK MEIK | QVQLVESGGGVVQPGRSLRLSCAASGFTFSNYGM HWVRQAPGKGLEWVAVIWHDGSNKYYGDSVKGR FTISRDNSKNTLYLQMNSLRAEDTAVYYCARENSS SYYFDYWGQGTLVTVSS |
| | | | SEQ ID NO: 24676 | SEQ ID NO: 28682 |
| iPS:393102 | 21-225_33F1 | NA | GACATCCAGATGACCCAGTCTCCATCCTCCCT GTCTGCATCTGTAGGAGACAGAGTCACCATCA CTTGCCGGGACAAGTCAGGACATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAATT TATTACTGTCTACAGCATAATATTACCCCTCCT ACTTTCGGCGGAGGGACCAAGGTGGAGATCA AA | GAGGTGCAGCTGTTGGAGTCTGGGGGAGGCTTGC TACAGCCGGGGGGGTCCCTGAGACTCTCCTGTGC AGCCTCTGGATTCACCTTTAGCAGCTATAGCCATG AGCTGGGTCCGCCAGGCTCCAGGGAAGGGGCTG GAGTGGGTCTCTCTATTAGTGGTGGTGGTGGTA GCACATTCCACGCAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGTGAAGGGGGAGCTAC TTGAGGACTACTACTTCTACGGTATGGACTCTG GGGCAAGGGACCACGGTCACCGTCTCCTCA |
| | | | SEQ ID NO: 24677 | SEQ ID NO: 28683 |

FIGURE 50
(Continued)

| | | | | |
|---|---|---|---|---|
| | | | AA | DIQMTQSPSSLSASVGDRVTITCRTSQDIRSDLG WYQQKPGKAPKRLIYAASSLQSGVPSRFSGSGS GTEFTLTISSLQPEDFAIYYCLQHTIYPPTFGGGT KVEIK | EVQLLESGGGLLQPGGSLRLSCAASGFTFSSYAMS WVRQAPGKGLEWVSSISGRGGSTFHADSVKGRFTI SRDNSKNTLYLQMNSLRAEDTAVYYCVKGELLED YFYGMDVWGQGTTVTVSS |
| | | | | SEQ ID NO: 24678 | SEQ ID NO: 28684 |
| iPS:393104 | 21-225_33A7 | | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAGCAGAAACCAGGAAAG CCCCTAAGCGCCTGATCTATGTTGCATCCAGT TGCAAAGTGGGGTCCCATCAAGGTTCAGCGGC AGTGGATCTGGGACAGAGAATTCACTCTCACAAT CAGCAGCCTGCAGCCTGAAGATTTTGCAGCAT ATTACTGTCTACAGCATACTATTTACCCTCCTA CTTTCGGCGGAGGGACCAAGGTGGAGATCAA A | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTGTGCCAT GAGCTGGGTCCGCCAGGCTCCAGGGAAGGGGCT GGAGTGGGTCTCCGCTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAAGGGAACT ACTAGAGGACTACTTCTACGGTATGGACGTC TGGGGCCAAGGGACCACGGTCACCGTCTCCTCA |
| | | | | SEQ ID NO: 24679 | SEQ ID NO: 28685 |
| | | | AA | DIQMTQSPSSLSASVGDRVTITCRASQDIRSDLG WYQQKPGKAPKRLIYVASSLQSGVPSRFSGSGS GTEFTLTISSLQPEDFAAYYCLQHTIYPPTFGGGT KVEIK | EVQLLESGGGLVQPGGSLRLSCAASGFTFSSCAMS WVRQAPGKGLEWVSAISGRGGSTFHADSVKGRFTI SRDNSKNTLYLQMNSLRAEDTAVYYCVKGELLED YFYGMDVWGQGTTVTVSS |
| | | | | SEQ ID NO: 24680 | SEQ ID NO: 28686 |

FIGURE 50
(Continued)

| | | | | |
|---|---|---|---|---|
| iPS:393106 | 21-225_34A6 | NA | GACATCCAGATGACCCAGTCTCCATCCTCCCT GTCTGCATCTGTAGGAGACAGAGTCACCATCA CTTGCCGGACAAGTCAGGACATCAGAAATGAT TTAGGCTGGTATCAGCAGAAACCAGGGAAAG CCCCTAAGCGCCTGATCTTTGCTGCATCCAGTT TGCAAAGTGGGGTCCCATCAAGATTCAGCGGC AGTGGATCTGGGACAGAATTCACTCTCACAGT CAGCAGCCTGCAGCCTGAAGATTTTGCAACTT ATTACTGTCTACAGCATAATAGTTACCCTCCTA CTTTCGGCGGAGGGACCAAGGTGGAGATCAA A | GAGGTGCAGCTGTTGGAGTCTGGGGAGGCTTG GTACAGCCTGGGGGGTCCCTGAGACTCTCCTGTG CAGCCCTCTGATTCACCTTTAACAACTATGCCAT GAACTGGGTCCGCCAGGCTCCAGGGAAGGGCT GGAGTGGGTCTCAGTATTAGTCGTCGTGGTGGT AGCACATTCTACGCAGACTCCGTGAAGGGCCGGT TCACCATCTCCAGAGACAATTCCAAGAACACTCT GTATCTCCAAATGAACAGCCTGAGAGCCGAGGA CACGGCCGTATATTACTGTGCGAAAGGGGAGCT ACTAGAGGACTACTACTCTGCTATGACGTC TGGGGCCAAGGGACCACGGTCACCGTCTCCTCA |
| | | | SEQ ID NO: 24681 | SEQ ID NO: 28687 |
| | | AA | DIQMTQSPSSLSASVGDRVTITCRTSQDIRNDLG WYQQKPGKAPKRLIFAASSLQSGVPSRFSGSGSG TEFTLTVSSLQPEDFATYYCLQHNSYPPTFGGGT KVEIK | EVQLLESGGGLVQPGGSLRLSCAASGFTFNNYAMN WVRQAPGKGLEWVSAISRRGGSTFYADSVKGRFTI SRDNSKNTLYLQMNSLRAEDTAVYYCAKGELLED YYYFAMDVWGQGTTVTVSS |
| | | | SEQ ID NO: 24682 | SEQ ID NO: 28688 |
| iPS:393108 | 21-225_34G11 | NA | GACATCCAGATGACCCAGTCTCCATCCTCCCT GTCTGCATCTGTGGGAGACAGAGTCACCATCA CTTGCCGGGCAAGTCAGAGACATTAACCAGTAT TTAAATTGGTATCAGCAGAAACCAGGGAAAG CCCCTAAGCTCCTGATCTATGGTGCATCCAGTT TGCAAAGTGGGGTCCCATCAAGGTTCAGTGGC AGTGGATCTGGGACAGATTTCACTCTCACCAT CAGCAGCCTGCAACAGATGAAGATTTTGCAACTT ACTACTGTCAACAGACTTACATTACCCCGCTC ACTTTCGGCGGAGGGACCAAGGTGGAGATCA AA | CAGGTGCAGCTGCAGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAGGGGC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGCTGAGATCTGA CGACACGGCCGTGTATTACTGTGCGAGAGATATT AGTAATTTCAGCAGCTGGTACGATTACTACGCTA TGGACGTCTGGGGGCCAAGGGACCACGGTCACCG TCTCCTCA |
| | | | SEQ ID NO: 24683 | SEQ ID NO: 28689 |

FIGURE 50
(Continued)

| | | | | |
|---|---|---|---|---|
| | | AA | DIQMTQSPSSLSASVGDRVTITCRASQNINRYLN WYQQKPGKAPKLLIYGASSLQSGVPSRFSGSGS GTDFTLTISTLQPEDFATYYCQQTYITPLTFGGGT KVEIK | QVQLVQSGAEVKKPGASVKVSCKASGYTFTGYYM HWVRQAPGQGLEWMGWINPNSGGTNYAQKFQGR VTMTRDTSISTAYMELSRLRSDDTAVYYCARDISNF SSWYDYYAMDVWGQGTTVTVSS |
| | | | SEQ ID NO: 24684 | SEQ ID NO: 28690 |
| iPS:393110 | 21-225_35B7 | NA | GACATCCAGATGACCCAGTCTCCATCCTCCCT GTCTGCATCTGTAGGAGACAGAATCACCATCA CTTGCCGGGCAAGTCAGGACATTAGAAGTGAT TTAGGCTGGTATCAGCAGAAACCAGGAAAG CCCCTGAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATACTATTTACCCTCCT ACTTTCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTGTGGTGGT AGCACATTCCACGCAGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAAGGGGAGCT ACTAGAGGACTACTACTTCTACGGTATGGACGTC TGGGGCCAAGGGACCACGGTCACCGTCTCCTCA |
| | | | SEQ ID NO: 24685 | SEQ ID NO: 28691 |
| | | AA | DIQMTQSPSSLSASVGDRITITCRASQDIRSDLGW YQQKPGKAPERLIYAASSLQSGVPSRFSGSGSGT EFTLTISSLQPEDFATYYCLQHTIYPPTFGGGTKV EIK | EVQLLESGGGLVQPGGSLRLSCAASGFTFSSYAMS WVRQAPGKGLEWVSAISGRGGSTFHADSVKGRFTI SRDNSKNTLYLQMNSLRAEDTAVYYCVKGELLED YYFYGMDVWGQGATVTVSS |
| | | | SEQ ID NO: 24686 | SEQ ID NO: 28692 |

FIGURE 50
(Continued)

| | | | |
|---|---|---|---|
| iPS:393112 | 21-225_33G1 | NA | GACATCCAGATGACCCAGTCTCCATCTTCCGT GTCTGTGTCTGTGGGAGACAGAGTCACCATCA CTTGTCGGGCGAGTCAGGGTATTAGCAGGTGG TTAGCCTGGTATCAGCAGAAACCTGGGAAAGC CCCAAAGCTCCTGATCTATGGTGCATACAGTC TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A |
| | | | SEQ ID NO: 24687 |
| | | AA | DIQMTQSPSSVSVSVGDRVTITCRASQGISRWLA WYQQKPGKAPKLLIYGAYSLQSGVPSRFSGSGS GTDFTLTISSLQPEDFATYYCQQANSFPFTFGPGT KVDIK |
| | | | SEQ ID NO: 24688 |
| iPS:393114 | 21-225_33G12 | NA | GACATCCAGATGACCCAGTCTCCATCTCCCT GTCTGCATCTGTAGGAGACAGAGTCACCATCA CTTGCCGGGCAAGTCAGAGCATTAGCAACTAT TTAAATTGGTATCAACAGCAAACAGGGAAAG CCCCTAAGTCTCCTGATTTATGCTGCATCCAGT TGCAAAGTGGGGTCCCATCAAGGTTCAGTGGC AGTGGATCTGGGACAGATTTCACTCTCACCAT CAGCAGTCTGCAACCTGAAGATTACAGTCCAT ACTACTGTCAACAGAGTTACAGTACCCCATTC ACTTTCGGCGGCCCTGGGACCAAAGTGGATATCAA A |
| | | | SEQ ID NO: 24689 |

| | | | |
|---|---|---|---|
| | | | CAGGTGCAGTTGGCGGCAGTCTGGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGGTGGATCAGCCCTAACAATGG TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGAGATGG AACTGGGTCCTTTGACTACTGGGGCCAGGGAACC CTGGTCACCGTCTCCTCA |
| | | | SEQ ID NO: 28693 |
| | | | QVQLAQSGAEVKKPGASVKVSCKASGYTFTGYYM HWVRQAPGQGLEWMGWISPNNGGTNYAQKFQGR VTMTRDTSISTAYMELSRLRSDDTAVYYCARDGTG SFDYWGQGTLVTVSS |
| | | | SEQ ID NO: 28694 |
| | | | GAGGTGCAGCTGTTGGAGTCTGGGGGAGACATG GTCCAGCCTGGGGGGTCCCTGAGACTCTCCTGTG CAGCCTCCGGATTCACCTTTAGCAGTCATGCCAT GAGCTGGGTCCGCCAGGCTCCAGGGAAGGGGCT GGAGTGGGTCTCAGTTATTAGTGGTAGTGGTGGT AGTCATTCTACGCAGATCCGTGAAGGGCCGGT TCACCATCTCCAGAGACAATTCCAAGAACACGCT GTATCTGCAAATGAACAGCCTGAGGGCCGAGGA CACGGCCGTATATTACTGTGCGAAAGATGGGTG AGAGCTCATGATGGTTTGATATCTGGGGCCAAG GGACAAATGGTCACCGTCTCTTCA |
| | | | SEQ ID NO: 28695 |

FIGURE 50
(Continued)

| | | AA | DIQMTQSPSSLSASVGDRVTITCRASQSISNYLN WYQQKPGKAPKFLIYAASSLQSGVPSRFSGSGS GTDFTLTISSLQPEDFATYYCQQSYSTPFTFGPGT KVDIK<br><br>SEQ ID NO: 24690 | EVQLLESGGDMVQPGGSLRLSCAASGFTFSSYAMS WVRQAPGKGLEWVSVISGSGSSFYADSVKGRFTI SRDNSKNTLYLQMNSLRAEDTAVYYCAKDRVRAH DGFDIWGQGTMVTVSS<br><br>SEQ ID NO: 28696 |
|---|---|---|---|---|
| iPS:393116 | 21-225_34G7 | NA | GACATCCAGATGACCCAGTCTCCATCTTCCGT GTCTGCATCTGTAGGAGACAGAGTCACCATCA CTTGTCGGGCGAGTCAGTTATTAGCAAGTGG TTAGCCTGGTATCAGCAGAAACCAGGAAAG CCCCTAAACTCCTGATCTATGCTGCATCCAGTT TGCAAAGTGGGGTCCCATTAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A<br><br>SEQ ID NO: 24691 | CAGGTGCAGCTGGTGCAGTCTGGGGCTGAGGTG AAGAAGCCTGGGGCCTCAGTGAAGGTCTCCTGC AGGGCTTCTGGATACACCTTCACCGACTACCATA TTCACTGGGTGCGACAGGCCCCTGGACAAGGCT TGAGTGGATGGGATGGATCAACCCTAACAATGGT GGCACACACTATGCACAGAAGTTTCAGGGCAGG GTCACCATGACCAGGGACACGTCCATCAGCACA GCCTACATGGAGCTGAGCAGGCTGAGATCTGAC GACACGGCCGTGTATTATTGTGCGAGAGATGAA CTGGGTCCTTTGACTACTGGGGCCAGGGAAACCT GGTCACCGTCTCCTCA<br><br>SEQ ID NO: 28697 |
| | | AA | DIQMTQSPSSVSASVGDRVTITCRASQLISKWLA WYQQKPGKAPKLLIYAASSLQSGVPLRFSGSGS GTDFTLTISSLQPEDFATYYCQQANSFPFTFGPGT KVDIK<br><br>SEQ ID NO: 24692 | QVQLVQSGAEVKKPGASVKVSCRASGYTFTDYHIH WVRQAPGQGLEWMGWINPNNGGTHYAQKFQGRV TMTRDTSISTAYMELSRLRSDDTAVYYCARDGTGS FDYWGQGNLVTVSS<br><br>SEQ ID NO: 28698 |

FIGURE 50
(Continued)

| | | | | |
|---|---|---|---|---|
| iPS:393118 | 21-225_34H11 | NA | GACATCCAGATGACCCAGTCTCCATCCTCCT GTCTGCATCTGTCGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCTCCT ACTTTCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAGGGCT GGAGTGGGTCTCCGCTATTAGTGGTGTGGTGGT AGCACATTCTACGCAGACTCCGTGAAGGGCCGGT TCACCATCTCCAGAGACAATTCCAAGAACACGCT GTTTCTGCAAATGAACAGCCTGAGAGCCGAGGA CACGGCCGTTTATTACTGTGCGAAAGGGAGCTA CTAGAGGACTACTACTACGTATGGACGTCT GGGGCCAAGGGACCACGGTCACCGTCTCCTCA |
| | | | SEQ ID NO: 24693 | SEQ ID NO: 28699 |
| | | AA | DIQMTQSPSSLSASVGDRVTITCRASQDIRNDLG WYQQKPGKAPKRLIYATSSLQSGVPSRFSGSGSG TEFTLTISSLQPEDFATYYCLQHNSYPPTFGGGTK VEIK | EVQLLESGGGLVQPGGSLRLSCAASGFTFSSYAMN WVRQAPGEGLEWVSAISGRGGSTFYADSVKGRFTI SRDNSKNTLFLQMNSLRAEDTAVYYCAKGELLED YYYYGMDVWGQGTTVTVSS |
| | | | SEQ ID NO: 24694 | SEQ ID NO: 28700 |
| iPS:393120 | 21-225_35H8 | NA | GACATCCAGATGACCCAGTCTCCATCCTCACT GTCTGCATCTGTAGGAGACAGAGTCACCATCA CTTGTCGGGCGAGTCAGGCCATTAGTAATTAT TTAGCCTGGTTTCAGCAGAAACCAGGGAAAGC CCCTAAGTCCCTGATCTATGGTGCGTCCGGTTT GCAAAGTGGGGTCCCATCAAGTTCAGCGGCA GTGGATCTGGGACAGATTTCACTCTCACCATC AGCAGCCTGCAGCCTGAAGATATAATAGTTACTTA TTACTGCCAACAGTATATAGTTACCAACTTA CTTTCGGCGGCGGGACCAAGGTGGATTTCAAA | GAGGTTCAACTGGTGGAGTCTGGGGGAGGCCTG GTCAAGCCTGGGGGGTCCCTGAGACTCTCCTGTG CAGCCTCTGGATTCACCTTCAGTAGTTATAGCAT GAACTGGGTCCGCCAGGCTCCAGGGAAGGGCT GGAGTGGGTCTCGTCCATTAGTGGTACTGGTAGT TTCATATACTACGCAGACTCAGTGAAGGGCCGAT TCACCATCTCCAGAGACAACAAGCCAAGAAATCAG TGTATCTGCAAATGAACAGCCTGAGAGCCGAGG ACACGGCTGTGTATTACTGTGCGAGAGTCTCTGG CTTTGACTACTGGGGCCAGGGAACCCTGGTCACC GTCTCCTCA |
| | | | SEQ ID NO: 24695 | SEQ ID NO: 28701 |

FIGURE 50
(Continued)

| | | | |
|---|---|---|---|
| iPS:393122 | 21-225_33B2 | AA | DIQMTQSPSSLSASVGDRVTITCRASQAISNYLA WFQQKPGKAPKSLIYGASGLQSGVPSKFSGSGS GTDFTLTISSLQPEDFATYYCQQYNSYPFTFGPG TKVDFK<br><br>SEQ ID NO: 24696 | EVQLVESGGGLVKPGGSLRLSCAASGFTFSSYSMN WVRQAPGKGLEWVSSISGTGSFIYYADSVKGRFTIS RDNAKKSVYLQMNSLRAEDTAVYYCARVSGFDY WGQGTLVTVSS<br><br>SEQ ID NO: 28702 |
| | | NA | GACATCCAGATGACCCAGTCTCCATCCTCCCT GTCTACATCTGTCGGAGACAAAGTCACCATCA CTTGCCGGGCAAGTCAGAGCATTATCAGTTAT TTAAATTGGTATCAGCAGAAACCAGGGAAAG CCCCTAAACTCCTGATCTATGGTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCGTAC ACTTTCGGCGGGGGGACTAAGGTGGAGATCA AA | CAGGTGCAGTTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGCAGTGATGGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAAATA GCAGCTCGTACTACTTTGACTACTGGGGCCAGGG AACCCTGGTCACCGTCTCCTCA<br><br>SEQ ID NO: 28703 |
| | | AA | DIQMTQSPSSLSTSVGDKVTITCRASQSIISYLNW YQQKPGKAPKLLIYVASSLQSGVPSRFSGSGSGT DFTLTISSLQPEDFATYYCQQSYSTPYTFGGGTK VEIK<br><br>SEQ ID NO: 24698 | QVQLVESGGGVVQPGRSLRLSCAASGFTFSNYGM HWVRQAPGKGLEWVAVIWHDGSNKYYADSVKGR FTISRDNSKNTLYLQMNSLRAEDTAVYYCARENSS SYYFDYWGQGTLVTVSS<br><br>SEQ ID NO: 28704 |

FIGURE 50
(Continued)

| | | | | |
|---|---|---|---|---|
| iPS:393124 | 21-225_33G7 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGATTTCACTCTCACAATCAGCAGCCTGCAGCCTGAAGATTTTGCAACATATTACTGTCTACAGCATTATAGTTACCCTCCTACTTTCGGCGGAGGGACCAAGGTGGAGATCAAA SEQ ID NO: 24699 | GAGGTTCAATTGTTGGAGTCTGGGGGAGGCTTGGTACAGCCTGGGGGGTCCCTGAGACTCTCCTGTGCAGCCTCTGGATTCACCTTTAGCAACTATGCCATGAGCTGGGTCCGCCAGGCTCCAGGGAAGGGCTGGAGTGGGTCTAGTTACTATTAGTCGTGTGGTGTAGCACATTCTACGCAGACTCCGTGAAGGGCCAGTTCACCATTTCCAGAGACAATTCCAAGAACACGCTGTATCTGCAAATGAACAGCCTGAGAGCCGAGGACACGGCCGTGTATTACTGTGCGAAAGGGAGCTACTAGAGGACTACTCCTACTACGGTATGGACGTCTGGGGCCAGGGGACCACGGTCACCGTCTCCTCA SEQ ID NO: 28705 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHYSYPPTFGGGTKVEIK SEQ ID NO: 24700 | EVQLLESGGGLVQPGGSLRLSCAASGFTFSNYAMSWVRQAPGKGLEWVSAISRRGGSTFYADSVKGQFTISRDNSKNTLYLQMNSLRAEDTAVYYCAKGELLEDYSYYGMDVWGQGTTVTVSS SEQ ID NO: 28706 |
| iPS:393126 | 21-225_35D1 | NA | GACATCCAGATGACCCAGTCTCCATCCTCCCTGTCTGCATCTGTAGGAGACAGAGTCACCATCACTTGCCGGGCAAGTCAGGACAGTCATTAGAAGTGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGATTTCACTCTCACAATCAGCAGCCTGCAGCCTGAAGATTTTGCAACTTATTACTGTCTACAGCATACTATTTACCCTCCCACTTTCGGCGGGGGGACCAAGGTGGAGATCA SEQ ID NO: 24701 | GAGGTGCAACTGTTGGAGTCTGGGGGAGGCTTGGTACAGCCTGGGGGGTCCCTGAGACTCTCCTGTGCAGCCTCTGGATTCACCTTTAGCAGTATGCCATGAGCTGGGTCCGCCAGGCTCCAGGGAAGGGGCTGGAGTGGGTCTCCGCTATTAGTGGTCGTGGTGGTAGCACATTCTACGCAGACTCCGTGAAGGGCCGGTTCACCATCTCCAGAGACAATTCCAACACGCTGTATCTGCAAATGAACAGCCTGAGAGCCGAGGACACGGCCGTGTATTACTGTGTGAAGGGAGTTACTAGAGGACTACTTCTACGGTATGGACGTCTGGGGCCAAGGGGCCACGGTCACCGTCCTCA SEQ ID NO: 28707 |

FIGURE 50
(Continued)

| | | | | |
|---|---|---|---|---|
| iPS:393128 | 21-225_35F11 | AA | DIQMTQSPSSLSASVGDRVTITCRASQDIRSDLG WYQQKPGKAPKRLIYAASSLQSGVPSRFSGSGS GTEFTLTISSLQPEDFATYYCLQHTIYPPTFGGGT KVEIK | EVQLLESGGGLVQPGGSLRLSCAASGFTFSSYAMS WVRQAPGKGLEWVSAISGRGGSTFHADSVKGRFTI SRDNSNNTLYLQMNSLRAEDTAVYYCVKGELLED YFYGMDVWGQGATVTVSS |
| | | | SEQ ID NO: 24702 | SEQ ID NO: 28708 |
| | | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATATACTGTTACCCTCCT ACTTTCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTCGTGGTGGT AGCACATTCCACGCAGACTCCATGAAGGGCCGG TTCACCATCTCCAGAGACAACAATTCCAAGAACACGC TGTATCTGCAAATGAACAGCCTGAGAGCCGAGG ACACGGCCGTATATTACTGTGTGAAAGGGGAGCT ACTAGAGGACTACTACTTCTACGGTATGGACGTC TGGGGCCAAGGGACCACGGTCACCGTCTCCTCA |
| | | | SEQ ID NO: 24703 | SEQ ID NO: 28709 |
| | | AA | DIQMTQSPSSLSASVGDRVTITCRASQDIRSDLG WYQQKPGKAPKRLIYAASSLQSGVPSRFSGSGS GTEFTLTISSLQPEDFATYYCLQHTVPPTFGGG TKVEIK | EVQLLESGGGLVQPGGSLRLSCAASGFTFSSYAMS WVRQAPGKGLEWVSAISGRGGSTFHADSMKGRFTI SRDNSKNTLYLQMNSLRAEDTAVYYCVKGELLED YFYGMDVWGQGTTVTVSS |
| | | | SEQ ID NO: 24704 | SEQ ID NO: 28710 |

FIGURE 50
(Continued)

| | | | |
|---|---|---|---|
| iPS:393130 | 21-225_33C2 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCAGAAACCAGTGAAAGC CCCTAAGCGCCTGATCTATGCTGCACCCAGTT TGCAAAGTGGGGTCCCATCAAGGTTCAGCGGC AGTGGATCTGGGACAGAATTCACTCTCACAAT CAGCAGCCTGCAGCCTGAACATTACCCGTGG ATTACTGTCTACAGCATAATAGTTACCCTTGG ACGTTCGGCCAGGGACCAAGGTGGAAATCA AA<br><br>SEQ ID NO: 24705 | GAGGTGCAACTGGTGGAGTCTGGGGGAGGCTG GTCAAGCCGGGGGGGTCCCTGAGACTCTCCTGTG CAGCCTCTGGATTCACCTTCAGTAGCTATACCAT GAACTGGGTCCGCCAGGCTCCAGGGAAGGGGCT GCAGTGGGTCTCATCCATTAGTGGTAGTAGTAGT TACATATACTACGGGACTCAGTGAAGGCCGAT TCACCATCTCCAGAGACAACGCCAAGAACTCACT GTTTCTGCAAATGAACAGCCTGAGAGCCGAGGA CACGGCTATCTTTTACTGTGCGCGAGATCGGGGG GGGACCTGGGGCCAGGGAACCCTGGTCACCGTC TCCTCA<br><br>SEQ ID NO: 28711 |
| | | AA | DIQMTQSPSSLSASVGDRVTITCRASQGIRNDLG WYQQKPVKAPKRLIYAAPSLQSGVPSRFSGSGS GTEFTLTISSLQPEHFATYYCLQHNSYPWTFGQG TKVEIK<br><br>SEQ ID NO: 24706 | EVQLVESGGGLVKPGGSLRLSCAASGFTFSSYTMN WVRQAPGKGLQWVSSISGSSSYIYYADSVKGRFTIS RDNAKNSLFLQMNSLRAEDTAIFYCARDRGGTWG QGTLVTVSS<br><br>SEQ ID NO: 28712 |
| iPS:393132 | 21-225_33H7 | NA | GACATCCAGATGACCCAGTCTCCATCTTCCGT GTCTGCATCTGTAGGCGACAGAGTCACCATCA CTTGTCGGGCGAGTCAGGGTATTAGCAGGTGG TTAGCCTGGTATCAGCAGAAAGTGGGGAAAGT CCCCAAACTCCTGATCTATGCTGCATCCAGGT TGCAAAGTGGGGTCCCATCAAGGTTCAGCGGC AGTGGATCTGGGACAGATTTCACTCTCACAAT CGGCAGCCTGCAGCCTGAAGATTTTGCAACTT ACTATTGTCAACAGGCTAACATTTTCCGTTCA CTTTCGGCCCTGGGACCAAAGTGGATCTCAAA<br><br>SEQ ID NO: 24707 | CAGGTGCAGCTGGTGCAGTCTGGGGCTGACGTG AAGAAGCCTGGGGCCTCAGTGAAGGTCTCCTGC AAGGCTTCTGGATACACCTTCACCGACTACCATA TACACTGGGTGCGACAGGCCCCTGGACAAGGGC TTGAGTGGATGGGATGGATCAACCTAACAATGG TGGCACACACTATGCACAGGAGTTCAGGGCAG GGTCACCATGACCAGGGACACGTCCATCAGCAC AGCCTACATGGAACTGAGTAGCCTGAGATCTGAC GACACGGCCGTGTATCACTGTGCGAGAGATGGA ACTGGGTCCTTTGACTACTGGGGCCAGGGAACCC TGGTCACCGTCTCCTCA<br><br>SEQ ID NO: 28713 |

FIGURE 50
(Continued)

| | | | |
|---|---|---|---|
| | | AA | DIQMTQSPSSVSASVGDRVTITCRASQGISRWLAWYQQKVGKVPKLLIYAASRLQSGVPSRFSGSGSGTDFTLTIGSLQPEDFATYYCQQANIFPFTFGPGTKVDLK<br>SEQ ID NO: 24708 | QVQLVQSGADVKKPGASVKVSCKASGYTFTDYHIHWVRQAPGQGLEWMGWINPNNGGTHYAQEFQGRVTMTRDTSISTAYMELSSLRSDDTAVYHCARDGTGSFDYWGQGTLVTVSS<br>SEQ ID NO: 28714 |
| iPS:393134 | 21-225_34C2 | NA | GACATCCAGATGACCCAGTCTCCATCCTCCCTGTCTACATTTGTAGGAGACAGAGTCACCATCCTTGTCGGGCAAGTCAGAGTCAGAGAATTATCAGTGATTTAAATTGGTTTCAGCAGAAACCAGGGAAAGCCCCTAAACTCCTGATCTATGTTGCATCCAGTTTGCAAAGTGGGGTCCCGTCAAGGTTCAGTGGCAGTGGATCTGGGACATATTTCACTCTCACCATCAGCAGTCTGCAACCTGCAACAGATTTTGCGACTTACTACTGTCAACAGAGTTACAGTACCCCGTACACCTTTCGGCGGAGGGACCAAGATGGAGATCAAA<br>SEQ ID NO: 24709 | CAGGTGCAGTTGGTGGAGTCTGGGGGAGGCGTGGTCCAGCCTGGGAGGTCCCTGAGACTCTCCTGTGCAGCGTCTGGATTCACCTTCAGTAACTATGTCATGCACTGGGTCCGCCAGGCTCCAGGCAAGGGGCTGGAGTGGGTGGCACTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAAATAGCAGCTCGTACTACTTTGACTACTGGGGCCAGGGAACCCTGGTCACCGTCTCCTCA<br>SEQ ID NO: 28715 |
| | | AA | DIQMTQSPSSLSTFVGDRVTITCRASQRIISYLNWFQQKPGKAPKLLIYVASSLQSGVPSRFSGSGSGTYFTLTISSLQPEDFATYYCQQSYSTPYTFGGGTKMEIK<br>SEQ ID NO: 24710 | QVQLVESGGGVVQPGRSLRLSCAASGFTFSNYVMHWVRQAPGKGLEWVALIWYDGSNKYYADSVKGRFTISRDNSKNTLYLQMNSLRAEDTAVYYCARENSSSYYFDYWGQGTLVTVSS<br>SEQ ID NO: 28716 |

FIGURE 50
(Continued)

| | | | | |
|---|---|---|---|---|
| iPS:393136 | 21-225_34D8 | NA | GACATCCAGATGACCCAGTCTCCATCCTCCT GTCTACATCTGTAGGAGACAGAGTCACCATCA CTTGCCGGGCAAGTCAGATCATTATCAGCTAT TTAAATTGGTATCAGCAGAAACCAGGGAAAG CCCCTAAACTCCTGATCTTTGTTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCGTAC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAATAG CAGCTCGTACTACTTTGACTACTGGGGCCAGGGA ACCCTGGTCACCGTCTCCTCA |
| | | | SEQ ID NO: 24711 | SEQ ID NO: 28717 |
| | | AA | DIQMTQSPSSLSTSVGDRVTITCRASQIISYLNW YQQKPGKAPKLLIFVASSLQSGVPSRFSGSGSGT DFTLTISSLQPEDFATYYCQQSYSTPYTFGGGTK VEIK | QVQLVESGGGVVQPGRSLRLSCAASGFTFSNYGM HWVRQAPGKGLEWVAVIWYDGSNKYYADSVKGR FTISRDNSKNTLYLQMNSLRAEDTAVYYCARENSS SYYFDYWGQGTLVTVSS |
| | | | SEQ ID NO: 24712 | SEQ ID NO: 28718 |
| iPS:393138 | 21-225_35E3 | NA | GACATCCAGATGACCCAGTCTCCATCCTCCCT GTCTGCATCTGTAGGAGACAGAGTCACCATCA CTTGCCAGGCGAGTCAGGACAGTCAACTAT TTAAATTGGTATCAGCAGAAACCAGGAAAAG CCCCTAAACTCCTGATCTACGATGCCTCCAATT TGGAAACAGGGGTCCCATCAAGGTTCAGTGGA AGTGGATCTGGGACAGATTTTACTTTCACCAT CAGCAGCCTGCAGCCTGAAGATATTGCGACAT ATTTCTGTCAACAGTATGATAATCTCCCGATC ACCTTCGGCCAAGGGACACGACTGGATATTAG A | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGCAT GCACTGGGTCCGCCAGGCTCCAGGCAAGGGCT GGAGTGGGTGGCAGTTATATCATATGGTGAAGT AATAAATACTATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGTGAGAGGGGTA TAGCAGTGGAGGCTACGGTATGACGTCTGGGG CCAAGGGACCAAGGTCACCGTCTCCTCA |
| | | | SEQ ID NO: 24713 | SEQ ID NO: 28719 |

FIGURE 50
(Continued)

| | | | |
|---|---|---|---|
| iPS:393140 | | AA | DIQMTQSPSSLSASVGDRVTITCQASQDIFNYLN WYQQKPGKAPNLLIYDASNLETGVPSRFSGSGS GTDFTFTISSLQPEDIATYFCQQYDNLPITFGQGT RLDIR<br>SEQ ID NO: 24714 | QVQLVESGGGVVQPGRSLRLSCAASGFTFSSYGMH WVRQAPGKGLEWVAVISYGGSNKYYADSVKGRFT ISRDNSKNTLYLQMNSLRAEDTAVYYCVRRGYSSG GYGMDVWGQGTTVTVSS<br>SEQ ID NO: 28720 |
| | | NA | GACATCCAGATGACCCAGTCTCCATCTTCCGT GTCTGCATCTGTAGGAGACAGAGTCACCATCA CTTGTCGGGCGAGTCAGGGTATTAGCAGATGG TTAGCCTGGTATCAGCAGAAACCAGGGAAAG CCCCTGAACTCCTGATCTATGCTGCATCCCGTT TGCAAAGTGGATCCCATCCAGGTTCAGCGGC AGTGGATCTGGGACAGACTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A<br>SEQ ID NO: 24715 | CAGGTGCAGCTGGTGCAGTCTGGGGCTGAGGTG AAGAAGCCTGGGGCCTCAGTGAAGGTCTCCTGC AAGGCTTCTGGATACACCTTCACCGACTACTATA TACACTGGGTGCGACAGGCCCCTGGACAAGGGC TTGAGTGGATGGGATGGATCAACCTAATAGGG GTGGCACAAACTATGCACAGAAGTTTCAGGGCA GGGTCACCATGACCAGGGACACGTCCATCAGCA CAGCCTACATGGAACTGAGCAGGCTGAGATCTG ACGACACGGCCGTGTATTACTGTGCGAGAGATG GAACTGGGTCCTTTGACTACTGGGGCCAGGGAAC CCTGGTCACCGTCCTCA<br>SEQ ID NO: 28721 |
| | 21-225_35H12 | AA | DIQMTQSPSSVSASVGDRVTITCRASQGISRWLA WYQQKPGKAPELLIYAASRLQSGIPSRFSGSGSG TDFTLTISSLQPEDFATYYCQQANSFPFTFGPGTK VDIK<br>SEQ ID NO: 24716 | QVQLVQSGAEVKKPGASVKVSCKASGYTFTDYYIH WVRQAPGQGLEWMGWINPNRGGTNYAQKFQGRV TMTRDTSISTAYMELSRLRSDDTAVYYCARDGTGS FDYWGQGTLVTVSS<br>SEQ ID NO: 28722 |

FIGURE 50
(Continued)

| | | | |
|---|---|---|---|
| iPS:393142 | 21-225_33A3 | NA | GACATCCAGATGACCCAGTCTCCATCCTCACT GTCTGCATCTGTAGGAGACAGAGTCACCATCA CTTGTCGGGCGAGTCAGGGCATTAACAATTAT TTAGCCTGGTTTCAACAGAAACCAGGGAAAGC CCCTAAGTCCCTGATCTACGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTTTAATAGTTACCCTCCGA CGTTCGGCCAAGGGACCAAGGTGGAAATCAA A <br><br>SEQ ID NO: 24717 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATGGCAT GAACTGGGTCCGCCAGGCTCCAGGGAAGGGGCT GGAGTGGGTCTCATCCATTAGTGGTAGTAGTACT TACATATACTACGCAGAGTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAACAAACGGT ATGGACGTCTGGGGCCAAGGGACCACGGTCACC GTCTCCTCA <br><br>SEQ ID NO: 28723 |
| | | AA | DIQMTQSPSSLSASVGDRVTITCRASQGINNYLA WFQQKPGKAPKSLIYAASSLQSGVPSKFSGSGSG TDFTLTISSLQPEDFATYYCQQFNSYPPTFGQGT KVEIK <br><br>SEQ ID NO: 24718 | EVQLVESGGGLVKPGGSLRLSCAASGFTFSSYGMN WVRQAPGKGLEWVSSISGSSTYIYYADSVKGRFTIS RDNAKNSLYLQMNSLRAEDTAVYYCARTNGMDV WGQGTTVTVSS <br><br>SEQ ID NO: 28724 |
| iPS:393144 | 21-225_34D2 | NA | GATATTGTGATGACCCAGACTCCACTCTCT GTCCGTCACCCCTGGACAGCCGGCCTCCATCT CCTGCAAGTCTAGTCAGAGCCTCCTGCATAGT GATGGAAAGACCTATTTGTATTGGTACCTGCA GAAGCCAGGCCAGCCTCCACAGCTCCTGATCT ATGAAGTTTCCAACCGGTTCTCTGGAGTGCCA GATAGGTTCAGTGGCAGCGGGTCAGGGACAG ATTTCACACTAAAAATCAGCGGGTGGAGGCT GAGGATGTTGGGGTTTATTACTGCATGCAAAG TAAACAGCTTCCTCCTTTCGGCGGAGGGACCA AGGTGGAGATCAGA <br><br>SEQ ID NO: 24719 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGACA TTAACTGGGTGCGACAGGCCACTGGACAAGGGC TTGAGTGGATGGGATGGTGCACCTAACAGTGG TACCACAGGCTTTGCACAGAAGTTCCGGGCAG AGTCACCATGACCAGAAACACCTCCATAAGCAC AGCCTACTTGGAACTGAGCAGCCTGAGATCTGAG GACACGGCCGTGTATTACTGTGCGAGCAGCAGTG GCTGGTACTTTTTTGACTACTGGGGCCAGGGAAC CCTGGTCACCGTCTCCTCA <br><br>SEQ ID NO: 28725 |

FIGURE 50
(Continued)

| | | | |
|---|---|---|---|
| iPS:393146 | | AA | DIVMTQTPLSLSVTPGQPASISCKSSQSLLHSDGK TYLYWYLQKPGQPPQLLIYEVSNRFSGVPDRFSG SGSGTDFTLKISRVEAEDVGVYYCMQSKQLPPF GGGTKVEIR<br>SEQ ID NO: 24720 | QVQLVQSGAEVKKPGASVKVSCKASGYTFTNYDIN WVRQATGQGLEWVGWLHPNSGTTGFAQKFRGRV TMTRNTSISTAYLELSSLRSEDTAVYYCASSSGWYF FDYWGQGTLVTVSS<br>SEQ ID NO: 28726 |
| | 21-225_34G8 | NA | GACATCCAGATGACCCAGTCTCCATCCTCCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATATACTATTACCCTCCT ACTTTCGGCGGAGGGACCAAGGTGGAGATCA AA<br>SEQ ID NO: 24721 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTGGTGGTGGT AGCACATTCCACGACAGACTCCGTGAAGGGCCGG TTCACCATCTCCAGAGACAATTCCAAGAACACGC TGTATCTGCAAATTAACAGCCTGAGAGCCGAGG ACACGGCCGTATATTACTGTGTGAAAGGGGAGCT ACTAGAGGACTACTACTTCTACGGTATGGACGTC TGGGGCCAAGGGACCACGGTCACCGTCTCCTCA<br>SEQ ID NO: 28727 |
| | | AA | DIQMTQSPSSLSASVGDRVTITCRASQDIRSDLG WYQQKPGKAPKRLIYAASSLQSGVPSRFSGSGS GTEFTLTISSLQPEDFATYYCLQHTIYPPTFGGGT KVEIK<br>SEQ ID NO: 24722 | EVQLLESGGGLVQPGGSLRLSCAASGFTFSSYAMS WVRQAPGKGLEWVSAISGRGGSTFHADSVKGRFTI SRDNSKNTLYLQINSLRAEDTAVYYCVKGELLEDY YFYGMDVWGQGTTVTVSS<br>SEQ ID NO: 28728 |

FIGURE 50
(Continued)

| | | | |
|---|---|---|---|
| iPS:393148 | 21-225_35E5 | NA | GACATCCAGATGATCCAGTCTCCATCCTCCT GTCTGCATCTGTAGGAGACAGAGTCACCATCA CTTACCGGGCAAGTCAGAGCATTAGCAGCTAT TTAAAATTGGTATCAGCAGAAACCAGGGAAAGC CCCTAAGCTCCACATCTATGGTGCATCCAGTTT CCAAAGTTGGGTCCCATCAAGGTTCAGTGGCA GTGGATCTCGACAGATTTCACGCTCACCATC ATCAGTATGCAACCTGGAGATTATGCAACTTA CTACTGTCACCAGAGTTACAATCTCCCGATCA CCTTCGGCCAAGGGACCCGACTGGAGATTAAA<br>SEQ ID NO: 24723 | CAGGTGCAGCTGGTGCAGTCTGGGGCTGAGGTG AAGAAGCCTGGGGCCTCAGTGAAGGTCCTGC AAGGCTTCTGGATACACCTTCACCAGTTATGATA TCAACTGGGTGCGACAGGCCACTGGACAAGGGC TTGAGTGGATGGGATGGATGAACCCTAACAGTG GTAACACAGGCTATGCACAGAAGTTCCAGGCA GAGTCACCATGACCAGGAACACCTCCATAAGCA CAGCCTACATGGAGCTGAGCAGCCTGAGATCTG AGGACACGGCCGTGTATTACTGTGCGAGAAAGA AGTCTAACGACTACTGGGGCCAGGGAACCCTGG TCACCGTCTCCTCA<br>SEQ ID NO: 28729 |
| | | AA | DIQMIQSPSSLSASVGDRVTITYRASQSISSYLNW YQQKPAKAPKLIIYGASSFQSWVPSRFSGSGSST DFTLTIISMQPGDYATYYCHQSYNLPITFGQGTR LEIK<br>SEQ ID NO: 24724 | QVQLVQSGAEVKKPGASVKVSCKASGYTFTSYDIN WVRQATGQGLEWMGWMNPNSGNTGYAQKFQGR VTMTRNTSISTAYMELSSLRSEDTAVYYCARKKSN DYWGQGTLVTVSS<br>SEQ ID NO: 28730 |
| iPS:393150 | 21-225_36A5 | NA | GACATCCAGATGACCCAGTCTCCATCCTCCCT GTCTGCATCTGTAGGAGACAGAGTCACCATCA CTTGCCGGACAAGTCAGGACATTAGAAATGAT TTAGGCTGGTATCAGCAGAAACCAGGGAAAG CCCCTAAGCGCCTGATCTTTGCTGCATCCAGTT TGCAAAGTGGGGTCCCATCAAGATTCAGCGGC AGTGGATCTGGGACAGAATTCACTCTCACAAT CAGCAGCCTGCAGCCTGAAGATTTTGCAACTT ATTACTGTCTACACCACAATAGTTACCCTCCTA AGTTTGGCCGAGGGATCAAGGTTGAGATCAC A<br>SEQ ID NO: 24725 | GAGGTGCAGCTGTTGGAGTCTGGGGGAGGCTTG GTACAGCCTGGGGGGTCCCTGAGACTCTCCTGTG CAGCCCTCTGGATTCACCTTTAACAACTATGCCAT GAACTGGGTCCGCCAGGCTCCAGGGAAGGGGCT GGAGTGGGTCTCAGTATTAGTCGTCGTGGTGGT AACACATTCTACGCAGACTCCGTGAAGGGCCGGT TCACCATCTCCAGAGACAATTCCAAGAACACGCT GTATCTCCAAATGAACAGCCTGAGAGCCGAGGA CACGGCCGTATATTACTGTGCGAAAGGGGAGCT ACTAGAGGACTACTACTACTACTACGTCTATGGACGTC TGGGGCCAAGGGACCACGGTCACCGTCTCCTCA<br>SEQ ID NO: 28731 |

FIGURE 50
(Continued)

| | | | | |
|---|---|---|---|---|
| iPS:393152 | 21-225_25B3 | AA | DIQMTQSPSSLSASVGDRVTITCRTSQDIRNDLG WYQQKPGKAPKRLIFAASSLQSGVPSRFSGSGSG TEFTLTISSLQPEDFATYYCLHHNSYPPKFGGGIK VEIT<br>SEQ ID NO: 24726 | EVQLLESGGGLVQPGGSLRLSCAASGFTFNNYAMN WVRQAPGKGLEWVSAISRRGGNTFYADSVKGRFTI SRDNSKNTLYLQMNSLRAEDTAVYYCAKGELLED YYYYAMDVWGQGTTVTVSS<br>SEQ ID NO: 28732 |
| | | NA | GACATCCAGATGACCCAGTCTCCCTCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGCC AGTGGATCTGGGACAGATTTCACTCTCACCAT CAGCAGCCTGCAGCCTGAAGATTTTGCGACTT ACTGTTGTCAACAGTCTGACAGTTCCCTCGG ACGTTCGGCCAAGGGACCAAGGTGGAAATCA AA<br>SEQ ID NO: 24727 | CAGGTGCAGCTGGTGGAGTCTGGGGGAGGCGTG GTCCAGCCTGGGAGGTCCCTGAGACTCTCCTGTG CAGCGTCTGGATTCACCTTCAGCAGCTATGCAT GCACTGGGTCCGCCAGGCTCCAGGCAAGGGGCT GGAGTGGGTGGCAGTTATATGGTATGGAAGT AATAAATATTATGCAGACTCCGTGAAGGGCCGAT TCACCATCTCCAGAGACAATTCCAAGAACACGCT ATATCTACAAATGAACAGCCTGAGAGCCGAGGA CACGGCTGTGTATTACTGTGCGAGAGATTCCTCC CCCTACGGTATGGACGTCTGGGGCCAAGGGACC ACGGTCACCGTCTCCTCA<br>SEQ ID NO: 28733 | 
| | | AA | DIQMTQSPSSVSASVGDRVTITCRASQGISSWLA WYQQKPGKAPKLLIYGASSLQSGVPSRFSASGS GTDFTLTISSLQPEDFATYCCQQSDSFPRTFGQGT KVEIK<br>SEQ ID NO: 24728 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARDSSPY GMDVWGQGTTVTVSS<br>SEQ ID NO: 28734 |

FIGURE 50
(Continued)

| | | | |
|---|---|---|---|
| iPS:393166 | 21-225_27G6 | NA | TCCTATGAGCTGACTCAGCCACCCTCAGTGTCCGTGTCCCCAGGACAGAGCCAGCATCACCTGCTCTGGAGATAAATTGGGGGATAAATATGCTTGCTGGTATCAGCAGAAGCCAGGCCAGTCCCCTGTGTTGGTCATCTATCAAGATAGGAAGCGGCCCTCAGGGATCCCTGAGCGATTCTCTGGCTCCAACTCTGGGAACACAGCCACTCTGACCATCAGCGGGACCCAGACTATGGATGAGGCTGACTATTACTGTCAGGCGTGGGACACAGCAGCTCTATGTGGTATTCGGCGGAGGGACCAAGCTGACCGTCCTA |
| | | | SEQ ID NO: 24729 |
| | | | CAGGTGCAGCTGGTGGAGTCTGGGGGAGGCGTGGTCCAGCCTGGGAGGTCCCTGAGACTCTCCTGTGCAGCGTCTGGATTCACCTTCAGTGGCTATGGCATGCACTGGGTCCGCCAGGCTCCAGGCAAGGGCTGGAGTGGGTGGCAATTATATGGTATGATGGAAGTAAAAATACAATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATAGGGTATATTGTAGTAGTACCAGCTGCTCCCCTTACTACTACTACGGTATGGACGTCTGGGGCCAAGGGACCACGGTCACCGTCTCCTCA |
| | | AA | SEQ ID NO: 28735 |
| | | | SYELTQPPSVSVSPGQTASITCSGDKLGDKYACWYQQKPGQSPVLVIYQDRKRPSGIPERFSGSNSGNTATLTISGTQTMDEADYYCQAWDSSSYVFGGGTKLTVL |
| | | | SEQ ID NO: 24730 |
| | | | QVQLVESGGGVVQPGRSLRLSCAASGFTFSGYGMHWVRQAPGKGLEWVAIIWYDGSKKYNADSVKGRFTISRDNSKNTLYLQMNSLRAEDTAVYYCARDRVYCSSTSCSPYYYYGMDVWGQGTTVTVSS |
| | | | SEQ ID NO: 28736 |

FIGURE 50
(Continued)

| | | | | |
|---|---|---|---|---|
| iPS:393168 | 21-225_32B11 | NA | TCCTATGAACTGACTCAGCCACCCTCAGTGTC CGTGTCCCCAGGACAGACAGCCAGCATCACCT GCTCTGGAGATAAATTGGGGGATAAATATGCT TACTGGTATCAGCAGAAGCCAGGCCAGTCCCC TGTGTTGGTCATCTATCAAGATAGTAAGCGGT CCCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAACAGCACTGTGTA TTCGGCGGAGGGACCAAGCTGACCGTCCTA<br><br>SEQ ID NO: 24731 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGA TGGCACTAACTATGCACAGAAGTTTCAGGGCAG GGTCACCATGACCAGGGACACGTCCATCAGCAC AGCCTACATGGAGCTGAACAGGCTGAGATCTGA CGACACGGCCGTGTATTACTGTGCGAGGGGGTT TACTATGGTTCGGGGAGTTATTATAACGACCTCG ACCCCTGGGGCCAGGGAACCCTGGTCACCGTCTC CTCA<br><br>SEQ ID NO: 28737 |
| | | AA | SYELTQPPSVSVSPGQTASITCSGDKLGDKYAY WYQQKPGQSPVLVIYQDSKRSSGIPERFSGSNSG NTATLTISGTQAMDEADYYCQAWDNSTVVFGG GTKLTVL<br><br>SEQ ID NO: 24732 | QVQLVQSGAEVKKPGASVKVSCKASGYTFTGYYM HWVRQAPGQGLEWMGWINPNSDGTNYAQKFQGR VTMTRDTSISTAYMELNRLRSDDTAVYYCARGFYY GSGSYYNDLDPWGQGTLVTVSS<br><br>SEQ ID NO: 28738 |
| iPS:393172 | 21-225_3B12 | NA | TCCTATGAGCTGAGTCAGCCACCCTCAGTGTC CGTGTCCCCAGGACAGACAGCCAGCATCACCT GCTCTGGAGATAAATTGGGGGAAAAATATGCT TGCTGGTATCAGCAGAAGCCAGGCCAGTCCCC TGTGCTGGTCGTCATCAAGATAGGAAGCGGC CCCTCAGGGATCCCTGAGCGATTCTCTGGCTCC AACTCTGGGAACAAAAGCCACTCTGACCATCAG CGGGACCCAGGCGTGGGTCAACAACACTATGATA ACTGTCAGGCGTGGGTCAACAACACTATGATA TTCGGCGGAGGGACCAAGCTGACCGTCCTA<br><br>SEQ ID NO: 24733 | CAGGTGCACCTGGTGGAGTCTGGGGGAGGCGTG GTCCAGCCTGGGAGGTCCCTGAGACTCTCCTGTG CAGCCTCTGGATTCACCTTCAGTAGTTACTATGGCAT GCACTGGGTCCGCCAGGCTCCAGGCAAGGGGCT GGAGTGGGTGGCAGTTATATCAGACTCCGTGAAGT AATAAATACTATGCAGACTCCGTGAAGGGCCGA TTCACCATCTCCAGAGACAATTCCAAGAACACGC TGCATCTGCAAATGAACAGCCTGAGAGCTGAGG ACACGGCTGTGTATTACTGTGCGAGAGATCGGAG GGGGGCTATGGAGTCCCGATGCTTTTGATATC TGGGGCCAAGGGACAATGGTCACCGTCTCTTCA<br><br>SEQ ID NO: 28739 |

FIGURE 50
(Continued)

| | | | |
|---|---|---|---|
| iPS:393174 | 21-225_15D8 | AA | SYELSQPPSVSVSPGQTASITCSGDKLGEKYACW YQQKPGQSPVLVIYQDRKRPSGIPERFSGSNSGN KATLTISGTQAMDEADYYCQAWVNNTMIFGGG TKLTVL<br>SEQ ID NO: 24734 | QVHLVESGGGVVQPGRSLRLSCAASGFTFSYYGM HWVRQAPGKGLEWVAVISYDGSNKYYADSVKGR FTISRDNSKNTLHLQMNSLRAEDTAVYYCARDRRG GYGVPDAFDIWGQGTMVTVSS<br>SEQ ID NO: 28740 |
| | | NA | CTGCCTGTGCTGACTCAGCCCCCGTCTGCATCT GCCTTGCTGGGAGCCTCAGTCAAGTCACCTG CACCCTAAGCAGTGAGCACAGACCAGGAGTC TCGAATGGTATCAACAGAGACCAGGAGGTATG CCCCCAGTATATCAAGGTTAAGAGAGTGATG GCAGCCACAGCAAGGGGACGGGATCCCCGA TCGCTTCATGGGCTCCAGTTCTGGGGCTGACC GCTACATCACCTTCTCCAACCTCCAGTCTGAC GATGAGGAGGAGTATCACTGTGAGAGAGCC ACACGATCGATGCCAAGTCGGTGTGTTATTC GGCGGAGGGACCAAGCTGACCGTCCTA<br>SEQ ID NO: 24735 | CAGGTGCAGTTGGTGGAGTCTGGGGGAGGCGTG GTCCAGACTGGGAGGTCCCTGAGACTCTCCTGTG CAGCCTCTGGATTCACCTTCAGTGAGCTATGGCAT GCACTGGGTCCGCCAGGCTCCAGGCAAGGGGCT GGAGTGGGTGTCAGTTATATCATATGATGGAAGT AATAAATACTATGCAGACTCCGTGAAGGGCCGA TTCACCATCTCCAGAGACAATTCCAAGAACACGC TGTATCTGCAAATGAACAGCTGAGAGCTGAGG ACACGGCTGTGTATTACTGTGCGAGAGATCGGGT CTATTGTAGTAGTACCAGCTGCGTCCCTTACTAC GACTACGGTATGGACGTCTGGGGCCAAGGG ACCACGGTCACCGTCTCCTCA<br>SEQ ID NO: 28741 |
| | | AA | LPVLTQPPSASALLGASIKLTCTLSSEHSTYTIEW YQQRPGRSPQYIMKVKSDGSHSKGDGIPDRFMG SSSGADRYITFSNLQSDDEEEYHCGESHTIDGQV GVVFGGGTKLTVL<br>SEQ ID NO: 24736 | QVQLVESGGGVVQTGRSLRLSCAASGFTFSGYGM HWVRQAPGKGLEWVSVISYDGSNKYYADSVKGRF TISRDNSKNTLYLQMNSLRAEDTAVYYCARDRVY CSSTSCVPYYDYYGMDVWGQGTTVTVSS<br>SEQ ID NO: 28742 |

FIGURE 50
(Continued)

| | | | |
|---|---|---|---|
| iPS:393176 | 21-225_27E7 | NA | TCCTATGAGCTGACTCAGCCACCCTCAGTGTC CGTGTCCCCAGGACAGAGACAGCCAGCATCACCT GCTCTGGAGATAAATTGGGGAATAAATATGCT TGCTGGTATCAGCAGAAGCCAGGCCAGTCCCC TGTGGAGGTCATCTATCAAGATAGCAAGCGGC CCTTAGGGATCCCTGAGCGATTCTCTGCTCC AACTCTGGGAACACAGCCACTCTGACCATCAG CGGGACCCAGGCTATGGAGACAGTAGTACTGTGT ACTGTCAGGCGTGGGACAGTAGTACTGTGGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGATTC CTATTGTAGTAGTACCAGCTGCCCTTACTACTAC TACTACGGTATGGACGTCTGGGGCCAAGGGACC ACGGTCACCGTCTCCTCA |
| | | | SEQ ID NO: 24737 | SEQ ID NO: 28743 |
| | | AA | SYELTQPPSVSVSPGQTASITCSGDKLGNKYACW YQQKPGQSPVEVIYQDSKRPLGIPERFSGSNSGN TATLTISGTQAMDEADYYCQAWDSSTVFGGG TKLTVL | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCAREDSYC SSTSCPYYYYGMDVWGQGTTVTVSS |
| | | | SEQ ID NO: 24738 | SEQ ID NO: 28744 |

FIGURE 50
(Continued)

| | | | |
|---|---|---|---|
| iPS:393178 | 21-225_34D7 | NA | TCCTATGAGCTGACTCAGCCACCCTCAGTGTCCGTGTCCCCAGGACAGACAGCCAGCATCACCTGCTCTGGAGATAAATTGGGGGAGAAATATGCTTACTGGTATCAGCAGAAGCCAGGCCAGTCCCCTGTGCTGGTCCTCTATCAAGATAGCAAGCGGCCCTCAGGGATCCCTGAGCGATTCTCTGGCTCCAACTCTGGGAACACAGCCACTCTGACCATCAGCGGGACCCAGACTATGGATGAGGCTGACTTTTACTGTCAGGCGTGGGACAACACCACTGTGGTATTCGGCGGAGGGACCAAGCTGACCGTCCTA SEQ ID NO: 24739 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGGATGGATCAACCCTAACAGTGGTGGCACAAACTATGCACAGGAGTTTCAGGGCAGGGTCACCATGACCAGGGACACGTCCATCAGCACAGCCTACATGGAGCTGAGCAGGCTGAGATCTGACGACACGGCCGTGTATTACTGTGCGAGGGGGTATTACTATGTTCGGGGAGTTATTATAACGACCTGGACCCCTGGGGTCAGGGAACCCTGGTCACCGTCTCCTCA SEQ ID NO: 28745 |
| | | AA | SYELTQPPSVSVSPGQTASITCSGDKLGEKYAYWYQQKPGQSPVLVLYQDSKRPSGIPERFSGSNSGNTATLTISGTQTMDEADFYCQAWDNTTVVFGGGTKLTVL SEQ ID NO: 24740 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGYYYGSGSYYNDLDPWGQGTLVTVSS SEQ ID NO: 28746 |
| iPS:393180 | 21-225_4G12 | NA | CAGTCTGTGCTGACTCAGCCACCCTCAGCGTCTGGGACCCCCGGGCAGAGGGTCACCATGTCTTGTTCTGGAACCAACTCCAACATCGGAAGTTATACTGTAAACTGGTACCAGCAGCTCCCAGGAACGGCCCCCAAACTCCTCATCTATATAATCAGCGGGCCCTCAGGGGTCCCTGACCGATTCTCTGGCTCCAAGTCTGGCTCAGTCAGTGGGCTCCAGTCTGAGGATGAGGCTGATTATTACTGTGCAGCATGGGACGACAGCCTGAATGGTCATGTGGTATTCGGCGGAGGGACCAAGCTGACCGTCCTA SEQ ID NO: 24741 | GAGGTGCAGCTGGTGTTGGAGTCTGGGGGAGGCTTGGTACAGCCGGGGGGGTCCCTGAGACTCTCCTGTGCAGCCTCTGGATTCACCTTTAGCAGTCAGTATGCCATGAGCTGGGTCCGCCAGGCTCCAGGGAAGGGGCTGGAGTGGGTCTCAACTCTTAGTGGTGTCGTGGTGGTAGCACATACTACGCAGACTCCGTGAAGGGCCGGTTCACCATCTCCAGAGACAATTCCAAGAACACGCTGTATCTGCAAATGAGCAGCCTGAGAGCCGAGGACACGGCCGTATACAGCTATGAGTACTACGGTATGGAGTGGATACAGCTATGAGTACTACGGTATGGAGTCTGGGGCCAAGGGACCACGGTCACCGTCTCCTCA SEQ ID NO: 28747 |

FIGURE 50
(Continued)

| | | | | |
|---|---|---|---|---|
| | | AA | QSVLTQPPSASGTPGQRVNMSCSGTNSNIGSYTV NWYQQLPGTAPKLLIYINNQRPSGVPDRFSGSKS GTSASLAISGLQSEDEADYYCAAWDDSLNGHVV FGGRTKLTVL<br>SEQ ID NO: 24742 | EVQLLESGGGLVQPGGSLRLSCAASGFTFSSYAMS WVRQAPGKGLEWVSTLSGRGGSTYADSVKGRST ISRDNSKNTLYLQMSSLRAEDTAVYYCAKWGRGY SYEYYYGMDVWGQGTTVTVSS<br>SEQ ID NO: 28748 |
| iPS:393182 | 21-225_4B3 | NA | TCCTATGAGCTGACTCAGCCACCCTCAGTGTC CGTGTCCCAAGAGACAGTCAGCATCACCT GCTCTGGAGATAAATTGGGGGATAAATATGCT TGCTGGTATCAGCAGAAGCCAGGCCAGTCCCC TGTGCTGGTCATCTATCAAGATCGCAAGCGGC CCTCAGGGATCCCTGAGCGATTCTCTGGCTCC AACTCTGGGAACACAGGCTATGAGGCTGACTATT CGGGACCCAGGCTGTGGGACAACAACACTGTGATA ACTGTCAGGCGTGGGACCAAGCTGACCGTCCTA<br>SEQ ID NO: 24743 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCTAACAGTGG TGGCACAAACTCTGCACAGAAGTTCAGGCAG GGTCACCATGACCAGGGACACGTCCATCAGCAC AGCCTACATGGAGCTGAGCAGGCTGAGATCTGA CGACACGGCCGTATATTACTGTGCGAGGTCCTAT TACTATGGTTCGGGGAGTTATTATAACGAGTTTG ACTACTGGGGCCAGGGAACCCTGGTCACCGTCTC CTCA<br>SEQ ID NO: 28749 |
| | | AA | SYELTQPPSVSVSPRQTVSITCSGDKLGDKYACW YQQKPGQSPVLVIYQDRKRPSGIPERFSGSNSGN TATLTISGTQAMDEADYYCQAWDNNTVIFGGG TKLTVL<br>SEQ ID NO: 24744 | QVQLVQSGAEVKKPGASVKVSCKASGYTFGYYM HWVRQAPGQGLEWMGWINPNSGGTNSAQKFQGR VTMTRDTSISTAYMELSRLRSDDTAVYYCARSYYY GSGSYYNEFDYWGQGTLVTVSS<br>SEQ ID NO: 28750 |

FIGURE 50
(Continued)

| | | | |
|---|---|---|---|
| iPS:393184 | 21-225_15H11 | NA | TCCTATGAGCTGACTCAGCCACCCTCAGTGTCCGTGTCCCCAGGACAGACAGCCAGCATCACCTGCTCTGGAGATAAATTGGGGGAGAAATATGCTTGCTGGTATCAGCAGAAGCCAGGCCAGTCCCCTGTGGTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATAGATGAGGCTGACTATTACTGTCAGGCGTGGGACAGCAGCACTGCGGTATTCGGCGGAGGGACCAAGTTGACCGTCCTA | CAGATCACCTTGAAGGAGTCTGGTCTTACGCTGACTGAAACCCACACAGACCCTCACGCTGACCTGCACCTTCTCTGGGTTCTCACTCAGCACTGGTGGAGTGGGTGTGGGCTGGATCCGTCAGCCCCCAGAAAGGCCCTGGAGTGGCTTGCACTCATTTATTGGCATGATGATAAGGCTACAGTCCATCTGAGGAGCAGGCTCACCATCACCAAGGACACCTCCAAAAACCAGGTGGTCCTTACAATGACCAACATGGACCCTGTGACACAGCCACATATTACTGTGCACGTATAGTAGCAGTTGCCTTTGACTACTGGGGCCAGGGAACCCTGATCACCGTCTCCTCA |
| | | | SEQ ID NO: 24745 | SEQ ID NO: 28751 |
| | | AA | SYELTQPPSVSVSPGQTASITCSGDKLGEKYACWYQQKPGQSPVVVIYQDRKRPSGIPERFSGSNSGNTATLTISGTQAIDEADYYCQAWDSSTAVFGGGTKLTVL | QITLKESGLTLTMKPTQTLTLTCTFSGFSLSTGGVGVGWIRQPPGKALEWLALIYWHDDKRYSPSLRSRLTITKDTSKNQVVLTMTNMDPVDTATYYCARIVAVAFDYWGQGTLITVSS |
| | | | SEQ ID NO: 24746 | SEQ ID NO: 28752 |
| iPS:393186 | 21-225_27D9 | NA | TCCTATGAGCTGACTCAGCCACCCTCAATGTCCGTGTCCCCAGGACAGACAGCCAGCATCACCTGCTCTGGATATAAATTGGGGGATAAATATGCTTGCTGGTTTCAGCAGAAGCCAGGCCAGTCCCCTGTGCTGGTCATCTATCAAGATAGCAAGCGGCCCTCAGGGATCCCTGAGCGATTCTCTGGCTCCAACTCTGGGAACACAGCCACTCTGACCATCAGCGGGACCCAGGCTATGATGAGGCTGACTATTACTGTCAGGCGTGGGTCAACAACACTGTATTCGGCGGAGGGACCAAGCTGACCGTCCTA | CAGGTGCAGTTGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGGATGGATCAACCCTAACAGTGGTGGCACAAAGTATGCACAGAAGTTTCAGGGCAGGGTCACCATGACCAGGGACACGTCCATCAGCACAGCCTACATGGAGCTGAACAGGCTGAGATCTGACGACACGGCCGTGTATTACTGTGCGAGAGAGAGGTGTAGTACTACCAGTTGCTATTTAGGAATTACGGGCTACTACGGTATGGACGTCTGGGGCCAAGGGACCACGGTCACCGTCTCCTCA |

FIGURE 50
(Continued)

| | | | | |
|---|---|---|---|---|
| iPS:393188 | | AA | SEQ ID NO: 24747<br>SYELTQPPSMSVSPGQTASITCSGYKLGDKYAC<br>WFQQKPGQSPVLVIYQDSKRPSGIPERFSGSNSG<br>NTATLTISGTQAMDEADYYCQAWVNNTVFGGG<br>TKLTVL | SEQ ID NO: 28753<br>QVQLVQSGAEVKKPGASVKVSCKASGYTFTGYYM<br>HWVRQAPGQGLEWMGWINPNSGGTKYAQKFQGR<br>VTMTRDTSISTAYMELNRLRSDDTAVYYCARERCS<br>TTSCYLGHTGYYGMDVWGQGTTVTVSS |
| | | NA | SEQ ID NO: 24748<br>TCCTATGAGCTGACTCAGCCACCCTCAGTGTC<br>CGTGTCCCCAGGACAGACAGCCAGCATCACCT<br>GCTCTGGAGATAAATTGGGGGAGAAATATGTT<br>TCCTGGTATCAGGAGAAGCCAGGCCAGTCCCC<br>TGTGCTGGTCATCTATCAAGATAGTAAGCGGC<br>CCTCAGGGATCCCGAGCGATTCTCTGGCTCC<br>AACTCTGGGAACACAGCCACTCTGACCATCAG<br>CGGGACCCAGGCTATGGATGAGGCTGACTATT<br>ACTGTCAGGCGTGGGACAGCAGCACTGTATTC<br>GGCGGAGGGACCAAGCTGACCGTCCTA | SEQ ID NO: 28754<br>CAGATCACCTTGAGGGAGTCCTGGTCCTACGCTGG<br>TGAAACCCACACAGACCCTCACGCTGACCTGCAC<br>CTTCTCTGGGTTCTCACTCAGCACTAGTGGAGTG<br>GGTGTGGCTGGATCCGTCAGCCCCCAGGAAAG<br>GCCCTGGAGTGGCTTGCACTCATTTATTGGAATG<br>ATGATAAGCGCTACAGCCCATCTCTGAAGAGCA<br>GACTCACCATCACCAAGGACACCTCCAAAACC<br>AGGTGGTCCTTACAATGACCAACATGACCCTGT<br>GGACACAGCCACATATTACTGTGCACACTTAATA<br>GCAGTGACTTTTGACTCCTGGGGCCAGGGATCCC<br>TGGTCACCGTCCTCA |
| 21-225_34B9 | | AA | SEQ ID NO: 24749<br>SYELTQAPSVSVSPGQTASITCSGDKLGEKYVSW<br>YQEKPGQSPVLVIYQDSKRPSGIPERFSGSNSGNT<br>ATLTISGTQAMDEADYYCQAWDSSTVFGGGTK<br>LTVL | SEQ ID NO: 28755<br>QITLRESGPTLVKPTQTLTLTCTFSGFSLSTSGVGVG<br>WIRQPPGKALEWLALIYWNDDKRYSPSLKSRLTIT<br>KDTSKNQVLTMTNMDPVDTATYYCAHLIAVTFD<br>SWGQGSLVTVSS |
| | | | SEQ ID NO: 24750 | SEQ ID NO: 28756 |

FIGURE 50
(Continued)

| | | | |
|---|---|---|---|
| iPS:393192 | 21-225_12B1 | NA | TCCTATGAGCTGACTCAGCCACCCTCAGTGTC CGTGTCCCCAGGACAGACAGTCAGCATCACCT GCTCTGGAGATATCAGCAGTAAATATGCT TGCTGGTATCAGCAGAAGCCAGGCCAGTCCCC TGTGCTGGTCATCTATCAAGATGCAAGCGGC CCTCAGGGATCCCGAGCGATTCTCTGGCTCC AACTCTGGGAACACAGCCACTCTGACCATCAG CGGGACCCAGGCTATGGATGAGGCTGACTATT ACTGTCAGGCGTGGGACAACAAGCTGACCGTGATA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGGCGTCTGATTCACCTTCAGTAGCTATGGCAT GCACTGGGTCCGCCAGGCTCCAGGCAAGGGCT GGAGTGGGTGGCAGTTATATGAGACTCCGTGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGATCGGG TAGACAGCTGGTACCCCTACTACTACTACGG TATGGACGTCTGGGGCCAAGGGACCACGGTCAC CGTCTCCTCA |
| | | | SEQ ID NO: 24751 |
| | | AA | SYELTQPPSVSVSPRQTVSITCSGDKLGDKYACW YQQKPGQSPVLVIYQDRKRPSGIPERFSGSNSGN TATLTISGTQAMDEADYYCQAWDNNTVIFGGG TKLTVL | QVQLVESGGGVVQPGRSLRLSCAASGFTFSSYGMH WVRQAPGKGLEWVAVIWNDGSNKYYADSVKGRF TISRDNSKNTLYLQMNSLRAEDTAVYYCARDRVA AAGTPYYYYGMDVWGQGTTVTVSS |
| | | | SEQ ID NO: 24752 | SEQ ID NO: 28757 |
| iPS:393194 | 21-225_16D2 | NA | TCCTATGAGCTGACTCAGCCACCCTCAGTGTC CGTGTCCCCAGGACAGACAGTCAGCATCACCT GCTCTGGAGATATCAGCAGTAAATATGCT TGCTGGTATCAGCAGAAGCCAGGCCAGTCCCC TGTGCTGGTCATCTATCAAGATAGCAAGCGGC CCTCAGGGATCCCGAGCGATTCTCTGGCTCC AACTCTGGGAACACAGCCACTCTGACCATCAG CGGGACCCAGGCTATGGACAGCAGCACTTATGTG ACTGTCAGGCGTGGGAGGGACCAAGCTGACCGTCCT GTATTCGGCGGAGGGACCAAGCTGACCGTCCT A | GAGGTGCAGCTGGTGGAGTCTGGGGGAGGCTTG GTAAAGCCTGGGGGGTCCTTAGACTCTCCTGTG CAGCCTCTGGATTCACTTTCAGTAACGCTGGAT GAACTGGGGTCCGCCAGGCTCCAGGGAAGGGCT GGAGTGGGTTGGCCGTATTAAAAGCAAACTGA TGTGGGACAACAGACTACGCTGCACCGTGAA AGGCAGATTCACCATCTCAAGAGATGATTCAAA AACACGCTGTATCTGCAAATGCACAGCCTGAA AACCGAGGACACAGCCGTGTATTACTGTACCACA GATACGGGTCCTATAGCAGTCGTCTGCTTACT ACTACTACTACGCTATGGACGTCTGGGGCCAAGG GACCACGGTCACCGTCTCCTCA |
| | | | | SEQ ID NO: 28758 |

FIGURE 50
(Continued)

| | | | SEQ ID NO: 24753 | SEQ ID NO: 28759 |
|---|---|---|---|---|
| iPS:393196 | 21-225_16G8 | AA | SYELTQPPSVSVSPGQTASITCSGDKLGDKYACW YQQKPGQSPVLVIYQDSKRPSGIPERFSGSNSGN TATLTISGTQAMDEADYYCQAWDSSTYVFGG GTKLTVL | EVQLVESGGGLVKPGGSLRLSCAASGFTFSNAWM NWVRQAPGKGLEWVGRIKSKTDGGTTDYAAPVK GRFTISRDDSKNTLYLQMHSLKTEDTAVYYCTTDT GPIAARLAYYYYAMDVWGQGTTVTSS |
| | | | SEQ ID NO: 24754 | SEQ ID NO: 28760 |
| | | NA | TCCTATGAGCTGAGTCAGCCACCCTCAGTGTC CGTGTCCCCAGGACAGACAGCCAGCATCACCT GCTCTGAGATAAATTGGGGAGACCAGGGAAAATATGCT TGCTGGTATCAGCAGAAGCCAGGCCAGTCCCC TGTGTCTGGTCATCTATCAAGATAGGAAGCGGC CCTCAGGGATCCCGAGCGATTCTCTGGCTCC AACTCTGGGAACAAAGCCACTCTGACCATCAG CGGGACCCAGGCTATGGAGGCTGAGGCTGACTATT ACTGTCAGGCGTGGGTCAATAACACTATGATA TTCGGCGGAGGGACCAAGCTGACCGTCCTA | GAGGTGCAGCTGTTGGAGTCTGGGGGAGGCTTG GTACAGCCTGAGGGGTCCCTGAGACTCTCCTGTG CAGCCTCTGGATTCACCTTTAGCAGCAGTATGCCAT GAGCTGGGTCCGCCAGGCTCCAGGGAAGGGCT GGAGTGGGTCTCAGGTATTAGTGGTAGTGGTGGT AGCACATACTACGCAGACTCCGTGAAGGGCCGG TTCACCATCTCCAGAGACAATTCCAAGAACACGC TGTGTCTGCAACATGAACAGCCTGAGAGCCGAGG ACACGGCCGTATATTACTGTGCAAAGAATATTG TGGTGGTGACTGCTATTCCCCCTTACTACTACTACT ACGGTATGAGCGTCTGGGGCCAAGGGACCACGG TCACCGTCTCCTCA |
| | | | SEQ ID NO: 24755 | SEQ ID NO: 28761 |
| | | AA | SYELSQPPSVSVSPGQTASITCSGDKLGEKYACW YQQKPGQSPVLVIYQDRKRPSGIPERFSGSNSGN KATLTISGTQAMDEADYCQAWVNNTMIFGGG TKLTVL | EVQLLESGGGLVQPEGSLRLSCAASGFTFSSYAMS WVRQAPGKGLEWVSGISGSGGSTYYADSVKGRFTI SRDNSKNTLCLHMNSLRAEDTAVYYCAKEYCGGD CYSPYYYYGMDVWGQGTTVTSS |
| | | | SEQ ID NO: 24756 | SEQ ID NO: 28762 |

FIGURE 50
(Continued)

| | | | |
|---|---|---|---|
| iPS:393198 | 21-225_28A11 | NA | TCCTATGAGTTGACTCAGCCACCCTCAGTGTCCGTGTCCCCAGGACAGAGCAGCCATCACCTGCTCTGGAGATAAATTGGGGGATAAATATGCTTGCTGGTATCAGCAGAAGCCAGGCCAGTCCCCTGTGCTCTGGTCATCTATCAAGATAGCAAGCGGCCCTCAGGGATCCCTGAGCGATTCTCTGCTCCAACTCTGGGAACACAGCCACTCTGACCATCAGCGGGACCCAGGCTATGGATGAGGCTGACTATTACTGTCAGGCGTGGGACAGTAGCACTTATGTGGTATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCTTCAGTGGCTATGGCCTGCACTGGGTCCGCCAGGCTCCAGGCAAGGGCTGGAGTGGGTGGCACTTATATGGTATGATGGAAATAATACATACTATGCAGACTCCGTGAAGGGCCGATTCACCATCTCCAGAGACAATTCCAAGAACACGCTGTATCTGCAAATGAACAGCCTGAGAGCCGAAGACACGGCTGTGTATTACTGTGCGAGAGATAGGGTATATTGTAGTAGTACCAGCTGTCCCCTTACTACTACTACTACGGTATGGACGTCTGGGGCCAAGGGACCACGGTCACCGTCTCCTCA |
| | | | SEQ ID NO: 24757 | SEQ ID NO: 28763 |
| | | AA | SYELTQPPSVSVSPGQTASITCSGDKLGDKYACWYQQKPGQSPVLVIYQDSKRPSGIPERFSGSNSGNTATLTISGTQAMDEADYYCQAWDSSTYVFGGGTKLTVL | QVQLVESGGGVVQPGRSLRLSCAASGFTFSGYGLHWVRQAPGKGLEWVALIWYDGNNTYYADSVKGRFTISRDNSKNTLYLQMNSLRAEDTAVYYCARDRVYCSSTSCSPYYYYGMDVWGQGTTVTVSS |
| | | | SEQ ID NO: 24758 | SEQ ID NO: 28764 |

FIGURE 50
(Continued)

| | | | |
|---|---|---|---|
| iPS:393200 | 21-225_35E1 | NA | TCCTATGAGCTGACTCAGCCACCCTCAGTGTCCGTGTCCCAGGACAGACAGCAGCCATCACCTGCTCTGGAGATAAATTGGGGGAAAATATGCTTACTGGTTTCAGCAGAAGCCAGGCCAGTCCCCTGTGATAGTCATCTATCAAGATAGGAAGCGGCCCTCAGGGATCCCTGAGCGATTCTCTGGCTCCAACTCTGGGAACACAGCCACTCTGACCATCAGCGGGACGCAGGCTATGGATGAGGCTGACTATTACTGTCAGGCGTGGGACAACAGCACTGCGGTATTCGGCGGAGGGACCAAGCTGACCGTCCTA SEQ ID NO: 24759 | CAGGTGAAGCTGGTGCAGTCTGGGGCTGAGGTGAAGAAGCCTGGGGCCTCAGTGAAGGTCTCCTGCAAGGCTTCAGGATACACCTTCACCGGCTACTATATGCACTGGGTGCGACAGGCCCCTGGACAAGGGCTTGAGTGGATGGGATGGATCAACCCTAAAAGTGGTGGCACAAATTATGCACAGAAGTTTCAGGGCAGGGTCACCATGACCAGGGACACGAGCCAGCAGGCTCATCAGCACAGTCTACATGGAGCTGAGCAGCCTGAGATCTGACGACACGGCCGTGTATTACTGTGCGAGAGTGTATTACCATGGTTCGGGGAGTTATTATAACGAGTTTGATTATTGGGGCCAGGGAACCCTGGTCACCGTCTCCTCA SEQ ID NO: 28765 |
| | | AA | SYELTQPPSVSVSPGQTASITCSGDKLGEKYAYWFQQKPGQSPVLVIYQDRKRPSGIPERFSGSNSGNTATLTISGTQAMDEADYYCQAWDNSTAVFGGGTKLTVL SEQ ID NO: 24760 | QVKLVQSGAEVKKPGASVKVSCKASGYTFTGYYMHWVRQAPGQGLEWMGWINPKSGGTNYAQKFQGRVTMTRDTSISTVYMEPSRLRSDDTAVYYCARVYYHGSGSYYNEFDYWGQGTLVTVSS SEQ ID NO: 28766 |
| iPS:393202 | 21-225_6B4 | NA | TCCTATGAGCTGACTCAGCCACCCTCAGTGTCCGTGTCCCCAAGACAGACAGTCAGCATCACCTGCTCTGGAGATAAATTGGGGGATAAATATGCTTGCTGGTATCAGCAGAAGCCAGGCCAGTCCCCTGTGCTGGTGGTTATCAGTCGCGAAGATCGCCAAGCGGCCCTCAGGGATCCCTGAGCGATTCTCTGGCTCCAACTCTGGGAACACAGCCACTCTGACCATCAGCGGGACCCAGGCCATGGATGAGGCTGACTATTACTGTCAGGCGTGGGACAACAGCACTGTGATATTCGGCGGAGGGACCAAGCTGACCGTCCTA SEQ ID NO: 24761 | GAGGTGCAGCTGTTGGAGTCTGGGGGAGGCTTGGTACAGCCTGAGGGGTCCCTGAGACTCTCCTGTGCAGCCTCTGGATTCACCTTTAGCAGTCAGTATGCCATGAGCTGGGTCCGCCAGGCTCCAGGGAAGGGGCTGGAGTGGGTCTCAGCTATTAGTGGTAGTGGTAGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGAATATTGTGGTGGTGACTGCTATTCCCCTTACTACTACTACGGTATGGACGTCTGGGGCCAAGGGACCACGGTCACCGTCTCCTCA SEQ ID NO: 28767 |

FIGURE 50
(Continued)

| | | | |
|---|---|---|---|
| | | AA | SYELTQPPSVSVSPRQTVSITCSGDKLGDKYACW YQQKPGQSPVLVIYQDRKRPSGIPERFSGSNSGN TATLTISGTQAMDEADYYCQAWDNNTVIFGGG TKLTVL<br><br>SEQ ID NO: 24762 | EVQLLESGGGLVQPEGSLRLSCAASGFTFSSYAMS WVRQAPGKGLEWVSAISGSGSSTYYADSVKGRFTI SRDNSKNTLCLQMNSLRAEDTAVYYCAKEYCGGD CYSPYYYYGMDVWGQGTTVTVSS<br><br>SEQ ID NO: 28768 |
| | | NA | TCCTATGAGCTGACTCAGCCACACTCAGTGTC AGTGCCACAGCACAGATGGCCAGGATCACCT GTGGGGGAAACAACATTGGAAGTAAAGCTGT GCACTGGTACCAGCAAAAGCCAGGCCAGGAC CCTGTGCTGGTCATCTATAGCGATAGCAACCG GCCCTCAGGGATCCCTGAGCGATTCTCTGGCT CCAACCCAGGGAACACCGCCACCCTAACCATC AGCAGGATGAGGCTGGGGATGAGGCTGACT ATTACTGTCAGGTGTGGGACAGTAGTAGTGAT CATGTGGTATTCGGCGGAGGGACCAAGCTGAC CGTCCTA<br><br>SEQ ID NO: 24763 | CAGGTGCAGTTGGTGGAGTCTGGGGGAGGCGTG GTCCAGCCTGGGAGGTCCCTGAGACTCTCCTGTG CAGCGTCTGGATTCACCTTCGGTAGCTATGGCAT GCACTGGGTCCGCCAGGCTCCAGGCAAGGGGCT GGAGTGGGTGGCACTTATATGGTATGATGGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGATCGGGT ATCTTGTAGTAGTTCCAGCTGCTATCCTTACTACT ACTACTACGGTATGGACGTCTGGGGCCAAGGGA CCACGGTCACCGTCTCCTCA<br><br>SEQ ID NO: 28769 |
| iPS:393204 | 21-225_8C12 | AA | SYELTQPHSVSVATAQMARITCGGNNIGSKAVH WYQQKPGQDPVLVIYSDSNRPSGIPERFSGSNPG NTATLTISRIEAGDEADYYCQVWDSSSDHVVFG GGTKLTVL<br><br>SEQ ID NO: 24764 | QVQLVESGGGVVQPGRSLRLSCAASGFTFGSYGM HWVRQAPGKGLEWVALIWYDGSNKYYADSVKGR FTISRDNSKNTLYLQMNSLRAEDTAVYYCARDRVS CSSSSCYPYYYYGMDVWGQGTTVTVSS<br><br>SEQ ID NO: 28770 |

FIGURE 50
(Continued)

| | | | | |
|---|---|---|---|---|
| iPS:393206 | 21-225_13F6 | NA | TCCTATGAGCTGACTCAGCCACCTCAGTGTC CGTGTCCCAGGAACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGGACAACACTGCTGTG GTATTCGGCGGAGGGACCAAGCTGACCGTCCT G SEQ ID NO: 24765 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCGCAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTGTATTTCTGTGCGAGGTCGTTT TACTATGGTTCGGGGACTTATTATAACGAGTTTG ACTACTGGGGCCAGGGAACCCTGGTCACCGTCTC CTCA SEQ ID NO: 28771 |
| | | AA | SYELTQPPSVSVSPGQTASITCSGDKLGDKYACW YQQKPGQSPVLVIYQDSKRPSGIPERFSGSNSGN TATLTISGTQAMDEADYYCQAWGNSTAVVFGG GTKLTVL SEQ ID NO: 24766 | QVQLVQSGAEVKKPGASVKVSCKASGYTFTGYYM HWVRQAPGQGLEWMGWINPNSGGANYAQKFQGR VTMTRDTSISTAYMELSRLRSDDTAVYFCARSFYY GSGTYYNEFDYWGQGTLVTVSS SEQ ID NO: 28772 |
| iPS:393208 | 21-225_16F3 | NA | TCCTATGTGCTGACTCAGCCACCTCGGTGTC AGTGTCCCCAGGAACGGACAGCGGCCAGGATTACCT GTGGGGAAACAACATTGGAAGTAAAAGTGT GCACTGGTACCAGCAGAAGCCAGGCCAGGAC CCTGTGCTGGTCGTCTATGATGATACCGACCG GCCCTCAGGGATCCCTGAGCGATTCTCTGGCT CCAACTCTGGGAACACGGCCACCCTGACCATC AGCAGGGTCGAAGCCGGGATGAGGCCGACT ATTACTGTCAGGTGTGGGATAGTAGCAAGTGAT CATGTGGTATTCGGCGGAGGGACCAAGCTGAC CGTCCTA SEQ ID NO: 24767 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGGCACTATA TGCACTGGGTGCGACAGGCCCCTGGACAAGGAC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGGTCGTAT TACTATGGTTCGGGGACTTATTATAACGAGTTTG ACTACTGGGGCCAGGGAACCCTGGTCACCGTCTC CTCA SEQ ID NO: 28773 |

FIGURE 50
(Continued)

| | | | |
|---|---|---|---|
| iPS:393210 | 21-225_17D3 | AA | SYVLTQPPSVSVAPGQTARITCGGNNIGSKSVHW YQQKPGQAPVLVVYDDTDRPSGIPERFSGSNSG NTATLTISRVEAGDEADYYCQVWDSSSDHVVFG GGTKLTVL<br><br>SEQ ID NO: 24768 | QVQLVQSGAEVKKPGASVKVSCKASGYTFTGHYM HWVRQAPGQGLEWMGWINPNSGGTNYAQKFQGR VTMTRDTSISTAYMELSRLRSDDTAVYYCARSYYY GSGTYYNEFDYWGQGTLVTVSS<br><br>SEQ ID NO: 28774 |
| | | NA | TCCTATGAGCTGACGCAGTCACCCTCAGTGTC CGTGTCCCCAGGACAGACAGCCAGCATCACCT GCTCTGGAGATAAATTGGGGGATAAATATGTT TACTGGTATCAGCAGAAGCCAGGCCAGTCCC TGTGGTGGTCATCTATCAAGATAGGAAGCGGC CCTCAGGGATCCCTGAGCGATTCTCTGGCTCC AACTCTGGGAACACAGGCTATGAGGACTGACTATT CGGGACCCAGGCTGTGGGACAGCAGCATCAGTA ACTGTCAGGCGTGGAGGGACCAAGCTGACCGTCCGA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGGCTGAGATCGGA CGACACGGCCGTGTATTACTGTGCGAGAGCGAAT TACTATGGTTCGGGGAGTTATTATAACGACTTTG ACTACTGGGGCCAGGGAACCCTGGTCACCGTCTC CTCA<br><br>SEQ ID NO: 28775 |
| | | AA | SYELTQSPSVSVSPGQTASITCSGDKLGDKYVY WYQQKPGQSPVVVIYQDRKRPSGIPERFSGSNSG NTATLTISGTQAMDEADYYCQAWDSITAVFGGG TKLTVR<br><br>SEQ ID NO: 24770 | QVQLVQSGAEVKKPGASVKVSCKASGYTFTGYYM HWVRQAPGQGLEWMGWINPNSGGTNYAQKFQGR VTMTRDTSISTAYMELSRLRSDDTAVYYCARANYY GSGSYYNDFDYWGQGTLVTVSS<br><br>SEQ ID NO: 28776 |

FIGURE 50
(Continued)

| | | | | |
|---|---|---|---|---|
| iPS:393212 | 21-225_30H6 | NA | TCCTATGAGCTGACTCAGCCACCCTCAGTGTC CGTGTCCCCAGGACAGACAGCCAGCATCACCT GCTCTGGAGATAAATTGGGTAATAAATATGCT TGCTGGTATCAGCAGAAGCCAGGCCAGTCCCC TGTGTTGGTCATCTATCAAGATAGCAAGCGGC CCTCAGGGATCCCGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTGTTTTC GGCGGAGGGACCAAGCTGACCGTCCTA<br><br>SEQ ID NO: 24771 | CAGATCACCTTGAAGGAGTCTGGTCCTACGCTGG TGAAACCCACACAGACCCTCACGCTGACCTGCAC CTTCTCTGGATTCTCACTCAGCACTGGTGGAGTG GGTGTGGGCTGATCCGTCAGCCCCAGGAAAG GCCCTGGAGTGGCTTGCACTCATTTATTGGCATG ATGATAAGCGCTACAGTCCCTCTCTGAAGAGCAG GCTCGCCATCACCAAGGACACCTCCAAAAACCA GGTGGTCCTTACAATTACCAACATGGACCCTGTG GACACAGCCACATATTACTGTGCTCACTTAATAG CAGTGGCTTTGACTATTGGGGCCAGGGAACCCT GGTCACCGTCTCCTCA<br><br>SEQ ID NO: 28777 |
| | | AA | SYELTQPPSVSVSPGQTASITCSGDKLGNKYACW YQQKPGQSPVLVIYQDSKRPSGIPERFSGSNSGN TATLTISGTQAMDEADYYCQAWDSSTVFGGGT KLTVL<br><br>SEQ ID NO: 24772 | QITLKESGPTLVKPTQTLTLTCTFSGFSLSTGGVVG WIRQPPGKALEWLALIYWHDDKRYSPSLKSRLAIT KDTSKNQVVLTITNMDPVDTATYYCAHLIAVAFDY WGQGTLVTVSS<br><br>SEQ ID NO: 28778 |
| iPS:393214 | 21-225_33A1 | NA | TCCTATGAGCTGACTCAGCCACCCTCAGTGTC CGTGTCCCCAGGACAGACAGCCAGCATCACCT GCTCTGGAGATAAATTGGGGGATAAATTGTT TATTGGTATCAGCAGAAGCCAGGCCAGTCCCC TGTGCTCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGGACAGCAGCACCGTGGTA ACTGTCAGGCGTGTGGGACCAAGCTGACCGTCCTA TTCGGCGGAGGGACCAAGCTGACCGTCCTA<br><br>SEQ ID NO: 24773 | CAGGTGCAGCTGGTGCAGTCTGGGGCTGAGGTG AAGAAGCCTGGGGCTTCAGTGAAGGTCTCCTGC AAGGCTTCTGGATACACCTTCAGCGGCTACTATA TGCACTGGGTGCGACAGGCCCCTGGACAAGGAC TTGAGTGGATGGGATGGATCAACCCTAACAATGG TGGCACACACTATGCACAGAAGTTTCAGGGCAG GGTCACCATGACCAGGGACACGTCCATCGCAC AGCCTCCATGGAGCTGAGCAGGCTGAGATCTGA CGACACGGCCGTGTATTTCTGTGCGAGGGATAT TATTATGCTTCGGGGAGTTATTATAACGACCTCG ACCCCTGGGGCCAGGGAACCCTGGTCACCGTCTC CTCA<br><br>SEQ ID NO: 28779 |

FIGURE 50
(Continued)

| | | AA | SYELTQPPSVSVSPGQTASITCSGDKLGDKFVYW YQQKPGQSPVLVIYQDSKRPSGIPERFSGSNSGN TATLTISGTQAMDEADYYCQAWDSTTVFGGG TKLTVL | QVQLVQSGAEVKKPGASVKVSCKASGYTFSGYYM HWVRQAPGQGLEWMGWINPNNGGTHYAQKFQGR VTMTRDTSIRTASMELSRLRSDDTAVYFCARGYYY ASGSYYNDLDPWGQGTLVTSS |
|---|---|---|---|---|
| | | | SEQ ID NO: 24774 | SEQ ID NO: 28780 |
| iPS:393218 | 21-225_14G3 | NA | TCCTATGAGCTGACTCAGCCACCCTCAGTGTC CGTGTCCCCAGGACAGACAGCCAGCATCACCT GCTCTGGAGATAAATTGGGGGATAAATATGTT TGCTGGTATCAGCAGAAGCCAGGCCAGTCCCC TGCTGGTCATCTATCAAGATCGCAAGCGGC CCTCAGGGATCCCTGAGCGATTCTCTGGCTCC AACTCTGGGAACACAGCCACTCTGACCATCAG CGGGACCCAGGCTATGGAGGCTGATTATT ACTGTCAGGCGTGGGGACAACAGCACTGTGTG GTATTCGGCGGAGGGACCAAGCTGACCGTCCT G | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTTCAGGGCAG GGTCACCATGACCAGGGACACAGTCCATCAGCAC AGCCTACATGGAGCTGAGCAGGCTGAGATCTGA CGACACGGCCGTTTATTACTGTGCGAGGTCGTAT TTTTATGGTTCGGGGAGTTATTATAACGAGTTTG ACTACTGGGGCCAGGGAACCCTGGTCACCGTCTC CTCA |
| | | | SEQ ID NO: 24775 | SEQ ID NO: 28781 |
| | | AA | SYELTQPPSVSVSPGQTASITCSGDKLGDKYVCW YQQKPGQSPVLVIYQDRKRPSGIPERFSGSNSGN TATLTISGTQAMDEADYYCQAWGNSTAVVFGG GTKLTVL | QVQLVQSGAEVKKPGASVKVSCKASGYTFTGYYM YWVRQAPGQGLEWMGWINPNSGGTNYAQKFQGR VTMTRDTSISTAYMELSRLRSDDTAVYYCARSYFY GSGSYYNEFDYWGQGTLVTSS |
| | | | SEQ ID NO: 24776 | SEQ ID NO: 28782 |

FIGURE 50
(Continued)

| | | | | |
|---|---|---|---|---|
| iPS:393222 | 21-225_17F5 | NA | TCCTATGAGCTGACTCAGCCACCCTCAGTGTC CGTGTCCCCAGGACAGACAGCAGCCAGCATCACCT GCTCTGGAGATAAATTGGGGACAAAATATGCT TGCTGGTATCAGCAGAAGCCAGGCCAGTCCCC TGTGCTGGTCATCTATCAAGATAGAAAGCGGC CCTCAGGGATCCCTGAGCGATTCTCTGGCTCC AACTCTGGGAACAGCCACTCTGACCATCAG CGGGACCCAGGCTATGGATGAGGCTGACTATT ACTGTCAGGCGTGGGACAGCAGCACGTATTC GGCGGAGGGACCAAACTGACCGTCCTA SEQ ID NO: 24777 | CAGATCACCTTGAAGGAGTCTGGTCCTTCGCTGG TGAAGCCACACAGACCCTCACGCTGACCTGCAC CTTCTCTGGATTCTCACTCAGCACTAGTGGAGTG GGTGTGGGCTGATCCGTCAGCCCCCGGAAAG GCCCCTGGAGTGGCTTGCACTCATTTATTGGGATG ATGATAAGCGCTACAGCCCATCTCTGAAGAGCA GGCTCACCATCTCCAAGGACACCTCCAAAACC AGTTGGTCCTGACAATGACCAACATGGACCCTGT GGACACAGCCACATATTCCTGTGCACACATTATA GCAGTGGCTTTGACTACTGGGGCCAGGGAACCC TGGTCACCGTCTCCTCA SEQ ID NO: 28783 |
| | | AA | SYELTQPPSVSVSPGQTASITCSGDKLGEKYACW YQQKPGQSPVLVIYQDRKRPSGIPERFSGSNSGN TATLTISGTQAMDEADYYCQAWDSSTVFGGGT KLTVL SEQ ID NO: 24778 | QITLKESGPSLVKPTQTLTLTCTFSGFSLSTSGVVG WIRQPPGKALEWLALIYWDDDKRYSPSLKSRLTIT KDTSKNQVVLTMTNMDPVDTATYSCAHIIAVAFD YWGQGTLVTVSS SEQ ID NO: 28784 |
| iPS:393224 | 21-225_31C2 | NA | TCCTATGAGCTGACTCAGCCACCCTCAGTGTC CGTGTCCCCAGGGCAGACAGCAGCCAGCATCACCT GCTCTGGAGATAAATTGGGGAAATAAATATGCT TGCTGGTATCAGCAGAAGCCAGGCCAGTCCCC TGTGCTGGTCGGTCATCTATCAAGATTCCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTGTATTC GGCGGAGGGACCAAACTGACCGTCCTA SEQ ID NO: 24779 | CAGATCACCTTGAAGGAGTCTGGTCCTACGCTGG TGAAACCCACACAGACCCTCACGCTGACCTGCAC CTTCTCTGGTTCTCCCTCAACACTGGTGGAGTG GGTGTGGGCTGATCCGTCAGCCCCCAGGAAAG GCCCCTGGAGTGGCTTGCACTCATTTATTGGAATG ATGATGAGCGCTACAGCCCATCTCTGAAGAGCA GGCTCACCATCACCAAGGACACCTCCAAAACC AGTTGGTCCTTACAATGACCAACATGGACCCTTT GGACACAGCCTCATATTACTGTGCACACTTAATA GCAGTTTCCTTTGACTACTGGGGCCAGGGAGCCC TGGTCACCGTCTCCTCA SEQ ID NO: 28785 |

FIGURE 50
(Continued)

| | | | |
|---|---|---|---|
| iPS:393226 | 21-225_33E6 | AA | SYELTQPPSVSVSPGQTASITCSGDKLGNKYACW YQQKPGQSPVLVIYQDSKRPSGIPERFSGSNSGN TATLTISGTQAMDEADYYCQAWDSSTVFGGGT KLTVL<br>SEQ ID NO: 24780 | QITLKESGPTLVKPTQTLTLTCTFSGFSLNTGGVGV GWIRQPPGKALEWLALIYWNDDERYSPSLKSRLTIT KDTSKNQVVLTMTNMDPLDTASYYCAHLIAVSFD YWGQGALVTVSS<br>SEQ ID NO: 28786 |
| | | NA | TCCTATGAGCTGACTCAGCCACCCTCAGTGTC CGTGTCCCAGGACAGACAGCCAGCATCACCT GCTCTGGAGATAAATTGGGGAATACAGCCAGGC CAGGATATAAATGCT TACTGGTTTCAGCAGAAGCCAGGCCAGTCCCC TGTGATAGTCATCTATCAAGATAGGAAGCGGC CCTCAGGGATCCCTGAGCGATTCTCTGGCTCC AACTCTGGGAACACAGGCTATGGATGAGGCTGACTATT ACTGTCAGGCGTGGGACAACAGCACTGCGGTA TTCGGCGGAGGGACCAAGCTGACCGTCCTA<br>SEQ ID NO: 24781 | CAGGTGAAGCTGGTGCAGTCTGGGGCTGAGGTG AAGAAGCCTGGGGCCTCAGTGAAGGTCTCCTGC AAGGCTTCAGGATACACCTTCACCGGCTACTATA TGCACTGGGTGCGACAGGCCCCTGGACAAGGGC TTGAGTGGATGGGATGGATCAACCTAACAGTGG TGGCACAAACTATGCACAGAAGTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGAGTGTAT TACTATGGTTCGGGAGTTATTATAACGAGTTTG ACTACTGGGGCCAGGGAACCCTGGTCACCGTCTC CTCA<br>SEQ ID NO: 28787 |
| | | AA | SYELTQPPSVSVSPGQTASITCSGDKLGDKYAY WFQQKPGQSPVIVIYQDRKRPSGIPERFSGSNSG NTATLTISGTQAMDEADYYCQAWDNSTAVFGG GTKLTVL<br>SEQ ID NO: 24782 | QVKLVQSGAEVKKPGASVKVSCKASGYTFTGYYM HWVRQAPGQGLEWMGWINPNSGGTNYAQKFQGR VTMTRDTSISTAYMELSRLRSDDTAVYYCARVYYY GSGSYYNEFDYWGQGTLVTVSS<br>SEQ ID NO: 28788 |

FIGURE 50
(Continued)

| | | | |
|---|---|---|---|
| iPS:393230 | 21-225_9G9 | NA | CAGTCTGTGCTGACTCAGCCACCCTCAGCGTC TGGGACCCCGGGCAGAGGGTCAACATGTCTT GTTCTGGAACCAACTCCAACATCGGAAGTTAT ACTGTAAACTGGTACCAGCAGCTCCCAGGAAC GGCCCCAAACTCCTCATCTATATTAATAATC AGCGGCCCTCAGGGGTCCCTGACCGATTCTCT GGCTCCAAGTCTGGCACCTCAGCTCTCCTGGC CATCAGTGGGCTCCAGTCTGAGGATGACAGCTG ATTATTACTGTGCAGCATGGGATGACAGCCTG AATGGTCATGTGGTATTCGGCGGAAGGACCAA GCTGACCGTCCTA<br/>SEQ ID NO: 24783 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGACAAGGAC TTGAGTGGATGGGATGGATCAACCTAACAGTGG TGGCACAGACTATGCACAGAAGTTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGGTCGTAT TACTATGGTTCGGGGACTTATTATAACGAGTTTG ACTACTGGGGCCAGGGAACCCTGGTCACCGTCTC CTCA<br/>SEQ ID NO: 28789 |
| | | AA | QSVLTQPPSASGTPGQRVNMSCSGTNSNIGSYTV NWYQQLPGTAPKLLIYINNQRPSGVPDRFSGSKS GTSASLAISGLQSEDEADYYCAAWDDSLNGHVV FGGRTKLTVL<br/>SEQ ID NO: 24784 | QVQLVQSGAEVKKPGASVKVSCKASGYTFTGYYIH WVRQAPGQGLEWMGWINPNSGGTDYAQKFQGRV TMTRDTSISTAYMELSRLRSDDTAVYYCARSYYYG SGTYYNEFDYWGQGTLVTVSS<br/>SEQ ID NO: 28790 |
| iPS:393232 | 21-225_17F12 | NA | CAGTCTGCCCTGACTCAGCCTGCCTCCGTGTCT GGGTCTCCTGGACAGTCGATCACCATCTCCTG CACTGGAGCCAGCAGTGACGTTGGTGTTATA ACTTCTGTCTCCTGGTACCAACAGCACCCAGGC AAAGCCCCCAAACTCATGATTTATGAGGTCAG TAATCGGCTCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAGTCATATACAAGCAGCAT CACTGTGGTATTCGGCGGAGGGACCAAACTGA CCGTCCTA<br/>SEQ ID NO: 24785 | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATGCCATG AGCTGGGTCCGCCAGGCTCCAGGGAAGGGGCTG GAGTGGGTCTCAGCTATTAGTGGTGGTGGTGGTA GCACATACTACGCAGACTCCGTGAAGGGCCGG TCACCATCTCCAGAGACAATTCCAAGAACACGCT GTATCTGCAAATGAACAGCCTGAGAGCCGAGGA CACGGCCGTATATTACTGTGCGAAATGGGGACGT GGATACAACTATGAGTACTACGGTATGGACG TCTGGGGCCAAGGGACCACGGTCACCGTCTCCTC A<br/>SEQ ID NO: 28791 |

FIGURE 50
(Continued)

| | | | |
|---|---|---|---|
| iPS:393234 | 21-225_26C10 | AA | QSALTQPASVSGSPGQSITISCTGASSDVGDYNSVSWYQQHPGKAPKLMIYEVSNRPSGVSNRFSGSKSGNTASLTISGLQAEDEADYYCSSYTSSITVFGGGTKLTVL<br><br>SEQ ID NO: 24786 | EVQLLESGGGLVQPGGSLRLSCAASGFTFSSYAMSWVRQAPGKGLEWVSAISGGGSTYYADSVKGRVTISRDNSKNTLYLQMNSLRAEDTAVYYCAKWGRGYNYEYYYGMDVWGQGTTVTSS<br><br>SEQ ID NO: 28792 |
| | | NA | TCCTATGAAGTGACTCAGCCACCCTCAATGTCCGTGTCCCCAGGACAGAGCCAGCATCACCTGCTCTGGAGATAAATATGGGGATAAATATATGTTTGCTGGTTTCAGCAGAAGCCAGGCCAGTCCCCTGTGTTGGTCATCTATCAAGATAGCAAGCGGCCCTCAGGGATCCCTGAGCGATTCTCTGGCTCCAACTCTGGGAACACAGCCACTCTGACCATCAGCGGGACCCAGGCTATGATGAGGCTGACTATTACTGTCAGGCGTGGGTCAACAACACTGTATTCGGCGGAGGGACCAAGCTGACCGTCCTA<br><br>SEQ ID NO: 24787 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATGTGCACTGGGTGCGACAGGCCCCTGGACAAGGCCTTGAGTGGATGGGATGGATCAACCCTAACAGTGGTGGCACAAACTATGCACAGAAGTTTCAGGGCAGGGTCACCATGACCAGGGACACGTCCATCAGCACAGCCTACATGGAGCTGAGCAGGCTGAGATCTGACGACACGGCCGTGTATTACTGTGCGAGAGAGGTGTAGTACTACCAGCTGCTATTAGGAATTACGGGCTACTACGGTATGGACGTCTGGGGCCAAGGGACCACGGTCACCGTCTCCTCA<br><br>SEQ ID NO: 28793 |
| | | AA | SYEVTQPPSMSVSPGQTASITCSGDKLGDKYVCWFQQKPGQSPVLVIYQDSKRPSGIPERFSGSNSGNTATLTISGTQAMDEADYYCQAWVNNTVFGGGTKLTVL<br><br>SEQ ID NO: 24788 | QVQLVQSGAEVKKPGASVKVSCKASGYTFTGYYVHWVRQAPGQGLEWMGWINPNSGGTNYAQKFQGRVTMTRDTSISTAYMELSRLRSDDTAVYYCARERCSTTSCYLGITGYYGMDVWGQGTTVTSS<br><br>SEQ ID NO: 28794 |

FIGURE 50
(Continued)

| | | | |
|---|---|---|---|
| iPS:393345 | 21-225_5G7 | NA | TCCTATGAGCTGACTCAGCCACCCTCAGTGTC CGTGTCCCCAGGACAGACAGCCAGCATCACCT GCTCTGGAGATAAATTGGGGATAAATATGCT TGGTGGTATCAGCAGAAGCCAGGCCAGTCCCC TGTGCTGGTCATCTATCAAGATAGGAAGCGGC CCTCAGGGATCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAACAGCACTGTGGTT TTCGGCGGAGGGACCAAACTGACCGTCCTA SEQ ID NO: 24789 | GAGGTGCAGCTGTTGGAGTCTGGGGGAGGCTTG GTACAGCCTGAGGGGTCCCTGAGACTCTCCTGTG CAGCCTCTGGATTCACCTTTAGCAGTTATGCCAT GAGCTGGGTCCGCCAGGCTCCAGGGAAGGGGCT GGAGTGGGTCTCAGCTATTAGTGGTAGTGGTGGT AGCACATACTACGCAGACTCCGTGAAGGGCCGG TTCACCATCTCCAGAGACAATTCAAGAACACGC TGTGTCTGCAAATGAACAGCCTGAGAGCCGAGG ACACGGCCGTATATTACTGTGCGAAAGAATATTG TGGTGGTGACTGCTATTCCCCTTACTACTACT ACGGTATGGACGTCTGGGGCCAAGGGACCACGG TCACCGTCTCCTCA SEQ ID NO: 28795 |
| | | AA | SYELTQPPSVSVSPGQTASITCSGDKLGNKYAW WYQQKPGQSPVLVIYQDRKRPSGIPERFSGSNSG NTATLTISGTQAMDEADYYCQAWDNSTVVFGG GTKLTVL SEQ ID NO: 24790 | EVQLLESGGGLVQPEGSLRLSCAASGFTFSSYAMS WVRQAPGKGLEWVSAISGSGSTYYADSVKGRFTI SRDNSKNTLCLQMNSLRAEDTAVYYCAKEYCGGD CYSPYYYYGMDVWGQGTTVTVSS SEQ ID NO: 28796 |
| iPS:393368 | 21-225_29H8 | NA | GACATCGTGATGACCCAGTCTCCAGACTCCCT GGCTGTGTCTCTGGGCGAGAGGGCCACCATCA ACTGCAAGTCCAGCCAGTCACTTTTACACAGC TCCAACAATTACAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTATTGTCAGCAA TATTATTGTACTCCTCCGACGTTCGGCCAAGG GACCAAGGTGAAAATCAAA SEQ ID NO: 24791 | CAGGTGCAGCTGGTGCAGTCTGGGGCTGAGGTG AAGAAGCCTGGGGCCTCAGTGAAGGTCTCCTGCA AGGCTTCTGGATACACCTTCACCAATTATGATAT CAACTGGGTGCGACAGGCCACTGGACAAGGCT TGAGTGGATGGGCTGGATGAACCCTAACAGTGGT AACACAGGCTATGCACAGAGGTTCCAGGGCAGA GTCACCATGACCAGGAACACCTCCATAAGCGCA GCCTACATGGAGCTGAGCAGCCTGAGATCTGAG GACACGGCCGTATACTTTGACTGTGCGAGTAGTG GCTGGTACTACTTTGACTACTGGGGCCAGGGAAC CCTGGTCACCGTCTCCTCA SEQ ID NO: 28797 |

FIGURE 50
(Continued)

| | | | |
|---|---|---|---|
| iPS:393565 | 21-225_34B11 | AA | DIVMTQSPDSLAVSLGERATINCRSSQTILHSSNN YNYLAWYQQKPGQPPKLLIYWASTRESGVPDRF SGSGSGTDFTLTISSLQAEDVAVYYCQQYYCTPP TFGQGTKVEIK<br>SEQ ID NO: 24792 | QVQLVQSGAEVQKPGASVKVSCKASGYTFTNYDIN WVRQATGQGLEWMGWMNPNSGNTGYAQRFQGR VTMTRNTSISAAYMELSSLRSEDTAVYYCASSSGW YYFDYWGQGTLVTVSS<br>SEQ ID NO: 28798 |
| | | NA | TCCTATGAGCTGACTCAGCCACCCTCAGTGTC CGTGTCCCCAGGACAGAGCAGCCATCACCT GCTCTGGAGATAAATTGGGGGATAAATATGCT TGCTGGTATCAGCAGAAGCCAGGCCAGTCCC TGTGGTGGTCATCTATCAAGATATGAAGCGGC CCTCAGGGATCCCTGAGCGATTCTCTGGCTCC AACTCTGGGAACACAGGCTATGATGAGGCTGACTATT CGGGACGCAGGCTGGGACACAGCACTGCGGTA ACTGTCAGGCGTGGGACAACAGCACTGCGGTA TTCGGCGGAGGGACCAAGCTGACCGTCCTA<br>SEQ ID NO: 24793 | CAGGTGAAACTGGTGCAGTCTGGGGCTGAGGTG AAGAAGCCTGGGGCCTCAGTGAAGGTCTCCTGC AAGGCTTCAGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGAGTGTAT TTCTATGGTTCGGGAGTTATTATAACGAGTTTG ACTACTGGGGCCAGGGAACCCTGGTCACCGTCTC CTCA<br>SEQ ID NO: 28799 |
| | | AA | SYELTQPPSVSVSPGQTASITCSGDKLGDKYACW YQQKPGQSPVVVIYQDMKRPSGIPERFSGSNSGN TATLTISGTQAMDEADYYCQAWDNSTAVFGGG TKLTVL<br>SEQ ID NO: 24794 | QVKLVQSGAEVKKPGASVKVSCKASGYTFGYYM HWVRQAPGQGLEWMGWINPNSGGTNYAQKFQGR VTMTRDTSISTAYMELSRLRSDDTAVYYCARVYFY GSGSYYNEFDYWGQGTLVTVSS<br>SEQ ID NO: 28800 |

FIGURE 50
(Continued)

| | | | | |
|---|---|---|---|---|
| iPS:393802 | 21-225_3D12 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGC TACTTAGCCTGGTACCAGCAGAAACCTGGCCA GGCTCCCAGGCTCCTCATCTATGGTACATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAGTTCACGC AGTTTTGGCCAGGGGACCAAGCTGGAGATCAA A SEQ ID NO: 24795 | GAGGTGCAGCTGGTGGAGTCTGGGGGAGGCTTG GTAAAGCCTGGGGGGTCCCTTAGACTCTCCTGTG CAGCCTCTGGATTCACTTTCAGTAGTACCGCTGAT GAACTGGGTCCGCCAGGCTCCAGGGAAGGGGCT GGAGTGGGTTGGCCGGATTAAAAACAAAATTGA TGGTGGGACAACAGACTACGTTGCACCGTGAA AGGCAGATTCACCATCTCAAGAGATGATTCAAA AAACACGTGTATCTGCAAATGAACAGCCTGAA AACCGAGGACACAGCCGTATATTACTGTACCACA GAAGGCTGAACACGGACTACTGGGGCCAGGGA ACCCTGGTCACCGTCTCCTCA SEQ ID NO: 28801 |
| | | AA | EIVLTQSPGTLSLSPGERATLSCRASQSVSSSYLA WYQQKPGQAPRLLIYGTSSRATGIPDRFSGSGSG TDFTLTISRLEPEDFAVYYCQQYGSSRSFGQGTK LEIK SEQ ID NO: 24796 | EVQLVESGGGLVKPGGSLRLSCAASGVTFSTAWM NWVRQAPGKGLEWVGRIKNKIDGGTTDYVAPVKG RFTISRDDSKNTLYLQMNSLKTEDTAVYYCTTEGW NTDYWGQGTLVTVSS SEQ ID NO: 28802 |
| iPS:393804 | 21-225_5H7 | NA | GACATCCAGATGACCCAGTCTCCATCTCCCT GTCTGCATCTGTTGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGTTACATCCAGTT TGCAAGGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAACATAATAGTTACCCGCTC ACTTTCGGCGGAGGGACCAAGGTGGAGATCA AA SEQ ID NO: 24797 | CAGCTGCAGCTGCAGGAGTCGGGCCCAGGACTG GTGAAGCCTTCGGAGACCCTGTCCCTCACCTGCA CTGTCTCTGGTGGCTCCATCAACAGAAGTAGTTA TTACTGGGGCTGGATCCGCCAGCCCCCAGGGAA GGGACCACTACTACAACCCGTCCCTCAAGAGTC GAGTCACCATATCCGTAGACACGTCCAAGAACC AGTTCTCCCTGAACCTGAGCTCTGTGACCGCCGC AGACACGGCTGTATATTCCTGTGCGAGACATGGA AAAGACTGGGGCTTGACTACTGGGGCCAGGGA ACCCTGGTCACCGTCTCCTCA SEQ ID NO: 28803 |

FIGURE 50
(Continued)

| | | | | |
|---|---|---|---|---|
| | | AA | DIQMTQSPSSLSASVGDRVTITCRASQGIRNDLG WYQQKPGKAPKRLIYVTSSLQGGVPSRFSGSGS GTEFTLTISSLQPEDFATYYCLQHNSYPLTFGGG TKVEIK | QLQLQESGPGLVKPSETLSLTCTVSGGSINRSSYYW GWIRQPPGKGLEWIGNIYSGTTYNPSLKSRVTIS VDTSKNQFSLNLSSVTAADTAVYSCARHGKDWGL DYWGQGTLVTVSS |
| | | | SEQ ID NO: 24798 | SEQ ID NO: 28804 |
| iPS:393806 | 21-225_6A6 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAGTAGTTACCCGTC ACTTTCGGCGGAGGGACCAAGGTGGAGATCA AA | CAGCTGCAGCTGCAGGAGTCGGGCCCAGGACTG GTGAAGCCTTCGGAGACCCTGTCCTCACCTGCA CTGTCTCTGGTGGCTCCATCAGCAGAAGTAGTTA CTACTGGGGCTGGATCCGCCAGCCCCCAGGGAA GGGGCTGGAGTGGATTGGAATATCTATTATAGT GGGATCCCTACTACAACCGTCCTCAAGAGTC GGGTCAACATATCCGTAGACAGTCCAAGAACC AGTTCTCCTGAAGCTGAACTCTGTGACCGCCGC AGACACGGCTGTATTACTGTGCGAGACACAGC AGCAGCTGGTCTCTTGACTACTGGGGCCAGGAA CCCTAGTCACCGTCTCCTCA |
| | | | SEQ ID NO: 24799 | SEQ ID NO: 28805 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHSSYPLTFGGGT KVEIK | QLQLQESGPGLVKPSETLSLTCTVSGGSISRSSYYW GWIRQPPGKGLEWIGNIYSGIPYNPSLKSRVNIS VDTSKNQFSLKLNSVTAADTAVYYCARHSSSWSL DYWGQGTLVTVSS |
| | | | SEQ ID NO: 24800 | SEQ ID NO: 28806 |

FIGURE 50
(Continued)

| | | | | |
|---|---|---|---|---|
| iPS:393808 | 21-225_1A2 | NA | GACATCCAGATGACCCAGTCTCCATCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTGCAACT TATTACTGTCTACAGCATAATAGTCACCCTC ACTTTCGGCGGAGGGACCAAGGTGGAGATCA AA | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGTACCAT GAACTGGGTCCGCCAGGCTCCAGGAAGGGCT GGAGTGGGTCTCATCCATTAGTGGTAGTGGTAGT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGGAGCAG CTCGTCCGGGTTTGACTACTGGGGCCAGGGAACC CTGGTCACCGTCTCCTCA |
| | | | SEQ ID NO: 24801 | SEQ ID NO: 28807 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSHPLTFGGG TKVEIK | EVQLVESGGGLVKPGGSLRLSCAASGFTFSSYTMN WVRQAPGKGLEWVSSISGSGSYIYYADSVKGRFTIS RDNAKNSLYLQMNSLRAEDTAVYYCARGSSSSGF DYWGQGTLVTVSS |
| | | | SEQ ID NO: 24802 | SEQ ID NO: 28808 |
| iPS:393810 | 21-225_5A4 | NA | GACATCCAGATGACCCAGTCTCCATCTTCCGT GTCTGCATCTGTAGGAGACAGAGTCACCATCA CTTGTCGGGCGAGTCAGGGTATTAGCAGCACCTGG TTAGCCTGGTATCAACAGAAACCAGGGAAAG CCCCTAAACTCCTGATCTATGATGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCGTGG ACGTTCGGCCAAGGGACCAAGGTGGAAATCA AA | GAGGTGCAGGTGTTGGAGTCTGGGGGAGGCTTG GTACAGCCTGGGGGGTCCCTGAGAGACTCTCCTGTG CAGCCTCTGGACTCACCTTAGCAGCTCTGCCAT GAGCTGGGTCCGCCAGGCTCCAGGGAAGGGGCT GGAGTGGGTCTCAGTTATTACAGACTCCGTGGTGGT AACACATTCTACACAGACTCCGTGAAGGGCCGGT TCACCATTTCCAGAGACAATTCCAAGAACACGCT GTATCTGCAAATGAACAGCCTGAGAGCCGAGGA CACGGCCGTATATTACTGTGCGAAACTGGGAA AGACTACTACTACGGTATGGACGTCTGGGGGC CAAGGGACCACGGTCACCGTCTCCTCA |
| | | | SEQ ID NO: 24803 | SEQ ID NO: 28809 |

FIGURE 50
(Continued)

| | | | |
|---|---|---|---|
| iPS:393812 | 21-225_6A11 | AA | DIQMTQSPSSVSASVGDRVTITCRASQGISTWLA WYQQKPGKAPKLLIYDASSLQSGVPSRFSGSGS GTDFTLTISSLQPEDFATYYCQQANSFPWTFGQG TKVEIK<br>SEQ ID NO: 24804 | EVQVLESGGGLVQPGGSLRLSCAASGLTFSSSAMS WVRQAPGKGLEWVSAISGRGNTFYTDSVKGRFTI SRDNSKNTLYLQMNSLRAEDTAVYYCAKLGKDYY YYGMDVWGQGTTVTVSS<br>SEQ ID NO: 28810 |
| | | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATATTGCAACT TATTACTGTCTACAGCATAATAGTTACCCGTG GACGTTCGGCCAAGGGACCAAGGTGGAAATC AAA<br>SEQ ID NO: 24805 | CAGGTGCAGTCTGGTGGAGTCTGGGGGAGGCGTG GTCCAGCCTGGGAGGTCCCTGAGACTCTCCTGTG CAGCGTCTGGATTCACCTTCAGTGACTGACTGGCAT GCACTGGGTCCGCCAGGCTCCAGGCAAGGGGCT GGAGTGGGTGGCAGTTATATGTTTGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATGACTGTGCGAGAGATCTTGG CTGGACGGAAGAGTACTGGGGCCAGGGAACCCT GGTCACCGTCTCCTCA<br>SEQ ID NO: 28811 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPWTFGQG TKVEIK<br>SEQ ID NO: 24806 | QVQLVESGGGVVQPGRSLRLSCAASGFTFSDYGM HWVRQAPGKGLEWVAVIWFDGSNKYYADSVKGR FTISRDNSKNTLYLQMNSLRAEDTAVYDCARDLG WTEEYWGQGTLVTVSS<br>SEQ ID NO: 28812 |

FIGURE 50
(Continued)

| | | | | |
|---|---|---|---|---|
| iPS:393814 | 21-225_7F4 | NA | GACATCCAGATGACCCAGTCTCCATCTCCT GTCTGCATCTGTAGGAGACAGAGTCACCATCA CTTGCCGGCAAGTCAGGGACAGAGTCACCATCA TTAGGCTGGTATCAGCAGCAGAAACCAGGGAAAG CCCCTAAGCGCCTGATTTATGCTGCATCCAATT TGCAAAGTGGGGTCCATCAAGGTTCAGCGGC AGTGGATCTGGGACAGAATTCACTCTCACAAT CAGCAGCCTGCAGCCTGAAGATTTTGCAACTT ATTACTGTCTACAGCATAGTGTTCACCGCTC ACTTTCGGCGGAGGGACCAAGGTGGAGATCA AA<br><br>SEQ ID NO: 24807 | CAACTGCAGCTGCAGGAGTCGGGCCCAGGACTG GTGAAGCCTTCGGAGACCCTGTCCCTCACCTGCA CTGTCTCTGGTGGCTCCATCAGCAGGAGTAGTTA CTACTGGGGCTGGATCCGCCAGCCCCCAGGGAA GGGGCTGGAGTGGATTGGGAATATCTATTATAGT GGGGCCACTACTACAACCCGTCCCTCAAGAGTC GAGTCACCATCTCCGTAGACACGTCCACGAACCA GTTCTCCCTGAAGCTGAGCTCTGTGACCGCCGCA GACACGGCTGTGTATTACTGTGCGAGACATAGCG GCAGCTGGTCCCTGACTACTGGGGCCAGGGAAC CCTGGTCACCGTCTCCTCA<br><br>SEQ ID NO: 28813 |
| | | AA | DIQMTQSPSSLSASVGDRVTITCRTSQGIRNDLG WYQQKPGKAPKRLIYAASNLQSGVPSRFSGSGS GTEFTLTISSLQPEDFATYYCLQHSAYPLTFGGG TKVEIK | QLQLQESGPGLVKPSETLSLTCTVSGGSISRSSYYW GWIRQPPGKGLEWIGNIYYSGATYYNPSLKSRVTIS VDTSTNQFSLKLSSVTAADTAVYYCARHSGSWSLD YWGQGTLVTVSS |
| | | | SEQ ID NO: 24808 | SEQ ID NO: 28814 |
| iPS:393816 | 21-225_6D4 | NA | GACATCCAGATGACCCAGTCTCCATCTCCCT GTCTGTCTCTGTAGGAGACAGAGTCACCATCA CTTGCCGGGCAAGTCAGGGCCATTAGAAATGAT TTAGGCTGGTATCAGCAGCAGAAACCAGGGAAAG CCCCTAAGCGTCTGATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATAGTAGTTACCCGCTC ACTTTCGGCGGAGGGACCAAGGTGGAGATCA AA<br><br>SEQ ID NO: 24809 | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTC CTACTGGGGCTGGATCCGCCAGCCCCCAGGGAA GGGGCTGGAGTGGATTGGAAATATCTATTATAGT GGGAGCCGCTACTACATTCCGTCCCTCAAGAGTC GAGTCACCATATCCGTAGCCACGTCCAAGAACCA GTTCTCCCTGAACCTGACCTCTGTGACCGCCGCA GACACGGCTGTCTTGACTGCGCGACACAGCA GCAGCTGGTCTTTGACTGCTGGGGCCAGGGAAC CCTGGTCACCGTCTCCTCA<br><br>SEQ ID NO: 28815 |

FIGURE 50
(Continued)

| | | | |
|---|---|---|---|
| | | AA | DIQMTQSPSSLSASVGDRVTITCRASQAIRNDLG WYQQKPGKAPKRLIYAASSLQSGVPSRFSGSGS GTEFTLTISSLQPEDFATYYCLQHSSYPLTFGGGT KVEIK<br>SEQ ID NO: 24810 | QLQLQESGPGLVKPSETLSLTCTVSGGSISRSSSYW GWIRQPPGKGLEWIGNIYYSGSAYYIPSLKSRVTISV ATSKNQFSLNLTSVTAADTAVYYCARHSSSWSLDC WGQGTLVTVSS<br>SEQ ID NO: 28816 |
| iPS:393818 | 21-225_6G12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCACTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAATAGTTACCCGCTC ACTTTCGGCGGAGGGACCAAGGTGGAGATCA AA<br>SEQ ID NO: 24811 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATTTGGTATGATAGAAGT AATAACTACTATGCAGACTCCGTGAAGGGCCGAT TCACCATCTCAAGAGACAATTCCAAGAATACGCT GTATCTGCAAATGAACAGCCTGAGAGCCGAGGA CACGGCTGTGTATTACTGTGCGAGAGAACTGGGG TTCCGGTCGACTACTGGGGCCAGGGAACCCTGG TCACCGTCTCCTCA<br>SEQ ID NO: 28817 |
| | | AA | DIQMTQSPSSLSASVGDRVTITCRASQGIRNDLG WYQQKPGKAPKRLIYAASTLQSGVPSRFSGSGS GTEFTLTISSLQPEDFATYYCLQHNSYPLTFGGG TKVEIK<br>SEQ ID NO: 24812 | QVQLVESGGGVVQPGRSLRLSCAASGFTFSSYGMH WVRQAPGKGLEWVAVIWYDRSNNYYADSVKGRF TISRDNSKNTLYLQMNSLRAEDTAVYYCARELGFR SDYWGQGTLVTVSS<br>SEQ ID NO: 28818 |

FIGURE 50
(Continued)

| | | | |
|---|---|---|---|
| iPS:393820 | 21-225_8H7 | NA | GACATCCAGATGACCCAGTCTCCATCCTCCT GTCTGCATCTGTAGGAGACAGAGTCACCATCA CTTGCCGGGCAAGTCAGGACAGTCATTAGAAATGAT TTAGGCTGGTATCAGCAGAAACCAGGGAAAG CCCCTAAGCGCCTGATTTATGCTGCATCCAGT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATAATAGTTACCCGTTC ACTTTCGGCGGAGGGACCAAGGTGGAGATCA AA |
| | | | SEQ ID NO: 24813 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGGGT KVEIK |
| | | | SEQ ID NO: 24814 |
| | | | CAGGTGCAGCTGGTGGAGTCTGGGGGAGGCGTG GTCCAGCCTGGGAGGTCCCTGAGACTCTCCTGTC CAGCCGTCTGGATTCACCTTCAGTGACTTTGGCAT GCACTGGGTCCGCCAGGCTCCAGGCAAGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGA CACGGCTGTGTATTACTGTGCGAGAGAGCTGGGG TTCCGGTCGACTACTGGGGCCAGGGAACCCTGG TCACCGTCTCCTCA |
| | | | SEQ ID NO: 28819 |
| | | | QVQLVESGGGVVQPGRSLRLSCPASGFTFSDFGMH WVRQAPGKGLEWVAVIWYEENNQYYADSVKGRF TISRDNSKNTLYLQMNSLRAEDTAVYYCARELGFR SDYWGQGTLVTVSS |
| | | | SEQ ID NO: 28820 |
| iPS:393822 | 21-225_15B11 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCGGCCCTGGGACCAAGGTGGATATCAA A |
| | | | SEQ ID NO: 24815 |
| | | | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAACTATGGCAT GCACTGGGTCCGCCAGGCTCCAGGCAAGGGCT GGAATGGGTGGCAGTTATATGGTATGAGGAAAG TAATAAATACTATACAGACTCCGTGAAGGGCCG ATTCACCATCTCCAGAGACAATTCCAAGAACACG CTGTATCTGCAAATGAACAGCCTGAGACCCGAG GACACGGCTGTGTATTACTGTGCGAGAGAAGTGG GATTCACTAGGACTACTGGGGCCAGGGAACCC TGGTCACCGTCTCCTCA |
| | | | SEQ ID NO: 28821 |

FIGURE 50
(Continued)

| | | | |
|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br>SEQ ID NO: 24816 | QVQLVESGGGVVQPGRSLRLSCAASGFTFSNYGM HWVRQAPGKGLEWVAVIWYEESNKYYTDSVKGR FTISRDNSKNTLYLQMNSLRPEDTAVYYCAREVGF TEDYWGQGTLVTVSS<br>SEQ ID NO: 28822 |
| iPS:393824 | 21-225_10F12 | NA | GACATCCAGATGACCCAGTCTCCATCCTCCCT GTCTGCATCTGTAGGAGACAGAGTCACCATCA CTTGCCGGGCAAGTCAGAACAGAACATTAGTAGTTAT TTAAATTGGTATCAGCAGAAACCAGGGAAAG CCCCTAAACTCCTGATCTATGCTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAATACCCCCTTC TTCACTTTCGGCCCTGGGACCAAAGTGGATAT CAAA<br>SEQ ID NO: 24817 | GAGGTGCAGCTGTTGGAGTCTGGGGGAGGCTTG GTACAGCCTGGGGGGTCCCTGAGACTCTCCTGTG CAGCCTCTGAATTCACCTTTAGCAGCTATGCCAT GAGCTGGGTCCGCCAGGCTCCAGGGAAGGGGCT GGAGTGGGTCTCAATTATTAGTGGTCGTGGTGGT AACACATTCTACGCAGACTCCGTGAAGGGCCGGT TCACCATCTCCAGAGACAATTCCAAGAACACTCT GTATCTGCAAATGAACAGCCTGAGAGCCGAGGA CACGGCCGTATATTACTGTGCGTCCCGTAGCA GTGGCTGGCTCGGAGGCTTTGCTATCTGGGGCC AAGGGACAATGGTCACCGTCTCTCA<br>SEQ ID NO: 28823 |
| | | AA | DIQMTQSPSSLSASVGDRVTITCRASQNISSYLN WYQQKPGKAPKLLIYAASSLQSGVPSRFSGSGS GTDFTLTISSLQPEDFATYYCQQSYNTPFFTFGPG TKVDIK<br>SEQ ID NO: 24818 | EVQLLESGGGLVQPGGSLRLSCAASEFTFSSYAMS WVRQAPGKGLEWVSIISGRGGNTFYADSVKGRFTI SRDNSKNTLYLQMNSLRAEDTAVYYCASRVAVAG SEAFAIWGQGTMVTVSS<br>SEQ ID NO: 28824 |

FIGURE 50
(Continued)

| | | | |
|---|---|---|---|
| iPS:393826 | 21-225_10G5 | NA | GACATCCAGATGACCCAGTCTCCATCCCCT GTCTGCATCTGTAGGAGACAGAGTCACCATCA CTTGCCGGGCAAGTCAGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA SEQ ID NO: 24819 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAACTATGGCAT GCACTGGGTCCGCCAGGCTCCAGGCAAGGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTTTATTACTGTACGAGAGAACTGGGG TTCCGGTCTGACTACTGGGGCCAGGGAACCCTGG TCACCGTCTCCTCA SEQ ID NO: 28825 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK SEQ ID NO: 24820 | QVQLVESGGGVVQPGRSLRLSCAASGFTFSNYGM HWVRQAPGKGLEWVAVIWYEENNQYYADSVKGR FTISRDNSKNTLYLQMNSLRAEDTAVYYCTRELGF RSDYWGQGTLVTVSS SEQ ID NO: 28826 |
| iPS:393828 | 21-225_10H12 | NA | GACATCCAGATGACCCAGTCTCCATCCCCT GTCTGCATCTGTAGGAGACAGAGTCACCATCA CTTGCCGGGCAAGTCAGGCATTAGAAATGAT TTAGGCTGGTATCAGCAGAAACCAGGGAAAG CCCCTAAGCGCCTGATCTATGGTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAAGTTACCCGCTC ACTTTCGGCGGAGGGACCAAGGTGGAGATCA AA SEQ ID NO: 24821 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATTTGGTATGAAGACAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG TTCCGGTCTGACTACTGGGGCCAGGGAACCCTGG TCACCGTCTCCTCA SEQ ID NO: 28827 |

FIGURE 50
(Continued)

| | | | |
|---|---|---|---|
| iPS:393830 | 21-225_12.A1 | AA | DIQMTQSPSSLSASVGDRVTITCRASQGIRNDLG WYQQKPGKAPKRLIYGASSLQSGVPSRFSGSGS GTEFTLTISSLQPEDFATYYCLQHNSYPLTFGGG TKVEIK<br>SEQ ID NO: 24822 | QVQLVESGGGVVQPGRSLRLSCAASGFTFSDYGM HWVRQAPGKGLEWVAVIWYEDNNQYYADSVKGR FTISRDNSKNTLYLQMNSLRAEDTAVYYCARELGF RSDYWGQGTLVTVSS<br>SEQ ID NO: 28828 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24823 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG TTCCGGTCTGACTACTGGGGCCAGGGAACCCTGG TCACCGTCTCCTCA<br>SEQ ID NO: 28829 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 24824 | QVQLVESGGGVVQPGRSLRLSCAASGFTFSSYGMH WVRQAPGKGLEWVAVIWYEENNQYYADSVKGRF TISRDNSKNTLYLQMNSLRAEDTAVYYCARELGFR SDYWGQGTLVTVSS<br>SEQ ID NO: 28830 |

FIGURE 50
(Continued)

| | | | |
|---|---|---|---|
| iPS:393832 | 21-225_14B2 | NA | GACATCCAGATGACCCAGTCTCCATCCTCCT GTCTGCATCTGTTGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGTTACATCCAGTT TGCAAGGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAACATATAATAGTTACCCGCTC ACTTTCGGCGGAGGGACCAAGGTGGAGATCA AA | CAGCTGCAGCTGCAGGAGTCGGGGCCAGGACTG GTGAAGCCTTCGGAGAGCCTGTCCCTCACCTGCA CTGTCTCTGGTGGCTCCATCAACAGAAGTAGTTA TTACTGGGGTTGGATCCGCCAGCCCCCAGGGAAG GGGCTGGAGTGGATTGGGAATATCTATTATAGTG GGACCACCTACTACAACCCGTCCCTCAAGAGTCG AGTCACCATATCCGTAGACACGTCCAAGAACCA GTTCTCCCTGAACCTGAGCTCTGTGACGCCGCA GACACGGCTGTATATTCCTGTGCGAGACATGAA AAGACTGGGGCCTTGACTACTGGGGCCAGGGAG CCCTGGTCACCGTCTCCTCA |
| | | AA | DIQMTQSPSSLSASVGDRVTITCRASQGIRNDLG WYQQKPGKAPKRLIYVTSSLQGGVPSRFSGSGS GTEFTLTISSLQPEDFATYYCLQHNSYPLTFGGG TKVEIK | QLQLQESGPGLVKPSETLSLTCTVSGGSINRSSYYW GWIRQPPGKGLEWIGNIYYSGTTYYNPSLKSRVTIS VDTSKNQFSLNLSSVTAADTAVYSCARHGKDWGL DYWGQGALVTVSS |
| | | | SEQ ID NO: 24825 | SEQ ID NO: 28831 |
| | | | SEQ ID NO: 24826 | SEQ ID NO: 28832 |
| iPS:393836 | 21-225_15A2 | NA | GACATCCAGATGACCCAGTCTCCATCCTCACT GTTTGCATTTATAGGAGACAGAGTCACCATCA CTTGTCGGGCGAGTCAGGGCATTAGCAATTAT TTAGCCTGGTTTCAGCAGAAACCTGGAAAAGC CCCTAAGTCCCTGATTTTTGCTGTGCATCCAGTT GCAAAGTGGGGTCCCATCAAAGTTTAGCGGCA GTGGATTTGGGACAGATTTCACTTTTCCCATCA GCAGCCTGCAGCCTGAAGATTTTGCAAATTAT TACTGCCAACAGTATTATAGTTACCCATTCACT TTCGGCCCTGGGACCCAAGTGGATGTCAAA | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATACCAT GAACTGGGTCCGCCAGGCTCCAGGGAAGGGGCT GGAGTGGGTCTCATCCATTAGTAGTGGTAGTGGT TACATATACTACGCAGACTCAGTGAAGGGCCGAT TCACCATCTCCAGAGACAACGCCAAGAACTCACT GTATCTGCAAATGAACGCCCTGAGAGCCGAGGA CACGGCTGTGTATTACTGTGCGAGAGTGGCTTCA TTTGACTACTGGGGCCAGGGAACCCTGGTCACCG TCTCCTCA |
| | | | SEQ ID NO: 24827 | SEQ ID NO: 28833 |

FIGURE 50
(Continued)

| | | | |
|---|---|---|---|
| iPS:393838 | 21-225_6G2 | AA | DIQMTQSPSSLSAFIGDRVTITCRASQGISNYLAW FQQKPGKAPKSLIFAASSLQSGVPSKFSGSGFGT DFTFPISSLQPEDFANYYCQQYSYPFTFGPGTQ VDVK<br>SEQ ID NO: 24828 | EVQLVESGGGLVKPGGSLRLSCAASGFTFSSYTMN WVRQAPGKGLEWVSSISGSGSYIYYADSVKGRFTIS RDNAKNSLYLQMNALRAEDTAVYYCARVASFDY WGQGTLVTVSS<br>SEQ ID NO: 28834 |
| | | NA | GACATCCAGATGACCCAGTCTCCATCCTCCG GTCTGCATTTGTTGGAGACAGAGTCACCATCA CTTACCGGGCAAGTCAGGGCATTAGAAATGAT TAGGCTGGTATCAGCAGAAACCAGGAAAG CCCCTCAGCGCCTGATCTATGCTGCATCCAGT CTGCAAAGTGGGGTCCCATCAAGGTTCAGCGG CAGTGGATATGGGACTGAATTCAATATCACAA TCAGCAGCTTGCAGCTGAAGATTTTGCAATT TATTACTGTATACAGCATAATAGTTACCTGTG GACGTTCGGCCAAGGGACCAAGGTGGAAATC ACA<br>SEQ ID NO: 24829 | CTGGTGCAGTCTGGTGGAGTCTGGGGGAGGCGTG GTCCAGCCTGGGAAGTCCCTGAGACTCTCCTGTG CAGCGTCTGGATTCACCTTCAGTGACTATGGCAT ACACTGGGTCCGCCAGGCTCCAGGCAAGGGGCT GGAGTGGGTGGCAGTCATTTGGTTTGATGAAGT AATAAATACTATGCAGACTCCGTGAAGGGCCGA TTCACCATCTCCAGCGACAATTCCAAAAACACGC TGTATCTGCAAATGAACAGCCTGAGAGCCGAGG ACACGGCTGTGTATTACTGTGCGAGAGATCTTGG CTGGACGGAAGAGTACTGGGGCCAGGGAACCCT GGTCACCGTCTCCTCA<br>SEQ ID NO: 28835 |
| | | AA | DIQMTQSPSSRSAFVGDRVTITYRASQGIRNDLG WYQQKPGKAPQRLIYAASSLQSGVPSRFSGSGY GTEFNITISSLQPEDFAIYYCIQHNSYLWTFGQGT KVEIT<br>SEQ ID NO: 24830 | LVQLVESGGVVQPGKSLRLSCAASGFTFSDYGIH WVRQAPGKGLEWVAVIWFDGSNKYYADSVKGRF TISSDNSKNTLYLQMNSLRAEDTAVYYCARDLGW TEEYWGQGTLVTVSS<br>SEQ ID NO: 28836 |

FIGURE 50
(Continued)

| | | | | |
|---|---|---|---|---|
| iPS:393840 | 21-225_3F8 | NA | GACTTCCAGATGACCCAGTCTCCATCTCCCT GTCTGCATCTGTAGGAGACAGAGTCACCATCA CTTGCCGGGCAAGTCAGAGTATTCTCAGTAT TTAAATTGGTATCGGCAGAAACCAGGGAGAG CCCCTCAGGTCCTGATCCATACTACATCCAGTT TGCAAAGTGGGGTCCCATCAAGGTTCAGTGGC AGTGGATCTGGGACAGTTTTCACTCTCACCAT CAGCAGTCTGCAACCTGAAGATTTTGCAACTT ACTACTGTCAACAGAGTTACAGTACCCGCTC ACTTTCGGCGGAGGGACCAGGGTGGAGATCA AC<br><br>SEQ ID NO: 24831 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGGGGCAGTTATATGCAGACTCCGTGAAGGGCCG TAATAAATACTATGCAGACACAATGCCAAGAACAC ATTCACCATCTCCAGAGACAATGCCAAGAACAC GCTGTATCTGCAAATGAACAGCCTGAGAGCCGA GGACACGGCTGTGTATTACTGTGCGAGAGATCTG AGTATGGGCGGTATGGACGTCTGGGGCCAAGGG ACCACGGTCACCGTCTCCTCA<br><br>SEQ ID NO: 28837 |
| | | AA | DFQMTQSPSSLSASVGDRVTITCRASQSILSYLN WYRQKPGRAPQVLIHTTSSLQSGVPSRFSGSGSG TVFTLTISSLQPEDFATYYCQQTYSTPLTFGGGTR VEIN<br><br>SEQ ID NO: 24832 | QVQLVESGGGVVQPGRSLRLSCAASGFTFSSYGMH WVRQAPGKGLEWGAVIWHDGSNKYYADSVKGRF TISRDNAKNTLYLQMNSLRAEDTAVYYCARDLSM GGMDVWGQGTTVTVSS<br><br>SEQ ID NO: 28838 |
| iPS:393844 | 21-225_3G7 | NA | GACATCCAGATGACCCAGTCTCCATCTCCCT GTCTGCATCTGTCGGAGACAGAGTCACCGTCA CTTGCCGGGCAAGTCAGAACATTTACAGGTAT TTAAATTGGTATCAGGGGAGACCAGGGAGAG CCCCTAAACTCCTCATCTATGCTGCATCCAGTT CGCAAAGTGGGGTCCCATCAAGATTCAGTGGC AGTGGATCTGGGACAGATTTCACTGTCACCAT CAGTAGTCTTCAACAGAGTTACAGTCCCCCTTC ATTACTGTCAACAGAGTTACAGTCCCCCTTC ACTTTCGGCGGAGGGGCCAAGGTGGAGATCG<br><br>SEQ ID NO: 24833 | CAGGTGCAGCTGGTGGAGTCTGGGGGAGGCGTG GTCCAGCCTGGGAGGTCCCTGAGACTCTCCTGTG CAGCGTCTGGATTCAACTTCAGTAACTATGGCAT GCACTGGGTCCGCCAGGCTCCAGGCAAGGGCT GGAGTGGGTGGCAGTCATATGACTCCGTGAAGGCCGA TAATAAATACTATGTAGACTCCGTGAAGGGCCGA TTCACCATCTCCAGAGACAATTCCAAGAACACGG TGTATCTGCAAATGAACAGCCTGAGAGCCGAGG ACACGGCTGTGTATTACTGTGCGAGAGATGAGAG GCTGGGGATTTTGACTACTGGGGCCAGGGAACC CTGGTCACCGTCTCCTCA<br><br>SEQ ID NO: 28839 |

FIGURE 50
(Continued)

| | | | | |
|---|---|---|---|---|
| | | AA | DIQMTQSPSSLSASVGDRVTVTCRASQNIYRYLN WYQGRPGRAPKLMIYAASSSQSGVPSRFSGSGS GTDFTVTISSLQPEDFATYYCQQSYSPPFTFGGG AKVEID | QVQLVESGGGVVQPGRSLRLSCAASGFNFSNYGM HWVRQAPGKGLEWVAVIWHDGSNKYYVDSVKGR FTISRDNSKNTVYLQMNSLRAEDTAVYYCARDERL GIFDYWGQGTLVTVSS |
| | | | SEQ ID NO: 24834 | SEQ ID NO: 28840 |
| iPS:393848 | 21-225_4H2 | NA | GACATCCAGATGACCCTGTCTCCATCCTCCT GTCTGCATCTGTAGGAGACAGAGTCACCATCA CTTGCCGGGCAATTCAGAACATTAGCAGCTAT TTAAATTGGTATCAGCAGAAACCAGGAAAG CCCCTAAACTGATGATCTATGCTGCATCCAGC TTGCAAAGTGGGGTCCCATCAAGGTTCAGTGG CAGAGGATCTGGGACAGATTCACTCTCACCA TCGGTTGTGTGCAAGCTGAAGATTTTGCAACT TACTACTGTCAACAGAGTTACAGAACCCCCTT ATTCACTTTCGGCCCTGGGACCAAGGTTGATA TCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCGGCTATGCCAT GAACTGGGTCCGCCAGGCTCCAGGGATGGGGCT GGAGTGGGTCTCAGTTATTAGTCGTAGTGGTGGT TACACATACTACGGACTCCGTGAAGGGCCGGT TCACCATCTCCAGAGACAATTCCAAGAACACGCT GTATCTGCAAATGAACAGCCTGAGAGCCGAGGA CACGGCCGTCTATTACTGTGCGTCCCGTTTAGCA CGTGGCTGGCTCGGAGGCTTTTGATATCTGGGCC AAGGGACAATGGTCACCGTCTCTTCA |
| | | | SEQ ID NO: 24835 | SEQ ID NO: 28841 |
| | | AA | DIQMTLSPSSLSASVGDRVTITCRAIQNISSYLNW YQQKPGKAPKLVIYAASSLQSGVPSRFSGRGSGT DFTLTIGCVQREDFATYYCQQSYRTPLFTFGPGT KVDIK | EVQLLESGGGLVQPGGSLRLSCAASGFTFSGYAMN WVRQAPGMGLEWVSVISRSGGYTYYADSVKGRFT ISRDNSKNTLYLQMNSLRAEDTAVYYCASRLAVAG SEAFDIWGQGTMVTVSS |
| | | | SEQ ID NO: 24836 | SEQ ID NO: 28842 |

FIGURE 50
(Continued)

| | | | |
|---|---|---|---|
| iPS:393852 | 21-225_12A10 | NA | GACGTCCAGATGACCCAGTCTCCATCCTCCT GTCTGCATCTGTAGGAGACAGAGTCACCATCA CTTGCCGGGCAAGTCAGAACATTTACAGCTAT TTAAATGGTATCAGCAGAAACCAGGGAGAG CCCCTAAGGTCCTGATCCATACTGCATCCAGT TTGCAAAGTGGGGTCCCATCAAGGTTCAGTG CAGTGGATCTGGGCAGATTTCACTCTCACCA TCAACAGTCTGCAACCTGAAGATTTTGCAACT TACTACTGTCAGCAGAGTTACAGTCCCCCTCT CACTTTCGGCGGAGGGACCAAGGTAGAGATC AAA SEQ ID NO: 24837 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATACAGACTCGTGAAGAC TAATAAATACTATACAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGACGAG AGGCTGGGGGATTTTTGACTACTGGGCCAGGGAA CCCTGGTCACCGTCTCCTCA SEQ ID NO: 28843 |
| | | AA | DVQMTQSPSSLSASAGDRVTITCRASQNIYSYLN WYQQKPGRAPKVLIHTASSLQSGVPSRFSGSGSG ADFTLTINSLQPEDFATYYCQQSYSPPLTFGGGT KVEIK SEQ ID NO: 24838 | QVQLVESGGGVVQPGRSLRLSCAASGFTFSSYGMH WVRQAPGKGLEWVAVIWHDESNKYYTDSVKGRF TISRDNSKNTLYLQMNSLRAEDTAVYYCARDERLG IFDYWGQGTLVTVSS SEQ ID NO: 28844 |
| iPS:393854 | 21-225_7H11 | NA | GACATCCAGATGACCCAGTCTCCATCCTCCGC ATCTGCATCTGTAGGAGTCAGAGTCACCATCA TTTGCCTGGCAAGTCAGGGCATTAGAAATGAT TTAGGCTGGTATCAGCAGAAACCAGGGAAAG CCCCTAAGGCATAATCTATGTTGCATGTAGT TTCCAAAGTGGGGTCCCATCAAGGTTCAGCGG CAGTGGATATGGGACAGAATTCACTCTCACAA TCAGCATCATGCAGCCTGAAGATTTCGCAACT TATTACTGTCTACAACATATCTTTACCCGCTC ACTTTCGGCGGAGGGACCAAGGTGGAGATCA AA SEQ ID NO: 24839 | CAGGTGCAGCTGGTGGAGTCTGGGGGAGGCGTG GTCCAGCCTGGGAGGTCCCTGAGACTCTCCTGTT CAGCGTCTGGATTCACCTTCAGTGACTATGGCAT GCACTGGGTCCGCCAGGCTCCAGGCAAGGGGCT GGAGTGGGTGGCAGTTATATGGCATGATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GTTCCGGTCTGACTACTGGGGCCAGGGAACCCTG GTCACCGTCTCCTCA SEQ ID NO: 28845 |

FIGURE 50
(Continued)

| | | | |
|---|---|---|---|
| iPS:393856 | 21-225_14C2 | AA | DIQMTQSPSSASASVGVRVTITCLASQGIRNDLG WYQQKPGKAPKRIIYVACSFQSGVPSRFSGSGY GTEFTLTISIMQPEDFATYYCLQHNLYPLTFGGG TKVEIK<br>SEQ ID NO: 24840 | QVQLVESGGGVVQPGRSLRLSCSASGFTFSDYGMH WVRQAPGKGLEWVAVIWYDENNKYYADSVKGRF TISRDNSKNTLYLQMNSLRAEDTAVYYCARELGFR SDYWGQGTLVTVSS<br>SEQ ID NO: 28846 |
| | | NA | GACATCCAGATGATCCAGTCTCCATCCTCCCT GTTTGCATGTGTAGGAGACAGAGTCATCATCA CTTGCCGGGCAAGTCAGGGCATTAGAAATGAT TTAGACTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGACAGAATTCACTCTCACAA TCAGCAGCGTGCAGCGTGAAGATTTTGCAACT TATTACTGTGTACAGCATAATAGTTACCCGCT CACTTTCGGCGGAGGGACCAAGGTGGAGATC AGA<br>SEQ ID NO: 24841 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGAAGACTCCGTGAAGGCCG AATCACCATCTCCAGAGACAATTCCAAGAACACG CTGTATCTGCAAATGAACAGCCTGAGAGCCGAG GACACGGGTGTTATTACTGTGCGAGAGAAGTG GGATTCCGGTCTGACTACTGGGGCCAGGGAACCC TGGTCACCGTCTCCTCA<br>SEQ ID NO: 28847 |
| | | AA | DIQMIQSPSSLFACVGDRVIITCRASQGIRNDLDW YQQKPGKAPKRLIYAASSLQSGVPSRFSGSGSGT EFTLTISSVQREDFATYYCCVQHNSYPLTFGGGTK VEIR<br>SEQ ID NO: 24842 | QVQLVESGGGVVQPGRSLRLSCAASGFTFSDYGM HWVRQAPGKGLEWVAVIWYDESNKYYEDSVKGR FTISRDNSKNTLYLQMKSLRAEDTGVYYCAREVGF RSDYWGQGTLVTVSS<br>SEQ ID NO: 28848 |

FIGURE 50
(Continued)

| | | | | |
|---|---|---|---|---|
| iPS:393862 | 21-225_5G2 | NA | GACATCCAGATGACCCAGTCTCCATCCTCCCC GTCTGCATCTGTAGGAGACAGAGTCACCATCA CTTTCCGGGCAAGTCAGAACATTATTAGTTAT TTAAATTGGTATCAGCAGAAACCAGGAAAG CCCGTAAGCTCGTGATCTATGGTGCATCCAGT TTGCAAAGTGGGGTCCCATCAAGGTTCAGTGG CAGTGGATCTGGGACAGATTTCACTCTCAACA TCAGAAGTCTGCAACCTGAAGATTTTGCAACT TACTACTGTCAACAGAGTTACAGTACTCCCTT ATTCACTTTCGGCCCTGGGACCAAAGTGGATA TCAAA SEQ ID NO: 24843 | GAGGTGCAGCTGTTGGAGTCTGGGGGAGGCTTG GTACAGCCTGGGGGGTCCCTGAGACTCTCCTGTG CAGCCCTCTGAATTCACCTTTAGCAGCTATGCCAT GAGCTGGGTCCGCCAGGCTCCAGGGAAGGGGCT GGAGTGGGTCTCAGTTATTAGTGGTCGTGGTGTT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGTCCGTATAGCA GTGGCTGCTCGGAGGCTTTTGATATCTGGGGCC AAGGGACAATGGTCACCGTCTCTTCA SEQ ID NO: 28849 |
| | | AA | DIQMTQSPSSPSASVGDRVTITFRASQNIISYLNW YQQKPGKARKLVIYGASSLQSGVPSRFSGSGSGT DFTLNIRSLQPEDFATYYCQQSYSTPLFTFGPGTK VDIK SEQ ID NO: 24844 | EVQLLESGGGLVQPGGSLRLSCAASEFTFSSYAMS WVRQAPGKGLEWVSVISGRGVNTFYADSVKGRFTI SRDNSKNTLYLQMNSLRAEDTAVYYCASRIAVAGS EAFDIWGQGTMVTVSS SEQ ID NO: 28850 |
| iPS:393864 | 21-225_4C5 | NA | GACATCCAGATGACCCAGTCTCCATCCTCCCT GTCTGCATCTGTAGGACACAGAGTCACCTCA CTTGCCGGGCAAGTCGGGGCATCAGAGGTGAT TTAGGTTGGTATGCGCCAGAAACCAGGGAAAGC CCCTAAGGCGCTTATCTATGCTGCATCCAGTT GCAAAGTGGGGTCCCATCAAGGTTCAGGCA GTGGATATGGGACAGATTCACTCTCACAATC GGCAGCCTGCAGCTGAAGATTTTGCAACTTA TTACTGTCTACAGCATTATAGTTACCCTCGGAC GTTCGGCCAAGGGACCAAGGTGGAAATCAAA SEQ ID NO: 24845 | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGTCCT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TATATCTGCAAATGAACAGCCTGAGAGCCGAGG ACACGGCTGTTTATTACTGTGCGCGAGAAAGTA TACCAGCAGCTGGTACGACTACGGTATGGACGTC TGGGGCCAAGGGACCACGGTCACCGTCTCCTCA SEQ ID NO: 28851 |

FIGURE 50
(Continued)

| | | | |
|---|---|---|---|
| iPS:393866 | 21-225_14E3 | AA | DIQMTQSPSSLSASVGHRVHLTCRASRGIRGDLG WYRQKPGKAPKRLIYAASNLQSGVPSRFSGSGY GTEFTLTIGSLQPEDFATYYCLQHYSYPRTFGQG TKVEIK<br>SEQ ID NO: 24846 | QVQLVESGGGVVQPGRSLRLSCAASGFTFSSYVLH WVRQAPGKGLEWVAVIWYDGSNKYYADSVKGRF TISRDNSKNTLYLQMNSLRAEDTAVYYCAREKYTS SWYDYGMDVWGQGTTVTVSS<br>SEQ ID NO: 28852 |
| | | NA | GACATCCAGATGACCCAGTCTCCATCCTCCCT GTCTGCATCTGTAGGAGACAGAGTCCACCATCA CTTGCCGGGCAAGTCAGGGCATTAGAGAATGAT TTAGGCTGGTATCAACAAAAACCAGGGAAAG CCCCTAAGCGCATTATTTATTCTGCATCCAGTT TGCAAAGTGGGGTCCCATCAAGGTTCATCGGC AGTGGATGTGGGACTGAATTCACTCTCACAAT CAGCAGCCTGCAGCGTGAAGATTATAGTTAGCAGCTT ATTACAGTGTACAGCATTATAGTTACCCGTTC ACTTTCGGCGGAGGGACCAAGGTGGAGATCA AA<br>SEQ ID NO: 24847 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTTTGGCAT GCACTGGGTCCGCCAGGCTCCAGGCAAGGGCT GGAGTGGGTGGCAGTTATTTGGTATGAAGAAAAT AATCAATACTATGCAGACTCCGTGAAGGGCCGAT TCACCATCTCCAGAGACACAATTCCAAGAACACGCT GTATCTGCAAATGAACAGCCTGAGAGCCGAGGA CACGGCTTTTTATTACTGTGCGAGAGAGAGCTGGGG TTCCGGTCTGACTACTGGGGCCAGGGAACCCTGG TCACCGTCTCCTCA<br>SEQ ID NO: 28853 |
| | | AA | DIQMTQSPSSLSASVGDRVTITCRASQGIRNDLG WYQQKPGKAPKRIIYSASSLQSGVPSRFIGSGSCG TEFTLTISSLQREDFAAYYSVQHYSYPFTFGGGT KVEIK<br>SEQ ID NO: 24848 | QVQLVESGGGVVQPGRSLRLSCAASGFTFSDFGMH WVRQAPGKGLEWVAVIWYEENNQYYADSVKGRF TISRDNSKNTLYLQMNSLRAEDTAFYYCARELGFR SDYWGQGTLVTVSS<br>SEQ ID NO: 28854 |

FIGURE 50
(Continued)

| | | | |
|---|---|---|---|
| iPS:393868 | 21-225_9C11 | NA | GACATCCAGATGACCCAGTCTCCATCCTCCT GTCTGCATCTGTAGGAGACAGAGTCACCATCA CTTGCCGGGCAAGTCAGAACATTAGAAATTAT TTAAATTGGTATCAGCAGAAATCAGGAGAGC CCCTAAGCTCCTGATCTATGTTGCATCCAGTTT GCAAAGTGGGGTCCCATCAAGGTTCAGTGGCA GTGGATCTGGGACAGAATTCACTCTCACCATC AACAGTCTGCAACCTGAAGATTTTGCAATTTA TCACTGTCATCAGAGTAACAGTACTCCTCTCA CGTTCGGCCAAGGGACCAAGGTGGAAATCAA A | CAGGTGCAGCTGGTGGAGTCTGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGCATGATGAAACT AATAAATACTATGCAGATTCCGTGAAGGGCCGAT TCACCATCTCCAGAGACAATTCCAAGAACACGCT GTCTCTGCAAATGAACAGCCTGAGAGCCGAGGA CACGGCTGTGTATTACTGTGCGAGAGACGAGAG GCTGGGGATTTTGACTACTGGGGCCAGGGAACC CTGGTCACCGTCTCCTCA |
| | | | SEQ ID NO: 24849 | SEQ ID NO: 28855 |
| | | AA | DIQMTQSPSSLSASVGDRVTITCRASQNIRNYLN WYQQKSGRAPKLLIYVASSLQSGVPSRFSGSGSG TEFTLTINSLQPEDFAIYHCQSNSTPLTFGQGTK VEIK | QVQLVESGGGVVQPGRSLRLSCAASGFTFSSYGMH WVRQAPGKGLEWVAVIWHDETNKYADSVKGRF TISRDNSKNTLSLQMNSLRAEDTAVYYCARDERLG IFDYWGQGTLVTVSS |
| | | | SEQ ID NO: 24850 | SEQ ID NO: 28856 |
| iPS:393870 | 21-225_7B1 | NA | GATATCCAGATGACCCAGTCTCCATCCTCCACT GTCTGCTTCTGTAGGAGACAGAGTCACCATCA CTTGCCGGGCGAGTCAGGACATTAGCAATCAT TTAGTCTGGTTTCAGCAGAAACCAGGGAAAGC CCCTAAGTCCCTGATCTTTGCTGCATCCAGTTT ACAAAGTGGGGTCCCATCACACGTTCAGCGGCA GTGGATCTGGAACAGATTTCACTCTCACCATC AGCAGCCTGCAGCCTGAGGATTTTGCAACTTA TTACTGTCACCACCAGTATAATAGTTACCCCTCAC TTTCGGCCCTGGGACCAAAGTGGATTTCAAA | GAGGTGCAGCTGTGTTGGAGTCTGGGGGAGGCTTG GTACAGCCTGGGGGGGTCCCTGAGACTCTCCTGTG CAGCCTCTGGATTCACCTTTAGCAGCTATGACAT GAGCTGGGTCCGCCAGGCTCCAGGGAAAGGGGCT GGAGTGGGTCTCAACTATTAGTGGTAGTGGTGT ATCACATACTACGCAGACTCCGTGAAGGGCCGGT TCACCATCTCCAGAGACAACAGCCTGAAGAAACGCT GTATCTGCAAATGAACAGCCTGAGAGCCGAGGA CACGGCCGTATATTCTGTGCGAGAGATCGGGGC AGGGTGGGGCCAGGGAACCCTGGTCACCGTCT CCTCA |
| | | | SEQ ID NO: 24851 | SEQ ID NO: 28857 |

FIGURE 50
(Continued)

| | | | |
|---|---|---|---|
| iPS:393872 | 21-225_2A11 | AA | DIQMTQAPSSLSASVGDRVTITCRASQDISNHLV WFQQKPGKAPKSLIFAASSLQSGVPSQFSGSGSG TDFTLTISILQPEDFATYYCHQYNSYPFTFGPGTK VDFK<br>SEQ ID NO: 24852 | EVQLLESGGGLVQPGGSLRLSCAASGFTFSSYDMS WVRQAPGKGLEWVSTISGSGGITYADSVKGRFTI SRDNSKKTLYLQMNSLRAEDTAVYFCARDRGSVW GQGTLVTSS<br>SEQ ID NO: 28858 |
| | | NA | GACATCCAGATGACCCAGTCTCCATCCTCCCT GTCTCCATCTGTAGGAGACAGAGTCACCATCA CTTGCCGGGCAAGTCAGGGCATTAGAAATGAT TTAGGCTGGTATCAGCAGAAACCAGGGAAAG CCCCTCAGCTCCTGATCTCTGCTGCATCCAGTT TGCAAAGTGGGGTCCCATCAAGGTTCAGCGGC AGTGGATCTGGGACAGATTTCACTCTCACAAT CAGCAGTTTGCAGCCTGAAGATTTTGCAACTT ATTACTGTCTACAGCATAATAGTTACCCGCTC ACTTTCGGCGGAGGGACCAAGATGGAGATCA AA<br>SEQ ID NO: 24853 | CAGCTGCAGCTGCAGGAGTCGGGGCCAGGACTG GTGAAGCCTTCGGAGACCCTGTCCCTCACCTGCA CTGTCTCTGGTGGCTCCATCAGTAGAGTAGTTA CTACTGGGGCTGGATCCGGCAGCCCCCAGGGAA GGGGCTGGAGTGGATTGGGAATATCTATTATAGT GGGAGCACCTACTACAACCCGTCCGTCAAGAGTC GAGTCACCATATCGTAGACACGTCCAAGAACC AGTTCTCCCTGAAGCTGAGTACTGTGACCGCCGC AGACACGGCTGTGTATTACTGTGCGAGACATGGA AAAGACTGGGGCCTTGAAGACTGGGGCCAGGGA ACCCTGGTCACCGTCTCCTCA<br>SEQ ID NO: 28859 |
| | | AA | DIQMTQSPSSLSPSVGDRVTITCRASQGIRNDLG WYQQKPGKAPQRLISAASSLQSGVPSRFSGSGSG TDFTLTISSLQPEDFATYYCLQHNSYPLTFGGGT KMEIK<br>SEQ ID NO: 24854 | QLQLQESGPGLVKPSETLSLTCTVSGGSISRSSYYW GWIRQPPGKGLEWIGNIYYSGSTYYNPSVKSRVTIS VDTSKNQFSLKLSTVTAADTAVYYCARHGKDWGL EDWGQGTLVTVSS<br>SEQ ID NO: 28860 |

FIGURE 50
(Continued)

| | | | |
|---|---|---|---|
| iPS:393874 | 21-225_4C8 | NA | GACATCCAGATGATCCAGTCTCCATCCTTCCT GTTTGCATGTGTAGGAGACAGAGTCACCATCA CTTGCCGGGCAAGTCAGGCATTAGAAATGAT TTAGGCTGGTATCAGCAGAAACCAGGAAAG CCCCTAAGCGCCTGATATATGCTGCATCCAGT TTGCAAAGTGGGGTCCCATCAAGGTTCAGCGG CAGTGTATCTGGGACAGAATTCACTCTCACAA TCAGCAGCCTGCAGCCTGAAGATTTCGCAACT TATTACTGTCTACAGCATAATAGTTACCCGCTC ACTTTCGGCGGAGGGACCAAGGTGGAGATCA AA SEQ ID NO: 24855 | CAGGTGCAGCTGGTGGAGTCTGGGGGAGGCGTG GTCCAGCCTGGGAGGTCCCTGAGACTCTCCTGT CAGCGTCTGGATTCACCTTCAGTAACTATGGCAT GCACTGGGTCCGCCAGGCTCCAGGCAAGGGGCT GGAGTGGGTGGCAGTTATTTGGTATGAAGAAAAT AATCAATACTATGCAGACTCCGTGAAGGGCCGAT TCACCATCTCCAGAGACAATTCCAAGAACACGCT GTATCTGCAAATGAACAGCCTGACAGCCGAGGA CACGGCTGTTTATTACAGTCCGAGAGAAATGGGG TTCCTGTCTGACTACTGGGGCCAGGGAACCCTGG TCACCGTCTCCTCA SEQ ID NO: 28861 |
| | | AA | DIQMIQSPSFLFACVGDRVTITCRASQGIRNDLG WYQQKPGKAPKRLIYAASSLQSGVPSRFSGSVS GTEFTLTISSLQPEDFATYYCLQHNSYPLTFGGG TKVEIK SEQ ID NO: 24856 | QVQLVESGGGVVQPGRSLRLSCAASGFTFSNYGM HWVRQAPGKGLEWVAVIWYEENNQYYADSVKGR FTISRDNSKNTLYLQMNSLTAEDTAVYYSPREMGF LSDYWGQGTLVTVSS SEQ ID NO: 28862 |
| iPS:393876 | 21-225_9A1 | NA | GACATCCAGATGACCCAGTCTCCATCCTCCCG GTCTGCATTTGTTGGAGACAGAGTCACCATCA CTTGCCGGGCAAGTCAGGGCATTAGAAATGAT TTAGGGTGGTATCAGCAGAAAACCAGGAAAG CCCGTAAGCGCCTGATCTATACTGCATCCAGT TTGCAAAGTGGGGTCCCATCAAGGTTCAGCGG CAGTGGATATGGGACTGAATTCACTATCACAA TCAGCAGCTTGCAGCCTGAAGATTTTGCAACT TATTACTGTATACAGCATAATAAGTTACCTGTG GACGTTCGGCCAAGGGACCAAGGTGGAAATC AAA SEQ ID NO: 24857 | CAGGTGCAGGTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGGTTTGATGAAGT AATAAATACTATGCAGACTCCGTGAAGGGCCGA TTCACCATCTCCAGAGACAATTCCAAGAACACGC TGTATCTGCAAATGAACAGTCTGAGAGCCGAGG ACACGGCTGTGTATTACTGTGCGAGAGATCTTGG CTGGACGGAAGAGTACTGGGGCCAGGGAACCCC GGTCACCGTCTCCTCA SEQ ID NO: 28863 |

FIGURE 50
(Continued)

| | | | |
|---|---|---|---|
| | | AA | DIQMTQSPSSRSAFVGDRVTITCRASQGIRNDLG WYQQKPGKARKRLIYTASSLQSGVPSRFSGSGY GTEFTITISSLQPEDFATYYCIQHNSYLWTFGQGT KVEIK | QVQVVESGGGVVQPGRSLRLSCAASGFTFSDYGM HWVRQAPGKGLEWVAVIWFDGSNKYYADSVKGR FTISRDNSKNTLYLQMNSLRAEDTAVYYCARDLG WTEEYWGQGTPVTVSS |
| | | | SEQ ID NO: 24858 | SEQ ID NO: 28864 |
| iPS:393878 | 21-225_7G12 | NA | GACATCCAGATGACCCAGTCTCCATCCTCCCT GTCTGCATCTGTAGGAGACAGAGTCTCCATCA CTTGCCGGGCAAGTCAGATTCAGAATATTAACAACTAT TTAAATTGGTATCAGCAGAAACCAGGGAAAG GCCCTAAGGTCCTGATCCTTACTGCATCCAGTT TGCAAAGTGGGTCCCATCAAGGTTCAGTGGC AGTGGATCTGGGACAGATTTCACTCTCACCAT CAACAGTCTGCAACCTGAAGATTTTGCAACTT ACTACTGTCAACAGAGTTACACTACCCCCACG TGGACGTTCGGCCAAGGGACCAAGGTGGAAA TCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGTTATTAGTGGTAGTGGTGGT AGCACATACTACGCAGACTCCGTGAAGGGCCGG TTCACCATCTCCAGAGACAATTCCAAGAACACGC TGTATTTGCAAATGAACACCCTGAGAGCCGAGG ACACGGCCGTATATTACTGTGCGAAAAGGTATAC CAGTGACTGGCATGATGCTTTTGATATCTGGGGC CAAGGGACAAATGGTCACCGTCTCTCA |
| | | | SEQ ID NO: 24859 | SEQ ID NO: 28865 |
| | | AA | DIQMTQSPSSLSASVGDRVSITCRASQNINNYLN WYQQKPGKGPKVLILTASSLQSGVPSRFSGSGSG TDFTLTINSLQPEDFATYYCQQSYTTPTWTFGQG TKVEIK | EVQLLESGGGLVQPGGSLRLSCAASGFTFSSYAMN WVRQAPGKGLEWVSVISGSGGSTYYADSVKGRFTI SRDNSKNTLYLQMNTLRAEDTAVYYCAKRYTSDW HDAFDIWGQGTMVTVSS |
| | | | SEQ ID NO: 24860 | SEQ ID NO: 28866 |

FIGURE 50
(Continued)

| | | | |
|---|---|---|---|
| iPS:393880 | 21-225_15A1 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGTTCTGGGACAGAATTCACTCTCACAG TCAGCAGCCTGCAGCCTGAAGATTTTGCAAGT TATTACTGTCTACACAACAGTAGTTACCCTGTT AAGTTTGGGGGAGGGATAAAGGTGGAGATCA CA |
| | | | SEQ ID NO: 24861 |
| | | AA | DIQMTQSPSSLSASVGDRVTITCRASQGIRNDLG WYQQKPGKAPKRLIYAASSLQSGVPSRFSGSGS GTEFTLTVSSLQPEDFASYYCLHNSSYPVKFGGG IKVEIT |
| | | | SEQ ID NO: 24862 |
| iPS:393882 | 21-225_15E3 | NA | GACATCCAGATGACCCAGTCTCCATCCTCCCT GTCTGCATCTGTAGGAGACAGAGTCACCATCA CTTGCCCGGGCAAGTCAGGGCATTAGAAATGAT TTAGGCTGGTATCAGCAGAAACCAGGGAAAG CCCCTAAGCGCCTGATCTATGCTGCATCCAGT TCGCAAAGTGGGTGTCCCATCAAGGTTCAGCGG CAGTGGTTCTGGGACAGAATTCACTCTCACAA TCAGCAGCCTGCAGCCTGAAGATTCTTGCAGT TATTACTGTCTACAGCATCATAGTTACCCGCTC ACTTTCGGCGGAGGGACCGAGGTGGAGATCTA C |
| | | | SEQ ID NO: 24863 |

| | |
|---|---|
| | CAGCTGCATCTGCAGGAGTCGGGCCCAGGACTG GTGAAGCCTTCGGAGAGACCCTGTCCCTCACTGCA CTGTCTCTGGTGGCTCCATCAGCAGAAGTAGTTA CTACTGGGGCTGGATCCGCCAGCCCCCAGGGAA GGGGCTGGAGTGGATTGGGAGTATCTATTATAGT GGGAGCGCCAGTACAAACCGTCCTCAAGAGT CGAGTCACCATATCTGTAGACACGAGCAAGAAC CAGTTCTCCCTGACGCTGAGCTCTGTGACCGCCG CAGACACGGCTGTATATTACTGTGCGAGACTGAG CAGCAGCTGGTCTTTTGACTACTGGGGCCAGGGA ACCCTGGTCACCGTCTCCTCA |
| | SEQ ID NO: 28867 |
| | QLHLQESGPGLVKPSETLSLTCTVSGGSISRSSYYW GWIRQPPGKGLEWIGSIYYSGSAQYNPSLKSRVTIS VDTTKNQFSLTLSSVTAADTAVYYCARLSSSWSFD YWGQGTLVTVSS |
| | SEQ ID NO: 28868 |
| | CAGGTGCAGTTGGTGGAGTCTGGGGGAACCGTG GTCCAGCCTGGGAGGTCCTGAGACTCTCCTGTG CAGCGTCTGATTCACCTTCAGTAGTAGTATGGCAT GCACTGGGTCCGCCAGGCTCCAGGCAAGGGGCT GGAGTGGGTGGCAGTTATATGGTATGGAAAA TAATAAACACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAGCTGG GGTTCCTCTCTGACTACTGGGGCCAGGGAACCCT GGTCACCGTCTCCTCA |
| | SEQ ID NO: 28869 |

FIGURE 50
(Continued)

| | | | |
|---|---|---|---|
| iPS:393884 | 21-225_16F4 | AA | DIQMTQSPSSLSASVGDRVTITCRASQGIRNDLG WYQQKPGKAPKRLIYAASSSQSGVPSRFSGSRSG TEFTLTISSLQPEDLAAYYCLQHHSYPLTFGGGT EVEIY SEQ ID NO: 24864 | QVQLVESGGTVVQPGRSLRLSCAASGFTFSSYGMH WVRQAPGKGLEWVAVIWYEENNKHYADSVKGRF TISRDNSKNTLYLQMNSLRAEDTAVYYCARELGFL SDYWGQGTLVTVSS SEQ ID NO: 28870 |
| | | NA | GACATCCAGATGATCCAGTCTCCATCCTCCCC GTCTGCATCTGTAGGAGACAGAGTCACCATCA CTTGCCGGGCAAGTCAGGGCATTAGAAATGAT TTAGGCTGGTATCAGCAGAAATCAGGGAAAG CCCCTAAGCGCCTGATATATGTTGCATCCAGT TTGCAAAGTGGGGTCCCATCAAGGTTCAGCGG CAGTGGATCTGGGACAGAATTCACTATCACAA TCAGCAGCGTGCAGCCTGAAGATTTTGCAACT TATTACTGTATACAGCATATAGTTATCCGTTC ACTTTCGGCGGAGGGACCAAGGTGGAGATCA AA SEQ ID NO: 24865 | CAGGTGCAGTTGGTGGAGTCTGGGGGAGGCGTG GTCCAGCCTGGGAGGTCCCTGAGACTCTCCTGTG CAGCGTCTGGATTCACCTTCAGTAGCTAACTATGGCAT GCACTGGGTCCGCCAGGCTCCAGGCAAGGGGCT GGAGTGGGTGGCAGTTATATGGTATGAAGGAAAG TAATCAATACTATGCAGACTCCGTGAAGGGCCG ATTCACCATCTCCAGAGACAATTCCAAGAACACG GTGTATCTGCAAATGCACAGCCTGAGAGCCGAG GACACGGCTGTGTATTACTGTGCGAGAGAGCTGG GGTTCCTCTGACTACTGGGGCCAGGGAACCCT GGTCACCGTCTCCTCA SEQ ID NO: 28871 |
| | | AA | DIQMIQSPSSPSASVGDRVTITCRASQGIRNDLG WYQQKSGKAPKRLIYVASSLQSGVPSRFSGSGS GTEFTITISSVQPEDFATYYCIQHNSYPFTFGGGT KVEIK SEQ ID NO: 24866 | QVQLVESGGGVVQPGRSLRLSCAASGFTFSNYGM HWVRQAPGKGLEWVAVIWYEGSNQYYGDSVKGR FTISRDNSKNTVYLQMHSLRAEDTAVYYCARELGF LSDYWGQGTLVTVSS SEQ ID NO: 28872 |

FIGURE 50
(Continued)

| | | | |
|---|---|---|---|
| iPS:393886 | 21-225_2G9 | NA | GACATCCAGATGACCCAGTCTCCATCCTCCT GTTTGCATCTGTGGAGACAGAGTCACCATCA CTTGCCGGGCAAGTCAGGGCATTAGAAATGAT TTAGGTTGGTATCAGCAGAAACCAGGGAAAG CCCCTCAGCGCCTGATCTATGCTGCATCCAGT TGCAAAGTGGAGTCCCATCAAGGTTCAGCGGC AGTGGATTTGGGACAGAATTCACTCTCACAAT CAGCAGCCTGCAGCTTGAAGATTTTGCAACTT ATTACTGTTTACAGCATGAAAGTTACCCTCTC ACTTTCGGCGGAGGGACCAAGGTGGAAATCA AA<br><br>SEQ ID NO: 24867 | CAACTGCAGCTGCAGGAGTCGGGCCCAGGACTG GTGAAGCCTTCGGAGACCCTGTCCCTCACCTGCA CTGTCTCTGGTGGCTCCATCAGACTAATTACTA CTGGGGCTGGATCCGCCAGCCCCCAGGGAAGG GCTGGAGTGGATTGGTAGTATCTATTATAGTGGA AGCACCTCCTACAACCCGTCCCTCAACAGTCGAG TCACCATATCCGTGGACACGTCCAAGAACCAGTT CTCCCTGAAGCTGAACTCTGTGACCGCCGCAGAC ACGGCTGTGTATTACTGTGCGAGACTAAGCAGCA ACTGGGACTTTGACAACTGGGGCCAGGGAACCC TGGTCACCGTCTCCTCA<br><br>SEQ ID NO: 28873 |
| | | AA | DIQMTQSPSSLFASVGDRVTITCRASQGIRNDLG WYQQKPGKAPQRLIYAASSLQSGVPSRFSGSGF GTEFTLTISSLQLEDFATYYCLQHESYPLTFGGGT KVEIK<br><br>SEQ ID NO: 24868 | QLQLQESGPGLVKPSETLSLTCTVSGGSIRPNYYWG WIRQPPGKGLEWIGSIYYSGSTSYNPSLNSRVTISVD TSKNQFSLKLNSVTAADTAVYYCARLSSNWDFDN WGQGTLVTVSS<br><br>SEQ ID NO: 28874 |
| iPS:393888 | 21-225_3E3 | NA | GACATCCAGATGACCCAGTCTCCATCCTCCCC GTCTGCATCTGTAGGAGACAGAGTCACCATCA CTTTCCGGGCAAGTCAGAGCATTAGAAGTTAT TTAAATTGGTATCAGCAGAAACCAGGGAAAG CCCATAAACTCGTGATCTATGCTGCATCCAGT TTGCAAAGTGGGGTCCCATCAAGGTTCAGTGG CAGTGGATCTGGGACAGATTCACTCTCACCA TCAGCAGTCTGCAACCTGAAGATTTTGCAACT TACTACTGTCAACAGAGTTACAGTACCCCCTT GTTCACTTTCGGCCCTGGGACCAAAGTGGATA TCAAA<br><br>SEQ ID NO: 24869 | GAGGTGCAGCTGTTGGAGTCTGGGGGAACCTTGG TACAGCCTGGGGGGTCCCTGAGACTCTCCTGTGC AGCCTCTGAATTCACCTTTAGCAGCTATGTCATG AGCTGGGTCCGCCAGGCTCCAGGGAAGGGGCTG GAGTGGGTCTCAATTATTAGTGGTCGTGGTGTA ACACATTCTACGCAGACTCCGTGAAGGGCCGGTT CCACCATCTCCAGAGACAATTCCAAGAACACGCTG TATCTGCAAATGAACAGCCTGAGAGCCGAGGAC ACGGCCTTATATTACTGTGTCGTCCCGTTTAGCAG TGGCTGGCTCGGAGGCTTTGATATCTGGGGCCA AGGGACAATGGTCACCGTCTCTTCA<br><br>SEQ ID NO: 28875 |

FIGURE 50
(Continued)

| | | | |
|---|---|---|---|
| iPS:393890 | 21-225_4B1 | AA | DIQMTQSPSSPSASVGDRVTITFRASQSIRSYLNWYQQKPGKAHKLVIYGTSSLQSGVPSRFSGSGSGTDFTLTISSLQPEDFATYYCQQSYSTPLFTFGPGTKVDIK<br>SEQ ID NO: 24870 | EVQLLESGGTLVQPGGSLRLSCAASEFTFSSYVMSWVRQAPGKGLEWVSIISGRGGNTFYADSVKGRFTISRDNSKNTLYLQMNSLRAEDTALYYCASRLAVAGSEAFDIWGQGTMVTVSS<br>SEQ ID NO: 28876 |
| | | NA | GACATCCAGATGACCCAGTCTCCATCCTCCCTGTCTGCATCTGTAGGGACAGAGTCACCATCACTTGCCGGGCAAGTCATCAGCAGTCATTAGAACCTATTTAAACTGGTATCAGCAGAAACCAGGGAAAGCCCCTAAGCTCCTGATCTATGCTGCATCCAGTTTGCAAAGTGGGGTCCCATCAAGGATCAATGGCAGTGGATCTGGGACAGATTTCACTCTCACCATCAGCAATCTACAGCCTGAAGATTTTGCAACTTACTACTGTCAACAGAGTTACAATATCTCATTCACTTTCGGCCCTGGGACCAAAGTGGATATCAAA<br>SEQ ID NO: 24871 | CAGGTGCAGCTGCAGGAGTCGGGCCCAGGACTGGTGAAGCCTTCGGAGACCCTGTCCCTCACCTGTGTGTCTCTGGTGACTCCATCAGTAGTTACTCCTGGAGCTGGATCCGGCAGCCCGCGGGAAGGGACTGGAATGGATTGGGCGTATCTATACCAGTGGAGCACCAACTACAATCCCTCCCTCAAGAGTCGAATCACCATGTCAGTAGACACGTCCAAGAAGCAGTTCTCCCTGAAGCTGAGCTCTGTGACCGCCGCGGACACGGCCGTGTATTACTGTGCGAGAGATTTGAAGAGCAGTGGCTGCCTTTTCTTTGACTACTGGGGCCAGGGAACCCTGGTCACCGTCTCCTCA<br>SEQ ID NO: 28877 |
| | | AA | DIQMTQSPSSLSASVGDRVTITCRASHTIRTYLNWYQQKPGKAPKLLIYAASSLQSGVPSRINGSGSGTDFTLTITNLQPEDFATYYCQQSYNISFTFGPGTKVDIK<br>SEQ ID NO: 24872 | QVQLQESGPGLVKPSETLSLTCSVSGDSISSYSWSWIRQPAGKGLEWIGRIYTSGSTNYIPSLKSRITMSVDTSKKQFSLKLSSVTAADTAVYYCARDLKSSGCLFFDYWGQGTLVTVSS<br>SEQ ID NO: 28878 |

FIGURE 50
(Continued)

| | | | |
|---|---|---|---|
| iPS:393892 | 21-225_6G7 | NA | GACATCCAGATGACCCAGTCTCCATCCTCCG GTCTGCATCTGTAGGAGACAGAGTCACCATCA CTTGCCAGGCGAGTCAGGACATTAGCAACTAT TTAAATTGGTGTCAACAGAAACCAGGGAAAG CCCTTAAGCTCTGATATACGATGCATCCACTT TGGAAACAGGGGTCCCCTCAAGGTTCAGTGGA AGTGGATCTGGGACAGATTTTACTTTCACCAT CAGCAGCCTGCAGCCTGAAGATATTGCAACAT ATTACTGCCAACAGTATGATAATGTCCCGATC ACCTTCGGCCAAGGGACACGACTGGAGATTAA A | CAGGTGCAGCTGGTGGAGTCTGGGGGAGGCGTG GTCCAGCCTGGGGAGGTCCCTGAGACTCTCCTGTG CAGCCTCTGGATTTACCTTCAGTAGCTATGGCAT GCACTGGGTCCGCCAGACTCCAGGCAAGGGGCT GGAGTGGGTGGCAATTATATCATATGTTGGAAAG AATAAATATTATGCAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGCGAGACGGGGAAA CAGGTATGGCGGGTACGGTATGGACGTCTGGGG CCAAGGGACTACGGTCACCGTCTCCTCA |
| | | | SEQ ID NO: 28879 |
| | | AA | DIQMTQSPSSRSASVGDRVTITCQASQDISNYLN WCQQKPGKALKLLIYDASTLETGVPSRFSGSGS GTDFTFTISSVQPEDIATYYCQQYDNVPITFGQGT RLEIK | QVQLVESGGGVVQPGRSLRLSCAASGFTFSSYGMH WVRQTPGKGLEWVAIISYVGKNKYADSVKGRFTI SRDNSKNTLYLQMNSLRAEDTAVYYCARRGNSYG GYGMDVWGQGTTVTVSS |
| | | | SEQ ID NO: 24873 | SEQ ID NO: 28880 |
| iPS:393894 | 21-225_5E11 | NA | GTCATCCAGATGACCCAGTCTCCATCCTCACT GTCTGCCTCTGTGGGCGACAGAGTCACCATCA CTTGTCGGGCGAGTCAGGGCATTAGCAATTAT TTAGCCTGGTTTCAGCAGAAACCAGGGAAAGC CCCTAAGTCCCTGATCAATGCTGCATCCAGTG TGCAGAGTGGGGTCCCATCAAATTCAGCGGC AATGGATCTGGGACAGCTTCACTCTCACCAT CAGCAGCCTGCAGCCTGAGGATTTTGCAACTT ATTACTGCCACCAGTATCACAGTTACCCATTC ACTTTCGGCCCTGGGACCAAAGTGGATATCAA A | GAGGTGCAGCTGCTGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTGGTAGTACT TACATATACTACGCAGACTCAGTGAAGGGCCGAT TCACCATCTCCAGAGACAACGCCAAGAACTACT GTATCTGCAAATGAACAGCCTGAGAGCCGAGGA CACGGCTGTGTTTTACTGTGCGAGAGTGGCTTCA TTTGACTACTGGGGCCAGGGAACCCTGGTCACCG TCTCCTCA |
| | | | SEQ ID NO: 24874 | |
| | | | SEQ ID NO: 24875 | SEQ ID NO: 28881 |

FIGURE 50
(Continued)

| | | | |
|---|---|---|---|
| iPS:393896 | 21-225_2A4 | AA | VIQMTQSPSSLSASVGDRVTITCRASQGISNYLA WFQQKPGKAPKSLINAASSVQSGVPSKFSGNGS GTDFTLTISSLQPEDFATYYCHQYHSYPFTFGPG TKVDIK<br>SEQ ID NO: 24876 | EVQLVESGGGLVKPGGSLRLSCAASGFTFSSYSMN WVRQAPGKGLEWVSSISGSSTYIYYADSVKGRFTIS RDNAKNSLYLQMNSLRAEDTAVFYCARVASFDYW GQGTLVTVSS<br>SEQ ID NO: 28882 |
| | | NA | GACATCCAGATGACCCAGTCTCCATCCTCACT GTTTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGCGCCTGATCTATACTGCATCCAGTT GCAAAGTGGGGTCCCATCAAAGTTCAGCGGCA GTGGATTTGGGACAGATTTCACTCTCACCATC AGCAGCCTGCAGCCTGAAGATTTTGCAACTTA TTACTGCCAACACAGTATATAGTTACCCATTCA CTTTCGGCCCTGGGACCAAAGTGGATATCAAA<br>SEQ ID NO: 24877 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTACT TACATATACTACGCAGACTCAGTGAAGGGCCGA ATCGCCATCTCCAGAGACAACGCCAAGAACTCG CTGTATCTGCAAATGAACAGCCTGAGAGCCGAG GACACGGCTGTATATTACTGTGCGAGAGTGGCTT CATTTGACTACTGGGGCCAGGGAACCCTGGTCAC CGTCTCCTCA<br>SEQ ID NO: 28883 |
| | | AA | DIQMTQSPSSLFASVGDRVTITCRASQGISNYLA WFQQKPGKAPKRLIYTASSLQSGVPSKFSGSGFG TDFTLTISSLQPEDFATYYCQQYNSYPFTFGPGT KVDIK<br>SEQ ID NO: 24878 | EVQLVESGGGLVKPGGSLRLSCAASGFTFSSYSMN WVRQAPGKGLEWVSSISGSSTYIYYADSVKGRIAIS RDNAKNSLYLQMNSLRAEDTAVYYCARVASFDY WGQGTLVTVSS<br>SEQ ID NO: 28884 |

FIGURE 50
(Continued)

| | | | | |
|---|---|---|---|---|
| iPS:393898 | 21-225_5F7 | NA | GACATTCAGATGACCCAGTCTCCATCCTCCCC GTCTGCATCTGTAGGAGACAGAGTCACCATCA CTTTCCGGGCAAGTCAGACAGCAGTCACATCA CTTTCCGGGCAAGTCAGACAGCAGTCATATT TTAAATTGGTATCAGCAGAAACCAGGGAAAG CCCCTAAACTCCTGATCTCTGCTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAATACCCCTTA TTCACTTTCGGCCCTGGGACCAAAGTGTGTTAT CAAA SEQ ID NO: 24879 | GAGGTGCAGTTGTTGGAGTCTGGGGGAGGCTTGG TACAGCCTGGGGGGTCCCTGAGACTCTCCTGTGC AGCCTCTGAATTCACCTTTAGCAGCTATGCCATG AGCTGGGTCCGCCAGGCTCCAGGGAAGGGGCTG GAGTGGGTCTCAATTATTAGTGGTCGTGGTGTA ACACATTCTACGCAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGCGTCCGTATAGCAG TGGCTGGCTCGGAGGCTTTGCTATCTGGGGCCA AGGGACAATGGTCACCGTCTCTTCA SEQ ID NO: 28885 |
| | | AA | DIQMTQSPSPSASVGDRVTITFRASQTISSYLNW YQQKPGKAPKLLISAASSLQSGVPSRFSGSGSGT DFTLTISSLQPEDFATYYCQQSYNTPLFTFGPGTK VVIK SEQ ID NO: 24880 | EVQLLESGGGLVQPGGSLRLSCAASEFTFSSYAMS WVRQAPGKGLEWVSIISGRGGNTFYADSVKGRFTI SRDNSKNTLYLQMNSLRAEDTAVYYCASRIAVAGS EAFAIWGQGTMVTVSS SEQ ID NO: 28886 |
| iPS:393900 | 21-225_10E12 | NA | GACATCCAGATGACCCAGTCTCCATCCTCCCT GTCTGCATCTGTAGGAGACAGAGTCACCATCA CTTGCCGGGCAAGTCAGAGCATTTACAGTTAT TTAAATTGGTATCAGCAGAAACCAGGGAGAG CCCCTAAGCTCCTGATCTATGCTACATCCAGTT TGCAAAGTGGGGTCCCATCAAGGTTCGGTGGC AGTGGATCTGGGACAGATTTCACTCTCACCAT CAGCAGTCTACAACCTGAAGATTTTGCAACTT ACTACTGTCAACAGAATTACAGTCCCCCTCTC ACTTTCGGCGGAGGGACCAAGGTGGAGATCG AA SEQ ID NO: 24881 | CAGGTGCAGCTGGTGGAGTCGGGGGGAGGCGTG GTCCAGCCTGGGAGGTCCCTGAGACTCTCCTGTG CAGCGTCTGGATTCAACTTCAGTAACTATGGCAT GCACTGGGTCCGCCAGGTTCAGGCAAGGGGCT GGAGTGGGTGGCAGTTATATGACTCCGTGAAGGGCCGA TAATAAATACTATGTAGACTCCGTGAAGGGCCGA TTCACCATCTCCAGAGACAATTCCAAGAACACGC TGTCTCTGCAAATGAACAGCCTGAGAGCCGAGG ACACGGCTGTGTATTGCTGTGTGCGAGAGATGAGAG GCTGGGGATTTTGACTACTGGGGCCAGGGAACC CTGGTCACCGTCTCCTCA SEQ ID NO: 28887 |

FIGURE 50
(Continued)

| | | | |
|---|---|---|---|
| iPS:393902 | 21-225_14E10 | AA | DIQMTQSPSSLSASVGDRVTITCRASQNIYSYLNWYQEKPGRAPKLLIYATSSLQSGVPSRFGGSGSGTDFTLTISSLQPEDFATYYCQQNYSPPLTFGGGTKVEIE<br>SEQ ID NO: 24882 | QVQLVESGGGVVQPGRSLRLSCAASGFNFSNYGMHWVRQVPGKGLEWVAVIWHDGSNKYYVDSVKGRFTISRDNSKNTLSLQMNSLRAEDTAVYCCARDERLGIFDYWGQGTLVTVSS<br>SEQ ID NO: 28888 |
| | | NA | GACATCCAGATGACCCAGTCTCCATCCTCCCTGTCTGCATCTGTAGGAGACCGAGTCACCATCACTTGCCGGACAAGTCAGGGCATTAGAAATGATTTAGGCTGGTATCAGCACAAACCAGGGCAAGCCCCTAAGCGCCTGATCTATGCTGCATCCAGTTTACAAAGTGGGGTCCCATCAAGGTTCAGCGGCAGTGGATCTGGGACAGACTTCACTCTCACAATCAGCAGCCTGCAGCCTGAAGATTTTGCAACTTATTACTGTCTGCAGCATTATAGTTACCCTCGGACGTTCGGCCAAGGGACCAAGGTGGAAATCAAG<br>SEQ ID NO: 24883 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGGCATGCACTGGGTCCGCCAGGCTCCAGGCAAGGGGCTGGAGTGGGTGGCAGTTATATGGCATGATGGAAGTAATAAATACTATGCAGACTCCGTGAAGGGCCGATTCACCATCTCCAGAGACAATTCCAAGAACACGCTCTATCTGCAAATGAACAGCCTGAGAGCCGAGGACACGGCTGTGTATTACTGTGCGAGAGAAGTATAGCAGCAGCTGGTACGACTACGGTATGGACGTCTGGGGCCAAGGGACCACGGTCACCGTCTCCTCA<br>SEQ ID NO: 28889 |
| | | AA | DIQMTQSPSSLSASVGDRVTITCRTSQGIRNDLGWYQHKPGQAPKRLIYAASSLQSGVPSRFSGSGSGTEFTLTISSLQPEDFTAYYCLQHYSYPRTFGQGTKVEIK<br>SEQ ID NO: 24884 | QVQLVESGGGVVQPGRSLRLSCAASGFTFSDYGMHWVRQAPGKGLEWVAVIWYDGSNKYYADSVKGRFTISRDNSKNTLYLQMNSLRAEDTAVYYCAREKYSSSWYDYGMDVWGQGTTVTVSS<br>SEQ ID NO: 28890 |

FIGURE 50
(Continued)

| | | | |
|---|---|---|---|
| iPS:393904 | 21-225_8H11 | NA | GACATCCAGATGACCCAGTCTCCATCCTCCTGTCTGCATTTGTAGGAGACAGAGTCACCATCACTTGCCGGGCAAGTCAGAACATTATCAGCTATTTAAATGGTATCAACAGAAACCAGGGAAAGCCCCTAACCTCATGATCTATATGTTACATCCAGTTTGCACAGTGGGGTCCCATCAAGGTTCAGTGGCAGTGGATCTGGGACAGATTTCTCTCACCATCAGCAGTCTCCAACCTGAGGATTTTGCAACTTACTACTGTCAACAGAGTTACAGTACCCCTTTCACTTTCGGCCCTGGGACCAAAGTGGATATCAAA |
| | | | SEQ ID NO: 24885 |
| | | AA | DIQMTQSPSSLSASFVGDRVTITCRASQNIISYLNWYQQKPGKAPNLMIYTSSLHSGVPSRFSGSGSGTDFSLTISSLQPEDFATYYCQQSYSTPFTFGPGTKVDIK |
| | | | SEQ ID NO: 24886 |
| iPS:393906 | 21-225_13D3 | NA | GAAATAGTGATGACGCAGTCTCCAGCCACCCTGTCTGTGTCTCCAGGGGAAAGCGCCACCCTCTCCTGCAGGGCCAGTCAGAGACTGTTAGCAGCAACTTAGCCTGGTTCCAGCAGAAAGCCTGGCCAGGCTCCCAGGCTCCTCATCAATGGTGCATCCACCAGGGCCACTGGTATCCCAGCAGAGTTCACTCTCACCATCAGCAGCCTGCAGTCTGAAGATTTTGCAGTTATTTCTGTCAGCAGTATCATGACTGGCCTCCGACGTTCGGCCAAGGGACCAAGGTGGAAATCAAAA |
| | | | SEQ ID NO: 24887 |
| | | | CAGGTGCAGCTGGTGGAGTCTGGGGGAGGCGTGGTCCAGCCTGGGAGGTCCCTGAGACTCTCCTGTGCAGCGTCTGGATTCACCTTCAGTACCTATAACATGCACTGGGTCCGCCAGGCTCCAGGCAAGGGGCTGGAGTGGGTGGCAGTTATATGGTATGATGGAAGTGATAGATACTCTGCAGACTCCGTGAAGGGCCGATTCACCATCTCCCGAGACAATTCCAAGAACACGCTGTATCTGCAAATGAACAGCCTGAGAGCCGAGGACACGGCTGTATTACTGTGCGAGAGATCGGGCCTATAGCAGCTGTCTGACTTCTGGGGCCAGGGAACCCTGGTCACCGTCTCCTCA |
| | | | SEQ ID NO: 28891 |
| | | | QVQLVESGGGVVQPGRSLRLSCAASGFTFSTYNMHWVRQAPGKGLEWVAVIWYDGSDRYSADSVKGRFTISRDNSKNTLYLQMNSLRAEDTAVYYCARDRAYSSSSDFWGQGTLVTVSS |
| | | | SEQ ID NO: 28892 |
| | | | GAGGTGCAGCTGGTGGAGTCTGGGGGAGGCCTGGTCAAGCCTGGGGGGTCCCTGAGACTCTCCTGTGCAGCCTCTGGATTCACCTTCAGTAGTTATACCATGAACTGGGTCCGCCAGGCTCCAGGGAAGGGGCTGGAGTGGGTCTCATCATTAGTGGTAGTAGTGGTAGTACCATACTACGCGGACTCAGTGAAGGGCCGATTCACCATCTCCAGAGACAACGCCAAGAACTCACTGTATCTGCAAATGAACAGCCTGAGAGCTGAGGACACGGCTGTGTATTACTGTGCGAGAGATCGGGCCAGTGGCTGGGGCCAGGGAACCCTGGTCACCGTCTCCTCA |
| | | | SEQ ID NO: 28893 |

FIGURE 50
(Continued)

| | | | |
|---|---|---|---|
| iPS:393908 | 21-225_10E9 | AA | EIVMTQSPATLSVSPGESATLSCRASQTVSSNLA WFQQKPGQAPRLLINGASTRATGIPARFSGSGSG TEFTLTISSLQSEDFAVYFCQQYHDWPPTFGQGT KVEIK<br><br>SEQ ID NO: 24888 | EVQLVESGGGLVKPGGSLRLSCAASGFTFSSYTMN WVRQAPGKGLDWVSSISGSSSYIYYADSVKGRFTIS RDNAKNSLYLQMNSLRAEDTAVYYCARDRGSGW GQGTLVTVSS<br><br>SEQ ID NO: 28894 |
| | | NA | GACATCCAGATGACCCAGTCTCCATCCTCCCT GTCTGCATCTGTAGGAGACAGAGTCACCTTCA CTTGCCGGGCAAGTCAGGACATTAGAAGTGAT TTAGGCTGGTATCAGCAGAAACCAGGGAAAG CCCCTACGCGCCCTGATCTTTGCTGCATCCAGTT TGCAAAGTGGGGTCCCATCCAAGGTTCAGCGGC AGTGGATCTGGGACAGAATTCACTCTCACAAT CAACAGCCTGCAGCCTGAAGATTTTGCAACTT ATTACTGTCTACAGCATTATAGTTACCCTCGG ACGTTCGGCCAAGGGACCAAGGTGGAAATCA AA<br><br>SEQ ID NO: 24889 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTACTATGTCAT ACACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAAGTA TAGCAGCAGCTGGTACGACTACGGTATGGACGTC TGGGGCCAAGGGACCACGGTCACCGTCTCCTCA<br><br>SEQ ID NO: 28895 |
| | | AA | DIQMTQSPSSLSASVGDRVTFTCRASQDIRSDLG WYQQKPGKAPTRLIFAASSLQSGVPSRFSGSGSG TEFTLTINSLQPEDFATYYCLQHYSYPRTFGQGT KVEIK<br><br>SEQ ID NO: 24890 | QVQLVESGGGVVQPGRSLRLSCAASGFTFSNYVIH WVRQAPGKGLEWVAVIWYDGSNKYYADSVKGRF TISRDNSKNTLYLQMNSLRAEDTAVYYCAREKYSS SWYDYGMDVWGQGTTVTVSS<br><br>SEQ ID NO: 28896 |

FIGURE 50
(Continued)

| | | | |
|---|---|---|---|
| iPS:393910 | 21-225_15F10 | NA | GACATCCAGATGACCCAGTCTCCATCCTCCT GTCTGCTTCTGTAGGAGACAGAGTCACCATCA CTTGCCAGGCGAATCAGGACATTACCAACTTT TAAAATTGGTATCAGCTGAAACCAGGGAAAGC CCCTAACCTCCTGATCTCCGATGCATCCAATTT GGAAACAGGGGTCCCATCAAGGTTCAGTGGA AGTGGATCTGGGACAGATTTTACTTTCACCAT CAGCAGCCTGCAGCCTGAAGATGTTGCGACAT ATTACTGTCAACAGTATGATAATCTCCCGATC ACCTTCGGCCAAGGGACACGACTGGAGATTAA A<br>SEQ ID NO: 24891 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGTCAGTTATATCATATGGTGAAGT AATAATTACTATGCAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGTGAGACGGGATAC AGCTATGGCGGGTACGGTTATGGACGTCTGGGGC CAAGGGACCACGGTCACCGTCTCCTCA<br>SEQ ID NO: 28897 |
| | | AA | DIQMTQSPSSLSASVGDRVTITCQANQDITNFLN WYQLKPGKAPNLLISDASNLETGVPSRFSGSGSG TDFTFTISSLQPEDVATYYCQQYDNLPITFGQGT RLEIK<br>SEQ ID NO: 24892 | QVQLVESGGGVVQPGRSLRLSCAASGFTFSSYGMH WVRQAPGKGLEWVSVISYGGSNNYYADSVKGRFT ISRDNSKNTLYLQMNSLRAEDTAVYYCVRRGYSY GGYGMDVWGQGTTVTVSS<br>SEQ ID NO: 28898 |
| iPS:393912 | 21-225_16F6 | NA | GACATCCAGATGACCCAGTCTCCATCCTCCT GTCTGCTTCTGTAGGAGACAGAGTCACCATCA CTTGCCAGGCGAATCAGGACATTACCAACTTT TAAAATTGGTATCAGCTGAAACCAGGGAAAGC CCCTAACCTCCTGATCTCCGATGCATCCAATTT GGAAACAGGGGTCCCATCAAGGTTCAGTGGA AGTGGATCTGGGACAGCCTGAAGATGTTGCGACAT CAGCAGCCTGCAGCCTGAAGATGTTGCGACAT ATTACTGTCAACAGTATGATAATCTCCCGATC ACCTTCGGCCAAGGGACACGACTGGAGATTAA A<br>SEQ ID NO: 24893 | CAGGTGCAGCTGGTGGAGTCTGGGGGAGGCGTG GTCCAGCCTGGGAGGTCCCTGAGACTCTCCTGTG CAGCCTCTGATTCACCTTCAGTAACTATGGCAT GCACTGGGTCCGCCAGGCTCCAGGCAAGGGGCT GGAGTGGGTGGCAGTTATATGGTATGAAGGAAG TAATCAATACTATGGAGACTCCGTGAAGGGCCG ATTCACCATCTCCAGAGACAATTCCAAGAACACG GTGTATCTGCAAATGCACAGCTGAGAGCCGAG GACACGGCTGTGTATTACTGTGCGAGAGAGCTGG GGTTCCTCTGTGATTACTGGGGCCAGGGAACCCT GGTCACCGTCTCCTCA<br>SEQ ID NO: 28899 |

FIGURE 50
(Continued)

| | | | |
|---|---|---|---|
| iPS:393914 | | AA | DIQMTQSPSSLSASVGDRVTITCQANQDITNFLN WYQLKPGKAPNLLISDASNLETGVPSRFSGSGSG TDFTFTISSLQPEDVATYYCQQYDNLPITFGQGT RLEIK<br>SEQ ID NO: 24894 | QVQLVESGGGVVQPGRSLRLSCAASGFTFSNYGM HVRQAPGKGLEWVAVIWYEGSNQYYGDSVKGR FTISRDNSKNTVYLQMHSLRAEDTAVYYCARELGF LSDYWGQGTLVTVSS<br>SEQ ID NO: 28900 |
| | 21-225_16B8 | NA | GACATCCAGATGACCCAGTCTCCATCCTCACT GTCTGCCTCTGTAGGAGACAGAGTCACCATCA CTTGTCGGGCGAGTCAGGGCATTAACAATTAT TTAGCCTGGTTTCAGCAGAAACCAGGGAAAGC CCCTTAAGTCCCTGATCAATGCTGCATCCAGTG TGCAGAGTGGGGTCCCATCAAAGTTCAGCGGC AGTGGATCTGGGACAGACTTCACTCTCACCAT CAGCAGCCTGCAGCCTGAAGATTTTGCAACTT ATTACTGCCACCAGTATCACAGTTACCCATTC ACTTTCGGCCCTGGGACCAAAGTGGATATCGT A<br>SEQ ID NO: 24895 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGATCTCATCCATTAGTGGTAGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGTGGCTTCA TTCGACTACTGGGGCCAGGGAACCCTGGTCACCG TCTCCTCA<br>SEQ ID NO: 28901 |
| | | AA | DIQMTQSPSSLSASVGDRVTITCRASQGINNYLA WFQQKPGKALKSLINAASSVQSGVPSKFSGSGS GTDFTLTISSLQPEDFATYYCHQHSYPFTFGPG TKVDIV<br>SEQ ID NO: 24896 | EVQLVESGGGLVKPGGSLRLSCAASGFTFSSYSMN WVRQAPGKGLEWISSISGSSTYIYADSVKGRFTIS RDNAKNSLYLQMNSLRAEDTAVYYCARVASFDY WGQGTLVTVSS<br>SEQ ID NO: 28902 |

FIGURE 50
(Continued)

| | | | | |
|---|---|---|---|---|
| iPS:393916 | 21-225_2G4 | NA | GACATCCAGATGACCCAGTCTCCATCTCCT GTCTGCTTCTGTAGGCGACAGAGTCACCATCA CTTGCCGGGCAAGTCAGGGCATTAGAAATGAT TTAGGCTGGTATCAGCAGAAACCAGGGAAAG CCCCTACGCGCCTGATCTATGCTGCATCCAGTT TGCACAGTGGGGTCCCATCACGGTTCAGCGGC AGTGGATCTGGGACAGAATTCACTCTCACAAT CAGCAGCCTGCAGCCTGAAGATCTTGCAACTT ATTACTGTCTACAACATTATAGTTTCCCTCGGA CGTTCGGCCGAGGGACCAAGGTGGAAATCAA A | CAGGTGCAGTTGGTGGAGTCTGGGGGAGGCGTG GTCCAGCCTGGGAGGTCCCTGAGACTCTCCTGTG CAGCGTCTGATTCACCTTCAGTAGTAGTCAT GCACTGGGTCCGCCAGGCTCCAGGCAAGGGCT GGAGTGGGTGGCAGTTATATGGTATGATGAAGT AATAAATACTATGCAGAGACTCCGTGAAGGGCGA TTCACCATCTCCAGAGACAATTCCAAGAACACGC TGTATCTGCAAATGAACAGCCTGAGAGCCGAGG ACACGGCTGTGTATTACTGTGCGAGAGAAGTA TAGCAGCAGCTGGTACGACTACGGTATGGACGTC TGGGGCCACGGGACCACGGTCACCGTCTCCTCA |
| | | | SEQ ID NO: 24897 | SEQ ID NO: 28903 |
| | | AA | DIQMTQSPSSLSASVGDRVTITCRASQGIRNDLG WYQQKPGKAPTRLIYAASSLHSGVPSRFSGSGSG TEFTLTISSLQPEDLATYYCLQHYSFPRTFGRGTK VEIK | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCAREKYSS SWYDYGMDVWGHGTTVTVSS |
| | | | SEQ ID NO: 24898 | SEQ ID NO: 28904 |
| iPS:393920 | 21-225_1H12 | NA | GACATCCAGATGACCCAGTCTCCATCTCCCT GTCTGCATCTGTTGGAGACAGAGTCACCATCA CTTGCCGGGCAAGTCAGAACATTTACAGGTAT TTAAATTGGTATCAGCAGAAACCAGGGAGAG CCCCTAAGCTCCTGATCTATACTGCATCCAGTT TACAAAGTGGGGTCCCATCAAGGTTCAGTGGC AGTGACTGGGACAGATTTCACTCTCACCAT CAGCAGTCTGCAACCTGAAGATTTTGCAACTT ACTACTGTCAACAGAGTTACAGTTCCCCCTC ACTTTCGGCGGAGGGACCAAGGTGGAGATCA AA | CAGGTGCAGCTGGTGGAGTCTGGGGGAGGCGTG GTCCAGTCTGGGAGGTCCCTGAGACTCTCCTGTG CAGCGTCTGATTCAACTTCAGTAGTCATGGCAT GCACTGGGTCCGCCAGGCTCCAGGCAAGGGCT GGAGTGGGTGGCAATTATATGACTCCGTGAAGGGCGA TAATAAATACTATGTAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGAGAG GCTGGGGATTTTTGACTACTGGGGCCAGGGAACC CTGGTCACCGTCTCCTCA |
| | | | SEQ ID NO: 24899 | SEQ ID NO: 28905 |

FIGURE 50
(Continued)

| | | AA | DIQMTQSPSSLSASVGDRVTITCRASQNIYRYLN WYQEKPGRAPKLLIYTASSLQSGVPSRFSGSDSG TDFTLTISSLQPEDFATYYCQQSYSPPLTFGGGTK VEIK<br><br>SEQ ID NO: 24900 | QVQLVESGGGVVQSGRSLRLSCAASGFNFSSYGMH WVRQAPGKGLEWVAIIWHDGSNKYYVDSVKGRFT ISRDNSKNTLYLQMNSLRAEDTAVYYCARDERLGI FDYWGQGTLVTVSS<br><br>SEQ ID NO: 28906 |
|---|---|---|---|---|
| iPS:393922 | 21-225_2B2 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGCAAG CCCCTAAGCGCCTGATCTATGCTGCATCCAGT TTACAAAGTGGGGTCCCATCCAAGGTTCAGCGG CAGTGGATCTGGGACAGACAATTCACTCTCACAA TCAGCAGCCTGCAGCCTGAAGATCTTGCAACT TATCACTGTCTACAGCATAATAGTTACCCGCT CACTTTCGGCGGAGGGACCAAGGTGGAGATC AAA<br><br>SEQ ID NO: 24901 | CAGGTGCAGCTGGTGGAGTCTGGGGGAGGCGTG GTCCAGCCTGGGAGGTCCCTGAGACTCTCCTGTG CAGCGTCTGGATTCAACTTCAGTAGCTATGGCAT GCACTGGGTCCGCCAGGCTCCAGGCAAGGGCT GGAGTGGGTGGCAGTTATATGTGATGGAAAA TAATAAATACTATGTAGACTCCGTGAAGGGCCGA TTCACCATCTCCAGAGACAATTCCAAGAGCACGC TGTATCTGCAAATGAACAGCCTGAGAGCCGAGG ACACGGCTGTGTATTACTGTGTGAGAGAACTAGG CTTCCAGTCTGACTACTGGGGCCAGGGAACCCCG GTCACCGTCTCCTCA<br><br>SEQ ID NO: 28907 |
| | | AA | DIQMTQSPSSLSASVGDRVTITCRASQGIRNDLG WYQQKPGQAPKRLIYAASSLQSGVPSRFSGSGS GTEFTLTISSLQPEDLATYHCLQHNSYPLTFGGG TKVEIK<br><br>SEQ ID NO: 24902 | QVQLVESGGGVVQPGRSLRLSCAASGFTFSSYGMH WVRQAPGKGLEWVAVIWYEENNKYYVDSVKGRF TISRDNSKSTLYLQMNSLRAEDTAVYYCVRELGFQ SDYWGQGTPVTVSS<br><br>SEQ ID NO: 28908 |

FIGURE 50
(Continued)

| | | | | |
|---|---|---|---|---|
| iPS:393926 | 21-225_4G4 | NA | GACATCCAGATGACCCAGTCTCCATCCTCCCT GGCTGCATCTGTAGGAGACAGAGTCACCATCA CTTGCCGGGCAAGTCAGAGACCATTATCAGCTAT TTAAATTGGTATCAGCAGAAACCAGGGAAAG CCCCTAAACTTCTGATCCATACTGCATCCAGTT TGCAAAGTGGGGTCCCATCAAGGTTCAGTGGC AGTGGATCTGGGACAGATTTCACTCTCTCCAT CAGCAGTCTGCAACCTGAAGATTTTGCAACTT ACTACTGTCAACAGAGTTACAGTACTCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCCGGATTCACCTTCAGTAGCTATGGCAT GCACTGGGTCCGCCAGGCTCCAGGCAAGGGCT GGAGTGGGGGCAGTTATATGCAGACTCCGTGAAGGGCCG TAATAAATACTATGCAGACACCAAGAAACAC ATTCACCATCTCCAGAGACAATGCCAAGAACAC GCTGTATCTGCAAATGAACAGCCTGAGAGCCGA GGACACGGCTGTGTATTACTGTGCGAGAGATCTG AGAATGGGCGGTATGGACGTCTGGGGCCAAGGG ACCACGGTCACCGTCTCCTCA |
| | | | SEQ ID NO: 24903 | SEQ ID NO: 28909 |
| | | AA | DIQMTQSPSSLAASVGDRVTITCRASQTIISYLNW YQQKPGKAPKLLIHTASSLQSGVPSRFSGSGSGT DFTLSISSLQPEDFATYYCQQTYSTPLTFGGGTK VEIK | QVQLVESGGGVVQPGRSLRLSCAASGFTFSSYGMH WVRQAPGKGLEWGAVIWHDGSNKYYADSVKGRF TISRDNAKNTLYLQMNSLRAEDTAVYYCARDLRM GGMDVWGQGTTVTVSS |
| | | | SEQ ID NO: 24904 | SEQ ID NO: 28910 |
| iPS:393928 | 21-225_4E10 | NA | GACATCCAGATGACCCAGTCTCCATCCTCCCT GTTTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATTTGGGACAGATTTCACTCTCACAA TCAGCAGCCTGCAGCCTGAAGATTTTGCAACT TATTACTGTCAGCAGCATGATAATTACCCTCTC ACTTTCGGCGGAGGGACCAAGGTGGAGATCA AA | CAGCTGCAGCTACAGGAGTCGGGCCCAGGACTG GTGAAGCCTTCGGAGACCCTGTCCCTCACCTGCA CTGTCTCTGGTGGCTCCATCAGCCGTAGTAGTTA CTACTGGGGCTGGATCCGCCAGCCCCCAGGGAA GGGGCTGGAGTGGATTGGGAGTATCTATTATAGT GAGTCACCATATCCGTAGACACGTCCAAGAACC AGTTTCCCTGAAGCTGAACTCTGTGACCGCCGC AGACACGGCTTTGTATTACTGTGTGAGACTAAGC AGCAACTGGGACTTGACTACTGGGGCCAGGGA ACCCTGGTCACCGTCTCCTCA |
| | | | SEQ ID NO: 24905 | SEQ ID NO: 28911 |

FIGURE 50
(Continued)

| | | | |
|---|---|---|---|
| iPS:393930 | | AA | DIQMTQSPSSLFASVGDRVTITCRASQGIRNDLG WYQQKPGKAPKRLIYAASSLQSGVPSRFSGSGF GTEFTLTISSLQLEDFATYYCLQHDNYPLTFGGG TKVEIK SEQ ID NO: 24906 | QLQLQESGPGLVKPSETLSLTCTVSGGSISRSSYYW GWIRQPPGKGLEWIGSVYYSGATSYNPSLKSRVTIS VDTSKNQFSLKLNSVTAADTALYYCVRLSSNWDF DYWGQGTLFTVSS SEQ ID NO: 28912 |
| | | NA | GACATCCAGATGACCCAGTCTCCATCCTCCCT GTCTGCATCTGTAGGAGACAGAGTCACCATCG CTTGCCGGGCAAGTCAAAACATTATCAGCTAT TTAAATTGGTATCAACAGAAACCAGGGAAAG CCCCTAAATTCCTGATCTATATCCAAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGGACCAAGGTGGAGATCA AA SEQ ID NO: 24907 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATATGCAGTGATGAAG TAATAAATACTATGCAGACTCCGTGAAGGGCCG ATTCACCATCTCCAGAGACAATTCCAACAACACG CTGTATCTGCAAATGAGCAGCCTGCGAGCCGAG GACACGGCTGTGTATTACTGTGCGAGAGATCTGA GTATGGGCGGTATGGACGTCTGGGGCCAAGGGA CCACGGTCACCGTCTCCTCA SEQ ID NO: 28913 |
| 21-225_7E11 | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK SEQ ID NO: 24908 | QVQLVESGGGVVQPGRSLRLSCAASGFTFSSFGMH WVRQAPGKGLEWVAIIWHDGSNKYYADSVKGRFT ISRDNSNNTLYLQMSSLRAEDTAVYYCARDLSMGG MDVWGQGTTVTVSS SEQ ID NO: 28914 |

FIGURE 50
(Continued)

| | | | |
|---|---|---|---|
| iPS:393932 | 21-225_10F5 | NA | GACATCCAGATGACCCAGTCTCCATCCTCCT GTCTGCATCTGTTGGAGACAGAGTCACCATCA CTTGCCGGGCAAGTCAGAACATTTACAGGTAT TTAAATGGTATCAGGAGAAACCAGGAGAG CCCCTAAACTCCTGATCTATACTGCATCCAGTT TGCAAAGTGGGGTCCCATCAAGGTTCAGTGGC AGTGACTCTGGGACAGATTTCACTCTCACCAT CAGCAGTCTGCAACCTGAAGATTTTGCAACTT ACTACTGTCAACAGAGTTACAGTCCCCCTCTC ACTTTCGGCGGAGGGACCAAGGTGGAGATCA AA<br>SEQ ID NO: 24909 | CAGGTGCAGCTGGTGGAGTCTGGGGGAGGCGTG GTCCAGCCTGGGAGGTCCCTGAGACTCTCCTGTG CAGCGTCTGGATTCAACTTCAGTAGTTATGGCAT GCACTGGGTCCGCCAGGCTCCAGGCAAGGGGCT GGAGTGGGTGTCAATTATATGGACTCATGATGAAGT AATAAATATTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATGAGAGG CTGGGGATTTTGACTACTGGGGCCAGGGAACCC TGGTCACCGTCTCCTCG<br>SEQ ID NO: 28915 |
| | | AA | DIQMTQSPSSLSASVGDRVTITCRASQNIYRYLN WYQEKPGRAPKLLIYTASSLQSGVPSRFSGSDSG TDFTLTISSLQPEDFATYYCQQSYSPPLTFGGGTK VEIK<br>SEQ ID NO: 24910 | QVQLVESGGGVVQPGRSLRLSCAASGFNFSSYGMH WVRQAPGKGLEWVSIIWHDGSNKYYVDSVKGRFT ISRDNSKNTLYLQMNSLRAEDTAVYYCARDERLGI FDYWGQGTLVTVSS<br>SEQ ID NO: 28916 |
| iPS:393934 | 21-225_13E6 | NA | GACATCCAGATGACCCAGTCTCCATCTTCCCT GTCTGCATCTGTAGGAGACAGAGTCACCATCA CTAGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTGTACAGCATAATAGTTACCCGCT CACTTTCGGCGGAGGGACCAAGGTGGCGATCA AA<br>SEQ ID NO: 24911 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAACTATGGCAT GCACTGGGTCCGCCAGGCTCCAGGCAAGGGGCT GGAGTGGGTGGCAGTTATATGGTATGATGAAAAT TCACCATCCAGAGACAACTCCAAGAACACGCT GTATCTGCAAATGAACAGCCTGAGAGCCGAGGA CACGGCTGTGTATTACTGTGCGAGAGAATTGGGG TTCCGGTCTGACTACTGGGGCCAGGGAACCCTGG TCACCGTCTCCTCA<br>SEQ ID NO: 28917 |

FIGURE 50
(Continued)

| | | | |
|---|---|---|---|
| | | AA | DIQVTQSPSSLSASVGDRVTITSRASQGIRNDLG WYQQKPGKAPKRLIYAASSLQSGVPSRFSGSGS GTEFTLTISSLQPEDFATYYCVQHNSYPLTFGGG TKVAIK<br><br>SEQ ID NO: 24912 | QVQLVESGGGVVQPGRSLRLSCAASGFTFSNYGM HWVRQAPGKGLEWVAVIWYDENNKYYIDSVKGR FTISRDNSKNTLYLQMNSLRAEDTAVYYCARELGF RSDYWGQGTLVTVSS<br><br>SEQ ID NO: 28918 |
| iPS:393936 | 21-225_14A11 | NA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGTTATTAGTGGTAGAGGTGGT AGTACATACTACGCAGACTCCGTGAAGGGCCGG TTCACCATCTCAAGAGACAATTCCAAGAACACGC TGTATCTGCAAATGAACAGCCTGAGAGCCGAGG ACACGGCCGTATATTACTGTGCGAAAAGGATAG CAGCTGGTATGGAGTACTTCGATCTCTGGGGCCG TGGCACCCTGGTCACTGTCTCCTCA<br><br>SEQ ID NO: 28919 | |
| | | AA | DIQMTQSPSSLSASIGDRVTITCRASQSISSYLNW YQQKPGKAPKLLIFAASSLQNGVPSRFSGSGSGT DFTLTISSLQPEDFATYYCQQTYSSPPFTFAPGTK VDIK<br><br>SEQ ID NO: 24914 | EVQLLESGGGLVQPGGSLRLSCAASGFTFSSYAMN WVRQAPGKGLEWVSVISGRGGSTYYADSVKGRFTI SRDNSKNTLYLQMNSLRAEDTAVYYCAKRIAAGM EYFDLWGRGTLVTVSS<br><br>SEQ ID NO: 28920 |

FIGURE 50
(Continued)

| | | | | |
|---|---|---|---|---|
| iPS:393940 | 21-225_16B2 | NA | GGCGTCCAGATGACCCAGTCTCCATCCTCCCT GTCTGCATCTGTAGGAGACAGAGTCACCATCA CTTGCCGGGCAAGTCAGAGACATTAGCGGCTAT TTAAATTGGTATCAGCAGAAACCAGGGAAAG CCCCTAAGCTCCTGATCTATGCTGCATCCAGTT TGCAAAGTGGGGTCCCATCAAGGTTCAGTGGC GGTGGATCTGGGACAGATTTCACTCTCACCAT CAGCAGTCTACAACCTGAAGATTTTGCAACTT ACTACTGTCAACAGACTTACAATACCCCTCCG GAGCGCAGTTTTTGGCCAGGGGACCAAGCTGG AGATCAAA SEQ ID NO: 24915 | GAGGTGCAGTTGTTGGAGTCTGGGGGAGGCTTGG TACAGCCGGGGGGGTCCTGAGACTCTCCTGTGC AGCCTCTGGATTCACCTTTAGCAGCAGCTATGCCATG ACCTGGGTCCGCCAGGCTCCAGGGAAGGGCCG GAGTGGGTCTCAGTTATTAGTGGTAGTGGTGGTA GCACATTCTACGCAGACTCCGTGAAGGGCCGGTT CACCATCTCCAGAGACAATTCCAAGAACACGCTT TATCTGCAAATGAGCAGCCTGAGAGCCGAGGAC ACGGCCGTTTATTTCTGTGCCGATATTGTAGTA GTACCAGGTGCCCTTATGATGCTTTGATATCTG GGGCCAAGGGACAATGGTCACCGTCTCCTCA SEQ ID NO: 28921 |
| | | AA | GVQMTQSPSSLSASVGDRVTITCRASQSISGYLN WYQQKPGKAPKLLIYAASSLQSGVPSRFSGGGS GTDFTLTISSLQPEDFATYCQQTYNTPPERSFG QGTKLEIK SEQ ID NO: 24916 | EVQLLESGGGLVQPGGSLRLSCAASGFTFSSYAMT WVRQAPGKGPEWVSVISGSGSTFYADSVKGRFTI SRDNSKNTLYLQMSSLRAEDTAVYFCARYCSSTRC PYDAFDIWGQGTMVTVSS SEQ ID NO: 28922 |
| iPS:393942 | 21-225_11E5 | NA | GACATCGTGATGACCCAGTCTCCAGACTCCCT GGCTGTGTCTCTGGGCGAGAGGGCCACCCTCA ACTGCAAGTCCAGCCAGAGTGTTTTATACAGC TCCAACAATAACAACTACTTAACTTGGTACCA GCAGAAACCTGGACAGCGACCTAAGTTGCTCA TTTACTGGGCATCTACCCGGGAATCCGGGGTC CCTGACCGATTCAGTGGCAGCGGGTCTGGGAC AGTCACCATGACCAGGAACACCTCCATAAGCAC AGCCTACATGGAGCTGAGCAGCCTGAGATCTGA CTGAAGATGTGGCAGTTTATTATTACTGTCAGCAA TATTATAGTACTCCTCGACGTTCGGCCAAGG GACCAAGGTGAAATCAAA SEQ ID NO: 24917 | CAGGTGCAACTGGTGCAGTCTGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAATCCCAACAGTGG TGCCACGGCTATGCACAGAGGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGACAAGCAGT GGCTGGGAGGTCTTTGACTACTGGGGCCAGGGA ACCCTGGTCACCGTCTCCTCA SEQ ID NO: 28923 |

FIGURE 50
(Continued)

| | | | |
|---|---|---|---|
| iPS:393944 | | AA | DIVMTQSPDSLAVSLGERATLNCKSSQSVLYSSN NNNYLTWYQQKPGQRPKLLIYWASTRESGVPD RFSGSGSGTNFTLTISSLQAEDVAVYYCQQYYST PPTFGQGTKVEIK<br>SEQ ID NO: 24918 | QVQLVQSGPEVKKPGASVKVSCKASGYTFTNYDIN WVRQATGQGLEWMGWMHPNSGATGYAQRFQGR VTMTRNTSISTAYMELSSLRSEDTAVYYCATSSGW EVFDYWGQGTLVTVSS<br>SEQ ID NO: 28924 |
| | 21-225_14D6 | NA | GACATCCAAATGACCCAGTCTCCATCCTCCCT GTCTGCATCTGTCGGAGACAGTGTCACCATCA CTTGCCGGGCAAGTCAGGACATTAGAAATCAT TTAGGCTGGTATCAGCATAAACCAGGAAAGC CCCTAAGCGCCTGATCTATGCTGCATCCAGTT GCAAAGTGGGGTCCCATCTAGGTTCAGCGGCA GTGGATCTGGGACAGACCTGAAGATTTTGCAACTTA AGCAGCCTGAGCCAGAATTCACTCTCACAATC AGCAGCCTGCAGCCTGAAGATTTTGCAACTTA TTACTGTCTACAGTATAATAGTTACCCATTCAC TTTCGGCCCTGGGACCAAAGTGGATATCAAC<br>SEQ ID NO: 24919 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGTTATACCAT GAACTGGGTCCGCCAGGCTCCAGGGAAGGGGCT GGAGTGGGTCTCATCCATTAGTGGTAGTGGTAGT TACATATACTACGCAGACTCAGTGAAGGGCCGAT TCACCATGTCCAGAGACAACGCCAAGAACTCACT GTATCTGCAAATGAACAGCCTGAGAGCCGAGGA CACGGCTGTGTATTACTGTGCGAGAGTAGCAGCC TTTGACTCCTGGGGCCAGGGAACCCTGGTCTCCG TCTCCTCA<br>SEQ ID NO: 28925 |
| | | AA | DIQMTQSPSSLSASVGDSVTITCRASQDIRNHLG WYQHKPGKAPKRLIYAASSLQSGVPSRFSGSGS GTEFTLTISSLQPEDFATYYCLQYNSYPFTFGPGT KVDIN<br>SEQ ID NO: 24920 | EVQLVESGGGLVKPGGSLRLSCAASGFTFSSYTMN WVRQAPGKGLEWVSSISGSGSYIYYADSVKGRFTM SRDNAKNSLYLQMNSLRAEDTAVYYCARVAAFDS WGQGTLVSVSS<br>SEQ ID NO: 28926 |

FIGURE 50
(Continued)

| | | | |
|---|---|---|---|
| iPS:393946 | 21-225_16A4 | NA | GACATCCAGATGACCCAGTCTCCATCCTCACT GTCTGCATCTGTAGGAGACAGAGTCACCATCA CTTGTCGGGCGAGTCAGGACATTAGTAATTAT TTAGCCTGGTTTCAGCAGAAACCAGGGAAAGC CCCTAAGTCCCTGATCTCTGCTGCATCCAGTT GCAAAGTGGGGTCCCATCAAAATTCAGCGGCA GTGGATCTGGGACAGATTTCACTCTCACCATC AGCAGCCTGCAGCCTGAAGATTTTGCAACTTA TTACTGCCAACAGTATCATAGTTACCCGTGGA CGTTCGGCCAAGGGACCAAGGTGGAAATCAA T<br>SEQ ID NO: 24921 | GAGGTGCAGCTGGTGGAGTCTGGGGGAGGCTG GTCAAGCCTGGGGGGTCCCTGAGACTCTCCTGTG CAGCCTCTGGATTCACCTTCAGCAGCAGTATAGCAT GAACTGGGTCCGCCAGGCTCCAGGGAAGGGCT GGAGTGGGTCTCATCCATTAGTGGTAGTAGTACT TACAAATACTACGCAGACTCAGTGAAGGGCCGA TTCACCATCTCCAGAGACAACGCCAAGAACTCAC TGTATCTGCAAATGAACAGCCTGAGAACCGAGG ACACGGCTGTGTATTACTGTGCGAGAGATCGTGG GAGCTACTGGGGCCAGGGAACCCAGTCACCGT CTCCTCA<br>SEQ ID NO: 28927 |
| | | AA | DIQMTQSPSSLSASVGDRVTITCRASQDISNYLA WFQQKPGKAPKSLISAASSLQSGVPSKFSGSGSG TDFTLTISSLQPEDFATYYCQQYHSYPWTFGQGT KVEIN<br>SEQ ID NO: 24922 | EVQLVESGGGLVKPGGSLRLSCAASGFTFSSYSMN WVRQAPGKGLEWVSSISGSSTYKYYADSVKGRFTI SRDNAKNSLYLQMNSLRTEDTAVYYCARDRGSYW GQGTQVTVSS<br>SEQ ID NO: 28928 |
| iPS:393948 | 21-225_16A5 | NA | GACATCCAGATGACCCAGTCTCCTTCCTCCCT GTCTGCATCTGTAGGAGACAGAGTCACCATCA CTTGCCGGGCAAGTCAGGGCATTAGAAATGAT TTAGGCTGTGCTATCAGCAGAAACCAGGAAAG CCCCTAAGCGCCTGATCTATGCTGCATCCAGT TTGCAAAGTGGGGTCCCATCAAGGTTCAGCGG CAATGGATATGGGACAGATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br>SEQ ID NO: 24923 | CAGGTGCAGCTGGTGGAGTCTGGGGGAGGCGTG GTCCAGCCTGGGAGGTCCCTAAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGGTTTGATGAAGT AATAAATACTATGTAGACTCCGTGAAGGGCCGAT TCACCATCTCCAGAGACAATTCCAAGAACACGCT GTATCTGCAAATGAGCAGCCTGAGAGCCGAGGA CACGGCTGTGTATTACTGTGCGAGAGATCTTGGC TGGACGGAAGAGTACTGGGGCCAGGGAACCCTG GTCACCGTCTCCTCA<br>SEQ ID NO: 28929 |

FIGURE 50
(Continued)

| | | | |
|---|---|---|---|
| | | AA | DIQMTQSPSSLSASVGDRVTITCRASQGIRNDLG CYQQKPGKAPKRLIYAASSLQSGVPSRFSGNGY GTEFTLTISSLQPEDFATYYCLQHNSYPWTFGQG TKVEIK | QVQLVESGGGVVQPGRSLRLSCAASGFTFSDYGM HWVRQAPGKGLEWVAVIWFDGSNKYYVDSVKGR FTISRDNSKNTLYLQMSSLRAEDTAVYYCARDLGW TEEYWGQGTLVTVSS |
| | | | SEQ ID NO: 24924 | SEQ ID NO: 28930 |
| iPS:393950 | 21-225_3H10 | NA | TCCTATGAGCTGAGTCAGCCACCCTCAGTGTC CGTGTCCCAGGACAGACAGCCAGCATCACCT GCTCTGAGATAAATTGGGGAAAATATGCT TGCTGGTATCAGCAGAAGCCAGGCCAGTCCCC TGTGCTGGTCATCTATCAAGATAGGAAGCGGC CCTCAGGGATCCCTGAGCGATTCTCTGGCTCC AACTCTGGGAACAAAGCCACTCTGACCATCAG CGGGACCCAGGCTATGGATGAGGCTGACTATT ACTGTCAGGCCGTGGGTCAACAACACTATGATA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGGCT GGAGTGGGTGGCAGTTATATGGTTTGATGGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGAGATA TAGCAGTGGCTGGTATGACTACGGTTTGGACGTC TGGGGCCAAGGGACCACGGTCACCGTCTCCTCA |
| | | | SEQ ID NO: 24925 | SEQ ID NO: 28931 |
| | | AA | SYELSQPPSVSVSPGQTASITCSGDKLGEKYACW YQQKPGQSPVLVIYQDRKRPSGIPERFSGSNSGN KATLTISGTQAMDEADYYCQAWVNNTMIFGGG TKLTVL | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCARERYSS GWYDYGLDVWGQGTTVTVSS |
| | | | SEQ ID NO: 24926 | SEQ ID NO: 28932 |

FIGURE 50
(Continued)

| | | | |
|---|---|---|---|
| iPS:393952 | 21-225_1F1 | NA | GACATCCAGATGACCCAGTCTCCATCCTCACT GTCTGCATCTGTAGGAGACAGAGTCACCATCA CTTGTCGGGCGAGTCAGGCATTAACAATTAT TTAGCCTGGTTTCAGCAGAAATCAGGGAAAGC CCCTAAGTCCCTGATCTCTGTTGCATCCAGTT GCAAACTGGGGTCCCATCAAGGTTCAGCGGCA GTGGATCTGGGACAGATTTCACTCTCACCATC AGCAGCCTGCAGCCTGAAGATTTTGCAACTTA TTACTGCCAACAGTATAATAGTTACCCTCTCA CTTTCGGCGGAGGGACCAAGGTGGAGATCAA A SEQ ID NO: 24927 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAACAT GAACTGGGTCCGCCAGGCTCCAGGGAAGGGGCT GGAGTGGGTCTCATCCATTAGTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGTTAACCTC TTTGACTACTGGGGCCAGGGAACCCTGGTCACCG TCTCCCTCA SEQ ID NO: 28933 |
| | | AA | DIQMTQSPSSLSASVGDRVTITCRASQGINNYLA WFQQKSGKAPKSLISVASSLQTGVPSRFSGSGSG TDFTLTISSLQPEDFATYYCQQYNSYPLTFGGGT KVEIK SEQ ID NO: 24928 | EVQLVESGGGLVKPGGSLRLSCAASGFTFSSYNMN WVRQAPGKGLEWVSSISSSSYIYYADSVKGRFTIS RDNAKNSLYLQMNSLRAEDTAVYYCARVNLFDY WGQGTLVTVSS SEQ ID NO: 28934 |
| iPS:393954 | 21-225_4H6 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ATTATTGTCAACAGGCTAACAGTTTCCCATTC ACTTTCGGCGGCCCTGGGACCAAAGTGGATATCAA A SEQ ID NO: 24929 | CAGGTGCAGCTGGTACAGTCTGGGGCTGAGGTG AAGAAGCCTGGGGCTCAGTGAAGGTCTCCTGC AAGGCTTCTGGATACACCTTCACCGACTACTATT TGCACTGGGTGCGACAGGCCCCTGGACAAGGTCT TGAGTGGATGGGATGATCCACCTAACAGTGGT GGCACAAACTATGCACAGAAGTTCAGGGCAGG GTCACCATGACCAGGGACACGTCCATCAGCACA GCCTACATGGGGCTGAGCAGTCTGAGATCGACG ACACGGCCGTGTATTACTGTGCGAGAGATGGTAC CAGCTCGTTTGACTACTGGGGCCAGGGAACCCTG GTCACCGTCTCCTCA SEQ ID NO: 28935 |

FIGURE 50
(Continued)

| | | | |
|---|---|---|---|
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGPGT KVDIK | QVQLVQSGAEVKKPGASVKVSCKASGYTFTDYYL HWVRQAPGQGLEWMGWIHPNSGGTNYAQKFQGR VTMTRDTSISTAYMGLSSLRSDDTAVYYCARDGTS SFDYWGQGTLVTVSS |
| | | | SEQ ID NO: 24930 | SEQ ID NO: 28936 |
| iPS:393956 | 21-225_4D7 | NA | GACATCCAGATGACCCAGTCTCCATCCTCCCT GTCTGCATCTGTAGGAGACAGAGTCACCATCA CTTGCCGGGCAAGTCAGAGCATTAGCGACTAT TTAAATTGGTATCAGCAGAAACCAGGGAAAG CCCCTAAACTCCTGATCTTTGATACAACCAGT TGCAAAGTGGGGTCCCATCAAGGTTCAGTGGC AGTGGATCTGGGACAGATTTCACTCTCACCAT CAACAGTCTGCAACCTGAAGATTTTGCAACTT ACTACTGTCAACAGAGTTACAATACCCCTCCG GAGCGCAGTTTTGGCCAGGGGACCAAGCTGG AGATCAAA | GAGGTGAAGCTGTTGGAGTCTGGGGGAGGCTTG GTACAGCCGGGGGGGTCCTGAGACTCTCCTGTG CAGCCTCTGGATTCACCTTCAGCAGCTATGCCAT GAGCTGGGTCCGCCAGGCTCCAGGGAAGGGGCT GGAGTGGGTCTCAGTTCTTAGTGGTAGTGGTGGT AGCACATTCTACGCAGACTCCGTGAAGGGCCGGT TCACCATCTCCAGAGACAATTCCAAGAACACGCT GTATCTGCAAATGAGCAGCCTGAGAGCCGGGGA CACGGCCGTATATTCTGTGCCCGATATTGTAGT AGTGCCAGGTGCCCTTATGATGCTTTGATATCT GGGGCCAAGGGACAATGGTCACCGTCTCCTCA |
| | | | SEQ ID NO: 24931 | SEQ ID NO: 28937 |
| | | AA | DIQMTQSPSSLSASVGDRVTITCRASQSISDYLN WYQQKPGKAPKLLIFDTTSLQSGVPSRFSGSGSG TDFTLTINSLQPEDFATYYCQQTYNTPPERSFGQ GTKLEIK | EVKLLESGGGLVQPGGSLRLSCAASGFTFSSYAMS WVRQAPGKGLEWVSVLSGSGGSTFYADSVKGRFTI SRDNSKNTLYLQMSSLRAGDTAVYFCARYCSSARC PYDAFDIWGQGTMVTVSS |
| | | | SEQ ID NO: 24932 | SEQ ID NO: 28938 |

FIGURE 50
(Continued)

| | | | |
|---|---|---|---|
| iPS:393958 | 21-225_5H2 | NA | GACATCCAGATGACCCAGTCTCCATCTCCCT GTCTGCATCTGTAACAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCAGTCTCACAA TCAGCAGCCTGCAGCCTGAAGATTTTGCAACT TATTACTGTCTACAACATAATAGTTACCCTCTC ACTTTCGGCGGAGGGACCAAGGTGGAGATCA AA SEQ ID NO: 24933 | GAGGTGCAGCTGGTGGAGTCTGGGGGAGGCTG GTCAAGCCTGGGGGGTCCTTGAGACTCTCCTGTG CAGCCTCTGGATTCACATTCAGTAGTAGTTATACCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAAGCCAAGAACTCATT GTATCTGCAAATGAACAGCCTGAGAGCCGAGGA CACGGCTGTGTATTACTGTGCGAGAGGGAGCAG CTCGTCCGGCTTTGACTACTGGGGCCAGGGAACC CTGGTCACCGTCTCCTCA SEQ ID NO: 28939 |
| | | AA | DIQMTQSPSSLSASVTDRVTITCRASQGIRNDLG WYQQKPGKAPKRLIYAASSLQSGVPSRFSGSGS GTEFSLTISSLQPEDFATYYCLQHNSYPLTFGGGT KVEIK SEQ ID NO: 24934 | EVQLVESGGGLVKPGGSLRLSCAASGFTFSSYTMN WVRQAPGKGLEWVSSISGSSSYIYYADSVKGRFTIS RANAKNSLYLQMNSLRAEDTAVYYCARGSSSSGF DYWGQGTLVTVSS SEQ ID NO: 28940 |
| iPS:393960 | 21-225_7G2 | NA | GACATCCAGATGACCCAGTCTCCATCTCCCT GTCTGCGTCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATACTGCATCCAGT TTGCAAAGTGGGGTCCCATCAAGGTTCAGCGG CAGTGGATCTGGGACAGCCTCACTCTCACAA TCAGCAGCCTGCAGCCTGAAGATTTTGCAACT TATTACTGTCTACAACATAATAGTTACCCGTG GACGTTCGGCCCTAGGGACCAAGGTGGTCATCA AA SEQ ID NO: 24935 | CAGGTGCAACTGGTGGAGTCTGGGGGAGGCGTG GTCCAGCCTGGGAGGTCCCTGAGACTCTCCTGTG CAGCGTCAGGATTCACCTTCAGTGACTATGGCAT GCACTGGGTCCGCCAGGCTCCAGGCAAGGGGCT GGAGTGGATGGCAGTTATATGCAGACTCGTGTAACT AATAAATACTATGCAGACTCCGTGAAGGGCCGA TTCACCATCTGCAACTGAACAGCCTGAGAGCCGAGG TGTATCTGCAACTGAACAGCCTGAGAGCCGAGG ACACGGCTGTTTATTACTGTGCGAGAGAACTTGG CTGTACGAGGACTACTGGGGCCAGGGAACCCT GGTCACCGTCTCCTCA SEQ ID NO: 28941 |

FIGURE 50
(Continued)

| | | | |
|---|---|---|---|
| iPS:393962 | 21-225_7H7 | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNSYPWTFGLGT KVVIK<br>SEQ ID NO: 24936 | QVQLVESGGGVVQPGRSLRLSCAASGFTFSDYGM HWVRQAPGKGLEWMAVIWYDVTNKYYADSVKG RFTISRDNSKNTLYLQLNSLRAEDTAVYYCARELG WYEDYWGQGTLVTVSS<br>SEQ ID NO: 28942 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCACATCAAGGTTCAGCGG CAGTGGATCTGGGACAGAATTCACTCTCACAA TCAGCAGCCTGCAGCCTGAAGATTTTGCAACT TATTACTGTCTACAGCATAGTAGTTACCCGTTC ACTTTCGGCGGAGGGACCAAAGTGGAGATCAA A<br>SEQ ID NO: 24937 | CAGCTGCAGCTGCAGGAGTCGGGCCCAGGACTG GTGAAGCCTTCGGAGACCCTGTCCTCACCTGCA CTGTCTCTGGTGGCTCCATCAGCAGAAGTAGTTA CTACTGGGGCTGGATCCGCCAGCCCCCAGGGAA GGGGCTGGAGTGGATTGGGAATATCTATTATAGT GGGAGCACCTACTACATCCCGTCCCTCAAGAGTC AGTCACCATATCCGTTGACACGTCCAAGAACCA GTTCTCCCTGAAACTGAGCTCTGTGACCGCCGCA GACACGGCTGTGTATTACTGTGCGAGACACAGTA CCAGCTGGTCTCTTGACCACTGGGGCCAGGGAAC CCTGGTCACCGTCTCCTCA<br>SEQ ID NO: 28943 | |
| | | AA | DIQMTQSPSSLSASVGDRVTITCRASQGIRNDLG WYQQKPGKAPKRLIYAASSLQSGVTSRFSGSGS GTEFTLTISSLQPEDFATYYCLQHSSYPFTFVGGT KVEIK<br>SEQ ID NO: 24938 | QLQLQESGPGLVKPSETLSLTCTVSGGSISRSSYYW GWIRQPPGKGLEWIGNIYYSGSTYYIPSLKSRVTISV DTSKNQFSLKLSSVTAADTAVYYCARHSTSWSLDH WGQGTLVTVSS<br>SEQ ID NO: 28944 |

FIGURE 50
(Continued)

| | | | | |
|---|---|---|---|---|
| iPS:393964 | 21-225_6G1 | NA | GACATCCAGATGACCCAGTCTCCATCCTCCT GTCTGCATCTGTAGGAGACAGAGTCACCATCA CTTGCCGGACAAGTCAGAACATTATCAGCTAT TTAAATTGGTATCAGCAGAAACCAGGGAAAG CCCCTAAGGTCCTGATCTATACTGCATCCAATT TGCAAACTGGGGTCCCATCAGGGTTCAGTGGC AGTGGATCTGGGACAGATTTCACTCTCACCAT CAGCAGTCTGCAAACCTGAACCTGAAGATTTTGCAACTT ACTACTGTCAACAGCCTCACAGTCCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCATCTTCAGTAGCTATGGCAT GCACTGGGTCCGCCAGGCTCCAGGCAAGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTGCGAGAGATCTGAG TATGGGCGGTATGGACGTCTGGGGCCAAGGGAC CACGGTCACCGTCCTCA |
| | | | SEQ ID NO: 24939 | SEQ ID NO: 28945 |
| | | AA | DIQMTQSPSSLSASVGDRVTITCRTSQNIISYLNW YQQKPGKAPKVLIYTASNLQTGVPSGFSGSGSGT DFTLTISSLQPEDFATYYCQQPHSPPLTFGGGTK VEIK | QVQLVESGGGVVQPGRSLRLSCAASGFIFSSYGMH WVRQAPGKGLEWVAIIWYDGSNKYYADSVKGRFT ISRDNSKNTLYLQMNSLRAEDTAMYYCARDLSMG GMDVWGQGTTVTVSS |
| | | | SEQ ID NO: 24940 | SEQ ID NO: 28946 |
| iPS:393966 | 21-225_7F8 | NA | GACATCCAGATGACCCAGTCTCCATCCTCCCT GTCTGCATCTGTGGGAGACAGAGTCACCATCA CTTGCCGGGCAAGTCAGGGCATTAGCAATGAT TTAGGCTGGTATCAGCAGAAACCAGGGAAAG CCCCTAAGGCGCCTGATCTATGCTGCATCCAGT TTGCAAAGTGGGGTCCCATCACGGTTCAGCGG CAGTGTATCTGGGACAGATCACTCTCCAA TCAGCAGCCTGCAGCCTGAAGATTTTGCAACT TATTACTGTCTACAACATTATACTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTGTGTCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAATAACACGC TGTATCTGCAAATGAACAGCCTGAGAGCCGAGG ACACGGCTGTGTATTACTGTGCGAGAGAAAGTA TACCAGTGGCTGGCACGACTACGGTATGGACGTC TGGGGCCAAGGGACCACGGTCACCGTCTCCTCG |
| | | | SEQ ID NO: 24941 | SEQ ID NO: 28947 |

FIGURE 50
(Continued)

| | | | |
|---|---|---|---|
| iPS:393968 | 21-225_5A5 | AA | DIQMTQSPSSLSASVGDRVTITCRASQGIGNDLG WYQQKPGKAPKRLIYAASSLQSGVPSRFSGSVS GTEFTLPISSLQPEDFATYYCLQHYTYPRTFGQG TKVEIK<br>SEQ ID NO: 24942 | QVQLVESGGGVVQPGRSLRLSCAASGFTFSSCVMH WVRQAPGKGLEWVAVIWYDGSNKYYADSVKGRF TISRDNSNNTLYLQMNSLRAEDTAVYYCARERYTS GWHDYGMDVWGQGTTVTVSS<br>SEQ ID NO: 28948 |
| | | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTCTGCTGCATCCAGTTT GCAAAGTGGGGTCCCATCAAAGTTCAGCGGCA GTGGATCTGGGACAGACCTGAAGATTTTGCAACT AGCAGCCTGCAGCCTGAAGATTTTGCAACTTA TTACTGCCAACACAGTATATAGTTACCCATTCA CTTTCGGCCCTGGGACCAAAGTGGATATCAAA<br>SEQ ID NO: 24943 | GAGGTGCAGCTGTGTGGGAGTCTGGGGGAGGCTTG GTACAGCCTGGGGGGTCCCTGAGACTCTCCTGTG CAGCCTCCGGATTCACCTTCAGCAGCTATGCCAT GAACTGGGTCCGCCAGGCTCCAGGGAAGGGGCT GGAGTGGGTCTCAGCTATTAGTGGTAGTGGTGGT TACACATACTACGCAGACTCCGTGAAGGGCCGGT TCACCATCTCCCGAGACAATTCCAAGAACACGCT GTATCTGCAAATGAGCAGCCTGAGAGCCGAGGA CACGGCCGTTTATTACTGTGCGAAAGGGGGGTCC CTCTTCTACTGGGGCCAGGGAACCTTGGTCACCG TCTCTTCA<br>SEQ ID NO: 28949 |
| | | AA | DIQMTQSPSSLSASVGDRVTITCRASQGISNYLA WFQQKPGKAPKSLISAASSLQSGVPSKFSGSGSG TDFTLTISSLQPEDFATYYCQQYNSYPFTFGPGT KVDIK<br>SEQ ID NO: 24944 | EVQLWESGGGLVQPGGSLRLSCAASGFTFSSYAMN WVRQAPGKGLEWVSAISGSGGYTYADSVKGRFT ISRDNSKNTLYLQMSSLRAEDTAVYYCAKGGSLFY WGQGTLVTVSS<br>SEQ ID NO: 28950 |

FIGURE 50
(Continued)

| | | | |
|---|---|---|---|
| iPS:393972 | 21-225_7C9 | NA | GACATCCAGATGACCCAGTCTCCATCCTCCT GTCTGCATCTGTGGAGGAGACAGAGTCACCATCA CTTGCCGGGCAAGTCAGGGCATTAGAAACGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGTTTTATAGTTACCCTCGG ACGTTCGGCCAAGGGACCAAGGTGGATATCA AA SEQ ID NO: 24945 | CAGGTGCAGCTGGTGGAGTCTGGGGGAGGCGTG GTCCAGCCTGGGAGGTCCCTGAGACTCTCCTGTG CAGCGTCTGACTTCACCTTCAGTAACTATGTCAT GCACTGGGTCCGCCAGGCTCCAGGCAAGGGGCT GGAGTGGGTGGCTGTTATATGGTATGATGGAAGT AATAAATACTATGCAGACTCCGTGAAGGGCCGA TTCACCATCTCCAGAGACAATTCCAAGAACACGT TGTATCTGCAAATGAACAGCTGAGAGCCGAGG ACACGGCTGTGTATTACTGTGCGAGAGAAGTA TAGCAGCAGCTGTACGACTATGGTATGGACGTC TGGGGCCAAGGGACCACGGTCACCGTCTCCTCA SEQ ID NO: 28951 |
| | | AA | DIQMTQSPSSLSASGGDRVTITCRASQGIRNDLG WYQQKPGKAPKRLIYAASSLQSGVPSRFSGSGS GTEFTLTISSLQPEDFATYYCLQLYSYPRTFGQGT KVDIK SEQ ID NO: 24946 | QVQLVESGGGVVQPGRSLRLSCAASGLTFSNYVM HWVRQAPGKGLEWVAVIWYDGSNKYYADSVKGR FTISRDNSKNTLYLQMNSLRAEDTAVYYCAREKYS SSWYDYGMDVWGQGTTVTVSS SEQ ID NO: 28952 |
| iPS:393974 | 21-225_7C4 | NA | GACATCCAGATGACCCAGTCTCCATCCTCCCT GTTTGCATCTGTAGGAGACAGAGTCACCATCA CTTGCCGGGCAAGTCAGGGCATTAGAAATGAT TTAGGCTGGTATCAGCAGAAACCAGGGAAAG CCCATAAGCGCCTTATATATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA SEQ ID NO: 24947 | CAGGTGCAGCTGGTGGAGTCTGGGGGAGGCGTG GTCCAGCCTGGGAAGTCCCTGAGACTCTCCTGTG CAGCGTCTGGATTCACCTTCAGTAACTATGGCAT GCACTGGGTCCGCCAGGCTCCAGGCAAGGGGCT GGAATGGGTGGCAGTTATTTGGTATGAAGAAAAT TCAACCATCTCCAGAGACAACTCCAAGAACACGCT GTATCTGCAAATGAACAGCCTGAGAGCCGAGGA TTCCGGTCTGACTACTGGGGCCAGGGAACCCTGG TCACCGTCTCCTCA SEQ ID NO: 28953 |

FIGURE 50
(Continued)

| | | | |
|---|---|---|---|
| iPS:393976 | | AA | DIQMTQSPSSLFASVGDRVTITCRASQGIRNDLG WYQQKPGKAHKRLIYAASSLQSGVPSRFSGSGS GTEFTLTISSLQPEDFATYYCLQHNSYPLTFGGG TKVEIK<br>SEQ ID NO: 24948 | QVQLVESGGGVVQPGKSLRLSCAASGFTFSNYGM HWVRQAPGKGLEWVAVIWYEENNQYYADSVKGR FTISRDNSKNTLYLQMNSLRAEDTAVYYCARELGF RSDYWGQGTLVTVSS<br>SEQ ID NO: 28954 |
| | 21-225_7E9 | NA | GACATCCAGATGACCCAGTCTCCATCCTCCCT GTTTGCATCTGTAGGAGACAGAGTCACCATCA CTTGCCGGGCAAGTCAGGGCATTAGAAATGAT TTAGGCTGGTATGAGCAGAAACCAGGAGAAAG CCCCTAAGCGCCTGATCTATACTGCATCCAGT TTGCAAAGTGGGGTCCCATCACGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 24949 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGTAGACTCCGTGAAGGGCCGAT AATAAATACTATGTAGACTCCGTGAAGGGCCGAT TCACCATCTCCAGAGACAACTCCAAGAACACGCT GTATCTGCAAATGAACAGCCTGAGAGCCGAGGA CACGGCTGTATATTATTGTGCGAGAGAATTGGGG TTCCGGTCTGACTACTGGGGCCAGGGAACCCTGG TCACCGTCTCCTCA<br>SEQ ID NO: 28955 |
| | | AA | DIQMTQSPSSLFASVGDRVTITCRASQGIRNDLG WYEQKPGKAPKRLIYTASSLQSGVPSRFSGSGSG TEFTLTISSLQPEDFATYYCLQHNSYPLTFGGGT KVEIK<br>SEQ ID NO: 24950 | QVQLVESGGGVVQPGRSLRLSCAASGFTFSDYGM HWVRQAPGKGLEWVAVIWYDENNKYYVDSVKGR FTISRDNSKNTLYLQMNSLRAEDTAVYYCARELGF RSDYWGQGTLVTVSS<br>SEQ ID NO: 28956 |

FIGURE 50
(Continued)

| | | | | |
|---|---|---|---|---|
| iPS:393978 | 21-225_4C12 | NA | GACATCCAGATGACCCAGTCTCCATCCTCCT GTCTGCTCTGTAGGCGACAGAGTCACCATCA CTTGCCGGGCAAGTCAGGGACATTAGAAATGAT TTAGGCTGGTATCAGCAGAAACCAGGGAAAG CCCCTACGCGCCTGATCTATGCTGCATCCAGTT TGCACAGTGGGGTCCCATCACGGTTCAGCGGC AGTGGATCTGGGACAGAATTCACTCTCACAAT CAGCAGCCTGCAGCCTGAAGATCTTGCAACTT ATTACTGTCTACAACATTATAGTTTCCCTCGA CGTTCGGCCAAGGGACCAAGGTGGAAATCAA A <br><br> SEQ ID NO: 24951 | CAGGTGCAGTTGGTGGAGTCTGGGGGAGGCGTG GTCCAGCCTGGGAGGTCCCTGAGACTCTCCTGTG CAGCCTCTGATTCACCTTCAGTAGTAGTCAT GCACTGGGTCCGCCAGGCTCCAGGCAAGGGCT GGAGTGGGTGGCAGTTATATGGTATGATGAAGT AATAAATACTATGCAGAGACTCCGTGAAGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAGTA TAGCAGCAGCTGGTACGACTACGGTATGGACGTC TGGGGCCACGGGACCACGGTCACCGTCTCCTCA <br><br> SEQ ID NO: 28957 |
| | | AA | DIQMTQSPSSLSASVGDRVTITCRASQGIRNDLG WYQQKPGKAPTRLIYAASSLHSGVPSRFSGSGSG TEFTLTISSLQPEDFATYYCLQHYSFPRTFGQGTK VEIK <br><br> SEQ ID NO: 24952 | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCAREKYSS SWYDYGMDVWGHGTTVTVSS <br><br> SEQ ID NO: 28958 |
| iPS:393980 | 21-225_6D3 | NA | GACATCCAGATGACCCAGTCTCCATCCTCCCT GTCTGCATCTGTAGGAGACAGAGTCACCATCA CTTGCCGGACAAGTCAGAGCATTAGTAGTTAT TTAAATTGGTATCAGCAGAAACCAGGGAAAG CCCCTAAGCTCCTGATCTTTGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTTCTGTCTCAACAGAGTTACAGAACCCCTTT TTCACTTTCGGCCCTGGGACCAAAGTGGATAT CAAA <br><br> SEQ ID NO: 24953 | GAGGTGCAGCTGTTGGAGTCTGGGGGAGGCTTG GTACAGCCTGGGGGGTCCCTGAGACTCTCCTGTG CAGCCTCTGAATTCACCTTTAGCAGTCAGTGCCAT GAACTGGGTCCGCCAGGCTCCAGGGAAGGGCT GGAGTGGGTCTCAGTTATTAGTAGTGGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATATTCTGTGCGTCCCGTTTGGCA GTGGCTGGCCTCGGAGGCTTTTGATATCTGGGGCC AAGGGACAATGGTCACCGTCTCTTCA <br><br> SEQ ID NO: 28959 |

FIGURE 50
(Continued)

| | | | |
|---|---|---|---|
| | | AA | DIQMTQSPSSLSASVGDRVTITCRTSQSISTYLNW YQQKPGKAPKLLIFAASSLQSGVPSRFSGSGSGT DFTLTISSLQPEDFATYFCQQSYRTPFFTFGPGTK VDIK<br><br>SEQ ID NO: 24954 | EVQLLESGGGLVQPGGSLRLSCAASEFTFSSYAMN WVRQAPGKGLEWVSVISGRGNTFYADSVKGRFTI SRDNSKNTLYLQMNSLRAEDTAVYFCASRLAVAG SEAFDIWGQGTMVTVSS<br><br>SEQ ID NO: 28960 |
| iPS:393982 | 21-225_6C12 | NA | GACATCCAGATGACCCAGTCTCCATCCTCCCT GTCTGCATCTGTAGGAGACAGAGGCACCATCA CTTGCCGGGCAAGTCAGGGCATTAGAAGTAAT CAGCCCTCTGGATTCACCTTCAGTAGCTATAGCAT TTAGGCTGGTATCAGCAGAAACCAGGAAAG CCCCTAAGCGCCTGATCTATGCTGCATCCAGT TTGGAAAGTGGGGTCCCATCAAGGTTCAGCGG CAGTGGATCTGGGACAGAATTCACTCTCACAA TCAGCAGCCTGCAGCCTGAAGATTTTGCAACT TATTTCTGTCTACAGGATAATAGTTATCCGTTC ACTTTCGGCGGAGGGACCAAGGTGGAGATCA AA<br><br>SEQ ID NO: 24955 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGCT GGAGTGGGTCTCATCCATTAGTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGTGGG AGCCTCTGGGGCCAGGGAACCCTGGTCACCGTCT CCTCA<br><br>SEQ ID NO: 28961 |
| | | AA | DIQMTQSPSSLSASVGDRGTITCRASQGIRSNLG WYQQKPGKAPKRLIYAASSLESGVPSRFSGSGSG TEFTLTISSLQPEDFATYFCLQDNSYPFTFGGGTK VEIK<br><br>SEQ ID NO: 24956 | EVQLVESGGGLVKPGGSLRLSCAASGFTFSSYSMN WVRQAPGKGLEWVSSISSSSYIYADSVKGRFTIS RDNAKNSLYLQMNSLRAEDTAVYYCARDRGSLW GQGTLVTVSS<br><br>SEQ ID NO: 28962 |

FIGURE 50
(Continued)

| | | | |
|---|---|---|---|
| iPS:393984 | 21-225_4F12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CGGTGGATCTGGGACAATATTCACTCTCACAA TCAGCAGCCTGCAGCCTGAAGATTTTGCAACT TATTACTGTCTACAGCATAATAGTTACGCGCT CACTTTCGGCGGAGGGACCAAGGTGGAGATC AAA |
| | | | SEQ ID NO: 24957 |
| | | AA | DIQMTQSPSSLSASVGDRVTITCRASQGIRNDLG WYQQKPGKAPKRLIYAASSLQSGVPSRFSGGGS GTIFTLTISSLQPEDFATYYCLQHNSYALTFGGGT KVEIK |
| | | | SEQ ID NO: 24958 |
| iPS:393986 | 21-225_7G4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCGGGACAGAGCCTGAAGATTCTGCAACT TCAGCAGCCTGCAGCCTGAAGATTCTGCAACT TATTACTGTCTACATCAATATAGTTACCCTCGG ACGTTCGGCCAAGGGACCAAGGTGGAAATCA AA |
| | | | SEQ ID NO: 24959 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGTTACT AATAAAAAGTATGCAGACTCCGTGAAGGGCCGA TTCACCATCTCCAGAGACAATTCCAAGAACACGC TGTATCTGCAAATGAACAGCCTGACACCAGAGA ACACGGGTGGATATGAGAACCAGAGAAAAGG GGGTCTATTTGACTACTGGGGCCAGGGAACCCT GGTCACCGTCTCCTCA |
| | | | SEQ ID NO: 28963 |
| | | AA | QVQLVESGGGVVQPGRSLRLSCAASGFTFSSYGMH WVRQAPGKGLEWVAVIWYDVTNKKYADSVKGRF TISRDNSKNTLYLQMNSLTPENFGGYENQREKGGL FDYWGQGTLVTVSS |
| | | | SEQ ID NO: 28964 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAATAACTATGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGACCAGCCTGAGAGCCGAGG ACACGGCTGTGTATTACTGTGCGAGAGAAGTA TAGCAGCAACTGGTACGACTACGGTATGGACGTC TGGGGCCAAGGGACCACGGTCACCGTCTCCTCA |
| | | | SEQ ID NO: 28965 |

FIGURE 50
(Continued)

| | | | |
|---|---|---|---|
| iPS:393988 | 21-225_7F10 | AA | DIQMTQSPSSLSASVGDRVTITCRASQGIRNDLG WYQQRPGKAPKRLIYAASSLQSGVPSRFSGSGS GTEFTLTISSLQPEDSATYYCLHQYSYPRTFGQG TKVEIK<br>SEQ ID NO: 24960 | QVQLVESGGGVVQPGRSLRLSCAASGFTFNNYVM HWVRQAPGKGLEWVAVIWYDGSNKYYADSVKGR FTISRDNSKNTLYLQMTSLRAEDTAVYYCAREKYS SNWYDYGMDVWGQGTTVTVSS<br>SEQ ID NO: 28966 |
| | | NA | GACATCCAGATGACCCAGTCGCCATCCGCACT GTCTGCATCTGTAGGAGACAGAGTCACCATCA CTTGTCGGGCGAGTCAGGACATTAGGAATTAT TTAGCCTGGTTTCAGCAGAAACCAGGAAAGC CCCTAAGTCCCTGATCTCTGTTGCATCCAGTTT GCAAAGTGGGGTCCCATCCAAGGTTCAGCGGT AGTGGATCTGGGACAGATTTCACTCTCACCAT CAGCAGCCTGCAGCCTGAAGATTTTGCAACTT ATTATTGCCAACAGTATAATAGTTACCCCTCTC ACTTTCGGCGGAGGGACCAAGGTGGAGATCA AA<br>SEQ ID NO: 24961 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAACCGAGGA CACGGCTGTGTATTACTGTGCGAGAGCTAACCTC TTTGACTACTGGGGCCAGGGAACCCTGGTCACCG TCTCCTCA<br>SEQ ID NO: 28967 |
| | | AA | DIQMTQSPSPALSASVGDRVTITCRASQDIRNYLA WFQQKPGKAPKSLISVASSLQSGVPSRFSGSGSG TDFTLTISSLQPEDFATYYCQQYNSYPLTFGGGT KVEIK<br>SEQ ID NO: 24962 | EVQLVESGGGLVKPGGSLRLSCAASGFTFSSYSMN WVRQAPGKGLEWVSSISSSSYIYADSVKGRFTIS RDNAKNSLYLQMNSLRTEDTAVYYCARANLFDY WGQGTLVTVSS<br>SEQ ID NO: 28968 |

FIGURE 50
(Continued)

| | | | | |
|---|---|---|---|---|
| iPS:393990 | 21-225_11G7 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGACCTCACTCTCACAA TCAGCAGCCTGCAGCCTGAAGATTTTGCAACT TATTACTGTCTACAGCATAGTAATTACCCTCTC ACTTTCGGCGGAGGGACCATGGTGGAGATCAG A | CAGCTGCAGCTGCAGGAGTCGGGCCCAGGACTG GTGAAGCCTTCGGAGAGACCCTGTCCCTCACTGCA CTGTCTCTGGTGGCTTCATCAGCAGGAGTACTTA CTACTGGGGCTGGATCCGCCAGCCCCAGGGAA GGGGCTGGAGTGGATTGGGAGTATCTATTATAGT GGGAGCACCTGCTACAGCCCGTCCCTCAAGAGTC GAGTCACCATATCGTAGAACACGTCAAAAACC AGTTCTCCCTGAAGTTGAGCTCTGTGACCGCCGC AGACACGGCTGTGTATTACTGTGCGAGACTGAAC AGCAGCTGGTCTTTTGACTACTGGGGCCAGGGAA CCCTGGTCACCGTCTCCTCA |
| | | | SEQ ID NO: 24963 | SEQ ID NO: 28969 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHSNYPLTFGGG TMVEIR | QLQLQESGPGLVKPSETLSLTCTVSGGFISRSTYYW GWIRQPPGKGLEWIGSIYYSGSTSYSPSLKSRVTISV DTSKNQFSLKLSSVTAADTAVYYCARLNSSWSFDY WGQGTLVTVSS |
| | | | SEQ ID NO: 24964 | SEQ ID NO: 28970 |
| iPS:393992 | 21-225_14H8 | NA | GACATCCAGATGACCCAGTCTCCATCCTCACT GTCTGCATCTGTAGGAGACAGAGTCACCATCA CTTGTCGGGCGAGTCAGGGCATTAGCAGTTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATATTGCAACTTA TTACTGCCAACAGAGTATATAGTTACCCATTCA CTTTCGGCCCTGGGACCAAAGTGGATATCAAT | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTAGCAATAGCAT GAACTGGGTCCGCCAGGCTCCAGGGAAGGGCT GGAGTGGGTTTCATACATTAGTAGTAGTAGTAGT ACCATATACTACCCAGAGACTCTGTGAAGGGCCGAT TCACCATCCAGAGACAATGAACCAAGAACTCACT GTATCTGCAAATGAACAGCCTGAGAGAGGTGG CACGGCTGTGTATTACTGTGCGAGAGAGGTTGGG AGCCCTTTGACTACTGGGGCCAGGGAACCCTGG TCACCGTCTCCTCA |
| | | | SEQ ID NO: 24965 | SEQ ID NO: 28971 |

FIGURE 50
(Continued)

| | | | |
|---|---|---|---|
| iPS:393994 | | AA | DIQMTQSPSSLSASVGDRVTITCRASQGISYYLA WFQQKPGKAPKSLIYAASSLQSGVPSKFSGSGSG TDFTLTISSLQPEDFATYYCQQYNSYPFTFGPGT KVDIN<br>SEQ ID NO: 24966 | EVQLVESGGGLVQPGGSLRLSCAASGFTFSSNSMN WVRQAPGKGLEWVSYISSSSSTIYYADSVKGRFTIA RDNAKNSLYLQMNSLRDEDTAVYYCARGGGSPFD YWGQGTLVTVSS<br>SEQ ID NO: 28972 |
| | 21-225_8C9 | NA | GACATCCAGATGACCCAGTCTCCATCCTCCCT GTCTGCATCTATAGGAGACAGAGTCACCATCA CTTGCCGGGCAAGTCAGGCATTAGAAATGAT TTAGACTGGTATCAGCAGAAACCAGGAAAG CCCCTAAGCGCCTTATCTATGCTGCATCCAGTT TGCAAAGTGGGGTCCCATCAAGGTTCAGCGGC AGTGGATCTGGGACAGATCACTCTCACAAT CAGCAGCCTGCAGACTGAAGATTTTGCAACTT ATTACTGTCTACAGCATATAGTTATCCGCTC ACTTTCGGCGGAGGGACCAAGGTGGAGATCA AA<br>SEQ ID NO: 24967 | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAGCTATGGCAT GCACTGGGTCCGCCAGGCTCCAGGCAAGGGGCT GGAGTGGGTGGCAGTTATATGTAGACTCCGTGAAGGCCGAT AATAAATACTATGTAGACTCCGTGAAGGGCCGAT TCACCATCTCCAGAGACAACTCCAAGAACACGCT GTATCTGCAAATGAACAGCCTGAGAGCCGAGGA CACGGCTGTGTATTACTGTGCGAGAGAATTGGGG TTCCGGTCTGACTACTGGGGCCAGGGAACCCTGG TCACCGTCTCCTCA<br>SEQ ID NO: 28973 |
| | | AA | DIQMTQSPSSLSASIGDRVTITCRASQAIRNDLD WYQQKPGKAPKRLIYAASSLQSGVPSRFSGSGS GTEFTLTISSLQTEDFATYYCLQHNSYPLTFGGG TKVEIK<br>SEQ ID NO: 24968 | QVQLVESGGGVVQPGRSLRLSCAASGFTFSSYGMH WVRQAPGKGLEWVAVIWYDENNKYYVDSVKGRF TISRDNSKNTLYLQMNSLRAEDTAVYYCARELGFR SDYWGQGTLVTVSS<br>SEQ ID NO: 28974 |

FIGURE 50
(Continued)

| | | | |
|---|---|---|---|
| iPS:393996 | 21-225_15C11 | NA | GACATCCAGATGACCCAGTCTCCATCTCCT GTCTGCATCTGTAGGAGACAGAGTCACCATCA CTTGCCGGGCAAGTCAGGGCATTAGAAATGAT TTAGGCTGGTATCAGCAGAAGCCAGGGAAAG TCCCTAAGCGCCTGATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACTGCATTATAGTTACCCTCGGA CGTTCGGCCGAGGGACCAAGGTGGAAATCAA A |
| | | | SEQ ID NO: 24969 |
| | | AA | DIQMTQSPSSLSASVGDRVTITCRASQGIRNDLG WYQQKPGKVPKRLIYAASSLQSGVPSRFSGSGS GTEFTLTISSLQPEDFATYYCLLHYSYPRTFGRGT KVEIK |
| | | | SEQ ID NO: 24970 |
| iPS:393998 | 21-225_12B12 | NA | GACATCCAGATGACCCAGTCTCCATCTCCCT GTCTGCGTCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAACATAATAGTTACCCGTG GACGTTCGGCCTAGGGACCAAGGTGGTCATCA AA |
| | | | SEQ ID NO: 24971 |

| | |
|---|---|
| | CAGGTGCAGCTGGTGGAGTCTGGGGGAGGCGTG GTCCAGCCTGGGAGGTCCCTGAGACTCTCCTGTG CAGCGTCTGATTCACCTTCAGTGACTATGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAAG ACACGGCTGTATTACTGTGCGAGAGAAGTA TAGCAGCAGCTGGTACGACTACGGTTTGGACGTC TGGGGCCAAGGGACCACGGTCACCGTCTCCTCA |
| | SEQ ID NO: 28975 |
| | QVQLVESGGGVVQPGRSLRLSCAASGFTFSDYVM HWVRQAPGKGLEWVAVIWYDGSNKYYADSVKGR FTISRDNSKNTLYLQMNSLRAEDTAVYYCAREKYS SSWYDYGLDVWGQGTTVTVSS |
| | SEQ ID NO: 28976 |
| | CAGGTGCAACTGGTGGAGTCTGGGGGAGGCGTG GTCCAGCCTGGGAGGTCCCTGAGACTCTCCTGTG CAGCGTCTGATTCACCTTCAGTGACTATGGCAT GCACTGGGTCCGCCAGGCTCCAGGCAAGGGGCT GGAGTGGATGGCAGTTATATGGTATGATGTAACT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTACGAGGACTACTGGGGCCAGGGAACCCT CTGGTACGAGGACTACTGGGGCCAGGGAACCCT GGTCACCGTCTCCTCA |
| | SEQ ID NO: 28977 |

FIGURE 50
(Continued)

| | | | | |
|---|---|---|---|---|
| | | AA | DIQMTQSPSSLSASVGDRVTITCRASQGIRNDLGWYQQKPGKAPKRLIYTASSLQSGVPSRFSGSGSGTEFTLTISSLQPEDFATYYCLQHNSYPWTFGLGTKVVIK<br>SEQ ID NO: 24972 | QVQLVESGGGVVQPGRSLRLSCAASGFTFSDYGMHWVRQAPGKGLEWMAVIWYDVTNKYYADSVKGRFTISRDNSKNTLYLQMNSLRAEDTAVYYCARELGWYEDYWGQGTLVTVSS<br>SEQ ID NO: 28978 |
| iPS:394000 | 21-225_11A2 | NA | GACATCCAGATGACCCAGTCTCCATCCTCCCTGTCTGCATCTGTAGGAGACAGAGTCACCATCACTTGCCAGGCGAGTCAGGACAGATTAGCAACTATTTAAATTGGTATCAGCAGAAACCAGGGAAAGCCCCTAAGCTCCTGATCTACGATGCATCCAATTTGGAAACAGGGGTCCCCTCAAGATTTCAGTGGAAGTGGATCTGGGACAGATTTTACTTTCACCATCAGCAGCCTGCAACCTGCAAGATGTTGCAACATATTACTGTCAACAGTATGATAATCTCCCGATCACCTTCGGCCAAGGGACCACGACTGGACATTAAA<br>SEQ ID NO: 24973 | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATCATATGGTGGAAGTAATAAAGACTCTGCAGACTCCGTGAAGGGCCGATTCATCTCCAGAGACAATTCCAAGAACACGCTGTATCTGCAAATGAACAGCCTGAGAGCTGAGGACACGGCTGTGTATTACTGTGTGAGACGGGGATACAGCTATGGCGGGTACGGTATGGACGTCTGGGGCCAAGGGACCACGGTCACCGTCTCCTCA<br>SEQ ID NO: 28979 |
| | | AA | DIQMTQSPSSLSASVGDRVTITCQASQDISNYLNWYQQKPGKAPKLLIYDASNLETGVPSRFSGSGSGTDFTFTISSLQPEDVATYYCQQYDNLPITFGQGTRLDIK<br>SEQ ID NO: 24974 | QVQLVESGGGVVQPGRSLRLSCAASGFTFSSYGMHWVRQAPGKGLEWVAVISYGGSNKDSADSVKGRFIISRDNSKNTLYLQMNSLRAEDTAVYYCVRRGYSYGGYGMDVWGQGTTVTVSS<br>SEQ ID NO: 28980 |

FIGURE 50
(Continued)

| | | | | |
|---|---|---|---|---|
| iPS:394002 | 21-225_15G7 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGAAAGCCCCTAAGCGCCTGATCTATGCTGCATCCAGTTTGCAAAGTGGGGATCCCATCAAGGTTCAGCGGCAGTGGATTTGGGACAGAATTCACTCTCACAATCAGCAGCCTGCAGCCTGAAGATTTTGCAACTTATTACTGTCTACAGCATAGTAATTACCCTCTCACTTTCGGCGGAGGGACCAAGGTGGAGATCAAAA | CAGCTGCAGCTGCAGGAGTCGGGCCCAGGACTGGTGAAGCCTTCGGAGACCCTGTCCCTCACCTGCACTGTCTCTGGTGGCTCCATCAGCAGGAGTAGTTCCTACTGGGGCTGGATCCGCCAGCCCCAGGAAGGGACTGGAGTGGATTGGGAGTATCTATTATAGTGGGTACACCTATTACAACCCGTCCCTCAAGAGTCGAGTCACCATATCCGTGGACACGTCCAAGAACCAGTTCTCCCTGAGGCTGAGCTCTGTGACCGCGCAGACACGGCTTCGTATTACTGTGCGAGACTGAGCAGCAGTTGGTCTTTTGACTTCTGGGGCCAGGGAACCCTGGTCACCGTCTCCTCA |
| | | | SEQ ID NO: 24975 | SEQ ID NO: 28981 |
| | | AA | DIQMTQSPSSLSASVGDRVTITCRASQGIRNDLGWYQQKPGKAPKRLIYAASSLQSGIPSRFSGSGFGTEFTLTISSLQPEDFATYYCLQHSNYPLTFGGGTKVEIK | QLQLQESGPGLVKPSETLSLTCTVSGGSISRSSSYWGWIRQPPGKGLEWIGSIYYSGYTYTPSLKSRVTISVDTSKNQFSLRLSSVTAADTASYYCARLSSSWSFDFWGQGTLVTVSS |
| | | | SEQ ID NO: 24976 | SEQ ID NO: 28982 |
| iPS:394004 | 21-225_13A1 | NA | GACATCCAGATGACCCAGTCTCCATCCTCCCTGTCTGCATCTGTAGGAGACAGAGTCACCATCACTTGCCAGGCGAGTCAGGACATTAACAACTATTTAAATTGGTATCAGCAGAAACCAGGGACAGCCCCTAAGCTCCTGATCTACGATGGATCCAATTTGGAAACAGGGGTCCCATCAAGGTTCAGTGGAAGTGGATCTGGGACAGATTTTACTTTCACCATCAGCAGCCTGCAGCCTGAAGATATTGCAACATATTACTGTCAACAGTATGAAAATCTCCCGATCACTTTCGGCCAAGGGACACGACTGGAGATTAAA | CAGGTGCAGTTGGTGGAGTCTGGGGGAGGCGTGGTCCAGCCTGGGAGGTCCCTGAGACTCTCCTGTGCAGCCTCTGGATTCACCTTCAGCAGCTATGGCATGCACTGGGTCCGCCAGGCTCCAGGCAAGGGGCTGGAGTGGGTGGCAGTTATATCATATGATGGAAGCAATAATACTATGCAGACTCCGTGAAGGGCCGATTCACCATTCCAGAGACAATTCCAAGAACACGCTCTATCTGCAAATGAACAGCCTGAGAGCTGAGGACACGGCTGTGTTTATTGTGTGACGCGGGATACAGCTATGGCGGGTACGGTATGGACGTCTGGGGCCAAGGGACCACGGTCACCGTCTCCTCA |
| | | | SEQ ID NO: 24977 | SEQ ID NO: 28983 |

FIGURE 50
(Continued)

| | | | | |
|---|---|---|---|---|
| iPS:394006 | 21-225_15C2 | AA | DIQMTQSPSSLSASVGDRVTITCQASQDINNYLN WYQQKLGTAPKLLIYDGSNLETGVPSRFSGSGS GTDFTFTISSLQPEDIATYYCQQYENLPITFGQGT RLEIK | QVQLVESGGGVVQPGRSLRLSCAASGFTFSSYGMH WVRQAPGKGLEWVAVISYAGTNQYYADSVKGRF TISRDNSKNTLYLQMNSLRAEDTAVYYCVRRGYSY GGYGMDVWGQGTTVTSS |
| | | | SEQ ID NO: 24978 | SEQ ID NO: 28984 |
| | | NA | GACATCCAGATGACCCAGTCTCCATCCTCCCT GTCTGCATCTGTAGGAGACAGAGTCACCATCA CTTGCCAGGCGAGTCAGGACATTACCAACTAT TTAAATTGGTATCAGCAGAAACCAGGGAAAG CCCCTAACCTCCTGATCTACGATGCATCCAATT TGGAAAACAGGGGTCCCATCAAGGTTCAGTGGA AGTGGATCTGGGACAGATTTTACTTTCACCAT CAGCAGCCTGCAGCCTGAAGATATTGCGACAT ATTACTGTCAACAGTATGATAATCTCCCGATC ACCTTCGCCCAAGGGACACGACTGGAGATTAA A | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGTCAATAATATCAGACTCCGTGAAGGGCCGAT TCACCATCTCCAGAGACAATTCCAAGAACACGCT GTATCTGCAAATGAACAGCTGAGAGCTGAGGA CACGGCTGTGTATTACTGTGTGAGACGGGGATAC AGCTATGGCGGGTACGGTATGGACGTCTGGGGC CAAGGGACCACGGTCACCGTCTCCTCA |
| | | | SEQ ID NO: 24979 | SEQ ID NO: 28985 |
| | | AA | DIQMTQSPSSLSASVGDRVTITCQASQDITNYLN WYQQKPGKAPNLLIYDASNLETGVPSRFSGSGS GTDFTFTISSLQPEDIATYYCQQYDNLPITFAQGT RLEIK | QVQLVESGGGVVQPGRSLRLSCAASGFTFSSYGMH WVRQAPGKGLEWVSIISYGGRNNHYADSVKGRFTI SRDNSKNTLYLQMNSLRAEDTAVYYCVRRGYSYG GYGMDVWGQGTTVTSS |
| | | | SEQ ID NO: 24980 | SEQ ID NO: 28986 |

FIGURE 50
(Continued)

| | | | |
|---|---|---|---|
| iPS:394008 | 21-225_15H8 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGGCGCCTGATCTTTGCTGCATCCAGTT TGCAAAGTGGGCGTCCCATCACGGTTCAGCGGC AGTGGATCTGGGACAGAATTCACTCTCACAAT CAGCAGCCTGCAGCCTGAAGATTTTGCAACTT ATTACTGTCTACAGCATATAATAGTTACCCGCTC ACTTTCGGCGGAGGGACCAAGGTGGAGATCA GA<br>SEQ ID NO: 24981 | GAGGTGCAGCTGGTGGAGTCTGGGGGAGGCGTG GTCAAGCCTGGGGGGTCCCTGAGACTCTCCTGTG CAGCCTCTGGATTCACCTTCAGCAGCTATGTCAT GAACTGGGTCCGCCAGGCTCCAGGGAAGGGGCT GGAGTGGGTCTCATCATTAGTGGTAGTAGTACT TACATATACTGGCGGAGACTCAATCAAGGGCCGAT TCACCATCTCCCGAGACAACGCCAAGAACTCT GTATCTGCAAATGAACAGCCTGAGAGCCGATGA CACGGCTGTGTATTACTGTGCGAGAGATCGAGGC TCCATCTGGGGCCAAGGGACAATGGTCACCGTCT CTTCA<br>SEQ ID NO: 28987 |
| | | AA | DIQMTQSPSSLSASVGDRVTITCRASQGIRNDLG WYQQKPGKAPKRLIFAASSLQSGVPSRFSGSGSG TEFTLTISSLQPEDFATYYCLQHNSYPLTFGGGT KVEIR<br>SEQ ID NO: 24982 | EVQLVESGGGLVKPGGSLRLSCAASGFTFSSYVMN WVRQAPGKGLEWVSSISGSSTYIYCADSIKGRFTIS RDNAKNSLYLQMNSLRADDTAVYYCARDRGSIWG QGTMVTVSS<br>SEQ ID NO: 28988 |
| iPS:394010 | 21-225_12G5 | NA | GACATCCAGATGACCCAGTCTCCATCCTCCCT GTCTGCCTCTGTAGGAGACAGAGTCACCATCC CTGCCGGGCGAGTCAGGACATTAGCAGTCAGT TTAGCCTGGTATCAGCAGAAACCAGGGAAAGT TCCTAAGCTCCTGATCTATGCTGCATACATTTT GCAATCAGGGGTCCCATCTCGGTTCAGTGGCA GTGGATCTGGGACAGATTTCACTCTCACCATC AGCAGCCTGCAGCCTGAAGATGTTGCAGCTTA TTACTGTCAAAAGTATGACAGTGCCCATTCA CTTTCGGCCCTGGGACCAAAGTGGATATCAAA<br>SEQ ID NO: 24983 | CAGGTGCAGCTGCAGGAGTCGGGGGAGGCGTG GTCCAGCCTGGGAGGTCCCTGAGACTCTCCTGTG CAGCCTCTGGATTCACCTTCAGTAACTATGGCAT CTACTGGGTCCGCCAGGCTCCAGGCAAGGGGCT GGAGTGGGTGGCAGTTATATCATATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGCGAGAGATCGGGG AGCAGGTGGCTGCTACTACTACGGTATAGAC GTCTGGGGCCAAGGGACCACGGTCACCGTCTCCT CA<br>SEQ ID NO: 28989 |

FIGURE 50
(Continued)

| | | AA | DIQMTQSPSSLSASVGDRVTIPCRASQDISNYLA WYQQKPGKVPKLLIYAAYILQSGVPSRFSGSGSG TDFTLTISSLQPEDVAAYYCQKYDSAPFTFGPGT KVDIK | QVQLVESGGGVVQPGRSLRLSCAASGFTFSNYGIY WVRQAPGKGLEWVAVISYDGSNKYYADSVKGRFT ISRDNSKNTLYLQMNSLRAEDTAVYYCARDRGAV AAYYYYGIDVWGQGTTVTVSS |
|---|---|---|---|---|
| | | | SEQ ID NO: 24984 | SEQ ID NO: 28990 |
| iPS:394012 | 21-225_15A3 | NA | GACATCCAGATGACCCAGTCTCCATCCTCCCT GTCTGCATCTGTAGGAGACAGAGTCACCATCA CTTGCCGGGCAAGTCAGAGCATTATCAGTAT TTAAATTGGTATCTGCAGAAACCAGGGAAAGC CCCTAAGTTCCTGATCTATACTGCATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTACTGTCAACAGACTTACAGTACCCCGCTCA CTTTCGGCGGAGGGACCAAGGTGGAGATCAA G | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT TCACTGGGTCCGCCAGGCTCCAGGCAAGGGGCT GGAGTGGGTGGCAGTTATATGCAGACTCCGTGAAGGCCG ATTCACCATCTCCAGAGACACAATTCCAAGAACACG CTGTATCTGCAAATGAACAGCCTGAGAGCCGAG GACACGGCTGTGTATTACTGTGCGAGAGATCTGA GTATGGGCGGTATGGACGTCTGGGGCCAAGGA CCACGGTCACCGTCTCCTCA |
| | | | SEQ ID NO: 24985 | SEQ ID NO: 28991 |
| | | AA | DIQMTQSPSSLSASVGDRVTITCRASQSIISYLNW YLQKPGKAPKFLIYTASSLQSGVPSRFSGSGSGT DFTLTISSLQPEDFATYYCQQTYSTPLTFGGGTK VEIK | QVQLVESGGGVVQPGRSLRLSCAASGFTFSSYGIH WVRQAPGKGLEWVAVIWHDGSNKYYADSVKGRF TISRDNSKNTLYLQMNSLRAEDTAVYYCARDLSM GGMDVWGQGTTVTVSS |
| | | | SEQ ID NO: 24986 | SEQ ID NO: 28992 |

FIGURE 50
(Continued)

| | | | | |
|---|---|---|---|---|
| iPS:394014 | 21-225_8G6 | NA | GACATCCAGATGACCCAGTCTCCATCCTCCCT GTCTGCATCTGTAGGAGACAGAGTCACCATCA CTTGCCGGGCAAGTCAGAGCATTAGTAGTTAT TTAAATTGGTATCAGCAGAAACCAGGGAAAG CCCCCAAGCTCCTGATCTTTGCTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTTCTGTCAACAGAGTTACAGAACCCCCTTT TTCACTTTCGGCCCTGGGACCAAAGTGGATAT CAAA | GAGGTGCAGCTGTTGGAGTCTGGGGGAGGCTTG GTACAGCCTGGGGGGTCCCTGAGACTCTCCTGTG TAGCCCTCTGAATTCACCTTTAGCAGCTATGTCAT GAACTGGGTCCGCCAGGCTCCAGGGAAGGGCT GGAGTGGGTCTCAGTTATTAGTGGTCGTGGTGGT AACACATTCTACGCAGACTCCGTGAAGGGCCGGT TCACCATCTCCAGAGACACAATTCCAAGAACACGCT GTATCTGCAAATGAACAGCCTGAGAGCCGAGGA CACGGCCGTATATTACTGTGCGTCCCGTTTGGCA GTGGCTGCTCGGAGGCTTTTGTATATCTGGGGCC AAGGGACAAATGGTCAGGTCTCTTCA |
| | | | SEQ ID NO: 24987 | SEQ ID NO: 28993 |
| | | AA | DIQMTQSPSSLSASVGDRVTITCRASQSISSYLNW YQQKPGKAPKLLIFAASSLQSGVPSRFSGSGSGT DFTLTISSLQPEDFATYFCQQSYRTPFFTFGPGTK VDIK | EVQLLESGGGLVQPGGSLRLSCVASEFTFSSYVMN WVRQAPGKGLEWVSVISGRGGNTFYADSVKGRFTI SRDNSKNTLYLQMNSLRAEDTAVYYCASRLAVAG SEAFDIWGQGTMVSVSS |
| | | | SEQ ID NO: 24988 | SEQ ID NO: 28994 |
| iPS:394016 | 21-225_13D4 | NA | GACCTCCAGATGACCCAGTCTCCATCCTCCCT GTCTGCATCTGTAGGAGACCGAGTCACCATCA CTTGCCGGGCAAGTCAGAGCAGTTTCAGCTAC TTAAATTGGTATCAGCAGAAACCAGGGAAAG CCCCTAAGCTCCTGATCTGTACTGCATCCAGT TGCAAAATGGGGTCCCATCAAGGTTCAGTGGC AGTGGATCTGGGACAGATTTCACTCTCACCAT CAGCAGTCTACAGCCTGAGGATTTTGCAACTT ACTACTGTCAACAGACTTACAGTCTTCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGCAGACTCCGTGAAGGGCCG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGATCTGA GTATGGCGGTATGGACGTCTGGGGCCAAGGGA CCACGGTCACCGTCTCCTCA |
| | | | SEQ ID NO: 24989 | SEQ ID NO: 28995 |

FIGURE 50
(Continued)

| | | AA | DLQMTQSPSSLSASVGDRVTITCRASQSIFSYLN WYQQKPGKAPKLLICTASSLQNGVPSRFSGSGS GTDFTLTISSLQPEDFATYYCQQTYSLPLTFGGG TKVEIK<br><br>SEQ ID NO: 24990 | QVQLVESGGGVVQPGRSLRLSCAASGFTFSSYGMH WVRQAPGKGLEWVAVIWHDGSNKYYADSVKGRF TISRDNSKNTLYLQMNSLRAEDTAVYYCARDLSM GGMDVWGQGTTVTVSS<br><br>SEQ ID NO: 28996 |
|---|---|---|---|---|
| iPS:394018 | 21-225_15B1 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTAATCTCTGCTGCATCCAGTTT GCAAAGTGGGGTCCCATCAAACTTCAGCGGCA GTGGATCTGGGACAGATTTCACTCTCACCATC AGCAGCCTGCAGCCTGAAGATTTTGCAACTTA TTACTGCCAACAGTATCATAGTTACCCATTCA CTTTCGGCCCTGGGACCAAAGTGGATATCAAA<br><br>SEQ ID NO: 24991 | GAGGTGCAGCTGTTGGAGTCTGGGGGAGGCTTG GTACAGCCGGGGGGGTCCCTGAGACTCTCCTGTG CAACCTCAGGATTCACCTTTAGCAGCTATGTCAT GAGCTGGGTCCGCCAGGCTCCAGGGAAGGGGCT GGAGTGGGTCTCAGGTATTAGTGGTAGTGGTGGT AGCACAAACAACGCAGACTCCGTGAAGGGCCGG TTCACCATCTCCAGAGACACAATTCCAAGAACACGC TGTATCTGCAAGTGAACAGCCTGAGAGCCGAGG ACACGGCCGTATATTACTGTGCCCGCAGTCCTT GTTTGACTACTGGGGCCAGGGAACCCTGGTCACC GTCTCCTCA<br><br>SEQ ID NO: 28997 |
| | | AA | DIQMTQSPSSLSASVGDRVTITCRASQGISNYLA WFQQKPGKAPKSLISAASSLQSGVPSNFSGSGSG TDFTLTISSLQPEDFATYYCQQYHSYPFTFGPGT KVDIK<br><br>SEQ ID NO: 24992 | EVQLLESGGGLVQPGGSLRLSCATSGFTFSSYVMS WVRQAPGKGLEWVSGISGSGGSTNNADSVKGRFTI SRDNSKNTLYLQVNSLRAEDTAVYYCARSSLFDY WGQGTLVTVSS<br><br>SEQ ID NO: 28998 |

FIGURE 50
(Continued)

| | | | |
|---|---|---|---|
| iPS:394020 | 21-225_15H10 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAAGT TATTACTGTCTACACAGCATAATAGTTACCCGCTC ACTTTCGGCGGAGGGACCAAGGTGGAGATCA AT SEQ ID NO: 24993 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAGTTATATGGTATGATGAAAGT AATAAATACTATGAAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGTGAGGGAAGTGGG GTTTCTTTCTGACTACTGGGGCCAGGGAATCCTG GTCACCGTCTCCTCA SEQ ID NO: 28999 |
| | | AA | DIQMTQSPSSLSASVGDRVTITCRASQGIRNDLG WYQQKPGKAPKRLIYAASSLQSGVPSRFSGSGS GTEFTLTISSLQPEDFASYYCLQHNSYPLTFGGGT KVEIN SEQ ID NO: 24994 | QVQLVESGGGVVQPGRSLRLSCAASGFTFSNYGM HWVRQAPGKGLEWVAVIWYDESNKYYEDSVKGR FTISRDNSKNTLYLQMNSLRAEDTAVYYCVREVGF LSDYWGQGILVTVSS SEQ ID NO: 29000 |
| iPS:394022 | 21-225_16H6 | NA | GACATCCAGATGACCCAGTCTCCATCCTCCCT GTCTGCATCTGTAGGAGACAGAGTCACCATCA CTTGCCGGGCAAGTCAGAACATTAGCAGTAT TTAAATTGGTATCAGCAGAAACCAGGGAAAG CCCCTAAGCTCCTGATCTATGCTGCATCCAGT TGCAAAGTGGGGTCCCATCAAGGTTCAGTGGC AGAGGATCTGGGACAGATTTCACTCTCACCAT CAGTAGTCTGCAACCTGAAGATTTTGCAACTT ACTACTGTCAACAGAGTTACAGAACCCCTTA TTCACTTTCGGCCCTGGGACCAAGGTTGATTTC AAA SEQ ID NO: 24995 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGTTATTAGTGGTAGTGGTGGT TACACATACTACGGAGACTCCGTGAAGGGCCGGT TCACCATCTCCAGAGACAACAGCCAAGAACGCT GTATCTGCAAATGAACAGCCTGAGAGCCGAGGA CACGGCCGTCTATTACTGTGCGCCCGTTTAGCA GTGGCTGGCTCGGAGCGCTTTTGATATCTGGGGCC AAGGGACAATGGTCACCGTCTCTTCA SEQ ID NO: 29001 |

FIGURE 50
(Continued)

| | | | |
|---|---|---|---|
| iPS:394024 | | AA | DIQMTQSPSSLSASVGDRVTITCRASQNISSYLN WYQQKPGKAPKLLIYAASSLQSGVPSRFSGRGS GTDFTLTISSLQPEDFATYYCQQSYRTPLTFGPG TKVDFK<br>SEQ ID NO: 24996 | EVQLLESGGGLVQPGGSLRLSCAASGFTFSSYAMN WVRQAPGMGLEWVSVISRSGGYTYYADSVKGRFT ISRDNSKNTLYLQMNSLRAEDTAVYYCASRLAVAG SEAFDIWGQGTMVTVSS<br>SEQ ID NO: 29002 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGTTCAA T<br>SEQ ID NO: 24997 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCAT GCACTGGGTCCGCCAGGCTCCAGGCAAGGGCT GGAGTGGGTGGCAGTTATATGGTATGAAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGAACTGGG GTTTCTCTGACTACTGGGGCCAGGGAACCCTG GTCACCGTCTCCTCA<br>SEQ ID NO: 29003 |
| 21-225_16B7 | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEFN<br>SEQ ID NO: 24998 | QVQLVESGGGVVQPGRSLRLSCAASGFTFSSYGMH WVRQAPGKGLEWVAVIWYDESNKYYADSVKGRF TISRDNSKNTLYLQMNSLRAEDTAVYYCARELGFL SDYWGQGTLVTVSS<br>SEQ ID NO: 29004 |

FIGURE 50
(Continued)

| | | | |
|---|---|---|---|
| iPS:394026 | 21-225_16C7 | NA | GACATCCAGATGACCCAGTCTCCATCCTCACT GTCTGCTTCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTCTGCTGCATCCAGTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATAATAGTTACCCATTCA CTTTCGGCCCTGGGACCAAAGTGGATATCAAA | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGTCAT GACCTGGGTCCGCCAGGCTCCAGGGAAGGGGCT GGAGTGGGTCTCAACTATTAGTGGTAGTGGTGGT TGGACATATTATGCAGACTCCGTGAAGGGCCGGT TCACCATTTCCAGAGACAATTCCAAGAACACGCT GTATCTGCAAATGAACAGCCTGAGAGCCGAGA CACGGCCGAATATTACTGTGCCCGCAGCTCCTTG TTTGACTATTGGGGCCAGGGAACCCTGGTCACCG TCTCCTCA |
| | | | SEQ ID NO: 24999 | SEQ ID NO: 29005 |
| | | AA | DIQMTQSPSSLSASVGDRVTITCRASQGISNYLA WFQQKPGKAPKSLISAASSLQSGVPSKFSGSGSG TDFTLTISSLQPEDFATYYCQQYNSYPFTFGPGT KVDIK | EVQLLESGGGLVQPGGSLRLSCAASGFTFSSYVMT WVRQAPGKGLEWVSTISGSGGWTYYADSVKGRFT ISRDNSKNTLYLQMNSLRAEDTAEYYCARSSLFDY WGQGTLVTVSS |
| | | | SEQ ID NO: 25000 | SEQ ID NO: 29006 |
| iPS:394029 | 21-225_1B12 | NA | GACATCCAGATGACCCAGTCTCCATCCTCCCT GTCTGCATCTGTAGGAGACAGAGTCACCATCA CTTGCCAGGCGAGTCAGGACATTAACAACTAT TTAAATTGGTATCAACAGAAACCAGGGAAAG CCCCTAAGCTCCTGATATACGATGCATCCAAT TTGGAAACAGGGGTCCCATCAAGGTTCAGTGG AAGTGGATCTGGGACAGATTTCACTTTCACCA TCAGCAGTCTGCAGCCTGAAGATATTACAACA TATTACTGTCAACAGTATGAAAATCTCCCGAT CACCTTCGGCCAAGGGACACGACTGGAGATTA AA | CAGGTGCAGCTGGTAGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAATTATATATCATGGTGGAAGT AATAAATCCTATGCAGACTCCGTGAAGGGCCGAT TCACCATCTCCAGAGACAATTCCAAGAACATGCT GTATCTGCAAATGAATAGCCTGAGAGCTGAGGA CACGGCTGTGTATTACTGTGTGAGACGGGATAC AGCTATGGCGGGTACGTATGGACGTCTGGGGC CAAGGGGCCACGGTCACCGTCTCCTCA |
| | | | SEQ ID NO: 25001 | SEQ ID NO: 29007 |

FIGURE 50
(Continued)

| | | | |
|---|---|---|---|
| iPS:394033 | 21-225_5F4 | AA | DIQMTQSPSSLSASVGDRVTITCQASQDINNYLN WYQQKPGKAPKLLIYDASNLETGVPSRFSGSGS GTDFTFTISSLQPEDITTYYCQQYENLPITFGQGT RLEIK<br>SEQ ID NO: 25002 | QVQLVESGGGVVQPGRSLRLSCAASGFTFSSYGMH WVRQAPGKGLEWVAIISYAGSNKSYADSVKGRFTI SRDNSKNMLYLQMNSLRAEDTAVYYCVRRGYSY GGYGMDVWGQGATVTVSS<br>SEQ ID NO: 29008 |
| | | NA | GACATCCAGATGACCCAGTCTCCATCCTCCCT GTCTGCATCTGTAGGAGACAGAGTCACCATCA CTTGCCGGGCAAGTCAGGGCATTCGAAATCAT TTAGGCTGGTATCAGCAGAAACCAGGGAAAG CCCCTAAGCGCCTGATCTATGCTGCCTCCAGTT TGCAAAGTGGGGTCCCATCAAGGTTCAGCGGC AGTGGATCTGGGACAGACTTCACTCTCACAGT CAGCAGCCTGCAGCCTGAAGATTTTGCAACTT ATTACTGTCTACAGTATATAATGGTTACCCATTCA CTTTCGGCCCTGGGACCAAAGTGGATATCAAA<br>SEQ ID NO: 25003 | GAGGTGCAGTTGGTGGAGTCTGGGGGAGGCCTG GTCAAGCCTGGGGGGTCCCTGAGACTCTCCTGTG TAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTTTCTGCAAATGAACAGCTGAGAGCCGAGGA CACGGCTGTGTATTACTGTGCGAGAGTTAACAAC TTTGACTACTGGGGCCAGGGAACCCTGGTCACCG TCTCCTCA<br>SEQ ID NO: 29009 |
| | | AA | DIQMTQSPSSLSASVGDRVTITCRASQGIRNHLG WYQQKPGKAPKRLIYAASSLQSGVPSRFSGSGS GTEFTLTVSSLQPEDFATYYCLQYNGYPFTFGPG TKVDIK<br>SEQ ID NO: 25004 | EVQLVESGGGLVKPGGSLRLSCVASGFTFSSYSMN WVRQAPGKGLEWVSSISGSSSYIYYADSVKGRFTIS RDNAKNSLFLQMNSLRAEDTAVYYCARVNNFDY WGQGTLVTVSS<br>SEQ ID NO: 29010 |

FIGURE 50
(Continued)

| | | | | |
|---|---|---|---|---|
| iPS:394035 | 21-225_5G9 | NA | GACATCCAGATGACCCAGTCTCCATCCTCCCT GTCTGCATCTGTAGGAGACAGAGTCACCATCA CTTGCCAGGCGAGTCAGGGCATTAGCAACTCT TTAAATTGGTATCAGCAGAAACCAGGAAAAG CCCCTAAACTCCTGATCTACGATGCATCCAAT TTGGAAACAGGGGTCCCATCAAGGTTCAGTGG AAGTGGAGCTGGGACAGATTTTACTTTCACCA TCAGCAGCCTGCAGCCTGAAGATATTGCAACA TATTACTGTCAACAATATGATAATCTCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGT CAGCCCTCTGATTCACCTTCAGTAATTATGGCAT GCACTGGGTCCGCCAGGCTCCAGGCAAGGGCT GGAGTGGGTGGCAATTATATCATATGCTGAAGT AATAAATACTATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGTGAGACGTATAAC AGCTGTCTCTACTACGGTATGGACGTCTGGGGC CAAGGGACCACGGTCACCGTCTCCTCA |
| | | | SEQ ID NO: 25005 | SEQ ID NO: 29011 |
| | | AA | DIQMTQSPSSLSASVGDRVTITCQASQGISNSLN WYQQKPGKAPKLLIYDASNLETGVPSRFSGSGA GTDFTFTISSLQPEDIATYYCQQYDNLPLTFGGG TKVEIK | QVQLVESGGGVVQPGRSLRLSCAASGFTFSNYGM HWVRQAPGKGLEWVAIISYAGSNKYYADSVKGRF TISRDNSKNTLYLQMNSLRAEDTAVYYCVRRITAR LYYGMDVWGQGTTVTVSS |
| | | | SEQ ID NO: 25006 | SEQ ID NO: 29012 |
| iPS:394037 | 21-225_4F4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCGTCCAGT GTGCAAACTGGGGTCCCATCAAGGTTCAGCGG CAGTGGATCTGGGACAGCAGCCTCACTCACAA TCAGCAGCCTGCAGCCTGAAGATTTTGCAATT TATTACTGTCTACAGCATAATAGTTACCCGCTC ACTTTCGGCGGAGGGACCAAGGTGGAGATCA AA | CAGCTGCAGCTGCAGGAGTCGGGCCCAGGACTG GTGAGGCCTTCGGTGGCTCCGTCCCTCACCTGCA CTGTCTCTGGTGGCTCCATCAGTAGGAGTAGTTA CTACTGGGGCTGGATCCGCCAGCCCCCAGGAAA GGGGCTGGAGTGGATTGGGAATATTATTATAGT CGAGCCACCTACGACAACCCGTCCCTCAAGAGT CGAGTCACCATATCGTAGACACGTCCAAGAACC AGTTCTCCCTGAAGCTGAGCTCTGTGACCGCGC GGACACGGCTGTTTATTACTGTGGGAGACATGGA AAAGACTGGGGCCTTGACTACTGGGGCCAGGGA ACCCTGGTCACCGTCTCCTCA |
| | | | SEQ ID NO: 25007 | SEQ ID NO: 29013 |

FIGURE 50
(Continued)

| | | | |
|---|---|---|---|
| | | AA | DIQMTQSPSSLSASVGDRVTITCRASQGIRNDLG WYQQKPGKAPKRLIYAASSVQTGVPSRFSGSGS GTEFTLTISSLQPEDFAIYYCLQHNSYPLTFGGGT KVEIK | QLQLQESGPGLVRPSETLSLTCTVSGGSISRSSYYW GWIRQPPGKGLEWIGNIYYSGSTYDNPSLKSRVTIS VDTSKNQFSLKLSSVTAADTAVYYCGRHGKDWGL DYWGQGTLVTVSS |
| | | | SEQ ID NO: 25008 | SEQ ID NO: 29014 |
| iPS:394041 | 21-225_5E5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGATTCACCTTCAGTAACTATGTCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTCTCCTCA |
| | | | SEQ ID NO: 25009 | SEQ ID NO: 29015 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDGSNKYYADSVKGR FTISRDNSKNTLYLQMNSLRAEDTAVYYCTREVYS SGWYDYGMDVWGQGTTVTVSS |
| | | | SEQ ID NO: 25010 | SEQ ID NO: 29016 |

FIGURE 50
(Continued)

| | | | | |
|---|---|---|---|---|
| iPS:394043 | 21-225_3B1 | NA | GACATCCAGATGACCCAGTCTCCATCCTCCT GTCTGCATCTGTAGGAGACAGAGTCACCATCA CTTGCCGGGCAAGTCAGAGTATTAATAATTAT TTAAATTGGTATCAGCAGAAACCAGGGAAAG CCCCTAAGCTCCTGATCTATGCTACATCCAGTT TGCAAAAATGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCTTA TTCACTTTCGGCCCTGGGACCAAAGTGGATAT CAAT SEQ ID NO: 25011 | GAGGTGCAGCTGTTGGAGTCTGGGGGAGGCTTG GTACAGCCTGGGGGGTCCCTGAGACTCTCCTGTG CAGCCCTCTGAATTCACCTTTAGCAGCTATGCCAT GAACTGGGTCCGCCAGGCTCCAGGAAGGGCT GGAGTGGGTCTCAGTTATTAGTGGTCGTGGTATT AACACATTCTACGCAGACTCCGTGAAGGGCCGGT TCACCATTTCCAGAGACAATTCCAAGAACACGCT GTATCTGCAAATGAACAGCCTGAGAGCCGAGGA CACGGCCGTATATTACTGTGCGTCCCGTTTAGCA GTGGCTGCTCGGAGGCTTTTGATATCTGGGGCC AAGGGACAATGGTCACCGTCTCTTCA SEQ ID NO: 29017 |
| | | AA | DIQMTQSPSSLSASVGDRVTITCRASQSINNYLN WYQQKPGKAPKLLIYATSSLQNGVPSRFSGSGS GTDFTLTISSLQPEDFATYYCQQSYSTPLFTFGPG TKVDIN SEQ ID NO: 25012 | EVQLLESGGGLVQPGGSLRLSCAASEFTFSSYAMN WVRQAPGKGLEWVSVISGRGINTFYADSVKGRFTI SRDNSKNTLYLQMNSLRAEDTAVYYCASRLAVAG SEAFDIWGQGTMVTVSS SEQ ID NO: 29018 |
| iPS:394045 | 21-225_4H4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCGGGGAAAG CCCCTAAGCTCCTGATCTATGCTGCATCCAGT GTGCAAAGTGGGGTCCCATCAAGGTTCAGCGG CAGTGGATCTGGGACAGATTCACTCTCACAA TCAGCAGCCTGCAGCCTGAAGATTTTGCAATT TATTACTGTCTACAGCATCATAATAGTTACCCGCTC ACTTTCGGCGGAGGGACCAAGGTGGAGATCA AA SEQ ID NO: 25013 | CAGCTGCAGCTGCAGGAGTCGGGCCCAGGACTG GTGAAGCCTTCGGAGACCCTGTCCCTCACCTGCA CTGTCTCTGGTGGCTCCATCAGTAGGAGTAGTTA CTACTGGGGCTGGATCCGCCAGCCCCCAGGGATG GGGCTGGAATGGATTGGAATATTATTATAGTG GGAACACCTACAACAACCCGTCCCTCAAGAGTC GAGTCACCATATCCGTAGACACGTCCAAGAACC AGTTCTCCCTGAAGCTGAACTCTGTGACCGCGC AGACACGGCTGTGTATTACTGTGGGAGACATGGA AAGACTGGGGCCTTGACTACTGGGGCCAGGGA ACCCTGGTCATCGTCTCCTCA SEQ ID NO: 29019 |

FIGURE 50
(Continued)

| | | | |
|---|---|---|---|
| iPS:394047 | | AA | DIQMTQSPSSLSASVGDRVTITCRASQGIRNDLG WYQQKPGKAPKRLIYAASSVQSGVPSRFSGSGS GTEFTLTISSLQPEDFAIYYCLQHNSYPLTFGGGT KVEIK<br>SEQ ID NO: 25014 | QLQLQESGPGLVKPSETLSLTCTVSGGSISRSSYYW GWIRQPPGMGLEWIGNIYYSGNTYNNPSLKSRVTIS VDTSKNQFSLKLNSVTAADTAVYYCGRHGKDWGL DYWGQGTLVIVSS<br>SEQ ID NO: 29020 |
| | | NA | GACATCCAGATGACCCAGTCTCCATCCTCCCT GTCTGCATCTGTAGGAGACAGAGTCACCATCA CTTGCCAGGCGAGTCAGGACATTAACAACTAT TTAAATTGGTATCAGCAGAAACCAGGGAAAG CCCCTAAGCTCTTGATATACGATGCATCCAAT TTGGAAACAGGGGTCCCATCAAGGTTCAGTGG AAGTGGATCTGGGACAGATTTTACTTTCACCA TCAGCAGCCTGCAGCCTGAAGATATTGCAACA TATTACTGTCAACAGTATGATAATCTCCCGAT CACCTTCGGCCAAGGGACACGACTGGAGATTA AA<br>SEQ ID NO: 25015 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAATTATATCATATGTTGAAAT AATAAATACTATGCAGACTCCGTGAAGGGCCGA TTCACCATCTCCAGAGACAATTCCAAGAACACGC TGTATCTGCAAATGAACAGCTGAGAGTTGAGGA CACGGCTGTGTATTACTGTGCGAGACGGGGATAC AGCTATGGCGGGTACGGTCACCGTCACCGTCTCCTCA<br>SEQ ID NO: 29021 |
| 21-225_5E6 | | AA | DIQMTQSPSSLSASVGDRVTITCQASQDINNYLN WCQQKPGKAPKLLIYDASNLETGVPSRFSGSGS GTDFTFTISSLQPEDIATYYCQQYDNLPITFGQGT RLEIK<br>SEQ ID NO: 25016 | QVQLVESGGGVVQPGRSLRLSCAASGFTFSSYGMH WVRQAPGKGLEWVAIISYVGNNKYYADSVKGRFT ISRDNSKNTLYLQMNSLRVEDTAVYYCARRGYSY GGYGMDVWGQGTTVTVSS<br>SEQ ID NO: 29022 |

FIGURE 50
(Continued)

| | | | |
|---|---|---|---|
| iPS:394049 | 21-225_13H5 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAACTGGGGTCCCATCAAGATTCAGCGG CAGTGGATCTGGGACAGATTTCATTCTCACAA TCAGCAGCCTGCAGCCTGAAGATTTTGCAACT TATTACTGTCTACAGCATAATAGTTACCCTCTC ACTTTCGGCGGAGGGACCAAGGTGGAGATCA AA SEQ ID NO: 25017 | CAGCTGCAGCTGCAGGAGTCGGGCCCAGGACTG GTGAAGCCTGCGGAGACCCTGTCCCTCACCTGCA CTGTCTCTGGTGGCTCCATCAGCAGAAGTAGTTA CTACTGGGGCTGGATCCGCCAGCCCCCAGGAA GGGGCTGGAGTGGATTGGGAGTATCTATTATAGT GGGAGCACCTACTACAACCCGTCCCTCAAGAGTC GAGTCACCATATCCGTGGACACGTCCAAGAACC AGTTCTCCCTGAAGCTGAGCTCTGTGACCGCGC AGACACGGCTGTGTATTACTGTGCGAGCCTTAGC AGCAGCTGGGACTTCCAGCACTGGGGCCAGGGC ACCCTGGTCACCGTCTCCTCA SEQ ID NO: 29023 |
| | | AA | DIQMTQSPSSLSASVGDRVTITCRASQGIRNDLG WYQQKPGKAPKRLIYAASSLQTGVPSRFSGSGS GTEFILTISSLQPEDFATYYCLQHNSYPLTFGGGT KVEIK SEQ ID NO: 25018 | QLQLQESGPGLVKPAETLSLTCTVSGGSISRSSYYW GWIRQPPGKGLEWIGSIYYSGSTYYNPSLKSRVTIS VDTSKNQFSLKLSSVTAADTAVYYCASLSSSWDFQ HWGQGTLVTVSS SEQ ID NO: 29024 |
| iPS:394051 | 21-225_9E5 | NA | GACATCCAGATGACCCAGTCTCAATCCTCCCT GTCTGCATCTGTAGGAGACAGAGTCACCATCA CTTGCCGGGCAAGTCAGAGCATTGCCAGTTAT TTAAATTGGTATCAGCAGAAACCAGGGAAAG CCCCTAAACTCCTGATCTATGGTGCAAACAGTT TGCAAAGTGGGGTCCCATCAAGGTTCAGTGGC AGTGGATCTGGGACAGATTTCACTCTCACCAT CAGCAGTCTCCAACAGAGTTACAGTACCCCTTA ACTACTGTCAACAGAGTTACAGTACCCCCTA TTCAGTTTCGGCCCTGGGACCAAAGTGGATAT CAAA SEQ ID NO: 25019 | GAGGTGCAGCTGTTGGAGTCTGGGGGAGGCTTG GTACAGCCTGGGGGGTCCCTGAGACTCTCCTGTG CAGCCTCTGGATTCACCTTTAGCAACTATGCCAT GAACTGGGTCCGCCAGGCTCCAGGGAAGGGGCT GGAGTGGGTCTCAGTTATTAGTGGTGGTGGTGGT AACACATTCTACGCAGACTCCGTGAAGGGCCGGT TCACCATCTCCAGAGACAATTCCAAGAACACGCT GTATCTGCAAATGAACGGCCTGAGAGCCGAGGA CACGGCCGTATATTACTGTGCGTCCCGTATAGCA GTGGCTGGCTGGAGGCTTTTGCTATCTGGGGCC AAGGGACATTGGTCACCGTCTCTTCA SEQ ID NO: 29025 |

FIGURE 50
(Continued)

| | | | | |
|---|---|---|---|---|
| iPS:394053 | 21-225_11F10 | AA | DIQMTQSQSSLSASVGDRVTITCRASQSIASYLN WYQQKPGKAPKLLIYGASSLQSGVPSRFSGSGS GTDFTLTISSLQPEDFATYYCQQSYSTPLFSFGPG TKVDIK<br>SEQ ID NO: 25020 | EVQLLESGGGLVQPGGSLRLSCAASGFTFSNYAMN WVRQAPGKGLEWVSAISGGGGNTFYADSVKGRFT ISRDNSKNTLYLQMNGLRAEDTAVYYCASRIAVAG SEAFAIWGQGTLVTVSS<br>SEQ ID NO: 29026 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGTTCTGGGACAGAATTCACTCTCACAG TCAGCAGCCTGCAGCCTGAAGATTTTGCAACT TATTACTGTCTACAGCATAGTAGTTACCCTCTC ACTTTCGGCGGAGGGACCAAGGTGGAGATCA AA<br>SEQ ID NO: 25021 | CAGCTGCATCTGCAGGAGTCGGGCGGACTG GTGAAGCCTTCGGAGACCCTGTCCTCACCTGCA CTGTCTCTGGTGCTCATCAGCAGAAGTAGTTA CTACTGGGGCTGGATCCGCCAGCCCCCAGGGAA GGGGCTGGAGTGGATTGGAGTATTATTATAGT GGGAGCGCCCAGTACAACCCGTCCCTCAAGAGT CGAGTCACCATATCCGTAGACACGTCCAAGAACC AGTTCTCCCTGACGCTGAGCTCTGTGACCGCCGC AGACACGGCTGTATATTACTGTGCGAGACTGAGC AGCAGCTGGTCTTTTGACTACTGGGGCCAGGGAA CCCTGGTCACCGTCTCCTCA<br>SEQ ID NO: 29027 |
| | | AA | DIQMTQSPSSLSASVGDRVTITCRASQGIRNDLG WYQQKPGKAPKRLIYAASSLQSGVPSRFSGSGS GTEFTLTVSSLQPEDFATYYCLQHSSYPLTFGGG TKVEIK<br>SEQ ID NO: 25022 | QLHLQESGPGLVKPSETLSLTCTVSGASISRSSYYW GWIRQPPGKGLEWIGSIYYSGSAQYNPSLKSRVTIS VDTSKNQFSLTLSSVTAADTAVYYCARLSSSWSFD YWGQGTLVTVSS<br>SEQ ID NO: 29028 |

FIGURE 50
(Continued)

| | | | |
|---|---|---|---|
| iPS:394055 | 21-225_9C8 | NA | GACATCCAGATGACCCAGTCTCCATCCTCACT GTCTGCATCTGTAGGAGACAGAGTCACCATCA CTTGTCGGGCGAGTCAGGGCATTAGTACTTAT TTAGCCTGGTTTCAGCAGAAACCAGGGAAAGC CCCTAAGTCCCTGATCTATGTTGCATCCAGTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATGATAGTTACCCATTCA CTTTCGGCCCTGGGACCAAAGTGGATATCAAA AA SEQ ID NO: 25023 | GAGGTGCAACTGGTGCAGTCTGGGGGAGGCTTG GTACAGCCTGGGGGGTCCCTGAGACTCTCCTGTG TAGTCTCTGGATTCACCTTCAGTAGCCAGAGCAT GAACTGGGTCCGCCAGGCTCCAGGGAAGGGGCT GGAGTGGGTCTCATACATTAGTATTAGTAGTACC ATATACTATGCAGACTCTGTGAAGGGCCGATTCA CCATCTCCAGAGACAATGCCAAGAACTCACTGTA TCTGCAAATGAACAGCCTGAGAGACGAGGACAC GGCTGTGTATTACTGTGCGAGAGAGGAGGTGGAG CCCTTTTGACTCCTGGGGCCAGGGAACCCTGGTC ACCGTCTCCTCA SEQ ID NO: 29029 |
| | | AA | DIQMTQSPSSLSASVGDRVTITCRASQGISYYLA WFQQKPGKAPKSLIYVASSLQSGVPSKFSGSGSG TDFTLTISSLQPEDFATYYCQQYDSYPFTFGPGT KVDIK SEQ ID NO: 25024 | EVQLVESGGGLVQPGGSLRLSCVVSGFTFSSQSMN WVRQAPGKGLEWVSYISISSTIYYADSVKGRFTISR DNAKNSLYLQMNSLRDEDTAVYYCARGGGSPFDS WGQGTLVTVSS SEQ ID NO: 29030 |
| iPS:394057 | 21-225_15H1 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTACATCCAGT TTGCAAAGTGGGGTCCCATCAAGGTTCAACGG CAGTGGATCTGGGACAGAATTCACTCTCACAA TCAGCAGCCTGCAGCCTGAAGATTTTGCAACT TATTACTGTCTACAGCATAGTAGTTACCCGCTC ACTTTCGGCGGAGGGACCAAGGTGGAGATCA AA SEQ ID NO: 25025 | CAGCTGCAGTGCAGGAGTCGGGCCCAGGACTG GTGAAGTTTTCGGAGACCCTGTCCCTCACCTGCA CTGTCTCTGGTGGCTCCATCAGCAGAAGTAGTTA CTACTGGGGCTGGATCCGCCAGCCCCCAGGGAA GGGGCTGGAGTGGATAGGGAATATCTATTATAGT GGGTACCACCATATCCGTAGACACGTCCAAGAAC AGTTCCCTGAAGCTGAGCTCTGTGACCGCCGC AGACACGGCTGTGTATTACTGTGCGAGACATAGC ACCAGCTGTCCCTTGACTACTGGGGCCAGGGAA CCCTGGTCACCGTCTCCTCA SEQ ID NO: 29031 |

FIGURE 50
(Continued)

| | | | |
|---|---|---|---|
| iPS:394059 | 21-225_9E8 | AA | DIQMTQSPSSLSASVGDRVTITCRASQGIRNDLG WYQQKPGKAPKRLIYTASSLQSGVPSRFNGSGS GTEFTLTISSLQPEDFATYYCLQHSSYPLTFGGGT KVEIK<br><br>SEQ ID NO: 25026 | QLQLQESGPGLVKFSETLSLTCTVSGGSISRSSYYW GWIRQPPGKGLEWIGNIYYSGYPYNPSLKSRVTIS VDTSKNQFSLKLSSVTAADTAVYYCARHSTSWSLD YWGQGTLVTVSS<br><br>SEQ ID NO: 29032 |
| | | NA | GACATCCAGATGACCCAGTCTCCATCCTCCCT GTTTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTTATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAGTTACCCGCTC ACTTTCGGCGGAGGGACCAAGGTGGAGATCA AA<br><br>SEQ ID NO: 25027 | CAGGTGCAGCTGGTGGAGTCTGGGGGAGGCGTG GTCCAGCCTGGGAGGTCCCTGAGACTCTCCTGTG AAGCGTCTGGATTCACCTTCAGTAGCTATGGCAT GCACTGGGTCCGCCAGGCTCCAGGCAAGGGCT GGAGTGGGTGGCAGTTATTGGTATGAAGAAAAT AATCAATACTATGCAGACTCCGTGAAGGGCCGAT TCACCATCTCAAGAGACAATTCCAAGAACACGCT GTATCTACAAATGAACAGCCTGAGAGCCGAGGA CACGGCTGTGTATTACTGTGCGAGAGAACTGGGG TTCCGGTCTGACTACTGGGGCCAGGGAACCCTGG TCACCGTCTCCTCA<br><br>SEQ ID NO: 29033 |
| | | AA | DIQMTQSPSSLFASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br><br>SEQ ID NO: 25028 | QVQLVESGGGVVQPGRSLRLSCEASGFTFSSYGMH WVRQAPGKGLEWVAVIWYEENNQYYADSVKGRF TISRDNSKNTLYLQMNSLRAEDTAVYYCARELGFR SDYWGQGTLVTVSS<br><br>SEQ ID NO: 29034 |

FIGURE 50
(Continued)

| | | | |
|---|---|---|---|
| iPS:394061 | 21-225_12D2 | NA | GATATTGTGATGACTCAGTCTCCACTCTCCCTG<br>CCCGTCACCCCTGGTGAGCCGGCCTCCATCTC<br>CTGCAGGTCTAGTCAGAGCCTCCTCCATAGTA<br>ATGGATACAACTATTTGGATTGGTACCTGCAG<br>AAGCCAGGGCAGTCTCCACAGGCTCCTGATCTA<br>TTTGGGTTCTAATCGGGCCTCCGGGTCCCTG<br>ACAGGTTCAGTGGCAGTGGATCAGGCACAGAT<br>TTTACTCTGAAAATCAGCAGAGTGGAGGCTGA<br>GGATGTTGGGGTTTATTACTGCATGCAAGCTC<br>TACAAACTCCTATCACCTTCGGCCAAGGGACA<br>CGACTGGAGATTAAA<br>SEQ ID NO: 25029 | GAGGTGCAGCTGGTGGAGTCTGGGGGAGGCCTG<br>GTCAAGCCTGGGGGGTCCCTGAGACTCTCCTGTG<br>CAGCCTCTGGATTCACCTTCAGTAGCTATAGCAT<br>GAACTGGGTCCGCCAGGCTCCAGGGAAGGGGCT<br>GGAGTGGGTCTCATCCATTAGTAGTAGTAGTAGT<br>TACATATACTACGCAGAGACTCAGTGAAGGGCCGAT<br>TCACCATCTCCAGAGACAACGCCAAGAACTCACT<br>GTATCTGCAAATGAACAGCCTGAGAGCCGAGA<br>CACGGCTGTGTATTACTGTGCGAGATTAGGGGAC<br>TACTGGGGCCAGGGAACCCTGGTCGCCGTCTCCT<br>CA<br>SEQ ID NO: 29035 |
| | | AA | DIVMTQSPLSLPVTPGEPASISCRSSQSLLHSNGY<br>NYLDWYLQKPGQSPQVLIYLGSNRASGVPDRFS<br>GSGSGTDFTLKISRVEAEDVGVYYCMQALQTPIT<br>FGQGTRLEIK<br>SEQ ID NO: 25030 | EVQLVESGGGLVKPGGSLRLSCAASGFTFSSYSMN<br>WVRQAPGKGLEWVSSISSSSYYYADSVKGRFTIS<br>RDNAKNSLYLQMNSLRAEDTAVYYCARLGDYWG<br>QGTLVAVSS<br>SEQ ID NO: 29036 |
| iPS:394063 | 21-225_16A1 | NA | GACATCCAGATGACCCAGTCTCCATCCTCCCT<br>GTCTGCATCTGTAGGAGACAGAGTCACCATCA<br>CTTGCCGGGCAAGTCAGGGCATTAGAAATGAT<br>TTAGGCTGGTATCAGCAGAAAACCAGGGAAAG<br>CCCCTAAGCGCCTGATCTATGCTGCGTCCAGT<br>TTGCAAAGTGGGGTCCCATCAAGGTTCAGCGG<br>CAGTGGATCTGGGACAGAATTCACTCTCACAA<br>TCAGCAGCCTGCAGCCTGAAGATTTTGCAACT<br>TATTACTGTCTACACCATAGTAATTACCCTCTC<br>ACTTTCGGCGGAGGGACCAAGGTGGAGATCG<br>AA<br>SEQ ID NO: 25031 | CAGCTGCAGCTGCAGGAGTCGGGCCCAGGACTG<br>GTGAAGCCTTCGGAGACCCTGTCCTCATTTGTA<br>CTGTCTCTGGGGCTGGATGGCTCATGACAGGAGTAGTTA<br>CTACTGGGGCTGGATCCGCCAGCCCCCAGGGAA<br>GGGGCTGGAGTGGATTGGGAGTATCTATTATAGT<br>GGGAGCGCTATCACAACCGTCCCTCAAGAGTC<br>GAGGCACCATATCCGTAGATACGTCCAAGAACC<br>AGTTCTCCCTGAAGCTGAGCTCTGTGACCGCCGC<br>AGACACGGCTGCGTATTACTGTGCGAGACTGAGC<br>AGCAGCTGGTCCTTGACTACTGGGGCCAGGGAA<br>CCCTGGTCACCGTCTCCTCT<br>SEQ ID NO: 29037 |

FIGURE 50
(Continued)

| | | | |
|---|---|---|---|
| iPS:394065 | | AA | DIQMTQSPSSLSASVGDRVTITCRASQGIRNDLG WYQQKPGKAPKRLIYAASSLQSGVPSRFSGSGS GTEFTLTISSLQPEDFATYYCLHHSNYPLTFGGG TKVEIE<br>SEQ ID NO: 25032 | QLQLQESGPGLVKPSETLSLICTVSGGSIDRSSYYW GWIRQPPGKGLEWIGSIYSGSAYHNPSLKSRGTIS VDTSKNQFSLKLSSVTAADTAAYYCARLSSSWSFD YWGQGTLVTSS<br>SEQ ID NO: 29038 |
| | 21-225_11E2 | NA | GACATCGTGATGACCCAGTCTCCAGACTCCCT GGCTGTGTCTCTGGGCGAGAGAGAGTTTATCCAGC ACTGCAAGTCCAACCAGAGAGTTTATTCTGGTACCA TCCAACAATCACACACTACTTAGCTTGGTACCA GCAGAGACCAGGACAGCCTCCTAAGCTGCTCA TTTACTGGGCATCTCACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTTTAGTACTCCATTCACTTTCGGCCCTGGG ACCAAAGTGGATATCAAA<br>SEQ ID NO: 25033 | CAGGTGCAGGTTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACACTAACAGTG GTAACACAGGCTATGCACAGAAGTTCCAGGCA GAGTCACCATGACCAGGAACACCTCCATAAGCA CAGCCTACATGGACCTGAGCAGCCTGAGATCTGA GGACACGGCCGTATATTACTGTGCGTAGTCAT GGCTGGTTCCTCTTTGACTACTGGGGCCAGGAA TCCTGGTCACCGTCCTCA<br>SEQ ID NO: 29039 |
| | | AA | DIVMTQSPDSLAVSLGERATINCKSNQRVLSSSN NHNYLAWYQQRPGQPPKLLIYWASTRESGVPD RFSGSGSGTDFTLTISSLQAEDVAVYYCQQYFST PFTFGPGTKVDIK<br>SEQ ID NO: 25034 | QVQVVQSGAEVKKPGASVKVSCKASGYTFTNYDI NWVRQATGQGLEWMGWMNTNSGNTGYAQKFQG RVTMTRNTSISTAYMDLSSLRSEDTAVYYCAYSHG WFLFDYWGQGILVTVSS<br>SEQ ID NO: 29040 |

FIGURE 50
(Continued)

| | | | | |
|---|---|---|---|---|
| iPS:394067 | 21-225_12F2 | NA | GACATCCAGATGACCCAGTCTCCATCCTCCCT GTCTGCATCTGTAGGAGACAGAGTCACCATCA CTTGCCGGGCAAGTCAGGACAGTCATTAGAAATGAT TTAGGCTGGTACCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGTAACT TATTACTGTCTACAGCATAATAGTTATCCGTG GACGTTCGGCCAAGGGACCAAGGTGGAAATC AAA SEQ ID NO: 25035 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGTAGATTCCGTGAAAAT AATAAATACTATGTAGATTCCGTGAAGGGCCGAT TCACCATCTCCAGAGACAATTCCAAGAACACGCT GTTTCTGCAAATGAACAGCCTGAGAGCTGAGGA CACGGCTGTGTATTACTGTGTGAGAGAGCTTGCC TGGTCCGAGGACTACTGGGGCCAGGGAACCCTG GTCACCGTCTCCTCA SEQ ID NO: 29041 |
| | | AA | DIQMTQSPSSLSASVGDRVTITCRASQGIRNDLG WYQQKPGKAPKRLIYAASSLQSGVPSRFSGSGS GTEFTLTISSLQPEDFVTYYCLQHNSYPWTFGQG TKVEIK SEQ ID NO: 25036 | QVQLVESGGGVVQPGRSLRLSCAASGFTFSDYGM HWVRQAPGKGLEWVAVIWFDGNNKYYVDSVKGR FTISRDNSKNTLFLQMNSLRAEDTAVYYCVRELAW SEDYWGQGTLVTVSS SEQ ID NO: 29042 |
| iPS:394069 | 21-225_16H1 | NA | GACATCCAGATGACCCAGTCTCCATCCTCCCT GTCTGCATCTGTAGGAGACAGAGTCACCATCA CTTGCCGGGCAAGTCAGGACAGTCATTAGAGATATT TTAGGCTGGTATCAGCAGAAACCAGGGAAAG CCCCTAAGCGCCTGATCTATGCTGCATCCAGT TTGCAAAATGGGGTCCCATCAAGGTTCAGCGG CAGTGGATCTGGGACAGCCTGAAGATTTTGCAACT TCAGCAGCCTGCAGCCTGAAGATTTTGCAACT TATTACTGTCTACAGTATCATAGTTACCATTC ACTTTCGGCCCTGGGACCAAAGTGGATGTCAA A SEQ ID NO: 25037 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGTGCAGAGTAGCAGCC TTTGACTACTGGGGCCAGGGAACCCTGGTCACCG TCTCCTCA SEQ ID NO: 29043 |

FIGURE 50
(Continued)

| | | | |
|---|---|---|---|
| iPS:394071 | 21-225_10C7 | AA | DIQMTQSPSSLSASVGDRVTITCRASQGIRDILG WYQQKPGKAPKRLIYAASSLQNGVPSRFSGSGS GTEFTLTISSLQPEDFATYYCLQYHSYPFTFGPGT KVDVK<br>SEQ ID NO: 25038 | EVQLVESGGGLVKPGGSLRLSCAASGFTFSSYSMN WVRQAPGKGLEWVSSISGSSTYIYYADSVKGRFTIS RDNAKNSLYLQMNSLRAEDTAVYYCARVAAFDY WGQGTLVTVSS<br>SEQ ID NO: 29044 |
| | | NA | GATATTGTGATGACTCAGTCTCCACTCTCCCTG CCCGTCACCCCTGGAGAGCCGGCCTCCATCTC CTGCAGGTCTAGTCAGAGCCTCCTGCATAGTA AGGGATACAACTATTTGGATTGGTACCTGCAG AAGCCAGGGCAGTCTCCACAGGTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTGGAGGCTGA GGATGTTGGGGTTTATTACTGCATGCAAGCTC TACAAACTCCTCTCCACCTTCGGCCAAGGGACA CGACTGGAGATTAAA<br>SEQ ID NO: 25039 | GAGGTGCAGCTGGTGGAGTCTGGGGGAGGCCTG GTCAAGCCGGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAATAAT TACATATACTACGCAGACTCAGTGAAGGGCCGAT TCACCATCTCCAGAGACAACGCCAAGAACTCACT GTATCTGCAAATGAACAGCCTGAGAGCCGAGGA CTCGGCTGTGTATTACTGTGCGAGATTAGGGGTC TACTGGGGCCAGGGAACCCTGGTCACCGTCTCCT CA<br>SEQ ID NO: 29045 |
| | | AA | DIVMTQSPLSLPVTPGEPASISCRSSQSLLHSKGY NYLDWYLQKPGQSPQVLIYLGSNRASGVPDRFS GSGSGTDFTLKISRVEAEDVGVYYCMQALQTPL TFGQGTRLEIK<br>SEQ ID NO: 25040 | EVQLVESGGGLVKPGGSLRLSCAASGFTFSSYSMN WVRQAPGKGLEWVSSISSSNNYIYYADSVKGRFTIS RDNAKNSLYLQMNSLRAEDSAVYYCARLGVYWG QGTLVTVSS<br>SEQ ID NO: 29046 |

FIGURE 50
(Continued)

| | | | | |
|---|---|---|---|---|
| iPS:394073 | 21-225_15C9 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAACAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAG TCAGCAGCCTGCAGCCTGAAGATTTTGCTACT TATTACTGTCTACAACATACTAGTTACCCGCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTA CTACTGGGGCTGGATCCGCCAGCCCCCAGGGAA GGGGCTGGAGTGGATTGGGAATATCTATTATAGT GGGAGCACCTACAACAACCGTCCCTCAAGAGT CGAGTCACCATATCGTAGACACGTCCAAGAACC AGTTCTCCCTGAAGCTGAGCTCTGTGACCGCGC AGACACGGCTGTGTATTACTGTGCGAGACAGGG CAGTGGCTGGGAGGTTGACTACTGGGGCCAGGG AACCCTGGTCACCGTCTCCTCA |
| | | | SEQ ID NO: 25041 | SEQ ID NO: 29047 |
| | | AA | DIQMTQSPSSLSASVGDRVTITCRASQGIRNDLG WYQQKPGKAPKRLIYAASSLQSGVPSRFSGSGS GTEFTLTVSSLQPEDFATYYCLQHTSYPLTFGGG TKVEIK | QLQLQESGPGLVKPSETLSLTCTVSGGSISRSSYYW GWIRQPPGKGLEWIGNIYYSGSTYNNPSLKSRVTIS VDTSKNQFSLKLSSVTAADTAVYYCARQGSGWEV DYWGQGTLVTVSS |
| | | | SEQ ID NO: 25042 | SEQ ID NO: 29048 |
| iPS:394075 | 21-225_8D12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAACAGAAACCAGGGAAAG CCCCTAAGCGCCTGATCTATGCTGCATCCAGT TTGCAAAGTGGGGTCCCATCAAGGTTCAACGG CAGTGGATCTGGGACAGAATTCACTCTCACAA TCAGCAGCCTGCAGCCTGAAGATTTTGCAACT TATTACTGTCTACAGCATAGTAGTTACCCGCTC ACTTTCGGCGGAGGGACCAAGGTGGAGATCA AA | CAGCTGCAGTTGCAGGAGTCGGGCCCAGGACTG GTGAAGTTTTCGGAGACCCTGTCCCTCACCTGCA CTGTCTCTGGTGGCTCCATCAGCAGAAGTAGTTA CTACTGGGGCTGGATCCGCCAGCCCCCAGGGAA GGGGCTGGAGTGGATAGGAATATCTATTATAGT GGGTATCCCTACTACATCCGTCCCTCAAGAGTC GAGTCACCATATCCATAGACACGTCCAAGAACC AGTTCTCCCTGAAGCTGAGCTCTGTGACCGCGC AGACACGGCTGTGTATTACTGTGCGAGACATAGC ACCAGCTGGTCCCTTGACTACTGGGGCCAGGAA CCCTGGTCACCGTCTCCTCA |
| | | | SEQ ID NO: 25043 | SEQ ID NO: 29049 |

FIGURE 50
(Continued)

| | | | |
|---|---|---|---|
| | | AA | DIQMTQSPSSLSASVGDRVTITCRASQGIRNDLG WYQQKPGKAPKRLIYAASSLQSGVPSRFNGSGS GTEFTLTISSLQPEDFATYYCLQHSSYPLTFGGGT KVEIK | QLQLQESGPGLVKFSETLSLTCTVSGGSISRSSYYW GWIRQPPGKGLEWIGNIYYSGYPYYNPSLKSRVTISI DTSKNQFSLKLSSVTAADTAVYYCARHSTSWSLDY WGQGTLVTVSS |
| | | | SEQ ID NO: 25044 | SEQ ID NO: 29050 |
| iPS:394077 | 21-225_8E12 | NA | GACATCCAGATGACCCAGTCTCCATCCTCCCT GTCTGCATCTGTAGGAGACAGAGTCACCATCA CTTGCCGGGCAAGTCAGAGCATTAGTAATTAT TTAAATTGGTATCAGCAGAAACCAGGGAAAG CCCCTAAGCTCCTGATCTATGCTGCATCCAGTT TACAAAGTGGTGGGTCCCATCAAGGTTCAGTGGC AGTGGATCTGGGACAGATTTCACTCTCACCAT CAGCAGTCTGCAACCTGAAGATTTTGCAACTT ACTTCTGTCAACAGAGTTACAGAACCCCCTTT TTCACTTTCGGCCCTGGGACCAAAGTGGATAT CAAA | GAGGTGCAGCTGTTGGAGTCTGGGGGAGGCTTG GTACAGCCTGGGGGGTCCCTGAGACTCTCCTGTG CAGCCTCTGAATTCACCTTTAGCAGCTATGCCAT GAGCTGGGTCCGCCAGGCTCCAGGGAAGGGGCT GGAGTGGGTCTCAATTATTAGTGGTGGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGCGCCGTATGGCA GTGGCTGGCTCGGAGGCTTTGATATCTGGGGCC AAGGGACAATGGTCACCGTCTCTCA |
| | | | SEQ ID NO: 25045 | SEQ ID NO: 29051 |
| | | AA | DIQMTQSPSSLSASVGDRVTITCRASQSISNYLN WYQQKPGKAPKLLIYAASSLQSGVPSRFSGSGS GTDFTLTISSLQPEDFATYFCQQSYRTPFFTFGPG TKVDIK | EVQLLESGGGLVQPGGSLRLSCAASEFTFSSYAMS WVRQAPGKGLEWVSIISGRGGNTFYADSVKGRFTI SRDNSKNTLYLQMNSLRAEDTAVYYCASRMAVAG SEAFDIWGQGTMVTVSS |
| | | | SEQ ID NO: 25046 | SEQ ID NO: 29052 |

FIGURE 50
(Continued)

| | | | |
|---|---|---|---|
| iPS:394079 | 21-225_11F5 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGTCTGATCTATGCTGCATCCAGTGTGCAAAGTGGGGTCCCATCAAGGTTCAGCGGCAGTGGATCTGGGACAGAGAATTCACTCTCACAATCAGCAGCCTGCAGCCTGAAGATTTTGCAATTTATTACTGTCTACAGCATAATAGTTACCCGCTCACTTTCGGCGGAGGGACCAAGGTGGAGATCAA | CAGCTGCAGCTGCAGGAGTCGGGCCCAGGACTGGTGAAGCCTTCGGAGACCCTGTCCCTCACCTGCACTGTCTCTGGTGGCTCCATCAGTAGGAGTAGTTACTACTGGGGCTGGATCCGCCAGCCCCCAGGGAAGGGGCTGGAATGGATTGGAAATATTTATTATAGTGGGAGCACCTACACCAACCGTCCCTCAAGAGTCGAGTCACCATATCCGTAGACACGTCCAAGAACCACTTCTCCCTGAAGCTGAGCTCTGTGACCGCCGCAGACACGGCTGTGTATTACTGTGGGAGACATGGAAAAGACTGGGGCCTTGACAACTGGGGCCAGGGAACCCTGGTCACCGTCTCCTCA |
| | | | SEQ ID NO: 25047 | SEQ ID NO: 29053 |
| | | AA | DIQMTQSPSSLSASVGDRVTITCRASQGIRNDLGWYQQKPGKAPKRLIYAASSVQSGVPSRFSGSGSGTEFTLTISSLQPEDFAIYYCLQHNSYPLTFGGGTKVEIK | QLQLQESGPGLVKPSETLSLTCTVSGGSISRSSYYWGWIRQPPGKGLEWIGNIYYSGSTYTNPSLKSRVTISVDTSKNHFSLKLSSVTAADTAVYYCGRHGKDWGLDNWGQGTLVTVSS |
| | | | SEQ ID NO: 25048 | SEQ ID NO: 29054 |
| iPS:394081 | 21-225_16B3 | NA | GACATCCAGATGACCCAGTCTCCATCCTCCCTGTCTGCATCTGTAGGAGACAGAGTCACCATCACTTGCCAGGCGAGTCAGGACAGTCATTAACAACTATTTAAATTGGTATCAGCAGAAACCAGGGAAGCCCCTAAGCTCCTGATCTACGATGCATCCAATTTGGAAACAGGGGTCCCATCAAGGTTCAGTGGAAGTGGCTCTGGGACAGATTTTACTTTCACCATCAGCAGCCTGCAGCCTGAAGATATTGCAACATATTACTGTCTGCAAGTTGATAATATCTCCCGATCACCTTCGGCCAAGGGACACGACTGGAGATTAAA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATCATATGATGGAAGTAATAAATCCTATGCAGACTCCGTGAAGGGCCGATTCACCATCTCCAGAGACAATTCCAATAACGCTGTATCTGCAAATGAACAGCCTGAGAGCTGAGGACACGGCTGTGTATTACTGTGTGAGACGGGATACAGCTATGGCGGGTATGGTGATGGACGTCTGGGGCCAAGGGGCCACGGTCACCGTCTCCTCA |
| | | | SEQ ID NO: 25049 | SEQ ID NO: 29055 |

FIGURE 50
(Continued)

| | | | | |
|---|---|---|---|---|
| iPS:394083 | | AA | DIQMTQSPSSLSASVGDRVTITCQASQDINNYLN WYQQKPGRAPKLLIYDASNLETGVPSRFSGSGS GTDFTFTISSLQPEDIATYYCQQFDNLPITFGQGT RLEIK<br><br>SEQ ID NO: 25050 | QVQLVESGGGVVQPGRSLRLSCVASGFTFSSYGMH WVRQAPGKGLEWVAVISYAGINKSYADSVKGRFTI SRDNSNNTLYLQMNSLRAEDTAVYYCVRRGYSYG GYGMDVWGQATVTVSS<br><br>SEQ ID NO: 29056 |
| | 21-225_16E6 | NA | GACATCCAGATGACCCAGTCTCCATCCTCCCT GTCTGCATCTGTAGGAGACAGAGTCACCATCA CTTGCCGGGCAAGTCAGAGCATTATCAGTAT TTAAATTGGTATCAGCAGAAACCAGGGAAAG CCCCTAAGTTCCTGATCTATACATCCAGTT TGCAAAGTGGTGGGTCCCATCAAGGTTCAGTGGC AGTGGATCTGGGACAGATTTCACTCTCACCAT CAGTAGTCTGCAACCTGAAGATTTTGCAACTT ACTACTGTCAGCAGAGATTACAGTACCCCGCTC ACTTTCGGCGGAGGGACCAAGGTGGAGATCA AA<br><br>SEQ ID NO: 25051 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGACTCCGTGAAGGGCCGA TAATAAATACTATGTAGACTCCGTGAAGGGCCGA TTCACCATCTCCAGAGACAATTCCAAGAACACGC TGAATCTGCAAATGAACAGCCTGAGAGCCGAGG ACACGGCTGTGTATTACTGTGCGAGAGATCTGAG TATGGGCGGTATGGACGTCTGGGGCCAAGGGAC CACGGTCACCGTCTCCTCA<br><br>SEQ ID NO: 29057 |
| | | AA | DIQMTQSPSSLSASVGDRVTITCRASQSIISYLNW YQQKPGKAPKFLIYTTSSLQSGVPSRFSGSGSGT DFTLTISSLQPEDFATYYCQQTYSTPLTFGGGTK VEIK<br><br>SEQ ID NO: 25052 | QVQLVESGGGVVQPGRSLRLSCAASGFTFSSYGMH WVRQAPGKGLEWVAVIWHDGSNKYYVDSVKGRF TISRDNSKNTLNLQMNSLRAEDTAVYYCARDLSM GGMDVWGQGTTVTVSS<br><br>SEQ ID NO: 29058 |

FIGURE 50
(Continued)

| | | | | |
|---|---|---|---|---|
| iPS:394085 | 21-225_8B11 | NA | GACATCGTGATGACCCAGTCTCCAGACTCCCT GGCTGTGTCTCTGGGCGAGAGGGCCACCATCA ACTGCAAGTCCAGCCAGAATGTTTTATACAAC TCCAACAATAACAACTACTTAGCTTGGTACCA GCAGAAACCAGGACAGCCTCCTAAGCTGCTCA TTTACTGGGCATCTACCCGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATACTCCGTGCAGTTTTGGCCAGGG GACCAAGCTGGAGATCAAA SEQ ID NO: 25053 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCGTGACAAGGGC TTGAGTGGATGGGATGGATGCACCTAACAGTGG TAACACAGGCTATGCACAGAAGTTCAGGGCAG AGTCACCATGACCAGGAACACCTCCAGAAGCAC AGCCTACATGGAGCTGAGCAGCCTGAGATCTGA GGACACGGCCGTGTACTACTGTGCGTATAGCAGT GGCTGGTACTTCTTTGACTACTGGGGCCAGGGAA CCCTGGTCACCGTCTCCTCA SEQ ID NO: 29059 |
| | | AA | DIVMTQSPDSLAVSLGERATINCKSSQNVLYNSN NNNYLAWYQQKPGQPPKLLIYWASTRKSGVPD RFSGSGSGTDFTLTISSLQAEDVAVYYCQQYYTI PCSFGQGTKLEIK SEQ ID NO: 25054 | QVQLVQSGAEVKKPGASVKVSCKASGYTFTNYDIN WVRQAAGQGLEWMGWMHPNSGNTGYAQKFQGR VTMTRNTSRSTAYMELSSLRSEDTAVYYCAYSSG WYFFDYWGQGTLVTVSS SEQ ID NO: 29060 |
| iPS:394087 | 21-225_11A5 | NA | GACATCCAGATGACCCAGTCTCCATCCTCCCT GTCTGCATCTGTAGGAGACAGAGTCACCATCA CTTGCCGGGCAAGTCAGAGTCAGAAACATTTATAGTTAT TTAAATTGGTATCAGCAGAAACCAGGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTACAACCTGAAGATTTTGCAACTT ACTACTGTCAACAGAGTTACAATACCCCCTA TTCACTTTCGGCCCTGGGACCAAAGTGGATAT CAAA SEQ ID NO: 25055 | GAGGTGCAGCTGTTGGAGTCTGGGGGAGACTTG GTTCAGCCTGGGGGGTCCCTGAGACTCTCCTGTG CAGCCTCTGAATTCACCTTTAGCAGTCAGTGCCAT GAGCTGGGTCCGCCAGGCTCCAGGGAAGGGCT GGAGTGGATCTCAGTTATTAGTGGTCGTGGTGTT AACACATTCTACGCAGACTCCGTGAAGGGCCGGT TCACCATCTCCAGAGACAATTCCAAGAACACGCT CTATCTACAAAATGAACAGCCTGAGAGCCGAGGA CACGGCCGTATATTACTGTGCGTCCCGTATCGCA GTGGCTGGCTCGGAGGCTTTTGATATCTGGGGCC AAGGGACAATGGTCACCGTCTCTTCA SEQ ID NO: 29061 |

FIGURE 50
(Continued)

| | | | |
|---|---|---|---|
| iPS:394089 | 21-225_12E6 | AA | DIQMTQSPSSLSASVGDRVTITCRASQNIYSYLN WYQQKPGKAPKLLIYAASSLQSGVPSRFSGSGS GTDFTLTISSLQPEDFATYYCQQSYNTPLFTFGPG TKVDIK<br>SEQ ID NO: 25056 | EVQLLESGGDLVQPGGSLRLSCAASEFTFSSYAMS WVRQAPGKGLEWISVISGRGVNTFYADSVKGRFTI SRDNSKNTLYLQMNSLRAEDTAVYYCASRIAVAGS EAFDIWGQGTMVTVSS<br>SEQ ID NO: 29062 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAGTGAT TTAGGCTGGTATCAGCAGAAACCAGGGAAAG CCCCTAAGCGCCTGATCTATGCTGCATCCAGT TTGCAAAGTGGGGTCCCATCCAAGGTTCAGCGG CAGTGGATCTGGGACAGAGATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br>SEQ ID NO: 25057 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTGACTGGCAT GCACTGGGTCCGCCAGGCTCCAGGCAAGGGGCT GGAGTGGGTGACAGTTATATGGTATGAAGGTCCCGTGAAGGGCCGA AATAAATACTATGCAGACTCCGTGAAGGGCCGA TTCACCATCTCAGAGACGATTCCAAAAACACGC TGTATCTGCAAATGAACAGTCTGAGAGCCGAGG ACACGGCTGTGTATTACTGTGCGAGAGAGCTTGC CTGGTACGAGGACTACTGGGGCCAGGGAACCCT GGTCACCGTCTCCTCA<br>SEQ ID NO: 29063 |
| | | AA | DIQMTQSPSSLSASVGDRVTITCRASQGIRSDLG WYQQKPGKAPKRLLIYAASSLQSGVPSRFSGSGS GTEFTLTISSLQPEDFATYYCLQHNSYPWTFGQG TKVEIK<br>SEQ ID NO: 25058 | QVQLVESGGGVVQPGRSLRLSCAASGFTFSDYGM HWVRQAPGKGLEWVTVIWYDESNKYYADSVKGR FTISRDDSKNTLYLQMNSLRAEDTAVYYCARELAW YEDYWGQGTLVTVSS<br>SEQ ID NO: 29064 |

FIGURE 50
(Continued)

| | | | |
|---|---|---|---|
| iPS:394091 | 21-225_13H3 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA<br>SEQ ID NO: 25059 | CAGGTGCAGCTGGTGGAGTCTGGGGGAGGCTG GTCCAGCCTGGGAGGTCCCTGAGACTCTCCTGTG CAGCGTCTGGATTCACCTTCAGTAGTAGTTATGGCAT GCACTGGGTCCGCCAGGCTCCAGGCAAGGGCT GGAGTGGGTGGCAGTTATTTGGTATGAGGAAAGT AATAAATACTATGTAGACTCCGTGAGGGCCGAT TCACCATCTCCAGAGACAATTCCAAGAGCACGCT GTATCTGCAAATGAACAGCCTGAGAGCCGAGGA CACGGCTGTGTATTACTGTGTGAGAGAACTAGGC TTCCAGTCTGACTTCTGGGGCCAGGGAACCCCGG TCACCGTCTCCTCA<br>SEQ ID NO: 29065 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 25060 | QVQLVESGGGLVQPGRSLRLSCAASGFTFSSYGMH WVRQAPGKGLEWVAVIWYEESNKYYVDSVRGRF TISRDNSKSTLYLQMNSLRAEDTAVYYCVRELGFQ SDFWGQGTPVTVSS<br>SEQ ID NO: 29066 |
| iPS:394093 | 21-225_9D12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br>SEQ ID NO: 25061 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGCAGACTCGTGAAGGGCCGAT TCACCATCTCCAGAGACAATTCCAAGAACACGCT GTATCTGCAAATGAACAGCCTGAGAGCCGAGGA CACGGCTGTGTATTACTGTGTGCAGAGAGCTTGCC TGGTACGAGGACTTCTGGGGCCAGGGAACCCTG GTCACCGTCTCCTCA<br>SEQ ID NO: 29067 |

FIGURE 50
(Continued)

| | | | |
|---|---|---|---|
| iPS:394095 | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPWTFGQG TKVEIK<br>SEQ ID NO: 25062 | QVQLVESGGGVVQPGRSLRLSCAASGFTFSDYGM HWVRQAPGKGLEWVAVIWYDGNNNYYADSVKG RFTISRDNSKNTLYLQMNSLRAEDTAVYYCARELA WYEDFWGQGTLVTVSS<br>SEQ ID NO: 29068 |
| | 21-225_16H4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAAGTTACCCGTGG ACGTTCGGCCAAGGGACCAAGGTGGAAATCA AA<br>SEQ ID NO: 25063 | CAGGTGCAGCTGGTGGAGTCTGGGGGAGGCGTG GTCCAGCCTGGGAGGTCCCTGAGACTCTCCGTG CAGCGTCTGGATTCACCTTCAGTAACTATGGCAT GCACTGGGTCCGCCAGGCTCCAGGCAAGGGGCT GGAGTGGGTGGCAGTTATATGGTATGATGGTAAGT AATAAATACTATGCAGACTCCGTGAAGGGCCGA TTCACCATCTCCAGAGACAATTCCAAGAACATGT TGTATCTGCAAATGAACAGCCTGAGAGCCGAGG ACACGGCTGTGTATTACTGTGCGCGAGAATGGG CTGGACCGATGACTGCTGGGGCCAGGGAACCCT GGTCACCGTCTCCTCA<br>SEQ ID NO: 29069 |
| | | AA | DIQMTQSPSSLSASVGDRVTITCRASQGIRNDLG WYQQKPGKAPKRLIYTASSLQSGVPSRFSGSGSG TEFTLTISSLQPEDFATYYCLQHNSYPWTFGQGT KVEIK<br>SEQ ID NO: 25064 | QVQLVESGGGVVQPGRSLRLSCAASGFTFSNYGM HWVRQAPGKGLEWVAVIWYDVSNKYYADSVKGR FTISRDNSKNMLYLQMNSLRAEDTAVYYCAREMG WTDDCWGQGTLVTVSS<br>SEQ ID NO: 29070 |

FIGURE 50
(Continued)

| | | | | |
|---|---|---|---|---|
| iPS:394097 | 21-225_16G7 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAACATAATAGTTACCCGTGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCCTCTGGATTCACCTTCACTGACTATGGCATGCACTGGGTCCGCCAGGCTCCAGGCAAGGGGCTGGAGTGGGTGGCAGTTATTTGGTATGATGAAAATAATGAATACTATGCAGACTCCGTGAAGGGCCGATTCACCATCTCCAGAGCCAATTCCAAGAACACGCTGTATCTGCAAATGAACAGCCTGAGAGCCGAGGACACGGCTGTGTATTACTGTGCGAGAGAGCTTGCCTGGTACGAGGACTACTGGGGCCAGGGAACCCTGGTCACCGTCTCCTCA |
| | | | SEQ ID NO: 25065 | SEQ ID NO: 29071 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKVEIK | QVQLVESGGGVVQPGRSLRLSCAASGFTFTDYGMHWVRQAPGKGLEWVAVIWYDENNEYYADSVKGRFTISRANSKNTLYLQMNSLRAEDTAVYYCARELAWYEDYWGQGTLVTVSS |
| | | | SEQ ID NO: 25066 | SEQ ID NO: 29072 |
| iPS:398470 | 21-225_14B7 | NA | TCCTATGAGCTGACTCAGCCACCCTCAGTGTCCGTGTCCCCAGGACAGACGGCCAGCATCACCTGCTCTGGAGATAAATTGGGGAATAAATATGCTTACTGGTATCAGCAGAAGCCAGGCCAGTCCCCTGTGCTGGTCATCTATCAAGATAGAAAGCGGCCCTCAGGGATCCCTGAGCGATTCTCTGGCTCCAACTCTGGGAACACAGCCACTCTGACCATCAGCGGACCCAGATATGGAACAACAGCACTGTGGTATTCGGCGGAGGGACCAAGCTGACCGTCCTA | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGCCTTGAGTGGATGGGATGGATCAACCCTAACAGTGGTGGCACAAACTATGCACAGAAGTTTCAGGGCAGGGTCACCATGACCAGGGACACGTCCATCAGCACAGCCTACATGGAGCTGAGCAGGCTGAGATCTGAAGACACGGCCGTGTATTTCTGTGCGAGGTCGTTTTCTATGGTTCGGGGAGTTATTATAACGAATTTGACTACTGGGGCCAGGGAACCCTGGTCACCGTCTCCTCA |
| | | | SEQ ID NO: 25067 | SEQ ID NO: 29073 |

FIGURE 50
(Continued)

| | | | |
|---|---|---|---|
| | | AA | SYELTQPPSVSVSPGRTASITCSGDKLGNKYAYWYQQKPGQSPVLVIYQDRKRPSGIPERFSGSNSGNTATLTISGTQTMDEADYYCQAWNNSTVFGGGTKLTVL | QVQLVQSGAEVKKPGASVKVSCKASGYTFTGYYMHWVRQAPGQGLEWMGWINPNSGGTNYVQKFQGRVTMTRDTSISTACMELSRLKSDDTAVYFCARSFFYGSGSYYNEFDYWGQGTLVTVSS |
| | | | SEQ ID NO: 25068 | SEQ ID NO: 29074 |
| iPS:398472 | 21-225_16E4 | NA | CCCTATGAGCTGACTCAGCCACCCTCAGTGTCCGTGTCCCAGGACAGCAGCCATCACCTGCTCTGGAGATAAATTGGGGGATAAATATGTTTACTGGTATCAGCAGAAGTCAGGCCAGTCCCCTGTGCTGGTCATCTATCAAGATAGCAAGCGGCCCTCAGGGATCCCTGAGCGATTCTCTGGCTCCAACTCTGGAAACACAGGCTATGAGGCTGACTATTCGGGACCCAGGCGTGGGACAGCAGCACTGTGGTTTTCGGCGGAGGGACCAAGCTGACCGTCCTA | GAGGTGCAGCTGTTGGAGTCTGGGGGAGGCTTGATACAGCCTGGGGGGTCCCTGAGACTCTCCTGTGCAGCCTCTGGATTCACCTTTAGTAGCTATGTCATGAGCTGGGTCCGCCAGGCTCCAGGGAAGGGGCTGGAGTGGGTCTCCACTATTAGTGTTGGTGGTGGTACCACATACTACGCAGACTCCGTGAAGGGCCGGTTCACCATCTCCAGAGACAATTCCAAGAATACGCTGTATCTGCAAATGAACAGCCTGAGAGCCGAGGACACGGCCGTATATTACTGTGCGAAATGGGGACGTGGCAACAGCTATGAGTACTACTACGGTATGGACGTCTGGGGCCAAGGGACCACGGTCACCGTCTCCTCA |
| | | | SEQ ID NO: 25069 | SEQ ID NO: 29075 |
| | | AA | PYELTQPPSVSVSPGQTASITCSGDKLGDKYVYWYQQKSGQSPVLVIYQDSKRPSGIPERFSGSNSGNTAALTISGTQAMDEADYYCQAWDSSTVVFGGGTKLTVL | EVQLLESGGGLIQPGGSLRLSCAASGFTFSSYVMSWVRQAPGKGLEWVSTISVGGGTTYADSVKGRFTISRDNSKNTLYLQMNSLRAEDTAVYYCAKWGRGNSYEYYYGMDVWGQGTTVTVSS |
| | | | SEQ ID NO: 25070 | SEQ ID NO: 29076 |

FIGURE 50
(Continued)

| | | | | |
|---|---|---|---|---|
| iPS:398474 | 21-225_17B10 | NA | GACATCCAGATGACCCAGTCTCCATCCTCCCT ATCTGCATCTGTAGGAGACAGAGTCACCATCA CTTGCCGGGTCAAGTCAGAGACATTAACAGCTAT TTAAATTGGTATCAGCAGAAACCTGGGAAAGC CCCTAAGCTCCTGATCTTTGCTGCATCCAGTT GCACAGTGGGGTCCCATCAAGGTTCAGTGGCA GTGGATCTGGGACGGATTTCACTCTCACCATC AGCAGTCTGCAACCTGAAGATTTTGCAACTTA CTACTGTCAACAGGGTTACAATACCCCACGT GGACGTTCGGCCAAGGGACCAAGGTGGAAAT CAAT SEQ ID NO: 25071 | GAGGTGCAGCTGTTGGAGTCTGGGGAGGCTTG GTACAGCCTGGGGGGTCCCTGAGACTCTCCTGTG CAGCCTCTGGATTCACCTTTAGAAGCTATGCCAT GAGCTGGGTCCGCCAGGCTCCAGGGAAGGGCT GGAGTGGGTCTCAGTTATTAGTGGTAGTGGTGGT AACACATACTTCGCAGACTCCGTGAAGGGCCGGT TCACCATCTCCAGAGACACAATTCCAAGAACACGCT GTATCTGCAAATGGACAGCCTGAGAGCCGAGGA CACGGCCGTATATTACTGTGCGAAAAGGGGTATA CCAGAGGGCTGATGCTTTTGATATCTGGGGCCAAG GGACAATGGTCACTGTCTCTTCA SEQ ID NO: 29077 |
| | | AA | DIQMTQSPSSLSASVGDRVTITCRSSQSINSYLNW YQQKPGKAPKLLIFAASSLHSGVPSRFSGSGSGT DFTLTISSLQPEDFATYYCQQGYNTPTWTFGQGT KVEIN SEQ ID NO: 25072 | EVQLLESGGGLVQPGGSLRLSCAASGFTFRSYAMS WVRQAPGKGLEWVSVISGSGGNTYFADSVKGRFTI SRDNSKNTLYLQMDSLRAEDTAVYYCAKRGIPEAD AFDIWGQGTMVTVSS SEQ ID NO: 29078 |
| iPS:398476 | 21-225_17C1 | NA | GACATCCAGATGACCCAGTCTCCATCCTCCCT GTCTGCATCTGTAGGAGACAGAGTCACCATCA CTTGCCGGGCAAGTCAGAGACAGTCAACGACTAT TTAAATTGGTATCAGCAGAAACCAGGGAAAG CCCCTAAGCTCCTGATCTATGCTGCATCCAATT TGCAAAGTGGGGTCCCAGCAAGGTTCAGTGGC AGTCGATCTGGGACAGATTTCACTCTCACCAT CAGCAGTCTGCAACCTGAAGATTTTGCAACTT ACTACTGTCAACAGACTTACAATACCCCCTCCG GAGCGCAGTTTTGGCCAGGGGACCAAGCTGG AGATCAAA SEQ ID NO: 25073 | GAGGTGCAGCTGTTGGAGTCTGGGGGAGGCTTG GAACAGCCGGGGGGTCCCTGAGACTCTCCTGTG CAGCCTCTGGATTCACCTTTAGCAGTCATGCCAT GAGCTGGGTCCGCCAGGCTCCAGGGAAGGGCT GGAGTGGGTCTCAGTTATTAGTGGTAGTGGTGGT ACCACATTCTACGCAGACTCCGTGAAGGGCCGGT TCACCATCTCCAGAGACAATTCCAAGAACACGCT GTATCTGCAAATGAGCAGCCTGAGAGCCGAGGA CACGGCCGTATATTCTGTGCCCGATATTGTAGT AGTACCAGGTGTCCTTATGATGCTTTGATATCT GGGGCCAAGGGACAAATGGTCACCGTCTCCTCA SEQ ID NO: 29079 |

FIGURE 50
(Continued)

| | | | |
|---|---|---|---|
| | | AA | DIQMTQSPSSLSASVGDRVTITCRASQNINDYLN WYQQKPGKAPKLLIYAASNLQSGVPARFSGSRS GTDFTLTISSLQPEDFATYYCQQTYNTPPERSFG QGTKLEIK<br><br>SEQ ID NO: 25074 | EVQLLESGGGLEQPGGSLRLSCAASGFTFSSYAMS WVRQAPGKGLEWVSISGSGGTTFYADSVKGRFTI SRDNSKNTLYLQMSSLRAEDTAVYFCARYCSSTRC PYDAFDIWGQGTMVTVSS<br><br>SEQ ID NO: 29080 |
| iPS:398478 | 21-225_17C10 | NA | GACATCCAGATGACCCAGTCTCCATCCTCCA GTCTGCATCTGTAGGAGACAGAGTCACCATCA CTTGCCGGGCGAGTCAGGGCATTAGCAATTAT TTAGCCTGGTATCAGCAGAAACCAGGGAGAGT TCCTAAGCTCCTGATCTATGCTGCATCCACTTT GCAATCAGGGGTCCCATCTCGGTTCAGTGGCA GTGGATCTGGGACAGATTTCACTCTCACCATC AGCAGCCTGCAGCCTGACGATGTTGCAACTTA TTACTGTCAAAAGTATAACAGTGCCCCTCCGC TCACCTTCGGCCAAGGGACACGACTGGAGATT AAA<br><br>SEQ ID NO: 25075 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATGTACTACGCAGACTCAGTGAAGGGCCGAT TCACCATCTCCAGAGACAACGCCAAGAACTCACT GTATCTGCAAATGAACAGCCTGCAGCCGAGGA CACGGCTCTGTATTACTGTGCGAGAGATCGTGGG AGCTCCTGGGGCCAGGGAACCCTGGTCACCGTCT CCTCA<br><br>SEQ ID NO: 29081 |
| | | AA | DIQMTQSPSSQSASVGDRVTITCRASQGISNYLA WYQQKPGRVPKLLIYAASTLQSGVPSRFSGSGS GTDFTLTISSLQPDDVATYYCQKYNSAPPLTFGQ GTRLEIK<br><br>SEQ ID NO: 25076 | EVQLVESGGGLVKPGGSLRLSCAASGFTFSSYSMN WVRQAPGKGLEWVSSISGSSSYMYYADSVKGRFTI SRDNAKNSLYLQMNSLRAEDTALYYCARDRGSSW GQGTLVTVSS<br><br>SEQ ID NO: 29082 |

FIGURE 50
(Continued)

| | | | |
|---|---|---|---|
| iPS:398480 | 21-225_17G4 | NA | GACATCCAGATGACCCAGTCTCCATCCTCCT GTCTGCATCTGTAGGAGACAGAGTCACCATCA CTTGCCGGACAAGTCAGAATATTAGCAACTAT TTAAATTGGTATCAGCAGAAACCAGGAAAAG CCCCTAAGCTCCTGATCTATGTTGCGTCCAGTT TCCCAAGTGGGGTCCCATCAAGGTTCAGTGGC AGTGGATCTGGGACAGAGTTCACTCTCACCAT CAGCAGTCTGCAACCTGAAGATTTTGCAACTT ACTACTGTCAACAGAGTAACTTTTTCCCGTC ACTTTCGGCGGAGGGACCAAGGTGGAGATCAT A | CAGGTGCAGTTGGTGCAGTCTGGGGCTGAGGTGA AGAAGCCTGGGGCCTCAGTGAAGGTCTCCTGCA AGACTTCTGGATACACCTTCACCGACTATTATAT GCACTGGGTGCGACAGGCCCCTGGACAAGGGCT TGAGTGGATGGGATGGATCAACCCTAACAGTGGT GGCACAAACTATGAACAGAAGTTCAGGGCAGG GTCACCATGACCAGGGACACGTCCATCAGCACA GCCTACATGGAACTGAGTAGGCTGAGATCTGAC GACACGGCCGTGTATTACTGTGCGAGTGGATACA GCTATGGGTACAACTGGTTCGACCCCTGGGGCCA GGGAACCCTGGTCACCGTCTCCTCA |
| | | | SEQ ID NO: 25077 | SEQ ID NO: 29083 |
| | | AA | DIQMTQSPSSLSASAGDRVTITCRTSQNISNYLN WYQQKPGKAPKLLIYVASSFPSGVPSRFSGSGSG TEFTLTISSLQPEDFATYYCQQSNFFPLTFGGGTK VEII | QVQLVQSGAEVKKPGASVKVSCKTSGYTFTDYYM HWVRQAPGQGLEWMGWINPNSGGTNYEQKFQGR VTMTRDTSISTAYMELSRLRSDDTAVYYCASGYSY GYNWFDPWGQGTLVTVSS |
| | | | SEQ ID NO: 25078 | SEQ ID NO: 29084 |
| iPS:398482 | 21-225_17H6 | NA | GACATCCAGATGACCCAGTCTCCATCCTCACT GTCTGCATCTGTAGGAGACAGAGTCACCATCA CTTGTCGGGCGAGTCGGACAGATTAGCAATTAT TTAGCCTGGTTTCAGCAGAAACCAGGGAAAGC CCCTAAGTCCCTGATCTCTACTGCATCCAGTTT GCAAAGTGGGGTCCCATCAAGGTTCAGTGGCA GTGGATCTGGGACAGATTTCACTCTCACCATC AGCAGCCTGCAGCCTGAAGATTTTGCAATTTA TTACTGTCCAACAGTATCATAGTTACCATTCA CTTTCGGCCCTGGGACCAAAGTGGATATCCAA | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTTCAAATGAACAGCCTCAAGAACTCACT GTATCTGCAAATGAACAGCCTGTGCGAGAGCCGAGGA CACGGCTGTGTATTACTGTGCGCAGAGTGGCTTCA TTTGACTACTCGGGCCAGGGAACCCTGGTCACCG TCTCCTCA |
| | | | SEQ ID NO: 25079 | SEQ ID NO: 29085 |

FIGURE 50
(Continued)

| | | | |
|---|---|---|---|
| iPS:398484 | | AA | DIQMTQSPSSLSASVGDRVTITCRASRDISNYLA WFQQKPGKAPKSLISTASSLQSGVPSKFSGSGSG TDFTLTISSLQPEDFAIYYCQQYHSYPFTFGPGTK VDIQ<br>SEQ ID NO: 25080 | EVQLVESGGGLVKPGGSLRLSCAASGFTFSSYSMN WVRQAPGRGLEWVSSISGSSSYIYYADSVKGRFTIF RDNAKNSLYLQMNSLRAEDTAVYYCARVASFDY WGQGTLVTVSS<br>SEQ ID NO: 29086 |
| | | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGGAAAGTGGGGTCCCATCCAAGGTTCAGCGG CAGTGGATCTGGGACAGATTCACTCTCACAG TCAGCAGCCTGCAGCCTGAAGATTTTGCAACT TATTACTGTCTACATCATAATAATTACCTCCCC ATCACCTTCGGCCAAGGGACACGACTGGAGAT TAAA<br>SEQ ID NO: 25081 | CAGGTGCAACTGGTGCAGTCTGGGGCTGAGGTG AAGAAGCCTGGGGCCTCCGTGAAGGTCTCCTGCA AGGCTTCTGGATACACCTTCACCGGCTACTATTT GCACTGGGTGCGACAGGCCCCTGGACAAGGGCT TGAGTGGCTGGGATGGATCAACCCTAACAGTAAT GGCACAATCTCTGCACAGAAGTTTCAGGGCAGG GTCACCATGACCAGGGACACGTCCATCAGCACA GCCTACATGGAGCTGAGCAGGCTGATATCTGACG ACACGGCCGTATATTACTGTGCGAGAGATGGTAC CAGTCGCTTGACTACTGGGGCCAGGGAACCCTG GTCACCGTCTCCTCA<br>SEQ ID NO: 29087 |
| | 21-225_18D4 | AA | DIQMTQSPSSLSASVGDRVTITCRASQGIRNDLG WYQQKPGKAPKRLIYAASSLESGVPSRFSGSGSG TEFTLTVSSLQPEDFATYYCLHHNNYLPITFGQG TRLEIK<br>SEQ ID NO: 25082 | QVQLVQSGAEVKKPGASVKVSCKASGYTFTGYYL HWVRQAPGQGLEWLGWINPNSNGTISAQKFQGRV TMTRDTSISTAYMELSRLISDDTAVYYCARDGTSSL DYWGQGTLVTVSS<br>SEQ ID NO: 29088 |

FIGURE 50
(Continued)

| | | | | |
|---|---|---|---|---|
| iPS:398486 | 21-225_19A1 | NA | GACATCCAGATGACCCAGTCTCCATCCTCCT GTCTGCATCTGTAGGAGACAGAGTCACCATCA CTTGCCGGGCAAGTCAGAGTCATTACCAGTAT TTAAATTGGTATCAGCAGAAACCAGGAAAG CCCCTAAGTTCCTGATCTATGCTACATCCAATC TCCAAAGTGGGGTCCCATCAAGGTTCAGTGGC AGTGGATCTGGGACAGATTTCACTTTTACCAT CAGCAGTCTGCAACCTGAAGATTTTGCAATTT ACTACTGTCAACAGAGTTACAACTTCCCGCTC ACTTTCGGCGGAGGGACCAAGGTGGAGATCA AA | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAATCCTAACAGTGG TGGCACAAACTATGCACAGAAGTTTCAGGGCAG GGTCACCATGACCAGGACACGTCCATCAGCAC AGCCTACATGGAGCTGAGCAGGCTGAGATCTGA CGACACGGCCGTGTATTACTGTGCGAGTGGATAC AGCTATGGGTACAACTGGTTCGACCCCTGGGGCC AGGGAACCCTGGTCACCGTCTCCTCA |
| | | | SEQ ID NO: 25083 | SEQ ID NO: 29089 |
| | | AA | DIQMTQSPSSLSASVGDRVTITCRASHTITSYLN WYQQKPGKAPKFLIYATSNLQSGVPSRFSGSGS GTDFTFTISSLQPEDFAIYYCQQSYNFPLTFGGGT KVEIK | QVQLVQSGAEVKKPGASVKVSCKASGYTFTGYYM HWVRQAPGQGLEWMGWINPNSGGTNYAQKFQGR VTMTRDTSISTAYMELSRLRSDDTAVYYCASGYSY GYNWFDPWGQGTLVTVSS |
| | | | SEQ ID NO: 25084 | SEQ ID NO: 29090 |
| iPS:398488 | 21-225_19F6 | NA | TCCTATGAGCTGACTCAGCCACCCTCAGTGTC CGTGTCCCCAGGACAGACAGTCAGCATCACCT GCTCTGGAGATAAATTGGGGGATAAATATGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGATGAGGCTGACTATT ACTGTCAGGCGTGGGACAACACTGTGGTA TTCGGCGGAGGGACCAAGCTGACCGTCCTA | GAGGTGCAGCTGGTGGAGTCTGGGGGAGGCTTG GTGAAGCCTGGGGGGTCCTTAGACTCTCCTGTG CAGCCTCTGGATTCACTTTCAGTAACGCTGGAT GAACTGGGTCCGCCAGGCTCCAGGAAGGGCT GGAGTGGGTTGGCCGTATTAAAAGCAAAACTGA TGTTGGGACAACAGACTACGCTGCACCGTGAA AGGCAGATTCACCATCTCAAGAGATGATTCAAA AAACACGTGTATCTGCAAATGAACAGCCTGAA AACCGAGGACACAGCCGTGTATTACTGTACCACA GATACGGGTCCTATAGCAGCTCGTCTGCTTACT ACTACTATTAGCTATGGACGTCTGGGGCCACGG GACCACGGTCACCGTCTCCTCA |

FIGURE 50
(Continued)

| | | | SEQ ID NO: 25085 | SEQ ID NO: 29091 |
|---|---|---|---|---|
| iPS:398490 | 21-225_21D12 | AA | SYELTQPPSVSVSPGQTVSITCSGDKLGDKYACW YQQKPGQSPVLVIYQDSKRPSGTPERFSGSNSGN TATLTISGTQAMDEADYYCQAWDNNTVFGGG TKLTVL | EVQLVESGGGLVKPGGSLRLSCAASGFTFSNAWM NWVRQAPGKGLEWVGRIKSKTDGGTTDYAAPVK GRFTISRDDSKNTLYLQMNSLKTEDTAVYYCTTDT GPIAARLAYYYYAMDVWGHGTTVTVSS |
| | | | SEQ ID NO: 25086 | SEQ ID NO: 29092 |
| | | NA | TCCTATGAGCTGACTCAGCCACCCTCAGTGTC CGTGTCCCCAGGACAGACAGCCAGCATCACCT GCTCTGGAGATAAATTGGGGACAAGTATGCT TACTGGTATCAGCAGAAGCCAGGCCAGTCCC TGTGTTGGTCATCTATCAAGATAGAAAGAGGC CCTCAGGGATCCCGAGCGATTCTCTGGCTCC AACTCTGGGAACACAGCCACTCTGACCATCAG CGGGACCCAGGCTATGGATGAGGCTGACTTTT ACTGTCAGGCGTGGGACAACAGCACTGTGGTA TTCGGCGGAGGGACCAAGGCTGACCGTCCTA | CAGGTGCAGCTGGTGCAGTCTGGGGCTGAGGTG AAGAAACCTGGGGCCTCAGTGAAGGTCTCCTGC AAGGCTTCTGGATACACACCTTCACCGACTACTA AGGCTTCTGGATACACACCTTCACCGACTACTATA TTCACTGGGTGCGACAGGCCCCTGGACAAGGCT TGAGTGGATGGGATGGATCAACCTAACAGTGGT GGGACAAACAATGCACAGAAGTTTCAGGGCAGG GTCACCATGACCAGGACACGTCATCAGTACA GCCTACATGAGCTGAGCAGGCTGAGATCTGAC GATACGGCCGTGTATTCCTGTGCGAGGTCGTATT ACTATGGTTCGGGGACTTATTATAACGAATTTGA CTACTGGGGCCAGGGAACCCTGGTCACCGTCTCC TCA |
| | | | SEQ ID NO: 25087 | SEQ ID NO: 29093 |
| | | AA | SYELTQPPSVSVSPGQTASITCSGDKLGNKYAY WYQQKPGQSPVLVIYQDRKRPSGIPERFSGSNSG NTATLTISGTQAMDEADFYCQAWDNSTVFGG GTRLTVL | QVQLVQSGAEVKKPGASVKVSCKASGYTFTFDYYIH WVRQAPGQGLEWMGWINPNSGGTNNAQKFQGRV TMTRDTSISTAYMELSRLRSDDTAVYSCARSYYYG SGTYNEFDYWGQGTLVTVSS |
| | | | SEQ ID NO: 25088 | SEQ ID NO: 29094 |

FIGURE 50
(Continued)

| | | | |
|---|---|---|---|
| iPS:398494 | 21-225_21H4 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ACTCTGTCTCCTGGTACCAACAGCACCCAGAC AAAGCCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAGTCATATACAAGGAGCAG CACTGTGGTATTCGGCGGAGGGACCAAGCTGA CCGTCCTA | GAGGTGCAGCTGTTGGAGTCTGGGGGAGGCTTG GTACAGCCTGGGGGGTCCCTGAGACTCTCCTGTG CAGCCTCTGATTCACCTTTAGCAGTCAGTATGCCAT GAGCTGGGTCCGCCAGGCTCCAGGGAAGGGGCT GGAGTGGGTCTCAGCTCTTAGTGGTCGTGGTGGT AGCACATACTACGCAGACTCCGTGAAGGGCCG TTCACCATCTCCAGAGACAATTCAAGAACACGC TGTATCTGCAAATGAACAGCCTGAGAGCCGAGG ACACGGCCGTATATTACTGTGCGAAATGGGGAC GTGGATACAGCTATGAGTACTACTACGGTATGA CGTCTGGGGCCAAGGGACCACGGTCACCGTCTCC TCA |
| | | | SEQ ID NO: 25089 | SEQ ID NO: 29095 |
| | | AA | QSALTQPASVSGSPGQSITISCTGTSSDVGGYNSV SWYQQHPDKAPKLMIYEVSNRPSGVSNRFSGSK SGNTASLTISGLQAEDEADYYCSSYTRSSTVVFG GGTKLTVL | EVQLLESGGGLVQPGGSLRLSCAASGFTFSSYAMS WVRQAPGKGLEWVSALSRGGSTYYADSVKGRFT ISRDNSKNTLYLQMNSLRAEDTAVYYCAKWGRGY SYEYYYGMDVWGQGTTVTVSS |
| | | | SEQ ID NO: 25090 | SEQ ID NO: 29096 |
| iPS:398496 | 21-225_22D2 | NA | GACATCGTGATGACCCAGTCTCCAGACTCCCT GGCTGTGTCTCTGGGCGAGAGGGCCACCATCA CCTGCAAGTCCAGCCAGAGTGTTTTACACAGC TCCAACAATAACAACTACTTAGCTTGGTACCA GCAGAAACCAGGACAGCCTCCTAAGCTACTCA TTTACTGGGCATCTACCCGGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTTCTGTCAGCAA TATTATAGTACTCCGTGCAGTTTGGCCAGGG GACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCATAAATTATGATA TCAACTGGGTGCGACAGGCCACTGGACAAGGC TTGAGTGGATGGGATGGATGCACCTGACAGTGG TAACACAGGCTATGCACAGAAGTTCCAGGCAG AGTCACCATGACCAGGAACACCTCCATAAGCAC AGCCTACATGGAGCTGAGCAGTTTGAGATCTGAG GACACGGCCGTGTATTATTGTGCGTATAGTAGTG GCTGGTACTACTTTGACTACTGGGGCCAGGGAAC CCTGGTCACCGTCTCCTCA |
| | | | SEQ ID NO: 25091 | SEQ ID NO: 29097 |

FIGURE 50
(Continued)

| | | | |
|---|---|---|---|
| iPS:398498 | 21-225_22E6 | AA | DIVMTQSPDSLAVSLGERATITCKSSQSVLHSSN NNNYLAWYQQKPGQPPKLLIYWASTRKSGVPD RFSGSGSGTDFTLTISSLQAEDVAVYFCQQYYST PCSFGQGTKLEIK<br>SEQ ID NO: 25092 | QVQLVQSGAEVKKPGASVKVSCKASGYTFINYDIN WVRQATGQGLEWMGWMHPDSGNTGYAQKFQGR VTMTRNTSISTAYMELSSLRSEDTAVYYCAYSSGW YYFDYWGQGTLVTVSS<br>SEQ ID NO: 29098 |
| | | NA | TCCTATGAGCTGACTCAGCCACCCTCAGTGTC CGTGTCCCCAGGACAGAGCCAGCATCACCT GCTCTGAGATAAATTGGGGAGAAATATGCT TGCTGGTATCAGCAGAAGCCAGGCCAGTCCCG TGTGTTGGTCATCTATCAAGATAGAAGCGGC CCTCAGGGATCCCTGAGCGATACTCTGGCTCC AACACTGGGAACACAGCCACTCTGACCATCAG CGGGACCCAGGCTATGAGGATGAGGCTGACTATT ACTGTCAGGGCGTGGGACAGCAGCACTGCGGTA TTCGGCGGAGGGACCAAGCTGACCGTCCTA<br>SEQ ID NO: 25093 | CAGATCACCTTGAAGGAGTCTGGTCCTACGCTGG TGAAACCCACACAGACCCTCACGCTGACCTGCAC CTTCTCTGGGTTCTCACTCAGCACTGGTGGAGTG GGTGTGGGCTGGATCCGTCAGCCCCCAGGAAAG GCCCTGGAGTGGCTTGCACTCATTTATTGGAATG ATGATAAGCGCTACAGCCCATCTGAAGAGCA GGCTCACCATCACCAGGGACACCTCCAAAAACC AGGTGGTCCTTACAAGCCACCACATTACTGTGCACACTATA GCAGTTCGTGGCTTTGACTACTGGGGCCAGGGAA CCCTGGTCACCGTCTCCTCA<br>SEQ ID NO: 29099 |
| | | AA | SYELTQPPSVSVSPGQTASITCSGDKLGEKYACW YQQKPGQSPVLVIYQDRKRPSGIPERYSGSNTGN TATLTISGTQAMDEADYYCQAWDSSTAVFGGG TKLTVL<br>SEQ ID NO: 25094 | QITLKESGPTLVKPTQTLTLTCTFSGFSLSTGGVGVG WIRQPPGKALEWLALIYWNDDKRYSPSLKSRLTIT RDTSKNQVVLTMTNMDPVDTATYYCAHTIAVRGF DYWGQGTLVTVSS<br>SEQ ID NO: 29100 |

FIGURE 50
(Continued)

| | | | |
|---|---|---|---|
| iPS:398500 | 21-225_23A11 | NA | GACATCCAGATGACCCAGTCTCCATCCTCACT GTCTACATCTGTAGGAGACAGAGTCACCATCA CTTGTCGGGCGAGTCAGGACATTAGCAATTAT TTAGCCTGGTTTCAGCAGAAACCAGGGAAAGC CCCTAAGCGCCTGATCTATGCTGCATCCACTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATAATAGTTACCCATTCA CTTTCGGCCCTGGGACCAAAGTGGATCTCAAG SEQ ID NO: 25095 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGTTATAGCAT GAACTGGATCCGCCAGGCTCCAGGGAAGGGGCT GGAGTGGGTCTCATCCATTAGTGGTAGTAGTACT TACATATACTACGCAGACTCAGTGAAGGGCCGA ATCGCCATCTCCAGAGACAACGCCAAGAACTCA CTGTATCTGCAAATGAACAGCCTGAGAGCCGAG GACACGGCTGTGTATTACTGTGCGAGAGTGGCTT CATTTGACTACTGGGGCCAGGGAACCCTGGTCAC CGTCTCCTCA SEQ ID NO: 29101 |
| | | AA | DIQMTQSPSSLSTSVGDRVTITCRASQDISNYLA WFQQKPGKAPKRLIYAASTLQSGVPSKFSGSGS GTDFTLTISSLQPEDFATYYCQQYNSYPFTFGPG TKVDLK SEQ ID NO: 25096 | EVQLVESGGGLVKPGGSLRLSCAASGFTFSSYSMN WIRQAPGKGLEWVSSISGSSTYIYYADSVKGRIAIS RDNAKNSLYLQMNSLRAEDTAVYYCARVASFDY WGQGTLVTVSS SEQ ID NO: 29102 |
| iPS:398502 | 21-225_23B11 | NA | GACATCCAGATGACCCAGTCTCCATCTTCCGT GTCTGCATCTGTAGGAGACAGAGTCACCATCA CTTGTCGGGCGAGTCAGGGTATTACCAAGTGG TTAGCCTGGTATCAGCAGAAACCAGGGAAAG CCCCTAAAGTCCTGATCTATGCTGCATCCAGTT TGCAAAGTGGGGTCCCATCAAGGTTCAGCGGC AGTAGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A SEQ ID NO: 25097 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATC TGCACTGGGTGCGACAGGCCCCTGGACAAGGGC TTGAGTGGATGGGATGGATCAACCCTAACAATAA TGGCACAAACTATGCACAGAAGTTTCAGGGCAG GGTCACCATGACCAGGGACACGTCCATCAGCAC AGCCTACATGGAGCTGAGCCGGCTGAGATCTGA CGACACGGCCGTGTATTACTGTGCGAGAGATGGT ACCAGCTCGTTTGACTACTGGGGCCAGGGAACCC TGGTCACCGTCTCCTCA SEQ ID NO: 29103 |

FIGURE 50
(Continued)

| | | | |
|---|---|---|---|
| iPS:398504 | 21-225_23D7 | AA | DIQMTQSPSSVSASVGDRVTITCRASQGITKWLAWYQQKPGKAPKVLIYAASSLQSRVPSRFSGSRSGTDFTLTISSLQPEDFATYYCQQANSFPFTFGPGTKVDIK<br>SEQ ID NO: 25098 |
| | | | QVQLVQSGAEVKKPGASVKVSCKASGYTFTGYLHWVRQAPGQGLEWMGWINPNNNGTNYAQKFQGRVTMTRDTSISTAYMELSRLRSDDTAVYYCARDGTSSFDYWGQGTLVTVSS<br>SEQ ID NO: 29104 |
| | | NA | TCCTATGAACTGACTCAGCCACCCTCAGTGTCCGTGTCCCCAGGACAGAGCCAGCATCACCTGCTCTGGAGAAAAATTGGGGGATAAAATATGTTTGTTGGTATCAGCAGAAGCCAGGCCAGTCCCCTGTGGTGGTCATCTATCAAGATAGCAAGCGGCCCTCAGGGATCCCTGAGCGATTCTCTGGCTCCAACTCTGGGAACACAGGCTATGGATGAGGCTGACTATTACTGTCAGGCGTGGAACAGCAGCAATGTGGTATTCGGCGGAGGGACCAAGCTGACCGTCCTA<br>SEQ ID NO: 25099 |
| | | | CAGATCACCTTGAAGGAGTCTGGTCCTACGCTGGTGAAACCCACACAGACCCTCACGCTGACCTGCACCTTCTCTGGGTTCTCACTCAGCACTAGTGGAGTGGGTGTGGGGCTGGATCCGTCAGCCCCCAGGAAAGGCCCTGGAGTGCTTTCACTCATTATTGAATAATGATAAGGTCTACAGCCCATCTGAAGAGCAGCTCACCATCACCAAGTACACCTCCAAAAACCAGGTGGTCCTTACAATGTCCAACATGTGCACAGGGACAGCAGCTGGCCCTGACTACTGGGGCCAGGGAACCCTGGTCACCGTCCTCA<br>SEQ ID NO: 29105 |
| | | AA | SYELTQPPSVSVSPGQTASITCSGEKLGDKYVCWYQQKPGQSPVVVIYQDSKRPSGIPERFSGSNSGNTATLTISGTQAMDEADYYCQAWNSSNVVFGGGTKLTVL<br>SEQ ID NO: 25100 |
| | | | QITLKESGPTLVKPTQTLTLTCTFSGFSLSTSGVGVGWIRQPPGKALECLSLIYWNNDKVYSPSLKSRLTITKYTSKNQVVLTMSNMDPVDTATYYCAHRGQQLALDYWGQGTLVTVSS<br>SEQ ID NO: 29106 |

FIGURE 50
(Continued)

| | | | | |
|---|---|---|---|---|
| iPS:398506 | 21-225_23G12 | NA | GACATCGTGATGACCCAGTCTCCAGACTCCCT GGCTGTGTCTCTGGGGAGAGGGCCACCATCA ACTGCAAGTCCAGCCAGAGTATTTTATTCAGC TCCAACAATAACAACTACTTAGCTTGGTACCA GCAGAAACCAGGACAAACCTCCTAAGTTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTTCTGTCAGCAA TATTCTAGTACTCCGTGGACGTTCGGCCAAGG GACCAAGGTGGAAATCAAA<br><br>SEQ ID NO: 25101 | CAGGTGCAGCTGCTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGTACCCTAACAGTGG TAACACGGGCTATGCACAGAAGTTCAGGGCAG AGTCACCATGACCATGAACACCTCCATAAGCACA GCCTACATGGAGTTGAGCAGCCTGAGATCTGAG GACACGGCCGTGTATTACTGTGCGATTAGCGGTG GCTGGTACTACTTTGACTACTGGGGCCAGGGAAC CCTGGTCACCGTCTCCTCT<br><br>SEQ ID NO: 29107 |
| | | AA | DIVMTQSPDSLAVSLGERATINCKSSQSILFSSNN NNYLAWYQQKPGQPPKLLIYWASTRESGVPDRF SGSGSGTDFTLTISSLQAEDVAVYFCQQYSSTPW TFGQGTKVEIK<br><br>SEQ ID NO: 25102 | QVQLLQSGAEVKKPGASVKVSCKASGYTFTNYDIN WVRQATGQGLEWMGWMYPNSGNTGYAQKFQGR VTMTMNTSISTAYMELSSLRSEDTAVYYCAISGGW YYFDYWGQGTLVTVSS<br><br>SEQ ID NO: 29108 |
| iPS:398508 | 21-225_24B1 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTACTTGAATTGGTTTCAGCAG AGGCCAGGCCAATCTCCAAGGCGCCTAATTTA TAAGGTTTCTAACTGGGACTCTGGGGTCCCAG ACAGATTCAGCGGCAGTGGGTCAGGCACTGAT TTCACACTGAAAATCAGCTGGGTGGAGGCTGA GGATGTTGGGGTTTGTTACTGCATGCAAGGTG CACACTGCCTCCGATCACCTTCGGCCAAGGG ACACGACTGGAGATTAAA<br><br>SEQ ID NO: 25103 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTCAGTGCCAT GAGCTGGGTCCGCCAGGCTCCAGGGAAGGGGCT GGAGTGGGTCTCAGTATTAGTGGTGGTGGTGGT AGCACATACTACGCAGACTCCGTGAAGGGCCG TTCACCATCCAGAGACAATTCCAAGAACACGC TGTATCTGCAAATGAACAGCCTGAGAGCCGAGG ACACGGCCGTATACAGTATGAGTACTACGTATGA CGTCTGGGGCCAGGGGACCACGGTCACCGTCTCC TCA<br><br>SEQ ID NO: 29109 |

FIGURE 50
(Continued)

| | | | |
|---|---|---|---|
| | | AA | DVVMTQSPLSLPVTLGQPASISCRSSQSLVYSDG<br>NTYLNWFQQRPGQSPRRLIYKVSNWDSGVPDRF<br>SGSGSGTDFTLKISWVEAEDVGVCYCMQGAHW<br>PPITFGQGTRLEIK<br>SEQ ID NO: 25104 | EVQLLESGGGLVQPGGSLRLSCAASGFTFSSYAMS<br>WVRQAPGKGLEWVSAISGRGGSTYYADSVKGRFTI<br>SRDNSKNTLYLQMNSLRAEDTAVYYCAKWGRGY<br>SYEYYYGMDVWGQGTTVTVSS<br>SEQ ID NO: 29110 |
| iPS:398510 | 21-225_25A3 | NA | GACATCGTGATGACCCAGTCTCCAGACTCCCT<br>GACTGTGTCTCTGGGCGAGAGGGCCACCATCA<br>ACTGCAAGTCCAGCCAGAGTGTTTATACAGC<br>TCCAACAATAAGAACTACTTAGCTTGGTACCA<br>GCAGAAACCTGGACAGCCTCCTAAGCTGCTCA<br>TTTACTGGGCATCTACCCGGGAATCCGGGGTC<br>CCTGACCGATTCAGTGGCAGCGGGTCTGGGAC<br>AGATTTCACTCTCACCATCAGCAGCCTGCAGG<br>CTGAAGATGTGGCAGTTTATTACTGTCAGCAA<br>TATTATAGTACTCCGTGCAGTTTGGCCAGGG<br>GACCAGGCTGGAGATCAAA<br>SEQ ID NO: 25105 | CAGGTGCAGCTGGTGCAGTCTGGGGCTGAGGTG<br>AAGAAGCCTGGGGCCTCAGTGAAGGTCTCCTGC<br>AAGGCTTCTGGATACATCTTCACCAATTATGATA<br>TCAACTGGGTGCGACAGGCCACTGGACAAGGC<br>TTGAGTGGATGGGATGGATGCACCTAACAGTGG<br>TAACACAGGCTATGCACAGAAGTTCCAGGGCAG<br>AGTCACCATGACCTGAACACCTCCATAAGCACA<br>GCCAACATGGAGCTGAGCAGCCTGAGATCTGAG<br>GACACGGCCGTGTATTACTGTGCGAGTAGCAGTG<br>GCTGGTATTGGTTCGACCCCTGGGGCCAGGGAAC<br>CCTGGTCACCGTCTCCTCA<br>SEQ ID NO: 29111 |
| | | AA | DIVMTQSPDSLTVSLGERATINCKSSQSVLYSSN<br>NKNYLAWYQQKPGQPPKLLIYWASTRESGVPD<br>RFSGSGSGTDFTLTISSLQAEDVAVYYCQQYYST<br>PCSFGQGTRLEIK<br>SEQ ID NO: 25106 | QVQLVQSGAEVKKPGASVKVSCKASGYIFTNYDIN<br>WVRQATGQGLEWMGWMHPNSGNTGYAQKFQGR<br>VTMTWNTSISTANMELSSLRSEDTAVYYCASSSGW<br>YWFDPWGQGTLVTVSS<br>SEQ ID NO: 29112 |

FIGURE 50
(Continued)

| | | | | |
|---|---|---|---|---|
| iPS:398512 | 21-225_25E12 | NA | GACATCGTGCTGACCCAGTCTCCAGACTTCCTGGCTATGTCTCTGGGCGAGAGGGCCACCATCAACTGCAAGTCCAGCCAGAGTGTTTATACCACTCCAACAATTACAACAGCTACTTAGCTTGGTACCAGCAGAAACCAAAACAGCCTCCTAAGCTGCTCATTTACTGGGCATCTACCCGGGAGTCCGGGGTCCCTGACCGATTCAGTGGCAGCGGGTCTGGGACATATTTCACTCTCACCATCAGCAGCCTCCAGGCTGAAGATGTGGCAGTTTATTACTGTCAGCAATATTACAGTACTCCGTCAGTTTGGCCAGGGACCAACCTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGCAGAGTCACCATGACCAGGAACACCTCCATAAGCACAGCCTACCTGGAGTCTGAGCAGCCTGAGATCTGAGGACACGGCCGTGTATTACTGTGCGGGGAGCAATGGCTGGTACTACTTTGACTACTGGGGCCAGGGAACCCTGGTCACCGTCTCCTCA |
| | | | SEQ ID NO: 25107 | SEQ ID NO: 29113 |
| | | AA | DIVLTQSPDFLAMSLGERATINCKSSQSVYTHSNNYNYLAWYQQKPKQPPKLLIYWASTRESGVPDRFSGSGSGTYFTLTISSLQAEDVAVYYCQQYYSTPCSFGQGTNLEIK | QVQLVQSGAEVKKPGASVKVSCKASGYTFTNYDINWVRQATGQGLEWMGWMNPNSGNTGYAQKFQGRVTMTRNTSISTAYLELSSLRSEDTAVYYCAGSNGWYYFDYWGQGTLVTVSS |
| | | | SEQ ID NO: 25108 | SEQ ID NO: 29114 |
| iPS:398516 | 21-225_26A9 | NA | GACATCGTGATGACCCAGTCTCCAGACTCCCTGGCTGTGTCTCTGGGCGAGAGGGCCACCATCAACTGCAAGTCCAGCCAGAGTGTTTATACCACTCCAACAATAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGACTTCACTCTCACTATCAGCAGCCTGCAGGCTGAAGATGTGGCAGTTTATTACTGTCAGCAATATTATAGTAGTCCGTCAGTTTGGCCAGGGACCAGGCTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAATGGATGGGATGGATGCACAGAAGTTCCAGGCAGTAACACAGGCTGTGCACAGAAGTTCCAGGCAGAGTCACCATGACCTGGAACATGTCCATAAGCACAGCCTACATGGAGCTGAGCAGCCTGAGATCTGAGGACACGGCCGTATATTACTGTGCGAGTAGCAGTGGCTGGTACTGGTTCGACCCCTGGGGCCAGGAACCCTGGTCACCGTCTCCTCA |
| | | | SEQ ID NO: 25109 | SEQ ID NO: 29115 |

FIGURE 50
(Continued)

| | | | |
|---|---|---|---|
| iPS:398520 | | AA | DIVMTQSPDSLAVSLGERATINCKSSQSVLYSSN NKNYLAWYQQKPGQPPKLLIYWASTRESGVPD RFSGSGSGTDFTLTISSLQAEDVAVYYCQQYYSS PCSFGQGTRLEIK<br>SEQ ID NO: 25110 | QVQLVQSGAEVKKPGASVKVSCKASGYTFTNYDIN WVRQATGQGLEWMGWMHPNSGNTGCAQKFQGR VTMTWNMSISTAYMELSSLRSEDTAVYYCASSSG WYWFDPWGQGTLVTVSS<br>SEQ ID NO: 29116 |
| | 21-225_31C4 | NA | CAGGTGCAGTTGGTGCAGTCTGGGACTGAGGTGA AGAAGCCTGGGGCCTCAGTGAAGGTCTCCTGCA AGGCTTCTGGATACACCTTCACCGGCGATTATAT GCACTGGGTGCGACAGGCCCCTGGACAAGGGCT TGAGTGGATGGGATGGATCAGCCTAAAAATGG TGGCACAAACTATGCACAGAAGTTTCAGGGCAG GGTCACCATGACCAGGGACACGTCCATCAGCAC AGTCTACATGGAGCTGAACAGGCTGAGATCTGA CGACACGGCCGTGTATTACTGTGCGAGAGATGG AACTGGGTCCTTTGACTACTGGGGCCAGGGAACC CTAGTCACCGTCTCCTCA<br>SEQ ID NO: 29117 | |
| | | AA | DIQMTQSPSSVSASVGDRVTITCRASQGISKWLA WYQQKPGKAPKPLIYAASSLQSGVPTRFSGSGS GTDFTLTISSLQPEDFAIYYCQQANSFPFTFGPGT KVDIK<br>SEQ ID NO: 25112 | QVQLVQSGTEVKKPGASVKVSCKASGYTFTGDYM HWVRQAPGQGLEWMGWISPKNGGTNYAQKFQGR VTMTRDTSISTVYMELNRLRSDDTAVYYCARDGT GSFDYWGQGTLVTVSS<br>SEQ ID NO: 29118 |

FIGURE 50
(Continued)

| | | | | |
|---|---|---|---|---|
| iPS:398522 | 21-225_32A1 | NA | GACATCGTGATGACCCAGTCTCCAGACTCCCT GGCTGTGTCTCTGGGCGAGAGGGCCACCATCA ACTGCAAGTCCAGCAGTGTTTATACAGC TCCAACAATTACAACTACTTAGCTTGGTACCA GCTGAAACCAGGACAGCCTCCTAAGCTGCTCA TTTACTGGGCATCTACCCGGAAATCGGGGTC CCTGACCGATTCAGTGGCAGCGGGTCTGGGAC AGATTTCACTCTCACCATCAGCAGCTGCAGA CTGAAGATGTGGCACTTTATTACTGTCAACAA TATTATACTTCTCCGTGCAGTTTTGGCCAGGGG ACCAAGGTGGAGATCAAA<br><br>SEQ ID NO: 25113 | CAGGTGCAGCTGGTGCAGTCTGGGGCTGAGGTG AAGAAGCCTGGGGCCTCAGTGAAGGTCTCCTGC AAGGCTTCTGGATACACCTTCACCAACTATGATA TTAACTGGGTGCGACAGGCCACTGGACAAGGGC TTGAGTGGATGGGATGGATGAACCCTAACAGTG GTAACACAGGCTATGCACAGAAGTTCCAGGGC GAGTCACCATGACCAGGAACACCTCCATAAGCA CAGCCTACATGGAGCTGAGCAGCCTGAGATCTG AGGACACGGCCGTGTATTACTGTGCGAGCAGCA GTGGCTGGTACTTTTTTGACTACTGGGGCCAGGG AACCCTGGTCACCGTCTCCTCA<br><br>SEQ ID NO: 29119 |
| | | AA | DIVMTQSPDSLAVSLGERATINCKSSQSVLYSSN NYNYLAWYQLKPGQPPKLLIYWASTRKSGVPD RFSGSGSGTDFTLTISSLQTEDVALYYCQQYYTS PCSFGQGTKLEIK<br><br>SEQ ID NO: 25114 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YFFDYWGQGTLVTVSS<br><br>SEQ ID NO: 29120 |
| iPS:398524 | 21-225_32A5 | NA | GACATCGTGATGACCCAGTCGCCAGACTCCCT GGCTGTGTCTCTGGGCGAGAGGGCCACCATCA ACTGCAAGTCCAGCCAGAGTGTTTTACACAGC TCCAACAATAAGAACTACTTAGCTTGGTATCA GCAGAAACCAGGACAGCCTCCTAAGCTGCTCA TTTACTGGGCATCTACCCGGGAATCCGGGGTC CCTGACCGCTTCAGTGGCAGCGGGTCTGGGAC AGATTTCACTCTCGCCATCAGCAGCTGTCAGCAGG CTGAAGATGTGGCACTTTATCACTGTCAGCAA TATTATAGTTCTCCGTGCAGTTTTGGCCAGGG GACCGGGCTGGAGATCAAA<br><br>SEQ ID NO: 25115 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGACA TCAACTGGGTGCGACAGGCCACTGGACAAGGC TTGAGTGGATGGGATGGATGCACCTAACAGTGG TAACACAGGCTTTGCACAGAAGTTCCGGGGCAG AGTCACCATGACCAGAAACACCTCCATAAGCAC AGCCTACATGAACTGAGCAGCCTGAGATCTGA GGACACGGCCGTGTATTACTGTGCGAGCAGAGT GGCTGGTACTTTTTGACTACTGGGGCCAGGAA CCCTGGTCACCGTCTCCTCA<br><br>SEQ ID NO: 29121 |

FIGURE 50
(Continued)

| | | | |
|---|---|---|---|
| iPS:398526 | 21-225_32B3 | AA | DIVMTQSPDSLAVSLGERATINCKSSQSVLHSSN NKNYLAWYQQKPGQPPKLLIYWASTRESGVPD RFSGSGSGTDFTLAISSLQAEDVALYHCQQYYSS PCSFGQGTGLEIK<br>SEQ ID NO: 25116 | QVQLVQSGAEVKKPGASVKVSCKASGYTFTNYDIN WVRQATGQGLEWMGWMHPNSGNTGFAQKFRGR VTMTRNTSISTAYMELSSLRSEDTAVYYCSSSSGW YFFDYWGQGTLVTVSS<br>SEQ ID NO: 29122 |
| | | NA | GACATCCAGATGACCCAGTCTCCATCCTCACT GTCTGCATCTATAGGAGACAGAGTCACCATCA CTTGTCGGGCGAGTCAGGGCATTAGCAATTAT TTAGCCTGGTTTCAGCAGAAACCAGGGAAAGC CCCTAGGTCCCTGATCTATGCTGCATCCAGTTT ACAAAAGTGGGGTCCCATCAACGTTCAGCGGCA GTGGATCTGGGACAGATTTCACTCTCACCATC AGCAGCCTGCAGCCTGAAGATTTTGCAACTTA TTACTGCCAACAGTATATAATAGTTATCCATTCA CTTTCGGCCCTGGGACCAAAGTGGATATCAAA<br>SEQ ID NO: 25117 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGTGGCTGGC TTTGACTACTGGGGCCAGGGAACCCTGGTCACCG TCTCCTCA<br>SEQ ID NO: 29123 |
| | | AA | DIQMTQSPSSLSASIGDRVTITCRASQGISNYLAW FQQKPGKAPRSLIYAASSLQSGVPSTFSGSGSGT DFTLTISSLQPEDFATYYCQQYNSYPFTFGPGTK VDIK<br>SEQ ID NO: 25118 | EVQLVESGGGLVKPGGSLRLSCAASGFTFSSYSMN WVRQAPGKGLEWVSSISGSSTYIYYADSVKGRFTIS RDNAKNSLYLQMNSLRAEDTAVYYCARVAGFDY WGQGTLVTVSS<br>SEQ ID NO: 29124 |

FIGURE 50
(Continued)

| | | | |
|---|---|---|---|
| iPS:398528 | 21-225_32G1 | NA | GACATCCAGATGACCCAGTCTCCATCCTCCT<br>GTCTGCATCTGTAGGAGACAGAGTCACCATCA<br>CTTGCCGGGCAAGTCAGGACATGAGAAGTGAT<br>TTAGGCTGGTATCAGCAGAAACCAGGGAAAG<br>CCCCTAAGCGCCTGATCTATGCTGCATCCAGT<br>TTGCAAAGTGGGGTCCCATCAAGGTTCAGCGG<br>CAGTGGATCTGGGACAGAATTCACTCTCACAA<br>TCAGCAGCCTGCAGCCTGAAGATTTTGCAACT<br>TATTACTGTCTACAGCATACTATTTCCCCTCCT<br>ACTTTCGGCGGAGGGACCAAGGTGGAGATCA<br>AA |
| | | | GAGGTGCAGCTGTTGGAGTCTGGGGGAGGCTTG<br>GCACAGCCTGGGGGGTCCCTGAGACTCTCCTGTG<br>CAGCCTCTGGATTCACCTTTAGCAGCTATGCCAT<br>GAGCTGGGTCCGCCAGGCTCCAGGGAAGGGGCT<br>GGAGTGGGTCTCCGCTATTAGTGGTCGTGGTGGT<br>AGCACATTCCACGCAGACTCCGTGAAGGGCCGG<br>TTCACGATCTCCAGAGACAATTCAAGAACACGC<br>TGTATCTGCAAATGAACAGCCTGAGAGCCGAGG<br>ACACGGCCGTATATTACTGTGTGAAAGGGGAGCT<br>ACTAGAGGACTACTACTTCTACGGTATGGACGTC<br>TGGGGCCAAGGGACCACGGTCACCGTCTCCTCA |
| | | | SEQ ID NO: 25119 |
| | | | SEQ ID NO: 29125 |
| | | AA | DIQMTQSPSSLSASVGDRVTITCRASQDMRSDLG<br>WYQQKPGKAPKRLIYAASSLQSGVPSRFSGSGS<br>GTEFTLTISSLQPEDFATYYCLQHTISPPTFGGGT<br>KVEIK |
| | | | EVQLLESGGGLAQPGGSLRLSCAASGFTFSSYAMS<br>WVRQAPGKGLEWVSAISGRGGSTFHADSVKGRFTI<br>SRDNSKNTLYLQMNSLRAEDTAVYYCVKGELLED<br>YYFYGMDVWGQGTTVTSS |
| | | | SEQ ID NO: 25120 |
| | | | SEQ ID NO: 29126 |
| iPS:398530 | 21-225_32G4 | NA | GATGTTGTGATGACTCAGTCTCCACTCTCCCTG<br>TCCGTCACCCTTGGACAGCCGGCCTCCATCTC<br>CTGCAGGTCAAGTCAAAGCCTCGTATACAGTG<br>ATGGAAACACCTACTTGAATTGGTTTCAGCAG<br>AGGCCAGGCCAATCTCCAAGGCGCCTAATTTA<br>TAAGGTTTCTAACTGGGACTCTGGGGTCCCAG<br>ACAGATTCAGCGGCAGTGGGTCAGGCACAGA<br>TTTCACACTGAAAATCAGCAGGGTGGAGGCTG<br>AGGATGTTGGGGTTTATTACTGCATGCAAGGT<br>ATACACTGGCTCACTTTCGGCGGAGGGACCAA<br>GGTGGAGATCAAA |
| | | | CAGGTGCAGCTGGTGCAGTCTGGGGCTGAGGTG<br>AAGAAGCCTGGGGCCTCAGTGAAGGTCTCCTGC<br>AAGGCTTCTGGATACACCTTCACCAGTTATGATA<br>TCAACTGGGTGCGACAGGCCACTGGACAAGGC<br>TTGAGTGGATGGGATGGATGAACCTAACAGTG<br>GTAACACAGGCTATGCACAGAAGTTCCAGGGCA<br>GAGTCACCATGACCAGGAACACCTCCATAAGCA<br>CAGCCTACATGGAGCTGAGCAGCCTGAGATCTG<br>AGGACACGGCCGTGTATTACTGTGCGCGAAAGA<br>AGGCTAACGACTACTGGGGCCAGGGAACCCTGG<br>TCACCGTCTCCTCA |
| | | | SEQ ID NO: 25121 |
| | | | SEQ ID NO: 29127 |

FIGURE 50
(Continued)

| | | | |
|---|---|---|---|
| iPS:398532 | 21-225_33B7 | AA | DVVMTQSPLSLSVTLGQPASISCRSSQSLVYSDG NTYLNWFQQRPGQSPRRLIYKVSNWDSGVPDRF SGSGSGTDFTLKISRVEAEDVGVYYCMQGIHWL TFGGGTKVEIK<br>SEQ ID NO: 25122 | QVQLVQSGAEVKKPGASVKVSCKASGYTFTSYDIN WVRQATGQGLEWMGWMNPNSGNTGYAQKFQGR VTMTRNTSISTAYMELSSLRSEDTAVYYCARKKAN DYWGQGTLVTVSS<br>SEQ ID NO: 29128 |
| | | NA | GACATCCAGATGACCCAGTCTCCATCCTCACT GTCTGCATCTGTAGGAGACAGAGTCACCATCA CTTGTCGGGCGAGTCAGGACATTAGCAATTAT TTGGCCTGGTTTCAGCAGAAACCAGGGAAAGC CCCTACGTCCCTGATCTATGCTGCATCTAGTTT GCAAAGTGGGGTCCCATCAAAGTTCAGCGGCA GTGGATCTGGGACAGATTTCACTCTCACCATC AGCAGCCTGCAGCCTGAAGATTATAGTTACTGC TTACTGCCAACAGTATCATAGTTACCCGCTCA CCTTCGGCCAAGGGACACGACTGGAAATTAAA<br>SEQ ID NO: 25123 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAACAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGGTTAAATGGT TTTGACTACTGGGGCCAGGGAACCCTGGTCACCG TCTCCTCA<br>SEQ ID NO: 29129 |
| | | AA | DIQMTQSPSSLSASVGDRVTITCRASQDISNYLA WFQQKPGKAPTSLIYAASSLQSGVPSKFSGSGSG TDFTLTISSLQPEDFATFYCQQYHSYPLTFGQGT RLEIK<br>SEQ ID NO: 25124 | EVQLVESGGGLVKPGGSLRLSCAASGFTFSSYNMN WVRQAPGKGLEWVSSISGSSSYIYYADSVKGRFTIS RDNAKNSLYLQMNSLRAEDTAVYYCARLNGFDY WGQGTLVTVSS<br>SEQ ID NO: 29130 |

FIGURE 50
(Continued)

| | | | |
|---|---|---|---|
| iPS:398534 | 21-225_33B8 | NA | GACATCCAGATGACCCAGTCTCCATCCTCCT GTCTGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTTCTGTCTACAGCATACTATTTACCCTCCT ACTTTCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCCGCTATTAGTGGTGCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGTGAAAGGGAGCT ACTAGAGGACTACTACTTCTACGTATGGACGTC TGGGGCCAAGGGACCACGGTCACCGTCTCCTCA |
| | | | SEQ ID NO: 25125 | SEQ ID NO: 29131 |
| | | AA | DIQMTQSPSSLSASVGDRVTITCRASQDIRSDLG WYQQKPGKAPKRLIYAASSLQSGVPSRFSGSGS GTEFTLTISSLQPEDFATYFCLQHTIYPPTFGGGT KVEIK | EVQLLESGGGLVQPGGSLRLSCAASGFTFSSYAMS WVRQAPGKGLEWVSAISGRGGSTFHADSVKGRFTI SRDNSKNTLYLQMNSLRAEDTAVYYCVKGELLED YYFYGMDVWGQGTTVTSS |
| | | | SEQ ID NO: 25126 | SEQ ID NO: 29132 |
| iPS:398536 | 21-225_33D12 | NA | GACGTCCAGATGACCCAGTCTCCATCCTCCCT GTCTGCATCTTTAGGAGACAGAGTCACCATCA CTTGCCGGGCAAGTCAGAGCATTAGAAGCTAT TTAAATTGGTATCAGCAGAAACCAGGGAAAG CCCCTAAGCTCCTGATCTATAGTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTATCCCGATC ACCTTCGGCCAAGGGACACGACTGGAGATTAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAGCTGGGTGCGACTGGCCACTGGACAAGGGC TTGAGTGGATGGGATGGATGAACCCTAACAGTG GTAACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGAGAAAGA GGGCTAACGACTACTGGGGCCAGGGAACCCTGG TCACCGTCTCCTCA |
| | | | SEQ ID NO: 25127 | SEQ ID NO: 29133 |

FIGURE 50
(Continued)

| | | | |
|---|---|---|---|
| | | AA | DVQMTQSPSSLSASLGDRVTITCRASQSIRSYLN WYQQKPGKAPNLLIYSASSLQSGVPSRFSGSGSG TDFTLTISSLQPEDFANYYCQQSYSIPITFGQGTR LEIK<br>SEQ ID NO: 25128 | QVQLVQSGAEVKKPGASVKVSCKASGYTFTSYDIS WVRLATGQGLEWMGWMNPNSGNTGYAQKFQGR VTMTRNTSISTAYMELSSLRSEDTAVYYCARKRAN DYWGQGTLVTVSS<br>SEQ ID NO: 29134 |
| iPS:398538 | 21-225_34H7 | NA | GACATCGTGATGACCCAGTCTCCAGACTCCCT GGCTGTGTCTCTGGGCGAGAGGGCCACCATCA ACTGCAAGTCCAGCCAGAGTGTTTATACAGC TCCAACAATTACAACTACTTAGCTTGGTACCA GCTGAAACCAGGACAGCCTCCTAAGCTGCTCA TTTACTGGGCATCTACCCGGAAATCCGGGGTC CCTGACCGATTCAGTGGCAGCGGGTCTGGGAC AGATTTCACTCTCACCATCAGCAGCCTGCAGA CTGAAGATGTGGCACTTTATTACTGTCAGCAA TATTATACTTCTCCGTCCAGTTTTGGCCAGGGG ACCAAGCTGGAGATCAAA<br>SEQ ID NO: 25129 | CAGGTGCAGCTGGTGCAGTCTGGGGCTGAGGTG AAGAAGCCTGGGGCCTCAGTGAAGGTCTCCTGC AAGGCTTCTGGATACACCTTCACCAACTATGATA TTAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAACAGCCTGAGATCTG AGGACACGGCCGTGTATTACTGTGCGAGCAGCA GTGGCTGGTACTTTTTTGACTACTGGGGCCAGGG AACCCTGGTCACCGTCTCCTCA<br>SEQ ID NO: 29135 |
| | | AA | DIVMTQSPDSLAVSLGERATINCKSSQSVLYSSN NYNYLAWYQLKPGQPPKLLIYWASTRKSGVPD RFSGSGSGTDFTLTISSLQTEDVALYYCQQYYTS PCSFGQGTKLEIK<br>SEQ ID NO: 25130 | QVQLVQSGAEVKKPGASVKVSCKASGYTFTNYDIN WVRQATGQGLEWMGWMNPNSGNTGYAQKFQGR VTMTRNTSISTAYMELNSLRSEDTAVYYCASSSGW YFFDYWGQGTLVTVSS<br>SEQ ID NO: 29136 |

FIGURE 50
(Continued)

| | | | |
|---|---|---|---|
| iPS:398540 | 21-225_35A6 | NA | GACATCCAGATGACCCAGTCTCCATCCTCCCT GTCCGCATCTGTAGGAGACAGAGTCACCATCA CTTGCCGGGCAAGTCAGGACATTAGAAGTGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGATTTCACTCTCACAA TCAGCAGCCTGCAGCCTGAAGATTTTGCAACT TATTACTGTCTACAGCATACTATTTACCCTCCT ACTTTCGGCGGAGGGACCAAGGTGGAGATCA AA |
| | | | SEQ ID NO: 25131 |
| | | AA | DIQMTQSPSSLSASVGDRVTITCRASQDIRSDLG WYQQKPGKAPKRLIYATSSLQSGVPSRFSGSGSG TEFTLTISSLQPEDFATYYCLQHTIYPPTFGGGTK VEIK |
| | | | SEQ ID NO: 25132 |
| | | | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGCT GGAGTGGGTCTCCACTATTAGTGGTCGTGGTGGT AGCACATTCCACGCAGACTCCGTGAAGGGCCGG TTCACCATCTCCAGAGACAATTCCAAGAACACGC TGTATCTGCAAATGAACAGCCTGAGAGCCGAAG ACACGGCCGTATATTACTGTGTGAAAGGGAGCT ACTAGAGGACTACTACTTCTACGTATGGACGTC TGGGGCCAAGGGACCACGGTCACCGTCTCCTCA |
| | | | SEQ ID NO: 29137 |
| | | AA | EVQLLESGGGLVQPGGSLRLSCAASGFTFSSYAMS WVRQAPGKGLEWVSTISGRGGSTFHADSVKGRFTI SRDNSKNTLYLQMNSLRAEDTAVYYCVKGELLED YFYGMDVWGQGTTVTVSS |
| | | | SEQ ID NO: 29138 |
| iPS:398544 | 21-225_7C8 | NA | CTGCCTGTGCTGACTCAGCCCCCGTCTGCATCT GCCTTGCTGGGAGCCTCGATCAAGCTCACCTG CACCCTAAGCAGTGAGCACAGACCCTACACCA TCGAATGGTATCAACAGAGACCAGGGAGGTC CCCCCAGTATATAATGAAGGTTAAGAGTGATG GCAGCCACAGCAAGGGGGACGGGATCCCGA TCGCTTCATGGGCTCCAGTTCTGGGGGTGACC GCTACCTCACCTTCTCCAACCTCCAGTCTGACG ATGAGGATGAGTATCACTGTGGAGAGACAA CCCGATTGATGGCCAAGTGCGGTGTGTATTCG GCGGAGGGACCAAGCTGACCGTCCTA |
| | | | |

FIGURE 50
(Continued)

| | | | SEQ ID NO: 25133 | | SEQ ID NO: 29139 |
|---|---|---|---|---|---|
| | | AA | LPVLTQPPSASALLGASIKLTCTLSSEHSTYTIEW YQQRPGRSPQYIMKVKSDGSHSKGDGIPDRFMG SSSGGDRYLTFSNLQSDDEDEYHCGESHPIDGQV GVVFGGGTKLTVL | | EVQLVESGGGLVKPGGSLRLSCAASGFTFSNARMN WVRLAPGKGLEWVGRIKSKTDGGTTDYAAPVKGR FTISRDESENTLYLQMNSLKTEDTGVYYCSTDTGPI AARLAYYYYAMDVWGQGTTVTVSS |
| iPS:398546 | 21-225_9H10 | | SEQ ID NO: 25134 | | SEQ ID NO: 29140 |
| | | NA | TCCTATGAGCTGACTCAGCCACCCTCAGTGTC CGTGTCCCCAGGACAGAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGGCGTGGGACAGCAGCACTTATGTG GTATTCGGCGGAGGGACCAAGCTGACCGTCCT A | | CAGATCACCTTGAAGGAGTCTGGTCCTACGCTGG TGAAACCCACACAGACCCTCACGCTGACCTGCAC CTTCTCTGGGTTCTCACTCACCACTAGTGGAGTG GGTGTGGCTGGATCCGTCAGCCCCAGGAAAG GCCCTGGAATGGCTTGCACTCATTTATTGGAGTG ATGATAAGCGCTACAGCCCATCTCTGAAGAGCA GGCTCACCATCACCAAGGACACACCTCAAAACC AGGTGGTCCTTACAATGACCAACATGGCCCTGT GGACACAGCCACATATTACTGTGCACACCGGT TCTAGCTGCTGCTATTTGACTACTGGGGCCAGG GAACCCTGGTCACCGTCCTCTCA |
| | | | SEQ ID NO: 25135 | | SEQ ID NO: 29141 |
| | | AA | SYELTQPPSVSVSPGQTASITCSGDKLGDKYACW YQQKPGQSPVLVIYQDSKRPSGIPERFSGSNSGN TATLTISGIQAMDEADYYCQAWDSSTYVFGG GTKLTVL | | QITLKESGPTLVKPTQTLTLTCTFSGFSLTTSGVGVG WIRQPPGKALEWLALIYWSDDKRYSPSLKSRLTITK DTSKNQVVLTMTNMAPVDTATYYCAHTGSSCCYF DYWGQGTLVTVSS |
| | | | SEQ ID NO: 25136 | | SEQ ID NO: 29142 |

FIGURE 50
(Continued)

| | | | |
|---|---|---|---|---|
| iPS:402219 | 21-225_1C12 | NA | GACATCCAGATGACCCAGAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAACATAATAGTTACCCGCTC ACTTTCGGCGGAGGGACCAAGGTGGCGATCA AA SEQ ID NO: 25137 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGTAGACTCCGTGAAAAT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAATTGGGG TTCCGGTCTGACTACTGGGGCCAGGGAACCCTGG TCACCGTCTCCTCA SEQ ID NO: 29143 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVAIK SEQ ID NO: 25138 | QVQLVESGGGVVQPGRSLRLSCAASGFTFSNYGM HWVRQAPGKGLEWVAVIWYDENNKYYVDSVKGR FTISRDNSKNTLYLQMNSLRAEDTAVYYCARELGF RSDYWGQGTLVTVSS SEQ ID NO: 29144 |
| iPS:402221 | 21-225_2C12 | NA | GACATCCAGATGACCCAGTCTCCATCCTCCACT GTCTGCATCTGTAGGAGACAGAGTCACCATCA CTTGTCGGGCGAGTCAGGGCATTAGCAGTTAT TTAGCCTGGTTTCAGCAGAAATCAGGGAAAGC CCCTAAGTCCCTGATCTCTGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTTGCAACTTA TTACTGCCAACAGTATTATAGTTACCCGATCA CCTTCGGCCAAGGGACACGACTGGAGATTAAA SEQ ID NO: 25139 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGT TACATGTACTACGCAGACTCAGTGAAGGGCCGAT TCACCATCTCCAGAGACAACGCCAAGGACTCACT GTATCTGCAAATGAACAGCTGAGAGCCGAGGA CACGGCTGTGTATTACTGTGTGCGAGAGTGAATCTC TTTGACTACTGGGGCCAGGGAACCCTGGTCACCG TCTCCCTCA SEQ ID NO: 29145 |

FIGURE 50
(Continued)

| | | | | |
|---|---|---|---|---|
| | | AA | DIQMTQSPSSLSASVGDRVTITCRASQGISNYLA WFQQKSGKAPKSLISAATSLQSGVPSQFSGSGSG TDFTLTISSLQPEDFATYYCQQYSYPITFGQGTR LEIK<br><br>SEQ ID NO: 25140 | EVQLVESGGGLVKPGGSLRLSCAASGFTFSSYSMN WVRQAPGKGLEWVSSISGSSSYMYYADSVKGRFTI SRDNAKDSLYLQMNSLRAEDTAVYYCARVNLFDY WGQGTLVTVSS<br><br>SEQ ID NO: 29146 |
| iPS:402223 | 21-225_30A11 | NA | GACATCCAGATGACCCAGTCTCCATCTTCCGT GTCTGCATCTGTAGGAGACAGAGTCACCATCA CTTGTCGGGCGAGTCAGGGTATTAGCAGATGG TTAGCCTGGTATCAGCAGAAACCAGGGAGAG CCCCTGAACTCCTGATCTATGCTGCATCCCGTT TGCAAAGTGGATCCCATCCAGGTTCAGCGGC AGTGGATCTGGGACAGACTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATAACAA A<br><br>SEQ ID NO: 25141 | CAGGTGCAGCTGGTGCAGTCTGGGGCTGAGGTG AAGAAGCCTGGGGCCTCAGTGAAGGTCTCCTGC AAGGCTTCTGGATACACCTTCACCGACTATCATA TGCACTGGGTGCGACAGGCCCCTGGACAAGGGC TTGAGTGGATGGGATGGATCAACCTAATAGGG GTGGCACAAACTATGCACAGAAGTTTCAGGACA GGGTCACCATGACCAGGGACACGTCCATCAGCA CAGCCTACATGGAACTGAGCAGGCTGAGATCTG ACGACACGGCCGTCTATTTCTGTGCGAGAGATGG AACTGGGTCCTTTGACTACTGGGGCCAGGGAACC CTGGTCACCGTCTCCTCA<br><br>SEQ ID NO: 29147 |
| | | AA | DIQMTQSPSSVSASVGDRVTITCRASQGISRWLA WYQQKPGRAPELLIYAASRLQSGIPSRFSGSGSG TDFTLTISSLQPEDFATYYCQQANSFPFTFGPGTK VDNK<br><br>SEQ ID NO: 25142 | QVQLVQSGAEVKKPGASVKVSCKASGYTFTDYHM HWVRQAPGQGLEWMGWINPNRGGTNYAQKFQDR VTMTRDTSISTAYMELSRLRSDDTAVYFCARDGTG SFDYWGQGTLVTVSS<br><br>SEQ ID NO: 29148 |

FIGURE 50
(Continued)

| | | | |
|---|---|---|---|
| iPS:402225 | 21-225_2B1 | NA | TCCTATGAGCTGACTCAGCCACCCTCAGTGTC CGTGTCCCCAGGACAGACAGTCAGCATCACCT GCTCTGGAGATAAATTGGGGGATAAATATGCT TGCTGGTATCAGCAGAAGCCAGGCCAGTCCCC TGTGCTGGTCATCTATCAAGATCGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCTGGGACAACAACACTGTGGTA TTCGGCGGAGGGACCAAGCTGACCGTCCTA<br><br>SEQ ID NO: 25143 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGTAGT TACATATACTACGCAGACTCAGTGAAGGGCCGAT TCACCATCTCCAGAGACAACAGCCAAGAACTCACT GTATCTGCAAATGAACAGCCTGAGAGCCGAGGA CACGGCTGTGTATTACTGTGCGCGTCTGGGAAC TACTGGGGCCAGGGAACCCTGGTCACCGTCTCCT CA<br><br>SEQ ID NO: 29149 |
| | | AA | SYELTQPPSVSVSPGQTVSITCSGDKLGDKYACW YQQKPGQSPVLVIYQDRKRPSGIPERFSGSNSGN TATLTISGTQAMDEADYYCQAWDNNTVFGGG TKLTVL<br><br>SEQ ID NO: 25144 | EVQLVESGGGLVKPGGSLRLSCAASGFTFSSYSMN WVRQAPGKGLEWVSSISSSSYIYYADSVKGRFTIS RDNAKNSLYLQMNSLRAEDTAVYYCARLGNYWG QGTLVTVSS<br><br>SEQ ID NO: 29150 |
| iPS:402229 | 21-225_16H9 | NA | GACATCCAGATGACCCAGTCTCCATCCTCCCT GTCTGCATCTGTAGGAGACAGAGTCACCATCA CTTGCCGGGCAAGTCAGGGCATTAGAAATTAT TTAGGCTGGTTTCAGCAGAAACCAGGGAAAGC CCCTAAGCGCCTGATCTATGGTGCATCCAGTT TGCAAAGTGGGGTCCCATCAAGGATCAGCGGC AGTGGATCTGGGACAGAATTCACTCTCACAAT CAGCAGCCTGCAGCCTGAAGATTTTGCAACTT ATTACTGTCTACAGTATCATAGTTATCTATTCA CTTTCGGCCCTGGGACCAAAGTGGATATCAAA<br><br>SEQ ID NO: 25145 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGT TACATATACTACGCAGACTCAGTGAAGGGCCGAT TCACCATCTCCAGAGACAACAGCCAAGAACTCACT GTATCTGCAAATGAACAGCCTGAGAGCCGAGGA CACGGCTGTGTATTACTGTGCGAGAGTCAACGGT ATGGACGTCTGGGGCCAAGGGACCACGGTCACC GTCTCCTCA<br><br>SEQ ID NO: 29151 |

FIGURE 50
(Continued)

| | | | |
|---|---|---|---|
| iPS:402231 | 21-225_6D9 | AA | DIQMTQSPSSLSASVGDRVTITCRASQGIRNYLG WFQQKPGKAPKRLIYGASSLQSGVPSRISGSGSG TEFTLTISSLQPEDFATYYCLQYHSYLFTFGPGTK VDIK<br><br>SEQ ID NO: 25146 | EVQLVESGGGLVKPGGSLRLSCAASGFTFSSYSMN WVRQAPGKGLEWVSSISGSSSYIYYADSVKGRFTIS RDNAKNSLYLQMNSLRAEDTAVYYCARVNGMDV WGQGTTVTVSS<br><br>SEQ ID NO: 29152 |
| | | NA | TCCTATGAGCTGACTCAGCCACCCTCAGTGTC CGTGTCCCCAGGACAGACAGCCAGCATCACCT GCTCTGGAGATATCAGCAGAAAAATATGCT TGCTGGTATCAGCAGAAGCCAGGCCAGTCCCC TGTACTGGTCATCTATCAAGATAAGAAGCGGC CCTCAGGGATCCCTGAGCGATTCTCTGGCTCC AACTCTGGGAACACAGCCACTCTGACCATCAG CGGGACCCAGGCTATGATGAGGCTGACTATT ACTGTCAGGCGTGGGACAGCAGCACTGTATTC GGCGGAGGGACCAAACTGACCGTCCTA<br><br>SEQ ID NO: 25147 | GAGGTGCAGCTGGTGGAGTCTGGGGGAGGCTTG GTAAAGCCTGGGGGGTCCCTTAGACTCTCCTGTG CAGCCTCTGGATTCACTTTCAGTAACGCCTGAT GAACTGGGTCCGCCTGGCTCCAGGGAAGGGCT GGAGTGGGTTGGCCGTATTAAAAGCAAAACTGA TGGTGGGACAACAGACTACGCTGCACCGTGAA AGGCAGATTCACCATCTCAAGAGATGATTCAGA AACACGTTGTATCTGCAAATGAACAGCCTGAA AACCGAGGACACAGCCGTGTATTACTGTTCCACA GATACGGTCCTATAGCAGCTCGTCTGCTTACT ACTACTACGCTATGGACGTCTGGGGCCAAGG GACCACGGTCACCGTCTCCTCA<br><br>SEQ ID NO: 29153 |
| | | AA | SYELTQPPSVSVSPGQTASITCSGDKLGEKYACW YQQKPGQSPVLVIYQDKKRPSGIPERFSGSNSGN TATLTISGTQAMDEADYYCQAWDSSTVFGGGT KLTVL<br><br>SEQ ID NO: 25148 | EVQLVESGGGLVKPGGSLRLSCAASGFTFSNAWM NWVRLAPGKGLEWVGRIKSKTDGGTTDYAAPVKG RFTISRDDSENTLYLQMNSLKTEDTAVYYCSTDTGP IAARLAYYYYAMDVWGQGTTVTVSS<br><br>SEQ ID NO: 29154 |

FIGURE 50
(Continued)

| | | | | |
|---|---|---|---|---|
| iPS:402233 | 21-225_16D10 | NA | GACATCCAGATGACCCAGTCTCCATCCTCACT GTCTGCATCTGTAGGAGACAGAGTCACCATCA CTTGTCGGGCGAGTCAGGACATCAGCAATAAGTAATTAT TTAGCCTGGTTTCAGCAGAAACCAGGGAAAGC CCCTAAGTCCCTGATCTATGCTACACCCAGTTT GCAGAGTGGGGTCCCATCAAAGTTCAGCGGCA GTGGATCTGGGACAGAGTTCACTCTCACCATC AGCAGCCTGCAGCTGAAGATTTTGCAACTTA TTACTGCCAACAGTATATAATAGTTACCCGCTCA CTTTCGGCGGAGGGACCAAGGTGGAGATCAA A <br> SEQ ID NO: 25149 | GAGGTGCAACTGGTGGAGTCTGGGGAGGCTG GTCAAGCCTGGGGGGTCCCTGAGACTCTCCTGTG CAGCCTCTGGATTCACCTTCAGTAGTACTTAT AACTTGAACTGGGTCCGCCAGGCTCCAGGGAAGGGCT GGAGTGGGTCTCATCCATTAGTGGTGTGCCCGGT CACATATATTACTCAGAGACAACGCCAAGAACTACT TCACCATCTCCAGAGACAATGAACAGCCTGAGAGCCGAGGA GTATCTGCAAATGAACAGCCTGAGAGCCGAGGA CACGGCTGTGTATTACTGTGCGAGGGACTAATGG TTTGACTTCTGGGGCCAGGGAACCCTGGTCACCG TCTCCCTCA <br> SEQ ID NO: 29155 |
| | | AA | DIQMTQSPSSLSASVGDRVTITCRASQDISNYLA WFQQKPGKAPKSLIYATPSLQSGVPSKFSGSGSG TEFTLTISSLQPEDFATYYCQQYNSYPLTFGGGT KVEIK <br> SEQ ID NO: 25150 | EVQLVESGGGLVKPGGSLRLSCAASGFTFSTYNLN WVRQAPGKGLEWVSSISGGAGHIYYSDSVKGRFTI SRDNAKNSLYLQMNSLRAEDTAVYYCARTNGFDF WGQGTLVTVSS <br> SEQ ID NO: 29156 |
| iPS:402235 | 21-225_20F10 | NA | GACATCCAGATGACCCAGTCTCCATCCTCACT GTCTGCATCTGTCGGAGACAGAGTCACCATCA CTTGTCGGGCGAGTCAGGACATCAGCAATAAGTAATTAT TTAGCCTGGTTTCAGCAGAAACCAGGGAAAGC CCCTAAGTCCCTGATTTATGCTGCATCCAGTTT GCAAAGTGGGGTCCCATCAAGGTTCAGCGGCA GTGGATTTGGGACAGAATTCACTCTCACCATC AGCAGCCTGCAGCAATAATAGTTACCCATTCA CTTTTGGCCCTGGGACCAAAGTGGATAAACAAA <br> SEQ ID NO: 25151 | GAGGTGCAGCTGGTGGAGTCTGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGCT GGAGTGGGTCTCATCCATTAGTAGTACTAGTTTC ATATACTACGCAGATTCAGTGAAGGGCCGATTCA CCATCTCAAGAGACAACGCCAAGAACTACTCACTGT ATCTGCAAATGAACAGCCTGAGAGCCGAGGACA CGGCTGTGTATTACTGTGCGAGAAAGGCTGGCT TGATATCTGGGGCCAAGGGACAATGGTCACCGTC TCTTCA <br> SEQ ID NO: 29157 |

FIGURE 50
(Continued)

| | | | |
|---|---|---|---|
| | | AA | DIQLTQSPSSLSASVGDRVTITCRASQGINNYLA WFQQKPGKAPKSLIYAASSLQSGVPSRFSGSGFG TDFTLTISSLQPEDFATFYCQQYNSYPFTFGPGTK VDNK<br>SEQ ID NO: 25152 | EVQLVESGGGLVKPGGSLRLSCAASGFTFSSYSMN WVRQAPGKGLEWVSSISTSTFIYADSVKGRFTISR DNAKNSLYLQMNSLRAEDTAVYYCARKAGLDIWG QGTMVTVSS<br>SEQ ID NO: 29158 |
| iPS:402237 | 21-225_23D11 | NA | GACATCCAGATGACCCAGTCTCCATCCTCACT GTCTGCATCTGTAGGGGACAGAGTCACCATCA CTTGTCGGGCGAGTCAGGGCATTCAGGGCATTTAT TTAGCCTGGTTTCAGCAGAGACCAGGGAAAGC CCCTAAGTCCCTGATCTCTGCTGCATCCAGTTT GCAAAGTGGGGTCCCATCAAGGTTCAGCGGCA GTGGATCTGGGACAGAGTTCACTCTCACCATC AGCAGCCTGCAGCCTGAAGATTTTGCAACTTA TTACTGCCAACAGTATCATAGTTACCCGCTCA CTTTCGGCGGAGGGTCCAAGGTGGAGATCAAA<br>SEQ ID NO: 25153 | GAGGTGCAGCTGGTGGAGTCTGGGGGAGGCCTG GTCAAGCCTGGGGGGTCCCTGAGACTCTCCTGTG CAGCCCTCTGATTCACCTTCAGTAGCTATAACAT AAACTGGGTCCGCCAGGCTCCAGGGAAGGGGCT GGAGTGGGTCTCATCCATTAGTGGTAATAGTGGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGCGAACTAACCTC TTTGACTACTGGGGCCAGGGAACCCTGGTCACCG TCTCCTCA<br>SEQ ID NO: 29159 |
| | | AA | DIQMTQSPSSLSASVGDRVTITCRASQGIANYLA WFQQRPGKAPKSLISAASSLQSGVPSKFSGSGSG TEFTLTISSLQPEDFATYYCQQYHSYPLTFGGGS KVEIK<br>SEQ ID NO: 25154 | EVQLVESGGGLVKPGGSLRLSCAASGFTFSSYNIN WVRQAPGKGLEWVSSISGNSGYIYYADSVKGRFTI SRDNAKNSLYLQMNSLRAEDTAVYYCARTNLFDY WGQGTLVTVSS<br>SEQ ID NO: 29160 |

FIGURE 50
(Continued)

| | | | |
|---|---|---|---|
| iPS:403868 | 21-225_19D11 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGAAAGCCCCTAAGCGCCTGATCTATGCTACATCCAGTTTGCAAAGTGGGGTCCCATCAAGGTTCAGCGGCAGTGGATCTGGGACAGAATTCACTCTCACAATCAGCAGCCTGCAGCCTGAGGATTTTGCAACTTATTACTGTCTACAGTATTATAGTTACCCGCTCACTTTCGGCGGAGGGACCGAGGTGGAGATCAA<br>SEQ ID NO: 25155 | CAGCTGCAGCTGCAGGAGTCGGGCCCAGGACTGGTGAAGCCTTCGGAGACCCTGTCCTCACCTGCACTGTCTCTGGTGGCTCCATCAGCAGAAGTAGTTATTACTGGGGCTGGATCCGCCAGCCCCCGGAAGGGGCTGGACTGGATTGGGAGTATCTATTATAGTGGGAGCGCCAACTACAACCCGTCCCTCAAGAGTCGAGTCACCATATCCGTAGACACGTCCAAGAACCAGTTCTCCCTGAAACTGAGTTCCGTGACCGCGCAGACGCGGCTGTGTATTACTGTGCGAGACTGGACAGGGGCTGGTCCTTTGACTACTGGGGCCAGGGAACCCTGGTCACCGTCTCCTCA<br>SEQ ID NO: 29161 |
| | | AA | DIQMTQSPSSLSASVGDRVTITCRASQGIRNDLGWYQQKPGKAPKRLIYATSSLQSGVPSRFSGSGSGTEFTLTISSLQPEDFATYYCLQYYSYPLTFGGGTEVEIK<br>SEQ ID NO: 25156 | QLQLQESGPGLVKPSETLSLTCTVSGGSISRSSYYWGWIRQPPGKGLDWIGSIYYSGSANYNPSLKSRVTISVDTSKNQFSLKLSSVTAADAAVYYCARLDRGWSFDYWGQGTLVTVSS<br>SEQ ID NO: 29162 |
| iPS:403870 | 21-225_23G4 | NA | GACATCCAGATGACCCAGTCTCCATCCTCCCTGTCTGCATCTGTGGGAGACAGAGTCACCATCACTTGCCGGGCAAGTCAGAGCATTTACAGCTATTTAAATTGGTATCAGCAGAAACCTGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCTGCAACAGAGTTACAATACCCCTCCGGAGTGCAATTTTGGCCAGGGACCAAGCTGGAGATCAAA<br>SEQ ID NO: 25157 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGTTATTAGTGGCGTGGTGGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGGGGGATAGTGGAGCTACTGAGGCTTTTGATATCTGGGGCCAAGGGACAATGGTCACCGTCTCTTCA<br>SEQ ID NO: 29163 |

FIGURE 50
(Continued)

| | | | |
|---|---|---|---|
| | | AA | DIQMTQSPSSLSASVGDRVTITCRASQNIYSYLN WYQQKPGKAPKLLIYAASSLQSGVPSRFSGSGS GTEFTLTISILQPEDFATYYCQQSYNTPPECNFGQ GTKLEIK<br>SEQ ID NO: 25158 | EVQLLESGGGLVQPGGSLRLSCAASGFTFSSYAMS WVRQAPGKGLEWVSVISGRGGSTYYADSVKGRFTI SRDNSKNTLYLQMNSLRAEDTAVYYCAKRGIVGA TEAFDIWGQGTMVTVSS<br>SEQ ID NO: 29164 |
| iPS:403872 | 21-225_8F11 | NA | GACATCCAGATGACCCAGTCTCCATCCTCCCT GTCTGCATCTGTAGGAGACAGAGTCACCATCA CTTGCCGGGCAAGTCAGGGCATTAGGAGTGAT TTAGGCTGGTTTCAGCAGAAACCAGGGAAAGC CCCTAAGCGCCTGATCTTTGATGCATCCAGTG TGCAAAGTGGGGTCCCATCAAGGTTCAGCGGC AGTGGATCTGGGACAGAGAATTCACTCTCACAAT CAGCAGCCTGCAGCCTGAAGATTTTGCAATTT ATTACTGTCTACAACATTATACTTACCGCTCA CTTTCGGCGGAGGGACCAAGGTGGAGATCAA G<br>SEQ ID NO: 25159 | CAGCTGCAGCTGCAGGAGTCGGGCCCAGGACTG GTGCAGCCTTCCGAGACCCTGTCCCTCACCTGCA CTGTCTCTGGTGTCTCCATCAGTAGGACTAGTTA CTACTGGGGCTGGCTCCGCCAGCCCCCAGGGAA GGGGCTGGAGTGGATTGGCAATATTATTATAGT GGGAGCGCCTACAACAACCCGTCCTCCAAGAGT CGAGTCACCATATCCGTTGACACGTCCAAGAACC AGTTCTCCCTGAAGCTGAGTTCTGTGACCGCCGC AGACACGGCTGTGTATTACTGTGGGAGACATGGA CAAGACTGGGGCCTTGACTACTGGGGCCAGGGA ACCCTGGTCACCGTCTCCTCA<br>SEQ ID NO: 29165 |
| | | AA | DIQMTQSPSSLSASVGDRVTITCRASQGIRSDLG WFQQKPGKAPKRLIFDASSVQSGVPSRFSGSGSG TEFTLTISSLQPEDFAIYYCLQHYTYPLTFGGGTK VEIK<br>SEQ ID NO: 25160 | QLQLQESGPGLVQPSETLSLTCTVSGVSISRTSYYW GWLRQPPGKGLEWIGNIYYSGSAYNNPSLKSRVTIS VDTSKNQFSLKLSSVTAADTAVYYCGRHGQDWGL DYWGQGTLVTVSS<br>SEQ ID NO: 29166 |

FIGURE 50
(Continued)

| | | | |
|---|---|---|---|
| iPS:404090 | 21-225_8D8 | NA | TCCTATGAGCTGACTCAGCCACCCTCAGTGTC CGTGTCCCCAGGACAGAGCCAGCATCACCT GCTCTGGAGATAAATTGGGGGAGAAATATGCT TGCTGGTATCAGCAGAAGCCAGGCCAGTCCC TGTGGTGGTCTCATCTATCAAGATAGGAAGCGGC CCTCAGGGATCCCTGAGCGATTCTCTGGCTCC AACTCTGGGAACACAGGCCACTCTGACCATCAG CGGGACCCAGGCTATAGATGAGGCTGACTATT ACTGTCAGGCGTGGGACAGCAGCACTGCCGTA TTCGGCGGAGGGACCAAGTTGACCGTCCTA | GAGGTGCAGCTGTGGAGTCTGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGTAGT TACATATACTACGCAGAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGCGTCTGGGTAAC TACTGGGGCCAGGGAACCCTGGTCACCGTCTCCT CA |
| | | | SEQ ID NO: 25161 | SEQ ID NO: 29167 |
| | | AA | SYELTQPPSVSVSPGQTASITCSGDKLGEKYACW YQQKPGQSPVVVIYQDRKRPSGIPERFSGSNSGN TATLTISGTQAIDEADYYCQAWDSSTAVFGGGT KLTVL | EVQLVESGGGLVKPGGSLRLSCAASGFTFSSYSMN WVRQAPGKGLEWVSSISSSSYIYADSVKGRFTIS RDNAKNSLYLQMNSLRAEDTAVYYCARLGNYWG QGTLVTVSS |
| | | | SEQ ID NO: 25162 | SEQ ID NO: 29168 |
| iPS:412232 | 21-225_4A2 | NA | GACATCGTGATGACCCAGTCTCCAGACTCCCT GGCTGTGTCTCTGGGCGAGAGGGCCACCATCA ACTGCAAGTCCAGCCAGAGTGTATTTTACACAGC TCCAACAATAACAGGACAACTACTAGCTTGTTCCA GCAGAAACCAGGACAGCCTCCTAAACTGCTCC TTTACTGGGCATCTACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATACTCCAGTCACTTTCGGCCCTGGG ACCAAAGTGGGGTATCAAA | CAGGTGCAGCTGGTGCAGTCTGGGACTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG AGTCACCTTGACCAGGAACACCTCCATAAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTCTCCTCA |
| | | | SEQ ID NO: 25163 | SEQ ID NO: 29169 |

FIGURE 50
(Continued)

| | | | |
|---|---|---|---|
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNTP VTFGPGTKVGIK<br>SEQ ID NO: 25164 | QVQLVQSGTEVKKPGASVKVSCKASGYTFTNYDIN WVRQATGQGLEWMGWMHPNSGNTGYAQKFQGR VTLTRNTSISTAYMELSSLRSEDTAVYYCASSSGWY YFDYWGQGTLVTVSS<br>SEQ ID NO: 29170 |
| iPS:422894 | 21-225_4A2.001 | NA | GACATCGTGATGACCCAGTCTCCAGACTCCCT GGCTGTGTCTCTGGGCGAGAGGGCCACCATCA ACTGCAAGTCCAGCCAGAGTATTTTACACAGC TCCAACAATAACAACTACTTAGCTTGGTTCCA GCAGAAACCAGGACAGCCTCCTAAACTGCTCC TTTACTGGGCATCTCACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATACTCCAGTCACTTTCGGCCCTGGG ACCAAAGTGGGTATCAAA<br>SEQ ID NO: 25165 | CAGGTGCAGCTGGTGCAGTCTGGGACTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCTTGACCAGGAACACCTCCATAAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br>SEQ ID NO: 29171 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNTP VTFGPGTKVGIK<br>SEQ ID NO: 25166 | QVQLVQSGTEVKKPGASVKVSCKASGYTFTNYDIN WVRQATGQGLEWMGWMHPNSGNTGYAQKFQGR VTLTRDTSISTAYMELSSLRSEDTAVYYCASSSGWY YFDYWGQGTLVTVSS<br>SEQ ID NO: 29172 |

FIGURE 50
(Continued)

| | | | | |
|---|---|---|---|---|
| iPS:423018 | 21-225_31D12_LC2 | NA | TCCTATGAGCTGACTCAGCCACCCTCAGTGTCCGTGTCCCCAGGACAGAGACAGCCAGCATCACCTGCTCTGGAGATAAATTGGGGGATAAATATGCTTACTGGTTTCAGCAGAAGCCAGGCCAGTCCCCTGTGATAGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACAACAGCACTGCGGTATTCGGCGGAGGGACCAAGCTGACCGTCCTA<br>SEQ ID NO: 25167 | CAGGTGAAGCTGGTGCAGTCTGGGGCTGAGGTGAAGAAGCCTGGGGCCTCAGTGAAGGTCTCCTGCAAGGCTTCAGGATACACCTTCACCGGCTACTATATGCACTGGGTGCGACAGGCCCCTGGACAAGGGCTTGAGTGGATGGGATGGATCAACCCTAACAGTGGTGGCACAAACTATGTACAGAAGTTTCAGGGCAGGGTCACCATGACCAGGGACACGTCCATCAGCACAGCCTACATGGAGCTGAGCAGGCTGAGATCTGACACGGCCGTGTATTACTGTGCGAGAGTGTATTACTATGGTTCGGGGAGTTATTATAACGAGTTTGACTACTGGGGCCAGGGAACCCTGGTCACCGTCTCCTCA<br>SEQ ID NO: 29173 |
| | | AA | SYELTQPPSVSVSPGQTASITCSGDKLGDKYAYWFQQKPGQSPVIVIYQDRKRPSGIPERFSGSNSGNTATLTISGTQAMDEADYYCQAWDNSTAVFGGGTKLTVL<br>SEQ ID NO: 25168 | QVKLVQSGAEVKKPGASVKVSCKASGYTFTGYYMHWVRQAPGQGLEWMGWINPNSGGTNYVQKFQGRVTMTRDTSISTAYMELSRLRSDDTAVYYCARVYYYGSGSYYNEFDYWGQGTLVTVSS<br>SEQ ID NO: 29174 |
| iPS:423019 | 21-225_31D12_LC1 | NA | GATGTTGTGATGACTCAGTCTCCACTCTCCCTGCCCGTCACCCTTGGACAGCCGGCCTCCATCTCCTGCAGGTCTAGTCAAAGCCTCATATACAGTGATGGAAACACCTTCTTGAATTGGTTTCAGCAGAGGCCAGGCCAATCTCCAAGGCGCCTAATTTATAAGGTTTCTAATTGGGACTCTGGGGTCCCAGACAGATTCAGCGGCAGTGGGTCAGGCACTGATTTCACACTGAAAATCAGCAGGGTGGAGGCTGAGGATGTTGGGGATTTATTACTGCATGCAAGGTACACACTGGCCTCTCACCTTCGGCCAAGGGACACGACTGGAGATTAAA<br>SEQ ID NO: 25169 | CAGGTGAAGCTGGTGCAGTCTGGGGCTGAGGTGAAGAAGCCTGGGGCCTCAGTGAAGGTCTCCTGCAAGGCTTCAGGATACACCTTCACCGGCTACTATATGCACTGGGTGCGACAGGCCCCTGGACAAGGGCTTGAGTGGATGGGATGGATCAACCCTAACAGTGGTGGCACAAACTATGTACAGAAGTTTCAGGGCAGGGTCACCATGACCAGGGACACGTCCATCAGCACAGCCTACATGGAGCTGAGCAGGCTGAGATCTGACACGGCCGTGTATTACTGTGCGAGAGTGTATTACTATGGTTCGGGGAGTTATTATAACGAGTTTGACTACTGGGGCCAGGGAACCCTGGTCACCGTCTCCTCA<br>SEQ ID NO: 29175 |

FIGURE 50
(Continued)

| | | | |
|---|---|---|---|
| | | AA | DVVMTQSPLSLPVTLGQPASISCRSSQSLIYSDGN TFLNWFQQRPGQSPRRLIYKVSNWDSGVPDRFS GSGSGTDFTLKISRLEAEDVGIYYCMQGTHWPL TFGQGTRLEIK<br>SEQ ID NO: 25170 | QVKLVQSGAEVKKPGASVKVSCKASGYTFTGYYM HWVRQAPGQGLEWMGWINPNSGGTNYVQKFQGR VTMTRDTSISTAYMELSRLRSDDTAVYYCARVYYY GSGSYYNEFDYWGQGTLVTVSS<br>SEQ ID NO: 29176 |
| iPS:423314 | 21-225_12F11 | NA | GACATCGTGATGACCCAGTCTCCAGACTCCCT GGCTGTGTCTCTGGGCGAGAGGGCCACCATCA ATTGCAAGTCCAGCCAGAGTGTTTACACAGC TCCAACAATTATAACTACTTAGCTTGGTACCA GCAGAAACCAGGACAGCCTCCTAACCTGCTCA TTTTCTGGGCATCTACCCGGGAATCCGGGGTC CCTGACCGATTCAGTGGCAGCGGGTTTGGGAC AGATTTCACTCTCAACATCAGCAGCCTGCAGG CTGAAGATGTGGCAGTTTATTACTGTCAGCAA TATTATGATACTCCATTCACTTTCGGCCCTGGG ACCAAAGTGGATATCAAA<br>SEQ ID NO: 25171 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC CTGAGTGGATGGGATGGATGCACCTAACAGTG GTAACACAGGCTATGCAAAGAAGTTCCAGGCA GAGTCACCATGACCAGGAACACCTCCATAAGCG CAGCCTATATGGTTCTGAGCAGCCTGAGATCTGA GGACACGGCCGTGTATTACTGTGCGCTTAGCAGT GGCTGGTACTTTGACTACTGGGGCCAGGGAA CCCTGTCACCGTCCTCCTCA<br>SEQ ID NO: 29177 |
| | | AA | DIVMTQSPDSLAVSLGERATINCKSSQSVLHSSN NYNYLAWYQQKPGQPPNLLIFWASTRESGVPDR FSGSGFGTDFTLNISSLQAEDVAVYYCQQYYDTP FTFGPGTKVDIK<br>SEQ ID NO: 25172 | QVQLVQSGAEVKKPGASVKVSCKASGYTFTNYDIN WVRQATGQPEWMGWMHPNSGNTGYAKKFQGR VTMTRNTSISAAYMVLSSLRSEDTAVYYCALSSGW YYFDYWGQGTLVTVSS<br>SEQ ID NO: 29178 |

FIGURE 50
(Continued)

| | | | |
|---|---|---|---|
| iPS:424419 | 21-225_25A4.001 | NA | GACATCGTGATGACCCAGTTTCCAGACTCCCTGGCTGTGTCTCTGGGCGAGAGGGCCACCATCAAGTGTAAGTCCAGCCAGAGTGTTTTATACAGCTCCCACAATAACAACTACTTAGCTTGGTACCAGCAGAAACCAGGACAGCCTCCTAAGTTGCTCCTTTACTGGGCATCTACCCGGGAATCCGGGGTCCCTGACCGATTCAGTGGCAGCGGGTCTGGGACAGAATTCACTCTCACCATCAGCAGCCTGGAGGCTGAAGATGTGGCAGTTTATTACTGTCAGCAGTATTATAGTACTCCTCGACGTTCGGCCAAGGGACCAAGGTGGAAATCAAA |
| | | | CAGGTGCTCCTGGTGCAGTCTGGGGCTGAGGTGAAGAGGCCTGGGGCCTCAGTGAAGGTCTCCTGCAAGGCTTCTGGATACACCTTCACCAATTATGATATTAATTGGGTGCGACAGGCCACTGGACAAGGGCTTGAGTGGATGGGATGGATGTACCCTAACAGTGGTAACACAGGCTATGCACAGAAATTCCAGGGCAGAGTCACCATGACCAGGGACACCTCCATCAGCACAGCCTACATGGAGCTGAGCAGCCTGAGATCTGAGGACACGGCCGTCTATTACTGTGCGAGTAGCAGTGGCTGGTACTACTTTGACTACTGGGGCCAGGGAACCCTGGTCACCGTGTCCTCA |
| | | | SEQ ID NO: 25173 | SEQ ID NO: 29179 |
| | | AA | DIVMTQFPDSLAVSLGERATIKCKSSQSVLYSSHNNNYLAWYQQKPGQPPKLLLYWASTRESGVPDRFSGSGSGTEFTLTISSLEAEDVAVYYCQQYYSTPPTFGQGTKVEIK | QVLLVQSGAEVKRPGASVKVSCKASGYTFTNYDINWVRQATGQGLEWMGWMYPNSGNTGYAQKFQGRVTMTRDTSISTAYMELSSLRSEDTAVYYCASSSGWYYFDYWGQGTLVTVSS |
| | | | SEQ ID NO: 25174 | SEQ ID NO: 29180 |
| iPS:424460 | 21-225_7E11.001 | NA | GACATCCAGATGACCCAGTCTCCATCCTCCCTGTCTGCATCTGTAGGAGACAGAGTCACCATCGCTTGCCGGGCAAGTCAAAACATTATCAGCTATTTAAATTGGTATCAACAGAAACCAGGAAAGCCCCTAAATTCCTGATCTATACTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGACTTACAGTACCCCGCTCACTTTCGGCGGGGGACCAAGGTGGAGATCAA | CAGGTGCAGCTGGTGGTGCAGTCTGGGGGAGGCGTGGTCCAGCCTGGGAGGTCCCTGCGACTCTCCTGTGCAGCGTCTGGATTCACCTTCAGTGAGTACTGCATGCACTGGGTCCGCCAGGCTCCAGGCAAGGGGCTGGAGTGGGTGGCAATTATCTGGACTGGGATGAAGTAATAAATACTATGCAGACTCCGTGAAGGGCCGATTCACCATCTCCAGAGACAATTCCAAAAACACGCTGTATCTGCAAATGAGCAGCCTGCGAGCCGAGGACACGGCTGTGTATTACTGTGCGAGAGATCGAGTATGGGCGGTATGGACGTCTGGGGCCAAGGGACCACGGTCACCGTGTCCTCA |
| | | | SEQ ID NO: 25175 | SEQ ID NO: 29181 |

FIGURE 50
(Continued)

| | | | |
|---|---|---|---|
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK SEQ ID NO: 25176 | QVQLVESGGGVVQPGRSLRLSCAASGFTFSSFGMH WVRQAPGKGLEWVAIIWHDGSNKYYADSVKGRFT ISRDNSKNTLYLQMSSLRAEDTAVYYCARDLSMGG MDVWGQGTTVTVSS SEQ ID NO: 29182 |
| iPS:426108 | 21-225_10G6 | NA | GACATCCAGATGACCCAGTCTCCATCTTCCGT GTCTGCATCTGTGGGAGACAGAGTCACCATCA CTTGTCGGGCGAGTCAGGGTATTAGCAAATGG TTAGCCTGGTATCAGCAGAAACCAGGGAAAG CCCCTAAGATCCTGATATATGCTGCATATAGT TTACAAAGTGGGGTCCCAGCAAGGTTCAGCGG CAGTGGATCTGGGACAGATTTCACTCTCACCA TCAGGAGCCTGCAGCCTGAAGATTTTGCAACT TACTATTGTCAACAGGCTAACAGTTTCCCATTC ACTTTCGGCCCTGGGACCAAAGTGGATATCAA A SEQ ID NO: 25177 | CAGGTGCAGCTGGTGCAGTCTGGGGCTGAGGTG AAGAAGCCTGGGGCCTCAGTGAAGGTCTCCTGC AAGGCTTCTGGATACACCTTCACCGCCTACCATA TGCACTGGGTGCGACAGGCCCCTGGACAAGGAC TGGAGTGGATGGGATGGATCAACCCTAACAATAA TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTTTATTACTGTGGGAGAGATGTT ACCAGTCGTTTGACTATTGGGGCCAGGGAACCC TGGTCACCGTCTCCTCA SEQ ID NO: 29183 |
| | | AA | DIQMTQSPSSVSASVGDRVTITCRASQGISKWLA WYQQKPGKAPKILIYAAYSLQSGVPARFSGSGS GTDFTLTIRSLQPEDFATYYCQQANSFPFTFGPGT KVDIK SEQ ID NO: 25178 | QVQLVQSGAEVKKPGASVKVSCKASGYTFTAYHM HWVRQAPGQGLEWMGWINPNNNGTNYAQKFQGR VTMTRDTSISTAYMELSRLRSDDTAVYYCGRDVTS SFDYWGQGTLVTVSS SEQ ID NO: 29184 |

FIGURE 50
(Continued)

| | | | |
|---|---|---|---|
| iPS:426110 | 21-225_12E9 | NA | GACATCCAGATGACCCAGTCTCCATCTTCCGT GTCTGCATCTGTAAGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCTGCATCCAGG TTGCAAAGTGGGGTCCCATCAAGGTTCAGCGG CAGTGGATCTGGGACAGATTTCACTCTCACCA TCAGCAGCCTGCAGCCTGAAGATTTTGCAACT TACTATTGTCAACAGGCTAACAGTTTCCCATTC ACTTTCGGCCCTGGGACCAAAGTGGATATCAA A | CAGGTGCAGCTGTGTACAGTCTGGGGCTGAGGTG AAGAAGCCTGGGGCCTCAGTGAAGGTCTCCTGC AAGGCTTCTGGATACACCTTCACCGACTACTATT TGCACTGGGTGCGACAGGCCCCTGGACAAGGTCT TGAGTGGATGGGATGGGTCCACCCTAACAGTGGT GGCACAAACTTTGCACAGAAGTTTCAGGACAGG GTCACCATGACCAGGGACACGTCCATCAGCACA GCCTACATGGAGCTGAGCAGCCTGAGATCTGAC GACACGGCCATATATTCCTGTGCGCGAGATGGTA CCAGCTCGTTTGACTACTGGGGCCAGGGAACCCT GGTCACCGTCTCCTCA |
| | | | SEQ ID NO: 25179 | SEQ ID NO: 29185 |
| | | AA | DIQMTQSPSSVSASVRDRVTITCRASQGISSWLA WYQQKPGEAPKLLIYAASRLQSGVPSRFSGSGS GTDFTLTISSLQPEDFATYYCQQANSFPFTFGPGT KVDIK | QVQLVQSGAEVKKPGASVKVSCKASGYTFTDYYL HWVRQAPGQGLEWMGWIHPNSGGTNFAQKFQD RVTMTRDTSISTAYMELSSLRSDDTAIYSCARDGTS SFDYWGQGTLVTVSS |
| | | | SEQ ID NO: 25180 | SEQ ID NO: 29186 |
| iPS:426112 | 21-225_12F12 | NA | GACATCGTGATGACCCAGTCTCCAGACTCCCT GGCTGTGTCTCTGGGCGAGAGGGCCACCATCA ACTGCAAGTCCAGCCAGAGTGTTTATTCAGC TCCAACAATAACCACTACTTAGCACTGGTACCA GCAGAAACCAGGACAGCCTCCTAAGCTCCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTAGTCCGTTGACGTTCGGCCAAGG GACCAAGGTGGAAATCAAA | CAGGTGCAGCTGCTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCTAACAGTGG TAACACGGGCTATGCACAGAAGTTCCAGGGCAG AGTCACCATGACCATGACCATGACCCATAAGCACA GCCTACATGGAGTTGAGCAGCCTGAGATCTGAG GACACGGCCGTGTATTACTGTGCGAGCAGTGAG GCTGGTACTACTTTGACTTCTGGGGCCAGGGAAC CCTGGTCACCGTCTCCTCA |
| | | | SEQ ID NO: 25181 | SEQ ID NO: 29187 |

FIGURE 50
(Continued)

| | | | |
|---|---|---|---|
| | | AA | DIVMTQSPDSLAVSLGERATINCKSSQTVLFSSN NNHYLAWYQQKPGQPPNLLIYWASTRASGVPD RFSGSGSGTDFTLTISSLQAEDVAVYYCQQYYSS PWTFGQGTKVEIK<br>SEQ ID NO: 25182 | QVQLLQSGAEVKKPGASVKVSCKASGYTFTNYDIN WVRQATGQGLEWMGWMYPNSGNTGYAQKFQGR VTMTMNTSISTAYMELSSLRSEDTAVYYCAMSSG WYYFDFWGQGTLVTVSS<br>SEQ ID NO: 29188 |
| iPS:426114 | 21-225_28H2 | NA | GACATCCAGATGACCCAGTCTCCTTCCTCCT GTCTGCATCTATAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATTTATGCTGCATCCAGTT TGCAAAGTGGGGTCCCATCAAGGTTCAGCGGC AGTGGATCTGGGACAGACCTGAAGATTTTGCAACTT ATTACTGTCTACAACATTATAGTTACCCTCGCA GTTTTGGCCAGGGGACCAAGCTGGAGATCAAA<br>SEQ ID NO: 25183 | CAGGTGCAGCTGGTGGAGTCTGGGGGAGGCGTG GTCCAGCCTGGGAGGTCCCTGAGACTCTCCTGTG CAGCGTCTGATTCACCTTCAGTAACTATGTCAT GCACTGGGTCCGCCAGGCTCCAGGCAAGGGCT GGAGTGGGTGGCAGTTATATGCAGACTCCGTGAAGT AATAAGTACTATGCAGACTCCGTGAAGGGCCGA TTCACCATCTCCAGAGACAATTCCAAGAACACGC TGTATCTACAAATGAACAGCCTGAGAGCCGTGG ACACGGCTGTGTATTACTGTGCGAGAGAGGAGTA TAGCAGTGGCTGGTACGACTACGGTATGGACGTC TGGGGCCAAGGGACCACGGTCACCGTCTCCTCA<br>SEQ ID NO: 29189 |
| | | AA | DIQMTQSPSSLSASIGDRVTITCRASQGIRNDLG WYQQKPGKAPKRLIYAASSLQSGVPSRFSGSGS GTEFTLTISSLQPEDFATYYCLQHYSYPRSFGQG TKLEIK<br>SEQ ID NO: 25184 | QVQLVESGGGVVQPGRSLRLSCAASGFTFSNYVM HWVRQAPGKGLEWVAVIWYDGSNKYYADSVKGR FTISRDNSKNTLYLQMNSLRAVDTAVYYCAREEYS SGWYDYGMDVWGQGTTVTVSS<br>SEQ ID NO: 29190 |

FIGURE 50
(Continued)

| | | | | |
|---|---|---|---|---|
| iPS:426116 | 21-225_29E2 | NA | GACATCCAGATGACCCAGTCTCCATCCTCCT GTCTGCATCTGTAGGAGACAGAGTCACCATCA CTTGCCGGGCAAGTCAGCAGCCATTAGAAATGAT TTAGGCTGGTATCAGCAGAAACCAGGGAAAG CCCCTAAGCGCCTGATCTATCTGCATCCAGT TTGCAAAGTGGGGTCCCATCAAGGTTCAGCGG CAGTGGATCTGGGACAGAATTTATTCTCACAA TCAGCAGCCTGCAGCCTGAAGATTTTGCAACT TATTACTGTTTACAGCATTATAATTACCCTGC AGTTTTTGGCCAGGGGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGATTCACCTTCAGTAACTGTGTCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA ATCACCATCTCCAGAGACAATTCCAAGAACACGC TGTATCTGCAAATGAACAGCCTGAGAGCCGAGG ACACGGCTGTGTATTACTGTGCGAGAGAGGAGTA TAGCAGTGGCTGGTACGACTACGGTATGGACGTC TGGGGCCAAGGGACCACGGTCACCGTCTCCTCA |
| | | | SEQ ID NO: 25185 | SEQ ID NO: 29191 |
| | | AA | DIQMTQSPSSLSASVGDRVTITCRASQAIRNDLG WYQQRPGKAPKRLIYAASSLQSGVPSRFSGSGS GTEFILTISSLQPEDFATYYCLQHYNYPRSFGQGT KLEIK | QVQLVESGGGVVQPGRSLRLSCAASGFTFSNCVMH WVRQAPGKGLEWVAVIWYDGSNKYYADSVKGRI TISRDNSKNTLYLQMNSLRAEDTAVYYCAREEYSS GWYDYGMDVWGQGTTVTVSS |
| | | | SEQ ID NO: 25186 | SEQ ID NO: 29192 |
| iPS:426118 | 21-225_7A10 | NA | GACATCCAGATGACCCAGTCTCCATCCTCCCT GTCTGCATCTGTAGGAGACAGAGTCACCATCA CTTGCCGGGCAAGTCAGAGCAGTTACAGCTAT TTAAATTGGTATCAGCAGAAACCAGGGAGAG CCCCTAAACTCGTGATCTATTCTACATCCAGTT TGCAAAGTGGGGTCCCATCAAGGTTCAGTGGC AGTGGATCTGGGACAGATTTCAGTCTCACCAT CAGCAATCTGCAACAGAGTTACAGTCCCCCTC ACTTTCGGCGGAGGGACCAAGGTGGAGATCA GA | CAGGTGCAGCTGGTGGAGTCTGGGGGAGGCGTG GTCCAGCCTGGGAGGTCCCTGAGACTCTCCTGTG CAGCGTCTGATTCAACTTCAGTAGCTATGGCAT GCACTGGGTCCGCCAGGCTCCAGGCAAGGGCT GGAGTGGATGGCAGTTATATGGTATGATGGAAGT AATAAATACTATGCAGACTCCGTGAAGGGCCGA TTCACCATCTCCAGAGACAATTCCAAGAACACGC TGTATCTGCAAATGCACAGCCTGAGAGCCGAGG ACACGGCTGTGTATTACTGTGCGAGAGATGAGAG GCTGGGGATTTTTGACTACTGGGGCCAGGGAACC CTGGTCACCGTCTCCTCA |
| | | | SEQ ID NO: 25187 | SEQ ID NO: 29193 |

FIGURE 50
(Continued)

| | | | | |
|---|---|---|---|---|
| | | AA | DIQMTQSPSSLSASVGDRVTITCRASQNIYSYLN WYQQKPGRAPKLVIYSTSSLQSGVPSRFSGSGSG TDFSLTISNLQPEDFSTYYCQQSYSPPLTFGGGTK VEIR | QVQLVESGGGVVQPGRSLRLSCAASGFNFSSYGMH WVRQAPGKGLEWMAVIWYDGSNKYYADSVKGRF TISRDNSKNTLYLQMHSLRAEDTAVYYCARDERLG IFDYWGQGTLVTVSS |
| | | | SEQ ID NO: 25188 | SEQ ID NO: 29194 |
| iPS:426124 | 21-225_32D6 | NA | GACATCCAGATGACCCAGTCTCCATCCTCCCT GTCTACATCTGTAGGAGACAGAGTCACCATCA CTTGCCGGGCAAGTCAGAACATTATCAGTTAT TTAAATTGGTATCAGCAGAAACCAGGGAAAG CCCCTAAGCTCCTGATGTATGTTGCATCCGTT TGCAAAGTGGGGTCCCATCAAGGTTCAGTGGC AGTGGATCTGGGACAGATTTCACTCTCACCAT CAGCAGTCTGCAAGCTGAAGATTTTGCAACTT ACTACTGTCAACAGAGAGTTACAGTACCCGTAC ACTTTCGGCGGAGGGACCAAGGTGGCGATCA AA | CAGGTGCAGTTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGACT GGAGTGGGTGACAGTTATATGCAGTCATGAAAG TAATGCATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAAATAG CAGCTCGTACTACTTTGACTACTGGGGCCAGGGA ACCCTGGTCACCGTCTCCTCA |
| | | | SEQ ID NO: 25189 | SEQ ID NO: 29195 |
| | | AA | DIQMTQSPSSLSTSVGDRVTITCRASQNIISYLNW YQQKPGKAPKLLMYVASRLQSGVPSRFSGSGSG TDFTLTISSLQAEDFATYYCQQSYSTPYTFGGGT KVAIK | QVQLVESGGGVVQPGRSLRLSCAASGFTFSSYGMH WVRQAPGKGLEWVTVIWHDGSNAYYADSVKGRF TISRDNSKNTLYLQMNSLRAEDTAVYYCARENSSS YYFDYWGQGTLVTVSS |
| | | | SEQ ID NO: 25190 | SEQ ID NO: 29196 |

FIGURE 50
(Continued)

| | | | |
|---|---|---|---|
| iPS:426126 | 21-225_6G6 | NA | GACATCGTGATGACCCAGTCTCCAGACTCCCT GGCTGTGTCTCTGGGCGAGAGGGCCACCATCA ATTGCAAGTCCAGCAGTGTTTACACAAC TCCAACAATTATAACTATTTAGCTTGGTACCA GCAGAAACCAGGACAGCCTCCTAACCTGCTCA TTTTCTGGGCATCTACCCGGGAATCCGGGGTC CCTGACCGATTCAGTGGCAGCGGGTTTGGGAC AGATTTCACTCTCAACATCAGCAGCCTGCAGG CTGAAGATGTGGCAGTTTATTACTGTCAGCAA TATTATGATACTCCATTCACTTTCGGCCATGGG ACCAAAGTGGATATCAAA<br>SEQ ID NO: 25191 | CAGGTGCAGCTGGTGCAGTCTGGGGCTGAGGTG AGGAAGCCTGGGCCTCAGTGAAGGTCTCCTGC AAGGCTTCTGGATACACCTTCACCAATTATGATA TCAACTGGGTGCGACAGGCCACTGGACAAGGGC CTGAGTGGATGGATGGATGCACCTAACAGTG GTAACACAGGCTATGCAAAGAAGTTCCAGGGCA GAGTCACCATGACCAGGAACACCTCATAAGCG CAGCCTATATGTTCTGAGCAGCCTGAGATCTGA GGACACGGCCGTGTATTACTGTGCGCTTAGCAGT GGCTGGTACTACTTTGACTACTGGGGCCAGGGAA CCCTGGTCACCGTCTCCTCA<br>SEQ ID NO: 29197 |
| | | AA | DIVMTQSPDSLAVSLGERATINCKSSQSVLHNSN NYNYLAWYQQKPGQPPNLLIFWASTRESGVPDR FSGSGFGTDFTLNISSLQAEDVAVYYCQQYYDTP FTFGHGTKVDIK<br>SEQ ID NO: 25192 | QVQLVQSGAEVRKPGASVKVSCKASGYTFTNYDIN WVRQATGQGPEWMGWMHPNSGNTGYAKKFQGR VTMTRNTSISAAYMVLSSLRSEDTAVYYCALSSGW YYFDYWGQGTLVTVSS<br>SEQ ID NO: 29198 |
| iPS:433895 | 21-225_43E1 | NA | GACATCCAGATGACCCAGTCTCCATCCTCCCT GTCTGCATCTGTAGGAGACAGAGTCACCATCA CTTGCCCGGGCAAGTCAGGGACAGATTAGAAATGAT TTAGGCTGGTATCAGAAAGAAACCAGGGAAAG CCCCTAAGCGCCTGATCAATGCTGCATCCAGT TTGCAAAGTGGGGTCCCATCAAGGTTCACTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br>SEQ ID NO: 25193 | GAGGTGCAGCTGGTGGAGTCTGGGGGAGGCCTG GTCAAGCCTGGGGGGTCCCTGAGACTCTCCTGTG TCAAGCCTCTGGATTCACCTTCAGTAGCTATAGCAT GAACTGGGTCCGCCAGGCTCCAGGGAAGGGCT GGAGTGGGTCTCCGCCATTAGTGGTAATAGTACT TACATATACTACCAGAGACTCGTTGAAGGGCCGAT TCACCATCTCCAGAGACAACGCCAAGAACTCACT GTTTCTGCAACTGAACAGCCTGAGAGCCGAGGA CACGGCTGTTATTACTGTGCGAGAGATCGGGGC AGTGAATGGGGCAGGGAACCCTGGTCACCGTC TCCTCA<br>SEQ ID NO: 29199 |

FIGURE 50
(Continued)

| | | | |
|---|---|---|---|
| iPS:433897 | | AA | DIQMTQSPSSLSASVGDRVTITCRASQGIRNDLG WYQKKPGKAPKRLINAASSLQSGVPSRFSGSGS GTEFTLTISSLQPEDFATYYCLQHNSYPFTFGPGT KVDIK SEQ ID NO: 25194 | EVQLVESGGGLVKPGGSLRLSCAASGFTFSSYSMN WVRQAPGKGLEWVSAISGNSTYYYADSLKGRFTI SRDNAKNSLFLQLNSLRAEDTAVYYCARDRGSEW GQGTLVTVSS SEQ ID NO: 29200 |
| | 21-225_43C2 | NA | GACATCCAGATGACCCAGTCTCCATCTTCCGT GTCTGCATCTGTAGGAGACAGAGTCACCATCA CTTGTCGGGCGAGTCAGGGTATTAGCGACTGG TTAGCCTGGTATCAGCAGAAACCAGGGAAAG CCCCTAGGCTCCTGATCTATGCTGCATCCAGTT TGCAAAGTGGGGTCCCATCAAGGTTCAGCGGC AGTGGATCTGGGACAGATTTCACTCTCACCAT CAGCAACCTGCAGCCTGAAGATTTTGCAACTT ACTATTGTCAACAGAGTAACAGTTTCCCGTGG ACGTTCGGCCAAGGGACCAAGGTGGAAATCA AA SEQ ID NO: 25195 | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGT AACACATTCGACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAGGAAAGGA GTGGGAGCTATTTTGACTACTGGGGCCAGGGAAC CCTGGTCACCGTCTCCTCA SEQ ID NO: 29201 |
| | | AA | DIQMTQSPSSVSASVGDRVTITCRASQGISDWLA WYQQKPGKAPRLLIYAASSLQSGVPSRFSGSGSG TDFTLTISNLQPEDFATYYCQQTNSFPWTFGQGT KVEIK SEQ ID NO: 25196 | EVQLLESGGGLVQPGGSLRLSCAASGFTFSSYAMS WVRQAPGKGLEWVSAISGRGVNTFDADSVKGRFTI SRDNSKNTLYLQMNSLRAEDTAVYYCAKERSGSY FDYWGQGTLVTVSS SEQ ID NO: 29202 |

FIGURE 50
(Continued)

| | | | |
|---|---|---|---|
| iPS:433899 | 21-225_43C3 | NA | GACATCCAGATGACCCAGTCTCCATCCTCCCT GTCTGCATCTGTAGGAGACAGAGTCACCATCA CTTGCCGGGCAAGTCAGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCTCTC ACTTTCGGCGGAGGGACCAAGGTGGGGATCA CA<br><br>SEQ ID NO: 25197 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTATGGCAT ACACTGGGTCCGCCAGGCTCCAGGCAAGGGCT GGAGTGGGTGGCAGTTATATGCAGACTCCGTGATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGTAGG ATTTTCCAATGACTACTGGGGCCAGGGAACCCTG GTCACCGTCTCCTCA<br><br>SEQ ID NO: 29203 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVGIT<br><br>SEQ ID NO: 25198 | QVQLVESGGGVVQPGRSLRLSCAASGFTFSSYGIH WVRQAPGKGLEWVAVIWYDENNKYYADSVKGRF TISRDNSKNTLYLQMNSLRAEDTAVYYCARELGFS NDYWGQGTLVTVSS<br><br>SEQ ID NO: 29204 |
| iPS:433901 | 21-225_43A4 | NA | GACATCCAGATGACCCAGTCTCCATCCTCACT GTCTGCATCTGTAGGAGACAGAGTCACCATCA CTTGTCGGGCGAGTCAGGCAGTTAACAATTAT TTAGCCTGGTTTCAGCAGAAACCAGGGAAAGC CCCTAAGTCCCTGATCAATGCTGCATCCAGTTT GCAAAGTGGGGTCCCATCAAGGTTCAGCGGCA GTGGATCTGGGACAGATTTCACTCTCGCCATC AGCAGCCTACAGCCTGAAGATTTTGCAACTTA TTACTGCCAACAGTATTATAGTTACCATTCAC TTTCGGCCCTGGGACCAAAGTGGATATCAAA<br><br>SEQ ID NO: 25199 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATACCAT GAACTGGGTCCGCCAGGTTCCAGGGAAGGGCT GGAGTGGGTCTCATCATTAGTGGAAGTAGTACT TACATATACTACGCAGACTCAGTGAAGGGCCGAT TCACCATCTCCAGAGACAACGCCCAGAACTCACT GTATCTGCAAATGAACAGCCTGAGAGGCGAGGA CACGGCTGTGTATTACTGTGCGAGGGTGACCTCT TTGACTACTGGGGCCAGGGAGCCCTGGTCACCG TCTCCTCA<br><br>SEQ ID NO: 29205 |

FIGURE 50
(Continued)

| | | | |
|---|---|---|---|
| iPS:433903 | | AA | DIQMTQSPSSLSASVGDRVTITCRASQGINNYLA WFQQKPGKAPKSLINAASSLQSGVPSRFSGSGSG TDFTLAISSLQPEDFATYYCQQYYSYPFTFGPGT KVDIK<br>SEQ ID NO: 25200 | EVQLVESGGGLVKPGGSLRLSCAASGFTFSSYTMN WVRQVPGKGLEWVSSISGSSTYIYYADSVKGRFTIS RDDAQNSLYLQMNSLRGEDTAVYYCARVTSFDY WGQGALVTVSS<br>SEQ ID NO: 29206 |
| | | NA | GACATCCAGATGACCCAGTCTCCATCTTCCGT GTCTGCATCTGTAGGAGACAGAGTCACCATCA CTTGTCGGGCGAGTCAGGGTATTATCAACTGG TTAGCCTGGTATCAACAGAAACCAGGGAAAG CCCCTAAGTCTCTGATCTATGCTGCATCCAGTT TGCAAAGTGGGGTCCCATCAAGGTTCAGCGGC AGTGGATCTGGGACAGATTTCACTCTCACCAT CAGCAACCTGCAGCCTGAAGATTTTGCAACTT ACTATTGTCAACAGATACAACAGTTTCCCGTGG ACGTTCGGCCAAGGGACCAAGGTGGAAATCA AA<br>SEQ ID NO: 25201 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTATT AACACATTGACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAGGAAAGGA GTGGGAGCTATTTTGACTACTGGGGCCAGGGAAC CCTGGTCACCGTCCTCCTCA<br>SEQ ID NO: 29207 |
| 21-225_43H4 | | AA | DIQMTQSPSSVSASVGDRVTITCRASQGIHNWLA WYQQKPGKAPKLLIYAASSLQSGVPSRFSGSGS GTDFTLTISNLQPEDFATYYCQQTNSFPWTFGQG TKVEIK<br>SEQ ID NO: 25202 | EVQLLESGGGLVQPGGSLRLSCAASGFTFSSYAMS WVRQAPGKGLEWVSAISGRGINTFDADSVKGRFTI SRDNSKNTLYLQMNSLRAEDTAVYYCAKERSGSY FDYWGQGTLVTVSS<br>SEQ ID NO: 29208 |

FIGURE 50
(Continued)

| | | | |
|---|---|---|---|
| iPS:433905 | 21-225_43E5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGGTGCATCCAAT TTGCAAAGTGGGGTCCATCAAGGTTCAGCGG CAGTGGATCTGGGACAGAATTCACTCTCACAG TCAGCAGCCTGCAGCCTGAAGATTTTGCAACT TATTTCTGTCTACAGCATACTAGTTTCCCATTC ACTTTCGGCCCTGGGACCAAAGTGGATATCAA A | CAGGTGCAGCTGGTGGTGGAGTCTGGGGGAGGCTTG GTCAAGCCTGGAGGGTCCCTGAGACTCTCCTGTG CAGCCTCTGGATTCACCTTCAGTGACTACTACAT GATCTGGGATCCGCCAGGCTCCAGGGAAGGGGCT GGAGTGGGGTTCATACTACCAGACTCTATGAAGGGCGA ACCAAATACTACGCAGACTCTATGAAGGGCCGA TTCACCATCTCCAGGGACAAGCCAAGAACTCAC TGTATCTGCAAATGAACAGCCTGAGAGCCGAGG ACACGGCCGTGTATTACTGTGCGGCCGATACAAT CTACTGGGGCCAGGGAACCCTGGTCACCGTCTCC TCA |
| | | | SEQ ID NO: 25203 | SEQ ID NO: 29209 |
| | | AA | DIQMTQSPSSLSASVGDRVTITCRASQGIRNDLG WYQQKPGKAPKRLIYGASNLQSGVPSRFSGSGS GTEFTLTVSSLQPEDFATYFCLQHTSFPFTFGPGT KVDIK | QVQLVESGGGLVKPGGSLRLSCAASGFTFSDYYMI WIRQAPGKGLEWVSYISSSGITKYYADSMKGRFTIS RDNAKNSLYLQMNSLRAEDTAVYYCAADTIYWGQ GTLVTVSS |
| | | | SEQ ID NO: 25204 | SEQ ID NO: 29210 |
| iPS:433909 | 21-225_43D8 | NA | GACATCGTGATGACCCAGTCTCCAGACTCCCT GGCTGTGTCTCTGGGCGAGAGGGCCACCATCA ACTGCAAGTCCAGCCAGAGTGTTTAATGACC TCCAACGATAAGAACTACTTAACTTGGTACCA GCAGAAACCAGGACAGGCCTCCTAAGCTGCTCA TTTACTGGGCTTCTACCCGGGGAATCCGGGGTC CCTGACCGATTCAGTGGCGGCGGGTCTGGGAC AGATTTCACTCTCACCATCAGCAGCCTGCAGG CTGAAGATGTGGCAGTTTATTACTGCCAGCAA TATTATAGTACTCCTCCGACGTTCGGCCAAGG GACCAAGGTGGAAATCAAG | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGACATCTGA GGACACGGCCGTGTATTACTGTGCCATAGCAGT GGCTGGACCCCTCTTTGACTACTGGGGCCAGGGAA CCCTGGTCACCGTCTCCGCA |
| | | | SEQ ID NO: 25205 | SEQ ID NO: 29211 |

FIGURE 50
(Continued)

| | | | |
|---|---|---|---|
| iPS:433911 | 21-225_43E8 | AA | DIVMTQSPDSLAVSLGERATINCKSSQSVLMTSN DKNYLTWYQQRPGQPPKLLIYWASTRESGVPDR FSGGGSGTDFTLTISGLQAEDVAVYYCQQYYST PPTFGQGTKVEIK<br>SEQ ID NO: 25206 | QVQLVQSGAEVKKPGASVKVSCKASGYTFNYDIN WVRQATGQGLEWMGWMHPNSGNTGYAQKFQGR VTMTRNTSISTAYMELSSLTSEDTAVYYCAHSSGW TLFDYWGQGTLVTVSA<br>SEQ ID NO: 29212 |
| | | NA | GACATCCAGATGAACCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAGAG CCCCTAAGCTCCTGATCTATGCTGCATCCAGTT TGCAAAGTGGGGTCCCTTCAAGGTTCAGCGGC AGTGGATCTGGGACAGATTTCACTCTCACCAT CAGCAACCTGCAGCCTGAAGATTTTGCAACTT ACTATTGTCAACAGACTAACAGTTTCCCGTGG ACGTTCGGCCAAGGGACCAAGGTGGAAATCA AA<br>SEQ ID NO: 25207 | GAGGTGCAGCTGTTGGAGTCTGGGGGAGGCTTG GTACAGCCTGGGGGGTCCCTGAGACTCTCCGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTATT AACACATTGGACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAGGAAAGGA GTGGGAGCTATTTTGACTACTGGGGCCAGGGAAC CCTGGTCACCGTCTCCTCA<br>SEQ ID NO: 29213 |
| | | AA | DIQMNQSPSSVSASVGDRVTITCRASQGISNWLA WYQQKPGRAPKLLIYAASSLQSGVPSRFSGSGSG TDFTLTISNLQPEDFATYYCQQTNSFPWTFGQGT KVEIK<br>SEQ ID NO: 25208 | EVQLLESGGGLVQPGGSLRLSCAASGFTFSSYAMS WVRQAPGKGLEWVSAISRGRINTFDADSVKGRFTI SRDNSKNTLYLQMNSLRAEDTAVYYCAKERSGSY FDYWGQGTLVTVSS<br>SEQ ID NO: 29214 |

FIGURE 50
(Continued)

| | | | |
|---|---|---|---|
| iPS:433913 | 21-225_43H8 | NA | GACATCCAGATGACCCAGTCTCCATCTTCCCT GTCTGCATCTGTAGGAGACAGAGTCACCATCA CTTGCCGGGCAAGTCAGGCATTAGAAATGAT TTAGGCTGGTGGATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCTCAA TCAGCAGCCTGCAGCCTGAAGATTTTGCAACT TATTACTGTCTACAGCATAATAGTTTCCCATTC ACTTTCGGCCCTGGGACCAAAGTGGATATCAA A SEQ ID NO: 25209 | CAGGTGCAGCTGGTGGAGTCTGGGGGAGGCTTG GTCAAGCCTGGAGGGTCCCTGAGACTCTCCTGTG CAGCCTCTGGAATCACCTTCAGTGACTACTACAT GAACTGGATCCGCCAGGCTCCAGGGAAGGGGCT GGAGTGGGTTCATACATTAGTAGTAGTGGTAGA ACCATATTCTACGCAGACTCTTTGAAGGGCGAT TCACCATCTCCAGGGACAACGCCAAGAACTCACT GTATCTGCAAATGAACAGCCTGAGAGCCGAGGA CACGGCCGTGTATTACTGTGCGGGCCGATACAATC TACTGGGGCCAGGGAACCCTGGTCACCGTCTCCT CA SEQ ID NO: 29215 |
| | | AA | DIQMTQSPSSLSASVGDRVTITCRASQGIRNDLG WHQQKPGKAPKRLIYAASSLQSGVPSRFSGSGS GTEFTLSISSLQPEDFATYYCLQHNSFPFTFGPGT KVDIK SEQ ID NO: 25210 | QVQLVESGGGLVKPGGSLRLSCAASGITFSDYYMN WIRQAPGKGLEWVSYISSSGRTIFYADSLKGRFTISR DNAKNSLYLQMNSLRAEDTAVYYCAADTIYWGQ GTLVTVSS SEQ ID NO: 29216 |
| iPS:433915 | 21-225_43H9 | NA | GACATCCAGATGACCCAGTCTCCATCTTCCGT GTCTGCATCTGTAGGAGACAGAGTCACCATCA CTTGTCGGGCGAGTCAGGATATTAGCAGCTGG TTAGCCTGGTATCAGAAGAAAGCCAGGGAAAG CCCCTAAACTCCTGATCTATGATGCATCCAGT TGCAAAGTGGGGTCCCATCAAGGTTCAGCGGC AGTGGATCTGGGACAGATTTCATTCTCACCAT CAGCAGCCTGCAGCCTGAAGATTTTGCAACTT ACTTTTGTCAACAGGCTAACAGTCTCCCATTC ACTTTCGGCCCTGGGACCAAAGTGGATATCAA A SEQ ID NO: 25211 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGTTGGGTCCGCCAGGCTCCAGGGATGGGGCT GGAGTGGGTCTCAGTATTAGTGGTAGTGGTAGT AACACATTCTACGCAGACTCCGTGAAGGGCCGGT TCACCATCTCCAGAGACAATTCCAAGAACACGCT GTATCTGCAACATGAACAGCTGAGAGCCGAGGA CACTGCCGTATATTTCTGTGCGAAACGAACGCCC TCTGATGTTTTTGATATCTGGGGCCAAGGGACAA TGGTCACCGTCTCTTCA SEQ ID NO: 29217 |

FIGURE 50
(Continued)

| | | | |
|---|---|---|---|
| iPS:433917 | 21-225_43E11 | AA | DIQMTQSPSSVSASVGDRVTITCRASQDISSWLAWYQKKPGKAPKLLIYDASSLQSGVPSRFSGSGSGTDFILTISSLQPEDFATYFCQQANSLPFTFGPGTKVDIK | EVQLLESGGGLVQPGGSLRLSCAASGFTFSSYAMSWVRQAPGMGLEWVSAISGSGSNTFYADSVKGRFTISRDNSKNTLYLHMNSLRAEDTAVYFCAKRTPSDVFDIWGQGTMVTVSS |
| | | | SEQ ID NO: 25212 | SEQ ID NO: 29218 |
| | | NA | GATATTGTGATGACCCAGACTCCACTCTCTCTGTCCGTCACCCCTGGACAGCCGGCCTCCATCTCCTGCAAGTCTAGTCAGAGCCTCCTGCACAGTGATGGAAGGACCTATTTGTATTGGTACCTTCAGAAGCCAGGCCAGGCTCCGCAGCTCCTGATCTATGAAGTTTCCAACCGGTTCTCTGGAGTGCCAGATAGGTTCAGTGGCAGCGGGTCAGGGACAGACTTCACACTGAAAATCAGCCGGGTGGAGGCTGAGGATGTTGGGGTTTATTACTGTATGCAAGGTATACAGCTTCCGTGGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCGTCTGGATTCTCCTTCAGTGACTATGGCATGCACTGGGTCCGCCAGGCTCCAGGCAAGGGGCTGGAGTGGGTGGCAGTTATATGTGATGGAAGTAATAAATACTATGCAGACTCCGTGAAGGGCCGACTCACCATCTCCAGAGACAATTCCAAGAACACGCTGTATCTGCAAATGAACAGCCTGAGAGCCGAGGACACGGCTGTGTATTACTGTGCGAGGCGGTATGTCAGAAGCTGGGTGGGAGGTATGGACGTCTGGGGCCAAGGGACCACGGTCACCGTCTCCTCA |
| | | | SEQ ID NO: 25213 | SEQ ID NO: 29219 |
| | | AA | DIVMTQTPLSLSVTPGQPASISCKSSQSLLHSDGRTYLYWYLQKPGQPPQLLIYEVSNRFSGVPDRFSGSGSGTDFTLKISRVEAEDVGVYYCMQSIQLPWTFGQGTKVEIK | QVQLVESGGGVVQPGRSLRLSCAASGFSFSDYGMHWVRQAPGKGLEWVAVIWYDGSNKYYADSVKGRLTISRDNSKNTLYLQMNSLRAEDTAVYYCARRYVRSWVGGMDVWGQGTTVTVSS |
| | | | SEQ ID NO: 25214 | SEQ ID NO: 29220 |

FIGURE 50
(Continued)

| | | | |
|---|---|---|---|
| iPS:433919 | 21-225_44B3 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAACAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACTGCATTATAATTACCCTCGG ACGTTCGGCCAAGGGACCAAGGTGGAAATCA AG | CAGGTGCAGCTGGTGGAGTCTGGGGGAGGCGTG GTCCAGCCTGGGAGGTCCCTGAGACTCTCCTGTA CAGCGTCTGGATTCACCTTCAGTGACTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGTA TAGCAGTGGCTGGTACGACTACGGTATGGACGTC TGGGGCCAAGGGACCACGGTCACCGTCTCCTCA |
| | | | SEQ ID NO: 25215 | SEQ ID NO: 29221 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLLHYNYPRTFGQG TKVEIK | QVQLVESGGGVVQPGRSLRLSCTASGFTFSDYGMH WVRQAPGKGLEWVAVIWYDGSNKYYADSVKGRF TISRDNSKNTLYLQMNSLRAEDTAVYYCARERYSS GWYDYGMDVWGQGTTVTVSS |
| | | | SEQ ID NO: 25216 | SEQ ID NO: 29222 |
| iPS:433921 | 21-225_44C3 | NA | GACATCCAGATGACCCAGTCTCCATCCTCCCT GTCTGCATCTGTAGGAGACAGAGTCACCATCA CTTGCCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CGGTGGATCTGGGACAGACCTGAAGATTTTGCGACT TCAGCAGCCTGCAGCCTGAAGATTTTGCGACT TATTACTGTCTACAGCATAGTAGTTACCCTCTC ACTTTCGGCGGAGGGACCAAGGTGGAGATCA AG | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGCAT GCACTGGGTCCGCCAGGCTCCAGGCAAGGGGCT GGAGTGGGTGGCAGTTATATGGTTTGAAGGAAGT AATAAATACTATGCAGACAATTCCGTGAAGGGCCGAT TCACCATCTCCAGAGACAATGAGCAGCCTGAGAGCT GTATCTGCAAATGAGCAGCCTGAGAGAACTAGGA CACGGCTGTGTTCCACCGACTACTGGGGCCAGGGAACCCTGG TCACCGTCTCCTCA |
| | | | SEQ ID NO: 25217 | SEQ ID NO: 29223 |

FIGURE 50
(Continued)

| | | | | |
|---|---|---|---|---|
| | | AA | DIQMTQSPSSLSASVGDRVTITCRASQGIRNDLGWYQQKPGKAPKRLIYAASSLQSGVPSRFSGGGSGTEFTLTISSLQPEDFATYYCLQHSSYPLTFGGGTKVEIK<br>SEQ ID NO: 25218 | QVQLVESGGGVVQPGRSLRLSCAASGFTFSSYGMHWVRQAPGKGLEWVAVIWFEGSNKYYADSVKGRFTISRDNSKNTLYLQMSSLRAEDTAVYYCVRELGFSTDYWGQGTLVTVSS<br>SEQ ID NO: 29224 |
| iPS:433923 | 21-225_44D3 | NA | GACATCCAGATGACCCAGTCTCCATCCTCCCTGTCTGCATCTGTGGGAGACAGAGTCACCTTCACTTGCCGGGCAAGTCAGGGCATTAGAGATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTAGATCTGGGAGAGACAATTCACTCTCACAATCAGCAGCCTGCAACCTGAAGATTTTGCAACTTATTACTGTCTACAGCATTATAGTTACCCTCGGACGTTCGGCCAAGGGACCAAGGTGGAAATCAAA<br>SEQ ID NO: 25219 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGTCATGCACTGGGTCCGCCAGGCTCCAGGCAAGGGGCTGGAGTGGGTGGCAGTTATATGTGATGGAAGTAATAAATACTATGCTGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGACTACGGTATGGACGTCTAGCAGTGGCTTGTGACTACGGTATGGACGTCTGGGGCCAAGGGACCACGGTCACCGTCTCCTCA<br>SEQ ID NO: 29225 |
| | | AA | DIQMTQSPSSLSASVGDRVTFTCRASQGIRDDLGWYQQKPGKAPKRLIYAASSLQSGVPSRFSGSRSGREFTLTISSLQPEDFATYYCLQHYSYPRTFGQGTKVEIK<br>SEQ ID NO: 25220 | QVQLVESGGGVVQPGRSLRLSCAASGFTFSSYVMHWVRQAPGKGLEWVAVIWYDGSNKYYADSVKGRFTISRDNSKNTLYLQMNSLRAEDTAVYYCARERYSSGLYDYGMDVWGQGTTVTVSS<br>SEQ ID NO: 29226 |

FIGURE 50
(Continued)

| | | | |
|---|---|---|---|
| iPS:433925 | 21-225_44F3 | NA | GACATCCAGATGACCCAGTCTCCATCTTCCGT GTCTGCATCTGTAGGAGACAGAGTCACCATCA CTTGTCGGGCGAGTCAGGGTATTAGCGACTGG TTAGCCTGGTATCAGCAGAAACCAGGGAAAG CCCCTAAGCTCCTGATTTATGCTGCATCCAGTT TACAAAGTGGAGTCCCATCAAGGTTCAGCGGC AGTGGATTTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A |
| | | | SEQ ID NO: 25221 |
| | | AA | DIQMTQSPSSVSASVGDRVTITCRASQGISDWLA WYQQKPGKAPKLLIYAASSLQSGVPSRFSGSGF GTDFTLTISSLQPEDFATYYCQQANSFPFTFGPGT KVDIK |
| | | | SEQ ID NO: 25222 |
| | | | GAGGTGCACCTGTTGGAGTCTGGGGGAGGCTTGG TACAGCCTGGGGGGTCCTGAGACTCTCCTGTGC AGCCTCTGGATTCACCTTTAGCAGCTATGCCATG AGCTGGGTCCGCCAGGCTCCAGGGAAGGGGCTG GAGTGGGTCTCAATTCTCAGTGGTGGTGGTAAGA CCCATACTACGCAGACTCCGTGAAGGGCCGTT CACCATCTCCAGAGACAATTCCAAGAACACGCTG TTTCTGCAAATGAACAGCTGAGAGCCGAGGAC ACGGCCGTATATTACTGTGCGAAACGAACGCCT CTGATGCTTTTGATATCTGGGGCCAAGGGACAAT GGTCACCGTCTCTTCA |
| | | | SEQ ID NO: 29227 |
| | | | EVHLLESGGGLVQPGGSLRLSCAASGFTFSSYAMS WVRQAPGKGLEWVSILSGGGKTTYYADSVKGRFTI SRDNSKNTLFLQMNSLRAEDTAVYYCAKRTPSDAF DIWGQGTMVTVSS |
| | | | SEQ ID NO: 29228 |
| iPS:433929 | 21-225_44D5 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGCCTGGTATCAGCAGAAAACCAGGGAAAG CCCCTAAGCGCCTGATCTATGCTGCATCCACTT TGGAAAGTGGGGTCCCATCAAGGTTCAGCGGC AGTGGATCTGGGACAGATTTCACTCTCACAAT CAGCAGCCTGCAGCCTGAAGATTTTGCAACTT ATTACTGTCTACAGCATTATAGTTTCCCGTGGA CGTTCGGCCAAGGGACCAAGGTGGAAATCAA A |
| | | | SEQ ID NO: 25223 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGTCCCGTA TAGCAGCAGCTGGTACGACTACGGTATGGACGTC TGGGGCCAAGGGACCACGGTCACCGTCTCCTCA |
| | | | SEQ ID NO: 29229 |

FIGURE 50
(Continued)

| | | | |
|---|---|---|---|
| | | AA | DIQMTQSPSSLSASVGDRVTITCRASQDIRKDLG WYQQKPGKAPKRLIYAASTLESGVPSRFSGSGS GTEFTLTISSLQPEDFATYYCLQHYSFPWTFGQG TKVEIK<br><br>SEQ ID NO: 25224 | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCARVPYSS SWYDYGMDVWGQGTTVTVSS<br><br>SEQ ID NO: 29230 |
| iPS:433931 | 21-225_44F6 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGTGGAAGC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TTTATTACTGTCAGCAGTATGGTAGTTCACCGT GGACGTTCGGCCAAGGGACCAAGGTGAAAT CAAA<br><br>SEQ ID NO: 25225 | CAGGTGCACCTGCAGGAGTCGGGCCCAGGACTG GTGAAGCCTTCGGAGACCCTGTCCCTCACCTGCA CTGTCTCTGGTGGCTCCATCAGTAGTTACTACTG GAGCTGGATCCGGCAGCCCCCAGGGAAGGGACT GGAGTGGATTGGGTATATCTATTACAGTGGAAAC ACCAACTACAACCCCTCCCTCAAGAGTCGAGTCA CCATATCAGTAGACACGTCCAAGAACCAGTTCTC CCTGAAGCTGAGCTCTGTGACCGCTGCGGACACG GCCGTGTATTACTGTGTGAGAGGGGTGGCTATAA AGAACTACTGGGGCCAGGGAATCCTGGTCACCG TCTCCCTCA<br><br>SEQ ID NO: 29231 |
| | | AA | EIVLTQSPGTLSLSPGERATLSCRASQSVSGSYLA WYQQKPGQAPRLLIYGASSRATGIPDRFSGSGSG TDFTLTISRLEPEDFAVYYCQQYGSSPWTFGQGT KVEIK<br><br>SEQ ID NO: 25226 | QVHLQESGPGLVKPSETLSLTCTVSGGSISSYYWSW IRQPPGKGLEWIGYIYYSGNTNYNPSLKSRVTISVD TSKNQFSLKLSSVTAADTAVYYCVRGVAIKNYWG QGILVTVSS<br><br>SEQ ID NO: 29232 |

FIGURE 50
(Continued)

| | | | |
|---|---|---|---|
| iPS:433933 | 21-225_44C8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAAT TTGCAAAGTGGGGTCCCATCAAGGTTCAGCGG CAGTAGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A SEQ ID NO: 25227 | CAGGTGCAGCTGGTGGAGTCTGGGGGAGGCGTG GTCCAGCCTGGGAGGTCCCTGAGACTCTCCTGTG CAGCGTCTGGATTCACCTTCAATAACTATGGCAT GCACTGGGTCCGCCAGGCTCCAGGCAAGGGCT GGAGTGGGTGGCAGTTATATGGTATGAAGGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGTGAGAGAACTGG GGTTCCTCTGACTACTGGGGCCAGGGAACCCT GGTCACCGTCTCCTCA SEQ ID NO: 29233 |
| | | AA | DIQMTQSPSSLSASVGDRVTITCRASQGIRNDLG WYQQKPGKAPKRLIYAASNLQSGVPSRFSGSRS GTEFTLTISSLQPEDFATYYCLQHNSYPFTFGPGT KVDIK SEQ ID NO: 25228 | QVQLVESGGGVVQPGRSLRLSCAASGFTFNNYGM HWVRQAPGKGLEWVAVIWYEGSNKYYADSVKGR FTISRDNSKNTLYLQMNSLRAEDTAVYYCVRELGF LSDYWGQGTLVTVSS SEQ ID NO: 29234 |
| iPS:433935 | 21-225_44F9 | NA | GACGTCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTCATCTATGCTGCATCCAGTT TGCAAAGTGGGGTCCCATCAAGGTTCAGCGGC AGTGGATCTGGGACAGCCTGCAGCCTGCAACTT TATTACTGTCTCCACCATTATAATTACCCTCCGA CGTTCGGCCAAGGGACCAAGGTGGAAATCAC A SEQ ID NO: 25229 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTGTCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAG ACACGGCTGTGTATTACTGTGTGAGAGAACCATA TAGCAGCAGCTGTAGCGACTACGGTATGACGTC GGGGGCCAAGGGACCACGGTCACCGTCCTCA SEQ ID NO: 29235 |

FIGURE 50
(Continued)

| | | | |
|---|---|---|---|
| iPS:433937 | 21-225_44B10 | AA | DVQMTQSPSSLSASVGDRVTITCRASQGIRNDLG WYQQKPGKAPKRLIYAASSLQSGVPSRFSGSGS GTEFTLTISSLQPEDFATYYCLHHYNYPRTFGQG TKVEIT<br>SEQ ID NO: 25230 | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCAREPYSS SWYDYGMDVGGQGTTVTVSS<br>SEQ ID NO: 29236 |
| | | NA | CATATTGTGATGACCCAGACTCCACTCTCTCTG TCCGTCACCCCTGGACAGCCGGCCTCCATCTC CTGCAAGTCTAGTCAGAGCCTCCTGCATAGTG AGGGAAGGACCTATTTGTATTGGTACCTGCAG AAGCCAGGCCAGTCCACCAGCTCCTGATCTA TGAAATTTCCAACCGGTTCTCTGGAGTGCCAG ATAGATTCAGTGGCAGGGGTCAGGACAGA TTTCACACTGAAAATCAGCCGGGTGGAGGCTG AGGATGTTGGGGTTTATTACTGCATGCAAAGT ATCCACCTTCGTTCACTTTCGGCGGAGGGAC CAAGGTGGAGATCAAA<br>SEQ ID NO: 25231 | CAGGTGCAGTTGGTGGAGTCTGGGGAGGCGTG GTCCAGCCTGGGAGGTCCCTGAGACTCTCCTGTG TAGCGTCTGAGTTCACCTTCAGTAGCTATGCAT GCACTGGGTCCGCCAGGCTCCAGGCAAGGGCT GGAGTGGGTGGCAGTTATATGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTATTGTGCGAGGCGGTATAG CAGCAGCTGGGTGGGGGTATGGACGTCTGGGG CCAAGGGACCACGGTCACCGTCCTCCTCA<br>SEQ ID NO: 29237 |
| | | AA | HIVMTQTPLSLSVTPGQPASISCKSSQSLLHSEGR TYLYWYLQKPGQPPQLLIYEISHRFSGVPDRFSG SGSGTDFTLKISRVEAEDVGVYYCMQSIHLPFTF GGGTKVEIK<br>SEQ ID NO: 25232 | QVQLVESGGGVVQPGRSLRLSCVASGFTFSSYGMH WVRQAPGKGLEWVAVIWYDGSNKYYADSVKGRF TISRDNSKNTLYLQMNSLRAEDTAVYYCARRYSSS WVGGMDVWGQGTTVTVSS<br>SEQ ID NO: 29238 |

FIGURE 50
(Continued)

| | | | |
|---|---|---|---|
| iPS:433939 | 21-225_44C10 | NA | GACATCCAGATGACCCAGTCTCCATCCTCCT GTCTGCATCTGTAGGAGACAGAGTCACCTTCA CTTGCCGGGCAAGTCAGGGCATTAGAGATGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCCTCTGGATTCACCTTCAGTGACTGTGTCAT GCACTGGGTCCGCCAGGCTCCAGGCAAGGGGCT GGAGTGGGTGGCAGTTATATGTGATGGAAGT AATAAATACTATGCTGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAAAGTAT AGCAGTGGCTTGTACGACTACGGTATGGACGTCT GGGGCCAAGGGACCACGGTCACCGTCTCCTCA |
| | | | SEQ ID NO: 25233 | SEQ ID NO: 29239 |
| | | AA | DIQMTQSPSSLSASVGDRVTFTCRASQGIRDDLG WYQQKPGKAPKRLIYATSSLQSGVPSRFSGSGSG TEFTLTISSLQPEDFATYYCLQHYSYPRTFGQGT KVEIK | QVQLVESGGGVVQPGRSLRLSCAASGFTFSDCVMH WVRQAPGKGLEWVAVIWYDGSNKYYADSVKGRF TISRDNSKNTLYLQMNSLRAEDTAVYYCARERYSS GLYDYGMDVWGQGTTVTVSS |
| | | | SEQ ID NO: 25234 | SEQ ID NO: 29240 |
| iPS:433941 | 21-225_44D10 | NA | GACATCCAGATGACCCAGTCTCCATCTTCCGT GTCTGCATCTGTAGGAGACAGAGTCACCATCA CTTGTCGGGCGAGTCAGGGTATTAGCGACTGG TTAGCCTGGTATCAACAGAAACCAGGGAAAG CCCCTAAGGCTCTGATCTATGCTGCATCCAGTT TGCAAAGTGGGGTCCCATCAAAATTCAGCGGC AGTGGATCTGGGACAGATTTCACTCTCACAAT CAGCAACCTGCAGCCTGAAGATTTTGCAACTT ACTATTGTCAACAGACTAACAGTTTCCCGTGG ACGTTCGGCCAAGGGACCAAGGTGGAAATCA AA | GAGGTGCAGCTGTGTTGGAGTCTGGGGGAGGCTTG GTACAGCCTGGGGGGTCCCTGAGACTCTCCTGTG CAGCCTCTGGATTCACCTTTAGCAGCTATGCCAT GAGTTGGGTCCGCCAGGCTCCAGGGAAGGGGCT GGAGTGGGTCTCAGCTATTAGTGGTGTGGTGTT AACACATTGCACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAGGAAAGA GTGGGAGCTATTTTGACTACTGGGGCCAGGGAAC CCTGGTCACCGTCTCCTCA |
| | | | SEQ ID NO: 25235 | SEQ ID NO: 29241 |

FIGURE 50
(Continued)

| | | | | |
|---|---|---|---|---|
| iPS:433943 | 21-225_44E10 | AA | DIQMTQSPSSVSASVGDRVTITCRASQGISDWLA WYQQKPGKAPRLLIYAASSLQSGVPSKFSGSGS GTDFTLTISNLQPEDFATYYCQQTNSFPWTFGQG TKVEIK<br><br>SEQ ID NO: 25236 | EVQLLESGGGLVQPGGSLRLSCAASGFTFSSYAMS WVRQAPGKGLEWVSAISGRGVNTFDADSVKGRFTI SRDNSKNTLYLQMNSLRAEDTAVYYCAKERSGSY FDYWGQGTLVTVSS<br><br>SEQ ID NO: 29242 |
| | | NA | GATATTGTGATGACTCAGTCTCCACTCTCCCTG CCCGTCACCCCTGGAGAGCCGGCCTCCATCTC CTGCAGGTCTAGTCAGAGCCTCCTGCATAGTA ATGGATACAGCTATTTGGAGTGGTACCTGCAG AAGCCAGGACAGTCTCCACAACTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTAGAGGCTGA GGATGTTGGGGTTTATTACTGCATGCAAACTC TACAAACTCCATTCACTTTCGGCCCTGGGACC AAAGTGGATATCAAA<br><br>SEQ ID NO: 25237 | GAGGTGCAGCTGTTGGAGTCTGGGGGAGGCTTG GTACAGTCTGGAGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGGTGTTGTTGGTAGTGGTGGT AGAACATACTACGCAGACTCCGTGAAGGGCCGG TTCATCATCTCCAGAGACAATTCCAAGAACACGC TGTATCTGCAAATGAACAGCCTGAGAGCCGAGG ACACGGCCGTATATTACTGTGCGAAAGATCGGG GGCAGTGGCTCCTAGGCGGTATGGACGTCTGGG GCCAAGGGACCACGGTCACCGTCTCCTCA<br><br>SEQ ID NO: 29243 |
| | | AA | DIVMTQSPLSLPVTPGEPASISCRSSQSLLHSNGY SYLEWYLQKPGQSPQLLIYLGSNRASGVPDRFSG SGSGTDFTLKISRVEAEDVGVYYCMQTLQTPFTF GPGTKVDIK<br><br>SEQ ID NO: 25238 | EVQLLESGGGLVQSGGSLRLSCAASGFTFSSYAMN WVRQAPGKGLEWVSGVVGSGGRTYYADSVKGRFI ISRDNSKNTLYLQMNSLRAEDTAVYYCAKDRGQW LLGGMDVWGQGTTVTVSS<br><br>SEQ ID NO: 29244 |

FIGURE 50
(Continued)

| | | | |
|---|---|---|---|
| iPS:433945 | 21-225_44C12 | NA | GACATCCAGATGACCCAGTCTCCATCTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTCTGCTGCATTCAGT TGCAAAGTGGGGTCCCATCAAGGTTCAGCGGC AGTGGATCTGGGACAGATTTCACTCTCAGCAT CAGCAGCCTGCAGCCTGAAGATTTTGCAACTT ACTATTGTCAACAGTCTAACAGTTTCCCGTGG ACGTTCGGCCAAGGGACCAAGGTGGAAATCA AA |
| | | | SEQ ID NO: 25239 |
| | | AA | DIQMTQSPSSVSASVGDRVTITCRASQGISNWLA WYQQKPGKAPKLLISAAFSLQSGVPSRFSGSGSG TDFTLSISSLQPEDFATYYCQQSNSFPWTFGQGT KVEIK |
| | | | SEQ ID NO: 25240 |
| | | NA | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTATAGCGT GAACTGGGTCCGCCAGGCTCCAGGGAAGGGGCT GGAGTGGGTTTCATACATTAGTAGTAGTAGTAGT ACCATATACTACGCAGACTCTGTGAAGGGCCGAT TCACCATCTCCAGAGACAATGCCAAGAACTACT GTATCTGCAAATGAACAGCCTGAGAGACGAGGA CACGGCTGTGTATTACTGTGCGAGAAGTGGATAC AGCTATGCTTACTACTACGGTATGGACG TCTGGGGCCAAGGGACCACGGTCACCGTCTCCTC A |
| | | | SEQ ID NO: 29245 |
| | | | EVQLVESGGGLVQPGGSLRLSCAASGFTFSSYSVN WVRQAPGKGLEWVSYISSSSSTIYYADSVKGRFTIS RDNAKNSLYLQMNSLRDEDTAVYYCARSGYSYAY YYYYGMDVWGQGTTVTVSS |
| | | | SEQ ID NO: 29246 |
| iPS:433947 | 21-225_44E12 | NA | GACATCCAGATGACCCAGTCTCCATCTCCCT GTCTGCATCTGTAGGAGACAGAGTCACCATCA CTTGCCGGGACAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGACCTGGAAATCA TATTACTGTCTACAACATAATAGTTACCCGCTC ACTTTCGGCGGAGGGACCAAGGTGGAGATCA AA |
| | | | SEQ ID NO: 25241 |
| | | | CAGGTGCACCTGGCGGAGTCTGGGGGAGGCGTG GTCCAGCCTGGGAGGTCCCTGAGACTCTCCTGTG AAGCGTCTGGATTCACCCTCAGTAGCGATGACAC GCACTGGGTCCGCCAGCCTCCAGGCAAGGGGCT GGAGTGGGTGGCAGTTATATGGTTTGATGAATAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACGCGGCTGTGTATTACTGTGCGAGAGATCTAAT AGCAGCAGCTGGGACGGGAGACTACTGGGGCCA GGGAACCCTGGTCACCGTCTCCTCA |
| | | | SEQ ID NO: 29247 |

FIGURE 50
(Continued)

| | | | |
|---|---|---|---|
| iPS:433949 | 21-225_45H2 | AA | DIQMTQSPSSLSASVGDRVTITCRTSQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 25242 | QVHLAESGGGVVQPGRSLRLSCEASGFTLSSDDTH WVRQPPGKGLEWVAVIWFDEYNKYADSVKGRF TISRDNSKNTLYLQMNSLRAEDAAVYYCARDLIAA AGTGDYWGQGTLVTVSS<br>SEQ ID NO: 29248 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAAG CCCCTAAGCGCCTGATCTATGGTGCATCCAAT TTGCAAAGTGGGGGTCCCATCAAGGTTCAGCGG CAGTGGATCTGGGACAGATTCACTCTCACAG TCAGCAGCCTGCAGCCTGAAGATTTTGCAACT TATTTCTGTCTACAGCATACTAGTTTCCCATTC ACTTTCGGCCCTGGGACCAAAGTGGATATCAA A<br>SEQ ID NO: 25243 | CAGGTGCAGCTGGTGGAGTCTGGGGGAGGCTTG GTCAAGCCTGGAGGGTCCCTGAGACTCTCCTGTG CAGCCTCTGGATTCACCTTAGTGACTACTACAT GAACTGGATCCGCCAGGCTCCAGGGAAGGGGCT GGAGTGGGTTCATACATTAGTAGTAGTGGTATT ACCAAATACTACGCAGACTCTGTGAAGGGCCGA TTCACCATCTCCAGGGACAACGCCAAGAACTCAC TGTATCTGCAAATGAACAGCCTGAGAGCCGAGG ACACGGCCGTGTATTACTGTGCGGCCGATACAAT CTACTGGGGCCAGGGAACCCTGGTCACCGTCTCC TCA<br>SEQ ID NO: 29249 |
| | | AA | DIQMTQSPSSLSASVGDRVTITCRASQGIRNDLG WYQQKPGKAPKRLIYGASNLQSGVPSRFSGSGS GTEFTLTVSSLQPEDFATYFCLQHTSFPFTFGPGT KVDIK<br>SEQ ID NO: 25244 | QVQLVESGGGLVKPGGSLRLSCAASGFTFSDYYMN WIRQAPGKGLEWVSYISSSGITKYYADSVKGRFTIS RDNAKNSLYLQMNSLRAEDTAVYYCAADTIYWGQ GTLVTVSS<br>SEQ ID NO: 29250 |

FIGURE 50
(Continued)

| | | | |
|---|---|---|---|
| iPS:433951 | 21-225_45B4 | NA | GACATCCAGATGACCCAGTCTCCATCTCCT GTCTGCATCTGTAGGAGACAGAGTCACCTTCA CTTGCCGGGCAAGTCAGGGCATTAGAGATGAT TTAGGCTGGTATCAACAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTGTGTCAT GCACTGGGTCCGCCAGGCTCCAGGCAAGGGGCT GGAGTGGGTGGCAGTTATATGTGATGGAAGT AATAAATACTATGCTGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAAAGTAT AGCAGTGGCTTGTACGACTACGGTATGGACGTCT GGGGCCAAGGGACCACGGTCACCGTCTCCTCA |
| | | | SEQ ID NO: 25245 | SEQ ID NO: 29251 |
| | | AA | DIQMTQSPSSLSASVGDRVTFTCRASQGIRDDLG WYQQKPGKAPKRLIYAASSLQSGVPSRFSGSGS GTEFTLTISSLQPEDFATYYCLQHYSYPRTFGQG TKVEIK | QVQLVESGGGVVQPGRSLRLSCAASGFTFSDCVMH WVRQAPGKGLEWVAVIWYDGSNKYYADSVKGRF TISRDNSKNTLYLQMNSLRAEDTAVYYCARERYSS GLYDYGMDVWGQGTTVTVSS |
| | | | SEQ ID NO: 25246 | SEQ ID NO: 29252 |
| iPS:433953 | 21-225_45H4 | NA | GACATCCAGATGACCCAGTCTCCATCTTCCGT GTCTGCATCTGTAGGAGACAGAGTCACCATCA CTTGTCGGGCGAGTCAGGATATTAGCAGCTGG TTAGCCTGGTATCAGAAGAAACCAGGGAAAG CCCCTAAGTCCCTGATCTATGATGCATCCAGT TTGCAAAGTGGGGTCCCATCAAGGTTCAGCGG CAGTGGATCTGGGACAGATTTCATTCTCACCA TCAGCAGCCTGCAGCCTGAAGATTTTGCAATT TACTTTTGTCAACAGGCTAACAGTCTCCCTTTC ACTTTCGGCCCTGGGACCAAAGTGGATATCAA A | GAGGTGCAGCTGTGTTGGAGTCTGGGGGAGGCTTG GTACAGCCTGGGGGGTCCCTGAGACTCTCCTGTG CAGCCTCTGGATTCACCTTTAGCAGCTATGCCAT GAGTTGGGTCCGCCAGGCTCCAGGGATGGGGCT GGAGTGGGTCTCAGCTATTAGTGGTAGTGGTAGT AACACATTCTACGCAGACTCCGTGAAGGGCCGGT TCACCATCTCCAGAGACAATTCCAAGAGCCGCT GTATCTGCAAATGAACAGCCTGAGAGCCGAGGA CACTGCCGTATATTTCTGTGCGAAACGAACGCCC TCTGATGTTTTTGATATCTGGGGCCAAGGGACAA TGGTCACCGTCTCTTCA |
| | | | SEQ ID NO: 25247 | SEQ ID NO: 29253 |

FIGURE 50
(Continued)

| | | | | |
|---|---|---|---|---|
| | | AA | DIQMTQSPSSVSASVGDRVTITCRASQDISSWLAWYQKKPGKAPKYLIYDASSLQSGVPSRFSGSGSGTDFILTISSLQPEDFAIYFCQQANSLPFTFGPGTKVDIK | EVQLLESGGGLVQPGGSLRLSCAASGFTFSSYAMSWVRQAPGMGLEWVSAISGSGSNTFYADSVKGRFTISRDNSKNTLYLHMNSLRAEDTAVYFCAKRTPSDVFDIWGQGTMVTVSS |
| | | | SEQ ID NO: 25248 | SEQ ID NO: 29254 |
| iPS:433955 | 21-225_45B8 | NA | GACATCCAGATGACCCAGTCTCCATCCTCCCTGTCTGCATCTGTAGGAGACAGAGTCACCTTCACCTTGCCGGGCAAGTCAGGACATTAGAGATGATTTAGGCTGGTATCAGCAGAAACCAGGGAAAGCCCCTAAGCGCCTGATCTATGCTGCATCCAGTTTGCAAAGTGTGGGGTCCCATCAAGGTTCAGCGGCAGTGGATCTGGGACAGATCTCACTCTCACAACTCAGCAGCCTGCAGCCTGAAGATTTTGCAACTTATTACTGTCTACAGCATTATAATTACCCTCGGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTGTGTCATGCACTGGGTCCGCCAGGCTCCAGGCAAGGGGCTGGAGTGGGTGGCAGTTATATGTGATGGAAGTAATAAATACTATGCTGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGACTACGGTATGGACGTCTAGCAGTGGCTTGTACGACTACGGTATGGACGTCTGGGGCCAAGGGACCACGGTCACCGTCTCCTCA |
| | | | SEQ ID NO: 25249 | SEQ ID NO: 29255 |
| | | AA | DIQMTQSPSSLSASVGDRVTFTCRASQDIRDDLGWYQQKPGKAPKRLIYAASSLQSGVPSRFSGSGSGTEFTLTISSLQPEDFATYYCLQHYNYPRTFGQGTKVEIK | QVQLVESGGGVVQPGRSLRLSCAASGFTFSDCVMHWVRQAPGKGLEWVAVIWYDGSNKYYADSVKGRFTISRDNSKNTLYLQMNSLRAEDTAVYYCARERYSSGLYDYGMDVWGQGTTVTVSS |
| | | | SEQ ID NO: 25250 | SEQ ID NO: 29256 |

FIGURE 50
(Continued)

| | | | | |
|---|---|---|---|---|
| iPS:433957 | 21-225_45F8 | NA | GACATCCAGATGACCCAGTCTCCATCTTCCGT GTCTGCATCTGTAGGAGACAGAGTCACCATCA CTTGTCGGGCGAGTCAGGTATTAGCGACTGG TTAGCCTGGTATCAGCAGAAACCAGGGAAAG CCCCTAGGCTCCTGATCTATGGTGCATCCAGTT TGCAAAGTGGGGTCCCATCAAGGTTCAGCGGC AGTGGATCTGGGACAGATTTCACTCTCACCAT CAGCAACCTGCAGCCTGAAGATTTTGCAACTT ACTATTGTCAACAGATCTAACAGTTCCCGTGG ACGTTCGGCCAAGGGACCAAGGTGGAAATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCAGTATGCCAT GAGCTGGGTCCGCCAGGCTCCAGGGAAGGGGCT GGAGTGGGTCTCAGTATTAGTGGTCGTGGTGTT AACACATTCGACGCAGACTCCGTGAAGGGCCGG TTCACCATATCCAGAGACAATTCCAAGAACACGC TGTATCTGCAAATGAACAGCCTGAGAGCCGAGG ACACGGCCGTATATTACTGTGCGAAGGAAAGA GTGGGAGCTATTTTGACTACTGGGGCCAGGAAAC CCTGGTCACCGTCTCCTCA |
| | | | SEQ ID NO: 25251 | SEQ ID NO: 29257 |
| | | AA | DIQMTQSPSSVSASVGDRVTITCRASQGISDWLA WYQQKPGKAPRLLIYGASSLQSGVPSRFSGSGSG TDFTLTISNLQPEDFATYYCQQTNSFPWTFGQGT KVEIK | EVQLLESGGGLVQPGGSLRLSCAASGFTFSSYAMS WVRQAPGKGLEWVSAISGRGVNTFDADSVKGRFTI SRDNSKNTLYLQMNSLRAEDTAVYYCAKERSGSY FDYWGQGTLVTVSS |
| | | | SEQ ID NO: 25252 | SEQ ID NO: 29258 |
| iPS:433959 | 21-225_45C9 | NA | GACATCCAGATGACCCAGTCTCCATCTTCCGT GTCTGTTTCTGGGCGAGTCAGGATCAGCAGTCACCATCA CTTGTCGGGCGAGTCAGGATATTAGCGACTGG TTAGCTTGGTATCAGCAGGACCAGGGAAAGC CCCTAAGCTCTTGATCTATGCTGCATCAGTTT GGAAAGTGGGGTCCCATCAAGGTTCAGCGGC AGTGGATCTGGGACAGCTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A | GAGGTGCAGCTGTTGGAGTCTGGGGGAGGCTTG GTACAGCCTGGGGGGTCCCTGAGACTCTCCTGTG CAGCCTCTGCTGATTCACCTTTAACACAGCTATGCCAT GAGCTGGGTCCGCCAGGCTCCAGGGAAGGGGCT GGAGTGGGTCTCAGTTATTAGTGGTCGTGGTGGT ACCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAACGAACGCC CTCTGATGCTTTTGATATCTGGGGCCAAGGGACA ATGGTCACCGTCTCTTCA |
| | | | SEQ ID NO: 25253 | SEQ ID NO: 29259 |

FIGURE 50
(Continued)

| | | | |
|---|---|---|---|
| iPS:433961 | 21-225_45D9 | AA | DIQMTQSPSSLSVSVGDRVTITCRASQDISDWLA WYQQRPGKAPKLLIYAASSLESGVPSRFSGSGSG TDFTLTISSLQPEDFATYYCQQANSFPFTFGPGTK VDIK<br><br>SEQ ID NO: 25254 | EVQLLESGGGLVQPGGSLRLSCAASGFTFNSYAMS WVRQAPGKGLEWVSVISGRGTTYYADSVKGRFT ISRDNSKNTLYLQMNSLRAEDTAVYYCAKRTPSDA FDIWGQGTMVTVSS<br><br>SEQ ID NO: 29260 |
| | | NA | GACATCCAGATGACCCAGTCTCCATCCTCACT GTCTGCATCTGTAGGAGACAGAGTCACCATCA CTTGTCGGGCGAGTCAGGGCATTAACAATTAT TTAGCCTGGTTTCAGCAGAAACCAGGGAAAGC CCCTAAGTCCCTGATCAATGCTGCATCCAGTTT GCAAAGTGGGGTCCCATCAAGGTTCAGCGGCA GTGGATCTGGGACAGATTTCACTCTCGCCATC AGCAGCCTACAGCCTGAAGATTTTGCAACTTA TTACTGCCAACACTATTATTAGTTACCATTCAC TTTCGGCCCTGGGACCAAAGTGGATATCAAA<br><br>SEQ ID NO: 25255 | GAGGTGCAGCTGGTGGAGTCTGGGGGAGGCCTG GTCAAGCCGGGGGGGTCCCTGAGACTCTCCTGTG CAGCCTCTGGATTCACCTTCAGTAGCTATACCAT GAACTGGGTCCGCCAGGTTCCAGGGAAGGGGCT GGAGTGGGTCTCATCCATTAGTGGAAGTAGTACT TACATATACTACGCAGACTCAGTGAAGGGCCGAT TCACCATCTCCAGAGACAACGCCAGAACTCACT GTATCTGCAAATGAACAGCTGAGAGGCGAGA CACGGCTGTGTATTACTGTGCGAGGGTGACCTCT TTTGACTACTGGGGCCAGGGAGCCCTGGTCACCG TCTCCTCA<br><br>SEQ ID NO: 29261 |
| | | AA | DIQMTQSPSSLSASVGDRVTITCRASQGINNYLA WFQQKPGKAPKSLINAASSLQSGVPSRFSGSGSG TDFTLAISSLQPEDFATYYCQHYYSYPFTFGRGT KVDIK<br><br>SEQ ID NO: 25256 | EVQLVESGGGLVKPGGSLRLSCAASGFTFSSYTMN WVRQVPGKGLEWVSSISGSSTYIYYADSVKGRFTIS RDDAQNSLYLQMNSLRGEDTAVYYCARVTSFDY WGQGALVTVSS<br><br>SEQ ID NO: 29262 |

FIGURE 50
(Continued)

| | | | | |
|---|---|---|---|---|
| iPS:433963 | 21-225_46B1 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAGGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA | CAGGTGCACCTGGCGGAGTCTGGGGGAGGCGTG GTCCAGCCTGGGAGGTCCCTGAGACTCTCCTGTG AAGCGTCTGGATTCACCCTCAGTAGCGATGACTC GCACTGGGTCCGCCAGCTCCAGGCAAGGGCT GGAGTGGGTGGCAGTTATATGGTTTGATGAATAT ACTAAATACTATGCAGACTCCGTGAAGGGCCGAT TCACCATCTCCAGAGACAACAATTCCAAGAACACGCT GTATCTGCAAATGAACAACCTGAGAGCCGAGGA CGCGGCTGTGTATTACTGTGCGAGAGATCTAATA GCAGCAACTGGGACGGGAGACTACTGGGGCCAG GGAACCCTGGTCACCGTCTCCTCA |
| | | | SEQ ID NO: 25257 | SEQ ID NO: 29263 |
| | | AA | DIQMTQSPSSLSASVGDRVTITCRASQGIRNDLG WYQQKPGKAPKRLIYAASSLQGGVPSRFSGSGS GTEFTLTISSLQPEDFATYYCLQHNSYPLTFGGG TKVEIK | QVHLAESGGGVVQPGRSLRLSCEASGFTLSSDDSH WVRQPPGKGLEWVAVIWFDEYTKYYADSVKGRFT ISRDNSKNTLYLQMNNLRAEDAAVYYCARDLIAAT GTGDYWGQGTLVTVSS |
| | | | SEQ ID NO: 25258 | SEQ ID NO: 29264 |
| iPS:433965 | 21-225_46F2 | NA | GATATCGTGATGACCCAGACTCCACTCTCT GACCGTCACCCCTGGACAGCCGGCCTCCATCT CCTGCAAGTCTAGTCAGAGCCTCCTGCATGGT GATGAAAGACATATTGTATTGGTACCTGCA GAAGCCAGGCCAGCCTCCACAGGTCCTGATCT ATGAAGTTTCCAATCGGTTCTCTGGAGTGCCA GATAGGTTCAGTGGCAGCGGGTCAGGGACAG ATTTCACACTGAAACTCAGCGGGGTGGAGGCT GAGGATGTTGGGGTTTATTACTGCATGCAAAG TATACAGCTTCCGTGGACGTTCGGCCAAGGGA CCAAGGTGGAAATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAATTATATGACTCCGTGAAGT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATCGATAC GATTTTTGGAGTGGTTACTTGACTACTGGGGCC AGGGAACCCTGGTCACCGTCCTCA |
| | | | SEQ ID NO: 25259 | SEQ ID NO: 29265 |

FIGURE 50
(Continued)

| | | | | |
|---|---|---|---|---|
| | | AA | DIVMTQTPLSLTVTPGQPASISCKSSQSLLHGDG KTYLYWYLQKPGQPPQVLIYEVSNRFSGVPDRF SGSGSGTDFTLKLSRVEAEDVGVYYCMQSIQLP WTFGQGTKVEIK<br>SEQ ID NO: 25260 | QVQLVESGGGVVQPGRSLRLSCAASGFTFSSYGMH WVRQAPGKGLEWVAIIHWYDGSNKYYVDSVKGRFT ISRDNSKNTLYLQMNSLRAEDTAVYYCARDRYDF WSGYFDYWGQGTLVTVSS<br>SEQ ID NO: 29266 |
| iPS:433967 | 21-225_46C3 | NA | GACATCCAGATGACCCAGTCTCCATCCTCCCT GTCTGCATCTGTAGGAGACAGAGTCACCTTCA CTTGCCGGGCAAGTCAGGGCATTAGAGATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTAGATCTGGGACAGAATTCACTCTCACAA TCAGCAGCCTGCAACCTGAAGATTTTGCAACT TATTACTGTCTACAGCATTATAGTTACCCTCGG ACGTTCGGCCAAGGGACCAAGGTGGAAATCA AA<br>SEQ ID NO: 25261 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGGCT GGAGTGGGTGGCAGTTATATGTGACTCCGTGAAGT AATAAATACTATGCTGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAAAGTAT AGCAGTGGCTTGTACGACTACGGTATGGACGTCT GGGGCCAAGGGACCACGGTCACCGTCTCCTCA<br>SEQ ID NO: 29267 |
| | | AA | DIQMTQSPSSLSASVGDRVTFTCRASQGIRDDLG WYQQKPGKAPKRLIYAASSLQSGVPSRFSGSRS GTEFTLTISSLQPEDFATYYCLQHYSYPRTFGQG TKVEIK<br>SEQ ID NO: 25262 | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCARERYSS GLYDYGMDVWGQGTTVTVSS<br>SEQ ID NO: 29268 |

FIGURE 50
(Continued)

| | | | |
|---|---|---|---|
| iPS:433969 | 21-225_46F3 | NA | GACATCCAGATGACCCAGTCTCCATCCTCCT GTCTGCATCTGTAGGAGACAGAGTCACCATCA CTTGCCGGGCAAGTCAGGGACATTAGAAAAGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCAGTCTCACAA TCAGCAGCCTGCAGCCTGAAGATTTTGCAACT TATTACTGTCTACAGCATAATAGTTACCCTCTC ACTTTCGGCGGAGGGACCAAGGTGGAGATCA AG SEQ ID NO: 25263 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGATTATGGCAT GCACTGGGTCCGCCAGGCTCCAGGCAAGGGCT GGAGTGGGTGGCAGTTATATGGTTTGAAGGAAGT AATAAATACTATGCAGATTCCGTGAAGGGCCGAT TCACCATCTCCAGAGACAATTCCAAGAACACGCT GTATGTGCAAATGAACAGCCTGAGAGCCGAGGA CACGGCTGTGTATTACTGTGTGAGAGAACTAGGA TTTTCCAATGACTACTGGGGCCAGGGAACCCTGG TCACCGTCTCCTCA SEQ ID NO: 29269 |
| | | AA | DIQMTQSPSSLSASVGDRVTITCRASQGIRKDLG WYQQKPGKAPKRLIYAASSLQSGVPSRFSGSGS GTEFSLTISSLQPEDFATYYCLQHNSYPLTFGGGT KVEIK SEQ ID NO: 25264 | QVQLVESGGGVVQPGRSLRLSCAASGFTFSDYGM HWVRQAPGKGLEWVAVIWFEGSNKYYADSVKGR FTISRDNSKNTLYVQMNSLRAEDTAVYYCVRELGF SNDYWGQGTLVTVSS SEQ ID NO: 29270 |
| iPS:433971 | 21-225_46D4 | NA | GACATCCAGATGACCCAGTCTCCATCCTCCT GTCTGCATCTGTAGGAGACAGAGTCACCATCA CTTGCCGGACAAGTCAGGACATTAGAAAAGAT TTAGGCTGGTATCAGCAGAAAGTAGGGAAAG CCCCTAAGCGCCTGATCTATGCTGCATCCAGT TTGGAAAGTGGGGTCCCATCAAGGTTCAGCGG CAGTGGATCTGGGACACAGAATTCACTCTCACAA TCAGCAGCCTGCAGCCTGAAGATTTTGCAACT TATTACTGTCTACAGCATTATAGTTTCCCGTGG ACGTTCGGCCAAGGGACCAAGGTGGAAATCA AA SEQ ID NO: 25265 | CAGGTGCAGCTGGTGGAGTCTGGGGGAGGCGTA GTCCAGCCTGGGAGGTCCCTGAGACTCTCCTGTG CAGCGTCTGGATTCACCTTCAGTGATTAGTGTCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAACATTCCAAGAACACGC TGTATCTGCAAATGAACAGCCTGAGAGCCGAGG ACACGGCTGTGTATTACTGTGTGAGAGTCCGTA TAGCAGCAGTTGGTACGACTACGGTATGGACGTC TGGGGCCAAGGGACCACGGTCACCGTCTCCTCA SEQ ID NO: 29271 |

FIGURE 50
(Continued)

| | | | |
|---|---|---|---|
| iPS:433973 | 21-225_46A6 | AA | DIQMTQSPSSLSASVGDRVTITCRTSQDIRKDLG WYQQKVGKAPKRLIYAASSLESGVPSRFSGSGS GTEFTLTISSLQPEDFATYYCLQHYSFPWTFGQG TKVEIK<br>SEQ ID NO: 25266 | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCARVPYSS SWYDYGMDVWGQGTTVTVSS<br>SEQ ID NO: 29272 |
| | | NA | GACATCCAGATGAACCAGTCTCCATCTTCCGT GTCTGCATCTGTAGGAGACAGAGTCAACATCA CTTGTCGGGCGAGTCAGGGTATTAGCAACTGG TTAGCCTGGTATCAGCAGAAACCAGGGAAAGT CCCTAAGCTCCTGATCTATGCTGCATCCAGTTT GCAAAGTGGGGTCCCATCAAGGTTCAGCGGCA GTGGATCTGGGACAGATTTCACTCTCACCATC AGCAACCTGCAGCCTGAAGATTTTGCAACTTA CTATTGTCAACAGACTAACAGTTTCCCGTGGA CGTTCGGCCAAGGGACCAAGGTGGAAATCAA A<br>SEQ ID NO: 25267 | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTATT AACACATTCGACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAGGAAAGGA GTGGGAGCTATTTTGACTACTGGGGCCAGGGAAC CCTGGTCACCGTCTCCTCA<br>SEQ ID NO: 29273 |
| | | AA | DIQMNQSPSSVSASVGDRVNITCRASQGISNWLA WYQQKPGKVPKLLIYAASSLQSGVPSRFSGSGS GTDFTLTISNLQPEDFATYYCQQTNSFPWTFGQG TKVEIK<br>SEQ ID NO: 25268 | EVQLLESGGGLVQPGGSLRLSCAASGFTFSSYAMS WVRQAPGKGLEWVSAISRGRINTFDADSVKGRFTI SRDNSKNTLYLQMNSLRAEDTAVYYCAKERSGSY FDYWGQGTLVTVSS<br>SEQ ID NO: 29274 |

FIGURE 50
(Continued)

| | | | | |
|---|---|---|---|---|
| iPS:433975 | 21-225_46C6 | NA | GACATCCAGATGACCCAGTCTCCATCCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCTCTC ACTTTCGGCGGAGGGACCAAGGTGGAGATCA CA  SEQ ID NO: 25269 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTATGGCAT ACACTGGGTCCGCCAGGCTCCAGGCAAGGGGCT GGAGTGGGTGGCAGTTATATGCAGACTCCGTGATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGTAGG ATTTTCCAATGACTACTGGGGCCAGGGAACCCTG GTCACCGTCTCCTCA  SEQ ID NO: 29275 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIT  SEQ ID NO: 25270 | QVQLVESGGGVVQPGRSLRLSCAASGFTFSSYGIH WVRQAPGKGLEWVAVIWYDENNKYYADSVKGRF TISRDNSKNTLYLQMNSLRAEDTAVYYCARELGFS NDYWGQGTLVTVSS  SEQ ID NO: 29276 |
| iPS:433977 | 21-225_46D8 | NA | GACATCCAGATGACCCAGTCTCCATCCCCT GTCTGCATCTGTAGGAGACAGAGTCACCATCA CTTGCCGGGCAAGTCAGGGCATTAGAAAAGAT TTAGGCTGGTATCAGCAGAAACCAGGGAAAG CCCCTAAGCGCCTGATCTATGCTGCATCCAGT TTGCAAAGTGGGGTCCCATCAAGGTTCAGTGG CAGTGGATCTGGGACAGCCTGAGCATCAGTCTCACAA TCAGCAGCCTGCAGCCTGAAGATTTTGCAACT TATTACTGTCTACAGCATAATAGTTACCCTCTC ACTTTCGGCGGAGGGACCAAGGTGGAGATCA AG  SEQ ID NO: 25271 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGATTATGGCAT ACACTGGGTCCGCCAGGCTCCAGGCAAGGGGCT GGAGTGGGTGGCAGTTATATGGTTTGAAGGAAGT AATAAATACTATGCAGATTCCGTGAAGGGCCGAT TCACCATCTCCAGAGACAATTCCAAGAACACGCT GTATGTGCAAATGAACAGCCTGAGAGCCGAGGA CACGGCTGTGTATTACTGTGTGAGAGAACTAGGA TTTTCCAATGACTACTGGGGCCAGGGAACCCTGG TCACCGTCTCCTCA  SEQ ID NO: 29277 |

FIGURE 50
(Continued)

| | | | |
|---|---|---|---|
| iPS:433979 | 21-225_46B9 | AA | DIQMTQSPSSLSASVGDRVTITCRASQGIRKDLG WYQQKPGKAPKRLIYAASSLQSGVPSRFSGSGS GTEFSLTISSLQPEDFATYYCLQHNSYPLTFGGGT KVEIK<br>SEQ ID NO: 25272 | QVQLVESGGGVVQPGRSLRLSCAASGFTFSDYGIH WVRQAPGKGLEWVAVIWFEGSNKYYADSVKGRF TISRDNSKNTLYVQMNSLRAEDTAVYYCVRELGFS NDYWGQGTLVTVSS<br>SEQ ID NO: 29278 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GAGGGAAAGACCTATTTGTATTGGTACCTGCA GAAGCCAGGCCAGCCTCCACAGCTCCTGATCT ATGAAGTTTCTTACCGGTTCTCTGGAGTGCCA GATAGGTTCAGTGGCAGCGGGTCAGGGACAG ATTTCACACTGAAAATCAGCGGATGGAGGCT GAGGATGTTGGGGTTTATTACTGCATGCACAG TATACAGTATCCGCTCACGTTTGGCGGAGGGA CCAAGGTGGAGATCCAA<br>SEQ ID NO: 25273 | CAGGTGCAGCTGGTGGAGTCTGGGGGAGGCGTG GTCCAGCCTGGGAGGTCCCTGAGACTCTCCTGT CAGCGTCTGGATTCACCTTCAGTAGTAGTGGCAT GCACTGGGTCCGCCAGGCTCCAGGCAAGGGGCT GGAGTGGGTGGCAGTTATATGGTATGAAG AATAAATACTATGCAGACTCCGTGAAGGGCCG AATCACCATCTCCAGAGACAATTCCAAGAACAC GCTGTATCTGCAAATGAACAGCTGAGAGCCGA GGACACGGCTGTGTATTACTGTGCGAGGCGGTAT AGCAGCAGCTGGATGGGAGGTATGACGTCTGG GGCCAAGGGACCACGGTCACCGTCTCCTCA<br>SEQ ID NO: 29279 |
| | | AA | DIVMTQTPLSLSVTPGQPASISCKSSQSLLHSEGK TYLYWYLQKPGQPPQLLIYEVSYRFSGVPDRFSG SGSGTDFTLKISRMEAEDVGVYYCMHSIQYPLTF GGGTKVEIQ<br>SEQ ID NO: 25274 | QVQLVESGGGVVQPGRSLRLSCSASGFTFSSYGMH WVRQAPGKGLEWVAVIWYDGRNKYYADSVKGRI TISRDNSKNTLYLQMNSLRAEDTAVYYCARRYSSS WMGGMDVWGQGTTVTVSS<br>SEQ ID NO: 29280 |

FIGURE 50
(Continued)

| | | | |
|---|---|---|---|
| iPS:433981 | 21-225_46E9 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGAAAG CCCCTAAGCGCCTGATCTATGCTGCATCCAGT TGCAAAGTGGGGTCCCATCAAGGTTCAGCGG CAGTGGATCTGGGACAGAATTCACTCTCACAG TCAGCAGCCTGCAGCCTGAAGATTTTGCAACT TATTTCTGTCTTCAGCATACTAGTTTCCCATTC ACTTTCGGCCCTGGGACCAAAGTGGATATCAA A SEQ ID NO: 25275 | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTACAT GAACTGGATCCGCCAGGCTCCAGGGAAGGGGCT GGAGTGGGTTTCATACATTAATAGTAATGGTTTT ACCATATACTACGCAGACTCTGTGAAGGGCCGAT TCACCATCTCCAGGGACAACAGCCAAGAACTACT GTATCTGCAAATGAACAGCCTGAGAGCCGAGGA CACGGCCGTGTATTACTGTGCGGCCGATACAATC TACTGGGGCCAGGGAACCCTGGTCACCGTCTCCT CA SEQ ID NO: 29281 |
| | | AA | DIQMTQSPSSLSASVGDRVTITCRASQGIRNDLG WYQQKPGKAPKRLIYAASSLQSGVPSRFSGSGS GTEFTLTVSSLQPEDFATYFCLQHTSFPFTFGPGT KVDIK SEQ ID NO: 25276 | QVQLVESGGGLVKPGGSLRLSCAASGFTFSDYYMN WIRQAPGKGLEWVSYINSNGFTIYYADSVKGRFTIS RDNAKNSLYLQMNSLRAEDTAVYYCAADTIYWGQ GTLVTVSS SEQ ID NO: 29282 |
| iPS:433983 | 21-225_47A1 | NA | GACATCCAGATGACCCAGTCTCCATCCTCCCT GTCTGCATCTGTAGGAGACAGAGTCACCATCA CTTGCCGGGCAAGTCAGGACAGAGTCACCATCA TTAGGCTGGTATCAGCAGAAACCAGGGAAAG CCCCTAAGCGCCTGATCTATGCTGCATCCAGT TGCAAAGTGGGGTCCCATCAAGGTTCAGTT AGTAGATCTGGGACAGAATTCACTCTCACAAT CAGCAGCCTGCAGCCTGAAGATTTTGCAACTT ATTACTGTCTGCAACATAATAGTTACCCGCTC ACTTTCGGCGGAGGGACCAAGGTGGAGATCA AA SEQ ID NO: 25277 | CAGGTGCAGCTGGTGGAGTCGGGGGGAGGCGTG GTCCAGCCTGGGAGGTCCCTGAGACTCTCCTGTG CAGCGTCTGGATTCACCTTCAGTGACTATGGCAT GCACTGGGTCCGCCAAGCTCCAGGCAAGGGCT GGAGTGGGTGGCAGTTATATGGTATGATGACTAT AATAAAAAGTATGCAGACTCCGTGAAGGGCCGA TTCACCATCTCCAGAGACAATGCCAAGAACACGC TGTATCTGCAAGTGAACAGCCTGAGAGTGGAAG ACACGGCTGTGTATTACTGTGCGACAGAACTGGG GATGCTCTTTGACTACTGGGGCCAGGGAACCCTG GTCACCGTCTCCTCA SEQ ID NO: 29283 |

FIGURE 50
(Continued)

| | | | |
|---|---|---|---|
| iPS:433985 | 21-225_47C1 | AA | DIQMTQSPSSLSASVGDRVTITCRASQDIRNDLG WYQQKPGKAPKRLIYAAFSLQSGVPSRFSGSRS GTEFTLTISSLQPEDFATYYCLQHNSYPLTFGGG TKVEIK<br><br>SEQ ID NO: 25278 | QVQLVESGGGVVQPGRSLRLSCAASGFTFSDYGM HWVRQAPGKGLEWVAVIWYDDYNKKYADSVKG RFTISRDNAKNTLYLQVNSLRVEDTAVYYCATELG MLFDYWGQGTLVTVSS<br><br>SEQ ID NO: 29284 |
| | | NA | GATATTGTGATGACCCAGACTCCACTCTCTCT GTCCGTCACCCCTGGACAGCCGGCCTCCATCT CCTGCACGTCTAGTCAGAGCCTCCTGCATAGT GAAGGAAAGACCTATTTGTATTGGTACCTCCA GAAGCCAGGCCAGCCTCCACAGCTCCTGATCT ATGAAGTTTCCAACCGGTTCTCTGGAGTGCCA GATAGGTTCAGTGGCAGCGGGTCAGGACAG ATTTCACACTAAAAATCAGCCGGGTGGAGGCT GAGGATGTTGGGGTTTTTACTGTATGCAAAG TATACAGCTTCCGTGGACGTTCGGCCAAGGGA CCAAGGTGGAAATCAAA<br><br>SEQ ID NO: 25279 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTGACTGGCAT GCACTGGGTCCGCCAGACTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTTTCTGCAAATGAACAGCCTGAGAGACGAGG ACACGGCTGTGTATTACTGTGCGAGACGGTATAG CCGCAGCTGGGTGGGAGGTATGGACGTCTGGGG CCAAGGGACCACGGTCACCGTCTCCTCA<br><br>SEQ ID NO: 29285 |
| | | AA | DIVMTQTPLSLSVTPGQPASISCTSSQSLLHSEGK TYLYWYLQKPGQPPQLLIYEVSNRFSGVPDRFSG SGSGTDFTLKISRVEAEDVGVFYCMQSIQLPWTF GQGTKVEIK<br><br>SEQ ID NO: 25280 | QVQLVESGGGVVQPGRSLRLSCAASGFTFSDYGM HWVRQTPGKGLEWVAVIWYDGSNKYADSVKGR FTISRDNSKNTLFLQMNSLRDEDTAVYYCARRYSR SWVGGMDVWGQGTTVTVSS<br><br>SEQ ID NO: 29286 |

FIGURE 50
(Continued)

| | | | |
|---|---|---|---|
| iPS:433987 | 21-225_47A5 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCCGTCTGATTCACCTTCAGTGACGATGACAC ACACTGGGTCCGCCAGGCTCCAGGCAAGGGCT GGAGTGGGTGGCAGTTATATGGTTTGATGAAGT AATAAATACTATGCAGAGACTCCGTGAAGGGCCGA TTCACCATCTCCAGAGACAATTCCAAGAACACGC TGTATCTGCAAATGAACAGCCTGAGCGCCGAGG ACACGGCTGTGTATTACTGTGCGAGAGATCTTAT AGCAGCAGCTGGTACAGTTGACTACTGGGGCCA GGGAACCCTGGTCACCGTCTCCTCA |
| | | | SEQ ID NO: 25281 | SEQ ID NO: 29287 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK | QVQLVESGGGVVQPGRSLRLSCAASGFTFSDDDTH WVRQAPGKGLEWVAVIWFDGSNKYYADSVKGRF TISRDNSKNTLYLQMNSLSAEDTAVYYCARDLIAA AGTVDYWGQGTLVTVSS |
| | | | SEQ ID NO: 25282 | SEQ ID NO: 29288 |
| iPS:433989 | 21-225_47C7 | NA | GATATTGTGATGACTCAGTCTCCACTCTCCCCG CCCGTCACCCTGGAGAGCCGGCCTCCATCTC CTGCAGGTCTAGTCAGAGCCTCCTGCATAGTA ATGGATACAACTATTTGGAATGTACCTGCAG AAGTCAGGGCAGTCTCCACAGTTCCTGATCTA TTTGGGTTTAATCGGGCCTCCGGGGTCCCTG ACAGGTTCACTGGCAGTGGATCAGGCACAGAT TTTACACTGAAAATCAGCAGAGTGGAGGCTGA GGATGTTGGGGTTTATTACTGCATGCAAGTTC TACAAACTCCATTCACTTTCGGCCCTGGGACC AAAGTGGATATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGTAACTATGCCAT GAGCTGGGTCCGCCAGGCTCCAGGGAAGGGCT GGAGTGGGTCTCAGTATTAGTAGTGGTAGTAGT CGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAAGATCGGG GGCAGTGGCTCATAGGCGGTATGACGTCTGGG GCCAAGGGACCACGGTCACCGTCTCCTCA |
| | | | SEQ ID NO: 25283 | SEQ ID NO: 29289 |

FIGURE 50
(Continued)

| | | | |
|---|---|---|---|
| | | AA | DIVMTQSPLSPPVTPGEPASISCRSSQSLLHSNGY NYLEWYLQKSGQSPQFLIYLGFNRASGVPDRFT GSGSGTDFTLKISRVEAEDVGVYYCMQVLQTPF TFGPGTKVDIK<br><br>SEQ ID NO: 25284 | EVQLLESGGGLVQPGGSLRLSCAASGFTFSNYAMS WVRQAPGKGLEWVSGISGSGSRTYYADSVKGRFTI SRDNSKNTLYLQMNSLRAEDTAVYYCAKDRGQW LIGGMDVWGQGTTVTVSS<br><br>SEQ ID NO: 29290 |
| iPS:433991 | 21-225_47E7 | NA | GATATTGTGATGACCCAAACTCCACTCTCTCT GTCCGTCACCCCTGGACAGCCGGCTCCATCT CCTGCAAGTCTAGTCAGAGCCTCCTGCATAGT GATGGAAGGACCTATTTGTATTGGTACCTGCA GAAGCCAGGCCAGTCCACAGCTCCTGATCT ATGAAGTTTCCAGCCGTTCTCTGGAGTGCCA GATAGGTTCAGTGGCAGCGGGTCAGGACAG ATTTCGCACTGAAAATCAGCCGGGTGGAGCT GAGGATGTTGGGGTTTATTACTGCATGCAAAG TACACAACTTCCGTGGACGTTCGGCCAAGGGA CCAAGGCGGAAATCAAA<br><br>SEQ ID NO: 25285 | CAGGTGCAGCTGTTGGAGTCTGGGGGAGGCGTG GTCCAGCCTGGGAGGTCCCTGAGACTCTCCTGTG CAGCGTCTGGATTCACCTTCAGTATCTATGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACACAATTCCAAGAACACGC TGTATCTTCAAATGAACAGCCTGAGAGCCGAGG ACACGGCTGTGTATTACTGTGCGAGACGGTATAG CAGAAGCTGGGTGGGAGGTATGGACGTCTGGGG CCAAGGGACCACGGTCACCGTCTCCTCA<br><br>SEQ ID NO: 29291 |
| | | AA | DIVMTQTPLSLSVTPGQPASICKSSQSLLHSDGR TYLYWYLQKPGQPPQLLIYEVSSRFSGVPDRFSG SGSGTDFALKISRVEAEDVGVYYCMQSTQLPWT FGQGTKAEIK<br><br>SEQ ID NO: 25286 | QVQLVESGGGVVQPGRSLRLSCAASGFTFSIYGMH WVRQAPGKGLEWVAVIWYDGSNKYYADSVKGRF TISRDNSKNTLYLQMNSLRAEDTAVYYCARRYSRS WVGGMDVWGQGTTVTVSS<br><br>SEQ ID NO: 29292 |

FIGURE 50
(Continued)

| | | | |
|---|---|---|---|
| iPS:433993 | 21-225_47G7 | NA | GACATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTTTGCTGCCTCCAATT TGCAAAGTGGGGTCCCATCAAGGTTCAGCGGC AGTGGATCTGGGACAGATTTCACTCTCACCAT CAGCAGTCTGCAGCCTGCAGATTTTGCAACTT ACTGTTGTCAACAGTTAACAGTTCCCGTGG ACGTTCGGCCAAGGGACCAAGGTGGAAATCA AA | GAGGTGCAGTTGTTGGACTCTGGGGGAGGCTTGG TGCAGCCTGGGGGGGTCCTGAGACTCTCCTGTGC AGCCTCTGGATTCACCTTTAGCAGCTATGCCATG AGTTGGGTCCGCCAGGCTCCAGGGAAGGGGCTG GAGTGGGTCTCAGCTATTAGTGGTCGTGGTGTA ACACATTCTACGCAGAGTCCGTGAGGGGCCGTT CACCATCTCCAGAGACAATTCCAAGAACACGCTG TATCTGCAAATGAACAGCCTGAGAGCCGAGAC ACGGCCGTATATTACTGTGCGAAGATTATCCGG AGCAGTGGGCCTTTGACTACTGGGGCCAGGGAA CCCTGGTCACCGTCTCCTCA |
| | | | SEQ ID NO: 25287 | SEQ ID NO: 29293 |
| | | AA | DIQMTQSPSSVSASVGDRVTITCRASQGISNWLA WYQQKPGKAPKLLIFAASNLQSGVPSRFSGSGS GTDFTLTISSLQPADFATYCQQVNSFPWTFGQG TKVEIK | EVQLLDSGGGLVQPGGSLRLSCAASGFTFSSYAMS WVRQAPGKGLEWVSAISGRGGNTFYAESVRGRFTI SRDNSKNTLYLQMNSLRAEDTAVYYCAKIIREQWA FDYWGQGTLVTVSS |
| | | | SEQ ID NO: 25288 | SEQ ID NO: 29294 |
| iPS:433995 | 21-225_47H7 | NA | GACATCCAGATGACCCAGTCTCCATCTCCCT GTCTGCATCTGTAGGAGACAGAGTCACCATCA CTTGCCGGACAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGACTTCACTCTCACAG TCAGCAGCCTGCAGCCTGAAGATTTTGCAACT TATTTCTGTCTACAACATACTAGTTTCCCATTC ACTTTCGGCCCTGGGACCAAAGTGGATATCAA A | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTACAT GATCTGGATCCGCCAGGCTCCAGGGAAGGGGCT GGAGTGGGTTTCATACATTAATAGTAATGGTTTT ACCAAATACTACGCAGACTCTGTGAAGGGCCGA TTCACCATCTCCAGGGACAACGCCAAGAATTCAC TGTATCTGCAAATGAACAGTCTGAGAGCCGAGG ACACGGCCGTGTATTACTGTGCGGCCGATACAGT CTACTGGGGCCAGGGAACCCTGGTCACCGTCTCC TCA |
| | | | SEQ ID NO: 25289 | SEQ ID NO: 29295 |

FIGURE 50
(Continued)

| | | | |
|---|---|---|---|
| iPS:433997 | | AA | DIQMTQSPSSLSASVGDRVTITCRTSQGIRNDLG WYQKKPGKAPKRLIYAASSLQSGVPSRFSGSGS GTEFTLTVSSLQPEDFATYFCLQHTSFPFTFGPGT KVDIK SEQ ID NO: 25290 | QVQLVESGGGLVKPGGSLRLSCAASGFTFSDYYMI WIRQAPGKGLEWVSYINSNGFTKYYADSVKGRFTI SRDNAKNSLYLQMNSLRAEDTAVYYCAADTVYW GQGTLVTVSS SEQ ID NO: 29296 |
| | | NA | GACATCCAGATGACCCAGTCTCCATCCTCCCT GTCTGCATCTGTAGGAGACAGAGTCACCATCA CTTGCCGGACAAGTCAGGGCATTAGAAATGAT TTAGGCTGGTATCAGCAGAAACCAGGGAAAG CCCCTAAGCGCCTGATCTATGCAGCATCCAGT TTGCAAAGTGGGGTCCCAGCAAGGTTCAGCGG CAGTGGATCTGGGACAGAATTCACTCTTACAA TCAGCAGCCTGCAGCCTGAAGATTTTGCAATT TATTACTGTCTACAGCATATAATTTTACCCGTGG ACGTTCGGCCAAGGGACCAAGGTGGAAATCA AA SEQ ID NO: 25291 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTGTATGGTATGATGAAATT AATAAAAAGTATCCAGACTCCGTGAAGGGCCGA GTCACCATCTCCAGAGACAATTCCAAGAACACGC TGTATCTGCAAATGAACAGCCTGAGAGCCGAGG ACACGGCTATGTATTACTGTGCGAGAGAATTAGG GTGGGAGGCTGACTACTGGGGCCAGGGAACCCT GGTCACCGTCTCCTCA SEQ ID NO: 29297 |
| 21-225_48C1 | | AA | DIQMTQSPSSLSASVGDRVTITCRTSQGIRNDLG WYQQKPGKAPKRLIYRASSLQSGVPARFSGSGS GTEFTLTISSLQPEDFAIYYCLQHNFYPWTFGQG TKVEIK SEQ ID NO: 25292 | QVQLVESGGGVVQPGRSLRLSCAASGFTFSSYGMH WVRQAPGKGLEWVAVVWYDEINKKYADSVKGRV TISRDNSKNTLYLQMNSLRAEDTAMYYCARELGW EADYWGQGTLVTVSS SEQ ID NO: 29298 |

FIGURE 50
(Continued)

| | | | |
|---|---|---|---|
| iPS:433999 | 21-225_48D1 | NA | GACATCCAGATGACCCAGTCTCCATCCTCCT GTCTGCGTCTGTAGGAGACAGAGTCAACATCA CTTGCCGGGCAAGTCAGAGACATTAGCAGTAT TTAATTTGGTATCAGCAGAAACCAGGGAAAGC CCCTAAGCTCCTGATCTATGCTGCATCCAGTT GCAAAGTGGGGTCCCATCAAGGTTCAGTGCCA GTGGATCTGGGACAGATTTCACTCTCACCATC AGCAGTCTGCAACCTGAAGATTTTGCAAGTTA CTACTGTCAACAGAGTAACAGTATTCCATTCA CTTTCGGCCCTGGGACCAAAGTGGATATCAAA<br>SEQ ID NO: 25293 | GAGGTGCAGCTGTTGGAGTCTGGGGGAGGCTTG GTACAGCCTGGGGGGTCCCTGAGACTCTCCTGTG CAGCCCTCTAGATTCACCTTTAGCAGTTATGCCAT GAGCTGGGTCCGCCAGGCTCCAGGGAAGGGCT GGAGTGGGTCTCAGTTATTAGTGGTCGTGGTGGT AGCACATTCTACGCAGACTCCGTGAAGGGCCGGT TCACCATCTCCAGAGACAACAATTCCAAGAACACGCT GTATCTGCAAATGAACAGCCTGAGAGCCGAGGA CACGGCCGTATATTACTGTGCCGGCGTATAGCA GTGGCTGGGAATGAGGCTTTTGATATCTGGGGCC AAGGGACAATGGTCACCGTCTCTTCA<br>SEQ ID NO: 29299 |
| | | AA | DIQMTQSPSSLSASVGDRVNITCRASQSISSYLIW YQQKPGKAPKLLIYAASSLQSGVPSRFSASGSGT DFTLTISSLQPEDFASYYCQQSNSIPFTFGPGTKV DIK<br>SEQ ID NO: 25294 | EVQLLESGGGLVQPGGSLRLSCAASRFTFSSYAMS WVRQAPGKGLEWVSVISGRGGSTFYADSVKGRFTI SRDNSKNTLYLQMNSLRAEDTAVYYCARRIAVAG NEAFDIWGQGTMVTVSS<br>SEQ ID NO: 29300 |
| iPS:434001 | 21-225_48F2 | NA | GACATCCAGATGACCCAGTCTCCATCCTCCCT GTCTGCATCTGTAGGAGACAGAGTCACCATCA CTTGCCGGGCAAGTCGGGGACAGTCATTAGAGATGAT TTAGGCTGGTATCAACAGAAACCAGGGAAAC CCCCTAAGCGCCTGATCTATGCTGCATCCAGT TTGCAAAGTGGGGTCCCATCAAGGTTCAACGG CAGTGGATCTGGGACAGATTCACTCTCACAA TCAGCAGCCTGCAGTCTGAAGATCTTGCAACT TATTACTGTCTACAGCAATATAGTTATCTCCTG ACGTTCGGCCAAGGGACCAAGGTGGAAATCA AA<br>SEQ ID NO: 25295 | CAGGTGCAGCTGTGGTGGAGTCTGGGGGAGGCGTG GTCCAGCCTGGGAGGTCTCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGTA TAGCAGCAGCTGGTACGACTACGGTCTGGACGTC TGGGGCCAAGGGACCACGGTCACCGTCTCCTCA<br>SEQ ID NO: 29301 |

FIGURE 50
(Continued)

| | | | |
|---|---|---|---|
| iPS:434003 | 21-225_48C3 | AA | DIQMTQSPSSLSASVGDRVTITCRASRGIRDLG WYQQKPGKPPKRLIYAASSLQSGVPSRFNGSGS GTEFTLTISSLQSEDLATYYCLQQYSYPRTFGQG TKVEIK<br>SEQ ID NO: 25296 | QVQLVESGGGVVQPGRSLRLSCAASGFTFSNYVM HWVRQAPGKGLEWVAVIWYDGSNKYYADSVKGR FTISRDNSKNTLYLQMNSLRAEDTAVYYCARERYS SSWYDYGLDVWGQGTTVTVSS<br>SEQ ID NO: 29302 |
| | | NA | GACATCCAGATGACCCAGTCTCCATCCCCT GTCTGCGTCTGTAGGAGACAGAGTCAACATCA CTTGCCGGGCAAGTCAGAGCATTATCAGCTAT TTAATTTGGTATCAGCAGAAACCAGGGAAAGC CCCTAGGCTCCTGATCTATGCTGCATCCAGTTT GCAAAGTGGGGTCCCATCAAGGTTCAGTGCCA GTGGATCTGGGACAGATTTCACTCTCACCATC AGCAGTCTGCAACCTGAAGATTTTGCAAGTTA CTACTGTCAACAGATACTAACAGTATTCCATTCA CTTTCGGCCCTGGGACCAAAGTGGATATCAAA<br>SEQ ID NO: 25297 | GAGGTGCAGCTGTTGGAGTCTGGGGGAGGCTTG GTACAGCCTGGGGGGTCCCTGAGACTCTCCTGTG CAGCCTCTAGATTCACCTTTAGCAGTTATGCCAT GAGCTGGGTCCGCCAGGCTCCAGGGAAGGGGCT GGAGTGGGTCTCAGTTATTAGTGGTCGTGGTGGT AGCACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGCGTCGTATAGCA GTGGCTGGGAATGAGGCTTTTGATATCTGGGGCC AAGGGACAATGGTCACCGTCTCTCTCA<br>SEQ ID NO: 29303 |
| | | AA | DIQMTQSPSSLSASVGDRVNITCRASQSIISYLIW YQQKPGKAPRLLIYAASSLQSGVPSRFSASGSGT DFTLTISSLQPEDFASYYCQQTNSIPFTFGPGTKV DIK<br>SEQ ID NO: 25298 | EVQLLESGGGLVQPGGSLRLSCAASRFTFSSYAMS WVRQAPGKGLEWVSVISGRGGSTFYADSVKGRFTI SRDNSKNTLYLQMNSLRAEDTAVYYCARRIAVAG NEAFDIWGQGTMVTVSS<br>SEQ ID NO: 29304 |

FIGURE 50
(Continued)

| | | | |
|---|---|---|---|
| iPS:434007 | 21-225_48D7 | NA | GACATCCAGATGACCCAGTCTCCATCTTCCGT GTCTGCATCTGTAGGAGACAGAGTCACCATCA CTTGTCGGGCGAGTCAAATATTACCAGCTGG TTAGCCTGGTATCAGCAGAAACCAGGGAAAG CCCCTAAGCTCCTGATCTATAGTGCATCCAGTT TGCAAAATGGGGTCCCATCAAGGTTCAGCGGC AGTGGATCTGGGACAGATTTCACTCTCACCAT CAGCAGCCTGCAGCCTGAAGATTTTGTAACTT ACTGTTGTCAACAGGCTAACAGTTCCGTGG ACGTTCGGCCAAGGGACCAAGGTGGAAATCA AA SEQ ID NO: 25299 |
| | | AA | DIQMTQSPSSVSASVGDRVTITCRASQNITSWLA WYQQKPGKAPKLLIYSASSLQNGVPSRFSGSGS GTDFTLTISSLQPEDFVTYCCQQANSFPWTFGQG TKVEIK SEQ ID NO: 25300 |
| | | NA | GAGGTGCAGCTGTTGGAGTCTGGGGGAGGCTTG GTACAGCCGGGGGGGTCCCTGAGACTCTCCTGTG CAGCCTCTGGATTCACCTTTAGAAACTGCCAT GAACTGGGTCCGCCAGGCTCCAGGGAAGGGCT GGAGTGGGTCTCAGTATTAGTGGTAGTGGTGGT ACCACATTCTACGCAGACTCCGTGAAGGGCCGGT TCACCATCTCCAGAGACAATTCCAAGAACACGTT GTATCTGCAAATAAACAGCCTGAGAGCCGAGGA CACGGCCGTATATTACTGTGCGAAATGTGGCGG GAGCAGTGGCTTGACTACTGGGGCCAGGGAACC CTGGTCACCGTCTCCTCA SEQ ID NO: 29305 |
| | | AA | EVQLLESGGGLVQPGGSLRLSCAASGFTFRNSAMN WVRQAPGKGLEWVSAISGSGGTTFYADSVKGRFTI SRDNSKNTLYLQMNSLRAEDTAVYYCAKCGREQW LDYWGQGTLVTVSS SEQ ID NO: 29306 |
| iPS:434009 | 21-225_48A9 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATATTGCATCCAGTT TGCAAAGTGGGGTCCCATCAAGGTTCAGCGGC AGTGGATCTGGGACAGAATTCACTCTCACTAT ATTACTGTCTACAGCATAATATCGTTACCCGTGG ACGTTCGGCCAAGGGACCAAGGTGGAAATCA AA SEQ ID NO: 25301 |
| | | NA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCCCCAGGCAAGGGGCT GGAGTGGGTGGCAGTTATATACTAGATGGTATGGAGAAA TAAGAAATACTATGCAGACTCCGTGAAGGGCCG ATTCACCATCTCCAGAGACAATTCCAAGAACACG CTGTTTCTGCAAATGAATAGCCTGAGAGCCGAGG ACACGGCTATGTATTTCTGTGCGAGAGAACTTGC CTGTACGAGGACTACTGGGGCCAGGGAACCCT GGTCACCGTCTCCTCA SEQ ID NO: 29307 |

FIGURE 50
(Continued)

| | | | | |
|---|---|---|---|---|
| | | AA | DIQMTQSPSSLSASVGDRVTITCRASQGIRNDLG WYQQKPGKAPKRLIYIASSLQSGVPSRFSGSGSG TEFTLTISGLQPEDFAIYYCLQHNRYPWTFGQGT KVEIK | QVQLVESGGGVVQPGRSLRLSCAASGFTFSSYGMH WVRQAPGKGLEWVAVIWYEENKKYYADSVKGRF TISRDNSKNTLFLQMNSLRAEDTAMYFCARELAWY EDYWGQGTLVTVSS |
| | | | SEQ ID NO: 25302 | SEQ ID NO: 29308 |
| iPS:434011 | 21-225_48B10 | NA | GACATCCAGATGACCCAGTCTCCATCCTCCCT GTCTGCGTCTGTAGGAGACAGAGTCACCATCA CTTGCCGGGCAAGTCAGAGACATTAGGAAGTAT TTAAATTGGTATCAGAGAAGACACCAGGGAAAG CCCCTAAACTCTTGATCTATGCTGCTTCCAGTT TGCAAAGTGGGGTCCCATCAAGGTTCAGTGGC AGTGGATCTGGGACAGATTTCACTCTCACCAT CAGCAGTGTGCAACCTGAAGATTTTGCAACTT ACTACTGTCAACAGAGACTTACAGTAACCCACTC ACTTTCGGCGGAGGGACCAAGGTGGAGTTCAC A | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTTCAT GACCTGGATCCGCCAGGCTCCAGGGCAGGGGCT GGAGTGGGTTCATACATTAGTAGTGCTGGTGGT GCCATATACTACGCAGACTCTGTGAAGGGCCGAT TCACCATCTCCAGGGACAACGCCAAAAACTCACT GTATCTGCAAATGAACAGCCTGAGAGCCGAGGA CACGGCCGTGTATTACTGTGCAATAGCAGTGGCT GCCCCTGGTGTTTTGATATCTGGGGCCAAGGGA CAATGGTCACCGTCTCTTCA |
| | | | SEQ ID NO: 25303 | SEQ ID NO: 29309 |
| | | AA | DIQMTQSPSSLSASVGDRVTITCRASQSIRKYLN WYQKTPGKAPKLLIYAASSLQSGVPSRFSGSGSG TDFTLTISSVQPEDFATYYCQQTYSNPLTFGGGT KVEFT | QVQLVESGGGLVKPGGSLRLSCAASGFTFSDYFMT WIRQAPGQGLEWVSYISSAGGAIYYADSVKGRFTIS RDNAKNSLYLQMNSLRAEDTAVYYCAIAVAAPGV FDIWGQGTMVTVSS |
| | | | SEQ ID NO: 25304 | SEQ ID NO: 29310 |

FIGURE 50
(Continued)

| | | | |
|---|---|---|---|
| iPS:434013 | 21-225_48D12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGGCGCCTATCTATGCTGCATCCACTT TGCAAAGTGGGGTCCCATCAAGGATCAGCGGC AGTGGATCTGGGACAGAATTCACTCTCACAAT CAGCAGCCTGCAGCCTGAAGATTTTGCAACTT ATTACTGTCTACAGCATAATAGTTACCCGCTC ACTTTCGGCGGAGGGACCAAGGTGGAGATCA AA<br>SEQ ID NO: 25305 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAGGGCCT GGAGTGGGTGGCAGTTATATGACTCGGTGATGTAAGT AATAAATACTATGTAGACTCCGTGAAGGGCCGAT TCACCATCTCCAGAGACAATTCCAAGAACACGCT GTATCTGCAAATGAACAGCCTGAGAGCCGAGA CACGGCTGTGTATTACTGTGCGAGAGAACTGGGG ATGAGATCGACTACTGGGGCCAGGGAACCCTG GTCACCGTCTCCTCA<br>SEQ ID NO: 29311 |
| | | AA | DIQMTQSPSSLSASVGDRVTITCRASQGIRNDLG WYQQKPGKAPKRLIYAASTLQSGVPSRISGSGSG TEFTLTISSLQPEDFATYYCLQHNSYPLTFGGGT KVEIK<br>SEQ ID NO: 25306 | QVQLVESGGGVVQPGRSLRLSCAASGFTFSDYGM HWVRQAPGRGLEWVAVIWYDSVKGR FTISRDNSKNTLYLQMNSLRAEDTAVYYCARELGM RSDYWGQGTLVTVSS<br>SEQ ID NO: 29312 |
| iPS:434015 | 21-225_48F12 | NA | GACATCCAGATGACCCAGTCTCCATCCTCCCT GTCTGCGTCTGTAGGAGACAGAGTCACCATCA CTTGCCGGGCAAGTCAGGGCATTAGGAAGTAT TTAAATTGGTATCAGCAGAAACACCAGGGAAAG CCCCTAAACTCTTGATCTATGCTGCTTCCAGTT TGCAAAGTGGGGTCCCATCAAGGTTCAGTGGC AGTGGATCTGGGACAGATTTCACTCTCACCAT CAGCAGTCTGCAACAGACTGAAGATTTGCAAATT ATTACTGTCAACAGAGTTACAGTAACCCGCTC ACTTTCGGCGGAGGGACCAAGGTGGAGATCA CA<br>SEQ ID NO: 25307 | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTTCAT GACCTGGATCCGCCAGGCTCCAGGCAAGGGGCT GGAGTGGGTTCATACATTAGTAGTAGTGGTGGT GCCATATACTACGCAGACTCTGTGAAGGGCCGAT TCACCATCTCCAGGGACAACGCCAAGAACTCACT GTTTCTGCAAATGAACAGCTGAGAGCCGAGGA CACGGCCGTGTATTACTGTGCTATAGCAGTGGCT GCCCCTGGTGCTTTTGATATCTGGGGCCAAGGGA CATTGGTCACCGTCTCTCA<br>SEQ ID NO: 29313 |

FIGURE 50
(Continued)

| | | | | |
|---|---|---|---|---|
| | | AA | DIQMTQSPSSLSASVGDRVTITCRASQSIRKYLN WYQKTPGKAPKLLIYAASSLQSGVPSRFSGSGSG TDFTLTISSLQPEDFANYYCQQTYSNPLTFGGGT EVEIT | QVQLVESGGGLVKPGGSLRLSCAASGFTFSDYFMT WIRQAPGQGLEWVSYISSAGGAIYYADSVKGRFTIS RDNAKNSLFLQMNSLRAEDTAVYYCAIAVAAPGA FDIWGQGTLVTVSS |
| | | | SEQ ID NO: 25308 | SEQ ID NO: 29314 |
| iPS:434017 | 21-225_48G12 | NA | GACATCCAGATGACCCAGTCTCCATCCTCCCT GTCTGCGTCTGTAGGAGACAGAGTCACCATCA CTTGCCGGGCAAGTCAGAGACATTAGGAAGTAT TTAAATTGGTATCAGAAGACACCAGGAAAG CCCCTAAACTCTTGATATATGCTGCTTCCAGTT TGCAAAGTGGGGTCCCATCAAGGTTCAGTGGC AGTGGATCTGGGACAGATTTCACTCTCACCAT CAGCAGTGTGCAACCTGCAAGATTTTGCAAATT ATTACTGTCAACAGATTACAGTAACCCGCTC ACTTTCGGCGGAGGGACCGAGGTGGAGATCA CA | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTTCAT GACCTGGATCCGCCAGGCTCCAGGGCAGGGGCT GGAGTGGGTTTCATACATTAGTAGTGCTGGTGGT GCCATATACTACGCAGACTCTGTGAAGGGCCGAT TCACCATCTCCAGGGACAACGCCAAGAACTCACT GTTTCTGCAAATGAACAGCTGAGAGCCGAGGA CACGGCCGTGTATTACTGTGCTATAGCAGTGGCT GCCCCTGGTGCTTTTGATATCTGGGGCCAAGGGA CATTGGTCACCGTCTCTTCA |
| | | | SEQ ID NO: 25309 | SEQ ID NO: 29315 |
| | | AA | DIQMTQSPSSLSASVGDRVTITCRASQSIRKYLN WYQKTPGKAPKLLIYAASSLQSGVPSRFSGSGSG TDFTLTISSVQPEDFANYYCQQTYSNPLTFGGGT EVEIT | QVQLVESGGGLVKPGGSLRLSCAASGFTFSDYFMT WIRQAPGQGLEWVSYISSAGGAIYYADSVKGRFTIS RDNAKNSLFLQMNSLRAEDTAVYYCAIAVAAPGA FDIWGQGTLVTVSS |
| | | | SEQ ID NO: 25310 | SEQ ID NO: 29316 |

FIGURE 50
(Continued)

| | | | |
|---|---|---|---|
| iPS:434019 | 21-225_49A1 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGACTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGTAGCCTGCAGCCTGAAGATTTTGCAACT TATTACTGTCTACAGCATAATAGTTACCCGCTC ACTTTCGGCGGAGGGACCAAGGTGGAGATCA AA |
| | | | SEQ ID NO: 25311 |
| | | AA | DIQMTQSPSSLSASVGDRVTITCRASQGIRNDLD WYQQKPGKSPKRLIYAASSLQSGVPSRFSGSGS GTEFTLTISSLQPEDFATYYCLQHNSYPLTFGGG TKVEIK |
| | | | SEQ ID NO: 25312 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGG GAAGGAAAGACCTATTTGTACTGGTACCTGCA GAAGCCAGGCCAGCCTCCACAGTTCCTGATCT TTGAAGTTTCCCACCGGTTCTCTGGCGTGCCA GATAGGTTCAGTGGCAGCGGGTCAGGGACAG ATTTCACACTGAAAATCAGCCGGGTGGAGGCT GAGGATGTGGGGTTTATTACTGCATGCAAAGT TATACAGATTCCGATCACCCTCGGCCAAGGGA CACGACTGGAGATTAAA |
| iPS:434021 | 21-225_49C1 | | |
| | | | SEQ ID NO: 25313 |

| | | | |
|---|---|---|---|
| | | | CAGGTGCAGCTGGTGGTGGAGTCTGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGTAGACTCCGTGAAGGGCCGAT AATAAATATTATGTAGACTCCGTGAAGGGCCGAT TCACCATCTCCAGAGACAATTCCAAGAACACGCT GTATCTGCAAATGAACAGCCTGAGAGCCGAGA CACGGCTGTGTATTACTGTGCGAGAGAACTGGGG TTCCTCTCTGACTACTGGGGCCAGGGAACCCTGG TCACCGTCTCCTCA |
| | | | SEQ ID NO: 29317 |
| | | | QVQLVESGGGVVQPGRSLRLSCAASGFTFSDYGM HWVRQAPGKGLEWVAVIWYDEDNKYYVDSVKGR FTISRDNSKNTLYLQMNSLRAEDTAVYYCARELGF LSDYWGQGTLVTVSS |
| | | | SEQ ID NO: 29318 |
| | | | CAGGTGCAGCTGGTGGAGTCTGGGGAGGCGTG GTCCAGCCTGGGAGGTCCCTGAGACTCTCCTGTA CAGCGTCTGGATTCACCTTCAGTAGTATGGCAT GCACTGGGTCCGCCAGGCTCCAGGCAAGGGGCT GGAGTGGGTGGCAGTTATATGTATGGTATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCTGGGCGGTATGGACGTCTGGGG CCAAGGGACCACGGTCACCGTCTCCTCA |
| | | | SEQ ID NO: 29319 |

FIGURE 50
(Continued)

| | | | |
|---|---|---|---|
| | | AA | DIVMTQTPLSLSVTPGQPASISCKSSQSLLHREGK TYLYWYLQKPGQAPQFLIFEVSHRFSGVPDRFSG SGSGTDFTLKISRVEAEDVGVYYCMQSIQPITLG QGTRLEIK | QVQLVESGGGVVQPGRSLRLSCTASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTVSS |
| | | | SEQ ID NO: 25314 | SEQ ID NO: 29320 |
| iPS:434023 | 21-225_49F1 | NA | GACATCCAGATGACCCAGTCTCCATCTTCCGT GTCTGCATCTGTAGGAGACAGAGTCACCATCA CTTGTCGGGCGAGTCGGATATATTAACGGCTGG TTAGCCTGGTATCAGCAGAAACCAGGGAAAG CCCCTAAGCTCCTGATCTATACTGTCTCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGTCTAACAGTTTCCCATTCA CTTTCGGCCCTGGGACCAAAGTGGATATCAAA | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGACTGGGTCTCAGTTATTAGTGGTAGTGGTGGT AGCACATTCTACGCAGACTCCGTGAAGGGCCGGT TCACCATCTCCAGAGACAATCCAAGAGCACGCT GTATCTGCAAATGAACAGCCTGAGAGCCGAGA CACGGCCGTATATTATTGTGCGAGCGCTATAGCA GGGGCTGGTGCCCACTATTTTGACTACTGGGGCC AGGGAACCCTGGTCACCGTCTCCTCA |
| | | | SEQ ID NO: 25315 | SEQ ID NO: 29321 |
| | | AA | DIQMTQSPSSVSASVGDRVTITCRASRDINGWLA WYQQKPGKAPKLLIYTVSSLQSGVPSRFSGSGSG TDFTLTISSLQPEDFATYYCQQSNSFPFTFGPGTK VDIK | EVQLLESGGGLVQPGGSLRLSCAASGFTFSSYAMS WVRQAPGKGLDWVSVISGSGGSTFYADSVKGRFTI SRDNSKSTLYLQMNSLRAEDTAVYYCASAIAAAGA HYFDYWGQGTLVTVSS |
| | | | SEQ ID NO: 25316 | SEQ ID NO: 29322 |

FIGURE 50
(Continued)

| | | | | |
|---|---|---|---|---|
| iPS:434025 | 21-225_49G3 | NA | GATATTGTGATGACCCAGACTCCACTCTCT GTCCGTCACCCCTGGACAGCCGGCCTCCATG CCTGCAAGTCTAGTCAGAGCCTCCTGCATAGT GAAGGAAAGACCTATTTGTATTGGTACCTGCA GAAGACAGGCCAGCTCCACACCTCCTGATCT ATGAAGTTTCCAACCGCTCTCTGGCGTGCCA GATAGGTTCAGTGGCAGCGGGTCAGGGACAG ATTTCACACTGAAAATCAGCCGATGGAGGCT GAGGATGTTGGGGTTTATTTCTGCATGCAAAG TATGCAGCTTCCGATCACACCTTCGGCCAGGGGA CACGACTGGAGATTAAA<br><br>SEQ ID NO: 25317 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCGGGCGGAATGGACGTCTGGGG CCAAGGGACCACGGTCACCGTCTCCTCA<br><br>SEQ ID NO: 29323 |
| | | AA | DIVMTQTPLSLSVTPGQPASMSCKSSQSLLHSEG KTYLYWYLQKTGQPPHLLIYEVSNRLSGVPDRF SGSGSGTDFTLKISRMEAEDVGVYFCMQSMQLP ITFGQGTRLEIK<br><br>SEQ ID NO: 25318 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTVSS<br><br>SEQ ID NO: 29324 |
| iPS:434027 | 21-225_49H5 | NA | GACATCCAGATGACCCAGTCTCCATCTTCCGT GTCTGCATCTGTAGGAGACAGAGTCACCATCA CTTGTCGGGCGAGTCAGGGTTTTAGCAGCTGG TTAGCCTGGTATCAGCAGAAACCAGGGAAAGC CCCTAAGCTCCTGATCTATGCTGCATCCAGTTT GCAAAGATGGGGTCCCATCAAGGTTCAGCGGCA GTGGATCTGGGACAGATTTCACTCTCACCATC AGCAGCCTGCAGCCTGAAGATTTTGCAACTTA CTATTGTCAACAGACTAACAGTTTCCCGTTCA CTTTCGGCCCTGGGACCAAAGTGGATATCAAA<br><br>SEQ ID NO: 25319 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GACCTGGGTCCGCCAGGCTCCAGGGAAGGGGCT GGAGTGGGTCTCAGCTATTAGTGGTAGTGGTGGT AACTCATTCTACGCAGACTCCGTGAAGGGCCGGT TCACCATCTCCAGAGACAATTCCGAGAACACGTT GTATCTGCAAATGAACAGCCTGAGAGCCGAGGA CACGGCCGTATATTACTGTGCGAAAGCAAGGGC AGTGGCTGGGTCACACTGGTTCGACCCCTGGGGC CAGGGAACCCTGGTCACCGTCTCCTCA<br><br>SEQ ID NO: 29325 |

FIGURE 50
(Continued)

| | | | |
|---|---|---|---|
| iPS:434029 | | AA | DIQMTQSPSSVSASVGDRVTITCRASQGFSTWLA WFQQKPGKAPKLLIYAASSLQDGVPSRFSGSGS GTDFTLTISSLQPEDFATYYCQQTNSFPFTFGPGT KVDIK<br>SEQ ID NO: 25320 | EVQLLESGGGLVQPGGSLRLSCAASGFTFSSYAMT WVRQTPGKGLEWVSAISGSGGNSFYADSVKGRFTI SRDNSENTLYLQMNSLRAEDTAVYYCAKARAVAG SHWFDPWGQGTLVTVSS<br>SEQ ID NO: 29326 |
| | | NA | GACATCCAGATGACCCAGTCTCCATCCTCCCT GTCTGCATCTGTCGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGTTTCCCATCCAAGGTTCAGCGG CAGTGGATCTGGGACAGAATTCACTCTCACAA TCAGCAGCCTGCAGCCTGAAGATTTTGCAACT TATTACTGTCTACAGACATAATAGTTACCCTCTC ACTTTCGGCGGAGGGACCAAGGTGGAGATCA AA<br>SEQ ID NO: 25321 | CAGGTGCAGTTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGACTCCGTGAAGGGCCGA AATAAAAGTATGTAGACTCCGTGAAGGGCCGA TTCACCATCTCCAGAGACAATTCCAAGAACACGC TGTATCTGCAAATGAGCAGCCTGAGAGCCGAGG ACACGGCTGTGTATTATTGTGCGAGAGATCTGG GATGATCGAGGACTACTGGGGCCAGGGAACCCT GGTCACCGTCTCCTCA<br>SEQ ID NO: 29327 |
| 21-225_49C6 | | AA | DIQMTQSPSSLSASVGDRVTITCRASQGIRNDLG WYQQKPGKAPKRLIYAASSLQSGFPSRFSGSGSG TEFTLTISSLQPEDFATYYCLQHNSYPLTFGGGT KVEIK<br>SEQ ID NO: 25322 | QVQLVESGGGVVQPGRSLRLSCAASGFTFSNYGM HWVRQAPGKGLEWVAVIWFDVSNKKYVDSVKGR FTISRDNSKNTLYLQMSSLRAEDTAVYYCARDLGM IEDYWGQGTLVTVSS<br>SEQ ID NO: 29328 |

FIGURE 50
(Continued)

| | | | | |
|---|---|---|---|---|
| iPS:434031 | 21-225_49E7 | NA | GATATTGTGATGACCCAGACTCCACTCTCT GTCTGTCACCCCTGGACAGCCGGCCTTCATGT CCTGCAAGTCTAGTAGTCAGATCTTCTGTACATAGT GAAGGAAAGACCTATTTGTATTGGTACCTGCA GAAGACAGGCCAGCTCCACACCTCCTGATCT ATGAAGTTTCCAAGCGGCTCTCGGCGTGCCA GATAGGTTCAGTGGCAGCGGGTCAGGGACAG ATTTCACACTGAAAATCAGCCGATGGAGGCT GAGGATGTGCGGGGTTTATTACTGCATGCAAAG TATGCAGCTTCCGATTATCTTCGGCCAGGGGA CACGACTGGAGATTAAA SEQ ID NO: 25323 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTAGTGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTCTGTATTACTGTGCGAGAAGGTATAG CAGCAGCTGGTCGGGCGGTATGGACGTCTGGGG CCAAGGGACCACGGTCACCGTCTCCTCA SEQ ID NO: 29329 |
| | | AA | DIVMTQTPLSLSVTPGQPAFMSCKSSQIFLHSEG KTYLYWYLQKTGQPPHLLIYEVSKRLSGVPDRF SGSGSGTDFTLKISRMEAEDVGVYYCMQSMQLP IIFGQGTRLEIK SEQ ID NO: 25324 | QVQLVESGGGVVQPGRSLRLSCAASGFTFSSYGMH WVRQAPGKGLEWVAVIWYDGSNKYYADSVKGRF TISRDNSKNTLYLQMNSLRAEDTALYYCARRYSSS WSGGMDVWGQGTTVTVSS SEQ ID NO: 29330 |
| iPS:434033 | 21-225_49F9 | NA | GATATTGTGATGACCCAGACTCCACTCTCT GTCCGTCACCCTGGACAGCCGGCCTCCATCT CCTGCAAGTCTAATCAGAGCCTCGTGTATAAT GAAGGAAAGACCTATTTGTATTGGTATTTGCA GAAGCCAGGCCAGCCTCCACAGCTCCTGATCT TTGAAGTTTCCAACCGGTTCTCTGGAGTGCCA GATAGGTTCAGTGGCAGCGGGTCAGGGACAG ATTTCACACTGAAAATCAGTGGGTGGAGGCT GAGGATGTTGGGGTTTATTACTGCATGCAAAG TATACAGTATCCGATCACCTTCGGCCAAGGGA CACGACTGGAGATTAAA SEQ ID NO: 25325 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTTATGCAT GCACTGGGTCCGCCAGGCTCCAGGCAAGGGCT GGAGTGGGTGGCACTTATATGGTATGATGGAAG GAATAAATACTATGCAGACTCCGTGAAGGGCCG ATTCACCATCTCCAGAGACAATCCAAGAACACG CTGTATCTGCAAATGAACAGCCTGAGAGCCGAG GACACGGCTGTGTATCACTGTGCGAGAAGGTATA GCAGCAGCTGGTCGGGCGGTATGGACGTCTGGG GCCAAGGGACCACGGTCACCGTCTCCTCA SEQ ID NO: 29331 |

FIGURE 50
(Continued)

| | | | |
|---|---|---|---|
| iPS:434035 | 21-225_49F10 | AA | DIVMTQTPLSLSVTPGQPASISCKSNQSLVHNEG KTYLYWYLQKPGQPPQLLIFEVSNRFSGVPDRFS GSGSGTDFTLKISRVEAEDVGVYYCMQSIQYPIT FGQGTRLEIK<br><br>SEQ ID NO: 25326 | QVQLVESGGGVVQPGRSLRLSCAASGFTFSSYGMH WVRQAPGKGLEWVALIWYDGRNKYYADSVKGRF TISRDNPKNTLYLQMNSLRAEDTAVYHCARRYSSS WSGGMDVWGQGTTVTVSS<br><br>SEQ ID NO: 29332 |
| | | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGGTCCTGATCTATGCTGCATCCACTT TGCAAAGTGGGGTCCCATCAAGGTTCAGCGGC AGTGGATCTGGGACAGATTTCACTCTCACCAT CAGCAGCCTGCAACCTGAAGATTTTGCAACTT ACTATTGTCAACAGGCTAACAGTTTCCCATTC ACTTTCGGCCCTGGGACCAAAGTGGATATCAA A<br><br>SEQ ID NO: 25327 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACCATA TGCACTGGGTGCGACAGGCCCCTGGACAAGGGC TTGAGTGGATGGGATGGATCAACCCTAATAACAA TGCCACAAACTATGCTCAGAACTTTCAGGGCAGG GTCACCCTGACCAGGGACACGTCCATCAGCACA GCCTACATGGAGCTGAGCAGGCTGAGATCTGAC GACACGGCCGTGTATTACTGTGCGAGAGACGGT ACCAGCAGTTTGACTTCTGGGGCCAGGGAACCC TGGTCACCGTCTCCTCA<br><br>SEQ ID NO: 29333 |
| | | AA | DIQMTQSPSSVSASVGDRVTITCRASQGISRWLA WYQQKPGKAPKVLIYAASTLQSGVPSRFSGSGS GTDFTLTISSLQPEDFATYYCQQANSFPFTFGPGT KVDIK<br><br>SEQ ID NO: 25328 | QVQLVQSGAEVKKPGASVKVSCKASGYTFTGYHM HWVRQAPGQGLEWMGWINPNNNATNYAQNFQGR VTLTRDTSISTAYMELSRLRSDDTAVYYCARDGTSS FDFWGQGTLVTVSS<br><br>SEQ ID NO: 29334 |

FIGURE 50
(Continued)

| | | | |
|---|---|---|---|
| iPS:434037 | 21-225_49G12 | NA | GACATCCAGATGACCCAGTCTCCATCCTCCT GTCTGCGTCTGTAGGAGACAGAGTCACCATCA CTTGCCGGTCAAGTCAGAGCATTAGTACCTAT TTAATGTGGTATCAGCAGCAGAAACCAGGAAAG CCCCTAAGCTCTTGATCTATGCTGCATCCAGTT TGCAAATTGGGGTCCCATCAAGGTTCAGTGCC AGTGGATCTGGGACAGATTTCACTCTCACCAT CAGCAGTCTGCAACCTGAAGATTTTGCAACTT ACTACTGTCAACAGAGTTACAGTATCCCATTC ACTTTCGGCCCTGGGACCAAAGTGGATATCAA A | GAGGTGCAGCTGTTGGAGTCTGGGGGAGGCTTG GTACAGCCTGGGGGGTCCCTGAGACTCTCCTGTA CAGCCTCTGGATTCACCTTTAGCAGCTATGCCAT GAGCTGGGTCCGCCAGGCTCCAGGGAAGGGGCT GGAGTGGGTCTCAGTTATTAGTGGTAGTGGTGGT ACCACATTCTACGCAGACTCCGTGAAGGGCCGGC TCACCATCTCCAGAGACAATTCCAAGAACACACT GTATCTGCAAATGAACAGCCTGAGAGCCGAGGA CACGGCCGTATATTACTGTGCGCGTCGTATAGCA GTGGCTGGGAATGATGCTTTTGATATCTGGGGCC AAGGGACAATGGTCACCGTCTCTTCA |
| | | | SEQ ID NO: 29335 |
| | | AA | DIQMTQSPSSLSASVGDRVTITCRSSQSISTYLM WYQQKPGKAPKLLIYAASSLQIGVPSEFSASGSG TDFTLTISSLQPEDFATYYCQQSYSIPFTFGPGTK VDIK | EVQLLESGGGLVQPGGSLRLSCTASGFTFSSYAMS WVRQAPGKGLEWVSVISGSGGTTFYADSVKGRLTI SRDNSKNTLYLQMNSLRAEDTAVYYCARRIAVAG NDAFDIWGQGTMVTVSS |
| | | | SEQ ID NO: 25329 | SEQ ID NO: 29336 |
| iPS:434039 | 21-225_43B1 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAG TCAGCAGCCTGCAGCCTGAAGATTTTGCAACT TATTTCTGTCTACAGCATACTAGTTTCCCATTC ACTTTCGGCCCTGGGACCAAAGTGGATATCAA A | CAGGTGCAGCTGTGGTGGAGTCTGGGGGAGGCTTG GTCAAGCCTGGAGGGTCCCTGAGACTCTCCTGTG CAGCCTCTGGATTCACCTTCAGTGACTACTACAT GAACTGGATCCGCCAGGCTCCAGGGAAGGGGCT GGAGTGGGTTTCATACATTAATAGTAGTGGTTTT ACCATATACTACCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGCCGATACAATC TACTGGGGCCAGGGAACCCGGGTCACCGTCTCCT CA |
| | | | SEQ ID NO: 25331 | SEQ ID NO: 29337 |

FIGURE 50
(Continued)

| | | | | |
|---|---|---|---|---|
| | | AA | DIQMTQSPSSLSASVGDRVTITCRASQGIRNDLGWYQQKPGKAPKRLIYAASSLQSGVPSRFSGSGSGTEFTLTVSSLQPEDFATYFCLQHTSPFTFGPGTKVDIK | QVQLVESGGGLVKPGGSLRLSCAASGFTFSDYYMNWIRQAPGKGLEWVSYINSNGFTIYYADSVKGRFTISRDNAKNSLYLQMNSLRAEDTAVYYCAADTIYWGQGTRVTVSS |
| | | | SEQ ID NO: 25332 | SEQ ID NO: 29338 |
| iPS:434041 | 21-225_50H8 | NA | GACATCCAGATGACCCAGTCTCCATCCCCTGTCTGCGTCTGTAGGAGACAGAGTCAACATCACTTGCCGGGCAAGTCAGAGCATTAGCAGCTATCTTAATTTGGTATCAGCAGAAACCAGGGAAAGCCCCTAAGCTCCTGATCTATGCTGCATCCAGTCTGCAAAGTGGGGTCCCATCAAGGTTCAGTGCCAGTGGATCTGGGACAGATTTCACTCTCACCATCAGCAGTCTGCAACCTGAAGATTTTGCAAGTTACTACTGTCAACAGAGTAACAGTCTTCCATTCACTTTCGGCCCTGGGACCAAAGTGGATATCAAA | GAGGTGCAGCTGTTGGAGTCTGGGGGAGGCTTGGTACAGCCTGGGGGGTCCCTGAGACTCTCCTGTGCAGCCTCTAGATTCACCTTTAGCAGTTATGCCATGAGCTGGGTCCGCCAGGCTCCAGGGAAGGGGCTGGAGTGGGTCTCAGTTATTAGTGGTGGTGGTGTACCACATTCTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGCGTCGTATAGCAGTGGCTGGGAATGAGGCTTTTGATATCTGGGGCCAAGGGACAATGGTCACCGTCTCTCA |
| | | | SEQ ID NO: 25333 | SEQ ID NO: 29339 |
| | | AA | DIQMTQSPSSLSASVGDRVNITCRASQSISSYLIWYQQKPGKAPKLLIYAASSLQSGVPSRFSASGSGTDFTLTISSLQPEDFASYYCQQSNSLPFTFGPGTKVDIK | EVQLLESGGGLVQPGGSLRLSCAASRFTFSSYAMSWVRQAPGKGLEWVSVISGRGGTTFYADSVKGRFTISRDNSKNTLYLQMNSLRAEDTAVYYCARRIAVAGNEAFDIWGQGTMVTVSS |
| | | | SEQ ID NO: 25334 | SEQ ID NO: 29340 |

FIGURE 50
(Continued)

| | | | |
|---|---|---|---|
| iPS:434043 | 21-225_50G10 | NA | GACATCCAGATGACCCAGTCTCCATCTCCCT GTCTGCATCTGTAGGAGACAGAGTCACCATCA CTTGCCGGGCAAGTCAGGGCATTAGAAATAAT TTAGGCTGGTATCAGCAGAAACCAGGGAAAG TCCCTAAGCGCCTGATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGTATAATAGTTACCCGTTCA CTTTCGGCGGAGGGACCAAGGTGGAGAGCAA A SEQ ID NO: 25335 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGTAGCAACT TTTGACTACTGGGGCCAGGGAACCCTGGTCACCG TCTCCTCA SEQ ID NO: 29341 |
| | | AA | DIQMTQSPSSLSASVGDRVTITCRASQGIRNNLG WYQQKPGKVPKRLIYAASSLQSGVPSRFSGSGS GTEFTLTISSLQPEDFATYYCLQYNSYPFTFGGGT KVESK SEQ ID NO: 25336 | EVQLVESGGGLVKPGGSLRLSCAASGFTFSSYSMN WVRQAPGKGLEWVSSISGSSSYIYYADSVKGRFTIS RDNAKNSLYLQMNSLRAEDTAVYYCARVATFDY WGQGTLVTVSS SEQ ID NO: 29342 |
| iPS:434045 | 21-225_50H10 | NA | GACATCCAGATGACCCAGTCTCCATCTCCCT GTCTGCGTCTGTAGGAGACAGAGTCACCATCA CTTGCCGGGCAAGTCAGAGCATTACAGAGCTAT TTAATTTGGTATCAGCAGAAACCAGGGAAAGC CCCTAAGCTCCTGATCTATGCTGCATCCAGTTT GCAAAGTGGGGTCCCATCAAGGTTCAGTGCAA GTGGATCTGGGACAGATTTCACTCTCACCATC AGCAGTCTGCAACCTGAAGATTTTGCAAGTTA CTACTGTCAACAGAGTAACAGTATTCCATTCA CTTTCGGCCCTGGGACCAAAGTGGATATCAAA SEQ ID NO: 25337 | GAGGGGCAGTTGTTGGAGTCTGGGGGAGGCTTG GTACAGCCTGGGGGGTCCCTGAGACTCTCCTGTG CAGCCTCTAGATTCACCTTTAGCAGTTATGCCAT GAGCTGGGTCCGCCAGGCTCCAGGGAAGGGGCT GGAGTGGGTCTCAGTTATTAGTGGTCGTGGTGGT AGCACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGCGTGTAGCA GTGGCTGGGAATGAGGCTTTTGATATCTGGGGCC AAGGGACAATGGTCACCGTCTCTTCA SEQ ID NO: 29343 |

FIGURE 50
(Continued)

| | | | |
|---|---|---|---|
| iPS:434047 | 21-225_50A12 | AA | DIQMTQSPSSLSASVGDRVNITCRASQSIYSYLIW YQQKPGKAPKLLIYAASSLQSGVPSRFSASGSGT DFTLTISSLQPEDFASYYCQQSNSIPFTFGPGTKV DIK<br>SEQ ID NO: 25338 | EGQLLESGGGLVQPGGSLRLSCAASRFTFSSYAMS WVRQAPGKGLEWVSVISGRGGSTFYADSVKGRFTI SRDNSKNTLYLQMNSLRAEDTAVYYCARRIAVAG NEAFDIWGQGTMVTVSS<br>SEQ ID NO: 29344 |
| | | NA | GACATCCAGATGACCCAGTCTCCATCCTCCCT GTCTGCATCTGTAGGAGACAGAGTCAACATCA CTTGCCGGGCAAGTCAGGGCATTAGAAATGAT TTAGGCTGGTATCAGCAGAAACCAGGAAAG CCCCTAAGCGCCTGATCTATACTGCATCCAAT TTACAAAGTGGGGTCCCATCCAAGGTTCAGCGG CAGTGGATCTGGGACAGATCTCACTCTCACAA TCAGCAGCCTGCAGCCTGAAGATTTTGCAACT TATTACTGTCTACAGCATAATAGTATTCCCGTG GACGTTCGGCCAAGGGACCAAGGTGGAAATC AAA<br>SEQ ID NO: 25339 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCCACTATA TAAACTGGGTGCGACAGGCCCCTGGACAAGGC CTGAGTGGATGGCATGGGTCAACCTAACAGTG GTGGCACAAACTCTGCACAGAAGTTTCAGGGCA GGGTCACCATGACCAGGGACACGTCCATCAGCA CAGTCTACATGGAGCTGAGCAGGCTGAGATCTG ACGACACGGCCGTGTATTACTGTGCGAGGGGAG GGCTCGGCGGGTTAACTACTACTACTACGG TATGGACGTCTGGGGCCAAGGGACCACGGTCAC CGTCTCCTCA<br>SEQ ID NO: 29345 |
| | | AA | DIQMTQSPSSLSASVGDRVTITCRASQGIRNDLG WYQQKPGKAPKRLIYTASNLQSGVPSRFSGSGS GTEFTLTISSLQPEDFATYYCLQHNSYPWTFGQG TKVEIK<br>SEQ ID NO: 25340 | QVQLVQSGAEVKKPGASVKVSCKASGYTFTFGHYIN WVRQAPGQGPEWMAWVNPNSGGTNSAQKFQGRV TMTRDTSISTVYMELSRLRSDDTAVYYCARGGQLG GFNYYYGMDVWGQGTTVTVSS<br>SEQ ID NO: 29346 |

FIGURE 50
(Continued)

| | | | | |
|---|---|---|---|---|
| iPS:434049 | 21-225_50B12 | NA | GACATCCAGATGACCCAGTCTCCATCCTCCCTGTCTGCATCTGTGGGAGACAGAGTCACCATCACTTGTGTCGGGCAAGTCAGAGCATTAGTAGTTATTTAAATTGGTATCAGCATAAACCAGGGAAAGCCCCTAGGCTCCTGATCTATGCTGCATCCAGTTTGCAAAGTGGGGTCCCATCAAGGTTCAGTGGCAGTGAATCTGGGACAGATTTCATTCTCACTATCAGCAGTCTGCAACCTGAAGATTTTACAACTTATTACTGTCAACAGAGTTACATTGCCCCATTCACTTTCGGCCCTGGGACCAAAGTGGATATCAAA SEQ ID NO: 25341 | GAGGTGCAGCTGGTGGAGTCTGGGGGAGGCCTGGTCAAGCCTGGGGGGTCCCTGAGACTCTCCTGTCAGCCTCTGATTCACCTTCAGTAGCCATAGCATGAACTGGGTCCGCCAGGCTCCAGGGAAGGGCTGGAGTGGGTCTCATCATCGAGACTCAGTAGTAGTAATTACATATACTACGCAGACTCAGTGAAGGGCCGATTCACCATCTCCAGAGACAACGCCAAGAACTCACTTTATCTGCAAATGAACAGCCTGAGAGCCGAGACACGGCTGTGTATTACTGTGCGAGAGATCGGAGCATAGTAGTGGCTGGTCCCTGGGACTACTACGGTATGGACGTCTGGGGCCAAGGGACCACGGTCACCGTCTCCTCA SEQ ID NO: 29347 |
| | | AA | DIQMTQSPSSLSASVGDRVTITCRASQSISSYLNWYQHKPGKAPRLLIYAASSLQSGVPSRFSGSGSGTDFTLTISSLQPEDFTTYYCQQSYIAPFTFGPGTKVDIK SEQ ID NO: 25342 | EVQLVESGGGLVKPGGSLRLSCAASGFTFSSHSMNWVRQAPGKGLEWVSSISSSSNYIYYADSVKGRFTISRDYAKNSLYLQMNSLRAEDTAVYYCARDRSIVVAGPWDYYGMDVWGQGTTVTVSS SEQ ID NO: 29348 |
| iPS:434053 | 21-225_51E1 | NA | GATATTGTGATGACCCAGACTCCACTCTCTGTCCGTCACCCCTGGACAGCCGGCCTCCATGTCCTGCAAGTCTAGTCAGAGCCTCCTGCATAGTGAGGGAAAGACCTATTTGTATTGGTACCTGCGGAAGCCAGGCCAGCCTCCACAGTTCCTGATCTTTGAAGTTTCCAACCGGTTCTCTGGAGTGCCAGATAGGTTCAGTGGCAGCGGGTCAGGGACAGAATTCACACTGAAAATCAGCCGGGTGGAGGCTGAGGATGTTGGGGTTTATTACTGCATGCAAAGTATACAGCTTCCATTCACTTTCGGCGGAGGGACCAAGGTGGATATCAAA SEQ ID NO: 25343 | CAGGTGCAGCTGGTGGAGTCTGGGGGAGGCGTGGTCCAGCCTGGGAGGTCCCTGAGACTCTCCTGTCAGCGTCTGGATTCACCTTCAGTAGCTATGCCATGCACTGGGTCCGCCAGGCTCCAGGCAAGGGGCTGGAGTGGGTGGCAGTTATATGGTATGATGGAAGTAGTAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAAGGTATAGCAGCAGTTGGTCGGGGTATGGACGTCTGGGGCCAAGGGACCACGGTCACCGTCTCCTCA SEQ ID NO: 29349 |

FIGURE 50
(Continued)

| | | | |
|---|---|---|---|
| iPS:434055 | | AA | DIVMTQTPLSLSVTPGQPASMSCKSSQSLLHSEG KTYLYWYLRKPGQPPQFLIFEVSNRFSGVPDRFS GSGSGTEFTLKISRVEAEDVGVYYCMQSIQLPFT FGPGTKVDIK<br>SEQ ID NO: 25344 | QVQLVESGGGVVQPGRSLRLSCAASGFTFSSYGMH WVRQAPGKGLEWVAVIWYDGSSKYYADSVKGRF TISRDNSKNTLYLQMNSLRAEDTAVYYCARRYSSS WSGGMDVWGQGTTVTSS<br>SEQ ID NO: 29350 |
| 21-225_51B4 | | NA | GACATCCAGATGACCCAGTCTCCATCCTCCCT GTCTGCATCTGTAGGAGACAGAGTCACCATCA CTTGCCAGGCGAGTCGGGACATTACCTTCTAT TTAAATTGGTATCAGCAGAAACCAGGAAAG CCCCTAAGCTCCTGATCTACGATGCATCCAAT TTGGAAACAGGGGGTCCCATCAAGGTTCAGTGG CAGTGGATCTGGGACAGATTTTACTTTCACCA TCAGCTGCGTGCATCCTGAAGATATTGCAACA TATTTATGTCAACAGTATGATAATCTTCCATTC ACTTTCGGCCCAGGGACCACAGTGGATATCAA A<br>SEQ ID NO: 25345 | GAGGTGCAGCTGTTGGAGTCTGGGGGAGGCTTG GTACAGCCTGGGGGGTCCCTGAGTCTCTCCTGT GCAGCCTCTGGATTCACCTTTAGAAGTATGTCAT GAGCTGGGTCCGCCAGGCTCCAGGGAAGGGGCT GGAGTGGGTCTCAGTATTAGTGGTCGTGGTAGT AACACATTCTACACAGACTCCGTGAAGGGCCGGT TCACCATCTCCAGAGACAATCCAAGAACACGCT GTATCTGCAAATGAACAGCCTGAGAGCCGAGA CACGGCCGTATATTACTGTGCGAAAGGGATAACT GGATCACACGGTGCTTTTGATATCTGGGGCCAAG GGACAAATGGTCACCGTCTCTCTCA<br>SEQ ID NO: 29351 |
| | | AA | DIQMTQSPSSLSASVGDRVTITCQASRDITFYLN WYQQKPGKAPKLLIYDASNLETGVPSRFSGSGS GTDFTFTISCVHPEDIATYLCQQYDNLPFTFGPGT TVDIK<br>SEQ ID NO: 25346 | EVQLLESGGGLVQPGGSLSLSCAASGFTFRSYVMS WVRQAPGKGLEWVSAISGRGSNTFYTDSVKGRFTI SRDNSKNTLYLQMNSLRAEDTAVYYCAKGITGSH GAFDIWGQGTMVTVSS<br>SEQ ID NO: 29352 |

FIGURE 50
(Continued)

| | | | | |
|---|---|---|---|---|
| iPS:434057 | 21-225_51E4 | NA | GACATCCAGATGACCCAGTCTCCATCCTCCCT GTCTGCATCTGTGGGAGACAGAGTCACCATCA CTTGCCGGGCAAGTCAGGGACAGTTAGAAATGAT TAGGCTGGTATCAGCAGAAACCAGGGAAAG CCCCTCAGCGCCTGATCTATGCTGCATCCAGT TGCAAAGTGGGGTCCCATCAAGGTTCAGCGGC AGTGGATCTGGGACAGAATTCACTCTCACAAT CAGCAGCCTGCAGCCTGAGGATTTTGCAGCTT ATTATTGTCTACAGCATAATAGTTACCCATTCA CTTTCGGCCCTGGGACCAAAGTGGATATCAAA SEQ ID NO: 25347 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGTAGTTATGCAT GCACTGGGTCCGCCAGGCTCCAGGCAAGGGGCT GGAGTGGGTGGCAGTTATATGCAGACTCCGTGAAGGGCCGA AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGAACTGG ATTTCTCTGACTACTGGGGCCAGGGAACCCTG GTCACCGTCTCCTCA SEQ ID NO: 29353 |
| | | AA | DIQMTQSPSSLSASVGDRVTITCRASQGIRNDLG WYQQKPGKAPQRLIYAASSLQSGVPSRFSGSGS GTEFTLTISSLQPEDFAAYYCLQHNSYPFTFGPGT KVDIK SEQ ID NO: 25348 | QVQLVESGGGVVQPGRSLRLSCAASGFTFSSYGMH WVRQAPGKGLEWVAVIWYDESNKYYADSVKGRF TISRDNSKNTLYLQMNSLRAEDTAVYYCARELGFL SDYWGQGTLVTVSS SEQ ID NO: 29354 |
| iPS:434059 | 21-225_51C5 | NA | GACATCCAGATGACCCAGTCTCCATCCTCACT GTCTGCATCTGTAGGAGACAGAGTCACCATCA CTTGTCCGGGCGAGTCAGGGCATTAGCAGTTAT TTAGCCTGGTTTCAGCAGAAACCAGGGAAAGC CCCTAAGTCCCTGATCTATGCTGCATCCAGTTT GCGAAGTGGGGTCCCATCACAGTTCAGCGGCA GTGGATCTGGAACAGATTTCATTCTCACCATC AGCAGCCTGCAGCCTGAAGATTTTGCAACTTA TTACTGCCAACAGTATTATAGTTACCCATTCAC TTTCGGCCCTGGGACCAAAGTGGATATCAAA SEQ ID NO: 25349 | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATGTCATG AGCTGGGTCCGCCAGACTCCAGGGAAGGGGCTG GAGTGGGTCTCAACTATGCAGACTCGTGAGTGGTGGTC GCACATACTACGCAGACTCCGTGAACGGCCGATT CACCGTCTCCAGAGACAATTCCAAGAACACGCTG TATTTGCAAATGAGCAGCCTGAGAGCCGAGGAC ACGGCCGTATATTACTGTGCGCGGGGTGTGACTGCTT TGACTACTGGGGCCAGGGAACCCTGGTCACCGT CTCCTCA SEQ ID NO: 29355 |

FIGURE 50
(Continued)

| | | | | |
|---|---|---|---|---|
| iPS:434061 | 21-225_51C7 | AA | DIQMTQSPSSLSASVGDRVTITCRASQGISNYLAWFQQKPGEAPKSLIYAASSLRSGVPSQFSGSGSGTDFILTISSLQPEDFATYYCQQYSYPFTFGPGTKVDIK<br>SEQ ID NO: 25350 | EVQLLESGGGLVQPGGSLRLSCAASGFTFSSYVMSWVRQTPGKGLEWVSTMSGSGGRTYYADSVNGRFTVSRDNSKNTLYLQMSSLRAEDTAVYYCARVTAFDYWGQGTLVTVSS<br>SEQ ID NO: 29356 |
| | | NA | GACATCCAGATGACCCAGTCTCCATCTTCCGTGTCTGCATCTGTAGGAGACAGAGTCACCATCACTTGTCGGGCGAGTCAGGATGTTAACAACTACTTAGCCTGGTTTCAGCAGAAACCAGGGAAAGCCCCTAAGTCTCTGATCTATGCTGCATCCAGTTTGCAAAATGGGGTCCCATCAAGGTTCAGCGGCAGTGGATCTGGGACAGATTTCACTCTCACCATCAGCAGCCTGCTGCCTGAAGATTTTGCAACTACTATTGTCAACAAAACTAACAGTTTCCCATTCACTTTCGGCCCTGGGACCAAAGTGGATATCAAA<br>SEQ ID NO: 25351 | GAGGTGCAGCTGTTGGAGTCTGGGGGAGGCTTGGTGCAGCCTGGGGGGTCCCTGAGACTCTCCTGTGCAGCCTCTGGATTCACCATTAGCAACTATGCCATGACCTGGGTCCGCCAGACTCCAGGGAAGGGGCTGGAGTGGGTCTCAGTTATTAGTGCTAGTGGTGGTAACTCATTCTACGCAGACTCCGTGAAGGGCCGGTTCACCATCTCCAGAGACAACAATTCGAGAACACGTTCTATCTGCAAATGAACAGCCTGAGAGCCGAGGACACGGCCGTATATTACTGTGCGAAAGCAAGGCAGTGGCTGGGTCACACTGGTTCGACCCTGGGGCCAGGGAACCCTGGTCACCGTCTCCTCA<br>SEQ ID NO: 29357 |
| | | AA | DIQMTQSPSSVSASVGDRVTITCRASQDVNNYLAWFQQKPGKAPKLLIYAASSLQNGVPSRFSGSGSGTDFTLTISSLLPEDFATYYCQQTNSFPFTFGPGTKVDIK<br>SEQ ID NO: 25352 | EVQLLESGGGLVQPGGSLRLSCAASGFTISNYAMTWVRQTPGKGLEWVSASGGNSFYADSVKGRFTISRDNSENTFYLQMNSLRAEDTAVYYCAKARAVAGSHWFDPWGQGTLVTVSS<br>SEQ ID NO: 29358 |

FIGURE 50
(Continued)

| | | | |
|---|---|---|---|
| iPS:434063 | 21-225_51G7 | NA | GACATCCAGATGACCCAGTCTCCATCTTCCGTGTCTGCATCTGTAGGAGACAGAGTCACCATCACTTGTCGGGCGAGTCAGGATCAGGGTATTAGCAGTTGGTTAGCCTGGTATCAGCAGAAACCAGGGAAAGCCCCTAAGGTCCTGATCTATGCTGCATCCAATTTGCAAAGTGCGGTCCCATCAAGGTTCAGCGGCAGTGGATCTGGGACAGATTTCACTCTCACCATCAGCAGCCTGCAGCCTGAAGATTTTGCAACTTACTATTGTCAACAGGCTCACAGTTTCCCGTGGACGTTCGGCCAAGGGACCAAGGTGGAAATCAAA SEQ ID NO: 25353 | GAGGTGCAGCTGGTGGAGTCTGGGGGAGGCTGGTCAAGCCTGGGGGGTCCCTGAGACTCTCCTGTGCAGCCTCTGGATTCACCTTCAGTAGTAGCTATAGCATGAACTGGGTCCGCCAGGCTCCAGGGAAGGGGCTGGAGTGGGTCTCATCCATTAGTAGTAGTAGTAGTTACATATACTACGCAGACTCAGTGAAGGGCCGATTCACCATCTCCAGAGACAACGCCAAGAACTCACTGTATCTGCAAATGAACAGCCTGAGAGCCGAGGACACGGCTGTGTATTACTGTGCGAGAGCTCGCCTTGACTACTGGGGCCAGGGAACCCTGGTCACCGTCTCCTCA SEQ ID NO: 29359 |
| | | AA | DIQMTQSPSSVSASVGDRVTITCRASQDISSWLAWYQQKPGKAPKVLIYAPSNLQSAVPSRFSGSGSGTDFTLTISSLQPEDFATYYCQQAHSFPWTFGQGTKVEIK SEQ ID NO: 25354 | EVQLVESGGGLVKPGGSLRLSCAASGFTFSSYSMNWVRQAPGKGLEWVSSISSSSYIYYADSVKGRFTISRDNAKNSLYLQMNSLRAEDTAVYYCARARLDYWGQGTLVTVSS SEQ ID NO: 29360 |
| iPS:434065 | 21-225_50D4 | NA | GACATCCAGATGACCCAGTCTCCATCTTCCGTGTCTGCATCTGTGGGAGACAGAGTCACCATCACTTGTCGGGCGAGTCAGGGTATTAGCAGTTGGTTAGCCTGGTATCAGCAGAAACCAGGGAAAGCCCCTAAGGTCCTGATCTATGCTGCATCCACTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTATTGTCAACAGGCTAACAGTTTCCCATTCACTTTCGGCCCTGGGACCAAAGTGGATATCAGA SEQ ID NO: 25355 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACCATATGCACTGGGTGCGACAGGCCCCTGGACAAGGGCTTGAGTGGATGGGATGGATCAACCCTAATAATAATGCCACAAACTATGCTCAGAGCTTTCAGGGCAGGGTCACCCTGACCAGGGACACGTCCATCAGCACAGCCTACATGGAGCTGAGCAGGCTGAGATCTGACGACACGGCCGTGTATTACTGTGCGAGAGACGGTACCAGCAGTTTGACTTCTGTGGGGCCAGGGAACCCTGGTCACCGTCTCCTCA SEQ ID NO: 29361 |

FIGURE 50
(Continued)

| | | | | |
|---|---|---|---|---|
| iPS:434067 | 21-225_51H8 | AA | DIQMTQSPSSVSASVGDRLTITCRASQGISRWLAWYQQKPGKAPKVLIYAASTLQSGVPSRFSGSGSGTDFTLTISSLQPEDFATYYCQQANSFPFTFGPGTKVDIR<br>SEQ ID NO: 25356 | QVQLVQSGAEVKKPGASVKVSCKASGYTFTGYHMHWVRQAPGQGLEWMGWINPNNATNYAQSFQGRVTLTRDTSISTAYMELSRLRSDDTAVYYCARDGTSSFDFWGQGTLVTVSS<br>SEQ ID NO: 29362 |
| | | NA | GACATCCAGATGACCCAGTCTCCATCCTCCCTGTCTGCATCTGTAGGAGACAGAGTCACCATCACTTGCCGGGCAAGTCAGGGCATTAGAAATGATTGGGCTGGTATCAGCAGAAACCAGGGAAAGCCCCTAAGCGCCTGATCTATGCTGCTTCCAGTTTGCAAAGTGGGGTCCCATCAAGGTTCAGCGGCGGTGGATCTGGGACACATTCACTCTCACAATCAGCAGCCTGCAGCCTGAAGATATAGTTACCCGTGGACGTTCGGCCAAGGGACCAAGGTGGAAATCAAA<br>SEQ ID NO: 25357 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCCACTATATGAACTGGGTGCGACAGGCCCCTGGACAAGGACTTGAGTGGATGGGATGGGTCAACCTAACAGTGGTGGCTCAAACTCTGCACAGACAGTTTCAGGGCAGGGTCACCATGACCAGGGACACGTCCATCAGCACAGTCTACATGGAGCTGAGCAGGCTGAGTTCTGACGACACGGCCGTGTATTACTGTGCGAGGGAGGGCAGCTGCGGCGGCTTTAACTTCTACTACTACGGTATGGACGTCTGGGGCCAAGGGACCACGGTCACCGTCTCCTCA<br>SEQ ID NO: 29363 |
| | | AA | DIQMTQSPSSLSASVGDRVTITCRASQGIRNDLGWYQQKPGKAPKRLIYAASSLQSGVPSRFSGGGSGTHFTLTISSLQPEDFATYYCLQHNSYPWTFGQGTKVEIK<br>SEQ ID NO: 25358 | QVQLVQSGAEVKKPGASVKVSCKASGYTFTGHYMNWVRQAPGQGLEWMGWVNPNSGGSNSAQQFQGRVTMTRDTSISTVYMELSSDDTAVYYCARGGQLGGFNFYYGMDVWGQGTTVTVSS<br>SEQ ID NO: 29364 |

FIGURE 50
(Continued)

| | | | |
|---|---|---|---|
| iPS:434069 | 21-225_51E9 | NA | GACATCCAGATGACCCAGTCTCCATCTTCCGT GTCTGCCTCTGTAGGAGACAGAGTCACCATCA CTTGTCGGGCGAGTCAGGTATTAGCAGTTGG TTAGCCTGGTATCAGCAGAAACCAGGGAAAG CCCCTAAGCTCCTGATCTATGTTGCATCCAGTT TGCAAAGTGGGGTCCCATCAAGGTTCAGCGGC AGTGGATCTGGGACAGATTTCACTCTCACCAT CAGGAGCCTGCAGCCTGAAGATTTTGCAACTT ACTATTGTCAACAGGCTAAAAGTTTCCCATTC ACTTTCGGCCCTGGGACCAAAGTGGATATCAA A SEQ ID NO: 25359 | CAGGTGCAGCTGGTGCAGTCTGGGGCTGAGGTG AAGAAGCCTGGGGCCTCAGTGAAGGTCTCCTGC AAGGCTTCTAGATACACCTTCACCGGCTACCATA TACACTGGGTGCGACAGGCCCCTGGACAAGGC TTGAGTGGATGGGATGGATCAACCCTAACACTAA TGGCACACAGTATGCACAGAAGTTTCAGGGCCG GGTCACCATGACCAGGGACACGTCCATCAGCAC AGCCTACATGGAGCTGAGCAGCCTGAGATCTGA CGACACGGCCGTGTATTACTGTGCGAGAGATGGC ACCTCGTCCTTTGACTACTGGGGCCAGGGAACCC TGGTCACCGTCTCCTCA SEQ ID NO: 29365 |
| | | AA | DIQMTQSPSSVSASVGDRVTITCRASQGISSWLA WYQQKPGKAPKLLIYVASSLQSGVPSRFSGSGS GTDFTLTIRSLQPEDFATYYCQQAKSFPFTFGPGT KVDIK SEQ ID NO: 25360 | QVQLVQSGAEVKKPGASVKVSCKASRYTFTGYHIH WVRQAPGQGLEWMGWINPNTNGTQYAQKFQGRV TMTRDTSISTAYMELSSLRSDDTAVYYCARDGTSS FDYWGQGTLVTVSS SEQ ID NO: 29366 |
| iPS:434071 | 21-225_51F9 | NA | GACATCCAGATGACCCAGTCTCCATCTCCCT GTCTGCATCTGTAGGAGACAGAGTCACCATCA CTTGCCGGGCAAGTCAGGGCATTAGGACTGAT TAGGCTGGTATCAGCAGAAACCAAGGAAAG CCCCTAAGCGCCTGATCTATGCTGCATCCAGTT TGCAAAGTGGGGTCCCATCTATGCTGCATCCAGTT AGTGGATCTGGGACAGATTTCACTCTCACAAT CAGCAGCCTGCAGCCTGAAGATTTTGCATCTT ATTACTGTCTACAGCATAATAGTTACCCATTC ACTTTCGGCCCTGGGACCAAAGTGGATATCAA A SEQ ID NO: 25361 | CAGGTGCAGCTGGTGGAGTCTGGGGAGGCGTG GTCCAGCCGGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGCAGACTCCGTGAAAT AATAAATACTATGCAGACTCCGTGAAGGGCCGA TTCACCATCTCCAGAGACAATTCCAAGAACACGC TGTATCTGCAAATGAACAGCCTGAGGCGCGAGG ACACGGCTGTGTATTACTGTGCGAGGAGGAGCTGGG ATTTCTCTCTGACTACTGGGGCCAGGGAACCCTG GTCACCGTCTCCTCA SEQ ID NO: 29367 |

FIGURE 50
(Continued)

| | | | |
|---|---|---|---|
| | | AA | DIQMTQSPSSLSASVGDRVTITCRASQGIRTDLG WYQQKPRKAPQRLLIYAASSLQRGVPSRFSGSGS GTDFTLTISSLQPEDFASYYCLQHNSYPFTFGPGT KVDIK<br><br>SEQ ID NO: 25362 | QVQLVESGGGVVQPGRSLRLSCAASGFTFSDYGM HWVRQAPGKGLEWVAVIWFDGNNKYYADSVKGR FTISRDNSKNTLYLQMNSLSAEDTAVYYCARELGF LSDYWGQGTLVTVSS<br><br>SEQ ID NO: 29368 |
| iPS:434073 | 21-225_51H10 | NA | GACATCCAGATGACCCAGTCTCCATCCTCCCT GTCTGCGTCTGTAGGAGACAGAGTCACCATCA CTTGCCGGGCAAGTCAGAGACATTAGTACCTAT TTAATGTGGTATCAGCAGAAACCAGGGAAAG CCCCTAAGCTCTTGATATATGCTGCATCCAGTT TGCAAAGTGGGGTCCCATCAGAGTTCAGTGCC AGTGGATCTGGGACAGATTTCACTCTCACCAT CAGCAGTCTGCAACCTGAAGATTTTGCAACTT ACTACTGTCAACAGAGAGTTACAGTATCCCATTC ACTTTCGGCCCTGGGACCAAAGTGGATATCAA A<br><br>SEQ ID NO: 25363 | GAGGTGCAGCTGTTGGAGTCTGGGGGAGGCTTG GTACAGCCTGGGGGGTCCCTGAGACTCTCCTGTA CAGCCTCTGGATTCACCTTTAGCAGCTATGCCAT GAGCTGGGTCCGCCAGGCTCCAGGGAAGGGGCT GGAGTGGGTCTCAGTTATTAGTGGTAGTGGTGGT ACCACATTCTACGCAGACTCCGTGAAGGGCCGGC TCACCATCTCCAGAGACAATTCCAAGAACACACT GTATCTGCAAATGAACAGCCTGAGAGCCGAGGA CACGGCCGTATATTACTGTGCCGCGTCGTATAGCA GTGGCTGGGAATGATGCTTTTGATATCTGGGGCC AAGGGACAAATGGTCACCGTCTCCTCA<br><br>SEQ ID NO: 29369 |
| | | AA | DIQMTQSPSSLSASVGDRVTITCRASQSISTYLM WYQQKPGKAPKLLIYAASSLQSGVPSEFSASGSG TDFTLTISSLQPEDFATYYCQQSYSIPFTFGPGTK VDIK<br><br>SEQ ID NO: 25364 | EVQLLESGGGLVQPGGSLRLSCTASGFTFSSYAMS WVRQAPGKGLEWVSVISGSGGTTFYADSVKGRLTI SRDNSKNTLYLQMNSLRAEDTAVYYCARRIAVAG NDAFDIWGQGTMVTVSS<br><br>SEQ ID NO: 29370 |

FIGURE 50
(Continued)

| | | | | |
|---|---|---|---|---|
| iPS:434075 | 21-225_51B11 | NA | GCATCCAGATGACCCAGTCTCCATCCTCCCT GTCTGCATCTGTAGGAGACAGAGTCACCATCA CTTGCCGGACAAGTCAGGGCATTAGAAATGAT TTAGGCTGGTATCAGCAGAAACCAAGGAAAG CCCCTAAAGCGCCTAAATCTATGCTGATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAGGTGGATATCAA A SEQ ID NO: 25365 | CAGGTGCAGCTGGTGGAGTCTGGGGGAGGCGTG GTCCAGCCGGGGAGGTCCCTGAGACTCTCCTGTG CAGCGTCTGGATTCACCTTCAGTGACTGGTGTG GCACTGGGTCCGCCAGGCTCCAGGCAAGGGGCT GGAGTGGGTGGCAGTTATATGGAGTTGGTGAAAT AATAAATACTATGGAGACTCCGTGAAGGGCCGA TTCACCATCTCCAGAGACAATTCCAAGAACACGC TGTATCTGCAAATGAACAGCCTGAGCGCCGAGG ACACGGCTGTGTATTACTGTGCGAGGGAGCTGGG AATTTCTCTGACTACTGGGGCCAGGGAACCCTG GTCACCGTCTCCTCA SEQ ID NO: 29371 |
| | | AA | AIQMTQSPSSLSASVGDRVTITCRTSQGIRNDLG WYQQKPRKAPKRLIYAASSLQSGVPSRFSGSGS GTEFTLTISSLQPEDFATYYCLQHNSYPFTFGPGT KVDIK SEQ ID NO: 25366 | QVQLVESGGGVVQPGRSLRLSCAASGFTFSDYGM HWVRQAPGKGLEWVAVIWFGGNNKYYGDSVKGR FTISRDNSKNTLYLQMNSLSAEDTAVYYCARELGF LSDYWGQGTLVTVSS SEQ ID NO: 29372 |
| iPS:434077 | 21-225_51F11 | NA | GACATCCAGATGACCCAGTCTCCATCCGCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGCCTGAAGATTCACTCTCACAA TCAGCAGCCTGCAGCCTGAAGATTTTGCAACT TATTACTGTCTACAGCATAATAGTTACCCGTTC ACTTTCGGCGGAGGGACCAAGGTGGAGATCA AA SEQ ID NO: 25367 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTTTGGCAT GCACTGGGTCCGCCAGGCTCCAGGCAAGGGGCT GGAGTGGGTGGCAGTTATATGGTATGAGGAAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAACTGG GGTTCCTCTCTGACTTCTGGGGCCAGGGAACCCT GGTCACCGTCTCCTCA SEQ ID NO: 29373 |

FIGURE 50
(Continued)

| | | | |
|---|---|---|---|
| iPS:434079 | | AA | DIQMTQSPSALSASVGDRVTITCRASQGIRNDLG WYQQKPGKAPKRLIYAASSLQSGVPSRFSGSGS GTEFTLTISSLQPEDFATYYCLQHNSYPFTFGGGT KVEIK<br><br>SEQ ID NO: 25368 | QVQLVESGGGVVQPGRSLRLSCAASGFTFSNFGMH WVRQAPGKGLEWVAVIWYEESNKYYADSVKGRF TISRDNSKNTLYLQMNSLRAEDTAVYYCARELGFL SDFWGQGTLVTSS<br><br>SEQ ID NO: 29374 |
| | 21-225_52B1 | NA | GACATCCAGATGACCCAGTCTCCATCTTCCGT GTCTACATTTGTAGGAGACAGAGTCACCATCA CTTGTCGGGCGAGTCAGGATCAGGATATTCGCACCTGG TTAGCCTGGTATCAGCAGAAACCTGGGAAAGC CCCTAAGCTCCTGATCTATGCTGCATCCAGTTT GCAAAATGGGGTCCCATCAAGGTTCAGCGGCA GTGGATCTGGGACAGATTTCACTCTCACCATC AGTAGCCTGCAGCCTGAAGATTTTGCAACTTA CTTTTGTCAACAGGCTAAAAGTTTCCCATTCAC TTTCGGCCCTGGGACCAAAGTGGATATCAAA<br><br>SEQ ID NO: 25369 | CAGGTGCAGTTGGTGCAGTCTGGGGGCTGAGGTGA AGAAGCCTGGGGCCTCAGTGAAGGTCTCCTGCA AGGCTTCTGATACACCTTCACCGGCTATCATAT GCAGTGGGTGCGACAGGCCCCTGGACAAGGGCT TGAGTGATGGGATGGGATCAACCTAACAGTGGT GCCACAAACTATGCACAGAACTTTCAGGGCAGG GTCACCATGACCCGGGACACGTCCATCAGCACA GCCTACCTGCAGTGGAGCCTGAGCAGGCTGAGATCTGACG ACACGGCCGTGTATTACTGTGCGAGAGATGGCAC CTGTCCTTTGACTACTGGGGCCAGGGAACCCTG GTCACCGTCTCCTCA<br><br>SEQ ID NO: 29375 |
| | | AA | DIQMTQSPSSVSTFVGDRITITCRASQDIRTWLA WYQQKPGKAPKLLIYAASSLQNGVPSRFSGSGS GTDFTLTISSLQPEDFATYFCQQAKSFPFTFGPGT KVDIK<br><br>SEQ ID NO: 25370 | QVQLVQSGAEVKKPGASVKVSCKASGYTFTGYHM QWVRQAPQGLEWMGWINPNSGATNYAQNFQGR VTMTRDTSISTAYLDLSRLRSDDTAVYYCARDGTS SFDYWGQGTLVTVSS<br><br>SEQ ID NO: 29376 |

FIGURE 50
(Continued)

| | | | |
|---|---|---|---|
| iPS:434081 | 21-225_52B2 | NA | GACATCCAGATGACCCAGTCTCCATCGTCACTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAGGCGCCTGATCTATGCTGCATCCTTTTGCAAAGTGGGGTCCCATCGACATTCAGCGGCAGTGGATCTGGGACAGACTTCACTCTCACAATCAGCAGCCTGCAGCCTGAAGATTTTGCAACTTATTACTGTCTGCAGCATAATAGCTACCCTCACTTTCGGCGGAGGGACCAAGGTGGAGATCAAA SEQ ID NO: 25371 |
| | | AA | DIQMTQSPSSLSASVGDRVTITCRASQGIRNDLGWYQQKPGKAPRRLIYAASFLQSGVPSTFSGSGSGTEFTLTISSLQPEDFATYYCLQHNSYPLTFGGGTKVEIK SEQ ID NO: 25372 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGTAACTATGGCATGCACTGGGTCCGCCAGGCTCCAGGCAAGGGGCTGGAGTGGGTGGCAGTTACATGGTTTGATGGAAGTAATCAACGCTATGCAGACTCCGTGAAGGGCCGATTCACCATCTCCAGAGACATTTCCAAGAACACGCTGTATCTGCAAATGAACAGCCTGAGTGCCGAGACACGGCTGTGTATTACTGTGCGAGAGATCTGGGATGATCGAGGACTTCTGGGGCCAGGGAACCCTGGTCACCGTCTCCTCA SEQ ID NO: 29377 |
| | | | QVQLVESGGGVVQPGRSLRLSCAASGFTFSNYGMHWVRQAPGKGLEWVAVTWFDGSNQRYADSVKGRFTISRDISKNTLYLQMNSLSAEDTAVYYCARDLGMIEDFWGQGTLVTVSS SEQ ID NO: 29378 |
| iPS:434083 | 21-225_52H2 | NA | GACATCCAGATGACCCAGTCTCCATCTTCCGTGTCTGCATCTGTAGGAGACAGAGTCACCATCACTTGTGTCGGGAGTCAGGAGTCAGAATATTACCAACTGGTTAGCCTGGTTTCAGCAGAAACCAGGGAGAGCCCCTAAGCTCCTGATCTATACTACATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTGTCAACAGACTAACAGTTTCCCGTGACGTTCGGCCAAGGGACCAAGGTAGAAGTCAAA SEQ ID NO: 25373 | GAGGTGCAGCTGTTGGAGTCTGGGGGAGGCTTGGTACAGCCGGGGGGGTCCCTGAGACTCTCCTGTGCAGCCTCTGGATTCACCTTTAGCAGAAATGCCATGAGCTGGGTCCGCCAGGCTCCAGGGAAGGGGCTGGAGTGGGTCTCAGTTATTAGTGGTGGTGGTGGTAATACATTCTACGCAGACTCCGTGAAGGGCCGGTTCACCGTCTCCAGAGACAATTCCAAGAACACGCTGTTTCTGCAAATGAACAGCCTGAGAGCCGAGGACACGGCCGTATATTACTGTGCGAAAAATGGGCGAGAGCAGTGGCTTGACTACTGGGGCCAGGGAACCCTGGTCACCGTCTCCTCA SEQ ID NO: 29379 |

FIGURE 50
(Continued)

| | | | |
|---|---|---|---|
| iPS:434085 | | AA | DIQMTQSPSSVSASVGDRVTITCRASQNITNWLA WFQQKPGRAPKLLIYTTSSLQSGVPSRFSGSGSG TDFTLTISSLQPEDFATYCCQQTNSFPWTFGHGT KVEVK<br>SEQ ID NO: 25374 | EVQLLESGGGLVQPGGSLRLSCAASGFTFSRNAMS WVRQAPGMGLEWVSAISGRGGNTFYADSVKGRFT VSRDNSKNTLFLQMNSLRAEDTAVYYCAKNGREQ WLDYWGQGTLVTVSS<br>SEQ ID NO: 29380 |
| | 21-225_52E3 | NA | GACATCCAGATGACCCAATCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCAATGCTGCATCCAGTTT ACAAAGTGGGGTCCCATCAAAGTTCAGCGGCA GTGGATCTGGGACAGATTTCACTCTCACTATC AGCAGCCTGCAGCCTGAAGATTTTGCAACTTA TTACTGCCAACAGTATATAAGTTTCCCTTTCAC TTTCGGCCCTGGGACCAAAGTGGATATCAAA<br>SEQ ID NO: 25375 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAAAAT GAACTGGGTCCGCCAGGCTCCAGGGAAGGGGCT GGAGTGGGTCTCATCCATTAGTAGTGGTAATAGT TCCATATACTACGCAGACTCAGTGAAGGGCCGAT TCACCATCTCCAGAGACAACGCCGAAAACTCACT GTATCTGCAAATGAACAGCCTGAGAGCCGAAGA CACGGCTGTGTATTACTGTGCGAGAGTTAGCAGT AATGACTACTGGGGCCAGGGAACCCTGGTCACT GTCTCCTCA<br>SEQ ID NO: 29381 |
| | | AA | DIQMTQSPSSLSASVGDRVTITCRASQGISNYLA WFQQKPGKAPKSLINAASSLQSGVPSKFSGSGSG TDFTLTISSLQPEDFATYYCQQYNSFPFTFGPGTK VDIK<br>SEQ ID NO: 25376 | EVQLVESGGGLVKPGGSLRLSCAASGFTFSSYKMN WVRQAPGKGLEWVSSISSGNSSIYADSVKGRFTIS RDNAENSLYLQMNSLRAEDTAVYYCARVSSNDY WGQGTLVTVSS<br>SEQ ID NO: 29382 |

FIGURE 50
(Continued)

| | | | |
|---|---|---|---|
| iPS:434087 | 21-225_52F6 | NA | GACATCCAGATGACCCAGTCTCCATCCTCCT GTCTGCATCTGTAGGAGACAGAGTCACCATCA CTTGCCAGGCGAGTCAGGACATTAGTAACTAT TTACATTGGTATCAGCAGAAACCAGGGAAAGC CCCTAAACTCCTGATCTACGATGCATCCACTTT GGGAACAGGGGTCCCATTAAGGTTCAGTGGA AGTGGATCTGGGACAGATTTACTTTCACCAT TAACAGCCTGCAGCCTGAAGATATTGCAACAT ATTCCTGTCAACAGTGTGATAATCTCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAATTATATCATATGGAGGAAG TAATAAATACTATGCAGACTCCGTGAAGGGCCG ATTCACCATCTCCAGAGACAATTCCAAGAATACG CTGTATCTGCAAATGAACAGCCTGAGAGTCGATG ACACGGCTGTGTATTACTGTGCGAGAAGGTCAGC AGCTCGGCCGGCTACGGTATGGACGTCTGGGG CCAGGGGACCACGGTCACCGTCTCCTCA |
| | | | SEQ ID NO: 25377 | QVQLVESGGGVVQPGRSLRLSCAASGFTFSSYGMH WVRQAPGKGLEWVAIISYGGSNKYYADSVKGRFTI SRDNSKNTLYLQMNSLRADDTAVYYCARRSAARP GYGMDVWGQGTTVTVSS |
| | | AA | DIQMTQSPSSLSASVGDRVTITCQASQDISNYLH WYQQKPGKAPKLLIYDASTLGTGVPLRFSGSGS GTEFTFTINSLQPEDIATYSCQQCDNLPLTFGGGT KVEIK | SEQ ID NO: 29383 |
| | | | SEQ ID NO: 25378 | SEQ ID NO: 29384 |
| iPS:434091 | 21-225_52B9 | NA | GCCATCCAGATGACCCAGTCTCCATCCTCCCT GTCTGCATCTGTAGGAGACAGAGTCACCATCA CTTGCCCGGGCAAGTCAGGGACAGAGTCATTAGAAATGAT TTAGGCTGGTATCAGCAGAAACCAAGGAAAG CCCCTAAGGCCTGATCTATGCTGCATCCAGT TTGCAAAGTGGGGTCCCATTAAGGTTCAGCGG CAGTGGATCTGGGACAGATTCACTCTCACAA TCAGAAGCCTGCAGCCTGAAGATTTTGCAACT TATTACTGTCTACAGCATAATAGTTACCCATTC ACTTTCGGCCCTGGGACCAAAGTGGATATCAA A | CAGGTGCAGCTGGTGGAGTCTGGGGGAGGCGTG GTCCAGCCTGGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTTTGATGGAAAT AATAAATACTATGCAGACTCCGTGAAGGGCCGA TTCACCATCTCCAGAGACAATTCCAAGAACACGC TGTATCTGCAAATGAACAGCCTGAGCGCCGAGG ACACGGCTGTGTATTACTGACTGGGGCCAGGGAGCTGGG ATTTCTCTGACTACTGGGGCCAGGGAACCCTG GTCACCGTCTCCTCA |
| | | | SEQ ID NO: 25379 | SEQ ID NO: 29385 |

FIGURE 50
(Continued)

| | | | |
|---|---|---|---|
| iPS:434093 | 21-225_52D10 | AA | AIQMTQSPSSLSASVGDRVTITCRASQGIRNDLG WYQQKPRKAPKRLIYAASSLQSGVPLRFSGSGS GTEFTLTIRSLQPEDFATYYCLQHNSYPFTFGPGT KVDIK<br>SEQ ID NO: 25380 | QVQLVESGGGVVQPGRSLRLSCAASGFTFSDYGM HWVRQAPGKGLEWVAVIWFDGNNKYYADSVKGR FTISRDNSKNTLYLQMNSLSAEDTAVYYCARELGF LSDYWGQGTLVTVSS<br>SEQ ID NO: 29386 |
| | | NA | GATGTTATGATGACCCAGATTCCACTCTCTCTG TCCGTCACCCTGGACAGCCGGCCTCCATCC CTGCAAGTCTAGTGCAGAGCCTCCTGCATAGTG AAGGAAAGACCTATTTGTATTGGTACTTGCAG AAGCCAGGCAGCCTCCAACGGGTCTCTGATCTT TGAAGTTTCCAACCGGGTCTCTGGAGTGCCAG ATAGGTTCAGTGGCAGAGGGTCAGGACAGA TTTCACACTGAAAATCAGCCGGGTGGAGGCTG AGGATGTTGGGGTTTATTACTGCATGCAAAGT ATACAGTATCCGATCACCTTCGGCCAAGGGAC ACGACTGGAGATTAAA<br>SEQ ID NO: 25381 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGCAT GCACTGGGTCCGCCAGGCTCCAGGCAAGGGCT GGAGTGGGTGGCACTTATATGGTATGATGGAAGT AATAAATACCATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTGGGGCGGTATGGACGTCTGGGG CCAAGGGACCACGGTCACCGTCTCCTCA<br>SEQ ID NO: 29387 |
| | | AA | DVMMTQIPLSLSVTPGQPASISCKSSQSLLHSEG KTYLYWYLQKPGQPPQLLIFEVSNRVSGVPDRFS GRGSGTDFTLKISRVEAEDVGVYYCMQSIQYPIT FGQGTRLEIK<br>SEQ ID NO: 25382 | QVQLVESGGGVVQPGRSLRLSCAASGFTFSSYGMH WVRQAPGKGLEWVALIWYDGSNKYHADSVKGRF TISRDNSKNTLYLQMNSLRAEDTAVYYCARRYSSS WSGGMDVWGQGTTVTVSS<br>SEQ ID NO: 29388 |

FIGURE 50
(Continued)

| | | | |
|---|---|---|---|
| iPS:434095 | 21-225_52F10 | NA | GACATCCAGATGACCCAGTCTCCATCCTCACTGTCTGTATCTGTAGGAGACAGAGTCACCATCACTTGTCGGGCGAGTCAGGGTATTAGTAATTATTTAGGCTGGTTTCAGCAGAAACCAGGGAAAGCCCCGAAGTCCCTGATTTATGCTGCATCTAGTTTGCAAAGTGGGGTCCCATCAAGGTTCAGCGGCAGTGGATCTGGGACAGATTTCACTCTCACCATCAGCAGCCTACAGCCTGAAGATTTTGCAACTTATTACTGCCAACAGTATAATAGTTATCCTCCGACGTTCGGCCAAGGGACCAAGGTGGAAATCAAA | CAGGTGCAGCTGGTGGAGTCTGGGGGAGGCGTGGTCCAGCCTGGGGAGGTCCCTGAGACTCTCCTGTGCAGCGTCTGATTCACCTTCAGTTTCTATGGCATGCACTGGGTCCGCCAGGCTCCAGGCAAGGGGCTGGAGTGGGTGGCAGTTATATGGACGATGGAAGTAATAAATACTATCCAGACGACAATTCCAAGAACACGCTGTTTCTGCAAATGATGAGCCTGAGAGCCGAGGACACGGCTGTGTATTACTGTGCGAGAGATTCTGTATAGCAGCAGCTGGTTGTTGACTACTGGGGCCAGGGAACCCTGGTCACCGTCTCCTCA |
| | | | SEQ ID NO: 29389 |
| | | AA | DIQMTQSPSSLSVSVGDRVTITCRASQGISNYLGWFQQKPGKAPKSLIYAASSLQSGVPSRFSGSGSGTDFTLTISSLQPEDFATYYCQQYNSYPPTFGQGTKVEIK | QVQLVESGGGVVQPGRSLRLSCAASGFTFSFYGMHWVRQAPGKGLEWVAVIWDDGSNKYYADSVKGRFTISRDNSKNTLFLQMMSLRAEDTAVYYCARDSLYSSSWLFDYWGQGTLVTVSS |
| | | | SEQ ID NO: 25383 |
| iPS:434097 | 21-225_52H10 | NA | GACATCCAGATGACCCAGTCTCCATCTTCCGTGTCTGCATCTGTAGGAGACAGAGTCACCATCACTTGTCGGGCGAGTCAGGATATTAACAGTTGGTTAGCCTGGTATCAGCAGAAACCAGGGAAAGCCCCTAAACTCCTGATCTATGTTGCATCCAGTTTGCAAAGTGGGGTCCCATCAAGGTTCAGCGGCAGTGGATCTGGGACAGATTTCACTCTCACCATCAGGAGCCTGCAGCCTGAAGATTTTGCTACTTACTATTGTCAACAGGCTAAAAGTTTCCCATTCACTTTCGGCCCTGGGACCAAAGTGGATATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTACATATGCAGTGGGTGCGACAGGCCCCTGGACAAGGCTTGAGTGGATGGGATGGATCAACCCTAACAATGGTGGCACACAGTATGCACAGAAGTTTCAGGGCGGGTCACCATGACCAGGGACACGTCCATCAGCACAGCCTACATGGAACTGAGCAGGCTGAGATCTGACCTGTACACGGCCGTGTATTACTGTGCGAGAGATGGCCGACACGGCGTCCTTTGACTACTGGGGCCAGGGAACCCTGGTCACCGTCTCCTCG |
| | | | SEQ ID NO: 29390 |
| | | | SEQ ID NO: 25385 |
| | | | SEQ ID NO: 29391 |

FIGURE 50
(Continued)

| | | | |
|---|---|---|---|
| iPS:434101 | 21-225_52H12 | AA | DIQMTQSPSSVSASVGDRVTITCRASQDINSWLAWYQQKPGKAPKLLIYVASSLQSGAPSRFSGSGSGTDFTLTIRSLQPEDFATYYCQQAKSFPFTFGPGTKVDIK<br>SEQ ID NO: 25386 | QVQLVQSGAEVKKPGASVKVSCKASGYTFTGYHMQWVRQAPGQGLEWMGWINPNNGGTQYAQKFQGRVTMTRDTSISTAYMELSRLRSDDTAVYYCARDGTSSFDYWGQGTLVTVSS<br>SEQ ID NO: 29392 |
| | | NA | GACATCCAGATGACCCAGTCTCCATCCTCCCTGTCTGCATCTGTAGGAGACAGAGTCACCATCACTTGCCGGGCAAGTCAGGGCATAAGAAATAATTTAGGCTGGTATCAGCAGAAACCAGGGAAAGCCCCTAAGCGCCTGATCTATGTGCATCCAGTTTGCAAAGTGGGGTCCCATCAAGGTTCAGCGGCAGTGGATCTGGGACAGATTCACTCTCACAACAGCAGCCTGCAGCCTGAAGATTTTGCAACTTATTACTGTCTACAGTATAATAGTTATCCATTCACTTTCGGCCCTGGGACCAAAGTGGATATCAAA<br>SEQ ID NO: 25387 | GAGGTGCAGCTGGTGGAGTCTGGGGGAGGCCTGGTCAAGCCTGGGGGGTCCCTGAGACTCTCCTGTGCAGCCTCTGGATTCACCTTCAGTAGCTATAGCATGAACTGGGTCCGCCAGGCTCCAGGGAAGGGGCTGGAGTGGGTCTCATCCATTAGTGGTAGTAGTACTTACATATACTACGCAGACTCAGTGAAGGGCCGATTCACCGTCTCCAGAGACAACGCCAAGAACTCACTGTATCTGCAAGTGAACAGCCTGAGAGCCGAGGACACGGCTGTGTATTACTGTGCGAGAGTCAACTCCTTTGACTACTGGGGCCAGGGAACCCTGGTCACCGTCTCCTCA<br>SEQ ID NO: 29393 |
| | | AA | DIQMTQSPSSLSASVGDRVTITCRASQGIRNNLGWYQQKPGKAPKRLIYGASSLQSGVPSRFSGSGSGTEFTLTISSLQPEDFATYYCLQYNSYPFTFGPGTKVDIK<br>SEQ ID NO: 25388 | EVQLVESGGGLVKPGGSLRLSCAASGFTFSSYSMNWVRQAPGKGLEWVSSISGSSTYIYYADSVKGRFTVSRDNAKNSLYLQVNSLRAEDTAVYYCARVNSFDYWGQGTLVTVSS<br>SEQ ID NO: 29394 |

FIGURE 50
(Continued)

| | | | |
|---|---|---|---|
| iPS:434103 | 21-225_53G1 | NA | GACATCCAGATGACCCAGTCTCCATCTCCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTATCCTGCATCCAGTT TACAAAGTGGGGTCCCATCAAGGTTCAGCGGC AGCGGATCTGGGACAGAATTCAGTCTCACAAT CAGCAGCCTGCAGCCTGAAGATTTTGCAACTT ATTACTGTCTACAGGATAATAGTTACCCATTC ACTTTCGGCCCTGGGACCAAAGTGGATATCAA A<br>SEQ ID NO: 25389 | GAGGTGCAGCTGGTGGAGTCTGGGGGAGGCTG GTCAAGCCTGGGGAGTCCCTGAGACTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGGGGC AGCACCTGGGGCCAGGGAACCCTGGTCACCGTCT CCTCA<br>SEQ ID NO: 29395 |
| | | AA | DIQMTQSPSSLSASVGDRVTITCRASQGIRNDLG WYQQKPGKAPKRLIYPASSLQSGVPSRFSGSGSG TEFSLTISSLQPEDFATYYCLQDNSYPFTFGPGTK VDIK<br>SEQ ID NO: 25390 | EVQLVESGGGLVKPGESLRLSCAASGFTFSSYSMN WVRQAPGKGLEWVSSISGSSSYIYYADSVKGRFTIS RDNAKNSLYLQMNSLRAEDTAVYYCARDRGSTW GQGTLVTVSS<br>SEQ ID NO: 29396 |
| iPS:434105 | 21-225_53D2 | NA | GACATCCAGATGACCCAGTCTCCATCTCCCT GTCTGCATCTGTAGGAGACAGAGTCACCATCA CTTGCCGGGCAAGTCAGGACAGAGTCACCATCA TTAGGCTGGTATCAGCAGAAAACCAGGGAAAG CCCCTAAGCGCCTGATCTATGCTGCATCCAGT TTGCAAAGTGGGGTCCCATCAAGGTTCAGCGG CAGTGGATCTGGGACAGCCTGAAGATTTGCAACT TCAGCAGCCTGCAGCCTGAAGATTTTGCAACT TATTACTGTCTACAACATATAGATACCCGCT CACTTTCGGCGGAGGGACCAAGGTGGAGATC AAA<br>SEQ ID NO: 25391 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAACTATGGCAT GCACTGGGTCCGCCAGGCTCCAGGCAAGGGCT GGAATGGGTGACAGTTGTATGGGATGATGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTACGAGAGGGCCTTG GCTTTACGGAGACTACTGGGGCCAGGGAGCCC TGGTCACCGTCTCCTCA<br>SEQ ID NO: 29397 |

FIGURE 50
(Continued)

| | | | | |
|---|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNRYPLTFGGG TKVEIK | QVQLVESGGGVVQPGRSLRLSCAASGFTFSNYGM HWVRQAPGKGLEWVTVVWDDGSNKYYADSVKG RFTISRDNSKNTLYLQMNSLRAEDTAVYYCTRGLG FTGDYWGQGALVTVSS |
| | | | SEQ ID NO: 25392 | SEQ ID NO: 29398 |
| iPS:434107 | 21-225_53E2 | NA | GACATCCAGATGACCCAGTCTCCATCCTCCCT GTCTGCATCTGTAGGAGACAGAGTCACCATCA CTTGCCGGGCAAGTCAGAGTTTAGCCACTAT TTAAATTGGTATCAGCAGAAACCAGGGAAAG CCCCTAAGCTCCTGATCTTTGCTGTATCCAGTT TGCAAAGTGGGGTCCCATCACGGTTCAGTGGC AGTGGATCTGGGACAGATTTCACTCTCCCAT CAGTAGTTTGCAACCTGAAGATTTTGCAATTT ACTTCTGTCAACACAGAGTTTCAGTACCCCATTC ACTTTCGGCCCTGGGACCAAAGTGGATATCAA A | GAGGTGCAGTTGTTGGAGTCTGGGGGAGGCTTGA TACAGCCTGGGGGGTCCCTGAGACTCTCCTGTGC AGCCTCTGGATTCACCTTTAGGAGAGTATGCCATG AGCTGGGTCCGCCAGGCTCCAGGGAAGGGGCTG GAGTGGGTCTCAGCTATTAGTGGTAGTGGTGTA ACACATTCTACGCAGCAGACTCCGTGAAGGGCCGGTT CCACTCCAGAGACAATTCCAAGAACACGCTG TATTTGCAAATGAACACCCTGAGAGCCGACGAC ACGGCCGTATATTACTGTGCGAAAAAGGTCGTGG ATACAGCCATGGCTCTTGACTACTGGGGCCAGGG AACCCTGGTCACCGTCTCCTCA |
| | | | SEQ ID NO: 25393 | SEQ ID NO: 29399 |
| | | AA | DIQMTQSPSSLSASVGDRVTITCRASQSFSHYLN WYQQKPGKAPNLLIFAVSSLQSGVPSRFSGSGSG SDFTLPISSLQPEDFAIYFCQQSFSTPFTFGPGTKV DIK | EVQLLESGGGLIQPGGSLRLSCAASGFTFRSYAMS WVRQAPGKGLEWVSAISGSGGNTFYADSVKGRFTI SRDNSKNTLYLQMNTLRADDTAVYYCAKKVVDT AMALDYWGQGTLVTVSS |
| | | | SEQ ID NO: 25394 | SEQ ID NO: 29400 |

FIGURE 50
(Continued)

| | | | |
|---|---|---|---|
| iPS:434111 | 21-225_53H2 | NA | GACATCCAGATGACCCAGTCTCCATCCTCCT GTCTGCATCTGTAGGAGACAGAGTCACCATCA CTTGCCAGGCGAGTCAGGACATTAGCAACTAT TTACATTGGTATCAGCAGAAACCAGGGAAAGC CCCTCAGCTCCTGATCTACGATGCATCCAATTT GGAAACAGGGGTCCCATCAAGGTTCACTGGA AGTGGATCTGGGACAGATTTTACTTTCACCAT CAGCAGCCTGCAGCCTGAAGATATTGCAACAT ATTACTGTCATCAGTATGATAATCTCCCGCTCA CTTTCGGCGGAGGGACCAAGGTGGAGATCAA A |
| | | | SEQ ID NO: 25395 |
| | | AA | DIQMTQSPSSLSASVGDRVTITCQASQDISNYLH WYQQKPGKAPQLLIYDASNLETGVPSRFTGSGS GTDFTFTISSLQPEDIATYYCHQYDNLPLTFGGG TKVEIK |
| | | | SEQ ID NO: 25396 |
| iPS:434115 | 21-225_53E4 | NA | GACATCCAGATGACCCAGTCTCCATCCTCACT GTCTGCATCTGTAGGAGACAGAGTCACCATCA CTTGTCGGGCGAGTCAGGTCAGTCATTAGCAAAGC TTAGCCTGGTTTCAGCAGAAACCAGGGAAAGC CCCTAAGTCCCTGATCTCTGCTGATCCAGTTT GCAAAGTGGGGTCCCATCAAAGTTCAGCGGCA GTGGATCTGGGACAGATTTCACTCTCACCATC AGCAGCCTGCCAACAGTATCATAGTTACCACTCA CTACTGCCAACAGTATCATAGTTACCACTCA CTTTCGGCCGTGGACCAAAGTGGATATCAAA |
| | | | SEQ ID NO: 25397 |

| | | |
|---|---|---|
| | CAGGTGCAGCTGGTGGAGTCTGGGGGAGGCGTG GTCCAGCCTGGGAGGTCCCTGAGACTCTCCTGTG CAGCCCTCTGGATTCACCTTCAGTAGCTATGGCAT GCACTGGGTCCGCCAGGCTCCAGGCAAGGGGCC GGAGTGGGTGGCAGTTATATCATATGGTGAAGT AATAAATACATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGCGAGGCGGGGAG CAGCTCGTCCTGGCTACGGTATGGACGTCTGGGG CCAAGGGACCACGGTCACCGTCTCCTCA | |
| | SEQ ID NO: 29401 | |
| | QVQLVESGGGVVQPGRSLRLSCAASGFTFSSYGMH WVRQAPGKGPEWVAVISYGGSNKYHADSVKGRFT ISRDNSKNTLYLQMNSLRAEDTAVYYCARRGAAR PGYGMDVWGQGTTVTVSS | |
| | SEQ ID NO: 29402 | |
| | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGTCAT GAGCTGGGTCCGCCAGGCTCCAGGGAAGGGGCT GGAGTGGGTCTCAGGTATTAGTGGTAGTGGTGGT CGCACATACTACGCAGACTCCGTGAAGGGCCGG TTCAACATCTCCAGAGACAATTCCAAGAACACGC TGTATCTGCAAATGAACAGCCTGAGAGCCGAGG ACACGGCCGTCTATTACTGTGCGAGGGTTGCCCT TTTTGACTACTGGGGCCAGGGAACCCTGGTCACC GTCTCCTCA | |
| | SEQ ID NO: 29403 | |

FIGURE 50
(Continued)

| | | | | |
|---|---|---|---|---|
| | | AA | DIQMTQSPSSLSASVGDRVTITCRASQVISNYLAWFQQKPGKAPKSLISAASSLQSGVPSKFSGSGSGTDFTLTISSLQPEDFATYYCQQYHSYPLTFGRGTKVDIK<br><br>SEQ ID NO: 25398 | EVQLLESGGGLVQPGGSLRLSCAASGFTFSSYVMSWVRQAPGKGLEWVSGISGSGGRTYYADSVKGRFNISRDNSKNTLYLQMNSLRAEDTAVYYCARVALFDYWGQGTLVTVSS<br><br>SEQ ID NO: 29404 |
| iPS:434117 | 21-225_53C6 | NA | GACATCCAGATGACCCAGTCTCCATCCTCCCTGTCTGCATCTGTAGGAGACAGAGTCACCATCACTTGCCGGGCAAGTCAGTACAGTAGCGACTATTTAAATTGGTATCAGCAGAAACCAGGGAAAGCCCCTAAGGTCCTGATCTTTGCTGCATCCAGTTTGAAAAGTGGGGTCCCATCAAGGTTCAGTGGCAGTGGATCTGGGACAGATTTCACTCTCACCATCAGCAGTCTGGAACCTGAAGATTTTGCGACTTACTTCTGTCAACAGAGTTACAGTACCCCGTTCACCTTCGGCCAAGGGACACGACTGGAGATTAAA<br><br>SEQ ID NO: 25399 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAACTGGGTCCGCCAGGCTCCAGGGAAGGGGCTGGAGTGGGTCTCAGCTATTAGTGGTAGTGGTGGTGCCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTATTGTGCGAAACCTCTAGTGGGAGCCCATGATGCTTTTGAAATCTGGGGCCAAGGGACAAATGGTCACCGTCTCTTCA<br><br>SEQ ID NO: 29405 |
| | | AA | DIQMTQSPSSLSASVGDRVTITCRASQYSSDYLNWYQQKPGKAPKVLIFAASSLKSGVPSRFSGSGSGTDFTLTISSLEPEDFATYFCQQSYSTPFTFGQGTRLEIK<br><br>SEQ ID NO: 25400 | EVQLLESGGGLVQPGGSLRLSCAASGFTFSSYAMNWVRQAPGKGLEWVSAISGSGGATYYADSVKGRFTISRDNSKNTLYLQMNSLRAEDTAVYYCAKPLVGAHDAFEIWGQGTMVTVSS<br><br>SEQ ID NO: 29406 |

FIGURE 50
(Continued)

| | | | |
|---|---|---|---|
| iPS:434119 | 21-225_53E6 | NA | GACATCCAGATGACCCAGTCTCCATCCTCCT GTCTGCCTCTGTAGGCGCCAGAGTCACCATCA CTTGCCGGGCAAGTCAGGGCATTAGAAATGAT TTAGGCTGGTATCAGCAGAAATCCGGGGAAAGC CCCTAAGCGCCTGATCTATGCTGCATCCAATT CCCAAAGTGGGGTCCCATCAAGGTTCAGCGGCA GTGGATCTGGGACAGACTTCACTCTCACTATC AGCAGCCTGCAGCCTGAAGATTTTGCAACTTA TTTCTGTCTACAACATAATCGTTACCCGCTCAC TTTCGGCGGAGGGACCAAGGTGGAGATCAAA SEQ ID NO: 25401 | CAGGTCCAGCTGGTGGAGTCTGGGGGAGGCGTG GTCCAGCCTGGGAGGTCCCTGAGACTCTCCTGTA CAACGTCTGGATTCACCTTCAGTGACTATGGCAT CCACTGGGTCCGCCAGGCTCCAGGCAAGGGGCT GGAGTGGGTGGCAGTTATATGGTATGATGAAAGT AATAAATACTATGGAGACTCCGTGAAGGGCCGA TTCGCCATCTCCAGAGACAATTCCAAGAACACGC TGTATCTGCAAATGAACAGCCTGAGAGCCGAGG ACACGGCTGTGTATTATTGTGTGAGAGAACTGGG GATGACGTCTGACTACTGGGGCCAGGGAACCCT GGTCACCGTCTCCTCA SEQ ID NO: 29407 |
| | | AA | DIQMTQSPSSLSASVGARVTITCRASQGIRNDLG WYQQNPGKAPKRLIYAASNLQSGVPSRFSGSGS GTEFTLTISSLQPEDFATYFCLQHNRYPLTFGGGT KVEIK SEQ ID NO: 25402 | QVQLVESGGGVVQPGRSLRLSCTTSGFTFSDYGIH WVRQAPGKGLEWVAVIWYDESNKYYGDSVKGRF AISRDNSKNTLYLQMNSLRAEDTAVYYCVRELGM TSDYWGQGTLVTVSS SEQ ID NO: 29408 |
| iPS:434121 | 21-225_53F6 | NA | GACATCCAGATGACCCAGTCTCCATCCTCCCT GTCTGCATCTGTAGGAGACAGAGTCACCATCA CTTGCCAGGCGAGTCAAGACATTACCAACTAT TTAGATTGGTATCAGCAGAAACCGGGGAAAG CCCCTAAACTCCTGATCTACGATGCATCCAAT TTGGGAACAGGGGTCCCATCAAGGTTCAGTGG AAGTGGATCTGGGACAGATTTTACTTTCACCA TCAGCAGCCTGCAGCCTGAAGATATTGCAACA TATTACTGTCAACAGTGTGATAATCTCCCGCTC ACTTTCGGCGGAGGGACCAAGGTGGAGATCA AA SEQ ID NO: 25403 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCATATGGTGGAAGT AATAAATACGATGCAGACTCCGTGAAGGGCCGA TTCACCATCTCCAGAGACAATTCCAAGAACACGC TGTATCTGCAAATGACCAGCCTGAGAGCTGAGG ACACGGCTGTGTATTACTGTGCGAGAGACGGGC AGCTCGTCCAGGTACGGTATGGACGTCTGGGGC CAAGGGACCACGGTCACCGTCTCCTCA SEQ ID NO: 29409 |

FIGURE 50
(Continued)

| | | | |
|---|---|---|---|
| iPS:434123 | 21-225_53F7 | AA | DIQMTQSPSSLSASVGDRVTITCQASQDITNYLD WYQQKPGKAPKLLIYDASNLGTGVPSRFSGSGS GTDFTFTISSLQPEDIATYYCQQCDNLPLTFGGGT KVEIK<br><br>SEQ ID NO: 25404 | QVQLVESGGGVVQPGRSLRLSCAASGFTFSSYGMH WVRQAPGKGLEWVAVISYGGSNKYDADSVKGRFT ISRDNSKNTLYLQMTSLRAEDTAVYYCARRRAARP GYGMDVWGQGTTVTVSS<br><br>SEQ ID NO: 29410 |
| | | NA | GACATCCAGATGTCCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAACCTCCTGATCTATGCTGCATCCAGTT TGCAAAGTGGGGTCCCATCAAGGTTCAGCGGC AGTGGCTCTGGGACAGATTTCACTCTCACCAT CAGCAGCCTGCAGCCTGAAGATTTTGCAATTT ACTATTGTCAGCAGGCTAACAGTTTCCCATTC ACTTTCGGCCCTGGGACCAAAGTGGATATCAA A<br><br>SEQ ID NO: 25405 | CAGGTGCAGCTGGTGCAGTCTGGGGCTGAGGTG AAGAAGCCTGGGGCCTCAGTGAAGGTCCTGC AAGGCTTCTGATACACCTTCACCGGCTACCATA TGCACTGGGTGCGACAGGCCCCTGGACAAGGGC TTGAGTGGATGGGATGGATCAACAGAAGTTCAGGGCAG CGGCACAAACTATGCACAGAAGTTCAGGGCAG GGTCACCATGACCAGGGACACGTCCATCAGCAC AGCCTACATGGAGCTGAACAGGCTGACATCTGA CGACACGGCCGTGTATTACTGTGCGAGAGACGGT ACCAGCAGTTTGACTACTGGGGCCAGGGAACC CTGGTCACCGTCTCCTCA<br><br>SEQ ID NO: 29411 |
| | | AA | DIQMSQSPSSVSASVGDRVTITCRASQGISRWLA WYQQKPGKAPNLLIYAASSLQSGVPSRFSGSGS GTDFTLTISSLQPEDFAIYYCQQANSFPFTFGPGT KVDIK<br><br>SEQ ID NO: 25406 | QVQLVQSGAEVKKPGASVKVSCKASGYTFTGYHM HWVRQAPGQGLEWMGWINPNNNGTNYAQKFQGR VTMTRDTSISTAYMELNRLTSDDTAVYYCARDGTS SFDYWGQGTLVTVSS<br><br>SEQ ID NO: 29412 |

FIGURE 50
(Continued)

| | | | | |
|---|---|---|---|---|
| iPS:434127 | 21-225_53H8 | NA | GAAATTGTGTTGACGCAGTCTCCAGGCACCCT GTCTTTGTCTCCAGGGGAAAGAGCCACCCTCT CCTGCAGGGCCAGTCAGTCAGATATTACAAGCAGC TACTTAGCCTGGTACCAGCAGAAACCTGGCCA GGCTCCCAGGCTCCTCATCTATGGTGCGTCCG GCAGGGCCACTGGCATCCCAGACAGTTCAGT GGCAGTGGGTCTGGGACAGACTTCACCCTCAC CATCAGCAGACTGGAGCCTGAAGATTTTGCAG TGTATTACTGTCAGCAGTTTGAAAGCTCACC ATGTGCAGTTTTGGCCAGGGGACCAACCTGGA GATCAAA <br><br>SEQ ID NO: 25407 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTATGGCAT GCACTGGGTCCGCCAGGCTCCAGGCAAGGGGCT GGAGTGGGTGGCAGTTATATGCAGACTCCGTGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGCCGTAT TGGGTACTTTGACTCCTGGGGCCAGGGAACCCTG GTCACCGTCTCCTCA <br><br>SEQ ID NO: 29413 |
| | | AA | EIVLTQSPGTLSLSPGERATLSCRASQSITSSYLA WYQQKPGQAPRLLIYGASGRATGIPDRFSGSGS GTDFTLTISRLEPEDFAVYYCQQFESSPMCSFGQ GTNLEIK <br><br>SEQ ID NO: 25408 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARARIGY FDSWGQGTLVTVSS <br><br>SEQ ID NO: 29414 |
| iPS:434129 | 21-225_53B12 | NA | GACATCCAGATGACCCAGTCTCCATCCTCCCT GTCTGCATCTGTAGGAGACAGAGTCACCATCA CTTGTCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A <br><br>SEQ ID NO: 25409 | CAGGTGCAGCTGGTGGAGTCTGGGGGAGGCGTG GTCCAGCCTGGGGAGGTCCCTGAGACTCTCCTGTG CAGCGTCTGGATTCACCTTCAGTAACTTTGGCAT GCACTGGGTCCGCCAGGCTCCAGGCAAGGGGCT GGAGTGGGTGGCAGTTGTATGCAGACTCCGTGAAAT AATAGATACTATGCAGACTCCGTGAAGGGCCGA TTCACCATCTCCAGAGACAATTCCAAGAACACGC TCTATCTGCAAATGCACAGCCTGAGAGCCGAGG ACACGGCTGTGTATTACTGTGCGAGGAACTGGG ATTTCTCTCTGACTTCTGGGGCCAGGGAACCCTCA GTCACCGTCTCCTCA <br><br>SEQ ID NO: 29415 |

FIGURE 50
(Continued)

| | | | |
|---|---|---|---|
| iPS:434131 | 21-225_54D3 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br><br>SEQ ID NO: 25410 | QVQLVESGGGVVQPGRSLRLSCAASGFTFSNFGMH WVRQAPGKGLEWVAVVWYDGNNRYYADSVKGR FTISRDNSKNTLYLQMHSLRAEDTAVYYCARELGF LSDFWGQGTLVTVSS<br><br>SEQ ID NO: 29416 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGGTCCCATCAAGATTCAGCGG CAGTGGATCTGGGACAGAATTCACTCTCACAA TCAGCAGCCTGCAGCCTGAAGATTTTGCAACT TATTACTGTCTACAACATAATAGTTACCCATTC ACTTTCGGCCCTGGGACCAAAGTGGATATCAA A<br><br>SEQ ID NO: 25411 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAACTATGGCAT GCACTGGGTCCGCCAGGCTCCAGGCAAGGGGCT GGAGTGGGTGGCAGTTACATGATTTGATGAAAT AATAACTACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACTGGGG TTCCTTTCTGATTATTGGGGCCAGGGAACCCTGG TCACCGTCTCCTCA<br><br>SEQ ID NO: 29417 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br><br>SEQ ID NO: 25412 | QVQLVESGGGVVQPGRSLRLSCAASGFTFSNYGM HWVRQAPGKGLEWVAVTWFDGNNNYYADSVKG RFTISRDNSKNTLYLQMNSLRAEDTAVYYCARELG FLSDYWGQGTLVTVSS<br><br>SEQ ID NO: 29418 |

FIGURE 50
(Continued)

| | | | |
|---|---|---|---|
| iPS:434133 | 21-225_54G3 | NA | GACATCCAGATGACCCAGTCTCCATCTTCCGT GTCTGCATCTGTAGGAGACAGAGTCACCATCA CTTGTCGGGCGAGTCAGGTATTAGCAGCTGG TTAGCCTGGTATCAGCAGAAACCAGGGAAAG CCCCTAAACTCCTGATCTATGATGCATCCAGTT TGCAAAGTGGGGTCCCATCAAGGTTCAGCGGC AGTGGATCTGAGACAGATTTCACTCTCACCAT CAGCAGCCTGCAGCCTGAAGATTTTGCAACTT ACTATTGTCAACAGGCTAACAGTTTCCCGTGG ACGTTCGGCCAAGGGACCAAGGTGGAAATCA AA<br><br>SEQ ID NO: 25413 | GAGGTGCAGCTGTTGGAGTCTGGGGGAGGCTTG GTACAGCCTGGGGGGTCCCTGAGACTCTCCTGTG CAGCCTCTGGATTCACCTTTAGCACCTATGCCAT GAGTTGGGTCCGCCAGGCTCCAGGGAAGGGGCT GGAGTGGGTCTCAGCTATTAGTGGTAGTGGTGTT AACACATTCTACGCAGACTCCGTGAAGGGCCGGT TCACCATCTCCAGAGACAATTCCAAGAACACGCT GTTTCTGCAAATGAACAGCCTGAGAGCCGAGGA CACGGCCGTATATTACTGTGCGAAACTGGGGAA GGACTACTACTACGGTATGGACGTCTGGGGC CAAGGGACCACGGTCACCGTCTCCTCA<br><br>SEQ ID NO: 29419 |
| | | AA | DIQMTQSPSSVSASVGDRVTITCRASQGISSWLA WYQQKPGKAPKLLIYDASSLQSGVPSRFSGSGSE TDFTLTISSLQPEDFATYYCQQANSFPWTFGQGT KVEIK<br><br>SEQ ID NO: 25414 | EVQLLESGGGLVQPGGSLRLSCAASGFTFSTYAMS WVRQAPGKGLEWVSAISGSGVNTFYADSVKGRFTI SRDNSKNTLFLQMNSLRAEDTAVYYCAKLGKDYY YYGMDVWGQGTTVTVSS<br><br>SEQ ID NO: 29420 |
| iPS:434135 | 21-225_54H3 | NA | GACATCCAGATGACCCAATCTCCATCTCCCT GTCTGCATCTGTTGGAGACAGAGTCACCATCA CTTGCCGGGCAAGTCAGGACATTAGAAATATT TTAGGCTGGTATCAGCAGACAGAAACCAGGGAAAG CCCCTAAGCGCCTGATCTATGCTGCATCCAAT TTGCAAAGTGGAGTGCCATCAAGGTTCAGCGG CAGTGGATCTGGGACAGATTTCACTCTCACAA TCAGCAGCCTGCAGCCTGAGGATTTCGCAACT TATTACTGTCTACAGTATAATAGTTACCCGTG GACGTTCGGCCAAGGGACCAAGGTGGAAATC AAA<br><br>SEQ ID NO: 25415 | GAGGTGCAGCTGTGGTGGAGTCTGGGGGAGGCCTG GTCAAGCCTGGGGGGTCCCTGAGACTCTCCTGTG CAGCCTCTGGATTCACCTTCAGTAGCTATAGCAT GATCTGGGTCCGCCAGGCTCCAGGGAAGGGGCT GGAGTGGGTCTCATCCATTAGTGGTACTAGTAGT TACATATACTACGCAGAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGGGAATGACTACA GTAATTTGGGGCCAGGGAACCCTGGTCACCGTCT CCTCA<br><br>SEQ ID NO: 29421 |

FIGURE 50
(Continued)

| | | | |
|---|---|---|---|
| | | AA | DIQMTQSPSSLSASVGDRVTITCRASQDIRNILG WYQQKPGKAPKRLIYAASNLQSGVPSRFSGSGS GTEFTLTISSLQPEDFATYYCLQYNSYPWTFGQG TKVEIK<br>SEQ ID NO: 25416 | EVQLVESGGGLVKPGGSLRLSCAASGFTFSSYSMI WVRQAPGKGLEWVSSISGTSSYIYYADSVKGRFTIS RDNAKNSLYLQMNSLRAEDTAVYYCAGMTTVIW GQGTLVTVSS<br>SEQ ID NO: 29422 |
| iPS:434137 | 21-225_54D4 | NA | GATATTGTGATGACCCAGACTCCACTCTCTCT GTCCGTCACCCCTGGACAGCCGGCTCCATGT CCTGCAAGTCTAGTCAGAGCCTCCTGCATAGT GAGGGAAAGACCTATTTGTATTGGTACCTGCG GAAGCCAGGCCAGCCTCCACAGTTCCTGATCT TTGAAGTTTCCAACGGGTTCTCTGGAGTGCCA GATAGGTTCAGTGGCAGCGGGTCAGGGACAG AATTCACACTGAAAATCAGCCGGTGGAGGCT GAGGATGTTGGGATTTATTACTGCATGCAAAG TATACAGTTTCCATTCACTTTCGGCCCTGGGAC CAAAGTGGATATCAAA<br>SEQ ID NO: 25417 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTATGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAACATTCCAAGAACACGC TGTATCTGCAAATGAACAGCCTGAGAGCCGAGG ACACGGCTGTGTATTACTGTGCGAGAAGGTATAG CAGCAGCTGTGTGGGGCGTATGGACGTCTGGGG CCAAGGGACCACGGTCACCGTCTCCTCA<br>SEQ ID NO: 29423 |
| | | AA | DIVMTQTPLSLSVTPGQPASMSCKSSQSLLHSEG KTYLYWYLRKPGQPPQFLIFEVSNRFSGVPDRFS GSGSGTEFTLKISRVEAEDVGIYYCMQSIQPPFTF GPGTKVDIK<br>SEQ ID NO: 25418 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTVSS<br>SEQ ID NO: 29424 |

FIGURE 50
(Continued)

| | | | |
|---|---|---|---|
| iPS:434141 | 21-225_54C6 | NA | GACATCCAGATGACCCAGTCTCCATCCCCT GTCTGCCTCTGTAGGCGCCAGAGTCACCATCA CTTGCCGGGCAAGTCAGGGCCATTAGAAATGAT TTAGGCTGGTATCAGCAGAAACCGGGAAAGC CCCTAAGCGCCTGATCTATGCTGCATCCAATT GCAAAGTGGGGTCCCATCAAGGTTCAGCGGCA GTGGATCTGGGACAGAGAATTCACTCTCACTTA AGCAGCCTGCAGCCTGAAGATTTTGCAACTTA TTTCTGTCTACAGCATAATCGTTACCGCTCAC TTTCGGCGGAGGGACCAAGGTGGAGATCAAA SEQ ID NO: 25419 | CAGGTCCAGCTGGTGGAGTCTGGGGGAGGCGTG GTCCAGCCTGGGAGGTCCCTGAGACTCTCCTGTA CAACGTCTGGATTCACCTTCAGTGACTATGGCAT CCACTGGGTCCGCCAGGCTCCAGGCAAGGGGCT GGACTGGGTGGCAGTTATATGGTATGATGAAAAT AATAAATACTATGCAGACTCCGTGAAGGGCCGA TTGGCCATCTCCAGAGACAATTCCAAGAACACGC TGTATCTGCAAATGAACAGCCTGAGAGCCGAGG ACACGGCTGTGTATTATTGTGTGAGAGAACTGGG GATGACGTCTGACTACTGGGGCCAGGGAACCCT GGTCACCGTCTCCTCA SEQ ID NO: 29425 |
| | | AA | DIQMTQSPSSLSASVGARVTITCRASQGIRNDLG WYQQNPGKAPKRLIYAASNLQSGVPSRFSGSGS GTEFTLTISSLQPEDFATYFCLQHNRYPLTFGGGT KVEIK SEQ ID NO: 25420 | QVQLVESGGGVVQPGRSLRLSCTTSGFTFSDYGIH WVRQAPGKGLDWVAVIWYDENNKYYADSVKGRF AISRDNSKNTLYLQMNSLRAEDTAVYYCVRELGM TSDYWGQGTLVTVSS SEQ ID NO: 29426 |
| iPS:434143 | 21-225_54G7 | NA | GACATCCAGATGACCCAGTCTCCATCCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCTAGGTTCAGCGG CAGTGGATCTGGGACAGAATTCACTCTCACAA TCAGCAGCCTGCAGCCTGAAGATTTTGCAACT TATTACTGTCTACATCATAATACTTACCCATTC ACTTTCGGCCCTGGGACCAAAGTGGATATCAA A SEQ ID NO: 25421 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGGTATGAGGAAAG TAATAAATACTATCCAGAGACTCCGTGAAGGCCG ATTCACCATCTCCAAATGAACAGCCTGAGAGCCGAG CTGTATCTGCAAATGAACAGCCTGAGAGCCGAG GACACGGCTGTGTATTACTGTGCGAGAGAATTGG GGTTCCTCTGACTACTGGGGCCAGGGAACCCT GGTCACCGTCTCCTCA SEQ ID NO: 29427 |

FIGURE 50
(Continued)

| | | | | |
|---|---|---|---|---|
| iPS:434145 | 21-225_55B1 | AA | DIQMTQSPSSLSASVGDRVTITCRASQGIRNDLG WYQQKPGKAPKRLIYAASSLQSGVPSRFSGSGS GTEFTLTISSLQPEDFATYYCLHHNTYPFTFGPGT KVDIK<br><br>SEQ ID NO: 25422 | QVQLVESGGGVVQPGRSLRLSCAASGFTFSNYGM HWVRQAPGKGLEWVAVIWYEESNKYYGDSVKGR FTISRDNSKNTLYLQMNSLRAEDTAVYYCARELGF LSDYWGQGTLVTVSS<br><br>SEQ ID NO: 29428 |
| | | NA | GACATCCAGATGACCCAGTCTCCATCTTCCGT GTCTGCATCTGTAGGGGACAGAGTCACCATCA CTTGTCGGGCGAGTCAGGTTATTAGCCGCTGG TTAGCCTGGTATCAGCAGAAACCAGGGAAAG CCCCTAACCTCCTGATCTATGCTGCATCCAGTT TGCAAAGTGGGGTCCCATCAAGGTTCAGCGGC AGTGGATCTGGGACAGATTTCACTCTGACCAT CAGCAGCCTGCAGCCTGAAGATTTTGCAACTT ACTATTGTCAACAGGCTAACAGTTTCCCATTC ACTTTCGGCCCTGGGACCAAAGTGGATCTCAA A<br><br>SEQ ID NO: 25423 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATT TCCACTGGGTGCGACAGGCCCCTGGTCAAGGGCT TGAGTGGATGGGATGGATCCACCTAACAATAAT GCCACAAACTATGCACAGAAGTTTCAGGGCAGG GTCACCATGACCAGGGACACGTCCATCAGCACA GCCTACATGGAGCTGAGCAGGCTGAGATCTGAC GACACGGCCGTGTATTACTGTGCGAAGGATGGC AGATGTCCTTTGACTACTGGGGCCAGGGAACCC TGGTCACCGTCTCCTCA<br><br>SEQ ID NO: 29429 |
| | | AA | DIQMTQSPSSVSASVGDRVTITCRASQVISRWLA WYQQKPGKAPNLLIYAASSLQSGVPSRFSGSGS GTDFTLTISSLQPEDFATYYCQQANSFPFTFGPGT KVDLK<br><br>SEQ ID NO: 25424 | QVQLVQSGAEVKKPGASVKVSCKASGYTFTGYYF HWVRQAPGQGLEWMGWIHPNNNATNYAQKFQGR VTMTRDTSISTAYMELSRLRSDDTAVYYCAKDGRS SFDYWGQGTLVTVSS<br><br>SEQ ID NO: 29430 |

FIGURE 50
(Continued)

| | | | | |
|---|---|---|---|---|
| iPS:434147 | 21-225_55E1 | NA | GAAATAGTGATGACGCAGTCTCCAGCCACCCT GTCTGTGTCTCCAGGGGAAAGAGCCACCCTCT CCTGCAGGGCCAGTCAGTGTTAGCAGCGAC TTAGCCTGGTACCAGCTGAAACCTGGCCAGGC TCCCAGGCTCCTCATCTATGATGCATCCGCCA GGGCCACTGGTATCCCAGCCAGGTTCAGTGGC AGTGGGTCTGGGACAGAGTTCACTCTCACCAT CAGCAGCCTGCAGTCTGAAGATTTTGCATTTT ATTACTGTCAGCAGTATTATAACTGGCCTCTC ACTTTCGGCGGAGGGACCAAGGTGGAGATCA AA | GAGGTGCAACTGTTGGAGTCTGGGGGAGGCTTG GTACAGCCTGGGGGGTCCCTGAGACTCTCCTGTG CAGCCCTCTGATTCACCTTTAGCAGCTATGCCAT GAGCTGGGTCCGCCAGGCTCCAGGGAAGGGCT GGAGTGGGTCTCAGTATTAGTGGTCGTGGTAGT AGCACATTCTACGCAGACTCCGTGAAGGGCCGGT TCACCATCTCCAGAGACACAATTCCAAGAACACGT GTATCTGCAAATGAACAGCCTGAGAGCCGAGGA CACGGCCGTTTTTACTGTGCGAAAGATCACGGT ATAGTGGGAACCTGTTTACTTTGACTACTGGGGCC AGGGAACCCTGGTCACCGTCCTCCTCA |
| | | | SEQ ID NO: 25425 | SEQ ID NO: 29431 |
| | | AA | EIVMTQSPATLSVSPGERATLSCRASQSVSSDLA WYQLKPGQAPRLLIYDASARATGIPARFSGSGSG TEFTLTISSLQSEDFAFYYCQQYYNWPLTFGGGT KVEIK | EVQLLESGGGLVQPGGSLRLSCAASGFTFSSYAMS WVRQAPGKGLEWVSAISGRGSSTFYADSVKGRFTI SRDNSKNTLYLQMNSLRAEDTAVFYCAKDHGIVG TIYFDYWGQGTLVTVSS |
| | | | SEQ ID NO: 25426 | SEQ ID NO: 29432 |
| iPS:434149 | 21-225_55H1 | NA | GATATTGTGATGACCCAGACTCCACTCTCTCT GTCCGTCACCCTGGACAGCCGGCCTCCATCT CCTGCAAATCTAGTCAGAGCCTCCTGCATAGT GAAGGAAAGACCTATTTGTATTGGTACCTGCA GAAGCCAGGCCAGCCTCCACAGTTCCTGATCT TTGAAGTTTCCCACCGGTTCTGGAGTGCCA GATAGGTTCAGTGGCAGCGGGTCAGGGACAG ATTTCACTCTGAAAATCAGCGGGGTGGAGGCT GAGGATGTTGGGGTTTATTACTGCATGCAAAG TATACAGCTTCCATTCACTTTCGGCCCTGGGAC CAAAGTGGATATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCGGGGGTATGGACGTCTGGGG CCAAGGGACCACGGTCACCGTCTCCTCA |
| | | | SEQ ID NO: 25427 | SEQ ID NO: 29433 |

FIGURE 50
(Continued)

| | | | |
|---|---|---|---|
| | | AA | DIVMTQTPLSLSVTPGQPASISCKSSQSLLHSEGK TYLYWYLQKPGQPPQFLIFEVSHRFSGVPDRFSG SGSGTDFTLKISRVEAEDVGVYYCMQSIQLPFTF GPGTKVDIK<br>SEQ ID NO: 25428 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTSS<br>SEQ ID NO: 29434 |
| iPS:434151 | 21-225_55C2 | NA | GATGTTATGATGACCCAGATTCCACTCTCTCTG TCCGTCACCCCTGGACAGCCGGCCTCCATCTC CTGCAAGTCTAGTCAGAGCCTCGTGCATAGTG AAGGAAAGACCTATTTGTATTGGTATTTGCAG AAGCCAGGCCAGCCTCCACAGCTCCTGATCTT TGAAGTTTCCAACCGGGTCTCTGGAGTGCCAG ATAGGTTCAGTGGCAGAGGGTCAGGGACAGA TTTCACACTGAAAATCAGCCGGGTGGAGGCTG AGGATGTTGGGGTTTATTACTGCATGCAAAGT ATACTGTATCCGATCACCTTCGGCCAAGGGAC ACGACTGGAGATTAAA<br>SEQ ID NO: 25429 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGGCT GGAGTGGGTGGCACTTATATGGTATGATGGAAGT AATAAATACCATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGCGCGAGAAGGTATAG CAGCAGCTGGTCGGGCGGTATGGACGTCTGGGG CCAAGGGACCACGGTCACCGTCCTCCTCA<br>SEQ ID NO: 29435 |
| | | AA | DVMMTQIPLSLSVTPGQPASISCKSSQSLVHSEG KTYLYWYLQKPGQPPQLLIFEVSNRVSGVPDRFS GRGSGTDFTLKISRVEAEDVGVYYCMQSILYPIT FGQGTRLEIK<br>SEQ ID NO: 25430 | QVQLVESGGGVVQPGRSLRLSCAASGFTFSSYGMH WVRQAPGKGLEWVALIWYDGSNKYHADSVKGRF TISRDNSKNTLYLQMNSLRAEDTAVYYCARRYSSS WSGGMDVWGQGTTVTSS<br>SEQ ID NO: 29436 |

FIGURE 50
(Continued)

| | | | |
|---|---|---|---|
| iPS:434155 | 21-225_55B3 | NA | GACATCCAGATGACCCAGTCTCCATCCTCCT GTCTGCATCTGTAGGAGACAGAGTCACCATCA CTTGCCGGGCAAGTCAGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTAGATCTGGGACAGAATTCACTCTCACAA TCAGCAGCCTGCAGCCTGAAGATTTTGCATCT TATTACTGTCTACAACATATAGTTACCCATTC ACTTTCGGCCCTGGGACCAAAGTGGATATCAA A SEQ ID NO: 25431 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGGCT GGAGTGGGTGGCAGTTATATGGTTTGATGAAAT AATAAATACTATGAAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGTGAGGGAACTGG ATTTCTCTGACTACTGGGGCCAGGGAACCCTG GTCACCGTCTCCTCA SEQ ID NO: 29437 |
| | | AA | DIQMTQSPSSLSASVGDRVTITCRASQGIRNDLG WYQQKPGKAPKRLIYAASSLQSGVPSRFSGSRS GTEFTLTISSLQPEDFASYYCLQHNSYPFTFGPGT KVDIK SEQ ID NO: 25432 | QVQLVESGGGVVQPGRSLRLSCAASGFTFSSYGMH WVRQAPGKGLEWVAVIWFDGNNKYEDSVKGRF TISRDNSKNTLYLQMNSLRAEDTAVYYCVRELGFL SDYWGQGTLVTVSS SEQ ID NO: 29438 |
| iPS:434157 | 21-225_55D4 | NA | GACATCCAGATGACCCAGTCTCCATCCTCTCT GTTTGCATCTGTAGGAGACAGAGTCACCATCA CTTGTCGGGCGAGTCAGGACATTAGCAATTAT TTAATCTGGTTTCAGCAGAAACCAGGGAAAGC CCCTAAGTCCCTGATTTATACTGCATCCAGTT GCAAAGTGGGGTCCCCTCAAAGTTCAGCGGCA GTGGATTTGGGACAGATTCACTCTCACCATC AGCAACCTGCAGCCTGAAGATTTTGCGACTTA TTACTGCCAACAGTATCATAGTTTCCCTCTCAC TTTCGGCGGAGGGACCAAGGTGGAGATCAGA SEQ ID NO: 25433 | GAGGTGCAACTGGTGGAGTCTGGGGGAGGCTG GTCAAGCCTGGGGGGTCCCTGAGACTCTCCTGTG CAGCCTCTGGATTCACCTTCAATAGTTATAGGAT GAACTGGGTCCGCCAGGCTCCAGGGAAGGGGCT GGAGTGGGTCTCATCCATTAGTAGTAGTAGTAAT CACATAGACTACGCAGACTCAGTGAAGGCCGA TTCACCATCTCCAGAGACAACGCCAAAAACTCAC TATATTTGCAAATGAACAGCCTGAGAGCCGAGG ACACGGCTTTATATTACTGTGCAGAGAGGACTGA CTACTGGGGCCAGGGAACCCTGGTCTCCGTCTCC TCA SEQ ID NO: 29439 |

FIGURE 50
(Continued)

| | | | |
|---|---|---|---|
| iPS:434159 | 21-225_55B8 | AA | DIQMTQSPSSLFASVGDRVTITCRASQDISNYLIW FQQKPGKAPKSLIYTASSLQSGVPSKFSGSGFGT DFTLTISNLQPEDFATYYCQQYHSFPLTFGGGTR VEIR<br>SEQ ID NO: 25434 | EVQLVESGGGLVKPGGSLRLSCAASGFTFNSYRMN WVRQAPGKGLEWVSSISSSSNHIDYADSVKGRFTIS RDNAKNSLYLQMNSLRAEDTALYYCARGTDYWG QGTLVSVSS<br>SEQ ID NO: 29440 |
| | | NA | GACATCCAGATGACCCAGTCTCCATCCTCCCT GTCTTCATCTGTAGGAGACAGAGTCACCATCA CTTGCCGGGCAAGTCAGGCCATTAGAAATGAT TTAGGCTGGTATCAGCAGAAACCAGGAAAG CCCCTAAGCGCCTGATCATGTCATTCAGG TTGCAAAGTGGGGTCCCATCCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCTCTC ACTTTCGGCGGAGGGACCAAGGTGGGGATCA AA<br>SEQ ID NO: 25435 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGATGAAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAATGTT TGACTACTGGGGCCAGGGAACCCTGGTCACCGTC TCCTCA<br>SEQ ID NO: 29441 |
| | | AA | DIQMTQSPSSLSSSVGDRVTITCRASQAIRNDLG WYQQKPGKAPKRLIHAAFRLQSGVPSRFSGSGS GTEFTLTISSLQPEDFATYYCLQHNSYPLTFGGG TKVGIK<br>SEQ ID NO: 25436 | QVQLVESGGGVVQPGRSLRLSCAASGFTFSDYGM HWVRQAPGKGLEWVAVIWYDENNKYYADSVKGR FTISRDNSKNTLYLQMNSLRAEDTAVYYCTREWFD YWGQGTLVTVSS<br>SEQ ID NO: 29442 |

FIGURE 50
(Continued)

| | | | | |
|---|---|---|---|---|
| iPS:434161 | 21-225_55F9 | NA | GATATTGTGATGACCCAGACTCCACTCTCT GTCCGTCACCCCTGGACAGTCGGCCTCCATCT CCTGCAAGTCTAGTCAAAGCCTCCTGCATAGT GAAGGAAAGACCTATTTGTATTGGTACTTGCA GAAGCCAGGCCAGCCTCCACAGTCTCTGATCT ATGAAGTTTCCAACCGGTTCTCTGGAGTGCCA GATAGGTTCAGCGGCAGCGGGTCAGGACAG ATTTTACACTGAAAATCAGCGGGTGGAGGCT GAGGATGTTGGGGTTTATTACTGCATACAAAG TATACAACTTCCGATCACCTTCGGCCAAGGGA CACGACTGGAGATTAAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATGGTATGATGAAAT GGCAAATATTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGGTCGGGCGGTATGGACGTCTGGGG CCAAGGGACCACGGTCACCGTCTCCTCA |
| | | | SEQ ID NO: 25437 | SEQ ID NO: 29443 |
| | | AA | DIVMTQTPLSLSVTPGQSASISCKSSQSLLHSEGK TYLYWYLQKPGQPPQLLIYEVSNRFSGVPDRFSG SGSGTDFTLKISRVEAEDVGVYYCIQSIQLPITFG QGTRLEIK | QVQLVESGGGVVQPGRSLRLSCAASGFTFSSYGMH WVRQAPGKGLEWVAVIWYDGNGKYYADSVKGRF TISRDNSKNTLYLQMNSLRAEDTAVYYCARRYSSS WSGGMDVWGQGTTVTVSS |
| | | | SEQ ID NO: 25438 | SEQ ID NO: 29444 |
| iPS:434163 | 21-225_50H1 | NA | GACATCCAGATGACCCAGTCTCCATCCTCCC GTCTGTCTTCTGTAGGAGACAGAGTCACCATCA CTTGCCAGGCGAGTCAAGACATTAGCAACTAT TTAGATTGGTATCAGCAGAAACCAGGGAAAG CCCCTAAACTCCTGATATACGATGCATCCAAT TTGGAAACAGGGGTCCCATCAAGGTTCAGTGG AAGTGGATCTGGGACAGATTTGCTTTCACCA TCAGCAGCCTGCAGCCTGAAGATATTGCAACA TATTACTGTCAACAGTGTGATAATCTCCCGCTC ACTTTCGGCGGAGGGACCAAGGTGGAGATCA AA | CAGGTGCAGTTGGTGGAGTCTGGGGGAGGCGTG GTCCAGCCTGGGAGGTCCCTGAGACTCTCCTGTG CAGCCTCTGGATTCACCTTCAGTAGCTATGCAT GCACTGGGTCCGCCAGGCTCCAGGCAAGGGCT GGAGTGGGTGGTCAATTATATCATATGTGGAAGT AATAAATACGATGCAGACTCCGTGAAGGGCCGA TTCACCATCTCCAGAGACAATTCCAAGAACACGC TGTATCTGCAAATGACCAGCCTGAGAGCTGAGG ACACGGCTGTGTATTACTGTGCGAGACGACGGGC AGTCGTCCAGGTACGGTATGGACGTCTGGGGC CAAGGGATCACGGTCACCGTCTCCTCA |
| | | | SEQ ID NO: 25439 | SEQ ID NO: 29445 |

FIGURE 50
(Continued)

| | | | | |
|---|---|---|---|---|
| iPS:434165 | 21-225_50F2 | AA | DIQMTQSPSPSASVGDRVTITCQASQDISNYLDWYQQKPGKAPKLLIYDASNLETGVPSRFSGSGSGTDFAFTISSLQPEDIATYYCQQCDNLPLTFGGGTKVEIK<br>SEQ ID NO: 25440 | QVQLVESGGGVVQPGRSLRLSCAASGFTFSSYGMHWVRQAPGKGLEWVSIISYGGSNKYDADSVKGRFTISRDNSKNTLYLQMTSLRAEDTAVYYCARRRAARPGYGMDVWGQGITVTVSS<br>SEQ ID NO: 29446 |
| | | NA | GACATCCAGATGACCCAGTCTCCATCCTCCCTGTCTGCATCTGTAGGAGACAGAGTCACCATCACTTGCCGGGCAAGTCAGAGCATTCTCAGCTATTTGAATTGGTATCAGCAGAAACCAGGAAAGGCCCCTAAACTCCTGATCTATGTTGCATCCAGTTTCCAAAGTGGGGTCCCATCAAGGTTCAGTGGCAGTGGATCTGGGACAGATTTCACTCTCACCATCAGCAGTCTGCAACCTGATGATTTTGCAACTTACTACTGTCAACAGAGTTACAGTCCCCCTCTCACTTTCGGCGGAGGGACCAAGGTGGAGATCAAAA<br>SEQ ID NO: 25441 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGACTCCAGGCAAGGGGCTGGAGTGGGTGGCAGTTATATGCATGATGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGACGAGCAGCTCGGGACCTTTGACTACTGGGGCCAGGGAACCCTGGTCACCGTCTCCTCA<br>SEQ ID NO: 29447 |
| | | AA | DIQMTQSPSSLSASVGDRITITCRASQSILSYLNWYQQKPGKAPKLLIYVASSFQSGVPSRFSGSGSGTDFTLTISSLQPDDFATYYCQQSYSPPLTFGGGTKVEIK<br>SEQ ID NO: 25442 | QVQLVESGGGVVQPGRSLRLSCAASAFTFSSYGMHWVRQTPGKGLEWVAVIWHDGSNKYYADSVKGRFTISRDNSKNTLYLQMNSLRAEDTAVYYCARDEQLGTFDYWGQGTLVTVSS<br>SEQ ID NO: 29448 |

FIGURE 50
(Continued)

| | | | |
|---|---|---|---|
| iPS:434167 | 21-225_50F3 | NA | GACATCCAGATGACCCAGTCTCCATCTCCCT<br>GTCTGCATCTGTAGGAGACAGAGTCACCATCA<br>CTTGTCGGGCGAGTCAGGATATTAGCAGTGG<br>TTGGCCTGGTTTCAGCAGAAACCAGGGAAAGC<br>CCCTAAGCTCCTGATCTATGCTGCATCCAGTTT<br>GCAAAATGGGGTCCCGTCAAGGTTCAGCGGCA<br>GTGGATCTGGGACAGATTCACTCTCACCATC<br>AGCAGCCTGCAACAGACTAACAGTTTCCATTCA<br>CTATTGCCAACAGACTAACAGTTTCCATTCA<br>CTTTCGGCCCTGGGACCAAAGTGGATATCAAA | GAGGTGCAGCTGTTGGAGTCTGGGGGAGGCTTG<br>GTACAGCCTGGGGGGTCCCTGAGACTCTCCTGTG<br>CAGCCTCTGGATTCACCTTTAGAACCTATGCCAT<br>GACCTGGGTCCGCCAGGCTCCAGGGAAGGGCT<br>GGAGTGGGTCTCAGCTATCAGTGGTAGTGGTGTT<br>AACTCATTCTACGCAGACTCCGTGAAGGGCCGGT<br>TCACCATCTCCAGAGACAATTCCAGAACACGCT<br>GTATCTGCAAATGAACAGCCTGAGAGCCGAGGA<br>CACGGCCGTATATTACTGTGCGAAAGCAAGGC<br>AGTGGCTGGGTCACACTGGTTGCACCCTGGGGC<br>CAGGGAACCCTGGTCACCGTCTCCTCA |
| | | | SEQ ID NO: 25443 | SEQ ID NO: 29449 |
| | | AA | DIQMTQSPSSVSASVGDRVTITCRASQDISSWLA<br>WFQQKPGKAPKLLIYAASSLQNGVPSRFSGSGS<br>GTDFTLTISSLQPEDFATYYCQQTNSFPFTFGPGT<br>KVDIK | EVQLLESGGGLVQPGGSLRLSCAASGFTFRTYAMT<br>WVRQAPGKGLEWVSAISGSGVNSFYADSVKGRFTI<br>SRDNSENTLYLQMNSLRAEDTAVYYCAKARAVAG<br>SHWFDPWGQGTLVTVSS |
| | | | SEQ ID NO: 25444 | SEQ ID NO: 29450 |
| iPS:434169 | 21-225_50C4 | NA | GACATCCAGATGACCCAGTCTCCATCCTCCCT<br>GTCTGCATCTGTAGGAGACAGAGTCACCATCA<br>CTTGCCGGGCAAGTCAGGGCATTAGAAATGAT<br>TTAGGCTGGTATCAGCAGAAACCAGGGATAGC<br>CCCTAAGCGCCTGATCTATGCTGCATCCAGTT<br>GCAAAGTGGGGTCCCATCAAGGTTCAGCGGCA<br>GTGGATCTGGGACAGACTTCACTCTCACAATC<br>AGCAGCCTGCAGCCTGAAGATTTTGCAACTTA<br>TTACTGTCTACAGCATATAATCGTTACCCATTCAC<br>TTTCGGCCCTGGGACCAAAGTGGATATCAA | CAGGTGCAGCTGGTGGAGTCTGGGGGAGGCGTG<br>GTCCAGCCTGGGAGGTCCCTGAGACTCTCCTGTG<br>CAGCCGTCTGATTCACCTTCAGTGACTATGGCAT<br>GCACTGGGTCCGCCAGGCTCCAGGCAAGGGCT<br>GGAGTGGGTGGCAGTTATATGGTATGAAGAAAC<br>TAATAAATACTATCCAGAGACAATCCAAGAACACG<br>ATTCACCATCTCCAGAGACAATTCCAAGAACACG<br>CTGTATCTGCAAATGAACAGCTGAGAGGCGAG<br>GACACGGCTGTGTATTACTGTGCGAGAGAAGTGG<br>GGTTCCTGAATGACTACTGGGGCCAGGGAATCCT<br>GGTCACCGTCTCCTCA |
| | | | SEQ ID NO: 25445 | SEQ ID NO: 29451 |

FIGURE 50
(Continued)

| | | | | |
|---|---|---|---|---|
| iPS:434171 | 21-225_50G4 | AA | DIQMTQSPSSLSASVGDRVTLTCRASQGIRNDLG WYQQKPGIAPKRLIYAASSLQSVPSRFSGSGSG TEFTLTISSLQPEDFATYYCLQHNRYPFTFGPGTK VDIK | QVQLVESGGGVVQPGRSLRLSCAASGFTFSDYGM HWVRQAPGKGLEWVAVIWYEETNKYYADSVKGR FTISRDNSKNTLYLQMNSLRGEDTAVYYCAREVGF LNDYWGQGILVTVSS |
| | | | SEQ ID NO: 25446 | SEQ ID NO: 29452 |
| | | NA | GACATCCAGATGACCCAGTCTCCAACCTCCCT GTCTGCATCTGTGGGAGACAGAGTCACCATCA CTTGCCAGGCGAGTCAGGACATTACCAACTTT TTAAATTGGTATCAGCAGAAACCAGGGAAAG CCCCTAAGCTCCTGATCTACGATGCCTCCAATT TGGAAACAGGGGTCCCATCAAGGTTCAGTGGA AGTGGATCTGGGACAGATTTTACTTTCACCAT CAGCAGCCTCAGCCTGAAGATATTGCAACAT ATTACTGTCAACAGTATGATAATCTGATCACC TTCGGCCAAGGGACACGACTGGAGATTAAA | CAGGTGCAGCTGGTGCAGTCTGGGGCTGAGGTG AAGGAGCCTGGGGCTCAGTGAAGGTTTCCTGCA AGGCATCTGGATACACCTTCACCAGTTACTATAT ACACTGGGTGCGACAGGCCCCTGGACAAGGGCT TGAGTGGATGGGAGTAATCAACCCTAGTAATGGT AGAACAAGCTACGCACAGAAGTTCCAGGGCAGA GTCACCATGACCAGGGACACGTCCACGAGCACA GTCTACATGGAGCTGAGCAGCCTGAGATCTGAG GACACGGCCGTGTATTACTGTGCGAGATCGA GGAGATGGTTACTACTTCTACTACGGTATGGACG TCTGGGGCCAAGGGACCACGGTCACCGTCTCCTC A |
| | | | SEQ ID NO: 25447 | SEQ ID NO: 29453 |
| | | AA | DIQMTQSPTSLSASVGDRVTITCQASQDITNFLN WYQQKPGKAPKLLIYDASNLETGVPSRFSGSGS GTDFTFTISSLQPEDIATYYCQQYDNLITFGQGTR LEIK | QVQLVQSGAEVKEPGASVKVSCKASGYTFTSYYIH WVRQAPGQGLEWMGVINPSNGRTSYAQKFQGRVT MTRDTSTSTVYMELSSLRSEDTAVYYCARDRGDG YYFYYGMDVWGQGTTVTVSS |
| | | | SEQ ID NO: 25448 | SEQ ID NO: 29454 |

FIGURE 50
(Continued)

| | | | |
|---|---|---|---|
| iPS:434175 | 21-225_55A11 | NA | GACATCCAGATGACCCAGTCTCCATCCTCACT GTCTGCATCTGTAGGAGACAGAGTCACCATCA CTTGTGTCGGGCGAGTCAGGACATTAACATTTAT TTAGCCTGGTTTCAGCAGAAACCAGGGAAAGC CCCTAAGTCCCTGATCTATGCTGCATCCAGTTT GCAAAGTGGGGTCCCATCGAAGTTCAGCGGCA GTGGATCTGGGACAGATTTCACTCTCACCATC AGCAGTCTGCAGCCTGAAGATTTTGCAACTTA TTACTGCCAACAGTATAATAGTTATCCTCTCAC TTTCGGCGGAGGGACCAAGGTGGAGATCAAA SEQ ID NO: 25449 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGACTCCAGGCAAGGGCT GGAGTGGGTGGCAGTTATATCATATGTTGGAAGT ACTAAATACTATGCAGACTCCGTGAGGGGCCGAT TCACCATCTCCAGAGACAATTCCAAGAACACGCT GTATCTGCAAATGAACAGCCTGAGAACTGAGGA CACGGCTGTGTATTACTGTGCGAGAGGGAGAGGT CGATATAGTGACTACGGTCATGATGCTTTTGATA TCTGGGGCCAAGGGACAATGGTCACCGTCTCTTC A SEQ ID NO: 29455 |
| | | AA | DIQMTQSPSSLSASVGDRVTITCRASQDINIYLA WFQQKPGKAPKSLIYAASSLQSVPSKFSGSGSG TDFTLTISSLQPEDFATYYCQQYNSYPLTFGGGT KVEIK SEQ ID NO: 25450 | QVQLVESGGGVVQPGRSLRLSCAASGFTFSSYGMH WVRQTPGKGLEWVAVISYVGSTKYYADSVRGRFT ISRDNSKNTLYLQMNSLRTEDTAVYYCARGRGRYS DYGHDAFDIWGQGTMVTVSS SEQ ID NO: 29456 |
| iPS:434177 | 21-225_56A1 | NA | GACATCGTCATGACCCAGTCTCCAGACTCCCT GGCTGTGTCTCTGGGCGAGAGGGCCACCATCA ACTGCAAGTCCAGCCAGAGTGTTTTATACATAGT TCCAACAATAAGAACTACTTAGTTTGGTACCA GCAGAAACCAGGACAGCCTCCTAACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTGCAGCAA TATTATAGTACTCCTCGACGTTCGGCCAAGG GACCAAGGTGGAAATCAAA SEQ ID NO: 25451 | CAGGTACAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGCTGGGATGGATGCACCTAACAGTGG TAACACAGGCTATGCACAGAAGTTCCAGGCAG AGTCACCATGACCAGGAACACCTCCATAAGCAC AGCCTACATGGAGCTGAGCAGCCTGAGATCTGA GGACACGGCCGTGTATTACTGTGCATATAGCAGT GGCTGGTACGTTTTGACTACTGGGGCCAGGAA CCCTGGTCACCGTCTCCTCA SEQ ID NO: 29457 |

FIGURE 50
(Continued)

| | | | |
|---|---|---|---|
| iPS:434179 | | AA | DIVMTQSPDSLAVSLGERATINCKSSQSVLHSSN NKNYLVWYQQRPGQPPNLLIYWASTRESGVPD RFSGSGSGTDFTLTISSLQAEDVAVYYCQQYYST PPTFGQGTKVEIK<br>SEQ ID NO: 25452 | QVQLVQSGAEVKKPGASVKVSCKASGYTFTNYDIN WVRQATGQGLEWLGWMHPNSGNTGYAQKFQGR VTMTRNTSISTAYMELSSLRSEDTAVYYCAYSSGW YVFDYWGQGTLVTVSS<br>SEQ ID NO: 29458 |
| | | NA | GACATCCAGATGACCCAGTCTCCATCCTCCCT GTCTGCATCTGTAGGAGACAGAGTCACCATCA CTTGCCGGGCAAGTCAGGACATTAGAAATAAT TTAGGCTGGTATCAGCAGAAACCAGGGAAAG CCCCTAAGCGCCTGATCAATGCTGCATCCAGT TTACAAAGTGGGGTCCCATCCAAGGTTCAGCGG CAGTGGATCTGGGACAGATTCACTCTCACAA TCAGCAGCCTGCAGCCTGAAGATATTGCAACT TATTACTGTCTACAGGATAATAGTCACCCGTT CACTTTCGGCGGAGGGACCAAGGTGGAGATC AAA<br>SEQ ID NO: 25453 | GAGGTGCAGCTGGTGGAGTCTGGGGGAGGCCTG GTCAAGTTTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGTACT TACATATACTACGGAGACTCAGTGAAGGGCCGA TTCACCATCTCCGAGACAACGCCAAGAACTCAC TATATCTGCAGATGAACAGCCTGAGAGCCGAGG ACACGGCTGTGTATTACTGTGCGAGAGATCGGGG CAGCAGCTGGGGCCAGGGAACCCTGGTCACCGT CTCCTCA<br>SEQ ID NO: 29459 |
| | 21-225_56F1 | AA | DIQMTQSPSSLSASVGDRVTITCRASQDIRNNLG WYQQKPGKAPKRLINAASSLQSGVPSRFSGSGS GTEFTLTISSLQPEDFATYYCLQDNSHPFTFGGGT KVEIK<br>SEQ ID NO: 25454 | EVQLVESGGGLVKFGGSLRLSCAASGFTFSSYSMN WVRQAPGKGLEWVSSISSSSTYIYGDSVKGRFTIS RDNAKNSLYLQMNSLRAEDTAVYYCARDRGSSW GQGTLVTVSS<br>SEQ ID NO: 29460 |

FIGURE 50
(Continued)

| | | | |
|---|---|---|---|
| iPS:434181 | 21-225_56B2 | NA | GACATCCAGATGACCCAGTCTCCATCCTCCT GTCTGCATCTGTAGGAGACAGAGTCACCATCA CTTGCCGGGCAAGTCAGAGTTTAGCCACTAT TTAAATGGTATCAGCAGAAACCAGGGAAAG CCCCTAACCTCCTGATCTTTGCTGTATCCAGTT TGCAAAGTGGGGTCCCATCAAGGTTCAGTGGC AGTGGATCTGGGACAGATTTCACTCTCACCAT CAGTAGTCTGCAACCTGAAGATTTTGCAATTT ACTTCTGTCAACAGAGTTACAGTACCCCATTC ACTTTCGGCCCTGGGACCAAAGTGGATATCAA A | GAGGTGCAGTTGTTGGAGTCTGGGGGAGGCTTGA TACAGCCTGGGGGGGTCCCTGAGACTCTCCTGTGC AGCCTCTGGATTCACCTTTAGGAGCTATGCCATG AGCTGGGTCCGCCAGGCTCCAGGGAAGGGGCTG GAGTGGGTCTCAGCTATTAGTGGTAGTGGTGTA ACACATTCTACGCAGACTCCGTGAAGGGCCGGTT CACCATCTCCAGAGACAATTCCAAGAACACGCTG TATTTGCAAATGAACACCCTGAGAGCCGACGAC ACGGCCGTATATTACTGTGCGAAAAAGGTCGTGG ATACAGCCATGGCTCTTGACTACTGGGGCCAGGG AACCCTGGTCACCGTCCTCTCA |
| | | | SEQ ID NO: 25455 | SEQ ID NO: 29461 |
| | | AA | DIQMTQSPSSLSASVGDRVTITCRASQSFSHYLN WYQQKPGKAPNLLIFAVSSLQSGVPSRFSGSGSG TDFTLTISSLQPEDFAIYFCQQSYSTPFTFGPGTK VDIK | EVQLLESGGGLIQPGGSLRLSCAASGFTFRSYAMS WVRQAPGKGLEWVSAISGSGGNTFYADSVKGRFTI SRDNSKNTLYLQMNTLRADDTAVYYCAKKVVDT AMALDYWGQGTLVTVSS |
| | | | SEQ ID NO: 25456 | SEQ ID NO: 29462 |
| iPS:434187 | 21-225_56A5 | NA | GACATCCAGATGACCCAGTCTCCATCCTCCCT GTCTGCATCTGTAGGAGACAGAGTCACCATCA CTTGCCGCGGGCAAGTCAGGACATTAGAAATCTT TTAGGCTGGTATCAGCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGACCTTCACTCTCACAT CAGCAGCCTGCAGCCTGAAGATTTTGCAACTT ATTACTGTCTACAGTATAATAGTTACCACCTCA CTTTCGGCGGAGGGACCAAGGTGGATATCAGA | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGT TACATATACTACCGCAGAGACAGTGAAGGGCCGAT TCACCATCTCCAGAGACAACGCCAAGAACTCACT ATATCTGCAAATGAACAGCCTGAGAGAGCCGAGGA CACGGCTGTGTATTACTGTGCGAGAGAGTGGCTACT TTTGACTACTGGGGCCAGGGAACCCTGGTCACCG TCTCCTCA |
| | | | SEQ ID NO: 25457 | SEQ ID NO: 29463 |

FIGURE 50
(Continued)

| | | | |
|---|---|---|---|
| iPS:434189 | | AA | DIQMTQSPSSLSASVGDRVTITCRASQDIRNLLG WYQQKPGKAPKRLIYAASSLQSGVPSRFSGSGS GTEFTLTISSLQPEDFATYYCLQYNSYPFTFGPGT KVDIR<br>SEQ ID NO: 25458 | EVQLVESGGGLVKPGGSLRLSCAASGFTFSSYSMN WVRQAPGKGLEWVSSISGSSSYIYYADSVKGRFTIS RDNAKNSLYLQMNSLRAEDTAVYYCARVATFDY WGQGTLVTVSS<br>SEQ ID NO: 29464 |
| | 21-225_56E5 | NA | GACATCCAGATGACCCAGTCTCCATCTTCCGT GTCTGCATCTGTAGGCGACAGAGTCACCATCA CTTGTCGGGCGAGTCAGGGTATTAGGAAGTGG TTAGCCTGGTATCAGCAGAAACCAGGGAAAG CCCCTAAGCTCCTGATCTATGCTGCATCCAGTT TGCAAAGTGGGGTCCCGTCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A<br>SEQ ID NO: 25459 | CAGGTGCAGCTGGTGCAGTCTGGGGCTGAGGTG AAGAAGCCTGGGGCCTCAGTGAAGGTCTCCTGCC AGGCTTCTGGATACACCTTCACCGGCTACCATAT GCACTGGGTGCGACAGGCCCCTGGACAAGGGCT TGAGTGGATGGGATGGATCAACCCTAACAATAAT GCCACAAACTATGCACAGAAGTTTCAGGGCAGG GTCACCATGACCAGGGACACGTCCATCAGCACA GCCTACATGGAACTGAGGAGGCTGAGATCTGAC ACCTGTCTTTGACTACTGTGCGAGAGATGGC ACCTGTCTTTGACTACTGGGGCCAGGGAACCC TGGTCACCGTCTCCTCA<br>SEQ ID NO: 29465 |
| | | AA | DIQMTQSPSSVSASVGDRVTITCRASQGIRKWLA WYQQKPGKAPKLLIYAASSLQSGVPSRFSGSGS GTDFTLTISSLQPEDFATYYCQQANSFPFTFGPGT KVDIK<br>SEQ ID NO: 25460 | QVQLVQSGAEVKKPGASVKVSCQASGYTFTGYHM HWVRQAPGQGLEWMGWINPNNNATNYAQKFQGR VTMTRDTSISTAYMELRRLRSDDTAVYHCARDGTS VTMTRDTSISTAYMELRRLRSDDTAVYHCARDGTS SFDYWGQGTLVTVSS<br>SEQ ID NO: 29466 |

FIGURE 50
(Continued)

| | | | | |
|---|---|---|---|---|
| iPS:434191 | 21-225_56B6 | NA | GACATCCAGATGACCCAGTCTCCATCCTCCT GTCTGTATCTGTAGGAGACAGAGTCACCATCA CTTGCCGGGCAAGTCAGAGACATTTTCAGATAT TTAAATTGGTATCAGCAGAAACCAGGAAAGAG CCCCTAAGCTCCTGATCTTTGCTGCATCCAGTT TCCAAAGTGGGGTCCCATCAAGGTTCAGTGGC AGTGGATCTGGGACAGACTTCACTCTCACCAT CAGCAGCCTACAACCTGAAGATTTTGCAACTT ACTACTGTCAACAGACTTACAGTCCCCCTCC ACTTTCGGCGGAGGGACCAAGGTGGAGATCA AA | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTAGACTCCGTGA TAATAAATATTATGTAGACTCCGTGAAGGGCCGA TTCACCATCTCCAGAGACAATTCCAAGAATACGC TGTATCTGCAAATGAACAGCCTGAGACCGAGG ACACGGCTGTGTATTACTGTGCGAGAGACGAGC AGCTCGGGACCTTTGACTACTGGGGCCAGGGAA CCCTGGTCACCGTCTCCTCA |
| | | | SEQ ID NO: 25461 | SEQ ID NO: 29467 |
| | | AA | DIQMTQSPSSLSVSVGDRVTITCRASQSIFRYLN WYQQKPGRAPKLLIFAASSFQSGVPSRFSGSGSG TDFTLTISSLQPEDFATYYCQQTYSPPLTFGGGTK VEIK | QVQLVESGGGVVQPGRSLRLSCAASGFTFSSYGMH WVRQAPGKGLEWVAVIWHDGSNKYYVDSVKGRF TISRDNSKNTLYLQMNSLRAEDTAVYYCARDEQLG TFDYWGQGFLVTVSS |
| | | | SEQ ID NO: 25462 | SEQ ID NO: 29468 |
| iPS:434193 | 21-225_56C6 | NA | GACATCCAGATGACCCAGTCTCCATCCTCCGT GTCTGCATCTGTGGGAGACAGAGTCACCATCA CTTGTCGGGCGAGTCAGGGTATTAGCAGCTGG TTAGCCTGGTATCAGCAGAAATCAGGAAATGC CCCTAAGCTCCTGATCTATGCTGCATCCAGATT GCAAAGTGGGGTCCCATCAAGGTTCAGCGGCA GTGGATCTGGGTACATATTTCACTCTCATTATCA GCAGCCTGCAGTCTGAAGATTTTGCAACTTAC TATTGTCAACAGGCTAACAGTTTCCCATTCACT TTCGGCCCTGGGACCAAAGTGGATATCAAA | CAGGTGCAGCTGCAGCTGGTGCAGTCTGGGGCTGAGGTG AAGAAGCCTGGGGCCTCAGTGAAGGTCTCCTGC AAGGCTTCTGGATACACCTTCACCGACTACCATA TGCACTGGGTGCGACAGGCCCCTGGACAAGGGC TTGAGTGGATGGGATGGATCAACCCTAACAGAG GTGGCACAAATTATGTACAGAAGTTTCAGGGTAG GGTGCGCCATGACCAATGACACACGTCCATCAGCACA GCCTATATGGAGCTGAGTGGGCTGAGATCTGACG ACACGGCCGTGTATTACTGTGCGAGAGATGGCAC CTGTCTTTGACTATTGGGGCCGGGGAACCCTG GTCACCGTCTCCTCA |
| | | | SEQ ID NO: 25463 | SEQ ID NO: 29469 |

FIGURE 50
(Continued)

| | | | |
|---|---|---|---|
| iPS:434195 | 21-225_56F6 | AA | DIQMTQSPSSVSASVGDRVTITCRASQGISSWLA WYQQKSGNAPKLLIYAASRLQSGVPSRFSGSGS GTYFTLIISSLQSEDFATYYCQQANSFPFTFGPGT KVDIK<br>SEQ ID NO: 25464 | QVQLVQSGAEVKKPGASVKVSCKASGYTFTDYHM HWVRQAPGQGLEWMGWINPNRGGTNYVQKFQGR VAMTNDTSISTAYMELSGLRSDDTAVYYCARDGTS SFDYWGRGTLVTVSS<br>SEQ ID NO: 29470 |
| | | NA | GACATCCAGATGACCCAGTCTCCATCTTCTGT GTGTGCATATGTAGGAGACAGAGTCACCATCA CTTGTCGGGTGAGTCAGGATATTAGCAGCAAATGG TTAGCCTGGTTTCAGCAGAAACCAGGGAAAGC CCCTAAATTCTTGATATATGTTGCATCCGGTTT GCAAAGTGGGGTCCCATCAAGGTTCAGCGGCA GTGGATCTGGGACAGATTTCACTTTCACCATC AGCAGCCTGCAGCCTGAAGATTTTGCAACTTA CTATTGTCAACAGGCTAACAGTTTCCCATTCA CTTTCGGCCCTGGGACCAAAGTGGATATCAAA<br>SEQ ID NO: 25465 | CAGGTGCAGCTGGTGCAGTCTGGGGCTGAGGTG AAGAAGCCTGGGGCCTCAGTGAAGGTCTCCTGC AAGGCTTCTGGATTCACCTTCACCGACTACTATA TGCACTGGGTGCGACAGGCCCCTGGACAAGGGC TTGAGTGGATGGGATGGATCAACCCTAACAGTGG TGGCACAAACTATGCACAGAGAGGTTTCAGGGCAG GGTCACCATGACCAGGGACACGTCCATCAGCAC AGCCTACATGGAACTGAGCAGACTGAGATCTGA CGACACGGCCGTGTATTACTGTACGAGAGAGGG AGCAACTCGTCCGACGGGTTTTGACTACTGGGGC CAGGGAACCCTGGTCACCGTCTCCTCA<br>SEQ ID NO: 29471 |
| | | AA | DIQMTQSPSSVCAYVGDRVTITCRVSQDISKWLA WFQQKPGKAPKFLIYVASGLQSGVPSRFSGSGSG TDFTFTISSLQPEDFATYYCQQANSFPFTFGPGTK VDIK<br>SEQ ID NO: 25466 | QVQLVQSGAEVKKPGASVKVSCKASGFTFTDYYM HWVRQAPGQGLEWMGWINPNSGGTNYAQRFQGR VTMTRDTSISTAYMELSRLRSDDTAVYYCTREGAT RPTGFDYWGQGTLVTVSS<br>SEQ ID NO: 29472 |

FIGURE 50
(Continued)

| | | | |
|---|---|---|---|
| iPS:434197 | 21-225_56C7 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATACTGCATCCAAT TTACAAAGTGGGGTCCCATCAAGGTTCAGCGG CAGTGGATCTGGGACAGAATTCACTCTCACAA TCAGCAGCCTGCAGCCTGAAGATATTGCAACT TATTACTGTCTACAGCATAATAGTTATCCGTG GACGTTCGGCCAAGGGACCAAGGTGGAAATC AAA<br><br>SEQ ID NO: 25467 | CAGGTGCAGCTGGTGGTGCAGTCTGGGGCTGAGGTG AAGAAGCCTGGGGCCTCAGTGAAGGTCTCCTGC AAGGCTTCTGGATACACCTTCACCGGCCACTATA TAAACTGGGTGCGACAGGCCCCTGGACAAGGGC TTGAGTGGATGGCATGGGTCAACCCTAACAGTGG TGGCACAAACTCTGCACAGAAGTTTCAGGGCAG GGTCACCATGACCAGGGACACGTCCATCAGCAC AGTCTACATGGAGCTGAGCAGGCTGAGATCTGA CGACACGGCCGTGTATTACTGTGCGAGGGGAGG GCAGCTCGGCGGGTTTAACTACTACTACTACGGT ATGGACGTCTGGGGCCAAGGGACCACGGTCACC GTCTCCTCA<br><br>SEQ ID NO: 29473 |
| | | AA | DIQMTQSPSSLSASVGDRVTITCRASQGIRNDLG WYQQKPGKAPKRLIYTASNLQSGVPSRFSGSGS GTEFTLTISSLQPEDFATYYCLQHNSYPWTFGQG TKVEIK<br><br>SEQ ID NO: 25468 | QVQLVQSGAEVKKPGASVKVSCKASGYTFTGHYIN WVRQAPGQGLEWMAWVNPNSGGTNSAQKFQGR VTMTRDTSISTVYMELSRLRSDDTAVYYCARGGQL GGFNYYYGMDVWGQGTTVTVSS<br><br>SEQ ID NO: 29474 |
| iPS:434199 | 21-225_59F11 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATGTGTTACCCTTC ACTTTCGGCCCTGGGACCAAAGTGGATTTCAA A<br><br>SEQ ID NO: 25469 | CAGGTGCAGCTGGTGGTGCAGTCTGGGGAGGCGTG GTCCAGCCTGGGAGGTCCCTGAGACTCTCCTGTG CAGCGTCTGGATTCACCTTCAGTAGCTAACTATGGCAT GCACTGGGTCCGCCAGGCTCCAGGCAAGGGGCT GGAGTGGGTGGCAGTTATATGGTATGATGAAAGT AATAAACACTATGCAGACTCCGTGAAGGGCCGA TTCACCATCTCCAGAGACAATTCCAAGACCACGC TGTATCTGCAAATGAGCAGCCTGAGAGCCGAGG ACACGGCTGTGTATTATTGTTCGAGAGAACTGGG GATGAACGGAGACTACTGGGGCCAGGGAACCCT GGTCACCGTCTCCTCA<br><br>SEQ ID NO: 29475 |

FIGURE 50
(Continued)

| | | | |
|---|---|---|---|
| iPS:434201 | 21-225_59A12 | AA | DIQMTQSPSSLSASVGDRVTITCRASQGIRNDLGWYQQKPGKAPKRLIYAASSLQSGVPSRFSGSGSGTEFTLTISSLQPEDFATYYCLQHNRYPFTFGPGTKVDFK<br>SEQ ID NO: 25470 | QVQLVESGGGVVQPGRSLRLSCAASGFTFSNYGMHWVRQAPGKGLEWVAVIWYDESNKHYADSVKGRFTISRDNSKTTLYLQMSSLRAEDTAVYYCSRELGMNGDYWGQGTLVTVSS<br>SEQ ID NO: 29476 |
| | | NA | GATATTGTGATGACCCAGACTCCACTCTCTCTGTCCGTCACCCCTGGACAGCCGGCCTCCATCTCCTGCAAGTCTAGTCAGAGCCTCCAGCATGGTGAAGGAAAGACCTATTTGTATTGGTACGTGCAGAAGCCAGGCCAGCCTCCACAGCTCCTGATCTATGAAGTTTCCTATCGGTTTTCTGGAGTGCCAGATAGGTTCAGTGGCAGTGGGTCAGGGACAGATTTCACACTGAAAATCAGCCGGGTGGAGGTTGAGGATGTTGGGGTTTATTACTGCATGCAAAGTACACAGCTTCCGCTCACCTTCGGCGGAGGGACCAAGGTGGAGATCAAA<br>SEQ ID NO: 25471 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGTATGGATGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGGGGTATAGCAGCAGCTGGGACGGGGGTATGGACGTCTGGGGCCAAGGGACCACGGTCACCGTCTCCTCA<br>SEQ ID NO: 29477 |
| | | AA | DIVMTQTPLSLSVTPGQPASISCKSSQSLQHGEGKTYLYWYVQKPGQPPQLLIYEVSYRFSGVPDRFSGSGSGTDFTLKISRVEVEDVGVYYCMQSTQLPLTFGGGTKVEIK<br>SEQ ID NO: 25472 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARRYSSSWDGGMDVWGQGTTVTVSS<br>SEQ ID NO: 29478 |

FIGURE 50
(Continued)

| | | | | |
|---|---|---|---|---|
| iPS:434203 | 21-225_60E2 | NA | GACATCCAGATGACCCAGTCTCCATCCTCCCT GTCTGCATCTGTAGGAGACAGAGTCACCATCA CTTGCCGGGCAAGTCAGGGCATTAGAAAAGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA | CAGGTGCAGCTGGTGGAGTCTGGGGGAGGCGTG GTCCAGCCTGGGAGGTCCCTGAGACTCTCCTGTG CAGCGTCTGGATTCACCTTCAATGACTATGGCAT GCACTGGGTCCGCCAGGCTCCAGGCAAGGGCT GGAGTGGGTGGCAATTATATGGTATGATGAAAAT AATAAATACTATGCAGACTCCGTGAAGGGCCGA TTCACCATCTCCAGAGACAATTCCAAGAACACGC TGTATCTGCAAATGAGCAGCCTGAGAGCCGAGG ACACGGCTGTATATTACTGTGCGAGAGATGTTCT GGACCCTTTTGACTACTGGGGCCAGGGAACCCTG GTCACCGTCTCCTCA |
| | | | SEQ ID NO: 25473 | SEQ ID NO: 29479 |
| | | AA | DIQMTQSPSSLSASVGDRVTITCRASQGIRKDLG WYQQKPGKAPKRLIYAASSLQSGVPSRFSGSGS GTEFTLTISSLQPEDFATYYCLQHNSYPWTFGQG TKVEIK | QVQLVESGGGVVQPGRSLRLSCAASGFTFNDYGM HWVRQAPGKGLEWVAIIWYDENNKYYADSVKGR FTISRDNSKNTLYLQMSSLRAEDTAVYYCARDVLD PFDYWGQGTLVTVSS |
| | | | SEQ ID NO: 25474 | SEQ ID NO: 29480 |
| iPS:434205 | 21-225_60G2 | NA | GATATTGTGATGACCCAGACTCCACTCTCTCT GTCCGTCACACCTGGACAGTCGGCCTCCATCT CCTGCAAGTCTAGTCAGAGCCTCCTGCATAGT GAAGGAAAGACCTATTTGTATTGGTACCTGCA GAAGCCAGGCCAGTCTCCACAGCTCCTGATCT ATGAAGTTTCCAACCGGATCTCTGGAGTGCCA GATAGGTTCAGTGGCAGCGGGTCAGGGACAG ATTTCACACTGAAAATCAGCCGGGTGGAGGCT GAGGATGTTGGGGTTTATTACTGCATGCAAAG TATACAGCTTCCGCTCACTTTCGGCGGAGGGA CCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGAAGCTGACGGGAGGCATGACGTCTGGCG CCAAGGGACCACGGTCACCGTCTCCTCA |
| | | | SEQ ID NO: 25475 | SEQ ID NO: 29481 |

FIGURE 50
(Continued)

| | | | | |
|---|---|---|---|---|
| iPS:434207 | 21-225_60A3 | AA | DIVMTQTPLSLSVTPGQSASISCKSSQSLLHSEGK TYLYWYLQKPGQPPQLLIYEVSNRISGVPDRFSG SGSGTDFTLKISRVEAEDVGVYYCMQSIQLPLTF GGGTKVEIK<br><br>SEQ ID NO: 25476 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSRS WTGGMDVWGQGTTVTVSS<br><br>SEQ ID NO: 29482 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATTTAGTT TGCAAAGTGGGGTCCCATCAAGGTTCAGCGGC AGTGGATCTGGGACAGACCTCACAAT CAGCAGCCTGCAGCCTGAAGATTTTGCAACTT ATTACTGTCTACAGCATATAAGTTACCCTTTCA CTTTCGGCCCTGGGACCAAAGTGGATATCAAA<br><br>SEQ ID NO: 25477 | CAGGTGCAACTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGCT GGAGTGGGTGGCAGTTATATGGTATGAAGAAAG TAATAAATACTATGCAGACTCCGTGAAGGCCG ATTCACCATCTCCAGAGACAATTCCAAGAACACG CTGTATCTGCAAATGAACAGCCTGAGAGCCGAG GACACGGCTGTATATTACTGTGCGAGAGAACTGG GGATGACCGGAGACTACTGGGGCCAGGGAACCC TGGTCACCGTCTCCTCA<br><br>SEQ ID NO: 29483 |
| | | AA | DIQMTQSPSSLSASVGDRVTITCRASQGIRNDLG WYQQKPGKAPKRLIYAAFSLQSGVPSRFSGSGS GTEFTLTISSLQPEDFATYYCLQHNSYPFTFGPGT KVDIK<br><br>SEQ ID NO: 25478 | QVQLVESGGGVVQPGRSLRLSCAASGFTFSSYGMH WVRQAPGKGLEWVAVIWYEESNKYYADSVKGRF TISRDNSKNTLYLQMNSLRAEDTAVYYCARELGMT GDYWGQGTLVTVSS<br><br>SEQ ID NO: 29484 |

FIGURE 50
(Continued)

| | | | |
|---|---|---|---|
| iPS:434209 | 21-225_60C3 | NA | GACATCCAGATGACCCAGTCTCCATCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATTCTGCATCCAGT TACAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAATAGTTACCCGTGG ACGTTCGGCCTAGGGACCAAGGTGGAAATCA AA | CAGGTGCAACTAGTGCAGTCTGGGGCTGAGGTG AAGAAGCCTGGGGCCTCAGTGAAGGTCTCCTGC AAGGCTTCTGGATACAGTTTCACCGGCCACTATA TACACTGGGTGCGACAGGCCCCTGGACAAGGGC TTGAGTACATGGGATGGATCAACCCTAACAGCG GTGGCACAAACTATGTACAGAGAAATTTCAGGGCA GGGTCACCATGACCAGGGACACGTCCATCAGCA CAGCCTACATGGAGCTGAGCAGGCTGAGATCTG ACGACACGGCCATATATTACTGTTCGAGAGGGG GCCTACTGGGAGCTACCAACTACTATTATTACGG TATGGACGTCTGGGGCCAAGGACCACGGTCAC CGTCTCCTCA |
| | | | SEQ ID NO: 25479 | SEQ ID NO: 29485 |
| | | AA | DIQMTQSPSSLSASVGDRVTITCRASQGIRNDLG WYQQKPGKAPKRLIYSASSLQSGVPSRFSGSGSG TEFTLTISSLQPEDFATYYCLQHNSYPWTFGLGT KVEIK | QVQLVQSGAEVKKPGASVKVSCKASGYSFTGHYIH WVRQAPGQGLEYMGWINPNSGGTNYVQKFQGRV TMTRDTSISTAYMELSRLRSDDTAIYYCSRGGLLGA TNYYYYGMDVWGQGTTVTVSS |
| | | | SEQ ID NO: 25480 | SEQ ID NO: 29486 |
| iPS:434211 | 21-225_60F3 | NA | GACATCGTGATGACCCAGTCTCCAGACTCCT GACTGTGTCTCTGGGCGAGAGGGCCACCATCA ACTGCAAGTCCAGCCAGAGTGTTTTATACAGC TCCAACAATAAGAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAATTTATTATTACTGTCAGCAA TATTATAGTACTCCGTGCAGTTTGGCCAGGG GACCAAGCTGGAGATCAAC | CAGGTGCTGCTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGCT TGAGTGGATGGGATGGATGCACCCTAACAGTGGT AACACAGGCTATGCACAGAAGTTCCAGGGCAGA GTCACCATGACCAGGAACACCTCCATAAGCACA GCCTACATGGAGCTGAGCAGCCTGAGATCTGAG GACACGGCCGTGTATTACTGTGCGTATAGCAGTG GCTGGTACTTCTTTGACTACTGGGGCCAGGGAAC CCTGGTCACCGTCTCCTCA |
| | | | SEQ ID NO: 25481 | SEQ ID NO: 29487 |

FIGURE 50
(Continued)

| | | | | |
|---|---|---|---|---|
| iPS:434213 | | AA | DIVMTQSPDSLTVSLGERATINCKSSQSVLYSSN NKNYLAWYQQKPGQPPKLLIYWASTRESGVPD RFSGSGSGTDFTLTISSLQAEDVAIYYCQQYSTP CSFGQGTKLEIN<br>SEQ ID NO: 25482 | QVLLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YFFDYWGQGTLVTVSS<br>SEQ ID NO: 29488 |
| | 21-225_60A4 | NA | GACATCCAGATGACCCAGTCTCCATCCTCACT GTCTGCATCTGTAGGAGACAGAGTCACCATCA CATGTCGGGCGAGTCAGGGCATTAGCAATTAC TTAGCCTGGTTTCAGCAGAAACCAGGGAAAGC CCCTAAGTCCCTGATCTATGCTGCATCCAGTTT GCAAAGTGGGGTCCCATCAAGGTTCAGCGGCA GTGGATCTGGGACAGATCTGAACTCTCACCATC AGCAGCCTGCAGTCTGAAGATTTTGCAACGTA CTACTGCCAACAATATAAAAGTCACCATTCA CTTTCGGCCCTGGGACCAAAGTGGATATCAAA<br>SEQ ID NO: 25483 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGTCAT GAGCTGGGTCCGCCAGGCTCCAGGGAAGGGGCT GGAGTGGGTCTCATCTATTAGTGGTAGTGGTGGT TGGACAAACTACGCAGACTCCGTGAAGGGCCGA TTCACCACCTCCAGAGACAATTCCAAGAACACGC TGTATCTGCAAATGAACAGCCTGAGAGCCGAGG ACACGGCCGTTTATTACTGTGCGAGACTAACTGG ATTTGACTATTGGGGCCAGGGAACCCTGGTCACC GTCTCCTCA<br>SEQ ID NO: 29489 |
| | | AA | DIQMTQSPSSLSASVGDRVTITCRASQGISNYLA WFQQKPGKAPKSLIYAASSLQSGVPSKFSGSGSG TDFTLTISSLQSEDFATYYCQQYKSHPFTFGPGT KVDIK<br>SEQ ID NO: 25484 | EVQLLESGGGLVQPGGSLRLSCAASGFTFSSYVMS WVRQAPGKGLEWVSSISGSGGWTNYADSVKGRFT TSRDNSKNTLYLQMNSLRAEDTAVYYCARLTGFD YWGQGTLVTVSS<br>SEQ ID NO: 29490 |

FIGURE 50
(Continued)

| | | | |
|---|---|---|---|
| iPS:434215 | 21-225_60F7 | NA | GACATCCAGATGACCCAGTCTCCATCCTCACT GTCTGCATCTGTAGGAGACAGAGTCACCATCT CTTGTCGGGCGAGTCAGGTCATTAAGAATTAT TTAGTCTGGGTTCAGCAGAAACCAGGGAAAGC CCCTAAGTCCCTGATCTATGCTGCGTCCAGTTT GCAAAAGTGGGGTCCCATCAACGTTCAGGGCA GTGGATCTGGGACAGATTTCACTCTCACCATC AGCAGCCTGCAGCCTGAAGATTTTGCAACTTA TTACTGCCTACAGTTCATAGTTACCCATTCAC TTTCGGCCCTGGGACCAAAATGGATATCAAA  SEQ ID NO: 25485 |
| | | AA | DIQMTQSPSSLSASVGDRVTISCRASQVIKNYLV WVQQKPGKAPKSLIYAASSLQSGVPSTFSGSGSG TDFTLTISSLQPEDFATYYCLQFHSYPFTFGPGTK MDIK  SEQ ID NO: 25486 | GAGGTGCAGCTGTTGGAGTCTGGGGGAGGCTTG GTACAGCCTGGGGGGTCCCTGAGACTCTCGTG CAGCCTCTGGATTCACCTTTAGCAGCTATGTCAT GAGCTGGGTCCGCCAGGTCCAGGGAAGGGGCT GGAGTGGGTCTCAGGTATTAGTGGTAGTGGTAAT AGAACATACTACGCAGACTCCGTGAAGGGCCGG TTCACCATCTCCAGAGACAATTCCAAGAATACGC TGTATCTGCAAATGAACAGCCTGAGAGCCGAGG ACTCGGCCGTTTATTACTGTGGGAGTTTGGGGAT TGACTGGGGCCAGGGAACCCTGGTCACCGTCTCC TCA  SEQ ID NO: 29491 |
| | | | EVQLLESGGGLVQPGGSLRLSCAASGFTFSSYVMS WVRQAPGKGLEWVSGISGSGNRTYYADSVKGRFTI SRDNSKNTLYLQMNSLRAEDSAVYYCGSLGIDWG QGTLVTVSS  SEQ ID NO: 29492 |
| iPS:434217 | 21-225_60E8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTTTCAGCAGAAACCAGGGAAAGC CCCTAAGCGCCTGATCTATGCTGCATCCAGTTT GCAAAGTGGGGTCCCATCAAGGTTCAGCGGCA GTGGATCTGGGACAGAATTCACTCTCACAATC AGCAGCCTGCAGCCTGAAGATTTTGCAACTTA TTACTGTCTACAGCATAGTAGTTACCCGCTCA CTTTCGGCGGAGGGACCAAGGTGGAGATCAAA  SEQ ID NO: 25487 | CAGGTGCAGCTGCAGGAGTCGGGCCCAGGACTG GTGAGGCCTTCGGCGACCCTGTCCCTCACCTGCA CTGTCTCTGGTGGCTCCATCAGCAGGAGTAGTTA CTACTGGGGCTGGATCCGCCAGCCCCCAGGGAA GGGAGCGCCTCTACAACCCGTCCCTCAAGAGTC GAGTCACCATATCCGTAGACACGTCCGAGAACC AATTCTCCCTGAGGCTGAGCTCTGTGACCGCCGC AGACACGGCTGTGTATTACTGTGCGAGACTGGAC AGTGGCTGTCGTTGACTACTGGGGCCAGGGAA CCCTGGTCACCGTCTCCTCA  SEQ ID NO: 29493 |

FIGURE 50
(Continued)

| | | | | |
|---|---|---|---|---|
| iPS:434219 | 21-225_60E9 | AA | DIQMTQSPSSLSASVGDRVTFTCRASQGIRNDLG WFQQKPGKAPKRLIYAASSLQSGVPSRFSGSGSG TEFTLTISSLQPEDFATYYCLQHSSYPLTFGGGTK VEIK | QVQLQESGPGLVRPSATLSLTCTVSGGSISRSSYYW GWIRQPPGKGLEWIGSIYYSGSASYNPSLKSRVTIS VDTSENQFSLRLSSVTAADTAVYYCARLDSGWSFD YWGQGTLVTVSS |
| | | | SEQ ID NO: 25488 | SEQ ID NO: 29494 |
| | | NA | GAAATAGTGATGACGCAGTCTCCAGCCACCCT GTCTGTGTCTCCAGGGGAAAGAGCCACCCTCT CCTGTAGGGCCAGTCAGAGTGTTAGCAGTCA TTAGCCTGGTACCGGCAGAAACCTGGCCAGGC TCCCAGGCTCCTCATCTATGGTGCATCCACCA GGGCCACTGGTATCCCGGCCAGGTTCAGTGGC AGTGGGTCTGGGACAGAGTTCACTCTCACCAT CAGCAGCCTGCAGTCTGAAGATTTTGCAGTTT ATTGCTGTCAGCAGTAATAATAACTGGCCATTC ACTTTCGGCCCTGGGACCAAAATAGATATCAA A | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATGCCATG AGCTGGGTCCGCCAGGCTCCAGGGAAGGGGCTG GAGTGGGTCTCAGCTATTAGTGGTAGTGGTGGTA ACACATTCTACGCAGACTCCGTGAAGGGCCGGTT CACCATCTCCAGAGACAATTCCAAGAACACGCTG TATCTTCAAATGAACAGCCTGAGAGCCGAGGACA CGGCCGTATATTACTGTGCGAAATTTTCGGTAT AGTGGGAGCCGGGTACTTTGACTACTGGGGCCA GGGAACCCTGGTCACCGTCTCCTCA |
| | | | SEQ ID NO: 25489 | SEQ ID NO: 29495 |
| | | AA | EIVMTQSPATLSVSPGERATLSCRASQSVSSSLA WYRQKPGQAPRLLIYGASTRATGIPARFSGSGSG TEFTLTISSLQSEDFAVYCCQQYNNWPFTFGPGT KIDIK | EVQLLESGGGLVQPGGSLRLSCAASGFTFSSYAMS WVRQAPGKGLEWVSAISGSGGNTFYADSVKGRFTI SRDNSKNTLFLQMNSLRAEDTAVYYCAKFFGIVGA GYFDYWGQGTLVTVSS |
| | | | SEQ ID NO: 25490 | SEQ ID NO: 29496 |

FIGURE 50
(Continued)

| | | | | |
|---|---|---|---|---|
| iPS:434221 | 21-225_60A11 | NA | GACATCCAGATGACCCAGTCTCCATCTTCCGT GTCTGCATCTGTAGGAGACAGAGTCACCATCA CTTGTCGGGCGAGTCAGGTTATTAGCAACTGG TTAGCCTGGTATCAGCTGAAACCAGGAAAGC CCCTAAGCTCCTGATCTATACTGCATCCAGTTT GCAAAGTGGGGTCCCATCAAGGTTCAGCGGCA ATGAATCTGGGACAGATTTCACTCTCACCATC AGCAGCCTGCAGCCTGAAGATTTTGCAACTA CTATTGTCAACAGGCTAACAGTTTCCCGTGA CGTTCGGCCAAGGGACCAAGGTGGAAATCAA A | GAGGTGCAGCTGTTGGAGTCTGGGGGAGGCTTG GTACAGCCGGGGGGGTCCCTGAGACTCTCCTGTG CAGCCCTCTGGATTCACCTTTAGCAACTATGCCAT GACCTGGGTCCGCCAGGCTCCAGGGAAGGGCT GGAGTGGGTCTCAGTTATTAGTGGTAGTGGTGGT AACACATTCTACGCAGACTCCGTGACGGGCCGG GTCACCATCTCCAGAGACAATTCCAAGAACACGC TGTATCTGCAAATGAACAGTCTGAGAGCCGAGG ACACGGCCGTATATTACTGTGCGAAACTGGGA AGGACTACTACTACGGTATGACGTCTGGGG CCAAGGGACCACGGTCACCGTCTCCTCA |
| | | | SEQ ID NO: 25491 | SEQ ID NO: 29497 |
| | | AA | DIQMTQSPSSVSASVGDRVTITCRASQVISNWLA WYQLKPGKAPKLLIYTASSLQSGVPSRFSGNESG TDFTLTISSLQPEDFATYYCQQANSFPWTFGQGT KVEIK | EVQLLESGGGLVQPGGSLRLSCAASGFTFSNYAMT WVRQAPGKGLEWVSAISGSGGNTFYADSVTGRVTI SRDNSKNTLYLQMNSLRAEDTAVYYCAKLGKDYH YYGMDVWGQGTTVTVSS |
| | | | SEQ ID NO: 25492 | SEQ ID NO: 29498 |
| iPS:434223 | 21-225_60C12 | NA | GACATTGTGATGACCCAGACTCCACTCTCT GTCCGTCACCCCTGGACAGCCGGCCTCCATCT CCTGCAAGTCTAGTCAGAGCCTCCTGCATAGT GAGGAAAGAACCTATTTGTATTGGTACCTGCA GAAGCCAGGCCAGCCTCCACAGTTCCTGATCT ATGAAGTTTCCAACCGGTTCTGGAGTGCCA GATAGGTTCAGTGGCAGCGGGTCAGGGACAG ATTTCACACTGAAAATCAGCGGGGTGGAGGCT GAGGATGTTGGGATTTATTACTGCATGCAAAG TATAAAGTATCCGCTCACTTTCGGCGGAGGGA CCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGTAGACTCCGTGAAGT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAAGGTATAGC AGAAGTGGACGGGAGGTATGGACGTCTGGGGC CAGGGGACCACGGTCACCGTCTCCTCA |
| | | | SEQ ID NO: 25493 | SEQ ID NO: 29499 |

FIGURE 50
(Continued)

| | | | |
|---|---|---|---|
| iPS:434225 | | AA | DIVMTQTPLSLSVTPGQPASISCKSSQSLLHSEGK TYLYWYLQKPGQPPQFLIYEVSNRFSGVPDRFSG SGSGTDFTLKISRVEAEDVGIYYCMQSIKYPLTF GGGTKVEIK<br>SEQ ID NO: 25494 | QVQLVESGGGVVQPGRSLRLSCAASGFTFSSYGMH WVRQAPGKGLEWVAVIWYDGSNKYYVDSVKGRF TISRDNSKNTLYLQMNSLRAEDTAVYYCARRYSRS WTGGMDVWGQGTTVTVSS<br>SEQ ID NO: 29500 |
| | | NA | GACATCCAGATGACCCAGTCTCCATCCTCCCT GTCTGCATCTGTAGGAGACAGAGTCACCATCA CTTGCCGGGCAAGTCAGAGTCAGCAGCATTAGCAGCTAT TTAAATTGGTATCAGCAGAAACCAGGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCACCTT ACTACTGTCAACAGAGAGTTACAATATTTCATTC ACTTTCGGCCCTGGGACCAAAGTGGATATCAA A<br>SEQ ID NO: 25495 | CAGGTGCAGCTGCAGGAGTCGGGCGGAGGACTG GTGAAGCCTTCGGAGACCCTGTCCCTCACCTGCA CTGTCTCTGGTGGCTCCATCAGTAGTTACTTCTGG AGCTGGATCCGGCAGCCCGCCGGGAAGGACTG AGTGGATTGGGCGCATCTATACCAGGGGAGC ACCAACTACAACCCCTCCCTCAAGAGTCGAGTCA CCATGTCAGTAGACACGTCCAAGAACCAGTTCTC CCTGAAGCTGAGCTCTGTGACCGCCGCGGACACG GCCGTGTATTACTGTGCGAGAGAGGAAAAACT GGGGGGGTTTCTTACTTTGACTTACTGGGGCCAGG GAACCCTGGTCACCGTCTCCTCA<br>SEQ ID NO: 29501 |
| 21-225_60E12 | | AA | DIQMTQSPSSLSASVGDRVTITCRASQSISSYLNW YQQKPGKAPKLLIYAASSLQSGVPSRFSGSGSGT DFTLTISSLQPEDFAPYYCQQSYNISFTFGPGTKV DIK<br>SEQ ID NO: 25496 | QVQLQESGPGLVKPSETLSLTCTVSGGSISSYFWSW IRQPAGKGLEWIGRIYTRGSTNYNPSLKSRVTMSVD TSKNQFSLKLSSVTAADTAVYYCAREGKTGGVSYF DYWGQGTLVTVSS<br>SEQ ID NO: 29502 |

FIGURE 50
(Continued)

| | | | |
|---|---|---|---|
| iPS:434227 | 21-225_61A1 | NA | GACATCCAGATGACCCAGTCTCCATCCTCCT GTCTGCATCTGTAGGAGACAGAGTCACCATCA CTTGCCGGGCAAGTCAGAGCATTAGCAGCTAT TTAAATTGGTATCAGCAGAAACCAGGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCACCTT ACTACTGTCAACAGAGTTACAATATTTCATTC ACTTTCGGCCCTGGGACCAAGGTGGATATCAA A | CAGGTGCAGCTGCAGGAGTCGGGCCCAGGACTG GTGAAGCCTTCGGAGAGACCCTGTCCCTCACTGCA CTGTCTCTGGTGGCTCCATCAGTAGTCACTTCTG GAGCTGGATCCGGCAGCCCGCCGGGAAGGGACT GGAGTGGATTGGGCGCATCTATATCAGGGGAG CACCAACTACAACCCCTCCCTCAAGAGTCGAGTC ACCATGTCAGTAGACACGTCCAAGAACCAGTTCT CCCTGAAGCTGAGCTCTGTGACCGCCGCGGACAC GGCCGTGTATTACTGTGCGAGAGAGGAAAAAC TGGGGGGGTTCTTACTTTGACTACTGGGGCCAG GGAACCCTGGTCACCGTCTCCTCA |
| | | | SEQ ID NO: 25497 | SEQ ID NO: 29503 |
| | | AA | DIQMTQSPSSLSASVGDRVTITCRASQSISSYLNW YQQKPGKAPKLLIYAASSLQSGVPSRFSGSGSGT DFTLTISSLQPEDFAPYYCQQSYNISFTFGPGTKV DIK | QVQLQESGPGLVKPSETLSLTCTVSGGSISSHFWSW IRQPAGKGLEWIGRIYIRGSTNYNPSLKSRVTMSVD TSKNQFSLKLSSVTAADTAVYYCAREGKTGGVSYF DYWGQGTLVTVSS |
| | | | SEQ ID NO: 25498 | SEQ ID NO: 29504 |
| iPS:434229 | 21-225_61H1 | NA | GACATCCAGATGACCCAGTCTCCATCCTCCCT GTCTGCATCTGTAGGAGACAGAGTCACCATCA CTTGCCGGGCAAGTCAGGGCATTAGAAAAGAT TTAGGCTGGTATCAGCAGAAACCAGGGAAAG CCCCTAAGCGCCTGATCTTTGCTGCATCCAGTT TGCAAAGTGGGGTCCCATCAAGGTTCAGCGGC AGTGGATCTGGGACAGCCTTGGGACACTGCAACTT CAGCAGCCTGCAGCCTGAAGATTTTGCAACTT ATTACTGTCTACAGCATAATAGTTACCCGTGG ACGTTCGGCCAAGGGACCAAGGTGGAAATCA AA | CAGGTGCAGCTGGTGCAGTCTGGGGGAGGCGTG GTCCAGCCTGGGAGGTCCCTGAGACTCTCCTGTG CAGCCGTCTGATTCACCTTCAATGACTATGGCAT GCACTGGGTCCGCCAGGCTCCAGGCAAGGGCT GGAGTGGGTGGCAATTATATGGTATGGATGAAAGT AATAATATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGATGTTCT GGACCCTTTTGACTACTGGGGCCAGGGAACCCTG GTCACCGTCTCCTCA |
| | | | SEQ ID NO: 25499 | SEQ ID NO: 29505 |

FIGURE 50
(Continued)

| | | | | |
|---|---|---|---|---|
| iPS:434231 | 21-225_61F2 | AA | DIQMTQSPSSLSASVGDRVTITCRASQGIRKDLG WYQQKPGKAPKRLIFAASSLQSGVPSRFSGSGSG TEFTLTISSLQPEDFATYYCLQHNSYPWTFGQGT KVEIK<br>SEQ ID NO: 25500 | QVQLVESGGGVVQPGRSLRLSCAASGFTFNDYGM HWVRQAPGKGLEWVAIIWYDESNKYYADSVKGRF TISRDNSKNTLYLQMNSLRAEDTAVYYCARDVLDP FDYWGQGTLVTVSS<br>SEQ ID NO: 29506 |
| | | NA | GACATCCAGATGACCCAGTCTCCATCCTCCCT GTCTGCATCTGTAGGAGACAGAGTCACCGTCA CTTGCCGGGCAAGTCAGGGCATTAGAGATGAT TTAGGCTGGTATCAGCAGAAACCAGGGAAAG CCCCTGAGCGCCTGATCTATGCTGCATCCAGT TTGCAAAGTGGGGTCCCATCAAGGTTCAGCGG CAGTGGATCTGGGACAGAGTTCACTCTCACAA TCAGCAGCCTGCAGCCTGAAGATTTTGCAACT TATTACTGTCTACAGCATTATAGTTACCCTCGC AGTTTTGGCCAGGGGACCAAGCTGGAGATCAA A<br>SEQ ID NO: 25501 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGAGGTA TAGCAGTGGCTGGTACGACTACGGTATGGACGTC TGGGGCCAAGGGACCACGGTCACCGTCTCCTCA<br>SEQ ID NO: 29507 |
| | | AA | DIQMTQSPSSLSASVGDRVTVTCRASQGIRDDLG WYQQKPGKAPERLIYAASSLQSGVPSRFSGSGSG TEFTLTISSLQPEDFATYYCLQHYSYPRSFGQGT KLEIK<br>SEQ ID NO: 25502 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARERYSS GWYDYGMDVWGQGTTVTVSS<br>SEQ ID NO: 29508 |

FIGURE 50
(Continued)

| | | | |
|---|---|---|---|
| iPS:434233 | 21-225_61B3 | NA | GATATTGTGATGACCCAGACTCCACTCTCT GTCCGTCACACCTGGACAGCCGGCCTCCATCT CCTGCAAGTCTAGTCAGAGCCTCCTGCATAGT GAAGGAAAAGACCTATTTGTATTGGTACCTGCA GAAGCCAGGCCAGCCTCCACAGCTCCTGATCT ATGAAGTTTCCAACCGATCTCTGGAGTGCCA GATAGGTTCAGTGGCAGCGGGTCAGGACAG ATTTCACACTGAAAATCAGCCGGGTGGAGGCT GAGGATGTTGGGGTTTATTACTGCATGCAAAG TATACAGGTTCCGCTCACTTTCGGCGGAGGGA CCAAGGTGGAGATCAAA SEQ ID NO: 25503 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAATACTATGCAGACACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGAAGCTGGGCGGGAGGCATGACGTCTGGGG CCAAGGGACCACGGTCACCGTCTCCTCA SEQ ID NO: 29509 |
| | | AA | DIVMTQTPLSLSVTPGQPASISCKSSQSLLHSEGK TYLYWYLQKPGQPPQLLIYEVSNRISGVPDRFSG SGSGTDFTLKISRVEAEDVGVYYCMQSIQLPLTF GGGTKVEIK SEQ ID NO: 25504 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSRS WAGGMDVWGQGTTVTVSS SEQ ID NO: 29510 |
| iPS:434235 | 21-225_61E3 | NA | GACATCGTGATGACCCAGTCTCCAGACTCCCT GGCTGTGTCTCTGGGCGAGAGGGCCACCATCA ACTGCAAGTCCAGCCAGAGTGTTTTACACATC TCCAACAATAACAATTACTTAGCTTGGTACCA GCAGCAACCAGGACAGCCTCCTAAACTGCTCA TTTACTGGGCATCTATCCGGGAATCCGGGGTC CCTGACCGATTCAGTGGCAGCGGGTCTGGGAC AGATTTCACTCTCACCATCAGCAGCCTGCAGG CTGAAGATGTGGCAGTTATTATTACTGTCAGCAA TATTATAGTATTCCGTGCAGTTTTGGCCAGG GACCAAGCTGGAGATCAAA SEQ ID NO: 25505 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAAATCTGA GGACACGGCCGTGTATTACTGTGCGTATAGCAGT GGCTGGTACCGCTTTGACTACTGGGGCCAGGAA CCCTGGTCACCGTCTCCTCA SEQ ID NO: 29511 |

FIGURE 50
(Continued)

| | | | |
|---|---|---|---|
| iPS:434237 | 21-225_61B5 | AA | DIVMTQSPDSLAVSLGERATINCKSSQSVLHISN NNNYLAWYQQKPGQPPKLLIYWASIRESGVPDR FSGSGSGTDFTLTISSLQAEDVAVYYCQQYYSIP CSFGQGTKLEIK<br>SEQ ID NO: 25506 | QVQLVQSGAEVKKPGASVKVSCKASGYTFTNYDIN WVRQATGQGLEWMGWMTPNSGNTGYAQKFQGR VTMTRNTSISTAYMELSSLKSEDTAVYYCAYSSGW YRFDYWGQGTLVTVSS<br>SEQ ID NO: 29512 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATAACAACTCCTTAACTTGGTACCA GCTGAAACCAGGACAGCCTCCTAAGAAGCTCA TTTACTGGGCATCTACCCGGCAGCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACCTCCTCCGACGTTCGGCCAAGG GTCCAAGGTGGAAATCAAA<br>SEQ ID NO: 25507 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAGCACAGGCTATGCACAGAAGTTCCAGGGCAG AGTCACCATGACCAGGAACACCTCATAAGCAC AGCCTACATGAGCTGAGCAGCCTGAGATCTGA GGACACGGCCGTGTATTACTGTGCGTATAGCAGT GGCTGGTACTACTTTGACTACTGGGGCCAGGGAA CCCTGGTCACCGTCTCCTCA<br>SEQ ID NO: 29513 |
| | | AA | DIVMTQSPDSLAVSLGERATINCKSSQSVLYSSN NNNSLTWYQLKPGQPPKKLIYWASTRESGVPDR FSGSGSGTDFTLTISSLQAEDVAVYYCQQYYSTP PTFGQGSKVEIK<br>SEQ ID NO: 25508 | QVQLVQSGAEVKKPGASVKVSCKASGYTFTNYDIN WVRQATGQGLEWMGWMHPNSGSTGYAQKFQGR VTMTRNTSISTAYMELSSLRSEDTAVYYCAYSSGW YYFDYWGQGTLVTVSS<br>SEQ ID NO: 29514 |

FIGURE 50
(Continued)

| | | | |
|---|---|---|---|
| iPS:434239 | 21-225_58F1 | NA | GACATCCAGATGACCCAGTCTCCATCCTCCT GTCTGCATCTGTAGGAGACAGAGTCACCATCA CTTGCCGGGCAAGTCAGAGCATTACCAACTTT TTAAATTGGTATCAGCAGAAACCAGGGAAAG CGCCTAAACTCCTGATCTTCGCTGCATCCAGTT TGCAAAGTGGAATCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTATCCCGTGG ACGTTCGGCCAAGGGACCAAGGTGGAAATCA AA<br>SEQ ID NO: 25509 | GAGGTGCAGCTGTTGGAGTCTGGGGGAGGCTTG GTTCAGCCTGGGGGGTCCCTGAGACTCTCCTGTG CAGCCTCTGGATTCACCTTTAGCAGCTATGCCAT GAGTTGGGTCCGCCAGGCTCCAGGGAAGGGGCT GGAGTGGGTCTCAGCTATTAGTAGTACTGGTGGT AACACATACTACGCAGACTCCGTGAAGGGCCGG TTCACCATTTCCAGAGACAATTCCAAGAACACGC TGTATCTGCAAATGAACAGCCTGAGAGCCGAGG ACACGGCCGTATATTACTGTGCGAAACGGGGGG TCTACGGTGACTTTGATGCTTTTGATATCTGGGGC CAAGGGACAATGGTCACCGTCTCTTCA<br>SEQ ID NO: 29515 |
| | | AA | DIQMTQSPSSLSASVGDRVTITCRASQSITNFLN WYQQKPGKAPKLLIFAASSLQSGIPSRFSGSGSG TDFTLTISSLQPEDFATYYCQQSYSIPWTFGQGT KVEIK<br>SEQ ID NO: 25510 | EVQLLESGGGLVQPGGSLRLSCAASGFTFSSYAMS WVRQAPGKGLEWVSAISTGGGNTYYADSVKGRFT ISRDNSKNTLYLQMNSLRAEDTAVYYCAKRGVYG DFDAFDIWGQGTMVTVSS<br>SEQ ID NO: 29516 |
| iPS:434241 | 21-225_61E6 | NA | GACATCCAGATGACCCAGTCTCCATCCTCCCT GTCTGCATCTGTAGGAGACAGAGTCACCATCA CTTGCCGGGCAAGTCAGGGACAGGCATTAGCA TTAGGCTGGTATCAGCAGAAACCAGGGAAAG CCCCTGAGCGCCTGATCTATGCTGCATCCAGT TTGCAAAGTGGGGTCCCATCAAGGTTCAGCGG CAGTGGATCTGGGACAGACCTGAAGATTTTGCAACT TCAGCAGCCTGAAGATTTTGCAACT TATTACTGTCTACAACATAATAGTTTCCCTCCG TGGACGTTCGGCCAAGGGACCAAGGTGGAAA TCAAA<br>SEQ ID NO: 25511 | GAGGTGCAGCTGTGTTGGAGTCTGGGGGAGGCTTG GTACAGCCTGGGGGGTCCCTGAGACTCTCCTGTG CAGCCTCTGGATTCACCTTTAGAAGCTATGCCAT GAGCTGGGTCCGCCAGGCTCCAGGGAAGGGGCT GGAGTGGGTCTCAGCTACTAGTGGTAGTGGTGTT AACACATTCTACGCAGACTCCGTGAAGGGCCGGT TCACCATTCCAGAGACAAGCCTGAGAGCCGAGGA GTATCTGCAAATGAACAGCCTGAGAGCCGAGGA CACGGCCGTTTTACTGTGCGAAATTGGAACTG GGGATCTTTGACTACTGGGGCCAGGGAACCCTGG TCACCGTCTCCTCA<br>SEQ ID NO: 29517 |

FIGURE 50
(Continued)

| | | AA | DIQMTQSPSSLSASVGDRITITCRASQGIGNDLG WYQQKPGKAPERLIYAASSLQSGVPSRFSGSGSG TEFTLTISSLQPEDFATYYCLQHNSFPPWTFGQG TKVEIK SEQ ID NO: 25512 | EVQLLESGGGLVQPGGSLRLSCAASGFTFRSYAMS WVRQAPGKGLEWVSATSGSGVNTFYADSVKGRFT ISRDNSKNTLYLQMNSLRAEDTAVYYCAKLELGIF DYWGQGTLVTVSS SEQ ID NO: 29518 |
| iPS:434243 | 21-225_62C1 | NA | GATATTGTGATGACTCAGTCTCCACTCTCCCTG CCCGTCACCCCTGGAGAGCCGGCCTCCATCTC CTGCAGGTCTAGTCAGAGCCTCCTACATAGTA ATGGATACAACTATTTGGATTGGTACCTGCAG AAGCCAGGGCAGTCTCCACAGTCTCCTGATCTA TTTGGTTTCTAATCGGCCTCCGGGGTCCCTGA CAGGTTCAGTGGCAGTGGATCAGGCACAGATT TTACACTGAAAATCAGCAGAGTGGGGGCTGA GGATGTTGGGGTTTATTTCTGCCTGCAAGCTCT ACAAACTCCTCACCTTCGGCCAAGGGACAC GACTGAGAGATTAAA SEQ ID NO: 25513 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGACT GGAGTGGGTCTCATCCATTAGTAGTAGTAGTAGT TACATATACTACGCAGACTCAGTGAAGGGCCGAT TCACCATCTCAGAGACAACGCCAAGAACTCACT GTATCTGCAAATGAACAGCTGAGAGCCGAGGA CACGGCTGTGTATTACTGTGCGATTTTGGAGTG GACTGGGGCCAGGGAACCCTGGTCACCGTCTCCT CA SEQ ID NO: 29519 |
| | | AA | DIVMTQSPLSLPVTPGEPASISCRSSQSLLHSNGY NYLDWYLQKPGQSPQLLIYLVSNRASGVPDRFS GSGSGTDFTLKISRVGAEDVGVYFCLQALQTPLT FGQGTRLEIK SEQ ID NO: 25514 | EVQLVESGGGLVKPGGSLRLSCAASGFTFSSYSMN WVRQAPGKGLEWVSSISSSSSYIYADSVKGRFTIS RDNAKNSLYLQMNSLRAEDTAVYYCAIFGVDWGQ GTLVTVSS SEQ ID NO: 29520 |

FIGURE 50
(Continued)

| | | | | |
|---|---|---|---|---|
| iPS:434245 | 21-225_62H1 | NA | GACATCCAGATGACCCAGTCTCCATCCTCCCT GTCTGCATATGTAGGAGACAGAGTCACCATCA CTTGCCGGGCAAGTCAGAACAGATTTCAGCTAT TTAAATTGGTATCAGCAGAAACCAGGGAAAG CCCCTAAGGTCCTGATCTATGCTGTGATTTAGTT TGCAAAGTGGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCATTC ACTTTCGGCCCTGGGACCAAAGTGGATATCAA A SEQ ID NO: 25515 | CAGGTGCAGCTGGTGGAGTCTGGGGGAGGCGTG GTCCAGCCTGGGAGGTCCCTGAGACTCTCCTGTG CAGCGTCTGATTCACCTTCAGTAGTACTATGGCAT GCACCGTCCGCCAGGCTCCAGGCAGGGCT GGAGTGGATGGCAATTATATGTATGATGGAAGT AATAAATACTATGCAGACTCCGTGAAGGGCCGA TTCACCATCTCCAGAGACAATTCCAAGAACACGC TGTATCTGCAAATCAACAGCCTGAGAGCCGAGG ACACGGCTGTGTATTACTGTGCGAGAGAAGACCC GCGTACCAGCTGCTCTGACTACTGGGGCCAGGGA ACCCTGGTCACCGTCTCCTCA SEQ ID NO: 29521 |
| | | AA | DIQMTQSPSSLSAYVGDRVTITCRASQNIFSYLN WYQQKPGKAPKVLIYAVFSLQSGVPSRFSGSGS GTDFTLTISSLQPEDFATYCQQSYSTPFTFGPGT KVDIK SEQ ID NO: 25516 | QVQLVESGGGVVQPGRSLRLSCAASGFTFSSYGMH WVRQAPGQGLEWMAIIWYDGSNKYYADSVKGRF TISRDNSKNTLYLQINSLRAEDTAVYYCAREDPRTS CSDYWGQGTLVTVSS SEQ ID NO: 29522 |
| iPS:434247 | 21-225_62D2 | NA | GACATCCAGATGACCCAGTCTCCATCCTCCCT GTCTGCATCTGTAGGAGACAGAGTCACCATCA TTTGCCGGGCAAGTCAGAGCATTAGTCAGTTAT TTAAATTGGTATCAGCAGAAACCAGGGAAAG CCCCTAAGCTCCTGATCTATGCTACATCCAGTT TGCAAAGTGGGGTCCCATCAAGGTTCAGTGGC AGTGGATCTGGGACAGATTTCACTCTCACCAT CAGCAGTCTGCAACAGACTTACAGTCCCCCGCTC ACTACTGTCAACAGAGTTACAGTCCCCCCGCTC ACTTTCGGCGGAGGGACCAAGGTGGAGATCA AA SEQ ID NO: 25517 | CAGGTGTATCTGGTGGAGTCTGGGGGAGGCGTG GTCCAGCCTGGGAGGTCCCTGAGACTCTCCTGTG CAGCGTCTGATTCACCTTCAGTAGCTATGGCAT GCACCGTCCGCCAGGCTCCAGGCAAGGGCT GGAGTGGGTGGCAGTTATATGTATGATGGAAGT AATAAATACTCTGCAGACTCCGTGAAGGGCCGAT TCACCATCTCCAGAGACAATTCCAAGAACACGC GGATCTGCAAATGAACAGCCTGAGAGCCGAGGA CACGGCTGTGTATTACTGTGCGAGAGATAATGGT AACTGGAACTACCTTGACTACTGGGGCCAGGGA ACCCTGGTCACCGTCTCCTCA SEQ ID NO: 29523 |

FIGURE 50
(Continued)

| | | | |
|---|---|---|---|
| iPS:434249 | 21-225_62E2 | AA | DIQMTQSPSSLSASVGDRVTITCRASQSIISYLNW YQQKPGKAPKLLIYATSSLQSGVPSRFSGSGSGT DFTLTISSLQPEDFATYYCQQTYSPPLTFGGGTK VEIK<br>SEQ ID NO: 25518 | QVYLVESGGGVVQPGRSLRLSCAASGFTFSSYGMH WVRQAPGKGLEWVAVIWYDGSNKYSADSVKGRF TISRDNSKNTLDLQMNSLRAEDTAVYYCARDNGN WNYLDYWGQGTLVTVSS<br>SEQ ID NO: 29524 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCCGTT TGCAAAGTGGGGTCCCATCAAGGTTCAGCGGC AGTGGATCTGGGACAGACCTGAAGATTTTGCAACTT ATTACTGTCTACAGCATAGTAATTACCCTCTCA CTTTCGGCGGAGGGACCAGGGTTGAGATCAAA<br>SEQ ID NO: 25519 | CAGCTGCAGCTGCAGGAGTCGGGCCCAGGACTG GTGAAGCCTTCGGAGACCCTGTCCCTCACCTGTA TTGTCTCTGGTGGCTCCATCAGCAGAAGTAGTTA CTACTGGGGCTGGATCCGCCAGCCCCCAGGGAA GGGGCTGGAGTGGATTGGGAGCATCTATTATAGT GGGATCGCCTCCTATAATCCGTCCTCAAGAGTC GAGTCACCATATCCGTAGACACGTCCAAGAACC AGTTCTCCCTGAAGCTGAACTCTGTGACCGCCAC AGACACGGCTGTATATTACTGTGCGAGACTGAGC AGTGGCTGGTCCTTTGACTACTGGGGCCAGGGAA CCCTGGTCACCGTCTCCTCA<br>SEQ ID NO: 29525 |
| | | AA | DIQMTQSPSSLSASVGDRVTITCRASQGIRNDLG WYQQKPGKAPKRLIYAASRLQSGVPSRFSGSGS GTEFTLTISSLQPEDFATYYCLQHSNYPLTFGGG TRVEIK<br>SEQ ID NO: 25520 | QLQLQESGPGLVKPSETLSLTCIVSGGSISRSSYYWG WIRQPPGKGLEWIGSIYYSGIASYNPSLKSRVTISVD TSKNQFSLKLNSVTATDTAVYYCARLSSGWSFDY WGQGTLVTVSS<br>SEQ ID NO: 29526 |

FIGURE 50
(Continued)

| | | | | |
|---|---|---|---|---|
| iPS:434251 | 21-225_62G3 | NA | GACATCCATATGACCCAGTCTCCATCTCCT GTCTGCATCTGTAGGAGACAGAGTCACCATCA CTTGCCGGGCAAGTCAGGACATTAGAAATAAT TTAGGCTGGTATCAGCAGAAACCAGGGAAAG CCCCTAAGCGCCTGATCTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCGACT TATTACTGTCTACAGTATAATAGTTACCCATTC ACTTTCGGCCCTGGGACCAAAGTGGATATCAA A | GAGGTGCAGCTGGTGGAGTCTGGGGGAGGCTG GTCAAGCCTGGGGGGTCCCTGAGACTCTCCTGTG CAGCCTCTGGATTCACCTTCAGTAGTAGCTATAGCAT GAACTGGGTCCGCCAGGCTCCAGGGAAGGGGCT GGAGTGGGTCTCATCCATTAGTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTATATTACTGTGCGAGGGTTAACTCT TTTGACTCCTGGGGCCAGGGAACCCTGGTCACCG TCTCCTCA |
| | | | SEQ ID NO: 25521 | SEQ ID NO: 29527 |
| | | AA | DIHMTQSPSSLSASVGDRVTITCRASQDIRNNLG WYQQKPGKAPKRLIYTASSLQSGVPSRFSGSGSG TEFTLTISSLQPEDFATYYCLQYNSYPFTFGPGTK VDIK | EVQLVESGGGLVKPGGSLRLSCAASGFTFSSYSMN WVRQAPGKGLEWVSSISSSSYIYYADSVKGRFTIS RDNAKNSLYLQMNSLRAEDTAVYYCARVNSFDSW GQGTLVTVSS |
| | | | SEQ ID NO: 25522 | SEQ ID NO: 29528 |
| iPS:434253 | 21-225_62E4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAAACCAGGGAAAG CCCCTAAGCGCCTAATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAGTTATCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGCAGACTCCGTGAAGGGCCGA AATAAATACTATGCAGACTCCGTGAAGGGCCGA TTCACCATCTCCAGAGACAATTCCAAGAACACGC TGTATCTGCAAATGAACAGCCTGAGAGTGGAGG ACACGGCTGTATCACTGTGCGAGAGAGCTTGG GTTCAGCAGTGACTACTGGGGCCAGGGAACCCT GGTCACCGTCTCCTCA |
| | | | SEQ ID NO: 25523 | SEQ ID NO: 29529 |

FIGURE 50
(Continued)

| | | | | |
|---|---|---|---|---|
| iPS:434255 | 21-225_62E6 | AA | DIQMTQSPSSLSASVGDRVTITCRASQGIRNDLGWYQQKPGKAPKRLIYAAFSLQSGVPSRFSGSGSGTEFTLTISSLQPEDFATYYCLQHNSYPLTFGGGTKVEIK<br>SEQ ID NO: 25524 | QVQLVESGGGVVQPGRSLRLSCAASGFTFSDYGMHWVRQAPGKGLEWVAVIWYDRSNKYYADSVKGRFTISRDNSKNTLYLQMNSLRVEDTAVYHCARELGFSSDYWGQGTLVTVSS<br>SEQ ID NO: 29530 |
| | | NA | GAAATAGTGATGACGCAGTCTCCAGCCACCTGTCTGTGTCTCCAGGGGAAAGAGCCACCCTCCTGCAGGGCCAGTCAGAGTGTTAACAGCAACTTAGCCTGGTACCAGCAGAAACCTGGCCAGGCTCCCAGGCTCCTCATCTCTGTTGCATCCACCAGGGCCACTGGTATCCCAGCCAGGTTCAATGGCAGTGGGTCTGGGACAGAGTTCACTCTCACCATCAGCAGCCTGCAGTCTGAAGATAATGACTGGCCGTGTATTACTGTCAGCAGTATAATGACTGGCCGTGTAGTTTTGGCCAGGGGACCAAGCTGGAGATCAAA<br>SEQ ID NO: 25525 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGAGTCACCATCTCCAGAGACAATTCCAAGAACTCGCTGCATCTGCAAATGAACAGCCTGAGAGCCGAGGACACGGCTGTGTATTATTGTGCGAGAGATCAGGGCATAGTGGGAGCTACTTGGTTTGACTACTGGGGCCAGGGAACCCTGGTCACCGTCTCCTCA<br>SEQ ID NO: 29531 |
| | | AA | EIVMTQSPATLSVSPGERATLSCRASQSVNSNLAWYQQKPGQAPRLLISVASTRATGIPARFNGSGSGTEFTLTISSLQSEDFAVYYCQQYNDWPCSFGQGTKLEIK<br>SEQ ID NO: 25526 | QVQLVESGGGVVQPGRSLRLSCAASGFTFSSYGMHWVRQAPGKGLEWVAAIWYDGSNKYGDSVKGRVTISRDNSKNSLHLQMNSLRAEDTAVYYCARDQGIVGATWFDYWGQGTLVTVSS<br>SEQ ID NO: 29532 |

FIGURE 50
(Continued)

| | | | |
|---|---|---|---|
| iPS:434257 | 21-225_62F7 | NA | GACATCCAGATGACCCAGTCTCCATCCTCCCT GTCTGCATCTGTAGGAGACAGAGTCACCATCA CTTGCCGGGCAAGTCAGGCCATTAGAAATGAT TTAGGCTGGTATCAGCAGAAACCAGGGAAAG CCCCTAAGCGCCTGATCTATCCTGCATCCCGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGTATAATAGTTACCCTCCGT GGACGTTCGGCCAAGGGGTCCAAGGTGGAAAT CAAA<br><br>SEQ ID NO: 25527 | GAGGTGCAGCTGTTGGAGTCTGGGGGAGGCTTG GTTCAGCCTGGGGGGTCCCTGAGACTCTCCTGTG CAGCCCTCTGATTCACCTTTAGCAGCTATGTTAT GAGCTGGGTCCGCCAGGCTCCAGGGAAGGGCT GGAGTGGGTCTCAGTTATTAGTGGTAGTGGTGCT AAACATACTATGCAGACTCCGTGAAGGGCCGA TTCACCATCTCCAGAGACAATTCCAAGAACACGC TGTATCTGCAAATGAACAGCCTGAGAGCCGAGG ACACGGCCGTATATTACTGTGCGGAACTGGGGAT AGACTACTACTACGGTATGGACGTCTGGGGCCAA GGGACCACGGTCACCGTCTCCTCA<br><br>SEQ ID NO: 29533 |
| | | AA | DIQMTQSPSSLSASVGDRVTITCRASQAIRNDLG WYQQKPGKAPKRLIYPASRLQSGVPSRFSGSGS GTEFTLTISSLQPEDFATYYCLQYNSYPPWTFGQ GSKVEIK<br><br>SEQ ID NO: 25528 | EVQLLESGGGLVQPGGSLRLSCAASGFTFSSYVMS WVRQAPGKGLEWVSGISGSGAKTYYADSVKGRFT ISRDNSKNTLYLQMNSLRAEDTAVYYCAELGIDYY YGMDVWGQGTTVTVSS<br><br>SEQ ID NO: 29534 |
| iPS:434259 | 21-225_62G7 | NA | GACATCCAGATGACCCAGTCTCCATCTTCCGT GTCTGCATCTGTAGGAGACAGAGTCACCATCA CTTGTCGGGCGAGTCAGGATATTAGCAGCTGG TTAGCCTGGTATCAGCAGAAATCCAGGGAAGGC CCCTAAACTCCTGATCTATGCTGCATCCAGTTT GCAAAGTGGGGTCCCATCAAGGTTCAGCGGCA GTGGATCTGGGACAAATTCACTCTCACCATC AGCAGCCTCCAGCCTGAAGATTTTGCAACTTA CTATTGTCAACAGACTAACAGTTTCCCTCTCAC TTTCGGCGGAGGGACCAAGGTGGAGATCAAA<br><br>SEQ ID NO: 25529 | CAGGTGCAGCTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGAC TTGAGTGGATGGGATGGATCAACCACAGAAGTTTCAGGCA GTGGCACAAACCAAGCACAGGACACGTCCATCAGA GGTCACCATGACCAGGGACACGTCCATCAGCA CAGCCTACATGGAGCTGAGCAGTCTGAGATCTGA CGACACGGCCGTGTATTACTGTGCGAGAGCTCCG GGTATAGCAGCAGTGGTACATGGGATACTTTG ACTACTGGGGCCAGGGAACCCTGGTCACCGTCTC CTCA<br><br>SEQ ID NO: 29535 |

FIGURE 50
(Continued)

| | | | |
|---|---|---|---|
| iPS:434261 | | AA | DIQMTQSPSSVSASVGDRVTFTCRASQDISSWLA WYQQNPGKAPKLLIYAASSLQSGVPSRFSGSGS GTNFTLTISSLQPEDFATYYCQQTNSFPLTFGGGT KVEIK<br>SEQ ID NO: 25530 | QVQLVQSGAEVKKPGASVKVSCKASGYTFTGYYM HWVRQAPGQGLEWMGWIKPKSGGTNQAQKFQGR VTMTRDTSISTAYMELSSLRSDDTAVYYCARAPGI AAAGTWGYFDYWGQGTLVTVSS<br>SEQ ID NO: 29536 |
| | | NA | GACATCCTGATGACCCAGTCTCCATCCTCACT GTCTGCATCTGTAGGAGACAGAGTCACCATCA CTTGTCGGGCGAGTCAGGGCATTAGCAGTTAT TTAGCCTGGTTTCAGCAGAACACCAGGGACAGC CCCTAAGTCCCTGATCTATGCTGCATCCAGTTT GCAAGGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAATCAGTATAATAGTTTCCCATTTAA GTTCGGGACGTGGGACCAAAGTGGATATCACA<br>SEQ ID NO: 25531 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGTCTT AAACTGGGTCCGCCAGGCTCCAGGGAAGGGGCT GGAGTGGGTCTCAGTATGAGTGGTAGTGGTGGT AGAACATACTACGCAGACTCCGTGAAGGGCCGG TTCACCATCTCCAGAGACAACAATTCCAAGAACACGC TGTATCTGCAAATGAACAGCCTGAGAGCCGAGG ACACGGCCGTATATTTCTGTGCGATGACTACGCA CTTTGACTACTGGGGCCAGGGAACCCTGGTCACC GTCTCCTCA<br>SEQ ID NO: 29537 |
| 21-225_56F7 | | AA | DILMTQSPSSLSASVGDRVTITCRASQGISTYLA WFQQTPGTAPKSLIYAASSLQGGVPSKFSGSGSG TDFTLTISSLQPEDFATYYCHQYNSFPFKFGRGT KVDIT<br>SEQ ID NO: 25532 | EVQLLESGGGLVQPGGSLRLSCAASGFTFSSYVLN WVRQAPGKGLEWVSAMSGSGGRTYADSVKGRF TISRDNSKNTLYLQMNSLRAEDTAVYFCAMTTHFD YWGQGTLVTVSS<br>SEQ ID NO: 29538 |

FIGURE 50
(Continued)

| | | | |
|---|---|---|---|
| iPS:434263 | 21-225_56H7 | NA | GACATCCAGTGACCCAGTCTCCATCCTCCT GTCTGCATCTGTAGGAGACAGAGTCACCATCA CTTGCCGGGCAAGTCAGGACATTAGAAATGAT TTAGGCTGGTATCAGCAGAGGCCAGGGAAAG CCCCTAAGCGCCTGATCTATCCTGCATCCAGTT TGCTAAGTGGGGTCCCATCAAGGTTCAGCGGC AGTGGATCTGGGACAGAATTCACTCTCACAAT CAGCAGCCTGCAGCCTGAAGATTTTGCAACTT ACTACTGTCTACAGGATAATAGTTACCCATCC ACTTTCGGCCCTGGGACCAAAGTGGATATCAA A<br>SEQ ID NO: 25533 | GAGGTGCAGCTGGTGGAGTCTGGGGGAGGCTG GTCAAGCCTGGGGGGTCCCTGAGACTCTCCTGTG CAGCCCTCTGGATTCTCCTTCAGTAGCTATAGCAT GAACTGGGTCCGCCAGGCTCCAGGGAAGGGGCT GGAGTGGGTCTCATCCATTAGTAGTAGTAGTACT TACATATACTACGGAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGATCGGGG CAGCAGCTGGGGCCAGGGAACCCTGGTCACCGT CTCCTCA<br>SEQ ID NO: 29539 |
| | | AA | DIQLTQSPSSLSASVGDRVTITCRASQDIRNDLG WYQQRPGKAPKRLIYPASSLLSGVPSRFSGSGSG TEFTLTISSLQPEDFATYYCLQDNSYPFTFGPGTK VDSK<br>SEQ ID NO: 25534 | EVQLVESGGGLVKPGGSLRLSCAASGFSFSSYSMN WVRQAPGKGLEWVSSISSSSTYIYYGDSVKGRFTIS RDNAKNSLYLQMNSLRAEDTAVYYCARDRGSSW GQGTLVTVSS<br>SEQ ID NO: 29540 |
| iPS:434265 | 21-225_57B2 | NA | GACATCCAGATGACCCAGTCTCCATCCTCCCT GTCTGTATCTGTAGGAGACAGAGTCACCATCA CTTGCCGGGCAAGTCAGGGCATTAGAAATGCT TTAGGCTGGTATCAGCAGAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br>SEQ ID NO: 25535 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGT TACATAAACTACACAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGTGGCTGG CTTTGACTACTGGGGCCAGGGAACCCTGGTCACC GTCTCCTCA<br>SEQ ID NO: 29541 |

FIGURE 50
(Continued)

| | | | | |
|---|---|---|---|---|
| iPS:434267 | 21-225_57F2 | AA | DIQMTQSPSSLSVSVGDRVTITCRASQGIRNALG WYQQKPGKAPKRLIYAASSLQSGVPSRFSGSGS GTEFTLTISSLQPEDFATYYCLQHNSYPFTFGPGT KVDIK<br>SEQ ID NO: 25536 | EVQLVESGGGLVKPGGSLRLSCAASGFTFSSYSMN WVRQAPGKGLEWVSSISGSSSYINYTDSVKGRFTIS RDNAKNSLYLQMNSLRAEDTAVYYCARVAGFDY WGQGTLVTVSS<br>SEQ ID NO: 29542 |
| | | NA | GACATCCAGATGACCCAGTCTCCATCCTCCCT GTCTGCATCTGTAGGAGACAGAGTCACCATCA CTTGCCGGGCAAGTCAGAGTCAGAGCATTAGCAGCTAT TTAAATTGGTATCAGCAGAAACCAGGGAAAG CCCCTAAGCTCCTGATCTATGCTGCATCCAGT TGCAAAGTGGGGTCCCATCAAGGTTCAGTGGC AGTGGATCTGGGACAGAGATTTCACTCTCACCAT CAGCAGTCTGCAACCTGAAGATTTTGCACCTT ACTACTGTCAACAGAGAGTTACAATATTTCATTC ACTTTCGGCCCTGGGACCAAAGTGGATATCAA A<br>SEQ ID NO: 25537 | CAGGTGCAGCTGCAAGGAGTCGGGGCCAGGACTG GTGAAGCCTTCGGAGACCCTGTCCCTCACCTGCA CTGTCTCTGGTGGCTCCATCAGTAGTTACTACTG GAGCTGGATCCGGCAGCCCGCGGGAAGGGACT GGAGTGGATTGGGCGCATCTATACCAGGGGAG CACCAACTACAACCCCCTCCTCAAGAGTCGAGTC ACCATGTCAATAGACACGTCAAGAACCAGTTCT CCCTGAAGCTGAGCTCTGTGACCGCCGCGGACAC GGCCGTGTATTACTGTGCGAGAGAGGAAAAAC TGGGGGGTTTCTTACTTTGACTACTGGGGCCAG GGAACCCTGGTCACCGTCTCCTCA<br>SEQ ID NO: 29543 |
| | | AA | DIQMTQSPSSLSASVGDRVTITCRASQSISSYLNW YQQKPGKAPKLLIYAASSLQSGVPSRFSGSGSGT DFTLTISSLQPEDFAPYYCQQSYNISFTFGPGTKV DIK<br>SEQ ID NO: 25538 | QVQLQESGPGLVKPSETLSLTCTVSGGSISSYYWSW IRQPAGKGLEWIGRIYTRGSTNYNPSLKSRVTMSID TSKNQFSLKLSSVTAADTAVYYCAREGKTGGVSYF DYWGQGTLVTVSS<br>SEQ ID NO: 29544 |

FIGURE 50
(Continued)

| | | | | |
|---|---|---|---|---|
| iPS:434269 | 21-225_57H3 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCAGC TTAGCCTGGTACCAGCAGAAACCTGGCCAGGC TCCCAGGCTCCTCATCTATGGTGCATCCACCA GGGCCACTGGTTCCCAGCCAGGTTCAATGGC AGTGGGTCTTGGACAGAATTCACTCTCACCAT CAGCAGCCTGCAGTCAGTATGACTGCTGCGTGC ATTACTGTCAGCAGTATAATGACTGGCCGTGC AGTTTTGGCCAGGGACCAAGCTGGAGATCAA A | CAGGTGCAGTTGGTGGAGTCTGGGGGAGGCGTG GTCCAGCCTGGGAGGTCCCTGAGACTCTCCTGTG CAGCGTCTGATTCACCTTCAGTAGCTATGGCAT GCACTGGGTCCGCCAGGCTCCAGGCAAGGGGCT GGAGTGGGTGGCAGTATAGACTCCGTGAAGGGCG TAATAAATACTATCCAGAGACAATTCCAAGAACACG CTGTATCTGCAAATGAACAGCCTGAGAGCCGAG GACACGGCTGTGTATTACTGTGCGAGAGATTATG GTATAGTGGGAGCTACATATTTGACTACTGGGG CCAGGGAACCCTGGTCACCGTCTCCTCA |
| | | | SEQ ID NO: 25539 | SEQ ID NO: 29545 |
| | | AA | EIVMTQSPATLSVSPGERATLSCRASQSVSSSLA WYQQKPGQAPRLLIYGASTRATGFPARFNGSGS GTEFTLTISSLQSEDFAIYYCQQYNDWPCSFGQG TKLEIK | QVQLVESGGGVVQPGRSLRLSCAASGFTFSSYGMH WVRQAPGKGLEWVAAIWYDGSNKYYADSVKGRF TISRDNSKNTLYLQMNSLRAEDTAVYYCARDYGIV GATYFDYWGQGTLVTVSS |
| | | | SEQ ID NO: 25540 | SEQ ID NO: 29546 |
| iPS:434271 | 21-225_57A4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCTGCAGAAACCAGGGAAAGC CCCTAAGCGCCTGATCTATGCTGCATCCAGTTT GCTAAGTGGGGTCCCATCAAGGTTCAGCGGCA GTGGATCTGGGACAGAATTCACTCTCACAATC AGCAGCCTGCAGCCTGAAGATTTTGCAACTTA TTACTGTCTACACAGCATAATAGTACCATTCAC TTTCGGCCCTGGGACCAAAGTGGATATCAAA | CAGGTGCAGCTGGTGGTGGAGTCTGGGGGAGGCGTG GTCCAGCCTGGGAGGTCCCTGAGACTCTCCTGTG TAGCGTCTGGATTCACCTTCAGTGACTATGGCAT GCACTGGGTCCGCCAGGCTCCAGGCAAGGGGCT GGAGTGGGTGGCAGTTATATGTGAGTGGAAGT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGGGAACTGGGG ATGAGGTCTGACTACTGGGGCCAGGGAACCCTG GTCACCGTCTCCTCA |
| | | | SEQ ID NO: 25541 | SEQ ID NO: 29547 |

FIGURE 50
(Continued)

| | | | |
|---|---|---|---|
| | | AA | DIQMTQSPSSLSASVGDRVTITCRASQGIRNDLG WYLQKPGKAPKRLIYAASSLLSGVPSRFSGSGSG TEFTLTISSLQPEDFATYYCLQHNSYPFTFGPGTK VDIK<br><br>SEQ ID NO: 25542 | QVQLVESGGGVVQPGRSLRLSCVASGFTFSDYGM HWVRQAPGKGLEWVAVIWYAGSNKYYVDSVKGR FTISRDNSKNTLYLQMNSLRAEDTAVYYCARELGM RSDYWGQGTLVTVSS<br><br>SEQ ID NO: 29548 |
| iPS:434273 | 21-225_57E4 | NA | GACATCCAGATGACCCAGTCTCCATCTTCCGT GTCTGCATCTGTAGGAGACAGAGTCTCCATCA CTTGTCGGGCGAGTCAGGATATTAGCAACTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGTTCTGGGACAGATTTCACTCTCACCAT CAGCAGCCTGCAGCCTGAAGATTTTGCAACTT ACTCTTGTCAACAGGGTAACAGTTTCCCATTC ACTTTCGGCCCTGGGACCAAAGTGGATATCAA A<br><br>SEQ ID NO: 25543 | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGTTATTAGTGGTAGTGGTGGT AGTACATTCTACGCAGACTCCGTGAAGGGCCGGT TCACCATCTCCAGAGACAATTCCAAGACCACGCT GTATCTGCAAATGAACAGCCTGAGAGCCGAGGA CACGGCCGTATATTACTGTGCGAAAAGGGACTG GAACGACGTTTTGACTACTGGGGCCAGGGAACC CTGGTCACCGTCTCCTCA<br><br>SEQ ID NO: 29549 |
| | | AA | DIQMTQSPSSVSASVGDRVSITCRASQDISNWLA WYQQKPGKAPKLLIYAASSLQSGVPSRFSGSGS GTDFTLTISSLQPEDFATYSCQQGNSFPFTFGPGT KVDIK<br><br>SEQ ID NO: 25544 | EVQLLESGGGLVQPGGSLRLSCAASGFTFSSYAMS WVRQAPGKGLEWVSVISGSGGSTFYADSVKGRFTI SRDNSKTTLYLQMNSLRAEDTAVYYCAKRDWND VFDYWGQGTLVTVSS<br><br>SEQ ID NO: 29550 |

FIGURE 50
(Continued)

| | | | |
|---|---|---|---|
| iPS:434275 | 21-225_57F4 | NA | GACATCCAGATGACCCAGTCTCCATCCTCCT GTCTGCATCTGTAGGAGACAGAGTCACCATCA CTTGCCGGGCAAGTCAGTCATTAGAAATGAT TTAGGCTGGTATCAGCAGAAGCCAGGGAAAG CCCCTAAGCGCTTGATCTATGCTGCATCCAGT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATCACTGTCTACAGTATGTAGTTTCCCATTCA CTTTCGGCCCTGGGACCAAAGTGGATATCAAA<br>SEQ ID NO: 25545 | CAGGTGCAGCTGGTGGAGTCTGGGGGAGGCTTG GTCAAGCCTGGAGGGTCCCTGAGACTGTCCTGTG CAGCCTCTGGATTCATCTTCAGTGACTACTACAT GAACTGGATCCGCCAGGCTCCAGGGAAGGGGCT GGAGTGGGTTTCATACATTAGTAGTAGTGGTAGT ACCATATACTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGATATGATT ACGTGGGGCCAGGGAACCCTGGTCACCGTCTCCT CA<br>SEQ ID NO: 29551 |
| | | AA | DIQMTQSPSSLSASVGDRVTITCRASQVIRNDLG WYQQKPGKAPKRLIYAASSLQSGVPSRFSGSGS GTEFTLTISSLQPEDFATYHCLQYGSFPFTFGPGT KVDIK<br>SEQ ID NO: 25546 | QVQLVESGGGLVKPGGSLRLSCAASGFIFSDYYMN WIRQAPGKGLEWVSYISSSGSTIYYADSVKGRFTIS RDNAKNSLYLQMNSLRAEDTAVYYCARDMITWG QGTLVTVSS<br>SEQ ID NO: 29552 |
| iPS:434277 | 21-225_57A7 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAAACCAGGGAAAG CCCCTAACCTCCTGATCTATGCTGCATCCAATT TGCAAAGTGGGGTCCCATCAAGGTTCAGCGGC AGTGGATCTGGGACAGCCTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTAGATATCAA A<br>SEQ ID NO: 25547 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACCATA TACACTGGGTGCGACAGGCCCCTGGACAAGATCT TGAGTGGATGGGATGGATCAACATGAACAATAAT GGCACAAACTATGCACAGAAGTTTCAGGGCAGG GTCACCATGACCAGGGACACGTCCATCAGCACA GCCTACATGGAGCTGAGCAGGCTGAGATCTGAC GACACGGCCGTGTATTACTGTGCGAGAGATGGG AGAAGTGGTTTTGACTACTGGGGCCAGGGAACC CTGGTCACCGTCTCCTCA<br>SEQ ID NO: 29553 |

FIGURE 50
(Continued)

| | | | | |
|---|---|---|---|---|
| iPS:434279 | 21-225_57F7 | AA | DIQMTQSPSSVSASVGDRVTITCRASQGISRWLA WYQQKPGKAPNLLIYAASNLQSGVPSRFSGSGS GTDFTLTISSLQPEDFATYYCQQANSFPFTFGPGT KVDIK<br><br>SEQ ID NO: 25548 | QVQLVQSGAEVKKPGASVKVSCKASGYTFTGYHIH WVRQAPGQDLEWMGWINPNNNGTNYAQKFQGRV TMTRDTSISTAYMELSRLRSDDTAVYYCARDGRSG FDYWGQGTLVTVSS<br><br>SEQ ID NO: 29554 |
| | | NA | GAAATAGTGATGACGCAGTCTCCAGCCATCCT GTCTGTGTTTCCAGGGGAAAGAGCCACCCTCT CCTGCAGGGCCAGTCAGAGTGTTAGCAGCGAC TTAGCCTGGTACCAGCAGAAACCTGGCCAGGC TCCCAGGCTCCTCATCTATGGTGCATCCACCA GGGCCACTGGTGTATGCCAGCCAGGTTCAGTGGC GGTGGGTCTGGGACAGAGTTCACTCTCACCAT CAGCAGCCTGCAGTCTGAACATTTGCAGTTT ATTACTGTCAGCAGTAGTAACTGGCCATTC ACTTTCGGCCCTGGGACCAAAGTGGATATCAA A<br><br>SEQ ID NO: 25549 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATCTCCAGAGACAATCCAAGAACACGCT GTATTGCAAATGAACAGCTGAGAGCCGAGGA CACGGCCGTATATTACTGTGCGAAATTTTTCGGT GTAGTGGGAGTCGGGTGCTTTGACTACTGGGCC AGGGAACCCTGGTCACCGTCTCCTCA<br><br>SEQ ID NO: 29555 |
| | | AA | EIVMTQSPAILSVFPGERATLSCRASQSVSSDLA WYQQKPGQAPRLLIYGASTRATGMPARFSGGGS GTEFTLTISSLQSEHFAVYYCQQYSNWPFTFGPG TKVDIK<br><br>SEQ ID NO: 25550 | EVQLLESGGGLVQPGGSLRLSCAASGFTFSSYAMS WVRQAPGKGLEWVSAISGSGGNTFYADSVKGRFTI SRDNSKNTLYLQMNSLRAEDTAVYYCAKFFGVVG VGCFDYWGQGTLVTVSS<br><br>SEQ ID NO: 29556 |

FIGURE 50
(Continued)

| | | | |
|---|---|---|---|
| iPS:434281 | 21-225_57B8 | NA | GACATCCAGATGACCCAGTCTCCATCCTCCCT GTCTGCATCTGTAGGAGACAGAATCACCATCA CTTGCCGGGCAAGTCAGGGCATTGGAAATGAT TTAGGCTGGTATCAGCAGAAACCAGGGAAAG CCCCTGAGGCGCCTATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAACATAATAGTTTCCCTCCG TGGACGTTCGGCCAAGGGACCAAGGTGGAAA TCAAA<br>SEQ ID NO: 25551 | GAGGTGCAGCTGTTGGAGTCTGGGGGAGGCTTG GTACAGCCTGGGGGGTCCCTGAGACTCTCCTGTG CAGCCTCTGGATTCACCTTTAGAAGCTATGCCAT GAGCTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGA CACGGCCGTATATTACTGTGCGAAATTGGAACTG GGGATCTTTGACTACTGGGGCCAGGGAACCCTGG TCACCGTCTCCTCA<br>SEQ ID NO: 29557 |
| | | AA | DIQMTQSPSSLSASVGDRITITCRASQGIGNDLG WYQQKPGKAPERLIYAASSLQSGVPSRFSGSGSG TEFTLTISSLQPEDFATYYCLQHNSFPPWTFGQG TKVEIK<br>SEQ ID NO: 25552 | EVQLLESGGGLVQPGGSLRLSCAASGFTFRSYAMS WVRQAPGKGLEWVSAISGSGGNTFYADSVKGRFTI SRDNSKNTLYLQMNSLRAEDTAVYYCAKLELGIFD YWGQGTLVTVSS<br>SEQ ID NO: 29558 |
| iPS:434283 | 21-225_57F8 | NA | GACATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTATACTGCATCCAGTT TGCAAAGTGGGGTCCCATCAAGGTTCAGCGGC AATGAATCTGGGACAGATTTCACTCTCACCAT CAGCAGCCTGCAGCCTGAAGATTTTGCAACTT ACTATTGTCAACAGGCTAACAGTTTCCCGTGG ACGTTCGGCCAAGGGACCAAGGTGGAAATCA AA<br>SEQ ID NO: 25553 | GAGGTGCAGCTGTTGGAGTCTGGGGGAGGCTTG GTACAGCCTGGGGGGTCCCTGAGACTCTCCTGTG TAGTCTCTGGATTCACCTTTAGCAACTATGCCAT GAGCTGGGTCCGCCAGGCTCCAGGGAAGGGGCT GGAGTGGGTCTCAGCTAGCAGACTCCGTGAAGGGCCGG AACACATTCTACGCAGACTCCGTGAAGGGCCGG GTCACCATCTCCAGAGACAATTCCAAGAACACGC TGTATCTGCAAATGAACAGTCTGAGAGCCGAGG ACACGGCCGTATATTACTGTGCGAAACTGGGGA AGGACTACCACTACTACGGTATGGACGTCTGGGG CCAAGGGACCACGGTCACCGTCTCCTCA<br>SEQ ID NO: 29559 |

FIGURE 50
(Continued)

| | | | |
|---|---|---|---|
| iPS:434285 | 21-225_57A11 | AA | DIQMTQSPSSVSASVGDRVTITCRASQGISNWLAWYQQKPGKAPKLLIYTASSLQSGVPSRFSGNESGTDFTLTISSLQPEDFATYYCQQANSFPWTFGQGTKVEIK<br>SEQ ID NO: 25554 |
| | | | EVQLLESGGGLVQPGGSLRLSCVVSGFTFSNYAMSWVRQAPGKGLEWVSASSGSGNTFYADSVTGRVTISRDNSKNTLYLQMNSLRAEDTAVYYCAKLGKDYHYYGMDVWGQGTTVTVSS<br>SEQ ID NO: 29560 |
| | | NA | GACATCGTGATGACCCAGTCTCCAGACTCCCTGACTGTGTCTCTGGGCGAGAGGGCCACCATCAACTGCAAGTCCAGCCAAAGTGTTTTACACAGCTCCAACAATTATAACTACTTAGCTTGGTACCAGCAGAGACCAGGACAGCCTCCTAAGCTGGTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATATGGCAGTTTATTACTGTCAGCAATATTATAGTACTCCGTGGACGTTCGGCCAAGGGACCAAGGTGGAATTCAAA<br>SEQ ID NO: 25555 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCCTTGAGTGGATGGGATGGATGAACCCTAACAGTGTTAACACAGGCTATGCACAGAAGTTCCAGGGCAGAGTCACCATGACCAGGGACACATCGACAGCCTACATGGAGCTGAGCAGCCTGAGATCTGAGGACACGGCCGTGTATTACTGTGCGATCAGCAGTGGCTGGAACTGGTTCGACCCCTGGGGCCAGGAACCCTGGTCACCGTCTCCTCA<br>SEQ ID NO: 29561 |
| | | AA | DIVMTQSPDSLTVSLGERATINCKSSQSVLHSSNNYNYLAWYQQRPGQPPKLVIYWASTRASGVPDRFSGSGSGTDFTLTISSLQAEDMAVYYCQQYYSTPWTFGQGTKVEFK<br>SEQ ID NO: 25556 | QVQLVQSGAEVKKPGASVKVSCKASGYTFTNYDINWVRQATGQGLEWMGWMNPNSVNTGYAQKFQGRVTMTRDTSISTAYMELSSLRSEDTAVYYCAISSGWNWFDPWGQGTLVTVSS<br>SEQ ID NO: 29562 |

FIGURE 50
(Continued)

| | | | | |
|---|---|---|---|---|
| iPS:434287 | 21-225_57F12 | NA | GACATCGTGATGACCCAGTCTCCAGACTCCCT GGCTGTGTCTCTGGGCGAGAGGGCCACCATCA ACTGCAAGTCCAGCCAGAGTGTTTTATTCAGC TCCAACAATTACAATTACTTAGCTTGGTACCA GCAGAAACAGGACAGCCTCCAAGCTGATC ATTTACTGGGCATCTACCCGGGAATCCGGGT CCCTGACCGATTCAGTGGCAGCGGGTCTGGA CAGATTTCACTCTCACCATCAGCAGCCTGCAG GCTGAAGATGTGGCAATTTATTACTGTCAGCA ATATTATAGTAATCCGTGTAGTTTTGGCCAGG GGACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGATAAGCA GTGGCTGGTACCGGTTCGACCCCTGGGGCCAGGG AACCCTGGTCACCGTCTCCTCA SEQ ID NO: 29563 |
| | | | SEQ ID NO: 25557 | |
| | | AA | DIVMTQSPDSLAVSLGERATINCKSSQSVLFSSN NYNYLAWYQQKTGQPPKLIIYWASTRESGVPDR FSGSGSGTDFTLTISSLQAEDVAIYYCQQYYSNP CSFGQGTKLEIK | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAISSGW YRFDPWGQGTLVTVSS |
| | | | SEQ ID NO: 25558 | SEQ ID NO: 29564 |
| iPS:434289 | 21-225_57H12 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCGAC TTAGCCTGGTACCAGCAGAAACCTGGCCAGGC TCCCAGGCTCCTCCTCATCTATGCTGCATCTACCAG GGCCACTGGTATCCAGCCAGGTTCAGTGGCA GTGGGTCTGGGACAGAGTTCACTCTCACCATC AGCAGCCTGCAGTCTGAAGATTTTGCAGTTTA TTACTGTCAGCAGTATGATAACTGGCATTCA CTTTCGGCCCTGGGACCAAAGTGGATAACAAG | GAGGTGCAGCTGTTGGAGTCTGGGGGAGGCTTG GTACAGCCGGGGGGGTCCCTGAGACTCTCCTGTG CAGCCTCTGGATTAACGTTTAGTAGCTACGCCAT GAGCTGGGTCCGCCAGGATCCAGGGAAGGGGCT GGAGTGGGTCTCAGCTATTAGTGGTAGTGGTGGT AACACATTCTACGGAGACTCCGTGAAGGGCCGG TTCACCATCTCCAGAGACAATTCCAAGAAAACGC TGTATCTGCAAATGAACAGCCTGAGAGCCGAGG ACACGGCCGTATATTACTGTGCGAAATTTTTCGG TATAGTGGGTGCCGGGTACTTTGACTACTGGGGC CAGGGAACCCTGGTCACCGTCTCCTCA |
| | | | SEQ ID NO: 25559 | SEQ ID NO: 29565 |

FIGURE 50
(Continued)

| | | AA | EIVMTQSPATLSVSPGERATLSCRASQSVSSDLA WYQQKPGQAPRLLIYAASTRATGIPARFSGSGSG TEFTLTISSLQSEDFAVYYCQQYDNWPFTFGPGT KVDNK | EVQLLESGGGLVQPGGSLRLSCAASGLTFSSYAMS WVRQDPGKGLEWVSAISGSGGNTFYGDSVKGRFTI SRDNSKKTLYLQMNSLRAEDTAVYYCAKFFGIVGA GYFDYWGQGTLVTVSS |
| | | | SEQ ID NO: 25560 | SEQ ID NO: 29566 |
| iPS:434291 | 21-225_58A4 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCGAC TTAGCCTGGTACCAGCAGAAACCTGGCCAGGC TCCCAGGCTCCTCATCTATGCTGCATCTACCAG GGCCACTGGTATCCCAGCAGGTTCAGTGGCA GTGGGTCTGGGACAGAGTTCACTCTCACCATC AGCAGCCTGCAGTCTGAGGATTTTGCAGTTTA TTACTGTCAGCAGTTTAATAACTGGCCATTCA CTTTCGGCCCTGGGACCAAAGTGGATATCAAA | GAGGTGCAGCTGTTGGAGTCTGGGGGAGGCTTG GTACAGCCTGGGGGGTCCCTGAGACTCTCCTGTG CAGCCTCTGGATTAACGTTAGTAGTACGCCAT GAGCTGGGTCCGCCAGGATCCAGGGAAGGGCT GGAGTGGGTCTCAGCTATTAGTGGTAGTGGTGGT AACACATTCTACGGAGACTCCGTGAAGGGCCGG TTCACCATCTCCAGAGACAACAATTCCAAGAAAACGC TGTATCTGCAAATGAACAGCCTGAGAGCCGAGG ACACGGCCGTATATTACTGTGCGAAATTTTCGG TATAGTGGGAGCCGGGTTCTTTGACTCCTGGGGC CAGGGAACCCTGGTCACCGTCTCCTCA |
| | | | SEQ ID NO: 25561 | SEQ ID NO: 29567 |
| | | AA | EIVMTQSPATLSVSPGERATLSCRASQSVSSDLA WYQQRPGQAPRLLIYAASTRATGIPARFSGSGSG TEFTLTISSLQSEDFAVYYCQQFNNWPFTFGPGT KVDIK | EVQLLESGGGLVQPGGSLRLSCAASGLTFSSYAMS WVRQDPGKGLEWVSAISGSGGNTFYGDSVKGRFTI SRDNSKKTLYLQMNSLRAEDTAVYYCAKFFGIVGA GFFDSWGQGTLVTVSS |
| | | | SEQ ID NO: 25562 | SEQ ID NO: 29568 |

FIGURE 50
(Continued)

| | | | | |
|---|---|---|---|---|
| iPS:434293 | 21-225_58F5 | NA | GACATCCAGATGACCCAGTCTCCATCCTCCCT GTCTGCATCTGTAGGGGACAGAGTCACCATCA CTTGCCGGGCAAGTCAGGGCATTAGAAATGAT TTAGGCTGGTTTCTGCAGACACCAGGGAAAGC CCCTAAGCGCCTGATCTATGCTGCATCCAGTTT GCTAAGTGGGGTCCCATCACGGTTCGGCGGCA GTGGATCTGGGACAGATTCACTCTCACAATC AGCAGCCTGCAGCCTGAAGATTTTGCAACTTA TTACTGTCTACAGCATAATAGTTACCCATTCAC TTTCGGCCCTGGGACCAAAGTGGAGATCAAA SEQ ID NO: 25563 | CAGGTGCAGCTGGTGGAGTCTGGGGGAGGCGTG GTCCAGCCTGGGAGGTCCCTGAGACTCTCCTGTG TAGCGTCTGGATTCACCTTCAGTGACTATGGCAT GCACTGGGTCCGCCAGGCTCCAGGCAAGGGGCT GGAGTGGGTGGCAGTTATATGACTCCGTGAAGGGCCGA AATAAATACCATGTAGAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGAACTGG GATGAGGTCTGACTACTGGGGCCAGGGAACCCT GGTCACCGTCTCCTCA SEQ ID NO: 29569 |
| | | AA | DIQMTQSPSSLSASVGDRVTITCRASQGIRNDLG WFLQTPGKAPKRLIYAASSLLSGVPSRFGGSGSG TEFTLTISSLQPEDFATYYCLQHNSYPFTFGPGTK VEIK SEQ ID NO: 25564 | QVQLVESGGGVVQPGRSLRLSCVASGFTFSDYGM HWVRQAPGKGLEWVAVIWYAGSNKYHVDSVKGR FTISRDNSKNTLYLQMNSLRAEDTAVYYCARELGM RSDYWGQGTLVTVSS SEQ ID NO: 29570 |
| iPS:434295 | 21-225_58B9 | NA | GACATCGTGATGACCCAGTCTCCAGACTCCCT GGCTGTGTCTCTGGGCGAGAGGGCCACCATCA ACTGCAAGTCCGGCCAGAGTATTTTATACAGC TCCAACAATAACAACTACTTAGCTTGGTACCA GCAGAAACCAGGACAGCCTCCTAAGAAACTC ATTTACTGGGCATCTACCCGGGATTCCGGGGT CCCTGCCCGATTCAGTGGCAGCGGGTCTGGGA CAGATTTCACTCTCACCATCAGCAGCCTGCAG GCTGAAGATGTGGCAGTTTATTACTGTCAGCA ATATTATAGTACTCCTCCGACGTTCGGCCAAG GGTCCAAGGTGGAAATCAAA SEQ ID NO: 25565 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAGCACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGTATAGCAG TGGCTGGTACTACTTTGACTACTGGGGCCAGGGA ACCCTGGTCACCGTCTCCTCA SEQ ID NO: 29571 |

FIGURE 50
(Continued)

| | | | | |
|---|---|---|---|---|
| iPS:434297 | 21-225_58A10 | AA | DIVMTQSPDSLAVSLGERATINCKSGQSILYSSN NNNYLAWYQQKPGQPPKKLIYWASTRDSGVPA RFSGSGSGTDFTLTISSLQAEDVAVYYCQQYYST PPTFGQGSKVEIK<br><br>SEQ ID NO: 25566 | QVQLVQSGAEVKKPGASVKVSCKASGYTFTNYDIN WVRQATGQGLEWMGWMNPNSGSTGYAQKFQGR VTMTRNTSISTAYMELSSLRSEDTAVYYCAYSSGW YYFDYWGQGTLVTVSS<br><br>SEQ ID NO: 29572 |
| | | NA | GAAATAGTGATGACGCAGTCTCCAGCCACCCT GTCTGTGTCCAGGGGAAAGAGCCACCCTCT CCTGCAGGGCCAGTCAGAGTGTTAGCAGCTCC TTAGCCTGGTACCAGCAGAAACCTGGCCAGGC TCCCAGGCTCCTCATCTATGGTGCATCCACCA GGGCCACTGGTATCCCCAGCCAGGTTCAGTGGC AGTGGGTCTGGGACAGAGAATTCACTCTCACCAT CAGCAGCCTGCAGTCTGAAGATTTTGCAGTTT ATTACTGTCAGCAGTATATAACTGGCCATTC ACTTTCGGCCCTGGGACCAAAGTGGATATCAA A<br><br>SEQ ID NO: 25567 | GAGGTGCAGCTGTTGGAGTCTGGGGGAGGCTTG GTACAGCCTGGGGGGTCCCTGAGACTCTCCTGTG CAGCCTCTGGATTCACCTTCAGAAGTATGCCAT GAGCTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATCTCCAGAGACAATTCCAAGAACACGCT GTTTCTCCAAATGAACAGCCTGAGAGCCGAGGAC ACGGCCGTATATATTACTGTGCGAAATTTTTCGTA TAGTGGGAGCCGGGTACTTTGACTACTGGGGCCA GGGAACCCTGGTCACCGTCTCCTCA<br><br>SEQ ID NO: 29573 |
| | | AA | EIVMTQSPATLSVCPGERATLSCRASQSVSSSLA WYQQKPGQAPRLLIYGASTRATGIPARFSGSGSG TEFTLTISSLQSEDFAVYYCQQYNNWPFTFGPGT KVDIK<br><br>SEQ ID NO: 25568 | EVQLLESGGGLVQPGGSLRLSCAASGFTFRSYAMS WVRQAPGKGLEWVSAISGSGGNTFYADSVKGRFTI SRDNSKNTLFLQMNSLRAEDTAVYYCAKFFGIVGA GYFDYWGQGTLVTVSS<br><br>SEQ ID NO: 29574 |

FIGURE 50
(Continued)

| | | | | |
|---|---|---|---|---|
| iPS:434299 | 21-225_58D11 | NA | GACATCCAGATGACCCAGTCTCCATCCTCCT GTCTGCATCTGTAGGAGACAGAGTCACCATCA CTTGCCGGGCAAGTCAGGGCATTAGAAGTGAT TTAGACTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTGCAA TCAGCAGCCTGCGCGGCCTGAAGATTTTGCAACT TATTACTGTCTCCAGCATATAATAATTTCCCATTC ACTTTCGGCCCTGGGACCAAGGTGGATATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGACAT ACACTGGGTCCGCCAGTCTCCAGGCAAGGGGCT GGAGTGGGTGGCAGTTATATGGTATGATGAAGT AAAAAATATTATGCAGACTCCGTGAAGGGCCGA TTCACCATCTCCAGAGACAATTCCAAGAACACGT TGTATCTGCAAATGAACAGCCTGAGAGCCGAGG ACACGGCTCTGTATTACTGTGCGAGAGATCGGGT CACTTTTGACTACTGGGGCCAGGGAACCCTGGTC ACCGTCTCCTCA |
| | | | SEQ ID NO: 25569 | SEQ ID NO: 29575 |
| | | AA | DIQMTQSPSSLSASVGDRVTITCRASQGIRSDLD WYQQKPGKAPKRLIYAASSLQSGVPSRFSGSGS GTEFTLAISSLRPEDFATYYCLQHNNFPFTFGPGT KVDIK | QVQLVESGGGVVQPGRSLRLSCAASGFTFSDYDIH WVRQSPGKGLEWVAVIWYDGSKKYYADSVKGRF TISRDNSKNTLYLQMNSLRAEDTALYYCARDRVTF DYWGQGTLVTVSS |
| | | | SEQ ID NO: 25570 | SEQ ID NO: 29576 |
| iPS:434301 | 21-225_58F11 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAGCGAC TTAGTCTGGTACCAGCAGAAACCTGGCCAGGC TCCCAGGCTCCTCATCTATGGTGTATCCACCA GGGCCACTGGTATCCCAGCCAGGTTCAGTGGC AGTGGGTCTGGGACAGAGTTCACTCTCACCAT CAGCAGCCTGCAGTCTGAAGATTTTGCAGTT ATTACTGTCAGCAGTATAATAACTGGCCATTC ACTTTCGGCGGCCCTGGGACCAAAGTGGATATCAA A | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATAGCAGC AGCTGGTCCGCCAGGCTCCAGGGAAGGGGCTG GAGTGGGTCTCAGTATTAGTGGTAGTGGTGGTA ACACATTCTACGCAGACTCCGTGAAGGGCCGGTT CACCATCTCCAGATACAACAGCCTGAGAGCCGAGGAC TATCTGCAAATGAACAGCCTGAGAGCCGAGGAC ACGGCCGTATATTACTGTGCGAAATTTTCGGTA TGGTGGGAGCCGGATTCTTTGACTACTGGGGCCA GGGAACCCTGGTCACCGTCTCCTCA |
| | | | SEQ ID NO: 25571 | SEQ ID NO: 29577 |

FIGURE 50
(Continued)

| | | | | |
|---|---|---|---|---|
| iPS:434303 | 21-225_58H11 | AA | EIVMTQSPATLSVSPGERATLSCRASQSVSSDLV WYQQKPGQAPRLLIYGVSTRATGIPARFSGSGSG TEFTLTISSLQSEDFAVYYCQQYNNWPFTFGPGT KVDIK<br>SEQ ID NO: 25572 | EVQLLESGGGLVQPGGSLRLSCAASGFTFSSYAMS WVRQAPGKGLEWVSAISGSGGNTFYADSVKGRFTI SRYNSKNTLYLQMNSLRAEDTAVYYCAKFFGMVG AGFFDYWGQGTLVTVSS<br>SEQ ID NO: 29578 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GAGGGAAAGACCTATTTGTATTGGTACGTGCA GAAGCCAGGCCAGCCTCCACAACTCCTGATCT ATGAAGTTTCCTATCGGTTTTCTGGAGTGCCA GATAGGTTCAGTGGCAGCGGGTCAGGACAG ATTTCACACTGAAAATCAGCCGGGTGGAGGCT GAGGATGTTGGGGTTTATTACTGCATGCAAAG TATACAGCTTCCGCTCACTTTCGGCGGAGGGA CCAAGGTGGAGATCAAA<br>SEQ ID NO: 25573 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGCCAT GCACTGGGTCCGCCAGGCTCCAGGCAAGGGGCT GGAGTGGGTGGCAGTTATATGTGATGGAAGT AATAAATACCATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGGGGTATAG CAGCAGCTGGGACGGGGTATGGACGTCTGGGG CCAAGGGACCACGGTCACCGTCCTCCTCA<br>SEQ ID NO: 29579 |
| | | AA | DIVMTQTPLSLSVTPGQPASISCKSSQSLLHSEGK TYLYWYVQKPGQPPQLLIYEVSYRFSGVPDRFS GSGSGTDFTLKISRVEAEDVGVYYCMQSIQLPLT FGGGTKVEIK<br>SEQ ID NO: 25574 | QVQLVESGGGVVQPGRSLRLSCAASGFTFSSYGMH WVRQAPGKGLEWVAVIWYDGSNKYHADSVKGRF TISRDNSKNTLYLQMNSLRAEDTAVYYCARRYSSS WDGGMDVWGQGTTVTVSS<br>SEQ ID NO: 29580 |

FIGURE 50
(Continued)

| | | | | |
|---|---|---|---|---|
| iPS:434305 | 21-225_59E1 | NA | GACATCGTGATGACCCAGTCTCCAGACTCCCT GGCTGTGTCTCTGGGCGAGAGGGCCACCATCA ACTGCAAGTCCAGCCAGAGTGTTTATACAGC TCCAACAATAACAACTACTTAGCTTGGTACCA GCAGAGACCAGGACAGCCTCCTAAGTTGCTCA TTTACTGGTCATCTACCCGGGAATCCGGGGTC CCTGACCGATTCAGTGGCAGCGGGGTCTGGGAC AGATTTCACTCTCACCATCAGCAGCCTGCAGG CTGAAGATGTGGCAGTTTATTACTGTCAGCAA TATTTTAGTATTCCGTGCAGTTTGGCCAGGGG ACCAAGCTGGAGATCAAA SEQ ID NO: 25575 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGACTCCTAACAGTGG TAACACAGGCTATGCACAGAAGTTCCAGGGCAG AGTCACCATGACCAGGACCACCTCCATAAGCAC AGCCTACATGGAGCTGAGCAGCCTGAGATCTGA GGACACGGCCGTGTATTACTGTGCGTTTAGCAGT GGCTGGTACTTCTTTGACTACTGGGGCCAGGGAA CCCTGGTCACCGTCTCCTCA SEQ ID NO: 29581 |
| | | AA | DIVMTQSPDSLAVSLGERATINCKSSQSVLYSSN NNNYLAWYQQRPGQPPKLLIYWSSTRESGVPDR FSGSGSGTDFTLTISSLQAEDVAVYYCQQYFSIPC SFGQGTKLEIK SEQ ID NO: 25576 | QVQLVQSGAEVKKPGASVKVSCKASGYTFTNYDIN WVRQATGQGLEWMGWMTPNSGNTGYAQKFQGR VTMTRTTSISTAYMELSSLRSEDTAVYYCAFSSGW YFFDYWGQGTLVTVSS SEQ ID NO: 29582 |
| iPS:434307 | 21-225_59B2 | NA | GAAATTGTGTTGACGCAGTCTCCAGGCACCCT GTCTTTGTCTCCAGGGGAAAGAGCCACCCTCT CCTGCTGGGCCAGTCAGAGTGTTACAGCAGC TTCTTAGCCTGGTTCCAGCAGAAATCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTTTTACTGTCAGCAATATGGTACCTCACCGT GGACGTTCGGCCAAGGGACCAAGGTGGAAAT CAAA SEQ ID NO: 25577 | CAGGTGCAGTTGGTGCAGTCTGGGGCTGAGGTGA AGAAGCCTGGGGCCTCAGTGAAGGTCTCCTGCA AGGCTTCTGGATACACCTTCGCCGGCTACTATAT ACACTGGGTGCGACAGGCCCCTGGACAAGGACT TGAGTGGTTGGGTTGGATCAACCCTAACAGTGGT GGCACAAACTATGCACAGGAGTTTCAGGCAGG GTCACCATGACCAGGGACACGTCCATCAGCACA GCCTACATGGAGCTGAGCAGGCTGAGATTTGAC GACACGGCCGTGTATTACTGGGGCCAGGAGATCCGG GGCCCTTTGACTACTGGGGCCAGGGAACCCTGGT CACCGTCTCCTCA SEQ ID NO: 29583 |

FIGURE 50
(Continued)

| | | | |
|---|---|---|---|
| iPS:434309 | 21-225_59B5 | AA | EIVLTQSPGTLSLSPGERATLSCWASQSVYSSFLA WFQQKSGQAPRLLIYGASSRATGIPDRFSGSGSG TDFTLTISRLEPEDFAVFYCQQYGTSPWTFGQGT KVEIK<br>SEQ ID NO: 25578 | QVQLVQSGAEVKKPGASVKVSCKASGYTFAGYYI HWVRQAPGQGLEWLGWINPNSGGTNYAQKFQGR VTMTRDTSISTAYMELSRLRFDDTAVYYCARDPGP FDYWGQGTLVTVSS<br>SEQ ID NO: 29584 |
| | | NA | GACATCCAGATGACCCAGTCTCCATCCTCCCT GTCTGCATCTGTAGGAGACAGAGTCACCATCA CTTGCCGGGCAAGTCAGAGCATTATCAGTTAT TTAAATTGGTATCAGCAGAAACCAGGGAAAG CCCCTAAACTCCTGATCTATGGTGCATCCAGT TGCAGAGTGGGGTCCCATCAAGGTTCAGTGGC AGTGGATCCGGGACAGATTTCACTCTCACCAT CAGCAGTCTGCAACCTGAAGATTTTGCAACTT ACTACTGTCAACAGAGTTACAGTACCCCTATG TTCAGTTTTGGCCAGGGGACCAAGCTGGAGAT CAAA<br>SEQ ID NO: 25579 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATTTCCAGAGACAATTCCAAGAACACGCT GTATCTGCAAATGAACAGCCTGAGAGCCGAGGA CACGGCCGTATATTACTGTGCGAAAAGGGGGGT CTACGGTGACTACGAGGCTTTTGATATCTGGGGC CAAGGGACAAATGGTCACCGTCTCTTCA<br>SEQ ID NO: 29585 |
| | | AA | DIQMTQSPSSLSASVGDRVTITCRASQSIISYLNW YQQKPGKAPKLLIYGASSLQSGVPSRFSGSGSGT DFTLTISSLQPEDFATYYCQQSYSTPMFSFGQGT KLEIK<br>SEQ ID NO: 25580 | EVQLLESGGGLVQPGGSLRLSCAASGFTFSSYAMN WVRQAPGKGLEWVSAISGSGGNTFYADSVKGRFTI SRDNSKNTLYLQMNSLRAEDTAVYYCAKRGVYGD YEAFDIWGQGTMVTVSS<br>SEQ ID NO: 29586 |

FIGURE 50
(Continued)

| | | | | |
|---|---|---|---|---|
| iPS:434311 | 21-225_59H5 | NA | GAAATTGTGTTGACGCAGTCTCCAGGCACCCTGTCTTTGTCTCCAGGGGAAAGAGCCACCCTCTCCTGCAGGGCCAGTCAGAGTGTTAGCAGCATCTACTTAGCCTGGTTCCTGCAGAAACCTGGCCAGGCTCCCAGGCTCCTCATCTATGGTGCATCCAGCAGGGCCACTGGCATCCCAGACAGCAGGTTCAGTGGCAGTGGGTCTGGGACAGACTTCACTCTGACCATCAGCAGACTGGAGCCTGAAGATTTTGCAGTGTATTACTGTCACCAGTATGGTAACTCACCATTCACTTTCGGCCCTGGGACCAAAGTGATTTCAAA | CAGGTACAACTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGGGGTATAGCAGTGGGGTACTACGGTTATGGACGTCTGGGGCCAAGGGACCACGGTCACCGTCTCCTCA |
| | | | SEQ ID NO: 25581 | SEQ ID NO: 29587 |
| | | AA | EIVLTQSPGTLSLSPGERATLSCRASQSVSSIYLAWFLQKPGQAPRLLIYGASSRATGIPDRFSGSGSGTDFTLTISRLEPEDFAVYYCHQYGNSPFTFGPGTKVDFK | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARERGIAVGYYGMDVWGQGTTVTVSS |
| | | | SEQ ID NO: 25582 | SEQ ID NO: 29588 |
| iPS:434313 | 21-225_59E6 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGACGCCTGAAGATTCACTCTCACAATCAGCAGCCTGCAGCCTGAAGATTTTGCAACTTATTACTGTCTACAGCATAATAGTTACCCGCTCACTTTCGGCGGAGGGACCAAGGTGGAGATCAAA | CAGCTGCAGCTGCAGGAGTCGGGCCCAGGACTGGTGAAGCCTTCGGAGACCCTGTCCCTCACCTGCACTGTCTCTGGTGGCTCCATCAGTAGAAGTAGTTACTACTGGGGCTGGATCCGCCAGCCCCCAGGGAAGGGGCTGGAGTGGATTGGGAGTATCTATTATAGTGGGAGCACCTACTACAACCCGTCCCTCAAGAGTCGAGTCACCATATCCGTAGACACGTCCAAGAACCAGTTCTCCCTGAAGCTGAGCTCTGTGACCGCCGCAGCAGCCGCTCTGTGTATTACTGTGCGAGACATAGCAGCAGTGGTCCCTTGACTACTGGGGCCAGGGAACCCTGGTCACCGTCTCCTCA |
| | | | SEQ ID NO: 25583 | SEQ ID NO: 29589 |

FIGURE 50
(Continued)

| | | | | |
|---|---|---|---|---|
| iPS:434315 | 21-225_59G7 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TRVEIK<br><br>SEQ ID NO: 25584 | QLQLQESGPGLVKPSETLSLTCTVSGGSISRSSYYW GWIRQPPGKGLEWIGNIYSGSTYYNPSLKSRVTIS VDTSKNQFSLKLSSVTAADTALYYCARHSSSWSLD YWGQGTLVTVSS<br><br>SEQ ID NO: 29590 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATTCTGCATCCAGTT TACAAAGTGGGGTCCCATCCAAGGTTCAGCGGC AGTGGATCTGGGACAGAATTCACTCTCACAAT CAGCAGCCTGCAGCCTGAAGATATTTGCAACTT ATTACTGTCTACAGCATAATAGTTACCCGTGG ACGTTCGGCCAAGGGACCAAGGTGGAAATCA AA<br><br>SEQ ID NO: 25585 | CAGGTGCAACTAGTGCAGTCTGGGGCTGAGGTG AAGAAGCCTGGGGCCTCAGTGAAGGTCTCCTGC AAGGCTTCTGGATACAGTTTCACCGGCCACTATA TACACTGGGTGCGACAGGCCCCTGGACAAGGGC TTGAGTACATGGGATGGATCAACCCGAACAGTG GTGGCACAAACTATGTACCAGGGACAGTCCATCAGCA CAGCCTACATGGAGCTGAGCAGGCTGAGATCTG ACGACACGGCCATATATTACTGTGTCGAGAGGGG GCCTACTGGGAGCTACCAACTACTACTACTACGG TATGGACGTCTGGGGCCAAGGGACCACGGTCAC CGTCACCTCA<br><br>SEQ ID NO: 29591 |
| | | AA | DIQMTQSPSSLSASVGDRVTITCRASQGIRNDLG WYQQKPGKAPKRLIYSASSLQSGVPSRFSGSGSG TEFTLTISSLQPEDFATYYCLQHNSYPWTFGQGT KVEIK<br><br>SEQ ID NO: 25586 | QVQLVQSGAEVKKPGASVKVSCKASGYSFTGHYIH WVRQAPGQGLEYMGWINPNSGGTNYVQKFQGRV TMTRDTSISTAYMELSRLRSDDTAIYYCSRGGLLGA TNYYYGMDVWGQGTTVTVTS<br><br>SEQ ID NO: 29592 |

FIGURE 50
(Continued)

| | | | |
|---|---|---|---|
| iPS:434317 | 21-225_59E8 | NA | GACATCCAGATGACCCAGTCTCCATCCTCCT GTCTGCATCTGTAGGAGACAGAGTCACCATCA CTTGCCGGGCAAGTCAGAGACATTAGCAGCTAT TTAAATTGGTATCAGCAGAAACCAGGAAAG CCCCTAAGCTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACTGAAGATTTTGCAACTT ACTTCTGTCAACAGAGTTTCAGTAATTCGATC ACCTTCGGCCAAGGGACACGACTGGAGATTAA A | GAGGTGCAGCTGGTGGAGTCTGGGGGAGGCTTG GTACAGCCTGGGGGGTCCCTGAGACTCTCCTGTG CAGCCCTCTGATTCACTTTCAGTAGTAGCAT GAATTGGGTCCGCCAGGCTCCAGGGAAGGGCT GGGGTGGGTGTCATACATTAGTAGTAGTGG ACCATATACTACGCAGACTCTGTGAAGGGCCGAT TCACCATCTCCAGAGACAATGCCAAGAACTACT GTATCTGCAAATGAACAGCCTGAGAGACGAGGA CACGGCTGTGTATTACTGTGCGAGAGAATGGGGA ATGGCAGTGGCTGGCCCGTTGACTACTGGGGCC AGGGAACCCTGGTCACCGTCTCCTCA |
| | | | SEQ ID NO: 25587 | SEQ ID NO: 29593 |
| | | AA | DIQMTQSPSSLSASVGDRVTITCRASQSISSYLNW YQQKPGKAPKLLIYAASSLQSGVPSRFSGSGSGT DFTLTISSLQPEDFATYFCQQSFSNSITFGQGTRL EIK | EVQLVESGGGLVQPGGSLRLSCAASGFTFSSYSMN WVRQAPGKGLGWVSYISSSSGTIYYADSVKGRFTIS RDNAKNSLYLQMNSLRDEDTAVYYCAREWGMAV AGPFDYWGQGTLVTVSS |
| | | | SEQ ID NO: 25588 | SEQ ID NO: 29594 |
| iPS:434319 | 21-225_59B9 | NA | GACATCCAGATGACCCAGTCTCCATCCTCCCT GTCTGCATCTGTAGGAGACAGAGTCACCATCA CTTGCCGGGCAAGTCAGGACAGTTAGGACAATTAGGACA TTAGGCTGGTATCAGCAGCACCAGGGAAAGC CCCTAAGCGCCTGATCTATGCTGCATCCAGTTT ACAAAGTGGGGTCCCATCAAGGTTCAGCGGCA CTAGATCTGGGACAGATTCACTCTCACAATC AGCAGCCTGCAGCCTGAAGATTTTGCAACTTA TTACTGTCTACAGCATATAATAGTTACCCGTGGA CGTTCGGCCAAGGGACCAAGGTGGAAATCAA A | CAGGTGCAGCTGCAGGTGCAGTCTGGGCCTGAGGTG AAGAAGCCTGGGGCCTCAGTGAAGGTCTCCTGC AAGGCTTCTGGATACATCTTCACCGGCAATTATA TACACTGGGTGCGACAGGCCCCTGGACAAGGGC TTGAGTACATGGGATGGATCAACCCTAACAGTGG TGGCACAAACTATGTACAGAAGTTTCAGGGCAG GGTCACCATGACCAGGGACACGTCCATCAGCAC AGCCAACATGGAACTGACCAGTCTGAGATCTGA CGACACGGCCGTGTATTACTGTGTTGAGAGGGGGC CTACTGGGAGCTACTACTACTACTACTACGGTA TGGACGTCTGGGGCCAAGGGACCACGGTCACCG TCTCCTCA |
| | | | SEQ ID NO: 25589 | SEQ ID NO: 29595 |

FIGURE 50
(Continued)

| | | | |
|---|---|---|---|
| iPS:434321 | 21-225_59F10 | AA | DIQMTQSPSSLSASVGDRVTITCRASQDIRNDLG WYQQHPGKAPKRLIYAASSLQSGVPSRFSGTRS GTEFTLTISSLQPEDFATYYCLQHNSYPWTFGQG TKVEIK<br>SEQ ID NO: 25590 | QVQLVQSGPEVKKPGASVKVSCKASGYIFTGNYIH WVRQAPGQGLEYMGWINPNSGGTNYVQKFQGRV TMTRDTSISTANMELTSLRSDDTAVYYCSRGGLLG ATYYYYGMDVWGQGTTVTVSS<br>SEQ ID NO: 29596 |
| | | NA | GACATCGTGATGACCCAGTTTCCAGACTCCCT GGCTGTGTCTCTGGGCGAGAGGGCCACCATCA ACTGCAAGTCCAGCCAGACTGTTTATACAGG TCCAACAATTACAACTACTTAGCTTGGTACCA GCAGAAACCAGGACAGGCCTCCTAAGCTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTTTAGTACTCCTCCGACGTTCGGCCAAGG GACCAAGGTGGAAATCAAA<br>SEQ ID NO: 25591 | CAGGTGCAGCTGGTGCAGTCTGGGGCTGAGGTG AAGAAGCCTGGGGCCTCAGTGAAGGTCTCCTGC AAGGCTTCTGGATACACCTTCACAAATTATGATA TCAACTGGGTGCGACAGGCCACTGGACAAGGC TTGAGTGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATAACTGTGCGGTTAGCA GTGGCTGGTACTACTTTGACTACTGGGGCCAGGG AACCCTGGTCACCGTCTCCTCA<br>SEQ ID NO: 29597 |
| | | AA | DIVMTQFPDSLAVSLGERATINCKSSQTVLYRSN NYNYLAWYQQKPGQPPKLLIYWASTRESGVPD RFSGSGSGTDFTLTISSLQAEDVAVYYCQQYFST PPTFGQGTKVEIK<br>SEQ ID NO: 25592 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYNCAVSSGW YYFDYWGQGTLVTVSS<br>SEQ ID NO: 29598 |

FIGURE 50
(Continued)

| | | | | |
|---|---|---|---|---|
| iPS:434323 | 21-225_62H8 | NA | GACATCCAGATGACCCAGTCTCCATCCTCCCT GTCTGCATCTGTAGGAGACAGAGTCACCATCA CTTGCCGGGCAAGTCAGAGACATTTCAGCTAT TTAAATTGGTATCAGCAGAAATCCGGGAAAGC CCCTAAGCTCCTGATCTATGCGTCATCCAGTTT GCAAAGTGGGGTCCCATCAAGGTTAAGTGGCA ATGGATCTGGGACAGATTTCATTCTCACCATC AGCAGTCTGCAACCTGAAGATTTTGCAACTTA CTACTGTCAACAGAGTTACAGTACCCCATTCA CTTTCGGCCCTGGGACCAGAGTGGATATCAAA<br><br>SEQ ID NO: 25593 | CAGGTGCAGCTGGTGGAGTCTGGGGGAGGCGTG GTCCAGCCTGGGAGGTCCCTGAGACTCTCCTGTG CAGCGTCTGGATTCACCTTCAGCACCTATGGCAT GCACTGGGTCCGCCAGGCTCCAGGCAAGGGCT GGAGTGGGTGGCAGTTATATGGACATGATGGAAG TGATAAATATTATGTAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGACCC GCGTACCAGCTGCTCTGACTACTGGGGCCAGGGA ACCCTGGTCACCGTCTCCTCA<br><br>SEQ ID NO: 29599 |
| | | AA | DIQMTQSPSSLSASVGDRVTITCRASQSIFSYLNW YQQNPGKAPKLLIYASSSLQSGVPSRLSGNGSGT DFTLTISSLQPEDFATYYCQQSYSTPFTFGPGTRV DIK<br><br>SEQ ID NO: 25594 | QVQLVESGGGVVQPGRSLRLSCAASGFTFSTYGMH WVRQAPGKGLEWVAVIWHDGSDKYYVDSVKGRF TISRDNSKNTLYLQMNSLRAEDTAVYYCAREDPRT SCSDYWGQGTLVTVSS<br><br>SEQ ID NO: 29600 |
| iPS:434327 | 21-225_63G6 | NA | GACATCCAGATGACCCAGTCTCCATCCTCCCT GTCTGCATCTGTAGGAGACAGAGTCACCATCA CTTGCCGGGCAAGTCAGAGCATTTCAGCTAT TTAAATTGGTATCAGCAGAAACCAGGGAAAGC CCCTAAGCTCCTGATCTATGATACATCCACTTT GCAAAGTGGGGTCCCATCAAGGTTCAGTGGCA GTGGATCTGGGACAGATTTCACTCTCACCATC AACAGTCTGCAACCTGAAGATTTTGCAACTTA CTACTGTCAACAGAGTTACGGTATCCCATCA CCTTCGGCCAAGGGACACGACTGGAGATTCAA<br><br>SEQ ID NO: 25595 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATAGCCT CTGGGTATAGCAGCAGTTTGACTACTGGGGC CAGGGAACCCTGGTCACCGTCTCCTCA<br><br>SEQ ID NO: 29601 |

FIGURE 50
(Continued)

| | | AA | DIQMTQSPSSLSASVGDRVIISCRASQSIFSYLNW YQVKPGKAPKLLIYDTSTLQTGVPSRFSGSGSGT DFTLTINSLQPEDFATYYCQQSYGIPITFGQGTRL EIQ<br><br>SEQ ID NO: 25596 | QVQLVESGGGVVQPGRSLRLSCAASGFTFSSYGMH WVRQAPGKGLEWTVIWYDGSNKYYADSVKGRF TISRDNSKNTLYLQMNSLRAEDTAVYYCARDSLSG IAAAFDYWGQGTLVTVSS<br><br>SEQ ID NO: 29602 |
|---|---|---|---|---|
| iPS:434331 | 21-225_63H8 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCATAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAACAATATCATAGTTACCCATTCA CTTTCGGCCCTGGGACCAAAGTGGATATCAGA<br><br>SEQ ID NO: 25597 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAACAT GAACTGGGTCCGCCAGGCTCCAGGGAAGGGGCT GGAGTGGGTCTCATCCATTAGTGGTAGTAGCACT TACATGAACTACACAGACTCAGTGAAGGGCCGA TTCACCATCTCAAGAGACAACGCCAAGAACTCAC TGTATCTGCAAATGAACAGCCTGAGAGCCGAGG ACACGGCTGTGTATTACTGTGCGAGACTACGTAA TTTGACTACTGGGGCCAGGGAACCCTGGTCACC GTCTCCTCA<br><br>SEQ ID NO: 29603 |
| | | AA | DIQMTQSPSSLSASVGDRVTITCRASQGISNYLA WFQQKPGKAHKSLIYAASSLQSGVPSKFSGSGS GTDFTLTISSLQPEDFATYYCQQYHSYPFTFGPG TKVDIR<br><br>SEQ ID NO: 25598 | EVQLVESGGGLVKPGGSLRLSCAASGFTFSSYNMN WVRQAPGKGLEWVSSISGSSTYMNYTDSVKGRFTI SRDNAKNSLYLQMNSLRAEDTAVYYCARLRNFDY WGQGTLVTVSS<br><br>SEQ ID NO: 29604 |

FIGURE 50
(Continued)

| | | | |
|---|---|---|---|
| iPS:434333 | 21-225_63C9 | NA | GACATCCAGATGACCCAGTCTCCATCTTCCGT GTCTGCATCTGTGGAGACAGAGTCACCATCA CTTGTCGGGCGAGTCAGGGTATTAGCAGCTGG TTAGCCTGGTATCAGCAGAAACCAGGGAAAG CCCCTAACCTCCTGATCTATGCTGCATCAGTT TGCAAAGTGGGGTCCCATCAAGGTTCAGCGGC AGTGGATCTGGGACAGATTTCACGCTCACCAT CAGCGGCCTGCAGCCTGAAGATTTTGCAACTT ACTTTTGTCAACAGATTAACAGTTTCCCTCTCA CTTTCGGCGGAGGGACCAAGGTGGCGATCAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTTTGCACAGAAGTTTCAGGGCAG GGTCACCATGACCAGGGACGCGTCCATCAACAC AGCCTACATGGAGCTGCGCAGCCTGATATCTGAC GACACGGCCGTATATTACTGTGCGAGAGCTCCGG GTGTAGCAGCAGCTGGTTCATGGGGATACTTTGA CTACTGGGGCCAGGGAACCCTGGTCACCGTCTCC TCA |
| | | | SEQ ID NO: 29605 |
| | | AA | DIQMTQSPSSVSASVGDRVTITCRASQGISSWLA WYQQKPGKAPNLLIYAASSLQSGVPSRFSGSGS GTDFTLTISGLQPEDFATYFCQQINSFPLTFGGGT KVAIK | QVQLVQSGAEVKKPGASVKVSCKASGYTFTGYYM HWVRQAPGQGLEWMGWINPNSGGTNFAQKFQGR VTMTRDASINTAYMELRSLISDDTAVYYCARAPGV AAAGSWGYFDYWGQGTLVTVSS |
| | | | SEQ ID NO: 25600 | SEQ ID NO: 29606 |
| iPS:434335 | 21-225_63C10 | NA | GACATCCAGATGACCCAGTCTCCGTCCCCT GTCTACATCTGTAGGAGACAGAGTCACCATCA CTTGCCGGGCAAGTCAGAGCATTTTCAGCTAT TTACATTGGTATCAGCAGAAACCAGGGAAAGC CCCTAAGCTCCTGATCTCTGCTGCATCCAGTTT ACAAAGTGGGGTCCCATCAAGGTTCAGTGGCA GTGGATCTGGGACAGATTTCACTCTCACCATC AGTAGTCTGCAACCTGAAGATTTTGCAACTTT CTACTGTCAACAGACTTACAGTCCCCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGACTGGGTGGCAGTCATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGATCC CAGATCCTCGCCGGGACTACTGGGGCCAGG AACCCTGGTCACCGTCTCCTCA |
| | | | SEQ ID NO: 25601 | SEQ ID NO: 29607 |

FIGURE 50
(Continued)

| | | | | |
|---|---|---|---|---|
| iPS:434337 | 21-225_64E1 | AA | DIQMTQSPSSLSTSVGDRVTITCRASQSIFSYLHWYQQKPGKAPKLLISAASSLQSGVPSRFSGSGSGTDFTLTISSLQPEDFATFYCQQTYSPPLTFGGGTKVEIK<br>SEQ ID NO: 25602 | QVQLVESGGGVVQPGRSLRLSCAASGFTFSSYGMHWVRQAPGKGLDWVAVIWYDGSNKYYADSVKGRFTISRDNSKNTLYLQMNSLRAEDTAVYYCARDDPRSSAGDYWGQGTLVTVSS<br>SEQ ID NO: 29608 |
| | | NA | GACATCCAGATGACCCAGTCTCCATCCTCCCTGTCTGCATCTGTAGGAGACAGAGTCACCATCACTTGCCGGGCAAGTCAGGGCATTAGCAGTTATTTACATTGGTATCAGCAGAAACCAGGGAAAGCCCCTAAGCGCCTGATCTATGCTGCATCCAGTTTGCAAAGTGGGGTCCCATCACGGTTCAGCGGCAGTAAATCTGGGACAGAATTCACTCTCACAATCAGCAGCCTGCAGCCTGAAGATTTTGCAACTTATTACTGTCTACAGCATATAAGTTACCCGCTCACTTTCGGCGGAGGGACCAAGGTGGAGATCAAA<br>SEQ ID NO: 25603 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTTTGATGAAACTAATAAATACTATGGAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGCTTGGGTTCAGCAGTGACTATTGGGGCCAGGGAACCCTGGTCACCGTCTCCTCA<br>SEQ ID NO: 29609 |
| | | AA | DIQMTQSPSSLSASVGDRVTITCRASQGIRNDLGWYQQKPGKAPKRLIYAASSLQSGVPSRFSGSKSGTEFTLTISSLQPEDLATYYCLQHNSYPLTFGGGTKVEIK<br>SEQ ID NO: 25604 | QVQLVESGGGVVQPGRSLRLSCVASGFTFSSYGMHWVRQAPGKGLEWVAVIWFDETNKYYGDSVKGRFTISRDNSKNTLYLQMNSLRAEDTAVYYCARELGFSSDYWGQGTLVTVSS<br>SEQ ID NO: 29610 |

FIGURE 50
(Continued)

| | | | | |
|---|---|---|---|---|
| iPS:434339 | 21-225_64A4 | NA | GACATCCAGATGACCCAGTCTCCATCCTCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAACGCCTGATCTATGCTGCATCCAGT TTGCAAAGTGGGGTCCCATCAAGGTTCAGCGG CAGTGGATCTGGGACAGAATTCACTCTCACAA TCAGCAGCCTACAGCCTGAAGATCTTTGCAACT TATTACTGTCTACAGCATTATAGTTACCCTCGG ACGTTCGGCCAAGGGACCAAGGTGGAAATCA AA | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGCGATTATGTCAT GCACTGGGTCCGCCAGGCTCCAGCAAGGGCT GGAGTGGGTGGCAGTCATATGGTATGATGGAAG TAATAAATACTATGCAGACTCCGTGAAGGGCCG ATTCACCATCTCCAGAGACAATTCCCAGAACACG CTGTATCTGCAAATGAATAGCCTGAGAGCCGAG GACACGGCTGTGTATTACTGTGCGAGAGAAAGGT ATAGCAGCAGCTGGTACGACTACGGTATGGACG TCTGGGGCCAAGGGACCACGGTCACCGTCTCCTC A |
| | | | SEQ ID NO: 25605 | SEQ ID NO: 29611 |
| | | AA | DIQMTQSPSSLSASVGDRVTITCRASQGIRNDLG WYQQKPGKAPKRLIYAASSLQSGVPSRFSGSGS GTEFTLTISSLQPEDLATYYCLQHYSYPRTFGQG TKVEIK | QVQLVESGGGVVQPGRSLRLSCAASGFTFSDYVM HWVRQAPGKGLEWVAVIWYDGSNKYYADSVKGR FTISRDNSQNTLYLQMNSLRAEDTAVYYCARERYS SSWYDYGMDVWGQGTTVTVSS |
| | | | SEQ ID NO: 25606 | SEQ ID NO: 29612 |
| iPS:434341 | 21-225_64F7 | NA | GACATCCAGATGACCCAGTCTCCATCCTCCT GTCTGCATCTGTAGGAGACAGAGTCACCATCA CTTGCCGGGCAAGTCAGAACATTAAGAAATAT TTAAATTGGTATCAGCAGAAACCAGGGAAAG CCCCTAAGTTCCTAAGTCTATGGTGCATCCAGT TGCAAAGTGGGGTCCATCAAGGTTCAGTGGC AGTGGATCTGGGACAGAACTTCACTCTCACCAT CAGTAGTCTGCAACCTGAAGATTTTGCAGTT ACTACTGTCAACAGAGTTACAATATTTCGTTC ACTTTCGGCGGAGGGACCAAGGTGGAGCTCA AA | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTTCTGG AGCTGGATCCGGCAGCCCCCCGGGAAGGGACTG GAGTGGATTGGGCGTATCTATACCAGTGGGATCT CCAACTACAACCCCTCCCTCAAGAGTCGAGTCAC CATGTCAGTTGACACGTCCAAGAACCAGTTCTCC CTGAAGCTGAGCTCTGTGACCGCCGCGGACACG GCCGTGTATTACTGTGCGAGGTTTAGCAGTGGCT TTTTTGACTACTGGGGCCAGGGTACCCTGGTCAC CGTCTCCTCA |
| | | | SEQ ID NO: 25607 | SEQ ID NO: 29613 |

FIGURE 50
(Continued)

| | | | |
|---|---|---|---|
| iPS:434343 | 21-225_64C8 | AA | DIQMTQSPSSLSASVGDRVTITCRASQNKKYLN WYQQKPGKAPKFLIYGASSLQSGVPSRFSGSGSG TDFTLTISSLQPEDFAAYYCQQSYNISFTFGGGTK VELK<br>SEQ ID NO: 25608 | QVQLQESGPGLVKPSETLSLTCTVSGGSISSYFWSW IRQPAGKGLEWIGRIYTSGISNYNPSLKSRVTMSVD TSKNQFSLKLSSVTAADTAVYYCARPSSGFFDYWG QGTLVTVSS<br>SEQ ID NO: 29614 |
| | | NA | GACATCCAGATGACCCAGTCTCCATCCTCCCT GTCTGCAGCTGTAGGAGACAGAGTCACCATCA CTTGCCGGGCAAGTCAGGGCATTAGAAATGAT TTAGGCTGGTATCAGCAGAAACCAGGGAAAG CCCCTAAGTGCCTGATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTATTGTCTACACACCATTATAGTTACCCTCGGA CGTTCGGCCAAGGGACCAAGGTGGAAATCAA A<br>SEQ ID NO: 25609 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGGCAGTTATATGTATGATGGAAGT AATAAATACTATGCAGACTCCATGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGAACGGTA TAGCAGTGGCTGGTACGACTACGGTATGGACGTC TGGGGCCAAGGGACCACGGTCACCGTCTCCTCA<br>SEQ ID NO: 29615 |
| | | AA | DIQMTQSPSSLSAAVGDRVTITCRASQGIRNDLG WYQQKPGKAPKCLIYAASSLQSGVPSRFSGSGS GTEFTLTISSLQPEDFATYYCLHHYSYPRTFGQG TKVEIK<br>SEQ ID NO: 25610 | QVQLVESGGGVVQPGRSLRLSCAASGFTFSDYVM HWVRQAPGKGLEWVAVIWYDGSNKYYADSMKG RFTISRDNSKNTLYLQMNSLRAEDTAVYYCARERY SSGWYDYGMDVWGQGTTVTVSS<br>SEQ ID NO: 29616 |

FIGURE 50
(Continued)

| | | | | |
|---|---|---|---|---|
| iPS:434345 | 21-225_64H9 | NA | GAAATTGTGATGACCCAGACTCCACTCTCT GTCCGTCACCCCTGGACAGCCGGCCTCCATCT CCTGCAAGTCTAGTCAGAGTCTCCTTCATGGT GATGGAAAGACCTATTTGTTTGTGGTACCTGCA GAAGCCAGGCCAGCCTCCACAGGTCCTGATCT ATGAAGTTTCCAACCGGTTGTGTGAGTGCCA GACAGGTCAGTGGCAGCGGGTCAGGACAG ATTTCTCATTGAAAATCAGCCGGGTGGAGGCT GAGGACGTTGGGGTTTATTACTGCATGCAAAG TATACAGGTTCCGTGGACGTTCGGCCAAGGGA CCAAGGTGGAAATCACA SEQ ID NO: 25611 | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TATATCTACAAATGAACAGCCTGAGAGCCGAGG ACACGGCTGTGTATTACTGTGCGAGAGATACATA CGATTTTGGAGTGGTTATTTGGGCTACTGGGGC CAGGGAACCCTGGTCACCGTCTCCTCA SEQ ID NO: 29617 |
| | | AA | EIVMTQTPLSLSVTPGQPASISCKSSQSLLHGDGK TYLFWYLQKPGQPPQVLIYEVSNRLCGVPDRFS GSGSGTDFSLKISRVEAEDVGVYYCMQSIQVPW TFGQGTKVEIT SEQ ID NO: 25612 | QVQLVESGGGVVQPGRSLRLSCAASGFTFSTYGMH WVRQAPGKGLEWVAIIWYDGSNKYYADSVKGRFT ISRDNSKNTLYLQMNSLRAEDTAVYYCARDTYDF WSGYLGYWGQGTLVTVSS SEQ ID NO: 29618 |
| iPS:434347 | 21-225_64H10 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCTTAAGCTCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGATTAACAGTTTCCCTCTCA CTTTCGGCGGAGGGACCAAGGTGGAGATCAA A SEQ ID NO: 25613 | CAGGTGCAGCTGCAGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCACAGAAGTG GTGGCACAAACCAAGCACAGGACACAGAAGTTTCAGGGCA GGGTCACCATGACCAGGGACACGTCCATCAGCA CAGCCTACATGGAGCTGAGCGGGCTGAGATCTG ACGACACGGCCGTGTATTACTGTGCGAGAGCTCC GGGTACTGCAGCAACTGGTACATGGGATACTTT GACTACTGGGGCCAGGGAACCCTGGTCACCGTCT CCTCA SEQ ID NO: 29619 |

FIGURE 50
(Continued)

| | | | |
|---|---|---|---|
| iPS:434351 | 21-225_64A12 | AA | DIQMTQSPSSVSASVGDRVTITCRASQGISSWLA WYQQKPGKALKLLIYAASSLQSGVPSRFSGSGS GTDFTLTISSLQPEDFATYYCQQINSFPLTFGGGT KVEIK<br>SEQ ID NO: 25614 | QVQLVQSGAEVKKPGASVKVSCKASGYTFTGYYM HWVRQAPGQGLEWMGWIKPNSGGTNQAQKFQGR VTMTRDTSISTAYMELSGLRSDDTAVYYCARAPGT AATGTWGYFDYWGQGTLVTVSS<br>SEQ ID NO: 29620 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTACACGCCTGATCTATACTGCATCCACTT TGCAAAGTGGGGTCCCATCAAGGTTCAGCGGC AGTGGATCTGGGACAGATTCACTCTCACAAT CAGCAGCCTGCAGCCTGAAGATTTTGCAACTT ATTACTGTCTACAGCATAATGGTTACCCATTC ACTTTCGGCCCTGGGACCAAAGTGGATATCAA A<br>SEQ ID NO: 25615 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATAGACTCCGTGAAGT AATAAATACTATGTAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGGGAACTCGGG TTCCTCTCTGACCACTGGGGCCAGGGAACCCTGG TCACCGTCTCCTCA<br>SEQ ID NO: 29621 |
| | | AA | DIQMTQSPSSLSASVGDRVTITCRASQGIRNDLG WYQQKPGKAPTRLIYTASTLQSGVPSRFSGSGSG TEFTLTISSLQPEDFATYYCLQHNGYPFTFGPGTK VDIK<br>SEQ ID NO: 25616 | QVQLVESGGGVVQPGRSLRLSCAASGFTFSSYGMH WVRQAPGKGLEWVAVIWYDESNKYYVDSVKGRF TISRDNSKNTLYLQMNSLRAEDTAVYYCARELGFL SDHWGQGTLVTVSS<br>SEQ ID NO: 29622 |

FIGURE 50
(Continued)

| | | | | |
|---|---|---|---|---|
| iPS:434353 | 21-225_64B12 | NA | GACATCCAGATGACCCAGTCTCCATCCTCCT GTCTGCATCTGTAGGAGACAGAGTCACCATCA CTTGCCGGGCGAGTCAGGACATTAGCAATTAT TTAAATTGGTATCAGCAGAAACCAGGGACAGC CCCTAACCTCCTGATCTCTGATGCATCCATTT GGAAACAGGGGTCCCATCAACGTTCAGTGGA AGTGGATCTGGGACAGATTTTACTTTCACCAT CAGCAGCCTGCAGCCTGAAGATATTGCAACAT ATTACTGTCAACAGAGTGATAATCTCCCGTGC AGTTTTGGCCAGGGGACCAAGGTGGAGATCA AA | CAGCTGCAGCTGCAGGAGTCGGGCCCAGGACTG GTGAAGCCTTCGGAGAGACCCTGTCCCTCACCTGCA CTGTCTCTGGTGTCTCCATCAGCAGAAGTAGTTA CTACTGGGGCTGGATCCGCCAGCCCCCAGGGAA GGGGCTGGAGTGGATTGGGAGTATCTATTACAGT GGGAGCACCTCCTACAACCGTCCCTCAAGAGTC GAGTCACCATATCGTAGACACGTCCAAGAACC AGTTCTCCCTGAAGCTGAGCTCTGTGACCGCCGC AGACACGGCTGTGTATTATTGTGCGAGACTGGAC AGTGGCTGGTCCTTTGACTACTGGGGCCAGGGAA CCCTGGTCACCGTCTCCTCA |
| | | | SEQ ID NO: 25617 | SEQ ID NO: 29623 |
| | | AA | DIQMTQSPSSLSASVGDRVTITCRASQDISNYLN WYQQKPGTAPNLLISDASILETGVPSTFSGSGSG TDFTFTISSLQPEDIATYYCQQSDNLPCSFGQGTK VEIK | QLQLQESGPGLVKPSETLSLTCTVSGVSISRSSYYW GWIRQPPGKGLEWIGSIYYSGSTSYNPSLKSRVTISV DTSKNQFSLKLSSVTAADTAVYYCARLDSGWSFD YWGQGTLVTVSS |
| | | | SEQ ID NO: 25618 | SEQ ID NO: 29624 |
| iPS:434355 | 21-225_64G12 | NA | GACATCCAGATGACCCAGTCTCCCTCTTCCGT GTCTGCATCTGTAGGAGACAGAGTCACCATCA CTTGTCGGGCGAGTCAGAATATTACCAACCTGG TTAGCCTGGTATCAGCAGAAACCAGGGAAAG CCCCTAAACTCCTGATCTCTGCTGATCCAGTT TGCAAAGTGGGGTCCCATCAAGGTTCAGCGGC AGTGGATCTGGGACAGGCCTGAAGATTTCACTCTCACCAT CAGCAGCCTGCAGCCTGAAGATTTTGCAACTT ATATTTGTCAACAGGCTAACAGTTTTCCATTCA CTTTCGGCCCTGGGACCAAACTGGATATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTAATGCCAT GAGCTGGGTCCGCCAGGCTCCAGGGAAGGGGCT GGAGTGGGTCTCAGTTATTAGTGGTAGTGGTGGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCTTATATTACTGTGCGAAAAGGAACTA CGACGATGCTTTTGATATCTGGGGCCAAGGGACA ATGGTCACCGTCTCTTCA |
| | | | SEQ ID NO: 25619 | SEQ ID NO: 29625 |

FIGURE 50
(Continued)

| | | | |
|---|---|---|---|
| iPS:434357 | | AA | DIQMTQSPSSVSASVGDRVTITCRASQNITTWLA WYQQKPGKAPKLLISAASSLQSGVPSRFSGSGSG TDFTLTISSLQPEDFATYICQQANSFPFTFGPGTK LDIK<br>SEQ ID NO: 25620 | EVQLLESGGGLVQPGGSLRLSCAASGFTFSSNAMS WVRQAPGKGLEWVSVISGSGGSTYYADSVKGRFTI SRDNSKNTLYLQMNSLRAEDTALYYCAKRNYDDA FDIWGQGTMVTVSS<br>SEQ ID NO: 29626 |
| | | NA | GACATCCAGTTGACCCAGTCTCCATCCTCCCT GTCTGCATCTGTAGGAGACAGAGTCACCATCA CTTGCCGGGCGAGTCAGGTCATTAGCAGTTAT TTACATTGGTATCAGCAGAAACCAGGGAAAGT TCCTAAGGTCCTGATCTATAGTGCATCCAATTT GCAATGTGGAGTCCCATCTCGGTTCAGCGGCA GTGGATCTGGGACAGATTTCACTCTCACCTTC AGCAGCCTGCAGCCTGAAGATGTTGCAACTTA TTACGGTCAACGGCCTTACAATGCCCCGCTCA CTTTCGGCGGAGGGACCAAGGTGGAGATCAA A<br>SEQ ID NO: 25621 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTGATATGGTTTGAGGGAAG TAATAAACACTATACAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAACTTG GGTTCAGCAGTGACTACTGGGGCCAGGGAACCC TGGTCACCGTCTCCTCA<br>SEQ ID NO: 29627 |
| | 21-225_65C1 | AA | DIQLTQSPSSLSASVGDRVTITCRASQVISSYLHW YQQKPGKVPKVLIYSASNLQCGVPSRFSGSGSGT DFTLTFSSLQPEDVATYYGQRPYNAPLTFGGGT KVEIK<br>SEQ ID NO: 25622 | QVQLVESGGGVVQPGRSLRLSCAASGFTFSDYGM HWVRQAPGKGLEWVAVIWFEGSNKHYTDSVKGR FTISRDNSKNTLYLQMNSLRAEDTAVYYCARELGF SSDYWGQGTLVTVSS<br>SEQ ID NO: 29628 |

FIGURE 50
(Continued)

| | | | | |
|---|---|---|---|---|
| iPS:434359 | 21-225_65G3 | NA | GACATCCAGATGACCCAGTCTCCATCCTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCTTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTTCTATTGTCAACAGGTTAACAGTTTCCCTCTCACTTTCGGCGGAGGGACCAAGGTGGAGATCAAA | CAGGTGCAACTGGTGCAGTCTGGGGCTGAGGTGAAGAAGCCTGGGGCCTCAGTGAAGGTCTCCTGCAAGGCTTCTGGATACACCTTCACCGGCTACTATATACACTGGGTGCGACAGGCCCCTGGACAAGGCTTGAGTGGATGGGATGGATCAACCCTAACAGTGGTGGCACAAACTGCACAGGACACGTCCATCAGCACGGTCACCATGACCAGGGACACGTCCATCAGCACAGCCTACATGGAGCTGAGCAGCCTGAGATCTGACGACACGGCCGTATATTACTGTGCGAGAGCTCCGGGTAAAGCAGCAGCTGGTACATGGGATACTTTGACTACTGGGGCCAGGGAACCCTGGTCACCGTCTCCTCA |
| | | | SEQ ID NO: 25623 | SEQ ID NO: 29629 |
| | | AA | DIQMTQSPSSLSASVGDRVTITCRASQGISSWLAWYQQKPGKAPKLLIYAASSLQSGVPSRFSGSGSGTDFTLTISSLQPEDFATYCQQVNSFPLTFGGGTKVEIK | QVQLVQSGAEVKKPGASVKVSCKASGYTFTGYYIHWVRQAPGQGLEWMGWINPNSGGTNSAQKFQGRVTMTRDTSISTAYMELSRLRSDDTAVYYCARAPGKAAGTWGYFDYWGQGTLVTVSS |
| | | | SEQ ID NO: 25624 | SEQ ID NO: 29630 |
| iPS:434361 | 21-225_65D5 | NA | GACATCCAGATGACCCAGTCTCCGTCCTCACTATCTGCATCTGTAGGAGACAGAGTCACCATCACTTGTCTGGGCGAGTCAGGACATTAACAATTATTTAGCCTGGTTTCAGCAGAAACCAGGGAAAGCCCCTAGGTCCCTAATTTATGCTGCAGAGTTTCAGGCCAGTGGGGTCCCATCACGTTTCAGCGGCAGTGGTTCTGGGTCAGATTTCACTCTCACTATCAGCGCCACTGCCCACTGTATAAAAGTTATCCACTCACTTTTGGCCCTGGGACCAAAGTGGATATCAAA | CAGGTTCAGCTGGTGCAGTCTGGAGCTGAGGTGAAGAAGCCTGGGGCCTCAGTGAAGGTCTCCTGCAAGGCTTCTGGTTACACCTTTCCAGTCTATGGTATCAGTTGGGTGCGACAGGCCCCTGGACAAGGACTTGAGTGGATGGGATGGATCAGCGCTTACAGTGGTGGTGACAAACTATGCACACAGAAGCTCCAGGGCAGAGTCACCATGACCACAGACACATCCACGAGCACAGCCTACATGGAGCTGAGGAGCCTGAGATCTGACGACACGGCCGTGTATTTCTGTGCGAGAGGGAAGCAGTGGTCTTGACCCCTGGGGCCAGGGAACCCTGGTCACCGTCTCCTCA |
| | | | SEQ ID NO: 25625 | SEQ ID NO: 29631 |

FIGURE 50
(Continued)

| | | | | |
|---|---|---|---|---|
| | | AA | DIQMTQSPSSLSASVGDRVTITCRASQDINNYLA WFQQKPGKAPRSLIYAASSLHSGVPSQFSASGSG SDFTLTISSLQPEDFATYYCPLYKSYPLTFGPGTK VDIK | QVQLVQSGAEVKKPGASVKVSCKASGYTFPSYGIS WVRQAPGQGLEWMGWISAYSGNTNYAQKLQGRV TMTDTSTSTAYMELRSLRSDDTAVYFCARGEAVA VFDPWGQGTLVTVSS |
| | | | SEQ ID NO: 25626 | SEQ ID NO: 29632 |
| iPS:434363 | 21-225_65A6 | NA | GAAATAGTGATGACGCAGTCTCCAGTCACCCT GTTTGTGTCTCCAGGGGAAAGAGCCACCCTCT CCTGCAGGGCCAGTCAGTGTTAACAGCAAC TTAGCCTGGTACCAGCAGAAACCTGGCCAGGC TCCCAGGCTCCTCATCTATGGTGCATCCACCA GGGCCACTGGTATCCCAGCCAGGTTCAATGGC AGTGGGTCTGGGACAGAGTTCACTCTCACCAT CAGCAGCCTGCAGTCTGAAGATTTTGCAGTTT ATTATTGTCAGCAGTATAATGACTGGCCGTGC AGTTTTGGCCTGGAGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGGTATGATGGAAGT AATAAATACTATGGAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGG CATAGTGGGAGCTACTTGGTTTGACTACTGGGGC CAGGGAACCCTGGTCACCGTCTCCTCA |
| | | | SEQ ID NO: 25627 | SEQ ID NO: 29633 |
| | | AA | EIVMTQSPVTLFVSPGERATLSCRASQSVNSNLA WYQQKPGQAPRLLIYGASTRATGIPARFNGSGS GTEFTLTISSLQSEDFAVYYCQQYNDWPCSFGLE TKLEIK | QVQLVESGGGVVQPGRSLRLSCAASGFTFSNYGM HWVRQAPGKGLEWVAVIWYDGSNKYYGDSVKGR FTISRDNSKNTLYLQMNSLRAEDTAVYYCARDQGI VGATWFDYWGQGTLVTVSS |
| | | | SEQ ID NO: 25628 | SEQ ID NO: 29634 |

FIGURE 50
(Continued)

| | | | | |
|---|---|---|---|---|
| iPS:434367 | 21-225_65H11 | NA | GACATCCAGATGACCCAGTCTCCATCCTCT GTCTGCATCTGTAGGAGACAGAGTCACCATCA CTTGTCGGGCGAGTCAGGACATTAGCACTTAT TTAGCCTGGTTCAGCAGAAACCAGGGAAAGC CCCTAAGTCACTGATCTATGCTGCATCCAGTT GCAAAGTGGGGTCCCATCAAAGTTCAGCGGCA GTGGATCTGGGACAGATTTCACTCTCACCATC AGTAGCCTGCAGCCTGAAGATTTTGCAACTTA TTACTGCCAACAGTATAATAGTTTCCCTCTCAC TTTCGGCGGAGGGACCAAGGTGGAGATCAAA | GAGGTGCAGCTGTGGAGTCTGGGGAGGCCTG GTCAAGCCGGGGGGGGTCCCTGAGACTCTCCTGTG CAGCCTCTGGATTCACCTTCAGTAGCTATAGGAT GAACTGGGTCCGCCAGGCTCCAGGGAAGGGGCT GGAGTGGGTCTCATCATTAGTAGTAGTAGTAGT TCCATATACTACGCAGACTCAGTGAAGGGCCGAT TCACCACCTCCAGAGACAACGCCAAGAACTCACT GTATCTGCAAATGAACAGCCTGAGAGCCGAGA CACGGCTGTGTATTACTGTACGAGTACAAGTGGG AGCTGGGGCCAGGGAACCCTGGTCACCGTCTCCT CA |
| | | | SEQ ID NO: 25629 | SEQ ID NO: 29635 |
| | | AA | DIQMTQSPSSLSASVGDRVTITCRASQDISTYLA WFQQKPGKAPKSLIYAASSLQSGVPSKFSGSGSG TDFTLTISSLQPEDFATYYCQQYNSFPLTFGGGT KVEIK | EVQLVESGGGLVKPGGSLRLSCAASGFTFSSYRMN WVRQAPGKGLEWVSSISSNSSIYADSVKGRFTTS RDNAKNSLYLQMNSLRAEDTAVYYCTSTSGSWGQ GTLVTVSS |
| | | | SEQ ID NO: 25630 | SEQ ID NO: 29636 |
| iPS:434369 | 21-225_66B1 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCTTAAGCTCTTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGAGTAACAGTTTCCCTCTC ACTTTCCGGCGGAGGGACCAAGGTGGAGATCA AA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCTAACAGTGG TGGCACAAACAATGCACAGAAGTTCAGGGCAG GGTCACCATGACCAGGGACACGTCCATCAGCAC AGCCTACATGGAACTGAGCAGGCTGAGAGTCTGA CGACACGGCCGTGTATTATTGTGCGAGAGCTCCG GGTACAGCAGCAGCTGGTACATGGGATACTTTG ACTACTGGGGCCAGGGAACCCTGGTCACCGTCTC CTCA |
| | | | SEQ ID NO: 25631 | SEQ ID NO: 29637 |

FIGURE 50
(Continued)

| | | | | |
|---|---|---|---|---|
| | | AA | DIQMTQSPSSVSASVGDRVTITCRASQGISSWLAWYQQKPGKALKLLIYAASSLQSGVPSRFSGSGSGTDFTLTISSLQPEDFATYYCQQTNSFPLTFGGGTKVEIK | QVQLVQSGAEVKKPGASVKVSCKASGYTFTGYYMHWVRQAPGQGLEWMGWINPNSGGTNAQKFQGRVTMTRATSISTAYMELSRLRSDDTAVYYCARAPGTAAAGTWGYFDYWGQGTLVTVSS |
| | | | SEQ ID NO: 25632 | SEQ ID NO: 29638 |
| iPS:434373 | 21-225_66A7 | NA | GACATCCAGATGACCCAGTCTCCATCTTCCGTGTCTGCATCTGTAGGGACAGAGTCACCATCACTTGTCGGGCGAGTCAGGGTATTAGCAGCTGGTTAGCCTGGTATCAGCAGAAACCAGGGAAAGCCCCTAAGCTCTTGATCTATGCTGCATCCAGTTTGCAAAGTGGGGTCCCTTCAAGGTTCAGCGGCAGTGGATCTGGGACAGATTTCACTCTCACCATCAGCAGCCTGCAGCCTGAAGATTTTGCAACTTACTATTGTCAACAGATTAATAGTTTCCCTCTCACTTTCGGCGGAGGGACCAAGGTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGGATGGATCAACCCTAACAGTGGTGGCACAAACCAAGCACAGAAGTTCCAGGGCAGGGTCACCATGACCAGGGACACGTCCATCAGCACAGGTTACATGGAGCTGAGCAGGCTGAGATCTGACGACACGGCCGTGTATTACTGTGCGAGAGCTCCGGGCACAGTAGCAGCTGGTACATGGGGATACTTTGACTATTGGGGCCAGGGAACCCTGGTCACCGTCTCCTCA |
| | | | SEQ ID NO: 25633 | SEQ ID NO: 29639 |
| | | AA | DIQMTQSPSSVSASVGDRVTITCRASQGISSWLAWYQQKPGKAPKLLIYAASSLQSGVPSRFSGSGSGTDFTLTISSLQPEDFATYYCQQINSFPLTFGGGTKVEIK | QVQLVQSGAEVKKPGASVKVSCKASGYTFTGYYMHWVRQAPGQGLEWMGWIKPNSGGTNQAQKFQGRVTMTRDTSISTGYMELSRLRSDDTAVYYCARAPGTVAAGTWGYFDYWGQGTLVTVSS |
| | | | SEQ ID NO: 25634 | SEQ ID NO: 29640 |

FIGURE 50
(Continued)

| | | | | |
|---|---|---|---|---|
| iPS:434375 | 21-225_66C7 | NA | GACATCCAGATGACCCAGTCTCCATCCTCCCT GTCTGCATCTGTAGGAGACAGAGTCACCATCA CTCGCCGGGCAGTCAGGGCATTAGCAATTAT TTACATTGGTATCAGCAGAAACAGGGAAAGC TCCTAAGCTCTTGATCTATGCTGCATCCAATT ACAATGTGGAGTCCCATCACGGTTCAGCGGCA GTGGATCTGGGACAGATTTCACTCTCACAATC AGCAGCCTGCAGCCTGAAGATGTTGCAACTTA TTACTGTCAACAGCATATAATTCCCCGCTCA CTTTCGGCGGAGGGACCAAGGTGGAGATCAA A | CAGGTGCAGCTGGTGGAGTCTGGGGAGGCGTG GTCCAGCCTGGGAGGTCCCTGAGACTCTCCTGTG TAGCGTCTGGATTCACCTTCAGTGACTATGGCAT GCACTGGGTCCGCCAGGCTCCAGGCAAGGGCT GGAGTGGGTGGCAGTTATATGGTTTGAGGGAAGT CATAAATACTATACAGACTCCGTGAAGGGCCGAT TCACCATCTCCAGAGACAATTCCAAGAACACGCT GTATCTGCAAATGAACAGCCTGAGAGCCGAGA CACGGCTGTGTATTACTGTGCGAGAGAACTTGGG TTCAGCAGTGACTACTGGGGCCAGGGAACCCTG GTCACCGTCTCCTCA |
| | | | SEQ ID NO: 25635 | SEQ ID NO: 29641 |
| | | AA | DIQLTQSPSSLSASVGDRVTITRRASQGISNYLH WYQQKPGKAPKLLIYCASNLQCVPSRFSGSGS GTDFTLTISSLQPEDVATYYCQQHNNSPLTFGGG TKVEIK | QVQLVESGGGVVQPGRSLRLSCVASGFTFSDYGM HWVRQAPGKGLEWVAVIWFEGSHKYYTDSVKGR FTISRDNSKNTLYLQMNSLRAEDTAVYYCARELGF SSDYWGQGTLVTVSS |
| | | | SEQ ID NO: 25636 | SEQ ID NO: 29642 |
| iPS:434379 | 21-225_66A9 | NA | GACATCCAGATGACCCAGTCTCCATCCTCCCT GTCTGCATCTGTAGGAGACAGAGTCACCATCA CTTGCCGGGCAAGTCAGAACATTTCAGTGCT GCACTGGTATCAGCAGAAACCAGGGAAAG CCCCTAAACTCCTGATCTTTGCTGCATCCAGTT TACAAAGTGGGGTCCCATCAAGGTTCAGTGGC AGTGGATCTGGGACAGATTTCACTCTCACCAT CAGCAGTCTGCAACAGACTACAGTGTCCCTTC ACTACTGTCAACAGAGCTACAGTCCCCTTC ACTTTCGGCGGGACCTAAGGTGGATTTCAA A | CAGGTGCAGCTGGTGGAGTCTGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGCAGACTATGAAG TGATAAATACTATGCAGAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAAGAC CCGGCGTACCCAGTTGTCTGACTACTGGGGCCAGG GAACCCTGGTCACCGTCTCCTCA |
| | | | SEQ ID NO: 25637 | SEQ ID NO: 29643 |

FIGURE 50
(Continued)

| | | | | |
|---|---|---|---|---|
| | | AA | DIQMTQSPSSLSASVGDRVTITCRASQNIFSYLN WYQQKPGKAPKLLIFAASSLQSGVPSRFSGSGSG TDFTLTISSLQPEDFATYYCQQTYSVPFTFGPGTK VDFK<br>SEQ ID NO: 25638 | QVQLVESGGGVVQPGRSLRLSCAASGFTFSSYGMH WVRQAPGKGLEWVAVIWHDGSDKYYADSVKGRF TISRDNSKNTLYLQMNSLRAEDTAVYYCAREDPRT SCSDYWGQGTLVTVSS<br>SEQ ID NO: 29644 |
| iPS:434383 | 21-225_66F9 | NA | GACATCCAGATGACCCAGTCTCCATCCTCCCT GTCTGCATCTGTAGGAGACAGAGTCACCATCA CTTGCCGGGCAAGTCAGAGACATTAGAAATGTT TTAGGCTGGTATCAGCAGAAACCAGGAAAG CCCCTAAGCGCCTGATCTATACTGCATCCAGT TTACAAAGTGGGGTCCCATCCAGGGTTCAGCGG CAGTGGATCTGGGACAGAATTCACTCTCACAA TCAGCAGCCTGCAGCCTGAAGATTTTGCAACT TATTACTGTCTACAGTATAATAGTTACCCATTC ACTTTCGGCCCTGGGACCAAAGTGGATATCAA A<br>SEQ ID NO: 25639 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGACT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACGGCCTGAGAGCCGAGGA CACGGCTGTGTATTTCTGTGCGAGAACCAATGCT TTTGATATCTGGGGCCAGGGGACAATGGTCACCG TCTCTTCA<br>SEQ ID NO: 29645 |
| | | AA | DIQMTQSPSSLSASVGDRVTITCRASQDIRNVLG WYQQKPGKAPKRLIYTASSLQSGVPSGFSGSGS GTEFTLTISSLQPEDFATYYCLQYNSYPFTFGPGT KVDIK<br>SEQ ID NO: 25640 | EVQLVESGGGLVKPGGSLRLSCAASGFTFSSYSMN WVRQAPGKGLEWVSSISGTSSYIYYADSVKGRFTIS RDNAKNSLYLQMNGLRAEDTAVYFCARTNAFDIW GQGTMVTVSS<br>SEQ ID NO: 29646 |

FIGURE 50
(Continued)

| | | | | |
|---|---|---|---|---|
| iPS:434385 | 21-225_66C10 | NA | GACATCCAGATGACCCAGTCTCCATCCCCT GTCTGCATCTGTAGGAGACAGAGTCACCATCA CTTGCCGGGCAAGTCAGGCAGAAACCAGGAAAG TTAGGCTGGTATCAGCAGAAACCAGGAAAG CCCCTAAGCGCCTGATCTATCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGTATAATAGTTACCCTCGT GGACGTTCGGCCAAGGGACCAAGGTGGAAAT CAAA | GAGGTGCAGCTGTTGGAGTCTGGGGGAGGCTTG GTACAGCCTGGGGGGTCCCTGAGACTCTCCTGTG CAGCCCTCTGATTCACCTTTAGCAGCTATGTTAT GAGCTGGGTCCGCCAGGCTCCAGGAAGGGCT GGAGTGGGTCTCAGTTATTAGTGGTAGTGGTGCT AGAACATACTACGCAGACTCCGTGAAGGGCCGA TTCACCATCTCCAGAGACAATTCCAAGAACACGC TGTATCTGCAAATGAACAGCCTGAGAGCCGAGG ACACGGCCGTATATTACTGTGCGGAACTGGGAT AGACTACTACTACGGTATGGACGTCTGGGGCCAA GGGACCACGGTCACCGTCTCCTCA |
| | | | SEQ ID NO: 25641 | SEQ ID NO: 29647 |
| | | AA | DIQMTQSPSSLSASVGDRVTITCRASQAIRNDLG WYQQKPGKAPKRLIYPASSLQSGVPSRFSGSGSG TEFTLTISSLQPEDFATYYCLQYNSYPPWTFGQG SKVEIK | EVQLLESGGGLVQPGGSLRLSCAASGFTFSSYVMS WVRQAPGKGLEWVSGISGSGARTYYADSVKGRFTI SRDNSKNTLYLQMNSLRAEDTAVYYCAELGIDYY YGMDVWGQGTTVTVSS |
| | | | SEQ ID NO: 25642 | SEQ ID NO: 29648 |
| iPS:434387 | 21-225_66D11 | NA | GATATCCAGATGACCCAGTTTCCATCCTCCCA GTCTGCATCTGTAGGAGACAGAGTCACCATCA CTTGCCGGGCAAGTCAGGGCATTAGAAATGAT TTAGGTTGGTATCAGCAGAAACCAGGGAAAG CCCATAAGCGCCTTGATCTATGCTGCATCCAGT TGTCAAAGTGGGGTCCCATCAAGGTTCAGCGG CAGTGGATGTGGGACAGAATTCACTACTCAA TCAGCAGCATGCAGCCTGAAGATTTTGCAACT TATTACTGTCTATATGTCATAATAGTTACCCTCG GACGTTCGGCCAAGGGACCAAGGTGGAAATC AAA | CAGGTGCAGCTGTGGTGGAGTCTGGGGGAGGCGTG GTCCAGCCTGGGAGGTCCCTGAGACTCTCCTGTG GAGCGTCTGGATTCACCTTCAGTAGTTATGCCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTCTCTGCAAATGAACAGCCTGAGAGCCGAGG ACACGGCTCTGTATTACTGTGCGAGAGAGATGTA TAGCAGCAACTGGTACGACTACGGTTTGGACGTC TGGGGCCAAGGGACCACGGTCACCGTCTCCTCA |
| | | | SEQ ID NO: 25643 | SEQ ID NO: 29649 |

FIGURE 50
(Continued)

| | | | |
|---|---|---|---|
| iPS:434389 | 21-225_66F11 | AA | DIQMTQFPSSQSASVGDRVTITCRASQGIRNDLG WYQQKPGKAHKRLIYAASSCQSGVPSRFSGSGC GTEFTISISSMQREDFATYYCIVHNSYPRTFGQGT KVEIK<br>SEQ ID NO: 25644 | QVQLVESGGGVVQPGRSLRLSCGASGFTFSSYGMH WVRQAPGKGLEWVAVIWYDGSNKYYADSVKGRF TISRDNSKNTLSLQMNSLRAEDTALYYCAREMYSS NWYDYGLDVWGQGTTVTVSS<br>SEQ ID NO: 29650 |
| | | NA | GACATCCAGATGACCCAGTCTCCATCTTCCGT GTGTGCATCTGTAGGAGACAGAGTCACCATCA CTTGTCGGGAGAGTCAGGGTATTAGCATCTGG TTAGCCTGGTATCAGCAGAAACCAGGGAAAG CCCCTAAGCTTTGATCTATGCTGCATCCAGTT TGCAAAGTGGGGTCCCATCAAGGTTCAGCGGC AGTGGATATGGGACAGATTTCACTCTCACCAT CAGCAGCGTGCAGCCTGAAGATTTTGCAACTT ACTATTGTCAACAGGCTAACAGTTTCCCATTC ACTTTCGGCCCTGGGACCAAAGTGGATATCAA A<br>SEQ ID NO: 25645 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACCATA TGCACTGGGTCCGACAGGCCCCTGGACAAGGGC TTGAGTGGATGGGATGGATCAACAGAAGTTTCAGGACTGG TGGCACACACTATGACCAGGAAGTTTCAGGACTGG GTCACCATGACCAGGGACACGTCCATCAGCACA GCCTATATGAACTGAGCAGGCTGAGATCTGAC GACACGGCCGTGTATTACTGTGCGAGAGATAGTA GAAGTTCGTGGGACTACTGGGGCCAGGGAACCC TGGTCTCCGTCTCCTCA<br>SEQ ID NO: 29651 |
| | | AA | DIQMTQSPSSVCASVGDRVTITCRESQGISIWLA WYQQKPGKAPKLLIYAASSLQSGVPSRFSGSGY GTDFTLTISSVQPEDFATYYCQQANSFPFTFGPGT KVDIK<br>SEQ ID NO: 25646 | QVQLVQSGAEVKKPGASVKVSCKASGYTFTGYHM HWVRQAPGQGLEWMGWINPNNGGTHYAQKFQD WVTMTRDTSISTAYMELSRLRSDDTAVYYCARDS RSSWDYWGQGTLVSVSS<br>SEQ ID NO: 29652 |

FIGURE 50
(Continued)

| | | | |
|---|---|---|---|
| iPS:434393 | 21-225_67C3 | NA | GAAATAGTGATGACGCAGTCTCCAGCCACCCT GTCTGTGTCTCCAGGGGAAAGAGCCACCCTCT CCTGCAGGGCCAGTCAGAGTGTTAACAGCAAC TTAGCCTGGTACCAGCAGAAACCTGGCCAGGC TCCCAGGCTCCTCATCTCTATTGCATCCACCAG GGCCACTGGTATCCCAGCCAGGTTCAATGGCA GTGGGTCTGGGACAGAGTTCACTCTCACCATC AGCAGCCTGCAGTCTGAAGATTTTGCAGTTTA TTACTGTCAGCAGTATAATGACTGGCCGTGTA GTTTTGGCCAGGGGACCAAGCTGGAGATCAAA<br><br>SEQ ID NO: 25647 | CAGGTGCAGCTGGTGGAGTCGGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGCT GGAGTGGGTGGCAGTTATATGGTATGATGGAAG TAATAAATATTATGGAGACTCCGTGAAGGGCCGA GTCACCATCTCCAGAGACAATTCCAAGAACTGC TGCATCTGCAAATGAACAGCCTGAGAGCCGAGG ACACGGCTGTGTATTACTGTGCGAGAGATCAGGG CATAGTGGGAGCTACTGGTTTGACTACTGGGGC CAGGGAACCCTGGTCACCGTCTCCTCA<br><br>SEQ ID NO: 29653 |
| | | AA | EIVMTQSPATLSVSPGERATLSCRASQSVNSNLA WYQQKPGQAPRLLISIASTRATGIPARFNGSGSG TEFTLTISSLQSEDFAVYYCQQYNDWPCSFGQGT KLEIK<br><br>SEQ ID NO: 25648 | QVQLVESGGGVVQPGRSLRLSCAASGFTFSSYGMH WVRQAPGKGLEWVAAIWYDGSNKYYGDSVKGRV TISRDNSKNSLHLQMNSLRAEDTAVYYCARDQGIV GATWFDYWGQGTLVTVSS<br><br>SEQ ID NO: 29654 |
| iPS:434397 | 21-225_67H4 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGAGTTAACAGTTTCCCTCTCA CTTTCGGCGGAGGGACCAAGGTGGAGATCAA A<br><br>SEQ ID NO: 25649 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTG GTGGCACAAACCAAGCACCAGAAGTTTCAGGGCA GGGTCACCATGACCAGGGACACGTCCATCAGCA CAGCCTACATGGAGCTGAGCGGGCTGAGATCTG ACGACACGGCCGTGTATTACTGTGCGAGAGCTCC GGGTACTGCAGCAACTGGTACATGGGGATACTTT GACTACTGGGGCCAGGGAACCCTGGTCACCGTCT CCTCA<br><br>SEQ ID NO: 29655 |

FIGURE 50
(Continued)

| | | | |
|---|---|---|---|
| iPS:434399 | | AA | DIQMTQSPSSVSASVGDRVTITCRASQGISSWLA WYQQKPGKAPKLLIYAASSLQSGVPSRFSGSGS GTDFTLTISSLQPEDFATYYCQQINSFPLTFGGT KVEIK<br>SEQ ID NO: 25650 | QVQLVQSGAEVKKPGASVKVSCKASGYTFTGYYM HWVRQAPGQGLEWMGWIKPNSGGTNQAQKFQGR VTMTRDTSISTAYMELSGLRSDDTAVYYCARAPGT AATGTWGYFDYWGQGTLVTVSS<br>SEQ ID NO: 29656 |
| | | NA | GACATCCAGATGACCCAGTCTCCATCCTCCCT GTCTGCATCTGTAGGAGACAGAGTCACCATCA CTTGCCGGGCAAGTCAGGCATTAGAAATGAT TTAGGCTGGTTTCAGCAGAAACCAGGGAAAGC CCCTAAGCGCCTGATCTATGCTGCATCCAGTTT GCAAAGTGGGGTCCCATCAAGGTTCAGCGGCA GTGGATCTGGGACAGAGCCTGAAGATTTTGCAACTTA TTACTGTCTACACCATAATAGTTATCCATTCAA ATTTGGCCCTGGGACCAAAGTGGATATCAAA<br>SEQ ID NO: 25651 | CAGGTGCAGCTGGTGCAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGCT GGAATGGGTGGCAGTTATATTATATGATGAAGT AAGAAATACTATGCAGACTCCGTGAAGGGCCGA TTCACCATCTCCAGAGACAATTCCAAGAACACGC TTTATCTGCAAATGAACAGCTGAGAGCTGAGGA CACGGCTGTGTATTACTGTGCGAGGAGTATCCCG GAATTGACTATTGGGGCCAGGGAACCCTGGTCA CCGTCTCCTCA<br>SEQ ID NO: 29657 |
| 21-225_67B7 | | AA | DIQMTQSPSSLSASVGDRVTITCRASQGIRNDLG WFQQKPGKAPKRLIYAASSLQSGVPSRFSGSGSG TEFSLTISSLQPEDFATYYCLHHNSYPFKFGPGTK VDIK<br>SEQ ID NO: 25652 | QVQLVESGGGVVQPGRSLRLSCAASGFTFSNYGM HWVRQAPGKGLEWVAVILYDGSKKYYADSVKGR FTISRDNSKNTLYLQMNSLRAEDTAVYYCARSIPEF DYWGQGTLVTVSS<br>SEQ ID NO: 29658 |

FIGURE 50
(Continued)

| | | | |
|---|---|---|---|
| iPS:434405 | 21-225_68E6 | NA | GACATCCAGATGACCCAGTCTCCATCCTCACT GTCTGCATCTGTAGGAGACAGAGTCACCATCA CTTGTCGGGCGAGTCAGGGCATTAGTAGTTAT TTAGCCTGGTTTCAGCAGAAACCAGGGAAAGC CCCTAAGTCCCTGATCTATGTTGCATCCAGTT GCAAAGTGGGGTCCCATCAAGGTTCAGCGGCA GTGGATCTGGGACAGATTTCACTCTCACCATC AGCAGCCTGCAGCCTGAAGATTTTGCAATTTA TTACTGCCAACAGTATGATAGTTACCATTCA CTTTCGGCCCTGGGACCAAAGTGGATATCAGA SEQ ID NO: 25653 | GAGGTGCAGCTGGTGGAGTCTGGGGGAGGCTG GTCAAGCCGGGGGGGTCCCTGAGACTCTCCTGT GCAGCCTCTGGATTCACCTTAAGTAGTAGTTTTGGCAT GAACTGGGTCCGCCAGGCTCCAGGGAAGGGGCT GGAGTGGGTCTCATACATTAGTAGAAGTAGTAGT CACATATACTACGCAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGGTCTCTAGTGG GAGCCCCTTTGACTACTGGGGCCAGGGAACCCTG GTCACCGTCTCCTCA SEQ ID NO: 29659 |
| | | AA | DIQMTQSPSSLSASVGDRVTITCRASQGISYYLA WFQQKPGRAPKSLIYVASSLQSGVPSRFSGSGSG TDFTLTISSLQPEDFAIYYCQQYDSYPFTFGPGTK VDIR SEQ ID NO: 25654 | EVQLVESGGGLVKPGGSLRLSCAASGFTLSSFGMN WVRQAPGKGLEWVSYISRSSSHYYADSVKGRFTIS RDNAKNSLYLQMNSLRAEDTAVYYCAVSSGSPFD YWGQGTLVTVSS SEQ ID NO: 29660 |
| iPS:434407 | 21-225_68G8 | NA | GACATCCAGATGACCCAGTCTCCATCCTCCCT GTCTGCATCTGTAGGAGACAGAGTCACCATCA CTTGCCGGGCAAGTCAGGGCATTAGAAATAAT TTAGGCTGGTATCAGCAGAGACCAGGGAAAG CCCCTAAGCGCCTGATCTATGCTGCATCCAGT GTGCAAAGTGGGGTCCCATCACGGTTCAGCGG CAGTGGATCTGGGACAGACCTGAAGATTCAACT TCAGCAGCCTGCAGCCTGAAGATTTTGCAACT TATTACTGTCTACAGTATAATAGTTACCCATTC ACTTTCGGCCCTGGGACCAAAGTGGATATCAA A SEQ ID NO: 25655 | GAGGTGCAGCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGT TACATATATTACGCAGACACAGTGATGGGCCGAT TCACCATCTCCAGAGACAACGCCAAGAACTCT GTATCTGCAAATGAACAGCCTGAGAGCCGAGGA CACGGCTGTGTATTACTGTGTGCGAGAGTCAACAGC TTTGACTCCTGGGGCCAGGAACCCTGGTCACCG TCTCCTCA SEQ ID NO: 29661 |

FIGURE 50
(Continued)

| | | AA | DIQMTQSPSSLSASVGDRVTITCRASQGIRNNLG WYQQRPGKAPKRLIYAASSVQSGVPSRFSGSGS GTEFTLTISSLQPEDFATYYCLQYNSYPFTFGPGT KVDIK<br>SEQ ID NO: 25656 | EVQLVESGGGLVKPGGSLRLSCAASGFTFSSYSMN WVRQAPGKGLEWVSSISGSSSYIYYADSVMGRFTIS RDNAKNSLYLQMNSLRAEDTAVYYCARVNSFDSW GQGTLVTVSS<br>SEQ ID NO: 29662 |
|---|---|---|---|---|
| iPS:434411 | 21-225_68F11 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGCCAGAATTCACTCTCTCAA TCAGCAGCCTGCAGCCTGAAGATATTTGCAACT TATTACTGTCTACAGCATATAGTTATCCGTTC ACTTTCGGCGGAGGGACCAAGGTGGAGATCA AA<br>SEQ ID NO: 25657 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCTGTTATATGGTATGATGTAAGT AATAAATACTATGCAGACTCCGTGAAGGGCCGA TTCACCATCTCAAGAGACAACAATTCCAAGAACACGC TGTATCTTCAAATGAACAGCCTGAGAGCCGAGG ACACGGCTGTGTATTACTGTGTGAGAGAACTGG GATGACCTGCTGCTGGGGCCAGGAACCCTG GTCACCGTCTCCTCA<br>SEQ ID NO: 29663 |
| | | AA | DIQMTQSPSSLSASVGDRVTITCRASQGIRNDLG WYQQKPGKAPKRLIYAASSLQSGVPSRFSGSGS GPEFTLSISSLQPEDFATYYCLQHNSYPFTFGGGT KVEIK<br>SEQ ID NO: 25658 | QVQLVESGGGVVQPGRSLRLSCAASGFTFSDYGM HWVRQAPGKGLEWVAVIWYDVSNKYYADSVKGR FTISRDNSKNTLYLQMNSLRAEDTAVYYCVRELGM TSDCWGQGTLVTVSS<br>SEQ ID NO: 29664 |

FIGURE 50
(Continued)

| | | | |
|---|---|---|---|
| iPS:434413 | 21-225_68D12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGATTCAGCGG CAGTGGATCTGGGACAGAATTCACTCTCACAA TCAGCAGCCTGCAGCCTGAAGATTTTGCAACT TATTACTGTCTACAGCATAGTACTTACCCGCTC ACTTTCGGCGGAGGGACCAAGGTGGAGATCA AA |
| | | | SEQ ID NO: 25659 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHSTYPLTFGGGT KVEIK |
| | | | SEQ ID NO: 25660 |
| iPS:434417 | 21-225_69C8 | NA | GACATCCAGATGACCCAGTCTCCATCCTCCCT GTCTGCATCTGTAGGAGACAGAGTCACCATCA CTTGCCGGGCAAGTCAGAGCATTAACCAATTAT TTAAATTGGTATCAGCAGAAACCAGGGAAAG CCCCTAAGCTCCTGATCTATGTTGCGTCCAGTT TGCAAAGTGGGGTCCCATCAAGGTTCAGTGGC AGTGGATCTGGGACAGATTTCACTCTCGTCAT ACTACTGTCAACAGAGTTACAGTACCCCATTC ACTTTCGGCCCTGGGACCAAAGTGGATATCAA A |
| | | | SEQ ID NO: 25661 |

| | | | |
|---|---|---|---|
| | | | CAGCTGCAGCTGCAGGAGTCGGGCCCAGGACTG GTGAAGCCTTCGGAGACCCTGTCCTCACCTGCA CTGTCTCTGGTGGCTCCATCAGCAGAAGTAGTTA CTACTGGGGCTGGATCCGCCAGCCCCCAGGAA GGGGCTGGAGTGGATTGGGAATATCTATTATAGT GGGAGCACCTATACATCCCGTCCCTCAAGAGTC GAGTCACCATATCCGTAGACACGTCCAAGAACC AGTTCTCCCTGAAGCTGACCTCTGTGACCGCGC AGACACGGCTGTGTATTACTGTGCGAGACATAGC ACCAGCTGGTCCATTGACTACTGGGGCCAGGGA ACCCTGGTCACCGTCTCCTCA |
| | | | SEQ ID NO: 29665 |
| | | | QLQLQESGPGLVKPSETLSLTCTVSGGSISRSSYYW GWIRQPPGKGLEWIGNIYYSGSTYYIPSLKSRVTISV DTSKNQFSLKLTSVTAADTAVYYCARHSTSWSIDY WGQGTLVTVSS |
| | | | SEQ ID NO: 29666 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGCCAT GCACTGGGTCCGCCAGGCTCCAGGCAAGGGGCT GGAGTGGGTGGCAGTTATATGGTATGATGGAAGT GATAAATACTATGCAGACTCCGTGAAGGGCCGA TTCACCATCTCCAGAGACAATTCCAAGAACACGC TGTATCTGCAAATGATCAGCCTGAGAGCCGAGG ACACGGCTGTTTATTACTGTGCGAGAGATATCC TAGCAACTCGGCGGGGACTACTGGGGCCAGGG AACCCTGGTCACCGTCTCCTCA |
| | | | SEQ ID NO: 29667 |

FIGURE 50
(Continued)

| | | | | |
|---|---|---|---|---|
| iPS:434423 | 21-225_70D1 | AA | DIQMTQSPSSLSASVGDRVTFTCRAGQTIYNYLN WYQQKPGKAPKLLIHVASSLQSGVPSRFSGSGS GTDFTLVISSLQPEDFATYYCQQSYSTPFTFGPGT KVDIK SEQ ID NO: 25662 | QVQLVESGGGVVQPGRSLRLSCAASGFTFSNYAM HWVRQAPGKGLEWVAVIWYDGSDKYYADSVKGR FTISRDNSKNTLYLQMISLRAEDTAVYYCARDIPSN SAGDYWGQGTLVTVSS SEQ ID NO: 29668 |
| | | NA | GACATCCAGATGACCCAGTCTCCATCTTCCGT GTCTGCATCTGTAGGAGACAGAGTCACCATCA CTTGTCGGGCGAGTCAGGGTGTTAGCAGGTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTTCACTGTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A SEQ ID NO: 25663 | CAGGTGCAGCTGGTGCAGTCTGGGGCTGAGGTG AAGAAGCCTGGGGCCTCAGTGAAGGTCTCCTGTA AGGCTTCTGGATACACCTTCACCGCTACCATAT GCACTGGGTGCGACAGGCCCCTGGACAAGGGCT TGAGTGGATGGGATGGATCAACCTAACAGTAAT GCCACAAACTATGCACAGAAGTTTCAGGGCAGG GTCACCATGACCAGGGACACGTCCATCAGCACA GCCTACATGGAACTGAGCAGGCTGAGATCTGAC GACACGGCCGTGTATTACTGTGCGAGAGATAGC ATATCGTCGTGGGACTACTGGGGCCAGGGAACC CTGGTCACCGTCTCCTCA SEQ ID NO: 29669 |
| | | AA | DIQMTQSPSSVSASVGDRVTITCRASQGVSRWL AWYQQKPGKAPKLLIYAASSLQSGVPSRFSGSG SGTDFTVTISSLQPEDFATYYCQQANSFPFTFGPG TKVDIK SEQ ID NO: 25664 | QVQLVQSGAEVKKPGASVKVSCKASGYTFTGYHM HWVRQAPQGLEWMGWINPNSNATNYAQKFQGR VTMTRDTSISTAYMELSRLRSDDTAVYYCARDSISS WDYWGQGTLVTVSS SEQ ID NO: 29670 |

FIGURE 50
(Continued)

| | | | | |
|---|---|---|---|---|
| iPS:434425 | 21-225_70A5 | NA | GAAATAGTGATGACGCAGTCTCCAGCCACCCT GTCTGTGTCTCCAGGGGAAAGAGCCACCCTCT CCTGCAGGGCCAGTCAGAGTGTTAACAGCAAC TTAGCCTGGTACCAGCTGAAACCTGGCCAGGC TCCCAGGCTCCTCATCTCTATTGCATCCACCAG GGCCACTGGTATCCACCCCGGTTCAATGGCA GTGGGTCTGGGACAGAGTTCACTCTCACCATC AGCAGCCTGCAGTCTGAAGATTTTGCAGTTTA TTACTGTCAGCAGTATAATGACTGGCCGTGTA GTTTTGGCCAGGGGACCAAGCTGGAGATCAAA<br>SEQ ID NO: 25665 | CAGGTTCAGCTGGTGGTGAGTCTGGGGGAGGCGTG GTCCAGCCTGGGGAGGTCCCTGAGACTCTCCTGTG CAGCGCTTCTGGATTCACCTTCAGTAGCTATGGCAT GCACTGGGTCCGCCAGGCTCCAGGCAAGGGCT GGAGTGGGTGGCAGTTATATGGTATGGATGAAGT AATAAATACTATGCAGACTCCGTGAAGGGCCGA TTCACCATCTCCAGAGACAATTCCAAGAACTCGC TGTATCTGCAAATGAACAGCCTGAGCGCCGAGG ACACGGCTGTTTATTACTGTGCGAGAGATCAGGG CATAGTGGGAGCTACTGGTTTGACTACTGGGGC CAGGGAACCCTGGTCACCGTCTCCTCA<br>SEQ ID NO: 29671 |
| | | AA | EIVMTQSPATLSVSPGERATLSCRASQSVNSNLA WYQLKPGQAPRLLISIASTRATGIPPRFNGSGSGT EFTLTISSLQSEDFAVYYCQQYNDWPCSFGQGT KLEIK<br>SEQ ID NO: 25666 | QVQLVESGGGVVQPGRSLRLSCAASGFTFSSYGMH WVRQAPGKGLEWVAVIWYDGSNKYYADSVKGRF TISRDNSKNSLYLQMNSLSAEDTAVYYCARDQGIV GATWFDYWGQGTLVTVSS<br>SEQ ID NO: 29672 |
| iPS:434427 | 21-225_70D6 | NA | GACATCCAGATGACCCAGTCTCCATCTTCCGT GTCTGCATCTGTAGGAGACAGAGTCACCATCA CTTGTCGGGCGAGTCAGGGTATTAGCAAATGG TTAGCCTGGTATCAGCAGAAATCAGGGAAAGC CCTTAAGCTCCTGATCTTTGCTGCATCCAGTTT GCAAAGTGGGGTCCCATCAAGGTTCAGCGGCA GTGGATCTGGGACAGATTTCACTCTCACCATC AGCAGCCTCCAGCCTGAAGATTTTGCAAATTA CTATTGTCAACAGACTAACAGTTTCCCTCTCAC TTTCGGCGGAGGGACCAAGGTGGAGATCAAA<br>SEQ ID NO: 25667 | CAGGTGCAGCTGGTGCAGTCTGGGGCTGAGGTG AAGAAGCCTGGGGCCTCAGTGAAGGTCTCCTGC AAGGCCTCTGGATACATCTTCACCGGCTACTATA TGCACTGGGTGCGACAGGCCCCTGGACAAGGGC TTGAGTGGATGGGATGGATCAACCTAAGAGTG GTGGCACAAACTCTGCACAGGACAGTCCATGGGCAC GGGTCTCCATGACCAGGGACAGTCCATCGGCAC AGCCTACATGGAGCTGCGCGGCTAAGATCTGA CGACACGGCCGAGTATTACTGTGCGAGAGCTCCG GGTAAAGCAGCAGCTGGTACATGGGGATTCTTTG ACTACTGGGGCCAGGGAACCCTGGTCACCGTCTC CTCA<br>SEQ ID NO: 29673 |

FIGURE 50
(Continued)

| | | | |
|---|---|---|---|
| | | AA | DIQMTQSPSSVSASVGDRVTITCRASQGISKWLA WYQQNPGKALKLLIFAASSLQSGVPSRFSGSGSG TDFTLTISSLQPEDFANYYCQQTNSFPLTFGGGT KVEIK | QVQLVQSGAEVKKPGASVKVSCKASGYIFTGYYM HWVRQAPGQGLEWMGWINPKSGGTNSAQKFQGR VSMTRDTSIGTAYMELRGLRSDDTAEYYCARAPGK AAAGTWGFFDYWGQGTLVTVSS |
| | | | SEQ ID NO: 25668 | SEQ ID NO: 29674 |
| iPS:434429 | 21-225_70H6 | NA | GACATCCAGATGACCCAGTCTCCATCCTCCCT GTCTGCATCTTTAGGAGACAGAGTCACCATCA CTTGCCGGACAAGTCAGAGACATTTCAACTAT TTAAATTGGTTTCAGCGGAAACCAGGAAAGC CCCTAAGGTCCTGATCTATACTGCATCCAGTTT GCAAAGTGGGATCCCATCAAGGTTCAGTGGCA GTGGATCTGGGACAGACTTCACTCTCACCATC AGCAGTCTGCAACCTGAAGATTCTGCAACTTA CTACTGTCAACAGAGTTACAGTATCCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGCAT GCACTGGGTCCGCCAGACTCCAGGCAAGGGCT GGACTGGGTGGCAGTTATATGCATGATGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGATGATCC CAGATCCTCGGCCGGGACTACTGGGGCCAGGG AACCCTGGTCACCGTCTCCTCA |
| | | | SEQ ID NO: 25669 | SEQ ID NO: 29675 |
| | | AA | DIQMTQSPSSLSASLGDRVTITCRTSQSIFNYLNW FQRKPGKAPKVLIYTASSLQSGIPSRFSGSGSGTD FTLTISSLQPEDSATYYCQQSYSIPLTFGGGTKVE IK | QVQLVESGGGVVQPGRSLRLSCAASGFTFSSYGMH WVRQTPGKGLDWVAVIWHDGSNKYYADSVKGRF TISRDNSKNTLYLQMNSLRAEDTAVYYCARDDPRS SAGDYWGQGTLVTVSS |
| | | | SEQ ID NO: 25670 | SEQ ID NO: 29676 |

FIGURE 50
(Continued)

| | | | |
|---|---|---|---|
| iPS:434431 | 21-225_70E7 | NA | GACATCGTGATGACCCAGTCTCCAGACTCCCTGGCTGTGTCTCTGGGCGAGAGGGCCACCCTCAACTGCAAGTCCAGCCAGAGTGTTTTATACAGCTCCAACAATAACAACTACTTGGCTTGGTACCAGCAGAAACCAGGACAGCCTCCTAAACTGCTCATTTACTGGGCATCTACCCGGGAATCCGGGGTCCCTGACCGATTCAGTGGCAGCGGGTCTGGGACAGATTTCACTCTCACTATCAGCAGCCTGCAGCTGAAGATGTGGCAGTTTATTACTGTCAGCAATATTATAATATTCTCCGACGTTCGGCCAAGGGACCAAGGTGGAAATCAAA<br><br>SEQ ID NO: 25671 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGGTGGATGCACCCTAACAGTGGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACGGCCGTGTATTACTGTGCGTATAGCAGTGGCTGGTACGTCTTTGACTACTGGGGCCAGGGAACCCTGGTCACCGTCTCCTCA<br><br>SEQ ID NO: 29677 |
| | | AA | DIVMTQSPDSLAVSLGERATLNCKSSQSVLYSSNNNNYLAWYQQKPGQPPKLLIYWASTRESGVPDRFSGSGSGTDFTLTISSLQAEDVAVYYCQQYYNILRRSAKGTKVEIK<br><br>SEQ ID NO: 25672 | QVQLVQSGAEVKKPGASVKVSCKASGYTFTNYDINWVRQATGQGLEWMGWMHPNSGNTGYAQKFQGRVTMTRNTSISTAYMELSSLRSEDTAVYYCAYSSGWYVFDYWGQGTLVTVSS<br><br>SEQ ID NO: 29678 |
| iPS:434433 | 21-225_70E8 | NA | GACATCCAGATGACCCAGTCTCCATCCTCCCTGTCTACATCTGTCGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAACAGCAGCCTGCAGCCTGAAGATTTTGCAACTTATTACTGTCTACAGCATAATGTTACCCGCTCACTTTCGGCGGAGGGACCAAGGTGGAGATCAAA<br><br>SEQ ID NO: 25673 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCTCTGGGTCCGCCAGGCTCCAGGCAAGGGTCTGGAGTGGGTGGCAATTATATGGAATGATGGAAAGTACCATCTCCAGAGACAATTCCAAGAGAGCCTGATTATCTGCAAATGAACAGCCTGAGAGCCGAGGACACGGCTGTGTATTACTGTGCGAGAGACCTACTGGACCCACGGGACTACTGGGGCCAGGGAACCCTGGTCACCGTCTCCTCA<br><br>SEQ ID NO: 29679 |

FIGURE 50
(Continued)

| | | | |
|---|---|---|---|
| | | AA | DIQMTQSPSSLSTSVGDRVTITCRASQGIRKDLG WYQQKPGKAPKRLIY AASSLQSGVPSRFSGSGS GTEFTLTISSLQPEDFATYYCLQHNRYPLTFGGG TKVEIK<br>SEQ ID NO: 25674 | QVQLVESGGGVVQPGRSLRLSCAASGFTFSSYGML WVRQAPGKGLEWVAIIWYDESNKYYADSVKGRFT ISRDNSKNTLYLQMNSLRAEDTAVYYCARDLLDPR DYWGQGTLVTVSS<br>SEQ ID NO: 29680 |
| iPS:434435 | 21-225_70G9 | NA | GACATCCAAATGACCCAGTCTCCATCTTCCGT GTCTGCATCTGTAGGAGACAGAGTCACCATCA CTTGTCGGGCGAGTCAGGATCAGGATATTAGCAGCTGG TTAGCCTGGTATCAGCAGAGAATCCAGGGAAAGC CCCTAAACTCTTGATCTATGCTGCATCCAGTTT GCAAAGTGGGGTCCCATCAAGGTTCAGCGGCA GTGGATCTGGGACAGATTTCACTCTCACCATC AGCAGCCTCCAGCCTGAAGATTTTGCAACTTA CTATTGTCAACAGAGACTAACAGTTTCCCTCTCAC TTTCGGCGGAGGGACCAAGGTGGAGATCAAA<br>SEQ ID NO: 25675 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGAC TTGAGTGGATGGGATGGATCAAACCTAACAGTG GTGGCACAAACCAAGCACAGAAGTTTCAGGGCA GGGTCACCATGACCAGGGACACGTCCATCAGCA CAGCCTACATGGAGCTGAGCAGTCTGAGATCTGA CGACACGGCCGTGTATTACTGTGCGAGAGCTCCG GGTATAGCAGCAGCTGGTACATGGGGATACTTTG ACTACTGGGGCCAGGGAACCCTGGTCACCGTCTC CTCA<br>SEQ ID NO: 29681 |
| | | AA | DIQMTQSPSSVSASVGDRVTITCRASQDISSWLA WYQQNPGKAPKLLIY AASSLQSGVPSRFSGSGS GTDFTLTISSLQPEDFATYYCQQTNSFPLTFGGGT KVEIK<br>SEQ ID NO: 25676 | QVQLVQSGAEVKKPGASVKVSCKASGYTFGYYM HWVRQAPGQGLEWMGWIKPNSGGTNQAQKFQGR VTMTRDTSISTAYMELSSLRSDDTAVYYCARAPGI AAAGTWGYFDYWGQGTLVTVSS<br>SEQ ID NO: 29682 |

FIGURE 50
(Continued)

| | | | |
|---|---|---|---|
| iPS:434437 | 21-225_70A12 | NA | GACATCCAGATGACCCAGTCTCCATCTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCTTAAGCTCTTGATATATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGATTAACAGTTTCCCTCTCA CTTTCGGCGGAGGGACCAAGGTGGAGATCAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAAACCAAACAGTG GTGGCACAAACCAAGCACACAGAAGTTTCAGGCA GGGTCACCATGACCAGGGACACGTCCATCAGCA CAGCCTACATGGAGCTGAGCGGGCTGAGATCTG ACGACACGGCCGTGTATTACTGTGCGAGAGCTCC GGGTACTGCAGCAACTGGTACATGGGATACTTT GACTACTGGGGCCAGGGAACCCTGGTCACCGTCT CCTCA |
| | | | SEQ ID NO: 25677 | SEQ ID NO: 29683 |
| | | AA | DIQMTQSPSSVSASVGDRVTITCRASQGISSWLA WYQQKPGKALKLLIYAASSLQSGVPSRFSGSGS GTDFTLTISSVQPEDFATYYCQQINSFPLTFGGGT KVEIK | QVQLVQSGAEVKKPGASVKVSCKASGYTFTGYYM HWVRQAPGQGLEWMGWIKPNSGGTNQAQKFQGR VTMTRDTSISTAYMELSGLRSDDTAVYYCARAPGT AATGTWGYFDYWGQGTLVTVSS |
| | | | SEQ ID NO: 25678 | SEQ ID NO: 29684 |
| iPS:434439 | 21-225_70E12 | NA | GACATCCAGATGACCCAGTCTCCATCCTCCCT ATCTGCATCTGTAGGAGACAGAGTCACCATCA CTTGCCGGGCAAGTCAGGGCATTAACAATAAT TTAAACTGGTTTCAGCAGAAACCAGGGAAAGC CCCTAAGCGCCTGATCTATGCTGCATCCAGTTT GCAAAGTGGGGTCCCATCAAGGTTCAGCGGCA GTGGATCTGGGACAGATTTCACTCTCACAATC AGCAGCCTGCAGCCTGAAGATTTTGCAACTTA TTACTGTCTACAGCATATAGTTACCCGCTCA CTTTCGGCGGAGGGTCCAAGGTGGAGATCAAA | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCTTCCATTAGTGGTAATAGTACT TACATATACTCCAGAGACAACGCCAAGAACTCACT TCACCATCTGCAAATGGACAGCCTGACAGCCGAGGA GTATCTGCAAATGGACAGCCTGACAGCCGAGGA CACGGCTGTGTATTACTGTGCGAGAGTGGCCGCC TTTGACTGCTGTGGGGCCAGGGAACCCTGGTCACCG TCTCCTCA |
| | | | SEQ ID NO: 25679 | SEQ ID NO: 29685 |

FIGURE 50
(Continued)

| | | | |
|---|---|---|---|
| iPS:434441 | | AA | DIQMTQSPSSLSASVGDRVTITCRASQGINNNLN WFQQKPGKAPKRLIYAASSLQSGVPSRFSGSGSG TEFTLTISSLQPEDFATYYCLQHNSYPLTFGGGSK VEIK SEQ ID NO: 25680 | EVQLVESGGGLVKPGGSLRLSCAASGFTFSSYSMN WVRQAPGKGLEWVSSISGNSTYIYYTDSVKGRFTIS RDNAKNSLYLQMDSLTAEDTAVYYCARVAAFDC WGQGTLVTVSS SEQ ID NO: 29686 |
| | 21-225_71A2 | NA | GACATCCAGATGACCCAGTCTCCATCCTCCCG GTCTGCATCTGTAGGAGACAGAGTCACCATCA CTTGCCGTGCAAGTCAGGGCATTAGAAATGAT TTAGGATGGTATCAGCAGAAACCAGGAAAAG CCCCTAAGCGCCTGATCTATATTGCATTCAGA TTGCAAATTGGGGTCCCATCAAGGTTCAGCGG CAGTGGATCTGGGACAGAATTCACTCTCACAA TCAGCAGCCTGCAGCCTGAAGATTTTGCAACT TATTACTGTATACACCATAATAGTTACCCGTG GACGTTCGGCCAAGGGACCAAGGTGGAAATC AAA SEQ ID NO: 25681 | CAGGTGCAGCTGGTGGAGTCTGGGGGAGGCGTG GTCCAGCCTGGGAGGTCCCTGAGACTCTCCTGTG CAACGTCTGGATTCACCTTCAGTGACTATGGCAT GCACTGGGTCCGCCAGGCTCCAGGCAAGGGGCT GGAGTGGGTGGCAGTGATATGGTATGATGAAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAATTGG GGTGGCAGGATGATTACTGGGGCCAGGGAACCC TGGTCACCGTCTCCTCA SEQ ID NO: 29687 |
| | | AA | DIQMTQSPSSRSASVGDRVTITCRASQGIRNDLG WYQQKPGKAPKRLIYIAFRLQIGVPSRFSGSGSG TEFTLTISSLQPEDFATYYCIHHNSYPWTFGQGT KVEIK SEQ ID NO: 25682 | QVQLVESGGGVVQPGRSLRLSCATSGFTFSDYGMH WVRQAPGKGLEWVAVIWYDESNKYYADSVKGRF TISRDNSKNTLYLQMNSLRAEDTAVYYCARELGW QDDYWGQGTLVTVSS SEQ ID NO: 29688 |

FIGURE 50
(Continued)

| | | NA | GACATCGTGATGACCCAGTCTCCAGACTCCCT GGCTGTGTCTCTGGGCGAGAGGGTCGCCATCA ATTGCAAGTCCAGCAGTGTTTACACAGC TCCAACAATAACAACTACTTAGATTGGTATCA GCAGAAACCAGGACAGCTTCCTAAACTGCTCA TTTTCTGGGCATCTACCCGGGAATTCGGGGTT CCTGACCGATTCAGTGGCAGCGGGGTTTGGGAC AGATTTCACTCTCACCATCAGCAGCCTGCAGG CTGAAGATGTGGCAGATTACTACTGTCAACAA TATTATATTACTCCGTGCAGTTTTGGCCAGGG GACCAAGCTGGAGATCAAA | CAGGTGCAACTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAGCACAGGCTATGCACAGAAGTTCCAGGGCAG AGTCACCATGACCAGGGACACCTCCGTCAGCAC AGCCTACATGGAGCTGAGCAGCCTGAGATCTGA GGACACGGCCGTCTATTACTGTGCATATAGCAGT GGCTGGTACTACTTTGACTACTGGGGCCAGGGAA CCCTGGTCACCGTCTCCTCA |
| iPS:434443 | 21-225_71G3 | | SEQ ID NO: 25683 | SEQ ID NO: 29689 |
| | | AA | DIVMTQSPDSLAVSLGERVAINCKSSQSVLHSSN NNNYLDWYQQKPGQLPKLLIFWASTREFGVPDR FSGSGFGTDFTLTISSLQAEDVADYYCQQYYITP CSFGQGTKLEIK | QVQLVQSGAEVKKPGASVKVSCKASGYTFTNYDIN WVRQATGQGLEWMGWMHPNSGSTGYAQKFQGR VTMTRDTSVSTAYMELSSLRSEDTAVYYCAYSSG WYFDYWGQGTLVTVSS |
| | | | SEQ ID NO: 25684 | SEQ ID NO: 29690 |
| | | NA | GACATCCAGATGACCCAGTCTCCATCCTCCCC GTCTGCATCTGTAGGAGACAGAGTCACCATCA CTTGCCGGGCAAGTCAGGGCATTAGAAATGAT TTAGATTGGTATCAGCAGAAGCCAGGGAAGG CCCCTCAGCCTCCATCTATGCTGCATCCAGTT TGCAAAGTGGGGTCCCATCAAGGTTCAGCGGC AGTGGATCTGGGACAGATTTCACTCTCACAAT CAGCAGCCTGCAGCCTGACGATTTTGCAACTT ATTACTGTCTACAGCATAATAGTTACCCATTC ACTTTCGGCCCTGGGACCAAAGTGGATATCAA A | CAGGTGCAACTGGTGCAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCCCCAGGCAAGGGGCT GGAGTGGGTGGCAGTTATTTGGTATGATAGAACA AATAAATACTATGCAGACTCCGTGAAGGGCCGA TTCACCATCTCCAGAGACAATTCCAAGAACACGC TGCATCTGCAAATGAACAGCCTGAGAGCCGAGG ACACGGCTGTGTATTACTGTGCGAGAGAACTGGG GATGTTGTCTGACTACTGGGGCCAGGGAACCCTG GTCACCGTCTCCTCA |
| iPS:434447 | 21-225_71B6 | | SEQ ID NO: 25685 | SEQ ID NO: 29691 |

FIGURE 50
(Continued)

| | | | |
|---|---|---|---|
| iPS:434449 | 21-225_71H6 | AA | DIQMTQSPSSPSASVGDRVTITCRASQGIRNDLD WYQQKPGKAPQRLIYAASSLQSGVPSRFSGSGS GTEFTLTISSLQPDDFATYYCLQHNSYPFTFGPGT KVDIK<br><br>SEQ ID NO: 25686 | QVQLVESGGGVVQPGRSLRLSCAASGFTFSNYGM HWVRQAPGKGLEWVAVIWYDRTNKYYADSVKGR FTISRDNSKNTLHLQMNSLRAEDTAVYYCARELGM LSDYWGQGTLVTVSS<br><br>SEQ ID NO: 29692 |
| | | NA | GACATCCAGATGACCCAGTCTCCATCCTCCCT GTCTGCATCTGTAGGAGACAGAGTCACCATCA CTTGCCGGGCAAGTCAGGGCATTAGAGAATGTT TTAGGCTGGTATCAGCAGAAACCAGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGATATAATAGTTACCCATTC ACTTTCGGCCCTGGGACCAAAGTGGATATCAA A<br><br>SEQ ID NO: 25687 | GAGGTGCAGCTGGTGGAGTCTGGGGGAGGCTG GTCAAGCCTGGGGGGTCCCTGAGACTGTCCTGTG CAGCCTCTGGATTCACCTTCAGTAGCTATAGCAT GAACTGGGTCCGCCAGGCTCCAGGGAAGGGACT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACGGCCTGAGAGCCGAGGA CACGGCTGTGTATTTCTGTGCGAAAACCAATGCT TTTGATATCTGGGGCCAGGGGACAATGGTCACCG TCTCTTCA<br><br>SEQ ID NO: 29693 |
| | | AA | DIQMTQSPSSLSASVGDRVTITCRASQGIRNVLG WYQQKPGKAPKRLIYAASSLQSGVPSRFSGSGS GTEFTLTISSLQPEDFATYYCLQYNSYPFTFGPGT KVDIK<br><br>SEQ ID NO: 25688 | EVQLVESGGGLVKPGGSLRLSCAASGFTFSSYSMN WVRQAPGKGLEWVSSISGTSSYIYYADSVKGRFTIS RDNAKNSLYLQMNGLRAEDTAVFCAKTNAFDIW GQGTMVTVSS<br><br>SEQ ID NO: 29694 |

FIGURE 50
(Continued)

| | | | |
|---|---|---|---|
| iPS:434451 | 21-225_71B7 | NA | GACATCCAGATGACCCAGTCTCCATCTCCGT GTCTGCATCTGTAGGAGACAGAGTCACCATCA CTTGTCGGGCGAGTCAGGGTATTAGCAGCTGG TTAGCCTGGTATCAGCAGAAATCCAGGGAAGC CCCTAAGCTCCTGATCTATGCTGCATCCAGTTT GCAAGGTGGGGTCCCATCAAGGTTCAGCGGCA GTGGATCTGGGACAGATTCACTCTCACCATC AGCAGCCTCCAGCTGAAGATTTTGCAAATTA CTATTGTCAACAGACTAATAGTTTCCCTCTCAC TTTCGGCGGAGGGACCAAGGTGGAGATCAAA<br><br>SEQ ID NO: 25689 | CAGGTGCAGCTGGTGCAGTCTGGGGCTGAGGTG AAGAAGCCTGGGGCCTCAGTGAAGGTCTCCTGC AAGGCTTCTGGATACATCTTCACCGGCTACTATA TGCACTGGGTGCGACAGGCCCCTGGACAAGGGC TTGAGTGGATGGGATGGATCAACCCTAACAGTGG TGGCACAAACTCTGCACAGAAGTTTCAGGGCAG GGTCACCATGACCAGGGACACGTCCATCGGCAC AGCCTACATGGAGCTGAGCGGGCTGAGATCTGA CGACACGGCCGTGTATTACTGTGCGAGAGCTCCG GGTAAAGCAGCAGCTGGTACATGGGGATTCTTTG ACTACTGGGGCCAGGGAACCCTGGTCACCGTCTC CTCA<br><br>SEQ ID NO: 29695 |
| | | AA | DIQMTQSPSSVSASVGDRVTITCRASQGISSWLA WYQQKPGKAPKLLIYAASSLQGGVPSRFSGSGS GTDFTLTISSLQPEDFANYYCQQTNSFPLTFGGG TKVEIK<br><br>SEQ ID NO: 25690 | QVQLVQSGAEVKKPGASVKVSCKASGYIFTGYYM HWVRQAPGQGLEWMGWINPNSGGTNSAQKFQGR VTMTRDTSIGTAYMELSGLRSDDTAVYYCARAPG KAAAGTWGFFDYWGQGTLVTVSS<br><br>SEQ ID NO: 29696 |
| iPS:434453 | 21-225_71B11 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGATTGGTATCAGCAGCACACCAGGGAAAGC CCCTAAGCGCCTGATCTATGCTGCATCCAGTTT GCAAAGTGGGGTCCCATCAAGGTTCAGCGGCG GTGGATCTGGGACAGATTCTCTCTCACAATC AGCAGCCTGCAGCCTGAAGATTTTACAACTTA TTACTGTCTACAGCATATAATACTTACCCATTCAC TTTCGGCCCTGGGACCAAAGTGGATGTCAAA<br><br>SEQ ID NO: 25691 | CAGGTGCAGCTGGTGGAGTCTGGGGGAGGCGTG GTCCAGCCTGGGAGGTCCCTGAGACTCTCCTGTG CAGCCGTCTGATTCACCTTCAGTGACTATGGCAT GCACTGGGTCCGCCAGGCTCCAGGCAAGGGGCT GGAGTGGGTGGCAGTTATATGGTATGATGAAAT AATAAATACTATGGAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACTGGG GATGTTGTCTGACTACTGGGGCCAGGGAACCCTG GTCACCGTCTCTCA<br><br>SEQ ID NO: 29697 |

FIGURE 50
(Continued)

| | | | |
|---|---|---|---|
| iPS:434455 | 21-225_72F5 | AA | DIQMTQSPSSLSASVGDRVTITCRASQGIRNDLD WYQQTPGKAPKRLIYAASSLQSGVPSRFSGSGS GTEFSLTISSLQPEDFTTYYCLQHNTYPFTFGPGT KVDVK<br><br>SEQ ID NO: 25692 | QVQLVESGGGVVQPGRSLRLSCAASGFTFSDYGM HWVRQAPGKGLEWVAVIWYDRNNKYYGDSVKG RFTISRDNSKNTLYLQMNSLRAEDTAVYYCARELG MLSDYWGQGTLVTVSS<br><br>SEQ ID NO: 29698 |
| | | NA | GACATCCAGATGACCCAGTCTCCATCCTCCCT GTCTGCATCTGTAGGAGACAGAGTCATCATCC CTTGCCGGGCAAGTCAGAACATTAGACGCTAT TTAAATTGGTATCAGCAGAAACCAGGGAAAG CCCCTAAACTCCTGATCTATGCTGCATCCAGTT TGCAAAGTGGGGTCCCATCAAGGTTCAGTGGC AGTGGATCTGGGACAGGCCTGAAGATTCACTCTGACCAT CAGCAGTCTGCAGCCTGAAGATTTTGCAACTT ACTCTGTCAACAGACATTACAGTACCCCACC TTCGGCCAAGGGACACGACTGGATATTAAT<br><br>SEQ ID NO: 25693 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GATCTGGGTCCGCCAGGCTCCAGGGAAGGGGCT GGAGTGGGTCTCAACTATTAGTGGTAGTGGTGGT TACACATACTCCGCAGACTCCGTGAAGGGCCGGT TCACCATCTCCAGAGACAATTCCAAGAACACGCT GTATCTTCAAATGAACAGCTGAGACGTAGCA CACGGCCGTATATTACTGTGCGAGACGTATAGCA GTGACTGGGACGGAATGGTACGACCCTGGGGC CAGGGAACCCTGGTCACCGTCTCCTCA<br><br>SEQ ID NO: 29699 |
| | | AA | DIQMTQSPSSLSASVGDRVIIPCRASQNISSYLNW YQQKPGKAPKLLIYAASSLQSGVPSRFSGSGSGT DFTLTISSLQPEDFATYSCQQTYSTPFGQGTRLD IN<br><br>SEQ ID NO: 25694 | EVQLLESGGGLVQPGGSLRLSCAASGFTFSSYAMI WVRQAPGKGLEWVSTISGSGGYTYSADSVKGRFTI SRDNSKNTLYLQMNSLRAEDTAVYYCARRIAVTGT EWYDPWGQGTLVTVSS<br><br>SEQ ID NO: 29700 |

FIGURE 50
(Continued)

| | | | |
|---|---|---|---|
| iPS:434457 | 21-225_72G12 | NA | GACATCCAGATGACCCAGTCTCCATCTCCT GTCTGCATCTGTAGGAGACAGAGTCACCATCA CTTGCCGGGCGAGTCAGGGCATTAGCAGTTAT TTAAATTGGTCTCAGCAGAAACCAGGGAAAGT TCCTAAGCTCCTGATCTGTGTGTCTTCCAATTT GCAATCTGGAGTCCCATCTCGGTTCAGCGGCA GTGCATCTGGGACAGAATTCATTCTCACTATC AGCAGCCTGCAGCCTGAAGATGTTACAACTTA TTACGGTCAACAGATTACAATGCCCCGCTCA CTTTCGGCGGAGGGACCAAGGTGGAGATCAA A<br><br>SEQ ID NO: 25695 | CAGGTGCAGCTGGTGGTGGAGTCTGGGGGAGGCGTG GTCCAGCCTGGGAGGTCCCTGAGACTCTCCTGTG CAGCCGTCTGGATTCACCTTCAGTAGTTATGGCAT GCACTGGGTCCGCCAGGCTCCAGACACGGGGCT GGAGTGGGTGGCAGTTATATGGTTTGATGAAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGCTTGG TTTCAGCAGTGACTACTGGGGCCAGGGAACCCTG GTCACCGTCTCCTCA<br><br>SEQ ID NO: 29701 |
| | | AA | DIQLTQSPSSLSASVGDRVTITCRASQGISSYLNW SQQKPGKVPKLLICGASNLQSGVPSRFSGSASGT EFILTISSLQPEDVTFYGQQNYNAPLTFGGGTK VEIK<br><br>SEQ ID NO: 25696 | QVQLVESGGGVVQPGRSLRLSCAASGFTFSSYGMH WVRQAPDTGLEWVAVIWFDESNKYADSVKGRFT ISRDNSKNTLYLQMNSLRAEDTAVYYCARELGFSS DYWGQGTLVTVSS<br><br>SEQ ID NO: 29702 |
| iPS:434459 | 21-225_71A7 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCTGGGAAAGC CCCTAAGCTCCTGATCTATGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTTGCAACTTA CTATTGTCAACAGGTTAACAGTTTCCCTCTCAC TTTTCGGCGGAGGGACCAAGGTGGAGATCAAA<br><br>SEQ ID NO: 25697 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGC TTGAGTGGATGGGATGGATCAACCCTAAAAGTG GTGGCACAAATTATGTACAGAAGTTTCAGGGCAG GGTCACCATGACCAGGGACACGTCCATCAGCAC AGCCTACATGGAGCTGAGCAGTCTGAGATCTGAC GACACGGCCGTGTATTACTGTGCGAGAGCTCGG GTACAGCACCAGCTGGGTCATGGGATACTTTGA CTACTGGGGCCAGGGAACCCTGGTCACCGTCTCC TCA<br><br>SEQ ID NO: 29703 |

FIGURE 50
(Continued)

| | | AA | DIQMTQSPSSVSASVGDRVTITCRASQGISSWLA WYQQKPGKAPKLLIYAASSLQSGVPSRFSGSGS GTDFTLTISSLQPEDFATYYCQQVNSFPLTFGGG TKVELK<br><br>SEQ ID NO: 25698 | QVQLVQSGAEVKKPGASVKVSCKASGYTFTGYYM HWVRQAPGQGLEWMGWINPKSGGTNYVQKFQGR VTMTRDTSISTAYMELSSLRSDDTAVYYCARAPGT APAGSWGYFDYWGQGTLVTVSS<br><br>SEQ ID NO: 29704 |
|---|---|---|---|---|
| iPS:434461 | 21-225_73A3 | NA | GACATCCAGATGACCCAGTCTCCATCTTCCGT GTCTGCATCTATAGGAGACAGAGTCACCATCA CTTGTCGGGCGAGTCAGGGTATTAGCAACTGG TTAGCCTGGTATCAGCAGAAACCAGGGAAAG CCCCTAAGCTCCTGATCTATGCTGCATCCAGTT TGCAAAGTGGGGGTCCCGTCAAGGTTCAGCGGC AGTGGATCTGAGACAGATTTCACTCTCACCAT CAGCAGCCTGCAGCCTGAAGATTTTGCAACTT ACTATTGTCAACAGGTTAACAGTTTCCCTCTCA CTTTCGGCGGAGGGACCAAGGTGGAGATCAA A<br><br>SEQ ID NO: 25699 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTACGACAGGCCCCTGGACAAGGAC TTGACTGGATGGGATGGATCAACCCTAAAAGTGG TGGCACGAACATCATGTCCAGAAGTTTCAGGGCAG GGTCGCCATGACCAGGGACACGTCCATCAGCAC AGCCTACATGGAGCTGAGCAGTCTGAGAGCTCCGG GACACGGCCGTGTATTACTGTGCGAGAGCTCCGG GTACAGCAGCAGCTGGGTCATGGGATGCTTTGA CTACTGGGGCCAGGGAACCCTGGTCACCGTCTCC TCA<br><br>SEQ ID NO: 29705 |
| | | AA | DIQMTQSPSSVSASIGDRVTITCRASQGISNWLA WYQQKPGKAPKLLIYAASSLQSGVPSRFSGSGSE TDFTLTISSLQPEDFATYYCQQVNSFPLTFGGGT KVEIK<br><br>SEQ ID NO: 25700 | QVQLVQSGAEVKKPGASVKVSCKASGYTFTGYYM HWVRQAPGQGLDWMGWINPKSGGTNHVQKFQGR VAMTRDTSISTAYMELSSLRSDDTAVYYCARAPGT AAAGSWGCFDYWGQGTLVTVSS<br><br>SEQ ID NO: 29706 |

FIGURE 50
(Continued)

| | | | |
|---|---|---|---|
| iPS:434463 | 21-225_73A6 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTTTCAGCAGAAACCAGGGAAAGC CCCTAAGCGCCTGATCTATGCTGCATCCAATT GCAAAGTGGGGTCCCATCAAGGTTCAGCGGCA GTGGATCTGGGACAGACTTCACTCTCACAATC AGCAGCCTGCAGCCTGAAGATTTTGCAACTTA TTACTGTCTACAGCATAATAGTTACCCATTCAC TTTCGGCCCTGGGACCAAAGTGGATATCAAA<br><br>SEQ ID NO: 25701 | CAGGTGCAGCTGGTGGTGGAGTCTGGGGGAGGCGTG GTCCAGCCTGGGAGGTCCCTGAGACTCTCCTGTG CAGCCTCTGGATTCACCTTCAGTTACTATGGCAT GCACTGGGTCCGCCAGGCTCCAGGCAAGGGCT GGAGTGGGTGGCAGTTATATTATATGATGGAAGT AAGAAATACTATGCAGCCTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGCGAGGAGTATCC GGACTTTGACTACTGGGGCCAGGGAACCCTGGTC ACCGTCTCCTCA<br><br>SEQ ID NO: 29707 |
| | | AA | DIQMTQSPSSLSASVGDRVTITCRASQGIRNDLG WFQQKPGKAPKRLIYAASNLQSGVPSRFSGSGS GTEFTLTISSLQPEDFATYYCLQHNSYPFTFGPGT KVDIK<br><br>SEQ ID NO: 25702 | QVQLVESGGGVVQPGRSLRLSCAASGFTFSYYGM HWVRQAPGKGLEWVAVILYDGSKKYYAASVKGR FTISRDNSKNTLYLQMNSLRAEDTAVYYCARSIPDF DYWGQGTLVTVSS<br><br>SEQ ID NO: 29708 |
| iPS:434467 | 21-225_73H8 | NA | GACATCCAGATGACCCAGTCTCCATCCTCCT GTATGCATCTGTAGGAGACAGAGTCACCATCA CTCGCCGGGCAAGTCAGGACATCAGAAATGAT TTAGGCTGGTATCAGCAGAAACCAGGGAAAG CCCTTAAGCGCCTGATCTATGCTGCATCCAGT TTGCAAAGTGGGGTCCCATCAAGCTTCAGCGG CAGTGGATCTGGGACAGAATTCACTCTCACAA TCAGCAGCTTGCAGCCTGAAGATTTTGCAACT TATTACGGTATACAGCATAATAGTTACCCTCC GATCACCCCTCTGCCAAGGGACACGACTGGAG ATTAAA<br><br>SEQ ID NO: 25703 | GAGGTGCAGTTACTGGAGTCTGGGGGAGGCTGG GTACAGTCTGGGGGGTCCCTGAGACTCTCCTGTG CAGCCTCTGGATTCACCTTTAGCAGCAATGCCAT GAGCTGGGTCCGCCAGGCTCCAGGGAAGGGCT GGAGTGGGTCTCAGACATTAGTGGTAGTGGTGGT ACCACATTCTACGCAGACTCCGTGAAGGGCCGT TCACCATCTCCAGAGACAATGAACAGCCTGAGAGCGAGGA GTATCTGCAAATGAACAGCCTGAGAGCCGAGGA CACGGCCGTATATTACTGTGCGAAATGGGATAGC AGCAGCTGTACGACGACTCCCTTTGACTACT GGGGCCAGGGAACCCTGGTCACCGTCTCCTCA<br><br>SEQ ID NO: 29709 |

FIGURE 50
(Continued)

| | | | |
|---|---|---|---|
| iPS:434469 | 21-225_73C9 | AA | DIQMTQSPSSLYASVGDRVTITRRASQDIRNDLG WYQQKPGKALKRVIYAASSLQSGVPSSFSGSGS GTEFTLTISSLQPEDFATYYGIQHNSYPPITVGQG TRLEIK<br>SEQ ID NO: 25704 | EVQLLESGGGWVQSGGSLRLSCAASGFTFSSNAMS WVRQAPGKGLEWVSDISRSGGTTFYADSVKGRFTI SRDNSKNTLYLQMNSLRAEDTAVYYCAKWDSSSW YDVTPFDYWGQGTLVTVSS<br>SEQ ID NO: 29710 |
| | | NA | CAGGTGCAGCTGTGGTGGAGTCTGGGGGAGGCGTG GTCCAGCCTGGGAGGTCCCTGAGACTCTCCTGTG CAGCGTCTGGATTCACCTTCAGCAATTATGTCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGAAAGTA TAGCAGCAGCTGGTTGACTACGGTATGGACGTC TGGGGCCAAGGGACCACGGTCACCGTCTCCTCA<br>SEQ ID NO: 29711 | CAGGTGCAGCTGTGGTGGAGTCTGGGGGAGGCGTG GTCCAGCCTGGGAGGTCCCTGAGACTCTCCTGTG CAGCGTCTGGATTCACCTTCAGCAATTATGTCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGAAAGTA TAGCAGCAGCTGGTTGACTACGGTATGGACGTC TGGGGCCAAGGGACCACGGTCACCGTCTCCTCA<br>SEQ ID NO: 29711 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEIK<br>SEQ ID NO: 25706 | QVQLVESGGGVVQPGRSLRLSCAASGFTFSNYVM HWVRQAPGKGLEWVAVIWYDGSNKYYADSVKGR FTISRDNSKNTLYLQMNSLRAEDTAVYYCARERYS SSWFDYGMDVWGQGTTVTVSS<br>SEQ ID NO: 29712 |

FIGURE 50
(Continued)

| | | | |
|---|---|---|---|
| iPS:434471 | 21-225_75G3 | NA | GAAATTGTGTTGACGCAGTCGCCAGGCACCCTGTCTTTGTCTCCAGGGGAAAGAGCCACCCTCTCCTGCAGGGCCCGTCAGTCAGAATGTTGACAGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTTTTACTGTCAGCAGTATGAACGCTCACGTGGACGTTCGGCCAAGGGACCAAGGTGGAGATCAAA SEQ ID NO: 25707 |
| | | AA | EIVLTQSPGTLSLSPGERATLSCRARQNVDSSYLAWYQQKPGQAPRLLIYGASSRATGIPDRFSGSGSGTDFTLTISRLEPEDFAVFYCQQYERSPWTFGQGTKVEIK SEQ ID NO: 25708 |
| | | NA | CAGGTGCAGCTACAGCAGTGGGGCGCAGGACTGTTGAAGCCTTCGGAGACCCTGTCCCTCACCTGCGCTGTCTATGGTGGGTCCAGTCAGTGGTTCTACTGGAGCTGGATCCGCCAGCCCCCAGGGAAGGGCTGGAGTGGATTGGGGAAATCAATCTTAGTGGAAGTACCAACTACAACCCGTCCCTCAAGAGTCGAGTCACCATATCAGTAGACACGTCCAAGAGCCAGTTCTCCCTGACGCTGCTCTGTGACCGCCGCCGGACACGGCTGTGTATTACTGTGCGAGAGATACGGTGGCCTGACTACTGGGGCCAGGGAACCCTGGTCACCGTCTCCTCA SEQ ID NO: 29713 |
| | | AA | QVQLQQWGAGLLKPSETLSLTCAVYGGSLSGSYWSWIRQPPGKGLEWIGEINLSGSTNYNPSLKSRVTISVDTSKSQFSLTLRSVTAADTAVYYCARDYGGLDYWGQGTLVTVSS SEQ ID NO: 29714 |
| iPS:434473 | 21-225_76D1 | NA | GAAATTGTGTTGACGCAGTCGCCAGGCACCCTGTCTTTGTCTCCAGGGGAAAGAGCCACCCTCTCCTGCAGGGCCAGTCAGAATATTACAGCAACTACCTAGCCTGGTACCAGGAGAAGCCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGTAGTGTATTACTGTCAGCAGTATGAAAGTTCACCGTGGACGTTCGGCCAAGGGACCAAGGTGGAAATCAAA SEQ ID NO: 25709 |
| | | NA | CAGGTACAACTACAGCAGTGGGGCGCAGGACTGTTGAAGCCTTCGGAGACCCTGTCCCTCACCTGCGCTGTCTATGGTGGGTCCTTCAGTGGTTGCTACTGGAGCTGGATCCGCCAGCCCCCAGGGAAGGGCTGGAGTGGATTGGGGAAATCAATCATAGTGGAAGAACCAACTACAACCCGTCCCTCAAGAGTCGAGTCACCATATCAGTAGACACGTCCAAGAACCAGTTCTCCCTGAAGCTGAGCTGTGTGACCGCCGCGGACACGGCTGTGTATTACTGTGCGGAGGACTACGGCGGTATGGACGTCTGGGGCCAGGGGACCACGGTCACCGTCTCCTCA SEQ ID NO: 29715 |

FIGURE 50
(Continued)

| | | | |
|---|---|---|---|
| iPS:434475 | 21-225_74F9 | AA | EIVLTQSPGTLSLSPGERATLSCRASQNIYSNYLAWYQEKPGQAPRLLIYGASSRATGIPDRFSGSGSGTDFTLTISRLEPEDFVVYYCQQYESSPWTFGQGTKVEIK | QVQLQQWGAGLLKPSETLSLTCAVYSGSFSGCYWSWIRQPPGKGLEWIGEINHSGRTNYNPSLKSRVTISVDTSKNQFSLKLSSVTAADTAVYYCARDYGGMDVWGQGTTVTVSS |
| | | | SEQ ID NO: 25710 | SEQ ID NO: 29716 |
| | | NA | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATTACAACTACTTAGCTTGGTACCAGCAGAAACCAGGACAGCCTCCTAAGAAGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTCCTGTCAGCAATATTATAGTAGTCCTCGACGTTCGGCCAAGGGACCAAGGTGGAAATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGAACCCTAACAGTGGTAACACAGGCTGTGCACCAGAAGTTCCAGGGCAGTCACCATGACCAGGAACACCTCCATAAGCACAGCCTACATGGAGCTGAGCAGCCTGAGATCTGAGGACACGGCCGTGTATTACTGTGCGAGTAGCAGTGGCTGGAACTTCTTTGACTACTGGGGCCAGGGAACCCTGGTCACCGTCTCCTCA |
| | | | SEQ ID NO: 25711 | SEQ ID NO: 29717 |
| | | AA | DIVMTQSPDSLAVSLGERATINCKSSQSVLYSSNNNYLAWYQQKPGQPPKKLIYWASTRESGVPDRFSGSGSGTDFTLTISSLQAEDVAVYSCQQYYSSPPTFGQGTKVEIK | QVQLVQSGAEVKKPGASVKVSCKASGYTFTNYDINWVRQATGQGLEWMGWMNPNSGNTGCAQKFQGRVTMTRNTSISTAYMELSSLRSEDTAVYYCASSSGWNFFDYWGQGTLVTVSS |
| | | | SEQ ID NO: 25712 | SEQ ID NO: 29718 |

FIGURE 50
(Continued)

| | | | | |
|---|---|---|---|---|
| iPS:434477 | 21-225_74A6 | NA | GACATCGTGATGACCCAGTCTCCAGACTCCCT GGCTGTGTCTCCGGGGAGAGGGCCACCATCA ACTGCAAGTCCAGCCAGAGTGTTTTACACAGC TCCAACAATAACAATTACTTAGCCTGGTACCA GCAGAAACCAGGACAGCCTCCTGACCTGCTCA TTTACTGGGCATCAACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTTTAGTACTCCGTGACGTTCGGCCAAGG GACCCAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCGGGGCAG AGTCACCATGACCTGAACACCTCCATAAGCACA GCCTACATGGAGCTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTCTCCTCA |
| | | | SEQ ID NO: 25713 | SEQ ID NO: 29719 |
| | | AA | DIVMTQSPDSLAVSPGERATINCKSSQSVLHSSN NNNYLAWYQQKPGQPPDLLIYWASTRESGVPD RFSGSGSGTDFTLTISSLQAEDVAVYYCQQYFST PWTFGQGTQVEIK | QVQLVQSGAEVKKPGASVKVSCKASGYTFTNYDIN WVRQATGQGLEWMGWMHPNSGNTGYAQKFRGR VTMTWNTSISTAYMELSSLRSEDTAVYYCASSSGW YYFDYWGQGTLVTVSS |
| | | | SEQ ID NO: 25714 | SEQ ID NO: 29720 |
| iPS:434479 | 21-225_76H1 | NA | GAATTTATGTTGACGCAGTCTCCAGGCACCCT GTATTGGTCTCCAGGGGAAAGAGCCACCCTCT CGTGCAGGGCCAGTCAGAGTGTTAGCAGCAGC TACTTAGTCTGGTATCAGCAGAAAACCTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTTGTCACCGC TCACTTTCGGCGGAGGGACCAAGGTGGAGATC ACA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGC TTGAGTGGATGGGATGGATGCACAGAAGTTCCAGGGCAG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA |
| | | | SEQ ID NO: 25715 | SEQ ID NO: 29721 |

FIGURE 50
(Continued)

| | | | |
|---|---|---|---|
| | | AA | EFMLTQSPGTLYWSPGERATLSCRASQSVSSSYL VWYQQKPGQAPRLLIYGASTRATGIPDRFSGSGS GTDFTLTISRLEPEYFAVYYCQQYGCSPLTFGGG TKVEIT | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25716 | SEQ ID NO: 29722 |
| iPS:434481 | 21-225_74B10 | NA | GACATCGTGATGACCCAGTCTCCAGACTCCCT GGCTGTGTCTCTGGGCGAGAGGGCCACCATCA ACTGCAAGTCCAGCCAGAGTGTTTACACAGC TCCAACAATAAGAACTACTTAACTTGGTACCA GCAGAAACCAGGACAGGCTCCTAAGCTGCTCA TTTACTGGGCATCTCACGATCGGGAATCCGGGGTC CCTGACCGATTCAGTGGCAGCGGGTCTGGGAC AGATTTCAGTCTCACGATCGGCAGCCTGCAGG CTGAAGATGTGGCAGTTTATTACTGTCAGCAA TATTATAGTATTCCTCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATTCACCTTCACCAATTATGATA TCAACTGGGTGCGACAGGCCACTGGACAAGGGC TTGAGTGGATGGGATGGATGCACCCTAACAGTGG TAACACAGGCTTTGCACAGAAGTTCCAGGGCAG AGTCACCATGACCAGGAACACCTCCATAAGCAC AGCCTACATGGAACTGAGCAGCCTGAGATCTGA GGACACGGCCGTGTATTACTGTGCGGTTTCCAGT GGCTGGTACTGGTTCGACCCCTGGGGCCAGGGA ACCCTGGTCACCGTCTCCTCA |
| | | | SEQ ID NO: 25717 | SEQ ID NO: 29723 |
| | | AA | DIVMTQSPDSLAVSLGERATINCKSSQSVLHSSN NKNYLTWYQQKPGQPPKLLIYWASTRESGVPDR FSGSGSGTDFSLTIGSLQAEDVAVYYCQQYYSIP PTFGQGTKVEIK | QVQLVQSGAEVKKPGASVKVSCKASGFTFTNYDIN WVRQATGQGLEWMGWMHPNSGNTGFAQKFQGR VTMTRNTSISTAYMELSSLRSEDTAVYYCAVSSGW YWFDPWGQGTLVTVSS |
| | | | SEQ ID NO: 25718 | SEQ ID NO: 29724 |

FIGURE 50
(Continued)

| | | | |
|---|---|---|---|
| iPS:434483 | 21-225_74C12 | NA | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATGCGAACTACTTAGCTTGGTACCAGCAGAAACCAGGACAGCCTCCTAACCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTCCGTGCAGTTTGGCCAGGGACCAAGCTGGAGATCAAA<br>SEQ ID NO: 25719 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGAACCCTAACAGTGGTAACACAGGCTATGCACAGAAGTTCCAGGCAGAGTCACCATGAGCACAGGAACACCTCCATAAGCACAGCCTACATGGAGCTGAGCAGCCTGAGATCTGAGGACACGGCCGTGTACTATTGTGCGATTAGCAGTGGCTGTACTGGTTCGACCCCTGGGGCCAGGGAACCCTGGTCACCGTCTCCTCA<br>SEQ ID NO: 29725 |
| | | AA | DIVMTQSPDSLAVSLGERATINCKSSQSVLYSSNNANYLAWYQQKPGQPPNLLIYWASTRESGVPDRFSGSGSGTDFTLTISSLQAEDVAVYYCQQYYSTPCSFGQGTKLEIK<br>SEQ ID NO: 25720 | QVQLVQSGAEVKKPGASVKVSCKASGYTFTNYDINWVRQATGQGLEWMGWMNPNSGNTGYAQKFQGRVTMTRNTSISTAYMELSSLRSEDTAVYYCAISSGWYWFDPWGQGTLVTVSS<br>SEQ ID NO: 29726 |
| iPS:434485 | 21-225_76D2 | NA | GAAATAGTGATGACCCAGTCTCCAGCCACCCCGTCTGTGTCTCTGGGGGAAAGAGCCACCCTCTCCTGCAGGGCCAGTGTGAGTGTTGTCAACAGCTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGTGTGCAGCCTGAAGATTTTGCAAGTTATTACTGTCAGCAGTATAATAATGACTGGCCGTGCAGTTTTGGCCAGGGGACCAAGCTGGAGATCAAA<br>SEQ ID NO: 25721 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATTTGGTATGATGGAAGTAATAAATACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTATTACTGTGCGAGCGATCGCAATATAGTGGAGCTACTTACTTTGAGTCCTGGGGCCAGGGAACCCTGGTCACCGTCTCCTCA<br>SEQ ID NO: 29727 |

FIGURE 50
(Continued)

| | | | |
|---|---|---|---|
| | | AA | EIVMTQSPATPSVSPGERATLSCRASVSVVNSLA WYQQKPGQAPRLLIHGASTRATGIPARFSGSGSG TEFTLTISSVQSEDFAIYYCQQYNDWPCSFGQGT KLEIK | QVQLVESGGGVVQPGRSLRLSCAASGFTFSSYGMH WVRQAPGKGLEWVAVIWYDGSNKYYADSVKGRF TISRDNSKNTLFLQMNSLRAEDTAVYYCASDRNIV GATYFESWGQGTLVTVSS |
| | | | SEQ ID NO: 25722 | SEQ ID NO: 29728 |
| iPS:434487 | 21-225_76G2 | NA | GACATCGTGATGACCCAGTCTCCAGACTCCCT GGCTGTGTCTCTGGGCGAGAGGGCCACCATCA ACTGCAAGTCCAGCCAGAGTGTTTACACAGC TCCAACAATTACAACTACTTAGCTTGGTACCA GCAGAGACCAGGACAGGCCTCCTAGGCTGCTCA TTTACTGGGCATCTCACCCGGGAATCCGGGGTC CCTGACCGATTCAGTGGCAGCGGTTCTGGGAC AGATTTCACTCTCACCATCAGCAGCCTGCAGG TTGAAGATGTGGCAGTTTATTACTGTCAGCAA TATTATAGTTCTCCTCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGAC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTATATGGAGCTGAGCAGCCTGAGATCTGA AGACACGGCCGTGTATTACTGTGCGGGTAGCAGT GGCTGGTACATGTTTGACTACTGGGGCCAGGGAA CCTCGGTCACCGTCTCCTCA |
| | | | SEQ ID NO: 25723 | SEQ ID NO: 29729 |
| | | AA | DIVMTQSPDSLAVSLGERATINCKSSQSVLHSSN NYNYLAWYQQRPGQPPRLLIYWASTRESGVPDR FSGSGSGTDFTLTISSLQVEDVAVYYCQQYYSSP PTFGQGTKVEIK | QVQLVQSGAEVKKPGASVKVSCKASGYTFNYDIN WVRQATGQGLEWMGWMNPNSGNTGYAQKFQGR VTMTRNTSISTAYMELSSLRSEDTAVYYCAGSSGW YMFDYWGQGTLVTVSS |
| | | | SEQ ID NO: 25724 | SEQ ID NO: 29730 |

FIGURE 50
(Continued)

| | | | | |
|---|---|---|---|---|
| iPS:434489 | 21-225_74E4 | NA | GACATCCAGATGACCCAGTCTCCATCCTCCT GTCTGCTCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCACTT TGCAAAGTGGGGGTCCCATCAAGGTTCAGCGGC AGTGGATCTGGGACAGAATTCACTCTCACAAT CAGCGGCCTGCAGCCTGAAGATTTTGCAACTT ATCACTGTCTACAGCATAGTAATTACCCGCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCATCGTA CTGTCTCTGGTGGCTCATCAGCAGTAGTAATTA CTACTGGGGCTGGATCCGCCAGCCCCAGGAA GGGGCTGGAGTGGATTGGGAGTATCTATTATAGT GGATACACCTCTACAACCCGTCCCTCAAGAGTC GAGTCACCATATCCGTAGACTCGTCCAAGAACCA CTTCTCCCTGAGGCTGAGCTCTGTGACCGCCGCA GACACGGCTGTGTATTACTGTGCGAGACTTGACT CTAACTGGGGTCTTGACTACTGGGGCCAGGGAAC CCTGGTCACCGTCTCCTCA<br>SEQ ID NO: 29731 |
| | | AA | DIQMTQSPSSLSASVGDRVTITCRASQGIRNDLG WYQQKPGKAPKRLIYAASTLQSGVPSRFSGSGS GTEFTLTISGLQPEDFATYHCLQHSNYPLTFGGG TKVEIK<br>SEQ ID NO: 25726 | QLQLQESGPGLVKPSETLSLICTVSGGSISSSNYYW GWIRQPPGKGLEWIGSIYYSGYTSYNPSLKSRVTIS VDSSKNHFSLRLSSVTAADTAVYYCARLDSNWGL DYWGQGTLVTVSS<br>SEQ ID NO: 29732 |
| iPS:434493 | 21-225_76F3 | NA | GACATCGTTATGACCCAGTCTCCAGACTCCCC GGCTGTGTCTCTGGGCGAGAGGGCCACCATCA ATTGCAAGTCCAGCCAGAGTGTTTTATTCAGC TCCAACAATTATAATTACTTAGCTTGGTACCA GCAGAGACCAGGACAGCCTCATGACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGCTGATGTTGGCAGTTTATTACTGTCAGCAA TATCATAGTTCCCTGACGTTCGGCCAAGG GACCACGGTCGAAATCAAA<br>SEQ ID NO: 25727 | CAGGTGCAGTTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGGCT TGAGTGGATGGGGATGGATGAACCCTAACAGTGG TAACACAGGCTATGCACAGAAGTTCCAGGGCAG AGTCACCATGACCAGGAACACCTCCACAAGCAC AGCCCACATGGAGCTGAGCAGCCTGAGATCTGA GGACACGGCCGTGTATTACTGTGCGGTCTCCAGT GGCTGGAACTGGTTCGACCCCTGGGGCCAGGGA ACCCTGGTCACCGTCTCCTCA<br>SEQ ID NO: 29733 |

FIGURE 50
(Continued)

| | | | |
|---|---|---|---|
| iPS:434495 | 21-225_74B2 | AA | DIVMTQCPDSPAVSLGERATINCKSSQSVLFSSN NYNYLAWYQQRPGQPHDLLIYWASTRESGVPD RFSGSGSGTDFTLTISSLQAADVAVYYCQQYHSS PLTFGQGTTVQIK<br>SEQ ID NO: 25728 | QVQLVQSGAEVKKPGASVKVSCKASGYTFNYDIN WVRQATGQGLEWMGWMNPNSGNTGYAQKFQGR VTMTRNTSTSTAHMELSSLRSEDTAVYYCAVSSGW NWFDPWGQGTLVTVSS<br>SEQ ID NO: 29734 |
| | | NA | GAACTTGTGTTGACGCAGTCTCCAGGCACCCT GTCTTTGTCTCCAGGGGAAAGAGCCACCCTCT CCTGCAGGGCCAGTCAGTCAGAATATTACAGCAGT TACTTAGCCTGGTACCAGCAGAAACCTGGCCA GGCTCCCAGGCTCCTCATCTATGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTGCTGTCAGCAGTATGAAAGCTCACCG TGGACCTTCGGCCAAGGGACCAAGGTGGAAA TCAAA<br>SEQ ID NO: 25729 | CAAGTGCAGTACAGCAGTGGGGCGCAGGACTG TTGAAGCCTTCGGAGACCTGTCCCTCACCTGCG CTGTCTATGTGGGTCCTTCAGTGGTCCCTACTG GAGCTGGATCCGCCAGCCCCGGGAAGGGGCT GGAGTGGATTGGGGAAATCAATCATAGTGGAAG CACCAACTACAACCCGTCCCTCCTCACGAGTCGAGTC ACCATATCAGTAGACACGTCAAGAACCAGTTCT CCCTGAAACTGACCTCTGTGACCGCCGCGACTC GGCTGTGTATTACTGTGCGAGAGACTACGGGGGT TTGGACGTCTGGGGCCAAGGGACCACGGTCACC GTCTCCTCA<br>SEQ ID NO: 29735 |
| | | AA | ELVLTQSPGTLSLSPGERATLSCRASQNIYSSYLA WYQQKPGQAPRLLIYGASSRATGIPDRFSGSGSG TDFTLTISRLEPEDFAVYCCQQYESSPWTFGQGT KVEIK<br>SEQ ID NO: 25730 | QVQLQQWGAGLLKPSEPLSLTCAVYGGSFSGPYW SWIRQPPGKGLEWIGEINHSGSTNYNPSLTSRVTISV DTSKNQFSLKLTSVTAADSAVYYCARDYGGLDVW GQGTTVTVSS<br>SEQ ID NO: 29736 |

FIGURE 50
(Continued)

| | | | |
|---|---|---|---|
| iPS:434497 | 21-225_76A4 | NA | GAAATTGTGTTGACGCAGTCTCCAGGCACCCT GTATTGTCTCCAGGGGAAAGAGCCACCCTCT CATGCAGGGCCAGTCAGTCAGAGTGTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTCTGATAACTCACCGT GGACGTTCGGCCAAGGGACCAAGGTGGAAAT CAAA<br><br>SEQ ID NO: 25731 | CAGGTGCAGCTACAGCAGTGGGCGCAGGACTG TTGAAGCCTTCGGAGACCGTCCCTCACCTGCG CTGTCCATGGTGGTCTTCAGTGGTTGCTACTG GAGCTGGATCCGCCAGCCCCAGGAAGGGCT GGAGTGGATTGGGGAAATCAATCATAGTGAAG CACCAACTACAACCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29737 |
| | | AA | EIVLTQSPGTLYLSPGERATLSCRASQSVYSSYLA WYQQKPGQAPRLLIYGASSRATGIPDRFSGSGSG TDFALTISRLEPEDFAVYYCQHSDNSPWTFGQGT KVEIK<br><br>SEQ ID NO: 25732 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29738 |
| iPS:434501 | 21-225_76G4 | NA | GAAATTGTGTTGACGCAGTCTCCAGGCACCCT GTCTTTGTCTCCAGGGGAAAGAGCCACCCTCT CATGCAGGGCCAGTCAGTCAGAGTGTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA<br><br>SEQ ID NO: 25733 | CAGGTGCAGCTACAGCAGTGGGCGCAGGACTG TTGAAGCCTTCGGAGACCGTCCCTCACCTGCG CTGTCCATGGTGGTCTTCAGTGGTTGCTACTG GAGCTGGATCCGCCAGCCCCAGGAAGGGCT GGAGTGGATTGGGGAAATCAATCATAGTGAAG CACCAACTACAACCGTCCCTCAAGAGTCGAGTC ACCATTTCAGTAGACACGTCAAGAACCAGTCT CCCTGAAGCTGAGCTGTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29739 |

FIGURE 50
(Continued)

| | | | | |
|---|---|---|---|---|
| iPS:434503 | 21-225_74D7 | AA | EIVLTQSPGTLSLSPGERATLSCRASQSVYSSYLA WYQQKPGQAPRLLIYGASSRATGIPDRFSGSGSG TDFALTISRLEPEDCAVYYCQHSDNSPWTFGQG TKVEIK<br><br>SEQ ID NO: 25734 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br><br>SEQ ID NO: 29740 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATTTGGGACAGAATTCACTCTCACCA TCAGCAGCCTGCAGCCTGAAGATTTTGCAACT TATTACTGTCTTCAGCATAGTAATTACCCGCTC ACTTTCGGCGGAGGGACCAAGGTGGAGATCA AA<br><br>SEQ ID NO: 25735 | CAACTGCAGCTGCAGGAGTCGGGCCAGGACTG GTGAAGCCTTCGGAGACCCTGTCCTCACCTGCA GTGTCTCTGGTGCTCCATCTTCAGAAGTAGTTA CTACTGGGGCTGGATCCGCCAGCCCCCAGGGAA GGGGCTGGAGTGGATTGGGGTATCTATTATAGT GGGAGCACCTCCTACAACCCGTCCTCAAGAGTC GAGTCACCATATCCGTAGACACGTCCGAGAACC AGTTCTCCCTGAAGCTGAGCTCTGTGACCGCCGC AGACACGGCTGTATTACTGTGCGAGACTGCGA CCTAACTGGGACTTTGACTACTGGGGCCAGGAA CCCTGGTCACCGTCTCCTCA<br><br>SEQ ID NO: 29741 |
| | | AA | DIQMTQSPSSLSASVGDRVTITCRASQGIRNDLG WYQQKPGKAPKRLIYAASSLQSGVPSRFSGSGF GTEFTLTISSLQPEDFATYYCLQHSNYPLTFGGG TKVEIK<br><br>SEQ ID NO: 25736 | QLQLQESGPGLVKPSETLSLTCSVSGGSIFRSSYYW GWIRQPPGKGLEWIGGIYYSGSTSYNPSLKSRVTIS VDTSENQFSLKLSSVTAADTAVYYCARLRPNWDF DYWGQGTLVTVSS<br><br>SEQ ID NO: 29742 |

FIGURE 50
(Continued)

| | | | | |
|---|---|---|---|---|
| iPS:434507 | 21-225_74C5 | NA | GAAATTGTGTTGACGCAGTCTCCAGGCACCCT GTCTTTGTCTCCAGGGGAAAGAGCCACCCTCT CTTGCAGGGCCAGTCAGAGTGTTAACAGCAAC TACTTAGCCTGGTACCAGCAGAAACCTGGCCA GGCTCCCAGGCTCCTCATCTATGGTGCATTCA GCAGGGCCACTGGCATCCCAGACAGGGTCAGT GGCAGTGGGTCTGGGACAGACTTCAATCTCAT CATCAGCAGACTGGAGCCTGAAGATTTTGCAG TGTATTACTGTCAGCAGTATGAAAGCTCACCG TGGACGTTCGGCCAAGGGACCAAGGTGGAAA TCAAA | CAGGTGCAGCTACAACAGTGGGGCGCAGGACTG TTGAAGCCTTCGGAGACCCTGTCCCTCACTTGCG CTGTCTATGGTGGGTCCTTCAGTGGTTGCTACTG GAGCTGGATCCGCCAGCCCCCAGGGAAGGGGCT GGAGTGGAATTGGGGAAATCAATCATAGTGGATG CACCAACTTCAACCGTCCCTCAAGAGTGGAGTC ACCATATCAGTTGACAGTCCAAGAACCAGTTCT CCCTGAAGCTGAGCTCTGTGACCGCCGGACAC GGCTGTGTATTACTGTGCGAGAGACTACGGCGGT ATGGACGTCTGGGGCCAAGGGACCACGGTCACC GTCTCCTCA |
| | | AA | EIVLTQSPGTLSLSPGERATLSCRASQSVNSNYLA WYQQKPGQAPRLLIYGAFSRATGIPDRVSGSGS GTDFNLIISRLEPEDFAVYYCQQYESSPWTFGQG TKVEIK | QVQLQQWGAGLLKPSETLSLTCAVYGGSFSGCYW SWIRQPPGKGLEWIGEINHSGCTNFNPSLKSRVTISV DTSKNQFSLKLSSVTAADTAVYYCARDYGGMDV WGQGTTVTVSS |
| | | | SEQ ID NO: 25737 | SEQ ID NO: 29743 |
| | | | SEQ ID NO: 25738 | SEQ ID NO: 29744 |
| iPS:434509 | 21-225_76F5 | NA | GTCATCGTGTTGACCCAGTCTCCAGACTCCCT GGCTGTGTCTCTGGGCGAGAGGGCCACCATCA ACTGCAAGTCCAGCCAGAGTGTATTACACAGC TCCAACAGTTACAACTACTTAGCTGGTACCA GCAGAAACCAGGACAGTCTCCTAAGGTGCTCA TTTACTGGGACATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTAGTCCTCCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTATATGGAGCTGAGCAGCCTGAGATCTGA GGACACGGCCGTGTATTACTGTGCGAGTAGCAGT GGCTGGTACTGGTTCGACCCCTGGGGCCAGGGA ACCCTGGTCACCGTCTCCTCA |
| | | | SEQ ID NO: 25739 | SEQ ID NO: 29745 |

FIGURE 50
(Continued)

| | | | | |
|---|---|---|---|---|
| | | AA | VIVLTQSPDSLAVSLGERATINCKSSQSVLHSSNS YNYLAWYQQKPGQSPKVLIYWTSTRESGVPDRF SGSGSGTDFLTISSLQAEDVAVYYCQQYYSSPP TFGQGTKVEIK<br><br>SEQ ID NO: 25740 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YWFDPWGQGTLVTVSS<br><br>SEQ ID NO: 29746 |
| iPS:434511 | 21-225_74B11 | NA | GATATCGTGATGACCCAGTCTCCAGACTCCCT GACTGTGTCTCTGGGCGAGAGGGCCACCATCA ACTGCAAGTCCAGCCAGAGTGTATTTATACAAC TCCAACAATAACAAGGACAACTACTTGGTACCA GCAGAAACCAGGACAGCCTCCTAAGCTGCTCA TTTACTGGGCATCTCACCCGGGAATCCGGGGTC CCTGACCGATTCAGTGGCAGCGGGTCTGGGAC AGATTTCATTCTCACCATCAGCAGCCTGCAGG CTGAAGATGTGGCAGTTTACTACTGTCAGCAA TATTATAGCACTCCCTACTTTCGGCGGAGG GACCAAGGTGGAGATCAAA<br><br>SEQ ID NO: 25741 | CAGGTGCAGCTGGTGCAGTCTGGGGCTGAGGTG AAGAAGCCTGGGGCCTCAGTGAGGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGTATAGCAGT GGCTGGTACTACTTTGACTACTGGGGCCAGGGAA CCCTGGTCACCGTCTCCTCA<br><br>SEQ ID NO: 29747 |
| | | AA | DIVMTQSPDSLTVSLGERATINCKSSQSILYNSNN NNYLAWYQQKPGQPPKLLIYWASTRESGVPDRF SGSGSGTDFILTISSLQAEDVAVYYCQQYYSTPP TFGGGTKVEIK<br><br>SEQ ID NO: 25742 | QVQLVQSGAEVKKPGASVRVSCKASGYTFTNYDIN WVRQATGQGLEWMGWMHPNSGNTGYAQKFQGR VTMTRNTSISTAYMELSSLRSEDTAVYYCAYSSGW YYFDYWGQGTLVTVSS<br><br>SEQ ID NO: 29748 |

FIGURE 50
(Continued)

| | | | |
|---|---|---|---|
| iPS:434513 | 21-225_76A6 | NA | GAAATTGTGTTGACGCAGTCTCCAGGCACCCG GTCTTGGTCTCCAGGGGAAAGAGCCACCCTCT CGTGCAGGGCCAGTCAGAGTGTTAGCAGCAGC TACTTAGCCTGGTACCAGCAGAAACCTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCTGAAGCCTGAATATTTTGCAG TTTATTACTGTCAGCAGTATGGTAACTCACCG CTCACTTTCGGCGGAGGGACCAAGGTGGAGAT CAAA SEQ ID NO: 25743 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAATGG TAACACAGGCTATGCACAGAAGTTCCAGGGCAG AGTCACCATGACCAGGAACACCTCCATAAGCAC AGCCTACATGGAGCTGAACAGCCTGAGATCTGA GGACACGGCCGTGTATTACTGTGCGATTAGCAGT GGCTGGTACTTCGATCCCCGGGGCCAGGGA ACCCTGGTCACCGTCTCCTTA SEQ ID NO: 29749 |
| | | AA | EIVLTQSPGTRSWSPGERATLSCRASQSVSSSYL AWYQQKPGQAPRLLIYGASTRATGIPDRFSGSGS GTDFTLTISRLEPEYFAVYYCQQYGNSPLTFGGG TKVEIK SEQ ID NO: 25744 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL SEQ ID NO: 29750 |
| iPS:434515 | 21-225_74A5 | NA | GAATTTATGTTGACGCAGTCTCCAGGCACCCT GTCTTTGTCTCCAGGGGAAAGAGCCACCCTCT CGTGCAGGGCCAGTCAGAGTGTTAGCAGCAGC TACTTAGTCTGTATCAGCAGAAACCTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTTGCTCACCGC TCACTTTCGGCGGAGGGACCAAGGTGGAGATC ACA SEQ ID NO: 25745 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCTGGACAAGGGC TTGAGTGGATGGGATGGATGCACCCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA SEQ ID NO: 29751 |

FIGURE 50
(Continued)

| | | | | |
|---|---|---|---|---|
| iPS:434517 | | AA | EFMLTQSPGTLSLSPGERATLSCRASQSVSSSYL VWYQQKPGQAPRLLIYGASTRATGIPDRFSGSGS GTDFTLTISRLEPEYFAVYYCQQYGCSPLTFGGG TKVEIT<br>SEQ ID NO: 25746 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br>SEQ ID NO: 29752 |
| | 21-225_76A7 | NA | GAAATTGCGTTGACGCAGTCTCCAGGCACCCT GTCTTTGTCTCCAGGGGAAAGAGCCACCCTCT CCTGCAGGGCCAGTCCGAGTGTTGACAGCAGC TACTTAGCCTGGTACCAGCAGAGACCTGGCCA GGCTCCCAGGCTCCTCATCTATGGTGCATCCA GCAGGGCCCCTGCATCCCAGACAGGTTCAGT GGCAGTGGGTCTGGGACAGATTCACTCTCAC CATCAGCAGACTGGAGCCTGAAGATTTTGCAG TGTATTACTGTCAGCAGTATGAAAGTTCACCG TGGACGTTCGGCCAAGGGACCAAGGTGGAAA TCAAA<br>SEQ ID NO: 25747 | CAGGTGCAGTCTACAGCAGTGGGGCGCAGGACTG TTGAAGCCTTCGGAGACCCTGTCCCTCACCTGCG CTGTCTATGTGGGTCCTTCAGTGGTTGCTACTG GAGCTGGATCCGCCAGCCCCCAGGGAAGGGGCT GGAGTGGATTGGGGAAATCAATCATAGTGGAAG GACCAACTACAACCGTCCCTCAAGAGTCGAGTC ACCATATCAGTAGACACGTCCGAGAACCAGTTCT CCCTGAAGCTGAGCTCTGTGACCGCCGCGGACAC GGCTGTGTATTACTGTGCGAGAGACTACGGTGGG CTTGACTACTGGGGCCAGGGAGCCCTGGTCACCG TCTCCTCA<br>SEQ ID NO: 29753 |
| | | AA | EIALTQSPGTLSLSPGERATLSCRASPSVDSSYLA WYQQRPGQAPRLLIYGASSRAPGIPDRFSGSGSG TDFTLTISRLEPEDFAVYYCQQYESSPWTFGQGT KVEIK<br>SEQ ID NO: 25748 | QVQLQQWGAGLLKPSETLSLTCAVYGGSFSGCYW SWIRQPPGKGLEWIGEINHSGRTNYNPSLKSRVTIS VDTSENQFSLKLSSVTAADTAVYYCARDYGGLDY WGQGALVTVSS<br>SEQ ID NO: 29754 |

FIGURE 50
(Continued)

| | | | |
|---|---|---|---|
| iPS:434519 | 21-225_74C7 | NA | GAAATTGTGTTGACGCAGTCGCCAGGCACCCT GTCTTTGTCTCCAGGGGAGAGAGCCACCCTCT CCTGCAGGACCAGTCCGAATGTTGACAGCAGC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTTTTACTGTCAGCAGTATGAACGCTCACG TGGACGTTCGGCCAAGGGACCAAGGTGGAAA TCAAA<br>SEQ ID NO: 25749 |
| | | AA | EIVLTQSPGTLSLSPGERATLSCRTSPNVDSSYLA WYQQKPGQAPRLLIYGASSRATGIPDRFSGSGSG TDFTLTISRLEPEDFAVFYCQQYERSPWTFGQGT KVEIK<br>SEQ ID NO: 25750 | CAGGTGCAGTTACAGCAGTGGGGCGCAGGACTG TTGAAGCCTTCGGAGACCCTGTCCCTCACCTGCG CTGTCTATGGTGGGTCCCTCAGTGGTTCTACTG GAGCTGGATCCGCCAGCCCCCAGGAAGGGCT GGAGTGGATTGGGGAAATCAATCTTAGTGGAAG CACCAACTACACAACCGTCCCTCAAGAGTCGAGTC ACCATATCAGTAGACACGTCAAGAGCCAGTTCT CCCTGACGCTGCGCTCTGTGACGCCGCGGACAC GGCTGTGTATTACTGTGCGAGAGACTACGGTGGC CTTGACTACTGGGGCCAGGGAACCCTGGTCACCG TCTCCTCA<br>SEQ ID NO: 29755 |
| | | | QVQLQQWGAGLLKPSETLSLTCAVYGGSLSGSYW SWIRQPPGKGLEWIGEINLSGSTNYNPSLKSRVTISV DTSKSQFSLTLRSVTAADTAVYYCARDYGGLDYW GQGTLVTVSS<br>SEQ ID NO: 29756 |
| iPS:434523 | 21-225_75C3 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGG TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TATATTACTGTCAGCAGTATTATGATAGCTCACCGT GGACGTTCGGCCAAGGGACCAAGGTGGAAAT CAAA<br>SEQ ID NO: 25751 | CAGGTGCAGTACAGCAGTGGGGCGCAGGACCG TTGAAGCCTTCGGAGACCCTGTCCCTCACCTGCG CTGTCTATGGTGGGTCCTTCAGTGGTTGCTACTG GAGCTGGATCCGCCAGCCCCCAGGAAGGGCT GGAGTGGATTGGGGAAATCAATTATAGTGGAAG AACCAACTACACAACCGTCCCTCAAGAGTCGAGTC ACCATATCAGTAGACACGTCAAGAAACCAGTTCT CCCTGAAGCTGAGCTCTGTGACGCCGCGGACAC GGCTGTGTATTACTGTGCGAGAGATACGCGCGGT ATGGACGTCTGGGGCCAAGGGACCACGGTCACC GTCTCCTCA<br>SEQ ID NO: 29757 |

FIGURE 50
(Continued)

| | | | |
|---|---|---|---|
| iPS:434525 | 21-225_76E8 | AA | EIVLTQSPGTLSLSQGERATLSCRASQSVSSRYLAWYQQKPGQAPRLLIYGASSRATGIPDRFSGSGSGTDFTLTISRLEPEDFAVYYCQHYDSSPWTFGQGTKVEIK<br>SEQ ID NO: 25752 | QVQLQQGGAGPLKPSFTLSLTCAVYGGSFSGCYWSWIRQPPGKGLEWIGEINYSGRTNYNPSLKSRVTISVDTSKNQFSLKLSSVTAADTAVYYCARDYGGMDVWGQGTTVTVSS<br>SEQ ID NO: 29758 |
| | | NA | GACATCGTGATGACCCAGTCTCCAGACTCCCTGGCTGTGTCTCTGGGCGAGAGGGCCACCATCAACTGCAAGTCCAGCCAGAGTGTTTTACACAGCTCCAACAATTATAACTACTTAGCTTGGTACCAGCAGAAGCCAGGACAGCCCCCTAAGGTGCTCATTTACTGGGACATCTACCCGGGAATCCGGGGTCCCTGACCGATTCAGTGGCAGGGGTCTGGGACAGATTTCACTCTCACCATCAGCAGCCTGCAGGCTGAAGATGTGGCAGTTTATTACTGTCAGCAATATTTTAGTAGTCCCTCTGACGTTCGGCCAAGGGACCAAGGTGGAAATCAAA<br>SEQ ID NO: 25753 | CAGGTGCAGCTGGTGCAGTCTGGGGCTGAGGTGAAGAAGCCTGGGGCCTCAGTGAAGGTCCTGCAAGGCTTCTGGATACACCTTCCCAATTATGATATCAACTGGGTGCGACAGGCCACTGGACAAGGCTTGAGTGGATGGGATGAACCTAACAGTGGTAACACAGGCTATGCCACAGAAGTTCCAGGCAGTCACCATGACCAGGAACACCTCCATAAGCACAGCCTACATGGAGCTGAGCAGCCTGAGATCTGAGGACACGGCCGTGTATTATTGTGCGGTTTCCAGTGGCTGGCACTGGTTCGACCCCTGGGGCCAGGGAACCCTGGTCACCGTCGCCTCA<br>SEQ ID NO: 29759 |
| | | AA | DIVMTQSPDSLAVSLGERATINCKSSQTVLHSSNNYNYLAWYQQKPGQPPKVLIYWSTRESGVPDRFSGSGSGTDFTLTISSLQAEDVAVYYCQQYFSSPLTFGQGTKVEIK<br>SEQ ID NO: 25754 | QVQLVQSGAEVKKPGASVKVSCKASGYTFPNYDINWVRQATGQGLEWMGWMNPNSNGTYAQKFQGRVTMTRNTSISTAYMELSSLRSEDTAVYYCAVSSGWHWFDPWGQGTLVTVAS<br>SEQ ID NO: 29760 |

FIGURE 50
(Continued)

| | | | |
|---|---|---|---|
| iPS:434529 | 21-225_76B9 | NA | GAATTTATGTTGACGCAGTCTCCAGGCACCCT GTCTTGGTCTCCAGGGGAAAGAGCCACCCTCT CGTGCAGGGCCAGTCAGTGTTAGCAGCAGC TACTTAGTCTGGTATCAGCAGAAACCTGGCCA GGCTCCCAGGCTCCTCATCTATGGTGCATCCA CCAGGGCCACTGGCATCCCAGACAGGTTCAGT GGCAGTGGGTCTGGGACAGATTCACTCTCAC CATCAGCAGACTGGAGCTGAATATTTGCAG TTTATTACTGTCAGCAGTATGGTTGCTCACCGC TCACTTTCGGCGGAGGGACCAAGGTGGAGATC ACA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGC TTGAGTGGATGGGATGGATGCACCCTAACAGTGG TAACACAGGCTATGCACAGAAGTTCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA |
| | | | SEQ ID NO: 25755 | SEQ ID NO: 29761 |
| | | AA | EFMLTQSPGTLSWSPGERATLSCRASQSVSSSYL VWYQQKPGQAPRLLIYGASTRATGIPDRFSGSGS GTDFTLTISRLEPEYFAVYYCQQYGCSPLTFGGG TKVEIT | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25756 | SEQ ID NO: 29762 |
| iPS:434531 | 21-225_76C9 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGT TACTTATCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTGGAGCCTGAAGATTTTGCAG TGTATTACTGTCAGCAGTATGGTAGGTCACGG ACGTTCGGCCAAGGGACCAAGGTGGAAATCA GA | GAGGTGCAGCTGGTGGAGTCTGGGGGAGGCTTG GTAAAGCCTGGGGGGTCCCTTAGACTCTCCTGTG CAGCCTCTGGATTCAGTTTCAGTAACGCCTGGAT GAACTGGGTCCGCCAGGCTCCAGGGAAGGGGCT GGAGTGGGTTGGCCGTATTAAAAACAAAGCTGA TGGTGGGACAACAGACTTCGCTGCACCCGTGAA AGGCAGATTCACCATCTCAAGAGATGATTCAAA ACACACGTGTATCTGCAAATGAACAGCCTGAA AACCGAGGACACAGCCGTGTATTACTGTACCACA GTGGGACCTACTACGACTACTGGGGCCAGGGA ACCCTGGTCACCGTCTCCTCA |
| | | | SEQ ID NO: 25757 | SEQ ID NO: 29763 |

FIGURE 50
(Continued)

| | | AA | EIVLTQSPGTLSLSPGERATLSCRASQSVSSSYLS WYQQKPGQAPRLLIYGASSRATGIPDRFSGSGSG TDFTLTISRLEPEDFAVYYCQQYGRSRTFGQGTK VEIR<br><br>SEQ ID NO: 25758 | EVQLVESGGGLVKPGGSLRLSCAASGFSFSNAWM NWVRQAPGKGLEWVGRIKNKADGTTDFAAPVK GRFTISRDDSKHTLYLQMNSLKTEDTAVYYCTTVG PTTDYWGQGTLVTVSS<br><br>SEQ ID NO: 29764 |
|---|---|---|---|---|
| iPS:434533 | 21-225_85F7 | NA | GAACCTGTGTTGACGCAGTCTCCAGGCACCCT GTCTTTGTCTCCAGGGGAAAGAGCCACCCTCT CCTGCAGGGCCAGTCAGAATATTACAGCAAC TACTTAGCCTGGTACCAGCAGAAACCTGGCCA GGCTCCCAGGCTCCTCATCTATGGTGCATCCA GCAGGGGCCACTGGCATCCCAGACAGGTTCAGT GGCAGTGGGTCTGGGACAGACTTCACTCTCAC CATCAGCAGACTGGAGCCTGAAGATTTTGCAG TGTATTGCTGTCAGCAGTATGAAAGCTCACCG TGGACCTTCGGCCAAGGGACCAAGGTGGAAA TCAAA<br><br>SEQ ID NO: 25759 | CAAGTGCAGCTACAGCAGTGGGGCGCAGGACTG TTGAAGCCTTCGGAGACCCTGTCCCTCACCTGCG CTGTCTATGGTGGGTCCTTCAGTGGTCCCTACTG GAGCTGGATCCGCCAGCCCCCGGGAAGGGGCT GGAGTGGATTGGGGAAATCAATCATAGTGGAAG CACCAACTACAACCGTCCCTCCAAGAGTCGAGTC ACCATATCAGTAGACACGTCAAGAACCAGTTCT CCCTGAAACTGACCTCTGTGACCGCCGCGGACAC GGCTGTGTATTACTGTGCGAGAGACTACGGGGGT TTGGACGTCTGGGGCCAAGGGACCACGGTCACC GTCTCCTCA<br><br>SEQ ID NO: 29765 |
| | | AA | EPVLTQSPGTLSLSPGERATLSCRASQNIYSNYLA WYQQKPGQAPRLLIYGASSRATGIPDRFSGSGSG TDFTLTISRLEPEDFAVYCCQQYESSPWTFGQGT KVEIK<br><br>SEQ ID NO: 25760 | QVQLQQWGAGLLKPSEPLSLTCAVYGGSFSGPYW SWIRQPPGKGLEWIGEINHSGSTNYNPSLKSRVTISV DTSKNQFSLKLTSVTAADTAVYYCARDYGGLDVW GQGTTVTVSS<br><br>SEQ ID NO: 29766 |

FIGURE 50
(Continued)

| | | | | |
|---|---|---|---|---|
| iPS:434535 | 21-225_74C8 | NA | GACATCCAGATGACCCAGTCTCCATCCTCACT GTCTGCATCAGTAGGAGACAGAGTCACCATCA CTTGTCGGGCGAGTCAGGGCATTGGCAAGTAT TTAGCCTGGTTTCAGCAGAAACCAGGGAAAGC CCCTAAGTCCCTGATCTATGCTGCATCCAATTT ACAAAGTGGGGCCCATCAAAGTTCAGCGGC AGTGGATCTGGGACAGATTTCACTCTCACCAT CAGCAGCCTGCAGTATGAAGATTTTGCAACTT ATTACTGCCAACAGTACAGTAATTACCCGCTC ACTTTCGGCGGAGGGACCAAGGTGGAGATCA AT | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGGCAG CTATGGTTATGACGGCCTTGACTACTGGGGCCAG GGAACCCTGGTCACCGTCTCCTCA |
| | | | SEQ ID NO: 25761 | SEQ ID NO: 29767 |
| | | AA | DIQMTQSPSSLSASVGDRVTITCRASQGIGKYLA WFQQKPGKAPKSLIYAASNLQSGAPSKFSGSGSG TDFTLTISSLQYEDFATYYCQQYSNYPLTFGGGT KVEIN | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDGSYG YDGLDYWGQGTLVTVSS |
| | | | SEQ ID NO: 25762 | SEQ ID NO: 29768 |
| iPS:434537 | 21-225_74E11 | NA | GAAATAGTGATGACGCAGTCTCCAGCCACCCT GTCTGTGTCTCCAGGGGAAAGAGCCACCCTCT CCTGCAGGGCCAGTCTGAGTGTTGTCAACAGC TTAGCCTGGTACCAGCAGAAACCTGGCCAGGC TCCCAGGCTCCTCATCTATGGTGCATCACCA GGGCCACTGGTATCCCAGCCAGGTTCAGTGGC AGTGGGTCTGGGACAGAGTTCACTCTCACCAT CAGCAGTCTGCAGTCTGAAGATTTTGCAGTTGC ATTACTGTCAGCAGTATAATGACTGGCCGTGC AGTTTTGGCCAGGGGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATTGGTATGATGAAGT AATAAATACTATGCAGACTCCGTGAAGGGCCGA TTCACCATCTCCAGAGACAATTCCAAGAACACGC TGTTTCTGCAAATGAACAGCCTGAGAGCCGAGG ACACGGCTGTGTATTACTGTGCGAGCGATCGCAA TATAGTGGAGCTACTTACTTTGAGTCCTGGGGC CAGGGAACCCTGGTCACCGTCTCCTCA |
| | | | SEQ ID NO: 25763 | SEQ ID NO: 29769 |

FIGURE 50
(Continued)

| | | | |
|---|---|---|---|
| iPS:434539 | 21-225_74A2 | AA | EIVMTQSPATLSVSPGERATLSCRASLSVVNSLA WYQQKPGQAPRLLIHGASTRATGIPARFSGSGSG TEFTLTISSLQSEDFAIYYCQQYNDWPCSFGQGT KLEIK<br>SEQ ID NO: 25764 | QVQLVESGGGVVQPGRSLRLSCAASGFTFSSYGMH WVRQAPGKGLEWVAVIWYDGSNKYYADSVKGRF TISRDNSKNTLFLQMNSLRAEDTAVYYCASDRNIV GATYFESWGQGTLVTVSS<br>SEQ ID NO: 29770 |
| | | NA | GATATTGTGATGACTCAGTCTCCACTCTCCCTG CCCGTCACCCCTGGAGAGCCGGCCTCCATCTC CTGCAGGTCTAGTCAGAGCCTCTGTGAATAGTA ATGGAACACAACTATTTGGATTGGTACCTACAG AAGCCAGGGCGGTCTCCACAGCTCCTGATCTA TTTGGGTTCTAATCGGGCTCCGGGGTCCCTG AGAGGTTCAGTGGCAGTGGATCAGGCACAGA TTTTACACTGAAAATCAGCAGAGTGGAGGCTG AGGATGTTGGGGTTTATTACTGCATGCAACCT CTACAAACTCCGTTCACTTTCGGCGGAGGGAC CAAGGTGGAGATCAAA<br>SEQ ID NO: 25765 | CAGGTGCAGGTACAGCAGTGGGGCGCAGGACTG TTGAAGCCTTCGGAGACCTGTCCCTCACCTGCG CTGTCTATGTGGGTCCTTCACTGTTACTACTGG AGCTGGATCCGCCAGCCCCAGGGAAGGGCTG GAGTGGATTGGGAAATCAATCATAGTGGAGAC ACCAACTACAACCCGTCCCTCAAGAGTCGAGTCA CCATATCAGTAGACACGTCCAAGAACCAGTTCTC CCTGAAGCTGAGTTCTGTGACCGCCGGACACG GCTGTGTATTACTGTGCGAGAGAGTTTCCATATA GTGGAAGCTACCTCTACTACTACGGTATGGACGT CTGGGGCCAAGGGACCACGGTCACCGTCTCCTCA<br>SEQ ID NO: 29771 |
| | | AA | DIVMTQSPLSLPVTPGEPASISCRSSQSLLHSNGH NYLDWYLQKPGRSPQLLIYLGSNRASGVPERFS GSGSGTDFTLKISRVEAEDVGVYYCMQPLQTPF TFGGGTKVEIK<br>SEQ ID NO: 25766 | QVQVQQWGAGLLKPSETLSLTCAVYGGSFTDYYW SWIRQPPGKGLEWIGEINHSGDTNYNPSLKSRVTIS VDTSKNQFSLKLSSVTAADTAVYYCAREFPYSGSY LYYYGMDVWGQGTTVTVSS<br>SEQ ID NO: 29772 |

FIGURE 50
(Continued)

| | | | |
|---|---|---|---|
| iPS:434547 | 21-225_74H5 | NA | GAAATTGTGTTGACGCAGTCTCCAGGCACCCT GTCTTTGTCTCCAGGGGAGAGAGCCACCTCT CCTGCAGGGCCAGTCAGTCAGAGTGTTAACAGCAAC TACTTAGCCTGGTACCGGCAGAAACCTGGCCA GGCTCCCAGGCTCCTCATCTATGGTGCATCA GCAGGGCCACTGGCATCCCAGACAGGTTCAGT GGCAGTGGGTCTGGGACAGACTTCATTCTCAT CATCAGCAGACTGGAGCCTGAGGATTTTGCAG TGTATTACTGTCAGCAGTATGAAAGCTCGCCG TGGACGTTCGGCCAAGGGACCAAGGTGGAAA TCAAA<br><br>SEQ ID NO: 25767 | CAGGTGCAGCTACAACAGTGGGGCGCAGGACTG TTGAAGCCTTCGGAGACCCTGTCCCTCACTTGCG CTGTCAATGGTGGGCCCTTCAGTGGTTGCTACTG GAGCTGGATCCGCCAGCCCCCAGGGAAGGGGCT GGAGTGGATTGGGGAAATCAATCATAGTGGAAG GACCAACTTCAACCCGTCCCTCAAGAGTCGAGTC ACCATATCAGTTGACAGTCCAAGAACCAGTTCT CCCTGAAGCTGAGCTCTGTGACCGCCGGACAC GGCTGTGTATTACTGTGCGAGAGACTACGGCGT ATGGACGTCTGGGGCCAAGGGACCACGGTCACC GTCTCCTCA<br><br>SEQ ID NO: 29773 |
| | | AA | EIVLTQSPGTLSLSPGERATLSCRASQSVNSNYLA WYRQKPGQAPRLLIYGASSRATGIPDRFSGSGSG TDFTLTISRLEPEDFAVYYCQQYESSPWTFGQGTK VEIK<br><br>SEQ ID NO: 25768 | QVQLQQWGAGLLKPSETLSLTCAVNGGPFSGCYW SWIRQPPGKGLEWIGEINHSGRTNFNPSLKSRVTISV DTSKNQFSLKLSSVTAADTAVYYCARDYGGMDV WGQGTTVTVSS<br><br>SEQ ID NO: 29774 |
| iPS:434549 | 21-225_76E11 | NA | GACATCGTGATGACCCAGTCTCCAGACTCCCT GGCTGTGTCTCTGGGCGAGGGGCCACCATCA ACTGCAAGTCCAGTCCCGCCAGAGTGTTTACACAGC TCCAACAATTACAACTACTTAGCTTGGTACCA GCAGAAAGCAGGACAGCCTCCTAAACTGCTCA TTTACTGGGCTTCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAGA<br><br>SEQ ID NO: 25769 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GACTCACCATGACCAGAACACCTCCATAAGCA CAGCCTACATGGAGCTGAGCAGCCTGAGATCTG AGGACACGGCCGTGTTTACTGCTGTGCATATAGCAG TGGCTGGTACTACTTGACTACTGGGGCCAGGGA ACCCTGGTCACCGTCTCCTCA<br><br>SEQ ID NO: 29775 |

FIGURE 50
(Continued)

| | | | | |
|---|---|---|---|---|
| iPS:434551 | 21-225_75C4 | AA | DIVMTQSPDSLAVSLGEGATINCKSRQSVLHSSN NYNYLAWYQQKAGQPPKLLIYWASTRESGVPD RFSGSGSGTDFTLTISSLQAEDVAVYYCQQYYST PPTFGQGTKVEIR<br>SEQ ID NO: 25770 | QVQLVQSGAEVKKPGASVKVSCKASGYTFTNYDIN WVRQATGQGLEWMGWMNPNSGNTGYAQKFQGR LTMTRNTSISTAYMELSSLRSEDTAVFYCAYSSGW YYFDYWGQGTLVTVSS<br>SEQ ID NO: 29776 |
| | | NA | GACATCGTGATGACCCAGTCTCCAGACTCCCT GGCTGTGTCTCTGGGCGAGGGGCCACCATCA ACTGTAAGTCCAGCCAGAGTGTATTTATACAGC TCCAACAATAATAACTACTTAGCTTGGTTCCA GCAGAAACCAGGACAGCCTCCTAAGCTGCTCA TTTATTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATATTACTCCTCCGACGTTCGGCCAAGG GACCAAGGTGGAAATCAAA<br>SEQ ID NO: 25771 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCATCCTAACAGTGG TAACACAGGCTATGCACAGAAGTTCCAGGGCAG AGTCACCATGACCAGGAACACCTCCATAAGCAC AGCCTACATGGAACTGAGCAGCCTGAGATCTGA GGACACGGCCGTGTATTACTGTGCGAGTAGCAGT GGCTGGTACTACTTTGACTACTGGGGCCAGGAA CCCTGGTCACCGTCTCCTCA<br>SEQ ID NO: 29777 |
| | | AA | DIVMTQSPDSLAVSLGERATINCKSSQSILYSSNN NNYLAWFQQKPGQPPKLLIYWASTRESGVPDRF SGSGSGTDFTLTISSLQAEDVAVYYCQQYYITPP TFGQGTKVEIK<br>SEQ ID NO: 25772 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCASSSGW YYFDYWGQGTLVTVSS<br>SEQ ID NO: 29778 |

FIGURE 50
(Continued)

| | | | |
|---|---|---|---|
| iPS:434559 | 21-225_74D11 | NA | GAAATTGTGTTGACGCAGTCTCCAGGCACCCT GTCTTTGTCTCCAGGGGAAAGAGCCACCCTCT CCTGCAGGGCCAGTCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCACCG TGGACGTTCGGCCAAGGGACCAAGGTGGAAA TCAAA SEQ ID NO: 25773 | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGGAAGGGCT GGAGTGGATTGGGGAAATCAATCATAGTGGAAG CACCAACTACACAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29779 |
| | | AA | EIVLTQSPGTLSLSPGERATLSCRASQSVYSSYLA WYQQKPGQAPRLLIYGASSRATGIPDRFSGSGSG TDFALTISRLEPEDFAVYYCQHYDNSPWTFGQG TKVEIK SEQ ID NO: 25774 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 29780 |
| iPS:434561 | 21-225_77G1 | NA | GAAATTGTGTTGACGCAGTCTCCAGGCACCCT GTATTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTACTGATAACTCACCG TGGACGTTCGGCCAAGGGACCAAGGTGGAAA TCAAA SEQ ID NO: 25775 | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGGAAGGGCT GGAGTGGATTGGGGAAATCAATCATAGTGGAAG CACCAACTACACAACCGTCCCTCAAGAGTCGAGTC ACCATTTCAGTAGACACGTCAAGAACCAGTTCT CCCTGAAGCTGAGCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29781 |

FIGURE 50
(Continued)

| | | | |
|---|---|---|---|
| iPS:434563 | 21-225_75D8 | AA | EIVLTQSPGTLYLSPGERATLSCRASQSVYSSYLA WYQQKPGQAPRLLIYGASSRATGIPDRFSGSGSG TDFALTISRLEPEDCAVYYCQHYDNSPWTFGQG TKVEIK<br>SEQ ID NO: 25776 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29782 |
| | | NA | GATATTGTGATGACTCAGTCTCCACTCTCCCTG CCCGTCACCCCTGGAGAGCCGGCCTCCATCTC CTGCAGGTCTAGTCAGAGCCTCCTGCATAGTA GTGGATACAACTATTTGGATTGGTACCTGCAG AAGCCAGGGCAGTCTCCACAGCTCCTGATCTA TTTGGGTTCTAATCGGGCCTCCGGGGTCCCTG ACAGGTTCAGTGGCAGTGGATCAGGCTCAGAT TTTACACTGAAGATCAGCAGAGTTGGAGGCTGA GGATGTTGGACTTTATTACTGCATGCAAGCTC TACACCCTCCTCCACTTTCGGCGGAGGGACC AAGGTGGAGATCAAA<br>SEQ ID NO: 25777 | GAGGTGCAGCTGGTGGAGTCTGGGGGAGGCTTG GTACAGCCGGGGGGGTCCCTGAGACTCTCCTGTG CAGCCTCTGGATTCACCTTCAGTAACTACGACAT GCACTGGGTCCGCCAAGCTACAGGAAAAGGTCT GGAGTGGGTCTCAGTTATTGGTACTGCTGGTGAC ACATACTATCCAGGCTCCGTGAAGGGCCGATTCA CCATCTCCAGAGAAATGCCAAGAACTCCTTGTA TCTTCAAATGAACAGCTGAGAGCCGGGGACAC GGCTGTGTATTACTGTGCAAGAGTTCTTGACTAC GGTGACTCCTTGGGCTACTACTACGGTATGG ACGTCTGGGGCCAAGGGACCACGGTCACCGTCTC CTCA<br>SEQ ID NO: 29783 |
| | | AA | DIVMTQSPLSLPVTPGEPASISCRSSQSLLHSSGY NYLDWYLQKPGQSPQLLIYLGSNRASGVPDRFS GSGSGSDFTLKISRVEAEDVGLYYCMQALHPPL TFGGGTKVEIK<br>SEQ ID NO: 25778 | EVQLVESGGGLVQPGGSLRLSCAASGFTFSNYDMH WVRQATGKGLEWVSAIGTAGDTYYPGSVKGRFTIS RENAKNSLYLQMNSLRAGDTAVYYCARVLDYGDS LGYYYYGMDVWGQGTTVTVSS<br>SEQ ID NO: 29784 |

FIGURE 50
(Continued)

| | | | |
|---|---|---|---|
| iPS:434565 | 21-225_75B10 | NA | GAAATTGTGTTGACGCAGTCTCCAGGCACCCTGTCTTTGTCTCCAGGGGAAAGAGCCACCCTCTCCTGCAGGGCCAGTCCGAGTGTTAACAGCTACTACTTAGCCTGGTACCAGCAGAAACCTGGCCAGGCTCCCAGGCTCCTCATCTATGGTGCAACCAGCAGGGCCACTGGCATCCCAGACAGGTTCAGTGGCAGTGGGTCTGGAACAGACTTCACTCTCACCATCAGCAGACTGGAGCCTGAAGATTTTGCAGTTTATTTCTGTCAGCAGTATGAAGACTCACCGTGGACGTTCGGCCAAGGGACCAAGGTGGAAATCAAAA<br><br>SEQ ID NO: 25779 | CAGGTGCAGCTACAGCAGTGGGGCGCAGGACTGTTGAAGCCTTCGGAGACCCTGTCCCTCAAATGCGATGTCTATGTGGGTCCTTCAGTGGTTACTACTGGAGCTGGATCGCCAGCCCCAGGGAAGGGCTGGAGTGGATTGGGGAAATCAATCACAGTGGAAGCACCAACTACAACCCGTCCCTCAAGAGTCGAGTCACCATATCAGTAGACACGTCCAAGAACCAGTTCTCCCTGAAGCTGAGCTCTGTGACCGCCGCGGACACGGCTGTGTATTACTGTGCGAGAGACTACGGTGGTTTGGACGTCTGGGGCCAAGGGACCACGGTCACCGTCTCCTCA<br><br>SEQ ID NO: 29785 |
| | | AA | EIVLTQSPGTLSLSPGERATLSCRASPSVNSYYLAWYQQKPGQAPRLLIYGATSRATGIPDRFSGSGSGTDFTLTISRLEPEDFAVYFCQQYEDSPWTFGQGTKVEIK<br><br>SEQ ID NO: 25780 | QVQLQQWGAGLLKPSETLSLKCDVYGGSFSGYYWSWIRQPPGKGLEWIGEINHSGSTNYNPSLKSRVTISVDTSKNQFSLKLSSVTAADTAVYYCARDYGGLDVWGQGTTVTVSS<br><br>SEQ ID NO: 29786 |
| iPS:434569 | 21-225_77H5 | NA | GAAATAGTGATGACGCAGTCTCCAGTCACCCTGTCTGTGTCTCCAGGGGAAAGAGCCACCCTCTCCTGCAGGGCCAGTCAGAGTGTTAGCAGCAGCTTAGCCTGGTACCAGCAGAAACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTTCTGTCAGCAGTATAATGACTGGCCGTGCAGTTTTTGGCCAGGGGCTCCAAGCTGGAGATCCAA<br><br>SEQ ID NO: 25781 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAATTATGGCATGCACTGGGTCCGCCAGGCTCCAGGCAAGGGGCTGGAGTGGGTGGCAGTTATATGGTATGATGGAAGAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTCTATATTACTGTGCGAGAGATCGGAGTATATTGGAGCTACTTCTTTGACTACTGGGGCCAGGGAACCCTGGTCACCGTCTCCTCA<br><br>SEQ ID NO: 29787 |

FIGURE 50
(Continued)

| | | | |
|---|---|---|---|
| | | AA | EIVMTQSPVTLSVSPGERATLSCRASQSVSSSLA WYQQKPGLAPRLLIYGASTRATGIPARFSGSGSG TEPSFTISSLQSEDFAVYFCQQYNDWPCSFGQGS KLEIQ<br>SEQ ID NO: 25782 | QVQLVESGGGVVQPGRSLRLSCAASGFTFSNYGM HWVRQAPGKGLEWVAVIWYDGRNKYYADSVKG RFTISRDNSKNTLYLQMNSLRAEDTALYYCARDRSI LGATFFDYWGQGTLVTSS<br>SEQ ID NO: 29788 |
| iPS:434571 | 21-225_74D2 | NA | GAAATTGTGTTGACGCAGTCTCCAGGCACCCT GTCTTTGTCTCCAGGGGAAAGAGCCACCCTCT CCTGCAGGGCCAGTCAGAGTGTTGACAGCAAC TACTTAGCCTGGTACCAGCAGAAACCTGGCCA GGCTCCCAGGCTCCTCATCTATGGTGCATCCA GCAGGGCCCCTGCATCCCAGACAGGTTCAGT GGCAGTGGGTCTGGGACAGACTTCACTCTCAC CATCAACAGACTGGAGCCTGAAGATTTTGCAG TGTATTTCTGTCAGCAGTATGAAAGCTCACCG TGGACGTTCGGCCAAGGGACCAAGGTGGAAA TCAAA<br>SEQ ID NO: 25783 | CAGGTGCAGTCTACAGCAGTGGGGCGCAGGACTG TTGAAGCCTTCGGAGACCCTGTCCCTCACCTGCG CTGTCTATGTGGGTCCTTCAGTGGTTGCTACTG GAGCTGGATCCGCCAGCCCCCAGGGAAGGGGCT GGAGTGGATTGGGGAAATCAATCATAGTGGAAG GACCAACTACAACCGTCCCTCAAGAGTCGAGTC ACCATCTCAGTAGACACGTCCGAGAACCAGTTCT CCCTGAAGTTGAGCTCTGTGACCGCCGCGGACAC GGCTGTGTATTACTGTGCGAGAGACTACGGTGGG CTTGACTACTGGGGCCAGGGAACCCTGGTCACCG TCTCCTCA<br>SEQ ID NO: 29789 |
| | | AA | EIVLTQSPGTLSLSPGERATLSCRASQSVDSNYLA WYQQKPGQAPRLLIYGASSRAPGIPDRFSGSGSG TDFTLTINRLEPEDFAVYFCQQYESSPWTFGQGT KVEIK<br>SEQ ID NO: 25784 | QVQLQQWGAGLLKPSETLSLTCAVYGGSFSGCYW SWIRQPPGKGLEWIGEINHSGRTNYNPSLKSRVTIS VDTSENQFSLKLSSVTAADTAVYYCARDYGGLDY WGQGTLVTSS<br>SEQ ID NO: 29790 |

FIGURE 50
(Continued)

| | | | |
|---|---|---|---|
| iPS:434573 | 21-225_77E6 | NA | GACATCCAGATGACCCAGTCTCCATCCTCACT GTCTGCATCTGTAGGAGACAGAGTCACCATCA CTTGTCGGGCGAGTCAGGGCATTAGCAAGTAT TTAGCCTGGTTTCAGCAGAAACCAGGGAAAGC CCCTAAGTCCCTGATCTATGCTGCATCCAGTTT GCAAGGTGGGGCCCCATCAAAGTTCAGCGGC AGTGGATCTGGGACAGATTTCACTCTCACCAT CAGCAGCCTGCAGCCTGAAGATTTTGCAACTT ATTACTGCCAACAGTACAGTAATTACCCGCTC ACTTTCGGCGGAGGGACCAAGGTGGAGATCA AA<br>SEQ ID NO: 25785 | CAGGTGCAGCTGGTGGAGTCTGGGGGAGGCGTG GTCCAGTCTGGGAGGTCCCTGAGACTCTCCTGTG CAGCGCTTCTGGATTCACCTTCAGTAGCTATGGCAT GCACTGGGTCCGCCAGGCTCCAGGCAAGGGCT GGAGTGGGTGGCAGTTATATGGTATGATGGAAGT AATCAAAACTATGCAGACTCCGTGAAGGGCCGA TTCACCATCTCCAGAGACAATTCCAAGAACACGC TGTTTCTGCAAATGAACAGCCTGAGAGCCGAGG ACACGGCTGTGTATTACTGTGCGAGAGATGGCAG CTATGTTACGACGGCCTTGACTACTGGGGCCAG GGAACCCTGGTCACCGTCTCCTCA<br>SEQ ID NO: 29791 |
| | | AA | DIQMTQSPSSLSASVGDRVTITCRASQGISKYLA WFQQKPGKAPKSLIYAASSLQGGAPSKFSGSGS GTDFTLTISSLQPEDFATYCQQYSNYPLTFGGG TRVEIK<br>SEQ ID NO: 25786 | QVQLVESGGGVVQSGRSLRLSCAASGFTFSSYGMH WVRQAPGKGLEWVAVIWYDGSNQNYADSVKGRF TISRDNSKNTLFLQMNSLRAEDTAVYYCARDGSYG YDGLDYWGQGTLVTVSS<br>SEQ ID NO: 29792 |
| iPS:434575 | 21-225_77C7 | NA | GACATCGTGATGACCCAGTCTCCAGACTCCCT GGCTGTGTCTCTGGGCGAGAGGGCCACCATCA ACTGCAAGTCCAGCCAGACTGTTTTACACAGC TCCAACAATTATAACTACTTAGCTTGGTACCA GCAGAAGCCAGGACAGCCCCCTAAGGTGCTCC TTTACTGGACATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTGTCAGCAA TATTTTAGTAGTCCTCCGACGTTCGGCCAAGG GACCAGGGTGGAAATCAAA<br>SEQ ID NO: 25787 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATCACAGAAGTTCCAGGGCA GTAACACAGGCTATGCACAGAACACCTCCATAAGCA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA<br>SEQ ID NO: 29793 |

FIGURE 50
(Continued)

| | | | |
|---|---|---|---|
| | | AA | DIVMTQSPDSLAVSLGERATINCKSSQTVLHSSN NYNYLAWYQQKPGQPPKVLLYWTSTRESGVPD RFSGSGSGTDFTLTISSLQAEDVAVYYCQQYFSS PPTFGQGTRVEIK<br><br>SEQ ID NO: 25788 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS<br><br>SEQ ID NO: 29794 |
| iPS:434579 | 21-225_77F7 | NA | GAAATTGTGTTGACGCAGTCTCCAGGCACCCT GTATTTGTCTCCAGGGGAAAGAGCCACCCTGT CATGCAGGGCCAGTCAGAGTGTTTACAGCAGC TACTTAGCGTGGTACCAGCAGAAACCTGGCCA GGCTCCCAGGCTCCTCATCATTTATGGTGCATCA GCCGGGCCACTGGCATCCCAGACAGGTTCAGT GGCAGTGGGTGTGGGACAGACTTCGCTCTCAC CATCAGCAGAGTGGAGCATGAAGATTGTGCA GTGTATTACTGTCAGCACTATGATAACTCACC GTGGACGTTCGGCCAAGGGACCAAGGTGGAA ATCAAA<br><br>SEQ ID NO: 25789 | CAGGTGCAGTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29795 |
| | | AA | EIVLTQSPGTLYLSPGERATLSCRASQSVYSSYLA WYQQKPGQAPRLIIYGASSRATGIPDRFSGSGSG TDFALTISRVEHEDCAVYYCQHYDNSPWTFGQG TKVEIK<br><br>SEQ ID NO: 25790 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29796 |

FIGURE 50
(Continued)

| | | | |
|---|---|---|---|
| iPS:434581 | 21-225_74B12 | NA | GAAATTGTGTTGACGCAGTCTCCAGGCACCCT GTATTTGTCTCCAGGGGAAAGAGCCACCCTCT CCTGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCACCG TGGACGTTCGGCCAAGGGACCAAGGTGGAAA TCAAA<br>SEQ ID NO: 25791 | CAGGTGCAGCTACAGCAGTGGGGCGCAGGACTG TTGAAGCCTTCGGAGACCCTGTCCCTCACCTGCG CTGTCCATGTGGGTCCTTCAGTGGTTGTTACTG GAGCTGGATCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGGACAC GGCTGTGTATTACTGTGCGAGGGACTACGGCGGT ATGGACGTCTGGGGCCAAGGGACCACGGTCACC GTCTCCTCA<br>SEQ ID NO: 29797 |
| | | AA | EIVLTQSPGTLYLSPGERATLSCRASQSVYSSYLA WYQQKPGQAPRLLIYGASSRSTGIPDRFSGSGSG TDFALTISRLEPEDFAVYYCQHYDNSPWTFGQG TKVEIK<br>SEQ ID NO: 25792 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTSS<br>SEQ ID NO: 29798 |
| iPS:434583 | 21-225_74B6 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGC TACTTAGCCTGGTACCAGCAGAAACCTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTAACTCACCG CTCACTTTCGGCGGAGGGACCAAGGTGGAGAT CAAA<br>SEQ ID NO: 25793 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGATGCACAGAAGTTCCAGGGCAG TAACACAGGCTATGCACCAGAACACCTCCATAAGCAC AGTCACCATGACCAGGAGCTGAACAGCCTGAGATCTGA AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCCTTA<br>SEQ ID NO: 29799 |

FIGURE 50
(Continued)

| | | | |
|---|---|---|---|
| | | AA | EIVLTQSPGTLSLSPGERATLSCRASQSVSSSYLA WYQQKPGQAPRLLIYGASTRATGIPDRFSGSGSG TDFTLTISRLEPEYFAVYYCQQYGNSPLTFGGGT KVEIK SEQ ID NO: 25794 | QVQLVQSGAEVKKPGASVKVSCKASGYTFTNYDIN WVRQATGQGLEWMGWMHPNGNTGYAQKFQGR VTMTRNTSISTAYMELNSLRSEDTAVYYCAISSGW YWFDPWGQGTLVTVSL SEQ ID NO: 29800 |
| iPS:434585 | 21-225_75A12 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGG TACTTAGCCTGGTACCAGCAGAAACCTGGCCA GGCTCCCAGACTCCTCATCTATGGTGCATCA GCAGGGCCACTGGCATCCCAGACAGGTTCAGT GGCAGTGGGTCTGGGACAGACTTCACTCTCAC CATCAGCAGACTGGAGCCTGAGATTTTGCAG TATATTACTGTCAGCATTATGATAGCTCACCGT GGACGTTCGGCCAAGGGACCAAGGTGGAAAT CAAA SEQ ID NO: 25795 | CAGGTGCAGCTACAGCAGGGGGGCGCAGGACCG TTGAAGCCTTCGGAGACCCTGTCCCTCACCTGCG CTGTCTATGGTGGGTCCTTCAGTGGTTGCTACTG GAGCTGGATCCGCCAGCCCCCAGGGAAGGGGCT GGAGTGGATTGGGGAAATCAATTATAGTGGAAG AACCAACTACAACCCGTCCCTCAAGAGTCGAGTC ACCATATCAGTAGACACGTCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA SEQ ID NO: 29801 |
| | | AA | EIVLTQSPGTLSLSPGERATLSCRASQSVSSRYLA WYQQKPGQAPRLLIYGASSRATGIPDRFSGSGSG TDFTLTISRLEPADFAVYYCQHYDSSPWTFGQGT KVEIK SEQ ID NO: 25796 | QVQLQQGGAGPLKPSETLSLTCAVYGGSFSGCYWS WIRQPPGKGLEWIGEINYSGRTNYNPSLKSRVTISV DTSKNQFSLKLSSVTAADTAVYYCARDYGGMDV WGQGTTVTVSS SEQ ID NO: 29802 |

FIGURE 50
(Continued)

| | | | |
|---|---|---|---|
| iPS:434587 | 21-225_74G3 | NA | GAAATTGTTATGTTGACGCAGTCTCCAGGCACCCT GTGTTGGTCTCCAGGGGAAAGAGCCACCCTCT CGTGCAGGGCCAGTCAGAGTGTTAGCAGCAGC TACTTAGTCTGGTATCAGCAGAAACCTGGCCA GGCTCCCAGGCTCCTCATCTATGGTGCATCCA CCAGGGCCACTGGCATCCCAGACACAGGTTCAGT GGCAGTGGGTCTGGGACAGACTTCACTCTCAC CATCAGCAGACTGGAGCCTGAAGTTTGCAG TTTATTACTGTCAGCAGTATGGTTGCTCACCGC TCACTTTCGGCGGAGGGACCAAGGTGGAGATC ACA |
| | | | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGATGGATGCACCTAACAGTGG TAACACAGGCTATGCACAGAAGTTCCAGGGCAG AGTCACCATGACCAGAAACACCTCCATCAGCAC AGCCTACATGGAGCTGAGCAGCCTGAGATCTGA GGACACGGCCGTGTATTACTGTGCGATTAGTAGT GGCTGGTACTGTTCGACCCCTGGGGCCAGGGA ACCCTGGTCACCGTCTCCTCA |
| | | | SEQ ID NO: 25797 | SEQ ID NO: 29803 |
| | | AA | EFMLTQSPGTLCWSPGERATLSCRASQSVSSSYL VWYQQKPGQAPRLLIYGASTRATGIPDRFSGSGS GTDFTLTISRLEPEYFAVYYCQQYGCSPLTFGGG TKVEIT | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25798 | SEQ ID NO: 29804 |
| iPS:434595 | 21-225_77A10 | NA | GAAATTGTGTTGACGCAGTCTCCAGGCACCCT GTCTTTGTCTCCAGGGGAGAGAGCCACCCTCT CCTGCAGGGCCAGTCAGAGTGTTCACAGCAGG TACTTAGCCTGGTACCAGCAGAAACCTGGCCA GGCTCCCAAACTCCTCATCTTTGGTGCATCCA GCAGGGCCACTGGCATCCCAGACAGGTTCAGT GGCAGTGGGTCTGGGACAGCCTCACTCTCAC CATCAGCAGACTGGAGCCTGAAGATTTTGCAG TATATTACTGTCAGCATTATGATAGCTCACCGT GGACGTTCGGCCAAGGGACCAAGGTGGAAAT CAAA | CAGGTGCAGCTACAACAGGGGGGGGCAGGACCG TTGAAGCCTTCGGAGACCCTGTCCCTCACCTGCG CTGTCTATGGTGGGTCCTTCAGTGGTTGCTACTG GAGCTGGATCCGCCAGCCCGCAGGGAAGGGCT GGAGTGGATTGGGGAAATCAATTATAGTGGAAG AACCAACTACAACCCGTCCCTCAAGAGTCGAGTC ACCATATCAGTAGACACGTCCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA |
| | | | SEQ ID NO: 25799 | SEQ ID NO: 29805 |

FIGURE 50
(Continued)

| | | | |
|---|---|---|---|
| iPS:434597 | 21-225_77C10 | AA | EIVLTQSPGTLSLSPGERATLSCRASQSVHSRYLAWYQQKPGQAPKLLIFGASSRATGIPDRFSGSGSGTDFTLTISRLEPEDFAVYYCQHYDSSPWTFGQGTKVEIK QVQLQQGGAGPLKPSETLSLTCAVYGGSFSGCYWSWIRQPPGKGLEWIGEINYSGRTNYNPSLKSRVTISVDTSKNQFSLKLSSVTAADTAVYYCARDYGGMDVWGQGTTVTVSS |
| | | | SEQ ID NO: 25800 SEQ ID NO: 29806 |
| | | NA | GACATCGTGATGACCCAGTCTCCAGATTGCCTGGCTGTGTCTCTGGGCGAGAGGGCCACCATCAACTGCAAGTCCAGCCAGAGTGTTTATACACCTCCAACAATAACAACTACTTAGCTTGGTACCAGCAGAAACCAGGACAGCCTCCTAAGCTGCTCATTTACTGGGCATCTCACCCGGGAATCCGGGTCCCTGACCGATTCAGTGGCAGCGGGTCTGGGACAGATTTCACTCTCACCATCAGCAGCCTGCAGGCTGAAGATGTTGCAGTTTATTATTGTCAGCACTATTATAATACTCCGTGGAAGTTTGTCCAAGGGACCAAGGTGGAAATCACA CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGCACAGAAGTTCCAGGGCAGTAACACAGGCTATGCACAGAAGAACACTCCATAAGCACAGTCACCATGACCAGGAACACCTCCATAAGCACAGCCTACATGGAGCTGAGCAGCCTGAGATCTGAGGACACGGCCGTGTATTACTGTGCGATTAGCAGTGGCTGGTACTGGTTCGACCCCTGGGGCCAGGGAACCCTGGTCACCGTCTCCTCA |
| | | | SEQ ID NO: 25801 SEQ ID NO: 29807 |
| | | AA | DIVMTQSPDCLAVSLGERATINCKSSQSVLYTSNNNNYLAWYQQKPGQPPKLLIYWASTRESGVPDRFSGSGSGTDFTLTISSLQAEDVAVYYCQHYYNTPWKFVQGTKVEIT QVQLVQSGAEVKKPGASVKVSCKASGYTFTNYDINWVRQATGQGLEWMGWMHPNSGNTGYAQKFQGRVTMTRNTSISTAYMELSSLRSEDTAVYYCAISSGWYWFDPWGQGTLVTVSS |
| | | | SEQ ID NO: 25802 SEQ ID NO: 29808 |

FIGURE 50
(Continued)

| | | | |
|---|---|---|---|
| iPS:434603 | 21-225_77D11 | NA | GAATTTATGTTGACGCAGTCTCCAGGCACCCT GTATTGGTCTCCAGGGGAAAGAGCCACCATCT CGTGCAGGGCCAGTCAGAGTGTTAGCAGCAGC TACTTAGTCTGGTATCAGCAGAAACCTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCCTGAAGATATTTTGCAG TTTATTACTGTCAGCAGTATGGTTGCTCACCGC TCACTTTCGGCGGAGGGACCAAGGTGGAGATC ACA <br><br>SEQ ID NO: 25803 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGATGGATGCACCCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGTTCGACCCCTGGGGCCAGGGA ACCCTGGTCACCGTCCTCA <br><br>SEQ ID NO: 29809 |
| | | AA | EFMLTQSPGTLYWSPGERATISCRASQSVSSSYL VWYQQKPGQAPRLLIYGASTRATGIPDRFSGSGS GTDFTLTISRLEPEYFAVYYCQQYGCSPLTFGGG TKVEIT <br><br>SEQ ID NO: 25804 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS <br><br>SEQ ID NO: 29810 |
| iPS:434611 | 21-225_77C12 | NA | GAAATTGTGTTGACGCAGTCTCCAGGCACCCT GTCTTTGTCTCCAGGGGAAAGAGCCACCCTCT CCTGCAGGGCCAGCAGTGTTGACAGCAGT TATTTAGCCTGGTACCAGCAGAAACGTGGCCA GGCTCCCAGGCTCCTCATCTATGGTGCATCCA GCAGGGCCACTGGCATCCCAGACAGGTTCAGT GGCAGTGGGTCTGGGACAGCCTCACTCTCAC CATCAGCAGCCTGGAGCCTGAAGATTTTGCAG TATATTACTGTCAGCAGTATGAAAGCTCACCG TGGACGTTCGGCCAAGGGACCAAGGTGGAAA TCAAA <br><br>SEQ ID NO: 25805 | CAGGTGCAGCTACAGCAGTGGGGCGCAGGACTG TTGAAGCCTTCGGAGACCCTGTCCCTCACCTGCG CTGTCTATGGTGGGGGCTTCAGTGGTTCCTACTG GAGCTGGATCCGCCAGTCCCCAGGGAAGGGGCT GGAGTGGATTGGGGAAATCAATTATAGGGGAAG CACCAACTACAACCCGTCCCTCAAGAGTCGAGTC ACCATATCAGTAGACACGTCCAAGAACCAGTTCT CCCTGAACCTGAGCTCTGTGACCGCCGGGACAC GGCTGTGTATTACTGTGCGAGGGACTACGGCGGT ATGGACGTCTGGGGCCAAGGGACCACGGTCACC GTCTCCTCA <br><br>SEQ ID NO: 29811 |

FIGURE 50
(Continued)

| | | | | |
|---|---|---|---|---|
| iPS:434613 | 21-225_77D12 | AA | EIVLTQSPGTLSLSPGERATLSCRARQSVDSSYLAWYQQKRGQAPRLLIYGASSRATGIPDRFSGSGSGTDFTLTISRLEPEDFAVYYCQQYESSPWTFGQGTKVEIK | QVQLQQWGAGLLKPSETLSLTCAVYGGAFSGSYWSWIRQSPGKGLEWIGEINYRGSTNYNPSLKSRVTISVDTSKNQFSLNLSSVTAADTAVYYCARDYGGMDVWGQGTTVTVSS |
| | | | SEQ ID NO: 25806 | SEQ ID NO: 29812 |
| | | NA | GACATCGTGATGACCCAGTCTCCAGACTCCCTGGCTGTGTCTCTGGGCGAGGGCCACCATCAATTGCAGGTCCAGCCAGAGTGTTTATACAGCTCCAACAATTATAACTACTTAGCTTGGTACCAGCAGAAACCAGGACAGGCTCCTAAGCTGCTCATTTACTGGGCATCTCACCCGGGGATTCCCGGGGTCCCTGACCGATTCAGTGGCAGCGGGTCTGGGACAGATTTCACTCTCACCATCAGCAGCCTGCAGGCTGAAGATGTGGCCGTTTATTACTGTCAGCAATATTATACTACTCCGTGCAGTTTTGGCCAGGGGACCAAGCTGGAGATCAAG | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGAACCTAACAGTGGTAACACAGGCTATGCACAGAAGTTCCAGGCAGAGTCACCATGACCAGGAACACCTCCATAAACAGCCTACATGGAGCTGAGCAGCCTGAGATCTGAGGACACGGCCGTGTATTACTGTGCGATTAGCAGTGGCTGGTACTGGTTCGACCCCTGGGGCCAGGGAACCCTGGTCACCGTCTCCTCA |
| | | | SEQ ID NO: 25807 | SEQ ID NO: 29813 |
| | | AA | DIVMTQSPDSLAVSLGARATINCRSSQSVLYSSNNYNYLAWYQQKPGQPPKLLIYWASTRDSGVPDRFSGSGSGTDFTLTISSLQAEDVAVYYCQQYYTTPCSFGQGTKLEIK | QVQLVQSGAEVKKPGASVKVSCKASGYTFTNYDINWVRQATGQGLEWMGWMNPNSGNTGYAQKFQGRVTMTRNTSINTAYMELSSLRSEDTAVYYCAISSGWYWFDPWGQGTLVTVSS |
| | | | SEQ ID NO: 25808 | SEQ ID NO: 29814 |

FIGURE 50
(Continued)

| | | | | |
|---|---|---|---|---|
| iPS:434615 | 21-225_76C5 | NA | GACATCCAGATGACCCAGTCTCCATCCTCACT GTCTGCATCTGTAGGAGACAGAGTCACCATCA CTTGTGTCGGGCGAGTCAGTCATTAGCAAGTAT TTAGCCTGGTTTCAGCAGAAACCAGGGAAAGC CCCTAAGTCCCTGATCTATGCTGCATCCAGTT GCAAAGTGGGGCCCATCAAAGTTCAGCGGC AGTGGATCTGGGACAGATTTCACTCTCACCAT CAGCAGCCTGCAGCCTGAAGATTTTGCAACTT ATTACTGCCAACAGTACAGTAATTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGATTCACCTTCAGTAGTAGTGGCAT GCACTGGGTCCGCCAGGCTCCAGGCAAGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGGCAG CTATGGTTACGACGGCCTTGACTACTGGGGCCAG GGAACCCTGGTCACCGTCTCCTCA |
| | | | SEQ ID NO: 25809 | SEQ ID NO: 29815 |
| | | AA | DIQMTQSPSSLSASVGDRVTITCRASQVISKYLA WFQQKPGKAPKSLIYAASSLQSGAPSKFSGSGSG TDFTLTISSLQPEDFATYYCQQYSNYPLTFGGGT KVEIK | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDGSYG YDGLDYWGQGTLVTVSS |
| | | | SEQ ID NO: 25810 | SEQ ID NO: 29816 |
| iPS:434617 | 21-225_74B8 | NA | GACAGCGTGATGACCCAGTCTCCAGACTCCCT GGCTGTGTCTCTGGGCGAGAGGGCCACCATCA ACTGCAAGTCCAGCCAGAGTGTTTTACACAGC AAGGCTTCTGGATACACCTTCACCAATTATGATA TCAACTGGGTGCGACAGGCCACTGGACAAGGC CTGGAGTGGATGGGATGGATGAATGCCACCTAATAGTGG TTGAGTGGATGGGATGGATGAACAGAAGTTCCAGGCAG TAACACAGGCTATGCACAGAAGTTCCAGGCAG AGTCACCCTGACCAGGAACACCTCCATAAGCAC AGCCTACATGGAGCTGAGCAGCCTGAGATCTGA GGAAGACACGGCCGTGTATTACTGTGCGGTTCCAGT GGCTGGTACTGGTTCGACCCCTGGGCCAGGGA ACCCTGGTCACCGTCTCCTCA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCCTAATAGTGG TAACACAGGCTATGCACAGAAGTTCCAGGCAG AGTCACCCTGACCAGGAACACCTCCATAAGCAC AGCCTACATGGAGCTGAGCAGCCTGAGATCTGA GGACACGGCCGTGTATTACTGTGCGGTTCCAGT GGCTGGTACTGGTTCGACCCCTGGGGCCAGGGA ACCCTGGTCACCGTCTCCTCA |
| | | | SEQ ID NO: 25811 | SEQ ID NO: 29817 |

FIGURE 50
(Continued)

| | | | |
|---|---|---|---|
| | | AA | DSVMTQSPDSLAVSLGERATINCKSSQSVLHSSN KKNYLAWYQQKPGQPPKLLIYWASTRESGVPD RFSGSGSGTDFTLTISSLQAEDVAVYYCQQYYRT PWTFGQGTKVEIK | QVQLVQSGAEVKKPGASVKVSCKASGYTFTNYDIN WVRQATGQGLEWMGWMHPNSGNTGYAQKFQGR VTLTRNTSISTAYMELSSLRSEDTAVYYCAVSSGW YWFDPWGQGTLVTVSS |
| | | | SEQ ID NO: 25812 | SEQ ID NO: 29818 |
| iPS:434619 | 21-225_78C1 | NA | GACATCGTGATGACCCAGTCTCCAGATTGCCT GGCTGTGTCTCTGGGCGAGAGGGCCACCATCA ACTGCAAGTCCAGCCAGAGTGTTTATACACC TCCAACAATAACAACTACTTAGCTTGGTACCA GCAGAAACCAGGACAGCCTCCTAAGCTGCTCA TTTACTGGGCATCTACCCGGGAATCCGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCACT ATTATAATACTCCGTGGAAGTTTGTCCAAGGG ACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA |
| | | | SEQ ID NO: 25813 | SEQ ID NO: 29819 |
| | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYYNT PWKFVQGTKVEIK | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25814 | SEQ ID NO: 29820 |

FIGURE 50
(Continued)

| | | | | |
|---|---|---|---|---|
| iPS:434621 | 21-225_74D1 | NA | GAAATAGTGATGACGCAGTCTCCAGCCACCCT GTCTGTGTCTCCAGGGGAAAGAGCCACCCTCT CCTGCAGGGCCAGTCAGTGTTAGCAGAAAT TTAGCCTGGTTCCAGCAGAAACCTGGCCAGGC TCCCAGGCTCCTCATCTATGGTGCATCCATCA GGGCCACTGGTATCCCAGCCAGGTTCAGTGGC AGTGGGTCTGGGACAGAGTTCACTCTCACCAT CTACAGCCTGCAGTCTGAAGATTTTGCAGTTT ATTACTGTCAGCAGTATAATAACTGGCCTCCG CTCACTTTCGGCGGAGGGACCAAGGTGGAGAT CAAA | CAGGTGCAGCTGGTGGAGTCTGGGGGAGGCGTG GTCCAGCCTGGGAGGTCCCTGAGACTCTCCTGTG CAGGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAATACCATGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTGCGAGAGATGAGGG GTTCGGGGAGTTCGACTACTACAACTACGGTATG GACGTCTGGGGCCAAGGGACCACGGTCACCGTC TCCTCA |
| | | | SEQ ID NO: 25815 | SEQ ID NO: 29821 |
| | | AA | EIVMTQSPATLSVSPGERATLSCRASQSVSRNLA WFQQKPGQAPRLLIYGASIRATGIPARFSGSGSG TEFTLTIYSLQSEDFAVYYCQQYNNWPPLTFGG GTKVEIK | QVQLVESGGGVVQPGRSLRLSCAASGFTFSSYGMH WVRQAPGKGLEWVAVIWYDGSNKYHADSVKGRF TISRDNSKNTLYLQMNSLRAEDTAMYYCARDEGF GEFDYYNYGMDVWGQGTTVTVSS |
| | | | SEQ ID NO: 25816 | SEQ ID NO: 29822 |
| iPS:434629 | 21-225_74C3 | NA | GAAATAGTGATGACGCAGTCTCCAGCCACCCT GTCTGTGTCTCCAGGGGAAAGAGCCACCCTCT CCTGCAGGGCCAGTCAGAGTGTTGCCAGCAGC TTAGCCTGGTACCAGCAGAAACCTGGCCAGGC TCCCAGGCTCCTCATCTTTGGTACATCCACCAG GGCCACTGGTATCCCAGCCAGGTTCAGTGGCA GTGGGTCTGGGACAGAGTTCACTCTCATAATC AGCAGCCTGCAGTCTGAAGATTTTGCAGTTTA TTACTGTCAGCAGTATAATGACTGGCCGTGCA GTTTTGGCCTGGGGACCAAGCTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTGGCAT GCACTGGGCCCGCCAGGCTCCAGGCAAGGGGCT GGAATGGGTGGCAGCTATTTGGTATGATGAAGT AATAAATACTGTGCAGACTCCGTGAAGGGCCGA TTCACCATCTCCAGAGACAATTCCAAGAACACAC TGTCTCTGCAAATGAACAGCCTGAGAGCCGAGG ACTCGGCTGTGTATTACTGTGCGAGAGATCGGAG TATACTGGGAGCTGTCTTCTTTGACTACTGGGGC CAGGGAACCCTGGTCACCGTCTCCTCA |
| | | | SEQ ID NO: 25817 | SEQ ID NO: 29823 |

FIGURE 50
(Continued)

| | | | | |
|---|---|---|---|---|
| | | AA | EIVMTQSPATLSVSPGERATLSCRASQSVASSLA WYQQKPGQAPRLLIFGTSTRATGIPARFSGSGSG TEFTLTISSLQSEDFAVYYCQQYNDWPCSFGLGT KLEIK<br>SEQ ID NO: 25818 | QVQLVESGGGVVQPGRSLRLSCAASGFTFSSFGMH WARQAPGKGLEWVAAIWYDGSNKYCADSVKGRF TISRDNSKNTLSLQMNSLRAEDSAVYYCARDRSILG AAFFDYWGQGTLVTVSS<br>SEQ ID NO: 29824 |
| iPS:434633 | 21-225_74G8 | NA | GAAATTGTGTTGACGCAGTCTCCAGGCACCCT GTCTTTGTCTCCAGGGGAAAGAGCCACCCTCT CCTGCAGGGCCAGTCAGAGTTTTAGCAGCGCC TACTTAGCCTGGTACCAGCAGAAACCTGGCCA GGCTCCCAGGCTCCTCATCTATGGTACTTCCA GCAGGGCCACTGGCATCCCAGACAGGTTCAGT GGCAGTGGGTCTGGGACAGATTTCACTCTCAC CATCGGCAGACTGGAGCCTGAAGATTTTGCAG TGTATTACTGTCAACAGTATGGTAACTCAAGG ACGTTCGGCCAAGGGACCAAGGTGGAAATCA AA<br>SEQ ID NO: 25819 | GAGGTGCAGCTGGTGGAGTCTGGGGGAGGCTTG GTAAAGCCTGGGGGGTCCCTTAGACTCTCCTGTG CAGCCTCTGGATTCACTTTCAGTAACGCCTGGAT GAACTGGGTCCGCCAGGCTCCAGGGAAGGGGCT GGAGTGGGTTGGCCGTATTAAAAACAAAGCTGA TGGTGGGACAACAGATACGCTGCACCCGTGAA AGGCAGATTCACCATCTCAAGAGATGATTCAAA AAACACGCTGTATCTGCAAATGAACAGCCTGAA AACCGAGGACACAGCCGTGTATTACTGTACCACA GTGGGAGCTACTACGGACTACTGGGGCCAGGA ACCCTGGTCACCGTCTCCTCA<br>SEQ ID NO: 29825 |
| | | AA | EIVLTQSPGTLSLSPGERATLSCRASQSFSSAYLA WYQQKPGQAPRLLIYGTSSRATGIPDRFSGSGSG TDFTLTIGRLEPEDFAVYYCQQYGNSRTFGQGT KVEIK<br>SEQ ID NO: 25820 | EVQLVESGGGLVKPGGSLRLSCAASGFTFSNAWM NWVRQAPGKGLEWVGRIKNKADGGTTDYAAPVK GRFTISRDDSKNTLYLQMNSLKTEDTAVYYCTTVG ATTDYWGQGTLVTVSS<br>SEQ ID NO: 29826 |

FIGURE 50
(Continued)

| | | | |
|---|---|---|---|
| iPS:434635 | 21-225_78E6 | NA | GACATCGTGATGACCCAGTCTCCAGACTCCCT GGCTGTGTCTCTGGGCGAGAGGGCCACCATCA ACTGCAAGTCCAGCCAGAGTGTTTGTACAGC TCCAACAGTCACAACTTAGCTTGTACCA GCAGAAACCAGGACAGCCTCCTAAACTGCTCA TTTACTGGGCATCTATCCGGGAATCCGGGGTC CCTGACCGATTCAGTGGCAGCGGGTCTGGGAC AGATTTCACTCTCTCCATCAGCAGCCTGCAGG CTGAAGATGTGGCAGTTTATTACTGTCAGCAA TATTATAGTACTCCGTGCAGTTTTGGCCAGGG GACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCTCTGGACAAGGAC TTGAGTGGATGGGATGGATGCACCTAACAGTGG TAACACAGGCTATGCACAGAAGTTCCAGGGCAG AGTCACCATGACCAGGAACACTTCCATAAGCAC AGCCTACATGGAGCTGAGCAGCCTGAGATCTGA GGACTCGGCCGTATATTACTGTGCGTATAGTAGT GGCTGGTACAAATTTGACTACTGGGAGCCAGGGA ACCCTGGTCACCGTCTCCTCA |
| | | | SEQ ID NO: 25821 | SEQ ID NO: 29827 |
| | | AA | DIVMTQSPDSLAVSLGERATINCKSSQSVLYSSN SHNYLAWYQQKPGQPPKLLIYWASIRESGVPDR FSGSGSGTDFTLSISSLQAEDVAVYYCQQYYSTP CSFGQGTKLEIK | QVQLVQSGAEVKKPGASVKVSCKASGYTFTNYDIN WVRQASGQQLEWMGWMHPNSGNTGYAQKFQGR VTMTRNTSISTAYMELSSLRSEDSAVYYCAYSSGW YKFDYWSQGTLVTVSS |
| | | | SEQ ID NO: 25822 | SEQ ID NO: 29828 |
| iPS:434637 | 21-225_78E7 | NA | GAAATTGTGTTGACGCAGTCGCCAGGCACCCT GTCTTTGTCTCCAGGGGAGAGAGCCACCCTCT CCTGCAGGGCCAGTCAGAGTGTTGACAGCAAC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTTTTACTGTCAGCAGTATGAACGCTCACCG TGGACGTTCGGCCAAGGGACCAAGGTGGAAA TCAAA | CAGGTGCAGCTACAGCAGTGGGGCGCAGGACTG TTGAAGCCTTCGGAGACCCTGTCCCTCACCTGCG CTGTCTATGGTGGGTCCCTCAGTGGTTCTACTG GAGCTGGATCCGCCAGCCCCCAGGGAAGGGGCT GGAGTGGATTGGGAAATCAATCTTAGTGGAAG CACCAACTACAACCCGTCCCTCAAGAGTCGAGTC ACCATATCAGTAGACACGTCCAAGAGCCAGTTCT CCCTGACGCTCTGTGCGAGAGACTACGGTGGC GGCTGTGTATTACTGTGCAGGGGCCAGGGAACCCTGGTCACCG CTTGACTACTGGGGCCAGGGAACCCTGGTCACCG TCTCCTCA |
| | | | SEQ ID NO: 25823 | SEQ ID NO: 29829 |

FIGURE 50
(Continued)

| | | | |
|---|---|---|---|
| | | AA | EIVLTQSPGTLSLSPGERATLSCRASQNVDSNYL AWYQQKPGQAPRLLIYGASSRATGIPDRFSGSGS GTDFTLTISRLEPEDFAVFYCQQYERSPWTFGQG TKVEIK<br>SEQ ID NO: 25824 | QVQLQQWGAGLLKPSETLSLTCAVYGGSLSGSYW SWIRQPPGKGLEWIGEINLSGSTNYNPSLKSRVTISV DTSKSQFSLTLRSVTAADTAVYYCARDYGGLDYW GQGTLVTVSS<br>SEQ ID NO: 29830 |
| iPS:434639 | 21-225_74B7 | NA | GACATCGTGATGACCCAGTCTCCAGACTCCCT GGCTGTGTCTCTGGGCGAGAGGGCCACCATCA ACTGCAAGTCCAGCCAGAGTGTTTTACACAGC TCCAACAATTATAACTACTTAGCTTGGTACCA GCAGAAGCCAGGACAGCCCCCTAAGGTGCTC ATTTACTGGACATCTACCCGGGAATCCGGGGT CCCTGACCGATTCAGTGGCAGCGGGTCTGGGA CAGATTTCACTCTCACCATCAGCAGCCTGCAG GCTGAAGATGTGGCAGTTTATTACTGTCAGCA ATATTTTAGTAGTCCTCCGACGTTCGGCCAAG GGACCAAGGTGGAAATCAAA<br>SEQ ID NO: 25825 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA<br>SEQ ID NO: 29831 |
| | | AA | DIVMTQSPDSLAVSLGERATINCKSSQTVLHSSN NYNYLAWYQQKPGQPPKVLIYWTSTRESGVPD RFSGSGSGTDFTLTISSLQAEDVAVYYCQQYFSS PPTFGQGTKVEIK<br>SEQ ID NO: 25826 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS<br>SEQ ID NO: 29832 |

FIGURE 50
(Continued)

| | | | | |
|---|---|---|---|---|
| iPS:434649 | 21-225_78E11 | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TTCAACAATTACAACTACTTAGCTTGGTACCA GCAGAAACCAGGACAGCCTCCTAAGAAGCTC ATTTACTGGGCATCTACCCGGGAATCCGGGGT CCCTGACCGATTCAGTGGCAGCGGGTCTGGA CAGATTTCACTCTCACCATCAGCAGCCTGCAG GCTGAAGATGTGGCAGTTTATTCCTGTCAGCA ATATTATAGTAGTCCCGACGTTCGGCCAAG GGACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTGTGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGAGTAGCA GTGGCTGGAACTTCTTTGACTACTGGGGCCAGGG AACCCTGGTCACCGTCTCCTCA |
| | | | SEQ ID NO: 25827 | SEQ ID NO: 29833 |
| | | AA | DIVMTQSPDSLAVSLGERATINCKSSQSVLYSFN NYNYLAWYQQKPGQPPKKLIYWASTRESGVPD RFSGSGSGTDFTLTISSLQAEDVAVYSCQQYYSS PPTFGQGTKVEIK | QVQLVQSGAEVKKPGASVKVSCKASGYTFTNYDIN WVRQATGQGLEWMGWMNPNSGNTGCAQKFQGR VTMTRNTSISTAYMELSSLRSEDTAVYYCASSSGW NFFDYWGQGTLVTVSS |
| | | | SEQ ID NO: 25828 | SEQ ID NO: 29834 |
| iPS:434653 | 21-225_74B5 | NA | GACATCGTTATGACCCAGTCTCCAGACTCCCT GGCTGTGTCTCTGGGCGAGAGGGCCACCATCA ACTGCAAGTCCAGCCAGAGTGTTTTATTCAGC TCCAACAATTATAACTACTTAGCTTGGTACCA GCAGAAACCAGGACAGCCTCCTAACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGCTGATGTGGCAGTTTATTACTGTCAGCAA TATTATAGTTCTCCTCCGACGTTCGGCCAAGG GACCACGGTGCAAATCAAA | CAGGTGCAGTTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGGCT TGAGTGGATGGGATGGATGCACAGAAGTTCCAGGGCAG TAACACAGGCTATGCACAGAAGTTCCAGGGCAG AGTCACCATGACCAGGAACACCTCCACAAGCAC AGCCCACATGGAGCTGAGCAGCCTGAGATCTGA GGACACGGCCGTGTATTACTGTGCGGTCTCCAGT GGCTGGAACTGGTTCGACCCCTGGGGCCAGGGA ACCCTGGTCACCGTCTCCTCA |
| | | | SEQ ID NO: 25829 | SEQ ID NO: 29835 |

FIGURE 50
(Continued)

| | | | |
|---|---|---|---|
| iPS:434655 | 21-225_78H12 | AA | DIVMTQSPDSLAVSLGERATINCKSSQSVLFSSN NYNYLAWYQQRPGQPPNLLIYWASTRESGVPD RFSGSGSGTDFTLTISSLQAADVAVYYCQQYYSS PPTFGQGTTVQIK<br>SEQ ID NO: 25830 | QVQLVQSGAEVKKPGASVKVSCKASGYTFTNYDIN WVRQATGQGLEWMGWMNPNSGNTGYAQKFQGR VTMTRNTSTSTAHMELSSLRSEDTAVYYCAVSSGW NWFDPWGQGTLVTVSS<br>SEQ ID NO: 29836 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTACACAGC TTCAACAATTATAACTACTTAGCTTGGTACCA GCAGAAGCCAGGACAGCCCCCTAAGGTGCTC ATTTACTGGACATCTACCCGGGAATCCGGGGT CCCTGACCGATTCAGTGGCAGCGGGTCTGGGA CAGATTTCACTCTCACCATCAGCAGCCTGCAG GCTGAAGATGTGGCAGTTTATTACTGTCAGCA ATATTTTAGTAGTCCTCCGACGTTCGGCCAAG GGACCAAGGTGGAAATCAAA<br>SEQ ID NO: 25831 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA<br>SEQ ID NO: 29837 | |
| | | AA | DIVMTQSPDSLAVSLGERATINCKSSQTVLHSFN NYNYLAWYQQKPGQPPKVLIYWTSTRESGVPD RFSGSGSGTDFTLTISSLQAEDVAVYYCQQYFSS PPTFGQGTKVEIK<br>SEQ ID NO: 25832 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS<br>SEQ ID NO: 29838 | |

FIGURE 50
(Continued)

| | | | |
|---|---|---|---|
| iPS:434657 | 21-225_79G1 | NA | GAAATTGTGTTGACGCAGTCTCCAGGCACCCT GTATTTGTCTCCAGGGGAAAGAGCCACCCTCT CCTGCAGGGCCAGTCAGAGTGTTTACAGCAGC TACTTAGCCTGGTACCAGCAGAAACCTGCCCA GGCTCCCAGGCTCCTCATTTATGGTGTCATCCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCACCG TGGACGTTCGGCCAAGGGACCAAGGTGGAAA TCAAA <br> SEQ ID NO: 25833 | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGGAAGGGCT GGAGTGGATTGGGGAAATCAATCATAGTGGAAG CACCAACTACACAACCCGTCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA <br> SEQ ID NO: 29839 |
| | | AA | EIVLTQSPGTLYLSSGERATLSCRASQSVYSSYLA WYQQKPAQAPRLLIYGASSRSTGIPDRFSGSGSG TDFALTISRLEPEDFAVYYCQHYDNSPWTFGQG TKVEIK <br> SEQ ID NO: 25834 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS <br> SEQ ID NO: 29840 |
| iPS:434663 | 21-225_79F3 | NA | GAAATTGTGTTGACGCAGTCTCCAGGCACCCT GTATTTGTCTCCAGGGGAAAGAGCCACCCTCT CCTGCAGGGCCAGTCAGAGTGTTTACAGCAGC TACTTAGCCTGGTACCAGCAGAAACCTGCCCA GGCTCCCAGGCTCCTCATCTATGGTGCATCCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTACTATGATAATCACCG TGGACGTTCGGCCAAGGGACCAAGGTGGAAA TCAAA <br> SEQ ID NO: 25835 | CAGGTGCAGCTACAGCAGTGGGGCGCAGGACTG TTGAAGCCTTCGGAGACCCTGTCCCTCACCTGCG CTGTCCATGGTGGGTCTTCAGTGGTTGCTACTG GAGCTGGATCCGCCAGCCCCAGGGAAGGGGCT GGAGTGGATTGGGGAAATCAATCATAGTGGAAG CACCAACTACACAACCCGTCCTCAAGAGTCGAGTC ACCATTTCAGTAGACACGTCAAGAACCAGTTCT CCCTGAAGCTGAGCTGTGTGACCGCCGCGGACAC GGCTGTGTATTACTGTGCGAGGGACTACGGCGGT ATGGACGTCTGGGGCCAAGGGACCACGGTCACC GTCTCCTCA <br> SEQ ID NO: 29841 |

FIGURE 50
(Continued)

| | | | |
|---|---|---|---|
| iPS:434665 | 21-225_74G4 | AA | EIVLTQSPGTLYLSPGERATLSCRASQSVYSSYLA WYQQKPAQAPRLLIYGASSRSTGIPDRFSGSGSG TDFALTISRLEPEDFAVYYCQHYDNSPWTFGQG TKVEIK<br>SEQ ID NO: 25836 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29842 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTATACAGT TCCAACAATAATAACTACTTAGCTTGGTACCA GCAGAAGGCAGGACAGCCTCCTAAGCTGCTCA TTTACTGGGCATCTACCCGGAATCCGGGGTC CCTGACCGATTCAGTGGCAGCGGGTCTGGGAC AGATTTCACTCTCACCATCAGCAGCCTGCAGG CGGAAGATGTGGCAGTTTATTACTGTCAGCAA TATTATAGTAATTCCTCCGACGTTCGGCCAAGG GACCAAGGTGGAAATCAAA<br>SEQ ID NO: 25837 | CAGGTGCAGCTGGTGCAGTCTGGGGCTGAGGTG AAGAAGCCTGGGGCCTCAGTGAAGGTCTCTGC AAGGCTTCTGGATACACCTTCACCAATTATGATG TCAACTGGGTGCGACAGGCCACTGGACAAGGGC TTGAATGGATGGGATGGATGCACAGAAGTTCAGGGCAG TAACACAGGCTATGCACAGAAGTTCCAGGGCAG AGTCACCATGACCAGGAACACCTCATACGCAC AGCCTACATGGAGCTGAGCAGCCTGAGATCTGA GGACACGGCCGTGTATTACTGTGCGAGTAGCAGT GGCTGGTACCATTTTGACTACTGGGGCCAGGGAA CCCTGGTCACCGTCTCCTCA<br>SEQ ID NO: 29843 |
| | | AA | DIVMTQSPDSLAVSLGERATINCKSSQSVLYSSN NNNYLAWYQQKAGQPPKLLIYWASTRESGVPD RFSGSGSGTDFTLTISSLQAEDVAVYYCQQYYSI PPTFGQGTKVEIK<br>SEQ ID NO: 25838 | QVQLVQSGAEVKKPGASVKVSCKASGYTFTNYDV NWVRQATGQGLEWMGWMHPNSGNTGYAQKFQG RVTMTRNTSIRTAYMELSSLRSEDTAVYYCASSSG WYHFDYWGQGTLVTVSS<br>SEQ ID NO: 29844 |

FIGURE 50
(Continued)

| | | | | |
|---|---|---|---|---|
| iPS:434669 | 21-225_79F4 | NA | GACATCCAGATGACCCAGTCTCCATCCTCACTGTCTGCATCTGTAGGAGACAGAGTCACCATCACTTGTCGGGCGAGTCAGGGCATTAGCAAGTATTTAGCCTGGTTTCAGCAGAAACCAGGGAAAGCCCCTAAGTCCCTGATCTATGCTGCATCCAGTTTGCAAGGTGGGGTCCCATCAAGTTCAGCGGCAGTGGATCTGGGACAGATTTCACTCTCACCATCAGCAGCCTGCAGCCTGAAGATTTTGCAACTTATTACTGTCCAACAGTACAGTAATTACCACTCACTTTCGGCGGAGGGACCAAGGGTGGAGATCAA A | CAGGTGCAGTTGGTGGAGTCTGGGGGAGGCGTGGTCCAGTCTGGGGAGGTCCCTGAGACTCTCCTGTGCAGCCGTCTGATTCACCTTCAGTAACTATGGCATGCACTGGGTCCGCCAGGCTCCAGGCAAGGGCTGGAGTGGGTGGCAGTTATATGGTATGATGAAGTAATCAAAACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTACTACTGTGCGAGAGATGGCAGCTATGGTTATGACGGCCTTGACTACTGGGGCCAGGGAACCCTGGTCACCGTCTCCTCA |
| | | | SEQ ID NO: 25839 | SEQ ID NO: 29845 |
| | | AA | DIQMTQSPSSLSASVGDRVTITCRASQGISKYLAWFQQKPGKAPKSLIYAASSLQGGAPSKFSGSGSGTDFTLTISSLQPEDFATYYCQQYSNYPLTFGGGTRVEIK | QVQLVESGGGVVQSGRSLRLSCAASGFTFSNYGMHWVRQAPGKGLEWVAVIWYDGSNQNYADSVKGRFTISRDNSKNTLFLQMNSLRAEDTAVYYCARDGSYGYDGLDYWGQGTLVTVSS |
| | | | SEQ ID NO: 25840 | SEQ ID NO: 29846 |
| iPS:434671 | 21-225_74F4 | NA | GAAATTGTGTTGACGCAGTCTCCAGGCACCCTGTCTTTGTCTCCAGGGGAAAGAGCCACCCTCTCCTGCAGGGCCAGTCAGAGTGTTTTAGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGTATGGTAGCTCACGGACGTTCGGCCAAGGGACCAAGGTGGAAATCAAA | GAGGTGCAGCTGGTGGAGTCTGGGGGAGGCTTGGTAAAGCCTGGGGGGTCCCTTAGACTCTCCTGTGCAGCCTCTGGATTCACTTTCAGTAACGCCTGATGAACTGGGTCCGCCAGGCTCCAGGGAAGGGCTGGAGTGGGTTGGCCGAATTAAAAACAAATTGATGGGACAACAGACTACGTGCACCCGTGAAAGGCAGATTCACCATCTCAAGAGATGATTCAAAAACACGTGTATCTGCAAATGAACAGCCTGAAAACCGAGGACACAGCCGTGTATTACTGTACCACAGTGGGAGCTACTACGGACTACTGGGGCCAGGGAACCCTGGTCACCGTCTCCTCA |
| | | | SEQ ID NO: 25841 | SEQ ID NO: 29847 |

FIGURE 50
(Continued)

| | | | |
|---|---|---|---|
| iPS:434673 | 21-225_74E3 | AA | EIVLTQSPGTLSLSPGERATLSCRASQIFSSSYLA WYQQKPGQSPRLLIYGASSRATGIPDRFSGSGSG TDFTLTISRLEPEDFAVYYCQQYGSSRTFGQGTK VEIK<br>SEQ ID NO: 25842 | EVQLVESGGGLVKPGGSLRLSCAASGFTFSNAWM NWVRQAPGKGLEWVGRIKNKIDGGTTDYAAPVKG RFTISRDDSKNTLYLQMNSLKTEDTAVYYCTTVGA TTDYWGQGTLVTVSS<br>SEQ ID NO: 29848 |
| | | NA | GAAATAGTGATGACGCAGTCTCCAGCCACCCT GTCTCTGTCTCCAGGGGAAAGAGCCACCCTCT CCTGCAGGGCCAGTCTGAGTGTTGTCAACAGC TTAGCCTGGTACCAGCAGAAACCTGGCCAGGC TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCAGCCTGCAGTCTGAAGATATAATGACTGGCCGTGC ATTACTGTCAGCAGTATGGTATAATGACTGGCCGTGC AGTTTTGGCCAGGGGACCAAGCTGGAGATCAA A<br>SEQ ID NO: 25843 | CAGGTGCAGCTGGTGGAGTCTGGGGGAGGCGTG GTCCAGCCTGGGAGGTCCCTGAGACTCTCCTGTA CAGCGTCTGGATTCACCTTCAGTAGCTATGGCAT GCACTGGGTCCGCCAGGCTCCAGGCAAGGGGCT GGAGTGGGTGGCAGTTATTTGGTATGATGAAGT AATAAATACTATGCAGACTCCGTGAAGGGCCGA TTCACCATCTCCAGAGACAATTCCAAGAACACGC TGTTTCTGCAAATGAACAGCTGAGAGCCGAGG ACACGGCTGTGTATTACTGTGCGAGCGATCGCAA TATAGTGGGAGCTACTACTTTGAGTCTCTGGGGC CAGGGAACCCTGGTCACCGTCTCCTCA<br>SEQ ID NO: 29849 |
| | | AA | EIVMTQSPATLSLSPGERATLSCRASLSVVNSLA WYQQKPGQAPRLLIYGASTRATGIPARFSGSGSG TEFTLTISSLQSEDFAIYYCQQYNDWPCSFGQGT KLEIK<br>SEQ ID NO: 25844 | QVQLVESGGGVVQPGRSLRLSCTASGFTFSSYGMH WVRQAPGKGLEWVAVIWYDGSNKYYADSVKGRF TISRDNSKNTLFLQMNSLRAEDTAVYYCASDRNIV GATYFESWGQGTLVTVSS<br>SEQ ID NO: 29850 |

FIGURE 50
(Continued)

| | | | | |
|---|---|---|---|---|
| iPS:434675 | 21-225_79G6 | NA | GACATCGTGATGACCCAGTCTCCAGACTGCCT GGCTGTGTCTCTGGGCGAGAGGGCCACCATCA GCTGCATGTCCAGCAGAGTGTTTACACAGC TTCAACAATAAGAACTACTTAACTTGGTACCA GCAGAAACCAGGACAGCCTCCTAAGCTGCTCA TTTACTGGGCATCTACTTGGGAATCCGGGGTC CCTGACCGATTCAGTGGCAGCGGGTCTGGGAC AGATTTCAGTCTCCGATCGGCAGCCTGCAGG CTGAAGATGTGGCAGTTTATTACTGTCAGCAA TATTATAGTATTCCTCCGACGTTCGGCCAAGG GACCAAGGTGGAAATCAAA SEQ ID NO: 25845 | CAGGTGCAGCTGGTGCAGTCTGGGGCTGAGGTG AAGAAGCCTGGGGCCTCAGTGAAGGTCTCCTGC AAGGCTTCTGGATTCACCTTCACCAATTATGATA TCAACTGGGTGCGACAGGCCACTGGACAAGGGC TTGAGTGGATGGGATGGATGCACCCTAACAGTGG TAACACAGGCTTTGCACAGAAGTTCCAGGCAG AGTCACCATGACCAGGAACACCTCCATAAGCAC AGCCTACATGGAACTGAGCAGCCTGAGATCTGA GGACACGGCCGTGTATTACTGTGCGGTTTCCAGT GGCTGGTACGTTGACCCCTGGGGCCAGGGA ACCCTGGTCACCGTCCTCTCA SEQ ID NO: 29851 |
| | | AA | DIVMTQSPDCLAVSLGERATISCMSSQSVLHSFN NKNYLTWYQQKPGQPPKLLIYWASTWESGVPD RFSGSGSGTDFSLPIGSLQAEDVAVYYCQQYYSI PPTFGQGTKVEIK SEQ ID NO: 25846 | QVQLVQSGAEVKKPGASVKVSCKASGFTFTNYDIN WVRQATGQGLEWMGWMHPNSGNTGFAQKFQGR VTMTRNTSISTAYMELSSLRSEDTAVYYCAVSSGW YWFDPWGQGTLVTVSS SEQ ID NO: 29852 |
| iPS:434679 | 21-225_79G7 | NA | GACATCGTGATGACCCAGTCTCCAGACTCCCT GGCTGTGTCTCTGGGCGAGAGGGCCACCATCA ACTGCAAGTCCAGCCAGAGTGTTTTGTACAGC TCCAACAGTCACAACTACTTAGCTTGGTACCA GCAGAAACCAGGACAGCCTCCTAAACTGCTCA TTTCTGGGCATCTATCCGGGAATCCGGGGTC CCTGACCGATTCAGTGGCAGCGGGTCTGGGAC AGATTTCACTCTCTCCATCAGCAGCATGCAGG CTGAAGATGTGGCAGTTTATTACTGTCAGCAA CTGTATAGTACTCCGTGCAGTTTGGCCAGGG GACCAAGCTGGAGATCAAA SEQ ID NO: 25847 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCTCTGGACAAGGAC TTGAGTGGATGGGATGGATGCACAGAAGTTCCAGGCAG TAACACAGGCTATGCACAGAAGTTCCAGGCAG AGTCACCATGACCAGGAACACCTCCATAAGCAC AGCCTACATGGAGCTGAGCAGCCTGAGATCTGA GGACACGGCCGTATATTACTGTGCGTATAGTAGT GGCTGGTACAAATTTGACTACTGGAGCCAGGGA ACCCTGGTCACCGTCCTCTCA SEQ ID NO: 29853 |

FIGURE 50
(Continued)

| | | | | |
|---|---|---|---|---|
| iPS:434685 | 21-225_79E9 | AA | DIVMTQSPDSLAVSLGERATINCKSSQSVLYSSN SHNYLAWYQQKPGQPPKLLIFWASIRESGVPDR FSGSGSGTDFTLSISSMQAEDVAVYYCQQYYSTP CSFGQGTKLEIK<br>SEQ ID NO: 25848 | QVQLVQSGAEVKKPGASVKVSCKASGYTFTNYDIN WVRQASGQGLEWMGWMHPNSGNTGYAQKFQGR VTMTRNTSISTAYMELSSLRSEDSAVYYCAYSSGW YKFDYWSQGTLVTVSS<br>SEQ ID NO: 29854 |
| | | NA | GACATCGTGATGACCCAGTCTCCAGACTCCCT GGCTGTGTCTCTGGGCGAGAGGGCCACCATCA ACTGTAAGTCCAGCCAGAGTGTATTTATACAGC TCCAACAATAATAACTACTTAGCTTGGTTCCA GCAGAAACCAGGACAGCCTCCTAAGCTGCTCA TTTATTGGGCATCTACCCGGGAATCCGGGGTC CCTGACCGATTCAGTGGCAGCGGGTGTGGGAC AGATTTCACTCTCACCATCAGCAGCCTGCAGG CTGAAGATGTGGCAGTTTATTACTGTCAGCAA TATTATATTACTCCTCCGACGTTCGGCCAAGG GACCAAGGTGGAAATCAAA<br>SEQ ID NO: 25849 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCATCCTAACAGTGG TAACACAGGCTATGCACAGAAGTTCCAGGGCAG AGTCACCATGACCAGGAACACCTCCATAAGCAC AGCCTACATGGAACTGAGCAGCCTGAGATCTGA GGACACGGCCGTGTATTACTGTGCGAGTAGCAGT GGCTGGTACTACTTTGACTACTGGGGCCAGGGAA CCCTGGTCACCGTCTCCTCA<br>SEQ ID NO: 29855 |
| | | AA | DIVMTQSPDSLAVSLGERATINCKSSQSILYSSNN NNYLAWFQQKPGQPPKLLIYWASTRESGVPDRF SGSGCGTDFTLTISSLQAEDVAVYYCQQYYITPP TFGQGTKVEIK<br>SEQ ID NO: 25850 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCASSSGW YYFDYWGQGTLVTVSS<br>SEQ ID NO: 29856 |

FIGURE 50
(Continued)

| | | | | |
|---|---|---|---|---|
| iPS:434687 | 21-225_75A5 | NA | GAAATTGTGTTGACGCAGTCTCCAGGCACCCTGTATTTGTCTCCAGGGGAAAGAGCCACCCTCTCATGCAGGGCCAGTCAGAGTGTTTACAGCAGCTACTTAGCCTGGTACCAGCAGAAACCTGGCCAGGCTCCCAGGCTCCTCATTTATGGTGCATCCAGCCGGGCCACTGGCATCCCAGACAGGTTCAGTGGCAGTGGGTCTGGGACAGACTTCGCTCTCACCATCAGCAGACTGGAGCCTGAAGATTTTGCAGTGTATTACTGTCAGCACTATGATAACTCACCGTGGACGTTCGGCCAAGGGACCAAGGTGGAAATCAAA SEQ ID NO: 25851 | CAGGTGCAGCTACAGCAGTGGGGCGCAGGACTGTTGAAGCCTTCGGAGACCCTGTCCCTCACCTGCGCTGTCCATGTGGGTCCTTCAGTGGTTGTACTGGAGCTGGATCCGCCAGCCCCAGGGAAGGGGCTGGAGTGGATTGGGGAAATCAATCAATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA SEQ ID NO: 29857 |
| | | AA | EIVLTQSPGTLYLSPGERATLSCRASQSVYSSYLAWYQQKPGQAPRLLIYGASSRATGIPDRFSGSGSGTDFALTISRLEPEDFAVYYCQHYDNSPWTFGQGTKVEIK SEQ ID NO: 25852 | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTVSS SEQ ID NO: 29858 |
| iPS:434689 | 21-225_79G10 | NA | GACATCGTTATGACCCAGTCTCCAGACTCCCTGGCTGTGTCTCTGGGCGAGAGGGCCACCATCAATTGCAAGTCCAGTCAGAGTGTTTATTCAGCTCCAACAATTATAATTACTTAGCTTGGTACCAGCAGAGACCAAGGACAGCCTCATAACCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGCTGATGTGGCAGTTTATTACTGTCAGCAATATCATAGTTTCCTCTGACGTTCGGCCAAGGGACCACGGTGCAAATCAAA SEQ ID NO: 25853 | CAGGTGCAGTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGAACCTAACAGTGGTAACACAGGCTATGCACAGAAGTTCCAGGGCAGAGTCACCATGACCAGGAACACCTCCACAAGCACAGCCCACATGGAGCTGAGCAGCCTGAGATCTGAGGACACGGCCGTGTATTACTGTGCGGTCTCCAGTGGCTGGAACTGTTCGACCCCTGGGCCAAGGAACCCTGGTCACCGTCTCCTCA SEQ ID NO: 29859 |

FIGURE 50
(Continued)

| | | | | |
|---|---|---|---|---|
| iPS:434691 | 21-225_75G7 | AA | DIVMTQSPDSLAVSLGERATINCKSSQSVLFSSN NYNYLAWYQQRPGQPHNLLIYWASTRESGVPD RFSGSGSGTDFTLTISSLQAADVAVYYCQQYHSS PLTFGQGTTVQIK<br><br>SEQ ID NO: 25854 | QVQLVQSGAEVKKPGASVKVSCKASGYTFTNYDIN NYNYLAWYQQRPGQPHNLLIYWASTRESGVPD<br>WVRQATGQGLEWMGWMNPNSGNTGYAQKFQGR<br>VTMTRNTSTSTAHMELSSLRSEDTAVYYCAVSSGW<br>NWFDPWGQGTLVTVSS<br><br>SEQ ID NO: 29860 |
| | | NA | GAAATTGTGTTGACGCAGTCTCCAGGCACCCT GTCTTTGTCTCCAGGGGAAAGAGCCACCCTCT CCTGCAGGGCCAGGCAGAGTGTTGACAGCAGT TATTTAGCCTGGTACCAGCAGAAACGTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGGCTGGAGCCTGAAGATTTTGCAG TATATTACTGTCAGCAGTATGAAAGCTCACCG TGGACGTTCGGCCAAGGGACCAAGGTGGAAA TCAAA<br><br>SEQ ID NO: 25855 | CAGGTGCAGCTACAGAGCAGTGGGGCGCAGGACTG TTGAAGCCTTCGGAGACCCTGTCCCTCACCTGCA CTGTCTCTATGTGGGGCCTTCAGTGGTTCCTACTG GAGCTGGATCCGCCAGTCCCCAGGGAAGGGGCT GGAGTGGATTGGGGAAATCAATTATAGGGGAAG CACCAACTACAACCCGTCCCTCAAGAGTCGAGTC ACCATATCAGTAGACACGTCCAAGAACCAGTTCT CCCTGAACCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br><br>SEQ ID NO: 29861 |
| | | AA | EIVLTQSPGTLSLSPGERATLSCRARQSVDSSYLA WYQQKRGQAPRLLIYGASSRATGIPDRFSGSGSG TDFTLTISRLEPEDFAVYYCQQYESSPWTFGQGT KVEIK<br><br>SEQ ID NO: 25856 | QVQLQQWGAGLLKPSETLSLTCTVYGGAFSGSYW SWIRQSPGKGLEWIGEINYRGSTNYNPSLKSRVTIS VDTSKNQFSLNLSSVTAADTAVYYCARDYGGMDV WGQGTTVTVSS<br><br>SEQ ID NO: 29862 |

FIGURE 50
(Continued)

| | | | |
|---|---|---|---|
| iPS:434693 | 21-225_79F11 | NA | GAAATTGTGTTGACGCAGTCTCCAGGCACCCT GTCTTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTCTGATAACTCACCGT GGACGTTCGGCCAAGGGACCAAGGTGGAAAT CAAA SEQ ID NO: 25857 |
| | | AA | EIVLTQSPGTLSLSPGERATLSCRASQSVYSSYLA WYQQKPGQAPRLLIYGASSRATGIPDRFSGSGSG TDFALTISRLEPEDFAVYYCQHSDNSPWTFGQGT KVEIK SEQ ID NO: 25858 | CAGGTGCAGCTACAGCAGTGGGGCGCAGGACTG TTGAAGCCTTCGGAGACCCTGTCCCTCACCTGCG CTGTCCATGTGGGTCCTTCAGTGGTTGTACTG GAGCTGGATCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGGACAC GGCTGTGTATTACTGTGCGAGGGACTACGGCGGT ATGGACGTCTGGGGCCAAGGGACCACGGTCACC GTCTCCTCA SEQ ID NO: 29863 |
| | | | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 29864 |
| iPS:434697 | 21-225_79F12 | NA | GACATCGTGATGACCCAGTCTCCAGACTCCCT GGCTGTGTCTCTGGGCGAGAGGGCCACCATCA ACTGCAAGTCCAGCCAGAGTGTATTTATACAGC TCCAACAATTACAACTACTTAGCTTGGTACCA GCAGAAACCAGGACAGCCTCCTAAGTTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGGTGACGTTCGGCCAAGG GACCAAGGTGGAAATCAAA SEQ ID NO: 25859 | CAGGTGCAGCTGGTGCAGTCTGGGGCTGAGGTG AAGAAGCCTGGGGCCTCTGTGAAGGTCTCCTGCA AGGCTTCTGGATACACCTTCACCAATTATGATAT CAACTGGGTGCGACAGGCCACTGGACAAGGGCT TGAGTGGATGGGATGGATGAACCCTAACAGTGG TAACACAGGCTATGCACAGAAGTTCCAGGGCAG AGTCACCATGACCAGAAACACCTCCATAAGCAC AGCCTACATGGAGCTGAGCAGCCTGAGATCTGA GGACACGGCCGTATATTACTGTGCGAGTAGCAGT GCTCGGTACTTCTTTGACTACTGGGGCCAGGGAA CCCTGGTCACCGTCTCCTCA SEQ ID NO: 29865 |

FIGURE 50
(Continued)

| | | | |
|---|---|---|---|
| iPS:434699 | | AA | DIVMTQSPDSLAVSLGERATINCKSSQSILYSSNNYNYLAWYQQKPGQPPKLLIYWASTRESGVPDRFSGSGSGTDFTLTISSLQAEDVAVYYCQQYYSTPWTFGQGTKVEIK<br>SEQ ID NO: 25860 | QVQLVQSGAEVKKPGASVKVSCKASGYTFTNYDINWVRQATGQGLEWMGWMNPNSGNTGYAQKFQGRVTMTRNTSISTAYMELSSLRSEDTAVYYCASSSGWYFFDYWGQGTLVTLSS<br>SEQ ID NO: 29866 |
| | | NA | GAAATTGTGTTGACGCAGTCTCCAGGCACCCTGTATTTGTCTCCAGGGGAAAGAGCCACCCTCTCATGCAGGGCCAGTCAGAGTGTTTACAGCAGCTACTTAGCCTGGTACCAGCAGAAACCTGGCCAGGCTCCCAGGCTCCTCATTTATGGTGCATCAGCGCGGTCCACTGGCATCCCAGACAGGTTCAGTGGCAGTGGGTCTGGGACAGACTTCGCTCTCACCATCAGCAGACTGGAGCCTGAAGATTGTGCAGTGTATTACTGTCAGCACTCTGATAACTCACCGTGGACGTTCGGCCAAGGGACCAAGGTGGAAATCAAA<br>SEQ ID NO: 25861 | CAGGTGCAGTCTACAGCAGTGGGGCGCAGGACTGTTGAAGCCTTCGGAGACCCTGTCCCTCACCTGCGCTGTCCATGGTGGGTCCTTCAGTGGTTGCTACTGGAGCTGGATCCGCCAGCCCCAGGGAAGGGGCTGGAGTGGATTGGGGAAATCAATCATAGTGGAAGCACCAACTACAACCCGTCCCTCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA<br>SEQ ID NO: 29867 |
| 21-225_79G12 | | AA | EIVLTQSPGTLYLSPGERATLSCRASQSVYSSYLAWYQQKPGQAPRLLIYGASSRSTGIPDRFSGSGSGTDFALTISRLEPEDCAVYYCQHSDNSPWTFGQGTKVEIK<br>SEQ ID NO: 25862 | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTVSS<br>SEQ ID NO: 29868 |

FIGURE 50
(Continued)

| | | | | |
|---|---|---|---|---|
| iPS:434701 | 21-225_80A1 | NA | GAAATTGTGTTGACGCAGTCTCCAGGCACCCG GTATTTGTCTCCAGGGGAAAGAGCCACCCTCT CATGCAGGGCCAGTCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTGTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA SEQ ID NO: 25863 | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGGAAGGGCT GGAGTGGATTGGGGAAATCAATCATAGTGGAAG CACCAACTACACAAACCCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29869 |
| | | AA | EIVLTQSPGTRYLSPGERATLSCRASQSVYSSYL AWYQQKPGQAPRLLIYGASSRSTGIPDRFSGSGC GTDFALTISRVEPEDCAVYYCQHSDNSPWTFGQ GTKVEIK SEQ ID NO: 25864 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 29870 |
| iPS:434703 | 21-225_80C1 | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTCTGATAATAACTCACCGT GGACGTTCGGCCAAGGGACCAAGGTGGAAAT CAAA SEQ ID NO: 25865 | CAGGTGCAGCTACAGCAGTGGGGCGCAGGACTG TTGAAGCCTTCGGAGACCCTGTCCCTCACCTGCG CTGTCCATGGTGGGTCTTCAGTGGTTGCTACTG GAGCTGGATCCGCCAGCCCCAGGGAAGGGCT GGAGTGGATTGGGGAAATCAATCATAGTGGAAG CACCAACTACACAAACCCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCCAC GTCTCCTCA SEQ ID NO: 29871 |

FIGURE 50
(Continued)

| | | | |
|---|---|---|---|
| iPS:434705 | 21-225_80A2 | AA | EIVLTQSPGTLYLSPGERATLSCRASQSVYSSYLA WYQQKPGQAPRLLIYGASSRSTGIPDRFSGSGSG TDFALTISRVEPEDCAVYYCQHSDNSPWTFGQG TKVEIK<br>SEQ ID NO: 25866 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29872 |
| | | NA | GAATTTATGTTGACGCAGTCTCCAGGCACCCT GTATTTGTCTCCAGGGGAAAGAGCCACCCTCT CGTGCAGGGCCAGTCAGAGTGTTAGCAGCAGC TACTTAGTCTGGTATCAGCAGAAACCTGGCCA GGCTCCCAGGCTCCTCATCTATGGTGCATCA CCAGGGCCACTGGCATCCCAGACAGGTTCAGT GGCAGTGGGTCTGGGACAGACTTCACTCTCAC CATCAGCAGACTGGAGCCTGAATATTTGCAG TTTATTACTGTCAGCAGTATGGTTGCTCACCGC TCACTTTCGGCGGAGGGACCAAGGTGGAGATC ACA<br>SEQ ID NO: 25867 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGC TTGAGTGGATGGGATGGATGCACAGAAGTTCCAGGGCAG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA<br>SEQ ID NO: 29873 |
| | | AA | EFMLTQSPGTLYLSPGERATLSCRASQSVSSSYL VWYQQKPGQAPRLLIYGASTRATGIPDRFSGSGS GTDFTLTISRLEPEYFAVYYCQQYGCSPLTFGGG TKVEIT<br>SEQ ID NO: 25868 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br>SEQ ID NO: 29874 |

FIGURE 50
(Continued)

| | | | |
|---|---|---|---|
| iPS:434707 | 21-225_80D3 | NA | GACATCGTGATGACCCAGTCTCCAGATTGCCT GGCTGTGTCTCTGGGCGAGAGGGCCACCATCA ACTGCAAGTCCAGCCAGAGTGTTTTATACACC TCCAACAATAACAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCACT ACAATGAAACTCCAGGAAGTTGTCCAAGTG ACCAAGGTGGAAATCACA SEQ ID NO: 25869 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGTTCGACCCCTGGGCCAGGGA ACCCTGGTCACCGTCTCCTCA SEQ ID NO: 29875 |
| | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYNET PGKFVQVTKVEIT SEQ ID NO: 25870 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS SEQ ID NO: 29876 |
| iPS:434709 | 21-225_80E3 | NA | GAAATTGTGTTGACGCAGTCTCCAGGCACCCT GTATTGTCTTCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCA GCCGGTCCACTGGCATCCCAGACAGGTTCAGT GGCAGTGGGTCTGGGACAGACTTCGCTCTCAC CATCAGCAGAGTGGAGCCTGAAGATTTTGCAG TGTATTACTGTCAGCATTCTGATAACTCACCGT GGACGTTCGGCCAAGGGACCAAGGTGGAAAT CAAA SEQ ID NO: 25871 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTGCTACTG GAGTCTGGATCCGCCAGCCCCCAGGGAAGGGCT GGAGTGGATTGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29877 |

FIGURE 50
(Continued)

| | | | | |
|---|---|---|---|---|
| iPS:434711 | 21-225_80H3 | AA | EIVLTQSPGTLYLSSGERATLSCRASQSVYSSYLA WYQQKPGQAPRLLIYGASSRSTGIPDRFSGSGCG TDFALTISRVEPEDFAVYYCQHSDNSPWTFGQG TKVEIK<br>SEQ ID NO: 25872 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br>SEQ ID NO: 29878 |
| | | NA | GACATCGTGATGACCCAGTCTCCAGACTCCCT GGCTGTGTCTCTGGGCGAGAGGGCCACCACCA ATTGTAAGTCCAGCCAGAGTGTTTTACACAGG TCCAACAATTACAACTACTTAGCGTGGTACCA GCAGAAACCAGGACAGGCTCCTAAGCTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAAA<br>SEQ ID NO: 25873 | CAGGTGCAGCTGGTGCAGTCTGGGGCTGAGGTG AAGAAGCCTGGGGCCTCAGTGAAGGTCTCCTGC AAGGCTTCTGGATACACCTTGACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGCA GAGTCACCATGACCAGGAACACCTCCATAAGCA CAGCCTACATGGAACTGAGCAGCCTGAGATCTG AGGACACGGCCGTGTATTACTGTGGGAGTACCA GTGGCTGGAACTTCTTTGACTACTGGGGCCAGGG AACCCTGGTCACCGTCTCCTCA<br>SEQ ID NO: 29879 |
| | | AA | DIVMTQSPDSLAVSLGERATTNCKSSQSVLHRSN NYNYLAWYQQKPGQPPKLLIYWASTRESGVPD RFSGSGSGTDFTLTISSLQAEDVAVYYCQQYYST PPTFGQGTKVEIK<br>SEQ ID NO: 25874 | QVQLVQSGAEVKKPGASVKVSCKASGYTLTNYDI NWVRQATGQGLEWMGWMNPNSGNTGYAQKFQG RVTMTRNTSISTAYMELSSLRSEDTAVYYCGSTSG WNFFDYWGQGTLVTVSS<br>SEQ ID NO: 29880 |

FIGURE 50
(Continued)

| | | | | |
|---|---|---|---|---|
| iPS:434715 | 21-225_80D5 | NA | GAACTTGTGTTGACGCAGTCTCCAGGCACCCT GTCTTTGTCTCCAGGGAAAGAGTCACCCTCT CCTGCAGGGCCAGTCAGTCAGAATATTTACAGCAGC TACTTAGCCTGGTACCAGCAGAAACCTGGCCA GGCTCCCAGACTCCTCATCTATGGTGCATCCA GCAGGGCCACTGGCATCCCAGACAGGTTCAGT GGCAGTGGGTCTGGGACAGACTTCACTCTCAC CATCACCAGACTGGAGCCTGAAGATTTTGCAG TGTATTGCTGTCAGCAGTATGAAAGCTCACCG TGGACCTTCGGCCAAGGGACCAAGGTGGAAA TCAAA SEQ ID NO: 25875 | CAAGTGCAGCTACAGCAGTGGGGCGCAGGACTG TTGAAGCCTTCGGAGACCCTGTCCCTCACCTGCG CTGTCTATGGTGGGTCCTTCAGTGGTCCTACTG GAGCTGGATCCGCCAGCCCCCGGGAAGGGCT GGAGTGGATTGGGGAAATCAATCATAGTGGAAG CACCAACTACAACCCGTCCCTCAAGAGTCGAGTC ACCATATCAGTAGACACGTCAAGAACCAGTTCT CCCTGAAACTGACCTCTGTGACCGCCGCGGACAT GGCTGTGTATTACTGTGCGAGAGACTACGGGGGT TTGGACGTCTGGGGCCAAGGGACCACGGTCACC GTCTCCTCA SEQ ID NO: 29881 |
| | | AA | ELVLTQSPGTLSLSPGKRVTLSCRASQNIYSSYLA WYQQKPGQAPRLLIYGASSRATGIPDRFSGSGSG TDFTLTITRLEPEDFAVYCCQQYESSPWTFGQGT KVEIK SEQ ID NO: 25876 | QVQLQQWGAGLLKPSEPLSLTCAVYGGSFSGPYW SWIRQPPGKGLEWIGEINHSGSTNYNPSLKSRVTISV DTSKNQFSLKLTSVTAADMAVYYCARDYGGLDV WGQGTTVTVSS SEQ ID NO: 29882 |
| iPS:434717 | 21-225_80A6 | NA | GAAATTGTGTTGACGCAGTCTCCAGGCACCCT GTCTTTGTCTCCAGGGGAAATACCACCCTCT CCTGCAGGGCCAGTCAGAGTGTTGACAGCGGC TACTTAGCCTGGTACCAGCAGAAACCTGGCCA GGCTCCCAGGCCCCTCATCTATGGTGCATCCA GCAGGGCCCCTGGCATCCCAGACAGGTTCAGT GGCAGTGGGTCTGGGACAGACTTCACTCTCAC CATCAGCAGACTGGAAGCTGAAGATTTTGCAG TGTATTACTGTCAGCAGTATGAAAGCTCACCG TGGACGTTCGGCCAAGGGACCAAGGTGGAAA TCAAA SEQ ID NO: 25877 | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTGCTACTG GAGCTGGATCCGCCAGCCCCCAGGAAAGGGGCT GGAGTGGATTGGGGAAATCAATCATAGTGGAAG GACCAACTACAACCCGTCCCTCAAGAGTCGAGTC ACCATATCAGTAGACACGTCCGAGAAGCAGTTCT CCCTGAAGCTGAGCTCTGTGACCGCCGCGGACAC GGCTGTGTATTACTGTGCGAGAGACTACGGTGGG CTTGACTACTGGGGCCAGGGAACCCTGGTCACCG TCTCCTCA SEQ ID NO: 29883 |

FIGURE 50
(Continued)

| | | | |
|---|---|---|---|
| iPS:434725 | 21-225_80H7 | AA | EIVLTQSPGTLSLSPGEIPTLSCRASQSVDSGYLA WYQQKPGQAPRLLIYGASSRAPGIPDRFSGSGSG TDFTLTISRLEPEDFAVYYCQQYESSPWTFGQGT KVEIK<br><br>SEQ ID NO: 25878 | QVQLQQWGAGLLKPSETLSLTCAVYGGSFSGCYW SWIRQPPGKGLEWIGEINHSGRTNYNPSLKSRVTIS VDTSEKQFSLKLSSVTAADTAVYYCARDYGGLDY WGQGTLVTVSS<br><br>SEQ ID NO: 29884 |
| | | NA | GAAATTGTGTTGACGCAGTCTCCAGGCACCCT GTCTTTGTCTCCAGGGGAAAGAGCCACCCTCT CCTGCAGGGCCAGTCAGAGTATTAACAGCAAC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTTTTACTGTCAGCAGTATGAGAGCTCACCG TGGACGTTCGGCCAAGGGACCAAGGTGGAAA TCAAA<br><br>SEQ ID NO: 25879 | CAGGTGCAGTTACAGCAGTGGGGCGCAGGACTG TTGAAGCCTTCGGAGACCCTGTCCCTCACCTGCG CTGTCTATGTTGGGTCCTTCAGTGGTTCCTACTGG AGCTGGATCCGCCAGCCCCCAGGGAAGGGGCTA GAGTGGATTGGGAAATCAATCAAAGTGGACGC ACCAACTACAACCCGTCCCTCAAGAGTCGAGTCA CCATATCAGTAGACACGTCCAAGAACCAGTTCTC CCTGAAGCTGAGCTCTGTGACCGCCGCGGACACG GCTGTGTATTACTGTGCGAGAGACTACGGGGGTA TAGACGTCTGGGGCCAAGGGACCACGGTCACCG TCTCCTCA<br><br>SEQ ID NO: 29885 |
| | | AA | EIVLTQSPGTLSLSPGERATLSCRASQSINSNYLA WYQQKPGQAPRLLIYGASSSRATGIPDRFSGSGSG TDFTLTISRLEPEDFAVFYCQQYESSPWTFGQGT KVEIK<br><br>SEQ ID NO: 25880 | QVQLQQWGAGLLKPSETLSLTCAVYVGSFSGSYW SWIRQPPGKGLEWIGEINQSGRTNYNPSLKSRVTIS VDTSKNQFSLKLSSVTAADTAVYYCARDYGGIDV WGQGTTVTVSS<br><br>SEQ ID NO: 29886 |

FIGURE 50
(Continued)

| | | | | |
|---|---|---|---|---|
| iPS:434729 | 21-225_80B12 | NA | GACATCGTGTTGACCCAGTCGCCAGACTCCCT GGCTGTGTCTCTGGGCGAGAGGGCCACCATCA ACTGCAAGTCCAGACAGAGTGTTTATACAGC TCCAACAATTACAACTACTTAACTTGGTACCA GCAGAAACCAGGACAGCCTCCTAAGCTGCTCA TTTACTGGGCATCTACCCGGAATCGGGGTC CCTGACCGATTCAGTGGCAGCGGGTCTGGGAC AGATTTCACTCTCACCATCAGCAGCCTGCAGG CTGAAGACGTGGCAGTTTATTACTGTCAGCAA TATTATAGTTCTCCTCCTACTTTCGGCGGAGGG ACCAAGGTGGAGATCAAA | CAGGTGCAGCTGGTGCAGTCTGGGGCTGAGGTG AAGAAGCCTGGGGCCTCAGTGAAGGTCTCCTGC AAGACTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGTCA GAGTCACCATGACCAGGAACACCTCCATAAGCA CAGCCTACATGGAGCTGAGCAGCCTGAGATCTG AGGACACGGCCGTCTATTACTGTGCGTATAGCAG TGGCTGGTACATCTTTGACTACTGGGGCCAGGGA ACCCTGGTCACCGTCTCCTCA |
| | | | SEQ ID NO: 25881 | SEQ ID NO: 29887 |
| | | AA | DIVLTQSPDSLAVSLGERATINCKSRQSVLYSSN NYNYLTWYQQKPGQPPKLLIYWASTRESGVPDR FSGSGSGTDFTLTISSLQAEDVAVYYCQQYYSSP PTFGGGTKVEIK | QVQLVQSGAEVKKPGASVKVSCKTSGYTFTNYDIN WVRQATGQGLEWMGWMNPNSGNTGYAQKFQVR VTMTRNTSISTAYMELSSLRSEDTAVYYCAYSSGW YIFDYWGQGTLVTVSS |
| | | | SEQ ID NO: 25882 | SEQ ID NO: 29888 |
| iPS:434731 | 21-225_80E9 | NA | GACATCGTGATGACCCAGTCTCCAGATTGCCT GGCTGTGTCTCTGGGCGAGAGGGCCACCATCA ACTGCAAGTCCAGCCAGAGTGTTTTATACAC TCCAACAATAACAACTACTTAGCTTGGTACCA GCAGAAACCAGGACAGCCTCCTAAGCTGCTCA TTTACTGGGCATCTACCCGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCAA TATTATAATACTCCGTGGACGTTCGTCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACAGAACAGTGG TAACACAGGCTATGCACAGAAGTTCCAGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA |
| | | | SEQ ID NO: 25883 | SEQ ID NO: 29889 |

FIGURE 50
(Continued)

| | | | |
|---|---|---|---|
| iPS:434735 | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQQYYNT PWTFVQGTKVEIK<br>SEQ ID NO: 25884 | QVQLVQSGAEVKKPGASVKVSCKASGYTFNYDIN WVRQATGQGLEWMGWMHPNSGNTGYAQKFQGR VTMTRNTSISTAYMELSSLRSEDTAVYYCAISSGW YWFDPWGQGTLVTVSS<br>SEQ ID NO: 29890 |
| | 21-225_80B10 | NA | GAAATTGTGTTGACGCAGTCTCCAGGCACCCT GTCTTTGTCTCCAGGGGAAAGAGCCACCCTCT CCTGCAGGGCCAGTCAGAGTGTTGACAGCAGC TACTTAGCCTGGTACCAGCAGAAACCTGGCCA GGCTCCCAGGCTCCTCATCTATGGTGCATCCA GCAGGGCCCCTGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGCTCACCG TGGACGTTCGGCCAAGGGACCAAGGTGGAAA TCAAA<br>SEQ ID NO: 25885 | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCGTCCTCCTCAAGAGTCGAGTC ACCATATCAGTAGACACGTCAAGAACCAGTTCT CCCTGAAGCTGAGCTCTGTGACCGCCGCGGACAC GGCTGTGTATTACTGTGCGAGAGACTACGGTGGG CTTGACTACTGGGGCCAGGGAACCCTGGTCACCG TCTCCTCA<br>SEQ ID NO: 29891 |
| | | AA | EIVLTQSPGTLSLSPGERATLSCRASQSVDSSYLA WYQQKPGQAPRLLIYGASSRAPGIPDRFSGSGSG TDFTLTISRLEPEDFAVYYCQQYESSPWTFGQGT KVEIK<br>SEQ ID NO: 25886 | QVQLQQWGAGLLKPSETLSLTCAVYGGSFSGCYW SWIRQPPGKGLEWIGEINHSGSTNYNPSLKSRVTISV DTSKNQFSLKLSSVTAADTAVYYCARDYGGLDYW GQGTLVTVSS<br>SEQ ID NO: 29892 |

FIGURE 50
(Continued)

| | | | | |
|---|---|---|---|---|
| iPS:434737 | 21-225_74G6 | NA | GACATCCAGATGACCCAGTCTCCATCCTCACT GTCTGCATCAGTAGGAGACAGAGTCACCATCA CTTGTCGGGCGAGTCAGGGCATTGGCAAGTAT TTAGCCTGGTTTCAGCAGAAACCAGGGAAAGC CCCTAAGTCCCTGATCTATACTGCATCCAGTTT GCAAAGTGGGGGCCCATCAAAGTTCAGCGGC AGTGGATCTGGGACAGATTTCACTCTCACCAT CAGCAGCCTGCAGTATGAAGATTTTGCAACTT ATTACTGCCAACAGTACAGTAATTACCCGCTC ACTTTCGGCGGAGGGACCAAGGTGGAGATCA AT SEQ ID NO: 25887 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGGCAG CTATGGTTATGACGGCCTTGACTACTGGGGCCAG GGAACCCTGGTCACCGTCTCCTCA SEQ ID NO: 29893 |
| | | AA | DIQMTQSPSSLSASVGDRVTITCRASQGIGKYLA WFQQKPGKAPKSLIYTTSSLQSGAPSKFSGSGSG TDFTLTISSLQYEDFATYYCQQYSNYPLTFGGGT KVEIN SEQ ID NO: 25888 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDGSYG YDGLDYWGQGTLVTVSS SEQ ID NO: 29894 |
| iPS:434741 | 21-225_80C11 | NA | GACATCCAGATGACCCAGTCTCCATCCTCACT GTCTGTCTCTGTGGGCGACAGAGTCACCATCA CTTGTCGGGCGAGTCAGGGCATTGGCAGGTAT TTAGCCTGGTTTCAGCAGAAACCAGGGAGAGC CCCTAAGTCCCTGATCTATACTGCATCCAGTTT GCAAAGTGGGGTCCCATCAAAGTTCAGCGGC AGTGGATCTGGGACAGATTTCACTCTCACCAT CAGCAGCCTGCAGCCTGAAGATTTTGCAACTT ATTACTGCCAACAGTACAGTAATTACCCGCTC ACTTTCGGCGGAGGGACCAAGGTGGAGATCA AT SEQ ID NO: 25889 | CAGGTGCAGCTGGTGGAGTCTGGGGGAGGCGTG GTCCAGCCTGGGAGGTCCCTGAGACTCTCCTGTG CAGCGTCTGGATTCACCTTCAGCAGCTATGGCAT GCACTGGGTCCGCCAGGCTCCAGGCAAGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTCTCTGCAAATGAACAGCCTGAGAGCCGAGG ACACGGCTGTGTATTACTGTGCGAGAGATGGCAG CTATGGGTATGACGGCCTTGACTACTGGGGCCAG GGAACCCTGGTCACCGTCTCCTCA SEQ ID NO: 29895 |

FIGURE 50
(Continued)

| | | | |
|---|---|---|---|
| iPS:434743 | 21-225_74A4 | AA | DIQMTQSPSSLSASVGDRVTITCRASQGIGRYLA WFQQKPGRAPKSLIYTASSLQSGAPSKFSGSGSG TDFTLTISSLQPEDFATYYCQQYSNYPLTFGGGT KVEIN<br>SEQ ID NO: 25890 | QVQLVESGGGVVQPGRSLRLSCAASGFTFSSYGMH WVRQAPGKGLEWVAVIWYDGSNKNYADSVKGRF TISRDNSKNTLSLQMNSLRAEDTAVYYCARDGSYG YDGLDYWGQGTLVTVSS<br>SEQ ID NO: 29896 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCA GCCGGTCCACTGGCATCCCAGACAGGTTCAGT GGCAGTGGGTGTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA<br>SEQ ID NO: 25891 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCTCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 29897 |
| | | AA | EIVLTQSPGTLYLSPGERATLSCRASQSVYSSYLA WYQQKPGQAPRLLIYGASSRSTGIPDRFSGSGCG TDFALTISRLEPEDCAVYYCQHSDNSPWTFGQG TKVEIK<br>SEQ ID NO: 25892 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29898 |

FIGURE 50
(Continued)

| | | | |
|---|---|---|---|
| iPS:434747 | 21-225_80C12 | NA | GAAATTGTGTTGACGCAGTCTCCAGGCACCCT GTATTGTCTGTCCAGGGGAAAGAGCCACCCTCT CGTGCAGGGCCAGTCAGAGTGTTAGCAGCAGC TACTTAGCCTGGTACCAGCAGAAACCTGGCCA GGCTCCCAGGCTCCTCATCTATGGTGCATCA CCAGGGCCACTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTAACTCACCG CTCACTTTCGGCGGAGGGACCAAGGTGGAGAT CAAA <br><br> SEQ ID NO: 25893 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAATGG TAACACAGGCTATGCACAGAAGTTCCAGGGCAG AGTCACCATGACCAGGAACACCTCCATAAGCAC AGCCTACATGGAGCTGAACAGCCTGAGATCTGA GGACACGGCCGTGTATTACTGTGCGATTAGCAGT GGCTGGTACTGTTCGACCCCTGGGGCCAGGGA ACCCTGGTCACCGTCTCCTTA <br><br> SEQ ID NO: 29899 |
| | | AA | EIVLTQSPGTLYLSPGERATLSCRASQSVSSSYLA WYQQKPGQAPRLLIYGASTRATGIPDRFSGSGSG TDFTLTISRLEPEYFAVYYCQQYGNSPLTFGGGT KVEIK <br><br> SEQ ID NO: 25894 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL <br><br> SEQ ID NO: 29900 |
| iPS:434751 | 21-225_80H12 | NA | GAAATTGTGTTGACGCAGTCTCCAGGCACCCT GTCTTTGTCTGTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCA GCCGGTCCACTGGCATCCCAGACAGGTTCAGT GGCAGTGGGTCTGGGACAGCCTGCTCTCAC CATCAGCAGACTGGAGCCTGAAGATTTTGCAG TGTATTACTGTCAGCAGCTCTGATAACTCACCGT GGACGTTCGGCCAAGGGACCAAGGTGGAAAT CAAA <br><br> SEQ ID NO: 25895 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTGCTACTG GAGCTGGATCCGCCAGCCCCAGGGAAGGGCT GGAGTGGATTGGGAAATCAATCATAGTGGAAG CACCAACTACAACCCGTCCCTCAAGAGTGGAGTC ACCATTTCAGTAGACACGTCCAAGAACCAGTTCT CCCTGAAGCTGAGCTCTGTGACCGCCGCGGACAC GGCTGTGTATTACTGTGCGGGACTACGGCGGT ATGGACGTCTGGGGCCAAGGGACCACGGTCACC GTCTCCTCA <br><br> SEQ ID NO: 29901 |

FIGURE 50
(Continued)

| | | AA | EIVLTQSPGTLSLSPGERATLSCRASQSVYSSYLA WYQQKPGQAPRLLIYGASSRSTGIPDRFSGSGSG TDFALTISRLEPEDFAVYYCQHSDNSPWTFGQGT KVEIK<br><br>SEQ ID NO: 25896 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29902 |
| | | NA | GAAATTGTGTTGACGCAGTCTCCAGGCACCCT GTATTTGTCTTCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTGTGGGACAGACTTCGCTCTCAC CATCAGCAGAGTTGGAGCCTGAAGATTGTGCAG TGTATTACTGTCAGCATTCTGATAACTCACCGT GGACGTTCGGCCAAGGGACCAAGGTGGAAAT CAAA<br><br>SEQ ID NO: 25897 | CAGGTGCAGCTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29903 |
| iPS:434759 | 21-225_81C5 | AA | EIVLTQSPGTLYLSSGERATLSCRASQSVYSSYLA WYQQKPGQAPRLLIYGASSRSTGIPDRFSGSGCG TDFALTISRVEPEDCAVYYCQHSDNSPWTFGQG TKVEIK<br><br>SEQ ID NO: 25898 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29904 |

FIGURE 50
(Continued)

| | | | |
|---|---|---|---|
| iPS:434761 | 21-225_81E5 | NA | GACATCGTTATGACCCAGTCTCCAGACTCCCT GGCTGTGTCTCTGGGCGAGAGGGCCACCATCA ATTGCAAGTCCAGCCAGAGTGTTTTATTCAGC TCCAACAATTATAATTACTTAGCTTGGTACCA GCAGAGACCAGGACAGGCCTCCTAACCTGCTCA TTTACTGGGCATCTACCCGGAGAATCCGGGGTC CCTGACCGATTCAGTGGCAGCGGGTCTGGGAC AGATTTCACTCTCACCATCAGCAGCCTGCAGG CTGCTGATGTGGCAGTTTATTACTGTCAGCAA TATTATAGTTCTCCTCGACGTTCGGCCAAGG GACCACGGTGCAAATCAAA SEQ ID NO: 25899 | CAGGTGCAGTTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGCT TGAGTGGATGGGATGGATGAACCCTAACAGTGG TAACACAGGCTATGCACAGAAGTTCCAGGGCAG AGTCACCATGACCAGGAACACCTCCACAAGCAC AGCCCACATGGAGCTGAGCAGCCTGAGATCTGA GGACACGGCCGTGTATTACTGTGCGGGTCCAGT GGCTGGAACTGGTTCGACCCCTGGGGCCAGGGA ACCCTGGTCACCGTCTCCTCA SEQ ID NO: 29905 |
| | | AA | DIVMTQSPDSLAVSLGERATINCKSSQSVLFSSN NYNYLAWYQQRPGQPPNLLIYWASTRESGVPD RFSGSGSGTDFTLTISSLQAADVAVYYCQQYYSS PLTFGQGTTVQIK SEQ ID NO: 25900 | QVQLVQSGAEVKKPGASVKVSCKASGYTFTNYDIN WVRQATGQGLEWMGWMNPNSGNTGYAQKFQGR VTMTRNTSTSTAHMELSSLRSEDTAVYYCAVSSGW NWFDPWGQGTLVTVSS SEQ ID NO: 29906 |
| iPS:434771 | 21-225_81F9 | NA | GACATCGTGATGACCCAGTCTCCAGATTGCCT GGCTGTGTCTCTGGGCGAGAGGGCCACCATCA ACTGCAAGTCCAGCCAGAGTGTTTTATACACC TCCAACAATAACAACTACTTAGCTTGGTACCA GCAGAAACCAGGACAGCCTCCTAAGCTGCTCA TTTACTGGGCATCTACCCGGAGAATCCGGGGTC CCTGACCGATTCAGTGGCAGCGGGTCTGGGAC AGATTTCACTCTCACCATCAGCAGCCTGCAGG CTGAAGATGTTGCAGTTTATTATCGTCAGCAC TACAATGATATACTCCAGGGAAGTTTGTCCAAGG CATCATGGTGGAAATCACA SEQ ID NO: 25901 | CAGGTGCAGCTGGTGCAGTCTGGGGCTGAGGTG AAGAAGCCTGGGGCCTCAGTGAAGGTCTCTGC AAGGCTTCTGGATACACCTTCACCAATTATGATA TCAACTGGGTGCGACAGGCCACTGGACAAGGC TTGAGTGGATGGGATGATGCACAGAAGTTCCAGGGCAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA SEQ ID NO: 29907 |

FIGURE 50
(Continued)

| | | | |
|---|---|---|---|
| | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYRQHYNDT PGKFVQGIMVEIT<br><br>SEQ ID NO: 25902 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29908 |
| iPS:434773 | 21-225_75D9 | NA | GAAATTGTGTTGACGCAGTCTCCAGGCACCCT GTCTTTGTCTCCAGGGGAAAGAGCCACCCTCT CCTGCAGGGCCAGTGCAGAGTGTTAGCAGCAGC TACTTAGCCTGGTACCAGCAGAAACGTGGCCA GGCTCCCAGGCTCCTCATCTATGGTGCATCCA GCAGGGCCACTGGCATTCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGCTCACCG TGGACGTTCGGCCAAGGGACCAAGGTGGAAA TCAAA<br><br>SEQ ID NO: 25903 | CAGGTGCAGTACAGCAGTGGGGCGCAGGACTG TTGAAGCCTTCGGAGACCCTGTCCCTCACCTGCG CTGTCTATGGTGGGTCCTTCAGTGGTCCCTACTG GAGCTGGATCCGCCAGCCCCCAGGGAAGGGGCT GGAGTGGATTGGGGAAATCAATTATAGGGGAAG CACCAACTACAACCGTCCCTCCAAGAGTCGAGTC ACCATTTCAGTAGACACGTCCAAGAACCAGTTCT CCCTGAACCTGAGCTCTGTGACCGCCGACACC GGCTGTGTATTACTGTGCGAGGGACTACGGCGGT ATGGACGTCTGGGGCCAAGGGACCACGGTCACC GTCTCCTCA<br><br>SEQ ID NO: 29909 |
| | | AA | EIVLTQSPGTLSLSPGERATLSCRASQSVSSSYLA WYQQKRGQAPRLLIYGASSRATGIPDRFSGSGSG TDFTLTISRLEPEDFAVYYCQQYESSPWTFGQGT KVEIK<br><br>SEQ ID NO: 25904 | QVQLQQWGAGLLKPSETLSLTCAVYGGSFSGPYW SWIRQPPGKGLEWIGEINYRGSTNYNPSLKSRVTIS VDTSKNQFSLNLSSVTAADTAVYYCARDYGGMDV WGQGTTVTVSS<br><br>SEQ ID NO: 29910 |

FIGURE 50
(Continued)

| | | | | |
|---|---|---|---|---|
| iPS:434777 | 21-225_81C11 | NA | GAAATTGTGTTGACGCAGTCTCCAGGCACCCTGTCTTTGTCTCCAGGGGAAAGAGCCACCCTCTCATGCAGGGCCAGTCAGAGTGTTTACAGCAGCTACTTAGCCTGGTACCAGCAGAAACCTGGCCAGGCTCCCAGGCTCCTCATTTATGGTGCATCAGCCCGGTCCACTGGCCTCCCAGACAGGTTCAGTGGCAGTGGGTGTGGGACAGACTTCGCTCTCACCATCAGCAGACAGAGTGGAGCCTGAAGATTGTGCAGTGTATTACTGTCAGCATTCTGATAACTCACCGTGGACGTTCGGCCAAGGGACCAAGGTGGAAATCAAA | CAGGTGCAGCTACAGCAGTGGGGCGCAGGACTGTTGAAGCCTTCGGAGACCCTGTCCCTCACCTGCGCTGTCCATGTGGGTCCTTCAGTGGTTGTACTGGAGCTGGATCGCCAGCCCCCAGGGAAGGGGCTGGAGTGGATTGGGGAAATCAATCATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGGACACGGCTGTGTATTACTGTGCGAGGGACTACGGCCGTATGGACGTCTGGGGCCAAGGGACCACGGTCACCGTCTCCTCA |
| | | AA | EIVLTQSPGTLSLPVERATLSCRASQSVYSSYLAWYQQKPGQAPRLLIYGASSRSTGLPDRFSGSGSGTDFALTISRVEPEDCAVYYCQHSDNSPWTFGQGTKVEIK | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTSS |
| | | | SEQ ID NO: 25905 | SEQ ID NO: 29911 |
| | | | SEQ ID NO: 25906 | SEQ ID NO: 29912 |
| iPS:434793 | 21-225_82A5 | NA | GAAATTGTGTTGACGCAGTCTCCAGGCACCCTGTCTTTGTCTCCAGGGGAAAGAGCCACCCTCTCGTGCAGGGCCAGTCAGAGTGTTAGCAGCAGCTACTTAGCCTGGTACCAGCAGAAACCTGGCCAGGCTCCCAGGCTCCTCATCTATGGTGCATCCAGGGCCACTGGCATCCCAGACAGGTTCAGTGGCAGTGGGTCTGGGACAGACTTCACTCTCACCATCAGCAGACTGGAGCCTGAATATTTTGCAGTTTATTACTGTCAGCAGTATGGTAACTCACCGCTCACTTTCGGCGGAGGGACCAAGGTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGCACCTAACAATGGTAACACAGGCTATGCACAGAAGTTCCAGGGCAGAGTCACCATGACCAGGAACACCTCCATAAGCACAGCCTACATGGAGCTGAACAGCCTGAGATCTGAGGACACGGCCGTGTATTACTGTGCGATTAGCAGTGGCTGGTACTGGTTCGACCCCTGGGGCCAGGGAACCCTGGTCACCGTCTCCTTA |
| | | | SEQ ID NO: 25907 | SEQ ID NO: 29913 |

FIGURE 50
(Continued)

| | | | | |
|---|---|---|---|---|
| iPS:434797 | 21-225_82G5 | AA | EIVLTQSPGTLSWSPGERATLSCRASQSVSSSYLA WYQQKPGQAPRLLIYGASTRATGIPDRFSGSGSG TDFTLTISRLEPEYFAVYYCQQYGNSPLTFGGGT KVEIK<br><br>SEQ ID NO: 25908 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL<br><br>SEQ ID NO: 29914 |
| | | NA | GAATTTATGTTGACGCAGTCTCCAGGCACCCT GTATTGGTCTCCAGGGGAAAGAGCCACCCTCT CGAGCAGGGCCAGTGAGAGTGTTAGCAGCAG CTACTTAGTCTGGTATCAGCAGAAACCTGGCC AGGCTCCCAGGCTCCTCATCTATGGTGCATCC ACCAGGGCCACTGGCATCCCAGACAGGTTCAG TGGCAGTGGGTCTGGGACAGACTTCACTCTCA CCATCAGCAGACTGGAGCCTGAATATTTTGCA GTTTATTACTGTCAGCAGTATGGTTGCTCACCG CTCACTTTCGGCGGAGGGACCAAGGTGGAGAT CACA<br><br>SEQ ID NO: 25909 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGC TTGAGTGGATGGGATGGATGCACCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA<br><br>SEQ ID NO: 29915 |
| | | AA | EFMLTQSPGTLYWSPGERATLSSRASESVSSSYL VWYQQKPGQAPRLLIYGASTRATGIPDRFSGSGS GTDFTLTISRLEPEYFAVYYCQQYGCSPLTFGGG TKVEIT<br><br>SEQ ID NO: 25910 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29916 |

FIGURE 50
(Continued)

| | | | |
|---|---|---|---|
| iPS:434805 | 21-225_82D9 | NA | GAATTTATGTTGACGCAGTCTCCAGGCACCCT GTCTTGGTCTCCAGGGAAAGAGCCACCCTCT CGTGCAGGGCCAGTGAGAGTGTTAGCAGCAG CTACTTAGTCTGGTATCAGCAGAAACCTGGCC AGGCTCCCAGGCTCCTCATCTATGGTGCATCC ACCAGGGCCACTGGCATCCCAGACAGGTTCAG TGGCAGTGGGTCTGGGACAGACTTCACTCTCA CCATCAGCAGAGACTGGAGCCTGAATATTTTGCA GTTTATTACTGTCAGCAGTATGGTTGCTCACCG CTCACTTTCGGCGGAGGGACCAAGGTGGAGAT CACA<br><br>SEQ ID NO: 25911 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGATGGATGCACCCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGACTGGTACTGTTCGACCCCTGGGGCCAGGGA ACCCTGGTCACCGTCTCCTCA<br><br>SEQ ID NO: 29917 |
| | | AA | EFMLTQSPGTLSWSPGERATLSCRASESVSSSYL VWYQQKPGQAPRLLIYGASTRATGIPDRFSGSGS GTDFTLTISRLEPEYFAVYYCQQYGCSPLTFGGG TKVEIT<br><br>SEQ ID NO: 25912 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29918 |
| iPS:434809 | 21-225_74F5 | NA | GAAATTGTGTTGACGCAGTCTCCAGGCACCCT GTATTGTCTCCAGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGCACTCTGATAACTCACCGT TGACGTTCGGCCAAGGGACCAAGGTGGAAAT CAAA<br><br>SEQ ID NO: 25913 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29919 |

FIGURE 50
(Continued)

| | | | |
|---|---|---|---|
| iPS:434813 | 21-225_82C12 | AA | EIVLTQSPGTLYLSPGERATLSCRASQSVYSSYLA WYQQKPGQAPRLLIYGASSRSTGIPDRFSGSGSG TDFALTISRLEPEDFAVYYCQHSDNSPWTFGQGT KVEIK<br>SEQ ID NO: 25914 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br>SEQ ID NO: 29920 |
| | | NA | GAAATTGTGTTGACGCAGTCTCCAGGCACCCT GTCTTGGTCTCCAGGGGAAAGAGCCACCCTCT CGTGCAGGGCCAGTCAGAGTGTTAGCAGCAGC TACTTAGCCTGGTACCAGCAGAAACCTGGCCA GGCTCCCAGGCTCCTCATCTATGGTGCATCCA CCAGGGCCCTCTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTAACTCACCG CTCACTTTCGGCGGAGGGACCAAGGTGGAGAT CAAA<br>SEQ ID NO: 25915 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAATGG TAACACAGGCTATGCACAGAAGTTCCAGGGCAG AGTCACCATGACCAGGAACACCTCCATAAGCAC AGCCTACATGGAGCTGAACAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTTA<br>SEQ ID NO: 29921 |
| | | AA | EIVLTQSPGTLSWSPGERATLSCRASQSVSSSYLA WYQQKPGQAPRLLIYGASTRASGIPDRFSGSGSG TDFTLTISRLEPEYFAVYYCQQYGNSPLTFGGGT KVEIK<br>SEQ ID NO: 25916 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL<br>SEQ ID NO: 29922 |

FIGURE 50
(Continued)

| | | | | |
|---|---|---|---|---|
| iPS:434815 | 21-225_74A11 | NA | GACATCCAGATGACCCAGTCTCCATCCTCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTGTGCTGCATCCAGT TTGCAAAGTGGGGTCCCATCAAGGTTCAGCGG CAGTGGATCTGGGACCGAGTTCACTCTCACAA TCAGCAGCCTGCAGCCTGAAGATTTTGCAACT TATTTCTGTCTACAGCATAATGATTACCCATTC ACTTTCGGCCCTGGGACCAAGTGGATATCAA A | CAGGTGCAGCTGGTGGTGCAGTCTGGGGCTGAGGTG AAGAAGCCTGGGGCCTCAGTGAAGGTCTCCTGTA AGGCTTCTGGATACACCTTCACCAGTTATGATAT CAACTGGGTGCGACAGGCCACTGGACAAGGGCT TGAGTGGATGGGATGGATGAACCCTAACAGTGG TAACACAGGCTATGCACAGAAGTTCCAGGGCAG AGTCACCATGACCTGGAACACCTCCAAAGCAC AGCCTACATGGAGCTGAGCAGCCTGAGATCTGA GGACACGGCCGTGTATTACTGTGCGAGAGGCTTT TACGATACTTTGACTGGTTCCGGCTACTACG TTATGGACGTCTGGGGCCAAGGGACCACGGTCA CCGTCTCCTCA |
| | | | SEQ ID NO: 25917 | SEQ ID NO: 29923 |
| | | AA | DIQMTQSPSSLSASVGDRVTITCRASQDIRNDLG WYQQKPGKAPKRLICAASSLQSGVPSRFSGSGS GTEFTLTISSLQPEDFATYFCLQHNDYPFTFGPGT KVDIK | QVQLVQSGAEVKKPGASVKVSCKASGYTFTSYDIN WVRQATGQGLEWMGWMNPNSGNTGYAQKFQGR VTMTWNTSKSTAYMELSSLRSEDTAVYYCARGFY DTLTGSGYYVMDVWGQGTTVTVSS |
| | | | SEQ ID NO: 25918 | SEQ ID NO: 29924 |
| iPS:434821 | 21-225_83G1 | NA | GAAATTGTGTTGACGCAGTCTCCAGGCACCCG GTATTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCA GCCGGGTCCACGGTCCTCCCAGACAGGTTCAGT GGCAGTGGGTCTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA | CAGGTGCAGCTACAGCAGTGGGGCGCAGGACTG TTGAAGCCTTCGGAGACCCTGTCCCTCACCTGCG CTGTCCATGGTGGGTCCTTCAGTGGTGCTACTG GAGCTGGATCCGCCAGCCCCCAGGGAAGGGCT GGAGTGGATTGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGGACAC GGCTGTGTATTACTGTGCGAGGGACTACGGCGT ATGGACGTCTGGGGCCAAGGGACCACGGTCACC GTCTCCTCA |
| | | | SEQ ID NO: 25919 | SEQ ID NO: 29925 |

FIGURE 50
(Continued)

| | | | |
|---|---|---|---|
| | | AA | EIVLTQSPGTRYLSPGERATLSCRASQSVYSSYLAWYQQKPGQAPRLLIYGASSRSTVLPDRFSGSGSGTDFALTISRVEPEDCAVYYCQHSDNSPWTFGQGTKVEIK<br>SEQ ID NO: 25920 | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTVSS<br>SEQ ID NO: 29926 |
| iPS:434825 | 21-225_83C2 | NA | GAATTTATGTTGACGCAGTCTCCAGGCACCCTGTGTTTGTCTCCAGGGGAAAGAGCCACCCTCTCGTGCAGGGCCAGTCAGAGTGTTAGCAGCAGCTACTTAGTCTGGTATCAGCAGAAACCTGGCCAGGCTCCCAGGCTCCTCATCTATGGTGCATCACCAGGGCCACTGCATCCCAGACAGGTTCAGTGGCAGTGGGTCTGGGACAGACTTCACTCTCACCATCAGCAGACTGGAGCTGAGCAGTATATTTGCAGTTTATTACTGTCAGCAGTATGGTTGCTCACCGCTCACTTTCGGCGGAGGGACCAAGGTGGAGATCACA<br>SEQ ID NO: 25921 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGTCCCTGGACAAGGCTTGAGTGGATGGGATGCACCTAACACAGGCTATGCACAGAAGTTCCAGGGCAGAGTCACCATGACCAGGAACACCTCCATCAGCACAGCCTACATGGAGCTGAGCAGCCTGAGATCTGAGGACACGGCCGTGTATTACTGTGCGATTAGTAGTGGCTGGTACTGGTTCGACCCCTGGGGCCAGGGAACCCTGGTCACCGTCTCCTCA<br>SEQ ID NO: 29927 |
| | | AA | EFMLTQSPGTLCLSPGERATLSCRASQSVSSSYLVWYQQKPGQAPRLLIYGASTRATGIPDRFSGSGSGTDFTLTISRLEPEYFAVYYCQQYGCSPLTFGGGTKVEIT<br>SEQ ID NO: 25922 | QVQLVQSGAEVKKPGASVKVSCKASGYTFTNYDINWVRQVPGQGLEWMGWMHPNSGNTGYAQKFQGRVTMTRNTSISTAYMELSSLRSEDTAVYYCAISSGWYWFDPWGQGTLVTVSS<br>SEQ ID NO: 29928 |

FIGURE 50
(Continued)

| | | | | |
|---|---|---|---|---|
| iPS:434827 | 21-225_83F3 | NA | GACATCGTGATGACCCAGTCTCCAGATTGCCT GGCTGTGTCTCTGGGCGAGAGGGCCACCATCA ACTGCAAGTCCAGCAGTGTTTTATACACC TCCAACAATAACAACTACTTAGCTTGGTACCA GCAGAAACCAGGACAGCCTCCTAAGCTGCTCA TTTACTGGGCATCTACCCGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCACT ATAATGATACTCCAATGGAAGTTTGTCCAAGGG ATCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA |
| | | AA | | |
| | | | SEQ ID NO: 25923 | SEQ ID NO: 29929 |
| | | | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYNDT PWKFVQGIKVEIK | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25924 | SEQ ID NO: 29930 |
| iPS:434829 | 21-225_83G3 | NA | GACATCGTGATGACCCAGTCTCCAGATTGCCT GGCTGTGTCTCTGGGCGAGAGGGCCACCATCA ACTGCAAGTCCAGCAGTGTTTTATACACC TCCAACAATAACAACTACTTAGCTTGGTACCA GCAGAAACCAGGACAGCCTCCTAAGCTGCTCA TTTACTGGGCATCTACCCGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCACT ATTATAATACTCCGTGGACGTTTGTCCAAGGG ACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA |
| | | | SEQ ID NO: 25925 | SEQ ID NO: 29931 |

FIGURE 50
(Continued)

| | | | |
|---|---|---|---|
| iPS:434833 | 21-225_83C5 | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYYNT PWTFVQGTKVEIK<br><br>SEQ ID NO: 25926 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29932 |
| | | NA | GAATTTATGTTGACGCAGTCTCCAGGCACCCT GTGTTGGTCTCCAGGGGAAAGAGCCACCCTCT CGTGCAGGGCCAGTGAGAGTGTTAGCAGCAG CTACTTAGTCTGGTATCAGCAGAAACCTGGCC AGGCTCCCAGGCTCCTCATCTATGGTGCATCC ACCAGGGCCACTGGCATCCCAGACAGGTTCAG TGGCAGTGGGTCTGGGACAGATTCACTCTCA CCATCAGCAGACTGAGCTGGACAGCCTGAATATTTGCA GTTTATTACTGTCAGCAGTATGGTTGCTCACCG CTCACTTTCGGCGGAGGGACCAAGGTGGAGAT CACA<br><br>SEQ ID NO: 25927 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGC TTGAGTGGATGGGATGGATGCACAGAAGTTCCAGGGCAG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA<br><br>SEQ ID NO: 29933 |
| | | AA | EFMLTQSPGTLCWSPGERATLSCRASESVSSSYL VWYQQKPGQAPRLLIYGASTRATGIPDRFSGSGS GTDFTLTISRLEPEYFAVYYCQQYGCSPLTFGGG TKVEIT<br><br>SEQ ID NO: 25928 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29934 |

FIGURE 50
(Continued)

| | | | |
|---|---|---|---|
| iPS:434835 | 21-225_83B6 | NA | GAAATTGTGTTGACGCAGTCTCCAGGCACTTT GTCTTTGTCTCCAGGGGAAAGAGCCACCCTCT CCTGCAGGGCCAGTCAGTGTTGACAGCGGC TACTTAGCCTGGTACCAGCAGAAACCTGGCCA GGCTCCCAGGCTCCTCATCTATGGTGCATCCA GCAGGACCCCTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGCTCACCG TGGACGTTCGGCCAAGGGACCAAGGTGGAAA TCAAA SEQ ID NO: 25929 | CAGGTGCAGCTACAGCAGTGGGGCGCAGGACTG TTGAAGCCTTCGGAGACCCTGTCCCTCACCTGCG CTGTCTATGGTGGGTCTTCAGTGGTTGTTACTGG AGCTGGATCCGCCAGCCCCCAGGGAAGGGCTG GAGTGGATTGGGAAATCAATCATAGTGGAAGG ACCAACTACAACCCTCCCTCAAGAGTCGAGTCA CCATATCAGTAGACACGTCCGAGAACCAGTTCTC CCTGAAGCTGAGCTCTGTGACCGCCGCGGACACG GCTGTGTATTACTGTGCGAGAGACTACGGTGGGC TTGACTACTGGGGCCAGGGAACCCTGGTCACCGT CTCCTCA SEQ ID NO: 29935 |
| | | AA | EIVLTQSPGTLSLSPGERATLSCRASQSVDSGYLA WYQQKPGQAPRLLIYGASSRTPGIPDRFSGSGSG TDFTLTISRLEPEDFAVYYCQQYESSPWTFGQGT KVEIK SEQ ID NO: 25930 | QVQLQQWGAGLLKPSETLSLTCAVYGGSFSGCYW SWIRQPPGKGLEWIGEINHSGRTNYNPSLKSRVTIS VDTSENQFSLKLSSVTAADTAVYYCARDYGGLDY WGQGTLVTVSS SEQ ID NO: 29936 |
| iPS:434839 | 21-225_83B7 | NA | GAAATTGTGTTGACGCAGTCTCCAGGCACCCG GTATTTGTCTCCAGTGGAAAGAGCCACCCTCT CATGCAGGGCCAGTCAGAGTGTTTACAGCAGC TACTTAGCGTGGTACCAGCAGAAACCTGGCCA GGCTCCCAGGCTCCTCATTTATGGTGCATCCA GCCGGGTCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCAGTACTCTGATAACTCACCGT GGACGTTCGGCCAAGGGACCAAGGTGGAAAT CAAA SEQ ID NO: 25931 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGTACTG GAGCTGGATCCGCCAGCCCCCAGGGAAGGGCT GGAGTGGATTGGGAAATCAATCATAGTGGAAG CACCAACTACAACCCTCCCTCAAGAGTCGAGTC ACCATTTCAGTAGACACGTCCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29937 |

FIGURE 50
(Continued)

| | | | |
|---|---|---|---|
| iPS:434841 | 21-225_83G7 | AA | EIVLTQSPGTRYLSSVERATLSCRASQSVYSSYL AWYQQKPGQAPRLLIYGASSRSTGIPDRFSGSGS GTDFALTISRLEPEDCAVYYCQHSDNSPWTFGQ GTKVEIK<br>SEQ ID NO: 25932 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29938 |
| | | NA | GACATCGTGATGACCCAGTCTCCAGACTCCCT GGCTGTGTCTCTGGGCGAGAGGGCCACCATCA TCTGCAAGTCCAGCCAGAGTGTTTACACAGC TCCAACAATTATAACTACTTAGCTTGGTACCA GCAGAAGCCAGGACAGGCCCCTAAGGTGCTC ATTTACTGGACATCTACCCGGGAATCCGGGGT CCCTGACCGATTCAGTGGCAGCGGGTCTGGGA CAGATTCACTCTCACCATCAGCAGCCTGCAG GCTGAAGATGTGGCAGTTTATTACTGTCAGCA ATATTTTAGTAGTCCTCTGACGTTCGGCCAAG GGACCAAGGTGGAAATCAAA<br>SEQ ID NO: 25933 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA<br>SEQ ID NO: 29939 |
| | | AA | DIVMTQSPDSLAVSLGERATIICKSSQTVLHSSNN YNYLAWYQQKPGQPPKVLIYWTSTRESGVPDRF SGSGSGTDFTLTISSLQAEDVAVYYCQQYFSSPL TFGQGTKVEIK<br>SEQ ID NO: 25934 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS<br>SEQ ID NO: 29940 |

FIGURE 50
(Continued)

| | | | | |
|---|---|---|---|---|
| iPS:434849 | 21-225_83C10 | NA | GAAATTGTGTTGACGCAGTCTCCAGGCACCCTGTCTTTGTCTCCAGGGGAAAGAGCCACCCTCTCCTGCAGGGCCAGTCCGAGTGTTCACAGCAACTACTTAGCCTGGTACCAGCAGAAACCTGGCCAGGCTCCCAGGCTCCTCATCTATGGTGCATCAGCAGGGCCACTGGCATCCCAGACAGGTTCAGTGGCAGTGGGTCTGGGACAGACTTCATTCTCACCATCAGCAGACTGGAGCCTGAAGATTTTGCAGTGTATTACTGTCAGCAGTATGAAAGTTCACCGTGGACGTTCGGCCAAGGGACCAAGGTGGAAATCAAA SEQ ID NO: 25935 | CAGGTGCAGCTACAGCAGTGGGGCGCAGGACTGTTGAAGCCTTCGGAGACCCTGTCCCTCACCTGCACTGTCTATGGTGGGTCCTTCAGTGGTTACTACTGGAGCTGGATCCGCCAGCCCCCAGGGAAGGGGCTGGAATGGATTGGGGAAATCAATCATAGTGGAAGCACCAACTTCAACCCGTCCCTCAAGAGTCGAGTCACCATATCAGTAGACACGTCCAAGAACCAGTTCTCCCTGAAGCTGAGCTCTGTGACCGCCGCGGACACGGCTGTGTTTTACTGTGCGAGAGACTACGGTGGCTTGACTACTGGGGCCAGGGAACCCTGGTCACCGTCTCCTCA SEQ ID NO: 29941 |
| | | AA | EIVLTQSPGTLSLSPGERATLSCRASPSVHSNYLAWYQQKPGQAPRLLIYGASSRATGIPDRFSGSGSGTDFILTISRLEPEDFAVYYCQQYESSPWTFGQGTKVEIK SEQ ID NO: 25936 | QVQLQQWGAGLLKPSETLSLTCTVYGGSFSGYYWSWIRQPPGKGLEWIGEINHSGSTNFNPSLKSRVTISVDTSKNQFSLKLSSVTAADTAVFYCARDYGGLDYWGQGTLVTVSS SEQ ID NO: 29942 |
| iPS:434851 | 21-225_75A6 | NA | GACATCGTGATGACCCAGTCGCCAGACTCCCTGGCTGTGTCTCTGGGCGAGAGGGCCACCATCAACTGCAAGTCCAGACAGAGTGTTTACACAGCTCCAACAATTACAACTACTAGCTTGGTACCAGCAGAAACCAGGACAGCCTCCTGAACTACTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAGGATGTGGCAGTTTATTACTGTCAGCAATATTATAGTACTCCTCCTCTACTTTCGGCGGAGGGACCAAGGTGGAGATCAAA SEQ ID NO: 25937 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGCAGAGTCACCATGACCAGGAACACCTCCATAAGCACAGCCTACATGGAGCTGAGCAGCCTGAGATCTGAGGACACGGCCGTGTACATCTTTGACTACTGGGGCCAGGGAACCCTGGTCACCGTCTCCTCA SEQ ID NO: 29943 |

FIGURE 50
(Continued)

| | | | |
|---|---|---|---|
| | | AA | DIVMTQSPDSLAVSLGERATINCKSRQSVLHSSN NYNYLAWYQQKPGQPPELLIYWASTRESGVPDR FSGSGSGTDFTLTISSLQAEDVAVYYCQQYYSTP PTFGGGTKVEIK<br>SEQ ID NO: 25938 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YIFDYWGQGTLVTVSS<br>SEQ ID NO: 29944 |
| iPS:434863 | 21-225_84G7 | NA | GACATCGTGATGACCCAGTCTCCAGACTCCCC GGCTGTGTCTCTGGGCGAGAGGGCCACCATCA TCTGCAAGTCCAGCCAGAGCTGTTTACACAGC TCCAACAATTATAACTACTTAGCTTGGTACCA GCAGAAGCCAGGACAGCCCCTAAGGTGCTC ATTTACTGGACATCTACCCGGGAATCCGGGGT CCCTGACCGATTCAGTGGCAGCGGGTCTGGGA CAGATTTCACTCTCACCATCAGCAGCCTGCAG GCTGAAGATGTGGCAGTTTATTACTGTCAGCA ATATTTTAGTAGTCCTCCGACGTTCGGCCAAG GGACCAAGGTGGAAATCAAA<br>SEQ ID NO: 25939 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGACA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA<br>SEQ ID NO: 29945 |
| | | AA | DIVMTQSPDSPAVSLGERATIICKSSQTVLHSSNN YNYLAWYQQKPGQPPKVLIYWTSTRESGVPDRF SGSGSGTDFTLTISSLQAEDVAVYYCQQYFSSPP TFGQGTKVEIK<br>SEQ ID NO: 25940 | QVQLVQSGAEVKKPGASVKVSCKASGYTFPNYDIN WVRQATGQGLEWMGWMNPNSGNTGYAQKFQDR VTMTRNTSISTAYMELSSLRSEDTAVYYCAVSSGW HWFDPWGQGTLVTVAS<br>SEQ ID NO: 29946 |

FIGURE 50
(Continued)

| | | | |
|---|---|---|---|
| iPS:434867 | 21-225_79A12 | NA | GACATCCAGATGACCCAGTCTCCATCCTCACT GTCTGCATCTGTAGGAGACAGAGTCACCATCA CTTGTCGGGCGAGTCAGGTCATTAGCAAGTAT TTAGCCTGGTTTCAGCAGAAACCAGGGAAAGC CCCTAAGTCCCTGATCTATGCTGCATCCAGTTT GCAAAGTGGGGCCCCATCAAAGTTCAGCGGC AGTGGATCTGGGACAGATTTCACTCTCACCAT CAGCAGCCTGCAGCCTGAAGATTTTGCAACTT ATTACTGCCAACAGTACAGTAATTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATGGCAG CTATGGTTACGACGGCCTTGACTACTGGGGCCAG GGAACCCTGGTCGCCGTCTCCTCA |
| | | | SEQ ID NO: 25941 | SEQ ID NO: 29947 |
| | | AA | DIQMTQSPSSLSASVGDRVTITCRASQVISKYLA WFQQKPGKAPKSLIYAASSLQSGAPSKFSGSGSG TDFTLTISSLQPEDFATYYCQQYSNYPLTFGGGT KVEIK | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDGSYG YDGLDYWGQGTLVAVSS |
| | | | SEQ ID NO: 25942 | SEQ ID NO: 29948 |
| iPS:434869 | 21-225_84E12 | NA | GAAATTGTGTTGACGCAGTCTCCAGGCACCCT GTCTTTGTCTCCAGGGGAAAGAGCCACCCTCT CCTGCAGGGCCAGTCAGAGTATTAACAGCAAC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGACGATTTTGCAG TGTTTTACTGTCAGCAGTATGAGAGCTCACCG TGGACGTTCGGCCAAGGGACCAAGGTGGAAA TCAAA | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTCCTACTGG AGCTGGATCCGCCAGCCCCCAGGGAAGGGCTA GAGTGGATTGGGGAAATCAATCAAAGTGGACGC ACCAACTACAACCGTCCCTCCAAGAGTCGAGTCA CCATATCAGTAGACACGTCCAAGAACCAGTTCTC CCTGAAGCTGAGCTCTGTGACCGCCGCGGACACG GCTGTGTATTACTGTGCGAGAGACTACGGGGGTA TAGACGTCTGGGGCAAGGGACCACGGTCACCG TCTCCTCA |
| | | | SEQ ID NO: 25943 | SEQ ID NO: 29949 |

FIGURE 50
(Continued)

| | | | | |
|---|---|---|---|---|
| | | AA | EIVLTQSPGTLSLSPGERATLSCRASQSINSNYLA WYQQKPGQAPRLLIYGASSRATGIPDRFSGSGSG TDFTLTISRLEPDDFAVFYCQQYESSPWTFGQGT KVEIK | QVQLQQWGAGLLKPSETLSLTCAVYGGSFSGSYW SWIRQPPGKGLEWIGENQSGRTNYNPSLKSRVTIS VDTSKNQFSLKLSSVTAADTAVYYCARDYGGIDV WGQGTTVTVSS |
| | | | SEQ ID NO: 25944 | SEQ ID NO: 29950 |
| iPS:434871 | 21-225_85H1 | NA | GAGATAGTGATGACGCAGTCTCCAGCCACCCT GTCTGTGTCTCCAGGGGAAAGAGCCACCCTCT CCTGCAGGGCCAGTCAGGATGTTATCACCTAC TTAGCCTGGTACCAGCAGAAACCTGGCCAGGC TCCCAGGCTCCTCATCTATGGTGCATCCACCA GGGCCACTGGTGTCCCAGCCAGGTTCAGTGGC AGTGGGTCTGGGACAGAGTTCACTCTCACCAT CAGCAGCCTGCAGTCTGAAGATATTGCACTTT ATTACTGTCAGGAGTATAATGACTGGCCGTGC AGTTTTGGCCAGGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT ACACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCCCTT TATAGTGGGAGCTACTACTTTGACTACTGGGGC CAGGGAACCCTGGTCACCGTCTCCTCA |
| | | | SEQ ID NO: 25945 | SEQ ID NO: 29951 |
| | | AA | EIVMTQSPATLSVSPGERATLSCRASQDVITYLA WYQQKPGQAPRLLIYGASTRATGVPARFSGSGS GTEFTLTISSLQSEDFALYYCQEYNDWPCSFGQG TKVEIK | QVQLVESGGGVVQPGRSLRLSCAASGFTFSSYGIH WVRQAPGKGLEWVAVIWYDGSNKYYADSVKGRF TISRDNSKNTLYLQMNSLRAEDTAVYYCARDPFIV GATYFDYWGQGTLVTVSS |
| | | | SEQ ID NO: 25946 | SEQ ID NO: 29952 |

FIGURE 50
(Continued)

| | | | | |
|---|---|---|---|---|
| iPS:434877 | 21-225_85H2 | NA | GACAGCATGATGACCCAGTCTCCAGACTCCCTGGCTGTGTCTCTGGGCGAGAGGGCCACCATCAACTGCAAGTCCAGCCAGAGTGTTTTACACAGCTCTAATAAAAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGTCTGCAGGCTGAAGATGTGGCAGTTTATTACTGTCAGCAATATTATAGGACTCCGTGACGTTCGGCCAAGGGACCAAGGTGGAAATCAAA<br>SEQ ID NO: 25947 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGCACCTAATAGTGGTAACACAGGCTATGCACAGAAGTTCCAGGGCAGAGTCACCCTGACCAGGAACACCTCCATAAGCACAGCCTACATGGAGCTGAGCAGCCTGAGATCTGAGGACACGGCCGTGTATTACTGTGCGGTTTCCAGTGGCTGGTACTGTTCGACCCCTGGGGCCAGGGAACCCTGGTCACCGTCCTCA<br>SEQ ID NO: 29953 |
| | | AA | DSMMTQSPDSLAVSLGERATINCKSSQSVLHSSNKKNYLAWYQQKPGQPPKLLIYWASTRESGVPDRFSGSGSGTDFTLTISSLQAEDVAVYYCQQYYRTPWTFGQGTKVEIK<br>SEQ ID NO: 25948 | QVQLVQSGAEVKKPGASVKVSCKASGYTFTNYDINWVRQATGQGLEWMGWMHPNSGNTGYAQKFQGRVTLTRNTSISTAYMELSSLRSEDTAVYYCAVSSGWYWFDPWGQGTLVTVSS<br>SEQ ID NO: 29954 |
| iPS:434879 | 21-225_85A3 | NA | GAAATTGTGTTGACGCAGTCTCCAGGCACCCTGTCTTTGTCTCCAGGGGAAAGAGCCACCCTCTCCTGCAGGGCCAGTCAGAGTGTTTACAGCAGCTACTTAGCCTGGTACCAGCAGAAACCTGCCCAGGCTCCCAGGCTCCTCATCTATGGTGCATCCAGCCGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCACTATGATAACTCACCGTGGACGTTCGGCCAAGGGACCAAGGTGGAAATCAAA<br>SEQ ID NO: 25949 | CAGGTGCAGCTACAGCAGTGGGGCGCAGGACTGTTGAAGCCTTCGGAGACCCTGTCCCTCACCTGCGCTGTCCATGGTGGGTCCTTCAGTGGTTGCTACTGGAGCTGGATCCGCCAGCCCCCAGGGAAGGGCTGGAGTGGATTGGGGAAATCAATCATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA<br>SEQ ID NO: 29955 |

FIGURE 50
(Continued)

| | | | |
|---|---|---|---|
| iPS:434881 | 21-225_85B4 | AA | EIVLTQSPGTLFLSPGERATLSCRASQSVYSSYLA WYQQKPAQAPRLLIYGASSRASGIPDRFSGSGSG TDFALTISRLEPEDFAVYYCQHYDNSPWTFGQG TKVEIK<br>SEQ ID NO: 25950 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29956 |
| | | NA | GAAATTGTGTTGACGCAGTCTCCAGGCACCCT GTTTTTGTCTCCAGGGGAAAGAGCACCCTCT CCTGCAGGGCCAGTCAGAGTGTTTACAGCAGC TACTTAGCCTGGTACCAGCAGAAACCTGGCCA GGCTCCCAGGCTCCTCATCTATGGTGCATCA GCCGGGCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAATCCACCG TGGACGTTCGGCCAAGGGACCAAGGTGGAAA TCAAA<br>SEQ ID NO: 25951 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 29957 |
| | | AA | EIVLTQSPGTLFLSPGERATLSCRASQSVYSSYLA WYQQKPGQAPRLLIYGASSRATGIPDRFSGSGSG TDFALTISRLEPEDFAVYYCQHYDNSPWTFGQG TKVEIK<br>SEQ ID NO: 25952 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 29958 |

FIGURE 50
(Continued)

| | | | | |
|---|---|---|---|---|
| iPS:434883 | 21-225_85B5 | NA | GAATTTATGTTGACGCAGTCTCCAGGCACCCT GTCTTTGTCTCAAGGGGAAAGAGCCACCCTCT CGTGCAGGTCCAGTCAGAGTGTTAGCAGCAGC TACTTAGTCTGGTATCAGCAGAAACCTGGCCA GGCTCCCAGGCTCCTCATCTATGGTGCATCA CCAGGGCCACTGGCATCCCAGACAGGTTCAGT GGCAGTGGGTCTGGGACAGATGGAGCCTGAAT ATTTTGCAG TTTATTACTGTCAGCAGTATGGTTGCTCACCGC TCACTTTCGGCGGAGGGACCAAGGTGGAGATC ACA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGATGGATGCACCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGTTCGACCCCTGGGGCCAGGGA ACCCTGGTCACCGTCTCCTCA |
| | | | SEQ ID NO: 25953 | SEQ ID NO: 29959 |
| | | AA | EFMLTQSPGTLSLSPGERATLSCRSSQSVSSSYLV WYQQKPGQAPRLLIYGASTRATGIPDRFSGSGSG TDFTLTISRLEPEYFAVYYCQQYGCSPLTFGGGT KVEIT | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS |
| | | | SEQ ID NO: 25954 | SEQ ID NO: 29960 |
| iPS:434887 | 21-225_85D6 | NA | GAAATTGTGTTGACGCAGTCTCCAGGCACCCT GTTTTTGTCTCAAGGGGAAAGAGCCACCCTCT CCTGCAGGGCCAGTCAGAGTGTTAGCAGCAGG TACTTAGCCTGGTATCAGCAGAAACCTGGCCA GGCTCCCAGACTCCTCATCTATGGTGCATCA GCAGGGCCACTGGCATCCCAGACAGGTTCAGT GGCAGTGGGTCTGGGACAGACTTCACTCTCAC CATCAGCAGACTGGAGCCTGAAGATAGCTCACCGT TATATTACTGTCAGCATTATGATAGCTCACCGT GGACGTTCGGCCAAGGGACCAAGGTGGAAAT CAAA | CAGGTGCAGCTACAGCAGGGGGGCGCAGGACCG TTGAAGCCTTCGGAGACCCTGTCCCTCACCTGCG CTGTCTATGGTGGGTCCTTCAGTGGTTGCTACTG GAGCTGGATCCGCCAGCCCCCAGGGAAGGGCT GGAGTGGATTGGGGAAATCAATTATAGTGGAAG AACCAACTACAACCGTCCCTCAAGAGTCGAGTC ACCATATCAGTAGACACGTCCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA |
| | | | SEQ ID NO: 25955 | SEQ ID NO: 29961 |

FIGURE 50
(Continued)

| | | | |
|---|---|---|---|
| | AA | EIVLTQSPGTLFLSQGERATLSCRASQSVSSRYLA WYQQKPGQAPRLLIYGASSRATGIPDRFSGSGSG TDFTLTISRLEPEDFAVYYCQHYDSSPWTFGQGT KVEIK<br><br>SEQ ID NO: 25956 | QVQLQQGGAGPLKPSETLSLTCAVYGGSFSGCYWS WIRQPPGKGLEWIGEINYSGRTNYNPSLKSRVTISV DTSKNQFSLKLSSVTAADTAVYYCARDYGGMDV WGQGTTVTVSS<br><br>SEQ ID NO: 29962 |
| iPS:434891 | NA | GAAATTGCGTTGACGCAGTCTCCAGGCACCCT GTCTTTGTCTCCAGGGGAAAGAGCCACCCTCT CCTGCAGGGCCAGTCCAGTGTTGACAGCAGC TACTTAGCCTGGTACCAGCAGAAACCTGGCCA GGCTCCCAGGCTCCTCATCTATGGTGCAGCCA GCAGGGCCCCTGGCATCCCAGACAGGTTCAGT GGCAGTGGGTCTGGGACAGACTTCACTCTCAC CATCAGCAGACTGGAGCCTGAAGACTTTGTAG TGTATTACTGTCAGCAGTATGAAAGTTCACCG TGGACGTTCGGCCAAGGGACCAAGGTGGAAA TCAAA<br><br>SEQ ID NO: 25957 | CAGGTGCAGTACAGCAGTGGGCGCAGGACTG TTGAAGCCTTCGGAGACCCTGTCCCTCACCTGCG CTGTCTATGGTGGGTCCTTCAGTGGTTGCTACTG GAGCTGGATCCGCCAGCCCCAGGGAAGGGGCT GGAGTGGATTGGGGAAATCAATCATAGTGGAAG GACCAACTACAACCGTCCCTCAAGAGTCGAGTC ACCATATCAGTAGACACGTCCGAGAACCAGTTCT CCCTGAAGCTGAGCTCTGTGACCGCCGCGGACAC GGCTGTGTATTACTGTGCGAGAGACTACGGTGGG CTTGACTACTGGGGCCAGGGAACCCTGGTCACCG TCTCCTCA<br><br>SEQ ID NO: 29963 |
| 21-225_85G6 | AA | EIALTQSPGTLSLSPGERATLSCRASPSVDSSYLA WYQQKPGQAPRLLIYGAASRAPGIPDRFSGSGSG TDFTLTISRLEPEDFVVYYCQQYESSPWTFGQGT KVEIK<br><br>SEQ ID NO: 25958 | QVQLQQWGAGLLKPSETLSLTCAVYGGSFSDCYW SWIRQPPGKGLEWIGEINHSGRTNYNPSLKSRVTIS VDTSENQFSLKLSSVTAADTAVYYCARDYGGLDY WGQGTLVTVSS<br><br>SEQ ID NO: 29964 |

FIGURE 50
(Continued)

| | | | |
|---|---|---|---|
| iPS:434895 | 21-225_74H7 | NA | GAACTTGTGTTGACGCAGTCTCCAGGCACCCT GTCTTTGTCTCCAGGGGAAAGAGCCACCCTCT CCTGCAGGGCCAGTCAGTCAGAATATTTACAGCAGC TACTTAGCCTGGTACCAACAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTGCTGTCAGCAGTATGAAAGCTCACCG TGGACCTTCGGCCAAGGGACCAAGGTGGAAA TCAAA<br><br>SEQ ID NO: 25959 |
| | | AA | ELVLTQSPGTLSLSPGERATLSCRASQNIYSSYLA WYQQKPGQAPRLLIYGASSRATGIPDRFSGSGSG TDFTLTISRLEPEDFAVYCCQQYESSPWTFGQGT KVEIK<br><br>SEQ ID NO: 25960 |
| | | | CAAGTGCAGTCTACAGCAGTGGGGCGCAGGACTG TTGAAGCCTTCGGAGTCCCTGTCCCTCACCTGCG CTGTCTATGGTGGGTCCTTCAGTGGTCCTACTG GAGCTGGATCCGCCAGCCCCCGGAAGGGCT GGAGTGGATTGGGGAAATCAATCATAGTGGAAG CACCAACTACACAACCGTCCCTCAAGAGTCGAGTC ACCATATCAGTAGACACGTCAAGAACCAGTTCT CCCTGAAACTGACCTCTGTGCGAGAGACTACGGGGT GGCTGTGTATTACTGTGCGAGAGACTACGGGGT TTGACGTCTGGGGCCAAGGGACCACGGTCACC GTCTCCTCA<br><br>SEQ ID NO: 29965 |
| | | | QVQLQQWGAGLLKPSEPLSLTCAVYGGSFSGPYW SWIRQPPGKGLEWIGEINHSGSTNYNPSLKSRVTISV DTSKNQFSLKLTSVTAADTAVYYCARDYGGLDVW GQGTTVTVSS<br><br>SEQ ID NO: 29966 |
| iPS:434899 | 21-225_85B9 | NA | GAAATTGTGTTGACGCAGTCTCCAGGCACCCT GTTTTTGTCTCCAGGGGAGAGAGCCACCCTCT CCTGCAGGGCCAGTCAGAGTGTTAACAGCAAC TACTTAGCCTGGTACCGGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCATTCTCAT CATCAGCAGACTGGAGCCTGAGGATTTTGCAG TGTATTACTGTCAGCAGTATGAAAGCTCGCCG TGGACGTTCGGCCAAGGGACCAAGGTGGAAA TCAAA<br><br>SEQ ID NO: 25961 |
| | | | CAGGTGCAGCTACAACAGTGGGGCGCAGGACTG TTGAAGCCTTCGGAGACCCTGTCCTCACTTGCG CTGTCAATGTGTGGGCCCTTCAGTGGTTGCTACTG GAGCTGGATCCGCCAGCCCCCAGGGAAGGGCT GGAGTGGATTGGGGAAATCAATCATAGTGGAAG GACCAACTTCAACCCGTCCCTCAAGAGTCGAGTC ACCATATCAGTGACACGTCAAGAACCAGTCT CCCTGAAGCTGAGCTGTGTGACGCCGCGGACAC GGCTGTGTATTACTGTGCGAGAGACTACGGCGTT ATGGACGTCTGGGGCCAAGGGACCACGGTCACC GTCTCCTCA<br><br>SEQ ID NO: 29967 |

FIGURE 50
(Continued)

| | | | | |
|---|---|---|---|---|
| iPS:434901 | 21-225_85H9 | AA | EIVLTQSPGTLFLSPGERATLSCRASQSVNSNYLAWYRQKPGQAPRLLIYGASSRATGIPDRFSGSGSGTDFTLTISRLEPEDFAVYYCQQYESSPWTFGQGTKVEIK<br>SEQ ID NO: 25962 | QVQLQQWGAGLLKPSETLSLTCAVNGGPFSGCYWSWIRQPPGKGLEWIGENHSGRTNFNPSLKSRVTISVDTSKNQFSLKLSSVTAADTAVYYCARDYGGMDVWGQGTTVTVSS<br>SEQ ID NO: 29968 |
| | | NA | GACATCGTGATGACCCAGTCTCCAGACTCCCTGGCTGTGTCTCTGGGCGAGAGGGCCACCACCAATTGTAAGTCCAGCCAGAGTGTTTTACACAGATCCAACAATTACAACTACTTAGCGTGTACCAGCAGAAACCAGGACAGGCCTCCTAAGCTGCTCATTTACTGGGCATCTCACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTCCTCCGACGTTCGGCCAAGGGACCAAGGTGGAAATCAAA<br>SEQ ID NO: 25963 | CAGGTGCAGCTGGTGCAGTCTGGGGCTGAGGTGAAGAAGCCTGGGGCCTCAGTGAAGGTCTCCTGCAAGGCTTCTGGATACACCTTGACCAATTATGATATCAACTGGGTGCGACAGGCCACTGGACAAGGCTTGAGTGGATGGGATGGATGAACCCTAACAGTGGTAACACAGGCTATGCCACAGAAGTTCCAGGGCAGTCACCATGACCAGGAACACCTCCATAAGCACAGCCTACATGGAACTGAGCAGCCTGAGATCTGAGGACACGGCCGTGTATTACCGTGGGAGTACCAGTGGCTGGAACTTCTTTGACTACTGGGGCCAGGGAACCCTGGTCACCGTCTCCTCA<br>SEQ ID NO: 29969 |
| | | AA | DIVMTQSPDSLAVSLGERATTNCKSSQSVLHRSNNYNYLAWYQQKPGQPPKLLIYWASTRESGVPDRFSGSGSGTDFTLTISSLQAEDVAVYYCQQYYSTPPITFGQGTKVEIK<br>SEQ ID NO: 25964 | QVQLVQSGAEVKKPGASVKVSCKASGYTLTNYDINWVRQATGQGLEWMGWMNPNSGNTGYAQKFQGRVTMTRNTSISTAYMELSSLRSEDTAVYYRGSTSGWNFFDYWGQGTLVTVSS<br>SEQ ID NO: 29970 |

FIGURE 50
(Continued)

| | | | | |
|---|---|---|---|---|
| iPS:434907 | 21-225_85G10 | NA | GAAATTGTGTTGACGCAGTCTCCAGGCTCCCTGTCTTTGTCTCCAGGGGAAAGAGCCACCCTCCCTGCAGGGCCAGTCAGAGTGTTTGGAGCGGCTACTTAGCCTGGTACCAGCAGAAACCTGGCCAGGCTCCCAGGCTCCTCATCTATGGTGCATCTAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTTCTGTCAGCAGTATGAGAGTTCACCGTGGACGTTCGGCCAAGGGACCAAGGTGGAAATCAAA | CAGGTACACAGCTACAGCAGCGGCGGCGGCAGGACTGTTGAAGCCTTCGGAGACCCTGTCCCTCACCTGCGCTGTCTATGGTGGGTCCTTCAGTGGTTGTTACTGGAGCTGGATCCGCCAGCCCCCGGGAAGGGGCTGGAGTGGATTGGGGAAATCAATCATAGTGGAATCACCAACTACAACCCGTCCCTCAAGAGTCGAGTCAACCATATCAGTAGACACGTCCAAGAACCAGTTCTCCCTGAAGCTGACCTCTGTGACCGCCGCGGACACGGCTGTGTATTACTGTGCGAGAGACTACGGTGGTTTGGACGTCTGGGGCCAAGGGACCACGGTCACCGTCTCCTCA |
| | | | SEQ ID NO: 25965 | SEQ ID NO: 29971 |
| | | AA | EIVLTQSPGSLSLSPGERATLSCRASQSVWSGYLAWYQQKPGQAPRLLIYGASSRATGIPDRFSGSGSGTDFTLTISRLEPEDFAVYFCQQYESSPWTFGQGTKVEIK | QVQLQQRGAGLLKPSETLSLTCAVYGGSFSGCYWSWIRQPPGKGLEWIGEINHSGITNYNPSLKSRVTISVDTSKNQFSLKLTSVTAADTAVYYCARDYGGLDVWGQGTTVTVSS |
| | | | SEQ ID NO: 25966 | SEQ ID NO: 29972 |
| iPS:434909 | 21-225_85C11 | NA | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATAAGAACTACTTAGCTTGGTACCAGCAGAAACCAGGACAGCCTCCTAAACTGCTCATTTTCTGGGCATTTATCCGGGAATCCGGGGTCCCTGAAAGGATTCAGTGGCAGCGGGTCTGGGACAGATTTCACTCTCTCCATCAGCGGCCTACAGGCAGAAGATGTGGCAGTTTATTACTGTCAGCAATATTATAGTACTCCCGTGCAGTTTTGGCCAGGGGACCAAGCTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCCTCTGACAAGGACTTGAGTGGATGGGATGGATGCACCTAACAGTGGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACTGCCGTATATTACTGTGCGTATAGTGGCTGGTACAAATTTGACTACTGGAGCCAGGGAACCCTGGTCACCGTCTCCTCA |
| | | | SEQ ID NO: 25967 | SEQ ID NO: 29973 |

FIGURE 50
(Continued)

| | | | | |
|---|---|---|---|---|
| iPS:434911 | 21-225_85D11 | AA | DIVMTQSPDSLAVSLGERATINCKSSQSVLYSSN SHNFLAWYQQNPGQPPKLLIFWAFIRESGVPEGF SGSGSGADFTLSISGLQAEDVAVYYCQQYYSTP CSFGQGTKLEIK<br><br>SEQ ID NO: 25968 | QVQLVQSGAEVKKPGASVKVSCKASGYTFTNYDIN WVRQASGQGLEWMGWMHPNSGNTGYAQKFQGR VTMTRNTSISTAYMELSSLRSEDSAVYYCAYSSGW YKFDYWSQGTLVTVSS<br><br>SEQ ID NO: 29974 |
| | | NA | GAATTTATGTTGACGCAGTCTCCAGGCACCCT GTCTTTGTCTACAGGGGAAAGAGCCACCCTCT CGTGCAGGTCCAGTCAGAGTGTTAGCAGCAGC TACTTAGTCTGGTATCAGCAGAAACCTGGCCA GGCTCCCAGGCTCCTCATCTATGTGCATCA CCAGGGCCACTGGCATCCCAGACAGGTTCAGT GGCAGTGGGTCTGGGACAGACTTCACTCTCAC CATCAGCAGACTGGAGCCTGAATATTTGCAG TTTATTACTGTCAGCAGTATGGTTGCTCACCGC TCACTTTCGGGCGGAGGGACCAAGGTGGAGATC ACA<br><br>SEQ ID NO: 25969 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGATGGATGCACCCTAACAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA<br><br>SEQ ID NO: 29975 |
| | | AA | EFMLTQSPGTLSLSTGERATLSCRSSQSVSSSYLV WYQQKPGQAPRLLIYGASTRATGIPDRFSGSGSG TDFTLTISRLEPEYFAVYYCQQYGCSPLTFGGGT KVEIT<br><br>SEQ ID NO: 25970 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br><br>SEQ ID NO: 29976 |

FIGURE 50
(Continued)

| | | | |
|---|---|---|---|
| iPS:434913 | 21-225_86C1 | NA | GAAATTGTGTTGACGCAGTCTCCAGGCACCCT GTATTTGTCTCCAGGGGCCAGTCAGTGTTTACAGCAGC CCTGCAGGGCCAGTCAGTCAGAGTGTTTACAGCAGC TACTTAGCCTGGTACCAGCAGAAACCTGCCCA GGCTCCCAGGCTCCTCATCTATGGTGCATCA GCCGGGCCACTGGCATCCCAGACAGGTTCAGT GGCAGTGGGTCTGGGACAGACTTCGCTCTCAC CATCAGCAGACTGGAGCCTGAAGATTGTGCAG TGTATTATTACTGTCAGCACTATGATAACTCACCG TGGACGTTCGGCCAAGGGACCAAGGTGGAAA TCAAA<br/><br/>SEQ ID NO: 25971 | CAGGTGCAGCTACAGCAGTGGGGCGCAGGACTG TTGAAGCCTTCGGAGACCGTCCTCACCTGCG CTGTCCATGGTGGTCTTCAGTGGTTGCTACTG GAGCTGGATCCGCCAGCCCCAGGGAAGGGCT GGAGTGGATTGGGAAATCAATCATAGTGGAAG CACCAACTACAACCGTCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br/><br/>SEQ ID NO: 29977 |
| | | AA | EIVLTQSPGTLYLSPGERATLSCRASQSVYSSYLA WYQQKPAQAPRLLIYGASSRATGIPDRFSGSGSG TDFALTISRLEPEDCAVYYCQHYDNSPWTFGQG TKVEIK<br/><br/>SEQ ID NO: 25972 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br/><br/>SEQ ID NO: 29978 |
| iPS:434921 | 21-225_86E4 | NA | GAAATTGTGTTGACGCAGTCTCCAGGCACCCG GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGTCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA<br/><br/>SEQ ID NO: 25973 | CAGGTGCAGCTACAGCAGTGGGGCGCAGGACTG TTGAAGCCTTCGGAGACCGTCCCTCACCTGCG CTGTCCATGGTGGTCCTTCAGTGGTTGCTACTG GAGCTGGATCCGCCAGCCCCAGGGAAGGGGCT GGAGTGGATTGGGAAATCAATCATAGTGGAAG CACCAACTACAACCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br/><br/>SEQ ID NO: 29979 |

FIGURE 50
(Continued)

| | | | |
|---|---|---|---|
| iPS:434935 | | AA | EIVLTQSPGTRYLSPGERATLSCRASQSVYSSYL AWYQQKPGQAPRLLIYGASSRSTGIPDRFSGSGS GTDFALTISRLEPEDCAVYYCQHSDNSPWTFGQ GTKVEIK<br>SEQ ID NO: 25974 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br>SEQ ID NO: 29980 |
| | 21-225_86E9 | NA | GACATCGTGATGACCCAGTCTCCAGACTCCCC GGCTGTGTCTCTGGGCGAGAGGGCCACCATCA ATTGCAAGTCCAGCCAGAGTGTTTGCACAGA TCCAACAATTATAATTACTTAGTTGGTACCA GCAGAAACCAGGACAGCCTCCTAACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGCTGATGTGGCAGTTATTACTGTCAGCAA TATCATAGTAGTCCACTGACGTTCGGCCAAGG GACCACGGTGGAAATCAAA<br>SEQ ID NO: 25975 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAGCACCTCCACAAGCA CAGCCCACATGAAGCTGAGCAGCCTGAGATCTG AGGACACGGCCGTGTATTACTGTGCGGTTCCAG TGGCTGGTCCTGGTTCGACCCTGGGCCAGGA ACCCTGGTCACCGTCTCCTCA<br>SEQ ID NO: 29981 |
| | | AA | DIVMTQCPDSPAVSLGERATINCKSSQSVLHRSN NYNYLAWYQQKPGQPPNLLIYWASTRESGVPD RFSGSGSGTDFTLTISSLQAADVAVYYCQQYHSS PLTFGQGTTVEIK<br>SEQ ID NO: 25976 | QVQLVQSGAEVKKPGASVKVSCKASGYTFTNYDIN WVRQATGQGLEWMGWMNPNSGNTGYAQKFQGR VTMTRSTSTSTAHMELSSLRSEDTAVYYCAVSSGW SWFDPWGQGTLVTVSS<br>SEQ ID NO: 29982 |

FIGURE 50
(Continued)

| | | | |
|---|---|---|---|
| iPS:434939 | 21-225_86C11 | NA | GAAATTGTGTTGACGCAGTCTCCAGGCACCCT GTATTTGTCTCCAGGGGAAAGAGCCACCCTCT CATGCAGGGCCAGTCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCCTCCCAGACAGGTTCAGT GGCAGTGGGTCTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA<br><br>SEQ ID NO: 25977 | CAGGTGCAGCTACAGCAGTGGGGCGCAGGACTG TTGAAGCCTTCGGAGACCCTGTCCCTCACCTGCG CTGTCCATGGTGGTTCTTCAGTGGTTGCTACTG GAGCTGGATCCGCCAGCCCCCAGGGAAGGGCT GGAGTGGATTGGGAAATCAATCATAGTGGAAG CACCAACTACAAACCCGTCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 29983 |
| | | AA | EIVLTQSPGTLYLSPGERATLSCRASQSVYSSYLA WYQQKPGQAPRLLIYGASSRSTGLPDRFSGSGSG TDFALTISRLEPEDCAVYYCQHSDNSPWTFGQG TKVEIK<br><br>SEQ ID NO: 25978 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29984 |
| iPS:434943 | 21-225_87H1 | NA | GAAATTGTGTTGACGCAGTCTCCAGGCACCCT GTCTTTGTCTCCAGGGGAAAGAGCCACCCTCT CCTGCAGGGCCAGTCAGAGTGTTGACAGCAAC TACTTAGCCTGGTACCAGCAGAAACCTGGCCA GGCTCCCAGGCTCCTCATCTATGGTGCATCTG CCAGGACCACTGGCATCCCAGACAGGTTCAGT GGCAGTGGGTCTGGGACAGACTTCACTCTCAC CATCAGCAGACTGGAGCCTGAAGATTTTGCAG TGTATTCCTGTCAGCAGTATGAAAGCTCACCG TGGACGTTCGGCCAAGGGACCAAGGTGGAAA TCAAA<br><br>SEQ ID NO: 25979 | CAGGTGCAGCTGCAGCCGTGGGGCGCAGGACTG TTGAAGCCTTCGGAGACCCTGTCCCTCACCTGCG CTGTCTATGGTGGGTCCTTCAGTGGTTACTACTG GAGCTGGATCCGCCAGCCCCCAGGGAAGGGGCT GGAGTGGATTGGGAAATCAATCATAGTGGACG CACCAACTACAACCCGTCCCTCAAGAGTCGAGTC ACCATATCAGTAGACACGTCAAGGACCAGTTCT CCCTGAAGCTGAGCTCTGTGACCGCCGCGGACAC GGCTGTGTATTACTGTGCGAGAGACTACGTGGT TTGGACGTCTGGGGCCAAGGGACCACGGTCACC GTCTCCTCA<br><br>SEQ ID NO: 29985 |

FIGURE 50
(Continued)

| | | AA | EIVLTQSPGTLSLSPGERATLSCRASQSVDSNYLA WYQQKPGQAPRLLIYGASARTTGIPDRFSGSGSG TDFTLTISRLEPEDFAVYSCQQYESSPWTFGQGT KVEIK SEQ ID NO: 25980 | QVQLQPWGAGLLKPSETLSLTCAVYGGSFSGYYW SWIRQPPGKGLEWIGEINHSGRTNYNPSLKSRVTIS VDTSKDQFSLKLSSVTAADTAVYYCARDYGGLDV WGQGTTVTVSS SEQ ID NO: 29986 |
|---|---|---|---|---|
| iPS:434945 | 21-225_87E5 | NA | GAATTTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCA GCGGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCATTCTGATAACTCACCGT GGACGTTCGGCCAAGGGACCAAGGTGGAAAT CAAA SEQ ID NO: 25981 | CAGGTGCAGTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29987 |
| | | AA | EFVLTQSPGTLYLSPGERATLSCRASQSVYSSYL AWYQQKPGQAPRLLIYGASSRSTGIPDRFSGSGS GTDFALTISRVEPEDCAVYYCQHSDNSPWTFGQ GTKVEIK SEQ ID NO: 25982 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 29988 |

FIGURE 50
(Continued)

| | | | |
|---|---|---|---|
| iPS:434947 | 21-225_87B7 | NA | GACATCCAGATGACCCAGTCTCCATCCTCACT<br>GTCTGCATCTGTAGGAGACAGAGTCACCATCA<br>CTTGTCGGGCGAGTCAGGGCATTAGCAATTAT<br>TTAGCCTGGTTTCAGCAGAAACCAGGGAAAGC<br>CCCTAAGTCCCTGATCTATGCTGCATCCAGTTT<br>GCACAGTGGGGTCCCATCAAAGTTCAGCGGCA<br>GTGGATCTGGGACAGATTTCACTCTCACCATC<br>AGCAGCCTGCAGCCTGAAGATTCTGCAACTTA<br>TTTCTGCCTACTCTATCTTACTTACCCGCTCAC<br>CTTCGGCCAAGGGACACGACTGGAGATTAAA | CAGGTGCAGCTGGTGGTGGAGTCTGGGGGAGGCGTG<br>GTCCAGCCTGGGGAGGTCCCTGAGACTCTCCTGTG<br>CAGCGTCTGATTCACCTTCAGTAGCTATGGCAT<br>GCACTGGGTCCGCCAGGCTCCAGGCAAGGGGCT<br>GGAGTGGGTGGCAGTTATATGTGTATGGAAGT<br>AATAAAACTATGCAGACTCCGTGAAGGGCCGA<br>TTCACCATCTCCAGAGACAATTCCAAGAACACGC<br>TGTATCTGCAAATGAACAGCCTGAGAGCCGAGG<br>ACACGGCTGTGTATTACTGTGCGAGAGATTTTGG<br>AGTGGGCTACTACGGTATGGACGTCTGGGGCCA<br>AGGGACCACGGTCACCGTCTCCTCA |
| | | | SEQ ID NO: 25983 | SEQ ID NO: 29989 |
| | | AA | DIQMTQSPSSLSASVGDRVTITCRASQGISNYLA<br>WFQQKPGKSPKLIYAASSLHSGVPSKFSGSGSG<br>TDFTLTISSLQPEDSATYFCLLYLTYPLTFGQGTR<br>LEIK | QVQLVESGGGVVQPGRSLRLSCAASGFTFSSYGMH<br>WVRQAPGKGLEWVAVIWYDGSNKNYADSVKGRF<br>TISRDNSKNTLYLQMNSLRAEDTAVYYCARDFGVG<br>YYGMDVWGQGTTVTVSS |
| | | | SEQ ID NO: 25984 | SEQ ID NO: 29990 |
| iPS:434955 | 21-225_87C9 | NA | GAAATTGTGTTGACGCAGTCTCCAGGCACCCT<br>GTATTTGTCTCCAGTGGAAAGAGCCACCCTCT<br>CATGCAGGGCCAGTCAGAGTGTTACAGCAGC<br>TACTTAGCCTGGTACCAGCAGAAACCTGGCCA<br>GGCTCCCAGGCTCCTCATTTATGGTGCATCA<br>GCCGGTCCACTGGCATCCCAGACAGGTTCAGT<br>GGCAGTGGGTCTGGGACAGCCTGCGCTCTCAC<br>CATCAGCAGACTGGAGCCTGAAGATTGTGCAG<br>TGTATTACTGTCAGCATTCTGATAACTCACCGT<br>GGACGTTCGGCCAAGGGACCAAGGTGGAAAT<br>CAAA | CAGGTGCAGCTACAGCAGTGGGGCGCAGGACTG<br>TTGAAGCCTTCGGAGACCCTGTCCCTCACCTGCG<br>CTGTCCATGGTGGGTCCTTCAGTGGTTGCTACTG<br>GAGCTGGATCCGCCAGCCCCCAGGGAAGGGCT<br>GGAGTGGATTGGGGAAATCAATCATAGTGGAAG<br>CACCAACTACAACCCGTCCCTCAAGAGTCGAGTC<br>ACCATTTCAGTAGACACGTCCAAGAACCAGTTCT<br>CCCTGAAGCTGAGCTCTGTGACCGCCGCGGACAC<br>GGCTGTGTATTACTGTGCGAGGGACTACGGCGGT<br>ATGGACGTCTGGGGCCAAGGGACCACGGTCACC<br>GTCTCCTCA |
| | | | SEQ ID NO: 25985 | SEQ ID NO: 29991 |

FIGURE 50
(Continued)

| | | | | |
|---|---|---|---|---|
| iPS:434957 | 21-225_87A10 | AA | EIVLTQSPGTLYLSPVERATLSCRASQSVYSSYLA WYQQKPGQAPRLLIYGASSRSTGIPDRFSGSGSG TDFALTISRLEPEDCAVYYCQHSDNSPWTFGQG TKVEIK<br><br>SEQ ID NO: 25986 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 29992 |
| | | NA | GAATTTGTGTTGACGCAGTCTCCAGGCACCCT GTATTTGTCTCCAGGGGAAAGAGCCACCCTCT CGTGCAGGGCCAGTCAGAGTGTTAGCAGCAGC TACTTAGCCTGGTACCAGCAGAAACCTGGCCA GGCTCCCAGGCTCCTCATCTATGGTGCATCA CCAGGGCCCTCTGGCATCCCAGACAGGTTCAGT GGCAGTGGGTCTGGGACAGACTTCACTCTCAC CATCAGCAGACTGGAGCCTGAATATTTGCAG TTTATTACTGTCAGCAGTATGGTAACTCACCG CTCACTTTCGGCGGAGGGACCAAGGTGGAGAT CAAA<br><br>SEQ ID NO: 25987 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAATGG TAACACAGGCTATGCACAGAAGTTCCAGGGCAG AGTCACCATGACCAGGAACACCTCCATAAGCAC AGCCTACATGGAGCTGAACAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA<br><br>SEQ ID NO: 29993 |
| | | AA | EFVLTQSPGTLYLSPGERATLSCRASQSVSSSYL AWYQQKPGQAPRLLIYGASTRASGIPDRFSGSGS GTDFTLTISRLEPEYFAVYYCQQYGNSPLTFGGG TKVEIK<br><br>SEQ ID NO: 25988 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL<br><br>SEQ ID NO: 29994 |

FIGURE 50
(Continued)

| | | | |
|---|---|---|---|
| iPS:434959 | 21-225_87E10 | NA | GACATCGTGATGACCCAGTCTCCAGACTCCCT GGCTGTGTCTCTGGGCGCCAGCAGTCTCCTCA AGTGCAAGTCCAGCAGAGTGTTTACACAGC TCCAACAATATGAACTACTTAGCTTGGTACCA GCAGAAACCTGGACAGCCTCCTAAACTGCTCA TTTACTGGGCATCTACCCGGAAATCCGGGGTC CCTGACCGATTCAGTGGCACGGGTCTGGGAC AGATTTCACTCTCACCATCAGCAGCCTGCAGG CTGAAGATGTGGCAGTTATTACTGTCAGCAA TATTATACTGTCCGTGCAGTTTTGGCCAGGG GACCAAGCTGAAGATCAAA SEQ ID NO: 25989 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCCTATAGCAG TGGCTGGTACTTCTTTGACTACTGGGGCCAGGGA ACCCTGGTCACCGTCTCCTCA SEQ ID NO: 29995 |
| | | AA | DIVMTQSPDSLAVSLGERATIKCKSSQSVLHSSN NMNYLAWYQQKPGQPPKLLIYWASTRKSGVPD RFSGSGSGTDFTLTISSLQAEDVAVYYCQQYYSS PCSFGQGTKLKIK SEQ ID NO: 25990 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YFFDYWGQGTLVTVSS SEQ ID NO: 29996 |
| iPS:434961 | 21-225_87A12 | NA | GAAATTGTGTTGACGCAGTCTCCAGGCACCCG GTATTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGTCCACTGTCATCCAGACAGGTTCAGT GGCAGTGGGTGTGGGACAGACTTCAGTCTCAC CATCAGCAGAGTGGAGCCTGAAGATTGTGCAG TGTATTACTGTCAGCACTCTGATAACTCACCGT GGACGTTCGGCCAAGGGACCAAGGTGGAAAT CAAA SEQ ID NO: 25991 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 29997 |

FIGURE 50
(Continued)

| | | | |
|---|---|---|---|
| | | AA | EIVLTQSPGTRYLSPGERATLSCRASQSVYSSYL AWYQQKPGQAPRLLIYGASSRSTVIPDRFSGSGC GTDFALTISRVEPEDCAVYYCQHSDNSPWTFGQ GTKVEIK<br><br>SEQ ID NO: 25992 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br><br>SEQ ID NO: 29998 |
| iPS:434965 | 21-225_88A1 | NA | AATATCGTGATGACCCAGTCTCCAGACTCCCT GGCTGTGTCTCTGGGCGAGGGCCACCATCA ACTGCAAGTCCAGCCAGAGTGTTTACACAGC TCCAACAATTACAACTACTTAACTTGGTACCA GCAGAAACCAGGACAGCCTCCTAAGCTGCTCC TTTACTGGGCATCTCAGTGGCAGGGTCTGGGAC CCTGACCGATTCAGTGGCAGCGGGTCTGGGAC AGATTTCACTCTCACCATCAGCAGCCTGCAGG CTGAAGATGTGGCAGTTTATTTCTGTCAGCAA TATTATAGTTCCTCCGACGTTCGGCCAAGG GACCAAGGTGGAAATCAAA<br><br>SEQ ID NO: 25993 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGTATAGCAG TGGCTGGTACTACTTTGACTACTGGGGCCAGGGA ACCCTGGTCACCGTCTCCTCA<br><br>SEQ ID NO: 29999 |
| | | AA | NIVMTQSPDSLAVSLGARATINCKSSQSVLHSSN NYNYLTWYQQKPGQPPKLLLYWASTRKSGVPD RFSGSGSGTDFTLTISSLQAEDVAVYFCQQYYSS PPTFGQGTKVEIK<br><br>SEQ ID NO: 25994 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YYFDYWGQGTLVTVSS<br><br>SEQ ID NO: 30000 |

FIGURE 50
(Continued)

| | | | |
|---|---|---|---|
| iPS:434969 | 21-225_88H1 | NA | GAAATTGTGTTGACGCAGTCTCCAGGCACCCT GTATTGTCTCCAGGGGAAAGAGCCACCCTGT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACGGTCATCCCAGACAGGTTCAGT GGCAGTGGGTGTGGGACAGACTTCGCTCTCAC CATCAGCAGACAGAGTGGAGCCTGAAGATTGTGCAG TGTATTACTGTCAGCATTCTGATAACTCACCGT GGACGTTCGGCCAAGGGACCAAGGTGAAAT CAAA<br><br>SEQ ID NO: 25995 | CAGGTGCAGCTACAGCAGTGGGGCGCAGGACTG TTGAAGCCTTCGGAGACCCTGTCCCTCACCTGCG CTGTCCATGTGGGTCCTTCAGTGGTTGTACTG GAGCTGGATCCGCCAGCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGGACAC GGCTGTGTATTACTGTGCGAGGGACTACGGCGGT ATGGACGTCTGGGGCCAAGGGACCACGGTCACC GTCTCCTCA<br><br>SEQ ID NO: 30001 |
| | | AA | EIVLTQSPGTLYLSPGERATLSCRASQSVYSSYLA WYQQKPGQAPRLLIYGASSRSTVIPDRFSGSGCG TDFALTISRVEPEDCAVYYCQHSDNSPWTFGQG TKVEIK<br><br>SEQ ID NO: 25996 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30002 |
| iPS:434971 | 21-225_88G2 | NA | GACATCGTGATGACCCAGTCTCCAGATTGCCT GGCTGTGTCTCTGGGCGAGAGGGCCACCATCA ACTGCAAGTCCAGCCAGAGTGTTTTATACACC TCCAACAATAACAACAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCAA TATTATAATACTCCGTGGACGTTTGGTCCAAGG GACCAAGGTGGAAATCAAA<br><br>SEQ ID NO: 25997 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCCTCA<br><br>SEQ ID NO: 30003 |

FIGURE 50
(Continued)

| | | | |
|---|---|---|---|
| iPS:434973 | 21-225_88B4 | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQQYYNT PWTFVQGTKVEIK | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTSS |
| | | | SEQ ID NO: 25998 | SEQ ID NO: 30004 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTATACATC TCCAACAATAATAATTACTTAGCTTGGTACCA GCAGAAACCAGGACAGCCTCCTAAACTGCTCA TTTACTGGGCATCTACCCGGGAATCCGGGGTC CCTGCCCGATTCAGTGGCAGCGGGTCTGGGAC AGATTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCCTAACAGTG GTGACACAGGCTATGCACAGAAGTTCCAGGCA GTGTCACCATGACCAGGAACACCTCCATAACCAC AGCCTACATGGAGCTGAGCAGCCTGAGATCTGA GGACACGGCCGTGTATTACTGTTCGTATAGCAGT GGCTGGTACTACTTTGACTACTGGGGCCAGGAA CCCTGGTCACCGTCTCCTCA |
| | | | SEQ ID NO: 25999 | SEQ ID NO: 30005 |
| | | AA | DIVMTQSPDSLAVSLGERATINCKSSQSVLYISN NNNYLAWYQQKPGQPPKLLIYWASTRESGVPA RFSGSGSGTDFTLTISSLQAEDVAVYYCQQYYST PPTFGQGTKVEIK | QVQLVQSGAEVKKPGASVKVSCKASGYTFTNYDIN WVRQATGQGLEWMGWMNPNSGDTGYAQKFQGS VTMTRNTSITTAYMELSSLRSEDTAVYYCSYSSGW YYFDYWGQGTLVTSS |
| | | | SEQ ID NO: 26000 | SEQ ID NO: 30006 |

FIGURE 50
(Continued)

| | | | | |
|---|---|---|---|---|
| iPS:434977 | 21-225_88A5 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATGATTACCCATTC ACTTTCGGCCCTGGGACCAAAGTGGAAATCAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCTGGAACACCTCCATACGAC TGCCTACATGGAGCTGAGCAGCCTGAGATCTGAG GACACGGCCGTGTATTACTGTGCGCGAGGGTTTT ACGATTTTTGACTGGTTATTCCCCACTACTAC TACTACGATATGGACGTCTGGGGCCAAGGGACC ACGGTCACCGTCTCCTCA |
| | | | SEQ ID NO: 26001 | SEQ ID NO: 30007 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNDYPFTFGPGT KVEIK | QVQLVQSGAEVKKPGASVKVSCKASGYTFTSYDIN WVRQATGQGLEWMGWMNPNSGNTGYAQKFQGR VTMTWNTSIRTAYMELSSLRSEDTAVYYCARGFYD FLTGYSPTYYYYDMDVWGQGTTVTVSS |
| | | | SEQ ID NO: 26002 | SEQ ID NO: 30008 |
| iPS:434981 | 21-225_88E7 | NA | GAAATTGTGTTGACGCAGTCTCCAGGCACCCT GTCTTTGTCTCCAGGGGAAAGAGCCACCCTCT CCTGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTCTGATAACTCACCGT GGACGTTCGGCCAAGGGACCAAGGTGGAAAT CAAA | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGGACAC GGCTGTGTATTACTGTGCGAGGGACTACGGCGGT ATGGACGTCTGGGGCCAAGGGACCACGGTCACC GTCTCCTCA |

FIGURE 50
(Continued)

| | | | SEQ ID NO: 26003 | SEQ ID NO: 30009 |
|---|---|---|---|---|
| iPS:434983 | 21-225_88F7 | AA | EIVLTQSPGTLSLSPGERATLSCRASQSVYSSYLA WYQQKPGQAPRLLIYGASSRSTGIPDRFSGSGSG TDFALTISRVEPEDCAVYYCQHSDNSPWTFGQG TKVEIK | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS |
| | | | SEQ ID NO: 26004 | SEQ ID NO: 30010 |
| | | NA | GAAATTGTGTTGACGCAGTCTCCAGGCACCCT GTCTTTGTCTCCAGGGGAAAGAGCCACCCTCT CATGCAGGGCCAGTCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA | CAGGTGCAGCTACAGCAGTGGGGCGCAGGACTG TTGAAGCCTTCGGAGACCCTGTCCTCACCTGCG CTGTCCATGGTGGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA |
| | | | SEQ ID NO: 26005 | SEQ ID NO: 30011 |
| | | AA | EIVLTQSPGTLSLSPGERATLSCRASQSVYSSYLA WYQQKPGQAPRLLIYGASSRSTGIPDRFSGSGSG TDFALTISRLEPEDCAVYYCQHSDNSPWTFGQG TKVEIK | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS |
| | | | SEQ ID NO: 26006 | SEQ ID NO: 30012 |

FIGURE 50
(Continued)

| | | | |
|---|---|---|---|
| iPS:434995 | 21-225_88G9 | NA | GAAATTGTGTTGACGCAGTCTCCAGGCACCCTGGTATTTGTCTCCAGGGGAAAGAGCCACCCTCTCCTGCAGGGCCAGTCAGAGTGTTTACAGCAGCTACTTAGCCTGGTACCAGCAGAAACCTGGCCAGGCTCCCAGGCTCCTCATTTATGGTGCATCCAGCCGGTCCACTGGCATCCCAGACAGGTTCAGTGGCAGTGGGTCTGGGACAGACTTCGCTCTCACCATCAGCAGCAGAGTGGAGCCTGAAGATTGTGCAGTGTATTACTGTCAGCACTCTGATAACTCACCGTTGGACGTTCGGCCAAGGGACCAAGGTGGAAAT CAAA<br><br>SEQ ID NO: 26007 | CAGGTGCAGCTACAGCAGTGGGGCGCAGGACTGTTGAAGCCTTCGGAGACCCTGTCCCTCACCTGCGCTGTCCATGTGGGTCCTTCAGTGGTTGTTACTGGAGCTGGATCCGCCAGCCCCCAGGGAAGGGCTGGAGTGGATTGGGGAAATCAATCATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA<br><br>SEQ ID NO: 30013 |
| | | AA | EIVLTQSPGTRYLSPGERATLSCRASQSVYSSYLAWYQQKPGQAPRLLIYGASSRSTGIPDRFSGSGSGTDFALTISRVEPEDCAVYYCQHSDNSPWTFGQGTKVEIK<br><br>SEQ ID NO: 26008 | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTVSS<br><br>SEQ ID NO: 30014 |
| iPS:434997 | 21-225_88C10 | NA | GACATCGTGATGACCCAGTCTCCAGACTCCCTGGCTGTGTCTCTGGGCGAGAGGGCCACCATCAACTGCAAGTCCAGCCAGAGTGTTTTACACGACAGCTCCAACAATTGGAATTACTTAGCTTGGCACCAGCAGAAACCAGGACAGCCTCCTAAGTTGCTCATTCACTGGGCATTTACTCGGAATCCGGGGTCCCTGACCGATTCAGTGGCGGCGGGTCTGGGACAGATTTCACTCTCACCATCAGCAGCCTGCAGGCTGAAGATGTGGCAGTTTATTACTGTCAGCAATATTATAGTAGCTCCCCGACGTTCGGCCAAGGGACCAAGGTGGAAATCAAA<br><br>SEQ ID NO: 26009 | CAGGTGCAGCTGGTGCAGTCTGGGGCTGAGGTGAAGAAGCCTGGGGCCTCAGTGAGGGTCTCCTGCAAGGCTTCTGGATACACCTTCAGCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACGGCCGTGTACTACTGTGCGAGTAGCAGTGGCTGGTACTACTTTGACTCCTGGGGCCAGGGAACCCTGGTCACCGTCTCCTTA<br><br>SEQ ID NO: 30015 |

FIGURE 50
(Continued)

| | | | | |
|---|---|---|---|---|
| iPS:434999 | 21-225_75A8 | AA | DIVMTQSPDSLAVSLGERATINCKSSQSVLHSSN NWNYLAWHQQKPGQPPKLLIHWAFTRKSGVPD RFSGGGSGTNFTLTISSLQAEDVAVYYCQQYYR APPTFGQGTKVEIK<br>SEQ ID NO: 26010 | QVQLVQSGAEVKKPGASVRVSCKASGYTFSNYDIN WVRQATGQGLEWMGWMTPNSGNTGYAQKFQGR VTMTRNTSISTAYMELSSLRSEDTAVYYCASSSGW YYFDSWGQGTLVTVSL<br>SEQ ID NO: 30016 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTCTGATAACTCACCGT GGACGTTCGGCCAAGGGACCAAGGTGAAAT CAAA<br>SEQ ID NO: 26011 | CAGGTGCAGCTACAGCAGTGGGGCGCAGGACTG TTGAAGCCTTCGGAGACCCTGTCCCTCACCTGCG CTGTCCATGGTGGGTCTCTTCAGTGGTTGCTACTG GAGCTGGATCCGCCAGCCCCAGGGAAGGGGCT GGAGTGGATTGGGGAAATCAATCATAGTGGAAG CACCAACTACAACCGTCCTCCTCAAGAGTCGAGTC ACCATTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30017 |
| | | AA | EIVLTQSPGTLYLSPGERATLSCRASQSVYSSYLA WYQQKPGQAPRLLIYGASSRATGIPDRFSGSGSG TDFALTISRVEPEDCAVYYCQHSDNSPWTFGQG TKVEIK<br>SEQ ID NO: 26012 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30018 |

FIGURE 50
(Continued)

| | | | |
|---|---|---|---|
| iPS:435009 | 21-225_89G4 | NA | GATATTGTGATGACTCAGTCTCCACTCTCCCTG CCCGTCACCCCTGGAGAGCCGGCCTCCATCTC CTGCAGGTCTAGTCAGAGCCTCCTGCATAGTA GTGGATACAACTATTTGGATTGGTACCTGCAG AAGCCAGGGCAGTCTCCACAGCTCCTGATCTA TTTGGGTTCTAATGGGCCTCCGGGGTCCCTG ACAGGTTCAGTGGCAGTGGTTCAGGCACAGAT TTTACACTGAAAATCAGCAGAGTGGAGGCTGA GGATATTGGGGTTTATTACTGCATGCAAGCTC TACATATTCCTCTCACTTTCGGCGGAGGGACC AAGGTGGAGATCAAA<br><br>SEQ ID NO: 26013 | GAGGTGCAGCTGGTGGTGGAGTCTGGGGGAGGCTTG GTACAGCCGGGGGGGGGGGGTCCCTGAGACTCTCCTGTG CAGCCTCTGGATTCACCTTCAGTAGTACGACAT GCACTGGGTCCGCAAGCTACAGGAGAAAGGTCT GGAGTGGGTCTCAGTACTATTGGTACTGCTGGTGAC ACATACTATCCAGGTCCGTGAAGGGCCGATTCA CCATCTCCAGAGAAATGCCAAGAACTCCTTGTA TCTTCAAATGAACAGCCTGAGAGCCGGGACAC GGCTGTGTATTTCTGTGCAAGAGCTCTTGACTAC GGTGACTCCTTGGGCTACTACTACGGTATGG ACGTCTGGGGCCAAGGGACCACGGTCACCGTCTC CTCA<br><br>SEQ ID NO: 30019 |
| | | AA | DIVMTQSPLSLPVTPGEPASISCRSSQSLLHSSGY NYLDWYLQKPGQSPQLLIYLGSNRASGVPDRFS GSGSGTDFTLKISRVEAEDIGVYYCMQALHIPLT FGGGTKVEIK<br><br>SEQ ID NO: 26014 | EVQLVESGGGLVQPGGSLRLSCAASGFTFSSYDMH WVRQATGKGLEWVSAIGTAGDTYYPGSVKGRFTIS RENAKNSLYLQMNSLRAGDTAVFCARALDYGDS LGYYYGMDVWGQGTTVTVSS<br><br>SEQ ID NO: 30020 |
| iPS:435013 | 21-225_89D5 | NA | GAAATTGTGTTGACGCAGTCTCCAGGCACCCT GTATTTGTCTTCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGTGCATCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCACCG TGGACGTTCGGCCAAGGGACCAAGGTGGAAA TCAAA<br><br>SEQ ID NO: 26015 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 30021 |

FIGURE 50
(Continued)

| | | | | |
|---|---|---|---|---|
| iPS:435015 | | AA | EIVLTQSPGTLYLSSGERATLSCRASQSVYSSYLA WYQQKPGQAPRLLIYGASSRSTGIPDRFSGSGSG TDFALTISRLEPEDFAVYYCQHYDNSPWTFGQG TKVEIK<br><br>SEQ ID NO: 26016 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30022 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTAACAGCAAC TACTTAGCCTGGTACCAGCAGAAACCTGGCCA GGCTCCCAGGCTCCTCATCTATGGTGCATTCA GCAGGGCCACTGGCATCCCAGACAGGTTCAGT GGCAGTGGGTCTGGGACAGACTTCAATCTCAT CATCAGCAGACTGGAGCCTGAAGATTTTGCAG TGTATTACTGTCAGCAGTATGAAAGTCAGTG TGGACGTTCGGCCAAGGGACCAAGGTGGAAA TCAAA<br><br>SEQ ID NO: 26017 | CAGGTGCAGCTACAACAGTGGGGCGCAGGACTG TTGAAGCCTTCGGAGACCCTGTCCCTCACTTGCG CTGTCTATGGTGGGTCCTTCAGTGGTTGCTACTG GAGCTGGATCCGCCAGCCCCAGGGAAGGGCT GGAGTGGATTGGGGAAATCAATTATAGTGGAAG CACCAACTTCAACCCGTCCCTCAAGAGTCGAGTC ACCATATCAGCTGACACGTCCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA<br><br>SEQ ID NO: 30023 |
| 21-225_89H5 | | AA | EIVLTQSPGTLSLSPGERATLSCRASQSVNSNYLA WYQQKPGQAPRLLIYGAFSRATGIPDRVSGSGS GTDFNLIISRLEPEDFAVYYCQQYESSVWTFGQG TKVEIK<br><br>SEQ ID NO: 26018 | QVQLQQWGAGLLKPSETLSLTCAVYGGSFSGCYW SWIRQPPGKGLEWIGEINYSGSTNFNPSLKSRVTISA DTSKNQFSLKLSSVTAADTAVYYCARDYGGMDV WGQGTTVTVSS<br><br>SEQ ID NO: 30024 |

FIGURE 50
(Continued)

| | | | |
|---|---|---|---|
| iPS:435025 | 21-225_89E10 | NA | GAAATTGTGTTGACGCAGTCTCCAGGCACCCT GTATTTGTCTTCAGGGGAAAGAGCCACCCTCT CCTGCAGGGCCAGTCAGTCAGAGTGTTTACAGCAGC TACTTAGCCTGGTACCAGCAGAAACCTGGCCA GGCTCCCAGGCTCCTCATTTATGGTGTCATCA GCCGGTCCACTGTCATCCCAGACAGGTTCAGT GGCAGTGGGTCTGGGACAGACTTCGCTCTCAC CATCAGCAGACTGGAGCCTGAAGATTTTGCAG TGTATTACTGTCAGCATTCTGATAACTCTCCGT GGACGTTCGGCCAAGGGACCAAGGTGGAAAT CAAA<br>SEQ ID NO: 26019 |
| | | AA | EIVLTQSPGTLYLSSGERATLSCRASQSVYSSYLA WYQQKPGQAPRLLIYGASSRSTVIPDRFSGSGSG TDFALTISRVEPEDFAVYYCQHSDNSPWTFGQG TKVEIK<br>SEQ ID NO: 26020 |
| | | NA | CAGGTGCAGCTGCAGCCGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGAAGGGCT GGAGTGGATTGGGGAAATCAATCATAGTGGAAG CACCAACTACAAACCCGTCCTCAAGAGTCGAGTC ACCATTTCAGTAGACACGTCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 30025 |
| iPS:435029 | 21-225_89A11 | AA | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30026 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTGACAGCAAC TTCTTAGCCTGGTACCAGCAGAAACCTGGCCA GGCTCCCAGGCTCCTCATCTATGGTGCATCTG CCAGGACCACTGGCATCCCAGACAGGTTCAGT GGCAGTGGGTCTGGGACAGACTTCACTCTCAC CATCAGCAGACTGGAGCCTGAAGATTTTGCAG TGTATTCCTGTCAGCAGTATGATGAAATCTCACCG TGGACGTTCGGCCAAGGGACCAAGGTGGAAA TCAAA<br>SEQ ID NO: 26021 | | | | CAGGTGCAGCTGCAGCCGTGGGGCGCAGGACTG TTGAAGCCTTCGGAGACCCTGTCCCTCACCTGCG CTGTCTATGGTGGGTCCTTCAGTGGTTACTACTG GAGCTGGATCCGCCAGCCCCAGGAAGGGCT GGAGTGGATTGGGGAAATCAATCATAGTGGACG CACCAGTACAACCCGTCCTCAAGAGTCGAGTC ACCATATCAGTAGACACGTCAAGAACCAGTTCT CCCTGAAGCTGAGCTCTGTGACCGCCGCGACAC GGCTGTGTATTACTGTGCGAGAGACTACGTGGT TTGGACGTCTGGGGCCAAGGGACCACGGTCACC GTCTCCTCA<br>SEQ ID NO: 30027 |

FIGURE 50
(Continued)

| | | | | |
|---|---|---|---|---|
| iPS:435039 | | AA | EIVLTQSPGTLSLSPGERATLSCRASQSVDSNFLAWYQQKPGQAPRLLIYGASARTTGIPDRFSGSGSGTDFTLTISRLEPEDFAVYSCQQYEISPWTFGQGTKVEIK<br>SEQ ID NO: 26022 | QVQLQPWGAGLLKPSETLSLTCAVYGGSFSGYYWSWIRQPPGKGLEWIGEINHSGRTSYNPSLKSRVTISVDTSKNQFSLKLSSVTAADTAVYYCARDYGGLDVWGQGTTVTVSS<br>SEQ ID NO: 30028 |
| | 21-225_90G4 | NA | GAAATTGTGTTGACGCAGTCTCCAGGCACCCTGTATTTGTCTCCAGGGGAAAGAGCCACCCTCTCATGCAGGGCCAGTCAGAGTGTTTACAGCAGCTACTTAGCCTGGTACCAGCAGAAACCTGGCCAGGCTCCCAGGCTCCTCATTTATGGTGCATCAGCGCGGTCCACTGTCATCCCAGACAGGTTCAGTGGCAGTGGGTCTGGGACAGACTTCGCTCTCACCATCAGCAGACTGGAGCCTGAAGATTGTGCAGTGTATTACTGTCAGCAGTATGAATAACTCACCGTGGACGTTCGGCCAAGGGACCAAGGTGGAAATCAAA<br>SEQ ID NO: 26023 | CAGGTGCAGCTACAGCAGTGGGGCGCAGGACTGTTGAAGCCTTCGGAGACCCTGTCCCTCACCTGCGCTGTCCATGGTGGGTCTTCAGTGGTTGCTACTGGAGCTGGATCCGCCAGCCCCCAGGGAAGGGGCTGGAGTGGATTGGGGAAATCAATCATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA<br>SEQ ID NO: 30029 |
| | | AA | EIVLTQSPGTLYLSPGERATLSCRASQSVYSSYLAWYQQKPGQAPRLLIYGASSRSTVIPDRFSGSGSGTDFALTISRVEPEDCAVYYCQHSDNSPWTFGQGTKVEIK<br>SEQ ID NO: 26024 | QVQLQQWGAGLLKPSETLSLTCAVHGGSFSGCYWSWIRQPPGKGLEWIGEINHSGSTNYNPSLKSRVTISVDTSKNQFSLKLSSVTAADTAVYYCARDYGGMDVWGQGTTVTVSS<br>SEQ ID NO: 30030 |

FIGURE 50
(Continued)

| | | | |
|---|---|---|---|
| iPS:435041 | 21-225_90A5 | NA | GAAATTGTGTTGACGCAGTCTCCAGGCACCCT GTATTTGTCTCCAGGGGAAAGAGCCACCCTCT CATGCAGGGCCAGTCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGAGTGGAGCATGAAGATTTTGCAG TGTATTACTGTCAGCACTATGATAACTCACCG TGGACGTTCGGCCAAGGGACCAAGGTGGAAA TCAAA<br>SEQ ID NO: 26025 | CAGGTGCAGCTACAGCAGTGGGGCGCAGGACTG TTGAAGCCTTCGGAGACCGTCCCTCCACCTGCG CTGTCCATGGTGGGTCTTCAGTGGTTGCTACTG GAGCTGGATCCGCCAGCCCCAGGGAAGGGCT GGAGTGGATTGGGAAATCAATCATAGTGGAAG CACCAACTACAACCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30031 |
| | | AA | EIVLTQSPGTLYLSPGERATLSCRASQSVYSSYLA WYQQKPGQAPRLLIYGASSRATGIPDRFSGSGSG TDFALTISRVEHEDFAVYYCQHYDNSPWTFGQG TKVEIK<br>SEQ ID NO: 26026 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30032 |
| iPS:435043 | 21-225_90G5 | NA | GAAATTGTGTTGACGCAGTCTCCAGGCACCCT GTATTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCATCATTTATGGTGCATCCA GCCGGGCCACTGGCATCCCAGACAGGTTCAGT GGCAGTGGGTCTGGGACAGACTTCGCTCTCAC CATCAGCAGAGTGGAGCATGAAGATTTTGCAG TGTATTACTGTCAGCACTACTATGATAACTCACCG TGGACGTTCGGCCAAGGGACCAAGGTGGAAA TCAAA<br>SEQ ID NO: 26027 | CAGGTGCAGCTACAGCAGTGGGGCGCAGGACTG TTGAAGCCTTCGGAGACCGTCCCTCCACCTGCG CTGTCCATGGTGGGTCCTTCAGTGGTTGCTACTG GAGCTGGATCCGCCAGCCCCAGGGAAGGGCT GGAGTGGATTGGGAAATCAATCATAGTGGAAG CACCAACTACAACCGTCCCTCAAGAGTCGAGTC ACCATTTCAGTAGACACGTCAAGAACCAGTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30033 |

FIGURE 50
(Continued)

| | | | |
|---|---|---|---|
| iPS:435045 | 21-225_90H5 | AA | EIVLTQSPGTLYLSPGERATLSCRASQSVYSSYLA WYQQKPGQAPRLIIYGASSRATGIPDRFSGSGSG TDFALTISRVEHEDFAVYYCQHYDNSPWTFGQG TKVEIK<br>SEQ ID NO: 26028 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30034 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATATAAGTTACCCGATC ACCTTCGGCCAAGGGACACGACTGGAGATTAA A<br>SEQ ID NO: 26029 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGTCTCCAGGCAAGGGGCT GGAGTGGGTGGCAGTTATATGGTATGAAGGAAG TAATACATACTATGCAGACTCCGTGAAGGGCCGA TTCACCATCTCAGAGACAATTCCAAGAACACGC TGTATCTGCAAATGAACAGCCTGAGAGCCGAGG ACACGGCTGTATATTACTGTGTGAGAGATGGG GTGGTTAGATGACTACTGGGGCCAGGGAACCCT GGTCACCGTCTCCTCA<br>SEQ ID NO: 30035 |
| | | AA | DIQMTQSPSSLSASVGDRVTITCRASQGIRNDLG WYQQKPGKAPKRLIYIASSLQSGVPSRFSGSGSG TEFTLTISSLQPEDFATYYCLQHNSYPITFGQGTR LEIK<br>SEQ ID NO: 26030 | QVQLVESGGGVVQPGRSLRLSCAASGFTFSDYGM HWVRQSPGKGLEWVAVIWYEGSNTYADSVKGR FTISRDNSKNTLYLQMNSLRAEDTAVYYCVREMG WLDDYWGQGTLVTVSS<br>SEQ ID NO: 30036 |

FIGURE 50
(Continued)

| | | | |
|---|---|---|---|
| iPS:435051 | 21-225_90D9 | NA | GACATCGTGATGACCCAGTCTCCAGACTCCCT GGCTGTGTCTCTGGGCGAGAGGGCCACCATCA TCTGCAAGTCCAGCAGTGTTTTACACAGC TCCAACAATTATAACTACTTAGCTTGGTACCA GCAGAAGCCAGGACAGTCCCCTAAGGTGCTC ATTTACTGGACATCTACCCGGGAATCCGGGGT CCCTGACCGATTCAGTGGCAGCGGGTCTGGA CAGATTTCACTCTCACCATCAGCAGCCTGCAG GCTGAAGATGTGGCAGTTTATTACTGTCAGCA ATATCTTAGTAGTCCTCGACGTTCGGCCAAG GGACCAAGGTGGAAATCAAA SEQ ID NO: 26031 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGCA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCCTGGGGCCAGGGA ACCCTGGTCACCGTCGCCTCA SEQ ID NO: 30037 |
| | | AA | DIVMTQSPDSLAVSLGERATIICKSSQTVLHSSNN YNYLAWYQQKPGQPPKVLIYWTSTRESGVPDRF SGSGSGTDFTLTISSLQAEDVAVYYCQQYLSSPL TFGQGTKVEIK SEQ ID NO: 26032 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS SEQ ID NO: 30038 |
| iPS:435053 | 21-225_75F9 | NA | GACATCGTGATGACCCAGTCTCCAGACTCCCT GCCTGTGTCTCTGGGCGAGAGGGCCACCGTCA ACTGCAAGTCCAGCAGAGTGTTTTACACAAC TCCAACAATAATAACTACTTGGCTTGGTACCA GCAGAAACCAGGACAGCCTCCTAAGCTGCTCA TTTACTGGGCATCTACGCGGGAGTCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAACAA TATTATAGTAGTCCTCCGACGTTCGGCCAAGG GACCAAGGTGGAAATCAAA SEQ ID NO: 26033 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACAGAAGTTCCAGGTGG TAACACAGGCTATGCACAGAAGTTCCAGGCAG AGTCACCATGACCAGGAACACCTCCATAAGCAC AGCCTACATGGAGCTGAGCAGCCTGAGATCTGA GGACACGGCCGTGTATTACTGTGCCTATAGCAGT GGCTGGTACATCTTTGACTACTGGGGCCAGGGAA CCCTGGTCACCGTCTCCTCA SEQ ID NO: 30039 |

FIGURE 50
(Continued)

| | | | |
|---|---|---|---|
| iPS:435055 | 21-225_90F10 | AA | DIVMTQSPDSLPVSLGERATVNCKSSQSVLHNSN NNNYLAWYQQKPGQPPKLLIYWASTRESGVPD RFSGSGSGTDFTLTISSLQAEDVAVYYCQQYYSS PPTFGQGTKVEIK SEQ ID NO: 26034 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YIFDYWGQGTLVTVSS SEQ ID NO: 30040 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGTCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTATGATAACTCACCG TGGACGTTCGGCCAAGGGACCAAGGTGGAAA TCAAA SEQ ID NO: 26035 | CAGGTGCAGTCACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCGTCCTCCTCAAGAGTCGAGTC ACCATTCAGTAGACACGTCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA SEQ ID NO: 30041 |
| | | AA | EIVLTQSPGTLYLSPGERATLSCRASQSVYSSYLA WYQQKPGQAPRLLIYGASSRSTGIPDRFSGSGSG TDFALTISRLEPEDCAVYYCQHYDNSPWTFGQG TKVEIK SEQ ID NO: 26036 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 30042 |

FIGURE 50
(Continued)

| | | | | |
|---|---|---|---|---|
| iPS:435059 | 21-225_90C11 | NA | GATATTGTGATGACTCAGTCTCCACTCTCCCTG CCCGTCACCCCTGGAGAGCGGCCTCCATCTC ATGCAGGTATAGTCAGAGCCTCGTGCATAGTA GTGGATACAACTATTTGGATTGGTACCTGCAG AAGCCAGGGCAGTCTCCACAGCTCGTTATCTA TTTGGGTTCTAATGGGCCTCCGGGGTCCCTG ACAGGTTCAGTGGCAGTGGATCAGGTTCAGAT TTTACACTGAAGATCAGCAGAGTGGAGGCTGA GGATGTTGGACTTTATTACTGCATGCAAGCTC TACACCCTCCTCACTTTCGGCGGAGGGACC AAGGTGGAGATCAAA | GAGGTGCAGCTGGTGGAGTCTGGGGGAGGCTTG GTACAGCCGGGGGGGTCCCTGAGACTCTCCTGTG CAGCCTCTGGATTCACCTTCAGTAACTACGACAT GCACTGGGTCCGCCAAGCTACAGGAAAAGGTCT GGAGTGGGTCTCAGTATTGGTACTGCTGGTGAC ACATACTATCCAGGCTCCGTGAAGGGCCGATTCA CCATCTCCAGAGAAAATGCCAAGAACTCCTTGTA TCTTCAAATGAACAGCCTGAGAGCCGGGGACAC GGCTGTGTATTACTGTGCAAGAGTTCTTGACTAC GGTGACTCCTGGGCTACTACTACTACGGTATGG ACGTCTGGGGCCAAGGGACCACGGTCACCGTCTC CTCA |
| | | | SEQ ID NO: 26037 | SEQ ID NO: 30043 |
| | | AA | DIVMTQSPLSLPVTPGEPASISCRYSQSLVHSSGY NYLDWYLQKPGQSPQLVIYLGSNRASGVPDRFS GSGSGSDFTLKISRVEAEDVGLYYCMQALHPPL TFGGGTKVEIK | EVQLVESGGGLVQPGGSLRLSCAASGFTFSNYDMH WVRQATGKGLEWVSAIGTAGDTYYPGSVKGRFTIS RENAKNSLYLQMNSLRAGDTAVYYCARVLDYGDS WAPTTTVGMDVWGQGTTVTVSS |
| | | | SEQ ID NO: 26038 | SEQ ID NO: 30044 |
| iPS:435071 | 21-225_91F1 | NA | GACATCGTGATGACCCAGTCTCCAGATTGCCT GGCTGTGTCTCTGGGCGAGAGGGCCACCATCA ACTGCAAGTCCAGCCAGAGTGTTTTATACAC TCCAACAATAACAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCACT ATTATAATACTCCGTGGAAGTTTGTCAAGGG ACCAAGGTGGAAATCAAA | CAGGTGCAGCTGGTGCAGTCTGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACAGTTCAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA |
| | | | SEQ ID NO: 26039 | SEQ ID NO: 30045 |

FIGURE 50
(Continued)

| | | | |
|---|---|---|---|
| iPS:435073 | 21-225_91B2 | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYYNT PWKFVQGTKVEIK<br>SEQ ID NO: 26040 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS<br>SEQ ID NO: 30046 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCA GCGGGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTATGATAATCACCG TGGACGTTCGGCCAAGGGACCAAGGTGGAAA TCAAA<br>SEQ ID NO: 26041 | CAGGTGCAGTCAGTACAGAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCGTCCCTCCAAGAGTCGAGTC ACCATTCAGTAGACACGTCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 30047 |
| | | AA | EIVLTQSPGTLYLSPGERATLSCRASQSVYSSYLA WYQQKPGQAPRLLIYGASSRSTGIPDRFSGSGSG TDFALTISRVEPEDCAVYYCQHYDNSPWTFGQG TKVEIK<br>SEQ ID NO: 26042 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTSS<br>SEQ ID NO: 30048 |

FIGURE 50
(Continued)

| | | | |
|---|---|---|---|
| iPS:435075 | 21-225_91B3 | NA | GAAATTGTGTTGACGCAGTCTCCAGGCACCCT GTATTGTCTCCAGGGGAAAGAGCCACCCTCT CATGCAGGGCCAGTCAGTCAGAGTGTTTACAGCAGC TACTTAGCCTGGTACCAGCAGAAACCTGGCCA GGCTCCCAGGCTCCTCATTTATGGTGTGCATCA GCCGGTCCACTGGCATCCCAGACAGGTTCAGT GGCAGTGGGTCTGGGACAGACTTCGCTCTCAC CATCAGCAGAGTGGAGCATGAAGATTGTGCA GTGTATTACTGTCAGCACTATGATAACTCACC GTGGACGTTCGGCCAAGGGACCAAGGTGGAA ATCAAA<br>SEQ ID NO: 26043 | CAGGTGCAGCTACAGCAGTGGGGCGCAGGACTG TTGAAGCCTTCGGAGACCGTCCCTGCACCTGCG CTGTCCATGGTGGGTCTTCAGTGGTTGCTACTG GAGCTGGATCCGCCAGCCCCAGGGAAGGGCT GGAGTGGATTGGGGAAATCAATCATAGTGGAAG CACCAACTACAAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30049 |
| | | AA | EIVLTQSPGTLYLSPGERATLSCRASQSVYSSYLA WYQQKPGQAPRLLIYGASSRSTGIPDRFSGSGSG TDFALTISRVEHEDCAVYYCQHYDNSPWTFGQG TKVEIK<br>SEQ ID NO: 26044 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30050 |
| iPS:435077 | 21-225_91F3 | NA | GAAATTGTGTTGACGCAGTCTCCAGGCACCCT GTATTGTCTCCAGGGGAAAGAGCCACCCTCT CATGCAGGGCCAGTCAGAGTGTTACAGCAGC TACTTAGCCTGGTACCAGCAGAAACCTGCCCA GGCTCCCAGGCTCCTCATTTATGGTGCATCA GCCGGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCATTCTGATAACTCACCGT GGACGTTCGGCCAAGGGACCAAGGTGGAAAT CAAA<br>SEQ ID NO: 26045 | CAGGTGCAGCTACAGCAGTGGGGCGCAGGACTG TTGAAGCCTTCGGAGACCGTCCCTGCACCTGCG CTGTCCATGTGTGGGTCTTCAGTGGTTGCTACTG GAGCTGGATCCGCCAGCCCCAGGGAAGGGGCT GGAGTGGATTGGGGAAATCAATCATAGTGGAAG CACCAACTACAAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30051 |

FIGURE 50
(Continued)

| | | | |
|---|---|---|---|
| iPS:435079 | 21-225_91B4 | AA | EIVLTQSPGTLYLSLSPGERATLSCRASQSVYSSYLA WYQQKPAQAPRLLIYGASSRSTGIPDRFSGSGSG TDFALTISRVEPEDCAVYYCQHSDNSPWTFGQG TKVEIK<br>SEQ ID NO: 26046 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30052 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATCATTTATGGTGCATCA GCGAGTCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTATGATAACTCACCG TGGACGTTCGGCCAAGGGACCAAGGTGGAAA TCAAA<br>SEQ ID NO: 26047 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30053 |
| | | AA | EIVLTQSPGTLYLSLSPGERATLSCRASQSVYSSYLA WYQQKPGQAPRLLIYGASSRSTGIPDRFSGSGSG TDFALTISRVEPEDCAVYYCQHYDNSPWTFGQG TKVEIK<br>SEQ ID NO: 26048 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30054 |

FIGURE 50
(Continued)

| | | | |
|---|---|---|---|
| iPS:435087 | 21-225_91G8 | NA | GACATCGTGATGACCCAGTCTCCAGATTGCCT GGCTGTGTCTCTGGGCGAGAGGGCCACCATCA ACTGCAAGTCCAGCCAGAGTGTTTATACACC TCCAACAATAACAACTACTTAGCTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTTGCAGTTTATTATTGTCAGCAA TATTATACTACTCCGTGGACGTTCGGCCAAGG GACCAAGGTGGAAATCAAA<br><br>SEQ ID NO: 26049 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGTTCGACCCCTGGGGCCAGGGA ACCCTGGTCACCGTCTCCTCA<br><br>SEQ ID NO: 30055 |
| | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQQYYTT PWTFGQGTKVEIK<br><br>SEQ ID NO: 26050 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS<br><br>SEQ ID NO: 30056 |
| iPS:435089 | 21-225_91E9 | NA | GAAATTGTGTTGACGCAGTCTCCAGGCACCCT GTATTTGTCTCCAGGGGAAAGAGCCACCCTGT CATGCAGGGCCAGTCAGAGTGTTACAGCAGC TACTTAGCCTGGTACCAGCAGAAACCTGGCCA GGCTCCCAGGCTCCTCATTTATGGTGCATCA GCCGGGCCACCGGCATCCCAGACAGGTTCAGT GGCAGTGGGTCTGGGACAGACTTCGCTCTCAC CATCAGCAGAGTGGAGCATGAAGATTGTGCA GTGTATTACTGTCAGCACTCTGATAACTCACC GTGGACGTTCGGCCAAGGGACCAAGGTGGAA ATCAAA<br><br>SEQ ID NO: 26051 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTGTTACTG GAGTCGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 30057 |

FIGURE 50
(Continued)

| | | | |
|---|---|---|---|
| iPS:435097 | | AA | EIVLTQSPGTLYLSLSPGERATLSCRASQSVYSSYLA WYQQKPGQAPRLLIYGASSRATGIPDRFSGSGCG TDFALTISRVEHEDCAVYYCQHSDNSPWTFGQG TKVEIK<br><br>SEQ ID NO: 26052 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30058 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTGGCAGCAAC TACTTAGCCTGGTACCAGCAGAAACGTGGCCA GGCTCCCAGGCTCCTCATCTATGGTGCATCCA GCAGGGCCACTGACATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGTTCACCG TGGACGTTCGGCCAAGGGACCAAGGTGGAAA TCAAA<br><br>SEQ ID NO: 26053 | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTCCTACTGG AGCTGGATCCGCCAGCCCCCAGGGAAGGGGCTG GAGTGGATTGGGAAATCAATTATAGGGGAAGC ACCAACTACAACCCGTCCCTCAAGAGTCGAGTCG CCATATCAGTAGACACGTCCAAGAACCAGTTCTC CCTGAACCTGACCTCTGTGCCGAGGGACTACGGCGTT GCTGTGTATTACTGTGCGAGGGACTACGGCGTT TGGACGTCTGGGGCCAAGGGACCACGGTCACCG TCTCCTCA<br><br>SEQ ID NO: 30059 |
| 21-225_92B1 | | AA | EIVLTQSPGTLSLSPGERATLSCRASQSVGSNYLA WYQQKRGQAPRLLIYGASSRATDIPDRFSGSGSG TDFTLTISRLEPEDFAVYYCQQYESSPWTFGQGT KVEIK<br><br>SEQ ID NO: 26054 | QVQLQQWGAGLLKPSETLSLTCAVYGGSFSGSYW SWIRQPPGKGLEWIGEINYRGSTNYNPSLKSRVAIS VDTSKNQFSLNLTSVTAADTAVYYCARDYGGLDV WGQGTTVTVSS<br><br>SEQ ID NO: 30060 |

FIGURE 50
(Continued)

| | | | | |
|---|---|---|---|---|
| iPS:435103 | 21-225_92B2 | NA | GATATTGTGATGACTCAGTCTCCACTCTCCCTC CCTGTCACCCCTGGAGAGCCGGCCTCCATCTC ATGCAGGTCTAGTCAGAGCCTCGTGCATAGTA GTGGATACAACTATTTGGATTGGTACCTGCAG AAGCCAGGGCAGTCTCCACAACTGGTGATCTA TTTGGGTTCTAATGGGCCTCCGGGGTCCCTG ACAGGTTCAGTGGCAGTGGTTCAGTCACAGAT TTTACACTGAGAATCAGCAGAGTGGAGGCTGA GGATATTGGGATTTATTATTGCATGCAAGCTC TACATATTCCTCTCACTTTCGGCGGAGGGACC AAGGTGGAGATCAAA | GAGGTGCAGCTGGTGGAGTCTGGGGGAGGCTTG GTACAGCCGGGGGGGTCCCTGAGACTCTCCTGTG CAGCCTCTGATTCACCTTCAGTAACTACGACAT GCACTGGGTCCGCCAAGCTACAGGAAAGGTCT GGAGTGGGTCTCAGTATTGGTACTGCTGGTGAC ACATACTATCCAGGCTCCGTGAAGGGCCGATTCA CCATCTCCAGAGAAAATGCCAAGAACTCCTTGTA TCTTCAAATGAACAGCCTGAGAGCCGGGACAC GGCTGTGTATTTCTGTGCAAGAGCTCTTGACTAC GGTGACTCCTGGGCTACTACTACTACGGTATGG ACGTCTGGGGCCAAGGGACCACGGTCACCGTCTC CTCA |
| | | | SEQ ID NO: 26055 | SEQ ID NO: 30061 |
| | | AA | DIVMTQSPLSLPVTPGEPASISCRSSSQSLVHSSGY NYLDWYLQKPGQSPQLVIYLGSNRASGVPDRFS GSGSVTDFTLRISRVEAEDIGIYYCMQALHIPLTF GGGTKVEIK | EVQLVESGGGLVQPGGSLRLSCAASGFTFSNYDMH WVRQATGKGLEWVSAIGTAGDTYYPGSVKGRFTIS RENAKNSLYLQMNSLRAGDTAVYFCARALDYGDS LGYYYYGMDVWGQGTTVTVSS |
| | | | SEQ ID NO: 26056 | SEQ ID NO: 30062 |
| iPS:435109 | 21-225_92H5 | NA | GAAATAGTGATGACTCAGTCTCCAGCCACCCT GTCTGTGTCTCCAGGGGAAAGAGCCACCCTCT CCTGCAGGGCCAGTCAGAGTGTTATCACCTAC TTAGCCTGGTACCAGCAGAAACCTGGCCAGGC TCCCAGGCTCCTCATCTATGGTGCATCCACCA GGGCCACTGGTCTGTCCCAGCCAGGTTCAGTGGC AGTGGGTCTGGGACAGAGTTCACTCTCACCAT CACCAGCCTGCAGTCTGAAGATTTTGCACTTT ATTACTGTCAGGAGGATATAATGACTGGCCGTGC AGTTTTTGGCCAGGGGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCCCT TATAGTGGAGCTACTTACTTTGACTACTGGGGC CAGGGAACCCTGGTCACCGTCTCCTCA |
| | | | SEQ ID NO: 26057 | SEQ ID NO: 30063 |

FIGURE 50
(Continued)

| | | | |
|---|---|---|---|
| | | AA | EIVMTQSPATLSVSPGERATLSCRASQDVITYLA WYQQKPGQAPRLLIYGASTRATGVPARFSGSGS GTEFTLTITSLQSEDFALYYCQEYNDWPCSFGQG TKLEIK<br><br>SEQ ID NO: 26058 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARDPFIV GATYFDYWGQGTLVTVSS<br><br>SEQ ID NO: 30064 |
| iPS:435111 | 21-225_92D6 | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGTCCACTGTCATCCCAGACAGGTTCAGT GGCAGTGGGTGTGGGACAGACTTCGCTCTCAC CATCAGCAGACTGGAGCCTGAAGATTGTGCAG TGTATTACTGTCAGCATTATGATAACTCTCCGT GGACGTTCGGCCAAGGGACCAAGGTGGAAAT CAAA<br><br>SEQ ID NO: 26059 | CAGGTGCAGTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 30065 |
| | | AA | EIVLTQSPGTLYLSPGERATLSCRASQSVYSSYLA WYQQKPGQAPRLLIYGASSRSTVIPDRFSGSGCG TDFALTISRLEPEDCAVYYCQHYDNSPWTFGQG TKVEIK<br><br>SEQ ID NO: 26060 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30066 |

FIGURE 50
(Continued)

| | | | | |
|---|---|---|---|---|
| iPS:435113 | 21-225_92E6 | NA | GACATCGTGATGACCCAGTCTCCAGACTCCCT GGCTGCGTCTCTGGCAGAGGGCCACCATCA ACTGCAAGTCCAGTCAGTCAGAATATTTTATCCAGC TCCAACAATAAGAACTACTTAACTTGGTACCA GCAGAAACCAGGACAGCCTCCTAAATACTCA TTTACTGGACATCTACCCGGGAATCCGGGGTC CCTGACCGATTCAGTGGCAGCGGGGTTTGGGAC AGATTTCACTCTCACCATCAGCAGCCTGCAGG CTGAAGATGTGGCTGTTATTACTGTCAGCAA TATTTTAGTGTTCCTCCGACGTTCGGCCAAGG GACCAAGGTGGAAATCAAA<br>SEQ ID NO: 26061 | CAGGTGCAGCTGGTGCAGTCTGGGGCTGAGGTG AAGAAACCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAGTGG TAACACAGGCTATGCACAGAAGTTCCAGGGCAG AGTCACCATGACCAGGAACACCTCCATGAGCAC AGCCTACATGGAGCTGAGCAGCCTGAGATCTGA GGACACGGCCGTGTATTACTGTGCCATAGCAGT GGCTGGTACTTTTTGACTACTGGGGCCAGGGAA CCCTGGTCACCGTCTCCTCA<br>SEQ ID NO: 30067 |
| | | AA | DIVMTQSPDSLAASLGERATINCKSSQNILSSSNN KNYLTWYQQKPGQPPKILIYWTSTRESGVPDRFS GSGFGTDFTLTISSLQAEDVAVYYCQQYFSVPPT FGQGTKVEIK<br>SEQ ID NO: 26062 | QVQLVQSGAEVKKPGASVRVSCKASGYTFTNYDIN WVRQATGQGLEWMGWMHPNSGNTGYAQKFQGR VTMTRNTSMSTAYMELSSLRSEDTAVYYCAHSSG WYFFDYWGQGTLVTVSS<br>SEQ ID NO: 30068 |
| iPS:435115 | 21-225_77C5 | NA | GAAATTGTGTTGACGCAGTCTCCAGGCACCCT GTCTTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCACCG TGGACGTTCGGCCAAGGGACCAAGGTGGAAA TCAAA<br>SEQ ID NO: 26063 | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30069 |

FIGURE 50
(Continued)

| | | | | |
|---|---|---|---|---|
| iPS:435167 | 21-225_92F12 | AA | EIVLTQSPGTLSLSPGERATLSCRASQSVYSSYLA WYQQKPGQAPRLLIYGASSRSTGIPDRFSGSGSG TDFALTISRLEPEDFAVYYCQHYDNSPWTFGQG TKVEIK<br><br>SEQ ID NO: 26064 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30070 |
| | | NA | GACATCGTGATGACCCAGTCTCCAGACTCCCT GGCTGTGTCTCTGGGCGAGAGGGCCACCACCA ATTGTAAGTCCAGCCAGAGTGTTTTACACAGG TCCAACAATTACAACTACTTAGCGTGGTACCA GCAGAAACCAGGACAGGCTCCTAAGCTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAAA<br><br>SEQ ID NO: 26065 | CAGGTGCAGCTGGTGCAGTCTGGGGCTGAGGTG AAGAAGCCTGGGGCCTCAGTGAAGGTCTCCTGC AAGGCTTCTGGATACACCTTGACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGCA GAGTCACCATGACCAGGAACACCTCCATAAGCA CAGCCTACATGGAACTGAGCAGCCTGAGATCTG AGGACACGGCCGTGTATTACCGTGGGAGTACCA GTGGCGGGAAGTTCTTCGACTACTGGGGCCAGG GAACCCTGGTCACCGTCTCCTCA<br><br>SEQ ID NO: 30071 |
| | | AA | DIVMTQSPDSLAVSLGERATTNCKSSQSVLHRSN NYNYLAWYQQKPGQPPKLLIYWASTRESGVPD RFSGSGSGTDFTLTISSLQAEDVAVYYCQQYYST PPTFGQGTKVEIK<br><br>SEQ ID NO: 26066 | QVQLVQSGAEVKKPGASVKVSCKASGYTLTNYDI NWVRQATGQGLEWMGWMNPNSGNTGYAQKFQG RVTMTRNTSISTAYMELSSLRSEDTAVYYRGSTSG GKFFDYWGQGTLVTVSS<br><br>SEQ ID NO: 30072 |

FIGURE 50
(Continued)

| | | | |
|---|---|---|---|
| iPS:435171 | 21-225_93C2 | NA | GAAATTGTGTTGACGCAGTCTCCAGGCACCCT GTATTTGTCTCCAGGGGAAAGAGCCACCCTCT CCTGCAGGGCCAGTCAGTCAGAGTGTTTACAGCAGC TACTTAGCCTGGTACCAGCAGAAACCTGGCCA GGCTCCCAGGCTCCTCATCTATGGTGCATCCA GCCGGGCCACTGGCATACCAGACAGGTTCAGT GGCAGTGGGTCTGGGACAGACTTCGCTCTCAC CATCAGCAGACTGGAGCATGAAGATTGTGCAG TGTATTACTGTCAGCACTATGATAACTCACCG TGGACGTTCGGCCAAGGGACCAAGGTGGAAA TCAAA<br>SEQ ID NO: 26067 |
| | | AA | EIVLTQSPGTLYLSPGERATLSCRASQSVYSSYLA WYQQKPGQAPRLLIYGASSRATGIPDRFSGSGSG TDFALTISRLEHEDCAVYYCQHYDNSPWTFGQG TKVEIK<br>SEQ ID NO: 26068 |
| | | NA | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCCAGGGAAGGGCT GGAGTGGATTGGGAAATCAATCATAGTGGAAG CACCAACTACAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30073 |
| iPS:435177 | 21-225_93E4 | AA | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30074 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGGTCCACTGGCATCCCAGACAGGTTCAGT GGCAGTGGGTGTGGGACAGAGCTTCGCTCTCAC CATCAGCAGAGTGGAGCCTGAAGATTTTGCAG TGTATTACTGTCAGCACTGTGATAACTCACCGT GGACGTTCGGCCAAGGGACCAAGGTGGAAAT CAAA<br>SEQ ID NO: 26069 |
| | | | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCCAGGGAAGGGCT GGAGTGGATTGGGAAATCAATCATAGTGGAAG CACCAACTACAACCGTCCCTCAAGAGTCGAGTC ACCATTTCAGTAGACACGTCAAGAACCAGTTCT CCCTGAAGCTGAGCTGTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30075 |

FIGURE 50
(Continued)

| | | | | |
|---|---|---|---|---|
| iPS:435183 | 21-225_93E9 | AA | EIVLTQSPGTLYLSLSPGERATLSCRASQSVYSSYLA WYQQKPGQAPRLLIYGASSRSTGIPDRFSGSGCG TDFALTISRVEPEDFAVYYCQHSDNSPWTFGQG TKVEIK<br><br>SEQ ID NO: 26070 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 30076 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTGACAGCAGC TACCTAGCCTGGTACCAGCAGAAAACTGGCCA GGCTCCCAGGCTCCTCATCTATGGTGCATCCA GCAGGGCCCCTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGCTCACCG TGGACGTTCGGCCAAGGGACCAAGGTGGAAA TCAAA<br><br>SEQ ID NO: 26071 | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTGCTACTG GAGCTGGATCCGCCAGCCCCCAGGGAAGGGGCT GGAGTGGATTGGGGAAATCAATCATAGTGGAAG GACCAACTACAACCGTCCCTCAAGAGTCGAGTC ACCATATCAGTAGACACGTCCGAGAACAAGTTCT CCCTGAAGCTGAGCTCTGTGACCGCCGCGGACAC GGCTGTGTATTACTGTGCGAGAGACTACGGTGGG CTTGACTACTGGGGCCAGGGAACCCTGGTCACCG TCTCCTCA<br><br>SEQ ID NO: 30077 |
| | | AA | EIVLTQSPGTLSLSPGERATLSCRASQSVDSSYLA WYQQKTGQAPRLLIYGASSRAPGIPDRFSGSGSG TDFTLTISRLEPEDFAVYYCQQYESSPWTFGQGT KVEIK<br><br>SEQ ID NO: 26072 | QVQLQQWGAGLLKPSETLSLTCAVYGGSFSGCYW SWIRQPPGKGLEWIGEINHSGRTNYNPSLKSRVTIS VDTSENKFSLKLSSVTAADTAVYYCARDYGGLDY WGQGTLVTVSS<br><br>SEQ ID NO: 30078 |

FIGURE 50
(Continued)

| | | | |
|---|---|---|---|
| iPS:435195 | 21-225_94D3 | NA | GAAATTGTGTTGACGCAGTCTCCAGGCACCCT GTCTTTGTCTCAAGGGACCAGTCTCCAGGCACCCT CCTGCAGGGCCAGTCAGAGTGTTAGCAGCAGG TACTTAGCCTGGTACCAGCAGAAACCTGGCCA GGCTCCCAGACTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TATATTACTGTCAGCATTATGATAGCTCACCGT GGACGTTCGGCCAAGGGACCAAGGTGAAAA TCAA |
| | | | SEQ ID NO: 26073 |
| | | AA | EIVLTQSPGTLSLSQGERATLSCRASQSVSSRYLA WYQQKPGQAPRLLIYGASSRATGIPDRFSGSGSG TDFTLTISRLEPEDFAVYYCQHYDSSPWTFGQGT KVENQ |
| | | | SEQ ID NO: 26074 |
| iPS:435197 | 21-225_94F3 | NA | GACATCCAGATGACCCAGTCTCCATCCTCCCT GTCTGCATCTGTAGGAGACAGAGTCACCATCA CTTGCCGGGCAAGTCAGGCCATTAGAGATGAT TTAGGCTGGTATCAGCAGAAACCAGGGAAAG CCCCTCAGCGCCTGATCTTTGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTCCAGCATTATAGTTACCCTCGGA CGTTCGGCCAGGGACCAAGGTGGCAATCAA |
| | | | SEQ ID NO: 26075 |
| | | NA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACGATATCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAACGCAGATTCCAAGAACACGC TGTATCTGCAAATTAACAGCCTGAGAGCCGAGG ACACGGCTGTGTATTCTGTGCGAGAGAAAATA TAGCAGTGGCTGGTACGACTACGGTATGGACGTC TGGGGCCAAGGGACCACGGTCACCGTCTCCTCA |
| | | | SEQ ID NO: 30081 |

Above continues (for iPS:435195 AA row SEQ ID NO: 30079 and NA row SEQ ID NO: 30080):

| | |
|---|---|
| NA | CAGGTGCAGCTACAGCAGTGGGGGCGCAGGACCG TTGAAGCCTTCGGAGACCCTGTCCCTCACCTGCG CTGTCTATGGTGGGTCCTTCAGTGGTTGCTACTG GAGCTGGATCCGCCAGCCCCCAGGGAAGGGGCT GGAGTGGATTGGGGAAATCAATTATAGTGGAAG AACCAACTACAACCCGTCCCTCAAGAGTCGAGTC ACCATATCAGTAGACACGTCCAAGAACCAGTTCT CCCTGAAGCTGAGCTCTGTGACCGCCGCGGACAC GGCTGTGTATTACTGTGCGAGAGACTACGGCGGT ATGGACGTCTGGGGCCAAGGGACCACGGTCACC GTCTCCTCA |
| | SEQ ID NO: 30079 |
| AA | QVQLQQGGAGPLKPSETLSLTCAVYGGSFSGCYWS WIRQPPGKGLEWIGEINYSGRTNYNPSLKSRVTISV DTSKNQFSLKLSSVTAADTAVYYCARDYGGMDV WGQGTTVTVSS |
| | SEQ ID NO: 30080 |

FIGURE 50
(Continued)

| | | | |
|---|---|---|---|
| iPS:435203 | 21-225_75A7 | AA | DIQMTQSPSSLSASVGDRVTITCRASQAIRDDLG WYQQKPGKAPQRLIFAASSLQSGVPSRFSGSGSG TEFTLTISSLQPEDFATYYCLQHYSYPRTFGRGT KVAIK<br>SEQ ID NO: 26076 | QVQLVESGGGVVQPGRSLRLSCAASGFTFSNDIMH WVRQAPGKGLEWVAVIWYDGSNKYYADSVKGRF TISRDNSKNTLYLQINSLRAEDTAVYFCAREKYSSG WYDYGMDVWGQGTTVTSS<br>SEQ ID NO: 30082 |
| | | NA | GACATCGTGATGACCCAGTCTCCAGACTCCCT GGCTGTGTCTCTGGGCGAGAGGGCCACCATCA ACTGCAAGTCCAGCCAGACTGTTTACACAGC TCCAACAATTATAACTACTTAGCTTGGTACCA GCAGAAGCCAGGACAGCCCCTAAGGTGCTC ATTTACTGGACATCTACCCGGGAATCCGGGGT CCCTGACCGATTCAGTGGCAGCGGGTCTGGGA CAGATTTCACTCTCACCATCAGCAGCCTGCAG GCTGAAGATGTGGCAGTTTATTACTGTCAGCA ATATTTTAGTAGTCCTCCGACGTTCGGCCAAG GGACCAAGGTGGAAATCAAA<br>SEQ ID NO: 26077 | CAGGTGCAGCTGGTGCAGTCTGGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGGC TTGAGTGGATGGGATGGATGAACCTAACAGTG GTAACACAGGCTATGCACAGAAGTTCCAGGACA GAGTCACCATGACCAGGAACACCTCCATAAGCA CAGCCTACATGGAGCTGAGCAGCCTGAGATCTG AGGACACGGCCGTGTATTATTGTGCGGTTTCCAG TGGCTGGCACTGGTTCGACCCTGGGGCCAGGGA ACCCGTCACCGTCGCCTCA<br>SEQ ID NO: 30083 |
| | | AA | DIVMTQSPDSLAVSLGERATINCKSSQTVLHSSN NYNYLAWYQQKPGQPPKVLIYWTSTRESGVPD RFSGSGSGTDFTLTISSLQAEDVAVYYCQQYFSS PPTFGQGTKVEIK<br>SEQ ID NO: 26078 | QVQLVQSGAEVKKPGASVKVSCKASGYTFPNYDIN WVRQATGQGLEWMGWMNPNSGNTGYAQKFQDR VTMTRNTSISTAYMELSSLRSEDTAVYYCAVSSGW HWFDPWGQGTLVTVAS<br>SEQ ID NO: 30084 |

FIGURE 50
(Continued)

| | | | |
|---|---|---|---|
| iPS:435209 | 21-225_75A10 | NA | AATATCGTGATGACCCAGTCTCCAGACTCCCT GGCTGTGTCTCTGGGCGAGGGCCACCATCA ACTGCAAGTCCAGCCAGAGTGTTTACACAAC TCCAACAATTACAACTACTTAACTGGTACCA GCAGAAACCAGGACAGCCTCCTAAGCTGCTCC TTTACTGGGCATCTACCCGGAAATCGGGGTC CCTGACCGATTCAGTGGCAGCGGGTCTGGGAC AGATTTCACTCTCACCATCAGCAGCCTGCAGG CTGAAGATGTGGCAGTTTATTTCTGTCAGCAA TATTATAGTTCTCCTCCGACGTTCGGCCAAGG GACCAAGGTGGAAATCAAA<br><br>SEQ ID NO: 26079 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGCA GAGTCACCATGACCAGGAACACCTCCATAAGCA CAGCCTACATGGAGCTGAGCAGCCTGAGATCTG AGGACACGGCCGTGTATTACTGTGCGTATAGCAG TGGCTGGTACTACTTTGACTACTGGGGCCAGGGA ACCCTGGTCACCGTCTCCTCA<br><br>SEQ ID NO: 30085 |
| | | AA | NIVMTQSPDSLAVSLGARATINCKSSQSVLHNSN NYNYLTWYQQKPGQPPKLLLYWASTRKSGVPD RFSGSGSGTDFTLTISSLQAEDVAVYFCQQYYSS PPTFGQGTKVEIK<br><br>SEQ ID NO: 26080 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YYFDYWGQGTLVTVSS<br><br>SEQ ID NO: 30086 |
| iPS:435211 | 21-225_94E11 | NA | GACATCGTTATGACCCAGTCTCCAGACTCCCT GGCTGTGTCTCTGGGCGAGAGGGCCACCATCA ATTGCAAGTCCAGCCAGAGTGTTTTATTCAGC TCCAACAATTATAATTACTTAGCTTGGTACCA GCAGAAGACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGCTGATGTGGCAGTTTATTACTGTCAGCAA TATCATAGTTCTCCTCTGACGTTCGGCCAAGG GACCACGGTGCAAATCAAA<br><br>SEQ ID NO: 26081 | CAGGTGCAGTTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGGCT TGAGTGGATGGGATGGATGAACCCTAACAGTGG TAACACAGGCTATGCACAGAAGTTCCAGGCAG AGTCACCATGACCAGGAACACCTCCACAAGCAC AGCCCACATGGAGCTGAGCAGCCTGAGATCTGA GGACACGGCCGTGTATTACTGTGCGGTCTCCAGT GGCTGGAAGTGGTTCGACCCCTGGGGCCAGGGA ACCCTGGTCACCGTCTCCTCA<br><br>SEQ ID NO: 30087 |

FIGURE 50
(Continued)

| | | | |
|---|---|---|---|
| iPS:435215 | 21-225_94E12 | AA | DIVMTQSPDSLAVSLGERATINCKSSQSVLFSSN NYNYLAWYQQRPGQPPNLLIYWASTRESGVPD RFSGSGSGTDFTLTISSLQAADVAVYYCQQYHSS PLTFGQGTTVQIK<br>SEQ ID NO: 26082 | QVQLVQSGAEVKKPGASVKVSCKASGYTFTNYDIN WVRQATGQGLEWMGWMNPNSGNTGYAQKFQGR VTMTRNTSTSTAHMELSSLRSEDTAVYYCAVSSGW KWFDPWGQGTLVTVSS<br>SEQ ID NO: 30088 |
| | | NA | GACATCGTGATGACCCAGTCTCCAGACTCCCT GGCTGTGTCTCTGGGCGAGAGGGCCACCACCA ATTGTAAGTCCAGCCAGAGTGTTTTACACAGG TCCAACAATTACAACTACTTAGCGTGGTACCA GCAGAAACCAGGACAGCCTCCTAAGCTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAAA<br>SEQ ID NO: 26083 | CAGGTGCAGCTGGTGCAGTCTGGGGCTGAGGTG AAGAAGCCTGGGGCCTCAGTGAAGGTCTCCTGC AAGGCTTCTGGATACACCTTGACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAACTGAGCAGCCTGAGATCTG AGGACACGGCCGTGTATTACCGTGGGAGTACCA GTGGCTGGAAGTTCTTTGACTACTGGGGCCAGGG AACCCTGGTCACCGTCTCCTCA<br>SEQ ID NO: 30089 |
| | | AA | DIVMTQSPDSLAVSLGERATTNCKSSQSVLHRSN NYNYLAWYQQKPGQPPKLLIYWASTRESGVPD RFSGSGSGTDFTLTISSLQAEDVAVYYCQQYYST PPITFGQGTKVEIK<br>SEQ ID NO: 26084 | QVQLVQSGAEVKKPGASVKVSCKASGYTLTNYDI NWVRQATGQGLEWMGWMNPNSGNTGYAQKFQG RVTMTRNTSISTAYMELSSLRSEDTAVYYRGSTSG WKFFDYWGQGTLVTVSS<br>SEQ ID NO: 30090 |

FIGURE 50
(Continued)

| | | | |
|---|---|---|---|
| iPS:435217 | 21-225_94F12 | NA | GAAATTGTGTTGACGCAGTCTCCAGGCACCCT GTATTTGTCTCCAGGGGAAAGAGCCACCTTCT CATGCAGGGCCAGTCAGTCAGAGTGTTTACAGCAGC TACTTAGCGGTGGTACCAGCAGAAACCTGGCCA GGCTCCCAGGCTCCTCATTTATGGTGTCATCCA GCCGGTCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCATTATGATAACTCACCGT GGACGTTCGGCCAAGGGACCAAGGTGGAAAT CAAA SEQ ID NO: 26085 | CAGGTGCAGCTACAGCAGTGGGGCGCAGGACTG TTGAAGCCTTCGGAGACCCTGTCCCTCACCTGCG CTGTCCATGGTGGTCTTCAGTGGTTGCTACTG GAGCTGGATCCGCCAGCCCCAGGGAAGGGCT GGAGTGGATTGGGGAAATCAATCATAGTGGAAG CACCAACTACACAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 30091 |
| | | AA | EIVLTQSPGTLYLSPGERATFSCRASQSVYSSYLA WYQQKPGQAPRLLIYGASSRSTGIPDRFSGSGSG TDFALTISRLEPEDFAVYYCQHYDNSPWTFGQG TKVEIK SEQ ID NO: 26086 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 30092 |
| iPS:435219 | 21-225_95D2 | NA | GAAATTGTGTTGACGCAGTCTCCAGGCACCCT GTCTTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATCTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTACTGATAACTCACCG TGGACGTTCGGCCAAGGGACCAAGGTGGAAA TCAAA SEQ ID NO: 26087 | CAGGTGCAGCTACAGCAGTGGGGCGCAGGACTG TTGAAGCCTTCGGAGACCCTGTCCCTCACCTGCG CTGTCCATGGTGGGTCTTCAGTGGTTGCTACTG GAGCTGGATCCGCCAGCCCCAGGGAAGGGGCT GGAGTGGATTGGGGAAATCAATCATAGTGGAAG CACCAACTACACAACCGTCCCTCAAGAGTCGAGTC ACCATTTCAGTAGACACGTCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA SEQ ID NO: 30093 |

FIGURE 50
(Continued)

| | | | | |
|---|---|---|---|---|
| iPS:435221 | 21-225_95G2 | AA | EIVLTQSPGTLSLSPGERATLSCRASQSVYSSYLA WYQQKPGQAPRLLIYGASSRATGIPDRFSGSGSG TDFALTISRLEPEDCAVYYCQHYDNSPWTFGQG TKVEIK<br>SEQ ID NO: 26088 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30094 |
| | | NA | GAAATAGTGATGACGCAGTCTCCAGCCACCCT GTCTCTGTCTCCAGGGGAAAGAGCCACCCTCT CCTGCAGGGCCAGTATGAGTGTTGTCAACAGC TTAGCCTGGTACCAGCAGAAACCTGGCCAGGC GCACTGGTCTCCGCCAGGCTCCAGGCAAGGGCT TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCAGCCTGAGCCTGAAGATTTTGCAATTT ATTACTGTCAGCAGTATAATGACTGGCCGTGC AGTTTTGGCCAGGGGACCAAGCTGGAGATCAA A<br>SEQ ID NO: 26089 | CAGGTGCAGCTGGTGGTGGAGTCTGGGGGAGGCGTG GTCCAGCCTGGGAGGTCCCTGAGACTCTCCTGTA CAGCGTCTGGATTCACCTTCAGTAGCTATGGCAT GCACTGGGTCCGCCAGGCTCCAGGCAAGGGGCT GGAGTGGGTGGCAGTTATTTGGTATGATGAAGT AATAAATACTATGCAGACTCCGTGAAGGGCCGA TTCACCATCTCCAGAGACAACATTCCAAGAACACGC TGTTTCTGCAAATGAACAGCCTGAGAGCCGAGG ACACGGCTGTGTATTACTGTGCGAGCGATCGCAA TATAGTGGGAGCTACTACTTTGAGTCCTGGGGC CAGGGAACCCTGGTCACCGTCTCCTCA<br>SEQ ID NO: 30095 |
| | | AA | EIVMTQSPATLSLSPGERATLSCRASMSVVNSLA WYQQKPGQAPRLLIYGASTRATGIPARFSGSGSG TEFTLTISSLQSEDFAIYYCQQYNDWPCSFGQGT KLEIK<br>SEQ ID NO: 26090 | QVQLVESGGGVVQPGRSLRLSCTASGFTFSSYGMH WVRQAPGKGLEWVAVIWYDGSNKYYADSVKGRF TISRDNSKNTLFLQMNSLRAEDTAVYYCASDRNIV GATYFESWGQGTLVTVSS<br>SEQ ID NO: 30096 |

FIGURE 50
(Continued)

| | | | |
|---|---|---|---|
| iPS:435227 | 21-225_95G4 | NA | GACATCGTTATGACCCAGTCTCCAGACTCCCTGGCTGTGTCTCTGGGCGAGAGGGCCACCATCAATTGCAAGTCCAGCAGAGTGTTTATTCAGATCCAACAATTATAATTACTTAGCTTGGTACCAGCAGAGACCAGGACAGCCTCATAACCTGCTCATTTACTGGGCATCTACCCGGGAATCCGGGGTCCCTGACCGATTCAGTGGCAGCGGGTATGGGACAGATTTCACTCTCACCATCAGCAGCGTGCAGGCTGCTGATGTGGCAGTTATTACTGTCAGCAATATCATAGTTCCTCTGACGTTCGGCCAAGGGACCACGGTCAAATCAAA | CAGGTGCAGTTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGGCAGAGTCACCATGACCAGGAACACCTCCACAAGCACAGCCCACATGGAGCTGAGCAGCCTGAGATCTGAGGACACGGCCGTGTATTACTGTGCGGTCTCAGTGGCTGAACTGGTTCGACCCCTGGGGCCAGGGAACCCTGGTCACCGTCTCCTCA |
| | | | SEQ ID NO: 26091 | SEQ ID NO: 30097 |
| | | AA | DIVMTQSPDSLAVSLGERATINCKSSQSVLFRSNNYNYLAWYQQRPGQPHNLLIYWASTRESGVPDRFSGSGYGTDFTLTISSVQAADVAVYYCQQYHSSPLTFGQGTTVQIK | QVQLVQSGAEVKKPGASVKVSCKASGYTFTNYDINWVRQATGQGLEWMGWMNPNSGNTGYAQKFQGRVTMTRNTSTSTAHMELSSLRSEDTAVYYCAVSSGWNWFDPWGQGTLVTVSS |
| | | | SEQ ID NO: 26092 | SEQ ID NO: 30098 |
| iPS:435235 | 21-225_95F9 | NA | GAAATTGTGTTGACGCAGTCTCCAGGCACCCTGTATTTGTCTCCAGGGGAAAGAGCCACCCTCTCCTGCAGGGCCAGTCAGAGTGTTACAGCAGCTACTTAGCCTGGTACCAGCAGAAACCTGGCCAGGCTCCCAGGCTCCTCATTTATGGTGCATCCAGCCGGTCCACTGGCATCCCAGACAGGTTCAGTGGCAGTGGGTGTGGGACAGACTTCGCTCTCACCATCAGCAGACTGGAGCCTGAAGATTTTGCAGTGTATTACTGTCAGCACTATGATAACTCACCGTGGACGTTCGGCCAAGGGACCAAGGTGGAAATCAAA | CAGGTGCAGCTACAGCAGTGGGGCGCAGGACTGTTGAAGCCTTCGGAGACCCTGTCCCTCACCTGCGCTGTCCATGGTGGGTCCTTCAGTGGTTGCTACTGGAGCTGGATCCGCCAGCCCCCAGGGAAGGGGCTGGAGTGGATTGGGGAAATCAATCATAGTGGAAGCACCAACTACAACCCGTCCCTCAAGAGTCGAGTCACCATTTCAGTAGACACGTCCAAGAACCAGTTCTCCCTGAAGCTGAGCTCTGTGACCGCCGCGGACACGGCTGTGTATTACTGTGCGAGGGACTACGGCGGTATGGACGTCTGGGGCCAAGGGACCACGGTCACCGTCTCCTCA |
| | | | SEQ ID NO: 26093 | SEQ ID NO: 30099 |

FIGURE 50
(Continued)

| | | | |
|---|---|---|---|
| iPS:435237 | 21-225_95G9 | AA | EIVLTQSPGTLYLSPGERATLSCRASQSVYSSYLA WYQQKPGQAPRLLIYGASSRSTGIPDRFSGSGCG TDFALTISRLEPEDFAVYYCQHYDNSPWTFGQG TKVEIK<br>SEQ ID NO: 26094 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30100 |
| | | NA | GAAATTGTGTTGACGCAGTCTCCAGGCACCCT GTATTTGTCTTCAGGGGAAAGAGCACCCTCT CATGCAGGGCCAGTCAGAGTGTTTACAGCAGC TACTTAGCGTGGTACCAGCAGAAACCTGGCCA GGCTCCCAGGCTCCTCATTTATGGTGCATCA GCCGGTCCACTGGCATCCCAGACAGGTTCAGT GGCAGTGGGTCTGGGACAGACTTCGCTCTCAC CATCAGCAGAGTGGAGCATGAAGATTGTGCA GTGTATTACTGTCAGCACTATGATAACTCACC GTGGACGTTCGGCCAAGGGACCAAGGTGGAA ATCAAA<br>SEQ ID NO: 26095 | CAGGTGCAGCTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br>SEQ ID NO: 30101 |
| | | AA | EIVLTQSPGTLYLSSGERATLSCRASQSVYSSYLA WYQQKPGQAPRLLIYGASSRSTGIPDRFSGSGSG TDFALTISRVEHEDCAVYYCQHYDNSPWTFGQG TKVEIK<br>SEQ ID NO: 26096 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30102 |

FIGURE 50
(Continued)

| | | | |
|---|---|---|---|
| iPS:435239 | 21-225_95H10 | NA | GAAATTGTGTTGACGCAGTCTCCAGGCATCCT GTATTTGTCTTCAGGGGAAAGAGCCACCCTCT CCTGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGACTGGAGCCTGAAGATTTTGCAG TGTATTACTGTCAGCACTATGATAACTCTCCGT GGACGTTCGGCCAAGGGACCAAGGTGGAAAT CAAA<br>SEQ ID NO: 26097 |
| | | AA | EIVLSQSPGILYLSSGERATLSCRASQSVYSSYLA WYQQKPGQAPRLLIYGASSRATGIPDRFSGSGSG TDFALTISRLEPEDFAVYYCQHYDNSPWTFGQG TKVEIK<br>SEQ ID NO: 26098 |
| | | NA | CAGGTGCAGTCTACAGCAGTGGGGCGCAGGACTG TTGAAGCCTTCGGAGACCCTGTCCCTCACCTGCG CTGTCCATGTGGGTCCTTCAGTGGTTGTACTG GAGCTGGATCCGCAGCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGCGAGGGACTACGGCCGT GGCTGTGTATTACTGTGCGAGGGACTACGGCGT ATGGACGTCTGGGGCCAAGGGACCACGGTCACC GTCTCCTCA<br>SEQ ID NO: 30103 |
| | | AA | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 30104 |
| iPS:435245 | 21-225_95E12 | NA | CAGGTGCAGTCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGGATTAGCAG TGGCTGGTACTGGTTCGACCCCTGGGGCCAGGGA ACCCTGGTCACCGTCTCCTCA<br>SEQ ID NO: 30105 |

FIGURE 50
(Continued)

| | | | | |
|---|---|---|---|---|
| | | | AA | DIVMTQSPDSLAVSLGERATINCKSSQSVLYSSN NANYLAWYQQKPGQPPNLFIYWASTRESGVPD RFSGSGSGTDFTLTISSLQAEDVAVYYCQQYYST PCSFGQGTKVEIK<br>SEQ ID NO: 26100 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAISSGW YWFDPWGQGTLVTVSS<br>SEQ ID NO: 30106 |
| iPS:435247 | 21-225_96G1 | | NA | GAAATTGTGTTGACGCAGTCTCCAGGCACCCT GTCTTTGTCTACAGGGGAAAGAGCCACCCTCT CGTGCAGGGCCAGTCAGAGTCGTTAGCAGCAG CTACTTAGCTTGGTACCAGCAGAAACCTGGCC AGCCTCCCAGGCTCCTCATTTATGGTGCATCC ACCAGGGCCTCTGGCATCCCAGACAGGTTCAG TGGCAGTGGGTCTGGGACAGACTTCACTCTCA CCATCAGCAGACTGGAGCCTGAATATTTTGCA GTTTATTACTGTCAGCAGTATGGTAACTCACC GCTCACTTTCGGCGGAGGGACCAAGGTGGAG ATCAAA<br>SEQ ID NO: 26101 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAATGG TAACACAGGCTATGCACAGAAGTTCCAGGGCAG AGTCACCATGACCAGGAACACCTCCATAAGCAC AGCCTACATGGAGCTGAACAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTTA<br>SEQ ID NO: 30107 |
| | | | AA | EIVLTQSPGTLSLSTGERATLSCRASQSVSSSYLA WYQQKPGQPPRLLIYGASTRASGIPDRFSGSGSG TDFTLTISRLEPEYFAVYYCQQYGNSPLTFGGGT KVEIK<br>SEQ ID NO: 26102 | QVQLVQSGAEVKKPGASVKVSCKASGYTFTNYDIN WVRQATGQGLEWMGWMHPNNGNTGYAQKFQGR VTMTRNTSISTAYMELNSLRSEDTAVYYCAISSGW YWFDPWGQGTLVTVSL<br>SEQ ID NO: 30108 |

FIGURE 50
(Continued)

| | | | | |
|---|---|---|---|---|
| iPS:435249 | 21-225_96E2 | NA | GACAGCGTGATGACCCAGTCTCCAGACTCCCT GGCTGTGTCTCTGGGCGAGAGGGCCACCATCA ACTGCAAGTCCAGCCAGAGTGTTTTACACAGC TCTAATAAAAGAAACTACTTAGCTTGGTACCA GCAGAAACCAGGACAGCCTCCTAAGCTGCTCA TTTACTGGGCATCTACCTGGGAATCCGGGGTC CCTGACCGATTCAGTGGCAGCGGGTCTGGGAC AGATTTCACTCTCACCATCAGCAGTCTGCAGG CTGAAGATGTGGCAGTTTATTACTGTCAGCAA TATTATAGGACTCCGTGACGTTCGGCCAAGG GACCAAGGTGGAAATCAAA

SEQ ID NO: 26103 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAATAGTGG TAACACAGGCTATGCACAGAAGTTCAGGGCAG AGTCACCCTGACCAGGAACACCTCCATAAGCAC AGCCTACATGGAGCTGAGCAGCCTGAGATCTGA GGACACGGCCGTGTATTACTGTGCGGTTTCCAGT GGCTGGTACTGGTTGACCCCTGGGGCCAGGGA ACCCTGGTCACCGTCTCCTCA

SEQ ID NO: 30109 |
| | | AA | DSVMTQSPDSLAVSLGERATINCKSSQSVLHSSN KKNYLAWYQQKPGQPPKLLIYWASTWESGVPD RFSGSGSGTDFTLTISSLQAEDVAVYYCQQYYRT PWTFGQGTKVEIK

SEQ ID NO: 26104 | QVQLVQSGAEVKKPGASVKVSCKASGYTFTNYDIN WVRQATGQGLEWMGWMHPNSGNTGYAQKFQGR VTLTRNTSISTAYMELSSLRSEDTAVYYCAVSSGW YWFDPWGQGTLVTVSS

SEQ ID NO: 30110 |
| iPS:435251 | 21-225_96A3 | NA | GACATCCAGATGACCCAGTCTCCATCCTCCCT GTCTGCTCTGTCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCACTT TGCAAAGTGGGGTCCCATCAAGGTTCAGCGGC AGTGGATCTGGGACAGAATTCACTCTCACAAT CAGCGGCCTGCAGCGTGAAGATTTTGCAACTT ATCACTGTCTACAGCATAGTAATTACCCGCTC ACTTTCGGCGGAGGGACCAAGGTGGAGATCA AA

SEQ ID NO: 26105 | CAGCTGCAGCTGCAGGAGTCGGGCCCAGGACTG GTGAAGCCTTCGGAGACCCTGTCCCTCATCTGTA CTGTCTCTGGTGGCTCCATCAGCAGTAGTAATTA CTACTGGGGCTGGATCCGCCAGCCCCCAGGGAA GGGGCTGGAGTGGATTGGGAGTATCTATTATAGT GGATACACCTCTACAACCCGTCCCTCAAGAGTC GAGTCACCATATCCGTAGACTCGTCCAAGAACCA CTTCTCCCTGAGGCTGAGCTCTGTGACCGCCGCA GACACGGCTGTGTATTACTGTGCGAGACTTGACT CTAACTGGGTCTTGACTACTGGGGCCAGGGAAC CCTGGTCACCGTCTCCTCA

SEQ ID NO: 30111 |

FIGURE 50
(Continued)

| | | | |
|---|---|---|---|
| iPS:435253 | 21-225_96A4 | AA | DIQMTQSPSSLSASVGDRVTITCRASQGIRNDLGWYQQKPGKAPKRLIYAASTLQSGVPSRFSGSGSGTEFTLTISGLQREDFATYHCLQHSNYPLTFGGGTKVEIK<br>SEQ ID NO: 26106 | QLQLQESGPGLVKPSETLSLICTVSGGSISSSNYYWGWIRQPPGKGLEWIGSIYYSGYTSYNPSLKSRVTISVDSSKNHFSLRLSSVTAADTAVYYCARLDSNWGLDYWGQGTLVTVSS<br>SEQ ID NO: 30112 |
| | | NA | GACATCCAGATGACCCAGTCTCCATCCTCCCTGTCTGCATCTGTAGGAGACAGAGTCACCATCACTTGCCGGGCAAGTCAGGACATTAGAAATGATCTTAGGCTGGTATCAGCAGAAACCAGGGAAAGCCCCTAAGCGCCTGATCTATGCTGTATCCAGTTTGCAAAGTGGGGTCCCATCCAAGGTTCAGCGGCAGTGGATCTGGGACGGACAGAATTCACTCTCACAATCAGCAGCCTGCAGCGTGAAGATTTTGCAACTTATTACTGTCTACAGCATAATGATTACCCATTCACTTTCGGCCCTGGGACCAAAGTGGATATCAAA<br>SEQ ID NO: 26107 | CAGGTGCAGCTGGTGCAGTCTGGGGCTGAGGTGAAGAAGCCTGGGGCCTCAGTGAAGGTCTCCTGCAAGGCTTCTGGATACACCTTCACCAGTTATGATATCAACTGGGTGCGACAGGCCACTGGACAGGGCTTGAGTGGATGGGATGAACCCTAACAGTGTAACACAGGCTATGCACAGAAGTTCCAGGGCAGAGTCACCATGACCTGGAACACCTCCAAAAGCACAGCCTACATGGAGCTGAGTAGCCTGAGATCTGAGGACACGGCCGTGTATTACTGTGCGAGAGGCTTTTACGATACTTTGACTGGTTCCGGCTACTACGTTATGACGTCTGGGGCCAAGGGACCACGGTCACCGTCTCCTCA<br>SEQ ID NO: 30113 |
| | | AA | DIQMTQSPSSLSASVGDRVTITCRASQDIRNDLGWYQQKPGKAPKRLIYGVSSLQSGVPSRFSGSGSGTEFTLTISSLQREDFATYYCLQHNDYPFTFGRGTKVDIK<br>SEQ ID NO: 26108 | QVQLVQSGAEVKKPGASVKVSCKASGYTFTSYDINWVRQATGHGLEWMGWMNPNSGNTGYAQKFQGRVTMTWNTSKSTAYMELSSLRSEDTAVYYCARGFYDTLTGSGYYVMDVWGQGTTVTVSS<br>SEQ ID NO: 30114 |

FIGURE 50
(Continued)

| | | | | |
|---|---|---|---|---|
| iPS:435255 | 21-225_96D5 | NA | GACATCGTGATGACCCAGTCTCCAGACTCCCT GGCTGTGTCTCTGGGCGAGAGGGCCACCATCA ACTGCAAGTCCAGCCAGAGTGTTTTGCACAGC TCCAACAATTATATACTTAGCTGGTACCA GCAGAAACCAGGACAGCCTCCTAACCTGCTCA TTTACTGGGCATCTACCCGGAATCGGGGTC CCTGACCGATTCAGTGGCAGCGGGTCTGGGAC AGATTTCACTCTCACCATCAGCAGCTGCAGG CTGCTGATGTGGCAGTTTATTACTGTCAGCAA TATTATAGTAGTCCACCGACGTTCGGCCAAGG GACCACGGTGGAAATCAAA<br><br>SEQ ID NO: 26109 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGCA GAGTCACCATGACCAGGAGCACCTCCACAAGCA CAGCCCACATGGAGCTGAGCAGCCTGAGATCTG AGGACACGGCCGTGTATTACTGTGCGGTTTCCAG TGGCTGGTCCTGGTTCGACCCCTGGGGCCAGGGA ACCCTGGTCACCGTCTCCTCA<br><br>SEQ ID NO: 30115 |
| | | AA | DIVMTQSPDSLAVSLGERATINCKSSQSVLHSSN NYNYLAWYQQKPGQPPNLLIYWASTRESGVPD RFSGSGSGTDFTLTISSLQAADVAVYYCQQYYSS PPTFGQGTTVEIK<br><br>SEQ ID NO: 26110 | QVQLVQSGAEVKKPGASVKVSCKASGYTFTNYDIN WVRQATGQGLEWMGWMNPNSGNTGYAQKFQGR VTMTRSTSTAHMELSSLRSEDTAVYYCAVSSGW SWFDPWGQGTLVTVSS<br><br>SEQ ID NO: 30116 |
| iPS:435257 | 21-225_96H5 | NA | GACATCGTGATGACCCAGTCTCCAGACTCCCT GGCTGTGTCTCTGGGCGAGAGGGCCACCATCA ACTGCAAGTCCAGCCAGAGTGTTTTGTACAGC TCCAACAGTACAACTACTTAGCTTGGTACCA GCAGAAACCAGGACAGCCTCCTAAACTGCTCA TTTACTGGGCATCTATCCGGGAATCGGGGTC CCTGACCGATTCAGTGGCAGCGGGTCTGGGAC AGCCACCATGACCAGGAACACCTCCATAAGCAC AGCCTACATGGAGCTGAGCAGCCTGAGATCTGA CTGAAGATGTGGCAGTTTATTACTGTCAGCAA TATTATAGTACTCCGTGCAGTTTGGCCAGGG GACCAAGGTGGAGATCAAA<br><br>SEQ ID NO: 26111 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCCTGGACAAGGAC TTGAGTGGATGGGATGATGCACAGAAGTTCCAGGCA GCCTACATGGAGCTGAGCAGCCTGAGATCTGA GGACACGGCCGTATATTACTGTGCGTATAGTAGT GGCTGGTACAAATTTGACTACTGGAGCCAGGGA ACCCTGGTCACCGTCTCCTCA<br><br>SEQ ID NO: 30117 |

FIGURE 50
(Continued)

| | | | |
|---|---|---|---|
| iPS:435259 | 21-225_96C6 | AA | DIVMTQSPDSLAVSLGERATINCKSSQSVLYSSN SHNYLAWYQQKPGQPPKLLIYWASIRESGVPDR FSGSGSGTDFTLSISSMQAEDVAVYYCQQYYSTP CSFGQGTKVEIK<br>SEQ ID NO: 26112 | QVQLVQSGAEVKKPGASVKVSCKASGYTFTNYDIN WVRQASGQGLEWMGWMHPNSGNTGYAQKFQGR VTMTRNTSISTAYMELSSLRSEDSAVYYCAYSSGW YKFDYWSQGTLVTVSS<br>SEQ ID NO: 30118 |
| | | NA | GACATCCAGATGACCCAGTCTCCATCCTCACT GTCTGCATCTGTAGGAGACAGAGTCACCATCA CTTGTCGGGCAGTCAGGGCATTAGCAGGGAAAGC TTAGCCTGGTTTCAGCAGAAACCAGGGAAAGC CCCTAAGTCCCTGATCTATGCTGCTTCCAGTTT GCAAAGTGGGGTCCCCTCAAAGTTCAGCGGCA GTGGATCTGGGACAGATTTCACTCTCACCATC AACAGCCTGCAGCCTGAAGATTTTGCAACTTA TTACTGCCACCAGTATATAATGATTACCCATCA CTTTCGGCCCTGGGACCAAAGTGGATATCAAA<br>SEQ ID NO: 26113 | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGTCAGGCCACTGGACAAGGC TTGAGTGGATGGGATGAACCCTAACAGTCG TAACACAGGCTATGCACAGAAGTTCCAGGCAG AGTCACCATGACCTGGAACACCTCCATAAGCACA GCCTACATGGAGCTGAGCAGCCTGAGATCTGAG GACACGGCCGTGTATTACTGTGCGAGAGGCGGCT ACGATGTTTGCCTGGGAATAACTACTACTACGA TATGGACGTCTGGGGCCAAGGGACCACGGTCAC CGTCTCCTCA<br>SEQ ID NO: 30119 |
| | | AA | DIQMTQSPSSLSASVGDRVTITCRASQGISNYLA WFQQKPGKAPKSLIYAASSLQSGVPSKFSGSGSG TDFTLTINSLQPEDFATYYCHQYNDYPFTFGPGT KVDIK<br>SEQ ID NO: 26114 | QVQLVQSGAEVKKPGASVKVSCKASGYTFTSYDIN WVRQATGQGLEWMGWMNPNSRNTGYAQKFQGR VTMTWNTSISTAYMELSSLRSEDTAVYYCARGGY DVLPGNNYYYDMDVWGQGTTVTVSS<br>SEQ ID NO: 30120 |

FIGURE 50
(Continued)

| | | | |
|---|---|---|---|
| iPS:435267 | 21-225_96D10 | NA | GACATCGTGATGACCCAGTCTCCAGACTCCCT GGCTGTGTCTCTGGGCGAGAGGGCCACCATCA ATTGCAAGTCCAGTCAGAATCAGAATATTTATCCAGC TCCAACAATAAGAACTACTTAACTTGGTACCA GCAGAAACCAGGACAGCCTCCTAAATACTCA TTTACTGGACATCTACCCGGGAATCCGGGGTC CCTGACCGATTCAGTGGCAGCGGGGTTTGGGAC AGATTTCACTCTCACCATCAGCAGCCTGCAGG CTGAAGATGTGGCTGTTTATTACTGTCAGCAA TATTTTAGTGTTCCTCCGACGTTCGGCCAAGG GACCAAGGTGGAAATCAAA |
| | | | CAGGTGCAGCTGGTGCAGTCTGGGGCTGAGGTG AAGAAACCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCAGGCAG AGCCACCATGACCAGGAACACCTCCATGAGCAC AGCCTACATGGAGCTGAGCAGCCTGAGATCTGA GGACACGGCCGTGTATTACTGTGCCCATAGCAGT GGCTGGTACTTTTTTGACTACTGGGGCCAGGGAA CCCTGGTCACCGTCTCCTCA |
| | | | SEQ ID NO: 26115 |
| | | | SEQ ID NO: 30121 |
| | | AA | DIVMTQSPDSLAVSLGERATINCKSSQNILSSSNN KNYLTWYQQKPGQPPKILIYWTSTRESGVPDRFS GSGFGTDFTLTISSLQAEDVAVYYCQQYFSVPPT FGGGTKVEIK |
| | | | QVQLVQSGAEVKKPGASVRVSCKASGYTFTNYDIN WVRQATGQGLEWMGWMHPNSGNTGYAQKFQGR VTMTRNTSMSTAYMELSSLRSEDTAVYYCAHSSG WYFFDYWGQGTLVTVSS |
| | | | SEQ ID NO: 26116 |
| | | | SEQ ID NO: 30122 |
| iPS:435273 | 21-225_97A2 | NA | GAAATTGTGTTGACGCAGTCTCCAGGCACCCT GTATTGTCTTCAGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCA GGCCGGTCCACTGGCATCCCAGACAGGTTCAGT GGCAGTGGGTGTGGGACAGACTTCGCTCTCAC CATCAGCAGACTGGAGCCTGAAGATTGTGCAG TGTATTACTGTCAGCATTTGATAACTCACCGT GGACGTTCGGCCAAGGGACCAAGGTGGAAAT CAAA |
| | | | CAGGTGCAGCTACAGCAGTGGGGCGCAGGACTG TTGAAGCCTTCAGGGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA |
| | | | SEQ ID NO: 26117 |
| | | | SEQ ID NO: 30123 |

FIGURE 50
(Continued)

| | | | |
|---|---|---|---|
| iPS:435279 | 21-225_97H4 | AA | EIVLTQSPGTLYLSSGERATLSCRASQSVYSSYLA WYQQKPGQAPRLLIYGASSRSTGIPDRFSGSGCG TDFALTISRLEPEDCAVYYCQHSDNSPWTFGQG TKVEIK<br>SEQ ID NO: 26118 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br>SEQ ID NO: 30124 |
| | | NA | GACATCGTGATGACCCAGTCTCCAGATTGCCT GGCTGTGTCTCTGGGCGAGAGGGCCACCATCA ACTGCAAGTCCAGCCAGAGTGTTTATACACC TCCAACAATAACAACTACTTAGCTTGGTACCA GCAGAAACCAGGACAGCCTCCTAAGCTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTTGCAGTTATTATTGTCAGCACT ACAATGATACTCCATGGAAGTTTGTCCAAGGG ACCAAGGTGGAAATCACA<br>SEQ ID NO: 26119 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGATTAGCAGT GGCTGGTACTGGTTCGACCCCTGGGGCCAGGGA ACCCTGGTCACCGTCTCCTCA<br>SEQ ID NO: 30125 |
| | | AA | DIVMTQSPDCLAVSLGERATINCKSSQSVLYTSN NNNYLAWYQQKPGQPPKLLIYWASTRESGVPD RFSGSGSGTDFTLTISSLQAEDVAVYYCQHYNDT PWKFVQGTKVEIT<br>SEQ ID NO: 26120 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAISSGW YWFDPWGQGTLVTVSS<br>SEQ ID NO: 30126 |

FIGURE 50
(Continued)

| | | | |
|---|---|---|---|
| iPS:435281 | 21-225_97E5 | NA | GAAATTGTGTTGACGCAGTCTCCAGGCACCCT GTCTTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTGTGGGACAGACTTCGCTCTCAC CATCAGCAGACTGGAGCCTGAAGATTGTGCAG TGTATTACTGTCAGCACTCTGATAACTCACCGT GGACGTTCGGCCAAGGGACCAAGGTGGAAAT CAAA SEQ ID NO: 26121 |
| | | AA | EIVLTQSPGTLSLSPGERATLSCRASQSVYSSYLA WYQQKPGQAPRLLIYGASSRATGIPDRFSGSGSG TDFALTISRVEPEDCAVYYCQHSDNSPWTFGQG TKVEIK SEQ ID NO: 26122 | CAGGTGCAGCTACAGCAGTGGGGCGCAGGACTG TTGAAGCCTTCGGAGACCCTGTCCCTCACCTGCG CTGTCCATGTGGGTCCTTCAGTGGTTGTACTG GAGCTGGATCGCCAGCCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGCGAGGGACTACGGCGGT GGCTGTGTATTACTGTGCGAGGGACTACGGCGGT ATGGACGTCTGGGGCCAAGGGACCACGGTCACC GTCTCCTCA SEQ ID NO: 30127 |
| | | | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS SEQ ID NO: 30128 |
| iPS:435291 | 21-225_146E1 | NA | GACATCAAGATGACCCAGTCTCCATCTTCCGT GTCTGCATCTGTAGGAGACAGAGTCACCATCA CTTGTCGGGCGAGTCAGGGTATTAACAACTGG TTAGTCTGGTATCAGCAGAAACCAGGGAAAGC CCCTAAGCTCCTGATCTATGCTGCATCCAGTTT GCAAAGTGGGGTCCCATCAAGGTTCAGCGGCA GTGGATCTGGGACAGATTTCACTCTCACCATC AGCAGCCTGCAACAGGCTAACGCTGAAGATTTTGCAACTTA CTATTGTCAACAGGCTAACAGTTTCCCATTCA CTTTCGGCCCTGGGACCAAAGTGGATATCAAA SEQ ID NO: 26123 | CAGGTGCAGCTGGTGGAGTCTGGGGGAGGCGTG GTCCAGCCTGGGAGGTCCCTGAGACTCTCCTGTG AAGCGTCTGGAATCACCTTCAGTAGCTATGGCAT GCACTGGGTCCGCCAGGCTCCAGGCAAGGGGCT GGAGTGGGTGGCAATTATATATGGTATGATGAAGT AATAAATACTATGCAGACTCCGTGAAGGGCCGA TTCACCATCTCCAGAGACAATTCCAAGAACACGC TGTTTCTGCAAATGAACAGCCTGAGAGCCGAGG ACACGGCTGTGTATTACTGTGCGAGAGATCGTTT AGTGGGAGCTACCGCTGATGCTTTTGATATCTGG GGCCAAGGGACAATGGTCACCGTCTCTTCA SEQ ID NO: 30129 |

FIGURE 50
(Continued)

| | | | |
|---|---|---|---|
| iPS:435293 | 21-225_146F1 | AA | DIKMTQSPSSVSASVGDRVTITCRASQGINNWLV WYQQKPGKAPKLLIYAASSLQSGVPSRFRGSGS GTDFTLTISSLQPEDFATYYCQQANSFPFTFGPGT KVDIK<br>SEQ ID NO: 26124 | QVQLVESGGGVVQPGRSLRLSCEASGITFSSYGMH WVRQAPGKGLEWVAIIWYDGSNKYYADSVKGRFT ISRDNSKNTLFLQMNSLRAEDTAVYYCARDRLVGA TADAFDIWGQGTMVTVSS<br>SEQ ID NO: 30130 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CGGTGGATCTGGGACAGAATTCACTCTCACAA TCAGCAGCCTGCAGCCTGAAGATTTTGCAACT TATTACTGTCTTCAGCATAGTACTTACCCGCTC ACTTTCGGCGGAGGGACCAAGGTGGAGATCA AA<br>SEQ ID NO: 26125 | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTA CTACTGGGGCTGGATCCGCCAGCCCCCAGGGAA GGGGCTGGAGTGGATTGGAGTATATTATATAGT GGGAGTACCTCCTACAACCCGTCCCTCAAGAGTC GAGTCACCATATCCGTCGACACGTCCAAGAACCA GTTCTCCCTGAAGCTGAGCTCTGTGACCGCCGCA GACACGGCTGTTTATTACTGTGCGAGACTTGATC TCCTGTGGAGTTTTGACTACTGGGGCCAGGGAAC CCTGGTCACCGTCTCCTCA<br>SEQ ID NO: 30131 |
| | | AA | DIQMTQSPSSLSASVGDRVTITCRASQGIRNDLG WYQQKPGKAPKRLIYAASSLQSGVPSRFSGGGS GTEFTLTISSLQPEDFATYYCLQHSTYPLTFGGGT KVEIK<br>SEQ ID NO: 26126 | QLQLQESGPGLVKPSETLSLTCTVSGGSISRSSYYW GWIRQPPGKGLEWIGSIYYSGSTSYNPSLKSRVTISV DTSKNQFSLKLSSVTAADTAVYYCARLDLLWSFDY WGQGTLVTVSS<br>SEQ ID NO: 30132 |

FIGURE 50
(Continued)

| | | | |
|---|---|---|---|
| iPS:435295 | 21-225_146H1 | NA | GACATCCAGATGACCCAGTCTCCATCCTCCT GTCTGCATCTGTAGGAGACAGAGTCACCATCA CTTGCCGGGCAAGTCAGAGACATTAGCGACTAT TTAAATTGGTATCAGCAAAAACCAGGAAAG CCCCTAAGGTCCTGATCTATACTACATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCCACT TTCGGCGGAGGGACCAAGGTGGAGATCAAA <br><br>SEQ ID NO: 26127 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGCTATTAGTGGTCGTGGTGGT AACACATTCTACGCAGACTCCGTGAAGGGCCGGT TCACCATCTCCAGAGACACAATTCCAAGAACACT ATATCTGCAAATGAACAGCCTGAGAGCCGAGGA CACGGCCGTATATTACTGTGCGAAACGGGTGACG GACTACGGTGTAACGACTGGTTCGACCCCTGGG GCCAGGGAACCCTGGTCACCGTCTCCTCA <br><br>SEQ ID NO: 30133 |
| | | AA | DIQMTQSPSSLSASVGDRVTITCRASQSISDYLN WYQQKPGKAPKVLIYTSSLQSGVPSRFSGSGSG TDFTLTISSLQPEDFATYYCQQSYSTPTFGGGTK VEIK <br><br>SEQ ID NO: 26128 | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKRVTDYG GNDWFDPWGQGTLVTVSS <br><br>SEQ ID NO: 30134 |
| iPS:435297 | 21-225_146B3 | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GATGAAAGACCTATTTGTATTGGTACCTGCA GAAGCCAGGCCAGCCTCCACAGTCTCCTGATCT ATGAAGTTTCCAACCGGTTCTCTGGAGTGCCA GATAGGTTCAGTGGCAGCGGGTCAGGGACAG ATTTCACACTGAAAATCAGCGCGGGTGGAGGCT GAGGATGTTGGCTTTATCACTGCATGCAAAG TATACAGCTTCCGTGGACGTTCGGCCAAGGGA CCAAGGTGGAAATCAAA <br><br>SEQ ID NO: 26129 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGCAGACTCCGTGAAGGGCCGAT TATAAATACTATGCAGACTCCGTGAAGGGCCGAT TCACCATCTCCAGAGACAATTCCAAGAACACGT GGATCTGCAAATGAACAGCCTGAGAGCCGAGGA CACGGCTGTGTATTACTGTGTGAAAATGGGTATA GAAGTGGCTGTGACTACTACTACGGTATGGACG TCTGGGGCCAAGGGACCACGGTCACCGTCTCTCTC A <br><br>SEQ ID NO: 30135 |

FIGURE 50
(Continued)

| | | | |
|---|---|---|---|
| iPS:435299 | 21-225_146D4 | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGLYHCMQSIQLPW TFGQGTKVEIK<br>SEQ ID NO: 26130 | QVQLVESGGGVVQPGRSLRLSCAASGFTFSSYGMH WVRQAPGKGLEWVAVIWYDGSYKYYADSVKGRF TISRDNSKNTLDLQMNSLRAEDTAVYYCVKMGIEV AVDYYYGMDVWGQGTTVTSS<br>SEQ ID NO: 30136 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATAACAACTACTTAGCTTGGTACCA GCAGAAACCAGGACAGCCTCCTAAGCTGGTCA TTTACTGGGCATCTCACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGTGCAGTTTTGGCCAGGG GACCAAGCTGGAGATCAAA<br>SEQ ID NO: 26131 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGGTGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTACTACTGTGCGGGAGCAG TGGCTGGTACTACTTTGACTACTGGGCCAGGGA ACCCTGTCACCGTCCTCCTCA<br>SEQ ID NO: 30137 |
| | | AA | DIVMTQSPDSLAVSLGERATINCKSSQSVLYSSN NNNYLAWYQQKPGQPPKLVIYWASTRESGVPD RFSGSGSGTDFTLTISSLQAEDVAVYYCQQYYST PCSFGQGTKLEIK<br>SEQ ID NO: 26132 | QVQLVQSGAEVKKPGASVKVSCKASGYTFTNYDIN WVRQATGQGLEWMGWVHPNSGNTGYAQKFQGR VTMTRNTSISTAYMELSSLRSEDTAVYYCAGSSGW YYFDYWGQGTLVTVSS<br>SEQ ID NO: 30138 |

FIGURE 50
(Continued)

| | | | | |
|---|---|---|---|---|
| iPS:435301 | 21-225_146G4 | NA | GAAATTGTATTGACGCAGTCTCCAGGCACCCT GTCTTTATTTCCAGGGAGAAAGAGCCACCCTCT CCTGCAGGGCCAGTCAGAATATTATCAGCAGC TATTTAGCCTGGTACCAGCAGAAACCTGGCCA GGCTCCCAGGCTCCTCATCTTTGGTGTATCTAG TCGGGCCACTGGCATCCCAGACAGACAGGTTCAGTG GCAGTGGGTCTGGGACAGACTTCACTCTCACC ATCAGCAGACTGGAGCCTGAAGATTTTGCAGT GTATTACTGTCAACAATATGGTAGGTCACCAT TCAATTTCGGCCCCTGGGACCAAAGTGGATATC AAC | CAGGTGCAGCTGCAGGAGTCGGGCCCAGGACTG GTGAAGCCTTCACAGACCCTGTCCCTCAATTGCA CTGTCTCTGGTGGCTCCATCAGCAACAGTGGTTA CTACTGGAGCTGGATCCGCCAGCACCCAGGGAA GGGCCTGGAATGGATTGGGTACAGTATTACAGT GGGAGCACCTACTACAACCCGTCCCTCAAGAGTC GAATTACCATATCAGTAGACACGTCTAACAACCA GTCTCCCTGAAGCTGACCTCTGTGACTGCCGCG GACACGGCCGTGTATTACTGTGCGAGAGGAAA TATAACTGGAACCATGCTTTTGATATCTGGGGCC AAGGGACAATGGTCACCGTCTCTTCA |
| | | | SEQ ID NO: 26133 | SEQ ID NO: 30139 |
| | | AA | EIVLTQSPGTLSLFPGERATLSCRASQNIISSYLA WYQQKPGQAPRLLIFGVSSRATGIPDRFSGSGSG TDFTLTISRLEPEDFAVYYCQQYGRSPFNFGPGT KVDIN | QVQLQESGPGLVKPSQTLSLNCTVSGGSISNSGYY WSWIRQHPGKGLEWIGYSYYSGSTYYNPSLKSRITI SVDTSNNQFSLKLTSVTAADTAVYYCARGKYNWN HAFDIWGQGTMVTVSS |
| | | | SEQ ID NO: 26134 | SEQ ID NO: 30140 |
| iPS:435303 | 21-225_146A6 | NA | GACATCCAGATGACCCAGTCTCCAGCTTCCGT GTCTGCATCTGTGGGAGACAGAGTCACCATCA CTTGTCGGGCGAGTCAGGGTATTAGCAACTGG TTAGCCTGGTATCAGCAGAAACCAGGGAAAG CCCCTAAACTCCTGATCTATGCTGCATCCAGTT TGCAAGGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGACTGACAGTTTCCCATTC ACTTTCGGCCCTGGGACCAAAGTGGATATCAA A | GAGGTGCAGCTGTTGGAGTCTGGGGGAGGCTTG GTACAGCCTGGGGGGTCCCTGAGACTCTCCTGTG CAGCCTCTGGATTCACCTTTAACAGCTATGCCAT GAACTGGGTCCGCCAGGCTCCAGGGAAGGGGCT GGAGTGGGTCTCAGTTATTAGTGGTAGTGGTGGT AACACATTCTACCGAGACTCCGTGAAGGGCCGCT TCACCATCTCCAGAGACAATTCCAAGAACACACT GTATCTGCAAATGAACAGCCTGAGAGCCGAGGA CACGGCCGTATATTACTGTGCGAAAAGGATAAT GATTACGTTTGGGGGAGTCCTTACTTTGACTACT GGGGCCAGGGAACCCTGGTCACCGTCTCCTCA |
| | | | SEQ ID NO: 26135 | SEQ ID NO: 30141 |

FIGURE 50
(Continued)

| | | | | |
|---|---|---|---|---|
| iPS:435305 | 21-225_146C9 | AA | DIQMTQSPASVSASVGDRVTITCRASQGISNWLA WYQQKPGKAPKLLIYAASSLQGGVPSRFSGSGS GTDFTLSISSLQPEDFATYYCQQTDSFPFTFGPGT KVDIK<br><br>SEQ ID NO: 26136 | EVQLLESGGGLVQPGGSLRLSCAASGFTFNSYAMN WVRQAPGKGLEWVSAISGSGGNTFYADSVKGRFTI SRDNSKNTLYLQMNSLRAEDTAVYYCAKKDNDYV WGSPYFDYWGQGTLVTVSS<br><br>SEQ ID NO: 30142 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTACACAGC TCCAACAATTATAATTACTTAGCTTGGTACCA GCAGAAACCAGGACAGCCTCCTAAGGTGCTCA TTTACTGGGCATCTACCCGGAAATCCGGGGTC CCTGACCGATTCAGTGGTAGCGGGTCTGGGAC AGATTTCACTCTCACCATCAGCAGCCTGCAGG CTGAAGATGTGGCAGTTTATTATTGTCAGCAA TATTATAGTACTCCGTGCAGTTTTGGCCAGGG GACCAAGCTGGAGATCAAA<br><br>SEQ ID NO: 26137 | CAGGTGCAGCTGGTGCAGTCTGGGGCTGAGGTG AAGAAGCCTGGGGCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCTGGAACACCTCCATAAGCACA GCCTACATGGCCCTGAGCAGCCTGAGATCTGAGG ACACGGCCGTGTATTACTGTGCGTATAGCAGTGG CTGGTACTCCTTTGACTACTGGGGCCAGGGAACC CTGGTCACCGTCTCCTCA<br><br>SEQ ID NO: 30143 |
| | | AA | DIVMTQSPDSLAVSLGERATINCKSSQSVLHSSN NYNYLAWYQQKPGQPPKVLIYWASTRKSGVPD RFSGSGSGTDFTLTISSLQAEDVAVYYCQQYYST PCSFGQGTKLEIK<br><br>SEQ ID NO: 26138 | QVQLVQSGAEVKKPGASVKVSCKASGYTFTNYDIN WVRQATGQGLEWMGWMHPNSGNTGYAQKFQGR VTMTWNTSISTAYMALSSLRSEDTAVYYCAYSSG WYSFDYWGQGTLVTVSS<br><br>SEQ ID NO: 30144 |

FIGURE 50
(Continued)

| | | | |
|---|---|---|---|
| iPS:435307 | 21-225_146E9 | NA | GACATCCAGATGACCCAGTCTCCATCCTCCCT GTCTGCATCTGTAGGAGACAGAGTCACCATCA CTTGCCGGGCAAGTCAGAGACATTAGCGACTAT TTAAATTGGTATCAGCTGAAACCAGGGAAAGC CCCTAAGGTCCTGATCTATACATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTTCTGTCAACAGAGTTACAGTACCCCACTTT CGGCGGAGGGACCAAGGTGGAGATCAAA |
| | | | SEQ ID NO: 26139 |
| | | AA | DIQMTQSPSSLSASVGDRVTITCRASQSISDYLN WYQLKPGKAPKVLIYTSSLQSGVPSRFSGSGSG TDFTLTISSLQPEDFATYFCQQSYSTPFGGGTKV EIK |
| | | | SEQ ID NO: 26140 |
| | | NA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCCGGT TCACCATCTCCAGAGACAATTCCAAGAAAACACT ATATCTGCAAATGAACAGCCTGAGAGCCGAGGA CACGGCCGTATATTACTGTGCGAAACGGGTGACG GACTACGGTGTAACGACTGGTTCGACCCCTGGG GCCAGGGAACCCTGGTCACCGTCTCCTCA |
| | | | SEQ ID NO: 30145 |
| | | AA | EVQLLESGGGLVQPGGSLRLSCAASGFTFSSYAMS WVRQAPGKGLEWVSAISGRGGNTFYADSVKGRFTI SRDNSKKTLYLQMNSLRAEDTAVYYCAKRVTDYG GNDWFDPWGQGTLVTVSS |
| | | | SEQ ID NO: 30146 |
| iPS:435309 | 21-225_146F9 | NA | GACATCGTGATGACCCAGTCTCCAGACTCCT GGCTGTGTCTCTGGGCGAGAGGGCCACCATCA ACTGCAAGTCCAGCCAGAGTATTTTACACAGC TCCAACAATAACAACTACTTAGCTTGGTACCA GCAGAAACCAGGACAGCCTCCTTACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTATTACTGTCAGCAA TATTATACTACTCCGTGCAGTTTTGGCCAGGG GACCAAGCTGGAGATCACT |
| | | | SEQ ID NO: 26141 |
| | | | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCACGAAGTCGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGAGTAGCAGT GGCTGGTACTTTTTGACTACTGGGGCCAGGGAA CCCTGGTCACCGTCTCCTCA |
| | | | SEQ ID NO: 30147 |

FIGURE 50
(Continued)

| | | | |
|---|---|---|---|
| iPS:435311 | | AA | DIVMTQSPDSLAVSLGERATINCKSSQNILHSSN NNNYLAWYQQKPGQPPYLLIYWASTRESGVPD RFSGSGSGTDFTLTITSLQAEDVAVYYCQQYYT PCSFGQGTKLEIT SEQ ID NO: 26142 | QVQLVQSGAEVKKPGASVKVSCKASGYTFNYDIN WVRQATGQGLEWMGWMHPNSGNTGYAQKFQGR VTMTRNTSISTAYMELSSLRSEDTAVYYCASSSGW YFFDYWGQGTLVTVSS SEQ ID NO: 30148 |
| | | NA | GACATCCAGATGACCCAGTCTCCATCCTCCCT GTCTGCATCTGTAGGAGACAGAGTCACCATCA CTTGCCGGGCAAGTCAGGACAGATTCAGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATATAAGTTACCCGCTC ACTTTCGGCGGAGGGACCAAGGTGGAGATCA AA SEQ ID NO: 26143 | CAGGTGCAGCTGGTGGAGTCTGGGGGAGGCGTG GTCCAGCCTGGGAGGTCCCTGAGACTCTCCTGTG CAGCGTCTGGATTCAGCTTCAGTAGCTATGGCAT GCACTGGGTCCGCCAGGCTCCAGGCAAGGGGCT GGAGTGGGTGGCAGTGATATGGTTTGATGAAAGT AATAAACACTATGGAGACTCCGTGAAGGGCCGA TTCACCATCTCCAGGGACAATTCCAAGAACACGC TGTATCTGCAAATGAACAGCCTGAGAGCCGAGG ACACGGCTGTGTATTACTGTGCGAGAGAATTGGG ATTTCTCTGACTATTGGGGCCAGGGAACCCTG GTCACCGTCTCCTCA SEQ ID NO: 30149 |
| 21-225_146H9 | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK SEQ ID NO: 26144 | QVQLVESGGGVVQPGRSLRLSCAASGFSFSSYGMH WVRQAPGKGLEWVAVIWFDESNKHYGDSVKGRF TISRDNSKNTLYLQMNSLRAEDTAVYYCARELGFL SDYWGQGTLVTVSS SEQ ID NO: 30150 |

FIGURE 50
(Continued)

| | | | | |
|---|---|---|---|---|
| iPS:435313 | 21-225_146G11 | NA | GACATCCAGATGACCCAGTCTCCATCCTCCT GTCTGCATCTGTAGGAGACAGAGTCACCATCA CTTGCCGGGCAAGTCAGGACATTAGAAATAAT TTTGGCTGTGTATCAGCAGAAACCAGGGAAAGC CCCTAAGCGCCTGATCTATGTGCATCCAGTTT GCAAAGTGGGGTCCCATTAAGGTTCAGCGGCA GTGGATCTGGGACAGAATTCACTCTCACAATC AGCAGCCTGCAGCCTGAAGATTTTGCAACTTA TTACTGTCTCCAACATGATAGTTACCCGCTCAC TTTCGGCGGAGGGACCAAGGTGGAGATCAAA<br><br>SEQ ID NO: 26145 | GAGGTGCAGCTGGTGGAGTCTGGGGGAGGCCTG GTCAAGCCTGGGGGGTCCCTGAGACTCTCCTGTG CAGCCCTCTGGATTCACCTTCAGTAGCTATAGCAT GAACTGGGTCCGCCAGGCTCCAGGGAAGGGCT GGAGTGGGTCTCATCCATTAGTGGTAGTGGTAGC TACCACATACTACGCAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGGTAGCAG CTCGTCCGGGTTTGACTACTGGGGCCAGGGAACC CTGGTCACCGTCTCCTCA<br><br>SEQ ID NO: 30151 |
| | | AA | DIQMTQSPSSLSASVGDRVTITCRASQDIRNNFG WYQQKPGKAPKRLIYAASSLQSGVPLRFSGSGS GTEFTLTISSLQPEDFATYYCLQHDSYPLTFGGG TKVEIK<br><br>SEQ ID NO: 26146 | EVQLVESGGGLVKPGGSLRLSCAASGFTFSSYSMN WVRQAPGKGLEWVSSISGSGSYTYYADSVKGRFTI SRDNAKNSLYLQMNSLRAEDTAVYYCARGSSSSGF DYWGQGTLVTVSS<br><br>SEQ ID NO: 30152 |
| iPS:435315 | 21-225_147B2 | NA | GATATTGTGATGACCCAGACTCCCCTCTCTCTG TCCGTCACGCCTGGACAGCCGGCCTCCATCTC CTGCAAGTCTAGTCAGAGCCTCCTGCATAGTG CTGCAAGTCTAGTCAGAGCCTCCTGCATAGTG AAGGAAAGACCTATTTGTATTGGTACCTGCAG AAGCCAGGCCAGCCTCCACAGCTCCTGATCTA TGAAGTTCCCAACCGGTTCAGTGGCCAG ATAGGTTCAGTGGCAGCGGGTCAGGGACAGA TTTCACAGTGAAAATCAGCGGGTGGAGGCTG AGGATGTTGGGGTTTATTACTGCATGCAAAGT ACACAAGTTTCCTCCCACTTTCGGCCCTGGGAC CAAAGTGGATATCAAA<br><br>SEQ ID NO: 26147 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGAGGTATAG CAGCAGCTGGTCGGGGGTATGGACGTCTGGGG CCAAGGGACCACGGTCACCGTCTCCTCA<br><br>SEQ ID NO: 30153 |

FIGURE 50
(Continued)

| | | | |
|---|---|---|---|
| iPS:435317 | 21-225_147D2 | AA | DIVMTQTPLSLSVTPGQPASISCKSSQSLLHSEGK TYLYWYLQKPGQPPQLLIYEVSHRVSGVPDRFS GSGSGTDFTVKISRVEAEDVGVYYCMQSTQFPP TFGPGTKVDIK<br>SEQ ID NO: 26148 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARRYSSS WSGGMDVWGQGTTVTSS<br>SEQ ID NO: 30154 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTGGCAGCAGC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAGCTTATTCA CTTTCGGCCCTGGGACCAAAGTGGATATCAAA<br>SEQ ID NO: 26149 | CAGGTGCTACTGCAGGAGTCGGGCCCAGGACTG GTGAAGCCTTCACAGACCCTGTCCCTCACCTGCG CTGTCTCTGGTGGCCCCATCAGCAGTGGTGATTA CTACTGGAACTGGATCCGCCAGCGCCAGGGAA GGGCTGGAGTGGATTGGGTTCATCTATTACACT GGGAGCACCTACTACAACCCGTCCCTCAAGAGTC GAGTTTCCATATCGGAAGACACGTCTGAGAACCA GTTCTCCCTGAACCTGAGTTCTGTGACTGCCGCG GACACGGCCGTGTATTACTGTGCGAGAGGGGA GCTTACTACTCCTACTACGGTATGGACGTCTGGG GCCAAGGGACCACGGTCACCGTCTCCTCA<br>SEQ ID NO: 30155 |
| | | AA | EIVLTQSPGTLSLSPGERATLSCRASQSVGSSYLA WYQQKPGQAPRLLIYGASSRATGIPDRFSGSGSG TDFTLTISRLEPEDFAVYYCQQYGSLFTFGPGTK VDIK<br>SEQ ID NO: 26150 | QVLLQESGPGLVKPSQTLSLTCAVSGGPISSGDYYW NWIRQRPGKGLEWIGFIYYTGSTYYNPSLKSRVSIS EDTSENQFSLNLSSVTAADTAVYYCARGGAYYSYY GMDVWGQGTTVTSS<br>SEQ ID NO: 30156 |

FIGURE 50
(Continued)

| | | | | |
|---|---|---|---|---|
| iPS:435319 | 21-225_147E3 | NA | GAAATTGTGTTGACGCAGTCTCCAGGCACCCT<br>GTCTTTGTCTCCAGGGGAAAGAGCCACCCTCT<br>CCTGCAGGGCCAGTCAGAGTGTTATCAGTAGC<br>TACTTAGCCTGGTACCAGCAGAAACCTGGCCA<br>GGCTCCCAGGCTCCTCATCTATGGTGCATCCA<br>GCAGGGCCACTGCCATCCCAGACAGGTTCAGT<br>GGCAGTGGGTCTGGGACAGACTTCACTCTCAC<br>CATCAGCAGACTGGAGCCTGAAGATTTTGCAG<br>TGTATTACTGTCAACAATATGTAGGTCACCA<br>TTCAATTTCGGCCCTGGGACCAAAGTGGATAT<br>CAAA<br><br>SEQ ID NO: 26151 | CAGGTGCAGCTGCAGGAGTCGGGCCCAGGACTG<br>GTGAAGCCTTCACAGACCCTGTCCCTCACCTGCA<br>CTGTCTCTGGTGGCTCCATCACCAATAGTGGTTA<br>CTACTATAGCTGGATCCGCCAGCACCCAGGGAA<br>GGGCCTGGAATGGATTGGGTACATCTATTACAGT<br>GGGGGCACTACTACAACCCGTCCCTCAAGAGTC<br>GAATTACCATATCAGTGGACACGTCTAACAACCA<br>GTTCTCCCTGAAGCTGAGCTCTGTGACTGCCGCG<br>GACACGGCCGTGTATTACTGTGCGAGAGGGGA<br>TATAACTGGAACCATGCTTTTGATTTCTGGGGCC<br>AAGGGACAATGGTCACCGTCTCTTCA<br><br>SEQ ID NO: 30157 |
| | | AA | EIVLTQSPGTLSLSPGERATLSCRASQSVISSYLA<br>WYQQKPGQAPRLLIYGASSRATAIPDRFSGSGSG<br>TDFTLTISRLEPEDFAVYYCQQYGRSPFNFGPGT<br>KVDIK<br><br>SEQ ID NO: 26152 | QVQLQESGPGLVKPSQTLSLTCTVSGGSITNSGYY<br>SWIRQHPGKGLEWIGYIYYSGGTYYNPSLKSRITISV<br>DTSNNQFSLKLSSVTAADTAVYYCARGGYNWNHA<br>FDFWGQGTMVTVSS<br><br>SEQ ID NO: 30158 |
| iPS:435321 | 21-225_147E4 | NA | GACATCGTGATGACCCAGTCTCCAGACTCCCT<br>GGCTGTGTCTCTGGGCGAGAGGGCCACCATCA<br>ACTGCAAGTCCAGCCAGAGTGTTTTACACAGC<br>TCCAACAATTACAACTACTTAGCTTGGTACCA<br>GCTGAAACCAGGACAGCCTCCTAAGCTGCTCA<br>TTTACTGGGCATCTACCCGGGAATCCGGGGTC<br>CCTGACCGATTCAGTGGCCGCGGGTCGGGGAC<br>AGACTTCACTCTCACCATCAGCAGCCTGCAGG<br>CTGAAGATGTGGCAATTATTATTACTGTGCAA<br>TATTATAGTACTCCATCCACTTTCGGCCCTGGG<br>ACCAAAGTGGAGATCAAA<br><br>SEQ ID NO: 26153 | CAGGTGCAGCTGGTGCAGTCTGGGGCTGAGGTG<br>AAGAAGCCTGGGGCCTCAGTGAAGGTCTCCTGC<br>AAGGCTTCTGGATACACCTTCACCAATTATGATA<br>TCAACTGGGTGCGACAGGCCACTGGACAAGGGC<br>TTGAGTGGATGGGATGGATGAACCCTAACAGTG<br>GTAACACAGGCTATGCACAGAAGTTCCAGGGCA<br>GAGTCACCATGACCAGGAACACCTCCATAAGCA<br>CAGCCTACATGGAGCTGAGCAGCCTGAGATCTG<br>AGGACACGGCCGTGTACTTTTGACTACTGGGGCCAGGG<br>GTGGCTGGTACTTTTGACTACTGTGCGAGTAGCA<br>AACCCTGGTCACCGTCCTCA<br><br>SEQ ID NO: 30159 |

FIGURE 50
(Continued)

| | | | |
|---|---|---|---|
| iPS:435323 | 21-225_147D5 | AA | DIVMTQSPDSLAVSLGERATINCKSSQSVLHSSN NYNYLAWYQLKPRQPPKLLIYWASTRESGVPDR FSGRGSGTDFTLTISSLQAEDVAIYYCQQYYSTPS TFGPGTKVEIK<br>SEQ ID NO: 26154 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YFFDYWGQGTLVTVSS<br>SEQ ID NO: 30160 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATAACAACTACTTAGCTTGGTACCA GCAGAAACCAGGACAGCCTCCTAAACTGCTCA TTTACTGGGCATCTCACCCGGGAATCCGGGGTC CCTGACCGATTCAGTGGCAGTGGGTCTGGGAC AGATTTCACTCTCTCCATCAGCAGCCTGCAGG CTGAAGATGTGGCAGTTTATTACTGTCACCAA TATTATAGTACTCCGTCAGTTTGGCCAGGG GACCAAAACTGGAGATCAAA<br>SEQ ID NO: 26155 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGG GGACACGGCCGTGTACTATTACTGTGCGGAGCAG TGGCTGGTACTACTTTGACTACTGGGGCCAGGGC ACCCTGGTCACCGTCTCCTCA<br>SEQ ID NO: 30161 |
| | | AA | DIVMTQSPDSLAVSLGERATINCKSSQSVLYSSN NNNYLAWYQQKPGQPPKLLIYWASTRESGVPD RFSGSGSGTDFTLSISSLQAEDVAVYYCHQYYST PCSFGQGTKLEIK<br>SEQ ID NO: 26156 | QVQLVQSGAEVKKPGASVKVSCKASGYTFTNYDIN WVRQATGQGLEWMGWVHPNSGNTGYAQKFQGR VTMTRNTSISTAYMELSSLRSGDTAVYYCAGSSGW YYFDYWGQGTLVTVSS<br>SEQ ID NO: 30162 |

FIGURE 50
(Continued)

| | | | | |
|---|---|---|---|---|
| iPS:435325 | 21-225_147H5 | NA | GACATCCAGATGACCCAGTCTCCATCCTCCCT GTCTGCATCTGTAGGAGACAGAGTCACCATCA CTTGCCGGGCAAGTCGGGCATTAGAGATGAT TTAGGCTGGTATCAGCAGAAACCAGGGAAAG CCCCTAAGCGCCTGATCTATGCTGCATCCAGT TTGCAGAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTATCCTCGG ACGTTCGGCCAAGGGACCAAGGTGAAATCA AA | CAGGTGCAGCTGGTGGAGTCTGGGGGAGGCGTG GCCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGGAAGT AATAAGTACTATGCAGACTCCGTGAAGGGCCGA CTCACCATCTCCAGAGACAATTCCAAGAACACGT TGTATCTGCAAATGAACAGCCTGAGCGCCGAGG ACACGGCTGTGTATTACTGTGCGAGAGAGAGGTA TAGCAGTGGCTGGTACGACTACGGTTTGGACGTC TGGGGCCAAGGGACCACGGTCACCGTCTCCTCA |
| | | | SEQ ID NO: 26157 | SEQ ID NO: 30163 |
| | | AA | DIQMTQSPSSLSASVGDRVTITCRASRGIRDDLG WYQQKPGKAPKRLIYAASSLQSGVPSRFSGSGS GTEFTLTISSLQPEDFATYYCLQHYSYPRTFGQG TKVEIK | QVQLVESGGGVAQPGRSLRLSCAASGFTFSDYGM HWVRQAPGKGLEWVAVIWYDGSNKYYADSVKGR LTISRDNSKNTLYLQMNSLSAEDTAVYYCARERYS SGWYDYGLDVWGQGTTVTVSS |
| | | | SEQ ID NO: 26158 | SEQ ID NO: 30164 |
| iPS:435327 | 21-225_147G6 | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAGTAACAACTACTTAGCTTGGTACCA GCAGAAACCAGGCCAGCCTCCTAAGCTGCTCA TTTACTGGGCATCTGCCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATACTACTCCTCCCCACTTTCGGCCCTGGG ACCAAAGTGGATATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGTTGGATGCACCCAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGTATAGCAGT GGCTGGTACTGGTTCGACCCCTGGGGCCAGGGA ACCCTGGTCACCGTCTCCTCA |
| | | | SEQ ID NO: 26159 | SEQ ID NO: 30165 |

FIGURE 50
(Continued)

| | | | |
|---|---|---|---|
| iPS:435329 | 21-225_147A8 | AA | DIVMTQSPDSLAVSLGERATINCKSSQSVLYSSN SNNYLAWYQQKPGQPPKLLIYWASARESGVPD RFSGSGSGTDFTLTISSLQAEDVAVYYCQQYYTT PPTFGPGTKVDIK<br>SEQ ID NO: 26160 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YWFDPWGQGTLVTVSS<br>SEQ ID NO: 30166 |
| | | NA | GATATTGTGATGACCCAGACTCCACTCTCTCT GTCCGTCACCCCTGGACAGCCGGCCTCCATCT CCTGCAAGACTAGTCAGAGCCTCCTGCATAGT GAAGGAAAGACCTATTTGTATTGGTACCTGCA GAAGCCAGGCCAGCCTCCACAGCTCCTGATCT ATGAAGTTTCCAACCGGTTCTCTGGAGTGCCA GATAGGTTCAGTGGCAGCGGGTCAGGACAG ATTTCACACACTGAAAATCAGCCGGGTGGAGCT GAGGATGTTGGGGTTTATTACTGCATGCAAAG TATACAGCTAATCACCTTCGGCCAAGGGACAC GACTGGAGATTAAA<br>SEQ ID NO: 26161 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAGGTATAG CAGCAGCTGACGGGGGTATGGACGTCTGGGG CCAAGGGACCACGGTCACCGTCTCCTCA<br>SEQ ID NO: 30167 |
| | | AA | DIVMTQTPLSLSVTPGQPASISCKTSQSLLHSEGK TYLYWYLQKPGQPPQLLIYEVSNRFSGVPDRFSG SGSGTDFTLKISRVEAEDVGVYYCMQSIQLITFG QGTRLEIK<br>SEQ ID NO: 26162 | QVQLVESGGGVVQPGRSLRLSCAASGFTFSSYGMH WVRQAPGKGLEWVAVIWYDGSNKYADSVKGRF TISRDNSKNTLYLQMNSLRAEDTAVYYCARRYSSS WTGGMDVWGQGTTVTVSS<br>SEQ ID NO: 30168 |

FIGURE 50
(Continued)

| | | | |
|---|---|---|---|
| iPS:435331 | 21-225_147G8 | NA | CAAATTGTGTTGACGCAGTCTCCAGGCACCCT GTCTTTGTCTCCAGGGGAAAGAGCCACCCTCT CCTGCAGGGCCAGTCAGTCAGAGAATTTCAGCAAC TACTTAGCCTGGTACCAGCAGAAAGCCTGGCCA GGCTCCCAGGATCCTCATCTATGGTGCATCCA GCAGGGCCACTGGCATCCCAGACAGGATCAGT GGCAGTGGGTCTGGGACAGACTTCACTCTCAC CATCACCAGACTGGAGCCTGAAGATTTTGCAG TGTATTACTGTCAGCAGTATGATAGCTCACCG TGGACGTTCGGCCAAGGGACCAAGGTGGAAA TCAAC<br><br>SEQ ID NO: 26163 | CAGGTGCAGCTACAGCAGTGGGGCGCAGGACTG TTGAAGCCTTCGGAGACCCTGTCCCTCACCTGCG GTGTCTATGGTGGGTCTTCAGTGCTTACTACTG GAGCTGGATCCGCCAGCCCCCAGGGAAGGGGCT GGAGTGGATTGGGGAAATCAATCATAGTGGAAG TACCAACTACAAACCGTCCCTCAAGAGTCGAGTC ACCATATCAGTAGACACGTCAAGAACCAGTTCT CCCTGAAGCTGAGCTCTGTGACCGCCGCGGACAC GGCTGTGTATTACTGTGCGAGAGACTACGGTGTT TTTGACTACTGGGGCCAGGGAACCCTGGTCACCG TCTCCTCA<br><br>SEQ ID NO: 30169 |
| | | AA | QIVLTQSPGTLSLSPGERATLSCRASQRIFSNYLA WYQQKPGQAPRILIYGASSRATGIPDRISGSGSGT DFTLTITRLEPEDFAVYYCQQYDSSPWTFGQGTK VEIN<br><br>SEQ ID NO: 26164 | QVQLQQWGAGLLKPSETLSLTCGVYGGSFSAYYW SWIRQPPGKGLEWIGEINHSGSTNYKPSLKSRVTISV DTSKNQFSLKLSSVTAADTAVYYCARDYGVFDYW GQGTLVTVSS<br><br>SEQ ID NO: 30170 |
| iPS:435333 | 21-225_147E9 | NA | GACATCCAGATGACCCAGTCTCCATCCTCACT GTCTGCATCTGTAGGAGACAGAGTCACCATCA CTTGTCGGGCGAGTCAGGACAGTCATTAACAATTAT TTAGCCTGGTTTCAGCAGAAACCAGGGAAAGC CCCTAAGTCCCTGATCGTGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATATAGTTACCCTCA TTACTGCCAACAGTATATAGTTACCCTCTCA CTTTCGGCGGAGGGACCAAGGTGGAGATCAA A<br><br>SEQ ID NO: 26165 | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTTTCATCCATTAGTGGTAGAAACACT ACCATATACTATGCAGACTCTGTGAAGGGCCGAT TCACCATCTCCAGAGACAACGCCAAGAACTCACT GTATCTGCAAATGAACAGCCTGAGAGACGAGGA CACGGCTGTTTATTACTGTTCGAGAGATCGGGGC AGTTGCTGGGGCCAGGGAACCCTGGTCACCGTCT CCTCA<br><br>SEQ ID NO: 30171 |

FIGURE 50
(Continued)

| | | | | |
|---|---|---|---|---|
| | | AA | DIQMTQSPSSLSASVGDRVTITCRASQDINNYLAWFQQKPGKAPKSLIVAASSLQSGVPSKFSGSGSGTDFTLTISSLQPEDFATYYCQQYNSYPLTFGGGTKVEIK | EVQLVESGGGLVQPGGSLRLSCAASGFTFSSYSMNWVRQAPGKGLEWVSSISGRNTIYYADSVKGRFTISRDNAKNSLYLQMNSLRDEDTAVYYCSRDRGSCWGQGTLVTVSS |
| | | | SEQ ID NO: 26166 | SEQ ID NO: 30172 |
| iPS:435335 | 21-225_147D10 | NA | GACATCCAGATGACCCAGTCTCCAGCTTCCGTGTCTGCATCTGTAGGAGACAGAGTCACCATAACTTGTCGGGCGAGTCAGATATTAGCAACTGGTTAACCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCTCCATCAGCAGCCTGCAACAGACTGACAGTTTCCCATTCACTATTGTCAACAGACTGACAGTTTCCCATTCACTTTCGGCCCTGGGACCAAAGTGGATGTCAAA | GAGGTGCAGCTGTTGGAGTCTGGGGGAGGCTTGGTACAGCCTGGGGGGTCCCTGAGACTCTCCTGTGCAGCCTCTGGATTCACCTTTAGCAGTTATAGCCATGAGCTGGGTCCGCCAGGCTCCAGGGAAGGGGCTGGAGTGGGTCTCAGCTATTAGTGGTGTGTGGTAACACATTCTACGCAGACTCCGTGAAGGGCCGCTTCACCATCTCCAGAGACAATTCCAAGAACACGCTCTATCTGCAAATGAACAGCCTGAGAGCCGAGGACACGGCCGTATATTACTGTGCGAAAAGGATTATGATTACGTTTGGGGGAGTCCTTACTTTGACTACTGGGGCCAGGGAACCCTGGTCACCGTCTCCTCA |
| | | | SEQ ID NO: 26167 | SEQ ID NO: 30173 |
| | | AA | DIQMTQSPASVSASVGDRVTITCRASQNISNWLTWYQQKPGKAPKLLIYAASSLQSGVPSRFSGSGSGTDFTLSISSLQPEDFATYYCQQTDSFPFTFGPGTKVDVK | EVQLLESGGGLVQPGGSLRLSCAASGFTFSSYAMSWVRQAPGKGLEWVSAISGRGGNTFYADSVKGRFTISRDNSKNTLYLQMNSLRAEDTAVYYCAKKDYDYVWGSPYFDYWGQGTLVTVSS |
| | | | SEQ ID NO: 26168 | SEQ ID NO: 30174 |

FIGURE 50
(Continued)

| | | | | |
|---|---|---|---|---|
| iPS:435339 | 21-225_147D12 | NA | GACATCCAGATGACCCAGTCTCCAGCTTCCGT GTCTGCATCTGTAGGAGACAGAGTCACCATA CTTGTGCGGGCGAGTCAGGGTATTAGCAACTGG TTAGCCTGGTATCAGGAGAAACCAGGGAAAG CCCCTAAACTCCTGATCTATGCTGCATCCAGTT TGCAAAGTGGGGGTCCCATCAAGGTTCAGCGGC AGTGGATCCGGGACAGATTTCACTCTCCAT CAGCAGCCTGCAGCCTGAAGATTTTGCAACTT ACTATTGTCAACAGACTGACAGTTTCCCATTC ACTTTCGGCCCTGGGACCAAAGTGGATGTCAA A | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCCGCT TCACCATCTCCAGAGACAACAATTCCAAGAACACGCT CTATCTGCAAATGAACAGCCTGAGAGCCGAGGA CACGGCCGTATATTACTGTGCGAAAAAGGATTAT GATTACGTTTGGGGGAGTCCTTACTTTGACTACT GGGGCCAGGGAACCCTGGTCACCGTCTCCTCA |
| | | | SEQ ID NO: 26169 | SEQ ID NO: 30175 |
| | | AA | DIQMTQSPASVSASVGDRVTITCRASQGISNWLA WYQEKPGKAPKLLIYAASSLQSGVPSRFSGSGSG TDFTLSISSLQPEDFATYYCQQTDSFPFTFGPGTK VDVK | EVQLLESGGGLVQSGGSLRLSCAASGFTFSSYAMS WVRQAPGKGLEWVSAISGRGGNTFYADSVKGRFTI SRDNSKNTLYLQMNSLRAEDTAVYYCAKKDYDYV WGSPYFDYWGQGTLVTVSS |
| | | | SEQ ID NO: 26170 | SEQ ID NO: 30176 |
| iPS:435341 | 21-225_148B2 | NA | GCTATTGTGATGACCCAGACTCCACTCTCTCTG TCCGTCACCCCTGGACAGCCGGCCTCCATCTC CTGCAAGTCTAGTCAGAGCCTCCTGCATGGTG CTGCAAGTCTAGTCAGAGCCTCCTGCATGGTG ATGGAAAGACCTATTTTATTGGTACCTGCAG AAGCCAGGCCAGCCTCCACAGCTCCTGATCTA TGAAGTTTCCCACCGGTTCTCTGGAGTGCCAG ATAGGTTCAGTGGCAGCGGGTCAGGGACAGA TTTCACACTGAAAATCAGCCGGGTGGAGGCTG AGGATGTTGGGGTTTATTACTGCATGCAAAGT ATACAGATTCCGTGACGTTCGGCCAAGGGAC CAAGGTGGAAATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGGCT GGAGTGGGTGGCAATTATCTGGTATGATGGAAGT TATAAATACTATGCAGACTCCGTGAAGGGCCGAT TCACCATCTCCAGAGACAATTCCAAGAACACGCT GTATCTGCAAATGAACAGCCTGAGTGCCGAGGA CACGGCTGTGTATTACTGTGCGAGAGATCATTTC GATTTTTGGAGTGGTCACTTGACTACTGGGGCC AGGGAACCCTGGTCACCGTCTCCTCA |
| | | | SEQ ID NO: 26171 | SEQ ID NO: 30177 |

FIGURE 50
(Continued)

| | | | |
|---|---|---|---|
| iPS:435343 | 21-225_148E2 | AA | AIVMTQTPLSLSVTPGQPASISCKSSQSLLHGDGKTYFYWYLQKPGQPPQLLIYEVSHRFSGVPDRFSGSGSGTDFTLKISRVEAEDVGVYYCMQSIQIPWTFGQGTKVEIK<br><br>SEQ ID NO: 26172 | QVQLVESGGGVVQPGRSLRLSCAASGFTFSSYGMHWVRQAPGKGLEWVAIIHWYDGSYKYYADSVKGRFTISRDNSKNTLYLQMNSLSAEDTAVYYCARDHFDFWSGHFDYWGQGTLVTVSS<br><br>SEQ ID NO: 30178 |
| | | NA | GACATCCAGATGACCCAGTCTCCAGCTTCCGTGTCTGCATCTGTAGGAGACAGAGTCACCATAACTTGTCGGGCGAGTCAGGGTATTAGCAACTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCTCCATCAGCAGCCTGCAGCCTGAAGATTTTGCAACTTACTATTGTCAACAGACTGACAGTTTCCCATTCACTTTCGGCCCTGGGACCAAAGTGGATGTCAAA<br><br>SEQ ID NO: 26173 | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTCGTGGTGGTAACACATTCTACGCAGACTCCGTGAAGGGCCGCTTCACCATCTCCAGAGACAATTCCAAGAACACGCTCTATCTGCAAATGAACAGCCTGAGAGCCGAGGACACGGCCGTATATTACTGTGCGAAAAAGGATTATGATTACGTTTGGGGGAGTCCTTACTTTGACTACTGGGGCCAGGGAACCCTGGTCACCGTCTCCTCA<br><br>SEQ ID NO: 30179 |
| | | AA | DIQMTQSPASVSASVGDRVTITCRASQGISNWLAWYQQKPGKAPKLLIYAASSLQSGVPSRFSGNESGTDFTLSISSLQPEDFATYYCQQTDSFPFTFGPGTKVDVK<br><br>SEQ ID NO: 26174 | EVQLLESGGGLVQPGGSLRLSCAASGFTFSSYAMSWVRQAPGKGLEWVSAISGRGGNTFYADSVKGRFTISRDNSKNTLYLQMNSLRAEDTAVYYCAKKDYDYVWGSPYFDYWGQGTLVTVSS<br><br>SEQ ID NO: 30180 |

FIGURE 50
(Continued)

| | | | | |
|---|---|---|---|---|
| iPS:435345 | 21-225_148G3 | NA | GACATCGTGATGACCCAGTCTCCAGACTCCCT GGCTGTGTCTCTGGGCGAGAGGGCCACCATCC ACTGCAAGTCCAGCCAACGTGTTTACACAGC TCCAACAATTATAATACTACTTAGCTTGGTACCA GCAGAAACCAGGACAGCCTCCTAAGCTGCTCA TTTACTGGGCATCTACCCGGATTCCGGGGTC CCTGACCGATTCAGTGGCAGCGGGTCTGGGC CGATTTCACTCTCACCATCAGCAGCCTGCAGG CTGAAGATGTGGCACTTTATTACTGTCAGCAA TATTATAGTACTCCATTCACTTTCGGCCCTGGG ACCAAAGTGGATATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCTCTGGACAAGGC TTGAGTGGATGGGATGGATGCACCTAACAGTGG TAACACAGGCTATGCACAGAACTTCCAGGGCAG AGTCACCATGACCAGGAACACCTCCATAAGCAC AGCCTACATGGAGCTGAGCAGCCTGAGATCTGA GGACACGGCCGTGTATTACTGTGCGAGTAGCAGT GGCTGGTACTTTTTGACTACTGGGGCCAGGGAA CCCTGGTCACCGTCTCCTCA |
| | | | SEQ ID NO: 26175 | SEQ ID NO: 30181 |
| | | AA | DIVMTQSPDSLAVSLGERATIHCKSSQRVLHSSN NYNYLAWYQQKPGQPPKLLIYWASTRDSGVPD RFSGSGSGADFTLTISSLQAEDVALYYCQQYYST PFTFGPGTKVDIK | QVQLVQSGAEVKKPGASVKVSCKASGYTFTNYDIN WVRQASGQGLEWMGWMHPNSGNTGYAQNFQGR VTMTRNTSISTAYMELSSLRSEDTAVYYCASSSGW YFFDYWGQGTLVTVSS |
| | | | SEQ ID NO: 26176 | SEQ ID NO: 30182 |
| iPS:435347 | 21-225_148C4 | NA | GACATCCAGATGACCCAGTCTCCATCCTCCCT GTCTGCATCTGTAGGAGACAGAGTCACCATCA CTTGCCGGGCAAGTCAGAGCATTATCAACTAT TTAAATTGGTATCAGCAGAAACCAGGGAAAG CCCCTAAGGTCCTGATCTATACTGCATCCAGTT TACAGAGTGGGGTCCCATCAAGGTTCAGTGGC AGTGGATCTGGGACAGATTTCACTCTCACCAT CAGCAGTCTGCAACCTGAAGATTTTACAACTT ACTACTGTCAACAGAGTTACAGTACCCCCACT TTCGGCGGAGGGACCAAGGTAGAGATCGAA | GAGGTGCAGCTCTTGGAGTCTGGGGGAGGCTTGG TACAGCCTGGGGGGTCCCTGAGACTCTCCTGTGC AGCCTCTGGATTCACCTTTAGCAGCTATGCCATG AACTGGGTCCGCCAGGCTCCAGGGAAGGGCTG GAGTGGGTCTCAGCTATTAGTGGTAGTGGTGGTA ACACATTCTACGCAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGCGAAACGGGTGACG GACTACGGTGGTAACGACTGGTTCGACCCTGGG GCCAGGGAACCCTGGTCACCGTCTCCTCA |
| | | | SEQ ID NO: 26177 | SEQ ID NO: 30183 |

FIGURE 50
(Continued)

| | | | |
|---|---|---|---|
| iPS:435349 | | AA | DIQMTQSPSSLSASVGDRVTITCRASQSIINYLNW YQQKPGKAPKVLIYTASSLQSGVPSRFSGSGSGT DFTLTISSLQPEDFTTYYCQQSYSTPTFGGGTKVE IE | EVQLLESGGGLVQPGGSLRLSCAASGFTFSSYAMN WVRQAPGKGLEWVSAISGSGGNTFYADSVKGRFTI SRDNSKNTLYLQMNSLRAEDTAVYYCAKRVTDYG GNDWFDPWGQGTLVTVSS |
| | | | SEQ ID NO: 26178 | SEQ ID NO: 30184 |
| | | NA | GATATTGTGATGACTCCAGACTCCACTCTCTCT GTCCGTCACCCTGGACAGCCGGGCCTCCATCT CCTGTAAGTCTAGTCAGAGCCTCCTGCATAGT GAAGGAAAGACCTATTTGTATTGGTACCTGCA GAAGCCAGGCCAGTCCTCCACAGCTCCTGATCT ATGAAGTTTCCTACCGGGTCTCTGGAGTGCCA GATAGATTCAGTGGCAGCGGGTCAGGGACAG ATTTCACACTGAAAATCAGCCGGGTGGAGGCA GAGGATGTTGGGGTCTATTTCTGCATGCAAAG TATACAGCTTCCGCTCACTTTCGGCGGAGGGA CCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGGTATAG CAGCAGCTGGTCGTGGGGGTATGGACGTCTGGGG CCAAGGGACCACGGTCACCGTCCTCCTCA |
| | | | SEQ ID NO: 26179 | SEQ ID NO: 30185 |
| | 21-225_148F5 | AA | DIVMTQTPLSLSVTPGQPASISCKSSQSLLHSEGK TYLYWYLQKPGQPPQLLIYEVSYRVSGVPDRFS GSGSGTDFTLKISRVEAEDVGVYFCMQSIQLPLT FGGGTKVEIK | QVQLVESGGGVVQPGRSLRLSCAASGFTFSSYGMH WVRQAPGKGLEWVAVIWYDGSNKYADSVKGRF TISRDNSKNTLYLQMNSLRAEDTAVYYCARRYSSS WSGGMDVWGQGTTVTVSS |
| | | | SEQ ID NO: 26180 | SEQ ID NO: 30186 |

FIGURE 50
(Continued)

| | | | |
|---|---|---|---|
| iPS:435351 | 21-225_148B6 | NA | GACATCCAGATGACCCAGTCTCCATCCTCACT GTCTGCATCTGTAGGAGACAGAGTCAGCATCA CTTGTCGGGCGAGTCAGGGCATTAGCAAATAT TTAGCCTGGTTTCAGCAGAAACCAGGGAAAGC CCCTAAGTCCCTGATCTTTGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATAATAGTTTCCCATTCAC TTTCGGCCCTGGGACCAAAGTGGATATCAAA SEQ ID NO: 26181 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGTCT TGAGTGGATGGGTTGGATCCACCTAACAATGGT GGCACAAACTATGCACAGAAGTTTCAGGGCAGG GTCACCATGACCAGGGACACGTCCATCAGCACA GTCTACATGGAGCTGAGCAGGCTGAGATCTGAC GACACGGCCGTGTATTACTGTGCGAGAGATCCTG TAGTAGTACCAGCTGCCCCTTTGACTACTGGGGG CCAGGGAACCCTGGTCACCGTCTCCTCA SEQ ID NO: 30187 |
| | | AA | DIQMTQSPSSLSASVGDRVSITCRASQGISKYLA WFQQKPGKAPKSLIFAASSLQSGVPSKFSGSGSG TDFTLTISSLQPEDFATYYCQQYNSFPFTFGPGTK VDIK SEQ ID NO: 26182 | QVQLVQSGAEVKKPGASVKVSCKASGYTFTGYYM HWVRQAPGQGLEWMGWIHPNNGTNYAQTFQGR VTMTRDTSISTVYMELSRLRSDDTAVYYCARDPVV VPAAPFDYWGQGTLVTVSS SEQ ID NO: 30188 |
| iPS:435353 | 21-225_148F8 | NA | GACATCGTGATGACCCAGTCTCTAGACTCCCT GGCTGTGTCTCTGGGCGAGAGGGCCACCATCA ACTGCAAGTCCAGCCAGAGTGTCTTACACAGC TCCAACAATTACAACTACTTAGCTTGGTACCA GCAGAAACCAGGACAGCCTCCTAAACTGCTCA TTTACTGGGCATCTACCCGGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTATTCCTCCGACGTTCGGCCAAGG GACCAAGGTGGAAATCAAA SEQ ID NO: 26183 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGCCAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTACTACTTGACTACTGGGGCCAGGG GTGGCTGGTACTACTTTGACTACTGGGGCCAGGG AACCCTGGTCACCGTCTCCTCA SEQ ID NO: 30189 |

FIGURE 50
(Continued)

| | | | |
|---|---|---|---|
| iPS:435355 | | AA | DIVMTQSLDSLAVSLGERATINCKSSQSALHSSN NYNYLAWYQQKPGQPPKLLIYWASTRKSGVPD RFSGSGSGTDFTLTISSLQAEDVAVYYCQQYYSI PPTFGQGTKVEIK<br>SEQ ID NO: 26184 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YYFDYWGQGTLVTVSS<br>SEQ ID NO: 30190 |
| | | NA | GACATCCAGATGACCCAGTCTCCATCCTCCCT GTCTGCATCTGTAGGAGACAGAGTCACCATCA CTTGCCGGGCAAGTCAGAGCATTAGTAACTAT TTAAATTGGTATCAGCAGAAACCAGGGAAAG CCCCTAAGGTCCTGATCTATATTGCATCCAGTT TGCAAAGTGGGGTCCCATCTAGGTTCAGTGGC AGTGGATCTGGGACAGATTTCACTCTCACCAT CAGCAGTCTGCAACCTGAAGATTTTGCAACTT ACTACTGTCAACAGAGTTACAGTACCCCCACT TTCGGCGGAGGGACCAAGGTGGAGATCAAA<br>SEQ ID NO: 26185 | GAGGTGCAGCTGTTGGAGTCTGGGGGAGGCTTG GTACAGCCGGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCCGGT TCACCATCTCCAGAGACAACAATTCCAAGAACACACT ATATTGCAAATGAACAGCTGAGAGCCGAGGA CACGGCCGTATATTACTGTGCGAAACGGGTGACG GACTACGGTGGTAACGACTGGTTCGACCCCTGGG GCCAGGGAACCCTGGTCACCGTCTCCTCA<br>SEQ ID NO: 30191 |
| 21-225_148H9 | | AA | DIQMTQSPSSLSASVGDRVTITCRASQSISNYLN WYQQKPGKAPKVLIYIASSLQSGVPSRFSGSGSG TDFTLTISSLQPEDFATYYCQQSYSTPTFGGGTK VEIK<br>SEQ ID NO: 26186 | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKRVTDYG GNDWFDPWGQGTLVTVSS<br>SEQ ID NO: 30192 |

FIGURE 50
(Continued)

| | | | | |
|---|---|---|---|---|
| iPS:435357 | 21-225_148G10 | NA | GATATTGTGATGACCCAGACTCCACTCTCT GTCCGTCACCCCTGGACAGCCGGCCTCCATCT CCTGCAAGTCTAGTCAGAGCCTCCTGCATGGT GATGGAAAGAACCTATTTGTATTGGTACCTGCA GAGGCCAGGCCAGCCTCCACAGCTCCTGATCT ATGAAGTTTCCAACCGGTTCTCTGGAGTGCCA GATAGGTTCAGTGGCAGCGGGTCAGGGACAG ATTTCACACTGAAAATCAGCGGGTGGAGGCT GAGGATGTTGGGGTTTATTACTGCATGCAAAG TATACAGCTTCCGTGACGTTCGGCCAAGGGA CCAAGGTGGAAATCAAA SEQ ID NO: 26187 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAAG ACACGGCTGTGTATTACTGTGCGAGAGATCGTTA CGATTTTTGGAGTGGTCACTTTGACTACTGGGGC CAGGGAACCCTGGTCACCGTCTCCTCA SEQ ID NO: 30193 |
| | | AA | DIVMTQTPLSLSVTPGQPASISCKSSQSLLHGDG KTYLYWYLQRPGQPPQLLIYEVSNRFSGVPDRFS GSGSGTDFTLKISRVEAEDVGVYYCMQSIQLPW TFGQGTKVEIK SEQ ID NO: 26188 | QVQLVESGGGVVQPGRSLRLSCAASGFTFSSYGMH WVRQAPGKGLEWVAIIWYDGSNKYYADSVKGRFT ISRDNSKNTLYLQMNSLRAEDTAVYYCARDRYDF WSGHFDYWGQGTLVTVSS SEQ ID NO: 30194 |
| iPS:435359 | 21-225_148H10 | NA | GATATTGTGATGACCCAGACTCCACTCTCT GTCCGTCACTCCTGGACAGCCGGCCTCCATCT CCTGCAAGTCTAGTCAGAGCCTCCTGCATAGT GAGGGAAAGAACCTATTTGTATTGGTACCTGCA GAAGCCAGGCCAGCCTCCACAGCTCCTGATCT ATGAAGTTTCCTACCGGGTCTCTGGAGTGCCA GATAGGTTCAGTGGCAGCGGGTCAGGGACAG ATTTCACACTGAAAATCAGCGGGTGGAGGCA GAGGATGTTGGGGTCTATTACTGCATGCAGAG TATACAGCTTCCGCTCACTTTCGGCGGAGGGA CCAAGGTGGAGATCAAA SEQ ID NO: 26189 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTATTGTGCGAGGAGGTATAG CAGCAGCTGGTCGGGGGTATGACGTCTGGGG CCAAGGGACCACGGTCACCGTCTCCTCA SEQ ID NO: 30195 |

FIGURE 50
(Continued)

| | | | |
|---|---|---|---|
| iPS:435361 | | AA | DIVMTQTPLSLSVTPGQPASISCKSSQSLLHSEGK TYLYWYLQKPGQPPQLLIYEVSYRVSGVPDRFS GSGSGTDFTLKISRVEAEDVGVYYCMQSIQLPLT FGGGTKVEIK<br>SEQ ID NO: 26190 | QVQLVESGGGVVQPCRSLRLSCAASGFTFSSYGMH WVRQAPGKGLEWVAVIWYDGSNKYYGDSVKGRF TISRDNSKNTLYLQMNSLRAEDTAVYYCARRYSSS WSGGMDVWGQGTTVTVSS<br>SEQ ID NO: 30196 |
| | | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTCTGCTGCATCCAGTT TGCAAAGTGGGGTCCCATCAAGGTTCACCGGC AGTGGATCTGGGACAGAGAATTCACTTTCACAAT CAGCAGCGTGCAGCCTGAAGATTTTGCAACTT ATTACTGTCTACAGCATCGTAATTACCCGCTC ACTTTCGGCGGAGGGACCAAGGTGGAGATCA AA<br>SEQ ID NO: 26191 | CAGCTGCAGCTGCAGGAGTCGGGCCCAGGACTG GTGAAGCCTTCGGAGACCCTGTCCTCACCTGCA CTGTCTCTGGTGTCTCCATCAGCAGAAGTAGTTA CTACTGGGGCTGGATCCGCCAGCCCCCAGGGAA GGGGCTGGAGTGGATTGGGAGTATCTATTATAGT GGGAGCACCTCCTACAACCCGTCCTCAAGAGTC GAGTCACCATATCCGTAGACACGTCCAAGAACC AGTTCTCCCTGAAGCTGAGCTCTGTGACCGCCGC AGACACGGCTGTGTTTACTGTGCGAGACTTGAT CCCCAGTGGAGTTTTGACTACTGGGGCCAGGAA TCCTGGTCACCGTCTCCTCA<br>SEQ ID NO: 30197 |
| | 21-225_148E11 | AA | DIQMTQSPSSLSASVGDRVTITCRASQGIRNDLG WYQQKPGKAPKRLISAASSLQSGVPSRFTGSGSG TEFTFTISSVQPEDFATYYCLQHRNYPLTFGGGT KVEIK<br>SEQ ID NO: 26192 | QLQLQESGPGLVKPSETLSLTCTVSGVSISRSSYYW GWIRQPPGKGLEWIGSIYYSGSTSYNPSLKSRVTISV DTSKNQFSLKLSSVTAADTAVFYCARLDPQWSFDY WGQGILVTVSS<br>SEQ ID NO: 30198 |

FIGURE 50
(Continued)

| | | | | |
|---|---|---|---|---|
| iPS:435363 | 21-225_148F12 | NA | GACATCCAGATGACCCAGTCTCCTTCCTCCCT GTCTGCATCTGTAGGAGACAGAGTCACCATCA CTTGCCGGGCAAGTCAGGGCATTAGAAATGCC TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTGCAACT TATTTCTGTCTACACAGCATAATAGTTACCCTCTC ATTTTCGGCGGAGGGACCAAGGTGGAGATCA AA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAACTGGATCCGCCAGCACCCAGGAA GGGCCTGGAGTGGATTGGGTACATCTATTACAGT GGGAGCACCTACTACAACCCGTCCCTCAAGAGTC AAATTACCATATCAGTGGACACGTCTAAGGACCA GTTCTCCCTGAGGCTGAGCTCTGTGACTGCCGCG GACACGGCCGTGTATTACTGTGCGAGGTACAGTA CCTACGACTACTACGGTATGGACGTCTGGGG CCAAGGGACCACGGTCACCGTCTCCTCA |
| | | AA | DIQMTQSPSSLSASVGDRVTITCRASQGIRNALG WYQQKPGKAPKRLIYAASSLQSGVPSRFSGSGS GTEFTLTISSLQPEDFATYFCLQHNSYPLIFGGGT KVEIK | QVQLQESGPGLVKPSQTLSLTCTVSGGSISNGGYY WNWIRQHPGKGLEWIGYIYYSGSTYYNPSLKSQITI SVDTSKDQFSLRLSSVTAADTAVYYCARYSTYDYY YGMDVWGQGTTVTVSS |
| | | | SEQ ID NO: 26193 | SEQ ID NO: 30199 |
| | | | SEQ ID NO: 26194 | SEQ ID NO: 30200 |
| iPS:435365 | 21-225_149F1 | NA | GATATTGTGATGACCCAGTCTCCACTCTCTG TTCGTCACTCCTGGACAGCCGGCCTCCATCTCC TACAAGTCTAGTCAAGAGCCTCTGCATGGTGA TGGAAAGAACCTATTTTTATTGGTACCTGCAGA AGCCAGGCCAGTCCACGGTTCTCTGAGTGCAGA GAAGTTCCCACCGGTTCTCTGAGTGCCAGA TAGGTTCAGTGGCAGCGGGTCAGGGACAGATT TCACACTGAAAATCAGCCGGGTGGAGGCTGA GGATGTTGGGGTTTATTACTGCATGCAAGTA TACAGATTCCGTGGACGTTCGGCCAAGGGACC AAGGTGGAAATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAATTATCTGGTATGATGGAAGT TATAAATACTATGCAGACTCCGTGAAGGGCCGAT TCACCATCTCCAGAGACAATTCCAAGAACACGCT GTATCTGCAAATGAACAGCCTGAGTGCCGAGGA CACGGCTGTGTATTACTGTGCGAGAGATCATTTC GATTTTTGGAGTGGTCACTTGACTACTGGGGCC AGGGAACCCTGGTCACCGTCTCCTCA |
| | | | SEQ ID NO: 26195 | SEQ ID NO: 30201 |

FIGURE 50
(Continued)

| | | | |
|---|---|---|---|
| iPS:435367 | | AA | DIVMTQSPLSLFVTPGQPASISYKSSQSLLHGDG KTYFYWYLQKPGQPPQLLIYEVSHRFSGVPDRFS GSGSGTDFTLKISRVEAEDVGVYCMQSIQIPWT FGQGTKVEIK<br>SEQ ID NO: 26196 | QVQLVESGGGVVQPGRSLRLSCAASGFTFSSYGMH WVRQAPGKGLEWVAIIWYDGSYKYYADSVKGRFT ISRDNSKNTLYLQMNSLSAEDTAVYYCARDHFDF WSGHFDYWGQGTLVTVSS<br>SEQ ID NO: 30202 |
| | 21-225_149G1 | NA | GACATCCAGATGACCCAGTCTCCATCCTCCCT GTCTGCATCTGTAGGAGCCAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAAT TTGCAAAGTGGGGTCCCATCAAGGTTCAGTGG CAGTGGATCTGGGACAGAATTCACTCTCACAA TCAGCAGCCTGCAGCCTGAAGATATTTGCAACT TATTACTGTCTACAGCATATAAGTTACCCGCTC ACTTTCGGCGGAGGGACCAAGGTGGAGATCA AA<br>SEQ ID NO: 26197 | CAGGTGCAGTTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGAAGGAAG TAATAAATACTATGCAGACTCCGTGAAGGGCCG ATTCACCATCTCCAGAGACAATTCCAAGAACATG TTGTATCTGCAAATGAACAGCCTGAGAGCCGAG GACACGGCTGTGTATTACTGTGCGAGAGAAATAG GATTCAGTGAGGACTACTGGGGCCAGGGAACCC TGGTCACCGTCTCCTCA<br>SEQ ID NO: 30203 |
| | | AA | DIQMTQSPSSLSASVGARVTITCRASQGIRNDLG WYQQKPGKAPKRLIYAASNLQSGVPSRFSGSGS GTEFTLTISSLQPEDFATYYCLQHNSYPLTFGGG TKVEIK<br>SEQ ID NO: 26198 | QVQLVESGGGVVQPGRSLRLSCAASGFTFSDYGM HWVRQAPGKGLEWVAVIWYEGSNKYYADSVKGR FTISRDNSKNMLYLQMNSLRAEDTAVYYCAREIGF SEDYWGQGTLVTVSS<br>SEQ ID NO: 30204 |

FIGURE 50
(Continued)

| | | | |
|---|---|---|---|
| iPS:435369 | 21-225_149A2 | NA | GACATCGTGATGACCCAGTCTCCAGACTCCCT GGCTGTGTCTCTGGGCGAGAGGGCCACCATCA ACTGCAAGTCCAGCCAGAGTGTTTATACAGT CCCAACAATAACAACTACTTAGCTTGGTACCA GCAGAAACCAGGACAGCCCCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGTGCAGTTTGGCCAGGG GACCAAGGTGGAGATCAAA<br>SEQ ID NO: 26199 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGGTGCACCTAACAGTGG TAACACAGGCTATGCACAGAAGTTCAGGGCAG AGTCACCATGACCAGGAACACCTCCATAAGCAC AGCCTACATGGAGCTGAGCAGCCTGAGATCTGA GGACACGGCCGTGTACTATTACTGTGCGGGAGCAG TGGCTGGTACTACTTTGACTACTGGGGCCAGGGA ACCCTGGTCACCGTCTCCTCA<br>SEQ ID NO: 30205 |
| | | AA | DIVMTQSPDSLAVSLGERATINCKSSQSVLYSPN NNNYLAWYQQKPGQPPKLLIYWASTRESGVPD RFSGSGSGTDFTLTISSLQAEDVAVYYCQQYYST PCSFGQGTKVEIK<br>SEQ ID NO: 26200 | QVQLVQSGAEVKKPGASVKVSCKASGYTFTNYDIN WVRQATGQGLEWMGWVHPNSGNTGYAQKFQGR VTMTRNTSISTAYMELSSLRSEDTAVYYCAGSSGW YYFDYWGQGTLVTVSS<br>SEQ ID NO: 30206 |
| iPS:435371 | 21-225_149A3 | NA | GACATCCAGATGACCCAGTCTCCATCCTCCCT GTCTGCATCTGTAGGAGACAGAGTCACCATCA CTTGCCGGGCAAGTCAGAGCATTAGCAGTTAT TTAAATTGGTATCAGCAGAAACCAGGGAAAG CCCCTAAGGTCCTGATCTATACTGCATCCAGT TTGCAAAGTGGGGTCCCATCAAGGTTCAGTGG CAGTGGATCTGGGACAGATTTCACTCTCACCA TCAACAGTCTGCAACCTGAAGATTTTGCAACT TACTACTGTCAACAGAGTTACAGTATCCCCAC TTTCGGCGGAGGGACCAAGGTGGAGATCAAA<br>SEQ ID NO: 26201 | GAGGTGCAGCTGTTGGAGTCTGGGGGAGGCTTG GTACAGCCTGGGGGGTCCCTGAGACTCTCCTGTG CAGCCTCTGGATTCACCTTTAGCAACTATGCCAT GACCTGGGTCCGCCAGGCTCCAGGGAAGGGGCT GGAGTGGGTCTCAGTTATTAGTGGTCGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTACGAAACGGGTGACG GACTACGGTGGTAACGACTGGTTCGACCCCTGGG GCCAGGGAACCCTGGTCACCGTCTCCTCA<br>SEQ ID NO: 30207 |

FIGURE 50
(Continued)

| | | | | |
|---|---|---|---|---|
| | | AA | DIQMTQSPSSLSASVGDRVTITCRASQSISSYLNWYQQKPGKAPKVMIYTASSLQSGVPSRFSGSGSGTDFTLTINSLQPEDFATYYCQQSYSIPTFGGGTKVEIK | EVQLLESGGGLVQPGGSLRLSCAASGFTFSNYAMTWVRQAPGKGLEWVSAISGRGNTFYADSVKGRFTISRDNSKNTLYLQMNSLRAEDTAVYYCTKRVTDYGGNDWFDPWGQGTLVTVSS |
| | | | SEQ ID NO: 26202 | SEQ ID NO: 30208 |
| iPS:435373 | 21-225_149E3 | NA | GACATCGTGATGACCCAGTCTCCAGACTCCCTGGCTGTGTCTCTGGGCGAGAGACTGTTTACACAGCGCTGCAAGTCCAGCCAGATCAGTATTAGCTACCTGAATTGGTACCATCCAATAATCACAATTACTTTGCTTGGTACCAGCAGAAACCAGGACAGGCTCCTAAGCTGCTCATTTACTGGGCATCTACCCTGAGATCCGGGGTCCCTGACCGATTCAGTGGCAGTGGGTCTGGGACAGATTTCACTCTCACCATCAGCAGCCTGCAGGCTGAAGATGTGGCAGTTTATTACTGTCAGCAATATTATAGTACTCCTCCGACGTTCGGCCAAGGGACCAAGGTGGAAATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCCTTGAGTGGATGGGATGGATGCACAGAAGTTCCAGGGCAGTAACACAGGCTATGCACAAGAACACTCCATAAGCACAGTCACCATGACCAGGAACACCTCCATAAGCACAGCCTACATGGAGCTGAGCAGCCTGACATCTGAGGACACGGCCGTGTATTACTGTGCATATAGCAGTGGCTGGTACTGGTTTGACTACTGGGGCCAGGGAACCCTGGTCACCGTCTCCTCA |
| | | | SEQ ID NO: 26203 | SEQ ID NO: 30209 |
| | | AA | DIVMTQSPDSLAVSLGERATISCKSSQTVLHNSNNHNYFAWYQQKPGQPPKLLIYWASTLRSGVPDRFSGSGSGTDFTLTISSLQAEDVAVYYCQQYYSTPPTFGQGTKVEIK | QVQLVQSGAEVKKPGASVKVSCKASGYTFNYDINWVRQATGQGLEWMGWMHPNSGNTGYAQKFQGRVTMTRNTSISTAYMELSSLTSEDTAVYYCAYSSGWYWFDYWGQGTLVTVSS |
| | | | SEQ ID NO: 26204 | SEQ ID NO: 30210 |

FIGURE 50
(Continued)

| | | | | |
|---|---|---|---|---|
| iPS:435375 | 21-225_149H4 | NA | GACATCGTGATGACCCAGTCTCCAGACTCCCT GGCTGTATCTCTGGGCGAGAGGGCCACCATCA ACTGCAAGTCCAGCCAGAGTGTTTTATCCAGC TCCAACGATAACAACAAGTACTTAGCTTGGTACCA ACAGAAACCAGGACAGCCTCCTAAGCTGCTCA TTTACTGGTCATCTCCGGGAATCCGGGGTC CCTGACCGATTCAGTGGCAGCGGGTCTGGGAC AGATTTCACTCTCACCATCAGCAGCTGCAGG CTGAAGATGTGGCAGTTTATTACTGTCACCAA TATTATAGTTATCCTCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGACTATGCACAGAAGTTCAGGGCAG AGTCACCATGACCAGGAACACCTCCATAACCAC AGTTTACATGGAGCTGAGCAGCTGAGATCTGAG GACACGGCCGTGTATTATTGTACGTTAGCAGTG GCTGGTACTACTTTGACTACTGGGGCCAGGGAAC CCTGGTCACCGTCTCCTCA |
| | | AA | SEQ ID NO: 26205 DIVMTQSPDSLAVSLGERATINCKSSQSVLSSSN DNNYLAWYQQKPGRPPKLLIYWSSTRESGVPDR FSGSGSGTDFTLTISSLQAEDVAVYYCHQYYSYP PTFGQGTKVEIK | SEQ ID NO: 30211 QVQLVQSGAEVKKPGASVKVSCKASGYTFTNYDIN WVRQATGQGLEWMGWMHPNSGNTDYAQKFQGR VTMTRNTSITVYMELSSLRSEDTAVYYCTFSSGW YYFDYWGQGTLVTVSS |
| | | | SEQ ID NO: 26206 | SEQ ID NO: 30212 |
| iPS:435377 | 21-225_149G5 | NA | GACATCCAGATGACCCAGTCTCCTTCCTCCCT GTCTGCATCTGTAGGAGACAGAGTCACCATCA CTTGCCGGGCAAGTCAGGGCATTAGAAATGCC TTAGGCTGGTTTCAGCAGAAACCAGGGAAAGC CCCTAAGCGCCTGATCTATGCTGCATCCAGTTT GCAAAGTGGGGTCCCATCAAGGTTCAGCGGCA GTGGATCTGGGACAGAATTCACTCTCACAATC AGCAGCCTGCAGCCTGAAGATTTTGCAACTTA TTACTGTCTACAGCATAATAGTTACCCTCTCAC TTTCGGCGGAGGGACCAAGGTGGAGATCAAA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAACTGGATCCGCCAGCACCCAGGAA GGGCCTGGAGTGGATTGGGTACATCTATTACAGT GGGAGCACCTACTACAACCCGTCCCTCAAGAGTC GAGTTACCATATCAGTAGACACGTCTAAGGACCA GTTCTCCCTGAGGCTGAGCTCTGTGACTGCCGCG GACACGGCCGTGTATTACTGTGCGAGGTACAGTA CCTACGACTACTACGGTATGGACGTCTGGGG CCAAGGGACCACGGTCACCGTCTCCTCA |
| | | | SEQ ID NO: 26207 | SEQ ID NO: 30213 |

FIGURE 50
(Continued)

| | | | |
|---|---|---|---|
| | | AA | DIQMTQSPSSLSASVGDRVTITCRASQGIRNALG WFQQKPGKAPKRLIYAASSLQSGVPSRFSGSGSG TEFTLTISSLQPEDFATYYCLQHNSYPLTFGGGT KVEIK<br>SEQ ID NO: 26208 | QVQLQESGPGLVKPSQTLSLTCTVSGGSISNGGYY WNWIRQHPGKGLEWIGYIYYSGSTYNPSLKSRVT ISVDTSKDQFSLRLSSVTAADTAVYYCARYSTYDY YYGMDVWGQGTTVTVSS<br>SEQ ID NO: 30214 |
| iPS:435379 | 21-225_149B6 | NA | GACATCCAGATGACCCAGTCTCCATCTTCCGT GTCGGCATCTGTAGGAGACAGAGTCACCATCA CTTGTCGGGCGAGTCAGGGTATTAGAAACCAGGA TTAGCCTGGTATCAGCAGAAACCAGGAAAAG CCCCTAAGCTCCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGGTAACAGTTTCCCATTC ACTTTCGGCCCTGGGACCAAAGTGGATATCAA A<br>SEQ ID NO: 26209 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTAGTGGTGGT AGCACAATTCTACGCAGACTCCGTGAAGGGCCGGT TCACCATCTCCAGAGACAATTCCAAGAACACGCT GTTTCTGCAAATGAACAGCTGAGAGCCGAGGA CACGGCCGTATATTACTGTGCGAAACGAACTCCG GAAGATGTTTTGATATCTGGGGCCAAGGGACAA TGGTCACCGTCTCTTCA<br>SEQ ID NO: 30215 |
| | | AA | DIQMTQSPSSVSASVGDRVTITCRASQGIISWLA WYQQKPGKAPKLLIYAASSLQSGVPSRFSGSGS GTDFTLTISSLQPEDFATYYCQQGNSFPFTFGPGT KVDIK<br>SEQ ID NO: 26210 | EVQLLESGGGLVQPGGSLRLSCAASGFTFSSYAMS WVRQAPGKGLEWVSVISGSGGSTFYADSVKGRFTI SRDNSKNTLFLQMNSLRAEDTAVYYCAKRTPEDVF DIWGQGTMVTVSS<br>SEQ ID NO: 30216 |

FIGURE 50
(Continued)

| | | | | |
|---|---|---|---|---|
| iPS:435381 | 21-225_149C6 | NA | GACATCCAGATGACCCAGTCTCCAGTTCCGT GTCTGCATCTGTAGGAGACAGAGTCACCATA CTTGTCGGGCGAGTCAGGGTATTAGCAACTGG TTAGCCTGGTATCAGCAGAAACCAGGAGAG CCCCTAAGCTCCTGATCTATGCTGCATCCAGTT TGCAAGGTGGGGTCCCATCAAGGTTCAGCGGC AGTGGATCTGGGACAGATTACACTCTCCAT CAGCAGCCTGCAGCCTGAAGATTTTGCAACTT ACTATTGTCAACAGACTGACAGTTCCATTC ACTTTCGGCCCTGGGACCAAAGTGGATATCAA A | GAGGTGCAGCTGTTGGAGTCTGGGGGAGGCTTA GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTATTAGTGGTAGTGGTGGT AACACATTCTACGCAGACTCCGTGAAGGGCCGCT TCACCATCTCCAGAGACAACAATTCCAAGAACACGCT GTATCTGCACATGAACAGCCTGAGAGCCGAGGA CACGGCCGTTTATTACTGTGCGAAAAGGATTAT GATTACGTTTGGGGGAGTCCTTACTTTGACTACT GGGGCCAGGGAACCCTGGTCACCGTCTCATCA |
| | | | SEQ ID NO: 26211 | SEQ ID NO: 30217 |
| | | AA | DIQMTQSPASVSASVGDRVTITCRASQGISNWLA WYQQKPGRAPKLLIYAASSLQGGVPSRFSGSGS GTDYTLSISSLQPEDFATYYCQQTDSPFTFGPGT KVDIK | EVQLLESGGGLVQPGGSLRLSCAASGFTFSSYAMS WVRQAPGKGLEWVSAISGSGGNTFYADSVKGRFTI SRDNSKNTLYLHMNSLRAEDTAVYYCAKKDYDYV WGSPYFDYWGQGTLVTVSS |
| | | | SEQ ID NO: 26212 | SEQ ID NO: 30218 |
| iPS:435383 | 21-225_149D7 | NA | GAAATTGTGTTGACGCAGTCTCCAGGCACCCT GTCTTTGTTTCCAGGGGAAAGAGTCACCCTCT CCTGCAGGGCCAGTCAGAGTATTATCAGCAAC TACTTAGCCTGGTACCAGCAGAAACCTGGCCA GGCTCCCAGGCTCCTCATCTTTGGTGTATCTAG TAGGGCCACTGGCATCCCAGACAGGTTCAGTG GCAGTGGGTCTGGGACAGACTTCACTCTCACC ATCAGCAGACTGGAGCCTGAAGATTTTGCAGT GTATTACTGTCAACAATATGGTCGGTCACCAT TCAATTTCGGCCCTGGGACCAAAGTGGATATC AAA | CAGGTGCAGCTGCAGGAGTCGGGCCCAGGACTG GTGAAGCCTTCACAGACCCTGTCCCTCAATTGCA CTGTCTCTGGTGGCTCCATCAGCAACAGTGGTTA CTACTGGAGCTGGATCCGCCAGCACCCAGGGAA GGGAGCACTACTACAACCCGTCCTCAAGAGTC GAATTACCATATCAGTAGACACGTCTAACAACCA GTTCTCCCTGAAGCTGAGCTCTGTGACTGCCGCG GACACGGCCGTGTATTACTGTGCGAGAGGGGGA TATAACTGGAACCATGCTTTTGATATCTGGGGCC AAGGGACAATGGTCATCGTCTCTTCA |
| | | | SEQ ID NO: 26213 | SEQ ID NO: 30219 |

FIGURE 50
(Continued)

| | | | |
|---|---|---|---|
| | | AA | EIVLTQSPGTLSLFPGERVTLSCRASQSIISNYLA WYQQKPGQAPRLLIFGVSSRATGIPDRFSGSGSG TDFTLTISRLEPEDFAVYYCQQYGRSPFNFGPGT KVDIK | QVQLQESGPGLVKPSQTLSLNCTVSGGSISNSGYY WSWIRQHPGKGLEWIGYSYYSGSTYYNPSLKSRITI SVDTSNNQFSLKLSSVTAADTAVYYCARGGYNWN HAFDIWGQGTMVIVSS |
| | | | SEQ ID NO: 26214 | SEQ ID NO: 30220 |
| iPS:435391 | 21-225_149F8 | NA | GACATCCAGATGACCCAGTCTCCAGCTTCCGT GTCTGCATCTGTAGGAGACAGAGTCACCATAA CTTGTCGGGCGAGTCAGGGTATTAGCAACTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AATGAATCTGGGACAGATTTCACTCTCTCCAT CAGCAGCCTGCAGCCTGACAGTTTCCCATTC ACTATTGTCAACAGAGACTGACAGTTTCCCATTC ACTTTCGGCCCTGGGACCAAAGTGGATGTCAA A | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGAGACTCCGTGAAGGGCCGCT TCACCATCTCCAGAGACAACAATTCCAAGAACACGCT CTATCTGCAAATGAACAGCCTGAGAGCCGAGGA CACGGCCGTATATTACTGTGCGAAAAAGGATTAT GATTACGTTTGGGGGAGTCCTTACTTTGACTACT GGGGCCAGGGAACCCTGGTCACCGTCTCCTCA |
| | | | SEQ ID NO: 26215 | SEQ ID NO: 30221 |
| | | AA | DIQMTQSPASVSASVGDRVTITCRASQGISNWLA WYQQKPGKAPKLLIYAASSLQSGVPSRFSGNES GTDFTLSISSLQPEDFAIYYCQQTDSFPFTFGPGT KVDVK | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKKDYDYV WGSPYFDYWGQGTLVTVSS |
| | | | SEQ ID NO: 26216 | SEQ ID NO: 30222 |

FIGURE 50
(Continued)

| | | | | |
|---|---|---|---|---|
| iPS:435393 | 21-225_149D10 | NA | GACATCCAGATGACCCAGTCTCCATCCTCCCT GTCTGCATCTGTAGGAGACAGAGTCACCATCA CTTGCCGGGCAAGTCGGGCATTAGAAATGAT TTAGGCTGGTATCAGCAGAAACCAGGGAAAG CCCCTAAGCGCCTGATCTATGCTGCATCCAGT TTGCAGAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATTATAGTTATCCTCGG ACGTTCGGCCAAGGGACCAAGGTGGAAATCA AA | CAGGTGCAGCTGGTGGAGTCTGGGGGAGGCGTG GCCCAGCCTGGGAGGTCCCTGAGACTCTCCTGTG CAGCCGTCTGATTCACCTTCAGTGACTATGGCAT GCACTGGGTCCGCCAGGCTCCAGGCAAGGGCT GGAGTGGGTGGCAGTTATATGGTATGATGGAAGT AATAAGTACTATGCAGACTCCGTGAAGGGCCGA CTCACCATCTCCAGAGACAATTCCAAGAACACGC TGTATCTGCAAATGAACAGCCTGAGAGCCGAGG ACACGGCTGTGTATTACTGTGCGAGAGAGAGGTA TAGCAGTGGCTGGTACGACTACGGTATGGACGTC TGGGGCCAAGGGACCACGGTCACCGTCTCCTCA |
| | | | SEQ ID NO: 26217 | SEQ ID NO: 30223 |
| | | AA | DIQMTQSPSSLSASVGDRVTITCRASRGIRNDLG WYQQKPGKAPKRLIYAASSLQSGVPSRFSGSGS GTEFTLTISSLQPEDFATYYCLQHYSYPRTFGQG TKVEIK | QVQLVESGGGVAQPGRSLRLSCAASGFTFSDYGM HWVRQAPGKGLEWVAVIWYDGSNKYYADSVKGR LTISRDNSKNTLYLQMNSLRAEDTAVYYCARERYS SGWYDYGMDVWGQGTTVTVSS |
| | | | SEQ ID NO: 26218 | SEQ ID NO: 30224 |
| iPS:435395 | 21-225_149D11 | NA | GACATCCAGATGACCCAGTCTCCAGCTTCCGT GTCTGCATCTGTAGGAGACAGAGTCACCATCA CTTGTCGGGCGAGTCAGAATATTAGCAACTGG TTAACCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTCACTCTCTCCAT CAGCAGCCTGCAGCCTGAAGATTTTGCAACTT ACTATTGTCAACAGAGCTGACAGTTTCCCATTC ACTTTCGGCCCTGGGACCAAAGTGGATGTCAA A | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTCAGTGCCAT GAGCTGGGTCCGCCAGGCTCCAGGGAAGGGCT GGAGTGGGTCTCAGTTATTAGTGGTGTGGGTGGT AACACATTCTACCGAGACTCCGTGAAGGGCCGCT TCACCATCTCCAGAGACAATTCCAAGAACACGCT CTATCTGCAAATGAACAGCCTGAGAGCCGAGGA CACGGCCGTATATTACTGTGCGAAAAGGATTAT GATTACGTTTGGGGGAGTCCTTACTTTGACTACT GGGGCCAGGGAACCCTGGTCACCGTCTCCTCA |
| | | | SEQ ID NO: 26219 | SEQ ID NO: 30225 |

FIGURE 50
(Continued)

| | | | |
|---|---|---|---|
| | | AA | DIQMTQSPASVSASVGDRVTITCRASQNISNWLT WYQQKPGKAPKLLIYAASSLQSGVPSRFSGSGS GTDFTLSISSLQPEDFATYYCQQTDSFPFTFGPGT KVDVK<br>SEQ ID NO: 26220 | EVQLLESGGGLVQPGGSLRLSCAASGFTFSSYAMS WVRQAPGKGLEWVSAISGRGNTFYADSVKGRFTI SRDNSKNTLYRQMNSLRAEDTAVYYCAKKDYDY VWGSPYFDYWGQGTLVTVSS<br>SEQ ID NO: 30226 |
| iPS:435397 | 21-225_149F12 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT CAGCGTCTGGATTCACCTTCAGTGACTGGCAT TTAGGCTGGTATCAGCAGAAACCAGGAAAG GCACTGGGTCCGCCAGGCTCCAGGCAAGGGCT CCCCTAAGCGCCTGATCTATGCTGCATCCAAT GGAGTGGGTGGCAGTTATATGGTATGAAGAAAA TTGCAAAGTGGGGTCCCATCCAAGGTTCAGCGG TAATAAATACTATGCAGACTCCGTGAAGGCCG CAGTGGATCTGGGACAGAATTCACTCTCACAA ATTCACCATCTCCAGAGACAATTCCAAGAACACG TCAGCAGCCTGCAGCCTGAAGATTTTGCAATT CTGTTTCTGCAAATGAACAGCCTGAGAGCCGAGG TATTACTGTCTACAGCATAATAGTTACCCGCTC ACACGGCTGTGTATTACTGTGCGAGAGAAATAGG ACTTTCGGCGGAGGGACCAAGGTGGAGATCA GTTCAGTGAGGACTACTGGGGCCAGGGAACCCT AA GGTCACCGTCTCCTCA<br>SEQ ID NO: 26221 | SEQ ID NO: 30227 |
| | | AA | DIQMTQSPSSLSASVGDRVTITCRASQGIRNDLG WYQQKPGKAPKRLIYAASNLQSGVPSRFSGSGS GTEFTLTISSLQPEDFAIYYCLQHNSYPLTFGGGT KVEIK<br>SEQ ID NO: 26222 | QVQLVESGGGVVQPGRSLRLSCAASGFTFSDYGM HWVRQAPGKGLEWVAVIWYEENNKYADSVKGR FTISRDNSKNTLFLQMNSLRAEDTAVYYCAREIGFS EDYWGQGTLVTVSS<br>SEQ ID NO: 30228 |

FIGURE 50
(Continued)

| | | | | |
|---|---|---|---|---|
| iPS:435399 | 21-225_150D2 | NA | GACATCGTGATGACCCAGTCTCCAGACTCCCT GGCTGTGTCTCTGGGCGAGAGGGCCACCATCA AGTGCAAGTCCAGCCAGAGTGTTTATACAGA TCCAACAGTAAGAAATACTTAACTTGGTACCA GCAGAAACCAGGACAGCCTCCTAAGCTGTTCA TTTATTGGGCATCTACCCGGAAATCCGGGGTC CCTGACCGATTCAGTGGCAGCGGGTCTGGGAC AGATTTCACTCTCACCATCAGCAACCTGCAGG CTGAAGATGTGGCAGTTTATTTCTGTCAGCAA TATTTTAGTACTCCGTACAATTTTGGCCAGGG GACCAAGAGGGAGAGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAGTGG TAACACAGGCTATGCACAGAAGTTCAGGGCAG AGTCACCATGACCAGGAACACCTCCATAAGCAC AGCCTACATGGAGCTGAGCAGCCTGAGATCTGA GGACACGGCCGTGTATTACTGTGCTTATAGCAGT GGCTGGTACTACTTTGACTACTGGGGCCAGGGAA CCCTGGTCACCGTCTCCTCA |
| | | | SEQ ID NO: 26223 | SEQ ID NO: 30229 |
| | | AA | DIVMTQSPDSLAVSLGERATIKCKSSQSVLYRSN SKKYLTWYQQKPGQPPKLFIYWASTRKSGVPDR FSGSGSGTDFTLTISNLQAEDVAVYFCQQYFSTP YNFGQGTKREIK | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YYFDYWGQGTLVTVSS |
| | | | SEQ ID NO: 26224 | SEQ ID NO: 30230 |
| iPS:435401 | 21-225_150E2 | NA | GACATCCAGATGACCCAGTCTCCATCCTCCCT GTCTGCATCTGTGGGAGACAGAGTCACCATCT CTTGCCGGGCAAGTCAGGGCATTGGAAATGAT TTAGGCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGAATTCACTCTCACTAT CAGCAGCCTGCAGCCTGAAGATTTTGCAACTT ATTACTGTCTACAACATTATAGTTTCCCGTACA GTTTTGGCCAGGGGACCAAGCTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGTCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGAGTA TAGCAGCAGCTGGTACGGGTACGGTATGGACGT CTGGGGCCAAGGGACCACGGTCACCGTCTCCTCA |
| | | | SEQ ID NO: 26225 | SEQ ID NO: 30231 |

FIGURE 50
(Continued)

| | | | | |
|---|---|---|---|---|
| | | | AA | DIQMTQSPSSLSASVGDRVTISCRASQGIGNDLG WYQQKPGKAPTRLIYAASSLQSGVPSRFSGSGSG TEFTLTISSLQPADFATYYCLQHYSFPYSFGQGT KLEIK | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVYYCAREEYSS SWYGYGMDVWGQGTTVTVSS |
| | | | | SEQ ID NO: 26226 | SEQ ID NO: 30232 |
| iPS:435403 | 21-225_150C5 | | NA | GACATCCAGATGACCCAGTCTCCAGGTTCCGT GTCTGCATCTGTAGGAGACAGAGTCACCATAA CTTGTCGGGCGAGTCAGGGTATTAACAACTGG TTAGCCTGGTATCAGCAGAAACCAGGGAAAG CCCCTAAGCTCCTGATCTATGCTGCATCCAGTT TGCAAGGTGGGTCCCATCAAGGTTCAGCGGC AGTGGATCTGGGACAGATTTCACTCTCTCCAT CAGCAGCCTGCAGCCTGAAGATTTTGCAACTT ACTATTGTCAACAGACTGACAGTTCCCATTC ACTTTCGGCCCTGGGACCAAAGTGGATATCAA A | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AACACATTCTACGGAGACTCCGTGAAGGGCCGCT TCACCATCTCCAGAGACAATTCCAAGAACACGCT GTATCTGCAAATGAACAGCCTGAGAGCCGAGGA CACGGCCGTATATTACTGTGCGAAAAAGGATTAT GATTACGTTTGGGGGAGTCCTTACTTTGACTACT GGGGCCAGGGAACCCTGGTCACCGTCTCCTCA |
| | | | | SEQ ID NO: 26227 | SEQ ID NO: 30233 |
| | | | AA | DIQMTQSPGSVSASVGDRVTITCRASQGINNWL AWYQQKPGKAPKLLIYAASSLQGGVPSRFSGSG SGTDFTLSISSLQPEDFATYYCQQTDSFPFTFGPG TKVDIK | EVQLLESGGGLVQPGGSLRLSCAASGFTFSSYAMS WVRQAPGKGLEWVSAISGSGGNTFYADSVKGRFTI SRDNSKNTLYLQMNSLRAEDTAVYYCAKKDYDYV WGSPYFDYWGQGTLVTVSS |
| | | | | SEQ ID NO: 26228 | SEQ ID NO: 30234 |

FIGURE 50
(Continued)

| | | | |
|---|---|---|---|
| iPS:435405 | 21-225_150B7 | NA | GACATCGTGATGACCCAGTCTCCAGACTCCCT GGCTGTGTCTCTGGGCGAGAGGGCCACCATCA ACTGCAAGTCCAGCCAGAATGTTTTATACAGC TCCCACACAATAACAACTACTTAGCTTGGTACCA GCAGAAACCAGGGCAGCCTCCTAAACTACTCA TTTACTGGGCATCTACCCGGAAATCCGGGGTC CCTGACCGATTCAGTGGCAGCGGGTCTGGGAC AGATTTCACTCTCACCATCACCAGCCTGCAGG CTGAAGATGTGGCAGTTTATTACTGTCAGCAA TATTATAGTACTCCATTCACTTTCGGCCCTGGG ACCAAAGTGGATATCAAA | CAGGTGCAGCTGGTGCAGTCTGGGGCTGAGGTA AAGAAGCCTGGGGCCTCAGTGACGGTTCCTGCA AGGCTTCTGGATTCCCCTTCACCAATTATGATAT CAACTGGGTGCGACAGGCCACTGGACAAGGCT TGAGTGGATGGGATGGATGCACCTAACAGTGGT AACACAGGCTATGCACAGAAGTTCCAGGGCAGA GTCACCATGACCAGGAACACCTCCATAAGCACA GCCTACTTGGAGCTGAGCAGCCTGAGATCTGAGG ACACGGCCGTGTATTACTGTGCGAGTAGCAGTGG CTGGTACTTTTTGACTACTGGGGCCAGGGAACC CTGGTCACCGTCTCCTCA |
| | | | SEQ ID NO: 26229 | SEQ ID NO: 30235 |
| | | AA | DIVMTQSPDSLAVSLGERATINCKSSQNVLYSSH NNNYLAWYQQKPGQPPKLLIYWASTRKSGVPD RFSGSGSGTDFTLTITSLQAEDVAVYYCQQYYST PFTFGPGTKVDIK | QVQLVQSGAEVKKPGASVTVSCKASGFPFTNYDIN WVRQATGQGLEWMGWMHPNSGNTGYAQKFQGR VTMTRNTSISTAYLELSSLRSEDTAVYYCASSSGWY FFDYWGQGTLVTVSS |
| | | | SEQ ID NO: 26230 | SEQ ID NO: 30236 |
| iPS:435407 | 21-225_150E7 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAAT TTGCAAAGTGGGGTCCCATTAAGGTTCAGCGG CAGTGGATCTGGGACAGATTCACTCTCACAA TCAGCAGCCTGCAGCCTGAAGATTTTGCAGCT TATTACTGTCTACAGCATAATAGTTACCCGCTC ACTTTCGGCGGAGGGACCAAGGTGGAGATCA AA | CAGGTGCAGCTGGTGCAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGAAGAAAA TAATAAATACTATGCAGACTCCGTGAAGGGCCG ATTCACCATCTCCAGAGACAATTCCAAGAACACG CTGTTTCTGCAAATGAACAGCCTGAGAGCCGAGG ACACGGCTGTGTATTACTGTGCGAGAGAAATAGG GTTCAGTGAGGACTACTGGGGCCAGGGAACCCT GGTCACCGTCTCCTCA |
| | | | SEQ ID NO: 26231 | SEQ ID NO: 30237 |

FIGURE 50
(Continued)

| | | | |
|---|---|---|---|
| iPS:435409 | | AA | DIQMTQSPSSLSASVGDRVTITCRASQGIRNDLG WYQQKPGKAPKRLIYAASNLQSGVPLRFSGSGS GTDFTLTISSLQPEDFAAYYCLQHNSYPLTFGGG TKVEIK SEQ ID NO: 26232 | QVQLVESGGGVVQPGRSLRLSCAASGFTFSDYGM HWVRQAPGKGLEWVAVIWYEENNKYYADSVKGR FTISRDNSKNTLFLQMNSLRAEDTAVYYCAREIGFS EDYWGQGTLVTVSS SEQ ID NO: 30238 |
| | | NA | GACATCCAGATGACCCAGTCTCCATCCTCACT GTCTGCATCTGTAGGAGACAGAGTCACCATCA CTTGTCGGGCGAGTCAGGGCATTAGCAATGAT TTAGCCTGGTTTCAGCAGAAACCAGGGAAAGC CCCTAAGTCCCTGATCTATGCTGCATCCAGTTT GCAAAATGGGGTCCCATCAAGGTTCAGCGGCA GTGGATCTGGGACAGATTTCACTCTCACCATC AGCAGCCTGCAGCCTGAAGATTTTGCAACTTA TTACTGCCAACAGTATAATAATTACCCGCTCA CTTTCGGCGGAGGGACCAAGGTGGAGATCAA A SEQ ID NO: 26233 | GAGGTGCAGCTGGTGGAGTCTGGGGGAGGCTTG GTGCAGCCTGGGGGGTCCCTGAGACTCTCCTGTG CAGCCTCGGGATTCACTTTCAGTGACTACGGCAT GACTTGGGTCCGCCAGGCTCCAGGGAAGGGGCT GGACTGGGTTTCATACATTAGTAGGAGTAGTAGT ACCATATACTACGCAGACTCTGTGAAGGGCCGAT TCTCCATCTCCAGAGACAATGCCAAGAACTCACT GTATCTGCAAATGAACAGCCTGAGAGACGAGGA CACGGCTCTGTATTACTGTGCGAGATCGGCATTT AGCCCTTTTGATTACTGGGGCCAGGGAACCCTGG TCACCGTCTCCTCA SEQ ID NO: 30239 |
| 21-225_150G8 | | AA | DIQMTQSPSSLSASVGDRVTITCRASQGISHYLA WFQQKPGKAPKSLIYVASSLQNGVPSRFSGSGSG TDFTLTISSLQPEDFATYYCQQYNNYPLTFGGGT KVEIK SEQ ID NO: 26234 | EVQLVESGGGLVQPGGSLRLSCAASGFTFSTYSMT WVRQAPGKGLDWVSYISRSSSTIYADSVKGRFSIS RDNAKNSLYLQMNSLRDEDTALYYCARSAFSPFD YWGQGTLVTVSS SEQ ID NO: 30240 |

FIGURE 50
(Continued)

| | | | | |
|---|---|---|---|---|
| iPS:435413 | 21-225_150B11 | NA | GATATTGTGATGACCCAGACTCCACTCTCTCTGTCCGTCACCCCTGGACAGCCGGCCTCCATCTCCTGCAAGTCTAGTGACAGCTCCGTCATGGTGATGGAAAGACTATTTGTATTGGTACCTGCAGAGGCCAGGCCAGCCTCCACAGCTCCTGATCTATGAAGTTTCCAACCGGTTCTCTGGAGTGCCAGATAGGTTCAGTGGCAGCGGGTCAGGGACAGATTTCACATTGAAAATCAGCGGGTGGAGGCTGAGGATGTTGGGGTTTATTACTGCATGCAAAGTATACAGCTTCCGTGGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAATTATATGGTATGAGGAAGTAATAAATACTATGCAGACTCCGTGAAGGGCCGATTCACCATCTCCAGAGACAATTCCAAGAACACGCTGTATCTGCAAATGAACAGCCTGAGAGCCGAAGACACGGCTGTGTATTACTGTGCGAGAGATCGTTACGATTTTGGAGTGGTCACTTTGACTACTGGGGCCAGGGAACCCTGGTCACCGTCTCCTCA |
| | | | SEQ ID NO: 26235 | SEQ ID NO: 30241 |
| | | AA | DIVMTQTPLSLSVTPGQPASISCKSSQSLVHGDGKTYLYWYLQRPGQPPQLLIYEVSNRFSGVPDRFSGSGSGTDFTLKISRVEAEDVGVYYCMQSIQLPWTFGQGTKVEIK | QVQLVESGGGVVQPGRSLRLSCAASGFTFSSYGMHWVRQAPGKGLEWVAIIWYDGSNKYYADSVKGRFTISRDNSKNTLYLQMNSLRAEDTAVYYCARDRYDFWSGHFDYWGQGTLVTVSS |
| | | | SEQ ID NO: 26236 | SEQ ID NO: 30242 |
| iPS:435415 | 21-225_150C11 | NA | GACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAACTCCTGATCTATACTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTATTTACACTTTCGGCGGAGGGACCAAGGTGGAGATCAAA | GAGGTGCAGCTGTTGGAGTCTGGGGGAGGCTTGGTACAGCCTGGGGGGTCCCTGAGACTCTCCTGTGCAGCCTCTGGATTCACCTTTAGCAGCTATGCCATGAACTGGGTCCGCCAGGCTCCAGGGAAGGGGCTGGAGTGGGTCTCAGCTATTAGTGGTAGTGGTGGTAACACATTCTACGCAGACTCCGTGAAGGGCCGGTTCACCATCTCCAGAGACAATTCCAAGAACACGCTGAATCTGCAAATGAGCAGCCTGAGAGCCGAGGACACGGCCGTATATTACTGCGCGAAACGGGTGACGGACTACGGTGGTAACGACTGGTTCGACCCCTGGGGCCAGGGAACCCTGGTCACCGTCTCCTCA |
| | | | SEQ ID NO: 26237 | SEQ ID NO: 30243 |

FIGURE 50
(Continued)

| | | | |
|---|---|---|---|
| | | AA | DIQMTQSPSSLSASVGDRVTITCRASQSISSYLNW YQQKPGKAPKLLIYTASSLQSGVPSRFSGSGSGT DFTLTISSLQPEDFATYYCQQSYSIYTFGGGSKVE IK | EVQLLESGGGLVQPGGSLRLSCAASGFTFSSYAMN WVRQAPGKGLEWVSAISGSGGNTFYADSVKGRFTI SRDNSKNTLNLQMSSLRAEDTAVYYCAKRVTDYG GNDWFDPWGQGTLVTVSS |
| | | | SEQ ID NO: 26238 | SEQ ID NO: 30244 |
| iPS:435417 | 21-225_150D11 | NA | GATATTGTGATGACTCCAGACTCCACTCTCTCT GTCCGTCACTCTGGACAGCCGGCCTCCATCT CCTGCAAGTCTAGTCAGAGCCTCCTGCATAGT GAGGGAAAGACCTATTTGTATTGGTACCTGCA GAAGCCAGGCCAGTCCTCCACAGCTCCTGATCT ATGAAGTTTCCTACCGGGTTCTCTGGAGTGCCA GATAGGTTCAGTGGCAGCGGGTCAGGGACAG ATTTCACACTGAAAATCAGCCGGGTGGAGGCT GAGGATGTTGGGGTTTATTACTGCATGCAAGG TATACAGCTTCCGCTCACTTTCGGCGGAGGGA CCAAGGTGGAGATCAAA | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATTCTATGATGAAGT AATAAACACTATGCAGACTCCGTGAAGGGCCGA TTCACCATCTCCAGAGACAATTCCAAGAACACGC TGTATCTGCAAATGAACAGCCTGAGAGCCGAGG ACTCGGCTGTGTATTACTGTACGAGGAGGTTTAG CAGCAGCTGGTCGGGGGTATGGACGTCTGGGG CCAAGGGACCACGGTCACCGTCTCCTCA |
| | | | SEQ ID NO: 26239 | SEQ ID NO: 30245 |
| | | AA | DIVMTQTPLSLSVTPGQPASISCKSSQSLLHSEGK TYLYWYLQKPGQPPQLLIYEVSYRFSGVPDRFSG SGSGTDFTLKISRVEAEDVGVYYCMQGIQLPLTF GGGTKVEIK | QVQLVESGGGVVQPGRSLRLSCAASGFTFSSYGMH WVRQAPGKGLEWVAVIFYDGSNKHYADSVKGRFT ISRDNSKNTLYLQMNSLRAEDSAVYYCTRRFSSSW SGGMDVWGQGTTVTVSS |
| | | | SEQ ID NO: 26240 | SEQ ID NO: 30246 |

FIGURE 50
(Continued)

| | | | |
|---|---|---|---|
| iPS:435419 | 21-225_150C12 | NA | GACATCCAGATGACCCAGTCTCCATCCTCCCT GTCTGCATCTGTAGGAGACAGAGTCACCATCA CTTGCCGGGCAAGTCAGAGCATTAGCGACTAT TTAAATTGGTATCAGCAGAAACCAGGGAAAG CCCCTAAGGTCCTGATCTATACTACATCCAGTT TGCAAAGTGGGGTCCCATCAAGGTTCAGTGGC AGTGGATCTGGGACAGATTTCACTCTCACCAT CAGCAGTCTGCAGCCTGAAGATTTTGCAACTT ACTACTGTCAACAGAGTTTCAGTACCCCCACT TTCGGCGGAGGGACCAAGGTGGAGATCAAA SEQ ID NO: 26241 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCGGT TCACCATCTCCAGAGACAATTCCAAGAACACACT ATATCTGCAAATGAACAGCCTGAGAGCCGAGGA CACGGCCGTATATTACTGTGCGAAACGGGTGACG GACTACGGTGGTAACGACTGGTTCGACCCCTGGG GCCAGGGAACCCTGGTCACCGTCTCCTCA SEQ ID NO: 30247 |
| | | AA | DIQMTQSPSSLSASVGDRVTITCRASQSISDYLN WYQQKPGKAPKVLIYTTSSLQSGVPSRFSGSGSG TDFTLTISSLQPEDFATYYCQQSFSTPTFGGGTKV EIK SEQ ID NO: 26242 | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKRVTDYG GNDWFDPWGQGTLVTVSS SEQ ID NO: 30248 |
| iPS:435421 | 21-225_151F1 | NA | GAAATGGTGATGACGCAGTCTCCAGCCACCCT GTCTGTGTCTCCAGGGGAAAGAGTCACCCTCT CCTGCAGGGCCAGTCAGAGTATTAACATCAAT ATAGCCTGGTACCAGCAGAAACCTGGCCAGGC GAACTGGGTCCGCCAGGCTCCAGGGAAGGGGCT TCCCAGGCTCCTCATCTATGGTGCATCCACCA GGGCCACTGGTATCCCAGCCAGGTTCAGTGGC AGTGGGTCTGGGACAGTCACTCTCACCAT CAGCAGCCTGCAGTCTGAAGATTTTGCAGTT ATTACTGTCAGCAGTATAATGACTGGCCTCCG TGGACGTTCGGCCAAGGGACCAAGGTGGAAA TCAAA SEQ ID NO: 26243 | GAGGTGCAGCTGTGGTGGAGTCTGGGGGAGGCCTG GTCAAGCCTGGGGGGTCCCTGAGACTCTCCTGTG CAGCCTCTGGATACACCTTCAGGAGCTTTAGCAT GAACTGGGTCCGCCAGGCTCCAGGGAAGGGGCT GGAGTGGGTCTCATCCATTAGTAGTAGTAGTTAT TACATATACTACGCAGACTCAGTGAAGGGCCGAT TCACCATCTCCAGAGACAACGCCAAGAACTCACT GTATCTGCAAATGAACAGCCTGAGAGCCGAAGA CACGGCTGTGTATTACTGTGCGAGAGATACACCA CTGGTTTACTGGGGCCAGGGAACCCTGGTCACCG TCTCCTCA SEQ ID NO: 30249 |

FIGURE 50
(Continued)

| | | | |
|---|---|---|---|
| iPS:435423 | 21-225_151G5 | AA | EMVMTQSPATLSVSPGERVTLSCRASQSINININA WYQQKPGQAPRLLIYGASTRATGIPARFSGSGSG TEFTLTISSLQSEDFAVYYCQQYNDWPPWTFGQ GTKVEIK<br>SEQ ID NO: 26244 | EVQLVESGGGLVKPGGSLRLSCAASGYTFRSFSMN WVRQAPGKGLEWVSSISSSSYIYYADSVKGRFTIS RDNAKNSLYLQMNSLRAEDTAVYYCARDTPLVY WGQGTLVTVSS<br>SEQ ID NO: 30250 |
| | | NA | GATATTGTGATGACCCAGACTCCACTCTCTCT GTCCGTCACCCCTGGACAGCCGGCCTCCATCT CCTGCAAGTCTAGTCAGCGCCTCCTGCATGGT GATGGAAAGACCTATTTGTATTGGTACCTGCA GAAGCCAGGCCAGCCTCCACAGCTCCTGCTCT ATGAAGTTTCCAACCGGTTCTCTGGAGTGCCA GATAGGTTCAGTGGCAGCGGGTCAGGGACAG ATTTCACACACTGAAAATCAGCCGGGTGGAGCT GAGGATGTTGGGGTTTATTACTGCATGCAAAG TATACAGGTTCCGTGGACGTTCGGCCAAGGGA CCAAGGTGGAAATCAAA<br>SEQ ID NO: 26245 | CAGGTGCAGCTGATGGAGTCTGGGGGAGGCGTG GTCCAGCCTGGGAGGTCCCTGAGACTCTCCTGTG CAGCGTCTGGATTCATCTTCAGTAGCTATGCAT GCACTGGGTCCGCCAGGCTCCAGGCAAGGGGCT GGAGTGGGTGGCAATTATATGTATGATGGAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGATCGATA CGATTTTTGGAGTGGTCACTTGACTACTGGGGC CAGGGAACCCTGGTCACCGTCTCCTCA<br>SEQ ID NO: 30251 |
| | | AA | DIVMTQTPLSLSVTPGQPASISCKSSQRLLHGDG KTYLYWYLQKPGQPPQLLLYEVSNRFSGVPDRF SGSGSGTDFTLKISRVEAEDVGVYYCMQSIQVP WTFGQGTKVEIK<br>SEQ ID NO: 26246 | QVQLMESGGGVVQPGRSLRLSCAASGFIFSSYGMH WVRQAPGKGLEWVAIIWYDGSNKYYADSVKGRFT ISRDNSKNTLYLQMNSLRAEDTAVYYCARDRYDF WSGHFDYWGQGTLVTVSS<br>SEQ ID NO: 30252 |

FIGURE 50
(Continued)

| | | | |
|---|---|---|---|
| iPS:435425 | 21-225_151B12 | NA | GACATACAGATGACCCAGTCTCCATCCTCCT GTCTGCGTCTGTAGGAGACAGAGTCACCATCA CTTGCCGGGCAAGTCAGAGACAGATTAGCAACTTT TTAAATTGGTATCAGCAGAAACCAGGGAAAG CCCCTAAGGTCCTGATCTATCGTGCATCCAGTT TGGAAAGTGGGGTCCCATCAAGGTTCAGTGGC AGTGAATCTGGGACAGATTTCACTCTCACCAT CAGCAGTCTGCAACCTGAAGATTTTGCAACTT ACTACTGTCAACAGAGTTACAGTACCCCCACT TTCGGCGGAGGGACCAGGGTGGAGATCAAA<br><br>SEQ ID NO: 26247 | GAGGTGCAGCTGTTGGAGTCTGGGGGAGGCTTG GTACAGCCTGGGGGGTCCCTGAGACTCTCCTGTG CAGCCCTCTGGATTCACCTTTAGCAGCTATGCCAT GAACTGGGTCCGCCACGTCCAGGGAAGGGCT GGAGTGGGTCTCAGTTATTAGTGGTAGTGGTAAA AACACATTCTACGCAGACTCCGTGAAGGGCCGGT TCACCATCTCCAGAGACAACAATTCCAAGAACACGCT GTATCTGCAAATGAACAGCCTGAGAGCCGAGGA CACGGCCGTATATTACTGTGCGAAAACGGGTGACG GACTACGGTGTAACGACTGGTTCGACCCTGGG GCCAGGGAACCCTGGTCACCGTCTCCTCA<br><br>SEQ ID NO: 30253 |
| | | AA | DIQMTQSPSSLSASVGDRVTITCRASQSISNFLNW YQQKPGKAPKVLIYTASSLESGVPSRFSGSESGT DFTLTISSLQPEDFATYYCQQSYSTPTFGGGTRV EIK<br><br>SEQ ID NO: 26248 | EVQLLESGGGLVQPGGSLRLSCAASGFTFSSYAMN WVRHAPGKGLEWVSAISGSGKNTFYADSVKGRFTI SRDNSKNTLYLQMNSLRAEDTAVYYCAKRVTDYG GNDWFDPWGQGTLVTVSS<br><br>SEQ ID NO: 30254 |
| iPS:435427 | 21-225_151C9 | NA | GACATCCAGATGACCCAGTCTCCATCCTCCACT GTCTGCTCTGTAGGAGACAGAGTCACCATCA CTTGTCGGGCGAGTCAGGGCATTAGCAAGTAT TTAGCCTGGTTTCAGCAGAAACCAGGGAAAGC CCCTAAGTCTCTGATCTATGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATATAAACATTACCGATCA TTACTGCCATCAGTATAAACATTACCCGATCA CCTTCGGCCAAGGGACACGACTGGAGATTAAA<br><br>SEQ ID NO: 26249 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTAGTGCAT GCACTGGGTCCGCCAGGCTCCAGGCAAGGGCT GGAGTGGGTGGCAGTTATATCATATGAAGT AATAAATACTATGCAGACTCCGTGAAGGGCCGA TTCACCATCTCCAGAGACAATTCCAAGAACAGC TGTATCTGCAAATGAACAGCCTGAGAGCCGAGG ACACGGCTGTGTATTACTGTGCGAGAAGATGACTGGTTC ACTATGGTTCGGGGAGCTAGAAAGATGACTGGTTC GACCCCTGGGGCCAGGGAACCCTGGTCACCGTCT CCTCA<br><br>SEQ ID NO: 30255 |

FIGURE 50
(Continued)

| | | | | |
|---|---|---|---|---|
| iPS:435429 | 21-225_151A10 | AA | DIQMTQSPSSLSASVGDRVTITCRASQGISKYLA WFQQKPGKAPKSLIYDASRLQSGVPSKFSGSGSG TDFTLTISSLQPEDFASYYCHQYKHYPITFGQGT RLEIK<br>SEQ ID NO: 26250 | QVQLVESGGGVVQPGRSLRLSCAASGFTFSSYGMH WVRQAPGKGLEWVAVISYDGSNKYYADSVKGRFT ISRDNSKNTLYLQMNSLRAEDTAVYYCARGVLLW FGELEDDWFDPWGQGTLVTVSS<br>SEQ ID NO: 30256 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GATGGAAAGACCTATTTGTATTGGTACCTACA GAAGCCAGGCCAGCCTCCACAGCTCCTGATCT ATGAAGTTTCCCACCGGTTCTCTGGAGTGCCA GATAGGTTCAGTGGCAGCGGGTCAGGGACAG ATTTCACACTGAAAATCAGCCGGGTGGAGGCT GAGGATGTTGGGGTTTATTACTGCATGCAAAG TATACAGATTCCGTGGACGTTCGGCCAAGGGA CCAAGGTGGAAATCAAA<br>SEQ ID NO: 26251 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTTGGCAATTATATGTATGATGGAAGT AATAAATACTATGCAGACTCCGTGAAGGGCCGA TTCACCATCTCCAGAGACAACAATTCCAAGAACACGC TGTATCTACAAATGAACAGCCTGAGAGCCGAGG ACACGGCTGTGTATTACTGTGCGAGAGATCATTA CGATTTTTGGAGTGGTCACTTGACTACTGGGGC CAGGGAACCCTGGTCACCGTCTCCTCA<br>SEQ ID NO: 30257 |
| | | AA | DIVMTQTPLSLSVTPGQPASISCKSSQSLLHGDG KTYLYWYLQKPGQPPQLLIYEVSHRFSGVPDRFS GSGSGTDFTLKISRVEAEDVGVYYCMQSIQIPWT FGQGTKVEIK<br>SEQ ID NO: 26252 | QVQLVESGGGVVQPGRSLRLSCAASGFTFSNYGM HWVRQAPGKGLEWLAIIWYDGSNKYYADSVKGRF TISRDNSKNTLYLQMNSLRAEDTAVYYCARDHYDF WSGHFDYWGQGTLVTVSS<br>SEQ ID NO: 30258 |

FIGURE 50
(Continued)

| | | | |
|---|---|---|---|
| iPS:435431 | 21-225_152D2 | NA | GACATCCAGATGACCCTGTCTCCATCTCCCT<br>GTCTGCATCTGTAGGAGACAGAGTCACCATCA<br>CTTGCCGGGCAAGTCAGAGACATTAGCGACTAT<br>TTAAATTGGTATCAGCTGAAACCAGGGAAAGC<br>CCCTAAGGTCTGATCTATACTACATCCAGTTT<br>GCAAAGTGGGGTCCCATCAAGGTTCAGTGGCA<br>GTGGATCTGGGACAGATTTCACTCTCACCATC<br>AGCAGTCTGCAACCTGAAGATTTTGCAACTTA<br>CTTCTGTCAACAGAGTTACAGTACCCCACTTT<br>CGGCGGAGGGACCAAGGTGGAGATCAAA | GAGGTGCAGCTGTTGGAGTCTGGGGGAGGCTTG<br>GTACAGCCTGGGGGGTCCTGAGACTCTCCTGTG<br>CAGCCTCTGGATTCACCTTTAGCAGCTATGCCAT<br>GAGCTGGGTCCGCCAGGCTCCAGGGAAGGGCT<br>GGAGTGGGTCTCAGTTATTAGTGGTCGTGGTGGT<br>AACACATTCTACGCAGACTCCGTGAAGGGCCGGT<br>TCACCATCTCCAGAGACAATTCCAAGAAAACACT<br>ATATCTGCAAATGAACAGCCTGAGAGCCGAGGA<br>CACGGCCGTATATTACTGTGCGAAACGGGTGACG<br>GACTACGGTGTAACGACTGGTTCGACCCCTGGG<br>GCCAGGGAACCCTGGTCACCGTCTCCTCA |
| | | | SEQ ID NO: 26253 | SEQ ID NO: 30259 |
| | | AA | DIQMTLSPSSLSASVGDRVTITCRASQSISDYLN<br>WYQLKPGKAPKVLIYTSSLQSGVPSRFSGSGSG<br>TDFTLTISSLQPEDFATYFCQQSYSTPFGGGTKV<br>EIK | EVQLLESGGGLVQPGGSLRLSCAASGFTFSSYAMS<br>WVRQAPGKGLEWVSAISGRGGNTFYADSVKGRFTI<br>SRDNSKKTLYLQMNSLRAEDTAVYYCAKRVTDYG<br>GNDWFDPWGQGTLVTVSS |
| | | | SEQ ID NO: 26254 | SEQ ID NO: 30260 |
| iPS:435433 | 21-225_152E3 | NA | GACATCGTGATGACCCAGTCTCCAGACTCCT<br>GGCTGTGTCTCTGGGCGAGAGGGCCACCATCA<br>ACTGCAAGTCCAGCCAGAGTGTTTTACACAGC<br>TCCAACAATTACAACTACTTAGTTTGGTACCA<br>GCAGAAACCAGGACAGTCTCCTAAGCGGCTCA<br>TTTACTGGGCATCTACCCGGGAATCCGGGGTC<br>CCTGACCGATTCAGTGGCAGCGGGTCTGGGAC<br>AGATTTCTCTCACCATCAGCAGCCTGCAGG<br>CTGAAGATGTGGCAGTTTATTACTGTCAGCAA<br>TATTACAGTACTCCATTCACTTTCGGCCCTGGG<br>ACCAAAGTGGATATCAAA | CAGGTGCAGCTGGTGCAGTCTGGGGCTGAGGTG<br>AAGAAGCCTGGGGCCTCAGTGAAGGTCTCCTGC<br>AAGGCTTCTGGATACACCTTCACCAATTATGATA<br>TCAACTGGGTGCGACAGGCCACTGGACAAGGC<br>TTGAGTGGATGGGATGGATGCACCTAACAGTGG<br>TAACACAGGCTATGCACAGAAGTTCCAGGGCAG<br>AGTCACCATGACCAGGAACACCTCCATAAGCAC<br>AGCCTACATGGAGCTGAGCAGCCTGAGATCTGA<br>GGACACGGCCGTGTATTACTGTGCGAGTAGCAGT<br>GGCTGGTACTTTTTGACTACTGGGGCCAGGGAA<br>CCCTGGTCACCGTCTCCTCA |
| | | | SEQ ID NO: 26255 | SEQ ID NO: 30261 |

FIGURE 50
(Continued)

| | | | |
|---|---|---|---|
| iPS:435435 | 21-225_152H3 | AA | DIVMTQSPDSLAVSLGERATINCKSSQSVLHSSN NYNYLVWYQQKPGQSPKRLIYWASTRESGVPD RFSGSGSGTDFSLTISSLQAEDVAVYYCQQYYST PFTFGPGTKVDIK<br>SEQ ID NO: 26256 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCASSSGW YFFDYWGQGTLVTVSS<br>SEQ ID NO: 30262 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTGCACAGC TCCAACAATTACAACTACTTAACTTGGTACCA GCAGAAACCAGGACAGCCTCCTAAACTGCTCA TTTACTGGGCATCTCACCCGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGTGCAGTTTGGCCAGGG GACCAAGCTGGAGATCAAA<br>SEQ ID NO: 26257 | CAGGTGCAGCTGGTGCAGTCTGGGGCTGAGGTG AAGAAGCCTGGGGCCTCAGTGAAGGTCTCCTGC AAGGCTTCTGGATACACCTTCCCAATTATGATA TCAACTGGGTGCGACAGGCCACTGGACAAGCC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCATATAGCAGT GGCTGGTACTGGTTTGACTACTGGGGCCAGGAA CCCTGGTCACCGTCCTCA<br>SEQ ID NO: 30263 |
| | | AA | DIVMTQSPDSLAVSLGEKATINCKSSQSVLHSSN NYNYLTWYQQKPGQPPKLLIYWASTRKSGVPD RFSGSGSGTDFTLTISSLQAEDVAVYYCQQYYST PCSFGQGTKLEIK<br>SEQ ID NO: 26258 | QVQLVQSGAEVKKPGASVKVSCKASGYTFPNYDIN WVRQATGQGLEWMGWMHPNSGNTGYAQKFQGR VTMTRNTSISTAYMELSSLRSEDTAVYYCAYSSGW YWFDYWGQGTLVTVSS<br>SEQ ID NO: 30264 |

FIGURE 50
(Continued)

| | | | | |
|---|---|---|---|---|
| iPS:435437 | 21-225_152F4 | NA | GACATCGTGATGACCCAGTCTCCAGACTCCCT GGCTGTGTCTCTGGGCGAGAGGGCCACCATCA ACTGCAAGTCCAGCCAGAGTGTTTATACAGC TCCAACAATTACAACTACTTAGCTTGGTACCA GCAGAAACCAGGGCAGCCTCCTAAACTGCTCA TTTACTGGGCATCTACCCGGAAATCGGGGTC CCTGACCGATTCAGTGGCAGCGGGTCTGGGAC AGATTTCACTCTCACCGTCAGCAGCTGCAGG CTGAAGATGTGGCAGTTTATTACTGTCAGCAA TATTTAATACTCCTCCCACTTTCGGCCCCTGGG ACCAAAGTGGATATCAAA<br><br>SEQ ID NO: 26259 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCAGGGCAG AGTCACCATGACCAGGAACACCTCCATAAGCAC AGCCTACATGGAGCTGAGCAGCCTGAGATCTGA CGACACGGCCGTGTATTACTGTGCGTATAGCAGT GGCTGGTACTGGTTCGACCCCTGGGGCCAGGGA ACCCTGGTCACCGTCTCCTCA<br><br>SEQ ID NO: 30265 |
| | | AA | DIVMTQSPDSLAVSLGERATINCKSSQSVLYSSN NYNYLAWYQQKPGQPPKLLIYWASTRKSGVPD RFSGSGSGTDFTLTVSSLQAEDVAVYYCQQYFN TPPTFGPGTKVDIK<br><br>SEQ ID NO: 26260 | QVQLVQSGAEVKKPGASVKVSCKASGYTFTNYDIN WVRQATGQGLEWMGWMHPNSGNTGYAQKFQGR VTMTRNTSISTAYMELSSLRSDDTAVYYCAYSSGW YWFDPWGQGTLVTVSS<br><br>SEQ ID NO: 30266 |
| iPS:435439 | 21-225_152G4 | NA | GACATCCAGATGACCCAGTCTCCATCCTCCCT GTCTGCATCTGTAGGAGACAGAGTCACCATCA CTTGCCGGGCAAGTCAGAGCATTAGCGACTAT TTAAATTGGTATCAGCAAAAACCAGGGAAAG CCCCTAAGGTCCTGATCTATGCTGCATCCAGTT TGCAAAGTGGGGTCCCATCAAGGTTCAGTGGC AGTGGATCTGGGACAGATTTCACTCTCACCAT CAGCAGTCTGCAACAGAGTTACAGTACCCCACT ACTTCTGTCAACAGAGTTACAGTACCCCCACT TTCGGCGGAGGGACCAAGGTGGAGATCAAA<br><br>SEQ ID NO: 26261 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTGTCGTGGTGGT AACACATTCTACCGAGACTCCGTGAAGGGCCGGT TCACCATCTCCAGAGACAATTCCAAGAACACACT ATATCTGCAAATGAACAGCCTGAGAGCCGAGGA CACGGCCGTATATTACTGTGCGAAACGGGTGACG GACTACGGTGGTAACGACTGGTTCGACCCCTGGG GCCAGGGAACCCTGGTCACCGTCTCCTCA<br><br>SEQ ID NO: 30267 |

FIGURE 50
(Continued)

| | | | |
|---|---|---|---|
| iPS:435441 | 21-225_152F6 | AA | DIQMTQSPSSLSASVGDRVTITCRASQSISDYLN WYQQKPGKAPKVLIYTSSLQSGVPSRFSGSGSG TDFTLTISSLQPEDFATYFCQQSYSTPTFGGGTKV EIK<br>SEQ ID NO: 26262 | EVQLLESGGGLVQPGGSLRLSCAASGFTFSSYAMS WVRQAPGKGLEWVSAISGRGNTFYADSVKGRFTI SRDNSKNTLYLQMNSLRAEDTAVYYCAKRVTDYG GNDWFDPWGQGTLVTVSS<br>SEQ ID NO: 30268 |
| | | NA | GATATTGTGATGACCCAGACTCCACTCTCTCT GTCCGTCACCCCTGGACAGCCGGCCTCCATCT CCTGCAAGTCTAGTCAGAGCCTCCGGCATGGT GATGGAAAGACCTATTTGACTTGGTACCTACA GAGGCCAGGCCAGCCTCCACAGGTCCTGATCC ATGAAATTTCCAAGCGGTTCACTGGAGTGCCA GATAGGTTCAGTGGCAGCGGGTCAGGGACAG ATTTCACACTGAACATCAGCCGGGTGGAGGCT GAGGATGTTGGCTTTTATTACTGCATGCAAAG TATACAGGTTCCGTGGACGTTCGGCCAAGGGA CCAAGGTGGAAATCAAA<br>SEQ ID NO: 26263 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGCCAT GCACTGGGTCCGCCAGGCTCCAGGCAAGGGCT GGAGTGGGTGGCAATTATATGTGATGGAAGT TATAAATACTATGCAGACTCCGTGAAGGGCCGAT TCACCATCTCCAGAGACAATTCCAAGAATACGCT GTATCTGCAAATGAACAGCCTGAGAGCCGAGGA CACGGCTGTGTATTACTGTGCGAGAGAGGGTAC GATTTTTGGAGTGGTTACCTTGGCTACTGGGGCC AGGGAACCCTGGTCACCGTCTCCCTCA<br>SEQ ID NO: 30269 |
| | | AA | DIVMTQTPLSLSVTPGQPASISCKSSQSLRHGDG KTYLTWYLQRPGQPPQVLIHEISKRFTGVPDRFS GSGSGTDFTLNISRVEAEDVGFYYCMQSIQVPW TFGQGTKVEIK<br>SEQ ID NO: 26264 | QVQLVESGGGVVQPGRSLRLSCAASGFTFSSYGMH WVRQAPGKGLEWVAIIWYDGSYKYYADSVKGRFT ISRDNSKNTLYLQMNSLRAEDTAVYYCAREGYDF WSGYLGYWGQGTLVTVSS<br>SEQ ID NO: 30270 |

FIGURE 50
(Continued)

| | | | | |
|---|---|---|---|---|
| iPS:435443 | 21-225_152E7 | NA | GAAATTGTGTTGACGCAGTCTCCAGGCACCCT GTCTTTGTTTCCAGGGGAAAGAGCCACCCTCT CCTGCAGGGCCAGTCAGAGTGTTATCAGCAGC TACTTAGCCTGGTACCAGCAGAAACCTGGCCA GGCTCCCAGGCTCCTCATCTTTGGTGTATCTAG TAGGGCCACTGGCATCCCAGACAGGTTCAGTG GCAGTGGGTCTGGGACAGACTCACTCTCACC ATCAGCAGACTGGAGCCTGAAGATTTTGCAGT GTATTACTGTCAACAATATGGTAGGTCACCAT TCAAATTTCGGCCCTGGGACCAAAGTGGATATC AAA<br>SEQ ID NO: 26265 | CAGGTGCAGCTGCAGGAGTCGGGCCCAGGACTG GTGAAGCCTTCACAGACCCTGTCCCTCAATTGCA CTGTCTCTGGTGGCTCCATCAGCAGCAACAGTGGTTA CTACTGGAGCTGGATCCGCCAGCACCCAGGCAA GGGCCTGGAATGGATTGGGTACAGTTATTACAGT GGGAGCACCTACTACAACCCGTCCCTCAAGAGTC GAATTACCATATCAGTAGACACGTCTAACAACCA GTCTCCCTGAACCTGAGCTCTGTGACTGCCGCG GACACGGCCGTGTATTACTGTGCGAGAGGGGA TATAACTGGAACCATGCTTTTGATATCTGGGGCC AAGGGACAATGGTCACCGTCTCTTCA<br>SEQ ID NO: 30271 |
| | | AA | EIVLTQSPGTLSLFPGERATLSCRASQSVISSYLA WYQQKPGQAPRLLIFGVSSRATGIPDRFSGSGSG TDFTLTISRLEPEDFAVYYCQQYGRSPFNFGPGT KVDIK<br>SEQ ID NO: 26266 | QVQLQESGPGLVKPSQTLSLNCTVSGGSISNSGYY WSWIRQHPGKGLEWIGYSYYSGSTYYNPSLKSRITI SVDTSNNQFSLNLSSVTAADTAVYYCARGGYNWN HAFDIWGQGTMVTVSS<br>SEQ ID NO: 30272 |
| iPS:435445 | 21-225_152F7 | NA | GACATCCAGATGACCCAGTCTCCATCCTCCCT GTCTGCATCTGTTGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGAATTCACTCTCACAA TCAGCAGCCTACAGCCTGAAGATTTTGCAACT TATTACTGTCTACAGCATTATAATTTCCCGTAC AGTTTTGGCCAGGGGACCAAGCTGGAGATCAA A<br>SEQ ID NO: 26267 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATATCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGAGTA TAGCAGCAGCTGGTACGGGTACGGTATGGACGT CTGGGGCCAAGGGACCACGGTCACCGTCTCCTCA<br>SEQ ID NO: 30273 |

FIGURE 50
(Continued)

| | | | |
|---|---|---|---|
| | | AA | DIQMTQSPSSLSASVGDRVTITCRASQGIRNDLG WYQQKPGKAPKRLIYATSSLQSGVPSRFSGSGSG TEFTLTISSLQPEDFATYYCLQHYNFPYSFGQGT KLEIK<br>SEQ ID NO: 26268 | QVQLVESGGGVVQPGRSLRLSCAASGFTFSSYIMH WVRQAPGKGLEWVAVIWYDGSNKYADSVKGRF TISRDNSKNTLYLQMNSLRAEDTAVYYCAREEYSS SWYGYGMDVWGQGTTVTSS<br>SEQ ID NO: 30274 |
| iPS:435447 | 21-225_152H7 | NA | GACATCCAGATGACCCAGTCTCCAGCTTCCGT GTCTGCATCTGTGGGAGACAGAGTCACCATAA CTTGTCGGGCGAGTCAGGATATTAGCAACTGG TTAGCCTGGTATCAGCAGAAACCAGGGAAAG CCCCTAAACTCCTGATCTATGCTGCATCCAGTT TGCAAGGTGGGGTCCCATCAAGGTTCAGCGGC AGTGGATCTGGGACAGATTTCACTCTCTCCAT CAGCAGCCTGCAGCCTGAAGATTTTGCAACTT ACTATTGTCAACAGACTGACAGTTTCCCATTC ACTTTCGGCCCTGGGACCAAAGTGGATATCAA A<br>SEQ ID NO: 26269 | GAGGTGCAGCTGTTGGAGTCTGGGGGAGGCTTG GTACAGCCTGGGGGGTCCCTGAGACTCTCCTGTG CAGCCCTCTGGATTCACCTTTAACAGTTATGCCAT GAACTGGGTCCGCCAGGCTCCAGGGAAGGGGCT GGAGTGGGTCTCAGTATTAGTGGTAGTGGTGGT AACACATTCTACGCAGACTCCGTGAAGGGCCGCT TCACCATCTCCAGAGACAATTCCAAGAACACACT GTATCTGCAAATGAACAGCCTGAGAGCCGAGGA CACGGCCGTATATTACTGTGCGAAAAAGGATAAT GATTACGTTTGGGGAGTCCTTACTTTGACTACT GGGGCCAGGGAACCCTGGTCACCGTCTCCTCA<br>SEQ ID NO: 30275 |
| | | AA | DIQMTQSPASVSASVGDRVTITCRASQDISNWLA WYQQKPGKAPKLLIYAASSLQGGVPSRFSGSGS GTDFTLSISTLQPEDFATYYCQQTDSFPFTFGPGT KVDIK<br>SEQ ID NO: 26270 | EVQLLESGGGLVQPGGSLRLSCAASGFTFNSYAMN WVRQAPGKGLEWVSAISGSGGNTFYADSVKGRFTI SRDNSKNTLYLQMNSLRAEDTAVYYCAKKDNDYV WGSPYFDYWGQGTLVTVSS<br>SEQ ID NO: 30276 |

FIGURE 50
(Continued)

| | | | | |
|---|---|---|---|---|
| iPS:435449 | 21-225_152H9 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCACCGG CAGTGGATCTGGGACAGAATTCACTTTCACAA TCAGCAGCCTGCAGCCTGAAGATTTTGCAACT TATTACTGTCTACAGCATAGTAATTACCCGCTC ACTTTCGGCGGAGGGACCAAGGTGGAGATCA AA | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTA CTACTGGGGCTGGATCCGCCAGCCCCAGGGAA GGGGCTGGAGTGGATTGGGAGTATCTATTATAGT GGGAGCGCCTCCTACAACCCGTCCCTCAAGAGTC GAGTCACCATATCCGTAGACACGTCCAAGAACC AGTTCTCCCTGAAGCTGAGCTCTGTGACCGCGC AGACACGGCTGTGTTTTACTGTGCGAGACTTGAT CTCCAGTGGAGTTTGACTTCTGGGGCCAGGGAA CCCTGGTCACCGTCCTCA |
| | | | SEQ ID NO: 26271 | SEQ ID NO: 30277 |
| | | AA | DIQMTQSPSSLSASVGDRVTITCRASQGIRNDLG WYQQKPGKAPKRLIYAASSLQSGVPSRFTGSGS GTEFTFTISSLQPEDFATYYCLQHSNYPLTFGGGT KVEIK | QLQLQESGPGLVKPSETLSLTCTVSGGSISRSSYYW GWIRQPPGKGLEWIGSIYYSGSASYNPSLKSRVTIS VDTSKNQFSLKLSSVTAADTAVFYCARLDLQWSFD FWGQGTLVTVSS |
| | | | SEQ ID NO: 26272 | SEQ ID NO: 30278 |
| iPS:435451 | 21-225_152D10 | NA | GGCATCGTGATGACCCAGTCTCCAGACTCCCT GGCTGTGTCTCTGGGCGCGAGGGCCACCATCG ACTGCAAGTCCAGCCAGAGTGTTTTATACAGC TCCAACAATAAGAACTACTTAGCTTGGTACCA GCAGAAACCAGGACAGCCTCCTAAGTTGCTCA TTTACTGGGCATCTACCCGGGAATCCGGGGTC CCTGACCGATTCAGTGGCAGCGGATCTGGGAC AGATTTCACTCTCACCATCTACAGCCTGCAGG CTGAAGATGTGGCAGTTTATTACTGTCAGCAA TATTATCGTAGTCCTAGTTTTGGCCAGGGAC CAAGCTGGAGATCAAA | CAGGTGCAGCTGCAGGAGTCGGGCCCAGGACTG GTGAAGCCTTCGGAGACCCTGTCCCTCACCTGCA CTGTCTCTGGTGGCTCCATCAGTAATTACTACTG GAGCTGGATCCGGCAGCCCCGCGGGAAGGGACT GGAGTGGATTGGGCGTATCGATACCAGTGGGATC ACCAACTACAACCCCTCCCTCAAGAGTCGAGTCA CCATGTCAGTGACACGTCCAAGAACCAGTTCTC CCTGAAGCTGACCTCTGTGACCGCCGCAGACACG GCCGTGTATTACTGTGCGAGAGAGGGGGATTG GGAGCTACCTTCTTTGACTACTGGGGCCAGGGAA CCCTGGTCACCGTCTCCTCA |
| | | | SEQ ID NO: 26273 | SEQ ID NO: 30279 |

FIGURE 50
(Continued)

| | | | |
|---|---|---|---|
| | | AA | GIVMTQSPDSLAVSLGARATIDCKSSQSVLYSSN NKNYLAWYQQKPGQPPKLLIYWASTRESGVPD RFSGSGSGTDFTLTIYSLQAEDVAVYYCQQYYR SPSFGQGTKLEIK<br>SEQ ID NO: 26274 | QVQLQESGPGLVKPSETLSLTCTVSGGSISNYYWS WIRQPAGKGLEWIGRIDTSGITNYNPSLKSRVTMSV DTSKNQFSLKLTSVTAADTAVYYCAREGGLGATFF DYWGQGTLVTVSS<br>SEQ ID NO: 30280 |
| iPS:435453 | 21-225_152G10 | NA | GACATCCAGATGACCCAGTCTCCAGCTTCCGT GTCTGCATCTGTAGGAGACAGAGTCACCATAA CTTGTCGGGCGAGTCAGGGTATTAGCAACTGG TTAGCCTGGTATCAGCAGAAACCAGGGAAAG CCCCTAAGCTCCTGATCTCTGCTGCATCCAGTT TGCAAAGTGGGGTCCCATCAAGGTTCAGCGGC AATGAATCTGGGACAGATTTCACTCTCTCCAT CAGCAGCCTGCAGCTGAAGATTTTGCAACTT ACTATTGTCAACAGACTGACAGTTTCCCATTC ACTTTCGGCCCTGGGACCAAAGTGGATGTCAA A<br>SEQ ID NO: 26275 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCCGCT TCACCATCTCCAGAGACAATTCCAAGAACACGCT CTATCTGCAAATGAACAGCCTGAGAGCCGAGGA CACGGCCGTATATTACTGTGCGAAAAGGATTAT GATTACGTTTGGGGGAGTCCTTACTTTGACTACT GGGGCCAGGGAACCCTGGTCACCGTCTCCTCA<br>SEQ ID NO: 30281 |
| | | AA | DIQMTQSPASVSASVGDRVTITCRASQGISNWLA WYQQKPGKAPKLLISAASSLQSGVPSRFSGNESG TDFTLSISSLQPEDFATYYCQQTDSFPFTFGPGTK VDVK<br>SEQ ID NO: 26276 | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKKDYDYV WGSPYFDYWGQGTLVTVSS<br>SEQ ID NO: 30282 |

FIGURE 50
(Continued)

| | | | | |
|---|---|---|---|---|
| iPS:435455 | 21-225_152B11 | NA | GACATCCAGATGACCCAGTCTCCATCCTCCCT GTCTGCATCTGTAGGAGACAGAGTCACCATCA CTTGCCGGGCAAGTCAGAGACATTAGCGACTAT TTAAATTGGTATCAGCAGAAACCAGGGAAAG CCCCTAAGGTCCTGATCTATACTACATCCAGTT TGCAAAGTGGGGGTCCCATCAAGGTTCAGTGGC AGTGGATCTGGGACAGATTTCACTCTCACCAT CAGCAGTCTGCAACCTGAAGATTTTGCAACTT ACTTCTGTCAACAGAGTTACAGTACCCCCACT TTCGGCGGAGGGACCAAGGTGGAGATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGCT GGAGTGGGTCTCAGTTATTAGTGGTCGTGGTGGT AACACATTCTACGCAGACTCCGTGAAGGGCCGGT TCACCATCTCCAGAGACAATTCCAAGAACACACT ATATCTGCAAATGAACAGCCTGAGAGCCGAGGA CACGGCCGTATATTACTGTGCGAAACGGGTGACG GACTACGGTGTAACGACTGGTTCGACCCCTGGG GCCAGGGAACCCTGGTCACCGTCTCCTCA |
| | | | SEQ ID NO: 26277 | SEQ ID NO: 30283 |
| | | AA | DIQMTQSPSSLSASVGDRVTITCRASQSISDYLN WYQQKPGKAPKVLIYTSSLQSGVPSRFSGSGSG TDFTLTISSLQPEDFATYFCQQSYSTPFGGGTKV EIK | EVQLLESGGGLVQPGGSLRLSCAASGFTFSSYAMN WVRQAPGKGLEWVSAISGRGGNTFYADSVKGRFTI SRDNSKNTLYLQMNSLRAEDTAVYYCAKRVTDYG GNDWFDPWGQGTLVTVSS |
| | | | SEQ ID NO: 26278 | SEQ ID NO: 30284 |
| iPS:435457 | 21-225_152C11 | NA | GATATTGTGATGACCCAGTCTCCACTCTCT GTCCGTCACCCTGGACAGCCGGCCTCCATCT CCTGCAAGTCTAGTCAGAGCCTCCTGCATGGT GATGGAAAGAACCTATTTATATTGGTACCTGCA GAAGCCAGGCCAGCCTCCACAGATCCTGATCT ATGAAGTTTCCAACCGGTTCTCTGGAGTGCCA GATAGGTTCAGTGGCAGCGGGTCAGGGACAG ATTTCACACTGAAACATCAGCGGGTGGAGGCT GAGGATGTTGGGGTTTATTACTGCATGCAAAG TATACAGATTCCGTGGACGTTCGGCCAAGGGA CCAAGGTGGACATCAAA | CAGGTACAACTGGTGGAGTCTGGGGGAGGCGTG GTCCAGCCTGGGAGGTCCCTGAGACTCTCCTGTG CAGCGTCTGGATTCACCTTCCGTAACTATGGCAT GCACTGGGTCCGCCAGGCTCCAGGCAAGGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGAGGCTTA ACACGGCTGTGTATTACTGTGCGAGAGAGGCTTA CGATTTTTGGAGTGGTTATTTTGACTACTGGGGC CAGGGAATTCTGGTCACCGTCTCCTCA |
| | | | SEQ ID NO: 26279 | SEQ ID NO: 30285 |

FIGURE 50
(Continued)

| | | | |
|---|---|---|---|
| iPS:435459 | 21-225_152E12 | AA | DIVMTQAPLSLSVTPGQPASISCKSSQSLLHGDGKTYLYWYLQKPGQPPQILIYEVSNRFSGVPDRFSGSGSGTDFTLNISRVEAEDFGFYCMQSIQIPWTFGQGTKVDIK<br>SEQ ID NO: 26280 |
| | | | QVQLVESGGGVVQPGRSLRLSCAASGFTFRNYGMHWVRQAPGKGLEWVAHWYDGSNKYYADSVKGRFTISRDNSKNTLYLQMNSLRAEDTAVYYCAREAYDFWSGYFDYWGQGILVTVSS<br>SEQ ID NO: 30286 |
| | | NA | GCCGTCGTGATGACCCAGTCTCCAGACTCCCTGGCTGTGTCTCTGGGCGAGAGGGCCACCATCAACTGCAGTCCAGCCAGAGTATTTACACAGCTCCAATAATTACAACTACTTAGTTGGTACCAGCAGAAACCAGGACAGCCTCCTAAATTGCTCATTTACTGGGCATCTACCCGGGAATCCGGGTCCCTGACCGATTCAGTGGCAGCGGGTCTGGGACAGATTTCACTCTCACCATCAGCAGCCTGCAGGCTGAAGATGTGGCAGTTTATTACTGTCAACAATATTATAGTGGTCCGTGCAGTTTTGGCCAGGGGACCAAGCTGGAGATCAAA<br>SEQ ID NO: 26281 |
| | | | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGAACCCTAACAGTGGTAACACAGGCTATGCCACAGAAGTTCCAGGGCAGAGTCACCATGACCAGGAACACCTCCATAAGCAGAGCCTACATGGAGCTGAGCAGCCTGAGATCTGAGGACACGGCCGTGTATTACTGTGCTTATAGCAGTGGCTGGTACTTTGACTACTGGGGCCAGGGAACCCTGGTCACCGTCCTCTCA<br>SEQ ID NO: 30287 |
| | | AA | AVVMTQSPDSLAVSLGERATINCTSSQSILHSSNNYNYLAWYQQKPGQPPKLLIYWASTRESGVPDRFSGSGSGTDFTLTISSLQAEDVAVYYCQQYYSGPCSFGQGTKLEIK<br>SEQ ID NO: 26282 |
| | | | QVQLVQSGAEVKKPGASVKVSCKASGYTFTNYDINWVRQATGQGLEWMGWMNPNSGNTGYAQKFQGRVTMTRNTSISTAYMELSSLRSEDTAVYYCAYSSGWYYFDYWGQGTLVTVSS<br>SEQ ID NO: 30288 |

FIGURE 50
(Continued)

| | | | |
|---|---|---|---|
| iPS:435461 | 21-225_153A1 | NA | GACATCCAGATGACCCAGTCTCCATCCTCACT GTCTGCATCTGTAGGAGACAGAGTCACCATCA CTTGTCGGGCGAGTCAGGTCATTAGCAATTAT TTAGCCTGGTTTCAGCAGAAACCAGGGAAAGC CCCTAAGTCCCCTGATCTCTGCTGCATCCAGTTT GCGAAGTGGGGTCCCATCAAACTTCAGCGGCA GTGGATCTGGGACAGATTTCACTCTCACCATC AGCAGCCTGCAGCCTGAAGATTTTGCAACTTA TTACTGCCAACAGTATCATAGTTACCCATTCA CTTTCGGCCCTGGGACCAAAGTGGATTTCAAA<br>SEQ ID NO: 26283 | GAGGTGCAGCTGTTGGAGTCTGGGGGAGGCCTG GTACAGCCTGGGGGGTCCCTGAGACTCTCCTGTG CAGCCCTGGATTCAGCTTTAGCAGCTATGTCAT GAGTTGGGTCCGCCAGGCCCCAGGGAAGGGGCT GGAGTGGGTCTCAGCTATTAGTGGAAGTGGTGAT AGAACATACTACGCAGACTCCGTGAAGGGCCGG TTCACCATCTCCAGAGACAATTCCAAGAACACGC TGTACCTGCAAATGAACAGCCTGAGAGCCGAGG ACACGGCCGTATATTACTGTGCGCGTACGGCGAC TAAGGACTACTGGGGCCAGGGAACCCTGGTCAC CGTCTCCTCA<br>SEQ ID NO: 30289 |
| | | AA | DIQMTQSPSSLSASVGDRVTITCRASQVISNYLA WFQQKPGKAPKSLISAASSLRSGVPSNFSGSGSG TDFTLTISSLQPEDFATYYCQQYHSYPFTFGPGT KVDFK<br>SEQ ID NO: 26284 | EVQLLESGGGLVQPGGSLRLSCAASGFSFSSYVMS WVRQGPGKGLEWVSAISGSGDRTYYADSVKGRFTI SRDNSKNTLYLQMNSLRAEDTAVYYCARTATKDY WGQGTLVTVSS<br>SEQ ID NO: 30290 |
| iPS:435463 | 21-225_153D2 | NA | GATATTGTGATGACCCAGACTCCACTCTCTCT GTCCGTCACCCCTGGACAGCCGGCCTCCATCT CCTGCAAGTCTAGTCAGAGCCTCCGGCATGGT GATGGAAAGAACCTATTTGACTTGGTACCTACA GAGGCCAGGCCAGCCTCCACAGGTCCTGATCC ATGAAGTTTCCAAGCGGTTCACTGGAGTGCCA GATAGGTTCAGTGGCAGCGGGTCAGGGACAG ATTTCACACTGAAACATCAGCGGGTGGAGGCT GAGGATGTGGGTTTATTACTGCATGCAAAG TATACAGGTTCCGTGGACGTTCGGCCAAGGGA CCAAGGTGGAAATCAAA<br>SEQ ID NO: 26285 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAATTATATGGTATGATGGAAGT TATAAATACTATGCAGACTCCGTGAAGGGCCGAT TCACCATCTCCAGAGACAATTCCAAGAACACGGT GTATCTGCAAATGAACAGCCTGAGAGCCGAGGA CACGGCTGTATATTACTGTGCGAGAGGGGGTAC GATTTTTGGAGTGGTTACCTTGCTACTGGGGCC AGGGAACCCTGGTCACCGTCTCCTCA<br>SEQ ID NO: 30291 |

FIGURE 50
(Continued)

| | | | |
|---|---|---|---|
| iPS:435465 | 21-225_153A6 | AA | DIVMTQTPLSLSVTPGQPASISCKSSQSLRHGDG KTYLTWYLQRPGQPPQVLIHEVSKRFTGVPDRFS GSGSGTDFTLNISRVEAEDVGFYYCMQSIQVPW TFGQGTKVEIK<br>SEQ ID NO: 26286 | QVQLVESGGGVVQPGRSLRLSCAASGFTFSSYGMH WVRQAPGKGLEWVAIIWYDGSYKYYADSVKGRFT ISRDNSKNTVYLQMNSLRAEDTAVYYCAREGYDF WSGYLGYWGQGTLVTVSS<br>SEQ ID NO: 30292 |
| | | NA | GAAATTGTGTTGACGCAGTCTCCAGGCACCCT GTCTTTGTTTCCAGGGGAAAGAGCCCCCTCT CCTGCAGGGCCAGTCAGAGTGTTATCAGCAGC TACTTAGCCTGGTACCAGCAGAAACCTGGCCA GGCTCCCAGGCTCCTCATCTTTGGTGTATCTAG TAGGGCCACTGGCATCCCAGACAGGTTCAGTG GCAGTGGGTCTGGGACAGACTTCACTCTCACC ATCAGCAGACTGGAGCCTGAAGATTTTGCAGT GTATTACTGTCAACAATATGGTAGGTCACCAT TCAATTTTCGGCCCTGGGACCAAAGTGGATATC AAA<br>SEQ ID NO: 26287 | CAGGTGCAGCTGCAGGAGTCGGGCCAGGACTG GTGAAGCCTTCACAGACCCTGTCCCTCAATTGCA CTGTCTCTGGTGGCTCCATCAGCAGCAGTGGTTA CTACTGGAGCTGGATCCGCCAGCACCCAGGCAA GGGCCTGGAATGGATTGGGTACAGCTATTACAGT GGGAGCACTTACTACAACCCGTCCCTCAAGAGTC GAATTACCATATCAGTAGACAGTCTAACAACCA GTTCTCCCTGAACCTGAGCTCTGTGACTGCCGCG GACACGGCCGTGTATTACTGTGCGAGAGGGGA TATAACTGGAACCATGGTCTTTGATATCTGGGCC AAGGGACAATGGTCACCGTCTCTCA<br>SEQ ID NO: 30293 |
| | | AA | EIVLTQSPGTLSLFPGERAPLSCRASQSVISSYLA WYQQKPGQAPRLLIFGVSSRATGIPDRFSGSGSG TDFTLTISRLEPEDFAVYYCQQYGRSPFNFGPGT KVDIK<br>SEQ ID NO: 26288 | QVQLQESGPGLVKPSQTLSLNCTVSGGSISNSGYY WSWIRQHPGKGLEWIGYSYYSGSTYYNPSLKSRITI SVDTSNNQFSLNLSSVTAADTAVYYCARGGYNWN HAFDIWGQGTMVTVSS<br>SEQ ID NO: 30294 |

FIGURE 50
(Continued)

| | | | | |
|---|---|---|---|---|
| iPS:435467 | 21-225_153B9 | NA | GGCATCGTGATGACCCAGACTCCAGATTCCCT GGCTGTGTCTCTGGGAGAGGGCCACCATCA ACTGCAAGTCCAGCAGAGTGTTTATACAGC TCCAACAATAAGAACTACTTAGCTTGGTACCA GCAGAAACCAGGACAGCCTCATAAGTTGCTCA TTTACTGGGCATCTACCCGGGAATTTGGGGTC CCTGACCGATTCAGTGGCAGCGGGTGTGGAC AGATTTCACTCTCACCATCTACAGCGTGCAGG CTGAAGATGTGGCAGTTTATTACTGTCAGCAA TATAATCGTAGTCTTAGTTTTTGGCCAGGGGAC CAAGCTGGAGATCAAA<br><br>SEQ ID NO: 26289 | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTACTG GAGCTGGATCCGGCAGCCCCCGGGAAGGACT GGAGTGGATTGGGCGTATCGATACCAGTGGGATC ACCAACTACAACCCCTCCCTCAAGAGTCGAGTCA CCATGTCAGTGCACACCTCCAAGAACCAGTTCTC CCTGAAGCTGAGCTCTGTGACCGCCGCGGACACG GCCGTGTATTACTGTGCGAGAGAGGGGGAGTG GGAGCTACTACTTTGACTACTGGGGCCAGGGA ACCCTGGTCACCGTCTCCTCA<br><br>SEQ ID NO: 30295 |
| | | AA | GIVMTQPPDSLAVSLGERATINCKSSQSVLYSSN NKNYLAWYQQKPGQPHKLLIYWASTREFGVPD RFSGSGCGTDFTLTISVTAADTAVYYCQQYNR SLSFGQGTKLEIK<br><br>SEQ ID NO: 26290 | QVQLQESGPGLVKPSETLSLTCTVSGGSISSYYWSW IRQPAGKGLEWIGRIDTSGITNYNPSLKSRVTMSVD TSKNQFSLKLTSVTAADTAVYYCAREGGVGATYF DYWGQGTLVTVSS<br><br>SEQ ID NO: 30296 |
| iPS:435469 | 21-225_153G9 | NA | GATATTGTGATGACCCAGACTCCACTCTCTCTG TCCGTCACCCCTGGACAGCCGGCCTCCATCTC CTGCAAGTCTAGTCAGAGCCTCCTGCATAGTG CTGCAAGTCTAGTGACCTATTGTATTGGTACCTGCAG ATGGAAAGACCAGGCCTATTGTATTGGTACCTGCAG AAGCCAGGCCAGCCTCCACAGTTCCTGATCTA TGAAGTTTCCAACCGGTTCTCTGGAGTGCCAG ATAGGTTCAGTGCAGCGGGTCAGGGACAGA TTTCACACTGAAAATCAGCCGGGTGGAGGCTG ACGATGTTGGGGTTTATTACTGCATGCAAAAT ATAAAGTATCCGCTCACTTTCGGCGGAGGGAC CAAGGTGGAGATCAAA<br><br>SEQ ID NO: 26291 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCACTTATATTCTATGATGGAAGT AATAAATACTATGCAGACTCCGTGAAGGGCCGA TTCACCATCTCCAGAGACAATTCCAAGAACACGC TGTATCTGCAAATAAACAGCCTGAGAGCCGAGG ACACGGCTGTGTATTTCTGTGCGCGACGCTATAG CCGCAGCTGGGCCGGGGTATGACGTCTGGGG CCAAGGGACCCGGGTCACCGTCCTCA<br><br>SEQ ID NO: 30297 |

FIGURE 50
(Continued)

| | | | |
|---|---|---|---|
| iPS:435471 | 21-225_153F11 | AA | DIVMTQTPFSLSVTPGQPASISCKSSQSLLHSDGK TYLYWYLQKPGQPPQFLIYEVSNRFSGVPDRFSG SGSGTDFTLKISRVEADDVGVYYCMQNIKYPLT FGGGTKVEIK<br>SEQ ID NO: 26292 | QVQLVESGGGVVQPGRSLRLSCAASGFTFSSYGMH WVRQAPGKGLEWVALIFYDGSNKYYADSVKGRFT ISRDNSKNTLYLQINSLRAEDTAVYFCARRYSRSW AGGMDVWGQGTAVTVSS<br>SEQ ID NO: 30298 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATTACAAGTACTTAGCTTGGTACCA GCAGAAACCAGGACAGCCTCCTAACCTGCTCA TTTACTGGGCATCTCACCCGGAAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGTCAGTTTGGCCAGGG GACCAAGCTGGAGATCAAA<br>SEQ ID NO: 26293 | CAGGTGCAGCTGGTGCAGTCTGGGGCTGAGGTG AAGGAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAATACCTCCATAAACAC AGCCTACATGGAGCTGAGCAGCCTGAGATCTGA GGACACGGCCGTGTATTACTGTGCGTATAGCAGT GGCTGGTACTTCTTTGACAACTGGGGCCAGGAA CCCTGGTCACCGTCTCCTCA<br>SEQ ID NO: 30299 |
| | | AA | DIVMTQSPDSLAVSLGERATINCKSSQSVLYSSN NYKYLAWYQQKPGQPPNLLIYWASTRKSGVPD RFSGSGSGTDFTLTISSLQAEDVAVYYCQQYYST PCSFGQGTKLEIK<br>SEQ ID NO: 26294 | QVQLVQSGAEVKEPGASVKVSCKASGYTFTNYDIN WVRQATGQGLEWMGWMHPNSGNTGYAQKFQGR VTMTRNTSINTAYMELSSLRSEDTAVYYCAYSSGW YFFDNWGQGTLVTVSS<br>SEQ ID NO: 30300 |

FIGURE 50
(Continued)

| | | | | |
|---|---|---|---|---|
| iPS:435475 | 21-225_154H6 | NA | GACATCGTGATGACCCAGTCTCCAGACTCCCT GGCTGTGTCTCTGGGCGAGAGGGCCACCATCA ACTGCAAGTCCAGCCAGTGTTTTACACAGT TCCAACAATTACAACTATTTAGCTGGTACCA GCAGAAACCAGGACAGCCTCCTAAGCTGCTCA TTTACTGGACATCTACCCGGAAATCGGGGTC CCTGACCGATTCAGTGGCAGCGGGTCTGGGAC ACATTTCACTCTCTCCATCAGCAGCCTGCAGG CTGAAGATGTGGCAGTTTATTACTGTCAGCAT TATTATAGTACTCCGTGCAGTTTGGCCAGGG GACCAAGCTGGAGATCAAA SEQ ID NO: 26295 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGTATAGCAG TGGCTGTGTACATCTTTGACTACTGGGGCCAGGGA ACCCTGGTCACCGTCTCCTCA SEQ ID NO: 30301 |
| | | AA | DIVMTQSPDSLAVSLGERATINCKSSQSVLHSSN NYNYLAWYQQKPGQPPKLLIYWTSTRKSGVPD RFSGSGSGTHFTLSISSLQAEDVAVYYCQHYYST PCSFGQGTKLEIK SEQ ID NO: 26296 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YIFDYWGQGTLVTVSS SEQ ID NO: 30302 |
| iPS:435479 | 21-225_154E9 | NA | GACATTCAGATGACCCTGTCTCACCTCCGT GTATGCATCTGTCGGAGACAGAGTCACCATCA CTTGTCGGGCGAGTCAGGATATTAGCAACTGG TTAGCCTGGTATCAGCAGAAGACCAGGGAAAG CCCCTAAGGTCCTTATCTATGCTGCATCCAGTT TGCAAAGTGGGGTCCCATCAAGATTCAGCGGC AGTGGATCTGGGACAGATTTCACTCTCACCAT CAGCAGCCTGCAGCCTGAAGATTTTGCAACTT ACTATTGTCAACAGGGTAACAGTTTCCCGCTC ACTTTCGGCGGAGGGACCAAGGTGGACATCA AA SEQ ID NO: 26297 | GAGGTGAAGTTGTTGGAGTCTGGGGGAGGCTTG GTACAGCCGGGGGGGTCCCTGAGACTCTCCTGTG CAGCCTCTGGATTCACCTTTAGCAGCAGTATGCCAT GAGCTGGGTCCGCCAGGCTCCAGGGAAGGGGCT GGAGTGGGTCTCAGTTATTACGGAGTCTATTAGTGGTCGTGGTGGT AACACATTCTACGCAGACTCCGTGAAGGGCCGGT TCACCATCTCCAGAGACAATTCCAAGAACACGCT GTTTCTGCAAATGAACAGCCTGAGAGCCGAGGA CACGGCCGTATATTACTGTGCGAAAGGGATTT CGATTTTTGGAGTGGTTGGGGGGCTTTGACTACT GGGGCCAGGGAACCCTGGTCACCGTCTCCTCA SEQ ID NO: 30303 |

FIGURE 50
(Continued)

| | | | | |
|---|---|---|---|---|
| iPS:435481 | 21-225_154A11 | AA | DIQMTLSPSSVYASVGDRVTITCRASQDISNWLA WYQQRPGKAPKVLIYAASSLQSGVPSRFSGSGS GTDFTLTISSVQPEDFATYYCQQGNSFPLTFGGG TKVDIK<br><br>SEQ ID NO: 26298 | EVKLLESGGGLVQPGGSLRLSCAASGFTFSSYAMS WVRQAPGKGLEWVSAISGRGNTFYADSVKGRFTI SRDNSKNTLFLQMNSLRAEDTAVYYCAKRGFRFLE WLGGFDYWGQGTLVTVSS<br><br>SEQ ID NO: 30304 |
| | | NA | GACATCGTGATGACCCAGTCTCCAGACTCCCT GGCTGTGTCTCTGGGCGAGAGGGCCACCATCA ACTGCAGGTCAAGTCAGAGTGTTTTACACAGC TCCAACAATTATAACTACTTAGCTTGGTACCA GCAGAAACCAGGACAGGCTCCTAAGCTGCTCA TTTACTGGGCATCTAAACGGGATTCCGGGGTC CCTGACCGATTCAGTGGCAGCGGGTCTGGGAC AGATTTCACTCTCACCATCAGCAGCCTGCAGG CTGAGGATGTGGCAGTTTATTACTGTCAGCAA TATTTTAGTTCTCCGGACGTTCGGCCAAGG GACCAAGGTGGAAATCAAG<br><br>SEQ ID NO: 26299 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGAGTAGCA GTGGCTGGTACTACTTCGACTACTGGGGCCAGG GAACCCTGGTCACCGTCTCCTCA<br><br>SEQ ID NO: 30305 |
| | | AA | DIVMTQSPDSLAVSLGERATINCRSSQSVLHSSN NYNYLAWYQQKPGQPPKLLIYWASKRDSGVPD RFSGSGSGTDFTLTISSLQAEDVAVYYCQQYFSS PRTFGQGTKVEIK<br><br>SEQ ID NO: 26300 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YYFDYWGQGTLVTVSS<br><br>SEQ ID NO: 30306 |

FIGURE 50
(Continued)

| | | | | |
|---|---|---|---|---|
| iPS:435483 | 21-225_155A4 | NA | GACATCCAGATGACCCAGTCTCCAGTTCCGT GTCTGCATCTGTAGGAGACAGAGTCACCATAA CTTGTCGGGCGAGTCAGGTATTAGCAACTGG TTAGCCTGGTATCACCAGAAACCAGGGAAAGC CCCTAAGCTCCTGATCTATGCTGCATCCAGTTT GCAAGGTGGGGTCCCATCAAGGTTCAGCGGCA GTGGATCTGGGACAGATTTCACTCTCTCCATC AGCAGCCTGCAGCCTGAAGATTTTGCAACTTA CTATTGTCACCAGACTGACAGTTTCCCATTCAC TTTCGGCCCTGGGACCAAAGTGGATATCAAA SEQ ID NO: 26301 | GAGGTGCAGCTGTTGGAGTCTGGGGGAGGCTTG GTACAGCCTGGGGGGTCCCTGAGACTCTCTGTG CAGCCTCTGATTCACCTTTAACAGCTATGCCAT GAGCTGGGTCCGCCAGGCTCCAGGGAAGGGCT GGAGTGGGTCTCAGTTATTAGTGGTAGTGGTGGT AACACATTCTACGCAGACTCCGTGAAGGGCCGCT TCACCATCTCCAGAGACACAATTCCAAGAACACGCT GTATCTGCAAATGAACAGCCTGAGAGCCGAGGA CACGGCCGTATATTACTGTGCGAAAAGGATTAT GATTACGTTTGGGGGAGTCCTTACTTTGACTACT GGGGCCAGGGAACCCTGGTCACCGTCTCCTCA SEQ ID NO: 30307 |
| | | AA | DIQMTQSPASVSASVGDRVTITCRASQGISNWLA WYHQKPGKAPKLLIYAASSLQGGVPSRFSGSGS GTDFTLSISSLQPEDFATYYCHQTDSFPFTFGPGT KVDIK SEQ ID NO: 26302 | EVQLLESGGGLVQPGGSLRLSCAASGFTFNSYAMS WVRQAPGKGLEWVSAISGSGGNTFYADSVKGRFTI SRDNSKNTLYLQMNSLRAEDTAVYYCAKKDYDYV WGSPYFDYWGQGTLVTVSS SEQ ID NO: 30308 |
| iPS:435485 | 21-225_155B4 | NA | GACATCCAGATGACCCAGTCTCCAGTTCCGT GTCTGCATCTGTAGGAGACAGAGTCACCATAA CTTGTCGGGCGAGTCAGGATATTAGCAACTGG TTAGCCTGGTATCAGCAGAAACCAGGGAAAG CCCCTAAGCTCCTGATCTATGCTGCATCCAGTT TGCAAGGTGGGGTCCCATCAAGGTTCAACGGC AGTGGATCTGGGACAGATTTCACTCTCTCCAT CAGCAGCCTGCAGCCTGAAGATTTTGCAACTT ACTATTGTCACCAGACTGACAGTTTCCCATTC ACTTTCGGCCCTGGGACCAAAGTGGATATCAA A SEQ ID NO: 26303 | GAGGTGCAGCTGTTGGAGTCTGGGGGAGGCTTG GTACAGCCTGGGGGGTCCCTGAGACTCTCCTGTG CAGCCTCTGATTCACCTTTAGCAGCTATGCCAT GAGCTGGGTCCGCCAGGCTCCAGGGAAGGGCT GGAGTGGGTCTCAGTTATTAGTGGTAGTGGTGGT AACACATTCTACGCAGACTCCGTGAAGGGCCGCT TCACCATCTCCAGAGACAATTCCAAGAACACGCT GTATCTGCAAATGAACAGCCTGAGAGCCGAGGA CACGGCCGTATATTACTGTGCGAAAAGGATTAT GATTACGTTTGGGGGAGTCCTTACTTTGACTACT GGGGCCAGGGAACCCTGGTCACCGTCTCCTCA SEQ ID NO: 30309 |

FIGURE 50
(Continued)

| | | | |
|---|---|---|---|
| | | AA | DIQMTQSPASVSASVGDRVTITCRASQDISNWLA WYQQKPGKAPKLLIYAASSLQGGVPSRFNGSGS GTDFTLSISSLQPEDFATYYCHQTDSFPFTFGPGT KVDIK | EVQLLESGGGLVQPGGSLRLSCAASGFTFSSYAMS WVRQAPGKGLEWVSAISGSGGNTFYADSVKGRFTI SRDNSKNTLYLQMNSLRAEDTAVYYCAKKDYDYV WGSPYFDYWGQGTLVTVSS |
| | | | SEQ ID NO: 26304 | SEQ ID NO: 30310 |
| iPS:435487 | 21-225_155C4 | NA | GACATCCAGATGACCCAGTCTCCATCCTCCCT GTCTGCATCTGTAGGAGACAGAGTCACCATCA CTTGCCGGGCAAGTCAGAGCATTAGCAGCTAT TTAAATTGGTATCAGCAGAAACCAGGGAAAG CCCCTAAGGCTCCTGATCTTACTGCATCCAGTT TGCAAAGTGGGGTCCCATCAAGATTCAGTGGC AGTGGATCTGGGACAGATTTCACTCTCACCAT CAGCAGTCTGCAACCTGAAGATTTTGCAACTT ACTACTGTCAACAGAGTACAGTACCCCCACT TTCGGCGGAGGGACCAGGGTGGAGATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGCCCGGT TCACCATCTCCAGAGACAATTCCAAGAACACGCT GTATCTGCAAATGAACAGTCTGAGAGCCGAGGA CACGGCCGTATATTACTGTGCGAAACGGGTGACG GACTACGGTGGTAAGACTGGTTCGACCCCTGGG GCCAGGGGAACCCTGGTCACCGTCTCCTCA |
| | | | SEQ ID NO: 26305 | SEQ ID NO: 30311 |
| | | AA | DIQMTQSPSSLSASVGDRVTITCRASQSISSYLNW YQQKPGKAPKVLIFTASSLQSGVPSRFSGSGSGT DFTLTISSLQPEDFATYYCQQSYSTPTFGGGTRV EIK | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKRVTDYG GNDWFDPWGQGTLVTVSS |
| | | | SEQ ID NO: 26306 | SEQ ID NO: 30312 |

FIGURE 50
(Continued)

| | | | | |
|---|---|---|---|---|
| iPS:435489 | 21-225_155A5 | NA | GATATTGTGATGACCCAGACTCCACTCTCT GTCCGTCACCCCTGGACAGCCGCCTCCATCT CCTGCAAGTCTAGTCAGAGCCTCCTGCATGT GATGGAAAGAACTATTTGTATTGGTACCTGCA GAAGCCAGGCCAGCCTCCACAGTCTCGATTT ATGAAGTTTCCAATCGGTTCTCTGAGTGCCA GATAGGTTCAGTGGCAGCGGTTCAGGGACAG ATTTCACACTGAAAATCAGCGGGTGGAGGCT GAGGATGTTGGATTTTATTACTGTATGCAAAG TATACAGGTTCCGTGCAGACGTTCGGCCAAGGGA CCAAGGTGGAAATCAAA | CAGGTGCAGCTAGTGGAGTCTGGGGGAGACGTG GTCCAGCCTGGGAGGTCCCTGAGCTCTCCTGTG CAGCCTCTGATTCACCTTCAGTAGTAGCTATGCCAT GCACTGGGTCCGCCAGGCTCCAGGCAAGGGCT GGAGTGGGTGGCAATTATATGGTATGATGGAAGT AGTAAATACTATGCAGACTCCGTGAAGGGCCGA TTCACCATCTCCAGAGACAATTCCAAGAACACGC TGTATCTGCACATGAACAGCCTGAGAGCCGAGG ACACGGCAGTGTATTACTGTGCGAGAGATGATA CGATTTTTGAGTGGTCACTTTGACTACTGGGGC CAGGGAACCCTGGTCACCGTCTCCTCA |
| | | | SEQ ID NO: 26307 | SEQ ID NO: 30313 |
| | | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGFYYCMQSIQVPW TFGQGTKVEIK | QVQLVESGGDVVQPGRSLRLSCAASGFTFSSYGMH WVRQAPGKGLEWVAIIWYDGSSKYYADSVKGRFT ISRDNSKNTLYLHMNSLRAEDTAVYYCARDRYDF WSGHFDYWGQGTLVTVSS |
| | | | SEQ ID NO: 26308 | SEQ ID NO: 30314 |
| iPS:435491 | 21-225_155E5 | NA | GACATCGTGATGACCCAGTCTCCAGACTCCCT GGCTGTGTCTCTGGGCGAGAGGGCCACCATCA ACTGCAAGTCCAGCCAGAGTGTTTTATCCAGC TCCAACAATAATAATTATTAGCTTGGTACCA GCAGAAACCAGGACAGCCTCCTAAGCTGCTCA TTTACTGGGCATCTACCCGGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCGTGCAGTTTGGCCAGGG GACCAAGCTGGAGATCAAG | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACAGAGGTTCCAGTGG TAGTACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGTTTAGCAGT GGCTGGTACTATTTGACTACTGGGGCCAGGGAA CCCTGGTCACCGTCTCCTCA |
| | | | SEQ ID NO: 26309 | SEQ ID NO: 30315 |

FIGURE 50
(Continued)

| | | | |
|---|---|---|---|
| iPS:435495 | | AA | DIVMTQSPDSLAVSLGERATINCKSSQSVLSSSN NNNYLAWYQQKPGQPPKLLIYWASTRKSGVPD RFSGSGSGTDFTLTISSLQAEDVAVYYCQQYYST PCSFGQGTKLEIK<br>SEQ ID NO: 26310 | QVQLVQSGAEVKKPGASVKVSCKASGYTFTNYDIN WVRQATGQGLEWMGWMHPNSGSTGYAQRFQGR VTMTRNTSISTAYMELSSLRSEDTAVYYCAFSSGW YYFDYWGQGTLVTVSS<br>SEQ ID NO: 30316 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTACACAGC TCCAATAATTACAACTACTTAGCTTGGTACCA GCAGAAACCAGGACAGCCCCCTAAACTGCTCA TTTACTGGACATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAACAA TATTATAGTACTCCGTGCAGTTTTGGCCAGGG GACCAAGTTGGAGATCAAA<br>SEQ ID NO: 26311 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACAGAAGTTCCAGGGCA GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCTTATAGCAG TGGCTGGTACTACTTTGACTACTGGGGCCAGGGA ACCCTGGTCACCGTCTCCTCA<br>SEQ ID NO: 30317 |
| 21-225_155B6 | | AA | DIVMTQSPDSLAVSLGERATINCKSSQSVLHSSN NYNYLAWYQQKPGQPPKLLIYWTSTRESGVPDR FSGSGSGTDFTLTISSLQAEDVAVYYCQQYYSTP CSFGQGTKLEIK<br>SEQ ID NO: 26312 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YYFDYWGQGTLVTVSS<br>SEQ ID NO: 30318 |

FIGURE 50
(Continued)

| | | | | |
|---|---|---|---|---|
| iPS:435497 | 21-225_155H9 | NA | GAAATAGTGATGACGCAGTCTCCAGCCACCCT GTCTGTGTCTCCAGGGGAAAGAGCCACCCTCT CCTGCAGGGCCAGTCAGTGTTAGTAGTAAC TTAGCCTGGTACCAGCAGAAACCTGGCCAGGC TCCCAGACTCCTCATCTATGGTGCATCCACCA GGGCCACTGGTATCCCAGCCAGGTTCAGTGGC AGTGGGTCTGGGACAGAGTTCACTCTCACCAT CAGCAGCCTGCAGTCTGAAGATTTTGCAGTTT ATTACTGTCAGCAGTATGATGACTGGCCTCCG TGGACGTTCGGCCAAGGGACCAAGGTGGAAA TCAAA SEQ ID NO: 26313 | GAGGTGCAACTATTGGAGTCTGGGGGAGGCTTG GTTCAGCCTGGGGGGTCCCTGAGACTCTCCTGTG CAGCCCTCTGATTCACCTTTAGCAGTCAGTATGCCAT GAACTGGGTCCGCCAGGCTCCAGGGAAGGGCT GGAATGGGTCTCAACTATTAGTGGTAGAGGTCTT GGCACATACTACGCAGACTCCGTGAAGGGCCGG TTCACCATCTCCAGAGACAATTCCAAGAACACGC TGTATCTGCAACTGAACAGCCTGAGAGCCGAGG ACACGGCCGTATATTACTGTGCGAAAGACCATGA CTACGGTGACTACAATATCTACTTTGACTACTGG GGCCAGGGAACCCTGGTCACCGTCTCCTCA SEQ ID NO: 30319 |
| | | AA | EIVMTQSPATLSVSPGERATLSCRASQSVSSNLA WYQQKPGQAPRLLIYGASTRATGIPARFSGSGSG TEFTLTISSLQSEDFAVYYCQQYDDWPPWTFGQ GTKVEIK SEQ ID NO: 26314 | EVQLLESGGGLVQPGGSLRLSCAASGFTFSSYAMN WVRQAPGKGLEWVSTISGRGLGTYYADSVKGRFTI SRDNSKNTLYLQLNSLRAEDTAVYYCAKDHDYGD YNIYFDYWGQGTLVTVSS SEQ ID NO: 30320 |
| iPS:435499 | 21-225_156G1 | NA | GACATCCAGATGACCCAGTCTCCATCCTCCCT GTCTGCATCTGTAGGAGACAGAGTCACCATCA CTTGCCGGGCAAGTCAGAGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAGTTCACTCTCACAA TCAGCAGCCTGCAGCCTGAAGATTTTGCAACT TATTACTGTCTACAGCATAGTAATTACCCGCTC ACTTTCGGCGGAGGGACCAAGGTGGAGATCA AA SEQ ID NO: 26315 | CAGCTGCAGCTGCAGGAGTCGGGCCCAGGACTG GTGAAGCCTTCGGAGACCCTGTCCCTCACCTGCA CTGTCTCTGGTGGCTCCATCAGCAGAAGTAGTTA CTACTGGGGCTGGATCCGCCAGCCCCCAGGGAA GGGAGCGCCTCCTACAACCCGTCCCTCAAGAGTC GAGTCACCATATCCGTAGACACGTCCAAGAACC AGTTCTCCCTGAAGCTGAGCTGTGTGACCGCGC AGACACGGCTGTGTTTACTGTGCGAGACTTGAT CTCCAGTGGAGTTTGACTTCTGGGGCCAGGGAA CCCTGGTCACCGTCTCCTCA SEQ ID NO: 30321 |

FIGURE 50
(Continued)

| | | | |
|---|---|---|---|
| iPS:435501 | 21-225_156H1 | AA | DIQMTQSPSSLSASVGDRVTITCRASQGIRNDLG WYQQKPGKAPKRLIYAASSLQSGVPSRFSGSGS GTEFTFTISSLQPEDFATYYCLQHSNYPLTFGGGT KVEIK<br>SEQ ID NO: 26316 | QLQLQESGPGLVKPSETLSLTCTVSGGSISRSSYYW GWIRQPPGKGLEWIGSIYSGSASYNPSLKSRVTIS VDTSKNQFSLKLSSVTAADTAVFYCARLDLQWSFD FWGQGTLVTSS<br>SEQ ID NO: 30322 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTATACAGC TCCAACAATAACAACTACTTAGCTTGGTACCA GCAGAAACCAGGACAGCCTCCTAAGCTGCTCA TTTACTGGGCATCTACCCGGGAATCCGGGTC CCTGCCCGATTCAGTGGCAGCGGGTCTGGGAC AGATTTCACTCTCACCATCAGCAGCCTGCAGG CTGAAGATGTGGCAGTTTATTACTGTCACCAA TATTATAGTACTCCGTGCAGTTTGGCCAGGG GACCAAGCTGGAGATCAAA<br>SEQ ID NO: 26317 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTACTATTACTGTGCGGGAGCAG TGGCTGGTACTACTTTGACTACTGGGGCCAGGGA ACCCTGTCACCGTCTCCTCA<br>SEQ ID NO: 30323 |
| | | AA | DIVMTQSPDSLAVSLGERATINCKSSQSVLYSSN NNNYLAWYQQKPGQPPKLLIYWASTRESGVPA RFSGSGSGTDFTLTISSLQAEDVAVYYCHQYYST PCSFGQGTKLEIK<br>SEQ ID NO: 26318 | QVQLVQSGAEVKKPGASVKVSCKASGYTFTNYDIN WVRQATGQGLEWMGWVHPNSGNTGYAQKFQGR VTMTRNTSISTAYMELSSLRSEDTAVYYCAGSSGW YYFDYWGQGTLVTVSS<br>SEQ ID NO: 30324 |

FIGURE 50
(Continued)

| | | | |
|---|---|---|---|
| iPS:435503 | 21-225_156E4 | NA | GACATCCAGATGACCCAGTCTCCATCCTCCCT GTCTGCATCTGTAGGAGACAGAGTCACCATCA CTTGCCGGGCAAGTCAGAGCATTAGCAGCTAT TTAAATTGGTATCAGCAGAAACCAGGGAAAG CCCCTAAGGTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTGCCCCCACT TTCGGCGGAGGGACCAAGGTGGAGATCAAA<br><br>SEQ ID NO: 26319 | DIQMTQSPSSLSASVGDRVTITCRASQSISSYLNW YQQKPGKAPKVLIYTASSLQSGVPSRFSGSGSGT DFTLTISSLQPEDFATYYCQQSYSAPTFGGGTKV EIK<br><br>SEQ ID NO: 26320 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTCGTGGTGGT AACACATTCTACGCAGACTCCGTGAAGGGCCGGT TCACCATCTCCAGAGACAATTCCAAGAACACACT ATATCTGCAAATGAACAGCCTGAGAGCCGAGGA CACGGCCGTATATTACTGTGCGAAACGGGTGACG GACTACGGTGGTAACGACTGGTTCGACCCCTGGG GCCAGGGAACCCTGGTCACCGTCTCCTCA<br><br>SEQ ID NO: 30325 | EVQLLESGGGLVQPGGSLRLSCAASGFTFSSYAMS WVRQAPGKGLEWVSAISGRGGNTFYADSVKGRFTI SRDNSKNTLYLQMNSLRAEDTAVYYCAKRVTDYG GNDWFDPWGQGTLVTVSS<br><br>SEQ ID NO: 30326 |
| iPS:435505 | 21-225_157C1 | NA | GACATCCAGATGACCCAGTCTCCATCCTCACT GTCTGCATCTATAGGAGACAGAGTCACCCTCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCTAAGTGGGGTCCCATCAAGGTTCAGCGGCA GTGGATCTGGGACAGATTTCACTCTCACCATC AGCAGCCTGCAGCCTGAAGATTTTGCAACTTA TTACTGCCAACAGTATAATAGTTTTCCATTCAC TTTCGGCGGAGGGACCAAGGTGGAGCTCAAA<br><br>SEQ ID NO: 26321 | | GAGGTGCAGCTGTGGTGGAGTCTGGGGGAGGCCTG GTCAAGCCTGGGGGGTCCCTGAGACTCTCCTGTG CAGCCTCTGGATTCACCTTCAGTAGCTATAGAAT GAACTGGGTCCGCCAGGCTCCAGGGAAGGGGCT GGAGTGGGTCTCATCATGAGTAATAGTAGTAGT TCCATATACTACGCAGAGAACGCCAAGAACTACT GTATCTGCAAATGAACAGCCTGAGAGCCGAGGA CACGGCTGTGTATTACTGTGCGAGACAGGCAGCC CAGGACTACTGGGGCCAGGGAACCCTGGTCACC GTCTCCTCA<br><br>SEQ ID NO: 30327 |

FIGURE 50
(Continued)

| | | | |
|---|---|---|---|
| iPS:435509 | 21-225_157H1 | AA | DIQMTQSPSSLSASIGDRITLTCRASQGISNYLAW FQQRPGKAPKSLIYAASSLLSGVPSKFSGSGSGT DFTLTISSLQPEDFATYYCQQYNSFPFTFGGGTK VELK SEQ ID NO: 26322 | EVQLVESGGGLVKPGGSLRLSCAASGFTFSSYRMN WVRQAPGKGLEWVSSMSNSSSSIYYADSVKGRFTI SRDNAKNSLYLQMNSLRAEDTAVYYCARQAAQD YWGQGTLVTVSS SEQ ID NO: 30328 |
| | | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGTCTGGTTTCAGCAGAGACCAGGGAAAGC CCCTAGGTCCCTGATCTATGCTGCATCCAGTTT GCAAAGTGGGGTCCCATCAAGTTCAGCGGCA GTGGATCTGGGACAGATTTCACTCTCACCATC AGCAGCCTGCAGCCTGAAGATTTTGCAACTTA TTACTGCCAACAATATCATAGTTACCCATTCA CTTTCGGCCCTGGGACCAAAGTGGATATCAAA SEQ ID NO: 26323 | GAGGTGCAGCTGTTGGAGTCTGGGGGAGGGTTG GTACAGCCTGGGGGGTCCCTGAGACTCTCCTGTG CAGCCTCTGGATTCACCTTTAGCAGTTATGCCAT GAGGTGGATCCGCCAGGCTCCAGGGAAGGGCT GCAGTGGGTCTCAGATATTAGTGTAGTGGTGGT ACCACATACTACGCAGACTCCGTGAAGGGCCGG TTCACCATCTCCAGAGACAATGAACAGCCTGAGAG TGTATCTGCAAATGAACAGCCTGAGAGCCGAGG ACACGGCCGTATATTACTGTGCGAAGACCTACCT CTGGGGCCAGGGAACCCTGGTCACCGTCTCCTCA SEQ ID NO: 30329 |
| | | AA | DIQMTQSPSSLSASVGDRVTITCRASQDISNYLV WFQQRPGKAPRSLIYAASSLQSGVPSKFSGSGSG TDFTLTISSLQPEDFATYYCQQYHSYPFTFGPGT KVDIK SEQ ID NO: 26324 | EVQLLESGGGLVQPGGSLRLSCAASGFTFSSYAMR WIRQAPGKGLQWVSDISGSGGTTYADSVKGRFTI SRDNSKNTLYLQMNSLRAEDTAVYYCAKTYLWGQ GTLVTVSS SEQ ID NO: 30330 |

FIGURE 50
(Continued)

| | | | |
|---|---|---|---|
| iPS:435511 | 21-225_157C3 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTCATCTATGCTGCATCCAGTTTGCAAAGTGGGGTCCCATCAAGGTTCAGCGGCAGTGGATCTGGGACAGACTTCACTCTCACAATCAGCAGCCTGCAGCCTGATGACTTTGCAACTTATTACTGTCTACAGCATAATAGTTACCCATTCACTTTCGGCCCTGGGACCAAAGTGGATATCAAA<br/>SEQ ID NO: 26325 | CAGGTGCAGCTGGTGGAGTCTGGGGGAGGCGTGGTCCAGCCTGGGAGGTCCCTGAGACTCTCCTGTGCAGCCTCTGGATTCACCTTCAGTACCTATGGCATGCACTGGGTCCGCCAGGCTCCAGGCAAGGGGCTGGAGTGGGTGGCAGTTATATGGTATGATGTAAATAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGCTGGGTTCCTCTCTGACTATTGGGGCCAGGGAACCCTGGTCACCGTCTCCTCA<br/>SEQ ID NO: 30331 |
| | | AA | DIQMTQSPSSLSASVGDRVTITCRASQGIRNDLGWYQQKPGKAPKRLIYAASSLQSGVPSRFSGSGSGTDFTLTISSLQPDDFATYYCLQHNSYPFTFGPGTKVDIK<br/>SEQ ID NO: 26326 | QVQLVESGGGVVQPGRSLRLSCAASGFTFSTYGMHWVRQAPGKGLEWVAVIWYDVNNKYYADSVKGRFTISRDNSKNTLYLQMNSLRAEDTAVYYCARELGFLSDYWGQGTLVTVSS<br/>SEQ ID NO: 30332 |
| iPS:435513 | 21-225_157F3 | NA | GACATCCAGATGACCCAGTCTCCATCCTCCCTGTCTGCATCTGTAGGAGACAGAGTCACCATCACTTGCCGGGCAAGTCAGAGCATTAGAACATTAGCAGTTTATTAAATTGGTATCAGCTGAAACCAGGGAAAGCCCCTAAACTCCTGATCTATACTGCATCCAGTTTGCAAAGTGGGGTCCCATCAAGGTTCAGTGGCAGTGGATCTGGGACAGACTTCACTCTCACCATCAGCAGTCTGCAACCTGAGGATTTTGCAACTTACTACTGTCAACAGAGTTACAATACCCCACGTGGACGTTCGGCCAAGGGACCAAGGTGAAAATCAAA<br/>SEQ ID NO: 26327 | GAGGTGCAACTGTTGGAGTCTGGGGGAGGCTTGGTACAGCCTGGGGGGTCCCTGAGACTCTCCTGTGCAGCCTCTGAATTCACCTTTAGCACCTATGCCATGAGCTGGGTCCGCCAGGCTCCAGGGAAGGGGCTGGAGTGGGTCTCAGTTATTAGTGGTAGTGGTGGTAGCACATACTACGCAGACTCCGTGAAGGGCCGGTTCACCATCTCCAGAGACAATGAACAGCCTGAGAGCCGAGGACACGGCCGTATATTACTGTGCGAAAGGAGCAGTGGCTGGTACGACGGATGCTCTTGATATCTGGGGCCAAGGGACAATGGTCACCGTCTCTTCA<br/>SEQ ID NO: 30333 |

FIGURE 50
(Continued)

| | | | | |
|---|---|---|---|---|
| iPS:435515 | | AA | DIQMTQSPSSLSASVGDRVTITCRASQNISSYLN WYQLKPGKAPKLLIYTASSLQSGVPSRFSGSGSG TDFTLTISSLQPEDFATYYCQQSYNTPTWTFGQG TKVEIK<br>SEQ ID NO: 26328 | EVQLLESGGGLVQPGGSLRLSCAASEFTFSTYAMS WVRQAPGKGLEWVSVISGSGGSTYYADSVKGRFTI SRDNSKNTLYLQMNSLRAEDTAVYYCAKRSSGWY EDALDIWGQGTMVTVSS<br>SEQ ID NO: 30334 |
| | 21-225_157E4 | NA | GACATCCAGATGACCCAGTCTCCATCCTCACT GTCTGCATCTGTAGGAGACAGAGTCACCTTCA CTTGTCGGGCGAGTCAGGGCATTAGCAATTAT TTAGCCTGGTTTCAGCAGAAACCAGGGAGAGC CCCTAAGTCCCTGATCTATGCTGCATCCAGTTT GCGAAGTGGGGTCCCATCACAGTTCAGCGGCA GTGGATCTGGGACAGATTTCACTCTCACCATC AACAGCCTGCAGCCTGAAGATTTTGCAACTTA TTACTGCCAACAGTATCATAGTTATCCATTCAC TTTCGGCCCTGGGACCAAAGTGGATATCAAA<br>SEQ ID NO: 26329 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGCTATACCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCAAGAGACAACGCCAAGAACTCACT GTATCTGCAAATGAACAGCCTGAAAGCCGAGGA CACGGCTGTGTATTACTGTGCGAGAGTAGCTACC TTTGACTACTGGGGCCAGGGAACCCTGGTCACCG TCTCCTCA<br>SEQ ID NO: 30335 |
| | | AA | DIQMTQSPSSLSASVGDRVTFTCRASQGISNYLA WFQQKPGKAPKSLIYAASSLRSGVPSQFSGSGSG TDFTLTINSLQPEDFATYYCQQYHSYPFTFGPGT KVDIK<br>SEQ ID NO: 26330 | EVQLVESGGGLVKPGGSLRLSCAASGFTFSSYTMN WVRQAPGKGLEWVSSISGSSSYIYYADSVKGRFTIS RDNAKNSLYLQMNSLKAEDTAVYYCARVATFDY WGQGTLVTVSS<br>SEQ ID NO: 30336 |

FIGURE 50
(Continued)

| | | | |
|---|---|---|---|
| iPS:435521 | 21-225_157H4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATCCTGCATCCAGTT TACAAACTGGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGGATAATAGTTACCCATTC ACTTTCGGCCCTGGGACCAAAGTGGATATCAA A | GAGGTGCAGCTGGTGGAGTCTGGGGGAGGCTG GTCAAGCCTGGGGGGTCCCTGAGACTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTAGTAGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATAGAGGG TCCATCTGGGGCCAGGGAACCCTGGTCACCGTCT CCTCA |
| | | | SEQ ID NO: 26331 | SEQ ID NO: 30337 |
| | | AA | DIQMTQSPSSLSASVGDRVTITCRASQGIRNDLG WYQQKPGKAPKRLIYPASSLQTGVPSRFSGSGSG TEFTLTISSLQPEDFATYYCLQDNSYPFTFGPGTK VDIK | EVQLVESGGGLVKPGGSLRLSCAASGFTFSSYSMN WVRQAPGKGLEWVSSISSSSTYIYYADSVKGRFTIS RDNAKNSLYLQMNSLRAEDTAVYYCARDRGSIWG QGTLVTVSS |
| | | | SEQ ID NO: 26332 | SEQ ID NO: 30338 |
| iPS:435523 | 21-225_157G5 | NA | GACATCCAGATGACCCAGTCTCCATCCTCACT GTCTGCATCTGTAGGGGACAGAGTCACCATCA CTTGTCGGGCGAGTCAGGGCATTAACAATTAT TTAGCCTGGTTTCAGCAGAAACCAGGGAAAGC CCCTGAGTCCCTGATCTATGCTGCATCCAGTTT ACAAAGTGGGGTCCCATCACAGTTCAGCGGCA GTGGATCTGGGACAGATTTCACTCTCACCATC AGCAGCCTGCAGCCTGAAGATTTTGCAACTTA TTACTGCCAACAGTATATAAGTTATCCATTCA CTTTCGGCCCTGGGACCAAAGTGGATATCAAA | GAGGTGCAGCTGTTGGAGTCTGGGGGAGGCTTG GTACAGCCGGGGGGTCCTGAGACTCTCCTGTG CAGCCTCTGGATTCACCTTTAGTAGCTATGTCAT GAGCTGGGTCCGCCAGGCTCCAGGGAAGGGACT GGAGTGGGTCTCAGCTATGAGTGGTAGTGGTGGT AGAACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTGTATTACTGTGCGAAGTATACCTG GAACGGCTACTGGGGCCAGGGAACCCTGGTCAC CGTCTCCTCA |
| | | | SEQ ID NO: 26333 | SEQ ID NO: 30339 |

FIGURE 50
(Continued)

| | | | |
|---|---|---|---|
| iPS:435525 | 21-225_157E7 | AA | DIQMTQSPSSLSASVGDRVTITCRASQGINNYLA WFQQKPGKAPESLIYAASSLQSGVPSRFSGSGSG TDFTLTISSLQPEDFATYYCQQYNSYPFTFGPGT KVDIK<br>SEQ ID NO: 26334 | EVQLLESGGGLVQPGGSLRLSCAASGFTFSSYVMS WVRQAPGKGLDWVSAMSGSGGRTYADSVKGRF TISRDNSKNTLYLQMNSLRAEDTAVYYCAKYTWN GYWGQGTLVTVSS<br>SEQ ID NO: 30340 |
| | | NA | GACATCCAGATGACCCAGTCTCCATCCTCCCT GTCTGCATCTGTAGGAGACAGAGTCACCATCA CTTGCCGGGCAAGTCAGAGTCAGAGTTTAGCAGTTAT TTAAATTGGTATCAGCAGAAACCAGGGATAGC CCCTAAACTCCTGATCTATGCTGCATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTACTGTCAAGAGAGTTATAGTATCCGCTTCG CCTTCGGCCAAGGGACACGACTGGAGATTAAA<br>SEQ ID NO: 26335 | CAGCTGCACCTGCAGGAGTCGGGCCCAGGACTG GTGAAGCCTTCGGAGACCCTGTCCTCACCTGCA CTGTCTCTGGTGGCTCCATCAGCAGTGGTAGTTA CTACTGGGGCTGGATCCGCCAGCCCCCAGGGAA GGGACTGGAGTGGATTGGAAGTATCTACTATAGT GGGAGCACCTACTACAATCCGTCCCTCAAGAGTC GAGTCACCATATCCGTAGACACGTCCAAGAACC AGTTCTCCCTGAACCTGAGCTCTGTGACCGCCGC AGACACGGCTGTCTATTACTGTGCGAGACATAAA GTGGCTGGTCCCTTTGACTACTGGGGCCAGGGAA CCCTGGTCACCGTCTCCTCA<br>SEQ ID NO: 30341 |
| | | AA | DIQMTQSPSSLSASVGDRVTITCRASQSFSSYLN WYQQKPGIAPKLLIYAASSLQSGVPSRFSGSGSG TDFTLTISSLQPEDFATYYCQESYSIRFAFGQGTR LEIK<br>SEQ ID NO: 26336 | QLHLQESGPGLVKPSETLSLTCTVSGGSISSGSYYW GWIRQPPGKGLEWIGSIYYSGSTYYNPSLKSRVTIS VDTSKNQFSLNLSSVTAADTAVYYCARHKVAGPF DYWGQGTLVTVSS<br>SEQ ID NO: 30342 |

FIGURE 50
(Continued)

| | | | |
|---|---|---|---|
| iPS:435527 | 21-225_157G7 | NA | GACATTCAGATGACTCAGTCTCCATCCTCCCT GTGTGCATCAGTAGGAGACAGAGTCACCATCA CTTGCCGGGCAAGTCAGGGACATTAGAAATGAT TTAGGCTGGTATCAGCAGAAACCAGGAAAG CCCCTAAGCGCTTGATCAATGTTGCATCCAGT TGCAAAGTGGGGTCCCATCAAGGTTCAGCGG CAGTGGATCTGGGACAGAATTCACTCTCACAA TCAGCAGCGTGCAGCCTGTGAAGATTTTGCAACT TATTACTGTATACAGGATAATAGTCACCCATT CACTTTCGGCCCTGGGACCAAAGTGGAAATCA AA<br><br>SEQ ID NO: 26337 | GAGGTGCAACTGGTGGAGTCTGGGGAGGCTG GTCAAGCCTGGGGGGTCCCTGAGATTCTCCTGTG CAGCCTCTGGATTCACCTTCAGTAGTTATAGCAT GAACTGGGTCCGCCAGGCTCCAGGGAAGGGCT GGAGTGGGTCTCATCCATTAGTGGTAGTAGTACG TACATATACTACGCAGACTCAGTGAAGGGCCGAT TCACCATCTCCAGAGACAACGCCAAGAACTCACT GTATCTGCAAATGAACAGCCTGAGAGCCGAAGA CACGGCTGTGTATTACTGTGCGAGAGATCGGGGC AGCAGCTGGGGCCAGGGAACCCTGGTCACCGTC TCCTCA<br><br>SEQ ID NO: 30343 |
| | | AA | DIQMTQSPSSLCASVGDRVTITCRASQGIRNDLG WYQQKPGKAPKRLINVASSLQSGVPSRFSGSGS GTEFTLTISSVQREDFATYYCIQDNSHPFTFGPGT KVEIK<br><br>SEQ ID NO: 26338 | EVQLVESGGGLVKPGGSLRFSCAASGFTFSSYSMN WVRQAPGKGLEWVSSISGSSTYIYYADSVKGRFTIS RDNAKNSLYLQMNSLRAEDTAVYYCARDRGSSW GQGTLVTVSS<br><br>SEQ ID NO: 30344 |
| iPS:435529 | 21-225_157H7 | NA | GACATCCAGATGACCCAGTCTCCATCCTCACT GTCTGCATCTGTAGGAGACAGAGTCACCATCA CTTGTCGGGCGAGTCAGGACATTAGCAATTTT TTAGCCTGGTTTCAGCAGAAACCAGGGAAAGC CCCTAAGTCCCTGATCTCTGCTGTCATCCAGTTT GCAAAGTGGGGTCCCATCAAGTTCAGCGGCA GTGGATCTGGGACAGATTTCACTCTCACCATC AGCAGCCTGCAGCCTGAAGATTTTGCAACTTA TTACTGCCAACAGTATCATAGTTACCGATCA CCTTCGGCCAAGGGACACGACTGGAGATTAAA<br><br>SEQ ID NO: 26339 | GAGGTGCAGCTGGTGGAGTCTGGGGGAGGCTG GTCAAGCCTGGGGGGTCCCTGAGACTCTCCTGTG CAGCCTCTGGATTCACATTCAGTAGCTATAGCAT GAACTGGGTCCGCCAGGCTCCAGGGAAGGGCT AGAGTGGGTCTCATGCATTAGTGGTAGTAGT TACATATATATGCAGACTCAGTGAAGGGCCGAT TCACCATGTCCAGAGACAACGCCAAGAACTCACT GTATCTGCAAATGAACAGCCTGAGAGCCGAGGA CACGGCTGTGTATTACTGTGTGAGAGATCGAGGG GGCTATTGGGGCCAGGGAACCCTGGTCACCGTCT CCTCA<br><br>SEQ ID NO: 30345 |

FIGURE 50
(Continued)

| | | | |
|---|---|---|---|
| iPS:435531 | 21-225_157G8 | AA | DIQMTQSPSSLSASVGDRVTITCRASQDISNFLAWFQQKPGKAPKSLVSTASSLQSGVPSKFSGSGSGTDFTLTISSLQPEDFATYYCQQYHSYPITFGQGTRLEIK<br>SEQ ID NO: 26340 | EVQLVESGGGLVKPGGSLRLSCAASGFTFSSYSMNWVRQAPGKGLEWVSCISGSSSYIYYADSVKGRFTMSRDNAKNSLYLQMNSLRAEDTAVYYCVRDRGGYWGQGTLVTVSS<br>SEQ ID NO: 30346 |
| | | NA | GATATTGTGATGACCCAGACTCCACTCTCTCTGTCCGTCACCCCTGGACAGCCGGCCTCCATCTCCTGCAAGTCTAGTCAGAGCCTCCTGCATGGTGATGGAAAGACCTATTTATATTGGTACCTGCAGAAGCCAGGCCAGTCTCCACAACTCCTGATCTATGAAATTTCCAAGCGGTTCTCTGGAGTGCCAGATAGGTTCAGTGGCAGCGGGTCAGGGACAGATTTCACACTGAAAATCAGCCGGGTGGAGGCTGAGGATGTTGGGGTTTACTACTGCATGCAAAGTATACAGGTTCCGTGGACGTTCGGCCAAGGGACCAAGGTGGAAATCAAA<br>SEQ ID NO: 26341 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAATTATGCATGCACTGGGTCCGCCAGGCTCCAGGCAAGGGCTGGAGTGGGTGGCAATTATATGGTATGATGGAAGTTATAAATACTATGCAGACTCCGTGAAGGGCCGATTCACCGTCTCCAGAGACAATTCCAAGAACACGCTGTATCTGCAAATGAACAGCCTGAGAGCCGAGGACACGGCTGTGTATTACTGTGCGAGAGAGGATACGATTTTTGGAGTGGTTTCTTTGACTCCTGGGCCAGGGAACCCTGGTCACCGTCTCCTCA<br>SEQ ID NO: 30347 |
| | | AA | DIVMTQTPLSLSVTPGQPASISCKSSQSLLHGDGKTYLYWYLQKPGQSPQLLIYEISKRFSGVPDRFSGSGSGTDFTLKISRVEAEDVGVYYCMQSIQVPWTFGQGTKVEIK<br>SEQ ID NO: 26342 | QVQLVESGGGVVQPGRSLRLSCAASGFTFSNYGMHWVRQAPGKGLEWVAIIWYDGSYKYYADSVKGRFTVSRDNSKNTLYLQMNSLRAEDTAVYYCAREGYDFWSGFFDSWGQGTLVTVSS<br>SEQ ID NO: 30348 |

FIGURE 50
(Continued)

| | | | |
|---|---|---|---|
| iPS:435533 | 21-225_157H8 | NA | GACATCCAGATGACCCAGTCTCCATCCTCCCT GTCTGCATCTGTAGGAGACAGAGTCACCATCA CTTGCCGGGCAAGTCAGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCG CAGTGGATCTGGGACAGACTTCACTCTCACAA TCAGCAGCCTGCAGCCTGATGACTTTGCAACT TATTACTGTCTACAGCATAATAGTTACCCATTC ACTTTCGGCCCTGGGACCAAAGTGGATATCAA A<br>SEQ ID NO: 26343 |
| | | AA | DIQMTQSPSSLSASVGDRVTITCRASQGIRNDLG WYQQKPGKAPKRLIYAASSLQSGVPSRFSGSGS GTDFTLTISSLQPDDFATYYCLQHNSYPFTFGPG TKVDIK<br>SEQ ID NO: 26344 |
| | | NA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTGGCAT GCACTGGGTCCGCCAGGCTCCAGGCAAGGGGCT GGAGTGGGTGGCTGTTATATGGTATGATGTAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGCTGGG GTTCCTCTGACTACTGGGGCCAGGGAACCCTG GTCACCGTCTCCTCA<br>SEQ ID NO: 30349 |
| | | AA | QVQLVESGGGVVQPGRSLRLSCAASGFTFSSYGMH WVRQAPGKGLEWVAVIWYDVNNKYYADSVKGRF TISRDNSKNTLYLQMNSLRAEDTAVYYCARELGFL SDYWGQGTLVTVSS<br>SEQ ID NO: 30350 |
| iPS:435535 | 21-225_157H10 | NA | GACATCCAGATGACCCAGTCTCCATCCTCACT GTCTGCATCTGTAGGAGACAGAGTCACCATCA CTTGTCGGGCGAGTCAGGGACATTAGCAATTAT TTAGCCTGGTTTCAGCAGAAACCAGGGAAAGC CCCTAAGTCCCTGATCTATACTGCATCCAATTT GCAAAGTGGGGTCCCATCAAGGTTCAGCGGCA GTGGATCTGGGACAGATTTCACTCTCACCATC AGCAGCCTGCAACAGTATCATAGTTACCCATTCA CTTTCGGCCCTGGGACCAAAGATTTGCAACTTA TTACTGCCAACAGTATCATAGTTACCCATTCA CTTTCGGCCCTGGGACCAAAGTGGATATCAAA<br>SEQ ID NO: 26345 | GAGGTGCAGCTGGTGGAGTCTGGGGGAGGCCTG GTCAAGCCTGGGGGGTCCCTGAGACTCTCCTGTG CAGCCCTCTGGATTCACCTTCAGTAGCTATACCAT GAACTGGGTCCGCCAGGCTCCAGGGAAGGGGCT GGAGTGGGTCTCATCCATTAGTGGTAGCAGTAGT TACATAAACTACGCAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGTGGCTCA CTTTGACTACTGGGGCCAGGGAACCCTGGTCACC GTCTCCTCA<br>SEQ ID NO: 30351 |

FIGURE 50
(Continued)

| | | | |
|---|---|---|---|
| | AA | DIQMTQSPSSLSASVGDRVTITCRASQGITNYLA WFQQKPGKAPKSLIYTASNLQSGVPSKFSGSGSG TDFTLTISSLQPEDFATYYCQQYHSYPFTFGPGT KVDIK<br><br>SEQ ID NO: 26346 | EVQLVESGGGLVKPGGSLRLSCAASGFTFSSYTMN WVRQAPGKGLEWVSSISGSSSYINYADSVKGRFTIS RDNAKNSLYLQMNSLRAEDTAVYYCARVAHFDY WGQGTLVTVSS<br><br>SEQ ID NO: 30352 |
| iPS:435537 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT CTTGGCTGGTATCAGCAGAAACCAGGGAAAGC CCCTAAGTCGCTGATTCATGCTGCATCCAGTTT ACAGAGTGGGGTCCCATCAAGGTTCAGCGGCA GTGGATCTGGGACAGACCTCACTCTCACAATC AGCAGCCTGCAGCCTGAAGATTATAGTTACTA TTACTGTCTACAGCATTATAGTTACCCATTCAC TTTCGGCCCTGGGACCAAAGTGGATATCAAA<br><br>SEQ ID NO: 26347 | GAGGTGCAGTGGGTGGAGTCTGGGGGAGGCCTG GTCAAGCCTGGGGGGTCCCTGAGACTCTCCTGTG CAGCCCTCTGATTCACCTTCAGTAGCTATAGCAT GAACTGGGTCCGCCAGGCTCCAGGGAAGGGGCT GGAGTGGGTCTCATCCATTAGTGGTAGTGGTAGT TACATAAACTACGCAGACTCAGTGAAGGGCCGG TTCACCATCTCCAGAGACAACGCAAGACTCAC TGTATCTGCAAGTGAACGGCCTGAGAGCCGAGG ACACGGCTGTGTATTACTGTGCGAGATCCAAGTT TGACTCCTGGGGCCAGGGAACCCTGGTCACCGTC TCCTCA<br><br>SEQ ID NO: 30353 |
| 21-225_157H12 | AA | DIQMTQSPSSLSASVGDRVTITCRASQGIRNDFG WYQQRPGKAPKCLIHAASSLQSGVPSRFSGSGS GTEFTLTISSLQPEDFATYYCLQHYSYPFTFGPGT KVDIK<br><br>SEQ ID NO: 26348 | EVQWVESGGGLVKPGGSLRLSCAASGFTFSSYSMN WVRQAPGKGLEWVSSISGSGSYINYADSVKGRFTIS RDNAKTSLYLQVNGLRAEDTAVYYCARSKFDSWG QGTLVTVSS<br><br>SEQ ID NO: 30354 |

FIGURE 50
(Continued)

| | | | |
|---|---|---|---|
| iPS:435539 | 21-225_158G1 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAAT TTGCAAAGTGGGGTCCCATCAAGGTTCAGCGG CAGTGGATGTGGGACAGAATTCACTCTCACAG TCAGCAGCCTGCAGCCTGAAGATTTTGCAACT TATTACTGTCTACAGCATAATAGTTACCCGTG GACGTTCGGCCAAGGGACCAAGGTGGAAATC AAA |
| | | | GAGGTGCAGCTGGTGGAGTCTGGGGGAGGCCTG GTCAAGCCTGGGGGGTCCCTGAGACTCTCCTGTG CAGCCCTCTGGATTCACCTTCAGTAGTTATGGCAT GAACTGGGTCCGCCAGGCTCCAGGGAAGGGGCT GGAGTGGATCTCATCCATTAGTGGTAGTGGTAGT TACATATACTACGCAGACTCAGTGAAGGGCCGAT TCACCATTTCCAGAGACAACGCCAAGAACTCACT GTATCTGCAAATGAACAGCCTGAGAGCCGAGA CACGGCTGTGTATTACTGTGCGATTAGCAGTGGC TGGTCTTGGGGCCAGGGAACCCTGGTCACCGTCT CCTCA |
| | | | SEQ ID NO: 26349 |
| | | | SEQ ID NO: 30355 |
| | | AA | DIQMTQSPSSLSASVGDRVTITCRASQGIRNDLG WYQQKPGKAPKRLIYTASNLQSGVPSRFSGSGC GTEFTLTVSSLQPEDFATYYCLQHNSYPWTFGQ GTKVEIK |
| | | | EVQLVESGGGLVKPGGSLRLSCAASGFTFSSYGMN WVRQAPGKGLEWISSSISGSGSYIYYADSVKGRFTIS RDNAKNSLYLQMNSLRAEDTAVYYCAISSGWSWG QGTLVTVSS |
| | | | SEQ ID NO: 26350 |
| | | | SEQ ID NO: 30356 |
| iPS:435543 | 21-225_158D4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAT TCAGCAGCCTGCAGCCTGAAGATTTTGCAACT TATTACTGTCTACAGCATTATAGTTACCCTCGG ACGTTCGGCCAAGGGACCAAGGTGGAAATCA AA |
| | | | CAGGTGCAGCTGGTGGAGTCTGGGGGAGGCGTG GTCCAGCCTGGGAGGTCCCTGAGACTCTCCTGTG CAGCGTCTGGATTCACCTCAGTGACTATGTCAT GCACTGGGTCCGCCAGGCTCCAGGCAAGGGGCT GGAGTGGGTGTCAGTTATATGGTATGATGGAAGT AATAAATACTATGCAGACTCCGTGAAGGGCCGA TTCACCATCTCCAGAGACAACATTCCAAGAACAC TGTATCTGCAAATGAACAGCCTGAGAGCCGAGG ACACGGCTGTGTATTACTGTGCGAGAGAACCGTA TACTAGTGGCTGGTACGACTACGGTATGGACGTC TGGGGCCAAGGGACCACGGTCACCGTCTCCTCA |
| | | | SEQ ID NO: 26351 |
| | | | SEQ ID NO: 30357 |

FIGURE 50
(Continued)

| | | AA | DIQMTQSPSSLSASVGDRVTITCRASQDIRKDLG WYQQKPGKAPKRLIYAASSLQSGVPSRFSGSGS GTEFTLTFSSLQPEDFATYYCLQHYSYPRTFGQG TKVEIK<br><br>SEQ ID NO: 26352 | QVQLVESGGGVVQPGRSLRLSCAASGFTFSDYVM HWVRQAPGKGLEWVSVIWYDGSNKYYADSVKGR FTISRDNSKNTLYLQMNSLRAEDTAVYYCAREPYT SGWYDYGMDVWGQGTTVTVSS<br><br>SEQ ID NO: 30358 |
|---|---|---|---|---|
| iPS:435545 | 21-225_158F4 | NA | GACATCCAGATGACCCAGTCTCCATCCCCT GCCTGCATCTGTAGGAGACAGAGTCACCATCA CTTGCCGGGCAAGTCAGAGACATTAGAAAGTAT TTACATTGGTATCAGTTCTTACCAGGGAAAGC CCCTAAGCTCCTGATCTATACTGCATCCACTTT ACAAAGTGGGGTCCCATCAAGGTTCAGTGGCA GCGGATCTGGGACAGAGATTTCACTCTCACCAT AGCAGTCTGCAACCTGAAGATTACAATATTTCA CTACTGTCAACAGAGTTACAATATTCATTCA CTTTCGGCCCTGGGACCAAAGTGGATATCAAA<br><br>SEQ ID NO: 26353 | CAGGTGCAGCTGCAGGAGTCGGGCCAGGACTG GTGAAGCCTTCGGAGACCCTGTCCCTCACTTGCA CTGTCTCTGGTGGCTCCATCAGTAGTCACTTCTG GAGCTGGATCCGGCAGCCCGCGGGAAGGGACT GGAGTGGATTGGCCGTATCTATACCAGTGGGACC ACCAACTACACCCCCTCCCTCAAGAGTCGAGTCA CCATGTCAGTAGACACGTCCAAGAACCAGTTCTC CCTGAAGCTGAGCTCTGTGACCGCCGCGGACACG GCCGTGTATTACTGTGCGAGATTGAGCAGTGGCT GGTTTGACTACTGGGGCCAGGGAACCCTGGTCAC CGTCTCCTCA<br><br>SEQ ID NO: 30359 |
| | | AA | DIQMTQSPSSLPASVGDRVTITCRASQNIRKYLH WYQFLPGKAPKLLIYTASTLQSGVPSRFSGSGSG TDFTLTISSLQPEDFATYYCQQSYNISFTFGPGTK VDIK<br><br>SEQ ID NO: 26354 | QVQLQESGPGLVKPSETLSLTCTVSGGSISSHFWSW IRQPAGKGLEWIGRIYTSGTTNYTPSLKSRVTMSVD TSKNQFSLKLSSVTAADTAVYYCARLSSGWFDYW GQGTLVTVSS<br><br>SEQ ID NO: 30360 |

FIGURE 50
(Continued)

| | | | |
|---|---|---|---|---|
| iPS:435547 | 21-225_158F5 | NA | GACATTCAGATGACCCAGTCTCCATCCTCCT GTCTGCATCTGTAGGAGACAGAGTCACCATCA CTTGCCGGGCAAGTCAGGCATTAGAAATGAT TTAGGCTGGTATCAGCAGAAACCAGGAAAG CCCCTAAGCGCCTGATCAATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGGATAATAGTCACCCATT CACTTTCGGCCCTGGGACCAAAGTGGAAATCA AA SEQ ID NO: 26355 | GAGGTGCAACTGGTGGAGTCTGGGGGAGGCTG GTCAAGCCTGGGGGGTCCCTGAGATTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTGGTAGTAGTACG TACATATACTACGCAGACTCAGTGAAGGGCCGAT TCACCATCTCCAGAGACAACAGCCAAGAACTCACT GTATCTGCAAATGAACAGCCTGAGAGCCGAAGA CACGGCTGTGTATTACTGTGCGAGAGATCGGGGC AGCAGCTGGGGCCAGGGAACCCTGGTCACCGTC TCCTCA SEQ ID NO: 30361 |
| | | AA | DIQMTQSPSSLSASVGDRVTITCRASQGIRNDLG WYQQKPGKAPKRLINAASSLQSGVPSRFSGSGS GTEFTLTISSLQPEDFATYYCLQDNSHPFTFGPGT KVEIK SEQ ID NO: 26356 | EVQLVESGGGLVKPGGSLRFSCAASGFTFSSYSMN WVRQAPGKGLEWVSSISGSSTYIYYADSVKGRFTIS RDNAKNSLYLQMNSLRAEDTAVYYCARDRGSSW GQGTLVTVSS SEQ ID NO: 30362 |
| iPS:435549 | 21-225_158H5 | NA | GACATCCAGATGATCCAGTCTCCATCCTTCCT GTTTGCATCTGTAGGAGACAGAGTTACCATCA CTTGCCGGGCAAGTCAGGGTCATGAGAATTGAT TTAGGGTGGTATCAGCAGAAACCAGGAAAAG CCCCTAAGCGCCTGATTTATCGTGCATCCAGT TGCAAAGTGTGGGACAGAGTTTATCGTGCATCCAGT AGTGGATCTGGGACAGAATTCACTCTCACAAT CAGCAGCGTGCAGCGTGAAGATTTTGCAAGTT ATTACTGTGTACAGCATATAATAGTTACCCTC ACTTTCGGCGGAGGGACCAAGGTGGAGATCA AA SEQ ID NO: 26357 | GAGGTGCAACTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATCAGTGGTAGTAGTACT TACATATACTACGCAGACTCAGTGAAGGGCCGAT TCACCATCTCCAGAGACAACAGCCAAGAACTCACT GCATCTGCAAATGAACAGCCTGAGAGCCGAGGA CACGGCTGTGTATTACTGTGTGCGAGAGATCGGGGC AGCAGCTGGGGCCAGGGAACCCTGGTCACCGTC TCCTCA SEQ ID NO: 30363 |

FIGURE 50
(Continued)

| | | AA | DIQMIQSPSPFLFASVGDRVTITCRASQGMRIDLG<br>WYQQKPGKAPKRLIYRASSLQSGVPSRFSGSGC<br>GTEFTLTISSVQREDFASYYCVQHNSYPLTFGGG<br>TKVEIK<br>SEQ ID NO: 26358 | EVQLVESGGGLVKPGGSLRLSCAASGFTFSSYSMN<br>WVRQAPGKGLEWVSSISGSSTYYYADSVKGRFTIS<br>RDNAKNSLHLQMNSLRAEDTAVYYCARDRGSSW<br>GQGTLVTVSS<br>SEQ ID NO: 30364 |
|---|---|---|---|---|
| iPS:435551 | 21-225_158H6 | NA | GACATCCAGATGACCCAGTCTCCATCCTCCCT<br>GTCTGCATCTGTAGGAGACAGAGTCACCATCA<br>CTTGCCGGGCAAGTCAGGGCATTAGAAGTGAT<br>TTAGGCTGGTATCAGCAGAAACCAGGGAAAG<br>CCCCTAAGCGCCTGATCTATACTGCATCCAGT<br>TTGCAAAGTGGGGTCCCATCAAGGTTCAGCGG<br>CAGTGGATCTGGGACAGGAATTCACTCTCACAA<br>TCAGCAGCCTGCAGCCTGAAGATTTTGCAACT<br>TATTACTGTCTACAGCATAATAGTTACCCATTC<br>ACTTTCGGCCCTGGGACCAAAGTGGACATCAA<br>A<br>SEQ ID NO: 26359 | CAGGTGCAGCTGGTGGTGGAGTCTGGGGGAGGCGTG<br>GTCCAGCCTGGGAGGTCCCTGAGACTCTCCTGTG<br>CAGTGTCTGGATTCACCTTCAGTAGCTATGGCAT<br>GCACTGGGTCCGCCAGGCTCCAGGCAAGGGGCT<br>GGAGTGGGTGGCAGTTATATGATGTAACT<br>AATAAATACTATGCAGACTCCGTGAAGGGCCGA<br>TTCACCATCTCCAGAGACAATTCCAAGAACACGC<br>TGTATCTGCAAATGAACAGCCTGAGAGACGAGG<br>ACACGGCTGTGTATTATTGTGTAGAGAAGAACTGGG<br>ATGGGCGGAGGACTACTGGGGCCAGGGAACCCT<br>GGTCACCGTCTCCTCA<br>SEQ ID NO: 30365 |
| | | AA | DIQMTQSPSSLSASVGDRVTITCRASQGIRSDLG<br>WYQQKPGKAPKRLIYTASSLQSGVPSRFSGSGSG<br>TEFTLTISSLQPEDFATYYCLQHNSYPFTFGPGTK<br>VDIK<br>SEQ ID NO: 26360 | QVQLVESGGGVVQPGRSLRLSCAVSGFTFSSYGMH<br>WVRQAPGKGLEWVAVIWYDVTNKYYADSVKGRF<br>TISRDNSKNTLYLQMNSLRDEDTAVYYCVRELGW<br>AEDYWGQGTLVTVSS<br>SEQ ID NO: 30366 |

FIGURE 50
(Continued)

| | | | |
|---|---|---|---|
| iPS:435553 | 21-225_158G8 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATGTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br><br>SEQ ID NO: 26361 | GAGGTGCAGCTGGTGGAGTCTGGGGGAGGCCTG GTCACGCCTGGGGGGTCCCTGAGACTCTCCTGTG CAGCCTCTGGATTCACCTTCAGTAGCTATACCAT GAACTGGGTCCGCCAGGCTCCAGGGAAGGGGCT GGAGTGGGTCTCATTGATTAGTGGCAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGATCGAGGC AGCCTCTGGGGCCAGGGAACCCTGGTCACCGTCT CCTCA<br><br>SEQ ID NO: 30367 |
| | | AA | DIQMTQSPSSLSASVGDRVTITCRASQDIRNDLG WYQQKPGKAPKRLMYTASSLQSGVPSRFSGSGS GTEFTLTISSLQPEDFATYYCLQHNSYPFTFGPGT KVDIK<br><br>SEQ ID NO: 26362 | EVQLVESGGGLVTPGGSLRLSCAASGFTFSSYTMN WVRQAPGKGLEWVSLISGSSSYIYADSVKGRFTIS RDNAKNSLYLQMNSLRAEDTAVYYCARDRGSLW GQGTLVTVSS<br><br>SEQ ID NO: 30368 |
| iPS:435557 | 21-225_158B12 | NA | GACATCGTGATGACCCAGTCTCCAGACTCCCC GGCTGTGTCTCTGGGCGAGAGGGCCACCATCA ACTGCAAGTCCAGCAGTGATGTTTACAGC TCCAACAATAACAACTACTTAACTTGGTACCA GCAGAAACCAGGACAGCCTCCTAAGTTGCTCA TTTACTGGGCATCTACCCGGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAA TATTATAGTACTCCTCTCGACGTTCGGCCAAGG GACCAAGGTGGAAATCAAA<br><br>SEQ ID NO: 26363 | CAGGTGCAGCTGGTGCAGTCTGGGGCTGAGGTG AGGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG ATTCACCATGACCAGGAACACCTCCATAAGCACA GCCTACATGGAGCTGAGCAGCCTGAGATCTGAG GACACGGCCGTGTATTACTGTGCCTATAGCAGTG GCTGGTACCGCTTTGACTACTGGGGCCAGGGAAC CCTGGTCACCGTCTCCTCA<br><br>SEQ ID NO: 30369 |

FIGURE 50
(Continued)

| | | | |
|---|---|---|---|
| iPS:435559 | 21-225_158H12 | AA | DIVMTQSPDSPAVSLGERATINCKSSQNVLHSSN NNNYLTWYQQRPGQPPKLLIYWASTRESGVPDR FSGSGSGTEFTLTISSLQAEDVAVYYCQQYYSTP PTFGQGTKVEIK<br>SEQ ID NO: 26364 | QVQLVQSGAEVRKPGASVKVSCKASGYTFTNYDIN WVRQATGQGLEWMGWMHPNSGNTGYAQKFQGR FTMTRNTSISTAYMELSSLRSEDTAVYYCAYSSGW YRFDYWGQGTLVTVSS<br>SEQ ID NO: 30370 |
| | | NA | GACATCCAGATGACCCAGTCTCCATCCTCACT GTCTGCATCTGTAGGAGACAGAGTCACCATCA CTTGTCGGGCGAGTCAGGGCATTAACAATTAT TTAGCCTGGTTTCAGCAGAAACCAGGGAAAGC CCCTAAGTCCCTGATCTCTGCTGCATCCAGTTT ACAAAGTGGGGTCCCATCAAAGTTCAGCGGCA GTGGATCTGGGACAGATTCACTCTCAGTATC AGCAGCCTACAGCCTGAAGATTTTGCAACTTA TTACTGTCAACAGTATCATAGTTACCCATTCAC TTTCGGCCCTGGGACCAAAGTGGATATCAAA<br>SEQ ID NO: 26365 | GAGGTGCAGCTGGTGGTGGAGTCTGGGGAGGCTTG GTACAGCCTGGGGGGTCCCTGAGACTCTCCTGTG CAGCCTCTGGATTCACCTTTAGCAGCTATGTCAT GAGCTGGGTCCGCCAGGCTCCAGGGAAGGGGCT GGAGTGGGTCTCAGTATTAGTGGTAGTGGTGGT AGGACAGACTACGCAGAGACTCCGTAAAGGCCGG TTCACCATCTCCAGAGACAATTCCAAGAACACGC TGTATCTGCAAATGAACAGCCTGAGAGCCGAGG ACACGGCCGTATATTACTGTGCGAAAGGGGGCT GGAACCACGACTGGGGCCAAGGGACCACGGTCA CCGTCTCCTCA<br>SEQ ID NO: 30371 |
| | | AA | DIQMTQSPSSLSASVGDRVTITCRASQGINNYLA WFQQKPGKAPKSLISAASSLQSGVPSKFSGSGSG TDFTLSISSLQPEDFATYYCQQYHSYPFTFGPGTK VDIK<br>SEQ ID NO: 26366 | EVQLVESGGGLVQPGGSLRLSCAASGFTFSSYVMS WVRQAPGKGLEWVSAISGSGGRTDYADSVKGRFTI SRDNSKNTLYLQMNSLRAEDTAVYYCAKGGWNH DWGQGTTVTVSS<br>SEQ ID NO: 30372 |

FIGURE 50
(Continued)

| | | | |
|---|---|---|---|
| iPS:435561 | 21-225_159F1 | NA | GACATCCAGATGACCCAGTCTCCATCCTCCCT GTCTGCATCGGTAGGAGACAGAGTCACCATCA CTTGCCGGGCAAGTCAGCGCGTCAGAAATGAT TTAGGCTGGTATCAGCAGAAACCAGGGAAAG CCCCTAAGCGCATCATTTTCGATGCATCCAATT TGCAAAAGTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATCATAGTTTCCGATCA CCTTCGGCCAAGGGACCCGACTGGAAGATTAAA<br>SEQ ID NO: 26367 | GAGGTGCAGCTGGTGGAGTCTGGGGGAGGCTG GTCAAGCCGGGGGGGTCCCTGAGACTCTCGTG CAGCCTCTGGATTCACCTTCAGTAGTTAGTATAGAAT GAACTGGGTCCGCCAGGCTCCAGGGAAGGGCT GGAGTGGGTCTCATCCATAAGTGGTAGTGTAAT TACATAGACTACGCAGACTCAGTGAAGGGCCGA TTCACCATCTCAGAGACAACGCCAAGAACTCAC TGTATCTGCAAATGAACAGCCTGAGAGCCGAGG ACACGGCTGTGTATTACTGTGCGAGAGGTTGGGA CGTCTGGGGCCAAGGGACCACGGTCACCGTCTCC TCA<br>SEQ ID NO: 30373 |
| | | AA | DIQMTQSPSSLSASVGDRVTITCRASQRVRNDLG WYQQKPAKAPKRIIFDASNLQSGVPSRFSGSGSG TEFTLTISSLQPEDFATYYCLQHHSFPITFGQGTR LEIK<br>SEQ ID NO: 26368 | EVQLVESGGGLVKPGGSLRLSCAASGFTFSSYRMN WVRQAPGKGLEWVSSISGSGNYIDYADSVKGRFTI SRDNAKNSLYLQMNSLRAEDTAVYYCARGWDVW GQGTTVTVSS<br>SEQ ID NO: 30374 |
| iPS:435563 | 21-225_159H2 | NA | GACATCCAGATGACCCAGTCTCCATCCTCCCT GTCTGCATCTGTAGGAGACAGAGTCACCATCA CTTGCCGGGCAAGTCAGAGTCAGAGCATTAGCAAATAT TTAAATTGGTATCAGCAGAAAACCAGGAAAG CCCCTGAACTCCTGATCTATGCTACATCCAATT TGCAAAGTGGGGTCCCATCAAGGTTCAGTGGC AGTGGATCTGGGACAGATTTCACTCTCACCAT CAGCACTCTGCAACCTGAAGATTTTGTAACTT ACTACTGTCAACAGAGTTACAGTCTCCCCGTC ACTTTCGGCGGAGGGACCAAGGTAGAGATCA AA<br>SEQ ID NO: 26369 | CAGGTGCAGCTGGTGCAGTCTGGGGCTGAGGTG AAGAAGCCTGGGGCTCAGTGAAGGTCTCCTGC AAGGCTTCTGGATACACCTTCACCAGTTATGATA TCAACTGGGTGCGACAGGCCACTGGACAAGGC TTGAGTGGATGGGATGGATGTACAGAAGTTCCAGGCA GTAACACAGGCTATGTACCAGGAAGTTCCAGGCA GAGTCACCATGACCAGGAACACCTCCATAAGCA CAGCCTACATGGAGCTGAGCAGCCTGAGATCTG AGGACACGGCCGTGTATTACTGTGCGAGAAAGA AAACTGGGGACTACTGGGGCCAGGGAACCCTGG TCACCGTCTCCTCA<br>SEQ ID NO: 30375 |

FIGURE 50
(Continued)

| | | AA | DIQLTQSPSSLSASVGDRVTITCRASQSISKYLNW YQQKPGKAPELLIYATSNLQSGVPSRFSGSGSGT DFTLTISTLQPEDFVTYYCQQSYSLPVTFGGGTK VEIK | QVQLVQSGAEVKKPGASVKVSCKASGYTFTSYDIN WVRQATGQGLEWMGWMNPNSGNTGYVQKFQGR VTMTRNTSISTAYMELSSLRSEDTAVYYCARKKTG DYWGQGTLVTVSS |
|---|---|---|---|---|
| | | | SEQ ID NO: 26370 | SEQ ID NO: 30376 |
| iPS:435565 | 21-225_159C4 | NA | GACATCCAGATGACCCAGTCTCCATCCTCCCT GTCTGCATCTGTAGGAGACAGAGTCACCATCA CTTGCCAGGCGAGTCAGGACATTAGCGACTAT TTAAATTGGTATCAACAGAAACCAGGGAAAG CCCCTAAACTCCTGATCTACGATGCCTCCACTT TGGAAACAGGGGTCCCATCAAGGTTCAGTGGA AGTGGATCTGGGACAGATTTTACTTTCACCAT CAGCAGCCTGCAGCCTGAAGATATTGCAACAT ATTTCTGTCAACAATATGATAATCTCCCGATC ACCTTCGGCCAAGGGACACGACTGGAGATTAA A | CAGGTGCAGCTGGTGGAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGGCT GGAGTGGGTGGCAGTTATATCAGACTCCGTGAAAC AATAAATACTATGCAGAGACTCCGTGAAGGCCGA TTCACCATCTCCAGAGACACAATTCCAAGAACACGC TGTATCTGCAGTTGAACAGCCTGAGAGCTGAGGA CATGGCTGTGTATTACTGTGCGAGACGGAGCAGC TCGTGGGGGGCTACGGTATGGACGTCTGGGGC CACGGGACCACGGTCACCGTCTCCTCA |
| | | | SEQ ID NO: 26371 | SEQ ID NO: 30377 |
| | | AA | DIQMTQSPSSLSASVGDRVTITCQASQDISDYLN WYQQKPGKAPKLLIYDASTLETGVPSRFSGSGS GTDFTFTISSLQPEDIATYFCQQYDNLPITFGQGT RLEIK | QVQLVESGGGVVQPGRSLRLSCAASGFTFSNYGM HWVRQAPGKGLEWVAVISYSGNNKYYADSVKGR FTISRDNSKNTLYLQLNSLRAEDMAVYYCARRSSS WGGYGMDVWGHGTTVTVSS |
| | | | SEQ ID NO: 26372 | SEQ ID NO: 30378 |

FIGURE 50
(Continued)

| | | | | |
|---|---|---|---|---|
| iPS:435569 | 21-225_159C5 | NA | GACATCCAGATGACCCAGTCTCCATCCTCCCT GTCTGCATCTGTAGGAGACAGAGTCACCATCA CTTGCCGGGACAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAGACTTCACTCTCACA TCATCAGCCTGCAGCCTGATGACTTTGCAACT TATTACTGTCTACAGCATAATAGTTATCCATTC ACTTTCGGCCCTGGGACCAAGTGGATATCAA A <br/> SEQ ID NO: 26373 | CAGGTGCAGCTGGTGGAGTCTGGGGAGGCGTG GTCCAGCCTGGGAGGTCCCTGAGACTCTCCTGTG CAGCCGTCTGGATTCACCTTCAGTAGTATGGCAT ACACTGGGTCCGCCAGGCTCCAGGCAAGGGGCT GGAGTGGGTGGCGTGTTGTATGGTATGATGTAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGTGGG GTTCCTCTGACTACTGGGGCCAGGGAACCCTG GTCACCGTCTCCTCA <br/> SEQ ID NO: 30379 |
| | | AA | DIQMTQSPSSLSASVGDRVTITCRTSQGIRNDLG WYQQKPGKAPKRLIYAASSLQSGVPSRFSGSGS GTDFTLTISLQPDDFATYYCLQHNSYPFTFGPGT KVDIK <br/> SEQ ID NO: 26374 | QVQLVESGGGVVQPGRSLRLSCAASGFTFSSYGIH WVRQAPGKGLEWVAVVWYDVNNKYYADSVKGR FTISRDNSKNTLYLQMNSLRAEDTAVYYCARELGF LSDYWGQGTLVTVSS <br/> SEQ ID NO: 30380 |
| iPS:435571 | 21-225_159C8 | NA | GACATCCAGATGACCCAGTCTCCATCCTCCCT GTCTGCATCTGTAGGAGACAGAGTCACCATCA CTTGCCGGGACAAGTCAGGACATTAGAAAGGAT TTAGGCTGGTATCAGCAGAAACCAGGGAAAG CCCCTAACCGCCTGATCTATGCTGCATCCAGT TGCAAAGTGGGGTCCCATCAAGGTTCAGCGGC AGTGGATCTGGGACAGAGCCTGCACTCTCACATT CAGCAGCCTGCAGCATCTGAAGATTTTGCAACTT ATTACTGTCTACAGCATCATAGTTATCCTCGG ACGTTCGGCCAAGGGACCAAGGTGGAAATCA AA <br/> SEQ ID NO: 26375 | CAGGTGCAACTGGTGGAGTCTGGGGAGGCGTG GTCCAGCCTGGGAGGTCCCTGAGACTCTCCTGTG CAGCGTCTGGATTCACCTTTAGTAGTACTATGCAT GCAGTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAACCGTA TAATAGTGGCTGGTACGACTACGGTATGGACGTC TGGGGCCAAGGGACCACGGTCACCGTCTCCTCA <br/> SEQ ID NO: 30381 |

FIGURE 50
(Continued)

| | | | |
|---|---|---|---|
| | | AA | DIQMTQSPSSLSASVGDRVTITCRASQDIRKDLGWYQQKPGKAPNRLIYAASSLQSGVPSRFSGSGSGTEFTLTFSSLQPEDFATYYCLQHSYPRTFGQGTKVEIK<br><br>SEQ ID NO: 26376 | QVQLVESGGGVVQPGRSLRLSCAASGFTFSDYVMQWVRQAPGKGLEWVAVIWYDGSNKYYADSVKGRFTISRDNSKNTLYLQMNSLRAEDTAVYYCAREPYNSGWYDYGMDVWGQGTTVTVSS<br><br>SEQ ID NO: 30382 |
| iPS:435573 | 21-225_159D8 | NA | GACATCCAGATGACCCAGTCTCCATCCTCCCTGTCTGCATCTGTTGGAGACAGAGTCACCATCACTTGCCGGGCAAGTCGGGACATTGGAAATGATTTAGGCTGGTATCAGCAGAAACCAGGAAAGCCCCTAAGCGCCTGATCTCTGCTGCATCCAGTTTGCAAAGTGGGGTCCCATCAAGGTTCAGCGGCAGTGGATCTGGGACAGATCACTCTCACATTCAGCAGCCTGCAGCCTGAAGATTTTGCAACTTATTACTGTCTACAGCATTATAGTACCTCGGACGTTCGGCCAAGGGACCAAGGTGGAAATCAAA<br><br>SEQ ID NO: 26377 | CAGGTGCAGCTGGTGGAGTCTGGGGGAGGCGTGGTCCAGCCTGGGAGGTCCCTGAGACTCTCCTGCGCAGCGTCTGGATTCACCTTCAGTGACTATGTCATGCACTGTGTCCGCCAGGCTCCAGGCAAGGGGCTGGAGTGGGTGGCAGTTATATGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAACCGTATAGTAGTGGCTGGTACGACTACGGTATGGACGTCTGGGGCCAAGGGACCACGGTCACCGTCTCCTCA<br><br>SEQ ID NO: 30383 |
| | | AA | DIQMTQSPSSLSASVGDRVTITCRASRDIGNDLGWYQQKPGKAPKRLISAASSLQSGVPSRFSGSGSGTEFTLTFSSLQPEDFATYYCLQHYSYPRTFGQGTKVEIK<br><br>SEQ ID NO: 26378 | QVQLVESGGGVVQPGRSLRLSCAASGFTFSNYVMHCVRQAPGKGLEWVAVIWYDGSNKYYADSVKGRFTISRDNSKNTLYLQMNSLRAEDTAVYYCAREPYSSGWYDYGMDVWGQGTTVTVSS<br><br>SEQ ID NO: 30384 |

FIGURE 50
(Continued)

| | | | |
|---|---|---|---|
| iPS:435575 | 21-225_159H11 | NA | GACATCCAGATGACCCAGTCTCCATCCTCACT GTCTGCATCTGTAGGAGACAGAGTCACCATCA CTTGTCGGGCGAGTCAGGGCATTAGCAAATAT TTAGTCTGGTTTCAGCAGAAACCAGGGAAAGC CCCTAAGTCCCTGATCTATGCTGCATCCAGTCT GCAAAGTGGGGTCCCATCAAAGTTCAGCGGCA GTGGATCTGGGACAGATTTCACTCTCACCATC AGCAACCTGCAGCCTGAAGATTTTGCAACTTA TTACTGCCAACAGTATAATAGTTACCCATTCA CTTTCGGCCCTGGGACCAAAGTGGATATCAAA<br>SEQ ID NO: 26379 | GAGGTGCAGCTGGTGGAGTCTGGGGGAGGCCTG GTCAAGCCTGGGGGGTCCCTAAGACTCTCCTGTG CAGCCCTGGATTCACCTTCAGTAGTAGTATACCAT GAACTGGGTCCGCCAGGCTCCAGGGAAGGGGCT GGAGTGGGTCTCATCCATTAGTGGTAGTAGTAGT TACATATACTACGCAGAGACTCAGTGAAGGGCCGAT TCACCATCTCCAGAGACAAACGCCAAGAACTCACT GTATCTGCAAATGAACAGCCTGAGAGCCGAGA CACGGCTGTATATTACTGTGCCGAGTGAGCTGG GCTGACTGCTGGGGCCAGGGAACCCTGGTCACC GTCTCCTCA<br>SEQ ID NO: 30385 |
| | | AA | DIQMTQSPSSLSASVGDRVTITCRASQGISKYLV WFQQKPGKAPKSLIYAASSLQSGVPSKFSGSGSG TDFTLTISNLQPEDFATYYCQQYNSYPFTFGPGT KVDIK<br>SEQ ID NO: 26380 | EVQLVESGGGLVKPGGSLRLSCAASGFTFSSYTMN WVRQAPGKGLEWVSSISGSSSYIYADSVKGRFTIS RDNAKNSLYLQMNSLRAEDTAVYYCARVSWADC WGQGTLVTVSS<br>SEQ ID NO: 30386 |
| iPS:435577 | 21-225_160B1 | NA | GATATTGTGATGACCCAGACTCCACTCTCT GTCCGTCACCCTGGACAGCCGGCCTCCATCT CCTGCAAGTCTAGTCAGAGCCTCCTGCATGT CAAGGGAAGAACCTATTTCTATTGGTACCTGCA GAAGCCAGGCCAGCTCCACAGGTCCTGATCT ATGAAGTATCCAAGCGGTTCTCTGAGTGTCA GAAAGGTTCAGTGGCAGCGGGTCAGGGACAG ATTTCACACTGAAAATCAGCGGGTGGAGGCT GAGGATGTGGGGTTTATTACTGCATGCAAAG TATACAGATTCCGTGACGTTCGGCCAAGGGA CCAAGGTGGAAATCAAA<br>SEQ ID NO: 26381 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTATGGCAT GCACTGGGTCCGCCAGGCTCCAGGCAAGGGGCT GGAGTGGGTGGCAGTTATATGGTATGATGAAGT TATAAATACTATGCAGACTCCGTGAAGGGCCGAT TCACCATCTCCAGAGACAATTCCAAGAACACGCT GTATCTTCAAATGAACAGCCTGAGAGCCGAGA CACGGCTGTGTATTACTGTGCGAGAGGCCTAC GATTTTTGGAGTGGTTATTATGACTACTGGGCC AGGGAACCCTGGTCACCGTCCTCTCA<br>SEQ ID NO: 30387 |

FIGURE 50
(Continued)

| iPS:435579 | 21-225_160G1 | AA | DIVMTQTPLSLSVTPGQPASISCKSSQSLLHGDG KTYFYWYLQKPGQPPQVLIYEVSKRFS GSGSGTDFTLKISRVEAEDVGVYYCMQSIQIPWT FGQGTKVEIK<br>SEQ ID NO: 26382 | QVQLVESGGGVVQPGRSLRLSCAASGFTFSSYGMH WVRQAPGKGLEWVAVIWYDGSYKYYADSVKGRF TISRDNSKNTLYLQMNSLRAEDTAVYYCAREAYDF WSGYYDYWGQGTLVTVSS<br>SEQ ID NO: 30388 |
|---|---|---|---|---|
| | | NA | GACATCCAGATGACCCAGTCTCCATCCTGCT GTCTGCCTCTGTAGGAGACAGAGTCACCATCA CTTGTCGGGCGAGTCAGGACATTAACAATTAT TTAGCCTGGTTTCAGCAGAAACCAGGAAAAGC CCCTACGTCCCTGATCTATGCTTCATCCAGTT GCAAAGTGGGGTCCCATCAAAGTTCAGCGGCA GTGGATCTGGGACAGATTTCACTCTCACCATC AGCAGCCTGCAGCCTGAAGATTCATAGTTACCAATCA TTACTGCCAACAATATATCATAGTTACCCATTCA CTTTCGGCCCTGGGACCAAAGTGGATATCAGA<br>SEQ ID NO: 26383 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGTCAT GAGCTGGGTCCGCCAGGCTCCAGGGAAGGGGCT GGAGTGGGTCTCAGCTATGAGTGGTAGTGGTGGT CACACATACTACGCAGACTCCGTGAAGGGCCGG TTCACCATCTCCAGAGACAATTCCAAGAACACGG TGTATCTGCAAATGAACAGCCTGAGAGCCGAGG ACACGGCCGTATATTACTGTGTGAAACATGGATA CAGCTGGGGCCAGGGAACCCTGGTCACCGTCTCC TCA<br>SEQ ID NO: 30389 |
| | | AA | DIQMTQSPSSLSASVGDRVTITCRASQDINNYLA WFQQKPGKAPTSLIYASSSLQSGVPSKFSGSGSG TDFTLTISSLQPEDFATYYCQQYHSYPFTFGPGT KVDIR<br>SEQ ID NO: 26384 | EVQLLESGGGLVQPGGSLRLSCAASGFTFSSYVMS WVRQAPGKGLEWVSAMSGSGHTYADSVKGRF TISRDNSKNTVYLQMNSLRAEDTAVYYCVKHGYS WGQGTLVTVSS<br>SEQ ID NO: 30390 |

FIGURE 50
(Continued)

| | | | |
|---|---|---|---|
| iPS:435581 | 21-225_160H1 | NA | GACATCCAGATGACCCAGTCTCCATCCTCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTATGCTGCATCCAGT TTGCAGAATGGGGTCCCATCAAGGTTCAGCGG CAGTGGATCTGGGACAGAATTCACTCTCACAA TCAGCAGCCTGCAGCCTGAAGATTTTACAACT TATTACTGTCTACAGCATAATAGTTTCCCGTGG ACGTTCGGCCAAGGGACCAAGGTGGAAATCA AA | GAGGTGCAGCTGGTGGAGTCTGGGGGAGGCTG GTCAAGCCTGGGGGGTCCCTGAGACTCTCCTGT GCAGCCTCTGGATTCACCTTCAGTAGTAGTTACAT GAACTGGGTCCGCCAGGCTCCAGGGAAGGGGCT GGAGTGGGTCTCATCATTAGTAGTAGTACTGGT TACATGTACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTTCTGTGCGAGAGATAAAGAT TACTGGGGCCAGGGAACCCTGGTCACCGTCTCCT CA |
| | | SEQ ID NO: 26385 | SEQ ID NO: 30391 |
| | | AA | DIQMTQSPSSLSASVGDRVTITCRASQDIRNDLG WYQQKPGKAPKRLIYAASSLQNGVPSRFSGSGS GTEFTLTISSLQPEDFTTYYCLQHNSFPWTFGQG TKVEIK | EVQLVESGGGLVKPGGSLRLSCAASGFTFSSYRMN WVRQAPGKGLEWVSSISSSTGYMYYADSVKGRFTI SRDNAKNSLYLQMNSLRAEDTAVYFCARDKDYW GQGTLVTVSS |
| | | SEQ ID NO: 26386 | SEQ ID NO: 30392 |
| iPS:435583 | 21-225_160F2 | NA | GACATCCAGATGACCCAGTCTCCATCCTCCT GTCTGCATCTGTAGGAGACAGAGTCACCATCA CTTGCCGGGCAAGTCAGGACAGTCATTAGAAATGAT TTAGGCTGGTATCAGCAGAGAAACCAGGGAAAG CCCCTAAGCGCCTGATCTATACTGCATCCAAT TTGCAAAGTGGGGTCCCATCAAGGTTCAGCGG CAGTGGATCTGGGACAGAATTCACTCTCACAG TCAGCAGCCTGCAGCCTGAAGATTTTGCAACT TATTACTGTCTACAGCATAATAGTTACCCGTG GACGTTCGGCCAAGGGACCAAGGTGGAAATC AAA | GAGGTGCAGCTGGTGGAATCTGGGGGAGGCTG GTCAAGCCTGGGGGGTCCCTGAGACTCTCCTGTG CAGCCTCTGGATTCACCTTCAGTAGTTATGGCAT GAACTGGGTCCGCCAGGCTCCAGGGAAGGGGCT GGAGTGGATCTCATCATTAGTGGTGGTAGT TACATATACTACGCAGACTCAGTGAAGGGCCGAT TCACCATTTCCAGAGACAACAGCCAAGAACTCACT GTATCTGCAAATGAACAGCCTGAGAGCCGAGGA CACGGCTGTGTATTACTGTGCGATTAGCAGTGGC TGGTCTTGGGGCCAGGGAACCCTGGTCACCGTCT CCTCA |
| | | SEQ ID NO: 26387 | SEQ ID NO: 30393 |

FIGURE 50
(Continued)

| | | | |
|---|---|---|---|
| | | AA | DIQMTQSPSSLSASVGDRVTITCRASQGIRNDLG WYQQKPGKAPKRLIYTASNLQSGVPSRFSGSGS GTEFTLTVSSLQPEDFATYYCLQHNSYPWTFGQ GTKVEIK<br><br>SEQ ID NO: 26388 | EVQLVESGGGLVKPGGSLRLSCAASGFTFSSYGMN WVRQAPGKGLEWISSISGSGSYIYYADSVKGRFTIS RDNAKNSLYLQMNSLRAEDTAVYYCAISSGWSWG QGTLVTVSS<br><br>SEQ ID NO: 30394 |
| iPS:435585 | 21-225_160G3 | NA | GACATCCAGATGACCCAGTCTCCATCCTCGCT GTCTGCCTCTGTAGGAGACAGAGTCACCATCA CTTGTGCGGGCAGTCAGGACATTAATTAT TTAGCCTGGTTTCAGCAGAACCAGGGAAAGC CCCTACGTCCCTGATCTATGCTTCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAATATATCATAGTTACCCATTCA CTTTCGGCCCTGGGACCAAAGTGGATATCAAA<br><br>SEQ ID NO: 26389 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGTCAT GAGCTGGGTCCGCCAGACTCCAGGGAAGGGACT GGAGTGGGTCTCAGTATGAGTGGTAGTGGTGGT CACACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCATATATTACTGTGTGAAACATGGATA CAGCTGGGGCCAGGGAACCCTGGTCACCGTCTCC TCA<br><br>SEQ ID NO: 30395 |
| | | AA | DIQMTQSPSSLSASVGDRVTITCRASQDINNYLA WFQQRPGKAPTSLIYASSSLQSGVPSKFSGSGSG TDFTLTISSLQPEDFATYYCQQYHSYPFTFGPGT KVDIK<br><br>SEQ ID NO: 26390 | EVQLLESGGGLVQPGGSLRLSCAASGFTFSSYVMS WVRQTPGKGLEWVSAMSGSGGHTYYADSVKGRF TISRDNSKNTLYLQMNSLRAEDTAIYYCVKHGYSW GQGTLVTVSS<br><br>SEQ ID NO: 30396 |

FIGURE 50
(Continued)

| | | | | |
|---|---|---|---|---|
| iPS:435587 | 21-225_160H3 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATTTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAGTAATACCCGCTCACTTTCGGCGGAGGGACCCAGGTGGAGAGCAAA | CAGCTGCAGCTGCAGGAGTCGGGCCCAGGACTGGTGAAGCCTTCGGAGACCCTGTCCCTCACCTGCACCGTCTCTGGTGGCTCCATCAGCAGAAGTAGTTACTACTGGGGCTGGATCCGCCAGCCCCAGGGAAGGGACTGGAGTGGATTGGGAGTATCTATTATAGTGGGAGTACCTCCTACAACCCGTCTCTCGAGAGTCGAGTTACCATATCCGTAGACACGTCCAAGAACCAGTTCTCCCTGAAGCTGAGCTCTGTGACCGCCGCCGACACGGCTGTGTTTTACTGTGCGAGACTCTCAACGGTGGGACTTTGACTACTGGGGCCAGGGAACCCTGGTCACCGTCTCCTCA |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHSNYPLTFGGGTQVESK | QLQLQESGPGLVKPSETLSLTCTVSGGSISRSSYYWGWIRQPPGKGLEWIGSIYYSGSTSYNPSLESRVTISVDTSKNQFSLKLSSVTAADTAVFYCARLSQRWDFDYWGQGTLVTVSS |
| | | | SEQ ID NO: 26391 | SEQ ID NO: 30397 |
| | | | SEQ ID NO: 26392 | SEQ ID NO: 30398 |
| iPS:435589 | 21-225_160A4 | NA | GACATCGTGATGACCCAGTCTCCAGACTCCCTGGCTGTGTCTCTGGGCGAGAGGGCCACCATCAACTGCAAGTCCAGCCAGAGTGTTTTACACAGCTCCAACAATAAGAACTACTTAGCTTGGTACCAGCAGAAACCAGGACAGCCTCCTAAGCTACTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAATAGTCCGTGCAGTTTTGGCCAGGGGACCAAGCTGGAGATCAAA | CAGGTGCAGCTGGTGCAGTCTGGGACTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGACCTGAGTGGATGGGATGGATGAACCCTAACAGTGGTAACACAGGCTATCCACAGAAGTTCCAGGGCAGAGTCACCATGACCAGGAACACCTCCATAAGCACAGCCTACATGGAGCTGAGCAGCCTGAGATCTGAGGACACGGCCGTGTATTACTGTGCTGTACTGGGCCAGGAAGGACACCTGGTACATTTTGACTACTGGGGCCAGGGAACCCTGGTCACCGTCTCCTCA |
| | | | SEQ ID NO: 26393 | SEQ ID NO: 30399 |

FIGURE 50
(Continued)

| | | | | |
|---|---|---|---|---|
| | | AA | DIVMTQSPDSLAVSLGERATINCKSSQSVLHSSN NNNYLAWYQQKPGQPPKLLIYWASTRESGVPD RFSGSGSGTDFTLTISSLQAEDVAVYYCQQYYNS PCSFGQGTKLEIK<br><br>SEQ ID NO: 26394 | QVQLVQSGTEVKKPGASVKVSCKASGYTFTNYDIN WVRQATGQPEWMGWMHPNSGNTGYPQKFQGR VTMTRNTSISTAYMELSSLRSEDTAVYYCAYSSGW YIFDYWGQGTLVTVSS<br><br>SEQ ID NO: 30400 |
| iPS:435591 | 21-225_160C4 | NA | GACATCCAGATGACCCAGTCTCCATCCTCCCT GTCTGCATCTGTAGGAGACAGAGTCACCATCA CTTGCCGGGCAAGTCAGGACATTAGAAAGGAT TTAGGGTGGTATCAGCAGAAACCAGGGAAAG CCCCTAACCGCCTGATCTATGCTGCATCCAGTT TGCAAAGTGGGGTCCCATCAAGGTTCAGCGGC AGTGGATCTGGGACAGAATTCACTCTCACAT CAGCAGCCTGCAGCCTGAAGATTTTGCAACTT ATTACTGTCTACAGCATTATAGTTATCCTCGGA CGTTCGGCCAAGGGACCAAGGTGGAAATCAA A<br><br>SEQ ID NO: 26395 | CAGGTGCAACTGGTGGAGTCTGGGGGAGGCGTG GTCCAGCCTGGGGAGGTCCCTGAGACTCTCCTGTG CAGCGTCTGGATTCACCTTAGTGACTATGTCAT GCAGTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACCGTA TAATAGTGGCTGGTACGACTACGGTATGGACGTC TGGGGCCAAGGGACCACGGTCACCGTCTCCTCA<br><br>SEQ ID NO: 30401 |
| | | AA | DIQMTQSPSSLSASVGDRVTITCRASQDIRKDLG WYQQKPGKAPNRLIYAASSLQSGVPSRFSGSGS GTEFTLTFSSLQPEDFATYYCLQHYSYPRTFGQG TKVEIK<br><br>SEQ ID NO: 26396 | QVQLVESGGGVVQPGRSLRLSCAASGFTFSDYVM QWVRQAPGKGLEWVAVIWYDGSNKYYADSVKGR FTISRDNSKNTLYLQMNSLRAEDTAVYYCAREPYN SGWYDYGMDVWGQGTTVTVSS<br><br>SEQ ID NO: 30402 |

FIGURE 50
(Continued)

| | | | |
|---|---|---|---|
| iPS:435593 | 21-225_160F4 | NA | GACATTCAGATGACCCAGTCTCCATCCTCCCC GTCTGCATCTGTAGGAGACAGAGTCACCATCA CTTGCCGGGCAAGTCAGGGACATTAGAAATGAT TTAGGCTGGTATCAGCAGAAACCAGGAAAG CCCCTAAGCGCTTGATCAATGTTGCATCCAGT TTGCAAAGTGGGGTCCCATCAAGGTTCAGCGG CAGTGGATCTGGGACAGATTCACTCTTACAA TCAGCAGCGTGCAGCCTGAAGATATAGTCAACT TATTACTGTATACAGGATAATAGTCACCCATT CACTTTCGGCCCTGGGACCAAAGTGGAAATCA AA<br><br>SEQ ID NO: 26397 | GAGGTGCAACTGGTGGAGTCTGGGGGAGGCTG GTCAAGCCTGGGGGGTCCCTGAGATTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTGGTAGTAGTACG TACATATACTACGCAGACTCAGTGAAGGGCCGAT TCACCATCTCCAGAGACAACGCCAAGAACTCACT GTATCTGCAAATGAACAGCCTGAGAGCCGAAGA CACGGCTGTGTATTACTGTGCGAGAGATCGGGGC AGCAGCTGGGGCCAGGGAACCCTGGTCACCGTC TCCTCA<br><br>SEQ ID NO: 30403 |
| | | AA | DIQMTQSPSSPSASVGDRVTITCRASQGIRNDLG WYQQKPGKAPKRLINVASSLQSGVPSRFSGSGS GTEFTLTISSVQPEDFATYYCIQDNSHPFTFGPGT KVEIK<br><br>SEQ ID NO: 26398 | EVQLVESGGGLVKPGGSLRFSCAASGFTFSSYSMN WVRQAPGKGLEWVSSISGSSTYIYYADSVKGRFTIS RDNAKNSLYLQMNSLRAEDTAVYYCARDRGSSW GQGTLVTVSS<br><br>SEQ ID NO: 30404 |
| iPS:435595 | 21-225_160H4 | NA | GACATCCAGATGACCCAGTCTCCATCCTCACT GTCTGCATCTGTAGGAGACAGAGTCACCATCA CTTGTCGGGCGAGTCAGGACATCAGTAATTAT TTAGTCTGGTTTCAGCAGAAATTAGGGAAAGC CCCTAAGTCCCTGATCTATGTTGCATCCAGTTT GCAAAGTGGGGTCCCATCAAGGTTCAGCGGCA GTGGATCTGGGACAGATTTCACTCTCACCATC AGCAGCCTGCAGCCTGAAGATATTGCAACTTA TTACTGCCAACAGAGTATATATAGTACCCTCA CTTTCGGCGGAGGGACCAAAGTAGAGATCAA A<br><br>SEQ ID NO: 26399 | GAGGTGCAGCTGGTGGAGTCTGGGGGAGGCTG GTCAAGTCTGGGGGGTCCCTGAGACTCTCCTGTG CAGCCTCTGGATTCACCTTCAGTAGCTATAGGAT GAACTGGGTCCGCCAGGCTCCAGGGAAGGGGCT GGAGTGGGTCTCATCCATTAGTGGTGTAGTAGT TACATAGACTACGCAGAGTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAAAGAGTTG GTTTGACTACTGGGGCCAGGGAACCCTGGTCACC GTCTCCTCA<br><br>SEQ ID NO: 30405 |

FIGURE 50
(Continued)

| | | AA | DIQMTQSPSSLSASVGDRVTITCRASQDISNYLV WFQQKLGKAPKSLIYVASSLQSGVPSRFSGSGSG TDFTLTISSLQPEDFATYYCQQYNSYPLTFGGGT KVEIK <br><br>SEQ ID NO: 26400 | EVQLVESGGGLVKSGGSLRLSCAASGFTFSSYRMN WVRQAPGKGLEWVSSISGSSSYIDYADSVKGRFTIS RDNAKNSLYLQMNSLRAEDTAVYYCARKSWFDY WGQGTLVTVSS <br><br>SEQ ID NO: 30406 |
|---|---|---|---|---|
| iPS:435599 | 21-225_160B10 | NA | GACATCCAGATGACCCAGTCTCCATCCTCCC GTCTGCATCTGTAGGAGACAGAGTCACCATCA CTTGCCGGGCAAGTCAGGGACATTAGAAATGAT TTAGGCTGGTATCAGCAGAAACCAGGGACAG CCCCTAAGCGCCTTATCTATGCTGCATCCAGTT TGCAAAGTGGGGTCCCATCAAGGTTCAGCGGC AGTGGATCTGGGACAGAATTCACTCTCACAAT CAGCAACCTGCAGCCTGAGGATTTTGCAACTT ATTACTGTCTACAGCATAGTAGTTACCCGCTC ACTTTCGGCGGAGGGACCAAGGTGGAGATCA AA <br><br>SEQ ID NO: 26401 | CAGCTGCAGCTGCAGGAGTCGGGGCCAGGACTG GTGAAGCCTTCGGAGACCCTGTCCCTCACCTGCA CTGTCTCTGGTGGCTCCATCAGTAGTAGTAGCTA CTACTGGGGCTGGATCCGCCAGTACCCAGGGAA GGGGCTGGAGTGGATTGGAAATATCTATTATAGT GGGAGCGCCTACCACATTCCGTCCCTCAAGAGTC GAGTCACCATATCGTAGACACGTCCAAGAACC AGTTCTCCCTGAAGTTGAACTCTGTGACCGCCGC AGACACGGCTGTGTATTACTGTGTGAGACATGAC CCAAACTGGGGAGTTGACTACTGGGGCCAGGA ACCCGTCACCGTCTCCTCA <br><br>SEQ ID NO: 30407 |
| | | AA | DIQMTQSPSSPSASVGDRVTITCRASQGIRNDLG WYQQKPGTAPKRLIYAASSLQSGVPSRFSGSGSG TEFTLTISNLQPEDFATYYCLQHSSYPLTFGGGT KVEIK <br><br>SEQ ID NO: 26402 | QLQLQESGPGLVKPSETLSLTCTVSGGSISRSSYYW GWIRQYPGKGLEWIGNIYYSGSAYHIPSLKSRVTIS VDTSKNQFSLKLNSVTAADTAVYYCVRHDPNWGV DYWGQGTLVTVSS <br><br>SEQ ID NO: 30408 |

FIGURE 50
(Continued)

| | | | |
|---|---|---|---|
| iPS:435601 | 21-225_160G10 | NA | GCTATTGTGATGACCCAGACTCCACTCTCTG<br>TCCGTCACCCCTGGACAGCCGGCCTCCATCTC<br>CTGCAAGTCTAGTCAGAGCCTCCTGCACGTG<br>ATGGAAAGACCTATTTGTATTGGTACCTGCAG<br>AAGCCAGGCCAGCCTCCACACCTCCTGATCTA<br>TGAAGTTTCCAAACGGTTCTCTGGAGTGCCAG<br>ATAGGTTCAGTGGCAGCGGGTCAGGGACAGA<br>TTTCACACTGAAAATCAGCCGGGTGGAGGCTG<br>AGGATGTTGGGCTTTATTACTGCATGCAAAGT<br>ATACAGCTTCCGTGGACGTTTGTCCAAGGGAC<br>CAAGGTGGAAATCACA<br><br>SEQ ID NO: 26403 | CAGGTGCAGCTGGTGGAGTCTGGGGGAGGCGTG<br>GTCCAGCCTGGGAGGTCCCTGAGACTCTCCTGTG<br>CAGCGTCTGATTCACCTTCACTTCAGTAGCTTTGGCAT<br>GCACTGGGTCCGCCAGGCTCCAGGCAAGGCCT<br>GGAGTGGGTGGCAGTCATATGGATATGATGAAG<br>TTATAAATACTATGCAGACTCCGTGAAGGGCCGA<br>TTCACCATCTCCAGAGACAATTCCAAGAACACGC<br>TGTATCTGCAAATGAACAGCCTGAGAGCCGAGG<br>ACACGGCTGTGTATTACTGTGCGAGAGTTGGTAT<br>AGAAGTGGCTGGTGACTACTACTTCGGTATGGAA<br>GTCTGGGGCCAAGGGACCACGGTCACCGTCTCCT<br>CA<br><br>SEQ ID NO: 30409 |
| | | AA | AIVMTQTPLSLSVTPGQPASISCKSSQSLLHGDG<br>KTYLYWYLQKPGQPPHLLIYEVSKRFSGVPDRFS<br>GSGSGTDFTLKISRVEAEDVGLYYCMQSIQLPW<br>TFVQGTKVEIT<br><br>SEQ ID NO: 26404 | QVQLVESGGGVVQPGRSLRLSCAASGFTFSSFGMH<br>WVRQAPGKGLEWVAVIWYDGSYKYYADSVKGRF<br>TISRDNSKNTLYLQMNSLRAEDTAVYYCARVGIEV<br>AGDYYFGMEVWGQGTTVTVSS<br><br>SEQ ID NO: 30410 |
| iPS:435605 | 21-225_161A4 | NA | GAAATAGTGATGACGCAGTCTCCAGCCACCCT<br>GTCTGTGTCTCCAGGGGAAAGAGCCTCCCTCT<br>CCTGCAGGTCCAGTCAGAGTGTTAACAGCAAC<br>TTAGCCTGGTACCAGCAGAGGCCTGGCCAGGC<br>TCTCAGGCTCCTCATCTATGGTGCATCCATCAG<br>GGCCACTGGTATCCCAGCCAGGTTCAATGGCA<br>GTGGGTCTGGGACAGAGTTCACTCTCACCATC<br>AGCAGCCTGCAGTCTGAAGATTTTGCAGTTTA<br>TTTCTGTCAGCAGTATATAATAACTGGTGACGT<br>TCGGCCAAGGGACCACGGTGGAAATCAAA<br><br>SEQ ID NO: 26405 | GAGGTGCAGCTGGTGGAGTCTGGAGGAGGCTTG<br>ATCCAGCCTGGGGGGTCCCTGAGACTCTCCTGTG<br>CAGCCTCTGGTTCACCGTCAGTAGCAACTACAT<br>GAGCTGGGTCCGCCAGGCTCCAGGGAAGGGGCT<br>GGAGTGGGTCTCAGTTATTATACCGGTGGTAGC<br>ACATACAACGCAGACTCCGTGAAGGGCCGATTC<br>ACCATCTCCAGAGACAATTCCAAGAACACGCTGT<br>ATCTTCAAATGAACAGCTGAGAGCCGAGGACA<br>CGGCCGTGTATTACTGTGCGAGAAATTGGGAAT<br>GGCTGGCCCCTTTGACTACTGGGGCCAGGGAACC<br>CTGGTCACCGTCTCCTCA<br><br>SEQ ID NO: 30411 |

FIGURE 50
(Continued)

| | | | | |
|---|---|---|---|---|
| iPS:435607 | 21-225_161G4 | AA | EIVMTQSPATLSVSPGERASLSCRSSQSVNSNLA WYQQKRPGQALRLLIYGASIRATDIPARFNGSGSG TEFTLTISSLQSEDFAVYFCQQYNNWWTFGQGT TVEIK<br><br>SEQ ID NO: 26406 | EVQLVESGGGLIQPGGSLRLSCAASGFTVSSNYMS WVRQAPGKGLEWVSVIYTGGSTYNADSVKGRFTIS RDNSKNTLYLQMNSLRAEDTAVYYCARNWGMAG PFDYWGQGTLVTVSS<br><br>SEQ ID NO: 30412 |
| | | NA | GACATCCAGATGACCCAGTCTCCATCCTCCCT GTCTGCATCTGTAGGAGACAGAGTCACCATCA CTTGCCAGGCGAGTCAGGACATTTACAATTAT TTAAATTGGTATCAGCAGAAACCAGGGAAAG CCCCTAAGCTCCTGATCTACGATGCATCCAAT TTGGAAACAGGGGTCCCATCAAGGTTCAGTGG AAGTGGATCTGGGACAGATTTTACTTTCGCCA TCAGCAGCCTGCAGCCTGAAGATATTGCAACA TATTACTGTCAACAGTATGATATTCTCCCGATC ACCTTCGGCCAAGGGACACGACTGGAGATTAA A<br><br>SEQ ID NO: 26407 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGGCT GGAGTGGGTGGCAGTTATATCATATGGTGGAAGT AATAAATACCATGCAGACTCCGTGAAGGGCCGA TTCACCATCTCCAGAGACAATTCCAAGAACACGC TGTATCTGCAAATGAACAGCCTGAGAGCTGAGG ACACGGCTGTGTATTACTGTGTGAGACGGAGCAG CTCGTCGGGGGCTACGGTATGGACGTCTGGGGC CAAGGGACCACGGTCACCGTCTCCTCA<br><br>SEQ ID NO: 30413 |
| | | AA | DIQMTQSPSSLSASVGDRVTITCQASQDIYNYLN WYQQKPGKAPKLLIYDASNLETGVPSRFSGSGS GTDFTFAISSLQPEDIATYYCQQYDILPITFGQGT RLEIK<br><br>SEQ ID NO: 26408 | QVQLVESGGGVVQPGRSLRLSCAASGFTFSSYGMH WVRQAPGKGLEWVAVISYGGSNKYHADSVKGRFT ISRDNSKNTLYLQMNSLRAEDTAVYYCVRRSSSSG GYGMDVWGQGTTVTVSS<br><br>SEQ ID NO: 30414 |

FIGURE 50
(Continued)

| | | | |
|---|---|---|---|
| iPS:435609 | 21-225_161F7 | NA | GACATCCAGATGACCCAGTCTCCATCCTCCCT GTCTGCATCTGTAGGCGACAGAGTCACCATCA CTTGCCGGGCAAGTCAGGGCATTAGAAATGAT TTGGGCTGGTATCAGCAGAAACCAGGAAAG CCCCTAAGCGCCTGATCTATGCTGCATCCACTT TGCAAAGTGGGGTCCCATCGCGGTTCAGCGGC AGTGGATCTGGGGCAGAATTCACTGTCACAAT CGGCAGCGTGCAGCGTGAAGATTTTGCAACTT ATTACGGTCTACTATATATTCGTTACCATTCA CTTTTGGCCCTGTGGGACCAAGTGGATATCAAA<br>SEQ ID NO: 26409 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTTTGGCTT GCACTGGGTCCGCCAGGCTCCAGGCCAGGACT GGAGTGGGTGGCAGTTATATGGTTTGATGGAAGT AATAAATACTATGCAGACTCCGTGAAGGGCCGA TTCACCATTTCAGAGACAATTCCAAGAACACGC TGTATCTGCAAATGAACAGCCTGAGAGCCGAGG ACACGGCTGTGTATTACTGTGCGAGAGAGATTGG CTGGCTCTGACTACTGGGGCCAGGGAACCCTG GTCACCGTCTCCTCA<br>SEQ ID NO: 30415 |
| | | AA | DIQMTQSPSSLSASVGDRVTITCRASQGIRNDLG WYQQKPGEAPKRLIYAASTLQSGVPSRFSGSGS GAEFTVTIGSVQREDFATYYGLLYIRYPFTFGRG TKVDIK<br>SEQ ID NO: 26410 | QVQLVESGGGVVQPGRSLRLSCAASGFTFSDFGLH WVRQAPGQGLEWVAVIWFDGSNKYYADSVKGRF TIFRDNSKNTLYLQMNSLRAEDTAVYYCAREIGWL SDYWGQGTLVTVSS<br>SEQ ID NO: 30416 |
| iPS:435611 | 21-225_161F10 | NA | GACATCCAGATGACCCAGTCTCCATCCTCCCT GTCTGCATCTGTAGGAGACAGAGTCACCATCA CTTGCCAGGCGAGTCAGGACATTTACAACCAT TTAAGTTGGTATCAGCAGAAACCAGGGAAAG CCCCTAAGCTCCTGATCTACGATGCATCCAAT TGGGAAACAGGGGTCCCATCCAGTTCAGTGG AGTGGATCTGGGACAGATTTTACTTTCACCA TCAGCAGCCTGCAGCCTGAAGATTTTGCAACA TATTACTGTCAACAGTATGAAAATCTCCCGCT CACCTTCGGCGGAGGGACCAAGGTGGAGATC AAA<br>SEQ ID NO: 26411 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGTAGTGCAT GCCACTGGGTCCGCCAGGCTCCAGGCAAGGGCT GGAATGGGTGGCAATTATATCATATTCTGAAGA AATGATTTCTATGCAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGCGAGACGTATAGCA GCAGCTGGTTCACTACCGGTATGACGTCTGGGGCC AAGGGACCACGGTCACCGTCTCCTCA<br>SEQ ID NO: 30417 |

FIGURE 50
(Continued)

| | | AA | DIQMTQSPSSLSASVGDRVTITCQASQDIYNHLSWYQQKPGKAPKLLIYDASNWETGVPSRFSGGGSGTDFTFTISSLQPEDFATYYCQQYENLPLTFGGGTKVEIK<br><br>SEQ ID NO: 26412 | QVQLVESGGGVVQPGRSLRLSCAASGFTFSSYGMHWVRQAPGKGLEWVAIISYSGRNDFYADSVKGRFTISRDNSKNTLYLQMNSLRAEDTAVYYCARRIAAAGHYGMDVWGQGTTVTVSS<br><br>SEQ ID NO: 30418 |
|---|---|---|---|---|
| iPS:435613 | 21-225_161D11 | NA | GACATCCAGATGACCCAGTCTCCATCCTCCCTGTCTGCATCTGTAGGCGACAGAGTCACCATCACTTGCCGGGCAAGTCAGGGCATTAGAAATGATTTGGGCTGGTATCAGCAGAAACCAGGAAAGCCCCTAAGCGCCTGATCTATGCTGCATCCACTTTGCAAAGTGGGGTCCCATCGCGGTTCAGCGGCAGTGGATCTGGGACAGAATTCACTCTCACAATCGGCAGCGTGCAGCTGAAGATTTTGCAACTTATTACGGTCTACAATATAATCGTTACCCATTCACTTTTGGCCCTGGGACCAAAGTGGATATCAAA<br><br>SEQ ID NO: 26413 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTTTGGCTTGCACTGGGTCCGCCAGGCTCCAGGCAAGGGACTGGAGTGGGTGGCAGTTATATGGTTTGATGAAGTAATAAATACTATGCAGACTCCGTGAAGGGCCGAT TCACCATTTCAGAGACAATTCAAGAACACGCTGTATCTGCAAATGAACAGCCTGAGAGCCGAGGACACGGCTGTGTATTACTGTGCGAGAGAGATTGGCTGGCTCTGACTACTGGGGCCAGGGAACCCTGGTCACCGTCTCCTCA<br><br>SEQ ID NO: 30419 |
| | | AA | DIQMTQSPSSLSASVGDRVTITCRASQGIRNDLGWYQQKPGEAPKRLIYAASTLQSGVPSRFSGSGSGAEFTLTIGSVQREDFATYYGLQYNRYPFTFGRGTKVDIK<br><br>SEQ ID NO: 26414 | QVQLVESGGGVVQPGRSLRLSCAASGFTFSDFGLHWVRQAPGQGLEWVAVIWFDGSNKYYADSVKGRFTIFRDNSKNTLYLQMNSLRAEDTAVYYCAREIGWLSDYWGQGTLVTVSS<br><br>SEQ ID NO: 30420 |

FIGURE 50
(Continued)

| | | | |
|---|---|---|---|
| iPS:435615 | 21-225_161G12 | NA | GACATCCAGATGACCCAGTCTCCATCCTCCG GTCTGCATCTGTAGGAGACAGAGTCACCATCA CTTGCCGGGCAAGTCAGGACATTAGAAAGGAT TTAGGGTGGTATCAGCAGAAACCAGGGAAAG CCCCTAACCGCCTGATCTATGCTGCATCCAGTT TGCAAAGTGGGGTCCCATCAAGGTTCAGCGGC AGTGGATCTGGGACAGAATTCACTCTCACATT CAGCAGCCTGCAGCCTGAAGATTTTGCAACTT ATTACTGTCTACAGCATCATAGTTATCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGATTCACCTTAGTGACTATGTCAT GCAGTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACCGTA TAATAGTGGCTGGTACGACTACGGTATGGACGTC TGGGGCCAAGGGACCACGGTCACCGTCTCCTCA |
| | | SEQ ID NO: 26415 | SEQ ID NO: 30421 |
| | | AA | DIQMTQSPSSSRSASVGDRVTITCRASQDIRKDLG WYQQKPGKAPNRLIYAASSLQSGVPSRFSGSGS GTEFTLTFSSLQPEDFATYYCLQHHSYPRTFGQG TKVEIK | QVQLVESGGGVVQPGRSLRLSCAASGFTFSDYVM QWVRQAPGKGLEWVAVIWYDGSNKYYADSVKGR FTISRDNSKNTLYLQMNSLRAEDTAVYYCAREPYN SGWYDYGMDVWGQGTTVTVSS |
| | | SEQ ID NO: 26416 | SEQ ID NO: 30422 |
| iPS:435617 | 21-225_162F2 | NA | GACATTCAGATGACCCAGTCTCCATCCTCCCT GTGTGCATCTGTAGGAGACAGAGTCACCATCA CTTGCCGGGCAAGTCAGGGACAGGCATTAGAAAATGAT TTAGGCTGGTATCAGCAGCAGAAACCAGGGAAAG CCCCTAAGGCTTGATCAATGCTGCATCCAGT TTGCAAAGTGGGGTCCCATCAAGGTTCAGCGCGG CAGTGGATCTGGGACAGAATTCACTCTCACAA TCAGCAGCGTGCAGCCTGAAGATTTTGCAACT TATTACTGTATACAGGATAATAGTCACCCATT CACTTTCGGCCCTGGGACCAAAGTGGAAATCA AA | GAGGTGCAACTGGTGGAGTCTGGGGGAGGCCTG GTCAAGCCTGGGGGGTCCCTGAGATTCTCCTGTG CAGCCTCTGGATTCACCTTCAGTAGTTATAGCAT GAACTGGGTCCGCCAGGCTCCAGGGAAGGGCT GGAGTGGGTCTCATCCATTAGTAGTGGTAGTACG TACATATACTACCAGAGACTCAGTGAAGGGCCGAT TCACCATCTCCAGAGACAACGCCAAGAACTCACT GTATCTGCAAATGAACAGCCTGAGAGCCGAAGA CACGGCTGTGTATTACTGTGCGCGAGAGATCGGGGC AGCAGCTGGGGCCAGGGAACCCTGGTCACCGTC TCCTCA |
| | | SEQ ID NO: 26417 | SEQ ID NO: 30423 |

FIGURE 50
(Continued)

| | | | |
|---|---|---|---|
| iPS:435621 | 21-225_162H3 | AA | DIQMTQSPSSLSLLCASVGDRVTITCRASQGIRNDLG WYQQKPGKAPKRLINAASSLQSGVPSRFSGSGS GTEFTLTISSVQPEDFATYYCIQDNSHPFTFGPGT KVEIK SEQ ID NO: 26418 | EVQLVESGGGLVKPGGSLRFSCAASGFTFSSYSMN WVRQAPGKGLEWVSSISGSSTYIYYADSVKGRFTIS RDNAKNSLYLQMNSLRAEDTAVYYCARDRGSSW GQGTLVTVSS SEQ ID NO: 30424 |
| | | NA | GACATTCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCTTGATCAATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGGATAATAGTCACCCATT CACTTTCGGCCCTGGGACCAAAGTGGAAATCA AA SEQ ID NO: 26419 | GAGGTGCAACTGGTGGAGTCTGGGGGAGGCCTG GTCAAGCCTGGGGGGTCCTTGAGATTCTCCTGTG CAGCCCTCTGGATTCACCTTCAGTAGTTATAGCAT GAACCGGGTCCGCCAGGCTCCAGGGAAGGGCT GGAGTGGGTCTCATCCATTAGTGGTAGTAGTACG TACATATACTACGCAGACTCAGTGAAGGGCCGAT TCACCATCTCCAGAGACAACGCCAAGAACTCACT GTATCTGCAAATGAACAGCCTGAGAGCCGAAGA CACGGCTGTGTATTACTGCGCGAGAGATCGGGGC AGCAGCTGGGGCCAGGGAACCCTGGTCACCGTC TCCTCA SEQ ID NO: 30425 |
| | | AA | DIQMTQSPSSLSASVGDRVTITCRASQGIRNDLG WYQQKPGKAPKRLINAASSLQSGVPSRFSGSGS GTEFTLTISSLQPEDFATYYCLQDNSHPFTFGPGT KVEIK SEQ ID NO: 26420 | EVQLVESGGGLVKPGGSLRFSCAASGFTFSSYSMN RVRQAPGKGLEWVSSISGSSTYIYYADSVKGRFTIS RDNAKNSLYLQMNSLRAEDTAVYYCARDRGSSW GQGTLVTVSS SEQ ID NO: 30426 |

FIGURE 50
(Continued)

| | | | | |
|---|---|---|---|---|
| iPS:435623 | 21-225_162D5 | NA | GACATTGTGATGACCCAGTCTCCAGACTTCCG TAATGTGTCTATGGGCGAGAGGGCCATCATCA ACTTCAAGTCCAACCATAGTGTTTATACAGG TCCAACAATAATCAATACTTAGCTTGGTACCA GCGGAAACCAGGACAGCCTCCTAAGTTGCTCA TTTACCGGACATCTATCCGGAAATCCGGGGTC CCTGACCGATTCAGTGGCAGCGGGTGTGGGAC AGATTTCACTCTCACCATGCACAGCCTGCAGG CTGAAGATGTGGCAGTTTATTACTGTCAGCAA TATTATAGTACTCCTCCCACTTTCGGCGGAGG GACCAAGGTGGAGATCAAA<br><br>SEQ ID NO: 26421 | CAGGTGCAGCTGGTGCAGTCTGGGTCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGCT TGAGTGGATGGGATGGATGCACAGTGGT AACACAGGCTATGCACAGAAGTTCCAGGGCAGA GTCACCATGACCAGGAACACCTCCATAGACACA GCCTACATGGAACTGAGCAGCCTGAGTCTGAGG ACACGGCCGTGTATTTCTGTGCGTTTAGCAGTGG CTGGTACTTCTTTGACTACTGGGGCCAGGGAACC CTGGTCACCGTCTCCTCA<br><br>SEQ ID NO: 30427 |
| | | AA | DIVMTQSPDFRNVSMGERAIINFKSNHSVLYRSN NNQYLAWYQRKPGQPPKLLIYRTSIRKSGVPDR FSGSGCGTDFTLTIDSLQAEDVAVYYCQQYYSTP PTFGGGTKVEIK<br><br>SEQ ID NO: 26422 | QVQLVQSGSEVKKPGASVKVSCKASGYTFTNYDIN WVRQATGQGLEWMGWMHPNSGNTGYAQKFQGR VTMTRNTSIDTAYMELSSLSSEDTAVYFCAFSSGW YFFDYWGQGTLVTVSS<br><br>SEQ ID NO: 30428 |
| iPS:435627 | 21-225_162F6 | NA | GACATCGTGATGACCCAGTCTCCAGACTTCCT GGCTGTGTCTCTGGGCGAGAGGGCCACCATCA ACTGCAAGTCCAGCCAGAATGTTTTACACAG TCCAACAATAACAATACTACTAACTTGGTACCA GCAGAGACCAGGACAGCCTCCTAAGTTGCTCA TTTACTGGGCATCTACCCGGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCGGCAAGG GACCAAGGTGGAAATCAAA<br><br>SEQ ID NO: 26423 | CAGGTGCAGCTGGTGCAGTCTGGGGCTGAGGTG AGGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGGATGGATGCACCTAACAGTGG TAACACAGGCTATGCACAGAAGTTCCAGGGCAG ATTCACCATGACCAGGAACACCTCCATAAGCACA GCCTACATGGAGCTGAGCAGCCTGAGATCTGAG GACACGGCCGTGTATTACTGTGCCTATAGCAGTG GCTGGTACCGCTTTGACTACTGGGGCCAGGGAAC CCTGGTCACCGTCTCCTCA<br><br>SEQ ID NO: 30429 |

FIGURE 50
(Continued)

| | | | |
|---|---|---|---|
| iPS:435629 | 21-225_162H6 | AA | DIVMTQSPDSLAVSLGERATINCKSSQNVLHSSN NNNYLTWYQQRPGQPPKLLIYWASTRESGVPDR FSGSGSGTEFTLTISSLQAEDVAVYYCQQYYSTP PTFGQGTKVEIK<br>SEQ ID NO: 26424 | QVQLVQSGAEVRKPGASVKVSCKASGYTFTNYDIN WVRQATGQGLEWMGWMHPNSGNTGYAQKFQGR FTMTRNTSISTAYMELSSLRSEDTAVYYCAYSSGW YRFDYWGQGTLVTVSS<br>SEQ ID NO: 30430 |
| | | NA | GATATTGTGATGACCCAGACTCCACTCTCTCT GTCCGTCACCCCTGGACAGCCGGCCTCCATCT CCTGCAAGTCTACTCAGAGCCTCCTGCATGGT GATGGAAAGACCTATTTGTATTGGTACCTGCA GAAGCCAGGCCAGCCTCCACAACTCCTGATCT ATGAAGTTTCCAAGCCGTTCTCTGGAGTGCCA GAAAGGTTCAGTGGCAGCGGGTCAGGGACAG ATTTCACACTGAAAATCAGCGGGTGGAGCT GAGGATGTTGGGGTTTATTACTGCAAGCAAAG TATACAGCTTCCGTGGACGTTCGGCCAAGGGA CCAAGGTGGAAATCAAA<br>SEQ ID NO: 26425 | CAGGTGCAGCTGGTGGAGTCTGGGGGAGGCGTG GTCCAGCCTGGGAGGTCCCTGAGACTCTCCTGTG CAGCGTCTGGATTCACCTTCAATAACTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAAAAGGTAT AGCAGCAGTTGGAGACTACTACTACGGTATGGA CGTCTGGGGCCAAGGGACCACGGTCACCGTCTCC TCA<br>SEQ ID NO: 30431 |
| | | AA | DIVMTQTPLSLSVTPGQPASISCKSTQSLLHGDG KTYLYWYLQKPGQPPQLLIYEVSKRFSGVPERFS GSGSGTDFTLKISRVEAEDVGVYYCKQSIQLPWT FGQGTKVEIK<br>SEQ ID NO: 26426 | QVQLVESGGGVVQPGRSLRLSCAASGFTFNNYGM HWVRQAPGKGLEWVAVIWYDGSNKYYADSVKGR FTISRDNSKNTLYLQMNSLRAEDTAVYYCARKGIA AVGDYYYGMDVWGQGTTVTVSS<br>SEQ ID NO: 30432 |

FIGURE 50
(Continued)

| | | | |
|---|---|---|---|
| iPS:435635 | 21-225_163F1 | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTATGCTGCATCCAGTT GCAAAGTGGGGTCCCATCAAAGTTCAGCGGCA GTGGATCGGGACAGATTCACTCTCACCATC AGCAGCCTGCAGCCTGAAGATTTTGCAGCTTA TTACTGCCAACAGTATAATAGTTACCCATTCA CTTTCGGCCCTGGGACCCAAGTGGATGATCCAA<br/>SEQ ID NO: 26427 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTAGTAGTGGTAGT TACATATACTACGCAGACTCAGTGAAGGGCCGAT TCACCACCTCCAGAGACAACGCCAAGAACTCACT GTATCTGCAAATGAACAGCCTGAGCGCCGACGA CACGGCTGTTTATTACTGTACGCTCTATAGCAGC TGCACTATTGGGGCCAGGGAACCCTGGTCACCG TCTCCTCA<br/>SEQ ID NO: 30433 |
| | | AA | DIQMTQSPSSLSASVGDRVTITCRASQDISNYLA WFQQKPGKAPKSLIYAASSLQSGVPSKFSGSGSG TDFTLTISSLQPEDFAAYYCQQYNSYPFTFGPGT QVDAQ<br/>SEQ ID NO: 26428 | EVQLVDSGGGLVKPGGSLRLSCAASGFTFSSYSMN WVRQAPGKGLEWVSSISGSGSYIYYADSVKGRFTT SRDNAKNSLYLQMNSLSADDTAVYYCTLYSSHY WGQGTLVTVSS<br/>SEQ ID NO: 30434 |
| iPS:435637 | 21-225_163E2 | NA | GACATCCAGATGACCCAGTCTCCATCCTCCCT GTCTGCATCTGTAGGAGACAGAGTCACCATCA CTTGCCGGGCAAGTCAGGACATTAGCAACTTT TTAGGCTGGTATCAGCAGAAACCAGGGAAAG CCCCTACGCTCCTGATCTATCCTGCATCCAGTT TGCAAAGTGGGGTCCCATCAAGGTTCAGCGGC AGTGGATCTGGGACAGAATTCACTCTCACTT CAGTAGCCTGCAGCCTGAAGATTTTGCAACTT ATTACTGTCTACAGCATATAAGTAGTCACCCAT ACTTTCGGCCCTGGGACCAAAGTGGATATCAA A<br/>SEQ ID NO: 26429 | GAGGTGCAACTGGTGGAGTCTGGGGGAGGCTG GTCCAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCTCACTAGTGGGAGTTCTACT TACATATACTACGCAGACTCAGTGAAGGGCCGAT TCACCATCTCCAGAGACAACGCCAAGAACTTAGT GTATCTGCAAATGAACAGCCTGAGACCCGAGGA CACGGCTGTGTATTACTGTGCGAGAGATCGAGGC AGCCCTCTGGGGCCAGGGAACCCTGGTCACCGTCT CCTCA<br/>SEQ ID NO: 30435 |

FIGURE 50
(Continued)

| | | | | |
|---|---|---|---|---|
| iPS:435639 | 21-225_163G6 | AA | DIQMTQSPSSLSASVGDRVTITCRASQDIRNDLG WYQQKPGKAPTRLIYPASSLQSGVPSRFSGSGSG TEFTLSISSLQPEDFATYYCLQHNSHPFTFGPGTK VDIK<br><br>SEQ ID NO: 26430 | EVQLVESGGGLVQPGGSLRLSCAASGFTFSSYSMN WVRQAPGKGLEWVSSTSGSSTYIYYADSVKGRFTI SRDNAKNLVYLQMNSLRPEDTAVYYCARDRGSLW GQGTLVTVSS<br><br>SEQ ID NO: 30436 |
| | | NA | GACATCCAGATGACCCAGTCTCCATCCTCACT GTCTGCATCTGTAGGAGACAGAGTCACCATCA CTTGTCGGGCGAGTCAGGACATTAGACATTAT TTAGTCTGGTTTCAGCAGAAACCAGGAAAGC CCCTAAGTCCCGATCTATGCTGCATCCAGTTT GCTAAGTGGGGTCCCTTCAAAGTTCAGCGGCA GTGGATCTGGGACAGATTTCACTCTCACCATC AGCAGCCTGCAGCCTGAAGATTTTGCAACTTA TTACTGCCAACAGTATCATAGTTACCCGCTCA CTTTCGGCGGAGGGACCAAGGTGGGATCAA A<br><br>SEQ ID NO: 26431 | GAGGTGCAGCTGGTGGAGTCTGGGGGAGGCCTG GTCAAGCCTGGGGGGTCCCTGAGACTCTCCTGTG CAGCCTCTGGATTCACCTTCAGTAGTTATAGCAT GAGCTGGGTCCGCCAGGCTCCAGGGAAGGGGCT GGAGTGGGTCTCATCCATTAGTGGTAGTGGTGCT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGATTGAGCGGT ATGGACGTCTGGGGCCAAGGGACCACGGTCACC GTCTCCTCA<br><br>SEQ ID NO: 30437 |
| | | AA | DIQMTQSPSSLSASVGDRVTITCRASQDISNYLV WFQQKPGKAPKSLIYAASSLLSGVPSKFSGSGSG TDFTLTISSLQPEDFATYYCQQYHSYPLTFGGGT KVAIK<br><br>SEQ ID NO: 26432 | EVQLVESGGGLVKPGGSLRLSCAASGFTFSSYSMS WVRQAPGKGLEWVSSISGSSAYIYYADSVKGRFTIS RDNAKNSLYLQMNSLRAEDTAVYYCARLSGMDV WGQGTTVTVSS<br><br>SEQ ID NO: 30438 |

FIGURE 50
(Continued)

| | | | |
|---|---|---|---|
| iPS:435641 | 21-225_163F9 | NA | GACATCCAGATGACCCAGTCTCCATCCTCCCT GTCTGCATCTGTAGGAGACAGAGTCACCATCA CTTGCCGGGCAAGTCAGGACATTAGAGATGAT TTAGGCTGGTATCAGCAGAAACCAGGAAAG CCCCTAAGCGCCTGATCTATCCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGCAGCTT ATTACTGTCTACAGGATATAGTTACCCATTC ACTTTCGGCCCTGGGACCAAAGTGGATATCAA A <br> SEQ ID NO: 26433 | GAGGTGCAGCTGGTGGAGTCTGGGGGAGGCCTG GTCCAGCCGGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTACT TACATATACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATCGAGGC AGCCTCTGGGGCCAGGGAACCCTGGTCACCGTCT CCTCA <br> SEQ ID NO: 30439 |
| | | AA | DIQMTQSPSSLSASVGDRVTITCRASQDIRDDLG WYQQKPGKAPKRLIYPASSLQSGVPSRFSGSGSG TEFTLTISSLQPEDFAAYYCLQDNSYPFTFGPGTK VDIK <br> SEQ ID NO: 26434 | EVQLVESGGGLVQPGGSLRLSCAASGFTFSSYSMN WVRQAPGKGLEWVSSISGSSTYIYYADSVKGRFTIS RDNAKNSLYLQMNSLRAEDTAVYYCARDRGSLW GQGTLVTVSS <br> SEQ ID NO: 30440 |
| iPS:435643 | 21-225_163G10 | NA | GACATCCAGATGACCCAGTCTCCATCCTCCCT GTCTGCATCTGTAGGAGACAGAGTCACCATCA CTTGCCGGGCAAGTCAGGACATTAGAGATGAT TTAGGCTGGTATCAGCAGAAACCAGGGAAAG CCCCTAAGCGCCTGATCTATCCTGCATCCAGTT TGCAAAGTGGGGTCCCATCAAGGTTCAGCGGC AGTGGATCTGGGACAGCTTCACTCTCACAAT CAGCAGCCTGCAGCCTGAAGATTTTGCAACTT ATTACTGTCTACAGGATTATAGTTACCATTCA CTTTCGGCCCTGGGACCAAAGTGGATATCAAA <br> SEQ ID NO: 26435 | GAGGTGCAGTTGGTGGAGTCTGGGGGAGGCCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGCT GGAGTGGGTCTCATCCATTAGTGGTAGTAGTACT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGTGCGAGAGCCCGTATG GACGTCTGGGGCCAAGGGACCACGGTCACCGTC TCCTCA <br> SEQ ID NO: 30441 |

FIGURE 50
(Continued)

| | | | |
|---|---|---|---|
| | | AA | DIQMTQSPSSLSASVGDRVTITCRASQDIRNNLG WYQQKPGKAPKRLIYPASSLQSGVPSRFSGSGSG TEFTLTISSLQPEDFATYYCLQDYSYPFTFGPGTK VDIK | EVQLVESGGGLVKPGGSLRLSCAASGFTFSSYSMN WVRQAPGKGLEWVSSISGSSTYIYYADSVKGRFTIS RDNAKNSLYLQMNSLRAEDTAVYYCARARMDVW GQGTTVTVSS |
| | | | SEQ ID NO: 26436 | SEQ ID NO: 30442 |
| iPS:435649 | 21-225_165H2 | NA | GACATCGTGATGACCCAGTCTCCAGACTCCCT GACTGTGTCTCCGGGCGAGAGGGCCACCATCA ACTGCAAGTCCAGCCAGAGTGTTTTACACAGC TCCAACAATAAGAACTACTTAACTTGGTACCA GCAGAAACCAGGACAGCCTCCTAAACTGCTCA TTTACTGGGCATCTCACCCGAGAATCCGGGGTC CCTGTCCGATTCAGTGGCAGCGGGTCGGGGAC AGATTCACTGTCCCCATCAGCAGCATGCAGG ATGATGATGTGGCAGTTTATTACCGTCAGCAA TCTTATAGTATTCCTCCCACTTTCGGCCCCGGG ACCAACGTGGATATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCCATTATGATA TCAACTGGGTGCGACAGGCCACTGGACAAGGC TTGAGTGGATGGGATGGATGCACCTAACAGTCA TAAGACAGGCTATGCACAGAAGTTCCAGGGCAG AGTCACCATGACCAGGAACACCTCAACAGCAC AGCCTACATGGACCTCAGCAGCCTGAGATCTGAG GACACGGCCGTGTATTACTGTGCTTATAGCAGTG GCTGGTACATGTTTGACTACTGGGGCCAGGGAAC CCTGGTCACCGTCTCCTCA |
| | | | SEQ ID NO: 26437 | SEQ ID NO: 30443 |
| | | AA | DIVMTQSPDSLTVSPGERATINCKSSQSVLHSSN NKNYLTWYQQKPGQPPKLLIYWASTRESGVPVR FSGSGSGTDFTVPISSMQDDDVAVYYRQQSYSIP PTFGPGTNVDIK | QVQLVQSGAEVKKPGASVKVSCKASGYTFTHYDIN WVRQATGQGLEWVGWMHPNSHKTGYAQKFQGR VTMTRNTSNSTAYMDLSSLRSEDTAVYYCAYSSG WYMFDYWGQGTLVTVSS |
| | | | SEQ ID NO: 26438 | SEQ ID NO: 30444 |

FIGURE 50
(Continued)

| | | | |
|---|---|---|---|
| iPS:435653 | 21-225_166H12 | NA | GACATCCAGATGACCCAGTCTCCATCCTCACT GTCTACATCTGTAGGAGACAGAGTCACCATCA CTTGTCGGGCGAGTCAGGACATTAGCCATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATATAAGTTTCCCGCTCA CTTTCGGCGGAGGGACCAAGGTGGAGATCAC A |
| | | | SEQ ID NO: 26439 |
| | | AA | DIQMTQSPSSLSTSVGDRVTITCRASQDISHYLA WFQQKPGKAPKSLIYAASSLQSGVPSKFSGSGSG TDFTLTISSLQPEDFATYYCQQYNSFPLTFGGGT KVEIT |
| | | | SEQ ID NO: 26440 |
| | | NA | GAGGTGCAGCTGGTGGAGTCTGGGGGAGGCGTG GTCAAGCCTGGGGGGTCCCTGAGACTCTCCTGTG CAGCCTCTGGATTCACCTTCAGTAGCTATAGCAT GAGCTGGGTCCGCCAGGCTCCAGGGAAGGGGCT GGGGTGGGTCTCATCATTAGTGGGAGTAGTAGT TACAGTTACTACCGCAGACTCAGTGAAGGGCCGAT TCACCATCTCCAGAGACAATGCCAAGAACTCACT GTATCTGCAAATGAACAGCCTGAGAGCCGAGA CACGGCTGTGTATTACTGTGCGAGACTAACTGGC TTTGACTACTGGGGCCAGGGAACCCTGGTCACCG TCTCCTCA |
| | | | SEQ ID NO: 30445 |
| iPS:435655 | 21-225_167E2 | AA | EVQLVESGGALVKPGGSLRLSCAASGFTFSSYSMS WVRQAPGKGLGWVSSISGSSSYYADSVKGRFTI SRDNAKNSLYLQMNSLRAEDTAVYYCARLTGFDY WGQGTLVTVSS |
| | | | SEQ ID NO: 30446 |
| | | NA | GATATTGTGATGACCCAGACTCCACTCTCTCT GTCCGTCACCCCTGGACAGCCGGCCTCCATCT CCTGTAAGTCTAGTCAGAGCCTCCTGCACGGT GATGGAAGACCTATTTGTATTGGTACCTGCA GAAGCCAGGCCAGCCTCCACACTCCTGATCT ATGAAGTTTCCAAACGGTTCTCTGGAGTGCCA GATAGGTTCAGTGGCAGCGGGTCAGGGACAG ATTTCACACTGAAGATCAGCGGGTGGAGGCT GAGGATGTTGGGCTTTATCACTGCATGCAAAG CATACACAGCTTCCGTGACGTTCGGCCAAGGGA CCAAGGTGGAAATCAAA |
| | | | SEQ ID NO: 26441 |
| | | | SEQ ID NO: 30447 |

FIGURE 50
(Continued)

| | | | |
|---|---|---|---|
| iPS:435657 | 21-225_167H10 | AA | DIVMTQTPLSLSVTPGQPASISCKSSQSLLHGDG KTYLYWYLQKPGQPPHLLIYEVSKRFSGVPDRFS GSGSGTDFTLKISRVEAEDVGLYHCMQSIQLPW TFGQGTKVEIK<br>SEQ ID NO: 26442 | QVQLVESGGGVVQPGRSLRLSCAASGFTFSSFGMH WVRQAPGKGLEWVAVIWYDGTYKYYADSVKGRF TISRDNSKNTLYLQMNSLRAEDTAVYYCARVGIEV AGDYYYGMEVWGQGTTVTVSS<br>SEQ ID NO: 30448 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCACGGT GATGGAAAGACCTATTTGTATTGGTACCTGCA GAAGCCAGGCCAGTCTCCACACCTCCTGATCT ATGAAGTTTCCAAACGGTTCTCTGGAGTGCCA GATAGGTTCAGTGGCAGCGGGTCAGGGACAG ATTTCACACTGAAAATCAGCCGGGTGGAGGCT GAGGATGTTGGGCTTTATCACTGCATGCAAAG CATACAGCTTCCGTGGACGTTCGGCCAAGGGA CCAAGGTGGAAATCAAA<br>SEQ ID NO: 26443 | CAGGTGCAGTTGGTGGAGTCTGGGGGAGGCGTG GTCCAGCCTGGGAGGTCCCAGAGACTCTCCTGTG CAGCGTCTGGATTCACCTTTAGTAGCTTTGGCAT GCACTGGGTCCGCCAGGCTCCAGGCAAGGGCT GGAGTGGGTGGCAGTCATATGGTATGATGGAAG TTATAAGTACCATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGTTGGTAT AGAAGTGGCTGGTGACTACTACTACGGTATGGAA GTCTGGGGCCAAGGGACCACGGTCACCGTCTCCT CA<br>SEQ ID NO: 30449 |
| | | AA | DIVMTQTPLSLSVTPGQPASISCKSSQSLLHGDG KTYLYWYLQKPGQPPHLLIYEVSKRFSGVPDRFS GSGSGTDFTLKISRVEAEDVGLYHCMQSIQLPW TFGQGTKVEIK<br>SEQ ID NO: 26444 | QVQLVESGGGVVQPGRSQRLSCAASGFTFSSFGMH WVRQAPGKGLEWVAVIWYDGSYKYHADSVKGRF TISRDNSKNTLYLQMNSLRAEDTAVYYCARVGIEV AGDYYYGMEVWGQGTTVTVSS<br>SEQ ID NO: 30450 |

FIGURE 50
(Continued)

| | | | |
|---|---|---|---|
| iPS:435659 | 21-225_167D12 | NA | GACATCCAGATGACCCAGTCTCCATCCTCACT GTCTGCATCTGTAGGGACAGAGTCACCATCA CTTGTCGGGCGAGTCAGGGCATTAACAATTAT TTAGCCTGGTTTCAGCAGAAACCAGGGAAAGC CCCTGAGTCCTGATCTATGCTGCATCCAGTTT GCAAAGTGGGGGTCCCATCAAAGTTCAGCGGCA GTGGATCTGGGACAGATTCACTCTCACCATC AGCAGCCTGCAGCCTGAAGATTTTGCAACTTA TTTCTGCCAACAGTATAATAGTTATCCATTCAC TTTCGGCCCTGGGACCAAAGTGGATATCAAA<br>SEQ ID NO: 26445 |
| | | AA | DIQMTQSPSSLSASVGDRVTITCRASQGINNYLA WFQQKPGKAPESLIYAASSLQSGVPSKFSGSGSG TDFTLTISSLQPEDFATYFCQQYNSYPFTFGPGTK VDIK<br>SEQ ID NO: 26446 |
| | | | GAGGTGCAGCTGTTGGAGTCTGGGGGAGGCTTG GTACAGCCGGGGGGGTCCCTGAGACTCTCCTGTG CAGCCTCTGGATTCACCTTTAGTAGCTATGTCAT GAGCTGGGTCCGCCAGGCTCCAGGGAAGGGGCT GGAGTGGGTCTCAGCTATGAGTGGTAGTGGTGGT AGAACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTGTATTACTGTGCGAAGTATACCTG GAACGGCTACTGGGGCCAGGGAACCCTGGTCAC CGTCTCCTCA<br>SEQ ID NO: 30451 |
| | | | EVQLLESGGGLVQPGGSLRLSCAASGFTFSSYVMS WVRQAPGKGLEWVSAMSGSGGRTYYADSVKGRF TISRDNSKNTLYLQMNSLRAEDTAVYYCAKYTWN GYWGQGTLVTVSS<br>SEQ ID NO: 30452 |
| iPS:435663 | 21-225_169B1 | NA | GACATCCAGATGACCCAATCTCCATCCTCCCT GTCTGCATCTGTAGGAGACAGAGTCACCATCA CTTGCCGGGCTAGTCAGGGCATTAGAAATGAT TTAGGCTGGTATCAGCAGAAACCAGGGAAAG CCCCTAAGCGCCTGATCGGTGCTGAATCCAGT TTGCAAAGTGGGGTCCCATCAAGGTTCAGCGG CAGTGGATCTGGGACAGAATTCACTCTCACAA TCAGCGGCCTGCAGCCTGAAGATTTTGCAACT TATTACTGTCTACAGCATTATAGTTACCCGCTC ACTTTCGGCGGAGGGACCAAAGTGGAGATCA AA<br>SEQ ID NO: 26447 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAGGGGCCGA TTCACCATCTCCAGAGACAATTCCAAGAACACGC TGTATCTGCAAATGAACAGCCTGAGAGCCGAAG ACACGGCTGTGTATTACTGTGCGAGAGATCCCTT ACGTGGATACAATGACCCGGTTATGGACTACTGG GGCCAGGGAACCCTGGTCACCGTCTCCTCA<br>SEQ ID NO: 30453 |

FIGURE 50
(Continued)

| | | | |
|---|---|---|---|
| | | AA | DIQMTQSPSSLSASVGDRVTITCRASQGIRNDLG WYQQKPGKAPKRLIGAESSLQSGVPSRFSGSGSG TEFTLTISGLQPEDFATYYCLQHYSYPLTFGGGT KVEIK | QVQLVESGGGVVQPGRSLRLSCAASGFTFSSYGMH WVRQAPGKGLEWVAVIWYDGSNKYYADSVRGRF TISRDNSKNTLYLQMNSLRAEDTAVYYCARDPLRG YNDPVMDYWGQGTLVTVSS |
| | | | SEQ ID NO: 26448 | SEQ ID NO: 30454 |
| iPS:435665 | 21-225_169F2 | NA | GACATCGTGATGACCCAGTCTCCAGACTCCCT GGCTGTGTCTCTGGGCGAGAGGGCCACCATCA ACTGCAAGTCCAGCCAGAGTGTTTATACATC TCCAACAATAAAAACTACTTAGCTTGGTACCA GCAGAAACCAGGACAGCCTCCTAAACTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATCGTGTCCCACCTTCGGCCAAGGGAC ACGACTGGAGATTAAA | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTACTG GAGTTGGATCCGGCAGCCCGCCGGGAAGGGACT GGAGTGGATTGGGCGTATCGATACCAGTGGGATC ACCAACTACAACCCCTCCCTCAAGAGTCGAGTCA CCATGTCAATAGACACGTCCAAGAGCCAGATCTC CCTGAAGCTGAGCTCTGTGACCGCCGCGGACACG GCCGTGTATTACTGTGCGAGAGAGGAGGAGTG GGAGCTACTACTTTGACTACTGGGGCCAGGGAA CCCTGGTCACCGTCTCCTCA |
| | | | SEQ ID NO: 26449 | SEQ ID NO: 30455 |
| | | AA | DIVMTQSPDSLAVSLGERATINCKSSQSVLYISN NKNYLAWYQQKPGQPPKLLIYWASTRESGVPD RFSGSGSGTDFTLTISSLQAEDVAVYYCQQYYR APTFGQGTRLEIK | QVQLQESGPGLVKPSETLSLTCTVSGGSISSYYWSW IRQPAGKGLEWIGRIDTSGITNYNPSLKSRVTMSIDT SKSQISLKLSSVTAADTAVYYCAREGGVGATYFDY WGQGTLVTVSS |
| | | | SEQ ID NO: 26450 | SEQ ID NO: 30456 |

FIGURE 50
(Continued)

| | | | | |
|---|---|---|---|---|
| iPS:435667 | 21-225_169E3 | NA | GACATTGTGATGACTCAGTCTCCACTCTCCCTG CCCGTCACCCCTGGAGAGCCGGCCTCCATCTC CTGCAGGTCAGTCAGAGCCTCCTGCATAATA ATGGATACAAGTATTTGGATTGGTACCTGCAG AAGCCAGGGCAGTCTCCACAGCTCCTGATCTA TTTGGGTTCTAATCGGGCCTCCGGGGTCCCTG ACAGGTTCAGTGCCAGTGGATCAGGCACAGAT TTTACACTGAAAATCAGCAGAGTGGAGGCTGA GGATGTTGGGGTTTATTACTGCATGCAAGTTC TACAAACTCCGTGGACGTTCGGCCAAGGGACC AAGGTGGAAATCAAA SEQ ID NO: 26451 | GAGGTGCAACTGGTGGAGTCTGGGGGAGGCTTG GTACAGCCGGGGGGGTCCCTGAGACTCTCCTGTG CAGCCTCAGGATTCACCTTCAGTGGCCATAGCAT GAACTGGGTCCGCCAGGCTCCAGGGAAGGGCT GGAGTGGGTTGCATACATTAGCCTTAGTGGTAGT ACCATAAAGTACGCAGACTCTGTGAAGGCCGA TTCACCATCTCCAGAGACAATGCCAGGACTCAC TGTATCTGCAAATGAACAGCCTGAGAGACGAGG ACACGGCTGTGTATTACTGTGCGAGAAGGGGAT TACTGTGGTTCGGAATGAGGACGGTTTGGACGTC TGGGGCCAAGGGACCACGGTCACCGTCTCCTCA SEQ ID NO: 30457 |
| | | AA | DIVMTQSPLSLPVTPGEPASISCRSSQSLLHNGY KYLDWYLQKPGQSPQLLIYLGSNRASGVPDRFS ASGSGTDFTLKISRVEAEDVGVYYCMQVLQTPW TFGQGTKVEIK SEQ ID NO: 26452 | EVQLVESGGGLVQPGGSLRLSCAASGFTFSGHSMN WVRQAPGKGLEWVAYISLSGSTIKYADSVKGRFTI SRDNARDSLYLQMNSLRDEDTAVYYCARRGITVV RNEDGLDVWGQGTTVTVSS SEQ ID NO: 30458 |
| iPS:435669 | 21-225_169F9 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTTTGCTGCATCCAGTT TGCAAAGTGGGGTCCCATCAAGGTTCAGCGGC AGTGGATCTGGGACAGATTCACTCTCACAAT CAGCAGCCTGCAGCCTGAAGATTTTGCAACTT ATTACTGTCTACAGCATTATAGTTACCCGCTCA CTTTCGGCGGAGGGACCAAGGTGGAGATCAA A SEQ ID NO: 26453 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTACTATGCAT GCACTGGGTCCGCCAGGCTCCAGGCAAGGGCT GGAGTGGGTGTCAATTATATGGATGATGGAACT AATAAATACTATGCAGACTCCGTGAAGGGCCGA TTCACCATCTCCAGAGACAATTCCAAGAACACGC TGTATCTGCAACTGAACAGCCTGAGAGCCGAGG ACACGGCTGTGTATTACTGTGCGCAGAGATCCCTT ACGTGGATACAATGACCGGTTATGACTACTGG GGCCAGGGAACCCTGGTCACCGTCTCCTCA SEQ ID NO: 30459 |

FIGURE 50
(Continued)

| | | | |
|---|---|---|---|
| iPS:435671 | 21-225_169H5 | AA | DIQMTQSPSSLSASVGDRVTITCRASQGIRNDLG WYQQKPGKAPKRLIFAASSLQSGVPSRFSGSGSG TEFTLTISSLQPEDFATYYCLQHYSYPLTFGGGT KVEIK<br><br>SEQ ID NO: 26454 |
| | | | QVQLVESGGGVVQPGRSLRLSCAASGFTFSTYGMH WVRQAPGKGLEWVSIIWYDGTNKYYADSVKGRFT ISRDNSKNTLYLQLNSLRAEDTAVYYCARDPLRGY NDPVMDYWGQGTLVTVSS<br><br>SEQ ID NO: 30460 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTATACATC TCCAACAATAAAAACTACTTAGCTTGGTACCA GCAGAAACCAGGACAGCCTCCTAAACTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATCGTGTCCCACCTTCGGCCAAGGGAC ACGACTGGAGATTAAA<br><br>SEQ ID NO: 26455 |
| | | | CAGGTGCAGCTGCAGGAGTCGGGCCAGGACTG GTGAAGCCTTCGGAGACCCTGTCCTCACCTGCA CTGTCTCTGGTGGCTCCATCAGTAGTTACTACTG GAGTTGGATCCGGCAGCCCGCCGGGAAGGGACT GGAGTGGATTGGGCGTATCGATACCAGTGGGATC ACCAACTACAACCCCTCCCTCAAGAGTCGAGTCA CCATGTCAGTAGACACGTCCAAGAGCCAGATCTC CCTGAAGCTGAGCTCTGTGACCGCCGCGGACACG GCCGTGTATTACTGTGCGAGAGAGGAGGAGTG GGAGCTACTACTTTGACTACTGGGGCCAGGGAA CCCTGGTCACCGTCTCCTCA<br><br>SEQ ID NO: 30461 |
| | | AA | DIVMTQSPDSLAVSLGERATINCKSSQSVLYISN NKNYLAWYQQKPGQPPKLLIYWASTRESGVPD RFSGSGSGTDFTLTISSLQAEDVAVYYCQQYYR APTFGQGTRLEIK<br><br>SEQ ID NO: 26456 |
| | | | QVQLQESGPGLVKPSETLSLTCTVSGGSISSYYWSW IRQPAGKGLEWIGRIDTSGITNYNPSLKSRVTMSVD TSKSQISLKLSSVTAADTAVYYCAREGGVGATYFD YWGQGTLVTVSS<br><br>SEQ ID NO: 30462 |

FIGURE 50
(Continued)

| | | | | |
|---|---|---|---|---|
| iPS:435673 | 21-225_169E6 | NA | GACATTGTGATGACTCAGTCTCCACTCTCCCTG CCCGTCACCCCTGGAGAGCCGGCCTCCATCTC CTGCAGGTCTAGTCAGAGCCTCCTGCATAATA ATGGATACAAGTATTTGGATTGGTACCTGCAG AAGCCAGGGCAGTCTCCACAGTCTCCTGATCTA TTTGGGTTCTAATCGGGCCTCCGGGGTCCCTGA ACAGGTTCAGTGCCAGTGGATCAGGCACAGAT TTTACACTGAAAATCAGCAGAGTGGAGGCTGA GGATGTTGGGGTTTATTACTGCATGCAAGTTC TACAAACTCCGTGACGTTCGGCCAAGGGACC AAGGTGGAAATCAAA<br><br>SEQ ID NO: 26457 | GAGGTGCAACTGGTGGAGTCTGGGGGAGGCTTG GTACAGCCTGGGGGGTCCCTGAGACTCTCCTGTG CAGCCTCAGGATTCACCTTCAGTGGCCATAGCAT GAACTGGGTCCGCCAGGCTCCAGGGAAGGGCT GGAGTGGGTTGCATACATTAGCATTAGTAGTAGT ACCATAAAGTACGCAGACTCTGTGAAGGGCCGA TTCACCATCTCCAGAGACACAATGCCAGGACTCAC TGTATCTGCAAATGAACAGCCTGAGAGACGAGG ACACGGCTGTGTATTACTGTGCGAGAAGGGGAT TACTGTGGTTTCGGAATGAGGACGGTTTGGACGTC TGGGGCCAAGGGACCACGGTCACCGTCTCCTCA<br><br>SEQ ID NO: 30463 |
| | | AA | DIVMTQSPLSLPVTPGEPASISCRSSQSLLHNNGY KYLDWYLQKPGQSPQLLIYLGSNRASGVPDRFS ASGSGTDFTLKISRVEAEDVGVYYCMQVLQTPW TFGQGTKVEIK<br><br>SEQ ID NO: 26458 | EVQLVESGGGLVQPGGSLRLSCAASGFTFSGHSMN WVRQAPGKGLEWVAYISISSTIKYADSVKGRFTIS RDNARDSLYLQMNSLRDEDTAVYYCARRGITVVR NEDGLDVWGQGTTVTVSS<br><br>SEQ ID NO: 30464 |
| iPS:435675 | 21-225_169D7 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCTCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATCATAGTTGCCCGTG GACGTTCGGCCAAGGGACCAAGGTGGAAATC AAA<br><br>SEQ ID NO: 26459 | CAGGTGCAGCTGCAGGAGTCGGGCCCAGGACTG GTGAAGCCTTCGGAGACCCTGTCCCTCACCTGCA CTGTCTCTGGTGGCTCCATCAGTAGTTACTACTG GAGCTGGATCCGGCAGCCCGCCGGGAAGGACT GGAGTGGATTGGGCGTATCTATCCAAGAGTCGAGTGCA CCAACTACAACCCCTCCCTCAAGAGTCGAGTCA CCATGTCAGTAGACACGTCCAAGAACCAGTTCTC CCTGAAGCTGAGCTCTGTGACCGCCGCGGACACG GCCGTGTATTCTGTGCGAAAGTCGGGAGGTACT ACTACGGTATGGACGTCTGGGGCCAAGGGACCA CGGTCACCGTCTCCTCA<br><br>SEQ ID NO: 30465 |

FIGURE 50
(Continued)

| | | | |
|---|---|---|---|
| iPS:435677 | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHHSCPWTFGQG TKVEIK<br>SEQ ID NO: 26460 | QVQLQESGPGLVKPSETLSLTCTVSGGSISSYYWTW IRQPAGKGLEWIGRIYTSGSTNYNPSLKSRVTMSVD TSKNQFSLKLSSVTAADTAVYFCAKVGRYYYGMD VWGQGTTVTVSS<br>SEQ ID NO: 30466 |
| | 21-225_169C10 | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGCCTGGTTTCAGCAGAAACCAGGGAAAGC CCCTAAGTCCCTAATCTTTCTGCATCCAGTTT GCAAAGTGGGGTCCCATCAAAATTCAGCGGCA GTGGATCTGGGACAGATTTCAATCTCACCATC AGCAGCCTGCAGCCTGAAGATTTTGCAACTTA TTACTGCCAACAATCTGATAGTTACCCTCTCAC TTTCGGCGGAGGGACCAAGGTGGAGATCAAA<br>SEQ ID NO: 26461 | CAGGTGCAGCTGGTGCAGTCTGGGGCTGAGGTG AAGAAGCCTGGGGCCTCAGTGAGGGTCTCTGC AAGGCTTCTGATACACCTTCACCGGCTACTTA TGCACTGGGTGCGACAGGCCCCTGGACAAGGGC TTGAGTGGATGGGATGGATCAAGCTAAGAGTG GTGCACAAAACTCTGCACAGAGGTTTCAGGGCA GGGTCACCATGACCAGGACACGTCCATCAACA CAGCCTACATGGAGCTGAACAGGCTGAGATCTG ACGACACGGCCGTGTATTACTGTGCGAGAGGG GGACTACGGTGGCTACGTGGGGGGTCTTTGACTA CTGGGGCCAGGGAACCCTGGTCACCGTCTCCTCA<br>SEQ ID NO: 30467 |
| | | AA | DIQMTQSPSSLSASVGDRVTITCRASQDISNYLA WFQQKPGKAPKSLIFSASSLQSGVPSKFSGSGSG TDFNLTISSLQPEDFATYYCQQSDSYPLTFGGGT KVEIK<br>SEQ ID NO: 26462 | QVQLVQSGAEVKKPGASVRVSCKASGYTFTGYFM HWVRQAPGQGLEWMGWIKPKSGGTNSAQRFQGR VTMTRDTSINTAYMELNRLRSDDTAVYYCARGGT TVATWGFDYWGQGTLVTVSS<br>SEQ ID NO: 30468 |

FIGURE 50
(Continued)

| | | | |
|---|---|---|---|
| iPS:435679 | 21-225_169D10 | NA | GACATCCAGATGACCCAGTCTCCATCTTCACTGTCTGCATCTGTAGGAGACAGAGTCACCATCACTTGTCGGGCGAGTCAGGACATTAGCAATTATTTAGCCTGGTTTCAGCAGAAACCAGGGAAAGCCCCTAAGTCCCTGATCTATGCTGCATCCAGTTTGCAAAGTGGGGTCCCATCAAAGGTTCAGCGGCAGTGGATCTGGGACAGATTTCACTCTCACCATCAGCAGCCTGCAGCCTGAAGATTTTGCAACTTATACTGCCAACAGTATCATAGTTACCCATTCACTTTCGGCCCTGGGACCAAAGTGGATATCAAA<br><br>SEQ ID NO: 26463 | GAGGTGCAGTTGTTGGAGTCTGGGGGAGGCTTGGTGCAGTCTGGGGGGTCCCTGAGACTCTCCTGTGCAGCCTCTGGATTCACCTTTAGCAGTCATGTCATGAGTTGGGTCCGCCAGGCTCCAGGGAAGGGGCTGGAGTGGGTCTCAGCTATTAGTGGTAGTGGTAGTAGAATATACTACGCGGACTCCGTGAAGGGCCGGTTCACCATCTCCAGAGACAATTCCAAGAACACGCTGTATCTGCAAATGAACAGCCTGAGAGCCGAGGACACGGCCTTATATTACTGTGCGAGAGTGGCTTTCTTTGACTATTGGGGCCAGGGAACCCTGGTCACCGTCTCCCTCA<br><br>SEQ ID NO: 30469 |
| | | AA | DIQMTQSPSSLSASVGDRVTITCRASQDISNYLAWFQQKPGKAPKSLIYAASSLQSGVPSKFSGSGSGTDFTLTISSLQPEDFATYYCQQYHSYPFTFGPGTKVDIK<br><br>SEQ ID NO: 26464 | EVQLLESGGGLVQSGGSLRLSCAASGFTFSSYVMSWVRQAPGKGLEWVSAISGSGSRIYYADSVKGRFTISRDNSKNTLYLQMNSLRAEDTALYYCARVAFFDYWGQGTLVTVSS<br><br>SEQ ID NO: 30470 |
| iPS:435681 | 21-225_169D11 | NA | GACATCCAGATGACCCAGTCTCCATCCTCCTGTCTGCATCTGTAGGAGACAGAGTCACCATCACTTGCCGGGCAAGTCAGGGCATTAGAGATGATTTAGGCTGGTATCAACAGAAACCAGGGAAAGTCCCTAAGCGCCTGATATATGCTGCATCCAGTTTGCAAAGTGGGGTCCCATCAAGGTTCAGCGGCAGTGGATCTGGGACAGATTCACTCTCACAACTCAGCAGCCTACAGCCTGAAGATTTTGCAACTTATTACTGTCTTCAGCATTATAGTTACCCTCGGACGTTCGGCCAAGGGACCAAGGTGGAAATCAAA<br><br>SEQ ID NO: 26465 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGTCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAATTGAACAGCCTGAGAGCCGAGGACACGGCTGTGTATTACTGTGCGAGAGAAGGTATAGCAGTGGCTGGTACGACTACGGTATGGACGTCTGGGGCCAAGGGACCACGGTCACCGTCTCCTCA<br><br>SEQ ID NO: 30471 |

FIGURE 50
(Continued)

| | | AA | DIQMTQSPSSLSASVGDRVTITCRASQGIRDDLG WYQQKPGKVPKRLIYAASSLQSGVPSRFSGSGS GTEFTLTISSLQPEDFATYYCLQHYSYPRTFGQG TKVEIK<br>SEQ ID NO: 26466 | QVQLVESGGGVVQPGRSLRLSCAASGFTFSDYVM HWVRQAPGKGLEWVAVIWYDGSNKYYADSVKGR FTISRDNSKNTLYLQLNSLRAEDTAVYYCARERYSS GWYDYGMDVWGQGTTVTVSS<br>SEQ ID NO: 30472 |
|---|---|---|---|---|
| iPS:435683 | 21-225_170A1 | NA | GAGATTGTGATGACCCAGACTCCACTCTCCT GTCCGTCACCCCTGGACAGCCGGCCTCCATCT CCTGCAAGTCTAGTCAGAGCCTCCTGCATGGT GATGGAAAGAACCTATTTGTTTGGTACCTGCA GAAGCCAGGCCAGTCCTCCACAGGTCCTGATCT ATGAAGTTTCCAACCGTTTCTCTGGAGTGCCA GATAGGTTCAGTGGCAGCGGGTCAGGGACAG ATTTCACACTGAAAATCAGCCGGGTGGAGGCT GAGGATGTTGGGGTTTATTACTGCATGCAAAG TATTCAGCTTCCGTGGACGTTCGGCCAAGGGA CCAAGGTGGAAATCAAA<br>SEQ ID NO: 26467 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGGCT GGAGTGGGTGGCAATTATATGTATGATGGAAGT TATAAATACTATGCAGATTCCGTGAAGGGCCGAT TCACCATCTCCAGAGACAATTCCAAGAACACACT GTATCTGCAAATGAACAGCCTGAGAGCCGAGGA CACGGCTGTGTATTACTGTGCGAGAGATGCCCAC GATTTTTGGAGTGGTTACTTTGACTCCTGGGGCC AGGGAACCCTGGTCACCGTCTCCTCA<br>SEQ ID NO: 30473 |
| | | AA | EIVMTQTPLFLSVTPGQPASISCKSSQSLLHGDGK TYLFWYLQKPGQPPQVLIYEVSNRFSGVPDRFSG SGSGTDFTLKISRVEAEDVGVYYCMQSIQLPWTF GQGTKVEIK<br>SEQ ID NO: 26468 | QVQLVESGGGVVQPGRSLRLSCAASGFTFSSYGMH WVRQAPGKGLEWVAIIWYDGSYKYYADSVKGRFT ISRDNSKNTLYLQMNSLRAEDTAVYYCARDAHDF WSGYFDSWGQGTLVTVSS<br>SEQ ID NO: 30474 |

FIGURE 50
(Continued)

| | | | |
|---|---|---|---|
| iPS:435685 | 21-225_170E1 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATCATAGTTACCCATTCA CTTTCGGCCCTGGGACCAAAGTGGATATCAAA SEQ ID NO: 26469 | GAGGTGCAGTTGTTGGAGTCTGGGGGAGGCTTGG TACAGCCTGGGGGGTCCTGAGACTCTCCTGTGC AGCCTCTGATTCACCTTTAGCAGCTATGTCATG AGTTGGGTCCGCCAGGCTCCAGGGAAGGGGCTG GAGTGGGTCTCAGCTATTAGTGGTAGTGGTAATA GAATATACTACGCAGACTCCGTGAAGGGCCGGTT CACCATCTCCAGAGACAATTCCAAGAACACGCTG TATCTGCAAATGAACAGCCTGAGAGCCGAGGAC ACGGCCTTATATTACTGTGCGAGAGTGGCTTTCT TTGACTATTGGGGCCAGGGAACCCTGGTCACCGT CTCCTCA SEQ ID NO: 30475 |
| | | AA | DIQMTQSPSSLSASEGDRVTITCRASQGISNYLA WFQQKPGKAPKSLIYAASSLQSGVPSKFSGSGSG TDFTLTISSLQPEDFATYYCQQYHSYPFTFGPGT KVDIK SEQ ID NO: 26470 | EVQLLESGGGLVQPGGSLRLSCAASGFTFSSYVMS WVRQAPGKGLEWVSAISGSGNRIYADSVKGRFTI SRDNSKNTLYLQMNSLRAEDTALYYCARVAFFDY WGQGTLVTVSS SEQ ID NO: 30476 |
| iPS:435687 | 21-225_170H1 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTATTGTCTACAGCATAGTAGTAACCCGTG GACGTTCGGCCAAGGGACCAAGGTGGAAAGC AAA SEQ ID NO: 26471 | CAGGTGCAGCTGCAGGAGTCGGGCCCAGGACTG GTGAAGCCTTCGGAGACCCTGTCCTCACCTGCA CTGTCTCTGGTGGCTCCATCAGTAGTTATTACTGG AGCTGGATCCGGCAGCCCCCAGGGAAGGGACTG GAGTGGATTGGGCGTATCTATACCAGTGGGAGCA CCAACTACAACCCCTCCCTCAAGAGTCGAGTCAC CATGTCAGTAGACACGTCCAAGAACCAGTTCTCC CTGAAGCTGAGCTCTGTGACCGCCGCGGACACG GCCGTGTATTACTGTGCGAGAGTCGGGAGGTACT ACTATGGTATGGACGTCTGGGGCCAAGGGACCA CGGTCACCGTCTCCTCA SEQ ID NO: 30477 |

FIGURE 50
(Continued)

| | | | |
|---|---|---|---|
| | | AA | DIQMTQSPSSLSASVGDRVTITCRASQGIRNDLG WYQQKPGKAPKRLIYATSSLQSGVPSRFSGSGSG TEFTLTISSLQPEDFATYYCLQHSSNPWTFGQGT KVESK | QVQLQESGPGLVKPSETLSLTCTVSGGSISSYYWSW IRQPAGKGLEWIGRIYTSGSTNYNPSLKSRVTMSVD TSKNQFSLKLSSVTAADTAVYYCARVGRYYYGMD VWGQGTTVTVSS |
| | | | SEQ ID NO: 26472 | SEQ ID NO: 30478 |
| iPS:435689 | 21-225_170F3 | NA | GACATCCAGATGACCCAGTCTCCATCCTCCCT GTCTGCTTCTGTACAAGACAGAGTCACCATCA CTTGCCGGGCAAGTCGGGGCATTAGAAATGAT TTAGGCTGGTATCAGCAGAAACCAGGAAAAG CCCCTAAGCGCCTGATCTATGCTGCATCCAGT TTGCAAAGTGGGGGTCCCATCCAAGGTTCAGCGG CAGTGGATCTGGGACAGAATTCACTCTCACAA TCAACAGCCTGCAGCCTGAAGATTTTGCAACT TATTACTGTCTACAGCATTATAGTAACCCTCGG ACGTTCGGCCAAGGGACCAAGGTGGAAATCA AA | CAGGTGCAGCTGGTGGAATCTGGGGGAGGCGTG GTCCAGCCTGGGAGGTCCCTGAGACTCTCCTGTG CAGCGTCTGGATTCTCCTTCAGTGACTATGTCAT GCACTGGGTCCGCCAGGCTCCAGGCAAGGGGCT GGAGTGGGTGGCAGTTATATAGACTCCGTGAAGGGCCGA AATAAATACTATGAAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGACGTA TAGCAGCAGCTGGTACGACTACGGTATGGACGTC TGGGGCCAAGGGACCACGGTCACCGTCTCCTCA |
| | | | SEQ ID NO: 26473 | SEQ ID NO: 30479 |
| | | AA | DIQMTQSPSSLSASVQDRVTITCRASRGIRNDLG WYQQKPGKAPKRLIYAASSLQSGVPSRFSGSGS GTEFTLTINSLQPEDFATYYCLQHYSYPRTFGQG TKVEIK | QVQLVESGGGVVQPGRSLRLSCAASGFSFSDYVMH WVRQAPGKGLEWVAVIWYDGSNKYYEDSVKGRF TISRDNSKNTLYLQMNSLRAEDTAVYYCARETYSS SWYDYGMDVWGQGTTVTVSS |
| | | | SEQ ID NO: 26474 | SEQ ID NO: 30480 |

FIGURE 50
(Continued)

| | | | | | | |
|---|---|---|---|---|---|---|
| iPS:435693 | 21-225_170G4 | NA | GACATCCAGATGACCCAGTCTCCATCCCCTGTCTGCATCTGTAGGAGACAGAGTCACCATCACTTGCCGGGCAAGTCAGGGCATTAGAAATGATTTAGGCTGGTATCACCAGAAACCGGGAAAGCCCCTAAGGCGCCTGATCTATGCTGCATCCACTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATTATAGTTACCCGCTCACTTTCGGCGGAGGGACCAAGGTGGAGATCAAA | SEQ ID NO: 26475 | CAGGTGCAGCTGGTGGAGTCTGGGGGAGGCGTGGTCCAGCCTGGGAGGTCCCTGAGACTCTCCTGTACAGCGTCTGGATTCACCTTCAGTACTTATGGCATGCACTGGGTCCGCCAGGCTCCAGGCAAGGGCTGGAGTGGGTGTCAATTATATGGTATGATGGAACTAATAAATACTATGCAGACTCCGTGAAGGGCCGATTCACCATCTCCAGAGACAATTCCAAGAACACGCTGTTTCTGCAACTGAACAGCCTGAGAGCCGAGGACACGGCTATACAATGACCCGGTTATGGACTACTGGGGCCAGGGAACCCTGGTCACCGTCTCCTCA | SEQ ID NO: 30481 |
| | | AA | DIQMTQSPSSLSASVGDRVTITCRASQGIRNDLGWYHQKPGKAPKRLIYAASTLQSGVPSRFSGSGSGTEFTLTISSLQPEDFATYYCLQHYSYPLTFGGGTKVEIK | SEQ ID NO: 26476 | QVQLVESGGGVVQPGRSLRLSCTASGFTFSTYGMHWVRQAPGKGLEWVSIIWYDGTNKYYADSVKGRFTISRDNSKNTLFLQLNSLRAEDTAMYYCARDPLRGYNDPVMDYWGQGTLVTVSS | SEQ ID NO: 30482 |
| iPS:435695 | 21-225_170D5 | NA | GACATCCAGATGACCCAGTCTCCATCCCCTGTCTGCATCTGTGGGAGACAGAGTCACCATCACTTGCCGGGCAAGTCAGGGCATTAGAAATGATTTAGGCTGGTATCAGCAGAAACCAGGGAAAGCCCCTAAACACCTGATCTATGCTGCATCCAGTTTGCAAAATGGGGTCCCATCAAGGTTCAGCGGCAGTGGATCTGGGACAGATTTCACTCTCACAATCAGCAGCCTGCAGCCTGAAGATTTTGCAACTTATTACTGTCTACAGCATTATAGTTTCCCGCTCACTTTCGGCGGAGGGACCAAGGTGGAGATCA | SEQ ID NO: 26477 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGCCATGCACTGGGTCCGCCAGGCTCCAGGCAAGGGCTGGAGTGGGTGGCAATTATATGGTATGATGGAAGCTAATAAATACTATGCAGACTCCGTGAAGGGCCGATTCACCATCTCCAGAGACAATTCCAAGAACACGCTGTATCTGCAACTGAACAGCCTGAGAGCCGAGGACACGGCTGTGTATTACTGCGCGAGATCCCCTTACGTGGATACAATGACCGGTTATGACTACTGGGGCCAGGGAACCCTGGTCACCGTCTCCTCA | SEQ ID NO: 30483 |

FIGURE 50
(Continued)

| | | | | |
|---|---|---|---|---|
| iPS:435697 | 21-225_170G5 | AA | DIQMTQSPSSLSASVGDRVTITCRASQGIRNDLG WYQEKPGKAPKHLIYAASSLQNGVPSRFSGSGS GTEFTLTISSLQPEDFATYYCLQHYSFPLTFGGGT KVEIK<br><br>SEQ ID NO: 26478 | QVQLVESGGGVVQPGRSLRLSCAASGFTFSSYGMH WVRQAPGKGLEWVAIHWYDGTNKYYADSVKGRF TISRDNSKNTLYLQLNSLRAEDTAVYYCARDPLRG YNDPVMDYWGQGTLVTVSS<br><br>SEQ ID NO: 30484 |
| | | NA | GACATCCAGATGACCCAGTCTCCATCCTCCCT GTCTGCATCTGTAGGAGACAGAGTCACCATCA CTTGCCGGGCAAGTCAGGGCATTAGAACTGAT TTAGGCTGGTTTCAGCAGAAACCAGGGAAAGC CCCTAAGCACCTGATCTATACTGCATCCAGTTT GCAAAGTGGGGTCCCATCAAGGTTCAGCGGCA GTGGATCTGGGACAGAATTCACTCTCACGATC AGCAGCCTGCAGCCTGAAGATTTTGCAACTTA TTACTGTCTACAGCATTATAGTTACCCGCTCAC TTTCGGCGGAGGGACCAAGGTGGAGATCAAA<br><br>SEQ ID NO: 26479 | CAGGTGCAGCTGGTGGAGTCTGGGGGAGGCGTG GTCCAGCCTGGGGGGTCCCTGAGACTCTCCTGTG CAGCGTCTGGCTTCACCTTCAGTACTACTATGCAT GCACTGGGTCCGCCAGGCTCCAGGCAAGGGGCT GGAGTGGGTGACAATTATATGTATGATGGGACT AATAAATACTATGCAGACTCCGTGAAGGGCCGA TTCACCATCTCCAGAGACAATTCCAAGAGCACGC TGTATCTGCAAATGAACAGCCTGAGAGCCGAGG ACACGGCTGTGTATTTCTGTGCGAGAGATCCCTT AGTGGATACAATGACCCGGTTATGGACTACTGG GGCCAGGGAACCCTGGTCACCGTCTCCTCA<br><br>SEQ ID NO: 30485 |
| | | AA | DIQMTQSPSSLSASVGDRVTITCRASQGIRTDLG WFQQKPGKAPKRLIYTASSLQSGVPSRFSGSGSG TEFTLTISSLQPEDFATYYCLQHYSYPLTFGGGT KVEIK<br><br>SEQ ID NO: 26480 | QVQLVESGGGVVQPGGSLRLSCAASGFTFSTYGMH WVRQAPGKGLEWVTIIWYDGTNKYYADSVKGRFT ISRDNSKSTLYLQMNSLRAEDTAVYFCARDPLRGY NDPVMDYWGQGTLVTVSS<br><br>SEQ ID NO: 30486 |

FIGURE 50
(Continued)

| | | | | |
|---|---|---|---|---|
| iPS:435699 | 21-225_170D6 | NA | GACATCCAGATGACCCAGTCTCCATCCTCTCT GTCTGCATCTGTAGGAGACAGAGTCGCCATCA CTTGTCGGGCGAGTCAGGACATTGGCAATTGT TAGCCTGGTTTCAGCAGAAACCAGGAAAGC CCCTAAGTCCCTGATCTATTCTGCGTCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAATCTGATAGTTACCCTCTCAC TTTCGGCGGAGGGACCAAGGTGGAGATCAAA | CAGGTGCAGCTGGTGCAGTCTGGGGCTGAGGTG AAGAAGCCTGGGGCCTCAGTGAGGGTCTCCTGC AAGGCTTCTGGATACACCTTCACCGGCTACTTTA TACACTGGGTGCGACAGGCCCCTGGACAAGGGC TTGAGTGGATGGGATGGATCAAGCCTAACAGTG GTGGCACAAACTCTGCACAGAGGTTTCAGGGCA GGGTCACCATGACCAGGGACACGTCCATCAACA CAGCCTACATGGAGCTGAACAGGTGAGATCTG ACGACACGGCCGTGTATTACTGTGCGAGAGGG GGACTACGGTGCTACGTGGGGGGTCTTTGACTA CTGGGGCCAGGGAACCCTGGTCACCGTCTCCTCA |
| | | | SEQ ID NO: 26481 | SEQ ID NO: 30487 |
| | | AA | DIQMTQSPSSLSASVGDRVAITCRASQDIGNCLA WFQQKPGKAPKSLIYSASSLQSGVPSKFSGSGSG TDFTLTISSLQPEDFATYYCQQSDSYPLTFGGGT KVEIK | QVQLVQSGAEVKKPGASVRVSCKASGYTFTGYFIH WVRQAPGQGLEWMGWIKPNSGGTNSAQRFQGRV TMTRDTSINTAYMELNRLRSDDTAVYYCARGGTT VATWGVFDYWGQGTLVTVSS |
| | | | SEQ ID NO: 26482 | SEQ ID NO: 30488 |
| iPS:435701 | 21-225_170F6 | NA | GACATCGTGATGACCCAGTCTCCAGACTCCCT GGCTGTGTCTCTGGGCGCGAGGGCCACCATCA ACTGCAAGTCCAGCCAGAGTGTTTTACACAGC TCCAACAATTACAACTACTTAGCTTGGTACCA GCAGAAGACCAGGACAGCCTCCTAAAGTGCTCA TTCACTGGGCATCTACCCGGGAAATCCGGGGTC CCTGACCGATTCAGTGGCAGCGTGTCTGGAC AGATTTCACTCTCACCATCAACAGCCTGCAGG CTGAAGATGTGGCAGTTTATTACTGTCAGCAA TATTATAGTACTCCGTGGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACAGAAGTTCCAGGACA GTAACACAGGCTATGCACAGAAGTTCCAGGACA GAGTCACCATGACCAGGGACACACCTCCATAAGCA CAGCCTACATGGAGCTGAGCAGCCTGAGATCTG AGGACACGGCCGTGTACTGTGCGATTAGCAG TGGCTGGTACTGGTTCGACCCCTGGGGCCAGGGA ACCCTGGTCACCGTCTCCTCA |
| | | | SEQ ID NO: 26483 | SEQ ID NO: 30489 |

FIGURE 50
(Continued)

| | | | |
|---|---|---|---|
| iPS:435703 | 21-225_170D11 | AA | DIVMTQSPDSLAVSLGARATINCKSSQSVLHSSN NYNYLAWYQQRPGQPPKVLIHWASTRKSGVPD RFSGSVSGTDFTLTINSLQAEDVAVYYCQQYYST PWTFGQGTKVEIK<br>SEQ ID NO: 26484 | QVQLVQSGAEVKKPGASVKVSCKASGYTFTNYDIN WVRQATGQGLEWMGWMNPNSGNTGYAQKFQDR VTMTRHTSISTAYMELSSLRSEDTAVYYCAISSGW YWFDPWGQGTLVTSS<br>SEQ ID NO: 30490 |
| | | NA | GACATCCAGATGACCCAGTCTCCATCCTCCCT GTCTGCATCTGTGGAGACAGAGTCACCATCA CTTGCCGGGCAAGTCAGGGCATTAGAAATGAT TTAGGCTGGTATCAGCAGAAACCAGGGAAAG CCCCTAAACACCTGATCTATGCTGCATCCAGT TTGCAAAATGGGGTCCCATCAAGGTTCAGCGG CAGTGGATCTGGGACAGAATTCACTCTCACAA TCAGCAGCCTGCAGCCTGAAGATTATAGTTTT TATTACTGTCTACAGCATTATAGTTTCCCGCTC ACTTTCGGCGGAGGGACCAAGGTGGAGATCA GA<br>SEQ ID NO: 26485 | CAGGTGCAGCTGGTGGAGTCTGGGGGAGGCGTG GTCCAGCCTGGGAGGTCCCTGAGACTCTCCTGTG TAGCGTCTGGATTCACCTTCAGTAGCTATGGCAT GCACTGGGTCCGCCAGGCTCCAGGCAAGGGCT GGAGTGGGTGGCAATTATATGGTATGATGGAACT AATAAATACTATGCAGACTCCGTGAAGGGCCGA TTCACCATCTCCAGAGACAATTCCAAGAACACGC TGTATCTGCAACTGAACAGCCTGAGAGCCGAGG ACACGGCTGTGTATTACTGTGCGCGAGATCCCTT AGTGGATACAATGACCCGGTTATGGACTACTGG GGCCAGGGAACCCTGGTCACCGTCTCCTCA<br>SEQ ID NO: 30491 |
| | | AA | DIQMTQSPSSLSASVGDRVTITCRASQGIRNDLG WYQQKPGKAPKHLIYAASSLQNGVPSRFSGSGS GTEFTLTISSLQPEDFATYYCLQHYSFPLTFGGGT KVEIR<br>SEQ ID NO: 26486 | QVQLVESGGGVVQPGRSLRLSCVASGFTFSSYGMH WVRQAPGKGLEWVAIIWYDGTNKYYADSVKGRF TISRDNSKNTLYLQLNSLRAEDTAVYYCARDPLRG YNDPVMDYWGQGTLVTVSS<br>SEQ ID NO: 30492 |

FIGURE 50
(Continued)

| | | | |
|---|---|---|---|
| iPS:435705 | 21-225_171C3 | NA | GACATCCAGATGACCCAGTCTCCATCCTCCCT GTCTGCATCTGTAGGAGACAGAGTCACCATCA CTTGCCGGGCAAGTCAGGGACATTAGAAACTGAT TTAGGCTGGTTTCAGCAGAAACCAGGGAAAGC CCCTAAGCGCCTGATCTATACTGCATCCAGTT GCAAAGTGGGGTCCCATCAAGGTTCAGCGGCA GTGGATCTGGGACAGATTTCACTCTCACGATC AGCAGCCTGCAGCCTGAAGATTTTGCAACTTA TTACTGTCTACAGCATTATAGTTACCCGCTCAC TTTCGGCGGAGGGACCAAGGTGGAGATCAAA SEQ ID NO: 26487 | CAGGTGCAGCTGGTGGAGTCTGGGGGAGGCGTG GTCCAGCCTGGGGGGTCCCTGAGACTCTCCTGTG CAGCCGTCTGGCTTCACCTTCAGTACTTATGGCAT GCACTGGGTCCGCCAGGCTCCAGGCAAGGGGCT GGAGTGGGTGACAATTATATGGTATGATGGACT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCCTT ACGTGGATACAATGACCCGGTTATGGACTACTGG GGCCAGGGAACCCTGGTCACCGTCTCCTCA SEQ ID NO: 30493 |
| | | AA | DIQMTQSPSSLSASVGDRVTITCRASQGIRTDLG WFQQKPGKAPKRLIYTASSLQSGVPSRFSGSGSG TEFTLTISSLQPEDFATYYCLQHYSYPLTFGGGT KVEIK SEQ ID NO: 26488 | QVQLVESGGGVVQPGGSLRLSCAASGFTFSTYGMH WVRQAPGKGLEWVTIIWYDGTNKYYADSVKGRFT ISRDNSKNTLYLQMNSLRAEDTAVYYCARDPLRGY NDPVMDYWGQGTLVTVSS SEQ ID NO: 30494 |
| iPS:435709 | 21-225_171A4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATACTGCATCCAGT TGCAAAGTGGGGTCCCATCAAGGTTCAGCGG CAGTGGATCTGGGACAGACTGGGACAGCTTGGGACTT TCAGCAGCCTGCAGCCTGAAGATTTTGCAACT TATTACTGTCTACAGCATTATAGTTACCCGCTC ACTTTCGGCGGAGGGACCAAGGTGGAGATCA AA SEQ ID NO: 26489 | CAGGTGCAACTGGTGGAGTCTGGGGGAGGCGTG GTCCAGCCTGGGGGGTCCCTGAGACTCTCCTGTG CAGCCGTCTGGCTTCACCTTCAGTACTTATGGCAT GCACTGGGTCCGCCAGGCTCCAGGCAAGGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAAG ACACGGCTGTGTATTACTGTGCGAGAGATCCCTT ACGTGGATACAATGACCGGTTATGGACTACTGG GGCCAGGGAACCCTGGTCACCGTCTCCTCA SEQ ID NO: 30495 |

FIGURE 50
(Continued)

| | | | |
|---|---|---|---|
| iPS:435711 | 21-225_171G4 | AA | DIQMTQSPSSLSASVGDRVTITCRASQGIRNDLG WYQQKPGKAPKRLIYTASSLQSGVPSRFSGSGSG TEFTLTISSLQPEDFATYYCLQHYSYPLTFGGGT KVEIK<br><br>SEQ ID NO: 26490 | QVQLVESGGGVVQPGGSLRLSCAASGFTFSTYGMH WVRQAPGKGLEWVAIIWYDGSNKYYADSVKGRFT ISRDNSKNTLYLQMNSLRAEDTAVYYCARDPLRGY NDPVMDYWGQGTLVTVSS<br><br>SEQ ID NO: 30496 |
| | | NA | GACATCCAGATGACCCAGTCTCCATCTTCCGT GTCTGCATCTGTAGGAGACAGAGTCACCATCA CTTGTCGGGCGAGTCAGGGTGTTAACGACTGG TTAGCCTGGTATCAGCAGAAACCAGGGAGAG CCCCTAAGCTCCTGATCTATGATGCATCAAGT TTGCAAAGTGGGGTCCCATCAAGGTTCAGCGG CAGTGGATCTGGGACAGAGATTTCACTCTCACCA TCAGCAGCCTGCAGCCTGAAGATTTTGCAACT TACTATTGTCAACAGGCTAACAGTTTCCCGTG GACGTTCGGCCAAGGGACCAAGGTGGAAATC AAA<br><br>SEQ ID NO: 26491 | GAGGTGCAGCTGTTGGAGTCTGGGGGAGACTTA GTACAGCCTGGGGGGTCCCTGAGACTCTCCTGTG CAGCCTCTGGATTCACCTTTAGCAGCTGTGCCAT GACCTGGGTCCGCCAGGCTCCAGGGAAGGGGCT GGAGTGGGTCTCAGCTATTAGTGGTCGTGGTGGT ACCACGTTCTACGCAGACTCCGTGAGGGGCCGGT TCACCATCTCAAGAGACAATTCCAAGAACACGCT GTTTCTGCAAATGAACAGCTGAGAGCCGAGGA CACGGCCGTATATTACTGTGCGAAAGATCTTATT GGGGAGCTACTTACTTTGACTACTGGGGCCAGG GAACCCTGGTCACCGTCTCCTCA<br><br>SEQ ID NO: 30497 |
| | | AA | DIQMTQSPSSVSASVGDRVTITCRASQGVNDWL AWYQQKPGRAPKLLIYDASSLQSGVPSRFSGSGS GTDFTLTISSLQPEDFATYYCQQANSFPWTFGQG TKVEIK<br><br>SEQ ID NO: 26492 | EVQLLESGGDLVQPGGSLRLSCAASGFTFSSCAMT WVRQAPGKGLEWVSAISGRGGTTFYADSVRGRFTI SRDNSKNTLFLQMNSLRAEDTAVYYCAKDLIGGAT YFDYWGQGTLVTVSS<br><br>SEQ ID NO: 30498 |

FIGURE 50
(Continued)

| | | | |
|---|---|---|---|
| iPS:435713 | 21-225_171D7 | NA | GATATTGTGATGACTCAGTCTCCACTCTCCTG CCCGTCACCCCTGAGAGCCGGCCTCCATCTC CTGCAGGTCTAGTCAGAGCCTCCTGTATCATA ATGGATACAACTATTTGGATTGGTACCTGCAG AAGACAGGGCAGTCTCCACAGTCTCCTGATCTA TGTGGGTTCTAATCGGGCCTCCGGGGTCCCTG ACAGGTTCAGTGGCAGTGGATCAGGCACAGAT TTTACACTGAAAATCAGCAGGTGGAGGCTGA GGATGTTGGGGTTTATTACTGCATGCAAACTC TACAAACTCCGCTCACTTTCGGCGGAGGGACC AAGGTGGAGATCAAA<br><br>SEQ ID NO: 26493 | CAGGTGCAGCTGGTGGAGTCTAGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCATATGACGGAAA CAATAGACACTATGCAGACTCCGTGCAGGGCCG ATTCACCATTTCCAGAGACAATTCCAAGAACACG CTGTCTCTGCAAATGAACAGCCTGGGAGCTGAGG ACACGGCTGTGTATTACTGTGCGAGAGATCGTCA CCGTTTGGACTACGCTTTGGACGTCTGGGGC CAAGGGACCACGGTCACCGTCTCCTCA<br><br>SEQ ID NO: 30499 |
| | | AA | DIVMTQSPLSLPVTPGEPASISCRSSQSLLYHNGY NYLDWYLQKTGQSPQLLIYVGSNRASGVPDRFS GSGSGTDFTLKISRVEAEDVGVYYCMQTLQTPL TFGGGTKVEIK<br><br>SEQ ID NO: 26494 | QVQLVESRGGVVQPGRSLRLSCAASGFTFSSYGMH WVRQAPGKGLEWVAVISYDGNNRHYADSVQGRF TISRDNSKNTLSLQMNSLGAEDTAVYYCARDRHRL DYYALDVWGQGTTVTVSS<br><br>SEQ ID NO: 30500 |
| iPS:435715 | 21-225_171A8 | NA | GCCATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAAACCTCTGATCTATGCTGCATTCAGTT TGCAAGGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGACTAACAGTTTCCCGTGG ACGTTCGGCCAAGGGACCAAGGTGGAAATCA AA<br><br>SEQ ID NO: 26495 | GAGGTGCAGTTGTTGGAGTCTGGGGGAGGCTTGG TACAGCCTGGGGGGTCCCTGAGACTCTCCTGTGC AGCCTCTGGATTCACCTTTAGGAGCTGCCATG AGCTGGGTCCGCCAGGCTCCAGGGAAGGGGCTG GAGTGGGTCTCAGTTATTAGTGGTAGTGGTGTA GCACATTCTACACAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGCGAAATCGAATAGCA GTGGCTGGTTTGACTACTGGGGCCAGGGAACCCT GGTCACCGTCTCCTCA<br><br>SEQ ID NO: 30501 |

FIGURE 50
(Continued)

| | | | | |
|---|---|---|---|---|
| | | AA | AIQMTQSPSSVSASVGDRVTITCRASQGISNWLA WYQQKPGKAPNLMIHAAFSLQGGVPSRFSGSGS GTDFTLTISSLQPEDFATYYCQQTNSFPWTFGQG TKVEIK | EVQLLESGGGLVQPGGSLRLSCAASGFTFRSSAMS WVRQAPGKGLEWVSVSGSGSTFYDSVKGRFTI SRDNSKNTLYLQMNSLRAEDTAVYYCAKSNSSGW FDYWGQGTLVTVSS |
| | | | SEQ ID NO: 26496 | SEQ ID NO: 30502 |
| iPS:435717 | 21-225_171A9 | NA | GACATCCAGATGACCCAGTCTCCATCTTCCGT GTCTGCATCTGTAGGAGACAGAGTCACCATCA CTTGTCGGGCGAGTCAGGATATTACCAACCTGG TTAGCCTGGTATCAGCAGAAACCAGGGAAAG CCCCTAAGCTCCTGATCTATGCATCCAGTT TGCAAAGTGCGGTCCCATCAAGGTTCAGCGGC AGTGGATCTGGGACAGATTTCACTCTCACCGT CAGCAGTTTGCAGCCTGAAGATTTTGCAACTT ACTATTGTCTACAGACTAACAGTTTCCCGTGG ACGTTCGGCCAAGGGACCAAGGTGGAGATCA AG | GAGGTGCAGTTGTTGGAGTCTGGGGGAGGCTTGG CACAGCCTGGGGGGTCCCTGAGACTCTCCTGTGC AGCCTCTGGATTCACCTTTAGCAGCTATGCCATG ACTTGGGTCCGCCAGGCTCCAGGGAAGGGGCTG GAGTGGGTCTCAGCTATTAGTGGTAGTGGTGTA ACACATTCAACGCAGACTCCGTGAAGGGCCGGTT CACCATCTCCAGAGACACAATTCCAAGAACACGCTG TATCTGCAAATGAACAGCCTGAGAGCCGAGGAC ACGGCCGTATATTACTGTGCAAAGTCTGGGGATCG ACTACTACTACGGTATGGACGTCTGGGGCCA AGGGACCACGGTCACCGTCTCCTCA |
| | | | SEQ ID NO: 26497 | SEQ ID NO: 30503 |
| | | AA | DIQMTQSPSSVSASVGDRVTITCRASQDITTWLA WYQQKPGKAPKLLIYDASSLQSAVPSRFSGSGS GTDFTLTVSSLQPEDFATYYCLQTNSFPWTFGQG TKVEIK | EVQLLESGGGLAQPGGSLRLSCAASGFTFSSYAMT WVRQAPGKGLEWVSAISGSGGNTFNADSVKGRFTI SRDNSKNTLYLQMNSLRAEDTAVYYCAKLGIDYY YYGMDVWGQGTTVTVSS |
| | | | SEQ ID NO: 26498 | SEQ ID NO: 30504 |

FIGURE 50
(Continued)

| | | | |
|---|---|---|---|
| iPS:435719 | 21-225_171A11 | NA | GACATCCAGATGACCCAGTCTCCATCCTCCCT GTCTGCATCTGTAGGAGACAGAGTCACCATCA CTTGCCGGGCAAGTCAGGGCATTAGAAATAAT TTAGGCTGGTATCAGCAGAAACCAGGGAAAG CCCCTAAGCGCCTGATCTATCCTGCATCCAGTT TGCAAAGTGGGGGTCCCATCAAGGTTCAGCGGC AGTGGATCTGGGACAGATTCACTCTCACAAT CAGCAGCCTGCAGCCTGAAGATTTTGCAACTT ATTACTGTCTACAGGATCATAGTTACCCATTC ACTTTCGGCCCTGGGACCAAAGTGGATATCAA A | GAGGTGCAGCTGTGTGGAGTCTGGGGAGGCCTG GTCAAGCCTGGGGGGTCCCTGAGACTCTCCTGTG CAGCCCTCTGGATTCACCTTCAGTAGCTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTACTGTGCGAGAGATAGGGGC AGCTCCTGGGGCCAGGGAATCCTGGTCACCGTCT CCTCA |
| | | | SEQ ID NO: 26499 | SEQ ID NO: 30505 |
| | | AA | DIQMTQSPSSLSASVGDRVTITCRASQGIRNNLG WYQQKPGKAPKRLIYPASSLQSGVPSRFSGSGSG TEFTLTISSLQPEDFATYYCLQDHSYPFTFGPGTK VDIK | EVQLVESGGGLVQPGGSLRLSCAASGFTFSSYSMN WVRQAPGKGLEWVSSISGSSSYIYYADSVKGRFTIS RDNAKNSLYLQMNSLRAEDTAVYYCARDRGSSW GQGILVTVSS |
| | | | SEQ ID NO: 26500 | SEQ ID NO: 30506 |
| iPS:435721 | 21-225_172B3 | NA | GACATCCAGATGACCCAATCTCCATCCTCCCT GTCTGCATCTGTAGGAGACAGAGTCACCATCA CTTGCCGGGCTAGTCAGGGCATTAGAAATGAT TTAGGCTGGTATCAGCAGAAACCAGGGAAAG CCCCTAAGCGCCTGATCGGTGCTGAATCCAGT TTGCAAAGTGGGGTCCATCAAGGTTCAGCGG CAGTGGATCTGGGACAGAATTCACTCTCACAA TCAGCGGCCTGCAGCCTGAAGATTTTGCAACT TATTACTGTCTACAGCATTATAGTTACCCGCTC ACTTTCGGCGGAGGGACCAAAGTGGAGATCA AA | CAGGTGCAGCTGGTGGAGTCTGGGGGAGGCGTG GTCCAGCCTGGGAGGCCCCTGAGACTCTCCTGTG CAGCGTCTGGATTCACCTTCAGTAGCTATATGGCAT GCACTGGGTCCGCCAGGCTCCAGGCAAGGGGCT GGAGTGGGTGGCAGTTATATGTGGTATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCCCTT ACGTGGATACAATGACCCGGTTATGGACTACTGG GGCCAGGGAACCCTGGTCACCGTCTCCTCA |
| | | | SEQ ID NO: 26501 | SEQ ID NO: 30507 |

FIGURE 50
(Continued)

| | | | |
|---|---|---|---|
| iPS:435723 | 21-225_172B7 | AA | DIQMTQSPSSLSASVGDRVTITCRASQGIRNDLG WYQQKPGKAPKRLIGAESSLQSGVPSRFSGSGSG TEFTLTISGLQPEDFATYYCLQHYSYPLTFGGGT KVEIK<br>SEQ ID NO: 26502 | QVQLVESGGGVVQPGRPLRLSCAASGFTFSTYGMH WVRQAPGKGLEWVAVIWYDGSNKYYADSVKGRF TISRDNSKNTLYLQMNSLRAEDTAVYYCARDPLRG YNDPVMDYWGQGTLVTVSS<br>SEQ ID NO: 30508 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GATGGAAAGAACCTATTTCTATTGGTACCTGCA GAAGCCAGGCCAGGGCCTCCACAGGTCCTGTTAT TTGAAGTTTCCCACCGGTTCTCTGGAGTGCCA GATAGGTTCAGTGGCGGGTCAGGGACAG ATTTCACACTGAAGATCAGCCGGGTGGAGCT GAGGATGTTGGGGTTTACTATTGCATGCAAAG TATACAGTTTCCGTGGACGTTCGGCCAAGGGA CCAGGGTGGACATCAAA<br>SEQ ID NO: 26503 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT AGAGTGGGTGGCAATTATATGTATGATGGAAGT AATAAATACTATGTAGACTCCGTGAAGGGCCGAT TCACCATCTCCAGAGACAATTCCAAGAACACGCT GTATCTCCAAATGAACAGCTGAGAGCCGAAGA CACGGCTGTGTACTATTGTGCGAGAGAGGGTAC GATTTTTGGAGTGGTTATTGGGACTACTGGGGCC AGGGAACCCTGGTCACCGTCTCCTCA<br>SEQ ID NO: 30509 |
| | | AA | DIVMTQTPLSLSVTPGQPASISCKSSQSLLHGDG KTYFYWYLQKPGQPPQVLLFEVSHRFSGVPDRF SGGGSGTDFTLKISRVEAEDVGVYYCMQSIQFP WTFGQGTRVDIK<br>SEQ ID NO: 26504 | QVQLVESGGGVVQPGRSLRLSCAASGFTFSNYGM HWVRQAPGKGLEWVAIIWYDGSNKYYVDSVKGR FTISRDNSKNTLYLQMNSLRAEDTAVYYCAREAYD FWSGYWDYWGQGTLVTVSS<br>SEQ ID NO: 30510 |

FIGURE 50
(Continued)

| | | | |
|---|---|---|---|
| iPS:435725 | 21-225_172G8 | NA | GACATCCAGATGACCCAGTCTCCATCCTCCCT GTCTGCATCTGTGGAGACAGAGTCACCATCA CTTGCCGGGCAAGTCAGGGCGTTAGAAATGAT TTAGGCTGGTATCAGCAGAAACCAGGAAAG CCCCTAAACACCTGATCTATGCTGCATCCAGT TTGCAAAATGGGGTCCCATCAAGGTTCAGTGG CAGTGGCTCTGGGACAGAATTCACTCTCACAA TCAGCAGCCTGCAGCCTGAAGATTTTGCCACT TATTACTGTCTACACCATTATAGTTTCCCGCTC ACTTTCGGCGGAGGGACCAAGGTGGAGATCA AA<br><br>SEQ ID NO: 26505 | CAGGTGCAGATGGTGGAGTCTGGGGGAGGCGTG GTCCAGCCTGGGAGGTCCCTGAGACTCTCCTGTG CAGCGTCTGGATTCACCTTCAGTACTTACTATGCAT GCACTGGGTCCGCCAGGCTCCAGGCAAGGGCT GGAATGGATGGCAATTATATGGTATGATGGAAACT AATAAATACTATGCAGACTCCGTGAAGGGCCGA TTCACCATCTCCAGAGACAATTCCAAGAACACGC TGTATCTGCAACTGAACAGCCTGAGAGCCGAGG ACACGGCTGTGTATTACTGTGCGCGAGATCCTT ACGTTGGATACAATGACCCGGTTATGGACTACTGG GGCCAGGGAACCCTGGTCACCGTCTCCTCA<br><br>SEQ ID NO: 30511 |
| | | AA | DIQMTQSPSSLSASVGDRVTITCRASQGVRNDLG WYQQKPGKAPKHLIYAASSLQNGVPSRFSGSGS GTEFTLTISSLQPEDFATYYCLHHYSFPLTFGGGT KVEIK<br><br>SEQ ID NO: 26506 | QVQMVESGGGVVQPGRSLRLSCAASGFTFSTYGM HWVRQAPGKGLEWMAIIWYDGTNKYYADSVKGR FTISRDNSKNTLYLQLNSLRAEDTAVYYCARDPLR GYNDPVMDYWGQGTLVTVSS<br><br>SEQ ID NO: 30512 |
| iPS:435727 | 21-225_172E11 | NA | GACATCGTGATGACCCAGTCTCCAGACTCCCT GGCGGTGTCTCTGGGCGAGAGGGCCACCATCA ACTGCAAGTCCAGCCAAGTGCTTTTACACAGC TCCAACAATAACAACTACTTAGCTTGGTACCA GCAGAAACCAGGACAGCCTCCTAAGCTGCTCA TTTACTGGGCATCTACTCGGGAATCCGGGGTC CCTGACCGATTCAGTGGCAGCGGGTCTGGGAC AGATTTCATTCTCACCATCAGCGGCCTGCAGG CTGAAGATGTGGCAGTTTATTACTGTCAGCAA TATTTTACTACTCCGTGCAGTTTGCCAGGGG ACCAAGCTGGAGATCAAA<br><br>SEQ ID NO: 26507 | CAGGTGCAGCTGGTGCAGTCTGGGGCTGAGGTG AAGAAGCCTGGGGCCTCAGTGATGTCTCCTGCA AGGCTTCTGATACACCTTCACCAATTATGATAT CAACTGGGTGCGACAGGCCACTGGACAAGGGCT TGAGTGGATGGGATGGATGCACCCTAACAGTGGT AACACAGGCTATGCACAGAAGTTCCAGGGCAGA GTCACCATGACCAGGAACACCTCCATAAGCACA GCCTACATGGAGCTGAGCAGCCTGAGATCTGAG GACACGGCCGTGTATTACTGTGTGCGTATAGCAGTG GACACGGCCGTGTATTACTGTGTGCGTATAGCAGTG GCTGGTACCGGTTTGACTACTGGGGCCAGGAAC CCTGGTCACCGTCTCCTCA<br><br>SEQ ID NO: 30513 |

FIGURE 50
(Continued)

| | | | | |
|---|---|---|---|---|
| | | | AA | DIVMTQSPDSLAVSLGERATINCKSSQSVLHSSN NNNYLAWYQQKPGQPPKLLIYWASTRESGVPD RFSGSGSGTDFILTISGLQAEDVAVYYCQQYFTT PCSFGQGTKLEIK<br>SEQ ID NO: 26508 | QVQLVQSGAEVKKPGASVMVSCKASGYTFTNYDI NWVRQATGQGLEWMGWMHPNSGNTGYAQKFQG RVTMTRNTSISTAYMELSSLRSEDTAVYYCAYSSG WYRFDYWGQGTLVTVSS<br>SEQ ID NO: 30514 |
| iPS:435729 | 21-225_173E7 | NA | GACATCCAGATGACCCAGTCTCCATCCTCCCG GTCTGCATGTATAGGAGACAGAGCCACCATCA CTTACCGTGCAAGTCAGACAGACCATTAGCAACTAT TTAAATTGGTATCAGCAGAAACCAGGAAAG CCCCTAAACTCCTTATCTATCTGCATCCAGTT TGCAAATTGGGGTCCCATCAAGGTTCAGTGGC AGTGGATCTGGGACAGATTTCACTCTCACCAT CAGCAGTGTGCAACCTGAAGATTTTGCAACTT ACTTCTGTCAACAGAGTTACAGAACCCCTCAG TGGACGTTCGGCCAAGGGACCAAGGTGGAAA TCAAA<br>SEQ ID NO: 26509 | GAGGTGCAGTTGTTGGAGTCTGGGGGAGGCTCG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCATTTATTAGTGGTAGTGGTGGT AACACATTCTACGCAGACTCCGTGAAGGGCCGGT TCACCATCTCCAGAGACAATTCCAAGAACACGCT GTATCTGCAAATGAACAGCCTGCAAGCCGAGGA CACGGCCGTATATTACTGTACGAAAAGGGATACC TACAAACGGTTGGGATGCTTTGATATCTGGGGCC AAGGGACAATGGTCACCGTCTCCTCA<br>SEQ ID NO: 30515 |
| | | AA | DIQMTQSPSSRSACIGDRATTYRASQTISNYLN WYQQKPGKAPKLLIYAASSLQIGVPSRFSGSGSG TDFTLTISSVQPEDFATYFCQQSYRTPQWTFGQG TKVEIK<br>SEQ ID NO: 26510 | EVQLLESGGGSVQPGGSLRLSCAASGFTFSSYAMS WVRQAPGKGLEWVSFISGSGGNTFYADSVKGRFTI SRDNSKNTLYLQMNSLQAEDTAVYYCTKRDTYNG WDAFDIWGQGTMVTVSS<br>SEQ ID NO: 30516 |

FIGURE 50
(Continued)

| | | | | |
|---|---|---|---|---|
| iPS:435731 | 21-225_173A11 | NA | GATATTGTGATGACCCAGACTCCACTCTCT GTCCGTCACCCCTGGACAGCCGGCCTCCATCT CCTGCAAGTCTAGTCAGAGCCTCCTGCATGGT GATGGAAAGAACTATTTGTATTGGTACCTGCA GAAGCCAGGCCAGCCTCCACAGCTCCTGATCT ATGAAGTTTCCAACCGGTTCTCTGGCGTGCCA GATAGGTTCAGTGGCAGCGGGTCAGGGACAG ATTTCACACTGAAAATCAGCCGGGTGGAGGCT GAGGATGTTGGGGTTTTTTGTCATGCAAAG TATACAGGTTCCGTGCGACGTTCGGCCAAGGGA CCAAGGTGGAAATCAAA<br><br>SEQ ID NO: 26511 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT AGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGCCTA CGATTTTTGGAGTGGTTTCTTTGACTCCTGGGGCC AGGGAACCCTGGTCACCGTCTCCTCA<br><br>SEQ ID NO: 30517 |
| | | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGVFFCMQSIQVPWT FGQGTKVEIK<br><br>SEQ ID NO: 26512 | QVQLVESGGGVVQPGRSLRLSCAASGFTFSSYGMH WVRQAPGKGLEWVAIIWYDGSNKYYADSVKGRFT ISRDNSKNTLYLQMNSLRAEDTAVYYCAREAYDF WSGFFDSWGQGTLVTVSS<br><br>SEQ ID NO: 30518 |
| iPS:435733 | 21-225_173C11 | NA | GATATTGTGATGACCCAGACTCCACTCTCT GTCCGTCACCCCTGGACAGCCGGCCTCCATCT CCTGCAAGTCTAGTCAGAGCCTCCTGCATAGT GAGGGAAAGAACTACTTGTATTGGTACCTGCA GAAGCCAGGCCAGCCTCCACAGCTCCTGATCT ATGAAGTTTCCCACCGGTTCTCTGGAGTGCCA GATAGGTTCAGTGGCAGCGGGTCAGGGACAG ATTTCACACTGAAAATCAGCGGGTGGAGGCT GAGGATGTTGGGGTTTATTACTGCATGCAAAG TATACAGCTTCTCACTTTCGGCGGAGGGACCA AGGTGGAGATCAAA<br><br>SEQ ID NO: 26513 | CAGGTGCAGCTGGTGGAGTCGGGGGGAGGCGTG GTCCAGCCTGGGAGGTCCCTGAGACTCTCCTGTG CAGCGTCTGGATTCACCTTCAGTAGCTATGGCAT ACACTGGGTCCGCCAGGCTCCAGGCAAGGGACT GGAGTGGGTGGCACTTATATTTATGGAGGT AATAAATACTATGCAGACTCCGTGAAGGGCCGA TTCACCATCTCCAGAGACAATTCCAAGAACACGC TGTATCTGCATATGAGCAGCCTGAGAGCCGAGG ACACGGCTGTGTATTACTGTGCGAGACGGTATAG CAGCAGCTGGTCCGGTGGTATGGACGTCTGGGGC CAAGGGACCACGGTCACCGTCTCCTCA<br><br>SEQ ID NO: 30519 |

FIGURE 50
(Continued)

| | | | |
|---|---|---|---|
| iPS:435735 | | AA | DIVMTQTPLSLSVTPGQPASISCKSSQSLLHSEGK TYLYWYLQKPGQPPQLLIYEVSHRFSGVPDRFSG SGSGTDFTLKISRVEAEDVGVYYCMQSIQLLTFG GGTKVEIK<br>SEQ ID NO: 26514 | QVQLVESGGGVVQPGRSLRLSCAASGFTFSSYGIH WVRQAPGKGLEWVALIFYDGSNKYYADSVKGRFT ISRDNSKNTLYLHMSSLRAEDTAVYYCARRYSSSW SGGMDVWGQGTTVTVSS<br>SEQ ID NO: 30520 |
| | 21-225_173H12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATACTATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAAGT TATTACTGTCTACAGCATTATAGTTTCCCGAAC ACTTTCGGCGGAGGGACCAAGGTGGAGATCA AA<br>SEQ ID NO: 26515 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGCT GGAGTGGGTGGCAATTATATCAGACTCCGTGAAGGGCCGA AACAAATACTATGCAGACTCCGTGAAGGGCCGA TTCACCATCTCCAGAGACAATTCCAAGAACACGC TGTATCTGCAACTGAACAGCCTGAGAGCCGAGG ACACGGCTGTGTATTACTGTGCGCGAGATCCCT AGTGGATACAATGACCCGGTTATGGACTACTGG GGCCAGGGAACCCTGGTCACCGTCTCCTCA<br>SEQ ID NO: 30521 |
| | | AA | DIQMTQSPSSLSASVGDRVTITCRASQGIRNDLG WYQQKPGKAPKRLIYTTSSLQSGVPSRFSGSGSG TEFTLTISSLQPEDFASYYCLQHYSFPNTFGGGTK VEIK<br>SEQ ID NO: 26516 | QVQLVESGGGVVQPGRSLRLSCAASGFTFSSYGMH WVRQAPGKGLEWVAIIWYDGTNKYYADSVKGRF TISRDNSKNTLYLQLNSLRAEDTAVYYCARDPLRG YNDPVMDYWGQGTLVTVSS<br>SEQ ID NO: 30522 |

FIGURE 50
(Continued)

| | | | |
|---|---|---|---|
| iPS:435737 | 21-225_174G5 | NA | GACATCGTGATGACCCAGTCTCCAGATTCCCT GGCTGTGTCTCTGGCGCGAGGGCCACCATCA ATTGCAAGTCCAGCAGTGTATTACACAGC TCCAACAATTACAACTACTTAACTGGTACCA GCAGAAATCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTATTACTGTCAGCAA TATTATGTGACTCCGTGGACGTTCGGCCAAGG GACCAAGGTGGAAATCAAA<br><br>SEQ ID NO: 26517 |
| | | AA | DIVMTQSPDSLAVSLGARATINCKSSQSVLHSSN NYNYLTWYQQKSGQPPKLLIYWASTRESGVPDR FSGSGSGTDFTLTISSLQAEDVAVYYCQQYYRTP WTFGQGTKVEIK<br><br>SEQ ID NO: 26518 |
| | | NA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGGTTAGCAGT GGCTGGTACTGGTTCGACCCCTGGGGCCAGGGA ACCCTGGTCACCGTCTCCTCA<br><br>SEQ ID NO: 30523 |
| | | | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAVSSGW YWFDPWGQGTLVTVSS<br><br>SEQ ID NO: 30524 |
| iPS:435739 | 21-225_174G7 | NA | GCCATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTATCAGCAGAAACCAGGGAAAG CCCCTAACCTCCTGATCCATGCTGCATTCAGTT TGCAAAGTGGGGTCCCATCAAGGTTCAGCGGC AGTGGATCTGGGACAGCCTGCAGTTCACTCTCACCAT CAGCAGCCTGCAGCCTGAAGATTTTGCAACTT ACTATTGTCAACAGACTAACAGTTTCCCGTGG ACGTTCGGCCAAGGGACCAAGGTGGAAATCA AA<br><br>SEQ ID NO: 26519 | GAGGTGCAGTTGTTGGAGTCTGGGGGAGGCTTGG TACAGCCTGGGGGGTCCCTGAGACTCTCCTGTGC AGCCTCTGGATTCACCTTTAGGAGCTGCCATG AGCTGGGTCCGCCAGGCTCCAGGGAAGGGGCTG GAGTGGGTCTCAGTTATTAGTGGTAGTGGTGTA GCACATTCTACACAGACTCCGTGAAGGGCCGGTT CACCATCTCCAGAGACAATTCCAAGAACACGCTG TATCTGCAAATGAACAGCCTGAGAGCCGAGGAC ACGGCCGTGTATTACTGTGCGAAATCGAATAGCA GTGGCTGGTTTGACTACTGGGGCCAGGGAACCCT GGTCACCGTCTCCTCA<br><br>SEQ ID NO: 30525 |

FIGURE 50
(Continued)

| | | | |
|---|---|---|---|
| iPS:435741 | 21-225_174G10 | AA | AIQMTQSPSSVSASVGDRVTITCRASQGISNWLA WYQQKPGKAPNLLIHAAFSLQGGVPSRFSGSGS GTDFTLTISSLQPEDFATYYCQQTNSFPWTFGQG TKVEIK<br><br>SEQ ID NO: 26520 | EVQLLESGGGLVQPGGSLRLSCAASGFTFRSSAMS WVRQAPGKGLEWVSVISGSGSTFYTDSVKGRFTI SRDNSKNTLYLQMNSLRAEDTAVYYCAKSNSSGW FDYWGQGTLVTVSS<br><br>SEQ ID NO: 30526 |
| | | NA | GACATCCAGATGACCCAGTCTCCATCCTCCCT GTCTGCATCTGTAGGAGACAGAGTCACCATCA CTTGCCGGGCAAGTCAGGGCATTAGAGATGAT TTAGGCTGGTATCAACAGAAACCAGGGAAAG TCCCTAAGCGCCTGATATATGCTGCATCCAGT TTGCAAAGTGGGGTCCCATCCAAGGTTCAGCGG CAGTGGATCTGGGACAGATTCACTCTCACAA TCAGCAGCCTACAGCCTGAAGATTTTGCAACT TATTACTGTCTTCAGCATCATAGTTACCCTCGG ACGTTCGGCCAAGGGACCAAGGTGGAAATCA AA<br><br>SEQ ID NO: 26521 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGGCAGTTATATGTGTATGGAAGT AATAAATACTATGCAGACTCCGTGAAGGGCCGA TTCACCATCTCCAGAGACAACAATTCCAAGAACACGC TGTATCTGCAATTGAACAGCCTGAGAGCCGAGG ACACGGCTGTGTATTACTGTGCGAGAGAAGGTA TAGCAGTGGCTGGTAGGACTACGGTTACGGTC TGGGGCCAAGGGACCACGGTCACCGTCTCCTCA<br><br>SEQ ID NO: 30527 |
| | | AA | DIQMTQSPSSLSASVGDRVTITCRASQGIRDDLG WYQQKPGKVPKRLIYAASSLQSGVPSRFSGSGS GTEFTLTISSLQPEDFATYYCLQHHSYPRTFGQG TKVEIK<br><br>SEQ ID NO: 26522 | QVQLVESGGGVVQPGRSLRLSCAASGFTFSDYVM HWVRQAPGKGLEWVAVIWYDGSNKYYADSVKGR FTISRDNSKNTLYLQLNSLRAEDTAVYYCARERYSS GWYDYGMDVWGQGTTVTVSS<br><br>SEQ ID NO: 30528 |

FIGURE 50
(Continued)

| | | | | |
|---|---|---|---|---|
| iPS:435743 | 21-225_175G1 | NA | GACATCCAGATGACCCAGTCTCCATCCTCCT GTCTGCATCTGTAGGAGACAGAGTCACCATCA CTTGCCGGGCAAGTCAGGGCATTAGAACTGAT TTAGGCTGGTATCAGCAGAAACCAGGGAAAG CCCCTAAGCGCCTGATCTATACTGCATCCAGT TTGCAAAGTGGGGTCCCATCAAGGTTCAGCGG CAGTGGATCTGGGACAGAATTCACTCTCACGA TCAGCAGCCTGCAGCCTGAAGATTTTGCAACT TATTACTGTCTACAGCATTATAGTTACCCGCTC ACTTTCGGCGGAGGGACCAAGGTGGAGATCA AG SEQ ID NO: 26523 | CAGGTGCAACTGGTGGAGTCTGGGGGAGGCGTG GTCCAGCCTGGGGGGTCCCTGAGACTCTCCTGT CAGCCTCTGGCTTCACCTTCAGTAGTACCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATATCCAGAGACAATTCCAAGAACACGC TGTATGTGCAAATGAACAGCCTGAGAGCCGAGG ACACGGCTGTGTATTACTGTGCGAGAGATCCTT ACGTGGATACAATGACCCGGTTATGGACTACTGG GGCCAGGGAACCCTGGTCACCGTCTCCTCA SEQ ID NO: 30529 |
| | | AA | DIQMTQSPSSLSASVGDRVTITCRASQGIRTDLG WYQQKPGKAPKRLIYTASSLQSGVPSRFSGSGSG TEFTLTISSLQPEDFATYYCLQHYSYPLTFGGGT KVEIK SEQ ID NO: 26524 | QVQLVESGGGVVQPGGSLRLSCAASGFTFSTYGMH WVRQAPGKGLEWVAVIWYDGSNKYYADSVKGRF TISRDNSKNTLYVQMNSLRAEDTAVYYCARDPLRG YNDPVMDYWGQGTLVTVSS SEQ ID NO: 30530 |
| iPS:435745 | 21-225_175G3 | NA | GACATCCAGATGACCCAGTCTCCATCCTCACT GTCTGCATCTGTAGGAGACAGAGTCACCATCA CTTGTCGGGCGAGTCAGGACATTAGCAATGAT TTAGCCTGGTTTCAGCAGAAACCAGGGAAAGC CCCTAAGTCCCTGATCTTTCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAATCTGATAGTTACCCTCTCAC TTTCGGCGGAGGGACCAAGGTTGAGATCAAA SEQ ID NO: 26525 | CAGGTACAGGTGGTGCAGTCTGGGGCTGAGGTG AAGAAGCCTGGGCCTCAGTGAAGGTCTCCTGC AAGGCTTCTGGATACACCTTCACCGGCTACTTTA TGCACTGGGTGCGACAGGCCCCTGGACAAGGGC TTGAATGGATGGGATGGATCAACCTAAAAGTG GTGGCACAAACTGTGCACAGAGGTTTCAGGGCA GGGTCACCATGACCAGGGACACGTCCATCACCA CAGCCTACATGGAACTGAGCAGGCTGCGATCTG ACGACACGGCCGTGTATTATTGTGTGAGAGGGG GACTACGGTGACTACGGTGGGGGTCTTTGACTAC TGGGGCCAGGGAACCATGGTCACCGTCCTCA SEQ ID NO: 30531 |

FIGURE 50
(Continued)

| | | AA | DIQMTQSPSSLSASVGDRVTITCRASQDISNDLA WFQQKPGKAPKSLIFSASSLQSGVPSKFSGSGSG TDFTLTISSLQPEDFATYYCQQSDSYPLTFGGGT KVEIK<br>SEQ ID NO: 26526 | QVQVVQSGAEVKKPGASVKVSCKASGYTFTGYFM HWVRQAPGQGLEWMGWIKPKSGGTNCAQRFQGR VTMTRDTSITTAYMELSRLRSDDTAVYYCVRGGTT VTTWGVFDYWGQGTMVTVSS<br>SEQ ID NO: 30532 |
|---|---|---|---|---|
| iPS:435747 | 21-225_175C4 | NA | GACATCCAGATGACCCAGTCTCCATCCTCACT GTCTGCATCTGTAGGAGACAGAGTCACCATCA CTTGTCGGGCGAGTCAGGGCATTAGTAATTAT TTAGCCTGGTTTCAGCAGAAACCAGGGAAAGC CCCTAAGTCCCTGATCTATGCTGCATCCGTTT GCAAAGTGGGTTCCCATCAAAATTCAGCGGCA GTGGATCTGGGACAGATTTCACTCTCACCATC AGCAGCCTACAGCCTGAAGATTTTGCAACTTA TTACTGCCAACAGTATTATAGTTACCCATTCAC TTTCGGCCCTGGGACCAAAGTGGATATCAAA<br>SEQ ID NO: 26527 | GAGGTGCAGCTGTTGGAGTCTGGGGGAGGCTTG GTGCAGCCTGGGGGGTCCCTGAGACTCTCCTGTG CAGCCTCTGCATTCACCTTTAGCAGCTATGTCAT GAGCTGGGTCCGCCAGGCTCCAGGGAAGGGGCT GGAGTGGGTCTCTGCTATTAGTGGTAGTGGTGAT AGAACATACTACGCAGACTCCGTGAAGGGCCGG TTCACCATCTCCAGAGACGAATTCCAATACCACGC TGTATCTGCAAATGAACAGCCTGAGAGCCGAGG ACACGGCCGTATATTACTGTGCGAGAACAGCGG GCTTTGACTACTGGGGCCAGGGAACCCTGGTCAC CGTCTCCTCA<br>SEQ ID NO: 30533 |
| | | AA | DIQMTQSPSSLSASVGDRVTITCRASQGIGNYLA WFQQKPGKAPKSLIYAASGLQSGFPSKFSGSGSG TDFTLTISSLQPEDFATYYCQQYYSYPFTFGPGT KVDIK<br>SEQ ID NO: 26528 | EVQLLESGGGLVQPGGSLRLSCAASAFTFSSYVMS WVRQAPGKGLEWVSAISGSGDRTYYADSVKGRFTI SRDDSNTTLYLQMNSLRAEDTAVYYCARTAGFDY WGQGTLVTVSS<br>SEQ ID NO: 30534 |

FIGURE 50
(Continued)

| | | | |
|---|---|---|---|
| iPS:435749 | 21-225_175C10 | NA | GACATCCAGATGACCCAGTCTCCATCTTCCGT GTCTGCATCTGTAGGAGACAGAGTCACCATCA CTTGTCGGGCGAGTCAGGGTATTACCGACTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTTCACTCTCACCTT CAGCAGCCTGCAGCCTGACGATTTGCAACTT ACTATTGTCAACAGACTAACAGTTCCCGTGG ACGTTCGGCCAAGGGACCAAGGTGGAAATCA AA <br> SEQ ID NO: 26529 | GAGGTGCAACTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCGTCTATTAGTGGTGTGGTGGT AGCACGTTCTACGGAGACTCCGTGAAGGGCCGGT TCACCGTCTCCAGAGACAATTCCAAGAACACGCT GTATCTGCAAATGAACAGCCTGAGAGCCGAGA CACGGCCGTATATTACTGTGCGAAATGAATAGC AGTGGCTGGTTTGACTACTGGGGCCAGGGAACCC TGGTCACCGTCTCCTCA <br> SEQ ID NO: 30535 |
| | | AA | DIQMTQSPSSVSASVGDRVTITCRASQGITDWLA WYQQKPGKAPKLLIYAASSLQSGVPSRFSGSGS GTDFTLTFSSLQPDDFATYYCQQTNSFPWTFGQ GTKVEIK <br> SEQ ID NO: 26530 | EVQLLESGGGLVQPGGSLRLSCAASGFTFSSYAMS WVRQAPGKGLEWVSSISGRGGSTFYADSVKGRFT VSRDNSKNTLYLQMNSLRAEDTAVYYCAKSNSSG WFDYWGQGTLVTVSS <br> SEQ ID NO: 30536 |
| iPS:435751 | 21-225_175D10 | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATAACAAGAACTACTTAGCTTGGTACCA GCAGAAACCAGGACAGCCTCCTAACCTGCTCA TTTACTGGACATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCTCGACGTTCGGCCAAGG GACCAAGGTGGAAATCAAA <br> SEQ ID NO: 26531 | CAGGTGCAGTCGTGCAGTCTGGGGCTGAGGTG AAGAAGCCTGGGGCCTCAGTGAAGGTCTCCTGC AAGGCTTCTGGTTACACCTTCACCAATTATGATC TCAACTGGGTGCGACAGGCCACTGGACAAGGGC TTGAGTGGATGGGATGGATGCACCTAACAGTGG TAACACAGGCTATGCACAGAAGTTCCAGGGCAG AGTCACCATGACCAGGAACACCTCCATAAGCAC AGTTTACATGGAGCTGAGCAGCCTGAGATCTGAG GACACGGCCGTGTATTACTGTGCGTATAGCAGTG GCTGGTACTACTTTGACTACTGGGGCCAGGGAAC CCTGGTCACCGTCTCCTCA <br> SEQ ID NO: 30537 |

FIGURE 50
(Continued)

| | | | |
|---|---|---|---|
| iPS:435753 | 21-225_175G10 | AA | DIVMTQSPDSLAVSLGERATINCKSSQSVLYSSN NNNYLAWYQQKPGQPPNLLIYWTSTRESGVPDR FSGSGSGTNFTLTISSLQAEDVAVYYCQQYYSTP PTFGQGTKVEIK<br>SEQ ID NO: 26532 | QVQLVQSGAEVKKPGASVKVSCKASGYTFTNYDL NWVRQATGQGLEWMGWMHPNSGNTGYAQKFQG RVTMTRNTSISTVYMELSSLRSEDTAVYYCAYSSG WYYFDYWGQGTLVTVSS<br>SEQ ID NO: 30538 |
| | | NA | GACATCCAGATGACCCAGTCTCCATCCTCCCT GTCTGCATCTGTAGGAGACAGAGTCATCATCA CTTGCCGGGCAAGTCAGAGACCATTGGCAACTAT TAAATTGGTATCAGCAGAAACCAGGGAGAG CCCCTAAGCTCCTGATCTATGCTGCATCCAGTT TGCACAGTGGGGTCCCATCAGGGTTCAGTGGC AGTGGATCTGGGACAGATTTCACTCTCACCAT CAGCAGTCTGCAACCTGAAGATTTTGCAACTT ACTTCTGTCAACAGAGTTACAGAACCCCTCAG TGGACGTTCGGCCAAGGGACCAAGGTGGAAA TCAAA<br>SEQ ID NO: 26533 | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATGCCATG AGCTGGGTCCGCCAGACTCCAGGGAAGGGGCTG GAGTGGGTCTCAATTATTAGTGGTAGTGGTGGTA ACACATACTACGCAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGCGAAAAGGGATACCT GGAACGGTTGGGATGCTTTTGATATCTGGGGCCA AGGGACAAATGGTCACCGTCTCTCTTTA<br>SEQ ID NO: 30539 |
| | | AA | DIQMTQSPSSLSASVGDRVIITCRASQTIGNYLN WYQQKPGRAPKLLIYAASSLHSGVPSGFSGSGS GTDFTLTISSLQPEDFATYFCQQSYRTPQWTFGQ GTKVEIK<br>SEQ ID NO: 26534 | EVQLLESGGGLVQPGGSLRLSCAASGFTFSSYAMS WVRQTPGKGLEWVSIISGSGGNTYYADSVKGRFTI SRDNSKNTLYLQMNSLRAEDTAVYYCAKRDTWN GWDAFDIWGQGTMVTVSL<br>SEQ ID NO: 30540 |

FIGURE 50
(Continued)

| | | | | |
|---|---|---|---|---|
| iPS:435755 | 21-225_176H4 | NA | GATATTGTGATGACCCAGACTCCACTCTCT GTCCGTCACCCCTGGACAGCCGGCCTCCATCT CCTGCAAGTCTAGTCAGAGCCTCCTGCATGT GATGGAAAGAACCTATTTGTATTGGTACCTGCA GAAGCCAGGCCAGCCTCCACAGTCTGATCT ATGAAGTTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGGATTTATTACTGCATGCAAAG TATACAGATTCCGTGGACGTTCGGCCAAGGGA CCAGGGTGGAAATCAAA<br><br>SEQ ID NO: 26535 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAATTATATGGTATGATGGAAGT TATAAATACTATGCAGACTCCGTGAAGGGCCGAT TCACCATCTCCAGAGACAATTCCAAGAACACGCT GTATCTGCAAATGAGCAGCCTGAGAGCCGAGGA CACGGCTGTGTATTACTGTGCGAGAGATGCCAC GATTTTTGGAGTGGTTACTTTGCCTACTGGGGCC AGGGAGCCCTGGTCACCGTCTCCTCA<br><br>SEQ ID NO: 30541 |
| | | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGIYYCMQSIQIPWT FGQGTRVEIK<br><br>SEQ ID NO: 26536 | QVQLVESGGGVVQPGRSLRLSCAASGFTFSSYGMH WVRQAPGKGLEWVAIIWYDGSYKYYADSVKGRFT ISRDNSKNTLYLQMSSLRAEDTAVYYCARDAHDF WSGYFAYWGQGALVTVSS<br><br>SEQ ID NO: 30542 |
| iPS:435759 | 21-225_176E6 | NA | GACATTGTGATGACTCAGTCTCCACTCTCCCTG CCCGTCACCCCTGGAGAGCCGGCCTCCATCTC CTGCAAGTCTAGTCAGAGCCTCCTGCATAATA ATGGATACAACTATTTGGATTGGTACCTGCAG AAGCCAGGCCAGTCTCCACAGCTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTGGAGGCTGA GGATGTTGGGGTTTATTACTGCATGCAAGTTC TACAAACTCCGTGGACGTTCGGCCAAGGGACC AAGGTGGAAATCAAA<br><br>SEQ ID NO: 26537 | GAGGTGCAACTGGTGGAGTCTGGGGGAGGCTTG GTACAGCCTGGGGGGTCCCTGAGACTCTCCTGTG CAGCCTCAGGATTCACCTTCAGTGGCCATAGTAT GAACTGGGTCCGCCAGGCTCCAGGAAGGGCT GGAGTGGGTTGCATACATTAGCATTAGTGGTAGT ACCATAAAGTACGCAGACTCTGTGAAGGGCCGA TTCATCATCTCCAGAGACAATGCCAGGATTCAC TGTATCTGCAAATGAACAGCCTGAGAGACGAGG ACACGGCTGTGTATTACTGTGCGAGAAGGGGGAT TACTGTGGTTCGGAATGAGGACGGTTTGGACGTC TGGGGCCAAGGGACCACGGTCACCGTCTCCTCA<br><br>SEQ ID NO: 30543 |

FIGURE 50
(Continued)

| | | | |
|---|---|---|---|
| | | AA | DIVMTQSPLSLPVTPGEPASISCRSSQSLLHNNGY KYLDWYLQKPGQSPQLLIYLGSNRASGVPDRFS ASGSGTDFTLKISRVEAEDVGVYYCMQVLQTPW TFGQGTKVEIK<br>SEQ ID NO: 26538 | EVQLVESGGGLVQPGGSLRLSCAASGFTFSGHSMN WVRQAPGKGLEWVAYISISGSTIKYADSVKGRFIIS RDNARDSLYLQMNSLRDEDTAVYYCARRGITVVR NEDGLDVWGQGTTVTVSS<br>SEQ ID NO: 30544 |
| iPS:435761 | 21-225_176B11 | NA | GACATCCAGATGACCCAGTCTCCATCCCCT GTCTGCATCTGTAGGAGACAGAGTCACCATCA CTTGCCGGGCAAGTCAGGCAGTTAGAAATGAT TTAGGCTGGTTTCAGCAGAAACCAGGGAAAGC CCCTAAGCGCCTGATCTATGCTGCATCCAGTTT GCAAAGTGGGGTCCCATCAAGGTTCAGCGGCA GTGGATCTGGGACAGACCTGAAGATTTGCAACTA AGCAGCCTGAGCGGCCTGAAGATTTTGCAACTA TTATTGTCTACAGCATTATAGTTACCCGCTCAC TTTCGGCGGAGGGACCAAGGTGGAGATCAAA<br>SEQ ID NO: 26539 | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGTCAATTATATGTATGATGGAACT AATAAATACTATGCAGACTCCGTGAAGGGCCGA TTCACCATCTCCAGAGACACAATTCCAAGAACACGC TGTTTCTGCAACTGAACAGCTGAGAGCCGAGGA CACGGCTGTCTATTACTGTGCGGAGATCCCTTA CGTGGATACAATGACCCGGTTTGGACTACTGGGG GCCAGGGAACCCTGGTCACCGTCTCCTCA<br>SEQ ID NO: 30545 |
| | | AA | DIQMTQSPSSLSASVGDRVTITCRASQGIRNDLG WFQQKPGKAPKRLIYAASSLQSGVPSRFSGSGSG TEFTLTLSSLQPEDFATYYCLQHYSYPLTFGGGT KVEIK<br>SEQ ID NO: 26540 | QVQLVESGGGVVQPGRSLRLSCAASGFTFSTYGMH WVRQAPGKGLEWVSIIWYDGTNKYYADSVKGRFT ISRDNSKNTLFLQLNSLRAEDTAVYYCARDPLRGY NDPVLDYWGQGTLVTVSS<br>SEQ ID NO: 30546 |

FIGURE 50
(Continued)

| | | | |
|---|---|---|---|
| iPS:435763 | 21-225_176H12 | NA | GACATCCAGATGACCCAGTCTCCATCCTCCT GTCTGCATCTGTAGGAGACAGAGTCACCATCA CTTGCCGGGCAAGTCAGGCATTAGAAATGAT TTAGGCTGGTATCAGCAGAAACCAGGGAAAG CCCCTAACCGCCTGATCTATGCTGCATCCAGT TGCAAAGTGGGGTCCCATCACGGTTCAGCGGC AGTGGATCTGGGACAGAATTCACTCTCACAAT CAGCAGCCTGCAGCCTGAAGATTTTGCAACTT ATTACGGTCTACAGCATATAGTTACCCTCGC AGTTTTGGCCAGGGGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGGCAGTTATATGGTATGATGGAAGT AATAAATACTATGCCGACTCCGTGAAGGGCCGAT TCACCATCTCCAGAGACAATTCCAAGAACACGCT GTATCTGCAAATGAACAGCCTGAGAGCCGAGGA CACGGCTGTATATTACTGTGCAGAGAAAAGTAT AGCAGCAACTGGTACGACTACGGTATGGACGTCT GGGGCCAAGGGACCACGGTCACCGTCTCCTCA |
| | | | SEQ ID NO: 26541 | SEQ ID NO: 30547 |
| | | AA | DIQMTQSPSSLSASVGDRVTITCRASQGIRNDLG WYQQKPGKAPNRLIYAASSLQSGVPSRFSGSGS GTEFTLTISSLQREDFATYYGLQHNSYPRSFPGQG TKLEIK | QVQLVESGGGVVQPGRSLRLSCAASGFTFSDYVM HWVRQAPGKGLEWVAVIWYDGSNKYYADSVKGR FTISRDNSKNTLYLQMNSLRAEDTAVYYCAREKYS SNWYDYGMDVWGQGTTVTVSS |
| | | | SEQ ID NO: 26542 | SEQ ID NO: 30548 |
| iPS:435765 | 21-225_177D3 | NA | GACATCCAGATGTCCCAGTCTCCATCCTCACT GTCTGCTCTGTAGGAGACAGAGTCACCATCA CTTGTCGGGCGAGTCAGGGCATTAGCAATCA TTAGCCTGGTTTCAGCAGAAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTATAGTTACCTA TTACTGCCAACAGTATATAGTTACCCATTCA CTTTCGGCCCTGGGACCAAAGTGGATATCAAA | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCTATGTCATG AACTGGGTCCGCCAGGCTCCAGGGAAGGGGCTG GAGTGGGTCTCAGGTATGAGCGGTAGTGGTGTA GAACATACTACGCAGACTCCGTGAAGGACCGGT TCACCATCTCCAGAGACAATTCCAAGAACAGCT GTCTCTGCAAATGAACAGCCTGAGGGCCGAGGA CACGGCCGTATATTACTGTGCGAGAGTGACTTTC TTTGACTATTGGGGCCAGGGAACCCTGGTCACCG TCTCCTCA |
| | | | SEQ ID NO: 26543 | SEQ ID NO: 30549 |

FIGURE 50
(Continued)

| | | | | |
|---|---|---|---|---|
| iPS:435767 | 21-225_177B4 | AA | DIQMSQSPSSLSASVGDRVTITCRASQGITNYLAWFQQKPGKAPKSLIYAASSLQSGVPSKFSGSGSGTDFTLTISSLQPEDFATYYCQQYNSYPFTFGPGTKVDIK<br><br>SEQ ID NO: 26544 | EVQLLESGGGLVQPGGSLRLSCAASGFTFSSYVMNWVRQAPGKGLEWVSGMSGSGGRTYYADSVKDRFTISRDNSKNTLSLQMNSLRAEDTAVYYCARVTFFDYWGQGTLVTVSS<br><br>SEQ ID NO: 30550 |
| | | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGAAAGCCCCTAAGCGCCTGATCTATGCTGCATCCAGTTTGCAAAGTGGGGTCCCATCCAAGGTTCAGCGGCAGTGGATCTGGGACAGAATTCACTCTCACAATCAGCAGCCTGCAGCCTGAAGATTTTGCAACTTATTACTGTCTACAGCATTATAGTTTCCCTCGCAGTTTTGGCCAGGGGACCAAGCTGGAGATCAAA<br><br>SEQ ID NO: 26545 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGTTATGTCATGAACTGGGTCCGCCAGGCTCCAGGCAAGGGGCTGGAGTGGGTGGCAGTTATATGCAGACTCCGTGAAGGGCCGATTCATAGTCTCCAGAGACAATTCCAAGAACACGCTGTATCTGCAAATGAACAGCCTGAGAGCCGAGGACACGGCTGTGTATTACTGTGCGAGAGAAAAGTATAGCAGCAGCTGGTACGACTACGGTTTGGACGTCTGGGGCCAAGGGACCACGGTCACCGTCTCCTCA<br><br>SEQ ID NO: 30551 |
| | | AA | DIQMTQSPSSLSASVGDRVTITCRASQGIRNDLGWYQQKPGKAPKRLIYAASSLQSGVPSRFSGSGSGTEFTLTISSLQPEDFATYYCLQHYSFPRSFGQGTKLEIK<br><br>SEQ ID NO: 26546 | QVQLVESGGGVVQPGRSLRLSCAASGFTFSDYYMHWVRQAPGKGLEWVAVIWYDGSNKYYADSVKGRFIVSRDNSKNTLYLQMNSLRAEDTAVYYCAREKYSSSWYDYGLDVWGQGTTVTVSS<br><br>SEQ ID NO: 30552 |

FIGURE 50
(Continued)

| | | | | |
|---|---|---|---|---|
| iPS:435769 | 21-225_177B6 | NA | GACATCCAGATGACCCAGTCTCCATCCTCCCTGTCTGCATCTGTAGGAGACAGAGTCACCATCACTTGCCGGGCAAGTCAGGACATTAGCAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGTTCTGGGACAGATTTCACTCTCACAATCAACAGCCTGCAGCCTGAAGATTTTGCAACTTATTACTGTCTACAGCTTAATAGTTACCCATTCACTTTCGGCCCTGGGACCAAAGTGGATATCAAA | DIQMTQSPSSLSASVGDRVTITCRASQDISNDLGWYQQKPGKAPKRLIYAASSLQSGVPSRFSGSGSGTEFTLTINSLQPEDFATYYCLQLNSYPFTFGPGTKVDIK | GAGGTGCAGCTGTTGGAGTCTGGGGGAGGCTTGGTACAGCCGGGGGGGTCCCGGAGACTCCTGTGAAGCCTCTGGATTCACCTTTAGCAGTTATGCCATGAGCTGGGTCCGCCAGGCTCCAGGGAAGGGGCTGGAGTGGGTCTCAGTTATTAGTGGTAGTGGTAGTAACACATACTACGTAGACTCCGTGAAGGGCCGGTTCACCATCTCCAGAGACAATTCCAAGAACACGCTGAATCTGCAAATGAACAGCCTGAGAGCCGAGGACTCGGCCGTATATTACTGTGTACGAAAGGTTACTAACTTTTGACTTCTTGATAGTAGTGGTTATTACTACCCTTTGACTTCTGGGGCCAGGGAACCCTGGTCACCGTCTCCTCA | EVQLLESGGGLVQPGGSRRLSCEASGFTFSSYAMSWVRQAPGKGLEWVSVISGSGSNTYYVDSVKGRFTISRDNSKNTLNLQMNSLRAEDSAVYYCTKGYYDSSGYYYPFDFWGQGTLVTVSS |
| | | | SEQ ID NO: 26547 | SEQ ID NO: 26548 | SEQ ID NO: 30553 | SEQ ID NO: 30554 |
| iPS:435771 | 21-225_177B11 | NA | GATATTGTGATGACCCAGACTCCACTCTCTCTGTCCGTCACTCCTGGACAGCCGGCCTCCATCTCCTGCAAGTCTAGTCAGAGCCTCCTGCATGGTGATGGAAAGACCTATTTGTATTGGTACCTGCAGAAGCCAGGCCAGCCTCCACAGACTCCTGATCTATGAAGTTTCCAACCGGTTCTCTGGAGTGCCAGATAGGTTCAGTGGCAGCGGGTCAGGGACAGAGTTCACACTTAAAATCAGCCGGGTGGAGGCTGAGGATGTTGGGGTTTATTACTGCATGCAAAGTATACAGATTCCGTGGACGTTCGGCCAAGGGACCAAGGTGGAAATCAAA | NA | CAGGTGCAACTGGTGGAGTCTGGGGGAGGCGTGGTCCAGCCTGGGAGGTCCCTGAGACTCACCTGTGCAGCGTCTGGATTCACCTTCAGTAGCTATGGCATGCACTGGGTCCGCCAGGCTCCAGGCAAGGGGCTGGAGTGGGTGGCAATTATATCGACTCCGTGAAGTGATGAAGTTATAAATACTATACAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGACTTACGATTTTTGGAGTGGTTATTTGTCTTCTGGGGCCAGGGAACCCTGGTCACCGTCTCCTCA | |
| | | | SEQ ID NO: 26549 | | SEQ ID NO: 30555 | |

FIGURE 50
(Continued)

| | | | |
|---|---|---|---|
| iPS:435773 | 21-225_177B12 | AA | DIVMTQTPLSLSVTPGQPASISCKSSQRLLHGDG KTYLYWYLQKPGQPPQILIYEVSNRFSGVPDRFS GSGSGTEFTLKISRVEAEDVGVYYCMQSIQIPWT FGQGTKVEIK<br>SEQ ID NO: 26550 | QVQLVESGGGVVQPGRSLRLTCAASGFTFSSYGMH WVRQAPGKGLEWVAIIWYDGSYKYYTDSVKGRFT ISRDNSKNTLYLQMNSLRAEDTAVYYCARETYDF WSGYFVFWGQGTLVTVSS<br>SEQ ID NO: 30556 |
| | | NA | GACATCGTGATGACCCAGTCTCCAGACTCCCT GGCTGTGTCTCTGGGCGAGAGGGCTACCGTCA ACTGCAAGTCCAGCCAGAGTGTTTACACAGC TCCAACAATAACAACTACTTAACTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTAGTCCCGACGTTCGGCCAAGG GACCAAGGTGGAAATCAAA<br>SEQ ID NO: 26551 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGTATAGCAGT GGCTGGTACTACTTTGACTTTCTGGGGCCAGGGAA CCCTGGTCACCGTCTCCTCA<br>SEQ ID NO: 30557 |
| | | AA | DIVMTQSPDSLAVSLGERATVNCKSSQSVLHSSN NNNYLTWYQQKPGQPPKLLIYWASTRESGVPDR FSGSGSGTDFTLTISSLQAEDVAVYYCQQYYSSP PTFGQGTKVEIK<br>SEQ ID NO: 26552 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YYFDFWGQGTLVTVSS<br>SEQ ID NO: 30558 |

FIGURE 50
(Continued)

| | | | |
|---|---|---|---|
| iPS:435775 | 21-225_178A5 | NA | GACATCCAGATGACCCAGTCTCCATCTTCCGT GTCTGCATCTGTAGGAGACAGAGTCACCATCA CTTGTCGGGCGAGTCAGGTATTAGCAACTGG TTAGCCTGGTATCAGCAGAAACCAGGGAAAG CCCCTAAGCTCCTGATCTATGCTGCTTCCAGTT TGCAAAGTGGGGTCCCATCAAGGTTCAACGGC AGTGGATCTGGGACAGATTTCACTCTCACCAT CAGCAGCCTGCAGCCTGAAGATTTTGCAACTT ACTGTTGTCAACAGGCTAACAGTTACCGTGG ACGTTCGGCCAAGGGACCAAGGTGGAAATCA AA SEQ ID NO: 26553 | GAGGTGCACCTGTTGGAGTCTGGGGGAGGCTTGG TACAGACTCTGGGGGGTCCCTGAGACTCTCCTGTGC AGCCTCTGGATTCACCTTTAGCAGCTATGCCATG ACCTGGGTCCGCCAGGCTCCAGGGAAGGGGCTG GAGTGGGGTCTCAGTTATTAGTGGTAGTGGTGTA ATACATTCTACGCAGACTCCGTGAAGGGCCGGTT CACCATCTCCAGAGACAATTCCAAGAATACGCTG TATCTGCAAATGAACAGCCTGAGAGCCGAGGAC ACGGCCGTATATTACTGTGCGCGCCGGGACGGTG ACTACTTTGACTACTGGGGCCAGGGAACCCTGGT CACCGTCTCCTCA SEQ ID NO: 30559 |
| | | AA | DIQMTQSPSSVSASVGDRVTITCRASQGISNWLA WYQQKPGKAPKLLIYAASSLQSGVPSRFNGSGS GTDFTLTISSLQPEDFATYCCQQANSLPWTFGQG TKVEIK SEQ ID NO: 26554 | EVHLLESGGGLVQTGGSLRLSCAASGFTFSSYAMT WVRQAPGKGLEWVSVSGSGGNTFYADSVKGRFTI SRDNSKNTLYLQMNSLRAEDTAVYYCARRDGDYF DYWGQGTLVTVSS SEQ ID NO: 30560 |
| iPS:435777 | 21-225_178F7 | NA | GACATCCAGATGACCCAGTCTCCATCTTCCGT GTCTGCATCTGTAGGAGACAGAGTCACCATCA CTTGTCGGGCGAGTCAGGATATTACTAACTGG TTAGCCTGGTATCAGCAGAAACCAGGGAAAG ACCTGGGTCCGCCAGGCTCCAGGGAAGGGCTG GAGTGGGGTCTCAGTTATTAGTGGTCATCCAGTT TGCAAGAGTGGGGTCCCATCAAGGTTCAGCGGC AGTGGATCTGGGACAGATTTCACTCTCGCCAT CAGCAGCCTGCAGCCTGAAGATTTTGCAACTT ACTATTGTCAACAGGCTAACAGGCTAACAGTTTACCGTGG ACGTTCGGCCAAGGGACCAAGGTGGAAATCA AA SEQ ID NO: 26555 | GAGGTGCACCTGTTGGAGTCTGGGGGAGGCTTGG TACAGACTCTGGGGGGTCCCTGAGACTCTCCTGTGC AGCCTCTGGATTCACCTTTAGCAGCTATGCCATG ACCTGGGTCCGCCAGGCTCCAGGGAAGGGCTG GAGTGGGTCTCAGTTATTAGTGGTAGTGGTGTA ACACATTCTACGCAGACTCCGTGAAGGGCCGGTT CACCATCTCCAGAGACAATTCCAAGAACACGCTG TATCTGCAAATGAACAGCCTGAGAGCCGAGGAC ACGGCCGTATATTACTGTGCGCGCCCGTACGGTG ACTACTTTGACTACTGGGGCCAGGGAACCCTGGT CACCGTCTCCTCA SEQ ID NO: 30561 |

FIGURE 50
(Continued)

| | | | |
|---|---|---|---|
| iPS:435779 | 21-225_178B10 | AA | DIQMTQSPSSVSASVGDRVTITCRASQDITDWLA WYQQKPGKAPKLLISAASSLQSGVPSRFSGSGSG TDFTLAISSLQPEDFATYYCQQANSLPWTFGQGT KVEIK<br>SEQ ID NO: 26556 | EVHLLESGGGLVQTGGSLRLSCAASGFTFSSYAMT WVRQAPGKGLEWVSVSGSGGNTFYADSVKGRFTI SRDNSKNTLYLQMNSLRAEDTAVYYCARRYGDYF DYWGQGTLVTVSS<br>SEQ ID NO: 30562 |
| | | NA | GACATCCAGATGACCCAGTCTCCATCCTCCCT GTCTGCATCTGTCGGAGACAGAGTCACCATCA CTTGCCGGGCAAGTCAGGGCATTAGAAATGAT TTAGGCTGGTATCAGCAGAAACCAGGAAAG CCCCTAAACACCTGATCTATGCTGCATCCAGT TTGCAAAATGGGGTCCCATCAAGGTTCAGCGG CAGTGGCTCTGGGACAGAATTCACTCTCACAA TCAGCAGCCTGCAGCCTGAAGATTTTGCCACT TATTACTGTCTACACCATTATAGTTTCCCGCTC ACTTTCGGCGGAGGGACCAAGGTGGAGATCA AA<br>SEQ ID NO: 26557 | CAGGTGCAGCTGGTGGAGTCGGGGGGAGGCGTG GTCCAGCCTGGGAGGTCCCTGAGACTCTCCTGTG TAGCGTCTGGATTCACCTCCAGTACTTACGGCAT GCACTGGGTCCGCCAGGCTCCAGGCAAGGGGCT GGAATGGATGGCAATTATATGGTATGATGGAACT AATAAATACTATGCAGACTCCGTGAAGGGCCGA TTCACCATCTCCAGAGACAATTCCAAGAACACGC TGTATCTGCAACTGAACAGCCTGAGAGCCGAGG ACACGGCTGTGTATTACTGTGCGCGAGATCCCTT AGTGGATACAATGACCCGGTTATGGACTACTGG GGCCAGGGAACCCTGGTCACCGTCTCCTCA<br>SEQ ID NO: 30563 |
| | | AA | DIQMTQSPSSLSASVGDRVTITCRASQGIRNDLG WYQQKPGKAPKHLIYAASSLQNGVPSRFSGSGS GTEFTLTISSLQPEDFATYYCLHHYSFPLTFGGGT KVEIK<br>SEQ ID NO: 26558 | QVQLVESGGGVVQPGRSLRLSCVASGFTSSTYGMH WVRQAPGKGLEWMAIIWYDGTNKYYADSVKGRF TISRDNSKNTLYLQLNSLRAEDTAVYYCARDPLRG YNDPVMDYWGQGTLVTVSS<br>SEQ ID NO: 30564 |

FIGURE 50
(Continued)

| | | | |
|---|---|---|---|
| iPS:435781 | 21-225_178G10 | NA | CATATTGTGATGACCCAGACTCCACTCTCTGTCCGTCACCCCTGGACAGCCGGCCTCCATCTCCTGCAAGTCTAGTCAGAGCCTCCTGCATGGTGATGGAAAGACCTATTTGTATTGGTACCTGCAGAAGCCAGGCCAGCCTCCACAGCTCCTGATCTATGAAGTTTCCAACCGGTTTCTGGAGTGCCAGTGAAGACTCAGTGGCGCGGGTCAGGGACAGATTTCACACTGAAATCAGCAGCGGGTGGAGGCTGAGGATGTTGGCATTTATTACTGCATGCAAAGTATACAGGTTCCGTGACGTTCGGCCAAGGGACCAAGGTGGAAATCAA | CAGGTGCAGCTGGTGGAGTCTGGGGGAGGCGTGGTCCAGCCTGGGGAGGTCCCTGAGACTCTCCTGTGCAGCGTCTGGATTCACCTTCAGTACCTATGGCATGCACTGGGTCCGCCAGGCTCCAGGCAAGGGGCTGGAGTGGGTGGCAGTTATATGGTATGATGGAAGTAATAAATACTACGCAGACTCCGTGAAGGGCCGATTCACCATCTCCAGAGACAATTTCAAGAACACGCTGTATCTGCAAATGAACAGCCTGAGAGCCGAGGACACGGCTGTTTATTACTGTGCGAGAGAACGGTAACGGTTTTGGAGTGGTCATTTGACTACTGGGGCCAGGGAACCCTGGTCACCGTCTCCTCA |
| | | | SEQ ID NO: 26559 | SEQ ID NO: 30565 |
| | | AA | HIVMTQTPLSLSVTPGQPASISCKSSQSLLHGDGKTYLYWYLQKPGQPPQLLIYEVSNRFSGVPDRLSGSGSGTDFTLKISRVEAEDVGIYYCMQSIQVPWTFGQGTKVEIK | QVQLVESGGGVVQPGRSLRLSCAASGFTFSTYGMHWVRQAPGKGLEWVAVIWYDGSNKYYADSVKGRFTISRDNFKNTLYLQMNSLRAEDTAVYYCARERYDFWSGHFDYWGQGTLVTVSS |
| | | | SEQ ID NO: 26560 | SEQ ID NO: 30566 |
| iPS:435783 | 21-225_179G1 | NA | GACATCCAGATGACCCAGTCTCCATCTTCCGTGTCTGCATCTGTAGGAGACAGAGTCACCATCACTTGTCGGGCGAGTCAGGATATTAGCGACTGGCTTAGCCTGGTATCAGCAGAAATCAGGGAAAGCCCCTAAACTCCTGATCTCTGCTGCATCCAGTTTGCAAAGTGGGGTCCCATCAAGGTTCGGCGGCAGTGGATCTGGGACAGATTTCACTCTCACCATCAGCAGCCTGCAGCCTGAAGATTTTGCAACTTACTATTGTCAACAGGCTAACAGTTTACCGTGACGTTCGGCCAAGGGACCAAGGTGGAAATCAAA | GAGGTGCACCTGTTGGAGTCGGGGGGAGGCTTGGTACAGACTGGGGGGTCCCTGAGACTCTCCTGTGCAGCCTCTGGATTCACCTTTAGCAGCTATGCCATGACCTGGGTCCGCCAGGCTCCAGGGAAGGGGCTGGAGTGGGTCTCAGTTATTAGTGGTTTGGTGGTAACACATTCTACGCAGAGACAATTCCAAGAGACACGCTCAATCTGCAAATGAACAGCCTGAGAGCCGAGGAGTATCTGCAAATGAACAGCCTGAGAGCCGAGGACACGGCCGTATATTACTGTGCGCGCCGGTACGGTGACTACTTTGACTACTGGGGCCAGGGAACCCTGGTCACCGTCTCCTCA |
| | | | SEQ ID NO: 26561 | SEQ ID NO: 30567 |

FIGURE 50
(Continued)

| | | | |
|---|---|---|---|
| iPS:435785 | 21-225_179C2 | AA | DIQMTQSPSSVSASVGDRVTITCRASQDISDWLA WYQQKSGKAPKLLISAASSLQSGVPSRFGGSGS GTDFTLTISSLQPEDFATYYCQQANSLPWTFGQG TKVEIK<br>SEQ ID NO: 26562 | EVHLLESGGGLVQTGGSLRLSCAASGFTFSSYAMT WVRQAPGKGLEWVSVISGFGGNTFYADSVKGRFTI SRDNSKNTLYLQMNSLRAEDTAVYYCARRYGDYF DYWGQGTLVTVSS<br>SEQ ID NO: 30568 |
| | | NA | GATATTGTGATGACCCAGACTCCACTCTCTCT GTCCGTCACCCCTGGACAGCCGGCCTCCATCT CCTGCAAATCTAGTCAGAGCCTCCTGCATAGT GAGGGAAAGACCTACTTTGTATTGGTACCTGCA GAAGCCAGGCCAGTCTCCACAGTCCTGATCT ATGAGGTTTCCCACCGGTTCTCTGGAGTGCCA GATAGGTTCAGTGGCAGCGGGTCAGGGACAG ATTTCACACTGAAATCAGCCGGGTGGAGGCT GAGGATGTTGGGGTTTATTACTGCATGCAAAG TATACAGGTTCTCACTTTCGGCGGAGGGACCA AGGTGGAGATCAAA<br>SEQ ID NO: 26563 | CAGGTGCAGCTGTTGGAGTCGGGGGAGGCGTG GTCCAGCCTGGGAGGTCCCTGAGACTCTCCTGTG CAGCGTCTGGATTCACCTTCAGTAGTTATGCCAT GCACTGGGTCCGCCAGGCTCCAGGCAAGGGGCT GGAGTGGGTGGCACTTATATATTTATGATGGAAGT AATAAATACTATGCAGACTCCGTGAAGGGCCGA TTCACCATCTCAGAGACAATTCCAAGAACACGC TGTTTCTGCAAATGAACAGCCTGAGAGCCGAGG ACACGGCTGTGTATTACTGTGCGAGACGGTATAG CGGCAGCTGGTCCGGTGGTATGGACGTCTGGGGC CAAGGGACCACGGTCACCGTCTCCTCA<br>SEQ ID NO: 30569 |
| | | AA | DIVMTQTPLSLSVTPGQPASISCKSSQSLLHSEGK TYLYWYLQKPGQPPQLLIYEVSHRFSGVPDRFSG SGSGTDFTLKISRVEAEDVGVYYCMQSIQVLTFG GGTKVEIK<br>SEQ ID NO: 26564 | QVQLVESGGGVVQPGRSLRLSCAASGFTFSSYGMH WVRQAPGKGLEWVALIFYDGSNKYYADSVKGRFT ISRDNSKNTLFLQMNSLRAEDTAVYYCARRYSGSW SGGMDVWGQGTTVTVSS<br>SEQ ID NO: 30570 |

FIGURE 50
(Continued)

| | | | |
|---|---|---|---|
| iPS:435787 | 21-225_180A3 | NA | GACATCCAGATGACCCAGTCTCCATCTTCCGT GTCTGCATCTGTAGGAGACAGAGTCACCATCA CTTGTCGGGCGAGTCAGGATATTACCAGCTGG TTAGCCTGGTATCAGCAGAAACCAGGGAAAG CCCCTAAGCTCCTGATCTATGCTGCATCCAGT TGCAAAGTGGGGTCCCATCAAGGTTCAGCGGC AGTGGATCTGGGACAGATTTCATTCTCACCAT CAGCAGCCTGCAGCCTGAAGATTTTGCATTTT ACCATTGTCAACAGGCTAACAGTATCCCATTC ACTTTCGGCCCTGGGACCAAAGTGGACATCAA C |
| | | | SEQ ID NO: 26565 |
| | | AA | DIQMTQSPSSVSASVGDRVTITCRASQDITSWLA WYQQKPGKAPKLLIYAASSLQSGVPSRFSGSGS GTDFILTISSLQPEDFAFYHCQQANSIPFTFGPGT KVDIN |
| | | | SEQ ID NO: 26566 |
| iPS:435789 | 21-225_180C4 | NA | GATATTGTGATGACCCAGACTCCACTCTCTCT GTCCGTCACCCCTGGACAGCCGGCCTCCATCT CCTGCAAGTCTAGTCAGAGCCTCCTGCATGGT GATGGAAAGACCTATTTGTATTGGTACCTGCA GAAGCCAGGCCAGTCCCCACAGCTCCTGATCT ATGCAACTTCCAACCGGTTCCCTGGAGTGTCA GATAGGTTCAGTGGCAGCGGGTCAGGTACAG ACTTCACACTGAAAATCAGCCGGGTGGAGGCT GAGGATGTTGGGGTTTATTACTGCATGCAAAG TATACAGGTTCCGTGGACGTTCGGCCAAGGGA CCAAGGTGGAAATCAAA |
| | | | SEQ ID NO: 26567 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTGCCTATGCAT GCACTGGGTCCGCCAGGCTCCAGGCAAGGGGCT GGAGTGGGTGGACAATTATTGGTATGATGGAAGT TATAAATACTATGCAGACTCCGTGAAGGGCCGAT TCGCCATCTCCAGAGACAACAGCCTGAGAGCCGA GTATCTGCAAATGAACAGCCTGAGAGCCGAGGA CACGGCTGTGTATTACTGTGCGAGAACCGGTGTG GATCCCTGGGACTACTACAACGGAATGGACGTCT GGGGCCAAGGGACCACGGTCACCGTCTCCTCA |
| | | | SEQ ID NO: 30573 |

| | | | GAGGTGCAGCTGTTGGAGTCTGGGGGAGGCTTG GAACAGCCTGGGGGGTCCCTGAGACTCTCCTGTG CAGCCTCTGGATTCACCTTTAGCAGCTTTGCCAT GAACTGGGTCCGCCAGGCTCCAGGGAAGGGGCT GGAGTGGGTCTCAGTTATTAGCGGTCGCGGTGT AACACATTCTACGCAGACTCCGTGAAGGGCCGGT TCACCATCTCCAGAGACAATTCCAAGAACACGCT GTTTCTGCAAATGAACAGCCTGAGAGCCGAGGA CACGGCCGTATATTCTGTGCGAAACGGACTGGG GATGATGTTTTTGATGTCTGGGGCCAAGGGACAA TGGTCACCGTCTCTTCA |
| | | | SEQ ID NO: 30571 |
| | AA | EVQLLESGGGLEQPGGSLRLSCAASGFTFSSFAMN WVRQAPGKGLEWVSVISGRGGNTFYADSVKGRFTI SRDNSKNTLFLQMNSLRAEDTAVYFCAKRTGDDV FDVWGQGTMVTVSS |
| | | SEQ ID NO: 30572 |

FIGURE 50
(Continued)

| | | | |
|---|---|---|---|
| iPS:435791 | 21-225_180H7 | AA | DIVMTQTPLSLSVTPGQPASISCKSSQSLLHGDG KTYLYWYLQKPGQPPQLLIYATSNRFPGVSDRFS GSGSGTDFTLKISRVEAEDVGVYYCMQSIQVPW TFGQGTKVEIK<br>SEQ ID NO: 26568 | QVQLVESGGGVVQPGRSLRLSCAASGFTFSAYGM HWVRQAPGKGLEWVTIIWYDGSYKYYADSVKGRF AISRDNSKNTLYLQMNSLRAEDTAVYYCARTGVDP WDYYNGMDVWGQGTTVTVSS<br>SEQ ID NO: 30574 |
| | | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGAAAG CCCCTAAGCGCCTGATCTATACTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCATCT TATTACTGTCTACAGCATAATAGTTACCCATTC ACTTTCGGCCCTGGGACCAAAGTGGATTTCAA A<br>SEQ ID NO: 26569 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGACT GGAGTGGGTGGCAGTTATATGGTATGATGGAAAT AATAAACACTATGCAGACTCCGCGAAGGGCCGA TTCACCATCTCAAGAGACAATTCCAAGAACACGC TGTATCTGCAAATGAACAGCCTGAGAGTCGAAG ACACGGCTGTGTATTACTGTGCGAGAGAGGTTGG CTGGTCCGATGACTACTGGGGCCAGGGAACCCTG GTCACCGTCTCCTCA<br>SEQ ID NO: 30575 |
| | | AA | DIQMTQSPSSLSASVGDRVTITCRASQGIRNDLG WYQQKPGKAPKRLIYTASSLQSGVPSRFSGSGSG TEFTLTISSLQPEDFASYYCLQHNSYPFTFGPGTK VDFK<br>SEQ ID NO: 26570 | QVQLVESGGGVVQPGRSLRLSCAASGFTFSDYGM HWVRQAPGKGLEWVAVIWYDENNKHYADSAKGR FTISRDNSKNTLYLQMNSLRVEDTAVYYCAREVG WSDDYWGQGTLVTVSS<br>SEQ ID NO: 30576 |

FIGURE 50
(Continued)

| | | | | |
|---|---|---|---|---|
| iPS:435793 | 21-225_180F8 | NA | GACATCCAGATGACCCAGTCTCCATCCTCCCTGTCTGCATCTGTAGGAGACGGAGTCACCATCACTTGCCGGGCAAGTCAGACAGCCATTCAGCTATTTAAATTGGTATCAGCAGAAACCAGGGAAAGCCCCTAAACTCCTGATCTATGGTGTATCCAGTTTACAAAGTGGGGTCCCATCAAGGTTCAGTGGCAGTGGATCTGGGACAGATTTTCTCTCTCACCATCAGCAGTCTGCAACCTGAAGATTTTGCAACTACTACTGTCAGCAGAGTTACAGTACCCCATTCACTTTCGGCCCTGGGACCAAAGTGGATATCAAA SEQ ID NO: 26571 | CAGGTGCAGCTGGTGGAGTCTGGGGGAGGCGTGGTCCAGCCTGGGAGGTCCCTGAGACTCTCCTGTCAGCCTCTGGATTCACCTTCAGTAGCTATGGCATGCACTGGGTCCGCCAGGCTCCAGGCAAGGGCTGGAGTGGGTGTCAGTTATATGGTATGAAGTGATAAATACTATGAAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCATCCCCGGGTGAGCTACGGAGACTACTGGGGCCAGGGAACCCTGGTCACCGTGTCCTCA SEQ ID NO: 30577 |
| | | AA | DIQMTQSPSSLSASVGDGVTITCRASQTILSYLNWYQQKPGKAPKLLIYGVSSLQSGVPSRFSGSGSGTDFSLTISSLQPEDFATYYCQQSYSTPFTFGPGTKVDIK SEQ ID NO: 26572 | QVQLVESGGGVVQPGRSLRLSCAASGFTFSSYGMHWVRQAPGKGLEWVSVIWYDGSDKYYEDSVKGRFTISRDNSKNTLYLQMNSLRAEDTAVYYCARDHPRWSYGDYWGQGTLVTVSS SEQ ID NO: 30578 |
| iPS:435795 | 21-225_181C2 | NA | GAAATTGTGATGACCCAGACTCCACTCTCTGTCCGTCACCCTGGACAGCCAGCCGGCCTCCATCTCCTGCAAGTCTAGTCAGAGCCTCCTGCATGGTGATGGAAAGACATCTATTTGTATTGGTACCTGCAGAAGCCAGGCCAGCCTCCACAGTCTCTGATCCATGAAGTTTCCAACCGGTTCTCTGGAGTGCCAGATAGGTTCAGTGGCAGCGGGTCAGGGACAGATTTCACACTGAAAATCAGCCGGGTGGAGGCTGAGGATGTTGGGGTTTATTACTGCATGCAAAGTATACAGGTTCCCTGGACGTTCGGCCAAGGGACCAAGGTGGAAATCAAA SEQ ID NO: 26573 | CAGGTGCAGCTGGTGGAGTCTGGGGGAGGCGTGGTCCAGCCTGGGAGGTCCCTGAGACTCTCCTGTAGCGTCTGGATTCACCTTCAGTAGCTATGGCATGCACTGGGTCCGCCAGGCTCCAGGCAAGGGCTGGAATGGGTGACAATTATATGCAGACTCCGTGAAGGGCCGATTATAAATACTATGCAGAGACTCCGTGAAGGGCCGATTCACCATCTCCAAGAGACAATTCCAAGAACACGCTGTATCTGCAAATGAACAGCCTGAGAGCCGAGGACACGGCTGTGTATTACTGTGCGAGAGATCATTACGATTTTTGGAGTGGGCACTTGACTTCTGGGGCCAGGGAACCCTGGTCACCGTCTCCTCA SEQ ID NO: 30579 |

FIGURE 50
(Continued)

| | | | |
|---|---|---|---|
| | | AA | EIVMTQTPPLSLSVTPGQPASISCKSSQSLLHGDGK TYLYWYLQKPGQPPQLLIHEVSNRFSGVPDRFSG SGSGTDFTLKISRVEAEDVGVYYCMQSIQVPWT FGQGTKVEIK<br><br>SEQ ID NO: 26574 | QVQLVESGGGVVQPGRSLRLSCVASGFTFSSYGMH WVRQAPGKGLEWVTIIWYDGSYKYYADSVKGRFT ISRDNSKNTLYLQMNSLRAEDTAVYYCARDHYDF WSGHFDFWGQGTLVTVSS<br><br>SEQ ID NO: 30580 |
| iPS:435797 | 21-225_181G2 | NA | GACATCCAGATGACCCAGTCTCCATCCTCACT GTCTGCATCTATAGGAGAGAGGTCACCATCA CTTGTCGGGCGAGTCAGGGCATTAGCAATTAT TTAGCCTGGATTCAGCAGAAACCAGGGACAGC CCCTAAGTCCCTGATCTATGCTGCATCCAGTTT GCAAAGTGGGGTCTCATCAAGGTTCAGCGGCA GTGGATTTGGGACAGATTTCACTCTCACCATC AGTAGTCTGCAGCCTGAAGATTTTGCAACTTA TTACTGCCAACAGTATATGGTTACCCATTCA CTTTCGGCCCTGGGACCAAAGTGGATATCAAA<br><br>SEQ ID NO: 26575 | CAGGTGCAGCTGGTGCAGTCTGGGGCTGAAGTG AAGAGGCCTGGGGCTCAGTGAAGGTCTCCTGCA GGGCTTCTGGATACACCTTCACCAGCTACAATAT GCACTGGGTGCGACAGGTCCCTGGACAAGGGCT TGAGTGGATGGGATGGATCAACCTAACAATGGT GGCTCAAACTATACACAGAAGTTTCAGGGCAGG GTCACCATGACCAGGGACACGTCCATCAGCACA GCCTACATGGAGCTGAGCAGGCTGAGATCTGAC GACACGGCCGTGTATTACTGTGCGAGAAAGTTTG GGGACTGGGGCCAGGGAACCCTGGTCACCGTCT CCTCA<br><br>SEQ ID NO: 30581 |
| | | AA | DIQMTQSPSSLSASIGERVTITCRASQGISNYLAW IQQKPGTAPKSLIYAASSLQSGVSSRFSGSGFGTD FTLTISSLQPEDFATYYCQQYNGYPFTFGPGTKV DIK<br><br>SEQ ID NO: 26576 | QVQLVQSGAEVKTPGASVKVSCRASGYTFTSYNM HWVRQVPGQGLEWMGWINPNNGGSNYTQKFQGR VTMTRDTSISTAYMELSRLRSDDTAVYYCARKFGD WGQGTLVTVSS<br><br>SEQ ID NO: 30582 |

FIGURE 50
(Continued)

| | | | | |
|---|---|---|---|---|
| iPS:435799 | 21-225_181G3 | NA | GACATCCAGATGACCCAGTCTCCATCCTCCCT GTCTGCATCTGTAGGAGACAGAGTCAACATCA CTTGCCGGGCAAGTCACAGACATTAGCAACTAT TTAAATTGGTATCAGCAGAAAGCAGGAAAG CCCCTAACCTCTTGATCTATACTACATTGAATT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTTACAGTTCTCCTCCG TGGACGTTCGGCCAAGGGACCAAGGTGAAA TCAAA | GAGGTGCAACTGTTGGAGTCTGGGGGAGGCTTG GTACAGCCTGGGGGTCCTGAGACTCTCCTGTG CAGCCCTCTGATTCACCTTTAGCAGCTATGCCAT GAGTTGGGTCCGCCAGGCTCCAGGAAGGCT GGAGTGGGTCTCAGTTATTAGTGGTAGTGGTGGT AACACATTCTACGGAGACTCCGTGAAGGGCCGG TTCACCATCTCCAGAGACAATTCCAAGAACACGC TGTATCTGCAAATGAACAGCCTGAGAGCCGAGG ACACGGCCATATATTACTGTGCGAAACGGGAGA CCTACGACTGGGGATCCGATGCTTTTGATATCTG GGGCCAAGGGACAATGGTCACCGTCTCTCA |
| | | | SEQ ID NO: 26577 | SEQ ID NO: 30583 |
| | | AA | DIQMTQSPSSLSASVGDRVNITCRASHSISNYLN WYQQKAGKAPNLLIYTLNLQSGVPSRFSGSGS GTDFTLTISSLQPEDFATYCQQSYSSPPWTFGQ GTKVEIK | EVQLLESGGGLVQPGGSLRLSCAASGFTFSSYAMS WVRQAPGKGLEWVSVISGSGGNTFYGDSVKGRFTI SRDNSKNTLYLQMNSLRAEDTAIYYCAKRETYDW GSDAFDIWGQGTMVTVSS |
| | | | SEQ ID NO: 26578 | SEQ ID NO: 30584 |
| iPS:435801 | 21-225_181E5 | NA | GACATCGTGATGACCCAGTCTCCAGACTCCCT GGCTGTGTCTCTGGGCGAGAGGGCCACCATCA ACTGCAAGTCCAGCCAGAGTGTTTTACACAGC TCCAACAATTACAACTACTTAACTTGGTACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCATCAG TATTTTATTACTCCGTTGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTACTTTGACTACTGGGGCCAGGGA ACCCTGGTCACCGTCTCCTCA |
| | | | SEQ ID NO: 26579 | SEQ ID NO: 30585 |

FIGURE 50
(Continued)

| | | | |
|---|---|---|---|
| iPS:435805 | 21-225_181A8 | AA | DIVMTQSPDSLAVSLGERATINCKSSQSVLHSSN NYNYLTWYQQKPGQPPKLLIYWASTRESGVPDR FSGSGSGTDFTLTISSLQAEDVAVYYCHQYFITP WTFGQGTKVEIK<br>SEQ ID NO: 26580 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YIFDYWGQGTLVTVSS<br>SEQ ID NO: 30586 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAAG CCCCTAAGCGCCTGATCTATACTGCATCCAGT TTGCAAAGTGGGGTCCCATCAAGGTTCAGCGG CAGTGGATCTGGGACAGATTTCACTCTCACAA TCAGCAGCCTGCAGCCTGAAGATTTTGCATCT TATTACTGTCTACAGCATAATAGTTACCCATTC ACTTTCGGCCCTGGGACCAAAGTGGATTTCAA A<br>SEQ ID NO: 26581 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGACT GGAGTGGGTGGCAGTTATATGGTATGATGAAAAT AATAAACACTATGCAGACTCCCGAAGGCCGA TTCACCATCTCCAGAGACAATTCCAAGAACACGC TGTATCTGCAAATGAACAGCCTGAGAGCCGAAG ACACGGCTGTGTATTACTGTGCGAGAGAGGTTGG CTGGTCCGATGACTACTGGGGCCAGGGAACCCTG GTCATCGTCTCCTCA<br>SEQ ID NO: 30587 |
| | | AA | DIQMTQSPSSLSASVGDRVTITCRASQGIRNDLG WYQQKPGKAPKRLIYTASSLQSGVPSRFSGSGSG TDFTLTISSLQPEDFASYYCLQHNSYPFTFGPGTK VDFK<br>SEQ ID NO: 26582 | QVQLVESGGGVVQPGRSLRLSCAASGFTFSDYGM HWVRQAPKGLEWVAVIWYDENNKHYADSAKGR FTISRDNSKNTLYLQMNSLRAEDTAVYYCAREVG WSDDYWGQGTLVIVSS<br>SEQ ID NO: 30588 |

FIGURE 50
(Continued)

| | | | |
|---|---|---|---|
| iPS:435807 | 21-225_181C10 | NA | GATATTGTGATGACCCAGACTCCACTCTCT GTCCGTCACCCCTGGACAGCCGGCCTCCATCT CCTGCAAGTCTAGTCAGAGCCTCCTGCATGGT GATGGAAAGACCTATTTGTATTGGTACCTGCA GAAGCCAGGCCAGCCTCCACAGTCTCCTGATCT ATGAAGTTTCCAATCGGTTCTCTGGAGTGCCA GATAGGTTCAGTGGCAGCGGGTCAGGGACAG ATTTCACACTTAAAATCAGCCGGGTGGAGGCT GAGGATGTTGGGGTTTATCACTGCATGCAAAG TATACAGATTCCCTGGACGTTCGGCCAAGGGA CCAAGGTGGAAATCAAA<br><br>SEQ ID NO: 26583 | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGATGGCAATTATATGGTATGATGGAAGT TATAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATCATTAC GATTTTGACTACTGGGGCCA GGGAACCCTGGTCACCGTCTCCTCA<br><br>SEQ ID NO: 30589 |
| | | AA | DIVMTQTPLSLSVTPGQPASISCKSSQSLLHGDG KTYLYWYLQKPGQPPQLLIYEVSNRFSGVPDRFS GSGSGTDFTLKISRVEAEDVGVYHCMQSIQPWT FGQGTKVEIK<br><br>SEQ ID NO: 26584 | QVQLVESGGGVVQPGRSLRLSCAASGFTFSSYGMH WVRQAPGKGLEWMAIIWYDGSYKYYADSVKGRF TISRDNSKNTLYLQMNSLRAEDTAVYYCARDHYDF WSGHFDYWGQGTLVTVSS<br><br>SEQ ID NO: 30590 |
| iPS:435809 | 21-225_182H5 | NA | GACATCCAGATGACCCAGTCTCCATCTTCCGT GTATGCATCTGTTGGAGACAGAGTCACCATCA CTTGTCGGGCGAGTCAGGATATTACCAGCTGG TTAGCCTGGTATCAGCAGAAACCAGGGAAAG CCCCTAAACTCCTGATCTATGCTGCATCCAGTT TACAAAGTGGGGTCCCATCAAGGTTCAGCGGC AGTGGATCTGGGACAGATTTCATTCTCACCAT CACCAGCGTGCAGCCTGATGATTTTGCAACTT ACTATTGTCAACAGGTTAACAGTTTCCCATTC ACTTTCGGCCACGGGACCAAAGTGGATATCAA A<br><br>SEQ ID NO: 26585 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGTTGGGTCCGCCAGGCTCCAGGGAAGGGGCT GGAGTGGGTCTCAGTTATTAGTGGTAGTGGTGGT ACCACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGAAAACGACTGGG GATGATGTTTTTGATATCTGGGGCCAAGGGACAA TGGTCACCGTCTCTTCA<br><br>SEQ ID NO: 30591 |

FIGURE 50
(Continued)

| | | | | |
|---|---|---|---|---|
| iPS:435811 | 21-225_183H6 | AA | DIQMTQSPSSVYASVGDRVTITCRASQDITSWLA WYQQKPGKAPKLLIYAASSLQSGVPSRFSGSGS GTDFILTITSVQPDDFATYYCQQVNSFPFTFGHG TKVDIK<br><br>SEQ ID NO: 26586 | EVQLLESGGGLVQPGGSLRLSCAASGFTFSSYAMS WVRQAPGKGLEWVSVISGRGGTTFYADSVKGRFTI SRDNSKNTLYLQMNSLRAEDTAVYYCAKRTGDDV FDIWGQGTMVTVSS<br><br>SEQ ID NO: 30592 |
| | | NA | GACATCCAGATGACCCAGTCTCCATCCTCCCT GTCTGCATCTGTAGGAGACAGAGTCACCATCG CTTGCCAGGCGAGTCAGGACATTAGCAACTAT TTAAATTGGTATCAGCAGAAACCAGGGAAAGC CCCTAAGGTCCTGATCTACGATGCATCCAATT TGGAAACAGGGGTCCCAGCAGGTTCAGTGG AAGTGGATCTGGGACAGATTTTACTTTCACCA TCAGCAGCCTGCAGCCTGAAGATATTGCAACA TATTACTGTCAACAGTATGATAATCTCCCTCTC ACTTTCGGCGGAGGGACCAAGGTGGACATCA AA<br><br>SEQ ID NO: 26587 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGCAT GCACTGGGTCCGCCAGGCTCCAGGCAAGGGCT GGAGTGGGTGGCAATTATATCATATGCTGAAGT ACTAAATTCTATGCAGACTCCGTGAAGGGCCGAT TCACCATCTCCAGAGACAATTCCAAGAACACGCT GTATCTGCAAATGAACAGCTGAGAGCTGAGGA CACGGCTGTGTATTACTGTGTGAGAAGGCCCCG CAGTGGCTGGTAGAGGGCTACGGTATGGACGTCT GGGGCCAAGGGACCACGGTCACCGTCTCCTCA<br><br>SEQ ID NO: 30593 |
| | | AA | DIQMTQSPSSLSASVGDRVTIACQASQDISNYLN WYQQTPGKAPKVLIYDASNLETGVPARFSGSGS GTDFTFTISSLQPEDIATYYCQQYDNLPLTFGGG TKVDIK<br><br>SEQ ID NO: 26588 | QVQLVESGGGVVQPGRSLRLSCAASGFTFSSYGMH WVRQAPGKGLEWVAIISYAGSTKFYADSVKGRFTI SRDNSKNTLYLQMNSLRAEDTAVYYCVRRPPQWL VEGYGMDVWGQGTTVTVSS<br><br>SEQ ID NO: 30594 |

FIGURE 50
(Continued)

| | | | | |
|---|---|---|---|---|
| iPS:435813 | 21-225_183A12 | NA | GACATCCAGATGACCCAGTCTCCATCCTCCT GTGTGCCTCTGTAGGAGACAGAGTCACCATCA CTTGCCGGGCAAGTCGGAACATCAGCAACTAT TTAAATTGGTATCAGCAGAAACCAGGGAAAG CCCCTAAGCTCCTGATCTATGTTGTATCCAGTT TGCAAAGTGGGGTCCCATCAAGGTTCAGTGGC AGTGGATCTGGGACAGATTTCACTCTCACCAT CAGCAGTCTACAACAGAGTTACAGTTCCCCTCG ACTACTGTCAACAGAGTTACAGTTCCCCTCG TGGACGTTCGGCCAAGGGACCAAGGTGGATAT CAGA<br><br>SEQ ID NO: 26589 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCATCTGTGAAGT AATAAATACTATGCAGACTCCGTGAAGGGCCGA TTCACCATCTCCAGAGACAATTCCAAGAACACGC TGTATCTGCAAATGAACAGCTGAGAGAGCTGAGG ACACGGCTGTGTATTATTGTGCGAGAAGGTATAG CAGTGGCTGGACTGGTTCGACCCCTGGGGCCAG GGAACCCTGGTCACCGTCTCCTCA<br><br>SEQ ID NO: 30595 |
| | | AA | DIQMTQSPSSLCASVGDRVTITCRASRNISNYLN WYQQKPGKAPKLLIYVVSSLQSGVPSRFSGSGS GTDFTLTISSLQPEDFATYYCQQSYSSPPWTFGQ GTKVDIR<br><br>SEQ ID NO: 26590 | QVQLVESGGGVVQPGRSLRLSCAASGFTFSSYGMH WVRQAPGKGLEWVAVISSAGSNKYYADSVKGRFT ISRDNSKNTLYLQMNSLRAEDTAVYYCARRYSSG WDWFDPWGQGTLVTVSS<br><br>SEQ ID NO: 30596 |
| iPS:435815 | 21-225_190G10 | NA | GAAATTGTGTTGACGCAGTCTCCAGGCACCCT GTCTTTGTCTCCAGGGAAAGAGCCACCCTCT CCTGCAGGGCCAGTCCGAGTGTTAGCAGCAGA TTCTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CAACAGCAGACTGGAGCCTGAAGATTTTGCAG TGTATTACTGTCAGCAGCAGTATGGTAGCTCACCT CCGTGGACGTTCGGCCAAGGGACCAAGGTAG AAATCAAA<br><br>SEQ ID NO: 26591 | GAGGTGCAGCTGGTGGAGTCTGGGGGAGGCCTG GTCAAGCCTGGGGGGTCCCTGAGACTCTCCTGTG CAGCCTCTGGATTCACCTTCAGGGACTATAGCAT GAACTGGGTCCGCCAGGCTCCAGGGAAGGGGCT GGAGTGGGTCTCATCTATTAGTAGTGGTAGTGGT TACATACACTCCAGAGACTCAGTGAAGGGCCGA TTCACCATCTGCAAATGAACAGCCAAGAACTCAC ACACGGCTGTGTATTACTGTGCGAGCAACTAT GGCCCTTGACTACTGGGGCCAGGGAACCCTGGTC ACCGTCTCCTCA<br><br>SEQ ID NO: 30597 |

FIGURE 50
(Continued)

| | | | |
|---|---|---|---|
| | | AA | EIVLTQSPGTLSLSPGERATLSCRASPSVSSRFLA WYQQKPGQAPRLLIYGASSRATGIPDRFSGSGSG TDFTLTNSRLEPEDFAVYYCQQYGSSPPWTFGQ GTKVEIK<br>SEQ ID NO: 26592 | EVQLVESGGGLVKPGGSLRLSCAASGFTFRDYSMN WVRQAPGKGLEWVSSISSGSGYIHYADSVKGRFTIS RDNAKNSLYLQMNSLRAEDTAVYYCARATMALD YWGQGTLVTVSS<br>SEQ ID NO: 30598 |
| iPS:435817 | 21-225_190B11 | NA | GAAATTGTGCTGACTCAGTCTCCAGACTTTCA GTCTGTGGCTCCAAAGGAGAAAGTCACCATCA CCTGCCGGGCCAGTCAGAGTATTGGTAGTAAC TTACACTGGTACCAGCAGAAACCAGATCAGTC TCCGAAACTCCTCATCAAGTCTGTCTCCCAGTC CTTCTCAGGGGTCCCCTCGAGGTTCAGTGGCA GTGGATCTGGGACAGATTTCACCCTCACCATC AATAGCCTGGAAACTGAAGATGCTGCAACGTA TTACTGTCAGCAGAGTAGTAGTTTACCGTGGA CGTTCGGCCAAGGGACCAAGGTGGAAATCAA A<br>SEQ ID NO: 26593 | CAGGTGCAGCTGCAGGAGTCGGGCCCAGGACTG GTGAAGCCTTCGGAGACCCTGTCCCTCACCTGCA CTGTCTCTGGTGGCTCCATCAATAATTACTACTG GAGCTGGATCCGGCAGCCCGCCGGGAAGGGACT GGAGTGGATTGGGCGTATTATACCAGTGGGAGC ACCAACTACAACCCCTCCCTCAAGAGTCGAGTCA CCATGTCAGTAGACACGTCCAAGAACCAGTTCTC CCTGAAGCTGAGCTCTGTGACCGCCGCGGACACG GCCGTGCATTACTGTGCGAGAGATCGGGGATACT ATGGCTACTACGGTATGGACGTCTGGGGCCAAG GGACCACGGTCACCGTCTCCTCA<br>SEQ ID NO: 30599 |
| | | AA | EIVLTQSPDFQSVAPKEKVTITCRASQSIGNSLHW YQQKPDQSPKLLIKSASQSFSGVPSRFSGSGSGT DFTLTINSLETEDAATYYCQQSSSLPWTFGQGTK VEIK<br>SEQ ID NO: 26594 | QVQLQESGPGLVKPSETLSLTCTVSGGSINNYYWS WIRQPAGKGLEWIGRIYTSGSTNYNPSLKSRVTMS VDTSKNQFSLKLSSVTAADTAVHYCARDRGYYGY YGMDVWGQGTTVTVSS<br>SEQ ID NO: 30600 |

FIGURE 50
(Continued)

| | | | | |
|---|---|---|---|---|
| iPS:435819 | 21-225_190C11 | NA | GACATCCAGATGACCCAGTCTCCTTCCTCACTGTCTGCATCTGTAGGAGACAGAGTCACCATCACTTGTCGACGAGTCAGGGCATTGGCAATTATTTAGCCTGGTTTCAGCAGAAACCAGGGAAAGCCCCTAAGTCCCGTCTCTATAAAACATCCAGTTTACAAAGTGGGGTCCCATCAAAGTTCAGCGGCAGTGGATCTGGGACAGATTTCACTCTCACCATCAGCAGCCTGCAGCCTGAAGATTTTGCAACTTATTACTGTCAACAGTATATGACTTACCCGCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCAGGGCGTGGGCTACGACGGTTTGGACGTCTGGGGCCAAGGGACCACGGTCACCGTCTCCTCA |
| | | AA | DIQMTQSPSSLSASVGDRVTITCRTSQGIGNYLAWFQQKPGKAPKSLLYKTSSLQSGVPSKFSGSGSGTDFTLTISSLQPEDFATYYCQQYMTYPLTFGGGTKVEIK | QVQLVESGGGVVQPGRSLRLSCAASGFTFSSYGMHWVRQAPGKGLEWVAVIWYDGSNKNYADSVKGRFTISRDNSKNTLYLQMNSLRAEDTAVYYCARDQGVGYDGLDVWGQGTTVTVSS |
| | | | SEQ ID NO: 26595 | SEQ ID NO: 30601 |
| | | | SEQ ID NO: 26596 | SEQ ID NO: 30602 |
| iPS:435821 | 21-225_190E11 | NA | GAAATAGTGATGACGCAGTCTCCAGCCACCCTGTCTGTGTCTCCAGGGGAAAGAGCCACCCTCTCCTGCAGGGCCAGTCAGAGTTTTCGCATCAACTTAGCCTGGTACCAGCAGAGACCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATAATAACTGGCCGCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTACAGCGTCTGGATTCACCTTCAGTAACTATGCCATGCACTGGGTCCGCCAGGCTCCAGGCAAGGGGCTGGAGTGGGTGGCAATTATATGGTTTGATGGAAGTAATAAATACTATGCAGACTCCGTGAAGGGCCGATTCACCATCTCCAGAGACAATTCCAATAACACGCTGTATCTGCAAATGAACAGCCTGCGAGCCGAGGACACGGCTGTGTATTACTGTGCGAAAGCCCAGGGGGTCTACTACTACGTTATGGACGTCTGGGGCCAAGGGACCACGGTCACCGTCTCCTCA |
| | | | SEQ ID NO: 26597 | SEQ ID NO: 30603 |

FIGURE 50
(Continued)

| | | | |
|---|---|---|---|
| | | AA | EIVMTQSPATLSVSPGERATLSCRASQSFRINLA WYQQRPGQAPRLLIYGASTRATGIPARFSGSGSG TEFTLTISSLQSEDFAVYYCQQYNNWPLTFGGGT KVEIK<br><br>SEQ ID NO: 26598 | QVQLVESGGGVVQPGRSLRLSCTASGFTFSNYGMH WVRQAPGKGLEWVAIIWFDGSNKYYADSVKGRFT ISRDNSNNTLYLQMNSLRAEDTAVYYCAKAQGVY YYVMDVWGQGTTVTVSS<br><br>SEQ ID NO: 30604 |
| iPS:435823 | 21-225_190F11 | NA | GAAATTGTGCTGACTCAGTTTCCAGACTCTCA GTCTGTGACTCCAAAGGAGAAGTCACCATCA CCTGCCGGGCCAGTCAGAATCAGTTTAGTGGT GTAGCTTACACTGGTACCAGCAGAAACCAGAAACAGTC TCCAAAGGTCCTCATCAAGTATGCTTCCCAGT CCTTCTCAGGGGTCCCCTCGAGTTCAGTGGC AGTGGATCTGGGACAGATTTCACCCTCACCAT CAATAGCCTGGAAGCTGAAGATGCTGCAACGT ATTACTGTCATCAGAGTAGTAGTTTCCCTCGG ACGTTCGGCCAAGGGACCAAGGTGGAAATCA AA<br><br>SEQ ID NO: 26599 | GAGGTGCAGCTGTTGGACTCTGGGGGAGGCTTGG GACAGCCTGGGGGGTCCCTGAGACTCTCCTGTGC AGCCTCTGGATTCACCTTTGACAGCTATGCCATG AACTGGGTCCGCCAGGCTCCAGGAAGGGGCTG GAGTGGGTCTCAACTATTAGTGGTACTGGTGTA GGACATACTACGCAGACTCCGTGAAGGGCCGGT TCACCATCTCCAGAGACAATTCCAAGAACACGCT GTATCTGCAAATGAATAGCCTGAGAGCCGAGGA CACGGCCGTATATTACTGTGCGAAAGAGGAGGA TTACTATGATAGTAGTGGCCCGGGGTTCGACCCC TGGGGCCAGGGAACCCTGGTCACCGTCTCCTCA<br><br>SEQ ID NO: 30605 |
| | | AA | EIVLTQFPDSQSVTPKEKVTITCRASQNIGSSLHW YQQKPEQSPKVLIKYASQSFSGVPSRFSGSGSGT DFTLTINSLEAEDAATYYCHQSSSFPRTFGQGTK VEIK<br><br>SEQ ID NO: 26600 | EVQLLDSGGGLGQPGGSLRLSCAASGFTFDSYAMN WVRQAPGKGLEWVSTISGTGRRTYADSVKGRFTI SRDNSKNTLYLQMNSLRAEDTAVYYCAKEEDYYD SSGPGFDPWGQGTLVTVSS<br><br>SEQ ID NO: 30606 |

FIGURE 50
(Continued)

| | | | | |
|---|---|---|---|---|
| iPS:435825 | 21-225_190G11 | NA | GACATCCAGATGACCCAGTCTCCTTCCTCACTGTCTGCATCTGTAGGAGACAGAGTCACCATCACTTGTCGGACGAGTCAGGGCATTGGCAATTATTTAGCCTGGTTTCAGCAGAAACCAGGGAAAGCCCCTAAGTCCCTGTCTATAAAGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGCCAACAGTATATGACTTACCCGCTCACTTTCGGCGGAGGGACCAAGGTGGAGATCAAA SEQ ID NO: 26601 | CAGGTGCAGCTGGTGGAGTCTGGGGGAGGCGTGGTCCAGCCTGGGAGGTCCCTGAGACTCTCCTGTGCAGCCTCTGGATTCACCTTCAGTATTTATGGCATGCACTGGGTCCGCCAGGCTCCAGGCAAGGGCTGGAGTGGGTGGCAGTTATATGGTATGATGGAAGTAATAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCAGGGCGTGGGCTACGACGGTTTGGACGTCTGGGGCCAAGGGACCACGGTCACCGTCTCCTCA SEQ ID NO: 30607 |
| | | AA | DIQMTQSPSSLSASVGDRVTITCRTSQGIGNYLAWFQQKPGKAPKSLLYKASSLQSGVPSKFSGSGSGTDFTLTISSLQPEDFATYYCQQYMTYPLTFGGGTKVEIK SEQ ID NO: 26602 | QVQLVESGGGVVQPGRSLRLSCAASGFTFSIYGMHWVRQAPGKGLEWVAVIWYDGSNKNYADSVKGRFTISRDNSKNTLYLQMNSLRAEDTAVYYCARDQGVGYDGLDVWGQGTTVTVSS SEQ ID NO: 30608 |
| iPS:435827 | 21-225_190H11 | NA | GATATTGTGATGACCCAGACTCCACTCTCTCTGTCCGTCACCCCTGGACAGCCGGCCTCCATCTCCTGCAAGTCTAGTCAGAGCCTCCTGCATAGTGATGGAAAGAACTATTTGTATTGGTACCTGCAGAAGCCAGGCCAGCCTCCACAGTCCTGATCTGTGAGGTTTCCAACCGGTTCGCTGGAGTGACAGATAGGTTCAGTGGCAGCGGGTCAGGGACAGATTTCACACTGAAAATCAGCCGGGTGGAGGCTGGGGATGTTGGGGTTTATTACTGCATGCAAAGTATACAGTTCCCTGGACGTTCGGCCAAGGGACCAAGGTGGAAATCAAA SEQ ID NO: 26603 | CAGCTGCAGCTGCAGGAGTCGGGCCCAGGACTGGTGAAGCCTTCGGAGACCCTGTCCCTCACCTGCACTGTCTCTGGTGGCTCCATCAGAAGTTACCACTGGAGCTGGATCCGGCAGCCCCCGGGAAGGGACTGGAGTGGATTGGGCGTATCTATACCAGTGGGAGCACCAATTTACAACCCTCCCTCAAGAGTCGAGTCACCCTGTCAGTAGACACGTCCAAGAACCAGTTCTCCCTGAAGCTGAGCTCTGTGACCGCCGCGGACACGGCCGTGTATTACTGTGCGAGACTCCGTATAACTGAACTTCCCTTACTTTGACTACTGGGGCCAGGGAACCCTGGTCACCGTCTCCTCA SEQ ID NO: 30609 |

FIGURE 50
(Continued)

| | | | |
|---|---|---|---|
| | | AA | DIVMTQTPLSLSVTPGQPASISCKSSQSLLHSDGR TYLYWYLQKPGQPPQLLICEVSNRFAGVTDRFS GSGSGTDFTLKISRVEAGDVGVYYCMQSIQFPW TFGQGTKVEIK | QLQLQESGPGLVKPSETLSLTCTVSGGSIRSYHWSW IRQPAGKGLEWIGLIYTSRSTIYNPSLKSRVTLSVDT SKNQFSLKLSSVTAADTAVYYCARLRYNWNFPYF DYWGQGTLVTVSS |
| | | | SEQ ID NO: 26604 | SEQ ID NO: 30610 |
| iPS:435829 | 21-225_190B12 | NA | GAAATTGTGCTGACTCAGTCTCCAGACTTTCA GTCTGTGACTCCAAAGGAGAAAGTCACCATCA CCTGCCGGGCCAGTCAGAGTATTGGTAGTAGC TTACACTGGTACCAGCAGAAACCAGATCAGTC TCCAAAGCTCCTCATCAAGTATGCTTCCCAGT CCTTCTCAGGGGACCCTGAGGTTCAGTGGC AGTGGATCTGGGACAGATTTCACCTCAACAT CAATAGCCTGGAAGCTGAAGATGCTGCAACGT ATTACTGTCATCAGACTAGAAGTTTACCTCTC ACTTTCGGCGGAGGGACCAAGGTGGAGATCA AA | CAGGTGCAGCTGCAGGAGTCGGGCCAGGACTG GTGAAGCCTTCACAGACCCTGTCCCTCACCTGCA CTGTCTCTGGTGGCTCCATCAGCAGTGGTGGTTA CTACTGGAACTGGATCCGCCAGCACCCAGGGAA GGGCCTGGAGTGGATTGGGTATATCTATTACAGT GGGAGCACCTACTACAACCCGTCCCTCAAGAGTC GAGTTACCATATCAGTAGACAGTCTAAGAACCA GTTTTTTCTGAAGCTGAACTCTGTGACTGCCGCG GACACGGCCGTGTATTACTGTGCGAGATCCGGT ATAATTGGGACGCCGGGGTCGACCCTGGGCC GGGGAACCCTGGTCACCGTCTCCTCA |
| | | | SEQ ID NO: 26605 | SEQ ID NO: 30611 |
| | | AA | EIVLTQSPDFQSVTPKEKVTITCRASQSIGSSLHW YQQKPDQSPKLLIKYASQSFSGDPSRFSGSGSGT DFTLTINSLEAEDAATYYCHQTRSLPLTFGGGTK VEIK | QVQLQESGPGLVKPSQTLSLTCTVSGGSISSGGYYW NWIRQHPGKGLEWIGYIYYSGSTYYNPSLKSRVTIS VDTSKNQFFLKLNSVTAADTAVYYCARSGYNWDA GVDPWGRGTLVTVSS |
| | | | SEQ ID NO: 26606 | SEQ ID NO: 30612 |

FIGURE 50
(Continued)

| | | | | |
|---|---|---|---|---|
| iPS:435831 | 21-225_190C12 | NA | GACATCCAGATGACCCAGTCTCCATCCTCCCT GTCTGCATCTGTAGGAGACAGAGTCACCATCA CTTGCCGGGCAAGTCAGGGACATTAGAAAAGAT TTAGGCTGGTATCAGCAGAAACCAGGGAAAG CCCCTAAGCGCCTGATCCATACTGCATCCAGT TTGCAAAGTGGGGGTCCCATTAAGGTTCAGCGG CAGTGGATCTGGGACAGAATTCACTCTCACAA TCAGCAGCCTGCAGCCTGAAGATTTGCAACT TATTACTGTCTACAGCATAATAGTTACCCGTG GACGTTCGGCCAAGGGACCAAGGTGGAAATC AAA | CAGGTGCAGCTGGTGGAGTCTGGGGGAGCCGTG GTCCAGCCTGGGAGGTCCCTGAGACTCTCCTGTG CAGCCCTCTGATTCACCTTCAGTAGTACTATGCAT GCACTGGGTCCGCCAGGCTCCAGGCAAGGGCT GGAGTGGGTGGCAGTTATATCATATGATGGAGGT TATAAAACTATGTAGACTCCGTGAAGGGCCGAT TCACCATCTCCAGAGACACAATTCCAAGAACACGCT GTATCTGCAAATGAATAGCCTGAGAGCTGAGGA CACGGCTGTGTATTACTGTGCGAGAGGTACCAC GGGTACTACTACGGTGTGGACGTCTGGGGCCAA GGGACCACGGTCACCGTCTCCTCA |
| | | | SEQ ID NO: 26607 | SEQ ID NO: 30613 |
| | | AA | DIQMTQSPSSLSASVGDRVTITCRASQGIRKDLG WYQQKPGKAPKRLIHTASSLQSGVPLRFSGSGS GTEFTLTISSLQPEDFATYYCLQHNSYPWTFGQG TKVEIK | QVQLVESGGAVVQPGRSLRLSCAASGFTFSSYGMH WVRQAPGKGLEWVAVISYDGGYKNYVDSVKGRF TISRDNSKNTLYLQMNSLRAEDTAVYYCARGTHG YYYGVDVWGQGTTVTVSS |
| | | | SEQ ID NO: 26608 | SEQ ID NO: 30614 |
| iPS:435833 | 21-225_190D12 | NA | GACATTCAGATGACCCAGTCTCCATCCTCCCT GTCTGCATCTGTAGGAGACAGAGTCACCATCA CTTGCCGGGCGAGTCAGGGCATTAGCAGCAATTAT TTAGCCTGGTATCAGCAGAAACCAGGGAAAGT CCCTAAACTCCTGATCTATGTTGCATCCACTTT GCAATCAGGGGTCCCATCTCGGTTCAGTGGCA GTGGATCTGGGACAGATTTCACTCTCACCATC AGCAGCCTGCAGCCTGAAGATATAACAGTGCCCATTCA TTACTGTCAAAAGTATAACAGTGCCCCATTCA CTTTCGGCCCTGGGACCAAAGTGGATATCAAA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTTACAGTATGCCAT GAGCTGGGTCCGCCAGGCTCCAGGGAAGGGGCT GGAGTGGGACTCAGCTATTATTGGTAATGGTGGT AGGACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAAGATATGGG TAGATACAGTATGGTTTCTTTGACTACTGGGGC CAGGGAACCCTGGTCACCGTCTCCTCA |
| | | | SEQ ID NO: 26609 | SEQ ID NO: 30615 |

FIGURE 50
(Continued)

| | | | |
|---|---|---|---|
| | | AA | DIQMTQSPSSLSASVGDRVTITCRASQGISNYLA WYQQKPGKVPKLLIYVASTLQSGVPSRFSGSGS GTDFTLTISSLQPEDVATYYCQKYNSAPFTFGPG TKVDIK<br>SEQ ID NO: 26610 | EVQLLESGGGLVQPGGSLRLSCAASGFTFSSYAMS WVRQAPGKGLEWDSAIIGNGGRTYYADSVKGRFTI SRDNSKNTLYLQMNSLRAEDTAVYYCAKDMGRYS YGFFDYWGQGTLVTVSS<br>SEQ ID NO: 30616 |
| iPS:435835 | 21-225_190F12 | NA | GACATCCAGATGACCCAGTCTCCATCCTCACT GTCTGCATCTGTGGGAGACAGAGTCACCATCA CTTGTCGGGCGAGTCAGGGCATTGGCAAGTAT TTAGCCTGGTTTCAGCAGAAACCAGGGAAAGC CCCTAAGTCACTGATCTATGCTGCATCCAGTTT GCAAAGTGGGGTCCCATCAAAATTCAGCGGCA GTGGATCTGGGACAGATTTCACTCTCACCATC AGCAGCCTGCAGCCTGACGATTTTGCAACTTA TTACTGCCAACGATATATGATACTTACCCATTCA CTTTCGGCCCTGGGACCAAAGTGGATATCAAA<br>SEQ ID NO: 26611 | CAGGTGCAGCTGGTGGAGTCTGGGGGAGGCGTG GTCCAGCCTGGGAGGTCCCTGAGACTCTCCTGTG CAGCGTCTGGATTCACCTTCAGGAACTATGGCAT GCACTGGGTCCGCCAGGCTCCAGGCAAGGGCT GGAGTGGGTGGCAGTTATATGGTTGATGGAAGT AATGACTACTATGCAGACTCCGTGAAGGGCCGAT TCACCATCTCCAGAGACAATTCCAAGAACACGCT GTCACTGCAAATGAACAGCTGAGAGCCGAGA CACGGCTGTGTATTACTGTGCAGAGATAGAAGC GTCGGCTACGACGGTTTAGATGTCTGGGGCCAAG GGACCACGGTCACCGTCTCCTCA<br>SEQ ID NO: 30617 |
| | | AA | DIQMTQSPSSLSASVGDRVTITCRASQGIGKYLA WFQQKPGKAPKSLIYAASSLQSGVPSKFSGSGSG TDFTLTISSLQPDDFATYYCQRYDTYPFTFGPGT KVDIK<br>SEQ ID NO: 26612 | QVQLVESGGGVVQPGRSLRLSCAASGFTFRNYGM HWVRQAPGKGLEWVAVIWFDGSNDYYADSVKGR FTISRDNSKNTLSLQMNSLRAEDTAVYYCARDRSV GYDGLDVWGQGTTVTVSS<br>SEQ ID NO: 30618 |

FIGURE 50
(Continued)

| | | | | |
|---|---|---|---|---|
| iPS:435837 | 21-225_198G3 | NA | GACATCCAGATGGCCCAGTCTCCTTCCTCACTGTCTGCATCTGTAGGAGACAGAGTCACCATCACTTGTCGGACGAGTCAGGGCATTGGCAAGTATTTAGCCTGGTTTCAGCAGAAGCCAGGGAAAGCCCCTAAGTCCCTGTCTATAAAGCATCCAGTTTGCAAGGTGGGGTCCCATCAAAGTTCAGCGGCAGTGGATCTGGGACAGATTTCACTCTCACCATCAGCAGCCTGCAACCAGTATATGACTATACCGCTCACTTTCGGCGGAGGGACCAAGGTGGAGATCAA A | CAGGTGCAGCTGGTGGAGTCTGGGGGAGGCGTGGTCCAGCCTGGGAGGTCCCTGAAACTCTCCTGTGCAGCCTCTGGATTCACCTTCAGTACCTATGGCATGCACTGGGTCCGCCAGGCTCCAGGCAAGGACTGGAGTGGGTGGCAGTTATATGGTATGATGGAACTAATAAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCAGGGCGTGGGCTACGACGGTTTGGACGTCTGGGGCCAAGGGACCACGGTCACCGTCTCCTCA SEQ ID NO: 30619 |
| | | AA | DIQMAQSPSSLSASVGDRVTITCRTSQGIGKYLAWFQQKPGKAPKSLLYKASSLQGGVPSKFSGSGSGTDFTLTISSLQPEDFATYYCQQYMTYPLTFGGGTKVEIK SEQ ID NO: 26614 | QVQLVESGGGVVQPGRSLKLSCAASGFTFSTYGMHWVRQAPGKGLEWVAVIWYDGTNKNYADSVKGRFTISRDNSKNTLCLQMNSLRAEDTAVYYCARDQGVGYDGLDVWGQGTTVTVSS SEQ ID NO: 30620 |
| iPS:435839 | 21-225_191B1 | NA | GACATTGTGATGACCCAGACTCCACTCTCTGTCCGTCACCCTGGACAGCCGGCCTCCATCTCCTGTAGGTCTAGTCAGAGCCTCCTGCATAGTGATGGAAAGAACTATTTGTTTGGTACCTGCAGAAGCCAGGCCAGCCTCCACAGGTCCTGATCTATGAAGTTTCCAACCGGTTCTCTGGAGTGCCAGATAGGTTCAGTGGCAGCGGGTCAGGGACAGATTTCACACTGAAAATCAGCGGGGTGGAGGCTGAGGATGTTGGGGTTTATTACTGCATGCAAAGTTTCCAGCTCCCTGGACGTTCGGTCAAGGGACCAAGGTGGAAATCAAT SEQ ID NO: 26615 | CAGGTGCAGCTGCAGGAGTCGGGCCCAGGACTGGTGAAGCCTTCGGAGACCCTGTCCCTCACCTGCACTGTCTCTGGTGGCTCCATCAGTAGTTATCACTGGAGCTGGATCCGGCAGCCCGCGGGAAGGGACTGGAGTGGATTGGCCATATCTATACCAGTGGGAGCACCAAGTACAACCCCTCCCTCAAGAGTCGAGTCACCATGTCAGTAGACACGTCAAGAACCAGTTCTCCCTGAAGCTGAGCTCTGTGACCGCCGCGGACACGGCCGTGTATTACTGTGCGAGACTCCGTATAACTGGAACTTCCCTTCTTGACTATTGGGGCCAGGGAACCCTGGTCACCGTCTCCTCA SEQ ID NO: 30621 |

FIGURE 50
(Continued)

| | | | |
|---|---|---|---|
| iPS:435841 | 21-225_191D8 | AA | DIVMTQTPLSLSVTPGQPASISCRSSQSLLHSDGK TYLFWYLQKPGQPPQVLIYELSNRFSGVPDRFSG SGSGTDFTLKISRVEAEDVGVYYCMQSFQLPWT FGQGTKVEIN<br>SEQ ID NO: 26616 | QVQLQESGPGLVKPSETLSLTCTVSGGSISSYHWSW IRQPAGKGLEWIGHIYTSGSTKYNPSLKSRVTMSVD TSKNQFSLKLSSVTAADTAVYYCARLRYNWNFPFF DYWGQGTLVTVSS<br>SEQ ID NO: 30622 |
| | | NA | GACATCATGATGACCCAGTCTCCAGACTCCCT GGCTGTGTCTCTGGGCGAGAGGGCCATCATCA GCTGCAGGTCCAGCCAGAGTGTTTACACAGC TCCAACAATTACAACTACTTAGCTTGGTACCA GCAGAAACCAGGACATCCTCCTAAACTGCTCA TTTACTGGGCATCTCACCCGGGAATCCGGGTC CCTGACCGATTCAGTGGCAGCGGGTCTGGGAC AGATTTCACTCTCACCATCAGCAGCCTGCAGG CTGAAGATGTGGCAGTTTATTACTGTCAACAA TATTATAGTACTCCTCCGACGTTCGGCCTAGG GACCAAGGTGGAAATCAAA<br>SEQ ID NO: 26617 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGCACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCCCATAGCAGT GGCTGGTACTACTTTGACTACTGGGGCCAGGGAA CCCTGGTCACCGTCTCCTCA<br>SEQ ID NO: 30623 |
| | | AA | DIMMTQSPDSLAVSLGERAIISCRSSQSVLHSSNN YNYLAWYQQKPGHPPKLLIYWASTRESGVPDRF SGSGSGTDFTLTISSLQAEDVAVYYCQQYYSTPP TFGLGTKVEIK<br>SEQ ID NO: 26618 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAHSSGW YYFDYWGQGTLVTVSS<br>SEQ ID NO: 30624 |

FIGURE 50
(Continued)

| | | | | |
|---|---|---|---|---|
| iPS:435843 | 21-225_191F1 | NA | GAAATTGTGTTGACGCAGTCTCCAGGCACCCT GTCTTTGTCTCCAGGGGAAAGAGCGCCCTCT CCTGCAGGGCCAGTCAGTCAGAGTATTAGCCTCAAC TTCTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAATAGACTGGAGCTGAAGATTTTGCAG TGTATTACTGTCAGCAGTATGGTAGGTCACCG TGGACGTTCGGCCAAGGGACCAAGGTGGAAG TCAAA | CAGGTGCAGCTGCAGGAGTCGGGCCCAGGACTG GTGAAGCCTTCACAGACCCTGTCCCTCACCTGCA CTGTTTCTGGTGGCTCCATCAACAGTGGTGTTA CTACTGGAACTGGATCCGCCAGCACCCAGGGAA GGGCCTGGAGTGGATTGGGTACATCTTTTACAGT GGGAGCACCTACTACAACCCGTCCCTCAAGAGTC GAGTCACCATATCAGTAGACACGTCTAAGAACC AGTTCTCCCTGAAGCTGAGCTCTGTGACTGCCGC GGACACGGCCGTGTATTACTGTGCGAGAGGGA TTACGATGGTTCGGGGAGTTATCACTACTATTAC GGTATGGACGTCTGGGGCCAAGGGACCACGGTC ACCGTCTCCTCA |
| | | | SEQ ID NO: 26619 | SEQ ID NO: 30625 |
| | | AA | EIVLTQSPGTLSLSPGERAALSCRASQSISLNFLA WYQQKPGQAPRLLIYGASSRATGIPDRFSGSGSG TDFTLTINRLEPEDFAVYYCQQYGRSPWTFGQG TKVEVK | QVQLQESGPGLVKPSQTLSLTCTVSGGSINSGYY WNWIRQHPGKGLEWIGYIFYSGSTYYNPSLKSRVTI SVDTSKNQFSLKLSSVTAADTAVYYCARGDYDGS GSYHYYYGMDVWGQGTTVTVSS |
| | | | SEQ ID NO: 26620 | SEQ ID NO: 30626 |
| iPS:435845 | 21-225_191G1 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGAACAGATTTCACTCTCACCATC AGCAGCCTGCAACATTATCTTACTACCCTCTCAC TTACTGCCAACATTATCTTACTCACCCTCTCAC TTTCGGCGGAGGGACCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATGAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATAGGGG GGTGGTTACTACGGTTTGGACGTCTGGGGCCAA GGGACCACGGTCACCGTCTCCTCA |
| | | | SEQ ID NO: 26621 | SEQ ID NO: 30627 |

FIGURE 50
(Continued)

| | | AA | DIQMTQSPSSLSASVGDRVTITCRASQGISNYLA WFQQKPGKAPKSLIYAASSLQSGVPSKFSGSGSG TDFTLTISSLQPEDFATYYCQHYLTYPLTFGGGT KVEIK<br><br>SEQ ID NO: 26622 | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARDRGV GYYGLDVWGQGTTVTVSS<br><br>SEQ ID NO: 30628 |
|---|---|---|---|---|
| iPS:435847 | 21-225_191A3 | NA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGATCCGCCAGCACCCAGGAA GGGCCTGGAGTGGATTGGGTACATCTTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGATT ACGATGGTTCGGGAGTTATCACTACTACTACGG TATGGACGTCTGGGGCCAAGGGACCACGGTCAC CGTCTCCTCA<br><br>SEQ ID NO: 30629 | GAAATTGTGTTGACGCAGTCTCCAGGCACCCT GTCTTTGTCTCCAGGGGAAAGAGCCACCCTCT CCTGCAGGGCCAGTGCAGAGTATTCGCAGCAGC TTCTTAGCCTGGTACCAGCAGAAACCTGGCCA GGCTCCCAGGCTCCTCATCTATGGTGCATCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAATATGGTAACTCACCG TGGGCGTTCGGCCAAGGGACCAAGGTGGAAG TCAAA<br><br>SEQ ID NO: 26623 |
| | | AA | EIVLTQSPGTLSLSPGERATLSCRASQSIRSSFLA WYQQKPGQAPRLLIYGASSRATGIPDRFSGSGSG TDFTLTISRLEPEDFAVYYCQQYGNSPWAFGQG TKVEVK<br><br>SEQ ID NO: 26624 | QVQLQESGPGLVKPSQTLSLTCTVSGGSISSGDYYW NWIRQHPGKGLEWIGYIFYSGSTYNPSLKSRVTIS VDTSKNQFSLKLSSVTAADTAVYYCARGDYDGSG SYHYYGMDVWGQGTTVTVSS<br><br>SEQ ID NO: 30630 |

FIGURE 50
(Continued)

| | | | |
|---|---|---|---|---|
| iPS:435849 | 21-225_191C3 | NA | GAAATTGTGTTGACGCAGTCTCCAGGCACCCT GTCTTTGTCTCTCCAGGGGAAAGAGCCACCCTCT CCTGCAGGGCCAGTCAGTATTCGCAGCAGC TTCTTAGCCTGGTATCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAACTCACCG TGGGCGTTCGGCCAAGGGACCAAGGTGGAAA TCAAA<br><br>SEQ ID NO: 26625 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGATCCGCCAGTCCCAGGGAA GGGCCTGGAGTGGATTGGGTACATCTTTACAGT GGGAGCACTACTACAACCCGTCCCTCAAGAGTC GACTTACCATATCAGTGGACACGTCTAAGAACCA GTTCTCCCTGAAACTGAACTCTGTGACTGCCGCG GACACGGCCGTGTATTACTGTGCGAGAGGGATT ACGATGGTTCGGGGAGTTATCACTTCTACTAGG TATGGACGTCTGGGGCCAAGGGACCACGGTCAC CGTCTCCTCA<br><br>SEQ ID NO: 30631 |
| | | AA | EIVLTQSPGTLSLSPGERATLSCRASQSIRSSFLA WYQQKPGQAPRLLIYGASSRATGIPDRFSGSGSG TDFTLTISRLEPEDFAVYYCQQYGNSPWAFGQG TKVEIK<br><br>SEQ ID NO: 26626 | QVQLQESGPGLVKPSQTLSLTCTVSGGSISSGDYYW NWIRQLPGKGLEWIGYIFYSGSTYYNPSLKSRLTISV DTSKNQFSLKLNSVTAADTAVYYCARGDYDGSGS YHFYYGMDVWGQGTTVTVSS<br><br>SEQ ID NO: 30632 |
| iPS:435851 | 21-225_191D3 | NA | GAAATTGTGTTGACGCAGTCTCCAGGCACCCT GTCTTTGTCTCTCCAGGGGAAAGCGCCACCCTCT CCTGCAGGGCCGGTCAAAGTATTAGAACCAAC TTCTTAGCCTGGTACCAGCAGCAGCCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAACAGACTGGAGCCTGAAGATGGTGCAG TGTATTACTGTCAGCAGTATGGTAGTCACCG TGGACGTTCGGCCAAGGGACCAAGGTGGAAA TCAAA<br><br>SEQ ID NO: 26627 | CAGGTGCAACTGAAGGAGTCGGGCCCAGGACTG GTGAAGCCTTCACAGACCCTGTCCCTCACCTGCA CTGTCTCTGGTGGCTCCATCAACAGTGGTGATTA CTACTGGAACTGGATCCGCCAGCACCCAGGGAA GGGCCTGGACTGGATTGGGTACATCTTTACAGT GGGAGCACTACTACAGTAGACACGTCTAAGAACCA GTTCTCCCTGAAGCTGAGCTCTGTGACTGCCGCG GACACGGCCGTGTATTACTGTGCGAGAGGGATT ACGATGGTTCGGGGAGTTATCACTACTATTACGG TATGGACGTCTGGGGCCAAGGGACCACGGTCAC CGTCTCCTCA<br><br>SEQ ID NO: 30633 |

FIGURE 50
(Continued)

| | | | |
|---|---|---|---|
| iPS:435853 | | AA | EIVLTQSPGTLSLSPGESATLSCRAGQSIRTNFLA WYQQKPGQAPRLLIYGASSRATGIPDRFSGSGSG TDFTLTINRLEPEDFAVYYCQQYGSSPWTFGQGT KVEIK<br>SEQ ID NO: 26628 | QVQLKESGPGLVKPSQTLSLTCTVSGGSINSGDYY WNWIRQHPGKGLDWIGYIFYSGSTYNPSLKSRVT ISVDTSKNQFSLKLSSVTAADTAVYYCARGDYDGS GSYHYYGMDVWGQGTTVTVSS<br>SEQ ID NO: 30634 |
| | | NA | GATATTGTAATGACCCAGACTCCACTCTCTCT GTCCGTCACCCCTGGACAGCCGGCCTCCATCT CCTGCAAGTCTAGTCAGAGCCTCCTCCATAGT GATGGAAGGACCTATTTGTATTGGTACCTGCA GAAGCCAGGCCAGTCTCCACAGCTCCTGATCT GTGAGGTTTCCAACCGGTTCGCTGGAGTGACA GATAGGTTCAGTGGCAGCGGGTCAGGGACAG ATTTCACACTGAAAATCAGCCGGGTGGAGGCT GGGGATGTTGGGGTTTATTACTGCATGCAAAG TATACAACTTCCCTGGACGTTCGGCCAAGGGA CCAAGGTGGAAATCAAA<br>SEQ ID NO: 26629 | CAGCTGCAGCTGCAGGAGTCGGGCCAGGACTG GTGAAGCCTTCGGAGACCCTGTCCCTCACCTGCA CTGTCTCTGGTGGCTCCATCAGAAGTACCACTG GAGCTGGATCGGCAGCCCGCGGAAGGGACT GGAGTGGATTGGACTTATCTATACCAGTAGGAGC ACCAATTACAACCCCTCCCTCAAGAGTCGAGTCA CCATGTCAGTTGACACGTCCAAGAACCAGTTCTC CCTGAAGCTGAACTCTGTGACCGCCGCGGACACG GCCGTGTATTACTGTGCGAGACTCCGGTATAACT GGAACTTCCCTTACTTTGACTACTGGGGCCAGGG AACCCGGTCACCGTCTCCTCA<br>SEQ ID NO: 30635 |
| | 21-225_191E3 | AA | DIVMTQTPLSLSVTPGQPASISCKSSQSLLHSDGR TYLYWYLQKPGQPPQLLICEVSNRFAGVTDRFS GSGSGTDFTLKISRVEAGDVGVYYCMQSIQLPW TFGQGTKVEIK<br>SEQ ID NO: 26630 | QLQLQESGPGLVKPSETLSLTCTVSGGSIRSYHWSW IRQPAGKGLEWIGLIYTSRSTNYNPSLKSRVTMSVD TSKNQFSLKLNSVTAADTAVYYCARLRYNWNFPY FDYWGQGTILVTVSS<br>SEQ ID NO: 30636 |

FIGURE 50
(Continued)

| | | | | |
|---|---|---|---|---|
| iPS:435855 | 21-225_191G3 | NA | GACATCGTGATGACCCAGTCTCCAGACTCCCT GGCTGTGTCTCTGGGCGAGAGGGCCACCATCG ACTGTAAGTCCAGCCAGAGTGTTTTACACAGC TCCAACAGTTACAACTACTTAGCTTGGTACCA GCAGAAATTAGGACAGCCTCCTAAACTGCTCA TTTACTGGGCATCTACCCGAAAATCGGGGTC CCTGACCGATTCAGTGGCAGGGGTCTGGGAC AGATTTCACTCTCACCATCAGCAGCCTGCAGG CTGAAGATGTGGCATTTTATTACTGTCAGCAA TATTATAGTAGTCCTCCCACTTTCGGCCCTGGG ACCAAAATGGATATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGACGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCCCATAGCAG TGGCTGGTACACTTTGACTACTGGGGCCAGGGA ACCCTGGTCACCGTCTCCTCA |
| | | | SEQ ID NO: 26631 | SEQ ID NO: 30637 |
| | | AA | DIVMTQSPDSLAVSLGERATIDCKSSQSVLHSSN SYNYLAWYQQKLGQPPKLLIYWASTRKSGVPD RFSGSGSGTDFTLTISSLQAEDVAFYYCQQYYSS PPTFGPGTKMDIK | QVQLVQSGAEVKKPGASVKVSCKASGYTFTNYDIN WVRQATGQGLEWMGRMNPNSGNTGYAQKFQGR VTMTRNTSISTAYMELSSLRSEDTAVYYCAHSSGW YIFDYWGQGTLVTVSS |
| | | | SEQ ID NO: 26632 | SEQ ID NO: 30638 |
| iPS:435857 | 21-225_191A4 | NA | GACATCCAGATGACCCAGTCTCCATCCTCCCT GTCTGCATCTGTAGGAGACAGAGTCACCATCA CTTGCCGGGCAAGTCAGGGCATTAGAAAAGAT CTTAGGCTGGTATCAGCAGAAACCAGGGAAAG CCCCTAAGCGCCTGATCTACCATCTGCATCCAGT TTGCAAAATGGGGGTCCCATTAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCAGACTCCGTGAGGG TATAAAAACTATGCAGACTCCGTGAAGGGCCGA TTCACCATCTCCAGAGACAATTCCAAGAACACGC TGTATCTGCAAATGAATAGCCTGAGAGCTGAGGA CACGGCTGTGTATTACTGTGCGAGAGGTACCCAC GGTACTACTACGGTGTGGACGTCTGGGGCCAA GGGACCACGGTCACCGTCTCCTCA |
| | | | SEQ ID NO: 26633 | SEQ ID NO: 30639 |

FIGURE 50
(Continued)

| | | | |
|---|---|---|---|
| iPS:435859 | 21-225_190E6 | AA | DIQMTQSPSSLSASVGDRVTITCRASQGIRKDLG WYQQKPGKAPKRLIHTASSLQNGVPLRFSGSGS GTEFTLTISSLQPEDFATYYCLQHNSYPWTFGQG TKVEIK<br>SEQ ID NO: 26634 | QVQLVESGGGVVQPGRSLRLSCAASGFTFSSYGMH WVRQAPGKGLEWVAVISYDGGYKNYADSVKGRF TISRDNSKNTLYLQMNSLRAEDTAVYYCARGTHG YYYGVDVWGQGTTVTVSS<br>SEQ ID NO: 30640 |
| | | NA | GACATCCAGATGACCCAGTCTCCTTCCTCACT GTCTGCATCTGTAGGAGACAGAGTCACCATCA CTTGTCGGACGAGTCAGGGCATTGGCAATTAT TTAGCCTGGTTTCAGCAGAAACCAGGGAAAGC CCCTAAGTCCCTGCTCTATAAAGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATATGACTTACCCGCTCA CTTTCGGCGGAGGGACCAAGGTGGAGATCAA A<br>SEQ ID NO: 26635 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGTATGATGGAAGT AATAAAACTATGCAGACTCCGTGAAGGCCGA TTCACCATCTCCAGAGACAACATTCCAAGAACACGC TGTATCTGCAAATGAACAGCCTGAGAGCCGAGG ACACGGCTGTGTATTACTGTGCGAGAGATCAGG CGTGGGCTACGACGGTTTGGACGTCTGGGCCAA GGGACCACGGTCACCGTCTCCTCA<br>SEQ ID NO: 30641 |
| | | AA | DIQMTQSPSSLSASVGDRVTITCRTSQGIGNYLA WFQQKPGKAPKSLLYKASSLQSGVPSKFSGSGS GTDFTLTISSLQPEDFATYYCQQYMTYPLTFGGG TKVEIK<br>SEQ ID NO: 26636 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS<br>SEQ ID NO: 30642 |

FIGURE 50
(Continued)

| | | | | | | |
|---|---|---|---|---|---|---|
| iPS:435861 | 21-225_190A5 | NA | GACATCCAGATGACCCAGTCTCCATCCTCACT GTCTGCATCTGTAGGAGACAGAGTCACCATCA CTTGTCGGGCGAGTCAGGGGATTGGCAATCAT TTAGCCTGGTTTCAGCAGAAACCAGGAAAGC CCCTAAGTCCCTGATCCATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATATTGCAACTTA TTACTGTCAACAGTATAGTAATTACCCAGTCA CTTTCGGCCCTGGGACCAAAGTGGATATCAAA | SEQ ID NO: 26637 | CAGGTGCAGTTGGTGGAGTCTGGGGGAGGCGTG GGCCAGCCTGGGAGGTCCCTGAGACTCTCCTGTG CAGCCTCTGGATTCACCTTCAGTAGTTATGGCAT GCACTGGGTCCGCCAGGCTCCAGGCAAGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATTTCTC TGTAGGGTACGACGGTATGGACGTCTGGGGCCA AGGGACCACGGTCACCGTCTCCTCA | SEQ ID NO: 30643 |
| | | AA | DIQMTQSPSSLSASVGDRVTITCRASQGIGNHLA WFQQKPGKAPKSLIHAASSLQSGVPSKFSGSGSG TDFTLTISSLQPEDFATYYCQQYSNYPVTFGPGT KVDIK | SEQ ID NO: 26638 | QVQLVESGGGVGQPGRSLRLSCAASGFTFSSYGMH WVRQAPGKGLEWVAVIWYDGSNKNYADSVKGRF TISRDNSKNTLYLQMNSLRAEDTAVYYCARDFSVG YDGMDVWGQGTTVTVSS | SEQ ID NO: 30644 |
| iPS:435863 | 21-225_191H4 | NA | GAAATTGTGCTGACTCAGTCTCCAGACTTTCA GTCTGTGACTCCAAAGGAGAAAGTCACCATCA CCTGCCGGGCCAATCAGAGCATTGGTAGTAGC TTACACTGGTACCAGCAGAAACCAGATCAGTC TCCAAAGCTCCTCATCAAGTATGCTTCCCAGT CCCTCTCAGGGGTCCCCTCGAGGTTCAGTGCC AGTGGATCTGGGACAGATTTCACCCTCACCAT CAATAGCCTGGATGCTGAAGATGCTGCAAGCGT ATTACTGTCATCAGACTGTAGGTTACCTCTC ACTTTCGGCGGAGGGACCAAGGTGGAGATCA AA | SEQ ID NO: 26639 | CAGGTGCAGCTGCAGGAGTCGGGCCCAGGACTG GTGAAGCCTTCACAGACCCTGTCCTCACCTGCA CTGTCTCTGGTGGCTCCATCAGCAGTGGTGTTA CTACTGGAACTGGATCCGCCAGCACCCAGGGAA GGGCCTGGAGTGGATTGGGTACATCTTTACAGT GGGAGCACTACTACAACCCGTCCTCAGGAGTC GACTTACCATATCAATAGACACGTCTAAGAACCA GTTCTCCCTGAAGCTGACCTCTGTGACTGCCGCG GACACGGCCGTATATTACTGTGTGGGAGATCCGGGT ATAACTGGACAACGGGTGCGACCCTGGGCC AGGGAACCTGGTCACCGTCTCCTCA | SEQ ID NO: 30645 |

FIGURE 50
(Continued)

| | | | |
|---|---|---|---|
| iPS:435865 | | AA | EIVLTQSPDFQSVTPKEKVTITCRANQSIGSSLHW YQQKPDQSPKLLIKYASQSLSGVPSRFSASGSGT DFTLTINSLDAEDAATYYCHQTGRLTFGGGT KVEIK<br>SEQ ID NO: 26640 | QVQLQESGPGLVKPSQTLSLTCTVSGGSISSGGYYW NWIRQHPGKGLEWIGYIFYSGSTYYNPSLRSRLTISI DTSKNQFSLKLTSVTAADTAVYYCGRSGYNWDNG VDPWGQGTLVTVSS<br>SEQ ID NO: 30646 |
| | 21-225_191A5 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGG TTCTTAGCCTGGTACCAGCAGAAACCTGGCCA GGCTCCCAGGCTCCTCATCTATGGTGCTTCCA ACAGGGCCACTGGCATCCCCGACAGGTTCAGT GGCAGTGGGTCTGGGACAGACTTCACTCTCAC CATCAGCAGACTGGAGCCTGAAGATTTTGCAG TGTATTACTGTCAGCAGTATGGTGGTTCACCTC CGTGGACGTTCGTCCAAGGGACCAAGGTGGA AATCAAA<br>SEQ ID NO: 26641 | GAGATACAGGTGGTGGTGGAGTCTGGGGGAGGCCTG GTCAAGCCTGGGGGGTCCCTGAGACTCTCCTGTG CAGCCTCTGGATTCACCTTCAGAGACTACTAGCAT GAACTGGGTCCGCCAGGCTCCAGGGAAGGGGCT GGAGTGGGTCTCATCATTAGTAGTGGTAGTGGT TACATATATTATGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGCTACTATG GCCCTTGACTACTGGGGCCAGGGGAGCCCTGGTCA CCGTCTCCTCA<br>SEQ ID NO: 30647 |
| | | AA | EIVLTQSPGTLSLSPGERATLSCRASQSVSSRFLA WYQQKPGQAPRLLIYGASNRATGIPDRFSGSGS GTDFTLTISRLEPEDFAVYYCQQYGGSPPWTFVQ GTKVEIK<br>SEQ ID NO: 26642 | EIQVVESGGGLVKPGGSLRLSCAASGFTFRDYSMN WVRQAPGKGLEWVSSISSGSGYIYYADSVKGRFTIS RDNAKNSLYLQMNSLRAEDTAVYYCARATMALD YWGQGALVTVSS<br>SEQ ID NO: 30648 |

FIGURE 50
(Continued)

| | | | | |
|---|---|---|---|---|
| iPS:435867 | 21-225_191E5 | NA | GAAATTGTGCTGACTCAGTTCCAGACTCTCA GTCTGTGACTCCAAAGGAGAAAGTCACCATCA CCTGCCGGGCCAGTCAGAGCAGCAGATTGTAGTAGC TTACACTGGTACCAGCAGAAAACCAGATCAGTC TCCAAAGCTCCTCATCAAGTATGCTTCCCAGT CCTTCTCAGGGGTCCCCTCGAGGTTCAGTGGC AGTGGATCTGGGACAGATTTCACCCTCACCAT CAATAGTCTGGAGGCTGAAGATGCTGCAACGT ATTACTGTCATCAGAGTAGTAGTTTCCCTCGG ACGTTCGGCCAAGGGACCAAGGTGGAAATCA AA | GAGGTGCAGCTGTTGGACTCTGGGGGAGGCTTGG GACAGCCTGGGGGGTCCCTGAGACTCTCCTGTGC AGCCTCTGGATTCACCTTTGACAGCTATGCCATG AACTGGGTCCGCCAGGCTCCAGGAAGGGCTG GAGTGGGTCTCAACTATTAGTGGTACTGGTCGTA GGACATACTACGCAGACTCCGTGAAGGGCCGGT TCACCATCTCCAGAGACAATTCCAAGAACACGCT GTATCTGCAAATGAATAGCCTGAGAGCCGAGGA CACGGCCGTATATTACTGTGCGAAAGAGGAGGA TTACTATGATAGTAGTGGCCCGGGGTTGACCCC TGGGGCCAGGGAACCCTGGTCACCGTCTCCTCA |
| | | | SEQ ID NO: 26643 | SEQ ID NO: 30649 |
| | | AA | EIVLTQFPDSQSVTPKEKVTITCRASQSIGSSLHW YQQKPDQSPKLLIKYASQSFSGVPSRFSGSGSGT DFTLTINSLEAEDAATYYCHQSSSFPRTFGQGTK VEIK | EVQLLDSGGGLGQPGGSLRLSCAASGFTFDSYAMN WVRQAPGKGLEWVSTISGTGRRTYYADSVKGRFTI SRDNSKNTLYLQMNSLRAEDTAVYYCAKEEDYYD SSGPGFDPWGQGTLVTVSS |
| | | | SEQ ID NO: 26644 | SEQ ID NO: 30650 |
| iPS:435869 | 21-225_190B1 | NA | GACATCCAGATGACCCAGTCTCCATCCTCACT GTCTGCATCTGTTGGAGACAGAGTCACCATCA CTTGTCGGGCGAGTCAGGGCATTAGAAATTAT TTAGCCTGGTTTCAGCAGAAACCAGGGAAAGC CCCTAAGTCCCTGATCTATGTTGCATCCAGTTT GGAAAGTGGGGTCCCATCAAAGTTCAGTGGCA GTGGATCTGGGACAGAGTTCACTCTCACCATC AGCAGCCTGCAACCTGAAGATATTTGAACTTA TTACTGCCAACAGTATCTTAATTACCCAGTCA CTTTCGGCCCTGGGACCAAAGTGGATATCAGA | CAGGTGCAGCTGGTGGAGTCTGGGGGAGGCGTG GTCCAGCCTGGGGAGGTCCCTGAGACTCTCCTGTG CAACGTCTGATTCACCTTCAGTAGCTATGGCAT GCACTGGGTCCGCCAGGCTCCAGGCAAGGGGCT GGAGTGGGTGGCAGTTATATGGTATGATGGAAGT AATAAACATTATGCAGACTCCGTGAAGGGCCGA TTCACCATCTCCAGAGACAATTCCAAGAACACAC TATATCTGCAAATGAACAGCCTGAGAGCCGAGG ACACGGCTGTTTATTACTGTGCGAGAGATAGAAC AGTGGATACTCCGTATGAGACGTCTGGGGCCA AGGGACCACGGTCACCGTCTCCTCA |
| | | | SEQ ID NO: 26645 | SEQ ID NO: 30651 |

FIGURE 50
(Continued)

| | | | | |
|---|---|---|---|---|
| iPS:435871 | 21-225_191E6 | AA | DIQMTQSPSSLSASVGDRVTITCRASQGIRNYLA WFQQKPGKAPKSLIYVASSLESGVPSKFSGSGSG TEFTLTISSLQPEDFGTYYCQQYLNYPVTFGPGT KVDIR<br><br>SEQ ID NO: 26646 | QVQLVESGGGVVQPGRSLRLSCATSGFTFSSYGMH WVRQAPGKGLEWVAVIWYDGSNKHYADSVKGRF TISRDNSKNTLYLQMNSLRAEDTAVYYCARDRTVG YSGMDVWGQGTTVTVSS<br><br>SEQ ID NO: 30652 |
| | | NA | GATATTGTGATGACCCAGACTCCACTCTCTCT GTCCGTCACCCCTGGACAGCCGGCCTCCATCT CCTGCAAGTCTAGTCAGAGCCTCCTCCATAGT GATGAAGGACCTATTTGTATTGGTACCTGCA GAAGCCAGGCCAGGCCTCCACAGCTCCTGATCT GTGAGGTTTCCAACCGGTTCGCTGCTGAGTGACA GATAGGTTCAGTGGCAGCGGGTCAGGGACAG ATTTCACACTGAAAATCAGCCGGGTGGAGGCT GGGGATGTTGGGATTTATTACTGCATGCAAAG TATACATTTTCCCTGGACGTTCGGCCAAGGGA CCAAGGTGGAAATCAAA<br><br>SEQ ID NO: 26647 | CAGCTGCAGCTGCAGGAGTCGGGCCAGGACTG GTGAAGCCTTCGGAGACCCTGTCCCTCACCTGCA CTGTCTCTGGTGGCTCCATCAGAAGTACCACTG GAGCTGGATCGGCAGCCCGCGGAAGGGACT GGAGTGGATTGGCTTATCTATACCAGTAGGAGC ACCAATTACAACCCCTCCCTCAAGAGTCGAGTCA CCATGTCAGTAGACACGTCCAAGAACCAGTTCTC CCTGAAGCTGAGCTCTGTGACCGCCGCGGACACG GCCGTGTATTACTGTGCGAGACTCCGGTATAACT GGAACTTCCCTACTTTGACTTCTGGGGCCAGGG AACCCTGGTCACCGTCTCCTCA<br><br>SEQ ID NO: 30653 |
| | | AA | DIVMTQTPLSLSVTPGQPASISCKSSQSLLHSDGR TYLYWYLQKPGQPPQLLICEVSNRFAGVTDRFS GSGSGTDFTLKISRVEAGDVGIYYCMQSIHFPWT FGQGTKVEIK<br><br>SEQ ID NO: 26648 | QLQLQESGPGLVKPSETLSLTCTVSGGSIRSYHWSW IRQPAGKGLEWIGLIYTSRSTNYNPSLKSRVTMSVD TSKNQFSLKLSSVTAADTAVYYCARLRYNWNFPYF DFWGQGTLVTVSS<br><br>SEQ ID NO: 30654 |

FIGURE 50
(Continued)

| | | | | |
|---|---|---|---|---|
| iPS:435873 | 21-225_190G4 | NA | GACATCCAGATGACCCAGTCTCCATCCTCACTGTCTGCATCTGTAGGAGACAGAGTCACCATCACTTGTCGGGCGAGTCAGGACATTGGCAGATATTTAGCCTGGTTTCAGCAGAAGCCAGGGAAAGCCCCTAAGTCCCTGATCTATGCTGCATCCAGTTTGCAAAGTGGGGTCCCATCAAAGTTCAGCGGCAGTGGATCTGGGACAGATTTCACTCTCACCATCAGCAGCCTGCAGCCTGAAAATTTTGCAACTTATTACTGTCAACAATATAGTACTTACCCGCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAAACTACGCAGACTCCGTGAAGGGCGAATTCACCATCTCCAGAGACAATTCCAAGAACACGCTGTATCTGCAAATGAACAGCCTGAGAGCCGAGGACACGGCTATGTATTACTGTGCGAGAGATCAGGGCGTGGGCTACGACGGTTTGGACGTCTGGGGCCAAGGGACCTCGGTCACCGTCTCCTCA |
| | | | SEQ ID NO: 26649 | SEQ ID NO: 30655 |
| | | AA | DIQMTQSPSSLSASVGDRVTITCRASQDIGRYLAWFQQKPGKAPKSLIYAASSLQSGVPSKFSGSGSGTDFTLTISSLQPENFATYYCQQYSTYPLTFGGGTKVEIK | QVQLVESGGGVVQPGRSLRLSCAASGFTFSSYGMHWVRQAPGKGLEWVAVIWYDGSNKYYADSVKGRFTISRDNSKNTLYLQMNSLRAEDTAMYYCARDQGVGYDGLDVWGQGTSVTVSS |
| | | | SEQ ID NO: 26650 | SEQ ID NO: 30656 |
| iPS:435875 | 21-225_190B9 | NA | GACATCCAGATGACCCAGTCTCCATCTTCCGTGTCTGCATCTGTAGGAGACAGAGTCACCATCACTTGTCGGGCGAGTCAGGGTATTAACAACTGGTTAGCCTGGTATCAGCAGAAACCAGGGAAAGCCCCTAAGCTCCTGATCTATGGTGTTTCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTCTTGTCAACAGGCTAACAGTTTCCCGTGGACGTTCGGCCAAGGGACCAAGGTGGAAATCAGA | GAGGTGCAGCTGTTGGAGTCTGGGGGAGGCTTGGTACAGCCTGGGGGGTCCCTGAGACTCTCCTGTGCAGCCTCTGGATTCACCTTTAGCACCTATGCCATGAGTTGGGTCCGCCAGGCTCCAGGGAAGGGGCTGGAGTGGGTCTCAGCTATTAGTGGTAGTGGTGGTAACACACTACGCAGACTCCGTGAAGGGCCGGTTCACCATCTCCAGAGACAATTCCAAGAATACGCTGTATCTGCAAATGAACAGCCTGAGAGCCGAGGACACGGCCGTATATTCCTGTGCGAAAGATGGATCGGTGGAGCTCCTACTTTGACTACTGGGGCCAGGGAACCCTGGTCACCGTCTCCTCA |
| | | | SEQ ID NO: 26651 | SEQ ID NO: 30657 |

FIGURE 50
(Continued)

| | | | |
|---|---|---|---|
| iPS:435877 | 21-225_184E7 | AA | DIQMTQSPSSVSASVGDRVTITCRASQGINNWLA WYQQKPGKAPKLLIYGVSSLQSGVPSRFSGSGS GTDFTLTISSLQPEDFATYSCQQANSFPWTFGQG TKVEIR<br><br>SEQ ID NO: 26652 | EVQLLESGGGLVQPGGSLRLSCAASGFTFSTYAMS WVRQAPGKGLEWVSAISRSGGNTHYADSVKGRFTI SRDNSKNTLYLQMNSLRAEDTAVYSCAKDGFGGS SYFDYWGQGTLVTVSS<br><br>SEQ ID NO: 30658 |
| | | NA | GACATCCAGATGACCCAGTCTCCATCCTCACG GTCTGCATCTATAGGAGAGAGGTCACCATCA CTTGTCGGGCGAGTCAGGGCATTAGCAATTAT TTAGCCTGGATTCAGCAGAAACCAGGGACAGC CCCTAAGTCCCTTATTTATGCTGCATCCAGTT GCAAAGTGGGGTTTCATCAAGGTTTAGCGGCA GTGGATTTGGGACAGATTTCACTATCACCATC AGTAGTGTGCAGCCTGAAGATTTTGCAACTTA TTACTGCCAACAGTATATGGTTACCCATTCA CTTTCGGCCATGGGACCAAAGTGGATATCAAA<br><br>SEQ ID NO: 26653 | CAGGTGCAGCTGGTGCAGTCTGGGGGCTGAAGTG AAGAGCGCCTGGGGCTCAGTGAAGGTCTCCTGCA GGGCTTCTGGATACACCTTCACCAGCTACAATAT GCACTGGGTGCGACAGGTCCCTGGACAAGGGCT TGAGTGGATGGGATGGATCAACCCTAACAATGGT GGCTCAAACTATACACAGAAGTTTCAGGGCAGG GTCACCATGACCAGGGACACGTCCATCAGCACA GCCTACATGGAGCTGAGCAGGCTGAGATCTGAC GACACGGCCGTGTATTACTGTGCGAGAAAGTTTG GGGACTGGGGCCAGGGAACCCTGGTCACCGTCT CCTCA<br><br>SEQ ID NO: 30659 |
| | | AA | DIQMTQSPSSRSASIGERVTITCRASQGISNYLAW IQQKPGTAPKSLIYAASSLQSGVSSSRFSGSGFGTD FTITISSVQREDFATYYCQQYNGYPFTFGHGTKV DIK<br><br>SEQ ID NO: 26654 | QVQLVQSGAEVKTPGASVKVSCRASGYTFTSYNM HWVRQVPGQGLEWMGWINPNNGGSNYTQKFQGR VTMTRDTSISTAYMELSRLRSDDTAVYYCARKFGD WGQGTLVTVSS<br><br>SEQ ID NO: 30660 |

FIGURE 50
(Continued)

| | | | |
|---|---|---|---|
| iPS:435879 | 21-225_184H10 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGAAAGCCCCTAAGCGCCTGATCTATTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATATAGTTACCCATTCACTTTCGGCCCTGGGACCAAAGTGGATATCAAA SEQ ID NO: 26655 |
| | | AA | DIQMTQSPSSLSASVGDRVTITCRASQGIRNDLGWYQQKPGKAPKRLIYIASSLQSGVPSRFSGSGSGTEFTLTISSLQPEDFATYYCLQHNSYPFTFGPGTKVDIK SEQ ID NO: 26656 | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGGCATGCACTGGGTCCGCCAGGCTCCAGGCAAGGGCTGGAGTGGGTGGCAGTTATTTGGTATGATGAAACTAATAAACACTATGGAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAGAGAGGTTGGCTGGCACGATGACTATTGGGGCCAGGGAACCCTGGTCACCGTCTCCTCA SEQ ID NO: 30661 |
| | | | QVQLVESGGGVVQPGRSLRLSCVASGFTFSDYGMHWVRQAPGKGLEWVAVIWYDETNKHYGDSVKGRFTISRDNSKDTLYLQMNSLRAEDTAVYYCAREVGWHDDYWGQGTLVTVSS SEQ ID NO: 30662 |
| iPS:435881 | 21-225_184D11 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAAACCAGGAAAGCCCCTAAGCGCCTGATCTATTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATATAGTTACCCATTCACTTTCGGCCCTGGGACCAAAGTGGATATCAAA SEQ ID NO: 26657 | CAGGTGCAGCTGGTGGAGTCTGGGGGAGGCGTGGTCCAGCCTGGGAGGTCCCTGAGACTCTCCTGTCAGCGTCTGGATTCACCTTCAGTGACTATGGCATGCACTGGGTCCGCCAGGCTCCAGGCAAGGGCTGGAGTGGGTGGCAGTTATTTGGTATGATGAAACTAATAAACACTATGGAGACTCCGTGAAGGGCCGATTCACCATCTCCAGAGACAATTCCAAGAACACGCTGTATCTGCAAATGAACAGCCTGAGAGAGAGGTTGGCTGGCACGATGACTATTGGGGCCAGGGAACCCTGGTCACCGTCTCCTCA SEQ ID NO: 30663 |

FIGURE 50
(Continued)

| | | | |
|---|---|---|---|
| iPS:435883 | 21-225_185A1 | AA | DIQMTQSPSSLSASVGDRVTITCRASQGIRNDLGWYQQKPGKAPKRLIYIASSLQSGVPSRFSGSGSGTEFTLTISSLQPEDFATYYCLQHNSYPFTFGPGTKVDIK<br>SEQ ID NO: 26658 | QVQLVESGGGVVQPGRSLRLSCAASGFTFSDYGMHWVRQAPGKGLEWVAVIWYDETNKHYGDSVKGRFTISRDNSKDTLYLQMNSLRAEDTAVYYCAREVGWHDDYWGQGTLVTVSS<br>SEQ ID NO: 30664 |
| | | NA | GACATCCAGATGACCCAGTCTCCATCCTCACTGTCTGCATCTGTAGGAGACAGAGTCACCATCACTTGTCGGGCGAGTCAGGGCATTAGCAATGATTTAGCCTGGTTTCAGCAGACACCAGGGAAAGCCCCTAAGTCCCTGATCTCTGTTGCATCCAGTTTGCAAAGTGGGGTCCCATCAAGATTCAGCGGCAGTGGATCTGGGACAGACCTGAAGATTTCACTCTCACCATCAGCAGCCTGCAGCCTGAAGATTTTGCAACTTATTACTGCCGACAATATATCATAGTTACCCATTCACTTTCGGGCCCTGGGACCAAAGTGGATATCAAA<br>SEQ ID NO: 26659 | GAGGTGCAGCTGGTGGTGGAGTCTGGGGGAGGCCTGGTCAAGCCTGGGGGGTCCCTGAGACTCTCCTGTGCAGCCCTCTGGATTCACCTTCAATAGCTATAGCATGAACTGGGTCCGCCAGGCTCCAGGGAAGGGGCTGGAGTGGGTCTCATCCATTAGCAGTAGTGGTAGTTACATATATTACCAGACTCAGTGAAGGGCCGATTCACCATCTCCAGAGACAACGCCAAGAACTCACTGTATCTGCAAATGCACAGCCTGAGAGCCGAGGACACGGCTGTGTATTACTGTGCGAGAAGCAACCTTTTTGACTGCTGGGGCCAGGGAACCCCGGTCACCGTCTCCTCA<br>SEQ ID NO: 30665 |
| | | AA | DIQMTQSPSSLSASVGDRVTITCRASQGISNYLAWFQQTPGKAPKSLISVASSLQSGVPSRFSASGSGTDFTLTISSLQPEDFATYYCRQYHSYPFTFGPGTKVDIK<br>SEQ ID NO: 26660 | EVQLVESGGGLVKPGGSLRLSCAASGFTFNSYSMNWVRQAPGKGLEWVSSISSSGSYIYYADSVKGRFTISRDNAKNSLYLQMHSLRAEDTAVYYCARSNLFDCWGQGTPVTVSS<br>SEQ ID NO: 30666 |

FIGURE 50
(Continued)

| | | | |
|---|---|---|---|
| iPS:435885 | 21-225_185E10 | NA | GACATCCAGATGACCCAGTCTCCATCCTCACG GTCTGCATCTATAGGAGAGAGTCACCATCA CTTGTCGGGCGAGTCAGGGCATTAGCAATTAT TTAGCCTGGATTCAGCAGAAACCAGGACAGC CCCTAAGTCCCTTATCTATGCTGCATCCAGTTT GCAAAGTGGGGTTTCATCAAGGTTTAGCGGCA GTGGATTTGGGACAGATTTCACTCTCACCATC AGTAGTCTGCAGCCTGAAGATATAATGGTTACCCATTCA CTTTCGGCCCTGGGACCAAGTGGATATCAAA <br> SEQ ID NO: 26661 | CAGGTGCAGCTGTGTGCAGTCTGGGGCTGAAGTG AAGACGCCTGGGGCCTCAGTGAAGGTCTCCTGCA GGGCTTCTGGATACACCTTCACCAGCTACAATAT GCACTGGGTGCGACAGGTCCCTGGACAAGGGCT TGAGTGGATGGGATGGATCAACCCTAACAATGGT GGCTCAAACTATACACAGAAGTTTCAGGCAGG GTCACCATGACCAGGGACACGTCCATCAGCACA GCCTACATGGAGCTGAGCAGCCTGAGATCTGAC GACACGGCCGTGTATTACTGTGCGAGAAAGTTTG GGGACTGGGGCCAGGGAACCCTGGTCACCGTCT CCTCA <br> SEQ ID NO: 30667 |
| | | AA | DIQMTQSPSSRSASIGERVTITCRASQGISNYLAW IQQKPGTAPKSLIYAASSLQSGVSSRFSGSGFGTD FTLTISSLQPEDFATYCQQYNGYPFTFGPGTKV DIK <br> SEQ ID NO: 26662 | QVQLVQSGAEVKTPGASVKVSCRASGYTFTSYNM HWVRQVPGQGLEWMGWINPNNGGSNYTQKFQGR VTMTRDTSISTAYMELSRLRSDDTAVYYCARKFGD WGQGTLVTVSS <br> SEQ ID NO: 30668 |
| iPS:435887 | 21-225_186F7 | NA | GATGTTGTGATGGCCCAGACTCCACTCTCTCT GTCCGTCACCCTGGACAGCAGCCGGTCCCATCT CCTGCAAGTCTAGTCAGAGCCTCCTGCATGGT GATGGAAAGACCTATTTGTGTTGGTACCTCCA GAAGCCAGGCCAGCTCCACAGCTCCTGATCT ATGAAGTTCCAAGCGGTTCTCTGGAGTGCCA GATAGGTTCAGTGGCAGCGGGTCAGGACAG ATTTCACACTGAAAATCAGCGGGTGGAGGCT GAGGATGTTGGGGTTCTATTACTGCATGCAAAG TATACAGGTTCCCTGACGTTCGGCCAAGGGA CCAAGGTGGAAATCAAA <br> SEQ ID NO: 26663 | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGGCT GGAGTGGGTGGCAATTATATGGTATGATGGAAGT TATAAATATTATGCAGATCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATCATTAC GATTTTTTGGAGTGGGCACTTTGACTACTGGGGCC AGGGAACCCTGGTCACCGTCTCCTCA <br> SEQ ID NO: 30669 |

FIGURE 50
(Continued)

| | | | |
|---|---|---|---|
| | | AA | DVVMAQTPLSLSVTPGQPASISCKSSQSLLHGDG KTYLCWYLQKPGQPPQLLIYEVSKRFSGVPDRFS GSGSGTDFTLKISRVEAEDVGVYYCMQSIQVPW TFGQGTKVEIK<br>SEQ ID NO: 26664 | QVQLVESGGGVVQPGRSLRLSCAASGFTFSTYGMH WVRQAPGKGLEWVAIIWYDGSYKYYADSVKGRFT ISRDNSKNTLYLQMNSLRAEDTAVYYCARDHYDF WSGHFDYWGQGTLVTVSS<br>SEQ ID NO: 30670 |
| iPS:435889 | 21-225_186A11 | NA | GACATCCAGATGACCCAGTCTCCATCTTCCGT GTCTGCATCTGTTGGAGACAGAGTCACCATCA CTTGTCGGGCGAGTCAGGATATTAGCAGCTGG TTAGCCTGGTATCAGCAGAAACCAGGGAAAG CCCCTAAACTCCTGATCTATGCTGCATCCAGTT TACAAAGTGGGGTCCCATCAAGGTTCAGCGGC AGTGGATCTGGGACAGATTTCATTCTCACCAT CACCAGCCTGCAGCCTGATGATTTGCAACTT ACTATTGTCAACAGGTTAACAGTTTCCCATTC ACTTTCGGCCATGGGACCAAAGTGGATATCAA A<br>SEQ ID NO: 26665 | GAGGTGCAGCTGTTGGAGTCTGGGGGAGGCTTG GTACAGCCTGGGGGGTCCCTGAGACTCTCCTGTG CAGCCTCTGGATTCACCTTCAGCAGCTATGCCAT GAGTTGGGTCCGCCAGGCTCCAGGGAAGGGGCT GGAGTGGGTCTCAGTTATTAGTGGTAGAGGTGGT ACCACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGAAACGGACTGGG GATGATGTTTTTGATATCTGGGGCCAAGGGACAA TGGTCACCGTCTCTTCA<br>SEQ ID NO: 30671 |
| | | AA | DIQMTQSPSSVSASVGDRVTITCRASQDITSWLA WYQQKPGKAPKLLIYAASSLQSGVPSRFSGSGS GTDFILTITSVQPDDFATYYCQQVNSFPFTFGHG TKVDIK<br>SEQ ID NO: 26666 | EVQLLESGGGLVQPGGSLRLSCAASGFTFSSYAMS WVRQAPGKGLEWVSVISGRGGTFYADSVKGRFTI SRDNSKNTLYLQMNSLRAEDTAVYYCAKRTGDDV FDIWGQGTMVTVSS<br>SEQ ID NO: 30672 |

FIGURE 50
(Continued)

| | | | |
|---|---|---|---|
| iPS:435891 | 21-225_188H5 | NA | GACATCCAGATGACCCAGTCTCCATCCTCACT GTCTGCATCTATAGGAGAGAGAGTCACCATCA CTTGTCGGGCGAGTCAGGGCATTAGCAATTAT TTAGCCTGGCTTCAGCAGAAACCAGGGACAGC CCCTAAGTCCCTGATCTATGCTGCTTCCAGTTT GCAAAGTGGGGTCTCATCAAGGTTCAGCGGCA GTGGATTTGGGACAGATTTCACTCTCACCATC AGTAGTCTGCAGCCTGAAGATTTTGCAACTTA TTACTGCCAACAGTATAATAGTTATCCATTCA CTTTCGGCCCTGGGACCAAAGTGGATATCAAA |
| | | | SEQ ID NO: 26667 |
| | | AA | DIQMTQSPSSLSASIGERVTITCRASQGISNYLAW LQQKPGTAPKSLIYAASSLQSGVSSRFSGSGFGT DFTLTISSLQPEDFATYYCQQYNSYPFTFGPGTK VDIK |
| | | | SEQ ID NO: 26668 |
| | | NA | CAGGTGCAGCTGGTGCAGTCTGGGGCTGAGGTG AAGACGCCTGGGGCCTCAGTGAAGGTCTCCTGCA AGGCTTCTGGATACACCTTCACCAGCTACAATAT GCACTGGGTACGACAGGTCCCTGGACAAGGGCT TGAGTGGATGGGATGGATCAACAGAAGTTTCAGT GGTCAAACTATACAAACCCTAACAGTGGTGGCTC ATCACCATGACCAGGGACACGTCCATCAGCACA GCCTACATGGAGCTGAGCAGGCTGAGATCTGAC GACACGGCCGTATATTACTGTGCGAGAAAGTTTG GGGACTGGGGCCAGGGAACCCTGGTCACCGTCT CCTCA |
| | | | SEQ ID NO: 30673 |
| iPS:435895 | 21-225_188E8 | NA | GACATCCAGATGACCCAGTCTCCATCTTCCGT GTCTGCATCTGTAGGAGACAGAGTCACCATCA CTTGTCGGGCGAATCAGGATATTTCCAGCTGG TTAGCCTGGTATCAGCAGAAACCAGGGAAAG CCCCTAAGCTCCTGATCTATGCTGCATCCAATT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAGCAGGCTAACAGTTTCCCGTGG ACGTTCGGCCAAGGGACCAAGGTGGAAATCA AG |
| | | | SEQ ID NO: 26669 |
| | | | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTGCCAT GAACTGGGTCCGCCAGGCTCCAGGGAAGGGGCT GGAGTGGGTCTCAGTTATTAGTGGTAGTGGTGGT TACACATACTACGCAGACTCCGTGAAGGGCCGGT TCACCATCTCCAGAGACAACAATTCCAAGAACACGCT GTATCTGCAAATGAACAGCCTGAGAGCCGAGGA CACGGCCGTATATTTCTGTGCGAAAAGAACACC GATGATGCTTTTGATATCTGGGGCCAAGGGACAA TGGTCACCGTCTCTTCA |
| | | | SEQ ID NO: 30675 |

FIGURE 50
(Continued)

| | | | |
|---|---|---|---|
| iPS:435897 | 21-225_188B9 | AA | DIQMTQSPSSVSASVGDRVTITCRANQDISSWLA WYQQKPGKAPKLLIYAASNLQSGVPSGFSGSGS GTDFTLTISSLQPEDFATYYCQQANSFPWTFGQG TKVEIK<br>SEQ ID NO: 26670 | EVQLLESGGGLVQPGGSLRLSCAASGFTFSSSAMN WVRQAPGKGLEWVSVISGSGGYTYYADSVKGRFT ISRDNSKNTLYLQMNSLRAEDTAVYFCAKRNTDDA FDIWGQGTMVTVSS<br>SEQ ID NO: 30676 |
| | | NA | GACATCCAGATGACCCAGTCTCCATCCTCACT GTCTGCATCTATAGGAGAGAGACGTCACCATCA CTTGTCGGGCGAGTCAGGGCATTAGCAATTAT TTAGCCTGGCTTCAGCAGAAACCAGGACAGC CCCTAAGTCCCTGATCTATGCTGCATCCAGTTT GCAAAGTGGGGTCTCATCAAGGTTCAGCGGCA GTGGATTTGGGACAGATTTCACTCTCACCATC AGTAGTCTGCAGCCTGAAGATTTTGCAACTTA TTACTGCCAACAGTATATAGTTACCCATTCA CTTTCGGCCCTGGGACCAAAGTGGATATCAAA<br>SEQ ID NO: 26671 | CAGGTGCAGCTGGTGCAGTCTGGGGCTGAGGTG AAGAGCCTGGGGCTCAGTGAAGGTCCTGCA GGGCTTCTGATACACCTTCACCAGCTACAATAT GCACTGGGTGCGACAGGTCCCTGGACAAGGCT TGAGTGGATGGGATGGATCAACCTAACAGTGGT GGCTCAAACTATACACAGAGAAGTTTCAGGCAGG GTCACCATGACCAGGGACACGTCCATCAGCACA GCCTACATGGAGCTGAGCAGGCTGAGATCTGAC GACACGGCCGTGTATTACTGTGCGAGAAAGTTTG GGGACTGGGGCCAGGGAACCCTGGTCACCGTCT CCTCA<br>SEQ ID NO: 30677 |
| | | AA | DIQMTQSPSSLSASIGERVTITCRASQGISNYLAW LQQKPGTAPKSLIYAASSLQSGVSSRFSGSGFGT DFTLTISSLQPEDFATYYCQQYNSYPFTFGPGTK VDIK<br>SEQ ID NO: 26672 | QVQLVQSGAEVKTPGASVKVSCRASGYTFTSYNM HWVRQVPGQGLEWMGWINPNSGGSNYTQKFQGR VTMTRDTSISTAYMELSRLRSDDTAVYYCARKFGD WGQGTLVTVSS<br>SEQ ID NO: 30678 |

FIGURE 50
(Continued)

| | | | | |
|---|---|---|---|---|
| iPS:435899 | 21-225_188G11 | NA | GATATTGTGATGACCCAGACTCCACTCTCT GTCCGTCACCCCTGGACAGCCGGCCTCCATCT CCTGCATGTCTAGTCAGAGCCTCCTGCATGGT GATGGAAAGACCTATTTATATTGGTACCTGCA GAAGCCCGGCCAGCCTCCACAGCTCCTGATCT ATGAAGTTTCCAACCGGTTCTCTGGAGTGCCA GATACGTTCAGTGGCAGCGGGTCAGGGACAG ATTTCACACTGAAAATCAGCGGGTGGAGGCT GAGGATGTTGGGGTTTATTACTGCATGCAAAG TATACAGATTCCGTGGACGTTCGGCCAAGGGA CCAAGGTGGAAATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGCT GGAGTGGGTGACAATTATATGGTATGATGGAAGT TATAAATACTATGCAGACTCCGTGAAGGGCCGAT TCACCATCTCCAGAGACAACAATTCCAAGAACACGCT GTTTCTGCAAATGAACAGCCTGAGAGCCGAAGA CACGGCTGTGTATTACTGTGCGAGAGAGATAC GATTTTTGGAGTGGTCATTTTGACTACTGGGGCC AGGGAACCCTGGTCACCGTCTCCTCA |
| | | | SEQ ID NO: 26673 | SEQ ID NO: 30679 |
| | | AA | DIVMTQTPLSLSVTPGQPASISCMSSQSLLHGDG KTYLYWYLQKPGQPPQLLIYEVSNRFSGVPDTFS GSGSGTDFTLKISRVEAEDVGVYYCMQSIQIPWT FGQGTKVEIK | QVQLVESGGGVVQPGRSLRLSCAASGFTFSSYGMH WVRQAPGKGLEWVTIIWYDGSYKYYADSVKGRFT ISRDNSKNTLFLQMNSLRAEDTAVYYCARERYDF WSGHFDYWGQGTLVTVSS |
| | | | SEQ ID NO: 26674 | SEQ ID NO: 30680 |
| iPS:435901 | 21-225_189G2 | NA | GATATTGTGATGACCCAGACTCCACTCTCT GTCCGTCACCCCTGGACAGCCGGCCTCCATCT CCTGCAAGTCTAGTCAGAGCCTCCTGCATGGT GATGGAAAGACCTATTTGTTTGGTACCTGCA GAAGCCCGGCCAGCCTCCACAACTCCTGATCT ATGAAGTTTCCAACCGGTTCTCTGGAGTGTCA GATAGGTTCAGTGGCAGCGGGTCAGGGACAG ATTTCACACTGAAAATCAGCGGGTGGAGGCT GAGGATGTTGGGGTTTACTACTGCATGCAAAG TATACAGATTCCGTGGACGTTCGGCCAAGGGA CCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCAGTTCAGTAACTATGCCAT GCACTGGGTCCGCCAGGCTCCAGGCAAGGGCT GGAGTGGGTGGCAATTATATGGTATGATGGAAGT TATAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTATTGTGCGAGAGATCGATTC GATTTTTGGAGTGGTTATTCCGACTACTGGGGCC AGGGAACCCTGGTCACCGTCTCCTCA |
| | | | SEQ ID NO: 26675 | SEQ ID NO: 30681 |

FIGURE 50
(Continued)

| | | | |
|---|---|---|---|
| iPS:435903 | | AA | DIVMTQTPLSLSVTPGQPASISCKSSQSLLHGDG KTYLFWYLQKPGQPPQLLIYEVSNRFSGVSDRFS GSGSGTDFTLKISRVEAEDVGVYYCMQSIQIPWT FGQGTKVEIK<br>SEQ ID NO: 26676 | QVQLVESGGGVVQPGRSLRLSCAASGFTFSNYGM HWVRQAPGKGLEWVAIIWYDGSYKYYADSVKGR FTISRDNSKNTLYLQMNSLRAEDTAVYYCARDRFD FWSGYSDYWGQGTLVTVSS<br>SEQ ID NO: 30682 |
| | 21-225_190E2 | NA | GACATCGTGATGACCCAGTCTCCAGACTCCCT GGCTGTGTCTCTGGGCGAGAGGGCCACCATCA ACTGCAAGTCCAGCCAGAGTGTTTATTCAAC TCCAACAATAAGAACTACTTAGCTTGGTACCA GCAGAAACCAGGTCAGCCTCCTAACCTGCTCA TTTACTGGGCATCTCACCCGGGAATCCGGGGTC CCTGACCGATTCAGTGGCAGCGGGTCTGGGAC AGATTTCACTCTCACCATCAGCAGCATGCAGG CTGAAGATGTGGCAGTTTATTACTGTCAGCAA TATTGTAGTCTTCCATTCACTTTCGGCCCTGGG ACCAAAGTGGATATCAGA<br>SEQ ID NO: 26677 | CAGGTGCAACTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGCTTTCATACATTAGTAGTAGTGGTACT ACCGTATTCTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGAATGGGTG GGAGCCGACTACTGGGGCCAGGGAACCCTGGTC ACCGTCTCCTCA<br>SEQ ID NO: 30683 |
| | | AA | DIVMTQSPDSLAVSLGERATINCKSSQSVLFNSN NKNYLAWYQQKPGQPPNLLIYWASTRESGVPD RFSGSGSGTDFTLTISSMQAEDVAVYYCQQYCS LPFTFGPGTKVDIR<br>SEQ ID NO: 26678 | QVQLVESGGGLVKPGGSLRLSCAASGFTFSDYYMS WIRQAPGKGLEWLSYISSSGTTVFYADSVKGRFTIS RDNAKNSLYLQMNSLRAEDTAVYYCAREWVGAD YWGQGTLVTVSS<br>SEQ ID NO: 30684 |

FIGURE 50
(Continued)

| | | | | |
|---|---|---|---|---|
| iPS:435905 | 21-225_190A3 | NA | GAAATTATGTTGACGCAGTCTCCAGGCACCCT GTCTTTGTCTCCAGGGGAAAGAGCCACCCTCT CCTGCAGGGCCAGTCAGAATATAAGGAGCAA CTTCTTAGCCTGGTACCAGCAGAAACCTGGCC AGGCTCCCAGGCTCCTCATCTATGGTGCATCC AGCAGGGCCACTGGCATCCCAGACAGATTCAG TGGCAGTGTGTCTGGGACAGACTTCACTCTCA CCATCAACAGACTGGAGCCTGAAGATTTTGCG GTGTATTACTGTCAGCAGTATGGTAACTCACC GTGGACGTTCGGCCAAGGGACCAAGGTGAAA ATCAAA<br><br>SEQ ID NO: 26679 | CAGGTGCAGCTGCAGGAGTCGGGCCCAGGACTG GTGAAGCCTTCACAGACCCTGTCCCTCACCTGCA CTGTCTCTGGTGGCTCCATCAACAGTGGTGTTTA CTACTGGAACTGGATCCGCCAGCACCCAGGGAA GGGCCTGGAGTGGATTGGGTTCATCTTTATAGT GGGAGCACTTACTACAACCCGTCCCTCAAGAGTC GAGTTACCATATCAGTAGACACGTCTAAGAACCA GTTCTCCCTGAAGCTGAACTCTGTGACTGCCGCG GACACGGCCGTGTATTACTGTGCGAGAGGGGATT ACGATGGTTCGGGGAGTTATCACTACTATTACGG TATGGACGTCTGGGGCCAAGGGACCACGGTCAC CGTCTCCTCA<br><br>SEQ ID NO: 30685 |
| | | AA | EIMLTQSPGTLSLSPGERATLSCRASQNIRSNFLA WYQQKPGQAPRLLIYGASSRATGIPDRFSGSVSG TDFTLTINRLEPEDFAVYYCQQYGNSPWTFGQG TKVEIK<br><br>SEQ ID NO: 26680 | QVQLQESGPGLVKPSQTLSLTCTVSGGSINSGVY WNWIRQHPGKGLEWIGFIFYSGSTYYNPSLKSRVTI SVDTSKNQFSLKLNSVTAADTAVYYCARGDYDGS GSYHYYYGMDVWGQGTTVTVSS<br><br>SEQ ID NO: 30686 |
| iPS:435907 | 21-225_190G3 | NA | GACATCCAGATGACCCAGTCTCCATCCTCCCT GTCTGCATCTGTAAGAGACAGAGTCACCATCA CTTGCCGGGCAAGTCAGGGCATTAGAAAAGAT TTAGGCTGGTATCAGCAGAAACCAGGGAAAG CCCCTAAGCGCCTGATCTATGCTGCATCCAGT TTGCAAAGTGGGGTCCCATTAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGTG GACGTTCGGCCAAGGGACCAAGGTGGAAATC AAA<br><br>SEQ ID NO: 26681 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAGTGGGTGGCAGTTATATCATATGATGGAAGT TATAAAACTATGTAGACTCCGTGAAGGGCCGAT TCACCATCTCCAGAGACAATTCCAAGAACACGCT GTATCTGCAAATGAATAGCCTGAGAGCTGAGGA CACGGCTGTGTATTACTGTGCGAGAGGTACCCAC GGTACTACTACGGTGTGGACGTCTGGGGCCAA GGGACCACGGTCACCGTCTCCTCA<br><br>SEQ ID NO: 30687 |

FIGURE 50
(Continued)

| | | | |
|---|---|---|---|
| iPS:435909 | 21-225_190H3 | AA | DIQMTQSPSSLSASVRDRVTITCRASQGIRKDLG WYQQKPGKAPKRLIHTASSLQSGVPLRFSGSGS GTEFTLTISSLQPEDFATYYCLQHNSYPWTFGQG TKVEIK<br>SEQ ID NO: 26682 | QVQLVESGGGVVQPGRSLRLSCAASGFTFSSYGMH WVRQAPGKGLEWVAVISYDGGYKNYVDSVKGRF TISRDNSKNTLYLQMNSLRAEDTAVYYCARGTHG YYYGVDVWGQGTTVTVSS<br>SEQ ID NO: 30688 |
| | | NA | GACATCCAGATGACCCAGTCTCCATCTTCCGT GTCTGCATCTGTAGGAGACAGAGTCACCATCA CTTGTCGGGCGAGTCAGGGTCTTAACAACTGG TTAGCCTGGTATCAGCTGAAACCAGGAAAGC CCCTAAGCTCCTGATCTATGCTGTGTCCAGTTT GCAAAGTGGGGTCCCATCAAGGTTCAGCGGCA GTGGATCTGGGTCAGCAGTTCACTCTCACCAT CAGCAGCCTGCAGCCTGAAGATTTTGCAACTTA CCATTGTCAACAGGCTAACAGTCTCCCGTGGA CGTTCGGCCAAGGGACCAAGGTGGAAATCAA A<br>SEQ ID NO: 26683 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTCGTGGTGGT AACACATACTACGCAGACTCCGTGAAGGGCCGG TTCACCATCTCCAGAGACAATTCCAAGAACACGC TGTATCTGCAAATGAACAGTTTGAGAGCCGAGA CACGGCCGTATATTACTGTGCGAAAGATGGATTC GGTGGGAGCTCCTATTTTGACTACTGGGGCCAGG GAACCCTGGTCACCGTCTCCTCA<br>SEQ ID NO: 30689 |
| | | AA | DIQMTQSPSSVSASVGDRVTITCRASQGLNNWL AWYQLKPGKAPKLLIYAVSSLQSGVPSRFSGSGS GSEFTLTISSLQPEDFATYHCQQANSLPWTFGQG TKVEIK<br>SEQ ID NO: 26684 | EVQLLESGGGLVQPGGSLRLSCAASGFTFSSYAMS WVRQAPGKGLEWVSAISGRGGNTYYADSVKGRFT ISRDNSKNTLYLQMNSLRAEDTAVYYCAKDGFGGS SYFDYWGQGTLVTVSS<br>SEQ ID NO: 30690 |

FIGURE 50
(Continued)

| | | | | |
|---|---|---|---|---|
| iPS:435911 | 21-225_190B4 | NA | GAAATTGTGTTGACGCAGTCTCCAGGCACCCTGTCTTTGTCTCTCCAGGGGAAAGAGCCACACTCTCCTGCAGGGCCAGTCAGAGTATTGCAGCAGCTTCTTAGCCTGGTACCAGCAGAAACCTGGCCAGGCTCCCAGGCTCCTCATCTATGGTGCATCCAGCAGGGCCACTGGCATCCCAGACAGCTTCACTCTCACCATCAGCAGACTGGAGCCTGAAGATTTTGCAGTGTATTACTGTCAGCAGTATGGTAACTCACCGTGGGCGTTCGGCCAAGGGACCAAGGTGGAAATCAAA | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGATTACTACTGGAACTGGATCCGCCAGCACCCAGGGAAGGGCCTGGAGTGGATTGGGTACATCTTTACAGTGGGAGCACTACTACAACCCGTCCCTCAAGAGTCGAGTTACCATATCAGTAGACACGTCTAAGAACCAGTTCTCCCTGAAGCTGAGCTCTGTGACTGCCGCGGACACGGCCGTATATTACTGTGCGAGAGGGGATTACGATGGTTCGGGGAGTTATCACTACTACTACGGTATGGACGTCTGGGGCCAAGGGACCACGGTCACCGTCTCCTCA |
| | | | SEQ ID NO: 26685 | SEQ ID NO: 30691 |
| | | AA | EIVLTQSPGTLSLSPGERATLSCRASQSIRSSFLAWYQQKPGQAPRLLIYGASSRATGIPDRFSGSGSGTDFTLTISRLEPEDFAVYYCQQYGNSPWAFGQGTKVEIK | QVQLQESGPGLVKPSQTLSLTCTVSGGSISSGDYYWNWIRQHPGKGLEWIGYIFYSGSTYYNPSLKSRVTISVDTSKNQFSLKLSSVTAADTAVYYCARGDYDGSGSYHYYYGMDVWGQGTTVTVSS |
| | | | SEQ ID NO: 26686 | SEQ ID NO: 30692 |
| iPS:435913 | 21-225_190A7 | NA | GAAATTGTGTTGACGCAGTCTCCAGGCACCCTGTCTTTGTCTCTCCAGGGGAAAGAGCCACACTCTCCTGCAGGGCCAGTCAGAGTGTTAGAAGCAACTTCTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAACAGACTGGAGCCTGAAGATTTTGCAGTGTATTACTGTCAGCAGTATGGTAACTCACCGTGGACGTTCGGCCAAGGGACCAAGGTGGAAATCAAA | CAGGTGCAGCTGCAGGAGTCGGGCCCAGGACTGGTGAACCCTTCACAGACCCTGTCCCTCACCTGCACTGTCTCTGGTGGCTCCATCAGCAGTGGTGTTTACTACTGGAGCTGGATCCGCCAGCACCCAGGGAAGGGCCTGGAGTGGATTGGAACATCTATTACAGTGGGAGCACCTACAACAACCCGTCCCTCAAGAGTCGAATTATCATATCAGTAGACACGTCTAAGAACCAGTTCTCCCTGAAGCTGAGCTCTGTGACTGCCGCGGACACGGCCGTGTATTACTGTGCGAGAGGGGATTACGATGGTTCGGGGAGTTATCACTACTACGGTTTGGACGTCTGGGGCCAAGGGACCACGGTCACCGTCTCCTCA |
| | | | SEQ ID NO: 26687 | SEQ ID NO: 30693 |

FIGURE 50
(Continued)

| | | | |
|---|---|---|---|
| iPS:435915 | | AA | EIVLTQSPGTLSLSPGERATLSCRASQSVRSNFLAWHQQKPGQAPRLLIYGAYRRATGIPDRFSGSGSGTDFTLTINRLEPEDFAVYYCQQYGNSPWTFGQGTKVEIK<br>SEQ ID NO: 26688 | QVQLQESGPGLVNPSQTLSLTCTVSGGSISSGVYYWSWIRQHPGKGLEWIGNIYSGSTYNNPSLKSRIIISVDTSKNQFSLKLSSVTAADTAVYYCARGDYDGSGSYHYYYGLDVWGQGTTVTVSS<br>SEQ ID NO: 30694 |
| | 21-225_190H4 | NA | GCCAACGTGATGACCCAGTCTCCAGACTCCCTGGCTGTGTCTCTGGGCGAGAGGACCACCATCAACTGCAAGTCCAGCCAGAGTGTTTTACACAGCTCCAACAATTACAACTACTTAGTTGGTACCGGCAGAAACCAGGACAGCCTCCTAAGCTGCTCATTTACTGGGCATCTACCCGGGAATCCGGGGTCCCTGACCGATTCAGTGGCAGCGGGTCTGGTACAGATTCACTCTCACCATCAGCAGCCTGCAGGCTGAAGATGTGGCAGTTTATTACTGTCAGCAATATTATAGTATTCCTCCCACTTTCGGCCCTGGGACCAAAGTGGATATCAAA<br>SEQ ID NO: 26689 | CAGGTGCAGCTGGTGCAGTCTGGGGCTGAGGTGAAGAAGCCTGGGGCCTCAGTGAAGGTCTCCTGCAAGGCTTCTGGAAACACCTTCACCAATTATGATATCAACTGGGTGCGACAGGCCACTGGACAAGGCCTTGAGTGGATGGGATGGATGAACCCTAACAGTGGTAACACAGGCTATGCCCAGAAGTTCCAGGGCAGAGTCACCATGACCAGGAACACCTCCATAAGCACAGCCTACATGGAGCTGAGCAGCCTGAGATCTGAGGACACGGCCGTGTACATCTTTGACTACTGGGGCCAGGGAACCCTGGTCACCGTCTCCTCA<br>SEQ ID NO: 30695 |
| | | AA | ANVMTQSPDSLAVSLGERTTINCKSSQSVLHSSNNYNYLAWYRQKPGQPPKLLIYWASTRESGVPDRFSGSGSGTDFTLTISSLQAEDVAVYYCQQYYSIPPTFGPGTKVDIK<br>SEQ ID NO: 26690 | QVQLVQSGAEVKKPGASVKVSCKASGNTFTNYDINWVRQATGQGLEWMGWMNPNSGNTGYAQKFQGRVTMTRNTSISTAYMELSSLRSEDTAVYYCAHSSGWYIFDYWGQGTLVTVSS<br>SEQ ID NO: 30696 |

FIGURE 50
(Continued)

| | | | | |
|---|---|---|---|---|
| iPS:435917 | 21-225_190D5 | NA | GAAATTGTGCTGACTCAGTCTCCAGACTTTCAGTCTGTGGCTCCAAAGGAGAAAGTCACCATCACCTGCCGGGCCAGTCAGAGTATTGGTAGTAACTTACACTGGTACCAGCAGAAACCTGATCAGTCTCCAAAGCTCCTCATCAAGTCTGTCTTCCAGTCCTTCTCAGGGGTCCCCTCGAGGTTCAGTGGCAGTGGATCTGGGACAGATTTCACCCTCACCATCAATAGCCTGGAAACTGAAGATGCTGCAAACGTATTACTGTCAGCAGAGTAGTTTACCGTGGACGTTCGGCCAAGGGACCAAGGTGGAAATCAAA | CAGGTGCAGCTGCAGGAGTCGGGCCCAGGACTGGTGAAGCCTTCGGAGACCCTGTCCCTCACCTGCACTGTCTCTGGTGGCTCCATCAATAATTACTACTGGAGCTGGATCCGGCAGCCCCCGGGAAGGACTGGAGTGGATTGGGCGTATCTATGCCAGTGGAGCACCAACTACAACCCCTCCCTCAAGAGTCGAGTCACCATGTCAATAGACACGTCCAAGAACCAGTTCTCCCTGAAGCTGAGCTCTGTGACCGCCGCGGACACGGCCGTGTATTACTGTGCGAGAGATCGGGGATACTATGGCTACTACGGTATGGACGTCTGGGGCCAAGGGACCACGGTCACCATCTCCTCA |
| | | | SEQ ID NO: 26691 | SEQ ID NO: 30697 |
| | | AA | EIVLTQSPDFQSVAPKEKVTITCRASQSIGSNLHWYQQKPDQSPKLLIKSASQSFSGVPSRFSGSGSGTDFTLTINSLETEDAATYYCQQSSSLPWTFGQGTKVEIK | QVQLQESGPGLVKPSETLSLTCTVSGGSINNYYWSWIRQPAGKGLEWIGRIYASGSTNYNPSLKSRVTMSIDTSKNQFSLKLSSVTAADTAVYYCARDRGYYGYYGMDVWGQGTTVTISS |
| | | | SEQ ID NO: 26692 | SEQ ID NO: 30698 |
| iPS:435919 | 21-225_190H5 | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGATTCACTCTCACAATCAGCAGCCTGCAGCCTGAAGATTTTGCAACTTATTACTGTCTACAGCATAATAATTACCCGTGGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAGTTATATCATATGATGGAAGTATAAAAACTATGCAGACTCCGTGAAGGGCCGATTCACCATCTCCAGAGACAATTCCAAGAACACGCTGTATCTGCAAATGAATAGCCTGAGAGCTGAGGACACGGCTGTGTATTACTGTGCGAGAGAGGTACCCACGGTACTACGGTGTGGACGTCTGGGGCCAAGGGACCACGGTCACCGTCTCCTCA |
| | | | SEQ ID NO: 26693 | SEQ ID NO: 30699 |

FIGURE 50
(Continued)

| | | | |
|---|---|---|---|
| iPS:435921 | 21-225_190D6 | AA | DIQMTQSPSSLSASVGDRVTITCRASQGIRKDLG WYQQKPGKAPKRLIHTASSLQSGVPLRFSGSGS GTEFTLTISSLQPEDFATYYCLQHNNYPWTFGQG TKVEIK<br>SEQ ID NO: 26694 | QVQLVESGGGVVQPGRSLRLSCAASGFTFSSYGMH WVRQAPGKGLEWVAVISYDGGYKNYADSVKGRF TISRDNSKNTLYLQMNSLRAEDTAVYYCARGTHG YYYGVDVWGQGTTVTVSS<br>SEQ ID NO: 30700 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCTGAAACCAGGGAAAGC CCCTAAGCGCCTGATTTATGCTGCATCCAGTT GCAAAGTGGGGTCCCATCAAGGTTCAGCGGCA GTGGATCTGGGCCAGCCTGAAGATTTTGCAACTTA AGCAGCCTGCAGCCTGAAGATTTTTGCAACTTA TTACTGTCTACAGCATTATAGTTTCCCATTCAC TTTCGGCCCTGGGACCAAAGTGGATATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTATCAT GCACTGGGTCCGCCAGGCTCCAGGCAGGGGCT GGAGTGGGTGGCAGTTATATGCAGACTCCGTAAGT AATAAATACTATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGAGGAGTA TAGCAGTGGCTGGTTCGGGTACGGTATGGACGTC TGGGGCCAAGGGACCACGGTCACCGTCTCCTCA |
| | | | SEQ ID NO: 26695 | SEQ ID NO: 30701 |
| | | AA | DIQMTQSPSSLSASVGDRVTITCRASQGIRNDLG WYQLKPGKAPKRLIYAASSLQSGVPSRFSGSGSG PEFTLTISSLQPEDFATYYCLQHYSFPFTFGPGTK VDIK<br>SEQ ID NO: 26696 | QVQLVESGGGVVQPGRSLRLSCAASGFTFSSFIMH WVRQAPGRGLEWVAVIWYDGSNKYYADSVKGRF TISRDNSKNTLYLQMNSLRAEDTAVYYCAREEYSS GWFGYGMDVWGQGTTVTVSS<br>SEQ ID NO: 30702 |

FIGURE 50
(Continued)

| | | | | |
|---|---|---|---|---|
| iPS:435923 | 21-225_190H6 | NA | GACATCGTGATGACCCAGTCTCCAGACTCCCT GGCTGTGTCTCTGGGCGAGAGGGCCACCATCA ACTGCAAGTCCAGCCAGAGTGTTTTATTCAAC TCCAACAATAAGAACTACTTAGCTTGGTACCA GCAGAAACCAGGTCAGCCTCCTAACCTGCTCA TTTACTGGGCATCTACCCGGGAATCCGGGGTC CCTGACCGATTCAGTGGCAGCGGGTGTGGAC AGATTTCACTCTCACCATCAGCAGCCTGCAGG CTGAAGATGTGGCAGTTTATTACTGTCAGCAA TATTGTAGTCTCCATTCACTTTCGGCCCTGGG ACCAAAGTGGATATCAGA | DIVMTQSPDSLAVSLGERATINCKSSQSVLFNSN NKNYLAWYQQKPGQPPNLLIYWASTRESGVPD RFSGSGCGTDFTLTISSLQAEDVAVYYCQQYCSL PFTFGPGTKVDIR |
| | | | SEQ ID NO: 26697 | SEQ ID NO: 30703 |
| | | AA | CAGGTGCAACTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGCT GGAGTGGCTTTCATACATTAGTAGTAGTGGTACT ACCGTATTCTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGAATGGGTG GGAGCCGACTACTGGGGCCAGGGAACCCTGGTC ACCGTCTCCTCA | QVQLVESGGGLVKPGGSLRLSCAASGFTFSDYYMS WIRQAPGKGLEWLSYISSSGTTVFYADSVKGRFTIS RDNAKNSLYLQMNSLRAEDTAVYYCAREWVGAD YWGQGTLVTVSS |
| | | | SEQ ID NO: 26698 | SEQ ID NO: 30704 |
| iPS:435925 | 21-225_190D7 | NA | GACATCGTGATGACCCAGTCTCCAGACTCCCT GGCTGTGTCTCTGGGCGAGAGGGCCACCATCA ACTGCAAGTCCAGCCAGAGTGTTTTATTCAGC TCCAACAATTACAACTATTTAGTTTGGTATCA GCAGAAACCAGGACAGCCTCCTAAGTCTGCTCA TTTACTGGGCATCTACCCGGGAATCCGGGGTC CCTGACCGATTCAGTGGCAGCGGGTCTGGGAC AGATTTTACTCTCACCATCAGCAGCCTGCAGG CTGATGACGTGGCAGTTTATTATTGTCAACAA TATTATCGTACTCCGTGGACGTTCGGCCAAGG GACCAAGGTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACAGAAGTTCCAGGGCAG TAATACAGGCTATGCACAGAAGTTCCAGGGCAG AGTCACCATGACCAGGAATACCTCCATAAGCAC AGCCTACATGGAGCTGAGCAGCCTGAGATCTGA GGACACGGCCGTGTATTACTGTGCGAGTAGCAGT GGCTGGTACTTCTTTGACTACTGGGGCCAGGAA CCCTGGTCACCGTCTCCTCA |
| | | | SEQ ID NO: 26699 | SEQ ID NO: 30705 |

FIGURE 50
(Continued)

| | | | |
|---|---|---|---|
| iPS:435927 | | AA | DIVMTQSPDSLAVSLGERATINCKSSQSVLSSSN NYNYLVWYQQKPGQPPKLLIYWASTRKSGVPD RFSGSGSGTDFTLTISSLQADDVAVYYCQQYYR TPWTFGQGTKVEIK<br>SEQ ID NO: 26700 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCASSSGW YFFDYWGQGTLVTVSS<br>SEQ ID NO: 30706 |
| | | NA | GATATTGTGTTGACCCAGACTCCACTCTCTCTG TCCGTCACCCCTGGACACGCCGGCCTCCATCTC CTGCAAGTCTAGTCAGAGCCTCCTCCATAGTG ATGGAAGGACCTATTTGTATTGGTACCTGCAG AAACCAGGCCAGCCTCCACAGGTCCTGATCTG TGAGGTTCCAACGGTTCTCTGGAGTGCCAG ATAGGTCAGTGGCAGGGTCAGGACAGA TTTCACACTGAAAATCAGCCGGGGTGGAGGCTG GAGATGTTGGGGTTTATTACTGCATGCAAAGT ATACAGTTCCCTGGACGTTCGGCCAAGGGAC CAAGGTGGAAATCAAA<br>SEQ ID NO: 26701 | CAGCTGCAGCTGCAGGAGTCGGGCCAGGACTG GTGAAGCCTTCGGAGACCCTGTCCCTCACCTGCA CTGTCTCTGGTGGCTCCATCAGAAGTTACCACTG GAGTTGGATCCGGCAGCCCGCGGAAGGGACT GGAGTGGATTGGGCATATCTATACCAGTAGGAGC ACCAACTACAACCCCTCCCTCAAGAGTCGAGTCA CCATTTCAGTAGACACGTCCAAGAACCAGTTCTC CCTGAAGCTGAGCTCTGTGACCGCCACGGACACG GCCGTGTATTACTGTGCGAGACTCCGGTATAACT GGAACTTCCCTACTTTGACTACTGGGGCCAGGG AACCCTGGTCACCGTCTCCTCA<br>SEQ ID NO: 30707 |
| 21-225_190E7 | | AA | DIVLTQTPLSLSVTPGQPASISCKSSQSLLHSDGR TYLYWYLQKPGQPPQVLICEVSNRFSGVPDRFS GSGSGTDFTLKISRVEAGDVGVYYCMQSIQLPW TFGQGTKVEIK<br>SEQ ID NO: 26702 | QLQLQESGPGLVKPSETLSLTCTVSGGSIRSYHWSW IRQPAGKGLEWIGHIYTSRSTNYNPSLKSRVTISVDT SKNQFSLKLSSVTATDTAVYYCARLRYNWNFPYFD YWGQGTLVTVSS<br>SEQ ID NO: 30708 |

FIGURE 50
(Continued)

| | | | |
|---|---|---|---|
| iPS:435929 | 21-225_190D9 | NA | GAAATTGTGCTGACTCAGTTCCAGACTCTCA GTCTGTGACTCCAAAGGAGAAAGTCACCATCA CCTGCCGGGCCAGTCAGAGCATTGGTAGTAGC TTACACTGGTACCAGCAGAAACCAGATCAGTC TCCAAAGCTCCTCATCAAGTATGCTTCCCAGT CCTTCTCAGGGGTCCCCTCGAGTTCAGTGGC AGTGGATCTGGGACAGATTTCACCCTCACCAT CAATAGCCTGGAAGCTGAAGATGCTGCAACAT ATTACTGTCATCAGAGTAGTAGTTTCCCTCGG ACGTTCGGCCAAGGGACCAAGGTGAAATCA AA |
| | | | SEQ ID NO: 26703 |
| | | AA | EIVLTQFPDSQSVTPKEKVTITCRASQSIGSSIHW YQQKPDQSPKLLIKYASQSFSGVPSRFSGSGSGT DFTLTINSLEAEDAATYYCHQSSSFPRTFGQGTK VEIK |
| | | | SEQ ID NO: 26704 |
| iPS:435933 | 21-225_190F8 | NA | GACATCCAGATGACCCAGTCTCCTTCCTCACT GTCTGCATCTGTAGGAGACAGAGTCACCATCA CTTGTCGGACAGTCAGGGCATTGGCAATTAT TTAGCCTGGTTTCAGCAGAAAACCAGGGAAAGC CCCTAAGTCCCTACTCTATAAAGCATCCAGTTT ACAAAGTGGGGTCCCATCAAAGTTCAGCGGCA GTGGATCTGGGACAGATTTCACTCTCACCATC AGCAGCCTGCAACAACAGTATATGACTTACCACTCA TTACTGCCAACAGTATATGACTTACCACTCA CTTTCGGCGGAGGGACCAAGGTGGAGATCAA A |
| | | | SEQ ID NO: 26705 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTACTATGGCAT GCACTGGGTCCGCCAGGCTCCAGGCAAGGGGCT GGAGTGGGTGGCAGTTATATGGTATGATGGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGGG CGTGGGCTACGACGGTTTGGACGTCTGGGGCCAA GGGACCACGGTCACCGTCTCCTCA |
| | | | SEQ ID NO: 30711 |

Note: The upper portion of the table (for iPS:435929, DNA variable heavy) contains sequence GAGGTGCAGCTGTTGGACTCTGGGGGAGGCTTGG GACAGCCTGGGGGGTCCCTGAGACTCTCCTGTGC AGCCTCTGGATTCACCTTTGACAGCTATGCCATG AGTTGGGTCCGCCAGGCTCCAGGGAAGGGGCTG GAGTGGGTCTCAACTATTAGTGGTACTGGTCGTA GGACATACTACGCAGACTCCGTGAAGGGCCGGT TCACCATCTCCAGAGACAATTCCAAGAACACGCT GTATCTGCAAATGAATAGCCTGAGAGCCGAGGA CACGGCCGTATATTACTGTGCGAAAGAGGAGGA TTACTATGATAGTAGTGGCCCGGGGTTGACCCC TGGGGCCAGGGAACCCTGGTCACCGTCTCCTCA (SEQ ID NO: 30709) and amino acid sequence EVQLLDSGGGLGQPGGSLRLSCAASGFTFDSYAMS WVRQAPGKGLEWVSTISGTGRRTYYADSVKGRFTI SRDNSKNTLYLQMNSLRAEDTAVYYCAKEEDYYD SSGPGFDPWGQGTLVTVSS (SEQ ID NO: 30710)

FIGURE 50
(Continued)

| | | | |
|---|---|---|---|
| | | AA | DIQMTQSPSSLSASVGDRVTITCRTSQGIGNYLA WFQQKPGKAPKSLLYKASSLQSGVPSKFSGSGS GTDFTLTISSLQPEDFATYYCQQYMTYPLTFGGG TKVEIK<br><br>SEQ ID NO: 26706 | QVQLVESGGGVVQPGRSLRLSCAASGFTFSTYGMH WVRQAPGKGLEWVAVIWYDGSNKNYADSVKGRF TISRDNSKNTLYLQMNSLRAEDTAVYYCARDQGV GYDGLDVWGQGTTVTVSS<br><br>SEQ ID NO: 30712 |
| iPS:435935 | 21-225_190H8 | NA | GAAATTGTGCTGACTCAGTTTCCAGACTCTCA GTCTGTGACTCCAAAGGAGAAAGTCACCATCA CCTGCCGGGCCAGTCAGAGTCAGAGCATTGGTAGTAGC TTACACTGGTACCAGCAGAAACCAGATCAGTC TCCAAAGCTCCTCATCAAGTATGCTTCCAGT CCTTCTCAGGGGTCCCCTCGAGGTTCAGTGGC AGTGGATCTGGGACAGATTTCACCCTCACCAT CAATAGCCTGGAAGCTGAAGATGCTGCAACGT ATTACTGTCATCAGAGTAGTAGTTTCCCTCGG ACGTTCGGCCAAGGGACCAAGGTGGAAATCA AA<br><br>SEQ ID NO: 26707 | GGGGTACAACTGTTGGACTCTCGGGGAGGCTTGG GACAGCCTGGGGGGTCCCTGAGACTCTCCTGTGC AGCCTCTGGATTCACCTTTGACAGCTATGCCATG AGCTGGGTCCGCCAGGCTCCAGGGAAGGGGCTG GAGTGGGTCTCAACTATTAGTGGTACTGGTGTA GGACATATTACGCAGACTCCGTGAAGGGCCGGTT CACCATCTCCAGAGACAATTCCAAGAACACACTG TATCTGCAGATGAATAGCCTGAGAGCCGAGGAC ACGGCCGTATATTACTGTGCGAAAGAGGAGGATT ACTATGATAGTAGTGGCCCGGGGTTGACCCCTG GGGCCAGGGAACCCTGGTCACCGTCTCCTCA<br><br>SEQ ID NO: 30713 |
| | | AA | EIVLTQFPDSQSVTPKEKVTITCRASQSIGSSLHW YQQKPDQSPKLLIKYASQSFSGVPSRFSGSGSGT DFTLTINSLEAEDAATYYCHQSSSFPRTFGQGTK VEIK<br><br>SEQ ID NO: 26708 | GVQLLDSGGGLGQPGGSLRLSCAASGFTFDSYAMS WVRQAPGKGLEWVSTISGTGRRTYADSVKGRFTI SRDNSKNTLYLQMNSLRAEDTAVYYCAKEEDYYD SSGPGFDPWGQGTLVTVSS<br><br>SEQ ID NO: 30714 |

FIGURE 50
(Continued)

| | | | |
|---|---|---|---|
| iPS:435937 | 21-225_190H9 | NA | GACATCCAGATGACCCAGTCTCCATCCTCACT GTCTGCATCTGTGGGAGACAGAGTCACCATCA CTTGTCGGGCGAGTCAGGGCATTGGCAAGTAT TTAGCCTGGTTTCAGCAGAAACCAGGGAAAGC CCTAAGTCACTGATCTATGCTGCATCCAGTTT GCAAAGTGGGGTCCCATCAAAATTCAGCGGCA GTGGATCTGGGACAGATTTCACTCTCACCATC AGCAGCCTGCAGCCTGACGATTTTGCAACTTA TTACTGCCAACGATATGATACTTACCCATTCA CTTTCGGCCCTGGGACCAAAGTGGATATCAAA<br><br>SEQ ID NO: 26709 | CAGGTGCAGCTGGTGGAGTCTGGGGGAGGCGTG GTCCAGCCTGGGAGGTCCCTGAGACTCTCCTGTG CAGCGTCTGGATTCACCTTCAGGAACTATGGCAT GCACTGGGTCCGCCAGGCTCCAGGCAAGGGCT GGAGTGGGTGGCAGTTATATGGTTTGATGAAGT AATGACTACTATGCAGACTCCGTGAAGGGCCGAT TCACCATCTCCAGAGACACAATTCCAAGAACACGCT GTCACTGCAAATGAACAGCCTGAGAGCCGAGA CACGGCTGTGTATTACTGTGCGAGAGATAGAAGC GTCGGCTACGACGGTTTAGATGTCTGGGGCCAAG GGACCACGGTCACCGTCTCCTCA<br><br>SEQ ID NO: 30715 |
| | | AA | DIQMTQSPSSLSASVGDRVTITCRASQGIGKYLA WFQQKPGKALKSLIYAASSLQSGVPSKFSGSGSG TDFTLTISSLQPDDFATYYCQRYDTYPFTFGPGT KVDIK<br><br>SEQ ID NO: 26710 | QVQLVESGGGVVQPGRSLRLSCAASGFTFRNYGM HWVRQAPGKGLEWVAVIWFDGSNDYYADSVKGR FTISRDNSKNTLSLQMNSLRAEDTAVYYCARDRSV GYDGLDVWGQGTTVTVSS<br><br>SEQ ID NO: 30716 |
| iPS:435939 | 21-225_191H7 | NA | GAAATTGTGTTGACGCAGTCTCCAGGCACCCT GTCTTTGTCTCCAGGGGAAAGCGCCACCCTCT CCTGCAGGGCCGGTCAAAGTATTAGAACCGAC TTCTTAGCCTGGTACCAGCAGCAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAACAGACTGGAGCCTGAAGATTTTGCAG TGTATTTCTGTCAGCAGTATGGTAGTCACCGT GGACGTTCGGCCAAGGGACCAAGGTGGAAAT CAAT<br><br>SEQ ID NO: 26711 | CAGGTGCAACTGCAGGAGTCGGGCCCAGGACTG GTGAAGCCTTCACAGACCCTGTCCTCACCTGCA CTGTCTCTGGTGGCTCCATCAACAGTGGTGATTA CTACTGGAACTGGATCCGCCAGCACCCAGGGAA GGGCCTGGAGTGGATTGGGTACATCTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGGATT ACGATGGTTCGGGGAGTTATCACTACTATTACGG TATGGACGTCTGGGGCCAAGGGACCACGGTCAC CGTCTCCTCA<br><br>SEQ ID NO: 30717 |

FIGURE 50
(Continued)

| | | | |
|---|---|---|---|
| iPS:435941 | 21-225_191E8 | AA | EIVLTQSPGTLSLSPGESATLSCRAGQSIRTDFLA WYQQQPGQAPRLLIYGPSSRATGIPDRFSGSGSG TDFTLTINRLEPEDFAVYFCQQYGSSPWTFGQGT KVEIN<br>SEQ ID NO: 26712 | QVQLQESGPGLVKPSQTLSLTCTVSGGSINSGDYY WNWIRQHPGKGLEWIGYIFYSGSTYYNPSLKSRVTI SVDTSKNQFSLKLSSVTAADTAVYYCARGDYDGS GSYHYYGMDVWGQGTTVTVSS<br>SEQ ID NO: 30718 |
| | | NA | GAAATAGTGATGACGCAGTCTCCAGCCACCCT GTCTGTGTCTCCAGGGGAAAGAGCCACCCTCT CCTGCAGGCCCAGTCCAGTCAGAGTTTAGCAGAAAC TTAGCCTGGTACCAGCAGCAGAAACCTGGCCAGGC GCACTGGTCCGCCAGGCTCCAGGCAAGGGCT TCCCAGGCTCCTCATCTATGGTGCACTA GGGCCACTGGTATCCCATCCAGGTTCAGTGGC AGTGGGTCTGGGACAGAGTTCACTCTCACCAT CAGCAGCCTGAGAGTCTGAAGATTTTGCAGTTT ACTACTGTCAGCAGTATATAACTGGCCGCTC ACTTTCGGGGGAGGGATCAAGGTGGAGATCA AA<br>SEQ ID NO: 26713 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAATTATATGCCGACTCCGTGAAGT AATCAATACTATGCCGACTCCGTGAAGGGCCGAT TCACCATCTCCAGAGACAATTCCAAGAACACGCT GTATCTGCAATTGAACAGCTGAGAGCCGAGGA CACGGCTGTCTATTACTGTGCGAGAGCCCACGG GTCTACTACGCTATGGACGTCTGGGGCCAAG GGACCACGGTCACCGTCTCCTCA<br>SEQ ID NO: 30719 |
| | | AA | EIVMTQSPATLSVSPGERATLSCRPSQSFSRNLA WYQQKPGQAPRLLIYGASTRATGIPSRFSGSGSG TEFTLTISSLESEDFAVYYCQQYNNWPLTFGGGI KVEIK<br>SEQ ID NO: 26714 | QVQLVESGGGVVQPGRSLRLSCAASGFTFSNYGM HWVRQAPGKGLEWVAIIWFDGSNQYYADSVKGRF TISRDNSKNTLYLQLNSLRAEDTAVYYCARAHGVY YYAMDVWGQGTTVTVSS<br>SEQ ID NO: 30720 |

FIGURE 50
(Continued)

| | | | | |
|---|---|---|---|---|
| iPS:435943 | 21-225_191C9 | NA | GAAATTGTGCTGACTCAGTCTCCAGACTTTCA GTCTGTGACTCCAAAGGAGAAAGTCACCATCA CCTGCCGGGCCAGTCAGAGCAGAGTATTGTAGTAGT TTACACTGGTACCAGCAGAAACCAGATCAGTC TCCAAAGCTCCTCATCAAGTATGCTTCCCAGT CCTTCTCAGGGGACCCCTCGAGTTCAGTGGC AGTGGATCTGGGACAGATTTCACCCTCACCAT CAATAGCCTGGAAGCTGAAGATGCTGCAACGT ATTACTGTCATCAGACTAGAAGTTTACCTCTC ACTTTCGGCGGAGGGACCAAGGTGGAGATCA AA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAACTGGATCCGCCAGCACCCAGGAA GGGCCTGGAGTGGATTGGATATATCTATTACAGT GGGAGCACCTACTACAACCCGTCCCTCAAGAGTC GAGTTACCATATCAGTAGACACGTCTAAGAACCA GTTCTCCCTGAAGCTGAACTCTGTGACTGCCGCG GACACGGCCGTGTATTACTGTGCGAGATCCGGGT ATAATTGGACGCCGGGGTCGACCCTGGGGCC AGGGAACCCTGGTCACCGTCTCCTCA |
| | | AA | EIVLTQSPDFQSVTPKEKVTITCRASQSIGSSLHW YQQKPDQSPKLLIKYASQSFSGDPSRFSGSGSGT DFTLTINSLEAEDAATYYCHQTRSLPLTFGGGTK VEIK | QVQLQESGPGLVKPSQTLSLTCTVSGGSISSGGYYW NWIRQHPGKGLDWIGYIYYSGSTYYNPSLKSRVTIS VDTSKNQFSLKLNSVTAADTAVYYCARSGYNWDA GVDPWGQGTLVTVSS |
| | | | SEQ ID NO: 26715 | SEQ ID NO: 30721 |
| | | | SEQ ID NO: 26716 | SEQ ID NO: 30722 |
| iPS:435945 | 21-225_191A10 | NA | GACATCCAGATGACCCAGTCTCCATCCTCACT GTCTGCATCTGTAGGAGACAGAGTCACCATCA CTTGTCGGGCGAGTCAGGGCATTGGCAAGTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATATGGGACAGATTTCACTCTCACCATC AGCAGCCTGCAACAGTAGTACTTACCCGCTCA TTACTGCCAACAGTATAGTACTTACCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGTGATGGAAGT AATAAAAACTACGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTGCGAGAGATCAGGG CGTGGGCTACGACGGTTTGGACGTCTGGGGCCAA GGGACCCTCGGTCACCGTCTCCTCA |
| | | | SEQ ID NO: 26717 | SEQ ID NO: 30723 |

FIGURE 50
(Continued)

| | | | | |
|---|---|---|---|---|
| | | AA | DIQMTQSPSSLSASVGDRVTITCRASQGIGKYLA WFQQKPGKAPKSLIYAASSLQSGVPSKFSGSGY GTDFTLTISSLQPENFAIYYCQQYSTYPLTFGGGT KVEIK<br><br>SEQ ID NO: 26718 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAMYYCARDQGV GYDGLDVWGQGTSVTVSS<br><br>SEQ ID NO: 30724 |
| iPS:435947 | 21-225_191E10 | NA | GACATCCAGATGACCCAGTCTCCATCCTCACT GTCTGCATCTGTAGGAGACAGAGTCACCATCA CTTGTCGGGCGAGTCAGGGCATTGGCAAGTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAAATTTGCAACTTA TTACTGCCAACAGTATAGTACTTACCCGCTCA CTTTCGGCGGAGGGACCAAGGTGGAGATCAA A<br><br>SEQ ID NO: 26719 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGGCT GGAGTGGGTGGCAGTTATATGGTATGATGGAAGT AATAAAAACTACGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTGCGAGAGATCAGGG GTGGGCTACGACGGTTTGGACGTCTGGGGCCAA GGGACCTCGGTCACCGTCTCCTCA<br><br>SEQ ID NO: 30725 |
| | | AA | DIQMTQSPSSLSASVGDRVTITCRASQGIGKYLA WFQQKPGKAPKSLIYAASSLQSGVPSKFSGSGSG TDFTLTISSLQPENFATYYCQQYSTYPLTFGGGT KVEIK<br><br>SEQ ID NO: 26720 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAMYYCARDQGV GYDGLDVWGQGTSVTVSS<br><br>SEQ ID NO: 30726 |

FIGURE 50
(Continued)

| | | | | |
|---|---|---|---|---|
| iPS:435953 | 21-225_191B12 | NA | GACATCCGTGATGACCCAGTCTCCAGACTCCCTGGCTGTGTCTCTGGGCGAGAGGGCCACCATCAACTGCAAGTCCAGCCAGAGTGTTTTATTCAACTCCAACAATAAGAACTACTTAGCTTGGTACCAGCAGAAACCAGGTCAGCCTCCTAAACTGCTCATTTACTGGGCCTCTACCCGGGAATCCGGGGTCCCTGACCGATTCAGTGGCAGCGGGTCTGGGACAGATTTCACTCTCACCATCAGCAGCCTGCAGGCTGAAGATGTGGCAATTTATTACTGTCAGCAATATTCTAGTCTTCCATTCACTTTCGGCCCTGGGACCAAAGTGGATATCAAA | CAGGTGCAGCTGGTGGAGTCTGGGGGAGGCTTGGTCAAGCCTGGAGGGTCCCTGAGACTCTCCTGTGCAGCCCTCTGATTCACCTTCAGTGACTACTACATGAGCTGGATCCGCCAGGCTCCAGGGAAGGGCTGGAGTGGGTTTCATACATTAGTAGTAGTGGTACTACCGTATTCTACGCAGACTCTGTGAAGGGCCGATTCACCATCTCCAGGGACAACGCCAAGAACTCACTGTATCTGCAAATGAACAGCCTGAGAGCCGAGGACACGGCCGTGTATTACTGTGCGAGAGAATGGGTGGGAGCCGACTACTGGGGCCAGGGAACCCTGGTCACCGTCTCCTCA |
| | | | SEQ ID NO: 26721 | SEQ ID NO: 30727 |
| | | AA | DIVMTQSPDSLAVSLGERATINCKSSQSVLFNSNNKNYLAWYQQKPGQPPKLLIYWASTRESGVPDRFSGSGSGTDFTLTISNLQAEDVAIYYCQQYSSLPFTFGPGTKVDIK | QVQLVESGGGLVKPGGSLRLSCAASGFTFSDYYMSWIRQAPGKGLEWVSYISSSGTTVFYADSVKGRFTISRDNAKNSLYLQMNSLRAEDTAVYYCAREWVGADYWGQGTLVTVSS |
| | | | SEQ ID NO: 26722 | SEQ ID NO: 30728 |
| iPS:435957 | 21-225_191G12 | NA | GACATCCAGATGACCCAGTCTCCTTCCTCACTGTCTGCATCTGTAGGAGACAGAGTCACCATCACTTGTCGGACGAGTCAGGGCATTGGCAATTATTTAGCCTGGTTTCAGCAGAAACCAGGGAAAGCCCCTAAGTCCCTGCTCTATAAAGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGCCAACAGTATATCACTTACCCGCTCACTTTCGGCGGAGGGTCCAAGGTGGAGATCAAA | CAGGTGCAGCTGGTGGAGTCTGGGGGAGGCGTGGTCCAGCCTGGAGGGTCCCTGAGACTCTCCTGTGCAGCGTCTGGATTCACCTTCAGTAGCTATGGCATCACTGGGTCCGCCAGGCTCCAGGCAAGGGCTGGAGTGGGTGGCAGTTATATGGTATGATGGAAGTAATAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCAGGGCGTGGGCTACGACGGTTTGGACGTCTGGGGCCAAGGGACCACGGTCACCGTCTCCTCA |
| | | | SEQ ID NO: 26723 | SEQ ID NO: 30729 |

FIGURE 50
(Continued)

| | | | |
|---|---|---|---|
| | | AA | DIQMTQSPSSLSASVGDRVTITCRTSQGIGNYLA WFQQKPGKAPKSLLYKASSLQSGVPSKFSGSGS GTDFTLTISSLQPEDFATYYCQQYITYPLTFGGGS KVEIK<br>SEQ ID NO: 26724 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS<br>SEQ ID NO: 30730 |
| iPS:435961 | 21-225_192A2 | NA | GACATCCAGATGACCCAGTCTCCATCCTCACT GTCTGCATCTGTAGGAGACAGAGTCACCATCA CTTGTCGGGCGAATCAGGGCATTAACAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAGTATATAAGTTACCCATTCA CTTTCGGCCCTGGGACCAAAGTGGATATCAAA<br>SEQ ID NO: 26725 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGTGGCAGTTATATGGTATGGGATGGAAGT TATAAATACTATGCAGACTCCGTGAAGGGCCGAT TCACCATCTCCAGAGACAATGAACAGCCTGAGAGCT GTATCTGCAAATGAACAGCCTGAGAGCCGAGGA CACGGCTGTGTATTACTGTGCGAGAGATTCC CCTTATAGTGGCTACGCCTTGGACTACTTCTACG GTATGGACGTCTGGGGCCAAGGGACCACGGTCA CCGTCTCCTCA<br>SEQ ID NO: 30731 |
| | | AA | DIQMTQSPSSLSASVGDRVTITCRANQGINNYLA WFQQKPGKAPKSLIYAASSLQSGVPSKFSGSGSG TDFTLTISSLQPEDFATYYCQQYNSYPFTFGPGT KVDIK<br>SEQ ID NO: 26726 | QVQLVESGGGVVQPGRSLRLSCAASGFTFSSYGMH WVRQAPGKGLEWLAVIWYDGSYKYYADSVKGRF TISRDNSKNTLYLQMNSLRAEDTAVYYCAREDSPY SGYALDYFYGMDVWGQGTTVTVSS<br>SEQ ID NO: 30732 |

FIGURE 50
(Continued)

| | | | | |
|---|---|---|---|---|
| iPS:435963 | 21-225_192D2 | NA | GACATCCAGATGATTCAGTCTCCATCCTCACTGTCTGCATCTGTAGGAGACAGAGTCACCATCACTTGTCGGGCGAGTCAGGGCATTAGCAATTATTTAGCCTGGTTTCAGCAGAAACCAGGGAAAGCCCCTAAGTCCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGCCAACATTATGTTACTTACCGAACACTTTCGGCGGAGGGACCAAGGTGGAGATCAAA<br>SEQ ID NO: 26727 | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAAACTATGCAGACTCCGTGAAGGGCCGATTCACCATCTCCAGAGACAATTCCAAGAACATGTAGCAGCCTGCGAGCTGAGAGCCGAGGTGTATCTGCAAATGAACAGCCTGAGAGCCGAGGAAACGGCTGTGTATTACTGTGCGAGAGATCGTGGGGTTGGCTACTACGGTATGACGTCTGGGGCCAAGGGACCACGGTCACCGTCTCCTCA<br>SEQ ID NO: 30733 |
| | | AA | DIQMIQSPSSLSASVGDRVTITCRASQGISNYLAWFQQKPGKAPKSLIYAASSLQSGVPSKFSGSGSGTDFTLTISSLQPEDFATYYCQHYVTYPNTFGGGTKVEIK<br>SEQ ID NO: 26728 | QVQLVESGGGVVQPGRSLRLSCAASGFTFSSYGMHWVRQAPGKGLEWVAVIWYDGSNKNYADSVKGRFTISRDNSKNMLYLQMNSLRAEETAVYYCARDRGVGYYGMDVWGQGTTVTVSS<br>SEQ ID NO: 30734 |
| iPS:435965 | 21-225_192H2 | NA | GACATCCAGATGACCCAGTCTCCATCTTCCGTGTCTGCATCTGTAGGAGACAGAGTCACCATCACTTGTCGGGCGAGTCAGGGTATAAGTAGTTGGATAGCCTGGTATCAGCAGAAACCAGGGAAAGCCCCCTAAGTCCCTGATCTATGTGCATCCAGTTTGCAAAGTGGGGTCCCATCTAGGTTCAGCGGCAGTGGATCTGGGACAGATTTCACTCTCACCATCAGCAGCCTGCAGCCTGAAGATTTTGCAACTTACTATTGTCAACAGTCTAACAGTTTCCCATTCACTTTCGGCCCTGGGACCAAAGTGGATGTCAAA<br>SEQ ID NO: 26729 | GAGGTGCAGCTGTTGGAATCTGGGGGAGACTTAATACAGCCTGGGGGGTCCCTGAGACTCTCCTGTGCAGCCTCTGGATTCACCTTTAGCAGCTCTGCCATGAGCTGGGTCCGCCAGGCTCCAGGGAAGGGCTGGAGTGGGTCTCAGCCATTAGTGGTAGTGGTGGTAACACATTCTACGCAGACTCCGTGAAGGGCCGGTTCACCATCTCCAGAGACAATTCCAAGAACACGCTGTATCTGCAAATGAACAGCCTGAGAGCCGAAGACACGGCCGTTTATTACTGTGCGAAAACTCATAGCAGTAGTTGGGTCCCACTACTTTGACTACTGGGGCCAGGGAACCCTGGTCACCGTCTCCTCA<br>SEQ ID NO: 30735 |

FIGURE 50
(Continued)

| | | | |
|---|---|---|---|
| iPS:435967 | 21-225_192B3 | AA | DIQMTQSPSSVSASVGDRVTITCRASQGISSWIA WYQQKPGKAPKLLIYGASSLQSGVPSRFSGSGS GTDFTLTISSLQPEDFATYYCQQSNSFPFTFGPGT KVDVK<br><br>SEQ ID NO: 26730 | EVQLLESGGDLIQPGGSLRLSCAASGFTFSSSAMSW VRQAPGKGLEWVSAISGSGGNTFYADSVKGRFTIS RDNSKNTLYLQMNSLRAEDTAVYYCAKLIAVVGS HYFDYWGQGTLVTVSS<br><br>SEQ ID NO: 30736 |
| | | NA | GAAATTGTTGTTGACGCAGTCTCCAGGCACCCT GTCTTTGTCTCCAGGGGAAAGAGCCACCCTCT CCTGCAGGGCCAGTCAGAGTGTTGCAGCAGC TTCCTTGCCTGGTACCAGCAGAAACCTGGCCA GGCTCCCAGGCTCCTCATCTATGGTGCATCTA GCAGGGCCACTGGCATCCCAGACAGGTTCAGT GGCAGTGGGTCTGGGACAGACTTCACTCTCAC CATCAGCAGACTGGAGCCTGAAGATTTTGCTG TGTATTACTGTCAGCAGTATGGTAACTCACCG TGGGCGTTCGGCCAAGGGACCAAGGTGGAAA TCAAA<br><br>SEQ ID NO: 26731 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGATCCGCCAGCACCCAGGGAA GGGCCTGGAATGGATTGGGTTCATCTTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGTCGCG GACACGGCCGTGTATTACTGTGCGAGAGGGATT ACGATGGTTCGGGGAGTTATCACCACTACGG TATGGACGTCTGGGGCCAAGGGACCACGGTCAC CGTCTCCTCA<br><br>SEQ ID NO: 30737 |
| | | AA | EIVLTQSPGTLSLSPGERATLSCRASQSVRSSFLA WYQQKPGQAPRLLIYGASSRATGIPDRFSGSGSG TDFTLTISRLEPEDFAVYYCQQYGNSPWAFGQG TKVEIK<br><br>SEQ ID NO: 26732 | QVQLQESGPGLVKPSQTLSLTCTVSGGSISSGDYYW NWIRQHPGKGLEWIGFIFYSGSTYNPSLKSRVTIS VDTSKNQFSLKLSSVTVADTAVYYCARGDYDGSG SYHHYYGMDVWGQGTTVTVSS<br><br>SEQ ID NO: 30738 |

FIGURE 50
(Continued)

| | | | |
|---|---|---|---|
| iPS:435971 | 21-225_192D3 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGAACAGATTTCACTCTCACCATC AGCAGCCTGCAGCCTGAAGATTTTGCAACTTA TTACTGCCTACATTATCTTACTTACCCTCTCAC TTTCGGCGGAGGGACCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTTAGGCAT GCACTGGGTCCGCCAGGCTCCAGGCAAGGGCT GGAGTGGGTGGCAGTTATATGGTATGATGGAAGT AATGAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATAGGGG GGTGGGTTACTACGGTTTGGACGTCTGGGGCCAA GGGACCACGGTCACCGTCTCCTCA |
| | | | SEQ ID NO: 26733 | SEQ ID NO: 30739 |
| | | AA | DIQMTQSPSSLSASVGDRVTITCRASQGISNYLA WFQQKPGKAPKSLIYAASSLQSGVPSKFSGSGSG TDFTLTISSLQPEDFATYYCLHYLTYPLTFGGGT KVEIK | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARDRGV GYYGLDVWGQGTTVTVSS |
| | | | SEQ ID NO: 26734 | SEQ ID NO: 30740 |
| iPS:435973 | 21-225_192H3 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAAC TTCTTAGCCTGGTACCAGCAGAAAACCTGGCCA GGCTCCCAGGCTCCTCATCTTTGGTGCATCCA GCAGGGCCACTGGCATCCCAGACAGGTTCAGT GGCAGTGGGTCTGGGACAGACTTCACTCTCAC CATCAACAGACTGGAGCCTGAAGATTTTGCAG TGTATTACTGTCAGCAATATGGTATCTCACCGT GGACGTTCGGCCAAGGGACCAAGGTGGAAAT CAAA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGTTAGTTA CTACTGGAGCTGGATCCGCCAGCGCCCAGGGAA GGGCTGGAGTGGATTGGGAACCTCTATTACAGT GGGAGCACCTACTACAACCCGTCCCTCAGGAGTC GAGTACCATATCAGTAGACACGTCTAAGAACC AGTTCTCCCTGAAGCTGAGTTCTGTGACTGCCGC GGACACGGCCGTGTATTACTGTGTACGAGAGGGGA TTACGATGGTTCGGGGAGTTATCACTACTACCAC GGTATGGACGTCTGGGGCCAAGGGACCACGGTC ACCGTCTCCTCA |
| | | | SEQ ID NO: 26735 | SEQ ID NO: 30741 |

FIGURE 50
(Continued)

| | | | |
|---|---|---|---|
| iPS:435977 | 21-225_192E4 | AA | EIVLTQSPGTLSLSPGERATLSCRASQSVSSNFLAWYQQKPGQAPRLLIFGASSRATGIPDRFSGSGSGTDFTLTINRLEPEDFAVYYCQQYGISPWTFGQGTKVEIK<br><br>SEQ ID NO: 26736 | QVQLQESGPGLVKPSQTLSLTCTVSGGSISSVSYYWSWIRQRPGKGLEWIGNLYYSGSTYYNPSLRSRATISVDTSKNQFSLKLSSVTAADTAVYYCTRGDYDGSGSYHYYHGMDVWGQGTTVTVSS<br><br>SEQ ID NO: 30742 |
| | | NA | GACATCCAGATGACCCAGTCTCCATCCTCACTGTCTGCATCTGTAGGAGACAGAGTCACCATCACTTGTCGGGCGAGTCAGGGCATTGGCAATTATTTAGCCTGGTTTCAGCAGAAACCAGGGAAAGCCCCTAAGTCCCTGATCTATGTTGTATCCAGTTTACAAAGTGGGGTCCCATCAAGGTTCAGCGGCAGTGGATCTGGGACAGATTTCACTCTCACCATCAGCAGCCTGCAGCCTGAAGATTTTGCGACTTATTACTGCCAACGGTATGATACTTACCCATTCACTTTCGGCCCTGGGACCAAAGTGGATATCAAA<br><br>SEQ ID NO: 26737 | CAGGTGCAGCTGGTGGTGGAGTCTGGGGGAGGCGTGGTCCAGCCTGGGAGGTCCCTGAGACTCTCCTGTGCAGCGTCTGGATTCACCTTCAGTAGTTATGGCATGCACTGGGTCCGCCAGGCTCCAGGCAAGGGGCTGGAGTGGGTGGCAGTTATATGATACTCCGTGAGGGGCCGAAACAAAACTATGTAGACTCCGTGAGGGGCCGATTCACCATCTCCAGAGACAACGCCAAGAACACGCTGTATCTGCAAATGAACAGCCTGAGAGCCGAGGACACGGCTGTGTATTATTGTGCGAGAGATAGAAGCGTCGGCTACGACGGTATGGACGTCTGGGGCCAAGGGACCACGGTCACCGTCTCCTCA<br><br>SEQ ID NO: 30743 |
| | | AA | DIQMTQSPSSLSASVGDRVTITCRASQGIGNYLAWFQQKPGKAPKSLIYVVSSLQSGVPSRFSGSGSGTDFTLTISSLQPEDFATYYCQRYDTYPFTFGPGTKVDIK<br><br>SEQ ID NO: 26738 | QVQLVESGGGVVQPGRSLRLSCAASGFTFSSYGMHWVRQAPGKGLEWVAVIWYDGSNKNYVDSVRGRFTISRDNSKNTLYLQMNSLRAEDTAVYYCARDRSVGYDGMDVWGQGTTVTVSS<br><br>SEQ ID NO: 30744 |

FIGURE 50
(Continued)

| | | | | |
|---|---|---|---|---|
| iPS:435979 | 21-225_192H4 | NA | GACATCCAGATGACCCAGTCTCCATCCTCACT GTCTGCATCTGTAGGAGACAGAGTCACCATCA CTTGTGTGGCGAGTCAGGACATTAGCAATTAT TTAGCCTGGTTTCAGCAGAAACCAGGGAAAGC CCCTAAGTCCCTGATCTCTGCTGCATCCAGTT GCAAAGTGGGGTCCCATCAAAGTTCAGCGGCA GTAGATCTGGGACAGATTTCACTCTCACCATC AGCAGCCTGCAGCCTGAAGATTTTGCAACTTA TTACGGCCTACATTACTCCGCTCAC TTTCGGCGGAGGGACCAGGGTGGAGATCAGA<br><br>SEQ ID NO: 26739 | CAGGTGCAGTTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATGGTATGATGAAG CAATAAAAACTATGCAGACTCCGTGAAGGCCG ATTCACCATCTCCAGAGACAATTCCAAGAACACG CTGTATCTGCAAATGAACAGCCTGAGAGCCGAG GACACGGCTGTGTATTACTGTGCGAGAGATCAAG GTGTGGGGTACTACGGTATGGACGTCTGGGGCCA AGGGACCACGGTCACCGTCCTCA<br><br>SEQ ID NO: 30745 |
| | | AA | DIQMTQSPSSLSASVGDRVTITCRASQDISNYLA WFQQKPGKAPKSLISAASSLQSGVPSKFSGSRSG TDFTLTISSLQPEDFATYYGLHYLNYPLTFGGGT RVEIR<br><br>SEQ ID NO: 26740 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYYGMDVWGQGTTVTVSS<br><br>SEQ ID NO: 30746 |
| iPS:435983 | 21-225_192E5 | NA | GAAATTGTTCTGACTCAGTCTCCAGATTTTCAG TCTGTGACTCCAAAGGAGAAAGTCACCATCAC CTGCCGGGCCAGTCAGAGCATTGGTAGGAGTT TACACTGGTACCAGCAGAAACCAGATCAGTCT CCAAAGCTCCTCATCAAGTATGCTTCCCAGTC ATTCTCAGGGGTCCCCTGAGGTTCAGTGGCA GTGGATCTGGGACAGATTTCACCCTCACCATC AATAGCCTGGAGGCTGAAGATGCTGCAACGTA TTACTGTCATCAGAGTAGTCGTTTACCGCTCAC TTTCGGCGGAGGGACCAAGGTGGAGATCAAA<br><br>SEQ ID NO: 26741 | CAGGTGCAGCTGCAGGAGTCGGGCCCAGGACTG GTGAAGCCTTCACAGACCCTGTCCCTCACCTGCA CTGTCTCTGGTGACTCCATCAATAATGGTGATA CTACTGGAGCTGGATCCGCCAGCACCCAGGGAA GGGCCTGGAGTGGATTGGATACATCTTTACAGC GGGAGCACTACTACAACCCGTCCCTCAAGAGTC GAGTTACCATATCAGTTGACACGTCTAAGAATCA GTTCTCCCTGAAACTGAACTCTGTGACTGCCGCG GACACGGCCGTGTATTTTGTGCGAGAGCGGGAT ATAACTGGACAACGGGTTTGACTACTGGGGCC AGGGAACCCTGGTCACCGTCCTCA<br><br>SEQ ID NO: 30747 |

FIGURE 50
(Continued)

| | | | |
|---|---|---|---|
| iPS:435985 | 21-225_192F6 | AA | EIVLTQSPDFQSVTPKEKVTITCRASQSIGRSLHWYQQKPDQSPKLLIKYASQSFSGVPSRFSGSGSGTDFTLTINSLEAEDAATYYCHQSSRLPLTFGGGTKVEIK<br>SEQ ID NO: 26742 | QVQLQESGPGLVKPSQTLSLTCTVSGDSINNGGYYWSWIRQHPGKGLEWIGYIFYSGSTYNPSLKSRVTISVDTSKNQFSLKLNSVTAADTAVYFCARAGYNWDNGFDYWGQGTLVTVSS<br>SEQ ID NO: 30748 |
| | | NA | GACATCCAGATGACCCAGTCTCCATCCCCTGTCTGCATCTGTAGGAGACAGAGTCACCATCACTTGCCGGGCAAGTCAGGCATTAGAAATGATTTAGGCTGGTATCAGCTGAAACCAGGGAAAGCCCCTAAGCGCCTGATCTATGCTGCATCCAGTTTGCAAAGTGGGGTCCCATCAAGGTTCAGCGGCAGTGGATCTGGGCCAGCCTGAGAATTCACTCTCACAATCAGCAGCCTGCAGCCTGAAGATTTTGCAACTTATTACTGTCTACACAGCATTATAGTTTCCCATTCACTTTCGGCCCTGGGACCAAAGTGGATATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTTTATCATGCACTGGGTCCGCCAGGCTCCAGGCAGGGGCTGGAGTGGGTGGCAGTTATATGTATGGTGAAGTAATAAATACTATGTAGACTCCGTGAAGGGCCGATTCACCATCTCCAGAGACACAATTCCAAGAACACGCTGTATCTGCAAATGAACAGCCTGAGAGCCGAGGACACGGCTGTGTACTACTGTGCGAGAGGAGTATAGTAGGCGGCTGGTTCGGGTACGGTATGGACGTCTGGGGCCAAGGGACCACGGTCACCGTCTCCTCA |
| | | | SEQ ID NO: 26743 | SEQ ID NO: 30749 |
| | | AA | DIQMTQSPSSLSASVGDRVTITCRASQGIRNDLGWYQLKPGKAPKRLIYAASSLQSGVPSRFSGSGSGPEFTLTISSLQPEDFATYYCLQHYSFPFTFGPGTKVDIK<br>SEQ ID NO: 26744 | QVQLVESGGGVVQPGRSLRLSCAASGFTFSSFIMHWVRQAPGRGLEWVAVIWYDGSNKYYVDSVKGRFTISRDNSKNTLYLQMNSLRAEDTAVYYCAREEYSSGWFGYGMDVWGQGTTVTVSS<br>SEQ ID NO: 30750 |

FIGURE 50
(Continued)

| | | | | |
|---|---|---|---|---|
| iPS:435987 | 21-225_192G6 | NA | GACATCCAGATGACCCAGTCTCCTTCCTCACTGTCTGCATCTGTAGGAGACAGAGTCACCATCACTTGTCGGACGAGTCAGGGCATTGGCAATTATTTAGCCTGGTTTCAGCAGAAACCAGGGAAAGCCCCTAAGTCCCGTCTATAAAGCATCCAGTTTGCAAAGTGGGGTCCCATCAAAGTTCAGGGCAGTGGATCTGGGACAGATTTCACTCTCACCATCAGCAGCCTGCAGCCTGAAGATTTTGCAACTTATTACTGCCAACAGTATATGACTTACCCGCTCACTTTCGGCGGGGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAGTTTATGTATGATGAACTAATAAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCAGGGCGTGGGCTACGACGGTTTGGACGTCTGGGGCCAAGGGACCACGGTCACCGTCTCCTCA |
| | | | SEQ ID NO: 26745 | SEQ ID NO: 30751 |
| | | AA | DIKMTQSPSSLSASVGDRVTITCRTSQGIGNYLAWFQQKPGKAPKSLLYKASSLQSGVPSKFSGSGSGTDFTLTISSLQPEDFATYCQQYMTYPLTFGGGGTKVEIK | QVQLVESGGGVVQPGRSLRLSCAASGFTFSSYGMHWVRQAPGKGLEWVAVLWYDGTNKNYADSVKGRFTISRDNSKNTLYLQMNSLRAEDTAVYYCARDQGVGYDGLDVWGQGTTVTVSS |
| | | | SEQ ID NO: 26746 | SEQ ID NO: 30752 |
| iPS:435989 | 21-225_192F7 | NA | GACATCCAGATGACCCAGTCTCCATCCTCCCTGTCTGCGTCTGTAGGAGACAGAGTCACCATCACTTGCCGGGCAAGTCAGGGCATTAGAAATGATTTAGGCTGGTATCAACAGAAACCAGGGAAAGCCCCTAAGCGCCTAATCTACTGCATCCAGTTTGCAAAGTGGGGTCCCATTAAGGTTCAGCGGCAGTGGATCTGGGACAGACAGAATTCACTCTCACAATCAGCAGCCTGCAGCCTGAAGATTTTGCAACTTATTACTGTCTACAGCATAGTAGTTACCCTGTGACGTTCGGCCAAGGGACCAAGGTGGAAATCTAC | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGCATGCACTGGGTCCGCCAGGCTCCAGGCAAGGGGCTGGAGTGGGTGGCAGTTATATCATATGAGGAGTTATAAAAACTATGCAGACTCCGTGAAGGGCCGATTCACCATCTCCAGAGACAATTCCAAGAACACGCTGTATCTGCAAATGAATAGCCTGAGAGCTGAGGACACGGCTGTGTATTACTGTGCGAGAGGTACCACGGTACTACTACGGTGTGGACGTCTGGGGCCAAGGGACCACGGTCACCGTCTCCTCA |
| | | | SEQ ID NO: 26747 | SEQ ID NO: 30753 |

FIGURE 50
(Continued)

| | | | | |
|---|---|---|---|---|
| iPS:435993 | 21-225_192C8 | AA | DIQMTQSPSSLSASVGDRVTITCRASQGIRKDLG WYQQKPGKAPKRLIHTASSLQSGVPLRFSGSGS GTEFTLTISSLQPEDFATYYCLQHTSYPWTFGQG TKVEIY<br><br>SEQ ID NO: 26748 | QVQLVESGGGVVQPGRSLRLSCAASGFTFSSYGMH WVRQAPGKGLEWVTVISYDGGYKNYADSVKGRF TISRDNSKNTLYLQMNSLRAEDTAVYYCARGTHG YYYGVDVWGQGTTVTVSS<br><br>SEQ ID NO: 30754 |
| | | NA | GACATCCAGATGACCCAGTCTCCATCCTCACT GTCTGCATCTGTAGGAGACAGAGTCACCATCA CTTGTCGGGCGAGTCAGGGCATTAGGAAAGAT TAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGAACAGATTTCACTCTCACCATC AGCAGCCTGCAGCCTGAGGATTTTGCTACTTA TTACTGCCAACATTATCTTACTTACCCTCTCAC TTTCGGCGGAGGGACCAAGGTGGAGATCAAA<br><br>SEQ ID NO: 26749 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGCT GGAGTGGGTGGCAGTTATATGTATGATGGAAGT AATGAACACTATGCAGACTCCGTGAAGGGCCGA TTCATGATCTCCAGAGACAATTCCAAGAACACGC TGTATCTGCAAATGAACAGCCTGAGAGCCGAGG ACACGGCTGTGTATTACTGTGCGAGAGATAGGGG AGTGGGTTACTACGGTATGGACGTCTGGGGCCAA GGGACCACGGTCACCGTCTCCTCA<br><br>SEQ ID NO: 30755 |
| | | AA | DIQMTQSPSSLSASVGDRVTITCRASQGISNYLA WFQQKPGKAPKSLIYAASSLQSGVPSKFSGSGSG TDFTLTISSLQPEDFATYYCQHYLTYPLTFGGGT KVEIK<br><br>SEQ ID NO: 26750 | QVQLVESGGGVVQPGRSLRLSCAASGFTFSSYGMH WVRQAPGKGLEWVAVIWYDGSNEHYADSVKGRF MISRDNSKNTLYLQMNSLRAEDTAVYYCARDRGV GYYGMDVWGQGTTVTVSS<br><br>SEQ ID NO: 30756 |

FIGURE 50
(Continued)

| | | | | |
|---|---|---|---|---|
| iPS:435995 | 21-225_192F8 | NA | GAAATTGTGTTGACGCAGTCTCCAGGCACCCTGTCTTTGTCTCCAGGGGAAAGAGCCACCCTCCTGCAGGGCCAGTCAGAGTATTAGCAGCAGCTACTTAGCCTGGTACCAGCAGAAACCTGGCCAGGCTCCCCGGCTCCTCATCTATGGTGCATCAGCAGGGCCACTGGCATCCCAGCCAGGTTCAGTGGCAGTGGGTCTGGGACAGACTTCACTCTCACCATCAGCAGACTGGAGCCTGAAGATTTTGCAGTGTATTACTGTCAGCAGTATGAGAGTTCACCTGGACGTTCGGCCAAGGGACCAAGGTGGAAATCAAA SEQ ID NO: 26751 | CAGGTGCAGCTACAGCAGTGGGGCGCAGGACTGTTGAAGCCTTCGGAGACCCTGTCCCTCACCTGCGCTGTCTATGGTGGGTCTTCAGTGGTTGTACTGGAGCTGGATCCGCCAGCCCCAGGGAAGGGCTGGAGTGGATTGGGGAAATCAATCAAGTGAAGGTCCAACTACAACCGTCCCTCAAGAGTCGAGTCACCATTTCAGTAGACACGTCCACGAACCAGTTCTCCCTGAAGCTGAGATCTGTGACCGCCGGACACGGCTGTGTATTACTGTGCGAGAGACTACGGTGTCTTTGACTACTGGGGCCAGGGCACCCTGGTCACCGTCTCCTCA SEQ ID NO: 30757 |
| | | AA | EIVLTQSPGTLSLSPGERATLSCRASQSISSSYLAWYQQKPGQAPRLLIYGASSRATGIPARFSGSGSGTDFTLTISRLEPEDFAVYYCQQYESSPWTFGQGTKVEIK SEQ ID NO: 26752 | QVQLQQWGAGLLKPSETLSLTCAVYGGSFSGCYWSWIRQPPGKGLEWIGEINQSGRSNYNPSLKSRVTISVDTSTNQFSLKLRSVTAADTAVYYCARDYGVFDYWGQGTLVTVSS SEQ ID NO: 30758 |
| iPS:435997 | 21-225_192G8 | NA | GACATCCAGATGACCCAGTCTCCTTCCTCACTGTCTGCATCTGTAGGAGACAGAGTCACCATCACTTGTCGGAGAGTCAGGGCATTGGCAATTATTTAGCCTGGTTTCAGCAGAAACCAGGGAAAGCCCCTAAGTCCCTGCTCTATAAAGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGCCAACAGTATATCACTTACCCGCTCACTTTCGGCGGAGGGACCAAGGTGGAGATCAAA SEQ ID NO: 26753 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGATGAAGTAATAAAAACTATGCAGACTCCGTGAAGGGCCGATTCACCATCTCCAGAGACAACGCCAAGAACACGCTGTATCTGCAAATGAACAGCCTGAGAGCCGAGGACACGGCTGTGTATTACTGTGCGAGAGATCAGGGCGTGGCTACGACGGTTTGGACGTCTGGGGCCAAGGGACCACGGTCACCGTCTCCTCA SEQ ID NO: 30759 |

FIGURE 50
(Continued)

| | | | | |
|---|---|---|---|---|
| iPS:435999 | 21-225_192F9 | AA | DIQMTQSPSSLSASVGDRVTITCRTSQGIGNYLA WFQQKPGKAPKSLLYKASSLQSGVPSKFSGSGS GTDFTLTISSLQPEDFATYYCQQYITYPLTFGGGT KVEIK<br>SEQ ID NO: 26754 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS<br>SEQ ID NO: 30760 |
| | | NA | GATATTGTAATGACCCAGACTCCACTCTCTCT GTCCGTCACCCCTGGAGACAGCGGCCTCCATCT CCTGCAAGTCTAGTCAGAGCCTCCTCCATAGT GATGGAAGGACCTATTTGTATTGGTACCTGCA GAGGCCAGGCCAGTCCACAGCTCCTGATCT GTGAGGTTTCCAACCGGTTCGCTGGAGTGACA GATAGGTTCAGTGGCAGCGGGTCAGGGACAG ATTTCACACTGAAAATCAGCCGGGTGGAGCT GGGGATGTTGGGGTTTATTACTGCATGCAAAG TATACAGCTTCCCTGGACGTTCGGCCAAGGGA CCAAGGTGGAAATCAAA<br>SEQ ID NO: 26755 | CAGCTGCAGCTGCAGGAGTCGGGCCAGGACTG GTGAAGCCTTCGGAGACCCTGTCCCTCACCTGCA CTGTCTCTGGTGGCTCCATCAGAAGTACCACTG GAGCTGGATCCGGCAGCCCGCGGGAAGGGACT GGAGTGGATTGGGCTTATCTATACCAGTAGGAGC ACCAATTACAACCCCTCCCTCAAGAGTCGAGTCA CCATGTCAGTTGACAGTCCAAGAACCAGTTCTC CCTGAAGCTGAACTCTGTGACCGCCGCGGACACG GCCGTGTATTACTGTGCGAGACTCCGGTATAACT GGAACTTCCCTACTTTGACTACTGGGGCCAGGG AACCCTGGTCACCGTCTCCTCA<br>SEQ ID NO: 30761 |
| | | AA | DIVMTQTPLSLSVTPGQPASISCKSSQSLLHSDGR TYLYWYLQRPGQPPQLLICEVSNRFAGVTDRFS GSGSGTDFTLKISRVEAGDVGVYYCMQSIQLPW TFGQGTKVEIK<br>SEQ ID NO: 26756 | QLQLQESGPGLVKPSETLSLTCTVSGGSIRSYHWSW IRQPAGKGLEWIGLIYTSRSTNYNPSLKSRVTMSVD TSKNQFSLKLNSVTAADTAVYYCARLRYNWNFPY FDYWGQGTILVTVSS<br>SEQ ID NO: 30762 |

FIGURE 50
(Continued)

| | | | |
|---|---|---|---|
| iPS:436001 | 21-225_192C10 | NA | GACATCCAGATGACCCAGTCTCCATCCTCACT GTCTGCATCTGTGGGAGACAGAGTCACCATCA CTTGTCGGGCGAGTCAGGGCATTGGCAAGTAT TTAGCCTGGTTTCAGCAGAAACCAGGGAAAGC CCCTAAGTCACTGATCTATGCTGCATCCAGTT TGCAAAGTGGGGTCCCATCAAAGTTCAGCGGCA GTGGGTCTGGGACAGATTTCACTCTCACCATC AGCAGCCTGCAGCCTGACGATTTTGCAACTTA TTACTGCCAACGATATGATACTTACCCATTCA CTTTCGGCCCTGGGACCAAAGTGGATTTCAAA<br><br>SEQ ID NO: 26757 | CAGGTGCAGCTGGTGGAGTCTGGGGGAGGCGTG GTCCAGCCTGGGAGGTCCCTGAGACTCTCCTGTG CATCGTCTGATTCACCTTCAGGAACTATGGCAT GCACTGGGTCCGCCAGGCTCCAGGCAAGGGCT GAAATGGGTGGCAGTTATATGGTTTGATGAAGT AATGACTACTATGCAGACTCCGTGAAGGGCCGAT TCACCATCTCCAGAGACACAATTCCAAGAACACGCT GTCACTGCAAATGAACAGCCTGAGAGCCGAGA CACGGCTGTGTATTACTGTGCGAGAGATAGAAGC GTCGGCTACGACGGTTTAGATGTCTGGGGCCAAG GGACCACGGTCACCGTCTCCTCA<br><br>SEQ ID NO: 30763 |
| | | AA | DIQMTQSPSSLSASVGDRVTITCRASQGIGKYLA WFQQKPGKAPKSLIYAASSLQSGVPSKFSGSGSG TDFTLTISSLQPDDFATYYCQRYDTYPFTFGPGT KVDFK<br><br>SEQ ID NO: 26758 | QVQLVESGGGVVQPGRSLRLSCASSGFTFRNYGMH WVRQAPGKGLKWVAVIWFDGSNDYYADSVKGRF TISRDNSKNTLSLQMNSLRAEDTAVYYCARDRSVG YDGLDVWGQGTTVTVSS<br><br>SEQ ID NO: 30764 |
| iPS:436003 | 21-225_192G10 | NA | GACATCCAGATGACCCAGTCTCCATCCTCCCT GTCTGCATCTGTAGGAGACAGAGTCACCATCA CTTGCCGGGCAAGTCAGAGCATTAGCAACTAT TTAAATTGGTATCAGCAGACACCAGGAAAAGC CCCTAAGCTCCTGATCTATGCTGAATCCAGTT ACAAAGTGGGGTCCCATCAAGGTTCAGTGGCA GTGGATCTGGGACAGATTTCACTCTCACCATC AGCAGTCTGCAACAGAGTTACAGTTCCCCTCGT CTCCTGTCAACAGAGTTACAGTTCCCCTCGT GGACGTTCGGCCAAGGGACCAAGGTGAAAT CAAA<br><br>SEQ ID NO: 26759 | GAGGTGCAGCTGTTGGAGTCTGGGGGAGGCTTG GTACAGCCTGGGGGGTCCCTGAGACTCTCCTGTT CAGCCTCTGATTCACCTTTAGCAGTATGCCAT GAGCCTCTGGGTCCGCCAGGCTCCAGGAAGGGCT GGAGTGGGTCTCAGTTATTAGTGGTAGAGGCGGT AGTACATTCTACGCAGACTCCGTGAAGGGCCGGT TCACCATCTCCAGAGACAATTCCAAGAACACGCT GTATCTGCAAATGAACAGCCTGAGAGCCGAGA CACGGCCGTCTATTACTGTGCGCGACGTTTAGCA CTGGATGGCTATGATGCTTTTGATATCTGGGGCC AAGGGACAAATGGTCACCGTCTCTTCA<br><br>SEQ ID NO: 30765 |

FIGURE 50
(Continued)

| | | | |
|---|---|---|---|
| iPS:436005 | 21-225_192H10 | AA | DIQMTQSPSSLSASVGDRVTITCRASQSISNYLN WYQQTPGKAPKLLIYAESSLQSGVPSRFSGSGSG TDFTLTISSLQPEDFATYSCQQSYSSPPWTFGQGT KVEIK<br>SEQ ID NO: 26760 | EVQLLESGGGLVQPGGSLRLSCSASGFTFSSYAMS WVRQAPGKGLEWVSAISGRGGSTFYADSVKGRFTI SRDNSKNTLYLQMNSLRAEDTAVYYCARRLALDG YDAFDIWGQGTMVTVSS<br>SEQ ID NO: 30766 |
| | | NA | GACATCCAGATGACCCAGTCTCCATCCTCACT GTCTGCATCTGTAGGAGACAGAGTCACCATCA CTTGTCGGGCGAGTCAGGGCATTGGCAAGTAT TTAGCCTGGTTTCAGCAGAAACCAGGGAAAGC CCCTAAGTCCCTGATCTATGCTGCATCCAGTTT GCAAAGTGGGGTCCCATCAAGGTTCAGCGGCA GTGGATATGGGACAGATTTCACTCTCACCATC AGCAGCCTGCAGCCTGAAAATTTGCAACTTA TTACTGCCAACAGAGTATACTTACCCGCTCA CTTTCGGCGGAGGGACCAAGGTGGAGATCAA G<br>SEQ ID NO: 26761 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTATGATGGAAGT AATAAAACTACGCAGACTCCGTGAAGGGCCGA TTCACCATCTCCAGAGACAATTCCAAGAACACGC TGTATCTGCAAATGAACAGCCTGAGAGCCGAGG ACACGGCTATGTATTACTGTGCGAGAGATCAGG CGTGGGGTACGACGGTTTGGACGTCTGGGGCCAA GGGACCTCGGTCACCGTCTCCTCA<br>SEQ ID NO: 30767 |
| | | AA | DIQMTQSPSSLSASVGDRVTITCRASQGIGKYLA WFQQKPGKAPKSLIYAASSLQSGVPSKFSGSGY GTDFTLTISSLQPENFATYYCQQYSTYPLTFGGG TKVEIK<br>SEQ ID NO: 26762 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAMYYCARDQGV GYDGLDVWGQGTSVTVSS<br>SEQ ID NO: 30768 |

FIGURE 50
(Continued)

| | | | | |
|---|---|---|---|---|
| iPS:436007 | 21-225_192G12 | NA | GAAATTGTGTTGACGCAGTCTCCAGGCACCCT GTCTTTGTCTCCAGGGGAAAGAGCCACCCTCT CCTGCAGGGCCAGTCAGTGTTCAGAAGCGA CTTCTTAGCCTGGCTCCAGCAGAAACCTGGCC AGGCTCCCAGGCTCCTCATCTATGGTGTATCC CGCAGGGGCCACTGGCATCCCAGACAGGTTCAG TGGCAGTGGGTCTGGGACAGACTTCACTCTCA CCATCAACAGACTGGAGCCTGAAGATTTTGCA GTGTATTACTGTCAGCAGTATGGTAACTCACC GTGGACGTTCGGCCAAGGGACCAAGGTGGAA ATCAAA<br><br>SEQ ID NO: 26763 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTTA CCACTGGAGCTGGATCCGCCAGCACCCAGGGAA GGGCCTGGAGTGGATTGGGAACATCCATTACAG CGGGAGCACCTACAACAACCCGTCCCTCAAGAG TCGAGTTACCATATCAGTAGACACGTCTAAGAAC CAGTTCTCCCTGAAGCTGAGCTCTGTGACTGCCG CGGACACGGCCGTGTATTACTGTGCGAGAGGG ATTACGATGGTTCGGGGAGTTATCACTACTA CGTATGGACGTCTGGGGCCAAGGGACCACGGT CACCGTCTCCTCA<br><br>SEQ ID NO: 30769 |
| | | AA | EIVLTQSPGTLSLSPGERATLSCRASQSVRSDFLA WLQQKPGQAPRLLIYGVSRRATGIPDRFSGSGSG TDFTLTINRLEPEDFAVYYCQQYGNSPWTFGQG TKVEIK<br><br>SEQ ID NO: 26764 | QVQLQESGPGLVKPSQTLSLTCTVSGGSISSGVYHW SWIRQHPGKGLEWIGNIHYSGSTYNNPSLKSRVTIS VDTSKNQFSLKLSSVTAADTAVYYCARGDYDGSG SYHYYGMDVWGQGTTVTVSS<br><br>SEQ ID NO: 30770 |
| iPS:436009 | 21-225_193A1 | NA | GAAATTGTGTTGACGCAGTCTCCAGGCACCCT GTCTTTGTCTCCAGGGGAAAGAGCCACCCTCT CTTGTAGGGCCAGTCAGTGTTAGAAGCAAC TTCTTAGCCTGGCACCAGCAGAAACCTGGCCA GGCTCCCAGGCTCCTCATCTATGGTGCATCCC GCAGGGCCACTGGCATCCCAGACAGGTTCAGT GGCAGTGGGTCTGGGACAGACTTCACTCTCAC CATCAACAGACTGGAGCCTGAAGATTTTGCAG TGTATTACTGTCAGCAGTATGGTAACTCACCG TGGACGTTCGGCCAAGGGACCAAGGTGGAAA TCAAA<br><br>SEQ ID NO: 26765 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTTA CTACTGGAGCTGGATCCGCCAGCACCCAGGGAA GGGCCTGGAGTGGATTGGGAACATCTATTACAGT GGGAGCACCTACAACAACCCGTCCCTCAAGAGT CGAGTTACCATATCAGCAGACACGTCTAAGAACC AGTTCTCCCTGAAGCTGAGCTCTGTGACTGCCGC GGACACGGCCGTGTATTACTGTGCGAGAGGGA TTACGATGGTTCGGGGAGTTATCACTACTAC GTATGGACGTCTGGGGCCAAGGGACCACGGTC ACCGTCTCCTCA<br><br>SEQ ID NO: 30771 |

FIGURE 50
(Continued)

| | | AA | EIVLTQSPGTLSLSPGERATLSCRASQSVRSNFLA WHQQKPGQAPRLFIYGASRRATGIPDRFSGSGSG TDFTLTINRLEPEDFAVYYCQQYGNSPWTFGQG TKVEIK<br>SEQ ID NO: 26766 | QVQLQESGPGLVKPSQTLSLTCTVSGGSISSGVYYW SWIRQHPGKGLEWIGNIYYSGSTYNNPSLKSRLTIS ADTSKNQFSLKLSSVTAADTAVYYCARGDYDGSG SYHYYYGMDVWGQGTTVTVSS<br>SEQ ID NO: 30772 |
|---|---|---|---|---|
| iPS:436011 | 21-225_193B1 | NA | GAAATTGTGTTGACGCAGTCTCCAGGCACCCT GTCTTTGTCTCCAGGGGACAGAGCCACCCTCT CTTGCAGGGCCAGTCAGAGTGTTAGAAGCAAC TTCTTAGCCTGGCACCAGCAGAAACCTGGCCA GGCTCCCAGGCTCCTCATCTATGGTGCATCCC GCAGGGCCACTGGCATCCCAGACAGGTTCAGT GGCAGTGGGTCTGGGACAGACTTCACTCTCAC CATCAACAGACTGGAACTGGAAGATTTTGCAG TGTATTTCTGTCAGCAGTATGGTAACTCACCGT GGACGTTCGGCCAAGGGACCAAGGTGGAAAT CAAA<br>SEQ ID NO: 26767 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTTA CTACTGGAGCTGGATCCGCCAGCACCCAGGGAA GGGCCTGGAGTGGATTGGGAACATCTATTACAGT GGGAGCACCTACAACAACCCGTCCCTCAAGAGT CGAGTTACCATATCAGTAGACACGTCTAAGAACC AGTTCTCCCTGAAGCTGAGCTCTGTGACTGCCGC GGACACGGCCGTGTATTACTGTGCGAGAGGGA TTACGATGGTTCGGGGAGTTATCACTACTACTAC GGTATGGACGTCTGGGGCCAAGGGACCACGGTC ACCGTCTCCTCA<br>SEQ ID NO: 30773 |
| | | AA | EIVLTQSPGTLSLSPGDRATLSCRASQSVRSNFLA WHQQKPGQAPRLLIYGASRRATGIPDRFSGSGSG TDFTLTINRLEPEDFAVYFCQQYGNSPWTFGQGT KVEIK<br>SEQ ID NO: 26768 | QVQLQESGPGLVKPSQTLSLTCTVSGGSISSGVYYW SWIRQHPGKGLEWIGNIYYSGSTYNNPSLKSRVTIS VDTSKNQFSLKLSSVTAADTAVYYCARGDYDGSG SYHYYYGMDVWGQGTTVTVSS<br>SEQ ID NO: 30774 |

FIGURE 50
(Continued)

| | | | | |
|---|---|---|---|---|
| iPS:436013 | 21-225_193F2 | NA | GACATCCAGATGACCCAGTCTCCATCTTCCGT GTCTGCATCTGTAGGAGACAGAGTCACCATCA CTTGTCGGGCGAGTCAGGGTATTAACAACTGG TTAGCCTGGTATCAGCAGAAACCAGGGAAAG CCCCTAAGCTCCTGATCTATGGTGTTTCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTCTTGTCAACAGGCTAACAGTTTCCCGTGG ACGTTCGGCCAAGGGACCAAGGTGGAAATCA GA | GAGGTGCAGCTGTTGGAGTCTGGGGGAGGCTTG GTACAGCCTGGGGGGTCCCTGAGACTCTCCTGTG CAGCCCTCTGATTCACCTTTAGCACCTTTGCCAT GAGTTGGGTCCGCCAGGCTCCAGGGAAGGGCT GGAGTGGGTCTCAGCTATTAGTCGTAGTGGTGGT AACACACTACGCAGACTCCGTGAAGGGCCGG TTCACCATCTCCAGAGACAATTCCAAGAATACGC TGTATCTGCAAATGAACAGCCTGAGAGCCGAGG ACACGGCCGTATATTCCTGTGCAAAGATGGATT CGGTGGGGAGCTCCTACTTTGACTACTGGGGCCAG GGAACCCTGGTCACCGTCCTCA |
| | | | SEQ ID NO: 26769 | SEQ ID NO: 30775 |
| | | AA | DIQMTQSPSSVSASVGDRVTITCRASQGINNWLA WYQQKPGKAPKLLIYGVSSLQSGVPSRFSGSGS GTDFTLTISSLQPEDFATYSCQQANSFPWTFGQG TKVEIR | EVQLLESGGGLVQPGGSLRLSCAASGFTFSTFAMS WVRQAPGKGLEWVSAISRSGGNTHYADSVKGRFTI SRDNSKNTLYLQMNSLRAEDTAVYSCAKDFGGS SYFDYWGQGTLVTVSS |
| | | | SEQ ID NO: 26770 | SEQ ID NO: 30776 |
| iPS:436015 | 21-225_193D3 | NA | GAAATTGTGTTGACGCAGTCTCCAGGCACCCT GTCTTTGTCTCCAGGGGAAAGAGCCACCCTCT CCTGCAGGGCCAGTCAGAGTATTCGCAGCAGC TTCTTAGCCTGGTATCAGCAGAAACCTGGCCA GGCTCCCAGGCTCCTCATCTATGGTGCATCCA ACAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGGTAGTCACCG TGGGCGTTCGGCCAAGGGACCAAGGTGGAAA TCAAA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGATCCGCCAGTCCCAGGAA GGGCTGGAGTGGATTGGGTACATCTTTACAGT GGGAGCACCTACTACAACCCGTCCCTCAAGAGTC GACTTACCATATCAGTGGACACGTCTAAGAACCA GTTCTCCCTGAAGCTGAGCTCTGTGACTGCCGCG GACACGGCCGTGTATTACTGTACAAGGGGGATT ACGATGGTTCGGGGAGTTATCACTTCTACTACGG TATGGACGTCTGGGGCCAAGGGACCACGGTCAC CGTCTCCTCA |
| | | | SEQ ID NO: 26771 | SEQ ID NO: 30777 |

FIGURE 50
(Continued)

| | | | |
|---|---|---|---|
| iPS:436017 | 21-225_193F3 | AA | EIVLTQSPGTLSLSPGERATLSCRASQSIRSSFLA WYQQKPGQAPRLLIYGASNRATGIPDRFSGSGS GTDFTLTISRLEPEDFAVYYCQQYGNSPWAFGQ GTKVEIK<br>SEQ ID NO: 26772 | QVQLQESGPGLVKPSQTLSLTCTVSGGSISSGDYYW NWIRQLPGKGLEWIGYIFYSGSTYNPSLKSRLTISV DTSKNQFSLKLSSVTAADTAVYYCTRGDYDGSGSY HFYYGMDVWGQGTTVTVSS<br>SEQ ID NO: 30778 |
| | | NA | GAAATTGTGTTGACGCAGTCTCCAGGCACCCT GTCTTTGTCTCCAGGGGAAAGCGCCACCCTCT CCTGCAGGGCCGGTCAAAGTATTAGAACCGAC TTCTTAGTCTGGTACCAGCAGCAACCTGGCCA GGCTCCCAGGCTCCTCATCTATGGTGCATCA GCAGGGCCACTGGCTTCCCAGAGAGGTTCAGT GGCAGTGGGTCTGGGACAGACTTCACTCTCAC CATCAACAGACTGGAGCCTGAAGATTTTGCAG TGTATTACTGTCAGCAGTATGGAAGTCACCG TGGACGTTCGGCCAAGGGACCAAGGTGGAAA TCAAT<br>SEQ ID NO: 26773 | CAGGTGCAACTGCAGGAGTCGGGCCCAGGACTG GTGAAGCCTTCACAGACCCTGTCCCTCACCTGCA CTGTCTCTGGTGGCTCCATCAACAGTGGTGATTA CTACTGGAACTGGATCCGCCAGCACCCAGGGAA GGGCCTGGAGTGGATTGGGTACATCTTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGGATT ACGATGGTTCGGGGAGTTATCACTACTATTACGG TATGGACGTCTGGGGCCAAGGGACCACGGTCAC CGTCTCCTCA<br>SEQ ID NO: 30779 |
| | | AA | EIVLTQSPGTLSLSPGESATLSCRAGQSIRTDFLV WYQQOPGQAPRLLIYGASSRATGFPERFSGSGSG TDFTLTINRLEPEDFAVYYCQQYGSSPWTFGQGT KVEIN<br>SEQ ID NO: 26774 | QVQLQESGPGLVKPSQTLSLTCTVSGGSINSGDYY WNWIRQHPGKGLEWIGYIFYSGSTYNPSLKSRVTI SVDTSKNQFSLKLSSVTAADTAVYYCARGDYDGS GSYHYYGMDVWGQGTTVTVSS<br>SEQ ID NO: 30780 |

FIGURE 50
(Continued)

| | | | |
|---|---|---|---|
| iPS:436019 | 21-225_193C4 | NA | GACATCCAGATGACCCAGTCTCCATCCCT GTCTGCATCTGTTGGAGACAGAGTCACCATCA CTTGCCGGCCGAGTCAGGCATTAGCATTTAT TTAGCCTGGTATCAGCAGAAACCAGGAATGT TCCTAAGCTCCTGATCTATGCTGCATCCACTTT ACAATCAGGGGTCCCATCTCGGTTCAGTGGCA GTGGATCTGGGACAGATTTCACTCTCACCATC AGCAGCCTGCAGCCTGAAGATGTTGCAACTTA TTACTGTCAAAAGTATAACAGTGCCCCATTCA CTTTCGGCCCTGGGACCAAAGTGGATATCAAA SEQ ID NO: 26775 | DIQMTQSPSSLSASVGDRVTITCRPSQGISIYLAW YQQKPGNVPKLLIYAASTLQSGVPSRFSGSGSGT DFTLTISSLQPEDVATYYCQKYNSAPFTFGPGTK VDIK SEQ ID NO: 26776 |
| | | AA | |
| | | | GAGGTGCAGCTGTTGGAGTCTGGGGGAGGCTTG GCACAGCCTGGGGGGTCCCTGAGACTCTCCTGTG CAGCCCTCTGATTCACCTTTAGCAGCTATGCCAT GAACTGGGTCCGCCAGGCTCCAGGAAGGGCT GGAGTGGGTCTCAGTTATTATTGGTAATGGTGGT AGAACATACTACGCAGACTCCGTGAAGGGCCGG TTCTCCATCTCCAGAGACAATTCCAAGAACACGC TGTTTCTGCAAATGAACAGCCTGAGAGCCGAGG ACACGGCCGTATATTACTGTGCGAAAGATCTGGG TAGATACAGCTATGTTTCTTTGACTACTGGGGC CAGGGAACCCTGGTCACCGTCTCCTCA SEQ ID NO: 30781 |
| | | | EVQLLESGGGLAQPGGSLRLSCAASGFTFSSYAMN WVRQAPGKGLEWVSAIIGNGGRTYADSVKGRFSI SRDNSKNTLFLQMNSLRAEDTAVYYCAKDLGRYS YGFFDYWGQGTLVTVSS SEQ ID NO: 30782 |
| iPS:436021 | 21-225_193G4 | NA | GACATCGTGATGACCCAGTCTCCAGACTCCCT GGCTGTGTCTCTGGGCGAGAGGGCCACCATCA ACTGCAAGTCCAGCCAGAGTGTTTTATACAGC TCCAACAATTATAACTACTTGACTTGGTACCA GCAGAAACCAGGACAGCCTCCTAAGCTGCTCA TTTACTGGGCATCTACCCGAAAATCCGGGGTC CCTGACCGATTCAGTGGCAGCGGGTCTGGGAC AGATTTCACTCTCACCATCAGCAGCCTGCAGG CTGACGATGTGGCAGTTATTACTGTCAGCAA TATTATATTACTCCGTGGACGTTCGGCCAAGG GACCAAGGTGGACATCAAA SEQ ID NO: 26777 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGAACAGTAACAGTG GTAACACAGGCTATGCACAGAAGTTCCAGGGCA GAGTCACCATGACCAGGAACACCTCCATAAGAA CAGCCTACATGGAGCTGAACAGCCTGAGATCTG AGGACACGGCCGTGTATTACTGTGCGAGTAGCA GTGGCTGGTACTTCTTTGACTACTGGGGCCAGGG AACCCTGGTCACCGTCTCCTCA SEQ ID NO: 30783 |
| | | AA | |

FIGURE 50
(Continued)

| | | | |
|---|---|---|---|
| iPS:436023 | 21-225_193A5 | AA | DIVMTQSPDSLAVSLGERATINCKSSQSVLYSSN NYNYLTWYQQKPGQPPKLLIYWASTRKSGVPD RFSGSGSGTDFTLTISSLQADDVAVYYCQQYYIT PWTFGQGTKVDIK<br>SEQ ID NO: 26778 | QVQLVQSGAEVKKPGASVKVSCKASGYTFTNYDIN WVRQATGQGLEWMGWMNPNSGNTGYAQKFQGR VTMTRNTSIRTAYMELNSLRSEDTAVYYCASSSGW YFFDYWGQGTLVTVSS<br>SEQ ID NO: 30784 |
| | | NA | GACATCCAGATGACCCAGTCTCCATCCTCCCT GTTTGCATCTGTAGGAGACAGAGTCATCATCT CTTGCCGGGCAAGTCAGGGCATTAGAAATGAT TTAGGGTGGTATCAGCAGTATCCAGGGAAAGC CCCTAAGCGCGTGATTTATGCTGCATCCAGTT GCAAAGTGGGGTCCCATCAAGGTTCAGCGGCA GTGGATTTGGGACAGATTCACTATCACAATC AGCAGGCGTGCAGCTGAAGATTTTGAAACTTA TTACTGTCTACAGCATAATGATTTCCCGTTCAC TTTCGGCGGAGGGACCAAGGTGGAGATCAAA<br>SEQ ID NO: 26779 | CAGGTGCAGCTGGTGCAGTCTGGGGCTGAGGTG AAGAAGCCTGGGGCCTCAGTGAAGGTCTCCTGC AAGGCTTCTGGATACACCTTCATCAGTTATGATA TCAACTGGGTGCGACAGGCCACTGGACAAGGC TTGAGTGGATGGGATGGATGAACCTAAAAGGG GTAACACAGGCTATGCACAGAAGTTCCAGGCA GAGTCACCATGACCAGGGACACCTCCATAAGCA CAGCCTACATGGAGCTGAGCAGCCTGAGATCTG AGGACACGGCCGTTTATTACTGTGCGAGAGGAG ACCCGTATAACTGGAACTCCTACGTATGGACGT CTGGGGCCAAGGGGCCACGGTCACCGTCTCCTCA<br>SEQ ID NO: 30785 |
| | | AA | DIQMTQSPSSLFASVGDRVIISCRASQGIRNDLG WYQQYPGKAPKRVIYAASSLQSGVPSRFSGSGF GTEFTITISSVQPEDFETYYCLQHNDFPFTFGGGT KVEIK<br>SEQ ID NO: 26780 | QVQLVQSGAEVKKPGASVKVSCKASGYTFISYDIN WVRQATGQGLEWMGWMNPKRGNTGYAQKFQGR VTMTRDTSISTAYMELSSLRSEDTAVYYCARGDPY NWNSYAMDVWGQGATVTVSS<br>SEQ ID NO: 30786 |

FIGURE 50
(Continued)

| | | | |
|---|---|---|---|
| iPS:436025 | 21-225_193B5 | NA | GAAATTGTGCTGACTCAGTCTCCAGACTTTCA GTCTGTGACTCCAAAGGAGAAAGTCACCATCA CCTGCCGGGCCAGTCAGAGCATTGGTAGTAGC TTACACTGGTACCAGCAGAAACCAGATCAGTC TCCAAAGCTCCTCATCAAGTATGCTTCCCAGT CCTTCTCAGGGGTCCCCTCGAGTTCAGTGGC AGTGGATCTGGGACAGATTTCACCCTCACCAT CAATAGCCTGGAAGCTGAAGATGCTGCAACGT ATTACTGTCATCAGAGTAGTCGTTTACCATTCA CTTTCGGCCCTGGGACCAAAGTGGATATCAAA SEQ ID NO: 26781 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAGCTGGATCCGCCAGCACCCAGGGAA GGGCCTGGAGTGGATTGGGTACATCTATTACAGT GGGAGCACCTACTACAACCCGTCCCTCAAGAGTC GAGTTACCATATCAGTAGACACGTCTAAGAACCA GTTCTCCCTGAAGCTGAGCTCTGTGACCGCCGCG GACACGGCCGTGTATTATTGTGCGAGAGGAGAGT ATAACTGGAACCACGGTATGGACGTCTGGGGCC AAGGGACCACGGTCACCGTCTCCTCA SEQ ID NO: 30787 |
| | | AA | EIVLTQSPDFQSVTPKEKVTITCRASQSIGSSLHW YQQKPDQSPKLLIKYASQSFSGVPSRFSGSGSGT DFTLTINSLEAEDAATYYCHQSSRLPFTFGPGTK VDIK SEQ ID NO: 26782 | QVQLQESGPGLVKPSQTLSLTCTVSGGSISSGGVYW SWIRQHPGKGLEWIGYIYYSGSTYYNPSLKSRVTIS VDTSKNQFSLKLSSVAADTAVYYCARGEYNWNH GMDVWGQGTTVTVSS SEQ ID NO: 30788 |
| iPS:436027 | 21-225_193E6 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGGAGCGGT TACTTAGCCTGGTACCAGCAGAAACCTGGCCA GGCTCCCAGGCTCCTCATCTATGGTGCATCCA GCAGGGCCACTGGCATCCCAGACAGGTTCGGT GGCAGTGGGTCTGGGACAGACTTCACTCTCAC CATCAGCAGACTGGAGCCTGAAGATTTTGCAG TGTATTACTGTCAGCAGTATGAGAGTTCACCG TGGACGTTCGGCCAAGGGACCAAGGTGGAAA TCAAA SEQ ID NO: 26783 | CAGGTGCAGCTACAGCAGTGGGGCGCAGGACTG TTGAAGCCTTCGGAGACCCTGTCCCTCACCTGCG CTGTCTTTGGTGGGTCCTCAGTGGTCCCTACTGG AGTTGGATCCGCCAGCCCCCAGGGAAGGGGCTG GAGTGGATTGGGAATCAATCATAGTGGACGC ACCAACTACAACCCGTCCCTCAAGAGTCGAGTCA CCATATCAGTAGACACGTCCAAGAACCAGTTCTC CCTGAGGCTGAGCTCTGTGACCGCGGACACG GCTGTGTATTACTGTGCGAGAGACTACGGTGGTT TGGACTACTGGGGCCAGGGAACCCTGGTCACCGT CTCCTCA SEQ ID NO: 30789 |

FIGURE 50
(Continued)

| | | | | |
|---|---|---|---|---|
| iPS:436029 | 21-225_193H6 | AA | EIVLAQSPGTLSLSPGERATLSCRASQSVRSGYL AWYQQKPGQAPRLLIYGASSRATGIPDRFGGSG SGTDFTLTISRLEPEDFAVYYCQQYESSPWTFGQ GTKVEIK<br><br>SEQ ID NO: 26784 | QVQLQQWGAGLLKPSETLSLTCAVFGGSFSGPYWS WIRQPPGKGLEWIGESNHSGRTNYNPSLKSRVTISV DTSKNQFSLRLSSVTAADTAVYYCARDYGGLDYW GQGTLVTVSS<br><br>SEQ ID NO: 30790 |
| | | NA | GAAATTGTGTTGACGCAGTCTCCAGGCACCCT GTCTTTGTCTCCAGGGGAAAGCGCCACCCTCT CCTGCAGGGCCGGTCAAAGTATTAGAACCAAC TTCTTAGCCTGGTACCAGCAGCAACCTGGCCA GGCTCCCAGGCTCCTCATCTATGGTGCATCA GCAGGGCCACTGGCATCCCAGACAGGTTCAGT GGCAGTGGGTCTGGGACAGACTTCACTCTCAC CATCAACAGACTGGAGCCTGAAGATTTTGCAG TGTATTTCTGTCAGCAGTATGGTAGCTCACCGT GGACGTTCGGCCAAGGGACCAAGGTGAAAT CAAT<br><br>SEQ ID NO: 26785 | CAGGTGCAACTGCAGGAGTCGGGCCCAGGACTG GTGAAGCCTTCACAGACCCTGTCCCTCACCTGCA CTGTCTCTGGTGGCTCCATCAACAGTGGTGATTA CTACTGGAACTGGATCCGCCAGCACCCAGGGAA GGGCCTGGAGTGGATTGGGTACATCTTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGATT ACGATGGTTCGGGGAGTTATCACTACTATTACGG TATGGACGTCTGGGGCCAAGGGACCACGGTCAC CGTCTCCTCA<br><br>SEQ ID NO: 30791 |
| | | AA | EIVLTQSPGTLSLSPGESATLSCRAGQSIRTNFLA WYQQOPGQAPRLLIYGASSRATGIPDRFSGSGSG TDFTLTINRLEPEDFAVYFCQQYGSSPWTFGQGT KVEIN<br><br>SEQ ID NO: 26786 | QVQLQESGPGLVKPSQTLSLTCTVSGGSINSGDYY WNWIRQHPGKGLEWIGYIFYSGSTYYNPSLKSRVTI SVDTSKNQFSLKLSSVTAADTAVYYCARGDYDGS GSYHYYGMDVWGQGTTVTVSS<br><br>SEQ ID NO: 30792 |

FIGURE 50
(Continued)

| | | | |
|---|---|---|---|
| iPS:436031 | 21-225_193C7 | NA | GACATCCAGATGACCCAGTCTCCATCCTCACTGTCTGCATCTGTAGGAGACAGAGTCACCATCACTTGTGTCGGGCGAGTCAGGGCATTGGCAAGTATTTAGCCTGGTTTCAGCAGAAACCAGGGAAAGCCCCTAAGTCCCTGATCTATGCTGCATCCAGTTTGCAAAGTGGGGTCCCATCAAGTTCAGCGGCAGTGGATCTGGGACAGATTTCACTCTCACCATCAGCAGCCTGCAGCCTGAAGATTTTGCAACTTACTGCCAACAGTATTACTTACCCGCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAAAACTACGCAGACTCCGTGAAGGGCCGATTCACCATCTCCAGAGACAATTCCAAGAACACGCTGTATCTGCAAATGAACAGCCTGAGAGCTGAGGACACGGCTATGTATTACTGTGCGAGAGATCAGGGCGTGGGCTACGACGGCTTGGACGTCTGGGGCCAAGGGACCTCGGTCACCGTCTCCTCA |
| | | | SEQ ID NO: 26787 | SEQ ID NO: 30793 |
| | | AA | DIQMTQSPSSLSASVGDRVTITCRASQGIGKYLAWFQQKPGKAPKSLIYAASSLQSGVPSKFSGSGSGTDFTLTISSLQPEDFATYYCQQYSTYPLTFGGGTKVEIK | QVQLVESGGGVVQPGRSLRLSCAASGFTFSSYGMHWVRQAPGKGLEWVAVIWYDGSNKNYADSVKGRFTISRDNSKNTLYLQMNSLRAEDTAMYYCARDQGVGYDGLDVWGQGTSVTVSS |
| | | | SEQ ID NO: 26788 | SEQ ID NO: 30794 |
| iPS:436033 | 21-225_193E7 | NA | GACATCCAGATGACCCAGTCTCCATCTCCCTGTCTGCATCTGTAGGAGACAGAGTCACCATCACTTGCCGGGCAAGTCAGGGCATTAGAAACCAGGAAAGTTAGGCTGGTATCAGCAGAAACCAGGGAAAGCCCCCTAAGCGCCTAATCTATTCTGCATCCAGTTTGCAAAGGGGGGTCCCATCAAGATTCAGCGGCAGTGGATCTGGGACAGCTTGGACACAGATTCACTCTCACAATCAGCAGCCTGCAGCCTGAAGATTTTGCAACTTATTACTGTCTACAGCATAAAGGTACCCGCTCACTTTCGGCGGAGGGACCAAGGTGGAGATCAA | CAGGTGCAGCTACAGCAGTGGGGCGCAGGACTGTTGAAGCCTTCGGAGACCCTGTCCCTCACCTGCGCTGTCTATGGTGGGTCCTTCAGTGGTTACTTCTGGAGCTGGATCCGCCAGCCCCCAGGGAAGGGGCTGGAGTGGATTGGGGAAATCAATCATAGTGGAAGCACCAACTACAACCCGTCCCTCAAGAGTCGCGTCACCATATCAGTAGACACGTCCAAGAACCAGTTCTCCCTGAAGCTGAGCTCTGTGACCGCCGACACGGCTGTGTATTACTGTGCGAGAGACTACGGTGCTGACTACTGGGGCCAGGGAACCCTGGTCGCCGTCTCCGCA |
| | | | SEQ ID NO: 26789 | SEQ ID NO: 30795 |

FIGURE 50
(Continued)

| | | | |
|---|---|---|---|
| iPS:436035 | 21-225_193C8 | AA | DIQMTQSPSSLSASVGDRVTITCRASQGIRNDLG WYQQKPGKAPKRLIYSASSLQRGVPSRFSGSGS GTEFTLTISSLQPEDFATYYCLQHKRYPLTFGGG TKVEIK<br>SEQ ID NO: 26790 | QVQLQQWGAGLLKPSETLSLTCAVYGGSFSGYFW TWIRQPPGKGLEWIGEINHSGSTNYNPSLKSRVTISV DTSKNQFSLKLSSVTAADTAVYYCARDYGADYWG QGTLVAVSA<br>SEQ ID NO: 30796 |
| | | NA | GAAATTGTGTTGACGCAGTCTCCAGGCACCCT GTTTTGTCTCCAGGGGAAAGAGCCACCCTCT CCTGCAGGGCCAGTCAGAGTATTCGCAGCAGC TTCTTAGCCTGGTACCAGCAGAAACCTGGCCA GGCTCCCAGGCTCCTCATCTATGGTGCATCA GCAGGGCCACTGGCATCCCAGACAGGTTCAGT GGCAGTGGGTCTGGGACAGACTTCACTCTCAC CATCAGCAGACTGGAGCTGAAGATTTTGCAG TGTATTACTGTCAGCAATATGGTAACTCACCG TGGGCGTTCGGCCAAGGGATCAAGGTGGAAG TCAAA<br>SEQ ID NO: 26791 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGATCCGCCAGCACCCAGGGAA GGGCCTGGAGTGGATTGGGTACATCTTTTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGGATT ACGATGGTTCGGGAGTTATCACTACTACTACGG TATGGACGTCTGGGGCCAAGGGACCACGGTCAC CGTCTCCTCA<br>SEQ ID NO: 30797 |
| | | AA | EIVLTQSPGTLFLSPGERATLSCRASQSIRSSFLA WYQQKPGQAPRLLIYGASSRATGIPDRFSGSGSG TDFTLTISRLEPEDFAVYYCQQYGNSPWAFGQGI KVEVK<br>SEQ ID NO: 26792 | QVQLQESGPGLVKPSQTLSLTCTVSGGSISSGDYYW NWIRQHPGKGLEWIGYIFYSGSTYNPSLKSRVTIS VDTSKNQFSLKLSSVTAADTAVYYCARGDYDGSG SYHYYGMDVWGQGTTVTVSS<br>SEQ ID NO: 30798 |

FIGURE 50
(Continued)

| | | | | |
|---|---|---|---|---|
| iPS:436037 | 21-225_193D8 | NA | GAAATTGTGTTGAAGCAGTCTCCAGGCACCCT GTTTTGTCTCCAGGGGAGAGAGCCACCCTCT CCTGCAGGGCCAGTCAGAGTATAAGGACCAA CTTCTTAGCCTGGTACCAGCAGAAACCTGGCC AGGCTCCCAGGCTCCTCATCTATGGTGCATCC AGCAGGGCCACTGGCATCCCAGACAGGTTCAG TGGCAGTGGGTCTGGGACAGACTTCACTCTCA CCATCAACAGACTGGAGCCTGAAGATTTTGCA GTGTATTACTGTCAGCAGTATGGTAACTCAC GTGGACGTTCGGCCAAGGGACCAAGGTGGAA ATCAAA<br><br>SEQ ID NO: 26793 | CAGGTGCAGCTGCAGGAGTCGGGCCCAGGACTG GTGAAGCCTTCACAGACCCTGTCCCTCACCTGCA CTGTCTCTGGTGGCTCCATCAACAGTGGTGTTA CTACTGGAACTGATCCGCCAGCACCCAGGGAA GGGCCTGGAGTGGATTGGGTTCATCTTTACAGT GGGAGCACTTACTACAACCCGTCCCTCAAGAGTC GAGTTTCCATATCAGTAGACACGTCTAAGAACCA GTTCTCCCTGAAGCTGAGCTCTGTGACTGCCCG GACACGGCCGTGTATTACTGTGCGAGAGGGATT ACGATGGTTCGGGGAGTTATCACTACTATTACGG TATGGACGTCTGGGGCCAGGGGACCACGGTCAC CGTCTCCTCA<br><br>SEQ ID NO: 30799 |
| | | AA | EIVLKQSPGTLFLSPGERATLSCRASQSIRTNFLA WYQQKPGQAPRLLIYGASSRATGIPDRFSGSGSG TDFTLTINRLEPEDFAVYYCQQYGNSPWTFGQG TKVEIK<br><br>SEQ ID NO: 26794 | QVQLQESGPGLVKPSQTLSLTCTVSGGSINSGVT WNWIRQHPGKGLEWIGFIFYSGSTYYNPSLKSRVSI SVDTSKNQFSLKLSSVTAADTAVYYCARGDYDGS GSYHYYGMDVWGQGTTVTVSS<br><br>SEQ ID NO: 30800 |
| iPS:436039 | 21-225_193F8 | NA | GACATCCAGATGATCCAGTCTCCATCCTCACT GTCTGCATCTGTAGGAGACAGAGTCACCATCA CTTGTCGGGCGAGTCAGGGCGTTAGCAATCAT TTAGCCTGGTTCAGCAGAAACCAGGGAAGAGC CCCTAAGTCCCTGATCTATGCTGCATCCAGTTT GCAAAGTGGGGTCCCATCAAAGTTCAGCGGCA GTGGATCTGGGACAGCCTTCACTCTCACCATC AGCAGCCTGCAACAGTATATAGTTACCATCAA TTACTGCCAACAGTATAATAGTTACCATTCA CTTTCGGCCCTGGGACCAAAGTGGATATCAAA<br><br>SEQ ID NO: 26795 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATCTATGGCAT GGACTGGGTCCGCCAGGCTCCAGGCAAGGGCT GGAGTGGGTGGCAGTTATATGCAGACTCCGTGAAGT TATAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTATTGTGTGAGAGAGATTCC CCTTATAGTGGCTACGGCTTGGACTACTACACG GTATGACGTCTGGGGCCAAGGGACCACGGTCA CCGTCTCCTCA<br><br>SEQ ID NO: 30801 |

FIGURE 50
(Continued)

| | | | | |
|---|---|---|---|---|
| iPS:436041 | 21-225_193G8 | AA | DIQMIQSPSSLSASVGDRVTITCRASQGVSNHLA WFQQKPGRAPKSLIYAASSLQSGVPSKFSGSGSG ADFTLTISSLQPEDFATYYCQQYNSYPFTFGPGT KVDIK<br><br>SEQ ID NO: 26796 | QVQLVESGGGVVQPGRSLRLSCAASGFTFSIYGMD WVRQAPGKGLEWVAVIWYDGSYKYYADSVKGRF TISRDNSKNTLYLQMNSLRAEDTAVYYCVREDSPY SGYGLDYYYGMDVWGQGTTVTVSS<br><br>SEQ ID NO: 30802 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTAGAACCAAC TTCTTAGCCTGGCACCAGCAGAAACCTGGCCA GGCTCCCAGGCTCCTCATCTATGGTGCATCC GCAGGGCCACTGGCATCCCAGACAGGTTCAGT GGCAGTGGGTCTGGGACAGACTTCACTCTCAC CATCAACAGACTGGAGCCTGAAGATTTTGCAC TGTATTACTGTCAGCAGTATGGTAACTCACCG TGGACGTTCGGCCAAGGGACCAAGGTGGAAA TCAAA<br><br>SEQ ID NO: 26797 | CAGGTGCAGCTGCAGGAGAAAGGCCCAGGACTG GTGAAGCCTTCACAGACCCTGTCCCTCACCTGCA CTGTCTCTGGTGGCTCCGTCAGCAGTGGTGTTTA CTACTGGAGCTGGATCCGCCAGCACCCAGGGAA GGGCCTGGAGTGGATTGGGAACATCTATTACAGT GGGAGCACCTACAACAACCCGTCCCTCAAGAGT CGAGTTACCATATCAGTAGACACGTCTAAGAACC AGTTCTCCCTGAAGCTGAACTCTGTGACTGCCGC GGACACGGCCGTCTATTACTGTGCGCGAGGGAT TACGATGGTTCGGGGAGTTATCACTTCTACTACG GTTTGGACGTCTGGGGCCATGGACCACGGTCAC CGTCTCCTCA<br><br>SEQ ID NO: 30803 |
| | | AA | EIVLTQSPGTLSLSPGERATLSCRASQSVRTNFLA WHQQKPGQAPRLLIYGASRRATGIPDRFSGSGSG TDFTLTINRLEPEDFALYYCQQYGNSPWTFGQG TKVEIK<br><br>SEQ ID NO: 26798 | QVQLQEKGPGLVKPSQTLSLTCTVSGGSVSSGVYY WSWIRQHPGKGLEWIGNIYYSGSTYNNPSLKSRVTI SVDTSKNQFSLKLNSVTAADTAVYYCARGDYDGS GSYHFYYGLDVWGHGTTVTVSS<br><br>SEQ ID NO: 30804 |

FIGURE 50
(Continued)

| | | | | |
|---|---|---|---|---|
| iPS:436043 | 21-225_193G9 | NA | GAAATTGTACTGACTCAGTCTCCAGATTTTCAGTCTGTGACTCCAAAGGAGAAAGTCACCATCACCTGCCGGGCCAGTCAGAGCATTGGTAGGAGTTTACACTGGTACCAGCAGAAACCAGATCAGTCTCTAAAGCTCCTCATCAAGTATGCTTCCCAGTCATTCTCAGGGGTCCCCTCGAGGTTCAGTGGCAGTGGATCTGGGACAGATTTCACCCTCACCATCAATAGCCTGGAGGCTGAAGATGCTGCAACGTATTTCTGTCATCAGAGTAGTCGTTTACCGCTCACTTTCGGCGGCGGGACCAAGGTGGAGATCAAA SEQ ID NO: 26799 | CAGGTGCAGCTGCAGGAGTCGGGCCCAGGACTGGTGAAGCCTTCACAGACCCTGTCCCTCACCTGCACTGTCTCTGGTGACTCCATCAATAATGGTGGATACTACTGGAGCTGGATCCGCCAGCACCCAGGGAAGGGCCTGGAGTGGATTGGGTACATCTTTTACAGCGGGAGCACCTACTACAACCCGTCCCTCAAGAGTCGAGTTACCATATCAGTTGACACGTCTAAGAATCAGTTCTCCCTGAAGCTGAACTCTGTGACTGCCGCGGACACGGCCGTGTATTTTTGTGCGAGAGCGGGATATAACTGGGACAACGGGTTTGACTACTGGGGCCAGGGAACCCTGGTCACCGTCTCCTCA SEQ ID NO: 30805 |
| | | AA | EIVLTQSPDFQSVTPKEKVTITCRASQSIGRSLHWYQQRPDQSLKLLIKYASQSFSGVPSRFSGSGSGTDFTLTINSLEAEDAATYFCHQSSRLPLTFGGGTKVEIK SEQ ID NO: 26800 | QVQLQESGPGLVKPSQTLSLTCTVSGDSINNGGYYWSWIRQHPGKGLEWIGYIFYSGSTYYNPSLKSRVTISVDTSKNQFSLKLNSVTAADTAVYFCARAGYNWDNGFDYWGQGTLVTVSS SEQ ID NO: 30806 |
| iPS:436045 | 21-225_193A10 | NA | GACATCCAGATGACCCAGTCTCCATCCTCACTGTCTGCATCTGTAGGAGACAGAGTCACCATCACTTGTGTGCGGGCGAGTCAGGGCATTAGCAATTATTTAGCCTGGTTTCAGCAGAAACCAGGGAAAGCCCCTAAGGTCCTGATCTATGCTGCATCCAGTTTGCAAAGTGGGGTCCCATCAAAGTTCAGCGGCAGTGGATCTGGAACAGATTTCACTCTCACCATCAGCAGCCTGCAGCCTGAAGATTTTGCAACTTATTTTCTGCCAACATTATCTTACTTACCCTCTCACTTTCGGCGGAGGGACCAAGGTGGAGATCAAA SEQ ID NO: 26801 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATGAAACATATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATAGGGGGGTGGTTACTACGGTTTGGACGTCTGGGGCCAAGGGACCACGGTCACCGTCTCCTCA SEQ ID NO: 30807 |

FIGURE 50
(Continued)

| | | | |
|---|---|---|---|
| iPS:436047 | 21-225_193B10 | AA | DIQMTQSPSSLSASVGDRVTITCRASQGISNYLA WFQQKPGKAPKSLIYAASSLQSGVPSKFSGSGSG TDFTLTISSLQPEDFATYFCQHYLTYPLTFGGGT KVEIK<br>SEQ ID NO: 26802 | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARDRGV GYYGLDVWGQGTTVTVSS<br>SEQ ID NO: 30808 |
| | | NA | GAAATTGTGTTGACGCAGTCTCCAGGCACCCT GTCTTTGTCTCCAGGGGAAAGAGCCACCCTCT CCTGCAGGGCCAGTCCGAGTGTTAGCAGCAGC TACTTAGCCTGGTACCAGCAAAAACCTGGCCA GGCTCCCAGGCTCCTCATCTATGGTGCATCCA GCAGGGCCACTGGCATCCCAGACACAGGTTCAG AGGCAGTGGGTCTGGGACAGACTTCACTCTCA CCATCAGTAGACTGAGAGCCTGAAGATTTTGCA GTGTATTACTGTCAGCAGTATGGTAGCTCACC TCCGTGGACGTTCGGCCAAGGGACCAAGGTGG AAATCAAA<br>SEQ ID NO: 26803 | GAGGTGCAGTTGGTGGAGTCTGGGGGAGGCCTG GTCAAGCCTGGGGGGTCCCTGAGACTCTCCTGTG CAGCCTCTGGATTCACCTTCAGGGACTACAGCAT GAACTGGGTCCGCCAGGCTCCAGGGAAGGGGCT GGAGTGGGTCTCATCCATTAGTAGTGTGGTGGT TACATATACTGCGAGACTCACTGAAGGGCCGAT TCACCATCTCCAGAGACAACGCCAAAAACTCACT GTATCTGCAAATGAACAGCCTGAGAGCCGAGGA CACGGCTGTGTATTACTGTGCGAGAGCAACTATG GCCCTTGACTACTGGGGCCAGGGAACCCTGGTCA CCGTCTCCTCA<br>SEQ ID NO: 30809 |
| | | AA | EIVLTQSPGTLSLSPGERATLSCRASPSVSSSYLA WYQQKPGQAPRLVIYGASRRATGIPDRFRGSGS GTDFTLTISRLEPEDFAVYYCQQYGSSPPWTFGQ GTKVEIK<br>SEQ ID NO: 26804 | EVQLVESGGGLVKPGGSLRLSCAASGFTFRDYSMN WVRQAPGKGLEWVSSISSAGGYIYYADSLKGRFTI SRDNAKNSLYLQMNSLRAEDTAVYYCARATMALD YWGQGTLVTVSS<br>SEQ ID NO: 30810 |

FIGURE 50
(Continued)

| | | | | |
|---|---|---|---|---|
| iPS:436049 | 21-225_193B12 | NA | GAAATTGTGTTGACGCAGTCTCCAGGCACCCTGTCTTTGTCTCCAGGGGAAAGAGCCACCCTCTCCTGCAGGGCCAGTCAGTATTAGCAGCAGCTTCTTAGCCTGGTATCAGCAGAAACCTGGCCAGGCTCCCAGGCTCCTCATCTATGATGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCAGTATGGTAACTCACCGTGGGCGTTCGGCCAAGGGACCAAGGTGGAAATCAAA | CAGGTGCAGCTGCAGGAGTCGGGCCCAGGACTGGTGAAGCCTTCACAGACCCTGTCCCTCACCTGCACTGTCTCTGGTGGCTCCATCAGCAGTGCTGATTACTACTGGAACTGGATCCGCCAGTCCCAGGAAGGGCCTGGAGTGGATTGGGTACATCTTTACAGTGGGAGCACCTACTACAACCCGTCCCTCAAGAGTCGACTTACCATATCAGTGGACACGTCTAAGAACCAGTTCTCCCTGAAGCTGAGCTCTGTGACTGCCGCGGACACGGCCGTGTATTACTGTGCGAGAGGGATTACGATGGTTCGGGGAGTTATCACTTCTACTACGGTATGGACGTCTGGGGCCAAGGGACCACGGTCACCGTCTCCTCA |
| | | | SEQ ID NO: 26805 | SEQ ID NO: 30811 |
| | | AA | EIVLTQSPGTLSLSPGERATLSCRASQSIRSSFLAWYQQKPGQAPRLLIYDASSRATGIPDRFSGSGSGTDFTLTISRLEPEDFAVYYCQQYGNSPWAFGQGTKVEIK | QVQLQESGPGLVKPSQTLSLTCTVSGGSISSADYYWNWIRQLPGKGLEWIGYIFYSGSTYYNPSLKSRLTISVDTSKNQFSLKLSSVTAADTAVYYCARGDYDGSGSYHFYYGMDVWGQGTTVTVSS |
| | | | SEQ ID NO: 26806 | SEQ ID NO: 30812 |
| iPS:436051 | 21-225_193G12 | NA | GAAATAGTGATGACGCAGTCTCCAGCCACCCTGTCTGTGTCTCCAGGGGAAAGAGCCACCCTCTCCTGCAGGGCCAGTCAGAGTGTTAGCAGCAGCTTAGCCTGGTATCAGCAGAAACCTGGCCAGGCTCCCAGGATCCTCATCTCTGGTGCATCCACCAGGGCCACTGGTATCCCAGCCAGGTTCAGTGGCAGTGGGTCTGGGACAGAGTTCACTCTCACCATCAGCAGCCTGCAGTCTGAGATTTTGCAGTTTATTACTGCCAGCAGTATAATAACTGGCCGTGCAGTTTTGGCCAGGGGACCAAGCTGGAGATCAAA | CAGGTGCAGCTGGTGGAGTCTGGGGGAGGCGTGGTCCAGCCTGGGAGGTCCCTGAGACTCTCCTGTGAGCGTCTGGATTCACCTTCAGTAGCTATGCCATGCACTGGGTCCGCCAGGCTCCAGGCAAGGGCTGGAGTGGGTGGCAGTTATATGGTATGATGAACTAATAAATACTATGGAGACTCCGTGAAGGGCCGATTCACCATCTCCAGAGACAATTCCAAGAACACGCTGAATCTGCAAATGAACAGCCTGAGAGCCGAGGACACGGCTGTCTATTACTGTGCGAGAGATTTCACTATAACTGGAGCTACATATTTGACTACTGGGGCCAGGGAACCCTGGTCACCGTCTCCTCA |
| | | | SEQ ID NO: 26807 | SEQ ID NO: 30813 |

FIGURE 50
(Continued)

| | | | | |
|---|---|---|---|---|
| iPS:436054 | 21-225_194C1 | AA | EIVMTQSPATLSVSPGERATLSCRASQSVSSSLA WYQQKPGQAPRILISGASTRATGIPARFSGSGSG TEFTLTISSLQSADFAVYYCQQYNNWPCSFGQG TKLEIK<br>SEQ ID NO: 26808 | QVQLVESGGGVVQPGRSLRLSCGASGFTFSSYAMH WVRQAPGKGLEWVAVIWYDGTNKYYGDSVKGRF TISRDNSKNTLNLQMNSLRAEDTAVYYCARDFTIT GATYFDYWGQGTLVTVSS<br>SEQ ID NO: 30814 |
| | | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGAACAGATTTCACTCTCACCATC AGCAGCCTGCAGCCTGAAGATTTTGCAACTTA TTACTGCCTACACATTATTACTTACCCTCTCAC TTTCGGCGGAGGGACCAAGGTGGAGATCAAA<br>SEQ ID NO: 26809 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATGAACACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGATAGGGG GGTGGGTTACTACGGTTTGGACGTCTGGGGCCAA GGGACCACGGTCACCGTCTCCTCA<br>SEQ ID NO: 30815 |
| | | AA | DIQMTQSPSSLSASVGDRVTITCRASQGISNYLA WFQQKPGKAPKSLIYAASSLQSGVPSKFSGSGSG TDFTLTISSLQPEDFATYYCLHYLTYPLTFGGGT KVEIK<br>SEQ ID NO: 26810 | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARNRGV GYYGLDVWGQGTTVTVSS<br>SEQ ID NO: 30816 |

FIGURE 50
(Continued)

| | | | |
|---|---|---|---|
| iPS:436056 | 21-225_194C3 | NA | GAAATTGTGCTGACTCAGTCTCCAGACTTCA GTCTGTGGCTCCAAAGGAGAAAGTCACCATCA CCTGCCGGGCCAGTCAGAGTATTGGTAGTAAC CTTACACTGGTACCAGCAGAAACCTGAGTCAGTC TTCCAAAGCTCCTCATCAAGTCTGTCTTCCCAGTC CTTCTCAGGGGTCCCCTCGAGGTTCAGTGGCA GTGGATCTGGGACAGATTTCACCCTCACCATC AATAGCCTGGAAACTGAAGATGTAGTTTACCGTGA TTACTGTCAGCAGAGTAGTAGTTTACCCGTGGA CGTTCGGCCAAGGGACCAAGGTGGAAATCAA A | CAGGTGCAGCTGCAGGAGTCGGGCCCAGGACTG GTGAAGCCTTCGGAGACCCTGTCCCTCACCTGCA CTGTCTCTGGTGGCTCCATCAATTACTACTG GAGCTGGATCCGGCAGCCCGCCGGGAAGGGACT GGAGTGGATTGGGCGTATCTATGCCAGTGGGAGC ACCAACTACAACCCCTCCCTCAAGAGTCGAGTCA CCATGTCAATAGACACGTCCAAGAACCAGTTCTC CCTGAAGCTGAGCTCTGTGACCGCCGCGGACACG GCCGTGCATTACTGTGCGAGAGATCGGGGGATACT ATGGCTACTACGGTATGGACGTCTGGGGCCAAG GGACCACGGTCACCATCTCCTCA |
| | | | SEQ ID NO: 26811 | SEQ ID NO: 30817 |
| | | AA | EIVLTQSPDFQSVAPKEKVTITCRASQSIGSNLHW YQQKPDQSPKLLIKSASQSFSGVPSRFSGSGSGT DFTLTINSLETEDAATYYCQQSSSLPWTFGQGTK VEIK | QVQLQESGPGLVKPSETLSLTCTVSGGSINNYYWS WIRQPAGKGLEWIGRIYASGSTNYNPSLKSRVTMSI DTSKNQFSLKLSSVTAADTAVHYCARDRGYYGYY GMDVWGQGTTVTISS |
| | | | SEQ ID NO: 26812 | SEQ ID NO: 30818 |
| iPS:436058 | 21-225_194A4 | NA | GAAATTGTGTTGACGCAGTCTCCAGGCACCCT GTCTTTGTCTCCAGGGGAAAGAGCCACCCTCT CCTGCAGGGCCAGTCGGGGTGTTAGCAACATC TACTTAGCCTGGTACCAACAGAAACCTGGCCA GGCTCCCAGGCTCCTCATCTATGGTGCTTCCA ACAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCACAATGATTACTCAATG TTCACTTTCGGCCCTGGGACCAAAGTGGATAT CAAA | CAGGTGCAGTTGGTGCAATCTGGGACTGAGGTGA AGAAGCCTGGGGCCTCTTTGAAGGTCTCCTGCAA GGCTTCTGGATACACCTTCACCGTCTACTATTTG AACTGGGTGCGACAGGCCCCTGGACAAGGGCTT GAGTGGATGGGATGGATCAACCCTAACACAGTGGT GGCACAAACTATGCACCAGGACACGTCCATCAGCACA GTCACCATGACCAGGGAACACGTGAGGCTGAGATCTGAC GCCTACATGGAACTGAGCAGCCTGAGATCTGAC GACACGGCCGTGTATTACTGTGCGAGAGGCTACG ATATTTTGACTGGTTGGGGCCAGGGAACCCTGGT CACCGTCTCCTCA |
| | | | SEQ ID NO: 26813 | SEQ ID NO: 30819 |

FIGURE 50
(Continued)

| | | | | |
|---|---|---|---|---|
| | | AA | EIVLTQSPGTLSLSPGERATLSCRASRGVSNIYLAWYQQKPGQAPRLLIYGASNRATGIPDRFSGSGSGTDFTLTISRLEPEDFAVYYCQHNDYSMFTFGPGTKVDIK | QVQLVQSGTEVKKPGASLKVSCKASGYTFTVYLNWVRQAPGQGLEWMGWINPNSGGTNYAQKFQGRVTMTRDTSISTAYMELSRLRSDDTAVYYCARGYDILTGWGQGTLVTVSS |
| | | | SEQ ID NO: 26814 | SEQ ID NO: 30820 |
| iPS:436060 | 21-225_194F4 | NA | GATATTGTGATGACCCAGACTCCACTCTCTCTGTCCGTCACCCCTGGACAGCCGGCCTCCATCTCCTGCAAGTCTAGTCAGAGCCTCCTCCATAGTGATGAAGGAACCTATTTGTATTGGTACCTGCAGAAGCCAGGCCAGTCTCCACAGCTCCTGATCTGTGAGGTTTCCAACCGGTTCTCTGGAGTGCCAGATAGGTTCAGTGGCAGCGGGTCAGGGACAGATTTCACACTGAAAATCAGCCGGGTGGAGGCTGGGGATGTTGGGGTTTATTACTGCATGCAAAGTATACAGCTTCCCTGGACGTTCGGCCAAGGGACCAAGGTGGAAATCAAA | CAGCTGCAGCTGCAGGAGTCGGGCCCAGGACTGGTGAAGCCTTCGGAGACCCTGTCCCTCACCTGCACTGTCTCTGGTGGCTCCATCAGTAGTTACCACTGGAGCTGGATCCGGCAGCCCGCGGAAGGGACTGGAGTGGATTGGACTTATCTATACCAGTAGGAGCACCAACTACAACCCCTCCCTCAAGAGTCGAGTCACCATGTCAGTAGACACGGTCCAAGACCAGTTCTCCCTGAAGCTGAGCTCTGTGACCGCCGCGGACACGGCCGTGTATTACTGTGCGAGAGACTCCGGTATAACTGGAACTTCCCTACTTTGACTACTGGGGCCAGGGAACCCTGGTCACCGTCTCCTCA |
| | | | SEQ ID NO: 26815 | SEQ ID NO: 30821 |
| | | AA | DIVMTQTPLSLSVTPGQPASISCKSSQSLLHSDGRTYLYWYLQKPGQPPQLLICEVSNRFSGVPDRFSGSGSGTDFTLKISRVEAGDVGVYYCMQSIQLPWTFGQGTKVEIK | QLQLQESGPGLVKPSETLSLTCTVSGGSISSYHWSWIRQPAGKGLEWIGLIYTSRSTNYNPSLKSRVTMSVDRSKSQFSLKLSSVTAADTAVYYCARLRYNWNFPYFDYWGQGTLVTVSS |
| | | | SEQ ID NO: 26816 | SEQ ID NO: 30822 |

FIGURE 50
(Continued)

| | | | |
|---|---|---|---|
| iPS:436062 | 21-225_194E5 | NA | GAAATTGTGTTGACGCAGTCTCCAGGCACCCT GTCTTTGTCTCTCCAGGGGAAAGCGCCACCCTCT CCTGCAGGGCCGGTCAAAGTATTAGAACCAAC TTCTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAACAGACTGGAGCCTAAAGATTTTGCAG TGTATTACTGTCAGCAGTATGGTAGTTCACCG TGGACGTTCGGCCAAGGGACCAAGGTGGAAA TCAAA<br>SEQ ID NO: 26817 | CAGGTGCAACTGCAGGAGTCGGGCCCAGGACTG GTGAAGCCTTCACAGACCCTGTCCTCACCTGCA CTGTCTCTGGTGCTCCATCAACAGTGGTGATTA CTACTGGAACTGGATCCGCCACCACCCAGGGAA GGGCCTGGAGTGGATTGGGTACATCTTTTACAGT GGGAGCACTTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTATATTACTGTGCGAGAGGGGATT ACGATGGTTCGGGGAGTTATCACTACTATTACGG TATGGACGTCTGGGGCCAAGGGACCACGGTCAC CGTCTCCTCA<br>SEQ ID NO: 30823 |
| | | AA | EIVLTQSPGTLSLSPGESATLSCRAGQSIRTNFLA WYQQKPGQAPRLLIYGASSRATGIPDRFSGSGSG TDFTLTINRLEPKDFAVYYCQQYGSSPWTFGQG TKVEIK<br>SEQ ID NO: 26818 | QVQLQESGPGLVKPSQTLSLTCTVSGGSINSGDYY WNWIRHHPGKGLEWIGYIFYSGSTYYNPSLKSRVTI SVDTSKNQFSLKLSSVTAADTAVYYCARGDYDGS GSYHYYGMDVWGQGTTVTVSS<br>SEQ ID NO: 30824 |
| iPS:436064 | 21-225_194E6 | NA | GAAATTGTGTTGACGCAGTCTCCAGGCACCCT GTCTTTGTCTCTCCAGGGGAAAGAGCCACCCTCT CCTGCAGGGCCAGTCAGAGTATTAGAAGCAAC TTCTTAGCCTGGTATCAGCAGAAACCTGGCCA GGCTCCCAGGCTCCTCATCTATGGTGCATCCA GCAGGGCCACTGGCATCCCAGACAGGTTCAGT GGCAGTGTGTCTGGGACAGACTTCACTCTCAC CATCAACAGACTGGAGCCTGAAGATTTTGCAG TGTATTACTGTCAGCAGTATGGTAGTCACCG TGGACGTTCGGCCAAGGGACCAAGGTGGAAA TCAAA<br>SEQ ID NO: 26819 | CAGGTGCAGCTGCAGGAGTCGGGCCCAGGACTG GTGAAGCCTTCACAGACCCTGTCCTCACCTGCA CTGTCTCTGGTGACTCCATCAACAGTGGTGATTA CTACTGGAACTGGATCCGCCAGCACCCAGGGAA GGGCCTGGAGTGGATTGGATTCATCTTTACAGT GGGAGCACTACTACAACCGTCCCTCAAGAGTC GAGTTACCATATCAATAGACACGTCTAAGAACCA GTTCTCCCTGAAGCTGAGCTCTGTGAATGTCGCG GACACGGCCGTGTATTACTGTGCGAGAGGGGATT ACGATGGTTCGGGGAGTTATCACTACTATTACGG TATGGACGTCTGGGGCCAAGGGACCACGGTCAC CGTCTCCTCA<br>SEQ ID NO: 30825 |

FIGURE 50
(Continued)

| | | | |
|---|---|---|---|
| iPS:436066 | 21-225_194B7 | AA | EIVLTQSPGTLSLSPGERATLSCRASQSIRSNFLA WYQQKPGQAPRLLIYGASSRATGIPDRFSGSVSG TDFTLTINRLEPEDFAVYYCQQYGSSPWTFGQGT KVEIK<br>SEQ ID NO: 26820 |
| | | | QVQLQESGPGLVKPSQTLSLTCTVSGDSINSGDYY WNWIRQHPGKGLEWIGFIFYSGSTYNPSLKSRVTI SIDTSKNQFSLKLSSVNVADTAVYYCARGDYDGSG SYHYYGMDVWGQGTTVTVSS<br>SEQ ID NO: 30826 |
| | | NA | GACATCCAGATGACCCAGTCTCCATCCTCACT GTCTGCATCTGTAGGAGACAGAGTCACCATCA CTTGTCGGGCGAGTCAGGGACATTAGCAGATAT TTAGCCTGGTTTCAGCAGAAACCAGGGAAAGC CCCTAAGTCCCTGATCTATGGTGCATCCAGGT TGCAAAGTGGGGTCCCATCAAAGTTCAGCGGC AGTGGATCTGGGACAGATTTCACTCTCACCAT CAGCAGCCTGCAGCCTGAAGATTTTGCAACTT ATTACTGCCAACATTATCTTAATTACCCTCTCA CCTTCGGCCAAGGGACACGACTGGAGATTAAA<br>SEQ ID NO: 26821 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGGTATGATGGAAGT AATAAAAACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTATTGTGCGAGAGATCGGTC TAAGGGTTACGACGGTATGGACGTCTGGGGCCA AGGGACCACGGTCACCGTCTCCTCA<br>SEQ ID NO: 30827 |
| | | AA | DIQMTQSPSSLSASVGDRVTITCRASQGISKYLA WFQQKPGKAPKSLIYGASRLQSGVPSKFSGSGSG TDFTLTISSLQPEDFATYYCQHYLNYPLTFGQGT RLEIK<br>SEQ ID NO: 26822 |
| | | | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDRSKG YDGMDVWGQGTTVTVSS<br>SEQ ID NO: 30828 |

FIGURE 50
(Continued)

| | | | |
|---|---|---|---|
| iPS:436068 | 21-225_194F7 | NA | GACATCCAGATGACCCAGTCTCCATCTTCCGT GTCTGCATCTGTAGGAGACAGAGTCACCATCA CTTGTCGGGCGAGTCAGGTATTAGCAGGTGG TTAGCCTGGTTTCAGCAGAAACCAGGGAAAGC CCCTAAGATCCTGATCTATGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTTGCAACTTA CTATTGTCAACAGGCTAACAGTTTCCCGTGA CGTTCGGCCAAGGGACCAAGGTGGAAATCAA A<br><br>SEQ ID NO: 26823 | CAGGTGCAGCTGGTGGTGCAGTCTGGGGCTGAGGTG AAGAAGCCTGGGGCCTCAGTGAAGGTCTCCTGC AAGGCTTCTGGATACACCTTCACCGACTACTACA TACACTGGGTGCGACAGGCCCCTGGACAAGGGC TTGAGTGGATGGGATGGATCAACCCTAACAATGG TGGCACAAACTATGCACAGAAATTTCAGGGCAG GGTCACCATGACCAGGGACACGTCCATCAGCAC AGCCTACATGGAGCTGAGCAGGCTGAGATCTGA CGACACGGCCGTGTATTACTGTGCGAGAGAACCC CTTGGTTACTATGGTTCGGGGAGTTATGGGCCT ACGGTATGGACGTCTGGGGCCAAGGGACCACGG TCACCGTCTCCTCA<br><br>SEQ ID NO: 30829 |
| | | AA | DIQMTQSPSSVSASVGDRVTITCRASQGISRWLA WFQQKPGKAPKILIYAASSLQSGVPSRFSGSGSG TDFTLTISSLQPEDFATYYCQQANSFPWTFGQGT KVEIK<br><br>SEQ ID NO: 26824 | QVQLVQSGAEVKKPGASVKVSCKASGYTFTDYYIH WVRQAPGQGLEWMGWINPNNGGTNYAQKFQGRV TMTRDTSISTAYMELSRLRSDDTAVYYCAREPLGY YGSGSYGAYGMDVWGQGTTVTVSS<br><br>SEQ ID NO: 30830 |
| iPS:436072 | 21-225_194C10 | NA | GAAATTGTGTTGACGCAGTCTCCAGGCACCCT GTCTTTGTCTCCAGGGGAAAGAGCCACCCTCT CCTGCAGGGCCAGTCCGAGTGTTAACAGCGGC TACTTAGCCTGGTACCAGCAGAAGCCTGGCCA GACTCCCAGGCTCCTCATCTTTGGTGCATCCA GCAGGGCCACTGGCATCCCCGACAGGTTCAGT GCCAGTGGGTCTGGGGCAGACTTCACTCTCAC CATCAGTAGACTGGAGCCTGAAGATTTTGCAG TGTATTTCTGTCAGCAGTATGAAAGCTCACCG TGGACGTTCGGCCAAGGGACCAAGGTGGAAA TCAAA<br><br>SEQ ID NO: 26825 | CAGGTGCAGCTACAGCAGTGGGGCGCAGGACTG TTGAAGCCTTCGGAGACCCTGTCCCTCACCTGCG CTGTCTCTGGTGGGTCCTTCAGTATTACTACTGG AGCTGGATCCGCCAGCCCCCGGGAAGGGGCTG GAGTGGATTGGGGAAATCAATCATAGTGGAAGC ACCAACTACAACCCGTCCCTCAAGAGTCGAGTCA CCATATCAATAGACACGTCCAAGAACCAGTTCTC CCTGAAGCTGAGTTCTGTGACCGCCGGACACG GGCTGTGTATTACTGTGCGAGAGACTACGGTGCT TTTGATATCTGGGGCCAAGGGACAATGGTCACCG TCTCTTCA<br><br>SEQ ID NO: 30831 |

FIGURE 50
(Continued)

| | | | | |
|---|---|---|---|---|
| | | AA | EIVLTQSPGTLSLSPGERATLSCRASPSVNSGYLA WYQQKPGQTPRLLIFGASSRATGIPDRFSASGSG ADFTLTISRLEPEDFAVYFCQQYESSPWTFGQGT KVEIK<br>SEQ ID NO: 26826 | QVQLQQWGAGLLKPSETLSLTCAVSGGSFRYYYW SWIRQPPGKGLEWFGEINHSGSTNYNPSLKSRVTISI DTSKNQFSLKLRSVTAADTAVYYCARDYGAFDIW GQGTMVTVSS<br>SEQ ID NO: 30832 |
| iPS:436074 | 21-225_194F10 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCTGAAACCAGGAAAGC CCCTAAGCGCCTGATCTATGCTGCATCCAGTTT ACAAAGTGGGGTCCCATCAAGGTTCAGCGGCA GTGGATCTGGGCCAGAATTCACTCTCACAATC AGCAGCCTGCAGCCTGAAGATTTTGCAACTTA TTACTGTCTACAGCATTATAGTTTCCCATTCAC TTTCGGCCCTGGGACCAAAGTGGATATCAAA<br>SEQ ID NO: 26827 | CAGGTGCAGCTGGTGGAGTCGGGGGGAGGCGTG GTCCAGCCTGGGAGGTCCCTGAGACTCTCCTGTG CAGCGTCTGGATTCACCTTCAGTAGCTTTATCAT GCACTGGGTCCGCCAGGCTCCAGGCAGGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGGAAATGAACAGCCTGAGAGTCGAGG ACACGGCTGTGTATTACTGTGCGAGAGAGGAGTA TAGCAGTGGCTGGTTCGGGTACGGTATGGACGTC TGGGGGCCAAGGGACCACGGTCACCGTCTCCTCA<br>SEQ ID NO: 30833 |
| | | AA | DIQMTQSPSSLSASVGDRVTITCRASQGIRNDLG WYQLKPGKAPKRLIYAASSLQSGVPSRFSGSGSG PEFTLTISSLQPEDFATYCLQHYSFPFTFGPGTK VDIK<br>SEQ ID NO: 26828 | QVQLVESGGGVVQPGRSLRLSCAASGFTFSSFIMH WVRQAPGRGLEWVAVIWYDGSNKYYADSVKGRF TISRDNSKNTLYLEMNSLRVEDTAVYYCAREEYSS GWFGYGMDVWGQGTTVTVSS<br>SEQ ID NO: 30834 |

FIGURE 50
(Continued)

| | | | |
|---|---|---|---|
| iPS:436076 | 21-225_194H11 | NA | GACATCCAGATGACCCAGTCTCCATCCTCACTGTCTGCATCTGTAGGAGACAGAGTCACCATCACTTGTGTCGGCGAGTCAGGGCATTAGCAATTATTTAGCCTGGTTTCAGCAGAAACCAGGGAAAGCCCCTAAGTCCCTGATCTATGCTGCATCCAGTTTACAAAGTGGGGTCCCATCAAAGTTCAGCGGCAGTGGATCTGGAACAGATTTCACTCTCACCATCAGCAGCCTGCAGCCTGAAGATTTTGCAACTTATTACTGCCAACATTATCTTACTTACCCTCTCACTTTCGGCGGAGGGACCAAGGTGGAGATCAAA SEQ ID NO: 26829 | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGCTGGAGTGGGTGGCAGTTATATGGTATGATGGAAGTAATGAACACTATGCAGACTCCGTGAAGGGCCGATTCACCATCTCCAGAGACAATTCCAAGAACACGCTGTCTCTGCAAATGAACAGCCTGAGAGCCGAGGACACGGCTGTGTATTACTGTGCGAGAGATAGGGGGGGTGGGTTATTACGGTTTGGACGTCTGGGGCCAAGGGACCACGGTCACCGTCTCCTCA SEQ ID NO: 30835 |
| | | AA | DIQMTQSPSSLSASVGDRVTITCRASQGISNYLAWFQQKPGKAPKSLIYAASSLQSGVPSKFSGSGSGTDFTLTISSLQPEDFATYYCQHYLTYPLTFGGGTKVEIK SEQ ID NO: 26830 | QVQLVESGGGVVQPGRSLRLSCAASGFTFSSYGMHWVRQAPGKGLEWVAVIWYDGSNEHYADSVKGRFTISRDNSKNTLSLQMNSLRAEDTAVYYCARDRGVGYYGLDVWGQGTTVTVSS SEQ ID NO: 30836 |
| iPS:436078 | 21-225_194H12 | NA | GACATCCAGATGACCCAGTCTCCATCCTCACTGTCTGCATCTGTGGGAGACAGAGTCACCATCACTCGTCGGGCGAGTCAGGGCATTGGCAAGTATTTAGCATGGTTTCAGCAGAAACCAGGGAAAGCCCTTAAGTCACTGATTTACTGATATGCTGCATCCAGTTTGCAAAGTGGGGTCCCATCAAAATTCAGCGGCAGTGGATCTGGGACAGATTTCACTCTCACCATTAGCAGCCTGCAACGATATGACTTACCATTCACTTTCGGCCCTGGGACCAAAGTGGATATCAAA SEQ ID NO: 26831 | CAGGTGCAGCTGGTGGAGTCTGGGGGAGGCGTGGTCCAGCCTGGGAGGTCCCTGAGACTCTCCTGTCAGCGTCTGGATTCACCTTCAGGAACTATGGCATGCACTGGGTCCGCCAGGCTCCAGGCAAGGGCTGGAGTGGGTGGCAGTTATATGGTTTGATGGAAGTAATGACTACTATGCAGACTCCGTGAAGGGCCGATTCACCATCTCCAGAGACAATTCCAAGAACACGCTGTCACTGCAAATGAACAGCCTGAGAGCCGAGGACACGGCTGTGTACGACGGTTTAGATGTCTGGGGCCAAGGTGGCTACGACGGTTTAGATGTCTGGGGCCAAGGGACCACGGTCACCGTCTCCTCA SEQ ID NO: 30837 |

FIGURE 50
(Continued)

| | | | |
|---|---|---|---|
| iPS:436080 | 21-225_195B1 | AA | DIQMTQSPSSLSASVGDRVTITRRASQGIGKYLA WFQQKPGKALKSLIYAASSLQSGVPSKFSGSGSG TDFTLTISSLQPDDFATYYCQRYDTYPFTFGPGT KVDIK<br>SEQ ID NO: 26832 | QVQLVESGGGVVQPGRSLRLSCAASGFTFRNYGM HWVRQAPGKGLEWVAVIWFDGSNDYADSVKGR FTISRDNSKNTLSLQMNSLRAEDTAVYYCARDRSV GYDGLDVWGQGTTVTVSS<br>SEQ ID NO: 30838 |
| | | NA | GAAATTGTGTTGACGCAGTCTCCAGGCACCCT GTCTTTGTCTTCAGGGGAAAGAGCCACCCTCT CCTGCAGGGCCAGTCCGAGTGTTAACAGTAAC TACTTAGCCTGGTATCAGCAGAAACCTGGCCA GACTCCCAGGCTCCTCATCTATGGTGCATCCA ACAGGGCCACTGGCGTCCCAGACAGGTTCAGT GCCAGTGGGTCTGGGACAGATTCACTCTCAC CATCAGAAGACTGGAGCCTGAAGATTTTGCAG TGTATTTCTGTCAGCAGTATGAAAGCTCACCG TGGACGTTCGGCCAAGGGACCAAGGTGGAAA TCAAA<br>SEQ ID NO: 26833 | CAGGTGCAGTTACAGCAGTGGGGCGCAGGACTG TTGAAGCCTTCGGAGACCCTGTCCCTCACCTGCG CTGTCTCTGGTGGGTCCTTCAGATATTACTTCTGG AGCTGGATCCGCCAGTCCCCGGAAGGGGCTG GAGTGGTTTGGGGAAATCAATCATAGTGGACGC ACCAACTACAACCCGTCCCTCAAGAGTCGAGTCA CCATATCAGTAGACACGTCCAAGAACCAGTTCTC CCTGAAGCTGAGGTCTGTGACCGCCGCGGACAC GGCTGTGTATTACTGTGCGAGAGACTACGGTGCT TTTGATATCTGGGGCCAAGGCACATTGGTCACCG TCTCTTCA<br>SEQ ID NO: 30839 |
| | | AA | EIVLTQSPGTLSLSSGERATLSCRASPSVNSNYLA WYQQKPGQTPRLLIYGASNRATGVPDRFSASGS GTDFTLTIRRLEPEDFAVYFCQQYESSPWTFGQG TKVEIK<br>SEQ ID NO: 26834 | QVQLQQWGAGLLKPSETLSLTCAVSGGSFRYYFW SWIRQSPGKGLEWFGEINHSGRTNYNPSLKSRVTIS VDTSKNQFSLKLRSVTAADTAVYYCARDYGAFDI WGQGTLVTVSS<br>SEQ ID NO: 30840 |

FIGURE 50
(Continued)

| | | | | |
|---|---|---|---|---|
| iPS:436082 | 21-225_195D9 | NA | GACATCCAGATGACCCAGTCTCCATCTTCCGT GTCTGCATCTGTAGGAGACAGAGTCACCATCA CTTGTGCGGGCGAGTCAGGGTATTAGCAGGTGG TTAGCCTGGTATCAGCAGAAACCAGGGAAAG CCCCTAAGCTCCTGATCTATGCTGCATCCAGT TGCTAGGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACGGGCTAACAGTTTCCCGTGC AGTTTTGGCCAGGGGACCAAGCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTCACTCACTATGTCAT GCACTGGGTCCGCCAGGCTCCAGGCAAGGGGCT GGAGTGGGTGGCAGTTATTTGGTATGATGAACT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATTGGTT CGGGGAGGGGAACTACTACGGTATGGACGTCTG GGGCCAAGGGACCACGGTCACCGTCTCCTCA |
| | | | SEQ ID NO: 26835 | SEQ ID NO: 30841 |
| | | AA | DIQMTQSPSSLSASVGDRVTITCRASQGISRWLA WYQQKPGKAPKLLIYAASSLLGGVPSRFSGSGS GTDFTLTISSLQPEDFATYYCQRANSFPCSFGQG TKLEIK | QVQLVESGGGVVQPGRSLRLSCAASGFTFSHYVM HWVRQAPGKGLEWVAVIWYDGTNKYYADSVKGR FTISRDNSKNTLYLQMNSLRAEDTAVYYCARDWF GEGNYYGMDVWGQGTTVTVSS |
| | | | SEQ ID NO: 26836 | SEQ ID NO: 30842 |
| iPS:436084 | 21-225_195F2 | NA | GAAATTGTGCTGACTCAGTCTCCAGACTTTCA GTCTGTGACTCCAAAGGAGAAAGTCACCATCA CCTGCCGGGCCAGTCAGAGCATTGGTAGTAGC CTGCACTGGTACCAGCAGAAACCAGATCAGTC TTACACTGGTACCAGCAGAAACCAGATCAGTC TCCAAAGCTCCTCATCAAGTATGCTTCCCAGT CCTTCTCAGGGGTCCCCTCGAGGTTCAGTGGC AGTGGATCTGGGACAGATTTCGCCCTCACCAT CAGTAGCCTGGAAGCTGAAGATGCTGCAACGT ATTACTGTCATCAGAGTAGAGTAGCGCAACTT ACTTTCGGCGGAGGGACCAAGGTGGAGATCA AA | CAGGTGCAGCTGCAGGAGTCGGGCCCAGGACTG GTGAAGCCTTCACAGACCCTGTCCTCACCTGCA CTGTCTCTGGTGACTCCATCAGCAGCGGTGGTTA CTACTGGAGCTGGATCCGCCAGCACCCAGGGAA GGGAGCACCAACTATATAACCGTCCCTCAAGAGTC GAGTTACCATATCAGTAGACATGTCTAAGAACCA GTTCTCCCTGAAGCTGAGCTCTGTGACTGACGCG GACACGGCCGTGTATTATTGTGCGAGAGGGGGGT ATAACTGGAACAACGGGTTTGACTACTGGGGCC AGGGAGCCCTGGTCACCGTCTCCTCA |
| | | | SEQ ID NO: 26837 | SEQ ID NO: 30843 |

FIGURE 50
(Continued)

| | | | |
|---|---|---|---|
| | | AA | EIVLTQSPDFQSVTPKEKVTITCRASQSIGSSLHW YQQKPDQSPKLLIKYASQSFSGVPSRFSGSGSGT DFALTISSLEAEDAATYYCHQSRTLPLTFGGGTK VEIK<br><br>SEQ ID NO: 26838 | QVQLQESGPGLVKPSQTLSLTCTVSGDSISSGGYYW SWIRQHPGKGLEWIGYSYYSGSTNYNPSLKSRVTIS VDMSKNQFSLKLSSVTDADTAVYYCARGGYNWN NGFDYWGQGALVTVSS<br><br>SEQ ID NO: 30844 |
| iPS:436086 | 21-225_191G10 | NA | GACATCCAGATGACCCAGTCTCCTTCCTCACT GTCTGCATCTGTAGGAGACAGAGTCACCATCA CTTGTCGAGCAGTCAGGGCATTGGCAAGTAT TTAGCCTGGTTTCAGCAGAAACCAGGGAAAGC CCCTAAGTCCCTGCTCTATAAAGTATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACACAGTATGACTTACCCGCTCA CTTTCGGCGGAGGGACCAAGGTGGAGATCAA A<br><br>SEQ ID NO: 26839 | CAGGTGCAGCTGGTGGAGTCTGGGGGAGGCGTG GTCCAGCCTGGGAGGTCCCTGAGACTCTCCTGTG CAGCGTCTGAGATTCACCTTCAGTAGCTATGGCAT GCACTGGGTCCGCCAGGCTCCAGGCAAGGGGCT GGAGTGGGTGGCAGTTATATGGTATGATGGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGG CGTGGGCTACGACGGTTTGGACGTCTGGGGCCAA GGGACCACGGTCACCGTCTCCTCA<br><br>SEQ ID NO: 30845 |
| | | AA | DIQMTQSPSSLSASVGDRVTITCRTSQGIGKYLA WFQQKPGKAPKSLLYKVSSLQSGVPSKFSGSGS GTDFTLTISSLQPEDFATYYCQQYMTYPLTFGGG TKVEIK<br><br>SEQ ID NO: 26840 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS<br><br>SEQ ID NO: 30846 |

FIGURE 50
(Continued)

| | | | | |
|---|---|---|---|---|
| iPS:436088 | 21-225_195C8 | NA | GAAATTGTGTTGACGCAGTCTCCAGGCACCCTGTCTTTGTCTCCAGGGGAAAGAGCCACCCTCTCCTGCAGGGCCAGTCAGTATTGCAGCAGCTTCTTAGCCTGGTACCAACAGAAACCTGGCCAGGCTCCCAGGCTCCTCATCTATGGTGCATTAGTAGGGCCACTGGCATCCCAGACAGCAGGTCAGTGGCAGTGGGTCTGGGACAGACTTCACTCTCACCATCAGCAGACTGGAGCCTGAAGATTTTGCAGTGTATTACTGTCAGCAGTATGGTAACTCACCGTGGGCGTTCGGCGGAGGGACCAAGGTGGAAATCAAA | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGATTACTACTGGAACTGGATCCGCCAGTCCCAGGAAGGGCCTGGAGTGGATTGGGTACATCTTTACAGTGGGAGCACCTACTACAACCCGTCCCTCAAGAGTCGACTTACCATATCAGTGGACACGTCTAAGAACCAGTTCTCCCTGAAGCTGAGCTCTGTGACTGCCGCGGACACGGCCGTGTATTACTGTGCGAGAGGGGATTACGATGGTTCGGGGAGTTATCACTTCTACTACGGTATGGACGTCTGGGGCCAAGGGACCACGGTCACCGTCTCCTCA |
| | | AA | EIVLTQSPGTLSLSPGERATLSCRASQSIRSSFLAWYQQKPGQAPRLLIYGAFSRATGIPDRFSGSGSGTDFTLTISRLEPEDFAVYYCQQYGNSPWAFGQGTKVEIK | QVQLQESGPGLVKPSQTLSLTCTVSGGSISSGDYYWNWIRQLPGKGLEWIGYIFYSGSTYYNPSLKSRLTISVDTSKNQFSLKLSSVTAADTAVYYCARGDYDGSGSYHFYYGMDVWGQGTTVTVSS |
| | | | SEQ ID NO: 26841 | SEQ ID NO: 30847 |
| | | | SEQ ID NO: 26842 | SEQ ID NO: 30848 |
| iPS:436090 | 21-225_195A9 | NA | GACATCCAGATGACCCAGTCTCCATCCTCACTGTCTGCATCTGTAGGAGACAGAGTCACCATCACTTGTGCGGGCGAGTCAGGGCATTAGCAATTATTTAGCCTGGTTTCAGCAGAAACCAGGGAAAGCCCCTAAGTCCCTGATCTATGCTGCATCCAGTTTGCAAAGTGGGGTCCCATCAAGGTTCAGCGGCAGTGGATCTGGGAACAGATTCACTCTCACCATCAGCAGCCTGCAACATTATCTTACCTCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGCAGTGGGTGGCAGTTATATGGTATGATGGAAGTAATGAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATAGGGGGGGGTTACTACGGTTTGACGTCTGGGGCCAAGGGACCACGGTCACCGTCTCCTCA |
| | | | SEQ ID NO: 26843 | SEQ ID NO: 30849 |

FIGURE 50
(Continued)

| | | | |
|---|---|---|---|
| | | AA | DIQMTQSPSSLSASVGDRVTITCRASQGISNYLAWFQQKPGKAPKSLIYAASSLQSGVPSKFSGSGSGTDFTLTISSLQPEDFATYYCQHYLTYPLTFGGGTKVEIK<br>SEQ ID NO: 26844 | QVQLVESGGGVVQPGRSLRLSCAASGFTFSSYGMHWVRQAPGKGLQWVAVIWYDGSNEHYADSVKGRFTISRDNSKNTLYLQMNSLRAEDTAVYYCARDRGVGYYGLDVWGQGTTVTVSS<br>SEQ ID NO: 30850 |
| iPS:436092 | 21-225_195B9 | NA | GACATCCAGATGACCCAGTCTCCATCCTCCCTGTCTGCATCTGTAGGAGACAGAGTCACCATCACTTGCCGGGCAAGTCAGGGCATAAGAACCAGGGAAATTTAGGCTGGTATCAGCAGAAACCAGGGAAAGCCCCTAAGCGCCTGATCTATGCTGCATCCGATTTGCAAAGTGGGGTCCCATCAAGGTTCAGCGGCAGTGGATCTGGGACAGATTTCACTCTCACAATCAGCAGCCTGCAGCCTGAAGATTTTGCAACTTATTGCTGTCTACAGCATTATCGTTACCCATTCACTTTCGGCCCTGGGACCAAAGTGGATTTCAAA<br>SEQ ID NO: 26845 | CAGGTGCAACTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGTGATGGAAGTAATAAATACTATGCAGACTCCGTGAAGGGCCGATTCACCATCTCCAGAGACAACAATTCCAAGAACACGCTGTATCTGCAAATGAACAGCCTGAGAGCCGAGGACACGGCTGTGTATTACTGTGCGAGAGAATGGCTACAATTCAGGTACTACTACGGTATGGACGTCTGGGGCCAAGGGACCACGGTCACCGTCTCCTCA<br>SEQ ID NO: 30851 |
| | | AA | DIQMTQSPSSLSASVGDRVTITCRASQGIRKDLGWYQQKPGKAPKRLIYAASDLQSGVPSRFSGSGSGTEFTLTISSLQPEDFATYCCLQHYRYPFTFGPGTKVDFK<br>SEQ ID NO: 26846 | QVQLVESGGGVVQPGRSLRLSCAASGFTFSSYGMHWVRQAPGKGLEWVAVIWYDGSNKYADSVKGRFTISRDNSKNTLYLQMNSLRAEDTAVYYCAREWLQFRYYYGMDVWGQGTTVTVSS<br>SEQ ID NO: 30852 |

FIGURE 50
(Continued)

| | | | | |
|---|---|---|---|---|
| iPS:436094 | 21-225_195B10 | NA | GAAATTGTGCTGACTCAGTCTCCAGACTTTCAGTCTGTGACTCCAAAGGAGAAAGTCACCATCACCTGCCGGGCCAGTCAGAGCAGTATTGGTAGTAGCTTACACTGGTACCAGCAGAAACCAGATCAGTCTCCAAAGCTCCTCATCAAGTATGCTTCCCAGTCCTTCTCAGGGGTCCCCTCGAGGTTCAGTGGCAGTGGATCTGGGACAGATTTCACCCTCACCATCAATAGCCTGGAAGCTGAAGATGCTGCAACGTATTACTGTCATCAGAGTGTCGTTTACCGCTCACTTTCGGCGGAGGGACCAAGGTGGAGATCAAA SEQ ID NO: 26847 | CAGGTGCAGCTGCAGGAGTCGGGCCCAGGACTGGTGAAGCCTTCACAGACCCTGTCCCTCACCTGCACTGTCTCTGGTGGCTCCATCAGCAGTAGTGGTTACTACTGGAGCTGGATCCGCCAGCACCCAGGGAAGGGCCTGGAATGGATTGGGTACATGTATTACAGTGGGAGCACTACTACAACCGTCCCTCAAGAGTCGGGTTTACCATATCTGTAGACACGTCTAAGAACCAGTTTTATCTGAAGCTGAGCGCTGTGACTGCCGCGGACACGGCCGTGTATTACTGTGCGAAAGGGGGGTATAAACTGGAACAATGGGTTTGACTGTTGGGGCCAGGGAACCCTGGTCACCGTCTCCTCA SEQ ID NO: 30853 |
| | | AA | EIVLTQSPDFQSVTPKEKVTITCRASQSSIGSSLHWYQQKPDQSPKLLIKYASQSFSGVPSRFSGSGSGTDFTLTINSLEAEDAATYYCHQSGRLPLTFGGGTKVEIK SEQ ID NO: 26848 | QVQLQESGPGLVKPSQTLSLTCTVSGGSISNSGYYWSWIRQHPGKGLEWIGYMYYSGSTYYNPSLKSRVTISVDTSKNQFYLKLSAVTAADTAVYYCAKGGYNWNNGFDCWGQGTLVTVSS SEQ ID NO: 30854 |
| iPS:436096 | 21-225_195E10 | NA | GAAATTGTGCTGACTCAGTCTCCAGACTTTCAGTCTGTGACTCCAAAGGAGAAAGTCACCATCACCTGCCGGGCCAGTCAGAGCAGTATTGGTAGTAGCTTACACTGGTACCAGCAGAAACCAGATCAGTCTCCAAAGCTCCTCATCAAGTATGCTTCCCAGTCCTTCTCAGGGGTCCCCTCGAGGTTCAGTGGCAGTGGATCTGGGACAGATTTCACCCTCACCATCAATAGCCTGGAAGCTGAAGATGCTGCAACGTATTACTGTCATCAGAGTAGTCGTTACCATTCACTTTCGGCCCTGGGACCAAAGTGGATATCAAA SEQ ID NO: 26849 | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTTACTACTGGAGCTGGATCCGCCAGCACCCAGGGAAGGGCCTGGAGTGGATTGGGTACATCTATTACAGTGGGAGCACTACTACAACCGTCCCTCAAGAGTCGAGTTACCATATCAGTAGACACGTCTAAGAACCAGTTCTCCCTGAAGCTGAGCTCTGTGACTGCCGCGGACACGGCCGTGTATTATTGTGCGAGAGGGGGTATAACTGGAACCACGGTATGGACGTCTGGGGCCAAGGGACCACGGTCACCGTCTCCTCA SEQ ID NO: 30855 |

FIGURE 50
(Continued)

| | | | |
|---|---|---|---|
| iPS:436098 | 21-225_195G11 | AA | EIVLTQSPDFQSVTPKEKVTITCRASQSIGSSLHW YQQKPDQSPKLLIKYASQSFSGVPSRFSGSGSGT DFTLTINSLEAEDAATYYCHQSSRLPFTFGPGTK VDIK<br>SEQ ID NO: 26850 | QVQLQESGPGLVKPSQTLSLTCTVSGGSISSGGYYW SWIRQHPGKGLEWIGYIYYSGSTYYNPSLKSRVTIS VDTSKNQFSLKLSSVAAADTAVYYCARGGYNWN HGMDVWGQGTTVTVSS<br>SEQ ID NO: 30856 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTATTCAAC TCCAACAATAAGAACTACTTAGCTTGGTACCA GCAGAAACCCGGTCAGCCTCCTAACCTGCTCA TTTACTGGGCATCTACCCTGGAATCTGGGGTC CCTGACCGATTCAGTGGCAGCGGGTGTGGGAC AGATTTCACTCTCACCATCAGCAGCATGCAGG CTGAAGATGTGGCAGTTTATTACTGTCAGCAA TATTGTAGTTTTCCATTCACTTTCGGCCCTGGG ACCAAAGTGGATATCAGA<br>SEQ ID NO: 26851 | CAGGTGCAACTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGCTTTCATACATTAGTAGTAGTGGTACT ACCGTATTCTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGAATGGGTG GGAGCCGACTACTGGGGCCAGGGAACCCTGGTC ACCGTCTCCTCA<br>SEQ ID NO: 30857 |
| | | AA | DIVMTQSPDSLAVSLGERATINCKSSQSVLFNSN NKNYLAWYQQKPGQPPNLLIYWASTLESGVPD RFSGSGCGTDFTLTISSMQAEDVAVYYCQQYCS FPFTFGPGTKVDIR<br>SEQ ID NO: 26852 | QVQLVESGGGLVKPGGSLRLSCAASGFTFSDYYMS WIRQAPGKGLEWLSYISSSGTTVFYADSVKGRFTIS RDNAKNSLYLQMNSLRAEDTAVYYCAREWVGAD YWGQGTLVTVSS<br>SEQ ID NO: 30858 |

FIGURE 50
(Continued)

| | | | | |
|---|---|---|---|---|
| iPS:436100 | 21-225_195G12 | NA | GACATCCAGATGACCCAGTCTCCATCTTCCGT GTCTGCATCTGTAGGAGACAGAGTCACCATCA CTTGTCGGGCGAGTCAGGGTATTAACAACTGG TTAGCCTGGTATCAGCAGAAACCAGGGAAAG CCCCTAAGCTCCTGATCTATGGTGTTTCCAGTT TGCAGAGTGGGGTCCCATCAAGGTTCAGCGGC AGTGGATCTGGGACAGATTTCACTCTCACCAT CAGCAGCCTGCAGCCTGAAGATTTTGCAACTT ACTCTTGTCAACAGGCTAACAGTTTCCGTGG ACGTTCGGCCGAGGGACCAAGGTGAAAATC AG<br><br>SEQ ID NO: 26853 | GAGGTGCAGCTGTTGGAGTCTGGGGGAGGCTTG GTACAGCCTGGGGGGTCCCTGAGACTCTCCTGTG CAGCCCTCTGATTCACCTTTAGCACCTATGCCAT GAGTTGGGTCCGCCAGGCTCCAGGGAAGGGCT GGAGTGGGTCTCAGTTATTAGTCGTAGTGGTGGT AACACACTACGCAGACTCCGTGAAGGGCCGG TTCACCATCTCCAGAGACAATTCCAAGAATACGC TGTATCTGCAAATGAACAGCCTGAGAGCCGAGG ACACGGCCGTATATTCCTGTGCGAAAGATGGATT CGGTGGGGAGCTCCTACTTTGACTACTGGGGCCAG GGAACCCTGGTCACCGTCTCCTCA<br><br>SEQ ID NO: 30859 |
| | | AA | DIQMTQSPSSVSASVGDRVTITCRASQGINNWLA WYQQKPGKAPKLLIYGVSSLQSGVPSRFSGSGS GTDFTLTISSLQPEDFATYSCQQANSFPWTFGRG TKVENQ<br><br>SEQ ID NO: 26854 | EVQLLESGGGLVQPGGSLRLSCAASGFTFSTYAMS WVRQAPGKGLEWVSAISRSGGNTHYADSVKGRFTI SRDNSKNTLYLQMNSLRAEDTAVYSCAKDGFGGS SYFDYWGQGTLVTVSS<br><br>SEQ ID NO: 30860 |
| iPS:436102 | 21-225_196B1 | NA | GACATCGTGATGACCCAGTCTCCAGACTCCCT GGCTGTGTCTCTGGGCGAGAGGGCCACCATCA ACTGCAAGTCCAGCCAGAGTGTACTTAGCAGC TCCAACAATAAGAAGAGTACTTAGCTTGGTATCA GCAGAAACCAGGACAGCCTCCTAAGCTGCTCA TTTACTGGGCATCTATCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTCTAGTCTTCCATTCACTTTCGGCCCTGGG ACCAAAGTGGATATCAAA<br><br>SEQ ID NO: 26855 | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGATTTCATACATTAGTAGTAGTGGTATT ACCATGTACTACCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGAATGGGTG GGAGCGACTACTGGGGCCAGGGAACCCTGGTC ACCGTCTCCTCA<br><br>SEQ ID NO: 30861 |

FIGURE 50
(Continued)

| | | | |
|---|---|---|---|
| | | AA | DIVMTQSPDSLAVFLGERATINCKSSQSILFSSNN KRYLAWYQQKPGQPPKLLIYWASIRESGVPDRF SGSGSGTDFTLTISSLQAEDVAVYYCQQYSSLPF TFGPGTKVDIK<br>SEQ ID NO: 26856 | QVQLVESGGGLVKPGGSLRLSCAASGFTFSDYYMS WIRQAPGKGLEWISYISSSGITMYYADSVKGRFTIS RDNAKNSLYLQMNSLRAEDTAVYYCAREWVGAD YWGQGTLVTVSS<br>SEQ ID NO: 30862 |
| iPS:436104 | 21-225_196C1 | NA | GACATCGTGATGACCCAGTCTCCAGACTCCCT GGCTGTGTCTCTGGGCGAGAGGGCCACCATCA ACTGCAAGTCCAGCCAGAGTGTTTATTCAAC TCCAACAATAAGAACTACTTAGCTTGGTACCA GCAGAAACCCGGTCAGCTTCCTAACCTGCTCA TTTACTGGGCATCTACCCTGGAATCTGGGGTC CCTGACCGATTCAGTGGCAGCGGGTGTGGGAC AGATTCACTCTCACCATCAGCAGCATGCAGG CTGAAGATGTGGCAGTTTATTACTGTCAGCAA TATTGTAGTTTTCCATTCACTTTCGGCCCTGGG ACCAAAGTGGATATCAGA<br>SEQ ID NO: 26857 | CAGGTGCAACTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGCTTTCATACATTAGTAGTAGTGGTACT ACCGTATTCTACGCAGACTCTGTGAAGGGCCGAT TCACCATCTCCAGGGACAACGCCAAGAACTCACT GTATCTGCAAATGAACAGCCTGAGAGCCGAGGA CACGGCCGTGTATTACTGTGCGAGAGAATGGGTG GGAGCCGACTACTGGGGCCAGGGAACCCTGGTC ACCGTCTCCTCA<br>SEQ ID NO: 30863 |
| | | AA | DIVMTQSPDSLAVSLGERATINCKSSQSVLFNSN NKNYLAWYQQKPGQLPNLLIYWASTLESGVPD RFSGSGCGTDFTLTISSMQAEDVAVYYCQQYCS FPFTFGPGTKVDIR<br>SEQ ID NO: 26858 | QVQLVESGGGLVKPGGSLRLSCAASGFTFSDYYMS WIRQAPGKGLEWLSYISSSGTTVFYADSVKGRFTIS RDNAKNSLYLQMNSLRAEDTAVYYCAREWVGAD YWGQGTLVTVSS<br>SEQ ID NO: 30864 |

FIGURE 50
(Continued)

| | | | | |
|---|---|---|---|---|
| iPS:436106 | 21-225_196F2 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAACTCCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGACTAACAGTGTCCCATTC ACTTTCGGCCCTGGGACCAAAGTAGATATCAA A | CAGGTGCAGCTGGTGGAGTCTGGGGGAGGCGTG GTCCAGCCTGGGGAGGTCCCTGAGACTCTCCTGTG CAGCCCTCTGATTCACCTTCAGTAGCTTTGGCAT GCACTGGGTCCGCCAGGCTCCAGGCAAGGGCT GGAGTGGGTGGCAGTTATATTAATGATGGAAGT AATAAAAAGTGTCAGACTCCGTGAAGGGCCGA TGCACCATTTCCAGAGACAACTCCAAGAACACGC TGTATCTGCAAATGAACAGCCTGAGAGCTGAGG ACACGGCTGTTTATTACTGTGCGAGAGACAGCA GTGGCTGGTAAACGGTGTGGACGTCTGGGGCCA GGGACCACGGTCACCGTCTCCTCA |
| | | | SEQ ID NO: 26859 | SEQ ID NO: 30865 |
| | | AA | DIQMTQSPSSVSASVGDRVTITCRASQGISSWLA WYQQKPGKAPKLLIYAASSLQSGVPSRFSGSGS GTDFTLTISSLQPEDFATYCQQTNSVPFTFGPGT KVDIK | QVQLVESGGGVVQPGRSLRLSCAASGFTFSSFGMH WVRQAPGKGLEWVAVILNDGSNKKCADSVKGRC TISRDNSKNTLYLQMNSLRAEDTAVYYCARGQQW LVNGVDVWGQGTTVTVSS |
| | | | SEQ ID NO: 26860 | SEQ ID NO: 30866 |
| iPS:436110 | 21-225_196F4 | NA | GACTTTCAGATGATCCAGTCTCCATCCTCCCTG TCTGCATCTGTAGGCGACAGAGTCACCATCAC TTGCCGGGCAAGTCAGAGTCATTCACAGCTATT TAAATTGGTATCAGCAGAAACCAGGGAAAGC TCCTAAGCTCCTGATCTACACTGCATCCAGTTT GCAAGGTGGGGTCCCATCAAGGTTCAGTGGCA GTGGATCTGGGACAGATTTCACTCTCACCATC AGCAGTCTGCAGCCTGAAGATTTTGCAACTTA CTACTGTCAACAGAGCTACGGTTCCCCTCTCA CTTTCGGCGGAGGGACCAAGGTGGAGATCAA A | GAGGTGCAGCTGTGTGGAGTCTGGGGGAGGCTTG GTACAGCCTGGGGGGTCCCTGAGATTCTCCTGTG CAGCCCTCTGGATTCACCTTTAGCAGCTGTGCCAT GACCTGGGTCCGCCAGGCTCCAGGGAAGGGGCT GGAGTGGGTCTCAGCTATTAGTAGTGGTGGTGT AGCACATACTACGCAGACTCCGTGAAGGGCCGG TTCACCATTTCCAGAGACAATTCCAAGAACACGC TGTATCTGCAAATGAACAGCCTGAGAGCCGAGG ACACGGCCGTATGGCTCCTACTACTACGGTATGA GTTTGACTGGCCAAGGGACCACGGTCACCGTCTCC TCA |
| | | | SEQ ID NO: 26861 | SEQ ID NO: 30867 |

FIGURE 50
(Continued)

| | | | |
|---|---|---|---|
| iPS:436112 | 21-225_196C7 | AA | DFQMIQSPSSLSASVGDRVTITCRASQRIHSYLN WYQQKPGKAPKLLIYTASSLQGGVPSRFSGSGS GTDFTLTISSLQPEDFATYYCQQSYGSPLTFGGG TKVEIK<br>SEQ ID NO: 26862 | EVQLLESGGGLVQPGGSLRFSCAASGFTFSSCAMT WVRQAPGKGLEWVSAISGSGGSTYYADSVKGRFTI SRDNSKNTLYLQMNSLRAEDTAVYYCAKVGGLTG SYYYYGMDVWGQGTTVTVSS<br>SEQ ID NO: 30868 |
| | | NA | GACATCCAGATGACCCAGTCTCCATCCTCACT GTCTGCATCTGTAGGAGACAGAGTCACCATCA CTTGTCGGGCGAATCAGGCATTAGCAGCCATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTGGATCTGGAACAGATTTCACTCTCACCATC AGCAGCCTGCAGCCTGAAGATTTTGCAACTTA TTACTGCCAACATTATCTCACTTACCCTCTCAC TTTCGGCGGAGGGACCAAGGTGGAGATCAAA<br>SEQ ID NO: 26863 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTGATGGAAGT AATGAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATAGGGG GGTGGGTTACTACGGTTTGGACGTCTGGGGCCAA GGGACCACGGTCACCGTCTCCTCA<br>SEQ ID NO: 30869 |
| | | AA | DIQMTQSPSSLSASVGDRVTITCRANQAISNYLA WFQQKPGKAPKSLIYAASSLQSGVPSKFSGSGSG TDFTLTISSLQPEDFATYYCQHYLTYPLTFGGGT KVEIK<br>SEQ ID NO: 26864 | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARDRGV GYYGLDVWGQGTTVTVSS<br>SEQ ID NO: 30870 |

FIGURE 50
(Continued)

| | | | |
|---|---|---|---|
| iPS:436114 | 21-225_196G8 | NA | GACATCGTGATGACCCAGTCTCCAGACTCCCTGACTGTGTCTCTGGGCGAGAGGGCCACCGTCAACTGCAAGTCCAGCAGTCAGAGTGTTTTACACAGCTCCAACAATAACAGTACTACTTAGCTTGGTACCAGCAGAAACCAGGACAGCCTCCTAAGCTGCTCATTTACTGGGCATCTACCCGGGAATCCGAGTCCCTGACCGATTCAGTGGCAGCGGGTCTGGGACAGATTTCACTCTCGCCATCAGCAGCCTGCAGGCTGAAGATGTGGCGGTTTATTACTGTCAGCAATATTATAATACTCCTCGACATTCGGCCAAGGGACCAAGGTGGAAATCAAA

SEQ ID NO: 26865 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGATGCGGCAGGCCACTGGTCAAGGCTTGAGTGGATGGGATGCACCTAACAGTGGTAACACAGGCTATGCACCGAAGTTCCAGGGCAGAGTCACCATGACCAGGGACACCTCCATAAGCACAGCCTTCATGGAGCTGAGCAGCCTGAGATCTGAGGACACGGCCGTGTACTGTGCCTATAGCGGTGGCTGGTACGTGTTCGACCCCTGGGGCCAGGGAACCCTGGTCACCGTCTCCTCA

SEQ ID NO: 30871 |
| | | AA | DIVMTQSPDSLTVSLGERATVNCKSSQSVLHSSNNNNYLAWYQQKPGQPPKLLIYWASTRESGVPDRFSGSGSGTDFTLAISSLQAEDVAVYYCQQYYNTPPTFGQGTKVEIK

SEQ ID NO: 26866 | QVQLVQSGAEVKKPGASVKVSCKASGYTFTNYDINWMRQATGQGLEWMGWMHLNSGNTGYAPKFQGRVTMTRDTSISTAFMELSSLRSEDTAVYYCAYSGGWYVFDPWGQGTLVTVSS

SEQ ID NO: 30872 |
| iPS:436116 | 21-225_196B9 | NA | GACATCCAGATGACCCAGTCTCCATCTTCCGTGTCTGCATCTGTAGGAGACAGAGTCACCATCACTTGTCGGGCGAGTCAGGGTATTAGCAACTGCTTAGCCTGGTATCAGCAGAAACCAGGGAAAGCCCCTAAGTTCCTGATCTGTGCTGCATCCAGTTTGCAAAGTGCGGTCCCATCAAGGTTCAGTGGCAGTGGATCTGGGACAGATTTCACTCTCACCATCAGCAGCCTGCAGCCTGAAGATTTTGCATCTTACTATTGTCAACAGGGTGACAGTTTCCCTCCGACGTTCGGCCAAGGGACCAAGGTGGAATTCAGA

SEQ ID NO: 26867 | CAGGTGCAGCTGGTGCAGTCTGGGGCTGAGGTGAAGAAGCCTGGGGCCTCAATGAAGGTCTCCTGCAAGGCTTCTGGATACACCTTCACCGGCTACTATAGCACTGGGTGCGACAGGCCCCTGGACAAGGGCTTGAGTGGATGGGATGGATCAACCCTAACAGTGGTGGCACAAACTTTGCACAGAAGTTCGGGCAGGGTCACCATGACCAGGGACACGTCCATCAGCACAGCCTACATGGAGCTGAGCAGCCTGAGCTCTGACACGGCCGTGTATTACTGTGCGAGAGGGGGGTTCGGGGAGTTCCAACTACTACTACGTTATGGACGTCTGGGGCCAAGGGACCACGGTCACCGTCTCCTCA

SEQ ID NO: 30873 |

FIGURE 50
(Continued)

| | | | | |
|---|---|---|---|---|
| iPS:436118 | 21-225_196A10 | AA | DIQMTQSPSSVSASVGDRVTITCRASQGISNCLAWYQQKPGKAPKFLICAASSLQSAVPSRFSGSGSGTDFTLTISSLQPEDFASYYCQQGDSFPPTFGQGTKVEFR<br>SEQ ID NO: 26868 | QVQLVQSGAEVKKPGASMKVSCKASGYTFTGYYMHWVRQAPGQGLEWMGWINPNSGGTNFAQKFRGRVTMTRDTSISTAYMELSRLSSDDTAVYYCARGGVRGVPNYYYVMDVWGQGTTVTVSS<br>SEQ ID NO: 30874 |
| | | NA | GACATCCAGATGACCCAGTATCCATCTTACGTGTCTGCATCTGTAGGAGACAGAGTCAGCATCACTTGTCGGGCGAGTCAGGGTATTAGCAGCAGGTGGTTAGCCTGGTATCAGCAGAAGCCAGGGAAAGCCGCCAAGTTCCTGATCTATGCTGCATCCAGTTTGCTAGGTGTGGGGTCTCATCAAGGTTCAGCGGCAGTGGATCTGGGACAGATTTCACTCTCACCATCAGCAGCCTGCAGCCTGAAGATTTTGCAATTTACTATTGTCAACGGGATAAACAGTTTACCGTGCAGTTTTGGCCAGGGGAGGACCAAGCTGGAGATCAAA<br>SEQ ID NO: 26869 | CAGGTGCAGCTGGTGGTGGAGTCTGGGGGAGGCGTGGTCCAGCCTGGGAGGTCCCTGAGACTCTCCTGTGCAGCGTCTGGATTCACCTTCACTGGCTACTATATGCATTGGGTCCGCCAGGCTCCAGGCAAGGGGCTGGAGTGGGTGGCAGTTATTGGTATGATGAACTAATAAATACTATGCAGACTCCGTGAAGGGCCGATTCACCATCTCCAGAGACACAATTCCAAGAACACGCTGTATCTGCAAATGAACAGCCTGAGAGCCGAGGACACGGCTGTGTATTACTGTGCGAGAGATTGGTTCGGGGAGGGAACTACTACGGTATGGACGTCTGGGGCCAAGGGACCACGGTCACCGTCTCCTCA<br>SEQ ID NO: 30875 |
| | | AA | DIQMTQYPSYVSASVGDRVSITCRASQGISRWLAWYQQKPGKAAKFLIYAASSLLGGVSSRFSGSGSGTDFTLTISSLQPEDFAIYYCQRDNSLPCSFGQGTKLEIK<br>SEQ ID NO: 26870 | QVQLVESGGGVVQPGRSLRLSCAASGFTFSHYVMHWVRQAPGKGLEWVAVIWYDGTNKYYADSVKGRFTISRDNSKNTLYLQMNSLRAEDTAVYYCARDWFGEGNYGMDVWGQGTTVTVSS<br>SEQ ID NO: 30876 |

FIGURE 50
(Continued)

| | | | |
|---|---|---|---|
| iPS:436120 | 21-225_196C10 | NA | GACATCCAGATGACCCAGTCTCCATCCTCCT<br>GTCTGCATCTGTAGGAGACAGAGTCACCATCA<br>CTTGCCGGGCAAGTCAGGCATTAGAAATGAT<br>TTAGGCTGGTATCAGCAGAAACCAGGGAAAG<br>CCCCTAAGCGCCTGATCTATGCTGCATCCAGT<br>TTGCAAAGTGGGGTCCCATCAAGGTTCAGCGG<br>CAGTGGTTCTGGGACAGAATTCACTCTCACAA<br>TCAGCAGCCTGCAGCCTGAAGATTTTGCAACT<br>TATTACTGTCTACAATATAATAGTTACCCTCTC<br>ACTTTCGGCGGAGGGACCAAGGTGGAGATCA<br>AA | CAGGTGCAGCTGCAGGAGTCGGGCCCAGGACTG<br>GTGAAGCCTTCACAGACCCTGTCCCTCACCTGCA<br>CTGTCTCTGGTGGCTCCATGAGGAGTGGTGGTGA<br>CTACTGGAGCTGGATCCGCCAGCACCCAGGGAA<br>GGGCCTGGAGTGGTTTGGGTTCATCTATTACAGT<br>GGGAGCACTACTACAATCCGTCCCTCAAGAGTC<br>GAGTTACCTTATCAGTAGACACGTCTAAGAACCA<br>GTTCTCCCTGAAGCTGAGCTCTGTGACTGCCGCG<br>GACACGGCCGTGTATTACTGTGCGAGAATGACT<br>ACAGTAACTACTACTACGGTATGGACGTCTGGGG<br>CCAAGGGACCACGGTCACCGTCTCCTCA |
| | | | SEQ ID NO: 26871 | SEQ ID NO: 30877 |
| | | AA | DIQMTQSPSSLSASVGDRVTITCRASQGIRNDLG<br>WYQQKPGKAPKRLIYAASSLQSGVPSRFSGSGS<br>GTEFTLTISSLQPEDFATYYCLQYNSYPLTFGGG<br>TKVEIK | QVQLQESGPGLVKPSQTLSLTCTVSGGSMRSGGDY<br>WSWIRQHPGKGLEWFGFIYYSGSTYYNPSLKSRVT<br>LSVDTSKNQFSLKLSSVTAADTAVYYCARMDYSN<br>YYYGMDVWGQGTTVTVSS |
| | | | SEQ ID NO: 26872 | SEQ ID NO: 30878 |
| iPS:436122 | 21-225_196G10 | NA | GAAATTGTGTTGACGCAGTCTCCAGGCACCCT<br>GTTATTGTCTCCGGGGAAAGAGCCACCCTCT<br>CCTGCAGGGCCAGTCCGAGTGTTAGCAACAGC<br>TTCTTAGCCTGGTACCAGCAGAAACCTGGCCA<br>GGCTCCCAGGCTCCTCATCTATGGTGCATCCA<br>GCAGGGCCACTGGCATCCCAGACTTCAGT<br>GGCAGTGGGTCTGGGACAGACTTCACTCTCAC<br>CAACAGCAGACTGGAGCCTGAAGATTTTGCAG<br>TGTATTACTGTCAGCAGTATGGTAGCTCACCT<br>CCGTGGACGTTCGGCCAAGGGACCAAGGTAG<br>AACTCAAA | GAGGTGCAGCTGGTGGAGTCTGGGGGAGGCCTG<br>GTCAAGCCTGGGGGGTCCCTGAGACTCTCCTGTG<br>CAGCCTCTGGATTCACCTTCAGGGACTATAGCAT<br>GAACTGGGTCCGCCAGGCTCCAGGGAAGGGCT<br>GGAGTGGGTCTCATCTATTAGTAGTGGTAGTGGT<br>TACATACACTACGCAGACTCAGTGAAGGGCCGA<br>TTCACCATCTCCAGAGACAACGCCAAGAACTCAC<br>TGTATCTGCAAATGAACAGCCTGAGAGCCGAGG<br>ACACGGCTGTGTATTACTGTGCGGAGCAACTAT<br>GGCCCTTGACTACTGGGGCCAGGGAACCCTGGTC<br>ACCGTCTCCTCA |
| | | | SEQ ID NO: 26873 | SEQ ID NO: 30879 |

FIGURE 50
(Continued)

| | | | |
|---|---|---|---|
| iPS:436132 | 21-225_196C12 | AA | EIVLTQSPGTLLLSPGERATLSCRASPSVSNSFLA WYQQKPGQAPRLLIYGASSRATGIPDRFSGSGSG TDFTLTNSRLEPEDFAVYYCQQYGSSPWTFGQ GTKVELK<br>SEQ ID NO: 26874 |
| | | | EVQLVESGGGLVKPGGSLRLSCAASGFTFRDYSMN WVRQAPGKGLEWVSSISSGSGYIHYADSVKGRFTIS RDNAKNSLYLQMNSLRAEDTAVYYCARATMALD YWGQGTLVTVSS<br>SEQ ID NO: 30880 |
| | | NA | GACATCCAGATGACCCTGTCTCCATCGTCCCT GTTTGCATGTGTAGGAGACAGAGTCATCATCA CTTGCCGGGCAAGTCAGGGCATTAGAAATGAT CTAGGCTGGTCTCAGCAGAAATCCAGGGAAAGC CCCTAAGCGCCTGATCTATGCTGCATCCAGTTT GCAAAGTGGGGTCCCATCAAGGTTCAGCGGCA GTGGATCTGGGACAGACGCTGAGAATTCACAATC AGCAGCCTGCAGCCTGAAGATATTGATTTGAAACTA TTACTGTCTACAGCATAATGATTTCCCGTTCAC TTTCGGCCGAGGGACCAAGGTGGAGATCAAA<br>SEQ ID NO: 26875 | CAGGTGCAGCTGGTGCAGTCTGGGGCTGAGGTG AAGAAGCCTGGGGCCTCAGTGAAGGTCTCCTGC AAGGCTTCTGGATACACCTTCATCAGTTATGATA TCAACTGGGTGCGACAGGCCACTGGACAAGGC TTGAGTGGATGGGATGGATGAACCATAAAGGG GTAACACAGGCTATGACCAGGACACCTCCATAAGCA GAGTCACCATGACCAGGGACACCTCCATAAGCA CAGCCTACATGGAGCTGAGCAGCCTGAGATCTG AGGACACGGCCGTTTATTACTGTGCGAGAGAG ACCCGTATAACTGAACTCCTACGTATGGACGT CTGGGGCCAAGGGGCCACGGTCACCGTCTCCTCA<br>SEQ ID NO: 30881 |
| | | AA | DIQMTLSPSSLFACVGDRVIITCRASQGIRNDLG WSQQNPGKAPKRLIYAASSLQSGVPSRFSGSGSG TEFTITISSLQPEDFETYYCLQHNDFPFTFGRGTK VEIK<br>SEQ ID NO: 26876 | QVQLVQSGAEVKKPGASVKVSCKASGYTFISYDIN WVRQATGQGLEWMGWMNPKRGNTGYAQKFQGR VTMTRDTSISTAYMELSSLRSEDTAVYYCARGDPY NWNSYAMDVWGQGATVTVSS<br>SEQ ID NO: 30882 |

FIGURE 50
(Continued)

| | | | | |
|---|---|---|---|---|
| iPS:436134 | 21-225_196H12 | NA | GAAATTGTGTTGACGCAGTCTCCAGGCACCCT GTTTTGTCTCCAGGGGAAAGAGCCACCCTCT CCTGCAGGGCCAGTCAGTGTTAGAAGCAAC TTCTTAGCCTGGCACCAGCAGAAACCTGGCCA GGCTCCCAGGCTCCTCATCTATGGTGCATAC GCAGGGCCACTGGCATCCCAGACAGGTTCAGT GGCAGTGGGTCTGGGACAGATTCACTCTCAC CATCAACAGACTGGAGCCTGAAGATTTTGCAG TGTATTACTGTCAGCAGTATGGTAACTCACCG TGGACGTTCGGCCAAGGGACCAAGGTGGAAA TCAAA | CAGGTGCAGCTGCAGGAGTCGGGCCCAGGACTG GTGAACCCTTCACAGACCCTGTCCCTCACCTGCA CTGTCTCTGGTGGCTCCATCAGCAGTGGTGTTTA CTACTGGAGCTGGATCCGCCAGCACCCAGGGAA GGGCCTGGAGTGGATTGGGAACATCTATTACAGT GGGAGCACCTACAACAACCCGTCCCTCAAGAGT CGAATTATCATATCAGTAGACACGTCTAAGAACC AGTTCTCCCTGAAGCTGAGCTCTGTGACTGCCGC GGACACGGCCGTGTATTACTGTGCGAGAGGGGA TTACGATGGTTCGGGGAGTTATCACTACTACTAC GGTTTGGACGTCTGGGGCCAAGGGACCACGGTC ACCGTCTCCTCA |
| | | AA | EIVLTQSPGTLFLSPGERATLSCRASQSVRSNFLA WHQQKPGQAPRLLIYGAYRRATGIPDRFSGSGS GTDFTLTINRLEPEDFAVYYCQQYGNSPWTFGQ GTKVEIK | QVQLQESGPGLVNPSQTLSLTCTVSGGSISSGVYYW SWIRQHPGKGLEWIGNIYYSGSTYNNPSLKSRIISV DTSKNQFSLKLSSVTAADTAVYYCARGDYDGSGS YHYYYGLDVWGQGTTVTVSS |
| | | | SEQ ID NO: 26877 | SEQ ID NO: 30883 |
| | | | SEQ ID NO: 26878 | SEQ ID NO: 30884 |
| iPS:436138 | 21-225_197F2 | NA | GACATCCAGATGATCCAGTCTCCTCCTCACT GTCTGCATCTGTAGGAGACAGAGTCACCATCA CTTGTCGGACGAGTCAGGGCATTGGCAATTAT TTAGCCTGGTTTCAGCAGAAACCAGGGAAAGC CCCTAAGTCCCTGATCTCTATAAAACATCCAGTTT GCAAAGTGGGGTCCCATCAAAGTTCAGCGGCA GTGGATCTGGGACAGATTTCACTCTCACCATC AGCAGCCTGCAACAATATATCACTTACCCGCTCAC TTTCGGCGGAGGGACCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGACT GGAGTGGGTGGCAGTTATATGGTATGATGGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGG CGTGGGCTACGACGGTTTGGACGTCTGGGGCCAA GGGACCACGGTCACCGTCTCCTCA |
| | | | SEQ ID NO: 26879 | SEQ ID NO: 30885 |

FIGURE 50
(Continued)

| | | | | |
|---|---|---|---|---|
| iPS:436140 | 21-225_197G3 | AA | DIQMIQSPSSLSASVGDRVTITCRTSQGIGNYLA WFQQKPGKAPKSLLYKTSSLQSGVPSKFSGSGS GTDFTLTISSLQPEDFATYFQQYITYPLTFGGGT KVEIK<br><br>SEQ ID NO: 26880 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS<br><br>SEQ ID NO: 30886 |
| | | NA | GACATCCAGATGACCCAGTCTCCGTCCTCACT GTCTGCATCTGTAGGAGACAGAGTCACCATCA CTTGTCGGGCGAGTCAGGGCATTGGCAATCAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA GTAGATCTGGGACAGACCTGAAGATTTCTCTCACCATC AGCAGCCTGCAGCCTGAAGATTTTGCAACTTA TTACTGCCAACAGTATATAGTAATTACCCGGTCA CTTTCGGCGGCCCTGGGACCAAAGTGGATATCAAG<br><br>SEQ ID NO: 26881 | CAGGTGCAACTGGTGGAGTCTGGGGGAGGCGTG GTCCAGCCTGGGAGGTCCCTGAGACTCTCCGTG TAGCGTCTGGGGTTCACCTTCAGTAGCCATGGCAT GCACTGGGTCCGCCAGGCTCCAGGCAAGGGCT GGAGTGGGTGGCAGTTATATGGTATGATGGAAGT AATAAAAACTATGCAGACTCCGTGAAGGGCCGA TTCACCATCTCCAGAGACAACATCAAGAACACGC TGTATCTGCAAATGAACAGCCTGAGAGCCGAGG ACACGGCTGTGTATTACTGTGCGAGAGATCCCTC TGTAGGGTACGACGGTATGGACGTCTGGGGCCA AGGGACCACGGTCACCGTCTCCTCA<br><br>SEQ ID NO: 30887 |
| | | AA | DIQMTQSPSSLSASVGDRVTITCRASQGIGNHLA WFQQKPGKAPKSLIYAASSLQSGVPSKFSGSRSG TDFSLTISSLQPEDFATYYCQQYSNYPVTFGPGT KVDIK<br><br>SEQ ID NO: 26882 | QVQLVESGGGVVQPGRSLRLSCVASGFTFSSHGMH WVRQAPGKGLEWVAVIWYDGSNKNYADSVKGRF TISRDNSKNTLYLQMNSLRAEDTAVYYCARDPSVG YDGMDVWGQGTTVTVSS<br><br>SEQ ID NO: 30888 |

FIGURE 50
(Continued)

| | | | |
|---|---|---|---|
| iPS:436146 | 21-225_197F4 | NA | GAAATTGTGTTGACGCAGTCTCCAGGCACCCT GTCTTTGTCTCCAGGGGAAGGAGCCACCCTCT CCTGCAGGGCCAGTCAGTATTCGCAGCAGC TTCTTAGCCTGGTACCTGCAGAAGCCTGGCCA GGCTCCCAGGCTCCTCATCTATGGTGCATCCA GCAGGGCCACTGGCATCCCAGACAGCAGGTTCAGT GGCAGTGGGTCTGGGACAGACTTCACTCTCAC CATCAGCAGACTGGAGCCTGAAGATTTTGCAG TGTATTACTGTCAGCAGTATGGAAACTCACCG TGGGCGTTCGGCCAAGGGACCAAGGTGGAAA TCAAA SEQ ID NO: 26883 | CAGGTGCAGCTGCAGGAGTCGGGCCCAGGACTG GTGAAGCCTTCACAGACCCTGTCCCTCACCTGCA CTGTCTCTGGTGCTCCATCAGCAGTGGTGATTA CTACTGGAACTGGATCCGCCAGCACCCAGGGAA GGGCCTGGAGTGGATTGGGTACATCTTTTACAGT GGGAGCACCTACTACAACCCGTCCCTCAAGAGTC GAATTACCATATCAGTAGACACGTCTAAGAACCA GTTCTCCCTGAAGCTGAGCTCTGTGACTGCCGCG GACACGGCCGTGTATTACTGTGCGAGAGGGGATT ACGATGGTTCGGGGAGTTATCACTACTACTACGG TTTGGACGTCTGGGGCCAAGGGACCACGGTCACC GTCTCCTCA SEQ ID NO: 30889 |
| | | AA | EIVLTQSPGTLSLSPGEGATLSCRASQSIRSSFLA WYLQKPGQAPRLLIYGASSRATGIPDRFSGSGSG TDFTLTISRLEPEDFAVYYCQQYGNSPWAFGQG TKVEIK SEQ ID NO: 26884 | QVQLQESGPGLVKPSQTLSLTCTVSGGSISSGDYYW NWIRQHPGKGLEWIGYIFYSGSTYYNPSLKSRITISV DTSKNQFSLKLSSVTAADTAVYYCARGDYDGSGS YHYYYGLDVWGQGTTVTVSS SEQ ID NO: 30890 |
| iPS:436150 | 21-225_197H4 | NA | GACATCATGATGACCCAGTCTTCAGACTCCCT GACTGTGTCTCTGGGCGAGAGGGCCATCATCA GCTGCAGGTCCAGCCAGAGTGTTTTACACAGC TTCAACAATTACAACTACTTAGCTTGGTACCA GCAGAAAGCAGGACATCCTCCTAACCTGCTCA TTTACTGGGCATCTACCCGGGAATCCGGGGTC CCTGACCGATTCAGTGGCAGCGGGTCTGGGAC AGATTTCACTCTCCCCATCAGCAGCCTGCAGG CTGAAGATGTGGCAGTTTATTACTGTCAACAA TATTATAGTACTCCTCGACGTTCGGCCTAGG GACCAAGGTGGAAATCAAA SEQ ID NO: 26885 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCCCATAGCAGT GGCTGGTACTACTTTGACTACTACTGGGGCCAGGAA CCCTGGTCACCGTCTCCTCA SEQ ID NO: 30891 |

FIGURE 50
(Continued)

| | | | | |
|---|---|---|---|---|
| iPS:436152 | 21-225_197B6 | AA | DIMMTQSSDSLTVSLGERATISCRSSQSVLHSFNN YNYLAWYQQKAGHPPNLLIYWASTRESGVPDR FSGSGSGTDFTLPISSLQAEDVAVYYCQQYYSTP PTFGLGTKVEIK<br>SEQ ID NO: 26886 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAHSSGW YYFDYWGQGTLVTVSS<br>SEQ ID NO: 30892 |
| | | NA | GACATCCAGATGACCCAGTCTCCATCCTCACT GTCTGCATCTGTAGGAGACAGAGTCACCATCA CTTGTCGGGCGAGTCAGGGCATTGGCAAATAT TTAGCCTGGTTTCAGCAGAAACCAGGGAAAGC CCCTAAGTCCCTGATCTATGGTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAATATAGTACTTACCCGCTCA CTTTCGGCGGAGGGACCAAGGTGGAGATCAA A<br>SEQ ID NO: 26887 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTGATGGAAGT AATAAAAACTACGCAGACTCCGTGAAGGGCCGA TTCACCATCTCCAGAGACAATTCCAAGAACATGT TGTATCTGCAAATGAACAGCCTGAGAGCCGAGG ACACGGCTATGTATTACTGTGCGAGAGATCAGG CGTGGGCTACGACGGTTTGGACGTCTGGGGCCAA GGGACCTCGGTCACCGTCTCCTCA<br>SEQ ID NO: 30893 |
| | | AA | DIQMTQSPSSLSASVGDRVTITCRASQGIGKYLA WFQQKPGKAPKSLIYGASSLQSGVPSKFSGSGSG TDFTLTISSLQPENFATYYCQQYSTYPLTFGGGT KVEIK<br>SEQ ID NO: 26888 | QVQLVESGGGVVQPGRSLRLSCAASGFTFSSYGMH WVRQAPGKGLEWVAVIWYDGSNKNYADSVKGRF TISRDNSKNMLYLQMNSLRAEDTAMYYCARDQGV GYDGLDVWGQGTSVTVSS<br>SEQ ID NO: 30894 |

FIGURE 50
(Continued)

| | | | | |
|---|---|---|---|---|
| iPS:436154 | 21-225_197C6 | NA | GACATCATGATGACCCAGTCTCCAGACTCCCTGGCTGTGTCTCTGGGCGAGAGGGCCATCATCAGCTGCAGGTCCAGCCAGAGTGTTTTACACAGCTCCAACAATTACAACTACTTAGCTTGGTACCAGCAGAAACCAGGACATCCTCCTAAACCTGCTCATTTACTGGGCATCTACCCGGAATCGGGGGTCCCTGACCGATTCAGTGGCAGCGGGTCTGGGACAGATTTCACTCTCACCATCAGCAGCCTGCAGGCTGAAGATGTGGCAGTTTATTACTGTCAACAATATTATAGTACTCCCTCCGACGTTCGGCCTAGGGACCAAGGTGGAAATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGCACCTAACAGTGGTAACACAGGCTATGCACAGAAGTTCCAGGGCAGAGTCACCATGACCAGGAACACCTCATAAGCACAGCCTACATGGAGCTGAGCAGCCTGAGATCTGAGGACACGGCCGTGTATTACTGTGCCCATAGCAGTGGCTGGTACTACTTTGACTACTGGGGCCAGGGAACCCTGGTCACCGTCTCTCA |
| | | | SEQ ID NO: 26889 | SEQ ID NO: 30895 |
| | | AA | DIMMTQSPDSLAVSLGERAIISCRSSQSVLHSSNNYNYLAWYQQKPGHPPNLIYWASTRESGVPDRFSGSGSGTDFTLTISSLQAEDVAVYYCQQYYSTPPTFGLGTKVEIK | QVQLVQSGAEVKKPGASVKVSCKASGYTFTNYDINWVRQATGQGLEWMGWMHPNSGNTGYAQKFQGRVTMTRNTSISTAYMELSSLRSEDTAVYYCAHSSGWYYFDYWGQGTLVTVSS |
| | | | SEQ ID NO: 26890 | SEQ ID NO: 30896 |
| iPS:436156 | 21-225_197C8 | NA | GACATCGTGATGACCCGTCTCCAGACTCCCTGGCTGTGTCTCTGGGCGAGAGGGCCACCATCAACTGCAAGTCCAGCCAGAGTGTTTTACACAGTTCCAACAATAAGAACTACTTAGCTTGGTACCAGCAGAAACCAGGACAGCCTCCTAAGCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGCTGAAGATGTGGCAGTTTATTATTGTCAGCAGTCTTATACTATTCACTTTCGGCCCTGGGACCAAAGTGGATAACAAA | GAGGTGCAACTATTGGAGTCTGGGGGAGGCTTGGTGCAGCCTGGGGGGTCCCTGAGACTCTCCTGTGCAGCCTCTGGATTCACCTTTAGCAGTCAGCTCTGCCATGACCTGGGTCCGCCAGGCTCCAGGGAAGGGACTGGAGTGGGTCTCAGTCTATCATTGGTAATGGTGGTAGAGCATACTACGCAGACTCCGTGAAGGGCCGGTTCACCATCTCCAGAGACAATTCCAAGAACACGCTGTATCTGCAAATGAACAGCCTGAGAACCGAGGACACGGCCGTATAGCAGGATAGCAGTGGCTGGTACTTTGAGATATACTGGGGCCAGGGAACCCTGGTCACCGTCTCCTCA |
| | | | SEQ ID NO: 26891 | SEQ ID NO: 30897 |

FIGURE 50
(Continued)

| | | | |
|---|---|---|---|
| iPS:436158 | 21-225_197G8 | AA | DIVMTPSPDSLAVSLGERATINCKSSQSVLHSSN NKNYLAWYQQKPGQPPKLLIYWASTRESGVPD RFSGSGSGTDFTLSISSLQAEDVAVYYCQQSYTIP FTFGPGTKVDNK<br>SEQ ID NO: 26892 | EVQLLESGGGLVQPGGSLRLSCAASGFTFSSSAMT WVRQAPGKGLEWVSAIIGNGGRAYYADSVKGRFT ISRDNSKNTLYLQMNSLRTEDTAVYYCAKDRGYSR IAVAGTFDYWGQGTLVTVSS<br>SEQ ID NO: 30898 |
| | | NA | GAGATTGTGATGACCCAGACTCCACTTTCTCT GTCCGTCATCCTGGACAGCCGGCCTCCATCT CCTGCAAGTCTAGTCAGAACCTCCTGCATAGT GATGGAAAGACCTATTTGTATTGGTACCTGCA GAAGCCAGGCCAGCTCCACAGGTCCTGATCT ATGAAGTTTCCAACCGGTTCTGTGGGGTGCCA GATAGGTTCAGTGGCAGCGGGTCAGGGACAG ATTTCACACTGAAAATTAGCCGGGTGGAGGCT GAGGATGTTGGGGTTTATTCCTGCATGCAAAG TATACAGCTTCCCTGGACGTTCGCCCAAGGGT CCAAGGTGGAAATCAAA<br>SEQ ID NO: 26893 | CAGGTGCATCTGCAGGAGTCGGGCCCAGGACTG GTGAAGCCTTCGGAGACCCTGTCCCTCACCTGCA CTGTCTCTGGTGGCTCCATCAGTGCTTACTCCTGG AGCTGGATCCGGCAGCCCGCCGGGAAGGGACTG GAGTGGATTGGGCGTCTCTCTCTGTGGGAGCA CCAACTTCAACCCCTCCCTCCAAGAGTCGAGTCAC CATGTCAGTAGACACGTCCAAGAACCAGTTCTCC CTGAGGCTGAGCTCTGTGACCGCCGCGGACACG GCCGTTATTACTGTGCGAGACTCCGGTATAACT GGAACTTCCCTACTTTGACTACTGGGGCCAGGG AGCCCCTGGTCACCGTCCTCTCCTCA<br>SEQ ID NO: 30899 |
| | | AA | EIVMTQTPLSLSVIPGQPASISCKSSQNLLHSDGK TYLYWYLQKPGQPPQVLIYEVSNRFSGVPDRFS GSGSGTDFTLKISRVEAEDVGVYSCMQSIQLPWT FAQGSKVEIK<br>SEQ ID NO: 26894 | QVHLQESGPGLVKPSETLSLTCTVSGGSISAYSWS WIRQPAGKGLEWIGRLSPGGSTNFNPSLKSRVTMSVD TSKNQFSLRLSSVTAADTAVYYCARLRYNWNFPYF DYWGQGALVTVSS<br>SEQ ID NO: 30900 |

FIGURE 50
(Continued)

| | | | | |
|---|---|---|---|---|
| iPS:436160 | 21-225_197C9 | NA | GACATCCAGATGACCCAGTCTCCATCTTCCGT GTCTGCATCTGTAGGAGACAGAGTCACCATCA CTTGTCGGGCGAGTCAGGGTATTAGCAACTGG TTAGCCTGGTTTCAGCAGAAACCAGGGAAAGC CCCTCAGCTCCTGATCTATGCTGCATCCAGTTT GCAAAGTGGGGTCCCATCAAGGTTCAGCGGCA GTGGATCTGGGACAGACTTCAGTCTCACCATC AGCAGCCTGCAGCCTGAAGATTTTGCAACTTA CTATTGTCAACAGGCTAACAGTTTCCCGTGGA CGTTCGGGCAAGGGACCAAGGTGGAAATCAA A SEQ ID NO: 26895 | GAGGTGCAGCTGTTGGAGTCTGGGGGAGGCTTG GCACAGCCGGGGGGGTCCCTGAGACTCTCCTGTG CAGCCTCTGGATTCACCTTTAGGAGCTATGCCAT GAGCTGGGTCCGCCAGGCTCCAGGGAAGGGCT GGAGTGGGTCTCAGTTATTAGTGGTAGAGGTGGT AACACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAAGGCATAGC AGTGGCTGGCTCGCACTACTTTGACTACTGGGGC CAGGGAACCCTGGTCACCGTCTCCTCA SEQ ID NO: 30901 |
| | | AA | DIQMTQSPSSVSASVGDRVTITCRASQGISNWLA WFQQKPGKAPQLLIYAASSLQSGVPSRFSGSGSG TDFSLTISSLQPEDFATYYCQQANSFPWTFGQGT KVEIK SEQ ID NO: 26896 | EVQLLESGGGLAQPGGSLRLSCAASGFTFRSYAMS WVRQAPGKGLEWVSVISGRGGNTYADSVKGRFT ISRDNSKNTLYLQMNSLRAEDTAVYYCAKGIAVAG SHYFDYWGQGTLVTVSS SEQ ID NO: 30902 |
| iPS:436164 | 21-225_197G10 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCTCCTGATCTATGGTGCATCCAGT TTACAAAGTGGGGTCCCATCGAGGTTCAGCGG CAGTGGATCTGGGACAGAATTCACTCTCACAA TCAGCAGCCTGCAGCCTGAAGATTTTGCAACT TATTACTGTCTACAGCATTATAGGTACCCATTC ACTTTCGGCCCTGGGACCAAAGTGGATATCAA A SEQ ID NO: 26897 | CAGGTGCAGCTGGTGGAGTCTGGGGGAGGCGTG GTCCAGCCTGGGAGGTCCCTGAGACTCTCCTGTG TAGCGTCTGGATTCACCTTCAGTAGCTATGGCAT GCACTGGGTCCGCCAGGCTCCAGGCAAGGGGCT GGAGTGGGTGGCAGTTACATGGTATGATGGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGAGAATGGC TACAATTTAGGTACTACTACGGTATAGACGTCTG GGGCCAAGGGACCACGGTCACCGTCTCCTCA SEQ ID NO: 30903 |

FIGURE 50
(Continued)

| | | | |
|---|---|---|---|
| iPS:436167 | | AA | DIQMTQSPSSLSASVGDRVTITCRASQGIRNDLG WYQQKPGKAPKRLIYGASSLQSGVPSRFSGSGS GTEFTLTISSLQPEDFATYYCLQHYRYPFTFGPGT KVDIK<br>SEQ ID NO: 26898 | QVQLVESGGGVVQPGRSLRLSCVASGFTFSSYGMH WVRQAPGKGLEWVAVTWYDGSNKYYADSVKGR FTISRDNSKNTLYLQMNSLRAEDTAVYYCAREWLQ FRYYYGIDVWGQGTTVTVSS<br>SEQ ID NO: 30904 |
| | 21-225_197E11 | NA | GACATCCAGATGACCCAGTCTCCATCCTCGCT GTCTGCATCTGTGGAGACAGAGTCACCATCA CTTGTCGGGCGAGTCAGGGCATTAACAAGTAT TTATCCTGGTTTCAGCAGAAACCAGGGAAAGC CCCTAAGTCATTGATCTATGCTGCATCCAGTGT GCAAAGTGGGGTCCCATCAAAATTCAGCGGCA GTGGATCTGGGACAGATTTCACTCTCACCATC AGCCCGCCTGCAGCCTGACGATTTTGCAACTTA TTACGGCCAACGATATGACACTTACCATTCA CTTTCGGCCCTGGGACCAAAGTGGATATCAAA<br>SEQ ID NO: 26899 | CAGGTGCAGCTGGTGGAGTCTGGGGGAGGCGTG GTCCAGCCTGGGAGGTCCCTGAGACTCTCCTGTG CAGCGTCTGGATTCACCTTCAGGAACTATGGCAT GCACTGGGTCCGCCAGGCTCCAGGCAAGGGCT GGAGTGGGTGGCAGTTATATGGTTTGATGGAAGT AATGACTACTATGCAGACTCCGTGAAGGGCCGAT TCACCATCTCCAGAGACAACAATTCCAAGAACACGCT GTCACTGCAAATGAACAGCCTGAGAGCCGAGA CACGGCTGTGTATTACTGTGCGAGAGATAGAAGC GTCGGCTACGACGGTTAGATGTCTGGGCCAAG GGACCACGGTCACCGTCTCCTCA<br>SEQ ID NO: 30905 | |
| | | AA | DIQMTQSPSSLSASVGDRVTITCRASQGINKYLS WFQQKPGKAPKSLIYAASSVQSGVPSKFSGSGSG TDFTLTISRLQPDDFATYYGQRYDTYPFTFGPGT KVDIK<br>SEQ ID NO: 26900 | QVQLVESGGGVVQPGRSLRLSCAASGFTFRNYGM HWVRQAPGKGLEWVAVIWFDGSNDYYADSVKGR FTISRDNSKNTLSLQMNSLRAEDTAVYYCARDRSV GYDGLDVWGQGTTVTVSS<br>SEQ ID NO: 30906 |

FIGURE 50
(Continued)

| | | | |
|---|---|---|---|
| iPS:436173 | 21-225_197G12 | NA | GACATCCAGATGATCCAGTCTCCTCCTCACT GTCTGCATCTGTAGGAGACAGAGTCACCATCA CTTGTCGGACGAGTCAGGGCATTGGCAATTAT TAGCCTGGTTTCAGCAGAAACCAGGAAAGC CCCTAAGTCCCTGCTCTATAAAACATCCAGTTT GCAAAGTGGGTTCCCATCAAAGTTCAGCGGCA GTGGATCTGGGACAGATTTCACTCTCACCATC AGCAGCCTGCAGCCTGAAGATTTTGCAACTTA TTACTTCCAACAATATATGACTTACCCGCTCAC TTTCGGCGGAGGGACCAAGGTGGAGATCAAA SEQ ID NO: 26901 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGACT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGGG CGTGGGCTACGACGGTTTGGACGTCTGGGGCCAA GGGACCACGGTCACCGTCTCCTCA SEQ ID NO: 30907 |
| | | AA | DIQMIQSPSSLSASVGDRVTITCRTSQGIGNYLA WFQQKPGKAPKSLLYKTSSLQSGFPSKFSGSGSG TDFTLTISSLQPEDFATYYFQQYMTYPLTFGGGT KVEIK SEQ ID NO: 26902 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYDGLDVWGQGTTVTVSS SEQ ID NO: 30908 |
| iPS:436177 | 21-225_198B1 | NA | GAAATTGTGTTGACGCAGTCTCCAGGCACCCT GTCTTTGTCTCCAGGGGAAAGCGCCACCCTCT CCTGCAGGGCCGGTCAAAGTATTAGAACCAAC TTCTTAGCCTGGTACCAGCAGCAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAACAGACTGGAGCCTGAAGATTTTGCAG TGTATTACTGTCAGCAGTATGGTAGTCACCG TGGACGTTCGGCCAAGGGACCAAGGTGGAAA TCAAA SEQ ID NO: 26903 | CAGGTGCAACTGAAGGAGTCGGGCCCAGGACTG GTGAAGCCTTCACAGACCCTGTCCCTCACCTGCA CTGTCTCTGGTGGCTCCATCAACAGTGGTGATTA CTACTGGAACTGGTTCCGCCAGCACCCAGGGAA GGGCCTGGAGTGGATTGGGTACATCTTCCACAGT GGGAGCACCTACTACAACCCGTCCCTCAAGAGTC GAGTAACCGTATCAGTAGACACGTCTAAGAACC AGTTCTCCCTGAAGCTGAGTTCTGTGACTGCCGC GGACACGGCCGTGTATTACTGTGCGAGAGGGGA TTACGATGGTTCGGGGAGTTATCACTATTAC GGTATGGACGTCTGGGGCCGAGGGACCACGGTC ACCGTCTCCTCA SEQ ID NO: 30909 |

FIGURE 50
(Continued)

| | | | |
|---|---|---|---|
| iPS:436179 | 21-225_198E1 | AA | EIVLTQSPGTLSLSPGESATLSCRAGQSIRTNFLA WYQQKPGQAPRLLIYGASSRATGIPDRFSGSGSG TDFTLTINRLEPEDFAVYYCQQYGSSPWTFGQGT KVEIK<br>SEQ ID NO: 26904 | QVQLKESGPGLVKPSQTLSLTCTVSGGSINSGDYY WNWFRQHPGKGLEWIGYIFHSGSTYYNPSLKSRVT VSVDTSKNQFSLKLSSVTAADTAVYYCARGDYDG SGSYHYYGMDVWGRGTTVTVSS<br>SEQ ID NO: 30910 |
| | | NA | GAAATTGTGTTGACGCAGTCTCCAGGCACCCT GTCTTTGTCTCCAGGGGAAAGAGCCACCCTCT CCTGCAGGGCCAGTCAGAGTATAAGGAGCAA CTTCTTAGCCTGGTACCAGCAGAAACCTGGCC AGGCTCCCAGGCTCCTCATCTATGGTGCATTC AGTAGGGCCACTGGCATCCCAGACAGGTTCAG TGGCAGTGGGTCTGGGACAGACTTCACTCTCA CCATCAACAGACTGGAGCCTGAAGATTTTGCA GTGTATTACTGTCAGCAGTATGGTAATTCACC GTGGACGTTCGGCCAAGGGACCAAGGTGGAA ATCAAA<br>SEQ ID NO: 26905 | CAGGTGCAGCTGCAGGAGTCGGGCCCAGGACTG GTGAAGCCTTCACAGACCCTGTCCCTCACCTGCA CTGTCTCTGGTGGCTCCATCAACAGTGGTGTTA CTACTGGAACTGGATCCGCCAGCACCAGGGAA GGGCCTGGAGTGGATTGGGTTCATCTTTTACAGT GGGAGCACCTACTACAACCCGTCCCTCAAGAGTC GACTTTCCATATCAGTAGACACGTCTAAGAACCA GTTCTCCCTGAAGCTGAGCTCTGTGACTGCCGCG GACACGGCCGTGTATTACTGTGCGAGAGGGATT ACGATGGTTCGGGGAGTTATCACTACTATTACGG TATGGACGTCTGGGGCCAAGGGACCACGGTCAC CGTCTCCTCA<br>SEQ ID NO: 30911 |
| | | AA | EIVLTQSPGTLSLSPGERATLSCRASQSIRSNFLA WYQQKPGQAPRLLIYGAFSRATGIPDRFSGSGSG TDFTLTINRLEPEDFAVYYCQQYGNSPWTFGQG TKVEIK<br>SEQ ID NO: 26906 | QVQLQESGPGLVKPSQTLSLTCTVSGGSINSGGYY WNWIRQHPGKGLEWIGFIFYSGSTYYNPSLKSRLSI SVDTSKNQFSLKLSSVTAADTAVYYCARGDYDGS GSYHYYYGMDVWGQGTTVTVSS<br>SEQ ID NO: 30912 |

FIGURE 50
(Continued)

| | | | | |
|---|---|---|---|---|
| iPS:436181 | 21-225_198C2 | NA | GAAATTGTGGTGACGCAGTCTCCAGGCACCCT GTTATTGTATCCGAGGAGAGATCCACCCTCT CCTGCAGGGCCAGTCAGAGTGTTAGAAGCAGC TACTTAGCCTGGTACCAGCAGAAACCTGGCCA GGCTCCCAGGCTCCTCATCTGTGGTCATTCA GCAGGGCCAGTGGCATCCCAGACAGGTTCAGT GGCAGTGGGTCTGGGACAGATTCACTCTCAC CATCAGCAGACTGGAGCCTGAAGATTTTGCAG TGTACTACTGTCAGCAGTATGGTAACTCACCG TGGACGTTCGGCCAAGGGACCAAGGTGGAAA TCAAA | CAGGTGCAGCTGCAGGAGTCGGGCCCAGGACTG GTGAAGCCCTCACAGACCCTATCCCTCACCTGCA CTGTCTCTGGTGGCTCCATCAGCAGTGGTGGTTA CTACTGGAGCTGGATCCGCCAGCACCCAGGGAA GGGCCTGGAGTGGATTGGGAACATCTATTACAGT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGGGATT ACTATGGTTCGGGAGTTATCACAACTACTACGG TTTGGACGTCTGGGGCCAAGGGACCACGGTCACC GTCTCCTCA |
| | | | SEQ ID NO: 26907 | SEQ ID NO: 30913 |
| | | AA | EIVVTQSPGTLLLYSEERSTLSCRASQSVRSSYLA WYQQKPGQAPRLLICGAFSRASGIPDRFSGSGSG TDFTLTISRLEPEDFAVYYCQQYGNSPWTLGHA TKVEIK | QVQLQESGPGLVKPSQTLSLTCTVSGGSISSGGYYW SWIRQHPGKGLEWIGNIYYSGSTYYNPSLKSRVTIS VDTSKNQFSLKLSSVTAADTAVYYCARGDYYGSG SYHNYYGLDVWGQGTTVTVSS |
| | | | SEQ ID NO: 26908 | SEQ ID NO: 30914 |
| iPS:436189 | 21-225_198B6 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAAGTTCAGCGGCA ATAGATCTGGGACAGATTTCACTCTCACCATC AGCAGCCTGCAGCCTGAAGATTTTGCAACTTA TTACTGTCAACAATATAGTACTTACCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCAGGG CGTGGGCTACTACGGTATGGACGTCTGGGGCCAA GGGACCACGGTCACCGTCTCCTCA |
| | | | SEQ ID NO: 26909 | SEQ ID NO: 30915 |

FIGURE 50
(Continued)

| | | | | |
|---|---|---|---|---|
| iPS:436191 | 21-225_198B9 | AA | DIQMTQSPSSLSASVGDRVTITCRASQGIGNYLAWFQQKPGKAPKSLIYAASSLQSGVPSKFSGNRSGTDFTLTISSLQPEDFATYYCQQYSTYPLTFGGGTKVEIK | QVQLVESGGGVVQPGRSLRLSCAASGFTFSSYGMHWVRQAPGKGLEWVAVIWYDGSNKHYADSVKGRFTISRDNSKNTLYLQMNSLRAEDTAVYYCARDQGVGYYGMDVWGQGTTVTVSS |
| | | | SEQ ID NO: 26910 | SEQ ID NO: 30916 |
| | | NA | GACATCCAGATGACCCAGTCTCCATCCTCCCTGTCTGCATCTGTAGGAGACAGAGTCACCATCACTTGCCGGGCAAGTCAGGGCATAAGAAAGATTTAGGCTGGTATCAGCAGAAACCAGGGAAAGCCCCTAAGCGCCTAATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATGTCTGTCTACAACATTATCGTTACCCTTTCACTTTCGGCGGCCTGGGACCAAAGTGGATTTCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATATGTTTGATGGAAGTAATAAATACTATGTAGACTCCGTGAAGGGCCGATTCACCATCTCCAGAGACAATTCCAAGAACACGCTGTTTCTGCAAATGAGCAGCCTGAGAGCCGAGGACACGGCTGTGTATTATTGCGCGAGAGAATGGCTACAATTCAGGTACTACTACGGTATGGACGTCTGGGGCCAAGGGACCACGGTCACCGTCTCCTCA |
| | | | SEQ ID NO: 26911 | SEQ ID NO: 30917 |
| | | AA | DIQMTQSPSSLSASVGDRVTITCRASQGIRKDLGWYQQKPGKAPKRLIYAASSLQSGVPSRFSGSGSGTEFTLTISSLQPEDFATYVCLQHYRYPFTFGPGTKVDFK | QVQLVESGGGVVQPGRSLRLSCAASGFTFSNYGMHWVRQAPGKGLEWVAIIWFDGSNKYYVDSVKGRFTISRDNSKNTLFLQMSSLRAEDTAVYYCAREWLQFRYYYGMDVWGQGTTVTVSS |
| | | | SEQ ID NO: 26912 | SEQ ID NO: 30918 |

FIGURE 50
(Continued)

| | | | | |
|---|---|---|---|---|
| iPS:436193 | 21-225_198A10 | NA | GATATTGTGTTGACCCAGACTCCACTCTCTG<br>TCCGTCACCCCTGGACAGCCGGCCTCCATATC<br>GTGCAAGTCTAGTGACAGCTCCTCTATAGTG<br>ATGGAAGGACCTATTTGTATTGGTACCTGCAG<br>AAACCAGGCCAGCCTCCACAGGTCCTGATCTG<br>TGAGGGTTCCAACCGGTTCTCTGGAGTGCCAG<br>ATAGGTTCAGTGGCAGCGGGTCAGGGACAGA<br>TTTCACACTGAAAATCAGCCGGGTGGAGGCAG<br>GAGATGTTGGGGTTTATTACTGCATGCAAAGT<br>ATACAGCTTCCCTGACGTTCGGCCAAGGGAC<br>CAAGGTGGAAATCAAA<br><br>SEQ ID NO: 26913 | CAGCTGCAGCTGCAGGAGTCGGGCCCAGGACTG<br>GTGAAGCCTTCGGAGACCCTGTCCCTCACCTGCA<br>CTGTCTCTGGTGGCTCCATCAGAAGTTACCACTG<br>GAGTTGGATCGGCAGCCCCCGGGAAGGACT<br>GGAGTGGATTGGGCATATCTATACCAGTAGGAGC<br>ACCAACTACAACCCCTCCCTCAAGAGTCGAGTCA<br>CCATTTCAGTAGACACGTCCAAGAACCAGTTCTC<br>CCTGAAGCTGAGCTCTGTGACCGCCACGGACACG<br>GCCGTGTATTACTGTGCGAGACTCCGGTATAACT<br>GGAACTTCCCTTACTTGACTACTGGGGCCAGGG<br>AACCCTGGTCACCGTCCTCA<br><br>SEQ ID NO: 30919 |
| | | AA | DIVLTQTPLSLSVTPGQPASISCKSSQSLLYSDGR<br>TYLYWYLQKPGQPPQVLICEVSNRFSGVPDRFS<br>GSGSGTDFTLKISRVEAGDVGVYYCMQSIQLPW<br>TFGQGTKVEIK<br><br>SEQ ID NO: 26914 | QLQLQESGPGLVKPSETLSLTCTVSGGSIRSYHWSW<br>IRQPAGKGLEWIGHIYTSRSTNYNPSLKSRVTISVDT<br>SKNQFSLKLSSVTATDTAVYYCARLRYNWNFPYFD<br>YWGQGTLVTVSS<br><br>SEQ ID NO: 30920 |
| iPS:436195 | 21-225_198G10 | NA | GAAATTGTGTTGACGCAGTCTCCAGGCACCCT<br>GTCTTTGTCTCCAGGGGAAAGAGCCACCCTCT<br>CCTGCAGGGCCAGTCAGAGTATTCGCAGCAGC<br>TTCTTAGCCTGGTATCAGCAGAAACCTGGCCA<br>GGCTCCCAGGCTCCTCATCTATGGTGCATCCA<br>GCAGGGCCACTGGCATCCCAGACAGGTTCAGT<br>GGCAGTGGGTCTGGGACAGACTTCACTCTCAC<br>CATCAGCAGACTGGAGCCTGAAGATTTTGCAG<br>TGTATTACTGTCAGCAGTATGGTAACTCACCG<br>TGGGCGTTCGGCCAAGGGACCAAGGTGGAAA<br>TCAAA<br><br>SEQ ID NO: 26915 | CAGGTGCAGCTGCAGGAGTCGGGCCCAGGACTG<br>GTGAAGCCTTCACAGACCCTGTCCCTCACCTGCA<br>CTGTCTCTGGTGGCTCCATCAGCAGTGGTGATTA<br>CTACTGGAACTGGATCCGCCAGCTCCCAGGGAA<br>GGGCCTGGAGTGGATTGGGTACATCTTTACAGT<br>GGGAGCACCTACTACAACCCGTCCCTCAAGAGTC<br>GACTTACCATATCAGTGGACACGTCTAAGAACCA<br>GTTCTCCCTGAAGCTGAGTTCTGTGACTGCCGCG<br>GACACGGCCGTGTATTACTGTGCGAGAGGGGATT<br>ACGATGGTTCGGGGGAGTTATCACTTCTACTACGG<br>TATGGACGTCTGGGGCCAAGGGACCACGGTCAC<br>CGTCTCCTCA<br><br>SEQ ID NO: 30921 |

FIGURE 50
(Continued)

| | | | |
|---|---|---|---|
| iPS:436197 | 21-225_199C2 | AA | EIVLTQSPGTLSLSPGERATLSCRASQSIRSSFLAWYQQKPGQAPRLLIYGASSRATGIPDRFSGSGSGTDFTLTISRLEPEDFAVYYCQQYGNSPWAFGQGTKVEIK<br>SEQ ID NO: 26916 | QVQLQESGPGLVKPSQTLSLTCTVSGGSISSGDYYWNWIRQLPGKGLEWIGYIFYSGSTYNPSLKSRLTISVDTSKNQFSLKLSSVTAADTAVYYCARGDYDGSGSYHFYYGMDVWGQGTTVTVSS<br>SEQ ID NO: 30922 |
| | | NA | GAAATTGTGTTGACGCAGTCTCCAGGCACCCTGTCTTTGTCTCCAGGGGAAAGAGCCACCCTCTCCTGCAGGGCCAGTCAGAGTATTCGCAGCAGCTTCTTAGCCTGGTACCAGCAGAAACCTGGCCAGGCTCCCAGGCTCCTCATCTATGGTGCATCAGCAGGGGCCACTGGCATCCCAGACAGGTTCAGTGGCAGTGGGTCTGGGACAGACTTCACTCTCACCATCAACAGACTGGAGCCTGAAGATTTTGCAGTGTATTACTGTCAGCAGTATGGTAACTCACCGTGGGCGTTCGGCCAAGGGACCAAGGTGGAAATCAAA<br>SEQ ID NO: 26917 | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGATTACTACTGGAACTGGCTCCGCCAGCACCAGGAAGGGCCTGGAGTGGATTGGGTACATCTTTTACAGTGGGAGCACCTACTACAACCCGTCCCTCAAGAGTCGAGTTACCATATCAGTGGACACGTCTATGACCCAGTTCTCCCTGAAGCTGACCTCTGTGACTGCCGCGGACACGGCCGTGTATTACTGTGCGAGAGGGGATTACGATGGTTCGGGGAGTTATCACTACTACGGTATGGACGTCTGGGGCCAAGGGACCACGGTCACCGTCTCCTCA<br>SEQ ID NO: 30923 |
| | | AA | EIVLTQSPGTLSLSPGERATLSCRASQSIRSSFLAWYQQKPGQAPRLLIYGASSRATGIPDRFSGSGSGTDFTLTINRLEPEDFAVYYCQQYGNSPWAFGQGTKVEIK<br>SEQ ID NO: 26918 | QVQLQESGPGLVKPSQTLSLTCTVSGGSISSGDYYWNWLRQHPEKGLEWIGYIFYSGSTYNPSLKSRVTISVDTSMTQFSLKLTSVTAADTAVYYCARGDYDGSGSYHYYGMDVWGQGTTVTVSS<br>SEQ ID NO: 30924 |

FIGURE 50
(Continued)

| | | | | |
|---|---|---|---|---|
| iPS:436199 | 21-225_199E3 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATTTCTCTGCATCCAGTT TGCAAAGGGGGTCCCATCAAGATTCAGCGGC AGTGGATCTGGGACAGAATTCACTCTCACAAT CAGCAGCCTGCAGCCTGAAGATTTTGCAACTT ATTACTGTCTACAGCATAAAAGGTACCCGCTC ACTTTCGGCGGAGGGACCAAGGTGGAGATCA AA<br>SEQ ID NO: 26919 | CAGGTGCAGCTGGTACAGCAGTGGGGCGCAGGACTG TTGAAGCCTTCGGAGACCCTGTCCCTCACCTGCG CTGTCTATGTGGGTCCTTCAGTGGTTACTTCTGG ACCTGGATCCGCCAGCCCCCAGGGAAGGGGCTG GAGTGGATTGGGGAAATCAATCATAGTGGAAGC ACCAACTACAACCGTCCCTCAAGAGTCGCGTCA CCATATCAGTAGACACGTCAAGAACCAGTTCTC CCTGAAGCTGAGCTCTGTGACCGCCGCGACACG GCTGTGTATTACTGTGCGAGAGACTACGGTGCTG ACTACTGGGGCCAGGGAACCCTGGTCGCCGTCTC CGCA<br>SEQ ID NO: 30925 |
| | | AA | DIQMTQSPSSLSASVGDRVTITCRASQGIRNDLG WYQQKPGKAPKRLISSASSLQRGVPSRFSGSGSG TEFTLTISSLQPEDFATYYCLQHKRYPLTFGGGT KVEIK<br>SEQ ID NO: 26920 | QVQLQQWGAGLLKPSETLSLTCAVYGGSFSGYFW TWIRQPPGKGLEWIGEINHSGSTNYNPSLKSRVTISV DTSKNQFSLKLSSVTAADTAVYYCARDYGADYWG QGTLVAVSA<br>SEQ ID NO: 30926 |
| iPS:436201 | 21-225_199C5 | NA | GACATCCAGATGACACAGTCTCCATCCTCACT GTCTGCATCTGTAGGAGACAGAGTCACCATCA CTTGTCGGGCGAGTCAGGACATTAGCAGTAT TTAGCCTGGTTTCAGCAGAAACCAGGGAAAGC CCCTAAGTCCCTGATCTATGCTGCATCCAGTTT GCAAAGTGGGGTCCCATCAAAGGTTCAGCGGCA GTGGATCTGGGACAGATTTCACTCTCACCATC AGCAGCCTGCAGCCTGAAGATTTTGCAGTTA TTACTGCCAACAGTATCTTACTTACCCGCTCAC TTTCGGCGGAGGGACCAAGGTGGAGATCAAA<br>SEQ ID NO: 26921 | CAGGTGCAGCTGGTGGAGTCTGGGGGAGGCGTG GTCCAGCCTGGGAGGTCCCTGAGACTCTCCTGTG CAGCGCTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAAACTATGCAGACTCCGTGAAGGGCCGA TTCACCATCTCCAGAGACAACGCCAAGAACACGC TGTATCTGCAAATGAACAGCCTGAGAGCCGAGG ACACGGCTGTGTATTACTGTGCGAGAGATCAGGG CGTGGCTACTACGGTATGGACGTCTGGGGCCAA GGGACCACGGTCACCGTCCTCA<br>SEQ ID NO: 30927 |

FIGURE 50
(Continued)

| | | | | |
|---|---|---|---|---|
| | | AA | DIQMTQSPSSLSASVGDRVTITCRASQGISKYLA WFQQKPGKAPKSLIYAASSLQSGVPSKFSGSGSG TDFTLTISSLQPEDFAAYYCQQYLTYPLTFGGGT KVEIK<br><br>SEQ ID NO: 26922 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDQGV GYYGMDVWGQGTTVTVSS<br><br>SEQ ID NO: 30928 |
| iPS:436203 | 21-225_199A6 | NA | GACATAGTGATGACGCAGTCTCCAGCCACCCT GTCTGTGTCTCCAGGGGATAGAGCCACCCTCT CCTGCAGGCCCAGTCAGAGTTTAGCAGAAAC TTAGCCTGGTACCAGCAGAAACCTGGCCAGGC TCCCAGGCTCCTCATCTATGGTGCATCCACTA GGGCCACTGGTATCCCAGCCAGGTTCAGTGGC AGTGGGTCTGGGACAGAGTTCACTCTCACCAT CAGCAGCCTGGAGTGTGAAGATTTTGCAGTT ACTACTGTCAGCAGTATAATAACTGGCCGCTC ACTTTCGGCGGAGGGACCAAGGTGGAGATCA AA<br><br>SEQ ID NO: 26923 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAATTATATGGTTTGATGGAAGT AATCAATACTATGCCGACTCCGTGAAGGGCCGAT TCACCATCTCCAGAGACAATTCCAAGAACACGCT GTATCTGCAATTGAACAGCTGAGAGCCGAGGA CACGGCTGTCTATTACTGTGCGGAGAGCCACGGG GTCTACTACGCTATGGACGTCTGGGGCCAAG GGACCACGGTCACCGTCTCCTCA<br><br>SEQ ID NO: 30929 |
| | | AA | DIVMTQSPATLSVSPGDRATLSCRPSQSFSRNLA WYQQKPGQAPRLLIYGASTRATGIPARFSGSGSG TEFTLTISSLECEDFAVYYCQQYNNWPLTFGGGT KVEIK<br><br>SEQ ID NO: 26924 | QVQLVESGGGVVQPGRSLRLSCAASGFTFSNYGM HWVRQAPGKGLEWVAIIWFDGSNQYYADSVKGRF TISRDNSKNTLYLQLNSLRAEDTAVYYCARAHGVY YYAMDVWGQGTTVTVSS<br><br>SEQ ID NO: 30930 |

FIGURE 50
(Continued)

| | | | |
|---|---|---|---|
| iPS:436205 | 21-225_199A7 | NA | GACATCCAGATGACCCAGTCTCCATCCTCCCT GTCTGCATCTGTAGGAGACAGAGTCACCATCA CTTGCCGGGCAAGTCAGGGCATAAGAAACGA TTTAGGCTGGTATCAGCAGAAACCAGGGAAA GCCCCTAAGCGCCTGATCTATGCTGCATCCAG TTTGCAAAGTGGGGTCCATCAAGGTTCAGCG GCAGTGGATCTGGGACAGAATTCACTCTCACA ATCAGCAGCCTGCAGCCTGAAGATTTTGCAAC TTATGTCTGTCTACAACATTATCGTTACCCTTT CACTTTCGGCCCTGGGACCAAAGTGGATTTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAATTATATGTTTGATGAAGT AATAAATACTATGCAGACTCCGTGAAGGGCCGA TTCACCATCTCCAGAGACAATTCCAAGAACACGC TGTTTCTGCAAATGAGCAGCCTGAGAGCCGAGG ACACGGCTGTGTATTACTGTGCGAGAGAATGGCT ACAATTCAGGTACTACTACGGTATGGACGTCTGG GGCCAAGGGACCACGGTCACCGTCTCCTCA |
| | | AA | SEQ ID NO: 26925 | SEQ ID NO: 30931 |
| | | | DIQMTQSPSSLSASVGDRVTITCRASQGIRKDLG WYQQKPGKAPKRLIYAASSLQSGVPSRFSGSGS GTEFTLTISSLQPEDFATYVCLQHYRYPFTFGPGT KVDFK | QVQLVESGGGVVQPGRSLRLSCAASGFTFSNYGM HWVRQAPGKGLEWVAIIWFDGSNKYYADSVKGRF TISRDNSKNTLFLQMSSLRAEDTAVYYCAREWLQF RYYYGMDVWGQGTTVTVSS |
| | | | SEQ ID NO: 26926 | SEQ ID NO: 30932 |
| iPS:436207 | 21-225_199C7 | NA | GAAATTGTGTTGACGCAGTCTCCAGGCACCCT GTCTTTGTCTCCAGGGGAAAGAGCCACCCTCT CCTGCAGGGCCAGTCAGTCAGAGTATAAGGACCAA CTTCTTAGCCTGGTACCAGCAGAAACCTGGCC AGGCTCCCAGGCTCCTCATCTATGGTGCATCC AGCAGGGCCACTGGCATCCCAGACAGGTTCAG TGGCAGTGGGTCTGGGACAGACTTCACTCTCA CCATCAACAGACTGGAGCCTGAAGATTTTGCA GTGTATTACTGTCAGCAGTATGGTAACTCACC GTGGACGTTCGGCCAAGGGACCAAGGTGGAA ATCAAA | CAGGTGCAGCTGCAGGAGTCGGGCCCAGGACTG GTGAAGCCTTCACAGACCCTGTCCCTCACCTGCA CTGTCTCTGGTGGCTCCATCAACAGTGGTGTTA CTACTGGAACTGGATCCGCCAGCACCCAGGGAA GGGCCTGGAGTGGATTGGGTTCATCTTTACAGT GGGAGCACCTACTACAACCCGTCCCTCAAGAGTC GAGTTTCATATCAGTAGACAGTCTAAGAACCA GTCTCCCTGAAGCTGAGCTCTGTGACTGCCGCG GACACGGCCGTGTATTACTGTGCGAGAGGGATT ACGATGGTTCGGGGAGTTATCACTACTATTACGG TATGGACGTCTGGGGCCAAGGGACCACGGTCAC CGTCTCCTCA |
| | | | SEQ ID NO: 26927 | SEQ ID NO: 30933 |

FIGURE 50
(Continued)

| | | | |
|---|---|---|---|
| iPS:436210 | 21-225_199G11 | AA | EIVLTQSPGTLSLSPGERATLSCRASQSIRTNFLAWYQQKPGQAPRLLIYGASSRATGIPDRFSGSGSGTDFTLTINRLEPEDFAVYYCQQYGNSPWTFGQGTKVEIK<br>SEQ ID NO: 26928 | QVQLQESGPGLVKPSQTLSLTCTVSGGSINSGGYYWNWIRQHPGKGLEWIGFIFYSGSTYNPSLKSRVSISVDTSKNQFSLKLSSVTAADTAVYYCARGDYDGSGSYHYYYGMDVWGQGTTVTVSS<br>SEQ ID NO: 30934 |
| | | NA | GAAATTGTGTTGACGCAGTCTCCAGGCACCCTGTCTTTGTCTCCAGGGGAAAGAGCCACCCTCCCTGCAGGGCCAGTGCAGTCAGAGTGTTAGAAGCAGCTACTTAGCCTGGTACCAGCAGAAACCTGGCCAGGCTCCCAGGCTCCTCATCTATGGTGCATTCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTACTACTGTCAGCAGTATGGTAACTCACCGTGGACGTTCGGCCAAGGGACCAAGGTGGAAATCAAA<br>SEQ ID NO: 26929 | CAGGTGCAGCTGCAGGAGTCGGGCCCAGGACTGGTGAAGCCCTCACAGACCCTCACCCTCACCTGCACTGTCTCTGGTGGCTCCATCAGCAGTGGTGGTTACTACTGGAGCTGGATCCGCCAGCACCCAGGGAAGGGCCTGGAGTGGATTGGGAACATCTATTACAGTGGGAGCACCTACTACAACCCGTCCCTCAAGAGTCGAGTTACCATATCAGTAGACACGTCTAAGAACCAGTTCTCCCTGAAGCTGAGCTCTGTGACTGCCGCGGACACGGCCGTGTATTACTGTGCGAGAGGGGATTACTATGGTTCGGGGAGTTATCACAACTACTACGGTTTGGACGTCTGGGGCCAAGGGACCACGGTCACCGTCTCCTCA<br>SEQ ID NO: 30935 |
| | | AA | EIVVTQSPGTLSLSPGERATLSCRASQSVRSSYLAWYQQKPGQAPRLLIYGAFSRATGIPDRFSGSGSGTDFTLTISRLEPEDFAVYYCQQYGNSPWTFGHGTKVEIK<br>SEQ ID NO: 26930 | QVQLQESGPGLVKPSQTLSLTCTVSGGSISSGGYYWSWIRQHPGKGLEWIGNIYSGSTYNPSLKSRVTISVDTSKNQFSLKLSSVTAADTAVYYCARGDYYGSGSYHNYYGLDVWGQGTTVTVSS<br>SEQ ID NO: 30936 |

FIGURE 50
(Continued)

| | | | | |
|---|---|---|---|---|
| iPS:436212 | 21-225_200G1 | NA | GACATCCAGATGACCCAGTCTCCATCCTCCCT GTCTGCATCTGTAGGAGACAGAGTCACCATCA CTTGCCGGGCAAGTCAGAGACATTAGCAGCTAT TTAAATTGGTTTCAGCAGAAACCAGGGAAAGC CCCTAAGCTCCTGATCTATGCTGAGTCCAGTTT ACAAAGTGGGGGTCCCATCAAGGTTCAGTGGCA GTGGATCTGGGACAGATTTCACTCTCACCATC AGCAGTCTGCAACCTGAAGATTTTGCAACTTA TTCCTGTCAACAGAGTTACAGTTCCCCTCCGTG GACGTTCGGCCAAGGGACCAAGGTGGAGTTC AAA | GAGGTGCAACTGTTGGAGTCTGGGGGAGGCTTG GTGCAGCCTGGGGGTCCCTGAGACTCTCCTGTG CAGCCCTCTGATTCACCTTTAGCAGCTATGCCAT GAGCTGGGTCCGCCAGGCTCCAGGGAAGGGCT GGAGTGGGTCTCAGTCATTAGTGGTAGAGGCGGT AATACATTCTACGCAGACTCCGTGAGGGGCCGGT TCACCATCTCCAGAGACAATTCCAAGAACACGCT GTATCTGCAAATGAACAGCCTGAGAGCCGAGGA CACGGCCGTATATTACTGTGCGACGTATAGCA GTGGATGGCTATGATGCTTTTGATGTCTGGGGCC AAGGGACAATGGTCACCGTCTCTTCA |
| | | | SEQ ID NO: 26931 | SEQ ID NO: 30937 |
| | | AA | DIQMTQSPSSLSASVGDRVTITCRASQSISSYLNW FQQKPGKAPKLLIYAESSLQSGVPSRFSGSGSGT DFTLTISSLQPEDFATYSCQQSYSSPPWTFGQGT KVEFK | EVQLLESGGGLVQPGGSLRLSCAASGFTFSSYAMS WVRQAPGKGLEWVSAISGRGGNTFYADSVRGRFTI SRDNSKNTLYLQMNSLRAEDTAVYYCARRIAVDG YDAFDVWGQGTMVTVSS |
| | | | SEQ ID NO: 26932 | SEQ ID NO: 30938 |
| iPS:436214 | 21-225_200F6 | NA | GACATCCAGATGACCCAGTCTCCATCCTCCCT GTCTGCATCTGTAGGAGACAGAGTCACCATCA CTTGCCGGGCAAGTCAGGACAGTCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTTCACTCTCACAA TCAGCAGCCTGCAGCCTGAAGATTTTGCAACT TATCACTGTCTCTACAGCATTATCGTTACCCATTC ACTTTCGGCCCTGGGACCAAAGTGGATATCAA A | CAGGTGCAGCTGGTGGAGTCTGGGGGAGGCGTG GTCCAGCCTGGAAGGTCCCTGAGACTCTCCTGTG CAGCGTCTGATTCACCTTCAGTAGTTATGCAT CACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTATTACTGTACGGTATGACGTCTGG ACAATTTAGGTATTACTGTACGGTATGACGTCTGG GGCCAAGGGACCACGGTCACCGTCTCCTCA |
| | | | SEQ ID NO: 26933 | SEQ ID NO: 30939 |

FIGURE 50
(Continued)

| | | | |
|---|---|---|---|
| iPS:436216 | | AA | DIQMTQSPSSLSASVGDRVTITCRASQDIRNDLG WYQQKPGKAPKRLIYAASSLQSGVPSRFSGSGS GTEFTLTISSLQPEDFATYHCLQHYRYPFTFGPGT KVDIK<br>SEQ ID NO: 26934 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCTREWLQF RYYYGMDVWGQGTTVTVSS<br>SEQ ID NO: 30940 |
| | | NA | GAAATTGTGCTGACTCAGTCTCCAGACTTTCA GTCTGTGACTCCAAAGGAGAAAGTCACCATCA CCTGCCGGGCCAGTCAGAACATTGGTAATACC TTGCACTGGTACCAGCAGAAACCAGATCAGTC TCCTAAGCTCCTCATCAAGTATGCTCCCAGTC CTTCTCAGGGTCCCCTGAGGTTCAGTGGCA GTGGGTCTGGGACAGATTTCATCCTCACCATC AATAGCCTGGAAGCTGAAGATGCTGCAACGTA TTACTGTCATCAGAGTGGTAGTTTACCTCAGA CGTTCGGCCAAGGGACCAAGGTGGAAATCAA A<br>SEQ ID NO: 26935 | CAGGTGCAGCTGCAGGAGTCGGGCCAGGACTG GTGAAGCCTTCACAGACCCTGTCCCTCACCTGCA CTGTCTCTGGTGGCTCCATCAGCAGTGGTGGTTA CTACTGGAGCTGGATCCGCCAGCACCCAGGGAA GGGCTGGAGTGGATTGGGTACATCTTTTACAGT GGGAGCACCAACTACAACCCGTCCCTCAGGAGT CGAGTTACCATATCAGTAGACACGTCTAAGAACC AGTTCTCCCTGAAACTGAGTTCTGTGACTGCCGC GGACACGGCCGTGTATTACTGTGCGAGAGCCGG GTATAACTGGAACAACGGTATGACGTCTGGGG CCAAGGGACCACGGTCACCGTCTCCTCA<br>SEQ ID NO: 30941 |
| | 21-225_200B7 | AA | EIVLTQSPDFQSVTPKEKVTITCRASQNIGNTLH WYQQKPDQSPKLLIKYASQSFSGVPSRFSGSGSG TDFILTINSLEAEDAATYYCHQSGSLPQTFGQGT KVEIK<br>SEQ ID NO: 26936 | QVQLQESGPGLVKPSQTLSLTCTVSGGSISSGGYYW SWIRQHPGKGLEWIGYIFYSGSTNYNPSLRSRVTIS VDTSKNQFSLKLSSVTAADTAVYYCARAGYNWNN GMDVWGQGTTVTVSS<br>SEQ ID NO: 30942 |

FIGURE 50
(Continued)

| | | | | |
|---|---|---|---|---|
| iPS:436218 | 21-225_200G7 | NA | GACATCGTGATGACCCAGTCTCCAGACTCCC GACTGCGTCTCTGGGGGAGAGGGCCACGTCA AATGCAAGTCCAGCCAGTGTTTACACAGC TCCAACAATAACAACTACTTAGCTTGGTACCA GCAGAAACCAGGACAGCCTCCTAAGCTGCTCA TTTACTGGGCATCTACCCGGGAATCCGAGTC CCTGACCGATTCAGTGGCAGCGGGTCTGGGAC AGATTTCACTCTCGCCATCAGCAGCTGCAGG CTGAAGATGTGGCGGTTTATTACTGTCAGCAA TATTATAATACTCCTCCGACATTCGGCCAAGG GACCAAGGTGGAAATCAAA<br><br>SEQ ID NO: 26937 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGATGCGGCAGGCCACTGGTCAAGGC TTGAGTGGATGGGATGGATGCACCTTAACAGTGG TAACACAGGCTATGCACCGAAGTTCCAGGGCAG AGTCACCATGACCAGGGACACCTCCATAAGCAC AGCCTTCATGGAGCTGAGCAGCCTGAGATCTGAG GACACGGCCGTGTACTGTGCCTATAGCGGTG GCTGGTACGTGTTCGACCCTGGGGCCAGGGAAC CCTGGTCACCGTCCTCA<br><br>SEQ ID NO: 30943 |
| | | AA | DIVMTQSPDSPTASLGERATVKCKSSQSVLHSSN NNNYLAWYQQKPGQPPKLLIYWASTRESGVPD RFSGSGSGTDFTLAISSLQAEDVAVYYCQQYYN TPPTFGQGTKVEIK<br><br>SEQ ID NO: 26938 | QVQLVQSGAEVKKPGASVKVSCKASGYTFTNYDIN WMRQATGQGLEWMGWMHLNSGNTGYAPKFQGR VTMTRDTSISTAFMELSSLRSEDTAVYYCAYSGGW YVFDPWGQGTLVTVSS<br><br>SEQ ID NO: 30944 |
| iPS:436220 | 21-225_200F8 | NA | GAAATTGTGCTGACTCAGTCTCCAGACTTTCA GTCTGTGACTCCAAAGGAGAAAGTCACCATCA CCTGCCGGCCAGTCAGAGTCAGATTAGTAAC TTACACTGGTACCAGCAGAAACCAGATCAGTC TCCGAAACTCCTCATCAAGTCTGCTCCCAGTC CTTCTCAGGGGTCCCCTCGAGGTTCAGTGGCA GTGGATCTGGGACAGATTTCACCCTCACCATC AATAGCCTGGAAACTGAAGATGCTGCAACGTA TTACTGTCAGCAGAGTAGTAGTTTACCGTGGA CGTTCGGCCAAGGGACCAAGGTGGAAATCAA A<br><br>SEQ ID NO: 26939 | CAGGTGCAGCTGCAGGAGTCGGGCCCAGGACTG GTGAAGCCTTCGGAGACCCTGTCCCTCACCTGCA CTGTCTCTGGTGGCTCCATCAATAATTACTACTG GAGCTGGATCCGGCAGCCCGCCGGGAAGGGACT GGAGTGGATTGGGCGTATCTATACCAGTGGGAGC ACCAACTACAACCCCTCCCTCAAGAGTCGAGTCA CCATGTCAGTAGACACGTCAAGAACCAGTTCTC CTGAAGCTGAGCTCTGTGACCGCCGGACACG GCCGTGTATTACTGTGCGAGAGATCGGGATACT ATGGCTACTACGGTATGGACGTCTGGGGCCAAG GGACCACGGTCACCGTCCTCA<br><br>SEQ ID NO: 30945 |

FIGURE 50
(Continued)

| | | | | |
|---|---|---|---|---|
| | | AA | EIVLTQSPDFQSVAPKEKVTITCRASQSIGSNLHW YQQKPDQSPKLLIKSASQSFSGVPSRFSGSGSGT DFTLTINSLETEDAATYYCQQSSSLPWTFGQGTK VEIK | QVQLQESGPGLVKPSETLSLTCTVSGGSINNYYWS WIRQPAGKGLEWIGRIYTSGSTNYNPSLKSRVTMS VDTSKNQFSLKLSSVTAADTAVYYCARDRGYYGY YGMDVWGQGTTVTVSS |
| | | | SEQ ID NO: 26940 | SEQ ID NO: 30946 |
| iPS:436222 | 21-225_200C9 | NA | GACATCCAGATGACCCAGTCTCCATCCTCCCT GTCTGCATCTGTTGGAGACAGAGTCACCATCA CTTGCCGGGCAACTCAGGGCATTAGAAAAGAT TTAGGCTGGTATCAGCAGAAACCAGGGAAAG CCCCTAAGCGCCTGATCCATACTGCATCCAGT TTGCAAAGTGGGGTCCCATTAAGGTTCAGCGG CAGTGGATCTGGGACAGAATTCACTCTCACAA TCAGCAGCCTGCAGCCTGAAGATTTTGCAACT TATTACTGTCTACAGACATAATAGTTACCCGTG GACGTTCGGCCAAGGGACCAAGGTGGAAATC AAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGCAT GCACTGGGTCCGCCAGGCTCCAGGCAAGGGCT GGAGTGGGTGGCAGTTATATCGACTCCGTGAAGGGCCGAT TATAAAACTATATAGACTCCGTGAAGGGCCGAT TCACCATCTCCAGAGACAATTCCAAGAACACGCT GTATCTGCAAATGAACAGCCTGAGAGCTGAGGA CACGGCTGTGTTTACTGTGCGAGAGGTACCAC GGGTACTACTACGGTGTGGACGTCTGGGGCCAA GGGACCACGGTCACCGTCTCCTCA |
| | | | SEQ ID NO: 26941 | SEQ ID NO: 30947 |
| | | AA | DIQMTQSPSSLSASVGDRVTITCRATQGIRKDLG WYQQKPGKAPKRLIHTASSLQSGVPLRFSGSGS GTEFTLTISSLQPEDFATYYCLQHNSYPWTFGQG TKVEIK | QVQLVESGGGVVQPGRSLRLSCAASGFTFSSYGMH WVRQAPGKGLEWVAVISYDGGYKNYIDSVKGRFT ISRDNSKNTLYLQMNSLRAEDTAVFYCARGTHGYY YGVDVWGQGTTVTVSS |
| | | | SEQ ID NO: 26942 | SEQ ID NO: 30948 |

FIGURE 50
(Continued)

| | | | |
|---|---|---|---|
| iPS:436226 | 21-225_200F10 | NA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGATTA CTACTGGAACTGGCTCCGCCAGCACCCAGAGAA GGGCCTGGAGTGGATTGGGTACATCTTTACAGT GGGAGCACCTACTACAACCGTCCCTCAAGAGTC GAATTACCATATCAGTGGACACGTCTATGACCCA GTTCTCCCTGAAGCTGACCTCTGTGACTGCCGCG GACACGGCCGTGTATTACTGTGCGAGAGGGGATT ACGATGGTTCGGGGAGTTATCACTACTACGG TATGGACGTCTGGGGCCAAGGGACCACGGTCAC CGTCTCCTCA<br>SEQ ID NO: 30949 |
| | | AA | EIVLTQSPGTLSLSPGERATLSCRASQNIRSSFLA WYQQKPGQAPRLLIYGASSRATGIPDRFSGSGSG TDFTLTINRLEPEDFAVYYCQQYGNSPWAFGQG TKVEIK<br>SEQ ID NO: 26943 | QVQLQESGPGLVKPSQTLSLTCTVSGGSISSGDYYW NWLRQHPEKGLEWIGYIFYSGSTYYNPSLKSRITISV DTSMTQFSLKLTSVTAADTAVYYCARGDYDGSGS YHYYGMDVWGQGTTVTVSS<br>SEQ ID NO: 30950 |
| iPS:436228 | 21-225_200F12 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAGAG CCCCTAAGCGCCTGATCTATTCTGCATCCAGTT TGCATACTGGGGTCCCATCAAGGTTCAGCGGC AGTGGATCTGGGACAGCCTGGGACACTCACAAT CAGCAGCCTGCAGCCTGAAGATTTTGCAACTT ATTACTGTCTACAGCATAAGAGTTACCCGCTC ACTTTCGGCGGAGGGACCAAGGTGGAGATCA AA<br>SEQ ID NO: 26944 | CAGGTGCAGCTGCAGGAGTCAGGGGGCGGCAGGACTG TTGAAGCCTTCACAGAGACCCTGTCCCTCACCTGCG CTGTCTATGGTGGGTCCTTCAGTGGTTACTTCTGG ACCTGGATACGCCAGCCCCAGGGAAGGGACTG GAGTGGATTGGGAAATCAGTCATAGTGGAAGC ACCAACTACAACCCGTCCCTCAAGAGTCGAGTCA CCATATCAGTAGACACGTCCAAGAACCAGTTCTC CCTGAAGTTGAGCTCTGTGACCGCCGCGACAC GGCTGTGTATTACTGTGCGAGGGACTACGGGGCG GACTACTGGGGCCAGGGAACCCTGGTCACCGTCT CCTCA<br>SEQ ID NO: 30951 |
| | | NA | SEQ ID NO: 26945 | |

FIGURE 50
(Continued)

| | | | | |
|---|---|---|---|---|
| | | AA | DIQMTQSPSSLSASVGDRVTITCRASQGIRNDLG WYQQKPGRAPKRLIYSASSLHTGVPSRFSGSGSG TEFTLTISSLQPEDFATYYCLQHKSYPLTFGGGT KVEIK<br><br>SEQ ID NO: 26946 | QVQLQQWGAGLLKPSETLSLTCAVYGGSFSGYFW TWIRQPPGKGLEWIGEISHSGSTNYNPSLKSRVTISV DTSKNQFSLKVSSVTAADTAVYYCARDYGADYW GQGTLVTVSS<br><br>SEQ ID NO: 30952 |
| iPS:436230 | 21-225_201A1 | NA | GACATCCAGATGACCCAGTCTCCATCCTCCCT GTCTGCATCTGTAGGAGACAGAGTCACCATCA CTTGCCGGGCAAGTCAGGGCATTAGGAATGAT TTAGGCTGGTATCAGCAGAAACCAGGAGAAAG CCCCTAAGCGCCTGATCTATTCTGCATCCATTT TACAAAGGGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATAAAAGTTACCCTCTC ACTTTCGGCGGAGGGACCAAGGTGGAGGTCA AA<br><br>SEQ ID NO: 26947 | CAGGTGCAGTCTACAGCAGTGGGGCGCAGGACTG TTGAAACCTTCGGAGACCTGTCCCTCACCTGCG CTGTCACTGGTGGTCCTTCAGTGGTTACTTCTGG ACCTGGATCCGCCAGCCCCCAGGGAAGGGGCTG GAGTGGATTGGGGAAATCAGTCATAGTGGACGC ACCAACTACAACCCGTCCCTCAAGAGTCGAGTCA CCATATCAGGAGACACGTCCAAGAACCAGTTCTC CCTGAAGCTGAGCTCTGTGACCGCCGCGGACACG GCTGTGTATTACTGTGCGAGGGACTACGGGGCGG ACTACTGGGGCCAGGGAACCCTGGTCACCGTCTC CTCA<br><br>SEQ ID NO: 30953 |
| | | AA | DIQMTQSPSSLSASVGDRVTITCRASQGIRNDLG WYQQKPGKAPKRLIYSASILQRGVPSRFSGSGSG TEFTLTISSLQPEDFATYYCLQHKSYPLTFGGGT KVEVK<br><br>SEQ ID NO: 26948 | QVQLQQWGAGLLKPSETLSLTCAVTGGSFSGYFWT WIRQPPGKGLEWIGEISHSGRTNYNPSLKSRVTISG DTSKNQFSLKLSSVTAADTAVYYCARDYGADYWG QGTLVTVSS<br><br>SEQ ID NO: 30954 |

FIGURE 50
(Continued)

| | | | |
|---|---|---|---|
| iPS:436232 | 21-225_201E1 | NA | GAAATTGTGTTGACGCAGTCTCCAGACACCCT<br>GTCTTTGTCTCCAGGGGAAAGAGCCACCCTCT<br>CCTGCAGGGCCAGTCCAGTATTAACAGCGGC<br>TTCTTAGCCTGGTACCAGCAGAAACCTGGCCA<br>AGCTCCCAGGCTCCTCATCTATGGTGCATCCA<br>GCAGGGCCACTGGCATCCCAGACAGGTTCAGT<br>GGCAGTGGGTCTGGGACAGACTTCACTCTCAC<br>CATCAGCAGACTGGAGCCTGAAGATTTTGCAA<br>TGTTTCACTGTCACCAGTATGATGAGACCTCACCG<br>TGGACGTTCGGCCAAGGGACCAAGGTGGAGA<br>TCAAA<br>SEQ ID NO: 26949 | CAGGTGCAGCTACAGCAGTGGGGCGCAGGACTG<br>TTGAAGCCTTCGGAGACCCTGTCCCTCACCTGCG<br>CTGTCTTTGATGGTCCTTCAGTCTTACTACTGG<br>AGCTGGATCCGCCAGCCCCCAGGGAAGGGGCTG<br>GAGTGGATTGGGGAAGTCAATCATAGTGGAAGC<br>ACCAACTACAACCGTCCTCAAGAGTCGAGTCA<br>CCATATCAGTAGACACGTCAAGAACCAGTTCTC<br>CCTGAAGCTGAGCTCTGTGACCGCCGCGACACG<br>GCTGTGTATTACTGTGCGAGAGACTACGGGGGTT<br>TAGACTACTGGGGCCAGGGAGCCCTGGTCACCGT<br>CTCCTCA<br>SEQ ID NO: 30955 |
| | | AA | EIVLTQSPDTLSLSPGERATLSCRASPSINSGFLA<br>WYQQKPGQAPRLLIYGASSRATGIPDRFSGSGSG<br>TDFTLTISRLEPEDFAMFHCHQYETSPWTFGQGT<br>KVEIK<br>SEQ ID NO: 26950 | QVQLQQWGAGLLKPSETLSLTCAVFDGSFSPYYWS<br>WIRQPPGKGLEWIGEVNHSGSTNYNPSLKSRVTISV<br>DTSKNQFSLKLSSVTAADTAVYYCARDYGGLDYW<br>GQGALVTVSS<br>SEQ ID NO: 30956 |
| iPS:436234 | 21-225_51E3 | NA | CAGTCTGTGCTGACTCAGCCACCCTCAGCGTC<br>TGGGACCCCCGGGCAGAGGGTCACCATCTCTT<br>GTTCTGGAAGCAACTCCAACATGGAAGTAAT<br>ATTGTAACCTGGTACCAGCAGCTCCCAGGAAC<br>GGCCCCCCAAACTCCTCATCTATAGTAATGATC<br>AGCGGCCCTCAGGGGTCCCTGACCGATTCTCT<br>GGCTCCAAGTCTGGCACCTCAGCCTCCCTGGC<br>CATCAGTGGGCTCCAGTCTGAGGATGAGGCTG<br>ATTATTACTGTACAGCATGGGATGACAGCCTG<br>AATGGTTGGGTGTTCGGCGGAGGTACCACGCT<br>GACCGTCCTA<br>SEQ ID NO: 26951 | CAGGTTCAGCTGGTGCAGTCTGGAGCTGAGGTGA<br>AGAAGCCTGGGGCCTCAGTGAAGGTCTCCTGCA<br>AGGCTTCAGGTTACACCTTTAACACAGTATGTAT<br>CAGCTGGGTGCGACTGGCCCCTGGACAAGGGCTT<br>GAGTGGATGGGATGGATCAGCGTTATAATGGTA<br>ACACAAAGAATGCACAGAGGTTCCAGGGCAGAG<br>TCACCATGACCACAGACACATCCACGAGCACCG<br>CCTACATGGAGCTGAGGAGCCTGAGATCTGACG<br>ACACGGCCGTTTATTACTGTGCGAGACACGATTT<br>TTGGAGTGGTTATTATAAGGTATGGACGTCTGG<br>GGCCAAGGGACCACGGTCACCGTCCTCA<br>SEQ ID NO: 30957 |

FIGURE 50
(Continued)

| | | | |
|---|---|---|---|
| | | AA | QSVLTQPPSASGTPGQRVTISCSGSGNSNIGSNIVT WYQQLPGTAPKLLIYSNDQRPSGVPDRFSGSKS GTSASLAISGLQSEDEADYYCTAWDDSLNGWVF GGGTTLTVL<br>SEQ ID NO: 26952 | QVQLVQSGAEVKKPGASVKVSCKASGYTFNSYGIS WVRLAPGQGLEWMGWISAYNGNTKNAQRFQGRV TMTDTSTSTAYMELRSLRSDDTAVYYCARHDFW SGYYKGMDVWGQGTTVTVSS<br>SEQ ID NO: 30958 |
| iPS:436236 | 21-225_201F7 | NA | GAAATAGTGATGACGCAGTCTCCAGGCACCCT GTCTGTGTCTCCAGGGGAAAGAGCCACCCTCT CCTGCAGGGCCAGTCAGTCTCAGAATATTAAAACAAC TTAGCCTGGTACCAGCAGAAACCTGGCCAGGC TCCCAGGCTCCTCATCTTTGTGCATCCACCAG GGCCACTGGTATCCCAGCCAGGTTCAGTGGCA GTGGGTCTGGGACAGAGTTCACTCTCACCATC AGCAGCCTGCAGTCTGAAGATTTTGCAGTTTA TTACTGTCAGCAGTTTATAACTGGCTGTGCA GTTTTGGCCAGGGGACCAAGCTGGAGCTCAAA | CAGGTACACAGCTGCAGCAGTCAGGTCCAGGACTG GTGAAGCCCTGCAGACCCTCACTCACCTGTG CCATCTCCGGGACAGTGTCTCTAGCAACAGTGC TGCTTGGAACTGGATCAGGCAGTCCCATCGAGA GGCCTTGAGTGGCTGGAAGGACATACTACAGG TCCAAGTGGTATAATTATTATGAAGTATCTGTGA GAAGTCGAATAACCATCAACCAGACACATCCA AGAACCAGTTCTCCCTGCAGCTGAACTCTGTGAC TCCCGAGGACACGGCTGTATATTTCTGTGCGAGA GATCAACGGTACTACGGTATGGACGTCTGGGGCC AAGGGACCACGGTCACCGTCTCCTCA<br>SEQ ID NO: 30959 |
| | | AA | EIVMTQSPATLSVSPGERATLSCRASQNIKNNLA WYQQKPGQAPRLLFGASTRATGIPARFSGSGSG TEFTLTISSLQSEDFAVYYCQQFYNWLCSFGQGT KLELK<br>SEQ ID NO: 26954 | QVQLQQSGPGLVKPSQTLSLTCAISGDSVSSNSAA WNWIRQSPSRGLEWLGRTYYRSKWYNYEVSVRS RITINPDTSKNQFSLQLNSVTPEDTAVYFCARDQRY YGMDVWGQGTTVTVSS<br>SEQ ID NO: 30960 |

FIGURE 50
(Continued)

| | | | | |
|---|---|---|---|---|
| iPS:436238 | 21-225_201B2 | NA | GAAATTGTGTTTGACGCAGTCTCCAGGCACCCTGTCTTTGTCTCCAGGGGAAAGAGCCACCCTCCTGCAGGGCCAGTCAGAGTGTTAGCAGCAACTACTTAGCCTGGTATCAGCAGAGACCTGGCCAGGCTCCCAGACTCCTCATCTATGGTGCATCAGCAGGGCCACTGGCATCCCAGACAGATTCAGTGGCAGTGGGTCTGGGACAGACTTCACTCTCACCATCAGCAGACTGGAGCCTGAAGATTTTGCAGTGTATTTCTGTCAGCAGTATGAAAACTCACCGTGGACGTTCGGCCAAGGGACCAAGGTGGAAATCAAA | CAGGTGCAGCTACAGCAGTGGGGCGCAGGACTGTTGAAGCCTTCGGAGACCCTGTCCCTCACCTGCGCTGTCTTTGGTGGGTCCATCAGTAGTTACTACTGGACCTGGATCCGCCAGCCCCCAGGGAAGGGGCTGGAGTGGATTGGGGAAATCAATCATAGTGGAAGCACCAACTACAACCCGTCCCTCAAGAGTCGAGTCACCATATCAGTAGACACGTCCAAGAACCAGTTCTCCCTGAAGCTGAGCTCTGTGACCGCCGCGGACACGGCTGTGTATTACTGTGCGAGGGACTATGGTGTCTTTGATTACTGGGGCCAGGGAACCCTGGTCACCGTCTCCTCA |
| | | | SEQ ID NO: 26955 | SEQ ID NO: 30961 |
| | | AA | EIVLTQSPGTLSLSPGERATLSCRASQSVSSNYLAWYQQRPGQAPRLLIYGASSRATGIPDRFSGSGSGTDFTLTISRLEPEDFAVYFCQQYENSPWTFGQGTKVEIK | QVQLQQWGAGLLKPSETLSLTCAVFGGSISVYYWTWIRQPPGKGLEWIGEINHSGSTNYNPSLKSRVTISVDTSKNQFSLKLSSVTAADTAVYYCARDYGVFDYWGQGTLVTVSS |
| | | | SEQ ID NO: 26956 | SEQ ID NO: 30962 |
| iPS:436240 | 21-225_201E8 | NA | GAAATTGTGCTGACTCAGTCTCCAGCCTTCAGTCTGTGACTCCAAAGGAGAAAGTCACCATCACCTGCCGGGCCAGTCAGAACATTGGTGTAGTTTACACTGGTACCAGCAGAAACCAGATGCTTCCCAGTTCCAAAACTCCTCATCAAGTATGCTTCCAGTCCTTCTCAGGGGTCCCCTCGAGTTCAGTGGCAGTGGATCTGGGACAAATCTGAAGATGTGAAGATGCTGTAACGTCAATAGCCTGTCATCAGAGTGAAGTTACCGCTCACTTTCGGCGGAGGGACCAAGGTAGAGATCAAAGA | CAGGTGCAGCTGGTACAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGGATGGATCGACACTAACAGTGGCACAAACTATCCACAGGAAGTTTCAGGGCAGGGTCACCATGACCAGGGACACGTCCATCAGCACAGCCTACATGGAACTGAGCAGGCTGAGATCTGACGACACGGCCGTGTTTACTGTGCGAAAGATCAAGGGTATAACTGGAACTCTTTTGACTACTGGGGCCAAGGGAACCCTGGTCACCGTCTCCTCA |
| | | | SEQ ID NO: 26957 | SEQ ID NO: 30963 |

FIGURE 50
(Continued)

| | | AA | EIVLTQSPAFQSVTPKEKVTITCRASQNIGRSLHW YQQKPDQSPKLLIKYASQSFSGVPSRFSGSGSGT NFTLTINSLEAEDAVTYYCHQSRSLPLTFGGGTK VEIR<br><br>SEQ ID NO: 26958 | QVQLVQSGAEVKKPGASVKVSCKASGYTFTGYYM HWVRQAPGQGLEWMGWIDPNSGGTNYPQKFQGR VTMTRDTSISTAYMELSRLRSDDTAVFYCAKDQGY NWNSFDYWGQGTLVTVSS<br><br>SEQ ID NO: 30964 |
|---|---|---|---|---|
| iPS:436242 | 21-225_201A10 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAGAG CCCCTAAGCGCCTGATCTATTCTACATCCAGTT TGCATTCTGGGGTCCCATCAAGGTTCAGCGGC AGTGGATCTGGGACAGAATTCACTCTCACAAT CAGCAGCCTGCAGCCTGAAGATTTTGCAACTT ATTACTGTCTACAGCATAATAGTTACCCGCTC ACTTTCGGCGGAGGGACCAAGGTGGAGATCA AA<br><br>SEQ ID NO: 26959 | CAGGTGCAGTCTACAGCAGTGGGGCGCAGGACTG TTGAAGCCTTCGGAGACCGTCCCTCACCTGCG CTGTCTATGTGGGTCCTTCAGTGGTTACTTCTGG ACCTGGATACGCCAGCCCCAGGGAAGGGACTG GAGTGGATTGGGAAATCAGTCATAGTGGAAGC ACCAACTACAACCCGTCCCTCAAGAGTCGAGTCA CCATATCAGTAGACACGTCCAAGAACCAGTTCTC CCTGAAGGTGAACTCTGTGACCGCCGCGGACAC GGCTGTGTATTACTGTGCGAGGGACTACGGGGCG GACTACTGGGGCCAGGGAACCCTGGTCACCGTCT CCTCA<br><br>SEQ ID NO: 30965 |
| | | AA | DIQMTQSPSSLSASVGDRVTITCRASQGIRNDLG WYQQKPGRAPKRLIYSTSSLHSGVPSRFSGSGSG TEFTLTISSLQPEDFATYYCLQHNSYPLTFGGGT KVEIK<br><br>SEQ ID NO: 26960 | QVQLQQWGAGLLKPSETLSLTCAVYGGSFSGYFW TWIRQPPGKGLEWIGEISHSGSTNYNPSLKSRVIISV DTSKNQFSLKVNSVTAADTAVYYCARDYGADYW GQGTLVTVSS<br><br>SEQ ID NO: 30966 |

FIGURE 50
(Continued)

| | | | | |
|---|---|---|---|---|
| iPS:436244 | 21-225_201H10 | NA | GACATCCAGATGACCCAGTCTCCATCCTCCCT GTCTGCATCTGTTGGAGACAGAGTCACCATCA CTTGCCGGGCAAGTCACAACATTAACAGCTAT TTAAATTGGTATCAGCAGAAATCAGGAAAGC CCCTAAACTCCTAATCTATGCTGCATCCAGTTT GCAAAGTGGGGTCCCGTCAAGGTTCAGTGGCA GTGGATCTGGGACAGATTTCACTCTCACCTTC AGTAGTCTACAACCTGAAGATTTTGCAACTTA CTACTGTCAACAGAGTTACAGTTTCCGCTCA CTTTCGGCGGAGGGACCAAGGTGGAGATGAG G | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TCCACTGGGTGCGACAGCCCCTGGACAAGGC TTGAGTGGATGGCATGGATCAACCCTAATAGTGG TGGCACAAACTATGCACAGAAGTTTCAGGGCAG GGTCACCATGACCAGGGACACGTCCATCACCAC AACCTACATGGAGCTGAGCAGGCTGAGATCTGA CGACACGGCCGTGTATTACTGTGCGAGAGGATAC AGCTATGGTTACAACTGGTTCGACCCCTGGGGCC AGGGAACCCTGGTCACCGTCCTCA |
| | | | SEQ ID NO: 26961 | SEQ ID NO: 30967 |
| | | AA | DIQMTQSPSSLSASVGDRVTITCRASHNINSYLN WYQQKSGKAPKLLIYAASSLQSGVPSRFSGSGS GTDFTLTFSSLQPEDFATYYCQQSYSFPLTFGGG TKVEMR | QVQLVQSGAEVKKPGASVKVSCKASGYTFTGYYIH WVRQAPGQGLEWMAWINPNSGGTNYAQKFQGRV TMTRDTSITTYMELSRLRSDDTAVYYCARGYSYG YNWFDPWGQGTLVTVSS |
| | | | SEQ ID NO: 26962 | SEQ ID NO: 30968 |
| iPS:436246 | 21-225_201G6 | NA | GATATTGTGATGACTCAGTCTCCACTCTCCCTG CCCGTCACCCCTGGAGAGCCGGCCTCCATCTC CTGCAGGTCTAGTCAGAGCCTCCTCCATAATA ATAGATACAACCATTTGGATTGGTACCTGCAG AAGCCAGGACAGTCTCCACAGCTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTGGAGGCTGA GGATGTTGGGGTTTATTACTGCATGCAAGCTC TACAAACTCCCACTTTCGGCGGAGGGACCAAG GTGGAGATCAAA | GAGGTGCAGCTGTTGGAGTCTGGGGGAGGCTTG GTACAGCCTGGGGGGTCCCTGAGACTCTCCTGTG TAGCCTCTGGATTCACCTTTAGCAGCTATGCCAT GAGCTGGGTCCGCCAGGCTCCAGGGAAGGGGCT GGAGTGGGTCTCAACTATTAGTAGTGGTAGTGGTT AGAACATACTACGCAGACTCCGTGAAGGGCCGG TTCACCATCTCCAGAGACAATTCCAAGAACACGC TGTTTCTGCAAATGAACAGCCTGAGAGCCGAGG ACACGGCCGTGTATTACTGTGCGAAAGGGGAG CTAGGAGCAGTGGTCGTTCCACTTTGACTACTG GGGCCAGGGAACCCTGGTCACCGTCCTCTCA |
| | | | SEQ ID NO: 26963 | SEQ ID NO: 30969 |

FIGURE 50
(Continued)

| | | | |
|---|---|---|---|
| iPS:436248 | 21-225_202A3 | AA | DIVMTQSPLSLPVTPGEPASISCRSSQSLLHNNRY NHLDWYLQKPGQSPQLLIYLGSNRASGVPDRFS GSGSGTDFTLKISRVEAEDVGVYYCMQALQTPT FGGGTKVEIK<br>SEQ ID NO: 26964 |
| | | AA | EVQLLESGGGLVQPGGSLRLSCVASGFTFSSYAMS WVRQAPGKGLEWVSTISGSGVRTYYADSVKGRFTI SRDNSKNTLFLQMNSLRAEDTAVYYCAKGGARSS GWFHFDYWGQGTLVTVSS<br>SEQ ID NO: 30970 |
| | | NA | GACATCCAGATGTCCCAATCTCCATCCTCCCT GTCTGCATCTGTTGGAGACAGAGTCACCATCA CTTGCCGGGCAAGTCAGGGACATTAGAAATGAT TTAGGCTGGTATCAGCAGAAACCAGGAAAG CCCCTAAGCGCCTGATCTGTGCTGCATCCAGG TTGCAAAGTGGGGTCCCATCAAGGTTCAGCGG CAGTGGATCTGGGACAGATTCACTCTCACAA TCAGCAGCCTGCAGCCTGAAGATTTTGCAATT TATTACTGTCTACAGACATCATGACTACCCATTC ACTTTCGGCCCTGGGACCAAAGTGGATATCAA A<br>SEQ ID NO: 26965 |
| | | NA | CAGGTGCAGCTGGAGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGACAGGCCACAGGACAAGGGC TTGAGTGGCTGGGATGGATGAACCCTAAGAGAG GTAACACAGGCTATGCACAGAAGTTCCAGGGCA GAGTCACCATGACCAGGAATACCTCCATAAGCA CAGCCCACATGGAGCTGAGCAGCCTGAGATCTG AGGACACGGCCGTGTATTACTGTGCGAGAGGAA GGTATAGCAGGGAGGAGATTACTACTACTATTATGA TATGGACGTCTGGGGCCAAGGGACCACGGTCAC CGTCTCCTCA<br>SEQ ID NO: 30971 |
| | | AA | DIQMSQSPSSLSASVGDRVTITCRASQGIRNDLG WYQQKPGKAPKRLICAASRLQSGVPSRFSGSGS GTEFTLTISSLQPEDFAIYYCLQHHDYPFTFGPGT KVDIK<br>SEQ ID NO: 26966 | QVQLEQSGAEVKKPGASVKVSCKASGYTFTSYDIN WVRQATGQGLEWLGWMNPKRGNTGYAQKFQGR VTMTRNTSISTAHMELSSLRSEDTAVYYCARGRYS REDYYYYDMDVWGQGTTVTVSS<br>SEQ ID NO: 30972 |

FIGURE 50
(Continued)

| | | | | |
|---|---|---|---|---|
| iPS:436250 | 21-225_201A4 | NA | GAAATAGTGATGACGCAGTCTCCAGCCACCCT GTCTGTGTCTCCAGGGGAAAGAGCCACCCTCT CCTGCAGGTCCAGTCACCAGCAGAATATTAAAAGCAAC TTAGCCTGGTACCAGCAGAAACCTGGCCAGGC TCCCAGGCTCCTCATCTTTGGTGCATCCACCAG GGCCACTGGTATCCCAGCCAGTTCAGTGGCA GTGGGTCTGGGACAGAGTTCACTCTCACCATC AGCAGCCTGCAGTCTGAAGATTTTGCAGTTTA TTACTGTCAGCAGTTTTATAACTGGCTGTGCA GTTTTTGGCCAGGGGACCAAGCTGGAGCTCAAA | CAGGTACAGCTGCAGCAGTCAGGTCCAGGACTG GTGAAGCCCTCGCAGACCCTCTCACTCACCTGTG CCATCTCCGGGGACAGTGTCTCTAGCAACAGTGC TGCTTGGAACTGGATCAGGCAGTCCCCATCGAGA GGCCTTGAGTGGCTGGGAAGGACATACTACAGG TCCAAGTGGTATAATTATTATGAAGTATCTGTGA AAAGTCGAATAACCATCAACCCAGACACATCCA AGAACCAGTTCTCCCTGCAGCTGAACTCTGTGAC TCCCGAGGACACGGCTGTATATTTCTGTGCGAGA GATCAACGGTACTACGGTATGGACGTCTGGGGCC AAGGGACCACGGTCACCGTCTCCTCA |
| | | | SEQ ID NO: 26967 | SEQ ID NO: 30973 |
| | | AA | EIVMTQSPATLSVSPGESATLSCRSSQNIKSNLA WYQQKPGQAPRLLIFGASTRATGIPARFSGSGSG TEFTLTISSLQSEDFAVYYCQQFYNWLCSFGQGT KLELK | QVQLQQSGPGLVKPSQTLSLTCAISGDSVSSNSAA WNWIRQSPSRGLEWLGRTYYRSKWYNYYEVSVKS RITINPDTSKNQFSLQLNSVTPEDTAVYFCARDQRY YGMDVWGQGTTVTVSS |
| | | | SEQ ID NO: 26968 | SEQ ID NO: 30974 |
| iPS:436252 | 21-225_202A8 | NA | GAAATAGTGATGACGCAGTCTCCAGCCACCCT GTCTGTGTCTCCAGGGGAAAGAGCCACCCTCT CCTGCAGGCCAGTCAGAGAATTAACAACAA CTTAGCCTGGTACCAGCAGAAACCCTGGCCAGG CTCCCAGGCTCCTCATTTATGGTGCATCCACCA GGGCCACTGGTCTGTCCCGGCCAGGTTCAGTGGC AGTGGGTCTGGGACAGAGTTCACTCTCACCAT CAGCAGCCTGCAGTCTGAAGACTTTACAGTTT ATTACTGTCAGCAGTATTATACTGGCTGTGC AGTTTTTGGCCAGGGGACCAAGCTGGAGATCAG A | CAGGTACAGCTGCAGCAGTCAGGTCCAGGACTG GTGAAGCCCTCGCAGACCCTCTCACTCACCTGTG CCATCTCCGGGGACAGTGTCTCTAGCAACAGTGC TGCTTGGAACTGGATCAGGCAGTCCCCATCGAGA GGCCTTGAGTGGCTGGGAAGGACATACTACAGG TCCAAGTGGTATAATGAGTATGCAGTATCTGTGA GAAGTCGAATAACCATCAACCCAGACACATCCA AGAACCAGTTCTCCCTGCAGCTGAACTCTGTGAC TCCCGAGGACACGGCTCTGTATTACTGTACAAGA GATCAACGGTACTACGGTATGGACGTCTGGGGCC AAGGGACCCCGGTCACCGTCCTCA |
| | | | SEQ ID NO: 26969 | SEQ ID NO: 30975 |

FIGURE 50
(Continued)

| | | | |
|---|---|---|---|
| iPS:436254 | 21-225_202C12 | AA | EIVMTQSPATLSVSPGERATLSCRASQRINNNLA WYQQNPGQAPRLLIYGASTRATGVPARFSGSGS GTEFTLTISSLQSEDFTVYYCQQYNWLCSFGQG TKLEIR<br>SEQ ID NO: 26970 | QVQLQQSGPGLVKPSQTLSLTCAISGDSVSSNSAA WNWIRQSPSRGLEWLGRTYYRSKWYNEYAVSVRS RITINPDTSKNQFSLQLNSVTPEDTALYYCTRDQRY YGMDVWGQGTPVTVSS<br>SEQ ID NO: 30976 |
| | | NA | GATATTGTGCTGACTCAGTCTCCACTCTCCCTG CCCGTCACCCCTGGAGAGCCGGCCTCCATCTC CTGCAGGTCTAGTCAGAGCCTCCTGCATAATA ATAAATACAACCATTTGGATTGGTACCTGCAG AAGCCAGGGCAGTCTCCACAGCTCCTGATCTA TTTGGGTTCTAATCGGGCCTCCGGGGTCCCTG ACAGGTTCAGTGCAGTGGATCAGGCACAGAT TTTACACTGAAAATCAGCAGAGTGGAGGCTGA GGATGTTGGGGTTTATTACTGCATGCAAGCTC TACAAACTCCCACTTTCGGCGGAGGGACCAAG GTGGAGATCAAA<br>SEQ ID NO: 26971 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAACTATTAGTGGTAGTGGTGTT AGAACATACTACGCAGACTCCGTGAAGGGCCGG TCCACCATCTCCAGAGACAATTCCAAGAATACGC TGTTTCTGCAAATGAACAGCCTGAGAGCCGAGG ACACGGCCGTATATTACTGTGCGAAAGGGGAG CTAGGAGCAGTGGCTGGTTCCACTTTGACTACTG GGGCCAGGGAACCCTGGTCACCGTCTCCTCA<br>SEQ ID NO: 30977 |
| | | AA | DIVLTQSPLSLPVTPGEPASISCRSSQSLLHNNKY NHLDWYLQKPGQSPQLLIYLGSNRASGVPDRFS GSGSGTDFTLKISRVEAEDVGVYYCMQALQTPT FGGGTKVEIK<br>SEQ ID NO: 26972 | EVQLLESGGGLVQPGGSLRLSCAASGFTFSSYAMS WVRQAPGKGLEWVSTISGSGVRTYYADSVKGRSTI SRDNSKNTLFLQMNSLRAEDTAVYYCAKGGARSS GWFHFDYWGQGTLVTVSS<br>SEQ ID NO: 30978 |

FIGURE 50
(Continued)

| | | | |
|---|---|---|---|
| iPS:436256 | 21-225_202D9 | NA | GAAATTGTGTTGACGCAGTCTCCAGACACCCT GTCTTTGTCTCCAGGGGAAAGAGCCACCCTCT CCTGCAGGGCCAGTCAGTGTTAACAGCGGC TACTTAGCCTGGTACCAGCAGAAACCTGGCCA GTCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGCATTACTGTCAACAATATGAGACCTCACCG TGGACGTTCGGCCAAGGGACCAAGGTGGAAA TCAAA<br>SEQ ID NO: 26973 | CAGGTGCAGCTACAGCAGTGGGGCGCAGGACTG TTGAAGCCTTCGGAGACCCTGTCCCTCACCTGCG CTGTCTATGATGGGTCCTTCAGTCCTTACTACTGG AGCTGGATCCGCCAGCCCCCAGGGAAGGGGCTG GAGTGGATTGGGGAAATCAATCATAGTGGAAGC ACCAACTACAATCCGTCCCTCAAGAGTCGAGTCA CCATATCAGTAGACACGTCCAAGAACCAGTTCTC CCTGAAGCTGAGCTCTGTGACCGCCGCGACACG GCTGTATATTACTGTGCGAGAGACTACGGGGGTT TAGACTACTGGGGCCAGGGAACCCTGGTCACCGT CTCCTCA<br>SEQ ID NO: 30979 |
| | | AA | EIVLTQSPDTLSLSPGERATLSCRASQSVNSGYLA WYQQKPGQSPRLLIYGASSRATGIPDRFSGSGSG TDFTLTISRLEPEDFAVHYCQQYETSPWTFGQGT KVEIK<br>SEQ ID NO: 26974 | QVQLQQWGAGLLKPSETLSLTCAVYDGSFSPYYW SWIRQPPGKGLEWIGEINHSGSTNYNPSLKSRVTISV DTSKNQFSLKLSSVTAADTAVYYCARDYGGLDYW GQGTLVTVSS<br>SEQ ID NO: 30980 |
| iPS:436258 | 21-225_202F12 | NA | GAAATAGTGATGACGCAGTCTCCAGCCACCCT GTCTGTGTCTCCAGGGGAAAGAGCCACCCTCT CCTGCAGGGCCAGTCAGAGTGTTGAACAAC TTAGCCTGGTACCACCAGAGACCTGGCCAGGC TCCCAGGCTCCTCATCTATGGTGCATCCACTA GGGCCACTGGTATCCCAGCCAGGTTCAGTGGC AGTGGGTCTGGGACAGAGTTCACTCTCACCAT CAGCAGCCTGCAGTCTGAAGATTTTGCAGTTT ATTACTGTCAGCAGTATGATAACTGGCCTCCG TGCAGTTTTGGCCAGGGGACCAAGCTGGAGAT CAAA<br>SEQ ID NO: 26975 | CAGGTGCAGCTGGTGGAGTCTGGGGGAGGCGTG GTCCAGCCTGGGAGGTCCCTGAGACTCTCCTGTG AAGCGTCTGGATTCACCTTCAGTTACTATGGCAT GCACTGGGTCCGCCAGGCTCCAGGCAAGGGACT GGAGTGGGTGGCAATTATATGGTATGATGGAAGT AATAAATTCTATGCAGAGACTCCGTGAAGGGCCGAT TCACCATCTCCAGAGACAACGCTTCCAAGAACACGCT GTATCTGCAAATGAACAGCCTGAGAGCCGAGGA CACGGCTGTGTATTACTGTGCGAGTAATATAGCA GCAGCTGCCCCTTACTTGACTACTGGGGCCAGG GAACCCTGGTCACCGTCTCCTCA<br>SEQ ID NO: 30981 |

FIGURE 50
(Continued)

| | | | |
|---|---|---|---|
| iPS:436260 | 21-225_203H1 | AA | EIVMTQSPATLSVSPGERATLSCRASQSVLNNLA WYQQRPGQAPRLLIYGASTRATGIPARFSGSGSG TEFTLTISSLQSEDFAVYYCQQYDNWPPCSFGQG TKLEIK<br><br>SEQ ID NO: 26976 | QVQLVESGGGVVQPGRSLRLSCEASGFTFSSYYGMH WVRQAPGKGLEWVAIIHWYDGSNKFYADSVKGRFT ISRDSSKNTLYLQMNSLRAEDTAVYYCASNIAAAA PYFDYWGQGTLVTVSS<br><br>SEQ ID NO: 30982 |
| | | NA | GACATCCAGATGACCCAGTCTCCATCCTCACT GTCTGCATCTGTCGGAGACAGAGTCACCATCA CTTGTCGGGCGAGTCAGGGCATTGGCAATTAT TTAGCCTGGTTTCAGCAGAAACCAGGGAAAGC CCCTAAGTCCCTGATCTATGTTGCATCCAGGTT GCAAAGTGGGGTCCCATCAAGTTCAGCGGCA CTGGATCTGGGTCAGATTTCACTCTCACCATC AGCAGCCTGCAGCCTGACGATTTTGCGACTTA TTACTGCCAACGGTATCATACTTACCCGCTCA CTTTCGGCGGAGGGACCAAGGTGGAGATCAA A<br><br>SEQ ID NO: 26977 | CAGGTGCAGCTGGTGGAGTCTGGGGGAGGCGTG GTCCAGCCTGGGAGGTCCCTGAGACTCTCCTGTG CAGCGTCTGAGTTCACCTTCAGTAGCTATGGCAT GCACTGGGTCCGCCAGGCTCCAGGCAAGGGGCT GGAGTGGGTGGCAGTTATATGTGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATAGAAC AGTTGGCTACAACGGTATGGACGTCTGGGGCCA AGGGACCACGGTCACCGTCTCCTCA<br><br>SEQ ID NO: 30983 |
| | | AA | DIQMTQSPSSLSASVGDRVTITCRASQGIGNYLA WFQQKPGKAPKSLIYVASRLQSGVPSKFSGTGS GSDFTLTISSLQPDDFATYYCQRYHTYPLTFGGG TKVEIK<br><br>SEQ ID NO: 26978 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDRTVG YNGMDVWGQGTTVTVSS<br><br>SEQ ID NO: 30984 |

FIGURE 50
(Continued)

| | | | | |
|---|---|---|---|---|
| iPS:436262 | 21-225_203E3 | NA | GACATCCAGATGACCCAGTCTCCATCCTCCCC<br>GTCTGCATCTGTTGGAGACAGAGTCACCATCA<br>CTCGCCGGGCAAGTCACAACATTAACAGCTAT<br>TTAAATTGGTATCAGCAGAAATCAGGAAAGC<br>CCCTAAACTCCTTATCTATGCTGCATCCAGTTT<br>GCAAAGTGGGGTCCCGTCAAGGTTCAGTGGCA<br>GTGGATCTGGGACAGATTTCACTCTCACTTTC<br>AGTAGTCTACAACCTGAAGATTTTGCAACTTA<br>CTACTGTCAACAGAGTTACAGTTTCCGCTCA<br>CTTTCGGCGGAGGGACCAAGGTGGAGATGAG<br>G<br>SEQ ID NO: 26979 | CAGGTGCAGCTGGTGCAGTCTGGGGCTGAGGTG<br>AAGAAGCCTGGGGCCTCAGTGAAGGTCTCCTGC<br>AAGGCTTCTGGATACACCTTCACCGGCTACTATA<br>TCCACTGGGTGCGACAGGCCCCTGGACAAGGGC<br>TTGAGTGGATGGCATGGATCAACCCTAATAGTGG<br>TGGCACAAACTATGCACAGAAGTTTCAGGGCAG<br>GGTCACCATGACCAGGGACACGTCCATCACCAC<br>AGCCTACATGGAGCTGAGCAGGCTGAGATCTGA<br>CGACACGGCCGTGTATTACTGTGCGAGAGGATAC<br>AGCTATGGTTACAACTGGTTCGACCCCTGGGGCC<br>AGGGAACCCTGGTCACCGTCTCCTCA<br>SEQ ID NO: 30985 |
| | | AA | DIQMTQSPSSPSASVGDRVTITRRASHNINSYLN<br>WYQQKSGKAPKLLIYAASSLQSGVPSRFSGSGS<br>GTDFTLTFSSLQPEDFATYYCQQSYSFPLTFGGG<br>TKVEMR<br>SEQ ID NO: 26980 | QVQLVQSGAEVKKPGASVKVSCKASGYTFTGYYIH<br>WVRQAPGQGLEWMAWINPNSGGTNYAQKFQGRV<br>TMTRDTSITTAYMELSRLRSDDTAVYYCARGYSYG<br>YNWFDPWGQGTLVTVSS<br>SEQ ID NO: 30986 |
| iPS:436264 | 21-225_203F7 | NA | GACATCCAGATGACCCAGTCTCCATCCTCCCG<br>TTTTGCATCTGTAGGAGACAGAGTCACCATCA<br>CTTGCCGGGCAAGTCAGGGCATTAGACATGAT<br>TTAGGCTGGTATCAGCAGCAGAAACCAGGGAAAG<br>CCCTTAAGCGCCTTGATATATGCTGCATCCAGTT<br>TGCAAAGTGGGGTCCCATCAAGGTTCAGCGGC<br>AGTGGATGTGGGACAGATTCACTCTCACAAT<br>CAGCAGCCTGCAGCCTGAAGATTTTGCAAATT<br>ATTACTGTCTACACAGCATTATAGTTCCCTCGGA<br>CGTTCGGCCAAGGGACCAAGGTGGAAATCAA<br>A<br>SEQ ID NO: 26981 | CAGGTGCAGCTGGTGGAGTCTGGGGGAGGCGTG<br>GTCCAGCCTGGGGAGGTCCCTGAGACTCTCCTGTG<br>CAGCGTCTGGATTCACCTTCAGTGACTATGTCAT<br>GCACTGGGTCCGCCAGGCTCCAGGCAAGGGGCT<br>GGAGTGGGTGGCAGTTATATGTCCGTGAAGGAAGT<br>AATAAATACTATGTAGACTCCGTGAAGGGCCGAT<br>TCACCATCTCCAGAGACAATTCCAAGAACACGCT<br>GTATCTGCAAATGAACAGCCTGAGAGCCGAGGA<br>CACGGCTGTGTATTACTGTGCGAGAGAACGTAT<br>AGCAGTGGCTTGTACGACTACGGTATGGACGTCT<br>GGGGCCAAGGGACCACGGTCACCGTCTCCTCA<br>SEQ ID NO: 30987 |

FIGURE 50
(Continued)

| | | | |
|---|---|---|---|
| iPS:436268 | 21-225_203B9 | AA | DIQMTQSPSSLSASVGDRVTITCRASQGIRHDLGWYQQKPGKAPKLLIYAASSLQSGVPSRFSGSGCGTEFTLTISSVQPEDFANYYCLQHYSFPRTFGQGTKVEIK<br>SEQ ID NO: 26982 | QVQLVESGGGVVQPGRSLRLSCAASGFTFSDYMHWVRQAPGKGLEWVAVIWYDGSNKYYVDSVKGRFTISRDNSRNTLYLQMNSLRAEDTAVYYCARERYSSGLYDYGMDVWGQGTTVTVSS<br>SEQ ID NO: 30988 |
| | | NA | GACATCCAGATGACCCAGTCTCCATCCTCCCTGTCTGCATCTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTGATCTATGCGGCATCCAGTGTGCAAAATGGGGTCCCATCAAGGTTCAGCGGCAGTGGATCTGGGACAGAATTCACTCTCACAATCAGCAGCCTGCAGCCTGAAGATTTTGCAACTTATCACTGTCTACAGCATAATAGTTACCCATTCACTTTCGGCCCTGGGACCAAAGTGGATATCAAA<br>SEQ ID NO: 26983 | CAGGTGCAGCTGGTGGAGTCTGGGGGAGGCGTGGTCCAGCCTGGGAGGTCCCTGAGACTCTCCTGTCAGCGTCAGGATTCACCTTCAGTAGTTTTGGCATGCACTGGGTCCGCCAGGCTCCAGGCAAGGGGCTGGAGTGGGTGGCAGTTATATGGTATGATGGAAATAAATACTATGCAGACTCCGTGAAGGGCCGATTCACAATCTCCAGAGACAATTCCAAGAACACGCTGTATCTCCAAATGAACAGCCTGAGACCCGAGGACACGGCTGTGTATTACTGTGCGAGAGAACTGGGGTTCCTCTCTGACTACTGGGCCAGGGAATCCTGGTCACCGTCTCCTCA<br>SEQ ID NO: 30989 |
| | | AA | DIQMTQSPSSLSASVGDRVTITCRASQGIRNDLGWYQQKPGKAPKRLIYRASSVQNGVPSRFSGSGSGTEFTLTISSLQPEDFATYHCLQHNSYPFTFGPGTKVDIK<br>SEQ ID NO: 26984 | QVQLVESGGGVVQPGRSLRLSCAASGFTLSSFGMHWVRQAPGKGLEWVAVIWYDVNNKYYADSVKGRFTISRDNSKNTLYLQMNSLRPEDTAVYYCARELGFLSDYWGQGILVTVSS<br>SEQ ID NO: 30990 |

FIGURE 50
(Continued)

| | | | | | |
|---|---|---|---|---|---|
| iPS:436270 | 21-225_203F10 | NA | GACATCGTGATGACCCAGTCTCCAGACTCCCT<br>GGCTGTGTCTCTGGGCGAGAGGGCCACCATCA<br>ACTGCAAGTCCAGCAGTGTTTTTTCCACT<br>CGAACAATAAGAACTACTTAGCTTGGTACCAG<br>CAGAAACCAGGACAGCCTCCTAAGTTGCTCAT<br>TTACTGGGCATCTACCCGGGAATCCGGGGTCC<br>CTGACCGATTCAGTGGCAGCGGGTCTGGGACA<br>GATTTCACTCTCACCATCAGCAGCCTGCAGGC<br>TGAAGATGTGACAGTTTATTACTGTCAACAAT<br>ATTTAGTCTTCCATTCACTTTCGGCCCTGGGA<br>CCAAAGTGGATATCACA | CAGGTGCAACTGGTGGAGTCTGGGGGAGGCTTG<br>GTCAAGCCTGGAGGGTCCCTGAGACTCTCCTGTG<br>CAGCCCTCTGATTCACCTTCAGTGACTACTACAT<br>GAGCTGGATCCGCCAGGCTCCAGGGAAGGGCT<br>GGAGTGGGTTTTATACATTAGTGGTAGTGGTACT<br>ACCACATACTACGCAGACTCTGTGAAGGGCCGAT<br>TCACCATCTCCAGGGACAACGCCAAGAACTCACT<br>GTATCTGCAAATGAACAGCCTGAGAGCCGAGGA<br>CACGGCCGTGTATTACTGTGCGAGAGATAGGGG<br>GGGTTTGACGTCTGGGGCCAAGGGACCACGGT<br>CACCGTCTCCTCA |
| | | | SEQ ID NO: 26985 | SEQ ID NO: 30991 |
| | | AA | DIVMTQSPDSLAVSLGERATINCKSSQSVFFHSN<br>NKNYLAWYQQKPGQPPKLLIYWASTRESGVPD<br>RFSGSGSGTDFTLTISSLQAEDVTVYYCQQYFSL<br>PFTFGPGTKVDIT | QVQLVESGGGLVKPGGSLRLSCAASGFTFSDYYMS<br>WIRQAPGKGLEWVLYISGSGTTYYADSVKGRFTIS<br>RDNAKNSLYLQMNSLRAEDTAVYYCARDRGGLD<br>VWGQGTTVTVSS |
| | | | SEQ ID NO: 26986 | SEQ ID NO: 30992 |
| iPS:436272 | 21-225_201F5 | NA | GACATCGTGATGACCCAGTCTCCAGAGTCCT<br>GGCTGTGTCTCTGGGCGAGAGGGCCACCATCA<br>ACTGCAAGTCCAGCCAGAGTGTTTTATACAGT<br>TCCAACAATAAGAACTACTTAGTTTGGTACCA<br>GCAGAAACCAGGACAGCCTCCTAAACTGCTCA<br>TTTACTGGGCATCTACCCGGGAATCCGGGGTC<br>CCTGACCGATTCAGTGGCAGCGGGTCTGGGAC<br>AGATTTCACTCTCACCATCAGCAGCCTGCAGG<br>CTGAAGATGTGGCAGTTTATTACTGTCAGCAA<br>TATTATAGTACTCCTCGACGTTCGGCCAAGG<br>GACCAAGGTGAAATCAAA | CAGGTGCAGCTGGTGCAGTCTGGGCTGGGTG<br>AAGAAGCCTGGGGCCTCAGTGAAGGTCTCTGC<br>AAGGCTTCTGGATACACCTTCACCAATTATGATA<br>TCAACTGGGTGCGACAGGCCACTGGACAAGGC<br>TTGAGTGGATGGGATGGATGCACCTAACAGTGG<br>TAACACAGGCTATGCACAGAAGTTCCAGGCAG<br>AGTCACCATGACCAGGAACACCTCCATAAGCAC<br>AGCCTACATGGAGCTGAGCAGCCTGAGATCTGA<br>GGACACGGCCGTGTATTACTGTGCCTATAGCAGT<br>GGCTGGTACTACTTTGACTACTGGGGCCAGGAA<br>CCCTGGTCACCGTCTCCTCA |
| | | | SEQ ID NO: 26987 | SEQ ID NO: 30993 |

FIGURE 50
(Continued)

| | | | |
|---|---|---|---|
| iPS:436274 | 21-225_204H3 | AA | DIVMTQSPESLAVSLGERATINCKSSQSVLYSSN NKNYLVWYQQKPGQPPKLLIYWASTRESGVPD RFSGSGSGTDFTLTISSLQAEDVAVYYCQQYYST PPTFGQGTKVEIK<br>SEQ ID NO: 26988 | QVQLVQSGAAVKKPGASVKVSCKASGYTFTNYDI NWVRQATGQGLEWMGWMHPNSGNTGYAQKFQG RVTMTRNTSISTAYMELSSLRSEDTAVYYCAYSSG WYYFDYWGQGTLVTVSS<br>SEQ ID NO: 30994 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTGAACTCCTGATCTATGCTGCAGCCAGT TTGCAAGGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAACTCC AA<br>SEQ ID NO: 26989 | CAGGTGCAGCTGGTGGAGTCTGGGGGAGGCGTG GCCCAGCCTGGGAGGTCCCTGAGACTCTCCTGTA CAGCGTCTGGATTCACCTTCAGTAGCTATGTCAT GCACTGGGTCCGCCAGGCTCCAGGCAAGGGGCT GGAGTGGGTGGCAGTTATATGCAGACTCCGTGAAGGGCCGA AATAAATATAATGCAGACTCCGTGAAGGGCCGA TTCACCATCTCCAGAGACACAATTCCAAGAACACGC TGTATCTGCAAATGAACAGCCTGAGAGCCGAGG ACACGGCTGTGTATTACTGTGCGAGAGAACCGTA TAGCAGCAGCTGGTACGACTACGGTATGGACGTC TCGGGCCAAGGGACCACGGTCACCGTCTCCTCA<br>SEQ ID NO: 30995 |
| | | AA | DIQMTQSPSSLSASVGDRVTITCRASQGIRNDLG WYQQKPGKAPELLIYAAASLQGGVPSRFSGSGS GTEFTLTISSLQPEDFATYYCLQHYSYPRTFGQG TKVELQ<br>SEQ ID NO: 26990 | QVQLVESGGGVGQPGRSLRLSCTASGFTFSSYVMH WVRQAPGKGLEWVAVIWYDGSNKYNADSVKGRF TISRDNSKNTLYLQMNSLRAEDTAVYYCAREPYSS SWYDYGMDVSGQGTFVTVSS<br>SEQ ID NO: 30996 |

FIGURE 50
(Continued)

| | | | |
|---|---|---|---|
| iPS:436276 | 21-225_204H4 | NA | GACATCCAGATGACCCTGTCTCCATCCTCCC GTCTGCATTTGTTGGAGACAGAGTCACCATCA CTCGCCGGGCAAGTCACAACATTAACAGCTAT TTAAATTGGTATCAGCAGAAATCAGGAAAGC CCCTAAACTCCTATCTATGCTGCATCCAGTTT GCAAAGTGGGGGTCCCGTCAAGGTTCAGTGGCA GTGGATCTGGGACAGATTTCACTCTCACTTTC AGTAGTCTACAAACCTGAAGATTTTGCAACTTA CTACTGTCAACAGAGTTACAGTTTCCGCTCA CTTTCGGCGGAGGGACCAAGGTGGAGATGAG G |  CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TCCACTGGGTGCGACAGCCCCTGGACAAGGGC TTGAGTGGATGGCATGGATCAACCCTAATAGTGG TGGCACAAACTATGCACAGAAGTTCAGGGCAG GGTCACCATGACCAGGGACACGTCCATCACCAC AGCCTACATGGAGCTGAGCAGGCTGAGATCTGA CGACACGGCCGTGTATTACTGTGCGAGAGGATAC AGCTATGGTTACAACTGGTTCGACCCCTGGGGCC AGGGAACCCTGGTCACCGTCTCCTCA |
| | | | SEQ ID NO: 26991 | SEQ ID NO: 30997 |
| | | AA | DIQMTLSPSPSPSAFVGDRVTITRRASHNINSYLN WYQQKSGKAPKLLIYAASSLQSGVPSRFSGSGS GTDFTLTFSSLQPEDFATYYCQQSYSFPLTFGGG TKVEMR | QVQLVQSGAEVKKPGASVKVSCKASGYTFTGYYIH WVRQAPGQGLEWMAWINPNSGGTNYAQKFQGRV TMTRDTSITTAYMELSRLRSDDTAVYYCARGYSYG YNWFDPWGQGTLVTVSS |
| | | | SEQ ID NO: 26992 | SEQ ID NO: 30998 |
| iPS:436278 | 21-225_201F2 | NA | GAGATAGTGATGACGCAGTCTCCAGCCACCCT GTCTGTGTCTCCAGGGGAAAGAGCCACCCTCT CCTGCAGGGCCAGTCAGAATATTAAAAGCAAC TTAGCCTGGTACCAGCAGAAACCTGGCCAGGC TCCCAGGCTCCTCATCTTTGGTGCATCCACCAG GGCCACTGGTATCCCAGCCAGGTTCAGTGGCA GTGGGTCTGGTACAGAGTTCACTCTCACCATC AGCAGCCTGCAGTCTGAAGATTTTGCAGTGTA TTACTGTCAGCAGTTTTATAACTGGCTGTGCA GTTTTGGCCAGGGGACCAAGCTGGAGCTCAAG |  CAGGTACAGCTGCAGCAGTCAGGTCAGGACTG GTGAAGCCCTCGCAGACCCTCACTCACCTGTG CCATCTCGGGGACAGTGTCTCTAGCAACAGTGC TGCTTGGAACTGGATCAGGCAGTCCCATCGAGA GGCCTTGAGTGGCTGGGAAGGACATACTACAGG TCCAAGTGGTATAATTATTATGAAGTATCTGTGA GAAGTCGAGTAACCATCAACCAGACACATCCA AGAACCAGTTCCCTGCAACTGAACTCTGTGAC TCCCGAGGACACGGCTGTGTATTTCTGTGCGAGA GATCAACGGTACTACGGTATGGACGTCTGGGGCC AAGGGACCACGGTCACCGTCTCCTCA |
| | | | SEQ ID NO: 26993 | SEQ ID NO: 30999 |

FIGURE 50
(Continued)

| | | | |
|---|---|---|---|
| | | AA | QVQLQQSGPGLVKPSQTLSLTCAISGDSVSSNSAA WNWIRQSPSRGLEWLGRTYYRSKWYNYYEVSVRS RVTINPDTSKNQFSLQLNSVTPEDTAVYFCARDQR YYGMDVWGQGTTVTSS<br><br>SEQ ID NO: 31000 |
| | | | GAGGTGCAGGTGTTGGAGTCTGGGGGAGGCTTG GTGCAGCCTGGGGGGTCCCTGCGACTCTCCTGTG CAGCCCTCTGGATTCACCTTTAGCACCTATGCCAT GAGCTGGGTCCGCCAGGCTCCAGGGAAGGGGCT GGAGTGGGTCTCAGTATTAGTGGTAGTGGTGGT AGCACATATTACGCAGACTCCGTGAAGGGCCGG TTCACCATCTCCAGAGACAATTCCAAGAACACGC TGTATCTGCAAATGGACAGCCTGAGAGCCGAGG ACACGGCCGTATATTACTGTGCGAAAGGGATAA GTGGAACCGGCTCCTACTACTACTACGGTGTGGA CGTCTGGGGCCAAGGGACCACGGTCACCGTCTCC TCA<br><br>SEQ ID NO: 31001 |
| iPS:436280 | 21-225_204D6 | AA | EIVMTQSPATLSVSPGERATLSCRASQNIKSNLA WYQQKPGQAPRLLIFGASTRATGIPARFSGSGSG TEFTLTISSLQSEDFAVYYCQQFYNWLCSFGQGT KLELK<br><br>SEQ ID NO: 26994 |
| | | NA | GACAGCCAGATGACCCAGTCTCCATCCTCCCT GTCTGCATCTGTAGGAGACAGAGTCACCATCA CTTGCCGGGCAAGTCGGAGCGGTTCACACCTAT TAAATTGGTATCAACAGAAGCCAGGGAAAG CCCCTAAGGTCCTGATCTATGGTGCATCCAGT TTGCAACGTGGGGTCCCATCAAGGTTCAGTGG CAGTGGATCTGGGACAGATTCACTCTCACCA TCAGCAGTCTGCAACCTGAAGATGTTGCAACT TACTACTGTCAACAGAGTTACAGTTCCCCGCT CACTTTCGGCGGGGGGACCAAGGTGGAGATCC AA<br><br>SEQ ID NO: 26995 |
| | | AA | DSQMTQSPSSLSASVGDRVTITCRASRSVHTYLN WYQQKPGKAPKVLIYGASSLQRGVPSRFSGSGS GTDFTLTISSLQPEDVATYYCQQSYSSPLTFGGG TKVEIQ<br><br>SEQ ID NO: 26996 |
| | | | EVQVLESGGGLVQPGGSLRLSCAASGFTFSTYAMS WVRQAPGKGLEWVSAISGSGGSTYYADSVKGRFTI SRDNSKNTLYLQMDSLRAEDTAVYYCAKGISGTGS YYYGVDVWGQGTTVTVSS<br><br>SEQ ID NO: 31002 |

FIGURE 50
(Continued)

| | | | | |
|---|---|---|---|---|
| iPS:436282 | 21-225_204G6 | NA | GACATCCGGATGACCCAGTCTCCATCCTCACTGTCTGCATCTGTAGGAGACAGAGTCACCATCACTTGTCGGGCGAGTCAGGGCATTGGCAATTATTTAGCCTGGTTTCAGCAGAAACCAGGGAAAGCCCCTAAGTCCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTACTGCCAACACTATCTTAGTTACCCTCTCACTTTCGGCGGAGGGACCAAGGTGGAGATCAAA SEQ ID NO: 26997 | CAGGTGCAGCTGGTGGAGTCTGGGGGAGGCGTGGTCCAGCCTGGGAGGTCCCTGAGACTCTCCTGTACAGCCTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGAGGTGTCGGCTACGACGGTATGGACGTCTGGGGCCAAGGGACCACGGTCACCGTCTCCTCA SEQ ID NO: 31003 |
| | | AA | DIRMTQSPSSLSASVGDRITITCRTSQGIGNYLAWFQQKPGKAPKSLIYAASSLQSGVPSRFSGSGSGTDFTLTISSLQPEDFATYYCQHYLSYPLTFGGGTKVEIK SEQ ID NO: 26998 | QVQLVESGGGVVQPGRSLRLSCTASGFTFSSYGMHWVRQAPGKGLEWVAVIWYDGSNKYADSVKGRFTISRDNSKNTLYLQMNSLRAEDTAVYYCARDRGVGYDGMDVWGQGTTVTVSS SEQ ID NO: 31004 |
| iPS:436284 | 21-225_204G8 | NA | GACATCCAGATGACCCAGTCTCCATCCTCACTGTCTGCATCTGTAGGAGACAGAGTCACCATCACTTGTCGGGCGAGTCAGGGCATAAGTAATCATCTTGTTTCAGCAGAAACCAGGGAAAGCCCCTAAGTCCCTGATCTTTGCTGCATCCAGTTTGCAAAGTGGGGTCCCATCACAGTTCAGCGGCAGTGGATCTGGGACCGAATTCACTCTCACCATCAGCAGCCTGCAGCCTGAAGATATTGCAACTTATTACTGTCAACAGTATAGTAATTACCCGGTCACTTTCGGCGGAGGGACCAAGGTGGAGATCAAA SEQ ID NO: 26999 | CAGGTGCAGCTGGTGGAGTCTGGGGGAGACGTGGTCCAGCCTGGGAGGTCCCTGAGACTCTCATGTGCAGCGTCTGGATTCACCTTCAGTAGCTATGGCATGCACTGGGCCGCCAGGCTCCAGGCAAGGGCTGGAGTGGGTGGCAGTTATATGTAGCCTCCGTGAAGGGCCGATAATGAAAATTATGTAGCCTCCGTGAAGGGCCGATTCACCATCTTCAGAGACAATTCCAAGAACACGCTGTATCTGCAAATGAACAGCCTGAGAGCCGAGGACACGGCTGTGTATTACGGTATGGACGTCTGGGGCCAAGATAGGGTATTACGGTATGGACGTCTGGGGCCAAGGGACCACGGTCACCGTCTCCTCA SEQ ID NO: 31005 |

FIGURE 50
(Continued)

| | | | | |
|---|---|---|---|---|
| iPS:436286 | 21-225_204H8 | AA | DIQMTQSPSSLSASVGDRVTITCRASQGISNHLA WFQQKPGKAPKSLIFAASSLQSGVPSQFSGSGSG TEFTLTISSLQPEDFATYYCQQYSNYPVTFGGGT KVEIK<br><br>SEQ ID NO: 27000 | QVQLVESGGDVVQPGRSLRLSCAASGFTFSSYGMH WGRQAPGKGLEWVAVIWYDGSNENYVASVKGRF TIFRDNSKNTLYLQMNSLRAEDTAVYYCARDLGIG YYGMDVWGQGTTVTVSS<br><br>SEQ ID NO: 31006 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGTCGCCTGATCTATTCTGCATCCAGTT TGCAAAGTGGGGTCCCATCAAGGTTCAGCGGC CGTGGATCTGGGACAGAATTCACTCTCACAGT CAGCAGCCTGCAGCCTGAAGATTTTGCAACTT ATTACTGTCTACAACATATAGTTACCCTCTCA CTTTCGGCGGAGGGACCAAGGTGGAGATCAA A<br><br>SEQ ID NO: 27001 | CAGGTGCAGCTACAGCAGTGGGGCGCAGGACTG TTGAAGCCTTCGGAGACCGTCCTCCTCACCTGCG CTGTCTATGGTGGGTCCTTCAGTGGTTACTTCTGG AGCTGGGTCCGCCAGCCCCCAGGGAAGGGACTG GAGTGGATTGGGAAATCAGTCAGTAGTGGAAGC ACCAGTTACAACCCGTCCCTCAAGAGTCGAGTCA CCATATCAGTAGACAAGTCCAAGAACCAGTTCTC CCTGAAGCTGAGCTCTGTGACCGCCGCGGACACG GCTGTGTATTACTGTGCGAGGGACTACGGGGCCG ACTACTGGGGCCAGGGAACCCTGGTCACCGTCTC CTCA<br><br>SEQ ID NO: 31007 |
| | | AA | DIQMTQSPSSLSASVGDRVTITCRASQGIRNDLG WYQQKPGKAPKRLIYSASSLQSGVPSRFSGRGS GTEFTLTVSSLQPEDFATYYCLQHNSYPLTFGGG TKVEIK<br><br>SEQ ID NO: 27002 | QVQLQQWGAGLLKPSETLFLTCAVYGGSFSGYFW TWVRQPPGKGLEWIGEISHSGSTSYNPSLKSRVTIS VDKSKNQFSLKLSSVTAADTAVYYCARDYGADY WGQGTLVTVSS<br><br>SEQ ID NO: 31008 |

FIGURE 50
(Continued)

| | | | |
|---|---|---|---|
| iPS:436290 | 21-225_205G3 | NA | GAAATCGTGTTGACGCAGTCTCCAGGCACCCT GTCTTTGTCTCCAGGGGAAAGAGCCACCCTCT CCTGCAGGGCCAGTCAGAATGTTAGTTACAGC TACTTAGCCTGGTACCAGCAGAAACCTGGCCA GGCTCCCAGGCTCCTCATCTATGGTGCATCCA GGAGGGCCACTGGCATCCCAGACAGTTCAGT GGCAGTGGGTCTGGGACAGACTTCACTCTCAC CATCAGCAGACTGGAGCCTGAAGATTTTGCAG TGTATTACTGTCAGCAGTATGGTAGCTCACCG TGCAGTTTTGGCCAGGGGACCAAGCTGGAGAT CAAA SEQ ID NO: 27003 | EIVLTQSPGTLSLSPGERATLSCRASQNVSYSYLA WYQQKPGQAPRLLIYGASRRATGIPDRFSGSGSG TDFTLTISRLEPEDFAVYYCQQYGSSPCSFGQGT KLEIK SEQ ID NO: 27004 | CAGGTGCAGCTACAGCAGTGGGGCGCAGGACTG TTGAAGCCTTCGGAGACCCTGTCCCTCACCTGCG CTGTCTTTGGTGGGTCCTTCAGTGGTCACTACTGG AGCTGGATCCGCCAGCCCCCAGGGAAGGGGCTG GAGTGGATTGGGGAAATGTATCATTTTGAAACA CCAACTACAACCGTCCCTCAAGAGTCGAGTCAC CATGTCAGTAGACACGTCCAAGAACAGTTCTCC CTGAAGCTGAGCTCTGTGACCGCCGCGGACACG GCTGTGTATTACTGTGCGAGAGTGGGGCAGTGGC TGGCTTTTGATATCTGGGGCCAAGGGACAATGGT CACCGTCTCTTCA SEQ ID NO: 31009 | QVQLQQWGAGLLKPSETLSLTCAVFGGSFSGHYW SWIRQPPGKGLEWIGEMYHFGNTNYNPSLKSRVTM SVDTSKQFSLKLSSVTAADTAVYYCARVGQWLA FDIWGQGTMVTVSS SEQ ID NO: 31010 |
| iPS:436292 | 21-225_205H3 | NA | GACATCCCGATGACCCAGTCTCCATCCTCACT GTCTGCATCTGTAGGAGACAGAGTCACCATCA CTTGTCGGGCGAGTCAGGCCATTAGTAATCAT TTAGCCTGGTTTCAGCTGAAACCAGGGAAAGC CCCTAAGTCCCTGATCTATGCTGCATCCAGTTT GCAAAGTGGGGTCCCATCAAAGTTCACTCTCAC GTGGATCGGGTCAGATTTCACTCTCACCATCA GCAGCCTGCAACAATATGTAATTACCCACTCA CTTTCGGCGGAGGGACCAAGGTGGAGATCAA A SEQ ID NO: 27005 | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGATAGATC AGTTGGCTACGACGGTACGACGTCTGGGGCCA AGGGACCACGGTCACCGTCTCCTCA SEQ ID NO: 31011 | |

FIGURE 50
(Continued)

| | | | | |
|---|---|---|---|---|
| iPS:436294 | 21-225_205G4 | AA | DIPMTQSPSSLSASVGDRVTITCRASQAISNHLAWFQLKPGKAPKSLIYAASSLQSGVPSKFSGSGSGSDFTLTISSLQPEDFATYYCQQYSNYPLTFGGGTKVEIK | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDRSVGYDGTDVWGQGTTVTSS |
| | | | SEQ ID NO: 27006 | SEQ ID NO: 31012 |
| | | NA | GAAATAGTGATGACGCAGTCTCCAGCCACCCTGTCTGTGTCTCCAGGGGAAAGAGCCACCCTCTCCTGCAGGGCCAGTCAGTAAAGCAACTTAGCCTGGTACCAGCAGAAACCTGGCCAGGCTCCCAGGCTCCTCATCTTTGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTTTATAACTGGCTGTGCAGTTTTGGCCAGGGACCAAGCTGGAGCTCAAA | CAGGTACAGCTGCAGCAGTCAGGTCCAGGACTGGTGAAGCCCTCGCAGACCCTCTCACTCACCTGTGCCATCTCCGGGGACAGTGTCTCTAGCAACAGTGCTGCTTGGAACTGGATCAGGCAGTCCCATCGAGAGGCCTGAGTGGCTGGAAGGACATATTACAGGTCCAAGTGGTATAATTATTATGAAGTATCTGTGAGAAGTCGAATAACCATCAACCAGACACATCCAAGAACCAGTTCTCCCTGCAGCTGAATTCTGTGACTCCCGAGGACACGGCTGTGTATTTCTGTGCGAGAGATCAAGGTACTACGGTATGGACGTCTGGGGCCAAGGGACCACGGTCACCGTCTCCTCA |
| | | | SEQ ID NO: 27007 | SEQ ID NO: 31013 |
| | | AA | EIVMTQSPATLSVSPGERATLSCRASQNIKSNLAWYQQKPGQAPRLLIFGASTRATGIPARFSGSGSGTEFTLTISSLQSEDFAVYYCQQFYNWLCSFGQGTKLELK | QVQLQQSGPGLVKPSQTLSLTCAISGDSVSSNSAAWNWIRQSPSRGLEWLGRTYYRSKWYNYEVSVRSRITINPDTSKNQFSLQLNSVTPEDTAVYFCARDQRYYGMDVWGQGTTVTSS |
| | | | SEQ ID NO: 27008 | SEQ ID NO: 31014 |

FIGURE 50
(Continued)

| | | | | |
|---|---|---|---|---|
| iPS:436296 | 21-225_205F5 | NA | GACATCCAGATGACCCAGTCTCCATCCTCACT GTCTGCATCTGTAGGAGACAGAGTCACCATCA CTTGTCGGGCGAGTCAGGCATTGGCAATTAT TTAGCCTGGTTTCAGCAGAAACCAGGGAAAGC CCCTAAGTCCCTGATCTATGGTGTCTCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TACCTGCCAACAATATAGTAATTACCCTCTCA CTTTCGGCGGAGGGACCAAGGTGGACATCAG A | CAGGTGCAGCTGGTGGAGTCTGGGGGAGGCGTG GTCCAGCCTGGGAGGTCCCTGAGACTCTCCTGTG CAGCGTCTGATTCACCTTCAGTAGATATGGCAT GCACTGGGTCCGCCAGGCTCCAGGCAAGGGACT GGAGTGGGTGGCAGTTATATGTAGATGATGAAGT AATGAGAATTATGTAGACTCCGTGAAGGGCCGAT TCACCATCTCCAGAGACACTTCCAAGAAAATGCT GTTTCTGCAAATGAACAGCCTGAGAACCGATGAC ACGGCTGTGTATTACTGTGCGAGAGATATGGGGA TAGGGTATTATGGTATGGACGTCTGGGGCCAAGG GACCACGGTCACCGTCTCCTCA |
| | | | SEQ ID NO: 27009 | SEQ ID NO: 31015 |
| | | AA | DIQMTQSPSSLSASVGDRVTITCRASQGIGNYLA WFQQKPGKAPKSLIYGVSSLQSGVPSKFSGSGSG TDFTLTISSLQPEDFATYTCQQYSNYPLTFGGGT KVDIR | QVQLVESGGGVVQPGRSLRLSCAASGFTFSRYGMH WVRQAPGKGLEWVAVIWYDGSNENYVDSVKGRF TISRDTSKKMFLQMNSLRTDDTAVYYCARDMGIG YYGMDVWGQGTTVTVSS |
| | | | SEQ ID NO: 27010 | SEQ ID NO: 31016 |
| iPS:436302 | 21-225_205G7 | NA | GAAATTGTGTTGACGCAGTCTCCAGGCACCCT GTCTTTGTCTCCAGGGGAAAGAGCCACCCTCT CCTGCAGGGCCAGTCAGAGTGTTTTCAGCAAC TACTTAGCCTGGTACCAGCAGAAACCTGGCCA GGCTCCCAGGCTCCTCATCTATGGTGCATCCA GCAGGGCCGCTGGCATCCCCGACAGGTTCAGT GGCAGTGGGTCTGGGACAGACTTCACTCTCAC CATCAGCAGACTGGAGCCTGAAAATTTTGCAG TGTATTACTGTCAGCAGTATGAAAGTTCACCG TGGACGTTCGGCCAAGGGACCAAGGTGGAAA TCAAA | CAGGTGCAGCTGCAGTACAGCAGTGGGGCGCAGGACTG TTGAAGCCTTCGGAGACCCTGTCCCTCACCTGCG CTGTCTATGGTGGGTCCTTCAGTGTTTATTACTGG AGCTGGATCCGCCAGCCCCCAGGGAAGGGGCTG GAGTGGATTGGGAAAGCAATCAGAGTGGACGC ACCACTACAACCGTCCCTCAAGAGTCGAGTCA CCATATCAGTAGACACGTCCAAGAACCAGTTCTC CCTGAATCTGATCTCTGTGACCGCCGACACG GCTGTGTATTACTGTGCGAGGGACTACGGTGTCT TTGACTACTGGGGCCAGGGAACCCTGGTCACCGT CTCCTCA |
| | | | SEQ ID NO: 27011 | SEQ ID NO: 31017 |

FIGURE 50
(Continued)

| | | | |
|---|---|---|---|
| | | AA | EIVLTQSPGTLSLSPGERATLSCRASQSVFSNYLA WYQQKPGQAPRLLIYGASSRAAGIPDRFSGSGSG TDFTLTISRLEPENFAVYYCQQYESSPWTFGQGT KVEIK | QVQLQQWGAGLLKPSETLSLTCAVYGGSFSVYYW SWIRQPPGKGLEWIGESNQSGRTTYNPSLKSRVTIS VDTSKNQFSLNLISVTAADTAVYYCARDYGVFDY WGQGTLVTVSS |
| | | | SEQ ID NO: 27012 | SEQ ID NO: 31018 |
| iPS:436304 | 21-225_201F3 | NA | GATATTGTGATGACTCAGTCTCCACTCTCCCTG CCCGTCACCCCTGGAGAGCCGGCCTCCATCTC CTGCAGGTCTAGTCAGAGCCTCCTGCATAATA ATAGATACAACCATTTGGATTGGTACCTGCAG AAGCCAGGGCAGTCTCCACAGCTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTTGAGGCTGA GGATGTTGGGGTTTATTACTGCATGCAAGCTC TACAAACTCCCACTTTCGGCGGAGGGACCAAG GTGGAGATCAAA | GAGGTGCAACTGTTGGAGTCTGGGGGAGGCTTG GTACAGCCTGGGGGGTCCCAGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAACTATTAGTGGTAGTGGTGTT AGAACATACTACGCAGACTCCGTGAAGGGCCGG TTCACCATCTCCAGAGACAACATTCCAATAACACGC TGTTTCTGCAAATGAACAGCCTGAGAGCCGAGG ACACGGCCGTATATTACTGTGCGAAAGGGGAG CTAGGAGCAGTGGCTGGTTCCACTTTGACTACTG GGGCCAGGGAACCCTGGTCACCGTCTCCTCA |
| | | | SEQ ID NO: 27013 | SEQ ID NO: 31019 |
| | | AA | DIVMTQSPLSLPVTPGEPASISCRSSSQSLLHNNRY NHLDWYLQKPGQSPQLLIYLGSNRASGVPDRFS GSGSGTDFTLKISRVEAEDVGVYYCMQALQTPT FGGGTKVEIK | EVQLLESGGGLVQPGGSQRLSCAASGFTFSSYAMS WVRQAPGKGLEWVSTISGSGVRTYYADSVKGRFTI SRDNSNNTLFLQMNSLRAEDTAVYYCAKGGARSS GWFHFDYWGQGTLVTVSS |
| | | | SEQ ID NO: 27014 | SEQ ID NO: 31020 |

FIGURE 50
(Continued)

| | | | |
|---|---|---|---|
| iPS:436306 | 21-225_201H4 | NA | GAAATAGTGATGACGCAGTCTCCAGCCACCCT GTCTGTGTCTCCAGGGGAAAGAGCCACCCTCT CCTGCAGGGCCAGTCAGAGTGTTAATAGCTAC TTAGCCTGGTACCAGCAGAAACCTGGCCAGGC TCCCAGGCTCCTCATCTATGGTGCATCCACCA GGGCCACTGGTATCCCAGCCAGGTTCAGTGGC AGTGGGTCTGGGACAGAATTCACTCTCACCAT CAGCAGCCTGCAGTCTGAAGATTTTGCAGTTT ATTACTGTCAAGAGTATAATGACTGGCCGTGC AGTTTTGGCCAGGGACCAACCTGGAGATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGGCT GGAGTGGGTGGCAGCTATATGCAGACTCCGTGAA GGGCCG TAATAAATACAATGCAGACTCCGTGAAGGGCCG ATTCACCATCTCCAGAGACAATTCCAAGAACACG CTGTATATGCAAATGAACAGCCTGAGAGCCGAG GACACGGCTGTATACTACTGTGCGAGAGATGTGG GTACAGTGGGAGCTACTACTTTGACTGCTGGGG CCCGGGAACCCTGGTCACCGTCTCCTCA |
| | | | SEQ ID NO: 27015 | SEQ ID NO: 31021 |
| | | AA | EIVMTQSPATLSVSPGERATLSCRASQSVNSYLA WYQQKPGQAPRLLIYGASTRATGIPARFSGSGSG TEFTLTISSLQSEDFAVYYCQEYNDWPCSFGQGT NLEIK | QVQLVESGGGVVQPGRSLRLSCAASGFTFSSYAMH WVRQAPGKGLEWVAAIWYDGSNKYNADSVKGRF TISRDNSKNTLYMQMNSLRAEDTAVYYCARDVGT VGATYFDCWGPGTLVTVSS |
| | | | SEQ ID NO: 27016 | SEQ ID NO: 31022 |
| iPS:436308 | 21-225_205H8 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACAAGGAAAG CCCCTAAGCTCCTGATCTATTCTGCATCCTTT TGCAAAGAGGGGTCCATCAAGATTCAGCGGC AGTGGATCTGGGACAGCCTGAAGATTCACTCT CAGCAGCCTGCAGTCTGAAGATTCTGCAGTT ATTACTGTCTACAGCATAATAGTTACCCGCTC ACTTTCGGCGGAGGGACCACGGTGAAGATCA AA | CAGGTGCAGCTACAGCAGTGGGGCGCAGGACTG TTGAAGCCTTCGGAGACCCTGTCCCTCACCTGCG CTGTCTATGGTGGGTCCTTCAGTGGTTACTTCTGG AGCTGGATCCGCCAGCCCCCAGGGAAGGGGCTG GAGTGGATTGGGAAATCAGTCATAGTGGACGC ACCAACTACAACCGTCTCCCTCAAGAGCCGAGTCA CCATATCAGTAGACACGTCCAAGAACCAGTTCTC CCTGAAGGTGAGCTCTGTGACCGCCGCGACAC GGCTGTGTATTACTGTGCGAGGGACTACGGGGCG GACTACTGGGGCCAGGGAACCCTGGTCACCGTCT CCTCA |
| | | | SEQ ID NO: 27017 | SEQ ID NO: 31023 |

FIGURE 50
(Continued)

| | | | |
|---|---|---|---|
| | | AA | DIQMTQSPSSLSASVGDRVTITCRASQGIRNDLG WYQQKQGKAPKLLIYSASFLQRGVPSRFSGSGS GTEFTLTISSLQPEDSAAYYCLQHNSYPLTFGGG TTVKIK<br><br>SEQ ID NO: 27018 | QVQLQQWGAGLLKPSETLSLTCAVYGGSFSGYFW SWIRQPPGKGLEWIGEISHSGRTNYNPSLKSRVTISV DTSKNQFSLKVSSVTAADTAVYYCARDYGADYW GQGTLVTVSS<br><br>SEQ ID NO: 31024 |
| iPS:436310 | 21-225_202D11 | NA | GAAATTGTGTTGACGCAGTCTCCAGGCACCCT GTCTTTGTCTCCAGGGGAAAGAGCCACCCTCT CCTGCAGGGCCAGTCAGAGTATTAACAGCAAC TACTTAGCCTGGTACCAGCGGAAGCCTGGCCA GGCTCCCAGGGTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTTTTACTGTCAGCAGTATGAAAACTCACCG TGGACGTTCGGCCAAGGGACCAAGGTGGAAA TCAAA<br><br>SEQ ID NO: 27019 | CAGGTGCAGTACAGCAGCGGGGCGCAGGACTG TTGAAGCCTTCGGAGACCCTGTCCCTCACCTGCG CTGCCTATGGTGGTCCTTCAGTGGTCCCTACTG GAGCTGGATCCGCCAGCCCCCAGGGAAGGGCCT GGAGTGGATTGGGGAAATCAATCATAGTGGAAG CACCAACTACAACCCGTCCCTCAAGAGTCGAGTC ACCATATCAGTAGACACGTCAAGAACCAGTTCT CCCTGAAGCTGAGCTCTGTGACCGCCGCGGACAC GGCTGTTTACTACTGTGCGAGGGACTACGGTGTC CTTGACTACTGGGGCCAGGGAACCCTGGTCACCG TCTCCTCA<br><br>SEQ ID NO: 31025 |
| | | AA | EIVLTQSPGTLSLSPGERATLSCRASQSINSNYLA WYQRKPGQAPRVLIYGASSRATGIPDRFSGSGSG TDFTLTISRLEPEDFAVFYCQQYENSPWTFGQGT KVEIK<br><br>SEQ ID NO: 27020 | QVQLQQRGAGLLKPSETLSLTCAAYGGSFSGPYWS WIRQPPGKGLEWIGEINHSGSTNYNPSLKSRVTISV DTSKNQFSLKLSSVTAADTAVYYCARDYGVLDYW GQGTLVTVSS<br><br>SEQ ID NO: 31026 |

FIGURE 50
(Continued)

| | | | | |
|---|---|---|---|---|
| iPS:436312 | 21-225_206A4 | NA | GACATCCAGATGACCCTGTCTCCATCTCCCCGTCTGCATTTGTTGGAGACAGAGTCACCATCACTCGCCGGGCAAGTCACAACATTAACAGCTATTTAAATTGGTATCAGCAGAAATCAGGAAAGCCCCTAAACTCCTTATCTGTGTGCATCCAGTTTGCAAAGTGGGGGTCCCGTCAAGGTTCAGTGGCAGTGGATCTGGGACAGATTTCACTCTCACTTTCAGTAGTCTACAACCTGAAGATTTTGCAACTTACTACTGTCAACAGAGTTACAGTTTCCGCTCACTTTCGGCGGAGGGACCAAGGTGGAGATGAGG | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATCCACTGGGTGCGACAGGCCCCTGGACAAGGCTTGAGTGGATGGCATGGATCAACCCTAATAGTGGTGGCACAAACTATGCACAGAAGTTTCAGGGCAGGGTCACCATGACCAGGGACACGTCCATCACCACAGCCTACATGGAGCTGAGCAGGCTGAGATCTGACGACACGGCCGTGTATTACTGTGCGAGAGGATACAGCTATGGTTACAACTGGTTCGACCCCTGGGGCCAGGGAACCCTGGTCACCGTCCTCA |
| | | | SEQ ID NO: 27021 | SEQ ID NO: 31027 |
| | | AA | DIQMTLSPSSPSAFVGDRVTITRRASHNINSYLNWYQQKSGKAPKLLICAASSLQSGVPSRFSGSGSGTDFTLTFSSLQPEDFATYYCQQSYSFPLTFGGGTKVEMR | QVQLVQSGAEVKKPGASVKVSCKASGYTFTGYYIHWVRQAPGQGLEWMAWINPNSGGTNYAQKFQGRVTMTRDTSITTAYMELSRLRSDDTAVYYCARGYSYGYNWFDPWGQGTLVTVSS |
| | | | SEQ ID NO: 27022 | SEQ ID NO: 31028 |
| iPS:436314 | 21-225_206G4 | NA | GAAATTGTGCTGACTCAGTCTCCAGACTTTCAGTCTGTGACTCCAAAGGAGAAAGTCACCATCACCTGCCGGGCCAGTCAGAGCATTGGTAGTAGCTTAGCCTGGTACCAGCAGAAACCAGATCAGTCTCCAAAACTCCTCATCAAGTATGCTTCCCAGTCCTTCTCAGGGGTCCCCTCGAGGTTCAGTGGCAGTGGATCTGGGACAGATTTCACCCTCACCATCAATAGCCTGGAAGCTGAAGATGCTGCAACGTATTACTGTCATCAGAGTAGAGAAGTTTACCGCTCACTTTCGGCGGAGGGACCAAGGTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATCCACTGGGTGCGACAGGCCCCTGGACAAGGCTTGAGTGGATGGGATGGATCAACAGAAGTTTCAGGGCAGTGGCACAAACATGACCAGGGACACGTCCATCAGTACAATCACCATGAACATGGAACTGAGCAGGCTGAGATCTGACGACACGGCCGTGTTTTACTGTGCGAAAGATCAAGGGTATAACTGGAACTCTTTGACTACTGGGGCCAGGGAACCCTGGTCACCGTCTCCTCA |
| | | | SEQ ID NO: 27023 | SEQ ID NO: 31029 |

FIGURE 50
(Continued)

| | | | | |
|---|---|---|---|---|
| iPS:436316 | 21-225_206A5 | AA | EIVLTQSPDFQSVTPKEKVTITCRASQSIGRSLHWYQQKPDQSPKLLIKYASQSFSGVPSRFSGSGSGTDFTLTINSLEAEDAATYYCHQSRSLPLTFGGGTKVEIK | QVQLVQSGAEVKKPGASVKVSCKASGYTFTGYYIHWVRQAPGQGLEWMGWIDPNSGGTNYAQKFQGRITMTRDTSISTAYMELSRLRSDDTAVFYCAKDQGYNWNSFDYWGQGTLVTVSS |
| | | | SEQ ID NO: 27024 | SEQ ID NO: 31030 |
| | | NA | GACATCCAGATGACCCAGTCTCCATCCTCCCCGTCTGCATCTGTTGGAGACAGAGTCACCATCACTCGCGGGCAAGTCACAGAGTTAACAGTATCTCGCCCGGGCAAGTCACACATTAACAGTATTAAATTGGTATCAGCAGAAATCAGGGAAAGCCCCTAAACTCCTTATCTGTGTCGCATCCAGTTTCAGCAAAGTGGGGTCCCGTCAAGGTTCAGTGGCAGTGGATCTGGGACAGATTTCACTCTCACTTCAGTAGTCTACAACCTGAAGATTTTGCAACTTACTACTGTCATCAACAGAGTTACAGTTTCCCGCTCACTTTCGGCGGAGGGACCAAGGTGGAGATGAAG | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATCCACTGGGTGCGACAGGCCCCTGGACAAGGCTTGAGTGGATGGCATGGATCAACAGAAGTTTCAGGGCAGTGGCACAAACTATGCACAGGAACACCTTCATCACCAGGTCACCATGACCAGGGACACGTCCATCACCACAGCCTACATGGAGCTGAGCAGGCTGAGATCTGACGACACGGCCGTGTATTACTGTGCGAGAGATACAGCTATGGTTACAACTGGTTCGACCCCTGGGCCAGGGAACCCTGGTCACCGTCTCCTCA |
| | | | SEQ ID NO: 27025 | SEQ ID NO: 31031 |
| | | AA | DIQMTQSPSSPSASVGDRVTITRRASHNINSYLNWYQQKSGKAPKLLICAASSLQSGVPSRFSGSGSGTDFTLTFSSLQPEDFATYYCQQSYSFPLTFGGGTKVEMR | QVQLVQSGAEVKKPGASVKVSCKASGYTFTGYYIHWVRQAPGQGLEWMAWINPNSGGTNYAQKFQGRVTMTRDTSITTAYMELSRLRSDDTAVYYCARGYSYGYNWFDPWGQGTLVTVSS |
| | | | SEQ ID NO: 27026 | SEQ ID NO: 31032 |

FIGURE 50
(Continued)

| | | | |
|---|---|---|---|
| iPS:436324 | 21-225_207G6 | NA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGTGATGGAAGT AATAAAACTATGCAGAGTCCGTGAAGGGCCGA TTCACCATCTCCAGAGACAATTCCAAGAACACGC TGTATCTGCAAATGAACAGCCTGAGAGCCGAGG ACACGGCTGTGTATTATTGTGCGAGAGATGCGGG TATTGGATACTACGGTATAGACGTCTGGGGCCAA GGGACCACGGTCACCGTCTCCTCA |
| | | | SEQ ID NO: 31033 |
| | | AA | DIQMTQSPSSLSASVGDRVTITCRASQGIRNYLA WLQQKPGKAPKSLIHAASSLQSGVPSKFSGNRS GTDFTLTISSLQPEDFATYYCQQYSNYPLTFGGG TKVEIK | QVQLVESGGGVVQPGRSLRLSCAASGFTFSSYGMH WVRQAPGKGLEWVAVIWYDGSNKNYAESVKGRF TISRDNSKNTLYLQMNSLRAEDTAVYYCARDAGIG YYGIDVWGQGTTVTVSS |
| | | | SEQ ID NO: 31034 |
| iPS:436328 | 21-225_207F12 | NA | GACATCCAGATGACCCAGTCTCCATCCTCCCT GTCTGCATCTGTAGGAGACAGAGTCACCATCA CTTGCCGGGCAAGTCAGGGCATTAGAAATTAT TTAGGCTGGTATCAGCAGAAACCAGGAAAG CCCCTAAGCTCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTTCTGTCTACAGCATAATAGTTACCCTCTC ACCTTCGGCCAAGGGACACGACTGGAAATTAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGGTATGATAGAAAT TCACCATCTCCAGAGACAACTCCGTGAAGGGCCGAT GTATCTGCAAATGAACAGCCTGAGAGCCGAGGA CACGGCTGTGTATTACTGTGCGAGAGAACTGGGG TTCCTCTTTGACTACTGGGGCCAGGGAACCCTGG TCACCGTCTCCTCA |
| | | | SEQ ID NO: 31035 |

FIGURE 50
(Continued)

| | | | |
|---|---|---|---|
| iPS:436332 | 21-225_208B2 | AA | DIQMTQSPSSLSASVGDRVTITCRASQGIRNDLG WYQQKPGKAPKRLIY AASSLQSGVPSRFSGSGS GTEFTLTISSLQPEDFATYFCLQHNSYPLTFGQGT RLEIK |
| | | | QVQLVESGGGVVQPGRSLRLSCAASGFTFSNYGM HWVRQAPGKGLEWVAVIWYDRNNKYYGDSVKG RFTISRDNSKNTLYLQMNSLRAEDTAVYYCARELG FLFDYWGQGTLVTVSS |
| | | | SEQ ID NO: 27030 |
| | | | SEQ ID NO: 31036 |
| | | NA | GACATCCAGATGACCCAGTCTCCATCCTCCCT GTCTGCATCTGTAGGAGACAGAGTCACCATCA CTTGCCGGGCAAGTCAGGGCATTAGACATGAT TTAGGCTGGTATCAACAGAAACCAGGAAAG CCCCTAAGCGCCTGATCTATGCTGCATCCAGT TTGCAAAGTGGGGTCCCATCAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAATCA AA |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTGTGTCAT GCACTGGGTCCGCCAGGCTCCAGGCAAGGGGCT GGAGTGGGTGGCAGTTATATGGTATGATGGAAGT AATAAATACTATGGAGACTCCGTGAAGGGCCGAT TCACCATCTCCAGAGACAATTCCAGGAACACGCT GTATCTGCAAATGAACAGCTGAGAGCCGAGGA CACGGCTGTGTATTACTGTGCGAGAGAACGGTAT AGCAGTGGCTTGTACGACTACGGTTTGGACGTCT GGGGCCAAGGGACCACGGTCACCGTCTCCTCA |
| | | | SEQ ID NO: 27031 |
| | | | SEQ ID NO: 31037 |
| | | AA | DIQMTQSPSSLSASVGDRVTITCRASQGIRHDLG WYQQKPGKAPKRLIY AASSLQSGVPSGFSGSGS GTEFTLTISSLQPEDFATYYCLQHYSYPRTFGQG TKVEIK |
| | | | QVQLVESGGGVVQPGRSLRLSCAASGFTFSDCVMH WVRQAPGKGLEWVAVIWYDGSNKYYVDSVKGRF TISRDNSRNTLYLQMNSLRAEDTAVYYCARERYSS GLYDYGLDVWGQGTLVTVSS |
| | | | SEQ ID NO: 27032 |
| | | | SEQ ID NO: 31038 |

FIGURE 50
(Continued)

| | | | |
|---|---|---|---|
| iPS:436334 | 21-225_208G3 | NA | GATATTGTGCTGACTCAGTCTCCACTCTCCCTG CCCGTCACCCCTGGAGAGCCGGCCTCCATCTC CTGCAGGTCTAGTCAGAGCCTCCTGCATAATA ATAAATACAACCATTTGGATTGGTACCTGCAG AAGCCAGGGCAGTCTCCACAGCTCCTGATCTA TTTGGGTTCTAATCGGGCCTCCGGGGTCCCTG ACAGGTTCAGTGGCAGTGGATCAGGCACAGAT TTTACACTGAAAATCAGCAGAGTGGAGGCTGA GGATGTTGGGGTTTATTACTGCATGCAAGCTC TACAAACTCCCACTTTCGGCGGAGGGACCAAG GTGGAGATCAAA SEQ ID NO: 27033 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAACTATTAGTGGTAGTGGTGTT AGAACATACTACGCAGACTCCGTGAAGGGCCGG TCCACCATCTCCAGAGACAATTCCAAGAATACGC TGTTTCTGCAAATGAACAGCCTGAGAGCCGAGG ACAAGGCCGTATATTACTGTGCGAAAGGGGGAG CTAGGAGCAGTGGCTGGTTCCACTTTGACTACTG GGGCCAGGGAACCCTGGTCACCGTCTCCTCA SEQ ID NO: 31039 |
| | | AA | DIVLTQSPLSLPVTPGEPASISCRSSQSLLHNNKY NHLDWYLQKPGQSPQLLIYLGSNRASGVPDRFS GSGSGTDFTLKISRVEAEDVGVYYCMQALQTPT FGGGTKVEIK SEQ ID NO: 27034 | EVQLLESGGGLVQPGGSLRLSCAASGFTFSSYAMS WVRQAPGKGLEWVSTISGSGVRTYYADSVKGRSTI SRDNSKNTLFLQMNSLRAEDKAVYYCAKGGARSS GWFHFDYWGQGTLVTVSS SEQ ID NO: 31040 |
| iPS:436336 | 21-225_208B5 | NA | GAAATTGTTTTGACGCAGTCTCCAGGCACCCT GTCTTTGTCTCCAGGGGAAAGAGCCACCCTCT CCTGCAGGGCCAGTCAGAGTGTTAGCAGCAAC TACTTAGCCTGGTATCAGCAGAAACCTGGCCA GGCTCCCAGACTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTTCTGTCAGCACTACGAAAACTCACCG TGGACGTTCGGCCAAGGGACCAAGGTGGAAA TCAAA SEQ ID NO: 27035 | CAGGTGCAGCTACAGCAGTGGGGCGCAGGACTG TTGAAGCCTTCGGAGACCCTGTCCCTCACCTGCG CTGTCTTTGGTGGGTCCATCAGTGTTACTACTGG ACCTGGATCCGCCAGCCCCCAGGGAAGGGGCTG GAGTGGATTGGGAAATCAATCAATCATAGTGAAGC ACCAACTACAACCCGTCCCTCAAGAGTCGAGTCA CCATATCAGTAGACACGTCCAAGAACCAGTTCTC CCTGAAGCTGAGCTCTGTGACCGCCGCGGACACG GCTGTGTATTACTGTGCGAGGGACGATGGTGTCT TTGATTACTGGGGCCAGGGAACCCTGGTCACCGT CTCCTCA SEQ ID NO: 31041 |

FIGURE 50
(Continued)

| | | | |
|---|---|---|---|
| iPS:436338 | 21-225_208E8 | AA | EIVLTQSPGTLSLSPGERATLSCRASQSVSSNYLA WYQQRPGQAPRLLIYGASSRATGIPDRFSGSGSG TDFTLTISRLEPEDFAVYFCQHYENSPWTFGQGT KVEIK<br>SEQ ID NO: 27036 |
| | | | QVQLQQWGAGLLKPSETLSLTCAVFGGSISVYYWT WIRQPPGKGLEWIGEINHSGSTNYNPSLKSRVTISV DTSKNQFSLKLSSVTAADTAVYYCARDYGVFDYW GQGTLVTVSS<br>SEQ ID NO: 31042 |
| | | NA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TCCACTGGGTGCGACAGGCCCCTGGACAAGGC TTGAGTGGATGGCATGGATCAACCTAATAGTGG TGGCACAAACTATGCACAGAAGTTTCAGGGCAG GGTCACCATGACCAGGGACACGTCCATCACCAC AGCCTACATGGAGCTGAGCAGGCTGAGATCTGA CGACACGGCCGTGTATTACTGTGCGAGAGGATAC AGCTATGGTTACAACTGGTTCGACCCCTGGGCC AGGGAACCCTGGTCACCGTCCTCCTCA<br>SEQ ID NO: 31043 |
| | | AA | DIQMTQSPSSPSAFVGDRVTITRRASHNINSYLN WYQQKSGKAPKLLIYAASSLQSGVPSRFSGSGS GTDFTLTFSSLQPEDFATYYCQQSYSFPLTFGGG TKVEMR<br>SEQ ID NO: 27038 |
| | | | QVQLVQSGAEVKKPGASVKVSCKASGYTFTFGYYIH WVRQAPGQGLEWMAWINPNSGGTNYAQKFQGRV TMTRDTSITTAYMELSRLRSDDTAVYYCARGYSYG YNWFDPWGQGTLVTVSS<br>SEQ ID NO: 31044 |

FIGURE 50
(Continued)

| | | | |
|---|---|---|---|
| iPS:436340 | 21-225_208A9 | NA | GAAATTGTTGTTGACGCAGTCTCCAGGCACCCTGTCTTTGTCTCCAGGGGAAAGAGCCACCCTCCTGCAGGGCCAGTCAGAGTGTTAGCAACAACTACTTAGCCTGGTACCAGCAGAAACCTGGCCAGGCTCCCAGGGTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGCACTATCATAGCTCACCGTGGACGTTCGGCCAAGGGACCAAGGTGGAAATCAAA<br><br>SEQ ID NO: 27039 |
| | | AA | EIVLTQSPGTLSLSPGERATLSCRASQSVSNNYLAWYQQKPGQAPRVLIYGASSRATGIPDRFSGSGSGTDFTLTISRLEPEDFAVYYCQHYHSSPWTFGQGTKVEIK<br><br>SEQ ID NO: 27040 | QVQLQQWGAGLLKPSEPLSLTCAVYGGSFSVSYWSWIRQPPGKGLEWIGEINHSGRANYNPSLKSRVTISIDTSKNQFSLKLSSVTAADTAVYYCARDYGVLDYWGQGTLVTVSS<br><br>SEQ ID NO: 31046 | CAGGTGCAGCTACAGCAGTGGGGCGCAGGACTGTTGAAGCCTTCGGAGCCCTGTCCTCACCTGCGCTGTCTATGTGGGTCCTTCAGTGTTTCTACTGGAGCTGGATCCGCCAGCCCCCAGGGAAGGGGCTGGAGTGGATTGGGGAAATCAATCATAGTGGACGCGCCAACTACAACCGTCCTCAAGAGTCGAGTCACCATATCAATAGACACGTCAAGAACCAGTTCTCCCTGAAGCTGAGCTCTGTGACCGCCGCGACACGGCTGTGTATTACTGTGCGAGGGACTACGGTGTCCTTGACTACTGGGGCCAGGGAACCCTGGTCACCGTCTCCTCA<br><br>SEQ ID NO: 31045 |
| iPS:436344 | 21-225_208B11 | NA | GACATCCAGATGACCCAGTCTCCATCCTCCCTGTCTGCATCTGTTGGAGACAGAGTCACCATCACTTGCCGGGCAAGTCAGAGCATTAACAGCTATTTAAATTGGTATCAGCAGAAATCAGGGAAAGCCCCTAAACTCCTTATCTATGCTGCATCCAGTTTGCAAAGTGGGGTCCCGTCAAGGTTCAGTGGCAGTGGATCTGGGACAGATTTCACTCTCACCATCAGTAGTCTACAACTGAAGATTTTGCAACTTACTACTGTCAACAGAGTTACAGTTTCCCGCTCACTTTCGGCGGAGGGACCAAGGTGGAGATCAAG<br><br>SEQ ID NO: 27041 | | CAGGTGCAGCTGGTGCAGTCTGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGCATGGATCAACCCTAATAGTGGTGGCACAAACTATGCACAGAAGTTTCAGGGCAGGGTCACCATGACCAGGGACACGTCCATCACCACAGCCTACATGGAGCTGAGCAGGCTGAGATCTGACGACACGGCCGTGTATTACTGTGCGAGAGGATACAGCTATGGTTACAACTGGTTCGACCCCTGGGGCCAGGGAACCCTGGTCACCGTCTCCTCA<br><br>SEQ ID NO: 31047 |

FIGURE 50
(Continued)

| | | | |
|---|---|---|---|
| iPS:436350 | 21-225_210E4 | AA | DIQMTQSPSSPSASVGDRVTITCRASHNINSYLN WYQQKSGKAPKLLIYAASSLQSGVPSRFSGSGS GTDFTLTFSSLQPEDFATYYCQQSYSFPLTFGGG TKVEMR<br>SEQ ID NO: 27042 | QVQLVQSGAEVKKPGASVKVSCKASGYTFTFGYYIH WVRQAPGQGLEWMAWINPNSGGTNYAQKFQGRV TMTRDTSITTAYMELSRLRSDDTAVYYCARGYSYG YNWFDPWGQGTLVTVSS<br>SEQ ID NO: 31048 |
| | | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br>SEQ ID NO: 27043 | CAGGTGCAGCTGGTGGTGGAGTCTGGGGGAGGCGTG GTCCAGCCTGGGAGGTCCCTGAGACTCTCCTGTG CAGCGTCTGGATTCACCCTCATTAACTATGGCAT GCACTGGGTCCGCCAGGCTCCAGGCAAGGGCT GGAGTGGGTGGCAGTTATATGTAGACTCCGTGAAGGGCCGAT TCACCATCTCCAGAGACGATTCCAAGAACACGCT GTATCTGCAAATGAACAGCCTGAGAGCCGAGGA CTCGGCTGTGTATTACTGTGCGAGAGAGACGGT TCTTGAGCGACTACTGGGGCCAGGGAACCCTGG TCACCGTCTCCTCA<br>SEQ ID NO: 31049 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br>SEQ ID NO: 27044 | QVQLVESGGGVVQPGRSLRLSCAASGFTLNYGMH WVRQAPGKGLEWVAVIWYDENNKYYVDSVKGRF TISRDDSKNTLYLQMNSLRAEDSAVYYCARETGFL SDYWGQGTLVTVSS<br>SEQ ID NO: 31050 |

FIGURE 50
(Continued)

| | | | |
|---|---|---|---|
| iPS:436352 | 21-225_210G5 | NA | GACATCCAGATGACCCAGTCTCCATCCTCCT GTCTGCATCTGTAGGAGACAGAGTCACCATCA CTTGCCGGGCAAGTCAGGGCATTAGACATGAT TTAGGCTGGTATCAACAGAAACCAGGGAAAG CCCCTAAGCGCCTGATCTATGCTGCATCCAGT TTGCAAAGTGGGGTCCCATCAGGGTTCAGCGG CAGTGGATCTGGGACAGAATTCACTCTCACAA TCAGCAGCCTGCAGCCTGAAGATTTTGCAACT TATTACTGTCTACACCATTATAGTTACCCTCGG ACGTTCGGCCAAGGGACCAAGGTGGAAATCA AA | CAGGTGCAGCTGGTGGAGTCTGGGGAGGCGTG GTCCAGCCTGGGAGGTCCCTGAGACTCTCCTG CAGCGTCTGATTCACCTTCAGTGACTGTGTCAT GCACTGGGTCCGCCAGGCTCCAGGCAAGGGCT GGAGTGGGTGGCAGTTATATGACTCCGTGAAGT AATAAATACTATGTAGACTCCGTGAAGGGCCGAT TCACCATCTCCAGAGACAATTCCAGGAACACGCT GTATCTGCAAATGAACAGCCTGAGAGCCGAGGA CACGGCTGTGTATTACTGTGCGAGAGAACGGTAT AGCAGTGGCTTGTACGACTACGGTTTGGACGTCT GGGGCCAAGGGACCACGGTCACCGTCTCCTCA |
| | | | SEQ ID NO: 27045 | SEQ ID NO: 31051 |
| | | AA | DIQMTQSPSSLSASVGDRVTITCRASQGIRHDLG WYQQKPGKAPKRLIYAASSLQSGVPSGFSGSGS GTEFTLTISSLQPEDFATYYCLHHYSYPRTFGQG TKVEIK | QVQLVESGGGVVQPGRSLRLSCAASGFTFSDCVMH WVRQAPGKGLEWVAVIWYDGSNKYYVDSVKGRF TISRDNSRNTLYLQMNSLRAEDTAVYYCARERYSS GLYDYGLDVWGQGTTVTVSS |
| | | | SEQ ID NO: 27046 | SEQ ID NO: 31052 |
| iPS:436354 | 21-225_210G10 | NA | GACATCCAGATGACCCAGTCTCCATCCTCCT GTCTGCATCTGTAGGAGACAGAGTCACCATCA CTTTCCGGACAAGTCAGGGCATTAGAAATGAT TTAGGCTGGTATCAGCAGCAACCAGGGAAAA CCCCTAAGCGCCATGATTTATGCTGCATCCAGT TTGTTTAGTGGGGTCCCATCAAGGTTCAGCGG CAGTAGATCTGGGACAGATTTCACTCTCACAA TCAGCAGCCTGCAGCCTGAAGATTTTGCAACT TATTACTGTCTACAGTATAATAGTTACCCTCCC ACCTTCGGCCAAGGGACACGACTGGAGATTAA A | CAGGTGCAGCTGCAGGAGTCGGGCCCAGGACTG GTGAAGCCTTCGGAGACCCTGTCCCTCAACTGCA CTGTCTCTGGTGGCTCCATCAGGAGTTACTACTG GAGCTGGATCCGGCAGCCCGCGGAAGGGACT GGAGTGGATTGGGCGTATCTATACCAGTGGGAGC ACCGACTACAACCCCTCCCTCAAGAGTCGAATCA CCATGTCAGTAGACACGTCCAAGAACCAGTTCTC TTTGAAGCTGAGCTCTGTGACCGCCGCGGACACG GCCGTGTATTACTGTGCGAGAGGGTTCGGTGACT GGGACTACTGGGGCCAGGGAACCCTGGTCACCG TCTCCTCA |
| | | | SEQ ID NO: 27047 | SEQ ID NO: 31053 |

FIGURE 50
(Continued)

| | | | |
|---|---|---|---|
| iPS:436356 | 21-225_210H10 | AA | DIQMTQSPSSLSASVGDRVTITFRTSQGIRNDLG WYQQQPGKTPKRMIYAASSLFSGVPSRFSGSRS GTDFTLTISSLQPEDFATYYCLQYNSYPPTFGQG TRLEIK<br>SEQ ID NO: 27048 | QVQLQESGPGLVKPSETLSLNCTVSGGSIRSYYWS WIRQPAGKGLEWIGRIYTSGSTDYNPSLKSRITMSV DTSKNQFSLKLSSVTAADTAVYYCARGFGDWDYW GQGTLVTVSS<br>SEQ ID NO: 31054 |
| | | NA | GAAATAGTGATGACGCAGTCTCCAGCCACCCT GTCTGTGTCTCCAGGGGAAAGAGCCACCCTCT CCTGCAGGGCCAGTCAGAGTGTTAAAAGCAAC TTAGCCTGGTACCAGCAGAAACCTGGCCAGGC TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCAGCCTGCAGTCTGAAGATTTTGCAGTTT ATTCCTGTCAGCAGTATTATAACTGGCTGTGC AGTTTTGGCCAGGGGACCAAGCTGGAGATCAA A<br>SEQ ID NO: 27049 | CAGGTACACAGTCTGCAGCAGTCAGGTCCAGGACTG GTGAAGCCCTGCAGACCCTCTCACTCACCTGTG CCATCTCCGGGACAGTGTCTCTAGCAACAGTGC TGCTTGGAACTGGATCAGGCAGTCCCATCGAGA GGCCTTGAGTGGCTGGAAGGACATACTACAGG TCCAAGTGGTATAATTATTATCCAGTATCTGTGA GAAGTGAATAACCATCAACCAGACACATCCA AGAACCAGTTCTCCCTGCTGCTGAACTCTGTGAC TCCCGAGGACACGGCTGTGTATTACTGTGCAAGA GATCAACGGTACTACGGTATGGACGTCTGGGGCC AAGGGACCACGGTCACCGTCTCCTCA<br>SEQ ID NO: 31055 |
| | | AA | EIVMTQSPATLSVSPGERATLSCRASQSVKSNLA WYQQKPGQAPRLLIYGASTRATGIPARFSGSGSG TEFTLTISSLQSEDFAVYSCQQYYNWLCSFGQGT KLEIK<br>SEQ ID NO: 27050 | QVQLQQSGPGLVKPSQTLSLTCAISGDSVSSNSAA WNWIRQSPSRGLEWLGRTYYRSKWYNYPVSVRS RITINPDTSKNQFSLLLNSVTPEDTAVYYCARDQRY YGMDVWGQGTTVTVSS<br>SEQ ID NO: 31056 |

FIGURE 50
(Continued)

| | | | | |
|---|---|---|---|---|
| iPS:436358 | 21-225_210D11 | NA | GACATCCAGATGACCCAGTCTCCATCTCCT GTCTGCATCTGTTGGAGACAGAGTCACCATCA CTTGCCGGGCAAGTCACAACATTAACAGCTAT TTAAATTGGTATCAGCAGAAATCAGGAAAGC CCCTAAACTCCTAATCTATGCTGCATCCAGTTT GCAAAGTGGGGTCCCGTCAAGGTTCAGTGGCA GTGGATCTGGGACAGATTTCACTCTCACCTTC AGTAGTCTACAACCTGAAGATTTTGCAACTTA CTACTGTCAACAGAGTTACAGTTTCCGCTCA CTTTCGGCGGAGGGACCAAGGTGGAGATGAG G | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TCCACTGGGTGCGACAGCCCCTGGACAAGGGC TTGAGTGGATGGCATGGATCAACCCTAATAGTGG TGGCACAAACTATGCACAGAAGTTCAGGCAG GGTCACCATGACCAGGGACACGTCCATCACCAC AGCCTACATGGAGCTGAGCAGGCTGAGATCTGA CGACACGGCCGTGTATTACTGTGCGAGAGGATAC AGCTATGGTTACAACTGGTTCGACCCCTGGGGCC AGGGAACCCTGGTCACCGTCTCCTCA |
| | | AA | DIQMTQSPSSLSASVGDRVTITCRASHNINSYLN WYQQKSGKAPKLLIYAASSLQSGVPSRFSGSGS GTDFTLTFSSLQPEDFATYYCQQSYSFPLTFGGG TKVEMR | SEQ ID NO: 31057 |
| | | | SEQ ID NO: 27051 | QVQLVQSGAEVKKPGASVKVSCKASGYTFTGYYIH WVRQAPGQGLEWMAWINPNSGGTNYAQKFQGRV TMTRDTSITTAYMELSRLRSDDTAVYYCARGYSYG YNWFDPWGQGTLVTVSS |
| | | | SEQ ID NO: 27052 | SEQ ID NO: 31058 |
| iPS:436360 | 21-225_210H11 | NA | GACATCCAGATGACCCAGTCTCCATCTTCCGT GTCTGCTTCTCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCTGCATCCAGTT TGCAAAGTGGAGTCCCATCAAGGTTCAGCGGC AGAGGATCTGGGACAGATTTCACTCTCACCAT CAGCAGCCTGCAGCCTGAAGATTTTGCAACTT ACTATTGTCAACAGGCTAAAAGTTTCCCATTC ACTTTCGGCCCTGGGACCAAAGTGGATATCAA A | CAGGTGCAGCTGGTGGAGTCTGGGGGAGGCGTG GTCCAGCCTGGGGAGTCCCTGAGACTCTCCTGTG CAGCGTCTGGATTCACCTTCAGTAGCTAGCCATGCAT GCCTGGGTCCGCCAGGCTCCAGGCAAGGGCT GGAGTGGGTGGCAGTTACATGGTATGATGGAAG TGATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTATATTACTGTGCGCGAGACCGGC TAGTGGGAGCTACTACCGATGCTTTTGATATCTG GGGCCAAGGGACAATGGTCACCGTCTCTTCA |
| | | | SEQ ID NO: 27053 | SEQ ID NO: 31059 |

FIGURE 50
(Continued)

| | | | |
|---|---|---|---|
| | | AA | DIQMTQSPSSVSASVGDRVTITCRASQGISIWLA WYQQKPGKAPNLLIYAASSLQSGVPSRFSGRGS GTDFTLTISSLQPEDFATYYCQQAKSFPFTFGPGT KVDIK<br><br>SEQ ID NO: 27054 | QVQLVESGGGVVQPGRSLRLSCAASGFTFSSHGMH WVRQAPGKGLEWVAVTWYDGSDKYYADSVKGR FTISRDNSKNTLYLQMNSLRAEDTAVYYCARDRLV GATTDAFDIWGQGTMVTVSS<br><br>SEQ ID NO: 31060 |
| iPS:436362 | 21-225_210C12 | NA | GATATTGTGATGACTCAGTCTCCACTCTCCCTG CCCGTCACCCCTGGAGAGCCGGCCTCCATCTC CTGCAGGTCTAGTCAGAGCCTCCTGCATTATA ATGGACACAACTTTTTGGATTGGTACCTGCAG AAGCCAGGGCAGTCTCCACAGCTCCTGATCTA TTTGGTTTCTAATCGGGCCTCCGGGGTCCCTGA CAGGTTCAGTGGCAGTGGATCAGGCACAGATT TTACACTGAAAATCAGCAGAGTGGAGGCTGA GGATGTTGGGGTTTATTACTGCATGCAAGCTC TACAAACTCCCATGTGCAGTTTTGGCCAGGGG ACCAAGTTGGAGATCAAA<br><br>SEQ ID NO: 27055 | CAGGTTCAGCTGGTGCAGTCTGGAGCTGAGGTGA CGAAGCCTGGGGCCTCAGTGAAGGTCTCCTGCAA GGCTTCTGGTTACACCTTTACCAACAATGGTATC AGCTGGGTGCGACAGGCCCCTGGACAAGGGCTT GAGTGGATGGGATGGATCAACGCTTACAATGGTC ACACAAACTATGCACAGAAGTTCCAGGGCAGAG TCACCATGACCACAGACACATCCACGAGCACAG CCTACATGGAGCTGAGGAGCCTGAGATCTGACG ACACGGCCGTGTATTACTGTGCGAGAGATCCTAC GGTGACCCACTACTATTACTACGGTATGGACGTC TGGGGCCAAGGGACCACGGTCACCGTCTCCTCA<br><br>SEQ ID NO: 31061 |
| | | AA | DIVMTQSPLSLPVTPGEPASISCRSSQSLLHYNGH NFLDWYLQKPGQSPQLLIYLVSNRASGVPDRFS GSGSGTDFTLKISRVEAEDVGVYYCMQALQTPM CSFGQGTKLEIK<br><br>SEQ ID NO: 27056 | QVQLVQSGAEVTKPGASVKVSCKASGYTFTNNGIS WVRQAPGQGLEWMGWINAYNGHTNYAQKFQGR VTMTDTSTSTAYMELRSLRSDDTAVYYCARDPTV THYYYGMDVWGQGTTVTVSS<br><br>SEQ ID NO: 31062 |

FIGURE 50
(Continued)

| | | | | |
|---|---|---|---|---|
| iPS:436364 | 21-225_211A11 | NA | GACATCCAGATGACCCAGTCTCCATCCTCACT GTCTGCATCTGTAGGAGACAGAGTCACCATCA CTTGTCGGGCGAGTCAGGGCATTGGCAATTAT TTAGCCTGGTTTCAGCAGAAACCAGGGAAAGC CCCTAAGGTCCCTGATCTATGATGCATCCAGTTT GGAAAGTGGGGTCCCATCAAAGTTCAGCGGC AGTAGGTCTGGGACAGATTTCACTCTCACCAT CGGCAGCCTGCAGCCTGAAGATTTTGCAACTT ATTACTGCCAACACTATGACTTACCGCTC ACTTTCGGCGCAGGGACCAAGGTGGAGATCA AA | CAGGTGCAGCTGGTGGTGGGTCTGGGGGAGGCGTG GTCCAGCCTGGGAGGTCCCTGAGACTCTCCTGTG CAGCCTCTGAATTCACCTTCAGTAGCTATGGCAT GCACTGGGTCCGCCAGGCTCCAGGCAAGGGCT GGAATGGGTGGCAGTTCTTTGGTTTGATGGAAGT AATAGAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGGG AGTGGGCTACTACGGTACGGACGTCTGGGGCCA AGGGACCACGGTCACCGTCTCCTCA |
| | | | SEQ ID NO: 27057 | SEQ ID NO: 31063 |
| | | AA | DIQMTQSPSSLSASVGDRVTITCRASQGIGNYLA WFQQKPGKAPRSLIYDASSLESGVPSKFSGSRSG TDFTLTIGSLQPEDFATYYCQHYMTYPLTFGAGT KVEIK | QVQLVQSGGGVVQPGRSLRLSCAASGFTFSSYGMH WVRQAPGKGLEWVAVLWFDGSNRNYADSVKGRF TISRDNSKNTLYLQMNSLRAEDTAVYYCARDRGV GYYGTDVWGQGTTVTVSS |
| | | | SEQ ID NO: 27058 | SEQ ID NO: 31064 |
| iPS:436366 | 21-225_211A3 | NA | GACATCCGGATGACCCAGTCTCCATCCTCACT GTCTGCATCTGTAGGAGACAGAGTCACCATCA CTTGTCGGGCGAGTCAGGCCATTGGGAAACAT TTAGCCTGGTTTCAGCAGAGGCCTGGGAAAGC CCCTAAGGTCCCTGATCTATGCTGCATCCAGATT GCAAAGTGGGGTCCCATCAAAGTTCAGCGGCA GTGGATCTGGGACAGATTTCACTCTCACCATC AGCAGCCTGCAGCCTGAAGATCTTGCAACTTA TTACTGTCAACAGTATAGTAATTATCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGTGTCTGGAATCACCTTCAGTAGTTATGGCAT GCACTGGGCCCGCCAGGCTCCAGGCAAGGGGCT GGAGTGGGTGGCAGTTATATGGTATGATGGAAGT AATAAAAACTATGAAGACTCCGTGAAGGGCCGA TTCACCATCTCCAGAGACAACTCCAAGAACACGC TGTATCTGCAAATGAACAGCCTGAGAGCCGAGG ACACGGCTGTGTATTACTGTGCGAGAGATGGGAG TTATGGTTACGACGTATGGACGTCTGGGGCCAA GGGACCACGGTCACCGTCTCCTCA |
| | | | SEQ ID NO: 27059 | SEQ ID NO: 31065 |

FIGURE 50
(Continued)

| | | | |
|---|---|---|---|
| iPS:436368 | 21-225_211G3 | AA | DIRMTQSPSSLSASVGDRVTITCRASQAIGKHLA WFQQRPGKAPKSLIYAASRLQSGVPSKFSGSGSG TDFTLTISSLQPEDLATYYCQQYSNYPLTFGGGT KVEIK<br><br>SEQ ID NO: 27060 | QVQLVESGGGVVQPGRSLRLSCAVSGITFSSYGMH WARQAPGKGLEWVAVIWYDGSNKNYEDSVKGRF TISRDNSKNTLYLQMNSLRAEDTAVYYCARDGSYG YDGMDVWGQGTTVTVSS<br><br>SEQ ID NO: 31066 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGC TTCTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGTTAGCTCACCG CTCACTTTCGGCGGAGGGACCAAGGTGGAGAT CAAA<br><br>SEQ ID NO: 27061 | CAGGTGCAGCTGGTGGAGTCTGGGGGAGGCGTG GTCCAGCCTGGGAGGTCCCTGAGACTCTCCTGTG CAGCGTCTGGAATTCACCTTCAGTAGTTATGGCAT GCACTGGGTCCGCCAGGCTCCAGGCAAGGGGCT GGAGTGGGTGGCAGTTATATGGTATGATGGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGGTTAGACT ACAGTAACTACGGGTGGTTCGACCCCTGGGGCCA GGGAACCCTGGTCACCGTCTCCTCA<br><br>SEQ ID NO: 31067 |
| | | AA | EIVLTQSPGTLSLSPGERATLSCRASQSVSSSFLA WYQQKPGQAPRLLIYGASSRATGIPDRFSGSGSG TDFTLTISRLEPEDFAVYYCQQYVSSPLTFGGGT KVEIK<br><br>SEQ ID NO: 27062 | QVQLVESGGGVVQPGRSLRLSCAASGFTFSNYGM HWVRQAPGKGLEWVAVIWHDGSNKYYADSVKGR FTISRDNSKNTLYLQMNSLRAEDTAVYYCARLDYS NYGWFDPWGQGTLVTVSS<br><br>SEQ ID NO: 31068 |

FIGURE 50
(Continued)

| | | | |
|---|---|---|---|
| iPS:436370 | 21-225_211A6 | NA | GACATCGAGATGACCCAGTCTCCATCCTCACT GTCTGCATCTGTAGGAGACAGCGTCACCATCA CTTGTCGGGCGAGTCAGGGCATTGCAAGTAT TTAGCCTGGTTTCAGCAGAAACCAGGGAAAGC CCCTAAGTCCCTGATCTATGCTGCATCCAGTTT GCTAAGTGGGGTCCCATCAAAGTTCAGCGGCA GTGGATCTGGGACAGATTTCACTCTCACCATC AGCAGCCTTCAGCCTGAAGATTTTGCCACTTA TTACTGCCAAAAGTATGATACTTACCCATTCA CTTTCGGCCCTGGGACCAAAGTGGATATCAAA<br><br>SEQ ID NO: 27063 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATAAAAACTATGCAGACTCCGTGAAGGGCCGA TTCACCATCTCCAGAGACAACTCCAAGAACACGC TGTATCTGCAAATGAACAGCCTGAGAGCCGAGG ACACGGCTGTGTTTACTGTGCGAGAGATAGGAC GGTGGGCTATGATGGTTTTGATATCTGGGGCCAA GGGACAATGGTCACCGTCTCTTCA<br><br>SEQ ID NO: 31069 |
| | | AA | DIQMTQSPSSLSASVGDSVTITCRASQGIGKYLA WFQQKPGKAPKSLIYAASSLLSGVPSKFSGSGSG TDFTLTISSLQPEDFATYYCQKYDTYPFTFGPGT KVDIK<br><br>SEQ ID NO: 27064 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVFYCARDRTVG YDGFDIWGQGTMVTVSS<br><br>SEQ ID NO: 31070 |
| iPS:436372 | 21-225_211A8 | NA | GACATCGAGATGACCCAGTCTCCACCCTCACT GTCTGCATTTGTAGGAGACAGAGTCACCATCA CTTGTCGGGCGAGTCAGGGCATTAGCAGATAT TTAGCCTGGTTCAGCAGAAACCAGGGAAAG CCCCTAAGTCCCTGATCTATGCTGCATCCAGTT TGCAAAGTGGGGTCTCATCAAGGTTCAGCGGC AGTGGATCTGGGACAGATTTCACTCTCACCAT CAGCAGCCTGCAGCCTGAAGATTTTGCAACTT ATTACTGCTCTACGGTATGATACTTACCCTCTCA TTTTCGGCGGAGGGACCAAGGTGGAGATCAA G<br><br>SEQ ID NO: 27065 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATGAACACTATGCAGACTCCGTGAAGGGCCGA TTCACCATCTCCAGAGACAATTCCAAGAAAACGC TGTATCTGCAAATGAACAGCCTGAGAGCCGAGG ACACGGCTGTGTATTACTGTGCGAGAGACCACGG TGTCGGGTACTACGGTATGGACGTCTGGGGCCAA GGGACCACGGTCACCGTCTCCTCA<br><br>SEQ ID NO: 31071 |

FIGURE 50
(Continued)

| | | | |
|---|---|---|---|
| iPS:436374 | | AA | DIEMTQSPPSLSAFVGDRVTITCRASQGISRYLA WVQQKPGKAPKSLIYAASSLQSGVSSRFSGSGSG TDFTLTISSLQPEDFATYYCLRYDTYPLIFGGGTK VEIK | QVQLVESGGGVVQPGRSLRLSCAASGFTFSSYGMH WVRQAPGKGLEWVAVIWYDGSNEHYADSVKGRF TISRDNSKKTLYLQMNSLRAEDTAVYYCARDHGV GYYGMDVWGQGTTVTVSS |
| | | | SEQ ID NO: 27066 | SEQ ID NO: 31072 |
| | 21-225_211C10 | NA | GATATTGTGATGACTCAGTCTCCACTCTCCCTG CCCGTCACCCCTGGAGAGCCAGGCCTCCATCTC CTGCAGGTCTAGTCAGAGCCTCCTCCATAGTA ATGGATACAACTATTTGGATTGGTACCTGCTG AAGCCAGGGCAGTCTCCACAGCTCCTGATCTA TTTGGGTTCTAATCGGGCCTCCGGGGTCCCTG ACAGGTTCAGTGGCAGTGGATCAGGCACAGAT TTTACACTGAAAATCAGCAGAATGGAGGCTGA GGATGTTGGGATTTATTACTGCATGCAAGCTC TACTAACTCCCGTGTGCAGTTTTGGCCAGGGG ACCAAGCTGGAGATCAAA | CAGGTTCAGCTGGTGCAGTCTGGAGCTGAGGTGA AGAAGCCTGGGGCCTCAGTGAAGGTCTCCTGCA AGGCTTCTGGTTACACCTTTACCAGGCATGGTAT CAGCTGGGTGCGACTGGCCCCTGGACAAGGGCTT GAGTGGATGGGATGGATCAGCGCTTACAATGGTC TCACAAACTATGCACAGAAGTTCCAGGGCAGAG TCACCATGACCACAGACACATCCACGAGCACAG GCTACATGGAGCTGCGAGCCTGAGATCTGACG ACACGGCCGTGTATTACTGTGCGAGAGATCCTAC GGTGACCCACTACTACTACGTATGGACGTC TGGGGCCAAGGGACCACGGTCACCGTCTCCTCA | 
| | | | SEQ ID NO: 27067 | SEQ ID NO: 31073 |
| | | AA | DIVMTQSPLSLPVTPGEPASISCRSSQSLLHSNGY NYLDWYLLKPGQSPQLLIYLGSNRASGVPDRFS GSGSGTDFTLKISRMEAEDVGHYYCMQALLTPV CSFGQGTKLEIK | QVQLVQSGAEVKKPGASVKVSCKASGYTFTRHGIS WVRLAPGQGLEWMGWISAYNGLTNYAQKFQGRV TMTTDTSTSTGYMELRSLRSDDTAVYYCARDPTVT HYYYYGMDVWGQGTTVTVSS |
| | | | SEQ ID NO: 27068 | SEQ ID NO: 31074 |

FIGURE 50
(Continued)

| | | | | |
|---|---|---|---|---|
| iPS:436376 | 21-225_212E6 | NA | GACATCCAGATGACCCAGTCTCCATCCTCACT GTCTGCATCTGTAGGAGACAGAGTCACCATCA CTTGTCGGGCGAGTCAGGGCATTAGCAATCAT TTAGCCTGGTTTCAGCAGAAACCAGGGCAAGC CCCTAAGTCCCTGATCTATGCTGCATCCAGTTT GCAAAGTGGGGTCCCATCAAAGTTCAGCGGCA GTAGATCTGGGACAGATTTCACTCTCACCATC AGCAGCCTGCAGCCTGAAGATTTTGCAACTTA TTACTGCCAACAGTATGTTACCTACCCTCTCAC TTTCGGCGGAGGGACCAAGGTGGAGATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGCT GGAGTGGGTGGCAGTTATATGTATGATGGAAGT AATAAAAACTATGTAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGACTACGG TGTCGGGTACTACGGTACGGACGTCTGGGGCCAA GGGACCACGGTCACCGTCTCCTCA |
| | | AA | DIQMTQSPSSLSASVGDRVTITCRASQGISNHLA WFQQKPGQAPKSLIYAASSLQSGVPSKFSGSRSG TDFTLTISSLQPEDFATYYCQQYVTYPLTFGGGT KVEIK SEQ ID NO: 27070 | QVQLVESGGGVVQPGRSLRLSCAASGFTFSSYGMH WVRQAPGKGLEWVAVIWYDGSNKNYVDSVKGRF TISRDNSKNTLYLQMNSLRAEDTAVYYCARDYGV GYYGTDVWGQGTTVTVSS SEQ ID NO: 31076 |
| | | | SEQ ID NO: 27069 | SEQ ID NO: 31075 |
| iPS:436378 | 21-225_212D7 | NA | GACATCCAGATGACCCAGTCTCCATCCTCACT GTCTGCATCTGTAGGAGACAGAGTCACCATCA CTTGTCGGGCGAGTCAGGGCATTAGCAATCAT TTAGCCTGGTTTCAGCAGAAACCAGGGAAAGC CCCTAAGTCCCTGATCTACATGCTGCATCCAGTTT GCAAAGTGGGGTCCCATCAAAATTCAGCGGCA ATAGATCTGGGACAGATTTCACTCTCACCATC AACAACCTGCAGCCTGAAGATATTGTAACTTA TTACTGCCAGCAGTATAGTAATTACCCTCTCA CTTTCGGCGGAGGGACCAAGGTGGAGATCAA A SEQ ID NO: 27071 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGTATGATGGAAGT AATAAAAATTATGCAGACTCCGTGAAGGGCCGA TTCACCATCTCCAGAGACAATTCCAAGAACACGC TGTCTCTGCAAATGAACAGCCTGAGAGCCGAGG ACACGGCTGTGTATTACTGTGCGAGAGACTACGG TGTCGGGTACTACGGTACGGACGTCTGGGGCCAA GGGACCACGGTCACCGTCTCCTCA SEQ ID NO: 31077 |

FIGURE 50
(Continued)

| | | | | |
|---|---|---|---|---|
| iPS:436380 | 21-225_212H9 | AA | DIQMTQSPSSLSASVGDRVTITCRASQGISNHLA WFQQKPGKAPKSLIHAASSLQSGVPSKFSGNRSG TDFTLTINNLQPEDFVTYYCQQYSNYPLTFGGGT KVEIK<br><br>SEQ ID NO: 27072 | QVQLVESGGGVVQPGRSLRLSCAASGFTFSSYGMH WVRQAPGKGLEWVAVIWYDGSNKNYADSVKGRF TISRDNSKNTLSLQMNSLRAEDTAVYYCARDYGVG YYGTDVWGQGTTVTVSS<br><br>SEQ ID NO: 31078 |
| | | NA | GACATCGAGATGACCCAGTCTCCATCCTCACT GTCTGCATCTGTAGGAGACAGAGTCACCATCA CTTGTCGGGCGAGTCAGGGCATTAGCAGTTAT TTAGCCTGGCTTCAGCAGAAACCAGGGAAAGC CCCTAAGTCCCTGATCTATGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTCGCAACTTA TTATTGCCTACGGTATGATACTTACCCTCTCAC TTTCGGCGGAGGGACCAAGGTGGAGATCAAG<br><br>SEQ ID NO: 27073 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGTATGATGGAAGT AATGAACACTATGCAGACTCCGTGAAGGGCCGA TTCACCATCTCCAGAGACAACAATTCCAAGAAAACGC TGTATCTGCAAATGAACAGCCTGAGAGCCGAGG ACACGGCTGTGTATTACTGTGCGAGAGACCACGG TGTCGGGTACTACGGTATGGACGTCTGGGGCCAA GGGACCACGGTCACCGTCTCCTCA<br><br>SEQ ID NO: 31079 |
| | | AA | DIEMTQSPSSLSASVGDRVTITCRASQGISSYLA WLQQKPGKAPKSLIYAASSLQSGVPSRFSGSGSG TDFTLTISSLQPEDFATYYCLRYDTYPLTFGGGT KVEIK<br><br>SEQ ID NO: 27074 | QVQLVESGGGVVQPGRSLRLSCAASGFTFSSYGMH WVRQAPGKGLEWVAVIWYDGSNEHYADSVKGRF TISRDNSKKTLYLQMNSLRAEDTAVYYCARDHGV GYYGMDVWGQGTTVTVSS<br><br>SEQ ID NO: 31080 |

FIGURE 50
(Continued)

| | | | |
|---|---|---|---|
| iPS:436382 | 21-225_212C10 | NA | GAAATAGTGATGACGCAGTCTCCAGCACCCT GTCTGTGTCTCCAGGGGAAAGAGCCACCCTCT CCTGCAGGGCCAGTCAGAGTGTTGCCAGCAGC TTAGCCTGGTACCAGCAGCAGAAGCCTGGCCAGGC TCCCAGGCTCCTCATCCATGGTACATCCACCA GGGCCACTGATGTCCCAGCCAGGTTCAGTGGC TTTGGGTCTGGGTCGGACTTCACTCTCACCATC AGCAGCCTGCAGTCTGAAGATTTTGCAGTTTA TTCCTGTCAGCAGTATAATGACTGGCCGTGCA GTTTTGGCCAGGGGACCAAGCTGGAGATCAAA<br><br>SEQ ID NO: 27075 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAATGGGTGACAGTATATGGTATGATGAAG TCATAAATACTATACAGATTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGAG TATAGTGGGAGCTACCTACTTTGACTACTGGGGC CAGGGAACCCTGGTCACCGTCTCCTCA<br><br>SEQ ID NO: 31081 |
| | | AA | EIVMTQSPATLSVSPGERATLSCRASQSVASSLA WYQQKPGQAPRLLIHGTSTRATDVPARFSGFGS GSDFTLTISSLQSEDFAVYSCQQYNDWPCSFGQG TKLEIK<br><br>SEQ ID NO: 27076 | QVQLVESGGGVVQPGRSLRLSCAASGFTFSSYGMH WVRQAPGKGLEWVTAIWYDGSHKYYTDSVKGRF TISRDNSKNTLYLQMNSLRAEDTAVYYCARDRSIV GATYFDYWGQGTLVTVSS<br><br>SEQ ID NO: 31082 |
| iPS:436384 | 21-225_212F10 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGACTGGTTTCAGCAGAAACCAGGGAAAGC CCCTAAGTCCCTGATCTATTCTGCATCCAATTT GCAAAGTGGGGTCCCATCAAAGTTCAGCGGCA GTAGATCTGGGACAGATTTCACTCTCACCATC AGCAGCCTGCAGCCTGAAGATTTTGCAACTTA TTACTGCCAACACTATAGTAATTACCCGCTCA CTTTCGGCGGAGGGACCAAGGTGGAGATCAA A<br><br>SEQ ID NO: 27077 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGATATGGCAT GCACTGGGTCCGCCAGGCTCCAGGCAAGGGGCT GGAGTGGGTGGCAGTTATATGGTATGATGGAAGT AATAAACACTATGCAGACTCCGTGAAGGGCCGA TTCACCATCTCCAGAGACAATTCCAAGAATACGT TGTATCTGCAAATGAACAGTCTGAGAGGCGAGG ACACGGCTGTGTATTACTGTGCGAGAGATCGGGG AGTGGGCTACAACGGTATGGACGTCTGGGGCCA AGGGACCACGGTCACCGTCTCCTCA<br><br>SEQ ID NO: 31083 |

FIGURE 50
(Continued)

| | | | |
|---|---|---|---|
| | | AA | DIQMTQSPSSLSASVGDRVTITCRASQGISNYLD WFQQKPGKAPKSLIYSASNLQSGVPSKFSGSRSG TDFTLTISSLQPEDFATYYCQHYSNYPLTFGGGT KVEIK | QVQLVESGGGVVQPGRSLRLSCAASGFTFSRYGMH WVRQAPGKGLEWVAVIWYDGSNKHYADSVKGRF TISRDNSKNTLYLQMNSLRGEDTAVYYCARDRGV GYNGMDVWGQGTTVTVSS |
| iPS:436386 | | | SEQ ID NO: 27078 | SEQ ID NO: 31084 |
| | 21-225_212B11 | NA | GACATCCAGATGACCCAGTCTCCATCTTCCCT GCCTGCATCTGTAGGAGACAGAGTCACCATCA CTTGCCGGGCAAGTCAGGGCATTAGAAATGAT TTAGGCTGGTATCAGCAGAAACCAGGGAAAG GCACTAAGCGCCTGATCTATGCTGCATCCAGT CCCCTAAGTGGGGTCCCATCAAGGTTCAGCGG CAGTGGATCTGGGACAGATCATTCTCACAA TCAGCAGCCTGCAGCCTGAAGATTTTGCAACT TATTACTGTCTACTGCATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGCT GGAGTGGGTGACAGTTATATGGTATGATGGAAGT AATAAATATTATGCAGACTCCGTGAAGGGCCGAT TCACCATCTCCAGAGACAACAATTCCAAGAACACGCT GTATCTGCAAATGAACAGCCTGAGAGCCGAGGA CACGGCTGTGTATTACTGTGCGAGAGAACGTTAT AGCAGTGGCTGTAGACTACGGTATGGACGTCT GGGGCCAAGGGACCACGGTCACCGTCTCCTCA |
| | | | SEQ ID NO: 27079 | SEQ ID NO: 31085 |
| | | AA | DIQMTQSPSSLPASVGDRVTITCRASQGIRNDLG WYQQKPGKAPKRLIYAASSLQSGVPSRFSGSGS GTEFILTISSLQPEDFATYYCLLHYSYPRTFGQGT KVEIK | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS |
| | | | SEQ ID NO: 27080 | SEQ ID NO: 31086 |

FIGURE 50
(Continued)

| | | | | |
|---|---|---|---|---|
| iPS:436388 | 21-225_212H11 | NA | GACATCCGGATGACCCAGTCTCCATCCTCACT GTCTGCATCTGTAGGAGACAGAGTCACCATCA CTTGTCGGGCGAGTCAGGACAGGCCATTGGAAACAT TTAGCCTGGTTTCAGCAGAGGCCTGGGAAAGC CCCTAAGTCCCTGATCTATGCTGCATCCAGATT GCAAAGTGGGGTCCCATCAAAGTTCAGCGGCA GTGGATCTGGGACAGATTTCACTCTCACCATC AGCAGCCTGCAGCCTGAAGATCTTGCAACTTA TTACTGTCAACACTACTATAGTAATATCCGCTCAC TTTTGTCGGAGGGACCAAGGTGGAGATCACA SEQ ID NO: 27081 | DIRMTQSPSSLSASVGDRVTITCRASQAIGKIHLA WFQQRPGKAPKSLIYAASRLQSGVPSKFSGSGSG TDFTLTISSLQPEDLATYYCQHYSNYPLTFVGGT KVEIT SEQ ID NO: 27082 | CAGGTGCAGCTGGTGGAGTCTGGGGGAGGCGTG GTCCAGCCTGGGAGGTCCCTGAGACTCTCCTGTG CAGTGTCTGAATCACCTTCAGTAGTAGTTATGGCAT GCACTGGGCCCGCCAGGCTCCAGGCAAGGGCT GGAGTGGGTGGCAGTTATATGGTATGATGGAAGT AATAAAAACTATGAAGACTCCGTGAAGGGCCGA TTCACCATCTCCAGAGACAACTCCAAGAACACGC TGTATCTGCAAATGAACAGCCTGAGAGCCGAGG ACACGGCTGTGTATTACTGTGCGAGAGATGGGAG TTATGGTTACGACGGTATGGACGTCTGGGGCCAA GGGACCACGGTCACCGTCTCCTCA SEQ ID NO: 31087 | QVQLVESGGGVVQPGRSLRLSCAVSGITFSSYGMH WARQAPGKGLEWVAVIWYDGSNKNYEDSVKGRF TISRDNSKNTLYLQMNSLRAEDTAVYYCARDGSYG YDGMDVWGQGTTVTVSS SEQ ID NO: 31088 |
| iPS:436390 | 21-225_213D2 | NA | GACATCCAGATGACCCAGTCTCCATCCTCACT GTCTGCATCTGTAGGAGACAGAGTCACCATCA CTTGTCGGGCGAGTCAGGGCATTAGCAATCAT TTAGCCTGGTTTCAGCAGAAACCAGGGAAAGC CCCTAAGTCCCTGATCTATGCTGTCATCCAGTTT GCAAAGTGGGGTCCCATCAAAATTCAGCGGCA ATAGATCTGGGACAGATTTCACTCTCACCATC AACAACCTGCACCAGTATAGTAATTACCCTCAC TTACTGCCACCAGTATAGTAATTACCCTCTCAC TTTCGGCGGAGGGACCAAGGTGGAGATCAAA SEQ ID NO: 27083 | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATAAAATTATGCAGACTCCGTGAAGGGCCGA TTCACCATCTCCAGAGACAATTCCAAGAACACGC TGTCTCTGCAAATGAACAGCCTGAGAGCCGAGG ACACGGCTGTGTATTACTGTGCGAGAGACTACGG TGTGGGTACTACGGTACGGACGTCTGGGGCCAA GGGACCACGGTCACCGTCTCCTCA SEQ ID NO: 31089 | |

FIGURE 50
(Continued)

| | | | |
|---|---|---|---|
| | | AA | DIQMTQSPSSLSASVGDRVTITCRASQGISNHLA WFQQKPGKAPKSLIHAASSLQSGVPSKFSGNRSG TDFTLTINNLQPEDFVTYYCHQYSNYPLTFGGGT KVEIK | QVQLVESGGGVVQPGRSLRLSCAASGFTFSSYGMH WVRQAPGKGLEWVAVIWYDGSNKNYADSVKGRF TISRDNSKNTLSLQMNSLRAEDTAVYYCARDYGVG YYGTDVWGQGTTVTVSS |
| | | | SEQ ID NO: 27084 | SEQ ID NO: 31090 |
| iPS:436392 | 21-225_213B3 | NA | GACATCCAGATGACCCAGTCTCCATCCTCACT GTCTGCATCTGTAGGAGACAGAGTCACCATCA CTTGTCGGGCGAGTCAGGGCATTAGCAATCAT TTAGCCTGGTTTCAGCAGAAACCAGGGAAAGC CCCTAAGTCCCTGATCTCTGCTGCATCCAGTGT GCTAAGTGGGGTCCCATCAAGTTCAGCGGCA GTGGATCTGGGACAGATTTCACTCTCACCATC AGCAGCCTTCAGCCTGAAGATTTTGCCACTTA TTACTGCCAAAAGTATATACTTACCCATTCA CTTTCGGCCCTGGGACCAAAGTGGATATCAAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGGCT GGAGTGGGTGGCAGTTATATGGTATGATGGAAGT AATAAAAACTATGCAGACTCCGTGAAGGGCCGA TTCACCATCTCCAGAGACAACAACTCCAAGAACACGC TGTATCTGCAAATGAACAGCCTGAGAGCCGAGG ACACGGCTGTGTATTACTGTGCGAGAGATAGGAC GGTGGGCTATGATGGTTTTGATATCTGGGGCCAA GGGACAATGGTCACCGTCTCTTCA |
| | | | SEQ ID NO: 27085 | SEQ ID NO: 31091 |
| | | AA | DIQMTQSPSSLSASVGDRVTITCRASQGIGKYLA WFQQKPGKAPKSLISAASSVLSGVPSKFSGSGSG TDFTLTISSLQPEDFATYYCQKYDTYPFTFGPGT KVDIK | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDRTVG YDGFDIWGQGTMVTVSS |
| | | | SEQ ID NO: 27086 | SEQ ID NO: 31092 |

FIGURE 50
(Continued)

| | | | | |
|---|---|---|---|---|
| iPS:436394 | 21-225_213C4 | NA | GACATCCATATGACCCAGTCTCCATCCTCACT GTCTGCATCTGTAGGAGACAGAGTCACCATCA CTTGTCGGGCGAGTCAGGCCATTAGGAATTAT TTAGCCTGGTGTCAGCAGAAACCAGGGAAAG CCCCTAAGACCCTGATCTATGCTGCATCCAGT TTGCAAAGTGGGGTCCCATCAAAGTTCAGCGG CAGTGGATCTGGGACAGATTTCACTCTCACCA TCAGCAGCCTGCAGCCTGAAGATTTTGCAACT TATTACTGCCAACAGTATAGTAATTACCCTCTC ACTTTCGGCGGAGGGACCAAGGTGGAGATCA AA<br><br>SEQ ID NO: 27087 | CAGGTGCAGTTGGTGGAGTCTGGGGGAGGCGTG GTCCAGCCTGGGAGGTCCCTGAGACTCTCCTGTG CAACGTCTGGATTCACCTTCAGTAGTAGTGGCAT GCACTGGGTCCGCCAGGCTCCAGGCAAGGGCT GGAGTGGGTGGCAGTTATATGGTATGATGAAGT AATAAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGACTACGG TGTCGGGTACGACGGTATGACGTCTGGGGCCA AGGGACCACGGTCACCGTCTCCTCA<br><br>SEQ ID NO: 31093 |
| | | AA | DIHMTQSPSSLSASVGDRVTITCRASQAIRNYLA WCQQKPGKAPKTLIYAASSLQSGVPSKFSGSGS GTDFTLTISSLQPEDFATYCQQYSNYPLTFGGG TKVEIK<br><br>SEQ ID NO: 27088 | QVQLVESGGGVVQPGRSLRLSCATSGFTFSSYGMH WVRQAPGKGLEWVAVIWYDGSNKHYADSVKGRF TISRDNSKNTLYLQMNSLRAEDTAVYYCARDYGV GYDGMDVWGQGTTVTVSS<br><br>SEQ ID NO: 31094 |
| iPS:436396 | 21-225_213E5 | NA | GACATCCGGATGACCCAGTCTCCATCCTCACT GTCTGCATCTGTAGGAGACAGAGTCACCATCA CTTGTCGGGCGAGTCAGGCCATTGGGAAACAT TTAGCCTGGTTTCAGCAGCCGCCAGGGAAAGC CCCTAAGTCCCTGATCTATGCTGCATCCAGATT GCAAAGTGGGGTCCCATCAAAGTTCAGCGGCA GTGGATCTGGGACAGATTTCACTCTCACCATC AGCAGCCTGCAGCCTGAAGATCTTGCAACTTA TTACTGTCAACACTATAGTAATTATCCGCTCAC TTTCGGCGGAGGGACCAAGGTGGAGATCAAA<br><br>SEQ ID NO: 27089 | CAGGTGCAGCTGGTGGAGTCTGGGGGAGGCGTG GTCCAGCCTGGGAGGTCCCTGAGACTCTCCTGTG CAGTGTCTGGAATCACCTTCAGTAGTTATGGCAT GCACTGGGCGCCCAGGCTCCAGGCAAGGGGCT GGAGTGGGTGGCAGTTATATGAAGTATGATGAAGT AATAAAAACTATGAAGACTCCGTGAAGGGCCGA TTCACCATCTCCAGAGACAACTCCAAGAACACGC TGTATCTGCAAATGAACAGCCTGAGAGCCGAGG ACACGGCTGTGTATTACTGTGCGAGAGATGGGAG TTATGGTTACGACGGTATGGACGTCTGGGGCCAA GGGACCACGGTCACCGTCTCCTCA<br><br>SEQ ID NO: 31095 |

FIGURE 50
(Continued)

| | | | |
|---|---|---|---|
| iPS:436398 | | AA | DIRMTQSPSSLSASVGDRVTITCRASQAIGKHLAWFQQRPGKAPKSLIYAASRLQSGVPSKFSGSGSGTDFTLTISSLQPEDLATYYCQHYSNYPLTFGGGTKVEIK<br>SEQ ID NO: 27090 | QVQLVESGGGVVQPGRSLRLSCAVSGITFSSYGMHWARQAPGKGLEWVAVIWYDGSNKNYEDSVKGRFTISRDNSKNTLYLQMNSLRAEDTAVYYCARDGSYGYDGMDVWGQGTTVTVSS<br>SEQ ID NO: 31096 |
| | 21-225_213B8 | NA | GACATCCAGATGACCCAGTCTCCATCCTCACTGTCTGCATCTGTAGGAGACAGAGTCACCATCACTTGTCGGGCGAGTCAGGGCATTAGCAATCATCTTAGCCTGGTTTCAGCAGAAACCAGGGAAAGCCCCTAAGTCCCTGATCTATGCTGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGCCAACAGTATAGTAATTACCCTCTCACTTTCGGCGGAGGGACCAAGGTGGAGATCAAA<br>SEQ ID NO: 27091 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAACACTATGCAGACTCCGTGAAGGGCCGATTCACCATCTCCAGAGACAACAATTCCAAGAACACGCTGTATCTGCAAATGAACAGCCTGAGAGCCGAGGACACGGCTGTGTATTACTGTGCGAGAGACTACGGTGTCGGGTACTACGGTACGGACGTCTGGGGCCAAGGGACCACGGTCACCGTCTCCTCA<br>SEQ ID NO: 31097 |
| | | AA | DIQMTQSPSSLSASVGDRVTITCRASQGISNHLAWFQQKPGKAPKSLIYAASSLQSGVPSKFSGSGSGTDFTLTISSLQPEDFATYYCQQYSNYPLTFGGGTKVEIK<br>SEQ ID NO: 27092 | QVQLVESGGGVVQPGRSLRLSCAASGFTFSSYGMHWVRQAPGKGLEWVAVIWYDGSNKHYADSVKGRFTISRDNSKNTLYLQMNSLRAEDTAVYYCARDYGVGYYGTDVWGQGTTVTVSS<br>SEQ ID NO: 31098 |

FIGURE 50
(Continued)

| | | | | |
|---|---|---|---|---|
| iPS:436400 | 21-225_213H7 | NA | GACATCGTGATGACCCAGTCTCCAGACTCCCT GGCTGTGTCTCTGGGCGAGAGGGCCACCATCA ACTGCAAGTCCAGCCAGAATGTTTTAGACATC TCCAACAATAAGAATTCCTTAGGTTGGTTCCA GCAGAAACCAGGTCAGCCTCCAAGCTGCTCA TTAACTGGGCATCTACCGGGAATCCGGGGTC CCTGACCGCTTCAGTGGCAGCGGGTCTGGGAC AGATTTCACTCTCACCATCAGCAGCCTGCAGA CTGAAGATGTGGCAGTTTATCACTGTCAGCAA TATTATAACATTCCTCGACGTTCGGCCGAGG GACCAAGGTGGAAATCAAA | CAGGTGCAGCTGGTGCAGTCTGGGGCTGAGGTG AAGAAGCCTGGGGCCTCAGTGAAGGTCTCTGC AAGGCTTCTGGATACACCTTCACCGGCTACCATA TGCACTGGGTGCGACAGGCCCCTGGACAAGGGC TTGAGTGGATGGGATGGATCAATCCTAAGAGTGA TGGCACAAACTATGCACAGAAGTTTCAGGGCAG GGTCACCATGACCAGGACACGTCCATCAGCAC AGCCTACATGGAGCTGAGCAGGCTGAGATCTGA CGACACGGCCGTGTATTACTGTGCGAGAGAAAA GCCTGGGAGCTACTACAAATACTGGGGCCAGGG AACCCTGGTCACCGTCCTCA |
| | | | SEQ ID NO: 27093 | SEQ ID NO: 31099 |
| | | AA | DIVMTQSPDSLAVSLGERATINCKSSQNVLDISN NKNSLGWFQQKPGQPPKLLINWASTRESGVPDR FSGSGSGTDFTLTISSLQTEDVAVYHCQQYYNIP PTFGRGTKVEIK | QVQLVQSGAEVKKPGASVKVSCKASGYTFTGYHM HWVRQAPGQGLEWMGWINPKSDGTNYAQKFQGR VTMTRDTSISTAYMELSRLRSDDTAVYYCAREKPG SYYKYWGQGTLVTVSS |
| | | | SEQ ID NO: 27094 | SEQ ID NO: 31100 |
| iPS:436402 | 21-225_213H12 | NA | GACATCGTGATGACCCAGTCTCCAGACTCCCT GGCTGTGTCTCTGGGCGAGAGGGCCACCATCA CCTGCAAGTCCAGCCAGAACTGTTTTAAAGACC TCCAACAATAGGAACTACTTAGCTTGGTACCA GCAGAAACCAGGACAGCCTCCTAAGGTGCTCA TTTACTGGGCATCTACCCGGGAATCCGGGGTC CCTGACCGATTCAGTGGCAGCGGGTCTGGGAC AGATTTCACTCTCATCATCAGCAGCCTGCAGG CTGAAGATGTGGCAGTTTATTCCGTGACCTTC ACTCACGTATACTGTCAGCAGACCTTCGGCCAAGG GACCAAGGTGGAAATCAAG | CAGGTTCAGCTGGTGCAGTCTGGAGCTGAGGTGA AGAAGCCTGGGGCCTCAGTGAAGGTCTCTGCA AGGCTTCTGGTTCACCTTACCAGTATGGTATC AACTGGGTGCGACAGGCCCCTGGACAAGGCTT GAGTGGATGGGATGGATCAGCGTTCACAATGGT AACACAGACTATGCACAGAAGTTCCAGGGCAGA GTCACCATGACCACAGACACATCCACGAGACA GCCTACATGGAACTGAGGAGCCTGAGATCTGAC GACACGGCCGTGTATGGACGTCTGGGGCCAAGGGA ACTACGGTATGGACGTCTGTGCGAGAGACTACT AGGTCACCGTCCTCA |
| | | | SEQ ID NO: 27095 | SEQ ID NO: 31101 |

FIGURE 50
(Continued)

| | | | | | |
|---|---|---|---|---|---|
| iPS:436404 | | AA | DIVMTQSPDSLAVSLGERATITCKSSQNVLKTSNNRNYLAWYQQKPGQPPKVLIYWASTRESGVPDRFSGSGSGTDFTLTISSLQAEDVAVYYCHQYYSIPWTFGQGTKVEIK<br><br>SEQ ID NO: 27096 | QVQLVQSGAEVKKPGASVKVSCKASGFTFTSYGINWVRQAPGQGLEWMGWISVHNGNTDYAQKFQGRVTMTDTSTSTAYMELRSLRSDDTAVYYCARDYYYGMDVWGQGTKVTVSS<br><br>SEQ ID NO: 31102 |
| | 21-225_214C3 | NA | GACATCCAGATGACCCAGTCTCCATCCTCACTGTCTGCATCTGTTGGAGACAGAGTCACCATAACTTGTCGGGCGAGTCAGGGCATTGGCAATTATTTAGCCTGGTTTCAGCAGAAACCAGGTAAAGTCCCTAAGTCCCTGATCTATGCTGCATCCAGTTTGCAAAGTGGGGTCCCATCAAAGTTCAGCGGCAGTGGATCTGGGACAGACCTGAAGATTTTACTTACTGTCAACAATATATGACTTACCCAATCACTTTCGGCCCTGGGACCAAAGTGGATATCAAA<br><br>SEQ ID NO: 27097 | CAGGTGCAGCTGGTGGAGTCTGGGGGAGGCGTGGTCCAGCCTGGGAGGTCCCTGAGACTCTCGTGAAGCGTCTGGATTCACCTTCAGTAGCTATGCATGCACTGGGTCCGCCAGGCTCCAGGCAAGGGCTGGAGTGGGTGGCAGTTATATGGAGACTCCGTGAAGGGCCGAAATAAAAACTATGGAGACACATCCGTGAAGGGCCGATTCACCATCTCCAGAGACAACAGCCTGAGAGCCGAGGACACGGCTGTGTATTACTGTGCGAGAGATCGGGGAGTGGGCTACGACGGAATGACGTCTGGGGCCAAGGGACCACGGTCACCGTCTCCTCA<br><br>SEQ ID NO: 31103 |
| | | AA | DIQMTQSPSSLSASVGDRVTITCRASQGIGNYLAWFQQKPGKVPKSLIYAASSLQSGVPSKFSGSGSGTDFTLTISSLQPEDFFTYYCQQYMTYPITFGPGTKVDIK<br><br>SEQ ID NO: 27098 | QVQLVESGGGVVQPGRSLRLSCEASGFTFSSYGMHWVRQAPGKGLEWVAVIWYDGSNKNYGDSVKGRFTISRDNSKNTLYLQMNSLRAEDTAVYYCARDRGVGYDGMDVWGQGTTVTVSS<br><br>SEQ ID NO: 31104 |

FIGURE 50
(Continued)

| | | | | |
|---|---|---|---|---|
| iPS:436406 | 21-225_214E4 | NA | GACATCCAGATGACCCAGTCTCCATCCTCACTGTCTGCATCTGTAGGAGACAGAGTCACCATCACTTGTGTGGGGCGAGTCAGGGCATTAGCAATTATTTAGCCTGGTTTCAGCAGAAACCAGGGAAAGCCCCTAAGTCCCTGATCTATGCTGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGTCCAACAGTATCTTACTTACCCATTCACTTTCGGCCCTGGGACCAAAGTGGATATCAAA SEQ ID NO: 27099 | CAGGTGCAGCTGGTGGTGGAGTCTGGGGGAGGCGTGGTCCAGCCTGGGAGGTCCCTGAGACTCTCCTGTCAGCGTTCTGGATTCACCTTCAGTAGCTATGGCATGCACTGGGTCCGCCAGGCTCCAGGCAAGGGCTGGAGTGGGTGGCAGTTATATGGTATGGATGAAGTAATGAAAACTATGCAGACTCCGTGAAGGGCCGAATCACCATCTCCAGAGACAATTCCAAGAACACGCTGTATCTGCAAATGAACAGCCTGAGAGCCGAGGACACGGCTGTGTATTACTGTGCGAGAGATAGGACGGTGGGCTATGATGGTGTGATATCTGGGGCCAAGGGCAATGGTCACCGTCTCTTCA SEQ ID NO: 31105 |
| | | AA | DIQMTQSPSSLSASVGDRVTITCRASQGISNYLAWFQQKPGKAPKSLIYAASSLQSGVPSKFSGSGSGTDFTLTISSLQPEDFATYYCQQYLTYPFTFGPGTKVDIK SEQ ID NO: 27100 | QVQLVESGGGVVQPGRSLRLSCAASGFTFSSYGMHWVRQAPGKGLEWVAVIWYDGSNENYADSVKGRITISRDNSKNTLYLQMNSLRAEDTAVYYCARDRTVGYDGCDIWGQGAMVTVSS SEQ ID NO: 31106 |
| iPS:436408 | 21-225_214H8 | NA | GAAATTGTGCTGACTCAGTCTCCAGACTTTCAGTCTGTGACTCCAAAGGAGAAAGTCACCATCACCTGCCGGCCAAGTCAGAGCATTGGTGTTAGCACTGTGGCTTGGTACCAGCAGAAACCAGATCAGTCTCCACAACTCCTCATCATCAAGTATGCTTCCCAGTCCTTCTCAGGGGTCCCCTCGAGGTTCAGTGGCAGTGGATCTGGGACAGATTTCACCCTCACCATCAATAGCCTGGAAGCTGAAGATGCTGCAACGTATTACTGTCATCAGAGTCGTAGTTTACCATTCACTTTCGGCCCTGGGTCCAAAGTGGATATCAAA SEQ ID NO: 27101 | CAGGTCCAGCTGGTGCAGTCTGGGGCTGAGGTGAAGAAGCCTGGGGCCTCAGTGAAGGTCTCCTGCAAGGCTTCTGGATACACCTTCACCGGCCACTATATACGCTGGGTGCGACAGGCCCCTGGACAAGGGCTTGAGTGGATGGGATGGATCAACACTAACAGTGGTGGCACAAACTATGCACAGAAGTTTCAGGGCAGGGTCACCATGACCAGGGACACGTCCATCAGCACAGCCTACATGGAGCTGAGCAGGCTGAGATCTGACACGGCCGTATATTACTGTGCGAAAGACGGAGATACAGCTATGTTACGACTGGTTGACCCGTGGGGCCAGGGAACCCTGGTCACCGTCCTCA SEQ ID NO: 31107 |

FIGURE 50
(Continued)

| | | | | |
|---|---|---|---|---|
| iPS:436410 | 21-225_212E10 | AA | EIVLTQSPDFQSVTPKEKVTITCRASQSIGVSLHWYQQKPDQSPQLLIKYASQSFSGVPSRFSGSGSGTDFTLTINSLEAEDAATYYCHQSRLPFTFGPGSKVDIK | QVQLVQSGAEVKKPGASVKVSCKASGYTFTGHYIHWVRQAPGQGLEWMGWINSNSGGTNYAQKFQGRVTMTRDTSISTAYMELSRLRSDDTAVYYCAKDGRYSYGYDWFDPWGQGTLVTVSS |
| | | | SEQ ID NO: 27102 | SEQ ID NO: 31108 |
| | | NA | GACATCCAGATGACCCAGTCTCCATCCTCACTGTCTGCATCTGTAGGAGACAGAGTCACCATCACTTGTCGGGCGAGTCAGGGCATTAGCGTCCTGCATTTAGCCTGGTTTCAGCAGAAACCAGGAGAAAGCCCCTAAGTCCCTGATCTATGCTGCATCCAGTTTGCAAAGTGGGGTCCCATCAAGTTCAGCGGCAGTGGATCTGGGACAGATTTCACTCTCACCATCAGCAGCCTGCAACAGTATGAATTACCCTCTCATTACTGCCACCAGAGTCGACTTCCAACTTACCCTCTCACTTTCGGCGGAGGGACCAAGGTGGAGATCAAA | CAGGTGCAGTTGGTGGAGTCTGGGGGAGGCGTGGTCCAGCCTGGGAGGTCCCTGAGACTCTCCTGTCAGCGTCTGATTCACCTTCAGTAGTACTGGCATGCACTGGGTCCGCCAGGCTCCAGGCAAGGGGCTGGAGTGGGTGGCAGTTATATGCAGACTCCGTGAAGGGCCGAAATAAATACTATGCAGACACTCCGTGAAGGGCCGATCCACCATCCAGAGACAATTCCAAGAACACGCACACGGCTGTGTATTACTGTGCGAGAGACTACGGTGTCGGGTACTACGGTACGGACGTCTGGGGCCAAGGGACCACGGTCACCGTCTCCTCA | |
| | | | SEQ ID NO: 27103 | SEQ ID NO: 31109 |
| | | AA | DIQMTQSPSSLSASVGDRVTITCRASQGISNHLAWFQQKPGKAPKSLIYAASSLQSGVPSKFSGSGSGTDFTLTISSLQPEDFATYYCQQYSNYPLTFGGGTKVEIK | QVQLVESGGGVVQPGRSLRLSCAASGFTFSSYGMHWVRQAPGKGLEWVAVIWYDGSNKYYADSVKGRFTISRDNSKNTLSLQMNSLRAEDTAVYYCARDYGVGYYGTDVWGQGTTVTVSS |
| | | | SEQ ID NO: 27104 | SEQ ID NO: 31110 |

FIGURE 50
(Continued)

| | | | | |
|---|---|---|---|---|
| iPS:436412 | 21-225_214H9 | NA | GACATCCAGATGACCCAGTCTCCATCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATTATAGTTACCCTCGG ACGTTCGGCGCCAAGGGACCAAGGTGAAATCA AA | CAGGTGCAGCTGGTGGAGTCTGGGGGAGGCGTG GTCCAGCCTGGGAGGTCCCTGAGACTCTCCTGTG CAGCGTCTGATTCACCTTCAGTAGTCATGTCAT GCACTGGGTCCGCCAGGCTCCAGGCAAGGGCT GGAGTGGGTGGCAGTTATATGGTATGATGGAAGT AATAAATACTATGCAGAGACTCCGTGAAGGGCCGA TTCACCATCTCCAGAGACAATTCCAAGAACACGC TGTATCTGCAAATGAACAGCCTGAGAGCCGAGG ACACGGCTGTATTTTACTGTGCGAGAGAGAGTA TACCAGCAGCTGGTACGACTACGGTATGGACGTC TGGGGCCAAGGGACCACGGTCACCGTCTCCTCA |
| | | | SEQ ID NO: 27105 | SEQ ID NO: 31111 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEIK | QVQLVESGGGVVQPGRSLRLSCAASGFTFSSYVMH WVRQAPGKGLEWVAVIWYDGSNKYYADSVKGRF TISRDNSKNTLYLQMNSLRAEDTAVFYCARERYTS SWYDYGMDVWGQGTTVTVSS |
| | | | SEQ ID NO: 27106 | SEQ ID NO: 31112 |
| iPS:436414 | 21-225_214G10 | NA | GACATCCAGATGACCCAGTCTCCATCTCCCC GCCTGCATCTGTTGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCATTCTCACAA TCAGCAGCCTGCAGCCTGAAGATTTTGCAACT TATTACTGTCTACTACTGTCATATAATAGTTACCCTCGG ACGTTCGGCGCCAAGGGACCAAGGTGAAATCA AA | CAGGTGCAGCTGGTGGAGTCTGGGGGAGGCGTG GTCCAGCCTGGGAGGTCCCTGAGACTCTCCTGTG CAGCGTCTGATTCACCTTCAGTGACTATGTCAT GCACTGGGTCCGCCAGGCTCCAGGCAAGGGCT GGAGTGGGTGGCAGTTATATGGTATGATGGAAGT AATAAATATTATGCAGACTCCGTGAAGGGCCGAT TCACCATCTCCAGAGACAATTCCAAGAACACGC GTATCTGCAAATGAACAGCCTGAGAGCCGAGGA CACGGCTGTGTATTACTGTGCGAGAGAACGTTAT AGCAGTGGCTGGTACGACTACGGTATGGACGTCT GGGGCCAAGGGACCACGGTCACCGTCTCCTCA |
| | | | SEQ ID NO: 27107 | SEQ ID NO: 31113 |

FIGURE 50
(Continued)

| | | | |
|---|---|---|---|
| | | AA | DIQMTLCPSSPPASVGDRVTITCRASQGIRNDLG WYQQKPGKAPKRLIYAASSLQSGVPSRFSGSGS GTEFILTISSLQPEDFATYYCLLHNSYPRTFGQGT KVEIK<br><br>SEQ ID NO: 27108 | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS<br><br>SEQ ID NO: 31114 |
| iPS:436416 | 21-225_214G12 | NA | GACATCCAGATGACCCAGTCTCCATCTTCCCC GCCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCTGCATCCAGT TGCAAAGTGGGGTCCCATCAAGGTTCAGCGGC AGTGGATCTGGGACAGATTCATTCTCACAAT CAGCAGCCTGCAGCCTGAAGATTTTGCAACTT ATTACTGTGTAATGCATTATAGTTACCCTCGG ACGTTCGGCCAAGGGACCAAGGTGGAAATCA AA<br><br>SEQ ID NO: 27109 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGTACGACTACGGTATGGACGTCT GGGGCCAAGGGACCACGGTCACCGTCTCCTCA<br><br>SEQ ID NO: 31115 |
| | | AA | DIQMTQSPSSPPASVGDRVTITCRASQGIRNDLG WYQQKPGKAPKRLIYAASSLQSGVPSRFSGSGS GTEFILTISSLQPEDFATYYCVMHYSYPRTFGQG TKVEIK<br><br>SEQ ID NO: 27110 | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS<br><br>SEQ ID NO: 31116 |

FIGURE 50
(Continued)

| | | | |
|---|---|---|---|
| iPS:436418 | 21-225_215E3 | NA | GACATCCAGATGACCCAGTCTCCATCCTCCC GCCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCTGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTGCAACTT ATTACTGTGTAATGCATAATAGTTACCCTCGG ACGTTCGGCCAAGGGACCAAGGTGGAAATCA AA |
| | | | SEQ ID NO: 27111 |
| | | AA | DIQMTQSPSPSSPASVGDRVTITCRASQGIRNDLG WYQQKPGKAPKRLIYAASSLQSGVPSRFSGSGS GTEFTLTISSLQPEDFATYYCVMHNSYPRTFGQG TKVEIK |
| | | | SEQ ID NO: 27112 |
| iPS:436420 | 21-225_215B5 | NA | GACATCCAGATGACCCAGTCTCCATCCTCACT GTCTGCATCTGTAGGAGACAGAGTCACCATCA CTTGTCGGGCGAGTCAGGGCATTAGCAATCAT TTAGCCTGGTTTCAGCAGAAACCAGGGAAAGC CCCTAAGTCCCTGATCTATGCTGCATCCAGTT GCAAAGTGGGGTCCCATCAAAATTCAGCGGCA ATAGATCTGGGACAGATTTCACTCTCACCATC AACAACCTGCCAGCAGTATTAATTACCCTCAC TTACTGCCAGCAGTATAATTACCCTCTCAC TTTCGGCGGAGGGACCAAGGTGGAGATCAAA |
| | | | SEQ ID NO: 27113 |

| | | | |
|---|---|---|---|
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT ACACTGGGTCCGCCAGGCTCCAGGCAAGGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGTGTGAGAGCCGAGGA CACGGCTGTGTATTACTGTGCGAGAGAACGTTAT AGCAGTGGCTGGTACGACTACGGTATGGACGTCT GGGGCCAAGGGACCACGGTCACCGTCTCCTCA |
| | | | SEQ ID NO: 31117 |
| | | | QVQLVESGGGVVQPGRSLRLSCAASGFTFSDYVIH WVRQAPGKGLEWVTVIWYDGSNKYYADSVKGRF TISRDNSKNTLYLQMNSVRAEDTAVYYCARERYSS GWYDYGMDVWGQGTTVTVSS |
| | | | SEQ ID NO: 31118 |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGGCT GGAGTGGGTGGCAGTTATATGGTATGATGGAAGT AATAAAATTATGCAGACTCCGTGAAGGGCCGA TTCACCATCTCCAGAGACAATTCCAAGAACACGC TGTCTCTGCAAATGAACAGCTGAGAGCCGAGG ACACGGCTGTGTATTACTGTGCGAGAGACTACGG TGTCGGGTACTACGGTACGGACGTCTGGGGCCAA GGGACCACGGTCACCGTCCTCA |
| | | | SEQ ID NO: 31119 |

FIGURE 50
(Continued)

| | | | | |
|---|---|---|---|---|
| iPS:436422 | 21-225_215D6 | AA | DIQMTQSPSSLSASVGDRVTITCRASQGISNHLAWFQQKPGKAPKSLIHAASSLQSGVPSKFSGNRSGTDFTLTINNLQPEDFVTYYCQQYINYPLTFGGGTKVEIK | QVQLVESGGGVVQPGRSLRLSCAASGFTFSSYGMHWVRQAPGKGLEWVAVIWYDGSNKNYADSVKGRFTISRDNSKNTLSLQMNSLRAEDTAVYYCARDYGVGYYGTDVWGQGTTVTVSS |
| | | | SEQ ID NO: 27114 | SEQ ID NO: 31120 |
| | | NA | GACATCCAGATGACCCAGTCTCCATCCTCACTGTCTGCATCTGTAGGAGACAGAGTCACCATCACTTGTCGGGCGAGTCAGGGCATTAGCAATCATTTAGCCTGGTTTCAGCAGAAACCAGGGAAAGCCCCTAAGTCCCTGATCTATGCTGCATCCAGTTTGCATAGTGGGGTCCCATCAAGTTCAGCGGCAGTAGATCTGGGACAGATTTCACTCTCACCATCAGCAGCCTGCAGCCTGAAGATTTTACTTACCCTCTCACTTACTGCCAACAGTATATTAACTACCCTCTCACTTTCGGCGGAGGGACCAAGGTGGAGATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAAAACTATGCAGATTCCGTGAAGGGCCGATTCACCATCTCCAGAGACAACAATTCCAAGAACACACTGTATCTGCAAATGAACAGCCTGAGAGCCGAGGACACGGCTGTGTATTACTGTGCGAGAGACTGCGGTGTCGGATACTACGGTACGGACGTCTGGGGCCAAGGGACCACGGTCACCGTCTCCTCA |
| | | | SEQ ID NO: 27115 | SEQ ID NO: 31121 |
| | | AA | DIQMTQSPSSLSASVGDRVTITCRASQGISNHLAWFQQKPGKAPKSLIYAASSLHSGVPSKFSGSRSGTDFTLTISSLQPEDFATYYCQQYVTYPLTFGGGTKVEIK | QVQLVESGGGVVQPGRSLRLSCAASGFTFSSYGMHWVRQAPGKGLEWVAVIWYDGSNKNYADSVKGRFTISRDNSKNTLYLQMNSLRAEDTAVYYCARDCGVGYYGTDVWGQGTTVTVSS |
| | | | SEQ ID NO: 27116 | SEQ ID NO: 31122 |

FIGURE 50
(Continued)

| | | | Sequence | SEQ ID NO |
|---|---|---|---|---|
| iPS:436424 | 21-225_215H6 | NA | GAAATTGTGCTGACTCAGTCTCCAGACTTTCAGTCTGTGACTCCAAAGGAGAAAGTCACCATCACCTGCCGGGCCAGTCAGAGCATCGGTGTTAGCTTACACTGGTACCAGCAGAAACCAGATCAGTCTCCACAGCTCCTCATCAAGTATGCTTCCCAGTCCCTCTCAGGGGTCCCCTCGAGGTTCAGTGGCAGTGGATCTGGGACAGATTTCACCCTCACCATCAATAGCCTGGAAGCTGAAGATGCTGCAACGTATTACTGTCATCAGAGTCGCAGTTTACCATTCACTTTCGGCCCTGGGTCCAAAGTGGATATCAAA | SEQ ID NO: 27117 |
| | | AA | EIVLTQSPDFQSVTPKEKVTITCRASQSIGVSLHWYQQKPDQSPQLLIKYASQSLSGVPSRFSGSGSGTDFTLTINSLEAEDAATYYCHQSRSLPFTFGPGSKVDIK | SEQ ID NO: 27118 |
| | | NA | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATACTGGGTGCGACAGGCCCCTGGACAAGGGCTTGAGTGGATGGGATGGATCAACTCTAACAGTGGTGGCACAAATTATGCAGAGAAGTTTCAGGGCAGGGTCACCATGACCAGGGACACGTCCATCAGCACAGCCTACATGGAGCTGAGCAGGCTGAGATCTGACACGGCCGTGTATTACTGTGCGAAAGACGGGAGATACAGCTATGTCACGACTGGTTCGACCCCTGGGGCCAGGGAACCCTGGTCACCGTCTCCTCA | SEQ ID NO: 31123 |
| | | AA | QVQLVQSGAEVKKPGASVKVSCKASGYTFTGYYTGWVRQAPGQGLEWMGWINSNSGGTNYAEKFQGRVTMTRDTSISTAYMELSRLRSDDTAVYYCAKDGRYSYGHDWFDPWGQGTLVTVSS | SEQ ID NO: 31124 |
| iPS:436426 | 21-225_215C7 | NA | GAAATTGTGTTGACGCAGTCTCCAGGCACCCTGTCTTTGTCTCCAGGGGAAAGAGTCACCCTCTCCTGCAGGGCCAGTCAGAGTGTTACCAGCAACTACCTAGCTTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTTTATTACTGTCAGCAGTATGGTAGTTCACTCACCTTCGGCGGAGGGACCAAGGTGGAGATCAAA | SEQ ID NO: 27119 |
| | | NA | CAGGTGCAGCTGGTGGAGTCTGGGGGAGGCGTGGTCCAGCCTGGGAGGTCCCTGAGACTCTCCTGTGCAGCGTCTGGATTCACCTTCAGTTACTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGGTTAGACTACAGTAATTACGGGTGGTTCGACCCCTGGGGCCAGGGAACCCTGGTCACCGTCTCCTCA | SEQ ID NO: 31125 |

FIGURE 50
(Continued)

| | | | |
|---|---|---|---|
| | | AA | EIVLTQSPGTLSLSPGERVTLSCRASQRITTNFLA WYQQKPGQAPRLLIYGASSRATGIPDRFSGSGSG TDFTLTISRLESEDFAVYYCQQYVSSLLTFGGGT KVEIK<br><br>SEQ ID NO: 27120 | QVQLVESGGGVVQPGRSLRLSCAASGFTFSYYGM HWVRQAPGKGLEWVAVIWHDGSNKYYADSVKGR FTISRDNSKNTLYLQMNSLRAEDTAVYYCARLDYS NYGWFDPWGQGTLVTVSS<br><br>SEQ ID NO: 31126 |
| iPS:436428 | 21-225_215E11 | NA | GACATCCAGATGACCCAGTCTCCATCTTCCCC GCCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCTGCATCCAGT TGCAAAGTGGGGTCCCATCCAAGGTTCAGCGGC AGTGGATCTGGGACAGATTCATTCTCACAAT CAGCAGCGTGCAGCGTGAAGATTTTGCAACTT ATTACTGTGTAATGCATTATAGTTACCCTCGG ACGTTCGGCCAAGGGACCAAGGTGGAAATCA AA<br><br>SEQ ID NO: 27121 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGCT GGAGTGGGTGACAGTTATATGTGATGGAAGT AATAAATATTATGCAGACTCCGTGAAGGGCCGAT TCACCATCTCCAGAGACAATCCAAGAACACGCT GTATCTGCAAATGAACAGCCTGAGAGCCGAGA CACGGCTGTGTATTACTGTGCGAGAGAACGTTAT AGCAGTGGCTGTACGACTACGGTATGGACGTCT GGGGCCAAGGGACCACGGTCACCGTCTCCTCA<br><br>SEQ ID NO: 31127 |
| | | AA | DIQMTQCPSSPPASVGDRVTITCRASQGIRNDLG WYQQKPGKAPKRLIYAASSLQSGVPSRFSGSGS GTEFILTISSVQREDFATYYCVMHYSYPRTFGQG TKVEIK<br><br>SEQ ID NO: 27122 | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS<br><br>SEQ ID NO: 31128 |

FIGURE 50
(Continued)

| | | | |
|---|---|---|---|
| iPS:436430 | 21-225_215A12 | NA | GACATCCAGATGACCCAGTCTCCATCCTCACT GTCTGCATCTGTAGGAGACAGAGTCACCATCA CTTGTCGGACGAGTCAGGACATTGGCAATTAT TTAGCCTGGTTTCAGCAGAAACCAGGGAAAGC CCCTAAGTCCCTGATCTATGCTGCATCCAGTTT ACAGAGTGGGGTCCCATCAAAGTTCAGCGGCA GTAGATCTGGGACAGATTTCACTCTCACCATC AGCAGCCTGCAGTCTGAAGATTTTGCAACTTA TTACTGCCAACAGTATGTTACTTACCCGCTCAC TTTCGGCGGAGGGACCAAGGTGGAGATCAAA | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAGT AATGAACACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGGG AGTGGGCTACTACGGTATGGACGTCTGGGGCCA AGGGACCACGGTCACCGTCTCCTCA |
| | | | SEQ ID NO: 27123 | SEQ ID NO: 31129 |
| | | AA | DIQMTQSPSSLSASVGDRITITCRTSQDIGNYLAW FQQKPGKAPKSLIYAASSLQSGVPSKFSGSRSGT DFTLTISSLQSEDFATYYCQQYVTYPLTFGGGTK VEIK | QVQLVESGGGVVQPGRSLRLSCAASGFTFSSYGMH WVRQAPGKGLEWVAVIWYDGSNEHYADSVKGRF TISRDNSKNTLYLQMNSLRAEDTAVYYCARDRGV GYYGMDVWGQGTTVTVSS |
| | | | SEQ ID NO: 27124 | SEQ ID NO: 31130 |
| iPS:436432 | 21-225_215H12 | NA | GAAATTGTGTTGACGCAGTCTCCAGGCACCCT GTCTTTGTCTCCAGGGGAAAGAGCCACCCTCT CCTGCAGGGCCAGTCAGAGTGTTAGCAGCAGC TTCTTAGCTTGGTACCAGCAGAAACCTGGCCA GGCTCCCAGGCTCCTCATGTATGGTGCATCCA GCAGGGCCATTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGTTAGTCACCG CTCACTTTCGGCGGAGGGACCAAGGTGGAGAT CAAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTAACTATGGCAT GCACTGGGTCCGCCAGGCTCCAGGCAAGGGGCT GGAGTGGGTGGCAGTTATATGGTATGATGGAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTGTGTATTACTGTGCGAGGTTAGACT ACAGTAACTACGGTGGTTGACCCCTGGGGCCA GGGAACCCTGGTCACCGTCTCCTCA |
| | | | SEQ ID NO: 27125 | SEQ ID NO: 31131 |

FIGURE 50
(Continued)

| | | | | |
|---|---|---|---|---|
| | | AA | EIVLTQSPGTLSLSPGERATLSCRASQSVSSSFLAWYQQKPGQAPRLLMYGASSRAIGIPDRFSGSGSGTDFTLTISRLEPEDFAVYYCQQYVSSPLTFGGGTKVEIK<br>SEQ ID NO: 27126 | QVQLVESGGGVVQPGRSLRLSCAASGFTFSNYGMHWVRQAPGKGLEWVAVIWHDGSNKYYADSVKGRFTISRDNSKNTLYLQMNSLRAEDTAVYYCARLDYSNYGWFDPWGQGTLVTVSS<br>SEQ ID NO: 31132 |
| iPS:436434 | 21-225_216B10 | NA | GAAATAGTGATGACGGAGTCTCCAGCCACCCTGTCTGTGTCTCCAGGGGAAAGAGCCACCCTCTCCTGCAGGGCCAGTCAGAGTGTTAACAACAACCTTAGCCTGGTACCGGCAGAAACCTGGCCAGGCTCCCAGGCTCCTCATCTATGGTGCATCCACCAGGGCCACTGGTATCCCACCAGGTTCAGTGGCAGTGGGTCTGGGACAGAGTTCACTCTCTCCATCAGCAGCCTGCAGTCTGAAGATTTTGCAGTTATTACTGTCAGCAGTATAATGACTGGCCGTGCAGTTTTGGCCAGGGGACCAAACTGGAGATCAGA<br>SEQ ID NO: 27127 | CAGGTGCAGCTGGTGGAGTCGGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGCGCACGCTGTATCTGCAGATGAACAGCCTGAGAGCCGAGGACACGGCTGTGTATTACTGTGCGAGAGATCCAAACATAGTGGGAGCTACTGGTTTGACTACTGGGGCCAGGGAACCCTGGTCACCGTCTCCTCA<br>SEQ ID NO: 31133 |
| | | AA | EIVMTESPATLSVSPGERATLSCRASQSVNNNLAWYRQKPGQAPRLLIYGASTRATGIPPRFSGSGSGTEFTLSISSLQSEDFAVYYCQQYNDWPCSFGQGTKLEIR<br>SEQ ID NO: 27128 | QVQLVESGGGVVQPGRSLRLSCAASGFTFSSYGMHWVRQAPGKGLEWVAAIWYDGSNKYYADSVKGRFTISRDNSKRTLYLQMNSLRAEDTAVYYCARDPNIVGATWFDYWGQGTLVTVSS<br>SEQ ID NO: 31134 |

FIGURE 50
(Continued)

| | | | | |
|---|---|---|---|---|
| iPS:436436 | 21-225_216F10 | NA | GAAGTTGTGTTGACGCAGTCTCCAGGCACCCT GTCTTTGTCTCCAGGGGAAAGAGCCACCTCT CCTGCAGGGCCAGTCAGAGTGTTAGCAGCAGC TTCTTAGCTGGTACCAGCAGAAACCTGGCCA GGCTCCCAGGCTCCTCATCTATGGTACATCA CCAGGGCCACTGGCATCCCTGACAGGTTCAGT GGCAGTGGGTCTGGGACAGACTTCATTCTCAC CATCAGCAGACTGGAGCCTGAAGATTTTGCAG TATATTACTGTCAACAGTATGATAGGTCACCA TTCACTTTCGGCCCTGGGACCAAAGTGGATAT CAAA | GAGGTACAGCTGTGGTGGAGTCTGGGGAGGCTTG GTACAGCCTGGGGAGGTCCCTGAGACTCTCCTGTG CAGCCTCTGGATTCTCCTTCAGAAGCTATAGCAT GAACTGGGTCCGCCAGGCTCCAGGGAAGGGGCT GGAGTGGGTTCATACATTACTGGTAGTAGTAGT ACCATATACTACGGAGACTCTGTGAAGGGCCGAT TCACCATCTCCAGAGACAATGCCAAGAACTCACT GTATCTGCAAATGAACAGCCTGAGAGACGAGGA CACGGCTGTGTATTACTGTGCGAGATCGGGTTTA GCAGTGGAGGACTACTGGGGCCAGGGAACCCTG GTCACCGTCTCCTCA |
| | | | SEQ ID NO: 27129 | SEQ ID NO: 31135 |
| | | AA | EVVLTQSPGTLSLSPGERATLSCRASQSVSSFLA WYQQKPGQAPRLLIYGTSTRATGIPDRFSGSGSG TDFILTISRLEPEDFAVYYCQQYDRSPFTFGPGTK VDIK | EVQLVESGGGLVQPGGSLRLSCAASGFSFRSYSMN WVRQAPGKGLEWVSYITGSSSTIYADSVKGRFTIS RDNAKNSLYLQMNSLRDEDTAVYYCARSGLAVED YWGQGTLVTVSS |
| | | | SEQ ID NO: 27130 | SEQ ID NO: 31136 |
| iPS:436438 | 21-225_216E8 | NA | GACATCCAGATGACCCAGTCTCCATCTTCCCT GCCTGCATCTGTAGGAGACAGAGTCACCATCA CTTGCCGGGCAAGTCAGGGCATTAGAAATGAT TTAGGCTGGTATCAGCAGAAAACCAGGGAAAG CCCCTAAGCGCCTTATCTATGCTGCATCCAGTT TGCAAAGTGGGGTCCCATCAAGGTTCAGCGGC AGTGGATCTGGGACAGAATTCATTCTCACAAT CAGCAGCCTGCAGCCTGAAGATTTTGCAACTT ATTACTGTCTAATGCATTATAGTTACCCTCGGA CGTTCGGCCAAGGGACCAAGGTGGAAATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAACGTTAT AGCAGTGGCTGTACGACTACGGTATGGACGTCT GGGGCCAAGGGACCACGGTCACCGTCTCCTCA |
| | | | SEQ ID NO: 27131 | SEQ ID NO: 31137 |

FIGURE 50
(Continued)

| | | | |
|---|---|---|---|
| iPS:436440 | 21-225_216H12 | AA | DIQMTQSPSSLPASVGDRVTITCRASQGIRNDLG WYQQKPGKAPKRLIYAASSLQSGVPSRFSGSGS GTEFILTISSLQPEDFATYYCLMHYSYPRTFGQGT KVEIK |
| | | | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS |
| | | | SEQ ID NO: 27132 |
| | | | SEQ ID NO: 31138 |
| | | NA | GACATCCAGATGACCCTGTCTCCATCTTCCCTG CCTGCATCTGTAGGAGACAGAGTCACCATCAC TTGCCGGGCAAGTCAGGGCATTAGAAATGATT TAGGCTGTATCAGCAGAAACCAGGGAAAGC CCCTAAGCGCCTTATCTATGCTGCATCCAGTTT GCAAAGTGGGGTCCCATCAAGGTTCAGCGGCA GTGGATCTGGGACAGAATTCATTCTCACAATC AGCAGCCTGCAGCCTGTAATGCATAATAGTTACCCTCGA CGTTCGGCCAAGGGACCAAGGTGAAATCAA A |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGTACGACTACGGTATGGACGTCT GGGGCCAAGGGACCACGGTCACCGTCTCCTCA |
| | | | SEQ ID NO: 27133 |
| | | | SEQ ID NO: 31139 |
| | | AA | DIQMTLSPSSLPASVGDRVTITCRASQGIRNDLG WYQQKPGKAPKRLIYGASSLQSGVPSRFSGSGS GTEFILTISSLQPEDFATYYCVMHNSYPRTFGQG TKVEIK |
| | | | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS |
| | | | SEQ ID NO: 27134 |
| | | | SEQ ID NO: 31140 |

FIGURE 50
(Continued)

| | | | | |
|---|---|---|---|---|
| iPS:436448 | 21-225_217A3 | NA | GAAATTGTGCTGACTCAGTCTCCAGACTTTAAGTCTGTGACTCCAAAGGAGAAAGTCACCATCACCTGCCGGGCCAGTCAGAGCAGAGAAACCAGATCAGTCCTTACACTGGTACCAGCAGAAACCAGATCAGTCTCCAAAGCTCCTCGTCAAGTATGCTTCCCAGTCCTTCTCAGGGGTCCCCTCGAGGTTCAGTGGCAGTGGATCTGGGACAGATTTCACCCTCACCATCAACAGCCTGGAGGCTGAAGATGTGCAAGGTATTACTGTCATCAGAGTAGAAGTTTACCCGTGGACGTTCGGCCAAGGGACCAAGGTGGAAATCAAA | GAGGTGCAACTGGTGGAGTCGGGGGGAGGCTTGGTACAGCCTGGGGGGTCCCTGAGACTCTCCTGTGCAGCCTCTGGATTCACCTTCAGTAGCTATATATGAACTGGGTCCGCCAGGCTCCAGGAAGGCTGGAGTGGGTTTCATACATTAGTAGTAGTCGTAATATCATATATTACGCAGACTCTGTGAAGGGCCGATTCACCATCTCCAGAGAAATGCCAAGAACTCACTGTCTCTGCAAATGGACAGCCTGAGAGACGAGGACACGGCTGTGTATTACTGTGCGCGAGATGGCTCTTATAGCAGTGGCTGGTACTGGGGTTTTGACTACTGGGGCCAGGGCACCCTGGTCACCGTCTCCTCA |
| | | | SEQ ID NO: 27135 | SEQ ID NO: 31141 |
| | | AA | EIVLTQSPDFKSVTPKEKVTITCRASQSQSIGSSLHWYQQKPDQSPKLLVKYASQSFSGVPSRFSGSGSGTDFTLTINSLEAEDGATYYCHQSRSLPWTFGQGTKVEIK | EVQLVESGGGLVQPGGSLRLSCAASGFTFSSYNMNWVRQAPGKGLEWVSYISSSRNIIYADSVKGRFTISRENAKNSLSLQMDSLRDEDTAVYYCARDGSYSSGWYWGFDYWGQGTLVTVSS |
| | | | SEQ ID NO: 27136 | SEQ ID NO: 31142 |
| iPS:436450 | 21-225_217E5 | NA | GACATCCAGATGACCCAGTCTCCATCTTCCCGCCTGCATTTGTAGGAGACAGAGTCACCATCACTTGCCGGGCAAGTCAGGGCATTAGAAATGATTTAGGCTGGTATCAGCAGAAACCAGGGAAAGCCCCTAAGCGCCTTATCTGTGCTGCATCCAGTTTGCAAAGTGGGGTCCCATCAAGGTTCAGCGGCAGTGGATCTGGGACAGAATTCATTCTCACAATCAGCAGCCTGCAGCCTGAAGATTTTGCAACTTATTACTGTGTAATGCATCATAATAGTAGTACCCCTCGGACGTTCGGCCAAGGGACCAAGGTGGAAATCAAA | CAGGTGCAGCTGGTGGAGTCTGGGGGAGGCGTGGTCCAGCCTGGGAGGTCCCTGAGACTCTCCTGTGCAGCGTCTGGATTCACCTTCAGTGACTATGTCATGCACTGGGTCCGCCAGGCTCCAGGCAAGGGGCTGGAGTGGGTGGCAGTTATATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAACGTTATAGCAGTGGCTGGTACGACTACGGTATGGACGTCTGGGGCCAAGGGACCACGGTCACCGTCTCCTCA |
| | | | SEQ ID NO: 27137 | SEQ ID NO: 31143 |

FIGURE 50
(Continued)

| | | | |
|---|---|---|---|
| | | AA | DIQMTQCPSSPPAFVGDRVTITCRASQGIRNDLG WYQQKPGKAPKRLICAASSLQSGVPSRFSGSGS GTEFILTISSLQPEDFATYYCVMHNSYPRTFGQG TKVEIK<br>SEQ ID NO: 27138 | QVQLVESGGGVVQPGRSLRLSCAASGFTFSDYVM HWVRQAPGKGLEWVTVIWYDGSNKYADSVKGR FTISRDNSKNTLYLQMNSLRAEDTAVYYCARERYS SGWYDYGMDVWGQGTTVTVSS<br>SEQ ID NO: 31144 |
| iPS:436452 | 21-225_217G5 | NA | GACATCCTGATGACCCAGTCTCCATCCTCACT GTCTGCATCTGTAGGAGACAGAGTCACCATCA CTTGTCGGGCGAGTCAGGCATTCAGGCAATTAT TTAGCCTGGTTTCAGCAGAAGACCAGGGAAAGC CCCTAAGTCCCTGATCTATGCTGCATCCAGTTT GCAAAGTGGGGTCCCATCAAAGTTCAGCGGCA CTGGATCTGGGACAGATTTCACTCTCACCATC AGCAGCCTGCAGCCTGACGATTTTGCAACTTA TTACTGCCAACAGTATGTTAATTACCCTCTCAC TTTCGGCGGAGGGACCAAGGTGGAGATCAAC<br>SEQ ID NO: 27139 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCGATTACAT GCACTGGGTCCGCCAGGCTCCAGGCAAGGGGCT GGAGTGGGTGGCAGTTATATGGTATGATGGAAGT AATAAAACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGACTACGG TGTCGGGTACTACGGTCTGGACGTCTGGGGCCAA GGGACCACGGTCACCGTCTCCTCA<br>SEQ ID NO: 31145 | 
| | | AA | DILMTQSPSSLSASVGDRVTITCRASQGIGNYLA WFQQRPGKAPKSLIYAASSLQSGVPSKFSGTRSG TDFTLTISSLQPDDFATYYCQQYVNYPLTFGGGT KVEIN<br>SEQ ID NO: 27140 | QVQLVESGGGVVQPGRSLRLSCAASGFTFSSNGMH WVRQAPGKGLEWVAVIWYDGSNKNYADSVKGR TISRDNSKNTLYLQMNSLRAEDTAVYYCARDYGV GYYGLDVWGQGTTVTVSS<br>SEQ ID NO: 31146 |

FIGURE 50
(Continued)

| | | | | |
|---|---|---|---|---|
| iPS:436454 | 21-225_217B10 | NA | GACATCCGGATGACCCAGTCTCCATCCTCACT GTCTGCATCTGTAGGAGACAGAGTCACCATCA CTTGTCGGGCGAGTCAGGCCATTGGGAAACAT TTAGCCTGGTTTCAGCAGAGACCTGGAAAGC CCCTAAGTCCCTGATCTATGCTGCATCCAGATT CCCTAAGTCCCTGATCTATGCTGCATCAAGT GCAAAGTGGGGGTCCCATCAAAGTTCAGCGGCA GTGGATCTGGGACAGATTTCACTCTCACCATC AGCAGCCTGCAGCCTGAAGATCTTGCAACTTA TTACCGTCAACACCACCAGTAAATCTCCAGTGC AGCTTGTCTGGAGGCACCAAGGTGGAGATCAC A | CAGGTGCAGCTGGTGGAGTCTGGGGGAGGCGTG GTCCAGCCTGGGAGGTCCCTGAGACTCTCCTGTG CAGTGTCTGAATCACCTTCAGTAGTAGTGCAT GCACTGGGCCCGCCAGGCTCCAGGCAAGGGCT GGAGTGGGTGGCAGTTATATGTATGATGGAAGT AATAAAAACTATGAAGACTCCGTGAAGGGCCGA TTCACCATCTCCAGAGACAACTCCAAGAACACGC TGTATCTGCAAATGAACAGCCTGAGAGCCGAGG ACACGGCTGTGTATTACTGTGCGAGAGATGGGAG TTATGGTTACGACGGTATGGACGTCTGGGGCCAA GGGACCACGGTCACCGTCTCCTCA |
| | | AA | DIRMTQSPSSLSASVGDRVTITCRASQAIGKIHLA WFQQRPGKAPKSLIYAASRLQSGVPSKFSGSGSG TDFTLTISSVQPEDLATYYRQHTSKSPVQLVGGT KVEIT | QVQLVESGGGVVQPGRSLRLSCAVSGITFSSYGMH WARQAPGKGLEWVAVIWYDGSNKNYEDSVKGRF TISRDNSKNTLYLQMNSLRAEDTAVYYCARDGSYG YDGMDVWGQGTTVTVSS |
| | | | SEQ ID NO: 27141 | SEQ ID NO: 31147 |
| | | | SEQ ID NO: 27142 | SEQ ID NO: 31148 |
| iPS:436456 | 21-225_217G10 | NA | GACATCCAGATGACCCAGTCTCCATCTCCCC GCCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCTGCATCCAGTT TGCAAAGTGGGGTCCCATCAAGGTTCAGCGGC AGTGGATCTGGGACAGAATTCATTCTCACTAT CAGCAGCCTGCAGCCTGAAGATTTTGCAACTT ATTACTGTGTAATGCATCATAATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGGACAGTTATATGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGGTACGACTACGGTATGGACGTCT GGGGCCAAGGGACCACGGTCACCGTCTCCTCA |
| | | | SEQ ID NO: 27143 | SEQ ID NO: 31149 |

FIGURE 50
(Continued)

| | | | |
|---|---|---|---|
| | | AA | DIQMTQSPSSPPASVGDRVTITCRASQGIRNDLG WYQQKPGKAPKRLIYAASSLQSGVPSRFSGSGS GTEFILTISSLQPEDFATYYCVMHNSYPRTFGQG TKVEIK<br><br>SEQ ID NO: 27144 | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS<br><br>SEQ ID NO: 31150 |
| iPS:436458 | 21-225_217H12 | NA | GACATCCAGATGACCCAGTCTCCATCTTCCCC GCCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTTATCTATGCTGCATCCAGTT TGCAAAGTGGATGGGTCCCATCAAGGTTCAGCGGC AGTGGATCTGGGACAGACTTCATTCTCACAAT CAGCAGCCTGCAGCCTGAAGATTTTGCAACTT ATTACTGTGTCTAATGCATTATAGTTACCCTCGA CGTTCGGCCAAGGGACCAAGGTGGAAATCAA A<br><br>SEQ ID NO: 27145 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGTAGGACTACGGTATGGACGTCT GGGGCCAAGGGACCACGGTCACCGTCTCCTCA<br><br>SEQ ID NO: 31151 |
| | | AA | DIQMTQSPSSPPASVGDRVTITCRASQGIRNDLG WYQQKPGKAPKRLIYAASSLQSGVPSRFSGSGS GTEFILTISSLQPEDFATYYCLMHYSYPRTFGQGT KVEIK<br><br>SEQ ID NO: 27146 | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS<br><br>SEQ ID NO: 31152 |

FIGURE 50
(Continued)

| | | | |
|---|---|---|---|
| iPS:436462 | 21-225_218C4 | NA | GACATCCAGATGACCCAGTCTCCATCTTCCCC GCCTGCATTTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTTATCTATGCTGCATCCAGTT TGCAAAGTGGGGTCCCATCAAGGTTCAGCGGC AGTGGATCTGGGACAGAATTCATTCTCACAAT CAGCAGGTGCAGCGTGAAGATTTTGCAACTT ATTACTGTGAATGCATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGAITCACCTTCAGTGACTATGTCAT GCACTGGGTCCGCCAGGCTCCAGGCAAGGGCT GGAGTGGGTGACAGTTATATGGTATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGGTACGACTACGGTATGGACGTCT GGGGCCAAGGGACCACGGTCACCGTCTCCTCA |
| | | SEQ ID NO: 27147 | SEQ ID NO: 31153 |
| | | AA | DIQMTQCPSSPPAFVGDRVTITCRASQGIRNDLG WYQQKPGKAPKRLIYAASSLQSGVPSRFSGSGS GTEFILTISSVQREDFATYYCVMHYSYPRTFGQG TKVEIK | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS |
| | | SEQ ID NO: 27148 | SEQ ID NO: 31154 |
| iPS:436464 | 21-225_219H1 | NA | GACATCCAGATGACCCAGTCTCCATCCTCACA GTCTGCATCTGTAGGAGACAGAGTCACCATCA CTTGTCGGGCGAGTCAGGGCATTAGCAATTAT TTAGACTGGTTTCAGCAGAAACCAGGGAAAGC CCCTAAGTCCCTGATCTATTCTGCATCCAATTT GCAAAGTGGGGTCCCATCAAAGTTCAGCGGCA GTAGATCTGGGACAGATTTCACTCTCACCATC AGCAGCCTGCAGCCTGAAGATTTTGCAACTTA TTACTGCCAACACTATAGTAATTACCCGCTCA CTTTCGGCGGAGGGACCAAGGTGGAGATCAA A | CAGGTGCAGCTGGTGGAGTCTGGGGGAGGCGTG GTCCAGCCTGGGAGGTCCCTGAGACTCTCCTGTG CAGCGTCTGAITCACCTTCAGTAGATATGGCAT GCACTGGGTCCGCCAGGCTCCAGGCAAGGGCT GGAGTGGGTGGCAGTTATATGGTATGGAAGT AATAAACACTATGCAGACTCCGTGAAGGGCCGA TTCACCATCTCCAGAGACAATTCCAAGAATACGT TGTATCTGCAAATGAACAGTCTGAGAGGCGAGG ACACGGCTGTGTATTACTGTGCGAGAGATCGGGG AGTGGGCTACAACGGTATGGACGTCTGGGGCCA AGGGACCACGGTCACCGTCTCCTCA |
| | | SEQ ID NO: 27149 | SEQ ID NO: 31155 |

FIGURE 50
(Continued)

| | | | |
|---|---|---|---|
| iPS:436472 | 21-225_220E1 | AA | DIQMTQSPSSSQSASVGDRVTITCRASQGISNYLD WFQQKPGKAPKSLIYSASNLQSGVPSKFSGSRSG TDFTLTISSLQPEDFATYYCQHYSNYPLTFGGGT KVEIK<br>SEQ ID NO: 27150 | QVQLVESGGGVVQPGRSLRLSCAASGFTFSRYGMH WVRQAPGKGLEWVAVIWYDGSNKHYADSVKGRF TISRDNSKNTLYLQMNSLRGEDTAVYYCARDRGV GYNGMDVWGQGTTVTVSS<br>SEQ ID NO: 31156 |
| | | NA | GAAATTGTGTTGACGCAGTCTCCAGGCACCCT GTCTTTGTCTCCAGGGGAAAGAGCCACCCTCT CCTGCAGGGCCAGTCAGAGTATTAGCCGCAGC CACTTAGTCTGGTACCAGCAGAAACCTAACCA GGCTCCCAGGCTCCTCTATGTTACATCCAG CAGGGCCACTGGCATCCCAGACACAGGTTTAGTG GCAGTGGGTCTGGGACAGACTTCACTCTCACC ATCAGAAGTCTGGAGCTGAAGATTTTGCAAT GTATTACTGTCAGCAGTATGGTAGTCACCGT GGACGTTCGGCCAAGGGACCAAGGTGAAAT CAAA<br>SEQ ID NO: 27151 | CAGGTGCAGCTGCAGGAGTCGGGCCCAGGACTG GTGAAGCCTTCGGAGACCCTGTCCCTCACCTGCA CTGTCTCTGGTGGCTCCATCAGTACTACTACTG GAGCTGGATCCGGCAGCCCCAGGGAAGGACT GGAGTGGATTGGGTATATCTATTACAGTGGGACC ACCAACTACAACCCCTCCCTCAAGAGTCGAGTCA CCATATCAGTAGACACGTCCAAGAACCAGTTCTC CCTGAAGCTGAGCTCTGTGACCGCTGCGGACACG GCCGTGTATTACTGTGCGAGAGACAACTAGTGGC TGGTACGTGGGAGGACAACTACTACTACGGTAT GGACGTCTGGGGCCAAGGGACCACGGTCACCGT CTCCTCA<br>SEQ ID NO: 31157 |
| | | AA | EIVLTQSPGTLSLSPGERATLSCRASQSISRSHLV WYQQKPGQAPRLLLYVTSSRATGIPDRFSGSGS GTDFTLTIRSLEPEDFAMYYCQQYGSSPWTFGQ GTKVEIK<br>SEQ ID NO: 27152 | QVQLQESGPGLVKPSETLSLTCTVSGGSISTYYWSW IRQPPGKGLEWIGYIYYSGTTNYNPSLKSRVTISVDT SKNQFSLKLSSVTAADTAVYYCARDQQWLVRGRD NYYYGMDVWGQGTTVTVSS<br>SEQ ID NO: 31158 |

FIGURE 50
(Continued)

| | | | |
|---|---|---|---|
| iPS:436480 | 21-225_220F8 | NA | GACATCCAGATGACCCTGTCTCCATCTTCCCC GCCTGCATTTGTAGGAGACAGAGTCACCATCA CTCGCCGGGCAAGTCAGGGCATTAGAAATGAT TTAGGCTGGTATCAGCAGAAACCAGGGAAAG CCCCTAAGCTCCTTATATGTGTGCATCCAGT TTGCAAAGTGGGGTCCATCAAGGTTCAGCGG CAGTGGATCTGGGACAGAATTCATTCTCACAA TCAGCAGCCTGCAGCGTGAAGATTTTGCAACT TATTACTGTGTAATGCATAATAGTTACCCTCG GACGTTCGGCCAAGGGACCAAGGTGGAAATC AAA |
| | | | SEQ ID NO: 27153 |
| | | AA | DIQMTLSPSSPPAFVGDRVTITRRASQGIRNDLG WYQQKPGKAPKLLCGASSLQSGVPSRFSGSGS GTEFILTISSLQREDFATYYCVMHNSYPRTFGQG TKVEIK |
| | | | SEQ ID NO: 27154 |
| iPS:436488 | 21-225_221A6 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATACTGCATCCAATT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A |
| | | | SEQ ID NO: 27155 |

| | |
|---|---|
| | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGTCAT GCACTGGGTCCGCCAGGCTCCAGGCAAGGGGCT GGAGTGGGTGACAGTTATATGGTATGATGGAAGT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGAACGTTAT AGCAGTGGCTGGTACGACTACGGTATGGACGTCT GGGGCCAAGGGACCACGGTCACCGTCTCCTCA |
| | SEQ ID NO: 31159 |
| | QVQLVESGGGVVQPGRSLRLSCAASGFTFSDYVM HWVRQAPGKGLEWVTVIWYDGSNKYYADSVKGR FTISRDNSKNTLYLQMNSLRAEDTAVYYCARERYS SGWYDYGMDVWGQGTTVTVSS |
| | SEQ ID NO: 31160 |
| | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAATTTCAGGGCAG GGTCACCCTGACCAGGGACACGTCCATCAGCAC AGCCTACATGGACCTGAGCAGGCTGAGATCTGA CGACACGGCCGTGTATTACTGTGCGAGAGATGG ACCAGCTCGTTTGACTACTGGGGCCAGGGAACC CTGGTCACCGTCTCCTCA |
| | SEQ ID NO: 31161 |

FIGURE 50
(Continued)

| | | | | |
|---|---|---|---|---|
| iPS:436490 | 21-225_221F6 | AA | DIQMTQSPSSVSASVGDRVTITCRASQGISSWLAWYQQKPGKAPKLLIYTASNLQSGVPSRFSGSGSGTDFTLTISSLQPEDFATYYCQQANSFPFTFGPGTKVDIK<br>SEQ ID NO: 27156 | QVQLVQSGAEVKKPGASVKVSCKTSGYTFTGYYMHWVRQAPGQGLEWMGWIHPNSGGTNYAQKFQGRVTLTRDTSISTAYMDLSRLRSDDTAVYYCARDGTSSFDYWGQGTLVTVSS<br>SEQ ID NO: 31162 |
| | | NA | GACATCCAGATGACCCAGTCTCCATCCTCACTGTCTGCATCTGTAGGAGACAGAGTCACCATCACTTGTCGGGCGAGTCAGGGCATTAGCAGTTGGTTAGCCTGGTTTCAGCAGAAACCAGGGAAAGCCCCTAAATCCCTGATCTATGCTGCATCCAATTTACAAAGTGGGGTCCCATCAAGGTTCAGCGGCAGTAGATCTGGGACAGATTTCACTCTCACCATCAGCAGCCTGCAGCCTGAAGATTTTGCAACTTATTACTGCCAACAGTATGACTTACCCGCTCACTTTCGGCGGAGGGACCAAGGTGGAGATCAAA<br>SEQ ID NO: 27157 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCAATGGCATGCACTGGGTCCGCCAGGCTCCAGGCAAGGGGCTGGAGTGGGTGGCAGTTATATGTACGATGGAAGTAATGAAAACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGAGAGTGGGCTACAACGGTATGACGTCTGGGGCCAAGGGACCACGGTCACCGTCTCCTCA<br>SEQ ID NO: 31163 |
| | | AA | DIQMTQSPSSLSGSVGDRVTITCRASQGISNYLAWFQQKPGKAPKSLIYAASNLQSGVPSKFSGSRSGTDFTLTISSLQPEDFATYYCQQYMTYPLTFGGGTRVEIK<br>SEQ ID NO: 27158 | QVQLVESGGGVVQPGRSLRLSCAASGFTFSSNGMHWVRQAPGKGLEWVAVIWYDGSNENYADSVKGRFTISRDNSKNTLYLQMNSLRAEDTAVYYCARDRTVGYNGMDVWGQGTTVTVSS<br>SEQ ID NO: 31164 |

FIGURE 50
(Continued)

| | | | |
|---|---|---|---|
| iPS:436494 | 21-225_221F12 | NA | GACATCCAGATGACCCAGTCTCCATCTTCCGT GTCTGCATCTGTAGGAGACAGAGTCACCATCA CTTGTCGGGCGAGTCAGGTATTAGCAGCTGG TTAGCCTGGTATCAGCAGAAACCAGGGAAAG CCCCTAAGCTCCTGATCTATACTGCATCCAATT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A <br> SEQ ID NO: 27159 | CAGGTGCAGCTGGTGCAGTCTGGGGCTGAGGTG AAGAAGCCTGGGGCCTCAGTGAAGGTCTCCTGC AAGACTTCTGGATACACCTTCACCGGCTACTATA TGCACTGGGTGCGACAGGCCCCTGGACAAGGGC TTGAGTGGATGGGATGGATCCACCCTAACAGTGG TGGCACAAACTATGCACAGAAATTTCAGGCAG GGTCACCCTGACCAGGGACACGTCCATCAGCAC AGCCTACATGGACCTGAGCAGGCTGAGATCTGA CGACACGGCCGTGTATTACTGTGCGAGAGATGG GACCAGTCGTTGACTACTGGGGCCAGGGAACC CTGGTCACCGTCTCCTCA <br> SEQ ID NO: 31165 |
| | | AA | DIQMTQSPSSVSASVGDRVTITCRASQGISSWLA WYQQKPGKAPKLLIYTASNLQSGVPSRFSGSGS GTDFTLTISSLQPEDFATYYCQQANSFPFTFGPGT KVDIK <br> SEQ ID NO: 27160 | QVQLVQSGAEVKKPGASVKVSCKTSGYTFTGYYM HWVRQAPGQGLEWMGWIHPNSGGTNYAQKFQGR VTLTRDTSISTAYMDLSRLRSDDTAVYYCARDGTS SFDYWGQGTLVTVSS <br> SEQ ID NO: 31166 |
| iPS:436496 | 21-225_222E1 | NA | GACATCCAGATGACCCAGTCTCCATCTTCCGT GTCTGCATCTGTAGGAGACAGAGTCACCATCA CTTGTCGGGCGAGTCAGGTATTAGCAGCTGG TTAGCCTGGTATCAGCAGAAACCAGGGAAAG CCCCTAAGCTCTTGATCTATACTGCATCCAATT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTTCCCATTC ACTTTCGGCCCTGGGACCAAAGTGGATATCAA A <br> SEQ ID NO: 27161 | CAGGTGCAGCTGGTGCAGTCTGGGGCTGAGGTG AAGAAGCCTGGGGCCTCAGTGAAGGTCTCCTGC AAGACTTCTGGATACACCTTCACCGGCTACTATA TGCACTGGGTGCGACAGGCCCCTGGACAAGGGC TTGAGTGGATGGGATGGATCCACCCTAACAGTGG TGGCACAAACTATGCACAGAAATTTCAGGCAG GGTCACCCTGACCAGGGACACGTCCATCAGCAC AGCCTACATGGACCTGAGCAGGCTGAGAGATG CGACACGGCCGTGTATTACTGTGCGAGAGATG GACCAGTCGTTTGACTACTGGGGCCAGGGAACC CTGGTCACCGTCTCCTCA <br> SEQ ID NO: 31167 |

FIGURE 50
(Continued)

| | | | | |
|---|---|---|---|---|
| | | AA | DIQMTQSPSSVSASVGDRVTITCRASQGISSWLA WYQQKPGKAPKLLIYTASNLQSGVPSRFSGSGS GTDFTLTISSLQPEDFATYYCQQANSFPFTFGRGT KVDIK | QVQLVQSGAEVKKPGASVKVSCKTSGYTFTGYYM HWVRQAPGQGLEWMGWIHPNSGGTNYAQKFQGR VTLTRDTSISTAYMDLSRLRSDDTAVYYCARDGTS SFDYWGQGTLVTVSS |
| | | | SEQ ID NO: 27162 | SEQ ID NO: 31168 |
| iPS:436500 | 21-225_222H3 | NA | GACATCGTGATGACCCAGTCTCCAGACTCCCT GGCTGTGTCTCTGGGCGAGAGGGCCACCATCA ACTGCAAGTCCAGCCAGAGTGTTTTGAAAAGT TCCAACCATAGGAACTACTTAGCTTGGTACCA ACAGAAACCAGGGCAGCCTCCTCAGCTTCTCA TTTACTGGGCATCTACCCGGGAATCCGGGTC CCTGACCGATTCAGTGGCAGCGGGTCTGGGAC AGATTTCACTCTCACCATCAGCAGCCTCAGG CTGAAGATGTGTCAGTTTATTCCTGTCAGCAA TATTCTTCTATTCCGTGGACGTTCGGCCAAGG GACCAAGGTGGAAATCAAT | CAGGTTCAGTCTGGTGCAGTCTGGAGCTGAGGTGA AGAAGCCTGGGGCCTCAGTGAAGGTCTCCTGCA AGGCTTCTGGTTTCACCTTTACCAGCTATGGTATC AACTGGGTGCGACAGGCCCCTGGACAAGGGCTT GAGTGGATGGGATGGATCAGGTTTACAATGGTA ACACAAACTATGCACAGAAGCTCCAGGGCAGAG TCACCATGACCAGACACATCCACGAGACAG CCTACATGGAGCTGAGGAGCCTGAGATCTGACG ACACGGCCGTGTATTACTGTGCGAGAGACTACTA CTACGGTTTGACGTCTGGGGCCAAGGGACCACG GTCACCGTCTCCTCA |
| | | | SEQ ID NO: 27163 | SEQ ID NO: 31169 |
| | | AA | DIVMTQSPDSLAVSLGERATINCKSSQSVLKSSN HRNYLAWYQQKPGQPPQLLIYWASTRETGVPD RFSGSGSGTDFTLTISSLQAEDVSVYSCQQYSSIP WTFGQGTKVEIN | QVQLVQSGAEVKKPGASVKVSCKASGFTFTSYGIN WVRQAPGQGLEWMGWISVYNGNTNYAQKLQGR VTMTDTSTSTAYMELRSLRSDDTAVYYCARDYY YGFDVWGQGTTVTVSS |
| | | | SEQ ID NO: 27164 | SEQ ID NO: 31170 |

FIGURE 50
(Continued)

| | | | |
|---|---|---|---|
| iPS:436502 | 21-225_222A11 | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTGGCCTGGTTTCAGCAGAAACCAGGGAAAGC CCCTAAGTCCCTGATCTACGCTGCATCCAGTTT GCAAAGTGGGGTCCCATCAAAGTTCAGCGGCA GTGGATCTGGGACAGATTTCACTCTCACCATC AGTAGCCTGCAGCCTGAAGATTTTGCAACTTA TTACTGCCTATATTATCTTAATTATCCGCTCAC TTTCGGCGGAGGGACCAAGGTGGAGATCAAA<br><br>SEQ ID NO: 27165 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAATGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGATCGGGA TGTCGGGTACAACGGTATGGACGTCTGGGGCCA AGGGACCACGGTCACCGTCTCCTCA<br><br>SEQ ID NO: 31171 |
| | | AA | DIQMTQSPSSLSASVGDRVTITCRASQGISNYLA WFQQKPGKAPKSLIYAASSLQSGVPSKFSGSGSG TDFTLTISSLQPEDFATYYCLYLNYPLFGGGT KVEIK<br><br>SEQ ID NO: 27166 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDRDV GYNGMDVWGQGTTVTVSS<br><br>SEQ ID NO: 31172 |
| iPS:436504 | 21-225_222H4 | NA | GACATCCAGATGACCCCATTCTCCATCCTCCCT GTCTGCATCTGTAGGAGACAGAGTCACCATCA CTTGCCGGGCAAGTCAGAACATTAGTAATTAT GTTAATTGGTATCAGCAGAAACCAGGGAAAG CCCCTAAGTCCCTGATCTATACTGCGTCCAGTT TGCAAAGTGGGGTCCGTCAGGTTCAGTGGC AGTGGATCTGGGACAGATTTCACTCTCACCAT CAGCAGTCTGCAACCGTGACGATTTTGCAATTT ACTATTGTCAGCAGTATTACTTACCCCATTCA CTTTCGGCCCTGGGACCAAAGTGGATATCAAA<br><br>SEQ ID NO: 27167 | GAGGTGCAGCTATTGGAGTCTGGGGGAGGCTTG GTACAGCCTGGGGGGTCCCTGAGACTCTCCTGTG CAGCCTCTGGTTCACCTTTAGCAACTTTGCCAT GAGTTGGGTCCGCCAGGCTCCAGGGAAGGGACT GGAGTGGGTCTCAAGTATTGTTGGTAGTGGTGGT CGCACGTACTACGCAGACTCCGTGAAGGGCGG TTCACCATCTCCAGAGACAATTCCAAGAACACGC TGTATCTGCAAATGAACAGCCTGAGAGCCGAGG ACACGGCCGTATATTATTGTGCGAAAGACCCTTA TCGTGTAGCAGTGGCTGGGGCCTTTGACTACTGG GGCCAGGGAACCCTGGTCACCGTCTCCTCA<br><br>SEQ ID NO: 31173 |

FIGURE 50
(Continued)

| | | | |
|---|---|---|---|
| iPS:436506 | 21-225_222C7 | AA | DIQMTHSPSSLSASVGDRVTITCRASQNISNYVN WYQQKPGKAPKFLIYTASSLQSGVSSRFSGSGSG TDFTLTISSVHRDDFAIYYCQQYFTPFTFGRGT KVDIK<br>SEQ ID NO: 27168 | EVQLLESGGGLVQPGGSLRLSCAASGFTFSNFAMS WVRQAPGKGLEWVSSIVGSGGRTYYADSVKGRFTI SRDNSKNTLYLQMNSLRAEDTAVYYCAKDPYRVA VAGAFDYWGQGTLITVSS<br>SEQ ID NO: 31174 |
| | | NA | GAAATTGTGTTGACGCAGTCTCCAGGCACCCT GTCTTTGTCTCCAGGGGAAAGAGCCACCCTCT CCTGCAGGGCCAGTCAGAGTGTTTACAGCAAC TACTTAGCCTGGTACCAGCAGAAACCTGGCCA GGCTCCCAGGCTCCTCATCTATGGTGCATCAA GCAGGGGCCACTGGCATCCCAGACAGGTTCGGT GGCAGTGGGTCTGGGACAGACTTCACTCTCGC CATAAGCAGACTGGAGCCTGAAGACTTTACAA TATATTACTGTCAGCAGTATGAAGACTCACCG TGGACGTTCGGCCAAGGGACCAAGGTGGAAA TCAAA<br>SEQ ID NO: 27169 | CAGGTGCAGTCTACAGCAGTGGGGCGCAGGACTG TTGAAGCCTTCGGAGACCCTGTCCCTCACCTGCG CTGTCTATGTGGGTCCTTCAGTGTCGCTACTG GAGCTGGATCCGCCAGCCCCAGGGAAGGGGCT GGAGTGGATTGGGGAAATCAATCATAGTGGAAG CGCCAACTACAACCCGTCCCTCAAGAGTCGAGTC ACCATATCAGTAGACACGTCAAGAACCAGTTCT CCCTGAAGCTGAGTTCTGTGACCGCCGCGGACAC GGCTGTATATTACTGTGCGAGAGATACGGCGCC CTTGATTTCTGGGGCCAAGGGACAATGGTCACCG TCTCTCTCA<br>SEQ ID NO: 31175 |
| | | AA | EIVLTQSPGTLSLSPGERATLSCRASQSVYSNYLA WYQQKPGQAPRLLIYGASSRATGIPDRFGSGS GTDFTLAISRLEPEDFTIYYCQQYEDSPWTFGQG TKVEIK<br>SEQ ID NO: 27170 | QVQLQQWGAGLLKPSETLSLTCAVYGGSFSGRYW SWIRQPPGKGLEWIGEINHSGSANYNPSLKSRVTIS VDTSKNQFSLKLSSVTAADTAVYYCARDYGALDF WGQGTMVTVSS<br>SEQ ID NO: 31176 |

FIGURE 50
(Continued)

| | | | |
|---|---|---|---|
| iPS:436508 | 21-225_222F7 | NA | GACATCCAGATGACCCAGTCTCCATCTTCCGT GTCTGCATCTGTAGGAGACAGAGTCACCATCA CTTGTCGGGCGAGTCAGGGTATTAGCAGCTGG TTAGCCTGGTATCAGCAGAAACCAGGGAAAG CCCCTAAGCTCCTGATCTATGCATCCAATT TGCAAAGTGGGGTCCCATCAAGGTTCAGCGGC AGTGGATCTGGGACAGATTTCACTCTCACCAT CAGCAGCGTGCAGCCTGAAGATTTTGCAACTT ACTATTGTCAACAGGCTAACAGTTTCCCATTC ACTTTCGGCCCTGGGACCAAAGTGGATATCAA A <br><br>SEQ ID NO: 27171 | CAGGTGCAGCTGGTGCAGTCTGGGGCTGAGGTG AAGAAGCCTGGGGCCTCAGTGAAGGTCTCCTGC AAGACTTCTGGATACACCTTCACCGGCTACTATA TGCACTGGGTGCGACAGGCCCCTGGACAAGGGC TTGAGTGGATGGGATGGATCCACCCTAACAGTGG TGGCACAAACTATGCACAGAAATTTCAGGGCAG GGTCACCCTGACCAGGGACACGTCCATCAGCAC AGCCTACATGGACCTGAGCAGGCTGAGATCTGA CGACACGGCCGTGTATTACTGTGCGAGAGATGG GACCAGTCGTTTGACTACTGGGGCCAGGGAACC CTGGTCACCGTCTCCTCA <br><br>SEQ ID NO: 31177 |
| | | AA | DIQMTQSPSSVSASVGDRVTITCRASQGISSWLA WYQQKPGKAPKLLIYASNLQSGVPSRFSGSGS GTDFTLTISSVQPEDFATYYCQQANSFPFTFGPGT KVDIK <br><br>SEQ ID NO: 27172 | QVQLVQSGAEVKKPGASVKVSCKTSGYTFTGYYM HWVRQAPGQGLEWMGWIHPNSGGTNYAQKFQGR VTLTRDTSISTAYMDLSRLRSDDTAVYYCARDGTS SFDYWGQGTLVTVSS <br><br>SEQ ID NO: 31178 |
| iPS:436510 | 21-225_222H8 | NA | GACATCCAGATGACCCAGTCTCCATCTTCCCTG TCTGCATCTGTAGGAGACAGAGTCACCATCAC TTGCCGGGCAAGTCAGAACAGTCATTAGTTATG TTAATTGGTATCAGCAGAAACCAGGGAAAGCC CCTAAGTTCCTGATCTATATTGCATCGAGTTTG CAAAGTGGGGTCTCGTCACGGTTCAGTGGCAG TGGATCTGGGACAGATTTCACTCTCACCATCA GCAGTGTGCACCGTGACGATTTTGCAATTTAC TACTGTCAGCAGTATTACTTTACCCCATTCACT TTCGGCCGTGGGACCAAAGTGGATATCAAA <br><br>SEQ ID NO: 27173 | GAGGTGCAGCTATTGGAGTCTGGGGGAGGCTTG GTACAGCCTGGGGGGTCCCTGAGACTCTCCTGTG CAGCCCTCTGGCTTCACCTTTAGCAACTTTGCCAT GAGTTGGGTCCGCCAGGCTCCAGGGAAGGGACT GGAGTGGGTCTCAAGTATTGTTGGTAGTGGTGGT CGCACGTACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATTATTGTGCGAAAGACCCTTA TCGTGTAGCAGTCAGTGGCTGGCCCTTTGACTACTCG GGCCAGGGAACCCTGATCACCGTCTCCTCA <br><br>SEQ ID NO: 31179 |

FIGURE 50
(Continued)

| | | | | |
|---|---|---|---|---|
| | | AA | DIQMTHSPSSLSASVGDRVTITCRASQNISNYVN WYQQKPGKAPKFLIYIASSLQSGVSSRFSGSGSG TDFTLTISSVHRDDFAIYYCQQYFTPFTFGRGT KVDIK<br><br>SEQ ID NO: 27174 | EVQLLESGGGLVQPGGSLRLSCAASGFTFSNFAMS WVRQAPGKGLEWVSSIVGSSGGRTYYADSVKGRFTI SRDNSKNTLYLQMNSLRAEDTAVYYCAKDPYRVA VAGAFDYWGQGTLTVSS<br><br>SEQ ID NO: 31180 |
| iPS:436514 | 21-225_222D10 | NA | GACATCCAGATGACCCAGTCTCCATCCTCACT GTCTGCATCTGTAGGAGACAGAGTCACCATCA CTTGTCGGGCGAGTCAGGACATTAGCAATTAT TTGGCCTGGTTTCAGCAGAAACCAGGGAAAGC CCCTAAGTCCCTGATCTACGCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCTACATTATCTTAATTACCCGCTCAC TTTCGGCGGAGGGACCAGGGTGGAGATCAAA<br><br>SEQ ID NO: 27175 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTATGGCAT GCACTGGGTCCGCCAGGCTCCAGGCAAGGGGCT GGAGTGGGTGGCAGTTATATGGTATGATGAAGT AATAAAAACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGGA TGTCGGGTACAACGGTATGGACGTCTGGGGCCA AGGGACCACGGTCACCGTCTCCTCA<br><br>SEQ ID NO: 31181 |
| | | AA | DIQMTQSPSSLSASVGDRVTITCRASQGISNYLA WFQQKPGKAPKSLIYAASSLQSGVPSKFSGSGSG TDFTLTISSLQPEDFATYYCLHYLNYPLTFGGGT RVEIK<br><br>SEQ ID NO: 27176 | QVQLVESGGGVVQPGRSLRLSCAASGFTFSSYGMH WVRQAPGKGLEWVAVIWYDGSNKNYADSVKGRF TISRDNSKNTLYLQMNSLRAEDTAVYYCARDRDV GYNGMDVWGQGTTVTVSS<br><br>SEQ ID NO: 31182 |

FIGURE 50
(Continued)

| | | | |
|---|---|---|---|
| iPS:436516 | 21-225_222C12 | NA | GACATCCAGATGACTCAGTGTCCATCTTCCGT GTCTGCATCTGTAGGAGACAGAGTCACCATCA CTTGTCGGGTGAGTCAGGGTATTAGCAGCTGG TTAGCCTGGTATCAGCAGAAACCAGGGAAAG CCCTTAAGCTCCTGATCTATACTGCATCCAATT TGCAAAGTGGGGTCCATCAAGGTTCAGCGGC AGTGGATCTGGGACAGATTTCACTCTCACCAT CAGCAGCGTGCAGCGTGAAGATTTTGCAACTT ACTATTGTCAACAGGATAACAGTTCCCATTC ACTTTCGGCCGAGGGACCAAAGTGGATATCAA A | CAGGTGCAGCTGGTGCAGTCTGGGGCTGAGGTG AAGAAGCCTGGGGCCTCAGTGAAGGTCCTGC AAGACTTCTGGATACACCTTCACCGGCTACTATA TGCACTGGGTGCGACAGGCCCCTGGACAAGGGC TTGAGTGGATGGATGGATCCACCTAACAGTGG TGGCACAAACTATGCACAGAAATTTCAGGGCAG GGTCACCCTGACCAGGGACACGTCCATCAGCAC AGCCTACATGGACCTGAGCAGGCTGAGATCTGA CGACACGGCCGTGTATTACTGTGCGAGAGATGG GACCAGCTCGTTTGACTACTGGGGCCAGGGAACC CTGGTCACCGTCTCCTCA |
| | | | SEQ ID NO: 27177 | SEQ ID NO: 31183 |
| | | AA | DIQMTQSPSSVSASVGDRVTITCRVSQGISSWLA WYQQKPGKALKLVIYTASNLQSGVPSRFSGSGS GTDFTLTISSVQREDFATYYCQQDNSFPFTFGRG TKVDIK | QVQLVQSGAEVKKPGASVKVSCKTSGYTFTGYYM HWVRQAPGQGLEWMGWIHPNSGGTNYAQKFQGR VTLTRDTSISTAYMDLSRLRSDDTAVYYCARDGTS SFDYWGQGTLVTVSS |
| | | | SEQ ID NO: 27178 | SEQ ID NO: 31184 |
| iPS:436520 | 21-225_223G10 | NA | GACATCGTGATGACCCAGTCTCCAGACTCCCT GGCTGTGTCTCTGGGCGAGAGGGCCACCATCA ACTGCAAGTCCAGCCAGAGTATTTTACTCAGC TCCAACAATAAGAACTACTTAGCTTGGCACCA GCAGAAACCAGGACAGCCTCCTAAGCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCTGCAA TATTTTAGTACTCCGTGGACGTTCGGCCAAGG GACCAAGGTGGAAATCAAA | CAGGTTCAGCTGGTGCAGTCTGGAGCTGAGGTGA AGAAGCCTGGGGCCTCAGTGAAGGTCCTCGCA AGGCTTCTGGTTCACCTTTACCAGCTATGGTATC AACTGGGTGCGACAGGCCCCTGGACAAGGACTT GAGTGGATGGGATGGATCAGCGTTTACAGTGGTA ACACAAACTATGCACACAGAAGTCCAGGGCAGAG TCACCATGACCACAGACTACATCCACGAGCACAG CCTACATGGAGCTGAGGAGCCTGAGATCTGACG ACACGGCCGTGTATTACTGTGCGAGAGACTACTA CTACGGTATGGACGTCTGGGGCCAAGGGACCAC GGTCACCGTCTCCTCA |
| | | | SEQ ID NO: 27179 | SEQ ID NO: 31185 |

FIGURE 50
(Continued)

| | | | |
|---|---|---|---|
| iPS:436522 | 21-225_223H10 | AA | DIVMTQSPDSLAVSLGERATINCKSSQSILLSSNN KNYLAWHQQKPGQPPKLLIYWASTRESGVPDRF SGSGSGTDFTLTISSLQAEDVAVYYCLQYFSTPW TFGQGTKVEIK<br>SEQ ID NO: 27180 | QVQLVQSGAEVKKPGASVKVSCKASGFTFTSYGIN WVRQAPGQGLEWMGWISVYSGNTNYAQKLQGRV TMTDTSTSTAYMELRSLRSDDTAVYYCARDYYY GMDVWGQGTTVTVSS<br>SEQ ID NO: 31186 |
| | | NA | GACATCCAGATGACCCAGTCTCCATCCTCACT GTCTGCATCTGTAGGAGACAGAGTCACCATCA CTTGTCGGGCGAGTCAGGCATTAGTAATTAT TTGGCCTGGTTTCAGCAGAAACCAGGGAAAGC CCCTAAGTCCCTGATCTACGCTGCATCCAATTT GCAAAGTGGGGTCCCATCAAGGTTCAGCGGCA GTGGGTCTGGGACAGATTTCACTCTCACCATC AGCAGCCTGCAGCCTGAAGATTTTAATTACCCACTCAC TTACTGCCTACACATTATCTATCCCACTCAC TTTCGGCGGAGGGACCAAGGTGGAGATCAAA<br>SEQ ID NO: 27181 | CAGGTGCAGCTGGTGGAGTCTGGGGGAGGCGTG GTCCAGCCTGGGAGGTCCCTGAGACTCTCCTGTG CAGCGTCTGATTCACCTTCAGTAGTAGTATGGCAT GCACTGGGTCCGCCAGGCTCCAGGCAAGGGGCT GGAGTGGGTGGCAGTTATATGTGATGGAAGT AATAAAAACTATGCAGACTCCGTGAAGGGCCGA TTCACCATCTCCAGAGACAACATTCCAAGAACACGC TGTATCTGCAAATGAACAGCCTGAGAGCCGAGG ACACGGCTGTGTATTACTGTGCGAGAGATCGGGA TGTCGGGTACAACGGTATGGACGTCTGGGGCCA AGGGACCACGGTCACCGTCTCCTCA<br>SEQ ID NO: 31187 |
| | | AA | DIQMTQSPSSLSASVGDRVTITCRASQGISNYLA WFQQKPGKAPKSLIYAASNLQSGVPSKFSGSGS GTDFTLTISSLQPEDFATYYCLHYLNYPLTFGGG TKVEIK<br>SEQ ID NO: 27182 | QVQLVESGGGVVQPGRSLRLSCAASGFTFSSYGMH WVRQAPGKGLEWVAVIWYDGSNKNYADSVKGRF TISRDHSKNTLYLQMNSLRAEDTAVYYCARDRDV GYNGMDVWGQGTTVTVSS<br>SEQ ID NO: 31188 |

FIGURE 50
(Continued)

| | | | | |
|---|---|---|---|---|
| iPS:436526 | 21-225_224A1 | NA | GACATCCAGATGACCCAGTCTCCATCCTCCT GTCTGCATCTGTAGGAGACAGAGTCACCATCA CTTGCCGGGCAAGTCAGGGACATTGAAAATGAT TTAGGCTGGTATCAGCAGAAGCCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTGCAACT TATTACTGTCTACAGCATAATAGTTACCCGCTC ACTTTCGGCGGAGGGACCAAGGTGGAGATCAA A | GAGGTGCAGGTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGCTATTAGTGGCAGAGGCGG CAGCACATACTACGCAGACGCCGTGAAGGGCCG GTTCACCATCTCCAGAGACAATTCCAAGAACACG CTGTATCTGCAAATGAACAGCCTGAGAGCCGAG GACACGGCCGTATATTACTGCGCGAAAGGCTCCT ACGATAGTAGTGGTTATTACCACTACTTAGACCA CTGGGGCCAGGGAACCCTGGTCACCGTCTCCTCA |
| | | | SEQ ID NO: 27183 | SEQ ID NO: 31189 |
| | | AA | DIQMTQSPSSLSASVGDRVTITCRASQGIENDLG WYQQKPGKAPKRLIYAASSLQSGVPSRFSGSGS GTEFTLTISSLQPEDFATYYCLQHNSYPLTFGGG TKVEIK | EVQVLESGGGLVQPGGSLRLSCAASGFTFSSYAMS WVRQAPGKGLEWVSAISGRGGSTYYADAVKGRFT ISRDNSKNTLYLQMNSLRAEDTAVYYCAKGSYDSS GYYHYLDHWGQGTLVTVSS |
| | | | SEQ ID NO: 27184 | SEQ ID NO: 31190 |
| iPS:436528 | 21-225_224B1 | NA | GACATCCAGATGACCCAGTCTCCATCCTCCCT GTCTGCATCTGTGGGAGACAGAGTCACCATCA CTTGCCGGGCAAGTCAGGGCATTAGTAATGAT TTAGGCTGGTATCAGCAGAAGCCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTGCAACT TATCACTGTCTCTACAGCATAATAGTTATCTCCT ACTTTCGGCGGAGGGACCAAGGTGGAGATCA AA | GAGGTGCAGGTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AACACATACTACGCAGACTCCGTGAAGGGCCGG TTCACCATCTCCAGAGACAATTCCAAGAACACGC TGTATCTGCACATGAACAGCCTGAGAGCCGAGG ACACGGCCGTATATTACTGTGCGGGAGAGGGGG GCTACTACTATTACTACGGTGTGACGTCTGGGG CCAAGGGACCACGGTCACCGTCTCCTCA |
| | | | SEQ ID NO: 27185 | SEQ ID NO: 31191 |

FIGURE 50
(Continued)

| | | | |
|---|---|---|---|
| | | AA | DIQMTQSPSSLSASVGDRVTITCRASQGISNDLG WYQQKPGKAPKRLIYAASSLQSGVPSRFSGSGS GTEFTLTISSLQPEDFATYHCLQHNSYPPTFGGGT KVEIK | EVQVLESGGGLVQPGGSLRLSCAASGFTFSSYAMS WVRQAPGKGLEWVSAISGSGGNTYADSVKGRFT ISRDNSKNTLYLHMNSLRAEDTAVYYCAGEGGYY YYYGVDVWGQGTTVTVSS |
| | | | SEQ ID NO: 27186 | SEQ ID NO: 31192 |
| iPS:436534 | 21-225_224F1 | NA | GCCATCCAGATGACCCAGTCTCCATCCTCCCT GTCTGCATCTGTAGGAGACAGAGTCACCATCA CTTGCCGGGCAAGTCAGGGACATTAGAGATGAT TTAGGCTGGTATCAGCAGAAACCAGGGAAAG CCCCTAAGCGCCTGATCTATGCTGCATCCAGT TTGCAAAGTGGGGTCCCGTCAAGGATCAGCGG CAGTGGATCTGGGACAGAATTCACTCTCACAA TCAGCAGCCTGCAGCCTGAAGATTTTGCAATT TATTACTGTCTACAGCATTATAGTTACCCTCGG ACGTTCGGCCAAGGGACCAAGGTGGAAATCA AA | CAGGTGCAGCTGGTGGAGTCTGGGGGAGGCGTG GTCCAGCCTGGGAGGTCCCTGAGACTCTCCTGTG CAGCGTCTGATTCACCTCAGTAGTATATCAT GCACTGGGTCCGCCAGGCTCCAGGCAAGGGCT GGAGTGGGTGGCAGTTATATGTATGATGAAGT AATAAATACTATGCAGACTCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGAGGTA TAGCAGCAACTGGTACGACTACGGTATGGACGTC TGGGGCCAAGGGACCACGGTCACCGTCTCCTCA |
| | | | SEQ ID NO: 27187 | SEQ ID NO: 31193 |
| | | AA | AIQMTQSPSSLSASVGDRVTITCRASQGIRDDLG WYQQKPGKAPKRLIYAASSLQSGVPSRISGSGSG TEFTLTISSLQPEDFAIYYCLQHYSYPRTFGQGTK VEIK | QVQLVESGGGVVQPGRSLRLSCAASGFTFSSYIMH WVRQAPGKGLEWVAVIWYDGSNKYADSVKGRF TISRDNSKNTLYLQMNSLRAEDTAVYYCARERYSS NWYDYGMDVWGQGTTVTVSS |
| | | | SEQ ID NO: 27188 | SEQ ID NO: 31194 |

FIGURE 50
(Continued)

| | | | | |
|---|---|---|---|---|
| iPS:436536 | 21-225_224G1 | NA | GATATTGTGATGACCCAGACTCCACTCTCT GTCCGTCACCCCTGGACAGCCGGCCTCCATCT CCTGCAAGTCTGTCAGAGCTCCTGCATAGT GATGGAAAGAACCTTTTGTCTTGGTACCTGCA GAAGCCAGGCCAGCCTCCACAGCTCCTGATCT ATGAAAATTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGATTTTTACTGCATGCAAAG TACACAGCTTCCTCGGACGTTCGGCCAAGGGA CCAAGGTGGAAATCAAA SEQ ID NO: 27189 | DIVMTQTPLSLSVTPGQPASISCKSGQSLLHSDG KTFLSWYLQKPGQPPQLLIYEISNRFSGVPDRFSG SGSGTDFTLKISRVEAEDVGIFYCMQSTQLPRTF GQGTKVEIK SEQ ID NO: 27190 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGACAAGGGC TTGAGTGGATGGGATGGATCAACCCTTACAGTGG TGACACAAACTATGCACAGGAGACACGTTCAGGGCAG AGTCACCATGACCATGGAACTGAGCAGGCTGAGACAC AGCCTACATGAACTGAGCAGGCTGAGATTTGA CGACACGGCCGTGTTTTACTGTGCGAGAGATTGG GGTGGCTACAGTTCTTACTACTACGGTATGGACG TCTGGGGCCAAGGGACCACGGTCACCGTCTCTTC A SEQ ID NO: 31195 QVQLVQSGAEVKKPGASVKVSCKASGYTFTGYYIH WVRQAPGQGLEWMGWINPYSGDTNYAQKFQGRV TMTRDTSISTAYMELSRLRFDDTAVFYCARDWGG YSSYYYGMDVWGQGTTVTVSS SEQ ID NO: 31196 |
| iPS:436538 | 21-225_224C3 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTATGCTACATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCGCTC ACTTTCGGCGGAGGGACCAAGGTGGAGATCA AA SEQ ID NO: 27191 | CAGCTGCAGCTGCAGGAGTCGGGCCCAGGACTG GTGAAGTCTTCGGAGACCCTGTCCCTCACCTGCA CTGTCTCTGGCGGCTCCATCAGCAGAAGTAGTTA CTACTGGGGCTGGATCCGCCAGCCCCCAGGGAA GGGACTGGAGTGGATTGGGAGAATATCATTATAGT GGGAGCACCTACTACAACCCGTCCCTCAAGAGTC GAGTCACCATATCCGTAGACACGTCCAAGAACC AGTTCTCCCTGAAGCTGAGCTCTGTGACCGCCGC AGAACACGCTGTGTATTACTGTGCGAGACAGGGT CGGGACTGGGGTGTTGACTACGGGGGCCAGGGA ACCCTAGTCACCGTCCTCA SEQ ID NO: 31197 |

FIGURE 50
(Continued)

| | | | |
|---|---|---|---|
| iPS:436540 | 21-225_224F3 | AA | DIQMTQSPSSLSASVGDRVTITCRASQDIRNDLG WYQQKPGKAPKRLIYATSSLQSGVPSRFSGSGSG TEFTLTISSLQPEDFATYYCLQHNSYPLTFGGGT KVEIK |
| | | | SEQ ID NO: 27192 |
| | | | QLQLQESGPGLVKSSETLSLTCTVSGGSISRSSYYW GWIRQPPGKGLEWIGNIYYSGSTYYNPSLKSRVTIS VDTSKNQFSLKLSSVTAADTAVYYCARQGRDWGV DYGGQGTLVTVSS |
| | | | SEQ ID NO: 31198 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAACAGAAACCAGGAAAG CCCCTGAGCGCCTGATCTATGCTGCATCCAGT TTGCAAAGTGGGGGTCCCATCCAAGGTTCAGCGG CAGTGGATCTGGGACAGAGAATTCACTCTCACAA TCAGCAGCCTGCAGCCTGAAGATTTTGCAACT TATTACTGTCTTCAGCATTATAATTACCCTCGG GCGTTCGGCCAAGGGACCAAGGTGGAAATCA AA |
| | | | SEQ ID NO: 27193 |
| | | | CAGGTGCAGCTGGTGGAGTCTGGGGGAGGCGTG GTCCAGCCTGGGAGGTCCCTGAGACTCTCCTGTG CAGCGTCTGGATTCAGCTTCAGTAGCTATGGCAT GCACTGGGTCCGCCAGGCTCCAGGCAAGGGGCT GGAGTGGGTGGCAGTTATATGCAGACTCCCTGAAGGCCGA TTCACCATCTCCAGAGACAACAATTCCAAGAACACGC TGTATCTGCAAATGAACAGCCTGAGAGCCGAGG ACACGGCTGTGTATTACTGTGCGAGAGAGGTA TAGCAGCAGCTGGTACGACTACGGTATGGACGTC TGGGGCCAAGGGACCACGGTCACCGTCTCCTCA |
| | | | SEQ ID NO: 31199 |
| | | AA | DIQMTQSPSSLSASVGDRVTITCRASQGIRNDLG WYQQKPGKAPERLIYAASSLQSGVPSRFSGSGSG TEFTLTISSLQPEDFATYYCLQHYNYPRAFGQGT KVEIK |
| | | | SEQ ID NO: 27194 |
| | | | QVQLVESGGGVVQPGRSLRLSCAASGFSFSSYGMH WVRQAPGKGLEWVAVIWYDGSNKYYADSVKGRF TISRDNSKNTLYLQMNSLRAEDTAVYYCARERYSS SWYDYGMDVWGQGTTVTVSS |
| | | | SEQ ID NO: 31200 |

FIGURE 50
(Continued)

| | | | | |
|---|---|---|---|---|
| iPS:436544 | 21-225_224H5 | NA | GACATCGTGATGACCCAGTCTCCAGACTCCCTGGCTGTGTCTCTGGGCGAGAGGGCCACCATCAACTGCAAGTCCAGCCAGAGTGTTTTATACAGCTCCAACAATTTCAACTACTTAACTGGTATCAGCAGAAACCAGGACAGCCTCCTAAGTTGCTCATTTACTGGGCATCTACCCGGGAATCCGGGGTCCCTGACCGATTCAGTGGCAGCGGGTCTGGGACAGATTTCACTCTCACCATCAACAGCCTGCAGGCTGAAGATGTGGCAGTTTATTACTGTCAGCAATATTATAGTACTCCCTCGACGTTCGGCCAAGGGACCAAGGTGGAAATCAAA SEQ ID NO: 27195 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGGCAGAGTCACCATGACCAGGAACACCTCCATAAGCAGCCTACATGGAGCTGAGCAGCCTGAGATCTGAGGACACGGCCGTGTATTACTGTGCGAGTTCCAGTGGCTGGAACTGGTTCGACCCCTGGGGCCAGGGAACCCTGGTCACCGTCTCCTCA SEQ ID NO: 31201 |
| | | AA | DIVMTQSPDSLAVSLGERATINCKSSQSVLYSSNNFNYLTWYQQKPGQPPKLLIYWASTRESGVPDRFSGSGSGTDFTLTINSLQAEDVAVYYCQQYYSTPPTFGQGTKVEIK SEQ ID NO: 27196 | QVQLVQSGAEVKKPGASVKVSCKASGYTFTNYDINWVRQATGQGLEWMGWMNPNSGNTGYAQKFQGRVTMTRNTSISTAYMELSSLRSEDTAVYYCASSSGWNWFDPWGQGTLVTVSS SEQ ID NO: 31202 |
| iPS:436546 | 21-225_224D6 | NA | GACATCCAGATGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGCTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTACTATTGTCAACAGGCTAACAGTTTCCCGTGACGTTCGGCCAAGGGACCAAGGTGGAAATCAA SEQ ID NO: 27197 | GAGGTGCAGGTGTTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTAGTGGTGATAACACATTCTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGTCTATAGTGCCTACGATTCTACTGGTTGACCCCTGGGGCCAGGGAACCCTGGTCACCGTCTCCTCA SEQ ID NO: 31203 |

FIGURE 50
(Continued)

| | | | |
|---|---|---|---|
| | | AA | DIQMTQSPSSVSASVGDRVTITCRASQGISSWLA WYQQKPGKAPKLLIYAASSLQSGVPSRFSGSGS GTDFTLTISSLQPEDFATYYCQQANSFPWTFGPG TKVEIK<br><br>SEQ ID NO: 27198 | EVQVLESGGGLVQPGGSLRLSCAASGSTFSSDAMS WVRQAPGKGLEWVSAISGSGDNTFYADSVKGRFTI SRDNSKNTLYLQMNSLRAEDTAVYYCAKVYSAYD SHWFDPWGQGTLVTVSS<br><br>SEQ ID NO: 31204 |
| iPS:436548 | 21-225_224A7 | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GATGGAAAGACCTTTTTGTATTGGTTCCTGCA GAAGCCAGGCCAGCCTCCACAGCTCCTGATCT ATGAAAATTTCCAACCGGTTCTCTGGAGTGCCA GATAGGTTCAGTGGCAGCGGGTCAGGGACAG ATTTCACACTGAAAATCAGCGCGGTGGAGCT GAGGATGTTGGGATTTATTACTGCATGCAAAG TACACAGCTTCCTCGGACGTTCGGCCAAGGGA CCAAGGTGGAAATCAAA<br><br>SEQ ID NO: 27199 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTTACAGTGG TGACACAAACTATGCACAGAAGTTTCAGGGCAG GGTCACCATGACCAGGGACACGTCCATCACCAC AGCCTACATGGAACTGAGCAGGCTGAGATTTGA CGACACGGCCGTGTTTTACTGTGCGAGAGATTGG GGTGGCTACAGTTCTTACTACTACGGTATGGACG TCTGGGGCCAAGGGACCACGGTCACCGTCTCTC A<br><br>SEQ ID NO: 31205 |
| | | AA | DIVMTQTPLSLSVTPGQPASISCKSSQSLLHSDGK TFLYWFLQKPGQPPQLLIYEISNRFSGVPDRFSGS GSGTDFTLKISRVEAEDVGIYYCMQSTQLPRTFG QGTKVEIK<br><br>SEQ ID NO: 27200 | QVQLVQSGAEVKKPGASVKVSCKASGYTFTFGYYIH WVRQAPGQGLEWMGWINPYSGDTNYAQKFQGRV TMTRDTSITTAYMELSRLRFDDTAVFYCARDWGG YSSYYYGMDVWGQGTTVTVSS<br><br>SEQ ID NO: 31206 |

FIGURE 50
(Continued)

| | | | | |
|---|---|---|---|---|
| iPS:436550 | 21-225_224D8 | NA | GACATCGTGATGACCCAGTCTCCAGACTCCCT GGCTGTTTCTCTGGCGAGAGGGCCACCATCA ACTGCAAGTCCAGCCAGAGTGTTTTATACAGC TCCAACAATAAGAACTACTTAGCTTGGTACCA GCAGAAACCAGGACAGCCTCCTAAGCTGCTCA TTTATTGGTCGTCTACCCGGAAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTTTAGTACTCCTCCGACGTTCGGCCAAGG GACCAAGGTGGAAATCAAA SEQ ID NO: 27201 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGTTGTACCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCTTATAGCAGT GGCTGGTACTACTTTGACTACTGGGGCCAGGGAA CCCTGGTCATCGTCTCCTCA SEQ ID NO: 31207 |
| | | AA | DIVMTQSPDSLAVSLGERAAINCKSSQSVLYSSN NKNYLAWYQQKPGQPPKLLIYWSSTRKSGVPD RFSGSGSGTDFTLTISSLQAEDVAVYYCQQYFST PPTFGQGTKVEIK SEQ ID NO: 27202 | QVQLVQSGAEVKKPGASVKVSCKASGYTFTNYDIN WVRQATGQGLEWMGWLYPNSGNTGYAQKFQGR VTMTRNTSISTAYMELSSLRSEDTAVYYCAYSSGW YYFDYWGQGTLVIVSS SEQ ID NO: 31208 |
| iPS:436554 | 21-225_224C10 | NA | GACATCGTGATGACCCAGTCTCCAGACTCCCT GGCTGCGTCTCTCTGGCGAGAGGGCCACCATCA CCTGCAAGTCCAGCCAGAGTGTTTTATACAAT TCCAACAATAAGAACTACTTAGCTTGGTACCA GCAGAAACCAGGACAGCCTCCTAAGCTGCTCA TTTACTGGGCATCTACCCGGGAGTCCGGGGTC CCTGACCGATTCAGTGGCAGCGGGTCTGGGAC AGATTTCACTCTCACCATCAGCAGCCTGCAGG CTGAAGATGTGGCAATTTATTACTGTCAACAA TATTATATTAATCCGTGCAGTTTTGGCCAGGG GACCAGGCTGGAGATCAAA SEQ ID NO: 27203 | CAGGTGCAGCTGGTGCAGTCTGGGGCTGAGGTG AAGAAGCCTGGGGCCTCAGTGAAGGTCTCCTGC AAGGCTTCTGGATCCACCTTCACCAATTATGATA TCAACTGGGTGCGACAGGCCACTGGACAAGGC TTGAGTGGATGGGATGATGCACAGAAGTTCCAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCCTATAGCAGT GGCTGGTACAAGTTTGACTACTGGGGCCAGGGA ACCCTGGTCACCGTCTCCTCA SEQ ID NO: 31209 |

FIGURE 50
(Continued)

| | | | |
|---|---|---|---|
| iPS:436556 | 21-225_224D10 | AA | DIVMTQSPDSLAASLGERATITCKSSQSVLYNSN NKNYLAWYQQKPGQPPKLLIYWASTRESGVPD RFSGSGSGTDFTLTISSLQAEDVAIYYCQQYYINP CSFGQGTRLEIK<br>SEQ ID NO: 27204 | QVQLVQSGAEVKKPGASVKVSCKASGSTFTNYDIN WVRQATGQGLEWMGWMHPNSGNTGYAQKFQGR VTMTRNTSISTAYMELSSLRSEDTAVYYCAYSSGW YKFDYWGQGTLVTVSS<br>SEQ ID NO: 31210 |
| | | NA | GACATCCTGATGACCCAGTCTCCATCCCCT GTCTGCATCTGTAGGAGACAGAGTCACCATCA CTTGCCGGGCAAGTCAGGACAGTCAGGCATTAGAAATGAT TTAGGCTGGTATCAGCAGAAACCAGGAAAG CCCCTAAGCGCCTGATCTATGCTGCATCCAGT TTACAAAGTGGGGTCCCATCGCGGTTCAGCGG CAGTGGATCTGGGACAGAATTCACTCTCACAA TCAGCAGCCTGCAGCCTGAAGATTTTGCAACT TATTACTGTCTACAACATAATAGTTACCCGCTC ACTTTTGGCGGAGGGACCAAGGTGGAGATCA AA<br>SEQ ID NO: 27205 | CAGGTGCAGCTGGTGCAGTCTGGGGGAGGCCTG GTCCAGCCTGGAAAGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGAGGGAAG TAATAAATACTATGTAGACTCCGTGAGGGGCCGA TTCACCATCTCCAGAGACAATTCCAAGAGTACGC TGTATCTGCAAATGAACAGCCTGCGAGCCGAGG ACACGGCTGTGTATTACTGTGTGAGAGAGCTAGG CTTCCAGTCTGACTACTGGGGCCAGGGAACCCCG GTCACCGTCTCCTCA<br>SEQ ID NO: 31211 |
| | | AA | DILMTQSPSSLSASVGDRVTITCRASQGIRNDLG WYQQKPGKAPKRLIYAASSLQSGVPSRFSGSGS GTEFTLTISSLQPEDFATYYCLQHNSYPLTFGGG TKVEIK<br>SEQ ID NO: 27206 | QVQLVESGGGLVQPGKSLRLSCAASGFTFSSYGMH WVRQAPGKGLEWVAVIWYEGSNKYYVDSVRGRF TISRDNSKSTLYLQMNSLRAEDTAVYYCVRELGFQ SDYWGQGTPVTVSS<br>SEQ ID NO: 31212 |

FIGURE 50
(Continued)

| | | | |
|---|---|---|---|
| iPS:436558 | 21-225_224C11 | NA | GATTTTGTGATGACCCAGACTCCACTCTCTG TCCGTCACCCCTGGACAGCCGGCTCCATCTC CTGCAAGTCTAGTCAGAGCCTCCTGCATAGTG ATGGAAAGAACCTTTTTGTATTGGTACCTGCAG AAGCCAGGCCAGCCTCCACAGCTCCTGATCTA TGAAATTTCAACCGGTTCTCTGGAGTGCCAG ATAGGTTCAGTGGCAGCGGGTCAGGGACAGA TTTCACACTGAAAATCAGCCGGGTGGAGGCTG AGGATGTTGGGATTTATTACTGTCATGCAAAGT ACACAGTTCCTCGACGTTCGGCCAAGGGAC CAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTTACAGTGG TGACACAAACTATGCACAGAAGTTTCAGGGCAG GGTCACCATGACCAGGGACACGTCCATCAGCAC AGCCTACATGGAACTGAGGAGGCTGAGATTTGA CGACAGCCGTGTTTTACTGTGCGAGAGATTGG GGTGGCTACAGTTCTTACTACTTCGGTATGGACG TCTGGGGCCAAGGGACCACGGTCACCGTCTCTTC A |
| | | | SEQ ID NO: 31213 |
| | | SEQ ID NO: 27207 | |
| | | AA | DFVMTQTPLSLSVTPGQPASISCKSSQSLLHSDG KTFLYWYLQKPGQPPQLLIYEISNRFSGVPDRFS GSGSGTDFTLKISRVEAEDVGIYYCMQSTQLPRT FGQGTKVEIK | QVQLVQSGAEVKKPGASVKVSCKASGYTFTGYYIH WVRQAPGQGLEWMGWINPYSGDTNYAQKFQGRV TMTRDTSISTAYMELRRLRFDDTAVFYCARDWGG YSSYYFGMDVWGQGTTVTVSS |
| | | | SEQ ID NO: 31214 |
| | | SEQ ID NO: 27208 | |
| iPS:436560 | 21-225_224F11 | NA | AACATCGTGATGACCCAGTCTCCAGACTCCCT GGCTGTGTCTCTGGGCGAGAGGGCCACCATCA ACTGCAAGTCCAGCCAGAGTGTTTTATCCAGC TCCAACAATCACAACTACTTAGCTTGGTACCA GCAGAAACCAGGACAGCCTCCTAAGATGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTATTACTGTCAGCAA TATTATACTACTCCGTGCAGTTTTGGCCAGGG GACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACAGAAGTTCCAGGGCA GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCCTATAGCAG TGGCTGGTACAAGTTTGACTACTGGGGCCAGGGA ACCCTGGTCACCGTCTCCTCA |
| | | | SEQ ID NO: 31215 |
| | | SEQ ID NO: 27209 | |

FIGURE 50
(Continued)

| | | | |
|---|---|---|---|
| iPS:436562 | 21-225_224H11 | AA | NIVMTQSPDSLAVSLDERATINCKSSQSVLSSSN NHNYLAWYQQKPGQPPKMLIYWASTRESGVPD RFSGSGSGTDFTLTISSLQAEDVAVYYCQQYYTT PCSFGQGTKLEIK<br><br>SEQ ID NO: 27210 | QVQLVQSGAEVKKPGASVKVSCKASGYTFTNYDIN WVRQATGQGLEWMGWMNPNSGNTGYAQKFQGR VTMTRNTSISTAYMELSSLRSEDTAVYYCAYSSGW YKFDYWGQGTLVTVSS<br><br>SEQ ID NO: 31216 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GATGGAAAGAACCTTTTTGTATTGGTACCTGCA GAAGCCAGGCCAGCCTCCACAGCTCCTGATCT ATGAAATTTCCAACCGGTTCTCTGGAGTGCCA GATAGGTTCAGTGGCAGCGGGTCAGGGACAG ATTTCACACACTGAAAATCAGCCGGGTGGAGCT GAGGATGTTGGGATTTATTACTGCATGCAAAG TACACAGCTTCCTCGGACGTTCGGCCAAGGGA CCAAGGTGGAAATCAAA<br><br>SEQ ID NO: 27211 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGACCCCTGGACAAGGGC TTGAGTGGATGGGATGGATGAATCAACAGAAGAGAGTTCAGGGCAG TGACACAAACTATGCACAGAAGTTCAGGGCAG GGTCACCATGACCAGGGACACGTCCATCAGCAC AGCCTACATGGAACTGCGCAGGCTGAGATTTGAC GACACGGCCGTCTTTACTGTGCGAGAGATTGGG GTGGCTACAGTTCTTACTACTACGGTATGGACGT CTGGGGCCAAGGGACCACGGTCACCGTCTCTCA<br><br>SEQ ID NO: 31217 |
| | | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK<br><br>SEQ ID NO: 27212 | QVQLVQSGAEVKKPGASVKVSCKASGYTFGYYIH WVRQTPGQGLEWMGWINPYSGDTNYAQKFQGRV TMTRDTSISTAYMELRRLRFDDTAVFYCARDWGG YSSYYYGMDVWGQGTTVTVSS<br><br>SEQ ID NO: 31218 |

FIGURE 50
(Continued)

| | | | | |
|---|---|---|---|---|
| iPS:436564 | 21-225_225A1 | NA | GACATCCAGATGACCCAGTCTCCATCCTCCCTGTCTGCATCTGTAGGAGACAGAGTCACCATCACTTGCCGGGCAAGTCAGGGCATTAGAGATGATTTAGGCTGGTATCAGCAGAAATACCAGGGAAAGCCCCTAAGGCGCCTGATCTATGTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTGCAGCATTATAGTTACCCTCGGACGTTCGGCCAAGGGACCAAGGTGGAAATCAAA SEQ ID NO: 27213 | CAGGTGCAGCTGGTGGAGTCTGGGGGAGGCGTGGTCCAGCCTGGGAGGTCCCTGAGACTCTCCTGTCAGCCTCTGGATTCACCTTCAGTGACTATGTCATCCACTGGGTCCGCCAGGCTCCAGGCAAGGGCTGGAGTGGGTGGCAGTTATATGTGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGACACGGCTGTGTATTACTGTGCGAGAGAGGTATAGCAGTGGCTGGTACGACTACGGTATGGACGTCTGGGGCCAAGGGACCACGGTCACCGTCTCCTCA SEQ ID NO: 31219 |
| | | AA | DIQMTQSPSSLSASVGDRVTITCRASQGIRDDLGWYQQIPGKAPKRLIYAASSLQSGVPSRFSGSGSGTEFTLTISSLQPEDFATYYCLQHYSYPRTFGQGTKVEIK SEQ ID NO: 27214 | QVQLVESGGGVVQPGRSLRLSCAASGFTFSDYVIHWVRQAPGKGLEWVAVIWYDGSNKYYADSVKGRFTISRDNSKNTLYLQMNSLRAEDTAVYYCARERYSSGWYDYGMDVWGQGTTVTVSS SEQ ID NO: 31220 |
| iPS:436568 | 21-225_225B3 | NA | GAAATTGTGCTGACGCAGTCTCCAGGCACCCTGTCTTTGTCTCCAGGGGAAAGAGCCACCCTCTCCTGCAGGGCCAGTCAGAGTCTTAGCAGCTACTTAGGCTGGTACCAGCAGAAACCTGGCCAGGCTCCCAGATGCCTCATCTATGATACATCCAGCAGGGCCACTGGCATCCCAGACAGGTTCAGTGGCAGTGGGTCTGGGACAGACTTCACTCTCACCATCAGCAGACTGGAGCCTGAAGATTTTGCAGTGTATTACTGTCAGGAGTATGGTAGCTCACTCATGTGCAGTTTTGGCCAGGGGACCAAGCTGGAGATCAAA SEQ ID NO: 27215 | CAGGTGCAACTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGCGACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTCCACGAGCACAGTCTACATGGAGCTGAGCAGCCTGAGATCTGCGGACACGGCCGTGTATTACTGTGCGAGGGATTTAGCAGTCGTTCTTACTACTACTCGTATGGACGTCTGGGGCCAAGGGACCACGGTCACCGTCTCCTCA SEQ ID NO: 31221 |

FIGURE 50
(Continued)

| | | | |
|---|---|---|---|
| | | AA | EIVLTQSPGTLSLSPGERATLSCRASQNLSSSYLG WYQQKPGQAPRLLIYDTSSRATGIPDRFSGSGSG TDFTLTISRLEPEDFAVYYCQEYGSSLMCSFGQG TKLEIK<br>SEQ ID NO: 27216 | QVQLVQSGAEVKKPGASVKVSCKASGYTFTSYYM HWVRQAPGQGLEWMGIINPSGGSTSYAQKFQGRV TMTRDTSTSTVYMELSSLRSADTAVYYCARDLAAR SYYYYFGMDVWGQGATVTVSS<br>SEQ ID NO: 31222 |
| iPS:436570 | 21-225_225F4 | NA | GACATCGTGATGACCCAGTCTCCAGACTCCCT GGCTGTGTCTCTGGGCGAGAGGGCCACCATCA ACTGCAAGTCCAGCCAGAGTGTTTTATATAGC TCCAACAATAAGAACTACTTAGCTTGGTACCA GCAGAAACCAGGACAGCCTCCTAAACTACTCA TTTACTGGGCATCTACCCGGGAATCCGGGGTC CCTGACCGATTCACTGGCAGCGGGTCTGGGAC AGATTTCACTCTCACCATCAGCTGCCTGCAGC CGGAAGATGTGGCAGTTTATTACTGTCACCAA TATCATAATTCTCCTCCCACTTTCGGCCACGGG ACCGAAGTGGATATCAAA<br>SEQ ID NO: 27217 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAGCACAGGCTATGCACAGAAGTTCCAGGGCAG ACTCACCATGACCAGGAACACCTCCATAAGCAC AGTCTACATGGAACTGAACAGCCTGAGATCTGA GGACACGGCCGTGTATTATTGTGCGAGTAGCAGT GGCTGGTACTGGTTCGACCCCTGGGGCCAGGGA ACCCTGGTCACCGTCTCCTCA<br>SEQ ID NO: 31223 |
| | | AA | DIVMTQSPDSLAVSLGERATINCKSSQSVLYSSN NKNYLAWYQQKPGQPPKLLIYWASTRESGVPD RFTGSGSGTDFTLTISCVQPEDVAVYYCHQYHN SPPTFGHGTEVDIK<br>SEQ ID NO: 27218 | QVQLVQSGAEVKKPGASVKVSCKASGYTFTNYDIN WVRQATGQGLEWMGWMHPNSGSTGYAQKFQGR LTMTRNTSISTVYMELNSLRSEDTAVYYCASSSGW YWFDPWGQGTLVTVSS<br>SEQ ID NO: 31224 |

FIGURE 50
(Continued)

| | | | | |
|---|---|---|---|---|
| iPS:436572 | 21-225_225G4 | NA | GATATTGTGATGACCCAGACTCCACTCTCT GTCCGTCACCCCTGGACAGCCGGCCTCCATCT CCTGCAAGTCTAGTCAGAGCTCCTGCATAGT GATGGAAAAGACCTTTTGTATTGGTACCTGCA GAAGCCAGGCCAGCCTCCACAGTCTCTGATCT ATGAAAATTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGATTTATTACTGCATGCAAAG TACACAGCTTCCTCGGACGTTCGGCCAAGGGA CCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTTACAGTGG TGACACAAACTATGACCAGGACACGTCCATCAGCAC GGTCACCATGACCAGGGACACGTCCATCAGCAC AGCCTACATGGAACTGCGCAGGCTGAGATTTGAC GACACGGCCGTCTTTTACTGTGCGAGAGATTGGG GTGGGCTACAGTTCTTACTACTGGTATGGACGT CTGGGCCAAGGGACCACGGTCACCGTCTCTTCA |
| | | | SEQ ID NO: 27219 | SEQ ID NO: 31225 |
| | | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK | QVQLVQSGAEVKKPGASVKVSCKASGYTFTGYYIH WVRQAPGQGLEWMGWINPYSGDTNYAQKFQGRV TMTRDTSISTAYMELRRLRFDDTAVFYCARDWGG YSSYYYGMDVWGQGTTVTVSS |
| | | | SEQ ID NO: 27220 | SEQ ID NO: 31226 |
| iPS:436574 | 21-225_225F5 | NA | GACATCGTGATGACCCAGTCTCCAGACTCCCT GGCTGTGTCTCTGGGCGAGAGGGCCACCATCA ACTGCAAGTCCAGCCAGAATGTTTTATACAAC TCCAACAATAACAACTACTTAGCTTGGTACCA GCAGAAACCAGGACAGCCTCCTAACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTTCTGTCAGCAA TATTATAGTTCTCCGACGTTCGGCCAAGG GACCAAGGTGGAAATCAAC | CAGGTGCAGCTGGTGCAGTCTGGGGCTGAGGTG AAGAAGCCTAGGGCCTCAGTGAAGGTCTCCTGC AAGGCTTCTGGACACACCTTCACCAATTATGATA TCAACTGGGTGCGACAGGCCACTGGACAAGGC TTGAGTGGATGGGATGGATGCATCCTAACAGTGG TAACACAGGCTTTGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCATATAGCAGT GGCTGGTACCGCTTTGACTACTGGGGCCAGGAA CCCTGGTCACCGTCCTCA |
| | | | SEQ ID NO: 27221 | SEQ ID NO: 31227 |

FIGURE 50
(Continued)

| | | | |
|---|---|---|---|
| | | AA | DIVMTQSPDSLAVSLGERATINCKSSQNVLYNSN NNNYLAWYQQKPGQPKPGQPPNLLIYWASTRESGVPD RFSGSGSGTDFTLTISSLQAEDVAVYFCQQYYSS PPTFGQGTKVEIN<br>SEQ ID NO: 27222 | QVQLVQSGAEVKKPRASVKVSCKASGHTFTNYDIN WVRQATGQGLEWMGWMHPNSGNTGFAQKFQGR VTMTRNTSISTAYMELSSLRSEDTAVYYCAYSSGW YRFDYWGQGTLVTVSS<br>SEQ ID NO: 31228 |
| iPS:436576 | 21-225_225B6 | NA | GACATCCAGATGACCCAGTCTCCATCCTCCCT GTCTGCATCTGTAGGAGACAGAGTCATCATCA CTTGCCGGGCAAGTCAGGGCATGAGAAAAGA TTTAGGCTGGTATCAGCAGAAACCAGGGAAA GCCCCTAAGCGCCTGATCTATGCCAACCAG TTTGCAAAGTGGGGTCCCATCAAGGTTCAGCG GCAGTGGATCTGGGACAGAATTCACTCTCACA ATCAGCAGCCTGCAGCTGAAGATTTTGCAAC TTATTACTGTCTACAGCATAATAGTTATCCATT CACTTTCGGCCCTGGGACCAAAGTGGATATCA AA<br>SEQ ID NO: 27223 | CAGGTGCGGCTGGTGGAGTCTGGGGAGGCGTG GTCCAGCCTGGGAGGTCCCTGAGACTCTCCTGTG CAGCGTCTGGATTCACCTTCAGTGACTGATGGCAT GCACTGGGTCCGCCAGGCTCCAGGCAAGGGGCT GGAGTGGGTGGCAGTTATATGGTATGATGAAAAT AATAAATACTATGCAGACTCCGTGAAGGGCCGA TTCACCATCTCAGAGACAATTCCAAGAACACGC TGTATCTGCAAATGAACAGCCTGAGAGCCGAGG ACACGGCTGTGTATTACTGTGCGAGAGAAGTGGG ATTCACTGAGGACTACTGGGGCCAGGGAACCCT GGTCACCGTCTCCTCA<br>SEQ ID NO: 31229 |
| | | AA | DIQMTQSPSSLSASVGDRVIITCRASQGMRKDLG WYQQKPGKAPKRLIYAATSLQSGVPSRFSGSGS GTEFTLTISSLQPEDFATYYCLQHNSYPFTFGPGT KVDIK<br>SEQ ID NO: 27224 | QVRLVESGGGVVQPGRSLRLSCAASGFTFSDYGMH WVRQAPGKGLEWVAVIWYDENNKYYADSVKGRF TISRDNSKNTLYLQMNSLRAEDTAVYYCAREVGFT EDYWGQGTLVTVSS<br>SEQ ID NO: 31230 |

FIGURE 50
(Continued)

| | | | | |
|---|---|---|---|---|
| iPS:436578 | 21-225_225D6 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTACAAAGTGGGGTCCCATCAAGGTTCAGCGG CAGTGGATCTGGGACAGAATTCACTCTCACAA TCAGCAGCCTGCAGCCTGAAGATTTTGCAACT TATTGCTGTCTTCAGCATAATACTTACCCATTC ACTTTCGGCCCTGGGACCAAAGTGGATATCAA A | CAGGTGCAGCTGTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGGTATGATGAAAAT AATAAATACTATGCAGACTCCGTGAAGGGCCGA TTCACCATCTCCAGAGACAATTCCCAGAACACGC TGTATCTGCAAATGACCAGCCTGAGAGCCGAGG ACACGGCTGTGTATTACTGTGCGAGAGAAGTGGG ATTCACTGAGGACTACTGGGGCCAGGGAACCCT GGTCACCGTCTCCTCA |
| | | | SEQ ID NO: 27225 | SEQ ID NO: 31231 |
| | | AA | DIQMTQSPSSLSASVGDRVTITCRASQGIRNDLG WYQQKPGKAPKRLIYAASSLQSGVPSRFSGSGS GTEFTLTISSLQPEDFATYCCLQHNTYPFTFGPGT KVDIK | QVQLVESGGGVVQPGRSLRLSCAASGFTFSNYGM HWVRQAPGKGLEWVAVIWYDENNKYADSVKGR FTISRDNSQNTLYLQMTSLRAEDTAVYYCAREVGF TEDYWGQGTLVTVSS |
| | | | SEQ ID NO: 27226 | SEQ ID NO: 31232 |
| iPS:436580 | 21-225_225E7 | NA | GAAATTGTGTTGACGCAGTCTCCAGGCACCCT GTCTTTGTCTCCAGGGGAAAGAGCCACCCTCT CCTGCAGGGCCAGTCAGAGTGTTACAGAGCAGC TACTTAGCCTGGTACCAGCAGAAACCTGGCCA GGCTCCCAGGCTCCTCATCTATGGTGCATCCA GCAGGGCCACTGGCATCCCAGACAGGTTCAGT GGCAGTGGGTCTGGGACAGACTTCACTCTCAC CATCAGCAGACTGGAGCCTGAAGATTTTGCAG TATATTACTGTCAGCAGTATGGTACCTCACCTC GGACGTTCGGCCAAGGGACCAAGGTGAAAT CAAA | CAGGTGCAGCTGCAGGAGTCGGGCCCAGGACTG GTGAAGCCTTCACAGACCCTGTCCCTCACCTGCA CTGTCTCTGGTAACTCATCAGCAGTGGTCATTA CTACTGGAGCTGGATCCGCCAGCACCCAGGGAA GGGCCTGGAGTGGATTGGGTTCATCTATTACACT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGAGGCC GGTGACTACGGCTACTACGGTATGGACGTCTGGG GCCAAGGGACCACGGTCACCGTCTCCTCA |
| | | | SEQ ID NO: 27227 | SEQ ID NO: 31233 |

FIGURE 50
(Continued)

| | | | |
|---|---|---|---|
| iPS:436582 | | AA | EIVLTQSPGTLSLSPGERATLSCRASQSVYSSYLA WYQQKPGQAPRLLIYGASSRATGIPDRFSGSGSG TDFTLTISRLEPEDFAVYYCQQYGTSPRTFGQGT KVEIK<br>SEQ ID NO: 27228 | QVQLQESGPGLVKPSQTLSLTCTVSGNSISSGHYYW SWIRQHPGKGLEWIGFIYYTGSTYNPSLKSRVTIS VDTSKNQFSLKLSSVTAADTAVYYCAREAGDYGY YGMDVWGQGTTVTVSS<br>SEQ ID NO: 31234 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATATATGCTGCATCCAGT TTGCTAGGTGGTCCCATCAAGATTCAGCGG CAGTGGATCTGGGACAGATTCACTCTCACAA TCAGCAGCCTGCAGCCTGAAGATTTTGCAACT TATTACTGTCTACAACATAATAGTTACCCATTC ACTTTCGGCCCTGGGACCAAGGTGGATATCAA A<br>SEQ ID NO: 27229 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGTAGACTCCGTGAAGGGCCGAT AATAAATACTATGTAGACTCCGTGAAGGGCCGAT TCACCATCTCCAGAGACAACAATTCCAAGAACACGCT GTATCTGCAAATGAACAGCCTGAGAGCCGAGGA CACGGCTGTGTATTACTGTGCAGAGAAGTGGGA TTTACTGAGGACTACTGGGGCCAGGGAACCCTGG TCACCGTCTCCTCA<br>SEQ ID NO: 31235 |
| 21-225_225F8 | | AA | DIQMTQSPSSLSASVGDRVTITCRASQGIRNDLG WYQQKPGKAPKRLIYAASSLLGGVPSRFSGSGS GTEFTLTISSLQPEDFATYYCLQHNSYPFTFGPGT KVDIK<br>SEQ ID NO: 27230 | QVQLVESGGGVVQPGRSLRLSCAASGFTFSSYGMH WVRQAPGKGLEWVAVIWYDENNKYYVDSVKGRF TISRDNSKNTLYLQMNSLRAEDTAVYYCAREVGFT EDYWGQGTLVTVSS<br>SEQ ID NO: 31236 |

FIGURE 50
(Continued)

| | | | | |
|---|---|---|---|---|
| iPS:436584 | 21-225_225B9 | NA | GACATCGTGATGACCCAGTCTCCAGATTCCT GGCTGTGTCTCTGGGCGAGAGGGCCACCATCA ACTGCAAGTCCAGCCAGAGTGTTTATACAGC TCCAACAATAACAACTACTTAGCTTGGTACCA ACAAAAACCAGGACAGCCTCCTAAGCTGCTCA TTTTCTGGGCATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAACAC TCCAAGAGTATTCCGTAAGTTTGGGCAGGG GATCAAACTGGAGATCCAA | CAGGTGCAGCTGGTGCAGTCTGGGACTGAGGTG AGGAAGCCTGGGCCTCAGTGAAGGTCTCCTGC AAGGCTTCTGGATACACCTTCACCAATTATGATA TCAACTGGGTACGACAGGCCACTGGACAAGGC TTGAGTGGATGGGATGGATGCACCTAACAGTGG TAACACAGGCTATGCACAGAAGTTCGGGGCAG AGTCACCATGACCAGGAACACCTCCATAAACAC AGCCTACATGGAGCTGAACAGCCTGAGATCTGA GGACACGGCCGTATATTATTGTGCATATAGCAGT GGCTGGACCCTTTTGACTACTGGGGCCAGGGAA CCCTGGTCACCGTCTCCTCA |
| | | AA | DIVMTQSPDSLAVSLGERATINCKSSQSVLYSSN NNNYLAWYQQKPGQPPKLLIFWASTRESGVPDR FSGSGSGTDFTLTISSLQAEDVAVYYCQHSKSIPG KFGQGIKLEIQ | QVQLVQSGTEVRKPGASVKVSCKASGYTFTNYDIN WVRQATGQRLEWMGWMHPNSGNTGYAQKFRGR VTMTRNTSINTAYMELNSLRSEDTAVYYCAYSSG WTLFDYWGQGTLVTVSS |
| | | | SEQ ID NO: 27231 | SEQ ID NO: 31237 |
| | | | SEQ ID NO: 27232 | SEQ ID NO: 31238 |
| iPS:436586 | 21-225_225F11 | NA | GACATCGTGATGACCCAGTCTCCAGACTCCT GGCTGTGTCTCTGGGCGAGAGGGCCACCATCA ACTGCAAGTCCAGCCAGAGTGTTTATACAGC TCCAACAATTACAACTACTTAGCTTGGTACCA GCAGAAGACCAGGACAGCCTCCTAAGCTGCTCA TTTACTGGGCTTCTACCCGGGAATCCGGGGTC CCTGACCGATTCAGTGGCAGCGGGTCTGGGCC AGATTTCACTCTCACCATCAGCAGCCTGCAGG CTGAAGATGTGGCAGTTTATTACTGTCAGCAA TATTATACTACTCCTCCGACGTTCGGCCAAGG GACCAAGGTGAAATCAAA | CAGGTGCAGCTGGTGCAGTCTGGGGCTGAGGTG AAGAAGCCTGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCATGACCAGGAACACCTCCATAAACAC AGCCTACATGGAGCTGAGCAGCCTGAGATCTGA GGACACGCCCGTGTATTACTGTGCGTATAGCAGT GGCTGGACCGCTTTGACTACTGGGGCCAGGGAA CCCTGGTCACCGTCTCCTCA |
| | | | SEQ ID NO: 27233 | SEQ ID NO: 31239 |

FIGURE 50
(Continued)

| | | | |
|---|---|---|---|
| | | AA | DIVMTQSPDSLAVSLGERATINCKSSQSVLYSSN NYNYLAWYQQRPGQPPKLLIYWASTRESGVPD RFSGSGSGPDFTLTISSLQAEDVAVYYCQQYYTT PPTFGQGTKVEIK<br>SEQ ID NO: 27234 | QVQLVQSGAEVKKPGASVKVSCKASGYTFTNYDIN WVRQATGQGLEWMGWMHPNSGNTGYAQKFQGR VTMTRNTSINTAYMELSSLRSEDTAVYYCAYSSGW YRFDYWGQGTLVTVSS<br>SEQ ID NO: 31240 |
| iPS:436588 | 21-225_225F12 | NA | CAGGTGCAGCTGGTGCAGTCTGGGGCTGAGGTG AAGAAGCCTGGGGCCTCAGTGAAGGTCTCTGC AAGGCTTCTGGATACACCTTCACCATTATGATA TCAACTGGGTGCGACAGGCCACTGGACAAGGC TTGAGTGGATGGGATGCACAGAAGTTCCAGGCA GTAACACAGGCTATGCCAGGAACAGTG GAGTCACCATGGCCAGGAACACCTCCATAAGCA CAGCCTACATGGAGCTGAGCAGCCTGAGATCTG AGGACACGGCCGTGTATTACTGTGCCTATAGCAG TGGCTGGTACAAGTTTGACTACTGGGGCCAGGGA ACCCTGGTCACCGTCTCCTCA<br>SEQ ID NO: 31241 | |
| | | AA | DIVMTQSPDSLAVSLGERATINCKSSQSVLYSSN NQNYLAWYQQKPGQPPRLLIYWTSTRESGVPDR FSGSGSGTDFTLTISNLQAEDVAVYYCQQYYITP CSFGQGTKLEIK<br>SEQ ID NO: 27236 | QVQLVQSGAEVKKPGASVKVSCKASGYTFTHYDIN WVRQATGQGLEWMGWMHPNSGNTGYAQKFQGR VTMARNTSISTAYMELSSLRSEDTAVYYCAYSSGW YKFDYWGQGTLVTVSS<br>SEQ ID NO: 31242 |

FIGURE 50
(Continued)

| | | | |
|---|---|---|---|
| iPS:436590 | 21-225_225H12 | NA | GACATCGTGATGACCCAGACTCCCTGGCTGTGTCTCTGGGGAGAGGCCACCATCAACTGCAAGTCCAGCAGTGTTTATACAACTCCAACAATAACAACTACTTAGCTTGGTACCAGCAGAAACCAGGACAGCCTCCTAACCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGACTGAAGATGTGGCAGTTTATTACTGTCAGCAATATTATATTACTCCCGTGCAGTTTTTGGCCAGGGGACCAAGCTGGAGATCAAA<br>SEQ ID NO: 27237 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCTTGAGTGGATGGGATGGATGCACCCTAACAGTGGTTGAGTGGATGGGATGGATGCACCCTAACAGTGGTAACACAGGCTATGCACAGAAGTTCAGGGCAGAGTCACCATGACCAGGAACACCTCCATAAGCACAGCCTACATGGAGCTGAGCAGCCTGAGATCTGAGGACACGGCCGTGTATTACTGTGCCTATAGCAGTGGCTGGTACAAGTTTGACTACTGGGGCCAGGGAACCCTGGTCACCGTCTCCTCA<br>SEQ ID NO: 31243 |
| | | AA | DIVMTQSPDSLAVSLGERATINCKSSQSVLYNSNNNNYLAWYQQKPGQPPNLLIYWASTRESGVPDRFSGSGSGTDFTLTISSLQTEDVAVYYCQQYYITPCSFGQGTKLEIK<br>SEQ ID NO: 27238 | QVQLVQSGAEVKKPGASVKVSCKASGYTFTNYDINWVRQATGQGLEWMGWMHPNSGNTGYAQKFQGRVTMTRNTSISTAYMELSSLRSEDTAVYYCAYSSGWYKFDYWGQGTLVTVSS<br>SEQ ID NO: 31244 |
| iPS:436592 | 21-225_226B1 | NA | GATATTGTGATGACCCAGACTCCACTCTCTGTCCGTCACCCTGGACAGCCGGCCTCCATCTCCTGCAAGTCTAGTCAGAGCCTCCTGCATGGTGATGGAAAGAACCTATTTGTATTGGTACCTGCAGAGGCCAGGCCAGCCTCCACAGCTCCTGATCAATGAAGTTTCCATCCGGTTCTCTGGAGTGCCAGATAGGTTCAGTGGCAGCGGGTCAGGGACAGATTTCACACTGAAAATCAGCAGGGTGGAGGCTGAGGATGTTGGGGTTTACTACTGCATGCAAGGTATACAGATTCCGTGGACGTTCGGCCAGGGGACCAAGGTGGACATCAAA<br>SEQ ID NO: 27239 | CAGGTGCAGCTGGTGGAGTCTGGGGGAGGCGTGGTCCAGCCTGGGAGGTCCCTGAGACTCTCCTGTGCAGCGTCTGGATTCACCTTCAGTACTACTATGCCATGCACTGGGTCCGCCAGGCTCCAGGCAAGGGCTGGAGTGGGTGGCAATTATATGGTATGATGGAAGTTATAAATACTATGCAGACTCCGTGAAGGGCCGATTCACCATCTCCAGAGACAATTCCAAGAACACGCTGTTTCTGCAAATGAACAGCCTGAGAGCTGAGGACACGGCTGTGTATTACTGTGCGAGAGATCACTACGATTTTTGGAGTGGTTATCTTACCCACTGGGGCCAGGGAACCCTGGTCACCGTCTCCTCA<br>SEQ ID NO: 31245 |

FIGURE 50
(Continued)

| | | | |
|---|---|---|---|
| iPS:436594 | 21-225_226A5 | AA | DIVMTQTPLSLSVTPGQPASISCKSSQSLLHGDGKTYLYWYLQRPGQPPQLLINEVSIRFSGVPDRFSGSGSGTDFTLKISRVEAEDVGVYYCMQSIQIPWTFGQGTKVDIK<br>SEQ ID NO: 27240 | QVQLVESGGGVVQPGRSLRLSCAASGFTFSTYGMHWVRQAPGKGLEWVAIIWYDGGYKYYADSVKGRFTISRDNSKNTLFLQMNSLRAEDTAVYYCARDHYDFWSGYLTHWGQGTLVTVSS<br>SEQ ID NO: 31246 |
| | | NA | GATATTGTGATGACCCAGACTCCACTCTCTCTGTCCGTCACCCCTGGACAGCCGGCCTCCATCTCCTGCAAGTCTAGTCAGAGCCTCCTACATGGTGATGGAAAGACCTATTTGTATTGGTACCTGCAGAAGCCAGGCCAGCCTCCACAGCTCCTGATCTATGAAGTTTCCAACCGGTTCTCTGGAGTGCCAGATAGGTTCAGTGGCAGCGGGTCAGGGACAGATTTCACACTGAAAATCAGCCGGGTGGAGGCTGAGGATGTTGGGGTTTATTACTGCATGCAAAGTATACAGATTCCGTGGACGTTCGGCCAAGGGACCAAGGTGGAGATCAAA<br>SEQ ID NO: 27241 | CAGGTGCAGCTGGTGGAGTCTGGGGGAGGCGTGGTCCAGCCTGGGAGGTCCCTGAGACTCTCCTGTGCAGCGTCTGGATTCACCTTCAGTACTATGGCATGCACTGGGTCCGCCAGGCTCCAGGCAAGGGGCTGGAGTGGGTGGCAATTATATGGTATGATGGAACTAATAAATACTATACAGACTCCGTGAAGGGCCGATTCACCATCTCCAGAGACAACAATTCCAAGAACACGCTGTATCTGCAAATGAACAGCCTGAGAGCCGAGGACACGGCTGTGTATTACTGTGCGAGAGAGGTCACGATTTTTGGAGTGGCTTTTTGTTACTGGGGCCAGGGAACCCTGGTCACCGTCTCCTCA<br>SEQ ID NO: 31247 |
| | | AA | DIVMTQTPLSLSVTPGQPASISCKSSQSLLHGDGKTYLYWYLQKPGQPPQLLIYEVSNRFSGVPDRFSGSGSGTDFTLKISRVEAEDVGVYYCMQSIQIPWTFGQGTKVEIK<br>SEQ ID NO: 27242 | QVQLVESGGGVVQPGRSLRLSCAASGFTFSNYGMHWVRQAPGKGLEWVAIIWYDGTNKYYTDSVKGRFTISRDNSKNTLYLQMNSLRAEDTAVYYCAREGHDFWSGFFCYWGQGTLVTVSS<br>SEQ ID NO: 31248 |

FIGURE 50
(Continued)

| | | | |
|---|---|---|---|
| iPS:436596 | 21-225_226C6 | NA | GACATCCAGATGACCCAGTCTCCATCCTCCCT GTCTGCATCTATAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGCTCCATCAAGGTTCAGCGG CAGTGGATCTGGGACAGAATTCACTCTCACAA TCAGCAACCTGCAGCCTGAAGATTTTGCAACT TATTACTGTCTACAGCATTATAATTACCCTCGG GCGTTCGGCCAAGGGACCAAGGTGGAAATCC AA<br>SEQ ID NO: 27243 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGTA TAGCAGCAGCTGGTACGACTACGGTATGGACGTC TGGGGCCAAGGGACCACGGTCACCGTCTCCTCA<br>SEQ ID NO: 31249 |
| | | AA | DIQMTQSPSSLSASIGDRVTITCRASQGIRNDLG WYQQKPGKAPKRLIYAASSLQSGLPSRFSGSGSG TEFTLTISNLQPEDFATYYCLQHYNYPRAFGQGT KVEIQ<br>SEQ ID NO: 27244 | QVQLVESGGGVVQPGRSLRLSCAASGFTFSDYGM HWVRQAPGKGLEWVAVIWYDGSNKYYADSVKGR FTISRDNSKNTLYLQTNSLRAEDTAVYYCARERYSS SWYDYGMDVWGQGTTVTVSS<br>SEQ ID NO: 31250 |
| iPS:436598 | 21-225_226D6 | NA | GACATCGTGATGACCCAGTCTCCAGACTCCCT GGCTGTGTCTCTGGGCGAGAGGGCCACCATCA ACTGCAGGTCCAGCAGTGATATTTATACATC AAGGCTTCTGGATACACCTTCACCAATTATGATA TCCAACAATAAGAACTACTTAGCTTGGTACCA GCAGAAAACCAGGACAGCCTCCTAAGATGCTCA TTTACTGGGCATCTACCCGGGAATCCGGGGTC CCTGACCGATTCAGTGGCAGCGGGTCTGGGAC AGTCACCATGACCAGGAACACCTCCATAAGCAC AGATTTCACTCTCACCATCAGCAGCCTGCAGG CTGAAGATGTGGCAGTTTATTACTGTCAGCAA TATTATATGTTCCCGTGCAGTTTTGGCCAGGG GACCAAGCTGGAGATCAAA<br>SEQ ID NO: 27245 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGCACAGAAGTTCAGGCAG TAACACAGGCTATGCACAGAAGTTCCAGGCAG AGTCACCATGACCAGGAACACCTCCATAAGCAC AGCCTACATGGAGCTGAGCAGCCTGAGATCTGA GGACACGGCCGTGTATTACTGTGCCTATAGCAGT GGCTGGTACAAGTTTGACTACTGGGGCCAGGGA ACCCTGGTCACCGTCTCCTCA<br>SEQ ID NO: 31251 |

FIGURE 50
(Continued)

| | | | |
|---|---|---|---|
| iPS:436600 | 21-225_226F6 | AA | DIVMTQSPDSLAVSLGERATINCRSSQSILYISNN KNYLAWYQQKPGQPPKMLIYWASTRESGVPDR FSGSGSGTDFTLTISSLQAEDVAVYYCQQYYSSP CSFGQGTKLEIK<br>SEQ ID NO: 27246 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YKFDYWGQGTLVTVSS<br>SEQ ID NO: 31252 |
| | | NA | GACATCGTGATGACCCAGTCTCCAGACTCCCT GGCTGTGTCTCTGGGCGAGAGGGCCACCATCA ACTGCAAGTCCAGCCAGAGTATTTATACAGC TCCAACAATTACAAACTACTTAGCTTGGTACCA GCAGAAGCCAGGACAGCCTCCTAAGCTGCTCA TTTACTGGGCTTCTACCCGGGAATCCGGGGTC CCTGACCGATTCAGTGGCAGCGGGTCTGGGCC AGATTTCACTCTCACCATCAGCAGCCTGCAGG CTGAAGATGTGGCAGTTTATTACTGTCAGCAA TATTATACTACTCCTCCGACGTTCGGCCAAGG GACCAAGGTGGAAATCAAA<br>SEQ ID NO: 27247 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACACAGAAGTTCCAGGGCAG TAACACAGGCTATGCACAGAAGTTCCAGGGCAG AGTCACCATGACCAGGAACACCTCCATAAACAC AGCCTACATGGAGCTGAGCAGCCTGAGATCTGA GGACACGGCCGTGTATTACTGTGCGTATAGCAGT GGCTGGTACCGCTTTGACTACTGGGGCCAGGGAA CCCTGGTCACCGTCCTCCTCA<br>SEQ ID NO: 31253 |
| | | AA | DIVMTQSPDSLAVSLGERATINCKSSQSILYSSNN YNYLAWYQQKPGQPPKLLIYWASTRESGVPDRF SGSGSGPDFTLTISSLQAEDVAVYYCQQYYTTPP TFGQGTKVEIK<br>SEQ ID NO: 27248 | QVQLVQSGAEVKKPGASVKVSCKASGYTFTNYDIN WVRQATGQGLEWMGWMHPNSGNTGYAQKFQGR VTMTRNTSINTAYMELSSLRSEDTAVYYCAYSSGW YRFDYWGQGTLVTVSS<br>SEQ ID NO: 31254 |

FIGURE 50
(Continued)

| | | | | |
|---|---|---|---|---|
| iPS:436602 | 21-225_226E7 | NA | GATATTGTGATGACCCAGACTCCACTCTCT GTCCGTCACCCCTGGACAGCCGGCCTCCATCT CCTGCAAGTCTAGTCAGAGCCTCCTGCATGGT GATGGAAAGAACCTATTTGTATTGGTACCAGCA GAAGCCAGGCCAGCCTCCACAGATCCTGATCT ATGAAGTTTCCAACCGGTTCTCTGGAGTGCCA GATAGGTTCAGTGGCAGCGGGTCAGGGACAG ACTTCACACTGAAAATCAGCGGGTGGAGGCT GAGGATGTTGGGGTTTATTACTGCATGCAAAG TATACAGGTTCCGTGGACGTTCGGCCAAGGGA CCAAGGTGGAGATCAAA | CAGGTGCAGCTGGTGGAGTCTGGGGGAGGCGTG GTCCAGCCTGGGAGGTCCCTGAGACTCTCCTGTG CAGCCTCTGGATTCACCTTCAGTACCTATGGCAT GCACTGGGTCCGCCAGGCTCCAGGCAAGGGCT GGAATGGGTGGCAATTATATGGTATGATGAAGT AATAAATACTATGCAGACTCCGTGAAGGGCCGA TTCACCATCTCCAGAGACAATTTCAAGAACACGC TGTATCTGCAAATGCACAGCCTGAGAGCCGACG ACACGGCTGTGTATTACTGTGCGAGAGAATTA CGATTTTGGAGTGGTTATTATGGCTACTGGGGC CAGGGAACCCTGGTCACCGTCTCCTCA |
| | | | SEQ ID NO: 27249 | SEQ ID NO: 31255 |
| | | AA | DIVMTQTPLSLSVTPGQPASISCKSSQSLLHGDG KTYLYWYQQKPGQPPQILIYEVSNRFSGVPDRFS GSGSGTDFTLKISRVEAEDVGVYYCMQSIQVPW TFGQGTKVEIK | QVQLVESGGGVVQPGRSLRLSCAASGFTFSTYGMH WVRQAPGKGLEWVAIIWYDGSNKYYADSVKGRFT ISRDNFKNTLYLQMHSLRADDTAVYYCARENYD F WSGYYWGQGTLVTVSS |
| | | | SEQ ID NO: 27250 | SEQ ID NO: 31256 |
| iPS:436604 | 21-225_226F7 | NA | GACATCCAGATGACCCAGTCTCCATCCTCCCT GTCTGCATCTGTTGGAGACAGAGTCACCATCA CTTGCCGGGCAAGTCAGGGCATTGGGAATGAT TTAGGCTGGTATCAGCAGAAACCAGGGAAAG CCCCTAAGCGCCTGATCTATGCTGCCTCCAGTT TGCAAAGTGGGGTCCCATCAAGGTTCAGCGGC AGTGTATCTGGGACAGAATTCATTCTCACAAT CAGCAGCCTGCAGCCTGAAGATTTTGCAACTT ATTACTGTCTACATCATTATTACTCCCTCGGA CGTTCGGCCAAGGGGACCAAGGTGGAAATCAA A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAATTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGGTA TAACAGCGGCTGGTACGACTACGGTTTGGACGTC TGGGGCCAAGGGACCACGGTCACCGTCTCCTCA |
| | | | SEQ ID NO: 27251 | SEQ ID NO: 31257 |

FIGURE 50
(Continued)

| | | | |
|---|---|---|---|
| iPS:436606 | 21-225_226G8 | AA | DIQMTQSPSSLSASVGDRVTITCRASQGIGNDLG WYQQKPGKAPKRLIYAASSLQSGVPSRFSGSVS GTEFILTISSLQPEDFATYYCLHHYSYPRTFGQGT KVEIK<br>SEQ ID NO: 27252 | QVQLVESGGGVVQPGRSLRLSCAASGFTFSSYGMH WVRQAPGKGLEWVAIHWYDGSNKYYADSVKGRFT ISRDNSKNTLYLQMNSLRAEDTAVYYCARERYNSG WYDYGLDVWGQGTTVTVSS<br>SEQ ID NO: 31258 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GATGGAAAGACCTTTTTGTATTGGTACCTGCA GAAGCCAGGCCAGCCTCCACAGCTCCTGATCT ATGAAATTTCCAACGGTTCTCTGGAGTGCCA GATAGGTTCAGTGGCAGCGGGTCAGGGACAG ATTTCACACTGAAAATCAGCGGGGTGGAGCT GAGGATGTTGGGGATTTATTACTGCATGCAAAG TACACAGCTTCCTCGGACGTTCGGCCAAGGGA CCAAGGTGGAAATCAAA<br>SEQ ID NO: 27253 | CAGGTGCAGCTGGTGCAGTCTGGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCTTACAGTGG TGACACAAAGTATGCACAGAAGTTTCAGGCAG GGTCACCATGACCAGGGACACGTCCATCAGCAC AGCCTACATGGAACTGAGCAGGCTGAGATTTGA CGACACGGCCGTGTTTTACTGTGCGAGAGATTGG GGTGGCTACAGTTCTTACTACTACGGTATGGACG TCTGGGGCCAAGGGACCACGGTCACCGTCTCTC A<br>SEQ ID NO: 31259 |
| | | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK<br>SEQ ID NO: 27254 | QVQLVQSGAEVKKPGASVKVSCKASGYTFTGYYIH WVRQAPGQGLEWMGWINPYSGDTKYAQKFQGRV TMTRDTSISTAYMELSRLRFDDTAVFYCARDWGG YSSYYYGMDVWGQGTTVTVSS<br>SEQ ID NO: 31260 |

FIGURE 50
(Continued)

| | | | |
|---|---|---|---|
| iPS:436608 | 21-225_226A9 | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A <br/><br/>SEQ ID NO: 27255 | CAGGTGCAGCTGGTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATGTGGTGAGGAAAG TAATAAATACTATACAGACTCCGTGAAGGGCCG ATTCACCATCTCCAGAGACAATTCCAAGAACACG CTGTTTCTGCAAATGAACAGCCTGAGAGCCGAGG ACACGGCTGTGTATTACTGTGCGAGAGAAGTGGG ATTCACTGAGGACTACTGGGGCCAGGGAACCCT GGTCACCGTCTCCTCA <br/><br/>SEQ ID NO: 31261 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK <br/><br/>SEQ ID NO: 27256 | QVQLVESGGGVVQPGRSLRLSCAASGFTFSNYGM HWVRQAPGKGLEWVAVIWYEESNKYYTDSVKGR FTISRDNSKNTLFLQMNSLRAEDTAVYYCAREVGF TEDYWGQGTLVTVSS <br/><br/>SEQ ID NO: 31262 |
| iPS:436610 | 21-225_226F9 | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GATGGAAAGACCTTTTGTATTGGTACCTGCA GAAGCCAGGCCAGCCTCCACAGCTCCTGATCT ATGAAATTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGATTTATTACTGCATGCAAAG TACACAGCTTCTCTCGACGTTCGGCCAAGGGA CCAAGGTGGAAATCAAA <br/><br/>SEQ ID NO: 27257 | CAGGTGCAGCTGCAGCTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTTACAGTGG TGACACAAAGTATGCACAGAAGTTTCAGGGCAG GGTCACCATGACCAGGGACACGTCCATCAGCAC AGCCTACATGGAACTGAGCAGGCTGAGATTTGA CGACACGGCCGTGTTTTACTGTGCGAGAGATTGG GGTGGCTACAGTTCTTACTACTACGGTATGGACG TCTGGGGCCAAGGGACCACGGTCACCGTCTCTTC A <br/><br/>SEQ ID NO: 31263 |

FIGURE 50
(Continued)

| | | | | |
|---|---|---|---|---|
| iPS:436612 | 21-225_226H9 | AA | DIVMTQTPLSLSVTPGQPASISCKSSQSLLHSDGKTFLYWYLQKPGQPPQLLIYEISNRFSGVPDRFSGSGSGTDFTLKISRVEAEDVGIYYCMQSTQLPRTFGQGTKVEIK<br>SEQ ID NO: 27258 | QVQLVQSGAEVKKPGASVKVSCKASGYTFTGYYIHWVRQAPGQGLEWMGWINPYSGDTKYAQKFQGRVTMTRATSISTAYMELSRLRFDDTAVFYCARDWGGYSSYYYGMDVWGQGTTVTVSS<br>SEQ ID NO: 31264 |
| | | NA | GATATTGTGATGACCCAGACTCCACTCTCTCTGTCCGTCACCCCTGGACAGCCGGCCTCCATCTCCTGCAAGTCTAGTCAGAGCCTCCTGCATAGTGATGGAAAGACCTTTTTGTATTGGTACCTGCAGAGGCCAGGCCAGCCTCCACAGCTCCTGATCTATGAAGTTTCCAACCGGTTCTCTGGAGTGCCAGATAGGTTCAGTGGCAGCGGGTCAGGGACAGATTTCACACTGAAAATCAGCCGGGTGGAGGCTGAGGATGTTGGGATTTATTACTGCATGCAAAGTACACAGCTTCCTCGGACGTTCGGCCAAGGGACCAAGGTGGAAATCAAA<br>SEQ ID NO: 27259 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATACACTGGGTGCGACAGGCCCCTGGACAAGGGCTTGAGTGGATGGGATGGATCAACCCTTACAGTGGTGACACAAACTCTGCACAGAAGTTTCAGGCCGGGTCACCATGACCAGGGACACGTCCATCAGCACAGCCTACATGGAACTGAGCAGGCTGAGATTTGACGACACGGCCGTGTTTTACTGTGCGAGAGATTGGGGTGGCTACAGTTCTTACTACTACGGTATGGACGTCTGGGGCCAAGGGACCACGGTCACCGTCTCTCA<br>SEQ ID NO: 31265 |
| | | AA | DIVMTQTPLSLSVIPGQPASISCKSSQSLLHSDGKTFLYWYLQRPGQPPQLLIYEVSNRFSGVPDRFSGSGSGTDFTLKISRVEAEDVGIYYCMQSTQLPRTFGQGTKVEIK<br>SEQ ID NO: 27260 | QVQLVQSGAEVKKPGASVKVSCKASGYTFTGYYIHWVRQAPGQGLEWMGWINPYSGDTNSAQKFQGRVTMTRDTSISTAYMELSRLRFDDTAVFYCARDWGGYSSYYYGMDVWGQGTTVTVSS<br>SEQ ID NO: 31266 |

FIGURE 50
(Continued)

| | | | | |
|---|---|---|---|---|
| iPS:436614 | 21-225_226F10 | NA | GATATTGTGATGACCCAGACTCCACTCTCT GTCCGTCACCCCTGACAGCGCCTCCATCT CCTGCAAGTCTAGTCAGAGCCTCCTGCATAGT GATGGAAAGAACCTTTTGTATTGGTACCTGCA GAAGCCAGGCCAGCCTCCACAGCTCCTGATCT ATGAAAATTTCCAACCGGTTCTCTGGGGTGCCA GATAGGTTCAGTGGCAGCGGGTCAGGACAG ATTTCACACTGAAAATCAGCGAGTGGAGGCT GAGGATGTTGGGATTTATTACTGCATGCAAAG TACACAGCTTCCTCGGACGTTCGGCCAAGGA CCAAGGTGGAAATCAAA SEQ ID NO: 27261 | CAGGTGCAGCTGGTGCAGTCTGGGGGTGAGGTG AAGAAGCTGAGGGCCTCAGTGAAGGTCTCCTGC AAGGCTTCTGGATACACCTTCACCGGCTATTATA TACACTGGGTGCGACAGGCCCCTGACAAGGGC TTGAGTGGATGGGATGGATCAACCATACAGTGG TGACACAAACTATGCACAGAAGTTTCAGGGCAG GGTCACCATGACCAGGGACACGTCCGTCAGCAC AGCCTACATGGAACTGAGCAGGTTGAGATTGA CGACACGGCCGTGTTTACTGTGCGAGAGATTGG GGTGGCTACAGTTCTTACTACTACGGTATGGACG TCTGGGGCCAAGGGACCCCGGTCACCGTCTCTTC A SEQ ID NO: 31267 |
| | | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK SEQ ID NO: 27262 | QVQLVQSGGEVKKLRASVKVSCKASGYTFTGYYIH WVRQAPGQGLEWMGWINPYSGDTNYAQKFQGRV TMTRDTSVSTAYMELSRLRLDDTAVFYCARDWGG YSSYYYGMDVWGQGTPVTVSS SEQ ID NO: 31268 |
| iPS:436616 | 21-225_226D11 | NA | GACATCGTGATGACCCAGTCTCCAGACTCCT GGCTGTGTCTCTGGGCGAGAGGGCCACCATCA ACTGCAAGTCCAGCCAGAGAATGTTTTACACAGC TCCAACAGTAATAACTACTTAGTTTGGTACCA GCAGAAACCAGGACAGCCTCCTAAACTGCTCA TTTACTGGGCATCTACCCGGGAATCCGGGGTC CCTGACCGATTCAGAGGCAGCGGGTCTGGGAC AGATTTCACTCTCACCATCAGCAGCCTGCAGG CTGAAGATGTGGCAGTTTATTACTGTGTCAGCAA TATTATAAAACTCCGTGACGTTCGGCCAAGG GACCAAGGTGGAAATCAAA SEQ ID NO: 27263 | CAGGTGCAGCTGGTGCAGTCTGGGGCTGAGGTG AAGAAGCCTGGGGCCTCAGTGAAGGTCTCCTGC AGGTCTTCTGGATACACCTTCACCAATTATGATA TCAACTGGGTGCGACAGGCCACTGGACAAGGC TTGAGTGGATGGGATGGATGCACAGAAGTTCAGGCAG TAACACAGGCTATGCACAGAAGTTCAGGGCAG AGTCACCATGACCAGGAACACCTCCATAAGCAC AGCCTACATGGAGCTGAGCAGCCTGAGATCTGA GGACACGGCCGTGTATTACTGTGCCTATAGCAGT GGCTGGTACTACTTTGACTACTGGGGCCAGGAA CCCTGGTCACCGTCTCCTCA SEQ ID NO: 31269 |

FIGURE 50
(Continued)

| | | | |
|---|---|---|---|
| iPS:436618 | 21-225_226E11 | AA | DIVMTQSPDSLAVSLGERATINCKSSQNVLHSSN SNNYLVWYQQKPGQPPKLLIYWASTRESGVPDR FRGSGSGTDFTLTISSLQAEDVAVYYCQQYYKTP WTFGQGTKVEIK<br>SEQ ID NO: 27264 | QVQLVQSGAEVKKPGASVKVSCRSSGYTFTNYDIN WVRQATGQGLEWMGWMHPNSGNTGYAQKFQGR VTMTRNTSISTAYMELSSLRSEDTAVYYCAYSSGW YYFDYWGQGTLVTVSS<br>SEQ ID NO: 31270 |
| | | NA | GATATTGTGATGACCCAGACTCCACTCTCTCT GTCCGTCACCCCTGGACAGCCGGCCTCCATCT CCTGCAAGTCTAGTCAGAGCCTCCTGCATAGT GATGGAAAGACCTTTTTGTATTGGTACCTGCA CAAGCCAGGCCAGTCCTCCACACTCCTGATCT ATGAAATTTCCAACCGGTTCTCTGGAGTGCCA GATAGGTTCAGTGGCAGCGGGTCAGGGACAG ATTTCACACACTGAAAATCAGCCGGGTGGAGCT GAGGATGTTGGGATTTATTACTGCATGCAAAG TACACAGCTTCCTCGGACGTTCGGGCAAGGGA CCAAGGTGGAAATCAAA<br>SEQ ID NO: 27265 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTTACAGTGG TGACACAAACTATGCACAGAAGTTCAGGGCAG GGTCACCATGACCAGGGACACGTCCATCAGCAC AGCCTACATGGAACTGAGCAGGCTGAGATTTGA CGACACGGCCGTGTTTACTGTGCAGAGATTGG GGTGGCTACAGTTCTTACTACTACGGTATGGACG TCTGGGGCCAAGGGACCACGGTCACCGTCTCTC A<br>SEQ ID NO: 31271 |
| | | AA | DIVMTQTPLSLSVTPGQPASISCKSSQSLLHSDGK TFLYWYLHKPGQPPHLLIYEISNRFSGVPDRFSGS GSGTDFTLKISRVEAEDVGIYYCMQSTQLPRTFG QGTKVEIK<br>SEQ ID NO: 27266 | QVQLVQSGAEVKKPGASVKVSCKASGYTFTGYYIH WVRQAPGQGLEWMGWINPYSGDTNYAQKFQGRV TMTRDTSISTAYMELSRLRFDDTAVFYCARDWGG YSSYYYGMDVWGQGTTVTVSS<br>SEQ ID NO: 31272 |

FIGURE 50
(Continued)

| | | | | |
|---|---|---|---|---|
| iPS:436620 | 21-225_226H11 | NA | GACATCCAGATGACCCAGTCTCCATCCTCCCTGTCTGCATCTGTAGGAGACAGAGTCACCATCACTTGCCGGACAAGTCAGGGCATTAGAAATGATTTAGGCTGGTATCAGCAGAAACCAGGAAAGCCCCTAAGCGCCTGATCTATGCTGCATCCAGTTTGCAAAGTGGGGTCCCATCAAGGTTCAGTGGCAGTGGATCTGGGACAGATTTCACTCTCACAATCAGCAGCCTGCAGCCTGAAGATTTTGCAACTTATTACTGTCTACAGCATTATAGTTACCCTCGGACGTTCGGCCAAGGGACCAAGGTGGAAATCAAA | CAGGTGCAGTTGGTGGAGTCTGGGGGAGGCGTGGTCCAGCCTGGGAGGTCCCTGAGACTCTCCTGTCAGCCTCTGGATTCACCTTCAGTAACTGTGGCATGCACTGGGTCCGCCAGGCTCCAGGCAAGGGCTGGAGTGGGTGACAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAGCTGTATAGCAGCAGCTGGTACGACTACGGTTTGGACGTCTGGGGCCAAGGGACCACGGTCACCGTCTCCTCA |
| | | | SEQ ID NO: 27267 | SEQ ID NO: 31273 |
| | | AA | DIQMTQSPSSLSASVGDRVTITCRTSQGIRNDLGWYQQKPGKAPKRLIYAASSLQSGVPSRFSGSGSGTDFTLTISSLQPEDFATYYCLQHYSYPRTFGQGTKVEIK | QVQLVESGGGVVQPGRSLRLSCAASGFTFSNCGMHWVRQAPGKGLEWVTVIWYDGSNKYYADSVKGRFTISRDNSKNTLYLQMNSLRAEDTAVYYCARELYSSSWYDYGLDVWGQGTTVTVSS |
| | | | SEQ ID NO: 27268 | SEQ ID NO: 31274 |
| iPS:436622 | 21-225_226A12 | NA | GACATCGTGATGACCCAGTCTCCAGACTCCCTGGCTGTGTCTCTCGGCGAGAGGGCCACCATCAACTGCAAGTCCAGCCAGAGTGTTTTATACAGTTCCAACAATAACAACTACTTAGCTTGGTACCAGCAGAAACCTGGACAGCCTCCTAAGCTGCTCATTTACTGGGCATCTACCCGGGAAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTCCTCCGACGTTCGGCCAAGGGACCAAGGTGGAAATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGCACAGAAGTTCAGGGCAGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACGGCCGTGTATTACTGTGCTTATAGCAGTGGCTGGTACTACTTTGACTACTGGGGCCAGGGAACCCTGGTCACCGTCTCCTCA |
| | | | SEQ ID NO: 27269 | SEQ ID NO: 31275 |

FIGURE 50
(Continued)

| | | | |
|---|---|---|---|
| iPS:436624 | 21-225_226H12 | AA | DIVMTQSPDSLAVSLGERATINCKSSQNVLYSSN NNNYLAWYQQTPGQPPKLLFYWASTRKSGVPD RFSGSGSGTDFTLTISSLQAEDVAVYYCQQYYSS PPTFGQGTKVEIK<br>SEQ ID NO: 27270 | QVQLVQSGAEVKKPGASVKVSCKASGYTFTNYDIN WVRQATGQGLEWMGWMHPNSGNTGYAQKFQGR VTMTRNTSISTAYMELSSLRSEDTAVYYCAYSSGW YYFDYWGQGTLVTVSS<br>SEQ ID NO: 31276 |
| | | NA | GATATTGTGATGACCCAGACTCCACTCTCTCT GTCCGTCACCCCTGGACAGCCGGCCTCCATCT CCTGCAAGTCTAGTAAGACCCTCCTGCATAGT GATGGAAAGACCTTTTTGTATTGGTACCTGCA GAAGCCAGGCCAGCCTCCACAGCCCCTGATCT ATGAAATTTCCAACCGGTTCTCTGGAGTGCCA GATAGGTTCAGTGGCAGCGGGTCAGGGACAG ATTTCACACTGAAAATCAGCCGGGTGGAGCT GAGGATGTTGGGATTTATTACTGCATGCAAAG TACACAGCTTCCTCGGACGTTCGGCCAAGGGA CCAAGGTGGAAATCAAA<br>SEQ ID NO: 27271 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCTTACAGTGG TGACACAAACTATGCACAGAAGTTCAGGGCAG GGTCACCATGACCAGGGACACGTCCATCAGCAC AGCCTACATGGAACTGAGGAGGCTGAGATTTGA CGACACGGCCGTGTTTACTGTGCAGAGATTGGA GGTGGCTACAGTTCTTACTACTACGGTATGGACG TCTGGGGCCAAGGGACCACGGTCACCGTCTCTC A<br>SEQ ID NO: 31277 |
| | | AA | DIVMTQTPLSLSVTPGQPASISCKSSKTLLHSDGK TFLYWYLQKPGQPPQPLIYEISNRFSGVPDRFSGS GSGTDFTLKISRVEAEDVGIYYCMQSTQLPRTFG QGTKVEIK<br>SEQ ID NO: 27272 | QVQLVQSGAEVKKPGASVKVSCKASGYTFGYIH WVRQAPGQGLEWMGWINPYSGDTNYAQKFQGRV TMTRDTSISTAYMELRRLRFDDTAVFYCARDWGG YSSYYYGMDVWGQGTTVTVSS<br>SEQ ID NO: 31278 |

FIGURE 50
(Continued)

| | | | | |
|---|---|---|---|---|
| iPS:436626 | 21-225_227C1 | NA | GATATTGTGATGACCCAGACTCCACTCTCT GTCCGTCACCCCTGGACAGCCGGCCTCCATCT CCTGCAAGTCTAGTCAGAGCCTCCTGCATAGT GATGGAAAGAACCTTTTGTATTGGTACCTGCA GAAGCCAGGCCAGCCTCCACAGCTCCTGATCT ATGAAATTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGATTTATTACTGCATGCAAAG TACACAGCTTCCTCGGACGTTCGGCCAAGGA CCAAGGTGGAAATCAAA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK |
| | | | SEQ ID NO: 27273 | SEQ ID NO: 27274 |
| | | AA | | QVQLVQSGAEVKKPGASVKVSCKASGYTFTGYYT HWVRQAPGQGLEWMGWINPYSGGTNYAQKFQGR VTMTRDTSISTAYMELSRLRFDDTAVYYCARDWG GYSSYYYGMDVWGQGTTVTVSS |
| | | | | SEQ ID NO: 31279 |
| | | | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA CACACTGGGTGCGACAGGCCCCTGGACAAGGGC TTGAGTGGATGGGATGGATCAACCCTTACAGTGG TGCACAAACTATGCACAGAAGTTTCAGGGCAG GGTCACCATGACCAGGGACACGTCCATCAGCAC AGCCTACATGGAACTGAGCAGGCTGAGATTTGA CGACACGGCCGTGTATTACTGTGCGAGAGATTGG GGTGGCTACAGTTCTTACTACTACGGTATGGACG TCTGGGGCCAAGGGACCACGGTCACCGTCTCTTC A | |
| | | | SEQ ID NO: 31280 | |
| iPS:436628 | 21-225_227F2 | NA | GATATTGTGATGACCCAGACTCCACTCTCT GTCCGTCACCCCTGGACAGCCGGCCTCCATCT CCTGCAAGTCTAGTCAGAGCCTCCTGCATAGT GATGGAAAGAACCTTTTGTATTGGTACCTGCA GAAGCCAGGCCAGCCTCCACAGCTCCTGATCT ATGAAATTTCCAACCGGTTCTCTGGAGTGCCA GATAGGTTCAGTGGCAGCGGGTCAGGACAG ATTTCACACTGAAAATCAGCGGGTGGAGGCT GAGGATGTTGGGATTTATTACTGCATGCAAAG TACACAGCTTCCTCGGACGTTCGGCCAAGGGA CCAAGGTGGAAATCAAA | |
| | | | SEQ ID NO: 27275 | |
| | | | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA CACACTGGGTGCGACAGGCCCCTGGACAAGGGC TTGAGTGGATGGGATGGATCAACCCTTACAGTGG TGACACAAAGTATGCACAGGACACGTCCATCAGC AGCCTACATGAACTGAGCAGGCTGAGATTTGA CGACACGGCCGTGTTTTACTGTACTACGGTATGGACG GGTGGCTACAGTTCTTACTACTACGGTATGGACG TCTGGGGCCAAGGGACCACGGTCACCGTCTCTTC A | |
| | | | SEQ ID NO: 31281 | |

FIGURE 50
(Continued)

| | | | |
|---|---|---|---|
| iPS:436630 | 21-225_227G3 | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTKVEIK<br>SEQ ID NO: 27276 | QVHLVQSGAEVKKPGASVKVSCKASGYTFTGYYIH WVRQAPGQGLEWMGWINPYSGDTKYAQKFQGRV TMTRDTSISTAYMELSRLRFDDTAVFYCARDWGG YSSYYYGMDVWGQGTTVTVSS<br>SEQ ID NO: 31282 |
| | | NA | GACATCCAGATGACCCAGTCTCCATCCTCCCT GTCTGCATCTGTAGGAGACAGAGTCACCATCA CTTGCCGGGCAAGTCAGGGACATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATGTTGCAACT TATTACTGTCTACACCATAATAGTTACCCATTC ACTTTCGGCCCTGGGACCAAAGTGGATATCAA A<br>SEQ ID NO: 27277 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGTTGGAAGT AATCAATACTATGCAGACTCCGTGAAGGGCCGAT TCACCATCTCCAGAGACAATTCCAAGAACACGCT GTATCTGCAAATGAGCAGCCTGAGAGCCGAGGA CACGGCTGTGTATTACTGTGCAGAGAAGTGGGA TTCACTGAGGACTACTGGGGCCAGGGAACCCTG GTCACCGTCTCCTCC<br>SEQ ID NO: 31283 |
| | | AA | DIQMTQSPSSLSASVGDRVTITCRASQGIRNDLG WYQQKPGKAPKRLIYAASSLQSGVPSRFSGSGS GTEFTLTISSLQPADFATYYCLHHNSYPFTFGPGT KVDIK<br>SEQ ID NO: 27278 | QVQLVESGGGVVQPGRSLRLSCAASGFTFSSYGMH WVRQAPGKGLEWVAVIWYVGSNQYYADSVKGRF TISRDNSKNTLYLQMSSLRAEDTAVYYCAREVGFT EDYWGQGTLVTVSS<br>SEQ ID NO: 31284 |

FIGURE 50
(Continued)

| | | | |
|---|---|---|---|
| iPS:436632 | 21-225_227E4 | NA | GACATCCTGATGACCCAGTCTCCATCTTCCGT GTCTGCATCTGTAGGAGACAGAGTCACCATCA CTTGTCGGGCGAGTCAGGGTATTATCAACTGG TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ACTATTGTCAACAGGCTAACAGTTTCCCGTGG ACGTTCGGCCAAGGGACCAAGGTGGAAATCA AA SEQ ID NO: 27279 | GAGGGGCAGCTATTGGAGTCTGGGGAGGCTTG GTACAGCCTGGGGGGTCACTGAGACTCTCCTGTA CAGCCTCTGGATTCACCTTTAGCACTTTTGCCATG ACCTGGGTCCGCCAGGCTCCAGGGAGGGGGCTG GAGTGGGTCTCAGTTATTAGTGGTAGAGGTGGTA GCTCATTCTACGCAGACTCCGTGAAGGGCCGGTT CACCATCTCCAGAGACAATACCAAGAACACGCT GTATCTGCAAATGAACAGCCTGAGAGCCGAGA CACGGCCGTATATTACTGTGCGAAAGATCAACTA TGGTTTGACTACTGGGGCCAGGGAACCCTGGTCA CCGTCTCCTCA SEQ ID NO: 31285 |
| | | AA | DILMTQSPSSVSASVGDRVTITCRASQGIINWLA WYQQKPGKAPKLLIYAASSLQSGVPSRFSGSGS GTDFTLTISSLQPEDFAIYYCQQANSFPWTFGQG TKVEIK SEQ ID NO: 27280 | EGQLLESGGGLVQPGGSLRLSCTASGFTFSTFAMT WVRQAPGRGLEWVSVISGRGGSSFYADSVKGRFTI SRDNTKNTLYLQMNSLRAEDTAVYYCAKDQLWFD YWGQGTLVTVSS SEQ ID NO: 31286 |
| iPS:436634 | 21-225_227H5 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAAACCAGGGAAAG CCCCTAAGCGCCTGATCTATGCTGCATCCAGT TTGCAAAGTGGGGTCCCATCAAGGTTCAGCGG CAGTGGATCTGGGACAGATCGGACACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A SEQ ID NO: 27281 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGGCT GGAGTGGGTGGCAGTTATATATGGTATGAAGAAAG TAATAAATACTATGCAGACTCCGTGAAGGGCCG ATTCACCATCTCCAGAGACAATTCCAAGAACACG CTGTATCTGCAAATGAACAGCCTGAGAGCCGAG GACACGGCTATGTATTACTGTGCGAGAGAAGTGG GATTCACTGAGGACTACTGGGGCCAGGGAACCC TGGTCACCGTCTCCTCA SEQ ID NO: 31287 |

FIGURE 50
(Continued)

| | | | |
|---|---|---|---|
| | | AA | DIQMTQSPSSLSASVGDRVTITCRASQDIRNDLGWYQQKPGKAPKRLIYAASSLQSGVPSRFSGSGSGTEFTLTISSLQPEDFATYYCLQHNSYPFTFGPGTKVDIK<br>SEQ ID NO: 27282 | QVQLVESGGGVVQPGRSLRLSCAASGFTFSNYGMHWVRQAPGKGLDWVAVIWYEESNKYYADSVKGRFTISRDNSKNTLYLQMNSLRAEDTAMYYCAREVGFTEDYWGQGTLVTVSS<br>SEQ ID NO: 31288 |
| iPS:436636 | 21-225_227E6 | NA | GACATCGTGATGACCCAGTCTCCAGACTCCCTGACTGTGTCTCTGGGCGAGAGGGCCACCATCAACTGCAAGTCCAGCCAGAGTGTGTTATACAGCTCCAACGATAAGAACTACTTAGCTTGGTACCAGCAGAAACCAGGACAGCCTCCTAAGATGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTACTGTCAGCAATATTATAGTACTCCGTGCAGTTTTGGCCAGGGGACCAAGCTGGAGATCAAA<br>SEQ ID NO: 27283 | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGCCTTGAGTGGATGGGATGGATGCACAGAAGTTCCAGGGCAGTAACACAGGCTATGCACAGAAGTTCCAGGGCAGAGTCACCATGACCAGGAACACCTCCATAAGCACAGCCTACATGGAGCTGAGCAGCCTGAGATCTGAGGACACGGCCGTGTATTACTGTGCCTATAGCAGTGGCTGGTACAAGTTTGACTACTGGGGCCAGGGAACCCTGGTCACCGTCTCCTCA<br>SEQ ID NO: 31289 |
| | | AA | DIVMTQSPDSLTVSLGERATINCKSSQSVLYSSNDKNYLAWYQQKPGQPPKMLIYWASTRESGVPDRFSGSGSGTDFTLTISSLQAEDVAVYYCQQYYITPCSFGQGTKLEIK<br>SEQ ID NO: 27284 | QVQLVQSGAEVKKPGASVKVSCKASGYTFNYDINWVRQATGQGLEWMGWMHPNSGNTGYAQKFQGRVTMTRNTSISTAYMELSSLRSEDTAVYYCAYSSGWYKFDYWGQGTLVTVSS<br>SEQ ID NO: 31290 |

FIGURE 50
(Continued)

| | | | |
|---|---|---|---|
| iPS:436638 | 21-225_227C7 | NA | GACATCGTGATGACCCAGTCTCCAGACTCCCTGGCTGTGTCTCTGGGCGAGAGGGCCACCATCAACTGCAGGTCCAGCCAGATTGTTTTATCCGACTCCAACAATAACAACTACTTAGCTTGGTACCAGCAGAAACCAGGACAGCCTCCTAACCTGCTCATTTACTGGGCATCTACCCGGGAATCCGGGGTCCCTGACCGATTCAGTGGCAGCGGGTCTGGGACAGATTTCACTCTCACCATCAGCAGCCTGCAGGCTGAAGATGTGGCAGTTTATTTCTGTCAGCAATATTATAGTTCTCCTCCGACGTTCGGCCAAGGGACCAAGGTGGAAATCAAA SEQ ID NO: 27285 | CAGGTGCAGCTGGTGCAGTCTGGGGCTGAGGTGAAGAAGCCTAGGGCCTCAGTGAAGGTCTCCTGCAAGGCTTCTGGAGACACCTTCACCAATTATGATATCAACTGGGTGCGACAGGCCACTGGACAAGGCTTGAGTGGATGGGATGGATGCATCCTAACAGTGGTAACACAGGCTATGCACAGAAGTTCAGGGCAGAGTCACCATGACCAGGAACACCTCCATAAGCACAGCCTACATGGAGCTGAGCAGCCTGAGATCTGAGGACACGGCCGTGTATTACTGTGCATATAGCAGTGGCTGGTACCGCTTTGACTACTGGGGCCAGGGAACCCTGGTCACCGTCTCTCA SEQ ID NO: 31291 |
| | | AA | DIVMTQSPDSLAVSLGERATINCRSSQIVLSDSNNNNYLAWYQQKPGQPPNLLIYWASTRESGVPDRFSGSGSGTDFTLTISSLQAEDVAVYFCQQYYSSPPTFGQGTKVEIK SEQ ID NO: 27286 | QVQLVQSGAEVKKPRASVKVSCKASGHTFTNYDINWVRQATGQGLEWMGWMHPNSGNTGYAQKFQGRVTMTRNTSISTAYMELSSLRSEDTAVYYCAYSSGWYRFDYWGQGTLVTVSS SEQ ID NO: 31292 |
| iPS:436640 | 21-225_227A8 | NA | GATATTGTGATGACCCAGACTCCACTCTCTCTGTCCGTCACCCTGGACAGTCAGCCGGCCTCCATCTCCTGCAAGTCTAGTCAGAGCCTCCTGCATAGTGATGGAAAGAACCTTTTGTATTGGTATCTGCAGAAGCCAGGCCAGCCTCCACAGCTCCTGATCTATGAAAATTTCCAACCGGTTCTCTGGGGTGCCAGATAGGTTCAGTGGCAGCGGGTCAGGGACAGATTTCACACTGAAAATCAGTGAGGTGGAGGCTGAGGATGTTGGGATTTATTACTGCATGCAAAGTACACAGTTCCTCCTCGACGTTCGGCCAAGGACCAAGGTGGAAATCAAA SEQ ID NO: 27287 | CAGGTGCAGCTGCAGGTGCAGTCTGGGGCTGAGGTGAAGAAGCCTGGGGCCTCAGTGAAGGTCTCCTGCAAGGCTTCTGGATACACCTTCACCGGCTACTATATACACTGGGTGCGACAGGCCCCTGGACAAGGCTTGAGTGGATGGGGATGATCAACCCTACAGTGGTGGCACAAACTATGCACAGAAGTTTCAGGGCAGGGTCACCATGACCAGGGACACGTCCGTCAGCACAGCCTACATGGAACTGAGCAGGCTGAGATTGACGACACGGCCGTGTTTTACTGTGCGAGAGATTGGGGTGGCTACAGTTCTTACTACTACGGTATGGACGTCTGGGGCCAAGGGACCACGGTCACCGTCTCTCA SEQ ID NO: 31293 |

FIGURE 50
(Continued)

| | | | |
|---|---|---|---|
| | | AA | DIVMTQTPLSLSVTPGQPASISCKSSQSLLHSDGK TFLYWYLQKPGQPPQLLIYEISNRFSGVPDRFSGS GSGTDFTLKISRVEAEDVGIYYCMQSTQLPRTFG QGTRVEIK<br><br>SEQ ID NO: 27288 | QVQLVQSGAEVKKPGASVKVSCKASGYTFTGYYIH WVRQAPGQGLEWMGWINPYSGDTNYAQKFQGRV TMTRDTSVSTAYMELSRLRFDDTAVFYCARDWGG YSSYYYGMDVWGQGTTVTVSS<br><br>SEQ ID NO: 31294 |
| iPS:436644 | 21-225_227G9 | NA | GACATCGTGATGACCCAGTCTCCAGACTCCCT GGCTGTGTCTCTGGGCGAGAGGGCCACCATCA ACTGCAAGTCCAGCCAGAGTGTTTTACACAGC TCCAACAATAACAACTACTTAGCTTGGTATCA GCAGAAACCAGGACAGCCTCCTAAGCTGCTCA TTTACTGGGGATCTACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTGCTCCGTACAGTTTTGGCCAGGG GACCAAGTTGGAGATCAAA<br><br>SEQ ID NO: 27289 | CAGGTGCAGCTGGTGCAGTCTGGGGCTGAGGTG AAGAAGCCTGGGGCCTCAGTGAAGGTCTCCTGC AGGGCTTCTGGATACACCTTCACCAATTATGATA TCAACTGGGTGCGACAGGCCACTGGACGAGGGC TTGAGTGGATGGGATGGATGTACCCTAACAGTGG TAACACAGGCTATGCACAGAAGTTCCAGGGCAG AGTCACCATGACCAGGAACACCTCCATAAGCAC AGCCTACATGGAGCTGAGCAGCCTGAGATCTGA GGACACGGCCGTGTATTACTGTGCGCTTAGCAGT GGCTGGTACTGGTTCGACCCCTGGGGCCAGGGA ACCCTGGTCACCGTCTCCTCA<br><br>SEQ ID NO: 31295 |
| | | AA | DIVMTQSPDSLAVSLGERATINCKSSQSVLHSSN NNNYLAWYQQKPGQPPKLLIYWGSTRESGVPD RFSGSGSGTDFTLTISSLQAEDVAVYYCQQYYSA PYSFGQGTKLEIK<br><br>SEQ ID NO: 27290 | QVQLVQSGAEVKKPGASVKVSCRASGYTFTNYDIN WVRQATGRGLEWMGWMYPNSGNTGYAQKFQGR VTMTRNTSISTAYMELSSLRSEDTAVYYCALSSGW YWFDPWGQGTLVTVSS<br><br>SEQ ID NO: 31296 |

FIGURE 50
(Continued)

| | | | |
|---|---|---|---|
| iPS:436646 | 21-225_227D11 | NA | GACATCGTGATGACCCAGTCTCCAGACTCCCTGGCTGTGTCTCTGGACGAGAGGGCCACCATCAACTGCAAGTCCAGCCAGAGTGTTTTACACAGTTCCAACAATAATAACTACTTAGCTTGGTACCAGCAGAAGCCAGGACAGCCTCCTAAGCTGCTCATTTACTGGGCATCTACCCGGGAATCCGGGATCCCTGACCGATTCAGTGGCAGCGGGTCTGGGACAGATTTCACTCTCACCATCAGCAGCCTGCAGGCTGAGGATGTGGCAGTTTATTACTGTCAGCAATATTATAATACTCCGTGCAGTTTTGGCCAGGGACCAAGCTGGAGATCAAA |
| | | | SEQ ID NO: 27291 |
| | | AA | DIVMTQSPDSLAVSLDERATINCKSSQSVLHSSNNNYLAWYQQKPGQPPKLLIYWASTRESGIPDRFSGSGSGTDFTLTISSLQAEDVAVYYCQQYYNTPCSFGQGTKLEIK |
| | | | SEQ ID NO: 27292 |
| iPS:436648 | 21-225_227F11 | NA | GATGTTGTGATGACTCAGTCTCCACTCTCCCTGCCCGTCACCCCTGGAGAGCCGGCCTCCATCTCCTGCTCTGGTCTAGTCAGAGCCTCCTGCATAGTAATGGATACAACTATTTGGATTGGTACCTGCAGAAGCCAGGCCAGTCTCCACAGGTCCTGATCTATTTGGGGTTCTAATCGGGCCTCCGGGGTCCCTGACAGGTTCAGTGGCAGTGGATCAGGTGGAGGCTGAAACACTGAAAATCAGCAGAGTGGAGGCTGAAGATGTTGGGGTTTATTACTGCATGCAAGCTCTACAAACTCCTCACCTTCGGCCAAGGGACACGACTGGAGATTAAA |
| | | | SEQ ID NO: 27293 |
| | | | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGCACCCTAACAGTGGTAACACAGGCTATGCACAGAAGTTCCAGGGCCGAGTCACCATGACCAGGAACACCTCCATAAGCACAGCCTACATGGAACTGAGCAGCCTGAGATCTGAGGACACGGCCGTGTATTACTGTGCGTATAGCAGTGGCTGGTACTACTTTGACTACTGGGGCCAGGGAACCCTGGTCACCGTCTCCTCA |
| | | | SEQ ID NO: 31297 |
| | | | QVQLVQSGAEVKKPGASVKVSCKASGYTFTNYDINWVRQATGQGLEWMGWMHPNSGNTGYAQKFQGRVTMTRNTSISTAYMELSSLRSEDTAVYYCAYSSGWYYFDYWGQGTLVTVSS |
| | | | SEQ ID NO: 31298 |
| | | | GAGGTGCAGCTGGTGGAGTCTGGGGGAGGCCTGGTCAAGCCTGGGGGGTCCCTGAGACTCTCCTGTGCAGTCTCTGGATTCACCTTCAGTAGCTACCTATAGCATGAACTGGGTCCGCCAGGCTCCAGGGAAGGGGCTGGAGTGGGTCTCATCCATTAGTAGTAGTAATTACATGTACTACCTCCAGAGACTCAGTGAAGGGCCGATTCACCATCTCCAGAGACAACGCCAAGAACTCACTGTATCTGCAAATGAACAGCCTGAGAGCCGAGGACTCGGCTGTGTATTACTGTGCGAGATTAGGGGTCTACTGGGGCCAGGGAACCCTGGTCACCGTCTCCTCA |
| | | | SEQ ID NO: 31299 |

FIGURE 50
(Continued)

| | | | |
|---|---|---|---|
| iPS:436650 | | AA | DVVMTQSPLSLPVTPGEPASISCWSSQSLLHSNG YNYLDWYLQKPGQSPQVLIYLGSNRASGVPDRF SGSGSGTDFTLKISRVEAEDVGVYCMQALQTP LTFGQGTRLEIK<br>SEQ ID NO: 27294 | EVQLVESGGGLVKPGGSLRLSCAVSGFTFSTYSMN WVRQAPGKGLEWVSSISSSINYMYYADSVKGRFTI SRDNAKNSLYLQMNSLRAEDSAVYYCARLGVYW GQGTLVTVSS<br>SEQ ID NO: 31300 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATCTGTCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTACAGCATAATAGTTACCCATTC ACTTTCGGCCCTGGGACCAAAGTGGATATCAA A<br>SEQ ID NO: 27295 | CAGGTGCAGCTGGTGGAGTCTGGGGGAGGCGTG GTCCAGCCTGGGAAGTCCCTGAGACTCTCCTGTG CAGCGTCTGGATTCACCTTCAGTAACTATAGCAT GCACTGGGTCCGCCAGGCTCCAGGCAAGGGCT GGAGTGGGTGGCAGTTATATGCGACTCCGTGAAGGCCGAT AATCAATACTATGCGACTCCGTGAAGGGCCGAT TCACCATCTCAGAGACAATTCCAAGAACACGCT GTATCTGCAAATGAGCAGCCTGAGAGCCGAGGA CACGGCTGTGTATTACTGTGCAGAGAAGTGGGA TTCACTGAGGACTACTGGGGCCAGGGAACCCTG GTCACCGTCTCCTCC<br>SEQ ID NO: 31301 |
| | 21-225_227C12 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHNSYPFTFGPGT KVDIK<br>SEQ ID NO: 27296 | QVQLVESGGGVVQPGKSLRLSCAASGFTFSNYGM HWVRQAPGKGLEWVAVIWYIGSNQYYADSVKGR FTISRDNSKNTLYLQMSSLRAEDTAVYYCAREVGF TEDYWGQGTLVTVSS<br>SEQ ID NO: 31302 |

FIGURE 50
(Continued)

| | | | | |
|---|---|---|---|---|
| iPS:436652 | 21-225_146B11 | NA | TCCTATGAGCTGACTCAGCCACCCTCAGTGTCCGTGTCCCCAGGACAGACAGCCAGCATCACCTGCTCTGGAGATAAATTGGGGGATAAATATGCTTCCTGGTATCAGCAGAAGCCAGGCCAGTCCCCTGTGCTGGTCATCTATCAAGATAGCAAGCGGCCCTCAGGGATCCCTGAGCGATTCTCTGGCTCCAACTCTGGGAACACAGCCACTCTGACCATCAGCGGGATCCAGGCTATGGATGAGGCTGACTATTACTGTCAGGCCGTGGGACAGCAGCACTGTGTATTCGGCGGAGGGACCAAGCTGACCGTCCTA | GAGGTGCAACTGTTGGAGTCTGGGGGAGGCTTGGTACAGCCTGGGGGGTCCCTGAGACTCTCCTGTGCAGCTTCTGGATTCACCTTTAGCAGCTATGCCATGAGCTGGGTCCGCCAGGCTCCAGGGAAGGGCTGGAGTGGGTCTCAGTTATTAGTGGTGGTAGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAATGGCGAGGTAACCCCACTGACTACGGTATGGACGTCTGGGGCCAAGGGACCACGGTCACCGTCTCCTCA |
| | | | SEQ ID NO: 27297 | SEQ ID NO: 31303 |
| | | AA | SYELTQPPSVSVSPGQTASITCSGDKLGDKYASWYQQKPGQSPVLVIYQDSKRPSGIPERFSGSNSGNTATLTISGIQAMDEADYYCQAWDSSTVVFGGGTKLTVL | EVQLLESGGGLVQPGGSLRLSCAASGFTFSSYAMSWVRQAPGKGLEWVSVISGGSSTYYADSVKGRFTISRDNSKNTLYLQMNSLRAEDTAVYYCAKWRGNPTDYGMDVWGQGTTVTVSS |
| | | | SEQ ID NO: 27298 | SEQ ID NO: 31304 |
| iPS:436654 | 21-225_146C11 | NA | TCCTATGAACTGACTCAGCCACCCTCAGTGTCCGTGTCCCCAGGACAGACAGCCAGCATCACCTGCTCTGGAGATAAATTGGGGGATAAATATGCTTCCTGGTATCAGCAGAAGCCAGGCCAGTCCCCTGTGCTGGTCATCTATCAAGATAGCAAGCGGCCCTCAGGGATCCCTGAGCGATTCTCTGGCTCCAACTCTGGGAACACAGCCACTCTGACCATCAGCGGGATCCAGGCTATGGATGAGGCTGACTATTACTGTCAGGCCGTGGGACAGCAGCACTGTGTATTCGGCGGAGGGACCAAGCTGACCGTCCTA | GAGGTGCAACTGTTGGAGTCTGGGGGAGGCTTGGTACAGCCTGGGGGGTCCCTGAGACTCTCCTGTGCAGCCTCTGGAATCACCTTTAGCAGCTATGCCATGAGCTGGGTCCGCCAGGCTCCAGGGAAGGGCTGGAGTGGGTCTCAGTTATTAGTGGTGGTAGTAGCACATACTACGCAGACTCCGTGAAGGGCCGGTTCACCATCTCCAGAGACAATTCCAAGAACACGCTGTATCTGCAAATGAACAGCCTGAGAGCCGAGACACGGCCGTATATTACTGTGCGAAATGGCGAGTAACCCCACTGACTACGGTATGGACGTCTGGGGCCAAGGGACCACGGTCACCGTCCTCA |
| | | | SEQ ID NO: 27299 | SEQ ID NO: 31305 |

FIGURE 50
(Continued)

| | | | | |
|---|---|---|---|---|
| iPS:436658 | 21-225_146A2 | AA | SYELTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL<br><br>SEQ ID NO: 27300 | EVQLLESGGGLVQPGGSLRLSCAASGFTFSSYAMS WVRQAPGKGLEWVSVISGGGSSTYYADSVKGRFTI SRDNSKNTLYLQMNSLRAEDTAVYYCAKWRGNPT DYGMDVWGQGTTVTSS<br><br>SEQ ID NO: 31306 |
| | | NA | TCCTATGAGCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGGCTATGATGAGGCTGACTATT CGGGATCCCAGGTATGATGAGGCTGACTATT ACTGTCAGGCGTGGGACAGCAGCACTGTGGTA TTCGGCGGAGGGACCAAGCTGACCGTCCTA<br><br>SEQ ID NO: 27301 | GAGGTGCAACTGTTGGAGTCTGGGGGAGGCCTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTGGTGGTAGT AGCACATACTACGCAGACTCCGTGAAGGGCCGG TTCACCATCTCCAGAGACAATTCCAAGAACACGC TGCATCTGCAAATGAACAGCCTGAGAGCCGAGG ACACGGCCGTATATTACTGTGCGAAATGGCGAG GTAACCCACTGACTACGGTATGGACGTCTGGGG CCAAGGGACCACGGTCACCGTCTCCTCA<br><br>SEQ ID NO: 31307 |
| | | AA | SYELTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL<br><br>SEQ ID NO: 27302 | EVQLLESGGGLVQPGGSLRLSCAASGFTFSSYAMS WVRQAPGKGLEWVSVISGGGSSTYYADSVKGRFTI SRDNSKNTLHLQMNSLRAEDTAVYYCAKWRGNPT DYGMDVWGQGTTVTSS<br><br>SEQ ID NO: 31308 |

FIGURE 50
(Continued)

| | | | |
|---|---|---|---|
| iPS:436660 | 21-225_146D8 | NA | CAGTCTGTACTGACTCAGCCACCTCAACGTCTGGGACCCCGGCAGAGGGTCACCATCTCTTGTTCTGGAAGCAGCTCCTACATCGGAAGTAATACTGTAGACTGGTACCAGCAGCTCCCAGGAACGGCCCCAAACTCCTCATCTATAGTAATAATCAGCGGCCCTCAGGGGTCCCTGACCGATTCTCTGGCTCCAAGTCTGGCACCTCAGCTCCCTGCCATCAGTGGGCTCCAGTCTGAGGATGACAGCCTTATTATTACTGTCAGCATGGGATGACAGCCTTAATGGCGTGGTATTCGGCGGAGGGACCAAACTGACCGTCCTA | GAGGTGCAGCTGGTGGAGTCTGGGGGAGGCTTGGTACAGCCTGGGGGGGTCCCTGAGACTCTCCTGTGCAGCCTCTGGATTCACCTTCAGTAACTATAACATGAACTGGGTCCGCCAGGCTCCAGGGAAGGGGCTGGAGTGGGTTTCATACATTAGTAGAAGTAGTAATACCAAATACTATGTAGACTCTGTGAAGGGCCGATTCACCATCTCCAGAGACAATGCCAAGAACTCATTGTATCTGCAAATGAACAGCCTGAGAGACGAGGACACGGCTGTGTATTACTGTGCGAGAGATAGGAGTGGGAGTACGGGTACTTCTACTACTAGGGTTTGGGGCCAAGGGACCACGGTCACCGTCTCCTCA |
| | | | SEQ ID NO: 27303 | SEQ ID NO: 31309 |
| | | AA | QSVLTQPPSTSGTPGQRVTISCSGSSSYIGSNTVDWYQQLPGTAPKLLIYSNNQRPSGVPDRFSGSKSGTSASLAISGLQSEDEADYYCAAWDDSLNGVVFGGGTKLTVL | EVQLVESGGGLVQPGGSLRLSCAASGFTFSNYNMNWVRQAPGKGLEWVSYISRSSNTKYYVDSVKGRFTISRDNAKNSLYLQMNSLRDEDTAVYYCARDRSGSYGYFYYGLDVWGQGTTVTVSS |
| | | | SEQ ID NO: 27304 | SEQ ID NO: 31310 |
| iPS:436662 | 21-225_147D7 | NA | TCCTATGAGTTGACTCAGCCACCTCAGTGTCCGTGTCCCCAGGACAGACAGGCCAGCATCACCTGCTCTGGAGATAAATTGGGGGATAAATTTGCTTGCTTGGTATCAGCAGAAGCCAGGCCAGTCCCCTGTACTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACAGCAGGAACACCGCTGTCTTCGGAACTGGGACCAAGGTCACCGTCCTA | CAGGTGCAGCTGGTGCAGTCTGGGGCTGAGGTGAAGAAGCCTGGGGCCTCAGTGAAGGTCTCCTGCAAGGCTTCTGGATACACCTTCACCAGTTATGATATCAACTGGGTGCGACAGGCCACTGGACAAGGGCTTGAGTGGATGGGATGGATGAACCCTAATAGTGGTAACACAGGCTATGCACAGAAGTTCCAGGGCAGAGTCACCATGACCAGGAACACCTCCATAAGCACAGCCTATATGGAGCTGAGAAGCCTGAGATCTGAGGACACGCCCGTGTATTACTGTGCGAGAGCGGATATTGTATTAGTACCAGCTGCTATCCCTTATAATTACTACTTCGCTATGGACGTCTGGGGCCAAGGGACCACGGTCACCGTCTCCTCA |

FIGURE 50
(Continued)

| | | | | SEQ ID NO: 27305 | | SEQ ID NO: 31311 | |
|---|---|---|---|---|---|---|---|
| | | | AA | SYELTQPPSVSVSPGQTASITCSGDKLGDKFACW YQQKPGQSPVLVIYQDRKRPSGIPERFSGSNSGN TATLTISGTQAMDEADYYCQAWDRNTAVFGTG TKVTVL | | QVQLVQSGAEVKKPGASVKVSCKASGYTFTSYDIN WVRQATGQGLEWMGWMNPNSGNTGYAQKFQGR VTMTRNTSISTAYMELRSLRSEDTAVYYCARADIV LVPAAIPYNYFAMDVWGQGTTVTVSS | |
| | | | | SEQ ID NO: 27306 | | SEQ ID NO: 31312 | |
| iPS:436664 | 21-225_147E7 | | NA | TCCTATGAGCTGACTCAGCCACCCTCAGTGTC CGTGTCCCCAGGACAGACAGCCAGCATCACCT GCTCTGGAGATAAATTGGGGGACAAGTTTGCT TCCTGGTATCAGCAGAAGCCAGGCCAGTCCCC TGTGCTGGTCATCTATCAAGATAGGAAGCGCC CCTCAGGGATCCCGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCAAGCTGTGGTA TTCGGCGGAGGGACCAAGCTGACCGTCCTA | | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTAGTGGTGGTAGT AGTACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTTTTTTACTGTGCGAAATGGCGAGG TAACCCACTGACTACGCTATGGACGTCTGGGGC CAAGGGACCACGGTCACCGTCTCCTCA | |
| | | | | SEQ ID NO: 27307 | | SEQ ID NO: 31313 | |
| | | | AA | SYELTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL | | EVQLLESGGGLVQPGGSLRLSCAASGFTFSSYAMS WVRQAPGKGLEWVSVISGGGSSTYYADSVKGRFT LSRDNSKNTLYLQMNSLRAEDTAVFYCAKWRGNP TDYGMDVWGQGTTVSS | |
| | | | | SEQ ID NO: 27308 | | SEQ ID NO: 31314 | |

FIGURE 50
(Continued)

| | | | |
|---|---|---|---|
| iPS:436666 | 21-225_147B8 | NA | TCCTATGAACTGACTCAGCCACCCTCAGTGTCCGTGTCCCCAGGACAGACAGCCAGTATCACCTGCTCTGGAGATAAATTGGGGGATAAATATGTTTGCTGTATCAGCAGAAGCCAGGCCAGTCCCCTGAGCTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGGACAGTAACACTGTGTGGTATTCGGCGGAGGGACCAAGCTGACCGTCCTA<br>SEQ ID NO: 27309 | CAGGTGCAGCTGGTGCAGTCTGGGGCTGAGGTGAAGAAGCCTGGGGCCTCAGTGAAGGTCTCCTGCAAGGCTTCTGGATACACCTTCACCGACTACTATTTGCACTGGGTGCGACAGGCCCCTGGACAAGGGCTTGAGTGGATGGGATGGATCAACCCTAACAGTGGTGACACAAACTATGCACAGAAGTTTCAGGGCAGGGTCACCATGACCAGGGACACGTCCATCAGCACAGCCTACATGGAGCTGAGCAGGCTGAGATCTGAGACACGGCCGTGTATTACTGTGCGAGAGATCGGGACTCTGTTCGGGGAGTTACCCCTACTACTACTACTACGGTATGGACGTCTGGGGCCAAGGGACCACGGTCACCGTCTCCTCA<br>SEQ ID NO: 31315 |
| | | AA | SYELTQPPSVSVSPGQTASITCSGDKLGDKYVCWYQQKPGQSPELVIYQDRKRPSGIPERFSGSNSGNTATLTISGTQAMDEADYYCQAWGSNTAVVFGGGTKLTVL<br>SEQ ID NO: 27310 | QVQLVQSGAEVKKPGASVKVSCKASGYTFTDYYLHWVRQAPGQGLEWMGWINPNSGDTNYAQKFQGRVTMTRDTSISTAYMELSRLRSDDTAVYYCARDRDSGSSYPYYYYYGMDVWGQGTTVTVSS<br>SEQ ID NO: 31316 |
| iPS:436668 | 21-225_147B9 | NA | TCCTATGAGCTGACTCAGCCACCCTCAGTGTCCGTGTCCCCAGGACAGACAGCCAGCATCACCTGCTCTGGAGATAAATTGGGGGATAAATATGTTTCCTGGTATCAGCAGAAGCCAGGCCAGTCCCCTGTGCTGGTCATCTATCAAGATAGGAAGCGGCCCTCAGGGATCCCTGAGCGATTCTCTGGCTCCAACTCTGGGAACACAGCCACTCTGACCATCAGCGGGACCCTGGCTGTGGATGAGGCTGACTATTACTGTCTGTGGGGTGGGACAGCAGCACTTTTGTGCTATTCGGCGGAGGGACCAAGTTGACCGTCCTA | CAGGTGCAGTTGGTGGAGTCTGGGGGAGGCGTGGTCCAGCCTGGGAGGTCCCTGAGACTCTCCTGTGCAGGGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGTGACTACGGTCTACGGTGACCCCCCTACTACTACTACGGTATGGACGTCTGGGGCCAAGGGACCACGGTCACCGTCTCCTCA |

FIGURE 50
(Continued)

| | | | |
|---|---|---|---|
| iPS:436670 | 21-225_147D9 | AA | SEQ ID NO: 27311<br>SYELTQPPSVSVSPGQTASITCSGDKLGDKYVSW<br>YQQRPGQSPVLVIYQDRKRPSGIPERFSGSNSGN<br>TATLTISGTLAVDEADYYCLAWDSSTFVVFGGG<br>TKLTVL | SEQ ID NO: 31317<br>QVQLVESGGGVVQPGRSLRLSCAASGFTFSSYGMH<br>WVRQAPGKGLEWVAVIWYDGSNKYYADSVKGRF<br>TISRDNSKNTLYLQMNSLRAEDTAVYYCARDRDY<br>GDPPYYYYGMDVWGQGTTVTVSS |
| | | NA | SEQ ID NO: 27312<br>TCCTATGAGCTGACTCAGCCACCCTCAGTGTC<br>CGTGTCCCCAGGACAGACAGCCAGCATCACCT<br>CCTCTGGAGATAAATTGGGTAATAAATATGTT<br>TGCTGGTATCAGCAGAGGCCAGGCCAGTCCCC<br>TGTGCTGGTCATCTATCAAGATAGCAAGCGGC<br>CCTCAGGGATCCCTGAGCGATTCTCTGGCTCC<br>AACTCCGGGAACACAGCCACTCTGACCATCAG<br>CGGGACCCAGGCTGTGGACAGGAACACTTATGTG<br>ACTGTCAGGCGTGGACAGGAACACTTATGTG<br>GTGTTCGGCGGAGGGACCAAGCTGACCGTCCT<br>A | SEQ ID NO: 31318<br>CAGGTGCAGCTGGTGGTGGAGTCTGGGGGAGGCGTG<br>GTCCAGCCTGGGAGGTCCCTGAGACTCTCCTGTG<br>CAGCGTCTGGATTCACCTTCAGTAGCTATGGCAT<br>GCACTGGGTCCGCCAGGCTCCAGGCAAGGGGCT<br>GGAGTGGGTGGCAGATATATGGTTTGATGGCAGT<br>AATAAATACTATGTAGACTCCGTGAAGGACCGAT<br>TCACCATCTCCAGAGACAATTCCAAGAACACGCT<br>GTATCTGCAAATGAACAGCCTGAGAGCCGAGGA<br>CACGGCTGTTTATTACTGTGCGAGAGATCGGGTG<br>GAGGGTTCGGGGACTCCCTACTACTACTACGTA<br>TGGACGTCTGGGGCCAAGGGACCACGGTCACCG<br>TCTCCTCA |
| | | AA | SEQ ID NO: 27313<br>SYELTQPPSVSVSPGQTASITSSGDKLGNKYVCW<br>YQQRPGQSPVLVIYQDSKRPSGIPERFSGSNSGN<br>TATLTISGTQAMDEADYYCQAWDRNTYVFGG<br>GTKLTVL | SEQ ID NO: 31319<br>QVQLVESGGGVVQPGRSLRLSCAASGFTFSSYGMH<br>WVRQAPGKGLEWVADIWFDGSNKYYVDSVKDRF<br>TISRDNSKNTLYLQMNSLRAEDTAVYYCARDRVEG<br>SGTPYYYYGMDVWGQGTTVTVSS |
| | | | SEQ ID NO: 27314 | SEQ ID NO: 31320 |

FIGURE 50
(Continued)

| | | | |
|---|---|---|---|
| iPS:436672 | 21-225_147F9 | NA | TCCTATGAGCTGACTCAGCCACCCTCAGTGTCCGTGTCCCCAGGACAGAGCCAGCATCACCTGTTCTGGAGATGAATGGGGAATAAATATGCTTGCTGGTATCAGCAGAAGCCAGGCCAGTCCCCTGTGCTGGTCTGTCATCTATCAAGATAGCAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGCACAGCAGCACTGTGGTATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCTTCAGTACCTATGGCATGCACTGGGTCCGCCAGGCTCCAGGCAAGGGCTGGAGTGGGTGGCAGTTATATGGTATGGTGGAAGTGATAAAGACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGATTATTGTAGTGGTGGTACTTGTCCTTACTACTACTACGGTATGGACGTCTGGGGCCAAGGGACCACGGTCACCGTCTCCTCA |
| | | | SEQ ID NO: 27315 | SEQ ID NO: 31321 |
| | | AA | SYELTQPPSVSVSPGQTASITCSGDELGNKYACWYQQKPGQSPVLVIYQDSKRPSGIPERFSGSNSGNTATLTISGTQAMDEADYYCQAWHSSTVVFGGGTKLTVL | QVQLVESGGGVVQPGRSLRLSCAASGFTFSTYGMHWVRQAPGKGLEWVAVIWYGGSDKDYADSVKGRFTISRDISKNTLYLQMNSLRAEDTAVYYCARDRDYCSGGTCPYYYYGMDVWGQGTTVTVSS |
| | | | SEQ ID NO: 27316 | SEQ ID NO: 31322 |

FIGURE 50
(Continued)

| | | | |
|---|---|---|---|
| iPS:436674 | 21-225_147G9 | NA | TCCTATGAGCTGACTCAGCCACCCTCAGTGTC CGTGTCCCCAGGACAGAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAGGAAGCGGC CCTCAGGGATCCCTGAGCGATTCTCTGGCTCC AACTCTGGGAACACAGCCACTCTGACCATTAG CGGAACCCAGGCTATGGACGCACAGCAGTACTGTGTA ACTGTCAGGCGTGGCACAGCAGTACTGTGGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGGCAGTTATATGGTATGGTGAAGT GATAAAGACTATGCAGACTCCGTGAAGGGCCGA TTCACCATCTCCAGAGACACATTTCCAAGAACACGC TGTATCTGCAAATGAACAGCCTGAGAGCCGAGG ACACGGCTGTGTATTACTGTGCGAGAGATCGGGA TTATTGTAGTGGTGGTAGCTGCCCTTACTACTACT ACTACGGTATGGACGTCTGGGGCCAAGGGACCA CGGTCACCGTCTCCTCA |
| | | | SEQ ID NO: 27317 | SEQ ID NO: 31323 |
| | | AA | SYELTQPPSVSVSPGQTASITCSGDKLGDKYACW YQQKPGQSPVLVIYQDRKRPSGIPERFSGSNSGN TATLTISGTQAMDEADYYCQAWHSSTVFGGG TKLTVL | QVQLVESGGGVVQPGRSLRLSCAASGFTFSTYGMH WVRQAPGKGLEWVAVIWYGGSDKDYADSVKGRF TISRDISKNTLYLQMNSLRAEDTAVYYCARDRDYC SGGSCPYYYYYGMDVWGQGTTVTVSS |
| | | | SEQ ID NO: 27318 | SEQ ID NO: 31324 |

FIGURE 50
(Continued)

| | | | | |
|---|---|---|---|---|
| iPS:436676 | 21-225_147E11 | NA | TCCTATGAGCTGACTCAGCCACCCTCAGTGTCCGTGTCCCCAGGACAGACAGCCAGCATCACCTGCTCTGGAGATAAATTGGGGGATAAATATGCTTCCTGGTATCAGCAGAAGCCAGGCCAGTCCCCTGTGTTGGTCATCTATCAAGATAGCAAGCGGCCCTCAGGGATCCCTGAGCGATTCTCTGGCTCCAACTCTGGGAACACAGCCACTCTGACCATCAGCGGGATCCAGGCTATGGATGAGGCTGACTATTACTGTCAGGCCGTGGGACAGCAGCACTGTGTATTCGGCGGAGGGACCAAGCTGACCGTCCTA<br>SEQ ID NO: 27319 | GAGGTGCAACTGTTGGAGTCTGGGGGAGGCTTGGTACAGCCTGGGGGGTCCCTGAGACTCTCCTGTGCAGCCTCTGGATTCACCTTTAGCAACTATGTCATGAGCTGGGTCCGCCAGGCTCCAGGGAAGGGCTGGAGTGGGTCTCAGTTATTAGTGGTGGTAGTAGTACATACTACGCAGACTCCGTGAAGGGCCGGTTCACCATCTCCAGAGACAATGAACAGCCTGAGAGCCGAGGTGTATCTGCAAATGAACAGCCTGAGAGCCGAGGACACGGCCGTATATTACTGTGCGAAATGGCGAGGTAACCCCACTGACTACGGTATGACGTCTGGGGCCAAGGGACCACGGTCACCGTCTCCTCA<br>SEQ ID NO: 31325 |
| | | AA | SYELTQPPSVSVSPGQTASITCSGDKLGDKYASWYQQKPGQSPVLVIYQDSKRPSGIPERFSGSNSGNTATLTISGIQAMDEADYYCQAWDSSTVVFGGGTKLTVL<br>SEQ ID NO: 27320 | EVQLLESGGGLVQPGGSLRLSCAASGFTFSNYVMSWVRQAPGKGLEWVSVISGGSSTYYADSVKGRFTISRDNSKNTLYLQMNSLRAEDTAVYYCAKWRGNPTDYGMDVWGQGTTVTVSS<br>SEQ ID NO: 31326 |
| iPS:436678 | 21-225_147B12 | NA | TCCTATGAGCTGACTCAGCCACCCTCAGTGTCCGTGTCCCCAGGACAGACAGCCAGCATCACCTGCTCTGGAGATAAATTGGGGGATAAATATGCTTCCTGGTATCAGCAGAAGCCAGGCCAGTCCCCTGTGCTGGTGGTCATCTATCAAGATAGCAAGCGGCCCTCAGGGATCCCTGAGCGATTCTCTGGCTCCAACTCTGGGAACACAGCCACTCTGACCATCAGCGGGATCCAGGCTATGGATGAGGCTGACTATTACTGTCAGGCCGTGGGACAGCAGCACTGTGTATTCGGCGGAGGGACCAAGCTGACCGTCCTA<br>SEQ ID NO: 27321 | GAGGTGCAACTGTTGGAGTCTGGGGGAGGCTTGGTACAGCCTGGGGGGTCCCTGAGACTCTCCTGTGCAGCCTCTGGATTCACCTTTAGCAGTATGCCATGAGCTGGGTCCGCCAGGCTCCAGGGAAGGGCTGGAGTGGGTCTCAGTTATTAGTGGTGGTAGTAGCACATACTACGCAGACTCCGTGAAGGGCCGGTTCACCATCTCCAGAGACAATGAACAGCCTGAGAGCCGAGGACACGGCCGTATATTACTGTGCGAAATGGCGAGGTAACCCCACTGACTACGGTATGACGTCTGGGGCCAAGGGACCACGGTCACCGTCTCCTCA<br>SEQ ID NO: 31327 |

FIGURE 50
(Continued)

| | | | |
|---|---|---|---|
| iPS:436680 | 21-225_147H12 | AA | SYELTQPPSVSVSPGQTASITCSGDKLGDKYASWYQQKPGQSPVLVIYQDSKRPSGIPERFSGSNSGNAATLTISGIQAMDEADYYCQAWDSSTVVFGGGTKLTVL | EVQLLESGGGLVQPGGSLRLSCAASGFTFSSYAMSWVRQAPGKGLEWVSVISGGGSSTYYADSVKGRFTISRDNSKNTLYLQMNSLRAEDTAVYYCAKWRGNPTDYGMDVWGQGTTVTSS |
| | | | SEQ ID NO: 27322 | SEQ ID NO: 31328 |
| | | NA | CAGTCTGTGTTGACTCAGCCACCCTCAGCGTCTGGGACCCCGGGCAGAGGGTCACCATCTCTTGTTCTGGAAGCAGTCCAACATCGGAAGTTATGCTGTAAACTGGTATCAGCAGCTCCCAGGAACGGCCCCCAAACTCCTCATTTATAGTAATAATCAGCCCTCAGGGGTCCCTGACCGATTCTCTGGCTCCAAGTCTGGCACCTCAGCCTCCCTGGCCATCAGTGGGCTCCAGTCTGAAGGCATGGGATGACAGCCTGATTATTACTGTGCAGCTGTGATTCGAGAGATTGGGAATGGTCCGGTATTCGGCGGAGGGACCAAGCTGACCGTCCTA | CAGGTGCAGCTGCAGGAGTCGGGCCCAGGACTGGTGAAATCCTTCACAGACCCTGTCCCTCACCTGCGCTGTCTCTGGTGGCTCCATCAGCAGTGGTTATTACCACTGGAGCTGGATCCGCCAGCACCCAGGGAAGGGGCTGGAGTGGATTGGGTACATCTATTACAGTGGGAGCACCTACTACAACCCGTCCCTCAAGAGTCGAGTTACCATATCAGTTGACACGTCTAAGAACCAGTTCTCCCTGAAGCTGACCTCTGTGACTGCCGCGGACACGGCCGTGTATTACTGTGCGAGAGATTGGGGTGGCTACGATTGGAGTGGCGTGGTTCGACCCTGGGGCCAGGGAACCCTGGTCACCGTCTCCTCA |
| | | | SEQ ID NO: 27323 | SEQ ID NO: 31329 |
| | | AA | QSVLTQPPSASGTPGQRVTISCSGSSSNIGSYAVNWYQQLPGTAPKLLIYSNNHRPSGVPDRFSGSKSGTSASLAISGLQSEDEADYYCEAWDDSLNGPVFGGGTKLTVL | QVQLQESGPGLVNPSQTLSLTCAVSGGSISSGYYHWSWIRQHPGKGLEWIGYIYYSGSTYYNPSLKSRVTISVDTSKNQFSLKLTSVTAADTAVYYCARDWGGYDSSGWFDPWGQGTLVTVSS |
| | | | SEQ ID NO: 27324 | SEQ ID NO: 31330 |

FIGURE 50
(Continued)

| | | | |
|---|---|---|---|
| iPS:436682 | 21-225_146A8 | NA | CAGTCTGTGCTGACTCAGCCACCCTCAGCGTCTGGGACCCCCGGGCAGAGGTCACCATCTCTTGTTCTGGAAGCAGCTCCAACATCGGAAGTAATTCTATAAACTGGTACCAGCAGCTCCCAGGAACGGCCCCCAAACTCCTCATCTATAGTAATGATCAGCGGCCCTCAGGGGTCCCTGACCGATTCTCTGGCTCCAAGTCTGGCACCTCAGCCTCCCTGGCCATCAGTGGGCTCCAGTCTGGAGGATGACAGCCTGATTATTACTGTGCAGCATGGGATGACAGCCTGAACGGCGTGGTATTCGGCGGAGGGACCAAGCTGACCGTCCTA SEQ ID NO: 27325 | GAGGTGAAGCTGGTGGAGTCTGGGGGAGGCTTGGTACAGCCTGGGGAGTCCCTGAGACTCTCCTGTGTAGCCTCTGATTCACCTTCAGTAACTATAACATGAACTGGGTCCGCCAGGCTCCAGGGAAGGACTGGAGTGGGTTCATACATTAGTAGAAGTAGTAATACCAAATACTACGCAGACTCTGTGAGGGCCGATTCACCATCTCCAGAGACAATGCCAAGAATTCACTATATCTGCAAATGAACAGCCTGAGAGACGAGGACACGGCTGTGTATTACTGTGCGAGAGATAGGAGTGGGAGCTACGGGTACTTCTACTACTACGGTTTGGACGTCTGGGGCCAAGGGACCACGGTCACCGTCTCCTCA SEQ ID NO: 31331 |
| | | AA | QSVLTQPPSASGTPGQRVTISCSGSSSNIGSNSINWYQQLPRTAPKLLIYSNDQRPSGVPDRFSGSKSGTSASLAISGLQSEDEADYYCAAWDDSLNGVVFGGGTKLTVL SEQ ID NO: 27326 | EVKLVESGGGLVQPGESLRLSCVASGFTFSNYNMNWVRQAPGKGLEWVSYISRSSNTKYYADSVRGRFTISRDNAKNSLYLQMNSLRDEDTAVYYCARDRSGSYGYFYYYGLDVWGQGTTVTVSS SEQ ID NO: 31332 |
| iPS:436684 | 21-225_146B6 | NA | CAGTCTGTGCTGACTCAGCCACCCTCAGCGTCTGGGACCCCCGGGCAGAGGGTCACCATCTCTTGTTCTGGAAGCAGCTCCAACATCGGAAGTAATGCTGTAAACTGGTACCAGCAGCTCCCAGGAACGGCCCCCAAACTCCTCATCTATAGTAATAATCAGCGGCCCTCAGGGGTCCCTGACCGGTTCTCTGGCTCCAAGTCTGGCACCTCAGCCTCCCTGGCCATCAGTGGGCTCCAGTCTGAGGATGACAGCCTGATTATTACTGTGCAGCATGGGATGACAGCCTGAATGGCGTGGTATTCGGCGGAGGGACCAAGCTGACCGTCCTA SEQ ID NO: 27327 | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAACATGAACTGGGTCCGCCAGGCTCCAGGGAAGGGGCTGGAGTGGGTTTCATACATTAGTAGAAGTAGTAATACCAAACACTACGCAGACTCTGTGAAGGGCCGATTCACCATCTCCAGAGACAATGCCAAGAACTCACTGTATCTGCAAATGGACAGCCTGAGAGACGAGGACACGGCTGTGTATTACTGTGCGAGAGATACGGTTTGTGGGAGCTACGGGTACTTCTACTACTACGGTTTGGACGTCTGGGGCCAAGGGACCACGGTCACCGTCTCCTCA SEQ ID NO: 31333 |

FIGURE 50
(Continued)

| | | | |
|---|---|---|---|
| | | AA | QSVLTQPPSASGTPGQRVTISCSGSSSNIGSNAVN WYQQLPGTAPKLLIYSNNQRPSGVPDRFSGSKS GTSASLAISGLQSEDEADYYCAAWDDSLNGVVF GGGTKLTVL<br>SEQ ID NO: 27328 | EVQLVESGGGLVQPGGSLRLSCAASGFTFSSYNMN WVRQAPGKGLEWVSYISRSSNTKHYADSVKGRFTI SRDNAKNSLYLQMDSLRDEDTAVYYCARDRSGSY GYFYYYGLDVWGQGTTVTVSS<br>SEQ ID NO: 31334 |
| iPS:436686 | 21-225_148G6 | NA | TCCTATGAGCTGACTCAGCCACCCTCAGTGTC CGTGTCCCAGGACAGACAGCCAGCATCACCT GCTCTCTGAGATAAATTGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGGCTATGATGAGGCTGACTATT CGGGATCCAGGTCAGGCGTGGGACAGCAGCACTGTGTA ACTGTCAGGGCGTGGGACAGCAGCACTGTGTA TTCGGCGGAGGGACCAAGCTGACCGTCCTA<br>SEQ ID NO: 27329 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTGGTGGTAGT AGCACATACTACGCAGACTCCGTGAAGGGCCGG TTCACCATCTCCAGAGACACCAATTCCAAGAACATGC TGCATCTGCAAATGAACAGCCTGAGAGCCGAGAG ACACGGCCGTATATTACTGTGCAAATGGCGAG GTAACCCCACTGACTACGGTATGGACGTCTGGGG CCAAGGGACCACGGTCACCGTCTCCTCA<br>SEQ ID NO: 31335 |
| | | AA | SYELTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL<br>SEQ ID NO: 27330 | EVQLLESGGGLVQPGGSLRLSCAASGFTFSSYAMS WVRQAPGKGLEWVSVISGGGSSTYYADSVKGRFTI SRDNSKNMLHLQMNSLRAEDTAVYYCAKWRGNP TDYGMDVWGQGTTVTVSS<br>SEQ ID NO: 31336 |

FIGURE 50
(Continued)

| | | | | |
|---|---|---|---|---|
| iPS:436688 | 21-225_148C8 | NA | TCCTATGAGCTGACTCAGCCGCCCTCAGTGTC CGTGTCCCAGGACAGACAGCAGCCATCACCT GCTCTGGAGATAAATTGGGGATAAATATGTT TCCTGGTATCAGCAGAAGCCAGGCCAGTCCCC TATACTGGTCATCTATCAAGATAGGAAGCGGC CCTCAGGGACCCCTGAGCGATTCTCTGGCTCC AACTCTGGGAACACAGCCACTCTGACCATCAG CGGGACCCAGGCTATGGATGAGGCTGATTATT ACTGTCTGCGCTGGGACAGCAGCACTTTTGTG GTATTCGGCGGAGGGACCAAGTTGACCGTCCT A | SYELTQPPSVSVSPGQTASITCSGDKLGDKYVSW YQQKPGQSPILVIYQDRKRPSGIPERFSGSNSGN TATLTISGTQAMDEADYYCLRWDSSTFVFGGG TKLTVL |
| | | | SEQ ID NO: 27331 | SEQ ID NO: 27332 |
| | | AA | | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARDRDY GDPPYYYYGMDVWGQGTTVTVSS |
| | | | | SEQ ID NO: 31338 |
| iPS:436690 | 21-225_148A9 | NA | TCCTATGAGCTGACTCAGCCACCCTCAGTGTC CGTGTCCCAGGACAGACAGCAGCCATCACCT GTTCTGGAGATAAATTGGGGAATAAATATGT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGCACAGCAGCACTGTGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGGTGAAGT GATAAAGACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGA TTATTGTAGTGGTGGTACTTGTCCTTACTACTACT ACTACGGTATGGACGTCTGGGGCCAAGGGACCA CGGTCACCGTCTCCTCA |
| | | | SEQ ID NO: 27333 | SEQ ID NO: 31339 |

FIGURE 50
(Continued)

| | | | |
|---|---|---|---|
| iPS:436694 | | AA | SYELTQPPSVSVSPGQTASITCSGDKLGNKYVCW YQQKPGQSPVLVIYQDSKRPSGIPERFSGSNSGN TATLTISGTQAMDEADYYCQAWHSSTVFGGG TKLTVL<br>SEQ ID NO: 27334 | QVQLVESGGGVVQPGRSLRLSCAASGFTFSTYGMH WVRQAPGKGLEWVAVIWYGGSDKDYADSVKGRF TISRDISKNTLYLQMNSLRAEDTAVYYCARDRDYC SGGTCPYYYYGMDVWGQGTTVTVSS<br>SEQ ID NO: 31340 |
| 21-225_148G11 | | NA | TCCTATGAGCTGACTCAGCCACCCTCAGTGTC CGTGTCCCCAGGACAGACAGCCAGCATCACCT GCTCTGGAGATAAATTGGGGGATAAATTTGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGGTGGGACAGCAGCACTGTGGTA TTCGGCGGAGGGACCAAGCTGACCGTCCTA<br>SEQ ID NO: 27335 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATCCCAT GAGCTGGGTCCGCCAGGCTCCCGGGAAGGGCT GGAGTGGGTCTCAGTTATTAGTGGTGGTGGTAGT AGTGCATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCTCCTCA<br>SEQ ID NO: 31341 |
| | | AA | SYELTQPPSVSVSPGQTASITCSGDKLGDKFASW YQQKPGQSPVLVIYQDSKRPSGIPERFSGSNSGN TATLTISGIQAMDEADYYCQAWDSSTVVFGGGT KLTVL<br>SEQ ID NO: 27336 | EVQLLESGGGLVQPGGSLRLSCAASGFTFSSYPMS WVRQAPGKGLEWVSVISGGGSSAYYADSVKGRFTI SRDNSKNTLYLQMNSLRAEDTAVYYCAKWRGNPT DYGMDVWGQGTTVTVSS<br>SEQ ID NO: 31342 |

FIGURE 50
(Continued)

| | | | |
|---|---|---|---|
| iPS:436696 | 21-225_149A1 | NA | CAGTCTGTGCTGACTCAGCCACCTCAGCGTCTGGGACCCCGGGCAGAGGGTCACCATCTCTTGTTCTGGAAGCAGCTCCAACATCGGAAGTAATGCTGTAAACTGGTACCAGCAGCTCCCAGGAACGGCCCCCAAACTCCTCATCTATAGTAATAATCAGCGGCCCTCAGGGGTCCCTGACCGGTTCTCTGGCTCCAAGTCTGGCACCTCAGCTCTCCTGGCCATCAGTGGGCTCCAGTCTGAAGGATGACAGCCTGATTATTACTGTGCAGCATGGGACCCTGAATGGCGTGGTATTCGGCGGAGGGACCAAGCTGACCGTCCTA<br><br>SEQ ID NO: 27337 | GAGGTGCAGCTGGTGGAGTCTGGGGGAGGCTTGGTACAGCCTGGGGGGTCCCTGAGACTCTCCTGTGCAGCCTCTGGATTCACCTTCAGTAGCTATAACATGAACTGGGTCCGCCAGGCTCCAGGGAAGGGGCTGGAGTGGGTTTCATACATTAGTAGAAGTAGTAATACCAAACATTACGCAGACTCTGTGAAGGGCCGATTCACCATCTCCAGAGACAATGCCAAGAACTCACTGTATCTGCAAATGAACAGCCTGAGAGACGAGGACACGGCTGTGTATTACTGTGCGAGAGATAGGAGTGGGAGCTACGGGTACTTCTACTACGGTTTGGACGTCTGGGGCCAAGGGACCACGGTCACCGTCTCCTCA<br><br>SEQ ID NO: 31343 |
| | | AA | QSVLTQPPSASGTPGQRVTISCSGSSSNIGSSNAVNWYQQLPGTAPKLLIYSNNQRPSGVPDRFSGSKSGTSASLAISGLQSEDEADYYCAAWDDSLNGVVFGGGTKLTVL<br><br>SEQ ID NO: 27338 | EVQLVESGGGLVQPGGSLRLSCAASGFTFSSYNMNWVRQAPGKGLEWVSYISRSSNTKHYADSVKGRFTISRDNAKNSLYLQMNSLRDEDTAVYYCARDRSGSYGYFYYYGLDVWGQGTTVTVSS<br><br>SEQ ID NO: 31344 |
| iPS:436698 | 21-225_149B5 | NA | TCCTATGAACTGACTCAGCCACCCTCAGTGTCCGTGTCCCCAGGACAGACAGCCAGCATCACCTGCTCTGGATATAAATTGGGGTATAAATATGTTGCTTGGTATCAGCAGAAGCCAGGCCAGTCCCCTGTACTGGTCATCTTTCAAAATAACCAGCGGCCCTCAGGGATCCCTGAGCGATTCTCTGGCTCCAACTCTGGGAACACAGCCTCTCTGACCATCAGCGGGACCCAGGCTATGGATGAGGCTGACTATTACTGTCAGGCGTGGGACAGCAGCACTGTGGTATTCGGCGGAGGGACCAAGCTGACCGTCCTA<br><br>SEQ ID NO: 27339 | GAGGTGCAGCTGGTGGAGTCTGGGGGAGGCTTGGTCCAGCCTGGGGGGTCCCTGAGACTCTCCTGTGCAGCCTCTGGATTCACCTTTAGTGGCTATTGGATGAACTGGGTCCGCCAGGCTCCAGGGAAGGGGCTGGAGTGGGTGGCCAACATAAAGCAAGATGGAAGTGAGAAATACTATGTGGACTCTGTGAAGGGCCGATTCACCATCTCCAGAGACAACGCCAAGAATTCACTGTATCTGCAAATGAACAGCCTGAGAGCCGAGGACACGGCTGTGTATTACTGTGCGAGAGGGATGTATAGCAGTGGCTGGTACGTCTTTGACTACTGGGGCCAGGGAACCCTGGTCACCGTCTCCTCA<br><br>SEQ ID NO: 31345 |

FIGURE 50
(Continued)

| | | | | |
|---|---|---|---|---|
| iPS:436700 | 21-225_149C7 | AA | SYELTQPPSVSVSPGQTASITCSGYKLGYKYVCWYQQKPGQSPVLVIFQNNQRPSGIPERFSGSNSGNTASLTISGTQAMDEADYYCQAWDSSTVFGGGTKLTVL | EVQLVESGGGLVQPGGSLRLSCAASGFTFSGYWMNWVRQAPGKGLEWVANIKQDGSEKYYVDSVKGRFTISRDNAKNSLYLQMNSLRAEDTAVYYCARGMYSSGWYVFDYWGQGTLVTVSS |
| | | | SEQ ID NO: 27340 | SEQ ID NO: 31346 |
| | | NA | TCCTATGAGCTGACTCAGCCACCCTCAGTGTCCGTGTCCCCAGGACAGACAGCCAGCATCACCTGCTCTGGAAATAAATTGGGGATAAAATATGCTTCCTGGTATCAGCAGAAGCCAGGCCAGTCCCCTGTGCTGGTCATCTATCAAGATAGCAAGCGGCCCTCAGGGATCCCTGAGCGATTCTCTGGCTCCAAGTCTGGGAACACAGGCTATGATGAGGCTGACTATTACTGTCAGGCGTGGGACAGCAGCACTGTGGTATTCGGCGGAGGGACCAAGCTGACCGTCCCA | GAGGTGCAACTGTTGGAGTCTGGGGGAGGCTTGGTACAGCCTGGGGGGTCCCTGAGACTCTCCTGTGCAGCCTCTGGATTCACCTTTAGCAGCTATATGCCATGAGCTGGGTCCGCCAGGCTCCAGGGAAGGGGCTGGAGTGGGTCTCAGTTATTAGTGGTGGTGGTAGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAATGGCGAGGTAACCCCACTGACTACGGTATGGACGTCTGGGGCCAAGGGACCACGGTCACCGTCTCCTCA |
| | | | SEQ ID NO: 27341 | SEQ ID NO: 31347 |
| | | AA | SYELTQPPSVSVSPGQTASITCSGNKLGDKYASWYQQKPGQSPVLVIYQDSKRPSGIPERFSGSGSKSGNTATLTISGIQAMDEADYYCQAWDSSTVFGGGTKLTVP | EVQLLESGGGLVQPGGSLRLSCAASGFTFSSYAMSWVRQAPGKGLEWVSVISGGGSSTYYADSVKGRFTISRDNSKNTLYLQMNSLRAEDTAVYYCAKWRGNPTDYGMDVWGQGTTVTVSS |
| | | | SEQ ID NO: 27342 | SEQ ID NO: 31348 |

FIGURE 50
(Continued)

| | | | | |
|---|---|---|---|---|
| iPS:436702 | 21-225_149E8 | NA | CAGGCTGTGTGACTCAGCCGTCTTCCCTCT GCATCTCCTGGAGCATCAGCCAGTCTCACCTG CACCTTACGCAGTGGCATCACTGTTACTACT ATAGGATATACTGGTACCAGCAGAAGCCAGG GAGTCCTCCCAGTTTCTCTGCGTACACATC AGACTCTCAGATAAACACCAGGGCTCTGGAGTCC CCAGCCGCTTCTCTGGATCCAAAGATGCTTCG GCCAATGCAGGGATTTTATTCATCTCTGGGCT CCAGTCTGAGGATGAGGCTGACTATTACTGTA TGATTTGGCACAGCAGCGCTTGGGTGTTCGGC GGAGGGACCAAGCTGACCGTCCTA | GAGGTGCAGCTGGTGGAGTCTGGGGGAGGCTG GTCAAGCCTGGGGGGTCCCTGAGACTCTCCTGTG CAGCCTCTGGATTCACCTTCAGTAGTAGCAT GAACTGGGTCCGCCAGGCTCCAGGAAGGGCT GGAGTGGGTCTCAGCCATTAGTAGTACTGGTAGT TACATATATTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGGACGGCAGTG GCTGGTACTGGGGTGGTTCGACCCCTGGGCCAGG GAACCCTGGTCACCGTCTCCTCA |
| | | | SEQ ID NO: 27343 | SEQ ID NO: 31349 |
| | | AA | QAVSTQPSSLSASPGASASLTCTLRSGITVTTYRI YWYQQKPGSPPQFLLRYTSDSDKHQGSGVPSRF SGSKDASANAGILFISGLQSEDEADYYCMIWHSS AWVFGGGTKLTVL | EVQLVESGGGLVKPGGSLRLSCAASGFTFSSYSMN WVRRAPGKGLEWVSAISSTGSYIYYADSVKGRFTIS RDNAKNSLYLQMNSLRAEDTAVYYCARTAVAGTG WFDPWGQGTLVTVSS |
| | | | SEQ ID NO: 27344 | SEQ ID NO: 31350 |
| iPS:436704 | 21-225_149C10 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTGGTCTCAGTTATCAAGATAACAAGCGG CCTCAGGGATCCCTGAGCGATTCTCTGGCTCC AACTCTGGGAACACAGCCACTCTGACCATCGG CGGGATCCAGGCTATGATGAGGCTGACTATT ACTGTCAGGCGGTGGGACAGCAGCACTGTGTA TTCGGCGGAGGGACCAAGCTGACCGTCCTA | GAGGTGCAACTGTTGGAGTCTGGGGGAGGCTG GTACAGCCTGGGGGGTCCCTGAGATTCTCCTGTG CAGCCTCTGGATTCACCTTTAGCAGCCACGCCAT GAGCTGGGTCCGCCAGGCTCCAGGGAAGGGGCT GGAGTGGGTCTCAGTTATAAGTGGAGGTGGTAGT AGCACATATTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCACTGACTACGGTATGACGTCTGGGG CCAAGGGACCACGGTCACCGTCTCCTCA |
| | | | SEQ ID NO: 27345 | SEQ ID NO: 31351 |

FIGURE 50
(Continued)

| | | AA | SYELTQPPSVSVSPGQTASITCSGDKLGDKYASW YQQKPGQSPVLVIYQDNKRPSGIPERFSGSNSGN TATLTIGGIQAMDEADYYCQAWDSSTVVFGGGT KLTVL | EVQLLESGGGLVQPGGSLRFSCAASGFTFSSHAMS WVRQAPGKGLEWVSVISGGGSSTYYADSVKGRFTI SRDNSKNTLYLQMNSLRAEDTAVYYCAKWRGNPT DYGMDVWGQGTTVTVSS |
| --- | --- | --- | --- | --- |
| | | | SEQ ID NO: 27346 | SEQ ID NO: 31352 |
| iPS:436706 | 21-225_149A11 | NA | TCCTATGAACTGACTCAGCCGCCCTCAGTGTC CGTGTCCCCAGGACAGACAGCCAGCATCACCT GCTCTGGAGATAAATTGGGAGCCAGCATATGTT TCCTGGTATCAGCAGAAGCCAGGCCAGTCCCC TGTGCTGGTCATCTATCAAGATAGCAGGCGGC CCTCAGGGATCCCTGAGCGATTCTCTGGCTCC AACTCTGGGAACACAGCCACTCTGACCATCAG CGGGACCCAGGCTATGGGACAGCAGCTGACTATT ACTGTCTGGCGTGGACAGCAGACACTTTTGTG GTCTTCGGCGGAGGGACCAAGTTGACCGTCCT A | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGTGA CTACGGTGACCCCCCTACTACTACTACTACGGT ATGGACGTCTGGGGCCAAGGGACCACGGTCACC GTCTCCTCA |
| | | | SEQ ID NO: 27347 | SEQ ID NO: 31353 |
| | | AA | SYELTQPPSVSVSPGQTASITCSGDKLGNKYVSW YQQKPGQSPVLVIYQDSRRPSGIPERFSGSNSGN TATLTISGTQAMDEADYYCLAWDSSTFVVFGGG TKLTVL | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARDRDY GDPPYYYYGMDVWGQGTTVTVSS |
| | | | SEQ ID NO: 27348 | SEQ ID NO: 31354 |

FIGURE 50
(Continued)

| | | | |
|---|---|---|---|
| iPS:436708 | 21-225_150D3 | NA | TCCTATGAGCTGACTCAGCCACCCTCAGTGTC CGTGTCCCCAGGACAGACAGCCAGCATCACCT GCTCTGGAGATGAATTGGGAATAAATATGCT TGCTGGTATCAGCAGAAGCCAGGCCAGTCCCC TGTGCTGGTCATCTATCAAGATAACAAGCGGC CCTCAGGGATCCCTGAGCGATTCTCTGGCTCC AGCTCTGGGAACACAGCCACTCTGACCATCAG CGGACCCAGGTATGAGGCTGACTATTT ACTGTCAGGCGTGCACAGCAGCACTGTGGTA TTCGGCGGAGGGACCAAGCTGACCGTCCTA<br><br>SEQ ID NO: 27349 | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGGCAGTTATATGGTATGGTGAAGT AATAAAGACTATGCAGACTCCGTGAAGGGCCGA TTCACCATCTCCAGAGACAATTCCAAGAACACGC TGTATCTGCAAATGAACAGTTTGAGAGCCGAGGA CACGGCTGTGTATTACTGTGCGAGAGATCGGAT TATTGTAGTGGTGGTACCTGCCCTTACTACTACTA CTACGGTATGGACGTCTGGGGCCAAGGGACCAC GGTCACCGTCTCCTCA<br><br>SEQ ID NO: 31355 |
| | | AA | SYELTQPPSVSVSPGQTASITCSGDELGNKYACW YQQKPGQSPVLVIYQDNKRPSGIPERFSGSSSGN TATLTISGTQAMDEADYYCQAWHSSTVFGGG TKLTVL<br><br>SEQ ID NO: 27350 | QVQLVESGGGVVQPGRSLRLSCAASGFTFSTYGMH WVRQAPGKGLEWVAVIWYGGSNKDYADSVKGRF TISRDNSKNTLYLQMNSLRAEDTAVYYCARDRDY CSGGTCPYYYYYGMDVWGQGTTVTVSS<br><br>SEQ ID NO: 31356 |

FIGURE 50
(Continued)

| | | | |
|---|---|---|---|
| iPS:436710 | 21-225_150F6 | NA | TCCTATGAGCTGACTCAGCCACCCTCAGTGTC CGTGTCCCAGGACAGACAGCCAGCATCACCT GCTCTGGAGATAAATTGGGGATAAATATGCT TCCTGGTATCAGCAGAAGCCAGGCCAGTCCC TGTGCTGGTCATCTGTCAAGATAGCAAGCGC CCTCAGGGATCCCTGAGCGATTCTCTGGCTCC AACTCTGGAAACACAGCCACTCTGACCATCAG CGGGATCCAGGCTATGGATGAGGCTGACTATT GCTGTCAGGCGTGGGACAGCAGCACTGTGTA TTCGGCGGAGGGACCAAGCTGACCGTCCTA | GAGGTGCAACTGTTGGAGTCTGGGGGAGGCTTG GTACAGCCTGGGGGTCCCTGAGACTCTCCTGTG CAGCCTCTGATTCACCTTTAGCAGCTATGCCAT GAGCTGGGTCCGCCAGGCTCCAGGGAAGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGACGTCTGGGG CCAAGGGACCACGGTCACCGTCCTCTCA |
| | | | SEQ ID NO: 27351 | SEQ ID NO: 31357 |
| | | AA | SYELTQPPSVSVSPGQTASITCSGDKLGDKYASW YQQKPGQSPVLVICQDSKRPSGIPERFSGSNSGN TATLTISGIQAMDEADYCCQAWDSSTVVFGGGT KLTVL | EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVTVSS |
| | | | SEQ ID NO: 27352 | SEQ ID NO: 31358 |
| iPS:436712 | 21-225_150F9 | NA | CAGTCTGTGCTGACTCAGCCACCCTCAGCGTC TGGGACCCCCGGGCAGAGGGTCACCATCTCT GTTCTGGAAGCAGCTCCAACATGGAAGTAAT GCTGTAAACTGGTACCAGCAGCTCCCAGGAAC GGCCCCCAAACTCCTCATCTATCATGTCTCT AGCGGCCCTCAAGTCTGGCACCTCAGCCTCCTGC GGCTCCAAGTCTGGCACCTCAGTCTGAGGATGACAGCTG CATCAGTGGGCTCCAGTCTGAGGATGACAGCTG ATTATTTCTGTGCAGCATGGGCGGAGGAGCT AATGGCGTGGTATTCGGCGGAGGGACCAAGCT GACCGTCCTA | GAGATGCAGCTGGTGGAGTCTGGGGGAGGCTTG GTACAGCCTGGGGGGTCCCTGAGACTCTCCTGTG CAGCCTCTGGATTCACCTTCAGTAGCTATAACAT GAACTGGGTCCGCCAGTTCCAGGGAAGGGGCT GGAGTGGGGTTCATACATTAGTAGAAGTAGTAAT ACCAAACACTACGCAGACTCTGTGAAGGGCCGA TTCACCATCTCCAGAGACAATGCCAAGAACTCAC TGTATCTGCAAATGAACAGCCTGAGAGACGAGG ACACGGCTGTGTATTACTGTGCGAGAGATAGGAG TGGGAGCTACGGTACTTCTACTACTACGGTTTG GACGTCTGGGGCCAAGGGACCACGGTCACCGTC TCCTCA |
| | | | SEQ ID NO: 27353 | SEQ ID NO: 31359 |

FIGURE 50
(Continued)

| | | | |
|---|---|---|---|
| | | AA | QSVLTQPPSASGTPGQRVTISCSGSSSNIGSNAVN WYQQLPGTAPKLLIYSNSQRPSGVPDRFSGSKSG TSASLAISGLQSEDEADYFCAAWDDSLNGVVFG GGTKLTVL<br>SEQ ID NO: 27354 | EMQLVESGGGLVQPGGSLRLSCAASGFTFSSYNMN WVRQVPGKGLEWVSYISRSSNTKHYADSVKGRFTI SRDNAKNSLYLQMNSLRDEDTAVYYCARDRSGSY GYFYYYGLDVWGQGTTVTVSS<br>SEQ ID NO: 31360 |
| iPS:436714 | 21-225_150H11 | NA | TCCTATGAGCTGACTCAGCCACCCTCAGTGTC CGTGTCCCCAGGACAGACAGCCAGCATCACCT GCTCTCTGAGATAAATTGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGGCCACTCTGACCATCAG CGGGATCCAGGCTATGATGAGGCTGACTTTT ACTGTCAGGCGTGGGACAGCAGCACTGTGGTA TTCGGCGGAGGGACCAAGCTGACCGTCCTA<br>SEQ ID NO: 27355 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATATGCCAT GAGCTGGGTCCGCCAGGCTCCAGGGAAGGGGCT GGAGTGGGTCTCAATTATTAGTGTGGTGTGTAGT AGCACATACTACGCAGACTCCGTGAAGGGCCGG TTCACCATCTCCAGAGACACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCTCCTCA<br>SEQ ID NO: 31361 |
| | | AA | SYELTQPPSVSVSPGQTASITCSGDKLGDKYASW YQQKPGQSPVLVIYQDSKRPSGIPERFSGSNSGN TATLTISGIQAMDEADFYCQAWDSSTVFGGGT KLTVL<br>SEQ ID NO: 27356 | EVQLLESGGGLVQPGGSLRLSCAASGFTFSTYAMS WVRQAPGKGLEWVSIISGGGSSTYYADSVKGRFTI SRDNSKNTLYLQMNSLRAEDTAVYYCAKWRGNPT DYGMDVWGQGTTVTVSS<br>SEQ ID NO: 31362 |

FIGURE 50
(Continued)

| | | | |
|---|---|---|---|
| iPS:436716 | 21-225_151F3 | NA | TCTTATGAGCTGACTCAGCCACCCTCAGTGTC CGTGTCCCCAGGACAGAGACAGCCAGCATCACCT GCTCTGGAGATAAATTGGGGGATAAATATGTT TGCTGGTATCAGCAGAAGCCAGGCCAGTCCCC TGTGCTGGTCATCTATCAAGATCGGCAAGGC CCTCAGGGATCCCTGAGCGATTCTCTGGCTCC AACTCTGGGAACACAGCCACTCTGACCATCAG CGGAACCCAGGCTATGAGGCTGACTATT ACTGTCAGGGTGCACAGCAGCACTGTGTA TTCGGCGGAGGGACCAAGCTGACCGTCCTA SEQ ID NO: 27357 | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGGCAGTTATATGGTATGGTGAAGT AATACAGACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGA TTATTGTAGTGTACTAGCTGCCCTTACTACTACT ACTACGGTATGGACGTCTGGGGCCAAGGGACCA CGGTCACCGTCTCCTCA SEQ ID NO: 31363 |
| | | AA | SYELTQPPSVSVSPGQTASITCSGDKLGDKYVCW YQQKPGQSPVLVIYQDRKRPSGIPERFSGSNSGN TATLTISGTQAMDEADYYCQAWHSSTVFGGG TKLTVL SEQ ID NO: 27358 | QVQLVESGGGVVQPGRSLRLSCAASGFTFSTYGMH WVRQAPGKGLEWVAVIWYGGSNTDYADSVKGRF TISRDISKNTLYLQMNSLRAEDTAVYYCARDRDYC SGTSCPYYYYGMDVWGQGTTVTVSS SEQ ID NO: 31364 |

FIGURE 50
(Continued)

| | | | | |
|---|---|---|---|---|
| iPS:436718 | 21-225_151H5 | NA | TCCTATGAGCTGACTCAGCCACCCTCAGTGTC CGTGTCCCCAGGACAGACAGCCAGCATGCCT GCTCTGGAGATAAATTGGGGATAAATATGCT TCCTGGTATCAACAGAAGCCAGGCCAGTCCCC TGTGCTGGTCATCTATCAAGATAGCAAGCGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGTA TTCGGCGGAGGGACCAAGCTGACCGTCCTA SEQ ID NO: 27359 | GAGGTGCAACTGTTGGAGTCTGGGGGAGGCTTG GTACAGCCTGGGGGGTCCCTGAGACTCTCCTGTG CAGCCTCTGGATTCACCTTCAGCAGCTATGCCAT GAGCTGGGTCCGCCAGGCTCCAGGGAAGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAG ACACGGCCGTATATTACTGTGCGAAATGGCGAG GTAACCCCACTGACTACGTATGACGTCTGGGG CCAAGGGACCACGGTCACCGTCTCCTCA SEQ ID NO: 31365 |
| | | AA | SYELTQPPSVSVSPGQTASIACSGDKLGDKYASW YQQKPGQSPVLVIYQDSKRPSGIPERFSGSNSGN TATLTISGIQAMDEADYYCQAWDSSTVFGGGT KLTVL SEQ ID NO: 27360 | EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVTVSS SEQ ID NO: 31366 |
| iPS:436720 | 21-225_151H6 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATACCAAGCGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTTATGTC TTCGGAACTGGGACCAAGGTCACCGTCCTA SEQ ID NO: 27361 | CAGGTGCAGCTGCAGTGGTGGAGTCTGGGGGAGGCGTG GTCCAGCCTGGGAGGTCCCTGAGACTCTCCTGTG CAGCGTCTGGATTCACCTTCAGTGACTGATGCAT GCACTGGGTCCGCCAGGCTCCAGGCAAGGGCT GGAGTGGGTGGCACTTATATGGTATGATGGAAGT AATAAATACTATGCAGACTCCGTGAAGGGCCGA TTCACCATCTCCAGAGACAATTCCAAGAACAGC TGTATCTACAAATGAACAGCCTGAGAGCCGAG ACACGGCTGTGTATTACTGTGCGAGAGATGACCG ATCTTGTAGTAGAACCAGCTGCCCTTACTACTAC TACTACGGTTTGGACGTCTGGGGCCAAGGGACCA CGGTCATCGTCTCCTCA SEQ ID NO: 31367 |

FIGURE 50
(Continued)

| | | | |
|---|---|---|---|
| iPS:436722 | 21-225_151H7 | AA | SYELTQPPSVSVSPGQTASITCSGDKLGDKYACW YQQKPGQSPVLVIYQDTKRPSGIPERFSGSNSGN TATLTISGTQAMDEADYYCQAWDSSTYVFGTGT KVTVL<br>SEQ ID NO: 27362 | QVQLVESGGGVVQPGRSLRLSCAASGFTFSDYGM HWVRQAPGKGLEWVALIWYDGSNKYYADSVKGR FTISRDNSKNTLYLQMNSLRAEDTAVYYCARDDRS CSRTSCPYYYYGLDVWGQGTTVISS<br>SEQ ID NO: 31368 |
| | | NA | TCCTATGACCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGTA TTCGGCGGAGGGACCAAGCTGACCGTCCTA<br>SEQ ID NO: 27363 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTTATTAGTGGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCCTCCTCA<br>SEQ ID NO: 31369 |
| | | AA | SYDLTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL<br>SEQ ID NO: 27364 | EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVSS<br>SEQ ID NO: 31370 |

FIGURE 50
(Continued)

| | | | | |
|---|---|---|---|---|
| iPS:436724 | 21-225_151B9 | NA | TCCTATGAGCTGACTCAGCCACCCTCAGTGTC CGTGTCCCCAGGACAGACAGCCAGCATGCCT GCTCTGGAGATAAATTGGGGGATAAATATGCT TCCTGGTATCAACAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGTA TTCGGCGGAGGGACCAAGCTGACCGTCCTA | GAGGTGCAACTGTTGGAGTCTGGGGGAGGCTTG GTACAGCCTGGGGGGTCCCTGAGACTCTCCTGTG CAGCCCTCTGGATTCACCTTCAGCAGCTATGCCAT GAGCTGGGTCCGCCAGGCTCCAGGGAAGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGGAG GTAACCCCACTGACTACGGTATGACGTCTGGGG CCAAGGGACCACGGTCACCGTCCTCTCA |
| | | | SEQ ID NO: 27365 | SEQ ID NO: 31371 |
| | | AA | SYELTQPPSVSVSPGQTASIACSGDNLGDKYASW YQQKPGQSPVLVIYQDSKRPSGIPERFSGSNSGN TATLTISGIQAMDEADYYCQAWDSSTVVFGGGT KLTVL | EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVTVSS |
| | | | SEQ ID NO: 27366 | SEQ ID NO: 31372 |
| iPS:436726 | 21-225_152G5 | NA | TCCTATGAGATGACTCAGCCACCCTCAGTGTC CGTGTCCCCAGGACAGACAGCCAGCATCACCT GCTCTGGAGATAAATTGGGGGATAAATATGCT TGCTGGTATCAACAGAAGCCAGGCCAGTCCCC TGTGCTGGTCGTCATCTATCAAGATTCCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGTGGGACAGCAGCACTTATGTC TTCGGAACTGGGACCAAGGTCACCGTCCTA | CAGGTGCAGCTGCAGTGGTGGAGTCTGGGGCGTG GTCCAGCCTGGGAGGTCCCTGAGACTCTCCTGTG CAGCGTCTGGATTCACCTTCAGTGACTGACTATGGCAT GCACTGGGTCCGCCAGGCTCCAGGCAAGGGCT GGAGTGGGTGGCACTTATATGGTATGATGGAAGT AATAAATACTATGCAGACTCCGTGAAGGGCCGA TTCACCATCTCCAGAGACAATTCCAAGAACAGC TGTATCTACAAATGAACAGCCTGAGAGCCGAGG ACACGGCTGTGTATTACTGTGCGAGAGATGACCG ATCTTGTAGTAGAACCAGCTGCCTTACTACTAC TACTACGGTTTGGACGTCTGGGGCCAAGGGACCA CGGTCATCGTCCTCA |
| | | | SEQ ID NO: 27367 | SEQ ID NO: 31373 |

FIGURE 50
(Continued)

| | | AA | SYEMTQPPSVSVSPGQTAIITCSGDKLGDKYAC WYQQKPGQSPVLVIYQDSKRPSGIPERFSGSNSG NTATLTISGTQAMDEADYYCQAWDSSTYVFGT GTKVTVL<br><br>SEQ ID NO: 27368 | QVQLVESGGGVVQPGRSLRLSCAASGFTFSDYGM HWVRQAPGKGLEWVALIWYDGSNKYYADSVKGR FTISRDNSKNTLYLQMNSLRAEDTAVYYCARDDRS CSRTSCPYYYYGLDVWGQGTTVISS<br><br>SEQ ID NO: 31374 |
|---|---|---|---|---|
| iPS:436728 | 21-225_152G6 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTCTGGATGAGGCTGACTATT ACTGTCAGGCGTGGGACAACAGCACTGTGGTA TTCGGCGCGAGGGACCAAGCTGACCGTCCTA<br><br>SEQ ID NO: 27369 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTTATTAGTGGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCTCCTCA<br><br>SEQ ID NO: 31375 |
| | | AA | SYELTQPPSVSVSPGQTASITCSGDKLGDKYASW YQQKPGQSPVLVIYQDSKRPSGIPERFSGSNSGN TATLTISGIQALDEADYYCQAWDNSTVVFGGGT KLTVL<br><br>SEQ ID NO: 27370 | EVQLLESGGGLVQPGGSLRLSCAASGFTFSSYAMS WVRQAPGKGLEWVSVISGGGSSTYYADSVKGRFTI SRDNSKNTLYLQMNSLRAEDTAVYYCAKWRGNPT DYGMDVWGQGTTVTSS<br><br>SEQ ID NO: 31376 |

FIGURE 50
(Continued)

| | | | | |
|---|---|---|---|---|
| iPS:436730 | 21-225_152D7 | NA | TCCTATGAGCTGACTCAGCCACCCTCAGTGTC CGTGTCCCCAGGACAGACAGCCAGCATCACCT GCTCTGGGAGATAAATTGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGTA TTCGGCGGAGGGACCAAGCTGACCGTCCTA | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTTATTAGTGGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGGAG GTAACCCCACTGACTCCGTATGACGTCTGGGG CCAAGGGACCACGGTCACCGTCTCCTCA |
| | | | SEQ ID NO: 27371 | SEQ ID NO: 31377 |
| | | AA | SYELTQPPSVSVSPGQTASITCSGDKLGDKYASW YQQKPGQSPVLVIYQDSKRPSGIPERFSGSNSGN TATLTISGIQAMDEADYYCQAWDSSTVVFGGGT KLTVL | EVQLLESGGGLVQPGGSLRLSCAASGFTFSSYAMS WVRQAPGKGLEWVSVISGGGSSTYYADSVKGRFTI SRDNSKNTLYLQMNSLRAEDTAVYYCAKWRGNPT DSGMDVWGQGTTVTVSS |
| | | | SEQ ID NO: 27372 | SEQ ID NO: 31378 |
| iPS:436732 | 21-225_152B12 | NA | TCCTATGAGCTGACTCAGCCACCCTCAGTGTC CGTGTCCCCAGGACAGACAGCCAGCATCACCT GCTCTGGGAGATAAATTGGGGAAATAAATATGCT TGCTGGTATCAGCAGAAGCCAGGCCAGTCCCC TGTGCTGGTCGTCATCTATCAAGATACCAAGCGC CCTCAGGGATCCCTGAGCGATTCTCTGGCTCC AACTCTGGGAACACAGCCACTCTGACCATCAG CGGGACCCAGGCTATGGACAGCAGCACTTATGTC ACTGTCAGGGCGTGGGACCAAGGTCACCGTCCTA TTCGGAACTGGGACCAAGGTCACCGTCCTA | CAGGTGCAGGTGGTGGAGTCTGGGGGAGGCGTG GTCCAGCCTGGGAGGTCCCTGAGACTCTCCTGTG CAGCGTCTGGATTCACCTTCAGTGACTGACTGGCAT GCACTGGGTCCGCCAGGCTCCAGGCAAGGGCT GGAGTGGGTGGCAGTTATATGCAGTTATGGAAGT AATAAATACTATGCAGACTCCGTGAAGGGCCGA TTCACCATCTCCAGAGACAATTCCAAGAACACGC TGTATCTACAAATGAACAGCCTGAGAGCCGAGG ACACGGCTGTGTATTACTGTGCGAGAGATGACCG ATCTTGTAGTAGTACCAGCTGCCCTTACTACTAC TACTACGGTTTGGACGTCTGGGGCCAAGGGACCA CGGTCACCGTCTCCTCA |
| | | | SEQ ID NO: 27373 | SEQ ID NO: 31379 |

FIGURE 50
(Continued)

| | | | |
|---|---|---|---|
| iPS:436734 | 21-225_153A8 | AA | SYELTQPPSVSVSPGQTASITCSGDKLGNKYACW YQQKPGQSPVLVIYQDTKRPSGIPERFSGSNSGN TATLTISGTQAMDEADYYCQAWDSSTYVFGTGT KVTVL<br>SEQ ID NO: 27374 | QVQVVESGGGVVQPGRSLRLSCAASGFTFSDYGM HWVRQAPGKGLEWVAVIWYDGSNKYYADSVKGR FTISRDNSKNTLYLQMNSLRAEDTAVYYCARDDRS CSSTSCPYYYYYGLDVWGQGTTVTVSS<br>SEQ ID NO: 31380 |
| | | NA | TCCTATGAGCTGACTCAGCCACCCTCAGTGTC CGTGTCCCCAGGGCAGACAGCCAGCATCACCT GCTCTGGAGATAAATTGGGGATAAATATGCT TGCTGGTATCAGCAGAAGCCAGGCCAGTCCC TGTGCTGGTCATCTATCAAGATACCAAGCGGC CCTCAGGGATCCCTGAGCGATTCTCTGGCTCC AACTCTGGGAACACAGGCTATGAGGCTGACTATT CGGGACCCAGGTCAGGCGTGGGACAGCAGCACTTATGTC ACTGTCAGGGCGTGGGACCAAGGTCACCGTCCTA TTCGGAACTGGGACCAAGGTCACCGTCCTA | CAGGTGCAGCTGATGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGCT GGAGTGGGTGGCACTTATATGGTATGGATGGAAGT AATAAATACTATGCAGACTCCGTGAAGGGCCGA TTCACCATCTCCAGAGACAATTCCAAGAACACGC TTTATCTACAAATGAACAGCCTGAGAGCCGAGG ACACGGCTGTGTATTACTGTGCGAGAGATGACCG ATCTTGTAGTAGAACCAGCTGCCCTTACTACTAC TACTACGGTTTGGACGTCTGGGGCCAAGGACCA CGGTCATCGTCTCCTCA<br>SEQ ID NO: 31381 |
| | | AA | SYELTQPPSVSVSPGQTASITCSGDKLGDKYACW YQQKPGQSPVLVIYQDTKRPSGIPERFSGSNSGN TATLTISGTQAMDEADYYCQAWDSSTYVFGTGT KVTVL<br>SEQ ID NO: 27376 | QVQLMESGGGVVQPGRSLRLSCAASGFTFSDYGM HWVRQAPGKGLEWVALIWYDGSNKYYADSVKGR FTISRDNSKNTLYLQMNSLRAEDTAVYYCARDDRS CSRTSCPYYYYYGLDVWGQGTTVIVSS<br>SEQ ID NO: 31382 |

FIGURE 50
(Continued)

| | | | | | |
|---|---|---|---|---|---|
| iPS:436736 | 21-225_153E8 | NA | TCCTATGAGCTGACTCAGCCACCCTCAGTGTCCGTGTCCCCAGGACAGACAGCCAGCATCACCTGCTCTGGAAGTAAATTGGGTAATAAATATGTTTGCTGGTATCAGCAGAAGCCAGGCCAGTCCCCTGTACTGGTCATCTATCAAGATAACAAGCGGCCCTCAGGGATCCCTGAGCGATTCTCTGGCTCCAACTCCGGAAACACAGCCACTCTGACCATCAGCGGGACCCAGGCTATGGATGAGGCTGGCTATTACTGTCAGGCGTGGGACAGCAGCACTACTGTGATATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCCTCAGTAGTAACTATGGCATGCACTGGGTCCGCCAGGCTCCAGGCAAGGGCTGGAGTGGGTGGCAGTTATATGTTTGATGGCAGTAATAAATACTATGTTGACTCCGTGAAGGACCGATTCACCATCTCCAGAGACAATTCCAAGAACACGCTATATCTGCAAATGAACAGCCTGAGAGCCGAAGACACGGCTGTGTATTACTGTGCGAGAGATCGGGTGGAGGGTTCGGGGACTCCCTACTACTACGGTATGGACGTCTGGGGCCAAGGGACCACGGTCACCGTCTCCTCA | |
| | | AA | SYELTQPPSVSVSPGQTASITCSGSKLGNKYVCWYQQRPGQSPVLVIYQDNKRPSGIPERFSGSNSGNTATLTISGTQAMDEAGYYCQAWDSSTYVIFGGGTKLTVL | QVQLVESGGGVVQPGRSLRLSCAASGFTLSSNYGMHWVRQAPGKGLEWVAVIWFDGSNKYYVDSVKDRFTISRDNSKNTLYLQMNSLRAEDTAVYYCARDRVEGSGTPYYYYGMDVWGQGTTVTVSS | |
| | | | SEQ ID NO: 27377 | SEQ ID NO: 31383 | |
| iPS:436738 | 21-225_153D9 | NA | TCCTATGAGCTGACTCAGCCACCCTCAGTGTCCGTGTCCCCAGGACAGACAGCGAGCATCACCTGCTCTGGAGATAAATTGGGGGATAAATATGCTTGTAGTGGTATCAGCAGAAGCCAGGCCAGTCCCCCTGTACTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACACCAGTACTACTGTGGTATTCGGCGGAGGGACCAAGGTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCGTCAGTAGTTACTATGGCATGCACTGGGTCCGCCAGGCTCCAGGCAAGGGCTGGAGTGGGTGGCAGTTATATGGTATGGTGAAGTAATAAAGACTATGCGAGACTCCGTGAAGGGCCGATTCACCATCTCCAAATGAACAGCTGAGAACACGCTGTATCTGCAAATGAACAGCCTGAGAGCCGAGGACACGGCTGTGTATTACTGTGCGAGAGATCGGGATTATTGTAGTGGTGGTAGCGTGTCCTTACTACTACTACTAGGGTATGGACGTCTGGGGCCAAGGGACCACGGTCACCGTCTCCTCA | |

SEQ ID NO: 27378 · SEQ ID NO: 31384

FIGURE 50
(Continued)

| | | | SEQ ID NO: 27379 | SEQ ID NO: 31385 |
|---|---|---|---|---|
| | | AA | SYELTQPPSVSVSPGQTASITCSGDKLGDKYACW YQQKPGQSPVLVIYQDRKRPSGIPERFSGSNSGN TATLTISGTQAMDEADYYCQAWHSSTVFGGG TKVTVL | QVQLVESGGGVVQPGRSLRLSCAASGFTVSTYGM HWVRQAPGKGLEWVAVIWYGGSNKDYADSVKGR FTISRDISKNTLYLQMNSLRAEDTAVYYCARDRDY CSGGSCPYYYYGMDVWGQGTTVTVSS |
| | | | SEQ ID NO: 27380 | SEQ ID NO: 31386 |
| iPS:436740 | 21-225_154C3 | NA | TCCTATGAGCTGACTCAGCCACCCTCAGTGTC CGTGTCCCCAGGACAGACAGCCAGCATCACCT GCTCTGGAGATAAATTGGGGGATAAATATGTT TGCTGGTATCAGCAGAAGCCAGGCCAGTCCCC TGTGTTGGTCATCTATCAAGATAGGAAGCGGC CCTCAGGGATCCCTGAGCGATTCTCTGGCTCC AACTCTGGGAACACAGCCACTCTGACCATCAC CGGAACCCAGGCTATGGATGAGGCTGACTATT ACTGTCAGGCGTGGCACAGCAGCACTGTGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTA CAGCGTCTGGATTCACCTTCAGTAGTACCTATGGCAT GCACTGGGTCCGCCAGGCTCCAGGCAAGGGGCT GGAGTGGGTGGCAGTTGTATGGTATGGTGGAAAT AATAAAGACTATGCAGACTCCGTGAAGGGCCGA TTCACCATCTCCAGAGACAATTCCAAGAACACAC TGTATCTGCAAATGAACAGCCTGAGAGCCGAGG ACACGGCTGTGTATTACTGTGCGAGAGATCGGGA TTATTGTAGTGGTGGTAGCTGCCCTTACTACTACT ACTACGGTATGGACGTCTGGGGCCAAGGGACCA CGGTCACCGTCTCCTCA |
| | | | SEQ ID NO: 27381 | SEQ ID NO: 31387 |
| | | AA | SYELTQPPSVSVSPGQTASITCSGDKLGDKYVCW YQQKPGQSPVLVIYQDRKRPSGIPERFSGSNSGN TATLTITGTQAMDEADYYCQAWHSSTVFGGG TKLTVL | QVQLVESGGGVVQPGRSLRLSCTASGFTFSTYGMH WVRQAPGKGLEWVAVVWYGGNNKDYADSVKGR FTISRDISKNTLYLQMNSLRAEDTAVYYCARDRDY CSGGSCPYYYYGMDVWGQGTTVTVSS |
| | | | SEQ ID NO: 27382 | SEQ ID NO: 31388 |

FIGURE 50
(Continued)

| | | | | |
|---|---|---|---|---|
| iPS:436742 | 21-225_154C4 | NA | TCCTATGAGCTGACTCAGCCACCCTCAGTGTC CGTGTCCCCAGGACAGACAGCCAGAATCACCT GCTCTGGAGATAAATTGGGGATAAATATGCT TCCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGGTA TTCGGCGGAGGGACCAAGCTGACCGTCCTA<br><br>SEQ ID NO: 27383 | GAGGTGCAACTGTTGGAGTCTGGGGGAGGCTTG ATACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGACGTCTGGGG CCAAGGGACCACGGTCACCGTCTCCTCA<br><br>SEQ ID NO: 31389 |
| | | AA | SYELTQPPSVSVSPGQTARITCSGDKLGDKYASW YQQKPGQSPVLVIYQDSKRPSGIPERFSGSNSGN TATLTISGIQAMDEADYYCQAWDSSTVVFGGGT KLTVL<br><br>SEQ ID NO: 27384 | EVQLLESGGGLIQPGGSLRLSCAASGFTFSSYAMSW VRQAPGKGLEWVSVISGGGSSTYYADSVKGRFTIS RDNSKNTLYLQMNSLRAEDTAVYYCAKWRGNPT DYGMDVWGQGTTVTVSS<br><br>SEQ ID NO: 31390 |
| iPS:436744 | 21-225_154F4 | NA | TCCTATGAGCTGACTCAGCCACCCTCAGTGTC CGTGTCCCCAGGACAGACAGCCAGCATCACCT GCTCTGGAGATAAATTGGGGAAATAATATGTT TGTTGGTATCAGCAGAAGCCAGGCCAGTCCCC TGTGGAAGTCATCTATAAAGATAGTAAGCGGC CCTCAGGGATCCCTGAGCGATTCTCTGGCTCC AATTCTGGGAACACAGCCACTCTGACCATCAG CGGGACCCAGGCTATGGATGAGGCTGACTATT ACTGTCAGGCGTGGGACACAGTACTTAGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCATTGGGTCCGCCAGGCTCCAGGCAAGGGCT GGAGTGGGTGGCAGTTATATGGTATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAGATTC CTATTGTAGTGGTACCAGCGCCCTACTACTAC TACTACGGTATGGACGTCTGGGGCCAAGGGACC ACGGTCACCGTCTCCTCA |

FIGURE 50
(Continued)

| | | | | |
|---|---|---|---|---|
| iPS:436746 | 21-225_154E10 | AA | SEQ ID NO: 27385<br>SYELTQPPSVSVSPGQTASITCSGDKLGNKYVCW<br>YQQKPGQSPVEVIYKDSKRPSGIPERFSGSNSGN<br>TGTLTISGTQAMDEADYYCQAWDNSTLVFGGG<br>TKLTVL<br>SEQ ID NO: 27386 | SEQ ID NO: 31391<br>QVQLVESGGVVQPGRSLRLSCAASGFTFSSYGMH<br>WVRQAPGKGLEWVAVIWYDGSNKYADSVKGRF<br>TISRDNSKNTLYLQMNSLRAEDTAVYYCAREDSYC<br>SGTSCPYYYYYGMDVWGQGTTVTVSS<br>SEQ ID NO: 31392 |
| | | NA | SEQ ID NO: 27387 | GAGGTGCAACTGTTGGAGTCTGGGGGAGGCTTG<br>GTACAGCCTGGGGGGTCCCTGAGACTCTCCTGTG<br>CAGCCTCTGGATTCACCTTTAGCAGCTATGCCAT<br>GAGCTGGGTCCGCCAGGCTCCAGGGAAGGGGCT<br>GGAGTGGGTCTCAGTTATTAGTGGTGGTGGTAGT<br>AGCACATACTACGCAGACTCCGTGAAGGGCCGG<br>TTCACCATCTCCAGAGACAATTCCAAGAACACGC<br>TGTATCTGCAAATGAACAGCCTGAGAGCCGAGG<br>ACACGGCCGTATATTACTGTGCGAAATGGGCAG<br>GTAACCCACTGACTACGGTATGACGTCTGGGG<br>CCAAGGGACCACGGTCACCGTCTCCTCA<br>SEQ ID NO: 31393 |
| | | AA | SEQ ID NO: 27388<br>SYELTQPPSVSVSPGQTASITCSGDKLGDKYASW<br>YQQKPGQSPVLVIYQDSKRPSGIPERFSGSNSGN<br>TATLTISGIQAMDEADYYCQAWDNSTVVFGGGT<br>KLTVL | EVQLLESGGGLVQPGGSLRLSCAASGFTFSSYAMS<br>WVRQAPGKGLEWVSVISGGGSSTYYADSVKGRFTI<br>SRDNSKNTLYLQMNSLRAEDTAVYYCAKWRGNPT<br>DYGMDVWGQGTTVTVSS<br>SEQ ID NO: 31394 |

FIGURE 50
(Continued)

| iPS:436748 | 21-225_154D11 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAAGAAGCGGC CCTCAGGGATCCCTGAGCGATTCTCTGGCTCC AACTCTGGGAACATAGCCACTCTGACCATCAG CGGGACCCAAGGCTATGAGGATGAGGCTGACTATT ACTGTCAGGCCGTGGCACAGCAGTATTGTGTA TTCGGCGGAGGGACCAAGCTGACCGTCCTA SEQ ID NO: 27389 | CAGGTGCAGCTGGTGGAGTCTGGGGGAGGGGTG GTCCAGCCTGGGAGGTCCCTGAGACTCTCCTGTG CAGCGTCTGGATTCAACGTCAGTACCTATGGCAT GCACTGGGTCCGCCAGGCTCCAGGCAAGGGCT GGAGTGGGTGGCAGTTATATGGTATGGTGAAGT AATAAAGACTATGCAGACTCTGTGAAGGGCGA TTCACCATCTCCAGAGACACAGTTCCAAGAACACGC TGTATCTGCAAATGAACAGCCTGAGAGCCGAGG ACACGGCTGTGTATTACTGTGCGAGAGATCGGA TTATTGTAGTTGGTGGTAGTTGCCCTTACTACTACT ACTACGGTATGGACGTCTGGGGCCAAGGGACCA CGGTCACCGTCTCCTCA SEQ ID NO: 31395 |
| | | AA | SYELTQPPSVSVSPGQTASITCSGDKLGDKYACW YQQKPGQSPVLVIYQDKKRPSGIPERFSGSNSGNI ATLTISGTQAMDEADYYCQAWHSSIVFGGGTK LTVL SEQ ID NO: 27390 | QVQLVESGGGVVQPGRSLRLSCAASGFNVSTYGM HWVRQAPGKGLEWVAVIWYGGSNKDYADSVKGR FTISRDSSKNTLYLQMNSLRAEDTAVYYCARDRDY CSGGSCPYYYYYGMDVWGQGTTVTVSS SEQ ID NO: 31396 |

FIGURE 50
(Continued)

| | | | |
|---|---|---|---|
| iPS:436750 | 21-225_154G12 | NA | CAGTCTGTACTGACTCAGCCACCCTCAGCGTC TGGGACCCCCGGGCAGAGGGTCACCATCTCT GTTCTGGAAGCAGCTCCAACATCGGAAATAAT GCTGTAAGCTGGTATCAGCAGCTCCCAGGAAC GGCCCCAAACTCCTCATCTATAGTAATGATC ACCGGCCCTCAGGGGTCCCTGACCGATTCTCT GGCTCCAAGTCTGGCACCTCAGCTCCCTGGC CATCAGTGGGCTCCAGTCTGGAGGATGACAGCTG ATTATTACTGTGCAGCATGGGATGACAGCCTG AAGGGGTCGGTATTCGGCGGAGGGACCAAGC TGACCGTCCTA <br> SEQ ID NO: 27391 | CAGGTGCAGCTGCAGGAGTCGGGCCCAGGACTG GTGAATCCTTCACAGACCCTGTCCCTCACCTGCG GTGTCTCTGGTGGCTCCATCAGCAGTGGTTATTA CTACTGGAGCTGGATCCGCCAGCACCCAGGGAA GGGCCTGGAGTGGATTGGGTACATCTATTATAGT GGGAGCACTTACTACAACCCGTCCCTCAAGAGTC GAGTTTCCATATCATTAGACACGCCTAAGAACCA GTTCTCCCTGAAGCTGACCTCTGTGACTGCCGCG GACACGGCCGTGTATTACTGTGCGAGAGATTGGG GTGGCTACGATTCGAGTGGCTGGTTCGACCCCTG GGGCCAGGGAACCCTGGTCACCGTCTCCTCA <br> SEQ ID NO: 31397 |
| | | AA | QSVLTQPPSASGTPGQRVTISCSGSSSNIGNNAVS WYQQLPGTAPKLLIYSNDHRPSGVPDRFSGSKS GTSASLAISGLQSEDEADYYCAAWDDSLKGPVF GGGTKLTVL <br> SEQ ID NO: 27392 | QVQLQESGPGLVNPSQTLSLTCGVSGGSISSGYYY WSWIRQHPGKGLEWIGYIYYSGSTYYNPSLKSRVSI SLDTPKNQFSLKLTSVTAADTAVYYCARDWGGYD SSGWFDPWGQGTLVTVSS <br> SEQ ID NO: 31398 |
| iPS:436752 | 21-225_155H1 | NA | CAGTCTGTGCTGACGCAGCCGCCCTCAGTGTC TGGGGCCCCAGGGCAGAGGGTCACCATCTCCT GCACTGGGAGCAGCTCCAATATCGGGGCAGGT TATGATGTACACTGGTACCAGCAGCTTCCAGG AACAGCCCCCAAACTCCTCATCTATGGTAACA GCAATCGGCCCTCAGGGGTCCCTGACCGATTC TCTGGCTCCAAGTCTGGCACCTCAGCTCTCT GGCCATCACTGGCCTCCAGGCTGAGGATGAGG CTGATTATTACTGCGCAGTCCTATGACAGCAGC CTGAGTGGTCCTGTGATATTCGGCGGAGGGAC CAAGCTGACCGTCCTA <br> SEQ ID NO: 27393 | GAGGTGCAGCTAGTGCAGTCTGGAGCAGAGGTG AAAAAGCCCGGGGAGTCTCTGAAGATCTCCTGTA AGGGTTCTGGATACAGCTTTACCAGCTACTGGAT CGGCTGGGTGCGCCAGATGCCCGGGAAAGGCCT GGAGTGGATGGGGCTCATCTATCCTGGTGCTCT GATACCAGATACAGCCCGTCCTTCCAAGGCCAGG TCACCATCTCAGCCGACAAGTCCATCAGCACCGC CTACCTGCAGTGGAGCAGCCTGAAGGCCTGGA CACCGCCATGTATTACTGTGCGAGACAGGCCATA GCAAGTCGAGGGAGGTACTACTACTACGGTATG GACGTCTGGGCCAAGGGACCACGGTCACCGTC TCCTCA <br> SEQ ID NO: 31399 |

FIGURE 50
(Continued)

| | | | |
|---|---|---|---|
| iPS:436754 | 21-225_155G3 | AA | QSVLTQPPSVSGAPGQRVTISCTGSSSNIGAGYDVHWYQQLPGTAPKLLIYGNSNRPSGVPDRFSGSKSGTSASLAITGLQAEDEADYHCQSYDSSLSGPVIFGGGTKLTVL<br><br>SEQ ID NO: 27394 | EVQLVQSGAEVKKPGESLKISCKGSGYSFTSYWIGWVRQMPGKGLEWMGLIYPGASDTRYSPSFQGQVTISADKSISTAYLQWSSLKASDTAMYYCARQAIASRGRYYYYGMDVWGQGTTVTVSS<br><br>SEQ ID NO: 31400 |
| | | NA | TCCTATGAGCTGACTCAGCCACCCTCAGTGTCCGTGTCCCCAGGACAGACAGCCAGCATCACCTGCTCTGGAGATAAAGTTGGGGGATAAATATGTTTGCTGGTATCAGCAGAAGCCAGGCCAGTCCCCTATGTTGTGATCTATCAAGATAGTAAGCGGCCCTCAGGGATCCCTGAGCGATTCTCTGGCTCCAACTCTGGGAACACAGGGCCACTCTGACCATCAGCGGGACCCAGGCTGTGGGACAATAGTATTTATGTCACTGTCAGGCGTGGGACCAAGGTCACCGTCCTA<br><br>SEQ ID NO: 27395 | CAGGTGCAGCTGGTGGTGGAGTCTGGGGGAGGCGTGGTCCAGCCTGGGAGGTCCCTGAGACTCTCCTGTCAGCCTCTGGATTCACCTTCAGTAGCTATGGCATGCACTGGGTCCGCCAGGCTCCAGGCAAGGGGCTGGAGTGGGTGGCAGTTATATCATATGATGGAAGTAATAAATACTATGCAGACTCCGTGAAGGGCCGATTCACCATCTCCAGAGACAACGCCAAGAACACGCTGTATCTGCAAATGAACAGCCTGAGAGCTGAGGACACGGCTGTGTATTACTGTGCGAGAGATACGGAGAGATGGCTACCATACTCCTACGGTATGGACGTCTGGGGCCAAGGGACCACGGTCACCGTCTCCTCA<br><br>SEQ ID NO: 31401 |
| | | AA | SYELTQPPSVSVSPGQTASITCSGDKLGDKYVCWYQQKPGQSPMLVIYQDSKRPSGIPERFSGSNSGNTATLTISGTQAMDEADYYCQAWDNSIYVFGTGTKVTVL<br><br>SEQ ID NO: 27396 | QVQLVESGGGVVQPGRSLRLSCTASGFTFSSYGMHWVRQAPGKGLEWVAVISYDGSNKYYADSVKGRFTISRDNSKNTLYLQMNSLRAEDTAVYYCARDTERWLPYSYGMDVWGQGTTVTVSS<br><br>SEQ ID NO: 31402 |

FIGURE 50
(Continued)

| | | | |
|---|---|---|---|
| iPS:436756 | 21-225_146A10 | NA | TCCTATGAGCTGACTCAGCCACCCTCAGTGTC CGTGTCCCCAGGACAGACAGCCAGCATCACCT GCTCTGGAGATAAATTGGGGGATAAATATGTT TGCTGGTATCAGCAGAAGCCAGGCCAGTCCCC TGTGCTGGTCATCTTTCAAGATAGAAAGCGGC CCTCAGGGATCCCTGAGCGATTCTCTGGCTCC AACTCTGGGAACACAGCCACTCTGACCATCAG CGGAACCCAGGCTATGGGACAGCAGCACTGTGGTG ACTGTCAGGCGTGGGACAGCAGCACTGTGGTG TTCGGCGGAGGGACCAAAGTTACCGTCCTA<br><br>SEQ ID NO: 27397 | CAGGTGCAGCTGGAGGAGTCTGGGGGAGGCGTG GTCCAGCCTGGGAGGTCCCTGAGACTCTCCTGTG CAGCGTCTGGATTCACCTTCAGTGGCTATGGCAT GCACTGGGTCCGCCAGGCTCCAGGCAAGGGGCT GGAGTGGATGACACTTATACGGTATGATGGAAG CGATAAAAACTATGCAGACTCCGTGAAGGGCCG ATTCACCATCTCCAGAGACAACTCCAAGAACACG CTGTATCTGCAAATGAACAGCCTGAGAGCCGAG GACACGGCTGTGTATTACTGTGCGAGAGATCGGG TTTTTGTAGTAGTACCAGCTGCCTCTCTTACTAC TACTACTACGGTATGGACGTCTGGGGCCAAGGG ACCACGGTCACCGTCCTCA<br><br>SEQ ID NO: 31403 |
| | | AA | SYELTQPPSVSVSPGQTASITCSGDKLGDKYVCW YQQKPGQSPVLVIFQDRKRPSGIPERFSGSNSGN TATLTISGTQAMDEADYYCQAWDSSTVFGGG TKVTVL<br><br>SEQ ID NO: 27398 | QVQLEESGGGVVQPGRSLRLSCAASGFTFSGYGMH WVRQAPGKGLEWMTLIRYDGSDKNYADSVKGRF TISRDNSKNTLYLQMNSLRAEDTAVYYCARDRVFC SSTSCLSYYYYYGMDVWGQGTTVTVSS<br><br>SEQ ID NO: 31404 |

FIGURE 50
(Continued)

| | | | |
|---|---|---|---|
| iPS:436758 | 21-225_155C10 | NA | TCCTATGAGCTGACTCAGCCACCCTCAGTGTC CGTGTCCCCAGGACAGACAGTCAGCATCACCT GCTCTGGATATCAGCAGACAGATAAATATGTT CCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGATCCAGGCTATGGATGAGGCTGACTATT ACTGTCAGGCGTGGGACAGCAGCACTGTGTA TTCGGCGGAGGGACCAAGCTGACCGTCCTA <br><br>SEQ ID NO: 27399 <br><br>SYELTQPPSVSVSPGQTVSITCSGDKLGDKYVSW YQQKPGQSPVLVIYQDSKRPSGIPERFSGSNSGN TATLTISGIQAMDEADYYCQAWDSSTVVFGGGT KLTVL <br><br>SEQ ID NO: 27400 | GAGGTGCAACTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGACGTCTGGGG CCAAGGGACCACGGTCACCGTCTCCTCA <br><br>SEQ ID NO: 31405 <br><br>EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVTVSS <br><br>SEQ ID NO: 31406 |
| iPS:436760 | 21-225_155E10 | NA | TCCTATGAGCTGACTCAGCCGCCCTCAGTGTC CGTGTCCCCAGGACAGACAGCCAGCATCACCT GCTCTGGAGATAAATTGGGGGATAAATATGTT CCTGGTATCAGCAGAAGCCAGGCCAGTCCCC TGTGCTGGTCATCTATCAAGATAGGAAGCGGC CCTCAGGGACCCTGAGCGATTCTCTGGCTCC AACTCTGGGAACACAGCCACTCTGACCATCAG CGGGACCCAGGCTATGGATGAGGCTGACTATT ACTGTCTGTCGGCGTGGGACAGCAGCACTTTGTG GTATTCGGCGGAGGGACCAAGTTGACCGTCCT A <br><br>SEQ ID NO: 27401 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGTGA CTACGGTGACCCCCTACTACTACTACTACGGT ATGGACGTCTGGGGCCAAGGGACCACGGTCACC GTCTCCTCA <br><br>SEQ ID NO: 31407 |

FIGURE 50
(Continued)

| | | | | |
|---|---|---|---|---|
| iPS:436762 | 21-225_156H2 | AA | SYELTQPPSVSVSPGQTASITCSGDKLGDKYVSW YQQKPGQSPVLVIYQDRKRPSGTPERFSGSNSGN TATLTISGTQAMDEADYYCLAWDSSTFVVFGGG TKLTVL | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARDRDY GDPPYYYYGMDVWGQGTTVTVSS |
| | | | SEQ ID NO: 27402 | SEQ ID NO: 31408 |
| | | NA | CAGTCTGTGGTGACTCAGCCACCCTCAGCGTC TGGGACCCCCGGGCAGAGGGTCACCATCTCTT GTTCTGGAAGCAGCTCCAACATCGGAAGTAAT ACTGTAAATTGGTACCAGCAGCTCCCAGGAAC GGCCCCCAAACTCCTCATCTATAGTAGTAATC AGCGGCCCTCAGGGGTCCCTGACCGATTGTCT GGCTCCAAGTCTGGCACCTCAGCCTCCCTGGC CATCAGTGGGCTCCAGTCTGCAGCATGGGATGACAGCCTG ATTATTACTGTGCAGCATGGGATGACAGCCTG AATGGCGTGGTATTCGGCGGAGGGACCAAGG TGACCGTCCTA | GAGGTGCAGCTGGTGGAGTCTGGGGGAGGCTTG ATACAGCCTGGGGGGTCCCTGAGACTCTCCTGTG CAGCCCTCTGGATTCACCTTCAGTAGCTATGGCCAT GAACTGGGTCCGCCAGGCTCCAGGGAAGGGCT GGAGTGGGTTCATACATTAGTAGAAGTAGTAAT ACCAAATACTACGCAGACTCTGTGAAGGGCCGA TTCACCATCTCCAGAGACAATGCCAAGAACTCAC TGTATCTGCAAATGAACAGCCTGAGAGACGAGG ACACGGCTGTGTATTACTGTGCGAGAGATAGGAG TGGGAGCTACGGGTACTTCTACTACTACGGTATG GACGTCTGGGGCCAAGGGACCACGGTCACCGTC TCCTCA |
| | | | SEQ ID NO: 27403 | SEQ ID NO: 31409 |
| | | AA | QSVVTQPPSASGTPGQRVTISCSGSSSNIGSNTVN WYQQLPGTAPKLLIYSSNQRPSGVPDRLSGKSG TSASLAISGLQSEDEADYYCAAWDDSLNGVVFG GGTKVTVL | EVQLVESGGGLIQPGGSLRLSCAASGFTFSNYNMN WVRQAPGKGLEWVSYISRSSNTKYYADSVKGRFTI SRDNAKNSLYLQMNSLRDEDTAVYYCARDRSGSY GYFYYGMDVWGQGTTVTVSS |
| | | | SEQ ID NO: 27404 | SEQ ID NO: 31410 |

FIGURE 50
(Continued)

| | | NA | TCCTATGACCTGACTCAGCCACCCTCAGTGTCCGTGTCCCCAGGACAGAGCCAGCATCACCTGCTCTGGAGATAAATTGGGGGATAAATATGTTTGCTGGTATCAGCAGAAGCCAGGCCAGTCCCCTGTGCTGGTCATCTATCAAGATAGTAAGCGGCCCTCAGGGATCCCTGAGCGATTCTCTGGCTCCAACTCTGGGAACACAGCCACTCTGACCATCACCGGGACCCAGGCTATGGATGAGGCTAACTATTACTGTCAGGCGTGGGACACCAGCAGTTTGTGCTATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGATGGAAGTAGTAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGTTTTTGTAGTGGTACCAGCTGCCCTTACTACTACTACTACGGTATGGACGTCTGGGGCCAAGGGACCACGGTCACCGTCTCCTCA |
| iPS:436764 | 21-225_158E9 | | | |
| | | AA | SYDLTQPPSVSVSPGQTASITCSGDKLGDKYVCWYQQKPGQSPVLVIYQDSKRPSGIPERFSGSNSGNTATLTITGTQAMDEANYYCQAWDNSSFVLFGGGTKLTVL | QVQLVESGGGVVQPGRSLRLSCAASGFTFSSYGMHWVRQAPGKGLEWVAVIWYDGSSKYYADSVKGRFTISRDNSKNTLYLQMNSLRAEDTAVYYCARDRVFCSGTSCPYYYYGMDVWGQGTTVTVSS |
| | | | SEQ ID NO: 27405 | SEQ ID NO: 31411 |
| | | | SEQ ID NO: 27406 | SEQ ID NO: 31412 |

FIGURE 50
(Continued)

| | | | |
|---|---|---|---|
| iPS:436766 | 21-225_158D10 | NA | TCCTATGAGCTGACTCAGCCACCCTCAGTGACCGTGTCCCCAGGACAGAGCAGCCAGCATCACCTGCTCTGGAGATAAATTGGGGGATAAATATGTTTGCTGGTATCAGCAGAAGCCAGGCCAGTCCCCTGTGCTCTGGTCATCTATCAAGATCGCAAGCGGCCCTCAGGGATCCCTGAGCGATTGTCTGGCTCCAACTCTGGGAACACAGCCACTCTGACCATCAGCGGGACCCAGGCTCTGGATGAGGCTGACTATTACTGTCAGGCGTGGGGACACAGCAGCTTTGTGGTATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGCAGACTCCGTGATGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGTTTCTTGTAGTAGTACCAGCTGCCCTTACTACTACTACTACGGTATGGACGTCTGGGGCCAAGGGACCACGGTCACCGTCTCCTCA |
| | | | SEQ ID NO: 27407 | SEQ ID NO: 31413 |
| | | AA | SYELTQPPSVTVSPGQTASITCSGDKLGDKYVCWYQQKPGQSPVLVIYQDRKRPSGIPERLSGSNSGNTATLTISGTQALDEADYYCQAWGNSSFVVFGGGTKLTVL | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDRVSCSSTSCPYYYYYGMDVWGQGTTVTVSS |
| | | | SEQ ID NO: 27408 | SEQ ID NO: 31414 |

FIGURE 50
(Continued)

| | | | |
|---|---|---|---|
| iPS:436768 | 21-225_159H8 | NA | TCCTATGAGCTGACTCAGCCACCCTCAGTGTCCGTGTCCCCAGGACAGAGCCAGCATCACCTGCTCTGGAGATAAATTGGGGGATAAATATGTTTGCTGGTATCAGCAGAAGCCAGGCCAGTCCCCTGTGTTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTCTGGATGAGGCTGACTATTACTGTCAGGCGTGGGGACAGCAGCTTTGTGTATTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTGCAGCGTCTGGATTCACCTTCAGTACCTATGGCATGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGTTTCTTGTAGTAGTACCAGCTGCCCTTACTACTACTACTACGGTATGGACGTCTGGGGCCAAGGGACCACGGTCACCGTCTCCTCA |
| | | | SEQ ID NO: 27409 | SEQ ID NO: 31415 |
| | | AA | SYELTQPPSVSVSPGQTASITCSGDKLGDKYVCWYQQKPGQSPVLVIYQDRKRPSGIPERFSGSNSGNTATLTISGTQALDEADYYCQAWGNSSFVVFGGGTKLTVL | QVQLVESGGGVVQPGRSLRLSCAASGFTFSTYGMHWVRQAPGKGLEWVAVIWYDGSNKYYADSVKGRFTISRDNSKNTLYLQMNSLRAEDTAVYYCARDRVSCSSTSCPYYYYYGMDVWGQGTTVTVSS |
| | | | SEQ ID NO: 27410 | SEQ ID NO: 31416 |

FIGURE 50
(Continued)

| | | | |
|---|---|---|---|
| iPS:436770 | 21-225_160B12 | NA | TCCGATGAGCTGACTCAGTCACCCTCAGTGTCCGTGTCCCCAGGACAGAGCCAGCATCACCTGCTCTGGAGATAAATTGGGGGATAAATATGTTTGCTGGTATCAGCAGAAGCCAGGCCAGTCCCCTGTGTTGGTCATCTATCAAGATAGCAAGCGGCCCTCAGGGATCCCTGAGCGATTCTCTGGCTCCAACTCTGGGAACACAGCCACTCTGACCATCAGCGGGACCCAGGCTCTGGATGAGGCTGACTATTACTGTGCTGTGTATTACTGCCAACAGCAGTTTGTGTATTCGGCGGAGGGACCAAGCTGACCGTCCTA |  CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGTTTCTTGTAGTAGTACCAGCTGCCCTTACTACTACTACTACGGTATGGACGTCTGGGGCCAAGGGACCACGGTCACCGTCTCCTCA |
| | | | SEQ ID NO: 31417 |
| | | AA | SDELTQSPSVSVSPGQTASITCSGDKLGDKYVCWYQQKPGQSPVLVIYQDSKRPSGIPERFSGSNSGNTATLTISGTQALDEADYYCQAWGNSSFVVFGGGTKLTVL | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDRVSCSSTSCPYYYYYGMDVWGQGTTVTVSS |
| | | | SEQ ID NO: 27412 | SEQ ID NO: 31418 |
| | | | SEQ ID NO: 27411 | |

FIGURE 50
(Continued)

| | | | | |
|---|---|---|---|---|
| iPS:436772 | 21-225_161H3 | NA | TCCTATGAGCTGACTCAGCCACCTCAGTGTC CGTGTCCCCAGGACAGACAGCCAGCATCACCT GCTCTGGAGATAGATTGGGGATAAATATGTT TGCTGTATCAGCAGAAGCCAGGCCAGTCCCC TGTACTGGTCATCTTTCAAGATAACAAGCGC CCTCAGGGATCCCTGAGCGATTCTCTGGCTCC AACTCTGGGAACACAGCCACTCTGACCATCAG CGGGACCCAGGCTCTGGATGAGGCTGACTATT ACTGTCAGGCGTGGGTCAACAACACTGCAGTG GTTTTCGGCGGAGGGACCAAGCTGACCGTCCT A | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAGTAGTGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGTCGGTA TAGCGGTGGCTGGTACATCTTTGACTACTGGGGC CAGGGAACCCTGGTCACCGTCTCCTCA |
| | | | SEQ ID NO: 27413 | SEQ ID NO: 31419 |
| | | AA | SYELTQPPSVSPGQTASITCSGDRLGDKYVCW YQQKPGQSPVLVFQDNKRPSGIPERFSGSNSGN TATLTISGTQALDEADYYCQAWVNNTAVVFGG GTKLTVL | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARVGYSG GWYIFDYWGQGTLVTVSS |
| | | | SEQ ID NO: 27414 | SEQ ID NO: 31420 |
| iPS:436774 | 21-225_161E10 | NA | TCCTTTGACCTGACTCAGCCACCCTCAGTGTCC GTGTCCCCAGGACAGACAGCCAGCATCACCTG CTCTGGAGATAAATTGGGGGATAAATATGTTT GCTGGTATCAGCAGAAGCCAGGCCAGTCCCCT GTGCTGGTCATCTATCAAGATAGCAAGCGGCC CTCAGGGATCCCTGAGCGAATCTCTGGCTCCA ACTCTGGGAACACAGCCACTCTGACCATCAGC GGGACCCAGGCTATGGATGAGGCTGACTATTA CTGTCAGACGTGGGACAACAGTAGTTTTGCGC TTTTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTAGTGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGAGATCGGTT TTTTGTAGTGGTACCAGCTGCCCTTACTACTACTA CTACGGTATGGACGTCTGGGGCCAAGGGACCAC GGTCACCGTCTCCTCA |
| | | | SEQ ID NO: 27415 | SEQ ID NO: 31421 |

FIGURE 50
(Continued)

| | | | |
|---|---|---|---|
| iPS:436776 | | AA | SFDLTQPPSVSVSPGQTASITCSGDKLGDKYVCW YQQKPGQSPVLVIYQDSKRPSGIPERISGSNSGNT ATLTISGTQAMDEADYYCQTWDNSSFALFGGGT KLTVL | QVQLVESGGGVVQPGRSLRLSCAASGFTFSSYGMH WVRQAPGKGLEWVAVIWYDGSNKYYVDSVKGRF TISRDNSKNTLYLQMNSLRAEDTAVYYCARDRVFC SGTSCPYYYYGMDVWGQGTTVTVSS |
| | | | SEQ ID NO: 27416 | SEQ ID NO: 31422 |
| | | NA | TCCTATGAGCTGACTCAGCCACCCTCAGTGTC CGTGTCCCCAGGACAGACAGCCAGCATCACCT GCTCTGGAGATAAATTGGGGTGATAAATATGCT TGCTGTGGTATCAGCAGAAGCCAGGACAGTCCCC TGTGTGCTGGTCATCTATCAAGATACCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGGTGGGACACAGCTGACCACTCTGGTT TTCGGCGGAGGGACCAAGCTGACCGTCCTA | CAGGTGCAGCTGCAGGAGTCGGGCCCAGGACTG GTGAAGCCTTCACAGACCCTGTCCTCACCTGCA CTGTCTCTGGTGCTCCATCAGCAGTGGTGGTTA CTACTGAGCTGGATCGCCAGCACCCAGGGAA GGGCCTGGAGTGGATTGGGTACATCTATTACAGT GGGAGCCCCTACTACAACCGTCCTCCTCAAGAGTC GAATTACCATATCAATAGACACGTCTAAGAACCA GTTCTCCCTGAAGCTGAACTCTGTGACTGCCGCG GACACGGCCGTGTATTACTGTGCGAGATCGAATT GTAGTAGTGCCAACTGCTATACGGTGGGGTTCTA CTACTACGGTTTGACGTCTGGGGCCGAGGACC ACGGTCACCGTCTCCTCA |
| | | | SEQ ID NO: 27417 | SEQ ID NO: 31423 |
| | 21-225_161F12 | AA | SYELTQPPSVSVSPGQTASITCSGDKLGDKYACW YQQKPGQSPVLVIYQDTKRPSGIPERFSGSNSGN TATLTISGIQAMDEADYYCQAWDSTTLVFGGG TKLTVL | QVQLQESGPGLVKPSQTLSLTCTVSGGSISSGGYYW SWIRQHPGKGLEWIGYIYYSGSPYYNPSLKSRITISI DTSKNQFSLKLNSVTAADTAVYYCARSNCSSANCY TVGFYYYGLDVWGRGTTVTVSS |
| | | | SEQ ID NO: 27418 | SEQ ID NO: 31424 |

FIGURE 50
(Continued)

| iPS:436780 | 21-225_165H3 | NA | TCCTATGAGCTGACTCAGCCACCCTCAGTGTC CGTGTCCCCAGGACAGAGCCAGCATCACCT GCTCTGGAGATAAATTGGGTGATAAATATGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGGCTATGATGAGCTGACTGACTATT ACTGTCAGGCGTGGACAGACCACTCTGGTT TTCGGCGGAGGGACCAAGCTGACCGTCCTA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTTA CTACTGGAGCTGGATCCGCCAGCACCCAGGAA GGGCCTGGAGTGGATTGGGTACATCTATTACAGT GGGAGCCCTACTACAATCCGTCCCTCAAGAGTC GAATTACCATATCAATAGACACGTCTAAGAACCA GTTCTCCCTGAAGCTGAACTCTGTGACTGCCGCG GACACGGCCGTGTATTACTGTGCGAGATCGAATT GTAGTAGTGCCAACTGCTATACGGTGGGGTTCTA CTACTACGGTATGGACGTCTGGGGCCAAGGAC CACGGTCACCGTCTCCTCA |
| | | | SEQ ID NO: 27419 | SEQ ID NO: 31425 |
| | | AA | SYELTQPPSVSVSPGQTASITCSGDKLGDKYACW YQQKPGQSPVLVIYQDSKRPSGIPERFSGSNSGN TATLTISGTQAMDEADYYCQAWDSTTLVFGGG TKLTVL | QVQLQESGPGLVKPSQTLSLTCTVSGGSISSGGYYW SWIRQHPGKGLEWIGYIYYSGSPYYNPSLKSRITISI DTSKNQFSLKLNSVTAADTAVYYCARSNCSSANCY TVGFYYYGMDVWGQGTTVTVSS |
| | | | SEQ ID NO: 27420 | SEQ ID NO: 31426 |

FIGURE 50
(Continued)

| | | | |
|---|---|---|---|
| iPS:436782 | 21-225_166G11 | NA | TCCTATGAGCTGAGTCAGCAGCCCTCAGTGTC CGTGTCCCCAGGACAGAGCCAGCATCACCT GCTCTGGAGATAAATTGGGGATAAATATGTT CACTGGTATCAGCAGAAGCCAGGCCAGTCCCC TGTGTTGGTCATCTATCAAGATAGCAAGCGGC CCTCAGGGATCCCTGAGCGATTCTCTGGCTCC AACTCTGGGAACACAGCCACTCTGACCATCAG CGGACCCAGGTATGAGGATGAGGCTGATTATT ACTGTCAGGCGTGGGACAACAGCACTGCGGTA TTCGGCGGAGGGACCAAGTTGACCGTCCTA<br><br>SEQ ID NO: 27421 | CAGGTGCAGCTGGTGGAGTCTGGGGGAGGCGTG GTCCAGCCTGGGAGGTCCCTGAGACTCTCCTGTG CAGCGTCTGGATTCACCTTCAATGGCTATGGCAT GCACTGGGTCCGCCAGGCTCCAGGCAAGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTTTCTGCAAATGAACAGCCTGACAGCCGAGGA CACGGCTGTGTATTACTGTGCGAGAGATGATAGA TATTGTAGTAGTCCCACCTGCCATCCTTACTACTA CTACTACGGTCTGGACGTCTGGGGCCAAGGGACC ACGGTCACCGTCTCCTCA<br><br>SEQ ID NO: 31427 |
| | | AA | SYELSQPPSVSVSPGQTASITCSGDKLGDKYVHW YQQKPGQSPVLVIYQDSKRPSGIPERFSGSNSGN TATLTISGTQAMDEADYYCQAWDNSTAVFGGG TKLTVL<br><br>SEQ ID NO: 27422 | QVQLVESGGGVVQPGRSLRLSCAASGFTFNGYGM HWVRQAPGKGLEWVAVIWYDGSNKYYADSVKGR FTISRDTSKNTLFLQMNSLTAEDTAVYYCARDDRY CSSPTCHPYYYYGLDVWGQGTTVTVSS<br><br>SEQ ID NO: 31428 |

FIGURE 50
(Continued)

| | | | |
|---|---|---|---|
| iPS:436784 | 21-225_169C1 | NA | TCCTATGAGCTGACTCAGCCACCCTCAGTGTC CGTGTCCCCAGGACAGAGACAGCCAGCATCACCT GCTCTGGAGATAAATTGGGGGATAAATATGTT TGTTGGTATCAGCAGAAGCCAGGCCAGTCCCC TTTGCTGGTCATCTATAAAGATATCAAGCGGC CCTCAGGGATCCCCTGAGCGATTCTCTGGCTCC AACTCTGGTAACACAGCCACTCTGACCATCAG CGGGACCCAGGCTATGGAGGATGAGGCTGACTATT ACTGTCAGGCGTGGGACACCAACACTGTGATA TTCGGCGGAGGGACCAAGCTGACCGTCCTA |
| | | | CAGGTGCAGTTGGTGGAGTCTGGGGGAGGCGTG GTCCAGCCTGGGAGGTCCCTGAGACTCTCCTGTG CAGCGTCTGGATTCACTTTGAGTAGCAATGGCAT GCACTGGGTCCGCCAGGCTCCAGGCAAGGGCT GGAGTGGGTGGCAGTTATATGCAGTATGATGAAGT AATAAATACTATGCAGAGACTCCGTGAAGGCCGA TTCACCATCTCCAGAGACAACAGCTTCCAAGAACACGC TGTATCTGCAAATGAACAGCCTGAGAGCCGAGG ACACGGCTGTGTATTACTGTGCGAGAGATCAGTA CAACCGGAACGACGACCACCAGCTTACTACTA CTACTACGGTTTGGACGTCTGGGGCCAAGGGACC ACGGTCACCGTCTCCTCA |
| | | AA | SYELTQPPSVSVSPGQTASITCSGDKLGDKYVCW YQQKPGQSPLLVIYKDIKRPSGIPERFSGSNSGNT ATLTISGTQAMDEADYYCQAWDTNTVIFGGGT KLTVL |
| | | | QVQLVESGGGVVQPGRSLRLSCAASGFTLSSNGMH WVRQAPGKGLEWVAVIWYDGSNKYYADSVKGRF TISRDTSKNTLYLQMNSLRAEDTAVYYCARDQYNR NDGPPAYYYYYGLDVWGQGTTVTVSS |
| | | SEQ ID NO: 27423 | SEQ ID NO: 31429 |
| | | SEQ ID NO: 27424 | SEQ ID NO: 31430 |

FIGURE 50
(Continued)

| | | | |
|---|---|---|---|
| iPS:436786 | 21-225_169A6 | NA | TCCTATGAGCTGACTCAGCCACCCTCAGTGTC CGTGTCCCCAGGACAGAGACAGCCAGCATCACCT GCTCTGGAGATAAATTGGGGGATAAATATGTT TGTTGGTATCAGCGGAAGCCAGGCCAGTCCCC TGTTCTGGTCATCTATCAGGATTACAAGCGGC CCTCAGGGATCCCTGAGCGATTCTCTGGCTCC AACTCTGGGAACACAGCCACTCTGACCATCAG CGGACCCAGGCTATGGAGGCTGACTATT ACTGTCAGGCGTGGGACACCAACACTGTGCTT TTCGGCGGAGGGACCAAGCTGACCGTCCTG<br><br>SEQ ID NO: 27425 | CAGGTGCAGCTGGTGGAGTCTGGGGGAGGCGTG GTCCAGCCTGGGAGGTCCCTGAGACTCTCCTGTG CAGCGTCTGGATTCACTTTGAGCAGCAATGGCAT GCACTGGGTCCGCCAGGCTCCAGGCAAGGGCT GGAGTGGGTGGCAGTTATATGGTATGATGAAGT AATAAATACTATGCAGAGACTCCGTGAAGGGCCGA TTCACCATCTCCAGAGACAATTCCAAGAACACGC TGTCTCTGCAAATGAACAGCCTGAGAGCCGAGG ACACGGCTGTGTATTACTGTGCGAGAGATCAGTA CAACCGGAACGACGGACCACCAGCTTACTACTA CTACTACGGTATGGACGTCTGGGGCCAAGGGAC CACGGTCACCGTCTCCTCA<br><br>SEQ ID NO: 31431 |
| | | AA | SYELTQPPSVSVSPGQTASITCSGDKLGDKYVCW YQRKPGQSPVLVIYQDYKRPSGIPERFSGSNSGN TATLTISGTQAMDEADYYCQAWDTNTVLFGGG TKLTVL<br><br>SEQ ID NO: 27426 | QVQLVESGGGVVQPGRSLRLSCAASGFTLSSNGMH WVRQAPGKGLEWVAVIWYDGSNKYYADSVKGRF TISRDNSKNTLSLQMNSLRAEDTAVYYCARDQYNR NDGPPAYYYYGMDVWGQGTTVTVSS<br><br>SEQ ID NO: 31432 |

FIGURE 50
(Continued)

| | | | |
|---|---|---|---|
| iPS:436788 | 21-225_169B7 | NA | GCCTATGACCTGACTCAGCCACCCTCAGTGTC CGTGTCCCCAGGACAGACAGCCAGAATCACCT GCTCTGGAGATATCAACAGAAGCCAGGCCAGTCCCC TGTGGTATCAACAGAAGCCAGGCCAGTCCCC TGTGCTGGTCATCTATCAAGATAGGAAGCGGC CCTCAGGGATCCCGAGCGATTCTCTGGCTCC AACTCTGGAACACAGCCACTCTGACCATCAG CGGGACCCAGGCTATGGATGAGGCTGACTATT ACTGTCAGGCGTGGGACAAGAACACTGTGGTA TTCGGCGGAGGGACCAAGCTGACCGTCCTA | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTATAGCTT GAACTGGGTCCGCCAGGCTCCAGGGAAGGGGCT GGAGTGGGTTTCATACATTGGTAGTAGTGGCAGT ATCATATTCTACGCAGACTCTGTGAAGGGCCGAT TCACCATCTCCAGAGACAATGCCAAGAACTCACT GTATCTGCAAATGAACAGCCTGAGAGACGAGGA CACGGCTGTGTATTACTGTGCGAGAGGGGATACA GCTGGGGTTACCTATTACTACGGTATGGACGTCT GGGGCCAAGGGACCACGGTCACCGTCTCCTCA |
| | | | SEQ ID NO: 27427 | SEQ ID NO: 31433 |
| | | AA | AYDLTQPPSVSVSPGQTARITCSGDKLGGKYAS WYQQKPGQSPVLVIYQDRKRPSGIPERFSGSNSG NTATLTISGTQAMDEADYYCQAWDKNTVFGG GTKLTVL | EVQLVESGGGLVQPGGSLRLSCAASGFTFSSYSLN WVRQAPGKGLEWVSYIGSSGSHFYADSVKGRFTIS RDNAKNSLYLQMNSLRDEDTAVYYCARGDTAGVT YYYGMDVWGQGTTVTVSS |
| | | | SEQ ID NO: 27428 | SEQ ID NO: 31434 |
| iPS:436790 | 21-225_169G11 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAGTAAGCGGC CCTCAGGGATCCCGAGCGATTCTCTGGCTCC AACTCTGGAACACAGCCACTCTGACCATCAG CGGGACCCAGGCCGTGGGACAACAGCACTGCGGTA ACTGTCAGGCGCTATGATGAGGCTGACTGGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGGTGTATTACTGTGCGAGAGAGGGGG CTACGTATTAACTACGGTTCGGGGAGTTATATCC GGCTACTAACTACGGTATGGACGTCTGGGGCCAA GGGACCACGGTCACCGTCTCCTCA |

FIGURE 50
(Continued)

| | | | | |
|---|---|---|---|---|
| iPS:436792 | 21-225_169D12 | AA | SEQ ID NO: 27429<br>SYELTQPPSVSVSPGQTASITCSGDKLGDKYACW YQQKPGQSPVLVIYQDSKRPSGIPERFSGSNSGN TATLTISGTQAMDEADYYCQAWDNSTAVFGGG TKLTVL<br>SEQ ID NO: 27430 | SEQ ID NO: 31435<br>QVQLVESGGGVVQPGRSLRLSCAASGFTFSSYGMH WVRQAPGKGLEWVAIIWYDGSNKYYADSVKGRFT ISRDNSKNTLYLQMNSLRAEDTGVYYCAREGATY YHGSGSYYPATNYGMDVWGQGTTVTVSS<br>SEQ ID NO: 31436 |
| | | NA | AATTTTATGCTGACTCAGCCCCACTCTGTGTCG GAGTCTCCGGGGAAGACGGTAACCATCTCCTG CACCCGCAGCAGTGGCAGCATTACCGGCAACT ATGTGCAGTGGCACCAGCAGCGCCCGGGCAAT TCCCCCCACCACTCTGATCTATATGAGGATAAAA AAGACCCTCGGGGTCCCTGATCGGTTCTCTG GCTCCATCGACAGCTCCTCCAACTCTGCCTCC CTCACCATCTCTGGACTGAAGACTGAGGACGA GGCTGACTATTACTGTCAGTCTTATTATAGCG GCAATTGGGTGTTCGGCGGAGGGACCAAGCTG ACCGTCCTG<br>SEQ ID NO: 27431 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATAGCAGACTCCGTGAAGGGCCGAT AATAAATATTATGCAGACTCCGTGAAGGGCCGAT TCACCATCTCCAGAGACAATTCCAAGAACACGCT GTATCTGCAAATGAACAGCCTGAGAGCCGAGGA CACGGCTGTGTATTACTGTGCGAGTCCCCTTTAC GATATGGGACTCTACTACGATATGGACGTCTGGG GCCAAGGGACCACGGTCACCGTCTCCTCA<br>SEQ ID NO: 31437 |
| | | AA | NFMLTQPHSVSESPGKTVTISCTRSSGSITGNYVQ WHQQRPGNSPTTLIYEDKKRPSGVPDRFSGSIDS SSNSASLTISGLKTEDEADYYCQSYYSGNWVFG GGTKLTVL<br>SEQ ID NO: 27432 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCASPLYDM GLYYDMDVWGQGTTVTVSS<br>SEQ ID NO: 31438 |

FIGURE 50
(Continued)

| | | | |
|---|---|---|---|
| iPS:436794 | 21-225_170F1 | NA | TCCTATGAGTTGAGTCAGCAGCCCTCAGTGTC CGTGTCCCCAGGACAGAGACAGCCAGCATCACCT GCTCTGGAGATAAATTGGGGGATAAATATTCT TGCTGGTATCAGCAGAAGCCAGGCCAGTCCCC TGTGCTGGTCATCTATCAAGATAGTAAGCGGC CCTCAGGGATCCCTGCACGATTCTCTGCTCC AACTCTGGGAACACAGCCACTCTGACCATCAG CGGGACCCAGGCTATGGAGGATGAGGCTGATTATT ACTGTCAGGCGTGGGACAGCAACACTGCGGTA TTCGGCGGAGGGACCAAACTGACCGTCCTA<br>SEQ ID NO: 27433 | CAGGTGCAGCTGGTGGAGTCTGGGGGAGGCGTG GTCCAGCCTGGGAGGTCCCTGAGACTCTCCTGTG CAGCGTCTGGATTCACCTTCAGTGGCTATGGCAT GAACTGGGTCCGCCAGGCTCCAGGCAAGGGCT GGAGTGGGTGGCAATTATATGGTATGATGGAAAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGGT TATTGTAGTAGTACCAGCTGCCATCCCTATTACT ACTACTACGTATGGACGTCTGGGGCCAAGGGA CCACGGTCACCGTCTCCTCA<br>SEQ ID NO: 31439 |
| | | AA | SYELSQPPSVSVSPGQTASITCSGDKLGDKYSCW YQQKPGQSPVLVIYQDSKRPSGIPARFSGSNSGN TATLTISGTQAMDEADYYCQAWDSNTAVFGGG TKLTVL<br>SEQ ID NO: 27434 | QVQLVESGGGVVQPGRSLRLSCAASGFTFSGYGM NWVRQAPGKGLEWVAIIWYDGNNKYYADSVKGR FTISRDNSKNTLYLQMNSLRAEDTAVYYCARDRVY CSSTSCHPYYYYAMDVWGQGTTVTVSS<br>SEQ ID NO: 31440 |

FIGURE 50
(Continued)

| | | | |
|---|---|---|---|
| iPS:436796 | 21-225_170A5 | NA | CAGGTGCAGCTGGTGGAGTCTGGGGGAGGCGTG GTCCAGCCTGGGAGGTCCCTGAGACTCTCCTGTG CAGCGTCTGGACTCACCTTCAGTAACTGTGGCAT GCACTGGGTCCGCCAGGCTCCAGGCAAGGGCT GGAGTGGGTGGCAATTATATGGTATGATGGAAGT AATAAATACTATGCAGACTCCGTGAAGGGCCGA TTCACCATCTCCAGAGACAATTCCAAGAACACGC TGGATCTGCAAATGAACAGCCTGAGAGCCGAGG ACACGGCTGTGTATTACTGTGCGAGAGATCAGTA CAACAGGAACGACGACCACCAGCTTACTACTA CTACTACGGTTTGGACGTCTGGGGCCAAGGGACC ACGGTCACCGTCTCCTCA |
| | | | SEQ ID NO: 31441 |
| | | TCCTATGACCTGACTCAGCCACCCTCAGTGTC CGTGTCCCCAGGACAGAGAGCCAGCATCACCT GCTCTGGAGATAAATTGGGGGATAAATATGCT TGTTGGTATCAGCAGAAGCCAGGCCAGTCCCC TATACTGGTCATCTATCAAGATTACAAGCGGC CCTCAGGGATCCCTGAGCGATTCTCTGGCTCC AACTCTGGGAACACAGCCACTCTGACCATCAG CGGGACCCAGGCTATGGGACAACAGCACTGTA ATTGTCAGGCGGTGCAACAGCACTATGTA TTCGGCGGAGGGACCAAGGCTGACCGTCCTA | |
| | | | SEQ ID NO: 27435 |
| | | AA | SYDLTQPPSVSVSPGQTASITCSGDKLGDKYAC WYQQKPGQSPILVIYQDYKRPSGIPERFSGSNSG NTATLTISGTQAMDEADYYCQAWDNSTMVFGG GTRLTVL |
| | | | SEQ ID NO: 27436 |
| | | | QVQLVESGGGVVQPGRSLRLSCAASGLTFSNCGM HWVRQAPGKGLEWVAIIWYDGSNKYYADSVKGR FTISRDNSKNTLDLQMNSLRAEDTAVYYCARDQYN RNDGPPAYYYYGLDVWGQGTTVTVSS |
| | | | SEQ ID NO: 31442 |

FIGURE 50
(Continued)

| | | | |
|---|---|---|---|
| iPS:436798 | 21-225_171F5 | NA | GCCTATGACCTGACTCAGCCACCCTCAGTGTC CGTGTCCCCAGGACAGAGCAGCCAGCATCACCT GCTCTGGAGATAAATTGGGGGGAAAATATGCT TCCTGGTATCAACAGAAGCCAGGCCAGTCCCC TGTGCTGGTCATCTATCAAGATAGGAAGCGGC CCCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAAGAACACTGTGTA TTCGGCGGAGGGACCAAGCTGACCGTCCTA<br><br>SEQ ID NO: 27437 | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTATAGCTT GAACTGGGTCCGCCAGGCTCCAGGGAAGGGGCT GGAGTGGGTTTCATACATTGGTAGTAGTGGCAGT ATCATATTCTACGCAGACTCTGTGAAGGGCCGAT TCACCATCTCCAGAGACAATGCCAAGAACTCACT GTATCTGCAAATGAACAGCCTGAGAGACGAGGA CACGGCTGTGTATTACTGTGCGAGAGGGATACA GCTGGGGTTACCTATTACTACGGTATGGACGTCT GGGGCCAAGGGACCACGGTCACCGTCTCCTCA<br><br>SEQ ID NO: 31443 |
| | | AA | AYDLTQPPSVSVSPGQTASITCSGDKLGKYAS WYQQKPGQSPVLVIYQDRKRPSGIPERFSGSNSG NTATLTISGTQAMDEADYYCQAWDKNTVFGG GTKLTVL<br><br>SEQ ID NO: 27438 | EVQLVESGGGLVQPGGSLRLSCAASGFTFSSYSLN WVRQAPGKGLEWVSYIGSSGSIIFYADSVKGRFTIS RDNAKNSLYLQMNSLRDEDTAVYYCARGDTAGVT YYYGMDVWGQGTTVTVSS<br><br>SEQ ID NO: 31444 |
| iPS:436800 | 21-225_171D12 | NA | TCTTCTGAGCTGACTCAGGACCCTGCTGTGTCT GTGGCCTTGGGACAGACAGTCAGGATCACATG CCAAGGAGACAGCCTCAGAAGCTATTATGCAA GCTGGTACCAGCAGAAGCCAGGACAGGCCC TATACTTGTCATCTATGCTAAAAACAACGGC CCTCAGGGGATCCCAGACCGATTCTCTGGCTCC AACTCAGGAAACACAGCTTCCTTGACCATCAC TGGGGCTCAGGCGGAAGATGAGGCTGACTATT ACTGTAACTCCCGGACACAGCAGTGGCAGCCAT GTGGTATTCGGCGGAGGGACCAAACTGACCGT CCTA<br><br>SEQ ID NO: 27439 | CAGGTGCAGCTGGTGGTGCAGTCTGGGGCTGAGGTG AAGAAGCCTGGGGCCTCAGTGAAGGTTTCCTGCA AGGCATCTGGATACACCTTCAACAGTTACTATAT GTATTGGGTGCGACAGGCCCCTGGACAAGGGCTT GAGTGGATGGGAATAATCAACCCTAGTGGTGGT AGCACAAACTACGCACAGAAGTTCCAGGGCAGA GTCACCATGACCAGGGACACGTCCACGAGCACA CTCTACATGGAGCTGAACAGCCTGAGATCTGAGG ACACGGCCGTGTATTACTGTGCGAGTGGTTGGGA GTTAAACTACTGGGGCCAGGGAACCCTGGTCACC GTCTCCTCA<br><br>SEQ ID NO: 31445 |

FIGURE 50
(Continued)

| | | | |
|---|---|---|---|
| | | AA | SSELTQDPAVSVALGQTVRITCQGDSLRSYYAS WYQQKPGQAPILVIYAKNNRPSGIPDRFSGSNSG NTASLTITGAQAEDEADYYCNSRDSSGSHVVFG GGTKLTVL<br><br>SEQ ID NO: 27440 | QVQLVQSGAEVKKPGASVKVSCKASGYTFNSYYM YWVRQAPGQGLEWMGIINPSGGSTNYAQKFQGRV TMTRDTSTSTLYMELNSLRSEDTAVYYCASGWELN YWGQGTLVTVSS<br><br>SEQ ID NO: 31446 |
| iPS:436802 | 21-225_171E12 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATCGCAAGCGGC CCTCAGGGATCCCTGAGCGATTCTCTGGCTCC AACTCTGGGAACACAGCCACCCTGACCATCAG CGGGACCCAGGCTATGGATGAGGCTGACTATT ACTGTCAGGCCGTGGACACATCAGCACTTATGTG GTATTCGGCGGAGGGACCAAAACTGACCGTCCT A<br><br>SEQ ID NO: 27441 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGCT GGAGTGGGTGGCAGTTATATGGAATGATGGAAG TAATAAATATAATGGAGACTCCGTGAAGGGCCG ATTCACCATCTCCAGAGACAACAATTCCAAGAACACG CTGTATCTGCAAATGAACAGTCTGAGAGCCGAG GACACGGCTGTGTATTACTGTGCGAGAGACCGTA CGTATTACTCTGGTTCGGGGAGCCCCCTACTA CTACTACTACGGTATGGACGTCTGGGGCCAAGGG ACCACGGTCACCGTCTCCTCA<br><br>SEQ ID NO: 31447 |
| | | AA | SYELTQPPSVSVSPGQTASITCSGDKLGDKYACW YQQKPGQSPVLVIYQDRKRPSGIPERFSGSNSGN TATLTISGTQAMDEADYYCQAWDISTYVVFGGG TKLTVL<br><br>SEQ ID NO: 27442 | QVQLVESGGGVVQPGRSLRLSCAASGFTFSSYGMH WVRQAPGKGLEWVAVIWNDGGNKYNGDSVKGRF TISRDNSKNTLYLQMNSLRAEDTAVYYCARDRTYY SGSGSPPYYYYGMDVWGQGTTVTVSS<br><br>SEQ ID NO: 31448 |

FIGURE 50
(Continued)

| | | | |
|---|---|---|---|
| iPS:436804 | 21-225_172C3 | NA | TCTTCTGAGCTGACTCAGGACCCTGCTGTGTCT GTGGCCTTGGGACAGACAGCCTCAGGATCACAG CCAAGGAGACAGCCTCAGAAACTATTATGTAA GCTGGTACCAGCAGAAGCCAGGACAGGCCCC TATACTTGTCATCTATACTAAAAACAGCGGC CCTCAGGGATCCCAGACCGATTCTCTGGCTCC ACCTCAGGAAACACAGCTTCCTTGACCATCAC TGGGACTCAGGCGCGGAAGATGAGGCTGACTATT ACTGTAACTCCCGGGACAGCAGTGGCAACCAT GTGGTATTCGGCGGAGGGACCAAGCTGACCGT CCTA<br><br>SEQ ID NO: 27443 | CAGGTGCAGCTGGTGCAGTCTGGGGCTGAGGTG AAGAAGCCTGGGGCCTCAGTGAAGGTTTCCTGCA AGGCATCTGGATACACCTTCAGAAGTTACTATAT GTATTGGGTGCGACAGGCCCCTGGACAAGGGCTT GAGTGGGTGGGAACAATCAACCCTAGTGGTGGT AGCACAAACTACGCACAGAAGTTCCAGGGCAGA GTCACCATGACCAGGGACACGTCCACGAGCACA CTCTACATGGAGCTGAACAGCCTGAGATCTGAGG ACACGGCCGTGTATTACTGTGCGAGTGGCTGGGA GTTAAACTACTGGGGCCAGGGAACCCTGGTCACC GTCTCCTCA<br><br>SEQ ID NO: 31449 |
| | | AA | SSELTQDPAVSVALGQTVRITCQGDSLRNYYVS WYQQKPGQAPILVIYTKNSRPSGIPDRFSGSTSG NTASLTITGTQAEDEADYYCNSRDSSGNHVVFG GGTKLTVL<br><br>SEQ ID NO: 27444 | QVQLVQSGAEVKKPGASVKVSCKASGYTFRSYYM YWVRQAPGQGLEWVGTINPSGGSTNYAQKFQGRV TMTRDTSTSTLYMELNSLRSEDTAVYYCASGWELN YWGQGTLVTVSS<br><br>SEQ ID NO: 31450 |
| iPS:436806 | 21-225_172B12 | NA | TCTTCTGAGCTGACTCAGGACCCTGCTGTGTCT GTGGCCTTGGGACAGACAGCCTCAGGATCACAG CCAAGGAGACAGCCTCAGAAACTATTATGCAA GCTGGTACCAGCAGAAGCCAGGACAGGCCCC TATACTTGTCATCTATACTAAAAACAGCGGC CCTCAGGGATCCCAGACCGATTCTCTGGCTCC ACCTCAGGAAACACAGCTTCCTTGACCATCAC TGGGGCTCAGGCGCGGAAGATGAGGCTGACTATT ACTGTAACTCCCGGGACAGCAGTGGCAACCAT GTGGTATTCGGCGGAGGGACCAAGCTGACCGT CCTA<br><br>SEQ ID NO: 27445 | CAGGTGCAGCTGGTGCAGTCTGGGGCTGAGGTG AAGAAGCCTGGGGCCTCAGTGACGGTTTCCTGCA AGGCATCTGGATACACCTTCAGAAGTTACTATAT GTATTGGGTGCGACAGGCCCCTGGACAAGGGCTT GAGTGGGTGGGAACAATCAACCCTAGTGGTGGT AGCACAGACTACGCACAGAAGTTCCAGGGCAGA GTCACCATGACCAGGGACACGTCCACGAGCACA CTCTACATGGAGCTGATTACTGTGCGAGTGGCTGGGA ACACGGCCGTGTATTACTGTGCGAGTGGCTGGGA ATTAAACTACTGGGGCCAGGGAACCCTGGTCACC GTCTCCTCA<br><br>SEQ ID NO: 31451 |

FIGURE 50
(Continued)

| | | | |
|---|---|---|---|
| iPS:436808 | 21-225_173F8 | AA | SSELTQDPAVSVALGQTVRITCQGDSLRNYYAS WYQQKPGQAPILVIYTKNSRPSGIPDRFSGSTSG NTASLTITGAQAEDEADYYCNSRDSSGNHVVFG GGTKLTVL<br>SEQ ID NO: 27446 | QVQLVQSGAEVKKPGASVTVSCKASGYTFRSYYM YWVRQAPGQGLEWVGTINPSGGSTDYAQKFQGRV TMTRDTSTSTLYMELNSLRSEDTAVYYCASGWELN YWGQGTLVTVSS<br>SEQ ID NO: 31452 |
| | | NA | TCCTATGAGCTGACTCAGCCACCCTCAGTGTC CGTGTCCCAGGACAGCAGCCAGCATCACCT GCTCTGGAAATAAATTGGGGAGGCCAGTCCCC TGCTGGTATCAGCAGAAGCCAGGCCAGTCCCC TGTGCTGGTCATCTCTCAAGATAGCAGGCGGC CCTCAGGGATCCCTGAGCGATTCTCTGGCTCC AACTCTGGGAACACAGGCTATGAGGCTGACTATT CGGGACCCAGGCTGTGGGACAGTTCACTGTGTA ACTGTCAGGGCGTGGGACAGTTCACTGTGTA TTCGGCGGAGGGACCAAGCTGACCGTCCTA<br>SEQ ID NO: 27447 | CAGGTGCAGCTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGGCT GGAATGGGTGGCAGTTATATCATATGATGGAAGT CCTAAATACTGTGCAGACTCCGTGAAGGGCCGAT TCACCATCTCCAGAGACAACAATTCCAAGAACACGCT GTTTCTCCAAATGAACAGCTGAGAGCTGAGGAC ACGGCTGTGTATTATTGTGCAGAGATGAAAGGC AGTGGCTGCCGCCCCTACGGTATGGACGTCTG GGGCCAAGGGACCACGGTCACCGTCTCCTCA<br>SEQ ID NO: 31453 |
| | | AA | SYELTQPPSVSVSPGQTASITCSGNKLGNKYVCW YQQRPGQSPVLVISQDSRRPSGIPERFSGSNSGNT ATLTISGTQAMDEADYYCQAWDSFTVVFGGGT KLTVL<br>SEQ ID NO: 27448 | QVQLVESGGGVVQPGRSLRLSCAASGFTFSSYGMH WVRQAPGKGLEWVAVISYDGSPKYCADSVKGRFT ISRDNSKNTLFLQMNSLRAEDTAVYYCARDERQW LPAPYGMDVWGQGTTVTVSS<br>SEQ ID NO: 31454 |

FIGURE 50
(Continued)

| | | | |
|---|---|---|---|
| iPS:436810 | 21-225_175F4 | NA | CAGGTCCAGCTGGTGCAGTCTGGGGCTGAGGTGAAGAAGCCTGGGGCCTCAGTGAAGGTCTCCTGCAAGGCTTCTGGATACACCTTCACTAGCTACGGTATCAGCTGGGTGCGACAGGCCCCTGGACAAGGGCTTGAGTGGATGGGATGGATCAGCGCTTACAATGGTAACACAAACTATGCACAGAAGCTCCAGGGCAGAGTCACCATGACCACAGACACATCCACGAGCACAGCCTACATGGAGCTGAGGAGCCTGAGATCTGACGACACGGCCGTGTATTACTGTGCGAGAGATAAGGCAGCTGGGAGGAATGACTTCTACTACTACGGTATGGACGTCTGGGGCCAAGGGACCACGGTCACCGTCTCCTCA |
| | | | SEQ ID NO: 31455 |
| | | AA | QVQLQQSGPGLVKPSQTLSLTCAISGDSVSSNSAAWNWIRQSPSRGLEWLGRTYYRSKWYNAYPVSMESRISINPDTSKNQFSLQLNSVTPEDTAVYYCARDKAAGRNDFYYYGMDVWGQGTTVTVSS |
| | | | SEQ ID NO: 31456 |
| iPS:436812 | 21-225_175C6 | NA | CAGGTGCAGCTGGTGGAGTCTGGGGGAGGCGTGGTCCAGCCTGGGAGGTCCCTGAGACTCTCCTGTGCAGCCTCTGGACTCACCTTCAGTAACTGTGGCATGCACTGGGTCCGCCAGGCTCCAGGCAAGGGGCTGGAGTGGGTGGCAATTATATGGTATGATGGAAGTAATAAATACTATGCAGACTCCGTGAAGGGCCGATTCACCGTCTCCAGAGACAATTCCAAGAACACGCTGTATCTGCAAATGAACAGCCTGAGAGCGAGGACACGGCTGTGTATTACTGTGCGAGAGATCAGTACAACGGAACGACGACCAGCTTACTACTACTACTACGGTTTGGACGTCTGGGGCCAAGGGACCACGGTCACCGTCTCCTCA |

FIGURE 50
(Continued)

| | | | SEQ ID NO: 27451 | SEQ ID NO: 31457 |
|---|---|---|---|---|
| | | AA | SYDLTQPPSVSVSPGQTASITCSGDKLGDKYAC WYQQKPGQSPILVIYQDYKRPSGIPERFSGSNSG NTATLTISGTQAMDEADYYCQAWDNSTMVFGG GTRLTVL | QVQLVESGGGVVQPGRSLRLSCAASGLTFSNCGM HWVRQAPGKGLEWVAIIWYDGSNKYYADSVKGR FTVSRDNSKNTLDLQMNSLRAEDTAVYYCARDQY NRNDGPPAYYYYYGLDVWGQGTTVTVSS |
| iPS:436814 | 21-225_178H10 | | SEQ ID NO: 27452 | SEQ ID NO: 31458 |
| | | NA | CAGTCTGCCCTGACTCAGCCTGCCTCCGTGTCT GGGTCTCCTGGACAGTCGATCACCATCTCCTG CACTGGAACCAGCAGTGATGTTGGACGTTTTA ACCTTGTCCTGGTACCAACACCACCAGGC AACGCCCCCAAACTCATGATTTATGAAGTCAG TAAGCGGGCCCTCAAGTCTGGCAACACGGCCTCTCT CTGGCTCCAAGTCTGGCTCCAGGCTGAGGACGAGGC ACAATCTCTGGGGCTCCAGGCTGAGGACGAGGC TGATTATTACTGCTGCTCATATGCAGGTAGTA GCACCTTTGTAGTATTCGGCGGAGGGACCAAG CTGACCGTCCTA | CAGGTACAGCTGCAGCAGTCAGGTCAGGACTG GTGAAGCCCTCGCAGACCCTCTCACTCACCTGTG CCATCTCCGGGACAGTGTCTCTAGCAACAGTGC TGCTTGAACTGATCAGGCAGTCCCCATGAGA GGCCTTGAGTGGCTGGGAAGGACATACTACAGG TCCAAGTGGTATAGTGCTTATCAGTATCTATGG AAAGTCGAGTATCCATCAACCAGACACATCCA AGAACCAGTCTCCCTGCAGCTGAACTCTGTGAC TCCGAGGACACGGCTGTTTATTACTGTGCAAGA GATAAGGCAGCTGGAGAGAATGACTTCTACTACT ACGGTATGGACGTCTGGGGCCAAGGGACCACGG TCACCGTCTCCTCA |
| | | | SEQ ID NO: 27453 | SEQ ID NO: 31459 |
| | | AA | QSALTQPASVSGSPGQSITISCTGTSSDVGRFNLV SWYQHHPGNAPKLMIYEVSKRPSGVSNRFSGSK SGNTASLTISGLQAEDEADYCCSYAGSSTFVVF GGGTKLTVL | QVQLQQSGPGLVKPSQTLSLTCAISGDSVSSNSAA WNWIRQSPSRGLEWLGRTYYRSKWYSAYPVSMES RVSINPDTSKNQFSLQLNSVTPEDTAVYYCARDKA AGRNDFYYGMDVWGQGTTVTVSS |
| | | | SEQ ID NO: 27454 | SEQ ID NO: 31460 |

FIGURE 50
(Continued)

| | | | |
|---|---|---|---|
| iPS:436816 | 21-225_179H5 | NA | TCTTCTGAGCTGACTCAGGACCCTGCTGTCT GTGGCCTTGGGACAGACAGTCAGGATCACATG CCAAGGAGACAGTCTCAGAAACTATTATGCAA GCTGGTACCAGCAGAAGCCAGGACAGGCCC TGTATTTGTCATCTATGGTAAAAACAACCGGC CCTCAGGGATCCCAGACCGATTCTCTGGCTCC AGGTCAGGAAACACAGCTTCCTTGACCATCAC TGGGGCTCAGGCGGAAGATGAGGCTGACTATT ACTGTAACTCCCGGGACAGCAGTGGTAACCAT TGGGTGTTCGGCGGAGGGACCAAACTGACCGT CCTA<br><br>SEQ ID NO: 27455 | CAGGTGCAGTTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAGT AATGAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATATCCG GAACTACTACGGTTTGGACGTCTGGGGCCAA GGGACCACGGTCACCGTCTCCTCA<br><br>SEQ ID NO: 31461 |
| | | AA | SSELTQDPAVSVALGQTVRITCQGDSLRNYYAS WYQQKPGQAPVFVIYGKNNRPSGIPDRFSGSRS GNTASLTITGAQAEDEADYYCNSRDSSGNHWVF GGGTKLTVL<br><br>SEQ ID NO: 27456 | QVQLVESGGGVVQPGRSLRLSCAASGFTFSSYGMH WVRQAPGKGLEWVAVIWYDGSNEYYADSVKGRF TISRDNSKNTLYLQMNSLRAEDTAVYYCARDIRNY YYGLDVWGQGTTVTVSS<br><br>SEQ ID NO: 31462 |
| iPS:436818 | 21-225_179C7 | NA | TCCTATGAGCTGACTCAGCCACCCTCAGTGTC CGTGTCCCAGGACAGACAGCCAGTATCACCT GCTCTGGAGATAAATTGGGGGATAAATATGTT GCTCTGGTATCAACAGAGGCCGGGCCAGTCCCC TGTGCTGGTCATCTATCAGGATAGTAAGCGGC CCTCAGGGATCCCTGAGCGATTCTCTGGCTCC AACTCTGGGAACACAGCCACTCTGACCATCCG CGGGACCCAGGCTATGGATGAGGCTGACTATT ACTGTCAGGCGTGGGACAGCAACACTGCAGTG GTATTCGGCGGAGGGACCAAGCTGACCGTCCT A<br><br>SEQ ID NO: 27457 | CAGGCGCAGCTGGTGGAGTCTGGGGGAGGCGTG GTCCAGCCTGGGAGGTCCCTGAGACTCTCCTGTG CAGCGTCTGGATTCACCTTCAGTAACTCTGGCAT GCACTGGGTCCGCCAGGTCCAGGCAAGGGGCT GGAGTGGGTGGCAGTTATATATTATGGAAGT TATAAAATACAATGCAGACTCCGTGAAGGGCCGA TTCACCATCTCCAGAGACAATTCCAAGAACACGC TGTATCTGCAAATGAACAGCCTGAGAGCCGAGG ACACGGCTGTATATTACTGTGCGAGAGACCGTCA TTACGATTTCCACGTTCCTACTATTACTATTACG GTATGGACGTCTGGGGCCAAGGGACCACGGTCA CCGTCTCCTCA<br><br>SEQ ID NO: 31463 |

FIGURE 50
(Continued)

| | | | |
|---|---|---|---|
| iPS:436820 | 21-225_179D10 | AA | SYELTQPPSVSVSPGQTASITCSGDKLGDKYVCW YQQRPGQSPVLVIYQDSKRPSGIPERFSGSNSGN TATLTIRGTQAMDEADYYCQAWDSNTAVVFGG GTKLTVL<br>SEQ ID NO: 27458 | QAQLVESGGGVVQPGRSLRLSCAASGFTFSNSGMH WVRQGPGKGLEWVAIIYDGSYKYNADSVKGRFT ISRDNSKNTLYLQMNSLRAEDTAVYYCARDRHYD FHVPYYYYGMDVWGQGTTVTVSS<br>SEQ ID NO: 31464 |
| | | NA | CAGTCTGTGTTGACGCAGCCGCCCTCAGTGTC TGGGGCCCCAGGGCAGAGGGTCACCATCTCCT GCACTGGGAGCAGCTCCAACTTCGGGACAGAT TATGATGTACACTGGTACCAGCAATTCCAGG AACAGCCCCAAACTCCTCATCTATGGTCACA GCAACCGGCCCTCAGGGGTCCCTGACCGATTT TCTGGCTCCAAGTCTGGCACCTCAGCTCCCT GGCCATCACTGGGCTCCAGGCTGAGGATGAGG CTGATTATTACTGCCAGTCCTATGATAGAAGC CTGAATGTGGTCTTCGGCGGAGGGACCAAGCT GACCGTCCTA<br>SEQ ID NO: 27459 | GAGGTGCAGCTGGTGGAGTCTGGGGGAGGCTTG GTACAGCCTGGGGGGTCCCTGAGATTCTCCTGTG CAGCCTCTGGATTCACCTTCAGTAGCTATAGCAT GAACTGGGTCCGCCAGGCTCCAGGGAAGGGGCT GGAGTGGGTTGCATACATTAGTAGTAGTGGAAGT ACCACATACTACGCAGACTCTGTGCAGGGCCGAT TCACCATCTCCAGAGACAATGCCAAGAACTCACT GTATCTGCAAATGAACAGCCTGAGAGACGAGGA CACGGCTGTGTATCGCTGTGCGAGAGATAGTAGG AAGGGGTTCTACTACGGTCTGGACGTCTGGGGCC AAGGGATCACCGTCACCGTCTCCTCA<br>SEQ ID NO: 31465 |
| | | AA | QSVLTQPPSVSGAPGQRVTISCTGSSSNFGTDYD VHWYQQFPGTAPKLLIYGHSNRPSGVPDRFSGS KSGTSASLAITGLQAEDEADYYCQSYDRSLNVV FGGGTKLTVL<br>SEQ ID NO: 27460 | EVQLVESGGGLVQPGGSLRFSCAASGFTFSSYSMN WVRQAPGKGLEWVAYISSSGSTTYYADSVQGRFTI SRDNAKNSLYLQMNSLRDEDTAVYRCARDSRKGF YYGLDVWGQGITVTVSS<br>SEQ ID NO: 31466 |

FIGURE 50
(Continued)

| | | | |
|---|---|---|---|
| iPS:436822 | 21-225_180D4 | NA | TCCTATGAGCTGACTCAGGACACCCTCAGTGTC CGTGTCCCCAGGACAGACAGCCAGCATCACCT GCTCTGGAGATAGCAGGATAAATATGCT TGCTGGTATCAGCAGAAGCCAGGCCAGTCCCC TGTGCTGGTCATCTATGAAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGGTGACTATT ACTGTCAGGCGTGGGACAGTAGGAAAGTGGT ATTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGCTTCTGGATTCACCTTCAGTAACTTTGGCAT GCACTGGGTCCGCCAGGCTCCAGGCAAGGGCT GGAGTGGGTGGCAATTATATGGTATGATGGAAGT GATAAATACTATGCAGACTCCGTGAAGGGCCGA TTCACCATCTCCAGAGACAATTCCAAGAACACGC TGTATCTGCAAATGAACACCCTGAGAGCCGAAG ACACGGCTGTGTATTTCTGTGCGAGAGGGGGCC CCGTTCTCTACGGTGACTATGTACTTTGACTACT GGGGCCAGGGAACCCTGGTCACCGTCTCCTA |
| | | | SEQ ID NO: 27461 | SEQ ID NO: 31467 |
| | | AA | SYELTQTPSVSVSPGQTASITCSGDRLGDKYACW YQQKPGQSPVLVIYEDRKRPSGIPERFSGSNSGN TATLTISGTQAMDEGDYYCQAWDSRKVVFGGG TKLTVL | QVQLVESGGGVVQPGRSLRLSCAASGFTFSNFGMH WVRQAPGKGLEWVAIIWYDGSDKYYADSVKGRFT ISRDNSKNTLYLQMNTLRAEDTAVYFCARGGPPFS TVTMYFDYWGQGTLVTVSS |
| | | | SEQ ID NO: 27462 | SEQ ID NO: 31468 |
| iPS:436824 | 21-225_180C5 | NA | TCCTATGAACTGACTCAGCCACCCTCAGTGTC CGTGTCCCCAGGACAGACAGCCAGCATCACCT GCTCTGGAGATAAATTGGGGGAAAAATATGCT TGCTGGTATCAGCAGAAGCCAGGCCAGTCCCC TGTACTGGTCATCTATCAAGATAGAAAGCGGC CCTCAGGGATCCCTGAGCGATTCTCTGGCTCC AACTCTGGGAACACAGCCACTCTGACCATCAG CGGGACCCAGGCTATGGGACAGCAGCACTGGGTA ACTGTCAGGCGTGGGACAGCAGCACTGGGGTA TTCGGCGGAGGGACCAAGCTGACCGTCCTA | CAGATCACCTTGAAGGAGTCTGGTCCTACGCTGG TGAAACCCACACAGACCCTCAGCTGACTCTGCAC CTTCTCTGGGTTCTCACTCAGCACTAGTGAGTG GGTGTGGGCTGGATCCGTCAGCCCCCAGGAAAG GCCCTGGAGTGGCTTGGATTCATTTCTTGGAATG ATGATAAGGCTACAACCCATCTCTGAAGAGCA GCCTCACCATCACCAAGGACACCTCCAAAAACC AGGTGGTTCTTATAATGACCAACATGACCCCTGT GGACACAGCCACATATTACTGTGCACAAAGC AGCAGCTGTTGCTTTGATATCTGGGGCCAAGGG ACAATGGTCACCGTCTCTTCA |
| | | | SEQ ID NO: 27463 | SEQ ID NO: 31469 |

FIGURE 50
(Continued)

| | | | |
|---|---|---|---|
| iPS:436826 | 21-225_180G5 | AA | SYELTQPPSVSVSPGQTASITCSGDKLGEKYACW YQQKPGQSPVLVIYQDRKRPSGIPERFSGSNSGN TATLTISGTQAMDEADYYCQAWDSSTAVFGGG TKLTVL<br>SEQ ID NO: 27464 | QITLKESGPTLVKPTQTLTLTCTFSGFSLSTSGVVG WIRQPPGKALEWLGFISWNDDKRYSPSLKSSLTITK DTSKNQVVLIMTNMDPVDTATYYCAHKAAAVAFD IWGQGTMVTVSS<br>SEQ ID NO: 31470 |
| | | NA | TCCTATGAGCTGACTCAGCCACCCTCAGTGTC CGTGTACCCAGGACAGACAGCCAGCATCACCT GCTCTGGAGATAAATTGGGGGATAAATATGTT AGCTGGTATCAACAGAAGCCAGGCCAGTCCCC TGTTCTGGTCATCTATCAAGATAGCAAGCGGC CCTCAGGGATCCCTGAGCGATTCTCTGGCTCC AACTCTGGGAACCCAGCTCTCTGACCATCAG CGGGACCCAGGCTATGGGGACATCACCACTGCGGTA ACTGTCAGGCGCTGTGGGAGGGACCAAGCTGACCGTCCTA TTCGGCGGAGGGACCAAGCTGACCGTCCTA<br>SEQ ID NO: 27465 | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGACAGGCCACTGGACAAGGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAGCTGAGCAGCCTGAGATCTG AGGACACGGCCGTGTATTACTGTGCGAGAGGGTT TTATTACTATGGTTCGGGAGTCATGTCCCTACC ACTACTACGGTTTGGACGTCTGGGGCCAAGG GACCACGGTCACCGTCTCCTCA<br>SEQ ID NO: 31471 |
| | | AA | SYELTQPPSVSVSPGQTASITCSGDKLGDKYVS WYQQKPGQSPVLVIYQDSKRPSGIPERFSGSNSG NPASLTISGTQAMDEADYYCQAWDITTAVFGGG TKLTVL<br>SEQ ID NO: 27466 | QVQLVQSGAEVKKPGASVKVSCKASGYTFTSYDIN WVRQATGQGLEWMGWMNPNSGNTGYAQKFQGR VTMTRNTSISTAYMELSSLRSEDTAVYYCARGFYY YGSGSHVPYHYYYGLDVWGQGTTVTVSS<br>SEQ ID NO: 31472 |

FIGURE 50
(Continued)

| | | | | |
|---|---|---|---|---|
| iPS:436828 | 21-225_181H1 | NA | TCCTATGAGCTGACTCAGACACCCTCAGTGTC CGTGTCCCCAGGACAGACAGCCAGCATCACCT GCTCTGGAGATATCAGCAGACCAGCCAGTGCT TGCTGGTATCAGCAGAAGCCAGGCCAGTCCCC TGTGCTGGTCATCTATGAAGATAGGAAGCGGC CCTCAGGGATCCCTGAGCGATTCTCTGGCTCC AACTCTGGAAACACAGCCACTCTGACCATCAG CGGGACCCAGGCTATGGATGAGCTGACTATT ACTGTCAGGCGTGGGACCAGCAGGAAAGTGGT ATTCGGCGGAGGGACCAAGCTGACCGTCCTA SEQ ID NO: 27467 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAATTATATGGTATGATGAAGT GATAAATACTATGCAGAGACAATTCCAAGAACACGC ATCACCATCTCCAGAGACAATTCCAAGAACACGC TGTATCTGCAAATGAACACCCTGAGAGCCGAAG ACACGGCTGTGTATTTCTGTGCGAGAGGGGGCC CCCGTTTCTACGGTGACTATGTACTTCGACTACT GGGGCCAGGGAACCCTGGTCACCGTCTCCTCA SEQ ID NO: 31473 |
| | | AA | SYELTQTPSVSVSPGQTASITCSGDKLGDKYAC WYQQKPGQSPVLVIYEDRKRPSGIPERFSGSNSG NTATLTISGTQAMDEADYYCQAWDSRKVVFGG GTKLTVL SEQ ID NO: 27468 | QVQLVESGGGVVQPGRSLRLSCAASGFTFSNYGM HWVRQAPGKGLEWVAIIWYDGSDKYYADSVKGRI TISRDNSKNTLYLQMNTLRAEDTAVYFCARGGPPF STVTMYFDYWGQGTLVTVSS SEQ ID NO: 31474 |
| iPS:436830 | 21-225_51F4 | NA | CAGTCTGTGCTGACTCAGCCACCCTCAGCGTC TGGGACCCCCGGGCAGAGGGTCACCATCTCTT GTTCTGGAAGCAGCTCCAACATCGGAAGTAAT ATTGTGACCTGGTACCAGCAGCTCCCAGGAAC GGCCCCCAAACTCCTCATCTATAGTAATGATC AGCGGCCCTCAGGGGTCCCTGACCGATTCTCT GGCTCCAAGTCTGGCACCTCAGTCTGAGGATGACACGCTG CATCAGTGGGCTCCAGTCTGAGGATGACACGCTG ATTATTACTGTACAGCATGGCGGAGGGACCACGCT AATGGTTGGTGTTCGGCGGAGGGACCAAGCTG GACCGTCCTA SEQ ID NO: 27469 | CAGGTTCAGCTGGTGCAGTCTGGAGCTGAGGTGA AGAAGCCTGGGGCCTCAGTGAAGGTCTCCTGCA AGGCTTCTGGTTACACCTTTAACAGTATGTAT CAGTGGGTGCGACAGGCCCCTGGACAAGGGCT TGAGTGGATGGGATGGATCAGCGTTATAATGGT AACACAAAGTATGCACAGAAGCTCCAGGGCAGA GTCACCATGACCACAGACACATCCACGAGCACA GCCTACATGGAGCTGAGGAGCCTGAGATCTGAC GACACGGCCGTGTATTACTGTGCGAGACACGATT TTTGGAGTGGTTATTATAAGGGTATGGACGTCTG GGGCCAAGGGACCACGGTCACCGTCTCCTCA SEQ ID NO: 31475 |

FIGURE 50
(Continued)

| | | | |
|---|---|---|---|
| | | AA | QSVLTQPPSASGTPGQRVTISCSGSSSNIGSNIVT WYQQLPGTAPKLLIYSNDQRPSGVPDRFSGSKS GTSASLAISGLQSEDETDYYCTAWDDSLNGWVF GGGTTLTVL<br><br>SEQ ID NO: 27470 | QVQLVQSGAEVKKPGASVKVSCKASGYTFNSYGIS WVRQAPGQGLEWMGWISAYNGNTKYAQKLQGR VTMTTDTSTSTAYMELRSLRSDDTAVYYCARHDF WSGYYKGMDVWGQGTTVTVSS<br><br>SEQ ID NO: 31476 |
| iPS:436832 | 21-225_51D8 | NA | CAGTCTGTGCTGACGCAGCCGCCCTCAGTGTC TGGGGCCCCAGGGCAGAGGGTCACCATCTCCT GCACTGGGAGCAGCTCCAACATCGGGGCAGG TTTTGAAGTACACTGGTACCAGCAGCTTCCAG GAACAGCCCCCAAACTCCTCATCTATGGTAAC AGCAATCGGCCCTCAGGGGTCCCTGACCGATT CTCTGGCTCCAAGTCTGGCACCTCAGCCTCCT GGCCATCACTGGGCTCCAGGCTGAGGATGAGG CTGATTATTACTGCCAGTCCTATGACAGCAGC CTGAGTGGTTATGTCTTCGGAACTGGGACCAA GGTCACCGTCCTA<br><br>SEQ ID NO: 27471 | CAGGTACAGCTGCAGCAGTCAGGTCCAGGACTG GTGAAGCCCTCGCAGACCCTCACTCACCTGTG CCATCTCCGGGACAGTGTCTCTAGTAACAGTGC TGCTTGGAACTGGATCAGGCAGTCCCCATCGAGA GGCCTTGAGTGGCTGGGAAGGACATACTACAGG TCCAAGTGGTATAATGATTATGCAGTATCTGTGA AAAGTCGAATAACCTTCAACCCGGACACATCCA AGAACCAGTTCTCCCTGCGGCTGTATTACTGTGCAAGA TCCCGAGGACACGGCTGTGTATTACTGTGCAAGA GACCGCTATAAACTGGAACTACCCCTACTGGTACT TCGATCTCTGGGGCCGTGGCACCCTGGTCACTGT CTCCTCA<br><br>SEQ ID NO: 31477 |
| | | AA | QSVLTQPPSVSGAPGQRVTISCTGSSSNIGAGFEV HWYQQLPGTAPKLLIYGNSNRPSGVPDRFSGSK SGTSASLAITGLQAEDEADYYCQSYDSSLSGYVF GTGTKVTVL<br><br>SEQ ID NO: 27472 | QVQLQQSGPGLVKPSQTLSLTCAISGDSVSSNSAA WNWIRQSPSRGLEWLGRTYYRSKWYNDYAVSVK SRITFNPDTSKNQFSLRLNSVTPEDTAVYYCARDRY NWNYPYWYFDLWGRGTLVTVSS<br><br>SEQ ID NO: 31478 |

FIGURE 50
(Continued)

| | | | |
|---|---|---|---|
| iPS:436834 | 21-225_52F1 | NA | CAGTCTGTGCTGACTCAGCCACCTCAGCGTCTGGGACCCCGGGAAGCAGCTCCAACATCGGAAGTAATGTTCTGAACCTGGTACCAGCAGTCCCAGGAACATTGTGACCTGGTGCGACAGGCCCCTGGACAAGGCTGGCCCCAAACTCCTCATCTATAGTAATGATCAGCGGCCCTCAGGGGTCCCTGACCGATTCTCTAGCGGCCTCCAAGTCTGGCACCTCAGCCTCCTGGCCATCAGTGGGCTCCAGTCTGAGGATGAGGCTGATTATTACTGTGCAGCATGGGATGACAGCCTGAATGGTGTGGTGTTCGGCGGAGGGACCACCGCTGACCGTCCTA<br/><br/>SEQ ID NO: 27473 | CAGGTTCAGCTGGTGCAGTCTGGAGCTGAGGTGAAGAAGCCTGGGGCCTCAGTGAAGGTCTCCTGCAAGGCTTCTGGTTACACCTTTAACAGCTATGGTGTCAGCTGGGTGCGACAGGCCCCTGGACAAGGCTTGAGTGGATGGGATGGATCAGCGCTTATAATGGTAACAGAAAGTATGCACAGAAGCTCCAGGGCAGAGTCTCCATGACCACAGACACATCCACGAGCACAGCCTACATGGAGCTGAGGAGCCTGAGATCGACGACACGGCCGTGTATTACTGTGCGAGACACGATTTTTGGAGTGGTTATTATAAGGGTATGGACGTCTGGGGCCAAGGGACCACGGTCACCGTCTCCTCA<br/><br/>SEQ ID NO: 31479 |
| | | AA | QSVLTQPPSASGTPGQRVTISCSGSSSNIGSNIVTWYQQLPGTAPKLLIYSNDQRPSGVPDRFSGSKSGTSASLAISGLQSEDEADYYCAAWDDSLNGWVFGGGTTLTVL<br/><br/>SEQ ID NO: 27474 | QVQLVQSGAEVKKPGASVKVSCKASGYTFNSYGVSWVRQAPGQGLEWMGWISAYNGNRKYAQKLQGRVSMTTDTSTSTAYMELRSLRSDDTAVYYCARHDFWSGYYKGMDVWGQGTTVTVSS<br/><br/>SEQ ID NO: 31480 |
| iPS:436836 | 21-225_52H1 | NA | TCCTATGAGCTGACTCAGCCACCTCAGTGTTCGTGTCCCAGGACAGACAGGCCAGCATCACCTCCTCTGAGATAAGCAGAAGCCAGGTCCAGTCCCTGGAGATAAATATGTTTCCTGGTATCAGCAGAAGCCAGGCCAGTCCCCTGTGCTGGTCATCTATCAAGATAGAAAGCGGCCCTCAGGGATCCCTGAGCGATTCTCTGGCTCCAATTCTGGGAATACAGCCACTCTGACCATCAGCGGGACCCAGGCTATGGATGAGGCTGACTATTATGTGTGGCGTGGGACAACAGCACTGTGGTATTCGGCGGAGGGACCAAGCTGACCGTCCTA | CAGGTGCAGCTGGTGGAGTCTGGGGGAGGCGTGGTCCAGCCCGGGAGGTCCCTGAGACTCTCCTGTGCAGCGTCTGGATTCACCTTCAGTGGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTTTATTACTGTGCGAGAGATCGGGTCTATTGTAGTAGTTCCAGCTGCTCATATTACTACTACTACTACGGTATGGACGTCTGGGGCCAAGGGACCACGGTCACCGTCCTCA |

FIGURE 50
(Continued)

| | | | | |
|---|---|---|---|---|
| | | | SEQ ID NO: 27475 | SEQ ID NO: 31481 |
| | | AA | SYELTQPPSVFVSPGQTASITSSGDKLGDKYVSW YQQKPGQSPVLVIYQDRKRPSGIPERFSGSNSGN TATLTISGTQAMDEADYYCQAWDNSTVFGGG TKLTVL | QVQLVESGGGVVQPGRSLRLSCAASGFTFSGYGM HWVRQAPGKGLEWVAVIWYDGSNKYYADSVKGR FTISRDNSKNTLYLQMNSLRAEDTAVYYCARDRVY CSSSSCSYYYYYGMDVWGQGTTVTVSS |
| | | | SEQ ID NO: 27476 | SEQ ID NO: 31482 |
| iPS:436838 | 21-225_52H4 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ACTATGTCTCTGGTACCAACAGCACCCAGGC AAAGCCCCCAAAACTCATGATTTATGAGGTCAG TAATCGGCCCTCAGGGGTTTCTAATCGCTTCTC TGGCTCCAAGTCTGGCAATACGGCCTCCCTGA CCATCTCTGGGCTCCAGGCTGAGGACGAGGCT GATTATTACTGCAACTCATATACAAGCAACAT CACTTGGGTGTTCGGCGGAGGGACCAAGCTGA CCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTCAGTTCACTTTGGCAT GCACTGGGTCCGCCAGGCTCCAGGCAAGGGGCT GAAATGGGTGGCAGTTATTTGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGGGACTG GAACTACGAGGGTTTGACTACTGGGGCCAGGG AACCCTGGTCACCGTCTCCTCA |
| | | | SEQ ID NO: 27477 | SEQ ID NO: 31483 |
| | | AA | QSALTQPASVSGSPGQSITISCTGTSSDVGGYNY VSWYQQHPGKAPKLMIYEVSNRPSGVSNRFSGS KSGNTASLTISGLQAEDEADYYCNSYTSNITWVF GGGTKLTVL | QVQLVESGGGVVQPGRSLRLSCAASGFTFSHFGMH WVRQAPGKGLKWVAVIWYDGSNKYYADSVKGRF TISRDNSKNTLYLQMNSLRAEDTAVYYCARGDWN YEGFDYWGQGTLVTVSS |
| | | | SEQ ID NO: 27478 | SEQ ID NO: 31484 |

FIGURE 50
(Continued)

| | | | |
|---|---|---|---|
| iPS:436840 | 21-225_53E9 | NA | TCCTATGAGCTGACTCAGCCACCCTCAGTGTC CGTGTCCCCAGGACAGACAGCCAGCATCACCT GCTCTGGAACTAAATTGGGGACATAAATATGT TGCTGGTATCAACAGAAGCCAGGCCAGTCCCC TGTGTTGGTCATCAATCAAGATACAATGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGACGTGGGACAGCAGCACTGCGGTT TTCGGCGGAGGGACCACGCTGACCGTCCTA <br>SEQ ID NO: 27479 | CAGGTGCAGCTGGTGCAGTCTGGGGCTGAGGTG AAGAAGCCTGGGGCCTCAGTGAAGGTCTCCTGC AAGGCTTCTGGAAACACCTTCACCGGCTACTATA TGCACTGGGTGCGACAGGCCCCTGGACAAGGGC TTGAGTGGATGGGATGGATCATCCCTAACAGTGG TGACACAAACTATGCACAGAAGTTTCAGGGCAG GGTCACCATGACCAGGACACGTCCATCAGCAC AGCCTACATGGAGCTGAGCAGGCTGAGATCTGA CGACACGGCCGTCTATTACTGTGCGAGAGATGGG TATAGCAGTGGCTGGTTCAACTGGTTCGACCCCT GGGGCCAGGGAACCCTGGTCACCGTCTCCTA <br>SEQ ID NO: 31485 |
| | | AA | SYELTQPPSVSVSPGQTASITCSGTKLGDKYVCW YQQKPGQSPVLVINQDTMRPSGIPERFSGSNSGN TATLTISGTQAMDEADYYCQTWDSSTAVFGGGT TLTVL <br>SEQ ID NO: 27480 | QVQLVQSGAEVKKPGASVKVSCKASGNTFTGYYM HWVRQAPGQGLEWMGWIIPNSGDTNYAQKFQGR VTMTRDTSISTAYMELSRLRSDDTAVYYCARDGYS SGWFNWFDPWGQGTLVTVSS <br>SEQ ID NO: 31486 |
| iPS:436842 | 21-225_54E9 | NA | CAGTCTGTGCTGACTCAGCCACCCTCAGCGTC TGGGACCCCCGGGCAGAGGGTCACCATCTCT TGTTCTGGAAGCAACTCCAACATCGAAATAAT ATTGTCACCTGGTACCAGCAGCTCCCAGGAAC GGCCCCCAAACTCCTCATCTATGTTAATGATC AGCGGCCCTCAGGGGTCCCTGACCGATTCTCT GGCTCCAAGTCTGGCACCTCTGCCTCCCTGGC CATCAGTGGGCTCCAGTCTGAGGATGAGGCTG ATTATTACTGTGCAGCATGGGATGACAGCCTG AATGGTTGGGTGTTCGGCGGAGGGACCACGCT GACCGTCCTA <br>SEQ ID NO: 27481 | CAGGTTCAGCTGGTGCAGTCTGGAGCTGAGGTGA AGAAGCCTGGGGCCTCAGTGAAGGTCTCCTGCA AGGCTTCTGTTACACCTTTAACAGTCATGGTAT CAGCTGGGTGCGACTGGCCCCTGGACAAGGGCTT GAGTGGATGGGATGATTAGTGCTTATAATGGTA ACACAAAGAATGCACAGAAGTCCAGGCAGAG TCACCATGACCACAGACACATCCACGAGCACAG CCTACATGGAGCTGAGGAGCTGAGATCTGACG ACACGGCCGTTTATTACTGTGCGAGACACGATTT TGGAGTGGTTATTATAAGGTATGGACGTCTGG GGCCAAGGGACCACGGTCACCGTCTCCTCA <br>SEQ ID NO: 31487 |

FIGURE 50
(Continued)

| | | | | |
|---|---|---|---|---|
| iPS:436844 | 21-225_56G1 | AA | QSVLTQPPSASGTPGQRVTISCSGSGNSNIGNNIVT WYQQLPGTAPKLLIYVNDQRPSGVPDRFSGSKS GTSASLAISGLQSEDEADYYCAAWDDSLNGWV FGGGTLTVL<br><br>SEQ ID NO: 27482 | QVQLVQSGAEVKKPGASVKVSCKASGYTFNSYGIS WVRLAPGQGLEWMGWISAYNGNTKNAQKLQGRV TMTDTSTSTAYMELRSLRSDDTAVYYCARHDFW SGYYKGMDVWGQGTTVTVSS<br><br>SEQ ID NO: 31488 |
| | | NA | CAGTCTGTGCTGACTCAGCCACCCTCAGCGTC TGGGACCCCGGGCAGAGGGTCACCATCTCTT GTTCTGGAAGCAGCTCCAACATCGGAAGTCAT ATTGTTACCTGGTACCAGCAGCTCCCAGGAAC GGCCCCCAAACTCCTCATCTACAGTAATGATC AGCGGCCCTCAGGGGTCCCTGACCGATTCTCT GGCTCCAAGTCTGGCACCTCAGCCTCCCTGGC CATCAGTGGGCTCCAGTCTGAGGATGAGGCTG ATTATTACTGTGCAGTATGGGATGACAGCCTG ATTGGTGGGTGTTCGGCGGAGGGACCACGCT GACCGTCCTA<br><br>SEQ ID NO: 27483 | CAGGTTCAGCTGGTGCAGTCTGGAGCTGAGGTGA AGAAGCCTGGGGCCTCAGTGAAGGTCTCCTGCA AGGCTTCTGGCTACACCTTTAACAGTATGGTAT CAGCTGGGTGCGACAGGCCCCTGGACAAGGGCT TGAGTGGATGGGATGGATCAGCGCTTATAATGGT AACACAAAGTATGCACAGAAGTTCCAGGCAGA GTCACCATGACCACAGACACATCCAGAGCACA GCCTACATGGAGCTGAGGAGCCTGAGATCTGAC GACACGGCCGTGTATTACTGTGCGAGACACGATT TTTGGAGTGGTTATTATAAGGGTATGGACGTCTG GGGCCAAGGGACCACGGTCACCGTCTCCTCA<br><br>SEQ ID NO: 31489 |
| | | AA | QSVLTQPPSASGTPGQRVTISCSGSGSSSNIGSHIVT WYQQLPGTAPKLLIYSNDQRPSGVPDRFSGSKS GTSASLAISGLQSEDEADYYCAVWDDSLIGWVF GGGTLTVL<br><br>SEQ ID NO: 27484 | QVQLVQSGAEVKKPGASVKVSCKASGYTFNSYGIS WVRQAPGQGLEWMGWISAYNGNTKYAQKFQGRV TMTDTSTSTAYMELRSLRSDDTAVYYCARHDFW SGYYKGMDVWGQGTTVTVSS<br><br>SEQ ID NO: 31490 |

FIGURE 50
(Continued)

| | | | |
|---|---|---|---|
| iPS:436846 | 21-225_56E3 | NA | CAGTCTGTGCTGACTCAGCCACCCTCAGCGTC TGGGACCCCGGGAAGCAGTCCAACATCGAAGTAAT GTTCTGTGGTTACCAGCAGCTCCCAGGAAC ATTGTTACCTGGTACCAGCAGCTCCCAGGAAC GGCCCCCAAACTCCTCATCTATAGTAATAATC AGCGGCCCTCAGGGGTCCCTGACCGATTCTCT GGCTCCAAGTCTGGCACCTCAGCTCCCTGGC CATCAGTGGACTCCAGTCTGAGCATGGATGACAGCCTG ATTATTGCTGTGCAGCATGGGATGACAGCCTG AATGGTTGGGTGTTCGGCGGAGGGACCACGCT GACCGTCCTA |
| | | | SEQ ID NO: 27485 |
| | | AA | QSVLTQPPSASGTPGQRVTISCSGSSSNIGSNIVT WYQQLPGTAPKLLIYSNNQRPSGVPDRFSGSKS GTSASLAISGLQSEDEADYCCAAWDDSLNGWVF GGGTTLTVL |
| | | | SEQ ID NO: 27486 |
| | | NA | CAGGTTCAACTGGTGCAGTCTGGAGCTGAGGTGA AGAAGCCTGGGGCCTCAGTGAAGGTCTCCTGCA AGGCTTCTGGTTACACCTTTAACAGCTATGGTTTC AGCTGGGTGCGACAGGCCCCTGGACAAGGCTT GAGTGGATGGGATGGATCAGCGCTTATAATGGTA ACACAAAGGAAGCACAGAAGTTCCAGGGCAGAG TCACCATGACCACAGACACATCCACGAGCACAG CCTACATGGAGCTGAGGAGCTGAGAGCTGACG ACACGGCCGTGTATTACTGTGCGAGACACGATTT TTGGAGTGGTTATTATAAGGGTATGGACGTCTGG GGCCAAGGGACCACGGTCACCGTCTCCTCA |
| | | | SEQ ID NO: 31491 |
| | | AA | QVQLVQSGAEVKKPGASVKVSCKASGYTFNSYGF SWVRQAPGQGLEWMGWISAYNGNTKEAQKFQGR VTMTTDTSTSTAYMELRSLRADDTAVYYCARHDF WSGYYKGMDVWGQGTTVTVSS |
| | | | SEQ ID NO: 31492 |
| iPS:436848 | 21-225_57F1 | NA | TCCTATGAGCTGACTCAGCCACCCTCAGCGTC CGTGTCCCAGGACAGACAGCAGCATCACCT GCTCTGGAGATAAACTGGGGGAAAAATATGCT TGCTGGTATCAGCAGAAGCCAGGCCAGTCCCC TGTGTTGGTCATCTATCAAGATAGGAAGCGGC CCTCAGGGATCCCTGAGCGATTCTCTGGCTCC AATTCTGGGAACACACGGCTATGGATGAGGCTGAGCAG CGGGACCCAGGCGTGGGACAGCAGCACTGTGTA ACTGTCAGGCGCTCCTACTGGGACAGTGGGTGACT TTCGGCGGAGGGACCAAACTGACCGTCCTA |
| | | | SEQ ID NO: 27487 |
| | | NA | CAGATCACCTTGAAGGAGTCTGGTCCTACGCTGG TGAAACCCACACAGACCCTCACGCTGACCTGCAC CTTCTCTGGGTTCTCACTCAGTACTAGTGAGTG GGTGTGGGCTGGATCCGTCAGCCCCCAGGAAAG GCCCTGGAGTGGCTTGCACTCATTATTGGCATG AAGATAAGCGCTACAGCCCATCTCTGAAGAGCA GGCTCACCATCACTGAGGACACCTCCAAAAACC AGGTGGACCTTACAATGACCAACATGCCCCTGT GGACACAGCCACATATTACTGTGCACACGTCACA GGTATAGCAGCTCCCTACTGGGGCCAGGGAACC CTGGTCACCGTCTCCTCA |
| | | | SEQ ID NO: 31493 |

FIGURE 50
(Continued)

| | | | | |
|---|---|---|---|---|
| iPS:436850 | 21-225_57D9 | AA | SYELTQPPSASVSPGQTASITCSGDKLGEKYACW YQQKPGQSPVLVIYQDRKRPSGIPERFSGSNSGN TATLTISGTQAMDEADYYCQAWDSSTVFGGG TKLTVL<br>SEQ ID NO: 27488 | QITLKESGPTLVKPTQTLTLTCTFSGFSLSTSGVG WIRQPPGKALEWLALIYWHEDKRYSPSLKSRLTITE DTSKNQVDLTMTNMAPVDTATYYCAHVTGIAAPY WGQGTLVTVSS<br>SEQ ID NO: 31494 |
| | | NA | TCCTATGAGCTGACTCAGCCACCCTCAGTGTC CGTGTCCCCAGGACAGACAGCCAGCATCACCT GCTCTGAGAGAAATTGGGGACAGCCAGTCACCT TGCTGGTCTCAGCAGAAGCCAGGCCAGTCCCC TGTGTTGGTCATCTATCAAGATAGCAAGCGGC CCTCAGGGATCCCTGAGCGATTCTCTGGCTCC AACTCTGGGAACACAGGCTATGAGGCTGACTCAG CGGGACCCAGGCTGTGGGACAGCAGCACTGTGTA ACTGTCAGGGCGTGGGACAGCAGCACTGTGGTA TTCGGCGGAGGGACCAAGCTGACCGTCCTA<br>SEQ ID NO: 27489 | CAGATCACCTTGAAGGAGTCTGGTCCTATGCTGG TGAAACCACACAGACCCTCACGCTGACCTGCAC CTTCTCTGGGTTCTCACTCAGCACTAGTGGAGTG GGTGTGGGCTGGATCCGTCAGCCCCCAGGAAAG GCCCTGGAGTGGCTTGCACTCATTTATTGGAATG ATGATAAGCGCTACAGTCCATCTCTGAAGAGCAG GCTCACCATCACCGAGGACACCTCAAAAACCA GGTGGTCCTTACAATGACCAACATGGACCCTGTG GACACAGCCACATATTACTGTGCACATGCAGTGG CTGTCTCCTTTGACTACTGGGGCCAGGGAACCCT GGTCACCGTCTCCTCA<br>SEQ ID NO: 31495 |
| | | AA | SYELTQPPSVSVSPGQTASITCSGEKLGEKFACW SQQKPGQSPVLVIYQDSKRPSGIPERFSGSNGNT ATLTIISGTQAMDEADYYCQAWDSSTVFGGGT KLTVL<br>SEQ ID NO: 27490 | QITLKESGPMLVKPTQTLTLTCTFSGFSLSTSGVGV GWIRQPPGKALEWLALIYWNDDKRYSPSLKSRLTI TEDTSKNQVLTMTNMDPVDTATYYCAHAVAVSF DYWGQGTLVTVSS<br>SEQ ID NO: 31496 |

FIGURE 50
(Continued)

| | | | | |
|---|---|---|---|---|
| iPS:436852 | 21-225_57H11 | NA | TCCTATGGCTGACTCAGCCACCCTCAGCGTC CGTGTCCCCAGGACAGACAGCCAGCATCACCT GCTCTGGAGATAAACTGGGGGAAAAATATGCT TGCTGGTATCAGCAGAAGCCAGGCCAGTCCCC TGTGTTGGTCATCTATCAAGATAGGAAGCGGC CCTCAGGGATCCCTGAGCGATTCTCTGGCTCC AATTCTGGGAACACAGCCACTCTGACCATCAG CGGGACCCAGGCTATGGATGAGGCTGACTATT ACTGTCAGGCGTGGGACAGCAGCACTGTGTA TTCGGCGGAGGGACCAAACTGACCGTCCTA SEQ ID NO: 27491 | CAGATCACCTTGAAGGAGTCTGGTCCTACGCTGG TGAAACCCACACAGACCCTCAGCGTGACCTGCAC CTTCTCTGGGTTCTCACTCACTACTAGTGGAGTG GGTGGCTGGATCCGTCAGCCCCCAGGAAAG GCCCTGGAGTGGCTTGCACTCATTTATTGGCATG AAGATAGGCGCTACAGCCCATCTCTGAAGAGCA GGCTCACCATCTCTGAGGACACCTCCAAAACC AGTTGGACCTTACAATGACCAACATGGCCCTGT GGACACAGCCACATATTACTGTGCACACGTCACA GGTATAGCAGCTCCTACTGGGGCCAGGGAACC CTGGTCACCGTCTCCTCA SEQ ID NO: 31497 |
| | | AA | SYALTQPPSASVSPGQTASITCSGDKLGEKYACW YQQKPGQSPVLVIYQDRKRPSGIPERFSGSNSGN TATLTISGTQAMDEADYYCQAWDSSTVVFGGG TKLTVL SEQ ID NO: 27492 | QITLKESGPTLVKPTQTLTLTCTFSGFSLTTSGVGVG WIRQPPGKALEWLALIYWHEDRRYSPSLKSRLTITE DTSKNQVDLTMTNMAPVDTATYYCAHVTGIAAPY WGQGTLVTVSS SEQ ID NO: 31498 |
| iPS:436854 | 21-225_58C1 | NA | TCCTATGAGCTGACTCAGCCACCCTCAGTGTC CGTGTCCCCAGGACAGACAGCCAGCATCACCT GCTCTGGAGATAAATTGGGGAATAAATATGCT TGCTGGTATCAGCAGAAGCCAGGCCAGTCCCC TGTATTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGGACAGCAGCACTGATT ACTGTCAGGCGTGGGACAGCAGCACTGTCCTC GGCGGAGGGACCAAGCTGACCGTCCTC SEQ ID NO: 27493 | CAGATCACCTTGAAGGAGTCTGGTCCTACGCTGG TGAAACCCACACAGACCCTCAGCGTGACCTGCAC CTTCTCTGGGTTCTCACTCACTCAGACTAGTGGAGTG GGTGGCTGGATCCGTCAGCCCCCAGGAAAG GCCCTGGAGTGGCTTGCACTCATTTATTGGGATG ATGATAAGGCTACAGCCCATCTCTGAAGAGCA GGCTCACCATCACCGAGGACACCTCCAAAACC AGTTGGTCCTTACAATGACCAACATGGACCCTGT GGACACAGCCACATATTACTGTGCACACCTTATA GCAGTGGCCTTTGACTCCTGGGGCCAGGAACCC TGGTCACCGTCTCCTCA SEQ ID NO: 31499 |

FIGURE 50
(Continued)

| | | | | |
|---|---|---|---|---|
| iPS:436856 | 21-225_58C5 | AA | SYELTQPPSVSVSPGQTANITCSGDKLGNKYAC WYQQKPGQSPVLVIYQDRKRPSGIPERFSGSNSG NTATLTISGTQAMDEADYYCQAWDSSTAFGGG TKLTVL<br><br>SEQ ID NO: 27494 | QITLKESGPTLVKPTQTLTLTCTFSGFSLSTSGVVG WIRQPPGKALEWLALIYWDDDKRYSPSLKSRLTITE DTSKNQVVLTMTNMDPVDTATYYCAHLIAVAFDS WGQGTLVTVSS<br><br>SEQ ID NO: 31500 |
| | | NA | CAGTCTGTGTGTTGACGCAGCCGCCCTCAGTGTC TGCGGCCCCAGGACAGAAGGTCACCATCTCCT GCTCTGGAAGCAGCTCCAACATTGGGAATAAT TATGTATCCTGGTACCAGCAGCTCCCAGGAAC AGCCCCCAAACTCCTCATTTATGACAATAATA AGCGACCCTCAGGGATTCCTGACCGATTTTCT GGCTCCAAGTCTGGCACGTCAGCCACCCTGG CATCACCGGACTCCAGACTGGGGACGAGGCC GATTATTACTGCGGAACATGGGATATCAGTCT GAGTGTTGGGGTATTCGGCGGAGGGACCAAG CTGACCGTCCTA<br><br>SEQ ID NO: 27495 | GAGGTGCAGTTGGTGGAGTCTGGGGGAGGCCTG GTCAAGCCTGGGGGGTCCCTGAGACTCTCCTGTG CAGCCTCTGGATTCACCTTCAATAGCTATAGCAT GAACTGGGTCCGCCAGGCTCCAGGGAAGGGGCT GGAGTGGATCTCATCCATTAGTAGTAGTTAT TACTTATATACTACGAGACTCAGTGAAGGGCCGAT TCACCATCTCCAGAGACAGCGCCAAGAATTCACT GTATCTGCAAATGAACAGCCTGAGAGCCGAGGA CACGGCTGTATATTACTGTGCGAGAGACCTATAGT GGGAGTTTTGACTACTGGGGCCAGGGAACCCTG GTCACCGTCTCCTCA<br><br>SEQ ID NO: 31501 |
| | | AA | QSVLTQPPSVSAAPGQKVTISCSGSSSNIGNNYVS WYQQLPGTAPKLLIYDNNKRPSGIPDRFSGSKSG TSATLGITGLQTGDEADYYCGTWDISLSVGVFG GGTKLTVL<br><br>SEQ ID NO: 27496 | EVQLVESGGGLVKPGGSLRLSCAASGFTFNSYSMN WVRQAPGKGLEWISSISSSSYLYLYADSVKGRFTIS RDSAKNSLYLQMNSLRAEDTAVYYCARTYSGSFD YWGQGTLVTVSS<br><br>SEQ ID NO: 31502 |

FIGURE 50
(Continued)

| | | | |
|---|---|---|---|
| iPS:436858 | 21-225_58E7 | NA | TCCTATGAACTGACTCAGTCAGCCACCCTCGGTGTC CGTGTCCCCAGGACAGACAGCCAGCATCACCT GTTCTGGAGATAAATTGGGGGATAAATATACT TGCTGGTATCAGAAGAAGCCAGGCCAGTCCCC TGTGCTGGTCATCTATCAAGATAACAAGCGGC CCTCAGGGATCCCTGAGCGATTCTCTGGCTCC AACTCTGGAACACAGCCACTCTGACCATCAG CGGGACCCAGGCTATGGATGAGGCTGACTATT TCTGTCAGGCGTGGAACAACTACACTGTGTA TTCGGCGGAGGGACCAAGCTGACCGTCCTA SEQ ID NO: 27497 | CAGGTGCAGTTGGTGGAGTCTGGGGGAGGCGTG GTCCAGCCTGGGAGGTCCCTGAGACTCTCCTGTG CAGCCTCTGGATTCACCTTCAGTTTCTATGGCAT GCACTGGGTCCGCCAGGCTCCAGGCAAGGGCT GGAGTGGGTGGCAGTTACATCATATGATGAAGT GATAAATACTATGCAGACTCCGTGAAGGGCCGA TTCTCCATCTCCAGAGACAATTCCAAGAACACGC TGTATCTGCAAATGAGCAGCCTGAGAGCTGAGG ACACGGCTATGTATTACTGTGCGAGAGATGACTA TGGTTCGGGAGTCCCCTATACTACGGTATGGAC GTCTGGGGCCAAGGGACCACGGTCACCGTCTCCT CA SEQ ID NO: 31503 |
| | | AA | SYELTQSPSVSVSPGQTASITCSGDKLGDKYTCW YQKKPGQSPVLVIYQDNKRPSGIPERFSGSNSGN TATLTISGTQAMDEADYFCQAWNNYTVVFGGG TKLTAL SEQ ID NO: 27498 | QVQLVESGGGVVQPGRSLRLSCAASGFTFSFYGMH WVRQAPGKGLEWVAVTSYDGSDKYYADSVKGRF SISRDNSKNTLYLQMSSLRAEDTAMYYCARDDYGS GSPLYYGMDVWGQGTTVTVSS SEQ ID NO: 31504 |
| iPS:436860 | 21-225_58F7 | NA | TCCTATGAGCTGACTCAGCCACCCTCAGTGTC CGTGTCCCCAGGACAGACAGCCAGCATCACCT GCTCTGGAGATAAATTGGGGGATAAATATGCT AGCTGGTATCAGCAGAAGCCAGGCCAGTCCCC TGTGCTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGGACAGCAGCACTGTGTA ACTGTCAGGCGTGGGACAGCAGCACTGTGTA TTCGGCGGAGGGACCAAGCTGACCGTCCTA SEQ ID NO: 27499 | GAGGTGCAGCTGGTGGAGTCTGGGGGAGGCTTG GTCCAGCCTGGGGGGTCCCTGAGACTCTCCTGTG CAGCCTCTGGATTCACCTTTAGTAGCTTTTGGATG AGCTGGGTCCGCCAGGCTCCAGGGAAGGGCTG GAGTGGGTGGCCCACATAAAGCAAGATGAAGT GAGAAATACTATGTGGACTCTGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGAGGGACCTC CCATACAGCTCGGGCTACTACTACGGTATGACG TCTGGGGCCAAGGGACCACGGTCACCGTCTCTCCT CA SEQ ID NO: 31505 |

FIGURE 50
(Continued)

| | | AA | SYELTQPPSVSVSPGQTASITCSGDKLGDKYACW YQQKPGQSPVLVIYQDRKRPSGIPERFSGSNSGN TATLTISGTQAMDEADYYCQAWDSSTVFGGG TKLTVL<br><br>SEQ ID NO: 27500 | EVQLVESGGGLVQPGGSLRLSCAASGFTFSSFWMS WVRQAPGKGLEWVAHIKQDGSEKYYVDSVKGRF TISRDNAKNSLYLQMNSLRAEDTAVYYCARGDLPY SSGYYYGMDVWGQGTTVTVSS<br><br>SEQ ID NO: 31506 |
|---|---|---|---|---|
| iPS:436862 | 21-225_58F8 | NA | TCCTATGAGCTGACTCAGCCACCCTCAGTGTC CGTGTCCCCAGGACAGACAGCCAGCATCACCT GCTCTGGAGATAAATTGGGAAATAAATATGCT TGCTGGTATCAGCAGAAGCCAGGCCAGTCCCC TGTACTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGAGGACAGCACTGTGTA ACTGTCAGGCGTGGGACAGCAGCACTGTGGTA TTCGGCGGAGGGACCAAACTGACCGTCCTA<br><br>SEQ ID NO: 27501 | CAGGTGCAACTGGTGGAGTCTGGGGGAGGCGTG GTCCAGCCTGGGAGGTCCCTGAGACTCTCCTGTG CAGCCTCTGGATTCACCTTCAGTAGCTATGGCAT GCACTGGGTCCGCCAGGCTCCAGGCAAGGGCT GGAGTGGGTGGCAGTTATATCATATGATGAAGT AATAAATACTATGCAGACTCCGTGAAGGGCCGA TTCACCATCTCCAGAGACAACGCTGAGAGCAAGACACGT TGTATCTGCAAATGAACAGCCTGAGAGCTGAGG ACACGGCTGTGTATTACTGTGCGAGAGAGGGATATTA ACGTGGATATGGTGGCTACGACGAGAGGGGATATTA CTACTACTACGGTATGGACGTCTGGGGCCAA GGGACCACGGTCACCGTCTCCTCA<br><br>SEQ ID NO: 31507 |
| | | AA | SYELTQPPSVSVSPGQTASITCSGDKLGNKYACW YQQKPGQSPVLVIYQDSKRPSGIPERFSGSNSGN TATLTISGTQAMDEADYYCQAWDSSTVFGGG TKLTVL<br><br>SEQ ID NO: 27502 | QVQLVESGGGVVQPGRSLRLSCAASGFTFSSYGMH WVRQAPGKGLEWVAVISYDGSNKYYADSVKGRFT ISRDNSKNTLYLQMNSLRAEDTAVYYCARDEGRG YGGYERGYYYYYGMDVWGQGTTVTVSS<br><br>SEQ ID NO: 31508 |

FIGURE 50
(Continued)

| | | | |
|---|---|---|---|
| iPS:436864 | 21-225_58G11 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTCATCTATCAAGATAACAAGCGGC CCTCAGGGATCCCTGAGCGCTTCTCTGGCTCC AACTCTGGAAACACAGCCACTCTGACCATCAG CGGGACCCAGGCTATGGATGAGGCTGACTATT ACTGTCAGGCGTGAACAACACACTGTAATG TTCGGCGGAGGGACCAAGCTGACCGTCCTA SEQ ID NO: 27503 | GAGGTGCAGCTGGTGGTGGAATCTGGGGGAGGCTTG GTACAGCCTGGGGGGTCCCTGAGACTCTCCTGTG CAGCCCTCTGGATTCACCTTCAGTAGCTATAGCAT GAACTGGGTCCGCCAGGCTCCAGGAAGGGCT GGAGTGGATTTCATACATTAGTACTAGTAGT ACCATATTCTACGCAGACTCTGTGAAGGGCCGAT TCACCATCTCCAGAGACAGTGCCAAGAACTCACT GTATCTGCAAATGAACAGCCTGAGAGACGAGGA CACGGCTGTGTATTACTGTGCGAGGGGGATACA GCTATGTCTCTACTACTACGGTATGGACGTCT GGGGCCAAGGGACCACGGTCACCGTCTCCTCA SEQ ID NO: 31509 |
| | | AA | SYELTQPPSVSVSPGQTASITCSGDKLGDKYASW YQQKPGQSPVLVIYQDNKRPSGIPERFSGSNSGN TATLTISGTQAMDEADYYCQAWNNNTVMFGGG TKLTVL SEQ ID NO: 27504 | EVQLVESGGGLVQPGGSLRLSCAASGFTFSSYSMN WVRQAPGKGLEWISYISTSSTIFYADSVKGRFTISR DSAKNSLYLQMNSLRDEDTAVYYCARGDTAMVL YYYGMDVWGQGTTVTVSS SEQ ID NO: 31510 |
| iPS:436866 | 21-225_59F2 | NA | TCCTATGAACTGACTCAGCCACCCTCAGTGTC CGTGTCCCCAGGACAGACAGCCAGCATCACCT GCTCTGGAGATAAATTGGGGGATAAATATGCT TCTTGGTATCAGCAGAGGCCAGGCCAGTCCCC TGTGTTGGTCATCTATCAAGATAACAAGCGGC CCTCAGGGATCCCTGAGCGATTCTCTGGCTCC AACTCTGGGAACACAGCCACTCTGACCATCAG CGGGACCCAGGCTATGGGACAACAACACTGTGGTC ACTGTCAGGCGTGGGACAACAACACTGTGGTC TTCGGCGGAGGGACCAAGCTGACCGTCCTA SEQ ID NO: 27505 | GAGGTGCAGCTGGTGGTGAGTCTGGGGGAGGCTTG GTACAGCCTGGGGGGTCCCTGAGACTCTCCTGTG GAGCCCTCTGGATTCACCTTCAGTAGCTATAGCAT GAACTGGGTCCGCCAGGCTCCAGGAAGGGACT GGAGTGGGTTTCATACATTAGTGGGAGTAGTAAT ATCATATACTACACAGACTCTGTGAAGGGCCGAT TCACCATCTCCAGAGACAATGCCAAGAACTCACT GTATCTGCAAATGAACAGCCTGAGAGACGAGGA CACGGCTGTGTATTACTGTGCGAGAGCGGATACA CCTATGGTCCTTTACTTCTACGGTATGGACGTCTG GGGCCAAGGGACCACGGTCACCGTCTCCTCA SEQ ID NO: 31511 |

FIGURE 50
(Continued)

| | | | |
|---|---|---|---|
| iPS:436868 | 21-225_59B11 | AA | SYELTQPPSVSVSPGQTASITCSGDKLGDKYASW YQQRPGQSPVLVIYQDNKRPSGIPERFSGSNSGN TATLTISGTQAMDEADYYCQAWDNNTVVFGGG TKLTVL<br><br>SEQ ID NO: 27506 | EVQLVESGGGLVQPGGSLRLSCGASGFTFSSYSMN WVRQAPGKGLEWVSYISGSSNIIYYTDSVKGRFTIS RDNAKNSLYLQMNSLRDEDTAVYYCARADTPMVL YFYGMDVWGQGTTVTVSS<br><br>SEQ ID NO: 31512 |
| | | NA | TCCTATGAGCTGACTCAGCCACCCTCAGTGTC CGTGTCCCCAGGACAGACAGCCAGCATCACCT GCTCTGGAGATAAAATTGGGGATAAATATGCT TGCTGGTATCAGCAGAAGCCAGGCCAGTCCCC TGTGCTGGTCATCTATCAAGATAGCAAGCGGC CCTCAGGGATCCTTGAGCGATTCTCTGGCTCC AATTCTGGGAACACAGCCACTCTGACCATCAG CGGAACCCAGGCTATGGAGGCTGACTATT ACTGTCAGGCGTGGGACAGCAGCACTGTGTG GTATTCGGCGGAGGGACCAAGCTGACCGTCCT A<br><br>SEQ ID NO: 27507 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCGT GCACTGGGTCCGCCAGGCTCCAGGCAAGGGCT GGAGTGGGTGGCAGCTATATGGTATGGATGAAG TAATAAATACTATGCAGACTCCGTGAAGGGCCG ATTCACCATCTCCAGAGACAATTCCAAGAACACG CTGTATCTGCTAATGAACAGCTGAGAGCCGAGG ACACGGCTGTGTATTACTGTGCGAGAGATAGGA CTATTGTAGTAGTTCCAGCTGCCCTTACTACTACT ACTACGGTATGGACGTCTGGGGCCAAGGGACCA CGGTCACCGTCTCCTCA<br><br>SEQ ID NO: 31513 |
| | | AA | SYELTQPPSVSVSPGQTASITCSGDKLGDKYACW YQQKPGQSPVLVIYQDSKRPSGILERFSGNSGN TATLTISGTQAMDEADYYCQAWDSSTYVFGG GTKLTVL<br><br>SEQ ID NO: 27508 | QVQLVESGGGVVQPGRSLRLSCAASGFTFSSYGVH WVRQAPGKGLEWVAAIWYDGSNKYYADSVKGRF TISRDNSKNTLYLLMNSLRAEDTAVYYCARDRDYC SSSSCPYYYYYGMDVWGQGTTVTVSS<br><br>SEQ ID NO: 31514 |

FIGURE 50
(Continued)

| | | | |
|---|---|---|---|---|
| iPS:436870 | 21-225_60B1 | NA | TCCTATGAGCTGACTCAGCCACCCTCAGCGTC CGTGTCCCAGGAGATAAACTGGGGACAGCCAGCATCACCT GCTCTGGAGATATCAGCAGAAGCCAGGCCAGTCCCC TGCTGGTATCAGCAGAAGCCAGGCCAGTCCCC TGTGTTGGTCATCTATCAAGATAGGAAGCGGC CCTCAGGGATCCCGAGCGATTCTCTGGCTCC AATTCTGGGAACACAGCCACTCTGACCATCAG CGGGACCCAGGCTATGGATGAGGCTGACTATT ACTGTCAGGCGTGGGACAGCAGCACTGTGTA TTCGGCGGAGGGACCAAACTGACCGTCCTA<br><br>SEQ ID NO: 27509 | CAGATCACCTTGAAGGAGTCTGGTCCTACGCTGG TGAAACCCACACAGACCCTCACGCTGACCTGCAC CTTCTCTGGGTTCTCACTCAGTACTAGTGGAGTG GGTGTGGGCTGATCCGTCAGCCCCCAGGAAAG GCCCTGGAGTGGCTTGCACTCATTTATTGGCATG AAGATAAGCGCTACAGCCCATCTCTGAAGAGCA GGCTCACCATCACTGAGGACACCTCCAAAACC AGTTGGACCTTACAATGACCAACATGGCCCTGT GGACACAGCCACATATTACTGTGCACACGTCACA TATATAGCAGCTCCCTACTGGGGCCAGGGAACCC TGGTCACCGTCTCCTCA<br><br>SEQ ID NO: 31515 |
| | | AA | SYELTQPPSASVSPGQTASITCSGDKLGEKYACW YQQKPGQSPVLVIYQDRKRPSGIPERFSGSNSGN TATLTISGTQAMDEADYYCQAWDSSTVVFGGG TKLTVL<br><br>SEQ ID NO: 27510 | QITLKESGPTLVKPTQTLTLTCTFSGFSLSTSGVGVG WIRQPPGKALEWLALIYWHEDKRYSPSLKSRLTITE DTSKNQVDLTMTNMAPVDTATYYCAHVTYIAAPY WGQGTLVTVSS<br><br>SEQ ID NO: 31516 |
| iPS:436872 | 21-225_60D2 | NA | TCCTATGAACTGACTCAGCCACCCTCAGTGTC CGTGTCCCAGGACAGACAGCCAGCATCACCT GCTCTGGAAATAAATTGGGGGATAAAGCCAGTCCCC TCTTGGTATCAGCAGAGGCCAGGCCAGTCCCC TGTATTAGTAGTCATCTATCAAGATAACAAGCGGC CCTCAGGGATCCCTGAGCGATTCTCTGGCTCC AACTCTGGAAACACAGCCACTCTGACCATCAG CGGGACCCAGACTATGGAGGCTGACTATT ACTGTCAGGCGTGGGACAACAACTGTGGTC TTCGGCGGAGGGACCAAGCTGACCGTCCTA<br><br>SEQ ID NO: 27511 | GAGGTGCAGCTGGTGGAGTCTGGGGGAGGCTTG GTACAGCCTGGGGGGTCCCTGAGACTCTCCTGTG GAGCCTCTGGATTCACCTTCAGTAGCTATAGCAT GAACTGGGTCCGCCAGGCTCCAGGGAAAGGACT GGAGTGGGTTTCATACATTAGTAGTAGAGTAGTAAT ATCATATACTACACAGACTCTGTGAAGGGCGAT TCACCATCTCCAGAGACAATGCCATGAACTACT GTATCTGCAAATGAACAGCCTGAGAGACGAGGA CACGGCTGTGTATTACTGTGCGAGAGCGGATACA CCTATGGTCCTTTACTTCTACGGTATGGACGTCTG GGGCCAAGGGACCACGGTCACCGTCTCCTCA<br><br>SEQ ID NO: 31517 |

FIGURE 50
(Continued)

| | | | |
|---|---|---|---|
| iPS:436874 | 21-225_60A12 | AA | SYELTQPPSVSVSPGQTASITCSGNKLGDKYASW YQQRPGQSPVLVIYQDNKRPSGIPERFSGSNSGN TATLTISGTQTMDEADYYCQAWDNNTVFGGG TKLTVL<br><br>SEQ ID NO: 27512 | EVQLVESGGGLVQPGGSLRLSCGASGFTFSSYSMN WVRQAPGKGLEWVSYISESSNIIYTDSVKGRFTIS RDNAMNSLYLQMNSLRDEDTAVYYCARADTPMV LYFYGMDVWGQGTTVTVSS<br><br>SEQ ID NO: 31518 |
| | | NA | TCCTATGAGCTGACTCAGCCACCCTCAGTGTC CGTGTCCCAGGACAGACAGCCAACATCACCT GCTCTGAGATAAATTGGGAATACAGCCTAACACTCACCT TGCTGGTATCAGCAGAAGCCAGGCCAGTCCCC TGTATTGGTCATTTATCAAGATAGGAAGCGGC CCTCAGGGATCCCTGAGCGATTCTCTGGCTCC AACTCTGGGAACACAGGCTATGATGAGGCTGACTATT CGGGACCCCAGGCTATGGGACAGCACTGCTTTC ACTGTCAGGCGTGGGACAGCAGCACTGCTTTC GGGCGGAGGGACCAAGCTGACCGTCCTC<br><br>SEQ ID NO: 27513 | CAGATCACCTTGAAGGAGTCTGGTCCTACGCTGG TGAAACCCACACAGACCCTCACGCTGACCTGCAC CTTCTCTGGGTTCTCACTCAGCACTAGTGGAGTG GGTGTGGGCTGGATCCGTCAGCCCCCAGGAAAG GCCCTGGAGTGGCTTGCACTCATTTATTGGGATG ATGATAAGCGCTACAGCCCATCTCTGAAGAGCA GGCTCACCATCACCGAGGACACCTCCAAAAACC AGGTGGTCCTTACAAGCCACCAACATGACCCTGT GGACACAGCCACATATTACTGTGCACACCTTATA GCAGTGGCCTTTGACTCCTCGGGGCCAGGGAACCC TGGTCACCGTCTCCTCA<br><br>SEQ ID NO: 31519 |
| | | AA | SYELTQPPSVSVSPGQTANITCSGDKLGNKYAC WYQQKPGQSPVLVIYQDRKRPSGIPERFSGSNSG NTAILTISGTQAMDEADYYCQAWDSSTAFGGGT KLTVL<br><br>SEQ ID NO: 27514 | QITLKESGPTLVKPTQTLTLTCTFSGFSLSTSGVGVG WIRQPPGKALEWLALIYWDDDKRYSPSLKSRLTITE DTSKNQVVLTMTNMDPVDTATYYCAHLIAVAFDS WGQGTLVTVSS<br><br>SEQ ID NO: 31520 |

FIGURE 50
(Continued)

| | | | | |
|---|---|---|---|---|
| iPS:436876 | 21-225_61F5 | NA | TCCTATGAGCTGACTCAGCCACCCTCAGTGTC CGTGTCCCCAGGACAGACAGCCAGCATCACCT GCTCTGGAGATAAATTGGGGGAAAAATATGCT TGCTGGTATCAGCAGAAGCCAGGCCAGTCCCC TGTGTTGGTCATCTATCAAGATAGCAAGCGGC CCTCAGGGATCCCTGAGCGATTCTCTGGCTCC AATTCTGGGAACACAGCCACTCTGACCATCAG CGGGACCCAGGCTATGGATGAGGCTGACTATT ACTGTCAGGCGTGGGACAGCAGCACTGTGGTT TTCGGCGGAGGGACCAAACTGACCGTCCTA SEQ ID NO: 27515 | CAGATCACCTTGAAGGAGTCTGGTCCTACGCTGG TGAAACCCACACAGACCCTCACGCTGACCTGCAC CTTCTCTGGGTTCTCACTCAGTACTAGTGGGTTGG GTGTGGGCTGATCGTCAGCCCCCAGGAAAGG CCCTGGAGTGGCTTGCACTCATTTATTCACATGA AGATAAGGCTACAGCCATCTCTGAAGAGCAG GCTCACCATCACTGAGGACACCTCCAAAACCA GGTGGACCTTACAATGACCAACATGGCCCTGTG GACACAGCCACATATTACTGTGCACACGTCACAG GTATAGCAGTCCCTACTGGGGCCAGGGAACCCT GGTCACCGTCTCCTCA SEQ ID NO: 31521 |
| | | AA | SYELTQPPSVSVSPGQTASITCSGDKLGEKYACW YQQKPGQSPVLVIYQDSKRPSGIPERFSGSNSGN TATLTISGTQAMDEADYYCQAWDSSTVVFGGG TKLTVL SEQ ID NO: 27516 | QITLKESGPTLVKPTQTLTLTCTFSGFSLSTSGLGVG WIRQPPGKALEWLALIYSHEDKRYSPSLKSRLTITE DTSKNQVDLTMTNMAPVDTATYYCAHVTGIAAPY WGQGTLVTVSS SEQ ID NO: 31522 |
| iPS:436878 | 21-225_62E3 | NA | TCCTATGACCTGACTCAGCCACCCTCAGTGTC CGTGTCCCCAGGACAGACAGCCAGCATCACCT GCTCTGGAGATAAATTGGGGAATAAATATGCT TGCTGGTATCAGCAGAAGCCAGGCCAGTCCCC TGTGGTGGTCATCTATCAAGATAGGAAGCGGC CCTCAGGGATCCCTGAGCGATTCTCTGGCTCC AATTCTGGGAACACAGCCACTCTGACCATCAG CGGGACCCAGGCTATGGATGAGGCTGACTATT ACTGTCAGGCGTGGGACAGCAGCACTGCGGTA TTCGGCGGAGGGACCAAGCTGACCGTCCTA SEQ ID NO: 27517 | CAGATCACCTTGAAGGAGTCTGGTCCTACGCTGG TGAAACCCACACAGACCCTCACGCTGACCTGCAC CTTCTCTGGGTTCTCGCTCAGCACTAGTGAGTG GGTGTGGGCTGGATCCGTCAGCCCCCAGGAAAG GCCCTGGAGTGGCTTGCACTCATTAATTGGAATG ATGATAAGGCTACAGCCATCTCTGAAGAGCA GGTTCACCATCACCAGGGACACCTCCAAAGACC AGGTGGTCCTTACAATGACCAACATGGACCCTGT GGACACAGCCACATATTACTGTGCACATAAAGCT ACCTGGGTGGCTTTGATATCTGGGGCCAAGGGA CAATGGTCACCGTCTCTTCA SEQ ID NO: 31523 |

FIGURE 50
(Continued)

| | | | |
|---|---|---|---|
| iPS:436880 | 21-225_62E8 | AA | SYDLTQPPSVSVSPGQTASITCSGDKLGNKYAC WYQQKPGQSPVVVIYQDRKRPSGIPERFSGSNSG NTATLTISGTQAMDEADYYCQAWDSSTAVFGG GTKLTVL<br>SEQ ID NO: 27518 | QITLKESGPTLVKPTQTLTLTCTFSGFSLSTSGVGVG WIRQPPGKALEWLALINWNDDKRYSPSLKSRFTITR DTSKDQVVLTMTNMDPVDTATYYCAHKATWVAF DIWGQGTMVTVSS<br>SEQ ID NO: 31524 |
| | | NA | TCCTATGACCTGACTCAGCCACCCTCAGTGTC CGTGTCCCCAGGACACAGACCAGCATCACCT GCTCTGAGATATAGATTGGGGAATAAATATGCT TCCTGGTATCAGCAGAAGCCAGGCCAGTCCCC TGTGGTGGTCATCTATCAGGATAGGAAGCGGC CCTCAGGGATCCCTGAGCGATTCTCTGGCTCC AACTCTGGGAACACAGGCTATGAGGCTGACTATT ACTGTCAGGCGTGGGACAGCAGCACTGCGGTA TTCGGCGGAGGGACCAAGCTGACCGTCCTA<br>SEQ ID NO: 27519 | CAGATCACCTTGAAGGAGTCTGGTCCTACGCTGG TGAAACCCACACAGACCCTCACGCTGACCTGTAC CTTCTCTGGGTTCTCACTCAGCACTAGTGGAGTG GGTGTGGGCTGGATCCGTCAGCCCCCAGGAAAG GCCCTGGAGTGGCTTGCACTCATTAATTGGAATG ATGATAAGCGCTACAGCCCATCTCTGAAGAGCA GGTTCACCATCACCAGGGACACCTCCAAAGACC AGGTGGTCCTTACAATGACCAACATGACCCTGT GGACACAGCCACATATTACTGTGCACATAAAGCT ACCTGGGTGGCTTTTGATATCTGGGGCCAAGGGA CAATGGTCACCGTCTCTTCA<br>SEQ ID NO: 31525 |
| | | AA | SYDLTQPPSVSVSPGQTASITCSGDRLGNKYASW YQQKPGQSPVVVIYQDRKRPSGIPERFSGSNSGN TATLTISGTQAMDEADYYCQAWDSSTAVFGGG TKLTVL<br>SEQ ID NO: 27520 | QITLKESGPTLVKPTQTLTLTCTFSGFSLSTSGVGVG WIRQPPGKALEWLALINWNDDKRYSPSLKSRFTITR DTSKDQVVLTMTNMDPVDTATYYCAHKATWVAF DIWGQGTMVTVSS<br>SEQ ID NO: 31526 |

FIGURE 50
(Continued)

| | | | |
|---|---|---|---|
| iPS:436882 | 21-225_62D10 | NA | TCCTATGACCTGACTCAGCCACCCTCAGTGTCCGTGTCCCCAGGACAGACAGCCAGCATCACCTGCTCTGGAGATAAATTGGGGATAAATATGCTTGCTGGTATCAGCAGAAGCCAGGCCAGTCCCCTGTGGTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCCGTGGGACAGCAGCACTGCGGTATTCGGCGGAGGGACCAAGCTGACCGTCCTA SEQ ID NO: 27521 | CAGATCACCTTGAAGGAGTCTGGTCCTACGCTGGTGAAATCACACAGACCCTCAGCGCTGACCTGCACCTTCTCTGGGTTCTCACTCAGCACTAGTGGAGTGGGTGGGCTGATCCGTCAGCCCCCAGGAAGGCCCTGGAGTGGCTTGCACTCATTAATTGGAATGATGATAAGCGCTACAGCCCATCTCTGAAGAGCAGGTTCACCATCTCCAAGGACACCTCCAAAGACCAGTGGTCCTTACAATGACCAACATGACCCTGTGGACACAGCCACATATTACTGTGCACATAAAGCTACCTGGGTGGCTTTTGATATCTGGGGCCAAGGGACAATGGTCACCGTCTCTTCA SEQ ID NO: 31527 |
| | | AA | SYDLTQPPSVSVSPGQTASITCSGDKLGNKYACWYQQKPGQSPVVVIYQDRKRPSGIPERFSGSNSGNTATLTISGTQAMDEADYYCQAWDSSTAVFGGGTKLTVL SEQ ID NO: 27522 | QITLKESGPTLVKSTQTLTLTCTFSGFSLSTSGVGVGWIRQPPGKALEWLALINWNDDKRYSPSLKSRFTITRDTSKDQVLTMTNMDPVDTATYYCAHKATWVAFDIWGQGTMVTVSS SEQ ID NO: 31528 |
| iPS:436884 | 21-225_62A12 | NA | TCCTATGACCTGACTCAGCCACCCTCAGTGTCCGTGTCCCCAGGACAGACAGCCAGCATCACCTGCTCTGGAGATAAATTGGGGATAAATATGCTTGCTGGTATCAGCAGAAGCCAGGCCAGTCCCCTGTGGTGGTCATCTATCAAGATAGGAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCCGTGGGACAGCAGCACTGCGGTATTCGGCGGAGGGACCAAGCTGACCGTCCTA SEQ ID NO: 27523 | CAGATCACCTTGAAGGAGTCTGGTCCTACGCTGGTGAAACCCACACAGACCCTCAGCGCTGACCTGCACCTTCTCTGGGTTCTCACTCAGCACTAGTGGAGTGGGTGGGCTGATCCGTCAGCCCCCAGGAAGGCCCTGGAGTGGCTTGCACTCATTAATTGGAATGATGATAAACGCTACAGCCCATCTCTGAAGAGCAGGTTCACCATCACCAGGGACACCTCCAAAGACCAGGTGGTCCTTACAATGACCAACATGACCCTCTGGACACAGCCACATATTACTGTGCACATAAAACTACCTGGGTGGCTTTTGATATCTGGGGCCAAGGGACAATGGTCACCGTCTCTTCA SEQ ID NO: 31529 |

FIGURE 50
(Continued)

| | | | |
|---|---|---|---|
| iPS:436886 | 21-225_62B12 | AA | SYDLTQPPSVSVSPGQTASITCSGDKLGNKYAC WYQQKPGQSPVVVIYQDRKRPSGIPERFSGSNSG NTATLTISGTQAMDEADYYCQAWDSSTAVFGG GTKLTVL<br>SEQ ID NO: 27524 | QITLKESGPTLVKPTQTLTLTCTFSGFSLSTSGVGVG WIRQPPGKALEWLALINWNDDKRYSPSLKSRFTITR DTSKDQVVLTMTNMDPLDTATYYCAHKTTWVAF DIWGQGTMVTVSS<br>SEQ ID NO: 31530 |
| | | NA | TCCTATGACCTGACTCAGCCACCCTCAGTGTC CGTGTCCCCAGGACAGACAGCCAGCATCACCT GCTCTGAGATAAATTGGGAATAAATATACT TGCTGGTATCAGCAGAAGCCAGGCCAGTCCCC TGTGGTGGTCATCTATCAAGATAGGAAGCGGC CCTCAGGGATCCCTGAGCGATTCTCTGGCTCC AATTCTGGGAACACAGGCTATGAGGCTGACTATT CGGGACCCAGGTGGGACAGCAGCACTGCGGTA TTCGGCGGAGGGACCAAGCTGACCGTCCTA<br>SEQ ID NO: 27525 | CAGATCACCTTGAAGGAGTCTGGTCCTACGCTGG TGAAACCCACACAGACCCTCACGCTGACCTGCAC CTTCTCTGGGTTCTCACTCAACACTAGTGGAGTG GGTGTGGGCTGGATCCGTCAGCCCCCAGGAAAG GCCCTGGAGTGGCTTGCACTCATTAATTGGAATG ATGATAAGCGCTACAGCCCGTCTCTGAAGAGCA GGTTCACCATCACCAGGGACACCTCCAAAGACC AGGTGGTCCTTACAATGACCAACATGACCCTGT GGACACAGCCACATATTACTGTGCACATAAAGCT ACCTGGGTGGCTTTTGATATCTGGGGCCAAGGGA CAATGGTCACCGTCTCTTCA<br>SEQ ID NO: 31531 |
| | | AA | SYDLTQPPSVSVSPGQTASITCSGDKLGNKYTCW YQQKPGQSPVVVIYQDRKRPSGIPERFSGSNSGN TATLTISGTQAMDEADYYCQAWDSSTAVFGGG TKLTVL<br>SEQ ID NO: 27526 | QITLKESGPTLVKPTQTLTLTCTFSGFSLNTSGVGVG WIRQPPGKALEWLALINWNDDKRYSPSLKSRFTITR DTSKDQVVLTMTNMDPVDTATYYCAHKATWVAF DIWGQGTMVTVSS<br>SEQ ID NO: 31532 |

FIGURE 50
(Continued)

| | | | |
|---|---|---|---|
| iPS:436888 | 21-225_63G7 | NA | AATTTTATGCTGACTCAGCCCCACTCTGTGTCG GAGTCTCCGGGGAAGACGGTAACCATCTCCTG CACCCGCAGCAGTGCAGCATTGTCAGCAACT ATGTGCAGTGGTACCAGCAGCGCCCGGGCAGT TCCCCCACCACTATGATCTATGAGGATAGCCG AAGACCCTCTGGGGTCCCTGATCGGTTCTCTG GCTCCATCGACAGCTCCTCCAACTCTGCCTCC CTCACCATCTCTGGACTGAAGACTGAGGACGA GGCTGACTACTCCTGTCAGTCTTATGATGCA TCAATGTGGTATTCGGGCGGAGGGACCAAGCTG ACCGTCCTA<br><br>SEQ ID NO: 27527 | GAGGTGCAGCTGGTGGAGTCTGGGGGAGGCTTG GTACAGCCTGGGGGGTCCCTGAGACTCTCCTGTG CAGCCTCTGGATTCACCTTCAGTAGCTATAGCAT GAACTGGGTCCGCCAGGCTCCGGGAAGGGGCT GGAGTGGGTTTCATACATTAGTAGTAGTACTAGT ACCATATACTACGCAGCCTCTGTGAAGGGCCGA TTCACCATCTCCAGAGACAATGCCAAGAACTACT GTATCTGCAAATGAACAGCCTGAGAGACGAGGA CACGGCTGTGTATTACTGTGCGAGAGATCACCGT TACTATGATAGTAGTGGTTATTACTCTGATGCTTT TGATATCTGGGGCCAAGGGACAATGGTCACCGTC TCTTCA<br><br>SEQ ID NO: 31533 |
| | | AA | NFMLTQPHSVSESPGKTVTISCTRSNGSIVSNYV QWYQQRPGSSPTTMIYEDSRRPSGVPDRFSGSID SSSNSASLTISGLKTEDEADYSCQSYDGINVFG GGTKLTVL<br><br>SEQ ID NO: 27528 | EVQLVESGGGLVQPGGSLRLSCAASGFTFSSYSMN WVRQAPGKGLEWVSYISSSTSTIYYAASVKGRFTIS RDNAKNSLYLQMNSLRDEDTAVYYCARDHRYYD SSGYYSDAFDIWGQGTMVTVSS<br><br>SEQ ID NO: 31534 |
| iPS:436890 | 21-225_63A10 | NA | AATTTTATGCTGACTCAGCCCCACTCTGTGTCG GAGTCTCCGGGGAAGACGGTAACCATCTCCTG CACCCGCAGCAGTGCAGCATTGTCAGCAACT ATGTGCAGTGGTACCAGCAGCGCCCGGGCAGT TCCCCCACCACTGTGATCTATGAGGATAAAAG AAGACCCTCTGGGGTCCCTGATCGGTTCTCTG GCTCCATCGACAGCTCCTCCAACTCTGCCTCC CTCACCATCTCTGGACTGAAGACTGAGGACGA GGCTGACTACTACTGTCAGTCTCTATGATAGCA TCAATGTGGTATTCGGGCGGAGGGACCAAGCTG ACCGTCCTA<br><br>SEQ ID NO: 27529 | GAGGTGCAGCTGGTGGTGGAGTCTGGGGGAGGCTTG GTACAGCCTGGGGGGTCCCTGAGACTCTCCTGTG CAGCCTCTGGATTCACCTTCAGTAGCTATAGCAT GAACTGGGTCCGCCAGGCTCCGGGAAGGGGCT GGAGTGGGTTTCATACATTAGTAGTAGTACTAGT ACCATATACTACGCAGCCTCTGTGAAGGGCCGAT TCACCATCTCCAGAGACAATGCCAAGAATTCACT GTATCTGCAAATGAACAGCCTGAGAGACGAGGA CACGGCTGTGTATTACTGTGCGAGAGATCACCGT TACTATGATAGTAGTGGTTATTACTCTGATGCTTT TGATATCTGGGGCCAAGGGACAATGGTCACCGTC TCTTCA<br><br>SEQ ID NO: 31535 |

FIGURE 50
(Continued)

| | | | |
|---|---|---|---|
| iPS:436892 | 21-225_65E9 | AA | NFMLTQPHSVSESPGKTVTISCTRSNGSIVSNYV QWYQQRPGSSPTTVIYEDKRRPSGVPDRFSGSID SSSNSASLTISGLKTEDEADYYCQSYDSINVVFG GGTKLTVL<br>SEQ ID NO: 27530 | EVQLVESGGGLVQPGGSLRLSCAASGFTFSSYSMN WVRQAPGKGLEWVSYISSSTSTIYYAASVKGRFTIS RDNAKNSLYLQMNSLRDEDTAVYYCARDHRYYD SSGYYSDAFDIWGQGTMVTVSS<br>SEQ ID NO: 31536 |
| | | NA | TCCTATGAGCTGACTCAGCCACCCTCAGTGTC CGTGTCCCAGGACAGCAGACAGCCAGCATCACCT GCTCTGGAGATAAATTGGGAATAAGCCAGGCCAGGAATAAATATGAT TACTGGTATCAGCAGAAGCCAGGCCAGTCCCC TGTGCTGGTCATCTATGAAGATAGAAAGCGGC CCTCAGGGATCCCTGAGCGATTCTCTGGCTCC AACTCTGGGAACACAGGCTATGATGAGGCTGACTATT ACTGTCAGGGCGTGGGACAACAGCACTGTGTA TTCGGCGGAGGGACCAAACTGACCGTCCTA<br>SEQ ID NO: 27531 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCTAACAGTGG TGGCACAAATTATGCACAGAAGTTTCAGGCAG GGTCACCATGACCAGGGACACGTCCATCAGCAC AGCCTACATGGAGCTGAGCAGGCTGAGATCTGA CGACACGGCCGTGTATTACTGTGCGAGAGGGTAT TATTATGGTTCGGGAGTTATTATAATGAATTTG ATATGTGGGGCCAAGGGACAATGGTCACCGTCTC TTCA<br>SEQ ID NO: 31537 |
| | | AA | SYELTQPPSVSVSPGQTASITCSGDKLGNKYDY WYQQKPGQSPVLVIYQDRKRPSGIPERFSGSNSG NTATLTISGTQAMDEADYYCQAWDNSTVVFGG GTKLTVL<br>SEQ ID NO: 27532 | QVQLVQSGAEVKKPGASVKVSCKASGYTFGYYM HWVRQAPGQGLEWMGWINPNSGGTNYAQKFQGR VTMTRDTSISTAYMELSRLRSDDTAVYYCARAYYY GSGSYYNEFDMWGQGTMVTVSS<br>SEQ ID NO: 31538 |

FIGURE 50
(Continued)

| | | | |
|---|---|---|---|
| iPS:436894 | 21-225_66G9 | NA | TCCTATGAACTGACTCAGCCACCCTCAGTGAC CGTGTCCCCAGGACAGACAGCCAGCATCACCT GCTCTGGAGATAAATTGGGACAGCCTGAATATGCT TGCTGGTATCAGCAGAAGCCAGGCCAGTCCCC TGTGGTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACATCAACACTGCGGTA TTCGGCGGAGGGACCAAGCTGACCGTCCTA | CAGATCACCTTGAAGGAGTCTGGTCCTACGCTGG TGAAACCCACACAGACCCTCACGCTGACCTGCAC CTTCTCTGGGTTCTCACTCAGCACTAGTGGAGTG GGTGTGGGCTGAATCCGTCAGCCCCCAGAAAG GCCCTGGAGTGGCTTGCACTCATTAATTGGAATG ATGATAAGGCGTTCAGCCCATCTCGAAGAGCAG GTTCACCATCACCAGGGACACCTCCAAAGACCA GGTGGTCCTTACAATGACCAACATGGACCCTGTG GACACAGCCACATATTACTGTGCACATAAAGCTA CCTGGGTGGCTTTTGATATCTGGGGCCAAGGGAC AATGGTCACCGTCTCTTCA |
| | | | SEQ ID NO: 27533 | SEQ ID NO: 31539 |
| | | AA | SYDLTQPPSVTVSPGQTASITCSGDKLGNKYAC WYQQKPGQSPVVVIYQDRKRPSGIPERFSGSNSG NTATLTISGTQAMDEADYYCQAWDINTAVFGG GTKLTVL | QITLKESGPTLVKPTQTLTLTCTFSGFSLSTSGVGVG WIRQPPGKALEWLALINWNDDKRFSPSLKSRFTITR DTSKDQVVLTMTNMDPVDTATYYCAHKATWVAF DIWGQGTMVTVSS |
| | | | SEQ ID NO: 27534 | SEQ ID NO: 31540 |
| iPS:436896 | 21-225_67F10 | NA | TCCTATGAACTGACTCAGCCACCCTCAGTTTCC GTGTCCCCAGGACAGACAGCCAGCATCACCTG CTCTGGAGATAAATTGGGGTATAAATATGCTT GGTGGTATCAGCAGAAGCCAGGCCAGTCCCCT GTGGTGGTCATCTTTGAAGATAGGAAGCGGCC CTCAGGGATCCCTGAGCGATTCTCTGGCTCCA ACTCTGGGAACACAGCCACTCTGACCATCAGC GGGACCCAGGCTATGGATGAGGCTGACTATTA CTGTCAGGCGTGGGACAACAGCACTGTGGTAT TCGGCGGAGGGACCAAGCTGACCGTCCTA | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTATATTACTGTGCGAGAACGTAT TTCTATGGTTCGGGGAGTTATTATAACGGCTTTG ACTACTGGGGCCAGGGAACCCTGGTCACCGTCTC CTCA |
| | | | SEQ ID NO: 27535 | SEQ ID NO: 31541 |

FIGURE 50
(Continued)

| | | | |
|---|---|---|---|
| iPS:436898 | 21-225_68D8 | AA | SYELTQPPSVSVSPGQTASITCSGDKLGYKYAW WYQQKPGQSPVLVIFEDRKRPSGIPERFSGSNSG NTATLTISGTQAMDEADYYCQAWDNSTVVFGG GTRLTVL<br>SEQ ID NO: 27536 | QVQLVQSGAEVKKPGASVKVSCKASGYTFTGYYM HWVRQAPGQGLEWMGWINPNSGGTNYGQKFQGR VTMTRDTSISTAYMELSRLRSDDTAVYYCARTYFY GSGSYYNGFDYWGQGTLVTVSS<br>SEQ ID NO: 31542 |
| | | NA | TCCTATGAGCTGACTCAGCCACCCTCAGTGTC CGTGTCCCAGGACAGACAGCCAGCATCACCT GCTCTGGAGATAAATTGGGGGATATAAATATGCT TGCTGGTATCAGCAGAAGCCAGGCCAGTCCCC TGTGTTGGTCATCTATCAAGATAGCAAGCGGC CCTCAGGGATCCCTGAGCGATTCTCTGGCTCC AACTCTGGGAACACAGGCTATGAGGCTGACTATT CGGGACCCAGGCTGTGGGACAACAGCACTGTGTA ACTGTCAGGCGTGGGACAACAGCACTGTGGTA TTCGGCGGAGGGACCAAGCTGACCGTCCTA<br>SEQ ID NO: 27537 | CAGGTACAGCTGCAGCAGTCAGGTCCAGGACTG GTGAAGCCCTCGCAGACCCTCACTCACCTGTG CCATCTCCGGGGACAGTGTCTCTAGCAACAGTGC TGCTTGGAACTGGATCAGGCAGTCCCATCGAGA GGCCTTGAGTGGCTGGGAAGGACATACTACAGG TCCGAGTGCTATAATGATTATGCAGTATCTGTGC AGAGTGCAATAACCATCAACCAGACACATCCA AGAACCAGTTCTCCCTGCACTGAACTCTGTGAC TCCCGAGGACACGGCTGTGTATTTCTGTGCAAGA GATAGAGGGCATAGAGGGTTCTACGGTATGGAC GTCTGGGGCCAAGGGACCACGGTCACCGTCTCCT CA<br>SEQ ID NO: 31543 |
| | | AA | SYELTQPPSVSVSPGQTASITCSGDKLGDKYACW YQQKPGQSPVLVIYQDSKRPSGIPERFSGSNSGN TATLTISGTQAMDEADYYCQAWDNSTVVFGGG TKLTVL<br>SEQ ID NO: 27538 | QVQLQQSGPGLVKPSQTLSLTCAISGDSVSSNSAA WNWIRQSPSRGLEWLGRTYYRSECYNDYAVSVQS RITINPDTSKNQFSLHLNSVTPEDTAVYFCARDRGH RGFYGMDVWGQGTTVTVSS<br>SEQ ID NO: 31544 |

FIGURE 50
(Continued)

| | | NA | TCCTATGAGCTGACTCAGCCACCCTCAGTGTC CGTGTCCCCAGGACAGACAGCCAGCATCACCT GCTCTGGAGATAAATTGGGGATAAATATGAT TACTGGTATCAGCAGAAGCCAGGCCAGTCCCC TGTGCTGGTCATCTATCAAGATAGAAAGCGGC CCTCAGGGATCCCTGAGCGATTCTCTGGCTCC AACTCTGGAAACAGCACCCTGACCATCAG CGGGACCCAGGCTATGGATGAGGCTGACTATT ACTGTCAGGCGTGGGACAACAGCACTGTGTA TTCGGCGGAGGGACCAAACTGACCGTCCTA<br><br>SEQ ID NO: 27539 | CAGGTGCAGATGGTGCAGTCTGGGGATGAGGTG AAGAAGCCTGGGGCCTCAGTGAAGGTCTCGTGC AAGGCTTCGGGATACACCTTCACCGGCTACCATA TGCACTGGGTGCGACAGGCCCCTGGACAAGGGC TTGAGTGGATGGGATGGATCAACCCTAACAGTGG TGGCACAAATTATGCACAGAAGTTCAGGCAG GGTCACCATGACCAGGGACACGTCCATCAGCAC AGCCTACATGGAGCTGAGCAGGATGAGATCTGA CGACACGGCCGTGTATTACTGTGCGAGAGCGTAT TATTATGTTCGGGGAGTTATTATAATGAATCTG ATATGTGGGGCCAAGGGACAATGGTCACCGTCTC TTCA<br><br>SEQ ID NO: 31545 |
|---|---|---|---|---|
| iPS:436900 | 21-225_69B9 | AA | SYELTQPPSVSVSPGQTASITCSGDKLGNKYDY WYQQKPGQSPVLVIYQDRKRPSGIPERFSGSNSG NTATLTISGTQAMDEADYYCQAWDNSTVFGG GTKLTVL<br><br>SEQ ID NO: 27540 | QVQMVQSGDEVKKPGASVKVSCKASGYTFTGYH MHWVRQAPGQGLEWMGWINPNSGGTNYAQKFQ GRVTMTRDTSISTAYMELSRMRSDDTAVYYCARA YYYVGSGSYYNESDMWGQGTMVTVSS<br><br>SEQ ID NO: 31546 |
| iPS:436902 | 21-225_69B11 | NA | TCCTATGAGCTGACTCAGCCACCCTCAGTGTC CGTGTCCCCAGGACAGACAGCCAGCATCACCT GCTCTGGAGATAAATTGGGGATAAATATGCT TGGTGGTATCAGCAGAAGCCAGGCCAGTCCCC TGTGCTGGTCATCTATGAAGATAGAAAGCGGC CCTCAGGGATCCCTGAGCGATTCTCTGGCTCC AACTCTGGGAACACAGCACTCTGACCATCAG CGGGACCCAGGCTATGGATGAGGCTGACTATT ACTGTCAGGCGTGGGACAACAGCACTGTGTA TTCGGCGGAGGGACCAAGCTGACCGTCCTA<br><br>SEQ ID NO: 27541 | CAGGTGCAGCTGGTGCAGTCCGGGGCTGAGGTG AAGAAGCCTGGGGCCTCAGTGAGGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTCAGGACAG GGTCACCATGACCAGGGACACGTCCATCAGCAC AGCCTTCATGGAGCTGAGCAGGCTGAGATCTGAC GACACGGCCGCATATTACTGTGCGAGAACGTATT ACTATGGTCGGGGAGTTATTATAACGGCTTTGA CTACTGGGGCCAGGGAACCCTGGTCACCGTCTCC TCA<br><br>SEQ ID NO: 31547 |

FIGURE 50
(Continued)

| | | | |
|---|---|---|---|
| iPS:436904 | 21-225_71D4 | AA | SYELTQPPSVSVSPGQAASITCSGDKLGDKYAW WYQQKPGQSPVLVIYEDRKRPSGIPERFSGSNSG NTATLTISGTQAMDEADYYCQAWDNSTVVFGG GTKLTVL<br>SEQ ID NO: 27542 | QVQLVQSGAEVKKPGASVRVSCKASGYTFTGYYM HWVRQAPGQGLEWMGWINPNSGGTNYGQKFQDR VTMTRDTSISTAFMELSRLRSDDTAAYYCARTYYY GSGSYYNGFDYWGQGTLVTVSS<br>SEQ ID NO: 31548 |
| | | NA | TCCTATGAGCTGACTCAGCCACCCTCAGTGTC CGTGTCTCCAGGACAGGCAGCAGCCATCACCT GCTCTGGAGATAAATTGGGGGATAAATATGCT TACTGGTATCAGCAGAAACCAGGCCAGTCCCC TGTGGTGGTCATCTATGAAGATAGGAAGCGGC CCTCAGGGATCCCTGAGCGATTCTCTGGCTCC AACTCTGGGAACACAGGCTATGAGGCTGACTATT CGGGACCCAGGCTGTGGGTCAACAGCACTGTGGTA ACTGTCAGGCGTGGGTCAACAGCACTGTGGTA TTCGGCGGAGGGACCAAGCTGACCGTCCTA<br>SEQ ID NO: 27543 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTGTA TGCACTGGGTGCGACAGGCCCCTGGACAAGGGC TTGAGTGGATGGGATGGATCAACCCTAACAGTGG TGGCACAAACTATGCACAGAAGTTCAGGTCAG GGTCACCATGACCAGGGACACGTCCGTCAGCAC AGTCTACATGGACCTGAGCAGGCTGAGATCTGAC GACACGGCCGTGTATTACTGTGCGAGAGCGTATT ACTATGGTTCGGGGACTTATCATAACGAATTTGA CTACTGGGGCCAGGGAAGTTTGGTCACCGTCTCC TCA<br>SEQ ID NO: 31549 |
| | | AA | SYELTQPPSVSVSPGQTASITCSGDKLGDKYAY WYQQKPGQSPVVVIYQDRKRPSGIPERFSGSNSG NTATLTISGTQAMDEADYYCQAWVNSTVVFGG GTKLTVL<br>SEQ ID NO: 27544 | QVQLVQSGAEVKKPGASVKVSCKASGYTFTGYCM HWVRQAPGQGLEWMGWINPNSGGTNYAQKFQVR VTMTRDTSVSTVYMDLSRLRSDDTAVYYCARAYY YGSGTYHNEFDYWGQGSLVTVSS<br>SEQ ID NO: 31550 |

FIGURE 50
(Continued)

| | | | |
|---|---|---|---|
| iPS:436906 | 21-225_72B4 | NA | TCCTATGAGCTGACTCAGCCACCCTCAGTGTC CGTGTCCCCAGGACAGACAGCCAGCATCACCT GCTCTGGAGATAAATTGGGGATAAATATGCT TGGTGGTATCAGCAGAGGCCAGGCCAGTCCT TGTGCTGGTCATCTATGAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAACAGCACTGTGTA TTCGGCGGAGGGACCAAGCTGACCGTCCTA SEQ ID NO: 27545 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTATATTACTGTGCGAGAACGTAT TACTATGTTCGGGGAGTTATTATAACGGCTTTG ACTACTGGGGCCAGGGAACCCTGGTCACCGTCTC CTCA SEQ ID NO: 31551 |
| | | AA | SYELTQPPSVSVSPGQTASITCSGDKLGDKYAW WYQQRPGQSPVLVIYEDRKRPSGIPERFSGSNSG NTATLTISGTQAMDEADYYCQAWDNSTVVFGG GTKLTVL SEQ ID NO: 27546 | QVQLVQSGAEVKKPGASVKVSCKASGYTFTGYYM HWVRQAPGQGLEWMGWINPNSGGTNYGQKFQGR VTMTRDTSISTAYMELSRLRSDDTAVYYCARTYYY VRGVIITAFDYWGQGTLVTVSS SEQ ID NO: 31552 |
| iPS:436908 | 21-225_72D5 | NA | TCCTATGACCTGACTCAGCCACCCTCAGTGTC CGTGTCCCCAGGACAGACAGCCAGCATCACCT GCTCTGGAGATAAATTGGGGAATAAATATGCT TGCTGGTATCAGCAGAAGCCAGGCCAGTCCCC TGTGGTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTGCGGTA TTCGGCGGAGGGACCAAGCTGACCGTCCTA SEQ ID NO: 27547 | CAGATCACCTTGAAGGAGTCTGGTCCTACGCTGG TGAAACCCACACAGACCCTCACGCTGACCTGCAC CTTCTCTGGGTTCTCACTCAGCACTAGTGGAGTG GGTGTGGGCTGGATCCGTCAGCCCCCAGGAAAG GCCCTGGAGTGGCTTGCACTCATTGATTGGAATG ATGATAAGCGCTACAGCCCATCTCTGAAGAGCA GGTTCACCATCACCAGGGACACCTCCAAAGACC AGGTGGTCTTTACAATGACCAACATGGACCCTGT GGACACAGGCACATATTACTGTGCACATAAAGCT ACCTGGGTGGCTTTGATATCTGGGGCCAAGGGA CAATGGTCACCGTCTCTTCA SEQ ID NO: 31553 |

FIGURE 50
(Continued)

| | | | |
|---|---|---|---|
| | | AA | SYDLTQPPSVSVSPGQTASITCSGDKLGNKYAC WYQQKPGQSPVVVIYQDRKRPSGIPERFSGSNSG NTATLTISGTQAMDEADYYCQAWDSSTAVFGG GTKLTVL<br>SEQ ID NO: 27548 | QITLKESGPTLVKPTQTLTLTCTFSGFSLSTSGVGVG WIRQPPGKALEWLALINWNDDKRYSPSLKSRFTITR DTSKDQVVFTMTNMDPVDTGTYYCAHKATWVAF DIWGQGTMVTVSS<br>SEQ ID NO: 31554 |
| iPS:436910 | 21-225_73G1 | NA | CAGACTGTGGTGACCCAGGAGCCATCGTTCTC AGTGTCCCCTGGAGGGACAGTCACACTCACTT GTGGCTTGAGCTCTGGCTCAGTCTCTACTAGTT ACTACCCCAGCTGGTACCAGCAGACCCCAGGC CAGGCTCCACGCTCACGCTCATCTACAAGACAAA CACTCGCTCTTCTCGGGGTCCCTGATCGCTTCTC TGGCTCCATCCTTGGGAACAAAGCTGCCCTCA CCATCACGGGGGCCCAGCAGATGATGAATCT GATTATTACTGTGTTCTATATATGGGTAGTGCC AITTGGGTGTTCGGCGGAGGGACCAAGTTGAC CGTCCTA<br>SEQ ID NO: 27549 | CAGGTGCAGCTGGTGGAGTCTGGGGGAGGCGTG GTCCAGCCTGGGAGGTCCCTGAGACTCTCCTGTG CAGGCACTGGATTCACCTTCAGTTACTATGGCAT GCACTGGGTCCGCCAGGCTCCAGGCAAGGGGCT GGAGTGGGTGGCAGTTACAACATATGATGAAG TAATAAATACTATGCAGACTCCGTGAAGGGCCG ATTCACCAGTCCAGAGACACAATTCCAAGAACAC GCTGTATCTGCAAATGAATAGCCTGAGAGCTGAG GACACGGCTGTGTATCACTGTGCGAGAGAGACT GGAACCTGGGCTTTTGATATCTGGGGCCAAGGGA CAATGGTCACCGTCTCTTTA<br>SEQ ID NO: 31555 |
| | | AA | QTVVTQEPSFSVSPGGTVTLTCGLSSGSVSTSYY PSWYQQTPGQAPRTLIYNTNTRSSGVPDRFSGSI LGNKAALTITGAQADDESDYYCVLYMGSAIWV FGGGTKLTVL<br>SEQ ID NO: 27550 | QVQLVESGGGVVQPGRSLRLSCAGTGFTFSYYGM HWVRQAPGKGLEWVAVTTYDGSNKYYADSVKGR FTSSRDNSKNTLYLQMNSLRAEDTAVYHCARETGT WAFDIWGQGTMVTVSL<br>SEQ ID NO: 31556 |

FIGURE 50
(Continued)

| | | | |
|---|---|---|---|
| iPS:436912 | 21-225_73C4 | NA | TCCTATGAGCTGACTCAGCCACCCTCAGTGTC CGTGTCCCCAGGACAGACAGCCAGCATCACCT GCTCTGGAGATAAATTGGGGATAAATATGCT TGCTGGTATCAGCAGAAGCCAGGCCAGTCCCC TGTGGTGGTCATCTATCAAGATATGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTGCGGTA TTCGGCGGAGGGACCAAGCTGACCGTCCTA | CAGATCACCTTGAAGGAGTCTGGTCCTACGCTGG TGAAACCCACAGACCCTCAGCTGACCTGCAC CTTCTCTGGGTTCTCACTCAGCACTAGTGGAGTG GGTGGGCTGATCCGTCAGCCCCCAGGAAAG GCCCTGGAGTGGCTTGCACTCATTAATTGGAATG ATGATAAGCGCTACAGCCCATCTCTGAAGAGCA GGTTCACCATCTCCAAGGACACCTCCAAAGACC AGTGGTCCTTACAATGACCAACATGGCACCTGT GGACACAGCCACATATTACTGTGCACATAAAACT ACCTGGGTGGCTTTGATATCTGGGGCCAAGGGA CAATGGTCACCGTCTCTTCA |
| | | | SEQ ID NO: 27551 | SEQ ID NO: 31557 |
| | | AA | SYDLTQPPSVSVSPGQTASITCSGDKLGNKYAC WYQQKPGQSPVVVIYQDMKRPSGIPERFSGSNS GNTATLTISGTQAMDEADYYCQAWDSSTAVFG GGTKLTVL | QITLKESGPTLVKPTQTLTLTCTFSGFSLSTSGVGVG WIRQPPGKALEWLALINWNDDKRYSPSLKSRFTITR DTSKDQVVLTMTNMDPVDTATYYCAHKTTWVAF DIWGQGTMVTVSS |
| | | | SEQ ID NO: 27552 | SEQ ID NO: 31558 |
| iPS:436914 | 21-225_76B4 | NA | CCCTATGAGCTGAATCAGACACCCTCAGTGTC CGTGTCCCCAGGACAGACAGCCAGCATCACCT GCTCTGGAGATAGATTGGGGACTAAATTTGCT TGCTGGTATCAGCAGAAGCCAGGCCAGTCCCC TGTGCTGGTCATTTATCAAGATAAGCAAGCGGC CCTCAGGGATCCCTGAGCGATTCTCTGGCTCC AACTCTGGGAACACACAGGCTATGGATGAGGCTGACTATT ACTGTCAGGCGTGGGACAGCAGCACTGTATTC GGCGGAGGGACCAAGCTGACCGTCCTA | CAGATCACCTTGAAGGAGTCTGGTCCTACGCTGG TGAAACCCACAGACCCTCAGCTGACCTGCAC CTTCTCTGGGTTCTCACTCAGCACTGGTGAGTG GGTGGGCTGATCCGTCAGCCCCCAGGAAAG GCCCTGGAGTGGCTTGCACTCATTATTGGGATG ATGATAAGCGCTACAGCCCATCTATTGGGATG GGCTCACCATCACCAAGGACACCCCAAAAACC AGTGGTCCTTACAATGACCAACATGGACCCTGT GGACACAGCCACATATTACTGTGCACACCTTATA GCAGTGGCCTTTGACTACTGGGGCCAGGAACCC TGGTCACCGTCTCCTCA |
| | | | SEQ ID NO: 27553 | SEQ ID NO: 31559 |

FIGURE 50
(Continued)

| | | | |
|---|---|---|---|
| iPS:436916 | 21-225_74A9 | AA | PYELNQTPSVSVSPGQTASITCSGDRLGTKFACW YQQKPGQSPVLVIYQDSKRPSGIPERFSGSNSGN TATLTISGTQAMDEADYYCQAWDSSTVFGGGT KLTVL<br>SEQ ID NO: 27554 | QITLKESGPTLVKPTQTLTLTCTFSGFSLSTGGVGVG WIRQPPGKALEWLALIYWDDDKRYSPSLKSRLTIT KDTPKNQVVLTMTNMDPVDTATYYCAHLIAVAFD YWGQGTLVTVSS<br>SEQ ID NO: 31560 |
| | | NA | TCCTATGAGCTGACTCAGCCACCCTCAGTGTC CGTGTCCCCAGGACAGACAGCCAGCATCACCT GCTCTGAGATAAATTGGGTAATAAATATGTT TGTTGGTATCAGCAGAAGCCAGGCCAGTCCCC TGTGCTGGTCATCTATCAAGATAACAGGCGGC CCTCAGGGATCCCTGAGCGATTCTCTGGCTCC AACTCTGGGAACACAGCCACTCTGACCATCAG CGGGACCCAGGCTATGGAGGCTGACTATT ACTGTCAGGGCTGGGACAGCAGTCCTGTGATA TTCGGCGGAGGGACCAAACTGACCGTCCTA<br>SEQ ID NO: 27555 | CAGGTGCAACTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGGAAAT AATAAATCCTATGCAGACTCCGTGAAGGGCCGAT TCACCATCTCCAGAGACATTTCCAAGAACACGCT GTTCTGCAAATGAACAGCTGAGAGCCGATGAC ACGGCTGTGTATTACTGTGCGAGAGATCGAGATT ATTGTAGTGGTACCAGCTGCCCTTATTATTACTAC TACGGTATGGACGTCTGGGGCCAAGGGACCACG GTCACCGTCTCCTCA<br>SEQ ID NO: 31561 |
| | | AA | SYELTQPPSVSVSPGQTASITCSGDKLGNKYVCW YQQKPGQSPVLVIYQDNRRPSGIPERFSGSNSGN TATLTISGTQAMDEADYYCQAWDSSPVIFGGGT KLTVL<br>SEQ ID NO: 27556 | QVQLVESGGGVVQPGRSLRLSCAASGFTFSSYGMH WVRQAPGKGLEWVAVIWYDGNNKSYADSVKGRF TISRDISKNTLFLQMNSLRADDTAVYYCARDRDYC SGTSCPYYYYGMDVWGQGTTVTVSS<br>SEQ ID NO: 31562 |

FIGURE 50
(Continued)

| | | | |
|---|---|---|---|
| iPS:436918 | 21-225_77A2 | NA | TCCTATGAGCTGACTCAGCCACCCTCAGTGTC CGTGTCCCCAGGACAGACAGCCAGCATCACCT GCTCTGGAGATAGATTGGGGGATAAATATGCT TGCTGGTATCAGCAGAAGCCAGGCCAGTCCCC TGTACTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGTACTGCGGTA TTCGGCGGAGGGACCAAGCTGACCGTCCTA SEQ ID NO: 27557 | CAGATCACCTTGAAGGAGTCTGGTCCTTCGCTGG TGAAACCCACACAGACCCTCACGCTGACCTGCAC CTTCTCTGGGTTCTCACTCAGCACTAGTGGAGTG GGTGGGCTGGATCGTCAGCCCCCAGAAAG GCCCTGGAGTGGCTTGTATTCATTTATTGGGATG ATGATAAGCGCTACAGCCCATCTCTGAAGAGCA GGCTCACCATCACCAAGGACACCTCCAAAAACC AGTGGTCCTTACAATGACCAACATGACCCTGT GGACACAGCCACATATTACTGTGCACACCTTATA GCAGTGGCCTTTGACTACTGGGGCCAGGGAACCC TGGTCACCGTCTCCTCA SEQ ID NO: 31563 |
| | | AA | SYELTQPPSVSVSPGQTASITCSGDRLGDKYACW YQQKPGQSPVLVIYQDRKRPSGIPERFSGSNSGN TATLTISGTQAMDEADYYCQAWDSSTAVFGGG TKLTVL SEQ ID NO: 27558 | QITLKESGPSLVKPTQTLTLTCTFSGFSLSTSGVVG WIRQPPGKALEWLVFIYWDDDKRYSPSLKSRLTIT KDTSKNQVLTMTNMDPVDTATYYCAHLIAVAFD YWGQGTLVTVSS SEQ ID NO: 31564 |
| iPS:436920 | 21-225_74E5 | NA | CAGACTGTGGTGACTCAGGAGCCCTCACTGAC TGTGTCCCCAGGAGGAGGACAGTCACTCTCACCT GTGCTTCCAGCACTGAAACAGTCACCAGTGGT TCTTATCCGAACTGGTTCCAGCAGAAACCTGG ACAAGCACCCAGGCACTGATTTATAGTACAA GCAACAAACACTCCTGGACCCTGCCCGTTC TCAGGCTCCCTCCTTGGGGCAAAGCTGCCCT GACACTGTCAGATGTGCAGCCTGAGGACGAG GCTGAGTATTACTGCCTGCTCTCTACTATGGTGGT GCTCAACTGGTATTCGGCGGAGGGACCAAGCT GACCGTCCTA SEQ ID NO: 27559 | CAGGTGCAGCTGCAGGAGTCGGGCCCAGGACTG GTGAAGCCTTCACAGACCCTGTCCTCCACCTGCA CTGTCTCTGGTGGCTCCATCAGAAGTGGTTA CTACTGGAGCTGGATCCGCCAGCACCCAGGGAA GGGACTGGAGTGGATTGGATACATCTATTACAGT GGGAGCACTACTACAACCCGTCCCTCAGGAGTC GAGCTTCCATATCAGTAGACACGTCTAAGAACCA GTTCTCCCTGAAGCTGAGCTCTGTGACTGCCGCG GACACGGCCGTGTATTACTGTGCGAGAGATTCAC CAGTGGCTGGTACTGACTACTGGGGCCAGGGAA CCCTGGTCACCGTCTCCTCA SEQ ID NO: 31565 |

FIGURE 50
(Continued)

| | | | |
|---|---|---|---|
| iPS:436922 | | AA | QTVVTQEPSLTVSPGGTVTLTCASSTETVTSGSY PNWFQQKPGQAPRALIYSTNKHSWTPARFSGS LLGGKAALTLSDVQPEDEAEYYCLLYYGGAQL VFGGGTKLTVL<br>SEQ ID NO: 27560 | QVQLQESGPGLVKPSQTLSLTCTVSGGSIRSGGYY WSWIRQHPGKGLEWIGYIYYSGSTYYNPSLRSRASI SVDTSKNQFSLKLSSVTAADTAVYYCARDSPVAGT DYWGQGTLVTVSS<br>SEQ ID NO: 31566 |
| | | NA | TCTTATGAGTTGACTCAGCCACCCTCAGAGTC TGTGTCCCCAGGACAGACAGCCAGCATCACGT GCTCAGGAGATAAATTGGGGAATAAATATGTT TCCTGGTATCAGCAGAAGCCAGGCCAGTCCCC TGTGCTGGTCATCTATCAAGATAACAGGCGGC CGTCAGGGATCCCTGAGCGATTTCTCTGGCTCC AACTCTGGGAGCACAGCCACTTTGACCATCAG CGGACCCAGGCTATGGAGCAGCCCTGTGATA ACTGTCAGGCGTGGGACAGCAGCCTGACCGTCC TTCGGCGGAGGGACCAAGCTGACCGTCCTA<br>SEQ ID NO: 27561 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCACTGGGTCCGCCAGGCTCCAGGCAAGGGGCT GGAGTGGGTGGCAGTTATATGGTATGATGGAAAT AATAAATCCTATGCAGACTCCGTGAAGGGCCGAT TCACCATCTCCAGAGACACATTTCCAAAAACACGCT GTATCTGCAAATGAACAGCTGAGAGCCGAGGA CACGGCTGTGTATTACTGTGCGAGGGATCGAGAT TATTGTAGTAGTACCAGCTGCCCTTATTATTACTA CTACGGTATGGACGTCTGGGGGCCAAGGGACCAC GGTCACCGTCTCCTCA<br>SEQ ID NO: 31567 |
| | 21-225_78E9 | AA | SYELTQPPSESVSPGQTASITCSGDKLGNKYVSW YQQKPGQSPVLVIYQDNRRPSGIPERFSGSNSGS TATLTISGTQAMDEADYCQAWDSSPVIFGGGT KLTVL<br>SEQ ID NO: 27562 | QVQLVESGGGVVQPGRSLRLSCAASGFTFSSYGMH WVRQAPGKGLEWVAVIWYDGNNKSYADSVKGRF TISRDISKNTLYLQMNSLRAEDTAVYYCARDRDYC SSTSCPYYYYGMDVWGQGTTVTVSS<br>SEQ ID NO: 31568 |

FIGURE 50
(Continued)

| | | NA | TCCTATGAGCTGACTCAGCCACCCTCAGTGTC CGTGTCCCCAGGACAGACAGCCAGCATCACCT GCTCTGGAGATAAATTGGGGATAAATATGCT TGCTGGTATCAGCAGAAGCCAGGCCAGTCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGAGACCCAGGCTATGAGGACACCACTGTGTA ACTGTCAGGCGTGGGACAGCAGCACCACTGTGTA TTCGGCGGAGGGACCAAGCTGACCGTCCTA<br><br>SEQ ID NO: 27563 | CAGGTGCAGCTGGTGGAGTCTGGGGGAGGCGTG GTCCAGCCTGGGAGGTCCCTGAGACTCTCCTGTG CAGCGTCGGATTCACCTTCAGTCGATATGGCAT GCACTGGGTCCGCCAGGCTCCAGGCAAGGGCT GGAGTGGGTGGCAGTTTTTGGTATGATGAAGT AATAAAGACTATGCAGACTCCGTGAAGGGCGA TTCACCATCTCCAGAGACAATTCCAAGAACACGC TGTATCTGCAAATGAACAGCCTGAGAGCCGAGG ACACGGCTGTGTATTACTGTGCGAGAGATCGAGA TTATTGTAGTAGTACCAGCTGCCCTTACTACTACT ACTACGGTATGGACGTCTGGGGCCAAGGGACCA CGGTCACCGTCTCCTCA<br><br>SEQ ID NO: 31569 |
| iPS:436924 | 21-225_74B3 | AA | SYELTQPPSVSVSPGQTASITCSGDKLGDKYACW YQQKPGQSPVLVIYQDSKRPSGIPERFSGSNSGN TATLTISGTQAMDEADYYCQAWDSTTVVFGGG TKLTVL<br><br>SEQ ID NO: 27564 | QVQLVESGGGVVQPGRSLRLSCAASGFTFSRYGMH WVRQAPGKGLEWVAVFWYDGSNKDYADSVKGRF TISRDNSKNTLYLQMNSLRAEDTAVYYCARDRDY CSSTSCPYYYYYGMDVWGQGTTVTVSS<br><br>SEQ ID NO: 31570 |

FIGURE 50
(Continued)

| | | | | |
|---|---|---|---|---|
| iPS:436926 | 21-225_78D10 | NA | CAGACTGTGGTGACTCAGGAGCCCTCACTGAC TGTGTCCCAGGAGGACAGTCAGTCACTCACCT GTGCTTCCAGCACTGGAGCAGTCAGTCACCTGGT TACTTTCCAAACTGGTTCCAGCAGAAACCTGG ACAAGCACCCAGGGCACTGATTTATAGTACAG ACAACAAACACTCCTGGACCCCTGCCCGGTTC TCAGGCTCCCTCCTTGGGGGCAAAGCTGCCT GACACTGTCAGGTGTGCAGCCTGAGGACGAG GCTGAGTATTACTGCCTCCTCTACTATGGTGGT GCTCAGCTGATGTTCGGCGGAGGGACCAAGCT GACCGTCCTA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAGCTGATCCGCCAGCACCCAGGAA GGGCCTGGAGTGGATTGGGTACATCTATTACATT GGGAGTGTTTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTACTACTGTGCGAGAGATGCCC CCGACTTCGGTATGGACGTCTGGGGCCAAGGGA CCACGGTCACCGTCTCCTCA |
| | | | SEQ ID NO: 27565 | SEQ ID NO: 31571 |
| | | AA | QTVVTQEPSLTVSPGGTVTLTCASSTGAVTSGYF PNWFQQKPGQAPRALIYSTDNKHSWTPARFSGS LLGGKAALTLSGVQPEDEAEYYCLLYYGGAQL MFGGGTKLTVL | QVQLQESGPGLVKPSQTLSLTCTVSGGSISSGGVYW SWIRQHPGKGLEWIGYIYYIGSVYYNPSLKSRVTIS VDTSKNQFSLKLSSVTAADTAVYYCARDAPDFGM DVWGQGTTVTVSS |
| | | | SEQ ID NO: 27566 | SEQ ID NO: 31572 |
| iPS:436928 | 21-225_79E7 | NA | TCCTATGAGCTGACTCAGCCACCCTCAGTGTC CGTGTCCCAGGACAGACAGCAGCATCACCT GCTCAGGAGATAAATTGGGGAATAAATATGTT TCCTGGTATCAGCAGAAGCCAGGCCAGTCCCC TGTGCTGGTCATCTATCAAGATAACAGGCGGC CCTCAGGGATCCCTGAGCGATTCTCTGGCTCC AACTCTGGGACACAGCCACTCTGACCATCAG CGGGACCCAGGCTATGGACAGCAGCCTGACTAT ACTGTCAGGGCTGTGGGACCAAGCTGACCGTCCTA TTCGGCGGAGGGACCAAGCTGACCGTCCTCA | CAGGTGCAGCTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGGAAAT AATAAATCTATGCAGACTCCGTGAAGGGCCGAT TCACCATCCAGAGACATTTCCAAAAACACGCT GTATCTGCAAATGAACAGCCTGAGAGCCGAGGA CACGGCTGTGTATTACTGTGCGAGGGATCGAGAT TATTGTAGTAGTACCAGCTGCCCTTATTATTACTA CTACGGTATGGACGTCTGGGGCCAAGGGACCAC GGTCACCGTCCTCA |
| | | | SEQ ID NO: 27567 | SEQ ID NO: 31573 |

FIGURE 50
(Continued)

| | | AA | SYELTQPPSVSVSPGQTASITCSGDKLGNKYVSW YQQKPGQSPVLVIYQDNRRPSGIPERFSGSNSGS TATLTISGTQAMDEADYYCQAWDSSPVIFGGGT KLTVL | QVQLVESGGGVVQPGRSLRLSCAASGFTFSSYGMH WVRQAPGKGLEWVAVIWYDGNNKSYADSVKGRF TISRDISKNTLYLQMNSLRAEDTAVYYCARDRDYC SSTSCPYYYYYGMDVWGQGTTVTVSS |
|---|---|---|---|---|
| | | | SEQ ID NO: 27568 | SEQ ID NO: 31574 |
| iPS:436932 | 21-225_92A4 | NA | TCCTATGAGCTGACTCAGCCACCCTCAGTGTC CGTGTCCCCAGGACAGACAGCCAGTCACCT GCTCTGGAGATAAATTGGGAAGCCAGCATAAATATGTT TGCTGGTATCAACAGAAGCCAGGCCAGTCCCC TGTGTTGGTCATCTATCAAGATAACAGGCGG CCTCAGGGATCCCTGAGCGATTCTCTGGCTCC AACTCTGGGAACACAGGCTACTCTGACCATCAG CGGGACCCAGGCTGTGGGACAGCAGCCCTGTGATA ACTGTCAGGGCGTGGGAGGGACCAAGCTGACCGTCCTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTATGATGAAAT AATAAATCCTATGCAGACTCCGTGAAGGGCCGAT TCACCATCTACAGAGACATTTCCAAGAACACGCT GTATCTGCAAATGAACAGCTGAGAGCCGAGGA CACGGCTGTGTATTACTGTGCGAGAGATCGAGAT TATTGTAGTAGTACCAGCTGCCCTTATTATTACTA CTACGGTATGGACGTCTGGGCCAAGGGACCAC GGTCACCGTCTCCTCA |
| | | | SEQ ID NO: 27569 | SEQ ID NO: 31575 |
| | | AA | SYELTQPPSVSVSPGQTANITCSGDKLGNKYVC WYQQKPGQSPVLVIYQDNRRPSGIPERFSGSNSG NTATLTISGTQAMDEADYYCQAWDSSPVIFGGG TKLTVL | QVQLVESGGGVVQPGRSLRLSCAASGFTFSSYGMH WVRQAPGKGLEWVAVIWYDGNNKSYADSVKGRF TIYRDISKNTLYLQMNSLRAEDTAVYYCARDRDYC SSTSCPYYYYYGMDVWGQGTTVTVSS |
| | | | SEQ ID NO: 27570 | SEQ ID NO: 31576 |

FIGURE 50
(Continued)

| | | | |
|---|---|---|---|
| iPS:436934 | 21-225_96B5 | NA | CCCTATGAGCTGAATCAGACACCCTCAGTGTC CGTGTCCCCAGGACAGACAGCCAGCATCACCT GCTCTGGAGATAGCAGGGACTAAATTTGCT TGCTGGTATCAGCAGAAGCCAGGCCAGTCCC TGTGCTGGTCATTTATCAAGATAGCAAGCGGC CCTCAGGGATCCCGAGCGATTCTCTGGCTCC AACTCTGGGAACAGCACTCTGACCATCAG CGGGACCCAGGCTATGGATGAGGCTGACTATT ACTGTCAGGCGTGGGACAGCAGCACTGTATTC GGCGGAGGGACCAAGCTGACCGTCCTA SEQ ID NO: 27571 | CAGATCACCTTGAAGGAGTCTGGTCCTACGCTGG TGAAACCACACAGACCCTCACGTGACCTGCAC CTTCTCTGGGTTCTCACTCAGCACTGGTGGAGTG GGTGTGGGCTGGATCCGTCAGCCCCCAGAAAG GCCCTGGAGTGGCTTGCACTCATTTATTGGGATG ATGATAAGCGCTACAGCCCATCTCTGAAGAGCA GGCTCACCATCACCAAGGACACCCCAAAACC AGTTGGTCCTTACAATGACCAACATGACCCTGT GGACACAGCCACATATTACTGTGCACACCTTATA GCAGTGGCTGTGACTACTGGGGCCAGGGAACC CTGGTCACCGTCTCCTCA SEQ ID NO: 31577 |
| | | AA | PYELNQTPSVSVSPGQTASITCSGDRLGTKFACW YQQKPGQSPVLVIYQDSKRPSGIPERFSGSNSGN TATLTISGTQAMDEADYYCQAWDSSTVFGGGT KLTVL SEQ ID NO: 27572 | QITLKESGPTLVKPTQTLTLTCTFSGFSLSTGGVG WIRQPPGKALEWLALIYWDDDKRYSPSLKSRLTIT KDTPKNQVLTMTNMDPVDTATYYCAHLIAVACD YWGQGTLVTVSS SEQ ID NO: 31578 |
| iPS:436936 | 21-225_97E6 | NA | TCCTATGAGCTGACTCAGCCACCCTCAGTGTC TGTGTCCCCAGGACAGACAGTCAGCATCACCT GCTCTGGAGATAAATTGGGGAATAAATATGTT TCCTGGTATCAGCAGAAGCCAGGCCAGTCCCC TGTGCTGGTCATCTATCAAGATAACAGGCGGC CGTCAGGGATCCCTGAGCGATTCTCTGGCTCC AACTCTGGGAGCACAGCCACTCTGACCATCAG CGGGACCCAGGCTATGGATGAGGCTGACTATT ACTGTCAGGCGTGGGACAGCAGCACCCCTGATA TTCGGGGAGGGACCAAGCTGACCGTCCTA SEQ ID NO: 27573 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGGTATGATGGAAAT AATAAATCTATGCAGACTCCGTGAAGGGCCGAT TCACCATCTCCAGAGACAATTCCAAAAACACGCT GTATCTGCAAATGAACAGCCTGAGAGCCGAGGA CACGGCTGTGTATTACTGTGCGAGGGATCGAGAT TATTGTAGTAGTACCAGCTGCCCTTATTATTACTA CTACGGTATGGACGTCTGGGGCCAAGGGACCAC GGTCACCGTCTCCTCA SEQ ID NO: 31579 |

FIGURE 50
(Continued)

| | | | |
|---|---|---|---|
| iPS:436938 | | AA | SYELTQPPSVSVSPGQTVSITCSGDKLGNKYVSW YQQKPGQSPVLVIYQDNRRPSGIPERFSGSNSGS TATLTISGTQAMDEADYYCQAWDSTPVIFGGGT KLTVL | QVQLVESGGGVVQPGRSLRLSCAASGFTFSSYGMH WVRQAPGKGLEWVAVIWYDGNNKSYADSVKGRF TISRDISKNTLYLQMNSLRAEDTAVYYCARDRDYC SSTSCPYYYYGMDVWGQGTTVTVSS |
| | | | SEQ ID NO: 27574 | SEQ ID NO: 31580 |
| | 21-225_146A3 | NA | TCCTATGCGATGACTCAGCCACCCTCAATGTC CGTGTCCCCAGGACAGACAGCCAGCATCACCT GCTCTGGAAATAAATTGGGAATAGAGCCAGTATGCT TGCTGGTATCAGCAGAAGCCAGGCCAGTCCCC TGTGCTGGTCATCTATCAAGATAGCAAGCGGC CCTCAGGGATCCCTGAACATAGCCACTCTGACCATCAG CGGGACCCAGGCTATGGATGAGGCTGACTATT ACTGTCAGGCGTGGGACAGCAGCACTGTGTA TTCGGCGGAGGGACCAAGCTGACCGTCCTA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGTTATTAGTGGTGGTACT ACCACATACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCTCCTCA |
| | | | SEQ ID NO: 27575 | SEQ ID NO: 31581 |
| | | AA | SYAMTQPPSMSVSPGQTASITCSGNKLGNRYAC WYQQKPGQSPVLVIYQDSKRPSGIPERFSGSNSG NIATLTISGTQAMDEADYYCQAWDSSTVFGGG TKLTVL | EVQLLESGGGLVQPGGSLRLSCAASGFTFSSYAMS WVRQAPGKGLEWVSVISGGTTTYYADSVKGRFTI SRDNSKNTLYLQMNSLRAEDTAVYYCAKWRGNPT DYGMDVWGQGTTVTVSS |
| | | | SEQ ID NO: 27576 | SEQ ID NO: 31582 |

FIGURE 50
(Continued)

| iPS:436940 | 21-225_146B8 | NA | TCCTATGAGCTGACTCAGCCACCCTCAGTGTC CGTGTCCCCAGGACAGAGACAGCCAGCATCACCT GCTCTGGAGATAAATTGGGGATAAATATGTT TGCTGGTATCAGCAGAAGCCAGGCCAGTCCC TGTGTTGGTCATCTATCAAGATAGGAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGCACAGCAGCACTGTGTA TTCGGCGGAGGGACCAAGCTGACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTCAGTACCTATGGCAT GCACTGGGTCCGCCAGGCTCCAGGCAAGGGCT GGAGTGGGTGGCAGTTGTATGGTATGGTGAAAT GATAAAGACTTTGCAGACTCCGTGACGGGCCGAT TCACCATCTCCAGAGACATTTCCAAGAACACACT GTATCTGCAAATGAACAGCCTGAGAGCCGAGGA CACGGCTGTGTATTACTGTGCGAGAGATCGGAT TATTGTAGTGGTGGTAGCTGCCCTTACTACTACT ACTACGGTATGGACGTCTGGGGCCAAGGGACCA CGGTCACCGTCTCCTCA |
| --- | --- | --- | --- | --- |
| | | | SEQ ID NO: 27577 | SEQ ID NO: 31583 |
| | | AA | SYELTQPPSVSVSPGQTASITCSGDKLGDKYVCW YQQKPGQSPVLVIYQDRKRPSGIPERFSGSNSGN TATLTISGTQAMDEADYYCQAWHSSTVFGGG TKLTVL | QVQLVESGGGVVQPGRSLRLSCAASGFTFSTYGMH WVRQAPGKGLEWVAVVWYGGNDKDFADSVTGR FTISRDISKNTLYLQMNSLRAEDTAVYYCARDRDY CSGGSCPYYYYYGMDVWGQGTTVTVSS |
| | | | SEQ ID NO: 27578 | SEQ ID NO: 31584 |

FIGURE 50
(Continued)

| | | | |
|---|---|---|---|
| iPS:436942 | 21-225_146H8 | NA | TCCTATGAGCTGACTCAGCCACCCTCAGTGTCCGTGTCCCCAGGACAGAGACAGCCAGCATCACCTGCTCTGGAGATAAATTGGGGGATAAATATGCTTGCTGGTATCAGCAGAAGCCAGGCCAGTCCCCTGTGCTGGTCATCTATCAAGATAAGAAGCGGCCCTCAGGGATCCCTGAGCGATTCTCTGGCTCCAACTCTGGGAACACAGCCACTCTGACCATCAGCGGGACCCAGGTTATGGATGAGGCTGACTATTACTGTCAGGCGTGGGACATCAGAACTGTGGTATTCGGCGGAGGGACCAAGCTGACCGTCCTA |
| | | | SEQ ID NO: 27579 |
| | | | CAGGTGCAGCTGGTGCAGTCTGGGGCTGAGGTGAAGAAGCCTGGGGCCTCAGTGAAGGTCTCCTGCAAGGCTTCTGGATACACCTTCATCAGTTATGATAATCAATTGGGTGCGACAGGCCACCTGACAAGGGCTTGAGTGGATGGGATGGATGAACCCTAACAGTGGTAACACAGGCTATGCACAGAAGTTCCAGGCAGAGTCACCATGACCAGGAACACCTCCAAAAGCACAGCCTACATGGAGCTGAGCAGCCTGAGATCTGAGGACACGGCCGTGTATTACTGTGCGAGAGAGATTATTACTATGATAGTAGTGGTCACCAGCCTTACTACTACTACGGTATGGACGTCTGGGGCCAAGGGACCACGGTCACCGTCTCCTCA |
| | | AA | SYELTQPPSVSVSPGQTASITCSGDKLGDKYACWYQQKPGQSPVLVIYQDKKRPSGIPERFSGSNSGNTATLTISGTQVMDEADYYCQAWDIRTVVFGGGTKLTVL |
| | | | SEQ ID NO: 27580 |
| | | | QVQLVQSGAEVKKPGASVKVSCKASGYTFISYDNWVRQATGQGLEWMGWMNPNSGNTGYAQKFQGRVTMTRNTSKSTAYMELSSLRSEDTAVYYCARGDYYYDSSGHQPYYYYGMDVWGQGTTVTVSS |
| | | | SEQ ID NO: 31586 |

FIGURE 50
(Continued)

| | | | |
|---|---|---|---|
| iPS:436944 | 21-225_182D12 | NA | TCCTATGAGCTGACTCAGCCACCCTCAGTGTCCGTGTCCCCAGGACAGACAGCCAGCATCACCTGCTCTGGAGATAAATTGGGGGAGAAATATGCTTGCTGGTATCAGCAGAAGTCAGGCCAGTCCCCTGTGTTGGTCATCTATCAAGATAGAAAGCGGCCCTCAGGGATCCCTGAGCGATTCTCTGGCTCCAACTCTGGGAACACAGCCACTCTGACCATCAGCGGGACCCAGGCTATGGATGAGGCTGACTATTACTGTCAGGCGTGGGACAGTAGAACTGCGGTATTCGGCGGAGGGACCAAGCTGACCGTCCTA SEQ ID NO: 27581 | |
| | | AA | SYELTQPPSVSVSPGQTASITCSGDKLGEKYACWYQQKSGQSPVLVIYQDRKRPSGIPERFSGSNSGNTATLTISGTQAMDEADYYCQAWDSRTAVFGGGTKLTVL SEQ ID NO: 27582 | QITLKESGPTLVKPTQPLTLTCTFSGFSLSTTGVGVGWIRQPPGKALEWLGILFWNDDERYSPSLKSRLTITKDTSKNQVLTMTNMDPVDTATYYCAHKSQLVYFDYWGQGTLVTVSS SEQ ID NO: 31588 |
| iPS:436946 | 21-225_183F4 | NA | TCCTATGAGCTGACTCAGCCACCCTCAGTGTCCGTGTCCCCAGGACAGACAGCCAGCATCACCTGCTCTGGAGATAAATTGGGGGATAAATATGCTTGCTGGTATCAGCAGAAGCCAGGCCAGTCCCCTGTTGTTGGTCATCTATCAAGATAAGAAACGGCCCTCAGGGATCCCTGAGCGATTCTCTGGCTCCAACTCTGGAAACACAGCCACTCTGACCATCAGCGGGACCCAGGCTATGGATGAGGCTGACTATTACTGTCAGGCGTGGGACAACAGCACTGTGATTATTCGGCGGAGGGACCAAGCTGACCGTCCTA SEQ ID NO: 27583 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGAAGGACGTATTGTAGTGGTACCACCTGCCCTACTACTACTACGGTCTGGGGTCTGGGCCAAGGGACCACGGTCACCGTCTCCTCA SEQ ID NO: 31589 |

FIGURE 50
(Continued)

| | | AA | SYELTQPPSVSVSPGQTASITCSGDKLGDKYACW YQQKPGQSPVLVIYQDKKRPSGIPERFSGSNSGN TATLTISGTQAMDEADYYCQAWDNSTAVVFGG GTKLTVL | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCARERTYC SGTTCPYYYYYGLGVWGQGTTVTVSS |
|---|---|---|---|---|
| iPS:436948 | | | SEQ ID NO: 27584 | SEQ ID NO: 31590 |
| | | NA | CAGGCTCCACGCACGCTCATCTACAACACAAA CACTCGCTCTTCTGGGGTCCCTGATCGCTTCTC TGGCTCCATCCTTGGGAACAAAGTGCCCTCA CCATCACGGGGCCCAGGCAGATGAATCT GATTATTACTGTGTGCTTTATATGGGTAGTGGC ATTTGGGTGTTCGGCGGAGGGACCAAGCTGAC CGTCCTA | CAGGTACAGCTGGTGGAGTCTGGGGGAGGCGTG GTCCAGCCTGGGAGGTCCCTGAGACTCTCCTGTG CAGCGTCTGGATTCACCTTCAGTAGTTATGGCAT GCTCTGGGTCCGCCAGGCTCCAGGCAAGGGGCT GGAGTGGGTGACAGTTATATGGTATGATGGAAGT GGTAAATACTATGCAGACTCCGTGAAGGGCCGA TTCACCATCTCCAGAGACAATTCCAAGAACACAC TGTATCTGCAAATGAACAGCCTGAGAGCCGAGG ACACGGCTGTTTATTACTGTGCGAGAGAGAATTT TTGGAGTGGTGACTACTGGGGCCAGGGAACCCT GGTCACCGTCTCCTCA |
| | 21-225_183F5 | | SEQ ID NO: 27585 | SEQ ID NO: 31591 |
| | | AA | QTVVTQEPSFSVSPGGTVTLTCGLSSGSVSTTFYP SWYQQTPGQAPRTLIYNTNTRSSGVPDRFSGSIL GNKAALTITGAQADDESDYYCVLYMGSGIWVF GGGTKLTVL | QVQLVESGGGVVQPGRSLRLSCAASGFTFSSYGML WVRQAPGKGLEWVTVIWYDGSGKYYADSVKGRF TISRDNSKNTLYLQMNSLRAEDTAVYYCARENFWS GDYWGQGTLVTVSS |
| | | | SEQ ID NO: 27586 | SEQ ID NO: 31592 |

FIGURE 50
(Continued)

| | | | | |
|---|---|---|---|---|
| iPS:436950 | 21-225_184G4 | NA | TCCTATGAGCTGACTCAGCCACCCTCAGTGTC CGTGTCCCCAGGACAGACAGCAGCCAGCATCACCT GCTCTGGAGATAAATTGGGGATAAATTTGCT TGCTGGTATCAGCAGAAGCCAGGCCAGTCCCC TGTGCTGGTCATCTATGAAGATAGGAAGCGGC CCTCAGGGATCCCTGAGCGATTCTCTGGCTCC AACTCTGGAACACAGCCACTCTGACCATCAG CGGGACCCAGGCTATGGATGAGGCTGACTATT ACTGTCAGGCGTGGGACCAGCCGCACTGTGTA TTCGGCGGAGGGACCCAGCTGACCGTCCTA SEQ ID NO: 27587 | CAGGTGCAGCTGGTGGAGTCTGGGGGAGGCGTG GTCCAGCCTGGGGAGGTCCCTGAGACTCTCCTGTG CAGTGTCTGATTCACCTTTAGTAGTAGCTATGGCAT GCACTGGGTCCGCCAGGCTCCAGGCAAGGGCT GGAGTGGGTGGCAATTATATGGTATGATGAAGT AATAAATACTATGCAGAGACAATTCCAAGAACACGC TTCACCATCTCCAGAGACAATTCCAAGAACACGC TGTATCTGCAAATGAACAGCCTGAGAGCCGAGG ACACGGCTGTGTATTACTGTGCGAGAGGGGGC CCCGGTTCTCTACGGTGACTATGTACTTTGACTAC TGGGGCCAGGGAACCCTGGTCACCGTCTCCTCA SEQ ID NO: 31593 |
| | | AA | SYELTQPPSVSVSPGQTASITCSGDKLGDKFACW YQQKPGQSPVLVIYEDRKRPSGIPERFSGSNSGN TATLTISGTQAMDEADYYCQAWDSRTVFGGG TQLTVL SEQ ID NO: 27588 | QVQLVESGGGVVQPGRSLRLSCAVSGFTFSSYGMH WVRQAPGKGLEWVAIIWYDGSNKYYADSVKGRFT ISRDNSKNTLYLQMNSLRAEDTAVYYCARGPPFS TVTMYFDYWGQGTLVTVSS SEQ ID NO: 31594 |
| iPS:436952 | 21-225_185D2 | NA | TCCTATGAGCTGACTCAGACACCCTCAGTGTC CGTGTCCCCAGGACAGACAGCAGCCAGCATCACCT GCTCTGGAGATAAATTGGGGATAAATATGCT TGCTGGTATCAGCAGAAGCCAGGCCAGTCCCC TGTGCTGGTCATCTATGAAGATAGGAAGCGGC CCTCAGGGATCCCTGACCGATTCTCTGGCTCC AACTCTGGAACACAGCCACTCTGACCATCAG CGGGACCCAGGCTATGGACAGCAGGAAAGTGGT ACTGTCAGGCGTGGGACCAAGCTGACCGTCCTA ATTCGGCGGAGGGACCAAGCTGACCGTCCTA SEQ ID NO: 27589 | CAGGTGCAGCTGGTGGAGTCTGGGGGAGGCGTG GTCCAGCCTGGGGAGGTCCCTGAGACTCTCCTGTG CAGCGTCTGATTCACCTTCAGTAACTATGGCAT GCACTGGGTCCGCCAGGCTCCAGGCAAGGGCT GGAGTGGGTGGCAATTATATGGTATGATGAAGT GATAAATACTATGCAGAGACAATTCCAAGAACACGC TTCACCATCTCCAGAGACAATTCCAAGAACACGC TGTATCTGCAAATGAACACCCTGAGAGCCGAAG ACACGGCTGTGTATTTCTGTGCGAGAGGGGGGCC CCGGTTCTCTACGGTGACTATGTACTTTGACTACT GGGGCCAGGGAACCCTGGTCACCGTCTCCTCA SEQ ID NO: 31595 |

FIGURE 50
(Continued)

| | | | | |
|---|---|---|---|---|
| iPS:436954 | 21-225_185G7 | AA | SYELTQTPSVSVSPGQTASITCSGDKLGDKYAC WYQQKPGQSPVLVIYEDRKRPSGIPDRFSGSNSG NTATLTISGTQAMDEADYYCQAWDSRKVVFGG GTKLTVL<br>SEQ ID NO: 27590 | QVQLVESGGGVVQPGRSLRLSCAASGFTFSNYGM HWVRQAPGKGLEWVAHWYDGSDKYYADSVKGR FTISRDNSKNTLYLQMNTLRAEDTAVYFCARGGPP FSTVTMYFDYWGQGTLVTVSS<br>SEQ ID NO: 31596 |
| | | NA | TCCTATGAGCTGACTCAGCCACCCTCAGTGTC CGTGTCCCCAGGACAGACAGCCAGCATCACCT GCTCTGGAGATAAATTGGGGACAAAATTTGTT TGCTGGTATCAGCAGAAGCCAGGCCAGTCCCC TGTGTTGGTCATCTATCAAGATCGCAAGCGGC CCTCAGGGATCCCTGAGCGATTCTCTGGCTCC AACTCTGGGAACACAGGCTATGAGGCTGACTATT CGGGACCCAGGCGTGGGACAGCAGCACGGTATTC ACTGTCAGGCGGACCAAGCTGACCGTCCTA<br>SEQ ID NO: 27591 | CAGATCACCCTGAAGGAGTCTGGTCCTACGCTGG TGAAACCCACACAGACCCTCACTCTCACTTGTCAC CTTCTCTGGGTTCTCACTCACCACTGGTGGAGTG GGTGTGGGCTGGATCCGTCAGCCCCCAGGAAAG GCCCTGGAGTGGCTTGCACTCATTTATTGGAATG ATGATGAGCGCTACAGCCCATCTCTGAAGAGCA GGCTCACCATCACCAAGGACACCTCCAAAAACC AGGTGGTCCTTACAATGACCAACATGGACCCTGT GGACACAGCCACATATTACTGTGCACACATTATA GCAGTGGCCTTCCAGCATTGGGGCCCAGGCACCC TGGTCACCGTCTCCTCA<br>SEQ ID NO: 31597 |
| | | AA | SYELTQPPSVSVSPGQTASITCSGDKLGHKFVCW YQQKPGQSPVLVIYQDRKRPSGIPERFSGSNSGN TATLTISGTQAMDEADYYCQAWDSSTVFGGGT KLTVL<br>SEQ ID NO: 27592 | QITLKESGPTLVKPTQTLTLTCTFSGFSLTTGGVGV GWIRQPPGKALEWLALIYWNDDERYSPSLKSRLTIT KDTSKNQVLTMTNMDPVDTATYYCAHIIAVAFQ HWGQGTLVTVSS<br>SEQ ID NO: 31598 |

FIGURE 50
(Continued)

| | | | |
|---|---|---|---|
| iPS:436956 | 21-225_186H6 | NA | TCCTATGAGCTGACTCAGCCACCCTCAGTGTC<br>CGTGTCCCCAGGACAGACAGCCAGCATCACCT<br>GCTCTGGAGATAAAATGGGGGAAAAATATGC<br>TTGCTGTATCAGCAGAAGCCAGGCCAGTCCC<br>CTGTGCTGGTCATTTATCAAGATAGAAAGCGG<br>CCCTCAGGGATCCTGAGCGATTCTCTGGCTC<br>CAACTCTGGGAACACAGCCACTCTGACCATCA<br>GCGGGACCCAGGCTATGGATGAGGCTGACTAT<br>TACTGTCAGGCGTGGGACAGCAGCACTGCGGT<br>ATTCGGCGGAGGGACCAAGCTGACCGTCCTA<br>SEQ ID NO: 27593 | CAGATCACCTTGAAGGAGTCTGGTCCTACGCTGG<br>TGAAACCACACAGACCCTCACTCAGCACTGACCTGCAC<br>CTTCTCTGGGTTCTCACTCAGCACTAGTGGAGTG<br>GGTGTGGGCTGGATCCGTCAGCCCCCAGGAAAG<br>GCCCTGGAGTGGCTTGGATTCATTTCTTGGAATG<br>ATGATAAGGCTACAGCCCATCTGAAGAGCA<br>GCCTCACCATCACCAAGGACACCTCCAAAACC<br>AGGTGGTCCTTACAATGACCAACATGACCCTGT<br>GGACACAGCCACATATTACTGTGCACACAAAGC<br>AGCAGCTGTGCTTTGATATCTGGGGCCAAGGG<br>ACAATGGTCACCGTCTCTTCA<br>SEQ ID NO: 31599 |
| | | AA | SYELTQPPSVSVSPGQTASITCSGDKMGEKYAC<br>WYQQKPGQSPVLVIYQDRKRPSGIPERFSGSNSG<br>NTATLTISGTQAMDEADYYCQAWDSSTAVFGG<br>GTKLTVL<br>SEQ ID NO: 27594 | QITLKESGPTLVKPTQTLTLTCTFSGFSLSTSGVGVG<br>WIRQPPGKALEWLGFISWNDDKRYSPSLKSSLTITK<br>DTSKNQVVLTMTNMDPVDTATYYCAHKAAVAF<br>DIWGQGTMVTVSS<br>SEQ ID NO: 31600 |
| iPS:436958 | 21-225_190D1 | NA | CAGACTGTGGTGACTCAGGAGCCCTCACTGAC<br>TGTGTCCCCAGGAGGGACAGTCACTCTCACCT<br>GTGCTTCCAGCACTGGAGCAGTCACCAGTGGT<br>TCCTATCCAAACTGGTTCCAGCAGAAACCTGG<br>ACAAGCACCCAGGCACTGATTTACAGTACAA<br>GTAACAAACACTCCTGGACCCTGCCCGGTTC<br>TCAGGCTCCCTCCTTGGGGGCAAAGCTGCCCT<br>GACACTGTCAGGTGTGCAGCCTGAGGACGAG<br>GCTGACTATTACTGCCTGCTCTACTATGTGGT<br>GCTCAGGTGGCATTCGGCGGAGGGACCAAGTT<br>GACCGTCCTA<br>SEQ ID NO: 27595 | CAGGTGCAGCTGCAGGAGTCGGGCCCAGGACTG<br>GTGAAGCCTTCACAGACCCTGTCCTCCACCTGCA<br>CTGTCTCTGGTGGCTCCATCAGCAGTGGTGTTA<br>CTACTGGAGCTGGATCCGCCAGCACCCAGGGAA<br>GGGAGCACTACTACAACCCGTCCTCAAGAGTC<br>GAGTCACCATATCAGTAGACACGTCTAAGAACC<br>AGTTCTCCCTGAAGCTGAGCTCTGTGACTGCCGC<br>GGACACGGCCGTTTATTACTGTGCGAGAGATTCC<br>CCACTACGAGGCTTGACTACTGGGGCCAGGGA<br>ACCCTGGTCACCGTCTCCTCA<br>SEQ ID NO: 31601 |

FIGURE 50
(Continued)

| | | | |
|---|---|---|---|
| iPS:436960 | 21-225_198D2 | AA | QTVVTQEPSLTVSPGGTVTLTCASSTGAVTSGSYPNWFQQKPGQAPRALIYSTSNKHSWTPARFSGSLLGGKAALTLSGVQPEDEADYYCLLYYGGAQVAFGGGTKLTVL<br>SEQ ID NO: 27596 | QVQLQESGPGLVKPSQTLSLTCTVSGGSISSGGYYWSWIRQHPGKGLEWIGYIYYSGSTYNPSLKSRVTISVDTSKNQFSLKLSSVTAADTAVYYCARDSPLRGFDYWGQGTLVTVSS<br>SEQ ID NO: 31602 |
| | | NA | CAGTCTGTGTTGACGCAGCCGCCCTCAGTGTCTGCGGCCCCAGGACAGAGAAGGTCACCATCCTGCTCTGGAAGCAGCTCCAACATTGGGAGTAATTATGTTTCCTGGTACCAACAGTCCCAGGAACAGCCCCAAAGTCCTCATTTATGACAATAATAAGCGACCCTCAGGGATTCCTGACCGATTCTCTGGCTCCAAGTCTGGCACGTCAGCCACCCTGGCATCACCGGACTCCAGACTGGGGACGAGGCCGATTATTACTGCGGAACATGGGATAGCAGACTGAATGTTGGGGTATTCGGCGGAGGGACCAAGCTGACCGTCCTA<br>SEQ ID NO: 27597 | CAGGTGCAGCTGGTGGAGTCTGGGGGAGGCGTGGTCCAGCCTGGGAGGTCCCTGAGACTCTCCTGTGCAGCCTCTGGATTCACCTTCAGAAGCTATGGCATGCATTGGGTCCGCCAGGCTCCAGGCAAGGGGCTGGAGTGGGTGGCAGTTATAATATGAGGAAGTTATAAGTACTATGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAGAACGTATAGCGGGGTATGGACGTCTGGGGCCAAGGGACCACGGTCACCGTCTCCTCA<br>SEQ ID NO: 31603 |
| | | AA | QSVLTQPPSVSAAPGQKVTISCSGSSSNIGSNYVSWYQQLPGTAPKVLIYDNNKRPSGIPDRFSGSKSGTSATLGITGLQTGDEADYYCGTWDSRLNVGVFGGGTKLTVL<br>SEQ ID NO: 27598 | QVQLVESGGGVVQPGRSLRLSCAASGFTFRSYGMHWVRQAPGKGLEWVAVIIYDGSYKYYADSVKGRFTISRDNSKNTLYLQMNSLRAEDTAVYYCARTYSGGMDVWGQGTTVTVSS<br>SEQ ID NO: 31604 |

FIGURE 50
(Continued)

| | | | |
|---|---|---|---|
| iPS:436962 | 21-225_190H1 | NA | TCCTATGAGTTGACTCAGCCACCCTCAGTGTC CGTGTCCCAGGAGATAAATTGGGGACAGCCAGCATCACCT GCTCTGGAGATATCAGCAGACAGCCAGCATTTGCT TACTGGTATCAGCAGAAGCCAGGCCAGTCCCC TGTACTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTAAGGCGTGGGACAGCAGCACTGTGGTA TTCGGCGGAGGGACCAAGCTGACCGTCCTA<br><br>SEQ ID NO: 27599<br><br>SYELTQPPSVSVSPGQTASITCSGDKLGDRFAYW YQQKPGQSPVLVIYQDSKRPSGIPERFSGSNSGN TATLTISGTQAMDEADYYCKAWDSSTVFGGG TKLTVL<br><br>SEQ ID NO: 27600 | CAGGTACAGCTGCAGCAGTCAGGTCCAGGACTG GTGAAGCCCTCGCAGACCCTCACTCACCTGTG ACATCTCCGGGGACAGTGTCTCTAGGAAAGTGC TACTTGGAACTGGATCAGCAGTCCCCATCGAGA GGCCTTGAGTGGCTGGGAAAGACATACTACAGG TCCAAGTGGTATAATGATTATGCAGTATCTGTGA AAAGTCGAATAACCATCAATCCAGACACATCCA AGAACCAGTTCTCCCTGCAATTGAACTCTGTGAC TCCCGAGGACACGGCTGTGTATTACTGTGCAAGA GATCCGGGGGCCTCTTTGACTACTGGGGCCAGG GAACCCTGGTCACCGTCTCCTCA<br><br>SEQ ID NO: 31605<br><br>QVQLQQSGPGLVKPSQTLSLTCDISGDSVSRKSAT WNWIRQSPSRGLEWLGKTYYRSKWYNDYAVSVK SRITINPDTSKNQFSLQLNSVTPEDTAVYYCARDPG GLFDYWGQGTLVTVSS<br><br>SEQ ID NO: 31606 |
| iPS:436964 | 21-225_190B3 | NA | TCTTCTGAGCTGACTCAGGACCCTGCTGTGTCT GTGGCCTTGGACAGAGCAGTCAGGATCACATG CCAAGGAGACAAAATCAGAACTCAGAAGCCAGG GCTGGTACCAGCAGAAGCCAGGACAGGCCCC TGTACTTGTCGTCTATGGAAAAACAACCGGC CCTCAGGGATCCCAGACCGATTCTCTGGCTCC AGCTCAGGGAAACACAGCTTCCTTGACCATCAC TGGGGCTCAGGCGGAAGATGAGGCTGACTATT ACTGTAACTCCCGGACAGCAGTGGTAACCAT CTTGTACTATTCGGCGGAGGGACCAAGCTGAC CGTCCTA<br><br>SEQ ID NO: 27601 | CAGGTGCAGCTGGTGGAATCTGGGGGAGGCGTG GTCCAGCCTGGGAGGTCCCTGAGACTCTCCTGTG CAGCGTCTGGATTCACCTTCAATAACTATGGCAT ACACTGGGTCCGCCAGGCTCCAGGCAAGGGCT GGAGTGGGTGGCAGTTATATGTTTGATGGAGAT AATAAATACTATGCAGACTCCGTGAAGGGCCGA TTCACCATCTCCAGAGACAATTCCAAGAACACGC TGTATCTGCAAATGAACAGCCTGAGAGCCGAAG ACACGGCTGTGTATTACTGCGAGAGATAACTG GAACTACGGCGATCACTACTACTTCGGTATG GACGTCTGGGGCCAAGGGACCACGGTCACCGTC TCCTCA<br><br>SEQ ID NO: 31607 |

FIGURE 50
(Continued)

| | | | |
|---|---|---|---|
| iPS:436966 | 21-225_190C3 | AA | SSELTQDPAVSVALGQTVRITCQGDKLRTYYAS WYQQKPGQAPVLVVYGKNNRPSGIPDRFSGSSS GNTASLTITGAQAEDEADYCNSRDSSGNHLVL FGGGTKLTVL<br>SEQ ID NO: 27602 | QVQLVESGGGVVQPGRSLRLSCAASGFTFNNYGIH WVRQAPGKGLEWVAVIWFDGDNKYYADSVKGRF TISRDNSKNTLYLQMNSLRAEDTAVYYCARDNWN YGDHYYFGMDVWGQGTTVTVSS<br>SEQ ID NO: 31608 |
| | | NA | CAGTCTGTGTTGACGCAGCCGCCCTCAGTGTC TGCGGCCCCAGGACAGAAGGTCACCATCTCCT GCTCTGGAAGCAGCTCCAACATTGGAAATAAT TATGTATCCTGGTACCAGCAGCTCCCAGGAAC AGCCCCCAAACTCCTCCTTTATGACAGTAATA AGCGGACCCTCAGGGATTCCTGGCCGATTCTCT GGCTCCAAGTCTGGCACGTCAGCACCCTGGG CATCACCGGCCTCCAGACTGGGGACGAGGCCG ATTATTACTGCGGAACATGGGATAGCAGCCTG AGTACTGTGGTATTCGGCGGAGGGACCAAGCT GACCGTCCTA<br>SEQ ID NO: 27603 | CAGGTGCAGCTGGTGGAGTCTGGGGGAGGCGTG GTCCAGCCTGGGAGGTCCCTGAGACTCTCCTGT CAGCGTCTGAGATTCACCTTCAGTAGTACTGGCAT GCAACTGGGTCCGCCAGGCTCCAGGCAAGGGCT GGAGTGGGTGGCAGTTATATGTGATGGAAGT AATAAATACTATGCAGACTCCGTGAAGGGCCGA TTCACCATCTCCAGAGACAACGCTCCAAGAACACGC TGTATCTGCAAATGAACAGCCTGAGAGCCGAGG ACACGGCTGTGTATTACTGTGCGAACTGGTACTA CTACTACGGTATGGACGTCTGGGGCCAAGGG ACCACGGTCACCGTCCTCCTCA<br>SEQ ID NO: 31609 |
| | | AA | QSVLTQPPSVSAAPGQKVTISCSGSSSNIGNNYVS WYQQLPGTAPKLLLYDSNKRPSGIPGRFSGSKSG TSATLGITGLQTGDEADYYCGTWDSSLSTVVFG GGTKLTVL<br>SEQ ID NO: 27604 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYYCANWYYY YYGMDVWGQGTTVTVSS<br>SEQ ID NO: 31610 |

FIGURE 50
(Continued)

| | | | |
|---|---|---|---|
| iPS:436968 | 21-225_190B10 | NA | CAGTCTGTGTTGACGCAGCCGCCCTCAGTGTC TGCGGCCCCAGGACAGCAGCTCCAACATTCCT GCTCTGGATTCCTGGTACCAGCATCTCCAGAAC TATGTATCCTGGTACCAGCATCTCCCAGAAC AGCCCCCAAACTCCTCATTTATGACAATAATA AGCGACCCTCAGGGATTCCTGACCGATTCTCT GGCTCCAAGTCTGGCACGTCAGCCACCCTGGG CATCACCGGACTCCAGACTGGGGACGAGGCC GATTATTACTGCGGAACATGGGATAGCAGCCT GAGTGCTGGGGTTTTCGGCGGAGGGACCAAGC TGACCGTCCTA<br><br>SEQ ID NO: 27605 | CAGGTGCAGCTGGTGGAGTCTGGGGGAGGCGTG GTCCAGCCTGGGAGGTCCCTGAGACTCTCCTGTG TAGCGTCTGGATTCACCTTCAGTAGCTATGGCAT GCACTGGGTCCGCCAGGCTCCAGGCAAGGGCT GGAGTGGGTGGCAGTTATATGGAATGATGAAAG TAAAAATACCATCTCCAGAGACAATTCCAAGAACACG CTGTATCTGCAAATGAACAGCCTGAGAGCCGAG GACACGGCTCTGTATTACTGTGCGAGAGATCTGG ATAAGAGGAACTTCCTTATTACTACTACGG TATGGACGTCTGGGGCCAAGGGACCACGGTCAC CGTCTCCTCA<br><br>SEQ ID NO: 31611 |
| | | AA | QSVLTQPPSVSAAPGQKVTISCSGSSSNIGNNYVS WYQHLPGTAPKLLIYDNNKRPSGIPDRFSGSKSG TSATLGITGLQTGDEADYYCGTWDSSLSAGVFG GGTKLTVL<br><br>SEQ ID NO: 27606 | QVQLVESGGGVVQPGRSLRLSCVASGFTFSSYGMH WVRQAPGKGLEWVAVIWNDGSKKYHVDSVKGRF TISRDNSKNTLYLQMNSLRAEDTALYYCARDLDKR NFPYYYYGMDVWGQGTTVTVSS<br><br>SEQ ID NO: 31612 |
| iPS:436970 | 21-225_190B8 | NA | TCTTCTGAGCTGACTCAGGACCCTGCTGTGTCT GTGGCCTTGGGACAGACAGTCAGGATCACATG CCAAGGAGACAGCACCCTCAGATCCTATTGTAA GCTGGTACCAGCAGAAGCCAGGACAGGCCC TGTACTTGTCATCTATGGTAAAAACAACCGGC CCTCAGGGATCCCAGACCGATTCTCTGGCTCC AGCTCAGGAAACACAGCTTCCTTGACCATCAC TGGGGCTCAGGCGGAAGATGAGGCTGACTATT ACTGTAACTCCCGGACACAGCAGTGGTAACCAT CTTGTGGTATTCGGCGGAGGGACCAAGCTGAC CGTCCTA<br><br>SEQ ID NO: 27607 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCAGTTATATGGTTGATGAAAGT AATAAATACTATACAGACTCCGTGAAGGGCCGA TTCACCATCTCCAGAGACAATTCCAAGAACAGC CTGTATCTGCAAATGAACAGCCTGAGAGCCGAGG ACACGGCTGTATATTATTGTGCGAGAGATAACTG GAACTACGGCGATTACTACTACTACTACGGTATG GACGTCTGGGGCCAAGGGACCACGGTCACCGTC TCCTCA<br><br>SEQ ID NO: 31613 |

FIGURE 50
(Continued)

| | | | |
|---|---|---|---|
| | | AA | SSELTQDPAVSVALGQTVRITCQGDTLRPYYVSWYQQKPGQAPVLVIYGKNNRPSGIPDRFSGSSSGNTASLTITGAQAEDEADYYCNSRDSSGNHLVVFGGGTKLTVL<br>SEQ ID NO: 27608 | QVQLVESGGGVVQPGRSLRLSCAASGFTFSSYGMHWVRQAPGKGLEWVAVIWFDGSNKYYTDSVKGRFTISRDNSKNTLYLQMNSLRAEDTAVYYCARDNWNYGDYYYYGMDVWGQGTTVTVSS<br>SEQ ID NO: 31614 |
| iPS:436972 | 21-225_190C7 | NA | CAGTCTGTGTTGACGCAGCCGCCCTCAGTGTCTGCGGCCCCAGGACAGAAGGTCACCATCTCTGCTCTGGAGGCAGCTCCAACATTGGGAATAATTATGTATCCTGGTTTCAGCAGTCCCAGGAACAGCCCCAAATTCCTCATTTATGACAATAATAAGGGACCCTCAGGGATTCCTGACCGATTCTCTGGCTCCAAGTCTGGCACGTCAGCCACCCTGGCATCACCGGACTCCAGACTGGTGACGAGGCCGATTATTACTGCGGAACATGGGATCGCACCAAGCTAGTGATTGGGTATTCGGCGGAGGGACCAAGCTGACCGTCCTA<br>SEQ ID NO: 27609 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATGCACTGGGTGCGACAGGCCCCTGGACAAGGGCTTGAGTGGATGGGATGGATCAACCTAACAGTGGTGGCACAAACTATGCACAGAAGTTCAGGGCAGGGTCACCATGACCAGGGACACGTCCATCAGCACAGCCTACATGGAACTGAGCAGGCTGAGATCTGACGACACGGCCGTGTATTACTGTGCGAGAGATAGAGCAGTGGCTGGAAACTACTTCTACTACGGTATGGACGTCTGGGGCCAAGGGACCACGGTCACCGTCTCCTCA<br>SEQ ID NO: 31615 |
| | | AA | QSVLTQPPSVSAAPGQKVTISCSGGSSNIGNNYVSWFQQFPGTAPKFLIYDNNKRPSGSKSGTSATLGITGLQTGDEADYYCGTWDRTLSDWVFGGGTKLTVL<br>SEQ ID NO: 27610 | QVQLVQSGAEVKKPGASVKVSCKASGYTFTFGYYMHWVRQAPGQGLEWMGWINPNSGGTNYAQKFQGRVTMTRDTSISTAYMELSRLRSDDTAVYYCARDRAVAGNYFYGMDVWGQGTTVTVSS<br>SEQ ID NO: 31616 |

FIGURE 50
(Continued)

| | | | |
|---|---|---|---|
| iPS:436974 | 21-225_190H7 | NA | CAGTCTGTGTTGACGCAGCCGCCCTCAGTGTCTGCGGGCCCAGGACAGAAGGTCACCATCCTCTGCTCTGGAAGCAGCTCCAACATTGGGAGTAATTATGTTTCCTGGTACCAACAGCTCCCAGGAACAGCCCCCAAAGTCCTCATTTATGACAATAATAAGCGACCCTCAGGGATTCCTGACCGATTCTCTGGCTCCAAGTCTGGCACGTCAGCCACCCTGGGCATCACCGGACTCCAGACTGGGGATGGCAGACTGAATGTTGGGTATTCGGGGACGGGGACCAAGCTGACCGTCCTA<br>SEQ ID NO: 27611 | CAGGTGCAGCTGGTGGAGTCTGGGGGAGGCGTGGTCCAGCCTGGGAGGTCCCTGAGACTCTCCTGTGCAGCCTCTGGATTCAACTTCAGAAGCTATGGCATGCATTGGGTCCGCCAGGCTCCAGGCAAGGGCTGGAGTGGGTGGCAGTTATATATATGGAAGTTATAAGTACTATGCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAGAACGTATAGCGGGGGTATGGACGTCTGGGGCCAAGGGACCACGGTCACCGTCTCCTCA<br>SEQ ID NO: 31617 |
| | | AA | QSVLTQPPSVSAAPGQKVTISCSGSSSNIGSNYVSWYQQLPGTAPKVLIYDNNKRPSGIPDRFSGSKSGTSATLGITGLQTGDEADYYCGTWDGRLNVGVFGGGTKLTVL<br>SEQ ID NO: 27612 | QVQLVESGGGVVQPGRSLRLSCAASGFNFRSYGMHWVRQAPGKGLEWVAVIIYDGSYKYYADSVKGRFTISRDNSKNTLYLQMNSLRAEDTAVYYCARTYSGGMDVWGQGTTVTVSS<br>SEQ ID NO: 31618 |
| iPS:436976 | 21-225_190D8 | NA | CAGTCTGTGTTGACGCAGCCGCCCTCAGTGTCTGCGGGCCCAGGACAGAAGGTCACCATCCTCTGCTCTGGAAGCAGCTCCAACATTGGGAATCATTATGTCTCCTGGTACCAGCAGCTTCCAGGAACAGCCCCCAAACTCCTCATTTATGACAGTAAGCGACCCTCAGAGATTCCTGACCGATTCTCTGGCTCCAAGTCTGGCACGTCCGCCACCCTGGGCATCACCGGACTCCAGACTGGGGACGAGGCCGATTATTACTGCGGAACATGGGATAGTGTCTGAGTACTGTGTATTCGGCGGAGGGACCAAGCTGACCGTCCTA<br>SEQ ID NO: 27613 | CAGGTGCAGCTGGTGGAGTCTGGGGGAGACGTGGTCCAGCCTGGAAGGTCCCTGAGACTCTCCTGTGAAGCGTCTGGATTCACCTTCAGTAGCTATGGCCTGCACTGGGTCCGCCAGGCTCCCGGCAAGGGACTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGGAACTGTACTAACTACTACGGTATGGACGTCTGGGGCCAAGGGACCACGGTCACCGTCTCCTCA<br>SEQ ID NO: 31619 |

FIGURE 50
(Continued)

| | | | |
|---|---|---|---|
| iPS:436978 | 21-225_190G9 | AA | QSVLTQPPSVSAAPGQKVTISCSGSSSNIGNHYVS WYQQLPGTAPKLLIYDSSKRPSEIPDRFSGSKSGT SATLGITGLQTGDEADYYCGTWDSSLSTVVFGG GTKLTVL<br>SEQ ID NO: 27614 | QVQLVESGGDVVQPGRSLRLSCEASGFTFSSYGLH WVRQAPGKGLEWVAVIWYDGSNKYYADSVKGRF TISRDNSKNTLYLQMNSLRAEDTAVYYCANWYYY YYGMDVWGQGTTVTVSS<br>SEQ ID NO: 31620 |
| | | NA | TCCTATGAGCTGACTCAGCCACCCTCAGTGTC CGTGTCCCCAGGACAGAGCCAGCATCACCT GCTCTGAGATAAATTGGGGATAGATTTGCT TACTGGTATCAGCAGAAGCCAGGCCAGTCCCC TGTGCTGGTCATCTATCAAGATAACAAGCGGC CCTCAGGGATCCCTGAGCGATTCTCTGGCTCC AACTCTGGGAACACAGCCTCTGATGAGGCTGACTATT ACTGTCAGGGCGTGGGACAGCAGCACTGTGTA TTCGGCGGAGGGACCAGGCTGACCGTCCTA<br>SEQ ID NO: 27615 | CAGGTACAGTTGCAGCAGTCAGGTCCAGGACTG GTGAAGCCCTGCAGACCCTCACTCACCTGTG CCATCTCCGGGACAGTGTCTCTAGGAAAGTGC TACTTGGAACTGGATCAGGCAGTCCCATCGAGA GGCCTTGAGTGGCTGGAAGGACATACTACAGG TCCAAGTGGTATAATGATTATGCAGTATCTGTGA AAAGTCGAATAATCATCAATCCAGACACATCCA AGAACCAGTTCTCCCTGCAGCTGAACTCTGTGAC TCCCGAGGACACGGCTGTGTATTACTGTGCAAGA GATCCGGGGTGGCCTCTTTGACTACTGGGGCCAGG GAACCCTGGTCACCGTCCTCCTCA<br>SEQ ID NO: 31621 |
| | | AA | SYELTQPPSVSVSPGQTASITCSGDKLGDRFAYW YQQKPGQSPVLVIYQDNKRPSGIPERFSGSNSGN TASLTISGTQAMDEADYYCQAWDSSTVVFGGG TRLTVL<br>SEQ ID NO: 27616 | QVQLQQSGPGLVKPSQTLSLTCAISGDSVSRKSAT WNWIRQSPSRGLEWLGRTYYRSKWYNDYAVSVK SRIIINPDTSKNQFSLQLNSVTPEDTAVYYCARDPGG LFDYWGQGTLVTVSS<br>SEQ ID NO: 31622 |

FIGURE 50
(Continued)

| | | | |
|---|---|---|---|
| iPS:436980 | 21-225_190C10 | NA | TCTTCTGAGCTGACTCAGGACCCTGCTGTCT GTGGCCTTGGGACAGAGACAGTCAGGATCAGATTCAGGAGACAGCCTCAGACCCTATTATGCAA CCAAGGAGACAGCCTCAGACCCTATTATGCAA GCTGGTACCAGCAGCAGAAGCCAGGACAGGCCC TGTACTTGTCATCTATGGTAAAAACAACGGC CCTCAGGGATCCCAGACCGATTCTCTGGCTCC AGTTCAGGAAACACAGCTTCCTGACCATCAC TGAGGCTCAGGCGGAAGATGAGGCTGACTATT ACTGTAACTCCCGGGACAGCAGTGGTAACCAT CTGTGTGGTATTCGGCGGAGGGACCAAGCTGAC CGTCCTA<br><br>SEQ ID NO: 27617 | CAGGTGCAGCTGGTGGAGTCTGGGAGGCGTG GTCCAGCCTGGGAGGTCCCTGAGACTCTCCTGTG CAGGCGTCTGGATTCACCCTCAGTAACTATGGCAT GCACTGGGTCCGCCAGGCTCCAGGCAAGGGGCT GGAGTGGGTGGCAGTTATATGGTTTGGTGGAGAT AATAAATACTATGCAGACTCCGTGAGGGGCCGA TTCACCATCTCCAGAGACAATTCCAAGAACACGC TGTATCTGCAAATGAACAGCCTGAGAGCTGAGG ACACGGCTGTGTTTACTGTGCGAGATAACTG GAACTACGGCGATCACTACTATTACGGAATG GACGTCTGGGGCCAAGGGACCACGGTCACCGTC TCCTCA<br><br>SEQ ID NO: 31623 |
| | | AA | SSELTQDPAVSVALGQTVRITCQGDSLRPYYAS WYQQKPGQAPVLVIYGKNNRPSGIPDRFSGSSSG NTASLTIEAQAEDEADYYCNSRDSSGNHLVVF GGGTKLTVL<br><br>SEQ ID NO: 27618 | QVQLVESGGGVVQPGRSLRLSCAASGFTLSNYGM HWVRQAPGKGLEWVAVIWFGGDNKYYADSVRGR FTISRDNSKNTLYLQMNSLRAEDTAVFYCARDNW NYGDHYYYGMDVWGQGTTVTVSS<br><br>SEQ ID NO: 31624 |
| iPS:436982 | 21-225_190D10 | NA | CAGTCTGTGTTGACGCAGCCGCCCTCAGTGTC TGCGGGCCCCAGGACAGAAGGTCACCATCCCT GCTCTGGAAGCAGCTCCAACATTGGGAGTAAT TATGTTTCCTGGTACCAACAGCTCCCAGGAAC AGTCCCAAAGTCCTCATTTATGACAATAATA AGCGACCCTCAGGGATTCCTGACCGATTCTCT GGCTCCAAGTCTGGCACGTCAGCCACCCTGGG CATCACCGGACTCCAGACTGGGGACGAGGCC GATTATTACTGCGGAACATGGGATAGCAGACT GAATGTTGGGTATTCGGCGGAGGGACCAAG CTGACCGTCCTA<br><br>SEQ ID NO: 27619 | CAGGTGCAGCTGGTGGAGTCTGGGGGAGGCGTG GTCCAGCCTGGGAGGTCCCTGAGACTCTCCTGTG CAGCCTCTGGATTCACCTTCAGAAGCTATGGCAT GCATTGGGTCCGCCAGGCTCCAGGCAAGGGGCT GGAGTGGGTGGCAGTTATAATATGATGGAAGT TATAAGTACTATGCAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGCGAGAACGTAGC GGGGTATGGACGTCTGGGGCCAAGGGACCACG GTCACCGTCTCCTCA<br><br>SEQ ID NO: 31625 |

FIGURE 50
(Continued)

| | | | |
|---|---|---|---|
| | | AA | QSVLTQPPSVSAAPGQKVTISCSGSSSNIGSNYVS WYQQLPGTVPKVLIYDNNKRPSGIPDRFSGSKSG TSATLGITGLQTGDEADYYCGTWDSRLNVGVFG GGTKLTVL | QVQLVESGGGVVQPGRSLRLSCAASGFTFRSYGMH WVRQAPGKGLEWVAVIIYDGSYKYYADSVKGRFT ISRDNSKNTLYLQMNSLRAEDTAVYYCARTYSGG MDVWGQGTTVTVSS |
| | | | SEQ ID NO: 27620 | SEQ ID NO: 31626 |
| iPS:436984 | 21-225_190F10 | NA | CAGACTGTGGTGACTCAGGAGCCCTCACTGAC TGTGTCCCCAGGAGGACAGTCACTCTCACTT GTGTTTTTAGCACTGGAGCAGTCACCAGTGGT TCCTTTCCAAACTGGTTCCAGCAGAAACTGG ACAAGCACCCAGGGCACTGATTTATGATAACAA GCAACAACACTCCTGGACCCCTGCCGGTTC TCAGGCTCCCTCCTTGGGGGCAAAGCTGCCCT GACACTGTCAGGTGTGCAGCCTGAGGACGAG GCTGACTATTACTGCCTGCTCTACTGTGGTGGT GCTCAGTGGTGTTCGGCGGAGGGACCAAGCT GACCGTCCTA | CAGGTGCAGCTGCAGGAGTCGGGGCCAGGACTG GTGAAGCCTTCACAGACCCTGTCCCTCACCTGCA CTGTCTCTGGTGGCTCCATCAGAAGTGGTGGTGA CTACTGGAGCTGGATCCGCCAGCACCCAGGGGA GGGCCTGGAGTGGATTGGGTACATCTATTACAGT GGGATCACCTACTACAATCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGATAGC AGCTCGCGGGGTATGGACGTCTGGGGCCAAGGG ACCACGGTCACCGTCTCCTCA |
| | | | SEQ ID NO: 27621 | SEQ ID NO: 31627 |
| | | AA | QTVVTQEPSLTVSPGGTVTLTCVFSTGAVTSGSF PNWFQQKPGQAPRALIYSTSNKHSWTPARFSGS LLGGKAALTLSGVQPEDEADYYCLLYCGGAQL VFGGGTKLTVL | QVQLQESGPGLVKPSQTLSLTCTVSGGSIRSGGDY WSWIRQHPGEGLEWIGYIYYSGITYYNPSLKSRVTI SVDTSKNQFSLKLSSVTAADTAVYYCARDSSSRGM DVWGQGTTVTVSS |
| | | | SEQ ID NO: 27622 | SEQ ID NO: 31628 |

FIGURE 50
(Continued)

| | | | |
|---|---|---|---|
| iPS:436986 | 21-225_191A1 | NA | CAGTCTGTGTTGACGCAGCCGCCCTCAGTGTC TGCGGCCCAGGAAGCAGCTCCAACCTTGGGGTCACCATCTCCT GCTCTCGGAAGCAGCTCCAACCTTGGAAATAAT TTTGTATCCTGGTACCAGCAGTTCCCAGGAAC AGCCCCAAACTCCTCATTTATGACAATTATA AGGGACCCTCAGGGATTCCTGACCGATTCTCT GTCTCCAAGTCTGGCACGTCAGCCACCCTGGG CATCACCGGACTCCAGACTGGGGACGAGGCC GATTATTACTGCGGAACATGGGATAGCAGCCT GAATACTGGGGTATTCGGCGGAGGGACCAAG CTGACCGTCCTA<br><br>SEQ ID NO: 27623 | CAGGTGCAGCTGCAGGAGTCGGGCCCAGGACTG GTGAAGCCTTCGGAGACCCTGTCCCTCACCTGCA CTGTCTCTGGTGGCTCCATCAGAAGTTACTACTG GATCTGGATCCGGCAGCCCCAGGAAGGACT GGAGTGGATTGGGTATATCTATTACAGTGGGAGT ACTAAGTACAACCCCTCCCTCAAGAGTCGAGTCA CCATATCAGTAGACACGTCCAAGAACCAGTTCTC CCTGAAACTGAGCTCTGTGACCGCTGCGGACACG GCCGTGTATTACTGTGCGAGAAAGGGAGTGGGA ACCATCCACTTTGACTACTGGGGCCAGGGAACCC TGGTCACCGTCTCCTCA<br><br>SEQ ID NO: 31629 |
| | | AA | QSVLTQPPSVSAAPGQRVTISCSGSSSNLGNNFV SWYQQFPGTAPKLLIYDNYKRPSGIPDRFSVSKS GTSATLGITGLQTGDEADYYCGTWDSSLNTGVF GGGTKLTVL<br><br>SEQ ID NO: 27624 | QVQLQESGPGLVKPSETLSLTCTVSGGSIRSYYWIW IRQPPGKGLEWIGYIYYSGSTKYNPSLKSRVTISVDT SKNQFSLKLSSVTAADTAVYYCARKGVGTIHFDY WGQGTLVTVSS<br><br>SEQ ID NO: 31630 |
| iPS:436988 | 21-225_191A2 | NA | CAGACTGTGGTGACTCAGGAGCCCTCACTGAC TGTGTCCCCAGGAGGGACAGTCACTCTCACTT GTGTTCTTAGCACTGGAGCAGTGAGTCACCAGTGGT TCCTTTCCAAACTGGTTCCAGCAGAAACTGG ACAAGCACCCAGGGCACTGATTTATAGTACAA GCAACAAACACTCCTGGACCCTGCCCGTTT TCAGGCTCCCTCCTTGGGGGGCAAAGCTGCCT GACACTGTCAGGTGTGCAGCCTGAGGACGAG GCTGACTATTACTGCATGTCTCTACTGTGGTGGT GCTCAGCTGGTTCGGCGGAGGGACCAAGCT GACCGTCCTA<br><br>SEQ ID NO: 27625 | CAGGTGCAGCTGCAGGAGTCGGGCCCAGGACTG GTGAAGCCTTCACAGACCCTGTCCCTCACCTGCA CTGTCTCTGGTGGCTCCATCAGAAGTGGTGGTGA CTACTGGAGCTGGATCCGCCAGCACCCAGGGAA GGGCCTGGAGTGGATTGGGTACATCTATTACAGT GGGATCACTACTACAATCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGATAGC AGCTGCGGGGTATGGACGTCTGGGGCCAAGGG ACCACGGTCACCGTCTCCTCA<br><br>SEQ ID NO: 31631 |

FIGURE 50
(Continued)

| | | | |
|---|---|---|---|
| | | AA | QTVVTQEPSLTVSPGTVTLTCVLSTGAVTSGSF PNWFQQKPGQAPRALIYSTSNKHSWTPARFSGS LLGGKAALTLSGVQPEDEADYYCMLYCGGAQL VFGGGTKLTVL<br><br>SEQ ID NO: 27626 | QVQLQESGPGLVKPSQTLSLTCTVSGGSIRSGGDY WSWIRQHPGEGLEWIGYIYYSGITYYNPSLKSRVTI SVDTSKNQFSLKLSSVTAADTAVYYCARDSSSRGM DVWGQGTTVTVSS<br><br>SEQ ID NO: 31632 |
| iPS:436992 | 21-225_191B8 | NA | TCTTCTGAGCTGACTCAGGACCCTGCTGTGTCT GTGGCCTTGGGACAGACAGTCAGGATCACATG CCAAGGAGACACCCTCAGACCCTATTATGCAA GTTGGTACCAGCAGAAGCCAGGACAGGCCCCT GTACTTGTCATCTATGGTAAAAACAACGGGC CTCAGGGATCTCAGACCGATTCTCTGGCTCCA GCTCAGGAAAACACAGCTTCCTTGACCATCACT GGGGCTCAGGCGGAAGATGAGGCTGACTATT ACTGTATGCTATGTGGACAGCAGTGGTAACCAT CTTGTGGTATTCGGGGGACAGGGGACCAAGCTGAC CGTCCTA<br><br>SEQ ID NO: 27627 | CAGGTGCAGCTGGTGGAGTCTGGGGGAGGCGTG GTCCAGCCTGGGAGGTCCCTGAGACTCTCCTGTG CAGCGTCTGGATTCACCCTCAGTAGCTATGGCAT GCACTGGGTCCGCCAGGCTCCAGGCAAGGGCT GGAGTGGGTGGCAGTTATATGGTTTGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCAGAGATAACTG GAACTACGGCGATCACTACTACTACTACGGTATG GACGTCTGGGGCCAAGGGACCACGGTCACCGTC TCCTCA<br><br>SEQ ID NO: 31633 |
| | | AA | SSELTQDPAVSVALGQTVRITCQGDTLRPYYAS WYQQKPGQAPVLVIYGKNNRPSGISDRFSGSSSG NTASLTITGAQAEDEADYYCNSRDSSGNHLVVF GGGTKLTVL<br><br>SEQ ID NO: 27628 | QVQLVESGGVVQPGRSLRLSCAASGFTLSSYGMH WVRQAPGKGLEWVAVIWFDGSNKYYADSVKGRF TISRDNSKNTLYLQMNSLRAEDTAVYYCARDNWN YGDHYYYGMDVWGQGTTVTVSS<br><br>SEQ ID NO: 31634 |

FIGURE 50
(Continued)

| | | | |
|---|---|---|---|
| iPS:436994 | 21-225_191A9 | NA | TCTTCTGAGCTGACTCAGGACCCTGCTGTGTCT GTGGCCTTGGGACAGACAGTCAGGATCACATG CCAAGGAGACAGCCTCAGACCCTATTATGCAA GCTGGTACCAGCAGAAGCCAGGACAGGCCCC TGTACTTGTCATCTATGGTAAAAACAACCGGC CCTCAGGGATCCCAGACCGATTCTCTGGCTCC AGCTCAGGAAACACAGCTTCCTTGACCATCAC TGAGGCTCAGGCGGAAGATGAGGCTGACTATT ACTGTAACTCCCGGGACAGCTGTGGTAACCAT CTTGTGTATTCGGCGGAGGGACCAAGCTGAC CGTCCTA SEQ ID NO: 27629 | CAGGTGCAGCTGGTGGAGTCTGGGGGAGGCGTG GTCCAGCCTGGGAGGTCCCTGAGACTCTCCTGTG CAGCGTCTGGATTCACCCTCAGTAATTATGGCAT GCACTGGGTCCGCCAGGCTCCAGGCAAGGGCT GGAGTGGGTGGCAGTTATATGGTTTGGTGGAGAT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTTTTACTGTGCAGAGATAACTG GAACTACGGCGATCACTACTATTACGGTATG GACGTCTGGGGCCAAGGGACCACGGTCACCGTC TCCTCA SEQ ID NO: 31635 |
| | | AA | SSELTQDPAVSVALGQTVRITCQGDSLRPYYAS WYQQKPGQAPVLVIYGKNNRPSGIPDRFSGSSSG NTASLTITEAQAEDEADYYCNSRDSCGNHLVVF GGGTKLTVL SEQ ID NO: 27630 | QVQLVESGGGVVQPGRSLRLSCAASGFTLSNYGM HWVRQAPGKGLEWVAVIWFGGDNKYYADSVKGR FTISRDNSKNTLYLQMNSLRAEDTAVFYCARDNW NYGDHYYYGMDVWGQGTTVTVSS SEQ ID NO: 31636 |
| iPS:436996 | 21-225_191B9 | NA | CAGTCTGTGTTGACGCAGCCGCCCTCAGTGTC TGCGGCCCCAGGACAGAAGGTCACCATCTCCT GCTCTGGAAGCAGCTCCAACATCGGAATAAT TATGTATCCTGGTACCAGCAGCTCCCAGGAAC AGCCCCCAAACTCCTCATTTATGACAATAAAA AGCGACCCTCAGGGATTCCTGACCTGTCT GGCTCCAAGTCTGGCACGTCAGCCACCCTGGG CATCACCGGACTCCAGACTGGGGACGAGGCC GATTATTACTGCGAACATGGATAGCAGCCT GAGTGTTGTCTTCGGAACTGGGACCAAGG TCACCGTCCTA SEQ ID NO: 27631 | CAGGTGCAGCTGGTGGAGTCTGGGGGAGGCGTG GTCCAGCCTGGGAGGTCCCTGAGACTCTCCTGTG CAGCGTCTGGATTCACCTTCAGTTCCATGGCAT GCACTGGGTCCGCCAGGCTCCAGGCAAGGGCT GGAGTGGGTGGCAGTTATATGGTATGATGGAAGT AAAAATACTATGCAGACTCCGTGAAGGGCCGA TTCACCATCTCCAGAGACAATTCCAAGAACACGC TGCATCTGCAAATGAACAGTCTGAGAGCCGAGG ACACGGCTGTGTATTACTGTGCGAAAGAAGGGTA TAGCAGTGGCTTTTACAGGGGGTTTGACAACTGG GGCCAGGGAACCCTGGTCACCGTCCTCA SEQ ID NO: 31637 |

FIGURE 50
(Continued)

| | | | |
|---|---|---|---|
| iPS:437000 | 21-225_191G9 | AA | QSVLTQPPSVSAAPGQKVTISCSGSSSNIGNNYVSWYQQLPGTAPKLLIYDNKKRPSGIPDRFSGSKSGTSATLGITGLQTGDEADYYCGTWDSSLSVCVFGTGTKVTVL<br>SEQ ID NO: 27632 | QVQLVESGGGVVQPGRSLRLSCAASGFTFSFHGMHWVRQAPGKGLEWVAVIWYDGSKKYYADSVKGRFTISRDNSKNTLHLQMNSLRAEDTAVYYCAKEGYSSGFYRGFDNWGQGTLVTVSS<br>SEQ ID NO: 31638 |
| | | NA | CAGGCTGTGTCGACTCGGCCGTCTTCCCTCTCTGCATCTCCTGGAGCATCAGCCAGTCTCACCTGCACCTTACGCAGTGGCATCAATGTTGTACCTACAGGATATACTGGTACCAGCAGAAGCCAGGGAGTCCTCCCAGTATCTCCTGAGGTACAAATCAGACTCAGATAAGCAGCAGGGCTCTGGAGTCCCCAGCCGCTTCTCTGGATCCAAAGATGCTTCGGCCAATGCAGGGATTTTACTCATCTCTGGCTCCAGTCTGAGGATGAGGCTGACTATTACTGTATGATTTGGCACAGCAGCGCTGTGGTATTCGGCGGAGGGACCAAGCTGACCGTCCTA<br>SEQ ID NO: 27633 | CAGGTGCAGCTGGTGGAGTCTGGGGGAGGCGTGGTCCAGCCTGGGAGGTCCCTGAGACTCTCCTGTGCAGCGTCTGGATTCACCTTCAGTAGTTTCCATGGCATGCACTGGGTCCGCCAGGCTCCAGGCAAGGGGCTGGAGTGGGTGGACACTTATATGGTTTGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATCGGGTGGGAGGTACTAGTCCTCCTACTACTACTACGGTATGGACGTCTGGGGCCAAGGGACCACGGTCACCGTCTCCTCA<br>SEQ ID NO: 31639 |
| | | AA | QAVSTRPSSLSASPGASASLTCTLRSGINVGTYRIYWYQQKPGSPPQYLLRYKSDSDKQQGSGVPSRFSGSKDASANAGILLISGLQSEDEADYYCMIWHSSAVVFGGGTKLTVL<br>SEQ ID NO: 27634 | QVQLVESGGGVVQPGRSLRLSCAASGFTFSTYGMHWVRQAPGKGLEWVTLIWFDGSNKYYADSVKGRFTISRDNSKNTLYLQMNSLRAEDTAVYYCARDRVGGTSPPYYYYGMDVWGQGTTVTVSS<br>SEQ ID NO: 31640 |

FIGURE 50
(Continued)

| | | | | |
|---|---|---|---|---|
| iPS:437002 | 21-225_191H9 | NA | CAGACTGTGTGGTGACTCAGGAGCCCTCACTGAC TGTGTCCCCAGGAGGGACAGTCAGTCACCTCACCT GTGCTTCCAGCACTGAGCAGTCAGTCACCAGTGCT TACTATCCAAACTGGTTGCAGCAGAAACCTGG ACAAGCACCCAGGACACTCTGGACCCCTGCCCGTTC ACAAACAAACACTCCTGGACCCCTGCCCGTTC TCAGGCTCCCTCCTTGGGGGCAAAGCTGCCT GACACTGTCAGATGTGCCTGATCTTCTATGGTGT GCTGAGTATTACTGCCTGATCTTCTATGGGGTGT GTACATGTGATATTTGGCGGAGGGACCAAGCT GACCGTCCTA<br><br>SEQ ID NO: 27635 | CAGGTGCAGCTGGTGCAGTCTGGGGCTGAGGTG AAGAAGCCTGGGGCCTCAGTGAAGGTCTCCTGTA AGGTTTCTGGATATACCTTCACCGGCTACAATAT GCACTGGGTGCGACAGGCCCCTGGACAAGGCT TGAGTGGATGGGATGGATCAACCTAATAGTGGT GGCACAAACTATGCACACAAGTTTCAGGGCAGG GTCACCATGACCAGGGACACGTCCATCAGCACA GCCTACATGGAGCTGAGCAGGCTGAGATCGAC GACACGCCGTGTATTACTGTGCGAGAGATTTCT ATGATAGTGGTGGAGAAGGGTGGTTCGACCCCTG GGGCCAGGGAACCCTGGTCACCGTCTCCTCA<br><br>SEQ ID NO: 31641 |
| | | AA | QTVVTQEPSLTVSPGGTVTLTCASSTGAVTSAYY PNWLQQKPGQAPRTLIYSTNKHSWTPARFSGS LLGGKAALTLSDVQPEDEAEYYCLIFYGGVHVIF GGGTKLTVL<br><br>SEQ ID NO: 27636 | QVQLVQSGAEVKKPGASVKVSCKVSGYTFTGYNM HWVRQAPGQGLEWMGWINPNSGGTNYAHKFQGR VTMTRDTSISTAYMELSRLRSDDTAVYYCARDFYD SGGEGWFDPWGQGTLVTVSS<br><br>SEQ ID NO: 31642 |
| iPS:437006 | 21-225_192G2 | NA | CAGTCTGTGTTGACGCAGCCGCCCTCAGTGTC TGCGGCCCAGGACAGAAGGTCACCATCTCCT GCTCTGGAAGCAGCTCCAACATTGGGAATAAT TATGTATCCTGGTACCAGCAGCTCCCAGGAAC AGCCCCCAAACTCCTCATTTATGACAATAATA AGCGACCCTCAAGGATTCCTGACCGATTCTCT GGCTCCAAGTCTGGCACGTCAGCCACCCTGGG CATCACCGGACTCCAGACTGGGGACGAGGCC GATTATTACTGCGAACATGGATAGCAGCCT GAGTGCTGGGGTATTCGGCGGAGGGACCAAG CTGACCGTCCTA<br><br>SEQ ID NO: 27637 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGACAGTTATATGGAATGATGGAAG TAATAAATACTATGCAGAGACAATTCCAAGAACACG CTGTATCTGCAAATGAACAGCCTGAGAGCCGAG GACACGGCTCTGTATTACTGTGCGAGAGATCTGG ATAAGAGGAACTTCCTTATTACTACTACTACGG TATGGACGTCTGGGGCCAAGGGACCACGGTCAC CGTCTCCTCA<br><br>SEQ ID NO: 31643 |

FIGURE 50
(Continued)

| | | | |
|---|---|---|---|
| iPS:437008 | 21-225_192E3 | AA | QSVLTQPPSVSAAPGQKVTISCSGSSSNIGNNYVS WYQQLPGTAPKLLIYDNNKRPSGSKSG TSATLGITGLQTGDEADYYCGTWDSSLSAGVFG GGTKLTVL |
| | | | SEQ ID NO: 27638 |
| | | NA | CAGGATCTGTGGTGACTCAGGAGCCCTCACTGAC TGTGTCCCAGGAGGACAGTCACTCTCACCT GTGCTTTCAGCACTGGATCAGTCACCAGTGGT TCCTATCCAAACTGGTTCCAGCAGAAACCTGG ACAAGCACCCAGGGCACTGATTATAGTACAA ACAACAAACACTCCTGGACCCCTGCCGGTTC TCAGGCTCCCTCCTTGGGGGCAAAGCTGCCCT GACACTGTCAGGTGTGCAGGTGAGGACGAG GCTGAGTATTACTGCCTGCTATACTATGGTGG TGCTCAGCTGGTGTTCGGCGGAGGGACCAAGC TGACCGTCCTA |
| | | | SEQ ID NO: 27639 |
| | | AA | QTVVTQEPSLTVSPGGTVTLTCAFSTGSVTSGSY PNWFQQKPGQAPRALIYSTNNKHSWTPARFSGS LLGGKAALTLSGVQREDEAEYYCLLYYGGAQL VFGGGTKLTVL |
| | | | SEQ ID NO: 27640 |
| | | AA | QVQLVESGGGVVQPGRSLRLSCAASGFTFSSYGMH WVRQAPGKGLEWVTVIWNDGSNKYYADSVKGRF TISRDNSKNTLYLQMNSLRAEDTALYYCARDLDKR NFPYYYYGMDVWGQGTTVTVSS |
| | | | SEQ ID NO: 31644 |
| | | NA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTTA CTACTGGAGCTGGATCCGCCAGCCCCAGGGAA GGGCTGGAGTGGATTGGGTACATCTATTACACT GGGAGCACCTACTACAACCCGTCCCTCAAGAGTC GAGTTACCATATCAGTAGACAGTCTAAGAACCA GTTCTCCCTGAAGCTGAGCTCTGTGACTGCCGCG GACACGGCCGTGTATTACTGTGCGAGAGACGATC CCCTCTACGGAATGACGTCTGGGGCCAAGGGA CCACGGTCACCGTCTCCTCA |
| | | | SEQ ID NO: 31645 |
| | | AA | QVQLQESGPGLVKPSQTLSLTCTVSGGSISSGGYYW SWIRQPPGKGLEWIGYIYTGSTYNPSLKSRVTIS VDTSKNQFSLKLSSVTAADTAVYYCARDDPLYGM DVWGQGTTVTVSS |
| | | | SEQ ID NO: 31646 |

FIGURE 50
(Continued)

| | | | |
|---|---|---|---|
| iPS:437010 | 21-225_192G3 | NA | CAGTCTGTGCTGACTCAGCCACCCTCAGCGTC TGGGACCCCGGACAGAGGGTCACCATGTCTT GTTCTGAAGCAGCTCCAACATCGGAAGTAAT ACTGTAAACTGGTACCAACAATTCCAGGAAC GGCCCCCAAACTCCTCATCTATGGTAATAAGC AGCGGCCCTCAAGGGTCCCTGACGATTCTCT GGCTCCAAGTCTGGCACCTCAGCCTCCCTGGC CATCAGTGGGCTCCAGTCTGAGGATGACAGCTG ATTATTACTGTGCAGCGGTGGGATGACAGCCTG AATGGTTGGGTGTTCGGCGGAGGGACCAAGCT GACCGTCCTA<br><br>SEQ ID NO: 27641 | CAGGTGCAGCTGCAGGAGTCGGGCCCAGGACTG GTGAAGCCGTCGGAGACCCTGTCCCTCACCTGCA CTGTCTCTGGTGGCTCCATCAGTAGTTACTACTG GAGCTGGATCCGGCAGCCCCCGGGAAGGGACT GGAGTGGATTGGGCGGATCTATTCCAGTGGGAGC ACCAACTACAACCCCTCCCTCAAGAGTCGAGTCA CCATGTCAGTAGACACGTCAAGAACCAGTTCTC CCTGAAGCTGAACTCTGTGACCGCCGCGACACG GCCGTGTATTACTGTGCGAAAGGGTGGGAGCTAA ACTACTGGGGCCAGGGAACCCTGGTCACCGTCTC CTCA<br><br>SEQ ID NO: 31647 |
| | | AA | QSVLTQPPSASGTPGQRVTMSCSGSSNIGSNTV NWYQQFPGTAPKLLIYGNKQRPSRVPDRFSGSK SGTSASLAISGLQSEDETDYYCAAWDDSLNGWV FGGGTKLTVL<br><br>SEQ ID NO: 27642 | QVQLQESGPGLVKPSETLSLTCTVSGGSISNYYWS WIRQPAGKGLEWIGRIYSSGSTNYNPSLKSRVTMS VDTSKNQFSLKLNSVTAADTAVYYCAKGWELNY WGQGTLVTVSS<br><br>SEQ ID NO: 31648 |
| iPS:437012 | 21-225_192G7 | NA | CAGACTGTGGTGACTCAGGAGCCCTCACTGAC TGTGTCCCCAGGAGGGACAGTCACCTCACCT GTGCTTCCAGCACTGGAGCAGTCACCAGTGGT AACTATCCACAGTGGTTCCAGCAGAAACCTGG ACAAGCACCCAGGGCACTGATTTACAGTACAA CCAACAGACATTCCTGGACCCCTGCCCGTTT CCAGGCTCCCTCCTGGGGGCAAAGCTGCCCT GACACTGTCAGGTGTGCAGCCTGAGGACGAG GCTGAGTATTACTGCCTGTTCTACTATGTGGT GCTCAGGTGATATTCGGCGGAGGGACCAAGCT GACCGTCCTA<br><br>SEQ ID NO: 27643 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTTA CTACTGGAGCTGGATCCGCCAGCACCCAGGGAA GGGCCTGGAGTGGATTGGGTACATCTATTACAGA GGGAGTACCTACTACAATCCGTCCCTCAAGAGTC GAGTTACCATATCAGTGGACACGTCTAAGAACCA GTTCTCCCTGAAACTGAACTCTGTGACTGCCGCG GACACGGCCGTGTATTACTGTGCGAGAGACTCCC CGGTGACAGGATTTGACTATTGGGGCCAGGGAAT CCTGGTCACCGTCCTCA<br><br>SEQ ID NO: 31649 |

FIGURE 50
(Continued)

| | | | | |
|---|---|---|---|---|
| iPS:437014 | 21-225_192H8 | AA | QTVVTQEPSLTVSPGGTVTLTCASSTGAVTSGNYPQWFQQKPGQAPRALIYSTTNRHSWTPARFSGSLLGGKAALTLSGVQPEDEAEYYCLFYYGGAQVIFGGGTKLTVL<br>SEQ ID NO: 27644 | QVQLQESGPGLVKPSQTLSLTCTVSGGSISSGGYYWSWIRQHPGKGLEWIGYIYRGSTYYNPSLKSRVTISVDTSKNQFSLKLNSVTAADTAVYYCARDSPVTGFDYWGQGILVTVSS<br>SEQ ID NO: 31650 |
| | | NA | CAGACTGTGGTGACTCAGGAACCCTCACTGACTGTGTCCCCAGGAGGGACAGTCACTCTCACCTGTGCTTTCAGCACTGGAACAGTCACCAGTGGTTTCTATCCAAACTGGTTCCAGCAGAAACCTGGACAAGCACCCAGGGACACTCCTGGACCCCTGCCCGGTTCTCAGGCTCCCTCCTTGGGGGCATGGCTGCCCTGACACTGTCAGGTGTGCAGCCTGAGGACGAGGCTGATTATTACTGCCTGTGCTACTATGGTGGTGCTCAGCTGATGTTCGGCGGAGGGACCAAGCTGACCGTCCTA<br>SEQ ID NO: 27645 | CAGGTGCAGCTGCAGGAGTCGGGCCAGGAGTGGTGAAGCCTTCACAGACCCTGTCCCTCACCTGCACTGTCTCTGGTGGCTCCATCAGCAGTGGTGGTGACTACTGGAGCTGGATCCGCCAGCACCCAGGGAAGGGCCTGGAGTGGATTGGGTACATCTATTACAGTGGGCCCACCTACTACAACCCGTCCTCAAGAGTCACCATTACCGTCGACAGAGACACGTCTAAGAACCAGTTCTCCCTGAAGCTGAGCTCTGTGACTGCCGCGGACACGGCCGTGTATTACTGTGCGAGAGATAGCTCCCTCTACGGTATGGACGTCTGGGGCCAAGGGACCACGGTCACCGTCCTCCTCA<br>SEQ ID NO: 31651 |
| | | AA | QTVVTQEPSLTVSPGGTVTLTCAFSTGTVTSGFYPNWFQQKPGQAPRALIYNTSNRHSWTPARFSGSLLGGMAALTLSGVQPEDEADYYCLLYYGGAQLMFGGGTKLTVL<br>SEQ ID NO: 27646 | QVQLQESGPGVVKPSQTLSLTCTVSGGSISSGGDYWSWIRQHPGKGLEWIGYIYYSGPTYYNPSLKSRLTMSADTSKNQFSLKLSSVTAADTAVYYCARDSSLYGMDVWGQGTTVTVSS<br>SEQ ID NO: 31652 |

FIGURE 50
(Continued)

| | | | |
|---|---|---|---|
| iPS:437016 | 21-225_193A6 | NA | TCTTCTCTGAGCTGACTCAGGACCCTGCTGTGTCT GTGGCCTTGGGACAGAGCAGTCAGGATCACATG CCAAGGAGACAGCCTCAGAAGCTTATGCAA ACTGGTACCAGCAGAAGCCAGGACAGGCCCC TGTACTTTCATCATCTATGCTAAGAACAACCGGC CCTCAGGGATCCCAGACCGATTCTCTGGCTCC AACTCAGGAAACACACAGTTCCTTGACCATCAC TGGGGCTCAGGCGGAAGATGAGGCTGACTATT ACTGTAATTCCCGGGACAGCAGTGGTAACCAT CTGGTATTCGGCGGAGGGACCAAGCTGACCGT CCTA<br><br>SEQ ID NO: 27647 | CAGGTGCAGCTGCAGGAGAGTCGGGCCAGGACTG GTGAAGCCTTCGGAGACCCTGTCCCTCACCTGCA CTGTCTCTGGTGGCTCCATCAGTAGTTACTACTG GAGCTGGATCCGGCAGCCCCCAGGGAAGGGACT GGAGTGGATTGGGTATATCTATTACAGTGGGAGC ACCAACTACAACCCCTCCCTCAAGAGTCGAGTCA CCATATCAGTAGACACGTCAAGAACCAGTTCTC CCTGAAGCTGAGCTCTGTGACCGCTGCGGACACG GCCGTGTATTACTGTGCGGGAGGATGGGAGCTAA ACTACTGGGGCCAGGGAACCCTGGTCACCGTCTC CTCA<br><br>SEQ ID NO: 31653 |
| | | AA | SSELTQDPAVSVALGQTVRITCQGDSLRSYYAN WYQQKPGQAPVLFIYAKNNRPSGIPDRFSGSNSG NTASLTITGAQAEDEADYYCNSRDSSGNHLVFG GGTKLTVL<br><br>SEQ ID NO: 27648 | QVQLQESGPGLVKPSETLSLTCTVSGGSISSYYWSW IRQPPGKGLEWIGYIYYSGSTNYNPSLKSRVTISVDT SKNQFSLKLSSVTAADTAVYYCAGGWELNYWGQ GTLVTVSS<br><br>SEQ ID NO: 31654 |
| iPS:437018 | 21-225_193H5 | NA | TCCTATGAACTGACTCAGCCACATCCTCAGTGTC CGTGTCCCCAGGACAGACAGCCAGCATCACCT GCTCTGGAGATAAATTGGGGGATAGATTTGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGACACAGCTGACTATT ACTGTCAGGCGTGGGACAGCAGCACTGCGGTA TTCGGCGGAGGGACCAAGCTGACCGTCCTA<br><br>SEQ ID NO: 27649 | GAGGTGCAGCTGGTGGAGTCTGGGGGAGGCTTG GTAATGCCTGGGGGGTCCCTTAGCCTCTCCTGTG CAGCCTCTGGATTCACTTTCAGTAACGCCTACAT GACCTGGGTCCGCCAGGCTCCAGGGAAGGGGCT GGAGTGGGTTGGCCGTATTAAAAGCAAAACTGA TGGTGGGACAACAGACTACGCTGCACCCGTGAA AGGCAGATTCACCATCTCAAGAGATGATTCAAA AAACACGCTGTATCTGCAAATGAACAGCCTGAA AACCGAGGACACAGCCGTGTATTACTGTGTACCACA GATCCCGGTGGTATCTTTGACTACTGGGGCCAGG GAACCCTGGTCACCGTCTCCTCA<br><br>SEQ ID NO: 31655 |

FIGURE 50
(Continued)

| | | | |
|---|---|---|---|
| | | AA | SYELTQPSSVSVSPGQTASITCSGDKLGDRFACW YQQKPGQSPVLVIYQDSKRPSGIPERFSGSNSGN TATLTISGTQAMDEADYYCQAWDSSTAVFGGG TKLTVL<br>SEQ ID NO: 27650 | EVQLVESGGGLVMPGGSLSLSCAASGFTFSNAYMT WVRQAPGKGLEWVGRIKSKTDGGTTDYAAPVKG RFTISRDDSKNTLYLQMNSLKTEDTAVYYCTTDPG GIFDYWGQGTLVTVSS<br>SEQ ID NO: 31656 |
| iPS:437020 | 21-225_193F11 | NA | CAGTATGTGTTGACGCAGCCGCCATCAGTGTC TGCGGCCCCAGGACAGAAGGTCACCATCTCCT GCTTCGGAGGCAGCTCCAACATTGGGAATAAT TATGTATCCTGGTTCCAGCAGTTCCCAGGAAC AGCCCCCAAATTCTCATTTATGACAATAATA AGCGACCCTCAGGGATTCTCTTGACCGATATCT GGCTCCAAGTCTGGCACGTCAGCCACCCTGGA CATCACCGGACTCCAGAATGGGGACGAGGC GATTATTACTGCGGAACATGGGATCGCACCAT GAGTGATTGGGTATTCGGCGGAGGGACCAAG CTGACCGTCCTA<br>SEQ ID NO: 27651 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGAC TTGAGTGGATGGGATGGATCAACCCTTACAGTGG TGGCACAAACTATGCACAGAAGTTCAGGGCAG GGTCACCATGACCAGGGACACGTCCATCAGCAC AGCCTACATGGAACTGAGCAGGCTGAGATCTGA CGACACGGCCGTGTATTACTGTGCGAGAGATAG AGCAGTGGCTGGAAACTACTTCTACTACGGTATG GACGTCTGGGGCCAAGGGACCACGGTCACCGTC TCCTCA<br>SEQ ID NO: 31657 |
| | | AA | QYVLTQPPSVSAAPGQKVTISCFGGSSNIGNNYV SWFQQFPGTAPKFLIYDNNKRPSGILDRLSGSKS GTSATLDITGLQNGDEADYYCGTWDRTMSDWV FGGGTKLTVL<br>SEQ ID NO: 27652 | QVQLVQSGAEVKKPGASVKVSCKASGYTFTFGYYM HWVRQAPGQGLEWMGWINPYSGGTNYAQKFQGR VTMTRDTSISTAYMELSRLRSDDTAVYYCARDRAV AGNYFYYGMDVWGQGTTVTVSS<br>SEQ ID NO: 31658 |

FIGURE 50
(Continued)

| | | | | |
|---|---|---|---|---|
| iPS:437022 | 21-225_194G5 | NA | CAGACTGTGGTGACTCAGGAGCCCTCACTGAC TGTGTCCCCAGGAGGGACAGTCACTCTCACCT GTGCTTCCAGCACTGACTGGAGCAGTCAGTGGT AACTATCCAAACTGGTTCCAGCAGAAACCTGG ACAAACACCCAGGGCACTGATTTATAGTACAA GCAAACAAACACTCCTGGACCCCTGCCCGGTTC TCAGGCTCCCTCCTTGGGGGCAAAGGTGCCCT GACACTGTCAGGTGTGCAGCCTGAGGACGAG GCTGAGTATTACTGCCTGATCTACTATGGTGG TGCTCAGCTGATGTTCGGCGGAGGGACCAAGC TGACCGTCCTA <br><br> SEQ ID NO: 27653 | QTVVTQEPSLTVSPGGTVTLTCASSTGAVTSGNY PNWFQQKPGQTPRALIYSTSNKHSWTPARFSGSL LGGKGALTLSGVQPEDEAEYYCLIYYGGAQLMF GGGTKLTVL <br><br> SEQ ID NO: 27654 | CAGGTGCAGCTGCAGGAGTCGGGCCCAGGACTG GTGAAGCCTTCACAGACCCTGTCCCTCATCTGCA CTGTCTCTGGTGGCTCCATCAGAAGTGGTGGTGA CTACTGGAGCTGGATCCGCCAGCACCCAGGGAA GGGCCTGGAGTGGATTGGGTACATCTATTACAGT GGGAGCACCTACTACAACCCGTCTCTCAAGAGTC GAGTTACCATATCAGTAGACACGTCTAAGAACCA GTTCTCCCTGAAGCTGAGCTCTGTGACTGCCGCG GACACGGCCGTTTATTACTGTGCGAGAGATCACT CCCTCTACGGTATGGACGTCTGGGGCCAAGGGAC CACGGTCACCGTCTCCTCA <br><br> SEQ ID NO: 31659 |
| | | AA | QVQLQESGPGLVKPSQTLSLICTVSGGSIRSGGDYW SWIRQHPGKGLEWIGYIYYSGSTYYNPSLKSRVTIS VDTSKNQFSLKLSSVTAADTAVYYCARDHSLYGM DVWGQGTTVTVSS <br><br> SEQ ID NO: 31660 | |
| iPS:437024 | 21-225_194F11 | NA | CAGTCTGTGTTGACGCAGCCGCCCTCAGTGTC TGCGGCCCAGGACAGAAGGTCACCATCTCCT GCTCTGGAAGCAGCTCCAACATTGGGAATAAT TATGTATCCTGGTACCAGCAGCTCCCAGGAAC AGCCCCCAAACTCCTCATTTATGACAATAATA AGCGACCCTCAGGGATTCCTGACCGATTCTCT GGCTCCAAGTCTGGCACGTCAGCCACCCTGGG CATCACCGGACTCCAGACTGGGGACGAGGCC GATTATTACTGCGAACATGGATAGCAGCCT GAGTGCTGGGGTTTTCGGCGGAGGGACCAAGC TGACCGTCCTA <br><br> SEQ ID NO: 27655 | CAGGTGCAGCTGCAGTGGTGGAGTCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGGCT GGAGTGGGTGGCAGTTATATGACTCCGTGAAGGGCCG TAAAATACCACATGTAGACTCCGTGAAGGGCCG ATTTACCATCTCCAGAGACAATTCCAAGAACACG CTGTATCTGCAAATGAACAGCCTGAGAGCCGAG GACACGGCTCTGTATTACTGTGCGAGAGATCTGG ATAAGAGGAACTTCCTTATTACTACTACTACGG TATGGACGTCTGGGGCCAAGGGACCACGGTCAC CGTCTCCTCA <br><br> SEQ ID NO: 31661 |

FIGURE 50
(Continued)

| | | | |
|---|---|---|---|
| iPS:437026 | 21-225_194D12 | AA | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSAGVFGGGTKLTVL<br>SEQ ID NO: 27656 | QVQLVESGGGVVQPGRSLRLSCAASGFTFSSYGMHWVRQAPGKGLEWVAVIWNDGSKKYHVDSVKGRFTISRDNSKNTLYLQMNSLRAEDTALYYCARDLDKRNFPYYYYGMDVWGQGTTVTVSS<br>SEQ ID NO: 31662 |
| | | NA | CAGAGTGTGGTGACTCAGGAGCCCTCACTGACTGTGTCCCCAGGAGGGACAGTCACTCTCACCTGTGCTTCCAGCACTGGAGCAGTCCAGTGGTGTCTCCAAGCTGGTTCCAGCAGAAACCTGGTCCTTTCCAAGCACCGGCACTGATTATAGTACAAGCAACAGACACTCTCGACCCTGCCCGGTTCTCAGGCTCCCTCCTTGGGGCAAAGCAGCCTGACACTGTCAGGTGTGCAGCTGAGGACGAGGCTGACTATTACTGCCTGATCTACTATGGTGGTGCTCAGCTGGCATTCGGCGGAGGGACCAAGCTGACCGTCCTA<br>SEQ ID NO: 27657 | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGTGACTACTGAGCTGGATCGCCAGCACCCAGGGAAGGGCCTGGAGTGGATTGGGTACATCTATTACAGTGGGAGTACCTACTACAACCCGTCCCTCAAGAGTCGAGTTACCATATCAGTAGACACGTCTAAGAACCAGTTCTCCCTGAAGCTGAGCTCTGTGACTGCCGCGGACACGGCCGTGTATTACTGTGCGAGAGATGGGGCTCGGCACGGTATGGACGTCTGGGGCCAAGGGACCACGGTCACCGTCTCCTCA<br>SEQ ID NO: 31663 |
| | | AA | QTVVTQEPSLTVSPGGTVTLTCASSTGAVTSGSFPSWFQQKPGQAPRALIYSTSNRHSSTPARFSGSLLGGKAALTLSGVQPEDEADYYCLIYYGGAQLAFGGGTKLTVL<br>SEQ ID NO: 27658 | QVQLQESGPGLVKPSQTLSLTCTVSGGSISSGGDYWSWIRQHPGKGLEWIGYIYYSGSTYNPSLKSRVTISVDTSKNQFSLKLSSVTAADTAVYYCARDGARHGMDVWGQGTTVTVSS<br>SEQ ID NO: 31664 |

FIGURE 50
(Continued)

| | | | | |
|---|---|---|---|---|
| iPS:437028 | 21-225_194G12 | NA | CAGTCTGTGTTGACGCAGCCGCCTCAGTGTC TGCGGCCCAGGACAGCAGAAGTCACCATCCT GCTCTGGAAGCAGCTCCAACATTGGAATAAT TATGTATCCTGGTACCAGCAGCTCCCAGGAAC AGCCCCAAACTCCTCATTTATGACAATAATA AGCGACCCTCAAGGATTCCTGACCGATTCTCT GGCTCCAAGTCTGGCACGTCAGCCACCCTGG CATCACCGGACTCCAGACTGGGGAGGAGGCC GATTATTACTGCGGAACATGGGATAGCAGCCT GAGTGTTGGGGTATTCGGCGGAGGGACCAAG CTGACCGTCTTA | CAGGTGCAGCTGGTGGAGTCTGGGGGAGGCGTG GTCCAGCCTGGGAGGTCCCTGAGACTCTCCTGTG CAGCGTCTGATTCACCTTCAGTAGCTATGGCAT GCACTGGGTCCGCCAGGCTCCAGGCAAGGGCT GGAGTGGGTGACAGTTATATGGAATGATGAAG TAATAAATACTATGCAGACTCCGTGAAGGGCCG ATTTACCATCTCCAGAGACAATTCCAAGAACACG CTGTATCTGCAAATGAACAGCCTGAGAGCCGAG GACACGGCTCTGTATTACTGTGCGAGAGATCTGG ATAAGAGGAACTTTCCTTATTACTACTACGG TATGGACGTCTGGGGCCAAGGGACCACGGTCAC CGTCTCCTCA |
| | | | SEQ ID NO: 27659 | SEQ ID NO: 31665 |
| | | AA | QSVLTQPPSVSAAPGQKVTISCSGSSSNIGNNYVS WYQQLPGTAPKLLIYDNNKRPSRIPDRFSGSKSG TSATLGITGLQTGEEADYYCGTWDSSLSVGVFG GGTKLTVL | QVQLVESGGGVVQPGRSLRLSCAASGFTFSSYGMH WVRQAPGKGLEWVTVIWNDGSNKYYADSVKGRF TISRDNSKNTLYLQMNSLRAEDTALYYCARDLDKR NFPYYYYGMDVWGQGTTVTVSS |
| | | | SEQ ID NO: 27660 | SEQ ID NO: 31666 |
| iPS:437030 | 21-225_195E3 | NA | TCCTATGAGCTGACTCAGCCACCCTCAGTGTC CGTGTCCCCAGGACAGACAGCCAGCATCACCT GCTCTGGAGATAAATTGGGGTATAGATCTGTT TGCTGGTATCAGCAGAAGCCAGGCCAGTCCCC TGTGCTGGTCATCTATGAAGATAGCAAGCGAC CCTCAGGGATCCCTGAGCGATTCTCTGGCTCC AACTCTGGGAACACACAGCCACTCTGACCATCAG CGGGACCCAGGCTATGGAGGCTGACTATT ACTGTCAGGCGTGGGACAGTGTCACTGTGGTA TTCGGCGGAGGGACCAAGCTGACCGTCCTA | CAGGTGCAGCTGGTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGGTTTCATATATTACTAGTAGTGGTAAT ACCATATACTACCAGACTCTGTGAAGGGCCGAT TCACCATCTCCAGGGACAACGCCAAGAACTCACT GTATCTGCAAATGAACAGCCTGAGAGCCGAGGA CACGGCCGTATATTACTGTGCGAGAGATAGTCGA TATTTTGACTGGTTTGACTACTGGGGCCAGGAA CCCTGGTCACCGTCTCTTCA |
| | | | SEQ ID NO: 27661 | SEQ ID NO: 31667 |

FIGURE 50
(Continued)

| | | | |
|---|---|---|---|
| iPS:437032 | | AA | SYELTQPPSVSVSPGQTASITCSGDKLGYRSVCW YQQKPGQSPVLVIYEDSKRPSGIPERFSGSNSGNT ATLTISGTQAMDEADYYCQAWDSVTVFGGGT KLIVL<br>SEQ ID NO: 27662 | QVQLVESGGGLVKPGGSLRLSCAASGFTFSDYYMS WIRQAPGKGLEWVSYITSSGNTIYYADSVKGRFTIS RDNAKNSLYLQMNSLRAEDTAVYYCARDSRYFD WFDYWGQGTLVTVSS<br>SEQ ID NO: 31668 |
| | | NA | CAGTCTGTGCTGACTCAGCCACCCTCAGCGTC TGGGACCCCGGGCAGAGGGTCACCATCTCTT GTTCTGGAAGCAGTCCAACATCGGAAGTCAT ACTGTAAACTGGTACCAGCAGAACTCCCAGAAC GGCCCCCAAACTCCTCATCTATAATAATTATC AGCGGCCCTCAGGGGTCCCTGACCGATTCTCT GGCTCCAAGTCTGGCACCTCAGCCTCCCTGAC CATCAGTGGGCTCCAGTCTGCAAACATGGGATGACAGCCTG ATTATTACTGTGCAACATGGGATGACAGCCTG AGTGTTTGGGTGTTCGGCGGAGGGACCAAGGT GACCGTCCTA<br>SEQ ID NO: 27663 | CAGGTGCAGCTGCAGGAGTCGGGCCCAGGACTG GTGAAGCCTTCGGAGACCCTGTCCCTCACCTGCA CTGTCTCTGGTGGCTCCATCAGGAATTACTACTG GAGCTGGATCCGGCAGCCCGCCGGGAAGGGACT GGAGTGGATTGGGCGTATCTATAGCAGTGGGAG CACCAACTACAACCCCTCCCTCAAGAGTCGAGTC TCCATGTCAGTAGACACGTCCAAGAACCAGTTCT CCCTGAAGCTGAGTTCTGTGACCGCCGCGGACAC GGCCGTGTATTACTGTACGAGAGAGGGTGGGAGCTA AACAACTGGGGCCAGGGAACCCTGGTCACCGTC TCCTCA<br>SEQ ID NO: 31669 |
| 21-225_195H6 | | AA | QSVLTQPPSASGTPGQRVTISCSGSSSNIGSHTVN WYQQLPGTAPKLLIYNNYQRPSGVPDRFSGSKS GTSASLTISGLQSEDEADYYCATWDDSLSVWVF GGGTKVTVL<br>SEQ ID NO: 27664 | QVQLQESGPGLVKPSETLSLTCTVSGGSIRNYYWS WIRQPAGKGLEWIGRIYSSGSTNYNPSLKSRVSMSV DTSKNQFSLKLSSVTAADTAVYYCTRGWELNNWG QGTLVTVSS<br>SEQ ID NO: 31670 |

FIGURE 50
(Continued)

| | | | |
|---|---|---|---|
| iPS:437034 | 21-225_195E9 | NA | TCCTATGAGCTGACTCAGCCACCCTCAGTGTC CGTGTCCCCAGGACAGACAGCCAGCATCACCT GCTCAGGAGATAAATTGGGGACAGCCAGCATATGCT TACTGTATCAGCAGAAGCCAGGCCAGTCCCC TGTGCTGGTCATCTATCAAGATAGGAAGCGGC CCCTCAGGGATCCCTGAGCGATTCTCTGGCTCC AATTCTGGGAACACAGGCACTTTGACCATCAG CGGGACCCAGGGTATGGATGAGGCTGACTATT ACTGTCAGGCGTGGGACAGAGGAATTGTGGTA TTCGGCGGAGGGACCAAGCTGACCGTCCTA<br>SEQ ID NO: 27665 | CAGGTGCAGGTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTAACAGTGG TGCCACAAACTATGCACAGAAGTTCAGGCAG GGTCACCATGACCAGGGACACGTCCATCAGCAC AGCCTACATGGAGCTGAACAGGCTGAGATCTGA CGACACGGCCGTGTATTACTGTGCGAGAGCCTAT TACTATGTTCGGGGACTTATTATAACGAGTTCG ACTACTGGGGCCAGGGAACCCTGGTCACCGTCTC CTCA<br>SEQ ID NO: 31671 |
| | | AA | SYELTQPPSVSVSPGQTASITCSGDKLGNKYAY WYQQKPGQSPVLVIYQDRKRPSGIPERFSGSNSG NTGTLTISGTQGMDEADYYCQAWDRGIVVFGG GTKLTVL<br>SEQ ID NO: 27666 | QVQVVQSGAEVKKPGASVKVSCKASGYTFTGYYM HWVRQAPGQGLEWMGWINPNSGATNYAQKFQGR VTMTRDTSISTAYMELNRLRSDDTAVYYCARAYY YGSGTYYNEFDYWGQGTLVTVSS<br>SEQ ID NO: 31672 |
| iPS:437036 | 21-225_195H9 | NA | CAGTATGTGTTGACGCAGCCGCCCTCAGTGTC TGCGGCCCAGGACAGAAGGTCACCATCTCCT GTTCTGGAGGCAGCTCCAACATTGGGAATAAT TATGTATCCTGGTTCCAGCAGTTCCCAGGAAC AGCCCCCAAATTCCTCATTTATGACAATAATA AGCGACCCTCAGGGATTCTTGACCGATTCTCT GGCTCCAAGTCTGGCACGTCAGCCACCCTGGG CATCACCGGACTCCAGACTGGGGACGAGGCC GATTATTACTGCGGAACATGGGATGCGACCAT GAGTGGATTGGGTATTCGGCGGAGGGACCAAGT TGACCGTCCTA<br>SEQ ID NO: 27667 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGGC TTGAGTGGATGGGATGGATCAACCCTTACAGTGG TGGCACAAACTATGCACAGAAGTTTCAGGACAG GGTCACCATGACCAGGGACACGTCCATCACCAC AGCCTACATGGAACTGAGCAGGCTGAGATCTGA CGACACGGCCGTGTATTACTGTGCGAGAGATAG AGCAGTGGCTGGAAACTACTTCTACTACGGTATG GACGTCTGGGGCCAGGGGACCACGGTCACCGTC TCCTCA<br>SEQ ID NO: 31673 |

FIGURE 50
(Continued)

| | | | |
|---|---|---|---|
| | | AA | QYVLTQPPSVSAAPGQKVTISCSGGSSNIGNNYV SWFQQFPGTAPKFLIYDNNKRPSGILDRFSGSKS GTSATLGITGLQTGDEADYYCGTWDRTMSDWV FGGGTKLTVL | QVQLVQSGAEVKKPGASVKVSCKASGYTFTGYYM HWVRQAPGQGLEWMGWINPYSGGTNYAQKFQDR VTMTRDTSITTAYMELSRLRSDDTAVYYCARDRAV AGNYFYYGMDVWGQGTTVTVSS |
| | | | SEQ ID NO: 27668 | SEQ ID NO: 31674 |
| iPS:437040 | 21-225_196E7 | NA | CAGACTGTGGTGACTCAGGAGCCCTCACTGAC TGTGTCCCCAGGAGGGACAGTCACTCTCACCT GTGCTTCCAGCACTGGAGCAGTCACCAGTGCT TACTATCCAAACTGGTTGCAGCAGAAACCTGG ACAAGCACCCAGGACACTGATTATAGTACAA ACAACAACACTCCTGGACCCCGGTTC TCAGGCTCCCTCCTTGGGGGCAAAGCTGCCCT GACACTGTCAGATGTGCAGCCTGAGGACGAG GCTGAGTATTACTGCCTGATTTCTATGGTGGT GTACATGTGATATTTGGCGGAGGGACCAAGCT GACCGTCCTA | CAGGTGCAGCTGGTGCAGTCTGGGGCTGAGGTG AAGAAGCCTGGGGCCTCAGTGAAGGTCTCCTGTA AGGTTTCTGGATATACCTTCACCGGCTACAATAT GCACTGGGTGCGACAGGCCCCTGGACAAGGGCT TGAGTGGATGGGATGGATCAACCCTAATAGTGGT GGCACAAACTATGCACACAAGTTTCAGGGCAGG GTCACCATGACCAGGGACACGTCCATCAGCACA GCCTACATGGAACTGAGCAGGCTGAGATCCGAC GACACGGCCGTGTATTACTGTGCGAGAGATTACT ATGATACTAGTGGAGAAGGGTGGTTCGACCCCTG GGGCCAGGGAACCCTGGTCACCGTCTCCTCA |
| | | | SEQ ID NO: 27669 | SEQ ID NO: 31675 |
| | | AA | QTVVTQEPSLTVSPGGTVTLTCASSTGAVTSAYY PNWLQQKPGQAPRTLIYSTNKHSWTPARFSGS LLGGKAALTLSDVQPEDEAEYYCLIFYGGVHVIF GGGTKLTVL | QVQLVQSGAEVKKPGASVKVSCKVSGYTFTGYNM HWVRQAPGQGLEWMGWINPNSGGTNYAHKFQGR VTMTRDTSISTAYMELSRLRSDDTAVYYCARDYYD TSGEGWFDPWGQGTLVTVSS |
| | | | SEQ ID NO: 27670 | SEQ ID NO: 31676 |

FIGURE 50
(Continued)

| | | | |
|---|---|---|---|
| iPS:437042 | 21-225_197E8 | NA | CAGTCTCTGTGTTGACGCAGCCGCCCTCAGTGTCTGCGGCCCCAGGACAGAAGGTCACCATCCCTGCTCTGGAAGCAGCTCCAACATTGGAATAAATATGTATCCTGGTACCAGCAGTTCCCAGGAACAGCCCCCAAACTCCTCATTTATGACAATAATAAGGACCCCTCAAAGATTCCTGACCGATTCTCTGGCTCCAAATCTGGCAGTCAGCCACCCTGGGCATCACCGGACTCCTGACTGGGGACGAGGCCGATTATTACTGCGGAATATGGGATCGCAGTCTGAGTGTTATGGTTCGGCGGAGGGACCAAGCTGACCGTCCTA SEQ ID NO: 27671 |
| | | | CAGGTGCAGCTGCTGCAGTCTGGGGCTGAGGTGAGGAAGCCTGGGGCCTCAGTGAAGGTCTCCTGCAAGGCTTCTGGATACACCTTCACCGGCTACTATATACACTGGGTGCGACAGGCCCCTGGACAAGGCTTGAGTGGATGGGATGGATCAACCCTAACAGTGGTGGCACAAACTATGCACAGAGGTTTCAGGGCAGGGTCACCATGACCAGGGACACGTCCATCAGCACAGCCTACATGGAGCTGAGCAGGCTGAGATCTGACGACACGGCCGTGTATTACTGTGCGAGAGAGATAGCAGTGGCTGGGAACTACTTCTACTACGGTATGGGCGTCTGGGGCCAAGGGACCACGGTCGCCGTCTCCTCA SEQ ID NO: 31677 |
| | | AA | QSVLTQPPSVSAAPGQKVTISCSGSSSNIGNKYVSWYQQFPGTAPKLLIYDNNKRPSKIPDRFSGSKSGTSATLGITGLLTGDEADYYCGIWDRSLSVMVFGGGTKLTVL SEQ ID NO: 27672 |
| | | | QVQLLQSGAEVRKPGASVRVSCKASGYTFTGYYIHWVRQAPGQGLEWMGWINPNSGGTNYAQRFQGRVTMTRDTSISTAYMELSRLRSDDTAVYYCAREIAVAGNYFYYGMGVWGQGTTVAVSS SEQ ID NO: 31678 |
| iPS:437044 | 21-225_197F9 | NA | CAGTCTCTGTGTTGACTCAGCCACCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATTTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGTATGAATGGTCCGTGTTCGGCGGAGGGACCAAGCTGACCGTCCTA SEQ ID NO: 27673 |
| | | | CAGGTGCAGCTGCAGGAGTCGGGCCCAGGACTGGTGAAGCCTTCGGAGACCCTGTCCCTCACCTGCACTGTCTCTGGTGGCTCCATCAGAATTTACTACTGGAGCTGGATCCGGCAGCCCCAGGGAAGGGACTGGAGTGGATTGGGTATGTCTATTACAGTGGGAGCACCACTACAACCCCTCCCTCAAGAGTCGAGTCACCATATCAGTAGACACGTCCAAGAACCAGTTCTCCCTGAAGCTGAACTCTGTGACCGCTGCGGACACGGCCGTGTATTACTGTGTGAGAGAAGGGGACTACTACGGAATGAGACGTCTGGGCCGAGGGACCACGGTCACCGTCTCCTCA SEQ ID NO: 31679 |

FIGURE 50
(Continued)

| | | AA | QSVLTQPPSASGTPGQRVTISCSGSSSNIGSNTVN WYQQLPGTAPKLLIYSNNQRPSGVPDRFSGSKS GTSASLAISGLQSEDEADYYCAAWDDSMNGPVF GGGTKLTVL<br><br>SEQ ID NO: 27674 | QVQLQESGPGLVKPSETLSLTCTVSGGSIRIYYWSW IRQPPGKGLEWIGYIVYSGSTTYNPSLKSRVTISVD TSKNQFSLKLNSVTAADTAVYYCVRERGSSHRWG DYYGMDVWGRGTTVTVSS<br><br>SEQ ID NO: 31680 |
|---|---|---|---|---|
| iPS:437048 | 21-225_197B11 | NA | CAGACTGTGGTGACTCAGGAGCCCTCACTGAC TGTGTCCCCAGGAGGGACAGTCACTCTCACCT GTGCTTTCAGCACTGGATCAGTCACCAGTGGT TCCTATCCAAACTGGTTCCAGCAGAAACCTGG ACAAGCACCCAGGGACACTGATTATAGTACAA ACAACAACACTCCTGGACCCCCGGTTC TCAGGCTCCCTCCTTGGGGGCAAAGCTGCCCT GACACTGTCAGGTGTGCAGCCTGAGGACGAG GCTGAGTATTACTGCCTGCTCTACTATGGTGGT GCTCAGCTGGTGTTCGGCGGAGGGACCAAGCT GACCGTCCTA<br><br>SEQ ID NO: 27675 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTTA CTACTGGAGCTGGATCCGCCAGCCCCCAGGGAA GGGGCTGGAGTGGATTGGGTACATCTATTACACT GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGACGATC CCCTCTACGGAATGACGTCTGGGGCAAGGGA CCACGGTCACCGTCTCCTCA<br><br>SEQ ID NO: 31681 |
| | | AA | QTVVTQEPSLTVSPGGTVTLTCAFSTGSVTSGSY PNWFQQKPGQAPRALIYSTNNKHSWTPARFSGS LLGGKAALTLSGVQPEDEAEYYCLLYYGGAQL VFGGGTKLTVL<br><br>SEQ ID NO: 27676 | QVQLQESGPGLVKPSQTLSLTCTVSGGSISSGGYYW SWIRQPPGKGLEWIGYIYTGSTYNPSLKSRVTIS VDTSKNQFSLKLSSVTAADTAVYYCARDDPLYGM DVWGQGTTVTVSS<br><br>SEQ ID NO: 31682 |

FIGURE 50
(Continued)

| | | | | |
|---|---|---|---|---|
| iPS:437050 | 21-225_197C11 | NA | CAGACTGTGGTGACTCAGGAGCCCTCACTGAC TGTGTCCCAGGAGGACAGTCAGTCACCT GTGCTTCCAGCACTGAGCAGTCAGTCACCAGTGCT TACTATCCAAACTGGTTGCAGCAGAAACCTGG ACAAGCACCCAGGACACTGATTTATAGTACAA GCAAACAAACACTCCTGGACCCCTGCCCGGTTC TCAGGCTCCCTCCTTGGGGGCAAGCTGCCCT GACACTGTCAGATGTGCAGCCTGAGGACGAG GCTGAGTATTACTGCCTGATCTTCTATGGTGGT GTACATGTGATATTTGGCGGAGGGACCAAGCT GACCGTCCTA | CAGGTGCAGCTGGTGCAGTCTGGGGCTGAGGTG AAGAAGCCTGGGCCTCAGTGAAGGTCTCCTGTA AGGTTTCTGGATATACCTTCACCGGCTACAATAT GCACTGGGTGCGACAGGCCCCTGGACAAGGGCT TGAGTGGATGGGATGGATCAACCTAATAGTGGT GGCACAAACTATGCACACAAGTTTCAGGGCAGG GTCACCATGACCAGGGACACGTCCATCAGCACA GCCTACATGGAGCTGAGCAGGCTGAGATCGAC GACACGGCCGTGTATTACTGTGCGAGAGATTACT ATGATAGTAGTGGAGAAGGGTGGTTCGACCCCTG GGGCCAGGGAACCCTGGTCACCGTCTCCTCA |
| | | | SEQ ID NO: 27677 | SEQ ID NO: 31683 |
| | | AA | QTVVTQEPSLTVSPGGTVTLTCASSTGAVTSAYY PNWLQQKPGQAPRTLIYSTSNKHSWTPARFSGS LLGGKAALTLSDVQPEDEAEYYCLIFYGGVHVIF GGGTKLTVL | QVQLVQSGAEVKKPGASVKVSCKVSGYTFTGYNM HWVRQAPGQGLEWMGWINPNSGGTNYAHKFQGR VTMTRDTSISTAYMELSRLRSDDTAVYYCARDYYD SSGEGWFDPWGQGTLVTVSS |
| | | | SEQ ID NO: 27678 | SEQ ID NO: 31684 |
| iPS:437054 | 21-225_194G3 | NA | CAGTCTGTGTTGACGCAGCCGCCCTCAGTGTC TGCGGCCCAGGACAGAAGGTCACCATCTCCT GCTCTGAAGCAGCTCCAACATCGGAATAAT TATATATCCTGGTACCAGCAGCTCCCAGGAAC AGCCCCCAAACTCCTCATTTATGACAATAAAA AGCGACCCTCAGGGATTCCTGACCGATTCTCT GGCTCCAAGTCTGGCACGTCAGCCACCCTGGG CATCACCGGACTCCAGACTGGGGACGAGGCC GATTATTACTGCGGAACATGGGATAGCAGCCT GAGTGTTTGGTCTTCGGAACTGGGACCAAGG TCACCGTCCTA | CAGGTGCAGCTGGTGGAGTCTGGGGGAGGCGTG GTCCAGCCTGGGAGGTCCCTGAGACTCTCCTGTG CAGCGTCTGGATTCACCTTAGTTTCCATGCAT GCACTGGGTCCGCAGGCTCCAGGCAAGGGCT GGAGTGGGTGGCAGTTATATGGTATGATGGAAGT AAAAAATACTATGCAGACTCCGTGAAGGGCCGA TTCACCATCTCCAGAGACAATTCCAAGAACACGC TGCATCTGCAAATGAACAGTCTGAGAGCCGAGG ACACGGCTGTGTATTACTGTGCGAAAGAAGGGTT TAGCAGTGGCTTTTACAGGGGGTTTGACAACTGG GGCCAGGGAACCCTGGTCACCGTCTCCTCA |
| | | | SEQ ID NO: 27679 | SEQ ID NO: 31685 |

FIGURE 50
(Continued)

| | | | |
|---|---|---|---|
| iPS:437056 | 21-225_198B8 | AA | QSVLTQPPSVSAAPGQKVTISCSGSSSNIGNNYIS WYQQLPGTAPKLLIYDNKKRPSGIPDRFSGSKSG TSATLGITGLQTGDEADYYCGTWDSSLSVCVFG TGTKVTVL<br><br>SEQ ID NO: 27680 | QVQLVESGGGVVQPGRSLRLSCAASGFTFSFHGMH WVRQAPGKGLEWVAVIWYDGSKKYYADSVKGRF TISRDNSKNTLHLQMNSLRAEDTAVYYCAKEGFSS GFYRGFDNWGQGTLVTVSS<br><br>SEQ ID NO: 31686 |
| | | NA | CAGGTGCAGCTGCAGGAGTCGGGCCAGGACTG TGTCTCTGGTGGCTCCATCAGAAGTGGTGGTGA CTACTGAGCTGGATCCGCCAGCACCCAGGGGA GGGCTGGAGTGGATTGGGTACATCTATTACAGT GGGATCACCTACTACATCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGATAGC AGCTCGCGGGGTATGGACGTCTGGGGCCAAGGG ACCACGGTCACCGTCTCCTCA<br><br>SEQ ID NO: 31687 | CAGGTGCAGCTGCAGGAGTCGGGCCAGGACTG GTGAAGCCTTCACAGACCCTGTCCCTCACCTGCA CTGTCTCTGGTGGCTCCATCAGAAGTGGTGGTGA CTACTGAGCTGGATCCGCCAGCACCCAGGGGA GGGCTGGAGTGGATTGGGTACATCTATTACAGT GGGATCACCTACTACATCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGATAGC AGCTCGCGGGGTATGGACGTCTGGGGCCAAGGG ACCACGGTCACCGTCTCCTCA<br><br>SEQ ID NO: 31687 |
| | | AA | QTVVTQESSLTVSPGGTVTLTCVLSTGAVTSGSF PNWFQQKPGQAPRALIYSTSNKHSWTPARFSGS LLGGKAALTLSGVQPEDEADYYFMLYSGGAQM VFGGGTKLTVL<br><br>SEQ ID NO: 27682 | QVQLQESGPGLVKPSQTLSLTCTVSGGSIRSGGDY WSWIRQHPGEGLEWIGYIYYSGITYYNPSLKSRVTI SVDTSKNQFSLKLSSVTAADTAVYYCARDSSSRGM DVWGQGTTVTVSS<br><br>SEQ ID NO: 31688 |

FIGURE 50
(Continued)

| | | | | |
|---|---|---|---|---|
| iPS:437058 | 21-225_199F3 | NA | CAGTCTGTGTTGACGCAGCCGCCCTCAGTGTCTGCGGCCCCAGGACAGAAGGTCACCATCCTGCTCTGGAAGCAGCTCCAACATTGGAATAATTATGTATCCTGGTACCAGCAACTCCCAGGAACAGCCCCCAAACTCCTCATTTATGACAATAATAAGCGCCCCTCAGGGATTCCTGACCGATTCTCTGGCTCCAAGTCTGGCAGTCAGCTGGGACCACCCTGGCATCACCGGCCTCCAGACTGGGGACATGGATAGCAGCCTGATTATTACTGCGGAACATGGAACTGGGAACTGGGACCAAGGTCACCGTCCTA | CAGGTGCAGCTGGTGGAGTCTGGGGGAGGCGTGGTCCAGCCTGGGAGGTCCCTGAGACTCTCCTGTGCAGCCGCTCTGGATTCACCTTCAGTTTCTATGGCATGCACTGGGTCCGCCAGGCTCCAGGCAAGGGCTGGAGTGGGTGGCAGTTATTTGGTATGATGGAAGTAGTAAATACTATGCAGACTCCGTGAAGGGCCGATTCACCGTCTCCAGAGACAATTCCAAGAACACGCTGTATCTGCAAATGAACAGCCTGAGAGCCGAGGACACGGCTGTGTATTATTGTGCGAAAGAAGGGTATAGCAGTGGCTTTTACAGGGGATTTGCCAACTGGGGCCAGGGAACCCTGGTCACCGTCTCCTCA |
| | | | SEQ ID NO: 27683 | SEQ ID NO: 31689 |
| | | AA | QSVLTQPPSVSAAPGQKVTISCSGSSSNIGNNYVSWYQQLPGTAPKLLIYDNNKRPSGIPDRFSGSKSGTSATLGITGLQTGDEADYYCGTWDSSLSACVFGTGTKVTVL | QVQLVESGGGVVQPGRSLRLSCAASGFTFSFYGMHWVRQAPGKGLEWVAVIWYDGSSKYYADSVKGRFTVSRDNSKNTLYLQMNSLRAEDTAVYYCAKEGYSSGFYRGFANWGQGTLVTVSS |
| | | | SEQ ID NO: 27684 | SEQ ID NO: 31690 |
| iPS:437060 | 21-225_199C3 | NA | CAGTCTGTGTTGACTCAGCCACCCTCAGCGTCTGGGACCCCCGGGCAGAGGGTCACCATCTCTTGTTCTGGAAGCAGCTCCAACATCGGAAGTAATACTGTAAACTGGTACCAGCAGCTCCCAGGAACGGCCCCCAAACTCCTCATTTATAGTAATAATCAGCGGCCCTCAGGGGTCCCTGACCGATTCTCTGGCTCCAAGTCTGGCACCTCAGCCTCCCTGGCCATCAGTGGGCTCCAGTCTGAGGATGAGGCTGATTATTACTGTGCAGCATGGGATGACAGCCTGAATGGTCCGGTGTTCGGCGGAGGGACCAAGCTGACCGTCCTA | CAGGTGCAGCTGCAGGAGTCGGGCCCAGGACTGGTGAAGCCTTCGGAGACCCTGTCCCTCACCTGCACTGTCTCTGGTGGCTCCATCAGAATTTACTACTGGAGCTGGATCCGGCAGCCCCCAGGGAAGGGACTGGAGTGGATTGGATATATCTATTACAGTGGGAGCACCACTACAACCCCCTCCCTCAAGAGTCGAGTCACCATATCAGTAGACACGTCCAAGAACCAGTTCTCCCTGAAGCTGAACTCTGTGACCGCTGCGGACACGGCCGTGTATTACTGTGTGAGAGAAACCAGTAGCCACAGATGGGGGACTACTACGGAATGACGTCTGGGGCCGAGGGACCACGGTCACCGTCTCCTCA |
| | | | SEQ ID NO: 27685 | SEQ ID NO: 31691 |

FIGURE 50
(Continued)

| | | | |
|---|---|---|---|
| iPS:437062 | 21-225_200H1 | AA | QSVLTQPPSASGTPGQRVTISCSGGSSNIGSNTVN WYQQLPGTAPKLLIYSNNQRPSGVPDRFSGSKS GTSASLAISGLQSEDEADYYCAAWDDSLNGPVF GGGTKLTVL |
| | | | SEQ ID NO: 27686 |
| | | NA | CAGACTGTGGTGACTCAGGAGCCCTCACTGAC TGTGTCCCCAGGAGGGACAGTCACTCTCACCT GTGCTTCCAACACTGGAGCAGTCACCAGTGGT TCCTATCCAAACTGGTTCCAGCAGAAACCTGG ACAGGCACCCAGGGACCACTGATTATCTACAA ACAACAACACTCCTGGACCCCTGCCCGGTTC TCAGGCTCCCTCCTTGGGGGCAAAGCTGCCCT GACACTGTCAGGTGTGCAGCCTGAGGACGAG GCTGAATATTACTGTCTGATCTACTATGGTGGT GCTCAGTGGTGTTCGGCGGAGGGACCAAGCT GACCGTCCTA |
| | | | SEQ ID NO: 27687 |
| | | AA | QTVVTQEPSLTVSPGGTVTLTCASNTGAVTSGSY PNWFQQKPGQAPRALIYHTNNKHSWTPARFSGS LLGGKAALTLSGVQPEDEAEYYCLIYYGGAQLV FGGGTKLTVL |
| | | | SEQ ID NO: 27688 |

| | |
|---|---|
| QVQLQESGPGLVKPSETLSLTCTVSGGSIRIYYWSW IRQTPGKGLEWIGYIYYSGSTYYNPSLKSRVTISVDT SKNQFSLKLNSVTAADTAVYYCVRERGSSHRWGD YYGMDVWGRGTTVTVSS |
| SEQ ID NO: 31692 |
| CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTGA CTATTGGAGCTGGATCCGCCAGCACCCAGGGAA GGGGCTGGAGTGGATTGGGTACATCTATTATAGT GGGAGCACCTACTACAACCCGTCCCTCAAGAGTC GAGTTACCATATCAGTAGACAGTCTAAGAACCA GTTCTCCCTGAAGCTGAACTCTGTGACTGCCGCG GACACGGCCGTGTATTACTGTGCGAGAGATGGA GCAGCTCTGGGTATGGACGTCTGGGGCCAAGGG ACCACGGTCACCGTCTCCTCA |
| SEQ ID NO: 31693 |
| QVQLQESGPGLVKPSQTLSLTCTVSGGSISSGGDYW SWIRQHPGKGLEWIGYIYSGSTYNPSLKSRVTIS VDTSKNQFSLKLNSVTAADTAVYYCARDGAALGM DVWGQGTTVTVSS |
| SEQ ID NO: 31694 |

FIGURE 50
(Continued)

| | | | |
|---|---|---|---|
| iPS:437064 | 21-225_200G8 | NA | CAGTCTGTGTTGACGCAGCCGCCCTCAGTGTCTGCGGCCCAGGACAGAGGGTCACCATCTCTGCTTCTGGAAGCAGCTCCAACTTGGAAATAATTTTGTATCCTGGTACCAGCAGTTCCCAGGAACAGCCCCAAACTCCTCATTTATGACAATTATAAGGGACCCTCAGGGATTCCTGACCGATTCTCTGTCTCCAAGTCTGGCACGTCAGCCACCCTGGCATCACCGGACTCCAGACTGGGGACGAGGCCGATTATTACTGCGGAACTTGGGATAGCAGCCTGAATACTGGGGTATTCGGCGGAGGGACCAAGCTGACCGTCCTA |
| | | | SEQ ID NO: 27689 |
| | | AA | QSVLTQPPSVSAAPGQRVTISCSGSSSNLGNNFVSWYQQFPGTAPKLLIYDNYKRPSGIPDRFSVSKSGTSATLGITGLQTGDEADYYCGTWDSSLNTGVFGGGTKLTVL |
| | | | SEQ ID NO: 27690 |
| | | | CAGGTGCAGCTGCAGGAGTCGGGCCCAGGACTGGTGAAGCCTTCGGAGACCCTGTCCCTCACCTGCACTGTCTCTGGTGGCTCCATCAGAAGTTACTACTGGAGCTGGATCCGGCAGCCCCCAGGGAAGGACTGGAGTGGATTGGGTATATCTATTACAGTGGGAGTACTAAGTACAACCCCTCCCTCAAGAGTCGAGTCACCATATCAGTAGACACGTCCAAGAACCAGTTCTCCCTGAAACTGAGTCTGTGCGAGAAGGGAGTGGAACCGTGTACTACTGTGCGAGAAAGGGAGTGGAACCCACCATCCACTTTGACTACTGGGGCCAGGGAACCCTGGTCACCGTCTCCTCA |
| | | | SEQ ID NO: 31695 |
| iPS:437066 | 21-225_200G9 | | QVQLQESGPGLVKPSETLSLTCTVSGGSIRSYYWSWIRQPPGKGLEWIGYIYYSGSTKYNPSLKSRVTISVDTSKNQFSLKLSSVTAADTAVYYCARKGVGTIHFDYWGQGTLVTVSS |
| | | | SEQ ID NO: 31696 |
| | | NA | CAGACTGTGGTGACTCAGGAGCCCTCACTGACTGTGTCCCCAGGAGGGACAGTCACTCTCACCTGTGCTTCCAACACTGGAGCAGTCACCAGTGGTTCCTATCCAAATTGGTTACAGCAGAAACCTGGACAAGCACCCAGGGCACTGATTTATCATACAGACAACAAACACTCCTGGACCTGGACCCCTGTTCTCAGGCTCCCCTTGGGGGCAAAGTGCCCTGACACTGTCAGGTGCGCAGCCTGAGGACGAGGCTGAATATTACTGTCTGATCTACTACTATGTGGTGCTCAGCTGGTGTTCGGCGGAGGGACCAAGCTGACCGTCCTA |
| | | | SEQ ID NO: 27691 |
| | | | CAGGTGCAGCTGCAGGAGTCGGGCCCAGGACTGGTGAAGCCTTCACAGACCCTGTCCCTCACCTGCACTGTCTCTGGTGGCTCCATCAGCAGTGGTGGTTACTACTGGAGCTGGATCCGGCAGCACCCAGGGAAGGGCCTGGAGTGGATTGGGTACATCTATTACAGTGGGAGCACCTACTACAACCCGTCCTCAAGAGTCGAGTTACCATATCAGTAGACACGTCTAAGAACCAGTTCTCCCTGAAGCTGAACTCTGTGACTGCCGCGGACACGGCCGTGTATTACTGTGCGAGAGATGAAGCAGCTCTGGTATGACGTCTGGGGCCAAGGGACCACGGTCACCGTCTCCTCA |
| | | | SEQ ID NO: 31697 |

FIGURE 50
(Continued)

| | | | |
|---|---|---|---|
| iPS:437068 | 21-225_200A11 | AA | QTVVTQEPSLTVSPGGTVTLTCASNTGAVTSGSY PNWLQQKPGQAPRALIYHTDNKHSWTPARFSGS LLGGKAALTLSGAQPEDEAEYYCLIYYGGAQLV FGGGTKLTVL<br>SEQ ID NO: 27692 | QVQLQESGPGLVKPSQTLSLTCTVSGGSISSGGDYW SWIRQHPGKGLEWIGYIYYSGSTYYNPSLKSRVTIS VDTSKNQFSLKLNSVTAADTAVYYCARDGAALGM DVWGQGTTVTVSS<br>SEQ ID NO: 31698 |
| | | NA | CAGACTGTGGTGACTCAGGAGCCCTCACTGAC TGTGTCCCAGGAGGGACAGTCACTCTCACCT GTGCTTCCAGCACTGGAGCAGTCACCAGTGGT TACTATCCAAACTGGTTCCAGCAGAAACCTGG ACAAGTACCCAGGGCACTGATTTATAGTACAA ACAACAAACACTCCTGGACCCTGCCGGTTC TCAGGCTCCCTCCTTGGGGGCAAAGCTGCCCT GACACTGTCAGGTGTGCAGCCTGAGGACGAG GCTGAATATTACTGCCTGCTCTATTATGGTGGT GCTCAACTGGCATTCGGCGGAGGGACCAAGCT GACCGTCCTG<br>SEQ ID NO: 27693 | CAGGTGCAGCTGCAGGAGTCGGGCCAGGACTG GTGAAGCCTTCACAGACCCTGTCCCTCACCTGCA CTGTCTCTGGTGGCTCCATCAGCAGTGGTGGTGA CTACTGGAGCTGGATCCGCCAGCACCCAGGGAA GGGGCTGGAGTGGATTGGGTACATCTATTACAGA GGGAGCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTACTGTGCGAGAGATGCA GCAGCCACGGCATGGAGGTCTGGGGCCAAGGG ACCACGGTCACCGTCTCCTCA<br>SEQ ID NO: 31699 |
| | | AA | QTVVTQEPSLTVSPGGTVTLTCASSTGAVTSGYY PNWFQQKPGQVPRALIYSTNNKHSWTPARFSGS LLGGKAALTLSGVQPEDEADYYCLLYYGGAHL AFGGGTKLTVL<br>SEQ ID NO: 27694 | QVQLQESGPGLVKPSQTLSLTCTVSGGSISSGGDYW SWIRQHPGKGLEWIGYIYYRGSTYYNPSLKSRVTIS VDTSKNQFSLKLSSVTAADTAVYYCARDAAAHGM DVWGQGTTVTVSS<br>SEQ ID NO: 31700 |

FIGURE 50
(Continued)

| | | | | |
|---|---|---|---|---|
| iPS:437070 | 21-225_201G11 | NA | TCCTATGAGCTGACTCAGCCACCCTCAGTGTC CGTGTCCCCAGGACAGACAGCCAGCATCACCT GTTCTGGAGATAAATTGGGGGATAGATTTGCT TGCTGGTATCAACAGAAGCCAGGCCAGTCCCC TGTGCTGGTCATCTATCAAGATAGCAAGCGGC CCTCAGGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGCACTGTGTA TTCGGCGGAGGGACCAAGCTGACCGTCCTA<br><br>SEQ ID NO: 27695 | CAGGTACAGCTGCAGCAGTCAGTCAGGACTG GTGAAGCCCTCGCAGACCCTCACTCACCTGTG CCATCTCCGGGACAGTGTCTCTGCATCAATCC TACTTGGAACTGGATCAGGCAGTCCCATCGAGA GGCCTTGAGTGGCTGGGAAGGACATACTACAGG TCCAAGTGGTATCATGTTTATGCAGTATCTGTA AAAGTCGAATAACCATCAACCCAGACACATCCA AGAACCAGTTCTCCCTGCAGCTGAATTCTGTGAC TCCCGAGGACACGGCAGTGTATTACTGTGCAAGA GATCCTGGGGGCTCTTTGACTACTGGGGCCAGG GAACCCTGGTCACCGTCTCCTCA<br><br>SEQ ID NO: 31701 |
| | | AA | SYELTQPPSVSVSPGQTASITCSGDKLGDRFACW YQQKPGQSPVLVIYQDSKRPSGIPERFSGSNSGN TATLTISGTQAMDEADYYCQAWDSSTVVFGGG TKLTVL<br><br>SEQ ID NO: 27696 | QVQLQQSGPGLVKPSQTLSLTCAISGDSVSRINPTW NWIRQSPSRGLEWLGRTYYRSKWYHVYAVSVKSR ITINPDTSKNQFSLQLNSVTPEDTAVYYCARDPGGL PDYWGQGTLVTVSS<br><br>SEQ ID NO: 31702 |
| iPS:437074 | 21-225_203B2 | NA | TCCTATGAGCTGACTCAGCCACTCTCAGTGTC AGTGGCCCTGGGACAGACAGGCCAGGATTACCT GTGGGGGAAACAACATTGGAAGAAAAAATGT GCACTGGTACCAGCAGAAGCCAGGCCAGTCCC CTGTGTTGATCATCTATAGGGATAGCGACCGG CCCTCTGGGATCCCTGAGCGATTCTCTGGCTCC AACTCGGGAACACGGCCACCCTGACCATCAG CAGAGCCCAAGCTGGGGATGAGGCTGACTATT ACTGTCAGGTGTGGGACAGCGGCACTGCGGTA TTCGGCGGAGGGACCAAGCTGCCCGTCCTA<br><br>SEQ ID NO: 27697 | CAGGTGCAGCTGGTGGAGTCTGGGGGAGGCGTG GTCCAGCCGGGGAGGTCCCTGAGACTCTCCTGTG CAGCGTCTGGATTCACCTTCAGTAACTATGCCAT GCACTGGGTCCGCCAGGCTCCAGGCAAGGGGCT GGAGTGGGTGGCAATTATATGGTTTGATGGAAGT AATGAATACTATGCAGACTCCGTGAAGGGCCGA TTCACCATCTCCAGAGACAATTCCATGAGCACGC TGTATCTGCAAATGAACAGCCTGAGAGCCGAGG ACACGGCTGTGTATTACTGTGCGAGAGAAAGTGG GAGCTATGCTCTTTATATCTGGGGCCAAGGGACA ATGGTCACCGTCTCTCA<br><br>SEQ ID NO: 31703 |

FIGURE 50
(Continued)

| | | | |
|---|---|---|---|
| iPS:437076 | 21-225_203G6 | AA | SYELTQPLSVSVALGQTARITCGGNNIGRKNVH WYQQKPGQSPVLIIHRDSDRPSGIPERFSGSNSGN TATLTISRAQAGDEADYYCQVWDSGTAVFGGG TKLPVL<br>SEQ ID NO: 27698 | QVQLVESGGGVVQPGRSLRLSCAASGFTFSNYGM HWVRQAPGKGLEWVAHWFDGSNEYYADSVKGRF TISRDNSMSTLYLQMNSLRAEDTAVYYCARESGSY ALYIWGQGTMVTVSS<br>SEQ ID NO: 31704 |
| | | NA | TCCTATGAACTGACTCAGCCACCCTCAGTGTC CGTGTCCCAGGACAGACAGCCAGCATCACCT GTTCTGGAGATAAATTGGGGATAGATTTGCT TGCTGGTATCAACAGAAGCCAGGCCAGTCCC TGTACTGGTCATCTATCAAGATAACAAGCGGC CCTCAGGGATCCCTGAGCGATTCTCTGGCTCC AACTCTGGGAACACAGTCTATGATGAGGCTGACTATT ACTGTCAGGCGTGGGACAGCAGCACTGTGTA TTCGGCGGAGGGACCAAGCTGACCGTCCTG<br>SEQ ID NO: 27699 | CAGGTTCAGGCTGCAGCAGTCAGGTCCAGGACTG GTGAAGCCCTGCAGACCCTCTCACTCACCTGTG CCATCTCCGGGGACAGTGTCTCTGCACCAATCC TACTTGGAACTGGATCAGGCAGTCCCATCGAGA GGCCTTGAGTGGCTGGGAAGGACATACTACAGG TCCAAGTGGTATCATGTTTATGCACTATCTGTGA AAAGTCGAATAACCATCACCCAGACACATCCA AGAACCAGTTCTCCCTGCAGCTGAACTCTGTGAC TCCCGAGGACACGGCTGTGTATTACTGTGCAAGA GATCCTGGGGGCCTCTTTGACTACTGGGGCCAGG GAACCCTGGTCACCGTCCTCTCCTCA<br>SEQ ID NO: 31705 |
| | | AA | SYELTQPPSVSVSPGQTASITCSGDKLGDRFACW YQQKPGQSPVLVIYQDNKRPSGIPERFSGSNSGN TATLTISGTQSMDEADYYCQAWDSSTVVFGGGT KLTVL<br>SEQ ID NO: 27700 | QVQLQQSGPGLVKPSQTLSLTCAISGDSVSRTNPTW NWIRQSPSRGLEWLGRTYYRSKWYHVYALSVKSRI TITPDTSKNQFSLQLNSVTPEDTAVYYCARDPGGLF DYWGQGTLVTVSS<br>SEQ ID NO: 31706 |

FIGURE 50
(Continued)

| | | | |
|---|---|---|---|
| iPS:437082 | 21-225_205E12 | NA | TCCTATGAGCTGACTCAGCCACTCTCAGTGTCAGCGGCCCTGGACAGACGGCCAGGATTACCTGTGGGGGAAACAACATTGGAAGAAAAATGTGCACTGGTACCAGCAGAAGCCAGGCCAGTCCCCTGTGTTGATCATCCATAGGGATAGCGACCGGCCCTCTGGGATCCCTGAGCGATTCTCTGGCTCCAACTCGGGGAACACGGCCACCCTGACCATCAGCAGAGCCCAAGCCGGGGATGAGGCTGACTATTACTGTCAGGTGTGGGACAGCGGCACTGCGGTATTCGGCGGAGGGACCAAGCTGACCGTCCTA<br>SEQ ID NO: 27701 | CAGGTGCAGCTGGTGGAGTCTGGGGGAGGCGTGGTCCAGCCGGGGAGGTCCCTGAGACTCTCCTGTGCAGCGTCTGGATTCACCTTCAGTAACTATGGCATGCACTGGGTCCGCCAGGCTCCAGGCAAGGGGCTGGAGTGGGTGGCAATTATATGGTTTGATGGAAGTAATGAATACTATGCAGACTCCGTGAAGGGCCGATTCACCATCTCCAGAGACAATTCCATGAGCACGCTGTATCTGCAAATGAACAGCCTGAGAGCCGAGGACACGGCTGTATTACTGTGCGAGAGAAAGTGGGAGCTATGCTCTTTATATCTGGGGCCAAGGGACAATGGTCACCGTCTCTTCA<br>SEQ ID NO: 31707 |
| | | AA | SYELTQPLSVSAALGQTARITCGGNNIGRKNVHWYQQKPGQSPVLIIHRDSDRPSGIPERFSGSNSGNTATLTISRAQAGDEADYYCQVWDSGTAVFGGGTKLPVL<br>SEQ ID NO: 27702 | QVQLVESGGGVVQPGRSLRLSCAASGFTFSNYGMHWVRQAPGKGLEWVAIIWFDGSNEYYADSVKGRFTISRDNSMSTLYLQMNSLRAEDTAVYYCARESGSYALYIWGQGTMVTVSS<br>SEQ ID NO: 31708 |
| iPS:437084 | 21-225_206B5 | NA | TCCTATGAATTGACTCAGCCACTCTCAGTGTCAGTGGCCCTGGGACAGACGGCCAGGATTGCCTGTGGGGGAAACAACATTGGAAGAAAAATGTGCACTGGTACCAGCAGAAGCCAGGCCTGGCCCCTGTGCGCGGTCATCCNTAGGGATAGCGACCGATCTTCTGGGATCCCTGACAGATTCTCTGGCTCCAACTGCGGGAACGACCACCGTGACCATCAGCAGAGCCCAAGCCGGGGAGGACGAGGCAGAGTATTATTGTCAGGATTGGGACGACAGCACTGTGGTGTTCGGCGGAGGGACCAAACTGACCGTCCTA<br>SEQ ID NO: 27703 | CAGGTGCAGCTGGTGGAGTCCGGGGGAGGCGTGGTCCAGCCTGGGAGGTCCCTGAGACTCTCCTGTGCAGCGTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATAACTGTGCGAGAGAGGGTGGGAGCTACCACCTTGACTACTGGGGCCAGGGAACCCTGGTCACCGTCTCCTCA<br>SEQ ID NO: 31709 |

FIGURE 50
(Continued)

| | | | |
|---|---|---|---|
| iPS:437086 | 21-225_209A8 | AA | SYELTQPLSVSVALGQTARIACGGNNIGRKNVH WYQQKPGQLAPVPVIXRDSYRSSGIPDRFSGSNCG NTTVTISRAQAGEEAEYYCQDWDSSTVFGGG TKLTVL SEQ ID NO: 27704 | QVQLVESGGGVVQPGRSLRLSCAASGFTFSSYGMH WVRQAPGKGLEWVAVIWYDGSNKYYADSVKGRF TISRDNSKNTLYLQMNSLRAEDTAVYNCAREGGSY HLDYWGQGILVTVSS SEQ ID NO: 31710 |
| | | NA | CAGTCTGTGTTGACGCAGCCGCCCTCAGTGTC TGCGGCCCCAGGACAGAAGGTCACCATCTCT GCTCTGGAAGCAGCTCCAACATTGGGAGTAAT TTTTTATCCTGGTACCAGCAGCTCCCAGGAAC AGCCCCAAACTCCTCATTTATGACAATAATA AGCGACCCTCAGGGATTCCTGACCGATTCTCT GGCTCCAAGTCTGGCACGTCAGCCACCCTGG CATCACCGGACTCCAGACTGGGGACGAGCC GATTATTACTGCGGAACATGGGATAGCAGCCT GAGTGCTGGGGTATTCGGCGGAGGGACCAAG CTGACCGTCCTA SEQ ID NO: 27705 | GAGGTGCAGCTGGTGGAGTCTGGGGGAGGCTTG GTACAGCCTGGGGGGTCCCTGAGACTCTCCTGTG CAGCCTCTGGATTCACTTTAGAAGTTATAGCAT GAACTGGGTCCGCCAGGCTCCAGGGAAGGGGCT GGAGTGGGTTTTATACATTAGTAGTAGTAGT ATCAAAAAGTACCGAGACTCTGTGAAGGGCCGA TTCACCATCTCCAGAGACAATGCCAAGAACTCAC TGTATCTGCAAATGAACAGCCTGAGAGACGAGG ACACGGCTGTGTATTACTGTGTGAGAGATGATGG GAGCTACTACTTTGACTACTGGGGCCAGGGAACC CTGGTCACCGTCTCCTCA SEQ ID NO: 31711 |
| | | AA | QSVLTQPPSVSAAPGQKVTISCSGSSSNIGSNFLS WYQQLPGTAPKLLIYDNNKRPSGIPDRFSGSKSG TSATLGITGLQTGDEADYYCGTWDSSLSAGVFG GGTKLTVL SEQ ID NO: 27706 | EVQLVESGGGLVQPGGSLRLSCAASGFTFRSYSMN WVRQAPGKGLEWVLYISSSSSIKKYADSVKGRFTIS RDNAKNSLYLQMNSLRDEDTAVYYCVRDDGSYYF DYWGQGTLVTVSS SEQ ID NO: 31712 |

FIGURE 50
(Continued)

| | | | |
|---|---|---|---|
| iPS:437088 | 21-225_209H10 | NA | TCCTATGAATGACTCAGCCACTCTCAGTGTCAGTGGCCCTGGGACAGACGGCCAGGATTGCCTGTGGGGGAAACAAACATTGGAAGAAAAATGTGCACTGGTACCAGCAGAAGCCAGGCTGGCCCCTGTGCCGGTCATCTTAGGGATAGTACCGGTCTTCTGGGATCCCTGACAGATTCTCTGGCTCCAACTGGGGAACACGGCCACCGTGACCATCAGCAGACCCAAGCCGGGGAGGAGGCAGAGTATTATTGTCAGGATTGGGACAGCAGCACTGTGGTGTTCGGCGGAGGGACCAAACTGACCGTCCTA SEQ ID NO: 27707 | CAGGTGCAGCTGGTGGTGGAGTCCGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATAACTGTGCGAGAGAGGGTGGGAGCTACCACCTTGACTACTGGGGCCAGGGAATCCTGGTCACCGTCTCCTCA SEQ ID NO: 31713 |
| | | AA | SYELTQPLSVSVALGQTARIACGGNNIGRKNVHWYQQKPGLAPVPVILRDSYRSSGIPDRFSGSNWGNTATVTISRAQAGEEAEYYCQDWDSSTVFGGGTKLTVL SEQ ID NO: 27708 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYNCAREGGSYHLDYWGQGILVTVSS SEQ ID NO: 31714 |
| iPS:437090 | 21-225_210F11 | NA | CAGACTGTGGTGACTCAGGAGCCCTCACTGACTGTGTCCCCAGGAGGGACAGTCACCTCTCACCTGTGCTTTCAGCACTGGAGCAGTGACCTGGTAATTATCCAAACTGGTTCCAGCAGAAACCTGGACAAGCACCAGGGACTGTTCCAGACTGATTTACAGTACAAGCAACAAACACTCTGGACCCCTGCCGGTTCTCAGGCTCCCTCCTTGGGGGCAAAGCTGCCCTGACACTGTCAGGTGTGCAGCCTGAGGACGAGGCTGAATATTACTGCCTGCTCTACTATGGTGGTGCTCAGCTGGTGTTCGGCGGAGGGACGACCAAGCTGACCGTCCTA SEQ ID NO: 27709 | CAGGTGCAGCTGCAGGAGTCGGGCCCAGGACTGGTGAAGCCGTCACAGACCCTGTCCCTCACCTGCACTGTCTCTGGTGGCTCCATCAGCAGTGGTGGTTCCTACTGGAGCTGGATCCGCCAGCACCCAGGGAAGGGCCTGGAGTGGATTGGGTACATCTATTACATTGGGACCACCTACTACAACCCGTCCCTCAAGAGTCGAGTTACCATATCAGTAGACACGTCTACGAACCACTTCTCCCTGAAACTGAGCTCTGTGACTGCTGCGGACACGGCCGTGTATTACTGTGCGAGAGATGAGCCATTGACCGGTATGGACGTCTGGGGCCAAGGGACCACGGTCACCGTCTCCTCA SEQ ID NO: 31715 |

FIGURE 50
(Continued)

| | | | |
|---|---|---|---|
| iPS:437092 | 21-225_210B12 | AA | QTVVTQEPSLTVSPGGTVTLTCAFSTGAVTSGNYPNWFQQKPGQAPRALIYSTSNKHSWTPARFSGSLLGGKAALTLSGVQPEDEAEYYCLLYYGGAQLVFGGGTKLTVL<br>SEQ ID NO: 27710 | QVQLQESGPGLVKPSQTLSLTCTVSGGSISSGGSYWSWIRQHPGKGLEWIGYIYYIGTTYYNPSLKSRVTISVDTSTNHFSLKLSSVTAADTAVYYCARDEPLTGMDVWGQGTTVTVSS<br>SEQ ID NO: 31716 |
| | | NA | CAGTCTGCCCTGACTCAGCCTGCCTCCGTGTCTGGGTCTCCTGGACAGTCGATCACCATCTGCACTGGAACCAGCAGTGACGTTGGTGGTTATAACTATGTCTCCTGGTACCAACAACACCCAGGCAAAGCCCCCAAATTCATGATTTATGAGGTCAGGAATCGGCCCTCAAGTCTGGCAACACGGCCTCCTGCTGGCTCCAAGTCTGGGCTCCAGGCTGAGGACGAGGCACCATCTCTGGGCTCCAGGCTCATATACCAGCAGCTGATTATTACTGCAGTCTCATATACCAGCAGCGCACTCTGGTATTCGGCGGAGGGACCAAGTTGACCGTCCTA<br>SEQ ID NO: 27711 | CAGGTGCAGCTGGTGCAGTCTGGGGCTGAGGTGAAGAAGCCTGGGGCCTCAGTGAAGATCTCCTGCAAGGCTTCTGGATTCACCTTCACCGACTACTATATGAACTGGGTGCGACAGGCCCCTGGACAAGGCTTGAGTGGATGGGATGGATCAACCTAACAGTGGTGGCACAAACTATGCACAGAAGTTTCAGGCAGGGTCACCATGACCAGGGACACGTCCATCAGCACAGCCTACATGGAGCTGAGTAGGCTGAGATCTGACGAACACGGCCGTGTATTACTGTGCGAGAGGGTATGACTCGTTCGCCCCTGGGGCCAGGGAACCCTGGTCACCGTCTCCTCA<br>SEQ ID NO: 31717 |
| | | AA | QSALTQPASVSGSPGQSITISCTGTSSDVGGYNYVSWYQQHPGKAPKFMIYEVRNRPSGVSNRFSGSKSGNTASLTISGLQAEDEADYYCSSYTSSRTLVFGGGTKLTVL<br>SEQ ID NO: 27712 | QVQLVQSGAEVKKPGASVKISCKASGFTFTDYYMNWVRQAPGQGLEWMGWINPNSGGTNYAQKFQGRVTMTRDTSISTAYMELSRLRSDDTAVYYCARGYDSFAPWGQGTLVTVSS<br>SEQ ID NO: 31718 |

FIGURE 50
(Continued)

| | | | | |
|---|---|---|---|---|
| iPS:437094 | 21-225_210D12 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ATTATGTCTCCTGGTACCAACAACACCAGTC AAAGCCCCCAAACTCTTGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAACTCATATACAAGCAGCAT CACTTGGGGTGTTCGGCGGAGGGACCAAGCTGA CCGTCCTA<br><br>SEQ ID NO: 27713 | CAGGTGCAGTTGGTGGAGTCTGGGGGAGGCGTG GTCCAGCCTGGGAGGTCCCTGAGACTCTCCTGTG CAGCGTCTGGATTCACCTTCAGTCACTATGGCAT GCACTGGGTCCGCCAGGCTCCAGGCAAGGGCT GGAGTGGGTGGCAGTTATATGGTATGATGAAGT AATAAATACTATGCAGAGACTCCGTGAAGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCCGAGGGTTTGGACGTCTGGGGCCAAGG GACCACGGTCACCGTCTCCTCA<br><br>SEQ ID NO: 31719 |
| | | AA | QSALTQPASVSGSPGQSITISCTGTSSDVGGYNY VSWYQQHPVKAPKLLIYEVSNRPSGVSNRFSGS KSGNTASLTISGLQAEDEADYYCNSYTSSITWVF GGGTKLTVL<br><br>SEQ ID NO: 27714 | QVQLVESGGGVVQPGRSLRLSCAASGFTFSHYGM HWVRQAPGKGLEWVAVIWYDGSNKYYADSVKGR FTISRDNSKNTLYLQMNSLRAEDTAVYYCARGDW NPEGLDVWGQGTTVTVSS<br><br>SEQ ID NO: 31720 |
| iPS:437096 | 21-225_210E12 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ACTATGTCTCCTGGTACCAACAACACCAGGC AAAGCCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCGGCTCATATGTAAAAGGCAT CACTTGGGGTGTTCGGCGGAGGGACCAGTCTAA CCGTCCTC<br><br>SEQ ID NO: 27715 | CAGGTGCACTTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAGTTATATGGTATGATGAAGT AATAAATACTATGCAGAGACTCCGTGAAGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCCGAGGGTATGACGTCTGGGGCCAAGG GACCACGGTCATCGTCTCCTCA<br><br>SEQ ID NO: 31721 |

FIGURE 50
(Continued)

| | | | |
|---|---|---|---|
| | | AA | QSALTQPASVSGSPGQSITISCTGTSSDVGGYNY VSWYQQHPGKAPKLMIYEVSNRPSGVSNRFSGS KSGNTASLTISGLQAEDEADYYCGSYVKGITWV FGGGTSLTVL<br>SEQ ID NO: 27716 | QVHLVESGGGVVQPGRSLRLSCAASGFTFSNYGM HWVRQAPGKGLEWVAVIWYDGSNKYYADSVKGR FTISRDNSKNTLYLQMNSLRAEDTAVYYCARGDW NPEGMDVWGQGTTVTVSS<br>SEQ ID NO: 31722 |
| iPS:437098 | 21-225_211C1 | NA | CAGTCTGCCCTGACTCAGCCTGCCTCCGTGTCT GGGTCTCCTGGACAGTCGATCACCATCTCCTG CACTGGAACCAGTAGTGACGTTGGTAGTTATA ACTATGTCTCCTGGTACCAACAGTACCCAGGC AAAGCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAACTCATATACAAGCAGCAT CACTTGGGTGTTCGGCGGAGGGACCAAGCTGA CCGTCCTA<br>SEQ ID NO: 27717 | CAGGTGCAGCTGGTGGAGTCTGGGGGAGGCGTG GTCCAGCCTGGGAGGTCCCTGAGACTCTCCTGTG CAGCGTCTGGATTCACCTTCAGTCAGTCACTATGGCAT GCACTGGGTCCGCCAGGCTCCAGGCAAGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACACCCTGAGAGCCGAGG ACACGGCTATCTATTACTGTGCGAGGGGGACTG GAACCCGAGGGTTTGGACGTCTGGGGCCAAGG GACCACGGTCACCGTCTCCTCA<br>SEQ ID NO: 31723 |
| | | AA | QSALTQPASVSGSPGQSITISCTGTSSDVGSYNYV SWYQQYPGKAPKLMIYEVSNRPSGVSNRFSGSK SGNTASLTISGLQAEDEADYYCNSYTSSITWVFG GGTKLTVL<br>SEQ ID NO: 27718 | QVQLVESGGGVVQPGRSLRLSCAASGFTFSHYGM HWVRQAPGKGLEWVAVIWYDGSNKYYADSVKGR FTISRDNSKNTLYLQMNTLRAEDTAIYYCARGDWN PEGLDVWGQGTTVTVSS<br>SEQ ID NO: 31724 |

FIGURE 50
(Continued)

| | | | |
|---|---|---|---|
| iPS:437100 | 21-225_211H2 | NA | TCCTATGAACTGACTCAGCCACTCTCAGTGTC AGTGGCCCTGGGACAGACGGCCAGGATTACCT GTGGGGAAACAACATTGGACGTAGAAATGT GCACTGGTACCAACAGAAGCCAGGCCAGGCC CCTATACTGGTCATCTATAGAGATCGCGACCG GCCCTCTGGGATCCCTGAGCGATTCTCTGGCT CCAACTCGGGGAACACGGCCACCCTGACCATC AGCAGAGCCCAAGCGGGGATGAGGCTGACT ATTTCTGTCAGGTGTGGGACAGCAGTACTGCG GTGTTCGGCGGAGGGACCAAACTGACCGTCCT A |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTATGCCAT GCACTGGGTCCGCCAGGCTCCAGGCAAGGGCT GGAGTGGGTGGCAGTTATATGTGTATGATGAAGT AATAAATACTATGCAGACTCCGTGAAGGGCCGA TTCACCATCGCCAGAGACAATTCCAAGAACACGC TGTATCTGCAAATGAACAGCCTGAGAGCCGAGG ACACGGCTGTGTATTACTGTGCGAGAGATCCTGG GAGCTACGGGTTCGACCCTGGGGCCAGGGAAC CCTGGTCACCGTCTCCTCA |
| | | | SEQ ID NO: 27719 |
| | | AA | SYELTQPLSVSVALGQTARITCGGNNIGRRNVH WYQQKPGQAPILVIYRDRDRPSGIPERFSGSNSG NTATLTISRAQAGDEADYFCQVWDSSTAVFGGG TKLTVL |
| | | | QVQLVESGGGVVQPGRSLRLSCAASGFTFSSYAMH WVRQAPGKGLEWVAVIWYDGSNKYYADSVKGRF TIARDNSKNTLYLQMNSLRAEDTAVYYCARDPGSY GFDPWGQGTLVTVSS |
| | | | SEQ ID NO: 31725 |
| | | | SEQ ID NO: 27720 |
| | | | SEQ ID NO: 31726 |
| iPS:437102 | 21-225_211E5 | NA | TCCTATGAGCTGACACAGCCACCCTCGGTGTC AGTGTCCCCAGGACAGACGGCCAGGATCACCT GTTCTGGAGATGCATTGCCAAAGCAATATGCT TATTGGTACCAGCAGAAGCCAGGCCAGGCCCC AGTGCTGGTGATATATAAAGACAGTGCGAGGC CCTCAGGGATCCCTGAGCGATTCTCTGGCTCC CGCTCAGGGACAACAGTCACGTTGACCGTCAG TGGAGTCCAGGCAGAAGACGAGGCTGACTATT ACTGTCAATTAGTGTACAGCAGTGATACTTAT GTCTTCCGGAACTGGGACCATGCTCACCGTCCT A |
| | | | CAGGTGCAGCTGGTGGAGTCTGGGGGAGGCGTG GTCCAGCCTGGGAGGTCCCTGAGACTCTCCTGTG CAGCGTCTGGATTCACCTTCAGGAACTATGGCAT GCACTGGGTCCGCCAGGCTCCAGGCAAGGGGCT GGAGTGGGTGTCAATTATATGGTTTGATGGAAGT GATCAATAATATGCAGACTCCGTGAAGGGCCGAT TCACCATCTCCAGAGACAACTCCAAGAACACGCT GTACCTGCAAATGAACAGCCTGAGAGCCGAGGA CACGGCTGTTTATTACTGTGCGAGAGGCCTCT GTCTACTACTACGGTATGGCGTCTGGGCCAAG GGACCACGGTCACCGTCTCCTCA |
| | | | SEQ ID NO: 27721 |
| | | | SEQ ID NO: 31727 |

FIGURE 50
(Continued)

| | | | |
|---|---|---|---|
| iPS:437104 | 21-225_211G5 | AA | SYELTQPPSVSVSPGQTARITCSGDALPKQYAYW YQQKPGQAPVLVIYKDSARPSGIPERFSGSRSGT TVTLTVSGVQAEDEADYYCQLVYSSDTYVFGTG TMLTVL |
| | | | SEQ ID NO: 27722 |
| | | AA | QVQLVESGGGVVQPGRSLRLSCAASGFTFRNYGM HWVRQAPGKGLEWVSIIWFDGSDQYYADSVKGRF TISRDNSKNTLYLQMNSLRAEDTAVYYCARGLSVY YYGMGVWGQGTTVTVSS |
| | | | SEQ ID NO: 31728 |
| | | NA | CAGGTGCAGCTGGTGGAGTCTGGGGGAGGCGTG GTCCAGCCTGGGAGGTCCCTGAGACTCTCCTGTG CAGCGTCTGGATTCACCTTCAGTCACTTCACTATGCAT GCACTGTGGGTCCGCCAGGCTCCAGGCAAGGGGCT GGAGTGGGTGGCAGTTATATGATGGAAGT AATAAATACTATGCAGACTCCGTGAAGGGCCGA TTCACCATCTCCAGAGACAACAATTCCAAGAACACGC TGTATCTACAAATGAACAGCCTGAGAGCCGAGG ACACGGCTGTGTATTACTGTGCGAGGGGGACTG GAACCCCGAGGGTTTGGACGTCTGGGGCCAAGG GACCACGGTCACCGTCTCCTCA |
| | | | SEQ ID NO: 31729 |
| | | AA | QVQLVESGGGVVQPGRSLRLSCAASGFTFSHYGM HWVRQAPGKGLEWVAVIWYDGSNKYYADSVKGR FTISRDNSKNTLYLQMNSLRAEDTAVYYCARGDW NPEGLDVWGQGTTVTVSS |
| | | | SEQ ID NO: 31730 |
| | | NA | CAGTCTGCCCTGACTCAGCCTGCCTCCGTGTCT GGGTCTCCTGGACAGTCGATAACCATCTCCTG CACTGGAACCAGCAGTGACGTTGGTGGTTATA ACTATGTCTCCTGGTACCAACAGCACCCAGGC AAAGCCCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAACTCATATACAAGAAGCAT CACTTGGGTGTTCGGCGGAGGGACCAAGCTGA CCGTCCTA |
| | | | SEQ ID NO: 27723 |
| | | AA | QSALTQPASVSGSPGQSITISCTGTSSDVGGYNY VSWYQQHPGKAPKLMIYEVSNRPSGVSNRFSGS KSGNTASLTISGLQAEDEADYYCNSYTRSITWVF GGGTKLTVL |
| | | | SEQ ID NO: 27724 |

FIGURE 50
(Continued)

| | | | | |
|---|---|---|---|---|
| iPS:437106 | 21-225_211H7 | NA | CAGACTGTGGTGACTCAGGAGCCCTCACTGAC TGTGTCCCCAGGAGGGACAGTCACTCTCACCT GTGCTTTCAGCACTGGAGCAGTCAGTCACCAGTGGT AACTATCCAAGTTGGTTCCAGCAGAAACCTGG ACAAGTCCAGGGCACTGATTTATAGTACAA GCAACAGACACTCCTGGACCCCTGCCCGGTTT TCTGGCTCCTCCTTGGGGCAAAGCTGCCCT GACACTGTCAGGTGTGCAGCCTGAGGACGAG GCTGAATATTACTGCCTGCTCTACTATGGTGT GCTCAGTGTGTTCGGCGGAGGGACCAAGCT GACCGTCCTA<br>SEQ ID NO: 27725 | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGTTA CTACTGGAGCTGGACCCGCCAGCACCAGGAA GGGCCTGGAGTGGATTGGGTACATCTATTACGTT GGGAGCACCTACTACAACCCGTCCCTCAAGAGTC GAGTTACCATATCAGTAGACACGTCTAAGAACCA GTTCTCCCTGAAGCTGAGTTCTGTGACTGCCGCG GACACGGCCGTGTATTACTGTGCGAGAGATGGG CCATTGAGCGGTATGACGTCTGGGGCCAAGGG ACCACGGTCACCGTCCTCA<br>SEQ ID NO: 31731 |
| | | AA | QTVVTQEPSLTVSPGGTVTLTCAFSTGAVTSGNY PSWFQQKPGQVPRALIYSTSNRHSWTPARFSGSL LGGKAALTLSGVQPEDEAEYYCLLYYGGAQLV FGGGTKLTVL<br>SEQ ID NO: 27726 | QVQLQESGPGLVKPSQTLSLTCTVSGGSISSGGYYW SWTRQHPGKGLEWIGYIYYVGSTYYNPSLKSRVTIS VDTSKNQFSLKLSSVTAADTAVYYCARDGPLSGM DVWGQGTTVTVSS<br>SEQ ID NO: 31732 |
| iPS:437108 | 21-225_211C9 | NA | CAGACTGTGGTGACTCAGGAGCCCTCACTGAC TGTGTCCCCAGGAGGGACAGTCACTCTCACCT GTGGTTCCAGCACTGATCAGTCAGCAGTGGT TACTTTCCAAACTGGTTCCAGCAGAAACCTGG ACAAGCACCAGCACTCCTGGACCCTGCCCGGTTC TCAGGCTCCCTCTTGGGGGCAAAGCTGCCCT GACACTGTCAGATGTGCAGCCTGAGGACGAG GCTGAATATTACTGCCTGCTCTACTATGGTGT GCTCAGCTGGCATTCGGCGGAGGGACCAAACT GACCGTCCTA<br>SEQ ID NO: 27727 | CAGGTGCAGCTGCAGGAGTCGGGCCCAGGACTG GTGAAGCCTTCACAGACCCTGTCCCTCACCTGCA CTGTCTCTGGTGGCTCCATCAGAAGTGGTGTGA CTACTGGAGCTGGATCCGCCAGCACCAGGAA GGGGAGCACCTACTACAACCCGTCCCTCAAGAGTC GAGTTACCATATTACTAGACACGTCTAAGAACCA GTTCTCCCTGAAGCTGAGCTCTGTGACTGTCGCG GACACGGCCGTGTATTACTGTGCGAGAGATTCAG CAGTGTACAATATGGACGTCTGGGGCCAAGGGA CCACGGTCACCGTCTCCTCA<br>SEQ ID NO: 31733 |

FIGURE 50
(Continued)

| | | | |
|---|---|---|---|
| | | AA | QTVVTQEPSLTVSPGGTVILTCGSSTGSVTSGYF PNWFQQKPGQAPRPLIYSTNNKHSWTPARFSGS LLGGKAALTLSDVQPEDEADYYCLLYYGGAQL AFGGGTKLTVL<br>SEQ ID NO: 27728 | QVQLQESGPGLVKPSQTLSLTCTVSGGSIRSGGDY WSWIRQHPGKGLEWIGYIYYSGSTYYNPSLKSRVTI LLDTSKNQFSLKLSSVTADTAVYYCARDSAVYN MDVWGQGTTVTVSS<br>SEQ ID NO: 31734 |
| iPS:437110 | 21-225_211E9 | NA | CAGACTGTGGTGACTCAGGAGCCCTCACTGAC TGTGTCCCCAGGAGGACAGTCACTCTCACCT GTGCTTCCAGCACTGGAGCAGTCACCAGTGGT AACTATTCCAAACTGGTTCCAGCAGAAACCTGG ACAAGCACCCAGGGCACTGATTATAGTACAA TCAACAAACACTCCGGGACCCGCCCGGTTT ACAGGCTTCCTCCTTGGGGGCAAAGCTGCCCT GACACTGTCAGGTGTACAGCCTGAGGACGAG GCTGAGTATTACTGCCTGCTCTACTATGGTGGT GCTCAGCTGGCATTCGGCGGAGGGACCAAGCT GACCGTCCTA<br>SEQ ID NO: 27729 | CAGGTGCAGCTGCAGGAGTCGGGCCAGGACTG GTGAAGCCTTCACAGACCCTGTCCCTCACCTGCA CTGTCTCTGGTGGCTCCATCAGCAGTGGTGGTGA CTACTGGAGCTGGATCCGCCAGCACCCAGGGAA GGGCCTGGAGTGGATTGGGTACATCTATTACACT GGGAGCAACTACTACAACCCGTCCCTCAAGAGTC GAGTTACCATATCAGTAGACACGTCTAAGAATCA GTTCTCCCTGAACCTGATCTCTGTGACTGCCGCG GACACGGCCGTGTATTACTGTGCGAGAGATTCAG CAGTGTACGTATGGACGTCTGGGGCCAAGGGA CCACGGTCACCGTCTCCTCA<br>SEQ ID NO: 31735 |
| | | AA | QTVVTQEPSLTVSPGGTVILTCASSTGAVTSGNY PNWFQQKPGQAPRALIYSTINKHSGTPARFTGFL LGGKAALTLSGVQPEDEAEYYCLLYYGGAQLA FGGGTKLTVL<br>SEQ ID NO: 27730 | QVQLQESGPGLVKPSQTLSLTCTVSGGSISSGGDYW SWIRQHPGKGLEWIGYIYYTGSNYNPSLKSRVTIS VDTSKNQFSLNLISVTAADTAVYYCARDSAVYGM DVWGQGTTVTVSS<br>SEQ ID NO: 31736 |

FIGURE 50
(Continued)

| | | | |
|---|---|---|---|
| iPS:437112 | 21-225_212C2 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ACTATGTCTCCTGGTACCAACAACACCAGGC AAAGCCCCCAAACTCATGATTTATGAGGTCAG AAATCGGCCCTCAAGGTTTCTAATCGCTTCT CTGGCTCCAAGTCTGGCAACACGGCCTCCCTG ACCATCTCTGGGCTCCAGCTGAGGACGAGGC TGATTATTACTGCAGCTCATATACACGCAGCA TCACTTGGGTGTTCGGCGGAGGGACCAAGCTG ACCGTCCTA |
| | | | SEQ ID NO: 27731 |
| | | AA | QSALTQPASVSGSPGQSITISCTGTSSDVGGYNY VSWYQQHPGKAPKLMIYEVRNRPSGVSNRFSGS KSGNTASLTISGLQAEDEADYYCSSYTRSITWVF GGGTKLTVL |
| | | | SEQ ID NO: 27732 |
| iPS:437114 | 21-225_212A4 | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ACTATGTCTCCTGGTACCAACAACACCAGGC AAAGCCCCCAAACTCATGATTTATGAGGTCAG TAATCGGCCCTCAAGGGTTTCTAATCGCTTCTC TGGCTCCAAGTCTGGCAACACGGCCTCCCTGA CCATCTCTGGGCTCCAGGCTGAGGACGAGGCT GATTATTACTGCGGCTCATATGTAAAGGCAT CACTTGGGTGTTCGGCGGAGGGACCAGTCTAA CCGTCCTC |
| | | | SEQ ID NO: 27733 |

| | |
|---|---|
| CAGGTGCAACTGGTGGAGTCTGGGGGAGGCGTG GTCCAGCCTGGGAGGTCCCTGAGACTCTCCTGTG CAGCCGTCTGGATTCACCTTCAGTCACTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCGAGGGTCACCGTCTCCTCA | |
| SEQ ID NO: 31737 | |
| QVQLVESGGGVVQPGRSLRLSCAASGFTFSHYGM HWVRQAPGKGLEWVAVIWYDGSNKYYADSVKGR FTISRDNSKNTLYLQMNSLRAEDTAVYYCARGDW NPEGMDVWGQGTSVTVSS | |
| SEQ ID NO: 31738 | |
| CAGGTGCACCTGGTGGAGTCTGGGGGAGGCGTG GTCCAGCCTGGGAGGTCCCTGAGACTCTCCTGTG CAGCCGTCTGGATTCACCTTCAGTAACTATGGCAT GCACTGGGTCCGCCAGGCTCCAGGCAAGGGCT GGAGTGGGTGGCAGTTATATGGTATGATGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGGACTG GAACCCGAGGGTATGGACGTCTGGGGCCAAGG GACCACGGTCATCGTCTCCTCA | |
| SEQ ID NO: 31739 | |

FIGURE 50
(Continued)

| | | | | |
|---|---|---|---|---|
| iPS:437116 | 21-225_212F6 | AA | QSALTQPASVSGSPGQSITISCTGTSSDVGGYNYVSWYQQHPGKAPKLMIYEVSNRPSGVSNRFSGSKSGNTASLTISGLQAEDEADYYCGSYTSSITWVFGGGTSLTVL<br>SEQ ID NO: 27734 | QVHLVESGGGVVQAGRSLRLSCAASGFTFSNYGMHWVRQAPGKGLEWVAVIWYDGSNKYYADSVKGRFTISRDNSKNTLYLQMNSLRAEDTAVYYCARGDWNPEGMDVWGQGTTVIVSS<br>SEQ ID NO: 31740 |
| | | NA | CAGTCTGCCCTGACTCAGCCTGCCTCCGTGTCTGGGTCTCCTGGACAGTCGATCACCATCTCCTGCACTGGAACCAGTAGTGACGTTGGTGGTTATAACTATGTCTCCTGGTACCAACAGCACCCAGGCAAAGCCCCCAAACTCATGATTTATGAGGTCAGTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCGGAACTCATATACAAGCAGCATCACTTGGGGTGTTCGGCGGAGGGACCAAGCTGACCGTCCTA<br>SEQ ID NO: 27735 | CAGGTGCAGCTGGTGGAGTCTGGGGGAGGCGTGGTCCAGCCTGGGAGGTCCCTGAGACTCTCCTGTGCAGCGTCTGGATTCACCTTCAGTCACTATGGCATGCACTGGGTCCGCCAGGCTCCAGGCAAGGGGCTGGAGTGGGTGGCAGTTATATGGTATGATGGAAGTAATAAATACTATGCGGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGGGGGACTGGAACCCGAGGGTTTGGACGTCTGGGGCCAAGGGACCACGGTCACCGTCTCCTCA<br>SEQ ID NO: 31741 |
| | | AA | QSALTQPASVSGSPGQSITISCTGTSSDVGGYNYVSWYQQYPGKAPKLMIYEVSNRPSGVSNRFSGSKSGNTASLTISGLQAEDEADYYCNSYTSSITWVFGGGTKLTVL<br>SEQ ID NO: 27736 | QVQLVESGGGVVQPGRSLRLSCAASGFTFSHYGMHWVRQAPGKGLEWVAVIWYDGSNKYYADSVKGRFTISRDNSKNTLYLQMNSLRAEDTAVYYCARGDWNPEGLDVWGQGTTVTVSS<br>SEQ ID NO: 31742 |

FIGURE 50
(Continued)

| | | | |
|---|---|---|---|
| iPS:437118 | 21-225_212G7 | NA | CAGTCTGCCCTGACTCAGCCTGCCTCCGTGTCT GGGTCTCCTGGACAGTCAGTCGATCACCATCCTG CACTGGAACCAGCAGTGACGTTGGTGGTTATA ATTATGTCTCCTGGTACCAACAGCACCCAGGC AAAACCCCAAACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAACTCATATACAAGCAGCAT CACTTGGGGTGTTCGGCGGAGGGACCAAGCTGA CCGTCCTA |
| | | | SEQ ID NO: 27737 |
| | | AA | QSALTQPASVSGSPGQSITISCTGTSSDVGGYNY VSWYQQHPGKTPKLMIYEVSNRPSGVSNRFSGS KSGNTASLTISGLQAEDEADYYCNSYTSSITWVF GGGTKLTVL |
| | | | SEQ ID NO: 27738 |
| | | NA | CAGGTGCAGTTGGTGGAGTCTGGGGGAGGCGTG GTCCAGCCTGGGAGGTCCCTGAGACTCTCCTGTG CAGCCTCTGGATTCACCTTCAGTCAGTCACTATGGCAT GCACTGGGTCCGCCAGGCTCCAGGCAAGGGCT GGAGTGGGTGGCAGTTATATGGTATGATGAAGT AATAAATACTGTGCAGACTCCGTGAAGGGCCGA TTCACCATCTCCAGAGACAATTCCACGAACACGC TGTATCTGCAAATGAACAGCCTGAGAGCCGAGG ACACGGCTGTGTATTACTGTGCGAGGGGAGACTG GAACCCCGAGGGTTTGGACGTCTGGGGCCAAGG GACCACGGTCACCGTCTCCTCA |
| | | | SEQ ID NO: 31743 |
| | | AA | QVQLVESGGGVVQPGRSLRLSCAASGFTFSHYGM HWVRQAPGKGLEWVAVIWYDGSNKYCADSVKGR FTISRDNSTNTLYLQMNSLRAEDTAVYYCARGDW NPEGLDVWGQGTTVTVSS |
| | | | SEQ ID NO: 31744 |
| iPS:437120 | 21-225_212A9 | NA | CAGACTGTGTGACTCAGGAGCCCTCACTGAC TGTGTCCCCAGGAGGGACAGTCACTCTCACCT GTGCTTCCAGCACTGGAGCAGTCACCAGTGGT TACTATCCAAACTGGTTCCAGCAGAAACCTGG GGGCCTGGAGTGGATTGGATTGGATTATATGTATATTACAGT ACAAGCACCCAGGCACTGATTTATAGTACAA ACAACAAACACTCCTGGACCCTGACCCGGTTC TCAGGCTCCCTCCTTGGGGGCAAAGTGCCCT GACACTGTCAGGTGTACAGCCTGACGACGAGG CTGACTATTACTGCCTGCTCTACTATGGTGTG CTCAGGTGGGATTCGGGCGGAGGGACCAAGCT GACCGTCCTA |
| | | | SEQ ID NO: 27739 |
| | | NA | CAGGTGCAGCTGCAGGAGTCGGGCCCAGGACTG GTGAAGCCTTCACAGACCCTGTCCCTCACCTGCA CTGTCTCTGGTGGCTCCATCAGAAGTGGTGGTGA CTACTGGAGCTGGATCCGCCAGCACCCAGGGAA GGGACTGGAGTGGATTGGGTATATGTATTACAGT GGGAGCACCTACTACAACCCGTCCCTCAAGAGTC GAGTTACCATATCAGTAGACACGTCTAAGAACCA GTTCTCCCTGAAGCTGAGTTCTGTGACTGTCGCG GACACGGCCGTGTATTACTGTGCGCGAGATTCAG CAGTGTACGGTATGGACGTCTGGGGCCAAGGGA CCACGGTCACCGTCTCCTCA |
| | | | SEQ ID NO: 31745 |

FIGURE 50
(Continued)

| | | | |
|---|---|---|---|
| iPS:437124 | 21-225_212H12 | AA | QTVVTQEPSLTVSPGGTVTLTCASSTGAVTSGYYPNWFQQKPGQAPRALIYSTNKHSWTPARFSGSLLGGKAALTLSGVQPDDEADYYCLLYYGGAQVGFGGGTKLTVL |
| | | | SEQ ID NO: 27740 |
| | | | QVQLQESGPGLVKPSQTLSLTCSVSGGSIRSGGDYWSWIRQHPGKGLEWIGYMYYSGSTYYNPSLKSRVTISVDTSKNQFSLKLSSVTAADTAVYYCARDSAVYGMDVWGQGTTVTVSS |
| | | | SEQ ID NO: 31746 |
| | | NA | CAGGTGCAGCTGCAGGAGTCGGGCCAGGACTGGTGAAGCCTTCACAGACCCTGTCCCTCACCTGCTGTCTCTGGTGGCTCCATCAGAAGTGGTGGTGACTACTGGAGTTGGATCCGCCAGCACCCAGGGAAGGGCCTGGAGTGGATTGGGTACATCTATTACAGTGGGAGCACCTACTACAACCCGTCCCTCAAGAGTCGAGTTACCATATCAGGAGACACAGTCTAAGAACCAGTTCTCCCTGAAGCTGAGCTCTGTGACTGCCGCGGACACGGCCGTGTATTACTGTGCGAGGGATAGCAGCTCCTACGGTATGGACGTCTGGGGCCAAGGGACCACGGTCACCGTCTCCTCA |
| | | | SEQ ID NO: 31747 |
| | | AA | QTVVTQEPSLTVSPGGTVTLTCASSTGAVTSGYYPNWFQQKPGQAPRALIYSTNKHSWTPARFSGSLLGGKAALTLSGVQPEDEAEYYCLLYYGGAHVVFGGGTKLTVL |
| | | | SEQ ID NO: 27742 |
| | | | QVQLQESGPGLVKPSQTLSLTCTVSGGSIRSGGDYWSWIRQHPGKGLEWIGYIYYSGSTYYNPSLKSRVTISGDTSKNQFSLKLSSVTAADTAVYYCARDSSSYGMDVWGQGTTVTVSS |
| | | | SEQ ID NO: 31748 |

FIGURE 50
(Continued)

| | | | | |
|---|---|---|---|---|
| iPS:437128 | 21-225_213G3 | NA | CTGTCTGCCCTGACTCAGCCTGCCTCCGTGTCT GGGTCTCCTGGACAGTCAGTCGATCACCATCCTG CACTGGAACCAGCAGTGACGTTGTGGTTATA ACTATGTCTCCTGGTACCAACAACACCCAGGC AAAGCCCCCAAACTCATGATTTCTGAGGTCAG GAATCGGCCCTCAAGGGTTCTAATCGCTTCT CTGGCTCCAAGTCTGGCAACACGGCCTCCCTG ACCATCTCTGGGCTCCAGGCTGAGGACGAGGC TGATTATTACTGCAACTCATATACACGCAGCA TCACTTGGGTGTTCGGCGGAGGGACCAAGCTG ACCGTCCTA | CAGGTGCAGCTGGTGGAGTCTGGGGGAGGCGTG GTCCAGCCTGGGAGGTCCCTGAGACTCTCCTGTG CAGCCGTCTGGATTCACCTTCAGTCACTATGGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGCATCTGCAAATGAACAGCCTGAGAGCCGAGG ACACGGCTGTGTATTACTGTGCGAGGGGGACTG GAACCCCGAGGGTCACCGTCTCGGGGCCAAGG GACCTCGGTCACCGTCTCCTCA |
| | | | SEQ ID NO: 27743 | SEQ ID NO: 31749 |
| | | AA | LSALTQPASVSGSPGQSITISCTGTSSDVGGYNYV SWYQQHPGKAPKLMISEVRNRPSGVSNRFSGSK SGNTASLTISGLQAEDEADYYCNSYTRSITWVFG GGTKLTVL | QVQLVESGGGVVQPGRSLRLSCAASGFTFSHYGM HWVRQAPGKGLEWVAVIWYDGSNKYYADSVKGR FTISRDNSKNTLHLQMNSLRAEDTAVYYCARGDW NPEGMDVWGQGTSVTVSS |
| | | | SEQ ID NO: 27744 | SEQ ID NO: 31750 |
| iPS:437130 | 21-225_213D5 | NA | CAGTCTGCCCTGACTCAGCCTGCCTCCGTGTCT GGGTCTCCTGGACAGTCAGTCGATCACCATCCTG CACTGAACCAGCAGTGACGTTGTGGTTATA ACTATGTCTCCTGGTACCAACAACACCCAGGC AAAGCCCCCAAACTCGTGATTATGAGGTCCG TAATCGGCCCTCAAGGGTTTCTACTCGCTTCTC TGGCTCCAAGTCTGGCAACAAGGCCTCCCTGA CCATCTCTGGGCTCCAGGCTGAGGACGAGGCT GATTATTACTGCTCATATACAAGAAGAAT CACTGGGTGTTCGGCGGAGGGACCAAGCTGA CCGTCCTG | CAGGTGCAGCTGGTGGAATCTGGGGGAGGCGTG GTCCAGCCTGGGAGGTCCCTGAGACTCTCCTGTG CAGCGTCTGGATTCACCTTCAGTCACTACTGCAT GCACTGGGTCCGCCAGGCTCCAGGCAAGGGGCT GGAGTGGGTGGCAGTTATATGGTATGATGGAAGT AATAAATACTATGCAGACTCCGTGAAGGGCCGA TTCACCATCTCCAGAGACAATTCCAAGAACACGC TGTTTCTGCAAATGAACAGCCTGAGAGTCGAGGA CACGGCTGTGTATTATTGTGCGAGGGGGGACTGG AACCCCGAGGGTATGGACGTCTGGGGCCAAGGG ACCACGGTCACCGTCTCCTCA |
| | | | SEQ ID NO: 27745 | SEQ ID NO: 31751 |

FIGURE 50
(Continued)

| | | | |
|---|---|---|---|
| | | AA | QSALTQPASVSGSPGQSITISCTGTSSDVGGYNY VSWYQQHPGKAPKLVIYEVRNRPSGVSTRFSGS KSGNKASLTISGLQAEDEADYYCCSYTRRITWV FGGGTKLTVL<br>SEQ ID NO: 27746 | QVQLVESGGGVVQPGRSLRLSCAASGFTFSHYGM HWVRQAPGKGLEWVAVIWYDGSNKYYADSVKGR FTISRDNSKNTLFLQMNSLRVEDTAVYYCARGDW NPEGMDVWGQGTTVTVSS<br>SEQ ID NO: 31752 |
| iPS:437132 | 21-225_213F5 | NA | CAGACTGTGGTGACTCAGGAGCCCTCACTGAC TGTGTCCCCAGGAGGACAGTCACTCTCACCT GTGGTTCCAGCACTGGATCAGTCACCAGTGGT TACTTTCCAAACTGGTTCCAGCAGAAACCTGG ACAAACACCCAGGCCACTGATTATAGTACAA ACAACAAGCACTCCTGGACCCTGCCGGTTC TCAGGCTCCCTCCTTGGGGCAAAACTGCCCT GACACTGTCAGATGTGCAGCCTGAGGACGAG GCTGACTATTACTGCCTGCTCTACTTTGGTGGT GCTCAGCTGGCATTCGGCGGAGGGACCAAACT GACCGTCCTA<br>SEQ ID NO: 27747 | CAGGTGCAGCTGCAGGAGTCGGGCCCAGGACTG GTGAAGCCTTCACAGACCCTGTCCCTCACCTGCA CTGTCTCTGGTGGCTCCATCAGAAGTGGTGGTGA CTACTGGAGCTGGATCCGCCAGCACCCAGGGAA GGGCTGGAGTGGATTGGGTACATCTATTATAGT GGGAGCACCTACTACAACCCGTCCCTCAAGAGTC GAGTTACCATATCACTAGACACGTCTAAGAACCA GTTCTCCCTGAAGCTGAGCTCTGTGACTGTCGCG GACACGGCCGTGTATTACTGTGCGAGAGATTCAG CAGTGTACAATATGGACGTCTGGGGCCAAGGGA CCACGGTCACCGTCTCCTCA<br>SEQ ID NO: 31753 |
| | | AA | QTVVTQEPSLTVSPGGTVTLTCGSSTGSVTSGYF PNWFQQKPGQTPRPLIYSTNNKHSWTPARFSGSL LGGKTALTLSDVQPEDEADYYCLLYFGGAQLAF GGGTKLTVL<br>SEQ ID NO: 27748 | QVQLQESGPGLVKPSQTLSLTCTVSGGSIRSGGDY WSWIRQHPGKGLEWIGYIYYSGSTYYNPSLKSRVTI SLDTSKNQFSLKLSSVTVADTAVYYCARDSAVYN MDVWGQGTTVTVSS<br>SEQ ID NO: 31754 |

FIGURE 50
(Continued)

| | | | |
|---|---|---|---|
| iPS:437134 | 21-225_213A7 | NA | CAGTCTGTGCCCTGACTCAGCCTCGCTCCGTGTCT<br>GGGTCTCCTGGACAGTCGATCACCATCTCCTG<br>CACTGGAACCAGCAGTGACGTTGGTGGTTATA<br>ACTATGTCTCTGGTACCAACAGCACCCAGGC<br>AAAGCCCCCAAATTCATGATTTATGAGGTCAG<br>GAATCGGCCCTCAAGGGGTTTCTAATCGCTTCT<br>CTGGCTCCAAGTCTGGCAACACGGCCTCCTG<br>ACCATCTCTGGGCTCCAGGCTGAGGACGAGGC<br>TGATTATTACTGCAGCTCATATACCAGCAGC<br>GCACTCTGGTATTCGGCGGAGGGACCAAGTTG<br>ACCGTCCTA<br>SEQ ID NO: 27749 | CAGGTGCAGCTGTGTGCAGTCTGGGGCTGAGGTG<br>AAGAAGCCTGGGGCCTCCGTGAAGATCTCCTGCA<br>GGGCTTCTGGATTCACCTTCACCGACTACTATAT<br>GAACTGGGTGCGACAGGCCCCTGGACAAGGGCT<br>TGAGTGGATGGGATGGATCAACCCTAAGAATGG<br>TGGCACAAACTATGCACAGAAGTTTCAGGGCAG<br>GGTCACCATGACCAGGGACACGTCCTCAGCAG<br>AGCCTACATGGAGCTGAGTAGGCTGAGATCTGA<br>CGACACGGCCGTGTATTACTGTGCGAAAGGGTAT<br>GATTCGTTCGCCCCCTGGGGCCAGGGAACCCTGG<br>TCACCGTCTCCTCA<br>SEQ ID NO: 31755 |
| | | AA | QSALTQPASVSGSPGQSITISCTGTSSDVGGYNY<br>VSWYQQHPGKAPKFMIYEVRNRPSGVSNRFSGS<br>KSGNTASLTISGLQAEDEADYYCSSYTSSRTLVF<br>GGGTKLTVL<br>SEQ ID NO: 27750 | QVQLVQSGAEVKKPGASVKISCRASGFTFTDYYMN<br>WVRQAPGQGLEWMGWINPKNGTNYAQKFQGRV<br>TMTRDTSLSRAYMELSRLRSDDTAVYYCAKGYDS<br>FAPWGQGTLVTVSS<br>SEQ ID NO: 31756 |
| iPS:437136 | 21-225_214H3 | NA | CAGACTGTGGTGACTCAGGAGCCCTCACTGAC<br>TGTGTCCCCAGGAGGACAGTCACTCACCT<br>GTGCTTCCAGCACTGGAGCAGTCAGAAACCTGG<br>TACTATCCAAACTGGTTCCAGCAGAAACCTGG<br>ACAAGCACCACCAGGGCACTGATTTATAGTACAA<br>GCAACAAACACTCCTGTACCCCTGCCCGTTC<br>TCAGGCTCCCCCTTGGGGGCAAAGCTGCCCT<br>GACACTGTCAGGTGTGCAGCCTGAGGACGAG<br>GCTGAGTATTACTGCCTGCTCTACTATGTGGT<br>GCTCATCATGCGGTATTCGGCGGAGGGACCAAGCT<br>GACCGTCCTA<br>SEQ ID NO: 27751 | CAGGTGCAGCTGCAGGAGTCGGGCCCAGGACTG<br>GTGAAGCCTTCACAGACCCTGTCCCTCACCTGCA<br>CTGTCTCTGGTGGCTCCATCAGAAGTGGTGGTGA<br>CTACTGGAGTTGGATCCGCCAGCACCCAGGGAA<br>GGGCCTGGAGTGGATTGGGTACATCTATTACAGT<br>GGGAGCACCTACTACAACCCGTCCCTCAAGAGTC<br>GAGTTACCATATCAGGAGACACGTCTAAGAACC<br>AGTTCTCCCTGAAGCTGAGCTCTGTGACTGCCGC<br>GGACACGGCCGTGTATTACTGTGCGAGGGATAG<br>CAGCTCCTACGGTATGGACGTCTGGGGCCAAGG<br>GACCACGGTCACCGTCTCCTCA<br>SEQ ID NO: 31757 |

FIGURE 50
(Continued)

| | | | |
|---|---|---|---|
| iPS:437138 | 21-225_214D8 | AA | QTVVTQEPSLTVSPGGTVTLTCASSTGAVTSGYYPNWFQQKPGQAPRALIYSTSNKHSCTPARFSGSLLGGKAALTLSGVQPEDEAEYYCLLYYGGAHVVFGGGTKLTVL<br>SEQ ID NO: 27752 | QVQLQESGPGLVKPSQTLSLTCTVSGGSIRSGDYWSWIRQHPGKGLEWIGYIYSGSTYYNPSLKSRVTISGDTSKNQFSLKLSSVTAADTAVYYCARDSSSYGMDVWGQGTTVTVSS<br>SEQ ID NO: 31758 |
| | | NA | CAGGTGCAGCTGCAGGAGTCGGGCCAGGACTGTGCGGCCCCAGGACAGAAGGTCACCATCTCTGTGAAGCCTTCACAGACCCTGTCCCTCACCTGCAGCTCTGGAAGCAGCTCCAACATTGGGAATAATCTGTCTCTGGTGGCTCCATCAGTACTGCTTTTACTATGTATCCTGGTACCAGCAGTCCCAGGAACTACTGGAGCTGGATCGGCCAGCACCCAGGAAGAGCCCCCAAACTCCTCATTCATGACAATAATAGGCCTGGAGTGGATTGGGTACATCTATTCAGTGAGGGACCCTCAGGGATTCCTGACCGATTCTCTGGAGCACCTACTACAACCGTCCCTCAAGAGTCGGCTCCAAGTCTGGCACGTCAGCCACCCTGGGAGTTACCATATCAGTAGACACGTCTAAGAACCAGCATCACCGGACTCCAGACTGGGGACAGCCTTTCTCCCTGAAGCTGAGCTCTGTGACTGCCGCGGGATTATTACTGCGGAGCATGGGATAGCAGCCTACACGGCCGTGTATTACTGTGCGGAGAGCAAGGGAGTGCTGTGGTAATCGGGGGAGGGGAGCAAGGATATCACTACAGTATCTTTGACTACTGGGGCCACTGACCGTCCTAGGGAACCCTGGTCACCGTCCTCTCCTCA<br>SEQ ID NO: 27753 | SEQ ID NO: 31759 |
| | | AA | QSVLTQPPSVSAAPGQKVTISCSGSSSNIGNNYVSWYQQFPGTAPKLLIHDNNKRPSGIPDRFSGSKSGTSATLGITGLQTGDEADYYCGAWDSSLSAVVIGGGSKLTVL<br>SEQ ID NO: 27754 | QVQLQESGPGLVKPSQTLSLTCTVSGGSISTAFYYWSWIRQHPGKGLEWIGYIYFSGSTYYNPSLKSRVTISVDTSKNQFSLNLSSVTAADTAVYYCARARGYHYSIFDYWGQGTLVTVSS<br>SEQ ID NO: 31760 |

FIGURE 50
(Continued)

| | | | | |
|---|---|---|---|---|
| iPS:437140 | 21-225_214E12 | NA | CAGACTGTGGTGACTCAGGAGCCCTCACTGAC TGTGTCCCCAGGAGGACAGTCACTCTCACCT GTGCTTCCAGCACTGGAGCAGTCAGTCACCGGC TACTATCCAAACTGGTTCCAACAGAAACCTGG ACAAGCACCCAGGGCACTGATTTATAGTACAA GCAATAAACACTCCTGGACCCTGCCCGGTTC TCAGGCTCCCTCCTTGGGGGCAAAGCTGCCT GACACTGTCAGATGTGCAGCCTGAGGACGAG GCTGAGTATTACTGCCTGCTCTACTGTGATGT GCCCAGTGGTGTTCGGCGGAGGGACCAAACT GACCGTCCTA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTGA TTACTGGAGCTGGATCCGCCAGCACCCAGGGAA GGGCCTGGAGTGGATTGGGTACATCTATTACAGT GGGCCACCTACTACAACCCGTCCTCAAGAGTC GAGTTACCATATCAGTAGACACGTCTAAGAACCA GTTCTCCCTGAAGCTGAGCTCTGTGACTGCCGCG GACACGGCCGTGTATTATTGTGCGAGAGATGGGG CTGCGGAGGGTATGACGTCTGGGGCCAAGGGA CCACGGTCACCGTCTCCTCA |
| | | | SEQ ID NO: 27755 | SEQ ID NO: 31761 |
| | | AA | QTVVTQEPSLTVSPGGTVTLTCASSTGAVTSGYY PNWFQQKPGQAPRALIYSTSNKHSWTPARFSGS LLGGKAALTLSDVQPEDEAEYYCLLYCDGAQL VFGGGTKLTVL | QVQLQESGPGLVKPSQTLSLTCTVSGGSISSGGDYW SWIRQHPGKGLEWIGYIYYSGPPTYYNPSLKSRVTIS VDTSKNQFSLKLSSVTAADTAVYYCARDGAAEGM DVWGQGTTVTVSS |
| | | | SEQ ID NO: 27756 | SEQ ID NO: 31762 |
| iPS:437142 | 21-225_215A3 | NA | CAGGTGCAGTTGCAGGAGTCGGGCCCAGGACTG GGTGTCCCCAGGAGGACACTGAGCGTCACTCTCACCT GTGCTTCCAGCACTGAAGCCGTCACCAGTGGT AACTATCCAAGCTGGTTCCAGCAGAAACCTGG ACAAGCACCCAGGGCACTGATTTATAGTACAA GCAACAAACACTCCGGTACCCTGCCCGGTTT ACAGGCTCCCTCCTTGGGGGCAAAGCTGCCT GACACTGTCAGGTGTACAGCCTGAGGACGAG GCTGAGTATTACTGCCTGCTCTCTACTGTGTG CGCTCAGGTGGCATTCGGCGGAGGGACCAAGC TGGCCGTCCTA | CAGGTGCAGTTGCAGGAGTCGGGCCCAGGACTG GTGAAGCCTTCACAGACCCTGTCCCTCACCTGCA CTGTCTCTGGTGGCTCCATCAGCAGTGGTGGTGA CTACTGGAGCTGGATCCGCCAGCACCCAGGGAA GGGCCTGGAGTGGATTGGGTACATCTATTACACT GGGAGCAACTACTACAACCCGTCCTCAAGAGTC GAGTTACCATATCAGTAGACACGTCTAAGAATCA GTTCTCCCTGAAGGTGATCTCTGTGACTGCCGCG GACACGGCCGTGTATTACTGTGCGAGAGATTCAG CAGTGTACGGTATGGACGTCTGGGGCCAAGGGA CCACGGTCACCGTCTCCTCA |
| | | | SEQ ID NO: 27757 | SEQ ID NO: 31763 |

FIGURE 50
(Continued)

| | | | | |
|---|---|---|---|---|
| | | | AA | QTVVTQEPSLTVSPGTVILTCASSTEAVTSGNY PSWFQQKPGQAPRALIYSTSNKHSGTPARFTGSL LGGKAALTLSGVQPEDEAEYYCLLYYGGAQLA FGGGTKLAVL | QVQLQESGPGLVKPSQTLSLTCTVSGGSISSGGDYW SWIRQHPGKGLEWIGYIYTGSNYYNPSLKSRVTIS VDTSKNQFSLKVISVTAADTAVYYCARDSAVYGM DVWGQGTTVTVSS |
| | | | | SEQ ID NO: 27758 | SEQ ID NO: 31764 |
| iPS:437144 | 21-225_215B3 | | NA | TCCTATGAGCTGACTCAGCCACCCTCAGTGTC CGTGTCCCCAGGACAGAGCAGCATCACCT GCTCTGAGATAAATTGGGGATAAATTTGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGGCTATGGATGAGGCTGACTATT CGGGACCCAGGCTGTGGGACAGCAGCACTGTGGTA ACTGTCAGGCGTGGGACAGCAGCACTGTGGTA TTCGGCGGAGGGACCAAGCTGACCGTCCTA | GAGGTGCAGCTGGTGGAGTCTCGGGGAGGCTTG GTAAAGCCTGGGGGGTCCCTTAGACTCTCCGTG CAGCCTCTGATTCACTTTCAGTAACGCCTGAT GCACTGGGTCCGCCAGGCTCCAGGGAAGGGCT GGAGTGGGTTGGCCGTATTAAAAGCAAAACTAA TGGTGGGACAACAGACTACGCTGCACCCGTGAA AGGCAGATTCACCATTTCAAGAGATGATTCAAAA AACACGCTGTATCTGCAAATGAACAGCCTGAAA ACCGAGGACACAGCCGTGTATTACTGTACCACAG ATCCGGGGGATCTTTGACTACTGGGGCCAGG GAACCCTGGTCACCGTCTCCTCA |
| | | | | SEQ ID NO: 27759 | SEQ ID NO: 31765 |
| | | | AA | SYELTQPPSVSVSPGQTASITCSGDKLGDKFACW YQQKPGQSPVLVIYQDSKRPSGIPERFSGSNSGN TATLTISGTQAMDEADYYCQAWDSSTVVFGGG TKLTVL | EVQLVESGGGLVKPGGSLRLSCAASGFTFSNAWM HWVRQAPGKGLEWVGRIKSKTNGGTTDYAAPVK GRFTISRDDSKNTLYLQMNSLKTEDTAVYYCTTDP GGIFDYWGQGTLVTVSS |
| | | | | SEQ ID NO: 27760 | SEQ ID NO: 31766 |

FIGURE 50
(Continued)

| | | | | |
|---|---|---|---|---|
| iPS:437146 | 21-225_215D3 | NA | CAGTCTGCCCTGACTCAGGAGCCCTGCCTCCGTGTCT GGGTCTCCTGGACAGTCACTATCTCCTG CACTGGAACCAGCAGTGACATTGGTGGTTATA ACTATGTCTCCTGGTACCAACAACACCAGC AAAGCCCCCACACTCATGATTTATGAGGTCAG TAATCGGCCCTCAGGGGTTTCTAATCGCTTCTC TGGCTCCAAGTCTGGCAACACGGCCTCCCTGA CCATCTCTGGGCTCCAGGCTGAGGACGAGGCT GATTATTACTGCAACTCATATAAAAGGGGCAG CACTTGGGTGTTCGGCGGAGGGACCAAGGTGA CCGTCCTA | CAGACGCAGCTGGTGGAGTCTGGGGGAGGCGTG GTCCAGCCTGGGAGGTCCCTGAGACTCTCCTGTG CAGCCTCTGGATTCACCTTCAGTGACTCACTATGGCAT GCACTGGGTCCGCCAGGCTCCAGGCAAGGGCT GGAATGGGTGGCAGTTATATGGTATGATGAAGT AATGAGTACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCGAGGGTATGGACGTCTGGGGCCAAGG GACCACGGTCACCGTCCTCCTCA |
| | | | SEQ ID NO: 27761 | SEQ ID NO: 31767 |
| | | AA | QSALTQPASVSGSPGQSITISCTGTSSDIGGYNYV SWYQQHPGKAPTLMIYEVSNRPSGVSNRFSGSK SGNTASLTISGLQAEDEADYYCNSYKRGSTWVF GGGTKVTVL | QTQLVESGGGVVQPGRSLRLSCAASGFTFSHYGMH WVRQAPGKGLEWVAVIWYDGSNEYYADSVKGRF TISRDNSKNTLYLQMNSLRAEDTAVYYCARGDWN PEGMDVWGQGTTVTVSS |
| | | | SEQ ID NO: 27762 | SEQ ID NO: 31768 |
| iPS:437148 | 21-225_215H3 | NA | CAGACTGTGTGACTCAGGAGCCCTCACTGAC TGTGTCCCCAGGAGGGACAGTCACTCTCACCT GTGCTTCTGGACACTGAGCAGTCACCAGTGGT TACTATCCAAACTGGTTCCAGCAGAAACCTGG ACAAGCACCCAGGGCACTGATTTATAGTACAA ACAACAAACACTCCTGTGACCTGTGCCCGTTT TCAGGCTCCCCCTTGGGGGCAAAGCTGCCT GACACTGTCAGGTGTACAGCCTGACGACGAGG CTGACTATTACTGCCTGCTCTACTATGGTGGTG CTCAGGTGGGATTCGGCGGAGGGACCAAGCT GACCGTCCTA | CAGGTGCAGCTGCAGGAGTCGGGCCCAGGACTG GTGAAGCCTTCACAGACCCTGTCCTCACCTGCA GTGTCTCTGGTGGCTCCATCAGAAGTGGTGGTGA CTACTGGAGCTGGATCCGCCAGCACCCAGGGAA GGGCCTGGAGTGGATTGGGTATATGTATTACAGT GGGAGCACCTACTACAACCCGTCCCTCAAGAGTC GAGTTACCATATCAGTAGACACGTCTAAGAACCA GTTCTCCCTGAAGCTGAGTTCTGTGACTGTCGCG GACACGGCCGTGTATTACTGTGCGCGAGATTCAG CAGTGTACGGTATGGACGTCTGGGGCCAAGGGA CCACGGTCACCGTCTCCTCA |
| | | | SEQ ID NO: 27763 | SEQ ID NO: 31769 |

FIGURE 50
(Continued)

| | | | |
|---|---|---|---|
| iPS:437150 | 21-225_216A3 | AA | QTVVTQEPSLTVSPGGTVTLTCASSTGAVTSGYY PNWFQQKPGQAPRALIYSTNNKHSCGPARFSGS LLGGKAALTLSGVQPDDEADYYCLLYYGGAQV GFGGGTKLTVL<br><br>SEQ ID NO: 27764 | QVQLQESGPGLVKPSQTLSLTCSVSGGSIRSGGDY WSWIRQHPGKGLEWIGYMYYSGSTYYNPSLKSRV TISVDTSKNQFSLKLSSVTVADTAVYYCARDSAVY GMDVWGQGTTVTSS<br><br>SEQ ID NO: 31770 |
| | | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ATTATGTCTCCTGGTACCAACAACACCCAGGC AAAGCCCCCAAACTCATGGGGTTTCTAATCGCTTCTC TAATCGGCCCTCAGGGGTTCAACACGGCCTCCCTGA TGGCTCCAAGTCTGGCAACACGGCCTCCCTGA CCATCTCTGGGCTCCAGGCTGAGGACGAGGCT GATTATTACTGCAACTCATATACAAGCAGCAT CACTTGGGTGTTCGGCGGAGGGACCAAGCTGA CCGTCCTA<br><br>SEQ ID NO: 27765 | CAGGTGCAGCTGGTGGAGTCTGGGGGAGGCGTG GTCCAGCCTGGGAGGTCCCTGAGACTCTCCTGTG CAGCGTCTGGATTCACCTTCAGTCACTATGGCAT GCACTGGGTCCGCCAGGCTCCAGGCAAGGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCCGAGGGTTTGGACGTCTGGGGCCAAGG GACCACGGTCACCGTCTCCTCA<br><br>SEQ ID NO: 31771 |
| | | AA | QSALTQPASVSGSPGQSITISCTGTSSDVGGYNY VSWYQQHPGKAPKLMIYEVSNRPSGVSNRFSGS KSGNTASLTISGLQAEDEADYYCNSYTSSITWVF GGGTKLTVL<br><br>SEQ ID NO: 27766 | QVQLVESGGGVVQPGRSLRLSCAASGFTFSHYGM HWVRQAPGKGLEWVAVIWYDGSNKYYADSVKGR FTISRDNSKNTLYLQMNSLRAEDTAVYYCARGDW NPEGLDVWGQGTTVTVSS<br><br>SEQ ID NO: 31772 |

FIGURE 50
(Continued)

| | | | | |
|---|---|---|---|---|
| iPS:437154 | 21-225_216A7 | NA | CAGACTGTGGTGACTCAGGAGCCCTCACTGAC TGTGTCCCCAGGAGGGACAGTCACTCACCT GTGCTTCCAGCACTGGAGCAGTCACCAGTGGT TACTATCCAAACTGGTTCCAGCAGAAACCTGG ACAAGCACCCAGGGCACTGTACCCTGCCGGTTC ACAACAAAACACTCCTGTGGGGCAAAGCTGCCT TCAGGCTCCCCTCCTTGGGGGCAAAGCTGCCT GACACTGTCAGGTGTACAGCTGACGACGAGG CTGACTATTACTGCCTGCTCTACTATGGTGGTG CTCAGGTGGGATTCGGCGGAGGGACCAAGCT GACCGTCCTA | CAGGTGCAGCTGACTCAGGAGTCGGGCCCAGGACTG GTGAAGCCTTCACAGACCCTGTCCCTCACCTGCA GTGTCTCTGGTGGCTCCATCAGAAGTGGTGGTGA CTACTGAGCTGGATCGCCAGCACCCAGGGAA GGGCCTGGAGTGGATTGGGTATATGTATTACAGT GGGAGCACTACTACAACCCGTCCCTCAAGAGTC GAGTTACCATATCAGTAGACACGTCTAAGAACCA GTTCTCCCTGAAGCTGAGTTCTGTGACTGTCGCG GACACGGCCGTGTATTACTGTGCGCGAGATTCAG CAGTGTACGGTATGGACGTCTGGGGCCAAGGGA CCACGGTCACCGTCTCCTCA |
| | | | SEQ ID NO: 27767 | SEQ ID NO: 31773 |
| | | AA | QTVVTQEPSLTVSPGGTVTLTCASSTGAVTSGYY PNWFQQKPGQAPRALIYSTNNKHSCTPARFSGSL LGGKAALTLSGVQPDDEADYYCLLYYGGAQVG FGGGTKLTVL | QVQLQESGPGLVKPSQTLSLTCSVSGGSIRSGGDY WSWIRQHPGKGLEWIGYMYYSGSTYYNPSLKSRV TISVDTSKNQFSLKLSSVTVADTAVYYCARDSAVY GMDVWGQGTTVTVSS |
| | | | SEQ ID NO: 27768 | SEQ ID NO: 31774 |
| iPS:437158 | 21-225_216H11 | NA | CAGACTGTGGTGACTCAGGAGCCCTCACTGAC TGTGTCCCCAGGAGGGACAGTCACTCACCT GTGCTTCCAGCACTGGAGCAGTCACCAGTGGC TACTATCCAAACTGGTTCAACAGAAACCTGG ACAAGCACCCAGGGCACTGATTTATAGTACAA GCAATAAACACTCCTGACCCCTGCCGGTTC TCAGGCTCCCTCCTTGGGGCAGCCTGCCCT GACACTGTCAGATGTGCAGCCTGAGGACGAG GCTGAGTATTACTGCCTGCTCTACTGTGATGGT GCTCAGCTGGTTCGGCGGAGGGACCAAACT GACCGTCCTA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTGGTGA TTACTGGAGCTGGATCGCCAGCACCCAGGGAA GGGCCTGGAGTGGATTGGGTACATCTATTACAGT GGGCCCACCTACTACAACCCGTCCCTCAAGAGTC GAGTTACCATATCAGTAGACACGTCTAAGAACCA GTTCTCCCTGAAGCTGAGCTCTGTGACTGCCGCG GACACGGCCGTGTATTGTGCGAGAGATGGGG CTGCGGAGGGTTTGGACGTCTGGGGCCAAGGGA CCACGGTCACCGTCTCCTCA |
| | | | SEQ ID NO: 27769 | SEQ ID NO: 31775 |

FIGURE 50
(Continued)

| | | | |
|---|---|---|---|
| | | AA | QTVVTQEPSLTVSPGTVTLTCASSTGAVTSGYYPNWFQQKPGQAPRALIYSTSNKHSWTPARFSGSLLGGKAALTLSDVQPEDEAEYYCLLYCDGAQLVFGGGTKLTVL<br><br>SEQ ID NO: 27770 | QVQLQESGPGLVKPSQTLSLTCTVSGGSISSGGDYWSWIRQHPGKGLEWIGYIYSGPTYYNPSLKSRVTISVDTSKNQFSLKLSSVTAADTAVYYCARDGAAEGLDVWGQGTTVTVSS<br><br>SEQ ID NO: 31776 |
| iPS:437160 | 21-225_216B12 | NA | TCCTATGAGCTGACTCAGCCACTCTCAGTGTCAGTGGCCCTGGGACAGACGGCCAGGATTACCTGTGGGGGAGACAAACATTAGAAGAAGAAATGTGCACTGGTACCAGCAGAAGCCAGGCCAGGCCCTGTGCTGGTCATCTATAGGGATAGCAACCGGCCCTCTGGGATCCCTGAGCGATTCTCTGGCTCCAACTCGGGGAACACGGCCACCCTGACCATCAGCAGAGCCCAAGCCGGGGACCAGCAGCTGGAGGCTGACTATTACTGTCAGTGTGTGGGACAGCAGCACTGGGGTGTTCGGCGGAGGGACCAAGCTGACCGTCCTA<br><br>SEQ ID NO: 27771 | CAGGTGCAGCTGGTGGTGGAGTCTGGGGGAGGCGTGGTCCAGCCTGGGAGGTCCCTGAGACTCTCCTGTGCAGCGTCTGGATTCACCTTCAGTAGCTATGCCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAACGCCAAGAACACGCTGTATCTGCAAATGAACAGCCTGAGAGCCGAGGACACGGCTGTGTATTACTGTGCGAGAGATCTGGACTGGGATACTTCTTTGACTACTGGGGCCAGGGAACCCTAGTCACCGTCTCCTCA<br><br>SEQ ID NO: 31777 |
| | | AA | SYELTQPLSVSVALGQTARITCGGDNIRRRNVHWYQQKPGQAPVLVIYRDSNRPSGIPERFSGSNSGNTATLTISRAQAGDEADYYCQVWDSSTGVFGGGTKLTVL<br><br>SEQ ID NO: 27772 | QVQLVESGGGVVQPGRSLRLSCAASGFTFSSYAMHWVRQAPGKGLEWVAVIWYDGSNKYYADSVKGRFTISRDNSKNTLYLQMNSLRAEDTAVYYCARDLGLGYFFDYWGQGTLVTVSS<br><br>SEQ ID NO: 31778 |

FIGURE 50
(Continued)

| | | | |
|---|---|---|---|
| iPS:437162 | 21-225_217B2 | NA | CAGTCTGCCCTGACTCAGCCTGCCTCCGTGTCTGGGTCTCCTGGACAGTCGATCACCATCCTGCACTGGAACCAGCAGTGACGTTGTGGTTATAACTATGTCTCCTGGTACCAACAACACCCAGGCAAAGCCCCAAACTCTTGATTTATGAGGTCAGTAATCGGCCCTCAGGGGTTTATAATGCTCTCTGGCTCCAAGTCTGGCAACACGGCCTCCCTGACCATCTCTGGGCTCCAGGCTGAGGACGAGGCTGATTATTACTGCGGCTCATATGTAAAAGGCATCACTTGGGGTGTTCGGCGGAGGGACCAGTCTGACCGTCCTC | CAGGTGCACCTGGTGGAGTCTGGGGGAGGCGTGGTCCAGCCTGGGAGGTCCCTGAGACTCTCCTGTGCAGCCTCTGGATTCACCTTCAGTAACTATGGCATGCACTGGGTCCGCCAGGCTCCAGGCAAGGGCTGGAGTGGGTGGCAGTTATATGGTATGATGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTATTGTGCGAGGGGGACTGGAACCCCGAGGGTATGGACGTCTGGGGCCAAGGGACCACGGTCATCGTCTCCTCA |
| | | AA | QSALTQPASVSGSPGQSITISCTGTSSDVGGYNYVSWYQQHPGKAPKLLIYEVSNRPSGVYNRFSGSKSGNTASLTISGLQAEDEADYYCGSYVKGITWVFGGGTSLTVL | QVHLVESGGGVVQPGRSLRLSCAASGFTFSNYGMHWVRQAPGKGLEWVAVIWYDGSNKYYADSVKGRFTISRDNSKNTLYLQMNSLRAEDTAVYYCARGDWNPEGMDVWGQGTTVIVSS |
| | | SEQ ID NO: 27774 | SEQ ID NO: 31779 |
| iPS:437164 | 21-225_217C6 | NA | TCCTATGAGCTGACACAGCCACCCTCGGTGTCAGTGTCCCAGGACAGAGACGGCCAGGATCACCTGCTCTGGAGATGCATTGCCAAAGCAATATGCTTATTGGTACCAGAAGCCAGGCCAGGCCCCAGTGCTGGTGATATATAAAGACAGTGAGAGCCCCTCAGGGATTCCTGAGCGATTCTCTGGCTCCGGCTCAGGGACAACAGTCACGTTGACCATCAGAGGAGTCCAGGCAGAAGACGAGGCTGACTATTACTGTCAATTAATAGTCAGCAGTGATACTTATGTCTTCGGAACTGGGACCAAGGTCACCGTCCTA | CAGGTGCAGCTGGTGGAGTCTGGGGGAGGCGTGGTCCAGCCTGGGAGGTCCCTGAGACTCTCCTGTGCAGCCTCTGGATTCACCTTCAGTAACTATGGCATGCACTGGGTCCGCCAGGCTCCAGGCAAGGGCTGGAGTGGGATGGCAATTATATGGTTTGATGAAGTGATGAATACTATGCAGACTCCGTGAAGGGCCGATTCACCATCTCCAGAGACAATTCCAAGAACACGATGTATCTGCAAATGAACAGCCTGAGAGGCCTATACACGGCTGTGTATTACTGTGCGAGAGGCCTATCTGTCTACTACTACGGTATGGACGTCTGGGGCCAAGGGACCACGGTCACCGTCTCCTCA |
| | | SEQ ID NO: 27775 | SEQ ID NO: 31781 |

FIGURE 50
(Continued)

| | | | | |
|---|---|---|---|---|
| iPS:437166 | 21-225_217G11 | AA | SYELTQPPSVSVSPGQTARITCSGDALPKQYAYW YQQKPGQAPVLVIYKDSERPSGIPERFSGSRSGTT VTLTIRGVQAEDEADYYCQLIVSSDTYVFGTGT KVTVL<br><br>SEQ ID NO: 27776 | QVQLVESGGGVVQPGRSLRLSCAASGFTFSNYGM HWVRQAPGKGLEWMAHWFDGSDEYYADSVKGRF TISRDNSKNTMYLQMNSLRAEDTAVYYCARGLSV YYYGMDVWGQGTTVTVSS<br><br>SEQ ID NO: 31782 |
| | | NA | TCCTATGAGCTGACACAGCCACCCTCGGTGTC AGTGTCCCAGGACAGGCCAGGATCACCT GCTCTGGAGATGCATTGCCAAAACAATATGCT TATTGGTACCAGCAGAAGCCAGGCCAGGCCCC AGTACTGGTGATATATAAAGACAGTGAGAGG CCCTCAGGGATCCCTGAGCGATTCTCTGGCTC CGGCTCAGGGACAACAGTCACGTTGACCGTCA GTGGAGTCCAGGCAGAAGACGAGGCTGACTA TTACTGTCAATTAGTGTACAGCAGTGATACTT ATGTCTTCGGAACTGGGACCAAGGTCACCGTC CTA<br><br>SEQ ID NO: 27777 | CAGGTGCAGTTGGTGGAGTCTGGGGGAGGCGTG GTCCAGCCTGGGAGGTCCCTGAGACTCTCCTGTG CAGCGTCTGGATTCACCTTCAGGAACTATGGCAT GCACTGGGTCCGCCAGGCTCCAGGCAAGGGGCT GGAGTGGGTGTCAATTATATGGTTTGATGGAAGT GATCAGTAGTACTATGCAGACTCCGTGAAGGGCCGAT TCACCATCTCCAGAGACAACAATTCCAAGAACACGCT GTATCTGCAAATGAACAGCCTGAGAGCCGAGGA CACGGCTGTATATTACTGTGCGAGAGGCCTCT GTCTACTACTACGGTATGGACGTCTGGGGCCAAG GGACCACGGTCACCGTCTCCTCA<br><br>SEQ ID NO: 31783 |
| | | AA | SYELTQPPSVSVSPGQTARITCSGDALPKQYAYW YQQKPGQAPVLVIYKDSERPSGIPERFSGSRSGTT VTLTIVSGVQAEDEADYYCQLVYSSDTYVFGTGT KVTVL<br><br>SEQ ID NO: 27778 | QVQLVESGGGVVQPGRSLRLSCAASGFTFRNYGM HWVRQAPGKGLEWVSIIWFDGSDQYYADSVKGRF TISRDNSKNTLYLQMNSLRAEDTAVYYCARGLSVY YYGMDVWGQGTTVTVSS<br><br>SEQ ID NO: 31784 |

FIGURE 50
(Continued)

| | | | | |
|---|---|---|---|---|
| iPS:437168 | 21-225_218G4 | NA | CAGTCTGTGTTGACGCAGCCGCCTCAGTGTCTGCGGCCCAGGACAGCAGCTCCAACATTGGGAATAATGCTCTGGAAGCAGCTCCAACATTGGGAATAATTATGTATCCTGGTACCAGCAGCTCCCAGGAACAGCCCCCAAACTCCTCTTTATGACAGTAATAAGGGACCCTCAGGGATTCCTGCCGATTCTCTGGCTCCAAGTCTGGCAGTCAGCCACCCTGGGCATCACCGGACTCCAGACTGGGGACGAGGCCGATTATTACTGCGGAACATGGGATAGCAGCCTGAATACTGTGGTATTCGGCGGAGGGACCAAGCTGACCGTCCTA | CAGGTGCAGCTGGTGGAGTCTGGGGGAGGCGTAGTCCAGCCTGGGAGGTCCCTGAGACTCTCCTGTGCAGCCTCTGGATTCACCTTCAGTAGCTATGGCTTGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGTCGAGGACACGGCTGTGTATTACTGTGCGAACTGTACTACTATTACTACGGTATGGACGTCTGGGGCCAAGGGACCACGGTCACCGTCTCCTCA |
| | | | SEQ ID NO: 27779 | SEQ ID NO: 31785 |
| | | AA | QSVLTQPPSVSAAPGQKVTISCSGSSSNIGNNYVSWYQQLPGTAPKLLLYDSNKRPSGIPARFSGSKSGTSATLGITGLQTGDEADYYCGTWDSSLNTVVFGGGTKLTVL | QVQLVESGGGVVQPGRSLRLSCAASGFTFSSYGLHWVRQAPGKGLEWVAVIWYDGSNKYYADSVKGRFTISRDNSKNTLYLQMNSLRVEDTAVYYCANWYYYYYGMDVWGQGTTVTVSS |
| | | | SEQ ID NO: 27780 | SEQ ID NO: 31786 |
| iPS:437170 | 21-225_218E5 | NA | TCCTATGAGCTGACACAGCCACCCTCGGTGTCAGTGTCCCCAGGACAGACGGCCAGGATCACCTGCTCTAGAGATGTATTGCCGAAGCAATATGCTTATTGGTACCAGCAGAAGCCAGGCCAGGCCCCAGTACTGGTGATATATAAAGACAGTGAGAGGCCCTCAGGGATCCCTGAGCGATTCTCTGGCTCCGGCTCAGGGACAACAGTCACGTTGACCATCAGAGGAGTCCAGGCAGAAGACGAGGCTGACTATTACTGTCAATTAGTTGTCAGCAGTGATACTTATGTCTTCGGAACTGGGACCAAGGTCACCGTCCTA | CAGGTGCAGTTGGTGGAGTCTGGGGGAGGCGTGGTCCAGCCTGGGAGGTCCCTGAGACTCTCCTGTGCAGCCTCTGGATTCACCTTCAGTAACTATGGCATGCACTGGGTCCGCCAGGCTCCAGGCAAGGGCTGGAGTGGATGGCAATTATATGGTTTGATGGAAGTGATGAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTATATTACTGTGCGAGAGGCCTATCTGTCTACTACTACGGTATGGACGTCTGGGGCCAAGGGACCACGGTCACCGTCTCCTCA |
| | | | SEQ ID NO: 27781 | SEQ ID NO: 31787 |

FIGURE 50
(Continued)

| | | | |
|---|---|---|---|
| iPS:437172 | 21-225_219A7 | AA | SYELTQPPSVSVSPGQTARITCSRDVLPKQYAYW YQQKPGQAPVLVIYKDSERPSGIPERFSGSRSGT T VTLTIRGVQAEDEADYYCQLVSSDTYVFGTGT KVTVL |
| | | | SEQ ID NO: 27782 |
| | | NA | CAGTCTGCCCTGACTCAGCCTGCCTCCGTGTCT GGGTCTCCTGGACAGTCGATCACCATCTCCTG CACTGGAACCAGCAGTGACGTTGGTGGTTATA ATTATGTCTCCTGGTACCAACAGCACCCAGGC AAAGCCCCCAAACTCATGATTTATGAGGTCAG AAATCGGCCCTCAAGTCTGGCAACACGGCCTCCTG CTGGCTCCAAGTCTGGCAACACGGCCTCCTG ACCATCTCTGGGCTCCAGGCTGAGGACGAGGC TGATTATTACTGCTGCTCATATACAAGGAGCA TCACTTGGGTGTTCGGCGGAGGGACCAAGTTG ACCGTCCTA |
| | | | SEQ ID NO: 27783 |
| | | AA | QSALTQPASVSGSPGQSITISCTGTSSDVGGYNY VSWYQQHPGKAPKLMIYEVRNRPSGVSNRFSGS KSGNTASLTISGLQAEDEADYYCCSYTRSITWVF GGGTKLTVL |
| | | | SEQ ID NO: 27784 |

| | |
|---|---|
| SYELTQPPSVSVSPGQTARITCSRDVLPKQYAYW YQQKPGQAPVLVIYKDSERPSGIPERFSGSRSGTT VTLTIRGVQAEDEADYYCQLVSSDTYVFGTGT KVTVL | QVQLVESGGGVVQPGRSLRLSCAASGFTFSNYGM HWVRQAPGKGLEWMAHWFDGSDEYYADSVKGRF TISRDNSKNTLYLQMNSLRAEDTAVYYCARGLSVY YYGMDVWGQGTTVTVSS |
| SEQ ID NO: 27782 | SEQ ID NO: 31788 |
| | CAGGTGCAGCTGGTGGAGTCTGGGGGAGGCGTG GTCCAGCCTGGGAGGTCCCTGAGACTCTCCTGTC CAGCGTCTGGATTCACCTTCAGTAACTACGGCAT GCACTGGGTCCGCCAGGCTCCAGGCAAGGGGCT GGAGTGGGTGGCAGTCATATGGTTTGATGGAAG TAATAATACTATGCAGAGACTCCGTGAAGGCCG ATTCACCATCTCCAGAGACAATTCCAAGAATATG CTGTATCTGCAAATGAACAGCCTGAGAGCCGAG GACACGGCTGTGTATTACTGTGCGAGGGGGACT GGAACCCGAGGGTATGGACGTCTGGGGCCAAG GGACCACGGTCACCGTCTCCTCA |
| | SEQ ID NO: 31789 |
| QSALTQPASVSGSPGQSITISCTGTSSDVGGYNY VSWYQQHPGKAPKLMIYEVRNRPSGVSNRFSGS KSGNTASLTISGLQAEDEADYYCCSYTRSITWVF GGGTKLTVL | QVQLVESGGGVVQPGRSLRLSCPASGFTFSHYGMH WVRQAPGKGLEWVAVIWYDGSNKYYADSVKGRF TISRDNSKNMLYLQMNSLRAEDTAVYYCARGDWN PEGMDVWGQGTTVTVSS |
| SEQ ID NO: 27784 | SEQ ID NO: 31790 |

FIGURE 50
(Continued)

| | | | | |
|---|---|---|---|---|
| iPS:437182 | 21-225_221H2 | NA | CTGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAACACCAGGCAAAGCCCCCAAACTCATGATTTCTGAGGTCAGGAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAACTCATATACACGCAGCATCACTTGGGTGTTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTCAGCGTCTGGATTCACCTTCAGTCACTATGGCATGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGCATCTGCAAATGAACAGCCTGAGAGCCGAGGACACGGCTGTGTATTACTGTGCGAGGGGGACTGGAACCCGAGGGTCACCGTCTCCTCA |
| | | | SEQ ID NO: 27785 | SEQ ID NO: 31791 |
| | | AA | LSALTQPASVSGSPGQSITISCTGTSSDVGGYNYVSWYQQHPGKAPKLMISEVRNRPSGVSNRFSGSKSGNTASLTISGLQAEDEADYYCNSYTRSITWVFGGGTKLTVL | QVQLVESGGGVVQPGRSLRLSCAASGFTFSHYGMHWVRQAPGKGLEWVAVIWYDGSNKYYADSVKGRFTISRDNSKNTLHLQMNSLRAEDTAVYYCARGDWNPEGMDVWGQGTTVTVSS |
| | | | SEQ ID NO: 27786 | SEQ ID NO: 31792 |
| iPS:437184 | 21-225_221G4 | NA | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAACACCAGGCAAAGCCCCCAAACTCATGATTTATGAGGTCAGGAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAACTCATATACACGCAGCATCACTTGGGTGTTCGGCGGAGGGACCAAGCTGACCGTCCTA | CAGGTGCAGCTGGTGGAGTCTGGGGGAGGCGTGGTCCAGCCTGGGAGGTCCCTGAGACTCTCCTGTCAGCGTCTGGATTCACCTTCAGTCACTACTGCATGCACTGGGTCCGCCAGGCTCCAGGCAAGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGCATCTGCAAATGAACAGCCTGAGAGCCGAGGACACGGCTGTGTATTACTGTGCGAGGGGGGACTGGAACCCCGAGGGTATGGACGTCTGGGGCCAAGGGACCCTGGTCACCGTCTCCTCA |
| | | | SEQ ID NO: 27787 | SEQ ID NO: 31793 |

FIGURE 50
(Continued)

| | | AA | QSALTQPASVSGSPGQSITISCTGTSSDVGGYNY VSWYQQHPGKAPKLMIYEVRNRPSGVSNRFSGS KSGNTASLTISGLQAEDEADYYCNSYTRSITWVF GGGTKLTVL<br>SEQ ID NO: 27788 | QVQLVESGGGVVQPGRSLRLSCAASGFTFSHYGM HWVRQAPGKGLEWVAVIWYDGSNKYYADSVKGR FTISRDNSKNTLHLQMNSLRAEDTAVYYCARGDW NPEGMDVWGQGTSVTVSS<br>SEQ ID NO: 31794 |
|---|---|---|---|---|
| iPS:437186 | 21-225_224H2 | NA | TCCTATGAGCTGACTCAGCCATCCTCAGTGTC CGTGTCCCCAGGACAGACAGCCAGCATCACCT GCTCTGGAGATAATTTGGGGGTTAAATATACT TACTGGTATCAGCAGAAGCCAGGCCAGTCCC TGTGCTAGTCGTCTATCAAGATAGCAAGCGGC CCTCAGGGATCCCTGAGCGATTCTCTGGCTCC AACTCTGGGAACACAGGCTACTCTGACCATCAG CGGGACCCAGGCTGTGGGACAGCAGCACTGTGTA ACTGTCAGGCGTGGGAGGGACCAAGCTGACCGTCCTA<br>SEQ ID NO: 27789 | CAGGTACAGCTGCAGCAGTCAGGTCCAGGACTG GTGAAGCCCTCGCAGACCCTCACTCAGCTGTG ACATCTCCGGGACAGTGTCTCTAGCAACAGTGC TGCTTGGAACTGGATCAGGCAGTCCCCATGCGA GGCCTTGAGTGGCTGGAAGGACATACTACAGG TCCAAGTGGTATAATGATTATGCAGTATCTGTGA AAAGTCGAGTAACCATCAACCCAGACACATCCA AGAACCAGTTCTCCCTGCAGCTGAACTCTGTGAC TCCCGAGGACACGGCTGTGTATTGTAGTAGTACCAGCT GAGGGGGCCTAGGATATGTAGTAGTACCAGCT GCTATGAGGCTGGTTGACCCCGTCCTCA GAACCCTGGTCACCGTCTCCTCA<br>SEQ ID NO: 31795 |
| | | AA | SYELTQPSSVSVSPGQTASITCSGDNLGVKYTYW YQQKPGQSPVLVVYQDSKRPSGIPERFSGSNSGN TATLTISGTQAMDEADYYCQAWDSSTVFGGG TKLTVL<br>SEQ ID NO: 27790 | QVQLQQSGPGLVKPSQTLSLTCDISGDSVSSNSAA WNWIRQSPSRGLEWLGRTYYRSKWYNDYAVSVK SRVTINPDTSKNQFSLQLNSVTPEDTAVYYCAREGG LGYCSSTSCYGGWFDPWGQGTLVTVSS<br>SEQ ID NO: 31796 |

FIGURE 50
(Continued)

| | | | |
|---|---|---|---|
| iPS:437188 | 21-225_224B11 | NA | CAGTCTGTGCTGACGCAGCCGCCCTCAGTGTCTGGGGCCCCAGGACAGAGGGTCACCATCTCCTGCACTGGGAGCAGCTCCAACATGGGGCAGGTTATGATGTACACCTGGTACCAGCAGCTTCCAGGAACAGCCCCCAAACTCCTCATCTTTGGTAACAGCAATCGGCCCTCAGGGGTCCCTGACCGATTCTCTGGCTCCAAGTCTGGCACCTCAGCCTCCCTGGCCATCACTGGGCTCCAGGCTGAGGATGAGGCTGATTATTACTGCCAGTCCTATGACAACAGCCTGAGTGGTGTTCGGCGGAGGGACCAAGCTGACCGTCCTA<br>SEQ ID NO: 27791 | CAGGTACACCTGGTGCAGTCTGGGGCTGAGGTGAAGAAGCCTGGGGCCTCAGTGAAGGTCTCCTGCAAGGCTTCTGGATACACCTTCACCGGCTACTATATACACTGGGTGCGACAGGCCCCTGGACAAGGCTTGAGTGGATGGGATGGATCAACAGAAGCTAAAATGGTGGCACAAACTATGACCAGGACGCGTCCATCAGCAGGGTCACCATGACCAGGGACACGTCCATCAGCACCACCTACATGGAGCTGAGCAGGCTGAGATCTGACGACACGGCCGTGTATTACTGCGCGAGAGAGCGTTTGATTACTTCTACTACTACGCTATGGACGTCTGGGGCCACGGGACCACGGTCACCGTCTCCTCA<br>SEQ ID NO: 31797 |
| iPS:437190 | 21-225_225A9 | AA<br>NA | QSVLTQPPSVSGAPGQRVTISCTGSSSNIGAGYDVHWYQQLPGTAPKLLIFGNSNRPSGVPDRFSGSKSGTSASLAITGLQAEDEADYHCQSYDNSLSGVFGGGTKLTVL<br>SEQ ID NO: 27792<br><br>CAGGTGCAGCTGGTGGAGTCTGGGGGAGGCGTGGTCCAGCCTGGGGGGTCCCTGAGACTCTCCTGTGCAGCGTCTGGATTCACCTTCAGTACCTATGGCATGCACTGGGTCCGCCAGGCTCCAGGCAAGGGGCTGGAGTGGGTGGCAGTTATATGGTATGATGGAAGTAATAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATAACCACTATTGTAGTAGTACCAGCTGCCCCATACTACTACTTCGGTATGGACGTCTGGGGCCAAGGGACCACGGTCACCGTCTCCTCA | QVHLVQSGAEVKKPGASVKVSCKASGYTFTGYYIHWVRQAPGQGLEWMGWINPKNGGTNYAQKFQGRVTMTRDASISTTYMELSRLRSDDTAVYYCARGAFDYFYYYAMDVWGHGTTVTVSS<br>SEQ ID NO: 31798 |

FIGURE 50
(Continued)

| | | | SEQ ID NO: 27793 | SYELTQPPSVSVSPGQTASITCSGDKLGNKYACW YQQKPGQSPVLVIYQDSKRPSGIPERFSGSNSGN TATLTISGTQAMDEADYYCQAWDSNTACVFGT GTKVTVL | SEQ ID NO: 31799 | QVQLVESGGGVVQPGGSLRLSCAASGFTFSTYGMH WVRLAPGKGLEWVAVIWYDGSNKYYADSVKGRF TISRDISQNTLYLQMNSLRAEDTAVYYCARDNHYC SSTSCSPYYYYFGMDVWGQGTTVTVSS |
| | | AA | | | | |
| | | | SEQ ID NO: 27794 | TCCTATGACCTGACTCAGCCACCCTCAGTGTC CGTGTCCCCAGGACAGACAGCCAGCATCACCT GCTCTGGAGATAAATTTGGGGACAAGCATCACCT TGCTGGTATCAGCAGAAGCCAGGCCAGTCCC TGTACTGGTCATGTATCAAGATCGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGGACAGCAGAACTGCTGTG GTATTCGGCGGAGGGACCAAGCTGACCGTCCT A | SEQ ID NO: 31800 | CAGGTGCAGTTGGTGGAGTCTGGGGGAGGCGTG GTCCAGCCTGGGAGGTCCCTGAGACTCTCCTGTG AAGCGTCTGGATTCATCTTCAGTAGCTATGGCAT GCACTGGGTCCGCCAGGCTCCAGGCAAGGGGCT GGAGTGGGTGGCAGTTATGTGGTATGATGGGT AATAAAGACTATGCAGACTCCGTGAAGGGCCGA TTCACCATCTCCAGAGACAATCCAAGAACACGC TGTATCTGCAAATGAACAGCCTGAGAGCCGAGG ACACGGCTGTGTATTACTGTGCGAGAGATCGGGA ATATTGTACTAGTACCAGCTGCCCTTACTACTAC TACTACGGTATGGACGTCTGGGGCCAAGGGACC ACGGTCACCGTCTCCTCA |
| | | NA | | | | |
| iPS:437192 | 21-225_225E9 | | SEQ ID NO: 27795 | SYDLTQPPSVSVSPGQTASITCSGDNLGNRYAC WYQQKPGQSPVLVMYQDRKRPSGIPERFSGSNS GNTATLTISGTQAMDEADYYCQAWDSRTAVVF GGGTKLTVL | SEQ ID NO: 31801 | QVQLVESGGGVVQPGRSLRLSCEASGFIFSSYGMH WVRQAPGKGLEWVAVMWYDGGNKDYADSVKGR FTISRDNSKNTLYLQMNSLRAEDTAVYYCARDREY CTSTSCPYYYYYGMDVWGQGTTVTVSS |
| | | AA | | | | |
| | | | SEQ ID NO: 27796 | | SEQ ID NO: 31802 | |

FIGURE 50
(Continued)

| | | | |
|---|---|---|---|
| iPS:437194 | 21-225_226B2 | NA | TCCTATGAGCTGACTCAGCCACCCTCAGTGTC CGTGTCCCCAGGACAGACAGCCAGCATCACCT GCTCTGGAGATACATTGGGGGTAAATATGCT TGGTGGTATCAGCAGAGGCCAGGCCAGTCCCC TGTGCTGGTCATCTATCAAGATGCAAGCGGC CCTCAGGGATCCCTGAGCGATTCTCTGGCTCC AGCTCTGGGAACACAGCCACTCTGACCATCAG CGGGACCCAGGCTATGGATGAGGCTGACTATT ACTGTCAGGCGTGGGACAACGGCGCTGCGGTT TTCGGCGGAGGGACCAAGCTGACCGTCCTA <br><br>SEQ ID NO: 27797 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTTTA TGCACTGGGTGCGACAGGCCCCTGGACAAGGGC TTGAGTGGATGGGATGGATCAACCCTAACAGTGG TGACACAAACTATGCACAGAAGTTTCAGGGCAG GGTCACCATGACCAGGGACACGTCCCTAACAC AGCCTACATGGAGCTGAGCAGGCTGAGATCTGA CGACACGGCCATTTATTACTGTGCGAGAGGGACT TACTATGGTTCGGGGAGTTATTTTAACGAACTTG ACTCCTGGGGCCAGGGAACCCTGGTCACCGTCTC CTCA <br><br>SEQ ID NO: 31803 |
| | | AA | SYELTQPPSVSVSPGQTASITCSGDTLGGKYAW WYQQRPGQSPVLVIYQDRKRPSGIPERFSGSSSG NTATLTISGTQAMDEADYYCQAWDNGAAVFGG GTKLTVL <br><br>SEQ ID NO: 27798 | QVQLVQSGAEVKKPGASVKVSCKASGYTFTGYFM HWVRQAPGQGLEWMGWINPNSGDTNYAQKFQGR VTMTRDTSLNTAYMELSRLRSDDTAIYYCARGTYY GSGSYFNELDSWGQGTLVTVSS <br><br>SEQ ID NO: 31804 |
| iPS:437196 | 21-225_226B7 | NA | TCCTTGAGCTGACACAGCCACCTCGGTGTC AGTGTCCCCAGGACAGACGGCCAGGATCACCT GCTCTGGAGATGCATTGCCAAGGCATTATGTT TATTGGTACCAGCAGCAGAACCCAGGCCAGGAC TGTGCTGGTGATATATAAAGACAGTGAGAGGC CCTCAGGGATCCCTGAGCGATTCTCTGGCTCC AGCTCAGGGACAACAGTCACGTTGACCATCAG TGGAGTCCAGGCAGAAGACGAGAGGCTGACTATT ACTGTCAATCAGCAGCAGCAGAGTGGTCACCTAT GTCTTCGGAACTGGGACCAAGGTCACCGTCCT A <br><br>SEQ ID NO: 27799 | CAGGTGCAGCTGCAGTCTGGGGCTGAGGTG AAGAAGCCTGGGGCCTCAGTGAAGGTCTCCTGC AAGGCTTCTGGATACACCTTCACCGGCTACTATA TGCACTGGGTGCGACAGGCCCCTGGACAAGGAC TTGAGTGGATGGGATGGATCAACCCTAACAGTGG AGGCACAAACTATGCACAGAAGTTTCAGGACAG GGTCACCATGACCAGGGACACGTCCATCAGCAC AGCCCACATGGAGCTGAGCAGGCTGAGATCTGA CGACACGGCCGTGTATTATTGTGCGAGAGGATAT TACTATGGTTCGGGGAGTTATTATAACTGGTTCG ACTCCTGGGGCCAGGGAACCCTGGTCACCGTCTC CTCA <br><br>SEQ ID NO: 31805 |

FIGURE 50
(Continued)

| | | | |
|---|---|---|---|
| iPS:437198 | 21-225_226F8 | AA | SFELTQPPSVSVSPGQTARITCSGDALPRHYVYW YQQNPGQAPVLVIYKDSERPSGIPERFSGSSSGTT VTLTISGVQAEDEADYYCQSADSSGTYVFGTGT KVTVL<br>SEQ ID NO: 27800 | QVQLVQSGAEVKKPGASVKVSCKASGYTFTGYYM HWVRQAPGQGLEWMGWINPNSGGTNYAQKFQDR VTMTRDTSISTAHMELSRLRSDDTAVYYCARGYYY GSGSYYNWFDSWGQGTLVTVSS<br>SEQ ID NO: 31806 |
| | | NA | CAGTCTGTGCTGACGCAGCCGCCCTCAGTGTC TGGGGCCCCAGGGCAGAGGGTCACCATCTCCT GCACTGGGAGCAGCTCCAACATCGGGGCAGG TTATGATGTACACTGGTACCAGCAGCTTCCAG GAACAGCCCCCAAACTCCTCATCTATGGTAAC AGCAATCGGCCCTCAGGGGTCCCTGACCGATT CTCTGGCTCCAAGTCTGACACCTCAGCCTCCCT GGCCATCACTGGGCTCCAGGCTGAGGATGAGG CTGATTATTACTGCCAGTCCTATGACAACAGC CTGAGTGGTGTGTTCGGCGGAGGGACCAAGCT GACCGTCCTA<br>SEQ ID NO: 27801 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGGC TTGAGTGGATGGGATGGATCAACCCTAACAGTGG TGGCACAAACTATGCACAGAAGTTTCAGGGCAG GGTCACCATGACCAGGGACACGTCCATCAGCAC AGCCTACATGGAGCTGAGCAGACTGAGATCTGA CGACACGGCCGTGTATTACTGTGCGAGAGGAGC GTTTGATTACTACTACTACTACGCTTTGGACGTCT GGGGCCAAGGGACCACGGTCACCGTCTCCTCA<br>SEQ ID NO: 31807 |
| | | AA | QSVLTQPPSVSGAPGQRVTISCTGSSSNIGAGYD VHWYQQLPGTAPKLLIYGNSNRPSGVPDRFSGS KSDTSASLAITGLQAEDEADYYCQSYDNSLSGV FGGGTKLTVL<br>SEQ ID NO: 27802 | QVQLVQSGAEVKKPGASVKVSCKASGYTFTGYYIH WVRQAPGQGLEWMGWINPNSGGTNYARKFQGRV TMTRDTSISTAYMELSRLRSDDTAVYYCARGAFDY YYYYALDVWGQGITVTVSS<br>SEQ ID NO: 31808 |

FIGURE 50
(Continued)

| | | | |
|---|---|---|---|
| iPS:437200 | 21-225_226A10 | NA | TCCTATGAGCTGACTCAGCCACCCTCAGTGTC CGTGTCCCCAGGACAGACAGCCAGCATCACCT GCTCTGGAGATACATTGGGGGGTAAATATGCT TGGTGGTATCAGCAGAAGCCAGGCCAGTCCCC TGTGCTGGTCATCTATCAAGATGCAAGCGGC CCTCAGGGATCCCTGAGCGATTCTCTGGCTCC AGCTCTGGGAACACAGCCACTCTGACCATCAG CGGGACCCAGGCTATGGATGAGGCTGACTATT ACTGTCAGGCGTGGGACAACGGCGCTGCGGTT TTCGGCGGAGGGACCAAGCTGACCGTCCTA<br/><br/>SEQ ID NO: 27803 | CAGGTGCAACTGGTGCAGTCTGGGGCTGAGGTG AAGAAGCCTGGGGCCTCAGTGAAGGTCTCCTGC AAGGCTTCTGGATACACCTTCACCGGCTACTTTA TGCACTGGGTGCGACAGGCCCCTGGACAAGGGC TTGAGTGGATGGGTTGGATCAACCCTAACAGTGG TGACACAAACTATGCACAGAAGTTTCAGGGCAG GGTCACCATGACCATGGAGTCGAGCAGGTCCCTGAGCAC AGCCTACATGGAGCTGAGCAGGCTGAGATCTGA CGACACGGCCATTTATTACTGTGCGAGAGGACT TACTATGTTCGGGGAGTTATTTTAACGAACTTG ACTCCTCGGGGCCAGGGAACCCTGGTCACCGTCTC CTCA<br/><br/>SEQ ID NO: 31809 |
| | | AA | SYELTQPPSVSVSPGQTASITCSGDTLGGKYAW WYQQKPGQSPVLVIYQDRKRPSGIPERFSGSSSG NTATLTISGTQAMDEADYYCQAWDNGAAVFGG GTKLTVL<br/><br/>SEQ ID NO: 27804 | QVQLVQSGAEVKKPGASVKVSCKASGYTFTGYFM HWVRQAPGQGLEWMGWINPNSGDTNYAQKFQGR VTMTRDTSLSTAYMELSRLRSDDTAIYYCARGTYY GSGSYFNELDSWGQGTLVTVSS<br/><br/>SEQ ID NO: 31810 |
| iPS:437202 | 21-225_227D3 | NA | CAGTCTGTGCTGACGCAGCCGCCCTCAGTGTC TGGGGCCCCAGGGCAGAGGGTCACCATCTCCT GCACTGGGAGCAGCTCCAACATCGGGGCAGG TTATGATGTACACTGGTACCAGCAGTTCCAG GAACAGCCCCCAAACTCCTCATCTATGGTAAC AGCAATCGGCCCTCAAGGGTCCCTGACCGATT CTCTGGCTCCAAGTCTGACACCTCAGCTCCCT GGCCATCACTGGGCTCCAGGCTGAGGATGAGG CTGATTATTACTGCCAGTCCTATGACAACAGC CTGAGTGGTGTGTTCGGCGGAGGGACCAAGCT GACCGTCCTA<br/><br/>SEQ ID NO: 27805 | CAGGTGCAATTGGTGCAGTCTGGGGCTGAGGTGA AGAAGCCTGGGGCCTCAGTGAAGGTCTCCTGCA AGGCTTCTGGATACACCTTCACCGGCTACTATAT GCACTGGGTGCGACAGGCCCCTGGACAAGGGCT TGAGCGGATGGGATGGATCAACCCTAAGAGTGG TGGCACAAACTTGCACAGAAGTTTCAGGGCAG GGTCACCATGACCAGGGACACGTCCATCAGCAC AGCCTACATGAACTGAGCAGGCTGAGATCTGA CGAACACGGCCGTGTATTACTGCGCGAGAGGAGC GTTTGATTACTTCTACTACTACGGTATGGACGTCT GGGGCCAAGGGACCACGGTCACCGTCTCCTCA<br/><br/>SEQ ID NO: 31811 |

FIGURE 50
(Continued)

| | | | |
|---|---|---|---|
| iPS:437204 | 21-225_227E5 | AA | QSVLTQPPSVSGAPGQRVTISCTGSSSNIGAGYD VHWYQQLPGTAPKLLIYGNSNRPSGVPDRFSGS KSDTSASLAITGLQAEDEADYYCQSYDNSLSGV FGGGTKLTVL<br>SEQ ID NO: 27806 | QVQLVQSGAEVKKPGASVKVSCKASGYTFTGYYM HWVRQAPGQGLERMGWINPKSGGTNFAQKFQGR VTMTRDTSISTAYMELSRLRSDDTAVYYCARGAFD YFYYYGMDVWGQGTTVTVSS<br>SEQ ID NO: 31812 |
| | | NA | TCCTATGAGCTGACTCAGCCACCCTCAGTGTC CGTGTCCCAGGACAGAGCCAGCATCACCT GCTCTGGAGATATAAATTGGGGAAAAATATGCT TGCTGGTATCAGCAGAAGCCAGGCCAGTCCC TGTGCTGGTCATCTATCAAGATAGGAAGCGGC CCTCAGGGATCCCTGAGCGATTCTCTGGCTCC AACTCTGGGAACAAAGCCACTCTGACCATCAG CGGGACCCAGGCTATGATGAGGCTGACTATT ACTGTCAGGGCGTGGGTCAACAACACTATGATA TTCGGCGGAGGGACCAAGCTGACCGTCCTA<br>SEQ ID NO: 27807 | GAGGTGCAGCTGTTGGAGTCTGGGGGAGGCTTG GTACAGCCTGGAGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AGCACATACTACGCAGACTCCGTGAAGGGCCGG TTCACCATCTCCAGAGACAATTCCAAGAACACGC TGTGTCTGCAAATGAACAGCCTGAGAGCCGAGG ACACGGCCGTATATTACTGTGCGAAAGAATATTG TGGTGGTGACTGCTATTCCCCTTACTACTACTACT ACGGTATGGACGTCTGGGGCCAAGGGACCACGG TCACCGTCTCCTCA<br>SEQ ID NO: 31813 |
| | | AA | SYELSQPPSVSVSPGQTASITCSGDKLGEKYACW YQQKPGQSPVLVIYQDRKRPSGIPERFSGSNSGN KATLTISGTQAMDEADYYCQAWVNNTMIFGGG TKLTVL<br>SEQ ID NO: 27808 | EVQLLESGGGLVQPEGSLRLSCAASGFTFSSYAMS WVRQAPGKGLEWVSAISGSGGSTYYADSVKGRFTI SRDNSKNTLCLQMNSLRAEDTAVYYCAKEYCGGD CYSPYYYYGMDVWGQGTTVTVSS<br>SEQ ID NO: 31814 |

FIGURE 50
(Continued)

| | | | |
|---|---|---|---|
| iPS:437208 | 21-225_227C10 | NA | CAGTCTCTGCTGACGCAGCCGCCCTCAGTGTC TGGGGCCCCAGGGAGCAGAGGGTCACCATCTCCT GCACTGGGAGCAGCTCCAACATGGGCAGG TTATGATGTACACTGGTACCAGCAGCTTCCAG GAACAGCCCCCAAACTCCTCATCTATGGTAAC AGCAATCGGCCCTCAGGGGTCCCTGACCGATT CTCTGGCTCCAAGTCTGACACCTCAGCTCCCT GGCCATCACTGGGCTCCAGGCTGAGGATGAGG CTGATTATTACTGCCAGTCCTATGACAACAAC CTGAGTGGTGTGTTCGGCGGAGGGACCAAGCT GACCGTCCTA<br>SEQ ID NO: 27809 | CAGGTGCAATTGGTGCAGTCTGGGGCTGAGGTGA AGAAGCCTGGGGCCTCAGTGAAGGTCTCCTGCA AGGCTTCTGATACACCTTCACCGGCTACTATAT GCACTGGGTGCGACAGGCCCCTGGACAAGGGCT TGAGCGGATGGGATGGATCAACCCTAAGAGTGG TGGCACAAACTATGCACAGAAGTTTCAGGGCAG GGTCACCATGACCAGGGACACGTCCATCAGCAC AGCCTACATGGAGCTGAGCAGGCTGAGATCTGA CGACACGGCCGTGTATTACTGCGCGAGAGGAGC GTTTGATTACTTCTACTACGGTATGGACGTCT GGGGCCAAGGGACCACGGTCACCGTCTCCTCA<br>SEQ ID NO: 31815 |
| | | AA | QSVLTQPPSVSGAPGQRVTISCTGSSSNIGAGYD VHWYQQLPGTAPKLLIYGNSNRPSGVPDRFSGS KSDTSASLAITGLQAEDEADYYCQSYDNNLSGV FGGGTKLTVL<br>SEQ ID NO: 27810 | QVQLVQSGAEVKKPGASVKVSCKASGYTFTGYYM HWVRQAPGQGLERMGWINPKSGGTNYAQKFQGR VTMTRDTSISTAYMELSRLRSDDTAVYYCARGAFD YFYYYGMDVWGQGTTVTVSS<br>SEQ ID NO: 31816 |
| iPS:437210 | 21-225_227E12 | NA | TCCTATGAACTGACTCAGCCACCCTCAGTGTC CGTGTCCCCAGGACAGACAGCCAGCATCACCT GCTCTGGAGATAAATTGGGGGATAAATATGTT TGTTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTATGGATGAGGCTGACTATT ACTGTCAGGCGTGGAACAGCAGCAATGTGGTA TTCGGCGGAGGGACCAAGCTGACCGTCCTA<br>SEQ ID NO: 27811 | CAGATCACCCTGAAGGAGTCTGGTCCTACGCTGG TGAAACCCACACAGACACCCTCAGCTGACCTGCAC CTTCTCTGGTTTCTCACTCAGCACTAGTGGAGTG GGTGTGGGCTGGATCCGTCAGCCCCCAGGAAAG GCCCTGGAGTGCTTCACTCATTATTGGAATG ATGATAAGGTCTACAGCCCATCTCTGAAGAGCAG GCTCACCATCACCAAGTACACCTCCAAAAACCAG GTGGTCCTTACAATGACCAACATGGACCCTGTGG ACACAGCCACATATTACTGTGCACACAGGGGAC AGCAGTCGCCCTGACTACTGGGGCCAGGAA CCCTGGTCACCGTCTCCTCA<br>SEQ ID NO: 31817 |

FIGURE 50
(Continued)

| | | | |
|---|---|---|---|
| iPS:437214 | | AA | SYELTQPPSVSVSPGQTASITCSGDKLGDKYVCW YQQKPGQSPVLVIYQDSKRPSGIPERFSGSNSGN TATLTISGTQAMDEADYYCQAWNSSNVFGGG TKLTVL<br>SEQ ID NO: 27812 | QITLKESGPTLVKPTQTLTLTCTFSGFSLSTSGVGVG WIRQPPGKALECLSLIYWNDDKVYSPSLKSRLTITK YTSKNQVVLTMTNMDPVDTATYYCAHRGQQLAL DYWGQGTLVTVSS<br>SEQ ID NO: 31818 |
| | 21-225_48B12 | NA | TCCTATGAGCTGACACAGCCACCCTCGGTGTC AGTGTCCCAGGACAAACGGCCAGGATCACCT GCTCTGGAGATGCATTGCCAAAAAATATGCT TATTGGTACCAGCAGAAGTCAGGCCAGGCCCC TGTGCTGGTCATCTATGAGGACAGCAAACGAC CCTCCGGGATCCCTGAGAGATTCTCTGGCTCC AGTCAGGGACAATGGCCACCTTGACTATCAG TGGGGCCCAGGTGGAGGATGAAGCTGACTACT ACTGTAACTCAACAGACAGCAGTGGTAATCAT GTGGTATTCGGGGGAGGGACCAAGCTGACCGT CCTA<br>SEQ ID NO: 27813 | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAACTGGGTCCGCCAGGCTCCAGGGAAGGGGCT GGAGTGGGTCTCAGCTATTAGTGGTCGTGGTGGT AACACATTCTACGCAGACTCCGTGAAGGGCCGT TCACCATCTCCAGAGACAATTCCAAGAACACGCT GTATCTGCAAATGAACAGCCTGAGAGCCGAGGA CACGGCCGTATATTACTGTGCGAAAAGAGAC GTATAACTGAACTACGAAGGGTTTGACTACTGG GGCCAGGGAACCCTGGTCACCGTCTCCTCA<br>SEQ ID NO: 31819 |
| | | AA | SYELTQPPSVSVSPGQTARITCSGDALPKKYAYW YQQKSGQAPVLVIYEDSKRPSGIPERFSGSSSGT MATLTISGAQVEDEADYYCNSTDSSGNHVFGG GTKLTVL<br>SEQ ID NO: 27814 | EVQLLESGGGLVQPGGSLRLSCAASGFTFSSYAMN WVRQAPGKGLEWVSAISGRGGNTFYADSVKGRFTI SRDNSKNTLYLQMNSLRAEDTAVYYCAKRETYNW NYEGFDYWGQGTLVTVSS<br>SEQ ID NO: 31820 |

FIGURE 50
(Continued)

| | | | |
|---|---|---|---|
| iPS:437216 | 21-225_51D5 | NA | GACATCCAGATGACCCAGTCTCCATCCTCCCT GTCTGCATCTGTAGGAGACAGAGTCACCATCA CTTGTCGGGCGAGTCAGGGCATTAACAATTAT TTAGCCTGGTTTCAGCAGAAACCAGGGAAGC CCCTAAGTCCCTGATCTATGCTGCATCCAGTT GCGAAGTGGGGTCCCATCACAGTTCAGCGGCA GTGGATCTGGAACAGATTCATTCTCACCATC AGCAGCCTGCAGCCTGAAGATTTTGCAACTTA TTACTGCCAACAGTATTATAGTTACCATTCAC TTTCGGCCCTGGGACCAAAGTGGATATCAAA<br>SEQ ID NO: 27815 | GAGGTGCAGTTGTTGGAGTCTGGGGGAGGCTTGG TACAGCCTGGGGGGTCCCTGAGACTCTCCTGTGC AGCCTCTGGATTCACCTTTAGCAGCAGTATGTCATG AGCTGGGTCCGCCAGACTCCAGGGAAGGGGCTG GAGTGGGTCTCAACTATGAGTGGTAGTGGTGGTC GCACATACTACGCAGACTCCGTGAACGGCCGATT CACCGTCTCCAGAGACAATTCCAAGAACACGCTG TATTTGCAAATGAGCAGCCTGAGAGCCGAGGAC ACGGCCGTATATTACTGTGCGCGGGTGACTGCTT TGACTACTGGGGCCAGGGAACCCTGGTCACCGT CTCCTCA<br>SEQ ID NO: 31821 |
| | | AA | DIQMTQSPSSLSASVGDRVTITCRASQGINNYLA WFQQKPGEAPKSLIYAASSLRSGVPSQFSGSGSG TDFILTISSLQPEDFATYYCQQYYSYPFTFGPGTK VDIK<br>SEQ ID NO: 27816 | EVQLLESGGGLVQPGGSLRLSCAASGFTFSSYVMS WVRQTPGKGLEWVSTMSGSGGRTYYADSVNGRFT VSRDNSKNTLYLQMSSLRAEDTAVYYCARVTAFD YWGQGTLVTVSS<br>SEQ ID NO: 31822 |
| iPS:437220 | 21-225_55H6 | NA | GACATCCAGATGACCCAGTCTCCATCCTCCCT GTCTGCATCTGTAGGAGACAGAGTCACCATCA CTTGCCGGGCAAGTCAGGGCATTAGAAACGAT TTAGGCTGGTATCAGCAGAAACCAGGGAAAG CCCCTAAGCGCCTGATCTATGGTGCATCCAGT TTGCAAAGTGGGGTCCCATCAAGATTCAGCGG CAGTGGATCTGGGACAGATTCACTCTCACAA TCAGCAGCCTGCAGCCTGAAGATTTTGCAGCT TATTACTGTCTACAGCGTGATAGTAGTTACCCGTTC ACTTTCGGCGGAGGGACCAAGGTGGAGATCA AA<br>SEQ ID NO: 27817 | GAGGTGCACCTGGTGGAGTCTGGGGGAGGCTG GTCAAGCCTGGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTGGTAGTAGTACT TACATATACTACGCAGACTCAGTGAAGGCCGAT TCACCATCTCCAGAGACAACAGCCAAGAACTACT GTATCTGCAAATGAACAGCCTGAGAGCCGAGA CACGGCTGTGTATTACTGTGCGAGAACCCTGGGGTC TTTGACTACTGGGGCCAGGGAACCCTGGTCACCG TCTCCTCA<br>SEQ ID NO: 31823 |

FIGURE 50
(Continued)

| | | AA | DIQMTQSPSSLSASVGDRVTITCRASQGIRNDLG WYQQKPGKAPKRLIYGASSLQSGVPSRFSGSGS GTEFTLTISSLQPEDFAAYYCLQRDSYPFTFGGG TKVEIK SEQ ID NO: 27818 | EVHLVESGGGLVKPGGSLRLSCAASGFTFSSYSMN WVRQAPGKGLEWVSSISGSSTYIYYADSVKGRFTIS RDNAKNSLYLQMNSLRAEDTAVYYCARTGVFDY WGQGTLVTVSS SEQ ID NO: 31824 |
|---|---|---|---|---|
| iPS:437224 | 21-225_56H1 | NA | GACATCCAGATGACCCAGTCTCCATCCTCACT GTCTGCATCTGTAGGAGACAGAGTCACCATCA CTTGTCGGGCGAGTCAGGGCATTAGCAATGAT TTAGCCTGGTTTCAGCAGAAACCAGGGAAAGC CCCTCAGTCCCTGATGTCTGCTGCATCCGGTTT GCAAAGTGGGGTCCCTTCAAGTTCAGCGGCA GTGGATCTGGGACAGATTTCACTCTCACCATC AGCAGCCTGCAGCCTGAAGATTTTGCAACTTA CTACTGTCAACAATATCAGAATTACCCCTTCA CTTTCGGCCCTGGGACCAAAGTGGATATCAAA SEQ ID NO: 27819 | GAGGTGCAGCTGGTGGAATCTGGGGGAGGCCTG GTCAAGCCGGGGGGGTCCCTGAGACTCTCCTGTG CAGCCTCTGGATTCACCTTCAGTAGTTAACTATAGAAT GAACTGGGTCCGCCAGGGTCCAGGGAAGGGCT GGAGTGGATCTCATCCATTAGTGGTAGTAGTACT GACATATACTACGCAGACTCAGTGAAGGGCCGA TTCACCATCTCCAGAGACAACGCCAAGAACTCAC TGTATCTGCAAATGAACAGCCTGAGAGCCGAGG ACACGGCTGTGTATTACTGTGCGAGAGTGGCCTC CTTTGACTACTGGGGCCAGGGAACCCTGGTCACC GTCTCCTCA SEQ ID NO: 31825 |
| | | AA | DIQMTQSPSSLSASVGDRVTITCRASQGISHYLA WFQQKPGKAPQSLMSAASGLQSGVPSKFSGSGS GTDFTLTISSLQPEDFATYYCQQYQNYPFTFGPG TKVDIK SEQ ID NO: 27820 | EVQLVESGGGLVKPGGSLRLSCAASGFTFSNYRMN WVRQPGKGLEWISSISGSSTIDIYADSVKGRFTIS RDNAKNSLYLQMNSLRAEDTAVYYCARVASFDY WGQGTLVTVSS SEQ ID NO: 31826 |

FIGURE 50
(Continued)

| | | | |
|---|---|---|---|
| iPS:437226 | 21-225_57C2 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTACTTGAATTGGTTTCAGCAG AGGCCAGGCCAATCTCCAAGGCGCCTAATTTA TGAGGTTTCTAACTGGGACTCTGGGGTCCAA ACAGATTCAGCGGCAGTGGTCAGGCACTGAT TTCACACTGAAAATCAGTGCGGTGGAGGCTGA GGATGTTGGGGTTTATTACTGCGTGCAAGTA CACACTGGCCTCGGACGTTCGGCCAAGGGACC AAGGTGGAAATCAAA<br>SEQ ID NO: 27821 | GAGGTGCAGCTGTTGGAGTCTGGGGAGGCCTG GTCAAGCCTGGGGGGGTCCCTGAGACTCTCCTGTG CAGCCCTCTGGATTCACCTTCAGTAGCTTTGGCAT GAACTGGGTCCGCCAGGCTCCAGGGAAGGGGCT GGAGTGGGTCTCATCTATTAGTAGTAGTACTGGT TACATATACAACGCAGACTCAGTGAAGGGCCGA TTCACCATCTCCAGAGACAACGCCAAGAACTCAC TGTATCTGCAAATGAACAGCCTGAGAGCCGAAG ACACGGCTGTGTATTACTGTGCGAGAACCTATAG TGGGAGCCTGGACGTCTGGGGCCAAGGGACCAC GGTCACCGTCTCCTCA<br>SEQ ID NO: 31827 |
| | | AA | DVVMTQSPLSLPVTLGQPASISCRSSQSLVYSDG NTYLNWFQQRPGQSPRRLYEVSNWDSGVPNRF SGSGSGTDFTLKISAVEAEDVGVYYCVQGTHWP RTFGQGTKVEIK<br>SEQ ID NO: 27822 | EVQLVESGGGLVKPGGSLRLSCAASGFTFSSFGMN WVRQAPGKGLEWVSSISSSTGYIYNADSVKGRFTIS RDNAKNSLYLQMNSLRAEDTAVYYCARTYSGSLD VWGQGTTVTVSS<br>SEQ ID NO: 31828 |
| iPS:437228 | 21-225_60C11 | NA | GAAATAGTGATGACGCAGTCTCCAGCCACCCT GTCTGTGTCTCCAGGGGAAAGAGCCACCCTCT CCTGCAGGGCCAGTCAGAGTGTTAGCAACGAC TTAGCCTGGTACCACCAGAAAACCTGGCCAGGC TCCCAGGCTCCTCATCTATGGTGCATCCACCA GGGCCACTGGTATCCCAGCCAGGTTCAGTGGC AGTGGGTCTGGGACAGAGTTCACTCTCACCAT CAGCGCCCCTGCAGTCTGAACATTTTGCAGTTT ATTACTGTCAGCAGTATATATAGTAACTGGCCATTC ACTTTCGGCCCTGGGACCAAAGTGGATATCAA A<br>SEQ ID NO: 27823 | GAGGTGCAGCTGTTGGAGTCTGGGGAGGCTTG GTACAGCCTGGGGGGTCCCTGAGACTCTCCTGTG CAGCCCTCTGGATTCCCCTTTAGCAGCTATGCCAT GAGCTGGGTCCGCCAGGCTCCAGGGAAGGGGCT GGAGTGGGTCTCAGTTATTAGTGGTAGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGAAATTTTCGGT GTAGTGGAGTCGGGTGCTTTGACTACTGGGGCC AGGGAACCCTGGTCACCGTCTCCTCA<br>SEQ ID NO: 31829 |

FIGURE 50
(Continued)

| | | AA | EIVMTQSPATLSVSPGERATLSCRASQSVSNDLA WYQQKPGQAPRLLIYGASTRATGIPARFSGGGS GTEFTLTISALQSEHFAVYYCQQYSNWPFTFGPG TKVDIK<br><br>SEQ ID NO: 27824 | EVQLLESGGGLVQPGGSLRLSCAASGFPSSYAMS WVRQAPGKGLEWVSAISGSGGNTFYADSVKGRFTI SRDNSKNTLYLQMNSLRAEDTAVYYCAKFFGVVG VGCFDYWGQGTLVTVSS<br><br>SEQ ID NO: 31830 |
|---|---|---|---|---|
| iPS:437230 | 21-225_62H10 | NA | GACATCCAGATGACCCAGTCTCCATCCTCCCT GTCTGCATCTGTAGGAGACAGAGTCACCATCA CTTGCCGGGCAAGTCAGAGTCAGAGCATTAGC CTTAAATTGGTATCAGCAGAAACCAGGGAAAGT CCCTAAGCTCCTGATCTCTACTGCATCCAGTTT GCAAAGTGGGGTCCCATCAAGGTTCAGTGGCA GTGGATCTGGGACAGATTTCACTCTCACCATC AGCAGTCTGCAACCTGAAGATTTTGCAACTTA CTACTGTCAACAGAGTCACAGTTTCCCATTCA CTTTCGGCCCTGGGACCAATGTGGATTTCAAA<br><br>SEQ ID NO: 27825 | GAGGTGCAGCTGTTGGAGTCTGGGGGAGGCCTG GTCAAGCCTGGGGGTCCCTGAGACTCTCCTGTG CAGCCTCTGGATTCACCTTCAGTAGCTATAGCAT GAACTGGGTCCGCCAGGCTCCAGGGAAGGGGCT GGAGTGGGTCTCATCCATTAGTAGTAGTAGT TACATATACTACGCAGACTCAGTGAAGGGCCGAT TCACCATCTCAAGAGACAACGCCAAGAACTCACT GTATCTGCAAATGAACAGCCTGAGAGCCGAGGA CACGGCTGTGTATTACTGTGCGAGAGGGGTTCG AGGGGGTTGACCCCTGGGGCCAGGGAACCCTG GTCACCGTCTCCTCA<br><br>SEQ ID NO: 31831 |
| | | AA | DIQMTQSPSSLSASVGDRVTITCRASQSITSYLN WYQQKPGKVPKLLISTASSLQSGVPSRFSGSGSG TDFTLTISSLQPEDFATYYCQQSHSFPFTFGPGTN VDFK<br><br>SEQ ID NO: 27826 | EVQLVESGGGLVKPGGSLRLSCAASGFTFSSYSMN WVRQAPGKGLEWVSSISSSSYIYADSVKGRFTIS RDNAKNSLYLQMNSLRAEDTAVYYCARGGSRGFD PWGQGTLVTVSS<br><br>SEQ ID NO: 31832 |

FIGURE 50
(Continued)

| | | | |
|---|---|---|---|
| iPS:437232 | 21-225_63E1 | NA | GACATTCAGATGACCCAGTCTCCATCTTCCGT GTATGCATCTGTAGGAGACAGAGTCACCATCA CTTGTCGTGCGAGTCAGGTATTAGCAGTAC TTAGCCTGGTATCAGCAGAAACCAGGGAAAG CCCCTAAGCTCCTGATCTATGCTGCATCCAGTT TGCAAAGTGGGGTCCCATCAAGATTCAGCGGC AGTGGGTCTGGGACAGATTTCACTCTCACCAT CAGCAGCCTGCAGCCTGAAGATTTTGCAACTT ACTATTGTCAACAGGCTAACAGTTTCCCGCTC ACTTTCGGCGGAGGGACCAAGGTGGAGATCA AA | GAGGTGCAGATGTTGGAGTCTGGGGGAGGCTTG GGACAGTCGGGGGGTCCCTGAGACTCTCCTGTA CAGCCTCTGGATTCACCTTCACCACTTCTGCCAT GAGCTGGGTCCGCCAGGCTCCAGGGAAGGGCT GGAGTGGGTCTCAGCTATTAGTGGTAGTGGTGCT AACACATTCTACGCAGACTCCGTGAAGGGCCGGT TCACCGTCTCCAGAGACAATTCCAAGAACACGCT GTATCTGCAAATGAACAGCCTGACAGCCGAGGA CACGGCCGTTTATTATTGTGTGAAAGTTATAGCA GTGGCTGGAGGGCACTTTTTCGACCCTGGGGCC AGGGAACCCTGGTCACCGTCTCCTCA |
| | | | SEQ ID NO: 31833 |
| | | AA | DIQMTQSPSSVYASVGDRVTITCRASQGISSYLA WYQQKPGKAPKLLIYAASSLQSGVPSRFSGSGS GTDFTLTISSLQPEDFATYYCQQANSFPLTFGGG TKVEIK | EVQMLESGGGLGQSGGSLRLSCTASGFTFTTSAMS WVRQAPGKGLEWVSAISGSGANTFYADSVKGRFT VTRDNSKNTLYLQMNSLTAEDTAVYYCVKVIAVA GGHFFDPWGQGTLVTVSS |
| | | | SEQ ID NO: 27828 | SEQ ID NO: 31834 |
| iPS:437234 | 21-225_64E2 | NA | GACATCCAGATGACCCAGTCTCCATCTTCCGT GTCTGCATCTGTAGGAGACAGAGTCACCATCA CTTGTCGGGCGAGTCAGGGTATTAGCAGCTAC TTAGCCTGGTATCAGCAGAAACCAGGGAAAG CCCCTAAGCTCCTGATCTATGCTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTCCCATTC ACTTTCGGCCCTGGGACCAAAGTGGATATCAA A | CAGGTGCAGCTGGTGCAGTCTGGGGCTGAGGTG AAGAAGCCTGGGGCCTCAGTGAAGGTCCTGC AAGGCTTCTGATACACCTTCACCGCTACTATA TGCACTGGGTGCGACAGGCCCCTGGACAAGGGC TTGAGTGGATGGGATGGATCAACCTAACAATAA TGGCACAAACTATGCACAGAAGTTTCAGGGCAG GGTCACCATGACCAGGGACACGTCCATCAGCAC AGCTACATGGAGCTGAGCAGGCTGAGATCGA CGACACGGCCGTGTATTACTGTGCGAGAGATGG GAGCAGTGGCTTTGACTACTGGGGCCAGGGAAC CCTGGTCACCGTCTCCTCA |
| | | | SEQ ID NO: 27829 | SEQ ID NO: 31835 |

FIGURE 50
(Continued)

| | | | |
|---|---|---|---|
| iPS:437248 | 21-225_97H3 | AA | DIQMTQSPSSVSASVGDRVTITCRASQGISRWLA WYQQKPGKAPKLLIYAASSLQSGVPSRFSGSGS GTDFTLTISSLQPEDFATYYCQQANSFPFTFGPGT KVDIK<br>SEQ ID NO: 27830 | QVQLVQSGAEVKKPGASVKVSCKASGYTFTGYYM HWVRQAPGQGLEWMGWINPNNNGTNYAQKFQGR VTMTRDTSISTAYMELSRLRSDDTAVYYCARDGSS GFDYWGQGTLVTVSS<br>SEQ ID NO: 31836 |
| | | NA | GATATTGTGATGATTCAGTCTCCACTCTCCCTG CCCGTCACCCCTGGAGAGCCGGCCTCCATCTC CTGCAGGTCTAGTCAGAGCCTCTGCATAGTA ATGGATACAAACTATTTGGATTGGTACCTACAG AAGCCAGGGCGGTCTCCACAGCTCTTGATCTA TTTGGGTTCTAATCGGGCTCCGGGGTCCCTG AGAGGTTCAGTGCAGTGGATCAGGCACAGA TTTTACACTGAAAATCAGCAGAGTGGAGGCTG AGGATGTTGGGGTTTATTACTGCATGCAACCT CTACAAACTCCGTTCACTTTCGGCGGAGGGAC CAAGGTGGAGATCAAA<br>SEQ ID NO: 27831 | CAGGTGCAGGTACAGCAGTGGGGCGCAGGACTG TTGAAGCCTTCGGAGACCCTGTCCCTCACCTGCG CTGTCTATGTGGGTCCTTCACTGATTACTACTGG AGCTGGATCCGCCAGCCCCCAGGGAAGGGCTG GAGTGGATTGGGAAATCAATCATAGTGGAGAC ACCAACTACAACCCGTCCCTCAAGAGTCGAGTCA CCATATCAGTAGACACGTCCAAGAACCAGTTCTC CCTGAAGCTGAGTTCTGTGACCGCCGGACACG GCTGTGTATTACTGTGCGAGAGAGTTCCATATA GTGAAGCTACCTCTACTACGGTATGGACGT CTGGGGCCAAGGGACCACGGTCACCGTCTCCTCA<br>SEQ ID NO: 31837 |
| | | AA | DIVMIQSPLSLPVTPGEPASISCRSSQSLLHSNGH NYLDWYLQKPGRSPQLLIYLGSNRASGVPERFS GSGSGTDFTLKISRVEAEDVGVYYCMQPLQTPF TFGGGTKVEIK<br>SEQ ID NO: 27832 | QVQVQQWGAGLLKPSETLSLTCAVYGGSFTDYYW SWIRQPPGKGLEWIGEINHSGDTNYNPSLKSRVTIS VDTSKNQFSLKLSSVTAADTAVYYCAREFPYSGSY LYYYGMDVWGQGTTVTVSS<br>SEQ ID NO: 31838 |

FIGURE 50
(Continued)

| | | | | |
|---|---|---|---|---|
| iPS:437250 | 21-225_148C6 | NA | GATGTTGTGATGACTCAGTCTCCACTCTCCCTG CCCGTCACCCTTGGACAGCCGGCCTCCATCTC CTGCAGGTCTAGTAGTCAGCCTCGTATACAGTG ATGGAAACACCTACTTGAATTGGTTTCAGCAG AGGCCAGGCCAATCTCCAAGGCGCCTAATTTA TAAGGTTTCTAACTGGGACTCTGGGGTCCCAG ACAGATTCAGCGGCAGTGGGTCAGGCACTGAT TTCACACTGAAAATCAGCAGGGTGGAGGCTGA GGATGTTGGGGTTTATTACTGCATGCAAGGTA CACACTGGTTCGCTCACTTTCGGCGGAGGGACC AAGGTGGAGATCAAA SEQ ID NO: 27833 | GAGGTGCAACTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGTTATTAGTGGTGGTAGT AGTACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGACGTCTGGGG CCAAGGGACCACGGTCACCGTCTCCTCA SEQ ID NO: 31839 |
| | | AA | DVVMTQSPLSLPVTLGQPASISCRSSQSLVYSDG NTYLNWFQQRPGQSPRRLIYKVSNWDSGVPDRF SGSGSGTDFTLKISRVEAEDVGVYYCMQGTHWS LTFGGGTKVEIK SEQ ID NO: 27834 | EVQLLESGGGLVQPGGSLRLSCAASGFTFSSYAMS WVRQAPGKGLEWVSVISGGSSTYYADSVKGRFTI SRDNSKNTLYLQMNSLRAEDTAVYYCAKWRGNPT DYGMDVWGQGTTVTVSS SEQ ID NO: 31840 |
| iPS:437252 | 21-225_148H11 | NA | GATGTTGTGATGACTCAGTCTCCACTCTCCCTG CCCGTCACCCTTGGACAGCCGGCCTCCATCTC CTGCAGGTCTAGTAGTCAGCCTCGTATACAGTG ATGGAAACACCTACTTGAATTGGTTTCAGCAG AGGCCAGGCCAATCTCCAAGGCGCCTAATTTA TAAGGTTTCTAACTGGGACTCTGGGGTCCCAG ACAGATTCAGCGGCAGTGGGTCAGGCACTGAT TTCACACTGAAAATCAGCAGGGTGGAGGCTGA GGATGTTGGGGTTTATTACTGCATGCAAGGTA CACACTGGTTGCTCACTTTCGGCGGAGGGACC AAGGTGGAGATCAAA SEQ ID NO: 27835 | GAGGTGCAACTGTTGGAGTCTGGGGGAGGCTTG GTACAGCCTGGGGGGTCCCTGAGACTCTCCTGTG CAGCCCTCTGGATTCACCTTTAGCAGCTATGCCAT GAGCTGGGTCCGCCAGGCTCCAGGGAAGGGGCT GGAGTGGGTCTCAGTTATTAGTGGTGGTAGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAATGGCGAG GTAACCCCACTGACTACGGTATGGACGTCTGGGG CCAAGGGACCACGGTCACCGTCTCCTCA SEQ ID NO: 31841 |

FIGURE 50
(Continued)

| | | | |
|---|---|---|---|
| iPS:437254 | | AA | DVVMTQSPLSLPVTLGQPASISCRSSQSLVYSDG NTYLNWFQQRPGQSPRRLIYKVSNWDSGVPDRF SGSGSGTDFTLKISRVEAEDVGVYYCMQGTHWL LTFGGGTKVEIK<br>SEQ ID NO: 27836 | EVQLLESGGGLVQPGGSLRLSCAASGFTFSSYAMS WVRQAPGKGLEWVSVISGGGSSTYYADSVKGRFTI SRDNSKNTLYLQMNSLRAEDTAVYYCAKWRGNPT DYGMDVWGQGTTVTSS<br>SEQ ID NO: 31842 |
| | 21-225_149F2 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTCCTTGAATTGGTTTCAGCAG AGGCCAGGCCAATCTCCAAGGCGCCTAATTTA TAAGGTTTCTAACTGGGACTCTGGGGTCCCAG TCAGATTCAGGGGCAGTGGGTCAGGCACTGAT TTCACACTGAAAATCAGCAGGGTGGAGGCTGA GGATGTTGGGATTTATTACTGCATGCAAGGTA CACACTGGCCTCCCACTTTCGGCGGAGGGACC AAGGTGGAGATCAAA<br>SEQ ID NO: 27837 | CAGGTGCAGCTGGGGGAGGCTGGGGGAGGCGTG GTCCAGCCTGGGAGGTCCCTGAGACTCTCCTGTG CAGCGTCTGGATTCACCTTCAGTAGCTATGGCAT GCACTGGGTCCGCCAGGCTCCAGGCAAGGGCT GGAGTGGGTGGCTTTTATATGGTATGGAAGT GAGAACTACTATGCAGACTCCGTGAAGGGCCGA TTCACCATCTCCAGAGTCAATTCCAGGAACACGC TGTATCTGCAAATGAACAGCCTGAGAGCCGAGG ACACGGCTGTGTATTACTGTGCGAGAGATCGGGT GGAGGGTTCGGGGACTCCCTACTACTACTACGGT ATGGACGTCTGGGGCCAAGGGACCACGGTCACC GTCTCCTCA<br>SEQ ID NO: 31843 |
| | | AA | DVVMTQSPLSLPVTLGQPASISCRSSQSLVYSDG NTSLNWFQQRPGQSPRRLIYKVSNWDSGVPVRF SGSGSGTDFTLKISRVEAEDVGIYYCMQGTHWP PTFGGGTKVEIK<br>SEQ ID NO: 27838 | QVQLGEAGGGVVQPGRSLRLSCAASGFTFSRYGM HWVRQAPGKGLEWVAFIWYDGSENYYADSVKGR FTISRVNSRNTLYLQMNSLRAEDTAVYYCARDRVE GSGTPYYYGMDVWGQGTTVTVSS<br>SEQ ID NO: 31844 |

FIGURE 50
(Continued)

| | | | |
|---|---|---|---|
| iPS:437256 | 21-225_150F11 | NA | GATGTTGTGATGAGTCAGTATCCACTCTCCT GCCCGTCACCTTGGACAGCCGGCCTCCATCT CATGCAGGTCTAGTCAAAGCCTCGTATACAGT GATGGAAACACCTCCTGAATTGGTTTCAGCA GAGGCCAGGCAATATCCAAGGCGCTTAATTT ATAAGGTTTCTAACTGGGACTATGGGTCCA GTCAGATTCAGCGGCAGTGGGTCAGGCACTGA TTTCACACTGAAAATCAGCAGGGTGGAGGCTG AGGATGTTGGGATTTATTACTGCATGCAAGGT ACACACTGGCCTCCCACTTTCGGCGGAGGGAC CAAGGTGGAGATCAAA |
| | | | SEQ ID NO: 27839 |
| | | AA | DVVMSQYPLSLPVTFGQPASISCRSSQSLVYSDG NTSLNWFQQRPGQYPRRLIYKVSNWDYGVPVR FSGSGSGTDFTLKISRVEAEDVGIYYCMQGTHW PPTFGGGTKVEIK |
| | | | SEQ ID NO: 27840 |
| | | NA | CAGGTGCAGCTGGTGGAGTCTGGGGGAGGCGTG GTCCAGCCTGGGAGGTCCCTGAGACTCTCCTGTG CAGCGTCTGATTCACCTTCACTTCAGTGCTATGCAT CACTGGGTCCGCCAGGCTCCAGGCAAGGGCT GGAGTGGGTGGCTTTTATATGGTATGATGAAGT GAGAACTACTATGCAGACTCCGTGAAGGGCCGA TTCACCATCTCCAGAGTCAATTCCAGGAACACGC TGTATCTGCAAATGAACAGCCTGAGAGCCGAGG ACACGGCTGTGTATTACTGTGCGAGAGATCGGGT GGAGGGTTGGGGGACTCCCTACTACTACTACGGT ATGGACGTCTGGGGCCAAGGGACCACGGTCACC GTCTCCTCA |
| | | | SEQ ID NO: 31845 |
| iPS:437258 | 21-225_153F9 | AA | QVQLGEAGGGVVQPGRSLRLSCAASGFTFSRYGM HWVRQAPGKGLEWVAFIWYDGSENYYADSVKGR FTISRVNSRNTLYLQMNSLRAEDTAVYYCARDRVE GSGTPYYYYGMDVWGQGTTVTVSS |
| | | | SEQ ID NO: 31846 |
| | | NA | GACATCCAGATGACCCAGTCTCCATCCTCACT GTCTGCATCTGTAGGAGACAGAGTCACCATCA CTTGTCGGGCGAGTCAGGGCATTAGCAATTAT TTAGCCTGGTTTCAGCAGAAAGCCAGGGAAAGC CCCTAAGTCCCTGATCTCTGCTGCATCCAGTTT GCAAAGTGGGGTCCCATCAAAGTTCAGCGGCA GTGGATCTGGGACAGATTTCACTCTCACCATC AGCAGCCTGCAACAGTATAATAGTTACCGCTCA TTACTGCCAACAGTATAATAGTTACCGCTCA GTTTCGGCGGAGGGACCAAGGTGGAGATCAA A |
| | | | CAGGTACACCTGGTGTGGAGTCTGGGGGAGGCGTG GTCCAGCCTGGGAGGTCCCTGAGACTCTCCTGTG CAGCGTCTGATTCACCATCAGTACTTCAGTGGCAT GCACTGGGTCCGCCAGGCTCCAGGCAAGGGGCT GGAGTGGGTGGCAGTTATATGGTATGGTGAAGT GATACAGACTATGCAGACTCCGTGAGGGCCGA TTCACCATCTCCAGAGACATTTCCAAGAACACGC TGTATCTGCAAATGAACAGCCTGAGAGCCGAGG ACACGGCTGTGTATTACTGTGCGAGAGATCGGGA TTATTGTAGTGGTGGTAACTGCCCTTACTACTACT ACTACGGTATGGACGTCTGGGGCCAAGGGACCA CGGTCACCGTCTCCTCA |

FIGURE 50
(Continued)

| | | | SEQ ID NO: 27841 | SEQ ID NO: 31847 |
|---|---|---|---|---|
| | | AA | DIQMTQSPSSLSASVGDRVTITCRASQGISNYLA WFQQKPGKAPKSLISAASSLQSGVPSKFSGSGSG TDFTLTISSLQPEDFATYYCQQYNSYPLSFGGGT KVEIK | QVHLVESGGGVVQPGRSLRLSCAASGFTISTYGMH WVRQGPGKGLEWVAVIWYGGSDTDYADSVRGRF TISRDISKNTLYLQMNSLRAEDTAVYYCARDRDYC SGGNCPYYYYGMDVWGQGTTVTVSS |
| | | | SEQ ID NO: 27842 | SEQ ID NO: 31848 |
| iPS:437260 | 21-225_170D1 | NA | GACATCCAGATGACCCAGTCTCCATCCTCACT GGCTGCATCTGTAGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTATGCTGCATCCAGTTT GCAAAGTGGGGTCCCATCAAGGTTCAGCGGCA GTGGATCTGGGACAGATTTCACTCTCACCATC AGCAGCCTGCAACAGTGTGATAGTTTCCCTCTCAC TTACTGCCAACAGTGTGATAGTTTCCCTCTCAC TTTCGGCGGAGGGACCAAGGTGGAGATCAAA | CAGGTGCAGTTGGTGCAGTCTGGGGCTGAGGTGA AGAAGCCTGGGGCTCAGTGAAGGTCTCCTGCA AGGCTTCTGGATACACCTTCACGGCTACTTTAT GCACTGGGTGCGACAGGCCCCTGGACAAGGGCT TGAGTGGATGGGATGGATCAAGCTAAAAGCGG TGGCACAAACTGTGCACAGAAGTTCAGGGCAG GGTCACCATGACCAGGGACACAGTCCAGCAGCAC AGCCTACATGAGCTGAGCAGGTGACATCTGA CGACACGGCCGTGTACTACTGTGCGAGAGGGG GGCTACGGTGACTACGTGGGGGTCTTTGACTAC TGGGGCCAGGGAACCCTGGTCACCGTCTCCTCA |
| | | | SEQ ID NO: 27843 | SEQ ID NO: 31849 |
| | | AA | DIQMTQSPSSLAASVGDRVTITCRASQDISNYLA WFQQKPGKAPKSLIYAASSLQSGVPSRFSGSGSG TDFTLTISSLQPEDFATYYCQQCDSFPLIFGGGT KVEIK | QVQLVQSGAEVKKPGASVKVSCKASGYTFTGYFM HWVRQAPGQGLEWMGWIKPKSGGTNCAQKFQGR VTMTRDTSSSTAYMELSRLTSDDTAVYYCARGGA TVTTWGVFDYWGQGTLVTVSS |
| | | | SEQ ID NO: 27844 | SEQ ID NO: 31850 |

FIGURE 50
(Continued)

| | | | | |
|---|---|---|---|---|
| iPS:437262 | 21-225_170E4 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTATTATCAGCAGAAACCAGGGAAGC CCCTAAGCGCCTGATCTATGTTGCATCCGGTTT GCAAAGTGGGGTCCCATCAAGGTTCAGCGGCA GTGGATCTGGGACAGAATTCACTCTCACAATC AGCAGCCTGCAGCCTGAAGATTTTGCAACTTA TTACTGTCTACAGCACAATAGTTACCCTCCGT GGACGTTCGGCCAAGGGACCAAGGTGGATAT CAAA<br>SEQ ID NO: 27845 | |
| | | AA | DIQMTQSPSSLSASVGDRVTITCRASQGIRNDLG YYQQKPGKAPKRLIYVASGLQSGVPSRFSGSGS GTEFTLTISSLQPEDFATYYCLQHNSYPPWTFGQ GTKVDIK<br>SEQ ID NO: 27846 | EVQLVESGGGSVQPGGSLRLSCAASGFTFSSYSMN WVRQAPGKGLEWVSYISSSGSTKYYADSVEGRFTI SRDNAKNSLDLQMNSLRDEDTAVYRCARDSRKGF YYGLDVWGQGTTVTVSS<br>SEQ ID NO: 31852 |
| iPS:437264 | 21-225_171H12 | NA | GACATCCAGATGACCCAGTCTCCATCCTCACT GTCTGCATCTGTAGGAGACAGAGTCACCATCA CTTGTCGGGCGAGTCAGGACATTAGCACTAT TTAGCCTGGTTTCAGCAGAAGCCAGGGAAAGC CCCTAAGTCCCTGATCTATTCTGCATCCAGTTT GCAAAGTGGGGTCCCATCAAAGTTCAGCGGCA GTGGATCTGGGACAGATTTCACTCTCACCATC AGCAGCCTGCCAACAATCTGATAGTTACCCTCAC TTACTGCCAACAATCTGATAGTTACCCTCTCAC TTTCGGGGGGAGGGACCAAGGTGGAGATCAAA<br>SEQ ID NO: 27847 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTTA TGCACTGGGTGCGACAGGCCCCTGGACAAGGGC TTGAGTGGATGGGATGGATCAAGCCTAAGAGTG GTGGCACAAACTCTGCACAGAGGTTTCAGGGCA GGGTCACCATGACCAGGGACACGTCCATCAACA CAGCCTACATGGAGCTGAACAGGCTGAGATCTG ACGACACGGCCGTATATTACTGTGCGAGAGGGG GGACTACGGTGGCTACGTGGGGGGTCTTTGACTA CTGGGGCCAGGGAACCCTGGTCACCGTCTCCTCA<br>SEQ ID NO: 31853 |

FIGURE 50
(Continued)

| | | | |
|---|---|---|---|
| iPS:437266 | 21-225_177A5 | AA | DIQMTQSPSSLSASVGDRVTITCRASQDISNYLA WFQQKPGKAPKSLIYSASSLQSGVPSKFSGSGSG TDFTLTISSLQPEDFATYYCQQSDSYPLTFGGGT KVEIK<br><br>SEQ ID NO: 27848 | QVQLVQSGAEVKKPGASVRVSCKASGYTFTGYFM HWVRQAPGQGLEWMGWIKPKSGGTNSAQRFQGR VTMTRDTSINTAYMELNRLRSDDTAVYYCARGGT TVATWGVFDYWGQGTLVTVSS<br><br>SEQ ID NO: 31854 |
| | | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGCCTGGTTTCAGCAGAAGCCAGGGAAAGC CCCTAAGTCCCTGATCTATTCTGCATCCAGTTT GCAAAGTGGGGTCCCATCAAAGTTCAGCGGCA GTGGATCTGGGACAGATTTCACTCTCACCATC AGCAGCCTGCAGCCTGAAGATTTTGCAACTTA TTACTGCCAACAATCTGATAGTTACCCTCTCAC TTTCGGCGGAGGGACCAAGGTGGAGATCAAA<br><br>SEQ ID NO: 27849 | CAGGTGCAGCTGGTACAGTCTGGGGCTGAGGTG AAGAAGCCTGGGGCCTCAGTGCGGGTCTCCTGCA AGGCTTCTGGATACACCTTCACCGCTACTTTAT GCACTGGGTGCGACAGGCCCCTGGACAAGGGCT TGAGTGGATGGGATGGATCAAGCCTAAGAGTGG TGGCACAAACTCTGCACAGAGAGTTTCAGGCAG GGTCACCATGACCAGGGACACGTCCATCAACAC AGCCTACATGGAGCTGAACTGGCTGAGATCTGAC GACACGGCCGTATATTACTGTGCGAGAGGGGGG ACTACGGTGGCTACGTGGGGGTCTTTGACTACT GGGGCCAGGGAACCCTGGTCACCGTCTCCTCA<br><br>SEQ ID NO: 31855 |
| | | AA | DIQMTQSPSSLSASVGDRVTITCRASQDISNYLA WFQQKPGKAPKSLIYSASSLQSGVPSKFSGSGSG TDFTLTISSLQPEDFATYYCQQSDSYPLTFGGGT KVEIK<br><br>SEQ ID NO: 27850 | QVQLVQSGAEVKKPGASVRVSCKASGYTFTGYFM HWVRQAPGQGLEWMGWIKPKSGGTNSAQRFQGR VTMTRDTSINTAYMELNWLRSDDTAVYYCARGGT TVATWGVFDYWGQGTLVTVSS<br><br>SEQ ID NO: 31856 |

FIGURE 50
(Continued)

| | | | |
|---|---|---|---|
| iPS:437268 | 21-225_177D2 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTACTTGAATTGGTTTCAGCAG AGGCCAGGCCAATCTCCAAGGCGCCTAATTTA TAAGGTTTCTAACTGGGACTGGGGTCCCAG ACAGATTCAGCGGCAGTGGGTCAGGCACTGAT TTCACACTGAAAATCAGCAGGGTGGAGGCTGA GGATGTTGGGGTTTATTACTGCAAGTA CACACTGGCCTCTCACTTTCGGCGGAGGGACC AAGGTGGAGATCAAA | CAGGTGCAGCTGGTGCAGTCTGGGGGAGGCGTG GTCCAGCCTGGGAGGTCCCTGAGACTCTCCTGTG CAGCGTCTGATTCACCTTCAGTAGCTATGGCAT GGACTGGGTCCGCCAGGCTCCAGGCAAGGGCT GGAGTGGGTGGCAATTATATGGTTTGATGGAAGT AATAAATACTATGCAGACTCCGTGAAGGGCCGA TTCACCATCTCCAGACAATTCCAAGAACACGC TGTATCTGCAAATGAACAGCGTGAGAGCCGAGG ACACGGCTGTGTATTACTGTGCGAGAGCATATTG TGGTGGTGACTGCTATTTCCCCATCTCCATTACT ACGGTATGGACGTCTGGGGCCAAGGGACCACGG TCACCGTCTCCTCA |
| | | | SEQ ID NO: 27851 | SEQ ID NO: 31857 |
| | | AA | DVVMTQSPLSLPVTLGQPASISCRSSQSLVYSDG NTYLNWFQQRPGQSPRRLIYKVSNWDSGVPDRF SGSGSGTDFTLKISRVEAEDVGVYYCMQGTHWP LTFGGGTKVEIK | QVQLVESGGGVVQPGRSLRLSCAASGFTFSSYGMD WVRQAPGKGLEWVAIIWFDGSNKYYADSVKGRFT ISRDNSKNTLYLQMNSLRAEDTAVYYCARAYCGG DCYFPHLHYYGMDVWGQGTTVTVSS |
| | | | SEQ ID NO: 27852 | SEQ ID NO: 31858 |
| iPS:437270 | 21-225_178H4 | NA | GACATCCAGATGACCCAGTCTCCATCCTCACT GTCTGCATCTGTAGGAGACAGAGTCACCATCA CTTGTCGGGCGAGTCAGGACATTAGCAATTAT TTAGCCTGGTTTCAGCAGAAACCAGGGAAAGC CCCTAAGTCCCTGATCTTTTCTGCATCCAGTTT GCAAAGTGGGGTCCCATCAAAGTTCAGCGGCA GTGGATCTGGGACAGATTTCACTCTCACCATC AGCAACCTGCAGCCTGAAGATTTTGCAACTTA TTACTGCCAACAATCTAATAGTTACCCTCTCAC TTTCGGCGGAGGGACCAAGGTGGAGATCAAA | CAGGTACAGCTGGTGCAGTCTGGGGCTGAGGTG AAGAAGCCTGGGGCCTCAGTGAAGGTCTCCTGc AAGGCTTCTGGATACACCTTCACCGGCTACTTTA TGCACTGGGTGCGACAGGCCCCTGGACAAGGGC TTGAGTGGATGGGATGGATCAAGCCTAAAAGTG GTGGCACAAACTGTGCACAGAAGTTTCAGGGCA GGGTCACCATGACCAGGGACACGTCCATCAGCA CAGCCTACATGGAACTGAGCAGGCTGAGATCTG ACGACACGGCCGTGTATTATTGTGTGAGAGGGGG GACTACGGTGACTACGTGGGGGTCTTTGACTAC TGGGGCCAGGGAACCATGGTCACCGTCTCCTCA |

FIGURE 50
(Continued)

| | | | |
|---|---|---|---|
| iPS:437274 | | AA | SEQ ID NO: 27853<br>DIQMTQSPSSLSASVGDRVTITCRASQDISNYLA<br>WFQQKPGKAPKSLIFSASSLQSGVPSKFSGSGSG<br>TDFTLTISNLQPEDFATYYCQQSNSYPLTFGGGT<br>KVEIK | SEQ ID NO: 31859<br>QVQLVQSGAEVKKPGASVKVSCKASGYTFTGYFM<br>HWVRQAPGQGLEWMGWIKPKSGGTNCAQKFQGR<br>VTMTRDTSISTAYMELSRLRSDDTAVYYCVRGGTT<br>VTTWGVFDYWGQGTMVTVSS |
| | | | SEQ ID NO: 27854<br>GACATCCAGATGACCCAGTCTCCATCCTCACT<br>GTCTGCATCTGTAGGAGACAGAGTCACCATCA<br>CTTGTCGGGCGAGTCAGGGCATTAGCAATTAT<br>TTAGCCTGGTTTCAGCAGAAACCAGGGAAAGC<br>CCCTAAGTCCCTGATCTATGCTGCATCCAGTTT<br>GCAAAGTGGGGTCCCATCAAAGTTCAGCGGCA<br>GTGGATGTGGGACAGATTTCACTCTCACCATC<br>AGCAGCCCGCAGCCTGAAGATGTTGCAACCTA<br>TTACTGCCAACATTATCTTAATTACCCTCTCAC<br>CTTCGGCCAAGGGACACGACTGGAGATTAAA | SEQ ID NO: 31860<br>CAGGTGCAGGTGGTGGAGTCTGGGGGAGGCGTG<br>GTCCAGCCTGGGAGGTCCCTGAGACTCTCCTGTG<br>CAGCGTCTGGATTCACCTTCAGTAGCTATGGCAT<br>GCACTGGGTCCGCCAGGCTCCAGGCAAGGGCT<br>GGAGTGGGTGGCAGTTATATGGTATGATGGAAGT<br>AATAGAAACTATGCAGACTCCGTGAAGGGCCGA<br>TTCACCATCTCCAGAGACAATTCCAAGAACACGC<br>TGTATCTGCAAATGAACAGCCTGAGAGTCGAGG<br>ACACGGCTGTGTATTACTGTGCGAGAGATCGGTC<br>TAAGGGTTACGACGGTATGGACGTCTGGGGCCA<br>AGGGACCACGGTCACCGTCTCCTCA |
| | | | SEQ ID NO: 27855 | SEQ ID NO: 31861 |
| | 21-225_196D4 | AA | DIQMTQSPSSLSASVGDRVTITCRASQGISNYLA<br>WFQQNPGKAPKSLIYAASSLQSGVPSKFSGSGCG<br>TDFTLTISSPQPEDVATYYCQHYLNYPLTFGQGT<br>RLEIK | QVQVVESGGGVVQPGRSLRLSCAASGFTFSSYGMH<br>WVRQAPGKGLEWVAVIWYDGSNRNYADSVKGRF<br>TISRDNSKNTLYLQMNSLRVEDTAVYYCARDRSKG<br>YDGMDVWGQGTTVTVSS |
| | | | SEQ ID NO: 27856 | SEQ ID NO: 31862 |

FIGURE 50
(Continued)

| | | | |
|---|---|---|---|
| iPS:437280 | 21-225_203C10 | NA | GACATCCAGATGACCCAGTCTCCATCCTCCCT GTCTGCATCTGTAGGAGACAGAGTCACCATCA CTTGCCGGGCAAGTCAGGACATTAGAAATGAT TTAGGCTGGTATCAGCAGAAACCAGGGAAAG CCCCTAAGCGCCTGATCTATCGCGCTTCAGCGG TTGCAAAGTGGGGTCCCATCACGCTTCAGCGG CAGTGGATCTGGGACAGAATTCACTCTCACAA TCAGCAGCCTGCAGCCTGAAGATTTTGCCGCT TATTACTGTCTACAGCATAATAGTTACCCGTG GACGTTCGGCCAAGGGACCAAGGTAGAGATC AAA | CAGGTGCAGCTGGTGGAGTCTGGGGGAGGCGTG GTCCAGCCTGGGAGGTCCCTGAGACTCTCCTGTG CAGCGTCTGGATTCACCTTCAGTGACTATGGCAT GCACTGGGTCCGCCAGGCTCCAGGCAAGGGGCT GGAGTGGGTGGCAGTTATATGGTATGATGAGGT AATACACATTATACAGACTCCGTGAAGGGCCGAT TCACCATCTCCAGAGACAATTCCAAGAACACGCT GTATCTGCAAATGAACAGCCTGAGAGCCGAGA CACGGCTGTATATTACTGTGCGAGAGAAGTGGT TGGCTTGATGACTACTGGGGCCAGGGAACCCTGG TCACCGTCTCCTCA |
| | | | SEQ ID NO: 27857 | SEQ ID NO: 31863 |
| | | AA | DIQMTQSPSSLSASVGDRVTITCRASQDIRNDLG WYQQKPAKAPKRLIYRASSLQSGVPSRFSGSGS GTEFTLTISSLQPEDFAAYYCLQHNSYPWTFGQG TKVEIK | QVQLVESGGGVVQPGRSLRLSCAASGFTFSDYGM HWVRQAPGKGLEWVAVIWYDGGNTHYTDSVKGR FTISRDNSKNTLYLQMNSLRAEDTAVYYCAREVG WLDDYWGQGTLVTVSS |
| | | | SEQ ID NO: 27858 | SEQ ID NO: 31864 |
| iPS:437282 | 21-225_207C9 | NA | GACAACCAGATGACCCAGTCTCCATCCTCCCT GTCTGCATCTGTAGGAGACAGAGTCACCATCA CTTGCCGGGCAAGTCAGGACAGAGTTAGTAACTA TTAAATTGGTATCAGCAGAAACCAGGGAAAG CCCCTAAGCTCCTGATCTATACTGCATCCAGTT TGCAAAGTGGGGTCCCATCAAGGTTCAGTGCC AGTGTCTCTGGGACAGACTTCACTCTCACCAT CAGCAGTCTGCAACCTGAAGAGTTGCAACTT ATTACTGTCAACAGAGTTACAGTATTCCGCTC ACTTCCGGCGGAGGGACCAAGGTGGAGATCA AA | GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AGCACATACTACGCAGACTCCGTGAAGGGCCGG TTCACCATCTCCAGAGACAATTCCAAGAACACGC TGTATCTGCAAATGAACAGCCTGAGAGCCGAGG ACACGGCCGTATATTACTGTGCGAAAGCTGGTGG AACTACGGGGAGCTACTACTACAACGGTATGA CGTCTGGGGCCAAGGGACCACGGTCACCGTCTCC TCA |
| | | | SEQ ID NO: 27859 | SEQ ID NO: 31865 |

FIGURE 50
(Continued)

| | | | | |
|---|---|---|---|---|
| iPS:437286 | 21-225_208F1 | AA | DNQMTQSPSSLSASVGDRVTITCRASQRFSNYLN WYQQKPGKAPKLLIYTASSLQSGVPSRFSASVSG TDFTLTISSLQPEDFATYYCQQSYSIPLTFGGGTK VEIK<br><br>SEQ ID NO: 27860 | EVQLLESGGGLVQPGGSLRLSCAASGFTFSSYAMS WVRQAPGKGLEWVSAISGSGGSTYYADSVKGRFTI SRDNSKNTLYLQMNSLRAEDTAVYYCAKAGGTTG SYYYNGMDVWGQGTTVTVSS<br><br>SEQ ID NO: 31866 |
| | | NA | GACATCCAGATGACCCAGTCTCCATCCTCCCT GTCTGCATCTGTAGGAGACAGAGTCACCATCA CTTGCCGGGCAAGTCAGGGACATTAGACATGAT TTAGGCTGGTATCAGCAGAAACCAGGGAAAG CCCCTAAGCGCCTGATCTTTGCTGCATCCAGTT TGCAAAGTGGGGTCCCATCTAGATTCAGCGGC AGTGGATCTGGGACAGAATTCACTCTCACAAT CAGCAGCCTGCAGCCTGAAGATTTTGCAACTT ATTACTGTCTACAGCATTATAGTTTCCCTCGGA CGTTCGGCCAAGGGACCAAGGTGGAAATCAA A<br><br>SEQ ID NO: 27861 | CAGGTGCAGCTGGTGGAGTCTGGGGGAGGCGTG GTCCAGCCTGGGAGGTCCCTGAGACTCTCCTGTG CAGCGTCTAGATTCACCTTCAGTGACTATGTCAT GCACTGGGTCCGCCAGGCTCCAGGCAAGGGCT GGAGTGGGTGGCAGTTATATGTAGACTCCGTGAAGT AATAAATACTATGTAGACTCCGTGAAGGGCCGAT TCACCATCTCCAGAGACAATTCCAGGAACACGCT GTATCTGCAAATGAACAGCTGAGAGCCGAGA CACGGCTGTATATTACTGTGCAGAGAACGGTAT AGCAGTGGCTTGTACGACTACGGTATGGACGTCT GGGGCCAAGGGACCACGGTCACCGTCTCCTCA<br><br>SEQ ID NO: 31867 |
| | | AA | DIQMTQSPSSLSASVGDRVTITCRASQGIRHDLG WYQQKPGKAPKRLIFAASSLQSGVPSRFSGSGSG TEFTLTISSLQPEDFATYYCLQHYSFPRTFGQGTK VEIK<br><br>SEQ ID NO: 27862 | QVQLVESGGGVVQPGRSLRLSCAASRFTFSDYVMH WVRQAPGKGLEWVAVIWYDGSNKYYVDSVKGRF TISRDNSRNTLYLQMNSLRAEDTAVYYCARERYSS GLYDYGMDVWGQGTTVTVSS<br><br>SEQ ID NO: 31868 |

FIGURE 50
(Continued)

| | | | | |
|---|---|---|---|---|
| iPS:437290 | 21-225_210G6 | NA | GACATCCAGATGACCCAGTCTCCATCCTCCG TTTTGCATTTGTAGGAGACAGAGTCACCATCA CTTGCCGGGCAAGTCAGGGCATTAGACATGAT TTAGGCTGGTATCAGCAGAAACCAGGGAAAG CCCTTAAGCGCTTGATATATGCTGCATCCAGT CGCAAAGTGGGGTCCATCAAGGTTCAGCGGC AGTGGATGTGGGACAGAATTCACTCTCACAAT CAGCAGCGTGCAGCGCGAAGATTTTGCAAAT ATTACTGTGTACAGCATTATAGTTTCCCTCGGA CGTTCGGCCAAGGGACCAAGGTGGAAATCAA A | CAGGTGCAGCTGGTGGAGTCTGGGGGAGGCGTG GTCCAGCCTGGGAGGTCCCTGAGACTCTCCTGTG CAGCGTCTGATTCACCTTCAGTGACTAGTCAT GCACTGGGTCCGCCAGGCTCCAGGCAAGGGCT GGAGTGGGTGGCAGTTATATGGTATGATGAAGT AATAAATACTATGTAGACTCCGTGAAGGGCCGAT TCACCATCTCCAGAGACAATTCCAGGAACACGCT GTATCTGCAAATGAACAGCCTGAGAGCCGAGGA CACGGCTGTGTATTACTGTGCGAGAGAACGTAT AGCAGTGGCTTGTACGACTACGGTATGACGTCT GGGGCCAAGGGACCACGGTCACCGTCTCCTCA |
| | | | SEQ ID NO: 27863 | SEQ ID NO: 31869 |
| | | AA | DIQMTQSPSSRFAFVGDRVTITCRASQGIRHDLG WYQQKPGKALKRLIYAASSSQSGVPSRFSGSGC GTEFTLTISSVQREDFANYYCVQHYSFPRTFGQG TKVEIK | QVQLVESGGGVVQPGRSLRLSCAASGFTFSDYVM HWVRQAPGKGLEWVAVIWYDGSNKYYVDSVKGR FTISRDNSRNTLYLQMNSLRAEDTAVYYCARERYS SGLYDYGMDVWGQGTTVTVSS |
| | | | SEQ ID NO: 27864 | SEQ ID NO: 31870 |
| iPS:437294 | 21-225_216D5 | NA | GATGTTGTGATGACTCAGTCTCCACTCTCCCTG CCCGTCACCCTTGGACAGCCGGCCTCCATCTC CTGCAGGTCTAGTCAAAGCCTCGTATACAGTG ATGGAAACACCTACTTGAATTGGTTTCAGCAG AGGCCAGGCCAATCTCCAAGGCGCCTCATTTA TAAGGTTTCTAACTGGGACTCTGGGGTCCCAG ACAGAATCAGCGGCAGTGGGTCAGGCACTGA TTTCACACTGAAAATCAGCAGGGTGGAGGCTG AGGATGTTGGGATTTATTACTGCATGCAAGGT GCACACTGGTTCACCTTCGGCCAAGGGACACG ACTGGAGATTAAA | CAGGTGCAGCTGCAGGAGTCGGGCCCAGGACTG GTGAAGCCTTCACAGACCCTGTCCCTCACCTGCA CTGTCTCTGGTGGCTCCATCAGCAGTGGTTA CTACTGGAGCTGGATCCGCCAGCACCCAGGGAA GGGAGCACTACTACCAACCCGTCCTCAAGAGTC GAGTTACCATATCAGTAGACACGTCTAAGAACCA ATTCTCCCTGAAACTGAACTCTGTGACTGCCGCG GACACGGCCGTGTATTTCTGTGCGAGAGATTCCC CTGACAGGGGGTTTGACTACTGGGGCCAGGGAA CCCTGGTCACCGTCTCCTCA |
| | | | SEQ ID NO: 27865 | SEQ ID NO: 31871 |

FIGURE 50
(Continued)

| | | | |
|---|---|---|---|
| | | AA | DVVMTQSPLSLPVTLGQPASISCRSSQSLVYSDG NTYLNWFQQRPGQSPRRLIYKVSNWDSGVPDRI SGSGSGTDFTLKISRVEAEDVGIYYCMQGAHWF TFGQGTRLEIK<br><br>SEQ ID NO: 27866 | QVQLQESGPGLVKPSQTLSLTCTVSGGSISSGGYYW SWIRQHPGKGLEWIGYIYYSGSTYYNPSLKSRVTIS VDTSKNQFSLKLNSVTAADTAVYFCARDSPDRGFD YWGQGTLVTVSS<br><br>SEQ ID NO: 31872 |
| iPS:437302 | 21-225_225B11 | NA | GACATCCAGATGACCCAGTCTCCATCCTCCCT GTCTGCATCTATAGGAGACAGAGTCACCATCA CTTGCCAGGCGAGTCAGGACATTTTCAACTAT TTAAATTGGTATCAGCAGAAACCAGGGAAAG CCCCTAAGCTCCTGATCTACGATGCATCCACTT TGGAAACAGGGGTCCCATCAAGGTTCAGTGGA AGTGGATCTGGGACAGATTTTACTTTCACCAT CAGCAGCCTGCAGCCTGAAGATATTGCAACAT ATTACTGTCAACAGTATGATAATCTCCCGATC ACCTTCGGCCAAGGGACACGACTGGAGATTAA A<br><br>SEQ ID NO: 27867 | CAGGTGCAGCTGGTGGAATCTGGGGGAGGCGTG GTCCAGCCTGGGAGGTCCCTGAGACTCTCCTGTG CAGCCTCTGGATTCACCTTCAGTAGCTATGCAT GCACTGGGTCCGCCAGGCTCCAGGCAAGGGCT GGAGTGGGTGACAATTATATCATATAGTGGAAGT AATAAATACTATGCAGACTCCGTGAAGGGCCGA TTCACCATCTCCAGAGACAACATCCAAGAACAGC TGTATCTGCAAATGAACAGCCTGAGAGCTGAGG ACACGGCTGTGTATTACTGTGCGAGACGGGGATA CAGCTATGGCGGGTACGGTATGGACGTCTGGGG CCAAGGGACCACGGTCACCGTCTCCTCA<br><br>SEQ ID NO: 31873 |
| | | AA | DIQMTQSPSSLSASIGDRVTITCQASQDIFNYLNW YQQKPGKAPKLLIYDASTLETGVPSRFSGSGSGT DFTFTISSLQPEDIATYCQQYDNLPITFGQGTRL EIK<br><br>SEQ ID NO: 27868 | QVQLVESGGGVVQPGRSLRLSCAASGFTFSSYGMH WVRQAPGKGLEWVTIISYSGSNKYYADSVKGRFTI SRDNSKNTLYLQMNSLRAEDTAVYYCARRGYSYG GYGMDVWGQGTTVTVSS<br><br>SEQ ID NO: 31874 |

FIGURE 50
(Continued)

| | | | | |
|---|---|---|---|---|
| iPS:437320 | 21-225_75A1 | NA | GATATTGTGATGACTCAGTCTCCACTCTCCCTG CCCGTCACCCCTGGAGAGCCGGCCTCCATCTC CTGCAGGTCAGTCAGAGCCTCCTGCATAGTA ATGGATACAACTATTTGGATTGGTACCTACAG AAGCCAGGGCGGTCTCCACAGCTCCTGATCTA TTTGGGTTCTAATCGGGCCTCCGGGGTCCCTG AGAGGTTCAGTGGCAGTGGATCAGGCACAGA TTTTACACTGAAAATCAGCAGAGTGGAGGCTG AGGATGTTGGGGTTTATTACTGCATGCAACCT CTACAAACTCCGTTCACTTTCGGCGGAGGGAC CAAGGTGGAGATCAAA SEQ ID NO: 27869 | CAGGTGCAGGTACAGCAGTGGGGCGCAGGACTG TTGAAGCATTCGGAGACCCTGTCCCTCACCTGCG CTGTCTATGGTGGGTCCTTCACTGATTACTACTGG AGCTGGATCCGCCAGCCCCCAGGGAAGGGGCTG GAGTGGATTGGGGAAATCAATCATAGTGGAGAC ACCAACTACAACCGTCCCTCAAGAGTCGAGTCA CCATATCAGTAGACACGTCCAAGAACCAGTTCTC CCTGAAGCTGAGTTCTGTGACCGCCGGACACG GCTGTGTATTACTGTGCGAGAGAGTTTCCATATA GTGGAAGCTACCTCTACTACTACGGTATGGACGT CTGGGGCCAAGGGACCACGGTCACCGTCTCCTCA SEQ ID NO: 31875 |
| | | AA | DIVMTQSPLSLPVTPGEPASISCRSSQSLLHSNGH NYLDWYLQKPGRSPQLLIYLGSNRASGVPERFS GSGSGTDFTLKISRVEAEDVGVYYCMQPLQTPF TFGGGTKVEIK SEQ ID NO: 27870 | QVQVQQWGAGLLKHSETLSLTCAVYGGSFTDYYW SWIRQPPGKGLEWIGEINHSGDTNYNPSLKSRVTIS VDTSKNQFSLKLSSVTAADTAVYYCAREFPYSGSY LYYYGMDVWGQGTTVTVSS SEQ ID NO: 31876 |
| iPS:437322 | 21-225_75B1 | NA | GAATTTATGTTGACGCAGTCTCCAGGCACCCT GTATTGGTCTCCAGGGGAAAGAGCCACCATCT CGAGCAGGCCAGTCAGAGTGTTAGCAGCAG CTACTTAGTCTGGTATCAGCAGAAACCTGGCC AGGCTCCCAGGCTCCTCATCTATGGTGCATCC ACCAGGGCCACTGGCATCCCAGACAGGTTCAG TGGCAGTGGGTCTGGGACAGACTTCACTCTCA CCATCAGCAGACTGGAGCCTGAATATTTTGCA GTTTATTACTGTCAGCAGTATGGTTGTTCACCG CTCACTTTCGGCGGAGGGACCAAGGTGGAGAT CACA SEQ ID NO: 27871 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGTCCCTGGACAAGGGC TTGAGTGGATGGGGATGGATGCACAGAAGTGG TAACACAGGCTATGCACAGAAGTTCCAGGGCAG AGTCACCATGACCAGGAACACCTCCATCAGCAC AGCCTACATGGAGCTGAGCAGCCTGAGATCTGA GGACACGGCCGTGTATTACTGTGCGATTAGTAGT GGCTGGTACTGGTTCGACCCCTGGGGCCAGGGA ACCCTGGTCACCGTCTCCTCA SEQ ID NO: 31877 |

FIGURE 50
(Continued)

| | | | |
|---|---|---|---|
| iPS:437324 | 21-225_75C2 | AA | EFMLTQSPGTLYWSPGERATISSRASQSVSSSYL VWYQQKPGQAPRLLIYGASTRATGIPDRFSGSGS GTDFTLTISRLEPEYFAVYYCQQYGCSPLTFGGG TKVEIT<br>SEQ ID NO: 27872 | QVQLVQSGAEVKKPGASVKVSCKASGYTFTNYDIN WVRQVPGQGLEWMGWMHPNSGNTGYAQKFQGR VTMTRNTSISTAYMELSSLRSEDTAVYYCAISSGW YWFDPWGQGTLVTVSS<br>SEQ ID NO: 31878 |
| | | NA | GAAATTGTGTTGACGCAGTCTCCAGGCACCCG GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATCTATGGTGCATCA GCCGGGCCACTGGCATCCCAGACAGGTTCAGT GGCAGTGGGTCTGGGACAGACTTCGCTCTCAC CATCAGCAGACTGGAGCCTGAAGATTGTGCAG TGTATTACTGTCAGCACTATGATAATCCACCG TGGACGTTCGGCGGAGGGACCAAGGTGGAAA TCAAA<br>SEQ ID NO: 27873 | CAGGTGCAGTACAGAGCAGTGGGGCGCAGGACTG TTGAAGCCTTCGGAGACCGTGTCCCTCACCTGCG CTGTCCATGGTGGTCTCCTCAGTGGTTGCTACTG GAGCTGGATCCGCCAGCCCCCAGGGAAGGGGCT GGAGTGGATTGGGGAAATCAATCATAGTGGAAG CACCAACTACAACCCGTCCCTCCAAGAGTCGAGTC ACCATTTCAGTAGACACGTCCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 31879 |
| | | AA | EIVLTQSPGTRYLSPGERATLSCRASQSVYSSYL AWYQQKPGQAPRLLIYGASSRATGIPDRFSGSGS GTDFALTISRLEPEDCAVYYCQHYDNSPWTFGR GTKVEIK<br>SEQ ID NO: 27874 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTSS<br>SEQ ID NO: 31880 |

FIGURE 50
(Continued)

| | | | | |
|---|---|---|---|---|
| iPS:437326 | 21-225_75C10 | NA | GACATCCAGATGACCCAGTCTCCGTCTTCCGT GTCTGTCTTCTGTAGGAGACAGAGTCATCATCA CTTGTCGGGCGAGTCAGGCATTAGCATCTGG TTAGCCTGGTATCAGCAGAAACCAGGGAAAG CCCCTAAGCTCCTGATCTATGCTGCATCCAGTT TGCAAAGTGGGGTCCCATTAAGGTTCAGCGGC AGTGGATCTGGGACAGATTTCACTCTCACCAT CAGCAGCCTGCAGCCTGAAGATTTTGCAACTT ACTATTGTCAACAGGCTAAAAGTTTCCCGCTC ACTTTCGGCGGAGGGACCAAGGTGGAGATCA AA | CAGGTGCAACTGGTGGAGTCTGGGGGAGGCGTG GTCCAGCCTGGGAGGTCCCTGAGACTCTCCTGTG CAGCGTCTGGATTCACCTTCAGTAGTTATGGCAT GCATTGGGTCCGCCAGGCTCCAGGCAAGGGGCT GGAGTGGGTGGCAGTTATATGGTATGATGGAAGT GATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGATCGTT AGTGGGAGCTACGGTTGATGCTTTTGATATCTGG GGCCAAGGGACAATGGTCACCGTCTCTTCA |
| | | | SEQ ID NO: 27875 | SEQ ID NO: 31881 |
| | | AA | DIQMTQSPSSVSASVGDRVIITCRASQGISIWLAW YQQKPGKAPKLLIYAASSLQSGVPLRFSGSGSGT DFTLTISSLQPEDFATYYCQQAKSFPLTFGGGTK VEIK | QVQLVESGGGVVQPGRSLRLSCAASGFTFSSYGMH WVRQAPGKGLEWVAVIWYDGSDKYYADSVKGRF TISRDNSKNTLYLQMNSLRAEDTAVYYCARDRLVG ATVDAFDIWGQGTMVTVSS |
| | | | SEQ ID NO: 27876 | SEQ ID NO: 31882 |
| iPS:437328 | 21-225_75D3 | NA | GAAATTGTGTTGACGCAGTCTCCAGGCACCCT GTATTGTCTCCAGGGAAAGAGCCACCCTCT CATGCAGGCCAGTCAGAGTGTTACAGCAGC TACTTAGCCTGGTACCAGCAGAAACCTGGCCA GGCTCCCAGGCTCCTCATCATTTATGGTGCATCCA GCCGGTCCACTGGCATACCAGACAGGTTCAGT GGCAGTGGGTGTGGGACAGACTTCGCTCTCAC CATCAGCAGAGTGGAGCATGAAGATTGTGCA GTGTATTACTGTCAGCACTATGATAACTCACC GTGGACGTTCGGCCAAGGGACCAAGGTGGAA ATCAAA | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA |
| | | | SEQ ID NO: 27877 | SEQ ID NO: 31883 |

FIGURE 50
(Continued)

| | | | | |
|---|---|---|---|---|
| iPS:437332 | 21-225_75F3 | AA | EIVLTQSPGTLYLSPGERATLSCRASQSVYSSYLA WYQQKPGQAPRLLIYGASSRSTGIPDRFSGSGCG TDFALTISRVEHEDCAVYYCQHYDNSPWTFGQG TKVEIK<br>SEQ ID NO: 27878 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 31884 |
| | | NA | GAAATTGTGTTGACGCAGTCTCCAGGCACCCT GTATTTGTCTCCAGGGGAAAGAGCCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCA GCCGGGCCACTGGCATCCCAGACAGGTTCAGT GGCAGTGGGTGTGGGACAGACTTCGCTCTCAC CATCAGCAGACTGGAGCATGAAGATTTTGCAG TGTATTACTGTCAGCACTATGATAACTCACCG TGGACGTTCGGCCAAGGGACCAAGGTGGAAA TCAAA<br>SEQ ID NO: 27879 | CAGGTGCAGTCGTACAGCAGTGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 31885 |
| | | AA | EIVLTQSPGTLYLSPGERATLSCRASQSVYSSYLA WYQQKPGQAPRLLIYGASSRATGIPDRFSGSGCG TDFALTISRLEHEDFAVYYCQHYDNSPWTFGQG TKVEIK<br>SEQ ID NO: 27880 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 31886 |

FIGURE 50
(Continued)

| | | | |
|---|---|---|---|
| iPS:437334 | 21-225_75F11 | NA | GAAATAGTGATGACGCAGTCTCCAGCCACCCT GTTTGTGTCTCCAGGGGAAAGAGCCACCCTCT CCTGCAGGGCCAGTCAGAGTGTTAGCAGAAAT TTAGCCTGGTTCCAGCAGAAACCTGGCCAGGC TCCCAGGCTCCTCTTTATGGTGCATCCATCAG GGCCACTGGTATCCCAGCCAGGTTCAGTGGCA GTGGGTCTGGGACAGAGTTCACTCTCACCATC TACAGCCTGCAGTGCAGTATGAAGATTTTGCAGTTTA TTACTGTCAGCAGTATAATAACTGGCCTCCGC TCACTTTCGGCGGAGGGACCAAGGTGGAGATC AAA | CAGATCACCTTGAAGGAGTCTGGTCCTACGCTGG TGAAACCCACACAGAGACCCTCACGTGACCTGCAC CTTCTCTGGGTTCTCACTCAGCACTGGTGGAGTG GGCTGTGGGCTGGATCCGTCAGCCCCCAGGAAAG GCCCTGGAGTGGCTTGCACTCATTTATTGGGATG ATGATAAGGCTACAGCCCATCTGAAGAGCA GGCTCACCATCACCAAGGACACCTCCAAAACC AGGTGGTCCTTACAATGACCAACATGGACCCTGT GGACACAGCCACATATTACTGTGCACACTTATA GCAGTGGCCTTTGACTACTGGGGCCAGGGAACCC TGGTCACCGTCTCCTCA |
| | | | SEQ ID NO: 27881 | SEQ ID NO: 31887 |
| | | AA | EIVMTQSPATLFVSPGERATLSCRASQSVSRNLA WFQQKPGQAPRLLFYGASIRATGIPARFSGSGSG TEFTLTIYSLQYEDFAVYYCQQYNNWPPLTFGG GTKVEIK | QITLKESGPTLVKPTQTLTLTCTFSGFSLSTGGVGVG WIRQPPGKALEWLALIYWDDDKRYSPSLKSRLTIT KDTPKNQVVLTMTNMDPVDTATYYCAHLIAVAFD YWGQGTLVTVSS |
| | | | SEQ ID NO: 27882 | SEQ ID NO: 31888 |
| iPS:437340 | 21-225_75G9 | NA | GAAATTGCGTTGACGCAGTCTCCAGGCACCCT GTCTTTGTCTCCAGGGGAAAGAGCCACCCTCT CCTGCAGGGCCAGTCCGAGTGTTGACAGCAGC TACTTAGCCTGGTACCAGCAGAAACCTGGCCA GGCTCCCAGGCTCCTCATCTATGGTGCATCCA GCAGGGCCCCTGGCATCCCAGACAGGTTCAGT GGCAGTGGGTCTGGGACAGACTTCACTCTCAC CATCAGCAGACTGGAGCCTGAAGATTTTGCAG TGTATTACTGTCAGCAGTATGAAAGTTCACCG TGGACGTTCGGCCAAGGGACCAAGGTGGAAA TCAAA | CAGGTGCAGCTACAGCAGTGGGGCGCAGGACTG TTGAAGCCTTCGGAGACCCTGTCCCTCACCTGCG CTGTCTATGGTGGGGTCCTTCAGTGGTTGCTACTG GAGCTGGATCCGCCAGCCCCAGGGAAGGGCT GGAGTGGATTGGGAAATCAATCATAGTGGAAG GACCAACTACAACCCGTCCCTCAAGAGTCGAGTC ACCATATCAGTAGACACGTCCGAGAACCAGTTCT CCCTGAAGCTGAGCTCTGTGCGAGAGACTACGGTGGG GGCTGTGTATTACTGTGGGGCCAGGGAACCCTGGTCACCG CTTGACTACTGGGGCCAGGGAACCCTGGTCACCG TCTCCTCA |
| | | | SEQ ID NO: 27883 | SEQ ID NO: 31889 |

FIGURE 50
(Continued)

| | | | | |
|---|---|---|---|---|
| | | AA | EIALTQSPGTLSLSPGERATLSCRASPSVDSSYLA WYQQKPGQAPRLLIYGASSRAPGIPDRFSGSGSG TDFTLTISRLEPEDFAVYYCQQYESSPWTFGQGT KVEIK<br><br>SEQ ID NO: 27884 | QVQLQQWGAGLLKPSETLSLTCAVYGGSFSGCYW SWIRQPPGKGLEWIGEINHSGRTNYNPSLKSRVTIS VDTSENQFSLKLSSVTAADTAVYYCARDYGGLDY WGQGTLVTVSS<br><br>SEQ ID NO: 31890 |
| iPS:437344 | 21-225_75G12 | NA | GAAATTGTGTTGACGCAGTCTCCAGGCACCCT GTATTTGTCTCCAGGGGAAAGAGCCACCCTGT CATGCAGGGCCAGTCAGAGTGTTTACAGCAGC TACTTAGCCTGGTACCAGCAGAAACCTGGCCA GGCTCCCAGGCTCCTCATTTATGGTGCATCCA GCCGGGCCACTGGCATCCCAGACAGGTTCAGT GGCAGTGGGTCTGGGACAGACTTCGCTCTCAC CATCAGCAGAGTGGAGCCTGAAGATTGTGCAG TGTATTACTGTCAGCACTATGATAATCACCG TGGACGTTCGGCCAAGGGACCAAGGTGGAAA TCAAA<br><br>SEQ ID NO: 27885 | CAGGTGCAGCTACAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA<br><br>SEQ ID NO: 31891 |
| | | AA | EIVLTQSPGTLYLSLSPGERATLSCRASQSVYSSYLA WYQQKPGQAPRLLIYGASSRATGIPDRFSGSGSG TDFALTISRVEPEDCAVYYCQHYDNSPWTFGQG TKVEIK<br><br>SEQ ID NO: 27886 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br><br>SEQ ID NO: 31892 |

FIGURE 50
(Continued)

| | | | |
|---|---|---|---|
| iPS:437346 | 21-225_75H7 | NA | GACATTCAGATGACCCAATCTCCATCCTCCG GTATGCATCTGTAGGAGACAGAGTCACCATCA ATAGCCGGGCAAGTCAGGGCATAAGAAATGA TTTAGGCTGGTATCAACAGAAACCAGGAGAAAT CCCCTCAGCGCCTGATTTATGATGCATCCAGTT TGCAAAGTGGGGTCCCATCAAGGTTCAGCGGC AGTGGATCTGGGACAGAATTCACTCTCACAAT CAGCAGCCTGCAGCCTGAAGATTTTGGTGTTT ATTACTGTATACAGCATAGTAATTACCCGCTC ACTTTCGGCGGAGGGACCAAGGTGGAGATCA AA |
| | | | SEQ ID NO: 27887 |
| | | AA | DIQMTQSPSSRYASVGDRVTINSRASQGIRNDLG WYQQKPGKSPQRLIYDASSLQSGVPSRFSGSGSG TEFTLTISSVQPEDFGVYYCIQHSNYPLTFGGGTK VEIK |
| | | | SEQ ID NO: 27888 |
| iPS:437350 | 21-225_74A3 | NA | GAAATTGTGTTGACGCAGTCTCCAGGCACCCT GTCTTTGTCTCCAGGGGAAAGAGCCACCCTCT CATGCAGGGCCAGTCAGAGTGTTACAGCAGC TACTTAGCCTGGTACCAGCAGAAACCTGGCCA GGCTCCCAGGCTCCTCATTTATGGTGCATCCA GCCGGTCCACTGGCATCCCAGACAGGTTCAGT GGCAGTGGGTGTGGGACAGACTTCGCTCTCAC CATCAGCAGACTGGAGCCTGAAGATTTTGCAG TGTATTACTGTCAGCACTCTGATAACTCACCGT GGACGTTCGGCCAAGGGACCAAGGTGGAAAT CAAA |
| | | | SEQ ID NO: 27889 |

| | | |
|---|---|---|
| | | CAGCTGCAGCTGCAGGAGTCGGGCCCAGGACTG GTGAAGCCTTCGGAGACCCTGTCCCTCACCTGCA CTGTCTCTGGGGGCTCCATCAGCAGGAGTAGTTA CTACTGGGGCTGGATCCGCCAGCCCCCAGGGAA GGGGCTGGAGTGGATTGGGAGTATCTATTATAGT GGGAGCGCCTACTCCAACCGTCCCTCAAGAGTC GAGTCACCATATCGTAGAACACGTCAAGAACC AGTTCTCCCTGAAGCTGAGCTCTGTGACCGCCGC GGACACGGCTGTCTGTTTACTGTGCGAGACTTGAC TCTAACTGGGGTCTTGACTACTGGGGCCAGGGAA CCCTGGTCACCGTCTCCTCA |
| | | SEQ ID NO: 31893 |
| | | QLQLQESGPGLVTPSETLSLTCTVSGGSISRSSYYW GWIRQPPGKGLEWIGSIYYSGSAYSNPSLKSRVTIS VDTSKNQFSLKLSSVTAADTALFYCARLDSNWGLD YWGQGTLVTVSS |
| | | SEQ ID NO: 31894 |
| | | CAGGTGCAGCTACAGCAGTGGGGCGCAGGACTG TTGAAGCCTTCGGAGACCCTGTCCCTCACCTGCG CTGTCCATGGTGGGTCCTTCAGTGGTTGCTACTG GAGCTGGATCCGCCAGCCCCCAGGGAAGGGGCT GGAGTGGATTGGGAAATCAATCATAGTGGAAG CACCAACTACAACCCGTCCCTCAAGAGTCGAGTC ACCATTTCAGTAGACACGTCCAAGAACCAGTTCT CCCTGAAGCTGAGCTCTGTGACCGCCGCGGACAC GGCTGTGTATTACTGTGCGAGGGACTACGGCGGT ATGGACGTCTGGGGCCAAGGGACCACGGTCACC GTCTCCTCA |
| | | SEQ ID NO: 31895 |

FIGURE 50
(Continued)

| | | | |
|---|---|---|---|
| iPS:437356 | 21-225_74B1 | AA | EIVLTQSPGTLSLSPGERATLSCRASQSVYSSYLA WYQQKPGQAPRLLIYGASSRSTGIPDRFSGSGCG TDFALTISRLEPEDFAVYYCQHSDNSPWTFGQGT KVEIK<br>SEQ ID NO: 27890 | QVQLQQWGAGLLKPSETLSLTCAVHGGSFSGCYW SWIRQPPGKGLEWIGENHSGSTNYNPSLKSRVTISV DTSKNQFSLKLSSVTAADTAVYYCARDYGGMDV WGQGTTVTVSS<br>SEQ ID NO: 31896 |
| | | NA | GACATCGTGATGACCCAGTCTCCAGACTTCCT GGCTGTGTCTCTGGGCGAGAGGGCCACCACCA ATTGTAAGTCCAGCCAGAGTGTTTTACACAGG TCCAACAATTACAACTACTTAGCGTGTACCA GCAGAAACCAGGACAGGCCTCCTAAGCTGCTCA TTTACTGGGCATCTCACCCGGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA TATTATAGTACTCCTCCGACGTTCGGCCAAGG GACCAAGGTGGAAATCAAA<br>SEQ ID NO: 27891 | CAGGTGCAGCTGGTGCAGTCTGGGGCTGAGGTG AAGAAGCCTGGGGCCTCAGTGAAGGTCCTGC AAGGCTTCTGGATACACCTTGACCAATTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCAGGAACACCTCCATAAGCA CAGCCTACATGGAACTGAGCAGCCTGAGATCTG AGGACACGGCCGTGTATTACTGTGGGAGTACCA GTGGCTGGAACTTCTTTGACTACTGGGGCCAGGG AACCCTGGTCACCGTCTCCTCA<br>SEQ ID NO: 31897 |
| | | AA | DIVMTQSPDFLAVSLGERATTNCKSSQSVLHRSN NYNYLAWYQQKPGQPPKLLIYWASTRESGVPD RFSGSGSGTDFTLTISSLQAEDVAVYYCQQYYST PPTFGQGTKVEIK<br>SEQ ID NO: 27892 | QVQLVQSGAEVKKPGASVKVSCKASGYTLTNYDI NWVRQATGQGLEWMGWMNPNSGNTGYAQKFQG RVTMTRNTSISTAYMELSSLRSEDTAVYYCGSTSG WNFFDYWGQGTLVTVSS<br>SEQ ID NO: 31898 |

FIGURE 50
(Continued)

| | | | | |
|---|---|---|---|---|
| iPS:437361 | 21-225_74C1 | NA | GACATCGTGATGACCCAGTCTCCAGACTCCCC GGCTGTGTCTCTGGGCGAGAGGGCCTCCATCA ATTGCAAGTCCAGCCAGAGTATTTACACAGC TCCAACAATTACAACTTAGCTTGGTACCA GCAGAAACCAGGACATCCTCATAAGCTGCTCA TTTACTGGGCATCTACCCGGAATCCGGGGTC CCTGACCGATTCAGTGGCAGCGGGTATGGGAC AGATTTCACTCTAACCATCAGCAGCCTGCAGG CTGAAGATGTGGCAGTTTATTACTGTCAGCAA TATTATAGTACTCCGTGGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCTGACAGTG GTAACACAGGCTTTGCACAGAAGTTCCAGGCA GAGTCACCATGACCAGGAACACCTCCATAAGCA CAGCCTACATGGAGCTGAGCAGCCTGAGATCTG AGGACACGGCCGTGTATTACTGTGCGGTTTCCAG TGGCTGGTACTGGTTCGACCCTGGGGCCAGGGA ACCCTGGTCACCGTCTCCTCA |
| | | | SEQ ID NO: 27893 | SEQ ID NO: 31899 |
| | | AA | DIVMTQCPDSPAVSLGERASINCKSSQSILHSSNN YNYLAWYQQKPGQHPHKLLIYWASTRESGVPDR FSGSGYGTDFTLTISSLQAEDVAVYYCQQYYSTP WTFGQGTKVEIK | QVQLVQSGAEVKKPGASVKVSCKASGYTFTNYDIN WVRQATGQGLEWMGWMNPDSGNTGFAQKFQGR VTMTRNTSISTAYMELSSLRSEDTAVYYCAVSSGW YWFDPWGQGTLVTVSS |
| | | | SEQ ID NO: 27894 | SEQ ID NO: 31900 |
| iPS:437363 | 21-225_74C10 | NA | GACATCGTGATGACCCAGTCTCCAGACTCCCT GGCTGTGTCTCTGGGCGAGAGGGCCACCATCA ACTGCAAGTCCAGCCAGAGTACTTAGCTTGGTACCA TCCAACAATGCGAACTACTTAGCTTGGTACCA GCAGAAACCAGGACAGCCTCCTAACCTGCTCA TTTACTGGGCATCTACCCGGAATCCGGGGTC CCTGACCGATTCAGTGGCAGCGGGTCTGGGAC AGATTTCACTCTCACCATCAGCAGCCTGCAGG CTGAAGATGTGGCAGTTTATTACTGTCAGCAA CTGGTTACTCCGTGCAGTTTGGCCAGGG GACCAAGCTGGAGATCAAA | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGAACCTGACAGTG GTAACATAGGCTATGCACAGAAGTTCCAGGCA GAGTCACCATGACCAGGAACACCTCCATAAGCA CAGCCTACATGGAGCTGAGCAGCCTGAGATCTG AGGACACGGCCGTGTATTACTGTGCGATTAGCAG TGGCTGGTACTGGTTCGACCCCTGGGGCCAGGGA ACCCTGGTCACCGTCTCCTCA |
| | | | SEQ ID NO: 27895 | SEQ ID NO: 31901 |

FIGURE 50
(Continued)

| | | | | |
|---|---|---|---|---|
| iPS:437369 | 21-225_74D6 | AA | DIVMTQSPDSLAVSLGERATINCKSSQSVLYSSN NANYLAWYQQKPGQPPNLLIYWASTRESGVPD RFSGSGSGTDFTLTISSLQAEDVAVYYCQQYYST PCSFGQGTKLEIK<br>SEQ ID NO: 27896 | QVQLVQSGAEVKKPGASVKVSCKASGYTFTNYDIN WVRQATGQGLEWMGWMNPNSGNIGYAQKFQGR VTMTRNTSISTAYMELSSLRSEDTAVYYCAISSGW YWFDPWGQGTLVTVSS<br>SEQ ID NO: 31902 |
| | | NA | GAAATTGTGTTGACGCAGTCTCCAGGCACCCT GTCTTTGTCTCCAGGGGAAAGAGCACCCTCT CATGCAGGGCCAGTCAGAGTGTTTACAGCAGC TACTTAGCCTGGTACCAGCAGAAACCTGGCCA GGCTCCCAGGCTCCTCATTTATGGTGCATCA GCCGGGCCACTGGCATCCCAGACAGGTTCAGT GGCAGTGGGTGTGGGACAGACTTCGCTCTCAC CATCAGCAGACTGGAGCCTGAAGATTTTGCAG TGTATTACTGTCAGCATTATGATAACTCACCGT GGACGTTCGGCCAAGGGACCAAGGTGGAAAT CAAA<br>SEQ ID NO: 27897 | CAGGTGCAGTACAGAGCAGTGGGGCGCAGGACTG TTGAAGCCTTCGGAGACCCTGTCCCTCACCTGCG CTGTCCATGGTGGTCCTTCAGTGGTTGCTACTG GAGCTGGATCCGCCAGCCCCAGGGAAGGGGCT GGAGTGGATTGGGGAAATCAATCATAGTGGAAG CACCAACTACAACCCGTCCTCCTCAAGAGTCGAGTC ACCATTTCAGTAGACACGTCCAAGAACCAGTTCT CCCTGAAGCTGAGCTCTGTGACCGCCGCGACAC GGCTGTGTATTACTGTGCGAGGGACTACGGCGGT ATGGACGTCTGGGGCCAAGGGACCACGGTCACC GTCTCCTCA<br>SEQ ID NO: 31903 |
| | | AA | EIVLTQSPGTLSLSPGERATLSCRASQSVYSSYLA WYQQKPGQAPRLLIYGASSRATGIPDRFSGSGCG TDFALTISRLEPEDFAVYYCQHYDNSPWTFGQG TKVEIK<br>SEQ ID NO: 27898 | QVQLQQWGAGLLKPSETLSLTCAVHGGSFSGCYW SWIRQPPGKGLEWIGEINHSGSTNYNPSLKSRVTISV DTSKNQFSLKLSSVTAADTAVYYCARDYGGMDV WGQGTTVTVSS<br>SEQ ID NO: 31904 |

FIGURE 50
(Continued)

| | | | | |
|---|---|---|---|---|
| iPS:437371 | 21-225_74D8 | NA | GATATTGTGATGACTCAGTCTCCACTCTCCCTG CCCGTCACCCCTGGAGAGCCGGCCTCCATCTC ATGCAGGTCTAGTCAGAGCCTCGTGCATAGTA GTGGATACAACTATTTGGATTGGTACCTGCAG AAGCCAGGGCAGTCTCCACAGCTCGTTATCTA TTTGGGTTCTAATGGGGCCTCCGGGGTCCCTG ACAGGTTCAGTGGCAGTGGATCAGGCTCAGAT TTTACACTGAAGATCAGCAGAGTGGAGGCTGA GGATGTTGGACTTTATTACTGCATGCAAGCTC TACACCCTCCTCTCACTTTCGGCGGAGGGACC AAGGTGGAGATCAAA | GAGGTGCAGCTGGTGGAGTCTGGGGGAGGCTTG GTACAGCCGGGGGGGTCCCTGAGACTCTCCTGTG CAGCCTCTGGATTCACCTTCAGTAACTACGACAT GCACTGGGTGCGCCAAGCTACAGGAAAAGGTCT GGAGTGGGTCTCAGCTATTGGTACTGCTGGTGAC ACATACTATCCAGGCTCCGTGAAGGGCCGATTCA CCATCTCCAGAGAAATGCCAAGAACTCCTTGTA TCTTCAAATGAACAGCCTGAGAGCCGGGGACAC GGCTGTGTATTACTGTGCAAGAGTTCTTGACTAC GGTGACTCCTGGGCTACTACTACGGTATGG ACGTCTGGGGCCAAGGGACCACGGTCACCGTCTC CTCA |
| | | | SEQ ID NO: 27899 | SEQ ID NO: 31905 |
| | | AA | DIVMTQSPLSLPVTPGEPASISCRSSQSLVHSSGY NYLDWYLQKPGQSPQLVIYLGSNRASGVPDRFS GSGSGSDFTLKISRVEAEDVGLYYCMQALHPPL TFGGGTKVEIK | EVQLVESGGGLVQPGGSLRLSCAASGFTFSNYDMH WVRQATGKGLEWVSAIGTAGDTYYPGSVKGRFTIS RENAKNSLYLQMNSLRAGDTAVYYCARVLDYGDS WGYYYGMDVWGQGTTVTVSS |
| | | | SEQ ID NO: 27900 | SEQ ID NO: 31906 |
| iPS:437377 | 21-225_74G9 | NA | GAATTTATTGTGACGCAGTCTCCAGGCACCCT GTCTTTGTCTCCAGGGGAAAGAGCCACCCTCT CCTGCAGGGCCAGTCAGAGTGTTAGCAGCAGC TACTTAGTCTGGTATCAGCAGAAAACTGGCCA GGCTCCCAGGCTCCTCATCTATGGTGCATCCA CCAGGGCCACTGGCATCCCAGACAGGTTCAGT GGCAGTGGGTCTGGGACAGACTTCACTCTCAC CATCAGCAGACTGGAGCCTGAATATTTTGCAG TTTATTACTGTCAGCAGTATGGTTGTCACCGC TCACTTTCGGCGGAGGGACCAAGGTGGAGATC ACA | CAGATCACCTTGAAGGAGTCTGGTCCTACGCTGG TGAAACCCACACAGACCCTCACGCTGACCTGCAC CTTCTCTGGGTTCTCACTCAGCACTGGTGAGTG GGTGTGGGCTGGATCCGTCAGCCCCCAGGAAAG GCCCCTGGAGTGGCTTGCACTCATTATTGGGATG ATGATAAGGCTACAAGCCCATCTCTGAAGAGCA GGCTCACCATCACCAAGGACACCCCCAAAAACC AGGTGGTCCTTACAATGACCAACATGACCCTGT GGACACAGCCACATATTACTGTGCACACCTTATA GCAGTGGCCTTTGACTACTGGGGCCAGGGAACCC TGGTCACCGTCTCCTCA |
| | | | SEQ ID NO: 27901 | SEQ ID NO: 31907 |

FIGURE 50
(Continued)

| | | | | |
|---|---|---|---|---|
| iPS:437379 | 21-225_74H2 | AA | EFMLTQSPGTLSLSPGERATLSCRASQSVSSSYL VWYQQKPGQAPRLLIYGASTRATGIPDRFSGSGS GTDFTLTISRLEPEYFAVYYCQQYGCSPLTFGGG TKVEIT | QITLKESGPTLVKPTQTLTLTCTFSGFSLSTGGVGVG WIRQPPGKALEWLALIYWDDDKRYSPSLKSRLTIT KDTPKNQVVLTMTMDPVDTATYYCAHLIAVAFD YWGQGTLVTVSS |
| | | | SEQ ID NO: 27902 | SEQ ID NO: 31908 |
| | | NA | GACATCGTGATGACCCAGTCTCCAGACTCCCT GGCTGTGTCTCTGGGCGAGAGGGCCACCATCA ACTGCAAGTCCAGCCAGAGTGTTTACACAGC TCCAACAATAAGAACTACTTAACTTGGTACCA GCAGAAACCAGGACAGCCTCATAAGCTCCTCA TTTACTGGGCATCTCAGATCCGGGGGTC CCTGACCGATTCAGTGGCAGCGGGTCTGGGAC AGATTCAGTCTCACGATCGGCAGCCTGCAGG CTGAAGATGTGGCAGTTTATTACTGTCAGCAA TATTATAGTATTCCTCCGACGTTCGGCCAAGG GACCAAGGTGGAAATCAAA | CAGGTGCAGCTGGTGCAGTCTGGGGCTGAGGTG AAGAAGCCTGGGGCCTCAGTGAAGGTCTCCTGC AAGGCTTCTGGATTCACCTTCACCAATTATGATA TCAACTGGGTGCGACAGGCCACTGGACAAGGC TTGAGTGGATGGGATGGATGCACCCTAACAGTGG TAACACAGGCTTTGCACAGAAGTTCCAGGGCAG AGTCACCATGACCAGGAACACCTCCATAAGCAC AGCCTACATGGAACTGAGCAGCCTGAGATCTGA GGACACGGCCGTGTATTACTGTGCGGTTTCCAGT GGCTGGTACTGGTTCGACCCCTGGGGCCAGGGA ACCCTGGTCACCGTCTCCTCA |
| | | | SEQ ID NO: 27903 | SEQ ID NO: 31909 |
| | | AA | DIVMTQSPDSLAVSLGERATINCKSSQSVLHSSN NKNYLTWYQQKPGQPHKLLIYWASTRESGVPD RFSGSGSGTDFSLTIGSLQAEDVAVYYCQQYYSI PPTFGQGTKVEIK | QVQLVQSGAEVKKPGASVKVSCKASGFTFTNYDIN WVRQATGQGLEWMGWMHPNSGNTGFAQKFQGR VTMTRNTSISTAYMELSSLRSEDTAVYYCAVSSGW YWFDPWGQGTLVTVSS |
| | | | SEQ ID NO: 27904 | SEQ ID NO: 31910 |

FIGURE 50
(Continued)

| | | | | |
|---|---|---|---|---|
| iPS:437383 | 21-225_74H8 | NA | GAAATTGTGTTGACGCAGTCTCCAGGCACCCT GTCTTTGTCTCTCCAGGGGAAAGAGCCACCCTCT CCTGCAGGGCCAGTCAGTTTAGCAGCAGC TACTTAGCCTGGTACCAGCAGAAACCTGGCCA GGCTCCCAGGCTCCTCATTTATGGTGCATCA GCAGGGCCACTGGCATCCCAGACAGCTTCAGT GGCAGTGGGTCTGGGACAGAGCCTGAAGATTT CATCAGCAGACTGGAGCTGAAGATTTTGCAG TGTATTACTGTCAGCAGTATGGTAGCTCAAGG ACGTTCGGCCAAGGGACCAAGGTGGAAATCA AA | GAGGTGCACCTGGTGGAGTCTGGGGGAGGCTTG GTAAAGCCTGGGGGGTCCCTGAGACTCTCCTGTG CAGCCTCTGGATTCACTTTCAGTAACGCCTGGAT GAACTGGGTCCGCCAGGCTCCAGGGAAGGGCT GGAGTGGGTTGGCCGTATTAAAAGCAAAACTGA TGGTGGGACAACAGACTACGCTGCACCGTGAA AGGCAGATTCACCATCTCAAGAGATGATTCAAA AACACGCTGTATCTGCAAATGAACAGCCTGAA AACCGAGGACACAGCCGTGTATTACTGTACCACA GTGGGGAGCTACTACGGACTACTGGGGCCAGGGA ACCCTGGTCACCGTCTCCTCA |
| | | | SEQ ID NO: 27905 | SEQ ID NO: 31911 |
| | | AA | EIVLTQSPGTLSLSPGERATLSCRASQSFSSSYLA WYQQKPGQAPRLLIYGASSRATGIPDRFSGSGSG TDFTLTISRLEPEDFAVYYCQQYGSSRTFGQGTK VEIK | EVHLVESGGGLVKPGGSLRLSCAASGFTFSNAWM NWVRQAPGKGLEWVGRIKSKTDGGTTDYAAPVK GRFTISRDDSKNTLYLQMNSLKTEDTAVYYCTTVG ATTDYWGQGTLVTVSS |
| | | | SEQ ID NO: 27906 | SEQ ID NO: 31912 |
| iPS:438664 | 21-225_216G1 | NA | GACATCGAGATGACCCAGTCTCCATCCTCACT GTCTGCATCTGTAGGAGACAGAGTCACCATCA CTTGTCGGGCGAGTCAGGGCATTAGCAGTTAT TTAGCCTGGTTTCAGCAGAAACCAGGGAAAGC CCCTAAGTCCCTGATCTATGCTGCATCCAGTTT GCAAAGTGGGGTCCCATCAAGGTTCAGCGGCA GTGGATCTGGGACAGATTTCACTCTCACCATC AGCAGCCTGCAGCCTGAAGATTTCGCAACTTA TTATTGCCTACGGTATGATACTTACCCTCTCAC TTTCGGCGGAGGGACCAAGGTGGAGATCAAG | CAGGTGCACCTGGTGGAGTCTGGGGGAGGCGTG GTCCAGCCTGGGAGGTCCCTGAGACTCTCCTGTG CAGCGTCTGGATTCACCTTCAGTAACTATGGCAT GCACTGGGTCCGCCAGGCTCCAGGCAAGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGGGGGACTG GAACCCGAGGTATGACGTCTGGGGCCAAGG GACCACGGTCATCGTCTCCTCA |
| | | | SEQ ID NO: 27907 | SEQ ID NO: 31913 |

FIGURE 50
(Continued)

| | | | |
|---|---|---|---|
| iPS:441468 | 21-225_25A4.001.001 | AA | DIEMTQSPSSLSASVGDRVTITCRASQGISSYLAWLQQKPGKAPKSLIYAASSLQSGVPSRFSGSGSGTDFTLTISSLQPEDFATYYCLRYDTYPLTFGGGTKVEIK<br>SEQ ID NO: 27908 | QVHLVESGGGVVQPGRSLRLSCAASGFTFSNYGMHWVRQAPGKGLEWVAVIWYDGSNKYYADSVKGRFTISRDNSKNTLYLQMNSLRAEDTAVYYCARGDWNPEGMDVWGQGTTVTVSS<br>SEQ ID NO: 31914 |
| | | NA | GACATCGTGATGACCCAGTTTCCAGACTCCCTGGCTGTGTCTCTGGGCGAGAGGGCCACCATCAAGTGTAAGTCCAGCCAGAGTGTTTTATACAGCTCCCACAATAACAACTACTTAGCTTGGTACCAGCAGAAACCAGGACAGCCTCCTAAGTTGCTCCTTTACTGGGCATCTCAGTGGGAATCCGGGGTCCCTGACCGATTCAGTGGCAGTGGGTCTGGGACAGAATTCACTCTCACCATCAGCAGCCTGGAGGCTGAAGATGTGGCAGTTTATTACTGTCAGCAGTATTATAGTACTCCTCGACGTTCGGCCAAGGGACCAAGGTGGAAATCAAA<br>SEQ ID NO: 27909 | CAGGTGCTCCTGGTGCAGTCTGGGGGCTGAGGTGAAGAGGCCTGGGGCCTCAGTGAAGGTCAGCTGCAAGGCTTCTGGATACACCTTCACCAATTATGATATTAATTGGGTGCGACAGGCCACTGGACAAGGGCTTGAGTGGATGGGATGGATGTACCTAACAGTGGTAGCACAGGCTATGCACAGAAATTCCAGGCAGAGTCACCATGACCAGGGACACCTCCATCAGCACAGCCTACATGGAGCTGAGCAGCCTGAGATCTGAGGACACGGCCGTCTATTACTGTGCGAGTAGCAGTGGCTGGTACTACTTTGACTACTGGGGCCAGGGAACCCTGGTCACCGTGTCCTCA<br>SEQ ID NO: 31915 |
| | | AA | DIVMTQFPDSLAVSLGERATIKCKSSQSVLYSSHNNNYLAWYQQKPGQPPKLLLYWASTRESGVPDRFSGSGSGTEFTLTISSLEAEDVAVYYCQQYYSTPPTFGQGTKVEIK<br>SEQ ID NO: 27910 | QVLLVQSGAEVKRPGASVKVSCKASGYTFTNYDINWVRQATGQGLEWMGWMYPNSGSTGYAQKFQGRVTMTRDTSISTAYMELSSLRSEDTAVYYCASSSGWYYFDYWGQGTLVTVSS<br>SEQ ID NO: 31916 |

FIGURE 50
(Continued)

| | | | | |
|---|---|---|---|---|
| iPS:441475 | 21-225_25A4.001.002 | NA | GACATCGTGATGACCCAGTTTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTC TTTACTGGGCATCTACCCGGAATCGGGGTC CCTGACCGATTCAGTGGCAGCGGGTCTGGAC AGAATTCACTCTCACCATCAGCAGCCTGGAGG CTGAAGATGTGGCAGTTTATTACTGTCAGCAG TATTATAGTACTCCCTCCGACGTTCGGCCAAGG GACCAAGGTGGAAATCAAA<br><br>SEQ ID NO: 27911 | CAGGTGCTCCTGGTGCAGTCTGGGGCTGAGGTGA AGAGGCCTGGGGCCTCAGTGAAGGTCAGCTGCA AGGCTTCTGGATACACCTTCACCAATTATGATAT TAATTGGGTGCGACAGGCCACTGGACAAGGGCT TGAGTGGATGGGATGGATGTACCCTAACAGTGGT AACGCAGGCTATGCACAGAAATTCCAGGGCAGA GTCACCATGACCAGGGACACCTCCATCAGCACA GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTGTCCTCA<br><br>SEQ ID NO: 31917 |
| | | AA | DIVMTQFPDSLAVSLGERATIKCKSSQSVLYSSH NNNYLAWYQQKPGQPPKLLLYWASTRESGVPD RFSGSGSGTEFTLTISSLEAEDVAVYYCQQYYST PPTFGQGTKVEIK<br><br>SEQ ID NO: 27912 | QVLLVQSGAEVKRPGASVKVSCKASGYTFTNYDIN WVRQATGQGLEWMGWMYPNSGNAGYAQKFQGR VTMTRDTSISTAYMELSSLRSEDTAVYYCASSSGW YYFDYWGQGTLVTVSS<br><br>SEQ ID NO: 31918 |
| iPS:441482 | 21-225_25A4.001.003 | NA | GACATCGTGATGACCCAGTTTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTC TTTACTGGGCATCTACCCGGAATCGGGGTC CCTGACCGATTCAGTGGCAGCGGGTCTGGAC AGAATTCACTCTCACCATCAGCAGCCTGGAGG CTGAAGATGTGGCAGTTTATTACTGTCAGCAAG TATTATAGTACTCCCTCCGACGTTCGGCCAAGG GACCAAGGTGGAAATCAAA<br><br>SEQ ID NO: 27913 | CAGGTGCTCCTGGTGCAGTCTGGGGCTGAGGTGA AGAGGCCTGGGGCCTCAGTGAAGGTCAGCTGCA AGGCTTCTGGATACACCTTCACCAATTATGATAT TAATTGGGTGCGACAGGCCACTGGACAAGGGCT TGAGTGGATGGGATGGATGTACCCTAACAGTGGT AACGTAGGCTATGCACAGAAATTCCAGGGCAGA GTCACCATGACCAGGGACACCTCCATCAGCACA GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTGTCCTCA<br><br>SEQ ID NO: 31919 |

FIGURE 50
(Continued)

| | | | | |
|---|---|---|---|---|
| | | | AA | DIVMTQFPDSLAVSLGERATIKCKSSQSVLYSSH NNNYLAWYQQKPGQPPKLLLYWASTRESGVPD RFSGSGSGTEFTLTISSLEAEDVAVYYCQQYYST PPTFGQGTKVEIK | QVLLVQSGAEVKRPGASVKVSCKASGYTFTNYDIN WVRQATGQGLEWMGWMYPNSGNVGYAQKFQGR VTMTRDTSISTAYMELSSLRSEDTAVYYCASSSGW YYFDYWGQGTLVTVSS |
| | | | | SEQ ID NO: 27914 | SEQ ID NO: 31920 |
| iPS:441489 | 21-225_25A4.001.004 | | NA | GACATCGTGATGACCCAGTTTCCAGACTCCCT GGCTGTGTCTCTGGGCGAGAGAGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTCACCCGGGAATCCGGGTC CCTGACCGATTCAGTGGCAGCGGGTCTGGGAC AGAATTCACTCTCACCATCAGCAGCCTGGAGG CTGAAGATGTGGCAGTTTATTACTGTCAGCAG TATTATAGTACTCCTCCGACGTTCGGCCAAGG GACCAAGGTGGAAATCAAA | CAGGTGCTCCTGGTGCAGTCTGGGGCTGAGGTGA AGAGGCCTGGGGCCTCAGTGAAGGTCAGCTGCA AGGCTTCTGGATACACCTTCACCAATTATGATAT TAATTGGGTGCGACAGGCCACTGGACAAGGCT TGAGTGGATGGGATGGATGTACCTAACAGTGGT CAAACAGGCTATGCACAGAAATTCCAGGGCAGA GTCACCATGACCAGGGACACCTCCATCAGCACA GCCTACATGGAGCTGAGCAGCCTGAGATCGAG GACACGGCCGTCTATTACTGTGCGAGTAGCAGTG GCTGGTACTACTTTGACTACTGGGGCCAGGGAAC CCTGGTCACCGTGTCCTCA |
| | | | | SEQ ID NO: 27915 | SEQ ID NO: 31921 |
| | | | AA | DIVMTQFPDSLAVSLGERATIKCKSSQSVLYSSH NNNYLAWYQQKPGQPPKLLLYWASTRESGVPD RFSGSGSGTEFTLTISSLEAEDVAVYYCQQYYST PPTFGQGTKVEIK | QVLLVQSGAEVKRPGASVKVSCKASGYTFTNYDIN WVRQATGQGLEWMGWMYPNSGQTGYAQKFQGR VTMTRDTSISTAYMELSSLRSEDTAVYYCASSSGW YYFDYWGQGTLVTVSS |
| | | | | SEQ ID NO: 27916 | SEQ ID NO: 31922 |

FIGURE 50
(Continued)

| | | | |
|---|---|---|---|
| iPS:441496 | 21-225_25A4.001.005 | NA | GACATCGTGATGACCCAGTCTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGAATCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCCTCGACGTTCGGCCAAGG GACCAAGGTGGAAATCAAA SEQ ID NO: 27917 | DIVMTQSPDSLAVSLGERATIKCKSSQSVLYSSH NNNYLAWYQQKPGQPPKLLLYWASTRESGVPD RFSGSGSGTEFTLTISSLQAEDVAVYYCQQYYST PPTFGQGTKVEIK SEQ ID NO: 27918 |
| | | AA | QVQLVQSGAEVKRPGASVKVSCKASGYTFTNYDIN WVRQATGQGLEWMGWMYPNSGSTGYAQKFQGR VTMTRDTSISTAYMELSSLRSEDTAVYYCASSSGW YYFDYWGQGTLVTVSS SEQ ID NO: 31923 |
| | | | CAGGTGCAACTGGTGCAGTCTGGGGCTGAGGTG AAGAGGCCTGGGGCCTCAGTGAAGGTCAGTGC AAGGCTTCTGGATACACCTTCACCAATTATGATA TTAATTGGGTGCGACAGGCCACTGGACAAGGC TTGAGTGGATGGGATGGATGTACCCTAACAGTGG TAGCACAGGCTATGCACAGAAATTCCAGGCAG AGTCACCATGACCAGGGACACCTCCATCAGCAC AGCCTACATGGAGCTGAGCAGCCTGAGATCTGA GGACACGGCCGTCTATTACTGTGCGAGTAGCAGT GGCTGGTACTACTTTGACTACTGGGGCCAGGGAA CCCTGGTCACCGTCCTCA SEQ ID NO: 31924 |
| iPS:441505 | 21-225_25A4.001.006 | NA | GACATCGTGATGACCCAGTCTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGGAATCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCCTCGACGTTCGGCCAAGG GACCAAGGTGGAAATCAAA SEQ ID NO: 27919 | CAGGTGCAACTGGTGCAGTCTGGGGCTGAGGTG AAGAGGCCTGGGGCCTCAGTGAAGGTCAGTGC AAGGCTTCTGGATACACCTTCACCAATTATGATA TTAATTGGGTGCGACAGGCCACTGGACAAGGC TTGAGTGGATGGGATGGATGTACCCTAACAGTGG TAACGCAGGCTATGCACAGAAATTCCAGGCAG AGTCACCATGACCAGGGACACCTCCATCAGCAC AGCCTACATGGAGCTGAGCAGCCTGAGATCTGA GGACACGGCCGTCTATTACTGTGCGAGTAGCAGT GGCTGGTACTACTTTGACTACTGGGGCCAGGGAA CCCTGGTCACCGTCCTCA SEQ ID NO: 31925 |

FIGURE 50
(Continued)

| | | | |
|---|---|---|---|
| | | AA | DIVMTQSPDSLAVSLGERATIKCKSSQSVLYSSH NNNYLAWYQQKPGQPPKLLLYWASTRESGVPD RFSGSGSGTEFTLTISSLQAEDVAVYYCQQYYST PPTFGQGTKVEIK | QVQLVQSGAEVKRPGASVKVSCKASGYTFTNYDIN WVRQATGQGLEWMGWMYPNSGNAGYAQKFQGR VTMTRDTSISTAYMELSSLRSEDTAVYYCASSSGW YYFDYWGQGTLVTSS |
| | | | SEQ ID NO: 27920 | SEQ ID NO: 31926 |
| iPS:441512 | 21-225_25A4.001.007 | NA | GACATCGTGATGACCCAGTCTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTC TTTACTGGGCATCTACCCGGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCTCCGACGTTCGGCCAAGG GACCAAGGTGGAAATCAAA | CAGGTGCAACTGGTGCAGTCTGGGGCTGAGGTG AAGAGGCCTGGGGCCTCAGTGAAGGTCAGCTGC AAGGCTTCTGGATACACCTTCACCAATTATGATA TTAATTGGGTGCGACAGGCCACTGGACAAGGC TTGAGTGGATGGGATGGATGTACCCTAACAGTGG TAACGTAGGCTATGCACAGAAATTCCAGGGCAG AGTCACCATGACCAGGGACACCTCCATCAGCAC AGCCTACATGGAGCTGAGCAGCCTGAGATCTGA GGACACGGCCGTCTATTACTGTGCGAGTAGCAGT GGCTGGTACTACTTTGACTACTGGGGCCAGGGAA CCCTGGTCACCGTCTCCTCA |
| | | | SEQ ID NO: 27921 | SEQ ID NO: 31927 |
| | | AA | DIVMTQSPDSLAVSLGERATIKCKSSQSVLYSSH NNNYLAWYQQKPGQPPKLLLYWASTRESGVPD RFSGSGSGTEFTLTISSLQAEDVAVYYCQQYYST PPTFGQGTKVEIK | QVQLVQSGAEVKRPGASVKVSCKASGYTFTNYDIN WVRQATGQGLEWMGWMYPNSGNVGYAQKFQGR VTMTRDTSISTAYMELSSLRSEDTAVYYCASSSGW YYFDYWGQGTLVTSS |
| | | | SEQ ID NO: 27922 | SEQ ID NO: 31928 |

FIGURE 50
(Continued)

| | | | |
|---|---|---|---|
| iPS:441519 | 21-225_25A4.001.008 | NA | GACATCGTGATGACCCAGTCTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCTCCGACGTTCGGCCAAGG GACCAAGGTGGAAATCAAA<br><br>SEQ ID NO: 27923 | CAGGTGCAACTGGTGCAGTCTGGGGCTGAGGTG AAGAGGCCTGGGCCCTCAGTGAAGGTCAGCTGC AAGGCTTCTGGATACACCTTCACCAATTATGATA TTAATTGGGTGCGACAGGCCACTGGACAAGGC TTGAGTGGATGGGATGGATGTACCCTAACAGTGG TCAAACAGGCTATGCACAGAAATTCAGGGCAG AGTCACCATGACCAGGGACACCTCCATCAGCAC AGCCTACATGGAGCTGAGCAGCCTGAGATCTGA GGACACGGCCGTCTATTACTGTGCGAGTAGCAGT GGCTGGTACTACTTTGACTACTGGGGCCAGGGAA CCCTGGTCACCGTGTCCTCA<br><br>SEQ ID NO: 31929 |
| | | AA | DIVMTQSPDSLAVSLGERATIKCKSSQSVLYSSH NNNYLAWYQQKPGQPPKLLLYWASTRESGVPD RFSGSGSGTEFTLTISSLQAEDVAVYYCQQYYST PPTFGQGTKVEIK<br><br>SEQ ID NO: 27924 | QVQLVQSGAEVKRPGASVKVSCKASGYTFTNYDIN WVRQATGQGLEWMGWMYPNSGQTGYAQKFQGR VTMTRDTSISTAYMELSSLRSEDTAVYYCASSSGW YYFDYWGQGTLVTVSS<br><br>SEQ ID NO: 31930 |
| iPS:441554 | 21-225_25A4.001.013 | NA | GACATCGTGATGACCCAGTTTCCAGACTCCCT GGCTGTGTCTCTGGGCGAGAGGGCCACCATCA AGTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGAATCCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCTCCGACGTTCGGCCAAGG GACCAAGGTGGAAATCAAA<br><br>SEQ ID NO: 27925 | CAGGTGCTCCTGGTGCAGTCTGGGGCTGAGGTGA AGAGGCCTGGGCCCTCAGTGAAGGTCAGCTGCA AGGCTTCTGGATACACCTTCACCAATTATGATAT TAATTGGGTGCGACAGGCCACTGGACAAGGCT TGAGTGGATGGGATGATGTACCCTAACAGTGGT AGCACAGGCTATGCACAGAAATTCAGGGCAGA GTCACCATGACCAGGGACACCTCCATCAGCACA GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTGTCCTCA<br><br>SEQ ID NO: 31931 |

FIGURE 50
(Continued)

| | | | |
|---|---|---|---|
| | | AA | DIVMTQFPDSLAVSLGERATIKCKSSQSVLYSSH NNNYLAWYQQKPGQPPKLLIYWASTRESGVPD RFSGSGSGTEFTLTISSLQAEDVAVYYCQQYYST PPTFGQGTKVEIK | QVLLLVQSGAEVKRPGASVKVSCKASGYTFTNYDIN WVRQATGQGLEWMGWMYPNSGSTGYAQKFQGR VTMTRDTSISTAYMELSSLRSEDTAVYYCASSSGW YYFDYWGQGTLVTVSS |
| | | | SEQ ID NO: 27926 | SEQ ID NO: 31932 |
| iPS:441595 | 21-225_25A4.001.019 | NA | GACATCGTGATGACCCAGTCTCCAGACTCCCT GGCTGTGTCTCTGGGCGAGAGGGCCACCATCA ACTGTAAGTCCAGCCAGAGTGTTTATACAGC TCCCACAATAACAACTACTTAGCTTGGTACCA GCAGAAACCAGGACAGCCTCCTAAGTTGCTC TTTACTGGGCATCTCACCCGGGAATCCGGGTC CCTGACCGATTCAGTGGCAGCGGGTCTGGGAC AGAATTCACTCTCACCATCAGCAGCCTGGAGG CTGAAGATGTGGCAGTTTATTACTGTCAGCAG TATTATAGTACTCCTCCGACGTTCGGCCAAGG GACCAAGGTGGAAATCAAA | CAGGTGCAACTGGTGCAGTCTGGGGCTGAGGTG AAGAGGCCTGGGGCCTCAGTGAAGGTCAGCTGC AAGGCTTCTGGATACACCTTCACCAATTATGATA TTAATTGGGTGCGACAGGCCCCTGGACAAGGCT TGAGTGGATGGGATGGATGTACCTAACAGTGGT AGCACAGGCTATGCACAGAAATTCCAGGGCAGA GTCACCATGACCAGGGACACCTCCATCAGCACA GCCTACATGGAGCTGAGCAGCCTGAGATCTGAG GACACGGCCGTCTATTACTGTGCGAGTAGCAGTG GCTGGTACTACTTTGACTACTGGGGCCAGGGAAC CCTGGTCACCGTGTCCTCA |
| | | | SEQ ID NO: 27927 | SEQ ID NO: 31933 |
| | | AA | DIVMTQSPDSLAVSLGERATINCKSSQSVLYSSH NNNYLAWYQQKPGQPPKLLIYWASTRESGVPD RFSGSGSGTEFTLTISSLEAEDVAVYYCQQYYST PPTFGQGTKVEIK | QVQLVQSGAEVKRPGASVKVSCKASGYTFTNYDIN WVRQAPGQGLEWMGWMYPNSGSTGYAQKFQGR VTMTRDTSISTAYMELSSLRSEDTAVYYCASSSGW YYFDYWGQGTLVTVSS |
| | | | SEQ ID NO: 27928 | SEQ ID NO: 31934 |

FIGURE 50
(Continued)

| | | | |
|---|---|---|---|
| iPS:441604 | 21-225_25A4.001.020 | NA | GACATCGTGATGACCCAGTCTCCAGACTCCCT GGCTGTGTCTCTGGGCGAGAGGGCCACCATCA ACTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGAATCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCCTCGACGTTCGGCCAAGG GACCAAGGTGGAAATCAAA

SEQ ID NO: 27929 | CAGGTGCTCCTGGTGCAGTCTGGGGCTGAGGTGA AGAGGCCTGGGGCCTCAGTGAAGGTCAGCTGCA AGGCTTCTGGATACACCTTCACCAATTATGATAT TAATTGGGTGCGACAGGCCCCTGGACAAGGCTT GAGTGGATGGGATGGATGTACCCTAACAGTGGTC AAACAGGCTATGCACAGAAATTCCAGGGCAGAG TCACCATGAGCCAGGAGACACCTCCATCAGCACAGC CTACATGGAGCTGAGCAGCCTGAGATCTGAGGA CACGGCCGTCTATTACTGTGCGAGTAGCAGTGGC TGGTACTACTTTGACTACTGGGGCCAGGGAACCC TGGTCACCGTCTCCTCA

SEQ ID NO: 31935 |
| | | AA | DIVMTQSPDSLAVSLGERATINCKSSQSVLYSSH NNNYLAWYQQKPGQPPKLLLYWASTRESGVPD RFSGSGSGTEFTLTISSLQAEDVAVYYCQQYYST PPTFGQGTKVEIK

SEQ ID NO: 27930 | QVLLVQSGAEVKRPGASVKVSCKASGYTFTNYDIN WVRQAPGQGLEWMGWMYPNSGQTGYAQKFQGR VTMTRDTSISTAYMELSSLRSEDTAVYYCASSSGW YYFDYWGQGTLVTVSS

SEQ ID NO: 31936 |
| iPS:441613 | 21-225_25A4.001.021 | NA | GACATCGTGATGACCCAGTCTCCAGACTCCCT GGCTGTGTCTCTGGGCGAGAGGGCCACCATCA ACTGTAAGTCCAGCCAGAGTGTTTTATACAGC TCCCACAATAACAACTACTTAGCTTGGTACCA GCAGAAACCAGGACAGCCTCCTAAGTTGCTCC TTTACTGGGCATCTACCCGGAATCGGGGTC CCTGACCGATTCAGTGGCAGCGGGTCTGGGAC AGAATTCACTCTCACCATCAGCAGCCTGCAGG CTGAAGATGTGGCAGTTTATTACTGTCAGCAG TATTATAGTACTCCCTCGACGTTCGGCCAAGG GACCAAGGTGGAAATCAAA

SEQ ID NO: 27931 | CAGGTGCAACTGGTGCAGTCTGGGGCTGAGGTG AAGAAGCCTGGGGCCTCAGTGAAGGTCAGCTGC AAGGCTTCTGGATACACCTTCACCAATTATGATA TTAATTGGGTGCGACAGGCCACTGGACAAGGC TTGAGTGGATGGGATGGATGTACCCTAACAGTGG TAACGCAGGCTATGCACAGAAATTCCAGGGCAG AGTCACCATGACCAGGGACACCTCCATCAGCAC AGCCTACATGGAGCTGAGCAGCCTGAGATCTGA GGACACGGCCGTCTATTACTGTGCGAGTAGCAGT GGCTGGTACTACTTTGACTACTGGGGCCAGGGAA CCCTGGTCACCGTCTCCTCA

SEQ ID NO: 31937 |

FIGURE 50
(Continued)

| | | | |
|---|---|---|---|
| iPS:441841 | 21-225_4A2.001.001 | AA | DIVMTQSPDSLAVSLGERATINCKSSQSVLYSSH NNNYLAWYQQKPGQPPKLLLYWASTRESGVPD RFSGSGSGTEFTLTISSLQAEDVAVYYCQQYYST PPTFGQGTKVEIK<br><br>SEQ ID NO: 27932 | QVQLVQSGAEVKRPGASVKVSCKASGYTFTNYDIN WVRQATGQGLEWMGWMYPNSGNAGYAQKFQGR VTMTRDTSISTAYMELSSLRSEDTAVYYCASSSGW YYFDYWGQGTLVTVSS<br><br>SEQ ID NO: 31938 |
| | | NA | GACATCGTGATGACCCAGTCTCCAGACTCCCT GGCTGTGTCTCTGGGCGAGAGAGTCCACCATCA ACTGCAAGTCCAGCCAGAGTGTATTTACACAGC TCCAACAATAACAACTACTTAGCTTGGTTCCA GCAGAAACCAGGACAGCCTCCTAAACTGCTCC TTTACTGGGCATCTACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAGTACTCCACTTTCGCGCCCTGGG ACCAAAGTGGGTATCAAA<br><br>SEQ ID NO: 27933 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCTTGACCAGGGACACCTCCATCAGCACA GCCTACATGGAACTGAGCAGCCTGAGATCGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31939 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGPGTKVGIK<br><br>SEQ ID NO: 27934 | QVQLVQSGTEVKKPGASVKVSCKASGYTFTNYDIN WVRQATGQGLEWMGWMHPNSGNTGYAQKFQGR VTLTRDTSISTAYMELSSLRSEDTAVYYCASSSGWY YFDYWGQGTLVTVSS<br><br>SEQ ID NO: 31940 |

FIGURE 50
(Continued)

| | | | | |
|---|---|---|---|---|
| iPS:441847 | 21-225_4A2.001.002 | NA | GACATCGTGATGACCCAGTCTCCAGACTCCCT GGCTGTGTCTCTGGGCGAGAGGGCCACCATCA ACTGCAAGTCCAGCCAGTCAGTATTTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATGCTCCAGTCACTTTCGGCCCTGGG ACCAAAGTGGGTATCAAA SEQ ID NO: 27935 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA SEQ ID NO: 31941 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNAP VTFGPGTKVGIK SEQ ID NO: 27936 | QVQLVQSGTEVKKPGASVKVSCKASGYTFTNYDIN WVRQATGQGLEWMGWMHPNSGNTGYAQKFQGR VTLTRDTSISTAYMELSSLRSEDTAVYYCASSSGWY YFDYWGQGTLVTVSS SEQ ID NO: 31942 |
| iPS:441853 | 21-225_4A2.001.003 | NA | GACATCGTGATGACCCAGTCTCCAGACTCCCT GGCTGTGTCTCTGGGCGAGAGGGCCACCATCA ACTGCAAGTCCAGCCAGTCAGTATTTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATCAAACTCCAGTCACTTTCGGCCTGG GACCAAAGTGGGTATCAAA SEQ ID NO: 27937 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA SEQ ID NO: 31943 |

FIGURE 50
(Continued)

| | | | | |
|---|---|---|---|---|
| iPS:441859 | 21-225_4A2.001.004 | AA | DIVMTQSPDSLAVSLGERATINCKSSQSILHSSNNNNYLAWFQQKPGQPPKLLLYWASTRESGVPDRFSGSGSGTDFTLTISSLQPEDVAVYYCQQYYQTPVTFGPGTKVGIK<br>SEQ ID NO: 27938 | QVQLVQSGTEVKKPGASVKVSCKASGYTFTNYDINWVRQATGQGLEWMGWMHPNSGNTGYAQKFQGRVTLTRDTSISTAYMELSSLRSEDTAVYYCASSSGWYYFDYWGQGTLVTVSS<br>SEQ ID NO: 31944 |
| | | NA | GACATCGTGATGACCCAGTCTCCAGACTCCCTGGCTGTGTCTCTGGGCGAGAGGGCCACCATCAACTGCAAGTCCAGCCAGAGTATTTTACACAGCTCCAACAATAACAACTACTTAGCTTGGTTCCAGCAGAAACCAGGACAGCCTCCTAAACTGCTCCTTTACTGGGCATCTCACCCGGGAATCCCGGGGTCCCTGACCGATTCAGTGGCAGCGGGTCTGGGACAGATTTCACTCTCACCATCAGCAGCCTGCAGCCTGAAGATGTGGCAGTTTATTACTGTCAGCAATATTATAATACTCCAGTCACTTTCGGCCCTGGGACCAAAGTGGGTATCAAA<br>SEQ ID NO: 27939 | CAGGTGCAGCTGGTGCAGTCTGGGACTGAGGTGAAGAAGCCTGGGGCCTCAGTGAAGGTGTCCTGCAAGGCTTCTGGATACACCTTCACCAATTATGATATCAACTGGGTGCGACAGGCCACTGGACAAGGCCTTGAGTGGATGGGATGGATGCACAGAAGTTCCAGGGCAGTAACGCAGGCTATGCACAGGAGACACCTCCATCAGCACAAGTCACCTTGACCAGGGACACATGGCTACATGGAACTGAGCAGCCTGAGATCTGAGGACACGGCCGTGTATTACTGTGCGAGTAGCAGTGGCTGGTACTACTTTGACTACTGGGGCCAGGGAACCCTGGTCACCGTGTCCTCA<br>SEQ ID NO: 31945 |
| | | AA | DIVMTQSPDSLAVSLGERATINCKSSQSILHSSNNNNYLAWFQQKPGQPPKLLLYWASTRESGVPDRFSGSGSGTDFTLTISSLQPEDVAVYYCQQYYNTPVTFGPGTKVGIK<br>SEQ ID NO: 27940 | QVQLVQSGTEVKKPGASVKVSCKASGYTFTNYDINWVRQATGQGLEWMGWMHPNSGNAGYAQKFQGRVTLTRDTSISTAYMELSSLRSEDTAVYYCASSSGWYYFDYWGQGTLVTVSS<br>SEQ ID NO: 31946 |

FIGURE 50
(Continued)

| | | | | |
|---|---|---|---|---|
| iPS:441866 | 21-225_4A2.001.005 | NA | GACATCGTGATGACCCAGTCTCCAGACTCCCT GGCTGTGTCTCTGGGCGAGAGGGCCACCATCA ACTGCAAGTCCAGCAGTGATATTTACACAGC TCCAACAATAACAACTACTTAGCTTGGTTCCA GCAGAAACCAGGACAGCCTCCTAAACTGCTCC TTTACTGGGCATCTACCCGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATACTCCAGTCACTTTCGGCCCTGGG ACCAAAGTGGGGTATCAAA SEQ ID NO: 27941 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAGCACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA SEQ ID NO: 31947 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNTP VTFGPGTKVGIK SEQ ID NO: 27942 | QVQLVQSGTEVKKPGASVKVSCKASGYTFTNYDIN WVRQATGQGLEWMGWMHPNSGSTGYAQKFQGR VTLTRDTSISTAYMELSSLRSEDTAVYYCASSSGWY YFDYWGQGTLVTVSS SEQ ID NO: 31948 |
| iPS:441873 | 21-225_4A2.001.006 | NA | GACATCGTGATGACCCAGTCTCCAGACTCCCT GGCTGTGTCTCTGGGCGAGAGGGCCACCATCA ACTGCAAGTCCAGCCAGTGATATTTACACAGC TCCAACAATAACAACTACTTAGCTTGGTTCCA GCAGAAACCAGGACAGCCTCCTAAACTGCTCC TTTACTGGGCATCTACCCGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATACTCCAGTCACTTTCGGCCCTGGG ACCAAAGTGGGGTATCAAA SEQ ID NO: 27943 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TCAAACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA SEQ ID NO: 31949 |

FIGURE 50
(Continued)

| | | | |
|---|---|---|---|
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNTP VTFGPGTKVGIK<br><br>SEQ ID NO: 27944 | QVQLVQSGTEVKKPGASVKVSCKASGYTFTNYDIN WVRQATGQGLEWMGWMHPNSGQTGYAQKFQGR VTLTRDTSISTAYMELSSLRSEDTAVYYCASSSGWY YFDYWGQGTLVTVSS<br><br>SEQ ID NO: 31950 |
| iPS:441880 | 21-225_4A2.001.007 | NA | GACATCGTGATGACCCAGTCTCCAGACTCCCT GGCTGTGTCTCTGGGCGAGAGGGCCACCATCA ACTGCAAGTCCAGCCAGAGTATTTACACAGC TCCAACAATAACAACTACTTAGCTTGGTTCCA GCAGAAACCAGGACAGCCTCCTAAACTGCTCC TTTACTGGGCATCTCACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAGTACTCCAGTCACTTTCGGCCCTGGG ACCAAAGTGGGTATCAAA<br><br>SEQ ID NO: 27945 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TCAAACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGCCTCA<br><br>SEQ ID NO: 31951 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGPGTKVGIK<br><br>SEQ ID NO: 27946 | QVQLVQSGTEVKKPGASVKVSCKASGYTFTNYDIN WVRQATGQGLEWMGWMHPNSGQTGYAQKFQGR VTLTRDTSISTAYMELSSLRSEDTAVYYCASSSGWY YFDYWGQGTLVTVSS<br><br>SEQ ID NO: 31952 |

FIGURE 50
(Continued)

| | | | | |
|---|---|---|---|---|
| iPS:441884 | 21-225_4A2.001.008 | NA | GACATCGTGATGACCCAGTCTCCAGACTCCCT GGCTGTGTCTCTGGGCGAGAGGGCCACCATCA ACTGCAAGTCCAGCCAGTCAGAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAGTACTCCAGTCACTTTCGGCCCTGGG ACCAAAGTGGGTATCAAA | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACGCAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA |
| | | | SEQ ID NO: 27947 | SEQ ID NO: 31953 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGPGTKVGIK | QVQLVQSGTEVKKPGASVKVSCKASGYTFTNYDIN WVRQATGQGLEWMGWMHPNSGNAGYAQKFQGR VTLTRDTSISTAYMELSSLRSEDTAVYYCASSSGWY YFDYWGQGTLVTVSS |
| | | | SEQ ID NO: 27948 | SEQ ID NO: 31954 |
| iPS:441888 | 21-225_4A2.001.009 | NA | GACATCGTGATGACCCAGTCTCCAGACTCCCT GGCTGTGTCTCTGGGCGAGAGGGCCACCATCA ACTGCAAGTCCAGCCAGTCAGAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATGCTCCAGTCACTTTCGGCCCTGGG ACCAAAGTGGGTATCAAA | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TCAAACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGTGAGTAGCAGTG GCTGGTACTACTTTGACTACTGGGGCCAGGGAAC CCTGGTCACCGTGTCCTCA |
| | | | SEQ ID NO: 27949 | SEQ ID NO: 31955 |

FIGURE 50
(Continued)

| | | | | |
|---|---|---|---|---|
| iPS:441892 | 21-225_4A2.001.010 | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNAP VTFGPGTKVGIK<br>SEQ ID NO: 27950 | QVQLVQSGTEVKKPGASVKVSCKASGYTFTNYDIN WVRQATGQGLEWMGWMHPNSGQTGYAQKFQGR VTLTRDTSISTAYMELSSLRSEDTAVYYCASSSGWY YFDYWGQGTLVTVSS<br>SEQ ID NO: 31956 |
| | | NA | GACATCGTGATGACCCAGTCTCCAGACTCCCT GGCTGTGTCTCTGGGCGAGAGGGCCACCATCA ACTGCAAGTCCAGCCAGAGTATTTACACAGC TCCAACAATAACAACTACTTAGCTTGGTTCCA GCAGAAACCAGGACAGCCTCCTAAACTGCTCC TTTACTGGGCATCTACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATCAAACTCCAGTCACTTTCGGCCCTGG GACCAAAGTGGGTATCAAA<br>SEQ ID NO: 27951 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAACGCAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br>SEQ ID NO: 31957 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYQTP VTFGPGTKVGIK<br>SEQ ID NO: 27952 | QVQLVQSGTEVKKPGASVKVSCKASGYTFTNYDIN WVRQATGQGLEWMGWMHPNSGNAGYAQKFQGR VTLTRDTSISTAYMELSSLRSEDTAVYYCASSSGWY YFDYWGQGTLVTVSS<br>SEQ ID NO: 31958 |

FIGURE 50
(Continued)

| | | | | |
|---|---|---|---|---|
| iPS:441896 | 21-225_4A2.001.011 | NA | GACATCGTGATGACCCAGTCTCCAGACTCCCT GGCTGTGTCTCTGGGCGAGAGGGCCACCATCA ACTGCAAGTCCAGCCAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGAC AGATTTCACTCTCACCATCAGCAGCCTGCAGC CTGAAGATGTGGCAGTTTATTACTGTCAGCAA TATTATCAAACTCCAGTCACTTTCGGCCCTGG GACCAAAGTGGGTATCAAA<br><br>SEQ ID NO: 27953 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TCAAACAGGCTATGCACAGAAGTTCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31959 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYQTP VTFGPGTKVGIK<br><br>SEQ ID NO: 27954 | QVQLVQSGTEVKKPGASVKVSCKASGYTFTNYDIN WVRQATGQGLEWMGWMHPNSGQTGYAQKFQGR VTLTRDTSISTAYMELSSLRSEDTAVYYCASSSGWY YFDYWGQGTLVTVSS<br><br>SEQ ID NO: 31960 |
| iPS:441900 | 21-225_4A2.001.012 | NA | GACATCGTGATGACCCAGTCTCCAGACTCCCT GGCTGTGTCTCTGGGCGAGAGGGCCACCATCA ACTGCAAGTCCAGCCAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATCAAACTCCAGTCACTTTCGGCCCTGG GACCAAAGTGGGTATCAAA<br><br>SEQ ID NO: 27955 | CAGGTGCAGCTGGTGCAGTCTGGGACTGAGGTG AAGAAGCCTGGGGCCTCAGTGAAGGTGTCCTGC AAGGCTTCTGGATACACCTTCACCAATTATGATA TCAACTGGGTGCGACAGGCCACTGGACAAGGC TTGAGTGGATGGGATGGATGCACCTAACAGTGG TAGCACAGGCTATGCACAGAAGTTCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31961 |

FIGURE 50
(Continued)

| | | | |
|---|---|---|---|
| iPS:441955 | 21-225_4A2.001.022 | AA | DIVMTQSPDSLAVSLGERATINCKSSQSILHSSNNNNYLAWFQQKPGQPPKLLLYWASTRESGVPDRFSGSGSGTDFTLTISSLQPEDVAVYYCQQYYQTPVTFGPGTKVGIK<br>SEQ ID NO: 27956 | QVQLVQSGTEVKKPGASVKVSCKASGYTFTNYDINWVRQATGQGLEWMGWMHPNSGSTGYAQKFQGRVTLTRDTSISTAYMELSSLRSEDTAVYYCASSSGWYYFDYWGQGTLVTVSS<br>SEQ ID NO: 31962 |
| | | NA | GACATCGTGATGACCCAGTCTCCAGACTCCCTGGCTGTGTCTCTGGGCGAGAGGGCCACCATCAACTGCAAGTCCAGCCAGAGTATTTACACAGCTCCAACAATAACAACTACTTAGCTTGGTTCCAGCAGAAACCAGGACAGCCTCCTAAACTGCTCCTTTACTGGGCATCTCACCCGGGAATCCGGGGTCCCTGACCGATTCAGTGGCAGCGGGTCTGGGACAGATTTCACTCTCACCATCAGCAGCCTGCAGCCTGAAGATGTGGCAGTTTATTACTGTCAGCAATATTATAGTACTCCAGTCACTTTCGGCCCTGGGACCAAAGTGGGTATCAAA<br>SEQ ID NO: 27957 | CAGGTGCAGCTGGTGCAGTCTGGGGCTGAGGTGAAGAAGCCTGGGGCCTCAGTGAAGGTGTCCTGCAAGGCTTCTGGATACACCTTCACCAATTATGATATCAACTGGGTGCGACAGGCCACTGGACAAGGCCTTGAGTGGATGGGATGGATGCACAGAAGTTCCAGGGCAGTAACACAGGCTATGCCACAGGACACCTCCATCAGCACAAGTCACCTTGACCAGGGACACCTCCATCAGCACAGCCTACATGGAACTGAGCAGCCTGAGATCTGAGGACACGGCCGTGTATTACTGTGCGAGTAGCAGTGGCTGGTACTACTTTGACTACTGGGGCCAGGGAACCCTGGTCACCGTGTCCTCA<br>SEQ ID NO: 31963 |
| | | AA | DIVMTQSPDSLAVSLGERATINCKSSQSILHSSNNNNYLAWFQQKPGQPPKLLLYWASTRESGVPDRFSGSGSGTDFTLTISSLQPEDVAVYYCQQYYSTPVTFGPGTKVGIK<br>SEQ ID NO: 27958 | QVQLVQSGAEVKKPGASVKVSCKASGYTFTNYDINWVRQATGQGLEWMGWMHPNSGNTGYAQKFQGRVTLTRDTSISTAYMELSSLRSEDTAVYYCASSSGWYYFDYWGQGTLVTVSS<br>SEQ ID NO: 31964 |

FIGURE 50
(Continued)

| | | | | |
|---|---|---|---|---|
| iPS:441962 | 21-225_4A2.001.023 | NA | GACATCGTGATGACCCAGTCTCCAGACTCCCTGGCTGTGTCTCTGGGCGAGAGGGCCACCATCAACTGCAAGTCCAGCCAGTCCATCAGAGTATTTACACAGCTCCAACAATAACAACAACTACTTAGCTTGGTTCCAGCAGAAACCAGGACAGCCTCCTAAACTGCTCCTTTACTGGGCATCTACCCGGAATCCGGGGTCCCTGACCGATTCAGTGGCAGCGGGTCTGGGACAGATTTCACTCTCACCATCAGCAGCCTGCAGCCTGAAGATGTGGCAGTTTATTACTGTGTCAGCAATATAGTACTCCAGTCACTTTCGGCCAAGGGACCAAAGTGGAAATCAAA<br><br>SEQ ID NO: 27959 | CAGGTGCAGCTGGTGCAGTCTGGGGCTGAGGTGAAGAAGCCTGGGGCCTCAGTGAAGGTGTCCTGCAAGGCTTCTGGATACACCTTCACCAATTATGATATCAACTGGGTGCGACAGGCCCCTGGACAAGGCTTGAGTGGATGGGATGGCACCTAACAGTGGTAACACAGGCTATGCACAGAAGTTCCAGGGCAGTCACCTTGACCAGGACACCTCCATCAGCACAGCCTACATGGAACTGAGCAGCCTGAGATCTGAGGACACGGCCGTGTATTACTGTGCGAGTAGCAGTGGCTGGTACTACTTTGACTACTGGGGCCAGGGAACCCTGGTCACCGTGTCCTCA<br><br>SEQ ID NO: 31965 |
| | | AA | DIVMTQSPDSLAVSLGERATINCKSSQSILHSSNNNNYLAWFQQKPGQPPKLLLYWASTRESGVPDRFSGSGSGTDFTLTISSLQPEDVAVYYCQQYYSTPVTFGQGTKVEIK<br><br>SEQ ID NO: 27960 | QVQLVQSGAEVKKPGASVKVSCKASGYTFTNYDINWVRQAPGQGLEWMGWMHPNSGNTGYAQKFQGRVTLTRDTSISTAYMELSSLRSEDTAVYYCASSSGWYYFDYWGQGTLVTVSS<br><br>SEQ ID NO: 31966 |
| iPS:441971 | 21-225_4A2.001.024 | NA | GACATCGTGATGACCCAGTCTCCAGACTCCCTGGCTGTGTCTCTGGGCGAGAGGGCCACCATCAACTGCAAGTCCAGCCAGTCCATCAGAGTATTTACACAGCTCCAACAATAACAACAACTACTTAGCTTGGTTCCAGCAGAAACCAGGACAGCCTCCTAAACTGCTCCTTTACTGGGCATCTACCCGGAATCCGGGGTCCCTGACCGATTCAGTGGCAGCGGGTCTGGGACAGATTTCACTCTCACCATCAGCAGCCTGCAGCCTGAAGATGTGGCAGTTTATTACTGTCAGCAACTGGTACTCCAGTCACTTTCGGGCCCTGGGACCAAAGTGGGTATCAAA<br><br>SEQ ID NO: 27961 | CAGGTGCAGCTGGTGCAGTCTGGGGCTGAGGTGAAGAAGCCTGGGGCCTCAGTGAAGGTGTCCTGCAAGGCTTCTGGATACACCTTCACCAATTATGATATCAACTGGGTGCGACAGGCCCCTGGACAAGGCTTGAGTGGATGGGATGGCACCTAACAGTGGTAAACAGGCTATGCACAGGAACACCTCCATCAGCACAGCCTACATGGAACTGAGCAGCCTGAGATCTGAGGACACGGCCGTGTATTACTGTGAGTAGCAGTGGCTGGTACTACTTTGACTACTGGGGCCAGGGAACCCTGGTCACCGTGTCCTCA<br><br>SEQ ID NO: 31967 |

FIGURE 50
(Continued)

| | | | | |
|---|---|---|---|---|
| iPS:441999 | 21-225_4A2.001.028 | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGPGTKVGIK<br><br>SEQ ID NO: 27962 | QVQLVQSGAEVKKPGASVKVSCKASGYTFTNYDIN WVRQATGQGLEWMGWMHPNSGQTGYAQKFQGR VTLTRDTSISTAYMELSSLRSEDTAVYYCASSSGWY YFDYWGQGTLVTVSS<br><br>SEQ ID NO: 31968 |
| | | NA | GACATCGTGATGACCCAGTCTCCAGACTCCCT GGCTGTGTCTCTGGGCGAGAGGGCCACCATCA ACTGCAAGTCCAGCCAGAGTATTTACACAGC TCCAACAATAACAACTACTTAGCTTGGTTCCA GCAGAAACCAGGACAGCCTCCTAAACTGCTCC TTTACTGGGCATCTCACCCGGGAATCCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAGTACTCCAGTCACTTTCGGCCAAGG GACCAAAGTGGAAATCAAA<br><br>SEQ ID NO: 27963 | CAGGTGCAGCTGGTGCAGTCTGGGGCTGAGGTG AAGAAGCCTGGGGCCTCAGTGAAGGTGTCCTGC AAGGCTTCTGGATACACCTTCACCAATTATGATA TCAACTGGGTGCGACAGGCCCCTGGACAAGGC TTGAGTGGATGGGATGGATGCACCCTAACAGTGG TCAAACAGGCTATGCACCAGGGACACCTCATCAGCACA AGTCACCTTGACCAGGGACACCTCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31969 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGQGTKVEIK<br><br>SEQ ID NO: 27964 | QVQLVQSGAEVKKPGASVKVSCKASGYTFTNYDIN WVRQAPGQGLEWMGWMHPNSGQTGYAQKFQGR VTLTRDTSISTAYMELSSLRSEDTAVYYCASSSGWY YFDYWGQGTLVTVSS<br><br>SEQ ID NO: 31970 |

FIGURE 50
(Continued)

| | | | | |
|---|---|---|---|---|
| iPS:442006 | 21-225_4A2.001.029 | NA | GACATCGTGATGACCCAGTCTCCAGACTCCCT GGCTGTGTCTCTGGGCGAGAGGGCCACCATCA ACTGCAAGTCCAGCCAGTCAGAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAGTACTCCAGTCACTTTCGGCCAAGG GACCAAAGTGGAAATCAAA<br><br>SEQ ID NO: 27965 | CAGGTGCAGCTGGTGCAGTCTGGGGCTGAGGTG AAGAAGCCTGGGGCCTCAGTGAAGGTGTCCTGC AAGGCTTCTGGATACACCTTCACCAATTATGATA TCAACTGGGTGCGACAGGCCCCTGGACAAGGC TTGAGTGGATGGGATGGATGCACCCTAACAGTGG TAGCACAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31971 |
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYSTP VTFGQGTKVEIK<br><br>SEQ ID NO: 27966 | QVQLVQSGAEVKKPGASVKVSCKASGYTFTNYDIN WVRQAPGQGLEWMGWMHPNSGSTGYAQKFQGR VTLTRDTSISTAYMELSSLRSEDTAVYYCASSSGWY YFDYWGQGTLVTVSS<br><br>SEQ ID NO: 31972 |
| iPS:442020 | 21-225_4A2.001.031 | NA | GACATCGTGATGACCCAGTCTCCAGACTCCCT GGCTGTGTCTCTGGGCGAGAGGGCCACCATCA ACTGCAAGTCCAGCCAGTCAGAGTATTTACACAGC TCCAACAATAACAACTACTTAGCTTGGTTCCA GCAGAAACCAGGACAGCCTCCTAAACTGCTCC TTTACTGGGCATCTACCCGGAATCGGGGTC CCTGACCGATTCAGTGGCAGCGGGTCTGGGAC AGATTTCACTCTCACCATCAGCAGCCTGCAGC CTGAAGATGTGGCAGTTTATTACTGTCAGCAA TATTATAATACTCCAGTCACTTTCGGCCCTGGG ACCAAAGTGGAAATCAAA<br><br>SEQ ID NO: 27967 | CAGGTGCAGCTGGTGCAGTCTGGGGGTGAGGTG AAGAAGCCTGGGGCCTCAGTGAAGGTGTCCTGC AAGGCTTCTGGATACACCTTCACCAATTATGATA TCAACTGGGTGCGACAGGCCGAAGGACAAGGC TTGAGTGGATGGGATGGATGCACCCTAACAGTGG TAACGAAGGCTATGCACAGAAGTTCCAGGGCAG AGTCACCTTGACCAGGGACACCTCCATCAGCACA GCCTACATGGAACTGAGCAGCCTGAGATCTGAG GACACGGCCGTGTATTACTGTGCGAGTAGCAGTG GCTGGTACTACTTTGACTACTGGGGCCAGGGAAC CCTGGTCACCGTGTCCTCA<br><br>SEQ ID NO: 31973 |

FIGURE 50
(Continued)

| | | | |
|---|---|---|---|
| | | AA | DIVMTQSPDSLAVSLGERATINCKSSQSILHSSNN NNYLAWFQQKPGQPPKLLLYWASTRESGVPDR FSGSGSGTDFTLTISSLQPEDVAVYYCQQYYNTP VTFGPGTKVEIK<br><br>SEQ ID NO: 27968 | QVQLVQSGGEVKKPGASVKVSCKASGYTFTNYDIN WVRQAEGQGLEWMGWMHPNSGNEGYAQKFQGR VTLTRDTSISTAYMELSSLRSEDTAVYYCASSSGWY YFDYWGQGTLVTVSS<br><br>SEQ ID NO: 31974 |
| iPS:442050 | 21-225_4H6.004 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ATTATTGTCAACAGGCTAACAGTTTCCCATTC ACTTTCGGCCCTGGGACCAAAGTGGATATCAA A<br><br>SEQ ID NO: 27969 | CAGGTGCAGCTGGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCAGAGAGATGGTAC CAGCTCGTTTGACTACTGGGGCCAGGGAACCCTG GTCACCGTGTCCTCA<br><br>SEQ ID NO: 31975 |
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGPGT KVDIK<br><br>SEQ ID NO: 27970 | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARDGTS SFDYWGQGTLVTVSS<br><br>SEQ ID NO: 31976 |

FIGURE 50
(Continued)

| | | | |
|---|---|---|---|
| iPS:442059 | 21-225_4H6.005 | NA | GACATCCAGATGACCCAGTCTCCATCTTCCGT GTCTGCATCTGTAGGAGACAGAGTCACCATCA CTTGTCGGGCGAGTCAGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ATTATTGTCAACAGGCTAACAGTTTCCCATTC ACTTTCGGCCAAGGGACCAAAGTGGATATCAA A SEQ ID NO: 27971 | CAGGTGCAGCTGGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGT GGCACAAACTATGCACAGAAGTTTCAGGGCAGG GTCACCATGACCAGGGACACGTCCATCAGCACA GCCTACATGGAGCTGAGCAGTCTGCGAGATCTGACG ACACGGCCGTGTATTACTGTGCGAGAGATGGTAC CAGCTCGTTTGACTACTGGGGCCAGGGAACCCTG GTCACCGTGTCCTCA SEQ ID NO: 31977 |
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGQGT KVDIK SEQ ID NO: 27972 | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARDGTS SFDYWGQGTLVTVSS SEQ ID NO: 31978 |
| iPS:442065 | 21-225_4H6.006 | NA | GACATCCAGATGACCCAGTCTCCATCTTCCGT GTCTGCATCTGTAGGAGACAGAGTCACCATCA CTTGTCGGGCGAGTCAGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ATTATTGTCAACAGGCTAACAGTGGATATCAA A SEQ ID NO: 27973 | CAGGTGCAGCTGGTACAGTCTGGGGCTGAGGTG AAGAAGCCTGGGGCCTCAGTGAAGGTCAGCTGC AAGGCTTCTGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGCGAGATCTGACG ACACGGCCGTGTATTACTGTGCGAGAGATGGTAC CAGCTCGTTTGACTACTGGGGCCAGGGAACCCTG GTCACCGTGTCCTCA SEQ ID NO: 31979 |

FIGURE 50
(Continued)

| | | | |
|---|---|---|---|
| iPS:442071 | 21-225_4H6.007 | AA | DIQMTQSPSSVSASVGDRVTITCRASQGISRWLA WYQQKPGKAPKLLIYGASSLQSGVPSRFSGSGS GTDFTLTISSLQPEDFATYYCQQANSFPFTFGQG TKVDIK<br>SEQ ID NO: 27974 | QVQLVQSGAEVKKPGASVKVSCKASGYTFTFDYYL HWVRQAPGQGLEWMGWIHPNSGGTNYAQKFQGR VTMTRDTSISTAYMELSSLRSDDTAVYYCARDGTS SFDYWGQGTLVTVSS<br>SEQ ID NO: 31980 |
| | | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ATTATTGTCAACAGGCTAACAGTTTCCCATTC ACTTTCGGCCCTGGGACCAAAGTGGATATCAA A<br>SEQ ID NO: 27975 | CAGGTGCAGCTGGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCGAGAGATGCTAC CAGCTCGTTTGACTACTGGGGCCAGGGAACCCTG GTCACCGTGTCCTCA<br>SEQ ID NO: 31981 |
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGPGT KVDIK<br>SEQ ID NO: 27976 | QVQLVQSGAEVKKPGASVKVSCKASGYTFTFDYYL HWVRQAPGQGLEWMGWIHPNSGGTNYAQKFQGR VTMTRDTSISTAYMELSSLRSDDTAVYYCARDATS SFDYWGQGTLVTVSS<br>SEQ ID NO: 31982 |

FIGURE 50
(Continued)

| | | | |
|---|---|---|---|
| iPS:442078 | 21-225_4H6.008 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATT ATTATTGTCAACAGGCTAACAGTTTCCCATTC ACTTTCGGCCCTGGGACCAAAGTGGATATCAA A SEQ ID NO: 27977 | CAGGTGCAGCTGGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCGAGAAGTGGTAC ACAGGCTCGTTTGACTACTGGGGCCAGGGAACCCTG GTCACCGTGTCCTCA SEQ ID NO: 31983 |
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGPGT KVDIK SEQ ID NO: 27978 | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARSGTSS FDYWGQGTLVTVSS SEQ ID NO: 31984 |
| iPS:442085 | 21-225_4H6.009 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATT ATTATTGTCAACAGGCTAACAGTTTCCCATTC ACTTTCGGCCCAAGGGACCAAGGTGGATATCAA A SEQ ID NO: 27979 | CAGGTGCAGCTGGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCGAGAAGTGGTAC ACAGGCTCGTTTGACTACTGGGGCCAGGGAACCCTG GTCACCGTGTCCTCA SEQ ID NO: 31985 |

FIGURE 50
(Continued)

| | | | |
|---|---|---|---|
| iPS:442089 | 21-225_4H6.010 | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGQGT KVDIK<br>SEQ ID NO: 27980 | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARSGTSS FDYWGQGTLVTVSS<br>SEQ ID NO: 31986 |
| | | NA | GACATCCAGATGACCCAGTCTCCATCTTCCGT GTCTGCATCTGTAGGAGATAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAATTT ATTATTGTCAACAGGCTAACAGTTTCCCATTC ACTTTCGGCCAAGGGACCAAAGTGGATATCAA A<br>SEQ ID NO: 27981 | CAGGTGCAGCTGGTACAGTCTGGGGCTGAGGTG AAGAAGCCTGGGGCTTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCGAGAGATGCTAC CAGCTCGTTTGACTACTGGGGCCAGGGAACCCTG GTCACCGTGTCCTCA<br>SEQ ID NO: 31987 |
| | | AA | DIQMTQSPSSVSASVGDRVTITCRASQGISRWLA WYQQKPGKAPKLLIYGASSLQSGVPSRFSGSGS GTDFTLTISSLQPEDFAIYYCQQANSFPFTFGQGT KVDIK<br>SEQ ID NO: 27982 | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARDATS SFDYWGQGTLVTVSS<br>SEQ ID NO: 31988 |

FIGURE 50
(Continued)

| | | | | |
|---|---|---|---|---|
| iPS:442093 | 21-225_4H6.011 | NA | GACATCCAGATGACCCAGTCTCCATCTTCCGT GTCTGCATCTGTAGGAGACAGAGTCACCATCA CTTGTCGGGCGAGTCAGGGTATTAGCAGGTGG TTAGCCTGGTATCAGCAGAAACCAGGGAAAG CCCCTAAGCTCCTGATCTATGTGCATCCAGTT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ATTATTGTCAACAGGCTAACAGTTTCCCATTC ACTTTCGGCCAAGGGACCAAAGTGGATATCAA A | CAGGTGCAGCTGTGTACAGTCTGGGGCTGAGGTG AAGAAGCCTGGGGCCTCAGTGAAGGTCAGCTGC AAGGCTTCTGGATACACCTTCACCGACTACTATT TGCACTGGGTGCGACAGGCCCCTGGACAAGGTCT TGAGTGGATGGGATGGATCCACCCTAACAGTGGT GGCACAAACTATGCACAGAAGTTTCAGGGCAGG GTCACCATGACCAGGGACACGTCCATCAGCACA GCCTACATGGAGCTGAGCAGTCTGAGATCTGACG ACACGGCCGTGTATTACTGTGCGAGAGATGCTAC CAGCTCGTTTGACTACTGGGGCCAGGGAACCCTG GTCACCGTGTCCTCA |
| | | | SEQ ID NO: 27983 | SEQ ID NO: 31989 |
| | | AA | DIQMTQSPSSVSASVGDRVTITCRASQGISRWLA WYQQKPGKAPKLLIYGASSLQSGVPSRFSGSGS GTDFTLTISSLQPEDFATYYCQQANSFPFTFGQG TKVDIK | QVQLVQSGAEVKKPGASVKVSCKASGYTFTDYYL HWVRQAPGQGLEWMGWIHPNSGGTNYAQKFQGR VTMTRDTSISTAYMELSSLRSDDTAVYYCARDATS SFDYWGQGTLVTVSS |
| | | | SEQ ID NO: 27984 | SEQ ID NO: 31990 |
| iPS:442115 | 21-225_5E5.003 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT CCCCTAAGCGCCTGATCTATGCTGCATCCAGT TTGCAAAGTGGGGTCCCATCAAGGTTCAGCGG CAGTGGATCTGGGACAGATCGGACACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATCTGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTGTCCTCA |
| | | | SEQ ID NO: 27985 | SEQ ID NO: 31991 |

FIGURE 50
(Continued)

| | | | | |
|---|---|---|---|---|
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br>SEQ ID NO: 27986 | QVQLVESGGGVVQPGRSLRLSCAASGFTFSNYVM HWVRQAPGKGLEWVAVIWYDASNKYYADSVKGR FTISRDNSKNTLYLQMNSLRAEDTAVYYCTREVYS SGWYDYGMDVWGQGTTVTVSS<br>SEQ ID NO: 31992 |
| iPS:442122 | 21-225_5E5.004 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATCTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA<br>SEQ ID NO: 27987 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATCTGGTATGATGAAGT AATAAATACTATGCAGAATCCGTGAAGGGCCGA TTCACCATCTCCAGAGACAACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTGTCCTCA<br>SEQ ID NO: 31993 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br>SEQ ID NO: 27988 | QVQLVESGGGVVQPGRSLRLSCAASGFTFSNYVM HWVRQAPGKGLEWVAVIWYDGSNKYYAESVKGR FTISRDNSKNTLYLQMNSLRAEDTAVYYCTREVYS SGWYDYGMDVWGQGTTVTVSS<br>SEQ ID NO: 31994 |

FIGURE 50
(Continued)

| | | | | |
|---|---|---|---|---|
| iPS:442129 | 21-225_5E5.005 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA<br>SEQ ID NO: 27989 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGATGGAAGT AATAAATACTATGCAGGCTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTCTCCTCA<br>SEQ ID NO: 31995 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br>SEQ ID NO: 27990 | QVQLVESGGGVVQPGRSLRLSCAASGFTFSNYVM HWVRQAPGKGLEWVAVIWYDGSNKYYAGSVKGR FTISRDNSKNTLYLQMNSLRAEDTAVYYCTREVYS SGWYDYGMDVWGQGTTVTVSS<br>SEQ ID NO: 31996 |
| iPS:442136 | 21-225_5E5.006 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTGCAACT TATTACTGTCTGTACAGCATTATAGTTACCCTCGG ACGTTCGGCCAAGGGACCAAGGTGGAAGTCA AA<br>SEQ ID NO: 27991 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGATGGAAGT AATAAATACTATGCAGACGCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTGTCCTCA<br>SEQ ID NO: 31997 |

FIGURE 50
(Continued)

| | | | | |
|---|---|---|---|---|
| iPS:442171 | 21-225_5E5.011 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br>SEQ ID NO: 27992 | QVQLVESGGGVVQPGRSLRLSCAASGFTFSNYVM HWVRQAPGKGLEWVAVIWYDGSNKYYADAVKG RFTISRDNSKNTLYLQMNSLRAEDTAVYYCTREVY SSGWYDYGMDVWGQGTTVTVSS<br>SEQ ID NO: 31998 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGACAGATCTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA<br>SEQ ID NO: 27993 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGATGGAAGT AATAAATACTATGCAGATCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTGTCCTCA<br>SEQ ID NO: 31999 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br>SEQ ID NO: 27994 | QVQLVESGGGVVQPGRSLRLSCAASGFTFSNYVM HWVRQAPGKGLEWVAVIWYDASNKYYAESVKGR FTISRDNSKNTLYLQMNSLRAEDTAVYYCTREVYS SGWYDYGMDVWGQGTTVTVSS<br>SEQ ID NO: 32000 |

FIGURE 50
(Continued)

| | | | | |
|---|---|---|---|---|
| iPS:442178 | 21-225_5E5.012 | NA | GACATCCAGATGACCCAGTCTCCATCTCCT GTCTGCATCTGTAGGAGACAGAGTCACCATCA CTTGCCGGGCAAGTCAGGGACAGTTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAACTATGTCAT GCACTGGGTCCGCCAGGCTCCAGGCAAGGGGCT GGAGTGGGTGGCAGTTATCTGGTATGATGCAAGT AATAAATACTATGCAGACGCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTCTCCTCA |
| | | | SEQ ID NO: 27995 | SEQ ID NO: 32001 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDASNKYYADAVKG RFTISRDNSKNTLYLQMNSLRAEDTAVYYCTREVY SSGWYDYGMDVWGQGTTVTVSS |
| | | | SEQ ID NO: 27996 | SEQ ID NO: 32002 |
| iPS:442199 | 21-225_5E5.015 | NA | GACATCCAGATGACCCAGTCTCCATCTCCCT GTCTGCATCTGTAGGAGACAGAGTCACCATCA CTTGCCGGGCAAGTCAGGGACAGTTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTCTACAGCATTATATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCCGTCTGGATTCACCTTCAGTAACTATGTCAT GCACTGGGTCCGCCAGGCTCCAGGCAAGGGGCT GGAGTGGGTGGCAGTTATCTGGTATGATGCAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTATTACGACTACGGTATGGACGTC TGGGGCCAAGGGACCACGGTCACCGTCTCCTCA |
| | | | SEQ ID NO: 27997 | SEQ ID NO: 32003 |

FIGURE 50
(Continued)

| | | | |
|---|---|---|---|
| iPS:442206 | 21-225_5E5.016 | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br><br>SEQ ID NO: 27998 | QVQLVESGGGVVQPGRSLRLSCAASGFTFSNYVM HWVRQAPGKGLEWVAVIWYDASNKYYADSVKGR FTISRDNSKNTLYLQMNSLRAEDTAVYYCTREVYS SGYYDYGMDVWGQGTTVTVSS<br><br>SEQ ID NO: 32004 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCCAAGGTTCAGCGG CAGTGGATCTGGGACAGATCTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA<br><br>SEQ ID NO: 27999 | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATCTGGTATGATGCAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTTCTACGACTACGGTATGGACGTC TGGGGCCAAGGGACCACGGTCACCGTGTCCTCA<br><br>SEQ ID NO: 32005 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK<br><br>SEQ ID NO: 28000 | QVQLVESGGGVVQPGRSLRLSCAASGFTFSNYVM HWVRQAPGKGLEWVAVIWYDASNKYYADSVKGR FTISRDNSKNTLYLQMNSLRAEDTAVYYCTREVYS SGFYDYGMDVWGQGTTVTVSS<br><br>SEQ ID NO: 32006 |

FIGURE 50
(Continued)

| | | | | |
|---|---|---|---|---|
| iPS:442213 | 21-225_5E5.017 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGGAAGT AATAAATACTATGCAGAATCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTATTACGACTACGGTATGGACGTC TGGGGCCAAGGGACCACGGTCACCGTCTCCTCA |
| | | | SEQ ID NO: 28001 | SEQ ID NO: 32007 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHSYPRTFGQG TKVEVK | QVQLVESGGGVVQPGRSLRLSCAASGFTFSNYVM HWVRQAPGKGLEWVAVIWYDGSNKYYAESVKGR FTISRDNSKNTLYLQMNSLRAEDTAVYYCTREVYS SGYYDYGMDVWGQGTTVTVSS |
| | | | SEQ ID NO: 28002 | SEQ ID NO: 32008 |
| iPS:442220 | 21-225_5E5.018 | NA | GACATCCAGATGACCCAGTCTCCATCCTCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGATTCACTCTCACAA TCAGCAGCCTGCAGCCTGAAGATTTTGCAACT TATTACTGTCTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTATTACGACTACGGTATGGACGTC TGGGGCCAAGGGACCACCGTCACCGTCTCCTCA |
| | | | SEQ ID NO: 28003 | SEQ ID NO: 32009 |

FIGURE 50
(Continued)

| | | | | |
|---|---|---|---|---|
| | | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDGSNKYYADSVKGR FTISRDNSKNTLYLQMNSLRAEDTAVYYCTREVYS SGYYDYGMDVWGQGTTVTVSS |
| | | | | SEQ ID NO: 28004 | SEQ ID NO: 32010 |
| iPS:442227 | 21-225_5E5.019 | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATCTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATCTGGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTTCTACGACTACGGTATGGACGTC TGGGGCCAAGGGACCACGGTCACCGTCTCCTCA |
| | | | | SEQ ID NO: 28005 | SEQ ID NO: 32011 |
| | | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDGSNKYYADSVKGR FTISRDNSKNTLYLQMNSLRAEDTAVYYCTREVYS SGFYDYGMDVWGQGTTVTVSS |
| | | | | SEQ ID NO: 28006 | SEQ ID NO: 32012 |

FIGURE 50
(Continued)

| | | | |
|---|---|---|---|
| iPS:442255 | 21-225_5E5.023 | NA | GACATCCAGATGACCCAGTCTCCATCTCCT GTCTGCATCTGTAGGAGACAGAGTCACCATCA CTTGCCGGGCAAGTCAGGGACATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGATGCAAGT AATAAATACTATGCAGAGACAATTCCAAGAACACGC TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTATTACGACTACGGTATGGACGTC TGGGGCCAAGGGACCACGGTCACCGTCTCCTCA |
| | | | SEQ ID NO: 28007 | SEQ ID NO: 32013 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDASNKYYAESVKGR FTISRDNSKNTLYLQMNSLRAEDTAVYYCTREVYS SGYYDYGMDVWGQGTTVTVSS |
| | | | SEQ ID NO: 28008 | SEQ ID NO: 32014 |
| iPS:442262 | 21-225_5E5.024 | NA | GACATCCAGATGACCCAGTCTCCATCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAACTATGTCAT GCACTGGGTCCGCCAGGCTCCAGGCAAGGGCT GGAGTGGGTGGCAGTTATCTGGTATGATGCAAGT AATAAATACTATGCAGACGCCGTGAAGGGCCGA TTCACCATCTCCAGAGACAATTCCAAGAACACGC TGTATCTGCAAATGAACAGCCTGAGAGCCGAGG ACACGGCTGTGTATTACTGTACGAGAGAGGTATA TAGCAGTGGCTATTACGACTACGGTATGGACGTC TGGGGCCAAGGGACCACGGTCACCGTGTCCTCA |
| | | | SEQ ID NO: 28009 | SEQ ID NO: 32015 |

FIGURE 50
(Continued)

| | | | | |
|---|---|---|---|---|
| iPS:442269 | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | QVQLVESGGGVVQPGRSLRLSCAASGFTFSNYVM HWVRQAPGKGLEWVAVIWYDASNKYYADAVKG RFTISRDNSKNTLYLQMNSLRAEDTAVYYCTREVY SSGYYDYGMDVWGQGTTVTVSS |
| | | | SEQ ID NO: 28010 | SEQ ID NO: 32016 |
| | 21-225_5E5.025 | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGAAAG CCCCTAAGCGCCTGATCTATGCTGCATCCAGT TTGCAAAGTGGGGTCCCATCAAGGTTCAGCGG CAGTGGATCTGGGACAGATCTCACTCTCACAA TCAGCAGCCTGCAGCCTGAAGATTTTGCAACT TATTACTGTCTACAGCATTATAGTTACCCTCGG ACGTTCGGCCAAGGGACCAAGGTGGAAGTCA AA | GAGGTGCAGCTGGTGGAGTCTGGGGGAGGCGTG GTCCAGCCTGGGGGGTCCCTGAGACTCTCCTGTG CAGCGTCTGGATTCACCTTCAGTAACTATGTCAT GCACTGGGTCCGCCAGGCTCCAGGCAAGGGGCT GGAGTGGGTGGCAGTTATCTGGTATGATGAAGT AATAAATACTATGCAGAATCCGTGAAGGGCCGA TTCACCATCTCCAGAGACAATGCCAAGAACACGC TGTATCTGCAAATGAACAGCCTGAGAGCCGAGG ACACGGCTGTGTATTACTGTACGAGAGAGGTATA TAGCAGTGGCTGGTACGACTACGGTATGGACGTC TGGGGCCAAGGGACCACGGTCACCGTGTCCTCA |
| | | | SEQ ID NO: 28011 | SEQ ID NO: 32017 |
| | | AA | DIQMTQSPSSLSASVGDRVTITCRASQGIRNDLG WYQQKPGKAPKRLIYAASSLQSGVPSRFSGSGS GTEFTLTISSLQPEDFATYYCLQHYSYPRTFGQG TKVEVK | EVQLVESGGGVVQPGGSLRLSCAASGFTFSNYVMH WVRQAPGKGLEWVAVIWYDGSNKYYAESVKGRF TISRDNAKNTLYLQMNSLRAEDTAVYYCTREVYSS GWYDYGMDVWGQGTTVTVSS |
| | | | SEQ ID NO: 28012 | SEQ ID NO: 32018 |

FIGURE 50
(Continued)

| | | | |
|---|---|---|---|
| iPS:442311 | 21-225_7E11.001.001 | NA | GACATCCAGATGACCCAGTCTCCATCCTCCCT GTCTGCATCTGTAGGAGACAGAGTCACCATTA CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGAATTTCACTCTCACCAT CAGCAGTCTGCAACCTGAAGATTTTGCAATTT ACTACTGTCAACAGACTTACAGTACCCCGCTC ACTTTCGGCGGCGGGACCAAGGTGGAGATCA AA<br>SEQ ID NO: 28013 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGCT GGAGTGGGTGGCAATTATCGAGATCCGTGATGGAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTCCTCA<br>SEQ ID NO: 32019 |
| | | AA | DIQMTQSPSSLSASVGDRVTITCRASQNISYLNW YQQKPGKAPKFLIYTASSLQSGVPSRFSGSGSGT DFTLTISSLQPEDFAIYYCQQTYSTPLTFGGGTKV EIK<br>SEQ ID NO: 28014 | QVQLVESGGGVVQPGRSLRLSCAASGFTFSSFGMH WVRQAPGKGLEWVAIIWHDGSNKYYADSVKGRFT ISRDNSKNTLYLQMSSLRAEDTAVYYCARDLSMGG MDVWGQGTTVTVSS<br>SEQ ID NO: 32020 |
| iPS:442317 | 21-225_7E11.001.002 | NA | GACATCCAGATGACCCAGTCTCCATCCTCCCT GTCTGCATCTGTAGGAGACAGAGTCACCATTA CTTGCCGGGCAAGTCAAAACATTATCAGCTAT TTAAATTGGTATCAACAGAAACCAGGGAAAG CCCCTAAACTCCTGATCTATACTGCATCCAGTT TGCAAAGTGGGGTCCCATCAAGGTTCAGTGGC AGTGGATCTGGGACAGAATTTCACTCTCACCAT CAGCAGTCTGCAACCTGAAGATTTCACTCTCCGCTC ACTTTCGGCGGCGGGACCAAGGTGGAGATCA AA<br>SEQ ID NO: 28015 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGCT GGAGTGGGTGGCAATTATCGAGATCCGTGATGGAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTCCTCA<br>SEQ ID NO: 32021 |

FIGURE 50
(Continued)

| | | | | |
|---|---|---|---|---|
| iPS:442323 | 21-225_7E11.001.003 | AA | DIQMTQSPSSLSASVGDRVTITCRASQNIISYLNW YQQKPGKAPKLLIYTASSLQSGVPSRFSGSGSGT DFTLTISSLQPEDFATYYCQQTYSTPLTFGGGTK VEIK<br><br>SEQ ID NO: 28016 | QVQLVESGGGVVQPGRSLRLSCAASGFTFSSFGMH WVRQAPGKGLEWVAIIWHDGSNKYYADSVKGRFT ISRDNSKNTLYLQMSSLRAEDTAVYYCARDLSMGG MDVWGQGTTVTVSS<br><br>SEQ ID NO: 32022 |
| | | NA | GACATCCAGATGACCCAGTCTCCATCCTCCCT GTCTGCATCTGTAGGAGACAGAGTCACCATG CTTGCCGGGCAAGTCAAAACATTATCAGTTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGGACCAAGGTGGAGATCA AA<br><br>SEQ ID NO: 28017 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGACGGAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA<br><br>SEQ ID NO: 32023 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK<br><br>SEQ ID NO: 28018 | QVQLVESGGGVVQPGRSLRLSCAASGFTFSSFGMH WVRQAPGKGLEWVAIIWHSGSNKYYADSVKGRFT ISRDNSKNTLYLQMSSLRAEDTAVYYCARDLSMGG MDVWGQGTTVTVSS<br><br>SEQ ID NO: 32024 |

FIGURE 50
(Continued)

| | | | |
|---|---|---|---|
| iPS:442330 | 21-225_7E11.001.004 | NA | GACATCCAGATGACCCAGTCTCCATCCTCCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGAGGGACCAAGGTGGAGATCA AA SEQ ID NO: 28019 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCGAGACTCCGTGAAGGAAG TAATAAATACTATGCAGACTCCGTGAAGGGCCG ATTCACCATCTCCAGAGACAATTCCAAAAACACG CTGTATCTGCAAATGAGCAGCCTGCGAGCCGAG GACACGGCTGTGTATTACTGTGCGAGAGATCGA GTATGGGCGGTATGGACGTCTGGGGCCAAGGGA CCACGGTCACCGTCCTCA SEQ ID NO: 32025 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK SEQ ID NO: 28020 | QVQLVESGGGVVQPGRSLRLSCAASGFTFSSFGMH WVRQAPGKGLEWVAIIWHEGSNKYYADSVKGRFT ISRDNSKNTLYLQMSSLRAEDTAVYYCARDLSMGG MDVWGQGTTVTVSS SEQ ID NO: 32026 |
| iPS:442337 | 21-225_7E11.001.005 | NA | GACATCCAGATGACCCAGTCTCCATCCTCCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGAGGGACCAAGGTGGAGATCA AA SEQ ID NO: 28021 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGATGCAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTCCTCA SEQ ID NO: 32027 |

FIGURE 50
(Continued)

| | | | | |
|---|---|---|---|---|
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHDASNKYYADSVKGRFT ISRDNSKNTLYLQMSSLRAEDTAVYYCARDLSMGG MDVWGQGTTVTVSS |
| | | | SEQ ID NO: 28022 | SEQ ID NO: 32028 |
| iPS:442344 | 21-225_7E11.001.006 | NA | GACATCCAGATGACCCAGTCTCCATCCTCCCT GTCTGCATCTGTAGGAGACAGAGTCACCATTG CTTGCCGGGCAAGTCAAAACATTATCAGTTAT TTAAATTGGTATCAACAGAAACCAGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGACCAAGGTGGAGATCA AA | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGATGAAGT AATAAATACTATGCAGAATCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTCTCCTCA |
| | | | SEQ ID NO: 28023 | SEQ ID NO: 32029 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHDGSNKYYAESVKGRFT ISRDNSKNTLYLQMSSLRAEDTAVYYCARDLSMGG MDVWGQGTTVTVSS |
| | | | SEQ ID NO: 28024 | SEQ ID NO: 32030 |

FIGURE 50
(Continued)

| | | | | |
|---|---|---|---|---|
| iPS:442351 | 21-225_7E11.001.007 | NA | GACATCCAGATGACCCAGTCTCCATCCTCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGATGAAGT AATAAATACTATGCAGACGCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA |
| | | | SEQ ID NO: 28025 | SEQ ID NO: 32031 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHDGSNKYYADAVKGRF TISRDNSKNTLYLQMSSLRAEDTAVYYCARDLSMG GMDVWGQGTTVTVSS |
| | | | SEQ ID NO: 28026 | SEQ ID NO: 32032 |
| iPS:442358 | 21-225_7E11.001.008 | NA | GACATCCAGATGACCCAGTCTCCATCCTCCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGAAGGAAAG TAATAAATACTATGCAGACGCCGTGAAGGGCCG ATTCACCATCTCCAGAGACAATTCCAAAAACACG CTGTATCTGCAAATGAGCAGCCTGCGAGCCGAG GACACGGCTGTGTATTACTGTGCGAGAGATCTGA GTATGGGCGGTATGGACGTCTGGGGCCAAGGGA CCACGGTCACCGTGTCCTCA |
| | | | SEQ ID NO: 28027 | SEQ ID NO: 32033 |

FIGURE 50
(Continued)

| | | | | |
|---|---|---|---|---|
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHEGSNKYYADAVKGRF TISRDNSKNTLYLQMSSLRAEDTAVYYCARDLSMG GMDVWGQGTTVTVSS |
| | | | SEQ ID NO: 28028 | SEQ ID NO: 32034 |
| iPS:442365 | 21-225_7E11.001.009 | NA | GACATCCAGATGACCCAGTCTCCATCCTCCCT GTCTGCATCTGTAGGAGACAGAGTCACCATTG CTTGCCGGGCAAGTCAAAACATTATCAGTTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGGACCAAGGTGGAGATCA AA | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATGAAGGAAG TAATAAATACTATGCAGAATCCGTGAAGGGCCG ATTCACCATCTCCAGAGACAATTCCAAAAACACG CTGTATCTGCAAATGAGCAGCCTGCGAGCCGAG GACACGGCTGTGTATTACTGTGCGAGAGATCTGA GTATGGGCGGTATGGACGTCTGGGGCCAAGGGA CCACGGTCACCGTGTCCTCA |
| | | | SEQ ID NO: 28029 | SEQ ID NO: 32035 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHEGSNKYYAESVKGRFT ISRDNSKNTLYLQMSSLRAEDTAVYYCARDLSMGG MDVWGQGTTVTVSS |
| | | | SEQ ID NO: 28030 | SEQ ID NO: 32036 |

FIGURE 50
(Continued)

| | | | | |
|---|---|---|---|---|
| iPS:442372 | 21-225_7E11.001.010 | NA | GACATCCAGATGACCCAGTCTCCATCTCCCT GTCTGCATCTGTAGGAGACAGAGTCACCATG CTTGCCGGGCAAGTCAAAACATTATCAGCTAT TTAAATTGGTATCAACAGAAACCAGGGAAAG CCCCTAAATTCCTGATCTATACTGCATCCAGT TGCAAAGTGGGGGTCCCATCAAGGTTCAGTGGC AGTGGATCTGGGACAGATTTCACTCTCACCAT CAGCAGTCTGCAACCTGAAGATTTTGCAATT ACTACTGTCAACAGAGACTTACAGTACCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGCGACTCTCCTGTG CAGCCTCTGGATTCACCTTCAGTAGCTTTGGCAT GCACTGGGTCCGCCAGGCTCCAGGCAAGGGCT GGAGTGGGTGGCAATTATCTGGCATAGTGAAGT AATAAATACTATGCAGAGACAATTCCAAAACACGC TTCACCATCTCCAGAGACAATTCCAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA |
| | | | SEQ ID NO: 28031 | SEQ ID NO: 32037 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHSGSNKYYAESVKGRFT ISRDNSKNTLYLQMSSLRAEDTAVYYCARDLSMGG MDVWGQGTTVTVSS |
| | | | SEQ ID NO: 28032 | SEQ ID NO: 32038 |
| iPS:442379 | 21-225_7E11.001.011 | NA | GACATCCAGATGACCCAGTCTCCATCTCCCT GTCTGCATCTGTAGGAGACAGAGTCACCATG CTTGCCGGGCAAGTCAAAACATTATCAGCTAT TTAAATTGGTATCAACAGAAACCAGGGAAAG CCCCTAAATTCCTGATCTATACTGCATCCAGT TGCAAAGTGGGGGTCCCATCAAGGTTCAGTGGC AGTGGATCTGGGACAGATTTCACTCTCACCAT CAGCAGTCTGCAACCTGAAGATTTTGCAATT ACTACTGTCAACAGAGACTTACAGTACCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGCGACTCTCCTGTG CAGCCTCTGGATTCACCTTCAGTAGCTTTGGCAT GCACTGGGTCCGCCAGGCTCCAGGCAAGGGCT GGAGTGGGTGGCAATTATCTGGCATAGTGAAGT AATAAATACTATGCAGAGACGCGTGAAGGGCCGA TTCACCATCTCCAGAGACAATTCCAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA |
| | | | SEQ ID NO: 28033 | SEQ ID NO: 32039 |

FIGURE 50
(Continued)

| | | | | |
|---|---|---|---|---|
| iPS:442386 | 21-225_7E11.001.012 | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK SEQ ID NO: 28034 | QVQLVESGGGVVQPGRSLRLSCAASGFTFSSFGMH WVRQAPGKGLEWVAIIWHSGSNKYYADAVKGRFT ISRDNSKNTLYLQMSSLRAEDTAVYYCARDLSMGG MDVWGQGTTVTVSS SEQ ID NO: 32040 |
| | | NA | GACATCCAGATGACCCAGTCTCCATCCTCCCT GTCTGCATCTGTAGGAGACAGAGTCACCATTA CTTGCCGGGCAAGTCAAAACATTATCAGCTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGGACCAAGGTGGAGATCA AA SEQ ID NO: 28035 | CAGGTGCAGCTGGTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATAGTGGAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA SEQ ID NO: 32041 |
| | | AA | DIQMTQSPSSLSASVGDRVTITCRASQNIISYLNW YQQKPGKAPKFLIYTASSLQSGVPSRFSGSGSGT DFTLTISSLQPEDFAIYYCQQTYSTPLTFGGGTKV EIK SEQ ID NO: 28036 | QVQLVESGGGVVQPGRSLRLSCAASGFTFSSFGMH WVRQAPGKGLEWVAIIWHSGSNKYYADSVKGRFT ISRDNSKNTLYLQMSSLRAEDTAVYYCARDLSMGG MDVWGQGTTVTVSS SEQ ID NO: 32042 |

FIGURE 50
(Continued)

| | | | |
|---|---|---|---|
| iPS:442390 | 21-225_7E11.001.013 | NA | GACATCCAGATGACCCAGTCTCCATCTCCCTGTCTGCATCTGTAGGAGACAGAGTCACCATTACTTGCCGGGCAAGTCAAACAGAAACCAGGAAAGCCCCTAAATTGGTATCAACAGAAACCAGGAAAGCCCCTAAATTCCTGATCTATACTGCATCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGACTTACAGTACCCCGCTCACTTTCGGCGGAGGGACCAAGGTGGAGATCAA |
| | | | SEQ ID NO: 28037 |
| | | AA | DIQMTQSPSSLSASVGDRVTITCRASQNIISYLNWYQQKPGKAPKFLIYTASSLQSGVPSRFSGSGSGTDFTLTISSLQPEDFAIYYCQQTYSTPLTFGGGTKVEIK |
| | | | SEQ ID NO: 28038 |
| iPS:442394 | 21-225_7E11.001.014 | NA | GACATCCAGATGACCCAGTCTCCATCTCCCTGTCTGCATCTGTAGGAGACAGAGTCACCATTACTTGCCGGGCAAGTCAAACAGAAACCAGGAAAGCCCCTAAATTGGTATCAACAGAAACCAGGAAAGCCCCTAAATTCCTGATCTATACTGCATCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGACTTACAGTACCCCGCTCACTTTCGGCGGAGGGACCAAGGTGGAGATCAA |
| | | | SEQ ID NO: 28039 |

| | | | |
|---|---|---|---|
| | | | CAGGTGCAGCTGGTGGAGTCTGGGGGAGGCGTGGTCCAGCCTGGGAGGTCCCTGCGACTCTCCTGTGCAGCGTCTGGATTCACCTTCAGTAGCTTTGGCATGCACTGGGTCCGCCAGGCTCCAGGCAAGGGGCTGGAGTGGGTGGCAGTTATCTGGCATGATGGAAGTAATAAATACTATGCAGAGACAATTCCAAAACACGCTTCACCATCTCCAGAGACAATGAGCAGCCTGCGAGCCGAGGTGTATCTGCAAATGAGCAGCCTGCGAGAGATCTGAGACACGGCTGTGTATTACTGTGCGAGAGATCTGAGTATGGGCGGTATGGACGTCTGGGGCCAAGGGACCACGGTCACCGTCCTCA |
| | | | SEQ ID NO: 32043 |
| | | | QVQLVESGGGVVQPGRSLRLSCAASGFTFSSFGMHWVRQAPGKGLEWVAIIWHDGSNKYYAESVKGRFTISRDNSKNTLYLQMSSLRAEDTAVYYCARDLSMGGMDVWGQGTTVTVSS |
| | | | SEQ ID NO: 32044 |
| | | | CAGGTGCAGCTGGTGGAGTCTGGGGGAGGCGTGGTCCAGCCTGGGAGGTCCCTGCGACTCTCCTGTGCAGCGTCTGGATTCACCTTCAGTAGCTTTGGCATGCACTGGGTCCGCCAGGCTCCAGGCAAGGGGCTGGAGTGGGTGGCAGTTATCTGGCATGATGGAAGTAATAAATACTATGCAGAGACAATTCCAAAACACGCTTCACCATCTCCAGAGACAATGAGCAGCCTGCGAGCCGAGGTGTATCTGCAAATGAGCAGCCTGCGAGAGATCTGAGACACGGCTGTGTATTACTGTGCGAGAGATCTGAGTATGGGCGGTATGGACGTCTGGGGCCAAGGGACCACGGTCACCGTCCTCA |
| | | | SEQ ID NO: 32045 |

FIGURE 50
(Continued)

| | | | |
|---|---|---|---|
| iPS:442398 | | AA | DIQMTQSPSSLSASVGDRVTITCRASQNIISYLNW YQQKPGKAPKFLIYTASSLQSGVPSRFSGSGSGT DFTLTISSLQPEDFAIYYCQQTYSTPLTFGGGTKV EIK<br><br>SEQ ID NO: 28040 | QVQLVESGGGVVQPGRSLRLSCAASGFTFSSFGMH WVRQAPGKGLEWVAIIWHSGSNKYYAESVKGRFT ISRDNSKNTLYLQMSSLRAEDTAVYYCARDLSMGG MDVWGQGTTVTVSS<br><br>SEQ ID NO: 32046 |
| | 21-225_7E11.001.015 | NA | GACATCCAGATGACCCAGTCTCCATCCTCCCT GTCTGCATCTGTAGGAGACAGAGTCACCATTA CTTGCCGGGCAAGTCAAAACATTATCAGTCTAT TTAAATTGGTATCAACAGAAACCAGGGAAAG CCCCTAAACTCCTGATCTATACTGCATCCAGT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGACTTACAGTACCCCGCTC ACTTTCGGCGGGGGGACCAAGGTGGAGATCA AA<br><br>SEQ ID NO: 28041 | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGGCT GGAGTGGGTGGCAATTATCTGGCATAGTGGAAGT AATAAATACTATGCAGACTCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA<br><br>SEQ ID NO: 32047 |
| | | AA | DIQMTQSPSSLSASVGDRVTITCRASQNIISYLNW YQQKPGKAPKLLIYTASSLQSGVPSRFSGSGSGT DFTLTISSLQPEDFATYYCQQTYSTPLTFGGGTK VEIK<br><br>SEQ ID NO: 28042 | QVQLVESGGGVVQPGRSLRLSCAASGFTFSSFGMH WVRQAPGKGLEWVAIIWHSGSNKYYADSVKGRFT ISRDNSKNTLYLQMSSLRAEDTAVYYCARDLSMGG MDVWGQGTTVTVSS<br><br>SEQ ID NO: 32048 |

FIGURE 50
(Continued)

| | | | | |
|---|---|---|---|---|
| iPS:442402 | 21-225_7E11.001.016 | NA | GACATCCAGATGACCCAGTCTCCATCCTCCT GTCTGCATCTGTAGGAGACAGAGTCACCATTA CTTGCCGGGCAAGTCAAAACATTATCAGCTAT TTAAATTGGTATCAACAGAAACCAGGGAAAG CCCCTAAACTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGACTTACAGTACCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTGGCAT GCACTGGGTCCGCCAGGCTCCAGGCAAGGGCT GGAGTGGGTGGCAATTATCGGCATAGTGGAAGT AATAAATACTATGCAGAGATCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA |
| | | | SEQ ID NO: 28043 | SEQ ID NO: 32049 |
| | | AA | DIQMTQSPSSLSASVGDRVTITCRASQNIISYLNW YQQKPGKAPKLLIYTASSLQSGVPSRFSGSGSGT DFTLTISSLQPEDFATYYCQQTYSTPLTFGGGTK VEIK | QVQLVESGGGVVQPGRSLRLSCAASGFTFSSFGMH WVRQAPGKGLEWVAIIWHSGSNKYYAESVKGRFT ISRDNSKNTLYLQMSSLRAEDTAVYYCARDLSMGG MDVWGQGTTVTVSS |
| | | | SEQ ID NO: 28044 | SEQ ID NO: 32050 |
| iPS:442406 | 21-225_7E11.001.017 | NA | GACATCCAGATGACCCAGTCTCCATCCTCCCT GTCTGCATCTGTAGGAGACAGAGTCACCATTA CTTGCCGGGCAAGTCAAAACATTATCAGCTAT TTAAATTGGTATCAACAGAAACCAGGGAAAG CCCCTAAACTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACAGACTTACAGTACCCCGCTC ACTTTCGGCGGCGGGACCAAGGTGGAGATCA AA | CAGGTGCAGCTGGTGGAGTCTGGGGGAGGCGTG GTCCAGCCTGGGAGGTCCCTGAGACTCTCCTGTG CAGCGTCTGGATTCACCTTCAGTAGCTTTGGCAT GCACTGGGTCCGCCAGGCTCCAGGCAAGGGCT GGAGTGGGTGGCAATTATCGGCATGAAGGAAG TAATAAATACTATGCAGAGACGCCGTGAAGGGCCG ATTCACCATCTCCAGAGACAATTCCAAAAACACG CTGTATCTGCAAATGAGCAGCCTGCGAGCCGAG GACACGGCTGTGTATTACTGTGCGAGAGATCTGA GTATGGGCGGTATGGACGTCTGGGGCCAAGGGA CCACGGTCACCGTGTCCTCA |
| | | | SEQ ID NO: 28045 | SEQ ID NO: 32051 |

FIGURE 50
(Continued)

| | | | | |
|---|---|---|---|---|
| iPS:442410 | 21-225_7E11.001.018 | AA | DIQMTQSPSSLSASVGDRVTITCRASQNIISYLNWYQQKPGKAPKLLIYTASSLQSGVPSRFSGSGSGTDFTLTISSLQPEDFATYYCQQTYSTPLTFGGGTKVEIK<br>SEQ ID NO: 28046 | QVQLVESGGGVVQPGRSLRLSCAASGFTFSSFGMHWVRQAPGKGLEWVAIIWHEGSNKYYADAVKGRFTISRDNSKNTLYLQMSSLRAEDTAVYYCARDLSMGGMDVWGQGTTVTVSS<br>SEQ ID NO: 32052 |
| | | NA | GACATCCAGATGACCCAGTCTCCATCCTCCCTGTCTGCATCTGTAGGAGACAGAGTCACCATCACTTGCCGGGCAAGTCAAAACATTATCAGTTATTTAAATTGGTATCAACAGAAACCAGGGAAAGCCCCTAAATTCCTGATCTATACTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAATTTACTACTGTCAACAGACTTACAGTACCCCGCTCACTTTCGGCGGGGGGACCAAGGTGGAGATCAAA<br>SEQ ID NO: 28047 | CAGGTGCAGCTGGTGGAGTCTGGGGGAGGCGTGGTCCAGCCTGGGAGGTCCCTGCGACTCTCCTGTGCAGCGTCTGGATTCACCTTCAGTAGCTTTGGCATGCACTGGGTCCGCCAGGCTCCAGGCAAGGGGCTGGAGTGGGTGGCAATTATCTGGCATGAGGGCAAGTAATAAATACTATGCAGAATCCGTGAAGGGCCGATTCACCATCTCCAGAGACAATCCAAAAACACGCTGTATCTGCAAATGAGCAGCCTGCGAGCCGAGGACACGGCTGTGTATTACTGTGCGAGAGATCTGAGTATGGGCGGTATGGACGTCTGGGGCCAAGGGACCACGGTCACCGTGTCCTCA<br>SEQ ID NO: 32053 |
| | | AA | DIQMTQSPSSLSASVGDRVTITCRASQNIISYLNWYQQKPGKAPKFLIYTASSLQSGVPSRFSGSGSGTDFTLTISSLQPEDFAIYYCQQTYSTPLTFGGGTKVEIK<br>SEQ ID NO: 28048 | QVQLVESGGGVVQPGRSLRLSCAASGFTFSSFGMHWVRQAPGKGLEWVAIIWHDASNKYYAESVKGRFTISRDNSKNTLYLQMSSLRAEDTAVYYCARDLSMGGMDVWGQGTTVTVSS<br>SEQ ID NO: 32054 |

FIGURE 50
(Continued)

| | | | | |
|---|---|---|---|---|
| iPS:442417 | 21-225_7E11.001.019 | NA | GACATCCAGATGACCCAGTCTCCATCCTCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGT TGCAAAGTGGGGTCCCATCAAGGTTCAGTGGC AGTGGATCTGGGACAGATTTCACTCTCACCAT CAGCAGTCTGCAACCTGCAAGATTTTGCAATT ACTACTGTCAACAGACTTACAGTACCCGCTC ACTTTCGGCGGCGGGACCAAGGTGGAGATCA AA | GAGGTGCAGCTGGTGGTGAGTCTGGGGAGGCGTG GTCCAGCCTGGGGGGTCCCTGCGACTCTCCTGTG CAGCGTCTGATTCACCTTCAGTAGCTTTGGCAT GCACTGGGTCCGCCAGGCTCCAGGCAAGGGCT GGAGTGGGTGGCAATTATCTGGCATGATGAAGT AATAAATACTATGCAGAGACAATCCGTGAAGGGCCGA TTCACCATCTCCAGAGACAATGCCAAAAACACGC TGTATCTGCAAATGAGCAGCCTGCGAGCCGAGG ACACGGCTGTGTATTACTGTGCGAGAGATCTGAG TATGGGCGTATGGACGTCTGGGGCCAAGGGAC CACGGTCACCGTGTCCTCA |
| | | | SEQ ID NO: 28049 | SEQ ID NO: 32055 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | EVQLVESGGGVVQPGGSLRLSCAASGFTSSFGMH WVRQAPGKGLEWVAIIWHDGSNKYYAESVKGRFT ISRDNAKNTLYLQMSSLRAEDTAVYYCARDLSMG GMDVWGQGTTVTVSS |
| | | | SEQ ID NO: 28050 | SEQ ID NO: 32056 |
| iPS:442431 | 21-225_7E11.001.021 | NA | GACATCCAGATGACCCAGTCTCCATCCTCCT GTCTGCATCTGTAGGAGACAGAGTCACCATTG CTTGCCGGGCAAGTCAAAACATTATCAGCTAT TTAAATTGGTATCAACAGAAACCAGGGAAAG CCCCTAAATTCCTGATCTATACTGCATCCAGT TGCAAAGTGGGGTCCCATCAAGGTTCAGTGGC AGTGGATCTGGGACAGATTTCACTCTCACCAT CAGCAGTCTGCAACCTGCAAGATTTTGCAATT ACTACTGTCAACAGACTTACAGTACCCCGCTC ACTTTCGGCGGCGGGACCAAGGTGGAGATCA AA | GAGGTGCAGCTGGTGGTGAGTCTGGGGAGGCGTG GTCCAGCCTGGGGGGTCCCTGCGACTCTCCTGTG CAGCGTCTGATTCACCTTCAGTAGCTTTGGCAT GCACTGGGTCCGCCAGGCTCCAGGCAAGGGCT GGAGTGGGTGGCAATTATCTGGCATGATGAAGT AATAAATACTATGCAGAGACAATCCGTGAAGGGCCGA TTCACCATCTCCAGAGACAATGCCAAAAACACGC TGTATCTGCAAATGAGCAGCCTGCGAGCCGAGG ACACGGCTGTGTATTACTGTGCGAGAGATCTGAG TATGGGCGTATGGACGTCTGGGGCCAAGGGAC CACGGTCACCGTGTCCTCA |
| | | | SEQ ID NO: 28051 | SEQ ID NO: 32057 |

FIGURE 50
(Continued)

| | | | |
|---|---|---|---|
| iPS:442438 | 21-225_7E11.001.022 | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK<br><br>SEQ ID NO: 28052 | EVQLVESGGGVVQPGGSLRLSCAASGFTFSSFGMH WVRQAPGKGLEWVAIIWHSGSNKYYAESVKGRFT ISRDNAKNTLYLQMSSLRAEDTAVYYCARDLSMG GMDVWGQGTTVTVSS<br><br>SEQ ID NO: 32058 |
| | | NA | GACATCCAGATGACCCAGTCTCCATCCTCCCT GTCTGCATCTGTAGGAGACAGAGTCACCATTA CTTGCCGGGCAAGTCAAAACATTATCAGTTAT TTAAATTGGTATCAACAGAAACCAGGAAAAG CCCCTAAATTCCTGATCTATACTGCATCCAGTT TGCAAAGTGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGGGGGACCAAGGTGGAGATCA AA<br><br>SEQ ID NO: 28053 | GAGGTGCAGCTGGTGGAGTCTGGGGGAGGCGTG GTCCAGCCTGGGGGGGTCCCTGCGACTCTCCTGT CAGCGTCTGGATTCACCTTCAGTAGCTTTGGCAT GCACTGGGTCCGCCAGGCTCCAGGCAAGGGGCT GGAGTGGGTGGCAATTATCTGGCATGAAGGAAG TAATAAATACTATGCAGAATCCGTGAAGGGCCG ATTCACCATCTCCAGAGACACAATGCCAAAACAC GCTGTATCTGCAAATGAGCAGCCTGCGAGCCGA GGACACGGCTGTGTATTACTGTGCGAGAGATCTG AGTATGGGCGGTATGGACGTCTGGGGCCAAGGG ACCACGGTCACCGTGTCCTCA<br><br>SEQ ID NO: 32059 |
| | | AA | DIQMTQSPSSLSASVGDRVTITCRASQNIISYLNW YQQKPGKAPKFLIYTASSLQSGVPSRFSGSGSGT DFTLTISSLQPEDFAIYYCQQTYSTPLTFGGGTKV EIK<br><br>SEQ ID NO: 28054 | EVQLVESGGGVVQPGGSLRLSCAASGFTFSSFGMH WVRQAPGKGLEWVAIIWHEGSNKYYAESVKGRFT ISRDNAKNTLYLQMSSLRAEDTAVYYCARDLSMG GMDVWGQGTTVTVSS<br><br>SEQ ID NO: 32060 |

FIGURE 50
(Continued)

| | | | | |
|---|---|---|---|---|
| iPS:442568 | 21-225_149D8 | NA | GAAATTGTGTTGACGCAGTCTCCAGGCACCCT GTCTTTGTTTCCAGGGGAAAGAGCCACCCTCT CCTGCAGGGCCAGTCAGAGTGTGATCAGCAGC TACTTAGCCTGGTACCAGCAGAAACCTGGCCA GGCTCCCAGGCTCCTCATCTTTGGTGTATCTAG TTGGGCCACTGGCATCCCAGACAGGTTCAGTG GCAGTGGGTCTGGGACAGACTTCACTCTCACC ATCAGCAGACTGGAGCCTGAAGATTTTGCAGT GTATTACTGTCAACAATATGGTAGGTCACCAT TCAATTTCGGCCCTGGGACCAAAGTGATATC AAA<br>SEQ ID NO: 28055 | CAGGTGCAGTCGACAGGAGTCGGGCCAGGACTG GTGAAGCCTTCACAGACCCTGTCCCTCAATTGCA CTGTCTCTGGTGGCTCCATCAGCAGCAGTGGTTA CTACTGGAGCTGGATCCGCCAGCACCCAGGAA GGGCCTGGAATGGATTGGGTACAGTATTACAGT GGGAGCACCTACTACAACCCGTCCCTCAAGAGTC GAATTACCATATCAGTAGACACGTCTAACAACCA GTCTCCCTGAAGCTGAGCTCTGTGACTGCCGCG GACACGGCCGTGTATTACTGTGCGAGAGGGGA TATAACTGGAACCATGCTTTTGATATCTGGGGCC AAGGGACAATGGTCACCGTCTCTTCA<br>SEQ ID NO: 32061 |
| | | AA | EIVLTQSPGTLSLFPGERATLSCRASQSVISSYLA WYQQKPGQAPRLLIFGVSSWATGIPDRFSGSGSG TDFTLTISRLEPEDFAVYYCQQYGRSPFNFGPGT KVDIK<br>SEQ ID NO: 28056 | QVQLQESGPGLVKPSQTLSLNCTVSGGSISNSGYY WSWIRQHPGKGLEWIGYSYYSGSTYYNPSLKSRITI SVDTSNNQFSLKLSSVTAADTAVYYCARGGYNWN HAFDIWGQGTMVTVSS<br>SEQ ID NO: 32062 |
| iPS:443003 | 21-225_43F11_LC2 | NA | CAGTCTGTGCTGACGCAGCCGCCCTCAGTGTC TGGGGCCCCAGGGCAGCAGAGGGTCACCATCCCT GCACTGGAGCAGCTCCAACATGGGGGCAGG TTATGATGTACACTGGTACCAGCAGCTTCCAG GAACAGCCCCCAAACTCCTCATCTATGGTAAC AGCAATCGGCCCTCAAGTCTGGCACCTCAGCCTCCCT CTCTGGCTCCAAGTCTGGCACCTCAGCCTCCCT GGCCATCACTGGGCTCCAGGCTGAGGATGAGG CTGATTATTACTGCCAGTCCTATGACAACAGC CTGAGTGGTTCGGTATTCGGCGGAGGGACCAA GCTGACCGTCCTA<br>SEQ ID NO: 28057 | CAGGTGCAGCTGGTGCAGTCTGGGGCTGAGGTG AAGAAGCCTGGGGCCTCAGTGAAGGTCTCCTGC AAGGCTTCTGGATACACCTTCACCGGCTACTATA TACACTGGGTGCGACAGGCCCCTGGACAAGGCC TTGAGTGGATGGGGATGGATCAACCCTAACAGTGG TGGCACAAACTATGCACAGAAGTTTCAGGGCGG GGTCACCATGACCAGGTCACGTCCATCAACACA GCCTACATGGACCTGAGCAGGCTGAGATCTGAC GACACGGCCGTGTATTACTGTGCGAGAGAGGG AATTACTTCTACAACCACGTTATGACGTCTGGG GCCAAGGGACCCCGGTCACCGTCCTCA<br>SEQ ID NO: 32063 |

FIGURE 50
(Continued)

| | | | |
|---|---|---|---|
| iPS:443005 | 21-225_43F11_LC1 | AA | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDNSLSGSVFGGGTKLTVL<br>SEQ ID NO: 28058 | QVQLVQSGAEVKKPGASVKVSCKASGYTFTGYYIHWVRQAPGQGLEWMGWINPNSGGTNYAQKFQGGVTMTRLTSINTAYMDLSRLRSDDTAVYYCARGGNYFYNHVMDVWGQGTPVTVSS<br>SEQ ID NO: 32064 |
| | | NA | GATGTTGTGATGACTCAGTCTCCACTCTCCCTGCCCGTCACCCTTGGACAGCCGGCCTCCATCTCTGCAGGTCTAGTCAAAGCCTCGTATACAGTGATGGAAACACTTACTTGAATTGGTTTCAGCAGAGGCCAGGCCAATCTCCAAGGCGCCTAATTTATAAGGTTTCTAACTGGGACTCTGGGGTCCCAGACAGATTCAGCGGCCAGTGGGTCAGGCACTGATTTCACACTGAAAATCAGCAGGGTGGAGGCTGAGGATGTGGGGGTTTATTACTGCAATGCAAGTACACACTGGCCGCTCACTTTCGGCGGAGGGACCAAGGTGGAGATCAAA<br>SEQ ID NO: 28059 | CAGGTGCAGCTGGTGCAGTCTGGGGCTGAGGTGAAGAAGCCTGGGGCCTCAGTGAAGGTCTCCTGCAAGGCTTCTGGATACACCTTCACCGGCTACTATATACACTGGGTGCGACAGGCCCCTGGACAAGGCCTTGAGTGGATGGGATGGATCAACCCTAACAGTGGTGGCACAAACTATGCACAGAAGTTTCAGGGCAGGGTCACCATGACCAGGCTCACGTCCATCAACACATACATGGACCTGAGCAGGCTGAGATCTGACGACACGGCCGTGTATTACTGTGCGAGAGGAGGGAATTACTTCTACAACCACGTTATGGACGTCTGGGGCCAAGGGACCCCGGTCACCGTCTCCTCA<br>SEQ ID NO: 32065 |
| | | AA | DVVMTQSPLSLPVTLGQPASISCRSSQSLVYSDGNTYLNWFQQRPGQSPRRLIYKVSNWDSGVPDRFSGSGSGTDFTLKISRVEAEDVGVYYCMQGTHWPLTFGGGTKVEIK<br>SEQ ID NO: 28060 | QVQLVQSGAEVKKPGASVKVSCKASGYTFTGYYIHWVRQAPGQGLEWMGWINPNSGGTNYAQKFQGGVTMTRLTSINTAYMDLSRLRSDDTAVYYCARGGNYFYNHVMDVWGQGTPVTVSS<br>SEQ ID NO: 32066 |

FIGURE 50
(Continued)

| | | | |
|---|---|---|---|
| iPS:443006 | 21-225_25A4.001.029 | NA | GACATCGTGATGACCCAGTTTCCAGACTCCCTGGCTGTGTCTCTGGGCGAGAGGGCCACCATCAAGTGTAAGTCCAGCCAGAGTGTTTTATACAGCTCCCACAATAACAACTACTTAGCTTGGTACCAGCAGAAACCAGGACAGCCTCCTAAGTTGCTCCTTTACTGGGCATCTACCCGGAATCCGGGGTCCCTGACCGATTCAGTGGCAGCGGGTCTGGGACAGAATTCACTCTCACCATCAGCAGCCTGCAGGCTGAAGATGTGGCAGTTTATTACTGTCAGCAGTATTATAGTACTCCTCGACGTTCGGCCAAGGGACCAAGGTGGAAATCAAA |
| | | | SEQ ID NO: 28061 |
| | | AA | DIVMTQFPDSLAVSLGERATIKCKSSQSVLYSSHNNNYLAWYQQKPGQPPKLLLYWASTRESGVPDRFSGSGSGTEFTLTISSLQAEDVAVYYCQQYYSTPPTFGQGTKVEIK |
| | | | SEQ ID NO: 28062 |
| | | NA | CAGGTGCTCCTGGTGCAGTCTGGGGCTGAGGTGAAGAGGCCTGGGGCCTCAGTGAAGGTCAGCTGCAAGGCTTCTGGATACACCTTCACCAATTATGATATTAATTGGGTGCGACAGGCCACTGGACAAGGCTTGAGTGGATGGGATGTACCTAACAGTGGTCAAACAGGCTATGCACAGAAATTCCAGGGCAGAGTCACCATGACCAGGGACACCTCCATCAGCACAGCCTACATGGAGCTGAGCAGCCTGAGATCTGAGGACACGGCCGTCTATTACTGTGCGAGTAGCAGTGGCTGGTACTACTTTGACTACTGGGGCCAGGGAACCCTGGTCACCGTGTCCTCA |
| | | | SEQ ID NO: 32067 |
| | | | QVLLVQSGAEVKRPGASVKVSCKASGYTFTNYDINWVRQATGQGLEWMGWMYPNSGQTGYAQKFQGRVTMTRDTSISTAYMELSSLRSEDTAVYYCASSSGWYYFDYWGQGTLVTVSS |
| | | | SEQ ID NO: 32068 |
| iPS:443016 | 21-225_4H6.014 | NA | GACATCCAGATGACCCAGTCTCCATCTTCCGTGTCTGCATCTGTAGGAGACAGAGTCACCATCACTTGTCGGGCGAGTCAGGGTATTAGCAGCTGGTTAGCCTGGTATCAGCAGAAACCAGGGAAAGCCCCTAAGCTCCTGATCTATGGTGCATCCAGTTTGCAAAGTGGGGTCCCATCAAGGTTCAGCGGCAGTGGATCTGGGACAGATTTCACTCTCACCATCAGCAGCCTGCAGCCTGAAGATTTTGCAACTTATTATTGTCAACAGGCTAACAGTTTCCCATTCACTTTCGGCCCTGGGACCAAAGTGGATATCAAA |
| | | | SEQ ID NO: 28063 |
| | | | CAGGTGCAGCTGGTACAGTCTGGGGCTGAGGTGAAGAAGCCTGGGGCCTCAGTGAAGGTCAGCTGCAAGGCTTCTGGATACACCTTCACCGACTACTATTTGCACTGGGTGCGACAGGCCCCTGGACAAGGTCTTGAGTGGATGGGATGGATCAACCCTAACAGTGGTGGCACAAACTATGCACAGGGACACGTCCATCAGCACAGCCTACATGGGGCTGAGCAGCCTGAGATCTGACGACACGGCCGTGTATTACTGTGCGAGAGATGCTACCAGCTCGTTTGACTACTGGGGCCAGGGAACCCTGGTCACCGTGTCCTCA |
| | | | SEQ ID NO: 32069 |

FIGURE 50
(Continued)

| | | | |
|---|---|---|---|
| iPS:443027 | | AA | DIQMTQSPSSVSASVGDRVTITCRASQGISRWLA WYQQKPGKAPKLLIYGASSLQSGVPSRFSGSGS GTDFTLTISSLQPEDFATYYCQQANSFPFTFGPGT KVDIK | QVQLVQSGAEVKKPGASVKVSCKASGYTFTDYYL HWVRQAPGQGLEWMGWIHPNSGGTNYAQKFQGR VTMTRDTSISTAYMGLSSLRSDDTAVYYCARDATS SFDYWGQGTLVTVSS |
| | | | SEQ ID NO: 28064 | SEQ ID NO: 32070 |
| | 21-225_7E11.001.023 | NA | GACATCCAGATGACCCAGTCTCCATCCTCCCT GTCTGCATCTGTAGGAGACAGAGTCACCATTG CTTGCCGGGCAAGTCAAAACATTATCAGTAT TTAAATTGGTATCAACAGAAACCAGGGAAAG CCCCTAAATTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAATTT ACTACTGTCAACAGACTTACAGTACCCCGCTC ACTTTCGGCGGAGGGACCAAGGTGGAGATCA AA | CAGGTGCAGCTGGTGGAGTCTGGGGGAGGCGTG GTCCAGCCTGGGAGGTCCCTGCGACTCTCCTGTG CAGCGTCTGGATTCACCTTCAGTAGCTTTGGCAT GCACTGGGTCCGCCAGGCTCCAGGCAAGGGCT GGAGTGGGTGGCAATTATCTGGCATGATGCAAGT AATAAATACTATGCAGACGCCGTGAAGGGCCGA TTCACCATCTCCAGAGACAATTCCAAAAACACGC TGTATCTGCAAATGAGCAGCCTGCGAGCCGAGG ACACGGCTGTGTATTACTGTGCGAGAGATCTGAG TATGGGCGGTATGGACGTCTGGGGCCAAGGGAC CACGGTCACCGTGTCCTCA |
| | | | SEQ ID NO: 28065 | SEQ ID NO: 32071 |
| | | AA | DIQMTQSPSSLSASVGDRVTIACRASQNIISYLN WYQQKPGKAPKFLIYTASSLQSGVPSRFSGSGSG TDFTLTISSLQPEDFAIYYCQQTYSTPLTFGGGTK VEIK | QVQLVESGGGVVQPGRSLRLSCAASGFTFSSFGMH WVRQAPGKGLEWVAIIWHDASNKYYADAVKGRF TISRDNSKNTLYLQMSSLRAEDTAVYYCARDLSMG GMDVWGQGTTVTVSS |
| | | | SEQ ID NO: 28066 | SEQ ID NO: 32072 |

FIGURE 50
(Continued)

| | | | | | |
|---|---|---|---|---|---|
| iPS:446086 | 21-225_94D8 | NA | GACATCGTGTTGACCCAGTCGCCAGACTCCCTGGCTGTGTCTCTGGGCGAGAGGGCCACCATCAACTGCAAGTCCAGACAGAGTGTTTATACAGCTCCAACAATTACAACTACTTAACTGGTACCAGCAGAAACCAGGACAGCCTCCTAAGCTGCTCATTTACTGGGCATCTACCCGGAATCCGGGGTCCCTGACCGATTCAGTGGCAGCGGGTCTGGGACAGATTTCACTCTCACCATCAGCAGCCTGCAGCTGAAGACGTGGCAGTTTATTACTGTCAGCAATATTATAGTTCTCCTACTTTCGGCGGAGGGACCAAGGTGGAGATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGAACCCTAACAGTGGTAACACAGGCTATGCACAGAAGTTCCAGGTCAGAGTCACCATGACCAGGAACACCTCCATAAGCACAGCCTACATGGAGTGAGCAGCCTGAGATCTGAGGACACGGCCGTCTATTACTGTGCGTATAGCAGTGGCTGGTACATCTTTGACTACTGGGGCCAGGGAACCCTGGTCACCGTCTCTTCA |
| | | | SEQ ID NO: 28067 | SEQ ID NO: 32073 |
| | | AA | DIVLTQSPDSLAVSLGERATINCKSRQSVLYSSNNYNYLTWYQQKPGQPPKLLIYWASTRESGVPDRFSGSGSGTDFTLTISSLQAEDVAVYYCQQYYSSPPTFGGGTKVEIK | QVQLVQSGAEVKKPGASVKVSCKTSGYTFTNYDINWVRQATGQGLEWMGWMNPNSGNTGYAQKFQVRVTMTRNTSISTAYMEVSSLRSEDTAVYYCAYSSGWYIFDYWGQGTLVTVSS |
| | | | SEQ ID NO: 28068 | SEQ ID NO: 32074 |
| iPS:446094 | 21-225_77E1 | NA | GACATCGTGATGACCCAGTCTCCAGACTCCCTGGCTGTGTCTCTGGGCGAGAGGGCCACCATCAACTGCAAGTCCAGCCAGAGTGTCTTATACACAGCTCCAACAATTATAACTACTTAGCTTGGTACCAGCAGAAACCAGGACAGCCTCCCCTAAGGTGCTCATTTACTGGACATCTACCCGGGAATCCGGGGTCCCATGACCGATTCAGTGGCAGCGGGTCTGGGACAGATTTCACTCTCACCATCAGCAGCCTGCAGGCTGAAGATGTGGCAGTTTATTACTGTCACAATATCTTAGTAGTTCTCCTGACGTTCGGCCAAGGGACCAAGGTGGAAATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCCCAATTATGATATCAACTGGGTGCGACAGGCCACTGGACAAGGCTTGAGTGGATGGGATGGATGAACCAGAAGTTCCAGGGCAGAGTCACCATGACCAGGAACACCTCCATAAGCACAGCCTACATGGAGCTGAGCAGCCTGAGATCTGAGGACACGGCCGTGTATTATTGTGCGGTTTCCAGTGGCTGGCACTGGTTCGACCCCTGGGGCCAGGGAACCCTGGTCACCGTCGCCTCA |
| | | | SEQ ID NO: 28069 | SEQ ID NO: 32075 |

FIGURE 50
(Continued)

| | | | |
|---|---|---|---|
| iPS:448904 | 21-225_65C12 | AA | DIVMTQSPDSLAVSLGERATINCKSSQTVLHSSN NYNYLAWYQQKPGQPKPGQPPKVLIYWTSTRESGVHD RFSGSGSGTDFTLTISSLQAEDVAVYYCHQYLSS PLTFGQGTKVEIK<br>SEQ ID NO: 28070 | QVQLVQSGAEVKKPGASVKVSCKASGYTFPNYDIN WVRQATGQGLEWMGWMNPNSGNTGYAQKFQGR VTMTRNTSISTAYMELSSLRSEDTAVYYCAVSSGW HWFDPWGQGTLVTVAS<br>SEQ ID NO: 32076 |
| | | NA | GAGATAGTGATGACGCAGTCTCCAGCCACCCT GTCTGTGTTTCCAGGGAAGGAGCCACCCTCT CCTGCAGGGCCAGTCAGAGTGTTAGCATCAAC TTAGCCTGGTACCAGCAGAAACCTGGCCAGGC TCCCAGACTCCTCATCTATGGTGCATCCACCA GGGCCACTGGTATCCCAGCCAGGTTCAATGCC AGTGGGTCTGGGACAGAGTTCACTCTCTCCAT CAGCAGCCTGCAGTCTGAAAATTTGCAGTT ATTACTGTCAGCAGTATAATACCTGGCCTCTC ACTTTCGGCGGAGGGACCAAGGTGGAAATCA AA<br>SEQ ID NO: 28071 | GAGGTGCAGCTGGTGGAGTCTGGGGGAGGCTG GTCAAGCCTGGGGGGTCCCTGAGACTCTCCTGTG CAGCCTCTGGATTCACCTTCAGGAGCTTTAGCTT GAACTGGGTCCGCCAGGCTCCAGGGAAGGGGCT GGAGTGGGTCTCATCATTAGTAGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGGA CACGGCTGTGTATTACTGTGCGAGAGATGCGTAT AGCCACTACTGGGGCCAGGGAACCCTGGTCACC GTCTCCTCA<br>SEQ ID NO: 32077 |
| | | AA | EIVMTQSPATLSVFPGEGATLSCRASQSVSINLA WYQQKPGQAPRLLIYGASFRATGIPARFNASGS GTEFTLSISSLQSENFAVYYCQQYNTWPLTFGGG TKVEIK<br>SEQ ID NO: 28072 | EVQLVESGGGLVKPGGSLRLSCAASGFTFRSFSLN WVRQAPGKGLEWVSSISSSSYIYADSVKGRFTIS RDNAKNSLYLQMNSLRAEDTAVYYCARDAYSHY WGQGTLVTVSS<br>SEQ ID NO: 32078 |

FIGURE 50
(Continued)

| | | | |
|---|---|---|---|
| iPS:448906 | 21-225_72G9 | NA | GACATCCAGATGACCCAGTCTCCATCCTCCCT GTCTGCATCTGTAGGAGACAGAGTCACCATCA CTTGCCGGGCAAGTCAGAGACATTACCAGCTAT TTAAATTGGTATCAGCAGAAACCAGGGAAAG CCCCTAAGCTCCTGATCTATACTGCATCCAGTT TGCAAAGTGGGGTCCCATCAAGGTTCAGTGGC AGTGGATCTGGGACAGATTTCACTCTCACCAT CAGCAGTCTGCAACCTGAAGATTTTGCAACTT ACTACTGTCAACAGAGTCACAGTTTCCCATTC ACTTTCGGCCCTGGGACCAAAGTGGATATCAA A<br>SEQ ID NO: 28073 | GAGGTGCAGCTGTTGGAGTCTGCGGGAGGCCTG GTCAAGCCTGGGGGGTCCCTGAGACTCTCCTGTG CAGCCTCTGGATTCACCTTCAGTAGTTATAGCAT GAACTGGGTCCGCCAGGCTCCAGGGAAGGGGCT GGAGTGGGTCTCATCCATTAGTGGTAGTAGTAGT TACATATACTACGCAGACTCAGTGAAGGGCCGAT TCACCATCTCCAGAGACAACGCCAAGAACTCACT GTATCTGCAAATGAACAGCCTGAGAGCCGAGA CACGGCTGTGTATTTCTGTGCGAGAGAGGGTTCG AGGGGGTTGACCCCTGGGGCCAGGGAACCCTG GTCACCGTCTCCTCA<br>SEQ ID NO: 32079 |
| | | AA | DIQMTQSPSSLSASVGDRVTITCRASQSITSYLN WYQQKPGKAPKLLIYTASSLQSGVPSRFSGSGSG TDFTLTISSLQPEDFATYYCQQSHSFPFTFGPGTK VDIK<br>SEQ ID NO: 28074 | EVQLVESGGGLVKPGGSLRLSCAASGFTFSSYSMN WVRQAPGKGLEWVSSISGSSSYIYYADSVKGRFTIS RDNAKNSLYLQMNSLRAEDTAVYFCARGGSRGFD PWGQGTLVTVSS<br>SEQ ID NO: 32080 |
| iPS:448908 | 21-225_50G9 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TGCTGGTATCAGCAGAAGCCAGGCCAGTCCCC TGTGCTGGTCATCTATCAAGATAGCAAGCGGC CCTCAGGGATCCCTGAGCGATTCTCTGGCTCC AACTCTGGGAACACAGCCACTCTGACCATCAG CGGGACCCAGGCTGCGGAACAGCCGCAGAGGGT ACTGTCAGGCGCGGAGGACCAGGCTGACCGTCCTA ATTCGGCGGAGGGACCAGGCTGACCGTCCTA<br>SEQ ID NO: 28075 | CAGGTGCAGCTGGTGGAGTCTGGGGGAGGCGTG GTCCAGCCTGGGAGGTCCCTGAGACTCTCCTGTG CAGCCTCCGGATTCATCTTCAGTAGCTATGGCAT GCACTGGGTCCGCCAGGCTCCAGGCAAGGGGCT GGAGTGGGTGGCAGTTATATCACAAGATGGAATT ATTAGATACTATGCAGAGACTCCGTGAAGGGCCGAT TCACCATCTCCAGAGACAATTCCAAGAACACGCT GTATCTGCAAATGAACAGCCTGAGAGCTGAGGA CACGGCTGTGTATTACTGTGCGAGAGATGTGAAG CAGTGGCTCGTACGGACCTACGGTATGGACGTCT GGGGCCAAGGGACCACGGTCACCGTCTCCTCA<br>SEQ ID NO: 32081 |

FIGURE 50
(Continued)

| | | | |
|---|---|---|---|
| | | AA | SYELTQPPSVSVSPGQTASITCSGDKLGDKYACW YQQKPGQSPVLVIYQDSKRPSGIPERFSGSNSGN TATLTISGTQARDEAEYYCQARNSRRGVFGGGT RLTVL<br><br>SEQ ID NO: 28076 | QVQLVESGGGVVQPGRSLRLSCAASGFIFSSYGMH WVRQAPGKGLEWVAVISQDGIIRYYADSVKGRFTI SRDNSKNTLYLQMNSLRAEDTAVYYCARDVKQW LVRTYGMDVWGQGTTVTVSS<br><br>SEQ ID NO: 32082 |
| iPS:451102 | 21-225_45F6 | NA | TCCTATGAGCTGACTCAGCCACCCTCAGTGTC CGTGTCCCCAGGACAGACAGCCAGCATCACCT GCTCTGGAGATAAATTGGGGGATAAATATGCT TCCTGGTATCAGCAGAAGCCAGGCCAGTCCCC TGTGCTGGTCATCTATCAAGATAGTAAGCGGC CCTCAGGGATCCCTGAGCGATTCTCTGGCTCC AACTCTGGAAACACAGCCACTCTGACCATCAG CGGGACCCAGGCTATGGATGAGGCTGACTATT ACTGTCAGGCTCGTGGGACAACAGAACTATGTA TTCGGCGGAGGGACCAAGCTGACCGTCCTA<br><br>SEQ ID NO: 28077 | CAGGTGCAGCTGGTGGAGTCTGGGGGAGGCGTG GTCCAGCCTGGGAGGTCCCTGAGACTCTCCTGTG CAGCCTCTGGATTCACCTTCAGTTACTACGGCTT GCACTGGGTCCGCCAGGCTCCAGGCAAGGGCT GGAGTGGGTGGCAGTTATATCATATGATGAAGT AATAAATATTATGCAGAGACTCCGTGAAGGGCCGAT TCACCATCTCCAGAGACAATTCCAAGAACACGCT GTATCTGCAAATGAACAACCTGAGAGCTGAGGA CACGGCTGTGTTTTACTGTGCGAGAGAGATCGA TATTGTAGTGGTACCAGCTGCCCTACTACTACT ACTACGGTATGGACGTCTGGGGCCAAGGGACCA CGGTCACCGTCTCCTCA<br><br>SEQ ID NO: 32083 |
| | | AA | SYELTQPPSVSVSPGQTASITCSGDKLGDKYASW YQQKPGQSPVLVIYQDSKRPSGIPERFSGSNSGN TATLTISGTQAMDEADYYCQAWDNRTMVFGGG TKLTVL<br><br>SEQ ID NO: 28078 | QVQLVESGGGVVQPGRSLRLSCAASGFTFSYYGLH WVRQAPGKGLEWVAVISYDGSNKYYADSVKGRFT ISRDNSKNTLYLQMNNLRAEDTAVFYCAREDRYCS GTSCPYYYYYGMDVWGQGTTVTVSS<br><br>SEQ ID NO: 32084 |

FIGURE 50
(Continued)

| | | | |
|---|---|---|---|
| iPS:451104 | 21-225_49C5 | NA | CAGTCTGTGCTGACTCAGCCACCCTCAGCGTCTGGGACCCCCGGGCAGAGGGTCACCATCTCTTGTTCTGGAAGCAGCTCCAACATCGGAAGTAATATTGTGACCTGGTACCAGCAGCTCCCAGGAACGGCCCCCAAACTCCTCATCTATAGTAATGATCAGCGGGCCCTCAGGGGTCCCTGACCGATTCTCTGGCTCCAAGTCTGGCACCTCAGCTCTGGCCTCATCAGTGGGCTCCAGTCTGAGGATGACAGCCTGATTATTACTGTGCAGCATGGGATGACAGACACAGCTAATGGTTGGGTGTTCGGCGGAGGGACCAAGCTGACCGTCCTA<br>SEQ ID NO: 28079 | CAGGTTCAGCTGGTGCAGTCTGGAGCTGAGGTGAAGAAGCCTGGGGCCTCAGTGAAGGTCTCCTGCAAGGCTTCTGGTTACACCTTTAACAGCTATGGTATCAGCTGGGTGCGACAGGCCCCTGGACAAGGGCTTGAGTGGATGGATGGATCAGCGTTATAATGGTAACACAAAGTATGCACAGAAGCTCCAGGCAGAGTCACCATGACCACAGACACATCCACGAGCACAGCCTACATGGAGCTGAGGAGCCTGAGATCGACGACACGGCCGTGTATTACTGTGCGAGACACGATTTTTGGAGTGGTTATTATAAGGGTATGGACGTCTGGGGCCAAGGGACCACGGTCACCGTCTCCTCA<br>SEQ ID NO: 32085 |
| | | AA | QSVLTQPPSASGTPGQRVTISCSGSSSNIGSNIVTWYQQLPGTAPKLLIYSNDQRPSGVPDRFSGSKSGTSASLAISGLQSEDEADYYCTAWDDSLNGWVFGGGTTLTVL<br>SEQ ID NO: 28080 | QVQLVQSGAEVKKPGASVKVSCKASGYTFNSYGISWVRQAPGQGLEWMGWISAYNGNTKYAQKLQGRVTMTTDTSTSTAYMELRSLRSDDTAVYYCARHDFWSGYYKGMDVWGQGTTVTVSS<br>SEQ ID NO: 32086 |
| iPS:451106 | 21-225_49D10 | NA | CAGTCTGTGCTGACTCAGCCACCCTCAGCGTCTGGGACCCCCGGGCAGAGGGTCACCATCTCTTGTTCTGGAAGCAACTCCAACATCGGAAGTAATATTGTAACCTGGTACCAGCAGCTCCCAGGAACGGCCCCCAAACTCCTCATCTATAGTAATGATCAGCGGGCCCTCAGGGGTCCCTGACCGATTCTCTGGCTCCAAGTCTGGCACCTCAGCTCTGGCCTCATCAGTGGGCTCCAGTCTGAGGATGACAGCCTGATTATTACTGTGCAGCATGGGATGACAGCCTGAATGGTTGGGTGTTCGGCGGAGGGACCAAGCTGACCGTCCTA<br>SEQ ID NO: 28081 | CAGGTTCAGCTGGTGCAGTCTGGAGCTGAGGTGAAGAAGCCTGGGGCCTCAGTGAAGGTCTCCTGCAAGGCTTCTGGTTACACCTTTAACAGCTATGGTATCAGCTGGGTGCGACTGGCCCCTGGACAAGGGTTTGAGTGGATGGATGGATCAGCGCTTATAATGGTAACACAAAGAATGCACACAGAAGCTCCAGGCAGAGTCACCATGACCACAGACACATCCACGAGCACAGCCTACATGGAGCTGAGGAGCTGAGATCTGACGACACGGCCGTTTATTACTGTGCGAGACACGATTTTGGAGTGGTTATTATAAGGGTATGGACGTCTGGGGCCAAGGGACCACGGTCACCGTCTCCTCA<br>SEQ ID NO: 32087 |

FIGURE 50
(Continued)

| | | | |
|---|---|---|---|
| iPS:451108 | 21-225_53E8 | AA | QSVLTQPPSASGTPGQRVTISCSGSGSNSNIGSNIVT WYQQLPGTAPKLLIYSNDQRPSGVPDRFSGSKS GTSASLAISGLQSEDEADYYCAAWDDSLNGWV FGGGTLTVL<br>SEQ ID NO: 28082 | QVQLVQSGAEVKKPGASVKVSCKASGYTFNSYGIS WVRLAPGQGFEWMGWISAYNGNTKNAQKLQGRV TMTDTSTSTAYMELRSLRSDDTAVYYCARHDFW SGYYKGMDVWGQGTTVTVSS<br>SEQ ID NO: 32088 |
| | | NA | CAGTCTGTGCTGACTCAGCCACCCTCAGCGTC TGGGACCCCGGGCAGAGGGTCACCATCTCTT GTTCTGAAGCTGCTCCAACATCGGAAGTAAT ATTGTGACCTGGTACCAGCAGCTCCCAGGAAC GGCCCCCAAACTCCTCATCTATAGTAATGATC AGCGGCCCTCAGGGGTCCCTGACCGATTCTCT GGCTCCAAGTCTGGCACCTCAGCCTCCCTGGC CATCAGTGGGCTCCAGTCTGAGGATGAGGCTG ATTATTACTGTGCAGCATGGGATGACAGCCTG AATGATTGGGTGTTCGGCGGAGGGACCACGCT GACCGTCCTA<br>SEQ ID NO: 28083 | CAGGTTCAGCTGGTGCAGTCTGGAGCTGAGGTGA AGAAGCCTGGGGCCTCAGTGAAGGTCTCCTGCA AGGCTTCTGGTTACACCTTTAACAGCTATGGTAT CAGCTGGGTGCGACAGGCCCCTGGACAAGGCT TGAGTGGATGGGATGGATCAGCGCTTATAATGGT AACACAAAGTTTGCACAGAAGCTCCAGGCAGA GTCACCATGACCACAGACACATCCAGAGCACA GCCTACATGGAACTGAGGAGCCTGAGATCTGAC GACACGGCCGTGTATTACTGTGCGAGACACGATT TTTGGAGTGGTTATTATAAGGGTATGGACGTCTG GGGCCAAGGGACCACGGTCACCGTCTCCTCA<br>SEQ ID NO: 32089 |
| | | AA | QSVLTQPPSASGTPGQRVTISCSGSGSCSNIGSNIVT WYQQLPGTAPKLLIYSNDQRPSGVPDRFSGSKS GTSASLAISGLQSEDEADYYCTAWDDSLNDWVF GGGTLTVL<br>SEQ ID NO: 28084 | QVQLVQSGAEVKKPGASVKVSCKASGYTFNSYGIS WVRQAPGQGLEWMGWISAYNGNTKFAQKLQGRV TMTDTSTSTAYMELRSLRSDDTAVYYCARHDFW SGYYKGMDVWGQGTTVTVSS<br>SEQ ID NO: 32090 |

FIGURE 50
(Continued)

| | | | |
|---|---|---|---|
| iPS:451110 | 21-225_74C9 | NA | TCTTATGAGCTGACTCAGCCACCCTCAGAGTCTGTGTCCCCAGGACAGCAGCCATCACCTGCTCAGGAGATAAATTGGGGACAAGCCAGGCCAGGCAGGCAATATGTTCCTGGTATCAGCAGAAGCCAGGCCAGTCCCCTGTGCTGGTCATCTATCAAGATAACAGGCGGCCGTCAGGGATCCCTGAGCGATTTCTGGCTCCAACTCTGGGAGCACAGCCACTTTGACCATCAGCGGGACCCAGGCTATGGATGAGGCTGACTATTACTGTCAGGCGTGGGACAGCACCCCTGACGTCCTATTCGGCGGAGGGACCAAGCTGACCGTCCTA |
| | | | SEQ ID NO: 28085 |
| | | AA | SYELTQPPSESVSPGQTASITCSGDKSGNKYVSWYQQKPGQSPVLVIYQDNRRPSGIPERFSGSNSGSTATLTISGTQAMDEADYYCQAWDSTPVIFGGGTKLTVL |
| | | | SEQ ID NO: 28086 |
| | | NA | CAGGTGCAGCTGGTGCAGTCTGGGGCTGAGGTGAAGAAGCCTGGGGCCTCAGTGAAGGTCTCCTGCAAGGCTTCTGGATACATTTTCACCGGCTACTATATACACTGGGTGCGACAGGCCCCTGGACAAGGGCTTGAGTGGATGGGATGGATCAACCCTAACAGTGGTGGCACAAACTATGCACAGAAGTTTCAGGGCAGGGTCACCATGACCAGGGACACGTCCATCAGCACAGCCTACATGGAGCTGATCAGGCTGAGATCTGACGACACGGCCGTGTATTATTGTGCGAGAGAAACGAAAGTCTAGCAACTCGTCTTTCTACGACTACTACGGTATGGACGTCTGGGGCCAAGGGACCACGGTCACCGTCTCCTCA |
| | | | SEQ ID NO: 32091 |
| iPS:451112 | 21-225_53D10 | | QVQLVESGGGVVQPGRSLRLSCAASGFTFSSYGMHWVRQAPGKGLEWVAVIWYDGNNKSYADSVKGRFTISRDISKNTLYLQMNSLRAEDTAVYYCARDRDYCSSTSCPYYYYYGMDVWGQGTTVTVSS |
| | | | SEQ ID NO: 32092 |
| | | | CAGGTGCAGCTGGTGCAGTCTGGGGCTGAGGTGAAGAAGCCTGGGGCCTCAGTGAAGGTCTCCTGCAAGGCTTCTGGATACATTTTCACCGGCTACTATATACACTGGGTGCGACAGGCCCCTGGACAAGGGCTTGAGTGGATGGGATGGATCAACCCTAACAGTGGTGGCACAAACTATGCACAGAAGTTTCAGGGCAGGGTCACCATGACCAGGGACACGTCCATCAGCACAGCCTACATGGAGCTGATCAGGCTGAGATCTGACGACACGGCCGTGTATTATTGTGCGAGAGAAACGAAAGTCTAGCAACTCGTCTTTCTACGACTACTACGGTATGGACGTCTGGGGCCAAGGGACCACGGTCACCGTCTCCTCA |

FIGURE 50
(Continued)

| | | | |
|---|---|---|---|
| | | SEQ ID NO: 28087 | SEQ ID NO: 32093 |
| | AA | SYELTQPPSVSVSPGQTASITCSGDKLGNKYACW YQQRPGQSPVLVIYQDRKRPSGIPERFSGSNSGN TATLTISGTQAMDEADYYCQAWDSSTVFGGG TKLTVL | QVQLVQSGAEVKKPGASVKVSCKASGYIFTGYYIH WVRQAPGQGLEWMGWINPNSGGTNYAQKFQGRV TMTRDTSISTAYMELIRLRSDDTAVYYCARENESLA TRPFYDYYGMDVWGQGTTVTVSS |
| | | SEQ ID NO: 28088 | SEQ ID NO: 32094 |
| iPS:451114 | NA | GACATCCAGATGACCCAGTCTCCATCCTCCCT GTCTGCATCTGTAGGAGACAGAGTCACCATCA CTTGCCGGGCAAGTCAGGACATTAGAAAGGAT TTAGGCTGGTATCAGCAGAAACCAGGGAAAG CCCCTAACCGCCTGATCTATCGTGCATCCAGTT TGCAAAGTGGGGTCCCATCAAGGTTCAGCGGC AGTGGATCTGGGACAGAATTCACTCTCACATT CAGCAGCCTGCAGCCTGAAGATTTTGCAACTT ATTACTGTCTACAGCATCATAGTTATCCTCGG ACGTTCGGCCAAGGGACCAAGGTGGAAATCA AA | CAGGTGCAGCTGGTGGAGTCTGGGGGAGGCGTG GTCCAGCCTGGGGAGGTCCCTGAGACTCTCCTGTG CAGCGTCTGGATTCACCTTTAGTGACTATGTCAT GCAGTGGGTCCGCCAGGCTCCAGGCAAGGGCT GGAGTGGGTGGCAGTTATATGTATGATGGAAGT AATAAATACTATGCAGACTCCGTGAAGGGCCGA TTCACCATCTCCAGAGACAATTCCAAGAACACGC TGTATCTGCAAATGAACAGCCTGAGAGCCGAGG ACACGGCTGTGTATTACTGTGCGAGAGAACCGTA TAATAGTGGCTGGTACGACTACGGTATGGACGTC TGGGGCCAAGGGACCACGGTCACCGTCTCCTCA |
| | | SEQ ID NO: 28089 | SEQ ID NO: 32095 |
| 21-225_159A3 | AA | DIQMTQSPSSLSASVGDRVTITCRASQDIRKDLG WYQQKPGKAPNRLIYAASSLQSGVPSRFSGSGS GTEFTLTFSSLQPEDFATYYCLQHHSYPRTFGQG TKVEIK | QVQLVESGGGVVQPGRSLRLSCAASGFTFSDYVM QWVRQAPGKGLEWVAVIWYDGSNKYYADSVKGR FTISRDISKNTLYLQMNSLRAEDTAVYYCAREPYNS GWYDYGMDVWGQGTTVTVSS |
| | | SEQ ID NO: 28090 | SEQ ID NO: 32096 |

FIGURE 50
(Continued)

| | | | | |
|---|---|---|---|---|
| iPS:451116 | 21-225_164A4 | NA | GACATCGTGATGACCCAGTCTCCAGACTCCCGGGCTGTGTCTCTGGGCGAGAGGGCCACCATCAAGTGCAAGTCCAGCCAGAGTGTTTATACAGCTCCAACAATAAGAACTACTTAACTTGGTACCAGCAGAAACCAGGACAGCCTCCAAACTGTTCATTTACTGGGCATCTACCCGGGAATCCGGGGTTCCTGACCGATTCAGTGGCAGCGGGTGTGGGACAGATTTCACTCTCACCATCAGCAGCGTGCAGGCCGAAGATGTGGCAGTTTATTACTGTCAGCAATATTTAGTACTCCGTGACGTTCGGCCAAGGGACCAAGGTGGAAATCAAA<br>SEQ ID NO: 28091<br><br>DIVMTQYPDSRAVSLGERATIKCKSSQSVLYSSNNKNYLTWYQQKPGQPPKLFIYWASTRESGVPDRFSGSGCGTDFTLTISSVQAEDVAVYYCQQYFSTPWTFGQGTKVEIK<br>SEQ ID NO: 28092 | CAGGTGCAGCTGGTGCAGTCTGGGGCTGAGGTGAAGAAGCCTGGGGCCTCAGTGAAGGTCTCCTGCAAGGCTTCTGGATTCACCTTCCCAATTATGATATCAACTGGGTGCGACAGGCCACTGGACAAGGCCTTGAGTGGATGGGATGGATGCACCTAACAGTGGTAACACAGGCTATGCACAGAAGTTCAGGGCAGAGTCACCATGACCAGGAACACCTCATAAGCACAGCCTACATGGAGCTGAGCAGCCTGAGATCTGAGGACACGGCCGTGTATTACTGTGCGAGTAGCAGTGGCTGGTACTTCTTTGACTACTGGGGCCAGGGAACCCTGGTCACCGTCTCCTCA<br>SEQ ID NO: 32097<br><br>QVQLVQSGAEVKKPGASVKVSCKASGFTFPNYDINWVRQATGQGLEWMGWMHPNSGNTGYAQKFQGRVTMTRNTSISTAYMELSSLRSEDTAVYYCASSSGWYFFDYWGQGTLVTVSS<br>SEQ ID NO: 32098 |
| iPS:451118 | 21-225_191C8 | NA | GAAATAGTGATGACGCAGTCTCCAGCCACCCTGTCTGTGTCTCCAGGGGAAAGAGCCACCCTCTCCTGCAGGGCCAGTCAGAGTGTTCGCAGTAACTTAGCCTGGTACCAGCAGGAAACCTGGCCAGGCTCCCAGGCTCCTCATCTATGGTGCATCCACCAGGGCCACTGGTATCCCAGCCAGGTTCAGTGGCAGTGGGTCTGGGACAGAATTCACTCTCACCATCAGCAGCCTGCAGTCTGAAGATTTTGCAGTTTATTACTGTCAGCAGTCTTTACCTGGCTCCGGACGTTCGGCGGAGGGACCAAGGTGGAAATCAAA<br>SEQ ID NO: 28093 | CAGGTGCAGCTGCAGGAGTCGGGCCCAGGACTGGTGAAGCCTTCGGAGACCCTGTCCCTCACCTGCACTGTCTCTAGTGGCTCCGTCAGCAGTGGTGTTACTACTGGAGCTGGATCCGGCAGCCCCCAGGGAAGGGACTGGAGTGGATTGGGTATATCTATTACAGTGGGACCACCATTTACAACCCCTCCCTCAAGAGTCGAGTCACCATATCAGTAGACACGTCCAAGAACCAGTTCTCCCTGAAGCTGACCTCTGTGACCGCTGCGGACACGGCCGTGTATTACTGTGCGAGACACGTTTTGCTTGATGGTTGTGGTTATTTCTTTGACTCCTGGGGCCAGGGAACCCTGGTCACCGTCTCCTCA<br>SEQ ID NO: 32099 |

FIGURE 50
(Continued)

| | | | | |
|---|---|---|---|---|
| iPS:451120 | 21-225_197D3 | AA | EIVMTQSPATLSVSPGERATLSCRASQSVRSNLAWYQQEPGQAPRLLIYGASTRATGIPARFSGSGSGTEFTLTISSLQSEDFAVYYCQQSFTWLRTFGQGTKVEIK<br>SEQ ID NO: 28094 | QVQLQESGPGLVKPSETLSLTCTVSSGSVSSGYYWSWIRQPPGKGLEWIGYIYYSGTTIYNPSLKSRVTISVDTSKNQFSLKLTSVTVADTAVYYCARDTFCFDGCGYFFDSWGQGTLVTVSS<br>SEQ ID NO: 32100 |
| | | NA | GACATCCAGATGACCCAGTCTCCATCCTCACTGTCTGCATCTGTAGGAGACAGAGTCACCATCACTTGTCGGGCGAGTCAGGGCATTAGAAATTATTTAGCCTGGTTTCAGCAGAAACCAGGGAAAGCCCCTAAGTCCCTGATCTATGCTGCATCCAGTTTGCAAAGTGGGGTCCCCTCAAGTTCAGCGGCAGTGGATCTGGGACAGATTTCACTCTCACCATCAGCAGCCTGCAGCCTGAAGATTTTGCAACTTATTACTGCCAACATTATCTTACTTACCCGCTCACTTTCGGCGGAGGGACCAAGGTGGAGATCAAA<br>SEQ ID NO: 28095 | CAGGTGCAGCTGGTGGAGTCTGGGGGAGGCGTGGTCCAGCCTGGGAGGTCCCTGAGACTCTCCTGTGCAGCGTCTGGATTCATCTTCAGTAGCCATGGCATGCACTGGGTCCGCCAGGCTCCAGGCAAGGGGCTGGAGTGGGTGGCAGTTATATGGTATGATGGAAGTAATGAACACTATGCAGACTCCGTGAAGGGCCGATTCACCATCTCCAGAGACAACAATTCCAAGAACACGCTGTATCTGCAAATGAACAGCCTGAGAGCCGAGGACACGGCTGTTTATTACTGTGCGAGAGATCAAGGTGTGGGGTACTACGGTATGGACGTCTGGGGCCAAGGGACCACGGTCACCGTCTCCTCA<br>SEQ ID NO: 32101 |
| | | AA | DIQMTQSPSSLSASVGDRVTITCRASQGIRNYLAWFQQKPGKAPKSLIYAASSLQSGVPSKFSGSGSGTDFTLTISSLQPEDFATYYCQHYLTYPLTFGGGTKVEIK<br>SEQ ID NO: 28096 | QVQLVESGGGVVQPGRSLRLSCAASGFIFSSHGMHWVRQAPGKGLEWVAVIWYDGSNEHYADSVKGRFTISRDNSKNTLYLQMNSLRAEDTAVYYCARDQGVGYYGMDVWGQGTTVTVSS<br>SEQ ID NO: 32102 |

FIGURE 50
(Continued)

| | | | | |
|---|---|---|---|---|
| iPS:451122 | 21-225_200A1 | NA | GAAATTGTGTTGACGCAGTCTCCAGGCATCCT GTCTTTGTATCCAGGGGAAAGAGCCACCCTCT CCTGTAGGGCCAGTCAGAGTGTTAACAGCAAC TATTTAGCCTGGTACCAGCAGAGACCTGGCCA GGCTCCCAGGTCCTCATTTATGGGGCATCCA GCAGGGCCACTTGCATCCTGGACAGGTTCAGT GGCAGTGGGTGTGGGACAGACTTCACTCTCAC GATCAGCAGACTGGAGCCTGAAGATTTTGCAG TGTATTGCTGTCAGCAGTATGAGATCTCACCG TGGACGTTCGGCCAAGGGACCAAGGTGGAAA GCAAA | CAGGTGCAGCTACAGCAGTGGGGCGCAGGACTG TTGAAGCCTTCGGAGACCCTGTCCCTCACCTGCG CTGTCTATGGTGGGTCCTTCAGTGTTTACTATTGG AGCTGGATCCGCCAGCCCCCAGGGAAGGGGCTG GAGTGGATTGGGGAAATCAATCATAGTGGAAGC ACCAACTACAACCGTCCCTCAAGAGTCGAGTCA CCATTTCACTAGACACGTCCAAGAACCAGTTCTC CCTGAAGCTGAGCTCTGTGACCGCCGCGACACG GCTGTGTATTACTGTGCGAGAGACTACGGTGTCT TTGACTACTGGGGCCAGGGAACCCTGGTCACCG TCTCCTCA |
| | | | SEQ ID NO: 28097 | SEQ ID NO: 32103 |
| | | AA | EIVLTQSPGTLSLSPGERATLSCRASQSVNSNYLA WYQQRPGQAPSLLIYGASSRATGIPDRFSGSGCG TDFTLTISRLEPEDFAVYCCQQYEISPWTFGQGT KVESK | QVQLQQWGAGLLKPSETLSLTCAVYGGSFSVYYW SWIRQPPGKGLEWIGEINHSGSTNYNPSLKSRVTISL DTSKNQFSLKLSSVTAADTAVYYCARDYGVFDYW GQGTLVTVSS |
| | | | SEQ ID NO: 28098 | SEQ ID NO: 32104 |
| iPS:451124 | 21-225_74F6 | NA | GACATCGTGATGACCCAGTCTCCAGACTCCCT GGCTGTGTCTCTGGGCGAGAGGGCCACCATCA ATTGCAAGTCCAGTCAGAATATTTTATCCAGC TCCAACAATAAGAACTACTTAACTTGGTACCA GCAGAAACCAGGACAGCCTCCTAAAATACTCA TTTACTACTGGACATCTACCCGGGAATCCGGGTC CCTGACCGATTCAGTGGCAGCGGGTTTGGGAC AGATTTCACTCTCACCATCAGCAGCCTGCAGG CTGAAGATGTGGCTGTTTATTACTGTCAGCAA TATTTTAGTGTTCCTCGTGACGTTCGGCCAAGGG ACCAAGGTGGAAATCAAA | CAGGTGCAGCTGGTGCAGTCTGGGGCTGAGGTG AAGAAACCTGGGGCCTCAGTGAGGGTCTCCTGC AAGGCTTCTGGATACACCTTCACCAATTATGATA TCAACTGGGTGCGACAGGCCACTGGACAAGGGC TTGAGTGGATGGATGGATGCACCTAACAGTGG TAACACAGGCTATGCACAGAAGTTCCAGGGCAG AGTCACCATGACCAGGAACACCTCCATGAGCAC AGCCTACATGGAGCTGAGCAGCCTGAGATCTGA GGACACGGCCGTGTATTACTGTGCCATAGCAGT GGCTGGTACTTTTTTGACTACTGGGGCCAGGGAA CCCTGGTCACCGTCTCCTCA |
| | | | SEQ ID NO: 28099 | SEQ ID NO: 32105 |

FIGURE 50
(Continued)

| | | | | |
|---|---|---|---|---|
| | | AA | DIVMTQSPDSLAVSLGERATINCKSSQNILSSSNN KNYLTWYQQKPGQPPKILIYWTSTRESGVPDRFS GSGFGTDFTLTISSLQAEDVAVYYCQQYFSVPLT FGQGTKVEIK <br> SEQ ID NO: 28100 | QVQLVQSGAEVKKPGASVRVSCKASGYTFTNYDIN WVRQATGQGLEWMGWMHPNSGNTGYAQKFQGR VTMTRNTSMSTAYMELSSLRSEDTAVYYCAHSSG WYFFDYWGQGTLVTVSS <br> SEQ ID NO: 32106 |
| iPS:451127 | 21-225_164A7 | NA | GACATCGTGATGACCCAGTCTCCAGACTCCCT GGCTGTGTCTCTGGGCGAGAGGGCCACCATCA ATTGCAAGTCCAGCAGCAGAGTGTTTACACAGC TCCAACAATAACAACTACTTAGCTTGGTACCA GCAGAAACCAGGACAGCCTCATAAGTTGCTCA TTTACTGGACATCTACCCGGGAATCCGGGGTC CCTGACCGATTCAGTGGCAGCGGGTATGGGAC AGATTTCTCTCACCATCAGCCAGCCTGCAGG CTGAAGATGTGGCAGTTTATTACTGTCAGCAA TATTATAGTATTCCTCTGACGTTCGGCCAAGG GACCAAGGTGGAAATCAAA <br> SEQ ID NO: 28101 | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATG TCAACTGGGTGCGACAGGCCACTGGACAAGGC TTGAGTGGATGGGATGGATGCACCCTAACAGTGG TAACACAGGCTATGCACAGAAGTTCCAGGGCAG AGTCACCATGACCAGGAACACCTCCACAAGCAC AGCCTACATGGAGCTGAGCAGCCTGAGATCTGA GGACTCGGCCGTGTATTACTGTGCGAGTAGCAGT GGCTGGTACCTCTTTGACTACTGGGGCCAGGAA CCCTGGTCACCGTCCTCCTCA <br> SEQ ID NO: 32107 |
| | | AA | DIVMTQCPDSLAVSLGERATINCKSSQSVLHSSN NNNYLAWYQQKPGQPHKLLIYWTSTRESGVPD RFSGSGYGTDFSLTIASLQAEDVAVYYCQQYYSI PLTFGQGTKVEIK <br> SEQ ID NO: 28102 | QVQLVQSGAEVKKPGASVKVSCKASGYTFTNYDV NWVRQATGQGLEWMGWMHPNSGNTGYAQKFQG RVTMTRNTSTSTAYMELSSLRSEDSAVYYCASSSG WYLFDYWGQGTLVTVSS <br> SEQ ID NO: 32108 |

FIGURE 50
(Continued)

| | | | | |
|---|---|---|---|---|
| iPS:451129 | 21-225_94D2 | NA | GACATCGTGATGACCCAGTCTCCAGACTCCCT GGCTGTGTCTCTGGGCGAGAGGGCCACCATCA ACTGCAAGTCCAGCCAGTGTTTTACACAGC TCCAACAATAAGAACTACTTAACTTGGTACCA GCAGAAACCAGGACAGCCTCATAAGCTGCTCA TTTACTGGGCATCTACTCGGGAATCCGGGGTC CCTGACCGATTCAGCGGCAGCGGGTCTGGGAC AGATTTCAGTCTCACGATCGGCAGCCTGCAGC ATGAAGATGTGGCAGTTTATTACTGTCAGCAA TATCATATAGTATTCCTCGACGTTCGGCCACGG GACCAAGGTGGAAATCAAA<br><br>SEQ ID NO: 28103 | CAGGTGCAGCTGGTGCAGTCTGGGGCTGAGGTG AAGAAGCCTGGGGCCTCAGTGAAGGTCTCCTGC AAGGCTTCTGGATTCACCTTCACCAATTATGATA TCAACTGGGTGCGACAGGCCACTGGACAAGGGC TTGAGTGGATGGGATGGATGCACCTAACAGTGG TAACACAGGCTTTGCACAGAAGTTCCAGGGCAG AGTCACAATGACCAGGAACACCTCCATAAGCAC AGCCTACATGGAACTGAGCAGCCTGAGATCTGA GGACACGGCCGTGTATTACTGTGCGGTTTCCAGT GGCTGGTACGTTGACCCCTGGGGCCAGGGA ACCCTGGTCACCGTCCTCA<br><br>SEQ ID NO: 32109 |
| | | AA | DIVMTQSPDSLAVSLGERATINCKSSQSVLHSSN NKNYLTWYQQKPGQPHKLLIYWASTRESGVPD RFSGSGSGTDFSLTIGSLQHEDVAVYYCQQYHSI PPTFGHGTKVEIK<br><br>SEQ ID NO: 28104 | QVQLVQSGAEVKKPGASVKVSCKASGFTFTNYDIN WVRQATGQGLEWMGWMHPNSGNTGFAQKFQGR VTMTRNTSISTAYMELSSLRSEDTAVYYCAVSSGW YWFDPWGQGTLVTVSS<br><br>SEQ ID NO: 32110 |
| iPS:451131 | 21-225_160A7 | NA | GACATCGTGCTGACCCAGTCTCCAGACTCCCC GGCTGTGTCTCTGGGCGAGAGGGCCACCATCA ATTGCAAGTCCAGCAGCACTGTTTATCCAAC TCCCACAATAACAACTACTTAGCTTGGTACCA GCAGAGACCAGGACATCTACCCGGGAATCCTCTA TTTTCTGGGCATCTACCCGGGAATCCGGGGTC CCTGACCGATTCAGTGGCAGCGGGTATGGGAC AGATTTCACTCTCACCATCAGCAGCCTGCAGG CTGAAGATGTGGCAGTTTATTACTGTCAGCAA TATTATAGTACTCCGTGCAGTTTGGCCAGGG GACCAAGCTGGAGATCAAA<br><br>SEQ ID NO: 28105 | CAGGTGCAGCTGGTGCAGTCTGGGGCTGAAGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGC TTGAGTGGATGGGATGGATGCACAGAAGTCACAGTGG TAACACAGGCTATGCACAGAAGTTCCAGGGCAG AGTCACAATGACCAGGAACACCTCCATAAACAC AGCCTACATGGAGCTGAGCAGCCTGAGATCTGA GGACACGGCCGTGTATTACTGTGCCCATAGCAGT GGCTGGTACTACTTTGACTACTGGGGCCAGGAA CCCTGGTCACCGTCCTCA<br><br>SEQ ID NO: 32111 |

FIGURE 50
(Continued)

| | | | |
|---|---|---|---|
| iPS:451133 | 21-225_95H4 | AA | DIVLTQSPDSPAVSLGERATINCKSSQSVLSNSHNNNYLAWYQQRPGHPHKLLIFWASTRESGVPDRFSGSGYGTDFTLTISSLQAEDVAVYYCQQYYSTPCSFGQGTKLEIK<br>SEQ ID NO: 28106 | QVQLVQSGAEVKKPGASVKVSCKASGYTFTNYDINWVRQATGQGLEWMGWMHPHSGNTGYAQKFQGRVTMTRNTSINTAYMELSSLRSEDTAVYYCAHSSGWYYFDYWGQGTLVTVSS<br>SEQ ID NO: 32112 |
| | | NA | GACATCGTTATGACCCAGTCTCCAGACTCCCTGGCTGTGTCTCTGGGCGAGAGGGCCACCATCAATTGCAAGTCCAGCCAGAGTGTTTTATTCAGCTCCAACAATTATATAATTACTTAGCTTGGTACCAGCAGAGACCAGGACAGCCTCATAACCTGCTCATTTACTGGGCATCTACCCGGGAATCCGGGGTCCCTGACCGATTCAGTGGCAGGTCTGGGACAGATTTCACTCTCACCATCAGCAGCCTGCAGGCTGCTGATGTGGCAGTTTATTACTGTCAGCAATATCATAGTTCTCCTGACGTTCGGCCAAGGGACCACGGTCGCAAATCAAA<br>SEQ ID NO: 28107 | CAGGTGCAGTTGGTGCAGTCTGGGGCTGAGGTGAAGAAGCCTGGGGCCTCAGTGAAGGTCTCCTGCAAGGCTTCTGGATACACCTTCACCAATTATGATATCAACTGGGTGCGACAGGCCACTGGACAAGGGCTTGAGTGGATGGGATGGATGCACAGAAGTTCCAGGGCAGTAACACAGGCTATGCACCAGGAACACCTCCACAAGCACAGTCACCATGACCAGGAGCTGAGCAGCCTGAGATCTGAAGCCCACATGGAGCCGTGTATTACTGTGCGGGTCTCCAGTGGACACGGCCGTGGAACTGGTTCGACCCTGACGACACCGTGGGGCCAGGGAACCCGTGGACCTGTCACCGTCCTCTCA<br>SEQ ID NO: 32113 |
| | | AA | DIVMTQCPDSLAVSLGERATINCKSSQSVLFSSNNYNYLAWYQQRPGQPHNLLIYWASTRESGVPDRFSGSGSGTDFTLTISSLQAADVAVYYCQQYHSSPLTFGQGTTVQIK<br>SEQ ID NO: 28108 | QVQLVQSGAEVKKPGASVKVSCKASGYTFTNYDINWVRQATGQGLEWMGWMNPNSGNTGYAQKFQGRVTMTRNTSTSTAHMELSSLRSEDTAVYYCAVSSGWNWFDPWGQGTLVTVSS<br>SEQ ID NO: 32114 |

FIGURE 50
(Continued)

| | | | |
|---|---|---|---|
| iPS:437240 | 21-225_84H12 | NA | GACATCCAGATGACCCAGTCTCCATCCTACCAGTCTGCATCTGTGGGAGACAGAGTCACCATCACTTGCCGGGCAAGTCAGGGCATTAGAAATGATTTAGGCTGGTTTCAGCAGAAACCAGGGAAAGCCCCTAAGCGCCTGATCTATGCTGCATCCAGTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTTTACAGCATAATGATTACCCATTCACTTTCGGCCCTGGGACCAAAGTGGATATCAAA<br><br>SEQ ID NO: 28109 | CAGGTGCAGCTGGTGCAGTCTGGGGCTGAGGTGAAGAAGCCTGGGGCCTCAGTGAAGGTCTCCTGCAAGGCTTCTGGATACACCTTCACCAGTTATGATATCAACTGGGTGCGACAGGCCACTGGACAAGGCTTGAGTTGGATGGGATGGCTGAACCCTCACAGTGGTAACACAGGCTATGCACAGAAGTTCCAGGGCAGAATCACCACGACCTGGAACACCTCCATACGCACTGCCTACATGGAGCTGAGCAGCCTGAGATCTGAGGACACGGCCGTGTATTACTGTGCGAGAGGTTTACGATATTTGACTGGTTATTCCCCACCTACTACTACGATATGGACGTCTGGGGCCAAGGGACCACGGTCACCGTCTCCTCA<br><br>SEQ ID NO: 32115 |
| | | AA | DIQMTQSPSYQSASVGDRVTITCRASQGIRNDLGWFQQKPGKAPKRLIYAASSLQSGVPSRFSGSGSGTEFTLTISSLQPEDFATYYCLQHNDYPFTFGPGTKVDIK<br><br>SEQ ID NO: 28110 | QVQLVQSGAEVKKPGASVKVSCKASGYTFTSYDINWVRQATGQGLEWMGWLNPHSGNTGYAQKFQGRITMTWNTSIRTAYMELSSLRSEDTAVYYCARGFYDILTGYSPTYYYYDMDVWGQGTTVTVSS<br><br>SEQ ID NO: 32116 |

FIGURE 50
(Continued)

| iPS:434577 | 21-225_75C11 | NA | GACATCCAGATGACCCAGTCTCCATCCTCCCTGTCTGCATCTGTGGGAGACAGAGTCACCATCACTTGCCGGGCAAGTCAGGGCATTAGAAATGATTTAGGCTGGTTTCAGCAGAAACCAGGAAAGCCCCTAAGCGCCTGATCTATGCTGCATCCAGTTTCCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCTACAGCATAATGATTACCCATTCACTTTCGGCCCTGGGACCAAAGTGGATATCAAA | CAGGTGCAGCTGGTGCAGTCTGGGGCTGAGGTGAAGAAGCCTGGGGCCTCAGTGAAGGTCTCCTGCAAGGCTTCTGGATACACCTTCACCAGTTATGATATCAACTGGGTGCGACAGGCCACTGGACAAGGCTTGAGTGGATGGGATGGCTGAACCCTCACAGTGGTAACACAGGCTATGCACAGAAGTTCCAGGGCAGAATCACCATGACCTGAGAACACCTCCATACGCACTGCCTACATGGAGCTGAGCAGCTGAGATCTGAGGACACGGCCGTGTATTACTGTGCGAGAGGGTTTTACGATATTTGACTGGTTATTCCCCACCTACTACTACTACGATATGGACGTCTGGGGCCAAGGGACCACGGTCACCGTCTCCTCA |
|  |  |  | SEQ ID NO: 28111 | SEQ ID NO: 32117 |
|  |  | AA | DIQMTQSPSSLSASVGDRVTITCRASQGIRNDLGWFQQKPGKAPKRLIYAASSLQSGVPSRFSGSGSGTEFTLTISSLQPEDFATYCLQHNDYPFTFGPGTKVDIK | QVQLVQSGAEVKKPGASVKVSCKASGYTFTSYDINWVRQATGQGLEWMGWLNPHSGNTGYAQKFQGRITMTWNTSIRTAYMELSSLRSEDTAVYYCARGFYDILTGYSPTYYYDMDVWGQGTTVTVSS |
|  |  |  | SEQ ID NO: 28112 | SEQ ID NO: 32118 |

FIGURE 50
(Continued)

| | | | | |
|---|---|---|---|---|
| iPS:435477 | 21-225_154E8 | NA | GACATCCAGATGACCCAGTCTCCATCTCCGT GTCTGCATCTATAGAGACAGAGTCACCATCA CTTGTCGGGCGAGTCAGTTATTAGCAGCTGG TTAGCCTGGTATCAGCAGAAACCAGGGAAAG CCCCTAAGCTCCTGATCTATACTGCATCCAGT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTGTTGTCAACAGGCTAACAGTTTCCCGTGG ACGTTCGGCCAAGGGACCAAGGTGGAATTCA AC | GAGGTGCAGCTGTTGGAGTCTGGGGGAGGCTTG GTACAGCCTGGGGGGTCCCTGAGACTCTCCTGTG CAGCCTCTGGATTCACCTTTAGCAGTTATGCCAT GAGCTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGATCACGGTATA GCAGTGGCTGGTACTGGGGCTCACTACTTTGACT ACTGGGGCCAGGGAACCCTGGCCACCGTCTCCTC A |
| | | | SEQ ID NO: 28113 | SEQ ID NO: 32119 |
| | | AA | DIQMTQSPSSVSASIGDRVTITCRASQFISSWLAW YQQKPGKAPKLLIYTASSLQSGVPSRFSGSGSGT DFTLTISSLQPEDFATYCCQQANSFPWTFGQGTK VEFN | EVQLLESGGGLVQPGGSLRLSCAASGFTFSSYAMS WVRQAPGRGLEWVSAISGSGGNTFYADSVKGRFTI SRDNSKNTLYLQMNSLRAEDTAVYYCAIHGIAVAG TGAHYFDYWGQGTLATVSS |
| | | | SEQ ID NO: 28114 | SEQ ID NO: 32120 |
| iPS:434553 | 21-225_76H12 | NA | GACATCCAGATGACCCAGTCTCCATCCTCCCT GTCTGCATCTGTGGGAGACAGAGTCACCATCA CTTGCCGGGCAAGTCAGGGCATTAGAAATGAT TTAGGCTGGTTTCAGCAGAAACCAGGGAAAGC CCCCAAGCGCCTGATCTATGCTGCATCCAGAT TGCAAAGTGGGGTCCCATCAAGGTTCAGCGGC AGTGGATCTGGGACAGGAATTCACTCTCACAAT CAGCAGCCTGCAGCCTGAAGATTTTGCAACTT ATTACTGTCTACAGCATATAATGATTACCCATTC ACTTTCGGCCCTGGGACCAAAGTGGATATCAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGACAGGCCACTGGACAAGGGC TTGAGTGGATGGGATGGCTGAACCCTCACAGTGG TAACACAGGCTATGCACAGAAGTTCCAGGCAG AATCACCATGACCTGGAACACTCCATACGCACT GCCTACATGGAGCTGAGCAGCCTGAGATCTGAG GACACGGCCGTGTATTACTGTGCGAGAGGGTTTT ACGATATTTGACTGGTTATTCCCCACTACTAC TACTACGATATGGACGTCTGGGGCCAAGGGACC ACGGTCACCGTCTCCTCA |

FIGURE 50
(Continued)

| | | | SEQ ID NO: 28115 | SEQ ID NO: 32121 |
|---|---|---|---|---|
| | | AA | DIQMTQSPSSLSASVGDRVTITCRASQGIRNDLG WFQQKPGKAPKRLIYAASRLQSGVPSRFSGSGS GTEFTLTISSLQPEDFATYYCLQHNDYPFTGPGT KVDIK | QVQLVQSGAEVKKPGASVKVSCKASGYTFTSYDIN WVRQATGQGLEWMGWLNPHSGNTGYAQKFQGRI TMTWNTSIRTAYMELSSLRSEDTAVYYCARGFYDI LTGYSPTYYYYDMDVWGQGTTVTVSS |
| iPS:434927 | 21-225_86E5 | | SEQ ID NO: 28116 | SEQ ID NO: 32122 |
| | | NA | GACATCCAGATGACCCAGTCTCCATCCTCCCT GTCTGCATCTGTAGGAGACAGAGTCACCATCA CTTGCCGGGCAAGTCAGGGCATTAGAAATGAT TTAGGCTGGTATCAGCAGAAACCAGGGAAAG CCCCTAAGCGCCTGATCTATGCTGCATCCAGT TTGCAAAGTGGGGTCCCATCAAGGTTCAGCGG CAGTGGATCTGGGACAGAATTCACTCTCACAA TCAGCAGCCTGCAGCCTGAAGATTTTGCAACT TATCACTGTCTACAGCATAATGATTACCCATTC ACTTTCGGCCCTGGGACCAAAGTGGAAATCAA A | CAGGTGCAGCTGGTGCAGTCTGGGGCTGAGGTG AAGAAGCCTGGGGCCTCAGTGAAGGTCTCCTGC AAGGCTTCTGGATACACCTTCACCAGTTATGATA TCAACTGGGTGCGACAGGCCACTGGACAAGGC TTGAGTGGATGGGATGGATGAACCCTAACAGTG GTAACACAGGCTATGCACAGAAGTTCCAGGGCA GAGTCACCATGACCTGGAACACCTCCATACGCAC TGCCTACATGGAGCTGAGCAGCCTGAGATCTGAG GACACGGCCGTGTATTACTGTGCGAGAGGGTTTT ACGATATTTTGACTGGTTATTCCCCACCTACTAC TACTACGATATGGACGTCTGGGGCCAAGGGACC ACGGTCACCGTCTCCTCA |
| | | | SEQ ID NO: 28117 | SEQ ID NO: 32123 |
| | | AA | DIQMTQSPSSLSASVGDRVTITCRASQGIRNDLG WYQQKPGKAPKRLIYAASSLQSGVPSRFSGSGS GTEFTLTISSLQPEDFATYHCLQHNDYPFTGPGT KVEIK | QVQLVQSGAEVKKPGASVKVSCKASGYTFTSYDIN WVRQATGQGLEWMGWMNPNSGNTGYAQKFQGR VTMTWNTSIRTAYMELSSLRSEDTAVYYCARGFYD ILTGYSPTYYYYDMDVWGQGTTVTVSS |
| | | | SEQ ID NO: 28118 | SEQ ID NO: 32124 |

FIGURE 50
(Continued)

| | | | |
|---|---|---|---|
| iPS:435385 | 21-225_149G7 | NA | GACATCCAGATGACCCAGTCTCCATCTTCCGT GTCTGCATCTGTAGGAGACAGAGTCACCATCA CTTGTCGGGCGAGTCAGTTTATTAGCAGCTGG TTAGCCTGGTATCAGCAGAAACCAGGGAAAG CCCCTAAGTTCCTGATCTATGCTGCATCCAGT TGCAAAGTGGGGTCCCATCAAGGTTCAGCGGC AGTGGATCTGGGACAGATTTCACTCTCACCAT CAGCAGCCTGCAGCCTGAAGATTTTGCAACTT ACTATTGTCAACAGGCTAACAGTTCCCGTGG ACGTTCGGCCAAGGGACCAAGGTGGAAATCA AC |
| | | | SEQ ID NO: 28119 |
| | | AA | DIQMTQSPSSVSASVGDRVTITCRASQFISSWLA WYQQKPGKAPKFLIYAASSLQSGVPSRFSGSGSG TDFTLTISSLQPEDFATYYCQQANSPWTFGQGT KVEIN |
| | | | SEQ ID NO: 28120 |

| | |
|---|---|
| GAGGTGCAGCTGTTGGAGTCTGGGGGAGGCTTG GTACAGCCTGGGGGGTCCCTGAGACTCTCCTGTG CAGCCTCTGGATTCACCTTTAGCAGCTATGCCAT GAGCTGGGTCCGCCAGGCTCCAGGGAAGGGGCT GGAGTGGGTCTCAGCTATTAGTGGTAGTGGTGGT AACACATTCTACGCAGACTCCGTGAAGGGCCGGT TCACCATCTCCAGAGACAATTCCAAGAACACGCT GTATCTGCAAATGAACAGCCTGAGAGCCGAGGA CACGGCCGTATATTACTGTGCGCATCACGGTATA GCAGTGGCTGGTACTGGGGCTCACTACTTTGACT ACTGGGGCCAGGGAACCCTGGCCACCGTCTCCTC A | |
| SEQ ID NO: 32125 | |
| EVQLLESGGGLVQPGGSLRLSCAASGFTFSSYAMS WVRQAPGKGLEWVSAISGSGGNTFYADSVKGRFTI SRDNSKNTLYLQMNSLRAEDTAVYYCAIHGIAVAG TGAHYFDYWGQGTLATVSS | |
| SEQ ID NO: 32126 | |

FIGURE 51 (Table 4)
Standard IgG Antibody Variable Region Protein Alignment
CDRs defined by Kabat
Alignment numbering defined by Amgen Reference (AHo)

| KAPPA_VARIABLE | Germline | SEQ ID NO: | K_FR1 | K_CDR1 | K_FR2 | K_CDR2 | K_FR3 | K_CDR3 | K_FR4 |
|---|---|---|---|---|---|---|---|---|---|
| VK4B3JK3 | | | DIVMTQSPDSLAV SLGERATINC | KSS--- QSVLHSSNNKN YLA | WYQQKPGQ PPKLLIY | W------ ASTRES | GVPDRFSGSGSG--- TDFTLTISSLQAEDVAVYYC | QQYYS------ ---------TPFT | FGPGT KVDIK |
| iPS:426 126 | 21-225_6G6 | VK4\|B3\|J K3 | DIVMTQSPDSLAV SLGERATINC | KSS--- QSVLHSNNYN YLA | WYQQKPGQ PPNLLIF | W------ ASTRES | GVPDRFSGSGFG--- TDFTLNISSLQAEDVAVYYC | QQYYD------ ---------TPFT | FGHGT KVDIK |
| iPS:412 232 | 21-225_4A2 | VK4\|B3\|J K3 | DIVMTQSPDSLAV SLGERATINC | KSS--- QSILHSSNNNN YLA | WFQQKPGQ PPKLLIY | W------ ASTRES | GVPDRFSGSGSG--- TDFTLTISSLQPEDVAVYYC | QQYYN------ ---------TPVT | FGPGT KVGIK |
| iPS:451 141 | 21-225_164B1 | VK4\|B3\|J K3 | DIVMTQSPDSLAV SLGERATINC | KSS--- QSLLKSSNNKS YLA | SYQQKPGQ LPKLLIY | W------ ASSRES | GVPDRFSGSGSG--- TDFTLTISSLQAEDVALYYC | QQYYS------ ---------IPPT | FGHGT NVDIT |
| iPS:423 314 | 21-225_12F11 | VK4\|B3\|J K3 | DIVMTQSPDSLAV SLGERATINC | KSS--- QNVLYSSHNNN YLA | WYQQKPGQ PPNLLIF | W------ ASTRES | GVPDRFSGSGFG--- TDFTLNISSLQAEDVAVYYC | QQYYD------ ---------TPFT | FGPGT KVDIK |
| iPS:435 327 | 21-225_147G6 | VK4\|B3\|J K3 | DIVMTQSPDSLAV SLGERATINC | KSS--- QSVLYSSNSNN YLA | WYQQKPGQ PPKLLIY | W------ ASARES | GVPDRFSGSGSG--- TDFTLTISSLQAEDVAVYYC | QQYYT------ ---------TPPT | FGPGT KVDIK |
| iPS:435 345 | 21-225_148G3 | VK4\|B3\|J K3 | DIVMTQSPDSLAV SLGERATINC | KSS--- QRVLHSSNNYN YLA | WYQQKPGQ PPKLLIY | W------ ASTRDS | GVPDRFSGSGSG--- ADFTLTISSLQAEDVALYYC | QQYYS------ ---------TPFT | FGPGT KVDIK |
| iPS:435 405 | 21-225_150B7 | VK4\|B3\|J K3 | DIVMTQSPDSLAV SLGERATINC | KSS--- QSVLYSSNNYN YLV | WYQQKPGQ SPKRLIY | W------ ASTRES | GVPDRFSGSGSG--- TDFSLTISSLQAEDVAVYYC | QQYYS------ ---------TPFT | FGPGT KVDIK |
| iPS:435 433 | 21-225_152E3 | VK4\|B3\|J K3 | DIVMTQSPDSLAV SLGERATINC | KSS--- QSVLHSSNNKN YLA | WYQQKPGQ PPKLLIY | W------ ASTRKS | GVPDRFSGSGSG--- TDFTLTISSLQAEDVAVYYC | QQYYS------ ---------TPFT | FGPGT KVDIK |
| iPS:435 437 | 21-225_152F4 | VK4\|B3\|J K3 | DIVMTQSPDSLAV SLGERATINC | KSS--- QSVLYSSNNYN YLA | WYQQKPGQ PPKLLIY | W------ ASTRES | GVPVRFSGSGSG--- TDFTVPISSMQDDDVAVYYR | QQYFN------ ---------TPPT | FGPGT KVDIK |
| iPS:435 649 | 21-225_165H2 | VK4\|B3\|J K3 | DIVMTQSPDSLTV SPGERATINC | KSS--- QSVLHSSNNKN YLT | WYQQKPGQ PPKLLIY | W------ ASTRES | GVPVRFSGSGSG--- TDFTVPISSMQDDDVAVYYR | QQSYS------ ---------IPPT | FGPGT NVDIK |
| iPS:435 855 | 21-225_191G3 | VK4\|B3\|J K3 | DIVMTQSPDSLAV SLGERATIDC | KSS--- QSVLHSSNSYN YLA | WYQQKLGQ PPKLLIY | W------ ASTRKS | GVPDRFSGSGSG--- TDFTLTISSLQAEDVAFYYC | QQYYS------ ---------SPPT | FGPGT KMDIK |

Figure 51 (Continued)

| ID | Germline | K_FR1 | K_CDR1 | K_FR2 | K_CDR2 | K_FR3 | K_CDR3 | K_FR4 |
|---|---|---|---|---|---|---|---|---|
| iPS:435_903 | 21-225_190E2 | VK4|B3/JK3 | DIVMTQSPDSLAV SLGERATINC | KSS---QSVLFNSNNKN YLA | WYQQKPGQ PPNLLIY | W------ASTRES | GVPDRFSGSGSG---TDFTLTISSMQAEDVAVYYC | QQYCS------LPFT | FGPGT KVDIR |
| iPS:435_915 | 21-225_190H4 | VK4|B3/JK3 | ANVMTQSPDSLAV SLGERTTINC | KSS---QSVLHSSNNYN YLA | WYRQKPGQ PPKLLIY | W------ASTRES | GVPDRFSGSGSG---TDFTLTISSLQAEDVAVYYC | QQYYS------IPFT | FGPGT KVDIK |
| iPS:435_923 | 21-225_190H6 | VK4|B3/JK3 | DIVMTQSPDSLAV SLGERATINC | KSS---QSVLFNSNNKN YLA | WYQQKPGQ PPNLLIY | W------ASTRES | GVPDRFSGSGSG---TDFTLTISSLQAEDVAVYYC | QQYCS------LPFT | FGPGT KVDIR |
| iPS:435_953 | 21-225_191B1_2 | VK4|B3/JK3 | DIVMTQSPDSLAV SLGERATINC | KSS---QSVLFNSNNKN YLA | WYQQKPGQ PPKLLIY | W------ASTRES | GVPDRFSGSGSG---TDFTLTISNLQAEDVAIYYC | QQYSS------LPFT | FGPGT KVDIK |
| iPS:436_098 | 21-225_195G1 | VK4|B3/JK3 | DIVMTQSPDSLAV SLGERATINC | KSS---QSVLFNSNNKN YLA | WYQQKPGQ PPNLLIY | W------ASTLES | GVPDRFSGSGSG---TDFTLTISSMQAEDVAVYYC | QQYCS------FPFT | FGPGT KVDIK |
| iPS:436_102 | 21-225_196B1 | VK4|B3/JK3 | DIVMTQSPDSLAV FLGERATINC | KSS---QSIFSSNNKR YLA | WYQQKPGQ PPKLLIY | W------ASIRES | GVPDRFSGSGSG---TDFTLTISSLQAEDVAVYYC | QQYSS------LPFT | FGPGT KVDIK |
| iPS:436_104 | 21-225_196C1 | VK4|B3/JK3 | DIVMTQSPDSLAV SLGERATINC | KSS---QSVLFNSNNKN YLA | WYQQKPGQ LPNLLIY | W------ASTLES | GVPDRFSGSGCG---TDFTLTISSMQAEDVAVYYC | QQYCS------FPFT | FGPGT KVDIK |
| iPS:436_156 | 21-225_197C8 | VK4|B3/JK3 | DIVMTQSPDSLAV SLGERATINC | KSS---QSVLHSSNNKN YLA | WYQQKPGQ PPKLLIY | W------ASTRES | GVPDRFSGSGSG---TDFTLTISSLQAEDVAVYYC | QQSYT------IPFT | FGPGT KVDNK |
| iPS:436_270 | 21-225_203F10 | VK4|B3/JK3 | DIVMTQSPDSLAV SLGERATINC | KSS---QSVFFHSNNKN YLA | WYQQKPGQ PPKLLIY | W------ASTRES | GVPDRFSGSGSG---TDFTLTISSLQAEDVTVYYC | QQYFS------LPFT | FGPGT KVDIT |
| iPS:436_570 | 21-225_225F4 | VK4|B3/JK3 | DIVMTQSPDSLAV SLGERATINC | KSS---QSVLYSSNNKN YLA | WYQQKPGQ PPKLLIY | W------ASTRES | GVPDRFTGSGSG---TDFTLTISCVPEDVAVYYC | HQYHN------SPPT | FGHGT EVDIK |
| iPS:394_065 | 21-225_11E2 | VK4|B3/JK3 | DIVMTQSPDSLAV SLGERATINC | KSN---QRVLSSSNNHN YLA | WYQQKPGQ PPKLLIY | W------ASTRES | GVPDRFSGSGSG---TDFTLTISSLQAEDVAVYYC | QQYFS------TPFT | FGPGT KVDIK |
| VK1A30/JK5 | Germline | | RAS---QGIR------SDLG | | | | | |
| iPS:473_253 | 21-225_7C3_L_C1 | VK1|A30/JK5 | DIQMTQSPSSLSA SVGDRVTITC | RAS---QGIR------SDLG | WYQQNPVK APKRLIY | A------ASSLQS | GVPSRFSGSGSG---TEFTLTVSSLQPEDFAFYYC | LQHNS------YLPIT | FGQGT RLEIK |
| iPS:473_256 | 21-225_9F12_LC2 | VK1|A30/JK5 | DIQMTQSPSSLSA SVGDRVTITC | RAS---QGIR------NDLG | WYQQKPVK APKRLIY | A------ASSLQS | GVPSRFSGSGSG---TEFTLTISSLQPEDFATYYC | LQHNS------YLPIT | FGQGT RLEIK |
| iPS:453_449 | 21-225_208A2 | VK1|A30/JK5 | DIQMTQSPSSLSA SVGDRVTITC | RTS---QGIR------NDLG | WYQQQPGK TPKRLIY | A------ASSLLS | GVPSRFSGSRSG---TDFTLTISSLQPEDFATYY | LQYNS------YPPIT | FGQGT RLEIK |
| iPS:434_467 | 21-225_73H8 | VK1|A30/JK5 | DIQMTQSPSSLYA SVGDRVTIIR | RAS---QDIR------NDLG | WYQQKPGK ALKRVIY | A------ASSLQS | GVPSSFSGSGSG---TEFTLTISSLQPEDFATYYG | IQHNS------YPPIT | VGQGT RLEIK |
| iPS:435_045 | 21-225_90H5 | VK1|A30/JK5 | DIQMTQSPSSLSA SVGDRVTITC | RAS---QGIR------NDLG | WYQQKPGK APKRLIY | I------ASSLQS | GVPSRFSGSGSG---TEFTLTISSLQPEDFATYYC | LQHNS------YFPIT | FGQGT RLEIK |

Figure 51 (Continued)

| ID | Name | V/J | K_FR1 | K_CDR1 | K_FR2 | K_CDR2 | K_FR3 | K_CDR3 | K_FR4 |
|---|---|---|---|---|---|---|---|---|---|
| iPS:435561 | 21-225_159F1 | VK1|A30/JK5 | DIQMTQSPSSLSASVGDRVTITC | RAS--QRVR------NDLG | WYQQKPAK APKRIIF | D-------ASNLQS | GVPSRFSGSGSG--TEFTLTISSLQPEDFATYYC | LQHHS-----------FPIT | FGQGTRLEIK |
| iPS:436328 | 21-225_207F12 | VK1|A30/JK5 | DIQMTQSPSSLSASVGDRVTITC | RAS--QGIR------NDLG | WYQQKPGK APKRLIY | A-------ASSLQS | TEFTLTISSLQPEDFATYFC | LQHNS-----------YFLT | FGQGTRLEIK |
| iPS:436354 | 21-225_210G10 | VK1|A30/JK5 | DIQMTQSPSSLSASVGDRVTITF | RTS--QGIR------NDLG | WYQQQPGK TPKRMIY | A-------ASSLFS | GVPSRFSGSRSG--TDFTLTISSLQPEDFATYYC | LQYNS-----------YPPT | FGQGTRLEIK |
| iPS:393094 | 21-225_34C4 | VK1|A30/JK5 | DIQMTQSPSSLSASVGDRVTITC | RAS--QGIR------NDLG | WYQQKPGK APKRLIY | T-------ASNLQS | GVPSRFSGSGSG--TEFTLTISSLQPEDFATYYC | LQHSS-----------FPIT | FGQGTRLEIK |
| iPS:398484 | 21-225_18D4 | VK1|A30/JK5 | DIQMTQSPSSLSASVGDRVTITC | RAS--QGIR------NDLG | WYQQKPGK APKRLIY | A-------ASSLES | GVPSRFSGSGSG--TEFTLTVSSLQPEDFATYYC | LHHNN-----------YLPIT | FGQGTRLEIK |
| | Germline VK1|L5J|K3 | | | | | | | | |
| iPS:473254 | 21-225_7C3_L_C2 | VK1|L5J K3 | DIQMTQSPSSVSASLGDRVTITC | RAS--QGIS------SWLA | WYQQKPGK APKLLIF | A-------ASRLQS | GAPSRFSGSGSG--TDFFLTISLLPEDFAIYYC | QQANS-----------FPFT | FGPGTKVDIK |
| iPS:473255 | 21-225_9F12_LC1 | VK1|L5J K3 | DIQMTQSPSSVSASVGDRVTITC | RAS--QGIS------RWLA | WYQQKPGK APKLLIY | A-------AVSLQS | GVPSRFSGSGSG--TDFFLTISLLPEDFAIYYC | QQANS-----------FPFT | FGPGTKVDPK |
| iPS:426108 | 21-225_10G6 | VK1|L5J K3 | DIQMTQSPSSVSASVGDRVTITC | RAS--QGIS------KWLA | WYQQKPGK APKLLIY | A-------ASRLQS | GVPSRFSGSGSG--TDFFLTISSLQPEDFATYYC | QQANS-----------FPFT | FGPGTKVDIK |
| iPS:426110 | 21-225_12E9 | VK1|L5J K3 | DIQMTQSPSSVSASVGDRVTITC | RAS--QGIS------SWLA | WYQQKPGE APKLLIY | A-------ASRLQS | GVPSRFSGSGSG--TDFFLTISSLQPEDFATYYC | QQANS-----------FPFT | FGPGTKVDIK |
| iPS:453447 | 21-225_65F10 | VK1|L5J K3 | DIQMTQSPSSVSASVGDRVTITC | RGG--QGIS------TWLA | WYQQKPGK APKLLIY | A-------ASILQS | GVPSRFSGSFGRGSG--TDFFLTISSLQPEDFATYYC | QQGNI-----------FPFT | FGPGTKVDIK |
| iPS:453451 | 21-225_52G11 | VK1|L5J K3 | DIQMTQSPSSVSASVGDRVTITC | RAS--QGIS------KWLA | WYQQKPGK APKLLLY | A-------ASSLQS | GVPSRFSASGSG--TDFFLTISSLQPEDFATYYC | QQANS-----------LPFT | FGPGTKVDVK |
| iPS:453453 | 21-225_53F2 | VK1|L5J K3 | DIQMTQSPSSVSASVGDRVTITC | RAS--QGIS------KWLA | WYQQKPGK APNLLIY | A-------ASSLQS | GVPSRFSGSGSG--TDFFLTISSLQPEDFATYYC | QQANS-----------FPFT | FGPGTKVDIK |
| iPS:433915 | 21-225_43H9 | VK1|L5J K3 | DIQMTQSPSSVSASVGDRVTITC | RAS--QGIS------SWLA | WYQQKPGK APKLLIY | D-------ASSLQS | GVPSRFSGSGSG--TDFFLTISSLQPEDFATYFC | QQANS-----------FPFT | FGPGTKVDIK |
| iPS:433925 | 21-225_44F3 | VK1|L5J K3 | DIQMTQSPSSVSASVGDRVTITC | RAS--QGIS------DWLA | WYQQKPGK APKLLIY | A-------ASSLQS | GVPSRFSGSFG--TDFFLTISSLQPEDFATYYC | QQANS-----------FPFT | FGPGTKVDIK |
| iPS:433953 | 21-225_45H4 | VK1|L5J K3 | DIQMTQSPSSVSASVGDRVTITC | RAS--QDIS------SWLA | WYQKKPGK APKYLIY | D-------ASSLQS | GVPSRFSGSGSG--TDFFLTISSLQPEDFATYPC | QQANS-----------LPFT | FGPGTKVDIK |
| iPS:433959 | 21-225_45C9 | VK1|L5J K3 | DIQMTQSPSSVSASVGDRVTITC | RAS--QDIS------DWLA | WYQQKPGK APKLLIY | A-------ASSLES | GVPSRFSGSGSG--TDFFLTISSLQPEDFATYYC | QQANS-----------FPFT | FGPGTKVDIK |
| iPS:434023 | 21-225_49F1 | VK1|L5J K3 | DIQMTQSPSSVSASVGDRVTITC | RAS--QGIS------GWLA | WYQQKPGK APKLLIY | T-------VSSLQS | GVPSRFSGSGSG--TDFFLTISSLQPEDFATYYC | QQSNS-----------FPFT | FGPGTKVDIK |
| iPS:434027 | 21-225_49H5 | VK1|L5J K3 | DIQMTQSPSSVSASVGDRVTITC | RAS--QGFS------GGFS | WFQQKPGK APKLLIY | A-------ASSLQD | GVPSRFSGSGSG--TDFFLTISSLQPEDFATYYC | QQTNS-----------FPFT | FGPGTKVDIK |
| iPS:434035 | 21-225_49F10 | VK1|L5J K3 | DIQMTQSPSSVSASVGDRVTITC | RAS--QGIS------EWLA | WYQQKPGK APKVLIY | A-------ASTLQS | GVPSRFSGSGSG--TDFFLTISSLQPEDFATYYC | QQANS-----------FPFT | FGPGTKVDIK |
| iPS:434061 | 21-225_51C7 | VK1|L5J K3 | DIQMTQSPSSVSASVGDRVTITC | RAS--QDVN------NYLA | WFQQKPGK APKLLIY | A-------ASSLQN | GVPSRFSGSGSG--TDFFLTISLLPEDFATYYC | QCTNS-----------FPFT | FGPGTKVDIK |

Figure 51 (Continued)

| | | | | | | | | | |
|---|---|---|---|---|---|---|---|---|---|
| iPS-434 065 | 21-225_50D4 | VK1\|L5\|J K3 | DIQMTQSPSSVSA SVGDRLIITC | RAS--QGIS -----RWLA | WYQQKPGK APKVLIY | A------- ASTLQS | GVPSRFSGSGSG--- TDFTLTISSLQPEDFATYYC | QQANS-- ------- | FGPGT KVDIR |
| iPS-434 069 | 21-225_51E9 | VK1\|L5\|J K3 | DIQMTQSPSSVSA SVGDRVTITC | RAS--QGIS -----SWLA | WYQQKPGK APKLLIY | V------- ASSLQS | GVPSRFSGSGSG--- TDFTLTIRSLQPEDFATYYC | QQAKS-- ------- | FGPGT KVDIK |
| iPS-434 079 | 21-225_52B1 | VK1\|L5\|J K3 | DIQMTQSPSSVST FVGDRIITIC | RAS--QDIR ----TWLA | WYQQKPGK APKLLIY | A------- ASSLQN | GVPSRFSGSGSG--- TDFTLTISSLQPEDFATYYC | QQAKS-- ------- | FGPGT KVDIK |
| iPS-434 097 | 21-225_52H10 | VK1\|L5\|J K3 | DIQMTQSPSSVSA SVGDRVTITC | RAS--QDIN -----SWLA | WYQQKPGK APKLLIY | V------- ASSLQS | GAPSRFSGSGSG--- TDFTLTIRSLQPEDFATYYC | QQAKS-- ------- | FGPGT KVDIK |
| iPS-434 123 | 21-225_53F7 | VK1\|L5\|J K3 | DIQMTQSPSSVSA SVGDRVTITC | RAS--QGIS -----RWLA | WYQQKPGK APNLLIY | A------- ASSLQS | GVPSRFSGSGSG--- TDFTLTISSLQPEDFATYYC | QQANS-- ------- | FGPGT KVDIK |
| iPS-434 145 | 21-225_55B1 | VK1\|L5\|J K3 | DIQMTQSPSSVSA SVGDRVTITC | RAS--QVIS -----RWLA | WYQQKPGK APNLLIY | A------- ASSLQS | GVPSRFSGSGSG--- TDFTLTISSLQPEDFATYYC | QQAKS-- ------- | FGPGT KVDIK |
| iPS-434 167 | 21-225_50F3 | VK1\|L5\|J K3 | DIQMTQSPSSVSA SVGDRVTITC | RAS--QDIS -----SWLA | WFQQKPGK APKLLIY | A------- ASSLQN | GVPSRFSGSGSG--- TDFTLTISSLQPEDFATYYC | QQTNS-- ------- | FGPGT KVDIK |
| iPS-434 189 | 21-225_56E5 | VK1\|L5\|J K3 | DIQMTQSPSSVSA SVGDRVTITC | RAS--QGIR -----KWLA | WYQQKPGK APKLLIY | A------- ASSLQS | GVPSRFSGSGSG--- TDFTLTISSLQPEDFATYYC | QQANS-- ------- | FGPGT KVDIK |
| iPS-434 193 | 21-225_56C6 | VK1\|L5\|J K3 | DIQMTQSPSSVSA SVGDRVTITC | RAS--QGIS -----SWLA | WYQQKSGN APKLLIY | A------- ASRLQS | GVPSRFSGSGSG--- TYFTLTISSLQSEDFATYYC | QQANS-- ------- | FGPGT KVDIK |
| iPS-434 195 | 21-225_56F6 | VK1\|L5\|J K3 | DIQMTQSPSSVCA YVGDRVTITC | RVS--QDIS -----KWLA | WFQQKPGK APKFLIY | V------- ASGLQS | GVPSRFSGSGSG--- TDFTLTISSLQPEDFATYYC | QQANS-- ------- | FGPGT KVDIK |
| iPS-434 273 | 21-225_57E4 | VK1\|L5\|J K3 | DIQMTQSPSSVSA SVGDRVTITC | RAS--QDIS -----NWLA | WYQQKPGK APKLLIY | A------- ASSLQN | GVPSRFSGSGSG--- TDFTLTISSLQPEDFATYYC | QQGNS-- ------- | FGPGT KVDIK |
| iPS-434 277 | 21-225_57A7 | VK1\|L5\|J K3 | DIQMTQSPSSVSA SVGDRVTITC | RAS--QGIR -----RWLA | WYQQKPGK APNLLIY | A------- ASNLQS | GVPSRFSGSGSG--- TDFTLTISSLQPEDFATYYC | QQANS-- ------- | FGPGT KVDIK |
| iPS-434 355 | 21-225_64G12 | VK1\|L5\|J K3 | DIQMTQSPSSVSA SVGDRVTITC | RAS--QNIT ----TWLA | WYQQKPGK APKLLIS | A------- ASSLQG | GVPSRFSGSGSG--- TDFTLTISSLQPEDFATYYC | QQANS-- ------- | FGPGT KLDIK |
| iPS-434 389 | 21-225_66F11 | VK1\|L5\|J K3 | DIQMTQSPSSVCA SVGDRVTITC | RES--QGIS ----IWLA | WYQQKPGK APKLLIY | A------- ASSLQS | GVPSRFSGSGYG--- TDFTLTISSVQPEDFATYYC | QQANS-- ------- | FGPGT KVDIK |
| iPS-434 423 | 21-225_70D1 | VK1\|L5\|J K3 | DIQMTQSPSSVSA SVGDRVTITC | RAS--QGVS -----RWLA | WYQQKPGK APKFLIY | A------- ASGLQS | GVPSRFSGSGSG--- TDFTVTISSLQPEDFATYYC | QQANS-- ------- | FGPGT KVDIK |
| iPS-435 291 | 21-225_146E1 | VK1\|L5\|J K3 | DIKMTQSPSSVSA SVGDRVTITC | RAS--QGIN -----NWLV | WYQQKPGK APKLLIY | A------- ASSLQS | GVPSRFRGSGSG--- TDFTLTISSLQPEDFATYYC | QQANS-- ------- | FGPGT KVDIK |
| iPS-435 303 | 21-225_146A6 | VK1\|L5\|J K3 | DIQMTQSPSSVSA SVGDRVTITC | RAS--QGIS -----RWLA | WYQQKPGK APKLLIY | A------- ASSLQG | GVPSRFSGSGSG--- TDFTLTISSLQPEDFATYYC | QQANS-- ------- | FGPGT KVDIK |
| iPS-435 335 | 21-225_147D1 | VK1\|L5\|J K3 | DIQMTQSPASVSA SVGDRVTITC | RAS--QNIS -----NWLT | WYQQKPGK APKLLIY | A------- ASSLQS | GVPSRFSGSGSG--- TDFTLTISSLQPEDFATYYC | QQTDS-- ------- | FGPGT KVDIK |
| iPS-435 339 | 21-225_147D10 | VK1\|L5\|J K3 | DIQMTQSPSSVSA SVGDRVTITC | RAS--QGIS -----NWLA | WYQEKPGK APKLLIY | A------- ASSLQS | GVPSRFSGNESG--- TDFTLSISLQPEDFATYYC | QQTDS-- ------- | FGPGT KVDVK |
| iPS-435 343 | 21-225_148E2 | VK1\|L5\|J K3 | DIQMTQSPSSVSA SVGDRVTITC | RAS--QGII -----SWLA | WYQQKPGK APKLLIY | A------- ASSLQS | GVPSRFSGSGSG--- TDFTLTISSLQPEDFATYYC | QQGNS-- ------- | FGPGT KVDIK |
| iPS-435 379 | 21-225_149B6 | VK1\|L5\|J K3 | DIQMTQSPASVSA SVGDRVTITC | RAS--QNIS -----NWLA | WYQQKPGR APKLLIY | A------- ASSLQG | GVPSRFSGSGSG--- TDYTLSISLQPEDFATYYC | QQTDS-- ------- | FGPGT KVDVK |
| iPS-435 381 | 21-225_149C6 | VK1\|L5\|J K3 | | | | | | | |

Figure 51 (Continued)

| | | | | | | | | | |
|---|---|---|---|---|---|---|---|---|---|
| iPS:435_391 | 21-225_149F8 | VK1|L5/J K3 | DIQMTQSPASVSA SVGDRVTITC | RAS---QGIS------NWLA | WYQQKPGK APKLLIY | A-------ASSLQS | GVPSRFSGNESG--- TDFTLSISSLQPEDFATYYC | QQTDS--------------FPFT | FGPGT KVDVK |
| iPS:435_395 | 21-225_149D1 | VK1|L5/J K3 | DIQMTQSPASVSA SVGDRVTITC | RAS---QNIS------NWLT | WYQQKPGK APKLLIY | A-------ASSLQS | GVPSRFSGSGSG--- TDFTLSISLQPEDFATYYC | QQTDS--------------FPFT | FGPGT KVDVK |
| iPS:435_403 | 21-225_150C5 | VK1|L5/J K3 | DIQMTQSPSSVSA SVGDRVTITC | RAS---QGIN------NWLA | WYQQKPGK APKLLIY | A-------ASSLQS | GVPSRFSGSGSG--- TDFTLTISSLQPEDFATYYC | QQTDS--------------FPFT | FGPGT KVDIK |
| iPS:435_447 | 21-225_152H7 | VK1|L5/J K3 | DIQMTQSPASVSA SVGDRVTITC | RAS---QDIS------NWLA | WYQQKPGK APKLLIY | A-------ASSLQG | GVPSRFSGSGSG--- TDFTLTISSLQPEDFATYYC | QQTDS--------------FPFT | FGPGT KVDIK |
| iPS:435_453 | 21-225_152G1 | VK1|L5/J K3 | DIQMTQSPASVSA SVGDRVTITC | RAS---QGIS------NWLA | WYQQKPGK APKLLIY | A-------ASSLQS | GVPSRFSGNESG--- TDFTLSISSLQPEDFATYYC | QQTDS--------------FPFT | FGPGT KVDVK |
| iPS:435_483 | 21-225_155A4 | VK1|L5/J K3 | DIQMTQSPASVSA SVGDRVTITC | RAS---QGIS------NWLA | WYHQKPGK APKLLIY | A-------ASSLQG | GVPSRFSGSGSG--- TDFTLSISSLQPEDFATYYC | HQTDS--------------FPFT | FGPGT KVDIK |
| iPS:435_485 | 21-225_155B4 | VK1|L5/J K3 | DIQMTQSPASVSA SVGDRVTITC | RAS---QDIS------NWLA | WYQQKPGK APKLLIY | A-------ASSLQG | GVPSRFNGSGSG--- TDFTLTISSLQPEDFATYYC | HQTDS--------------FPFT | FGPGT KVDIK |
| iPS:435_787 | 21-225_180A3 | VK1|L5/J K3 | DIQMTQSPSSVSA SVGDRVTITC | RAS---QDIT------SWLA | WYQQKPGK APKLLIY | A-------ASSLQS | GVPSRFSGSGSG--- TDFTLTISSLQPEDFAFYHC | QQANS--------------IPFT | FGPGT KVDIN |
| iPS:435_809 | 21-225_182H5 | VK1|L5/J K3 | DIQMTQSPSSVYA SVGDRVTITC | RAS---QDIT------SWLA | WYQQKPGK APKLLIY | A-------ASSLQS | GVPSRFSGSGSG--- TDFTLTISVQPEDFATYYC | QQVNS--------------FPFT | FGHGT KVDIK |
| iPS:435_889 | 21-225_186A1 | VK1|L5/J K3 | DIQMTQSPSSVSA SVGDRVTITC | RAS---QDIT------SWLA | WYQQKPGK APKLLIY | A-------ASSLQS | GVPSRFSGSGSG--- TDFTLTISVQPEDFATYYC | QQVNS--------------FPFT | FGHGT KVDIK |
| iPS:435_965 | 21-225_192H2 | VK1|L5/J K3 | DIQMTQSPSSVSA SVGDRVTITC | RAS---QGIS------SWLA | WYQQKPGK APKLLIY | G-------ASSLQS | GVPSRFSGSGSG--- TDFTLTISSLQPEDFATYYC | QQSNS--------------FPFT | FGPGT KVDVK |
| iPS:436_106 | 21-225_196F2 | VK1|L5/J K3 | DIQMTQSPSSVSA SVGDRVTITC | RAS---QGIS------SWLA | WYQQKPGK APKLLIY | A-------ASSLQS | GVPSRFSGSGSG--- TDFTLTISSLQPEDFATYYC | QQTNS--------------FPFT | FGPGT KVDIK |
| iPS:436_360 | 21-225_210H1 | VK1|L5/J K3 | DIQMTQSPSSVSA SVGDRVTITC | RAS---QDIT------IWLA | WYQQKPGK APKLLIY | A-------ASSLQS | GVPSRFSGSGSG--- TDFTLTISSLQPEDFATYYC | QQAKS--------------VPFT | FGPGT KVDIK |
| iPS:436_488 | 21-225_221A6 | VK1|L5/J K3 | DIQMTQSPSSVSA SVGDRVTITC | RAS---QGIS------SWLA | WYQQKPGK APKLLIY | T-------ASNLQS | GVPSRFSGSGSG--- TDFTLTISSLQPEDFATYYC | QQANS--------------FPFT | FGPGT KVDIK |
| iPS:436_496 | 21-225_222E1 | VK1|L5/J K3 | DIQMTQSPSSVSA SVGDRVTITC | RAS---QDIS------SWLA | WYQQKPGK APKLLIY | T-------ASNLQS | GVPSRFSGSGSG--- TDFTLTISSLQPEDFATYYC | QQANS--------------FPFT | FGRGT KVDIK |
| iPS:436_508 | 21-225_222F7 | VK1|L5/J K3 | DIQMTQSPSSVSA SVGDRVTITC | RAS---QGIS------SWLA | WYQQKPGK APKLLIY | T-------ASSFQS | GVPSRFSGSGSG--- TDFTLTISSVQPEDFATYYC | QQANS--------------FPFT | FGPGT KVDIK |
| iPS:436_516 | 21-225_222C1 | VK1|L5/J K3 | DIQMTQCPSSVSA SVGDRVTITC | RVS---QGIS------SWLA | WYQQKPGK ALKLVIY | T-------ASNLQS | GVPSRFSGSGSG--- TDFTLTISSLQREDFATYYC | QQDNS--------------FPFT | FGPGT KVDIK |
| iPS:437_234 | 21-225_64E2 | VK1|L5/J K3 | DIQMTQSPSSVSA SVGDRVTITC | RAS---QGIS------RWLA | WYQQKPGK APKLLIY | A-------ASSLQG | GVPSRFSGSGSG--- TDFTLTISSLQPEDFATYYC | QQANS--------------FPFT | FGPGT KVDIK |
| iPS:392_996 | 21-225_28B1 | VK1|L5/J K3 | DIQMTQSPSSVSA SVGDRVTITC | RAS---QAIN------DWLA | WYQQKPGK APKLLIY | A-------ASSFQS | GVPSRFSGSGSG--- TDFTLTISSLQPEDFATYYC | QQASS--------------FPFT | FGPGT KVDIK |
| iPS:393_010 | 21-225_25E11 | VK1|L5/J K3 | DIQMTQSPSSVSA SVGDRVTITC | RAS---QGIS------NWLA | WYQQKPGK APKLLIY | T-------ASSLQG | GVPSRFSGSGSG--- TDFTLTISSLQPEDFATYYC | QQANS--------------FPIT | FGPGT KVDIK |
| iPS:393_016 | 21-225_28F11 | VK1|L5/J K3 | DIQMTQSPSSVSA SVGDRVTITC | RAS---QGIS------NWLA | WYQQKPGK APKLLIS | A-------ASNLQS | GVPSRFRGSGSG--- TDFTLTISLQPEDFATYYC | QQANS--------------LPFT | FGPGT KVDIK |

Figure 51 (Continued)

| ID | Name | Germline | K_FR1 | K_CDR1 | K_FR2 | K_CDR2 | K_FR3 | K_CDR3 | K_FR4 |
|---|---|---|---|---|---|---|---|---|---|
| iPS:393 024 | 21-225_31H9 | VK1|L5/J K3 | DIQMTQSPSSVSA SVGDRVTITC | RAS--QGIT------SWLT | WYQQRPGK APKLLIY | D-------TSSLQS | GVPSRFSGSGSG-- TDFTFTISSLQPEDFATYYC | QQGNS---------PPFT | FGQGT KVDIK |
| iPS:393 080 | 21-225_34F3 | VK1|L5/J K3 | DIQMTQSPSSVSA TVGDRVTSTC | RAS--QGIS------KWLA | WYQQKPGK APKLIY | A-------ASSLQS | GVPSRFSGSGSG-- TDFTLTISSLQPEDSATYYC | QQANS---------PPFT | FGPGT KVDIK |
| iPS:393 084 | 21-225_35C6 | VK1|L5/J K3 | DIQMTQSPSSVSA SVGDRVTITC | RAS--QGIS------KWLA | WYQQKPGK APKPLIY | A-------ASSLQS | GVPTRFSGSGSG-- TDFTLTISSLQPEDFATYYC | QQANS---------PPFT | FGPGT KVDIK |
| iPS:393 086 | 21-225_36H5 | VK1|L5/J K3 | DIQMTQSPSSVSA SVGDRVTITC | RAS--QGIS------RWLA | WYQQKPGK APELLIY | A-------ASRLQS | GIPSRFSGSGSG-- TDFTLTISSLQPEDFATYYC | QQANS---------PPFT | FGPGT KVDIK |
| iPS:393 098 | 21-225_35G6 | VK1|L5/J K3 | DIQMTQSPSSVSA SVGDRLTITC | RAS--QGIS------RWLA | WYQQKVGK VPKLLIY | A-------ASRLQS | GVPSRFSGSGSG-- TAFTLTIGSLQPEDFATYYC | QQANS---------PPFT | FGPGT KVDLK |
| iPS:393 112 | 21-225_33G1 | VK1|L5/J K3 | DIQMTQSPSVSV SVGDRVTITC | RAS--QGIS------RWLA | WYQQKPGK APKLLIY | G-------AYSLQS | GVPSRFSGSGSG-- TDFTLTISSLQPEDFATYYC | QQANS---------PPFT | FGPGT KVDIK |
| iPS:393 116 | 21-225_34G7 | VK1|L5/J K3 | DIQMTQSPSSVSA SVGDRVTITC | RAS--QLIS------KWLA | WYQQKPGK APKLLIY | A-------ASSLQS | GVPLRFSGSGSG-- TDFTLTISSLQPEDFATYYC | QQANS---------PPFT | FGPGT KVDIK |
| iPS:393 132 | 21-225_33H7 | VK1|L5/J K3 | DIQMTQSPSSVSA SVGDRVTITC | RAS--QGIS------RWLA | WYQQKVGK VPKLLIY | A-------ASRLQS | GVPSRFSGSGSG-- TDFTLTIGSLQPEDFATYYC | QQANI---------PPFT | FGPGT KVDLK |
| iPS:393 140 | 21-225_35H12 | VK1|L5/J K3 | DIQMTQSPSSVSA SVGDRVTITC | RAS--QGIS------RWLA | WYQQKPGK APELLIY | A-------ASRLQS | GIPSRFSGSGSG-- TDFTLTISSLQPEDFATYYC | QQANS---------PPFT | FGPGT KVDIK |
| iPS:393 954 | 21-225_4H6 | VK1|L5/J K3 | DIQMTQSPSSVSA SVGDRVTITC | RAS--QGIS------RWLA | WYQQKPGK APKLLIY | G-------ASSLQS | GVPSRFSGSGSG-- TDFTLTISSLQPEDFATYYC | QQANS---------PPFT | FGPGT KVDIK |
| iPS:398 502 | 21-225_23B11 | VK1|L5/J K3 | DIQMTQSPSSVSA SVGDRVTITC | RAS--QGIT------KWLA | WYQQKPGK APKVLIY | A-------ASSLQS | RVPSRFSGSRSG-- TDFTLTISSLQPEDFATYYC | QQANS---------PPFT | FGPGT KVDIK |
| iPS:398 520 | 21-225_31C4 | VK1|L5/J K3 | DIQMTQSPSSVSA SVGDRVTITC | RAS--QGIS------KWLA | WYQQKPGK APKPLIY | A-------ASSLQS | GVPTRFSGSGSG-- TDFTLTISSLQPEDFATYYC | QQANS---------PPFT | FGPGT KVDIK |
| iPS:402 223 | 21-225_30A11 | VK1|L5/J K3 | DIQMTQSPSSVSA SVGDRVTITC | RAS--QGIS------RWLA | WYQQKPGR APELLIY | A-------ASRLQS | GIPSRFSGSGSG-- TDFTLTISSLQPEDFATYYC | QQANS---------PPFT | FGPGT KVDNK |
| | VK4|B3/JK1 | Germline | DIVMTQSPDSLAV SLGERATINC | KSS--QSVLSSNNN YLA | WYQQKPGQ PPKLLIY | W-------ASTRES | GVPDRFSGSGSG-- TDFTLTISSLQAEDVAVYYC | QQYYS | FGQGT KVEIK |
| iPS:426 112 | 21-225_12F12 | VK4|B3/J K1 | DIVMTQSPDSLAV SLGERATINC | KSS--QTVLFSSNNNH YLA | WYQQKPGQ PPNLLIY | W-------ASTRAS | GVPDRFSGSGSG-- TDFTLTISSLQAEDVAVYYC | QQYS----------SPWT | FGQGT KVEIK |
| iPS:451 137 | 21-225_74A7 | VK4|B3/J K1 | DIVMTQSPDSLAV SLGERATINC | KSS--QSVLFSSNNYN YLA | WYQQRPGQ PPNLLIY | W-------ASTRES | GVPDRFSGSGSG-- TDFTLTISSLQAADVAVYYC | QQHS----------SPPT | FGQGT TVQIK |
| iPS:433 909 | 21-225_43D8 | VK4|B3/J K1 | DIVMTQSPDSLAV SLGERATINC | KSS--QSVLMTSNDKN YLT | WYQQKPGQ PPKLLIY | W-------ASTRES | GVPDRFSGGGSG-- TDFTLTISGLQAEDVAVYYC | QQYYS---------TPPT | FGQGT KVEIK |
| iPS:434 177 | 21-225_56A1 | VK4|B3/J K1 | DIVMTQSPDSLAV SLGERATINC | KSS--QSVLHSSNNKN YLV | WYQQRPGQ PPNLLIY | W-------ASTRES | GVPDRFSGSGSG-- TDFTLTISSLQAEDVAVYYC | QQYYS---------TPPT | FGPGT KVEIK |
| iPS:434 237 | 21-225_61B5 | VK4|B3/J K1 | DIVMTQSPDSLAV SLGERATINC | KSS--QSVLYSSNNNN SLT | WYQLKPGQ PPKKLIY | W-------ASTRES | GVPDRFSGSGSG-- TDFTLTISSLQAEDVAVYYC | QQYYS---------TPPT | FGQGS KVEIK |

Figure 51 (Continued)

| | | | | | | | | | |
|---|---|---|---|---|---|---|---|---|---|
| iPS:434 285 | 21-225_57A11 | VK4jB3jJK1 | DIVMTQSPDSLTV SLGERATINC | KSS--- QSVLHSSNNYN YLA | WYQQRPGQ PPKLVIY | W------- ASTRAS | GVPDRFSGSGSG-- TDFTLTISSLQAEDMAVYYC | QQYYS----------- | ------TFWT | FGQGT KVEFK |
| iPS:434 295 | 21-225_58B9 | VK4jB3jJK1 | DIVMTQSPDSLAV SLGERATINC | KSG--- QSILYSSNNRM YLA | WYQQKPGQ PPKKLIY | W------- ASTRDS | GVPARFSGSGSG-- TDFTLTISSLQAEDVAVYYC | QQYYS----------- | ------TPPT | FGQGS KVEIK |
| iPS:434 321 | 21-225_59F10 | VK4jB3jJK1 | DIVMTQFPDSLAV SLGERATINC | KSS--- QIVLYRSNNYN YLA | WYQQKPGQ PPKLLIY | W------- ASTRES | GVPDRFSGSGSG-- TDFTLTISSLQAEDVAVYYC | QQYFS----------- | ------TPPT | FGQGT KVEIK |
| iPS:434 431 | 21-225_70E7 | VK4jB3jJK1 | DIVMTQSPDSLAV SLGERATINC | KSS--- QSVLYSGNNRN YLA | WYQQKPGQ PPKLLIY | W------- ASTRES | GVPDRFSGSGSG-- TDFTLTISSLQAEDVAVYYC | QQYYN----------- | ------IPPT | FGQGT KVEIK |
| iPS:434 475 | 21-225_74F9 | VK4jB3jJK1 | DIVMTQSPDSLAV SLGERATINC | KSS--- QSVLYSGNNYN YLA | WYQQKPGQ PPKKLIY | W------- ASTRES | GVPDRFSGSGSG-- TDFTLTISSLQAEDVAVYYC | QQYYS----------- | ------SFPT | FGQGT KVEIK |
| iPS:434 477 | 21-225_74A6 | VK4jB3jJK1 | DIVMTQSPDSLAV SPGERATINC | KSS--- QSVLHSSNNYN YLA | WYQQKPGQ PPDLLIY | W------- ASTRES | GVPDRFSGSGSG-- TDFTLTISSLQAEDVAVYSC | QQYFS----------- | ------TPWT | FGQGT QVEIK |
| iPS:434 481 | 21-225_74B10 | VK4jB3jJK1 | DIVMTQSPDSLAV SLGERATINC | KSS--- QSVLHSSNNRN YLT | WYQQKPGQ PPKLLIY | W------- ASTRES | GVPDRFSGSGSG-- TDFSLTISSLQAEDVAVYYC | QQYYS----------- | ------IPPT | FGQGT KVEIK |
| iPS:434 487 | 21-225_76G2 | VK4jB3jJK1 | DIVMTQSPDSLAV SLGERATINC | KSS--- QSVLHSSNNYN YLA | WYQQKPGQ PPKLLIY | W------- ASTRES | GVPDRFSGSGSG-- TDFTLTISSLQVEDVAVYYC | QQYYS----------- | ------SPPT | FGQGT KVEIK |
| iPS:434 493 | 21-225_76F3 | VK4jB3jJK1 | DIVMTQCPDSPAV SLGERATINC | KSS--- QSVLFSSNNYN YLA | WYQQRPGQ PHDLLIY | W------- ASTRES | GVPDRFSGSGSG-- TDFTLTISSLQAADVAVYYC | QQYHS----------- | ------SPLT | FGQGT TVQIK |
| iPS:434 509 | 21-225_76F5 | VK4jB3jJK1 | VIVLTQSPDSLAV SLGERATINC | KSS--- QSVLHSSNSYN YLA | WYQQKPGQ SPKVLIY | W------- TSTRES | GVPDRFSGSGSG-- TDFTLTISSLQAEDVAVYYC | QQYYS----------- | ------SPPT | FGQGT KVEIK |
| iPS:434 525 | 21-225_76E8 | VK4jB3jJK1 | DIVMTQSPDSLAV SLGERATINC | KSS--- QSVLHSSNNYN YLA | WYQQKPGQ PPKVLIY | W------- TSTRES | GVPDRFSGSGSG-- TDFTLTISSLQAEDVAVYYC | QQYFS----------- | ------SPLT | FGQGT KVEIK |
| iPS:434 549 | 21-225_76E11 | VK4jB3jJK1 | DIVMTQSPDSLAV SLGERATINC | KSR--- QSVLHSSNNYN YLA | WFQQKPGQ PPKLLIY | W------- ASTRES | GVPDRFSGSGSG-- TDFTLTISSLQAEDVAVYYC | QQYYS----------- | ------TPPT | FGQGT KVEIK |
| iPS:434 551 | 21-225_75C4 | VK4jB3jJK1 | DIVMTQSPDSLAV SLGERATINC | KSS--- QSILYSSNNNN YLA | WYQQKAGQ PPKLLIY | W------- ASTRES | GVPDRFSGSGSG-- TDFTLTISSLQAEDVAVYYC | QQYYI----------- | ------TPPT | FGQGT RVEIK |
| iPS:434 575 | 21-225_77C7 | VK4jB3jJK1 | DIVMTQSPDSLAV SLGERATINC | KSS--- QIVLHSSNNYN YLA | WYQQKPGQ PPKVLIY | W------- TSTRES | GVPDRFSGSGSG-- TDFTLTISSLQAEDVAVYYC | QQYFS----------- | ------SPPT | FGQGT KVEIK |
| iPS:434 597 | 21-225_77C10 | VK4jB3jJK1 | DIVMTQSPDSLAV SLGERATINC | KSS--- QSVLYTSNNMN YLA | WYQQKPGQ PPKLLIY | W------- ASTRES | GVPDRFSGSGSG-- TDFTLTISSLQAEDVAVYYC | QHYYN----------- | ------TPWK | FVQGT KVEIT |
| iPS:434 617 | 21-225_74B8 | VK4jB3jJK1 | DSVMTQSPDSLAV SLGERATINC | KSS--- QSVLHSSNKKN YLA | WYQQKPGQ PPKLLIY | W------- ASTRES | GVPDRFSGSGSG-- TDFTLTISSLQAEDVAVYYC | QQYYR----------- | ------TPWT | FGQGT KVEIK |

Figure 51 (Continued)

| | | | | | | | | | |
|---|---|---|---|---|---|---|---|---|---|
| iPS:434 619 | 21-225_78C1 | VK4jB3jJK1 | DIVMTQSPDCLAV SLGERATINC | KSS--- QSVLYTSNNNN YLA | WYQQKPGQ PPKLLIY | W------- ASTRES | GVPDRFSGSGSG--- TDFTLTISSLQAEDVAVYYC | QHYN------ ------------ | FVQGT KVEIK |
| iPS:434 639 | 21-225_74B7 | VK4jB3jJK1 | DIVMTQSPDSLAV SLGERATINC | KSS--- QTVLHSSNNYN YLA | WYQQKPGQ PPKVLIY | W------- TSTRES | GVPDRFSGSGSG--- TDFTLTISSLQAEDVAVYYC | QQYFS------ ------SFPPT | FGQGT KVEIK |
| iPS:434 649 | 21-225_78E11 | VK4jB3jJK1 | DIVMTQSPDSLAV SLGERATINC | KSS--- QSVLYSFNNYN YLA | WYQQKPGQ PPKKLIY | W------- ASTRES | GVPDRFSGSGSG--- TDFTLTISSLQAEDVAVYYC | QQYYS------ ------SPPT | FGQGT KVEIK |
| iPS:434 653 | 21-225_74B5 | VK4jB3jJK1 | DIVMTQSPDSLAV SLGERATINC | KSS--- QSVLFSGNNYN YLA | WYQQRPGQ PPNLLIY | W------- ASTRES | GVPDRFSGSGSG--- TDFTLTISSLQAADVAVYYC | QQYYS------ ------SFPPT | FGQGT TVQIK |
| iPS:434 655 | 21-225_78H12 | VK4jB3jJK1 | DIVMTQSPDSLAV SLGERATINC | KSS--- QTVLHSFNNYN YLA | WYQQKPGQ PPKVLIY | W------- TSTRES | GVPDRFSGSGSG--- TDFTLTISSLQAEDVAVYYC | QQYFS------ ------SFPPT | FGQGT KVEIK |
| iPS:434 665 | 21-225_74G4 | VK4jB3jJK1 | DIVMTQSPDSLAV SLGERATINC | KSS--- QSVLYSSNNNN YLA | WYQQKAGQ PPKLLIY | W------- ASTRES | GVPDRFSGSGSG--- TDFSLPIGSLQAEDVAVYYC | QQYYS------ ------IPPT | FGQGT KVEIK |
| iPS:434 675 | 21-225_79G6 | VK4jB3jJK1 | DIVMTQSPDSLAV SLGERATINC | MSS--- QSVLHSFNNKN YLT | WYQQKPGQ PPKLLIY | W------- ASTRES | GVPDRFSGSGSG--- TDFTLTISSLQAEDVAVYYC | QQYYI------ ------IPPT | FGQGT KVEIK |
| iPS:434 685 | 21-225_79E9 | VK4jB3jJK1 | DIVMTQSPDSLAV SLGERATINC | KSS--- QSILYSSNNNN YLA | WFQQKPGQ PPKLLIY | W------- ASTRES | GVPDRFSGSGCG--- TDFTLTISSLQAEDVAVYYC | QQYYI------ ------IPPT | FGQGT KVEIK |
| iPS:434 689 | 21-225_79G10 | VK4jB3jJK1 | DIVMTQSPDSLAV SLGERATINC | KSS--- QSVLFSSNNYN YLA | WYQQRPGQ PHNLLIY | W------- ASTRES | GVPDRFSGSGSG--- TDFTLTISSLQAADVAVYYC | QQYHS------ ------SPLI | FGQGT TVQIK |
| iPS:434 697 | 21-225_79F12 | VK4jB3jJK1 | DIVMTQSPDSLAV SLGERATINC | KSS--- QSILYSSNNYN YLA | WYQQKPGQ PPKLLIY | W------- ASTRES | GVPDRFSGSGSG--- TDFTLTISSLQAEDVAVYYC | QQYYS------ ------TPWT | FGQGT KVEIK |
| iPS:434 707 | 21-225_80D3 | VK4jB3jJK1 | DIVMTQSPDSLAV SLGERATINC | KSS--- QSVLYTSNNNN YLA | WYQQKPGQ PPKLLIY | W------- ASTRES | GVPDRFSGSGSG--- TDFTLTISSLQAEDVAVYYC | QHYNE------ ------TPGK | FVQVT KVEIT |
| iPS:434 711 | 21-225_80H3 | VK4jB3jJK1 | DIVMTQSPDSLAV SLGERATINC | KSS--- QSVLHRSNNYN YLA | WYQQKPGQ PPKLLIY | W------- ASTRES | GVPDRFSGSGSG--- TDFTLTISSLQAEDVAVYYC | QQYYS------ ------TPPT | FGQGT KVEIK |
| iPS:434 731 | 21-225_80E9 | VK4jB3jJK1 | DIVMTQSPDSLAV SLGERATINC | KSS--- QSVLYTSNNNN YLA | WYQQKPGQ PPKLLIY | W------- ASTRES | GVPDRFSGSGSG--- TDFTLTISSLQAEDVAVYYC | QQYYN------ ------TPWT | FGQGT KVEIK |
| iPS:434 761 | 21-225_81E5 | VK4jB3jJK1 | DIVMTQSPDSLAV SLGERATINC | KSS--- QSVLFSSNNYN YLA | WYQQRPGQ PPNLLIY | W------- ASTRES | GVPDRFSGSGSG--- TDFTLTISSLQAADVAVYYC | QQYYS------ ------SPLI | FGQGT TVQIK |
| iPS:434 771 | 21-225_81F9 | VK4jB3jJK1 | DIVMTQSPDSLAV SLGERATINC | KSS--- QSVLYTSNNNN YLA | WYQQKPGQ PPKLLIY | W------- ASTRES | GVPDRFSGSGSG--- TDFTLTISSLQAEDVAVYIR | QHYND------ ------TPGK | FVQGI MVEIT |
| iPS:434 827 | 21-225_83F3 | VK4jB3jJK1 | DIVMTQSPDSLAV SLGERATINC | KSS--- QSVLYTSNNNN YLA | WYQQKPGQ PPKLLIY | W------- ASTRES | GVPDRFSGSGSG--- TDFTLTISSLQAEDVAVYYC | QHYND------ ------TPWK | FVQGI KVEIK |

Figure 51 (Continued)

| | | | | | | | | |
|---|---|---|---|---|---|---|---|---|
| iPS:434 829 | 21-225_83G3 | VK4\|B3\|J K1 | DIVMTQSPDCLAV SLGERATINC | KSS---QSVLYTSNNNYN YLA | WYQQKPGQ PPKVLIY | W-------ASTRES | GVPDRFSGSGSG-TDFTLTISSLQAEDVAVYYC | QHYN---------- | ----TFWT | FVQGT KVEIK |
| iPS:434 841 | 21-225_83G7 | VK4\|B3\|J K1 | DIVMTQSPDSLAV SLGERATIIC | KSS---QIVLHSSNNYN YLA | WYQQKPGQ PPKVLIY | W-------TSTRES | GVPDRFSGSGSG-TDFTLTISSLQAEDVAVYYC | QQYFS---------- | ----SPLT | FGQGT KVEIK |
| iPS:434 863 | 21-225_84G7 | VK4\|B3\|J K1 | DIVMTQSPDSPAV SLGERATIIC | KSS---QIVLHSSNNYN YLA | WYQQKPGQ PPKVLIY | W-------TSTRES | GVPDRFSGSGSG-TDFTLTISSLQAEDVAVYYC | QQYFS---------- | ----SPPT | FGQGT KVEIK |
| iPS:434 877 | 21-225_85H2 | VK4\|B3\|J K1 | DSMMTQSPDSLAV SLGERATINC | KSS---QSVLHSGNKSN YLA | WYQQKPGQ PPKLLIY | W-------ASTRES | GVPDRFSGSGSG-TDFTLTISSLQAEDVAVYYC | QQYYR---------- | ----TFWT | FGQGT KVEIK |
| iPS:434 901 | 21-225_85H9 | VK4\|B3\|J K1 | DIVMTQSPDSLAV SLGERATNC | KSS---QSVLHRSNNYN YLA | WYQQKPGQ PPKLLIY | W-------ASTRES | GVPDRFSGSGSG-TDFTLTISSLQAEDVAVYYC | QQYYS---------- | ----TFPT | FGQGT KVEIK |
| iPS:434 935 | 21-225_86E9 | VK4\|B3\|J K1 | DIVMTQCPDSPAV SLGERATNC | KSS---QSVLHRSNNNYN YLA | WYQQKPGQ PPKLLIY | W-------ASTRES | GVPDRFSGSGSG-TDFTLTISSLQAEDVAVYYC | QQYHS---------- | ----SPLT | FGQGT TVEIK |
| iPS:434 965 | 21-225_88A1 | VK4\|B3\|J K1 | NIVMTQSPDSLAV SLGERATNC | KSS---QSVLHSSNNYN YLT | WYQQKPGQ PPKLLIY | W-------ASTRKS | GVPDRFSGSGSG-TDFTLTISSLQAEDVAVYYC | QQYYS---------- | ----SPPT | FGQGT KVEIK |
| iPS:434 971 | 21-225_88G2 | VK4\|B3\|J K1 | DIVMTQSPDSLAV SLGERATINC | KSS---QIVLHSSNNYN YLA | WYQQKPGQ PPKLLIY | W-------TSTRES | GVPARFSGSGSG-TDFTLTISSLQAEDVAVYYC | QQYYN---------- | ----TFWT | FVQGT KVEIK |
| iPS:434 973 | 21-225_88B4 | VK4\|B3\|J K1 | DIVMTQSPDSLAV SLGERATVNC | KSS---QSVLHSNSNNN YLA | WYQQKPGQ PPKLLIY | W-------ASTRES | GVPARFSGSGSG-TDFTLTISSLQAEDVAVYYC | QQYYS---------- | ----TFPT | FGQGT KVEIK |
| iPS:434 997 | 21-225_88C10 | VK4\|B3\|J K1 | DIVMTQSPDSLAV SLGERATINC | KSS---QSVLHSSNNWN YLA | WHQQKPGQ PPKLLIH | W-------AFTRKS | GVPDRFSGGSGG-TNTFLTISSLQAEDVAVYYC | QQYYR---------- | ----APPT | FGQGT KVEIK |
| iPS:435 051 | 21-225_90D9 | VK4\|B3\|J K1 | DIVMTQSPDSLAV SLGERATINC | KSS---QIVLHSSNNYN YLA | WYQQKPGQ PPKVLIY | W-------TSTRES | GVPDRFSGSGSG-TDFTLTISSLQAEDVAVYYC | QQYLS---------- | ----SPLT | FGQGT KVEIK |
| iPS:435 053 | 21-225_75F9 | VK4\|B3\|J K1 | DIVMTQSPDSLPV SLGERATVNC | KSS---QSVLHNSNNNN YLA | WYQQKPGQ PPKLLIY | W-------ASTRES | GVPDRFSGSGSG-TDFTLTISSLQAEDVAVYYC | QQYYS---------- | ----SPPT | FVQGT KVEIK |
| iPS:435 071 | 21-225_91F1 | VK4\|B3\|J K1 | DIVMTQSPDCLAV SLGERATINC | KSS---QSVLYTSNNNN YLA | WYQQKPGQ PPKLLIY | W-------ASTRES | GVPARFSGSGSG-TDFTLTISSLQAEDVAVYYC | QHYN---------- | ----TFWK | FGQGT KVEIK |
| iPS:435 087 | 21-225_91G8 | VK4\|B3\|J K1 | DIVMTQSPDSLAA SLGERATINC | KSS---QSVLYTSNNNN YLA | WYQQKPGQ PPKILIY | W-------TSTRES | GVPARFSGSGSG-TDFTLTISSLQAEDVAVYYC | QQYYT---------- | ----TFWT | FGQGT KVEIK |
| iPS:435 113 | 21-225_92E6 | VK4\|B3\|J K1 | DIVMTQSPDSLAV SLGERATINC | KSS---QNILSSSNNKN YLT | WYQQKPGQ PPKILIY | W-------TSTRES | GVPDRFSGSGFG-TDFTLTISSLQAEDVAVYYC | QQYFS---------- | ----VPPT | FGQGT KVEIK |
| iPS:435 167 | 21-225_92F12 | VK4\|B3\|J K1 | DIVMTQSPDSLAV SLGERATINC | KSS---QSVLHRSNNYN YLA | WYQQKPGQ PPKLLIY | W-------ASTRES | GVPDRFSGSGSG-TDFTLTISSLQAEDVAVYYC | QQYYS---------- | ----TFPT | FGQGT KVEIK |

Figure 51 (Continued)

| | | | | | | | | |
|---|---|---|---|---|---|---|---|---|
| iPS:435_203 | 21-225_75A7 | VK4\|B3\|JK1 | DIVMTQSPDSLAV SLGERATINC | KSS---QTVLHSSNNYN YLA | WYQQKPGQ PPKVLIY | W------TSTRES | GVPDRFSGSGSG-TDFTLTISSLQAEDVAVYYC | QQYFS---------SPPT | FGQGT KVEIK |
| iPS:435_209 | 21-225_75A10 | VK4\|B3\|JK1 | NIVMTQSPDSLAV SLGERATINC | KSS---QSVLHMSNNYN YLT | WYQQKPGQ PPKLLIY | W------ASTRKS | GVPDRFSGSGSG-TDFTLTISSLQAEDVAVYFC | QQYYS---------SPPT | FGQGT KVEIK |
| iPS:435_211 | 21-225_94E11 | VK4\|B3\|JK1 | DIVMTQSPDSLAV SLGERATINC | KSS---QSVLFSSNNYN YLA | WYQQKPGQ PPNLLIY | W------ASTRES | GVPDRFSGSGSG-TDFTLTISSLQAADVAVYYC | QQYHS---------SPLT | FGQGT TVQIK |
| iPS:435_215 | 21-225_94E12 | VK4\|B3\|JK1 | DIVMTQSPDSLAV SLGERATINC | KSS---QSVLHRGNNYN YLA | WYQQKPGQ PPKLLIY | W------ASTRES | GVPDRFSGSGSG-TDFTLTISSLQAEDVAVYYC | QQYYS---------TPPT | FGQGT KVEIK |
| iPS:435_227 | 21-225_95G4 | VK4\|B3\|JK1 | DIVMTQCPDSLAV SLGERATINC | KSS---QSVLFRGNNYN YLA | WYQQKPGQ PPNLLIY | W------ASTRES | GVPDRFSGSGYG-TDFTLTISSVQAADVAVYYC | QQYHS---------SPLT | FGQGT TVQIK |
| iPS:435_245 | 21-225_95E12 | VK4\|B3\|JK1 | DIVMTQSPDSLAV SLGERATINC | KSS---QSVLYSSNNAN YLA | WYQQKPGQ PPNLFIY | W------ASTRES | GVPDRFSGSGSG-TDFTLTISSLQAEDVAVYYC | QQYYS---------TPCS | FGQGT KVEIK |
| iPS:435_249 | 21-225_96E2 | VK4\|B3\|JK1 | DSVMTQSPDSLAV SLGERATINC | KSS---QSVLHSSNNKN YLA | WYQQKPGQ PPKLLIY | W------ASTWES | GVPDRFSGSGSG-TDFTLTISSLQAEDVAVYYC | QQYYR---------TPWT | FGQGT KVEIK |
| iPS:435_255 | 21-225_96D5 | VK4\|B3\|JK1 | DIVMTQSPDSLAV SLGERATINC | KSS---QSVLHSSNNYN YLA | WYQQKPGQ PPNNLIY | W------ASTRES | GVPDRFSGSGSG-TDFTLTISSLQAEDVAVYYC | QQYYS---------SPPT | FGQGT TVEIK |
| iPS:435_257 | 21-225_96H5 | VK4\|B3\|JK1 | DIVMTQSPDSLAV SLGERATINC | KSS---QSVLYSSNSHN YLA | WYQQKPGQ PPKLLIY | W------ASIRES | GVPDRFSGRGSG-TDFTLTISISSMQAEDVAVYYC | QQYYS---------TPCS | FGQGT KVEIK |
| iPS:435_267 | 21-225_96D10 | VK4\|B3\|JK1 | DIVMTQSPDSLAV SLGERATINC | KSS---QNILSSSNNKN YLT | WYQLKPRQ PPKLLIY | W------TSTRES | GVPDRFSGSGFG-TDFTLTISSLQAEDVAVYYC | QQYFS---------VPPT | FGQGT KVEIK |
| iPS:435_279 | 21-225_97H4 | VK4\|B3\|JK1 | DIVMTQSPDCLAV SLGERATINC | KSS---QSVLYTSNNNN YLA | WYQLKPGQ PPKLLIY | W------ASTLRS | GVPDRFSGSGSG-TDFTLTISSLQAEDVAVYYC | QHYND---------TPWK | FVQGT KVEIT |
| iPS:435_321 | 21-225_147E4 | VK4\|B3\|JK1 | DIVMTQSPDSLAV SLGERATINC | KSS---QSVLHSSNNYN YLA | WYQQKPGQ PPKLLIY | W------ASTRES | GVPDRFSGSGRG-TDFTLTISSLQAEDVAIYYC | QQYYS---------TPST | FGPGT KVEIK |
| iPS:435_353 | 21-225_148F8 | VK4\|B3\|JK1 | DIVMTQSLDSLAV SLGERATINC | KSS---QSALHSSNNYN YLA | WYQQKPGQ PPKLLIY | W------ASTRES | GVPDRFSGSGSG-TDFTLTISSLQAEDVAVYYC | QQYYS---------IPPT | FGQGT KVEIK |
| iPS:435_369 | 21-225_149A2 | VK4\|B3\|JK1 | DIVMTQSPDSLAV SLGERATINC | KSS---QSVLYSPNNNN YLA | WYQQKPGQ PPKLLIY | W------ASTRES | GVPDRFSGSGSG-TDFTLTISSLQAEDVAVYYC | QQYYS---------TPCS | FGQGT KVEIK |
| iPS:435_373 | 21-225_149E3 | VK4\|B3\|JK1 | DIVMTQSPDSLAV SLGERATISC | KSS---QTVLHNSNNHN YFA | WYQQKPGQ PPKLLIY | W------ASTLRS | GVPDRFSGSGSG-TDFTLTISSLQAEDVAVYYC | QQYYS---------TPPT | FGQGT KVEIK |
| iPS:435_375 | 21-225_149H4 | VK4\|B3\|JK1 | DIVMTQSPDSLAV SLGERATINC | KSS---QSVLSSSNDNN YLA | WYQQKPGR PPKLLIY | W------SSTRES | GVPDRFSGSGSG-TDFTLTISSLQAEDVAVYYC | HQYYS---------YPPT | FGQGT KVEIK |

Figure 51 (Continued)

| | | | | | | | | |
|---|---|---|---|---|---|---|---|---|
| iPS-435 481 | 21-225_154A1 | VK4|B3/J K1 | DIVMTQSPDSLAV SLGERATINC | RSS--- QSVLHSSNNYN YLA | WYQQKPGQ PPKLLIY | W------ ASKRES | GVPDRFSGSGSG- TDFTLTISSLQAEDVAVYYC | QQYFS---------SPRT | FGQGT KVEIK |
| iPS-435 557 | 21-225_158B1 | VK4|B3/J K1 | DIVMTQSPDSPAV SLGERATINC | RSS--- QNVLHSSNNNN YLT | WYQQRPGQ PPKLLIY | W------ ASTRES | GVPDRFSGSGSG- TDFTLTISSLQAEDVAVYYC | QQYYS---------TPPT | FGQGT KVEIK |
| iPS-435 627 | 21-225_162F6 | VK4|B3/J K1 | DIVMTQSPDSLAV SLGERATINC | KSS--- QNVLHSSNNNN YLT | WYQQRPGQ PPKLLIY | W------ ASTRES | GVPDRFSGSGSG- TDFTLTISSLQAEDVAVYYC | QQYYS---------TPPT | FGQGT KVEIK |
| iPS-435 701 | 21-225_170F6 | VK4|B3/J K1 | DIVMTQSPDSLAV SLGERATINC | KSS--- QSVLHSSNNYN YLA | WYQQRPGQ PPKVLIH | W------ ASTRKS | GVPDRFSGSVSG- TDFTLTISSLQAEDVAVYYC | QQYYR---------TPWT | FGQGT KVEIK |
| iPS-435 737 | 21-225_174G5 | VK4|B3/J K1 | DIVMTQSPDSLAV SLGERATINC | KSS--- QSVLHSSNNYN YLT | WYQQKSGQ PPKLLIY | W------ ASTRES | GVPDRFSGSGSG- TDFTLTISSLQAEDVAVYYC | QQYYR---------TPWT | FGQGT KVEIK |
| iPS-435 751 | 21-225_175D1 | VK4|B3/J K1 | DIVMTQSPDSLAV SLGERATISC | KSS--- QSVLYSSNNNN YLA | WYQQKPGQ PPNLLIY | W------ TSTRES | GVPDRFSGSGSG- TDFTLTISSLQAEDVAVYYC | QQYYS---------TPPT | FGQGT KVEIK |
| iPS-435 773 | 21-225_177B1 | VK4|B3/J K1 | DIVMTQSPDSLAV SLGERATVNC | KSS--- QSVLHSSNNYN YLT | WYQQKPGQ PPKLLIY | W------ ASTRES | GVPDRFSGSGSG- TDFTLTISSLQAEDVAVYYC | HQYFI---------SPPT | FGQGT KVEIK |
| iPS-435 801 | 21-225_181E5 | VK4|B3/J K1 | DIVMTQSPDSLAV SLGERATINC | RSS--- QSVLHSSNNYN YLT | WYQQKPGQ PPKLLIY | W------ ASTRES | GVPDRFSGSGSG- TDFTLTISSLQAEDVAVYYC | QQYYS---------TPPT | FGQGT KVEIK |
| iPS-435 841 | 21-225_191D8 | VK4|B3/J K1 | DIVMTQSPDSLAV SLGERATISC | KSS--- QSVLSSSNNNN YLV | WYQQKPGH PPKLLIY | W------ ASTRKS | GVPDRFSGSGSG- TDFTLAISSLQAEDVAVYYC | QQYYR---------TPPT | FGLGT KVEIK |
| iPS-435 925 | 21-225_190D7 | VK4|B3/J K1 | DIVMTQSPDSLAV SLGERATINC | KSS--- QSVLHSFNNYN YLA | WYQQKAGH PENLLIY | W------ ASTRES | GVPDRFSGSGSG- TDFLFISSLQAEDVAVYYC | QQYYI---------TPWT | FGQGT KVDIK |
| iPS-436 021 | 21-225_193G4 | VK4|B3/J K1 | DIVMTQSPDSLAV SLGERATINC | RSS--- QSVLYSSNNYN YLT | WYQQKPGQ PPKLLIY | W------ ASTRES | GVPDRFSGSGSG- TDFTLTISSLQADDVAVYYC | QQYYR---------TPWT | FGQGT KVEIK |
| iPS-436 114 | 21-225_196G8 | VK4|B3/J K1 | DIVMTQSPDSLIV SLGERATISC | KSS--- QSVLHSSNNYN YLA | WYQQKPGQ PPKLLIY | W------ ASTRES | GVPDRFSGSGSG- TDFTLTISSLQAEDVAVYYC | QQYYN---------TPPT | FGQGT KVEIK |
| iPS-436 150 | 21-225_197H4 | VK4|B3/J K1 | DIMMTQSSDSLIV SLGERAIISC | RSS--- QSVLHSFNNYN YLA | WYQQKAGH PFNLLIY | W------ ASTRES | GVPDRFSGSGSG- TDFTLTISSLQAEDVAVYYC | QQYYN---------TPPT | FGLGT KVEIK |
| iPS-436 154 | 21-225_197C6 | VK4|B3/J K1 | DIVMTQSPDSLAV SLGERAIISC | RSS--- QSVLHSSNNYN YLA | WYQQKPGH PFNLLIY | W------ ASTRES | GVPDRFSGSGSG- TDFTLTISSLQAEDVAVYYC | QQYYS---------TPPT | FGLGT KVEIK |
| iPS-436 218 | 21-225_200G7 | VK4|B3/J K1 | DIVMTQSPDSPTA SLGERATVKC | KSS--- QSVLHSSNNMN YLA | WYQQKPGQ PPKLLIY | W------ ASTRES | GVPDRFSGSGSG- TDFTLAISSLQAEDVAVYYC | QQYYN---------TPPT | FGQGT KVEIK |
| iPS-436 272 | 21-225_201F5 | VK4|B3/J K1 | DIVMTQSPDSLAV SLGERATINC | KSS--- QSVLYSSNNKN YLV | WYQQKPGQ PPKLLIY | W------ ASTRES | GVPDRFSGSGSG- TDFTLTISSLQAEDVAVYYC | QQYYS---------TPPT | FGQGT KVEIK |

Figure 51 (Continued)

| | | | | | | | | |
|---|---|---|---|---|---|---|---|---|
| iPS:436 400 | 21-225_213H7 | VK4|B3/J K1 | DIVMTQSPDSLAV SLGERATINC | KSS--- QNVLDISNNKN SLG | WFQQKPGQ PPKLLIN | W------- ASTRES | GVPDRFSGSGSG- TDFTLTISSLQTEDVAVYEC | QQYYN------------- | FGRGT KVEIK |
| iPS:436 402 | 21-225_213H1 2 | VK4|B3/J K1 | DIVMTQSPDSLAV SLGERATITC | KSS--- QNVLKTSNNRN YLA | WYQQKPGQ PPKVLIY | W------- ASTRES | GVPDRFSGSGSG- TDFTLTISSLQAEDVAVYYC | HQYYS-------------IPPT | FGQGT KVEIK |
| iPS:436 500 | 21-225_222H3 | VK4|B3/J K1 | DIVMTQSPDSLAV SLGERATINC | KSS--- QSVLRSSMHRN YLA | WYQQKPGQ PPQLLIY | W------- ASTRET | GVPDRFSGSGSG- TDFTLTISSLQAEDVSVYSC | QQYSS-------------IPWT | FGQGT KVEIN |
| iPS:436 520 | 21-225_223G1 0 | VK4|B3/J K1 | DIVMTQSPDSLAV SLGERATINC | KSS--- QSILLSSNNKN YLA | WHQQKPGQ PPKLLIY | W------- ASTRES | GVPDRFSGSGSG- TDFTLTISSLQAEDVAVYYC | LQYFS-------------TPWT | FGQGT KVEIK |
| iPS:436 544 | 21-225_224H5 | VK4|B3/J K1 | DIVMTQSPDSLAV SLGERATINC | KSS--- QSVLYSSNMFN YLT | WYQQKPGQ PPKLLIY | W------- ASTRES | GVPDRFSGSGSG- TDFTLTINSLQAEDVAVYYC | QQYYS-------------TPPT | FGQGT KVEIK |
| iPS:436 550 | 21-225_224D8 | VK4|B3/J K1 | DIVMTQSPDSLAV SLGERAAINC | KSS--- QNVLYSSNNRN YLA | WYQQKPGQ PPKLLIY | W------- SSTRKS | GVPDRFSGSGSG- TDFTLTISSLQAEDVAVYYC | QQYFS-------------TPPT | FGQGT KVEIK |
| iPS:436 574 | 21-225_225F5 | VK4|B3/J K1 | DIVMTQSPDSLAV SLGERATINC | KSS--- QNVLYNSNNNN YLA | WYQQKPGQ PPNLLIY | W------- ASTRES | GVPDRFSGSGSG- TDFTLTISSLQAEDVAVYYC | QQYYS-------------SPPT | FGQGT KVEIK |
| iPS:436 586 | 21-225_225F11 | VK4|B3/J K1 | DIVMTQSPDSLAV SLGERATINC | KSS--- QSVLYSSNNYN YLA | WYQQKPGQ PPKLLIY | W------- ASTRES | GVPDRFSGSGSG- PDFTLTISSLQAEDVAVYYC | QQYYT-------------TPPT | FGQGT KVEIK |
| iPS:436 600 | 21-225_226F6 | VK4|B3/J K1 | DIVMTQSPDSLAV SLGERATINC | KSS--- QSILYSSNNYN YLA | WYQQKPGQ PPKLLIY | W------- ASTRES | GVPDRFSGSGSG- TDFTLTISSLQAEDVAVYYC | QQYYT-------------TPPT | FGQGT KVEIK |
| iPS:436 616 | 21-225_226D1 1 | VK4|B3/J K1 | DIVMTQSPDSLAV SLGERATINC | KSS--- QNVLHSSNSNN YLV | WYQQKPGQ PFKLLIY | W------- ASTRES | GVPDRFSGSGSG- TDFTLTISSLQAEDVAVYYC | QQYYK-------------TPWT | FGQGT KVEIK |
| iPS:436 622 | 21-225_226A1 2 | VK4|B3/J K1 | DIVMTQSPDSLAV SLGERATINC | KSS--- QNVLYSSNNKN YLA | WYQQTPGQ PPKLLEY | W------- ASTRKS | GVPDRFSGSGSG- TDFTLTISSLQAEDVAVYYC | QQYYS-------------SPPT | FGQGT KVEIK |
| iPS:436 638 | 21-225_227C7 | VK4|B3/J K1 | DIVMTQSPDSLAV SLGERATINC | KSS--- QIVLSDSNNNN YLA | WYQQKPGQ PPNLLIY | W------- ASTRES | GVPDRFSGSGSG- TDFTLTISSLQAEDVAVYFC | QQYYS------------ | FGQGT KVEIK |
| iPS:437 356 | 21-225_74B1 | VK4|B3/J K1 | DIVMTQSPFLAV SLGERATINC | RSS--- QSVLHRSNNYN YLA | WYQQKPGQ PFKLLIY | W------- ASTRES | GVPDRFSGSGYG- TDFTLTISSLQAEDVAVYYC | QQYYT-------------TPPT | FGQGT KVEIK |
| iPS:437 361 | 21-225_74C1 | VK4|B3/J K1 | DIVMTQCPDSPAV SLGERASINC | KSS--- QSILHSSNNYN YLT | WYQQKPGH PHKLLIY | W------- ASTRES | GVPDRFSGSGSG- TDFTLTISSLQAEDVAVYYC | QQYYS-------------TPWT | FGQGT KVEIK |
| iPS:437 379 | 21-225_74H2 | VK4|B3/J K1 | DIVMTQSPDSLAV SLGERATINC | KSS--- QSVLHSSNNKN YLT | WYQQKPGQ PHKLLIY | W------- ASTRES | GVPDRFSGSGSG- TDFSLTIGSSLQAEDVAVYYC | QQYYS-------------IPPT | FGQGT KVEIK |
| iPS:446 094 | 21-225_77E1 | VK4|B3/J K1 | DIVMTQSPDSLAV SLGERATINC | KSS--- QTVLHSSNNYN YLA | WYQQKPGQ PPKVLIY | W------- TSTRES | GVHDRFSGSGSG- TDFTLTISSLQAEDVAVYYC | HQYLS-------------SPLT | FGQGT KVEIK |

Figure 51 (Continued)

| | | K FR1 | K CDR1 | K FR2 | K CDR2 | K FR3 | K CDR3 | K FR4 |
|---|---|---|---|---|---|---|---|---|
| iPS:451 116 | 21-225_164A4 | VK4|B3/J K1 | DIVMTQYPDSRAV SLGERATINC | KSS--- QSVLYSSNNKN YLT | WYQQKPGQ PPKLLFIY | W------ ASTRES | GVPDRFSGSGSG--- TDFTLTISSVQAEDVAVYYC | QQYFS--------- -------TPWT | FGQGT KVEIK |
| iPS:451 124 | 21-225_74F6 | VK4|B3/J K1 | DIVMTQSPDSLAV SLGERATINC | KSS--- QNLSSSNNKN YLT | WYQQKPGQ PPKLLIY | W------ TSTRES | GVPDRFSGSGFG--- TDFTLTISSLQAEDVAVYYC | QQYFS--------- -------VPLT | FGQGT KVEIK |
| iPS:451 127 | 21-225_164A7 | VK4|B3/J K1 | DIVMTQCPDSLAV SLGERATINC | KSS--- QSVLHSSNNNN YLA | WYQQKPGQ PHKLLIY | W------ TSTRES | GVPDRFSGSGYG--- TDFSLTIASLQAEDVAVYYC | QQYFS--------- -------IPLT | FGQGT KVEIK |
| iPS:451 129 | 21-225_94D2 | VK4|B3/J K1 | DIVMTQSPDSLAV SLGERATINC | KSS--- QSVLHSSNNKN YLT | WYQQKPGQ PHKLLIY | W------ ASTRES | GVPDRFSGSGSG--- TDFSLTIGSLQAEDVAVYYC | QQYHS--------- -------IPPT | FGHGT KVEIK |
| iPS:451 133 | 21-225_95H4 | VK4|B3/J K1 | DIVMTQCPDSLAV SLGERATINC | KSS--- QSVLFSSNNYN YLA | WYQQREPGQ PHNLLIY | W------ ASTRES | GVPDRFSGSGSG--- TDFTLTISSLQAADVAVYYC | QQHS---------- -------SPLT | FGQGT TVQIK |
| iPS:392 786 | 21-225_24E1 | VK4|B3/J K1 | DIVMTQSPDSLAV SLGERATINC | KSS--- QSVLYTSNNNN YLT | WYQQKPGQ RPNLLIY | W------ ASTRES | GVPDRFSGSGSG--- TDFTLTISSLQAEDVAVYYC | QQFYS--------- -------TPPT | FGQGT KVEIK |
| iPS:392 886 | 21-225_23A12 | VK4|B3/J K1 | DIVMTQSPDSLAV SLGERATINC | KSS--- QSVLYSSNNNN YLA | WYQQKPGQ PPKLLIY | W------ TSTRES | GVPDRFSGSGSG--- TDFTLTISSLRAEDVAVYYC | QQYD---------- -------TPPT | FGHGT KVEIK |
| iPS:392 928 | 21-225_25A4 | VK4|B3/J K1 | DIVMTQFPDSLAV SLGERATINC | KSS--- QTILHSSNNYN YLA | WYQQKPGQ PPKLLIY | W------ ASTRES | GVPDRFSGSGSG--- TDFTLTISSLBAEDVAVYYC | QQYYS--------- -------TPPT | FGQGT KVEIK |
| iPS:392 960 | 21-225_29E6 | VK4|B3/J K1 | DIVMTQFPDSLAV SLGERATINC | KSS--- QSVLYSSHNNY YLA | WYQQKPGQ PHKLLLY | W------ ASSRES | GVPDRFSGSGSG--- TEFTLTISSLQAEDVAVYYC | QQYYS--------- -------TPPT | FGQGT KVEIK |
| iPS:392 992 | 21-225_26C4 | VK4|B3/J K1 | DIVMTQSPDSLAV SLGERATINC | KSS--- QSVLYRSNNNY YLA | WYQHKPGQ PPKLLIY | W------ ASSLQS | GVPDRFSGSGSG--- TDFTLTISSLQAEDVAVYFC | QQYS---------- -------TPPT | FGQGT KVEFK |
| iPS:393 368 | 21-225_29H8 | VK4|B3/J K1 | DIVMTQSPDSLAV SLGERATINC | RSS--- QTILHSSNNYN YLA | WYQQKPGQ PPKLLIY | W------ ASTRES | GVPDRFSGSGSC--- TDFTLTISSLQAEDVAVYYC | QQYYC--------- -------TPPT | FGQGT KVEIK |
| iPS:393 942 | 21-225_11E5 | VK4|B3/J K1 | DIVMTQSPDSLAV SLGERATINC | KSS--- QSVLYSSNNNY YLA | WYQQKPGQ RPKLLIY | W------ ASTRES | GVPSRFSGSGSG--- TNFTLTISSLQAEDVAVYYC | QQYYS--------- -------TPPT | FGQGT KVEIK |
| iPS:398 506 | 21-225_23G12 | VK4|B3/J K1 | DIVMTQSPDSLAV SLGERATINC | KSS--- QSILFSSNNNN YLA | WYQQKPGQ PPKLLIY | W------ ASTRES | GVPDRFSGSGSG--- TDFTLTISSLQAEDVAVYFC | QQYSS--------- -------TPWT | FGQGT KVEIK |
| | Germline | | K FR1 | K CDR1 | K FR2 | K CDR2 | K FR3 | K CDR3 | K FR4 |
| VK1|A30/JK 2 | | | | | | | | | |
| iPS:426 114 | 21-225_28H2 | VK1|A30/ JK2 | DIQMTQSPSSLSA SIGDRVTIIC | RAS--QGIR- ----NDLG | WYQQKPGK APKRLIY | A------ ASSLQS | GVPSRFSGSGSG--- TEFTLTISSLQPEDFATYYC | LQHYS--------- -------YPRS | FGQGT KLEIK |
| iPS:426 116 | 21-225_29E2 | VK1|A30/ JK2 | DIQMTQSPSSLSA SVGDRVTITC | RAS--QAIR- ----NDLG | WYQQRPGK APKRLIY | A------ ASSLQS | GVPSRFSGSGSG--- TEFTLTISSLQPEDFATYYC | LQHYN--------- -------YPRS | FGQGT KLEIK |
| iPS:434 231 | 21-225_61F2 | VK1|A30/ JK2 | DIQMTQSPSSLSA SVGDRVTYTC | RAS--QGIR- ----DDLG | WYQQKPGK APERLIY | A------ ASSLQS | GVPSRFSGSGSG--- TEFTLTISSLQPEDFATYYC | LQHYS--------- -------YPRS | FGQGT KLEIK |

Figure 51 (Continued)

| ID | Name | V/J | K_FR1 | K_CDR1 | K_FR2 | K_CDR2 | K_FR3 | K_CDR3 | K_FR4 |
|---|---|---|---|---|---|---|---|---|---|
| iPS:435 401 | 21-225_150E2 | VK1|A30/ JK2 | DIQMTQSPSSLSA SVGDRVTISC | RAS--QGIG------NDLG | WYQQKPGK APTRLIY | A------ASSLQS | GVPSRFSGSGSG--TEFTLTISSLQPADFATYYC | LQHYS---------FPYS | FGQGT KLEIK |
| iPS:435 445 | 21-225_152F7 | VK1|A30/ JK2 | DIQMTQSPSSLSA SVGDRVTITC | RAS--QGIR------NDLG | WYQQKPGK APKRLIY | A------TSSLQS | GVPTLTISSLQPEDFATYYC | LQHYN---------FPYS | FGQGT RLEIK |
| iPS:435 763 | 21-225_176H1 | VK1|A30/ JK2 | DIQMTQSPSSLSA SVGDRVTITC | RAS--QGIR------NDLG | WYQQKPGK APNRLIY | A------ASSLQS | GVPSRFSGSGSG--TEFTLTISSLQREDFATYYC | LQHNS---------YPRS | FGQGT KLEIK |
| iPS:435 767 | 21-225_177B4 | VK1|A30/ JK2 | DIQMTQSPSSLSA SVGDRVTITC | RAS--QGIR------NDLG | WYQQKPGK APKRLIY | A------ASSLQS | GVPSRFSGSGSG--TEFTLTISSLQPEDFATYYC | LQHYS---------FPRS | FGQGT KLEIK |
| iPS:392 974 | 21-225_26A11 | VK1|A30/ JK2 | DIQMTQSPISLSA SVGDRVTITC | RAS--QAIR------NDLG | WYQQRPGK APKRLIY | A------ASSLQS | GVPSRFSGSGSG--TEFTLTISSLQPEDFATYYC | LQHYN---------YPRS | FGQGT KLEIK |
| iPS:393 046 | 21-225_25A12 | VK1|A30/ JK2 | DIQMTQSPSSLSA SVGDRVTVTC | RAS--QAIR------DDLG | WYQQKPGK APKRLIY | A------ASSLQS | GVPSRFSGSGSG--TEFTLTISSLQREDFATYYC | LQHYN---------YPRS | FGQGT KLEIK |
| | Germline | VK1|O12/JK4 | | | | | | | |
| iPS:426 118 | 21-225_7A10 | VK1|O12/ JK4 | DIQMTQSPSSLSA SVGDRVTITC | RAS--QNIY------SYLN | WYQQKPGE APKLVIY | S------TSSLQS | GVPSRFSGSGSG--TDFSLTISNLQPEDFSTYYC | QQSYS---------PPLT | FGGGT KVEIR |
| iPS:426 124 | 21-225_32D6 | VK1|O12/ JK4 | DIQMTQSPSSLST SVGDRITITC | RAS--QNII------SYLN | WYQQKPGK APKLLMY | V------ASRLQS | GVPSRFSGSGSG--TDFTLTISSLQAEDFATYYC | QQSYS---------TPYT | FGGGT KVAIK |
| iPS:451 135 | 21-225_64A11 | VK1|O12/ JK4 | DIQMTQSPFSLSA SVGDRVTITC | RAS--RSVS------RYLN | WYQQTLGK ALKLLIS | V------ASRLQS | GVPSRFSGSGSG--TDFTLTISSVQREDFATYYC | QQSDS---------FPLT | FGGGT KVEIK |
| iPS:434 011 | 21-225_48B10 | VK1|O12/ JK4 | DIQMTQSPSSLSA SVGDRVTITC | RAS--QSII------KYLN | WYQKTPGK APKLLIY | A------ASSLQS | GVPSRFSGSGSG--TDFTLTISSVQPEDFATYYC | QQTYS---------NPLT | FGGGT KVEFT |
| iPS:434 015 | 21-225_48F12 | VK1|O12/ JK4 | DIQMTQSPSSLSA SVGDRVTITC | RAS--QSIR------KYLN | WYQKTPGK APKLLIY | A------ASSLQS | GVPSRFSGSGSG--TDFTLTISSVQPEDFATYYC | QQTYS---------NPLT | FGGGT EVEIT |
| iPS:434 017 | 21-225_48G12 | VK1|O12/ JK4 | DIQMTQSPSSLSA SVGDRVTITC | RAS--QSIR------KYLN | WYQKTPGK APKLLIY | A------ASSLQS | GVPSRFSGSGSG--TDFTLTISSVQPEDFATYYC | QQTYS---------NPLT | FGGGT EVEIT |
| iPS:434 165 | 21-225_50F2 | VK1|O12/ JK4 | DIQMTQSPSSLSA SVGDRVTITC | RAS--QSIL------SYLN | WYQQKPGK APKLLIY | V------ASSFQS | GVPSRFSGSGSG--TDFTLTISSLQPDDFATYYC | QQSYS---------TPYT | FGGGT KVEIK |
| iPS:434 191 | 21-225_56B6 | VK1|O12/ JK4 | DIQMTQSPSSLSV SVGDRVTITC | RAS--QSIF------RYLN | WYQQTLGK APKLLIF | A------ASSFQS | GVPSRFSGSGSG--TDFTLTISSLQPDDFATYYC | QQTYS---------FPLT | FGGGT KVEIK |
| iPS:434 247 | 21-225_62D2 | VK1|O12/ JK4 | DIQMTQSPSSLSA SVGDRVTITC | RAS--QSII------SYLN | WYQQKPGK APKLLIY | A------TSSLQS | GVPSRFSGSGSG--TDFTLTISSLQPEDFATYYC | QQTYS---------PPLT | FGGGT KVEIK |
| iPS:434 335 | 21-225_63C10 | VK1|O12/ JK4 | DIQMTQSFSSLST SVGDRVTITC | RAS--QSIF------SYLH | WYQQKPGK APKLLIS | A------ASSLQS | GVPSRFSGSGSG--TDFTLTISSLQPEDFATYYC | QQTYS---------PPLT | FGGGT KVEIK |
| iPS:434 341 | 21-225_64F7 | VK1|O12/ JK4 | DIQMTQSPSSLSA SVGDRVTITC | RAS--QNIK------KYLN | WYQQKPGK APKFLIY | G------ASSLQS | GVPSRFSGSGSG--TDFTLTISSLQPEDFAAYYC | QQSYN---------ISFT | FGGGT KVELK |
| iPS:435 295 | 21-225_146H1 | VK1|O12/ JK4 | DIQMTQSPSSLSA SVGDRVTITC | RAS--QSIS------SYLN | WYQLKPGK APKVLIY | T------TSSLQS | GVPSRFSGSGSG--TDFTLTISSLQPEDFATYYC | QQSY----------STPT | FGGGT KVEIK |
| iPS:435 307 | 21-225_146E9 | VK1|O12/ JK4 | DIQMTQSPSSLSA SVGDRVTITC | RAS--QSIS------DYLN | WYQLKPGK APKVLIY | T------ASSLQS | GVPSRFSGSGSG--TDFTLTISSLQPEDFATYFC | QQSY----------STPT | FGGGT KVEIK |
| iPS:435 347 | 21-225_148C4 | VK1|O12/ JK4 | DIQMTQSPSSLSA SVGDRVTITC | RAS--QSII------DYLN | WYQLKPGK APKVLIY | T------ASSLQS | GVPSRFSGSGSG--TDFTLTISSLQPEDFTTYYC | QQSY----------STPT | FGGGT KVEIE |
| iPS:435 355 | 21-225_148H9 | VK1|O12/ JK4 | DIQMTQSPSSLSA SVGDRVTITC | RAS--QSIS------NYLN | WYQQKPGK APKVLIY | I------ASSLQS | GVPSRFSGSGSG--TDFTLTISSLQPEDFATYYC | QQSY----------STPT | FGGGT KVEIK |

Figure 51 (Continued)

| | | | | | | | | |
|---|---|---|---|---|---|---|---|---|
| iPS:435_371 | 21-225_149A3 | VK1\|O12/JK4 | DIQMTQSPSSLSA SVGDRVTITC | RAS--QSIS----SYLN | WYQQKPGK APKVMIY | T------ ASSLQS | GVPSRFSGSGSG-- TDFTLTINSSLQPEDFATYYC | QQSY-------STPT | FGGGT KVEIK |
| iPS:435_415 | 21-225_150C1 | VK1\|O12/JK4 | DIQMTQSPSSLSA SVGDRVTITC | RAS--QSIS-------SYLN | WYQQKPGK APKLLIY | T------ ASSLQS | GVPSRFSGSGSG-- IDFTLTISSLQPEDFATYYC | QQSY-------SIYT | FGGGS KVEIK |
| iPS:435_419 | 21-225_150C1_2 | VK1\|O12/JK4 | DIQMTQSPSSLSA SVGDRVTITC | RAS--QSIS-----DYLN | WYQQKPGK APKVLIY | T------ TSSLQS | GVPSRFSGSGSG-- IDFTLTISSLQPEDFATYYC | QQSF-------STPT | FGGGT KVEIK |
| iPS:435_425 | 21-225_151B1 | VK1\|O12/JK4 | DIQMTQSPSSLSA SVGDRVTITC | RAS--QSIS----NFLN | WYQQKPGK APKVLIY | T------ ASSLES | GVPSRFSGSESG-- IDFTLTISSLQPEDFATYYC | QQSY-------STPT | FGGGT KVEIK |
| iPS:435_431 | 21-225_152D2 | VK1\|O12/JK4 | DIQMTLSPSSLSA SVGDRVTITC | RAS--QSIS-----DYLN | WYQLKPGK APKVLIY | T------ TSSLQS | GVPSRFSGSGSG-- IDFTLTISSLQPEDFATYFC | QQSY-------STPT | FGGGT KVEIK |
| iPS:435_439 | 21-225_152G4 | VK1\|O12/JK4 | DIQMTQSPSSLSA SVGDRVTITC | RAS--QSIS-----DYLN | WYQQKPGK APKVLIY | T------ TSSLQS | GVPSRFSGSGSG-- IDFTLTISSLQPEDFATYYC | QQSY-------STPT | FGGGT KVEIK |
| iPS:435_455 | 21-225_152B1 | VK1\|O12/JK4 | DIQMTQSPSSLSA SVGDRVTITC | RAS--QSIS-----DYLN | WYQQKPGK APKVLIY | T------ TSSLQS | GVPSRFSGSGSG-- IDFTLTISSLQPEDFATYYC | QQSY-------STPT | FGGGT KVEIK |
| iPS:435_487 | 21-225_155C4 | VK1\|O12/JK4 | DIQMTQSPSSLSA SVGDRVTITC | RAS--QSIS-------SYLN | WYQLKPGK APKVLIF | T------ ASSLQS | GVPSRFSGSGSG-- IDFTLTISSLQPEDFATYYC | QQSY-------STPT | FGGGT RVEIK |
| iPS:435_503 | 21-225_156E4 | VK1\|O12/JK4 | DIQMTQSPSSLSA SVGDRVTITC | RAS--QSIS-------SYLN | WYQQKPGK APKVLIY | T------ ASSLQS | GVPSRFSGSGSG-- IDFTLTISSLQPEDFATYYC | QQSY-------SAPT | FGGGT KVEIK |
| iPS:435_563 | 21-225_159H2 | VK1\|O12/JK4 | DIQLTQSPSSLSA SVGDRVTITC | RAS--QSIS----KYLN | WYQQKPGK APELLIY | A------ TSNLQS | GVPSRFSGSGSG-- IDFTLTISLQPEDFVTYYC | QQSY-------LPVT | FGGGT KVEIK |
| iPS:436_110 | 21-225_196F4 | VK1\|O12/JK4 | DFQMTQSPSSLSA SVGDRVTITC | RAS--QRIH----SYLN | WYQQKPGK APKLLIY | T------ ASSLQG | GVPSRFSGSGSG-- IDFTLTISSLQPEDFATYYC | QQSYG------SPLT | FGGGT KVEIK |
| iPS:436_244 | 21-225_201H10 | VK1\|O12/JK4 | DIQMTQSPSSLSA SVGDRVTITC | RAS--HNIN----SYLN | WYQQKSGK APKLLIY | A------ ASSLQS | GVPSRFSGSGSG-- IDFTLTFSSLQPEDFATYYC | QQSYS------FPLT | FGGGT KVEMR |
| iPS:436_262 | 21-225_203E3 | VK1\|O12/JK4 | DIQMTQSPSPSA SVGDRVTITR | RAS--HNIN----SYLN | WYQQKSGK APKLLIY | A------ ASSLQS | GVPSRFSGSGSG-- IDFTLTFSSLQPEDFATYYC | QQSYS------FPLT | FGGGT KVEMR |
| iPS:436_276 | 21-225_204H4 | VK1\|O12/JK4 | DIQMTLSPSSPSA FVGDRVTITR | RAS--HNIN-------SYLN | WYQQKSGK APKLLIY | A------ ASSLQS | GVPSRFSGSGSG-- IDFTLTFSSLQPEDFATYYC | QQSYS------FPLT | FGGGT KVEMR |
| iPS:436_280 | 21-225_204D6 | VK1\|O12/JK4 | DSQMTQSPSSLSA SVGDRVTITC | RAS--ESVH----TYLN | WYQQKPGK APKVLIY | G------ ASSLQR | GVPSRFSGSGSG-- IDFTLTISSLQPEDFVTYYC | QQSY-------SPLT | FGGGT KVEIQ |
| iPS:436_312 | 21-225_206A4 | VK1\|O12/JK4 | DIQMTLSFSSPSA SVGDRVTITR | RAS--HNIN-------SYLN | WYQQKSGK APKLLIC | A------ ASSLQS | GVPSRFSGSGSG-- IDFTLTFSSLQPEDFATYYC | QQSYS------FPLT | FGGGT KVEMR |
| iPS:436_316 | 21-225_206A5 | VK1\|O12/JK4 | DIQMTQSPSSPSA FVGDRVTITR | RAS--HNIN-------SYLN | WYQQKSGK APKLLIY | A------ ASSLQS | GVPSRFSGSGSG-- IDFTLTFSSLQPEDFATYYC | QQSYS------FPLT | FGGGT KVEMR |
| iPS:436_338 | 21-225_208E8 | VK1\|O12/JK4 | DIQMTLSFSSPSA SVGDRVTITR | RAS--HNIN----SYLN | WYQQKSGK APKLLIC | A------ ASSLQS | GVPSRFSGSGSG-- IDFTLTFSSLQPEDFATYYC | QQSYS------FPLT | FGGGT KVEMR |
| iPS:436_344 | 21-225_208B1 | VK1\|O12/JK4 | DIQMTQSPSSLSA SVGDRVTITC | RAS--HNIN----SYLN | WYQQKSGK APKLLIY | A------ ASSLQS | GVPSRFSGSGSG-- IDFTLTFSSLQPEDFATYYC | QQSYS------FPLT | FGGGT KVEMR |
| iPS:436_358 | 21-225_210D1 | VK1\|O12/JK4 | DIQMTQSPSSLSA SVGDRVTITC | RAS--HNIN----SYLN | WYQQKSGK APKLLIY | A------ ASSLQS | GVPSRFSGSGSG-- IDFTLTFSSLQPEDFATYYC | QQSYS------FPLT | FGGGT KVEMR |

| | | | K_FR1 | K_CDR1 | K_FR2 | K_CDR2 | K_FR3 | K_CDR3 | K_FR4 |
|---|---|---|---|---|---|---|---|---|---|
| iPS:393930 | 21-225_7E11 | VK1IO12/JK4 | DIQMTQSPSSLSASVGDRVTIAC | RAS--QNII----SYEN | WYQQKPGKAPKFLIY | T------ASSLQS | GVPSRFSGSGSG--TDFTLTISSLQPEDEATYYC | QQTYS-------TPLT | FGGGTKVEIK |
| iPS:393932 | 21-225_10F5 | VK1IO12/JK4 | DIQMTQSPSSLSASVGDRVTITC | RAS--QNIY----RYLN | WYQEKPGRAPKLLIY | T------ASSLQS | GVSDRFSGSRFSGSDSG--TDFTLTISSLQPEDFATYYC | QQSYS-------FPLT | FGGGTKVEIK |
| iPS:393964 | 21-225_6G1 | VK1IO12/JK4 | DIQMTQSPSSLSASVGDRVTITC | RTS--QNII----SYEN | WYQQKPGKAPKVLIY | T------ASNLQT | GVPSGFSGSGSG--TDFTLTISSLQPEDEATYYC | QQPHS-------PPLT | FGGGTKVEIK |
| iPS:394012 | 21-225_15A3 | VK1IO12/JK4 | DIQMTQSPSSLSASVGDRVTITC | RAS--QSII----SYLN | WYLQKPGKAPKFLIY | T------ASSLQS | GVPSRFSGSGSG--TDFTLTISSLQPEDEATYYC | QQTYS-------TPLT | FGGGTKVEIK |
| iPS:394016 | 21-225_13D4 | VK1IO12/JK4 | DLQMTQSPSSLSASVGDRVTITC | RAS--QSIF----SYLN | WYQQKPGKAPKLLIC | T------ASSLQN | GVPSRFSGSGSG--TDFTLTISSLQPEDFATYYC | QQTYS-------LPLT | FGGGTKVEIK |
| iPS:394083 | 21-225_16E6 | VK1IO12/JK4 | DIQMTQSPSSLSASVGDRVTITC | RAS--QSII----SYLN | WYQQKPGKAPKFLIY | T------TSSLQS | GVPSRFSGSGSG--TDFTLTISSLQPEDFATYYC | QQTYS-------TPLT | FGGGTKVEIK |
| iPS:398480 | 21-225_17G4 | VK1IO12/JK4 | DIQMTQSPSSLSASAGDRVTITC | RTS--QNIS----NYLN | WYQQKPGKAPKLLIY | V------ASSFPS | TEFTLTISSLQPEDFATYYC | QQSNF-------FPLT | FGGGTKVEII |
| iPS:398486 | 21-225_19A1 | VK1IO12/JK4 | DIQMTQSPSSLSASVGDRVTITC | RAS--HTIT----SYIN | WYQQKPGKAPKFLIY | A------TSNLQS | GVPSRFSGSGSG--TDFTLTISSLQPEDFATYYC | QQSYN-------FPLT | FGGGTKVEIK |
| Germline | VK2IA18/JK4 | | DIVMTQTPLSLSVTPGQPASISC | KSS----QSLLHSD-GKTYLY | WYLQKPGQPPQLLIY | E------VSNRFS | GVSDRFSGSGSG--TDFTLKISRVEAEDVGVYYC | MQSIH-------LPLT | FGGGTKVEIK |
| iPS:451139 | 21-225_71A6 | VK2IA18/JK4 | DIVMTQTPLSLSVTPGQPASISC | KSS----QSLLHSD-GKTHLY | WYLQKPGQPPQLLIY | E------VSNRFS | GVSDRFSGSGSG--TDFTLKISRVEAEDVGVYYC | MQSKQ-------LPLT | FGGGTKVEFK |
| iPS:433937 | 21-225_44B10 | VK2IA18/JK4 | HIVMTQTPLSLSVTPGQPASISC | KSS----QSLLHSE-GRTYLY | WYLQKPGQPPQLLIY | E------ISHRFS | GVPDRFSGSGSG--TDFTLKISRVEAEDVGVYYC | MQSIH-------LPFT | FGGGTKVEIK |
| iPS:433979 | 21-225_46B9 | VK2IA18/JK4 | DIVMTQTPLSLSVTPGQPASISC | KSS----QSLLHSE-GKTYLY | WYLQKPGQPPQLLIY | E------VSYRFS | GVPDRFSGSGSG--TDFTLKISRMEAEDVGVYYC | MHSIQ-------YPLT | FGGGTKVEIQ |
| iPS:434201 | 21-225_59A12 | VK2IA18/JK4 | DIVMTQTPLSLSVTPGQPASISC | KSS----QSLQHGE-GKTYLY | WYVQKPGQPPQLLIY | E------VSYRFS | GVPDRFSGSGSG--TDFTLKISRVEVEDVGVYYC | MQSIQ-------LPLT | FGGGTKVEIK |
| iPS:434205 | 21-225_60G2 | VK2IA18/JK4 | DIVMTQTPLSLSVTPGQPASISC | KSS----QSLLHSE-GKTYLY | WYLQKPGQPPQLLIY | E------VSNRFS | GVPDRFSGSGSG--TDFTLKISRVEAEDVGVYYC | MQSIQ-------LPLT | FGGGTKVEIK |
| iPS:434223 | 21-225_60C12 | VK2IA18/JK4 | DIVMTQTPLSLSVTPGQPASISC | KSS----QSLLHSE-GKIYLY | WYLQKPGQPPQFLIY | E------VSNRFS | GVPDRFSGSGSG--TDFTLKISRVEAEDVG-YYC | MQSIK-------YPLT | FGGGTKVEIK |
| iPS:434233 | 21-225_61B3 | VK2IA18/JK4 | DIVMTQTPLSLSVTPGQPASISC | KSS----QSLLHSE-GKTYLY | WYLQKPGQPPQLLIY | E------VSNRIS | GVPDRFSGSGSG--TDFTLKISRVEAEDVGVYYC | MQSIQ-------LPLT | FGGGTKVEIK |
| iPS:434303 | 21-225_58H11 | VK2IA18/JK4 | DIVMTQTPLSLSVTPGQPASISC | KSS----QSLLHSE-GKTYLY | WYVQKPGQPPQLLIY | E------VSYRFS | GVPDRFSGSGSG--TDFTLKISRVEAEDVGVYYC | MQSIQ-------LPLT | FGGGTKVEIK |
| iPS:435349 | 21-225_148F5 | VK2IA18/JK4 | DIVMTQTPLSLSVTPGQPASISC | KSS----QSLLHSE-GKTYLY | WYLQKPGQPPQLLIY | E------VSYRVS | GVPDRFSGSGSG--TDFTLKISRVEAEDVGVYFC | MQSIQ-------LPLT | FGGGTKVEIK |

Figure 51 (Continued)

| ID | V/J | K_FR1 | K_CDR1 | K_FR2 | K_CDR2 | K_FR3 | K_CDR3 | K_FR4 |
|---|---|---|---|---|---|---|---|---|
| iPS:435_359 | VK2\|A18/JK4 | DIVMTQTPLSLSV TPGQPASISC | KSS---QSLLHSE-GKTYLY | WYLQKPGQ PPQLLIY | E------VSYRVS | GVPDRFSGSGSG-TDFTLKISRVEAEDVGVYYC | MQSIQ-------LPLT | FGGGT KVEIK |
| iPS:435_417 | VK2\|A18/JK4 | DIVMTQTPLSLSV TPGQPASISC | KSS---QSLLHSE-GKTYLY | WYLQKPGQ PPQLLIY | E------VSYRFS | GVPDRFSGSGSG-TDFTLKISRVEAEDVGVYYC | MQGIQ-------LPLI | FGGGT KVEIK |
| iPS:435_469 | VK2\|A18/JK4 | DIVMTQTFPSLSV TPGQPASISC | KSS---QSLLHSD-GKTYLY | WYLQKPGQ PPQFLIY | E------VSNRFS | GVPDRFSGSGSG-TDFTLKISRVEADDVGVYYC | MQNIK-------YPLI | FGGGT KVEIK |
| iPS:435_733 | VK2\|A18/JK4 | DIVMTQTPLSLSV TPGQPASISC | KSS---QSLLHSE-GKTYLY | WYLQKPGQ PPQLLIY | E------VSHRFS | GVPDRFSGSGSG-TDFTLKISRVEAEDVGVYYC | MQSI--------QLLT | FGGGT KVEIK |
| iPS:435_785 | VK2\|A18/JK4 | DIVMTQTPLSLSV TPGQPASISC | KSS---QSLLHSE-GKTYLY | WYLQKPGQ PPQLLIY | E------VSHRFS | GVPDRFSGSGSG-TDFTLKISRVEAEDVGVYYC | MQSI--------QVLT | FGGGT KVEIK |
| iPS:392_618 | VK2\|A18/JK4 | DIVMTQTPLSLSV IPGQPASISC | KSS---QSLLHSD-GKTHLN | WYLQKPGQ PPQLLIY | E------VSYRFS | GVPDRFSGSGSG-TVFTLEISRVEAEDVGVYYC | FQSIQ-------LPLI | FGGGT KVEIK |
| iPS:392_860 | VK2\|A18/JK4 | DIVMTQTPLSLSV TPGQPASISC | KSS---QSLLHSE-GKTYLY | WYLQKPGH PPQLLIY | E------VSNRFS | GVPDRFSGSGSG-TDFTLKISRVEAEDVGIYYC | MQSIQ-------LPLS | FGGGT KVEIN |
| iPS:392_888 | VK2\|A18/JK4 | DIVMNQTPLSLSV TPGQPASISC | KSS---QSLLHSD-GKTYLY | WYLQKPGQ PPQLLIY | E------ISNRFS | GVPARLSGSGSG-TDFTLKISRVEAEDVGVYYC | MQSTQ-------FPLI | FGGGT KVEIK |
| iPS:392_938 | VK2\|A18/JK4 | DIVMTQTPLSLSV TPGQPASFSC | KSS---QSLLHSE-GKTYLY | WYLQKPGQ PPQLLIF | E------VSHRFS | GLPDRFSGSGSG-TDFTLKISRVEAEDVGVYYC | MQSIQ-------HPFI | FGGGT RVEIK |
| iPS:392_994 | VK2\|A18/JK4 | DIVMTQTPLSLSV TPGQPASISC | KSS---QTLLHGE-GKTFLY | WYLQKPGQ PPMLLIY | E------VSNRFS | GVPDRFSGSGSG-TDFTLKISRVEAEDVGIYYC | MQSIK-------LPLI | FGGGT KVEIK |
| iPS:393_012 | VK2\|A18/JK4 | DILMTQTPLSLSV TPGQPASISC | KSS---QSLLHSE-GKTYLY | WYLQKPGQ PPQFLIY | E------VSHRLS | GVPDRFSGSGSG-TDFTLKISRVEAEDVGVYYC | MQSIQ-------LPLI | FGGGT KVEIK |
| iPS:393_144 | VK2\|A18/JK4 | DIVMTQTPLSLSV TPGQPASISC | KSS---QSLLHSD-GKTYLY | WYLQKPGQ PPQLLIY | E------VSNRFS | GVPDRFSGSGSG-TDFTLKISRVEAEDVGVYYC | MQSK--------QLPF | FGGGT KVEIR |
| Germline | | K_FR1 | K_CDR1 | K_FR2 | K_CDR2 | K_FR3 | K_CDR3 | K_FR4 |
| VK1\|L1/JK3 | | | | | | | | |
| iPS:451_143 | VK1\|L1/JK3 | DIQMTQFPSSLFA FVGDRVTITC | PAS--QGIS-----NYLA | WFQQKPGK APKSLIY | G------AFNLHS | GVPSKFSGSGFG-TDFTLTINSLQPEDFANYYC | QQYSC-------YPFT | FGHGT KVDIK |
| iPS:468_814 | VK1\|L1/JK3 | DIQMTQSPSSLSA SVGDRVTITC | RAS--QGIS-----NYLA | WFQQKPGK APKSLIY | A------ASTLQS | GVPSKFSGSRSG-TDFNITISMLQPEDFATYYC | QQYSG-------YPFT | FGPGT KVDTK |
| iPS:433_901 | VK1\|L1/JK3 | DIQMTQSPSSLSA SVGDRVTITC | RAS--QGIN-----NYLA | WFQQKPGK APKSLIN | A------ASSLQS | GVPSRFSGSGSG-TDFTLAISSLQPEDFATYYC | QQYYS-------YPFT | FGPGT KVDIK |
| iPS:433_961 | VK1\|L1/JK3 | DIQMTQSPSSLSA SVGDRVTITC | RAS--QGIN-----NYLA | WFQQKPGK APKSLIN | A------ASSLQS | GVPSRFSGSGSG-TDFTLAISSLQPEDFATYYC | QHYYS-------YPFT | FGRGT KVDIK |

Figure 51 (Continued)

| | | | | | | | | | |
|---|---|---|---|---|---|---|---|---|---|
| iPS:434 059 | 21- 225_51C5 | VK1|L1/J K3 | DIQMTQSPSSLSA SVGDRVTITC | RAS--QGIS- ----NYLA | WFQQKPGK APKSLIY | A------ ASSLRS | GVPSQFSGSGSG- TDFTLTISSLQPEDFATYYC | QQYYS------ --------YPFT | FGPGT KVDIK |
| iPS:434 085 | 21- 225_52E3 | VK1|L1/J K3 | DIQMTQSPSSLSA SVGDRVTITC | RAS--QGIS- ----NYLA | WFQQKPGK APKSLIN | A------ ASSLQS | GVPSKFSGSGSG- TDFTLTISSLQPEDFATYYC | QQYNS------ --------FPFT | FGPGT KVDIK |
| iPS:434 115 | 21- 225_53E4 | VK1|L1/J K3 | DIQMTQSPSSLSA SVGDRVTITC | RAS--QVIS- ----NYLA | WFQQKPGK APKSLIS | A------ ASSLQS | GVPSKFSGSGSG- TDFTLTISSLQPEDFATYYC | QQYHS------ --------YPLT | FGRGT KVDIK |
| iPS:434 213 | 21- 225_60A4 | VK1|L1/J K3 | DIQMTQSPSSLSA SVGDRVTITC | RAS--QGIS- ----NYLA | WFQQKPGK APKSLIY | A------ ASSLQS | GVPSKFSGSGSG- TDFTLTISSLQSEDFATYYC | QQYKS------ --------EPFT | FGPGT KVDIK |
| iPS:434 215 | 21- 225_60F7 | VK1|L1/J K3 | DIQMTQSPSSLSA SVGDRVTISC | RAS--QVIK- ----NYLV | WVQQKPGK APKSLIY | A------ ASSLQS | GVPSTFSGSGSG- TDFTLTISSLQPEDFATYYC | LQPHS------ --------YPFT | FGPGT KMDIK |
| iPS:434 261 | 21- 225_56F7 | VK1|L1/J K3 | DILMTQSPSSLSA SVGDRVTITC | RAS--QGIS- ----TYLA | WFQQTPGT APKSLIY | A------ ASSLQG | GVPSKFSGSGSG- TDFTLTISSLQPEDFATYYC | HQYNS------ --------EPFK | FGRGT KVDIT |
| iPS:434 331 | 21- 225_63H8 | VK1|L1/J K3 | DIQMTQSPSSLSA SVGDRVTITC | RAS--QGIS- ----NYLA | WFQQKPGK AHKSLIY | A------ ASSLQS | GVPSKFSGSGSG- TDFTLTISSLQPEDFATYYC | QQYHS------ --------YPFT | FGPGT KVDIR |
| iPS:434 361 | 21- 225_65D5 | VK1|L1/J K3 | DIQMTQSPSSLSA SVGDRVTITC | RAS--QDIN- ----NYLA | WFQQKPGK APKSLIY | A------ ASSLHS | GVPSQFSASGSG- SDFTLTISSLQPEDFATYYC | PLYKS------ --------YPLT | FGPGT KVDIK |
| iPS:434 405 | 21- 225_68E6 | VK1|L1/J K3 | DIQMTQSPSSLSA SVGDRVTITC | RAS--QGIS- ----YYLA | WFQQKPGK APKSLIY | V------ ASSLQS | GVPSRFSGSGSG- TDFTLTISSLQPEDFATYYC | QQYDS------ --------YPFT | FGPGT KVDIK |
| iPS:435 259 | 21- 225_96C6 | VK1|L1/J K3 | DIQMTQSPSSLSA SVGDRVTITC | RAS--QGIS- ----NYLA | WFQQKPGK APKSLIY | A------ ASSLQS | GVPSKFSGSGSG- TDFTLTINSLQPEDFATYYC | HQYND------ --------YPFT | FGPGT KVDIR |
| iPS:435 351 | 21- 225_148B6 | VK1|L1/J K3 | DIQMTQSPSSLSA SVGDRVSITC | RAS--QGIS- ----KYLA | WFQQKPGK APKSLIF | A------ ASSLQS | GVPSNFSGSGSG- TDFTLTISSLQPEDFATYYC | QQYNS------ --------FPFT | FGPGT KVDFK |
| iPS:435 461 | 21- 225_153A1 | VK1|L1/J K3 | DIQMTQSPSSLSA SVGDRVTITC | RAS--QVIS- ----NYLA | WFQQKPGK APKSLIS | A------ ASSLQS | GVPSKFSGSGSG- TDFTLTISSLQPEDFATYYC | QQYHS------ --------YPFT | FGPGT KVDIK |
| iPS:435 509 | 21- 225_157H1 | VK1|L1/J K3 | DIQMTQSPSSLSA SVGDRVTITC | RAS--QDIS- ----NYLV | WFQQRPGK APRSLIY | A------ ASSLQS | GVPSKFSGSGSG- TDFTLTISSLQPEDFATYYC | QQYNS------ --------YPFT | FGPGT KVDIK |
| iPS:435 515 | 21- 225_157E4 | VK1|L1/J K3 | DIQMTQSPSSLSA SVGDRVTFTC | RAS--QDIS- ----NYLA | WFQQKPGK APKSLIY | A------ ASSLRS | GVPSQFSGSGSG- TDFTLTINSLQPEDFATYYC | QQYHS------ --------YPFT | FGPGT KVDIK |
| iPS:435 523 | 21- 225_157G5 | VK1|L1/J K3 | DIQMTQSPSSLSA SVGDRVTITC | RAS--QGIN- ----NYLA | WFQQKPGK APESLIY | A------ ASSLRS | GVPSQFSGSGSG- TDFTLTISSLQPEDFATYYC | QQYNS------ --------YPFT | FGPGT KVDIK |
| iPS:435 535 | 21- 225_157H1 | VK1|L1/J K3 | DIQMTQSPSSLSA SVGDRVTITC | RAS--QGIT- ----NYLA | WFQQKPGK APTSLIY | T------ ASNLQS | GVPSKFSGSGSG- TDFTLTISNLQPEDFATYYC | QQYHS------ --------YPFT | FGPGT KVDIK |
| iPS:435 559 | 21- 225_158H1 2 | VK1|L1/J K3 | DIQMTQSPSSLSA SVGDRVTITC | RAS--QGIN- ----NYLA | WFQQKPGK APKSLIS | A------ ASSLQS | GVPSKFSGSGSG- TDFTLTISSLQPEDFATYYC | QQYNS------ --------YPFT | FGPGT KVDIK |
| iPS:435 575 | 21- 225_159H1 1 | VK1|L1/J K3 | DIQMTQSPSSLSA SVGDRVTITC | RAS--QDIS- ----KYLV | WFQQKPGK APKSLIY | A------ ASSLQS | GVPSKFSGSGSG- TDFTLTISSLQPEDFATYYC | QQYHS------ --------YPFT | FGPGT KVDIK |
| iPS:435 579 | 21- 225_160G1 | VK1|L1/J K3 | DIQMTQSPSSLSA SVGDRVTITC | RAS--QDIN- ----NYLA | WFQQKPGK APTSLIY | A------ SSSLQS | GVPSKFSGSGSG- TDFTLTISSLQPEDFATYYC | QQYHS------ --------YPFT | FGPGT KVDIR |
| iPS:435 585 | 21- 225_160G3 | VK1|L1/J K3 | DIQMTQSPSSLSA SVGDRVTITC | RAS--QDIN- ----NYLA | WFQQRPGK APTSLIY | A------ SSSLQS | GVPSKFSGSGSG- TDFTLTISSLQPEDFATYYC | QQYHS------ --------YPFT | FGPGT KVDIK |
| iPS:435 635 | 21- 225_163F1 | VK1|L1/J K3 | DIQMTQSPSSLSA SVGDRVTITC | RAS--QDIS- ----NYLA | WFQQKPGK APKSLIY | A------ ASSLQS | GVPSKFSGSGSG- TDFTLTISSLQPEDFAAYYC | QQYNS------ --------YPFT | FGPGT QVDAQ |

Figure 51 (Continued)

| | | | | | | | | |
|---|---|---|---|---|---|---|---|---|
| iPS:435 659 | 21-225_167D1 2 | VK1\|L1/J K3 | DIQMTQSPSSLSA SVGDRVTITC | RAS--QGIN- ----NYLA | WFQQKPGK APKSLIY | A------ ASSLQS | GVPSKFSGSGSG-- TDFTLTISSLQPEDFATYYC | QQYNS------------YPFT | FGPGT KVDIK |
| iPS:435 679 | 21-225_169D1 0 | VK1\|L1/J K3 | DIQMTQSPSSLSA SVGDRVTITC | RAS--QDIS- ----NYLA | WFQQKPGK APKSLIY | A------ ASSLQS | GVPSKFSGSGSG-- TDFTLTISSLQPEDFATYYC | QQYHS------------YPFT | FGPGT KVDIK |
| iPS:435 685 | 21-225_170E1 | VK1\|L1/J K3 | DIQMTQSPSSLSA SEGDRVTITC | RAS--QGIS- ----NYLA | WFQQKPGK APKSLIY | A------ ASSLQS | GVPSKFSGSGSG-- IDFTLTISSLQPEDFATYYC | QQYHS------------YPFT | FGPGT KVDIK |
| iPS:435 747 | 21-225_175C4 | VK1\|L1/J K3 | DIQMTQSPSSLSA SVGDRVTITC | RAS--QGIG- ----NYLA | WFQQKPGK APKSLIY | A------ ASGLQS | GFPSKFSGSGSG-- TDFTLTISSLQPEDFATYYC | QQYYS------------YPFT | FGPGT KVDIK |
| iPS:435 765 | 21-225_177D3 | VK1\|L1/J K3 | DIQMSQSPSSLSA SVGDRVTITC | RAS--QGIT- ----NYLA | WFQQKPGK APKSLIY | A------ ASSLQS | GVPSKFSGSGSG-- IDFTLTISSLQPEDFATYYC | QQYNS------------YPFT | FGPGT KVDIK |
| iPS:435 797 | 21-225_181G2 | VK1\|L1/J K3 | DIQMTQSPSSLSA SIGERVTITC | RAS--QGIS- ----NYLA | WIQQKPGT APKSLIY | A------ ASSLQS | GVSSRFSGSGFG-- TDFTLTISSLQPEDFATYYC | QQYNG------------YPFT | FGPGT KVDIK |
| iPS:435 835 | 21-225_190F12 | VK1\|L1/J K3 | DIQMTQSPSSLSA SVGDRVTITC | RAS--QGIG- ----KYLA | WFQQRPGK APKSLIY | A------ ASSLQS | GVPSKFSGSGSG-- TDFTLTISSLQPDDFATYYC | QRYDT------------YPFT | FGPGT KVDIR |
| iPS:435 861 | 21-225_190A5 | VK1\|L1/J K3 | DIQMTQSPSSLSA SVGDRVTITC | RAS--QGIG- ----NYLA | WFQQKPGK APKSLIH | A------ ASSLQS | GVPSKFSGSGSG-- TDFTLTISSLQPEDFATYYC | QQYSN------------YPVT | FGPGT KVDIK |
| iPS:435 869 | 21-225_190B1 | VK1\|L1/J K3 | DIQMTQSPSSLSA SVGDRVTITC | RAS--QGIR- ----NYLA | WFQQKPGK APKSLIY | V------ ASSLES | GFPSKFSGSGSG-- IEFTLTISSLQPEDFGTYYC | QQYLN------------YPFT | FGPGT KVDIR |
| iPS:435 877 | 21-225_184E7 | VK1\|L1/J K3 | DIQMTQSPSSRSA SIGERVTITC | RAS--QGIS- ----NYLA | WFQQKPGT APKSLIY | A------ ASSLQS | GVSSRFSGSGFG-- TDFTLTISSVQREDFATYYC | QQYNG------------YPFT | FGHGT KVDIK |
| iPS:435 883 | 21-225_185A1 | VK1\|L1/J K3 | DIQMTQSPSSLSA SVGDRVTITC | RAS--QGIS- ----NYLA | WFQQTPGK APKSLIS | V------ ASSLQS | GVPSRFSASGSG-- IDFTLTISSLQPEDFATYYC | RQYHS------------YPFT | FGPGT KVDIK |
| iPS:435 885 | 21-225_185E1 | VK1\|L1/J K3 | DIQMTQSPSSRSA SIGERVTITC | RAS--QGIS- ----NYLA | WIQQKPGT APKSLIY | A------ ASSLQS | GVSSRFSGSGFG-- TDFTLTISSLQPEDFATYYC | QQYNG------------YPFT | FGPGT KVDIK |
| iPS:435 891 | 21-225_188H5 | VK1\|L1/J K3 | DIQMTQSPSSLSA SIGERVTITC | RAS--QGIS- ----NYLA | WLQQKPGT APKSLIY | A------ ASSLQS | GVSSRFSGSGFG-- TDFTLTISSLQPEDFATYYC | QQYNS------------YPFT | FGPGT KVDIK |
| iPS:435 897 | 21-225_188B9 | VK1\|L1/J K3 | DIQMTQSPSSLSA SIGERVTITC | RAS--QGIS- ----NYLA | WLQQKPGT APKSLIY | A------ ASSLQS | GVSSRFSGSGFG-- TDFTLTISSLQPEDFATYYC | QQYNS------------YPFT | FGPGT KVDIK |
| iPS:435 937 | 21-225_190H9 | VK1\|L1/J K3 | DIQMTQSPSSLSA SIGERVTITC | RAS--QGIG- ----KYLA | WFQQKPGK ALKSLIY | A------ ASSLQS | GVPSKFSGSGSG-- TDFTLTISSLQPEDFATYYC | QRYDT------------YPFT | FGPGT KVDIK |
| iPS:435 961 | 21-225_192A2 | VK1\|L1/J K3 | DIQMTQSPSSLSA SVGDRVTITC | RAN--QGIN- ----NYLA | WFQQKPGK APKSLIY | A------ ASSLQS | GVPSKFSGSGSG-- IDFTLTISSLQPEDFATYYC | QQYNS------------YPFT | FGPGT KVDIK |
| iPS:435 977 | 21-225_192E4 | VK1\|L1/J K3 | DIQMTQSPSSLSA SVGDRVTITC | RAS--QGIS- ----NYLA | WFQQKPGK APKSLIY | V------ VSSLQS | GVPSKFSGSGSG-- TDFTLTISSLQPEDFATYYC | QRYDT------------YPFT | FGPGT KVDIK |
| iPS:436 001 | 21-225_192C1 0 | VK1\|L1/J K3 | DIQMTQSPSSLSA SVGDRVTITC | RAS--QGIG- ----KYLA | WFQQKPGK ALKSLIY | A------ ASSLQS | GVPSKFSGSGSG-- TDFTLTISSLQPEDFATYYC | QRYDT------------YPFT | FGPGT KVDIK |
| iPS:436 039 | 21-225_193F8 | VK1\|L1/J K3 | DIQMTQSPSSLSA SVGDRVTITC | RAS--QGVS- ----NHLA | WFQQKPGK APKSLIY | A------ ASSLQR | GVPSKFSGSRSG-- ADFTLTISSLQPEDFATYYC | QQYNS------------YPFT | FGPGT KVDIK |
| iPS:436 078 | 21-225_194H1 | VK1\|L1/J K3 | DIQMTQSPSSLSA SVGDRVTITR | RAS--QGIG- ----KYLA | WFQQKPGK ALKSLIY | A------ ASSLQS | GVPSKFSGSGSG-- TDFTLTISSLQPEDFATYYC | QRYDT------------YPFT | FGPGT KVDFK |
| iPS:436 140 | 21-225_197G3 | VK1\|L1/J K3 | DIQMTQSPSSLSA SVGDRVTITC | RAS--QGIG- ----NHLA | WFQQKPGK APKSLIY | A------ ASSLQS | GVPSKFSGSRSG-- TDFSLTISSLQPEDFATYYC | QQYSN------------YPVT | FGPGT KVDIK |

Figure 51 (Continued)

| | | | | | | | | |
|---|---|---|---|---|---|---|---|---|
| iPS:436 167 | 21- 225_197E1 | VK1jL1/J K3 | DIQMTQSPSSLSA SVGDRVTITC | RAS--QGIN- ----KYLS | WFQQKPGK APKSLIY | A------ ASSVQS | GVPSKFSGSGSG-- TDFTLTISRLQPEDFATYYG | QRYDT------ ------YPFT | FGPGT KVDIK |
| iPS:436 370 | 21- 225_211A6 | VK1jL1/J K3 | DIQMTQSPSSLSA SVGDSVTITC | RAS--QGIG- ----KYLA | WFQQKPGK APKSLIY | A------ ASSLLS | GVPSKFSGSGSG-- TDFTLTISSLQPEDFATYYC | QKYDT------ ------YPFT | FGPGT KVDIK |
| iPS:436 392 | 21- 225_213B3 | VK1jL1/J K3 | DIQMTQSPSSLSA SVGDRVTITC | RAS--QGIG- ----KYLA | WFQQKPGK APKSLIS | A------ ASSVLS | GVPSKFSGSGSG-- TDFTLTISSLQPEDFATYYC | QKYDT------ ------YPFT | FGPGT KVDIK |
| iPS:436 404 | 21- 225_214C3 | VK1jL1/J K3 | DIQMTQSPSSLSA SVGDRVTITC | RAS--QGIG- ----NYLA | WFQQKPGK VPKSLIY | A------ ASSLQS | GVPSKFSGSGSG-- TDFTLTISSLQPEDFTTYYC | QQYMT------ ------YPII | FGPGT KVDIK |
| iPS:436 406 | 21- 225_214E4 | VK1jL1/J K3 | DIQMTQSPSSLSA SVGDRVTITC | RAS--QGIS- ----NYLA | WFQQKPGK APKSLIY | A------ ASSLQS | GVPSKFSGSGSG-- TDFTLTISSLQPEDFATYYC | QQYLT------ | FGPGT KVDIK |
| iPS:437 216 | 21- 225_51D5 | VK1jL1/J K3 | DIQMTQSPSSLSA SVGDRVTITC | RAS--QGIN- ----NYLA | WFQQKPGE APKSLIY | A------ ASSLRS | GVPSQFSGSGSG-- TDFTLTISSLQPEDFATYYC | QQYYS------ ------YPFT | FGPGT KVDIK |
| iPS:437 224 | 21- 225_56H1 | VK1jL1/J K3 | DIQMTQSPSSLSA SVGDRVTITC | RAS--QGIS- ----HYLA | WFQQKPGK APQSLMS | A------ ASGLQS | GVPSKFSGSGSG-- TDFTLTISSLQPEDFATYYC | QQYQN------ ------YPFT | FGPGT KVDIK |
| iPS:392 620 | 21- 225_17H5 | VK1jL1/J K3 | DIQMTQSPSSLSA SVGDRVTITC | RAS--QGIS- ----NYLA | WFQQKPGK APKSLIY | A------ ASSLQS | GVPSKFSGSGSG-- TDFTLTISSLQPEDFATYYC | QQYHS------ ------YPFT | FGPGT KVDIK |
| iPS:392 692 | 21- 225_18G10 | VK1jL1/J K3 | DIQMTQSPSSLSA SVGDRVTITC | RAS--QDIS- ----YYLA | WFQQKPGK APKSLIY | V------ ASSLQS | GVPSKFGGSGFG-- TDFTLTISSLQPEDFATYYC | LQYNS------ ------YPFT | FGPGT KVDIK |
| iPS:392 708 | 21- 225_18D11 | VK1jL1/J K3 | DIQMTQSPSSLFA FVGDRVTITC | RAS--QGIG- ----YYLA | WFQQKPGK APKSLIY | V------ ASSLQS | GVPSKFSGSGFG-- TEFTLTISSLQPEDFASYYC | QQYNT------ ------YPFT | FGPGT TVDIK |
| iPS:392 714 | 21- 225_16G12 | VK1jL1/J K3 | DIQMTQSPSSLSA SVGDRVTITC | RAS--QDIS- ----NYLA | WFQQKPGK APKSLIY | A------ ASSLQS | GVPSKFRGSGSG-- TDFTLTISNLQPEDFATYYC | QQYHS------ ------FPFT | FGPGT KVDIK |
| iPS:392 746 | 21- 225_20H7 | VK1jL1/J K3 | DIQMTQSPSSLSA SVGDRVTITC | RTS--QGIN- ----NYLV | WFQQKPGK APKRLIY | A------ ASSLQS | GVPSKFSGSGSG-- TDFTLTISSLQPEDFATYYC | QQYYS------ ------YPFT | FGPGT KMDFK |
| iPS:392 782 | 21- 225_22B12 | VK1jL1/J K3 | DIQMTQSPSSLSA SVGDRVTITC | RAS--QDIS- ----NYLA | WFQEKPGK AHKSLIY | G------ ASSLRS | GVPSKFSGSGSG-- TDFNLTISSLQPEDLATYYC | QQYNS------ ------YPFT | FGPGT KVDEK |
| iPS:392 784 | 21- 225_23C7 | VK1jL1/J K3 | DIQMTQSPSSLSA SVGDRVTITC | RAS--QGIG- ----IYLA | WFQQKPGK APKSLIS | A------ ASSLQS | GVPSKFSGSGSG-- TDFTLTISSLQPEDFATYYC | QQYNS------ ------YPFT | FGPGT KVDIK |
| iPS:392 802 | 21- 225_23E7 | VK1jL1/J K3 | DIQMTQSPSSLSA SVGDRVTITC | RAS--QGIR- ----YYLA | WFQQIPGK APKSLII | V------ ASSLQS | GVPSQFSGSGFG-- TEFTLTISSLQPEDFATYYC | QQFYS------ ------YPFT | IGPGT KVDIN |
| iPS:392 826 | 21- 225_20B9 | VK1jL1/J K3 | DIQMTQSPSSLSA SVGDRVTITC | RAS--QGIS- ----NYLA | WFQQKPGK APKSLIY | V------ ASSLQS | GVPSKFSGSGSG-- TDFTLTISSLQPEDFATYYC | QQYNT------ ------YPFT | FGPGT KVDIK |
| iPS:392 840 | 21- 225_23G1 | VK1jL1/J K3 | DIQMTQSPSSLSA SVGDRVTITC | RAS--QGIS- ----NYLA | WFQQKPGK APKSLIS | A------ ASSLQS | GVPSQFSGSGFG-- TDFTLTISSLQPEDFATYYC | QQYNS------ ------YPFT | FGPGT KVDIK |
| iPS:392 842 | 21- 225_23G8 | VK1jL1/J K3 | DIQMTQSPSSLSA SVGDRVTITC | RAS--QGIS- ----NYLA | WFQQIPGK APKSLIY | A------ ASSLQS | GVPNFSGSGSG-- TDFTLTISSLQPEDFATYYC | QQYNS------ ------YPFT | FGPGT KVDIK |
| iPS:392 890 | 21- 225_20H9 | VK1jL1/J K3 | DIQMTQSPSSLSA SVGDRVTITC | RAS--QGIS- ----NYLA | WFQQKPGK APKSLIY | A------ ASSLRS | GVPSKFSGSGSG-- TDFTLTISSLQPEDFATYYC | QQYNS------ ------YPFT | FGPGT KVDIK |
| iPS:392 892 | 21- 225_20C11 | VK1jL1/J K3 | DIQMTQSPSSLSA SVGDRVTITC | RAS--QGIR- ----NYLA | WFQQKPGK APKSLIY | A------ ASSLQS | GVPSKFRGSGSG-- TDFTLTISSLQPEDFATYYC | QQYHS------ ------FPFT | FGPGT KVDVK |
| iPS:392 950 | 21- 225_25C10 | VK1jL1/J K3 | DIQMTQSPSSLSA SVGDRVTITC | RAS-------- ----NYLA | WFQQKPGK APKSLIY | A------ ASSLQS | GFPSKFSGSGSG-- TDFTLTISSLQPEDFATYYC | QQYHS------ ------YPFT | FGPGT KVDIK |
| iPS:392 952 | 21- 225_26G1 | VK1jL1/J K3 | DIQMTQSPSSLSA SVGDRVTITC | RAS--QDIS- ----NYLA | WFQQKPGK APKSLIY | A------ ASSLRS | GVPSNFSGSGSG-- TDFTLTISSLQPENFATYYC | QQYNS------ ------YPFT | FGPGT KVDIK |
| iPS:392 962 | 21- 225_30A1 | VK1jL1/J K3 | DIQMTQSPSSLSA SVGDRVTITC | RAS--QGIS- ----NYLA | WFQQKPGK APKSLIS | A------ ASSLQT | GVPSKFSGSGSG-- TDFTLTISSLQPEDFATYYC | QQYNS------ ------YPFT | FGPGT KVDIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:392976 | 21-225_27H12 | VKjL1/JK3 | DIQMTQSPSSLSA SVGDRVTITC | RAS--QGIS------NYLA | WFQQKPGK APKSLIN | G-------ASSLQS | GVPSKFSGSGSG--TDFTLTISSLQPEDFATYYC | QQYYS-------YPFT | FGPGT KVNIN |
| iPS:393090 | 21-225_33A5 | VKjL1/JK3 | DIQMTQSPSSLSA SVGDRVTITC | RAS--QGIS------NYLA | WFQQKPGK APKSLIS | A-------ASSLQS | GVPSKFSGSGSG--TDFTLTISSLQPEDFATYYC | QQYNS-------YPFT | FGPGT NVDIK |
| iPS:393120 | 21-225_35H8 | VKjL1/JK3 | DIQMTQSPSSLSA SVGDRVTITC | RAS--QAIS------NYLA | WFQQKPGK APKSLIY | G-------ASGLQS | GVPSKFSGSGSG--TDFTFPISSLQPEDFANYYC | QQYNS-------YPFT | FGPGT KVDFK |
| iPS:393836 | 21-225_15A2 | VKjL1/JK3 | DIQMTQSPSSLFA FIGDRVTITC | RAS--QGIS------NYLA | WFQQKPGK APKSLIF | A-------ASSLQS | GVPSKFSGSGSG--TDFTFPISSLQPEDFANYYC | QQYYS-------YPFT | FGPGT QVDVK |
| iPS:393870 | 21-225_7B1 | VKjL1/JK3 | DIQMTQAPSSLSA SVGDRVTITC | RAS--QDIS------NHLV | WFQQKPGK APKSLIF | A-------ASSLQS | GVPSQFSGSGSG--TDFTLTISLLQPEDFATYYC | HQYNS-------YPFT | FGPGT KVDFK |
| iPS:393894 | 21-225_5E11 | VKjL1/JK3 | VIQMTQSPSSLSA SVGDRVTITC | RAS--QGIS------NYLA | WFQQKPGK APKSLIN | A-------ASSVQS | GVPSKFSGNGSG--TDFTLTISSLQPEDFATYYC | HQYHS-------YPFT | FGPGT KVDIK |
| iPS:393896 | 21-225_2A4 | VKjL1/JK3 | DIQMTQSPSSLFA SVGDRVTITC | RAS--QGIS------NYLA | WFQQKPGK APKRLIY | T-------ASSLQS | GVPSKFSGSGSG--TDFTLTISSLQPEDFATYYC | QQYNS-------YPFT | FGPGT KVDIK |
| iPS:393914 | 21-225_16B8 | VKjL1/JK3 | DIQMTQSPSSLSA SVGDRVTITC | RAS--QGIN------NYLA | WFQQKPGK ALKSLIN | A-------ASSVQS | GVPSKFSGSGSG--TDFTLTISSLQPEDFATYYC | HQYHS-------YPFT | FGPGT KVDIV |
| iPS:393968 | 21-225_5A5 | VKjL1/JK3 | DIQMTQSPSSLSA SVGDRVTITC | RAS--QGIS------NYLA | WFQQKPGK APKSLIS | A-------ASSLQS | GVPSKFSGSGSG--TDFTLTISSLQPEDFATYYC | QQYNS-------YPFT | FGPGT KVDIK |
| iPS:393992 | 21-225_14H8 | VKjL1/JK3 | DIQMTQSPSSLSA SVGDRVTITC | RAS--QGIS------YYLA | WFQQKPGK APKSLIY | V-------ASSLQS | GVPSKFSGSGSG--TDFTLTISSLQPEDFATYYC | QQYNS-------YPFT | FGPGT KVDIN |
| iPS:394018 | 21-225_15B1 | VKjL1/JK3 | DIQMTQSPSSLSA SVGDRVTITC | RAS--QGIS------NYLA | WFQQKPGK APKSLIS | A-------ASSLQS | GVPSKFSGSGSG--TDFTLTISSLQPEDFATYYC | QQYHS-------YPFT | FGPGT KVDIK |
| iPS:394026 | 21-225_16C7 | VKjL1/JK3 | DIQMTQSPSSLSA SVGDRVTITC | RAS--QGIS------NYLA | WFQQKPGK APKSLIS | A-------ASSLQS | GVPSKFSGSGSG--TDFTLTISSLQPEDFATYYC | QQYDS-------YPFT | FGPGT KVDIK |
| iPS:394055 | 21-225_9C8 | VKjL1/JK3 | DIQMTQSPSSLSA SVGDRVTITC | RAS--QGIS------YYLA | WFQQKPGK APKSLIY | V-------ASSLQS | GVPSKFSGSGSG--TDFTLTISSLQPEDFATYYC | QQYHS-------YPFT | FGPGT KVDIK |
| iPS:398482 | 21-225_17H6 | VKjL1/JK3 | DIQMTQSPSSLSA SVGDRVTITC | RAS--RDIS------NYLA | WFQQKPGK APKSLIS | T-------ASTLQS | GVPSKFSGSGSG--TDFTLTISSLQPEDFATYYC | QQYHS-------YPFT | FGPGT KVDIQ |
| iPS:398500 | 21-225_23A11 | VKjL1/JK3 | DIQMTQSPSSLST SVGDRVTITC | RAS--QDIS------NYLA | WFQQKPGK APKRLIY | A-------ASTLQS | GVPSKFSGSGSG--TDFTLTISSLQPEDFATYYC | QQYNS-------YPFT | FGPGT KVDLK |
| iPS:398526 | 21-225_32B3 | VKjL1/JK3 | DIQMTQSPSSLSA SIGDRVTITC | RAS--QGIS------NYLA | WFQQKPGK APRSLIY | A-------ASSLQS | GVPSTFSGSGSG--TDFTLTISSLQPEDFATYYC | QQYNS-------YPFT | FGPGT KVDIK |
| iPS:402235 | 21-225_20F10 | VKjL1/JK3 | DIQLTQSPSPLSA SVGDRVTITC | RAS--QGIN------NYLA | WFQQKPGK APKSLIY | A-------ASSLQS | GVPSRFSGSGSG--TDFTLTISSLQPEDFATFYC | QQYNS-------YPFT | FGPGT KVDNK |
| | Germline | | K_FR1 | K_CDR1 | K_FR2 | K_CDR2 | K_FR3 | K_CDR3 | K_FR4 |
| VK3jA27/JK1 | | VK3jA27/JK1 | | | | | | QQYES-------SPWT | FGQGT KVEIK |
| iPS:468810 | 21-225_74D5 | VK3jA27/JK1 | EIVLTQSPGTLSL SPGERATLSC | RAS--QSVNS-----NYLA | WYRQKPGQ APRLLIY | G-------ASSRAT | GIPDRFSGSGSG--TDFTLLISRLEPEDFAVYYC | QQYES-------SPWT | FGQGT KVEIK |
| iPS:468834 | 21-225_94G10 | VK3jA27/JK1 | EIVLTQSPGTLSL SPGERATLSC | RAS--QSVNS-----NYLA | WYRQKPGQ APRLLIY | G-------ASSRAT | GIPDRFSGSGSG--TDFILIISRLEPEDFAVYYC | QQYES-------SPWT | FGQGT KVEIK |
| iPS:468838 | 21-225_80E12 | VK3jA27/JK1 | EIVLTQCPGTLSL SPGERATVSC | RAS--QSVNS-----NYLA | WYRQKPDQ APRLLIY | G-------ASSRAT | GIPDRFSGSGSG--TDFTLLISRLEPEDFAVYYC | QQYES-------SPWT | FGQGT KVEIK |
| iPS:468820 | 21-225_76E10 | VK3jA27/JK1 | EIVLTQSPGTLSL SPGERATLSC | RAS--QSVNS-----NYLA | WYRQKPGQ APRLLIY | G-------ASSRAT | GIPDRFSGSGSG--TDFTLIISRLEPEDFAVYYC | QQYES-------SPWT | FGQGT KVEIK |
| iPS:433931 | 21-225_44F6 | VK3jA27/JK1 | EIVLTQSPGTLSL SPGERATLSC | RAS--QSVSG-----SYLA | WYCQKPGQ APRLLIY | G-------ASSRAT | GIPDRFSGSGSG--TDFTLTISRLEPEDFAVYYC | QQYGS-------SPWT | FGQGT KVEIK |

Figure 51 (Continued)

| ID | | Family | | | | | | | |
|---|---|---|---|---|---|---|---|---|---|
| iPS:434_307 | 21-225_59B2 | VK3|A27/JK1 | EIVLTQSPGTLSL SPGERATLSC | WAS--QSVYS- ----SFLA | WFQQKSGQ APRLLIY | G------- ASSRAT | GIPDRFSGSGSG-- TDFTLTISRLEPEDFAVFYC | QQYGT- ----- | -----SPWT FGQGT KVEIK |
| iPS:434_471 | 21-225_75G3 | VK3|A27/JK1 | EIVLTQSPGTLSL SPGERATLSC | RAR--QNVDS- ----SYLA | WYQQKPGQ APRLLIY | G------- ASSRAT | GIPDRFSGSGSG-- TDFTLTISRLEPEDFAVFYC | QQYER- ----- | -----SPWT FGQGT KVEIK |
| iPS:434_473 | 21-225_76D1 | VK3|A27/JK1 | EIVLTQSPGTLSL SPGERATLSC | RAS--QNIYS- ----NYLA | WYQEKPGQ APRLLIY | G------- ASSRAT | GIPDRFSGSGSG-- TDFTLTISRLEPEDFVVYYC | QQYES- ----- | -----SPWT FGQGT KVEIK |
| iPS:434_495 | 21-225_74B2 | VK3|A27/JK1 | EIVLTQSPGTLSL SPGERATLSC | RAS--QNIYS- ----SYLA | WYQQKPGQ APRLLIY | G------- ASSRAT | GIPDRFSGSGSG-- TDFTLTISRLEPEDFAVYYC | QQYES- ----- | -----SPWT FGQGT KVEIK |
| iPS:434_497 | 21-225_76A4 | VK3|A27/JK1 | EIVLTQSPGTLSL SPGERATLSC | RAS--QSVYS- ----SYLA | WYQQKPGQ APRLLIY | G------- ASSRAT | GIPDFALTISRLEPEDFAVYYC TDFALTISRLEPEDFAVYYC | QHSDN- ----- | -----SPWT FGQGT KVEIK |
| iPS:434_501 | 21-225_76G4 | VK3|A27/JK1 | EIVLTQSPGTLSL SPGERATLSC | RAS--QSVYS- ----SYLA | WYQQKPGQ APRLLIY | G------- ASSRAT | GIPDRFSGSGSG-- TDFALTISRLEPEDCAVYYC | QHSDN- ----- | -----SPWT FGQGT KVEIK |
| iPS:434_507 | 21-225_74C5 | VK3|A27/JK1 | EIVLTQSPGTLSL SPGERATLSC | RAS--QSVNS- ----NYLA | WYQQKPGQ APRLLIY | G------- AFSRAT | GIPDRVSGSGSG-- TDFNLIISRLEPEDFAVYYC | QQYES- ----- | -----SPWT FGQGT KVEIK |
| iPS:434_517 | 21-225_76A7 | VK3|A27/JK1 | EIALTQSPGTLSL SPGERATLSC | RAS--PSVDS- ----SYLA | WYQQKPGQ APRLLIY | G------- ASSRAT | GIPDRFSGSGSG-- TDFTLTISRLEPEDFAVYYC | QQYES- ----- | -----SPWT FGQGT KVEIK |
| iPS:434_519 | 21-225_74C7 | VK3|A27/JK1 | EIVLTQSPGTLSL SPGERATLSC | RTS--PNVDS- ----SYLA | WYQQKPGQ APRLLIY | G------- ASSRAT | GIPDRFSGSGSG-- TDFILIISRLEPEDFAVYYC | QQYER- ----- | -----SPWT FGQGT KVEIK |
| iPS:434_523 | 21-225_75C3 | VK3|A27/JK1 | EIVLTQSPGTLSL SQGERATLSC | RAS--QSVSS- ----RYLA | WYQQKPGQ APRLLIY | G------- ASSRAT | GIPDRFSGSGSG-- TDFALTISRLEPEDFAVYYC | QHYDS- ----- | -----SPWT FGQGT KVEIK |
| iPS:434_531 | 21-225_76C9 | VK3|A27/JK1 | EIVLTQSPGTLSL SPGERATLSC | RAS--QSVSS- ----SYLS | WYQQKPGQ APRLLIY | G------- ASSRAT | GIPDRFSGSGSG-- TDFTLTISRLEPEDFAVYYC | QQYG-- ----- | -----RSRT FGQGT KVEIK |
| iPS:434_533 | 21-225_85F7 | VK3|A27/JK1 | EPVLTQSPGTLSL SPGERATLSC | RAS--QNIYS- ----NYLA | WYQQKPGQ APRLLIY | G------- ATSRAT | GIPDRFSGSGSG-- TDFTLTISRLEPEDFAVYFC | QQYES- ----- | -----SPWT FGQGT KVEIK |
| iPS:434_547 | 21-225_74H5 | VK3|A27/JK1 | EIVLTQSPGTLSL SPGERATLSC | RAS--QSVDS- ----SYLA | WYRQKPGQ APRLLIY | G------- ASSRAP | GIPDRFSGSGSG-- TDFILIINRLEPEDFAVYYC | QQYES- ----- | -----SPWT FGQGT KVEIK |
| iPS:434_559 | 21-225_74D11 | VK3|A27/JK1 | EIVLTQSPGTLSL SPGERATLSC | RAS--QSVYS- ----NYLA | WYQQKPGQ APRLLIY | G------- ASSRAT | GIPDRFSGSGSG-- TDFALTISRVEREDCAVYYC | QHYDN- ----- | -----SPWT FGQGT KVEIK |
| iPS:434_561 | 21-225_77G1 | VK3|A27/JK1 | EIVLTQSPGTLYL SPGERATLSC | RAS--QSVYS- ----SYLA | WYQQKPGQ APRLLIY | G------- ASSRST | GIPDRFSGSGSG-- TDFALTISRLEPEDFAVYYC | QHYDN- ----- | -----SPWT FGQGT KVEIK |
| iPS:434_565 | 21-225_75B10 | VK3|A27/JK1 | EIVLTQSPGTLSL SPGERATLSC | RAS--PSVNS- ----YYLA | WYQQKPGQ APRLLIY | G------- ASSRAT | GIPDRFSGSGSG-- TDFTLTISRLEPEDFAVYYC | QQYED- ----- | -----SPWT FGQGT KVEIK |
| iPS:434_571 | 21-225_74D2 | VK3|A27/JK1 | EIVLTQSPGTLSL SPGERATLSC | RAS--QSVHS- ----NYLA | WYQQKPGQ APRLLIY | G------- ASSRAP | GIPDRFSGSGSG-- TDFTLTISRLEPEDFAVYYC | QQYES- ----- | -----SPWT FGQGT KVEIK |
| iPS:434_579 | 21-225_77F7 | VK3|A27/JK1 | EIVLTQSPGTLYL SPGERATLSC | RAS--QSVYS- ----SYLA | WYRQKPGQ APRLLIY | G------- ASSRAT | GIPDRFSGSGCG-- TDFALTISRVEREDCAVYYC | QHYDN- ----- | -----SPWT FGQGT KVEIK |
| iPS:434_581 | 21-225_74B12 | VK3|A27/JK1 | EIVLTQSPGTLSL SPGERATLSC | RAS--QSVYS- ----SYLA | WYQQKPGQ APKLLIE | G------- ASSRAT | GIPDRFSGSGSG-- TDFALTISRLEPEDFAVYYC | QHYDN- ----- | -----SPWT FGQGT KVEIK |
| iPS:434_585 | 21-225_75A12 | VK3|A27/JK1 | EIVLTQSPGTLSL SPGERATLSC | RAS--QSVSS- ----RYLA | WYQQKRGQ APRLLIY | G------- ASSRAT | GIPDRFSGSGSG-- TDFALTISRLEPADFAVYYC | QHYDS- ----- | -----SPWT FGQGT KVEIK |
| iPS:434_595 | 21-225_77A10 | VK3|A27/JK1 | EIVLTQSPGTLSL SPGERATLSC | RAR--QSVHS- ----RYLA | WYQQKPGQ APKLLIF | G------- ASSRAT | GIPDRFSGSGSG-- TDFTLTISRLEPEDFAVYYC | QHYDS- ----- | -----SPWT FGQGT KVEIK |
| iPS:434_611 | 21-225_77C12 | VK3|A27/JK1 | EIVLTQSPGTLSL SPGERATLSC | RAS--QSVDS- ----SYLA | WYQQKPGQ APRLLIY | G------- ASSRAT | GIPDRFSGSGSG-- TDFTLTISRLEPEDFAVYYC | QQYES- ----- | -----SPWT FGQGT KVEIK |
| iPS:434_633 | 21-225_74G8 | VK3|A27/JK1 | EIVLTQSPGTLSL SPGERATLSC | RAS--QSFSS- ----AYLA | WYQQKPGQ APRLLIY | G------- TSSRAT | GIPDRFSGSGSG-- TDFTLTIGRLEPEDFAVYYC | QQYG-- ----- | -----NSRT FGQGT KVEIK |

Figure 51 (Continued)

| ID | Germline | FR1 | CDR1 | FR2 | CDR2 | FR3 | CDR3 | FR4 |
|---|---|---|---|---|---|---|---|---|
| iPS:434_637 | 21-225_78E7 | VK3|A27/ JK1 | EIVLTQSPGTLSL SPGERATLSC | RAS--QNVDS----NYLA | WYQQKPGQ APRLLIY | G-------ASSRAT | GIPDRFSGSGSG-- TDFTLTISRLEPEDFAVYYC | QQYER------SPWT | FGQGT KVEIK |
| iPS:434_657 | 21-225_79G1 | VK3|A27/ JK1 | EIVLTQSPGTLYL SSGERATLSC | RAS--QSVYS----SYLA | WYQQKPAQ APRLLIY | G-------ASSRST | GIPDRFSGSGSG-- TDFALTISRLEPEDFAVYYC | QHYDN------SPWT | FGQGT KVEIK |
| iPS:434_663 | 21-225_79F3 | VK3|A27/ JK1 | EIVLTQSPGTLYL SPGERATLSC | RAS--QSVYS----SYLA | WYQQKPGQ APRLLIY | G-------ASSRST | GIPDRFSGSGSG-- TDFALTISRLEPEDFAVYYC | QHYDN------SPWT | FGQGT KVEIK |
| iPS:434_671 | 21-225_74F4 | VK3|A27/ JK1 | EIVLTQSPGTLSL SPGERATLSC | RAS--QIFSS----SYLA | WYQQKPGQ SPRLLIY | G-------ASSRAT | GIPDRFSGSGSG-- TDFTLTISRLEPEDFAVYYC | QQYG-------SSRT | FGQGT KVEIK |
| iPS:434_687 | 21-225_75A5 | VK3|A27/ JK1 | EIVLTQSPGTLSL SPGERATLSC | RAS--QSVYS----SYLA | WYQQKPGQ APRLLIY | G-------ASSRAT | GIPDRFSGSGSG-- TDFTLTISRLEPEDFAVYYC | QHYDN------SPWT | FGQGT KVEIK |
| iPS:434_691 | 21-225_75G7 | VK3|A27/ JK1 | EIVLTQSPGTLSL SPGERATLSC | RAR--QSVDS----SYLA | WYQQKRGQ APRLLIY | G-------ASSRAT | GIPDRFSGSGSG-- TDFTLTISRLEPEDFAVYYC | QQYES------SPWT | FGQGT KVEIK |
| iPS:434_693 | 21-225_79F11 | VK3|A27/ JK1 | EIVLTQSPGTLSL SPGERATLSC | RAS--QSVYS----SYLA | WYQQKPGQ APRLLIY | G-------ASSRST | GIPDRFSGSGSG-- TDFALTISRLEPEDFAVYYC | QHSDN------SPWT | FGQGT KVEIK |
| iPS:434_699 | 21-225_79G12 | VK3|A27/ JK1 | EIVLTQSPGTLYL SPGERATLSC | RAS--QSVYS----SYLA | WYQQKPGQ APRLLIY | G-------ASSRST | GIPDRFSGSGSG-- TDFALTISRLEPEDCAVYYC | QHSDN------SPWT | FGQGT KVEIK |
| iPS:434_701 | 21-225_80A1 | VK3|A27/ JK1 | EIVLTQSPGTRYL SPGERATLSC | RAS--QSVYS----SYLA | WYQQKPGQ APRLLIY | G-------ASSRST | GIPDRFSGSGSG-- TDFALTISRVEPEDCAVYYC | QHSDN------SPWT | FGQGT KVEIK |
| iPS:434_703 | 21-225_80C1 | VK3|A27/ JK1 | EIVLTQSPGTLYL SPGERATLSC | RAS--QSVYS----SYLA | WYQQKPGQ APRLLIY | G-------ASSRAP | GIPDRFSGSGSG-- TDFALTISRLEPEDFAVYYC | QHSDN------SPWT | FGQGT KVEIK |
| iPS:434_709 | 21-225_80E3 | VK3|A27/ JK1 | EIVLTQSPGTLSL SSGERATLSC | RAS--QSVYS----SYLA | WYQQKPGQ APRLLIY | G-------ASSRAP | GIPDRFSGSGSG-- TDFALTISRVEPEDCAVYYC | QQYES------SPWT | FGQGT KVEIK |
| iPS:434_715 | 21-225_80D5 | VK3|A27/ JK1 | ELVLTQSPGTLSL SPGKRVTLSC | RAS--QNIYS----SYLA | WYQQKPGQ APRLLIY | G-------ASSRST | GIPDRFSGSGCG-- TDFTLTISRLEPEDFAVYYC | QHSDN------SPWT | FGQGT KVEIK |
| iPS:434_717 | 21-225_80D5 | VK3|A27/ JK1 | EIVLTQSPGTLSL SPGEIPTLSC | RAS--QSVDS----GYLA | WYQQKPGQ APRLLIY | G-------ASSRAP | GIPDRFSGSGSG-- TDFTLTISRLEPEDFAVYYC | QQYES------SPWT | FGQGT KVEIK |
| iPS:434_725 | 21-225_80H7 | VK3|A27/ JK1 | EIVLTQSPGTLSL SPGERATLSC | RAS--QSINS----NYLA | WYQQKPGQ APRLLIY | G-------ASSRST | GIPDRFSGSGCG-- TDFALTISRVEPEDCAVYYC | QHSDN------SPWT | FGQGT KVEIK |
| iPS:434_735 | 21-225_80B10 | VK3|A27/ JK1 | EIVLTQSPGTLSL SPGERATLSC | RAS--QSVDS----SYLA | WYQQKPGQ APRLLIY | G-------ASSRAP | GIPDRFSGSGSG-- TDFTLTISRLEPEDFAVYYC | QQYES------SPWT | FGQGT KVEIK |
| iPS:434_743 | 21-225_74A4 | VK3|A27/ JK1 | EIVLTQSPGTLSL SPGERATLSC | RAS--QSVYS----SYLA | WYQQKPGQ APRLLIY | G-------ASSRST | GIPDRFSGSGCG-- TDFALTISRLEPEDCAVYYC | QHSDN------SPWT | FGQGT KVEIK |
| iPS:434_751 | 21-225_80H12 | VK3|A27/ JK1 | EIVLTQSPGTLYL SPGERATLSC | RAS--QSVVS----SYLA | WYQQKPGQ APRLLIY | G-------ASSRST | GIPDRFSGSGSG-- TDFTLTISRLEPEDFAVYYC | QHSDN------SPWT | FGQGT KVEIK |
| iPS:434_759 | 21-225_81C5 | VK3|A27/ JK1 | EIVLTQSPGTLSL SPGERATLSC | RAS--QSVYS----GYLA | WYQQKRGQ APRLLIY | G-------ASSRST | GIPDRFSGSGCG-- TDFALTISRVEPEDCAVYYC | QQYES------SPWT | FGQGT KVEIK |
| iPS:434_773 | 21-225_75D9 | VK3|A27/ JK1 | EIVLTQSPGTLYL SPVERATLSC | RAS--QSVYS----SYLA | WYQQKPGQ APRLLIY | G-------ASSRST | GLPDRFSGSGSG-- TDFALTISRLEPEDFAVYYC | QHSDN------SPWT | FGQGT KVEIK |
| iPS:434_777 | 21-225_81C11 | VK3|A27/ JK1 | EIVLTQSPGTLYL SPGERATLSC | RAS--QSVYS----SYLA | WYQQKPGQ APRLLIY | G-------ASSRST | GIPDRFSGSGSG-- TDFALTISRLEPEDFAVYYC | QHSDN------SPWT | FGQGT KVEIK |
| iPS:434_809 | 21-225_74F5 | VK3|A27/ JK1 | EIVLTQSPGTRYL SPGERATLSC | RAS--QSVYS----SYLA | WYQQKPGQ APRLLIY | G-------ASSRST | VLPDRFSGSGSG-- TDFALTISRVEPEDCAVYYC | QHSDN------SPWT | FGQGT KVEIK |
| iPS:434_821 | 21-225_83G1 | VK3|A27/ JK1 | EIVLTQSPGTLYL SPGERATLSC | RAS--QSVYS----SYLA | WYQQKPGQ APRLLIY | G-------ASSRST | GIPDRFSGSGSG-- TDFALTISRLEPEDFAVYYC | QHSDN------SPWT | FGQGT KVEIK |
| iPS:434_835 | 21-225_83B6 | VK3|A27/ JK1 | EIVLTQSPGTLSL SPGERATLSC | RAS--QSVDS----GYLA | WYQQKPGQ APRLLIY | G-------ASSKIF | GIPDRFSGSGSG-- TDFTLTISRLEPEDFAVYYC | QQYES------SPWT | FGQGT KVEIK |

Figure 51 (Continued)

| | | | | | | | | | |
|---|---|---|---|---|---|---|---|---|---|
| iPS:434 839 | 21-225_83B7 | VK3}A27/ JK1 | EIVLTQSPGTRYL SSVERATLSC | RAS--QSVYS- ---SYLA | WYQQKPGQ APRLLIY | G------- ASSRST | GIPDRFSGSGSG- TDFALTISRLEPEDCAVYYC | QHSDN--- -------- | ----SPWT FGQGT KVEIK |
| iPS:434 849 | 21-225_83C10 | VK3}A27/ JK1 | EIVLTQSPGTLSL SPGERATLSC | RAS--PSVHS- ---NYLA | WYQQKPGQ APRLLIY | G------- ASSRAT | GIPDRFSGSGSG- TDFTLTISRLEPEDFAVYYC | QQYES--- -------- | ----SPWT FGQGT KVEIK |
| iPS:434 869 | 21-225_84E12 | VK3}A27/ JK1 | EIVLTQSPGTLSL SPGERATLSC | RAS--QSINS- ---NYLA | WYQQKPGQ APRLLIY | G------- ASSRAT | TDFTLTISRLEPEDFAVFYC | QQYES--- -------- | ----SPWT FGQGT KVEIK |
| iPS:434 879 | 21-225_85A3 | VK3}A27/ JK1 | EIVLTQSPGTLFL SPGERATLSC | RAS--QSVYS- ---SYLA | WYQQKPGAQ APRLLIY | G------- ASSRAS | GIPDRFSGSGSG- TDFALTISRLEPEDFAVYYC | QHYDN--- -------- | ----SPWT FGQGT KVEIK |
| iPS:434 881 | 21-225_85B4 | VK3}A27/ JK1 | EIVLTQSPGTLFL SPGERATLSC | RAS--QSVYS- ---SYLA | WYQQKPGQ APRLLIY | G------- ASSRAT | GIPDRFSGSGSG- TDFTLTISRLEPEDFAVYYC | QHYDS--- -------- | ----SPWT FGQGT KVEIK |
| iPS:434 887 | 21-225_85D6 | VK3}A27/ JK1 | EIVLTQSPGTLFL SQGERATLSC | RAS--QSVSS- ---RYLA | WYQQKPGQ APRLLIY | G------- ASSRAT | GIPDRFSGSGSG- TDFTLTISRLEPEDFAVYYC | QQYES--- -------- | ----SPWT FGQGT KVEIK |
| iPS:434 891 | 21-225_85G6 | VK3}A27/ JK1 | EIALTQSPGTLSL SPGERATLSC | RAS--PSVDS- ---SYLA | WYQQKPGQ APRLLIY | G------- AASRAP | GIPDRFSGSGSG- TDFTLTISRLEPEDFVVYYC | QQYES--- -------- | ----SPWT FGQGT KVEIK |
| iPS:434 895 | 21-225_74H7 | VK3}A27/ JK1 | EIVLTQSPGTLSL SPGERATLSC | RAS--QNIYS- ---SYLA | WYQQKPGQ APRLLIY | G------- ASSRAT | GIPDRFSGSGSG- TDFTLTISRLEPEDFAVYYC | QHSDN--- -------- | ----SPWT FGQGT KVEIK |
| iPS:434 899 | 21-225_85B9 | VK3}A27/ JK1 | EIVLTQSPGTLFL SPGERATLSC | RAS--QSVNS- ---NYLA | WYRQKPGQ APRLLIY | G------- ASSRAT | GIPDRFSGSGSG- TDFTLTISRLEPEDFAVYYC | QQYES--- -------- | ----SPWT FGQGT KVEIK |
| iPS:434 907 | 21-225_85G10 | VK3}A27/ JK1 | EIVLTQSPGSLSL SPGERATLSC | RAS--QSVWS- ---GYLA | WYQQKPGQ APRLLIY | G------- ASARTT | GIPDRFSGSGSG- TDFTLTISRLEPEDFAVYSC | QHYDN--- -------- | ----SPWT FGQGT KVEIK |
| iPS:434 913 | 21-225_86C1 | VK3}A27/ JK1 | EIVLTQSPGTLYL SPGERATLSC | RAS--QSVYS- ---SYLA | WYQQKPGQ APRLLIY | G------- ASSRST | GIPDRFSGSGSG- TDFALTISRLEPEDCAVYYC | QHSDN--- -------- | ----SPWT FGQGT KVEIK |
| iPS:434 921 | 21-225_86E4 | VK3}A27/ JK1 | EIVLTQSPGTLYL SPVERATLSC | RAS--QSVYS- ---SYLA | WYQQKPGQ APRLLIY | G------- ASSRST | GIPDRFSGSGCG- TDFALTISRLEPEDCAVYYC | QHSDN--- -------- | ----SPWT FGQGT KVEIK |
| iPS:434 939 | 21-225_86C11 | VK3}A27/ JK1 | EIVLTQSPGTRYL SPGERATLSC | RAS--QSVYS- ---SYLA | WYQQKPGQ APRLLIY | G------- ASSRST | GLPDRFSGSGSG- TDFALTISRVEPEDCAVYYC | QHSDN--- -------- | ----SPWT FGQGT KVEIK |
| iPS:434 943 | 21-225_87A12 | VK3}A27/ JK1 | EIVLTQSPGTLSL SPGERATLSC | RAS--QSVDS- ---NYLA | WYQQKPGQ APRLLIY | G------- ASSRST | GIPDRFSGSGSG- TDFTLTISRLEPEDFAVYYC | QQYES--- -------- | ----SPWT FGQGT KVEIK |
| iPS:434 945 | 21-225_87H1 | VK3}A27/ JK1 | EFVLTQSPGTLYL SPGERATLSC | RAS--QSVYS- ---SYLA | WYQQKPGQ APRLLIY | G------- ASSRST | GIPDRFSGSGSG- TDFALTISRLEPEDCAVYYC | QHSDN--- -------- | ----SPWT FGQGT KVEIK |
| iPS:434 955 | 21-225_87E5 | VK3}A27/ JK1 | EIVLTQSPGTLSL SPGERATLSC | RAS--QSVYS- ---SYLA | WYQQKPGQ APRLLIY | G------- ASSRST | GIPDRFSGSGSG- TDFALTISRLEPEDCAVYYC | QHSDN--- -------- | ----SPWT FGQGT KVEIK |
| iPS:434 961 | 21-225_87C9 | VK3}A27/ JK1 | EIVLTQSPGTRYL SPGERATLSC | RAS--QSVYS- ---SYLA | WYQQKPGQ APRLLIY | G------- ASSRST | VIPDRFSGSGSG- TDFALTISRVEPEDCAVYYC | QHSDN--- -------- | ----SPWT FGQGT KVEIK |
| iPS:434 969 | 21-225_88H1 | VK3}A27/ JK1 | EIVLTQSPGTLYL SPGERATLSC | RAS--QSVYS- ---SYLA | WYQQKPGQ APRLLIY | G------- ASSRST | VIPDRFSGSGCG- TDFALTISRVEPEDCAVYYC | QHSDN--- -------- | ----SPWT FGQGT KVEIK |
| iPS:434 981 | 21-225_88E7 | VK3}A27/ JK1 | EIVLTQSPGTLSL SPGERATLSC | RAS--QSVYS- ---NYLA | WYQQKPGQ APRLLIY | G------- ASSRST | GIPDRFSGSGSG- TDFTLTISRLEPEDFAVYYC | QQYES--- -------- | ----SPWT FGQGT KVEIK |
| iPS:434 983 | 21-225_88F7 | VK3}A27/ JK1 | EIVLTQSPGTLSL SPGERATLSC | RAS--QSVYS- ---SYLA | WYQQKPGQ APRLLIY | G------- ASSRAT | GIPDRFSGSGSG- TDFALTISRLEPEDCAVYYC | QHSDN--- -------- | ----SPWT FGQGT KVEIK |
| iPS:434 995 | 21-225_88G9 | VK3}A27/ JK1 | EIVLTQSPGTLSL SPGERATLSC | RAS--QSVYS- ---SYLA | WYQQKPGQ APRLLIY | G------- ASSRST | GIPDRFSGSGSG- TDFALTISRLEPEDCAVYYC | QHSDN--- -------- | ----SPWT FGQGT KVEIK |
| iPS:434 999 | 21-225_75A8 | VK3}A27/ JK1 | EIVLTQSPGTLYL SPGERATLSC | RAS--QSVYS- ---SYLA | WYQQKPGQ APRLLIY | G------- ASSRAT | GIPDRFSGSGSG- TDFALTISRVEPEDCAVYYC | QHYDN--- -------- | ----SPWT FGQGT KVEIK |
| iPS:435 013 | 21-225_89D5 | VK3}A27/ JK1 | EIVLTQSPGTLYL SSGERATLSC | RAS--QSVYS- ---SYLA | WYQQKPGQ APRLLIY | G------- ASSRST | GIPDRFSGSGSG- TDFALTISRLEPEDFAVYYC | QHYDN--- -------- | ----SPWT FGQGT KVEIK |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS-435_015 | VK3/A27/ JK1 | EIVLTQSPGTLSL SPGERATLSC | RAS--QSVNS- ----NYLA | WYQQKPGQ APRLLIY | G------ AFSRAT | GIPDRVSGSGSG-- TDFNLTISRLEPEDFAVYYC | QQYES--- ------- | ---SVWT | FGQGT KVEIK |
| iPS-435_025 | VK3/A27/ JK1 | EIVLTQSPGTLYL SSGERATLSC | RAS--QSVYS- ----SYLA | WYQQKPGQ APRLLIY | G------ ASSRST | VIPDRFSGSGSG-- TDFALTISRVEPEDHEDFAVYYC | QHSDN--- ------- | ---SPWT | FGQGT KVEIK |
| iPS-435_029 | VK3/A27/ JK1 | EIVLTQSPGTLSL SPGERATLSC | RAS--QSVDS- ----NFLA | WYQQKPGQ APRLLIY | G------ ASARTT | GIPDRFSGSGSG-- TDFTLTISRLEPEDFAVYSC | QQYEI--- ------- | ---SPWT | FGQGT KVEIK |
| iPS-435_039 | VK3/A27/ JK1 | EIVLTQSPGTLYL SPGERATLSC | RAS--QSVYS- ----SYLA | WYQQKPGQ APRLLIY | G------ ASSRST | VIPDRFSGSGSG-- TDFALTISRVEPEDCAVYYC | QHSDN--- ------- | ---SPWT | FGQGT KVEIK |
| iPS-435_041 | VK3/A27/ JK1 | EIVLTQSPGTLYL SPGERATLSC | RAS--QSVYS- ----SYLA | WYQQKPGQ APRLLIY | G------ ASSRAT | GIPDRFSGSGSG-- TDFALTISRVEHEDFAVYYC | QHYDN--- ------- | ---SPWT | FGQGT KVEIK |
| iPS-435_043 | VK3/A27/ JK1 | EIVLTQSPGTLYL SPGERATLSC | RAS--QSVYS- ----SYLA | WYQQKPGQ APRLLIY | G------ ASSRAT | TDFALTISRVEHEDFAVYYC | QHYDN--- ------- | ---SPWT | FGQGT KVEIK |
| iPS-435_055 | VK3/A27/ JK1 | EIVLTQSPGTLSL SPGERATLSC | RAS--QSVYS- ----SYLA | WYQQKPGQ APRLLIY | G------ ASSRST | GIPDRFSGSGSG-- TDFALTISRLEPEDFAVYYC | QHYDN--- ------- | ---SPWT | FGQGT KVEIK |
| iPS-435_073 | VK3/A27/ JK1 | EIVLTQSPGTLYL SPGERATLSC | RAS--QSVYS- ----SYLA | WYQQKPGQ APRLLIY | G------ ASSRST | VIPDRFSGSGSG-- TDFALTISRVEPEDCAVYYC | QHYDN--- ------- | ---SPWT | FGQGT KVEIK |
| iPS-435_075 | VK3/A27/ JK1 | EIVLTQSPGTLYL SPGERATLSC | RAS--QSVYS- ----SYLA | WYQQKPGQ APRLLIY | G------ ASSRST | GIPDRFSGSGSG-- TDFALTISRVEHEDCAVYYC | QHSDN--- ------- | ---SPWT | FGQGT KVEIK |
| iPS-435_077 | VK3/A27/ JK1 | EIVLTQSPGTLYL SPGERATLSC | RAS--QSVYS- ----SYLA | WYQQKPGQ APRLLIY | G------ ASSRST | GIPDRFSGSGSG-- TDFALTISRVEHEDCAVYYC | QHYDN--- ------- | ---SPWT | FGQGT KVEIK |
| iPS-435_079 | VK3/A27/ JK1 | EIVLTQSPGTLYL SPGERATLSC | RAS--QSVYS- ----SYLA | WYQQKPGQ APRLLIY | G------ ASSRST | GIPDRFSGSGSG-- TDFALTISRVEPEDCAVYYC | QHYDN--- ------- | ---SPWT | FGQGT KVEIK |
| iPS-435_089 | VK3/A27/ JK1 | EIVLTQSPGTLSL SPGERATLSC | RAS--QSVYS- ----SYLA | WYQQKPGQ APRLAQ | G------ ASSRST | TDFALTISRVEPEDCAVYYC | QHSDN--- ------- | ---SPWT | FGQGT KVEIK |
| iPS-435_097 | VK3/A27/ JK1 | EIVLTQSPGTLSL SPGERATLSC | RAS--QSVGS- ----SYLA | WYQQKRGQ APRLLIY | G------ ASSRST | DIPDRFSGSGSG-- TDFTLTISRLEPEDFAVYYC | QQYES--- ------- | ---SPWT | FGQGT KVEIK |
| iPS-435_111 | VK3/A27/ JK1 | EIVLTQSPGTLSL SPGERATLSC | RAS--QSVDS- ----NYLA | WYQQKPGQ APRLLIY | G------ ASSRAP | VIPDRFSGSGSG-- TDFALTISRLEPEDCAVYYC | QHYDN--- ------- | ---SPWT | FGQGT KVEIK |
| iPS-435_115 | VK3/A27/ JK1 | EIVLTQSPGTLYL SPGERATLSC | RAS--QSVSS- ----SYLA | WYQQKPGQ APRLLIY | G------ ASSRST | GIPDRFSGSGSG-- TDFALTISRLEPEDCAVYYC | QHYDS--- ------- | ---SPWT | FGQGT KVEIK |
| iPS-435_171 | VK3/A27/ JK1 | EIVLTQSPGTLSL SPGERATLSC | RAS--QSVYS- ----SYLA | WYQQKPGQ APRLLIY | G------ ASSRST | GIPDRFSGSGSG-- TDFALTISRLEPEDFAVYYC | QHYDN--- ------- | ---SPWT | FGQGT KVENQ |
| iPS-435_177 | VK3/A27/ JK1 | EIVLTQSPGTLYL SPGERATLSC | RAS--QSVYS- ----SYLA | WYQQKTGQ APRLLIY | G------ ASSRST | GIPDRFSGSGSG-- TDFALTISRLEPEDFAVYYC | QHYDN--- ------- | ---SPWT | FGQGT KVEIK |
| iPS-435_183 | VK3/A27/ JK1 | EIVLTQSPGTLSL SPGERATLSC | RAS--QSVDS- ------SYLA | WYQQKPGQ APRLLIY | G------ ASSRST | GIPDRFSGSGSG-- TDFALTISRLEPEDFAVYYC | QHYDN--- ------- | ---SPWT | FGQGT KVEIK |
| iPS-435_195 | VK3/A27/ JK1 | EIVLTQSPGTLSL SQGERATLSC | RAS--QSVSS- ----RYLA | WYQQKPGQ APRLLIY | G------ ASSRST | GIPDRFSGSGSG-- TDFTLTISRLEPEDFAVYYC | QHYDN--- ------- | ---SPWT | FGQGT KVEIK |
| iPS-435_217 | VK3/A27/ JK1 | EIVLTQSPGTLYL SPGERATLSC | RAS--QSVYS- ----SYLA | WYQQKPGQ APRLLIY | G------ ASSRST | GIPDRFSGSGSG-- TDFALTISRLEPEDFAVYYC | QHYDN--- ------- | ---SPWT | FGQGT KVEIK |
| iPS-435_219 | VK3/A27/ JK1 | EIVLTQSPGTLYL SPGERATFSC | RAS--QSVYS- ----SYLA | WYQQKPGQ APRLLIY | G------ ASSRST | GIPDRFSGSGSG-- TDFALTISRLEPEDCAVYYC | QHYDN--- ------- | ---SPWT | FGQGT KVEIK |
| iPS-435_235 | VK3/A27/ JK1 | EIVLTQSPGTLSL SPGERATLSC | RAS--QSVYS- ----SYLA | WYQQKPGQ APRLLIY | G------ ASSRST | GIPDRFSGSGCG-- TDFALTISRLEPEDCAVYYC | QHYDN--- ------- | ---SPWT | FGQGT KVEIK |
| iPS-435_237 | VK3/A27/ JK1 | EIVLTQSPGTLYL SSGERATLSC | RAS--QSVYS- ----SYLA | WYQQKPGQ APRLLIY | G------ ASSRST | GIPDRFSGSGSG-- TDFALTISRVEHEDCAVYYC | QHYDN--- ------- | ---SPWT | FGQGT KVEIK |

Figure 51 (Continued)

| ID | Gene | Seq1 | Seq2 | Seq3 | Seq4 | Seq5 | Seq6 | Seq7 |
|---|---|---|---|---|---|---|---|---|
| iPS-435 239 | 21-225_95H10 | VK3/A27/ JK1 | EIVLSQSPGILYL SSGERAILSC | RAS--QSVYS- ----SYLA | WYQQKPGQ APRLLIY | G------ ASSRAT | GIPDRFSGSGSG-- TDFALTISRLEPEDFAVYYC | QEYDN------- -------SPWT | FGQGT KVEIK |
| iPS-435 273 | 21-225_97A2 | VK3/A27/ JK1 | EIVLTQSPGTLYL ----SYLA | RAS--QSVYS- SSGERAALSC | WYQQKPGQ APRLLIY | G------ ASSRST | GIPDRFSGSGSG-- TDFALTISRLEPEDCAVYYC | QESDN------- -------SPWT | FGQGT KVEIK |
| iPS-435 281 | 21-225_97E5 | VK3/A27/ JK1 | EIVLTQSPGTLSL SPGERATLSC | RAS--QSVYS- ----SYLA | WYQQKPGQ APRLLIY | G------ ASSRAT | GIPDRFSGSGCG-- TDFALTISRVEPEDCAVYYC | QESDN------- -------SPWT | FGQGT KVEIK |
| iPS-435 331 | 21-225_147G8 | VK3/A27/ JK1 | QIVLTQSPGTLSL SPGERATLSC | RAS--QRIFS- ----NYLA | WYQQKPGQ APRLLIY | G------ ASSRAT | GIPDRISGSGSG-- TDFTLTITRLEPEDFAVYYC | QQYDS------- -------SPWT | FGQGT KVEIK |
| iPS-435 815 | 21-225_190G1 0 | VK3/A27/ JK1 | EIVLTQSPGTLSL SPGERATLSC | RAS--PSVSS- ------RFLA | WYQQKPGQ APRLLIY | G------ ASSRAT | GIPDRFSGSGSG-- TDFTLTNRLEPEDFAVYYC | QQYGS------- ------SPPWT | FGQGT KVEIK |
| iPS-435 843 | 21-225_191F1 | VK3/A27/ JK1 | EIVLTQSPGTLSL SPGERAALSC | RAS--QSISL- ----NFLA | WYQQKPGQ APRLLIY | G------ ASSRAT | GIPDRFSGSGSG-- TDFTLTINRLEPEDFAVYYC | QQYGN------- -------SPWT | FGQGT KVEVK |
| iPS-435 847 | 21-225_191A3 | VK3/A27/ JK1 | EIVLTQSPGTLSL SPGERATLSC | RAS--QSIRS- ----SFLA | WYQQKPGQ APRLLIY | G------ ASSRAT | GIPDRFSGSGSG-- TDFTLTISRLEPEDFAVYYC | QQYGN------- -------SFWA | FVQGT KVEVK |
| iPS-435 849 | 21-225_191C3 | VK3/A27/ JK1 | EIMLTQSPGTLSL SPGERATLSC | RAS--QNIRS- ----NFLA | WYQQKPGQ APRLLIY | G------ ASSRAT | GIPDRFSGSGVSG-- TDFTLTINRLEPEDFAVYYC | QQYGN------- -------SPWT | FGQGT KVEIK |
| iPS-435 851 | 21-225_191D3 | VK3/A27/ JK1 | EIVLTQSPGTLSL SPGESATLSC | RAG--QSIRT- ----NFLA | WYQQKPGQ APRLLIY | G------ ASSRAT | GIPARFSGSGSG-- TDFTLTINRLEPEDFAVYYC | QQYGS------- -------SPWA | FGQGT KVEIK |
| iPS-435 865 | 21-225_191A5 | VK3/A27/ JK1 | EIVLTQSPGTLSL SPGERATLSC | RAS--QSVSS- ------RFLA | WYQQKPGQ APRLLIY | G------ AYRRAT | GIPDRFSGSGSG-- TDFTLTINRLEPEDFAVYYC | QQYGN------- ------SPPWT | FGQGT KVEIK |
| iPS-435 905 | 21-225_190A3 | VK3/A27/ JK1 | EIVLTQSPGTLSL SPGESATLSC | RAS--QSIRT- ----DFLA | WYQQQPGQ APRLLIY | G------ PSSRAT | GIPDRFSGSVSG-- TDFTLTINRLEPEDFAVYYC | QQYGN------- -------SPWT | FGQGT KVEIN |
| iPS-435 911 | 21-225_190B4 | VK3/A27/ JK1 | EIVLTQSPGTLSL SPGERATLSC | RAS--QSIRS- ----SFLA | WYQQKPGQ APRLLIF | G------ ASSRAT | GIPDRFSGSGSG-- TDFTLTISRLEPEDFAVYYC | QQYES------- -------SPWA | FGQGT KVEIK |
| iPS-435 913 | 21-225_190A7 | VK3/A27/ JK1 | EIVLTQSPGTLSL SPGESATLSC | RAS--QSISS- ----SYLA | WYQQKPGQ APRLLIY | G------ ASNRAT | GIPDRFSGSGSG-- TDFTLTINRLEPEDFAVYYC | QQYGN------- -------SPWT | FGQGT KVEIK |
| iPS-435 939 | 21-225_191H7 | VK3/A27/ JK1 | EIVLTQSPGTLSL SPGESATLSC | RAS--QSVRS- ----NFLA | WLQQKPGQ APRLLIY | G------ VSRRAT | GIPDRFSGSGSG-- TDFTLTINRLEPEDFAVYYC | QQYGN------- -------SPWT | FGQGT KVEIN |
| iPS-435 967 | 21-225_192B3 | VK3/A27/ JK1 | EIVLTQSPGTLSL SPGERATLSC | RAS--QSVRS- ----SFLA | WHQQKPGQ APRLFIY | G------ ASRRAT | GIPDRFSGSGSG-- TDFTLTISRLEPEDFAVYYC | QQYGN------- -------SPWT | FGQGT KVEIK |
| iPS-435 973 | 21-225_192H3 | VK3/A27/ JK1 | EIVLTQSPGTLSL SPGESATLSC | RAS--QSVSS- ----NFLA | WHQQKPGQ APRLLIY | G------ ASSRAT | GIPDRFSGSGSG-- TDFTLTISRLEPEDFAVYFC | QQYGN------- -------SFWA | FGQGT KVEIK |
| iPS-435 995 | 21-225_192F8 | VK3/A27/ JK1 | EIVLTQSPGTLSL SPGERATLSC | RAS--QSISS- ----NFLA | WYQQKPGQ APRLLIF | G------ ASSRAT | GIPDRFSGSGSG-- TDFTLTINRLEPEDFAVYYC | QQYGI------- -------SPWT | FGQGT KVEIK |
| iPS-436 007 | 21-225_192G1 | VK3/A27/ JK1 | EIVLTQSPGTLSL SPGERATLSC | RAS--QSVRS- ----SYLA | WYQQKPGQ APRLLIY | G------ ASSRAT | GIFARFSGSGSG-- TDFTLTISRLEPEDFAVYYC | QQYES------- -------SPWT | FGQGT KVEIK |
| iPS-436 009 | 21-225_193A1 | VK3/A27/ JK1 | EIVLTQSPGTLSL SPGESATLSC | RAS--QSISL- ----NFLA | WHQQKPGQ APRLFIX | G------ ASRRAT | GIPDRFSGSGSG-- TDFTLTINRLEPEDFAVYFC | QQYGN------- -------SPWT | FGQGT KVEIK |
| iPS-436 011 | 21-225_193B1 | VK3/A27/ JK1 | EIVLTQSPGTLSL SPGERATLSC | RAS--QSVRS- ----NFLA | WHQQKPGQ APRLLIY | G------ ASSRAT | GIPDRFSGSGSG-- TDFTLTISRLEPEDFAVYYC | QQYGN------- -------SFWA | FGQGT KVEIK |
| iPS-436 015 | 21-225_193D3 | VK3/A27/ JK1 | EIVLTQSPGTLSL SPGERATLSC | RAS--QSIRS- ----SFLA | WYQQKPGQ APRLLIY | G------ ASNRAT | GIPDRFSGSGSG-- TDFTLTINRLEPEDFAVYYC | QQYGN------- -------SPWA | FGQGT KVEIK |
| iPS-436 017 | 21-225_193F3 | VK3/A27/ JK1 | EIVLTQSPGTLSL SPGESATLSC | RAG--QSIRT- ----DFLV | WYQQQPGQ APRLLIY | G------ ASSRAT | GFPERFSGSGSG-- TDFTLTINRLEPEDFAVYYC | QQYGS------- -------SPWT | FGQGT KVEIN |

Figure 51 (Continued)

| | | | | | | | |
|---|---|---|---|---|---|---|---|
| iPS:436 027 | 21-225_193E6 | VK3/A27/ JK1 | EIVLAQSPGTLSL SPGERATLSC | RAS---QSVRS- ----GYLA | WYQQKPGQ APRLLIY | G------- ASSRAT | GIPDRFGGSGSG-- TDFTLTISRLEPEDFAVYYC | QQYES----------SPWT | FGQGT KVEIK |
| iPS:436 029 | 21-225_193H6 | VK3/A27/ JK1 | EIVLTQSPGTLSL SPGESATLSC | RAG---QSIRT- ----NFLA | WYQQKPGQ APRLLIY | G------- ASSRAT | GIPDRFSGSGSG-- TDFTLTISRLEPEDFAVYYC | QQYGS----------SPWA | FGQGT KVEIN |
| iPS:436 035 | 21-225_193C8 | VK3/A27/ JK1 | EIVLTQSPGTIFL SPGERATLSC | RAS---QSIRS- ----SFLA | WYQQKPGQ APRLLIY | G------- ASSRAT | GIPDRFSGSGSG-- IDFTLTISRLEPEDFAVYYC | QQYGN----------SPWA | FGQGT KVEVK |
| iPS:436 037 | 21-225_193D8 | VK3/A27/ JK1 | EIVLKQSPGTLFL SPGERATLSC | RAS---QSIRI- ----NFLA | WYQQKPGQ APRLLIY | G------- ASSRAT | GIPDRFSGSGSG-- TDFTLTINRLEPEDFAVYYC | QQYGN----------SPWT | FGQGT KVEIK |
| iPS:436 041 | 21-225_193G8 | VK3/A27/ JK1 | EIVLTQSPGTLSL SPGERATLSC | RAS---QSVRT- ----NFLA | WHQQKPGQ APRLLIY | G------- ASPRAT | GIPDRFSGSGSG-- TDFTLTINRLEPEDFALYYC | QQYGN----------SPWT | FGQGT KVEIK |
| iPS:436 047 | 21-225_193B1 | VK3/A27/ JK1 | EIVLTQSPGTLSL SPGERATLSC | RAS---PSVSS- ----SYLA | WYQQKPGQ APRLVIY | G------- ASRRAT | GIPDRFRGSGSG-- TDFTLTISRLEPEDFAVYYC | QQYGS----------SPWT | FGQGT KVEIK |
| iPS:436 049 | 21-225_193B1 2 | VK3/A27/ JK1 | EIVLTQSPGTLSL SPGERATLSC | RAS---QSIRS- ----SFLA | WYQQKPGQ APRLLIY | D------- ASSRAT | GIPDRFSGSGSG-- TDFTLTISRLEPKDFAVYYC | QQYGN----------SPWA | FGQGT KVEIK |
| iPS:436 062 | 21-225_194E5 | VK3/A27/ JK1 | EIVLTQSPGSATLSC SSGERATLSC | RAG---QSIRT- ----NFLA | WYQQKPGQ APRLLIY | G------- ASSRAT | GIPDRFSGSGSG-- IDFTLTINRLEPKDFAVYYC | QQYGS----------SPWT | FGQGT KVEIK |
| iPS:436 064 | 21-225_194E6 | VK3/A27/ JK1 | EIVLTQSPGTLSL SPGESATLSC | RAS---QSIRT- ----SFLA | WYQQKPGQ APRLLIY | G------- ASSRAT | GIPDRFSGSVSG-- TDFTLTISRLEPEDFAVYYC | QQYGS----------SPWA | FGQGT KVEIK |
| iPS:436 072 | 21-225_194C1 | VK3/A27/ JK1 | EIVLTQSPGTLSL SPGERATLSC | RAS---PSVNS- ----GYLA | WYQQKPGQ TPRLLIF | G------- ASSRAT | GIPDRFSASGSG-- ADFTLTINSRLEPEDFAVYYC | QQYES----------SPWT | FGQGT KVEIK |
| iPS:436 080 | 21-225_195B1 | VK3/A27/ JK1 | EIVLTQSPGTLSL SPGERATLSC | RAS---PSVNS- ----NYLA | WYQQKPGQ TPRLLIY | G------- ASNRAT | GVPDRFSASGSG-- TDFTLTIRRLEPEDFAVYYC | QQYGS----------SPWT | FGQGT KVEIK |
| iPS:436 088 | 21-225_195C8 | VK3/A27/ JK1 | EIVLTQSPGTLSL SPGERATLSC | RAS---QSIRS- ----SFLA | WYQQKPGQ APRLLIY | G------- AFSRAT | GIPDRFSGSGSG-- TDFTLTISRLEPEDFAVYYC | QQYGN----------SPWA | FGQGT KVEIK |
| iPS:436 122 | 21-225_196G1 | VK3/A27/ JK1 | EIVLTQSPGTLLL SPGERATLSC | RAS---PSVSN- ----SFLA | WYQQKPGQ APRLLIY | G------- AFSRAT | GIPDRFSGSGSG-- TDFTLTINRLEPEDFAVYYC | QQYGS----------SPPWT | FGQGT KVEIK |
| iPS:436 134 | 21-225_196H1 2 | VK3/A27/ JK1 | EIVLTQSPGTLSL SPGERATLSC | RAS---QSVRS- ----NFLA | WHQQKPGQ APRLLIY | G------- AYRRAT | GIPDRFSASGSG-- TDFTLTIRRLEPEDFAVYYC | QQYES----------SPWT | FGQGT KVEIK |
| iPS:436 146 | 21-225_197F4 | VK3/A27/ JK1 | EIVLTQSPGTLSL SPGERATLSC | RAS---QSIRS- ----SFLA | WYLQKPGQ APRLLIY | G------- ASSRAT | GIPDRFSGSGSG-- TDFTLTINRLEPEDFAVYYC | QQYGN----------SPWA | FGQGT KVEIK |
| iPS:436 177 | 21-225_198B1 | VK3/A27/ JK1 | EIVLTQSPGSATLSC SPGESATLSC | RAG---QSIRT- ----NFLA | WYQQQPGQ APRLLIY | G------- ASSRAT | GIPDRFSGSGSG-- TDFTLTINRLEPEDFAVYYC | QQYGS----------SPWT | FGQGT KVEIK |
| iPS:436 179 | 21-225_198E1 | VK3/A27/ JK1 | EIVLTQSPGTLSL SPGERATLSC | RAS---QSIRS- ----NFLA | WYQQKPGQ APRLLIY | G------- AFSRAT | GIPDRFSGSGSG-- TDFTLTINRLEPEDFAVYYC | QQYGN----------SPWT | FGQGT KVEIK |
| iPS:436 181 | 21-225_198C2 | VK3/A27/ JK1 | EIVLTQSPGTILLL YSEERSTLSC | RAS---QSVRS- ----SYLA | WYQQKPGQ APRLLIC | G------- AFSRAS | GIPDRFSGSGSG-- TDFTLTISRLEPEDFAVYYC | QQYGN----------SPWT | LGHAT KVEIK |
| iPS:436 195 | 21-225_198G1 | VK3/A27/ JK1 | EIVLTQSPGTLSL SPGERATLSC | RAS---QSIRS- ----SFLA | WYQQKPGQ APRLLIY | G------- ASSRAT | GIPDRFSGSGSG-- TDFTLTISRLEPEDFAVYYC | QQYGN----------SPWT | FGQGT KVEIK |
| iPS:436 197 | 21-225_199C2 | VK3/A27/ JK1 | EIVLTQSPGTLSL SPGERATLSC | RAS---QSIRS- ----SFLA | WYQQKPGQ APRLLIY | G------- ASSRAT | GIPDRFSGSGSG-- TDFTLTINRLEPEDFAVYYC | QQYGN----------SPWA | FGQGT KVEIK |

Figure 51 (Continued)

| | | | | | | | | |
|---|---|---|---|---|---|---|---|---|
| iPS:436 207 | 21- 225_199C7 | VK3|A27/ JK1 | EIVLTQSPGTLSL SPGERATLSC | RAS--QSIRT- ----NFLA | WYQQKPGQ APRLLIY | G------- ASSRAT | GIPDRFSGSGSG-- TDFTLTINRLEPEDFAVYYC | QQYGN---------- --------SPWT | FGQGT KVEIK |
| iPS:436 210 | 21- 225_199G1 | VK3|A27/ JK1 | EIVVTQSPGPGTLSL SPGERATLSC | RAS--QSVKS- ----SYLA | WYQQKPGQ APRLLIY | G------- AFSRAT | GIPDRFSGSGSG-- TDFTLTISRLEPEDFAVYYC | QQYGN---------- --------SPWA | FGHGT KVEIK |
| iPS:436 226 | 21- 225_200F10 | VK3|A27/ JK1 | EIVLTQSPGTLSL SPGERATLSC | RAS--QNIRS- ----SFLA | WYQQKPGQ APRLLIY | G------- ASSRAT | GIPDRFSGSGSG-- TDFTLTINRLEPEDFAVYYC | QQYGS---------- --------SPWA | FGQGT KVEIK |
| iPS:436 232 | 21- 225_201E1 | VK3|A27/ JK1 | EIVLTQSPDTLSL SPGERATLSC | RAS--PSINS- ----GFLA | WYQQKPGQ APRLLIY | G------- ASSRAT | GIPDRFSGSGSG-- TDFTLTISRLEPEDFAMHC | HQYET---------- --------SPWT | FGQGT KVEIK |
| iPS:436 238 | 21- 225_201B2 | VK3|A27/ JK1 | EIVLTQSPGTLSL SPGERATLSC | RAS--QSVSS- ----NYLA | WYQQRPGQ APRLLIY | G------- ASSRAT | GIPDRFSGSGSG-- TDFTLTISRLEPEDFAVFC | QQYEN---------- --------SPWT | FGQGT KVEIK |
| iPS:436 256 | 21- 225_202D9 | VK3|A27/ JK1 | EIVLTQSPGTLSL SPGERATLSC | RAS--QSVNS- ----GYLA | WYQQKPGQ SPRLLIY | G------- ASSRAT | GIPDRFSGSGSG-- TDFTLTISRLEPEDFAVHYC | QQYET---------- --------SPWT | FGQGT KVEIK |
| iPS:436 302 | 21- 225_205G7 | VK3|A27/ JK1 | EIVLTQSPGTLSL SPGERATLSC | RAS--QSVFS- ----NYLA | WYQQKPGQ APRLLIY | G------- ASSRAT | GIPDRFSGSGSG-- TDFTLTIEPENFAVYYC | QQYES---------- --------SPWT | FGQGT KVEIK |
| iPS:436 310 | 21- 225_202D1 | VK3|A27/ JK1 | EIVLTQSPGTLSL SPGERATLSC | RAS--QSINS- ----NYLA | WYQRKPGQ APRVLIY | G------- ASSRAT | GIPDRFSGSGSG-- TDFTLTISRLEPEDFAVYYC | QQYEN---------- --------SPWT | FGQGT KVEIK |
| iPS:436 336 | 21- 225_208B5 | VK3|A27/ JK1 | EIVLTQSPGTLSL SPGERATLSC | RAS--QSVSS- ----NYLA | WYQQKPGQ APRLLIY | G------- ASSRAT | GIPDRFSGSGSG-- TDFTLTISRLEPEDFAVYFC | QEYEN---------- --------SPWT | FGQGT KVEIK |
| iPS:436 340 | 21- 225_208A9 | VK3|A27/ JK1 | EIVLTQSPGTLYL SPGERATLSC | RAS--QSVSN- ----NYLA | WYQQKPGQ APRVLIY | G------- ASSRAT | GIPDRFSGSGSG-- TDFTLTISRLEPEDFAVYYC | QEYHS---------- --------SPWT | FGQGT KVEIK |
| iPS:436 472 | 21- 225_220E1 | VK3|A27/ JK1 | EIVLTQSPGTLYL SPGERATLSC | RAS--QSISR- ----SHLV | WYQQKPNQ APRLLIY | V------- TSSRAT | GIPDRFSGSGSG-- TDFTLTISRLEPEDFAMYYC | QQYGS---------- --------SPWT | FGQGT KVEIK |
| iPS:436 506 | 21- 225_222C7 | VK3|A27/ JK1 | EIVLTQSPGTLSL SPGERATLSC | RAS--QSVYS- ----NYLA | WYQQKPGQ APRLLIY | G------- ASSRAT | GIPDRFGSGSGSG-- TDFTLAISRLEPEDFTIYC | QQYED---------- --------SPWT | FGQGT KVEIK |
| iPS:436 580 | 21- 225_225E7 | VK3|A27/ JK1 | EIALTQSPGTLSL SPGERATLSC | RAS--PSVDS- ----NYLA | WYQQKPGQ APRLLIY | G------- ASSRAP | GIPDRFSGSGSG-- TDFTLTISRLEPEDFAVYYC | QQYGT---------- --------SPRT | FGRGT KVEIK |
| iPS:437 324 | 21- 225_75C2 | VK3|A27/ JK1 | EIVLTQSPGTLSL SPGERATLSC | RAS--QSVYS- ----SYLA | WYQQKPGQ APRLLIY | G------- ASSRAT | GIPDRFSGSGSG-- TDFALTISRLEPEDCAVYYC | QEYDN---------- --------SPWT | FGQGT KVEIK |
| iPS:437 328 | 21- 225_75D3 | VK3|A27/ JK1 | EIVLTQSPGTLYL SPGERATLSC | RAS--QSVIS- ----SYLA | WYQQKPGQ APRLLIY | G------- ASSRST | GIPDRFSGSGCG-- TDFALTISRVEHEDCAVYYC | QEYDN---------- --------SPWT | FGQGT KVEIK |
| iPS:437 332 | 21- 225_75F3 | VK3|A27/ JK1 | EIVLTQSPGTLYL SPGERATLSC | RAS--QSVYS- ----SYLA | WYQQKPGQ APRLLIY | G------- ASSRAT | GIPDRFSGSGCG-- TDFALTISRLEHEDFAVYYC | QEYDN---------- --------SPWT | FGQGT KVEIK |
| iPS:437 340 | 21- 225_75G9 | VK3|A27/ JK1 | EIVLTQSPGTLSL SPGERATLSC | RAS--QSVYS- ----SYLA | WYQQKPGQ APRLLIY | G------- ASSRAP | GIPDRFSGSGSG-- TDFTLTISRLEPEDFAVYYC | QQYES---------- --------SPWT | FGQGT KVEIK |
| iPS:437 344 | 21- 225_75G12 | VK3|A27/ JK1 | EIVLTQSPGTLYL SPGERATLSC | RAS--QSVYS- ----SYLA | WYQQKPGQ APRLLIY | G------- ASSRST | GIPDRFSGSGCG-- TDFALTISRVEPEDCAVYYC | QEYDN---------- --------SPWT | FGQGT KVEIK |
| iPS:437 350 | 21- 225_74A3 | VK3|A27/ JK1 | EIVLTQSPGTLSL SPGERATLSC | RAS--QSVYS- ----SYLA | WYQQKPGQ APRLLIY | G------- ASSRST | GIPDRFSGSGCG-- TDFALTISRLEPEDFAVYYC | QESDN---------- --------SPWT | FGQGT KVEIK |
| iPS:437 369 | 21- 225_74D6 | VK3|A27/ JK1 | EIVLTQSPGTLSL SPGERATLSC | RAS--QSFSS- ----SYLA | WYQQKPGQ APRLLIY | G------- ASSRAT | GIPDRFSGSGSG-- TDFTLTISRLEPEDFAVYYC | QEYDN---------- --------SPWT | FGQGT KVEIK |
| iPS:437 383 | 21- 225_74H8 | VK3|A27/ JK1 | EIVLTQSPGTLSL SPGERATLSC | RAS--QSVNS- ----SYLA | WYQQKPGQ APSLLIY | G------- ASSRAT | GIPDRFSGSGCG-- TDFTLTISRLEPEDFAVYYC | QQYG----------- --------SSRT | FGQGT KVEIK |
| iPS:451 122 | 21- 225_200A1 | VK3|A27/ JK1 | EIVLTQSPGILSL YPGERATLSC | RAS--QSVNS- ----NYLA | WYQQKPGQ APSLLIY | G------- ASSRAT | CILDRFSGSGCG-- TDFTLTISRLEPEDFAVYCC | QQYEI---------- --------SPWT | FGQGT KVESK |

Figure 51 (Continued)

| iPS:392 864 | VK3JA27/ JK1 | | EIVLTQSPGTLSL SPGERATLSC | RAS--QNVYS- ---SYLA | WYQQKPGQ TPRLLIY | G------ ASSRAS | GIPDRFSGSGSG- TDFTLTISRLEPEDFAVYYC | QQYGS------- ------SPRT | FGQGT KVEIK |
|---|---|---|---|---|---|---|---|---|---|
| | Germline | | K_FR1 | K_CDR1 | K_FR2 | K_CDR2 | K_FR3 | K_CDR3 | K_FR4 |
| iPS:468 864 | VK1|A30|JK 4 | | | | | | | | |
| iPS:468 812 | VK1|A30/ JK4 | | DIQMTQFPSSLSA SVGDRVTITC | RAS--RDIR- ----NDLG | WYQQKPGK APKRLIY | A------ ASSLQS | GVPSRFSGSGSG-- TEFTLTISSLQPEDFATYYC | LQHYS------- ------YPLT | FGGGT KVEIK |
| iPS:468 824 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS------- ------YPLT | FGGGT KVEIK |
| iPS:468 818 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFETYYC | LQHND------- ------YPFT | FGGGT KVEIK |
| iPS:468 840 | VK1|A30/ JK4 | | DIQMTQSPSSLSA SVGDRVTITC | RAS--QGIR- ----NDLG | WYQQKPGK APKRLIY | A------ ASSLQS | GIPSRFSGSGSG-- TEFTLTISSLQPEDFATYYC | LQHNS------- ------YPLT | FGGGT KVEIK |
| iPS:468 868 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHDS------- ------YPLT | FGGGA KVEIK |
| iPS:392 920 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS------- ------YPLT | FGGGT KVEIT |
| iPS:433 899 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS------- ------YPLT | FGGGT KVGII |
| iPS:433 921 | VK1|A30/ JK4 | | DIQMTQSPSSLSA SVGDRVTITC | RAS--QGIR- ----NDLG | WYQQKPGK APKRLIY | A------ ASSLQS | GVPSRFSGGGSG-- TEFTLTISSLQPEDFATYYC | LQHSS------- ------YPLT | FGGGT KVEIK |
| iPS:433 947 | VK1|A30/ JK4 | | DIQMTQSPSSLSA SVGDRVTITC | RTS--QGIR- ----NDLG | WYQQKPGK APKRLIY | A------ ASSLQS | GVPSRFSGSGSG-- TEFTLTISSLQPEDFATYYC | LQHNS------- ------YPLT | FGGGT KVEIK |
| iPS:433 963 | VK1|A30/ JK4 | | DIQMTQSPSSLSA SVGDRVTITC | RAS--QGIR- ----NDLG | WYQQKPGK APKRLIY | A------ ASSLQG | GVPSRFSGSGSG-- TEFTLTISSLQPEDFATYYC | LQHNS------- ------YPLT | FGGGT KVEIK |
| iPS:433 969 | VK1|A30/ JK4 | | DIQMTQSPSSLSA SVGDRVTITC | RAS--QGIR- ----KDLG | WYQQKPGK APKRLIY | A------ ASSLQS | GVPSRFSGSGSG-- TEFTLTISSLQPEDFATYYC | LQHNS------- ------YPLT | FGGGT KVEIK |
| iPS:433 975 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS------- ------YPLT | FGGGT KVEIT |
| iPS:433 977 | VK1|A30/ JK4 | | DIQMTQSPSSLSA SVGDRVTITC | RAS--QGIR- ----KDLG | WYQQKPGK APKRLIY | A------ ASSLQS | GVPSRFSGSGSG-- TEFTLTISSLQPEDFATYYC | LQHNS------- ------YPLT | FGGGT KVEIK |
| iPS:433 983 | VK1|A30/ JK4 | | DIQMTQSPSSLSA SVGDRVTITC | RAS--QDIR- ----NDLG | WYQQKPGK APKRLIY | A------ AFSLQS | GVPSRFSGSRSG-- TEFTLTISSLQPEDFATYYC | LQHNS------- ------YPLT | FGGGT KVEIK |
| iPS:433 987 | VK1|A30/ JK4 | | DIQMTQSPSSLSA SVGDRVTITC | RAS--QGIR- ----NNLG | WYQQKPGK VPKRLIY | A------ ASSLQS | GVPSRFSGSGSG-- TEFTLTISSLQPEDFATYYC | LQHNS------- ------YPLT | FGGGT KVEIT |
| iPS:434 013 | VK1|A30/ JK4 | | DIQMTQSPSSLSA SVGDRVTITC | RAS--QGIR- ----NDLG | WYQQKPGK APKRLIY | A------ ASTLQS | GVPSRFSGSGSG-- TEFTLTISSLQPEDFATYYC | LQHNS------- ------YPLT | FGGGT KVEIK |
| iPS:434 019 | VK1|A30/ JK4 | | DIQMTQSPSSLSA SVGDRVTITC | RAS--QGIR- ----NDLD | WYQQKPGK APKRLIY | A------ ASSLQS | GVPSRFSGSGSG-- TEFTLTISSLQPEDFATYYC | LQHNS------- ------YPLT | FGGGT KVEIK |
| iPS:434 029 | VK1|A30/ JK4 | | DIQMTQSPSSLSA SVGDRVTITC | RAS--QGIR- ----NDLG | WYQQKPGK APKRLIY | A------ ASSLQS | GFPSRFSGSGSG-- TEFTLTISSLQPEDFATYYC | LQHNS------- ------YPLT | FGGGT KVEIK |
| iPS:434 043 | VK1|A30/ JK4 | | DIQMTQSPSALSA SVGDRVTITC | RAS--QGIR- ----NDLG | WYQQKPGK APKRLIY | A------ ASSLQS | GVPSRFSGSGSG-- TEFTLTISSLQPEDFATYYC | LQYNS------- ------YPFT | FGGGT KVESK |
| iPS:434 077 | VK1|A30/ JK4 | | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS------- ------YPFT | FGGGT KVEIT |
| iPS:434 081 | VK1|A30/ JK4 | | DIQMTQSPSSLSA SVGDRVTITC | RAS--QGIR- ----NDLG | WYQQKPGK APRRLIY | A------ ASFLQS | GVPSTFSGSGSG-- TEFTLTISSLQPEDFATYYC | LQHNS------- ------YPLT | FGGGT KVEIK |

Figure 51 (Continued)

| | | | | | | | | | |
|---|---|---|---|---|---|---|---|---|---|
| iPS:434 105 | 21-225_53D2 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSG--- TEFTLTISSLQPEDFATYYC | LQHNR------------- ---------------YPLT | FGGGT KVEIK |
| iPS:434 119 | 21-225_53E6 | VK1|A30/ JK4 | DIQMTQSPSSLSA SVGARVTITC | RAS---QGIR- ----NDLG | WYQQNPGK APKRLIY | A------ ASNLQS | GVPSRFSGSGSG--- TEFTLTISSLQPEDFATYYC | LQHNR------------- ---------------YPLT | FGGGT KVEIK |
| iPS:434 141 | 21-225_54C6 | VK1|A30/ JK4 | DIQMTQSPSSLSA SVGDRVTITC | RAS---QGIR- ----NDLG | WYQQNPGK APKRLIY | A------ ASNLQS | GVPSRFSGSGSG--- TEFTLTISSLQPEDFATYYC | LQHNR------------- ---------------YPLT | FGGGT KVEIK |
| iPS:434 159 | 21-225_55B8 | VK1|A30/ JK4 | DIQMTQSPSSLSS SVGDRVTITC | RAS---CAIR- ----NDLG | WYQQKPGK APKRLIH | A------ APRLQS | GVPSRFSGSGSG--- TEFTLTISSLQPEDFATYYC | LQHNS------------- ---------------YPLT | FGGGT KVGIK |
| iPS:434 179 | 21-225_56F1 | VK1|A30/ JK4 | DIQMTQSPSSLSA SVGDRVTITC | RAS---QDIR- ----NNLG | WYQQKPGK APKRLIN | A------ ASSLQS | GVPSRFSGSGSG--- TEFTLTISSLQPEDFATYYC | LQDNS------------- ---------------HPFT | FGGGT KVEIK |
| iPS:434 217 | 21-225_60E8 | VK1|A30/ JK4 | DIQMTQSPSSLSA SVGDRVTITC | RAS---QGIR- ----NDLG | WFQQKPGK APKRLIY | A------ ASSLQS | GVPSRFSGSGSG--- TEFTLTISSLQPEDFATYYC | LQHSS------------- ---------------YPLT | FGGGT KVEIK |
| iPS:434 249 | 21-225_62E2 | VK1|A30/ JK4 | DIQMTQSPSSLSA SVGDRVTITC | RAS---QGIR- ----NDLG | WYQQKPGK APKRLIY | A------ ASRLQS | GVPSRFSGSGSG--- TEFTLTISSLQPEDFATYYC | LQHSN------------- ---------------YPLT | FGGGT RVEIK |
| iPS:434 253 | 21-225_62E4 | VK1|A30/ JK4 | DIQMTQSPSSLSA SVGDRVTITC | RAS---QGIR- ----NDLG | WYQQKPGK APKRLIY | A------ AFSLQS | GVPSRFSGSGSG--- TEFTLTISSLQPEDFATYYC | LQHNS------------- ---------------YPLT | FGGGT KVEIK |
| iPS:434 313 | 21-225_59E6 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSKSG--- TEFTLTISSLQPEDFATYYC | LQHNS------------- ---------------YPLT | FGGGT KVEIK |
| iPS:434 337 | 21-225_64E1 | VK1|A30/ JK4 | DIQMTQSPSSLSA SVGDRVTITC | RAS---QGIR- ----NDLG | WYQQKPGK APKRLIY | A------ ASTLQS | GVPSRFSGSGSG--- PEFTLTISSLQPEDFATYYC | LQHNS------------- ---------------YPFT | FGGGT KVEIK |
| iPS:434 411 | 21-225_68F11 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSG--- TEFTLTISSLQPEDFATYYC | LQHST------------- ---------------YPLT | FGGGT KVEIK |
| iPS:434 413 | 21-225_68D12 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSG--- TEFTLTISSLQPEDFATYYC | LQHNR------------- ---------------YPLT | FGGGT KVEIK |
| iPS:434 433 | 21-225_70E8 | VK1|A30/ JK4 | DIQMTQSPSSLST SVGDRVTITC | RAS---QGIR- ----KDLG | WYQQKPGK APKRLIY | A------ ASTLQS | GVPSRFSGSGSG--- TEFTLTISSLQPEDFATYYC | LQHNS------------- ---------------YPLT | FGGGT KVEIK |
| iPS:434 439 | 21-225_70E12 | VK1|A30/ JK4 | DIQMTQSPSSLSA SVGDRVTITC | RAS---QGIN- ----NNLN | WFQQKPGK APKRLIY | A------ ASSLQS | GVPSRFSGSGSG--- TEFTLTISSLQPEDFATYYC | LQHNS------------- ---------------YPLT | FGGGS KVEIK |
| iPS:434 489 | 21-225_74E4 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSG--- TEFTLTISSLQPEDFATYYC | LQHSN------------- ---------------YPLT | FGGGT KVEIK |
| iPS:434 503 | 21-225_74D7 | VK1|A30/ JK4 | DIQMTQSPSSLSA SVGDRVTITC | RAS---QGIR- ----NDLG | WYQQKPGK APKRLIY | A------ ASSLQS | GVPSRFSGSGFG--- TEFTLTISSLQPEDFATYYC | LQHSN------------- ---------------YPLT | FGGGT KVEIK |
| iPS:435 251 | 21-225_96A3 | VK1|A30/ JK4 | DIQMTQSPSSLSA SVGDRVTITC | RAS---QGIR- ----NDLG | WYQQKPGK APKRLIY | A------ ASTLQS | GVPSRFSGSGSG--- TEFTLTISSLQPEDFATYYC | LQHST------------- ---------------YPLT | FGGGT KVEIK |
| iPS:435 293 | 21-225_146F1 | VK1|A30/ JK4 | DIQMTQSPSSLSA SVGDRVTITC | RAS---QGIR- ----NDLG | WYQQKPGK APKRLIY | A------ ASSLQS | GVPSRFSGSGSG--- TEFTLTISSLQPEDFATYYC | LQHNS------------- ---------------YPLT | FGGGT KVEIK |
| iPS:435 311 | 21-225_146H9 | VK1|A30/ JK4 | DIQMTQSPSSLSA SVGDRVTITC | RAS---QDIR- ----NDLG | WYQQKPGK APKRLIY | A------ ASSLQS | GVPLRFSGSGSG--- TEFTLTISSLQPEDFATYYC | LQHDS------------- ---------------YPLT | FGGGT KVEIK |
| iPS:435 361 | 21-225_148E1 | VK1|A30/ JK4 | DIQMTQSPSSLSA SVGDRVTITC | RAS---QGIR- ----NNFG | WYQQKPGK APKRLIS | A------ ASSLQS | GVPSRFTGSGSG--- TEFTLTISSVQPEDFATYYC | LQHRN------------- ---------------YPLT | FGGGT KVEIK |
| iPS:435 363 | 21-225_148F12 | VK1|A30/ JK4 | DIQMTQSPSSLSA SVGDRVTITC | RAS---QGIR- ----NALG | WYQQKPGK APKRLIY | A------ ASSLQS | GVPSRFSGSGSG--- TEFTFTTISSLQPEDFATYFC | LQHNS------------- ---------------YPLI | FGGGT KVEIK |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS:435 367 | 21-225_149G1 | VK1|A30/ JK4 | DIQMTQSPSSLSA SVGARVTITC | RAS--QGIR- ----NDLG | WYQQKPGK APKRLIY | A------- ASNLQS | GVPSRFSGSGSG-- TEFTLTISSLQPEDFATYYC | LQHNS------ ------YPLT | FGGGT KVEIK |
| iPS:435 377 | 21-225_149G5 | VK1|A30/ JK4 | DIQMTQSPSSLSA SVGDRVTITC | RAS--QGIR- ----NALG | WFQQKPGK APKRLIY | A------- ASSLQS | GVPSRFSGSGSG-- TEFTLTISSLQPEDFATYYC | LQHNS------ ------YPLT | FGGGT KVEIK |
| iPS:435 397 | 21-225_149F12 | VK1|A30/ JK4 | DIQMTQSPSSLSA SVGDRVTITC | RAS--QGIR- ----NDLG | WYQQKPGK APKRLIY | A------- ASNLQS | GVPSRFSGSGSG-- TEFTLTISSLQPEDFAIYYC | LQHNS------ ------YPLT | FGGGT KVEIK |
| iPS:435 407 | 21-225_150E7 | VK1|A30/ JK4 | DIQMTQSPSSLSA SVGDRVTITC | RAS--QGIR- ----NDLG | WYQQKPGK APKRLIY | A------- ASNLQS | GVPLRFSGSGSG-- TDFTLTISSLQPEDFAAYYC | LQHNS------ ------YPLT | FGGGT KVEIK |
| iPS:435 449 | 21-225_152H9 | VK1|A30/ JK4 | DIQMTQSPSSLSA SVGDRVTITC | RAS--QGIR- ----NDLG | WYQQKPGK APKRLIY | A------- ASSLQS | GVPSRFSGSGSG-- TEFTFTISSLQPEDFATYYC | LQHSN------ ------YPLT | FGGGT KVEIK |
| iPS:435 499 | 21-225_156G1 | VK1|A30/ JK4 | DIQMTQSPSSLSA SVGDRVTITC | RAS--QGIR- ----NDLG | WYQQKPGK APKRLIY | A------- ASSLQS | GVPSRFSGSGSG-- TEFTLTISSLQPEDFATYYC | LQHSN------ ------YPLT | FGGGT KVEIK |
| iPS:435 549 | 21-225_158H5 | VK1|A30/ JK4 | DIQMIQSPSFLFA SVGDRVTITC | RAS--QGMR- ----IDLG | WYQQKPGK APKRLIY | R------- ASSLQS | GVPSRFSGSGCG-- TEFTLTISSVQREDFASYYC | VQHNS------ ------YPLT | FGGGT KVEIK |
| iPS:435 587 | 21-225_160H3 | VK1|A30/ JK4 | DIQMTQSPSSLSA SVGDRVTITC | RAS--QGIR- ----NDLG | WYQQKPGK APKRLIY | A------- ASSLQS | GVPSRFSGSGSG-- TEFTLTISSLQPEDFATYYC | LQHSN------ ------YPLT | FGGGT QVESK |
| iPS:435 599 | 21-225_160B10 | VK1|A30/ JK4 | DIQMTQSPSFSA SVGDRVTITC | RAS--QGPGT ----NDLG | WYQQKPGT APKRLIY | A------- ASSLQS | GVPSRFSGSGSG-- TEFTLTISNLQPEDFATYYC | LQHSS------ ------YPLT | FGGGT KVEIK |
| iPS:435 663 | 21-225_169B1 | VK1|A30/ JK4 | DIQMTQSPSSLSA SVGDRVTITC | RAS--QGIR- ----NDLG | WYQQKPGK APKRLIY | A------- ESSLQS | GVPSRFSGSGSG-- TEFTLTISGLQPEDFATYYC | LQHYS------ ------YPLT | FGGGT KVEIK |
| iPS:435 669 | 21-225_169F9 | VK1|A30/ JK4 | DIQMTQSPSSLSA SVGDRVTITC | RAS--QGIR- ----NDLG | WYQQKPGK APKRLIF | A------- ASSLQS | GVPSRFSGSGSG-- TEFTLTISSLQPEDFATYYC | LQHYS------ ------YPLT | FGGGT KVEIK |
| iPS:435 693 | 21-225_170G4 | VK1|A30/ JK4 | DIQMTQSPSSLSA SVGDRVTITC | RAS--QGIR- ----NDLG | WYHQKPGK APKRLIY | A------- ASTLQS | GVPSRFSGSGSG-- TEFTLTISSLQPEDFATYYC | LQHYS------ ------YPLT | FGGGT KVEIK |
| iPS:435 695 | 21-225_170D5 | VK1|A30/ JK4 | DIQMTQSPSSLSA SVGDRVTITC | RAS--QGIR- ----NDLG | WYQEKPGK APKHLIY | A------- ASSLQN | GVPSRFSGSGSG-- TEFTLTISSLQPEDFATYYC | LQHYS------ ------FPLT | FGGGT KVEIK |
| iPS:435 697 | 21-225_170G5 | VK1|A30/ JK4 | DIQMTQSPSSLSA SVGDRVTITC | RAS--QGIR- ----TDLG | WFQQKPGK APKRLIY | T------- ASSLQS | GVPSRFSGSGSG-- TEFTLTISSLQPEDFATYYC | LQHYS------ ------YPLT | FGGGT KVEIK |
| iPS:435 703 | 21-225_170D1 | VK1|A30/ JK4 | DIQMTQSPSSLSA SVGDRVTITC | RAS--QGIR- ----NDLG | WYQQKPGK APKRLIY | A------- ASSLQS | GVPSRFSGSGSG-- TEFTLTISSLQPEDFATYYC | LQHYS------ ------FPLT | FGGGT KVEIR |
| iPS:435 705 | 21-225_171C3 | VK1|A30/ JK4 | DIQMTQSPSSLSA SVGDRVTITC | RAS--QGIR- ----IDLG | WFQQKPGK APKRLIY | T------- ASSLQS | GVPSRFSGSGSG-- TEFTLTISSLQPEDFATYYC | LQHYS------ ------YPLT | FGGGT KVEIK |
| iPS:435 709 | 21-225_171A4 | VK1|A30/ JK4 | DIQMTQSPSSLSA SVGDRVTITC | RAS--QGIR- ----NDLG | WYQQKPGK APKRLIG | A------- ASSLQS | GVPSRFSGSGSG-- TEFTLTISSLQPEDFATYYC | LQHYS------ ------YPLT | FGGGT KVEIK |
| iPS:435 721 | 21-225_172B3 | VK1|A30/ JK4 | DIQMTQSPSSLSA SVGDRVTITC | RAS--QGIR- ----NDLG | WYQEKPGK APKRLIG | A------- ESSLQS | GVPSRFSGSGSG-- TEFTLTISGLQPEDFATYYC | LQHYS------ ------YPLT | FGGGT KVEIK |
| iPS:435 725 | 21-225_172G8 | VK1|A30/ JK4 | DIQMTQSPSSLSA SVGDRVTITC | RAS--QGVR- ----NDLG | WYQQKPGK APKHLIY | A------- ASSLQN | GVPSRFSGSGSG-- TEFTLTISSLQPEDFATYYC | LEHYS------ ------FPLT | FGGGT KVEIK |
| iPS:435 735 | 21-225_173H1 | VK1|A30/ JK4 | DIQMTQSPSSLSA SVGDRVTITC | RAS--QGIR- ----NDLG | WYQQKPGK APKRLIY | T------- TSSLQS | GVPSRFSGSGSG-- TEFTLTISSLQPEDFASYYC | LQHYS------ ------FPNT | FGGGT KVEIK |
| iPS:435 743 | 21-225_175G12 | VK1|A30/ JK4 | DIQMTQSPSSLSA SVGDRVTITC | RAS--QGIR- ----TDLG | WYQQKPGK APKRLIY | A------- ASSLQS | GVPSRFSGSGSG-- TEFTLTISSLQPEDFATYYC | LQHYS------ ------YPLT | FGGGT KVEIK |

Figure 51 (Continued)

| | | | | | | | | | |
|---|---|---|---|---|---|---|---|---|---|
| iPS:435761 | 21-225_176B11 | VK1A30/JK4 | DIQMTQSPSSLSA SVGDRVTITC | RAS--QGIR-----NDLG | WFQQKPGK APKRLIY | A-------ASSLQS | GVPSRFSGSGSG---TEFTLTISSLQPEDFATYYC | LQHYS------------YPLT | FGGGT KVEIK |
| iPS:435779 | 21-225_178B1 | VK1A30/JK4 | DIQMTQSPSSLSA SVGDRVTITC | RAS--QGIR-----NDLG | WYQQKPGK APKRLIY | A-------ASSLQN | GVPSRFSGSGSG---TEFTLTISSLQPEDFATYYC | LHHYS------------FPLT | FGGGT KVEIK |
| iPS:436023 | 21-225_193A5 | VK1A30/JK4 | DIQMTQSPSSLFA SVGDRVIISC | RAS--QGIR-----NDLG | WYQQKPGK APKRVIY | A-------ASSLQS | GVPSRFSGSGFG---TEFTLTISSVQPEDFETYYC | LQHND------------FPFT | FGGGT KVEIK |
| iPS:436033 | 21-225_193E7 | VK1A30/JK4 | DIQMTQSPSSLSA SVGDRVTITC | RAS--QGIR-----NDLG | WYQQKPGK APKRLIY | S-------ASSLQR | GVPSRFSGSGSG---TEFTLTISSLQPEDFATYYC | LQHKR------------YPLT | FGGGT KVEIK |
| iPS:436120 | 21-225_196C1 | VK1A30/JK4 | DIQMTQSPSSLSA SVGDRVTITC | RAS--QGIR-----NDLG | WYQQKPGK APKRLIY | A-------ASSLQS | GVPSRFSGSGSG---TEFTLTISSLQPEDFATYYC | LQYNS------------YPLT | FGGGT KVEIK |
| iPS:436199 | 21-225_199E3 | VK1A30/JK4 | DIQMTQSPSSLSA SVGDRVTITC | RAS--QGIR-----NDLG | WYQQKPGK APKRLIS | S-------ASSLQR | GVPSRFSGSGSG---TEFTLTISSLQPEDFATYYC | LQHKR------------YPLT | FGGGT KVEIK |
| iPS:436228 | 21-225_200F12 | VK1A30/JK4 | DIQMTQSPSSLSA SVGDRVTITC | RAS--QGIR-----NDLG | WYQQKPGK APKRLIY | S-------ASSLHT | GVPSRFSGSGSG---TEFTLTISSLQPEDFATYYC | LQHKS------------YPLT | FGGGT KVEIK |
| iPS:436230 | 21-225_201A1 | VK1A30/JK4 | DIQMTQSPSSLSA SVGDRVTITC | RAS--QGIR-----NDLG | WYQQKPGK APKRLIY | S-------ASILQR | GVPSRFSGSGSG---TEFTLTISSLQPEDFATYYC | LQHKS------------YPLT | FGGGT KVEVK |
| iPS:436242 | 21-225_201A1 | VK1A30/JK4 | DIQMTQSPSSLSA SVGDRVTITC | RAS--QGIR-----NDLG | WYQQKPGK APKRLIY | S-------TSSLHS | GVPSRFSGSGSG---TEFTLTISSLQPEDFATYYC | LQHNS------------YPLT | FGGGT KVEIK |
| iPS:436286 | 21-225_204H8 | VK1A30/JK4 | DIQMTQSPSSLSA SVGDRVTITC | RAS--QGIR-----NDLG | WYQQKPGK APKRLIY | S-------ASSLQS | GVPSRFSGSGSG---TEFTLTVSSLQPEDFATYYC | LQHNS------------YPLT | FGGGT KVEIK |
| iPS:436308 | 21-225_205H8 | VK1A30/JK4 | DIQMTQSPSSLSA SVGDRVTITC | RAS--QGIR-----NDLG | WYQQKQGK APKRLLIY | S-------ASFLQR | GVPSRFSGSGSG---TEFTLTISSLQPEDSAAYYC | LQHNS------------YPLT | FGGGT TVKIK |
| iPS:436526 | 21-225_224A1 | VK1A30/JK4 | DIQMTQSPSSLSA SVGDRVTITC | RAS--QGIE-----NDLG | WYQQKPGK APKRLIY | D-------ASSLQS | GVPSRFSGSGSG---TEFTLTISSVQPEDFGVYYC | LQHNS------------YPLT | FGGGT KVEIK |
| iPS:436528 | 21-225_224B1 | VK1A30/JK4 | DIQMTQSPSSLSA SVGDRVTITC | RAS--QGIS-----NDLG | WYQQKPGK APKRLIY | A-------ASSLQS | GVPSRFSGSGSG---TEFTLTISSLQPEDFATYHC | LQHNS------------YPPI | FGGGT KVEIK |
| iPS:436538 | 21-225_224C3 | VK1A30/JK4 | DIQMTQSPSSLSA SVGDRVTITC | RAS--QGIR-----NDLG | WYQQKPGK APKRLIY | A-------TSSLQS | GVPSRFSGSGSG---TEFTLTISSLQPEDFATYYC | LQHNS------------YPLT | FGGGT KVEIK |
| iPS:436556 | 21-225_224D1 | VK1A30/JK4 | DIQMTQSPSSLSA SVGDRVTITC | RAS--QGIR-----NDLG | WYQQKPGK APKRLIY | A-------ASSLQS | GVPSRFSGSGSG---TEFTLTISSLQPEDFATYYC | LQHNS------------YPLT | FGGGT KVEIK |
| iPS:437220 | 21-225_55H6 | VK1A30/JK4 | DIQMTQSPSSLSA SVGDRVTITC | RAS--QGIR-----NDLG | WYQQKPGK APKRLIY | G-------ASSLQS | GVPSRFSGSGSG---TEFTLTISSLQPEDFATYYC | LQRDS------------YPFT | FGGGT KVEIK |
| iPS:437346 | 21-225_75H7 | VK1A30/JK4 | DIQMTQSPSSRYA SVGDRVTINS | RAS--QGIR-----NDLG | WYQQKPGK SPQRLIY | A-------ASSLQS | GVPSRFSGSGSG---TEFTLTISSVQPEDFGVYYC | LQHSN------------YPLT | FGGGT KVEIK |
| iPS:472730 | 21-225_14B1_LC1 | VK1A30/JK4 | DIQMTQSPSYLSA SVGDRVTITC | RAS--QDIR-----DNLG | WYQQKPGK APKRLIY | T-------AYSLQS | GVPSRFSGSGSG---TEFTLTISSLQPEDFATYYC | LQHYN------------YPLT | FGGGT KVEIK |
| iPS:392622 | 21-225_17H8 | VK1A30/JK4 | DILMTQSPSSLSA SVGDRVTITC | RAS--QGIR-----NDLG | WYQQKPGK APKRLIY | G-------ASSLQS | GVPSRFSGSGSG---TEFTLTISSLQPEDFTTYYC | LQHNS------------YPLT | FGGGT KVEIK |
| iPS:392624 | 21-225_17H12 | VK1A30/JK4 | DIQMTQSPSSLSA SVGDRVTITC | RAS--QDIR-----NDLG | WYQQKAGK APKRLIN | A-------ASSLQS | GVPSRFSGIGSG---TEFTLTITGLQPEDFATYYC | LQHYS------------YMFT | FGGGT KVEIK |

Figure 51 (Continued)

| ID | V/J | Seq1 | Seq2 | Seq3 | Seq4 | Seq5 | Seq6 | Seq7 | Seq8 | Seq9 |
|---|---|---|---|---|---|---|---|---|---|---|
| iPS:392 628 | 21-225_20C2 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHAS- ------ | ----YPLT | FGGGT KVEIE |
| iPS:392 630 | 21-225_20E5 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS- ------ | ----YPLT | FGGGT KVEIK |
| iPS:392 638 | 21-225_17F9 | VK1|A30/JK4 | DIQMTQSPSSLSA SVGDRVTITC | RAS--QVIR- ----NDLG | WYQQKPGK APKRLIY | A------ ASSLQS | GVPSRFSGSGSG-- TEFTLTISSLQPEDFATYYC | LQHNT- ------ | ----YPLT | FGGGT KVEIK |
| iPS:392 640 | 21-225_18A1 | VK1|A30/JK4 | DIQMTQSPSSLSA SVGDRVTITC | RAS--QGIR- ----NDLG | WYQQKPGK APKRLIY | A------ VSSLQS | GVPSRFSGSGSG-- TEFTLTISSLQPEDFATYYC | LQHNS- ------ | ----YPLT | FGGGT KVEIK |
| iPS:392 642 | 21-225_18C6 | VK1|A30/JK4 | DIQMTQSPSSLSA SVGDRVTITC | RTS--QGIR- ------NDLG | WYQQKPGK APKRLIY | A------ ASSLQS | GVPSRFSGSGSG-- TEFTLTISSLQPEDFATYYC | LQHSS- ------ | ----YPLT | FGGGT KVEIK |
| iPS:392 644 | 21-225_19E1 | VK1|A30/JK4 | DIQMTQSPSSLSA SVGDRVTITC | RAS--QGIR- ----NDLG | WYQQKPGK APKRLIY | A------ ASNLQS | GVPSRFSGSGSG-- TEFTLTISSLQPEDFATYYC | LQHNS- ------ | ----FPLT | FGGGT KVEIK |
| iPS:392 646 | 21-225_20G2 | VK1|A30/JK4 | DIQMTQSPSSLSA SVGDRVTITC | RAS--QGIR- ----NDLG | WYQQKPGK APKRLIY | A------ ASSFQS | GVPSRFSGSGSG-- TEFTLTISSLQPEDFASYYC | LQHNS- ------ | ----YPLT | FGGGT KVEIK |
| iPS:392 654 | 21-225_17A10 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHAS- ------ | ----YPLT | FGGGT KVEIK |
| iPS:392 656 | 21-225_1F2 | VK1|A30/JK4 | DIQMTQSPSSLSA SVGDRVTITC | RAS--QGIR- ----NDLG | WYQQKPGK APKRLIY | A------ ASSVQS | GVPSRFSGSGSG-- TEFTLTISSLQPEDFATYYC | LQHNS- ------ | ----YPLT | FGGGT KVEIK |
| iPS:392 658 | 21-225_18E8 | VK1|A30/JK4 | DIQMTQAPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS- ------ | ----YPLT | FGGGT KVEIK |
| iPS:392 666 | 21-225_16F11 | VK1|A30/JK4 | DIQMTQSPSSLSA SVGDRVTITC | RAS--QGIR- ----NDLG | WYQQKPGK APKRLIY | V------ ASSLQS | GVPSRFSGSGSG-- TEFTLTISSLQPEDFATYYC | LQHNS- ------ | ----YPLT | FGGGT KVEIK |
| iPS:392 676 | 21-225_19F3 | VK1|A30/JK4 | DIQMTQSPSSLSA SVGDRVTITC | RAS--QGIR- ----NDLG | WYQQKPGK APKRLIY | A------ ASNLQS | GVPSRFSGSGSG-- TEFSFTISSLQPEDFATYYC | LQHNS- ------ | ----YPLT | FGGGT KVEIK |
| iPS:392 680 | 21-225_20A7 | VK1|A30/JK4 | DIQMTQSPSSLSA SVGDRVTITC | RAS--QGIR- ----NDLG | WYQQKQGK APKRLIY | A------ ASSLQS | GVPSRFSGSGSG-- TEFSLTISSLQPEDFATYYC | LQHAS- ------ | ----YPLT | FGGGT KVEIK |
| iPS:392 700 | 21-225_16E12 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNR- ------ | ----YPLT | FGGGT KVEIK |
| iPS:392 706 | 21-225_18A3 | VK1|A30/JK4 | DIQMTQSPSSLSA SVGDRVTITC | RAS--QGIR- ----NDLG | WYQQKPGK APKRLIF | A------ ASSLQS | GVPSRFSGSGSG-- TEFTLTISSLQPEDFATYYC | LQHNS- ------ | ----YPLT | FGGGT KVEIK |
| iPS:392 716 | 21-225_17B5 | VK1|A30/JK4 | DIQMTQSPSSLSA SVGDRVTITC | RAS--QGIR- ----NDLG | WYQQKPGK APKRLIY | A------ ASNLQS | GVPSRFSGSGSG-- TEFTLTISSLQPEDFATYYC | LQHNS- ------ | ----YPFT | FGGGT KVEIK |
| iPS:392 744 | 21-225_20D5 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS- ------ | ----YPLT | FGGGT KVEIK |
| iPS:392 750 | 21-225_20A10 | VK1|A30/JK4 | DIQMTQSPSSLSA SVGDRVTITC | RAS--QGIR- ----NDLG | WYQQKQGK APKRLIY | A------ ASSLQS | GVPSRFSGSGSG-- TEFTLTISSLQPEDFATYYC | LQHNR- ------ | ----YPLT | FGGGT KVEIK |
| iPS:392 772 | 21-225_20E12 | VK1|A30/JK4 | DIQMTQSPSSLSA SVGDRVTITC | RAS--QGIR- ----NDLG | WYQQKPGK APKRLIF | A------ ASSLQS | GVPSRFSGSGSG-- TEFTLTISSLQPEDFATYYC | LQHNS- ------ | ----YPLT | FGGGT KVEIK |
| iPS:392 774 | 21-225_21F3 | VK1|A30/JK4 | DIQMTQSPSSLSA SVGDRVTITC | RAS--QGIR- ----NDLG | WYQQKPGK APKRLIY | T------ ASSLQS | GVPSRFSGSGSG-- TDFILTISSLQPEDFATYYC | LQHSS- ------ | ----YPLT | FGGGT KVEIK |
| iPS:392 780 | 21-225_22B7 | VK1|A30/JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNT- ------ | ----YPLT | FGGGT KVEIK |
| iPS:392 788 | 21-225_20C8 | VK1|A30/JK4 | DIQMTQSPSSLSA SVGDRVTITC | RAS--QGIR- ----NDLG | WYQQKPGK APKRLIN | A------ ASSLQS | GVPSRFSGSGSG-- TEFTLTISSLQPEDFATYYC | LQHNS- ------ | ----YPFT | FGGGT KVEIT |
| iPS:392 794 | 21-225_21H3 | VK1|A30/JK4 | DIQMTQSPSSLSA SVGDRVTITC | RAS--QGIR- -----NDLG | WYQQKPGK APKRLIY | A------ ASSVQT | GVPSRFSGSGSG-- TEFTLTISSLQAEDLAIYYC | LQHNS- ------ | ----YPLT | FGGGT KVEIK |

Figure 51 (Continued)

| | | | | | | | | | |
|---|---|---|---|---|---|---|---|---|---|
| iPS:392 800 | 21-225_22D12 | VK1/A30/ JK4 | DIQMTQSPSSLSA SVGDRVTITC | RAS--QGIR- ----NDLG | WYQQKPGK APKRLIY | A------ ASSLQS | GVPSRFSGSGSG-- TDFTLTISSLQPEDFATYYC | LQHST- ----YPLT | FGGGT KVEIK |
| iPS:392 810 | 21-225_20H12 | VK1/A30/ JK4 | DIQMTQSPSSLSA SVGDRVTITC | RAS--QGIR- ----NDLD | WYQQKPGK APKRLIY | A------ ASSLQS | GVPSRFSGSGSG-- TEFTLTISSLQPEDFATYYC | LQHNS- ----YPLT | FGGGT KVEIK |
| iPS:392 820 | 21-225_23D1 | VK1/A30/ JK4 | DIQMTQSPSSLSA SVGDRVTITC | RAS--QGIR- ----NDLG | WYQQKPGK APKRLIY | A------ ASSLQS | GVPSRFSGSGSG-- TEFTLTVSSLQPEDFATYYC | LQHSS- ----YPLT | FGGGT KVEIK |
| iPS:392 822 | 21-225_23C8 | VK1/A30/ JK4 | DIQMTQSPSSRSA SVGDRVTITC | RAS--QDIR- ----NDLG | WYQQKPGR APKRLIN | G------ ASSVQS | GVPSRFSGSGSG-- TEFTLTISSLQPEDFVIYYC | LQHNS- ----YPLT | FGGGT KVEIK |
| iPS:392 824 | 21-225_24E5 | VK1/A30/ JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHSN- ----YPLT | FGGGT KVEIK |
| iPS:392 834 | 21-225_22C1 | VK1/A30/ JK4 | DIQMTQSPSSLSA SVGDRVTITC | RTS--QGIR- ----NDLG | WYQQKPGK APKRLIY | A------ ASSLQS | GVPSRFSGSGSG-- TEFTLTISSLQPEDFATYYC | LQHST- ----YPLT | FGGGT KVEIK |
| iPS:392 838 | 21-225_22G8 | VK1/A30/ JK4 | DIQMTQSPSSLFA SVGDRVTITC | RTS--QGIR- ----NDLG | WYQQKPGK APKRLIY | A------ ASSLQS | GVPSRFSGSGSG-- TEFTLTISSLQPEDFATYYC | LQHNS- ----YPLT | FGGGT KVEIK |
| iPS:392 850 | 21-225_20H10 | VK1/A30/ JK4 | GIQMTQSPSSLSA SVGDRVTITC | RAS--QGIK- ----NNLG | WYQQKPGK GPKCLIY | A------ ASSVQS | GVPSRFSGSGSG-- TEFTLTISSLQPEDFATYYC | LQHNS- ----YPLT | FGGGT KVEIK |
| iPS:392 854 | 21-225_21E5 | VK1/A30/ JK4 | DIQMTQSPSSLSA SVGDRVTITC | RAS--QGIR- ----NDLG | WYQQKPGK APKRLIY | A------ TSSLQS | GVPSRFSGSGSG-- TEFTLTISSLQPEDFATYYC | LQHNS- ----YPLT | FGGGT KVEIK |
| iPS:392 858 | 21-225_22H4 | VK1/A30/ JK4 | DIQMTQSPSSLSA SVGDRVTITC | RAS--QGVR- ----NDLG | WYQQKPGK APKRLIY | A------ ASSVQS | GVPSRFSGSGSG-- TEFTLTISSLQPEDFATYFC | LQHNS- ----YPLT | FGGGT KVEIK |
| iPS:392 866 | 21-225_23H11 | VK1/A30/ JK4 | DIQMTQSPSSLSA SVGDRVTITC | RAS--QGIR- ----NDLD | WYQQKPGK APQRLIY | A------ ASSLQS | GVPSRFSGSGSG-- TEFTLTISSLQPEDFATYYC | LQHSS- ----YPLT | FGGGT KVEIK |
| iPS:392 870 | 21-225_20G9 | VK1/A30/ JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHST- ----YPLT | FGGGT KVEIK |
| iPS:392 880 | 21-225_22F9 | VK1/A30/ JK4 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS- ----YPLT | FGGGT KVEIK |
| iPS:392 882 | 21-225_23A3 | VK1/A30/ JK4 | DIQMTQSPSSLSA SVGDRVTITC | RAS--QDIR- ----DDLG | WYQQKPGK APRRLIY | G------ AFSLQS | GVPSRFSGSGSG-- TEFTLTISSLQPEDFATYYC | LQHTS- ----YPLT | FGGGT KVEIK |
| iPS:392 896 | 21-225_21G7 | VK1/A30/ JK4 | DIQMTQSPSSLSA SVGDRVTITC | RAS--QDIR- ----SDLG | WYQQKPGK AHKRITY | A------ ASSLQS | GVPSRFNGSGSG-- TEFTLTISSMQPDDFSNYYC | LQHNS- ----YPPT | FGGGT KVEIK |
| iPS:392 900 | 21-225_22F2 | VK1/A30/ JK4 | DIQMTQSPSSLSA SVGDRVTITC | RAS--QGIR- ----SDLG | WYQQKPGK APKRLIY | A------ ASSLQS | GVSKFSGSGSG-- TEFTLTISSLQPEDFATYYC | LQHNS- ----YPLT | FGGGT KVEIK |
| iPS:392 904 | 21-225_22G9 | VK1/A30/ JK4 | DIQMTQSPSSLSA SVGDRVTITC | RAS--QGIR- ----NDLG | WYQQKSGK TPKRLIY | A------ VSSLQS | GVPSRFSGSGSG-- TEFTLTISSLQPEDFATYYC | LQHAS- ----YPLT | FGGGT KVEIK |
| iPS:392 942 | 21-225_30E9 | VK1/A30/ JK4 | DIQMTQSPSSLSA SVGDRVTITC | RAS--QDIR- ----NDLG | WYQQKPGK APERLIY | A------ ASSLQS | GVPSRFSGSGSG-- TEFTLTISSLQPEDFATYYC | LQHTI- ----YPPT | FGGGT KVEIK |
| iPS:392 944 | 21-225_31H5 | VK1/A30/ JK4 | DIQMTQSPRFTISF | RAS--QDIR- ----SDLG | WYQQKPGK APKRLIY | A------ ASSLQS | GVPSRFSGSGSG-- TEFTLTISSMQPDDFSNYYC | LQHII- ----YPPT | FGGGT KVEIK |
| iPS:392 964 | 21-225_31A8 | VK1/A30/ JK4 | DIQMTQSPSSLSA SVGDRVTITC | RAS--QKSGK ----NDLG | WYQQKSGK TPKRLIY | A------ ASSLQS | GVPSRFSGSGSG-- TEFTLTISSLQPEDFATYYC | LQHNS- ----YPLT | FGGGT KVEIK |
| iPS:392 980 | 21-225_29H6 | VK1/A30/ JK4 | DIQMTQSPSSLSA SVGDRVTITC | RAS--QDIR- ----NDLG | WYQQKPGK APERLIY | A------ ASSLQS | GVPSRFSGSGSG-- TEFTLTISSLQPEDFATYYC | LQHTI- ----YPLT | FGGGT KVEIK |
| iPS:392 982 | 21-225_30D1 | VK1/A30/ JK4 | DIQMTQSPSSLSA SVGDRVTITC | RAS--QDIR- ----SDLG | WYQQKPGK APKRLIY | G------ ASSLQS | GVPSRFSGSGSG-- TEFTLTISSLQPEDFATYYC | LQHII- ----YPPT | FGGGT KVEIK |
| iPS:392 986 | 21-225_31B8 | VK1/A30/ JK4 | DIQMTQSPSSLSA SVGDRVTITC | RAS--QDIR- ----SDLG | WYQQKPGK APFKLIY | | | | |

Figure 51 (Continued)

| ID | Name | V/J | | | | | | | | |
|---|---|---|---|---|---|---|---|---|---|---|
| iPS:392988 | 21-225_25E6 | VK1|A30/JK4 | DIQMTQSPSSLSASVGDRVTIITC | RAS--QGIR-----NDLG | WYQRKPGKAPKRLIY | A-------ASSLQS | GVPSRFKGSGSG--TEFTLTISSLQPEDFATYYC | LQHNS-------YPLT | FGGGTKVEIK |
| iPS:392990 | 21-225_25H10 | VK1|A30/JK4 | DIQMTQSPSSLSASVGDRVTITC | RAS--RGIR-----NDLG | WYQQKPGKAPKRLIY | A-------AFSLQS | GVPSRFSGSGSG--TEFTLTISSLQPEDFATYYC | LQHNS-------YPLT | FGGGTKVEIK |
| iPS:393004 | 21-225_30G11 | VK1|A30/JK4 | DIQMTQSPSSLSASVGDRVTITC | RAS--QDIR-----SDLG | WYQQKPGKAPKRLIY | A-------ASSLQS | GVPSRFSGSGSG--TEFTLTISSLQPEDFATYYC | LQHTI-------YPPT | FGGGTKVEIK |
| iPS:393018 | 21-225_29B8 | VK1|A30/JK4 | DIQMTQSPSSLSASVGDRVTITC | RAS--QGIR-----NDLG | WYQQKPGKAPKRLIY | A-------ASSLQS | GVPSRFSGSRSG--TEFTLTISSLQPEDFATYYC | LQHNS-------YPLT | FGGGTKVEIK |
| iPS:393030 | 21-225_25H11 | VK1|A30/JK4 | DIQMTQSPSSLSASVGDRVTITC | RAS--QGIR-----TDLG | WYQQKPGKAPKRLIY | A-------ASSLQS | GVPSRFSGSGSG--TEFTLTISSLQPEDFATYYC | LQHNS-------YPLT | FGGGTKVEIK |
| iPS:393034 | 21-225_27F2 | VK1|A30/JK4 | DIQMTQSPSSLSASVGDRVTITC | RAS--QGIR-----NDLG | WYQQKPGKAPKRLIY | V-------ASSLQS | GVPSRFSGSGSG--TEFTLTISSLQPEDFATYYC | LQHNS-------YPLT | FGGGTKVEIK |
| iPS:393040 | 21-225_30E3 | VK1|A30/JK4 | DIQMTQSPSSLSASVGDRVTITC | RAS--QDIR-----DDLG | WYQQKPGKAPRRLIY | A-------AFSLQS | GVPSRFSGSGSG--TEFTLTISSLQPEDFATYYC | LQHTS-------YPPT | FGGGTKVEIK |
| iPS:393048 | 21-225_27C3 | VK1|A30/JK4 | DIQMTQSPSSLSASVGDRVTITC | RAS--QDIR-----NDLG | WYQQKPGKAPKRLIY | A-------ASSLQS | GVPSRFSGSGSG--TEFTLTISSLQPEDFATYYC | LQHNR-------YPLT | FGGGTKVEIK |
| iPS:393054 | 21-225_29G8 | VK1|A30/JK4 | DIQMTQSPSSLSASVGDRVTITC | RAS--QGIR-----NDLG | WYQLKPGKAPKRLIY | A-------ASSLQS | GVPSRFSGSGSG--TEFTLTISSLQPEDFATYYNC | LQHNS-------YPLT | FGGGTKVEIK |
| iPS:393056 | 21-225_30F3 | VK1|A30/JK4 | DIQMTQSPSSLSASVGDRVTITC | RAS--QGIR-----NDLG | WYQQKPGKAPKRLIY | T-------ASSLQS | GVPSRFSGSGSG--TDFTLTISSLQPEDFATYYC | LHHPI-------YPFT | FGGGTKVWTK |
| iPS:393058 | 21-225_31H3 | VK1|A30/JK4 | DIQMTQSPSSLSASVGDRVTITC | RAS--QDIR-----DDLG | WYQQKPGKAPRRLIY | A-------AFSLQS | GVPSRFSGSGSG--TEFTLTISSLQPEDFATYYC | LQHTS-------YPPT | FGGGTKVEVK |
| iPS:393060 | 21-225_32G12 | VK1|A30/JK4 | DIQMTQSPSSLSASVGDRVTITC | RTS--QDIR-----NDVG | WYQQRPGKAPKRLIY | A-------ASSLQR | GVPSRFSGSGSG--TEFTLTISSLQPEDFARYYC | LQHYS-------YPPT | FGGGTKVEIK |
| iPS:393068 | 21-225_34G9 | VK1|A30/JK4 | DIQMTQSPSSLSASVGDRVTITC | RAS--QDIR-----SDLG | WYQQKPGKAPKRLIY | A-------ASSLQS | GVPSRFTGSGSG--TEFTLTISSVQPEDFATYYC | LQHTI-------YPPT | FGGGTKVGIK |
| iPS:393072 | 21-225_36C5 | VK1|A30/JK4 | DIQMTQSPSSLSASVGDRVTITC | RAS--QDIR-----SDLG | WYQQKPGKAPKRLIY | A-------ASSLQS | GVPSRFSGSGSG--TEFTLTISSLQPEDFATYYC | LHHPI-------YPPT | FGGGTKVWTK |
| iPS:393074 | 21-225_33B1 | VK1|A30/JK4 | DIQMTQSPSSLSASVGDRVTITC | RTS--QDIR-----SDLG | WFQQKPGKAPKRLIY | T-------ASSLQS | GVPSRFSGSGSG--TEFTLTISSLQPEDFATYYC | LQHNS-------YPLT | FGGGTKVEVK |
| iPS:393076 | 21-225_33A4 | VK1|A30/JK4 | DIQMTQSPSSLSASVGDRVTITC | RAS--QDIR-----NDLG | WYQQKPGKAPERLIY | A-------ASSLQR | GVPSRFSGSGSG--TEFTLTISSLQPEDFARYYC | LQHYS-------YPPT | FGGGTKVEIK |
| iPS:393096 | 21-225_34D11 | VK1|A30/JK4 | DIQMTQSPSSLSASVGDRVTITC | RAS--QDIR-----SDLG | WYQQKPGKAPKRLIY | A-------ASSLQS | GVPSRFSGSGSG--TEFTLVISSLQPEDFATYYC | LQHTI-------YPPT | FGGGTKVEIK |
| iPS:393102 | 21-225_33F1 | VK1|A30/JK4 | DIQMTQSPSSLSASVGDRVTITC | RTS--QDIR-----SDLG | WYQQKPGKAPKRLIY | A-------ASSLQS | GVPSRFSGSGSG--TEFTLTISSLQPEAFAIYYC | LQHTI-------YPPT | FGGGTKVEIK |
| iPS:393104 | 21-225_33A7 | VK1|A30/JK4 | DIQMTQSPSSLSASVGDRVTITC | RAS--QDIR-----SDLG | WYQQKPGKAPKRLIY | V-------ASSLQS | GVPSRFSGSGSG--TEFTLTISSLQPEDFATYYC | LQHTI-------YPPT | FGGGTKVEIK |
| iPS:393106 | 21-225_34A6 | VK1|A30/JK4 | DIQMTQSPSSLSASVGDRVTITC | RAS--QDIR-----NDLG | WYQQKPGKAPERLIY | A-------ISSLQS | GVPSRFSGSGSG--TEFTLTISSLQPEDFAAYYC | LQHNS-------YPPT | FGGGTKVEIK |
| iPS:393110 | 21-225_35B7 | VK1|A30/JK4 | DIQMTQSPSSLSASVGDRITTTC | RAS--QDIR-----SDLG | WYQQKPGKAPKRLIF | A-------ASSLQS | GVPSRFSGSGSG--TEFTLTISSLQPEDFATYYC | LQHTI-------YPPT | FGGGTKVEIK |
| iPS:393118 | 21-225_34H11 | VK1|A30/JK4 | DIQMTQSPSSLSASVGDRVTITC | RTS--QDIR-----NDLG | WYQQKPGKAPKRLIY | A-------ASSLQS | GVPSRFSGSGSG--TEFTLTISSLQPEDFATYYC | LQHNS-------YPPT | FGGGTKVEIK |
| iPS:393124 | 21-225_33G7 | VK1|A30/JK4 | DIQMTQSPSSLSASVGDRVTITC | RAS--QGIR-----NDLG | WYQQKPCKAPKRLII | A-------ASSLQS | GVPSRFSGSGSG--TEFTLVSSLQPEDFATYYC | LQHYS------YPPT | FGGGTKVEIK |

Figure 51 (Continued)

| | | | | | | | | | |
|---|---|---|---|---|---|---|---|---|---|
| iPS:393 126 | 21-225_35D1 | VK1|A30/ JK4 | DIQMTQSPSSLSA SVGDRVTIIC | RAS----QDIR -----SDLG | WYQQKPGK APKRLIY | A------ ASSLQS | GVPSRFSGSGSG-- TEFTLTISSLQPEDFATYYC | LQHTI------------ ------YPPT | FGGGT KVEIK |
| iPS:393 128 | 21-225_35F11 | VK1|A30/ JK4 | DIQMTQSPSSLSA SVGDRVTIIC | RAS----QDIR -----SDLG | WYQQKPGK APKRLIY | A------ ASSLQS | GVPSRFSGSGSG-- TEFTLTISSLQPEDFATYYC | LQHTV------------ ------YPPT | FGGGT KVEIK |
| iPS:393 146 | 21-225_34G8 | VK1|A30/ JK4 | DIQMTQSPSSLSA SVGDRVTIIC | RAS----QDIR -----SDLG | WYQQKPGK APKRLIY | A------ ASSLQS | GVPSRFSGSGSG-- TEFTLTISSLQPEDFATYYC | LQHTI------------ ------YPPT | FGGGT KVEIK |
| iPS:393 150 | 21-225_36A5 | VK1|A30/ JK4 | DIQMTQSPSSLSA SVGDRVTIIC | RTS----QDIR -----SDLG | WYQQKPGK APKRLIF | A------ ASSLQS | GVPSRFSGSGSG-- TEFTLTISSLQPEDFATYYC | LHHNS------------ ------YPPK | FGGGT KVEIK |
| iPS:393 804 | 21-225_5H7 | VK1|A30/ JK4 | DIQMTQSPSSLSA SVGDRVTIIC | RAS----QGIR -----NDLG | WYQQKPGK APKRLIY | V------ ISSLQG | GVPSRFSGSGSG-- TEFTLTISSLQPEDFATYYC | LQHNS------------ ------YPLT | FGGGT KVEIK |
| iPS:393 806 | 21-225_6A6 | VK1|A30/ JK4 | DIQMTQSPSSLSA SVGDRVTIIC | RAS----QGIR -----NDLG | WYQQKPGK APKRLIY | A------ ASSLQS | GVPSRFSGSGSG-- TEFTLTISSLQPEDFATYYC | LQHSS------------ ------YPLT | FGGGT KVEIK |
| iPS:393 808 | 21-225_1A2 | VK1|A30/ JK4 | DIQMTQSPSSLSA SVGDRVTIIC | RAS----QGIR -----NDLG | WYQQKPGK APKRLIY | A------ ASSLQS | GVPSRFSGSGSG-- TEFTLTISSLQPEDFATYYC | LQHNS------------ ------HPLT | FGGGT KVEIK |
| iPS:393 814 | 21-225_7F4 | VK1|A30/ JK4 | DIQMTQSPSSLSA SVGDRVTIIC | RTS----QDIR -----NDLG | WYQQKPGK APKRLIY | A------ ASNLQS | GVPSRFSGSGSG-- TEFTLTISSLQPEDFATYYC | LQRSA------------ ------YPLT | FGGGT KVEIK |
| iPS:393 816 | 21-225_6D4 | VK1|A30/ JK4 | DIQMTQSPSSLSA SVGDRVTIIC | RAS----QAIR -----NDLG | WYQQKPGK APKRLIY | A------ ASSLQS | GVPSRFSGSGSG-- TEFTLTISSLQPEDFATYYC | LQHSS------------ ------YPLT | FGGGT KVEIK |
| iPS:393 818 | 21-225_6G12 | VK1|A30/ JK4 | DIQMTQSPSSLSA SVGDRVTIIC | RAS----QGIR -----NDLG | WYQQKPGK APKRLIY | A------ ASTLQS | GVPSRFSGSGSG-- TEFTLTISSLQPEDFATYYC | LQHNS------------ ------YPLT | FGGGT KVEIK |
| iPS:393 820 | 21-225_8H7 | VK1|A30/ JK4 | DIQMTQSPSSLSA SVGDRVTIIC | RAS----QGIR -----NDLG | WYQQKPGK APKRLIY | A------ ASSLQS | GVPSRFSGSGSG-- TEFTLTISSLQPEDFATYYC | ------------ ------YPFT | FGGGT KVEIK |
| iPS:393 826 | 21-225_10G5 | VK1|A30/ JK4 | DIQMTQSPSSLSA SVGDRVTIIC | RAS----QGIR -----NDLG | WYQQKPGK APKRLIY | A------ ACSFQS | GVPSRFSGSGSG-- IEFTLTISIMQPEDFATYYC | LQHNL------------ ------YPLT | FGGGT KVEIK |
| iPS:393 828 | 21-225_14C2 | VK1|A30/ JK4 | DIQMTQSPSSLSA SVGDRVTIIC | RAS----QGIR -----NDLD | WYQQKPGK APKRLIY | G------ ASSLQS | GVPSRFSGSGSG-- TEFTLTISSLQPEDFATYYC | VQHNS------------ ------YPLT | FGGGT KVEIK |
| iPS:393 830 | 21-225_10H12 | VK1|A30/ JK4 | DIQMTQSPSSLSA SVGDRVTIIC | RAS----QGIR -----NDLG | WYQQKPGK APKRLIY | S------ ASSLQS | GVPSRFSGSGCG-- TEFTLTISSLQREDFATYYC | VQHYS------------ ------YPLT | FGGGT KVEIK |
| iPS:393 832 | 21-225_12A1 | VK1|A30/ JK4 | DIQMTQSPSSLSA SVGDRVTIIC | RAS----QGIR -----NDLG | WYQQKPGK APKRLIY | A------ ASSLQS | GVPSRFSGSGSG-- TEFTLTISSLQREDFAAYYS | LQHNS------------ ------YPFT | FGGGT KVEIK |
| iPS:393 854 | 21-225_14B2 | VK1|A30/ JK4 | DIQMTQSPSSASA SVGDRVTIIC | LAS----QGIR -----NDLG | WYQQKPGK APKRLIY | V------ ISSLQG | GVPSRFSGSGYG-- IEFTLTISIMQPEDFATYYC | LQHNL------------ ------YPLT | FGGGT KVEIK |
| iPS:393 856 | 21-225_7H11 | VK1|A30/ JK4 | DIQMTQSPSSLFA CVGDRVIIIC | RAS----QGIR -----NDLD | WYQQKPGK APKRLIY | A------ ASSLQS | GVPSRFSGSGSG-- TEFTLTISSVQREDFATYYC | LQHNS------------ ------YPLT | FGGGT KVEIK |
| iPS:393 866 | 21-225_14E3 | VK1|A30/ JK4 | DIQMTQSPSSLSP SVGDRVTIIC | RAS----QGIR -----NDLG | WYQQKPGK APQRLIS | A------ ASSLQS | GVPSRFSGSGSG-- TEFTLTISSLQPEDFATYYC | LQHNS------------ ------YPLT | FGGGT KMEIK |
| iPS:393 872 | 21-225_2A11 | VK1|A30/ JK4 | DIQMTQSPSFLFA SVGDRVTIIC | RAS----QGIR -----NDLG | WYQQKPGK APKRLIY | A------ ASSSQS | GVPSRFSGSGSG-- TEFTLTIYSSLQPEDFASYYC | ------------ ------YPLT | FGGGT KVEIK |
| iPS:393 874 | 21-225_4C8 | VK1|A30/ JK4 | DIQMTQSPSPFSA CVGDRVTIIC | RAS----QGIR -----NDLG | WYQQKSCK APKRLIY | V------ ASSLQS | GVPSRFSGSGSG-- TEFTLTISSVQPEDFATYYC | LHNSS------------ ------YPVK | FGGGT KVEIT |
| iPS:393 880 | 21-225_15A1 | VK1|A30/ JK4 | DIQMTQSPSSLSA SVGDRVTIIC | RAS----QGIR -----NDLG | WYQQKPGK APKRLIY | A------ ASSLQS | GVPSRFSGSGSG-- TEFTLTISSLQPEDLAAYYC | LQHHS------------ ------YPLT | FGGGI EVEIY |
| iPS:393 882 | 21-225_15E3 | VK1|A30/ JK4 | DIQMIQSPSSLSA CVGDRVIIIC | RAS----QGIR -----NDLG | WYQQKPGK APKRLIY | V------ ASSSQS | GVPSRFSGSRSG-- TEFTLTISSLQPEDLAAYYC | LQHHS------------ ------YPLT | FGGGT KVEIK |
| iPS:393 884 | 21-225_16F4 | VK1|A30/ JK4 | DIQMTQSPSPSA SVGDRVTIIC | RAS----QGIR ------NDLG | WYQQKSCK APKRLIY | V------ ASSLQS | GVPSRFSGSGSG-- TEFTLTISSVQPEDFATYYC | IQHNS------------ ------YPFT | FGGGT KVEIK |

Figure 51 (Continued)

| | | | | | | | | | |
|---|---|---|---|---|---|---|---|---|---|
| iPS:393886 | 21-225_2G9 | VK1|A30/JK4 | DIQMTQSPSSLFA SVGDRVTITC | RAS--QGIR-----NDLG | WYQQKPGK APQRLIY | A------ ASSLQS | GVPSRFSGSGFG-- TEFTLTISSLQLEDFATYYC | LQHES--------YPLT | FGGGT KVEIK |
| iPS:393922 | 21-225_2B2 | VK1|A30/JK4 | DIQMTQSPSSLSA SVGDRVTITC | RAS--QGIR-----NDLG | WYQQKPGQ APKRLIY | A------ ASSLQS | GVPSRFSGSGSG-- TEFTLTISSLQPEDLATYHC | LQHNS--------YPLT | FGGGT KVEIK |
| iPS:393928 | 21-225_4E10 | VK1|A30/JK4 | DIQMTQSPSSLFA SVGDRVTITC | RAS--QGIR-----NDLG | WYQQKPGK APKRLIY | A------ ASSLQS | GVPSRFSGSGFG-- TEFTLTISSLQLEDFATYYC | LQHDN--------YPLT | FGGGT KVEIK |
| iPS:393934 | 21-225_13E6 | VK1|A30/JK4 | DIQVTQSPSSLSA SVGDRVTITS | RAS--QGIR-----NDLG | WYQQKPGK APKRLIY | A------ ASSLQS | GVPSRFSGSGSG-- TEFTLTISSLQPEDFATYYC | VQHNS--------YPLT | FGGGT KVAIK |
| iPS:393958 | 21-225_5H2 | VK1|A30/JK4 | DIQMTQSPSSLSA SVIDRVTITC | RAS--QGIR-----NDLG | WYQQKPGK APKRLIY | A------ ASSLQS | GVPSRFSGSGSG-- TEFTLTISSLQPEDFATYYC | LQHNS--------YPLT | FGGGT KVEIK |
| iPS:393962 | 21-225_7H7 | VK1|A30/JK4 | DIQMTQSPSSLSA SVGDRVTITC | RAS--QGIR-----NDLG | WYQQKPGK APKRLIY | A------ ASSLQS | GVTSRFSGSGSG-- TEFTLTISSLQPEDFATYYC | LQHSS--------YPFT | FVGGT KVEIK |
| iPS:393974 | 21-225_7C4 | VK1|A30/JK4 | DIQMTQSPSSLFA SVGDRVTITC | RAS--QGIR-----NDLG | WYQQKPGK AHKRLIY | A------ ASSLQS | GVPSRFSGSGSG-- TIFTLTISSLQPEDFATYYC | LQHNS--------YPLT | FGGGT KVEIK |
| iPS:393976 | 21-225_7E9 | VK1|A30/JK4 | DIQMTQSPSSLFA SVGDRVTITC | RAS--QGIR-----NDLG | WYEQKPGK APKRLIY | A------ ASSLQS | GVPSRFSGSGSG-- TEFTLTISSLQTEDFATYYC | LQHNS--------YPLT | FGGGT KVEIK |
| iPS:393982 | 21-225_6C12 | VK1|A30/JK4 | DIQMTQSPSSLSA SVGDRVTITC | RAS----QGIR---SNLG | WYQQKPGK APKRLIY | A------ ASSLES | GIPSRFSGSGSFG-- TEFTLTISSLQPEDFATYFC | LQDNS--------YPFT | FGGGT KVEIR |
| iPS:393984 | 21-225_4F12 | VK1|A30/JK4 | DIQMTQSPSSLSA SVGDRVTITC | RAS--QGIR-----NDLG | WYQQKPGK APKRLIF | A------ ASSLQS | GVPSRFSGSGSG-- TEFTLTISSLQPEDFATYYC | LQHNS--------YALT | FGGGT KVEIR |
| iPS:393990 | 21-225_11G7 | VK1|A30/JK4 | DIQMTQSPSSLFA SVGDRVTITC | RAS--QGIR-----NDLG | WYQQKPGK APKRLIY | A------ ASSLQS | GVPSRFSGSGSG-- TEFTLTISSLQPEDFATYYC | LQHSN--------YPLT | FGGGT NVEIR |
| iPS:393994 | 21-225_8C9 | VK1|A30/JK4 | DIQMTQSPSSLSA SIGDRVTITC | RAS--QAIR-----NDLD | WYQQKPGK APKRLIY | T------ ASSLQS | GVPSRFSGSGSG-- TEFTLTISSLQTEDFATYYC | LQHNS--------YPLT | FGGGT KVEIK |
| iPS:394002 | 21-225_15G7 | VK1|A30/JK4 | DIQMTQSPSSLSA SVGDRVTITC | RAS--QGIR-----NDLG | WYQQKPGK APKRLIY | A------ ASSVQS | GVPSRFSGSGFG-- TEFTLTISSLQPEDFATYYC | LQHNS--------YPLT | FGGGT KVEIK |
| iPS:394008 | 21-225_15H8 | VK1|A30/JK4 | DIQMTQSPSSLSA SVGDRVTITC | RAS--QGIR-----NDLG | WYQQKPGK APKRLIF | A------ ASSLQS | GVPSRFSGSGSG-- TEFTLTISSLQPEDFATYYC | LQHNS--------YPLT | FGGGT KVEIR |
| iPS:394020 | 21-225_15H10 | VK1|A30/JK4 | DIQMTQSPSSLSA SVGDRVTITC | RAS--QGIR-----NDLG | WYQQKPGK APKRLIY | A------ ASSLQS | GVPSRFSGSGSG-- TEFTLTISSLQPEDFASYC | LQHNS--------YPLT | FGGGT KVEIN |
| iPS:394024 | 21-225_16B7 | VK1|A30/JK4 | DIQMTQSPSSLSA SVGDRVTITC | RAS--QGIR-----NDLG | WYQQKPGK APKRLIY | A------ ASSLQS | GVPSRFSGSGSG-- TEFTLTISSLQPEDFATYYC | LQHNS--------YPLT | FGGGT KVEIN |
| iPS:394037 | 21-225_4F4 | VK1|A30/JK4 | DIQMTQSPSSLFA SVGDRVTITC | RAS--QGIR-----NDLG | WYQQKPGK APKRLIY | A------ ASSVQT | GVPSRFSGSGSG-- TEFTLTISSLQPEDFATYYC | LQHNS--------YPLT | FGGGT KVEIK |
| iPS:394045 | 21-225_4H4 | VK1|A30/JK4 | DIQMTQSPSSLSA SVGDRVTITC | RAS--QGIR-----NDLG | WYQQKPGK APKRLIY | A------ ASSVQS | GVPSRFSGSGSG-- TEFTLTISSLQPEDFATYYC | LQHNS--------YPLT | FGGGT KVEIK |
| iPS:394049 | 21-225_13H5 | VK1|A30/JK4 | DIQMTQSPSSLSA SVGDRVTITC | RAS--QGIR-----NDLG | WYQQKPGK APKRLIY | A------ ASSLQT | GVPSRFSGSGSG-- TEFTLTISSLQPEDFATYYC | LQHNS--------YPLT | FGGGT KVEIR |
| iPS:394053 | 21-225_11F10 | VK1|A30/JK4 | DIQMTQSPSSLSA SVGDRVTITC | RAS--QGIR-----NDLG | WYQQKPGK APKRLIY | T------ ASSLQS | GVPSRFNGSGSG-- TEFTLTVSSLQPEDFATYYC | LQHSS--------YPLT | FGGGT KVEIK |
| iPS:394057 | 21-225_15H1 | VK1|A30/JK4 | DIQMTQSPSSLSA SVGDRVTITC | RAS--QGIR-----NDLG | WYQQKPGK APKRLIY | A------ ASSLQS | GVPSRFSGSGSG-- TEFTLTISSLQPEDFATYYC | LQHNS--------YPLT | FGGGT KVEIK |
| iPS:394059 | 21-225_9E8 | VK1|A30/JK4 | DIQMTQSPSSLFA SVGDRVTITC | RAS--QGIR-----NDLG | WYQQKPGK APKRLIY | A------ ASSLQS | GVPSRFSGSGSG-- TEFTLTISSLQPEDFATYYC | LQHNS--------YPLT | FGGGT KVEIK |
| iPS:394063 | 21-225_16A1 | VK1|A30/JK4 | DIQMTQSPSSLSA SVGDRVTITC | RAS--QGIR-----NDLG | WYQQKPGK APKRLIY | A------ ASSLQS | GVPSRFSGSGSG-- TEFTLTISSLQPEDFATYYC | LHHSN--------YPLT | FGGGT KVEIE |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:394 073 | 21-225_15C9 | VK1\|A30/ JK4 | DIQMTQSPSSLSA SVGDRVTITC | RAS--QGIR------NDLG | WYQQKPGK APKRLIY | A-------ASSLQS | GVPSRFSGSGSG--TEFTLTISSLQPEDFATYYC | LQHTS-------------YPLT | FGGGT KVEIK |
| iPS:394 075 | 21-225_8D12 | VK1\|A30/ JK4 | DIQMTQSPSSLSA SVGDRVTITC | RAS--QGIR------NDLG | WYQQKPGK APKRLIY | A-------ASSLQS | GVPSRFNGSGSG--TEFTLTISSLQPEDFATYYC | LQHSS-------------YPLT | FGGGT KVEIK |
| iPS:394 079 | 21-225_11F5 | VK1\|A30/ JK4 | DIQMTQSPSSLSA SVGDRVTITC | RAS--QGIR------NDLG | WYQQKPGK AFKRLIY | A-------ASSVQS | GVPSRFSGSGSG--TEFTLTISSLQPEDFATYYC | LQHNS-------------YPLT | FGGGT KVEIK |
| iPS:394 091 | 21-225_13H3 | VK1\|A30/ JK4 | DIQMTQSPSSLSA SVGDRVTITC | RAS--QGIR------NDLG | WYQQKPGK APKRLIY | A-------ASSLQS | GVPSRFSGSGSG--TEFTLTISSLQPEDFATYYC | LQHNS-------------YPLT | FGGGT KVEIK |
| iPS:398 528 | 21-225_32G1 | VK1\|A30/ JK4 | DIQMTQSPSSLSA SVGDRVTITC | RAS--QDMR------SDLG | WYQQKPGK APKRLIY | A-------ASSLQS | GVPSRFSGSGSG--TEFTLTISSLQPEDFATYYC | LQHTI-------------SPPT | FGGGT KVEIK |
| iPS:398 534 | 21-225_33B8 | VK1\|A30/ JK4 | DIQMTQSPSSLSA SVGDRVTITC | RAS--QDIR------SDLG | WYQQKPGK APKRLIY | A-------ASSLQS | GVPSRFSGSGSG--TEFTLTISSLQPEDFATYYC | LQHTI-------------YPPT | FGGGT KVEIK |
| iPS:398 540 | 21-225_35A6 | VK1\|A30/ JK4 | DIQMTQSPSSLSA SVGDRVTITC | RAS--QDIR------SDLG | WYQQKPGK APKRLIY | A-------TSSLQS | TEFTLTISSLQPEDFATYYC | LQHTI-------------YPPT | FGGGT KVEIK |
| iPS:402 219 | 21-225_1C12 | VK1\|A30/ JK4 | DIQMTQSPSSLSA SVGDRVTITC | RAS--QGIR------NDLG | WYQQKPGK AFKRLIY | A-------ASSLQS | GVPSRFSGSGSG--TEFTLTISSLQPEDFATYYC | LQHNS-------------YPLT | FGGGT KVAIK |
| iPS:403 868 | 21-225_19D11 | VK1\|A30/ JK4 | DIQMTQSPSSLSA SVGDRVTITC | RAS--QGIR------NDLG | WYQQKPGK APKRLIY | A-------TSSLQS | GVPSRFSGSGSG--TEFTLTISSLQPEDFATYYC | LQYYS-------------YPLT | FGGGT EVEIK |
| iPS:403 872 | 21-225_8F11 | VK1\|A30/ JK4 | DIQMTQSPSSLSA SVGDRVTITC | RAS--QGIR------SDLG | WFQQKPGK APKRLIF | D-------ASSVQS | GVPSRFSGSGSG--TEFTLTISSLQPEDFATYYC | LQHYT-------------YPLT | FGGGT KVEIK |
| VK2\|A18/JK 5 | | Germline | | | | | | | FGQGT RLEIK |
| iPS:468 816 | 21-225_52G8 | VK2\|A18/ JK5 | DIVMTQTPLSLSV TPGQPASMSC | KSS--QSLLHSE-GKTYLY | WYLQKTGQ PPHLLIY | E-------VSKRLS | GVPDRFSGSGSG--TDFTLKISRMEAEDVGVYYC | MQSMQ-------------LPIT | FGQGT RLEIK |
| iPS:434 021 | 21-225_49C1 | VK2\|A18/ JK5 | DIVMTQTPLSLSV TPGQPASISC | KSS--QSLLHRE-GKTYLY | WYLQKPGQ APQFLIF | E-------VSHRFS | GVPDRFSGSGSG--TDFTLKISRVEAEDVGVYYC | MQSIQ-------------LPIT | LGQGT RLEIK |
| iPS:434 025 | 21-225_49G3 | VK2\|A18/ JK5 | DIVMTQTPLSLSV TPGQPASMSC | KSS--QSLLHSE-GKTYLY | WYLQKTGQ PPHLLIY | E-------VSNRLS | GVPDRFSGSGSG--TDFTLKISRMEAEDVGVYYC | MQSMQ-------------LPIT | FGQGT RLEIK |
| iPS:434 031 | 21-225_49E7 | VK2\|A18/ JK5 | DIVMTQTPLSLSV TPGQPAFMSC | KSS--QIPLHSE-GKTYLY | WYLQKTGQ PPHLLIY | E-------VSKRLS | GVPDRFSGSGSG--TDFTLKISRMEAEDVGVYYC | MQSMQ-------------LPIT | FGQGT RLEIK |
| iPS:434 033 | 21-225_49F9 | VK2\|A18/ JK5 | DIVMTQTPLSLSV TPGQPASISC | KSN--QSLVHNE-GKTYLY | WYLQKPGQ PPQLLIF | E-------VSNRFS | GVPDRFSGSGSG--TDFTLKISRVEAEDVGVYYC | MQSIQ-------------YPIT | FGQGT RLEIK |
| iPS:434 093 | 21-225_52D10 | VK2\|A18/ JK5 | DVMMTQIPLSLSV TPGQPASISC | KSS--QSLLHSE-PFQLLIY | WYLQKPGQ PFQLLIF | E-------VSNRVS | GVPDRFSGSGSG--TDFTLKISRVEAEDVGVYYC | MQSIQ-------------LPIT | FGQGT RLEIK |
| iPS:434 151 | 21-225_55C2 | VK2\|A18/ JK5 | DVMMTQIPLSLSV TPGQPASISC | KSS--QSLLHSE-GKTYLY | WYLQKPGQ PFQLLIF | E-------VSNRVS | GVPDRFSGRGSG--TDFTLKISRVEAEDVGVYYC | MQSIL-------------YPIT | FGQGT RLEIK |
| iPS:434 161 | 21-225_55F9 | VK2\|A18/ JK5 | DIVMTQTPLSLSV TPGQSASISC | KSS--QSLLHSE-GKTYLY | WYLQKPGQ PPQLLIY | E-------VSNRFS | GVPDRFSGSGSG--TDFTLKISRVEAEDVGVYYC | IQSIQ-------------LPIT | FGQGT RLEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:435 329 | VK2JA18/ JK5 | DIVMTQTPLSLSV TPGQPASISC | KTS------ QSLLHSE- GKTYLY | WYLQKPGQ PPLLIY | E-------- VSNRFS | GVPDRFSGSGSG-- TDFTLKISRVEAEDVGVYYC | MQSI------- ----------QLIT | FGQGT RLEIK |
| iPS:392 924 | VK2JA18/ JK5 | DIVMTQTPLSLSV TPGQPASISC | RSS------ QSLLHSD- GRTYLY | WYLQKPGQ PPLLIY | E-------- LSNRFS | GVPDRFSGSGSG-- TDFTLKISRVEAEDVGVYYC | LQSIQ------ ----------YPIT | FGQGT RLEIK |
| | Germline | K_FR1 | K_CDR1 | K_FR2 | K_CDR2 | K_FR3 | K_CDR3 | K_FR4 |
| VK2JA18JK 1 | | DIVMTQTPLSLSV TPGQPASISC | KSS------ QSLLHSD- GKTYLY | WYLQKPGQ PPQLLIY | E-------- VSNRFS | GVPDRFSGSGSG-- TDFTLKISRVEAEDVGVYYC | MQSIQ------ ----------LPWT | FGQGT KVEIK |
| iPS:468 822 | VK2JA18/ JK1 | AIVMTQTPLSLSV TPGQPASISC | KSS------ QRLLHGD- GKTYLY | WYLQKPGQ PPHLLIS | E-------- VSNRFS | GVPDRFSGSGSG-- TDFTLKISRVEAEDVGVYYC | MQSIQ------ ----------VPWT | FGQGT KVEIK |
| iPS:433 917 | VK2JA18/ JK1 | DIVMTQTPLSLSV TPGQPASISC | RSS------ QSLLHSD- GRTYLY | WYLQKPGQ PPQLLIY | E-------- LSNRFS | GVPDRFSGSGSG-- TDFTLKISRVEAEDVGVYYC | MQSIQ------ ----------LPWT | FGQGT KVEIK |
| iPS:433 965 | VK2JA18/ JK1 | DIVMTQTPLSLITV TPGQPASISC | KSS------ QSLLHGD- GKTYLY | WYLQRPGQ PPQVLIY | E-------- VSNRFS | GVPDRFSGSGSG-- TDFTLKLSRVEAEDVGVYYC | MQSIQ------ ----------LPWT | FGQGT KVEIK |
| iPS:433 985 | VK2JA18/ JK1 | DIVMTQTPLSLSV TPGQPASISC | TSS------ QSLLHSE- GKTYLY | WYLQKPGQ PPQLLIY | E-------- VSNRFS | GVPDRFSGSGSG-- TDFSLKISRVEAEDVGVYYC | MQSIQ------ ----------LPWT | FGQGT KVEIK |
| iPS:433 991 | VK2JA18/ JK1 | DIVMTQTPLSLSV TPGQPASISC | KSS------ QSLLHSD- GRTYLY | WYLQKPGQ PPQLLIY | E-------- VSSRFS | GVPDRFSGSGSG-- TDFALKISRVEAEDVGVYYC | MQSIQ------ ----------LPWT | FGQGT KARIK |
| iPS:434 345 | VK2JA18/ JK1 | EIVMTQTPLSLSV TPGQPASISC | KSS------ QSLLHGD- GKTYLF | WYLQRPGQ PPQVLIY | E-------- VSNRLC | GVPDRFSGSGSG-- TDFTLKISRVEAEDVGVYYC | MQSIQ------ ----------VPWT | FGQGT KVEIT |
| iPS:435 297 | VK2JA18/ JK1 | DIVMTQTPLSLSV TPGQPASISC | KSS------ QSLLHGD- GKTYLY | WYLQKPGQ PPQLLIY | E-------- VSNRFS | GVPDRFSGSGSG-- TDFTLKISRVEAEDVGVYYC | MQSIQ------ ----------LPWT | FGQGT KVEIK |
| iPS:435 341 | VK2JA18/ JK1 | AIVMTQTPLSLSV TPGQPASISC | KSS------ QSLLHGD- GKTYLY | WYLQKPGQ PPQLLIY | E-------- VSHRFS | GVPDRFSGSGSG-- TDFTLKISRVEAEDVGLYHC | MQSIQ------ ----------LPWT | FGQGT KVEIK |
| iPS:435 357 | VK2JA18/ JK1 | DIVMTQTPLSLSV TPGQPASISC | KSS------ QSLLHGD- GKTYLY | WYLQKPGQ PPQLLIY | E-------- VSNRFS | GVPDRFSGSGSG-- TDFTLKISRVEAEDVGVYYC | MQSIQ------ ----------LPWT | FGQGT KVEIK |
| iPS:435 365 | VK2JA18/ JK1 | DIVMTQSPLSLFV TPGQPASISY | KSS------ QSLLHGD- GKTYFY | WYLQKPGQ PPQLLIY | E-------- VSNRFS | GVPDRFSGSGSG-- TDFTLKISRVEAEDVGVYYC | MQSIQ------ ----------LPWT | FGQGT KVEIK |
| iPS:435 413 | VK2JA18/ JK1 | DIVMTQTPLSLSV TPGQPASISC | KSS------ QSLVHGD- GKTYLY | WYLQRPGQ PPQLLIY | E-------- VSNRFS | GVPDRFSGSGSG-- TDFTLKISRVEAEDVGVYYC | MQSIQ------ ----------LPWT | FGQGT KVEIK |
| iPS:435 423 | VK2JA18/ JK1 | DIVMTQTPLSLSV TPGQPASISC | KSS------ QRLLHGD- GKTYLY | WYLQKPGQ PPQLLIY | E-------- VSNRFS | GVPDRFSGSGSG-- TDFTLKISRVEAEDVGVYYC | MQSIQ------ ----------VPWT | FGQGT KVEIK |

Figure 51 (Continued)

| | | | | | | | | |
|---|---|---|---|---|---|---|---|---|
| iPS:435 429 | 21-225_151A1 | VK2|A18/ JK1 | DIVMTQTPLSLSV TPGQPASISC | KSS--- QSLLHGD- GKTYLY | WYLQKPGQ PPQLLIY | E------ VSKRFS | GVPDRFSGSGSG--- TDFTLKISRVEAEDVGVYYC | MQSIQ------- ------IPWT | FGQGT KVEIK |
| iPS:435 441 | 21-225_152F6 | VK2|A18/ JK1 | DIVMTQTPLSLSV TPGQPASISC | KSS--- QSLRHGD- GKTYLT | WYLQRPGQ PPQVLIH | E------ ISKRFT | GVPDRFSGSGSG--- TDFTLNISRVEAEDVGFYYC | MQSIQ------- ------VPWT | FGQGT KVEIK |
| iPS:435 457 | 21-225_152C1 | VK2|A18/ JK1 | DIVMTQAPLSLSV TPGQPASISC | KSS--- QSLRHGD- GKTYLY | WYLQRPGQ PPQILIY | E------ VSNRFS | GVPDRFSGSGSG--- TDFTLNISRVEAEDFGFYYC | MQSIQ------- ------IPWT | FGQGT KVDIK |
| iPS:435 463 | 21-225_153D2 | VK2|A18/ JK1 | DIVMTQTPLSLSV TPGQPASISC | KSS--- QSLRHGD- GKTYLT | WYLQKPGQ PPQVLIH | E------ VSKRFT | GVPDRFSGSGSG--- TDFTLNISRVEAEDVGFYYC | MQSIQ------- ------VPWT | FGQGT KVEIK |
| iPS:435 489 | 21-225_155A5 | VK2|A18/ JK1 | DIVMTQTPLSLSV TPGQPASISC | KSS--- QSLLHGD- GKTYLY | WYLQKPGQ PPQLLIY | E------ VSNRFS | GVPDRFSGSGSG--- TDFTLKISRVEAEDVGFYYC | MQSIQ------- ------VPWT | FGQGT KVEIK |
| iPS:435 531 | 21-225_157G8 | VK2|A18/ JK1 | DIVMTQTPLSLSV TPGQPASISC | KST--- QSLLHGD- GKTYLY | WYLQKPGQ SPQLLIY | E------ ISKRFS | GVPDRFSGSGSG--- TDFTLKISRVEAEDVGVYYC | MQSIQ------- ------VPWT | FGQGT KVEIK |
| iPS:435 577 | 21-225_160B1 | VK2|A18/ JK1 | DIVMTQTPLSLSV TPGQPASISC | KSS--- QSLLHGD- GKTYFY | WYLQKPGQ PPQVLIY | E------ VSKRFS | GVSERFSGSGSG--- TDFTLKISRVEAEDVGLYHC | MQSIQ------- ------IPWT | FGQGT KVEIK |
| iPS:435 601 | 21-225_160G1 | VK2|A18/ JK1 | AIVMTQTPLSLSV TPGQPASISC | KSS--- QSLLHGD- GKTYLY | WYLQKPGQ PPHLLIY | E------ VSKRFS | GVPDRFSGSGSG--- TDFTLKISRVEAEDVGLYHC | MQSIQ------- ------LPWT | FVQGT KVEIT |
| iPS:435 629 | 21-225_162H6 | VK2|A18/ JK1 | DIVMTQTPLSLSV TPGQPASISC | KSS--- QSLLHGD- GKTYLY | WYLQKPGQ PPQLLIY | E------ VSNRFS | GVPERFSGSGSG--- TDFTLKISRVEAEDVGVYYC | KQSIQ------- ------LPWT | FGQGT KVEIK |
| iPS:435 655 | 21-225_167E2 | VK2|A18/ JK1 | DIVMTQTPLSLSV TPGQPASISC | KSS--- QSLLHGD- GKTYLY | WYLQKPGQ PPHLLIY | E------ VSKRFS | GVPDRFSGGGSG--- TDFTLKISRVEAEDVGLYHC | MQSIQ------- ------LPWT | FGQGT KVEIK |
| iPS:435 657 | 21-225_167H1 | VK2|A18/ JK1 | DIVMTQTPLSLSV TPGQPASISC | KSS--- QSLLHGD- GKTYLY | WYLQKPGQ PPHLLIY | E------ VSKRFS | GVPDRFSGSGSG--- TDFTLKISRVEAEDVGLYHC | MQSIQ------- ------LPWT | FGQGT KVEIK |
| iPS:435 683 | 21-225_170A1 | VK2|A18/ JK1 | EIVMTQTPLFLSV TPGQPASISC | KSS--- QSLLHGD- GKTYLF | WYLQKPGQ PPQVLIY | E------ VSNRFS | GVPDRFSGSGSG--- TDFTLKISRVEAEDVGVYYC | MQSIQ------- ------LPWT | FGQGT KVEIK |
| iPS:435 723 | 21-225_172B7 | VK2|A18/ JK1 | DIVMTQTPLSLSV TPGQPASISC | KSS--- QSLLHGD- GKTYLY | WYLQKPGQ PPQLLIY | E------ VSNRFS | GVPDRFSGGGSG--- TDFTLKISRVEAEDVGVYYC | MQSIQ------- ------FPWT | FGQGT RVDIK |
| iPS:435 731 | 21-225_173A1 | VK2|A18/ JK1 | DIVMTQTPLSLSV TPGQPASISC | KSS--- QSLLHGD- GKTYFY | WYLQKPGQ PPQLLIF | E------ VSNRFS | GVPDRFSGSGSG--- TDFTLKISRVEAEDVGVFFC | MQSIQ------- ------VPWT | FGQGT KVEIK |
| iPS:435 755 | 21-225_176H4 | VK2|A18/ JK1 | DIVMTQTPLSLSV TPGQPASISC | KSS--- QSLLHGD- GKTYLY | WYLQKPGQ PPQLLIY | E------ VSNRFS | GVPDRFSGSGSG--- TDFTLKISRVEAEDVGIYYC | MQSIQ------- ------IPWT | FGQGT RVEIK |
| iPS:435 771 | 21-225_177B1 | VK2|A18/ JK1 | DIVMTQTPLSLSV TPGQPASISC | KSS--- QRLLHGD- GKTYLY | WYLQKPGQ PPQILIY | E------ VSNRFS | GVPDRFSGSGSG--- TDFTLKISRVEAEDVGVYYC | MQSIQ------- ------IPWT | FGQGI KVEIK |

Figure 51 (Continued)

| | | | | | | | | |
|---|---|---|---|---|---|---|---|---|
| iPS:435 781 | 21-225_178G10 | VK2|A18/ JK1 | HIVMTQTPLSLSV TPGQPASISC | KSS--- QSLLHSD- GKTYLY | WYLQKPGQ PPQLLIY | E------ VSNRFS | GVPDRLSGGGSG--- TDFTLKISRVEAEDVGIYYC | MQSIQ--- ------VPWT | FGQGT KVEIK |
| iPS:435 789 | 21-225_180C4 | VK2|A18/ JK1 | DIVMTQTPLSLSV TPGQPASISC | KSS--- QSLLHGD- GKTYLY | WYLQKPGQ PPQLLIY | A------ TSNRFF | GVSDRFSGSGSG--- TDFTLKISRVEAEDVGVYYC | MQSIQ--- ------VPWT | FGQGT KVEIK |
| iPS:435 795 | 21-225_181C2 | VK2|A18/ JK1 | EIVMTQTPLSLSV TPGQPASISC | KSS--- QSLLHGD- GKTYLY | WYLQKPGQ PPQLLIB | E------ VSNRFS | GVPDRFSGSGSG--- TDFTLKISRVEAEDVGVYYC | MQSIQ--- ------VPWT | FGQGT KVEIK |
| iPS:435 807 | 21-225_181C10 | VK2|A18/ JK1 | DIVMTQTPLSLSV TPGQPASISC | KSS--- QSLLHGD- GKTYLY | WYLQKPGQ PPQLLIY | E------ VSNRFS | GVPDRFSGSGSG--- TDFTLKISRVEAEDVGVYHC | MQSIQ--- ------IPWT | FGQGT KVEIK |
| iPS:435 827 | 21-225_190H1 | VK2|A18/ JK1 | DIVMTQTPLSLSV TPGQPASISC | KSS--- QSLLHSD- GKTYLY | WYLQKPGQ PPQLLIC | E------ VSNRFS | GVTDRFSGSGSG--- TDFTLKISRVEAGDVGVYYC | MQSIQ--- ------FPWT | FGQGT KVEIK |
| iPS:435 839 | 21-225_191B1 | VK2|A18/ JK1 | DIVMTQTPLSLSV TPGQPASISC | KSS--- QSLLHSD- GKTYLF | WYLQKPGQ PPQLLIY | E------ LSNRFS | GVSDRFSGSGSG--- TDFTLKISRVEAEDVGVYYC | MQSFQ--- ------LPWT | FGQGT KVEIK |
| iPS:435 853 | 21-225_191E3 | VK2|A18/ JK1 | DIVMTQTPLSLSV TPGQPASISC | KSS--- QSLLHSD- GRTYLY | WYLQKPGQ PPQLLIC | E------ VSNRFA | GVPDRFSGSGSG--- TDFTLKISRVEAGDVGVYYC | MQSIQ--- ------LPWT | FGQGT KVEIN |
| iPS:435 871 | 21-225_191E6 | VK2|A18/ JK1 | DIVMTQTPLSLSV TPGQPASISC | KSS--- QSLLHSD- GKTYLY | WYLQKPGQ PPQLLIC | E------ VSNRFA | GVTDRFSGSGSG--- TDFTLKISRVEAEDVGIYYC | MQSIH--- ------FPWT | FGQGT KVEIK |
| iPS:435 887 | 21-225_186F7 | VK2|A18/ JK1 | DIVMAQTPLSLSV TPGQPASISC | KSS--- QSLLHSD- GKTYLC | WYLQKPGQ PPQLLIY | E------ VSKRFS | GVPDRFSGSGSG--- TDFTLKISRVEAEDVGVYYC | MQSIQ--- ------VPWT | FGQGT KVEIK |
| iPS:435 899 | 21-225_188G1 | VK2|A18/ JK1 | DIVMTQTPLSLSV TPGQPASISC | MSS--- QSLLHSD- GKTYLF | WYLQKPGQ PPQLLIC | E------ VSNRFS | GVPDTFSGSGSG--- TDFTLKISRVEAEDVGVYYC | MQSIQ--- ------IPWT | FGQGT KVEIK |
| iPS:435 901 | 21-225_189G2 | VK2|A18/ JK1 | DIVMTQTPLSLSV TPGQPASISC | KSS--- QSLLHGD- GKTYLF | WYLQKPGQ PPQLLIY | E------ VSNRFA | GVSDRFSGSGSG--- TDFTLKISRVEAEDVGVYYC | MQSIQ--- ------IPWT | FGQGT KVEIK |
| iPS:435 927 | 21-225_190E7 | VK2|A18/ JK1 | DIVLIQTPLSLSV TPGQPASISC | KSS--- QSLLHSD- GKTYLY | WYLQKPGQ PPQVLIC | E------ VSNRFS | GVPDRFSGSGSG--- TDFTLKISRVEAGDVGVYYC | MQSIQ--- ------IPWT | FGQGT KVEIK |
| iPS:435 999 | 21-225_192F9 | VK2|A18/ JK1 | DIVMTQTPLSLSV TPGQPASISC | KSS--- QSLLHSD- GKTYLY | WYLQREGQ PPQLLIC | E------ VSNRFS | GVTIDRFSGSGSG--- TDFTLKISRVEAEDVGVYYC | MQSIQ--- ------LPWT | FGQGT KVEIK |
| iPS:436 060 | 21-225_194F4 | VK2|A18/ JK1 | DIVMTQTPLSLSV TPGQPASISC | KSS--- QSLLHSD- GKTYLY | WYLQKPGQ PPQLLIC | E------ VSNRFS | GVPDRFSGSGSG--- TDFTLKISRVEAGDVGVYYC | MQSIQ--- ------LPWT | FGQGT KVEIK |
| iPS:436 158 | 21-225_197G8 | VK2|A18/ JK1 | EIVMTQTPLSLSV IPGQPASISC | KSS--- QNLLHSD- GKTYLY | WYLQKPGQ PPQVLIY | E------ VSNRFS | GVPDRFSGSGSG--- TDFTLKISRVEAEDVGVYSC | MQSIQ--- ------LPWT | FAQGS KVEIK |
| iPS:436 193 | 21-225_198A10 | VK2|A18/ JK1 | DIVLIQTPLSLSV TPGQPASISC | KSS--- QSLLYSD- GRTYLY | WYLQKPGQ PPQVLIC | E------ VSNRFS | GVPDRFSGSGSG--- TDFTLKISRVEAGDVGVYYC | MQSIQ--- ------LPWT | FGQGT KVEIK |

Figure 51 (Continued)

| | | | | | | | |
|---|---|---|---|---|---|---|---|
| iPS:436 536 | 21-225_224G1 | VK2|A18/ JK1 | DIVMTQTPLSLSV TPGQPASISC | KSG---QSLLHSD-GKTFLS | WYLQKPGQ PPQLLIY | E------ISNRFS | GVPDRFSGSGSG-TDFTLKISRVEAEDVGIFYC | MQSTQ-------- | -------LPRT | FGQGT KVEIK |
| iPS:436 548 | 21-225_224A7 | VK2|A18/ JK1 | DIVMTQTPLSLSV TPGQPASISC | KSS---QSLLHSD-GKTFLY | WFLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 558 | 21-225_224C1 | VK2|A18/ JK1 | DFVMTQTPLSLSV TPGQPASISC | KSS---QSLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 562 | 21-225_224H1 | VK2|A18/ JK1 | DIVMTQTPLSLSV TPGQPASISC | KSS---QSLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 572 | 21-225_225G4 | VK2|A18/ JK1 | DIVMTQTPLSLSV TPGQPASISC | KSS---QSLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 592 | 21-225_226B1 | VK2|A18/ JK1 | DIVMTQTPLSLSV TPGQPASISC | KSS---QSLLHGD-GKTYLY | WYLQKPGQ PPQLLIY | E------VSIRFS | GVPDRFSGSGSG-TDFTLKISRVEAEDVGIYYC | MQSTQ-------- | -------IPWT | FGQGT KVDIK |
| iPS:436 594 | 21-225_226A5 | VK2|A18/ JK1 | DIVMTQTPLSLSV TPGQPASISC | KSS---QSLLHGD-GKTYLY | WYLQKPGQ PPQLLIY | E------VSNRFS | GVPDRFSGSGSG-TDFTLKISRVEAEDVGVYYC | MQSTQ-------- | -------IPWT | FGQGT KVEIK |
| iPS:436 602 | 21-225_226E7 | VK2|A18/ JK1 | DIVMTQTPLSLSV TPGQPASISC | KSS---QSLLHSD-GKTFLY | WYQQKPGQ PPQLLIY | E------VSNRFS | GVPDRFSGSGSG-TDFTLKISRVEAEDVGVYYC | MQSTQ-------- | -------VPWT | FGQGT KVEIK |
| iPS:436 606 | 21-225_226G8 | VK2|A18/ JK1 | DIVMTQTPLSLSV TPGQPASISC | KSS---QSLLHSD-GKTFLY | WYLHKPGQ PPHLLIY | E------ISNRFS | GVPDRFSGSGSG-TDFTLKISRVEAEDVGIYYC | MQSTQ-------- | -------LPRT | FGQGT KVEIK |
| iPS:436 610 | 21-225_226F9 | VK2|A18/ JK1 | DIVMTQTPLSLSV TPGQPASISC | KSS---QSLLHSD-GKTFLY | WYLQRPGQ PFQLLIY | E------VSNRFS | GVPDRFSGSGSG-TDFTLKISRVEAEDVGIYYC | MQSTQ-------- | -------LPRT | FGQGT KVEIK |
| iPS:436 612 | 21-225_226H9 | VK2|A18/ JK1 | DIVMTQTPLSLSV TPGQPASISC | KSS---QSLLHSD-GKTFLY | WYLQRPGQ PPQLLIY | E------VSNRFS | GVPDRFSGSGSG-TDFTLKISRVEAEDVGIYYC | MQSTQ-------- | -------LPRT | FGQGT KVEIK |
| iPS:436 614 | 21-225_226F10 | VK2|A18/ JK1 | DIVMTQTPLSLSV IPGQPASISC | KSS---QSLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 618 | 21-225_226E1 | VK2|A18/ JK1 | DIVMTQTPLSLSV TPGQPASISC | KSS---QSLLHSD-GKTFLY | WYLHKPGQ PPHLLIY | E------ISNRFS | GVPDRFSGSGSG-TDFTLKISRVEAEDVGIYYC | MQSTQ-------- | -------LPRT | FGQGT KVEIK |
| iPS:436 624 | 21-225_226H12 | VK2|A18/ JK1 | DIVMTQTPLSLSV TPGQPASISC | KSS---QSLLHSD-GKTFLY | WYLQKPGQ PPQPLIY | E------ISNRFS | GVPDRFSGSGSG-TDFTLKISRVEAEDVGIYYC | MQSTQ-------- | -------LPRT | FGQGT KVEIK |
| iPS:436 626 | 21-225_227C1 | VK2|A18/ JK1 | DIVMTQTPLSLSV TPGQPASISC | KSS---KTLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |
| iPS:436 628 | 21-225_227F2 | VK2|A18/ JK1 | DIVMTQTPLSLSV TPGQPASISC | KSS---QSLLHSD-GKTFLY | WYLQKPGQ PPQLLIY | E------ISNRFS | GVPDRFSGSGSG-TDFTLKISRVEAEDVGIYYC | MQSTQ-------- | -------LPRT | FGQGT KVEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:436 640 | 21-225_227A8 | VK2|A18/ JK1 | DIVMTQTPLSLSV TPGQPASISC | KSS------QSLLHSD-GKTFLY | WYLQKPGQ PPQLLIY | E-------VSNRFS | GVPDRFSGSGSG-TDFTLKISRVEAEDVGIYYC | MQSTQ-----------LPRT | FGQGT RVEIK |
| iPS:392 814 | 21-225_22A1 | VK2|A18/ JK1 | DIVMTQTPLSLSV TPGQPASISC | KSS------QSLLHSG-GKTYLY | WYLQKPGQ PPQLLIY | E-------VSNRFS | GLPDRFSGSGSG-TDFTLKISRVEAADVGVYYC | MQTLH-----------LPWT | FGQGT KVEIK |
| iPS:392 930 | 21-225_25H9 | VK2|A18/ JK1 | DIVMTQTPLSLSV TPGQPASISC | KSS------QSLLHGD-GKTYLF | WYLQKPGQ PPQLLIY | E-------VSNRFS | GVPDRFSGSGSG-TDFTLKISRVEAEDVGVYYC | MQSIQ-----------LPWT | FGQGT KVEIK |
| iPS:393 032 | 21-225_26F8 | VK2|A18/ JK1 | DIVMTQTPLSLSV TPGQPASISC | KSS------QSLLHGD-GKTYLY | WYLQKPGQ PPQLLIY | E-------VSNRFS | GVPDRFSGSGSG-TDFTLKISRVEAEDVGVYYC | MQSIQ-----------LPWT | FGQGT KVEIK |
| iPS:393 036 | 21-225_28G3 | VK2|A18/ JK1 | EIVMTQTPLSLSV TPGQPASISC | KSS------QSLLHGD-GKTYLY | WYLQKPGQ PPQLLIY | E-------VSNRFS | GVPERFSGSGSG-TDFTLKISRVEAEDVGVYYC | MQSIQ-----------IPWT | FGQGT KVEIK |
| | Germline | | | | K_FR2 | K_CDR2 | K_FR3 | K_CDR3 | K_FR4 |
| VK1|A30|JK1 | | | | | | | | | |
| iPS:468 826 | 21-225_201C5 | VK1|A30/ JK1 | DIQMTQSPSSLSA SVGDRVTITC | RAS---QGIR-----HDLG | WYQQKPGK APKRLIY | A-------ASSLQS | GVPSRFSGSGSG-TEFTLTISSLQPEDFATYYC | LQHYS-----------FPRT | FGQGT KVEIK |
| iPS:468 842 | 21-225_50H4 | VK1|A30/ JK1 | DIQMTQSPSSLSA SVGDRVTITC | RAS---QGIR-----NDLG | WYQQKPGK APKRLIY | A-------ASSLQS | GVPSRFSGSGSG-TEFTLTISLQPEDFATYYC | LQHYS-----------YPRT | FGQGT KVEIK |
| iPS:468 858 | 21-225_148C9 | VK1|A30/ JK1 | DIQMTQSPSSLSA SVGDRVTITC | RAS---RGIR-----GDLG | WYQQKPGK APKRLIY | A-------ASSLQS | GVPSRFSGSGSG-TEFTLTISSLQPEDFATYYC | LQHYS-----------YPRI | FGQGT KVEIK |
| iPS:468 860 | 21-225_224E7 | VK1|A30/ JK1 | DIQMTQSPSSLSA SVGDRVTITC | RAS---QGIR-----NDLG | WYQQKPGK APTRLIY | A-------ASTLES | GVPSRFSGSGSG-TEFTLTISLQPEDFATYYC | LLHYN-----------YPRI | FGQGT KVEIT |
| iPS:433 919 | 21-225_44B3 | VK1|A30/ JK1 | DIQMTQSPSSLSA SVGDRVTITC | RAS---QGIR-----NDLG | WYQQKPGK APKRLIY | A-------ASSLQS | GVPSRFSGSGSG-TEFTLTISLQPEDFATYYC | LQHYS-----------YPRT | FGQGT KVEIK |
| iPS:433 923 | 21-225_44D3 | VK1|A30/ JK1 | DIQMTQSPSSLSA SVGDRVTFTC | RAS---QGIR-----DDLG | WYQQKPGK APKRLIY | A-------ASSLQS | GVPSRFSGSGSG-REFTLTISLQPEDFATYYC | LQHYS-----------YPRT | FGQGT KVEIK |
| iPS:433 929 | 21-225_44D5 | VK1|A30/ JK1 | DIQMTQSPSSLSA SVGDRVTITC | RAS---QDIR-----DDLG | WYQQKPGK APKRLIY | A-------ASSLQS | GVPSRFSGSGSG-TEFTLTISLQPEDFATYYC | LQHYS-----------YPRI | FGQGT KVEIK |
| iPS:433 935 | 21-225_44F9 | VK1|A30/ JK1 | DVQMTQSPSSLSA SVGDRVTITC | RAS---QGIR-----KDLG | WYQQKPGK APKRLIY | A-------ASSLQS | GVPSRFSGSGSRSG-TEFTLTISLQPEDFATYYC | LHHYN-----------YPRI | FGQGT KVEIK |
| iPS:433 939 | 21-225_44C10 | VK1|A30/ JK1 | DIQMTQSPSSLSA SVGDRVTITC | RAS---QGIR-----DDLG | WYQQKPGK APKRLIY | A-------TSSLQS | GVPSRFSGSGSG-TEFTLTISLQPEDFATYYC | LQHYS-----------YPRT | FGQGT KVEIK |
| iPS:433 951 | 21-225_45B4 | VK1|A30/ JK1 | DIQMTQSPSSLSA SVGDRVTITC | RAS---QGIR-----DDLG | WYQQKPGK APKRLIY | A-------ASSLQS | GVPSRFSGSGSG-TEFTLTISLQPEDFATYYC | LQHYS-----------YPRI | FGQGT KVEIK |
| iPS:433 955 | 21-225_45B8 | VK1|A30/ JK1 | DIQMTQSPSSLSA SVGDRVTFTC | RAS---QDIR-----DDLG | WYQQKPGK APKRLIY | A-------ASSLQS | GVPSRFSGSGSG-TEFTLTISLQPEDFATYYC | LQHYN-----------YPRI | FGQGT KVEIK |
| iPS:433 967 | 21-225_46C3 | VK1|A30/ JK1 | DIQMTQSPSSLSA SVGDRVTITC | RAS---QGIR-----DDLG | WYQQKPGK APKRLIY | A-------ASSLQS | GVPSRFSGSRSG-TEFTLTISLQPEDFATYYC | LQHYS-----------YPRI | FGQGT KVEIK |
| iPS:433 971 | 21-225_46D4 | VK1|A30/ JK1 | DIQMTQSPSSLSA SVGDRVTITC | RTS---QDIR-----KELG | WYQQKVGK APKRLIY | R-------ASSLES | GVPSRFSGSGSG-TEFTLTISLQPEDFATYYC | LQHYS-----------FPWT | FGQGT KVEIK |
| iPS:433 997 | 21-225_48C1 | VK1|A30/ JK1 | DIQMTQSPSSLSA SVGDRVTITC | RTS---QGIR-----NDLG | WYQQKPGK APKRLIY | A-------ASSLQS | GVPARFSGSGSG-TEFTLTISLQPEDFAIYYC | LQHNF-----------YPWT | FGQGT KVEIK |

Figure 51 (Continued)

| ID | V/J | FR1 | CDR1 | FR2 | CDR2 | FR3 | CDR3 | FR4 |
|---|---|---|---|---|---|---|---|---|
| iPS:434_001 | VK1|A30/JK1 | DIQMTQSPSSLSA SVGDRVTITC | RAS--RGIR----DDLG | WYQQKPGK PPKRLIY | A--------- ASSLQS | GVPSRFNGSGSG------ TEFTLTISSLQSEDLATYYC | LQQYS--------- ---------YPRT | FGQGT KVEIK |
| iPS:434_009 | VK1|A30/JK1 | DIQMTQSPSSLSA SVGDRVTITC | RAS--QGIR----NDLG | WYQQKPGK APKRLIY | T--------- ASSLQS | GVPSRFSGSGSG------ TEFTLTISGLQPEDFAIYYC | LQHNR--------- ---------YPWT | FGQGT KVEIK |
| iPS:434_047 | VK1|A30/JK1 | DIQMTQSPSSLSA SVGDRVTITC | RAS--QGIR----NDLG | WYQQKPGK APKRLIY | T--------- ASNLQS | GVPSRFSGSGSG------ TEFTLTISSLQPEDFATYYC | LQHNS--------- ---------YPWT | FGQGT KVEIK |
| iPS:434_067 | VK1|A30/JK1 | DIQMTQSPSSLSA SVGDRVTITC | RAS--QGIR----NDLG | WYQQKPGK APKRLIY | A--------- ASSLQS | GVPSRFSGSGSG------ THFTLTISSLQPEDFATYYC | LQHNS--------- ---------YPWT | FGQGT KVEIK |
| iPS:434_135 | VK1|A30/JK1 | DIQMTQSPSSLSA SVGDRVTITC | RAS--QDIR----NILG | WYQQKPGK APKRLIY | A--------- ASNLQS | GVPSRFSGSGSG------ TEFTLTISSLQPEDFATYYC | LQYNS--------- ---------YPWT | FGQGT KVEIK |
| iPS:434_197 | VK1|A30/JK1 | DIQMTQSPSSLSA SVGDRVTITC | RAS--QGIR----NDLG | WYQQKPGK APKRLIY | T--------- ASNLQS | GVPSRFSGSGSG------ TEFTLTISSLQPEDFATYYC | LQHNS--------- ---------YPWT | FGQGT KVEIK |
| iPS:434_203 | VK1|A30/JK1 | DIQMTQSPSSLSA SVGDRVTITC | RAS--QGIR----KDLG | WYQQKPGK APKRLIY | A--------- ASSLQS | GVPSRFSGSGSG------ TEFTLTISSLQPEDFATYYC | LQHNS--------- ---------YPWT | FGLGT KVEIK |
| iPS:434_209 | VK1|A30/JK1 | DIQMTQSPSSLSA SVGDRVTITC | RAS--QGIR----NDLG | WYQQKPGK APKRLIY | S--------- ASSLQS | GVPSRFSGSGSG------ TEFTLTISSLQPEDFATYYC | LQHNS--------- ---------YPWT | FGQGT KVEIK |
| iPS:434_229 | VK1|A30/JK1 | DIQMTQSPSSLSA SVGDRVTITC | RAS--QGIR----KDLG | WYQQKPGK APKRLIF | A--------- ASSLQS | GVPSRFSGSGSG------ TEFTLTISSLQPEDFATYYC | LQHNS--------- ---------YPWT | FGQGT KVEIK |
| iPS:434_241 | VK1|A30/JK1 | DIQMTQSPSSLSA SVGDRVTITC | RAS--QGIG----NDLG | WYQQKPGK APERLIY | A--------- ASSLQS | GVPSRFSGSGSG------ TEFTLTISSLQPEDFATYYC | LQHNS--------- ---------FPPWT | FGQGT KVEIK |
| iPS:434_257 | VK1|A30/JK1 | DIQMTQSPSSLSA SVGDRVTITC | RAS--QGIR----NDLG | WYQQKPGK APKRLIY | P--------- ASRLQS | GVPSRFSGSGSG------ TEFTLTISSLQPEDFATYYC | LQYNS--------- ---------YPWT | FGQGS KVEIK |
| iPS:434_281 | VK1|A30/JK1 | DIQMTQSPSSLSA SVGDRVTITC | RAS--QAIR----NDLG | WYQQKPGK APERLIY | A--------- ASSLQS | GVPSRFSGSGSG------ TEFTLTISSLQPEDFATYYC | LQHNS--------- ---------FPPWT | FGQGT KVEIK |
| iPS:434_315 | VK1|A30/JK1 | DIQMTQSPSSLSA SVGDRVTITC | RAS--QGIR----MDLG | WYQQKPGK APKRLIY | S--------- ASSLQS | GVPSRFSGSGSG------ TEFTLTISSLQPEDFATYYC | LQHNS--------- ---------YFPWT | FGQGS KVEIK |
| iPS:434_319 | VK1|A30/JK1 | DIQMTQFPSQSA SVGDRVTITC | RAS--QGIR----NDLG | WYQQHPGK AHKRLIY | A--------- ASSCQS | GVPSRFSGTRSG------ TEFTSISSMQRDFATYYC | LQHNS--------- ---------YPWT | FGQGT KVEIK |
| iPS:434_339 | VK1|A30/JK1 | DIQMTQSPSSRSA SVGDRVTITC | RAS--QGIR----NDLG | WYQQKPGK APKRLIY | A--------- ASSLQS | GVPSRFSGSGSG------ TEFTLTISSLQPEDFATYYC | LQHYS--------- ---------YPWT | FGQGT KVEIK |
| iPS:434_343 | VK1|A30/JK1 | DIQMTQSPSSLSA AVGDRVTITC | RAS--QGIR----NDLG | WYQQKPGK AFKCLIY | A--------- ASRLQI | GVPSRFSGSGSG------ TEFTLTISSLQPEDFATYYC | LRHYS--------- ---------YPRT | FGQGT KVEIK |
| iPS:434_385 | VK1|A30/JK1 | DIQMTQSPSSLSA SVGDRVTITC | RAS--QAIR----NDLG | WYQQKPGK APERLIY | A--------- AFRLQI | GVPSRFSGSGSG------ TEFTLTISSLQPEDFATYYC | LQYNS--------- ---------YPRT | FGQGS KVEIK |
| iPS:434_387 | VK1|A30/JK1 | DIQMTQSPSSLSA SVGDRVTITC | RAS--QGIR----NDLG | WYQQKPGK APQRLIF | P--------- ASSLQS | GVPSRFSGSGSG------ TEFTLTISSLQPEDFATYYC | LQHNS--------- ---------YFPWT | FGQGS KVEIK |
| iPS:434_441 | VK1|A30/JK1 | DIQMTQFPSQSA SVGDRVTITC | RAS--QGIR----NDLG | WYQQHPGK AHKRLIY | A--------- ASSCQS | GVPSRFSGTRSG------ TEFTSISSMQRDFATYYC | IVHNS--------- ---------YPWT | FGQGT KVEIK |
| iPS:434_469 | VK1|A30/JK1 | DIQMTQSPSSLSA SVGDRVTITC | RAS--QGIR----NDLG | WYQQKPGK APKRLIY | T--------- ASSLQS | GVPSRFSGSGSG------ TEFTLTISSLQPEDFATYYC | IHHNS--------- ---------YPRT | FGQGT KVEIK |
| iPS:435_197 | VK1|A30/JK1 | DIQMTQSPSSLSA SVGDRVTITC | RAS--QAIR----DDLG | WYQQKPGK APQRLIF | A--------- ASSLQS | GVPSRFSGSGCG------ TEFTSISISMORDFATYYC | LQHYS--------- ---------YPRT | FGRGT KVAIK |
| iPS:435_325 | VK1|A30/JK1 | DIQMTQSPSSLSA SVGDRVTITC | RAS--QGIR----NDLG | WYQQKPGK APKRLIY | A--------- ASSLQS | GVPSRFSGSGSG------ TEFTLTISSLQPEDFATYYC | LQHYS--------- ---------YPRT | FGQGT KVEIK |
| iPS:435_393 | VK1|A30/JK1 | DIQMTQSPSSLSA SVGDRVTITC | RAS--RGIR----NDLG | WYQQKPGK APKRLIY | A--------- ASSLQS | GVPSRFSGSGSG------ TEFTLTISSLQPEDFATYYC | LQHYS--------- ---------YPRI | FGQGT KVEIK |

Figure 51 (Continued)

| | | | | | | | | |
|---|---|---|---|---|---|---|---|---|
| iPS:435_539 | 21-225_158G1 | VK1/A30/JK1 | DIQMTQSPSSLSA SVGDRVTITC | RAS--QGIR----NDLG | WYQQKPGK APKRLIY | T-------ASNLQS | GVPSRFSGSGSG-- TEFTLTFSSLQPEDFATYYC | LQHNS--------YPWT FGQGT KVEIK |
| iPS:435_543 | 21-225_158D4 | VK1/A30/JK1 | DIQMTQSPSSLSA SVGDRVTITC | RAS--QDIR----KDLG | WYQQKPGK APKRLIY | A-------ASSLQS | GVPSRFSGSGSG-- TEFTLTFSSLQPEDFATYYC | LQHYS--------YPRT FGQGT KVEIK |
| iPS:435_571 | 21-225_159C8 | VK1/A30/JK1 | DIQMTQSPSSLSA SVGDRVTITC | RAS--QDIR----KDLG | WYQQKPGK APNRLIY | A-------ASSLQS | GVPSRFSGSGSG-- TEFTLTFSSLQPEDFATYYC | LQHES--------YPRT FGQGT KVEIK |
| iPS:435_573 | 21-225_159D8 | VK1/A30/JK1 | DIQMTQSPSSLSA SVGDRVTITC | RAS--RDIG----NDLG | WYQQKPGK APKRLIS | A-------ASSLQS | GVPSRFSGSGSG-- TEFTLTFSSLQPEDFATYYC | LQHYS--------YPRT FGQGT KVEIK |
| iPS:435_581 | 21-225_160H1 | VK1/A30/JK1 | DIQMTQSPSSLSA SVGDRVTITC | RAS--QDIR----NDLG | WYQQKPGK APKRLIY | A-------ASSLQN | GVPSRFSGSGSG-- TEFTLTISSLQPEDFTTYYC | LQHNS--------FPWT FGQGT KVEIK |
| iPS:435_583 | 21-225_160F2 | VK1/A30/JK1 | DIQMTQSPSSLSA SVGDRVTITC | RAS--QGIR----NDLG | WYQQKPGK APKRLIY | T-------ASNLQS | GVPSRFSGSGSG-- TEFTLTVSSLQPEDFATYYC | LQHNS--------YPWT FGQGT KVEIK |
| iPS:435_591 | 21-225_160C4 | VK1/A30/JK1 | DIQMTQSPSSLSA SVGDRVTITC | RAS--QDIR----KDLG | WYQQKPGK APNRLIY | A-------ASSLQS | GVPSRFSGSGSG-- TEFTLTFSSLQPEDFATYYC | LQHYS--------YPRT FGQGT KVEIK |
| iPS:435_615 | 21-225_161G1 | VK1/A30/JK1 | DIQMTQSPSRSA SVGDRVTITC | RAS--QDIR----KDLG | WYQQKPGK APNRLIY | A-------ASSLQS | GVPSRFSGSGSG-- TEFTLTFSSLQPEDFATYYC | LQHES--------YPRT FGQGT KVEIK |
| iPS:435_675 | 21-225_169D7 | VK1/A30/JK1 | DIQMTQSPSSLSA SVGDRVTITC | RAS--QGIR----NDLG | WYQQKPGK APKRLIY | A-------ASSLQS | GVPSRFSGSGSG-- TEFTLTISSLQPEDFATYYC | LQHHS--------CPWT FGQGT KVEIK |
| iPS:435_681 | 21-225_169D1 | VK1/A30/JK1 | DIQMTQSPSSLSA SVGDRVTITC | RAS--QGIR----DDLG | WYQQKPGK VPKRLIY | A-------ASSLQS | GVPSRFSGSGSG-- TEFTLTISSLQPEDFATYYC | LQHYS--------YPRT FGQGT KVEIK |
| iPS:435_687 | 21-225_170H1 | VK1/A30/JK1 | DIQMTQSPSSLSA SVGDRVTITC | RAS--QGIR----NDLG | WYQQKPGK APKRLIY | T-------TSSLQS | GVPLRFSGSGSG-- TEFTLTISSLQPEDFATYYC | LQHNS--------NPWT FGQGT KVESK |
| iPS:435_689 | 21-225_170F3 | VK1/A30/JK1 | DIQMTQSPSSLSA SVGDRVTITC | RAS--RGIR----NDLG | WYQQKPGK APKRLIH | A-------ASSLQN | GVPSRFSGSGSG-- TEFTLTINSLQPEDFATYYC | LQHYS--------YPRT FGQGT KVEIK |
| iPS:435_741 | 21-225_174G10 | VK1/A30/JK1 | DIQMTQSPSSLSA SVGDRVTITC | RAS--QGIR----KDLG | WYQQKPGK APKRLIH | A-------ASSLQS | GVPLRFSGSGSG-- TEFTLTISSLQPEDFATYYC | LQHES--------YPRT FGQGT KVEIK |
| iPS:435_831 | 21-225_190C12 | VK1/A30/JK1 | DIQMTQSPSSLSA SVGDRVTITC | RAS--QGIR----DDLG | WSQQNPGK APKRLIH | A-------ASSLQS | GVPLRFSGSGSG-- TEFTLTISSLQPEDFATYYC | LQHNM--------YPWT FGQGT KVEIK |
| iPS:435_857 | 21-225_191A4 | VK1/A30/JK1 | DIQMTQSPSSLSA SVGDRVTITC | RAS--QGIR----KDLG | WYQQKPGK APKRLIY | T-------ASSLQN | GVPLRFSGSGSG-- TEFTLTISSLQPEDFATYYC | LQHTS--------YPWT FGQGT KVEIK |
| iPS:435_907 | 21-225_190G3 | VK1/A30/JK1 | DIQMTQSPSSLSA SVGDRVTITC | RAS--QGIR----KDLG | WYQQKPGK APKRLIH | A-------ASSLQS | GVPLRFSGSGSG-- TEFTLTISSLQPEDFATYYC | LQHES--------YPRT FGQGT KVEIK |
| iPS:435_919 | 21-225_190H5 | VK1/A30/JK1 | DIQMTQSPSSLSA SVGDRVTITC | RAS--QGIR----KDLG | WYQQKPGK APKRLIH | T-------ASSLQS | GVPLRFSGSGSG-- TEFTLTISSLQPEDFATYYC | LQHNN--------YPWT FGQGT KVEIK |
| iPS:435_989 | 21-225_192F7 | VK1/A30/JK1 | DIQMTQSPSSLSA SVGDRVTITC | RAS--QGIR----KDLG | WYQQKPGK APKRLIH | T-------ASSLQS | GVPLRFSGSGSG-- TEFTLTISSLQPEDFATYYC | LQHTS--------YPWT FGQGT KVEIY |
| iPS:436_132 | 21-225_196C1 | VK1/A30/JK1 | DIQMTLSPSSLFA CVGDRVTITC | RAS--QGIR----NDLG | WYQQNPGK ALKRLIY | A-------ASSLQS | GVPSRFSGSGSG-- TEFTLTISSLQPEDFATYYC | LQHND--------FPFT FGRGT KVEIK |
| iPS:436_222 | 21-225_200C9 | VK1/A30/JK1 | DIQMTQSPSSLSA SVGDRVTITC | RAS--QGIR----HDLG | WYQQKPGK APKRLIY | T-------ASSLQS | GVPSRFSGSGSG-- TEFTLTISSVQPEDFATYYC | LQHYS--------YPWT FGQGT KVEIK |
| iPS:436_264 | 21-225_203F7 | VK1/A30/JK1 | DIQMTQSPSRFA SVGDRVTITC | RAS--QGIR----HDLG | WYQQKPGK ALKRLIY | A-------ASSLQS | GVPSRFSGSGCG-- TEFTLTISSVQPEDFANYYC | LQHYS--------FPRT FGQGT KVEIK |

Figure 51 (Continued)

| ID | V/J | | | | | | | | |
|---|---|---|---|---|---|---|---|---|---|
| iPS:436 274 | 21-225_204H3 | VK1|A30/JK1 | DIQMTQSPSSLSA SVGDRVTITC | RAS---QGIR------NDLG | WYQQKPGK APELLIY | A------ AASLQG | GVPSRFSGSGSG-- TEFTLTISSLQPEDFATYYC | LQHYS----------YPRT | FGQGT KVEIQ |
| iPS:436 332 | 21-225_208B2 | VK1|A30/JK1 | DIQMTQSPSSLSA SVGDRVTITC | RAS---QGIR-------HDLG | WYQQKPGK APKRLIY | A------ ASSLQS | GVPSGFSGSGSG-- TEFTLTISSLQPEDFATYYC | LQHYS----------YPRT | FGQGT KVEIK |
| iPS:436 352 | 21-225_210G5 | VK1|A30/JK1 | DIQMTQSPSSLSA SVGDRVTITC | RAS---QGIR-------HDLG | WYQQKPGK APKRLIY | A------ ASSLQS | GVPSGFSGSGSG-- TEFTLTISSLQPEDFATYYC | LHHYS----------YPRT | FGQGT KVEIK |
| iPS:436 386 | 21-225_212B1 | VK1|A30/JK1 | DIQMTQSPSSLPA SVGDRVTITC | RAS---QGIR------NDLG | WYQQKPGK APKRLIY | A------ ASSLQS | GVPSRFSGSGSG-- TEFTLTISSLQPEDFATYYC | LLHYS----------YPRT | FGQGT KVEIK |
| iPS:436 412 | 21-225_214H9 | VK1|A30/JK1 | DIQMTQSPSSLSA SVGDRVTITC | RAS---QGIR------NDLG | WYQQKPGK APKRLIY | A------ ASSLQS | GVPSRFSGSGSG-- TEFTLTISSLQPEDFATYYC | LQHYS----------YPRT | FGQGT KVEIK |
| iPS:436 414 | 21-225_214G1 | VK1|A30/JK1 | DIQMTLCPSSPPA SVGDRVTITC | RAS---QGIR------NDLG | WYQQKPGK APKRLIY | A------ ASSLQS | GVPSRFSGSGSG-- TEFTLTISSLQPEDFATYYC | LLHNS----------YPRT | FGQGT KVEIK |
| iPS:436 416 | 21-225_214G10 | VK1|A30/JK1 | DIQMTQSPSSPPA SVGDRVTITC | RAS---QGIR------NDLG | WYQQKPGK APKRLIY | A------ ASSLQS | GVPSRFSGSGSG-- TEFTLTISSLQPEDFATYYC | VMHYS----------YPRT | FGQGT KVEIK |
| iPS:436 418 | 21-225_215E3 | VK1|A30/JK1 | DIQMTQSPSSPPA SVGDRVTITC | RAS---QGIR------NDLG | WYQQKPGK APKRLIY | A------ ASSLQS | GVPSRFSGSGSG-- TEFTLTISSLQPEDFATYYC | VMHNS----------YPRT | FGQGT KVEIK |
| iPS:436 428 | 21-225_215E1 | VK1|A30/JK1 | DIQMTQCPSSPPA SVGDRVTITC | RAS---QGIR------NDLG | WYQQKPGK APKRLIY | A------ ASSLQS | GVPSRFSGSGSG-- TEFTLTISSVQREDFATYYC | VMHYS----------YPRT | FGQGT KVEIK |
| iPS:436 438 | 21-225_216E8 | VK1|A30/JK1 | DIQMTQSPSSLPA SVGDRVTITC | RAS---QGIR------NDLG | WYQQKPGK APKRLIC | A------ ASSLQS | GVPSRFSGSGSG-- TEFTLTISSLQPEDFATYYC | LMHYS----------YPRT | FGQGT KVEIK |
| iPS:436 440 | 21-225_216H1 | VK1|A30/JK1 | DIQMTLSPSSLPA SVGDRVTITC | RAS---QGIR------NDLG | WYQQKPGK APERLIY | G------ ASSLQS | GVPSRFSGSGSG-- TEFTLTISSLQPEDFATYYC | VMHNS----------YPRT | FGQGT KVEIK |
| iPS:436 450 | 21-225_217E5 | VK1|A30/JK1 | DIQMTQSPSSPPA SVGDRVTITC | RAS---QGIR------NDLG | WYQQKPGK APKRLIY | A------ ASSLQS | GVPSRFSGSGSG-- TEFTLTISSLQPEDFATYYC | VMHYS----------YPRT | FGQGT KVEIK |
| iPS:436 456 | 21-225_217G1 | VK1|A30/JK1 | DIQMTQSPSSPPA FVGDRVTITC | RAS---QGIR------NDLG | WYQQKPGK APKRLIC | A------ ASSLQS | GVPSRISGSGSG-- TEFTLTISSLQREDFATYYC | VMHNS----------YPRT | FGQGT KVEIK |
| iPS:436 458 | 21-225_217H1 | VK1|A30/JK1 | DIQMTQSPSSLPA FVGDRVTITC | RAS---QGIR------NDLG | WYQQKPGK APKRLIY | A------ ASSLQS | GVPSRISGSGSG-- TEFTLTISSLQPEDFATYYC | LMHYS----------YPRT | FGQGT KVEIK |
| iPS:436 462 | 21-225_218C4 | VK1|A30/JK1 | AIQMTQSPSSLSA SVGDRVTITC | RAS---QGIR------DDLG | WYQQKPGK APKRLIY | A------ ASSLQS | GVPSRFSGSGSG-- TEFTLTISSLQPEDFATYYC | VMHYS----------YPRT | FGQGT KVEIK |
| iPS:436 480 | 21-225_220F8 | VK1|A30/JK1 | DIQMTQSPSSLSA SVGDRVTITR | RAS---QGIR------NDLG | WYQQKPGK APKRLIY | A------ ASSLQS | GVPSRFSGSGSG-- TEFTLTISSLQPEDFATYYC | LQHYS----------YPRT | FGQGT KVEIK |
| iPS:436 534 | 21-225_224F1 | VK1|A30/JK1 | DIQMTQSPSSLSA SVGDRVTITC | RAS---QGIR------DDLG | WYQQKPGK APKRLIY | A------ ASSLQS | GVPSRFSGSGSG-- TEFTLTISSLQPEDFATYYC | LQHYN----------YPRT | FGQGT KVEIK |
| iPS:436 540 | 21-225_224F3 | VK1|A30/JK1 | DIQMTQSPSSLSA SVGDRVTITC | RAS---QGIR------NDLG | WYQQKPGK APERLIY | A------ ASSLQS | GVPSRFSGSGSG-- TEFTLTISSLQPEDFATYYC | LQHYS----------YPRA | FGQGT KVEIK |
| iPS:436 564 | 21-225_225A1 | VK1|A30/JK1 | DIQMTQSPSSLSA SVGDRVTITC | RAS---QGIR------NDLG | WYQQIPGK APKRLIY | A------ ASSLQS | GVPSRFSGSGSG-- TEFTLTISSLQPEDFATYYC | LQHYS----------YPRT | FGQGT KVEIK |
| iPS:436 596 | 21-225_226C6 | VK1|A30/JK1 | DIQMTQSPSSLSA SIGDRVTITC | RAS---QGIR------NDLG | WYQQKPGK APKRLIY | A------ ASSLQS | GLPSRFSGSGSG-- TEFTLTISNLQPEDFATYYC | LQHYN----------YPRA | FGQGT KVEIQ |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS:436 604 | 21-225_226F7 | VK1|A30/JK1 | DIQMTQSPSSLSA SVGDRVTITC | RAS--QGIG----NDLG | WYQQKPGK APKRLIY | A------ ASSLQS | GVPSRFSGSVSG-- TEFTLTISSLQPEDFATYYC | LEHYS----------- ---------YPRT | FGQGT KVEIK |
| iPS:436 620 | 21-225_226H1 | VK1|A30/JK1 | DIQMTQSPSSLSA SVGDRVTITC | RTS--QGIR----NDLG | WYQQKPGK APKRLIY | A------ ASSLQS | GVPSRFSGSGSG-- TDFTLTISSLQPEDFATYYC | LQHNS----------- ---------YPPWT | FGQGT KVDIK |
| iPS:437 262 | 21-225_170E4 | VK1|A30/JK1 | DIQMTQSPSSLSA SVGDRVTITC | RAS--QGIR----NDLG | YYQQKPGK APKRLIY | V------ ASGLQS | GVPSRFSGSGSG-- TEFTLTFSSLQPEDFATYYC | LQHNS----------- ---------YPPWT | FGQGT KVDIK |
| iPS:437 280 | 21-225_203C1 | VK1|A30/JK1 | DIQMTQSPSSLSA SVGDRVTITC | RAS--QDIR----NDLG | WYQQKPAK APKRLIY | R------ ASSLQS | GVPSRFSGSGSG-- TEFTLTISSLQPEDFAAYYC | LQHNS----------- ---------YPRT | FGQGT KVEIK |
| iPS:437 286 | 21-225_208F1 | VK1|A30/JK1 | DIQMTQSPSSLSA SVGDRVTITC | RAS--QGIR----HDLG | WYQQKPGK APKRLIY | A------ ASSLQS | GVPSRFSGSGSG-- TEFTLTISSLQPEDFATYYC | LQHYS----------- ---------FPRT | FGQGT KVEIK |
| iPS:437 290 | 21-225_210G6 | VK1|A30/JK1 | DIQMTQSFSSRFA FVGDRVTITC | RAS--QGIR----HDLG | WYQQKPGK ALKRLIY | A------ ASSSQS | GVPSRFSGSGCG-- TEFTLTISVQREDFANYYC | VQHYS----------- ---------FPRT | FGQGT KVEIK |
| iPS:451 114 | 21-225_159A3 | VK1|A30/JK1 | DIQMTQSPSSLSA SVGDRVTITC | RAS--QDIR----KDLG | WYQQKPGK APNRLIY | A------ ASSLQS | GVPSRFSGSGSG-- TEFTLTFSSLQPEDFATYYC | LQHNS----------- ---------YPRT | FGQGT KVEIK |
| iPS:392 626 | 21-225_18A5 | VK1|A30/JK1 | DIQMTQSPSSLSA SVGDRVTITC | RAS--QGIR----NDLG | WYQQKPGK APKRLIY | A------ ASSLQS | GVPSRFSGSGSG-- TEFTLTISSLQPEDFATYYC | LQHNS----------- ---------YPWT | FGQGT KVEIK |
| iPS:392 634 | 21-225_17H3 | VK1|A30/JK1 | DIQMTQSPSSLSA SVGDRVTITC | RAS--QGIR----SDLG | WYQQKPGK APKRLIY | A------ ASSLQS | GVPSRFSGSGSG-- TEFTLTISSLQPEDFATYYC | LQQYS----------- ---------YPRT | FGQGT KVEIK |
| iPS:392 674 | 21-225_18C2 | VK1|A30/JK1 | DIQMTQSPSSLSA SVGDRVTIFTC | RAS--QGIR----HDLG | WYQQKPGK APKRLIY | T------ ASSLQS | GVPSRFSGSGFG-- TEFTLTISSLQPEDFATYYC | LQHNS----------- ---------YPWT | FGLGT KVVIK |
| iPS:392 686 | 21-225_17C7 | VK1|A30/JK1 | DIQMTQSPSSLSA SVGDRVTITC | RAS--QDIR----RDLG | WYQQKPGK APKRLIY | A------ ASSLQS | GVPSRFSGSGSG-- TEFTLTISLQPEDFATYYC | LQHNS----------- ---------YPWT | FGQGT KVEIK |
| iPS:392 690 | 21-225_18F2 | VK1|A30/JK1 | DIQMTQSPSSLSA SVGDRVTITC | RAS--QGIR----NDLG | WYQQKPGK APKRLIY | A------ ASSLQS | GVPSRFSGSGSG-- TEFTLTISRLQPEDFATYYC | LQHNN----------- ---------YPWT | FGQGT KVEIK |
| iPS:392 710 | 21-225_19A10 | VK1|A30/JK1 | DIQMTQSPSSLSA SVGDRVTITC | RAS--QGIR----TDLG | WYQQRPGK APKRLIY | T------ ASNLQS | GVPSRFSGSGSG-- TEFTLTISSLQPEDFATYYC | LQHYN----------- ---------YPRA | FGLGT KVDIK |
| iPS:392 740 | 21-225_18H12 | VK1|A30/JK1 | DIQMTQSPSSLSA SVGDRVTITC | RAS--QGIR----NDLG | WYQQKPGK ARKRLIY | A------ AYSLQS | GVPSRFSGSGSG-- TEFTLTISSLQPEDFATYYC | LQHNS----------- ---------YPWT | FGQGT KVVIK |
| iPS:392 742 | 21-225_20B2 | VK1|A30/JK1 | DIQMTQSPSSLSA SVGDRVTITC | RAS--QGIR----NDLG | WYQQKPGK APKRLIV | A------ ASSLQS | GVPSRFSGSGSG-- TEFTLTISSLQPEDFATYYC | LQHNS----------- ---------YPRA | FGQGT KVDIK |
| iPS:392 758 | 21-225_21G11 | VK1|A30/JK1 | DIQMTQSPSSLSA SVGDRVTITC | RAS--QGIR----NDLG | WYQQKPGK APKRLIY | T------ ASSLQS | GVPSRFSGSGSG-- TDFTLTISSLQPEDFATYYC | LQHNS----------- ---------YPWT | FGLGT KVVIK |
| iPS:392 790 | 21-225_20D10 | VK1|A30/JK1 | DIQMTQSPSSLSA FVGDRVTITC | RAS--QVIR----DDLG | WYQQKPGK APKRLIY | V------ ASSLQS | GVPSRFSGSGYG-- TDFTLTISSLQPEDFATYYC | IQQNS----------- ---------YPWT | FGQGT KVEIK |
| iPS:392 796 | 21-225_22A4 | VK1|A30/JK1 | DIQMTQSPSSLSA SVGDRVTITC | RAS--QDIR----NDLG | WYQQKPGK APKRLIY | A------ ASSLQS | GVPSRFSGSGSG-- TEFTLTISSLQPEDFATYYC | LQHNS----------- ---------YPWT | FGQGT KVEIK |
| iPS:392 832 | 21-225_21H8 | VK1|A30/JK1 | DIQMTQSPSSLSA SVGDRVTITC | RAS--QGIR----NDLG | WYQQKPGK APKRLIY | A------ ASSLQS | GVPSRFSGSGSG-- TEFTLTISSLQPEDFATYYC | LQHNS----------- ---------YPRA | FGQGT KVDIK |
| iPS:392 836 | 21-225_22F4 | VK1|A30/JK1 | DIQMTQSPSSLSA SVGDRVTITC | RAS--QGIR----NDLG | WYQQKPGK APKRLIY | A------ ASSLQS | GVPSRFSGSGSG-- TEFTLTISSLQPEDFATYYC | LEHYS----------- ---------YPRT | FGLGT KVVIK |
| iPS:392 844 | 21-225_23E11 | VK1|A30/JK1 | DIQMTQSPSSLSA SVGDRITITC | RAS--QDIR----DDLG | WYQQKPGK APKRLIY | P------ ASSLQS | GVPSRFSGSGSG-- TEFTLTISSLQPEDFATYYC | LQHNS----------- ---------YPWT | FGQGT KVEIK |
| iPS:392 846 | 21-225_24B6 | VK1|A30/JK1 | DIQMTQSPSSLSA SVGDRVTITC | RAS--QDIR----NDLG | WYQQKPGK APKRLIY | A------ ASSLHS | GVPSRFSGSGSG-- TEFTLTISSLQTEDFATYYC | LQHYS----------- ---------YPWT | FGQGT KVEVK |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS:392872 | 21-225_20B11 | VK1|A30/JK1 | DIQMTQSPSSLSA SVGDRVTITC | RAS--QGIG------NDLG | WYQQKPEK APKRLIY | A------ASSLHS | GVPSRFSGSGSG--TEFTLTISSLQPEDFATYYC | LQHYS-------YPRT | FGQGT KVEIK |
| iPS:392876 | 21-225_21F7 | VK1|A30/JK1 | DIQMTQSPSSLSA SVGDRVTITC | RAS--QDIR------NDLG | WYQQKPGK APKRLIY | A------ASNFQS | GVPSRFSGSGSG--TEFTLTISSLQPEDFATYYC | LQHNN-------YPWT | FGQGT KVEIK |
| iPS:392884 | 21-225_23A10 | VK1|A30/JK1 | DIQMTQSPSSLSA SVGDRVTITC | RAS--QGIR------NDLG | WYQQKPGK APKRLIY | A------ASSLQS | GVPSRFSGSGSG--TEFTLTISSLQPEDFATYYC | LQHYS-------YPWT | FGLGT KVEIK |
| iPS:392894 | 21-225_21G2 | VK1|A30/JK1 | DIQMTQSPSSLSA SVGDRVTITC | RAS--QGIR------NDLG | WYQQKPGK APKRLIY | T------SSSLQS | GVPSRFSGSGSG--TEFTLTISSLQPEDFATYYC | LQHNS-------YPWT | FGLGT KVVIK |
| iPS:392908 | 21-225_23F12 | VK1|A30/JK1 | DIQMTQSPSSLSA SVGDRVTITC | RAS--QGIR------NDLG | WYQQKPGK APKRLIY | V------ASSLQS | GVPSRFSGSGSG--TEFTLTISSLQPEDFATYYC | LQHYS-------YPWT | FGQGT KVEIK |
| iPS:392914 | 21-225_25D12 | VK1|A30/JK1 | DIQMTQSPSSLSA SVGDRVTITC | RTS--QGIR------NDLG | WYQQKPGK APKRLIY | A------ASSLQS | GVPSRFSGSGSG--TEFTLTISSLQPEDFATYYC | LQHYS-------FPRT | FGQGT KVEIK |
| iPS:392918 | 21-225_28F5 | VK1|A30/JK1 | DIQMTQSPSSLSA SVGDRVTITC | RAS--QGIR------NDLG | WYQQKPGK APKRLIY | T------ASSLQS | GVPSRFSGSGSG--TEFTLTISSLQPEDFATYYC | LQHNT-------YPWT | FGQGT KVEVK |
| iPS:392958 | 21-225_28C7 | VK1|A30/JK1 | DIQMTQSPSSLSA SVGDRVTITC | RAS--QGIR------NDLG | WYQQKPGK APKRLIY | I------ASSLQS | GVPSRFSGSGSG--TEFTLTISSLQPEDFATYYC | LQRNT-------YPWT | FGQGT KVEIK |
| iPS:392972 | 21-225_26A2 | VK1|A30/JK1 | DIQMTQSPSSLSA SVGDRVTITC | RAS--QGIR------SDLG | WYQQKPGK APKRLIY | I------ASSLQS | GVPSRFSGSGSG--TEFNITISSLQPEDFATYYC | LQHNR-------YPWT | FGQGT RVEIT |
| iPS:393026 | 21-225_32B6 | VK1|A30/JK1 | DIQMTQSPSSLSA SVGDRVTITC | RAS--QGIR------NDLG | WYQQKPGK APKRLIY | I------ASSLQS | GVPSRFSGSGSG--TEFTLTISSLQPEDFATYYC | LQHNS-------YPWT | FGQGT KVEIK |
| iPS:393130 | 21-225_33C2 | VK1|A30/JK1 | DIQMTQSPSSLSA SVGDRVTITC | RAS--QGIR------NDLG | WYQQKPVK APKRLIY | A------APSLQS | GVPSRFSGSGSG--TEFTLTISSLQPEHFATYYC | LQHNS-------YPWT | FGQGT KVEIK |
| iPS:393812 | 21-225_6A11 | VK1|A30/JK1 | DIQMTQSPSSLSA SVGDRVTITC | RAS--QGIR------NDLG | WYQHKPGQ ARKRLIY | A------ASSLQS | GVPSRFSGSGSG--TEFTLTISSLQPEDFTAYYC | LQHNS-------YPWT | FGQGT KVEIK |
| iPS:393838 | 21-225_14E10 | VK1|A30/JK1 | DIQMTQSPSSLSA FVGDRVTITC | RTS--QGIR------NDLG | WYQQKPGK APKRLIY | T------ASSLQS | GVPSRFSGSGYG--TEFTLTINSLQPEDFATYYC | IQHNS-------YLWT | FGQGT KVEIK |
| iPS:393864 | 21-225_10E9 | VK1|A30/JK1 | DIQMTQSPSSRSA SVGDRVHLTC | RAS--RGIR------GDLG | WYRQKPGK APTRLIF | A------ASSLHS | GVPSRFSGSGSG--TEFTLTISSLQPEDFATYYC | LQHYS-------YPRT | FGSGT KVEIK |
| iPS:393868 | 21-225_4C5 | VK1|A30/JK1 | DIQMTQSPSSLSA SVGDRVHLTC | RAS--QNIR------NYLN | WYQQKSGR APKLLIY | V------ASNLQS | GVPSRFSGSGSG--TEFTLTIGSLQPEDFATYYC | HQSNS-------TPLT | FGQGT KVEIK |
| iPS:393876 | 21-225_9A1 | VK1|A30/JK1 | DIQMTQSPSSRSA FVGDRVTITC | RAS--QGIR------NDLG | WYQQKPGK ARKRLIY | A------ASSLQS | GVPSRFSGSGYG--TEFTITISSLQPEDFATYYC | LQHYS-------YLWT | FGQGT KVEIK |
| iPS:393902 | 21-225_14E10 | VK1|A30/JK1 | DIQMTQSPSSLSA SVGDRVTITC | RAS--QGIR------NDLG | WYQHKPGQ APKRLIY | A------ASSLQS | GVPSRFSGSGSG--TEFTLTISSLQPEDFTAYYC | LQHYS-------YPRT | FGQGT KVEIK |
| iPS:393908 | 21-225_10E9 | VK1|A30/JK1 | DIQMTQSPSFSSLSA SVGDRVTFTC | RAS--QDIR------SDLG | WYQQKPGK APTRLIE | A------ASSLHS | GVPSRFSGSGSG--TEFTLTINSLQPEDFATYYC | LQHYS-------YPRT | FGQGT KVEIK |
| iPS:393916 | 21-225_2G4 | VK1|A30/JK1 | DIQMTQSPSSLSA SVGDRVTITC | RAS--QGIR------NDLG | WYRQKPGK APTRLIY | A------ASSLQS | GVPSRFSGSGSG--TEFTLTISSLQPEDFATYYC | LQHYS-------FPRT | FGSGT KVEIK |
| iPS:393948 | 21-225_16A5 | VK1|A30/JK1 | DIQMTQSPSSLSA SVGDRVTITC | RAS--QGIR------NDLG | CYQQKPGK APKRLIY | T------ASSLQS | GVPSRFSGSGSG--TEFTLTISSLQPEDFATYYC | LQHNS-------YPWT | FGQGT KVEIK |
| iPS:393960 | 21-225_7G2 | VK1|A30/JK1 | DIQMTQSPSSLSA SVGDRVTITC | RAS--QGIR------NDLG | WYQQKPGK APKRLIY | A------ASSLQS | GVPSRFSGNGYG--TEFTLTISSLQPEDFATYYC | LQHNS-------YPWT | FGLGT KVVIK |
| iPS:393966 | 21-225_7F8 | VK1|A30/JK1 | DIQMTQSPSSLSA SVGDRVTITC | RAS--QGIG------NDLG | WYQQKPGK APKRLIY | A------ASSLQS | GVPSRFSGSVSG--TEFTLPISSLQPEDFATYYC | LQHYT-------YPRT | FGQGT KVEIK |
| iPS:393972 | 21-225_7C9 | VK1|A30/JK1 | DIQMTQSPSSLSA SGGDRVTITC | RAS--QGIR------NDLG | WYQQKPGK APFKRLIY | A------ASSLQS | GVPSRFSGSGSG--TEFTLTISSLQPEDFATYYC | LCLYS-------YPRT | FGQGT KVDIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:393978 | 21-225_4C12 | VK1|A30/JK1 | DIQMTQSPSSLSASVGDRVTITC | RAS--QGIR----NDLG | WYQQKPGKAPTRLIY | A-------ASSLHS | GVPSRFSGSGSG--TEFTLTISSLQPEDLATYYC | LQHYS----------FPRT | FGQGTKVEIK |
| iPS:393986 | 21-225_7G4 | VK1|A30/JK1 | DIQMTQSPSSLSASVGDRVTITC | RAS--QGIR----NDLG | WYQQRPGKAPKRLIY | A-------ASSLQS | GVPSRFSGSGSG--TEFTLTISSLQPEDSATYYC | LHQYS----------YPRT | FGQGTKVEIK |
| iPS:393996 | 21-225_15C11 | VK1|A30/JK1 | DIQMTQSPSSLSASVGDRVTITC | RAS--QGIR----NDLG | WYQQKPGKVPKRLIY | A-------ASSLQS | GVPSRFSGSGSG--TEFTLTISSLQPEDFATYYC | LLHYS----------YPRT | FGRGTKVEIK |
| iPS:393998 | 21-225_12B12 | VK1|A30/JK1 | DIQMTQSPSSLSASVGDRVTITC | RAS--QGIR----NDLG | WYQQKPGKAPKRLIY | T-------ASSLQS | GVPSRFSGSGSG--TEFTLTISSLQPEDFATYYC | LQHNS----------YPWT | FGLGTKVVIK |
| iPS:394041 | 21-225_5E5 | VK1|A30/JK1 | DIQMTQSPSSLSASVGDRVTITC | RAS--QGIR----NDLG | WYQQKPGKAPKRLIY | A-------ASSLQS | GVPSRFSGSGSG--TEFTLTISSLQPEDFATYYC | LQHYS----------YPRT | FGQGTKVEIK |
| iPS:394067 | 21-225_12F2 | VK1|A30/JK1 | DIQMTQSPSSLSASVGDRVTITC | RAS--QGIR----NDLG | WYQQKPGKAPKRLIY | A-------ASSLQS | GVPSRFSGSGSG--TEFTLTISSLQPEDFVTYYC | LQHNS----------YPWT | FGQGTKVEIK |
| iPS:394089 | 21-225_12E6 | VK1|A30/JK1 | DIQMTQSPSSLSASVGDRVTITC | RAS--QGIR----SDLG | WYQQKPGKAPKRLIY | A-------ASSLQS | GVPSRFSGSGSG--TEFTLTISSLQPEDFATYYC | LQHNS----------YPWT | FGQGTKVEIK |
| iPS:394093 | 21-225_9D12 | VK1|A30/JK1 | DIQMTQSPSSLSASVGDRVTITC | RAS--QGIR----NDLG | WYQQKPGKAPKRLIY | A-------ASSLQS | GVPSRFSGSGSG--TEFTLTISSLQPEDFATYYC | LQHNS----------YPWT | FGQGTKVEIK |
| iPS:394095 | 21-225_16H4 | VK1|A30/JK1 | DIQMTQSPSSLSASVGDRVTITC | RAS--QGIR----NDLG | WYQQKPGKAPKRLIY | T-------ASSLQS | GVPSRFSGSGSG--TEFTLTISSLQPEDFATYYC | LQHNS----------YPWT | FGQGTKVEIK |
| iPS:394097 | 21-225_16G7 | VK1|A30/JK1 | DIQMTQSPSSLSASVGDRVTITC | RAS--QGIR----NDLG | WYQQKPGKAPKRLIY | A-------ASSLQS | GVPSRFSGSGSG--TEFTLTISSLQPEDFATYYC | LQHNS----------YPWT | FGQGTKVEIK |
| VK3|L2|JK2 | | Germline | EIVMTQSPATLSVSPGERATLSC | RAS--QSVS----SNLA | WYQQKPGQAPRLLIS | G-------ASTRAT | GIPARFSGSGSG--TEFTLTISSLQSEDFAVYFC | QQYND----------WPCS | FGQGTKLEIK |
| iPS:468828 | 21-225_162A10 | VK3|L2|K2 | EIVMTQSPATLSVSPGERATLSC | RAS--QTVN----SNLA | WYQQKSGQAPRLLIF | G-------ASTRAT | VIPARINGSGSG--TEFTLTISSLRSEDFAVYPC | QQYND----------WPCS | FGQGTKLEIK |
| iPS:434255 | 21-225_62E6 | VK3|L2|K2 | EIVMTQSPATLSVSPGERATLSC | RAS--QSVN----SNLA | WYQQKPGQAPRLLIS | V-------ASTRAT | GIPARFSGSGSG--TEFTLTISSLQSEDFAVYYC | QQYND----------WPCS | FGQGTKLEIK |
| iPS:434269 | 21-225_57H3 | VK3|L2|K2 | EIVMTQSPATLSVSPGERATLSC | RAS--QSVS----SSLA | WYQQKPGQAPRLLIY | G-------ASTRAT | GFPARFNGSGSG--TEFTLTISSLQSEDFAIYYC | QQYND----------WPCS | FGQGTKLEIK |
| iPS:434363 | 21-225_65A6 | VK3|L2|K2 | EIVMTQSPVTLFVSPGERATLSC | RAS--QSVN----SNLA | WYQQKPGQAPRLLIY | G-------ASTRAT | GIPARFSGSGSG--TEFTLTISSLQSEDFAVYYC | QQYND----------WPCS | FGLGTKLEIK |
| iPS:434393 | 21-225_67C3 | VK3|L2|K2 | EIVMTQSPATLSVSPGERATLSC | RAS--QSVN----SNLA | WYQLKPGQAPRLLIS | I-------ASTRAT | GIPPRFNGSGSG--TEFTLTISSLQSEDFAVYYC | QQYND----------WPCS | FGQGTKLEIK |
| iPS:434425 | 21-225_70A5 | VK3|L2|K2 | EIVMTQSPATLSVSPGERATLSC | RAS--QSVN----SNLA | WYQQKPGQAPRLLIS | I-------ASTRAT | GIPARFSGSGSG--TEFTLTISSLQSEDFAVYYC | QQYND----------WPCS | FGQGTKLEIK |
| iPS:434485 | 21-225_76D2 | VK3|L2|K2 | EIVMTQSPATFSVSPGERATLSC | RAS--VSVV----NSLA | WYQQKPGQAPRLLIH | G-------ASTRAT | GIPARFSGSGSG--TEFTLTISSLQSEDFAVYYC | QQYND----------WPCS | FGQGTKLEIK |
| iPS:434537 | 21-225_74E11 | VK3|L2|K2 | EIVMTQSPATLSVSPGERATLSC | RAS--LSVV----NSLA | WYQQKPGQAPRLLIH | G-------ASTRAT | GIPARFSGSGSG--TEFSLTISSLQSEDFAIYYC | QQYND----------WPCS | FGQGTKLEIK |
| iPS:434569 | 21-225_77H5 | VK3|L2|K2 | EIVMTQSPVTLSVSPGERATLSC | RAS--QSVS----SSLA | WYQQKPGLAPRLLIY | G-------ASTRAT | GIPARFSGSGSG--TEFTLTISSLQSEDFAVYFC | QQYND----------WPCS | FGQGSKLEIQ |
| iPS:434629 | 21-225_74C3 | VK3|L2|K2 | EIVMTQSPATLSVSPGERATLSC | RAS--QSVA----SSLA | WYQQKPGQAPRLLIF | G-------TSTRAT | GIPARFSGSGSG--TEFTLTISSLQSEDFAIYYC | QQYND----------WPCS | FGLGTKLEIK |
| iPS:434673 | 21-225_74E3 | VK3|L2|K2 | EIVMTQSPATLSLSPGERATLSC | RAS--LSVV----NSLA | WYQQKPGQAPRLLIY | G-------ASTRAT | GIPARFSGSGSG--TEFTLTISSLQSEDFAIYYC | QQYND----------WPCS | FGQGTKLEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:435109 | 21-225_92H5 | VK3lL2/J K2 | EIVMTQSPATLSV SPGERATLSC | RAS--QDVI------TYLA | WYQQKPGQ APRLLIY | G-------ASTRAT | GVPARFSGSGSG--- TEFTLTISSLQSEDFALYYC | QEYND------------MPCS | FGQGT KLEIK |
| iPS:435221 | 21-225_95G2 | VK3lL2/J K2 | EIVMTQSPATLSL SPGERATLSC | RAS--MSVV------NSLA | WYQQKPGQ AFRLLIY | G-------ASTRAT | GIPARFSGSGSG--- TEFTLTISSLQSEDFAIYYC | QQYND------------WPCS | FGQGT KLEIK |
| iPS:436051 | 21-225_193G12 | VK3lL2/J K2 | EIVMTQSPATLSV SPGERATLSC | RAS--QSVS------SSLA | WYQQKPGQ APRILIS | G-------ASTRAT | GIPARFSGSGSG--- TEFTLTISSLQSADFAVYYC | QQYNN------------MPCS | FGQGT KLEIK |
| iPS:436236 | 21-225_201F7 | VK3lL2/J K2 | EIVMTQSPATLSV SPGERATLSC | RAS--QNIK------NNLA | WYQQKPGQ APRLLIY | G-------ASTRAT | GIPARFSGSGSG--- TEFTLTISSLQSEDFAVYYC | QQFYN------------WLCS | FGQGT KLELK |
| iPS:436250 | 21-225_201A4 | VK3lL2/J K2 | EIVMTQSPATLSV SPGERATLSC | RSS--QNIK------SNLA | WYQQKPGQ APRLLIF | G-------ASTRAT | GIPARFSGSGSG--- TEFTLTISSLQSEDFAVYYC | QQFYN------------WLCS | FGQGT KLEIK |
| iPS:436252 | 21-225_202A8 | VK3lL2/J K2 | EIVMTQSPATLSV SPGERATLSC | RAS--QRIN------NNLA | WYQQNPGQ APRLLIY | G-------ASTRAT | GVPARFSGSGSG--- TEFTLTISSLQSEDFTVYYC | QQYNN------------WLCS | FGQGT KLEIK |
| iPS:436258 | 21-225_202F12 | VK3lL2/J K2 | EIVMTQSPATLSV SPGERATLSC | RAS--QSVL------NNLA | WYQQKPGQ APRLLIY | G-------ASTRAT | GIPARFSGSGSG--- TEFTLTISSLQSEDFAVYYC | QQYDN------------WPPCS | FGQGT KLEIK |
| iPS:436278 | 21-225_201F2 | VK3lL2/J K2 | EIVMTQSPATLSV SPGERATLSC | RAS--QNIK------SNLA | WYQQKPGQ APRLLIF | G-------ASTRAT | GIPARFSGSGSG--- TEFTLTISSLQSEDFAVYYC | QQFYN------------WLCS | FGQGT KLEIK |
| iPS:436294 | 21-225_205G4 | VK3lL2/J K2 | EIVMTQSPATLSV SPGERATLSC | RAS--QNIK------SNLA | WYQQKPGQ APRLLIF | G-------ASTRAT | GIPARFSGSGSG--- TEFTLTISSLQSEDFAVYYC | QQFYN------------WLCS | FGQGT KLEIK |
| iPS:436306 | 21-225_201H4 | VK3lL2/J K2 | EIVMTQSPATLSV SPGERATLSC | RAS--QSVN------SYLA | WYQQKPGQ APRLLIY | G-------ASTRAT | GIPARFSGSGSG--- TEFTLTISSLQSEDFAVYYC | QEYND------------WPCS | FGQGT NLEIK |
| iPS:436356 | 21-225_210H10 | VK3lL2/J K2 | EIVMTQSPATLSV SPGERATLSC | RAS--QSVK------SNLA | WYQQRPGQ APRLLIY | G-------ASTRAT | GIPARFSGSGSG--- TEFTLTISSLQSEDFAVYYC | QQYNN------------WLCS | FGQGT KLEIK |
| iPS:436382 | 21-225_212C1 | VK3lL2/J K2 | EIVMTQSPATLSV SPGERATLSC | RTS--QSVA------SSLA | WYHQKPGQ APRLLIH | G-------TSTRAT | DVPARFSGFGSG--- SDFTLTISSLQSEDFAVYYC | QQYND------------WPCS | FGQGT KLEIK |
| iPS:436434 | 21-225_216B10 | VK3lL2/J K2 | EIVMTQSPATLSV SPGERATLSC | RAS--QSVN------NNLA | WYQQKPGQ APRLLIY | G-------ASTRAT | GIPPRFSGSGSG--- TEFTLTISSLQSEDFAVYYC | QQYNN------------WPCS | FGQGT KLEIR |
| iPS:392806 | 21-225_24H3 | VK3lL2/J K2 | EIVMTQSPATLSV SPGERATLSC | RAS--QSVS------SNLA | WYQQKPGQ APRLLIY | F-------ASIRAT | GIPARFSGSGSG--- TEFTLTISSLQSEDFAVYYC | QQYNN------------MPMCS | FGQGT KLEIK |
| | Germline | VK3lL2/J4 | | K_CDR1 | K_FR2 | K_CDR2 | K_FR3 | K_CDR3 | K_FR4 |
| iPS:468830 | 21-225_191G11 | VK3lL2/J K4 | EIVMTQSPATLSV SPGERANLSC | RTS--QSVW------ISVA | WYHQKPGQ APRLLIY | G-------AATRAT | GIPARFSGSGSG--- TEFTLTISSLQSEDFAVYYC | QQINY------------WPLT | FGGGT KVEIK |
| iPS:434147 | 21-225_55E1 | VK3lL2/J K4 | EIVMTQSPATLSV SPGERAILSC | RAS--QSVS------SDLA | WYQLKPGQ APRLLIY | D-------ASARAT | GIPARFSGSGSG--- TEFTLTISSLQSEDFAFYYC | QQYNN------------WPLT | FGGGT KVEIK |
| iPS:434621 | 21-225_74D1 | VK3lL2/J K4 | EIVMTQSPATLSV SPGERAILSC | RAS--QSVS------RNLA | WFQQKPGQ APRLLIY | G-------ASIRAT | GIPARFSGSGSG--- TEFTLTIYSLQSEDFAVYYC | QQYNN------------WPPLT | FGGGI KVEIK |
| iPS:435821 | 21-225_190E11 | VK3lL2/J K4 | EIVMTQSPATLSV SPGERAILSC | RAS--QSFR------INLA | WYQQRPGQ APRLLIY | G-------ASTRAT | GIPARFSGSGSG--- TEFTLTISSLQSEDFAVYYC | QQYNN------------WPLT | FGGGT KVEIK |
| iPS:435941 | 21-225_191E8 | VK3lL2/J K4 | EIVMTQSPATLSV SPGERAILSC | RPS--QSFS------RNLA | WYQQKPGQ APRLLIY | G-------ASTRAT | GIPSRFSGSGSG--- TEFTLTISSLSEDFAVYYC | QQYNN------------WPLT | FGGGI KVEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:436_203 | 21-225_199A6 | VK3lL2/J K4 | DIVMTQSPATLSV SPGDRATLSC | RPS--QSFS-----RNLA | WYQQKPGQ APRLLIY | G-------ASTRAT | GIPARFSGSGSG--TEFTLTISSLECEDFAVYYC | QQYNN--------WPLT | FGGGT KVEIK |
| iPS:437_334 | 21-225_75F11 | VK3lL2/J K4 | EIVMTQSPATLFV SPGERATLSC | RAS--QSVS-----RNLA | WFCQKPGQ APRLLFY | G-------ASIRAT | GIPARFSGSGSG--TEFTLTIYSSLQTEDFAVYYC | QQYNN--------WPPLT | FGGGT KV5IK |
| iPS:448_904 | 21-225_65C12 | VK3lL2/J K4 | EIVMTQSPATLSV FPGEGATLSC | RAS--QSVS-----INLA | WYQQKPGQ APRLLIY | G-------ASTRAT | GIPARFNASGSG--TEFTLSISLQSENFAVYYC | QQYNT--------WPLT | FGGGT KVEIK |
| | Germline | VK1lA30/JK3 | | | K_FR2 | K_CDR2 | K_FR3 | K_CDR3 | K_FR4 |
| iPS:468_832 | 21-225_76H10 | VK1lA30/ JK3 | DIQMTQSPSSLSA SAGDRVTITC | RAS--QDIR------NYLG | WYQQKPGK APKRLIY | G-------ASSLQS | GVPSRFSGSGSG--TEFTLTISSLQPEDFATFYC | LQYNS---------YPFT | FGPGT KVDIK |
| iPS:468_836 | 21-225_198E3 | VK1lA30/ JK3 | DIQMTQSPSSLSA SVGDRVTITC | RAS--QGIR------KDLG | WYQQKPGK APKRLIY | A-------ASSLQS | GVPSRFSGSGSG--TEFTLTISSLQPEDFATYYC | LQHYR---------YPFT | FGPGT KVDIK |
| iPS:468_844 | 21-225_48E10 | VK1lA30/ JK3 | DIQMTQSPSSLSA SVGDRVTITC | RAS--QGIR------SDLG | WYQQKPGK APKRLIY | T-------ASSLQS | GVPSRFSGSGSG--IEFTLTISSLQPEDFATYYC | LQYNS---------YPFT | FGPGT KVDIK |
| iPS:468_846 | 21-225_53B10 | VK1lA30/ JK3 | DIQMTQSPSSLSA SAGDRVTITC | RAS--QDIR------NYLG | WYQQKPGK APKRLIY | G-------ASSLQS | GVPSRFSGSGSG--TEFTLTISSLQPEDFATFYC | LQYNS---------YPFT | FGPGT KVDIK |
| iPS:433_895 | 21-225_43E1 | VK1lA30/ JK3 | DIQMTQSPSSLSA SVGDRVTITC | RAS--QGIR------NDLG | WYQKKPGK APKRLIN | G-------ASSLQS | GVPSRFSGSGSG--TEFTLTISSLQPEDFATYYC | LQHNS---------YPFT | FGPGT KVDIK |
| iPS:433_905 | 21-225_43E5 | VK1lA30/ JK3 | DIQMTQSPSSLSA SVGDRVTITC | RAS--QGIR------NDLG | WYQQKPGK APKRLIY | G-------ASNLQS | GVPSRFSGSGSG--TEFTLTISSLQPEDFATYYC | LQHTS---------FPFT | FGPGT KVDIK |
| iPS:433_913 | 21-225_43H8 | VK1lA30/ JK3 | DIQMTQSPSSLSA SVGDRVTITC | RAS--QGIR------NDLG | WHQQKPGK APKRLIY | A-------ASSLQS | GVPSRFSGSGSG--IEFTLSISSLQPEDFATYYC | LQYNS---------FPFT | FGPGT KVDIK |
| iPS:433_933 | 21-225_44C8 | VK1lA30/ JK3 | DIQMTQSPSSLSA SVGDRVTITC | RAS--QGIR------NDLG | WYQQKPGK APKRLIY | A-------ASNLQS | GVPSRFSGSRSG--TEFTLTISSLQPEDFATYYC | LQHNS---------YPFT | FGPGT KVDIK |
| iPS:433_949 | 21-225_45H2 | VK1lA30/ JK3 | DIQMTQSPSSLSA SVGDRVTITC | RAS--QGIR------NDLG | WYQQKPGK APKRLIY | G-------ASSLQS | GVPSRFSGSGSG--TEFTLTVSSLQPEDFATYFC | LQHTS---------FPFT | FGPGT KVDIK |
| iPS:433_981 | 21-225_46E9 | VK1lA30/ JK3 | DIQMTQSPSSLSA SVGDRVTITC | RAS--QGIR------NDLG | WYQQKPGK APKRLIY | A-------ASSLQS | GVPSRFSGSGSG--TEFTLTVSSLQPEDFATYFC | LQHTS---------FPFT | FGPGT KVDIK |
| iPS:433_995 | 21-225_47H7 | VK1lA30/ JK3 | DIQMTQSPSSLSA SVGDRVTITC | RTS--QGIR------NDLG | WYQKKPGK APKRLIY | A-------ASSLQS | GVPLRFSGSGSG--TEFTLTIRSLQPEDFATYYC | LQHTS---------FPFT | FGPGT KVDIK |
| iPS:434_039 | 21-225_43B1 | VK1lA30/ JK3 | DIQMTQSPSSLSA SVGDRVTITC | RAS--QGIR------NDLG | WYQQKPGK APKRLIY | G-------ASSLQS | GVPSRFSGSGSG--TEFTLTVSSLQPEDFATYFC | LQHTS---------FPFT | FGPGT KVDIK |
| iPS:434_057 | 21-225_51E4 | VK1lA30/ JK3 | DIQMTQSPSSLSA SVGDRVTITC | RAS--QGIR------KNLG | WYQQKPGK APKRLIY | A-------ASSLQS | GVPSRFSGSGSG--TEFTLTISSLQPEDFAAYYC | LQYNS---------YPFT | FGPGT KVDIK |
| iPS:434_071 | 21-225_51F9 | VK1lA30/ JK3 | DIQMTQSPSSLSA SVGDRVTITC | RAS--QGIR------TDLG | WYQQKPRK APQRLIY | A-------ASSLQR | GVPSRFSGSGSG--TEFTLTISSLQPEDFASYYC | LQHNS---------YPFT | FGPGT KVDIK |
| iPS:434_075 | 21-225_51B11 | VK1lA30/ JK3 | AIQMTQSPSLSA SVGDRVTITC | RTS--QGIR------NDLG | WYQQKPGK APKRLIY | A-------ASSLQS | GVPLRFSGSGSG--TEFTLTIRSLQPEDFATYYC | LQHTS---------YPFT | FGPGT KVDIK |
| iPS:434_091 | 21-225_52B9 | VK1lA30/ JK3 | AIQMTQSPSSLSA SVGDRVTITC | RAS--QGIR------NDLG | WYQQKPGK APKRLIY | A-------ASSLQS | GVPLRFSGSGSG--TEFTLTIRSLQPEDFATYYC | LQYNS---------YPFT | FGPGT KVDIK |
| iPS:434_101 | 21-225_52H12 | VK1lA30/ JK3 | DIQMTQSPSSLSA SVGDRVTITC | RAS--QGIR------NNLG | WYQQKPGK APKRLIY | G-------ASSLQS | GVPSRFSGSGSG--TEFTLTISSLQPEDFATYYC | LQHNS---------YPFT | FGPGT KVDIK |
| iPS:434_103 | 21-225_53G1 | VK1lA30/ JK3 | DIQMTQSPSSLSA SVGDRVTITC | RAS--QGIR------NDLG | WYQQKPGK APKRLIY | P-------ASSLQS | GVPSRFSGSGSG--TEFSLTISSLQPEDFATYYC | LQHNS---------YPFT | FGPGT KVDIK |
| iPS:434_129 | 21-225_53B12 | VK1lA30/ JK3 | DIQMTQSPSSLSA SVGDRVTITC | RAS--QGIR------NDLG | WYQQKPGK APKRLIY | A-------ASSLQS | GVPSRFSGSGSG--IEFTLTISSLQPEDFATYYC | LQHNS---------YPFT | FGPGT KVDIK |

Figure 51 (Continued)

| ID | | | | | | | | | | |
|---|---|---|---|---|---|---|---|---|---|---|
| iPS:434_131 | 21-225_54D3 | VK1|A30/JK3 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNS---- -------YPFT | FGPGT KVDIK |
| iPS:434_143 | 21-225_54G7 | VK1|A30/JK3 | DIQMTQSPSSLSA SVGDRVTITC | RAS--QGIR- ----NDLG | WYQQKPGK APKRLIY | A------ ASSLQS | GVPSGT----FSGSGSG-- TEFTLTISSLQPEDFATYYC | LHHNT---- -------YPFT | FGPGT KVDIR |
| iPS:434_155 | 21-225_55B3 | VK1|A30/JK3 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFASYYC | LQHNS---- -------YPFT | FGPGT KVDIK |
| iPS:434_169 | 21-225_50C4 | VK1|A30/JK3 | DIQMTQSPSSLSA SVGDRVTITC | RAS--QGIR- ----NDLG | WYQQKPGI APKRLIY | A------ ASSLQS | GVPSRFSGSGSRSG-- TEFTLTISSLQPEDFATYYC | LQHNR---- -------YPFT | FGPGT KVDIK |
| iPS:434_187 | 21-225_56A5 | VK1|A30/JK3 | DIQMTQSPSSLSA SVGDRVTITC | RAS--QDIR- ----NLLG | WYQQKPGK APKRLIY | A------ ASSLQS | GVPSRFSGSGSG-- TEFTLTISSLQPEDFATYYC | LQYNS---- -------YPFT | FGPGT KVDIR |
| iPS:434_199 | 21-225_59F11 | VK1|A30/JK3 | DIQMTQSPSSLSA SVGDRVTITC | RAS--QGIR- ----NDLG | WYQQKPGK APKRLIY | A------ ASSLQS | GVPSRFSGSGSG-- TEFTLTISSLQPEDFATYYC | LQHNR---- -------YPFT | FGPGT KVDFK |
| iPS:434_207 | 21-225_60A3 | VK1|A30/JK3 | DIQMTQSPSSLSA SVGDRVTITC | RAS--QGIR- ----NDLG | WYQQKPGK APKRLIY | A------ AFSLQS | GVPSRFSGSGSG-- TEFTLTISSLQPEDFATYYC | LQHNS---- -------YPFT | FGPGT KVDIK |
| iPS:434_251 | 21-225_62G3 | VK1|A30/JK3 | DIHMTQSPSSLSA SVGDRVTITC | RAS--QDIR- ----NNLG | WYQQKPGK APKRLIY | T------ ASSLQS | GVPSRFSGSGSG-- TEFTLTISSLQPEDFATYYC | LQYGS---- -------YPFT | FGPGT KVDIK |
| iPS:434_263 | 21-225_56H7 | VK1|A30/JK3 | DIQLTQSPSSLSA SVGDRVTITC | RAS--QDIR- ----NDLG | WYQQKPGK APKRLIY | P------ ASSLLS | GVPSRFGSGSGSG-- TEFTLTISSLQPEDFATYYC | LQHNS---- -------YPFT | FGPGT KVDIK |
| iPS:434_265 | 21-225_57B2 | VK1|A30/JK3 | DIQMTQSPSSLSV SVGDRVTITC | RAS--QGIR- ----NALG | WYQQKPGK APKRLIY | A------ ASSLQS | GVPSRFSGSGSG-- TEFTLTISSLRPEDFATYYC | LQHNN---- -------YPFT | FGPGT KVDIK |
| iPS:434_271 | 21-225_57A4 | VK1|A30/JK3 | DIQMTQSPSSLSA SVGDRVTITC | RAS--QGIR- ----NDLG | WYQQKPGK APTRLIY | T------ ASTLQS | GVPSRFSGSGSG-- TEFTLTISSLQPEDFATYYC | LQYNS---- -------YPFT | FGPGT KVDIK |
| iPS:434_275 | 21-225_57F4 | VK1|A30/JK3 | DIQMTQSPSSLSA SVGDRVTITC | RAS--QVIR- ----NVLG | WYQQKPGK APKRLIY | A------ ASSLQS | GVPSGFGSGSGSG-- TEFTLTISSLQPEDFATYYC | LQYNS---- -------YPFT | FGPGT KVDIK |
| iPS:434_293 | 21-225_58F5 | VK1|A30/JK3 | DIQMTQSPSSLSA SVGDRVTITC | RAS--QGIR- ----NDLG | WFLQTPGK APKRLIY | A------ ASSLLS | GVPSRFSGSGSG-- TEFTLTISSLQPEDFATYYC | LHHNS---- -------YPFT | FGPGT KVDIK |
| iPS:434_299 | 21-225_58D11 | VK1|A30/JK3 | DIQMTQSPSSLSA SVGDRVTITC | RAS--QGIR- ----SDLD | WYQQKPGK APKRLIY | A------ ASSVQS | GVPSRFSGSGSG-- TEFTLAISSLRPEDFATYYC | LQYNS---- -------YPFT | FGPGT KVDIK |
| iPS:434_351 | 21-225_64A12 | VK1|A30/JK3 | DIQMTQSPSSLSA SVGDRVTITC | RAS--QGIR- ----NDLD | WYQQKPGK APQRLIY | A------ ASSLQS | GVPSRFSGSGSG-- TEFTLTISSLQPDDFATYYC | LQHNG---- -------YPFT | FGPGT KVDIK |
| iPS:434_383 | 21-225_66F9 | VK1|A30/JK3 | DIQMTQSPSSLSA SVGDRVTITC | RAS--QGIR- ----NDLG | WYQQKPGK APKRLIY | T------ ASSLQS | GVPSGFGSGSGSG-- TEFTLTISSLQPEDFATYYC | LQYNS---- -------YPFT | FGPGT KVDIK |
| iPS:434_399 | 21-225_67B7 | VK1|A30/JK3 | DIQMTQSPSSLSA SVGDRVTITC | RAS--QGIR- ----NVLG | WFQQKPGK APKRLIY | A------ ASSLQS | GVPSRFSGSGSG-- TEFTLTISSLQPEDFATYYC | LHHNS---- -------YPFK | FGPGT KVDIK |
| iPS:434_407 | 21-225_68G8 | VK1|A30/JK3 | DIQMTQSPSSLSA SVGDRVTITC | RAS--QGIR- ----NNLG | WYQQKPGK APKRLIY | A------ ASSLLS | GVPSRFSGSGSG-- TEFTLTISSLQPEDFATYYC | LQYNS---- -------YPFT | FGPGT KVDIK |
| iPS:434_447 | 21-225_71B6 | VK1|A30/JK3 | DIQMTQSPSPSA SVGDRVTITC | RAS--QGIR- ----NDLD | WYQQKPGK APQRLIY | A------ ASSLQS | GVPSRFSGSGSG-- TEFTLTISSLQPDDFATYYC | LQHNS---- -------YPFT | FGPGT KVDIK |
| iPS:434_449 | 21-225_71H6 | VK1|A30/JK3 | DIQMTQSPSSLSA SVGDRVTITC | RAS--QGIR- ----NVLG | WYQQTPGK APKRLIY | A------ ASSLQS | GVPSGFGSGSGSG-- TEFTLTISSLQPEDFTTYYC | LQYNS---- -------YPFT | FGPGT KVDVK |
| iPS:434_453 | 21-225_71B11 | VK1|A30/JK3 | DIQMTQSPSSLSA SVGDRVTITC | RAS--QGIR- ----NDLD | WFQQKPGK APKRLIC | A------ ASSLQS | GVPSRFSGSGSG-- TEFTLTISSLQPEDFATYYC | LQHNT---- -------YPFT | FGPGT KVDVK |
| iPS:434_463 | 21-225_73A6 | VK1|A30/JK3 | DIQMTQSPSSLSA SVGDRVTITC | RAS--QDIR- ----NDLG | WYQQKPGK APKRLIY | A------ ASNLQS | GVPSRFSGSGSG-- TEFTLTISSLQPEDFATYYC | LQHNS---- -------YPFT | FGPGT KVDIK |
| iPS:434_815 | 21-225_74A11 | VK1|A30/JK3 | DIQMTQSPSSLSA SVGDRVTITC | RAS--QDIR- ----NDLG | WYQQKPGK APKRLIC | A------ ASSLQS | GVPSRFSGSGSG-- TEFTLTISSLQPEDFATYFC | LQHND---- -------YPFT | FGPGT KVDIK |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS:434 977 | 21-225_88A5 | VK1A30/ JK3 | DIQMTQSPSSLSA SVGDRVTITC | RAS--QGIR- ----NDLG | WYQQKPGK APKRLIY | A--------- ASSLQS | GVPSRFSGSGSG-- TEFTLTISSLQPEDFATYYC | LQHND------ --------YPFT | FGPGT KVEIK |
| iPS:435 253 | 21-225_96A4 | VK1A30/ JK3 | DIQMTQSPSSLSA SVGDRVTITC | RAS--QDIR- ----NDLG | WYQQKPGK APKRLIY | G--------- VSSLQS | TDFTLTISSLQREDFATYYC | LQHND------ --------YPFT | FGRGT KVDIK |
| iPS:435 511 | 21-225_157C3 | VK1A30/ JK3 | DIQMTQSPSSLSA SVGDRVTITC | RAS--QGIR- ----NDLG | WYQQKPGK APKRLIY | A--------- ASSLQS | GVPSRFSGSGSG-- TDFTLTISSLQPDDFATYYC | LQHNS------ --------YPFT | FGPGT KVDIK |
| iPS:435 521 | 21-225_157H4 | VK1A30/ JK3 | DIQMTQSPSSLSA SVGDRVTITC | RAS--QGIR- ----NDLG | WYQQKPGK APKRLIY | P--------- ASSLQT | GVPSRFSGSGSG-- TEFTLTISSLQPEDFATYYC | LQDNS------ --------YPFT | FGPGT KVDIK |
| iPS:435 527 | 21-225_157G7 | VK1A30/ JK3 | DIQMTQSPSSLSA SVGDRVTITC | RAS--QGIR- ----NDLG | WYQQKPGK APKRLIN | V--------- ASSLQS | GVPSRFSGSGSG-- TEFTLTISSVQREDFATYYC | IQDNS------ --------HPFT | FGPGT KVEIK |
| iPS:435 533 | 21-225_157H8 | VK1A30/ JK3 | DIQMTQSPSSLSA SVGDRVTITC | RAS--QGIR- ----NDLG | WYQQKPGK APKRLIY | A--------- ASSLQS | GVPSRFSGSGSG-- TDFTLTISSLQPDDFATYYC | LQHNS------ --------YPFT | FGPGT KVDIK |
| iPS:435 537 | 21-225_157H1 2 | VK1A30/ JK3 | DIQMTQSPSSLSA SVGDRVTITC | RAS--QGIR- ----NDFG | WYQQRPGK APKCLIH | A--------- ASSLQS | GVPSRFSGSGSG-- TEFTLTISSLQPEDFATYYC | LQHYS------ --------YPFT | FGPGT KVDIK |
| iPS:435 547 | 21-225_158F5 | VK1A30/ JK3 | DIQMTQSPSSLSA SVGDRVTITC | RAS--QGIR- ----NDLG | WYQQKPGK APKRLIN | A--------- ASSLQS | GVPSRFSGSGSG-- TEFTLTISSLQPEDFATYYC | LQDNS------ --------HPFT | FGPGT KVEIK |
| iPS:435 551 | 21-225_158H6 | VK1A30/ JK3 | DIQMTQSPSSLSA SVGDRVTITC | RAS--QGIR- ----SDLG | WYQQKPGK APKRLIY | T--------- ASSLQS | GVPSRFSGSGSG-- TEFTLTISSLQPEDFATYYC | LQHNS------ --------YPFT | FGPGT KVDIK |
| iPS:435 553 | 21-225_158G8 | VK1A30/ JK3 | DIQMTQSPSSLSA SVGDRVTITC | RAS--QDIR- ----NDLG | WYQQKPGK APKRLMI | T--------- ASSLQS | GVPSRFSGSGSG-- TEFTLTISSLQPEDFATYYC | LQHNS------ --------YPFT | FGPGT KVDIK |
| iPS:435 569 | 21-225_159C5 | VK1A30/ JK3 | DIQMTQSPSSLSA SVGDRVTITC | RTS--QGIR- ----NDLG | WYQQKPGK APKRLIY | A--------- ASSLQS | GVPSRFSGSGSG-- TDFTLTISSLQPDDFATYYC | LQHNS------ --------YPFT | FGPGT KVDIK |
| iPS:435 593 | 21-225_160F4 | VK1A30/ JK3 | DIQMTQSPSSPSA SVGDRVTITC | RAS--QGIR- ----NDLG | WYQQKPGE APKRLIN | V--------- ASSLQS | GVPSRFSGSGSG-- TEFTLTISSVQPEDFATYYC | IQDNS------ --------HPFT | FGPGT KVEIK |
| iPS:435 609 | 21-225_161F7 | VK1A30/ JK3 | DIQMTQSPSSLSA SVGDRVTITC | RAS--QGIR- ----NDLG | WYQQKPGE APKRLIY | A--------- ASTLQS | AEFTVTIGSVQREDFATYYC | LLYIR------ --------YPFT | FGRGT KVDIK |
| iPS:435 613 | 21-225_161D1 | VK1A30/ JK3 | DIQMTQSPSSLSA SVGDRVTITC | RAS--QGIR- ----NDLG | WYQQKPGE APKRLIY | A--------- ASTLQS | AEFTVTIGSVQREDFATYYC | LQYNR------ --------YPFT | FGPGT KVDIK |
| iPS:435 617 | 21-225_162F2 | VK1A30/ JK3 | DIQMTQSPSSLCA SVGDRVTITC | RAS--QGIR- ----NDLG | WYQQKPGK APKRLIN | A--------- ASSLQS | GVPSRFSGSGSG-- TEFTLTISSVQPEDFATYYC | IQDNS------ --------HPFT | FGPGT KVEIK |
| iPS:435 621 | 21-225_162H3 | VK1A30/ JK3 | DIQMTQSPSSLSA SVGDRVTITC | RAS--QDIR- ----NDLG | WYQQKPGK APKRLIN | A--------- ASSLQS | GVPSRFSGSGSG-- TEFTLTISSLQPEDFATYYC | LQHNS------ --------YPFT | FGPGT KVDIK |
| iPS:435 637 | 21-225_163E2 | VK1A30/ JK3 | DIQMTQSPSSLSA SVGDRVTITC | RAS--QGIR- ----NDLG | WYQQKPGK APTRLIY | A--------- ASSLQS | GVPSRFSGSGSG-- TEFTLTISSLQPEDFATYYC | LQHNS------ --------HPFT | FGPGT KVDIK |
| iPS:435 641 | 21-225_163F9 | VK1A30/ JK3 | DIQMTQSPSSLSA SVGDRVTITC | RAS--QDIR- ----DDLG | WYQQKPGK APKRLIY | P--------- ASSLQS | GVPSRFSGSGSG-- TEFTLTISSLQPEDFATYYC | LQDNS------ --------YPFT | FGPGT KVDIK |
| iPS:435 643 | 21-225_163G1 | VK1A30/ JK3 | DIQMTQSPSSLSA SVGDRVTITC | RAS--QDIR- ----NNLG | WYQQKPGK APKRLIY | P--------- ASSLQS | GVPSRFSGSGSG-- TEFTLTISSLQPEDFATYYC | LQDYS------ --------YPFT | FGPGI KVDIK |
| iPS:435 719 | 21-225_171A1 | VK1A30/ JK3 | DIQMTQSPSSLSA SVGDRVTITC | RAS--QGIR- ----NNLG | WYQQKPGK APKRLIY | A--------- ASSLQS | GVPSRFSGSGSG-- TEFTLTISSLQPEDFATYYC | LQDHS------ --------HPFT | FGPGT KVDIK |
| iPS:435 769 | 21-225_177B6 | VK1A30/ JK3 | DIQMTQSPSSLSA SVGDRVTITC | RAS--QDIS- ----NDLG | WYQQKPGK APKRLIY | A--------- ASSLQS | GVPSRFSGSGSG-- TEFTLTINSLQPEDFATYYC | LQLMS------ --------YPFT | FGPGT KVDIK |

Figure 51 (Continued)

| ID | Family | | | | | | | | |
|---|---|---|---|---|---|---|---|---|---|
| iPS:435_791 | 21-225_180H7 | VK1/A30/JK3 | DIQMTQSPSSLSA SVGDRVTITC | RAS--QGIR-----NDLG | WYQQKPGK APKRLIY | T--------ASSLQS | GVPSRFSGSGSG-- TEFTLTISSLQPEDFASYYC | LQHNS-------------YPFT | FGPGT KVDFK |
| iPS:435_805 | 21-225_181A8 | VK1/A30/JK3 | DIQMTQSPSSLSA SVGDRVTITC | RAS--QGIR-----NDLG | WYQQKPGK APKRLIY | T--------ASSLQS | GVPSRFSGSGSG-- TDFTLTISSLQPEDFASYYC | LQHNS-------------YPFT | FGPGT KVDIK |
| iPS:435_879 | 21-225_184H1 | VK1/A30/JK3 | DIQMTQSPSSLSA SVGDRVTITC | RAS--QGIR-----NDLG | WYQQKPGK APKRLIY | I--------ASSLQS | GVPSRFSGSGSG-- TEFTLTISSLQPEDFATYYC | LQHNS-------------YPFT | FGPGT KVDIK |
| iPS:435_881 | 21-225_184D1 | VK1/A30/JK3 | DIQMTQSPSSLSA SVGDRVTITC | RAS--QGIR-----NDLG | WYQQKPGK APKRLIY | I--------ASSLQS | GVPSRFSGSGSG-- TEFTLTISSLQPEDFATYYC | LQHNS-------------YPFT | FGPGT KVDIK |
| iPS:435_921 | 21-225_190D6 | VK1/A30/JK3 | DIQMTQSPSSLSA SVGDRVTITC | RAS--QGIR-----NDLG | WYQLKPGK APKRLIY | A--------ASSLQS | GVPSRFSGSGSG-- PEFTLTISSLQPEDFATYYC | LQHYS-------------FPFT | FGPGT KVDFK |
| iPS:435_985 | 21-225_192F6 | VK1/A30/JK3 | DIQMTQSPSSLSA SVGDRVTITC | RAS--QGIR-----NDLG | WYQLKPGK APKRLIY | A--------ASSLQS | GVPSRFSGSGSG-- PEFTLTISSLQPEDFATYYC | LQHYS-------------FPFT | FGPGT KVDIK |
| iPS:436_074 | 21-225_194F10 | VK1/A30/JK3 | DIQMTQSPSSLSA SVGDRVTITC | RAS--QGIR-----NDLG | WYQLKPGK APKRLIY | A--------ASSLQS | GVPSRFSGSGSG-- TEFTLTISSLQPEDFATYYC | LQHYS-------------FPFT | FGPGT KVDIK |
| iPS:436_092 | 21-225_195B9 | VK1/A30/JK3 | DIQMTQSPSSLSA SVGDRVTITC | RAS--QGIR-----KDLG | WYQQKPGK APKRLIY | A--------ASDLQS | GVPSRFSGSGSG-- TEFTLTISSLQPEDFATYYC | LQHYR-------------YPFT | FGPGT KVDFK |
| iPS:436_164 | 21-225_197G1 | VK1/A30/JK3 | DIQMTQSPSSLSA SVGDRVTITC | RAS--QGIR-----NDLG | WYQQKPGK APKRLIY | G--------ASSLQS | GVPSRFSGSGSG-- TEFTLTISSLQPEDFATYYC | LQHYR-------------YPFT | FGPGT KVDIK |
| iPS:436_191 | 21-225_198B9 | VK1/A30/JK3 | DIQMTQSPSSLSA SVGDRVTITC | RAS--QGIR-----KDLG | WYQQKPGK APKRLIY | A--------ASRLQS | GVPSRFSGSGSG-- TEFTLTISSLQPEDFATYYC | LQHHD-------------YPFT | FGPGT KVDFK |
| iPS:436_205 | 21-225_199A7 | VK1/A30/JK3 | DIQMTQSPSSLSA SVGDRVTITC | RAS--QGIR-----NDLG | WYQQKPGK APKRLIY | R--------ASSVQN | GVPSRFSGSGSG-- TEFTLTISSLQPEDFATYHC | LQHYR-------------YPFT | FGPGT KVDIK |
| iPS:436_214 | 21-225_200F6 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPEDFATYYC | LQHYR-------------YPFT | FGPGT KVDIK |
| iPS:436_248 | 21-225_202A3 | VK1/A30/JK3 | DIQMTQSPSSLSA SVGDRVTITC | RAS--QGIR-----NDLG | WYQQKPGK APKRLIY | A--------ASSLQS | GVPSRFSGSG-G-- TEFTLTISSLQPEDFATYHC | LQHYR-------------YPFT | FGPGT KVDIK |
| iPS:436_268 | 21-225_203B9 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPEDFATYYC | LQHNS-------------YPFT | FGPGT KVDIK |
| iPS:436_350 | 21-225_210E4 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPEDFATYYC | LQHNS-------------YPFT | FGPGT KVDIK |
| iPS:436_576 | 21-225_225B6 | VK1/A30/JK3 | DIQMTQSPSSLSA SVGDRVTITC | RAS--QGMR-----NDLG | WYQQKPGK APKRLIY | A--------ATSLQS | GVPSRFSGSG-G-- TEFTLTISSLQPEDFATYYC | LQHNT-------------YPFT | FGPGT KVDIK |
| iPS:436_578 | 21-225_225D6 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPEDFATYYC | LQHNT-------------YPFT | FGPGT KVDIK |
| iPS:436_582 | 21-225_225F8 | VK1/A30/JK3 | DIQMTQSPSSLSA SVGDRVTITC | RAS--QGIR-----NDLG | WYQQKPGK APKRLIC | A--------ASSLLG | GVPSRFSGSGSG-- TEFTLTISSLQPEDFATYYC | LQHNS-------------YPFT | FGPGT KVDIK |
| iPS:436_608 | 21-225_226A9 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPEDFATYYC | LQHNS-------------YPFT | FGPGT KVDIK |
| iPS:436_630 | 21-225_227G3 | VK1/A30/JK3 | DIQMTQSPSSLSA SVGDRVTITC | RAS--QGIR-----NDLG | WYQQKPGK APKRLIY | A--------ASSLQS | GVPSRFSGSGSG-- TEFTLTISSLQPADFATYYC | LRHNS-------------YPFT | FGPGT KVDIK |
| iPS:436_634 | 21-225_227H5 | VK1/A30/JK3 | DIQMTQSPSSLSA SVGDRVTITC | RAS--QDIR-----NDLG | WYQQKPGK APKRLIY | A--------ASSLQS | GVPSRFSGSGSG-- TEFTLTISSLQPEDFATYYC | LQHNS-------------YPFT | FGPGT KVDIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:436650 | 21-225_227C12 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTISSLQPEDFATYYC | LQHNS--------YPFT | FGPGT KVDIK |
| iPS:392632 | 21-225_16A11 VK1|A30/JK3 | DIQMTQSPSSLSA SVGDRVTIISC | RAS--QGIR-----NHLG | WYQRNPGK APKRLIY | A-------ASSLQS | GVPSRFSGSGSG--TEFTLTISSLQPEDFATYYC | LQHNS--------YPFT | FGPGT KVDIK |
| iPS:392684 | 21-225_17F4 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTISSLQPEDFATYYC | LQHNS--------YPFT | FGPGT KVDIK |
| iPS:392732 | 21-225_17E5 VK1|A30/JK3 | DIQMTQSPSSLSA SVGDRVTIIC | RAS--QGIR-----NDLG | WYQQKPGK APKRLIY | T-------ASSLQS | GVPSRFSGSGSG--TEFTLTISSLQPEDFATYYC | LQHNS--------YPLI | FGPGT KVVIK |
| iPS:392778 | 21-225_22H3 VK1|A30/JK3 | DIQMTQSPSSLSA SVGDRVTITC | RAS--QDIR-----NNLG | WYQQKPGK APKRLIY | P-------ASSLQT | GVPSRFSGSGSG--TEFTLTISSLQPEDFATYPC | LQDNS--------YPFT | FGPGT KVDIK |
| iPS:392912 | 21-225_25A9 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTISSLQPEDFATYYC | LQHNS--------YPFT | FGPGT KVDIK |
| iPS:392934 | 21-225_27D5 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTISSLQPEDFATYYC | LQHNT--------YPFT | FGPGT KVDFK |
| iPS:392940 | 21-225_29D9 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTVSSLQPEDFATYYC | LQHNS--------YPFT | FGPGT KVDIK |
| iPS:392948 | 21-225_25G5 VK1|A30/JK3 | DIQMTQSPSSLSA SVGDRVTITC | RAS--QGIR-----NDLG | WYQQKPGK APKRLIY | R-------ASSLQS | GVPSRFSGSGSG--TEFTLTISSLQPEDFATYYC | LQHNS--------YPFT | FGPGT KVDIK |
| iPS:392968 | 21-225_25B6 VK1|A30/JK3 | DIQMTQSPSSLSA SVGDRVTITC | RAS--QGIR-----NDLG | WYQQKPGK APKRLIY | A-------ASSLQS | GVPSRFSGSGSG--TEFTLTISSLQPEDFATYYC | LQHNS--------YPFT | FGPGT KVDIN |
| iPS:392978 | 21-225_28B8 VK1|A30/JK3 | DIQMTQSPSSLSA SVGDRVTITC | RAS--QGIR-----NDLG | WYQHKPGK APKRLIY | A-------ASSLQS | GVPSRFSGSGSG--TEFTLTISSLQPEDFATYYC | LQHNR--------YPFT | FGPGT KVDIK |
| iPS:392998 | 21-225_28A9 VK1|A30/JK3 | DIQMTQSPSSLSA SVGDRVTITC | RAS--QGIR-----NDLG | WYQQKPGK APKRLIY | A-------ASSLQN | GVPSRFSGSGSG--TEFTLTISSLQPEDFATYYC | LQHNS--------YPFT | FGPGT KVDIK |
| iPS:393000 | 21-225_29D7 VK1|A30/JK3 | DIQMTQSPSSLSA SVGDRVTITC | RAS--QGIR-----NDLG | WYQQKPGK APKRLIY | P-------ASSLQS | GVPSRFSGSGSG--TEFTLTISSLQPEDFATYYC | LQDNS--------YPFT | FGPGT KVDIK |
| iPS:393006 | 21-225_31G9 VK1|A30/JK3 | DIQMTQSPSSLSA SVGDRVTITC | RAS--QGIR-----NDLG | WYQQKPGK APKRLIY | P-------ASSLQS | GVPSRFSGSGSG--TEFTLTISSLQPEDFATYYC | LQDNS--------YPFT | FGPGT KVDIK |
| iPS:393022 | 21-225_30H11 VK1|A30/JK3 | DIQMTQSPSSLSA SVGDRVTITC | RAS--QGIR-----NDLG | WYQQKPGK APKRLVI | A-------ASSLQS | GVPSRFSGSGSG--TEFTLTISSLQPEDFATYYC | LQDNS--------HPFT | FGPGT KVDII |
| iPS:393038 | 21-225_29D8 VK1|A30/JK3 | DIQMTQSPSSLSA SVGDRVTITC | RAS--QGIR-----NDLG | WYQQKPGK APKRLIY | T-------ASSLQS | GVPSRFSGSGSG--TEFTLTISSLQPEDFATYYC | LQHNS--------YPFT | FGPGT KVDIK |
| iPS:393822 | 21-225_15B11 VK1|A30/JK3 | DIQMTQSPSSLSA SVGDRVTITC | RAS--QGIR-----NDLG | WYQHKPGK APKRLIY | A-------ASSLQS | GVPSRFSGSGSG--TEFTLTISSLQPEDFATYYC | LQHNS--------YPFT | FGPGT KVDIK |
| iPS:393944 | 21-225_14D6 VK1|A30/JK3 | DIQMTQSPSSLSA SVGDRVTITC | RAS--QGIR-----NHLG | WYQQKPGK APKRLIY | A-------ASSLQS | GVPSRFSGSGSG--TEFTLTISSLQPEDFATYYC | LQYNG--------YPFT | FGPGT KVDIN |
| iPS:394033 | 21-225_5F4 VK1|A30/JK3 | DIQMTQSPSSLSA SVGDRVTITC | RAS--QGIR-----DILG | WYQQKPGK APKRLIY | A-------ASSLQN | GVPSRFSGSGSG--TEFTLTVSSLQPEDFATYYC | LQYHS--------YPFT | FGPGT KVDIK |
| iPS:394069 | 21-225_16H1 VK1|A30/JK3 | DIQMTQSPSSLSA SVGDRVTIIC | RAS--QGIR-----NYLG | WFQQKPGK APKRLIY | G-------ASSLQS | GVPSRFSGSGSG--TEFTLTISSLQPEDFATYYC | LQYHS--------YPFT | FGPGT KVDVK |
| iPS:402229 | 21-225_16H9 VK1|A30/JK3 | DIQMTQSPSSLSA SVGDRVTITC | RAS--QGIR-----NYLG | WYQQKPGK APKRLIY | A-------ASSLQS | GVPSRFSGSGSG--TEFTLTISSLQPEDFATYYC | LQYHS--------YLFT | FGPGT KVDIK |
| | VK1|O12/JK1 Germline | | | | | | | |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:468 848 | 21-225_54B1 | VK1|O12/ JK1 | DIQMTQSPSSLSA SIGDRVTITC | RAS--QNIS-----SYLN | WYQQKPGK APKFLIY | A------ ASSLHS | GVPPRFSGSGSG--TDFTLTISSLQPEDFATYYC | QQSYR-------TPLWT | FGQGT KVEIK |
| iPS:434 239 | 21-225_58F1 | VK1|O12/ JK1 | DIQMTQSPSSLSA SVGDRVTITC | RAS--QSIT-----NFLN | WYQQKPGK APKLLIF | A------ ASSLQS | GIPSRFSGSGSG--TDFTLTISSLQPEDFATYYC | QQSYS-------IPWT | FGQGT KVEIK |
| iPS:435 513 | 21-225_157F3 | VK1|O12/ JK1 | DIQMTQSPSSLSA SVGDRVTITC | RAS--QNIS-----SYLN | WYQLKPGK APKLLIY | T------ ASSLQS | GVPSRFSGSGSG--TDFTLTISSLQPEDFATYYC | QQSYN-------TPTWT | FGQGT KVEIK |
| iPS:435 729 | 21-225_173E7 | VK1|O12/ JK1 | DIQMTQSPSSRSA CIGDRATTY | RAS--QTIS-----NYLN | WYQQKPGK APKLLIY | A------ ASSLQI | GVPSRFSGSGSG--TDFTLTISSVQPEDFATYFC | QQSYR-------TPQWT | FGQGT KVEIK |
| iPS:435 753 | 21-225_175G10 | VK1|O12/ JK1 | DIQMTQSPSSLSA SVGDRVTITC | RAS--QTIG-----NYLN | WYQQKPGR APKLLIY | A------ ASSLHS | GVPSGFSGSGSG--TDFTLTISSLQPEDFATYFC | QQSYR-------TPQWT | FGQGT KVEIK |
| iPS:435 799 | 21-225_181G3 | VK1|O12/ JK1 | DIQMTQSPSSLSA SVGDRVNTIC | RAS--HSIS-----NYLN | WYQQKAGK APNLLIY | T------ TLNLQS | GVPSRFSGSGSG--TDFTLTISSLQPEDFATYSC | QQSYS-------SPPWT | FGQGT KVEFK |
| iPS:435 813 | 21-225_183A1 | VK1|O12/ JK1 | DIQMTQSPSSLCA SVGDRVTITC | RAS--RNIS-----NYLN | WYQQKPGK APKLLIY | V------ VSSLQS | GVPSRFSGSGSG--TDFTLTISSLQPEDFATYYC | QQSYS-------SPPWT | FGQGT KVDIR |
| iPS:436 003 | 21-225_192G10 | VK1|O12/ JK1 | DIQMTQSPSSLSA SVGDRVTITC | RAS--QSIS-----NYLN | WYQQTPGK APKLLIY | A------ ESSLQS | GVPSRFSGSGSG--TDFTLTISSLQPEDFATYSC | QQSYS-------SPPWT | FGQGT KVEIR |
| iPS:436 212 | 21-225_200G1 | VK1|O12/ JK1 | DIQMTQSPSSLSA SVGDRVTITC | RAS--QSIS-----SYLN | WFQQKPGK APKLLIY | A------ ESSLQS | GVPSRFSGSGSG--TDFTLTISSLQPEDFATYSC | QQSYS-------SPPWI | FGQGT KVEIK |
| iPS:392 730 | 21-225_17A1 | VK1|O12/ JK1 | DIQMTQSPSSLSA SVGDRVTITC | RAS--QNIS-----NYLN | WYQQKPGK GPKVLIF | T------ TSSLQS | GVPSRFSGSGSG--TDFTLTISSLQPEDFATYYC | QQSYT-------TPTWT | FGQGT KVEIK |
| iPS:392 736 | 21-225_17B12 | VK1|O12/ JK1 | DIQMTQSPSSLSA SVGDRVSITC | RAS--QNIN-----NYLN | WYQQKPGK GPKVLIL | T------ ASSLQS | GVPSRFSGSGSG--TDFTLTISSLQPEDFATYYC | QQYTT-------TPTWT | FGQGT KVEIK |
| iPS:392 766 | 21-225_23H4 | VK1|O12/ JK1 | DIQMTQSPSSLSA SVGDRVSITC | RAS--QSIS-----NYLN | WYQQKPGR GPKVLIL | S------ TSSLQS | GVPSRFSGSGSG--TDFTLTISSLQPEDFATYYC | QQSYS-------TPTWT | FGQGT KVEIR |
| iPS:392 770 | 21-225_20C10 | VK1|O12/ JK1 | DIHMTQSPSSLSA SVGDKVSITC | RAS--HHIS-----RYLN | WYQQKPGK APKLLIC | T------ TSSLQS | GVPSRFSGSGSG--TDFTLTISSLQPEDFATYYC | QQSYT-------TPTWT | FGQGT KVEIK |
| iPS:392 808 | 21-225_20F8 | VK1|O12/ JK1 | DIQMTQSPSSLSA SVGDRVTITC | RAS--QSIS-----RYLN | WYQQKPGK APELLIY | A------ ASSLQS | GVPSRFSGSGSG--TDFTLTISSLQPEDFATYYC | QQSYN-------TPTWT | FGQGT KVEIK |
| iPS:392 954 | 21-225_26A10 | VK1|O12/ JK1 | DIQMTQSPSSLSA SVGDRIITC | RAS--QSIS-----SYLN | WYQQKPGK APKVLIY | W------ ASTRES | GVPSRFSGSGSG--TDFTLTISSLQPEDFATYYC | QQSYS-------TPTWI | FGQGT KVEIK |
| iPS:393 878 | 21-225_7G12 | VK1|O12/ JK1 | DIQMTQSPSSLSA SVGDRVSITC | RAS--QNIN-----NYLN | WYQQKPGK GPKVLIL | W------ ASTRES | GVPSRFSGSGSG--TDFTLTISSLQPEDFATYYC | QQSYT-------TPTWT | FGQGT KVEIK |
| iPS:398 474 | 21-225_17B10 | VK1|O12/ JK1 | DIQMTQSPSSLSA SVGDRVTITC | RSS--QSIN-----SYLN | WYQQKPGK APKLLIF | A------ ASSLHS | GVPSGFSGSGSG--TDFTLTISSLQPEDFATYYC | QQGYN-------TPTWT | FGQGT KVEIN |
| | VK4|B3/JK2 | Germline | | | | | | | |
| iPS:468 850 | 21-225_63F4 | VK4|B3/ K2 | DIVMTQSPDSLAV SLGERATINC | KSS--QSVLSSSNNWNN YLA | WYQQKPGQ PPKLLIY | W------ ASTRES | GIPDRFSGSGSG--TGFTLTISSLQAEDVAVYYC | QQYYT-------TPCS | FGQGT KLEIK |
| iPS:468 852 | 21-225_71F3 | VK4|B3/ K2 | DIVMTQSPDSLAV SLGARATINC | KSS--QSVLSNSNWNN YLA | WYQQKPGQ PPKLLIY | W------ ASTRES | GIPDRFSGSGSG--TDFTLTINSLQAEDVAVYYC | QQYYT-------TPCS | FGQGI KLEIK |

Figure 51 (Continued)

| | | | | | | | | |
|---|---|---|---|---|---|---|---|---|
| iPS:468 870 | 21-225_74A8 | VK4jB3jJK2 | DIVMTQSPDSLAV SLGERATINC | KSS--- QSVLYSSNSHN YLA | WYQQKPGQ PPKLLIY | W------- ASTRES | GVPDRFSGSGSG--- TDFTLTISSLQAEDVAVYYC | QQYYS------ -------TPCS | FGQGT KLEIK |
| iPS:434 211 | 21-225_60F3 | VK4jB3jJK2 | DIVMTQSPDSLTV SLGERATINC | KSS--- QSVLYSSNNKM YLA | WYQQKPGQ PPKLLIY | W------- ASTRES | GVPDRFSGSGSG--- TDFTLTISSLQAEDVAVYYC | QQYYS------ -------TPCS | FGQGT KLEIN |
| iPS:434 235 | 21-225_61E3 | VK4jB3jJK2 | DIVMTQSPDSLAV SLGERATINC | KSS--- QSVLHISNNNN YLA | WYQQQPGQ PPKLLIY | W------- ASIRES | GVPDRFSGSGSG--- TDFTLTISSLQAEDVAVYYC | QQYYS------ -------TPCS | FGQGT KLEIK |
| iPS:434 287 | 21-225_57F12 | VK4jB3jJK2 | DIVMTQSPDSLAV SLGERATINC | KSS--- QSVLFSGNNYN YLA | WYQQKTGQ PPKIIIY | W------- ASTRES | GVPDRFSGSGSG--- TDFTLTISSLQAEDVAIYYC | QQYYS------ -------NPCS | FGQGT KLEIK |
| iPS:434 305 | 21-225_59E1 | VK4jB3jJK2 | DIVMTQSPDSLAV SLGERATINC | KSS--- QSVLYSSNNNN YLA | WYQQKPGQ PPKLLIY | W------- SSTRES | GVPDRFSGSGSG--- TDFTLTISSLQAEDVAVYYC | QQYFS------ -------TPCS | FGQGT KLEIK |
| iPS:434 443 | 21-225_71G3 | VK4jB3jJK2 | DIVMTQSPDSLAV SLGERVAINC | KSS--- QSVLHSSNNNN YLD | WYQQKPGQ LPKLLIF | W------- ASTREF | GVPDRFSGSGFG--- TDFTLTISSLQAEDVADYYC | QQYYI------ -------TPCS | FGQGT KLEIK |
| iPS:434 483 | 21-225_74C12 | VK4jB3jJK2 | DIVMTQSPDSLAV SLGERATINC | KSS--- QSVLYSSNNAN YLA | WYQQKPGQ PPNLLIY | W------- ASTRES | GVPDRFSGSGSG--- TDFTLTISSLQAEDVAVYYC | QQYYS------ -------TPCS | FGQGT KLEIK |
| iPS:434 613 | 21-225_77D12 | VK4jB3jJK2 | DIVMTQSPDSLAV SLGERATINC | KSS--- QSVLYSSNNYN YLA | WYQQKPGQ PPKLLIY | W------- ASTRDS | GVPDRFSGSGSG--- TDFTLTISSLQAEDVAVYYC | QQYYT------ -------TPCS | FGQGT KLEIK |
| iPS:434 635 | 21-225_78E6 | VK4jB3jJK2 | DIVMTQSPDSLAV SLGERATINC | KSS--- QSVLYSSNSHN YLA | WYQQKPGQ PPKLLIY | W------- ASIRES | GVPDRFSGSGSG--- TDFTLTISSLQAEDVAVYYC | QQYYS------ -------TPCS | FGQGT KLEIK |
| iPS:434 679 | 21-225_79G7 | VK4jB3jJK2 | DIVMTQSPDSLAV SLGERATINC | KSS--- QSVLYSSNSHN YLA | WYQQKPGQ PPKLLIF | W------- ASIRES | GVPDRFSGSGSG--- TDFTLSISSMQAEDVAVYYC | QQYYS------ -------TPCS | FGQGT KLEIK |
| iPS:434 909 | 21-225_85C11 | VK4jB3jJK2 | DIVMTQSPDSLAV SLGERATINC | KSS--- QSVLYSSNGHN FLA | WYQQNPGQ PPKLLIF | W------- AFIRES | GVPEGFSGSGSG--- ADFLSISLQAEDVAVYYC | QQYYS------ -------TPCS | FGQGT KLEIK |
| iPS:434 959 | 21-225_87E10 | VK4jB3jJK2 | DIVMTQSPDSLAV SLGERATIKC | KSS--- QSVLYSSNNNN YLA | WYQQKPGQ PPKLLIY | W------- ASTRKS | GVPDRFSGTGSG--- TDFTLTISSLQAEDVAVYYC | QQYYS------ -------SPCS | FGQGT KLKIK |
| iPS:435 299 | 21-225_146D4 | VK4jB3jJK2 | DIVMTQSPDSLAV SLGERATINC | KSS--- QSVLYSSNNNN YLA | WYQQKPGQ PPKLVIY | W------- ASTRKS | GVPDRFSGSGSG--- TDFTLTISSLQAEDVAVYYC | QQYYS------ -------TPCS | FGQGT KLEIK |
| iPS:435 305 | 21-225_146C9 | VK4jB3jJK2 | DIVMTQSPDSLAV SLGERATINC | KSS--- QSVLHSSNNYN YLA | WYQCKPGQ PPKVLIY | W------- ASTRES | GVPDRFSGSGSG--- TDFTLTISSLQAEDVAVYYC | QQYYS------ -------TPCS | FGQGT KLEIK |
| iPS:435 309 | 21-225_146F9 | VK4jB3jJK2 | DIVMTQSPDSLAV SLGERATINC | KSS--- QNLHSSNNNN YLA | WYQQKPGQ PPYLLIY | W------- ASTRES | GVPDRFSGSGSG--- TDFTLTITSSLQAEDVAVYYC | QQYYT------ -------TPCS | FGQGT KLEIT |
| iPS:435 323 | 21-225_147D5 | VK4jB3jJK2 | DIVMTQSPDSLAV SLGERATINC | KSS--- QSVLYSSNNNN YLA | WYQQKPGQ PPKLLIY | W------- ASTRES | GVPDRFSGSGSG--- TDFTLSISSLQAEDVAVYYC | HQYYS------ -------TPCS | FGQGT KLEIK |

Figure 51 (Continued)

| | | | | | | | | |
|---|---|---|---|---|---|---|---|---|
| iPS:435_399 | 21-225_150D2 | VK4|B3/JK2 | DIVMTQSPDSLAV SLGERATINC | KSS----- QSVLYRSNSKK YLT | WYQQKPGQ PPKLFIY | W------- ASTRKS | GVPDRFSGSGSG- TDFTLTISNLQAEDVAVYYC | QQYFS-------- --------TPYN | FGQGT KREIK |
| iPS:435_435 | 21-225_152H3 | VK4|B3/JK2 | DIVMTQSPDSLAV SLGERATINC | KSS----- QSVLHSSNNYN YLT | WYQQKPGQ PPKLLIY | W------- ASTRKS | GVPDRFSGSGSG- TDFTLTISSLQAEDVAVYYC | QQYYS-------- --------TPCS | FGQGT KLEIK |
| iPS:435_451 | 21-225_152D1 | VK4|B3/JK2 | GIVMTQSPDSLAV SLGERATIDC | KSS----- QSVLYSSNNKN YLA | WYQQKPGQ PPKLLIY | W------- ASTRES | GVPDRFSGSGSG- TDFTLTISSLQAEDVAVYYC | QQYY--------- --------RSFS | FGQGT KLEIK |
| iPS:435_459 | 21-225_152E1 | VK4|B3/JK2 | AVVMTQSPDSLAV SLGERATINC | ISS----- QSILHSSNNYN YLA | WYQQKPGQ PPKLLIY | W------- ASTRES | GVPDRFSGSGSCG TDFTLTISSLQAEDVAVYYC | QQYYS-------- --------GPCS | FGQGT KLEIK |
| iPS:435_467 | 21-225_153B9 | VK4|B3/JK2 | GIVMTQSPDSLAV SLGERATINC | KSS----- QSVLYSSNNRN YLA | WYQQKPGQ PPKLLIY | W------- ASTREF | GVPDRFSGSGSG- TDFTLTIYSVQAEDVAVYYC | QQYN--------- --------RSLS | FGQGT KLEIK |
| iPS:435_471 | 21-225_153F11 | VK4|B3/JK2 | DIVMTQSPDSLAV SLGERATINC | KSS----- QSVLYSSNNYK YLA | WYQQKPGQ PPNLLIY | W------- ASTRKS | GVPDRFSGSGSG- TDFTLTISSLQAEDVAVYYC | QQYYS-------- --------TPCS | FGQGT KLEIK |
| iPS:435_475 | 21-225_154H6 | VK4|B3/JK2 | DIVMTQSPDSLAV SLGERATINC | KSS----- QSVLHSSNNYN YLA | WYQQKPGQ PPKLLIY | W------- TSTRKS | GVPDRFSGSGSG- THFTLSISSLQAEDVAVYYC | QHYYS-------- --------TPCS | FGQGT KLEIK |
| iPS:435_491 | 21-225_155E5 | VK4|B3/JK2 | DIVMTQSPDSLAV SLGERATINC | KSS----- QSVLSSSNNNN YLA | WYQQKPGQ PPKLLIY | W------- ASTRKS | GVPDRFSGSGSG- TDFTLTISSLQAEDVAVYYC | QQYYS-------- --------TPCS | FGQGT KLEIK |
| iPS:435_495 | 21-225_155B6 | VK4|B3/JK2 | DIVMTQSPDSLAV SLGERATINC | KSS----- QSVLHSSNNYN YLA | WYQQKPGQ PPKMLIY | W------- TSTRES | GVPDRFSGSGSG- TDFTLTISSLQAEDVAVYYC | QQYYS-------- --------TPCS | FGQGT KLEIK |
| iPS:435_501 | 21-225_156H1 | VK4|B3/JK2 | DIVMTQSPDSLAV SLGERATINC | KSS----- QSVLYSSNNNN YLA | WYQQKPGQ PPKLLIF | W------- ASTRES | GVPARFSGSGSG- TDFTLTISSLQAEDVAVYYC | HQYYS-------- --------TPCS | FGQGT KLEIK |
| iPS:435_589 | 21-225_160A4 | VK4|B3/JK2 | DIVMTQSPDSLAV SLGERATINC | KSS----- QSVLHSSNNNN YLA | WYQQKPGQ PPRLLIY | W------- ASTRES | GVPDRFSGSGSG- TDFTLTISSLQAEDVAVYYC | QQYN--------- --------SPCS | FGQGT KLEIK |
| iPS:435_727 | 21-225_172E1 | VK4|B3/JK2 | NIVMTQSPDSLAV SLDERATINC | KSS----- QSVLSSSNNHN YLA | WYQQKPGQ PPKLLIY | W------- ASTRES | GVPDRFSGSGSG- TDFTLTISGLQAEDVAVYYC | QQYFT-------- --------TPCS | FGQGT KLEIK |
| iPS:436_560 | 21-225_224F11 | VK4|B3/JK2 | DIVMTQSPDSLAV SLGERATINC | KSS----- QSVLSSSNNHN YLA | WYQQKPGQ PPKLLIY | W------- ASTRES | GVPDRFSGSGSG- TDFTLTISSLQAEDVAVYYC | QQYT--------- --------TPCS | FGQGT KLEIK |
| iPS:436_584 | 21-225_225B9 | VK4|B3/JK2 | DIVMTQSPDSLAV SLGERATINC | KSS----- QSVLYSSNNNN YLA | WYQQKPGQ PPKLLIF | W------- ASTRES | GVPDRFSGSGSG- TDFTLTISSLQAEDVAVYYC | QHSKS-------- --------IPGK | FGQGI KLEIQ |
| iPS:436_588 | 21-225_225F12 | VK4|B3/JK2 | DIVMTQSPDSLAV SLGERATINC | KSS----- QSVLYSSNNQN YLA | WYQQKPGQ PPRLLIY | W------- TSTRES | GVPDRFSGSGSG- TDFTLTISNLQAEDVAVYYC | QQYI--------- --------TPCS | FGQGT KLEIK |
| iPS:436_590 | 21-225_225H12 | VK4|B3/JK2 | DIVMTQSPDSLAV SLGERATINC | KSS----- QSVLYNSNNNN YLA | WYQQKPGQ PPNLLIY | W------- ASTRES | GVPDRFSGSGSG- TDFTLTISSLQTEDVAVYYC | QQYI--------- --------TPCS | FGQGT KLEIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:436 598 | 21-225_226D6 | VK4\|B3/JK2 | DIVMTQSPDSLAV SLGERATINC | RSS--- QSILYISNNKN YLA | WYQQKPGQ PPKMLIY | W------ ASTRES | GVPDRFSGSGSG--- TDFTLTISSLQAEDVAVYYC | QQYYS-------SPCS | FGQGT KLEIK |
| iPS:436 636 | 21-225_227E6 | VK4\|B3/JK2 | DIVMTQSPDSLIV SLGERATINC | KSS--- QSVLYSSNMDKN YLA | WYQQKPGQ PPKMLIY | W------ ASTRES | GVPDRFSGSGSG--- TDFTLTISSLQAEDVAVYYC | QQYYI-------TPCS | FGQGT KLEIK |
| iPS:436 644 | 21-225_227G9 | VK4\|B3/JK2 | DIVMTQSPDSLAV SLGERATINC | KSS--- QSVLHSSNNNN YLA | WYQQKPGQ PPKLLIY | W------ GSTRES | GVPDRFSGSGSG--- TDFTLTISSLQAEDVAVYYC | QQYYS-------APYS | FGQGT KLEIK |
| iPS:436 646 | 21-225_227D1 1 | VK4\|B3/JK2 | DIVMTQSPDSLAV SLGERATINC | KSS--- QSVLYISNNKN YLA | WYQQKPGQ PPKLLIY | W------ ASTRES | GIPDRFSGSGSG--- TDFTLTISSLQAEDVAVYYC | QQYYN-------TPCS | FGQGT KLEIK |
| iPS:437 363 | 21-225_74C10 | VK4\|B3/JK2 | DIVMTQSPDSLAV SLGERATINC | KSS--- QSVLYSSNNAN YLA | WYQQKPGQ PPNLLIY | W------ ASTRES | GVPDRFSGSGSG--- TDFTLTISSLQAEDVAVYYC | QQYYS-------TPCS | FGQGT KLEIK |
| iPS:451 131 | 21-225_160A7 | VK4\|B3/JK2 | DIVLTQSPDSPAV SLGERATINC | KSS--- QSVLHSSNNNN YLA | WYQQRPGH PHKLLIF | W------ ASTRES | GVLDRFSGSGYG--- TDFTLTISSLQAEDVAVYYC | QQYYS-------TPCS | FGQGT KLEIK |
| iPS:393 088 | 21-225_33D1 | VK4\|B3/JK2 | DIVMTQSPDSLSV SLGERATINC | KSI--- QSVLYRSNNKN YLT | WYQQKPGQ PRKLFIY | W------ ASTRES | GVLDRFSGSGSG--- TDFTLTISSLQAEDVAVYYC | QQYYS-------SPCS | FGQGT KLEIK |
| iPS:394 085 | 21-225_8B11 | VK4\|B3/JK2 | DIVMTQSPDSLAV SLGERATINC | KSS--- QNVLYNSNNNN YLA | WYQQKPGQ PPKLLIY | W------ ASTRKS | GVPDRFSGSGSG--- TYFLTLTISSLQAEDVAVYYC | QQYYT-------TPCS | FGQGT KLEIK |
| iPS:398 496 | 21-225_22D2 | VK4\|B3/JK2 | DIVMTQSPDSLAV SLGERATITC | KSS--- QSVLHSSNNNN YLA | WYQQKPGQ PPKLLIY | W------ ASTRES | GVPDRFSGSGSG--- TDFTLTISSLQAEDVAVYYC | QQYYS-------TPCS | FGQGT KLEIK |
| iPS:398 512 | 21-225_25E12 | VK4\|B3/JK2 | DIVMTQSPDPLAM SLGERATINC | KSS--- QSVLYHSNNYN YLA | WYQQKPGQ PPKLLIY | W------ ASTRES | GVPDRFSGSGSG--- TDFTLTISSLQAEDVAVYYC | QQYYS-------SPCS | FGQGT NLEIK |
| iPS:398 522 | 21-225_32A1 | VK4\|B3/JK2 | DIVMTQSPDSLAV SLGERATINC | KSS--- QSVLYSSNNYN YLA | WYQLKPGQ PPKLLIY | W------ ASTRKS | GVPDRFSGSGSG--- TDFTLTISSLQEDVAVYYC | QQYYT-------SPCS | FGQGT KLEIK |
| iPS:398 524 | 21-225_32A5 | VK4\|B3/JK2 | DIVMTQSPDSLAV SLGERATINC | KSS--- QSVLHSSNNNN YLA | WYQQKPGQ PPKLLIY | W------ ASTRES | GVPDRFSGSGSG--- TDFTLAISSLQAEDVALYHC | QQYYS-------SPCS | FGQGT GLEIK |
| iPS:398 538 | 21-225_34H7 | VK4\|B3/JK2 | DIVMTQSPDSLAV SLGERATINC | KSS--- QSVLYSSNMNYN YLA | WYQLKPGQ PPKLLIY | W------ ASTRKS | GVPDRFSGSGSG--- TDFTLTISSLQTEDVALYYC | QQYYT-------SPCS | FGQGT KLEIK |
| | Germline | | DVVMTQSPLSLPVS TLGQPASISC | RSS--- QSLVYSD GNTYLN | WFQQRPGQ SPRRLIY | | GVPDRFSGSGSG--- TDFTLKISRVEAEDVGTYYC | MQGTH | FGSGT KVEIK |
| VK2A17JK 4 | | | | | | | | | |
| iPS:468 854 | 21-225_72C4 | VK2\|A17/JK4 | DVVMTQSPLSLPV TLGQPASISC | RSG--- QSLVYSD- GNTYLN | WFQQRPGQ SPRRLIY | E------ VSKWDS | GVPDRFSGSGSG--- TNFTLKISRVEAEDVGVFYC | MQGTH------WPLT | FGGGT KVEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:437 250 | 21-225_148C6 | VK2|A17/ JK4 | DVVMTQSPLSLPV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGTH-----------WSLT | FGGGT KVEIK |
| iPS:437 252 | 21-225_148H1 | VK2|A17/ JK4 | DVVMTQSPLSLPV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGTH-----------WLLT | FGGGT KVEIK |
| iPS:437 254 | 21-225_149F2 | VK2|A17/ JK4 | DVVMTQSPLSLPV TLGQPASISC | RSS---QSLVYSD-GNTYLN | WFQQRPGQ SPRRLIY | K-------VSNWDS | GVPVRFSGSGSG---TDFTLKISRVEAEDVGIYYC | MQGTH-----------WPPT | FGGGT KVEIK |
| iPS:437 256 | 21-225_150F11 | VK2|A17/ JK4 | DVVMSQVPLSLPV TFGQPASISC | RSS---QSLVYSD-GNTSLN | WFQQRPGQ YPRRLIY | K-------VSNWDY | GVPVRFSGSGSG---TDFTLKISRVEAEDVGIYYC | MQGTH-----------WPPT | FGGGT KVEIK |
| iPS:437 268 | 21-225_177D2 | VK2|A17/ JK4 | DVVMTQSPLSLPV TLGQPASISC | RSS---QSLVYSD-GNTSLN | WFQQRPGQ SPRRLIY | K-------VSNWDS | GVPDRFSGSGSG---TDFTLKISRVEAEDVGVYYC | MQGTH-----------WPLT | FGGGT KVEIK |
| iPS:443 005 | 21-225_43F11_LC1 | VK2|A17/ JK4 | DVVMTQSPLSLPV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGTH-----------WPLT | FGGGT KVEIK |
| iPS:398 530 | 21-225_32G4 | VK2|A17/ JK4 | DVVMTQSPLSLSV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGT------------HWLT | FGGGT KVEIK |
| VK2jA17JK 3 | | Germline | DVVMTQSPLSLPV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGTH----------- | K_FR4 FGPGT KVDIK |
| iPS:468 856 | 21-225_77C9 | VK2|A17/ JK3 | DVVMTQSPLSLPV TLGQPASISC | RSS---QSLVYSV-GNTSLS | WFQQRPGQ SPRRLIY | K-------VSNWDS | GVPDRFSGSGSG---TDFTLKISRVEAEDVGVYYR | MQGTH-----------WPFT | FGPGT KVDIK |
| iPS:392 936 | 21-225_28B6 | VK2|A17/ JK3 | DVVMTQSPLSLPV TLGQPASISC | RSS---QSLVYSD-GNTYLN | WFQQRPGQ SPRRQIY | K-------VSNWDS | GVPDRFSGSGSG---TDFTLNISRVEAEDVGIYFC | MHCT------------HWLL | FGPGT KVDIK |
| VK2jA17JK 5 | | Germline | DVVMTQSPLSLPV TLGQPASISC | RSS---QSLVYSD-GNTYLN | WFQQRPGQ SPRRLIY | K-------VSNWDS | GVPDRFSGSGSG---TDFTLKISRVEAEDVGVYYC | MQGTH----------- | K_FR4 FGQGT RLEIK |
| iPS:472 741 | 21-225_30D9_LC1 | VK2|A17/ JK5 | DVVMTQSPLSLPV TLGQPASISC | RSS---QSLVSSD-GNTFLN | WFQQRPGQ SPRRLIY | K-------VSNWDS | GVPDRFSGSGSG---TDFTLKISRLEAEDVGVYYC | LQGTH-----------WPLT | FGQGT RLEIK |
| iPS:437 294 | 21-225_216D5 | VK2|A17/ JK5 | DVVMTQSPLSLPV TLGQPASISC | RSS---QSLVYSD-GNTYLN | WFQQRPGQ SPRRLIY | K-------VSNWDS | GVPDRISGSGSG---TDFTLKISRVEAEDVGIYYC | MQGA------------HWFT | FGQGT RLEIK |
| iPS:472 732 | 21-225_2B10_LC1 | VK2|A17/ JK5 | DVVMTQSPLSLPV TLGQPASISC | RSS---QSLVYSD-GDTYLN | WFQQRPGQ SPRRLIY | K-------VSNWDS | GVPDRFSGSGSG---TGFTLKISRVEAEDVGVYYC | IQGTH-----------WPFP | FGQGT RLEIK |
| iPS:398 508 | 21-225_24B1 | VK2|A17/ JK5 | DVVMTQSPLSLPV TLGQPASISC | RSS---QSLVYSD-GNTYLN | WFQQRPGQ SPRRLIY | K-------VSNWDS | GVPDRFSGSGSG---TDFTLKISWVEAEDVGVCYC | MQGAH-----------WPPIT | FGQGT RLEIK |

Figure 51 (Continued)

| | VK2A17/JK5 | | | K_CDR1 | | K_CDR2 | | K_CDR3 | | |
|---|---|---|---|---|---|---|---|---|---|---|
| iPS:423 019 | 21-225_31D12 LC1 | Germline | DVVMTQSPLSLPV TLGQPASISC | RSS---QSLIYSD-GNTFLN | WFQQRPGQ SPRRLIY | K------VSNWDS | GVPDRFSGSGSG-TDFTLKISRLEAEDVGIYYC | MQGTH------WPLT | FGQGT PLEIK |
| | | K_FR1 | | K_CDR1 | K_FR2 | K_CDR2 | K_FR3 | K_CDR3 | | K_FR4 |
| iPS:433 897 | 21-225_43C2 | VK1L5J K1 | DIQMTQSPSSVSA SVGDRVTITC | RAS---QGIS-----DWLA | WYQQKPGK APRLLIY | A------ASSLQS | GVPSRFSGSGSG-TDFTLTISNLQPEDFATYYC | QQTNS------FPWT | FGQGT KVEIK |
| iPS:433 903 | 21-225_43H4 | VK1L5J K1 | DIQMTQSPSPSVSA SVGDRVTITC | RAS---QGII-----NWLA | WYQQKPGR APKLLIY | A------ASSLQS | GVPSRFSGSGSG-TDFTLTISNLQPEDFATYYC | QQTNS------FPWT | FGQGT KVEIK |
| iPS:433 911 | 21-225_43E8 | VK1L5J K1 | DIQMNQSPSSVSA SVGDRVTITC | RAS---QGIS-----NWLA | WYQQKPGR APKLLIY | A------ASSLQS | GVPSRFSGSGSG-TDFTLTISNLQPEDFATYYC | QQTNS------FPWT | FGQGT KVEIK |
| iPS:433 941 | 21-225_44D10 | VK1L5J K1 | DIQMTQSPSSVSA SVGDRVTITC | RAS---QGIS-----DWLA | WYQQKPGK APRLLIY | A------ASSLQS | GVPSRFSGSGSG-TDFTLTISNLQPEDFATYYC | QQSNS------FPWT | FGQGT KVEIK |
| iPS:433 945 | 21-225_44C12 | VK1L5J K1 | DIQMTQSPSSVSA SVGDRVTITC | RAS---QGIS-----NWLA | WYQQKPGK APKLLIS | A------AFSLQS | GVPSRFSGSGSG-TDFTLSISSLQPEDFATYYC | QQTNS------FPWT | FGQGT KVEIK |
| iPS:433 957 | 21-225_45F8 | VK1L5J K1 | DIQMNQSPSSVSA SVGDRVTITC | RAS---QGIS-----DWLA | WYQQKPGK APRLLIY | G------ASSLQS | GVPSRFSGSGSG-TDFTLTISNLQPEDFATYYC | QQTNS------FPWT | FGQGT KVEIK |
| iPS:433 973 | 21-225_46A6 | VK1L5J K1 | DIQMTQSPSSVSA SVGDRVTITC | RAS---QGIS-----NWLA | WYQQKPGK VPKLLIY | A------ASSLQS | GVPSRFSGSGSG-TDFTLTISNLQPEDFATYYC | QQVNS------FPWT | FGQGT KVEIK |
| iPS:433 993 | 21-225_47G7 | VK1L5J K1 | DIQMTQSPSSVSA SVGDEVTITC | RAS---QGIS-----NWLA | WYQQKPGK APKLLIP | A------ASNLQS | GVPSRFSGSGSG-TDFTLTISSLQPADFATYYC | QQANS------FPWT | FGQGT KVEIK |
| iPS:434 007 | 21-225_48D7 | VK1L5J K1 | DIQMTQSPSSVSA SVGDRVTITC | RAS---QNIT-----SWLA | WYQQKPGK APKLLIY | S------ASSLQN | GVPSRFSGSGSG-TDFTLTISSLQPEDFVTYYC | QQANS------FPWT | FGQGT KVEIK |
| iPS:434 063 | 21-225_51G7 | VK1L5J K1 | DIQMTQSPSSVSA SVGDRVTITC | RAS---QDIS-----SWLA | WYQQKPGR APKVLIY | A------ASSLQS | AVPSRFSGSGSG-TDFTLTISSLQPEDFATYYC | QQAHS------FPWT | FGQGT KVEIK |
| iPS:434 083 | 21-225_52H2 | VK1L5J K1 | DIQMTQSPSSVSA SVGDRVTITC | RAS---QNIT-----NWLA | WFQQKPGK APKLLIY | T------FSNLQS | TDFPSRFSGSGSG-TDFTLTISSLQPEDFATYYC | QQTNS------FPWT | FGHGT KVEVK |
| iPS:434 133 | 21-225_54G3 | VK1L5J K1 | DIQMTQSPSSVSA SVGDRVTITC | RAS---QGIS-----NWLA | WYQQKPGK APKLLIY | T------TSSLQS | GVPSRPSGSGSG-TDFTLTISSLQGSSP------FPWT | QQANS------FPWT | FGQGT KVEIK |
| iPS:434 221 | 21-225_60A11 | VK1L5J K1 | DIQMTQSPSSVSA SVGDRVTITC | RAS---QVIS-----NWLA | WYQLKPGK APKLLIY | T------ASSLQS | GVPSRFSGNESG-TDFTLTISSLQPEDFATYYC | QQANS------FPWT | FGQGT KVEIK |
| iPS:434 283 | 21-225_57F8 | VK1L5J K1 | DIQMTQSPSSVSA SVGDRVTITC | RAS---QGIS-----NWLA | WYQQKPGK APKLLIY | T------ASSLQS | GVPSRFSGNESG-TDFTLTISSLQPEDFATYYC | QQANS------FPWT | FGQGT KVEIK |
| iPS:435 711 | 21-225_174G4 | VK1L5J K1 | DIQMTQSPSSVSA SVGDRVTITC | RAS---QGVN-----DWLA | WYQQKPGR APKLLIY | D------ASSLQS | GVPSRFSGSGSG-TDFTLTISSLQPEDFATYYC | QQANS------FPWT | FGQGT KVEIK |
| iPS:435 715 | 21-225_171A8 | VK1L5J K1 | AIQMTQSPSSVSA SVGDRVTITC | RAS---QGIS-----NWLA | WYQQKPGK APNLMIH | A------AFSLQG | GVPSRFSGSGSG-TDFTLTISSLQPEDFATYYC | QQTNS------FPWT | FGQGT KVEIK |
| iPS:435 717 | 21-225_171A9 | VK1L5J K1 | DIQMTQSPSSVSA SVGDRVTITC | RAS---QDIT-----TWLA | WYQQKPGK APKLLIY | D------ASSLQS | AVPSRFSGSGSG-TDFTLTISSLQPEDFATYYC | LQTNS------FPWT | FGQGT KVEIK |
| iPS:435 739 | 21-225_174G7 | VK1L5J K1 | DIQMTQSPSSVSA SVGDRVTITC | RAS---QGIS-----NWLA | WYQLKPGK APNLLIH | A------AFSLQG | GVPSRFSGSGSG-TDFTLTISSLQPEDFATYYC | QQTNS------FPWT | FGQGT KVEIK |
| iPS:435 749 | 21-225_175C10 | VK1L5J K1 | DIQMTQSPSSVSA SVGDRVTITC | RAS---QGIT-----DWLA | WYQQKPGK APKLLIY | A------ASSLQS | GVPSRFSGSGSG-TDFTLTISSLQPEDFATYYC | QQTNS------FPWT | FGQGT KVEIK |
| iPS:435 775 | 21-225_178A5 | VK1L5J K1 | DIQMTQSPSSVSA SVGDRVTITC | RAS---QGIS-----NWLA | WYQQKPGK APKLLIY | A------ASSLQS | GVPSRFNGSGSG-TDFTLTISSLQPEDFATYYC | QQANS------LPWT | FGQGT KVEIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:435777 | 21-225_178F7 | VK1|L5/J K1 | DIQMTQSPSSVSA SVGDRVTITC | RAS--QDIT-----DWLA | WYQQKPGK APKLLIS | A-------ASSLQS | GVPSRFSGSGSG-TDFTLAISSLQPEDFATYYC | QQANS---------LPWT | FGQGT KVEIK |
| iPS:435783 | 21-225_179G1 | VK1|L5/J K1 | DIQMTQSPSSVSA SVGDRVTITC | RAS--QDIS-----DWLA | WYQQKSGK APKLLIS | A-------ASSLQS | GVPSRFGGSGSG-TDFTLTISSLQPEDFATYSC | QQANS---------LPWT | FGQGT KVEIK |
| iPS:435875 | 21-225_190B9 | VK1|L5/J K1 | DIQMTQSPSSVSA SVGDRVTITC | RAS--QGIN-----NWLA | WYQQKPGK APKLLIY | G-------VSSLQS | GVPSGFSGSGSG-TDFTLTISSLQPEDFATYSC | QQANS---------FPWT | FGQGT KVEIK |
| iPS:435895 | 21-225_188E8 | VK1|L5/J K1 | DIQMTQSPSSVSA SVGDRVTITC | RAN--QDIS-----SWLA | WYQQKPGK APKLLIY | A-------ASNLQS | GVPSGFSGSGSG-TDFTLTISSLQPEDFATYYC | QQANS---------FPWT | FGQGT KVEIK |
| iPS:435909 | 21-225_190H3 | VK1|L5/J K1 | DIQMTQSPSSVSA SVGDRVTITC | RAS--QGIN-----NWLA | WYQLKPGK APKLLIY | A-------VSSLQS | GVPSRFSGSGSG-SEFTLTISSLQPEDFATYHC | QQANS---------LPWT | FGQGT KVEIK |
| iPS:436013 | 21-225_193F2 | VK1|L5/J K1 | DIQMTQSPSSVSA SVGDRVTITC | RAS--QGIN-----NWLA | WYQQKPGK APKLLIY | G-------VSSLQS | GVPSRFSGSGSG-TDFTLTISSLQPEDFATYSC | QQANS---------FPWT | FGQGT KVEIR |
| iPS:436068 | 21-225_194F7 | VK1|L5/J K1 | DIQMTQSPSSVSA SVGDRVTITC | RAS--QGIS-----RWLA | WFQQKPGK APKILIY | A-------ASSLQS | GVPSRFSGSGSG-TDFTLTISSLQPEDFATYYC | QQANS---------FPWT | FGQGT KVEIK |
| iPS:436100 | 21-225_195G1 | VK1|L5/J K1 | DIQMTQSPSSVSA SVGDRVTITC | RAS--QGIN-----NWLA | WYQQKPGK APKLLIY | G-------VSSLQS | GVPSRFSGSGSG-TDFTLTISSLQPEDFATYSC | QQANS---------FPWT | FGKGT KVENQ |
| iPS:436116 | 21-225_196B9 | VK1|L5/J K1 | DIQMTQSPSSVSA SVGDRVTITC | RAS--QGIS-----NCLA | WYQQKPGK APKLFIC | A-------ASSLQS | AVPSRFSGSGSG-TDFTLTISSLQPEDFATYYC | QQGDS---------FPPT | FGQGT KVEIK |
| iPS:436160 | 21-225_197C9 | VK1|L5/J K1 | DIQMTQSPSSVSA SVGDRVTITC | RAS--QGIS-----NWLA | WFQQKPGK APQLLIY | A-------ASSLQS | GVPSRFSGSGSG-TDFSLTISSLQPEDFATYYC | QQANS---------FPWT | FGQGT KVEIK |
| iPS:436546 | 21-225_224D6 | VK1|L5/J K1 | DIQMTQSPSSVSA SVGDRVTITC | RAS--QGII-----SWLA | WYQQKPGK APKFLIY | A-------ASSLQS | GVPSRFSAGSGSG-TEFTLTISSLQPEDFATYYC | QQANS---------FPWT | FGQGT KVEIK |
| iPS:436632 | 21-225_227E4 | VK1|L5/J K1 | DIQMTQSPSSVSA SVGDRVTITC | RAS--QGII-----NWLA | WYQQKPGK APKLLIY | G-------ASSLQS | GVPSRFSGSGSG-TDFTLTISSLQPEDFATYYC | QQANS---------FPRT | FGQGT KVEIK |
| iPS:436650 | 21-225_17A4 | VK1|L5/J K1 | DIQMTQSPSSVSA SVGDRVTITC | RAS--QGIG-----NWLA | WYQQKPGK APKLLIF | A-------ASSLQS | GVPSRFSGSGSG-TDFTLTISSLQPEDFVTYYC | QQANS---------FPRT | FGQGT KVEIK |
| iPS:392728 | 21-225_20F7 | VK1|L5/J K1 | DIQMTQSPSSVSA SVGDRVTITC | RAS--QGIS-----SWLA | WYQQKPGK APKLLIY | A-------ASSLQS | GVPSRFSGSGSG-TDFTLTISSLQPEDFATYYC | QQANS---------FPRT | FGQGT KVEIK |
| iPS:392916 | 21-225_27C5 | VK1|L5/J K1 | DIQMTQSPSSVSA SVGDRVTITC | RAS--QGIS-----SWLA | WYQQKPGK APKFLIY | G-------ASSLQS | GVPSRFSASGSG-TEFTLTISSLQPEDFATYYC | QQYDS---------FPRT | FGQGT KVEIK |
| iPS:392956 | 21-225_27A11 | VK1|L5/J K1 | DIQMTQSPSSVSA SVGDRVTITC | RAS--QGIS-----SWLA | WYQQKPGK APKLLIY | A-------ASSLQS | GVPSRFSGSGSG-TDFTLTISSLQPEDFATYCC | QQSDS---------FPRT | FGQGT KVEIK |
| iPS:393014 | 21-225_26D12 | VK1|L5/J K1 | DILMIQSPSSVSA SVGDRVTITC | RAS--QGIS-----SWLA | WYQQKPGK APKLLIY | G-------ASSLQS | GVPSRFSASGSG-TDFTLTISSLQPEDFATYYC | QQSDS---------FPRT | FGQGT KVEIK |
| iPS:393028 | 21-225_25D7 | VK1|L5/J K1 | DIQMTQSPSSVSA SVGDRVTITC | RAS--QDIF-----DWLA | WYQQKPGT APKLLIY | A-------ASSLQS | GVPSRFSGSGSG-TNFTLTVSGLQPEDFATYYC | QQAYS---------FPWT | FGQGT KVEIR |
| iPS:393152 | 21-225_25B3 | VK1|L5/J K1 | DIQMTQSPSSVFC SVGDRVTITC | RAS--QGIS-----NWLA | WYQQKPGK APKLLIY | G-------ASSLQS | GVPSRFSGSGSG-TDFTLTISSLQPEDFATYYC | QQSDS---------FPRT | FGQGT KVEIK |
| iPS:393810 | 21-225_5A4 | VK1|L5/J K1 | DIQMTQSPSSVSA SVGDRVTITC | RAS--QGIS-----TWLA | WYQQKPGK APKLLIY | D-------ASSLQS | GVPSRFSGSGSG-TDFTLTISSLQPEDFATYYC | QQANS---------FPWT | FGQGT KVEIK |
| VK2A19/JK3 | Germline | | | | | | | | |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:433 943 | 21-225_44E10 | VK2|A19/ JK3 | DIVMTQSPLSLPV TPGEPASISC | RSS--QSLLHSN-GYSYLE | WYLQKPGQ SPQLLIY | L------GSNRAS | GVPDRFSGSGSG--TDFTLKISRVEAEDVGVYYC | MQTLQ------- | ---TPFT FGPGT KVDIK |
| iPS:433 989 | 21-225_47C7 | VK2|A19/ JK3 | DIVMTQSPLSPPV TPGEPASISC | RSS--QSLLHSN-GYNYLE | WYLQKSGQ SPQFLIY | L------GENRAS | GVPDRFTGSGSG--TDFTLKISRVEAEDVGVYYC | MQVLQ------- | ---TPFT FGPGT KVDIK |
| Germline | VK1|O12| K3 | | | | | | | | |
| iPS:433 999 | 21-225_48D1 | VK1|O12/ JK3 | DIQMTQSPSSLSA SVGDRVNITC | RAS--QSIS---SYLI | WYQQKPGK APKLLIY | A------ASSLQS | GVPSRFSASGSG--TDFTLTISSLQPEDFASYYC | QQSNS------- | ---IPFT FGPGT KVDIK |
| iPS:434 003 | 21-225_48C3 | VK1|O12/ JK3 | DIQMTQSPSSLSA SVGDRVNITC | RAS--QSII---SYLI | WYQQKPGK APRLLIY | A------ASSLQS | GVPSRFSASGSG--TDFLTISSLQPEDFASYYC | QQTNS------- | ---IPFT FGPGT KVDIK |
| iPS:434 037 | 21-225_49G12 | VK1|O12/ JK3 | DIQMTQSPSSLSA SVGDRVTITC | RSS--QSIS---TYLM | WYQQKPGK APKLLIY | A------ASSLQI | GVPSEFSASGSG--TDFTLTISSLQPEDFATYYC | QQSYS------- | ---IPFT FGPGT KVDIK |
| iPS:434 041 | 21-225_50H8 | VK1|O12/ JK3 | DIQMTQSPSSLSA SVGDRVNITC | RAS--QSIS---SYLI | WYQQKPGK APKLLIY | A------ASSLQS | GVPSRFSASGSG--TDFTLTISSLQPEDFASYYC | QQSNS------- | ---LPFT FGPGT KVDIK |
| iPS:434 045 | 21-225_50H10 | VK1|O12/ JK3 | DIQMTQSPSSLSA SVGDRVNITC | RAS--QSIS---SYLI | WYQHKPGK APRLLIY | A------ASSLQS | GVPSRFSGSESG--TDFTLTISSLQPEDFTTYYC | QQSNS------- | ---IPFT FGPGT KVDIK |
| iPS:434 049 | 21-225_50B12 | VK1|O12/ JK3 | DIQMTQSPSSLSA SVGDRVTITC | RAS--QSIS---SYLN | WYQQKPGK APKLLIY | A------ASSLQS | GVPSRFSASGSG--TDFTLTISSLQPEDFTTYYC | QQSYI------- | ---APFT FGPGT KVDIK |
| iPS:434 073 | 21-225_51H10 | VK1|O12/ JK3 | DIQMTQSPSSLSA SVGDRVTITC | RAS--QSIS---TYLM | WYQQKPGK APKLLIY | A------ASSLQS | GVPSRFSGSGSG--TDFLPISSLQPEDFAIYFC | QQSFS------- | ---IPFT FGPGT KVDIK |
| iPS:434 107 | 21-225_53E2 | VK1|O12/ JK3 | DIQMTQSPSSLSA SVGDRVTITC | RAS--QSFS---HYLN | WYQQKPGK APNLLIE | A------ASSLQS | GVPSRFSGSGSG--SDFTLPISSLQPEDFAIYFC | QQSFS------- | ---TPFT FGPGT KVDIK |
| iPS:434 181 | 21-225_56B2 | VK1|O12/ JK3 | DIQMTQSPSSLSA SVGDRVTITC | RAS--QSFS---HYLN | WYQQKPGK APNLLIF | V------VSSLQS | GVPSRFSGSGSG--TDFTLTISSLQPEDFAIYFC | QQSYS------- | ---TPFT FGPGT KVDIK |
| iPS:434 225 | 21-225_60E12 | VK1|O12/ JK3 | DIQMTQSPSSLSA SVGDRVTITC | RAS--QSIS-----SYLN | WYQQKPGK APKLLIY | A------ASSLQS | GVPSRFSGSGSG--TDFTLTISSLQPEDFAPYYC | QQSYN------- | ---ISFT FGPGT KVDIK |
| iPS:434 227 | 21-225_61A1 | VK1|O12/ JK3 | DIQMTQSPSSLSA SVGDRVTITC | RAS--QSIS---SYLN | WYQQKPGK APKLLIY | A------ASSLQS | GVPSRLSGSGSG--TDFTLTISSLQPEDFAPYYC | QQSYN------- | ---ISFT FGPGT KVDIK |
| iPS:434 245 | 21-225_62H1 | VK1|O12/ JK3 | DIQMTQSPSSLSA YVGDRVTITC | RAG--QNIF---NYLN | WYQQKPGK APKLLIF | A------ASSLQS | GVPSRFSGSGSG--TDFTLTISSLQPEDFATYYC | QQSYS------- | ---TPFT FGPGT KVDIK |
| iPS:434 267 | 21-225_57F2 | VK1|O12/ JK3 | DIQMTQSPSSIPA SVGDRVTITC | RAS--QNIR---KYLI | WYQFLPGK APKLLIY | T------ASTLQS | GVPSRFSGSGSG--TDFTLTISSLQPEDFAPYYC | QQSYN------- | ---ISFT FGPGT KVDIK |
| iPS:434 323 | 21-225_62H8 | VK1|O12/ JK3 | DIQMTQSPSSLSA SVGDRVTITC | RAS--QTIL---SYLN | WYQQNPGK APKLLIY | G------VSSLQS | GVPSRLSGSGSG--TDFTLTISSLQPEDFATYYC | QQSYS------- | ---TPFT FGPGT KVDIK |
| iPS:434 379 | 21-225_66A9 | VK1|O12/ JK3 | DIQMTQSPSSLSA SVGDRVTITC | RAS--QNIF---SYLN | WYQQKPGK APKLLIF | A------ASSLQS | GVPSRFSGSGSG--TDFTLTISSLQPEDFATYYC | QQTYS------- | ---VPFT FGRGT KVDFK |
| iPS:434 417 | 21-225_69C8 | VK1|O12/ JK3 | DIQMTQSPSSLSA SVGDRVIFTC | RAG--QTIY---NYLN | WYQQKPGK APKVLIY | V------ASSLQS | GVPSRFSGSGSG--TDFLVISSLQPEDFATYYC | QQSYS------- | ---TPFT FGPGT KVDIK |
| iPS:435 545 | 21-225_158F4 | VK1|O12/ JK3 | DIQMTQSPSSLSA SVGDRVTITC | RAS--QNIR---KYLI | WYQQKPGK APKLLIY | T------ASTLQS | GVPSRFSGSGSG--TDFTLTISSLQPEDFATYYC | QQSYN------- | ---ISFT FGPGT KVDIK |
| iPS:435 793 | 21-225_180F8 | VK1|O12/ JK3 | DIQMTQSPSSLSA SVGDGVIITC | RAS--QTIL---SYLN | WYQQKPGK APKLLIY | G------VSSLQS | GVPSRLSGSGSG--TDFLITISSLQPEDFAIYYC | QQSYS------- | ---TPFT FGPGT KVDIK |
| iPS:436 504 | 21-225_222H4 | VK1|O12/ JK3 | DIQMTHSPSSLSA SVGDRVTITC | RAS--QNIS---NYVN | WYQQKPGK APKFLIY | T------ASSLQS | GVSSRFSGSGSG--TDFLTISSVHRDDFAIYYC | QQYYF------- | ---TPFT FGRGT KVDIK |

Figure 51 (Continued)

| ID | V/J | Seq1 | Seq2 | Seq3 | Seq4 | Seq5 | Seq6 | Seq7 | Seq8 |
|---|---|---|---|---|---|---|---|---|---|
| iPS:436 510 | 21-225_222H8 | VK1O12/ JK3 | DIQMTHSPSSLSA SVGDRVTITC | RAS--QNIS- ---NYVN | WYQQKPGK APKFLIY | I------- ASSLQS | GVSSRFSGSGSG-- TDFTLTISSVHRDDFATYYC | QQYYF------ | ----TPFT | FGPGT KVDIK |
| iPS:437 230 | 21-225_62H10 | VK1O12/ JK3 | DIQMTQSPSSLSA SVGDRVTITC | RAS--QSIT- ---SYLN | WYQQKPGK VPKLLIS | T------- ASSLQS | GVPSRFSGSGSG-- TDFTLTISSLQPEDFATYYC | QQSHS------ | ----FPFT | FGPGT NVDFK |
| iPS:448 906 | 21-225_72G9 | VK1O12/ JK3 | DIQMTQSPSSLSA SVGDRVTITC | RAS--QSIT- ---SYLN | WYQQKPGK APKLLIY | T------- ASSLQS | GVPSRFSGSGSG-- TDFTLTISSLQPEDFATYYC | QQSHS------ | ----FPFT | FGPGT KVDIK |
| iPS:392 652 | 21-225_17C6 | VK1O12/ JK3 | DIQMTQSPSSLSA SVGDRVTITC | RAS--QSIN- ---TYLN | WYQQKPGK APKLLIY | A------- ASSLQS | GVPSRFSGSGSG-- TDFTLTISSLQPEDFATYYC | QQSYR------ | ----TPFFT | FGPGT KVDIK |
| iPS:392 660 | 21-225_19B3 | VK1O12/ JK3 | DIQMTQSPSSLSA SVGDRITIIC | RAG--QNII- ---NYLN | WYQQKPGK APNLLIY | V------- ASSLQS | GVPSRFNGSGSG-- TDFTLTISSLQPEDFATYYC | QQSYS------ | ----TPFT | FGPGT KVDIK |
| iPS:392 668 | 21-225_17B4 | VK1O12/ JK3 | DIQMTQSPSSLSA SVGDRVTITC | RAS--QNIS- ---SYLN | WYQQKPGK APKLLIF | G------- ASSLQT | GVPSRFSGSGSG-- TDFTLTISSLQPEDFATYYC | QQSYR------ | ----TPFFT | FGPGT KVDIK |
| iPS:392 678 | 21-225_20F3 | VK1O12/ JK3 | DIQMTQSPSSLSA SVGDRVSITC | RAS--QSIS- ---SYLY | WYQQKPGK APKLLIY | A------- ASSLQS | GVPSRFSGSGSG-- TDFTLTISSLQPEDFATYYC | QQSYS------ | ---APPFT | FGPGT KVDIK |
| iPS:392 694 | 21-225_19A5 | VK1O12/ JK3 | DIQMTQSPSSLSA PVGDRVSITC | RAS--QNII- ---NYLN | WYQQKPGK APKLLID | V------- ASNLQG | GVPSRFSGSGSG-- TDFTLTINSLQPEDFATYYC | QQSYS------ | ----TPFT | FGPGT KVDIK |
| iPS:392 696 | 21-225_20A4 | VK1O12/ JK3 | DIQMTQSPASLSA SVGDRVTITC | RAS--QSII- ---NYLN | WYQQRPGK SPKLLIY | A------- ASSLRS | GVPSRFSGRGSG-- TDFTLTISSLQPEDFATYYC | QQSYR------ | ----TPLFT | FGPGT KVDIK |
| iPS:392 702 | 21-225_17F7 | VK1O12/ JK3 | DIQMTQSPSSLSA SVGDRVTITC | RAS--QTIS- ---SFLN | WYQQKPGK APKLLIY | A------- ASSLQS | GVPSRFSGSGSG-- TDFTLTISSLQPEDFATYYC | QQSYR------ | ----TPFFT | FGPGT KVDIK |
| iPS:392 704 | 21-225_17F11 | VK1O12/ JK3 | DIQMTQSPSSLSA SIGDRVSITC | RAS--RTIN- ---NYLN | WYQQKPGK APKLLIF | I------- ISSLQS | GVPSRFSGSGSG-- TDFTLTISSLQPEDFATYYC | QQTYS------ | ----TPLFA | FGPGT KVDIK |
| iPS:392 720 | 21-225_17A12 | VK1O12/ JK3 | DIQMTQSPSSLSA SVGDRVTITC | RAS--QSIS- ---SYLN | WYHQKPGK APKLLIY | A------- ASSLQS | GVPSRFSGSGSG-- TDFTLTINSLQPEDFATYYC | QQSYN------ | ----TPLFT | FGPGT KVDFK |
| iPS:392 722 | 21-225_18E12 | VK1O12/ JK3 | DIQMTQSPSSLSA SVGDRVTITC | RAS--QSIS- ---SYLN | WYQQKPGK APTLLIY | A------- ASSLQS | GVPSRFSGSGSG-- TDFTLTISSLQPEDFATYYC | QQSYR------ | ----TPFFT | FGPGT KVDIK |
| iPS:392 760 | 21-225_22G3 | VK1O12/ JK3 | DIQMTQSPSSLSA SVGDRVTITC | RAS--QSIS- ---NYLN | WYQQKPGK APKLLIF | A------- ASSLQS | GVPSRFSGSGSG-- TDFTLTISGLQPEDFATYYC | QQSFR------ | ----TPFFT | FGPGT KVDIK |
| iPS:392 762 | 21-225_22G5 | VK1O12/ JK3 | DIQMTQSPSSLCA SVGDRVTITC | RAS--QTIS- ---SHLN | WYQRKPGK APKLLIY | A------- ASSLQN | GVPSRFSGSGSG-- TDFTLTISSVQPEDFATYYC | QQSYN------ | ----ISFT | FGPGT KVDIK |
| iPS:392 764 | 21-225_22G10 | VK1O12/ JK3 | DIQMTQSPSSLSA SVGDRVTITC | RAS--QSIF- ---SYLN | WYQQKPGK APKLLIY | A------- ASSLQS | GVPSRFSGSGSG-- TDFTLTISSLQPEDFATYYC | QQSYR------ | ----TPLFT | FGPGT KVDFK |
| iPS:392 812 | 21-225_21F4 | VK1O12/ JK3 | DIQMTQSPSSLSA SVGDRVTITC | RAS--QNIG- ---SYLN | WYQQKPGK APKLLIF | A------- ASSLQS | GIPSRFSGSGSG-- TDFTLTISSLQPEDFATYYC | QQSYR------ | ----TPFT | FGPGT KVDIK |
| iPS:392 816 | 21-225_22E4 | VK1O12/ JK3 | DIQMTQSPSSLSA SVGDRVTITC | RAS--QNIS- ---NYLN | WYQQKPGK APKLLIY | A------- ASSLQS | GVPSRFSGSGSG-- TDFTLTISSLQPEDFATYYC | QQSYN------ | ----TPLFT | FGPGT KVDIK |
| iPS:392 830 | 21-225_21A5 | VK1O12/ JK3 | DIQMTQSPSSLCA SVGDRVTITC | RAS--QTIS- ---SHLN | WYQRKPGK APKLLIY | A------- ASSLQN | GVPSRFSGSGSG-- TDFTLTISSVQPEDFATYYC | QQSYN------ | ----ISFT | FGPGT KVDIK |
| iPS:392 852 | 21-225_21A2 | VK1O12/ JK3 | DIQMTQSPSSLSA SVGDRVTITC | RAS--QNIS- ---SYLN | WYQQKPGK APKLLIY | A------- ASVLQH | GVPSRFSGSGSG-- TDFTLIIFSLQPEDFATYYC | QQSYR------ | ----TPFFT | FGPGT KVDFK |
| iPS:392 878 | 21-225_22C5 | VK1O12/ JK3 | DIQMTQSPASLSA SVGDRVTITC | RAS--QNIF- ---SYLN | WYQQKPGK APKLLIY | A------- ASSLQS | GVPSRFSGRGSG-- TDFTLTISSLQPEDFATYYC | QQSYR------ | ----TPLFT | FGPGT KVDIK |
| iPS:392 902 | 21-225_22D5 | VK1O12/ JK3 | DIQMTQSPSSLSA SVGDRVTITC | RAS--QSIS- ---SYLN | WYHQKPGK APKLLIY | A------- ASSLQS | GVPSRFSGSGSG-- TDFTLTINSLQPEDFATYYC | QQSYS------ | ----TPLFT | FGPGT KVDFK |
| iPS:392 984 | 21-225_30E11 | VK1O12/ JK3 | DIQMTQSPSSLSA SVGDRVTITC | RAS--QSIS- ---NYLN | WYQQQTCK APKFLIY | A------- ASSLQS | GVPSRFSGSGSG-- TDFTLTISSLQPEDFATYYC | QQSYS------ | ----TPFT | FGPGT KVDIK |

Figure 51 (Continued)

| ID | Clone | Germline | K_FR1 | K_CDR1 | K_FR2 | K_CDR2 | K_FR3 | K_CDR3 | K_FR4 |
|---|---|---|---|---|---|---|---|---|---|
| iPS-393 114 | 21-225_33G12 | VK1|O12/ JK3 | DIQMTQSPSSLSA SVGDRVTITC | RAS--QSIS------NYLN | WYQQKPGK APKFLIY | A------ ASSLQS | GVPSRFSGSGSG--- TDFTLTISSLQPEDFATYYC | QQSYS-------TPFT | FGPGT KVDIK |
| iPS-393 824 | 21-225_10F12 | VK1|O12/ JK3 | DIQMTQSPSSLSA SVGDRVTITC | RAS--QNIS------SYLN | WYQQKPGK APKLLIY | A------ ASSLQS | GVPSRFSGSGSG--- TDFTLTISSLQPEDFATYYC | QQSYN-------TPFFT | FGPGT KVDIK |
| iPS-393 848 | 21-225_4H2 | VK1|O12/ JK3 | DIQMTLSPSSLSA SVGDRVTITC | RAI--QNIS------SYLN | WYQQKPGK APKIVIY | A------ ASSLQS | GVPSRFSGSRGSG--- TDFTLTIGCVQREDFATYYC | QQSYR-------TPLFT | FGPGT KVDIK |
| iPS-393 862 | 21-225_5G2 | VK1|O12/ JK3 | DIQMTQSPSPSA SVGDRVTITC | RAS--QNII------SYLN | WYQQKPGK ARKLVIY | A------ ASSLQS | GVPSRFSGSGSG--- TDFTLNIRSLQPEDFATYYC | QQSYS-------TPLFT | FGPGT KVDIK |
| iPS-393 888 | 21-225_3E3 | VK1|O12/ JK3 | DIQMTQSPSSLSA SVGDRVTIE | RAS--QSIR------SYLN | WYQQKPGK AHKLVEY | G------ TSSLQS | GVPSRFSGSGSG--- TDFTLTISSLQPEDFATYYC | QQSYS-------TPLFT | FGPGT KVDIK |
| iPS-393 890 | 21-225_4B1 | VK1|O12/ JK3 | DIQMTQSPSSLSA SVGDRVTITC | RAS--HTIR------TYLN | WYQQKPGK APKLLIY | A------ ASSLQS | GVPSRINGSGSG--- TDFTLTITNLQPEDFATYYC | QQSYN-------ISFT | FGPGT KVDIK |
| iPS-393 898 | 21-225_5F7 | VK1|O12/ JK3 | DIQMTQSPSPSA SVGDRVTITE | RAS--QTIS------SYLN | WYQQKPGK APKLLIS | A------ ASSLQS | GVPSRFSGSGSG--- TDFTLTISSLQPEDFATYYC | QQSYR-------TPLFT | FGPGT KVVIK |
| iPS-393 904 | 21-225_8H11 | VK1|O12/ JK3 | DIQMTQSPSSLSA FVGDRVTITC | RAS--QNII------SYLN | WYQQKPGK APNLMIY | V------ TSSLHS | GVPSRFSGSGSG--- TDFSLTISSLQPEDFATYYC | QQTYS-------TPFT | FGPGT KVDIK |
| iPS-393 936 | 21-225_14A11 | VK1|O12/ JK3 | DIQMTQSPSSLSA SIGDRVTITC | RAS--QSIS------SYLN | WYQQKPGK APKLLIF | A------ ASSLQN | GVPSRFSGSGSG--- TDFTLTISSLQPEDFATYYC | QQTYS-------SPPFT | FAPGT KVDIK |
| iPS-393 980 | 21-225_6D3 | VK1|O12/ JK3 | DIQMTQSPSSLSA SVGDRVTITC | RTS--QSIS------TYLN | WYQQKPGK APKLLIF | A------ ASSLQN | GVPSRFSGSGSG--- TDFTLTISSLQPEDFATYFC | QQSYR-------TPFFT | FGPGT KVDIN |
| iPS-394 014 | 21-225_8G6 | VK1|O12/ JK3 | DIQMTQSPSSLSA SVGDRVTITC | RAS--QSIS------SYLN | WYQQKPGK APKLLIF | A------ ASSLQS | GVPSRFSGSGSG--- TDFTLTISSLQPEDFATYYC | QQSYS-------TPFFT | FGPGT KVDIK |
| iPS-394 022 | 21-225_16H6 | VK1|O12/ JK3 | DIQMTQSPSSLSA SVGDRVTITC | RAS--QNIS------SYLN | WYQQKPGK APKLLIY | A------ ASSLQS | GVPSRFSGSRGSG--- TDFTLTISSLQPEDFATYYC | QQSYR-------TPLFT | FGPGT KVDFK |
| iPS-394 043 | 21-225_3B1 | VK1|O12/ JK3 | DIQMTQSPSSLSA SVGDRVTITC | RAS--QSIN------NYLN | WYQQKPGK APKLLIY | A------ TSSLQN | GVPSRFSGSGSG--- TDFTLTISSLQPEDFATYYC | QQSYS-------TPLFT | FGPGT KVDIN |
| iPS-394 051 | 21-225_9E5 | VK1|O12/ JK3 | DIQMTQSQSLSA SVGDRVTITC | RAS--QSIA------SYLN | WYQQKPGK APKLLIY | G------ ASSLQS | GVPSRFSGSGSG--- TDFTLTISSLQPEDFATYYC | QQSYS-------TPLFS | FGPGT KVDIK |
| iPS-394 077 | 21-225_8E12 | VK1|O12/ JK3 | DIQMTQSPSSLSA SVGDRVTITC | RAS--QSIS------NYLN | WYQQKPGK APKLLIY | A------ ASSLQS | GVPSRFSGSGSG--- TDFTLTISSLQPEDFATYFC | QQSYR-------TPFFT | FGPGT KVDIK |
| iPS-394 087 | 21-225_11A5 | VK1|O12/ JK3 | DIQMTQSPSSLSA SVGDRVTITC | RAS--QNIY------SYLN | WYQQKPGK APKLLIY | A------ VSHRFS | GVPSRFSGSGSG--- TDFTLTISSLQPEDFATYYC | QQSYN-------TPLFT | FGPGT KVDIK |
| | VK2JA18/JK 3 | Germline | DIVMTQTPLSLSV TPGQPASISC | KSS-- QSLLHSE-- GKTYLY | WYLQKPGQ SPQLLIY | E------ VSNRFS | GVIPDRFSGSGSG--- TDFTLKISRVEAEDVGVYYC | MQSIQ-------LPFT | FGSGT KVLEIK |
| iPS-434 053 | 21-225_51E1 | VK2|A18/ JK3 | DIVMTQTPLSLSV TPGQPASMSC | KSS-- QSLLHSE-- GKTYLY | WYLRKPGQ PPQFLIF | E------ VSNRFS | GVPDRFSGSGSG--- TEFTLKISRVEAEDVGIYYC | MQSIQ-------LPFT | FGPGT KVDIK |
| iPS-434 137 | 21-225_54D4 | VK2|A18/ JK3 | DIVMTQTPLSLSV TPGQPASMSC | KSS-- QSLLHSE-- GKTYLY | WYLRKPGQ PPQFLIF | E------ VSNRFS | GVPDRFSGSGSG--- TEFTLKISRVEAEDVGIYYC | MQSIQ-------FPFT | FGPGT KVDIK |
| iPS-434 149 | 21-225_55H1 | VK2|A18/ JK3 | DIVMTQTPLSLSV TPGQPASISC | KSS-- QSLLHSE-- GKTYLY | WYLQKPGQ PPQFLIF | E------ VSHRFS | GVPDRFSGSGSG--- TDFTLKISRVEAEDVGVYYC | MQSIQ-------LPFT | FGPGT KVDIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:435 315 | 21-225_147B2 | VK2|A18/ JK3 | DIVMTQTPLSLSV TPGQPASISC | KSS-- QSLLHSE- GKTYLY | WYLQKPGQ PPQLLIY | E--- VSHRVS | GVPDRFSGSGSG-- TDFTLKISRVEAEDVGVYYC | MQSTQ---------FPPT | FGPGT KVDIK |
| | | Germline | | | | | | | K_FR4 |
| | VK1|O18/ JK3 | | | | | | | | |
| iPS:434 055 | 21-225_51B4 | VK1|O18/ JK3 | DIQMTQSPSSLSA SVGDRVTITC | QAS--RDIT- ----FYLN | WYQQKPGK APKLLIY | D--- ASNLET | GVPSRFSGSGSG-- TDFTFTISCVHPEDIATYLC | QQYDN---------LPFT | FGPGT TVLIK |
| | | Germline | | | | | | | K_FR4 |
| | VK1|O18/ JK4 | | | | | | | | |
| iPS:434 087 | 21-225_52F6 | VK1|O18/ JK4 | DIQMTQSPSSLSA SVGDRVTITC | QAS--QDIS- ----NYLH | WYQQKPGK APKLLIY | D--- ASTLGT | GVPLRFSGSGSG-- TEFTFTINSLQPEDIATYSC | QQCDN---------LPLT | FGGGT KVEIK |
| iPS:434 111 | 21-225_53H2 | VK1|O18/ JK4 | DIQMTQSPSSLSA SVGDRVTITC | QAS--QDIS- ----NYLH | WYQQKPGK APQLLIY | D--- ASNLET | GVPSRFTGSGSG-- TDFTTISSLQPEDIATYYC | HQYDN---------LPLT | FGGGT KVEIK |
| iPS:434 121 | 21-225_53F6 | VK1|O18/ JK4 | DIQMTQSPSSLSA SVGDRVTITC | QAS--QDIT- ----NYLD | WYQQKPGK APKLLIY | D--- ASNLGT | GVPSRFSGSGSG-- TDFTFTISSLQPEDIATYYC | QQCDN---------LPLT | FGGGT KVEIK |
| iPS:434 163 | 21-225_50H1 | VK1|O18/ JK4 | DIQMTQSPSSFSA SVGDRVTITC | QAS--QDIS- ----NYLD | WYQQKPGK APKLLIY | D--- ASNLGT | GVPSRFSGSGSG-- TDFAFTISSLQFEDIATYYC | QQCDN---------LPLT | FGGGT KVEIK |
| iPS:435 611 | 21-225_161F10 | VK1|O18/ JK4 | DIQMTQSPSSLSA SVGDRVTITC | QAS--QDIY- ----NHLS | WYQQKPGK APKLLIY | D--- ASNWET | GVPSRFSGSGSG-- TDFTLTISSLQPEDFATYYC | QQYEN---------LPLT | FGGGT KVEIK |
| iPS:435 811 | 21-225_183H6 | VK1|O18/ JK4 | DIQMTQSPSSLSA SVGDRVTIAC | QAS--QDIS- ----NYLN | WYQQTPGK APKVLIY | D--- ASNLET | GVPARFSGSGSG-- TDFTLTISSLQEEDIATYYC | QQYDN---------LPLT | FGGGT KVEIK |
| iPS:394 035 | 21-225_5G9 | VK1|O18/ JK4 | DIQMTQSPSSLSA SVGDRVTITC | QAS--QGIS- ----NSLN | WYQQKPGK APKLLIY | D--- ASNLET | GVPSRFSGSGAG-- TDFTLTISSLQPEDIATYYC | QQYDN---------LPLT | FGGGT KVEIK |
| | | Germline | | | | | | | K_FR4 |
| | VK1|L1/J K1 | | | | | | | | |
| iPS:434 095 | 21-225_52F10 | VK1|L1/J K1 | DIQMTQSPSSLSV SVGDRVTITC | RAS--QGIS- ----NYLG | WFQQKPGK APKSLIY | A--- ASSLQS | GVPSRFSGSGSG-- TDFTLTISSLQPEDFATYYC | QQYNS---------YPPT | FGQGT KVEIK |
| iPS:392 848 | 21-225_20F9 | VK1|L1/J K1 | DIQMTQSPSSLSA SVGDRITITC | RAS--QGIS- ----NYLA | WFQQKPGK APKSLIS | A--- ASSLQS | GVPSKFSGSGSG-- TDFTLTISSLQPEDFATYYC | QQYHS---------YPWT | FGQGT KVEIK |
| iPS:393 078 | 21-225_33H11 | VK1|L1/J K1 | DIQMTQSPSSLSA FVGDRVTITC | WAS--QGIN- ----SYLA | WFQQKRPGK AHKSLIY | A--- ASSLQG | GVPSKFSGSGSG-- TDFTLTISSLQREDIATYYC | QQFNS---------YPLT | FGQGT KVEIK |
| iPS:393 142 | 21-225_33A3 | VK1|L1/J K1 | DIQMTQSPSSLSA SVGDRVTITC | RAS--QGIN- ----NYLA | WFQQKPGK APKSLIY | A--- ASSLQG | GVPSRFSGSGSG-- TDFTLTISSLQPEDFATYYC | QQFNS---------YPPT | FGQGT KVEIK |
| iPS:393 946 | 21-225_16A4 | VK1|L1/J K1 | DIQMTQSPSSLSA SVGDRVTITC | RAS--QDIS- ----NYLA | WFQQKPGK APKSLIS | A--- ASSLQS | GVPSKFSGSGSG-- TDFTLTISSLQPEDFATYYC | QQYHS---------YPWT | FGQGT KVEIN |
| | | Germline | | | | | | | K_FR4 |
| | VK1|O12/J K1 | | | | | | | | |
| iPS:434 117 | 21-225_53C6 | VK1|O12/ JK5 | DIQMTQSPSSLSA SVGDRVTITC | RAS--QYSS- ----DYLN | WYQQKPGK APKVLIE | A--- ASSLKS | GVPSRFSGSGSG-- TDFTLTISSLEPEDFATYFC | QQSYS---------TPFT | FGGGT RLEIK |
| iPS:434 317 | 21-225_59E8 | VK1|O12/ JK5 | DIQMTQSPSSLSA SVGDRVTITC | RAS--QSIS- ----SYLN | WYQQKPGK APKLLIY | A--- ASSLQS | GVPSRFSGSGSG-- TDFTLTISSLQPEDFATYFC | QQSFS---------NSIT | FGGGT RLEIK |
| iPS:434 327 | 21-225_63G6 | VK1|O12/ JK5 | DIQMTQSPSSLSA SVGDRVTITC | RAS--QSIF- ----SYLN | WYQVKPGK APKLLIY | D--- TSTLQT | GVPSRFSGSGSG-- TDFTLTINSLQPEDFATYYC | QQSYG---------IPIT | FGGGT RLEIQ |

Figure 51 (Continued)

| ID | Germline | K_FR1 | K_CDR1 | K_FR2 | K_CDR2 | K_FR3 | K_CDR3 | K_FR4 |
|---|---|---|---|---|---|---|---|---|
| iPS:434_455 | 21-225_72F5 | VK1|O12/JK5 | DIQMTQSPSSLSA SVGDRVIIFC | RAS--QNIS------SYLN | WYQQKPGK APKLLIY | A------ASSLQS | GVPSRFSGSGSG--TDFTLTISSLQPEDFATYSC | QQTY-------STPT | FGQGT RLEIN |
| iPS:435_525 | 21-225_157E7 | VK1|O12/JK5 | DIQMTQSPSSLSA SVGDRVTITC | RAS--QSFS------SYLN | WYQQKPGI APKSLIY | A------ASSLQS | TDFTLTISSLQPEDFATYYC | QESYS------IRFA | FGQGT RLEIK |
| iPS:392_754 | 21-225_21D3 | VK1|O12/JK5 | DIQMTQSPSSLSA SVGDRVTITC | RAS--QSIT------GYSN | WYQQKPGK TPKLLIF | A------TYSLES | GVPSREGSGSFG--TNFTLTISSLQPEDFATYYC | QQSYS------TSIT | FGQGT RLEIK |
| iPS:392_818 | 21-225_22D8 | VK1|O12/JK5 | DIQMTQSPSSLSA SVGDRVTITC | RTS--QNSN------SYLN | WYQQKPGK APKLQIF | A------AYSLES | GVPSRFSGNRSG--TEFTLTISSLQPEDFATYYC | QQTYG------TSIT | FGQGT RLEIK |
| iPS:393_064 | 21-225_33A9 | VK1|O12/JK5 | DIQMTQSPSSLSA SVGDRVTITC | RAS--QSIS------RYLS | WYQQKPGR APNLQIY | A------ASSLQS | GVPSRFSGSGSG--TDFTLTISSLQPEDFATYYC | QQSYN------IPIT | FGQGT RLEIK |
| iPS:393_148 | 21-225_35E5 | VK1|O12/JK5 | DIQMTQSPSSLSA SVGDRVTITY | RAS--QSIS------SYLN | WYQQKPAK APKLHIY | G------ASSFQS | WVPSRESGSGSS--TDFTLTISMQPGDYATYYC | HQSYN------LPIT | FGQGT RLEIK |
| iPS:398_536 | 21-225_33D12 | VK1|O12/JK5 | DVQMTQSPSSLSA SLGDRVTITC | RAS--QSIR------SYLN | WYQQKPGK APNLLIY | S------ASSLQS | GVPSRFSGSGSG--TDFTLTISSLQPEDFANYYC | QQSYS------IPIT | FGQGT RLEIK |
| | Germline | K_FR1 | K_CDR1 | K_FR2 | K_CDR2 | K_FR3 | K_CDR3 | K_FR4 |
| | VK3|A27/JK2 | | | | | | | |
| iPS:434_127 | 21-225_53H8 | VK3|A27/JK2 | EIVLTQSPGTLSL SPGERATLSC | RAS--QSITS-----SYLA | WYQQKPGQ APRLLIY | G------ASGRAT | GIPDRFSGSGSG--TDFTLTISRLEPEDFAVYYC | QQFES------SPMCS | FGQGT NLEIK |
| iPS:436_290 | 21-225_205G3 | VK3|A27/JK2 | EIVLTQSPGTLSL SPGERATLSC | RAS--QNVSY-----SYLA | WYQQKPGQ APRLLIY | G------ASRRAT | GIPDRFSGSGSG--TDFTLTISRLEPEDFAVYYC | QQYGS------SPCS | FGQGT KLEIK |
| iPS:436_568 | 21-225_225B3 | VK3|A27/JK2 | EIVLTQSPGTLSL SPGERATLSC | RAS--QNLSS-----SYLG | WYQQKPGQ APRLLIY | D------TSSRAT | GIPDRFSGSGSG--TDFTLTISRLEPEDFAVYYC | QEYGS------SLMCS | FGQGT KLEIK |
| iPS:392_898 | 21-225_21H10 | VK3|A27/JK2 | EIVLTQSPGTLSL SPGERATLSC | RAS--QSFSS-----SYLA | WYQQKPGQ APRLLIY | G------ASSRAT | GIPDRFSGSGSG--TDFTLTISRLEPEDFAVYYC | QQYG-------SSRS | FGQGT RLEIK |
| iPS:393_802 | 21-225_3D12 | VK3|A27/JK2 | EIVLTQSPGTLSL SPGERATLSC | RAS--QSVSS-----SYLA | WYQQKPGQ APRLLIY | G------TSSRAT | GIPDRFSGSGSG--TDFTLTISRLEPEDFAVYYC | QQYG-------SSRS | FGQGT KLEIK |
| | Germline | K_FR1 | K_CDR1 | K_FR2 | K_CDR2 | K_FR3 | K_CDR3 | K_FR4 |
| | VK1|L1/JK4 | | | | | | | |
| iPS:434_157 | 21-225_55D4 | VK1|L1/JK4 | DIQMTQSPSSLFA SVGDRVTITC | RAS--QDIG------NYLI | WFQQKPGK APKSLIY | I------ASSLQS | GVPSKFSGSGSFG--TDFTLTISNLQPEDFATYYC | QQYHS------FPLT | FGGGT RVEIR |
| iPS:434_175 | 21-225_55A11 | VK1|L1/JK4 | DIQMTQSPSSLSA SVGDRVTITC | RAS--QDIN------IYLA | WFQQKPGK APKSLIY | A------ASSLQS | GVPSKFSGSGSG--TDFTLTISSLQPEDFATYYC | QQYNS------YPLT | FGGGT KVEIK |
| iPS:434_367 | 21-225_65H11 | VK1|L1/JK4 | DIQMTQSPSSLSA SVGDRVTITC | RAS--QDIS------TYLA | WFQQKPGK APKSLIY | A------ASSLQS | GVPSKFSGSGSG--TDFTLTISRLEPEDFAVYYC | QQYNS------FPLT | FGGGT KVEIK |
| iPS:434_429 | 21-225_70H6 | VK1|L1/JK4 | DIQMTQSPSSLSA SLGDRVTITC | RTS--QSIF------NYLN | WFQRKPGK APKVLIY | T------ASSLQS | GIPSRFSGSGSG--TDFTLTISRLEPEDFAVYYC | QQSYS------IPLT | FGGGT RVEIK |
| iPS:434_535 | 21-225_74C8 | VK1|L1/JK4 | DIQMTQSPSSLSA SVGDRVTITC | RAS--QGIG------NYLN | WFQQKPGK APKSLIY | T------TSNLQS | GAPSKFSGSGSG--TDFTLTISSLQYEDFATYYC | QQYSN------YPLT | FGGGT KVEIN |
| iPS:434_573 | 21-225_77E6 | VK1|L1/JK4 | DIQMTQSPSSLSA SVGDRVTITC | RAS--QGIS------KYLA | WFQQKPGK APKSLIY | A------ASSLQG | GAPSKFSGSGSG--TDFTLTISSLQPEDSATYYC | QQYNS------YPLT | FGGGT RVEIK |
| iPS:434_615 | 21-225_76C5 | VK1|L1/JK4 | DIQMTQSPSSLSA SVGDRVTITC | RAS--QVIS------KYLA | WFQQKPGK APKSLIY | A------ASSLQS | GAPSKFSGSGSG--TDFTLTISSLQPEDFATYYC | QQYSN------YPLT | FGGGT RVEIK |
| iPS:434_669 | 21-225_79F4 | VK1|L1/JK4 | DIQMTQSPSSLSA SVGDRVTITC | RAS--QGIS------KYLA | WFQQKPGK APKSLIY | A------ASSLQG | GAPSKFSGSGSG--TDFTLTISSLQPEDFATYYC | QQYSN------YPLT | FGGGT RVEIK |

Figure 51 (Continued)

| | | | | | | | | | |
|---|---|---|---|---|---|---|---|---|---|
| iPS:434 737 | 21-225_74G6 | VK1|L1/J K4 | DIQMTQSPSSLSA SVGDRVTITC | RAS--QGIG- ----KYLA | WFQQKPGK APKSLIY | T------- TSSLQS | GAPSKFSGSGSG-- TDFTLTISSLQPEDFATYYC | QQYSN--- -------- | ------YPLT FGGGT KVEIN |
| iPS:434 741 | 21-225_80C11 | VK1|L1/J K4 | DIQMTQSPSSLSA SVGDRVTITC | RAS--QGIG- ----RYLA | WFQQKPGK APKSLIY | A------- ASSLQS | GAPSKFSGSGSG-- TDFTLTISSLQPEDFATYYC | QQYSN--- -------- | ------YPLT FGGGT KVEIK |
| iPS:434 867 | 21-225_79A12 | VK1|L1/J K4 | DIQMTQSPSSLSA SVGDRVTITC | RAS--QVIS- ----KYLA | WFQQKPGK APKSLIY | A------- ASSLQS | GAPSKFSGSGSG-- TDFTLTISSLQPEDFATYYC | QQYSN--- -------- | ------YPLT FGGGT KVEIK |
| iPS:435 333 | 21-225_147E9 | VK1|L1/J K4 | DIQMTQSPSSLSA SVGDRVTITC | RAS--QDIN- ----NYLA | WFQQKPGK APKSLIV | A------- ASSLQS | GVPSRFSGSGSG-- TDFTLTISSLQPEDFATYYC | QQYNS--- -------- | ------YPLT FGGGT KVEIK |
| iPS:435 409 | 21-225_150G8 | VK1|L1/J K4 | DIQMTQSPSSLSA SVGDRVTITC | RAS--QGIS- ----HYLA | WFQQKPGK APKSLIY | V------- ASSLQN | GVPSRFSGSGSG-- TDFTLTISSLQPEDFATYYC | QQYNN--- -------- | ------YPLT FGGGT KVEIK |
| iPS:435 505 | 21-225_157C1 | VK1|L1/J K4 | DIQMTQSPSSLSA SIGDRILTC | RAS--QGIS- ----NYLA | WFQQRPGK APKSLIY | A------- ASSLLS | GVPSKFSGSGSG-- TDFTLTISSLQPEDFATYYC | QQYNS--- -------- | ------FPFT FGGGT KVELK |
| iPS:435 595 | 21-225_160H4 | VK1|L1/J K4 | DIQMTQSPSSLSA SVGDRVTITC | RAS--QDIS- ----NYLV | WFQQKLGK APKSLIY | V------- ASSLQS | GVPSRFSGSGSG-- TDFTLTISSLQPEDFATYYC | QQYNS--- -------- | ------YPLT FGGGT KVEIK |
| iPS:435 639 | 21-225_163G6 | VK1|L1/J K4 | DIQMTQSPSSLSA SVGDRVTITC | RAS--QDIS- ----NYLV | WFQQKPGK APKSLIF | A------- ASSLLS | GVPSRFSGSGSG-- TDFTLTISSLQPENFATYYC | QQYHS--- -------- | ------YPLT FGGGT KVAIK |
| iPS:435 653 | 21-225_166H1 | VK1|L1/J K4 | DIQMTQSPSSLST SVGDRVTITC | RAS--QDIS- ----HYLA | WFQQKPGK APKSLIY | A------- ASSLQS | GVPSKFSGSGSG-- IDFNLTISSLQPEDFATYYC | QQYNS--- -------- | ------FPLT FGGGT KVEIT |
| iPS:435 677 | 21-225_169C1 2 | VK1|L1/J K4 | DIQMTQSPSSLSA SVGDRVTITC | RAS--QDIS- ----NYLA | WFQQKPGK APKSLIF | S------- ASSLQS | GVPSKFSGSGSG-- TDFTLTISSLQPEDFATYYC | QQSDS--- -------- | ------YPLT FGGGT KVEIK |
| iPS:435 699 | 21-225_170D6 0 | VK1|L1/J K4 | DIQMTQSPSSLSA SVGDRVTITC | RAS--QGIG- ----NCLA | WFQQKPGK APKSLIY | S------- ASSLQS | GVPSKFSGSGSG-- TDFTLTISSLQPEDFATYYC | QQSDS--- -------- | ------YPLT FGGGT KVEIK |
| iPS:435 745 | 21-225_175G3 | VK1|L1/J K4 | DIQMTQSPSSLSA SVGDRVAITC | RAS--QDIS- ----NDLA | WFQQKPGK APKSLIF | S------- ASSLQS | GVPSKFSGSGSG-- TDFTLTISSLQPEDFATYYC | QQSDS--- -------- | ------YPLT FGGGT KVEIK |
| iPS:435 819 | 21-225_190C1 1 | VK1|L1/J K4 | DIQMTQSPSSLSA SVGDRVTITC | RTS--QGIG- ----NYLA | WFQQKPGK APKSLIY | K------- TSSLQS | GVPSKFSGSGSG-- TDFTLTISSLQPEDFATYYC | QQYMT--- -------- | ------YPLT FGGGT KVEIK |
| iPS:435 825 | 21-225_190G1 1 | VK1|L1/J K4 | DIQMTQSPSSLSA SVGDRVTITC | RTS--QGIG- ----NYLA | WFQQKPGK APKSLIY | K------- ASSLQS | GVPSKFSGSGSG-- TDFTLTISSLQPEDFATYYC | QQYMT--- -------- | ------YPLT FGGGT KVEIK |
| iPS:435 837 | 21-225_198G3 | VK1|L1/J K4 | DIQMAQSPSSLSA SVGDRVTITC | RTS--QGIG- ----KYLA | WFQQKPGK APKSLIY | K------- ASSLQG | GVPSKFSGSGSG-- TDFTLTISSLQPEDFATYYC | QQYMT--- -------- | ------YPLT FGGGT KVEIK |
| iPS:435 845 | 21-225_191G1 | VK1|L1/J K4 | DIQMTQSPSSLSA SVGDRVTITC | RAS--QGIS- ----NYLA | WFQQKPGK APKSLIY | K------- ASSLQS | GVPSKFSGSGSG-- TDFTLTISSLQPEDFATYYC | QHYLT--- -------- | ------YPLT FGGGT KVEIK |
| iPS:435 859 | 21-225_190E6 | VK1|L1/J K4 | DIQMTQSPSSLSA SVGDRVTITC | RTS--QGIG- ----NYLA | WFQQKPGK APKSLLY | K------- ASSLQS | GVPSKFSGSGSG-- TDFTLTISSLQPEDFATYYC | QQYMT--- -------- | ------YPLT FGGGT KVEIK |
| iPS:435 873 | 21-225_190G4 | VK1|L1/J K4 | DIQMTQSPSSLSA SVGDRVTITC | RAS--QDIG- ----RYLA | WFQQKPGK APKSLIY | A------- ASSLQS | GVPSKFSGSGSG-- TDFTLTISSLQPEDFATYYC | QQYST--- -------- | ------YPLT FGGGT KVEIK |
| iPS:435 933 | 21-225_190F8 | VK1|L1/J K4 | DIQMTQSPSSLSA SVGDRVTITC | RTS--QGIG- ----NYLA | WFQQKPGK APKSLLI | K------- ASSLQS | GVPSKFSGSGSG-- TDFTLTISSLQPEDFATYYC | QQYMT--- -------- | ------YPLT FGGGT KVEIK |
| iPS:435 945 | 21-225_191A1 0 | VK1|L1/J K4 | DIQMTQSPSSLSA SVGDRVTITC | RAS--QGIG- ----KYLA | WFQQKPGK APKSLIY | A------- ASSLQS | GVPSKFSGSGYG-- TDFTLTISSLQPENFAIYYC | QQYST--- -------- | ------YPLT FGGGT KVEIK |

Figure 51 (Continued)

| ID | | | | | | | | | | |
|---|---|---|---|---|---|---|---|---|---|---|
| iPS:435947 | 21-225_191E10 | VK1/L1/J K4 | DIQMTQSPSSLSA SVGDRVTITC | RAS--QGIG- ----KYLA | WFQQKPGK APKSLLY | A------- ASSLQS | GVPSKFSGSGSG- TDFTLTISSLQPEDFATYYC | QQYST---- -------- | ---------- ----YPLT | FGGGT KVEIK |
| iPS:435957 | 21-225_191G12 | VK1/L1/J K4 | DIQMTQSPSSLSA SVGDRVTITC | RTS--QGIS- ----NYLA | WFQQKPGK APKSLLY | K------- ASSLQS | GVPSKFSGSGSG- IDFTLTISSLQPEDFATYYC | QQYIT---- -------- | ---------- ----YPNT | FGGGS KVEIK |
| iPS:435963 | 21-225_192D2 | VK1/L1/J K4 | DIQMTQSPSSLSA SVGDRVTITC | RAS--QGIS- ----NYLA | WFQQKPGK APKSLIY | A------- ASSLQS | GVPSKFSGSGSG- IDFTLTISSLQPEDFATYYC | QHVVT---- -------- | ---------- ----YPLT | FGGGT KVEIK |
| iPS:435971 | 21-225_192D3 | VK1/L1/J K4 | DIQMTQSPSSLSA SVGDRVTITC | RAS--QGIS- ----NYLA | WFQQKPGK APKSLIY | A------- ASSLQS | GVPSKFSGSGSG- IDFTLTISSLQPEDFATYYC | LHYLT---- -------- | ---------- ----YPLT | FGGGT KVEIK |
| iPS:435979 | 21-225_192H4 | VK1/L1/J K4 | DIKMTQSPSSLSA SVGDRVTITC | RAS--QDIS- ----NYLA | WFQQKPGK APKSLIS | A------- ASSLQS | GVPSKFSGSGSG- TDFTLTISSLQPEDFATYYG | LHYLN---- -------- | ---------- ----YPLT | FGGGT RVEIR |
| iPS:435987 | 21-225_192G6 | VK1/L1/J K4 | DIQMTQSPSSLSA SVGDRVTITC | RTS--QGIG- ----KYLA | WFQQKPGK APKSLLY | K------- ASSLLY | GVPSKFSGSGSG- TDFTLTISSLQPEDFATYYC | QQYMT---- -------- | ---------- ----YPLT | FGGGT KVEIK |
| iPS:435993 | 21-225_192C8 | VK1/L1/J K4 | DIQMTQSPSSLSA SVGDRVTITC | RAS--QGIS- ----NYLA | WFQQKPGK APKSLIY | A------- ASSLQS | GVPSKFSGSGSG- IDFTLTISSLQPEDFATYYC | QHVLT---- -------- | ---------- ----YPLT | FGGGT KVEIK |
| iPS:435997 | 21-225_192G8 | VK1/L1/J K4 | DIQMTQSPSSLSA SVGDRVTITC | RTS--QGIG- ----NYLA | WFQQKPGK APKSLIY | K------- ASSLQS | GVPSKFSGSGSG- IDFTLTISSLQPEDFATYYC | QQYIT---- -------- | ---------- ----YPLT | FGGGT KVEIK |
| iPS:436005 | 21-225_192H10 | VK1/L1/J K4 | DIQMTQSPSSLSA SVGDRVTITC | RAS--QGIG- ----NYLA | WFQQKPGK APKSLIY | A------- ASSLQS | GVPSKFSGSGYG- TDFTLTISSLQPENFATYYC | QQYST---- -------- | ---------- ----YPLT | FGGGT KVEIK |
| iPS:436031 | 21-225_193C7 | VK1/L1/J K4 | DIQMTQSPSSLSA SVGDRVTITC | RAS--QGIS- ----KYLA | WFQQKPGK APKSLIY | A------- VSSLQS | GVPSKFSGSGSG- TDFTLTISSLQPEDFATYYC | QQYST---- -------- | ---------- ----YPLT | FGGGT KVEIK |
| iPS:436045 | 21-225_193A10 | VK1/L1/J K4 | DIQMTQSPSSLSA SVGDRVTITC | RTS--QGIS- ----NYLA | WFQQKPGK APKSLIY | A------- ASSLQS | GVPSKFSGSGSG- IDFTLTISSLQPEDFATYYC | QHVLT---- -------- | ---------- ----YPLT | FGGGT KVEIK |
| iPS:436054 | 21-225_194C1 | VK1/L1/J K4 | DIQMTQSPSSLSA SVGDRVTITC | RAS--QGIS- ----NYLA | WFQQKPGK APKSLIY | A------- ASSLQS | GVPSKFSGSGSG- TDFTLTISSLQPEDFATYYC | LHYLT---- -------- | ---------- ----YPLT | FGGGT KVEIK |
| iPS:436076 | 21-225_194H1 | VK1/L1/J K4 | DIQMTQSPSSLSA SVGDRVTITC | RAS--QGIS- ----NYLA | WFQQKPGK APKSLLY | A------- ASSLQS | GVPSKFSGSGSG- IDFTLTISSLQPEDFATYYC | QHYLT---- -------- | ---------- ----YPLT | FGGGT KVEIK |
| iPS:436086 | 21-225_191G11 | VK1/L1/J K4 | DIQMTQSPSSLSA SVGDRVTITC | RTS--QGIG- ----KYLA | WFQQKPGK APKSLLY | K------- VSSLQS | GVPSKFSGSGSG- TDFTLTISSLQPEDFATYYC | QQYMT---- -------- | ---------- ----YPLT | FGGGT KVEIK |
| iPS:436090 | 21-225_195A9 | VK1/L1/J K4 | DIQMTQSPSSLSA SVGDRVTITC | RAS--QGIS- ----NYLA | WFQQKPGK APKSLIY | A------- ASSLQS | GVPSKFSGSGSG- TDFTLTISSLQPEDFATYYC | QHYLT---- -------- | ---------- ----YPLT | FGGGT KVEIK |
| iPS:436112 | 21-225_196C7 | VK1/L1/J K4 | DIQMTQSPSSLSA SVGDRVTITC | RAN--QAIS- ----NYLA | WFQQKPGK APKSLIY | A------- ASSLQS | GVPSKFSGSGSG- TDFTLTISSLQPEDFATYYC | QHYLT---- -------- | ---------- ----YPLT | FGGGT KVEIK |
| iPS:436138 | 21-225_197F2 | VK1/L1/J K4 | DIQMTQSPSSLSA SVGDRVTITC | RAS--QGIS- ----NYLA | WFQQKPGK APKSLLY | A------- ASSLQS | GVPSKFSGSGSG- TDFTLTISSLQPEDFATYYF | QQYIT---- -------- | ---------- ----YPLT | FGGGT KVEIK |
| iPS:436152 | 21-225_197B6 | VK1/L1/J K4 | DIQMTQSPSSLSA SVGDRVTITC | RAS--QGIG- ----NYLA | WFQQKPGK APKSLIY | G------- ASSLQS | GVPSKFSGSGSG- TDFTLTISSLQPENFATYYC | QQYST---- -------- | ---------- ----YPLT | FGGGT KVEIK |
| iPS:436173 | 21-225_197G1 | VK1/L1/J K4 | DIQMIQSPSSLSA SVGDRVTITC | RTS--QGIS- ----NYLA | WFQQKPGK APKSLIY | K------- TSSLQS | GFPSKFSGSGSG- TDFTLTISSLQPEDFATYYC | QQYMT---- -------- | ---------- ----YPLT | FGGGT KVEIK |
| iPS:436189 | 21-225_198B6 | VK1/L1/J K4 | DIQMTQSPSSLSA SVGDRVTITC | RAS--QGIG- ----NYLA | WFQQKPGK APKSLIY | A------- ASSLQS | GVPSKFSGNRSG- IDFTLTISSLQPEDFATYYC | QQYST---- -------- | ---------- ----YPLT | FGGGT KVEIK |

Figure 51 (Continued)

| | | | | | | | | |
|---|---|---|---|---|---|---|---|---|
| iPS:436 201 | 21-225_199C5 | VK1¦L1/J K4 | DIQMTQSPSSLSA SVGDRVTITC | RAS--QGIS-- ----KYLA | WFQQKPGK APKSLIY | A------ ASSLQS | GVPSKFSGSGSG-- TDFTLTISSLQPEDFAAYYC | QQYLT------------YPLT | FGGGT KVEIK |
| iPS:436 260 | 21-225_203H1 | VK1¦L1/J K4 | DIQMTQSPSSLSA SVGDRVTIIC | RAS--QGIG-- ----NYLA | WFQQKPGK APKSLIY | V------ ASRLQS | GVPSKFSGTGSG-- SDFTLTISSLQPEDFATYYC | QRYNT------------YPLT | FGGGT KVEIK |
| iPS:436 282 | 21-225_204G6 | VK1¦L1/J K4 | DIRMTQSPSSLSA SVGDRITIC | RTS--QGIG-- ----NYLA | WFQQKPGK APKSLIY | A------ ASSLQS | GVPSRFSGSGSG-- TDFTLTISSLQPEDFATYYC | QHYLS------------YPLT | FGGGT KVEIK |
| iPS:436 284 | 21-225_204G8 | VK1¦L1/J K4 | DIQMTQSPSSLSA SVGDRVTIIC | RAS--QGIS-- ----MHLA | WFQQKPGK APKSLIF | A------ ASSLQS | GVPSQFSGSGSG-- TEFTLTISSLQPEDFATYYC | QQYSN------------YPVT | FGGGT KVEIK |
| iPS:436 292 | 21-225_205H3 | VK1¦L1/J K4 | DIPMTQSPSSLSA SVGDRVTIIC | RAS--QAIS-- ----NHLA | WFQLKPGK APKSLIY | A------ ASSLQS | GVPSKFSGSGSG-- SDFTLTISSLQPEDFATYYC | QQYSN------------YPLT | FGGGT KVEIK |
| iPS:436 296 | 21-225_205F5 | VK1¦L1/J K4 | DIQMTQSPSSLSA SVGDRVTIIC | RAS--QGIG-- ----NYLA | WFQQKPGK APKSLIY | G------ VSSLQS | GVPSKFSGSGSG-- TDFTLTISSLQPEDFATYYC | QQYSN------------YPLT | FGGGT KVDIR |
| iPS:436 324 | 21-225_207G6 | VK1¦L1/J K4 | DIQMTQSPSSLSA SVGDRVTIIC | RAS--QGIR-- ----NYLA | WLQQKPGK APKSLIH | A------ ASSLQS | GVPSKFSGNRSG-- TDFTLTISSLQPEDFATYYC | QQYSN------------YPLT | FGGGT KVEIK |
| iPS:436 364 | 21-225_211A1 | VK1¦L1/J K4 | DIQMTQSPSSLSA SVGDRVTIIC | RAS--QGIG-- ----NYLA | WFQQKPGR APRSLIY | D------ ASSLES | GVPSKFSGSRSG-- TDFTLTIGSLQPEDFATYYC | QHYMT------------YPLT | FGAGT KVEIK |
| iPS:436 366 | 21-225_211A3 | VK1¦L1/J K4 | DIRMTQSPSSLSA SVGDRVTIIC | RAS--QAIG-- ----KHLA | WFQQKPGK APKSLIY | A------ ASRLQS | GVPSKFSGSGSG-- TDFTLTISSLQPEDLATYYC | QQYSN------------YPLT | FGGGT KVEIK |
| iPS:436 372 | 21-225_211A8 | VK1¦L1/J K4 | DIEMTQSPSLSA FVGDRVTIIC | RAS--QGIS-- ----RYLA | WVQQKPGK APKSLIY | A------ ASSLQS | GVSSKFSGSGSG-- TDFTLTISSLQPEDFATYYC | LRYDT------------YPLI | FGGGT KVEIK |
| iPS:436 376 | 21-225_211F6 | VK1¦L1/J K4 | DIQMTQSPSSLSA SVGDRVTIIC | RAS--QGIS-- ----NHLA | WFQQKPGQ APKSLIY | A------ ASSLQS | GVPSRFSGSRSG-- TDFTLTISSLQPEDFATYYC | QQYSN------------YPLT | FGGGT KVEIK |
| iPS:436 378 | 21-225_212D7 | VK1¦L1/J K4 | DIRMTQSPSSLSA SVGDRVTIIC | RAS--QGIS-- ----NHLA | WFQQKPGK APKSLIH | A------ ASSLQS | GVPSKFSGNRSG-- TDFTLTINNLQPEDFVTYYC | QQYSN------------YPLT | FGGGT KVEIK |
| iPS:436 380 | 21-225_212H9 | VK1¦L1/J K4 | DIEMTQSPSLSA SVGDRVTIIC | RAS--QGIS-- ----SYLA | WLQQKPGK APKSLIY | A------ ASSLQS | GVPSKFSGSGSG-- TDFTLTISSLQPEDFATYYC | LRYDT------------YPLT | FGGGT KVEIK |
| iPS:436 384 | 21-225_212F10 | VK1¦L1/J K4 | DIQMTQSPSSLSA SVGDRVTIIC | RAS--QGIS-- ----NYLD | WFQQKPGK APKSLIY | S------ ASNLQS | GVPSKFSGSGSG-- TDFTLTISSLQPEDFATYYC | QHYSN------------YPLT | FGGGT KVEIK |
| iPS:436 388 | 21-225_212H1 | VK1¦L1/J K4 | DIQMTQSPSSLSA SVGDRVTIIC | RAS--QAIG-- ----KHLA | WFQQRPGK APKSLIY | A------ ASRLQS | GVPSKFSGSGSG-- TDFTLTISSLQPEDFATYYC | QHYSN------------YPLT | FVGGT KVEIT |
| iPS:436 390 | 21-225_213D2 | VK1¦L1/J K4 | DIQMTQSPSSLSA SVGDRVTIIC | RAS--QGIS-- ----NHLA | WFQQKPGK APKSLIH | A------ ASSLQS | GVPSKFSGNRSG-- TDFTLTINNLQPEDFVTYYC | HQYSN------------YPLT | FGGGT KVEIK |
| iPS:436 394 | 21-225_213C4 | VK1¦L1/J K4 | DIHMTQSPSSLSA SVGDRVTIIC | RAS--QAIR-- ----NYLA | WCQQKPGK AFKTLIY | A------ ASSLQS | GVPSKFSGSGSG-- TDFTLTIGSLQPEDFATYYC | QQYSN------------YPLT | FGGGT KVEIK |
| iPS:436 396 | 21-225_213E5 | VK1¦L1/J K4 | DIRMTQSPSSLSA SVGDRVTIIC | RAS--QAIG-- ----KHLA | WFQQRPGK APKSLIY | A------ ASRLQS | GVPSKFSGNRSG-- TDFTLTISSLQPEDFATYYC | QHYSN------------YPLT | FGGGT KVEIK |
| iPS:436 398 | 21-225_213B8 | VK1¦L1/J K4 | DIQMTQSPSSLSA SVGDRVTIIC | RAS--QGIS-- ----NHLA | WFQLKPGK APKSLIY | A------ ASRLQS | GVPSKFSGSGSG-- TDFTLTISSLQPEDFATYYC | QQYSN------------YPLT | FGGGT KVEIK |
| iPS:436 410 | 21-225_212E1 | VK1¦L1/J K4 | DIQMTQSPSSLSA SVGDRVTIIC | RAS--QGIS-- ----NHLA | WFQQKPGK APKSLIY | A------ ASSLQS | GVPSKFSGSGSG-- TDFTLTISSLQPEDFATYYC | QQYSN------------YPLT | FGGGT KVEIK |
| iPS:436 420 | 21-225_215B5 | VK1¦L1/J K4 | DIQMTQSPSSLSA SVGDRVTIIC | RAS--QGIS-- ----NHLA | WFQQKPGK APKSLIH | A------ ASSLHS | GVPSKFSGNRSG-- TDFTLTINNLQPEDFVTYYC | QQYIN------------YPLT | FGGGT KVEIK |
| iPS:436 422 | 21-225_215D6 | VK1¦L1/J K4 | DIQMTQSPSSLSA SVGDRVTIIC | RAS--QGIS-- ----MHLA | WFQQKPGK APKSLIY | A------ ASSLHS | GVPSKFSGSRSG-- TDFTLTISSLQPEDFATYYC | QQYVT------------YPLT | FGGGT KVEIK |

Figure 51 (Continued)

| | | | | | | | | | |
|---|---|---|---|---|---|---|---|---|---|
| iPS:436 430 | 21-225_215A1 2 | VK1|L1/J K4 | DIQMTQSPSSLSA SVGDRITTC | RTS--QDIG- ----NYLA | WFQQKPGK APKSLIY | A------- ASSLQS | GVPSKFSGSRSG--- TDFTLTISSLQSEDFATYYC | QQYVT---------- --------YPLT | FGGGT KVEIK |
| iPS:436 452 | 21-225_217G5 | VK1|L1/J K4 | DIMTQSPSSLSA SVGDRVTITC | RAS--QGIG- ----NYLA | WFQQRPGK APKSLIY | A------- ASSLQS | GVPSKFSGTRSG--- TDFTLTISSLQPDDFATYYC | QQYVN---------- --------YPLT | FGGGT KVEIN |
| iPS:436 454 | 21-225_217B1 | VK1|L1/J K4 | DIRMTQSPSSLSA SVGDRVTITC | RAS--QAIG- ----KHLA | WFQQRPGK APKSLIY | A------- ASRLQS | GVPSKFSGSGSG--- TDFTLTISVQPEDLATYYR | QHTSK---------- --------SFVQ | LVGGT KVEIT |
| iPS:436 464 | 21-225_219H1 | VK1|L1/J K4 | DIQMTQSPSSQSA SVGDRVTITC | RAS--QGIS- ----NYLD | WFQQKPGK APKSLIY | S------- ASNLQS | GVPSKFSGSRSG--- TDFTLTISSLQPEDFATYYC | QHYSN---------- --------YPLT | FGGGT KVEIK |
| iPS:436 490 | 21-225_221F6 | VK1|L1/J K4 | DIQMTQSPSSLSG SVGDRVTITC | RAS--QGIS- ----NYLA | WFQQKPGK APKSLIY | A------- ASNLQS | GVPSKFSGSRSG--- TDFTLTISSLQPEDFATYYC | QQYMT---------- --------YPLT | FGGGT RVEIK |
| iPS:436 502 | 21-225_222A1 | VK1|L1/J K4 | DIQMTQSPSSLSA SVGDRVTITC | RAS--QGIS- ----NYLA | WFQQKPGK APKSLIY | A------- ASSLQS | GVPSKFSGSGSG--- TDFTLTISSLQPEDFATYYC | LYYLN---------- --------YPLT | FGGGT KVEIK |
| iPS:436 514 | 21-225_222D1 0 | VK1|L1/J K4 | DIQMTQSPSSLSA SVGDRVTITC | RAS--QGIS- ----NYLA | WFQQKPGK APKSLIY | A------- ASSLQS | GVPSKFSGSGSG--- TDFTLTISSLQPEDFATYYC | LHYLN---------- --------YPLT | FGGGT RVEIK |
| iPS:436 522 | 21-225_223H1 | VK1|L1/J K4 | DIQMTQSPSSLSA SVGDRVTITC | RAS--QGIS- ----NYLA | WFQQKPGK APKSLIY | A------- ASSLQS | GVPSKFSGSGSG--- TDFTLTISSLQPEDFATYYC | LHYLN---------- --------YPLT | FGGGT KVEIK |
| iPS:437 258 | 21-225_163F9 | VK1|L1/J K4 | DIQMTQSPSSLSA SVGDRVTITC | RAS--QGIS- ----NYLA | WFQQKPGK APKSLIS | A------- ASSLQS | GVPSKFSGSGSG--- TDFTLTISSLQPEDFATYYC | QQYNS---------- --------YPLS | FGGGT KVEIK |
| iPS:437 260 | 21-225_170D1 | VK1|L1/J K4 | DIQMTQSPSSLSA SVGDRVTITC | RAS--QDIS- ----NYLA | WFQQRPGK APKSLIY | A------- ASSLQS | GVPSKFSGSGSG--- TDFTLTISSLQPEDFATYYC | QQCDS---------- --------PPLT | FGGGT KVEIK |
| iPS:437 264 | 21-225_174H1 2 | VK1|L1/J K4 | DIQMTQSPSSLSA SVGDRVTITC | RAS--QDIS- ----NYLA | WFQQKPGK APKSLIY | S------- ASSLQS | GVPSKFSGSGSG--- TDFTLTISSLQPEDFATYYC | QQSDS---------- --------YPLT | FGGGT KVEIK |
| iPS:437 266 | 21-225_177A5 | VK1|L1/J K4 | DIQMTQSPSSLSA SVGDRVTITC | RAS--QDIS- ----NYLA | WFQQKPGK APKSLIY | S------- ASSLQS | GVPSRFSGSGSG--- TDFTLTISSLQPEDFATYYC | QQSDS---------- --------YPLT | FGGGT KVEIK |
| iPS:437 270 | 21-225_178H4 | VK1|L1/J K4 | DIQMTQSPSSLSA SVGDRVTITC | RAS--QDIS- ----NYLA | WLQQKPGK APKSLIF | S------- ASSLQS | GVPSKFSGSGSG--- TEFTLTITSNLQPEDFATYYC | QQSNS---------- --------YPLT | FGGGT KVEIK |
| iPS:438 664 | 21-225_216G1 | VK1|L1/J K4 | DIQMTQSPSSLSA SVGDRVTITC | RAS--QGIS- ----SYLA | WFQQKPGK APKSLIY | A------- ASSLQS | GVPSRFSGSGSG--- TDFTLTISSLQPEDFASYYC | LRYDI---------- --------YPLT | FGGGT KVEIK |
| iPS:451 120 | 21-225_197D3 | VK1|L1/J K4 | DIQMTQSPSSLSA SVGDRVTITC | RAS--QGIR- ----NYLA | WFQQKPGK APKSLIY | A------- ASSLQS | GVPSKFSGSGSG--- TDFTLTISSLQPEDFATYYC | QHYLT---------- --------YPLT | FGGGT KVEIK |
| iPS:392 682 | 21-225_16A12 | VK1|L1/J K4 | DIQMTQSPSSLSA SVGDRVTITC | RAS--QAIN- ----TYLA | WFQQKPGK APKSLIS | A------- ASSLQS | GVPSKFSGSGSG--- TEFTLTITSNLQPEDFATYYC | QQYYS---------- --------YPLT | FGGGT KVEIK |
| iPS:392 856 | 21-225_22A2 | VK1|L1/J K4 | DIQMTQSPSSLSA SVGDRVTITC | RAS--QDIS- ----NYLA | WVQQKPGK APKSLIY | A------- ASSLQS | GVPSRFSGSGSG--- TDFTLTISSLQPEDFASYYC | QQYNS---------- --------PPLT | FGGGT KVEIK |
| iPS:392 966 | 21-225_32G3 | VK1|L1/J K4 | DIQMTQSPSTSLSA SVGDRVTITC | RAS--QAIS- ----NYLA | WFQQKPGK APKSLIY | D------- TSSLQS | GVPSRFSGSGSG--- TDFTLTISSLQPEDFATYYC | QQYHS---------- --------YPLT | FGGGT KVEIK |
| iPS:393 952 | 21-225_1F1 | VK1|L1/J K4 | DIQMTQSPSSLSA SVGDRVTITC | RAS--QGIN- ----NYLA | WFQQKPGK APKSLIS | V------- ASSLQT | GVPSRFSGSGSG--- TDFTLTISSLQPEDFATYYC | QQYNS---------- --------YPLT | FGGGT KVEIK |
| iPS:393 988 | 21-225_7F10 | VK1|L1/J K4 | DIQMTQSPSALSA SVGDRVTITC | RAS--QDIR- ----NYLA | WFQQKPGK APKSLIS | V------- ASSLQS | GVPSRFSGSGSG--- TDFTLTISSLQPEDFATYYC | QQYNS---------- --------YPLT | FGGGT KVEIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:402_233 | 21-225_16D10 | VK1|L1/JK4 | DIQMTQSPSSLSA SVGDRVTITC | RAS--QDIS-----NYLA | WFQQKPGK APKSLIY | A-----TPSLQS | GVPSKFSGSGSG------ | QQYNS-----------YPLT | FGGGT KVEIK |
| iPS:402_237 | 21-225_23D11 | VK1|L1/JK4 | DIQMTQSPSSLSA SVGDRVTITC | RAS--QGIA-----NYLA | WFCQRPGK APKSLIS | A-----ASSLQS | GVPSRFSGSGSG------TEFTLTISSLQPEDFATYYC | QQYHS-----------YPLT | FGGGS KVEIK |
| | Germline | VK1|O18/JK5 | | | | | | | |
| iPS:434_171 | 21-225_50G4 | VK1|O18/JK5 | DIQMTQSPSSLSA SVGDRVTITC | QAS--QDIT-----NFLN | WYQQKPGK APKLLIY | D-----ASNLET | GVPSRFSGSGSG------TDFTFTISSLQPEDIATYFC | QQYD-------------NLIT | FGGGT RLEIK |
| iPS:435_565 | 21-225_159C4 | VK1|O18/JK5 | DIQMTQSPSSLSA SVGDRVTITC | QAS--QDIS-----DYLN | WYQQKPGK APKLLIY | D-----ASTLET | GVPSRFSGSGSG------TDFTFTISSLQPEDIATYFC | QQYDN------------LPIT | FGGGT RLEIK |
| iPS:435_607 | 21-225_161G4 | VK1|O18/JK5 | DIQMTQSPSSLSA SVGDRVTITC | QAS--QDIY-----NYLN | WYQQKPGK APKLLIY | D-----ASNLET | GVPSRFSGSGSG------TDFTFAISSLQPEDIATYYC | QQYD1------------LPIT | FGGGT RLEIK |
| iPS:437_302 | 21-225_225B1 | VK1|O18/JK5 | DIQMTQSPSSLSA SIGDRVTITC | QAS--QDIF-----NYLN | WYQQKPGK APKLLIY | D-----ASTLET | GVPSRFSGSGSG------TDFTFTISSLQPEDIATYYC | QQYDN------------LPIT | FGGGT RLEIK |
| iPS:392_868 | 21-225_24D6 | VK1|O18/JK5 | DIQMTQSPSSLSA SVGDRVTITC | QAS--QDIN-----NYLN | WYQLKPGK ALKLLIY | D-----ASDLET | GVPSRFSGSGSG------TDFTFTISSLQPEDIATYYC | QQYEN------------LPIT | FGGGT RLEIK |
| iPS:393_020 | 21-225_30E2 | VK1|O18/JK5 | DIQMTQSPSHSLSA SVGDRVTITC | QAS--QYIS-----NYLN | WYCQKSGK APKLLIY | D-----GSSLET | GVPSRFSGSGSG------TDFTFTISSLQPEDIATYYC | QQYDN------------LPIT | FGGGT RLEIK |
| iPS:393_138 | 21-225_35E3 | VK1|O18/JK5 | DIQMTQSPSSLSA SVGDRVTITC | QAS--QDIF-----NYLN | WYQQKPGK APKLLIY | D-----ASTLET | GVPSRFSGSGSG------TDFTFTISSLQPEDVATYYC | QQYDN------------LPIT | FGGGT RLEIK |
| iPS:393_892 | 21-225_6G7 | VK1|O18/JK5 | DIQMTQSPSRSA SVGDRVTITC | QAS--QDIS-----NYLN | WCQQKPGK ALKLLIY | D-----ASTLET | GVPSRFSGSGSG------TDFTFTISSVQPEDIATYYC | QQYDN------------VPIT | FGGGT RLEIK |
| iPS:393_910 | 21-225_15F10 | VK1|O18/JK5 | DIQMTQSPSSLSA SVGDRVTITC | QAN--QDIT-----NFLN | WYQLKPGK APNLLIS | D-----ASNLET | GVPSRFSGSGSG------TDFTFTISSLQPEDIATYYC | QQYDN------------LPIT | FGGGT RLEIK |
| iPS:393_912 | 21-225_16F6 | VK1|O18/JK5 | DIQMTQSPSSLSA SVGDRVTITC | QAN--QDIT-----NFLN | WYQLKPGK APNLLIS | D-----ASNLET | GVPSRFSGSGSG------TDFTFTISSLQPEDVATYYC | QQYDN------------LPIT | FGGGT RLEIK |
| iPS:394_000 | 21-225_11A2 | VK1|O18/JK5 | DIQMTQSPSSLSA SVGDRVTITC | QAS--QDIS-----NYLN | WYQQKPGK APKLLIY | D-----ASNLET | GVPSRFSGSGSG------TDFTFTISSLQPEDVATYYC | QQYDN------------LPIT | FGGGT RLDIK |
| iPS:394_004 | 21-225_13A1 | VK1|O18/JK5 | DIQMTQSPSSLSA SVGDRVTITC | QAS--QDIN-----NYLN | WYCQRLGT APKLLIY | D-----GSNLET | GVPSRFSGSGSG------TDFTFTISSLQPEDIATYYC | QQYEN------------LPIT | FGGGT RLEIK |
| iPS:394_006 | 21-225_15C2 | VK1|O18/JK5 | DIQMTQSPSSLSA SVGDRVTITC | QAS--QDIT-----NYLN | WYQQKPGK APNLLIY | D-----ASNLET | GVPSRFSGSGSG------TDFTFTISSLQPEDIATYYC | QQYEN------------LPIT | FAQGT RLEIK |
| iPS:394_029 | 21-225_1B12 | VK1|O18/JK5 | DIQMTQSPSSLSA SVGDRVTITC | QAS--QDIN-----NYLN | WCQQKPGK AFKLLIY | D-----ASNLET | GVPSRFSGSGSG------TDFTFTISSLQDITTYYC | QQYDN------------LPIT | FGGGT RLEIK |
| iPS:394_047 | 21-225_5E6 | VK1|O18/JK5 | DIQMTQSPSSLSA SVGDRVTITC | QAS--QDIN-----NYLN | WYQQKPGR APKLLIY | D-----ASNLET | GVPSRFSGSGSG------TDFTFTISSLQPEDIATYYC | QQFDN------------LPIT | FGGGT RLEIK |
| iPS:394_081 | 21-225_16B3 | VK1|O18/JK5 | DIQMTQSPSSLSA SVGDRVTITC | QAS--QDIN-----NYLN | WYQQKPGQ APKLLIY | D-----ASTRAT | GVPSRFSGSGSG------TDFTFTISSLQPEDIATYYC | QQYSN------------LPIT | FGGGT RLEIK |
| | VK3|L2/3|K3 | | K_FR1 | K_CDR1 | K_FR2 | K_CDR2 | K_FR3 | K_CDR3 | K_FR4 |
| iPS:434_219 | 21-225_60E9 | VK3|L2/JK3 | EIVMTQSPATLSV SPGERATLSC | RAS--QSVS-----SSLA | WYRQKPGQ APRLLIY | G-----ASTRAT | GIPARFSGSGSG------TEFLTISSLQSEDFAVYCC | QQYNN------------WPFT | FGPGT KIDIK |
| iPS:434_279 | 21-225_57F7 | VK3|L2/JK3 | EIVMTQSPAILSC FPGERAILSC | RAS--QSVS-----SDLA | WYQQKPGQ APRLLIY | G-----ASTRAT | GMPARFSGSGSG------TEFTLTISSLQSEHFAVYYC | QQYSN------------WPFT | FGEGT KVDIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:434 289 | 21-225_57H12 | VK3lL2/J K3 | EIVMTQSPATLSV SPGERATLSC | RAS--QSVS-----SDLA | WYQQKPGQ APRLLIY | A-------ASTRAT | GIPARFSGSGSG--TEFTLTISSLQSEDFAVYYC | QQYDN-----------WPFT | FGPGT KVDNK |
| iPS:434 291 | 21-225_58A4 | VK3lL2/J K3 | EIVMTQSPATLSV SPGERATLSC | RAS--QSVS-----SDLA | WYQQKPGQ APRLLIY | A-------ASTRAT | GIPARFSGSGSG--TEFTLTISSLQSEDFAVYYC | QQFNN-----------WPFT | FGPGT KVDIK |
| iPS:434 297 | 21-225_58A10 | VK3lL2/J K3 | EIVMTQSPATLSV CPGERATLSC | RAS--QSVS-----SSLA | WYQQKPGQ APKLLIY | G-------ASTRAT | GIPARFSGSGSG--TEFTLTISSLQSEDFAVYYC | QQYNN-----------WPFT | FGPGT KVDIK |
| iPS:434 301 | 21-225_58F11 | VK3lL2/J K3 | EIVMTQSPATLSV SPGERATLSC | RAS--QSVS-----SDLV | WYQQKPGQ AFRLLIY | G-------VSTRAT | GIPARFSGSGSG--TEFTLTISSLQSEDFAVYYC | QQYNN-----------WPFT | FGPGT KVDIK |
| iPS:437 228 | 21-225_60C11 | VK3lL2/J K3 | EIVMTQSPATLSV SPGERATLSC | RAS--QSVS-----NDLA | WYQQKPGQ APRLLIY | G-------ASTRAT | GIPARFSGSGSG--TEFTLTISALQSEDFAVYYC | QQYSN-----------WPFT | FGPGT KVDIK |
| | Germline VK2lA19/K5 | | | | | | | | |
| iPS:434 243 | 21-225_62C1 | VK2lA19/ JK5 | DIVMTQSPLSLPV TPGEPASISC | RSS------QSLLHSN-GYNYLD | WYLQKPGQ SPQLLIY | L-------VSNRAS | GVPDRFSGSGSG--TDFTLKISRVGAEDVGVYFC | LQALQ-----------TPLT | FGQGT RLEIK |
| iPS:436 648 | 21-225_227F11 | VK2lA19/ JK5 | DVVMTQSPLSLPV TPGEPASISC | WSS------QSLLHSN-GYNYLD | WYLQKPGQ SPQVLIY | L-------GSNRAS | GVPDRFSGSGSG--TDFTLKISRVEAEDVGVYYC | MQALQ-----------TPLT | FGQGT RLEIK |
| iPS:394 061 | 21-225_12D2 | VK2lA19/ JK5 | DIVMTQSPLSLPV TPGEPASISC | RSS------QSLLHSN-GYNYLD | WYLQKPGQ SPQVLIY | L-------GSNRAS | GVPDRFSGSGSG--TDFTLKISRVEAEDVGVYYC | MQALQ-----------TPLT | FGQGT RLEIK |
| iPS:394 071 | 21-225_10C7 | VK2lA19/ JK5 | DIVMTQSPLSLPV TPGEPASISC | RSS------QSLLHSK-GYNYLD | WYLQKPGQ SPQVLIY | L-------GSNRAS | GVPDRFSGSGSG--TDFTLKISRVEAEDVGVYYC | MQALQ-----------TPLT | FGQGT RLEIK |
| | Germline VK1lL5/K4 | | | | | | | | |
| iPS:434 259 | 21-225_62G7 | VK1lL5/J K4 | DIQMTQSPSSVSA SVGDRVTFTC | RAS--QGIS-----SWLA | WYQQNPGK APKLLIY | A-------ASSLQS | GVPSRFSGSGSG--INFTLTISSLQPEDFATYYC | QQTNS-----------FPLT | FGGGT KVEIK |
| iPS:434 333 | 21-225_63C9 | VK1lL5/J K4 | DIQMTQSPSSVSA SVGDRVTITC | RAS--QGIS-----SWLA | WYQQKPGK APNLLIY | A-------ASSLQS | GVPSRFSGSGSG--TDFTLTISGLQPEDFATYYC | QQTNS-----------FPLT | FGGGT KVAIK |
| iPS:434 347 | 21-225_64H10 | VK1lL5/J K4 | DIQMTQSPSSVSA SVGDRVTITC | RAS--QGIS-----SWLA | WYQQKPGK ALKLLIY | A-------ASSLQS | GVPSRFSGSGSG--TDFTLTISSLQPEDFATYYC | QQINS-----------FPLT | FGGGT KVEIK |
| iPS:434 359 | 21-225_65G3 | VK1lL5/J K4 | DIQMTQSPSSVSA SVGDRVTITC | RAS--QGIS-----SWLA | WYQQKPGK APKLLIY | A-------ASSLQS | GVPSRFSGSGSG--TDFTLTISSLQPEDFATYYC | QQYNS-----------FPLT | FGGGT KVEIK |
| iPS:434 369 | 21-225_66B1 | VK1lL5/J K4 | DIQMTQSPSSVSA SVGDRVTITC | RAS--QGIS-----SWLA | WYQQKPGK ALKLLIF | A-------ASSLQS | GVPSRFSGSGSG--TDFTLTISSLQPEDFATYYC | QQTNS-----------FPLT | FGGGT KVEIK |
| iPS:434 373 | 21-225_66A7 | VK1lL5/J K4 | DIQMTQSPSSVSA SVGDRVTITC | RAS--QGIS-----SWLA | WYQQKPGK AFKLLIY | A-------ASSLQS | GVPSRFSGSGSG--TDFTLTISSLQPEDFATYYC | QQINS-----------FPLT | FGGGT KVEIK |
| iPS:434 397 | 21-225_67H4 | VK1lL5/J K4 | DIQMTQSPSSVSA SVGDRVTITC | RAS--QGIS-----SWLA | WYQQKPGK AFKLLIY | A-------ASSLQS | GVPSRFSGSGSG--TDFTLTISSLQPEDFATYYC | QQINS-----------FPLT | FGGGT KVEIK |
| iPS:434 427 | 21-225_70D6 | VK1lL5/J K4 | DIQMTQSPSSVSA SVGDRVTITC | RAS--QGIS-----KWLA | WYQQNPGK APKLLIY | A-------ASSLQS | GVPSRFSGSGSG--TDFTLTISSLQPEDFANYYC | QQTNS-----------FPLT | FGGGT KVEIK |
| iPS:434 435 | 21-225_70G9 | VK1lL5/J K4 | DIQMTQSPSSVSA SVGDRVTITC | RAS--QGIS-----SWLA | WYQQNPGK AFKLLIY | A-------ASSLQS | GVPSRFSGSGSG--TDFTLTISSLQPEDFATYYC | QQTNS-----------FPLT | FGGGT KVEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:434_437 | 21-225_70A12 | VK1|L5/JK4 | DIQMTQSPSSVSA SVGDRVTITC | RAS--QGIS------SWLA | WYQQKPGK ALKLLIY | A-------ASSLQS | GVPSRFSGSGSG--TDFTLTISSVQPEDFATYYC | QQINS--------FPLT | FGGGT KVEIK |
| iPS:434_451 | 21-225_71B7 | VK1|L5/JK4 | DIQMTQSPSSVSA SVGDRVTITC | RAS--QGIS------SWLA | WYQQNPGE APKLLIY | A-------ASSLQG | GVPSRFSGSGSG--TDFTLTISSLQPEDFANYYC | QQTNS--------FPLT | FGGGT KVEIK |
| iPS:434_459 | 21-225_71A7 | VK1|L5/JK4 | DIQMTQSPSSVSA SVGDRVTITC | RAS--QGIS------SWLA | WYQQKPGK APKLLIY | A-------ASSLQS | GVPSRFSGSGSG--TDFTLTISSLQPEDFATYYC | QQVNS--------FPLT | FGGGT KVEIK |
| iPS:434_461 | 21-225_73A3 | VK1|L5/JK4 | DIQMTQSPSSVSA SIGDRVTITC | RAS--QGIS------NWLA | WYQQKPGK APKLLIY | A-------ASSLQS | GVPSRFSGSGSE--TDFTLTISSLQPEDFATYYC | QQVNS--------FPLT | FGGGT KVEIK |
| iPS:434_479 | 21-225_154E9 | VK1|L5/JK4 | DIQMTLSPSSVYA SVGDRVTITC | RAS--QDIS------NWLA | WYQQKPGK APKVLIY | A-------ASSLQS | GVPSRFSGSGSG--TDFTLTISSVQPEDFATYYC | QQGNS--------FPLT | FGGGT KVDIK |
| iPS:437_232 | 21-225_63E1 | VK1|L5/JK4 | DIQMTQSPSSVYA SVGDRVTITC | RAS--QGIS------SYLA | WYQQKPGK APKLLIY | A-------ASSLQS | GVPSRFSGSGSG--TDFTLTISSLQPEDFATYYC | QQANS--------FPLT | FGGGT KVEIK |
| iPS:437_326 | 21-225_75C10 | VK1|L5/JK4 | DIQMTQSPSSVSA SVGDRVTITC | RAS--QGIS------IWLA | WYQQKPGK APKLLIY | A-------ASSLQS | GVPLRFSGSGSG--TDFTLTISSLQPEDFATYYC | QQAKS--------FPLT | FGGGT KVEIK |
| | Germline | | | K_CDR1 | K_FR2 | K_CDR2 | K_FR3 | K_CDR3 | K_FR4 |
| | VK1|O12/JK2 | | | | | | | | |
| iPS:434_309 | 21-225_59B5 | VK1|O12/JK2 | DIQMTQSPSSLSA SVGDRVTITC | RAS--QSII------SYLN | WYQQKPGK APKLLIY | G-------ASSLQS | GVPSRFSGSGSG--TDFTLTISSLQPEDFATYYC | QQSYS--------TPMFS | FGQGT KLEIK |
| iPS:392_874 | 21-225_21D2 | VK1|O12/JK2 | DIQMTQSPSSLFA SVGDRVTITC | RAS--QSIS------DYLN | WYQQKPGR APKLLIY | D-------ASSLQS | GVPSRFSGSGSG--TDFTLIINSLQPEDFATYYC | QQTYNI-------LPERS | FGRGT KLEIK |
| iPS:393_940 | 21-225_16B2 | VK1|O12/JK2 | GVQMTQSPSSLSA SVGDRVTITC | RAS--QGIS------GYLN | WYQQKPGK APKLLIY | A-------ASSLQS | GVPSRFSGSGSG--TDFTLTISSLQPEDFATYYC | QQTYNT-------PPERS | FGGGT KLEIK |
| iPS:393_956 | 21-225_4D7 | VK1|O12/JK2 | DIQMTQSPSSLSA SVGDRVTITC | RAS--QSIS------DYLN | WYQQKPGK APKLLIF | D-------TTSLQS | GVPSRFSGSGSG--TDFTLTINSLQPEDFATYYC | QQTYNT-------PPERS | FGGGT KLEIK |
| iPS:398_476 | 21-225_17C1 | VK1|O12/JK2 | DIQMTQSPSSLSA SVGDRVTITC | RAS--QNIN------DYLN | WYQQKPGK APKLLIY | A-------ASNLQS | GVPARFSGSRSG--TDFTLTISSLQPEDFATYYC | QQTYNT-------PPERS | FGGGT KLEIK |
| iPS:403_870 | 21-225_23G4 | VK1|O12/JK2 | DIQMTQSPSSLSA SVGDRVTITC | RAS--QNIY------SYLN | WYQQKPGK APKLLIY | A-------ASSLQS | GVPSRFSGSGSG--TEFTLTITSILQPEDFATYYC | QQSYNT-------PPECN | FGPGT KLEIK |
| | Germline | | K_FR1 | K_CDR1 | K_FR2 | K_CDR2 | K_FR3 | K_CDR3 | K_FR4 |
| | VK3|A27/JK3 | | | | | | | | |
| iPS:434_311 | 21-225_59H5 | VK3|A27/JK3 | EIVLTQSPGTLSL SPGERATLSC | RAS--QSVSS----IYLA | WFLQKPGQ APRLLIY | G-------ASSRAT | GIPDRFSGSGSG--TDFTLTISRLEPEDFAVYYC | HQYGN--------SPFT | FGPGT KVDFK |
| iPS:435_301 | 21-225_146G4 | VK3|A27/JK3 | EIVLTQSPGTLSL FPGERATLSC | RAS--QNIIS----SYLA | WYQQKPGQ APRLLIF | G-------VSSRAT | GIPDRFSGSGSG--TDFTLTISRLEPEDFAVYYC | QQYGR--------SPFN | FGPGT KVDIN |
| iPS:435_317 | 21-225_147D2 | VK3|A27/JK3 | EIVLTQSPGTLSL SPGERATLSC | RAS--QSVGS----SYLA | WYQQKPGQ APRLLIY | G-------ASSRAT | GIPDRFSGSGSG--TDFTLTISRLEPEDFAVYYC | QQYG---------SLFT | FGPGT KVDIK |
| iPS:435_319 | 21-225_147E3 | VK3|A27/JK3 | EIVLTQSPGTLSL SPGERATLSC | RAS--QSIS------SYLA | WYQQKPGQ APRLLIF | G-------ASSRAT | AIPDRFSGSGSG--TDFTLTISRLEPEDFAVYYC | QQYGR--------SPFN | FGPGT KVDIK |
| iPS:435_383 | 21-225_149D7 | VK3|A27/JK3 | EIVLTQSPGTLSL FPGERATLSC | RAS--QSIIS----NYLA | WYQQKPGQ APRLLIF | G-------VSSRAT | GIPDRFSGSGSG--TDFTLTISRLEPEDFAVYYC | QQYGR--------SPFN | FGPGT KVDIK |
| iPS:435_443 | 21-225_152E7 | VK3|A27/JK3 | EIVLTQSPGTLSL FPGERATLSC | RAS--QSVIS-----SYLA | WYQQKPGQ APRLLIF | G-------VSSRAT | GIPDRFSGSGSG--TDFTLTISRLEPEDFAVYYC | QQYGR--------SPFN | FGPGT KVDIK |
| iPS:435_465 | 21-225_153A6 | VK3|A27/JK3 | EIVLTQSPGTLSL FPGERAPLSC | RAS--QSVIS-----SYLA | WYQQKPGQ APRLLIF | G-------VSSRAT | GIPDRFSGSGSG--TDFTLTISRLEPEDFAVYYC | QQYGR--------SPFN | FGPGT KVDIK |

Figure 51 (Continued)

| ID | | Family | FR1 | CDR1 | FR2 | CDR2 | FR3 | CDR3 | FR4 |
|---|---|---|---|---|---|---|---|---|---|
| iPS:436 058 | 21- 225_194A4 | VK3|A27/ JK3 | EIVLTQSPGTLSL SPGERATLSC | RAS--RGVSN-----IYLA | WYQQKPGQ APRLLIY | G------ ASNRAT | GIPDRFSGSGSG- TDFTLTISRLEPEDFAVYYC | QHNDY-----------SMFT | FGPGT KVDIK |
| iPS:436 436 | 21- 225_216F10 | VK3|A27/ JK3 | EVLTQSPGTLSL SPGERATLSC | RAS--QSVSS-----SFLA | WYQQKPGQ APRLLIY | G------ TSTRAT | GIPDRFSGSGSG- TDFTLTISRLEPEDFAVYYC | QQYDR-----------SPFT | FGPGT KVDIK |
| iPS:442 568 | 21- 225_149D8 | VK3|A27/ JK3 | EIVLTQSPGTLSL FPGERATLSC | RAS--QSVIS-----SYLA | WYQQKPGQ APRLLIF | G------ VSSWAT | GIPDRFSGSGSG- TDFTLTISRLEPEDFAVYYC | QQYGR-----------SPFN | FGPGT KVDIK |
| | Germline | | K_FR1 | K_CDR1 | K_FR2 | K_CDR2 | K_FR3 | K_CDR3 | K_FR4 |
| | VK1|O18/ K1 | | | | | | | | |
| iPS:434 353 | 21- 225_64B12 | VK1|O18/ JK1 | DIQMTQSPSSLSA SVGDRVTITC | RAS--QDIS-----NYLN | WYQQKPGT APNLLIS | D------ ASILET | GVPSTFSGSGSG- TDFTLTISSLQPEDIATYYC | QQSDN-----------LPCS | FGQGT KVEIK |
| | Germline | | K_FR1 | K_CDR1 | K_FR2 | K_CDR2 | K_FR3 | K_CDR3 | K_FR4 |
| | VK1|A20|JK 4 | | | | | | | | |
| iPS:434 357 | 21- 225_65C1 | VK1|A20/ JK4 | DIQLTQSPSSLSA SVGDRVTITC | RAS--QVIS-----SYLH | WYQQKPGK VPKVLIY | S------ ASNLQC | GVPSRFSGSGSG- TDFTLTIFSSLQPEDVATYYG | QRPYN-----------APLT | FGGGT KVEIK |
| iPS:434 375 | 21- 225_66C7 | VK1|A20/ JK4 | DIQLTQSPSSLSA SVGDRVTITR | RAS--QGIS-----NYLH | WYQQKPGK APKLLIY | C------ ASNLQC | GVPSRFSGSGSG- TDFTLTISSLQPEDVATYYC | QQHNN-----------SPLT | FGGGT KVEIK |
| iPS:434 457 | 21- 225_72G12 | VK1|A20/ JK4 | DIQLTQSPSSLSA SVGDRVTITC | RAS--QGIS-----SYLN | WSQQKPGK VPKLLIC | G------ ASNLQS | GVPSRFSGSASG- TDFTLTISSLQPEDVTTYYG | QQNYN-----------APLT | FGGGT KVEIK |
| | Germline | | K_FR1 | K_CDR1 | K_FR2 | K_CDR2 | K_FR3 | K_CDR3 | K_FR4 |
| | VK3|A27|JK 4 | | | | | | | | |
| iPS:434 479 | 21- 225_76H1 | VK3|A27/ JK4 | EFMLTQSPGTLYM SPGERATLSC | RAS--QSVSS-----SYLV | WYQQKPGQ APRLLIY | G------ ASTRAT | GIPDRFSGSGSG- TDFTLTISRLEPEYFAVYYC | QQYGC-----------SPLT | FGGGT KVEIK |
| iPS:434 513 | 21- 225_76A6 | VK3|A27/ JK4 | EIVLTQSPGTRSW SPGERATLSC | RAS--QSVSS-----SYLA | WYQQKPGQ APRLLIY | G------ ASTRAT | GIPDRFSGSGSG- TDFTLTISRLEPEYFAVYYC | QQYGN-----------SPLT | FGGGT KVEIK |
| iPS:434 515 | 21- 225_74A5 | VK3|A27/ JK4 | EFMLTQSPGTLSL SPGERATLSC | RAS--QSVSS-----SYLA | WYQQKPGQ APRLLIY | G------ ASTRAT | GIPDRFSGSGSG- TDFTLTISRLEPEYFAVYYC | QQYGC-----------SPLT | FGGGT KVEIK |
| iPS:434 529 | 21- 225_76B9 | VK3|A27/ JK4 | EFMLTQSPGTLSW SPGERATLSC | RAS--QSVSS-----SYLV | WYQQKPGQ APRLLIY | G------ ASTRAT | GIPDRFSGSGSG- TDFTLTISRLEPEYFAVYYC | QQYGC-----------SPLT | FGGGT KVEIK |
| iPS:434 583 | 21- 225_74B6 | VK3|A27/ JK4 | EIVLTQSPGTLSL SPGERATLSC | RAS--QSVSS-----SYLA | WYQQKPGQ APRLLIY | G------ ASTRAT | GIPDRFSGSGSG- TDFTLTISRLEPEYFAVYYC | QQYGN-----------SPLT | FGGGT KVEIK |
| iPS:434 587 | 21- 225_74G3 | VK3|A27/ JK4 | EFMLTQSPGTLCW SPGERATLSC | RAS--QSVSS-----SYLA | WYQQKPGQ APRLLIY | G------ ASTRAT | GIPDRFSGSGSG- TDFTLTISRLEPEYFAVYYC | QQYGC-----------SPLT | FGGGT KVEIK |
| iPS:434 603 | 21- 225_77D11 | VK3|A27/ JK4 | EFMLTQSPGTLYM SPGERATISC | RAS--QSVSS-----SYLV | WYQQKPGQ APRLLIY | G------ ASTRAT | GIPDRFSGSGSG- TDFTLTISRLEPEYFAVYYC | QQYGC-----------SPLT | FGGGT KVEIT |
| iPS:434 705 | 21- 225_80A2 | VK3|A27/ JK4 | EFMLTQSPGTLYL SPGERATLSC | RAS--QSVSS-----SYLA | WYQQKPGQ APRLLIY | G------ ASTRAT | GIPDRFSGSGSG- TDFTLTISRLEPEYFAVYYC | QQYGN-----------SPLT | FGGGT KVEIT |
| iPS:434 747 | 21- 225_80C12 | VK3|A27/ JK4 | EIVLTQSPGTLYL SPGERATLSC | RAS--QSVSS-----SYLA | WYQQKPGQ APRLLIY | G------ ASTRAT | GIPDRFSGSGSG- TDFTLTISRLEPEYFAVYYC | QQYGN-----------SPLT | FGGGT KVEIK |
| iPS:434 793 | 21- 225_82A5 | VK3|A27/ JK4 | EIVLTQSPGTLYM SPGERATLSC | RAS--QSVSS-----SYLA | WYQQKPGQ APRLLIY | G------ ASTRAT | GIPDRFSGSGSG- TDFTLTISRLEPEYFAVYYC | QQYGN-----------SPLT | FGGGT KVEIK |
| iPS:434 797 | 21- 225_82G5 | VK3|A27/ JK4 | EFMLTQSPGTLYM SPGERATLSS | RAS--ESVSS-----SYLV | WYQQKPGQ APRLLIY | G------ ASTRAT | GIPDRFSGSGSG- TDFTLTISRLEPEYFAVYYC | QQYGC-----------SPLT | FGGGT KVEIK |
| iPS:434 805 | 21- 225_82D9 | VK3|A27/ JK4 | EFMLTQSPGTLSW SPGERATLSC | RAS--ESVSS-----SYLV | WYQQKPGQ APRLLIY | G------ ASTRAT | GIPDRFSGSGSG- TDFTLTISRLEPEYFAVYYC | QQYGC-----------SPLT | FGGGT KVEIT |

Figure 51 (Continued)

| | | | | | | | | | | |
|---|---|---|---|---|---|---|---|---|---|---|
| iPS:434 813 | 21-225_82C12 | VK3JA27/ JK4 | EIVLTQSPGTLSW SPGERATLSC | RAS--QSVSS- ----SYLA | WYQQKPGQ APRLLIY | G------- ASTRAS | GIPDRFSGSGSG- TDFTLTISRLEPEYFAVYYC | QQYGN------ ------SPLT | FGGGT KVEIK |
| iPS:434 825 | 21-225_83C2 | VK3JA27/ JK4 | EFMLTQSPGTLCL SPGERATLSC | RAS--QSVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIK |
| iPS:434 833 | 21-225_83C5 | VK3JA27/ JK4 | EFMLTQSPGTLCW SPGERATLSC | RAS--ESVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIT |
| iPS:434 883 | 21-225_85B5 | VK3JA27/ JK4 | EFMLTQSPGTLSL SPGERATLSC | RSS--QSVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIK |
| iPS:434 911 | 21-225_85D11 | VK3JA27/ JK4 | EFMLTQSPGTLSL STGERATLSC | RSS--QSVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIK |
| iPS:434 957 | 21-225_87A10 | VK3JA27/ JK4 | EFVLTQSPGTLYL SPGERATLSC | RAS--QSVSS- ----SFLA | WYQQKPGQ APRLLIY | G------- ASTRAS | GIPDRFSGSGSG- TDFTLTISRLEPEYFAVYYC | QQYGN------ ------SPLT | FGGGT KVEIK |
| iPS:435 247 | 21-225_87A10 | VK3JA27/ JK4 | EIVLTQSPGTLSL SPGERATLSC | RAS--QSVSS- ----SYLA | WYQQKPGQ PPRLLIY | G------- ASTRAS | GIPDRFSGSGSG- TDFTLTISRLEPEYFAVYYC | QQYGN------ ------SPLT | FGGGT KVEIK |
| iPS:436 368 | 21-225_211G3 | VK3JA27/ JK4 | EIVLTQSPGTLSL SPGERATLSC | RAS--QSVSS- ----SFLA | WYQQKPGQ APRLLIY | G------- ASSRAT | GIPDRFSGSGSG- TDFTLTISRLEPEDFAVYYC | QQYVS------ ------SPLT | FGGGT KVEIK |
| iPS:436 426 | 21-225_215C7 | VK3JA27/ JK4 | EIVLTQSPGTLSL SPGERVTLSC | RAS--QRITT- ----NFLA | WYQQKPGQ APRLLIY | G------- ASSRAT | GIPDRFSGSGSG- TDFTLTISRLESEDFAVYYC | QQYVS------ ------SLLT | FGGGT KVEIK |
| iPS:436 432 | 21-225_215H1 2 | VK3JA27/ JK4 | EIVLTQSPGTLSL SPGERATLSC | RAS--QSVSS- ----SFLA | WYQQKPGQ APRLLMY | G------- ASSRAI | GIPDRFSGSGSG- TDFTLTISRLEPEDFAVYYC | QQYVS------ ------SPLT | FGGGT KVEIK |
| iPS:437 322 | 21-225_75B1 | VK3JA27/ JK4 | EFMLTQSPGTLSS SPGERATISS | RAS--QSVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIK |
| iPS:437 377 | 21-225_74G9 | VK3JA27/ JK4 | EFMLTQSPGTLSL SPGERATLSC | RAS--QSVSS- ----SYLV | WYQQKPGQ APRLLIY | G------- ASTRAT | GIPDRFSGSGSG- TDFTLTISRLEPEYFAVYYC | QQYGC------ ------SPLT | FGGGT KVEIT |
| | | Germline | K_FR1 | K_CDR1 | K_FR2 | K_CDR2 | K_FR3 | K_CDR3 | K_FR4 |
| | | VK4JB3JK4 | DIVMTQSPDSLAV SLGERATINC | KSS--QSVLYSSNNKN YLA | WYQQKPGQ PPKLLIY | W------- ASTRES | GVPDRFSGSGSG- TDFTLTISSLQAEDVAVYYC | QQYYS------ ------TPPT | FGGGT KVEIK |
| iPS:434 511 | 21-225_74B11 | VK4JB3/J K4 | DIVMTQSPDSLTV SLGERATISS | KSS--- QSILYNSNNNN YLA | WYQQKPGQ PPKLLIY | W------- ASTRES | GVPDRFSGSGSG- TDFTLTISSLQAEDVAVYYC | QQYYS------ ------TPPT | FGGGT KVEIK |
| iPS:434 729 | 21-225_80B12 | VK4JB3/J K4 | DIVLTQSPDSLAV SLGERATINC | KSR--- QSVLYSSNNYN YLT | WYQQKPGQ PPKLLIY | W------- ASTRES | GVPDRFSGSGSG- TDFTLTISSLQAEDVAVYYC | QQYYS------ ------SPPT | FGGGT KVEIK |
| iPS:434 851 | 21-225_75A6 | VK4JB3/J K4 | DIVMTQSPDSLAV SLGERATINC | KSR--- QSVLHSSNNYN YLA | WYQQKPGQ PPELLIY | W------- ASTRES | GVPDRFSGSGCG- TDFTLIDSLQAEDVAVYYC | QQYYS------ ------TPPT | FGGGT KVEIK |
| iPS:435 623 | 21-225_162D5 | VK4JB3/J K4 | DIVMTQSPDFRNV SMGERAIINE | KSN--- HSVLYRSNNNQ YLA | WYQRKPGQ PPKLLIY | R------- TSIRKS | GVPDRFSGSGCG- TDFTLIDSLQAEDVAVYYC | QQYYS------ ------TPPT | FGGGT KVEIK |
| iPS:446 086 | 21-225_94D8 | VK4JB3/J K4 | DIVLTQSPDSLAV SLGERATINC | KSR--- QSVLYSSNNYN YLT | WYQQKPGQ PPKLLIY | W------- ASTRES | GVPDRFSGSGSG- TDFTLTISSLQAEDVAVYYC | QQYYS------ ------SPPT | FGGGT KVEIK |
| | | Germline | K_FR1 | K_CDR1 | K_FR2 | K_CDR2 | K_FR3 | K_CDR3 | K_FR4 |

Figure 51 (Continued)

| | VK2JA19/JK4 | | | | | | | | |
|---|---|---|---|---|---|---|---|---|---|
| iPS-434 539 | 21-225_74A2 | VK2JA19/JK4 | DIVMTQSPLSLPV TPGEPASISC | RSS-- QSLLHSN-GHNYLD | WYLQKPGR SPQLLIY | L------ GSNRAS | GVPERFSGSGSG-- TDFTLKISRVEAEDVGVYYC | MQPLQ---------- ------------TPFT | FGGGT KVEIK |
| iPS-434 563 | 21-225_75D8 | VK2JA19/JK4 | DIVMTQSPLSLPV TPGEPASISC | RSS-- QSLLHSS-GYNYLD | WYLQKPGQ SPQLLIY | L------ GSNRAS | GVPDRFSGSGSG-- SDFTLKISRVEAEDVGLYYC | MQALH---------- ------------PPLT | FGGGT KVEIK |
| iPS-435 009 | 21-225_89G4 | VK2JA19/JK4 | DIVMTQSPLSLPV TPGEPASISC | RSS-- QSLLHSS-GYNYLD | WYLQKPGQ SPQLLIY | L------ GSNRAS | GVPDRFSGSGSG-- TDFTLKISRVEAEDIGVYYC | MQALH---------- ------------IPLT | FGGGT KVEIK |
| iPS-435 059 | 21-225_90C11 | VK2JA19/JK4 | DIVMTQSPLSLPV TPGEPASISC | RYS-- QSLVHSS-GYNYLD | WYLQKPGQ SPQLVIY | L------ GSNRAS | GVPDRFSGSGSG-- SDFTLKISRVEAEDVGLYYC | MQALH---------- ------------PPLT | FGGGT KVEIK |
| iPS-435 103 | 21-225_92B2 | VK2JA19/JK4 | DIVMTQSPLSLPV TPGEPASISC | RSS-- QSLVHSS-GYNYLD | WYLQKPGQ SPQLVIY | L------ GSNRAS | GVPDRFSGSGSV-- TDFTLRISRVEAEDIGIYYC | MQTLQ---------- ------------IPLT | FGGGT KVEIK |
| iPS-435 713 | 21-225_171D7 | VK2JA19/JK4 | DIVMTQSPLSLPV TPGEPASISC | RSS-- QSLLYHN-RYNHLD | WYLQKIGQ SPQLLIY | V------ GSNRAS | GVPDRFSGSGSG-- TDFTLKISRVEAEDVGVYYC | MQAL----------- ------------TPFT | FGGGT KVEIK |
| iPS-436 246 | 21-225_201G6 | VK2JA19/JK4 | DIVMTQSPLSLPV TPGEPASISC | RSS-- QSLLHNN-RYNHLD | WYLQKPGQ SPQLLIY | L------ GSNRAS | GVPDRFSGSGSG-- TDFTLKISRVEAEDVGVYYC | MQAL----------- ------------QTPT | FGGGT KVEIK |
| iPS-436 254 | 21-225_202C1 2 | VK2JA19/JK4 | DIVMTQSPLSLPV TPGEPASISC | RSS-- QSLLHNN-KYNHLD | WYLQKPGQ SPQLLIY | L------ GSNRAS | GVPDRFSGSGSG-- TDFTLKISRVEAEDVGVYYC | MQAL----------- ------------QTPT | FGGGT KVEIK |
| iPS-436 304 | 21-225_201F3 | VK2JA19/JK4 | DIVLTQSPLSLPV TPGEPASISC | RSS-- QSLLHNN-RYNHLD | WYLQKPGQ SPQLLIY | L------ GSNRAS | GVPDRFSGSGSG-- TDFTLKISRVEAEDVGVYYC | MQAL----------- ------------QTPT | FGGGT KVEIK |
| iPS-436 334 | 21-225_208G3 | VK2JA19/JK4 | DIVMTQSPLSLPV TPGEPASISC | RSS-- QSLLHNN-KYNHLD | WYLQKPGQ SPQLLIY | L------ GSNRAS | GVPDRFSGSGSG-- TDFTLKISRVEAEDVGVYYC | MQAL----------- ------------QTPT | FGGGT KVEIK |
| iPS-437 248 | 21-225_97H3 | VK2JA19/JK4 | DIVMTQSPLSLPV TPGEPASISC | RSS-- QSLLHSN-GHNYLD | WYLQKPGR SPQLLIY | L------ GSNRAS | GVPERFSGSGSG-- TDFTLKISRVEAEDVGVYYC | MQPLQ---------- ------------TPFT | FGGGT KVEIK |
| iPS-437 320 | 21-225_75A1 | VK2JA19/JK4 | DIVMTQSPLSLPV TPGEPASISC | RSS-- QSLLHSS-GYNYLD | WYLQKPGQ SPQLLIY | L------ GSNRAS | GVPDRFSGSGSG-- SDFTLKISRVEAEDVGLYYC | MQPLQ---------- ------------PPLT | FGGGT KVEIK |
| iPS-437 371 | 21-225_74D8 | VK2JA19/JK4 | DIVMTQSPLSLPV TPGEPASISC | RSS-- QSLVHSS-GYNYLD | WYLQKPGQ SPQLVIY | L------ GSNRAS | GVPDRFSGSGSG-- TDFTLKISRVEAEDVGVYYC | MQALH---------- ------------TPFT | FGGGT KVEIK |
| iPS-392 718 | 21-225_17B8 | VK2JA19/JK4 | DIVMTQSPLSLPV TPGEPASISC | RSS-- QSLLHSN-GNNSLD | WYLQKPGQ SPQLLIY | L------ GSHRAS | GVPDRFSDSGSG-- TDFTLKISRVEAEDVGVYYC | MQVLQ---------- ------------TPPLT | FGGGT KVEIK |
| Germline | | | K_FR1 | K_CDR1 | K_FR2 | K_CDR2 | K_FR3 | K_CDR3 | K_FR4 |

Figure 51 (Continued)

| ID | | | FR1 | CDR1 | FR2 | CDR2 | FR3 | CDR3 | FR4 |
|---|---|---|---|---|---|---|---|---|---|
| iPS:434 871 | 21-225_85H1 | VK3lL2/J K1 | EIVMTQSPATLSV SPGERATLSC | RAS--QDVI -----TYLA | WYQQKPGQ APRLLIY | G------- ASTRAT | GVPARFSGSGSG-- TEFTLTISSLQSEDFALYYC | QEYND------ ----------WPCS | FGQGT KVEIK |
| iPS:435 421 | 21-225_151F1 | VK3lL2/J K1 | EMVMTQSPAILSV SPGERVTLSC | RAS--QSIN -----INIA | WYQQKPGQ APRLLIY | G------- ASTRAT | GIPARFSGSGSG-- TEFTLTISSLQSEDFAVYYC | QQYND------ ----------WPPWT | FGQGT KVEIK |
| iPS:435 497 | 21-225_155H9 | VK3lL2/J K1 | EIVMTQSPATLSV SPGERATLSC | RAS--QSVS -----SNLA | WYQQKPGQ APRLLIY | G------- ASTRAT | GIPARFSGSGSG-- TEFTLTISSLQSEDFAVYYC | QQYDD------ ----------WPPWT | FGQGT KVEIK |
| iPS:435 605 | 21-225_161A4 | VK3lL2/J K1 | EIVMTQSPATLSV SPGERASLSC | RSS--QSVN -----SNLA | WYQQRPGQ ALRLLIY | G------- ASTRAT | DIPARFNGSGSG-- TEFTLTISSLQSEDFAVYFC | QQYN------- ----------NWWT | FGQGT TVEIK |
| iPS:451 118 | 21-225_191C8 | VK3lL2/J K1 | EIVMTQSPATLSV SPGERATLSC | RAS--QSVR -----SNLA | WYQQEPGQ APRLLIY | G------- ASTRAT | GIPARFSGSGSG-- TEFTLTISSLQSEDFAVYYC | QQSFT------ ----------WLRT | FGQGT KVEIK |
| iPS:392 734 | 21-225_17D8 | VK3lL2/J K1 | EIVMTQSPSTLSV SPGERATLSC | RAS--QSVS -----SNLA | WFQQKPGQ APRLLIN | G------- ASTRAS | GIPARFSGSGSG-- TEFTLTISSLQSEDFAVYYC | QQYNN------ ----------WPLT | FGQGT KVEIK |
| iPS:392 768 | 21-225_20B8 | VK3lL2/J K1 | EIVMTQSPSTLSV SPGERVTLSC | RAS--QSVS -----SNLA | WFQQKPGQ APRLLIN | G------- ASTRAS | GIPARFSGSGSG-- TEFTLTISSLQSEDFAVYYC | QQYNN------ ----------CPLT | FGQGT KVEIK |
| iPS:393 044 | 21-225_25B8 | VK3lL2/J K1 | EIVMTQSPATLSV SPGERATLSC | RAS--QSVR -----SNLA | WYQQKPGQ APRLLIY | G------- ASTRAT | GIPARFSGSGSG-- TEFTLTISSLQSEDFALYYC | QQYNN------ ----------WPPWP | FGQGT KVEIK |
| iPS:393 050 | 21-225_28C5 | VK3lL2/J K1 | EIVMTQSPATLSV SPGERATLSC | RAS--QSVS -----SNLA | WYHQKPGQ APRLLIY | G------- ASTRAT | GIPARFSGSGSG-- TEFTLTISSLQSEDFAVYYC | QQYNN------ ----------WPPWP | FGQGT KVEIK |
| iPS:393 906 | 21-225_13D3 | VK3lL2/J K1 | EIVMTQSPATLSV SPGESATLSC | RAS--QTVS -----SNLA | WFQQKPGQ APRLLIN | G------- ASTRAT | GIPARFSGSGSG-- TEFTLTISSLQSEDFAVYFC | QQYHD------ ----------WPPT | FGQGT KVEIK |
| | Germline | | K_FR1 | K_CDR1 | K_FR2 | K_CDR2 | K_FR3 | K_CDR3 | K_FR4 |
| VK1lL1/JK5 | | | | | | | | | |
| iPS:434 947 | 21-225_87B7 | VK1lL1/J K5 | DIQMTQSPSSLSA SVGDRVTITC | RAS--QGIS -----NYLA | WFQQKPGK APKSLIY | A------- ASSLHS | GVPSKFSGSGSG-- TDFTLTISSLQPEDSATYFC | LLYLT------ ----------YPLT | FGQGT RLEIK |
| iPS:435 427 | 21-225_151C9 | VK1lL1/J K5 | DIQMTQSPSSLSA SVGDRVTITC | RAS--QGIS -----KYLA | WFQQKPGK APKSLIY | D------- ASRLQS | GVPSKFSGSGSG-- TDFTLTISSLQPEDFASYYC | HQYKH------ ----------YPIT | FGQGT RLEIK |
| iPS:435 529 | 21-225_157H7 | VK1lL1/J K5 | DIQMTQSPSSLSA SVGDRVTITC | RAS--QDIS -----NFLA | WFQQKPGK APKSLVS | T------- ASRLQS | GVPSKFSGSGSG-- TDFTLTISSLQPEDFATYYC | QQYHS------ ----------YPIT | FGQGT RLEIK |
| iPS:436 066 | 21-225_194B7 | VK1lL1/J K5 | DIQMTQSPSSLSA SVGDRVTITC | RAS--QGIS -----KYLA | WFQQKPGK APKSLIY | G------- ASRLQS | GVPSKFSGSGSG-- TDFTLTISSLQPEDFATYYC | QHYLN------ ----------YPLT | FGQGT RLEIK |
| iPS:437 274 | 21-225_196D4 | VK1lL1/J K5 | DIQMTQSPSSLSA SVGDRVTITC | RAS--QGIS -----NYLA | WFQQNPGK APKSLIY | A------- ASSLQS | GVPSKFSGSGCG-- TDFTLTISSPQPEDVATYYC | QHYLN------ ----------YPLT | FGQGT RLEIK |
| iPS:392 748 | 21-225_20A8 | VK1lL1/J K5 | DIQMTQSPSSLSA SVGDRVTITC | RAS--QGIN -----NYLV | WFQQKPGK APKSLIY | A------- ASSLLS | GVPSKFSGSGSG-- TDFTLTISSLQPEDFATYYC | QQYNS------ ----------YPLT | FGQGT RLEIK |
| iPS:393 062 | 21-225_33H3 | VK1lL1/J K5 | DIQMTQSPSSLSA SVGDRVTITC | QAS--QDIS -----NFLN | WFRQKPGK APNSLIY | D------- ASNLVT | GVPSRFSGSGSG-- TDFTFTISSLQPEDFATYYC | QQYDN------ ----------LPIT | FGQGT RLEIK |
| iPS:398 532 | 21-225_33B7 | VK1lL1/J K5 | DIQMTQSPSSLSA SVGDRVTITC | RAS--QDIS -----NYLA | WFQQKPGK APTSLIY | A------- ASSLQS | GVPSKFSGSGSG-- TDFTLTISSLQPEDFATYYC | QQYHS------ ----------YPIT | FGQGT RLEIK |
| iPS:402 221 | 21-225_2C12 | VK1lL1/J K5 | DIQMTQSPSSLSA SVGDRVTITC | RAS--QGIS -----NYLA | WFQQKSGK APKSLIS | A------- ATSLQS | GVPSQFSGSGSG-- TDFTLTISSLQPEDFATYYC | QQYYS------ ----------YPIT | FGQGT RLEIK |
| | Germline | | K_FR1 | K_CDR1 | K_FR2 | K_CDR2 | K_FR3 | K_CDR3 | K_FR4 |
| VK4lB3/JK5 | | | | | | | | | |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:435 665 | 21-225_169F2 | VK4|B3/JK5 | DIVMTQSPDSLAV SLGERATINC | KSS--QSVLYISNNKN YLA | WYQQKPGQ PFKLLIY | W-------ASTRES | GVPDRFSGSGSG--IDFTLTISSLQAEDVAVYYC | QQYY--------RAPT | FGQGT RLEIK |
| iPS:435 671 | 21-225_169H5 | VK4|B3/JK5 | DIVMTQSPDSLAV SLGERATINC | KSS--QSVLYISNNKN YLA | WYQQKPGQ PFKLLIY | W-------ASTRES | GVPDRFSGSGSG--IDFTLTISSLQAEDVAVYYC | QQYY--------RAPT | FGQGT RLEIK |
| iPS:436 554 | 21-225_224C10 | VK4|B3/JK5 | DIVMTQSPDSLAA SLGERATITC | KSS--QSVLYNSNNKN YLA | WYQQKPGQ PFKLLIY | W-------ASTRES | GVPDRFSGSGSG--IDFTLTISSLQAEDVAIYYC | QQYYI--------NPCS | FGQGT RLEIK |
| iPS:398 510 | 21-225_25A3 | VK4|B3/JK5 | DIVMTQSPDSLTV SLGERATINC | KSS--QSVLYSSNNKN YLA | WYQQKPGQ PFKLLIY | W-------ASTRES | GVPDRFSGSGSG--IDFTLTISSLQAEDVAVYYC | QQYYS--------TPCS | FGQGT RLEIK |
| iPS:398 516 | 21-225_26A9 | VK4|B3/JK5 | DIVMTQSPDSLAV SLGERATINC | KSS--QSVLYSSNNKN YLA | WYQQKPGQ PFKLLIY | W-------ASTRES | GVPDRFSGSGSG--IDFTLTISSLQAEDVAVYYC | QQYYS--------SPCS | FGQGT RLEIK |
| VK2|A19|JK1 | Germline | | | | | | | | |
| iPS:435 667 | 21-225_169E3 | VK2|A19/JK1 | DIVMTQSPLSLPV TPGEPASISC | RSS--QSLLHNN-GYKYLD | WYLQKPGQ SPQLLIY | L-------GSNRAS | GVPDRFSASGSG--IDFTLKISRVEAEDVGVYYC | MQVLQ--------TPWT | FGQGT KVEIK |
| iPS:435 673 | 21-225_169E6 | VK2|A19/JK1 | DIVMTQSPLSLPV TPGEPASISC | RSS--QSLLHNN-----SSLH | WYLQKPGQ SPQLLIY | L-------GSNRAS | GVPDRFSASGSG--IDFTLKISRVEAEDVGVYYC | MQVLQ--------TPWT | FGQGT KVEIK |
| iPS:435 759 | 21-225_176E6 | VK2|A19/JK1 | DIVMTQSPLSLPV TPGEPASISC | RSS--QSLLHNN-GYKYLD | WYLQKPGQ SPQLLIY | L-------GSNRAS | GVPDRFSASGSG--IDFTLKISRVEAEDVGVYYC | MQVLQ--------TPWT | FGQGT KVEIK |
| VK6|A26|JK1 | Germline | | | | | | | | |
| iPS:435 817 | 21-225_190B1 | VK6|A26/JK1 | EIVLTQFPDSQSV APKEKVTITC | RAS--QSIG------SNLH | WYQQKPDQ SPKLLIK | Y-------ASQSFS | GVPSRFSGSGSG--IDFTLTINSLEAEDAATYYC | QQSSS--------LPWT | FGQGT KVEIK |
| iPS:435 823 | 21-225_190F11 | VK6|A26/JK1 | EIVLTQFPDSQSV TPKEKVTITC | RAS--QNIG------SSLH | WYQQKPEQ SPKVLIK | Y-------ASQSFS | GVPSRFSGSGSG--IDFTLTINSLEAEDAATYYC | HQSSS--------FPRT | FGQGT KVEIK |
| iPS:435 867 | 21-225_191E5 | VK6|A26/JK1 | EIVLTQFPDSQSV TPKEKVTITC | RAS--QSIG------SSLH | WYQQKPDQ SPKLLIK | Y-------ASQSFS | GVPSRFSGSGSG--IDFTLTINSLEAEDAATYYC | HQSSS--------FPRT | FGQGT KVEIK |
| iPS:435 917 | 21-225_190D5 | VK6|A26/JK1 | EIVLTQFPDSQSV TPKEKVTITC | RAS--QSIG------SNLH | WYQQKPDQ SPKLLIK | S-------ASQSFS | GVPSRFSGSGSG--IDFTLTINSLETEDAATYYC | QQSSS--------LPWT | FGQGT KVEIK |
| iPS:435 929 | 21-225_190D9 | VK6|A26/JK1 | EIVLTQFPDSQSV TPKEKVTITC | RAS--QSIG------SSLH | WYQQKPDQ SFKLLIK | Y-------ASQSFS | GVPSRFSGSGSG--IDFTLTINSLEAEDAATYYC | HQSSS--------FPRT | FGQGT KVEIK |
| iPS:435 935 | 21-225_190H8 | VK6|A26/JK1 | EIVLTQFPDSQSV TPKEKVTITC | RAS--QSIG------SSLH | WYQQKPDQ SPKLLIK | Y-------ASQSFS | GVPSRFSGSGSG--IDFTLTINSLEAEDAATYYC | HQSSS--------FPRT | FGQGT KVEIK |
| iPS:436 056 | 21-225_194C3 | VK6|A26/JK1 | EIVLTQFPDSQSV TPKEKVTITC | RAS--QSIG------SNLH | WYQQKPDQ SPKLLIK | S-------ASQSFS | GVPSRFSGSGSG--IDFTLTINSLETEDAATYYC | QQSSS--------LPWT | FGQGT KVEIK |
| iPS:436 216 | 21-225_200B7 | VK6|A26/JK1 | EIVLTQSPDFQSV TPKEKVTITC | RAS--QNIG------NTLH | WYQQKPDQ SPKLLIK | Y-------ASQSFS | GVPSRFSGSGSG--IDFTLTINSLEAEDAATYYC | HQSGS--------LPQT | FGQGT KVEIK |

Figure 51 (Continued)

| | | K_FR1 | K_CDR1 | K_FR2 | K_CDR2 | K_FR3 | K_CDR3 | K_FR4 |
|---|---|---|---|---|---|---|---|---|
| iPS:436_220 | VK6|A26/JK1 | EIVLTQSPDFQSV APKEKVTITC | RAS--QSIG-----SMLH | WYQQKPDQ SPKLLIK | S-------ASQSFS | GVPSRFSGSGSG-TDFTLTINSLETDAATYYC | QQSSS--------LPWT | FGGGT KVEIK |
| iPS:436_448 | VK6|A26/JK1 | EIVLTQSPDFKSV TPKEKVTITC | RAS--QSIG-----SSLH | WYQQKPDQ SPKLLVK | Y-------ASQSFS | GVPSRFSGSGSG-TDFTLTINSLEAEDGATYYC | HQSRS--------LPWT | FGGGT KVEIK |
| VK6|A26|JK1 | Germline | | | | K_CDR2 | K_FR3 | K_CDR3 | K_FR4 |
| iPS:435_829 | VK6|A26/JK4 | EIVLTQSPDFQSV TPKEKVTITC | RAS--QSIG-----SSLH | WYQQKPDQ SPKLLIK | Y-------ASQSFS | GDPSRFSGSGSG-TDFTLTINSLEAEDAATYYC | HQTRS--------LPLT | FGGGT KVEIK |
| iPS:435_191H4 | VK6|A26/JK4 | EIVLTQSPDFQSV TPKEKVTITC | RAN--QSIG-----SSLH | WYQQKPDQ SPKLLIK | Y-------ASQSLS | GVPSRFSASGSG-TDFTLTINSLDAEDAATYYC | HQTRS--------LPLT | FGGGT KVEIK |
| iPS:435_191C9 | VK6|A26/JK4 | EIVLTQSPDFQSV TPKEKVTITC | RAS--QSIG-----SSLH | WYQQKPDQ SPKLLIK | Y-------ASQSFS | GDPSRFSGSGSG-TDFTLTINSLEAEDAATYYC | HQTRS--------LPLT | FGGGT KVEIK |
| iPS:435_192E5 | VK6|A26/JK4 | EIVLTQSPDFQSV TPKEKVTITC | RAS--QSIG-----RSLH | WYQQKPDQ SPKLLIK | Y-------ASQSFS | GVPSRFSGSGSG-TDFTLTINSLEAEDAATYYC | HQSSR--------LPLT | FGGGT KVEIK |
| iPS:436_043 | VK6|A26/JK4 | EIVLTQSPDFQSV TPKEKVTITC | RAS--QSIG-----RSLH | WYQQKPDQ SLRLLIK | Y-------ASQSFS | GVPSRFSGSGSG-TDFTLTINSLEAEDAATYYC | HQSSR--------LPLT | FGGGT KVEIK |
| iPS:436_084 | VK6|A26/JK4 | EIVLTQSPDFQSV TPKEKVTITC | RAS--QSIG-----SSLH | WYQQKPDQ SPKLLIK | Y-------ASQSFS | GVPSRFSGSGSG-TDFALTINSLEAEDAATYYC | HQSRT--------LPLT | FGGGT KVEIK |
| iPS:436_094 | VK6|A26/JK4 | EIVLTQSPDFQSV TPKEKVTITC | RAS--QSIG-----SSLH | WYQQKPDQ SPKLLIK | Y-------ASQSFS | GVPSRFSGSGSG-TDFTLTINSLEAEDAATYYC | HQSGR--------LPLT | FGGGT KVEIK |
| iPS:436_240 | VK6|A26/JK4 | EIVLTQSPAFQSV TPKEKVTITC | RAS--QNIG-----RSLH | WYQQKPDQ SPKLLIK | Y-------ASQSFS | GVPSRFSGSGSG-TNFTLTINSLEAEDAVTYYC | HQSRS--------LPLT | FGGGT KVEIK |
| iPS:436_201E8 | VK6|A26/JK4 | EIVLTQSPDFQSV TPKEKVTITC | RAS--QDIS-----RSLH | WYQQKPDQ SPKLLIK | Y-------ASQSFS | GVPSRFSGSGSG-TDFTLTINSLEAEDAATYYC | HQSRS--------LPLT | FGGGT KVEIK |
| iPS:436_206G4_314 | VK6|A26/JK4 | | | | K_CDR2 | K_FR3 | K_CDR3 | K_FR4 |
| VK1|A20|JK3 | Germline | | | | | | | |
| iPS:435_190D1 | VK1|A20/JK3 | DIQMTQSPSSLSA SVGDRVTITC | RAS--QGIS-----NYLA | WYQQKPGK VPKLLIY | A-------ASTLQS | GVPSRFSGSGSG-TDFTLTISSLQPEDVATYYC | QKYNS--------APFT | FGPGT KVDIK |
| iPS:436_019 | VK1|A20/JK3 | DIQMTQSPSSLSA SVGDRVTITC | RPS--QGIS-----IYLA | WYQQKPGN VPKLLIY | A-------ASTLQS | GVPSRFSGSGSG-TDFTLTISSLQPEDVATYYC | QKYNS--------APFT | FGPGT KVDIK |
| iPS:394_010 | VK1|A20/JK3 | DIQMTQSPSSLSA SVGDRVTIPC | RAS--QDIS-----NYLA | WYQQKPGK VPKLLIY | A-------AYILQS | GVPSRFSGSGSG-TDFTLTISSLQPEDVAAYYC | QKYDS--------APFT | FGPGT KVDIK |
| iPS:436_12G5 | VK1|A20/JK3 | | | | | | | |
| VK6|A26|JK3 | Germline | | | | K_CDR2 | K_FR3 | K_CDR3 | K_FR4 |
| iPS:436_025 | VK6|A26/JK3 | EIVLTQSPDFQSV TPKEKVTITC | RAS--QSIG-----SSLH | WYQQKPDQ SPKLLIK | Y-------ASQSFS | GVPSRFSGSGSG-TDFTLTINSLEAEDAATYYC | HQSSR--------LPFT | FGPGT KVDIK |
| iPS:436_096 | VK6|A26/JK3 | EIVLTQSPDFQSV TPKEKVTITC | RAS--QSIG-----SSLH | WYQQKPDQ SPKLLIK | Y-------ASQSFS | GVPSRFSGSGSG-TDFTLTINSLEAEDAATYYC | HQSSR--------LPFT | FGPGT KVDIK |
| iPS:436_408 | VK6|A26/JK3 | EIVLTQSPDFQSV TPKEKVTITC | RAS--QSIG-----VSLH | WYQQKPDQ SPQLLIK | Y-------ASQSFS | GVPSRFSGSGSG-TDFTLTINSLEAEDAATYYC | HQSRS--------LPFT | FGPGS KVDIK |

Figure 51 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:436_424 | 21-225_215H6 | VK6|A26/JK3 | EIVLTQSPDFQSV TPEKVTITC | RAS--QSIG-----VSLH | WYQQKPDQ SPQLLIK | Y-------ASQSLS | GVPSRFSGSGSG-- TDFTLTINSLEAEDAATYYC | HQSRS----------LPFT | FGPGS KVDIK |
| | | Germline | K_FR1 | K_CDR1 | K_FR2 | K_CDR2 | K_FR3 | K_CDR3 | K_FR4 |
| VK1|L5|JK2 | | | | | | | | | |
| iPS:436_082 | 21-225_195D9 | VK1|L5/J K2 | DIQMTQSPSSVSA SVGDRVTITC | RAS--QGIS-----RWLA | WYQQKPGK APKLLIY | A-------ASSLLG | GVPSRFSGSGSG-- TDFTLTISSLQPEDFATYYC | QRANS----------FPCS | FGQGT KLEIK |
| iPS:436_118 | 21-225_196A1 | VK1|L5/J K2 | DIQMTQSPSYVSA SVGDRVSITC | RAS--QGIS-----RWLA | WYQQKPGK AAKFLIY | A-------ASSLLG | GVSSRFSGSGSG-- TDFTLTISSLQPEDFAIYYC | QRDNS----------LPCS | FGQGT KLEIK |
| | | Germline | K_FR1 | K_CDR1 | K_FR2 | K_CDR2 | K_FR3 | K_CDR3 | K_FR4 |
| VK2|A19|JK2 | | | | | | | | | |
| iPS:436_362 | 21-225_210C1_2 | VK2|A19/ JK2 | DIVMTQSPLSLPV TPGEPASISC | RSS---QSLLHYN-GHNFLD | WYLQKPGQ SPQLLIY | L-------VSNRAS | GVPDRFSGSGSG-- TDFTLKISRVEAEDVGVYYC | MQALQ----------TPMCS | FGQGT KLEIK |
| iPS:436_374 | 21-225_211C1_0 | VK2|A19/ JK2 | DIVMTQSPLSLPV TPGEPASISC | RSS---QSLLHSN-GYNYLD | WYLLKPGQ SPQLLIY | L-------GSNRAS | GVPDRFSGSGSG-- TDFTLKISRMEAEDVGIYYC | MQALL----------TPVCS | FGQGT KLEIK |
| | | Germline | K_FR1 | K_CDR1 | K_FR2 | K_CDR2 | K_FR3 | K_CDR3 | K_FR4 |
| VK2|A17|JK1 | | | | | | | | | |
| iPS:437_226 | 21-225_57C2 | VK2|A17/ JK1 | DVVMTQSPLSLPV TLGQPASISC | RSS---QSLVYSD-GNTYLN | WFQQRPGQ SPRRLIY | E-------VSNWDS | GVPNRFSGSGSG-- TDFTLKISAVEAEDVGVYYC | VQGTH----------WPRT | FGQGT KVEIK |
| | | Germline | K_FR1 | K_CDR1 | K_FR2 | K_CDR2 | K_FR3 | K_CDR3 | K_FR4 |
| VK1|A20|JK5 | | | | | | | | | |
| iPS:392_726 | 21-225_20B5 | VK1|A20/ JK5 | DIQMTQSPSSLSA SVGDRVTITC | RAS--QGIN-----NYLA | WYQQKPGK IPKLLIY | A-------ASTLQS | GVPSRFSGSGSG-- TDFTLTISSLQPEDVATYCC | QKYNS----------APPIT | FGQGT RLEIK |
| iPS:392_792 | 21-225_20G12 | VK1|A20/ JK5 | DIQMTQSPSSLSA SVGDRVTITC | RAS--QGIS-----NYLA | WYQQKPGK VPKVLIY | A-------ASTLQS | GVPSRFSGSGSG-- TDFTLIVSSLQPEDVATYYC | QKYNS----------APPIT | FGQGT RLEIK |
| iPS:398_478 | 21-225_17C10 | VK1|A20/ JK5 | DIQMTQSPSSQSA SVGDRVTITC | RAS--QGIS-----NYLA | WYQQKPGR VPKLLIY | A-------ASTLQS | GVPSRFSGSGSG-- TDFTLTISSLQPDDVATYYC | QKYNS----------APPLT | FGQGT RLEIK |
| | | Germline | K_FR1 | K_CDR1 | K_FR2 | K_CDR2 | K_FR3 | K_CDR3 | K_FR4 |
| VK1|L1|JK2 | | | | | | | | | |
| iPS:392_776 | 21-225_21A12 | VK1|L1/J K2 | DIQMTQSPSSLSA SVGDRVTITC | RAS--QGIS-----KYLA | WFQQKPGK APKSLIY | A-------ASSLQS | GVPSRFSGSGSG-- TDFTLTISSLQPEDFATYYC | QQYNS----------YPFR | FGQGT KLEIK |
| | | Germline | K_FR1 | K_CDR1 | K_FR2 | K_CDR2 | K_FR3 | K_CDR3 | K_FR4 |
| VK1|A30|JK3 | | | | | | | | | |
| iPS:437_240 | 21-225_84H12 | VK1|A30/ JK3 | DIQMTQSPSYQSA SVGDRVTITC | RAS--QGIR-----NDLG | WFQQKPGK APKRLIY | A-------ASSLQS | GVPSRFSGSGSG-- TEFTLTITSSLQPEDFATYYC | LQHND----------YPFT | FGPGT KVDIK |

Figure 51 (Continued)

| | | | FR1 | CDR1 | FR2 | CDR2 | FR3 | CDR3 | FR4 |
|---|---|---|---|---|---|---|---|---|---|
| iPS:434577 | 21-225_75C11 | VK1A30/JK3 | DIQMTQSPSSLSASVGDRVTITC | RAS--QGIR-----NDLG | WFQQKPGKAPKRLIY | A------ASSLQS | GVPSRFSGSGSG--TEFTLTISSLQPEDFATYYC | LQHND--------YPFT | FGPGTKVDIK |
| iPS:434553 | 21-225_76H12 | VK1A30/JK3 | DIQMTQSPSSLSASVGDRVTITC | RAS--QGIR-----NDLG | WFQQKPGKAPKRLIY | A------ASRLQS | GVPSRFSGSGSG--TRFTLTISSLQPEDFATYYC | LQHND--------YPFT | FGPGTKVDIK |
| iPS:434927 | 21-225_86E5 | VK1A30/JK3 | DIQMTQSPSSLSASVGDRVTITC | RAS--QGIR-----NDLG | WYQQKPGKAPKRLIY | A------ASSLQS | GVPSRFSGSGSG--TEFTLTISSLQPEDFATYHC | LQHND--------YPFT | FGPGTKVEIK |
| | VK1A30/JK1 | Germline | | | | K_CDR2 | K_FR3 | K_CDR3 | K_FR4 |
| iPS:435477 | 21-225_154E8 | VK1L5/JK1 | DIQMTQSPSSVSASIGDRVTITC | RAS--QFIS-----SWLA | WYQQKPGKAPKLLIY | T------ASSLQS | GVPSRFSGSGSG--TDFTLTISSLQPEDFATYYC | QQANS--------FPWT | FGPGTKVEFN |
| iPS:435385 | 21-225_149G7 | VK1L5/JK1 | DIQMTQSPSSVSASVGDRVTITC | RAS--QFIS-----SWLA | WYQQKPGKAPKFLIY | A------ASSLQS | GVPSRFSGSGSG--TDFTLTISSLQPEDFATYYC | QQANS--------FPWT | FGPGTKVEIN |

LAMBDA VARIABLE

| | | | L_FR1 | L_CDR1 | L_FR2 | L_CDR2 | L_FR3 | L_CDR3 | L_FR4 |
|---|---|---|---|---|---|---|---|---|---|
| | VL3l3r/JL2 | Germline | SYELTQP-PSVSVSPGQTASITC | SGD---KLGD---KYAL | WYQQKPGQSPVLVIY | Q------DSKRPS | GIPERFSGSNSG--NTATLTISGTQAMDEADYYC | QAWDS | FGGGTKLTVL |
| iPS:453445 | 21-225_148E10 | VL3l3r/JL2 | SYELTQP-PSVSVSPGQTASITC | SGD---KLGN---KYVC | WYQQRPGHAAVLIIY | Q------DSKRPS | GIPERFSGSNSG--NTATLTISGTQAMDEADYYC | QAWDR--------NTYVV | FGGGTKLTVL |
| iPS:472742 | 21-225_30D9_LC2 | VL3l3r/JL2 | SYELTQP-PSVSVSPGQTASITC | SGD---KLGD---KYVY | WFQQKPGQSPVLVIY | Q------DRKRPS | GIPERFSGSNSG--NTATLTISGTQALDEADYYC | QAWDN--------STAV | FGGGTKLTVL |
| iPS:472743 | 21-225_68G6 | VL3l3r/JL2 | SYEVTQP-PSVSVSPGQTASITC | SGD---KLGD---KYTY | WYQQKAGQSPFIVIY | Q------DRKRPS | GIPDRFSGSNSG--NTATLTISGTQAMDAADFYC | QAWDN--------STAV | FGGGTKLTVL |
| iPS:436652 | 21-225_146B11 | VL3l3r/JL2 | SYELTQP-PSVSVSPGQTASITC | SGD---KLGD---KYAS | WYQQKPGQSPVLVIY | Q------DSKRPS | GIPERFSGSNSG--NTATLTISGTQAMDEADYYC | QAWDS--------STVV | FGGGTKLTVL |
| iPS:436654 | 21-225_146C11 | VL3l3r/JL2 | SYELTQP-PSVSVSPGQTASITC | SGD---KLGD---KYAS | WYQQKPGQSPVLVIY | Q------DSKRPS | GIPERFSGSNSG--NTATLTISGTQAMDEADYYC | QAWDS--------STVV | FGGGTKLTVL |
| iPS:436658 | 21-225_146A2 | VL3l3r/JL2 | SYELTQP-PSVSVSPGQTASITC | SGD---KLGD---KYAS | WYQQKPGQSPVLVIY | Q------DSKRPS | GIPERFSGSNSG--NTATLTISGTQAMDEADYYC | QAWDS--------STVV | FGGGTKLTVL |
| iPS:436664 | 21-225_147E7 | VL3l3r/JL2 | SYELTQP-PSVSVSPGQTASITC | SGD---KLGD---KYAS | WYQQKPGQSPVLVIY | Q------DSKRPS | GIPERFSGSNSG--NTATLTISGTQAMDEADYYC | QAWGS--------STVV | FGGGTKLTVL |
| iPS:436666 | 21-225_147B8 | VL3l3r/JL2 | SYELTQP-PSVSVSPGQTASITC | SGD---KLGD---KYVC | WYQQKPGQSPELVIY | Q------DRKRPS | GIPERFSGSNSG--NTATLTISGTQAMDEADYYC | QAWGS--------NTAVV | FGGGTKLTVL |
| iPS:436668 | 21-225_147B9 | VL3l3r/JL2 | SYELTQP-PSVSVSPGQTASITC | SGD---KLGD---KYVS | WYQQKPGQSPVLVIY | Q------DRKRPS | GIPERFSGSNSG--NTATLTISGTLAVDEADYYC | LAWDS--------STFVV | FGGGTKLTVL |
| iPS:436670 | 21-225_147D9 | VL3l3r/JL2 | SYELTQP-PSVSVSPGQTASITS | SGD---KLGN---KYVC | WYQQRPGQSPVLVIY | Q------DSKRPS | GIPERFSGSNSG--NTATLTISGTQAMDEADYYC | QAWDR--------NTYVV | FGGGTKLTVL |

Figure 51 (Continued)

| | | | | | | | | | |
|---|---|---|---|---|---|---|---|---|---|
| iPS:4 36672 | 21-225_147F9 | VL3J3r/JL2 | SYELTQP-PSVSVSPGQTASITC | SGD----ELGN-KYAC | WYQQKPGQ SPVLVIY | Q------DSKRPS | GIPERFSGSNSG-NTATLTISGTQAMDEADYYC | QAWHS---------STVV | FGGGT KLTVL |
| iPS:4 36674 | 21-225_147G9 | VL3J3r/JL2 | SYELTQP-PSVSVSPGQTASITC | SGD----KLGD-KYAC | WYQQKPGQ SPVLVIY | Q------DKRPS | GIPERFSGSNSG-NTATLTISGTQAMDEADYYC | QAWDS---------STVV | FGGGT KLTVL |
| iPS:4 36676 | 21-225_147E11 | VL3J3r/JL2 | SYELTQP-PSVSVSPGQTASITC | SGD----KLGD-KYAS | WYQQKPGQ SPVLVIY | Q------DSKRPS | GIPERFSGSNSG-NTATLTISGTQAMDEADYYC | QAWDS---------STVV | FGGGT KLTVL |
| iPS:4 36678 | 21-225_147B12 | VL3J3r/JL2 | SYELTQP-PSVSVSPGQTASITC | SGD----KLGD-KYAS | WYQQKPGQ SPVLVIY | Q------DSKRPS | GIPERFSGSNSG-NAATLTISGTQAMDEADYYC | QAWDS---------STVV | FGGGT KLTVL |
| iPS:4 36686 | 21-225_148G6 | VL3J3r/JL2 | SYELTQP-PSVSVSPGQTASITC | SGD----KLGD-KYAS | WYQQKPGQ SPVLVIY | Q------DSKRPS | GIPERFSGSNSG-NTATLTISGTQAMDEADYYC | QAWDS---------STVV | FGGGT KLTVL |
| iPS:4 36688 | 21-225_148C8 | VL3J3r/JL2 | SYELTQP-PSVSVSPGQTASITC | SGD----KLGD-KYVS | WYQQKPGQ SPVLVIY | Q------DKRPS | GIPERFSGSNSG-NTATLTISGTQAMDEADYYC | LAWDS---------STFVV | FGGGT KLTVL |
| iPS:4 36690 | 21-225_148A9 | VL3J3r/JL2 | SYELTQP-PSVSVSPGQTASITC | SGD----KLGN-KYVC | WYQQKPGQ SPILVIY | Q------DSKRPS | GIPERFSGSNSG-NTATLTISGTQAMDEADYYC | QAWHS---------STVV | FGGGT KLTVL |
| iPS:4 36694 | 21-225_148G11 | VL3J3r/JL2 | SYELTQP-PSVSVSPGQTASITC | SGD----KLGD-KFAS | WYQQKPGQ SPVLVIY | Q------DSRRPS | GIPERFSGSNSG-NTATLTISGTQAMDEADYYC | QAWDS---------STVV | FGGGT KLTVL |
| iPS:4 36698 | 21-225_149B5 | VL3J3r/JL2 | SYELTQP-PSVSVSPGQTASITC | SGY----KLGY-KYVC | WYQQKPGQ SPVLVIF | Q------MNQRPS | GIPERFSGSNSG-NTASLTISGTQAMDEADYYC | QAWDS---------STVV | FGGGT KLTVL |
| iPS:4 36700 | 21-225_149C7 | VL3J3r/JL2 | SYELTQP-PSVSVSPGQTASITC | SGN----KLGD-KYAS | WYQQKPGQ SPVLVIY | Q------DSKRPS | GIPERFSGGKSG-NTATLTISGTQAMDEADYYC | QAWDS---------STVV | FGGGT KLTVL |
| iPS:4 36704 | 21-225_149C10 | VL3J3r/JL2 | SYELTQP-PSVSVSPGQTASITC | SGD----KLGD-KYAS | WYQQKPGQ SPVLVIY | Q------DNKRPS | GIPERFSGSNSG-NTATLTIGGIQAMDEADYYC | QAWDS---------STVV | FGGGT KLTVL |
| iPS:4 36706 | 21-225_149A11 | VL3J3r/JL2 | SYELTQP-PSVSVSPGQTASITC | SGD----KLGN-KYVS | WYQQKPGQ SPVLVIY | Q------DSRRPS | GIPERFSGSNSG-NTATLTISGTQAMDEADYYC | LAWDS---------STFVV | FGGGT KLTVL |
| iPS:4 36708 | 21-225_150D3 | VL3J3r/JL2 | SYELTQP-PSVSVSPGQTASITC | SGD----ELGN-KYAC | WYQQKPGQ SPVLVIY | Q------DSKRPS | GIPERFSGSSSG-NTATLTISGTQAMDEADYCC | QAWDS---------STVV | FGGGT KLTVL |
| iPS:4 36710 | 21-225_150F6 | VL3J3r/JL2 | SYELTQP-PSVSVSPGQTASITC | SGD----KLGD-KYAS | WYQQKPGQ SPVLVIC | Q------DSKRPS | GIPERFSGSNSG-NTATLTISGTQAMDEADYYC | QAWDS---------STVV | FGGGT KLTVL |
| iPS:4 36714 | 21-225_150H11 | VL3J3r/JL2 | SYELTQP-PSVSVSPGQTASITC | SGD----KLGD-KYAS | WYQQKPGQ SPVLVIY | Q------DSKRPS | GIPERFSGSNSG-NTATLTISGTQAMDEADYIC | QAWDS---------STVV | FGGGT KLTVL |
| iPS:4 36716 | 21-225_151F3 | VL3J3r/JL2 | SYELTQP-PSVSVSPGQTASITC | SGD----KLGD-KYVC | WYQQKPGQ SPVLVIY | Q------DRKRPS | GIPERFSGSNSG-NTATLTISGTQAMDEADYYC | QAWHS---------STVV | FGGGT KLTVL |

Figure 51 (Continued)

| | | | | | | | | |
|---|---|---|---|---|---|---|---|---|
| iPS:4 36718 | 21-225_151H5 | VL3j3r/JL2 | SYELTQP-PSVSVSPGQTASIAC | SGD----KLGD-----KYAS | WYQQKPGQSPVLVIY | Q------DSKRPS | GIPERFSGSNSG-NTATLTISGIQAMDEADYYC | QAWDS--------STVV | FGGGTKLTVL |
| iPS:4 36722 | 21-225_151H7 | VL3j3r/JL2 | SYDLTQP-PSVSVSPGQTASITC | SGD----KLGD-----KYAS | WYQQKPGQSPVLVIY | Q------DSKRPS | GIPERFSGSNSG-NTATLTISGTQAMDEADYYC | QAWDS--------STVV | FGGGTKLTVL |
| iPS:4 36724 | 21-225_151B9 | VL3j3r/JL2 | SYELTQP-PSVSVSPGQTASIAC | SGD----NLGD-----KYAS | WYQQKPGQSPVLVIY | Q------DSKRPS | GIPERFSGSNSG-NTATLTISGTQAMDEADYYC | QAWDS--------STVV | FGGGTKLTVL |
| iPS:4 36728 | 21-225_152G6 | VL3j3r/JL2 | SYELTQP-PSVSVSPGQTASITC | SGD----KLGD-----KYAS | WYQQKPGQSPVLVIY | Q------DSKRPS | GIPERFSGSNSG-NTATLTISGIQALDEADYYC | QAWDN--------STVV | FGGGTKLTVL |
| iPS:4 36730 | 21-225_152D7 | VL3j3r/JL2 | SYELTQP-PSVSVSPGQTASITC | SGD----KLGD-----KYAS | WYQQKPGQSPVLVIY | Q------DSKRPS | GIPERFSGSNSG-NTATLTISGIQAMDEADYYC | QAWDS--------STVV | FGGGTKLTVL |
| iPS:4 36736 | 21-225_153E8 | VL3j3r/JL2 | SYELTQP-PSVSVSPGQTASITC | SGS----KLGN-----KYVC | WYQQKPGQSPVLVIY | Q------DNKRPS | GIPERFSGSNSG-NTATLTISGTQAMDEADYYC | QAWDS--------STYVI | FGGGTKLTVL |
| iPS:4 36738 | 21-225_153D9 | VL3j3r/JL2 | SYELTQP-PSVSVSPGQTASITC | SGD----KLGD-----KYAS | WYQQKPGQSPVLVIY | Q------DRKRPS | GIPERFSGSNSG-NTATLTISGTQAMDEADYYC | QAWHS--------STVV | FGGGTKLTVL |
| iPS:4 36740 | 21-225_154C3 | VL3j3r/JL2 | SYELTQP-PSVSVSPGQTASITC | SGD----KLGD-----KYVC | WYQQKPGQSPVLVIY | Q------DKKRPS | GIPERFSGSNSG-NTATLTISGTQAMDEADYYC | QAWDS--------STVV | FGGGTKLTVL |
| iPS:4 36742 | 21-225_154C4 | VL3j3r/JL2 | SYELTQP-PSVSVSPGQTARI | SGD----KLGD-----KYAS | WYQQKPGQSPVLVIY | Q------DSKRPS | GIPERFSGSNSG-NTATLTISGIQAMDEADYYC | QAWDS--------STVV | FGGGTKVTVL |
| iPS:4 36744 | 21-225_154F4 | VL3j3r/JL2 | SYELTQP-PSVSVSPGQTASITC | SGD----KLGN-----KYVS | WYQQKPGQSPVEVIY | K------DSKRPS | GIPERFSGSNSG-NTGLLTISGTQAMDEADYYC | QAWDN--------STLV | FGGGTKLTVL |
| iPS:4 36746 | 21-225_154E10 | VL3j3r/JL2 | SYELTQP-PSVSVSPGQTASITC | SGD----KLGD-----KYAS | WYQQKPGQSPVLVIY | Q------DSKRPS | GIPERFSGSNSG-NTATLTISGIQAMDEADYYC | QAWDN--------STVV | FGGGTKLTVL |
| iPS:4 36748 | 21-225_154D11 | VL3j3r/JL2 | SYELTQP-PSVSVSPGQTASITC | SGD----KLGD-----KYAC | WYQQKPGQSPVLVIF | Q------DKKRPS | GIPERFSGSNSG-NTATLTISGTQAMDEADYYC | QAWHS--------SIVV | FGGGTKVTVL |
| iPS:4 36756 | 21-225_146A10 | VL3j3r/JL2 | SYELTQP-PSVSVSPGQTASITC | SGD----KLGD-----KYVS | WYQQKPGQSPVLVIY | Q------DRKRPS | GIPERFSGSNSG-NTATLTISGTQAMDEADYYC | QAWDS--------STVV | FGGGTKLTVL |
| iPS:4 36758 | 21-225_155C10 | VL3j3r/JL2 | SYELTQP-PSVSVSPGQTVSITC | SGD----KLGD-----KYVS | WYQQKPGQSPVLVIY | Q------DSKRPS | GIPERFSGSNSG-NTATLTISGIQAMDEADYYC | QAWDS--------STVV | FGGGTKLTVL |
| iPS:4 36760 | 21-225_155E10 | VL3j3r/JL2 | SYELTQP-PSVSVSPGQTASITC | SGD----KLGD-----KYVS | WYQQKPGQSPVLVIY | Q------DRKRPS | GIPERFSGSNSG-NTATLTISGTQAMDEADYYC | LAWDS--------STFVV | FGGGTKLTVL |
| iPS:4 36764 | 21-225_158E9 | VL3j3r/JL2 | SYELTQP-PSVSVSPGQTASITC | SGD----KLGD-----KYVC | WYQQKPGQSPVLVIY | Q------DSKRPS | GIPERFSGSNSG-NTATLITGTQAMDEANYYC | QAWDN--------SSFVL | FGGGTKLTVL |

Figure 51 (Continued)

| | | | | | | | | |
|---|---|---|---|---|---|---|---|---|
| iPS:4 36766 | 21-225_158D10 | VL3j3r/JL2 | SYELTQP-PSVTVSPGQTASITC | SGD----KLGD-----KYVC | WYQQKPGQSPVLVIY | Q-------DKRPS | GIPERLSGSNSG-NTATLTISGTQALDEADYYC | QAWGN--------SSFVV | FGGGTKLTVL |
| iPS:4 36768 | 21-225_159H8 | VL3j3r/JL2 | SYELTQP-PSVSVSPGQTASITC | SGD----KLGD-----KYVC | WYQQKPGQSPVLVIY | Q-------DRKRPS | GIPERFSGSNSG-NTATLTISGTQALDEADYYC | QAWGN--------SSFVV | FGGGTKLTVL |
| iPS:4 36770 | 21-225_160B12 | VL3j3r/JL2 | SDELTQS-PSVSVSPGQTASITC | SGD----KLGD-----KYVC | WYQQKPGQSPVLVIY | Q-------DSKRPS | GIPERFSGSNSG-NTATLTISGTQALDEADYYC | QAWGN--------SSFVV | FGGGTKLTVL |
| iPS:4 36772 | 21-225_161H3 | VL3j3r/JL2 | SYELTQP-PSVSVSPGQTASITC | SGD----RLGD-----KYVC | WYQQKPGQSPVLVIF | Q-------DNKRPS | GIPERFSGSNSG-NTATLTISGTQALDEADYYC | QAWVN--------NTAVV | FGGGTKLTVL |
| iPS:4 36774 | 21-225_161E10 | VL3j3r/JL2 | SFDLTQP-PSVSVSPGQTASITC | SGD----KLGD-----KYVC | WYQQKPGQSPVLVIY | Q-------DSKRPS | GIPERISGSNSG-NTATLTISGTQALDEADYYC | QTWDN--------SSFAL | FGGGTKLTVL |
| iPS:4 36776 | 21-225_161F12 | VL3j3r/JL2 | SYELTQP-PSVSVSPGQTASITC | SGD----KLGD-----KYVH | WYQQKPGQSPVLVIY | Q-------DTKRPS | GIPERFSGSNSG-NTATLTISGTQAMDEADYYC | QAWDS--------TTLV | FGGGTKLTVL |
| iPS:4 36780 | 21-225_165H3 | VL3j3r/JL2 | SYELTQP-PSVSVSPGQTASITC | SGD----KLGD-----KYAC | WYQQKPGQSPVLVIY | Q-------DSKRPS | GIPERFSGSNSG-NTATLTISGTQAMDEADYYC | QAWDS--------STAV | FGGGTKLTVL |
| iPS:4 36782 | 21-225_166G11 | VL3j3r/JL2 | SYELTQP-PSVSVSPGQTASITC | SGD----KLGD-----KYVC | WYQQKPGQSPVLVIY | Q-------DSKRPS | GIPERFSGSNSG-NTATLTISGTQAMDEADYYC | QAWDT--------NTVI | FGGGTKLTVL |
| iPS:4 36784 | 21-225_169C1 | VL3j3r/JL2 | SYELTQP-PSVSVSPGQTASITC | SGD----KLGD-----KYVC | WYQRKPGQSPLLVIY | K-------DIKRPS | GIPERFSGSNSG-NTATLTISGTQAMDEADYYC | QAWDT--------NTVL | FGGGTKLTVL |
| iPS:4 36786 | 21-225_169A6 | VL3j3r/JL2 | SYELTQP-PSVSVSPGQTASITC | SGD----KLGD-----KYVC | WYQRKPGQSPVLVIY | Q-------DYKRPS | GIPERFSGSNSG-NTATLTISGTQAMDEADYYC | QAWDK--------NTVV | FGGGTKLTVL |
| iPS:4 36788 | 21-225_169B7 | VL3j3r/JL2 | AYDLTQP-PSVSVSPGQTASITC | SGD----KLGG-----KYAS | WYQQKPGQSPVLVIY | Q-------DRKRPS | GIPERFSGSNSG-NTATLTISGTQAMDEADYYC | QAWDN--------STAV | FGGGTKLTVL |
| iPS:4 36790 | 21-225_169G11 | VL3j3r/JL2 | SYELTQP-PSVSVSPGQTASITC | SGD----KLGD-----KYAC | WYQQKPGQSPILVIY | Q-------DSKRPS | GIPERFSGSNSG-NTATLTISGTQAMDEADYYC | QAWDN--------NTAV | FGGGTKLTVL |
| iPS:4 36794 | 21-225_170F1 | VL3j3r/JL2 | SYELSQP-PSVSVSPGQTASITC | SGD----KLGD-----KYSC | WYQQKPGQSPVLVIY | Q-------DSKRPS | GIPARFSGSNSG-NTATLTISGTQAMDEADYYC | QAWDS--------STMV | FGGGTKLTVL |
| iPS:4 36796 | 21-225_170A5 | VL3j3r/JL2 | SYDLTQP-PSVSVSPGQTASITC | SGD----KLGD-----KYAC | WYQQKPGQSPVLVIY | Q-------DYKRPS | GIPERFSGSNSG-NTATLTISGTQAMDEADYYC | QAWDN--------NTVI | FGGGTRLTVL |
| iPS:4 36798 | 21-225_171F5 | VL3j3r/JL2 | AYDLTQP-PSVSVSPGQTARITC | SGD----KLGG-----KYAS | WYQRKPGQSPVLVIY | Q-------DRKRPS | GIPERFSGSNSG-NTATLTISGTQAMDEADYYC | QAWDK--------NTVL | FGGGTKLTVL |
| iPS:4 36802 | 21-225_171E12 | VL3j3r/JL2 | SYELTQP-PSVSVSPGQTASITC | SGD----KLGD-----KYAC | WYQQKPGQSPVLVIY | Q-------DRKRPS | GIPERFSGSNSG-NTATLTISGTQAMDEADYYC | QAWDI--------STYVV | FGGGTKLTVL |

Figure 51 (Continued)

| | | | | | | | |
|---|---|---|---|---|---|---|---|
| iPS:4 36808 | 21-225_173F8 | VL3j3r/JL2 | SYELTQP-PSVSVSPGQTASITC | SGN----KLGN-----KYVC | WYQQRPGQSPVLVIS | Q-------DSRRPS | GIPERFSGSNSG-NTATLTISGTQAMDEADYYC | QAWDS----------------FTVV | FGGGTKLTVL |
| iPS:4 36812 | 21-225_175C6 | VL3j3r/JL2 | SYDLTQP-PSVSVSPGQTASITC | SGD----KLGD-----KYAC | WYQQKPGQSPILVIY | Q-------DYKRPS | GIPERFSGSNSG-NTATLTISGTQAMDEADYYC | QAWDN----------------STMV | FGGGTKLTVL |
| iPS:4 36818 | 21-225_179C7 | VL3j3r/JL2 | SYELTQP-PSVSVSPGQTASITC | SGD----KLGD-----KYVC | WYQQKPGQSPVLVIY | Q-------DSKRPS | GIPERFSGSNSG-NTATLTIRGTQAMDEADYYC | QAWDS----------------NTAVV | FGGGTKLTVL |
| iPS:4 36822 | 21-225_180D4 | VL3j3r/JL2 | SYELTQT-PSVSVSPGQTASITC | SGD----RLGD-----KYAC | WYQQKPGQSPVLVIY | E-------DRKRPS | GIPERFSGSNSG-NTATLTISGTQAMDEGDYYC | QAWDS----------------RKVV | FGGGTKLTVL |
| iPS:4 36824 | 21-225_180C5 | VL3j3r/JL2 | SYELTQP-PSVSVSPGQTASITC | SGD----KLGE-----KYAC | WYQQKPGQSPVLVIY | Q-------DRKRPS | GIPERFSGSNSG-NTATLTISGTQAMDEADYYC | QAWDS----------------STAV | FGGGTKLTVL |
| iPS:4 36826 | 21-225_180G5 | VL3j3r/JL2 | SYELTQP-PSVSVSPGQTASITC | SGD----KLGD-----KYVS | WYQQKPGQSPVLVIY | Q-------DSKRPS | GIPERFSGSNSG-NPASLTISGTQAMDEADYYC | QAWDI----------------TTAV | FGGGTKLTVL |
| iPS:4 36828 | 21-225_181H1 | VL3j3r/JL2 | SYELTQT-PSVSVSPGQTASITC | SGD----KLGD-----KYAC | WYQQKPGQSPVLVIY | E-------DRKRPS | GIPERFSGSNSG-NTATLTISGTQAMDEADYYC | QAWDS----------------RKVV | FGGGTKLTVL |
| iPS:4 36836 | 21-225_52H1 | VL3j3r/JL2 | SYELTQP-PSVFVSPGQTASITS | SGD----KLGD-----KYVS | WYQQKPGQSPVLVIY | Q-------DSKRPS | GIPERFSGSNSG-NTATLTISGTQAMDEADYYC | QAWDN----------------STVV | FGGGTKLTVL |
| iPS:4 36848 | 21-225_57F1 | VL3j3r/JL2 | SYELTQP-PSASVSPGQTASITC | SGD----KLGE-----KYAC | WYQKKPGQSPVLVIY | Q-------DRKRPS | GIPERFSGSNSG-NTATLTISGTQAMDEADYYC | QAWDS----------------STVV | FGGGTKLTVL |
| iPS:4 36850 | 21-225_57D9 | VL3j3r/JL2 | SYELTQP-PSVSVSPGQTASITC | SGE----KLGE-----KFAC | WSQQKPGQSPVLVIY | Q-------DSKRPS | GIPERFSGSNSG-NTATLTISGTQAMDEADYYC | QAWDS----------------STVV | FGGGTKLTVL |
| iPS:4 36852 | 21-225_57H11 | VL3j3r/JL2 | SYALTQP-PSASVSPGQTASITC | SGD----KLGE-----KYAC | WYQQKPGQSPVLVIY | Q-------DRKRPS | GIPERFSGSNSG-NTATLTISGTQAMDEADYYC | QAWDS----------------STVV | FGGGTKLTVL |
| iPS:4 36854 | 21-225_58C1 | VL3j3r/JL2 | SYELTQP-PSVSVSPGQTANITS | SGD----KLGN-----KYAC | WYQQKPGQSPVLVIY | Q-------DNKRPS | GIPERFSGSNSG-NTATLTISGTQAMDEADYYC | QAWD-----------------SSTA | FGGGTKLTVL |
| iPS:4 36858 | 21-225_58E7 | VL3j3r/JL2 | SYELTQS-PSVSVSPGQTASITC | SGD----KLGD-----KYTC | WYQKKPGQSPVLVIY | Q-------DRKRPS | GIPERFSGSNSG-NTATLTISGTQAMDEADYFC | QAWNN----------------YTVV | FGGGTKLTAL |
| iPS:4 36860 | 21-225_58F7 | VL3j3r/JL2 | SYELTQP-PSVSVSPGQTASITC | SGD----KLGD-----KYAC | WYQQKPGQSPVLVIY | Q-------DRKRPS | GIPERFSGSNSG-NTATLTISGTQAMDEADYYC | QAWDS----------------STVV | FGGGTKLTVL |
| iPS:4 36862 | 21-225_58F8 | VL3j3r/JL2 | SYELTQP-PSVSVSPGQTASITC | SGD----KLGN-----KYAC | WYQQKPGQSPVLVIY | Q-------DSKRPS | GIPERFSGSNSG-NTATLTISGTQAMDEADYYC | QAWDS----------------STVV | FGGGTKLTVL |
| iPS:4 36864 | 21-225_58G11 | VL3j3r/JL2 | SYELTQP-PSVSVSPGQTASITC | SGD----KLGD-----KYAS | WYQQKPGQSPVLVIY | Q-------DNKRPS | GIPERFSGSNSG-NTATLTISGTQAMDEADYYC | QAWNN----------------NTVM | FGGGTKLTVL |

Figure 51 (Continued)

| | | | | | | | | |
|---|---|---|---|---|---|---|---|---|
| iPS:4 36866 | 21-225_59F2 | VL3l3r/JL2 | SYELTQP-PSVSVSPGQTASI TC | SGD----KLGD-----KYAS | WYQQRPGQ SPVLVIY | Q-------DNKRPS | GIPERFSGSNSG-NTATLTISGTQAMDEADYYC | QAWDN--------NTVV | FGGGT KLTVL |
| iPS:4 36868 | 21-225_59B11 | VL3l3r/JL2 | SYELTQP-PSVSVSPGQTASI TC | SGD----KLGD-----KYAC | WYQQKPGQ SPVLVIY | Q-------DSKRPS | GILERFSGSNSG-NTATLTISGTQAMDEADYYC | QAWDS--------STYVV | FGGGT KLTVL |
| iPS:4 36870 | 21-225_60B1 | VL3l3r/JL2 | SYELTQP-PSASVSPGQTASI TC | SGD----KLGE-----KYAC | WYQQKPGQ SPVLVIY | Q-------DRKRPS | GIPERFSGSNSG-NTATLTISGTQAMDEADYYC | QAWDS--------STVV | FGGGT KLTVL |
| iPS:4 36872 | 21-225_60D2 | VL3l3r/JL2 | SYELTQP-PSVSVSPGQTASI TC | SGN----KLGD-----KYAS | WYQQRPGQ SPVLVIY | Q-------DNKRPS | GIPERFSGSNSG-NTATLTISGTQTMDEADYYC | QAWDN--------NTVV | FGGGT KLTVL |
| iPS:4 36874 | 21-225_60A12 | VL3l3r/JL2 | SYELTQP-PSVSVSPGQTANI TC | SGD----KLGN-----KYAC | WYQQKPGQ SPVLVIY | Q-------DRKRPS | GIPERFSGSNSG-NTATLTISGTQAMDEADYYC | QAWD---------SSTA | FGGGT KLTVL |
| iPS:4 36876 | 21-225_61F5 | VL3l3r/JL2 | SYELTQP-PSVSVSPGQTASI TC | SGD----KLGE-----KYAC | WYQQKPGQ SPVLVIY | Q-------DSKRPS | GIPERFSGSNSG-NTATLTISGTQAMDEADYYC | QAWDS--------STVV | FGGGT KLTVL |
| iPS:4 36878 | 21-225_62E3 | VL3l3r/JL2 | SYELTQP-PSVSVSPGQTASI TC | SGD----KLGN-----KYAC | WYQQKPGQ SPVLVIY | Q-------DRKRPS | GIPERFSGSNSG-NTATLTISGTQAMDEADYYC | QAWDS--------STAV | FGGGT KLTVL |
| iPS:4 36880 | 21-225_62E8 | VL3l3r/JL2 | SYELTQP-PSVSVSPGQTASI TC | SGD----RLGN-----KYAS | WYQQKPGQ SPVLVIY | Q-------DRKRPS | GIPERFSGSNSG-NTATLTISGTQAMDEADYYC | QAWDS--------STAV | FGGGT KLTVL |
| iPS:4 36882 | 21-225_62D10 | VL3l3r/JL2 | SYELTQP-PSVSVSPGQTASI TC | SGD----KLGN-----KYAC | WYQQKPGQ SPVVVIY | Q-------DRKRPS | GIPERFSGSNSG-NTATLTISGTQAMDEADYYC | QAWDS--------STAV | FGGGT KLTVL |
| iPS:4 36884 | 21-225_62A12 | VL3l3r/JL2 | SYELTQP-PSVSVSPGQTASI TC | SGD----KLGN-----KYAC | WYQQKPGQ SPVVVIY | Q-------DRKRPS | GIPERFSGSNSG-NTATLTISGTQAMDEADYYC | QAWDS--------STAV | FGGGT KLTVL |
| iPS:4 36886 | 21-225_62B12 | VL3l3r/JL2 | SYELTQP-PSVSVSPGQTASI TC | SGD----KLGN-----KYTC | WYQQKPGQ SPVVVIY | Q-------DRKRPS | GIPERFSGSNSG-NTATLTISGTQAMDEADYYC | QAWDS--------STAV | FGGGT KLTVL |
| iPS:4 36892 | 21-225_65E9 | VL3l3r/JL2 | SYELTQP-PSVSVSPGQTASI TC | SGD----KLGN-----KYDY | WYQQKPGQ SPVLVIY | Q-------DRKRPS | GIPERFSGSNSG-NTATLTISGTQAMDEADYYC | QAWDN--------NTAV | FGGGT KLTVL |
| iPS:4 36894 | 21-225_66G9 | VL3l3r/JL2 | SYELTQP-PSVSVSPGQTASI TC | SGD----KLGN-----KYAC | WYQQKPGQ SPVLVIF | Q-------DRKRPS | GIPERFSGSNSG-NTATLTISGTQAMDEADYYC | QAWDI--------STVV | FGGGT KLTVL |
| iPS:4 36896 | 21-225_67F10 | VL3l3r/JL2 | SYELTQP-PSVSVSPGQTASI TC | SGD----KLGY-----KYAW | WYQQKPGQ SPVLVIY | Q-------DRKRPS | GIPERFSGSNSG-NTATLTISGTQAMDEADYYC | QAWDN--------STVV | FGGGT RLTVL |
| iPS:4 36898 | 21-225_68D8 | VL3l3r/JL2 | SYELTQP-PSVSVSPGQTASI TC | SGD----KLGD-----KYAC | WYQQKPGQ SPVLVIY | E-------DRKRPS | GIPERFSGSNSG-NTATLTISGTQAMDEADYYC | QAWDN--------STVV | FGGGT KLTVL |
| iPS:4 36900 | 21-225_69B9 | VL3l3r/JL2 | SYELTQP-PSVSVSPGQTASI TC | SGD----KLGN-----KYDY | WYQQKPGQ SPVLVIY | Q-------DRKRPS | GIPERFSGSNSG-NTATLTISGTQAMDEADYYC | QAWDN--------STVV | FGGGT KLTVL |

Figure 51 (Continued)

| ID | Name | Segment | Col1 | Col2 | Col3 | Col4 | Col5 | Col6 | Col7 | Col8 |
|---|---|---|---|---|---|---|---|---|---|---|
| iPS:4 36902 | 21-225_69B11 | VL3j3r/JL2 | SYELTQP-PSVSVSPGQAASITC | SGD----KLGD-----KYAW | WYQQKPGQ SPVLVIY | E------- DRKRPS | GIPERFSGSNSG-NTATLTISGTQAMDEADYYC | QAWDN------- | --------STVV | FGGGT KLTVL |
| iPS:4 36904 | 21-225_71D4 | VL3j3r/JL2 | SYELTQP-PSVSVSPGQTASITC | SGD----KLGD-----KYAY | WYQQKPGQ SPVVVIY | Q------- DRKRPS | GIPERFSGSNSG-NTATLTISGTQAMDEADYYC | QAWVN------- | --------STVV | FGGGT KLTVL |
| iPS:4 36906 | 21-225_72B4 | VL3j3r/JL2 | SYELTQP-PSVSVSPGQTASITC | SGD----KLGD-----KYAW | WYQQKPGQ SPVLVIY | E------- DRKRPS | GIPERFSGSNSG-NTATLTISGTQAMDEADYYC | QAWDN------- | --------STVV | FGGGT KLTVL |
| iPS:4 36908 | 21-225_72D5 | VL3j3r/JL2 | SYDLTQP-PSVSVSPGQTASITC | SGD----KLGN-----KYAC | WYQQKPGQ SPVVVIY | Q------- DRKRPS | GIPERFSGSNSG-NTATLTISGTQAMDEADYYC | QAWDS------- | --------STAV | FGGGT KLTVL |
| iPS:4 36912 | 21-225_73C4 | VL3j3r/JL2 | SYDLTQP-PSVSVSPGQTASITC | SGD----KLGN-----KYAC | WYQQKPGQ SPVVVIY | Q------- DMKRPS | GIPERFSGSNSG-NTATLTISGTQAMDEADYYC | QAWDS------- | --------STAV | FGGGT KLTVL |
| iPS:4 36914 | 21-225_76B4 | VL3j3r/JL2 | PYELNQT-PSVSVSPGQTASITC | SGD----RLGT-----KFAC | WYQQKPGQ SPVLVIY | Q------- DSKRPS | GIPERFSGSNSG-NTATLTISGTQAMDEADYYC | QAWD-------- | --------SSTV | FGGGT KLTVL |
| iPS:4 36916 | 21-225_74A9 | VL3j3r/JL2 | SYELTQP-PSVSVSPGQTASITC | SGD----KLGN-----KYAC | WYQQKPGQ SPVVVIY | Q------- DNRRPS | GIPERFSGSNSG-NTATLTISGTQAMDEADYYC | QAWDS------- | --------SPVI | FGGGT KLTVL |
| iPS:4 36918 | 21-225_77A2 | VL3j3r/JL2 | SYELTQP-PSVSVSPGQTANITC | SGD----RLGD-----KYAC | WYQQKPGQ SPVLVIY | Q------- DRKRPS | GIPERFSGSNSG-NTATLTISGTQAMDEADYYC | QAWDS------- | --------STAV | FGGGT KLTVL |
| iPS:4 36922 | 21-225_78E9 | VL3j3r/JL2 | SYELTQP-PSESVSPGQTASITC | SGD----KLGN-----KYVS | WYQQKPGQ SPVLVIY | Q------- DNRRPS | GIPERFSGSNSG-STATLTISGTQAMDEADYYC | QAWDS------- | --------SPVI | FGGGT KLTVL |
| iPS:4 36924 | 21-225_74B3 | VL3j3r/JL2 | SYELTQP-PSVSVSPGQTASITC | SGD----KLGD-----KYAC | WYQQKPGQ SPVLVIY | Q------- DSKRPS | GIPERFSGSNSG-NTATLTISGTQAMDEADYYC | QAWDS------- | --------TTVV | FGGGT KLTVL |
| iPS:4 36928 | 21-225_79E7 | VL3j3r/JL2 | SYELTQP-PSVSVSPGQTASITC | SGD----KLGN-----KYVS | WYQQKPGQ SPVLVIY | Q------- DNRRPS | GIPERFSGSNSG-STATLTISGTQAMDEADYYC | QAWDS------- | --------SPVI | FGGGT KLTVL |
| iPS:4 36932 | 21-225_92A4 | VL3j3r/JL2 | SYELTQP-PSVSVSPGQTASITC | SGD----KLGN-----KYVC | WYQQKPGQ SPVLVIY | Q------- DRKRPS | GIPERFSGSNSG-NTATLTISGTQAMDEADYYC | QAWDS------- | --------SPVI | FGGGT KLTVL |
| iPS:4 36934 | 21-225_96B5 | VL3j3r/JL2 | PYELNQT-PSVSVSPGQTASITC | SGD----RLGT-----KFAC | WYQQKPGQ SPVLVIY | Q------- DNRRPS | GIPERFSGSNSG-NTATLTISGTQAMDEADYYC | QAWD-------- | --------SSTV | FGGGT KLTVL |
| iPS:4 36936 | 21-225_97E6 | VL3j3r/JL2 | SYELTQP-PSVSVSPGQTVSITC | SGD----KLGN-----KYVS | WYQQKPGQ SPVLVIY | Q------- DNRRPS | GIPERFSGSNSG-STATLTISGTQAMDEADYYC | QAWDS------- | --------TPVI | FGGGT KLTVL |
| iPS:4 36938 | 21-225_146A3 | VL3j3r/JL2 | SYAMTQP-PSMSVSPGQTASITC | SGN----KLGN-----RYAC | WYQQKPGQ SPVLVIY | Q------- DSKRPS | GIPERFSGSNSG-NIATLTISGTQAMDEADYYC | QAWDS------- | --------STVV | FGGGT KLTVL |
| iPS:4 36940 | 21-225_146B8 | VL3j3r/JL2 | SYELTQP-PSVSVSPGQTASITC | SGD----KLGD-----KYVC | WYQQKPGQ SPVLVIY | Q------- DRKRPS | GIPERFSGSNSG-NTATLTISGTQAMDEADYYC | QAWHS------- | --------STVV | FGGGT KLTVL |

Figure 51 (Continued)

| | | | | | | | | |
|---|---|---|---|---|---|---|---|---|
| iPS:4 36942 | 21-225_146H8 | VL3J3r/JL2 | SYELTQP-PSVSVSPGQTASITC | SGD----KLGD--KYAC | WYQQKPGQ SPVLVIY | Q------DKKRPS | GIPERFSGSNSG-NTATLTISGTQVMDEADYYC | QAWDI-------------RTVV | FGGGT KLTVL |
| iPS:4 36944 | 21-225_182D12 | VL3J3r/JL2 | SYELTQP-PSVSVSPGQTASITC | SGD----KLGE--KYAC | WYQQKSGQ SPVLVIY | Q------DKKRPS | GIPERFSGSNSG-NTATLTISGTQAMDEADYYC | QAWDS-------------RTAV | FGGGT KLTVL |
| iPS:4 36946 | 21-225_183F4 | VL3J3r/JL2 | SYELTQP-PSVSVSPGQTASITC | SGD----KLGD--KYAC | WYQQKPGQ SPVLVIY | Q------DKKRPS | GIPDRFSGSNSG-NTATLTISGTQAMDEADYYC | QAWDN-------------STAVV | FGGGT KLTVL |
| iPS:4 36952 | 21-225_185D2 | VL3J3r/JL2 | SYELTQT-PSVSVSPGQTASITC | SGD----KLGD--KYAC | WYQQKPGQ SPVLVIY | E------DRKRPS | GIPERFSGSNSG-NTATLTISGTQAMDEADYYC | QAWDS-------------RKVV | FGGGT KLTVL |
| iPS:4 36954 | 21-225_185G7 | VL3J3r/JL2 | SYELTQP-PSVSVSPGQTASITC | SGD----KLGH--KFVC | WYQQKPGQ SPVLVIY | Q------DKKRPS | GIPERFSGSNSG-NTATLTISGTQAMDEADYYC | QAWD--------------SSTV | FGGGT KLTVL |
| iPS:4 36956 | 21-225_186H6 | VL3J3r/JL2 | SYELTQP-PSVSVSPGQTASITC | SGD----KMGE--KYAC | WYQQKPGQ SPVLVIY | Q------DKKRPS | GIPERFSGSNSG-NTATLTISGTQAMDEADYYC | QAWDS-------------STAV | FGGGT KLTVL |
| iPS:4 36962 | 21-225_190H1 | VL3J3r/JL2 | SYELTQP-PSVSVSPGQTASITC | SGD----KLGD--RFAY | WYQQKPGQ SPVLVIY | Q------DKKRPS | GIPERFSGSNSG-NTASLTISGTQAMDEADYYC | KAWDS-------------STVV | FGGGT KLTVL |
| iPS:4 36978 | 21-225_190G9 | VL3J3r/JL2 | SYELTQP-PSVSVSPGQTASITC | SGD----KLGD--RFAY | WYQQKPGQ SPVLVIY | Q------DNKRPS | GIPERFSGSNSG-NTATLTISGTQAMDEADYYC | QAWDS-------------STVV | FGGGT RLTVL |
| iPS:4 37018 | 21-225_193H5 | VL3J3r/JL2 | SYELTQP-SSVSVSPGQTASITC | SGD----KLGD--RFAC | WYQQKPGQ SPVLVIY | Q------DSKRPS | GIPERFSGSNSG-NTATLTISGTQAMDEADYYC | QAWDS-------------STAV | FGGGT KLTVL |
| iPS:4 37030 | 21-225_195E3 | VL3J3r/JL2 | SYELTQP-PSVSVSPGQTASITC | SGD----KLGY--RSVC | WYQQKPGQ SPVLVIY | E------DSKRPS | GIPERFSGSNSG-NTATLTISGTQAMDEADYYC | QAWDS-------------VTVV | FGGGT KLTVL |
| iPS:4 37034 | 21-225_195E9 | VL3J3r/JL2 | SYELTQP-PSVSVSPGQTASITC | SGD----KLGN--KYAY | WYQQKPGQ SPVLVIY | Q------DKKRPS | GIPERFSGSNSG-NTGLITISGTQGMDEADYYC | QAWDR-------------GIVV | FGGGT KLTVL |
| iPS:4 37070 | 21-225_201G11 | VL3J3r/JL2 | SYELTQP-PSVSVSPGQTASITC | SGD----KLGD--RFAC | WYQQKPGQ SPVLVIY | Q------DKKRPS | GIPERFSGSNSG-NTATLTISGTQAMDEADYYC | QAWDS-------------STVV | FGGGT KLTVL |
| iPS:4 37076 | 21-225_203G6 | VL3J3r/JL2 | SYELTQP-PSVSVSPGQTASITC | SGD----KLGD--RFAC | WYQQKPGQ SPVLVIY | Q------DKKRPS | GIPERFSGSNSG-NTATLTISGTQSMDEADYYC | QAWDS-------------STVV | FGGGT KLTVL |
| iPS:4 37144 | 21-225_215B3 | VL3J3r/JL2 | SYELTQP-PSVSVSPGQTASITC | SGD----KLGD--KFAC | WYQQKPGQ SPVLVIY | Q------DSKRPS | GIPERFSGSNSG-NTATLTISGTQAMDEADYYC | QAWDS-------------STAV | FGGGT KLTVL |
| iPS:4 37186 | 21-225_224H2 | VL3J3r/JL2 | SYELTQP-SSVSVSPGQTASITC | SGD----NLGV--KYTY | WYQQKPGQ SPVLVVY | Q------DSKRPS | GIPERFSGSNSG-NTATLTISGTQAMDEADYYC | QAWDS-------------STVV | FGGGT KLTVL |
| iPS:4 37192 | 21-225_225E9 | VL3J3r/JL2 | SYELTQP-PSVSVSPGQTASITC | SGD----NLGN--RYAC | WYQQKPGQ SPVLVMY | Q------DRKRPS | GIPERFSGSNSG-NTATLTISGTQAMDEADYYC | QAWDS-------------RTAVV | FGGGT KLTVL |

Figure 51 (Continued)

| | | | | | | | | |
|---|---|---|---|---|---|---|---|---|
| iPS:4 37194 | 21-225_226B2 | VL3j3r/JL2 | SYELTQP-PSVSVSPGQTASITC | SGD----TLGG-KYAM | WYQQRPGQ SPVLVIY | Q------DRKRPS | GIPERFSGSSSG-NTATLTISGTQAMDEADYYC | QAMDN---------GAAV | FGGGT KLTVL |
| iPS:4 37200 | 21-225_226A10 | VL3j3r/JL2 | SYELTQP-PSVSVSPGQTASITC | SGD----TLGG-KYAW | WYQQKPGQ SPVLVIY | Q------DRKRPS | GIPERFSGSSSG-NTATLTISGTQAMDEADYYC | QAMDN---------GAAV | FGGGT KLTVL |
| iPS:4 37204 | 21-225_227E5 | VL3j3r/JL2 | STELSQP-PSVSVSPGQTASITC | SGD----KLGE-KYAC | WYQQKPGQ SPVLVIY | Q------DRKRPS | GIPERFSGGNSG-NKATLTISGTQAMDEADYYC | QAMVN---------NTMI | FGGGT KLTVL |
| iPS:4 37210 | 21-225_227E12 | VL3j3r/JL2 | SYELTQP-PSVSVSPGQTASITC | SGD----KLGD-KYVC | WYQQKPGQ SPVLVIY | Q------DSKRPS | GIPERFSGSNSG-NTATLTISGTQAMDEADYYC | QAWNS---------SNVV | FGGGT KLTVL |
| iPS:4 48908 | 21-225_50G9 | VL3j3r/JL2 | SYELTQP-PSVSVSPGQTASITC | SGD----KLGD-KYAC | WYQQKPGQ SPVLVIY | Q------DSKRPS | GIPERFSGSNSG-NTATLTISGTQARDEAEYYC | QARNS---------ERGV | FGGGT RLTVL |
| iPS:4 51102 | 21-225_45F6 | VL3j3r/JL2 | SYELTQP-PSVSVSPGQTASITC | SGD----KLGD-KYAS | WYQQKPGQ SPVLVIY | Q------DSKRPS | GIPERFSGSNSG-NTATLTISGTQAMDEADYYC | QAWDN---------RTMV | FGGGT KLTVL |
| iPS:4 51110 | 21-225_74C9 | VL3j3r/JL2 | SYELTQP-PSESVSPGQTASITC | SGD----KSGN-KYVS | WYQQKPGQ SPVLVIY | Q------DNRRPS | GIPERFSGSNSG-STATLTISGTQAMDEADYYC | QAWDS---------TPVI | FGGGT KLTVL |
| iPS:4 51112 | 21-225_53D10 | VL3j3r/JL2 | SYELTQP-PSVSVSPGQTASITC | SGD----KLGN-KYAC | WYQQKPGQ SFVLVIY | Q------DRKRPS | GIPERFSGSNSG-NTATLTISGTQAMDEADYYC | QAWDS---------STVV | FGGGT KLTVL |
| iPS:4 72731 | 21-225_14B1_LC2 | VL3j3r/JL2 | SFELTQP-PSVSVSPGQTASITC | SGD----KLGD-KYAY | WYQQKPGQ SFVLVIY | Q------DRKRPS | GIPERFSGSNSG-NTATLTISGTQAMDEADYYC | QAWDN---------STVV | FGGGT KLTVL |
| iPS:3 92583 | 21-225_10B10 | VL3j3r/JL2 | SYELTQP-PSVSVSPGQTASITC | SGD----KLGN-KYAW | WYQQKPGQ SPVLVIY | Q------DRKRPS | GIPERFSGSNSG-NTATLTISGTQAMDEADYYC | QAWDS---------STVV | FGGGT KLTVL |
| iPS:3 92585 | 21-225_14H11 | VL3j3r/JL2 | TYELTQP-SSVSVSPGQTASITC | SGE----KLGE-KYVC | WYQQKPGQ SPVLVIY | Q------DTKRPS | GIPERFSGSNSG-NTATLTISGTQAMDEADYYC | QAWD----------SSII | FGGGT KLTVL |
| iPS:3 92587 | 21-225_18G5 | VL3j3r/JL2 | SYELTQP-PSVSVSPGQTASITC | SGD----KLGD-KYVC | WYQQKPGQ SPVLVIY | Q------DSKRPS | GIPERFSGSNSG-NTATLTISGTQAMDEADYYC | QAWNS---------SNVV | FGGGT KLTVL |
| iPS:3 92589 | 21-225_27H2 | VL3j3r/JL2 | SYELTQP-PSVSVSPGQTASITC | SGD----KLGD-KYAS | WYQQKPGQ SPVLVIY | Q------DGKRPS | GIPERFSGSNSG-NTATLTISGTQAMDEADYYC | QAWDS---------STYVV | FGGGT KLTVL |
| iPS:3 92598 | 21-225_18E10 | VL3j3r/JL2 | SYELTQP-PSVSVSPGQTASITC | SGD----RLGD-KYAW | WYQQKPGQ SPVLVIY | Q------DRKRPS | GIPERFSGSNSG-NTATLTISGTQAMDEADYYC | QAWDS---------STVV | FGGGT KLTVL |
| iPS:3 93166 | 21-225_27G6 | VL3j3r/JL2 | SYELTQP-PSVSVSPGQTASITC | SGD----KLGD-KYAC | WYQQKPGQ SPVLVIY | Q------DRKRPS | GIPERFSGSNSG-NTATLTISGTQIMDEADYYC | QAWDS---------SSYVV | FGGGT KLTVL |
| iPS:3 93168 | 21-225_32B11 | VL3j3r/JL2 | SYELTQP-PSVSVSPGQTASITC | SGD----KLGD-KYAY | WYQQKPGQ SPVLVIY | Q------DSKRSS | GIPERFSGSNSG-NTATLTISGTQAMDEADYYC | QAWDN---------STVV | FGGGT KLTVL |

Figure 51 (Continued)

| | | | | | | | | | |
|---|---|---|---|---|---|---|---|---|---|
| iPS:3 93172 | 21-225_3B12 | VL3J3r/JL2 | SYELSQP-PSVSVSPGQTASITC | SGD----KLGE-------KYAC | WYQQKPGQSPVLVIY | Q-------DRKRPS | GIPERFSGSNSG-NKATLTISGTQAMDEADYYC | QAWVN--------------NTMI | FGGGTKLTVL |
| iPS:3 93176 | 21-225_27E7 | VL3J3r/JL2 | SYELTQP-PSVSVSPGQTASITC | SGD----KLGN-------KYAC | WYQQKPGQSPVEVIY | Q-------DSKRPL | GIPERFSGSNSG-NTATLTISGTQAMDEADYYC | QAWDS--------------STVV | FGGGTKLTVL |
| iPS:3 93178 | 21-225_34D7 | VL3J3r/JL2 | SYELTQP-PSVSVSPGQTASITC | SGD----KLGE-------KYAY | WYQQKPGQSPVLVIY | Q-------DSKRPS | GIPERFSGSNSG-NTATLTISGTQMDEADFYC | QAWDN--------------TTVV | FGGGTKLTVL |
| iPS:3 93182 | 21-225_4B3 | VL3J3r/JL2 | SYELTQP-PSVSVSPRQTVSITC | SGD----KLGD-------KYAC | WYQQKPGQSPVLVIY | Q-------DRKRPS | GIPERFSGSNSG-NTATLTISGTQAMDEADYYC | QAWDN--------------NTVI | FGGGTKLTVL |
| iPS:3 93184 | 21-225_15H11 | VL3J3r/JL2 | SYELTQP-PSVSVSPGQTASITC | SGD----KLGE-------KYAC | WYQQKPGQSPVVVIY | Q-------DSKRPS | GIPERFSGSNSG-NTATLTISGTQAIDEADYYC | QAWDS--------------STAV | FGGGTKLTVL |
| iPS:3 93186 | 21-225_27D9 | VL3J3r/JL2 | SYELTQP-PSMSVSPGQTASITC | SGY----KLGD-------KYAC | WFQQKPGQSPVLVIY | Q-------DSKRPS | GIPERFSGSNSG-NTATLTISGTQAMDEADYYC | QAWV---------------NNTV | FGGGTKLTVL |
| iPS:3 93188 | 21-225_34B9 | VL3J3r/JL2 | SYELTQA-PSVSVSPGQTASITC | SGD----KLGE-------KYVS | WYQEKPGQSPVLVIY | Q-------DSKRPS | GIPERFSGSNSG-NTATLTISGTQAMDEADYYC | QAWD---------------SSTV | FGGGTKLTVL |
| iPS:3 93192 | 21-225_12B1 | VL3J3r/JL2 | SYELTQP-PSVSVSPRQTVSITC | SGD----KLGD-------KYAC | WYQQKPGQSPVLVIY | Q-------DSKRPS | GIPERFSGSNSG-NTATLTISGTQAMDEADYYC | QAWDN--------------NTVI | FGGGTKLTVL |
| iPS:3 93194 | 21-225_16D2 | VL3J3r/JL2 | SYELTQP-PSVSVSPGQTASITC | SGD----KLGD-------KYAC | WYQQKPGQSPVLVIY | Q-------DRKRPS | GIPERFSGSNSG-NTATLTISGTQAMDEADYYC | QAWDS--------------STYVV | FGGGTKLTVL |
| iPS:3 93196 | 21-225_16G8 | VL3J3r/JL2 | SYELTQP-PSVSVSPGQTASITC | SGD----KLGE-------KYAC | WYQQKPGQSPVLVIY | Q-------DRKRPS | GIPERFSGSNSG-NKATLTISGTQAMDEADYYC | QAWVN--------------NTMI | FGGGTKLTVL |
| iPS:3 93198 | 21-225_28A11 | VL3J3r/JL2 | SYELTQP-PSVSVSPGQTASITC | SGD----KLGE-------KYAC | WYQQKPGQSPVLVIY | Q-------DSKRPS | GIPERFSGSNSG-NTATLTISGTQAMDEADYYC | QAWDS--------------STYVV | FGGGTKLTVL |
| iPS:3 93200 | 21-225_35E1 | VL3J3r/JL2 | SYELTQP-PSVSVSPGQTASITC | SGD----KLGE-------KYAY | WFQQKPGQSPVIVIY | Q-------DSKRPS | GIPERFSGSNSG-NTATLTISGTQAMDEADYYC | QAWDN--------------STAV | FGGGTKLTVL |
| iPS:3 93202 | 21-225_6B4 | VL3J3r/JL2 | SYELTQP-PSVSVSPRQTASITC | SGD----KLGD-------KYAC | WYQQKPGQSPVLVIY | Q-------DRKRPS | GIPERFSGSNSG-NTATLTISGTQAMDEADYYC | QAWDN--------------NTVI | FGGGTKLTVL |
| iPS:3 93206 | 21-225_13F6 | VL3J3r/JL2 | SYELTQP-PSVSVSPGQTASITC | SGD----KLGD-------KYAC | WYQQKPGQSPVLVIY | Q-------DSKRPS | GIPERFSGSNSG-NTATLTISGTQAMDEADYYC | QAWGN--------------STAV | FGGGTKLTVL |
| iPS:3 93210 | 21-225_17D3 | VL3J3r/JL2 | SYELTQS-PSVSVSPGQTASITC | SGD----KLGD-------KIVY | WYQQKPGQSPVLVIY | Q-------DRKRPS | GIPERFSGSNSG-NTATLTISGTQAMDEADYYC | QAWDS--------------ITAV | FGGGTKLTVR |
| iPS:3 93212 | 21-225_30H6 | VL3J3r/JL2 | SYELTQP-PSVSVSPGQTASITC | SGD----KLGN-------KYAC | WYQQKPGQSPVLVIY | Q-------DSKRPS | GIPERFSGSNSG-NTATLTISGTQMDEADYYC | QAWD---------------SSTV | FGGGTKLTVL |

Figure 51 (Continued)

| | | | | | | | | |
|---|---|---|---|---|---|---|---|---|
| iPS:3 93214 | 21-225_33A1 | VL3j3r/JL2 | SYELTQP- PSVSVSPGQTASI TC | SGD----KLGD- ----KFVY | WYQQKPGQ SPVLVIY | Q------- ------- | GIPERFSGSNSG- NTATLTISGTQAMDEADYYC | QAWDS---- -------TTVV | FGGGT KLTVL |
| iPS:3 93218 | 21-225_14G3 | VL3j3r/JL2 | SYELTQP- PSVSVSPGQTASI TC | SGD----KLGD- ----KYVC | WYQQKPGQ SPVLVIY | Q------- DRKRPS | GIPERFSGSNSG- NTATLTISGTQAMDEADYYC | QAWGN---- -------STAVV | FGGGT KLTVL |
| iPS:3 93222 | 21-225_17F5 | VL3j3r/JL2 | SYELTQP- PSVSVSPGQTASI TC | SGD----KLGE- ----KYAC | WYQQKPGQ SPVLVIY | Q------- DRKRPS | GIPERFSGSNSG- NTATLTISGTQAMDEADYYC | QAWD----- -------SSTV | FGGGT KLTVL |
| iPS:3 93224 | 21-225_31C2 | VL3j3r/JL2 | SYELTQP- PSVSVSPGQTASI TC | SGD----KLGN- ----KYAC | WYQQKPGQ SPVLVIY | Q------- DSKRPS | GIPERFSGSNSG- NTATLTISGTQAMDEADYYC | QAWD----- -------SSTV | FGGGT KLTVL |
| iPS:3 93226 | 21-225_33E6 | VL3j3r/JL2 | SYELTQP- PSVSVSPGQTASI TC | SGD----KLGD- ----KYAY | WFQQKPGQ SPVLVIY | Q------- DRKRPS | GIPERFSGSNSG- NTATLTISGTQAMDEADYYC | QAWDN---- -------STAV | FGGGT KLTVL |
| iPS:3 93234 | 21-225_26C10 | VL3j3r/JL2 | SYEVTQP- PSMSVSPGQTASI TC | SGD----KLGD- ----KYVC | WFQQKPGQ SPVVVIY | Q------- DSKRPS | GIPERFSGSNSG- NTATLTISGTQAMDEADYYC | QAWV----- -------NNTV | FGGGT KLTVL |
| iPS:3 93345 | 21-225_5G7 | VL3j3r/JL2 | SYELTQP- PSVSVSPGQTASI TC | SGD----KLGN- ----KYAW | WYQQKPGQ SPVLVIY | Q------- DRKRPS | GIPERFSGSNSG- NTATLTISGTQAMDEADYYC | QAWDN---- -------STVV | FGGGT KLTVL |
| iPS:3 93565 | 21-225_34B11 | VL3j3r/JL2 | SYELTQP- PSVSVSPGQTASI TC | SGD----KLGD- ----KYAC | WYQQKPGQ SPVLVIY | Q------- DMKRPS | GIPERFSGSNSG- NTATLTISGTQAMDEADYYC | QAWDN---- -------STAV | FGGGT KLTVL |
| iPS:3 93950 | 21-225_3H10 | VL3j3r/JL2 | SYELSQP- PSVSVSPGQTASI TC | SGD----KLGE- ----KYAC | WYQQKPGQ SPVLVIY | Q------- DRKRPS | GIPERFSGSNSG- NKATLTISGTQAMDEADYYC | QAWVN---- -------NTMI | FGGGT KLTVL |
| iPS:3 98470 | 21-225_14B7 | VL3j3r/JL2 | SYELTQP- PSVSVSPGRTASI TC | SGD----KLGN- ----KYAY | WYQQKPGQ SPVLVIY | Q------- DRKRPS | GIPERFSGSNSG- NTATLTISGTQTMDEADYYC | QAWNN---- -------STVV | FGGGT KLTVL |
| iPS:3 98472 | 21-225_16E4 | VL3j3r/JL2 | SYELTQP- PSVSVSPGQTASI TC | SGD----KLGD- ----KYVY | WYQQKSGQ SPVLVIY | Q------- DSKRPS | GIPERFSGSNSG- NTATLTISGTQAMDEADYYC | QAWDS---- -------STVV | FGGGT KLTVL |
| iPS:3 98488 | 21-225_19F6 | VL3j3r/JL2 | PYELTQP- PSVSVSPGQTASI TC | SGD----KLGD- ----KYAC | WYQQKPGQ SPVLVIY | Q------- DSKRPS | GIPERFSGSNSG- NTATLTISGTQAMDEADYYC | QAWDN---- -------NTVV | FGGGT KLTVL |
| iPS:3 98490 | 21-225_21D12 | VL3j3r/JL2 | SYELTQP- PSVSVSPGQTVSI TC | SGD----KLGN- ----KYAY | WYQQKPGQ SPVLVIY | Q------- DRKRPS | GIPERFSGSNSG- NTATLTISGTQAMDEADYYC | QAWDN---- -------STVV | FGGGT RLTVL |
| iPS:3 98498 | 21-225_22E6 | VL3j3r/JL2 | SYELTQP- PSVSVSPGQTASI TC | SGD----KLGE- ----KYAC | WYQQKPGQ SPVLVIY | Q------- DRKRPS | GIPERYSGSNTG- NTATLTISGTQAMDEADYYC | QAWDS---- -------STAV | FGGGT KLTVL |
| iPS:3 98504 | 21-225_23D7 | VL3j3r/JL2 | SYELTQP- PSVSVSPGQTASI TC | SGE----KLGD- ----KYVC | WYQQKPGQ SPVLVIY | Q------- DSKRPS | GIPERFSGSNSG- NTATLTISGTQAMDEADYYC | QAWNS---- -------SNVV | FGGGT KLTVL |
| iPS:3 98546 | 21-225_9H10 | VL3j3r/JL2 | SYELTQP- PSVSVSPGQTASI TC | SGD----KLGD- ----KYAC | WYQQKPGQ SPVLVIY | Q------- DSKRPS | GIPERFSGSNSG- NTATLTISGTQAMDEADYYC | QAWDS---- -------STYVV | FGGGT KLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 02225 | 21-225_2B1 | VL3|3r/JL2 | SYELTQP-PSVSVSPGQTVSI TC | SGD---KLGD------KYAC | WYQQKPGQ SPVLVIY | Q------DRKRPS | GIPERFSGSNSG-NTATLTISGTQAMDEADYYC | QAWDN------NTVV | FGGGT KLTVL |
| iPS:4 02231 | 21-225_6D9 | VL3|3r/JL2 | SYELTQP-PSVSVSPGQTASI TC | SGD---KLGE------KYAC | WYQQKPGQ SPVLVIY | Q------DKKRPS | GIPERFSGSNSG-NTATLTISGTQAMDEADYYC | QAWD------SSTV | FGGGT KLIVL |
| iPS:4 04090 | 21-225_8D8 | VL3|3r/JL2 | SYELTQP-PSVSVSPGQTASI TC | SGD---KLGE------KYAC | WYQQKPGQ SPVVVIY | Q------DRKRPS | GIPERFSGSNSG-NTATLTISGTQAIDEADYYC | QAWDS------STAV | FGGGT KLTVL |
| iPS:4 23018 | 21-225_31D12_L C2 | VL3|3r/JL2 | SYELTQP-PSVSVSPGQTASI TC | SGD---KLGD------KYAY | WFQQKPGQ SPVIVIY | Q------DRKRPS | GIPERFSGSNSG-NTATLTISGTQAMDEADYYC | QAWDN------STAV | FGGGT KLTVL |
| Germline | | | L_FR1 | L_CDR1 | L_FR2 | L_CDR2 | L_FR3 | L_CDR3 | L_FR4 |
| VL2|2a2/L3b | | | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | SSYTS------SITWV | FGGGT KLTVL |
| iPS:4 68862 | 21-225_178H8 | VL2|2a2/L3b | QSALTQS-ASVSGSPGQSITI SC | TGTS-SDVGGY----NFVS | WYQQHPGK VPKFMIY | E------VSNRPS | GVPNRFSGSKSG-NTASLTISGLQAEDEADYYC | SSYTS------SYTWV | FGGGT KLTVL |
| iPS:4 36838 | 21-225_52H4 | VL2|2a2/L3b | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | NSYTS------NITWV | FGGGT KLTVL |
| iPS:4 37094 | 21-225_210D12 | VL2|2a2/L3b | QSALTQP-ASVSGSPGQSITI SC | TGTS-SDVGGY----NYVS | WYQQHPVK APKLLIY | E------VSNRPS | GVSNRFSGSKSG-NTASLTISGLQAEDEADYYC | NSYTS------SITWV | FGGGT KLTVL |
| iPS:4 37096 | 21-225_210E12 | VL2|2a2/L3b | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | GSYVK------GITWV | FGGGT SLTVL |
| iPS:4 37098 | 21-225_211C1 | VL2|2a2/L3b | QSALTQP-ASVSGSPGQSITI SC | TGTS-SDVGSY----NYVS | WYQQHPGK APKLMIY | E------VSNRPS | GVSNRFSGSKSG-NTASLTISGLQAEDEADYYC | NSYTS------SITWV | FGGGT KLTVL |
| iPS:4 37104 | 21-225_211G5 | VL2|2a2/L3b | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | NSYTR------SITWV | FGGGT KLTVL |
| iPS:4 37112 | 21-225_212C2 | VL2|2a2/L3b | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | SSYTR------SITWV | FGGGT KLTVL |
| iPS:4 37114 | 21-225_212A4 | VL2|2a2/L3b | QSALTQP-ASVSGSPGQSITI SC | TGTS-SDVGGY----NYVS | WYQQHPGK APKLMIY | E------VSNRPS | GVSNRFSGSKSG-NTASLTISGLQAEDEADYYC | GSYVK------GITWV | FGGGT SLTVL |
| iPS:4 37116 | 21-225_212F6 | VL2|2a2/L3b | QSALTQP-ASVSGSPGQSITI SC | TGTS-SDVGGY----NYVS | WYQQYPGK APKLMIY | E------VSNRPS | GVSNRFSGSKSG-NTASLTISGLQAEDEADYYC | NSYTS------SITWV | FGGGT KLTVL |
| iPS:4 37118 | 21-225_212G7 | VL2|2a2/L3b | QSALTQP-ASVSGSPGQSITI SC | TGTS-SDVGGY----NYVS | WYQQHPGK TPKLMIY | E------VSNRPS | GVSNRFSGSKSG-NTASLTISGLQAEDEADYYC | NSYTS------SITWV | FGGGT KLIVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 37128 | 21-225_213G3 | VL2|a2/JL3b | LSALTQP-ASVSGSPGQSITISC | TGTS-SDVGGY----NYVS | WYQQHPGK APKLMIS | E------VRNRPS | GVSNRFSGSKSG-NTASLTISGLQAEDEADYYC | NSYTR--------SITWV | FGGGT KLTVL |
| iPS:4 37130 | 21-225_213D5 | VL2|a2/JL3b | QSALTQP-ASVSGSPGQSITISC | TGTS-SDVGGY----NYVS | WYQQHPGK APKLVIY | E------VRNRPS | GVSTRFSGSKSG-NKASLTISGLQAEDEADYYC | CSYTR--------RITWV | FGGGT KLTVL |
| iPS:4 37146 | 21-225_215D3 | VL2|a2/JL3b | QSALTQP-ASVSGSPGQSITISC | TGTS-SDIGGY----NYVS | WYQQHPGK APTLMIY | E------VSNRPS | GVSNRFSGSKSG-NTASLTISGLQAEDEADYYC | NSYKR-------GSTWV | FGGGT KVTVL |
| iPS:4 37150 | 21-225_216A3 | VL2|a2/JL3b | QSALTQP-ASVSGSPGQSITISC | TGTS-SDVGGY----NYVS | WYQQHPGK APKLMIY | E------VSNRPS | GVSNRFSGSKSG-NTASLTISGLQAEDEADYYC | NSYTS--------SITWV | FGGGT KLTVL |
| iPS:4 37162 | 21-225_217B2 | VL2|a2/JL3b | QSALTQP-ASVSGPGQSITISC | TGTS-SDVGCY----NYVS | WYQQHPGK APKLLIY | E------VSNRPS | GVYNRFSGSKSG-NTASLTISGLQAEDEADYYC | GSYVK--------GITWV | FGGGT SLTVL |
| iPS:4 37172 | 21-225_219A7 | VL2|a2/JL3b | QSALTQP-ASVSGSPGQSITISC | TGTS-SDVGGY----NYVS | WYQQHPGK APKLMIY | E------VRNRPS | GVSNRFSGSKSG-NTASLTISGLQAEDEADYYC | CSYTR--------SITWV | FGGGT KLTVL |
| iPS:4 37182 | 21-225_221H2 | VL2|a2/JL3b | LSALTQP-ASVSGSPGQSITISC | TGTS-SDVGGY----NYVS | WYQQHPGK APKLMIS | E------VRNRPS | GVSNRFSGSKSG-NTASLTISGLQAEDEADYYC | NSYTR--------SITWV | FGGGT KLTVL |
| iPS:4 37184 | 21-225_221G4 | VL2|a2/JL3b | QSALTQP-ASVSGSPGQSITISC | TGTS-SDVGGY----NYVS | WYQQHPGK APKLMIY | E------VRNRPS | GVSNRFSGSKSG-NTASLTISGLQAEDEADYYC | NSYTR--------SITWV | FGGGT KLTVL |
| | | Germline | | | | | | | |
| | VL1|1c|JL2 | | QSVLTQP-PSASGTPGQRVTISC | SGSS-SNIGS-----NTVN | WYQQLPGT APKLLIY | S------NNQRPS | GVPDRFSGSKSG-TSASLAISGLQSEDEADYYC | AAWDD | FGGGT KLTVL |
| iPS:4 68864 | 21-225_60D6 | VL1|1c|JL2 | QSVLTQP-PSASGTPGQRVTISC | SGSS-SNIGS-----NTVN | WYQQLPGT APKLLIY | S------NNQRPS | GVPDRFSGSKSG-TSASLAISGLQSEDEADYYC | AAWDD--------SLNGP | VGGGT KLTVL |
| iPS:4 36660 | 21-225_146D8 | VL1|1c|JL2 | QSVLTQP-PSTSGTPGQRVTISC | SGSS-SYIGS-----NTVD | WYQQLPGT APKLLIY | S------NNQRPS | GVPDRFSGSKSG-TSASLAISGLQSEDEADYYC | AAWDDS-------LNGVV | FGGGT KLTVL |
| iPS:4 36680 | 21-225_147H12 | VL1|1c|JL2 | QSVLTQP-PSASGTPGQRVTISC | SGSS-SNIGS-----YAVN | WYQQLPGT APKLLIY | S------NNHRPS | GVPDRFSGSKSG-TSASLAISGLQSEDEADYYC | EAWDDS-------LNGPV | FGGGT KLTVL |
| iPS:4 36682 | 21-225_146A8 | VL1|1c|JL2 | QSVLTQP-PSASGTPGQRVTISC | SGSS-SNIGS-----NSIN | WYQQLPRT APKLLIY | S------MDQRPS | GVPDRFSGSKSG-TSASLAISGLQSEDEADYYC | AAWDDS-------LNGVV | FGGGT KLTVL |
| iPS:4 36684 | 21-225_146B6 | VL1|1c|JL2 | QSVLTQP-PSASGTPGQRVTISC | SGSS-SNIGS-----NAVN | WYQQLPGT APKLLIY | S------NNQRPS | GVPDRFSGSKSG-TSASLAISGLQSEDEADYYC | AAWDDS-------LNGVV | FGGGT KLTVL |
| iPS:4 36696 | 21-225_149A1 | VL1|1c|JL2 | QSVLTQP-PSASGTPGQRVTISC | SGSS-SNIGS-----NAVN | WYQQLPGT APKLLIY | S------NNQRPS | GVPDRFSGSKSG-TSASLAISGLQSEDEADYYC | AAWDDS-------LNGVV | FGGGT KLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 36712 | 21-225_150F9 | VL1j1c/JL2 | QSVLTQP-PSASGTPGQRVTISC | SGSS-SNIGS-----NAVN | WYQQLPGTAPKLLIY | S-------NSQRPS | GVPDRFSGSKSG---TSASLAISGLQSEDEADYFC | AAWDDS-------------LNGVV | FGGGTKLTVL |
| iPS:4 36750 | 21-225_154G12 | VL1j1c/JL2 | QSVLTQP-PSASGTPGQRVTISC | SGSS-SNIGN-----NAVS | WYQQLPGTAPKLLIY | S-------NDHRPS | GVPDRFSGSKSG---TSASLAISGLQSEDEADYYC | AAWDDS-------------LKGPV | FGGGTKLTVL |
| iPS:4 36762 | 21-225_156H2 | VL1j1c/JL2 | QSVLTQP-PSASGTPGQRVTISC | SGSS-SNIGS-----NTVN | WYQQLPGTAPKLLIY | S-------SNQRPS | GVPDRLSGSKSG---TSASLAISGLQSEDEADYYC | AAWDDS-------------LNGVV | FGGGTKVTVL |
| iPS:4 37044 | 21-225_197F9 | VL1j1c/JL2 | QSVLTQP-PSASGTPGQRVTISC | SGSS-SNIGS-----NTVN | WYQQLPGTAPKLLIY | S-------NNQRPS | GVPDRFSGSKSG---TSASLAISGLQSEDEADYYC | AAWDDS-------------MNGPV | FGGGTKLTVL |
| iPS:4 37060 | 21-225_199C3 | VL1j1c/JL2 | QSVLTQP-PSASGTPGQRVTISC | SGSS-SNIGS-----NTVN | WYQQLPGTAPKLLIY | S-------NNQRPS | GVPDRFSGSKSG---TSASLAISGLQSEDEADYYC | AAWDDS-------------LNGPV | FGGGTKLTVL |
| iPS:3 93180 | 21-225_4G12 | VL1j1c/JL2 | QSVLTQP-PSASGTPGQRVNM | SGTN-SNIGS-----YTVN | WYQQLPGTAPKLLIY | I-------NNQRPS | GVPDRFSGSKSG---TSASLAISGLQSEDEADYYC | AAWDDS-------------LNGHVV | FGGGTKLTVL |
| iPS:3 93230 | 21-225_9G9 | VL1j1c/JL2 | QSVLTQP-PSASGTPGQRVNM | SGTN-SNIGS-----YTVN | WYQQLPGTAPKLLIY | I-------NNQRPS | GVPDRFSGSKSG---TSASLAISGLQSEDEADYYC | AAWDDS-------------LNGHVV | FGGRTKLTVL |
| VL3j3p/JL2 | | Germline | SYELTQPPSVSVSPGQTARITC | SGD---ALPK-----KYAY | WYQQKSGQAPVLVIY | E-------DSKRPS | GIPERFSGSSSG---TMATLTISGAQVEDEADYYC | YSTDSS-------------GNHVV | FGGGTKLTVL |
| iPS:4 68866 | 21-225_190C1 | VL3j3p/JL2 | SYELTQPPSVSVSPGQTARITC | TGD---AMPK-----KYAY | WDQQKSGQAPVLVIS | E-------DSKRPS | GIPERFSGSSSG---TMAPLTISGAQVEDFTDYDC | NSIDS--------------SGNRV | FGGGTKLTVL |
| iPS:4 37214 | 21-225_48B12 | VL3j3p/JL2 | SYELTQPPSVSVSPGQTARITC | SGD---ALPK-----KYAY | WYQQKSGQAPVLVIY | E-------DSKRPS | GIPERFSGSSSG---TMATLTISGAQVEDEADYYC | NSTDSS-------------GNHVV | FGGGTKLTVL |
| VL1j1c/JL3b | | Germline | QSVLTQP-PSASGTPGQRVTISC | SGSS-SNIGS-----NTVN | WYQQLPGTAPKLLIY | S-------NNQRPS | GVPDRFSGSKSG---TSASLAISGLQSEDEADYYC | AAWDDS-------------LNGWV | FGGGTTLTVL |
| iPS:4 36234 | 21-225_51E3 | VL1j1c/JL3b | QSVLTQP-PSASGTPGQRVTISC | SGSN-SNIGS-----NIVI | WYQQLPGTAPKLLIY | S-------NDQRPS | GVPDRFSGSKSG---TSASLAISGLQSEDEADYYC | TAWDDS-------------LNGWV | FGGGTTLTVL |
| iPS:4 36830 | 21-225_51F4 | VL1j1c/JL3b | QSVLTQP-PSASGTPGQRVTISC | SGSS-SNIGS-----NIVI | WYQQLPGTAPKLLIY | S-------NDQRPS | GVPDRFSGSKSG---TSASLAISGLQSEDETDYYC | TAWDDS-------------LNGWV | FGGGTTLTVL |
| iPS:4 36834 | 21-225_52F1 | VL1j1c/JL3b | QSVLTQP-PSASGTPGQRVTISC | SGSS-SNIGS-----NIVI | WYQQLPGTAPKLLIY | S-------NDQRPS | GVPDRFSGSKSG---TSASLAISGLQSEDEADYYC | AAWDDS-------------LNGWV | FGGGTTLTVL |
| iPS:4 36842 | 21-225_54E9 | VL1j1c/JL3b | QSVLTQP-PSASGTPGQRVTISC | SGSN-SNIGN-----NIVI | WYQQLPGTAPKLLIY | V-------NDQRPS | GVPDRFSGSKSG---TSASLAISGLQSEDEADYYC | AAWDDS-------------LNGWV | FGGGTTLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 36844 | 21-225_56G1 | VL1l1c/JL3b | QSVLTQP-PSASGTPGQRVTISC | SGSS-SNIGS-----HIVT | WYQQLPGT APKLLIY | S---------NDQRPS | GVPDRFSGSKSG---TSASLAISGLQSEDEADYYC | AVWDDS---------LIGWV | FGGGT TLTVL |
| iPS:4 36846 | 21-225_56E3 | VL1l1c/JL3b | QSVLTQP-PSASGTPGQRVTISC | SGSS-SNIGS-----NIVT | WYQQLPGT APKLLIY | S---------NNQRPS | GVPDRFSGSKSG---TSASLAISGLQSEDEADYCC | AAWDDS---------LNGWV | FGGGT TLTVL |
| iPS:4 37010 | 21-225_192G3 | VL1l1c/JL3b | QSVLTQP-PSASGTPGQRVTI | SGSS-SNIGS-----NTVN | WYQQFPGT APKLLIY | G---------NKQRPS | RVPDRFSGSKSG---TSASLAISGLQSEDETDYYC | AAWDDS---------LNGWV | FGGGT KLTVL |
| iPS:4 37032 | 21-225_195H6 | VL1l1c/JL3b | QSVLTQP-PSASGTPGQRVTISC | SGSS-SNIGS-----HTVN | WYQQLPGT APKLLIY | N---------NYQRPS | GVPDRFSGSKSG---TSASLTISGLQSEDEADYYC | ATWDDS---------LSVWV | FGGGT KVTVL |
| iPS:4 51104 | 21-225_49C5 | VL1l1c/JL3b | QSVLTQP-PSASGTPGQRVTISC | SGSS-SNIGS-----NIVI | WYQQLPGT APKLLIY | S---------NDQRPS | GVPDRFSGSKSG---TSASLAISGLQSEDEADYYC | TAWDDS---------LNGWV | FGGGT TLTVL |
| iPS:4 51106 | 21-225_49D10 | VL1l1c/JL3b | QSVLTQP-PSASGTPGQRVTISC | SGSN-SNIGS-----NIVI | WYQQLPGT APKLLIY | S---------NDQRPS | GVPDRFSGSKSG---TSASLAISGLQSEDEADYYC | AAWDDS---------LNGWV | FGGGT TLTVL |
| iPS:4 51108 | 21-225_53E8 | VL1l1c/JL3b | QSVLTQP-PSASGTPGQRVTISC | SGSC-SNIGS-----NIVI | WYQQLPGT APKLLIY | S---------NDQRPS | GVPDRFSGSKSG---TSASLAISGLQSEDEADYYC | TAWDDS---------LNDWV | FGGGT TLTVL |
| VL3l3r/JL1 | | Germline | SYELTQP-PSVSVSPGQTASITC | SGD----KLGD-----KFAC | WYQQKPGQ SPKRPS | Q---------DSKRPS | GIPERFSGSNSG---NTATLTISGTQAMDEADYYC | QAWDS | FGTGT KVTVL |
| iPS:4 36662 | 21-225_147D7 | VL3l3r/JL1 | SYELTQP-PSVSVSPGQTASITC | SGD----KLGD-----KFAC | WYQQKPGQ SPVLVIY | Q---------DRKRPS | GIPERFSGSNSG---NTATLTISGTQAMDEADYYC | QAWDR---------NTAV | FGTGT KVTVL |
| iPS:4 36720 | 21-225_151H6 | VL3l3r/JL1 | SYELTQP-PSVSVSPGQTASITC | SGD----KLGD-----KYAC | WYQQKPGQ SPVLVIY | Q---------DIKRPS | GIPERFSGSNSG---NTATLTISGTQAMDEADYYC | QAWDS---------STYV | FGTGT KVTVL |
| iPS:4 36726 | 21-225_152G5 | VL3l3r/JL1 | SYEMTQP-PSVSVSPGQTAIII TC | SGD----KLGD-----KYAC | WYQQKPGQ SPVLVIY | Q---------DSKRPS | GIPERFSGSNSG---NTATLTISGTQAMDEADYYC | QAWDS---------STYV | FGTGT KVTVL |
| iPS:4 36732 | 21-225_152B12 | VL3l3r/JL1 | SYELTQP-PSVSVSPGQTASITC | SGD----KLGN-----KYAC | WYQQKPGQ SPVLVIY | Q---------DIKRPS | GIPERFSGSNSG---NTATLTISGTQAMDEADYYC | QAWDS---------STYV | FGTGT KVTVL |
| iPS:4 36734 | 21-225_153A8 | VL3l3r/JL1 | SYELTQP-PSVSVSPGQTASITC | SGD----KLGD-----KYAC | WYQQKPGQ SPMLVIY | Q---------DSKRPS | GIPERFSGSNSG---NTATLTISGTQAMDEADYYC | QAWDS---------STYV | FGTGT KVTVL |
| iPS:4 36754 | 21-225_155G3 | VL3l3r/JL1 | SYELTQP-PSVSVSPGQTASITC | SGD----KLGD-----KYVC | WYQQKPGQ SPVLVIY | Q---------DSKRPS | GIPERFSGSNSG---NTATLTISGTQAMDEADYYC | QAWDN---------STYV | FGTGT KVTVL |
| iPS:4 37190 | 21-225_225A9 | VL3l3r/JL1 | SYELTQP-PSVSVSPGQTASITC | SGD----KLGN-----KYAC | WYQQKPGQ SPVLVIY | Q---------DSKRPS | GIPERFSGSNSG---NTATLTISGTQAMDEADYYC | QAWDS---------NTACV | FGTGT KVTVL |
| | | Germline | L_FR1 | L_CDR1 | L_FR2 | L_CDR2 | L_FR3 | L_CDR3 | L_FR4 |

Figure 51 (Continued)

| | | L_FR1 | L_CDR1 | L_FR2 | L_CDR2 | L_FR3 | L_CDR3 | L_FR4 |
|---|---|---|---|---|---|---|---|---|
| VL5j5c/JL3b | | QAVTQP-ASLSASPGASASL GITVT- | TLRS-GITVT-YRIY | WYQQKPGS FPQFLLR | YIS---DSDKHQGS | GVPSRFSGGKDASANAGILF ISGLQSEDEADYYC | MIWHS---SASWV | FGGGT KLTVL |
| iPS:436702 21-225_149E8 | VL5j5c/JL3b | QAVSTQP-SSLSASPGASASL GITVT-YRIY | TLRS-GITVT-YRIY | WYQQKPGS FPQFLLR | YIS---DSDKHQGS | GVPSRFSGGKDASANAGILF ISGLQSEDEADYYC | MIWHS---SAWV | FGGGT KLTVL |
| Germline | | | | | | | | |
| VL1f1e/JL2 | | QSVLTQP-PSVSGAPGQRVTI SNIGAG-YDVH | TGSS-SNIGAG-YDVH | WYQQLPGT APKLLIY | G---NSNRPS | GVPDRFSGSKSG-TSASLAITGLQAEDEADYYC | QSYDSS---LSGPVI | FGGGT KLTVL |
| iPS:436752 21-225_155H1 | VL1f1e/JL2 | QSVLTQP-PSVSGAPGQRVTI SC | TGSS-SNIGAG-YDVH | WYQQLPGT APKLLIY | G---NSNRPS | GVPDRFSGSKSG-TSASLAITGLQAEDEADYHC | QSYDSS---LSGPVI | FGGGT KLTVL |
| iPS:436820 21-225_179D10 | VL1f1e/JL2 | QSVLTQP-PSVSGAPGQRVTI SC | TGSS-SNFGTD-YDVH | WYQQFPGT APKLLIY | G---HSNRPS | GVPDRFSGSKSG-TSASLAITGLQAEDEADYYC | QSYDR---SLNVV | FGGGT KLTVL |
| iPS:437188 21-225_224B11 | VL1f1e/JL2 | QSVLTQP-PSVSGAPGQRVTI SC | TGSS-SNIGAG-YDVH | WYQQLPGT APKLLIF | G---HSNRPS | GVPDRFSGSKSG-TSASLAITGLQAEDEADYHC | QSYDN---SLSGV | FGGGT KLTVL |
| iPS:437198 21-225_226F8 | VL1f1e/JL2 | QSVLTQP-PSVSGAPGQRVTI SC | TGSS-SNIGAG-YDVH | WYQQLPGT APKLLIY | G---NSNRPS | GVPDRFSGSKSD-TSASLAITGLQAEDEADYYC | QSYDN---SLSGV | FGGGT KLTVL |
| iPS:437202 21-225_227D3 | VL1f1e/JL2 | QSVLTQP-PSVSGAPGQRVTI SC | TGSS-SNIGAG-YDVH | WYQQLPGT APKLLIY | G---NSNRPS | GVPDRFSGSKSD-TSASLAITGLQAEDEADYYC | QSYDN---SLSGV | FGGGT KLTVL |
| iPS:437208 21-225_227C10 | VL1f1e/JL2 | QSVLTQP-PSVSGAPGQRVTI SC | TGSS-SNIGAG-YDVH | WYQQLPGT APKLLIY | G---NSNRPS | GVPDRFSGSKSD-TSASLAITGLQAEDEADYYC | QSYDN---NLSGV | FGGGT KLTVL |
| iPS:43003 21-225_43F11_LC2 | VL1f1e/JL2 | QSVLTQP-PSVSGAPGQRVTI SC | TGSS-SNIGAG-YDVH | WYQQLPGT APKLLIY | G---NSNRPS | GVPDRFSGSKSG-TSASLAITGLQAEDEADYYC | QSYDNS---LSGSV | FGGGT KLTVL |
| Germline | | | | | | | | |
| VL6j6a/JL3b | | | | | | | | |
| iPS:436792 21-225_169D12 | VL6j6a/JL3b | NFMLTQP-HSVSESPGKTVTI SC | TRSS-GSITG-NYVQ | WHQQRPGN SPTTLIY | E---DKKRPS | GVPDRFSGSIDSSSNSASLT ISGLKTEDEADYYC | QSYYS---GNWV | FGGGT KLTVL |
| Germline | | | | | | | | |
| VL3j3l/JL2 | | | | | | | | |
| iPS:436800 21-225_171D12 | VL3j3l/JL2 | SSELTQD-PAVSVALGQTVRI TC | QGD---SLRS-YYAS | WYQQKPGQ APILVIY | A---KNNRPS | GIPDRFSGSNSG-NTASLTITGAQAEDEADYYC | NSRDSS---GSHVV | FGGGT KLTVL |
| iPS:436804 21-225_172C3 | VL3j3l/JL2 | SSELTQD-PAVSVALGQTVRI TC | QGD---SLRN-YYVS | WYQQKPGQ APILVIY | T---KNSRPS | GIPDRFSGSTSG-NTASLTITGTQAEDEADYYC | NSRDSS---GNHVV | FGGGT KLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 36806 | 21-225_172B12 | VL3l3l/JL2 | SSELTQD-PAVSVALGQTVRITC | QGD---SLRN------YYAS | WYQQKPGQ APILVIY | T-------KNSRPS | GIPDRFSGSTSG--NTASLTITGAQAEDEADYYC | NSRDSS----------GNHVV | FGGGT KLTVL |
| iPS:4 36964 | 21-225_190B3 | VL3l3l/JL2 | SSELTQD-PAVSVALGQTVRITC | QGD---KLRT------YYAS | WYQQKPGQ APVLVVY | G-------KNNRPS | GIPDRFSGSSSG--NTASLTITGAQAEDEADYYC | NSRDSS----------GNHLVL | FGGGT KLTVL |
| iPS:4 36970 | 21-225_190B8 | VL3l3l/JL2 | SSELTQD-PAVSVALGQTVRITC | QGD---TLRP------YYVS | WYQQKPGQ APVLVIY | G-------KNNRPS | GIPDRFSGSSSG--NTASLTITGAQAEDEADYYC | NSRDSS----------GNHLVV | FGGGT KLTVL |
| iPS:4 36980 | 21-225_190C10 | VL3l3l/JL2 | SSELTQD-PAVSVALGQTVRITC | QGD---SLRP------YYAS | WYQQKPGQ APVLVIY | G-------KNNRPS | GIPDRFSGSSSG--NTASLTITEAQAEDEADYYC | NSRDSS----------GNHLVV | FGGGT KLTVL |
| iPS:4 36992 | 21-225_191B8 | VL3l3l/JL2 | SSELTQD-PAVSVALGQTVRITC | QGD------TLRP------YYAS | WYQQKPGQ APVLVIY | G-------KNNRPS | GISDRFSGSSSG--NTASLTITGAQAEDEADYYC | NSRDSS----------GNHLVV | FGGGT KLTVL |
| iPS:4 36994 | 21-225_191A9 | VL3l3l/JL2 | SSELTQD-PAVSVALGQTVRITC | QGD---SLRP------YYAS | WYQQKPGQ APVLVIY | G-------KNNRPS | GIPDRFSGSSSG--NTASLTITEAQAEDEADYYC | NSRDSC----------GNHLVV | FGGGT KLTVL |
| iPS:4 37016 | 21-225_193A6 | VL3l3l/JL2 | SSELTQD-PAVSVALGQTVRITC | QGD---SLRS------YYAN | WYQQKPGQ APVLFIY | A-------KNNRPS | GIPDRFSGSNSG--NTASLTITGAQAEDEADYYC | NSRDSS----------GNHLVV | FGGGT KLTVL |
| VL2l2b2/JL2 | | Germline | QSALTQP-ASVSGSPGQSITI SC | TGTS--SDVGSY----NLVS | WYQQHPGK APKLMIY | E-------VSKRPS | GVSNRFSGSKSG--NTASLTISGLQAEDEADYYC | CSYAGS----------STYVV | FGGGT KLTVL |
| iPS:4 36810 | 21-225_175F4 | VL2l2b2/JL2 | QSALTQP-ASVSGSPGQSITI SC | TGTS---SDVGRF----NLVS | WYQQHPGY APKLMIY | E-------VSKRPS | GVSNRFSGSKSG--NTASLTISGLQAEDEADYYC | CSYAGS----------STYVV | FGGGT KLTVL |
| iPS:4 36814 | 21-225_178H10 | VL2l2b2/JL2 | QSALTQP-ASVSGSPGQSITI SC | TGTS---SDVGRF----NLVS | WYQQHPGN APKLMIY | E-------VSKRPS | GVSNRFSGSKSG--NTASLTISGLQAEDEADYYC | CSYAGS----------STFVV | FGGGT KLTVL |
| VL3l3l/JL3b | | Germline | SSELTQD-PAVSVALGQTVRITC | QGD---SLRN------YYAS | WYQQKPGQ APVLVIY | G-------KNNRPS | GIPDRFSGSSSG--NTASLTITGAQAEDEADYYC | NSRDSS----------GNHWV | FGGGT KLTVL |
| iPS:4 36816 | 21-225_179H5 | VL3l3l/JL3b | SSELTQD-PAVSVALGQTVRITC | QGD---SLRN------YYAS | WYQQKPGQ APVFVIY | G-------KNNRPS | GIPDRFSGSRSG--NTASLTITGAQAEDEADYYC | NSRDSS----------GNHWV | FGGGT KLTVL |
| VL1l1e/JL1 | | Germline | QSVLTQP-PSVSGAPGQRVTI SC | TGSS--SNIGAG----FEVH | WYQQLPGT APKLLIY | G-------NSNRPS | GVPDRFSGSKSG--TSASLAITGLQAEDEADYYC | QSYDSS----------LSGYV | FGTGT KVTVL |
| iPS:4 36832 | 21-225_51D8 | VL1l1e/JL1 | QSVLIQP-PSVSGAPGQRVTI SC | TGSS--SNIGAG----FEVH | WYQQLPGI APKLLIY | G-------NSNRPS | GVPDRFSGSKSG--TSASLAITGLQAEDEADYYC | QSYDSS----------LSGYV | FGTGI KVTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| | | VL3f/JL7 | | | | | | | |
| iPS:4 36840 | 21-225_53E9 | VL3f/JL7 | SYELTQP- PSVSVSPGQTASI TC | SGT---KLGD- ---KYVC | WYQQKPGQ SPVLVIN | Q------ DTMRPS | GIPERFSGSNSG- NTATLTISGTQAMDEADYYC | QTWDS------ -----STAV | FGGGT TLTVL |
| iPS:4 36950 | 21-225_184G4 | VL3f/JL7 | SYELTQP- PSVSVSPGQTASI TC | SGD---RLGD- ---KFAC | WYQQKPGQ SPVLVIY | E------ DRKRPS | GIPERFSGSNSG- NTATLTISGTQAMDEADYYC | QAWDS------ -----RTVV | FGGGT QLTVL |
| | Germline | | | | | | | | |
| | | VL1l/bJL2 | | | | | | | |
| iPS:4 36856 | 21-225_58C5 | VL1l/bJL2 | QSVLTQP- PSVSAAPGQKVTI SC | SGSS-SNIGN- ----NYVS | WYQQLPGT APKLLIY | D------ NNKRPS | GIPDRFSGSKSG- TSATLGITGLQTGDEADYYC | GTWDIS------ -----LSVGV | FGGGT KLTVL |
| iPS:4 36960 | 21-225_198D2 | VL1l/bJL2 | QSVLTQP- PSVSAAPGQKVTI SC | SGSS-SNIGS- ----NYVS | WYQQLPGT APKVLIY | D------ NNKRPS | GIPDRFSGSKSG- TSATLGITGLQTGDEADYYC | GTWDSR------ -----LNVGV | FGGGT KLTVL |
| iPS:4 36966 | 21-225_190C3 | VL1l/bJL2 | QSVLTQP- PSVSAAPGQKVTI SC | SGSS-SNIGN- ----NYVS | WYQQLPGT APKLLIY | D------ SNKRPS | GIPDRFSGSKSG- TSATLGITGLQTGDEADYYC | GTWDSS------ -----LSTVV | FGGGT KLTVL |
| iPS:4 36968 | 21- 225_190B10 | VL1l/bJL2 | QSVLTQP- PSVSAAPGQKVTI SC | SGSS-SNIGN- ----NYVS | WYQHLPGT APKLLIY | D------ NNKRPS | GIPDRFSGSKSG- TSATLGITGLQTGDEADYYC | GTWDSS------ -----LSAGV | FGGGT KLTVL |
| iPS:4 36974 | 21-225_190H7 | VL1l/bJL2 | QSVLTQP- PSVSAAPGQKVTI SC | SGSS-SNIGS- ----NYVS | WYQQLPGT APKLLIY | D------ NNKRPS | GIPDRFSGSKSG- TSATLGITGLQTGDEADYYC | GTWDGR------ -----LNVGV | FGGGT KLTVL |
| iPS:4 36976 | 21-225_190D8 | VL1l/bJL2 | QSVLTQP- PSVSAAPGQKVTI SC | SGSS-SNIGN- ----HYVS | WYQQLPGT APKLLIY | D------ SSKRPS | EIPDRFSGSKSG- TSATLGITGLQTGDEADYYC | GTWDSS------ -----LSTVV | FGGGT KLTVL |
| iPS:4 36982 | 21- 225_190D10 | VL1l/bJL2 | QSVLTQP- PSVSAAPGQKVTI SC | SGSS-SNIGS- ----NYVS | WYQQLPGT VPKVLIY | D------ NNKRPS | GIPDRFSGSKSG- TSATLGITGLQTGDEADYYC | GTWDSR------ -----LNVGV | FGGGT KLTVL |
| iPS:4 36986 | 21-225_191A1 | VL1l/bJL2 | QSVLTQP- PSVSAAPGQKVTI SC | SGSS-SNLGN- ----NFVS | WYQQFPGT APKLLIY | D------ NYKRPS | GIPDRFSVSKSG- TSATLGITGLQTGDEADYYC | GTWDSS------ -----LNTGV | FGGGT KLTVL |
| iPS:4 37006 | 21-225_192G2 | VL1l/bJL2 | QSVLTQP- PSVSAAPGQKVTI SC | SGSS-SNIGN- ----NYVS | WYQQLPGT APKLLIY | D------ NNKRPS | RIPDRFSGSKSG- TSATLGITGLQTGDEADYYC | GTWDSS------ -----LSAGV | FGGGT KLTVL |
| iPS:4 37024 | 21- 225_194F11 | VL1l/bJL2 | QSVLTQP- PSVSAAPGQKVTI SC | SGSS-SNIGN- ----NYVS | WYQQLPGT APKLLIY | D------ NNKRPS | GIPDRFSGSKSG- TSATLGITGLQTGDEADYYC | GTWDSR------ -----LSAGV | FGGGT KLTVL |
| iPS:4 37028 | 21- 225_194G12 | VL1l/bJL2 | QSVLTQP- PSVSAAPGQKVTI SC | SGSS-SNIGN- ----NYVS | WYQQLPGT APKLLIY | D------ NNKRPS | RIPDRFSGSKSG- TSATLGITGLQTGEEADYYC | GTWDSS------ -----LSVGV | FGGGT KLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 37042 | 21-225_197E8 | VL1|1b/JL2 | QSVLTQP-PSVSAAPGQKVTISC | SGSS-SNIGN-----KYVS | WYQQFPGT APKLLIY | D------NNKRPS | KIPDRFSGSKSG-TSATLGITGLLTGDEADYYC | GIWDRS------LSVMV | FGGGT KLTVL |
| iPS:4 37064 | 21-225_200G8 | VL1|1b/JL2 | QSVLTQP-PSVSAAPGQRVTISC | SGSS-SNLGN-----NFVS | WYQQFPGT APKLLIY | D------NYKRPS | GIPDRFSVSKSG-TSATLGITGLQTGDEADYYC | GTWDSS------LNTGV | FGGGT KLTVL |
| iPS:4 37086 | 21-225_209A8 | VL1|1b/JL2 | QSVLTQP-PSVSAAPGQKVTISC | SGSS-SNIGS-----MFLS | WYQQLPGT APKLLIY | D------NNKRPS | GIPDRFSGSKSG-TSATLGITGLQTGDEADYYC | GTWDSS------LSAGV | FGGGT KLTVL |
| iPS:4 37138 | 21-225_214D8 | VL1|1b/JL2 | QSVLTQP-PSVSAAPGQKVTISC | SGSS-SNIGN-----NYVS | WYQQFPGT APKLLIE | D------NNKRPS | GIPDRFSGSKSG-TSATLGITGLQTGDEADYYC | GAWDSS------LSAVV | IGGGS KLTVL |
| iPS:4 37168 | 21-225_218G4 | VL1|1b/JL2 | QSVLTQP-PSVSAAPGQKVTISC | SGSS-SNIGN-----NYVS | WYQQLPGT APKLLIY | D------SNKRPS | GIPARFSGSKSG-TSATLGITGLQTGDEADYYC | GTWDSS------LNTVV | FGGGT KLTVL |
| | Germline | VL6|6a/JL2 | | | | | | | L_FR4 |
| iPS:4 36888 | 21-225_63G7 | VL6|6a/JL2 | NFMLTQP-HSVSESPGKTVTISC | TRSN-GSIVS-----NYVQ | WYQQRPGS SPTTMIY | E------DSRRPS | GVPDRFSGSIDSSSNSASLT ISGLKTEDEADYSC | QSYDG------INVV | FGGGT KLTVL |
| iPS:4 36890 | 21-225_63A10 | VL6|6a/JL2 | NFMLTQP-HSVSESPGKTVTISC | TRSN-GSIVS-----NYVQ | WYQQRPGS SPTTVIY | E------DKRRPS | GVPDRFSGSIDSSSNSASLT ISGLKTEDEADYYC | QSYDS------INVV | FGGGT KLTVL |
| | Germline | VL8|8a/JL3b | | | | | | | L_FR4 |
| iPS:4 36910 | 21-225_73G1 | VL8|8a/JL3b | QTVVTQE-PSFSVSPGGTVTLTC | GLSS-----GSVSTS-YYPS | WYQQTPGQ APRFLIY | N------TNTRSS | GVPDRFSGSILG-NKAALTITGAQADDESDYYC | VLYMG------SAIWV | FGGGT KLTVL |
| iPS:4 36948 | 21-225_183F5 | VL8|8a/JL3b | QTVVTQE-PSFSVSPGGTVTLTC | GLSS-----GSVSTT-FYPS | WYQQTPGQ APRFLIY | N------TNTRSS | GVPDRFSGSILG-NKAALTITGAQADDESDYYC | VLYMG------SGIWV | FGGGT KLTVL |
| | Germline | VL7|7a/JL2 | | | | | | | L_FR4 |
| iPS:4 36920 | 21-225_74E5 | VL7|7a/JL2 | QTVVTQE-PSLTVSPGGTVTLTC | ASSI-----ETVTSG-SYFN | MFQQKPGQ APRALIY | S------TSNKHS | WTPARFSGSLLG-GKAALTLSGVQPEDEAEYYC | LLYYG------GAQLV | FGGGT KLTVL |
| iPS:4 36926 | 21-225_78D10 | VL7|7a/JL2 | QTVVTQE-PSLTVSPGGTVTLTC | ASSI-----GAVTSG-YFPN | MFQQKPGQ APRALIY | S------TDNKHS | WTPARFSGSLLG-GKAALTLSGVQPEDEAEYYC | LLYYG------GAQLM | FGGGT KLTVL |
| iPS:4 36958 | 21-225_190D1 | VL7|7a/JL2 | QTVVTQE-PSLTVSPGGTVTLTC | ASSI-----GAVTSG-SYFN | MFQQKPGQ APRALIY | S------TSNKHS | WTPARFSGSLLG-GKAALTLSGVQPEDEADYYC | LLYYG------GAQVA | FGGGT KLTVL |

Figure 51 (Continued)

| | | | | | | | | |
|---|---|---|---|---|---|---|---|---|
| iPS:4_36984 | 21-225_190F10 | VL7l7a/JL2 | QTVVTQE-PSLTVSPGGTVTLTC | VFST-GAVTSG-SFPN | WFQQKPGQAPRALIY | S------TSNKHS | WTPARFSGSLLG-GKAALTLSGVQPEDEADYYC | LLYCG--------GAQLV | FGGGT KLTVL |
| iPS:4_36988 | 21-225_191A2 | VL7l7a/JL2 | QTVVTQE-PSLTVSPGGTVTLTC | VLST-GAVTSG-SFPN | WFQQKPGQAPRALIY | S------TSNKHS | WTPARFSGSLLG-GKAALTLSGVQPEDEADYYC | MLYCG--------GAQLV | FGGGT KLTVL |
| iPS:4_37002 | 21-225_191H9 | VL7l7a/JL2 | QTVVTQE-PSLTVSPGGTVTLTC | ASST-GAVTSA-YYPN | WLQQKPGQAPRTLIY | S------TNNKHS | WTPARFSGSLLG-GKAALTLSDVQPEDEAEYYC | LIFYG--------GVHVI | FGGGT KLTVL |
| iPS:4_37008 | 21-225_192E3 | VL7l7a/JL2 | QTVVTQE-PSLTVSPGGTVTLTC | AFST-GSVTSG-SYPN | WFQQKPGQAPRALIY | S------TNNKHS | WTPARFSGSLLG-GKAALTLSGVQRDEAEYYC | LLYYG--------GAQLV | FGGGT KLTVL |
| iPS:4_37012 | 21-225_192G7 | VL7l7a/JL2 | QTVVTQE-PSLTVSPGGTVTLTC | ASST-GAVTSG-NYPQ | WFQQKPGQAPRALIY | S------TTNRHS | WTPARFSGSLLG-GKAALTLSGVQPEDEAEYYC | LFYYG--------GAQVI | FGGGT KLTVL |
| iPS:4_37014 | 21-225_192H8 | VL7l7a/JL2 | QTVVTQE-PSLTVSPGGTVTLTC | AFST-GIVTSG-PYPN | WFQQKPGQAPRALIY | N------TSNKHS | WTPARFSGSLLG-GMAALTLSGVQPEDEAEYYC | LLYYG--------GAQLM | FGGGT KLTVL |
| iPS:4_37022 | 21-225_194G5 | VL7l7a/JL2 | QTVVTQE-PSLTVSPGGTVTLTC | ASST-GAVTSG-NYPN | WFQQKPGQTPRALIY | S------TSNKHS | WTPARFSGSLLG-GKAALTLSGVQPEDEAEYYC | LIYYG--------GAQLM | FGGGT KLTVL |
| iPS:4_37026 | 21-225_194D12 | VL7l7a/JL2 | QTVVTQE-PSLTVSPGGTVTLTC | ASST-GAVTSG-SFPS | WFQQKPGQAPRTLIY | S------TSNRHS | STPARFSGSLLG-GKAALTLSGVQPEDEAEYYC | LIYYG--------GAQLA | FGGGT KLTVL |
| iPS:4_37040 | 21-225_196E7 | VL7l7a/JL2 | QTVVTQE-PSLTVSPGGTVTLTC | ASST-GAVTSA-YYPN | WLQQKPGQAPRTLIY | S------TNNKHS | WTPARFSGSLLG-GKAALTLSDVQPEDEAEYYC | LIFYG--------GVHVI | FGGGT KLTVL |
| iPS:4_37048 | 21-225_197B11 | VL7l7a/JL2 | QTVVTQE-PSLTVSPGGTVTLTC | AFST-GSVTSG-SYPN | WFQQKPGQAPRALIY | S------TNNKHS | WTPARFSGSLLG-GKAALTLSGVQPEDEAEYYC | LLYYG--------GAQLV | FGGGT KLTVL |
| iPS:4_37050 | 21-225_197C11 | VL7l7a/JL2 | QTVVTQE-PSLTVSPGGTVTLTC | ASST-GAVTSA-YYPN | WLQQKPGQAPRTLIY | S------TSNKHS | WTPARFSGSLLG-GKAALTLSDVQPEDEAEYYC | LIFYG--------GVHVI | FGGGT KLTVL |
| iPS:4_37056 | 21-225_198B8 | VL7l7a/JL2 | QTVVTQE-SSLTVSPGGTVTLTC | VLST-GAVTSG-SHPN | WFQQKPGQAPRALIY | S------TSNKHS | WTPARFSGSLLG-GKAALTLSGVQPEDEAEYYF | MLYSG--------GAQMV | FGGGT KLTVL |
| iPS:4_37062 | 21-225_200H1 | VL7l7a/JL2 | QTVVTQE-PSLTVSPGGTVTLTC | ASNT-GAVTSG-YYPN | WFQQKPGQAPRALIY | H------TNNKHS | WTPARFSGSLLG-GKAALTLSGVQPEDEAEYYC | LIYYG--------GAQLV | FGGGT KLTVL |
| iPS:4_37066 | 21-225_200G9 | VL7l7a/JL2 | QTVVTQE-PSLTVSPGGTVTLTC | ASNT-GAVTSG-SYPN | WLQQKPGQAPRALIY | H------TDNKHS | WTPARFSGSLLG-GKAALTLSGAQPEDEAEYYC | LIYYG--------GAHLA | FGGGT KLTVL |
| iPS:4_37068 | 21-225_200A11 | VL7l7a/JL2 | QTVVTQE-PSLTVSPGGTVTLTC | ASST-GAVTSG-YYPN | WFQQKPGQVPRALIY | S------TNNKHS | WTPARFSGSLLG-GKAALTLSGVQPEDEAEYYC | LLYYG--------GAHLA | FGGGT KLTVL |
| iPS:4_37090 | 21-225_210F11 | VL7l7a/JL2 | QTVVTQE-PSLTVSPGGTVTLTC | AFST-GAVTSG-NYPN | WFQQKPGQAPRALIY | S------TSNKHS | WTPARFSGSLLG-GKAALTLSGVQPEDEAEYYC | LLYYG--------GAQLV | FGGGT KLTVL |

Figure 51 (Continued)

| | | L_FR1 | L_CDR1 | L_FR2 | L_CDR2 | L_FR3 | L_CDR3 | L_FR4 |
|---|---|---|---|---|---|---|---|---|
| iPS:4 37106 | 21-225_211H7 | VL7\|7a/JL2 | QTVVTQE-PSLTVSPGGTVTLTC | AFST-GAVTSG-----NYPS | WFQQKPGQVPRALIY | S-------TSNRHS | WTPARFSGSLLG---GKAALTLSGVQPEDEAEYYC | LLYYG-----------GAQLV | FGGGTKLTVL |
| iPS:4 37108 | 21-225_211C9 | VL7\|7a/JL2 | QTVVTQE-PSLTVSPGGTVTLTC | GSST-GSVISG-----YFPN | WFQQKPGQAPRLIY | S-------TNNKHS | WTPARFSGSLLG---GKAALTLSDVQPEDEADYYC | LLYYG-----------GAQLA | FGGGTKLTVL |
| iPS:4 37110 | 21-225_211E9 | VL7\|7a/JL2 | QTVVTQE-PSLTVSPGGTVTLTC | ASST-GAVTSG-----NYPN | WFQQKPGQAPRALIY | S-------TINKHS | GTPARFTGFLLG---GKAALTLSDVQPEDEAEYYC | LLYYG-----------GAQLA | FGGGTKLTVL |
| iPS:4 37120 | 21-225_212A9 | VL7\|7a/JL2 | QTVVTQE-PSLTVSPGGTVTLTC | ASST-GAVTSG-----YYPN | WFQQKPGQAPRALIY | S-------TSNKHS | WTPARFSGSLLG---GKAALTLSGVQPEDEAEYYC | LLYYG-----------GAQVG | FGGGTKLTVL |
| iPS:4 37124 | 21-225_212H12 | VL7\|7a/JL2 | QTVVTQE-PSLTVSPGGTVTLTC | ASST-GAVTSG-----YYPN | WFQQKPGQAPRALIY | S-------TNNKHS | CTPARFSGSLLG---GKAALTLSGVQPEDEADYYC | LLYFG-----------GAHVV | FGGGTKLTVL |
| iPS:4 37132 | 21-225_213F5 | VL7\|7a/JL2 | QTVVTQE-PSLTVSPGGTVTLTC | GSST-GSVISG-----YFPN | WFQQKPGQAPRALIY | S-------TSNKHS | WTPARFSGSLLG---GKTALTLSDVQPEDEAEYYC | LLYYG-----------GAQLA | FGGGTKLTVL |
| iPS:4 37136 | 21-225_214H3 | VL7\|7a/JL2 | QIVVTQE-PSLTVSPGGTVTLTC | ASST-GAVTSG-----YYPN | WFQQKPGQAPRALIY | S-------TNNKHS | CTPARFSGSLLG---GKAALTLSGVQPEDEADYYC | LLYYG-----------GAHVV | FGGGTKLTVL |
| iPS:4 37140 | 21-225_214E12 | VL7\|7a/JL2 | QTVVTQE-PSLTVSPGGTVTLTC | ASST-GAVTSG-----YYPN | WFQQKPGQAPRALIY | S-------TSNKHS | WTPARFSGSLLG---GKAALTLSGVQPEDEAEYYC | LLYCD-----------GAQLV | FGGGTKLTVL |
| iPS:4 37142 | 21-225_215A3 | VL7\|7a/JL2 | QTVVTQE-PSLTVSPGGTVTLTC | ASST-EAVTSG-----NYPS | WFQQKPGQAPRALIY | S-------TSNKHS | GTPARFTGSLLG---GKAALTLSGVQPEDEAEYYC | LLYYG-----------GAQLA | FGGGTKLAVL |
| iPS:4 37148 | 21-225_215H3 | VL7\|7a/JL2 | QTVVTQE-PSLTVSPGGTVTLTC | ASST-GAVTSG-----YYPN | WFQQKPGQAPRALIY | S-------TNNKHS | CGPARFSGSLLG---GKAALTLSGVQPEDEADYYC | LLYYG-----------GAQVG | FGGGTKLTVL |
| iPS:4 37154 | 21-225_216A7 | VL7\|7a/JL2 | QTVVTQE-PSLTVSPGGTVTLTC | ASST-GAVTSG-----YYPN | WFQQFPGQAPRALIY | S-------TSNKHS | CTPARFSGSLLG---GKAALTLSGVQPEDEADYYC | LLYYG-----------GAQVG | FGGGTKLTVL |
| iPS:4 37158 | 21-225_216H11 | VL7\|7a/JL2 | QTVVTQE-PSLTVSPGGTVTLTC | ASST-GAVTSG-----YYPN | WFQQKPGQAPRALIY | S-------TSNKHS | WTPARFSGSLLG---GKAALTLSDVQPEDEAEYYC | LLYCD-----------GAQLV | FGGGTKLTVL |
| VL1\|1b/JL3b | | Germline | QSVLTQP-PSVSAAPGQKVTISC | SGGS-SNIGN-----NYVS | WYQQLPGT-APKLLIY | D-------NNKRPS | GIPDRFSGSKSG---TSATLGITLQTGLQTPEDEAEDYC | GTWDTS-----------LSAWV | FGGGTKLTVL |
| iPS:4 36972 | 21-225_190C7 | VL1\|1b/JL3b | QSVLTQP-PSVSAAPGQKVTISC | SGGS-SNIGN-----NYVS | WFQQFPGT-APKFLIY | D-------NNKRPS | GIPDRFSGSKSG---TSAILGITGLQTGDEADYYC | GTWDRT-----------LSDWV | FGGGTKLTVL |
| iPS:4 37020 | 21-225_193F11 | VL1\|1b/JL3b | QYVLTQP-PSVSAAPGQKVTISC | FGGS-SNIGN-----NYVS | WFQQFPGT-APKFLIY | D-------NNKRPS | GILDRLSGSKSG---TSATLDITGLQNGDEADYYC | GTWDRT-----------MSDWV | FGGGTKLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:4 37036 | 21-225_195H9 | VL1|1b/JL3b | QSVLTQP-PSVSAAPGQKVTISC | SGGS-SNIGN-----NYVS | WFQQFPGT APKLLIY | D-------NNKRPS | GILDRFSGSK3G-TSAILGITGLQTGDEADYYC | GTWDRT-------MSDWV | FGGGT KLTVL |
| | Germline | VL1|1b/JL1 | QSVLTQP-PSVSAAPGQKVTISC | SGSS-SNIGN-----NYVS | WYQQLPGT APKLLIY | D-------NKKRPS | GTPDRFSGSKSG-TSAILGITGLQTGDEADYYC | GTWDSS-------LSACV | FGTGT KLTVL |
| iPS:4 36996 | 21-225_191B9 | VL1|1b/JL1 | QSVLTQP-PSVSAAPGQKVTISC | SGSS-SNIGN-----NYVS | WYQQLPGT APKLLIY | D-------NKKRPS | GTPDRFSGSKSG-TSAILGITGLQTGDEADYYC | GTWDSS-------LSVCV | FGTGT KVTVL |
| iPS:4 37054 | 21-225_194G3 | VL1|1b/JL1 | QSVLTQP-PSVSAAPGQKVTISC | SGSS-SNIGN-----NYIS | WYQQLPGT APKLLIY | D-------NKKRPS | GIPDRFSGSKSG-TSAILGITGLQTGDEADYYC | GTWDSS-------LSVCV | FGTGT KVTVL |
| iPS:4 37058 | 21-225_199F3 | VL1|1b/JL1 | QSVLTQP-PSVSAAPGQKVTISC | SGSS-SNIGN-----NYVS | WYQQLPGT APKLLIY | D-------NNKRPS | GIPDRFSGSKSG-TSAILGITGLQTGDEADYYC | GTWDSS-------LSACV | FGTGT KVTVL |
| | Germline | VL5|5c/JL2 | QAVSTRP-SSLSASPGASASLTC | TLRS-GINVGT-----YRIY | WYQQKPGS FPQYLLR | YKS-------DSDKQQGS | GVPSRFSGSKDASANAGILL ISGLQSEDEADYYC | MIWHS-------SAVV | FGGGT KLTVL |
| iPS:4 37080 | 21-225_191G9 | VL5|5c/JL2 | QAVSTRP-SSLSASPGASASLTC | TLRS-GINVGT-----YRIY | WYQQKPGS FPQYLLR | YKS-------DSDKQQGS | GVPSRFSGSKDASANAGILL ISGLQSEDEADYYC | MIWHS-------SAVV | FGGGT KLTVL |
| | Germline | VL3|3/JL2 | SYELTQP-LSVSVALGQTARITC | | | | | | |
| iPS:4 37074 | 21-225_203B2 | VL3|3/JL2 | SYELTQP-LSVSVALGQTARITC | GGN----NIGR-----KNVH | WYQQKPGQ SPVLIIH | R-------DSDRPS | GIPERFSGSNSG-NTAILTISRAQAGDEADYYC | QVWDS-------GTAV | FGGGT KLPVL |
| iPS:4 37082 | 21-225_205E12 | VL3|3/JL2 | SYELTQP-LSVSAALGQTARITC | GGN----NIGR-----KNVH | WYQQKPGQ SPVLIIH | R-------DSDRPS | GIPERFSGSNSG-NTAILTISRAQGDEADYYC | QVWDS-------GTAV | FGGGT KLPVL |
| iPS:4 37084 | 21-225_206B5 | VL3|3/JL2 | SYELTQP-LSVSVALGQTARITC | GGN----NIGR-----KNVH | WYQQKPGL AFVPVIX | R-------DSYRSS | GIPDRFSGSNCG-NTTVTISRAQAGEEAEYYC | QDWDS-------STVV | FGGGT KLTVL |
| iPS:4 37088 | 21-225_209H10 | VL3|3/JL2 | SYELTQP-LSVSVALGQTARITC | GGN----NIGR-----KNVH | WYQQKPGL AFVPVIX | R-------DSYRSS | GIPERFSGSNWG-NTAIVTISRAQAGEFAEYYC | QDWDS-------STVV | FGGGT KLTVL |
| iPS:4 37100 | 21-225_211H2 | VL3|3/JL2 | SYELTQP-LSVSVALGQTARITC | GGN----NIGR-----RNVH | WYQQKPGL AFILVIY | R-------DRDRPS | GIPERFSGSNSG-NTAILTISRAQGDEADYFC | QVWDS-------STAV | FGGGT KLPVL |
| iPS:4 37160 | 21-225_216B12 | VL3|3/JL2 | SYELTQP-LSVSVALGQTARITC | GGD----NIRR-----RNVH | WYQQKPGQ APVLVIY | R-------DSNRPS | GIPERFSGSNSG-NTAILTISRAQAGDEADYYC | QVWDS-------STGV | FGGGT KLTVL |
| iPS:3 92593 | 21-225_3E10 | VL3|3/JL2 | SYELTQP-HSVSVATAQMARITC | GGN----NIGS-----KAVH | WYQQKPGQ DPVLVIY | S-------DSNRPS | GIPERFSGSNPG-NTAILTISRIEAGDEADYYC | QVWDSS-------SDHVV | FGGGT KLTVL |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:3 93204 | 21-225_8C12 | VL3j3jJL2 | SYELTQP-HSVSVATAQMARITC | GGN----NIGS-----KAVH | WYQQKPGQ DPVLVIY | S-------DSNRPS | GIPERFSGSNPG-NTATLTISRIEAGDEADYYC | QVWDSS-------SDHVV | FGGGT KLTVL |
| | Germline | | QSALTQP-ASVSGSPGQSITISC | TGTS-SDVGGY----NYVS | WYQQHPGK APKLMIY | E-------VSNRPS | GVSNRFSGSKSG-NTASLTISGLQAEDEADYYC | SSYTS-------SRTLV | FGGGT KLTVL |
| iPS:4 37092 | 21-225_210B12 | VL2j2a2/JL2 | QSALTQP-ASVSGSPGQSITISC | TGTS-SDVGGY----NYVS | WYQQHPGK APKFMIY | E-------VRNRPS | GVSNRFSGSKSG-NTASLIISGLQAEDEADYYC | SSYTS-------SRTLV | FGGGT KLTVL |
| iPS:4 37134 | 21-225_213A7 | VL2j2a2/JL2 | QSALTQP-ASVSGSPGQSITISC | TGTS-SDVGGY----NYVS | WYQQHPGK APKFMIY | E-------VRNRPS | GVSNRFSGSKSG-NTASLIISGLQAEDEADYYC | SSYTS-------SRTLV | FGGGT KLTVL |
| iPS:4 72733 | 21-225_2B10_LC2 | VL2j2a2/JL2 | QSALTQP-ASVSGSPGQSITISC | TGTS-SDVGGY----NFVS | WYQQHPDK APKLMIY | E-------VSNRPS | GVSNRFSGSKSG-NTASLIISGLQAEDEADYYC | SSYTS-------TGIVV | IGGGT KLTVL |
| iPS:3 92573 | 21-225_15G2 | VL2j2a2/JL2 | QSALTQP-ASVSGSPGQSITISC | TGTS-SDVGGY----NYVS | WYQQHPGK APKLMIY | E-------VSNRPS | GVSNRFSGSKSG-NTASLIISGLQAEDEADYYC | TSYTS-------TSIVV | FGGGT KLTVL |
| iPS:3 93232 | 21-225_17F12 | VL2j2a2/JL2 | QSALTQP-ASVSGSPGQSITISC | TGAS-SDVGDY----NSVS | WYQQHPGK APKLMIY | E-------VSNRPS | GVSNRFSGSKSG-NTASLIISGLQAEDEADYYC | SSYTS-------SITVV | FGGGT KLTVL |
| iPS:3 98494 | 21-225_21H4 | VL2j2a2/JL2 | QSALTQP-ASVSGSPGQSITISC | TGTS-SDVGGY----NSVS | WYQQHPDK APKLMIY | E-------VSNRPS | GVSNRFSGSKSG-NTASLIISGLQAEDEADYYC | SSYTR-------SSTVV | FGGGT KLTVL |
| | Germline | | | | | | | | |
| iPS:4 37102 | 21-225_211E5 | VL3j3m/JL1 | SYELTQP-PSVSVSPGQTARITC | SGD---ALPK-----QYAY | WYQQKPGQ APVLVIY | K-------DSARPS | GIPERFSGSRSG-TTVTLTVSGVQAEDEAPYYC | QLVYS-------SDTYV | FGTGT MLIVL |
| iPS:4 37164 | 21-225_217C6 | VL3j3m/JL1 | SYELTQP-PSVSVSPGQTARITC | SGD---ALPK-----QYAY | WYQQKPGQ APVLVIY | K-------DSERPS | GIPERFSGSRSG-TTVTLIRGVQAEDEADYYC | QLIVS-------SDTYV | FGTGT KVIVL |
| iPS:4 37166 | 21-225_217G11 | VL3j3m/JL1 | SYELTQP-PSVSVSPGQTARITC | SGD---ALPK-----QYAY | WYQQKPGQ APVLVIY | K-------DSERPS | GIPERFSGSRSG-TTVTLIVSGVQAEDEADYYC | QLVYS-------SDTYV | FGTGT KVIVL |
| iPS:4 37170 | 21-225_218E5 | VL3j3m/JL1 | SYELTQP-PSVSVSPGQTARITC | SRD---VLPK-----QYAY | WYQQKPGQ APVLVIY | K-------DSERPS | GIPERFSGSRSG-TTVTLIRGVQAEDEADYYC | QLVVS-------SDTYV | FGTGT KVIVL |
| iPS:4 37196 | 21-225_226B7 | VL3j3m/JL1 | SFELTQP-ASVSVSPGQTARITC | SGD---ALPR-----HYVY | WYQQNPGQ APVLVIY | K-------DSERPS | GIPERFSGSSSG-TTVTLIISGVQAEDEADYYC | QSADS-------SGTYV | FGTGT KVIVL |
| | Germline | | | | | | | | |

Figure 51 (Continued)

| | | | L_FR1 | L_CDR1 | L_FR2 | L_CDR2 | L_FR3 | L_CDR3 | L_FR4 |
|---|---|---|---|---|---|---|---|---|---|
| iPS:3 92596 | 21-225_12D8 | VL4|4c|JL2 | LPVLTQP-PSASALLGASIKLTC | TLSS-EHSTY------TIE | WYQQRPGRSPQYIMK | VKS------DGSHSKGD | GIPDRFMGSSSG--ADRYLTFSNLQSDDEDEYHC | GESHTID------GQVGVV | FGGGTKLTVL |
| iPS:3 93174 | 21-225_15D8 | VL4|4c|JL2 | LPVLTQP-PSASALLGASIKLTC | TLSS-EHSTY------TIE | WYQQRPGRSPQYIMK | VKS------DGSHSKGD | GIPDRFMGSSSG--ADRYITFSNLQSDEEEYHC | GESHTID------GQVGVV | FGGGTKLTVL |
| iPS:3 98544 | 21-225_7C8 | VL4|4c|JL2 | LPVLTQP-PSASALLGASIKLTC | TLSS-EHSTY------TIE | WYQQRPGRSPQYIMK | VKS------DGSHSKGD | GIPDRFMGSSSG--GDRYLTFSNLQSDEDEYHC | GESHPID------GQVGVV | FGGGTKLTVL |
| | VL3|3h|JL2 | Germline | SYVLTQP-PSVSAPPTARITC | SGN------NIGS-KSVH | WYQQKPGQAPVLVVY | SDDPPS | GIPERFSSGSNSG--NTATLTISRVEAGDADYYC | QVWDSS------SDHVV | FGGGTKLTVL |
| iPS:3 93208 | 21-225_16F3 | VL3|3h|JL2 | SYVLTQP-PSVSVAPGQTARITC | GGN------NIGS-KSVH | WYQQKPGQAPVLVVY | D------DTDRPS | GIPERFSSGSNSG--NTATLTISRVEAGDEADYYC | QVWDSS------SDHVV | FGGGTKLTVL |

HEAVY VARIABLE

| | | | H_FR1 | H_CDR1 | H_FR2 | H_CDR2 | H_FR3 | H_CDR3 | H_FR4 |
|---|---|---|---|---|---|---|---|---|---|
| | VH1|1-08/D6|6-19|RF1/JH4 | Germline | QVQLVQS-GAEVKKPGASVKVSCKASG-YTFT | S------YDIN | WVRQATGQGLEWMG | WMNPN--SGNTGYAQKFQG | RVTMTRNTSISTAYMELSSLRSEDTAVYYCAR | GYSSGW------YFDY | WGQGTLVTVSS |
| iPS:4 26126 | 21-225_6G6 | VH1|1-08/D6|6-19|RF1/JH4 | QVQLVQS-GAEVRKPGASVKVSCKASG-YTFT | N------YDIN | WVRQATGQGPEWMG | WMHPN--SGNTGYAKKFQG | RVTMTRNTSISAAYMVLSSLRSEDTAVYYCAL | SSGWY------YFDY | WGQGTLVTVSS |
| iPS:4 12232 | 21-225_4A2 | VH1|1-08/D6|6-19|RF1/JH4 | QVQLVQS-GTEVKKPGASVKVSCKASG-YTFT | N------YDIN | WVRQATGQGLEWMG | WMHPN--SGNTGYAQKFQG | RVTLTRNTSISTAYMELSSLRSEDTAVYYCAS | SSGWY------YFDY | WGQGTLVTVSS |
| iPS:4 26112 | 21-225_12F12 | VH1|1-08/D6|6-19|RF1/JH4 | QVQLLQS-GAEVKKPGASVKVSCKASG-YTFT | N------YDIN | WVRQATGQGLEWMG | WMYPN--SGNTGYAQKFQG | RVTMTRNTSISTAYMELSSLRSEDTAVYYCAM | SSGWY------YFDF | WGQGTLVTVSS |
| iPS:4 51141 | 21-225_164B11 | VH1|1-08/D6|6-19|RF1/JH4 | QVQLVQS-GAEVKKPGASVKVSCKASG-YTFT | N------YDIN | WVRQATGQGLEWMG | WMTPN--SGNTGYAQKFQG | RVTMTRNTSMSTAYMELSSLRSEDSAVYYCSY | SSGWY------MFDY | WGQGTLVTVSS |
| iPS:4 68850 | 21-225_63F4 | VH1|1-08/D6|6-19|RF1/JH4 | QVQLVQS-GAEVKKPGASVKVSCKASG-YTFT | N------YDVN | WVRQATGQGLEWMG | WMHPN--SGNTGYAQKERG | RVTMTRNTSLSTVYMELSSLRSEDTAVYYCAY | SSGWY------VFDY | WGQGTLVTVSS |
| iPS:4 68852 | 21-225_71F3 | VH1|1-08/D6|6-19|RF1/JH4 | QVQLVQS-GAEVKKPGASVKVSCKASG-YTFT | N------YDVN | WVRQATGQGLEWMG | WMHPN--SGNTGYAQKFQG | RVTMRRNTSISTAYMELSSLRSEDTAVYYCAY | SSGWY------VFDS | WGQGTLVTVSS |

Figure 51 (Continued)

| | | | | | | | | | |
|---|---|---|---|---|---|---|---|---|---|
| iPS:4 68854 | 21-225_72C4 | VH1|1-08|D6|6-19|RF1/JH4 | QVQLVQS-GAEVKKPGASVKVSCKASG-YTFT | N------YDIN | WVRQVTGQGLEWMG | WMHPN---SGNTGYAQKFQG | RVTMTRNTSISTAYMELNSLRSEDTAVYYCSH | SSGWY----------- | ------LFDYWGQGTLVTVSS |
| iPS:4 68870 | 21-225_74A8 | VH1|1-08|D6|6-19|RF1/JH4 | QVQLVQS-GAEVKKPGASVKVSCKASG-YTFT | N------YDIN | WVRQASGQGLEWMG | WMHPN---SGNTGYAQKFQG | RVTMTRNTSISTAYMELSSLRSEDSAVYYCAY | SSGWY----------- | ------KFDYWSQGTLVTVSS |
| iPS:4 23314 | 21-225_12F11 | VH1|1-08|D6|6-19|RF1/JH4 | QVQLVQS-GAEVKKPGASVKVSCKASG-YTFT | N------YDIN | WVRQATGQGPEWMG | WMHPN---SGNTGYAKKFQG | RVTMTRNTSSAAYMVLSSLRSEDTAVYYCAL | SSGWY----------- | ------YFDYWGQGTLVTVSS |
| iPS:4 33909 | 21-225_43D8 | VH1|1-08|D6|6-19|RF1/JH4 | QVQLVQS-GAEVKKPGASVKVSCKASG-YTFT | N------YDIN | WVRQATGQGLEWMG | WMHPN---SGNTGYAQKFQG | RVTMTRNTSISTAYMELSSLTSEDTAVYYCAH | SSGWT----------- | ------LFDYWGQGTLVTVSA |
| iPS:4 34177 | 21-225_56A1 | VH1|1-08|D6|6-19|RF1/JH4 | QVQLVQS-GAEVKKPGASVKVSCKASG-YTFT | N------YDIN | WVRQATGQGLEWLG | WMHPN---SGNTGYAQKFQG | RVTMTRNTSISTAYMELSSLRSEDTAVYYCAY | SSGWY----------- | ------VFDYWGQGTLVTVSS |
| iPS:4 34211 | 21-225_60F3 | VH1|1-08|D6|6-19|RF1/JH4 | QVLLVQS-GAEVKKPGASVKVSCKASG-YTFT | N------YDIN | WVRQATGQGLEWMG | WMHPN---SGNTGYAQKFQG | RVTMTRNTSISTAYMELSSLRSEDTAVYYCAY | SSGWY----------- | ------FFDYWGQGTLVTVSS |
| iPS:4 34235 | 21-225_61E3 | VH1|1-08|D6|6-19|RF1/JH4 | QVQLVQS-GAEVKKPGASVKVSCKASG-YTFT | N------YDIN | WVRQATGQGLEWMG | WMHPN---SGNTGYAQKFQG | RVTMTRNTSISTAYMELSSLRSEDTAVYYCAY | SSGWY----------- | ------RFDYWGQGTLVTVSS |
| iPS:4 34237 | 21-225_61B5 | VH1|1-08|D6|6-19|RF1/JH4 | QVQLVQS-GAEVKKPGASVKVSCKASG-YTFT | N------YDIN | WVRQATGQGLEWMG | WMTPN---SGSTGYAQKFQG | RVTMTRNTSISTAYMELSSLRSEDTAVYYCAY | SSGWY----------- | ------YFDYWGQGTLVTVSS |
| iPS:4 34295 | 21-225_58B9 | VH1|1-08|D6|6-19|RF1/JH4 | QVQLVQS-GAEVKKPGASVKVSCKASG-YTFT | N------YDIN | WVRQATGQGLEWMG | WMHPN---SGSTGYAQKFQG | RVTMTRNTSISTAYMELSSLRSEDTAVYYCAY | SSGWY----------- | ------YFDYWGQGTLVTVSS |
| iPS:4 34305 | 21-225_59E1 | VH1|1-08|D6|6-19|RF1/JH4 | QVQLVQS-GAEVKKPGASVKVSCKASG-YTFT | N------YDIN | WVRQATGQGLEWMG | WMTPN---SGNTGYAQKFQG | RVTMTRNTSISTAYMELSSLRSEDTAVYYCAF | SSGWY----------- | ------FFDYWGQGTLVTVSS |
| iPS:4 34321 | 21-225_59F10 | VH1|1-08|D6|6-19|RF1/JH4 | QVQLVQS-GAEVKKPGASVKVSCKASG-YTFT | N------YDIN | WVRQATGQGLEWMG | WMNPN---SGNTGYAQKFQG | RVTMTRNTSISTAYMELSSLRSEDTAVYNCAV | SSGWY----------- | ------YFDYWGQGTLVTVSS |
| iPS:4 34431 | 21-225_70E7 | VH1|1-08|D6|6-19|RF1/JH4 | QVQLVQS-GAEVKKPGASVKVSCKASG-YTFT | N------YDIN | WVRQATGQGLEWMG | WMHPN---SGNTGYAQKFQG | RVTMTRNTSISTAYMELSSLRSEDTAVYYCAI | SSGWY----------- | ------VFDYWGQGTLVTVSS |

Figure 51 (Continued)

| | | | | | | | | |
|---|---|---|---|---|---|---|---|---|
| iPS:4 34443 | 21-225_71G3 | VH1j1-08jD6j6-19jRF1/JH4 | QVQLVQS-GAEVKKPGASVKVSCKASG-YTFT | N------YDIN | WVRQATGQGLEWMG | WMHPN---SGSTGYAQKFQG | RVTMTRDISVSTAYMELSSLRSEDTAVYYCAI | SSGWY--------YFDY | WGQGTLVTVSS |
| iPS:4 34475 | 21-225_74F9 | VH1j1-08jD6j6-19jRF1/JH4 | QVQLVQS-GAEVKKPGASVKVSCKASG-YTFT | N------YDIN | WVRQATGQGLEWMG | WMNPN---SGNTGCAQKFQG | RVTMTRNISISTAYMELSSLRSEDTAVYYCAS | SSGWN--------FFDY | WGQGTLVTVSS |
| iPS:4 34477 | 21-225_74A6 | VH1j1-08jD6j6-19jRF1/JH4 | QVQLVQS-GAEVKKPGASVKVSCKASG-YTFT | N------YDIN | WVRQATGQGLEWMG | WMHPN---SGNTGYAQKFQG | RVTMTWNISISTAYMELSSLRSEDTAVYYCAS | SSGWY--------YFDY | WGQGTLVTVSS |
| iPS:4 34487 | 21-225_76G2 | VH1j1-08jD6j6-19jRF1/JH4 | QVQLVQS-GAEVKKPGASVKVSCKASG-YTFT | N------YDIN | WVRQATGQGLEWMG | WMHPN---SGNTGYAQKFRG | RVTMTRNISISTAYMELSSLRSEDTAVYYCAG | SSGWY--------MFDY | WGQGTLVTVSS |
| iPS:4 34511 | 21-225_74B11 | VH1j1-08jD6j6-19jRF1/JH4 | QVQLVQS-GAEVKKPGASVKVSCKASG-YTFT | N------YDIN | WVRQATGQGLEWMG | WMHPN---SGNTGYAQKFQG | RVTMTRNISISTAYMELSSLRSEDTAVYYCAY | SSGWY--------YFDY | WGQGTLVTVSS |
| iPS:4 34549 | 21-225_76E11 | VH1j1-08jD6j6-19jRF1/JH4 | QVQLVQS-GAEVKKPGASVKVSCKASG-YTFT | N------YDIN | WVRQATGQGLEWMG | WMHPN---SGNTGCAQKFQG | RLTMTRNISISTAYMELSSLRSEDTAVFYCAY | SSGWY--------YFDY | WGQGTLVTVSS |
| iPS:4 34551 | 21-225_75C4 | VH1j1-08jD6j6-19jRF1/JH4 | QVQLVQS-GAEVKKPGASVKVSCKASG-YTFT | N------YDIN | WVRQATGQGLEWMG | WMHPN---SGNTGYAQKFQG | RVTMTRNISISTAYMELSSLRSEDTAVYYCAY | SSGWY--------YFDY | WGQGTLVTVSS |
| iPS:4 34635 | 21-225_78E6 | VH1j1-08jD6j6-19jRF1/JH4 | QVQLVQS-GAEVKKPGASVKVSCKASG-YTFT | N------YDIN | WVRQASGQGLEWMG | WMHPN---SGNTGYAQKFQG | RVTMTRNISISTAYMELSSLRSEDSAVYYCAY | SSGWY--------KFDY | WGQGTLVTVSS |
| iPS:4 34649 | 21-225_78E11 | VH1j1-08jD6j6-19jRF1/JH4 | QVQLVQS-GAEVKKPGASVKVSCKASG-YTFT | N------YDIN | WVRQATGQGLEWMG | WMHPN---SGNTGCAQKFQG | RVTMTRNISISTAYMELSSLRSEDSAVYYCAS | SSGWN--------FFDY | WGQGTLVTVSS |
| iPS:4 34665 | 21-225_74G4 | VH1j1-08jD6j6-19jRF1/JH4 | QVQLVQS-GAEVKKPGASVKVSCKASG-YTFT | N------YDVN | WVRQATGQGLEWMG | WMHPN---SGNTGYAQKFQG | RVTMTRNISIRTAYMELSSLRSEDTAVYYCAY | SSGWY--------HFDY | WGQGTLVTVSS |
| iPS:4 34679 | 21-225_79G7 | VH1j1-08jD6j6-19jRF1/JH4 | QVQLVQS-GAEVKKPGASVKVSCKASG-YTFT | N------YDIN | WVRQASGQGLEWMG | WMHPN---SGNTGYAQKFQG | RVTMTRNISISTAYMELSSLRSEDSAVYYCAY | SSGWY--------KFDY | WGQGTLVTVSS |
| iPS:4 34885 | 21-225_79E9 | VH1j1-08jD6j6-19jRF1/JH4 | QVQLVQS-GAEVKKPGASVKVSCKASG-YTFT | N------YDIN | WVRQATGQGLEWMG | WMHPN---SGNTGYAQKFQG | RVTMTRNISISTAYMELSSLRSEDTAVYYCAS | SSGWY--------YFDY | WGQGTLVTVSS |

Figure 51 (Continued)

| | | | | | | | | | |
|---|---|---|---|---|---|---|---|---|---|
| iPS:4 34697 | 21-225_79F12 | VH1|1-08/D6|6-19|RF1/J H4 | QVQLVQS-GAEVKKPGASVKV SCKASG-YTFT | N------YDIN | WVRQATGQ GLEWMG | WMNPN---SGNTGYAQK FQG | RVTMTRNTSISTAYMELSSL RSEDTAVYYCAS | SSGWY--------FFDY | WGQGT LVTLS S |
| iPS:4 34729 | 21-225_80B12 | VH1|1-08/D6|6-19|RF1/J H4 | QVQLVQS-GAEVKKPGASVKV SCKISG-YTFT | N------YDIN | WVRQATGQ GLEWMG | WMNPN---SGNTGYAQK FQV | RVTMTRNTSISTAYMELSSL RSEDTAVYYCAY | SSGWY--------IFDY | WGQGT LVTVS S |
| iPS:4 34851 | 21-225_75A6 | VH1|1-08/D6|6-19|RF1/J H4 | QVQLVQS-GAEVKKPGASVKV SCKASG-YTFT | N------YDIN | WVRQATGQ GLEWMG | WMNPN---SGNTGYAQK FQG | RVTMTRNTSISTAYMELSSL RSEDTAVYYCAY | SSGWY--------IFDY | WGQGT LVTVS S |
| iPS:4 34909 | 21-225_85C11 | VH1|1-08/D6|6-19|RF1/J H4 | QVQLVQS-GAEVKKPGASVKV SCKASG-YTFT | N------YDIN | WVRQASGQ GLEWMG | WMHPN---SGNTGYAQK FQG | RVTMTRNTSISTAYMELSSL RSEDTAVYYCAY | SSGWY--------KFDY | WSQGT LVTVS S |
| iPS:4 34959 | 21-225_87E10 | VH1|1-08/D6|6-19|RF1/J H4 | QVQLVQS-GAEVKKPGASVKV SCKASG-YTFT | N------YDIN | WVRQATGQ GLEWMG | WMNPN---SGNTGYAQK FQG | RVTMTRNTSISTAYMELSSL RSEDTAVYYCAY | SSGWY--------FFDY | WGQGT LVTVS S |
| iPS:4 34965 | 21-225_88A1 | VH1|1-08/D6|6-19|RF1/J H4 | QVQLVQS-GAEVKKPGASVKV SCKASG-YTFT | N------YDIN | WVRQATGQ GLEWMG | WMNPN---SGNTGYAQK FQG | RVTMTRNTSISTAYMELSSL RSEDTAVYYCAY | SSGWY--------YFDY | WGQGT LVTVS S |
| iPS:4 34973 | 21-225_88B4 | VH1|1-08/D6|6-19|RF1/J H4 | QVQLVQS-GAEVKKPGASVRV SCKASG-YTFT | N------YDIN | WVRQATGQ GLEWMG | WMNPN---SGDTGYAQK FQG | SVTMTRNTSITTAYMELSSL RSEDTAVYYCSI | SSGWY--------YFDY | WGQGT LVTVS S |
| iPS:4 34997 | 21-225_88C10 | VH1|1-08/D6|6-19|RF1/J H4 | QVQLVQS-GAEVKKPGASVKV SCKASG-YTFS | N------YDIN | WVRQATGQ GLEWMG | WMIPN---SGNTGYAQK FQG | RVTMTRNTSISTAYMELSSL RSEDTAVYYCAS | SSGWY--------YFDS | WGQGT LVTVS L |
| iPS:4 35053 | 21-225_75F9 | VH1|1-08/D6|6-19|RF1/J H4 | QVQLVQS-GAEVKKPGASVKV SCKASG-YTFS | N------YDIN | WVRQATGQ GLEWMG | WMHPN---SGNTGYAQK FQG | RVTMTRNTSISTAYMELSSL RSEDTAVYYCAY | SSGWY--------IFDY | WGQGT LVTVS S |
| iPS:4 35113 | 21-225_92E6 | VH1|1-08/D6|6-19|RF1/J H4 | QVQLVQS-GAEVKKPGASVRV SCKASG-YTFT | N------YDIN | WVRQATGQ GLEWMG | WMHPN---SGNTGYAQK FQG | RVTMTRNTSMSTAYMELSSL RSEDTAVYYCAH | SSGWY--------FFDY | WGQGT LVTVS S |
| iPS:4 35209 | 21-225_75A10 | VH1|1-08/D6|6-19|RF1/J H4 | QVQLVQS-GAEVKKPGASVKV SCKASG-YTFT | N------YDIN | WVRQATGQ GLEWMG | WMNPN---SGNTGYAQK FQG | RVTMTRNTSISTAYMELSSL RSEDTAVYYCAY | SSGWY--------YFDY | WGQGT LVTVS S |
| iPS:4 35257 | 21-225_96H5 | VH1|1-08/D6|6-19|RF1/J H4 | QVQLVQS-GAEVKKPGASVKV SCKASG-YTFT | N------YDIN | WVRQASGQ GLEWMG | WMHPN---SGNTGYAQK FQG | RVTMTRNTSISTAYMELSSL RSEDSAVYYCAI | SSGWY--------KFDY | WSQGT LVTVS S |

Figure 51 (Continued)

| | | | | | | | | |
|---|---|---|---|---|---|---|---|---|
| iPS:4 35267 | 21-225_96D10 | VH1]1-08/D6]6-19]RF1/JH4 | QVQLVQS-GAEVKKPGASVRVSCKASG-YTFT | N-----YDIN | WVRQATGQGLEWMG | WMHPN---SGNTGYAQKFQG | RVTMTRNISMSTAYMELSSLRSEDTAVYYCAH | SSGWY---------FFDY | WGQGTLVTVSS |
| iPS:4 35299 | 21-225_146D4 | VH1]1-08/D6]6-19]RF1/JH4 | QVQLVQS-GAEVKKPGASVKVSCKASG-YTFT | N-----YDIN | WVRQATGQGLEWMG | WVHPN---SGNTGYAQKFQG | RVTMTRNTSISTAYMELSSLRSEDTAVYYCAG | SSGWY---------YFDY | WGQGTLVTVSS |
| iPS:4 35305 | 21-225_146C9 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTWNTSISTAYMALSSLRSEDTAVYYCAY | SSGWY---------SFDY | WGQGTLVTVSS |
| iPS:4 35309 | 21-225_146F9 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAS | SSGWY---------FFDY | WGQGTLVTVSS |
| iPS:4 35321 | 21-225_147E4 | VH1]1-08/D6]6-19]RF1/JH4 | QVQLVQS-GAEVKKPGASVKVSCKASG-YTFT | N-----YDIN | WVRQATGQGLEWMG | WMNPN---SGNTGYAQKFQG | RVTMTRNISISTAYMELSSLRSEDTAVYYCAS | SSGWY---------FFDY | WGQGTLVTVSS |
| iPS:4 35323 | 21-225_147D5 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLNSGDTAVYYCAG | SSGWY---------YFDY | WGQGTLVTVSS |
| iPS:4 35345 | 21-225_148G3 | VH1]1-08/D6]6-19]RF1/JH4 | QVQLVQS-GAEVKKPGASVKVSCKASG-YTFT | N-----YDIN | WVRQASGQGLEWMG | WMHPN---SGNTGYAQKFQG | RVTMTRNISISTAYMELSSLRSEDTAVYYCAS | SSGWY---------FFDY | WGQGTLVTVSS |
| iPS:4 35353 | 21-225_148F8 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAS | SSGWY---------YFDY | WGQGTLVTVSS |
| iPS:4 35369 | 21-225_149A2 | VH1]1-08/D6]6-19]RF1/JH4 | QVQLVQS-GAEVKKPGASVKVSCKASG-YTFT | N-----YDIN | WVRQATGQGLEWMG | WVHPN---SGNTGYAQKFQG | RVTMTRNISISTAYMELSSLRSEDTAVYYCAG | SSGWY---------YFDY | WGQGTLVTVSS |
| iPS:4 35373 | 21-225_149E3 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAS | SSGWY---------WFDY | WGQGTLVTVSS |
| iPS:4 35375 | 21-225_149H4 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNISITIVYMELSSLTSEDTAVYYCTF | SSGWY---------YFDY | WGQGTLVTVSS |
| iPS:4 35399 | 21-225_150D2 | VH1]1-08/D6]6-19]RF1/JH4 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAI | SSGWY---------YFDY | WGQGTLVTVSS |

Figure 51 (Continued)

| | | | | | | | | | |
|---|---|---|---|---|---|---|---|---|---|
| iPS:4 35405 | 21-225_150B7 | VH1|1-08|D6|6-19|RF1/J H4 | QVQLVQS-GAEVKKPGASVTV SCKASG-FPFT | N-----YDIN | WVRQATGQ GLEWMG | WMHPN--- SGNTGYAQK FQG | RVTMTRNISISTAYLELSSL RSEDTAVYYCAS | SSGWY--------FFDY | WGQGT LVTVS S |
| iPS:4 35433 | 21-225_152E3 | VH1|1-08|D6|6-19|RF1/J H4 | QVQLVQS-GAEVKKPGASVKV SCKASG-YTFT | N-----YDIN | WVRQATGQ GLEWMG | WMHPN--- SGNTGYAQK FQG | RVTMTRNTSISTAYMELSSL RSEDTAVYYCAS | SSGWY--------FFDY | WGQGT LVTVS S |
| iPS:4 35435 | 21-225_152H3 | VH1|1-08|D6|6-19|RF1/J H4 | QVQLVQS-GAEVKKPGASVKV SCKASG-YTFP | N-----YDIN | WVRQATGQ GLEWMG | WMHPN--- SGNTGYAQK FQG | RVTMTRNISISTAYMELSSL RSEDTAVYYCAY | SSGWY--------WFDY | WGQGT LVTVS S |
| iPS:4 35459 | 21-225_152E12 | VH1|1-08|D6|6-19|RF1/J H4 | QVQLVQS-GAEVKKPGASVKV SCKASG-YTFT | N-----YDIN | WVRQATGQ GLEWMG | WMHPN--- SGNTGYAQK FQG | RVTMTRNISISTAYMELSSL RSEDTAVYYCAY | SSGWY--------YFDY | WGQGT LVTVS S |
| iPS:4 35471 | 21-225_153F11 | VH1|1-08|D6|6-19|RF1/J H4 | QVQLVQS-GAEVKKPGASVKV SCKASG-YTFT | N-----YDIN | WVRQATGQ GLEWMG | WMHPN--- SGNTGYAQK FQG | RVTMTRNTSINTAYMELSSL RSEDTAVYYCAY | SSGWY--------FFDN | WGQGT LVTVS S |
| iPS:4 35475 | 21-225_154H6 | VH1|1-08|D6|6-19|RF1/J H4 | QVQLVQS-GAEVKKPGASVKV SCKASG-YTFT | N-----YDIN | WVRQATGQ GLEWMG | WMHPN--- SGNTGYAQK FQG | RVTMTRNISISTAYMELSSL RSEDTAVYYCAY | SSGWY--------YFDY | WGQGT LVTVS S |
| iPS:4 35481 | 21-225_154A11 | VH1|1-08|D6|6-19|RF1/J H4 | QVQLVQS-GAEVKKPGASVKV SCKASG-YTFT | N-----YDIN | WVRQATGQ GLEWMG | WMHPN--- SGSTGYAQR FQG | RVTMTRNISISTAYMELSSL RSEDTAVYYCAF | SSGWY--------YFDY | WGQGT LVTVS S |
| iPS:4 35491 | 21-225_155E5 | VH1|1-08|D6|6-19|RF1/J H4 | QVQLVQS-GAEVKKPGASVKV SCKASG-YTFT | N-----YDIN | WVRQATGQ GLEWMG | WMNPN--- SGNTGYAQK FQG | RVTMTRNISISTAYMELSSL RSEDTAVYYCAY | SSGWY--------YFDY | WGQGT LVTVS S |
| iPS:4 35495 | 21-225_155B6 | VH1|1-08|D6|6-19|RF1/J H4 | QVQLVQS-GAEVKKPGASVKV SCKASG-YTFT | N-----YDIN | WVRQATGQ GLEWMG | WVHPN--- SGNTGYAQK FQG | RVTMTRNISISTAYMELSSL RSEDTAVYYCAY | SSGWY--------YFDY | WGQGT LVTVS S |
| iPS:4 35501 | 21-225_156H1 | VH1|1-08|D6|6-19|RF1/J H4 | QVQLVQS-GAEVKKPGASVKV SCKASG-YTFT | N-----YDIN | WVRQATGQ GLEWMG | WMHPN--- SGNTGYAQK FQG | RVTMTRNISISTAYMELSSL RSEDTAVYYCAG | SSGWY--------YFDY | WGQGT LVTVS S |
| iPS:4 35557 | 21-225_158B12 | VH1|1-08|D6|6-19|RF1/J H4 | QVQLVQS-GAEVKKPGASVKV SCKASG-YTFT | N-----YDIN | WVRQATGQ GFEWMG | WMHPN--- SGNTGFPQK FQG | RPTMTRNISISTAYMELSSL RSEDTAVYYCAY | SSGWY--------RFDY | WGQGT LVTVS S |
| iPS:4 35589 | 21-225_160A4 | VH1|1-08|D6|6-19|RF1/J H4 | QVQLVQS-GTEVKKPGASVKV SCKASG-YTFT | N-----YDIN | WVRQATGQ GLEWMG | WMHPN--- SGNTGYAQK FQG | RVTMTRNISISTAYMELSSL RSEDTAVYYCAI | SSGWY--------IFDY | WGQGT LVTVS S |

Figure 51 (Continued)

| | | | | | | | | |
|---|---|---|---|---|---|---|---|---|
| iPS:4 35623 | 21-225_162D5 | VH1\|1-08/D6\|6-19\|RF1/J H4 | QVQLVQS-GSEVKKPGASVKV SCKASG-YTFT | N------YDIN | WVRQATGQ GLEWMG | WMHPN---SGNTGYAQK FQG | RVTMTRNISIDTAYMELSSL SSEDTAVYFCAF | SSGWY---------- | -----FFDY | WGQGT LVTVS S |
| iPS:4 35627 | 21-225_162F6 | VH1\|1-08/D6\|6-19\|RF1/J H4 | QVQLVQS-GAEVKKPGASVKV SCKASG-YTFT | N------YDIN | WVRQATGQ GLEWMG | WMHPN---SGNTGYAQK FQG | RFTMTRNTSISTAYMELSSL RSEDTAVYYCAY | SSGWY---------- | -----RFDY | WGQGT LVTVS S |
| iPS:4 35649 | 21-225_165H2 | VH1\|1-08/D6\|6-19\|RF1/J H4 | QVQLVQS-GAEVKKPGASVKV SCKASG-YTFT | H------YDIN | WVRQATGQ GLEWVG | WMHPN---SHKTGYAQK FQG | RVTMTRNTSNSTAYMDLSSL RSEDTAVYYCAY | SSGWY---------- | -----MFDY | WGQGT LVTVS S |
| iPS:4 35727 | 21-225_172E11 | VH1\|1-08/D6\|6-19\|RF1/J H4 | QVQLVQS-GAEVKKPGASVMV SCKASG-YTFT | N------YDIN | WVRQATGQ GLEWMG | WMHPN---SGNTGYAQK FQG | RVTMTRNTSISTAYMELSSL RSEDTAVYYCAY | SSGWY---------- | -----RFDY | WGQGT LVTVS S |
| iPS:4 35751 | 21-225_175D10 | VH1\|1-08/D6\|6-19\|RF1/J H4 | QVQLVQS-GAEVKKPGASVKV SCKASG-YTFT | N------YDLN | WVRQATGQ GLEWMG | WMHPN---SGNTGYAQK FQG | RVTMTRNISTVYMELSSL RSEDTAVYYCAY | SSGWY---------- | -----YFDY | WGQGT LVTVS S |
| iPS:4 35773 | 21-225_177B12 | VH1\|1-08/D6\|6-19\|RF1/J H4 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAY | SSGWY---------- | -----YFDF | WGQGT LVTVS S |
| iPS:4 35801 | 21-225_181E5 | VH1\|1-08/D6\|6-19\|RF1/J H4 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAH | SSGWY---------- | -----IFDY | WGQGT LVTVS S |
| iPS:4 35841 | 21-225_191D8 | VH1\|1-08/D6\|6-19\|RF1/J H4 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAY | SSGWY---------- | -----YFDY | WGQGT LVTVS S |
| iPS:4 35855 | 21-225_191G3 | VH1\|1-08/D6\|6-19\|RF1/J H4 | QVQLVQS-GAEVKKPGASVKV SCKASG-YTFT | N------YDIN | WVRQATGQ GLEWMG | RMNPN---SGNTGYAQK FQG | RVTMTRNISISTAYMELSSL RSEDTAVYYCAH | SSGWY---------- | -----IFDY | WGQGT LVTVS S |
| iPS:4 35915 | 21-225_190H4 | VH1\|1-08/D6\|6-19\|RF1/J H4 | QVQLVQS-GAEVKKPGASVKV SCKASG-YTFT | N------YDIN | WVRQATGQ GLEWMG | WMNPN---SGNTGYAQK FQG | RVTMTRNISISTAYMELSSL RSEDTAVYYCAH | SSGWY---------- | -----IFDY | WGQGT LVTVS S |
| iPS:4 35925 | 21-225_190D7 | VH1\|1-08/D6\|6-19\|RF1/J H4 | QVQLVQS-GAEVKKPGASVKV SCKASG-NTFT | N------YDIN | WVRQATGQ GLEWMG | WMNPN---SGNTGYAQK FQG | RVTMTRNISISTAYMELSSL RSEDTAVYYCAS | SSGWY---------- | -----YFDY | WGQGT LVTVS S |
| iPS:4 36021 | 21-225_193G4 | VH1\|1-08/D6\|6-19\|RF1/J H4 | QVQLVQS-GAEVKKPGASVKV SCKASG-YTFT | N------YDIN | WVRQATGQ GLEWMG | WMNPN---SGNTGYAQK FQG | RVTMTRNISIRTAYMELNSL RSEDTAVYYCAS | SSGWY---------- | -----FFDY | WGQGT LVTVS S |

Figure 51 (Continued)

| | | | | | | | | | |
|---|---|---|---|---|---|---|---|---|---|
| iPS:4 36150 | 21-225_197H4 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAH | SSGWY--------- | -------YFDY | WGQGTLVTVSS |
| iPS:4 36154 | 21-225_197C6 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | -------YFDY | WGQGTLVTVSS |
| iPS:4 36272 | 21-225_201F5 | VH1\|1-08/D6\|6-19\|RF1/JH4 | QVQLVQS-GAAVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | -------YFDY | WGQGTLVTVSS |
| iPS:4 36550 | 21-225_224D8 | VH1\|1-08/D6\|6-19\|RF1/JH4 | QVQLVQS-GAEVKKPGASVKVSCKASG-YTFT | N-----YDIN | WVRQATGQGLEWMG | WLYPN---SGNTGYAQKFQG | RVTMTRNTSISTAYMELSSLRSEDTAVYYCAY | SSGWY--------- | -------YFDY | WGQGTLVTVSS |
| iPS:4 36554 | 21-225_224C10 | VH1\|1-08/D6\|6-19\|RF1/JH4 | QVQLVQS-GAEVKKPGASVKVSCKASG-STFT | N-----YDIN | WVRQATGQGLEWMG | WMHPN---SGNTGYAQKFQG | RVTMTRNTSISTAYMELSSLRSEDTAVYYCAY | SSGWY--------- | -------KFDY | WGQGTLVTVSS |
| iPS:4 36560 | 21-225_224F11 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | -------KFDY | WGQGTLVTVSS |
| iPS:4 36574 | 21-225_225F5 | VH1\|1-08/D6\|6-19\|RF1/JH4 | QVQLVQS-GTEVRKPGASVKVSCKASG-YTFT | N-----YDIN | WVRQATGQRLEWMG | WMHPN---SGNTGYAQKFQG | RVTMTRNTSISTAYMELSSLRSEDTAVYYCAY | SSGWY--------- | -------RFDY | WGQGTLVTVSS |
| iPS:4 36584 | 21-225_225B9 | VH1\|1-08/D6\|6-19\|RF1/JH4 | QVQLVQS-GAEVKKPGASVKVSCKASG-YTFT | H-----YDIN | WVRQATGQGLEWMG | WMHPN---SGNTGYAQKFRG | RVTMARNTSINTAYMELNSLRSEDTAVYYCAY | SSGWT--------- | -------LFDY | WGQGTLVTVSS |
| iPS:4 36586 | 21-225_225F11 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELNSLRSEDTAVYYCAY | SSGWY--------- | -------RFDY | WGQGTLVTVSS |
| iPS:4 36588 | 21-225_225F12 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMARNTSISTAYMELSSLRSEDTAVYYCAY | SSGWY--------- | -------KFDY | WGQGTLVTVSS |
| iPS:4 36590 | 21-225_225H12 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | -------KFDY | WGQGTLVTVSS |
| iPS:4 36598 | 21-225_226D6 | VH1\|1-08/D6\|6-19\|RF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAI | SSGWY--------- | -------KFDY | WGQGTLVTVSS |

Figure 51 (Continued)

| | | | | | | | | | |
|---|---|---|---|---|---|---|---|---|---|
| iPS:4 36600 | 21-225_226F6 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQKFQG | RVTMTRNISINTAYMELSSLRSEDTAVYYCAY | SSGWY--------- | ------RFDY | WGQGTLVTVSS |
| iPS:4 36616 | 21-225_226D11 | VH1J1-08/D6J6-19JRF1/JH4 | QVQLVQS-GAEVKKPGASVKVSCRSSG-YTFT | N-----YDIN | WVRQATGQGLEWMG | WMHPN---SGNTGYAQKFQG | RVTMTRNTSISTAYMELSSLRSEDTAVYYCAY | SSGWY--------- | ------YFDY | WGQGTLVTVSS |
| iPS:4 36622 | 21-225_226A12 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | ------YFDY | WGQGTLVTVSS |
| iPS:4 36636 | 21-225_227E6 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMELSSLRSEDTAVYYCAY | SSGWY--------- | ------RFDY | WGQGTLVTVSS |
| iPS:4 36638 | 21-225_227C7 | VH1J1-08/D6J6-19JRF1/JH4 | QVQLVQS-GAEVKKPGASVKVSCKISG-HTFT | N-----YDIN | WVRQATGQGLEWMG | WMHPN---SGNTGYAQKFQG | RVTMTRNTSISTAYMELSSLRSEDTAVYYCAY | SSGWY--------- | ------RFDY | WGQGTLVTVSS |
| iPS:4 36646 | 21-225_227D11 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQKFQG | RVTMTRNTSISTAYMEVSSLRSEDTAVYYCAY | SSGWY--------- | ------YFDY | WGQGTLVTVSS |
| iPS:4 46086 | 21-225_94D8 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQKFQV | RVTMTRNISMSTAYMELSSLRSEDTAVYYCAS | SSGWY--------- | ------IFDY | WGQGTLVTVSS |
| iPS:4 51116 | 21-225_164A4 | VH1J1-08/D6J6-19JRF1/JH4 | QVQLVQS-GAEVKKPGASVKVSCKASG-FTFP | N-----YDIN | WVRQATGQGLEWMG | WMHPN---SGNTGYAQKFQG | RVTMTRNTSISTAYMELSSLRSEDTAVYYCAH | SSGWY--------- | ------FFDY | WGQGTLVTVSS |
| iPS:4 51124 | 21-225_74F6 | VH1J1-08/D6J6-19JRF1/JH4 | QVQLVQS-GAEVKKPGASVIRVSCKASG-YTFT | N-----YDIN | WVRQATGQGLEWMG | WMHPN---SGNTGYAQKFQG | RVTMTRNTSISTAYMELSSLRSEDSAVYYCAS | SSGWY--------- | ------FFDY | WGQGTLVTVSS |
| iPS:4 51127 | 21-225_164A7 | VH1J1-08/D6J6-19JRF1/JH4 | QVQLVQS-GAEVKKPGASVKVSCKASG-YTFT | N-----YDVN | WVRQATGQGLEWMG | WMHPN---SGNTGYAQKFQG | RVTMTRNTSISTAYMELSSLRSEDSAVYYCAS | SSGWY--------- | ------LFDY | WGQGTLVTVSS |
| iPS:4 51131 | 21-225_160A7 | VH1J1-08/D6J6-19JRF1/JH4 | QVQLVQS-GAEVKKPGASVKVSCKASG-YTFT | N-----YDIN | WVRQATGQGLEWMG | WMHPH---SGNTGYAQKFQG | RVTMTRNISINTAYMELSSLRSEDTAVYYCAH | SSGWY--------- | ------YFDY | WGQGTLVTVSS |
| iPS:3 92786 | 21-225_24E1 | VH1J1-08/D6J6-19JRF1/JH4 | QVQLVQS-GAEVKKPGASVKVSCKASG-YTFT | N-----YDIN | WVRQATGQGLEWMG | WMHPN---SGNTGYAQRFQG | RVTMTRNTSISTAYMELSSLRSEDTAVYYCAI | SSGWE--------- | ------VFDY | WGQGTLVTVSS |

Figure 51 (Continued)

| | | | | | | | | | |
|---|---|---|---|---|---|---|---|---|---|
| iPS:3 92886 | 21-225_23A12 | VH1|1-08|D6|6-19|RF1/J H4 | QVQLVQS-GAEVKKPGASVKV SCKASG-YPFT | N-----YDIN | WVRQATGQ GLEWMG | WMHPN---SGNTGYAQK FQG | RVTMTRNISINTAYMELSSL RSEDTAVYYCAG | SSGWY------- | -----YFDY | WGQGT LVTVS S |
| iPS:3 92928 | 21-225_25A4 | VH1|1-08|D6|6-19|RF1/J H4 | QVLLVQS-GAEVKRPGASVKV SCKASG-YTFT | N-----YDIN | WVRQATGQ GLEWMG | WMYPN---SGNTGYAQK FQG | RVTMTRNTSISTAYMELSSL RSEDTAVYYCAS | SSGWY------- | -----YFDY | WGQGT LVTVS S |
| iPS:3 92936 | 21-225_28B6 | VH1|1-08|D6|6-19|RF1/J H4 | QVLLVQS-GAEVKRPGASVKV SCKASG-YTFT | N-----YDIN | WVRQATGQ GLEWMG | WMHPD---SGNTGYAQK FQG | RVTMTRNISISTAYMELSSL RSEDTAVYYCAS | SSGWY------- | -----YFDY | WGQGT LVTVS S |
| iPS:3 92960 | 21-225_29E6 | VH1|1-08|D6|6-19|RF1/J H4 | QVLLVQS-GAEVKRPGASVKV SCKASG-YTFT | N-----YDIN | WVRQATGQ GLEWMG | WMHPN---SGNTGYAQK FQG | RVTMTRNISISTAYMELSSL RSEDTAVYYCAS | SSGWY------- | -----YFDY | WGQGT LVTVS S |
| iPS:3 92992 | 21-225_26C4 | VH1|1-08|D6|6-19|RF1/J H4 | QVQLVQS-GAEVKKPGASVKV SCKASG-YTFT | N-----YDIN | WVRQASGQ GLEWMG | WMNPN---SGNTGYAQR FQG | RVTMTRNISISTAYMELSSL RSEDTAVYYCAS | SSGWY------- | -----YFDY | WGQGT LVTVS S |
| iPS:3 93088 | 21-225_33D1 | VH1|1-08|D6|6-19|RF1/J H4 | QVQLVQS-GAEVKKPGASVKV SCKASG-YTFT | N-----YDIN | WVRQATGQ GLEWMG | WMHPN---SGNTGYAQK ERG | RVTMTRNISISTAYMELSSL RSEDTAVYYCAS | SSGWY------- | -----FFDY | WGQGT LVTVS S |
| iPS:3 93144 | 21-225_34D2 | VH1|1-08|D6|6-19|RF1/J H4 | QVQLVQS-GAEVKKPGASVKV SCKASG-YTFT | N-----YDIN | WVRQATGQ GLEWMG | WLHPN---SGTTGPAQK FRG | RVTMTRNISTAYLELSSL RSEDTAVYYCAS | SSGWY------- | -----FFDY | WGQGT LVTVS S |
| iPS:3 93368 | 21-225_29H8 | VH1|1-08|D6|6-19|RF1/J H4 | QVQLVQS-GAEVKKPGASVKV SCKASG-YTFT | N-----YDIN | WVRQATGQ GLEWMG | WMHPN---SGNTGYAQR FQG | RVTMTRNISISAAYMELSSL RSEDTAVYYCAS | SSGWY------- | -----YFDY | WGQGT LVTVS S |
| iPS:3 93942 | 21-225_11E5 | VH1|1-08|D6|6-19|RF1/J H4 | QVQLVQS-GPEVKKPGASVKV SCKASG-YTFT | N-----YDIN | WVRQATGQ GLEWMG | WMHPN---SGATGYAQR FQG | RVTMTRNISISTAYMELSSL RSEDTAVYYCAI | SSGWE------- | -----VFDY | WGQGT LVTVS S |
| iPS:3 94085 | 21-225_8B11 | VH1|1-08|D6|6-19|RF1/J H4 | QVQLVQS-GAEVKKPGASVKV SCKASG-YTFT | N-----YDIN | WVRQAAGQ GLEWMG | WMHPN---SGNTGYAQK FQG | RVTMTRNISRSTAYMELSSL RSEDTAVYYCAY | SSGWY------- | -----FFDY | WGQGT LVTVS S |
| iPS:3 98496 | 21-225_22D2 | VH1|1-08|D6|6-19|RF1/J H4 | QVQLVQS-GAEVKKPGASVKV SCKASG-YTFT | N-----YDIN | WVRQATGQ GLEWMG | WMHPD---SGNTGYAQK FQG | RVTMTRNISISTAYMELSSL RSEDTAVYYCAY | SSGWY------- | -----YFDY | WGQGT LVTVS S |
| iPS:3 98522 | 21-225_32A1 | VH1|1-08|D6|6-19|RF1/J H4 | QVQLVQS-GAEVKKPGASVKV SCKASG-YTFT | N-----YDIN | WVRQATGQ GLEWMG | WMNPN---SGNTGYAQK FQG | RVTMTRNISISTAYMELSSL RSEDTAVYYCAS | SSGWY------- | -----FFDY | WGQGT LVTVS S |

Figure 51 (Continued)

| | | | | H_FR1 | H_CDR1 | H_FR2 | H_CDR2 | H_FR3 | H_CDR3 | H_FR4 |
|---|---|---|---|---|---|---|---|---|---|---|
| iPS:3 98524 | 21-225_32A5 | VH1|1-08/D6|6-19|RF1/JH4 | | QVQLVQS-GAEVKKPGASVKV SCKASG-YTFT | N------YDIN | WVRQATGQ GLEWMG | WMHPN---SGNTGFAQK FRG | RVTMTRNTSISTAYMELSSL RSEDTAVYYCSS | SSGWY--------FFDY | WGQGT LVTVS S |
| iPS:3 98538 | 21-225_34H7 | VH1|1-08/D6|6-19|RF1/JH4 | | QVQLVQS-GAEVKKPGASVKV SCKASG-YTFT | N------YDIN | WVRQATGQ GLEWMG | WMNPN---SGNTGYAQK FQG | RVTMTRNTSISTAYMELNSL RSEDTAVYYCAS | SSGWY--------FFDY | WGQGT LVTVS S |
| | | Germline VH1|1-02D1|1-1|RF1/JH4 | | QVQLVQS-GAEVKKPGASVKV SCKASG-YTFT | Y------YYLH | WVRQAPGQ GLEWMG | WINPN---SGGTNYAQK FQG | RVTMTRDTSISTAYMELSSL RSEDTAVYYCAR | SDY---------SFDY | WGQGT LVTVS S |
| iPS:4 73253 | 21-225_7C3_LC1 | VH1|1-02D1|1-1|RF1/JH4 | | QVQLVQS-GAEVKKPGASVKV SCKASG-YTFN | D------YYLH | WVRQAPGQ GLEWMG | WIHPN---SGGTNYAQK FQG | RVTMTRDTSISTAYMELSSL RSEDTAVYSCAR | DGTS---------SFDY | WGQGT LVTVS S |
| iPS:4 73254 | 21-225_7C3_LC2 | VH1|1-02D1|1-1|RF1/JH4 | | QVQLVQS-GAEVKKPGASVKV SCKASG-YTFN | D------YYLH | WVRQAPGQ GLEWMG | WIHPN---SGGTNYAQK FQG | RVTMTRDTSISTAYMELSSL RSEDTAVYSCAR | DGTS---------SFDY | WGQGT LVTVS S |
| iPS:4 73255 | 21-225_9F12_LC1 | VH1|1-02D1|1-1|RF1/JH4 | | QVQLVQS-GAEVKKPGASVKV SCKASG-YTFA | D------YYLH | WVRQAPGQ GLEWMG | WIHPN---SGGTNFAQK FQG | RVTMTRDTSISTAYLELSSL RSEDTAFYYCAR | DGTS---------SFDY | WGQGT LVTVS S |
| iPS:4 73256 | 21-225_9F12_LC2 | VH1|1-02D1|1-1|RF1/JH4 | | QVQLVQS-GAEVKKPGASVKV SCKASG-YTFA | D------YYLH | WVRQAPGQ GLEWMG | WIHPN---SGGTNFAQK FQG | RVTMTRDTSISTAYLELSSL RSEDTAFYYCAR | DGTS---------SFDY | WGQGT LVTVS S |
| iPS:4 26108 | 21-225_10G6 | VH1|1-02D1|1-1|RF1/JH4 | | QVQLVQS-GAEVKKPGASVKV SCKASG-YTFT | A------YEMH | WVRQAPGQ GLEWMG | WIHPN---NRGTNYAQK FQG | RVTMTRDTSISTAYMELSRL RSEDTAVYYCGR | DVIS---------SFDY | WGQGT LVTVS S |
| iPS:4 26110 | 21-225_12E9 | VH1|1-02D1|1-1|RF1/JH4 | | QVQLVQS-GAEVKKPGASVKV SCKASG-YTFT | D------YYLH | WVRQAPGQ GLEWMG | WVHPN---SGGTNFAQK FQD | RVTMTRDTSISTAYMELSSL RSEDTAVYYCAR | DGTS---------SFDY | WGQGT LVTVS S |
| iPS:4 53451 | 21-225_52G11 | VH1|1-02D1|1-1|RF1/JH4 | | QVQLVQS-GAEVKKPGASVKV SCKASG-YTFT | G------YYLH | WVRQAPGQ GLEWMG | WINPN---RNGTNYAQK FQG | RVTMTRDTSISTAFMELSRL RSEDTAVYYCAR | DGTS---------SFDY | WGQGT LVTVS S |
| iPS:4 53453 | 21-225_53F2 | VH1|1-02D1|1-1|RF1/JH4 | | QVQLVQS-GAEVKKPGASVKV SCKASG-YTFT | G------YYLH | WVRQAPGQ GLEWMG | WINPN---RNGTNYAQN FQG | RVTMTRDTSISTAYMELSRL KSEDTAVYYCAR | DGTS---------SFDY | WGQGT LVTVS S |
| iPS:4 34035 | 21-225_49F10 | VH1|1-02D1|1-1|RF1/JH4 | | QVQLVQS-GAEVKKPGASVKV SCKASG-YTFT | G------YHMH | WVRQAPGQ GLEWMG | WINPN---NNATNYAQN FQG | RVLTIRDTSISTAYMELSRL RSDDTAVYYCAR | DGTS---------SFDF | WGQGT LVTVS S |

Figure 51 (Continued)

| | | | | | | | | | |
|---|---|---|---|---|---|---|---|---|---|
| iPS:4 34065 | 21-225_50D4 | VH1[1-02]D1[1-1]RF1/JH4 | QVQLVQS-GAEVKKPGASVKVSCKASG-YTFT | G-----YHMH | WVRQAPGQGLEWMG | WINPN---NNATNIAQSFQG | RVTLTRDISISTAYMELSRLRSDDTAVYYCAR | DGTS--------SFDF | WGQGTLVTVSS |
| iPS:4 34069 | 21-225_51E9 | VH1[1-02]D1[1-1]RF1/JH4 | QVQLVQS-GAEVKKPGASVKVSCKASR-YTFT | G-----YHIH | WVRQAPGQGLEWMG | WINPN---TNGTQYAQKFQG | RVTMTRDTSISTAYMELSRLRSDDTAVYYCAR | DGTS--------SFDY | WGQGTLVTVSS |
| iPS:4 34079 | 21-225_52B1 | VH1[1-02]D1[1-1]RF1/JH4 | QVQLVQS-GAEVKKPGASVKVSCKASG-YTFT | G-----YHMQ | WVRQAPGQGLEWMG | WINPN---SGATNYAQNFQG | RVTMTRDISISTAYLDLSRLRSDDTAVYYCAR | DGTS--------SFDY | WGQGTLVTVSS |
| iPS:4 34097 | 21-225_52H10 | VH1[1-02]D1[1-1]RF1/JH4 | QVQLVQS-GAEVKKPGASVKVSCKASG-YTFT | G-----YHMQ | WVRQAPGQGLEWMG | WINPN---NGGTQYAQKFQG | RVTMTRDISISTAYMELSRLRSDDTAVYYCAR | DGTS--------SFDY | WGQGTLVTVSS |
| iPS:4 34123 | 21-225_53F7 | VH1[1-02]D1[1-1]RF1/JH4 | QVQLVQS-GAEVKKPGASVKVSCKASG-YTFT | G-----YHMH | WVRQAPGQGLEWMG | WINPN---NNGTNYAQKFQG | RVTMTRDISISTAYMELNRLTSDDTAVYYCAR | DGTS--------SFDY | WGQGTLVTVSS |
| iPS:4 34189 | 21-225_56E5 | VH1[1-02]D1[1-1]RF1/JH4 | QVQLVQS-GAEVKKPGASVKVSCQASG-YTFT | G-----YHMH | WVRQAPGQGLEWMG | WINPN---NNATNYAQKFQG | RVTMTRDISISTAYMELRRLRSDDTAVYHCAR | DGTS--------SFDY | WGQGTLVTVSS |
| iPS:4 35677 | 21-225_169C10 | VH1[1-02]D1[1-1]RF1/JH4 | QVQLVQS-GAEVKKPGASVRVSCKASG-YTFT | G-----YFMH | WVRQAPGQGLEWMG | WIKFK---SGGTNSAQRFQG | RVTMTRDISINIAYMELNRLRSDDTAVYYCAR | GGTIVAT-----WGVFDY | WGQGTLVTVSS |
| iPS:4 35699 | 21-225_170D6 | VH1[1-02]D1[1-1]RF1/JH4 | QVQLVQS-GAEVKKPGASVKVSCKASG-YTFT | G-----YFIH | WVRQAPGQGLEWMG | WIKPN---SGGTNSAQRFQG | RVTMTRDISINIAYMELNRLRSDDTAVYYCAR | GGTIVAT-----WGVFDY | WGQGTLVTVSS |
| iPS:4 35797 | 21-225_181G2 | VH1[1-02]D1[1-1]RF1/JH4 | QVQLVQS-GAEVKTPGASVKVSCRASG-YTFT | S-----YNMH | WVRQVPGQGLEWMG | WINPN---NGGSNYTQKFQG | RVTMTRDISISTAYMELSRLRSDDTAVYYCAR | KF----------GD | WGQGTLVTVSS |
| iPS:4 35877 | 21-225_184E7 | VH1[1-02]D1[1-1]RF1/JH4 | QVQLVQS-GAEVKTPGASVKVSCRASG-YTFT | S-----YNMH | WVRQVPGQGLEWMG | WINPN---NGGSNYTQKFQG | RVTMTRDISISTAYMELSRLRSDDTAVYYCAR | KF----------GD | WGQGTLVTVSS |
| iPS:4 35885 | 21-225_185E10 | VH1[1-02]D1[1-1]RF1/JH4 | QVQLVQS-GAEVKTPGASVKVSCRASG-YTFT | S-----YNMH | WVRQVPGQGLEWMG | WINPN---NGGSNYTQKFQG | RVTMTRDISISTAYMELSRLRSDDTAVYYCAR | KF----------GD | WGQGTLVTVSS |
| iPS:4 35891 | 21-225_188H5 | VH1[1-02]D1[1-1]RF1/JH4 | QVQLVQS-GAEVKTPGASVKVSCRASG-YTFT | S-----YNMH | WVRQVPGQGLEWMG | WINPN---SGGSNYTQKFQG | RITMTRDISISTAYMELSRLRSDDTAVYYCAR | KF----------GD | WGQGTLVTVSS |

Figure 51 (Continued)

| | | | | | | | | | |
|---|---|---|---|---|---|---|---|---|---|
| iPS:4 35897 | 21-225_188B9 | VH1|1-02|D1|1-1|RF1|JH4 | QVQLVQS-GAEVKTPGASVKV SCRASG-YTFT | S------YNMH | WVRQVPGQ GLEWMG | WINPN---SGGSNITQK FQG | RVTMTRDISISTAYMELSRL RSDDTAVYYCAR | KF-------------------GD | WGQGT LVTVS S |
| iPS:4 36400 | 21-225_213H7 | VH1|1-02|D1|1-1|RF1|JH4 | QVQLVQS-GAEVKKPGASVKV SCKASG-YTFT | G------YHMH | WVRQAPGQ GLEWMG | WINPK---SDGTNYAQK FQG | RVTLTRDTSISTAYMELSRL RSDDTAVYYCAR | EKPGS--------YYKY | WGQGT LVTVS S |
| iPS:4 36488 | 21-225_221A6 | VH1|1-02|D1|1-1|RF1|JH4 | QVQLVQS-GAEVKKPGASVRV SCKISG-YTFT | G------YYMH | WVRQAPGQ GLEWMG | WIHPN---SGGTNYAQK FQG | RVTLTRDISISTAYMDLSRL RSDDTAVYYCAR | DGTS-----------SFDY | WGQGT LVTVS S |
| iPS:4 36494 | 21-225_221F12 | VH1|1-02|D1|1-1|RF1|JH4 | QVQLVQS-GAEVKKPGASVKV SCKISG-YTFT | G------YYMH | WVRQAPGQ GLEWMG | WIHPN---SGGTNYAQK FQG | RVTLTRDISISTAYMDLSRL RSDDTAVYYCAR | DGTS-----------SFDY | WGQGT LVTVS S |
| iPS:4 36496 | 21-225_222E1 | VH1|1-02|D1|1-1|RF1|JH4 | QVQLVQS-GAEVKKPGASVKV SCKISG-YTFT | G------YYMH | WVRQAPGQ GLEWMG | WIHPN---SGGTNYAQK FQG | RVTLTRDISISTAYMDLSRL RSDDTAVYYCAR | DGTS-----------SFDY | WGQGT LVTVS S |
| iPS:4 36508 | 21-225_222F7 | VH1|1-02|D1|1-1|RF1|JH4 | QVQLVQS-GAEVKKPGASVKV SCKISG-YTFT | G------YYMH | WVRQAPGQ GLEWMG | WIHPN---SGGTNYAQK FQG | RVTLTRDISISTAYMDLSRL RSDDTAVYYCAR | DGTS-----------SFDY | WGQGT LVTVS S |
| iPS:4 36516 | 21-225_222C12 | VH1|1-02|D1|1-1|RF1|JH4 | QVQLVQS-GAEVKKPGASVKV SCKISG-YTFT | G------YYMH | WVRQAPGQ GLEWMG | WIHPN---SGGTNYAQK FQG | RVTLTRDISISTAYMDLSRL RSDDTAVYYCAR | DGTS-----------SFDY | WGQGT LVTVS S |
| iPS:4 37264 | 21-225_171H12 | VH1|1-02|D1|1-1|RF1|JH4 | QVQLVQS-GAEVKKPGASVRV SCKASG-YTFT | G------YFMH | WVRQAPGQ GLEWMG | WIKPK---SGGTNSAQR FQG | RVTMTRDISINTAYMELNRL RSDDTAVYYCAR | GGTIVAT-------WGVFDY | WGQGT LVTVS S |
| iPS:4 37266 | 21-225_177A5 | VH1|1-02|D1|1-1|RF1|JH4 | QVQLVQS-GAEVKKPGASVKV SCKASG-YTFT | G------YHMH | WVRQAEGQ GLDWMG | WIKPK---SGGTNSAQR FQG | RVTMTRDISINTAYMELNWL RSDDTAVYYCAR | GGTIVAT-------WGVFDY | WGQGT LVTVS S |
| iPS:3 93080 | 21-225_34F3 | VH1|1-02|D1|1-1|RF1|JH4 | QVQLVQS-GAEVKKPGASVKV SCKASG-YTFT | G------YFMH | WVRQAPGQ GLDWMG | WINPN---SGGTNYAQK FQG | RVTMTRDISISTAYMELNRL RSDDTAVYYCAR | DGTS-----------SFDY | WGQGT LVTVS S |
| iPS:3 93084 | 21-225_35C6 | VH1|1-02|D1|1-1|RF1|JH4 | QVQLVQS-GTEVKKPGASVKV SCKASG-YTFT | G------DYMH | WVRQAPGQ GLEWMG | WISPK---NGGTNYAQK FQG | RVTMTRDISISTAYMELNRL RSDDTAVYYCAR | DGTG-----------SFDY | WGQGT LVTVS S |
| iPS:3 93086 | 21-225_36H5 | VH1|1-02|D1|1-1|RF1|JH4 | QVQLVQS-GAEVKKPGASMKV SCKASG-YTFT | D------YHMH | WVRQAPGQ GLEWMG | WINPN---RGGTNYAQK FQD | RVTMTRDISISTAYMELSRL RSDDTAVYFCAR | DGTG-----------SFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 93098 | 21-225_35G6 | VH1\|1-02D\|1-1\|RF1/JH4 | QVQLVQS-GADVKKPGASVKV SCKASG-YTFT | D-----YHIH | WVRQAPGQ GLEWMG | WINPN---NGGTHIAQE FQG | RVTMTRDISISTAYMELSSL RSDDTAVYYCAR | DGTG--------SFDY | WGQGT LVTVS S |
| iPS:3 93112 | 21-225_33G1 | VH1\|1-02D\|1-1\|RF1/JH4 | QVQLAQS-GAEVKKPGASVKV SCKASG-YTFT | G-----YYMH | WVRQAPGQ GLEWMG | WISPN---NGGTNYAQK FQG | RVTMTRDISISTAYMELSRL RSDDTAVYYCAR | DGTG--------SFDY | WGQGT LVTVS S |
| iPS:3 93116 | 21-225_34G7 | VH1\|1-02D\|1-1\|RF1/JH4 | QVQLVQS-GAEVKKPGASVKV SCKASG-YTFT | D-----YHIH | WVRQAPGQ GLEWMG | WINPN---NGGTHYAQK FQG | RVTMTRDISISTAYMELSRL RSDDTAVYYCAR | DGTG--------SFDY | WGQGN LVTVS S |
| iPS:3 93132 | 21-225_33H7 | VH1\|1-02D\|1-1\|RF1/JH4 | QVQLVQS-GADVKKPGASVKV SCKASG-YTFT | D-----YHIH | WVRQAPGQ GLEWMG | WINPN---NGGTHIAQE FQG | RVTMTRDISISTAYMELSSL RSDDTAVHCAR | DGTG--------SFDY | WGQGT LVTVS S |
| iPS:3 93140 | 21-225_35H12 | VH1\|1-02D\|1-1\|RF1/JH4 | QVQLVQS-GAEVKKPGASVKV SCKASG-YTFT | D-----YYIH | WVRQAPGQ GLEWMG | WINPN---RGGTNYAQK FQG | RVTMTRDISISTAYMELSRL RSDDTAVYYCAR | DGTG--------SFDY | WGQGT LVTVS S |
| iPS:3 93954 | 21-225_4H6 | VH1\|1-02D\|1-1\|RF1/JH4 | QVQLVQS-GAEVKKPGASVKV SCKASG-YTFT | D-----YYLH | WVRQAPGQ GLEWMG | WIHPN---SGGTNYAQK FQG | RVTMTRDISISTAYMGLSSL RSDDTAVYYCAR | DGTG--------SFDY | WGQGT LVTVS S |
| iPS:3 98484 | 21-225_18D4 | VH1\|1-02D\|1-1\|RF1/JH4 | QVQLVQS-GAEVKKPGASVKV SCKASG-YTFT | G-----YYLH | WVRQAPGQ GLEWLG | WINPN---SNGTISAQK FQG | RVTMTRDISISTAYMELSRL ISDDTAVYYCAR | DGTS--------SLDY | WGQGT LVTVS S |
| iPS:3 98502 | 21-225_23B11 | VH1\|1-02D\|1-1\|RF1/JH4 | QVQLVQS-GAEVKKPGASVKV SCKASG-YTFT | G-----YYLH | WVRQAPGQ GLEWMG | WINPN---NNGTNYAQK FQG | RVTMTRDISISTAYMELSRL RSDDTAVYYCAR | DGTS--------SFDY | WGQGT LVTVS S |
| iPS:3 98520 | 21-225_31C4 | VH1\|1-02D\|1-1\|RF1/JH4 | QVQLVQS-GIEVKKPGASVKV SCKASG-YTFT | G-----DYMH | WVRQAPGQ GLEWMG | WISPK---NGGTNYAQK FQG | RVTMTRDISISTVYMELNRL RSDDTAVYYCAR | DGTG--------SFDY | WGQGT LVTVS S |
| iPS:4 02223 | 21-225_30A11 | VH1\|1-02D\|1-1\|RF1/JH4 | QVQLVQS-GAEVKKPGASVKV SCKASG-YTFT | D-----YHMH | WVRQAPGQ GLEWMG | WINPN---RGGTNYAQK FQD | RVTMTRDISISTAYMELSRL RSDDTAVYFCAR | DGTG--------SFDY | WGQGT LVTVS S |
| Germline | VH1\|3-33\|D6\|6\|RF1/JH6 | | | | | | | | |
| iPS:4 26114 | 21-225_28H2 | VH3\|3-33\|D6\|6-6\|RF1/JH6 | QVQLVES-GGGVVQPGRSLRL SCAASG-FTFS | N-----YVMH | WVRQAPGK GLEWVA | VIWYD---GSNKYYADS VKG | RFTISRDNSKNTLYLQMNSL RAVDTAVYYCAR | EEYSSGW------YDYGMDV | WGQGT TVTVS S |

Figure 51 (Continued)

| | | | | | | | | |
|---|---|---|---|---|---|---|---|---|
| iPS:4 26116 | 21-225_29E2 | VH3J3-33/D6J6-6jRF1/JH6 | QVQLVES-GGGVVQPGRSLRLSCAASG-FTFS | N------CVMH | WVRQAPGK GLEWVA | VIWYD---GSNKYYADS VKG | RITISRDNSKNTLYLQMNSL RAEDTAVYYCAR | EEYSSGW------------YDYGMDV | WGQGT TVTVS S |
| iPS:4 68812 | 21-225_48H4 | VH3J3-33/D6J6-6jRF1/JH6 | QVQLVES-GGGVVQPGRSLRLSCAASG-FTFS | D------SLMH | WVRQAPGK GLEWVA | VIWYD---GSNKYYTDS VKG | RFTISRDNSKNTLYLQMNSL RAEDTAVYYCAR | ENYSSGW------------YGYGMDV | WGQGT TVTVS S |
| iPS:4 68816 | 21-225_52G8 | VH3J3-33/D6J6-6jRF1/JH6 | QVQLVES-GGGVVQPGRSLRLSCAASG-FTFS | S------YGMH | WVRQAPGK GLEWVA | VIWYD---GSNKYYADS VKG | RFTISRDNSKNTLYLQMNSL RAEDTALYYCAR | RYSSSW------------SGGMDV | WGQGT TVTVS S |
| iPS:4 68826 | 21-225_201C5 | VH3J3-33/D6J6-6jRF1/JH6 | QVQLVES-GGGVVQPGRSLRLSCAASG-FTFS | D------YVMH | WVRQAPGK GLEWVA | VIWYD---GSNKYYVDS VKG | RFTISRDNSRNTLYLQMNSL RAEDTAVYYCAR | ERYSSGL------------YDYGMDV | WGQGT TVTVS S |
| iPS:4 68842 | 21-225_50H4 | VH3J3-33/D6J6-6jRF1/JH6 | QVQLVES-GGGVVQPGRSLRLSCAASG-FTFS | S------YVMH | WVRQAPGK GLEWVA | AIWYD---GSNKYYADS VKG | RFTISRDNSKNTLCLQMNSL RAEDTAVYYCAR | ELYSSNW------------YDYGMDV | WGQGT TVTVS S |
| iPS:4 68858 | 21-225_148C9 | VH3J3-33/D6J6-6jRF1/JH6 | QVQLVES-GGGVAQPGRSLRLSCAASG-FTFS | D------YGMH | WVRQAPGK GLEWVA | VIWYD---GSNKYYADS VKG | RLTISRDNSKNTLYLQMNSL RAEDTAVYYCAR | ERYSSGW------------YDYGLDV | WGQGT TVTVS S |
| iPS:4 68860 | 21-225_224E7 | VH3J3-33/D6J6-6jRF1/JH6 | QVQLVES-GGGVVQPGRSLSLSCAASG-FTFS | S------YVMH | WVRQAPGK GLEWVA | VIWYD---GSNKYYADS VKG | RFTISRDNSKNTLYLQMNSL RAEDTAVYYCAR | EQYSSSW------------YDFGLDV | WGQGT TVTVS S |
| iPS:4 33917 | 21-225_43E11 | VH3J3-33/D6J6-6jRF1/JH6 | QVQLVES-GGGVVQPGRSLRLSCAASG-ESFS | D------YGMH | WVRQAPGK GLEWVA | VIWYD---GSNKYYADS VKG | RLTISRDNSKNTLYLQMNSL RAEDTAVYYCAR | RYVRSW------------VGGMDV | WGQGT TVTVS S |
| iPS:4 33919 | 21-225_44B3 | VH3J3-33/D6J6-6jRF1/JH6 | QVQLVES-GGGVVQPGRSLRLSCTASG-FTFS | D------YGMH | WVRQAEGK GLEWVA | VIWYD---GSNKYYADS VKG | RFTISRDNSKNTLYLQMNSL RAEDTAVYYCAR | ERYSSGW------------YDYGMDV | WGQGT TVTVS S |
| iPS:4 33923 | 21-225_44D3 | VH3J3-33/D6J6-6jRF1/JH6 | QVQLVES-GGGVVQPGRSLRLSCAASG-FTFS | S------YVMH | WVRQAEGK GLEWVA | VIWYD---GSNKYYADS VKG | RFTISRDNSKNTLYLQMNSL RAEDTAVYYCAR | ERYSSGL------------YDYGMDV | WGQGT TVTVS S |
| iPS:4 33929 | 21-225_44D5 | VH3J3-33/D6J6-6jRF1/JH6 | QVQLVES-GGGVVQPGRSLRLSCAASG-FTFS | S------YVMH | WVRQAPGK GLEWVA | VIWYD---GSNKYYADS VKG | RFTISRDNSKNTLYLQMNSL RAEDTAVYYCAR | VPYSSSW------------YDYGMDV | WGQGT TVTVS S |
| iPS:4 33935 | 21-225_44F9 | VH3J3-33/D6J6-6jRF1/JH6 | QVQLVES-GGGVVQPGRSLRLSCAASG-FTFS | S------YVMH | WVRQAPGK GLEWVA | VIWYD---GSNKYYADS VKG | RFTISRDNSKNTLYLQMNSL RAEDTAVYYCAR | EPYSSSW------------YDYGMDV | GGQGT TVTVS S |

Figure 51 (Continued)

| | | | | | | | | | |
|---|---|---|---|---|---|---|---|---|---|
| iPS:4 33937 | 21-225_44B10 | VH3J3-33/D6|6-6|RF1/JH6 | QVQLVES-GGGVVQPGRSLRLSCVASG-FTFS | S-----YGMH | WVRQAPGK GLEWVA | VIWYD---GSNKYYADS VKG | RFTISRDNSKNTLYLQMNSL RAEDTAVYYCAR | RYSSSW------VGGMDV | WGQGT TVTVS S |
| iPS:4 33939 | 21-225_44C10 | VH3J3-33/D6|6-6|RF1/JH6 | QVQLVES-GGGVVQPGRSLRLSCAASG-FTFS | D-----CVMH | WVRQAPGK GLEWVA | VIWYD---GSNKYYADS VKG | RFTISRDNSKNTLYLQMNSL RAEDTAVYYCAR | ERYSSGL------YDYGMDV | WGQGT TVTVS S |
| iPS:4 33951 | 21-225_45B4 | VH3J3-33/D6|6-6|RF1/JH6 | QVQLVES-GGGVVQPGRSLRLSCAASG-FTFS | D-----CVMH | WVRQAPGK GLEWVA | VIWYD---GSNKYYADS VKG | RFTISRDNSKNTLYLQMNSL RAEDTAVYYCAR | ERYSSGL------YDYGMDV | WGQGT TVTVS S |
| iPS:4 33955 | 21-225_45B8 | VH3J3-33/D6|6-6|RF1/JH6 | QVQLVES-GGGVVQPGRSLRLSCAASG-FTFS | D-----CVMH | WVRQAPGK GLEWVA | VIWYD---GSNKYYADS VKG | RFTISRDNSKNTLYLQMNSL RAEDTAVYYCAR | ERYSSGL------YDYGMDV | WGQGT TVTVS S |
| iPS:4 33967 | 21-225_46C3 | VH3J3-33/D6|6-6|RF1/JH6 | QVQLVES-GGGVVQPGRSLRLSCAASG-FTFS | S-----YVMH | WVRQAPGK GLEWVA | VIWYD---GSNKYYADS VKG | RFTISRDNSKNTLYLQMNSL RAEDTAVYYCAR | ERYSSGL------YDYGMDV | WGQGT TVTVS S |
| iPS:4 33971 | 21-225_46D4 | VH3J3-33/D6|6-6|RF1/JH6 | QVQLVES-GGGVVQPGRSLRLSCAASG-FTFS | S-----YVMH | WVRQAPGK GLEWVA | VIWYD---GSNKYYADS VKG | RFTISRDNSKNTLYLQMNSL RAEDTAVYYCAR | VPYSSSW------YDYGMDV | WGQGT TVTVS S |
| iPS:4 33979 | 21-225_46B9 | VH3J3-33/D6|6-6|RF1/JH6 | QVQLVES-GGGVVQPGRSLRLSCSASG-FTFS | S-----YGMH | WVRQAPGK GLEWVA | VIWYD---GRNKYYADS VKG | RITISRDNSKNTLYLQMNSL RAEDTAVYYCAR | RYSSSW------MCGMDV | WGQGT TVTVS S |
| iPS:4 33985 | 21-225_47C1 | VH3J3-33/D6|6-6|RF1/JH6 | QVQLVES-GGGVVQPGRSLRLSCAASG-FTFS | D-----YGMH | WVRQTPGK GLEWVA | VIWYD---GSNKYYADS VKG | RFTISRDNSKNTLFLQMNSL RDEDTAVYYCAR | RYSRSW------VGGMDV | WGQGT TVTVS S |
| iPS:4 33991 | 21-225_47E7 | VH3J3-33/D6|6-6|RF1/JH6 | QVQLVES-GGGVVQPGRSLRLSCAASG-FTFS | I-----YGMH | WVRQAPGK GLEWVA | VIWYD---GSNKYYADS VKG | RFTISRDNSKNTLYLQMNSL RAEDTAVYYCAR | RYSRSW------VGGMDV | WGQGT TVTVS S |
| iPS:4 34001 | 21-225_48F2 | VH3J3-33/D6|6-6|RF1/JH6 | QVQLVES-GGGVVQPGRSLRLSCAASG-FTFS | N-----YVMH | WVRQAPGK GLEWVA | VIWYD---GSNKYYADS VKG | RFTISRDNSKNTLYLQMNSL RAEDTAVYYCAR | ERYSSSW------YDYGLDV | WGQGT TVTVS S |
| iPS:4 34021 | 21-225_49C1 | VH3J3-33/D6|6-6|RF1/JH6 | QVQLVES-GGGVVQPGRSLRLSCAASG-FTFS | S-----YGMH | WVRQAEGK GLEWVA | VIWYD---GSNKYYADS VKG | RFTISRDNSKNTLYLQMNSL RAEDTAVYYCAR | RYSSSW------SGGMDV | WGQGT TVTVS S |
| iPS:4 34025 | 21-225_49G3 | VH3J3-33/D6|6-6|RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------SGGMDV | WGQGT TVTVS S |

Figure 51 (Continued)

| | | | | | | | | | |
|---|---|---|---|---|---|---|---|---|---|
| iPS:4 34031 | 21-225_49E7 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------SGGMDV | WGQGT TVTVS S |
| iPS:4 34033 | 21-225_49F9 | VH3]3-33/D6]6-6]RF1/JH6 | QVQLVES-GGGVVQPGRSLRLSCAASG-FTFS | S-----YGMH | WVRQAPGK GLEWVA | LIWYD---GRNKYYADS VKG | RFTISRDNPKNTLYLQMNSL RAEDTAVYHCAR | RYSSSW------SGGMDV | WGQGT TVTVS S |
| iPS:4 34053 | 21-225_51E1 | VH3]3-33/D6]6-6]RF1/JH6 | QVQLVES-GGGVVQPGRSLRLSCAASG-FTFS | S-----YGMH | WVRQAPGK GLEWVA | VIWYD---GSSKYYADS VKG | RFTISRDNSKNTLYLQMNSL RAEDTAVYYCAR | RYSSSW------SGGMDV | WGQGT TVTVS S |
| iPS:4 34093 | 21-225_52D10 | VH3]3-33/D6]6-6]RF1/JH6 | QVQLVES-GGGVVQPGRSLRLSCAASG-FTFS | S-----YGMH | WVRQAPGK GLEWVA | LIWYD---GSNKYHADS VKG | RFTISRDNSKNTLYLQMNSL RAEDTAVYYCAR | RYSSSW------SGGMDV | WGQGT TVTVS S |
| iPS:4 34137 | 21-225_54D4 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------SGGMDV | WGQGT TVTVS S |
| iPS:4 34149 | 21-225_55H1 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------SGGMDV | WGQGT TVTVS S |
| iPS:4 34151 | 21-225_55C2 | VH3]3-33/D6]6-6]RF1/JH6 | QVQLVES-GGGVVQPGRSLRLSCAASG-FTFS | S-----YGMH | WVRQAPGK GLEWVA | LIWYD---GSNKYHADS VKG | RFTISRDNSKNTLYLQMNSL RAEDTAVYYCAR | RYSSSW------SGGMDV | WGQGT TVTVS S |
| iPS:4 34161 | 21-225_55F9 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------SGGMDV | WGQGT TVTVS S |
| iPS:4 34201 | 21-225_59A12 | VH3]3-33/D6]6-6]RF1/JH6 | QVQLVES-GGGVVQPGRSLRLSCAASG-FTFS | S-----YGMH | WVRQAPGK GLEWVA | VIWYD---GNGKYYADS VKG | RFTISRDNSKNTLYLQMNSL RAEDTAVYYCAR | RYSSSW------SGGMDV | WGQGT TVTVS S |
| iPS:4 34205 | 21-225_60G2 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSRSW------DGGMDV | WGQGT TVTVS S |
| iPS:4 34223 | 21-225_60C12 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYVDS VKG | RFTISRDNSKNTLYLQMNSL RAEDTAVYYCAR | RYSRSW------TGGMDV | WGQGT TVTVS S |
| iPS:4 34231 | 21-225_61F2 | VH3]3-33/D6]6-6]RF1/JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | ERYSSGW------YDYGMDV | WGQGT TVTVS S |

Figure 51 (Continued)

| | | | | | | | | | |
|---|---|---|---|---|---|---|---|---|---|
| iPS:4 34233 | 21-225_61B3 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | RYSRSW------------AGGMDV | WGQGT TVTVS S |
| iPS:4 34303 | 21-225_58H11 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------------DGGMDV | WGQGT TVTVS S |
| iPS:4 34339 | 21-225_64A4 | VH3/3-33/D6/6-6/RF1/JH6 | QVQLVES-GGGVVQPGRSLRL SCAASG-FTFS | D-----YVMH | WVRQAPGK GLEWVA | VIWYD---GSNKYYADS VKG | RFTISRDNSQNTLYLQMNSL RAEDTAVYYCAR | ERYSSSW------------YDYGMDV | WGQGT TVTVS S |
| iPS:4 34343 | 21-225_64C8 | VH3/3-33/D6/6-6/RF1/JH6 | QVQLVES-GGGVVQPGRSLRL SCAASG-FTFS | D-----YVMH | WVRQAPGK GLEWVA | VIWYD---GSNKYYADS MKG | RFTISRDNSKNTLYLQMNSL RAEDTAVYYCAR | ERYSSGW------------YDYGMDV | WGQGT TVTVS S |
| iPS:4 34387 | 21-225_66D11 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLSLQMNSL RAEDTALYYCAR | EMYSSNW------------YDYGLDV | WGQGT TVTVS S |
| iPS:4 34469 | 21-225_73C9 | VH3/3-33/D6/6-6/RF1/JH6 | QVQLVES-GGGVVQPGRSLRL SCAASG-FTFS | N-----YVMH | WVRQAPGK GLEWVA | VIWYD---GSNKYYADS VKG | RFTISRDNSKNTLYLQMNSL RAEDTAVYYCAR | ERYSSSW------------FDYGMDV | WGQGT TVTVS S |
| iPS:4 35197 | 21-225_94F3 | VH3/3-33/D6/6-6/RF1/JH6 | QVQLVES-GGGVVQPGRSLRL SCAASG-FTFS | N-----DIMH | WVRQAPGK GLEWVA | VIWYD---GSNKYYADS VKG | RFTISRDNSKNTLYLQINSL RAEDTAVYYCAR | EKYSSGW------------YDYGMDV | WGQGT TVTVS S |
| iPS:4 35315 | 21-225_147B2 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------------SGGMDV | WGQGT TVTVS S |
| iPS:4 35325 | 21-225_147H5 | VH3/3-33/D6/6-6/RF1/JH6 | QVQLVES-GGGVAQPGRSLRL SCAASG-FTFS | D-----YGMH | WVRQAPGK GLEWVA | VIWYD---GSNKYYADS VKG | RLTISRDNSKNTLYLQMNSL SAEDTAVYYCAR | ERYSSGW------------YDYGLDV | WGQGT TVTVS S |
| iPS:4 35329 | 21-225_147A8 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------------TGGMDV | WGQGT TVTVS S |
| iPS:4 35349 | 21-225_148F5 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | RYSSSW------------SGGMDV | WGQGT TVTVS S |
| iPS:4 35359 | 21-225_148H10 | VH3/3-33/D6/6-6/RF1/JH6 | QVQLVES-GGGVVQPGRSLRL SCAASG-FTFS | S-----YGMH | WVRQAPGK GLEWVA | VIWYD---GSNKYYGDS VKG | RFTISRDNSKNTLYLQMNSL RAEDTAVYYCAR | RYSSSW------------SGGMDV | WGQGT TVTVS S |

Figure 51 (Continued)

| | | | | | | | | | |
|---|---|---|---|---|---|---|---|---|---|
| iPS:4 35393 | 21-225_149D10 | VH3J3-33/D6J6-6JRF1/JH6 | QVQLVES-GGGVAQPGRSLRL SCAASG-FTFS | D------YGMH | WVRQAPGK GLEWVA | VIWYD---GSNKYYADS VKG | RLTISRDNSKNTLYLQMNSL RAEDTAVYYCAR | ERYSSGW------YDYGMDV | WGQGT TVTVS S |
| iPS:4 35401 | 21-225_150E2 | VH3J3-33/D6J6-6JRF1/JH6 | QVQLVES-GGGVVQPGRSLRL SCAASG-FTFS | S------YVMH | WVRQAPGK GLEWVA | VIWYD---GSNKYYADS VKG | RFTISRDNSKNTLYLQMNSL RAEDTAVYYCAR | EEYSSSW------YGYGMDV | WGQGT TVTVS S |
| iPS:4 35417 | 21-225_150D11 | VH3J3-33/D6J6-6JRF1/JH6 | QVQLVES-GGGVVQPGRSLRL SCAASG-FTFS | S------YGMH | WVRQAPGK GLEWVA | VIFYD---GSNKHYADS VKG | RFTISRDNSKNTLYLQMNSL RAEDSAVYYCTR | RFSSSW------SGGMDV | WGQGT TVTVS S |
| iPS:4 35445 | 21-225_152F7 | VH3J3-33/D6J6-6JRF1/JH6 | QVQLVES-GGGVVQPGRSLRL SCAASG-FTFS | S------YIMH | WVRQAPGK GLEWVA | VIWYD---GSNKYYADS VKG | RFTISRDNSKNTLYLQMNSL RAEDTAVYYCAR | EEYSSSW------YGYGMDV | WGQGT TVTVS S |
| iPS:4 35469 | 21-225_153G9 | VH3J3-33/D6J6-6JRF1/JH6 | QVQLVES-GGGVVQPGRSLRL SCAASG-FTFS | S------YGMH | WVRQAEGK GLEWVA | LIFYD---GSNKYYADS VKG | RFTISRDNSKNTLYLQINSL RAEDTAVYFCAR | RYSRSW------AGGMDV | WGQGT AVTVS S |
| iPS:4 35573 | 21-225_159D8 | VH3J3-33/D6J6-6JRF1/JH6 | QVQLVES-GGGVVQPGRSLRL SCAASG-FTFS | N------YVMH | CVRQAPGK GLEWVA | VIWYD---GSNKYYADS VKG | RFTISRDNSKNTLYLQMNSL RAEDTAVYYCAR | EPYSSGW------YDYGMDV | WGQGT TVTVS S |
| iPS:4 35681 | 21-225_169D11 | VH3J3-33/D6J6-6JRF1/JH6 | QVQLVES-GGGVVQPGRSLRL SCAASG-FTFS | D------YVMH | WVRQAPGK GLEWVA | VIWYD---GSNKYYADS VKG | RFTISRDNSKNTLYLQLNSL RAEDTAVYYCAR | ERYSSGW------YDYGMDV | WGQGT TVTVS S |
| iPS:4 35689 | 21-225_170F3 | VH3J3-33/D6J6-6JRF1/JH6 | QVQLVES-GGGVVQPGRSLRL SCAASG-ESFS | D------YVMH | WVRQAPGK GLEWVA | VIWYD---GSNKYYEDS VKG | RFTISRDNSKNTLYLQMNSL RAEDTAVYYCAR | ETYSSSW------YDYGMDV | WGQGT TVTVS S |
| iPS:4 35733 | 21-225_173C11 | VH3J3-33/D6J6-6JRF1/JH6 | QVQLVES-GGGVVQPGRSLRL SCAASG-FTFS | S------YGIH | WVRQAPGK GLEWVA | LIFYD---GSNKYYADS VKG | RFTISRDNSKNTLYLHMSSL RAEDTAVYYCAR | RYSSSW------SGGMDV | WGQGT TVTVS S |
| iPS:4 35741 | 21-225_174G10 | VH3J3-33/D6J6-6JRF1/JH6 | QVQLVES-GGGVVQPGRSLRL SCAASG-FTFS | D------YVMH | WVRQAEGK GLEWVA | VIWYD---GSNKYYADS VKG | RFTISRDNSKNTLYLQLNSL RAEDTAVYYCAR | ERYSSGW------YDYGMDV | WGQGT TVTVS S |
| iPS:4 35763 | 21-225_176H12 | VH3J3-33/D6J6-6JRF1/JH6 | QVQLVES-GGGVVQPGRSLRL SCAASG-FTFS | D------YVMH | WVRQAEGK GLEWVA | VIWYD---GSNKYYADS VKG | RFTISRDNSKNTLYLQMNSL RAEDTAVYYCAR | EKYSSNW------YDYGMDV | WGQGT TVTVS S |
| iPS:4 35767 | 21-225_177B4 | VH3J3-33/D6J6-6JRF1/JH6 | QVQLVES-GGGVVQPGRSLRL SCAASG-FTFS | D------YVMH | WVRQAPGK GLEWVA | VIWYD---GSNKYYADS VKG | RFIVSRDNSKNTLYLQMNSL RAEDTAVYYCAR | EKYSSSW------YDYGLDV | WGQGT TVTVS S |

Figure 51 (Continued)

| | | | | | | | | | |
|---|---|---|---|---|---|---|---|---|---|
| iPS:4 35785 | 21-225_179C2 | VH3|3-33|D6|6-6|RF1|JH6 | QVQLVES-GGGVVQPGRSLRL SCAASG-FTFS | S-----YGMH | WVRQAPGK GLEWVA | LIFYD----GSNKYYADS VKG | RFTISRDNSKNTLFLQMNSL RAEDTAVYYCAR | RYSGW---------SGGMDV | WGQGT TVTVS S |
| iPS:4 35921 | 21-225_190D6 | VH3|3-33|D6|6-6|RF1|JH6 | QVQLVES-GGGVVQPGRSLRL SCAASG-FTFS | S-----FIMH | WVRQAPGR GLEWVA | VIWYD----GSNKYYADS VKG | RFTISRDNSKNTLYLQMNSL RAEDTAVYYCVR | EEYSSGW---------FGYGMDV | WGQGT TVTVS S |
| iPS:4 35961 | 21-225_192A2 | VH3|3-33|D6|6-6|RF1|JH6 | QVQLVES-GGGVVQPGRSLRL SCAASG-FTFS | S-----YGMH | WVRQAPGK GLEWLA | VIWYD----GSYKYYADS VKG | RFTISRDNSKNTLYLQMNSL RAEDTAVYYCAR | EDSPYSGYA---------LDYFYGMDV | WGQGT TVTVS S |
| iPS:4 35985 | 21-225_192F6 | VH3|3-33|D6|6-6|RF1|JH6 | QVQLVES-GGGVVQPGRSLRL SCAASG-FTFS | S-----FIMH | WVRQAPGK GLEWVA | VIWYD----GSNKYYVDS VKG | RFTISRDNSKNTLYLQMNSL RAEDTAVYYCAR | EEYSGGW---------FGYGMDV | WGQGT TVTVS S |
| iPS:4 36039 | 21-225_193F8 | VH3|3-33|D6|6-6|RF1|JH6 | QVQLVES-GGGVVQPGRSLRL SCAASG-FTFS | I-----YGMD | WVRQAPGK GLEWVA | VIWYD----GSYKYYADS VKG | RFTISRDNSKNTLYLQMNSL RAEDTAVYYCAR | EDSPYSGYG---------LDYYYGMDV | WGQGT TVTVS S |
| iPS:4 36074 | 21-225_194F10 | VH3|3-33|D6|6-6|RF1|JH6 | QVQLVES-GGGVVQPGRSLRL SCAASG-FTFS | S-----FIMH | WVRQAPGK GLEWVA | VIWYD----GSNKYYADS VKG | RFTISRDNSKNTLYLEMNSL NVEDTAVYYCAR | EEYSGGW---------FGYGMDV | WGQGT TVTVS S |
| iPS:4 36264 | 21-225_203F7 | VH3|3-33|D6|6-6|RF1|JH6 | QVQLVES-GGGVVQPGRSLRL SCAASG-FTFS | D-----YVMH | WVRQAPGK GLEWVA | VIWYD----GSNKYYVDS VKG | RFTISRDNSRNTLYLQMNSL RAEDTAVYYCAR | ERYSSGL---------YDYGMDV | WGQGT TVTVS S |
| iPS:4 36274 | 21-225_204H3 | VH3|3-33|D6|6-6|RF1|JH6 | QVQLVES-GGGVVQPGRSLRL SCTASG-FTFS | S-----YVMH | WVRQAPGK GLEWVI | VIWYD----GSNKYYADS VKG | RFTISRDNSKNTLYLQMNSL RAEDTAVYYCAR | EFYSSSW---------YDYGMDV | SGQGT TVTVS S |
| iPS:4 36332 | 21-225_208B2 | VH3|3-33|D6|6-6|RF1|JH6 | QVQLVES-GGGVVQPGRSLRL SCAASG-FTFS | D-----CVMH | WVRQAPGK GLEWVA | VIWYD----GSNKYYVDS VKG | RFTISRDNSKNTLYLQMNSL RAEDTAVYYCAR | ERYSSGL---------YDYGLDV | WGQGT TVTVS S |
| iPS:4 36352 | 21-225_210G5 | VH3|3-33|D6|6-6|RF1|JH6 | QVQLVES-GGGVVQPGRSLRL SCAASG-FTFS | D-----CVMH | WVRQAPGK GLEWVA | VIWYD----GSNKYYVDS VKG | RFTISRDNSRNTLYLQMNSL RAEDTAVYYCAR | ERYSSGL---------YDYGLDV | WGQGT TVTVS S |
| iPS:4 36386 | 21-225_212B11 | VH3|3-33|D6|6-6|RF1|JH6 | QVQLVES-GGGVVQPGRSLRL SCAASG-FTFS | D-----YVMH | WVRQAPGK GLEWVT | VIWYD----GSNKYYVDS VKG | RFTISRDNSKNTLYLQMNSL RAEDTAVYYCAR | ERYSSGW---------YDYGMDV | WGQGT TVTVS S |
| iPS:4 36412 | 21-225_214H9 | VH3|3-33|D6|6-6|RF1|JH6 | QVQLVES-GGGVVQPGRSLRL SCAASG-FTFS | S-----YVMH | WVRQAPGK GLEWVA | VIWYD----GSNKYYVDS VKG | RFTISRDNSKNTLYLQMNSL RAEDTAVFYCAR | ERYISSW---------YDYGMDV | WGQGT TVTVS S |

Figure 51 (Continued)

| | | | | | | | | |
|---|---|---|---|---|---|---|---|---|
| iPS:4 36414 | 21-225_214G10 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36416 | 21-225_214G12 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36418 | 21-225_215E3 | VH3j3-33/D6j6-6jRF1/JH6 | QVQLVES-GGGVVQPGRSLRLSCAASG-FTFS | D-----YVIH | WVRQAPGK GLEWVT | VIWYD---GSNKYYADS VKG | RFTISRDNSKNTLYLQMNSV RAEDTAVYYCAR | ERYSSGW-------YDYGMDV | WGQGT TVTVS S |
| iPS:4 36428 | 21-225_215E11 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36438 | 21-225_216E8 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36440 | 21-225_216H12 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36450 | 21-225_217E5 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36456 | 21-225_217G10 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36458 | 21-225_217H12 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36462 | 21-225_218C4 | VH3j3-33/D6j6-6jRF1/JH6 | QVQLVES-GGGVVQPGRSLRLSCAASG-FTFS | D-----YVMH | WVRQAPGK GLEWVT | VIWYD---GSNKYYADS VKG | RFTISRDNSKNTLYLQMNSL RAEDTAVYYCAR | ERYSSGW-------YDYGMDV | WGQGT TVTVS S |
| iPS:4 36480 | 21-225_220F8 | VH3j3-33/D6j6-6jRF1/JH6 | QVQLVES-GGGVVQPGRSLRLSCAASG-FTFS | D-----YVMH | WVRQAPGK GLEWVA | VIWYD---GSNKYYADS VKG | RFTISRDNSKNTLYLQMNSL RAEDTAVYYCAR | ERYSSGW-------YDYGMDV | WGQGT TVTVS S |
| iPS:4 36534 | 21-225_224F1 | VH3j3-33/D6j6-6jRF1/JH6 | QVQLVES-GGGVVQPGRSLRLSCAASG-FTFS | S-----YIMH | WVRQAPGK GLEWVT | VIWYD---GSNKYYADS VKG | RFTISRDNSKNTLYLQMNSL RAEDTAVYYCAR | ERYSNW-------YDYGMDV | WGQGT TVTVS S |

Figure 51 (Continued)

| | | | | | | | | | |
|---|---|---|---|---|---|---|---|---|---|
| iPS:4 36540 | 21-225_224F3 | VH3J3-33/D6J6-6JRF1/JH6 | QVQLVES-GGGVVQPGRSLRL SCAASG-FSFS | S-----YGMH | WVRQAPGK GLEWVA | VIWYD---GSNKYADS VKG | RFTISRDNSKNTLYLQMNSL RAEDTAVYYCAR | ERYSSSW------ ------YDYGMDV | WGQGT TVTVS S |
| iPS:4 36564 | 21-225_225A1 | VH3J3-33/D6J6-6JRF1/JH6 | QVQLVES-GGGVVQPGRSLRL SCAASG-FTFS | D-----YVIH | WVRQAPGK GLEWVA | VIWYD---GSNKYADS VKG | RFTISRDNSKNTLYLQMNSL RAEDTAVYYCAR | ERYSSGW------ ------YDYGMDV | WGQGT TVTVS S |
| iPS:4 36596 | 21-225_226C6 | VH3J3-33/D6J6-6JRF1/JH6 | QVQLVES-GGGVVQPGRSLRL SCAASG-FTFS | D-----YGMH | WVRQAPGK GLEWVA | VIWYD---GSNKYADS VKG | RFTISRDNSKNTLYLQTNSL RAEDTAVYYCAR | ERYSSSW------ ------YDYGMDV | WGQGT TVTVS S |
| iPS:4 36620 | 21-225_226H11 | VH3J3-33/D6J6-6JRF1/JH6 | QVQLVES-GGGVVQPGRSLRL SCAASG-FTFS | N-----CGMH | WVRQAPGK GLEWVI | VIWYD---GSNKYADS VKG | RFTISRDNSKNTLYLQMNSL RAEDTAVYYCAR | ELYSSSW------ ------YDYGLDV | WGQGT TVTVS S |
| iPS:4 36744 | 21-225_154F4 | VH3J3-33/D6J6-6JRF1/JH6 | QVQLVES-GGGVVQPGRSLRL SCAASG-FTFS | S-----YGMH | WVRQAEGK GLEWVA | VIWYD---GSNKYADS VKG | RFTISRDNSKNTLYLQMNSL RAEDTAVYYCAR | EDSYCSGTSC-- ----PYYYYGMDV | WGQGT TVTVS S |
| iPS:4 36946 | 21-225_183F4 | VH3J3-33/D6J6-6JRF1/JH6 | QVQLVES-GGGVVQPGRSLRL SCAASG-FTFS | S-----YGMH | WVRQAPGK GLEWVA | VIWYD---GSNKYADS VKG | RFTISRDNSKNTLYLQMNSL RAEDTAVYYCAR | ERTYCSGTTC-- ----PYYYYGLGV | WGQGT TVTVS S |
| iPS:4 37286 | 21-225_208F1 | VH3J3-33/D6J6-6JRF1/JH6 | QVQLVES-GGGVVQPGRSLRL SCAASG-FTFS | D-----YVMH | WVRQAPGK GLEWVA | VIWYD---GSNKYVDS VKG | RFTISRDNSRNTLYLQMNSL RAEDTAVYYCAR | ERYSSGL------ ------YDYGMDV | WGQGT TVTVS S |
| iPS:4 37290 | 21-225_210G6 | VH3J3-33/D6J6-6JRF1/JH6 | QVQLVES-GGGVVQPGRSLRL SCAASG-FTFS | D-----YVIH | WVRQAPGK GLEWVA | VIWYD---GSNKYVDS VKG | RFTISRDNSKNTLYLQMNSL RAEDTAVYYCAR | ERYSSGL------ ------YDYGMDV | WGQGT TVTVS S |
| iPS:3 92634 | 21-225_17H3 | VH3J3-33/D6J6-6JRF1/JH6 | QVQLVES-GGGVVQPGRSLRL SCAASG-FTFS | N-----CVMH | WVRQAPGK GLEWVA | VIWYD---GSNKYVDS VKG | RFTISRDNSKNTLYLQMNSL RAEDTAVYYCAR | EKYSSSW------ ------YDYGMDV | WGQGT TVTVS S |
| iPS:3 92742 | 21-225_20B2 | VH3J3-33/D6J6-6JRF1/JH6 | QVQLVES-GGGVVQPGRSLRL SCAASR-FTFS | N-----YVIH | WVRQAPGK GLEWVA | VIWYD---GSNKYADS VKG | RFTISRDNSKNTLYLQMNSL RAEDTAVYSCAR | EKYSSSW------ ------YDYGMDV | WGQGT TVTVS S |
| iPS:3 92836 | 21-225_22F4 | VH3J3-33/D6J6-6JRF1/JH6 | QVQLVES-GGGVVQPGRSLRL SCAASG-FTFS | D-----YGMH | WVRQAPGK GLEWVA | VIWYD---GSNKYADS VKG | RFTISRDNSKNTLYLQMNSL RAEDTAVYYCAR | EKYSSSW------ ------YDYGMDV | WGQGT TVTVS S |
| iPS:3 92846 | 21-225_24B6 | VH3J3-33/D6J6-6JRF1/JH6 | QVQLVES-GGGVVQPGRSPRL SCAASG-FIFS | N-----YVMH | WVRQAPGK GLEWVA | VIWYD---GSNKYADS VKG | RFTISRDNSKNTLYLQMNSL RAEDTAVYYCAR | EEYSSGW------ ------YDYGMDV | WGQGT TVTVS S |

Figure 51 (Continued)

| | | | | | | | | | |
|---|---|---|---|---|---|---|---|---|---|
| iPS:3 92884 | 21-225_23A10 | VH3J3-33/DJ6-6JRF1/JH6 | QVQLVES-GGGVVQPGRSLRLSCAASG-FTFS | S-----YGMH | WVRQAPGK GLEWVA | VIWYD----GSNKYYADS VKG | RFTISRDNSKNTLYLQMNSL RAEDTAVYYCAR | ERYSSGW--------HDYGMDV | WGQGT TVTVS S |
| iPS:3 92888 | 21-225_25A2 | VH3J3-33/DJ6-6JRF1/JH6 | QVQLVES-GGGVVQPGRSLRLSCAASG-FTFS | S-----YGMH | WVRQAPGK GLEWVA | VIWYD----GSNKYYADS VKG | RFTISRDNSKNTLYLQMNSL RAEDTAVYYCAR | RYSSSW--------SGGMDV | WGQGT TVTVS S |
| iPS:3 92914 | 21-225_25D12 | VH3J3-33/DJ6-6JRF1/JH6 | QVQLVES-GGGVVQPGRSLRLSCAASG-FTFS | S-----DGMH | WVRQAPGK GLEWVA | VIWYD----GSNKYYADS VKG | RFTISRDNSKNTLYLQMNSL RAEDTAVYYCAR | ERYSSSW--------YDYGMDV | WGQGT TVTVS S |
| iPS:3 92924 | 21-225_32H2 | VH3J3-33/DJ6-6JRF1/JH6 | QVQLVES-GGGVVQPGRSLRLSCAASG-FTFS | S-----YGMH | WVRQAPGK GLEWVA | VIWYD----GSNKYYADS VKG | RFTISRDNSKNTNLQMNSL RAEDTGVYYCAR | RYSSSW--------TGGMDV | WGQGT TVTVS S |
| iPS:3 92938 | 21-225_29H4 | VH3J3-33/DJ6-6JRF1/JH6 | QVQLVES-GGGVVQPGRSLRLSCAASG-FTFS | S-----YGIH | WVRQAPGK GLEWVA | VIWYD----GSNKYYADS VKG | RFTISRDNSKNTLYLQMNSL RAEDTAVYYCAR | RYSSSW--------SGGMDV | WGQGT TVTVS S |
| iPS:3 92974 | 21-225_26A11 | VH3J3-33/DJ6-6JRF1/JH6 | QVQLVES-GGGVVQPGRSLRLSCAASG-FTFS | N-----CVMH | WVRQAPGK GLEWVA | VIWYD----GSNKYYADS VKG | RFTISRDNSKNTLYLQMNSL RAEDTAVYYCAR | EEYSSGW--------YDYGMDV | WGQGT TVTVS S |
| iPS:3 93012 | 21-225_26G7 | VH3J3-33/DJ6-6JRF1/JH6 | QVQLVES-GGGVVQPGRSLRLSCAASG-FTFS | S-----YGMH | WVRQAPGK GLEWVA | VIWYD----GSNKYYADS VKG | RFTISRDNSKNTLYLQMNSL RAEDTAVYYCAR | RYSSSW--------SGGMDV | WGQGT TVTVS S |
| iPS:3 93176 | 21-225_27E7 | VH3J3-33/DJ6-6JRF1/JH6 | QVQLVES-GGGVVQPGRSLRLSCAASG-FTFS | S-----YGMH | WVRQAPGK GLEWVA | VIWYD----GSNKYYADS VKG | RFTISRDNSKNTLYLQMNSL RAEDTAVYYCAR | EDSYCSTSC--------PYYYYGMDV | WGQGT TVTVS S |
| iPS:3 93864 | 21-225_4C5 | VH3J3-33/DJ6-6JRF1/JH6 | QVQLVES-GGGVVQPGRSLRLSCAASG-FTFS | S-----YVLH | WVRQAPGK GLEWVA | VIWYD----GSNKYYADS VKG | RFTISRDNSKNTLYLQMNSL RAEDTAVYYCAR | EKYTSSW--------YDYGMDV | WGQGT TVTVS S |
| iPS:3 93902 | 21-225_14E10 | VH3J3-33/DJ6-6JRF1/JH6 | QVQLVES-GGGVVQPGRSLRLSCAASG-FTFS | D-----YGMH | WVRQAEGK GLEWVA | VIWYD----GSNKYYADS VKG | RFTISRDNSKNTLYLQMNSL RAEDTAVYYCAR | EKYSSSW--------YDYGMDV | WGQGT TVTVS S |
| iPS:3 93908 | 21-225_10E9 | VH3J3-33/DJ6-6JRF1/JH6 | QVQLVES-GGGVVQPGRSLRLSCAASG-FTFS | N-----YVIH | WVRQAEGK GLEWVA | VIWYD----GSNKYYADS VKG | RFTISRDNSKNTLYLQMNSL RAEDTAVYYCAR | EKYSSSW--------YDYGMDV | WGQGT TVTVS S |
| iPS:3 93916 | 21-225_2G4 | VH3J3-33/DJ6-6JRF1/JH6 | QVQLVES-GGGVVQPGRSLRLSCAASG-FTFS | S-----YVMH | WVRQAPGK GLEWVA | VIWYD----GSNKYYADS VKG | RFTISRDNSKNTLYLQMNSL RAEDTAVYYCAR | EKYSSSW--------YDYGMDV | WGHGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 93950 | 21-225_3H10 | VH3/3-33/D6/6-6/RF1/JH6 | QVQLVES-GGGVVQPGRSLRLSCAASG-FTFS | S-----YVMH | WVRQAPGK GLEWVA | VIWYD---GSNKYYADS VKG | RFTISRDNSKNTLYLQMNSL RAEDTAVYYCAR | ERYSSGW----------YDYGLDV | WGQGT TVTVS S |
| iPS:3 93972 | 21-225_7C9 | VH3/3-33/D6/6-6/RF1/JH6 | QVQLVES-GGGVVQPGRSLRLSCAASG-LTFS | N-----YVMH | WVRQAPGK GLEWVA | VIWYD---GSNKYYADS VKG | RFTISRDNSKNTLYLQMNSL RAEDTAVYYCAR | EKYSSSW----------YDYGMDV | WGQGT TVTVS S |
| iPS:3 93978 | 21-225_4C12 | VH3/3-33/D6/6-6/RF1/JH6 | QVQLVES-GGGVVQPGRSLRLSCAASG-FTFS | S-----YVMH | WVRQAPGK GLEWVA | VIWYD---GSNKYYADS VKG | RFTISRDNSKNTLYLQMNSL RAEDTAVYYCAR | EKYSSSW----------YDYGMDV | WGHGT TVTVS S |
| iPS:3 93986 | 21-225_7G4 | VH3/3-33/D6/6-6/RF1/JH6 | QVQLVES-GGGVVQPGRSLRLSCAASG-FTFN | N-----YVMH | WVRQAPGK GLEWVA | VIWYD---GSNKYYADS VKG | RFTISRDNSKNTLYLQMNSL RAEDTAVYYCAR | EKYSSNW----------YDYGMDV | WGQGT TVTVS S |
| iPS:3 93996 | 21-225_15C11 | VH3/3-33/D6/6-6/RF1/JH6 | QVQLVES-GGGVVQPGRSLRLSCAASG-FTFS | D-----YVMH | WVRQAPGK GLEWVA | VIWYD---GSNKYYADS VKG | RFTISRDNSKNTLYLQMNSL RAEDTAVYYCAR | EKYSSSW----------YDYGLDV | WGQGT TVTVS S |
| iPS:3 94041 | 21-225_5E5 | VH3/3-33/D6/6-6/RF1/JH6 | QVQLVES-GGGVVQPGRSLRLSCAASG-FTFS | N-----YVMH | WVRQAPGK GLEWVA | VIWYD---GSNKYYADS VKG | RFTISRDNSKNTLYLQMNSL RAEDTAVYYCTR | EVYSSSW----------YDYGMDV | WGQGT TVTVS S |
| | Germline | VH3/3-33/D2/2-8/RF3/JH4 | | | | | | | |
| iPS:4 26118 | 21-225_7A10 | VH3/3-33/D2/2-8/RF3/JH4 | QVQLVES-GGGVVQPGRSLRLSCAASG-FNFS | S-----YGMH | WVRQAPGK GLEWMA | VIWYD---GSNKYYADS VKG | RFTISRDNSKNTLYLQMHSL RAEDTAVYYCAR | DERLG-----------IFDY | WGQGT LVTVS S |
| iPS:3 93844 | 21-225_3G7 | VH3/3-33/D2/2-8/RF3/JH4 | QVQLVES-GGGVVQPGRSLRLSCAASG-FNFS | N-----YGMH | WVRQAPGK GLEWVA | VIWYD---GSNKYYVDS VKG | RFTISRDNSKNTVYLQMNSL RAEDTAVYYCAR | DERLG-----------IFDY | WGQGT LVTVS S |
| iPS:3 93852 | 21-225_12A10 | VH3/3-33/D2/2-8/RF3/JH4 | QVQLVES-GGGVVQPGRSLRLSCAASG-FTFS | S-----YGMH | WVRQAEGK GLEWVA | VIWHD---ESNKYYADS VKG | RFTISRDNSKNTLYLQMNSL RAEDTAVYYCAR | DERLG-----------IFDY | WGQGT LVTVS S |
| iPS:3 93868 | 21-225_9C11 | VH3/3-33/D2/2-8/RF3/JH4 | QVQLVES-GGGVVQPGRSLRLSCAASG-FTFS | S-----YGMH | WVRQAPGK GLEWVA | VIWHD---ETNKYYADS VKG | RFTISRDNSKNTLSLQMNSL RAEDTAVYYCAR | DERLG-----------IFDY | WGQGT LVTVS S |
| iPS:3 93900 | 21-225_10E12 | VH3/3-33/D2/2-8/RF3/JH4 | QVQLVES-GGGVVQPGRSLRLSCAASG-FNFS | N-----YGMH | WVRQVPGK GLEWVA | VIWHD---GSNKYYVDS VKG | RFTISRDNSKNTLSLQMNSL RAEDTAVYYCCAR | DERLG-----------IFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 93920 | 21-225_1H12 | VH3/3-33/D2/2-8/RF3/JH4 | QVQLVES-GGGVVQSGRSLRL SCAASG-FNFS | S-----YGMH | WVRQAPGK GLEWVA | IIWHD---GSNKYYVDS VKG | RFTISRDNSKNTLYLQMNSL RAEDTAVYYCAR | DERLG-------IFDY | WGQGT LVTVS S |
| iPS:3 93932 | 21-225_10F5 | VH3/3-33/D2/2-8/RF3/JH4 | QVQLVES-GGGVVQPGRSLRL SCAASG-FNFS | S-----YGMH | WVRQAPGK GLEWVS | IIWHD---GSNKYYVDS VKG | RFTISRDNSKNTLYLQMNSL RAEDTAVYYCAR | DERLG-------IFDY | WGQGT LVTVS S |
| | Germline | | H_FR1 | H_CDR1 | H_FR2 | H_CDR2 | H_FR3 | H_CDR3 | H_FR4 |
| | VH3/3-33/D6/6-6/RF1/JH4 | | QVQLVES-GGGVVQPGRSLRL SCAASG-FTFS | S-----YGMH | WVRQAPGK GLEWVS | VIWYD---GSNKYYADS VKG | RFTISRDNSKNTLYLQMNSL RAEDTAVYYCAR | ENSSS-------YYFDY | WGQGT LVTVS S |
| iPS:4 26124 | 21-225_32D6 | VH3/3-33/D6/6-6/RF1/JH4 | QVQLVES-GGGVVQPGRSLRL SCAASG-FTFS | S-----YGMH | WVRQAPGK GLEWVT | VIWHD---GSNAYYADS VKG | RFTISRDNSKNTLYLQMNSL RAEDTAVYYCAR | ENSSS-------YYFDY | WGQGT LVTVS S |
| iPS:3 92922 | 21-225_30G4 | VH3/3-33/D6/6-6/RF1/JH4 | QVQLVES-GGGVVQPGRSLRL SCAASG-FTFS | S-----YGMH | WVRQAPGK GLEWVA | VIWYD---GTDKYYVDS VKG | RFTISRDNSKNTLYLQMNSL RAEDSAVYYCAR | ENSSS-------YYFDY | WGQGT LVTVS S |
| iPS:3 93002 | 21-225_30G1 | VH3/3-33/D6/6-6/RF1/JH4 | QVQLVES-GGGVVQPGRSLRL SCAASG-FTFS | Y-----YGMH | WVRQAPGK GLEWVA | VIWHD---GSNKYYVDS VKG | RFTISRDNSKNTLYLQMNSL RAEDTAVYYCAR | ENSSS-------YYFDY | WGQGT LVTVS S |
| iPS:3 93066 | 21-225_34D3 | VH3/3-33/D6/6-6/RF1/JH4 | QVQLVES-GGGVVQPGRSLRL SCAASG-FTFS | Y-----YGMH | WVRQAPGK GLEWVA | VIWHD---GSNKYYADS VKG | RFTISRDNSKNTLYLQMNSL RAEDTAVYYCAR | ENSSS-------FYFDY | WGQGT LVTVS S |
| iPS:3 93092 | 21-225_33C12 | VH3/3-33/D6/6-6/RF1/JH4 | QVQLVES-GGGVVQPGRSLRL SCAASG-FTFS | H-----YGMH | WVRQAPGK GLEWVA | VIWYD---GSNKYYVDS VKG | RFTISRDNSKNTLYLQMNSL RAEDTAVYYCAR | ENSSS-------YYFDY | WGQGT LVTVS S |
| iPS:3 93100 | 21-225_36B8 | VH3/3-33/D6/6-6/RF1/JH4 | QVQLVES-GGGVVQPGRSLRL SCAASG-FTFS | N-----YGMH | WVRQAPGK GLEWVA | VIWHD---GSNKYYGDS VKG | RFTISRDNSKNTLYLQMNSL RAEDTAVYYCAR | ENSSS-------YYFDY | WGQGT LVTVS S |
| iPS:3 93122 | 21-225_33B2 | VH3/3-33/D6/6-6/RF1/JH4 | QVQLVES-GGGVVQPGRSLRL SCAASG-FTFS | N-----YGMH | WVRQAPGK GLEWVA | VIWHD---GSNKYYADS VKG | RFTISRDNSKNTLYLQMNSL RAEDTAVYYCAR | ENSSS-------YYFDY | WGQGT LVTVS S |
| iPS:3 93134 | 21-225_34C2 | VH3/3-33/D6/6-6/RF1/JH4 | QVQLVES-GGGVVQPGRSLRL SCAASG-FTFS | N-----YVMH | WVRQAPGK GLEWVA | LIWYD---GSNKYYADS VKG | RFTISRDNSKNTLYLQMNSL RAEDSAVYYCAR | ENSSS-------YYFDY | WGQGT LVTVS S |
| iPS:3 93136 | 21-225_34D8 | VH3/3-33/D6/6-6/RF1/JH4 | QVQLVES-GGGVVQPGRSLRL SCAASG-FTFS | N-----YGMH | WVRQAPGK GLEWVA | VIWYD---GSNKYYADS VKG | RFTISRDNSKNTLYLQMNSL RAEDTAVYYCAR | ENSSS-------YYFDY | WGQGT LVTVS S |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| | | VH3J3-30.3/D6J6-19JRF2/JH6 | QVQLVES-CGGVVQPGRSLRL SCAASG-FIFS | S------YGMH | WVRQAPGK GLEWVA | VISTD------ SNKYA | RFTISRDNSKNTLYLQMNIL RAEDTAVYYCAK | GIAVRGYY | WGQGT TVTVS S |
| iPS:4 51135 | 21-225_64A11 | VH3J3-30.3/D6J6-19JRF2/JH6 | QVQLVES-CGGVVQPGRSLRL SCAASG-FIFS | N------YGMH | WVRQAPGK GLEWVA | VISYV------ GSNKYYADS VKG | RFTISRDNSKNTLYLQMNIL RAEDTAVYYCAR | RGAVAP------YYGMDV | WGQGT TVTVS S |
| | | Germline | QVQLVQS-GAEVKKPGASVKV SCKASG-YTFT | S------YDIN | WVRQATGQ GLEWMG | WMNPT------ SGNTGYAQK FQG | RVTMTRDTSTSTVYMELSSL RSEDTAVYYCAR | GIYGGN----------YFDP | WGQGT LVTVS S |
| iPS:4 51137 | 21-225_74A7 | VH1J1-08/D6J6-19JRF1/JH5 | QVQLVQS-GAEVKKPGASVKV SCKASG-YTFT | N------YDIN | WVRQATGQ GLEWMG | WMNPN------ SGNTGYAQK FQG | RVTMTRNTSTSTAHMELSSL RSEDTAVYYCAV | SSGWN----------WFDP | WGQGT LVTVS S |
| iPS:4 34285 | 21-225_57A11 | VH1J1-08/D6J6-19JRF1/JH5 | QVQLVQS-GAEVKKPGASVKV SCKASG-YTFT | N------YDIN | WVRQATGQ GLEWMG | WMNPN------ SVNTGYAQK FQG | RVTMTRDTSTSTAYMELSSL RSEDTAVYYCAI | SSGWN----------WFDP | WGQGT LVTVS S |
| iPS:4 34287 | 21-225_57F12 | VH1J1-08/D6J6-19JRF1/JH5 | QVQLVQS-GAEVKKPGASVKV SCKASG-YTFT | N------YDIN | WVRQATGQ GLEWMG | WMNPN------ SGNTGYAQK FQG | RVTMTRNTSTSTAYMELSSL RSEDTAVYYCAI | SSGWY----------RFDP | WGQGT LVTVS S |
| iPS:4 34479 | 21-225_76H1 | VH1J1-08/D6J6-19JRF1/JH5 | QVQLVQS-GAEVKKPGASVKV SCKASG-YTFT | N------YDIN | WVRQVPGQ GLEWMG | WMHPN------ SGNTGYAQK FQG | RVTMTRNTSTSTAYMELSSL RSEDTAVYYCAI | SSGWY----------WFDP | WGQGT LVTVS S |
| iPS:4 34481 | 21-225_74B10 | VH1J1-08/D6J6-19JRF1/JH5 | QVQLVQS-GAEVKKPGASVKV SCKASG-FTFT | N------YDIN | WVRQATGQ GLEWMG | WMHPN------ SGNTGYAQK FQG | RVTMTRNTSTSTAYMELSSL RSEDTAVYYCAV | SSGWN----------WFDP | WGQGT LVTVS S |
| iPS:4 34483 | 21-225_74C12 | VH1J1-08/D6J6-19JRF1/JH5 | QVQLVQS-GAEVKKPGASVKV SCKASG-YTFT | N------YDIN | WVRQATGQ GLEWMG | WMNPN------ SGNTGYAQK FQG | RVTMTRNTSTSTAYMELSSL RSEDTAVYYCAV | SSGWY----------WFDP | WGQGT LVTVS S |
| iPS:4 34493 | 21-225_76F3 | VH1J1-08/D6J6-19JRF1/JH5 | QVQLVQS-GAEVKKPGASVKV SCKASG-YTFT | N------YDIN | WVRQATGQ GLEWMG | WMNPN------ SGNTGYAQK FQG | RVTMTRNTSTSTAHMELSSL RSEDTAVYYCAV | SSGWN----------WFDP | WGQGT LVTVS S |
| iPS:4 34509 | 21-225_76F5 | VH1J1-08/D6J6-19JRF1/JH5 | QVQLVQS-GAEVKKPGASVKV SCKASG-YTFT | N------YDIN | WVRQATGQ GLEWMG | WMHPN------ SGNTGYAQK FQG | RVTMTRNTSTSTAYMELSSL RSEDTAVYYCAS | SSGWY----------WFDP | WGQGT LVTVS S |
| iPS:4 34513 | 21-225_76A6 | VH1J1-08/D6J6-19JRF1/JH5 | QVQLVQS-GAEVKKPGASVKV SCKASG-YTFT | N------YDIN | WVRQATGQ GLEWMG | WMHPN------ NGNTGYAQK FQG | RVTMTRNTSTSTAYMELNSL RSEDTAVYYCAI | SSGWY----------WFDP | WGQGT LVTVS L |

Figure 51 (Continued)

| | | | | | | | | |
|---|---|---|---|---|---|---|---|---|
| iPS:4 34515 | 21-225_74A5 | VH1¦1-08¦D6¦6-19¦RF1/JH5 | QVQLVQS-GAEVKKPGASVKVSCKASG-YTFT | N-----YDIN | WVRQVPGQGLEWMG | WMHPN---SGNTGYAQKFQG | RVTMTRNTSISTAYMELSSLRSEDTAVYYCAI | SSGWY--------WFDP | WGQGTLVTVSS |
| iPS:4 34525 | 21-225_76E8 | VH1¦1-08¦D6¦6-19¦RF1/JH5 | QVQLVQS-GAEVKKPGASVKVSCKASG-YTFP | N-----YDIN | WVRQATGQGLEWMG | WMNPN---SGNTGYAQKFQG | RVTMTRNSISTAYMELSSLRSEDTAVYYCAV | SSGWH--------WFDP | WGQGTLVTVAS |
| iPS:4 34529 | 21-225_76B9 | VH1¦1-08¦D6¦6-19¦RF1/JH5 | QVQLVQS-GAEVKKPGASVKVSCKASG-YTFT | N-----YDIN | WVRQVPGQGLEWMG | WMHPN---SGNTGYAQKFQG | RVTMTRNTSISTAYMELSSLRSEDTAVYYCAI | SSGWY--------WFDP | WGQGTLVTVSS |
| iPS:4 34575 | 21-225_77C7 | VH1¦1-08¦D6¦6-19¦RF1/JH5 | QVQLVQS-GAEVKKPGASVKVSCKASG-YTFP | N-----YDIN | WVRQATGQGLEWMG | WMHPN---SGNTGYAQKFQG | RVTMTRNSISTAYMELSSLRSEDTAVYYCAV | SSGWH--------WFDP | WGQGTLVTVAS |
| iPS:4 34583 | 21-225_74B6 | VH1¦1-08¦D6¦6-19¦RF1/JH5 | QVQLVQS-GAEVKKPGASVKVSCKASG-YTFT | N-----YDIN | WVRQATGQGLEWMG | WMHPN---NGNTGYAQKFQG | RVTMTRNSISTAYMELNSLRSEDTAVYYCAI | SSGWY--------WFDP | WGQGTLVTVSL |
| iPS:4 34587 | 21-225_74G3 | VH1¦1-08¦D6¦6-19¦RF1/JH5 | QVQLVQS-GAEVKKPGASVKVSCKASG-YTFT | N-----YDIN | WVRQVPGQGLEWMG | WMHPN---SGNTGYAQKFQG | RVTMTRNSISTAYMELSSLRSEDTAVYYCAI | SSGWY--------WFDP | WGQGTLVTVSS |
| iPS:4 34597 | 21-225_77C10 | VH1¦1-08¦D6¦6-19¦RF1/JH5 | QVQLVQS-GAEVKKPGASVKVSCKASG-YTFT | N-----YDIN | WVRQATGQGLEWMG | WMHPN---SGNTGYAQKFQG | RVTMTRNSISTAYMELSSLRSEDTAVYYCAI | SSGWY--------WFDP | WGQGTLVTVSS |
| iPS:4 34603 | 21-225_77D11 | VH1¦1-08¦D6¦6-19¦RF1/JH5 | QVQLVQS-GAEVKKPGASVKVSCKASG-YTFT | N-----YDIN | WVRQVPGQGLEWMG | WMHPN---SGNTGYAQKFQG | RVTMTRNSISTAYMELSSLRSEDTAVYYCAI | SSGWY--------WFDP | WGQGTLVTVSS |
| iPS:4 34613 | 21-225_77D12 | VH1¦1-08¦D6¦6-19¦RF1/JH5 | QVQLVQS-GAEVKKPGASVKVSCKASG-YTFT | N-----YDIN | WVRQATGQGLEWMG | WMHPN---SGNTGYAQKFQG | RVTLTRNTSISTAYMELSSLRSEDTAVYYCAV | SSGWY--------WFDP | WGQGTLVTVSS |
| iPS:4 34617 | 21-225_74B8 | VH1¦1-08¦D6¦6-19¦RF1/JH5 | QVQLVQS-GAEVKKPGASVKVSCKASG-YTFT | N-----YDIN | WVRQATGQGLEWMG | WMHPN---SGNTGYAQKFQG | RVTMTRNSISTAYMELSSLRSEDTAVYYCAV | SSGWY--------WFDP | WGQGTLVTVSS |
| iPS:4 34619 | 21-225_78C1 | VH1¦1-08¦D6¦6-19¦RF1/JH5 | QVQLVQS-GAEVKKPGASVKVSCKASG-YTFT | N-----YDIN | WVRQATGQGLEWMG | WMNPN---SGNTGYAQKFQG | RVTMTRNSISTAYMELSSLRSEDTAVYYCAI | SSGWY--------WFDP | WGQGTLVTVSS |
| iPS:4 34639 | 21-225_74B7 | VH1¦1-08¦D6¦6-19¦RF1/JH5 | QVQLVQS-GAEVKKPGASVKVSCKASG-YTFP | N-----YDIN | WVRQATGQGLEWMG | WMNPN---SGNTGYAQKFQG | RVTMTRNSISTAYMELSSLRSEDTAVYYCAV | SSGWH--------WFDP | WGQGTLVTVAS |

Figure 51 (Continued)

| | | | | | | | | | |
|---|---|---|---|---|---|---|---|---|---|
| iPS:4 34653 | 21-225_74B5 | VH1｜1-08/D6｜6-19｜RF1/JH5 | QVQLVQS-GAEVKKPGASVKVSCKASG-YTFT | N-----YDIN | WVRQATGQGLEWMG | WMNPN---SGNTGYAQKFQG | RVTMTRNTSTAHMELSSLRSEDTAVYYCAV | SSGWN--------WFDP | WGQGTLVTVSS |
| iPS:4 34655 | 21-225_78H12 | VH1｜1-08/D6｜6-19｜RF1/JH5 | QVQLVQS-GAEVKKPGASVKVSCKASG-YTFP | N-----YDIN | WVRQATGQGLEWMG | WMNPN---SGNTGYAQKFQG | RVTMTRNTSTAYMELSSLRSEDTAVYYCAV | SSGWH--------WFDP | WGQGTLVTVAS |
| iPS:4 34675 | 21-225_79G6 | VH1｜1-08/D6｜6-19｜RF1/JH5 | QVQLVQS-GAEVKKPGASVKVSCKASG-FTFT | N-----YDIN | WVRQATGQGLEWMG | WMHPN---SGNTGFAQKFQG | RVTMTRNTSTAYMELSSLRSEDTAVYYCAV | SSGWY--------WFDP | WGQGTLVTVSS |
| iPS:4 34689 | 21-225_79G10 | VH1｜1-08/D6｜6-19｜RF1/JH5 | QVQLVQS-GAEVKKPGASVKVSCKASG-YTFT | N-----YDIN | WVRQATGQGLEWMG | WMNPN---SGNTGYAQKFQG | RVTMTRNTSTAHMELSSLRSEDTAVYYCAV | SSGWN--------WFDP | WGQGTLVTVSS |
| iPS:4 34705 | 21-225_80A2 | VH1｜1-08/D6｜6-19｜RF1/JH5 | QVQLVQS-GAEVKKPGASVKVSCKASG-YTFT | N-----YDIN | WVRQVPGQGLEWMG | WMHPN---SGNTGYAQKFQG | RVTMTRNTSTAYMELSSLRSEDTAVYYCAI | SSGWY--------WFDP | WGQGTLVTVSS |
| iPS:4 34707 | 21-225_80D3 | VH1｜1-08/D6｜6-19｜RF1/JH5 | QVQLVQS-GAEVKKPGASVKVSCKASG-YTFT | N-----YDIN | WVRQATGQGLEWMG | WMHPN---SGNTGYAQKFQG | RVTMTRNTSTAYMELSSLRSEDTAVYYCAI | SSGWY--------WFDP | WGQGTLVTVSS |
| iPS:4 34731 | 21-225_80E9 | VH1｜1-08/D6｜6-19｜RF1/JH5 | QVQLVQS-GAEVKKPGASVKVSCKASG-YTFT | N-----YDIN | WVRQATGQGLEWMG | WMHPN---SGNTGYAQKFQG | RVTMTRNTSTAYMELNSLRSEDTAVYYCAI | SSGWY--------WFDP | WGQGTLVTVSL |
| iPS:4 34747 | 21-225_80C12 | VH1｜1-08/D6｜6-19｜RF1/JH5 | QVQLVQS-GAEVKKPGASVKVSCKASG-YTFT | N-----YDIN | WVRQATGQGLEWMG | WMHPN---NGNTGYAQKFQG | RVTMTRNTSTAYMELSSLRSEDTAVYYCAV | SSGWN--------WFDP | WGQGTLVTVSS |
| iPS:4 34761 | 21-225_81E5 | VH1｜1-08/D6｜6-19｜RF1/JH5 | QVQLVQS-GAEVKKPGASVKVSCKASG-YTFT | N-----YDIN | WVRQATGQGLEWMG | WMHPN---SGNTGYAQKFQG | RVTMTRNTSTAYMELSSLRSEDTAVYYCAI | SSGWY--------WFDP | WGQGTLVTVSS |
| iPS:4 34771 | 21-225_81F9 | VH1｜1-08/D6｜6-19｜RF1/JH5 | QVQLVQS-GAEVKKPGASVKVSCKASG-YTFT | N-----YDIN | WVRQATGQGLEWMG | WMHPN---SGNTGYAQKFQG | RVTMTRNTSTAYMELSSLRSEDTAVYYCAI | SSGWY--------WFDP | WGQGTLVTVSS |
| iPS:4 34793 | 21-225_82A5 | VH1｜1-08/D6｜6-19｜RF1/JH5 | QVQLVQS-GAEVKKPGASVKVSCKASG-YTFT | N-----YDIN | WVRQVPGQGLEWMG | WMHPN---NGNTGYAQKFQG | RVTMTRNTSTAYMELNSLRSEDTAVYYCAI | SSGWY--------WFDP | WGQGTLVTVSL |
| iPS:4 34797 | 21-225_82G5 | VH1｜1-08/D6｜6-19｜RF1/JH5 | QVQLVQS-GAEVKKPGASVKVSCKASG-YTFT | N-----YDIN | WVRQVPGQGLEWMG | WMHPN---SGNTGYAQKFQG | RVTMTRNTSTAYMELSSLRSEDTAVYYCAI | SSGWY--------WFDP | WGQGTLVTVSS |

Figure 51 (Continued)

| | | | | | | | | | |
|---|---|---|---|---|---|---|---|---|---|
| iPS:4 34805 | 21-225_82D9 | VH1¦1-08/D6¦6-19¦RF1/J H5 | QVQLVQS-GAEVKKPGASVKV SCKASG-YTFT | N-----YDIN | WVRQVPGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34813 | 21-225_82C12 | VH1¦1-08/D6¦6-19¦RF1/J H5 | QVQLVQS-GAEVKKPGASVKV SCKASG-YTFT | N-----YDIN | WVRQAIGQ GLEWMG | WMHPN---NGNTGYAQK FQG | RVTMTRNTSISTAYMELNSL RSEDTAVYYCAI | SSGWY----------- | -------WFDP | WGQGT LVTVS L |
| iPS:4 34825 | 21-225_83C2 | VH1¦1-08/D6¦6-19¦RF1/J H5 | QVQLVQS-GAEVKKPGASVKV SCKASG-YTFT | N-----YDIN | WVRQVPGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34827 | 21-225_83F3 | VH1¦1-08/D6¦6-19¦RF1/J H5 | QVQLVQS-GAEVKKPGASVKV SCKASG-YTFT | N-----YDIN | WVRQAIGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34829 | 21-225_83G3 | VH1¦1-08/D6¦6-19¦RF1/J H5 | QVQLVQS-GAEVKKPGASVKV SCKASG-YTFT | N-----YDIN | WVRQAIGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34833 | 21-225_83C5 | VH1¦1-08/D6¦6-19¦RF1/J H5 | QVQLVQS-GAEVKKPGASVKV SCKASG-YTFT | N-----YDIN | WVRQVPGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34841 | 21-225_83G7 | VH1¦1-08/D6¦6-19¦RF1/J H5 | QVQLVQS-GAEVKKPGASVKV SCKASG-YTFT | N-----YDIN | WVRQAIGQ GLEWMG | WMHPN---SGNTGYAQK FQG | RVTMTRNISISTAYMELSSL RSEDTAVYYCAV | SSGWH----------- | -------WFDP | WGQGT LVTVS S |
| iPS:4 34863 | 21-225_84G7 | VH1¦1-08/D6¦6-19¦RF1/J H5 | QVQLVQS-GAEVKKPGASVKV SCKASG-YTFP | N-----YDIN | WVRQVPGQ GLEWMG | WMHPN---SGNTGYAQK FQG | RVTLTRNISISTAYMELSSL RSEDTAVYYCAV | SSGWH----------- | -------WFDP | WGQGT LVTVA S |
| iPS:4 34877 | 21-225_85H2 | VH1¦1-08/D6¦6-19¦RF1/J H5 | QVQLVQS-GAEVKKPGASVKV SCKASG-YTFP | N-----YDIN | WVRQVPGQ GLEWMG | WMHPN---SGNTGYAQK FQG | RVTMTRNISISTAYMELSSL RSEDTAVYYCAV | SSGWY----------- | -------WFDP | WGQGT LVTVA S |
| iPS:4 34883 | 21-225_85B5 | VH1¦1-08/D6¦6-19¦RF1/J H5 | QVQLVQS-GAEVKKPGASVKV SCKASG-YTFT | N-----YDIN | WVRQVEGQ GLEWMG | WMHPN---SGNTGYAQK FQG | RVTMTRNISISTAYMELSSL RSEDTAVYYCAI | SSGWY----------- | -------WFDP | WGQGT LVTVS S |
| iPS:4 34911 | 21-225_85D11 | VH1¦1-08/D6¦6-19¦RF1/J H5 | QVQLVQS-GAEVKKPGASVKV SCKASG-YTFT | N-----YDIN | WVRQAIGQ GLEWMG | WMNPN---SGNTGYAQK FQG | RVTMTRNISISTAYMELSSL RSEDTAVYYCAI | SSGWY----------- | -------WFDP | WGQGT LVTVS S |
| iPS:4 34935 | 21-225_86E9 | VH1¦1-08/D6¦6-19¦RF1/J H5 | QVQLVQS-GAEVKKPGASVKV SCKASG-YTFT | N-----YDIN | WVRQAIGQ GLEWMG | WMNPN---SGNTGYAQK FQG | RVTMTRSISTIAHMELSSL RSEDTAVYYCAV | SSGWS----------- | -------WFDP | WGQGT LVTVS S |

Figure 51 (Continued)

| | | | | | | | | | | |
|---|---|---|---|---|---|---|---|---|---|---|
| iPS:4 34957 | 21-225_87A10 | VH1[1-08/D6[6-19]RF1/JH5 | QVQLVQS-GAEVKKPGASVKVSCKASG-YTFT | N-----YDIN | WVRQATGQGLEWMG | WMHPN---NGNTGYAQKFQG | RVTMTRNISISTAYMELNSLRSEDTAVYYCAI | SSGWY--------WFDP | WGQGTLVTVSL |
| iPS:4 34971 | 21-225_88G2 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAI | SSGWY--------WFDP | WGQGTLVTVSS |
| iPS:4 35051 | 21-225_90D9 | VH1[1-08/D6[6-19]RF1/JH5 | QVQLVQS-GAEVKKPGASVKVSCKASG-YTFP | N-----YDIN | WVRQATGQGLEWMG | WMNPN---SGNTGYAQKFQG | RVTMTRNISISTAYMELSSLRSEDTAVYYCAV | SSGWH--------WFDP | WGQGTLVTVAS |
| iPS:4 35071 | 21-225_91F1 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAV | SSGWY--------WFDP | WGQGTLVTVSS |
| iPS:4 35087 | 21-225_91G8 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAI | SSGWY--------WFDP | WGQGTLVTVSS |
| iPS:4 35203 | 21-225_75A7 | VH1[1-08/D6[6-19]RF1/JH5 | QVQLVQS-GAEVKKPGASVKVSCKASG-YTFP | N-----YDIN | WVRQATGQGLEWMG | WMNPN---SGNTGYAQFQD | RVTMTRNISISTAYMELSSLRSEDTAVYYCAV | SSGWH--------WFDP | WGQGTLVTVAS |
| iPS:4 35211 | 21-225_94E11 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTMTRNISISTAHMELSSLRSEDTAVYYCAV | SSGWK--------WFDP | WGQGTLVTVSS |
| iPS:4 35227 | 21-225_95G4 | VH1[1-08/D6[6-19]RF1/JH5 | QVQLVQS-GAEVKKPGASVKVSCKASG-YTFT | N-----YDIN | WVRQATGQGLEWMG | WMNPN---SGNTGYAQKFQG | RVTMTRNISISTAHMELSSLRSEDTAVYYCAV | SSGWN--------WFDP | WGQGTLVTVSS |
| iPS:4 35245 | 21-225_95E12 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTMTRNISISTAYMELSSLRSEDTAVYYCAI | SSGWY--------WFDP | WGQGTLVTVSS |
| iPS:4 35247 | 21-225_96G1 | VH1[1-08/D6[6-19]RF1/JH5 | QVQLVQS-GAEVKKPGASVKVSCKASG-YTFT | N-----YDIN | WVRQATGQGLEWMG | WMHPN---NGNTGYAQKFQG | RVTMTRNISISTAYMELNSLRSEDTAVYYCAI | SSGWY--------WFDP | WGQGTLVTVSL |
| iPS:4 35249 | 21-225_96E2 | VH1[1-08/D6[6-19]RF1/JH5 | QVQLVQS-GAEVKKPGASVKVSCKASG-YTFT | N-----YDIN | WVRQATGQGLEWMG | WMHPN---SGNTGYAQKFQG | RVTLTRNISTAYMELSSLRSEDTAVYYCAV | SSGWY--------WFDP | WGQGTLVTVSS |
| iPS:4 35255 | 21-225_96D5 | VH1[1-08/D6[6-19]RF1/JH5 | QVQLVQS-GAEVKKPGASVKVSCKASG-YTFT | N-----YDIN | WVRQATGQGLEWMG | WMNPN---SGNTGYAQKFQG | RVTMTRSISTAHMELSSLRSEDTAVYYCAV | SSGWS--------WFDP | WGQGTLVTVSS |

Figure 51 (Continued)

| | | | | | | | | | |
|---|---|---|---|---|---|---|---|---|---|
| iPS:4 35279 | 21-225_97H4 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAI | SSGWY--------WFDP | WGQGT LVTVS S |
| iPS:4 35327 | 21-225_147G6 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQG | RVTMTRNTSISTAYMELSSL RSEDTAVYYCAY | SSGWY--------WFDP | WGQGT LVTVS S |
| iPS:4 35437 | 21-225_152F4 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAY | SSGWY--------WFDP | WGQGT LVTVS S |
| iPS:4 35701 | 21-225_170F6 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQD | RVTMTRHTSISTAYMELSSL RSEDTAVYYCAI | SSGWY--------WFDP | WGQGT LVTVS S |
| iPS:4 35737 | 21-225_174G5 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAV | SSGWY--------WFDP | WGQGT LVTVS S |
| iPS:4 36544 | 21-225_224H5 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGYAQK FQG | RVTMTRNISISTAYMELSSL RSEDTAVYYCAS | SSGWN--------WFDP | WGQGT LVTVS S |
| iPS:4 36570 | 21-225_225F4 | VH1|1-08/D6|6-19|RF1/J H5 | QVQLVQS-GAEVKKPGASVKV SCKASG-YTFT | N------YDIN | WVRQATGQ GLEWMG | WMHPN---SGSTGYAQK FQG | RLTMTRNISIVYMELNSL RSEDTAVYYCAI | SSGWY--------WFDP | WGQGT LVTVS S |
| iPS:4 36644 | 21-225_227G9 | VH1|1-08/D6|6-19|RF1/J H5 | QVQLVQS-GAEVKKPGASVKV SCKASG-YTFT | N------YDIN | WVRQATGR GLEWMG | WMYPN---SGNTGYAQK FQG | RVTMTRNISISTAYMELSSL RSEDTAVYYCAL | SSGWY--------WFDP | WGQGT LVTVS S |
| iPS:4 37322 | 21-225_75B1 | VH1|1-08/D6|6-19|RF1/J H5 | QVQLVQS-GAEVKKPGASVKV SCKASG-YTFT | N------YDIN | WVRQVPGQ GLEWMG | WMNPD---SGNTGYAQK FQG | RVTMTRNISISTAYMELSSL RSEDTAVYYCAV | SSGWY--------WFDP | WGQGT LVTVS S |
| iPS:4 37361 | 21-225_74C1 | VH1|1-08/D6|6-19|RF1/J H5 | QVQLVQS-GAEVKKPGASVKV SCKASG-YTFT | N------YDIN | WVRQATGQ GLEWMG | WMNPN---SGNIGYAQK FQG | RVTMTRNISISTAYMELSSL RSEDTAVYYCAV | SSGWY--------WFDP | WGQGT LVTVS S |
| iPS:4 37363 | 21-225_74C10 | VH1|1-08/D6|6-19|RF1/J H5 | QVQLVQS-GAEVKKPGASVKV SCKASG-YTFT | N------YDIN | WVRQATGQ GLEWMG | WMHPN---SGNTGFAQK FQG | RVTMTRNISISTAYMELSSL RSEDTAVYYCAI | SSGWY--------WFDP | WGQGT LVTVS S |
| iPS:4 37379 | 21-225_74H2 | VH1|1-08/D6|6-19|RF1/J H5 | QVQLVQS-GAEVKKPGASVKV SCKASG-FTFT | N------YDIN | WVRQATGQ GLEWMG | WMHPN---SGNTGFAQK FQG | RVTMTRNISISTAYMELSSL RSEDTAVYYCAV | SSGWY--------WFDP | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 46094 | 21-225_77E1 | VH1\|1-08/D6\|6-19\|RF1/JH5 | QVQLVQS-GAEVKKPGASVKV SCKASG-YTFP | N------YDIN | WVRQATGQ GLEWMG | WMNPN---SGNTGYAQK FQG | RVTMTRNTSISTAYMELSSL RSEDTAVYYCAV | SSGWH--------WFDP | WGQGT LVTVA S |
| iPS:4 51129 | 21-225_94D2 | VH1\|1-08/D6\|6-19\|RF1/JH5 | QVQLVQS-GAEVKKPGASVKV SCKASG-FTFT | N------YDIN | WVRQATGQ GLEWMG | WMHPN---SGNTGFAQK FQG | RVTMTRNTSISTAYMELSSL RSEDTAVYYCAV | SSGWY--------WFDP | WGQGT LVTVS S |
| iPS:4 51133 | 21-225_95H4 | VH1\|1-08/D6\|6-19\|RF1/JH5 | QVQLVQS-GAEVKKPGASVKV SCKASG-YTFT | N------YDIN | WVRQATGQ GLEWMG | WMNPN---SGNTGYAQK FQG | RVTMTRNTSTSTAHMELSSL RSEDTAVYYCAV | SSGWN--------WFDP | WGQGT LVTVS S |
| iPS:3 98510 | 21-225_25A3 | VH1\|1-08/D6\|6-19\|RF1/JH5 | QVQLVQS-GAEVKKPGASVKV SCKASG-YIFT | N------YDIN | WVRQATGQ GLEWMG | WMHPN---SGNTGYAQK FQG | RVTMTWNTSISTANMELSSL RSEDTAVYYCAS | SSGWY--------WFDP | WGQGT LVTVS S |
| iPS:3 98516 | 21-225_26A9 | VH1\|1-08/D6\|6-19\|RF1/JH5 | QVQLVQS-GAEVKKFGASVKV SCKASG-YTFI | N------YDIN | WVRQATGQ GLEWMG | WMHPN---SGNTGCAQK FQG | RVTMTWNMSISTAYMELSSL RSEDTAVYYCAS | SSGWY--------WFDP | WGQGT LVTVS S |
| | Germline | | H_FR1 | H_CDR1 | H_FR2 | H_CDR2 | H_FR3 | H_CDR3 | H_FR4 |
| | VH3\|3-30.3\|D5\|5-18\|RF3\|JH4 | | | | | | | | |
| iPS:4 51139 | 21-225_71A6 | VH3\|3-30.3/D5\|5-18\|RF3/JH4 | QVQLVES-CGGVVQPGRSLRL SCAASG-FTFS | N------YGMH | WVRQAPGK GLEWVA | VISYD---GSNEYADS VKG | RFTISRDNSKNTLYLQMNSL RAEDTAVYYCAR | DERYGV-------RGGFDY | WGQGT LVTVS S |
| | Germline | | H_FR1 | H_CDR1 | H_FR2 | H_CDR2 | H_FR3 | H_CDR3 | H_FR4 |
| | VH1\|1-18\|D6\|6-19\|RF2\|JH5 | | | | | | | | |
| iPS:4 51143 | 21-225_66H11 | VH1\|1-18/D6\|6-19\|RF2/JH5 | QVQLVQS-GAEVKKPGASVKV SCKASG-YTFA | T------YGIS | WVRQAPGQ GLEWMG | WISAY---NGNTNYAQK LQG | RVTMTDTSTSTAYMELRSL RSDDTAVYYCAR | GEAVA--------VFDP | WGQGT LVTVS S |
| iPS:4 34361 | 21-225_65D5 | VH1\|1-18/D6\|6-19\|RF2/JH5 | QVQLVQS-GAEVKKPGASVKV SCKASG-YTFP | S------YGIS | WVRQAPGQ GLEWMG | WISAY---SGNTNYAQK LQG | RVTMTTDTSTSTAYMELRSL RSEDDIAVYFCAR | GEAVA--------VFDP | WGQGT LVTVS S |
| | Germline | | H_FR1 | H_CDR1 | H_FR2 | H_CDR2 | H_FR3 | H_CDR3 | H_FR4 |
| | VH3\|3-33\|D3\|4-23\|RF2\|JH6 | | | | | | | | |
| iPS:4 53445 | 21-225_148E10 | VH3\|3-33/D4\|4-23\|RF2/JH6 | QVQLVES-CGGVVQPGRSLRL SCAASG-FTFS | S------YGMH | WVRQAPGK GLEWVA | VIWFD---GSNKYYVDS VKD | RFTISRDNSKNTLYLQMNSL RAEDTAVYYCAR | DEVEGSGTP----YYYYGMDV | WGQGT TVTVS S |

Figure 51 (Continued)

| | | | | | | | | | |
|---|---|---|---|---|---|---|---|---|---|
| iPS:4 36082 | 21-225_195D9 | VH3j3-33/D4|4-23|RF2/J H6 | QVQLVES-GGGVVQPGRSLRL SCAASG-FTFS | H-----YVMH | WVRQAPGK GLEWVA | VIWYD----GTNKYYADS VKG | RFTISRDNSKNTLYLQMNSL RAEDTAVYYCAR | DWFGEGN----------YYGMDV | WGQGT TVTVS S |
| iPS:4 36118 | 21-225_196A10 | VH3j3-33/D4|4-23|RF2/J H6 | QVQLVES-GGGVVQPGRSLRL SCAASG-FTFS | H-----YVMH | WVRQAPGK GLEWVA | VIWYD----GTNKYYADS VKG | RFTISRDNSKNTLYLQMNSL RAEDTAVYYCAR | DWFGEGN----------YYGMDV | WGQGT TVTVS S |
| iPS:4 36670 | 21-225_147D9 | VH3j3-33/D4|4-23|RF2/J H6 | QVQLVES-GGGVVQPGRSLRL SCAASG-FTFS | S-----YGMH | WVRQAPGK GLEWVA | DIMFD----GSNKYYVDS VKD | RFTISRDNSKNTLYLQMNSL RAEDTAVYYCAR | DRVEGSGTP----------YYYYGMDV | WGQGT TVTVS S |
| iPS:4 36720 | 21-225_151H6 | VH3j3-33/D4|4-23|RF2/J H6 | QVQLVES-GGGVVQPGRSLRL SCAASG-FTFS | D-----YGMH | WVRQAPGK GLEWVA | LIWYD----GSNKYYADS VKG | RFTISRDNSKNTLYLQMNSL RAEDTAVYYCAR | DDRSCSRTSC----------PYYYYGLDV | WGQGT TVTVS S |
| iPS:4 36726 | 21-225_152G5 | VH3j3-33/D4|4-23|RF2/J H6 | QVQLVES-GGGVVQPGRSLRL SCAASG-FTFS | D-----YGMH | WVRQAPGK GLEWVA | LIWYD----GSNKYYADS VKG | RFTISRDNSKNTLYLQMNSL RAEDTAVYYCAR | DDRSCSRTSC----------PYYYYGLDV | WGQGT TVTVS S |
| iPS:4 36732 | 21-225_152B12 | VH3j3-33/D4|4-23|RF2/J H6 | QVQVVES-GGGVVQPGRSLRL SCAASG-FTFS | D-----YGMH | WVRQAPGK GLEWVA | LIWYD----GSNKYYADS VKD | RFTISRDNSKNTLYLQMNSL RAEDTAVYYCAR | DDRSCSRTSC----------PYYYYGLDV | WGQGT TVTVS S |
| iPS:4 36734 | 21-225_153A8 | VH3j3-33/D4|4-23|RF2/J H6 | QVQLMES-GGGVVQPGRSLRL SCAASG-FTFS | D-----YGMH | WVRQAPGK GLEWVA | LIWYD----GSNKYYADS VKG | RFTISRDNSKNTLYLQMNSL RAEDTAVYYCAR | DDRSCSRTSC----------PYYYYGLDV | WGQGT TVTVS S |
| iPS:4 36736 | 21-225_153E8 | VH3j3-33/D4|4-23|RF2/J H6 | QVQLVES-GGGVVQPGRSLRL SCAASG-FTLS | N-----YGMH | WVRQAPGK GLEWVA | VIWFD----GSNKYYVDS VKG | RFTISRDNSKNTLYLQMNSL RAEDTAVYYCAR | DRVEGSGTP----------YYYYGMDV | WGQGT TVTVS S |
| iPS:4 36756 | 21-225_146A10 | VH3j3-33/D4|4-23|RF2/J H6 | QVQLEES-GGGVVQPGRSLRL SCAASG-FTFS | G-----YGMH | WVRQAEGK GLEWMT | LIRYD----GSGKNYADS VKG | RFTISRDNSKNTLYLQMNSL RAEDTAVYYCAR | DRVFCSTSCL----------SIYYYGMDV | WGQGT TVTVS S |
| iPS:4 36766 | 21-225_158D10 | VH3j3-33/D4|4-23|RF2/J H6 | QVQLVES-GGGVVQPGRSLRL SCAASG-FTFS | S-----YGMH | WVRQAEGK GLEWVA | VIWYD----GSNKYYADS VKG | RFTISRDNSKNTLYLQMNSL RAEDTAVYYCAR | DRVSCSSTSC----------PYYYYGMDV | WGQGT TVTVS S |
| iPS:4 36768 | 21-225_159H8 | VH3j3-33/D4|4-23|RF2/J H6 | QVQLVES-GGGVVQPGRSLRL SCAASG-FTFS | T-----YGMH | WVRQAEGK GLEWVA | VIWYD----GSNKYYADS VKG | RFTISRDNSKNTLYLQMNSL RAEDTAVYYCAR | DRVSCSSTSC----------PYYYYGMDV | WGQGT TVTVS S |
| iPS:4 36770 | 21-225_160B12 | VH3j3-33/D4|4-23|RF2/J H6 | QVQLVES-GGGVVQPGRSLRL SCAASG-FTFS | S-----YGMH | WVRQAPGK GLEWVA | VIWYD----GSNKYYADS VKG | RFTISRDNSKNTLYLQMNSL RAEDTAVYYCAR | DRVSCSSTSC----------PYYYYGMDV | WGQGT TVTVS S |

Figure 51 (Continued)

| | | | | | | | | |
|---|---|---|---|---|---|---|---|---|
| iPS:4 36782 | 21-225_166G11 | VH3J3-33\|D4\|4-23\|RF2\|J H6 | QVQLVES-GGGVVQPGRSLRL SCAASG-FTFN | G-----YGMH | WVRQAPGK GLEWVA | VIWYD---GSNKYYADS VKG | RFTISRDISKNTLFLQMNSL TAEDTAVYYCAR | DDRYCSSPICH-----PYYYYGLDV | WGQGT TVTVS S |
| iPS:4 36794 | 21-225_170F1 | VH3J3-33\|D4\|4-23\|RF2\|J H6 | QVQLVES-GGGVVQPGRSLRL SCAASG-FTFS | G-----YGMN | WVRQAPGK GLEWVA | IIWYD---GNNKYYADS VKG | RFTISRDNSKNTLYLQMNSL RAEDTAVYYCAR | DRVYCSSTSCH-----PYYYYAMDV | WGQGT TVTVS S |
| iPS:4 36836 | 21-225_52H1 | VH3J3-33\|D4\|4-23\|RF2\|J H6 | QVQLVES-GGGVVQPGRSLRL SCAASG-FTFS | G-----YGMH | WVRQAPGK GLEWVA | VIWYD---GSNKYYADS VKG | RFTISRDISKNTLYLQMNSL RAEDTAVYYCAR | DRVYCSSSCS-----YYYYYGMDV | WGQGT TVTVS S |
| iPS:4 36922 | 21-225_78E9 | VH3J3-33\|D4\|4-23\|RF2\|J H6 | QVQLVES-GGGVVQPGRSLRL SCAASG-FTFS | S-----YGMH | WVRQAPGK GLEWVA | VIWYD---GNNKSYADS VKG | RFTISRDISKNTLYLQMNSL RAEDTAVYYCAR | DRDYCSSTSC-----PYYYYGMDV | WGQGT TVTVS S |
| iPS:4 36924 | 21-225_74B3 | VH3J3-33\|D4\|4-23\|RF2\|J H6 | QVQLVES-GGGVVQPGRSLRL SCAASG-FTFS | R-----YGMH | WVRQAPGK GLEWVA | VFWYD---GSNKDYADS VKG | RFTISRDNSKNTLYLQMNSL RAEDTAVYYCAR | DRDYCSSTSC-----PYYYYGMDV | WGQGT TVTVS S |
| iPS:4 36928 | 21-225_79E7 | VH3J3-33\|D4\|4-23\|RF2\|J H6 | QVQLVES-GGGVVQPGRSLRL SCAASG-FTFS | S-----YGMH | WVRQAPGK GLEWVA | VIWYD---GNNKSYADS VKG | RFTISRDISKNTLYLQMNSL RAEDTAVYYCAR | DRDYCSSTSC-----PYYYYGMDV | WGQGT TVTVS S |
| iPS:4 36932 | 21-225_92A4 | VH3J3-33\|D4\|4-23\|RF2\|J H6 | QVQLVES-GGGVVQPGRSLRL SCAASG-FTFS | S-----YGMH | WVRQAPGK GLEWVA | VIWYD---GNNKSYADS VKG | RFTIYRDISKNTLYLQMNSL RAEDTAVYYCAR | DRDYCSSTSC-----PYYYYGMDV | WGQGT TVTVS S |
| iPS:4 36936 | 21-225_97E6 | VH3J3-33\|D4\|4-23\|RF2\|J H6 | QVQLVES-GGGVVQPGRSLRL SCAASG-FTFS | S-----YGMH | WVRQAPGK GLEWVA | VIWYD---GNNKSYADS VKG | RFTISRDISQNTLYLQMNSL RAEDTAVYYCAR | DRDYCSSTSC-----PYYYYGMDV | WGQGT TVTVS S |
| iPS:4 37190 | 21-225_225A9 | VH3J3-33\|D4\|4-23\|RF2\|J H6 | QVQLVES-GGGVVQPGGSLRL SCAASG-FTFS | T-----YGMH | WVRLAPGK GLEWVA | VIWYD---GSNKYYADS VKG | RFTISRDISKNTLYLQMNSL RAEDTAVYYCAR | DNHYCSSTSCS-----PYYYFGMDV | WGQGT TVTVS S |
| iPS:4 37254 | 21-225_149F2 | VH3J3-33\|D4\|4-23\|RF2\|J H6 | QVQLGEA-GGGVVQPGRSLRL SCAASG-FTFS | R-----YGMH | WVRQAEGK GLEWVA | FIWYD---GSENYADS VKG | RFTISRVNSRNTLYLQMNSL RAEDTAVYYCAR | DRVEGSGTP-----YYYYGMDV | WGQGT TVTVS S |
| iPS:4 37256 | 21-225_150F11 | VH3J3-33\|D4\|4-23\|RF2\|J H6 | QVQLGEA-GGGVVQPGRSLRL SCAASG-FTFS | R-----YGMH | WVRQAEGK GLEWVA | FIWYD---GSENYADS VKG | RFTISRVNSRNTLYLQMNSL RAEDTAVYYCAR | DRVEGSGTP-----YYYYGMDV | WGQGT TVTVS S |
| iPS:4 51110 | 21-225_74C9 | VH3J3-33\|D4\|4-23\|RF2\|J H6 | QVQLVES-GGGVVQPGRSLRL SCAASG-FTFS | S-----YGMH | WVRQAPGK GLEWVA | VIWYD---GNNKSYADS VKG | RFTISRDISKNTLYLQMNSL RAEDTAVYYCAR | DRDYCSSTSC-----PYYYYGMDV | WGQGT TVTVS S |

Figure 51 (Continued)

| | | | | H CDR1 | H FR2 | H CDR2 | H FR3 | H CDR3 | H FR4 |
|---|---|---|---|---|---|---|---|---|---|
| iPS:3 92589 | 21-225_27H2 | VH3-33/D4/4-23/RF2/JH6 | QVQLVES-GGGVVQPGRSLRLSCAASG-FTFS | G-----YGMH | WVRQAPGK GLEWVA | VIWYD---GSNKYADS VKG | RFTISRDNSKNTLFLQMNSL RAEDTAVYYCAR | DRVYCSTSCS-------PYYYYGMDV | WGQGT TVTVS S |
| iPS:3 93166 | 21-225_27G6 | VH3-33/D4/4-23/RF2/JH6 | QVQLVES-GGGVVQPGRSLRLSCAASG-FTFS | G-----YGMH | WVRQAPGK GLEWVA | IIWYD---GSKKYNADS VKG | RFTISRDNSKNTLYLQMNSL RAEDTAVYYCAR | DRVYCSTSCS-------PYYYYGMDV | WGQGT TVTVS S |
| iPS:3 93198 | 21-225_28A11 | VH3-33/D4/4-23/RF2/JH6 | QVQLVES-GGGVVQPGRSLRLSCAASG-FTFS | G-----YGLH | WVRQAPGK GLEWVA | LIWYD---GNNTYYADS VKG | RFTISRDNSKNTLYLQMNSL RAEDTAVYYCAR | DRVYCSTSCS-------PYYYYGMDV | WGQGT TVTVS S |
| iPS:3 93204 | 21-225_8C12 | VH3-33/D4/4-23/RF2/JH6 | QVQLVES-GGGVVQPGRSLRLSCAASG-FTFG | S-----YGMH | WVRQAPGK GLEWVA | LIWYD---GSNKYADS VKG | RFTISRDNSKNTLYLQMNSL RAEDTAVYYCAR | DRVSCSSSCY-------PYYYYGMDV | WGQGT TVTVS S |
| | Germline | | | | | | | | |
| iPS:4 53447 | 21-225_65F10 | VH1-02/D4/4-11/RF2/JH4 | QVQLVQS-GAEVKKPGASVKVSCKASG-YTFT | G-----YHMH | WVRQAPGQ GLEWMG | WINPN---NGGTSYAQK FQD | RVNMTRDTSISTAYMELSRL RSDDTAVYYCAR | DSRS-----------SWDY | WGQGT LVTVS S |
| iPS:4 34145 | 21-225_55B1 | VH1-02/D4/4-11/RF2/JH4 | QVQLVQS-GAEVKKPGASVKVSCKASG-YTFT | G-----YYFH | WVRQAPGQ GLERMG | WIHPN---NNATNYAQK FQG | RVTMTRDTSISTAYMELSRL RSDDTAVYYCAR | DGRS-----------SFDY | WGQGT LVTVS S |
| iPS:4 34277 | 21-225_57A7 | VH1-02/D4/4-11/RF2/JH4 | QVQLVQS-GAEVKKPGASVKVSCKASG-YTFT | G-----YHIH | WVRQAPGQ DLEWMG | WIHPN---NRGTNYAQK FQG | RVTMTRDTSISTAYMELSRL RSDDTAVYYCAK | DGRS-----------GFDY | WGQGT LVTVS S |
| iPS:4 34389 | 21-225_66F11 | VH1-02/D4/4-11/RF2/JH4 | QVQLVQS-GAEVKKPGASVKVSCKASG-YTFT | G-----YHMH | WVRQAPGQ GLEWMG | WINPN---NGGTHYAQK FQD | RVTMTRDTSISTAYMELSRL RSDDTAVYYCAR | DSRS-----------SWDY | WGQGT LVTVS S |
| iPS:4 34423 | 21-225_70D1 | VH1-02/D4/4-11/RF2/JH4 | QVQLVQS-GAEVKKPGASVKVSCKASG-YTFT | G-----YHMH | WVRQAPGQ GLERMG | WINPN---SNATNYAQK FQG | RVTMTRDTSISTAYMELSRL RSDDTAVYYCAR | DSIS-----------SWDY | WGQGT LVTVS S |
| iPS:4 37234 | 21-225_64E2 | VH1-02/D4/4-11/RF2/JH4 | QVQLVQS-GAEVKKPGASVKVSCKASG-YTFT | G-----YYMH | WVRQAPGQ GLEWMG | WINPN---NNGTNYAQK FQG | RVTMTRDTSISTAYMELSRL RSDDTAVYYCAR | DGSS-----------GFDY | WGQGT LVTVS S |
| | Germline | | | | | | | | |

Figure 51 (Continued)

| | | | H FR1 | H CDR1 | H FR2 | H CDR2 | H FR3 | H CDR3 | H FR4 |
|---|---|---|---|---|---|---|---|---|---|
| iPS:4 53449 | 21-225_208A2 | VH4J4-59/D7J7-27/RF1/JH4 | QVQLQES-GPGLVKPSETLSLNCTVSG-GSIR | S------YYWS | WIRQPAGK GLEWIG | RIYT----SGSTDYNPS LKS | RITMSVDTSKNQFSLKLSSV TAADTAVYYCAR | GFGD------------------WDY | WGQGT LVTVS S |
| iPS:4 35451 | 21-225_152D10 | VH4J4-59/D7J7-27/RF1/JH4 | QVQLQES-GPGLVKPSETLSL TCTVSG-GSIS | N------YYWS | WIRQPAGK GLEWIG | RIDT----SGITNYNPS LKS | RVTMSVDTSKNQFSLKLISV TAADTAVYYCAR | EGGLGA----------TFFDY | WGQGT LVTVS S |
| iPS:4 35467 | 21-225_153B9 | VH4J4-59/D7J7-27/RF1/JH4 | QVQLQES-GPGLVKPSETLSL TCTVSG-GSIS | S------YYWS | WIRQPAGK GLEWIG | RIDT----SGITNYNPS LKS | RVTMSVDTSKNQFSLKLISV TAADTAVYYCAR | EGGVGA----------TYFDY | WGQGT LVTVS S |
| iPS:4 35545 | 21-225_158F4 | VH4J4-59/D7J7-27/RF1/JH4 | QVQLQES-GPGLVKPSETLSL NCTVSG-GSIS | S------HFWS | WIRQPAGK GLEWIG | RIYT----SGTNYTPS LKS | RVTMSVDTSKNQFSLKLSSV TAADTAVYYCAR | LSSG------------------MFDY | WGQGT LVTVS S |
| iPS:4 35665 | 21-225_169F2 | VH4J4-59/D7J7-27/RF1/JH4 | QVQLQES-GPGLVKPSETLSL TCTVSG-GSIS | S------YYWS | WIRQPAGK GLEWIG | RIDT----SGITNYNPS LKS | RVTMSIDTSKSQISLKLSSV TAADTAVYYCAR | EGGVGA----------TYFDY | WGQGT LVTVS S |
| iPS:4 35671 | 21-225_169H5 | VH4J4-59/D7J7-27/RF1/JH4 | QVQLQES-GPGLVKPSETLSL TCTVSG-GSIS | S------YYWS | WIRQPAGK GLEWIG | RIDT----SGITNYNPS LKS | RVTMSVDTSKSQISLKLSSV TAADTAVYYCAR | EGGVGA----------TYFDY | WGQGT LVTVS S |
| iPS:4 36354 | 21-225_210G10 | VH4J4-59/D7J7-27/RF1/JH4 | QVQLQES-GPGLVKPSETLSL NCTVSG-GSIR | S------YYWS | WIRQPAGK GLEWIG | RIYT----SGSTDYNPS LKS | RVTMSVDTSKNQFSLKLSSV TAADTAVYYCAR | GFGD------------------WDY | WGQGT LVTVS S |
| VH4J4-34D4J4-17/RF2/JH6 | | Germline | | | | | | | |
| iPS:4 68810 | 21-225_74D5 | VH4J4-34D4J4-17/RF2/JH6 | QVQLQQW-GAGLLKPSETLSL TCAVNG-GPFS | G------CYWS | WIRQPPGK GLEWIG | EINY----SGRTNFNPS LKS | RVTISVDTSKNQFSLKLSSV TAADTAVYYCAR | DYGG------------------MDV | WGQGT TVTVS S |
| iPS:4 68832 | 21-225_76H10 | VH4J4-34D4J4-17/RF2/JH6 | QVQLQQW-GAGLLKPSETLSL TCAVNG-GPFS | G------CYWS | WIRQPEGK GLEWIG | EINY----SGRTNFNPS LKS | RVTISVDTSKNQFSLKLSSV TAADTAVYYCAR | DYGG------------------MDV | WGQGT TVTVS S |
| iPS:4 68834 | 21-225_94G10 | VH4J4-34D4J4-17/RF2/JH6 | QVQLQQW-GAGLLKPSETLSL TCAVNG-GPFS | G------CYWS | GIRQPPGK GREWIG | EINY----SGRTNFNPS LKS | RVTISVDTSKNQFSLKLSSV TAADTAVYYCAR | DYGG------------------MDV | WGQGT TVTVS S |
| iPS:4 68838 | 21-225_80E12 | VH4J4-34D4J4-17/RF2/JH6 | QVQLQQW-GAGLLKPSETLSL TCAVNG-GPFS | G------CYWS | WIRQPPGK GLEWIG | EINY----SGRTNFNPS LKS | RVTISVDTSKNQFSLKLSSV TAADTAVYYCAR | DYGG------------------MDV | WGQGT TVTVS S |

Figure 51 (Continued)

| ID | Clone | V gene | FR1 | CDR1 | FR2 | CDR2 | FR3 | CDR3 | FR4 |
|---|---|---|---|---|---|---|---|---|---|
| iPS:4 68820 | 21-225_76E10 | VH4|4-34|D4|4-17|RF2|J H6 | QVQLQQW-GAGLLKPSETLSL TCAVNG-GPFS | G------SYWS | WIRQPPGK GLEWIG | EINY----- SGRTNFNPS LKS | RVTISVDTSKNQFSLKLSSV TAADTAVYYCAR | DYGG----------MDV | WGQGT TVTVS S |
| iPS:4 34473 | 21-225_76D1 | VH4|4-34|D4|4-17|RF2|J H6 | QVQLQQW-GAGLLKPSETLSL TCAVYS-GSFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34495 | 21-225_74B2 | VH4|4-34|D4|4-17|RF2|J H6 | QVQLQQW-GAGLLKPSEPLSL TCAVYS-GSFS | G------PYWS | WIRQPPGK GLEWIG | EINH----- SGSTNYNPS LTS | RVTISVDTSKNQFSLKLITSV TAADSAVYYCAR | DYGG----------LDV | WGQGT TVTVS S |
| iPS:4 34497 | 21-225_76A4 | VH4|4-34|D4|4-17|RF2|J H6 | QVQLQQW-GAGLLKPSETLSL TCAVHG-GSFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34501 | 21-225_76G4 | VH4|4-34|D4|4-17|RF2|J H6 | QVQLQQW-GAGLLKPSETLSL TCAVHG-GSFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34507 | 21-225_74C5 | VH4|4-34|D4|4-17|RF2|J H6 | QVQLQQW-GAGLLKPSETLSL TCAVHG-GSFS | G------CYWS | WIRQPPGK GLEWIG | EINH----- SGCTNFNPS LKS | RVTISVDTSKNQFSLKLSSV TAADTAVYYCAR | DYGG----------MDV | WGQGT TVTVS S |
| iPS:4 34523 | 21-225_75C3 | VH4|4-34|D4|4-17|RF2|J H6 | QVQLQQG-GAGLLKPSEPLSL TCAVYG-GSFS | G------CYWS | WIRQPPGK GLEWIG | EINY----- SGRTNYNPS LKS | RVTISVDTSKNQFSLKLSSV TAADTAVYYCAR | DYGG----------MDV | WGQGT TVTVS S |
| iPS:4 34533 | 21-225_85F7 | VH4|4-34|D4|4-17|RF2|J H6 | QVQLQQW-GAGLLKPSEPLSL TCAVYG-GSFS | G------PYWS | WIRQPPGK GLEWIG | EINH----- SGSTNYNPS LKS | RVTISVDTSKNQFSLKLSSV TAADTAVYYCAR | DYGG----------LDV | WGQGT TVTVS S |
| iPS:4 34547 | 21-225_74H5 | VH4|4-34|D4|4-17|RF2|J H6 | QVQLQQW-GAGLLKPSETLSL TCAVHG-GPFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34559 | 21-225_74D11 | VH4|4-34|D4|4-17|RF2|J H6 | QVQLQQW-GAGLLKPSETLSL TCAVHG-GSFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34561 | 21-225_77G1 | VH4|4-34|D4|4-17|RF2|J H6 | QVQLQQW-GAGLLKPSETLSL TCAVHG-GSFS | G------CYWS | WIRQPPGK GLEWIG | EINH----- SGSTNYNPS LKS | RVTISVDTSKNQFSLKLSSV TAADTAVYYCAR | DYGG----------MDV | WGQGT TVTVS S |
| iPS:4 34565 | 21-225_75B10 | VH4|4-34|D4|4-17|RF2|J H6 | QVQLQQW-GAGLLKPSETLSL KCDVYG-GSFS | G------YYWS | WIRQPPGK GLEWIG | EINH----- SGSTNYNPS LKS | RVTISVDTSKNQFSLKLSSV TAADTAVYYCAR | DYGG----------LDV | WGQGT TVTVS S |

Figure 51 (Continued)

| | | | | | | | | |
|---|---|---|---|---|---|---|---|---|
| iPS:4 34579 | 21-225_77F7 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34581 | 21-225_74B12 | VH4J4-34/D4/4-17/RF2/J H6 | QVQLQQW-GAGPLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34585 | 21-225_75A12 | VH4J4-34/D4/4-17/RF2/J H6 | QVQLQQG-GAGPLKPSETLSL TCAVYG-GSFS | G------CYWS | WIRQPPGK GLEWIG | EINY---- SGRTNYNPS LKS | RVTISVDTSKNQFSLKLSSV TAADTAVYYCAR | DYGG---------- | -----MDV | WGQGT TVTVS S |
| iPS:4 34595 | 21-225_77A10 | VH4J4-34/D4/4-17/RF2/J H6 | QVQLQQG-GAGLLKPSETLSL TCAVYG-GSFS | G------CYWS | WIRQPPGK GLEWIG | EINY---- SGRTNYNPS LKS | RVTISVDTSKNQFSLKLSSV TAADTAVYYCAR | DYGG---------- | -----MDV | WGQGT TVTVS S |
| iPS:4 34611 | 21-225_77C12 | VH4J4-34/D4/4-17/RF2/J H6 | QVQLQQW-GAGLLKPSETLSL TCAVYG-GAFS | G------SYWS | WIRQSPGK GLEWIG | EINY---- RGSTNYNPS LKS | RVTISVDTSKNQFSLNLSSV TAADTAVYYCAR | DYGG---------- | -----MDV | WGQGT TVTVS S |
| iPS:4 34657 | 21-225_79G1 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34663 | 21-225_79F3 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34687 | 21-225_75A5 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34691 | 21-225_75G7 | VH4J4-34/D4/4-17/RF2/J H6 | QVQLQQW-GAGLLKPSETLSL TCTVYG-GAFS | G------SYWS | WIRQSPGK GLEWIG | EINY---- SGSTNYNPS LKS | RVTISVDTSKNQFSLNLSSV TAADTAVYYCAR | DYGG---------- | -----MDV | WGQGT TVTVS S |
| iPS:4 34693 | 21-225_79F11 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34699 | 21-225_79G12 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |
| iPS:4 34701 | 21-225_80A1 | VH4J4-34/D4/4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG---------- | -----MDV | WGQGT TVTVS S |

Figure 51 (Continued)

| | | | | | | | | |
|---|---|---|---|---|---|---|---|---|
| iPS:4 34703 | 21-225_80C1 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34709 | 21-225_80E3 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34715 | 21-225_80D5 | VH4J4-34/D4J4-17/RF2/J H6 | QVQLQQW-GAGLLKPSELLSL TCAVHG-GSFS | G------PYWS | WIRQPPGK GLEWIG | EINH---- SGSTNYNPS LKS | RVTISVDTSKNQFSLKLISV TAADMAVYYCAR | DYGG-------------- | ----LDV | WGQGT TVTVS S |
| iPS:4 34725 | 21-225_80H7 | VH4J4-34/D4J4-17/RF2/J H6 | QVQLQQW-GAGLLKPSETLSL TCAVYV-GSFS | G------SYWS | WIRQPPGK GLEWIG | EINQ---- SGRTNYNPS LKS | RVTISVDTSKNQFSLKLSSV TAADTAVYYCAR | DYGG-------------- | ----IDV | WGQGT TVTVS S |
| iPS:4 34743 | 21-225_74A4 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34751 | 21-225_80H12 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34759 | 21-225_81C5 | VH4J4-34/D4J4-17/RF2/J H6 | QVQLQQW-GAGLLKPSETLSL TCAVHG-GSFS | G------CYWS | WIRQPPGK GLEWIG | EINY---- RGSTNYNPS LKS | RVTISVDTSKNQFSLKLSSV TAADTAVYYCAR | DYGG-------------- | ----MDV | WGQGT TVTVS S |
| iPS:4 34773 | 21-225_75D9 | VH4J4-34/D4J4-17/RF2/J H6 | QVQLQQW-GAGLLKPSETLSL TCAVHG-GSFS | G------PYWS | WIRQPPGK GLEWIG | EINH---- SGSTNYNPS LKS | RVTISVDTSKNQFSLNLSSV TAADTAVYYCAR | DYGG-------------- | ----MDV | WGQGT TVTVS S |
| iPS:4 34777 | 21-225_81C11 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34809 | 21-225_74F5 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34821 | 21-225_83G1 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |
| iPS:4 34839 | 21-225_83B7 | VH4J4-34/D4J4-17/RF2/J H6 | QVQLQQW-GAGLLKPSETLSL TCAVHG-GSFS | G------CYWS | WIRQPPGK GLEWIG | EINH---- SGSTNYNPS LKS | RVTISVDTSKNQFSLKLSSV TAADTAVYYCAR | DYGG-------------- | ----MDV | WGQGT TVTVS S |

Figure 51 (Continued)

| | | | | | | | | | |
|---|---|---|---|---|---|---|---|---|---|
| iPS:4 34869 | 21-225_84E12 | VH4J4-34/D4J4-17/RF2/JH6 | QVQLQQW-GAGLLKPSETLSL TCAVYG-GSFS | G-----SYWS | WIRQPPGK GLEWIG | EINQ----SGRTNYNPS LKS | RVTISVDTSKNQFSLKLSSV TAADTAVYYCAR | DYGG-------- | -------iDV | WGQGT TVTVS S |
| iPS:4 34879 | 21-225_85A3 | VH4J4-34/D4J4-17/RF2/JH6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG-------- | -------MDV | WGQGT TVTVS S |
| iPS:4 34881 | 21-225_85B4 | VH4J4-34/D4J4-17/RF2/JH6 | QVQLQQW-GAGLLKPSETLSL TCAVYG-GSFS | G-----CYWS | WIRQPPGK GLEWIG | EINH----SGSTNYNPS LKS | RVTISVDTSKNQFSLKLSSV TAADTAVYYCAR | DYGG-------- | -------MDV | WGQGT TVTVS S |
| iPS:4 34887 | 21-225_85D6 | VH4J4-34/D4J4-17/RF2/JH6 | QVQLQQG-GAGPLKPSETLSL TCAVYG-GSFS | G-----CYWS | WIRQPPGK GLEWIG | EINY----SGRTNYNPS LKS | RVTISVDTSKNQFSLKLSSV TAADTAVYYCAR | DYGG-------- | -------MDV | WGQGT TVTVS S |
| iPS:4 34895 | 21-225_74H7 | VH4J4-34/D4J4-17/RF2/JH6 | QVQLQQW-GAGLLKPSEPLSL TCAVYG-GSFS | G-----PYWS | WIRQPPGK GLEWIG | EINH----SGSTNYNPS LKS | RVTISVDTSKNQFSLKLTSV TAADTAVYYCAR | DYGG-------- | -------LDV | WGQGT TVTVS S |
| iPS:4 34899 | 21-225_85B9 | VH4J4-34/D4J4-17/RF2/JH6 | QVQLQQW-GAGLLKPSETLSL TCAVHG-GPFS | G-----CYWS | WIRQPPGK GLEWIG | EINH----SGSTNFNPS LKS | RVTISVDTSKNQFSLKLSSV TAADTAVYYCAR | DYGG-------- | -------MDV | WGQGT TVTVS S |
| iPS:4 34907 | 21-225_85G10 | VH4J4-34/D4J4-17/RF2/JH6 | QVQLQQR-GAGLLKPSETLSL TCAVYG-GSFS | G-----CYWS | WIRQPPGK GLEWIG | EINH----SGRTNYNPS LKS | RVTISVDTSKNQFSLKLTSV TAADTAVYYCAR | DYGG-------- | -------LDV | WGQGT TVTVS S |
| iPS:4 34913 | 21-225_86C1 | VH4J4-34/D4J4-17/RF2/JH6 | QVQLQQW-GAGLLKPSETLSL TCAVYG-GSFS | G-----CYWS | WIRQPPGK GLEWIG | EINH----SGSTNYNPS LKS | RVTISVDTSKNQFSLKLSSV TAADTAVYYCAR | DYGG-------- | -------MDV | WGQGT TVTVS S |
| iPS:4 34921 | 21-225_86E4 | VH4J4-34/D4J4-17/RF2/JH6 | QVQLQQW-GAGLLKPSETLSL TCAVHG-GSFS | G-----CYWS | WIRQPPGK GLEWIG | EINH----SGRTNYNPS LKS | RVTISVDTSKNQFSLKLSSV TAADTAVYYCAR | DYGG-------- | -------MDV | WGQGT TVTVS S |
| iPS:4 34939 | 21-225_86C11 | VH4J4-34/D4J4-17/RF2/JH6 | QVQLQQW-GAGLLKPSETLSL TCAVYG-GSFS | G-----CYWS | WIRQPPGK GLEWIG | EINH----SGSTNYNPS LKS | RVTISVDTSKDQFSLKLSSV TAADTAVYYCAR | DYGG-------- | -------MDV | WGQGT TVTVS S |
| iPS:4 34943 | 21-225_87H1 | VH4J4-34/D4J4-17/RF2/JH6 | QVQLQPW-GAGLLKPSETLSL TCAVYG-GSFS | G-----YYWS | WIRQPPGK GLEWIG | EINH----SGRTNYNPS LKS | RVTISVDTSKNQFSLKLSSV TAADTAVYYCAR | DYGG-------- | -------LDV | WGQGT TVTVS S |
| iPS:4 34945 | 21-225_87E5 | VH4J4-34/D4J4-17/RF2/JH6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG-------- | -------MDV | WGQGT TVTVS S |

Figure 51 (Continued)

| | | | | | | | | | |
|---|---|---|---|---|---|---|---|---|---|
| iPS:4 34955 | 21-225_87C9 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG---------- | -----MDV | WGQGT TVTVS S |
| iPS:4 34961 | 21-225_87A12 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG---------- | -----MDV | WGQGT TVTVS S |
| iPS:4 34969 | 21-225_88H1 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG---------- | -----MDV | WGQGT TVTVS S |
| iPS:4 34981 | 21-225_88E7 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG---------- | -----MDV | WGQGT TVTVS S |
| iPS:4 34983 | 21-225_88F7 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG---------- | -----MDV | WGQGT TVTVS S |
| iPS:4 34995 | 21-225_88G9 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG---------- | -----MDV | WGQGT TVTVS S |
| iPS:4 34999 | 21-225_75A8 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDTSKNQFSLKLSSV TAADTAVYYCAR | DYGG---------- | -----MDV | WGQGT TVTVS S |
| iPS:4 35013 | 21-225_89D5 | VH4J4-34/D4J4-17/RF2/J H6 | QVQLQQW-GAGLLKPSETLSL TCAVHG-GSFS | G-----CYWS | WIRQPPGK GLEWIG | EINY----SGSTNYNPS LKS | RVTISVDISKNQFSLKLSSV TAADTAVYYCAR | DYGG---------- | -----MDV | WGQGT TVTVS S |
| iPS:4 35015 | 21-225_89H5 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNFNPS LKS | RVTISADISKNQFSLKLSSV TAADTAVYYCAR | DYGG---------- | -----MDV | WGQGT TVTVS S |
| iPS:4 35025 | 21-225_89E10 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG---------- | -----MDV | WGQGT TVTVS S |
| iPS:4 35029 | 21-225_89A11 | VH4J4-34/D4J4-17/RF2/J H6 | QVQLQPW-GAGLLKPSETLSL TCAVYG-GSFS | G-----YYWS | WIRQPPGK GLEWIG | EINH----SGRTSYNPS LKS | RVTISVDTSKNQFSLKLSSV TAADTAVYYCAR | DYGG---------- | -----LDV | WGQGT TVTVS S |
| iPS:4 35039 | 21-225_90G4 | VH4J4-34/D4J4-17/RF2/J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG---------- | -----MDV | WGQGT TVTVS S |

Figure 51 (Continued)

| | | | | | | | | |
|---|---|---|---|---|---|---|---|---|
| iPS:4 35041 | 21-225_90A5 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35043 | 21-225_90G5 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35055 | 21-225_90F10 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35073 | 21-225_91B2 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35075 | 21-225_91B3 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35077 | 21-225_91F3 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35079 | 21-225_91B4 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35089 | 21-225_91E9 | VH4J4-34/D4J4-17/RF2/JH6 | QVQLQQW-GAGLLKPSETLSLTCAVHG-GSFS | G------CYWS | WIRQPPGKGLEWIG | EINY----SGSTNYNPSLKS | RVTISVDTSKNQFSLNLISVTAADTAVYYCAR | DYGG----------- | -------LDV | WGQGTTVTVSS |
| iPS:4 35097 | 21-225_92B1 | VH4J4-34/D4J4-17/RF2/JH6 | QVQLQQW-GAGLLKPSETLSLTCAVYG-GSFS | G------SYWS | WIRQPPGKGLEWIG | EINY----RGSTNYNPSLKS | RVAISVDTSKNQFSLKLSSVTAADTAVYYCAR | DYGG----------- | -------MDV | WGQGTTVTVSS |
| iPS:4 35111 | 21-225_92D6 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35115 | 21-225_77C5 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |
| iPS:4 35171 | 21-225_93C2 | VH4J4-34/D4J4-17/RF2/JH6 | QVQLQQW-GAGLLKPSETLSLTCAVHG-GSFS | G------CYWS | WIRQPPGKGLEWIG | EINH----SGSTNYNPSLKS | RVTISVDTSKNQFSLKLSSVTAADTAVYYCAR | DYGG----------- | -------MDV | WGQGTTVTVSS |

Figure 51 (Continued)

| | | | | | | | | |
|---|---|---|---|---|---|---|---|---|
| iPS:4 35177 | 21-225_93E4 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35195 | 21-225_94D3 | VH4|4-34|D4|4-17|RF2|J H6 | QVQLQQG-GAGPLKPSETLSL TCAVYG-GSFS | G-----CYWS | WIRQPPGK GLEWIG | EINY----SGRTNYNPS LKS | RVTISVDTSKNQFSLKLSSV TAADTAVYYCAR | DYGG------- | ----MDV | WGQGT TVTVS S |
| iPS:4 35217 | 21-225_94F12 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35219 | 21-225_95D2 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35235 | 21-225_95F9 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35237 | 21-225_95G9 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35239 | 21-225_95H10 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35273 | 21-225_97A2 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 35281 | 21-225_97E5 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 37324 | 21-225_75C2 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 37328 | 21-225_75D3 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |
| iPS:4 37332 | 21-225_75F3 | VH4|4-34|D4|4-17|RF2|J H6 | QVQLQQW-GAGLLKPSETLSL TCAVHG-GSFS | G-----CYWS | WIRQPPGK GLEWIG | EINH----SGSTNYNPS LKS | RVTISVDISKNQFSLKLSSV TAADTAVYYCAR | DYGG------- | ----MDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 37344 | 21-225_75G12 | VH4|4-34|D4|4-17|RF2|JH6 | QVQLQQW-GAGLLKPSETLSLTCAVHG-GSFS | G-----CYWS | WIRQPPGKGLEWIG | EINH----SGSTNYNPSLKS | RVTISVDTSKNQFSLKLSSVTAADTAVYYCAR | DYGG----------MDV | WGQGTTVTVSS |
| iPS:4 37350 | 21-225_74A3 | VH4|4-34|D4|4-17|RF2|JH6 | QVQLQQW-GAGLLKPSETLSLTCAVHG-GSFS | G-----CYWS | WIRQPPGKGLEWIG | EINH----SGSTNYNPSLKS | RVTISVDTSKNQFSLKLSSVTAADTAVYYCAR | DYGG----------MDV | WGQGTTVTVSS |
| iPS:4 37369 | 21-225_74D6 | VH4|4-34|D4|4-17|RF2|JH6 | QVQLQQW-GAGLLKPSETLSLTCAVHG-GSFS | G-----CYWS | WIRQPPGKGLEWIG | EINH----SGSTNYNPSLKS | RVTISVDTSKNQFSLKLSSVTAADTAVYYCAR | DYGG----------MDV | WGQGTTVTVSS |
| | Germline VH3|3-33|D4|4-17|RF2|JH6 | | QVQLVES-GGGVVQPGRSLRLSCAASG-FTFS | S-----YGMH | WVRQAPGKGLEWVA | VIWYD---GSNKYADSVKG | RFTISRDNSKNTLYLQMNSLRAEDTAVYYCAR | DGGSGWYGLDV | WGQGTTVTVSS |
| iPS:4 68814 | 21-225_223D11 | VH3|3-33|D4|4-17|RF2|JH6 | QVQLVES-GGGVVQPGRSLRLSCAASG-FTFS | N-----YGMD | WVRQAPGKGLEWVA | VIWYD---GSNDYADSVKG | RFTISRDNSKNTLFLQMNSLRAEDTAVYYCAR | DRGIGY--------NDMDV | WGQGTTVTVSS |
| iPS:4 34621 | 21-225_74D1 | VH3|3-33|D4|4-17|RF2|JH6 | QVQLVES-GGGVVQPGRSLRLSCAASG-FTFS | S-----YGMH | WVRQAPGKGLEWVA | VIWYD---GSNKYHADSVKG | RFTISRDNSKNTLYLQMNSLRAEDTAMYYCAR | DEGFGRFD------YYNYGMDV | WGQGTTVTVSS |
| iPS:4 34947 | 21-225_87B7 | VH3|3-33|D4|4-17|RF2|JH6 | QVQLVES-GGGVVQPGRSLRLSCAASG-FTFS | S-----YGMH | WVRQAPGKGLEWVA | VIWYD---GSNKNYADSVKG | RFTISRDNSKNTLYLQMNSLRAEDTAVYYCAR | DFGVGY--------YGMDV | WGQGTTVTVSS |
| iPS:4 35819 | 21-225_190C11 | VH3|3-33|D4|4-17|RF2|JH6 | QVQLVES-GGGVVQPGRSLRLSCAASG-FTFS | S-----YGMH | WVRQAPGKGLEWVA | VIWYD---GSNKNYADSVKG | RFTISRDNSKNTLYLQMNSLRAEDTAVYYCAR | DQGVGY--------DGLDV | WGQGTTVTVSS |
| iPS:4 35825 | 21-225_190G11 | VH3|3-33|D4|4-17|RF2|JH6 | QVQLVES-GGGVVQPGRSLRLSCAASG-FTFS | I-----YGMH | WVRQAPGKGLEWVA | VIWYD---GSNKNYADSVKG | RFTISRDNSKNTLYLQMNSLRAEDTAVYYCAR | DQGVGY--------DGLDV | WGQGTTVTVSS |
| iPS:4 35837 | 21-225_198G3 | VH3|3-33|D4|4-17|RF2|JH6 | QVQLVES-GGGVVQPGRSLRLSCAASG-FTFS | T-----YGMH | WVRQAPGKGLEWVA | VIWYD---GTNKNYADSVKG | RFTISRDNSKNTLYLQMNSLRAEDTAVYYCAR | DQGVGY--------DGLDV | WGQGTTVTVSS |
| iPS:4 35845 | 21-225_191G1 | VH3|3-33|D4|4-17|RF2|JH6 | QVQLVES-GGGVVQPGRSLRLSCAASG-FTFS | S-----YGMH | WVRQAPGKGLEWVA | VIWYD---GSNEHYADSVKG | RFTISRDNSKNTLYLQMNSLRAEDTAVYYCAR | DRGVGY--------YGLDV | WGQGTTVTVSS |
| iPS:4 35859 | 21-225_190E6 | VH3|3-33|D4|4-17|RF2|JH6 | QVQLVES-GGGVVQPGRSLRLSCAASG-FTFS | S-----YGMH | WVRQAPGKGLEWVA | VIWYD---GSNKNYADSVKG | RFTISRDNSKNTLYLQMNSLRAEDTAVYYCAR | DQGVGY--------DGLDV | WGQGTTVTVSS |

Figure 51 (Continued)

| | | | | | | | | |
|---|---|---|---|---|---|---|---|---|
| iPS:4 35873 | 21-225_190G4 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAMYYCAR | DQGVGY----------DGLDV | WGQGT SVTVS S |
| iPS:4 35933 | 21-225_190F8 | VH3|3-33/D4|4-17|RF2|J H6 | QVQLVES-GGGVVQPGRSLRL SCAASG-FTFS | T-----YGMH | WVRQAPGK GLEWVA | VIWYD---GSNKNYADS VKG | RFTISRDNSKNTLYLQMNSL RAEDTAVYYCAR | DQGVGY----------DGLDV | WGQGT TVTVS S |
| iPS:4 35941 | 21-225_191E8 | VH3|3-33/D4|4-17|RF2|J H6 | QVQLVES-GGGVVQPGRSLRL SCAASG-FTFS | N-----YGMH | WVRQAPGK GLEWVA | IIMFD---GSNQYYADS VKG | RFTISRDNSKNTLYLQLNSL RAEDTAVYYCAR | AHGVYY----------YAMDV | WGQGT TVTVS S |
| iPS:4 35945 | 21-225_191A10 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAMYYCAR | DQGVGY----------DGLDV | WGQGT SVTVS S |
| iPS:4 35947 | 21-225_191E10 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY----------DGLDV | WGQGT SVTVS S |
| iPS:4 35957 | 21-225_191G12 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY----------DGLDV | WGQGT TVTVS S |
| iPS:4 35963 | 21-225_192D2 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNMLYLQMNSL RAEDTAVYYCAR | DRGVGY----------YGMDV | WGQGT TVTVS S |
| iPS:4 35971 | 21-225_192D3 | VH3|3-33/D4|4-17|RF2|J H6 | QVQLVES-GGGVVQPGRSLRL SCAASG-FTFS | S-----YGMH | WVRQAPGK GLEWVA | VLWYD---GTNKNYADS VKG | RFTISRDNSKNTLYLQMNSL RAEDTAVYYCAR | DRGVGY----------YGLDV | WGQGT TVTVS S |
| iPS:4 35979 | 21-225_192H4 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY----------YGMDV | WGQGT TVTVS S |
| iPS:4 35987 | 21-225_192G6 | VH3|3-33/D4|4-17|RF2|J H6 | QVQLVES-GGGVVQPGRSLRL SCAASG-FTFS | S-----YGMH | WVRQAEGK GLEWVA | VIWYD---GSNEHYADS VKG | RFTISRDNSKNTLYLQMNSL RAEDTAVYYCAR | DQGVGY----------DGLDV | WGQGT TVTVS S |
| iPS:4 35993 | 21-225_192C8 | VH3|3-33/D4|4-17|RF2|J H6 | QVQLVES-GGGVVQPGRSLRL SCAASG-FTFS | S-----YGMH | WVRQAEGK GLEWVA | VIWYD---GSNEHYADS VKG | RPMISRDNSKNTLYLQMNSL RAEDTAVYYCAR | DRGVGY----------YGMDV | WGQGT TVTVS S |
| iPS:4 35997 | 21-225_192G8 | VH3|3-33/D4|4-17|RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY----------DGLDV | WGQGT TVTVS S |

Figure 51 (Continued)

| | | | | | | | | | |
|---|---|---|---|---|---|---|---|---|---|
| iPS:4 36005 | 21-225_192H10 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAMYYCAR | DQGVGY--------EGLDV | WGQGT SVTVS S |
| iPS:4 36031 | 21-225_193C7 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAMYYCAR | DQGVGY--------DGLDV | WGQGT SVTVS S |
| iPS:4 36045 | 21-225_193A10 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DRGVGY--------YGLDV | WGQGT TVTVS S |
| iPS:4 36076 | 21-225_194H11 | VH3J3-33/D4J4-17/RF2/J H6 | QVQLVES-GGGVVQPGRSLRL SCAASG-FTFS | S-----YGMH | WVRQAPGK GLEWVA | VIWYD---GSNEHYADS VKG | RFTISRDNSKNTLSLQMNSL RAEDTAVYYCAR | DRGVGY--------YGLDV | WGQGT TVTVS S |
| iPS:4 36086 | 21-225_191G10 | VH3J3-33/D4J4-17/RF2/J H6 | QVQLVES-GGGVVQPGRSLRL SCAASG-FTFS | S-----YGMH | WVRQAPGK GLEWVA | VIWYD---GSNEHYADS VKG | RFTISRDNSKNTLYLQMNSL RAEDTAVYYCAR | DQGVGY--------DGLDV | WGQGT TVTVS S |
| iPS:4 36090 | 21-225_195A9 | VH3J3-33/D4J4-17/RF2/J H6 | QVQLVES-GGGVVQPGRSLRL SCAASG-FTFS | S-----YGMH | WVRQAPGK GLQWVA | VIWYD---GSNKNYADS VKG | RFTISRDNSKNTLYLQMNSL RAEDTAVYYCAR | DRGVGY--------YGLDV | WGQGT TVTVS S |
| iPS:4 36112 | 21-225_196C7 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DRGVGY--------YGLDV | WGQGT TVTVS S |
| iPS:4 36138 | 21-225_197F2 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAMYYCAR | DQGVGY--------DGLDV | WGQGT TVTVS S |
| iPS:4 36152 | 21-225_197B6 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNMLYLQMNSL RAEDTAMYYCAR | DQGVGY--------EGLDV | WGQGT SVTVS S |
| iPS:4 36173 | 21-225_197G12 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY--------DGLDV | WGQGT TVTVS S |
| iPS:4 36189 | 21-225_198B6 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY--------YGMDV | WGQGT TVTVS S |
| iPS:4 36201 | 21-225_199C5 | VH3J3-33/D4J4-17/RF2/J H6 | QVQLVES-GGGVVQPGRSLRL SCAASG-FTFS | S-----YGMH | WVRQAPGK GLEWVA | VIWYD---GSNKNYADS VKG | RFTISRDNSKNTLYLQMNSL RAEDTAVYYCAR | DQGVGY--------YGMDV | WGQGT TVTVS S |

Figure 51 (Continued)

| | | | | | | | | | |
|---|---|---|---|---|---|---|---|---|---|
| iPS:4 36203 | 21-225_199A6 | VH3J3-33/D4J4-17/RF2/J H6 | QVQLVES-GGGVVQPGRSLRL SCAASG-FTFS | N-----YGMH | WVRQAPGK GLEWVA | IIWFD--- GSNQYIADS VKG | RFTISRDNSKNTLYLQINSL RAEDTAVYYCAR | AHGVYY------- --------YAMDV | WGQGT TVTVS S |
| iPS:4 36282 | 21-225_204G6 | VH3J3-33/D4J4-17/RF2/J H6 | QVQLVES-GGGVVQPGRSLRL SCTASG-FTFS | S-----YGMH | WVRQAPGK GLEWVA | VIWYD--- GSNKNYADS VKG | RFTISRDNSKNTLYLQMNSL RAEDTAVYYCAR | DRGVGY------- --------DGMDV | WGQGT TVTVS S |
| iPS:4 36296 | 21-225_205F5 | VH3J3-33/D4J4-17/RF2/J H6 | QVQLVES-GGGVVQPGRSLRL SCAASG-FTFS | R-----YGMH | WVRQAPGK GLEWVA | VIWYD--- GSNENYVDS VKG | RFTISRDISKRMLFLQMNSL RTDDTAVYYCAR | DMGIGY------- --------YGMDV | WGQGT TVTVS S |
| iPS:4 36324 | 21-225_207G6 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNKNYAES VKG | RFTISRDNSKNTLYLQMNSL RAEDTAVYYCAR | DAGIGY------- --------YGIDV | WGQGT TVTVS S |
| iPS:4 36364 | 21-225_211A11 | VH3J3-33/D4J4-17/RF2/J H6 | QVQLVGS-GGGVVQPGRSLRL SCAASG-FTFS | S-----YGMH | WVRQAPGK GLEWVA | VLWFD--- GSNRNYADS VKG | RFTISRDNSKNTLYLQMNSL RAEDTAVYYCAR | DRGVGY------- --------YGTDV | WGQGT TVTVS S |
| iPS:4 36372 | 21-225_211A8 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNKHYADS VKG | RFTISRDNSKKTLYLQMNSL RAEDTAVYYCAR | DHGVGY------- --------YGMDV | WGQGT TVTVS S |
| iPS:4 36376 | 21-225_212E6 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNKNYVDS VKG | RFTISRDNSKNTLYLQMNSL RAEDTAVYYCAR | DYGVGY------- --------YGTDV | WGQGT TVTVS S |
| iPS:4 36378 | 21-225_212D7 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNKNYADS VKG | RFTISRDNSKNLSLQMNSL RAEDTAVYYCAR | DYGVGY------- --------YGTDV | WGQGT TVTVS S |
| iPS:4 36380 | 21-225_212H9 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNEHYADS VKG | RFTISRDNSKKTLYLQMNSL RAEDTAVYYCAR | DHGVGY------- --------YGMDV | WGQGT TVTVS S |
| iPS:4 36384 | 21-225_212F10 | VH3J3-33/D4J4-17/RF2/J H6 | QVQLVES-GGGVVQPGRSLRL SCAASG-FTFS | R-----YGMH | WVRQAEGK GLEWVA | VIWYD--- GSNKHYADS VKG | RFTISRDNSKNTLYLQMNSL RGEDTAVYYCAR | DRGVGY------- --------NGMDV | WGQGT TVTVS S |
| iPS:4 36390 | 21-225_213D2 | VH3J3-33/D4J4-17/RF2/J H6 | QVQLVES-GGGVVQPGRSLRL SCAASG-FTFS | S-----YGMH | WVRQAPGK GLEWVA | VIWYD--- GSNKNYADS VKG | RFTISRDNSKNTLSLQMNSL RAEDTAVYYCAR | DYGVGY------- --------YGTDV | WGQGT TVTVS S |
| iPS:4 36394 | 21-225_213C4 | VH3J3-33/D4J4-17/RF2/J H6 | QVQLVES-GGGVVQPGRSLRL SCAISG-FTFS | S-----YGMH | WVRQAPGK GLEWVA | VIWYD--- GSNKHYADS VKG | RFTISRDNSKNTLYLQMNSL RAEDTAVYYCAR | DYGVGY------- --------DGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36398 | 21-225_213B8 | VH3|3-33/D4|4-17/RF2|J H6 | QVQLVES-GGGVVQPGRSLRL SCAASG-FTFS | S-----YGMH | WVRQAPGK GLEWVA | VIWYD---GSNKHYADS VKG | RFTISRDNSKNTLYLQMNSL RAEDTAVYYCAR | DYGVGY------YGTDV | WGQGT TVTVS S |
| iPS:4 36404 | 21-225_214C3 | VH3|3-33/D4|4-17/RF2|J H6 | QVQLVES-GGGVVQPGRSLRL SCAASG-FTFS | S-----YGMH | WVRQAPGK GLEWVA | VIWYD---GSNKNYGDS VKG | RFTISRDNSKNTLYLQMNSL RAEDTAVYYCAR | DRGVGY------DGMDV | WGQGT TVTVS S |
| iPS:4 36410 | 21-225_212E10 | VH3|3-33/D4|4-17/RF2|J H6 | QVQLVES-GGGVVQPGRSLRL SCAASG-FTFS | S-----YGMH | WVRQAPGK GLEWVA | VIWYD---GSNKNTLSQMNSL VKG | RFTISRDNSKNTLSLQMNSL RAEDTAVYYCAR | DYGVGY------YGTDV | WGQGT TVTVS S |
| iPS:4 36420 | 21-225_215B5 | VH3|3-33/D4|4-17/RF2|J H6 | QVQLVES-GGGVVQPGRSLRL SCAASG-FTFS | S-----YGMH | WVRQAPGK GLEWVA | VIWYD---GSNKNYADS VKG | RFTISRDNSKNTLSLQMNSL RAEDTAVYYCAR | DYGVGY------YGTDV | WGQGT TVTVS S |
| iPS:4 36422 | 21-225_215D6 | VH3|3-33/D4|4-17/RF2|J H6 | QVQLVES-GGGVVQPGRSLRL SCAASG-FTFS | S-----YGMH | WVRQAPGK GLEWVA | VIWYD---GSNKHYADS VKG | RFTISRDNSKNTLYLQMNSL RAEDTAVYYCAR | DCGVGY------YGTDV | WGQGT TVTVS S |
| iPS:4 36430 | 21-225_215A12 | VH3|3-33/D4|4-17/RF2|J H6 | QVQLVES-GGGVVQPGRSLRL SCAASG-LTFS | S-----YGMH | WVRQAPGK GLEWVA | VIWYD---GSNEHYADS VKG | RFTISRDNSKNTLYLQMNSL RAEDTAVYYCAR | DRGVGY------YGMDV | WGQGT TVTVS S |
| iPS:4 36452 | 21-225_217G5 | VH3|3-33/D4|4-17/RF2|J H6 | QVQLVES-GGGVVQPGRSLRL SCAASG-FTFS | S-----NGMH | WVRQAPGK GLEWVA | VIWYD---GSNKNYADS VKG | RFTISRDNSKNTLYLQMNSL RAEDTAVYYCAR | DYGVGY------YGLDV | WGQGT TVTVS S |
| iPS:4 36464 | 21-225_219H1 | VH3|3-33/D4|4-17/RF2|J H6 | QVQLVES-GGGVVQPGRSLRL SCAASG-FTFS | R-----YGMH | WVRQAPGK GLEWVA | VIWYD---GSNKNYADS VKG | RFTISRDNSKNTLYLQMNSL RGEDTAVYYCAR | DRGVGY------NCMDV | WGQGT TVTVS S |
| iPS:4 51120 | 21-225_197D3 | VH3|3-33/D4|4-17/RF2|J H6 | QVQLVES-GGGVVQPGRSLRL SCAASG-FTFS | S-----HGMH | WVRQAPGK GLEWVA | VIWYD---GSNEHYADS VKG | RFTISRDNSKNTLYLQMNSL RAEDTAVYYCAR | DQGVGY------YGMDV | WGQGT TVTVS S |
| | Germline | | H_FR1 | H_CDR1 | H_FR2 | H_CDR2 | H_FR3 | H_CDR3 | H_FR4 |
| | VH3|3-33/D4|4-17/RF2|J H4 | | QVQLVES-GGGVVQPGKSLRL SCAASG-FTFS | YGMH | WVRQAPGK GLEWVA | VIWYD---GSNKYADS VKG | RFTISRDNSKNTLYLQMNSL RAEDTAVYYCAR | YFDY | WGQGT LVTVS S |
| iPS:4 68822 | 21-225_147E10 | VH3|3-33/D4|4-17/RF2|J H4 | QVQLVES-GGGVVQPGKSLRL SCAASG-FTFS | N-----YGLH | WVRQAPGK GLEWVA | IIWYD---GSNKYADS VKG | RFTISRDNSKNTLYLQMNSL RAEDTAVYYCAR | DHYDFW------SGHFDY | WGQGT LVTVS S |
| iPS:4 33965 | 21-225_46F2 | VH3|3-33/D4|4-17/RF2|J H4 | QVQLVES-GGGVVQPGRSLRL SCAASG-FTFS | S-----YGMH | WVRQAPGK GLEWVA | IIWYD---GSNKYVDS VKG | RFTISRDNSKNTLYLQMNSL RAEDTAVYYCAR | DRYDFW------SGYFDY | WGQGT LVTVS S |

Figure 51 (Continued)

| | | | | | | | | |
|---|---|---|---|---|---|---|---|---|
| iPS:4 34255 | 21-225_62E6 | VH3j3-33/D4j4-17jRF2/JH4 | QVQLVES-GGGVVQPGRSLRLSCAASG-FTFS | S------YGMH | WVRQAPGK GLEWVA | AIWYD---GSNKYYGDSVKG | RVTISRDNSKNSLRLQMNSL RAEDTAVYYCAR | DQGIVG------ATWFDY | WGQGT LVTVS S |
| iPS:4 34269 | 21-225_57H3 | VH3j3-33/D4j4-17jRF2/JH4 | QVQLVES-GGGVVQPGRSLRLSCAASG-FTFS | S------YGMH | WVRQAPGK GLEWVA | AIWYD---GSNKYYADSVKG | RFTISRDNSKNTLYLQMNSL RAEDTAVYYCAR | DYGIVG------ATYFDY | WGQGT LVTVS S |
| iPS:4 34345 | 21-225_64H9 | VH3j3-33/D4j4-17jRF2/JH4 | QVQLVES-GGGVVQPGRSLRLSCAASG-FTFS | T------YGMH | WVRQAPGK GLEWVA | IIWYD---GSNKYYADSVKG | RFTISRDNSKNTLYLQMNSL RAEDTAVYYCAR | DTYDFW------SGYLGY | WGQGT LVTVS S |
| iPS:4 34363 | 21-225_65A6 | VH3j3-33/D4j4-17jRF2/JH4 | QVQLVES-GGGVVQPGRSLRLSCAASG-FTFS | N------YGMH | WVRQAPGK GLEWVA | VIWYD---GSNKYYGDSVKG | RFTISRDNSKNSLHLQMNSL RAEDTAVYYCAR | DQGIVG------ATWFDY | WGQGT LVTVS S |
| iPS:4 34393 | 21-225_67C3 | VH3j3-33/D4j4-17jRF2/JH4 | QVQLVES-GGGVVQPGRSLRLSCAASG-FTFS | S------YGMH | WVRQAPGK GLEWVA | AIWYD---GSNKYYGDSVKG | RVTISRDNSKNSLHLQMNSL RAEDTAVYYCAR | DQGIVG------ATWFDY | WGQGT LVTVS S |
| iPS:4 34425 | 21-225_70A5 | VH3j3-33/D4j4-17jRF2/JH4 | QVQLVES-GGGVVQPGRSLRLSCAASG-FTFS | S------YGMH | WVRQAPGK GLEWVA | VIWYD---GSNKYYADSVKG | RFTISRDNSKNSLYLQMNSL SAEDTAVYYCAR | DQGIVG------ATWFDY | WGQGT LVTVS S |
| iPS:4 35341 | 21-225_148B2 | VH3j3-33/D4j4-17jRF2/JH4 | QVQLVES-GGGVVQPGRSLRLSCAASG-FTFS | S------YGMH | WVRQAPGK GLEWVA | IIWYD---GSYKYYADSVKG | RFTISRDNSKNTLYLQMNSL SAEDTAVYYCAR | DHFDFW------SGHFDY | WGQGT LVTVS S |
| iPS:4 35357 | 21-225_148G10 | VH3j3-33/D4j4-17jRF2/JH4 | QVQLVES-GGGVVQPGRSLRLSCAASG-FTFS | S------YGMH | WVRQAPGK GLEWVA | IIWYD---GSNKYYADSVKG | RFTISRDNSKNTLYLQMNSL RAEDTAVYYCAR | DRYDFW------SGHFDY | WGQGT LVTVS S |
| iPS:4 35365 | 21-225_149F1 | VH3j3-33/D4j4-17jRF2/JH4 | QVQLVES-GGGVVQPGRSLRLSCAASG-FTFS | S------YGMH | WVRQAPGK GLEWVA | IIWYD---GSYKYYADSVKG | RFTISRDNSKNTLYLQMNSL SAEDTAVYYCAR | DHFDFW------SGHFDY | WGQGT LVTVS S |
| iPS:4 35413 | 21-225_150B11 | VH3j3-33/D4j4-17jRF2/JH4 | QVQLVES-GGGVVQPGRSLRLSCAASG-FTFS | S------YGMH | WVRQAPGK GLEWVA | IIWYD---GSNKYYADSVKG | RFTISRDNSKNTLYLQMNSL RAEDTAVYYCAR | DRYDFW------SGHFDY | WGQGT LVTVS S |
| iPS:4 35423 | 21-225_151G5 | VH3j3-33/D4j4-17jRF2/JH4 | QVQLMES-GGGVVQPGRSLRLSCAASG-FTFS | S------YGMH | WVRQAPGK GLEWVA | IIWYD---GSNKYYADSVKG | RFTISRDNSKNTLYLQMNSL RAEDTAVYYCAR | DRYDFW------SGHFDY | WGQGT LVTVS S |
| iPS:4 35429 | 21-225_151A10 | VH3j3-33/D4j4-17jRF2/JH4 | QVQLVES-GGGVVQPGRSLRLSCAASG-FTFS | N------YGMH | WVRQAPGK GLEWLA | IIWYD---GSNKYYADSVKG | RFTISRDNSKNTLYLQMNSL RAEDTAVYYCAR | DHYDFW------SGHFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35489 | 21-225_155A5 | VH3|3-33|D4|4-17|RF2|JH4 | QVQLVES-GGGVVQPGRSLRL SCAASG-FTFS | S-----YGMH | WVRQAPGK GLEWVA | IIWYD---GSSKYYADS VKG | RFTISRDNSKNTLYLHMNSL RAEDTAVYYCAR | DRYDFW-------SGHFDY | WGQGT LVTVS S |
| iPS:4 35683 | 21-225_170A1 | VH3|3-33|D4|4-17|RF2|JH4 | QVQLVES-GGGVVQPGRSLRL SCAASG-FTFS | S-----YGMH | WVRQAPGK GLEWVA | IIWYD---GSYKYYADS VKG | RFTISRDNSKNTLYLQMNSL RAEDTAVYYCAR | DAHDFW-------SGYFDS | WGQGT LVTVS S |
| iPS:4 35755 | 21-225_176H4 | VH3|3-33|D4|4-17|RF2|JH4 | QVQLVES-GGGVVQPGRSLRL SCAASG-FTFS | S-----YGMH | WVRQAPGK GLEWVA | IIWYD---GSYKYYADS VKG | RFTISRDNSKNTLYLQMSSL RAEDTAVYYCAR | DAHDFW-------SGYFAY | WGQGA LVTVS S |
| iPS:4 35795 | 21-225_181C2 | VH3|3-33|D4|4-17|RF2|JH4 | QVQLVES-GGGVVQPGRSLRL SCVASG-FTFS | S-----YGMH | WVRQAPGK GLEWVT | IIWYD---GSYKYYADS VKG | RFTISRDNSKNTLYLQMNSL RAEDTAVYYCAR | DHYDFW-------SGHFDF | WGQGT LVTVS S |
| iPS:4 35807 | 21-225_181C10 | VH3|3-33|D4|4-17|RF2|JH4 | QVQLVES-GGGVVQPGRSLRL SCAASG-FTFS | S-----YGMH | WVRQAPGK GLEWMA | IIWYD---GSYKYYADS VKG | RFTISRDNSKNTLYLQMNSL RAEDTAVYYCAR | DHYDFW-------SGHFDY | WGQGT LVTVS S |
| iPS:4 35887 | 21-225_186F7 | VH3|3-33|D4|4-17|RF2|JH4 | QVQLVES-GGGVVQPGRSLRL SCAASG-FTFS | T-----YGMH | WVRQAPGK GLEWVA | IIWYD---GSYKYYADS VKG | RFTISRDNSKNTLYLQMNSL RAEDTAVYYCAR | DHYDFW-------SGHFDY | WGQGT LVTVS S |
| iPS:4 35901 | 21-225_189G2 | VH3|3-33|D4|4-17|RF2|JH4 | QVQLVES-GGGVVQPGRSLRL SCAASG-FTFS | N-----YGMH | WVRQAPGK GLEWVA | IIWYD---GSYKYYADS VKG | RFTISRDNSKNTLYLQMNSL RAEDTAVYYCAR | DREDFW-------SGYSDY | WGQGT LVTVS S |
| iPS:4 36594 | 21-225_226A5 | VH3|3-33|D4|4-17|RF2|JH4 | QVQLVES-GGGVVQPGRSLRL SCAASG-FTFS | N-----YGMH | WVRQAPGK GLEWVA | IIWYD---GTNKYTDS VKG | RFTISRDNSKNTLYLQMNSL RAEDTAVYYCAR | EGHDFW-------SGFFCY | WGQGT LVTVS S |
| iPS:3 92814 | 21-225_22A1 | VH3|3-33|D4|4-17|RF2|JH4 | QVQLVES-GGGVVQPGRSLRL SCAASG-FTFS | S-----YGMH | WVRQAPGK GLEWVA | VMWYD---GSNKYYADS VKG | RFTISRDNSKNTLYLQMNSL RAEDTAVYYCAR | DGGFL-------EWLDY | WGQGT LVTVS S |
| iPS:3 93036 | 21-225_28G3 | VH3|3-33|D4|4-17|RF2|JH4 | QVQLVES-GGGVVQPGRSLRL SCAASG-FTFS | T-----YGMH | WVRQAPGK GLEWVA | VIWYD---GSNKYYADS VKG | RFTISRDNSKNTLYLQMNSL RAEDTAVYYCAR | DRYDFW-------SGYFDY | WGQGT LVTVS S |
| Germline VH3|3-33|D7|7-27|RF1|JH4 | | | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | YDY | WGQGT LVTVS S |
| iPS:4 68824 | 21-225_73G6 | VH3|3-33|D7|7-27|RF1|JH4 | QVQLVES-GGGVVQPGRSLRL SCAASG-FTFS | S-----YGMH | WVRQAPGK GLEWVA | VIWYD---VSNKYYGDS VKG | RFTISRDNSKNTLYLQMNSL RAEDTAVYYCAR | EVGM-------TSDY | WGQGT LVTVS S |

Figure 51 (Continued)

| | | | | | | | | |
|---|---|---|---|---|---|---|---|---|
| iPS:4 34169 | 21-225_50C4 | VH3/3-33/D7/7-27/RF1/JH4 | QVQLVES-GGGVVQPGRSLRLSCAASG-FTFS | D------YGMH | WVRQAPGK GLEWVA | VIWYE---ETNKYYADS VKG | RFTISRDNSKNTLYLQMNSL RGEDTAVYYCAR | EVGF--------LNDY | WGQGT LVTVS S |
| iPS:4 35045 | 21-225_90H5 | VH3/3-33/D7/7-27/RF1/JH4 | QVQLVES-GGGVVQPGRSLRLSCAASG-FTFS | D------YGMH | WVRQSPGK GLEWVA | VIWYE---GSNTYYADS VKG | RFTISRDNSKNTLYLQMNSL RAEDTAVYYCVR | EMGW--------LDDY | WGQGT LVTVS S |
| iPS:4 35367 | 21-225_149G1 | VH3/3-33/D7/7-27/RF1/JH4 | QVQLVES-GGGVVQPGRSLRLSCAASG-FTFS | D------YGMH | WVRQAPGK GLEWVA | VIWYE---GSNKYYADS VKG | RFTISRDNSKNMLYLQMNSL RAEDTAVYYCAR | EIGF--------SEDY | WGQGT LVTVS S |
| iPS:4 35397 | 21-225_149F12 | VH3/3-33/D7/7-27/RF1/JH4 | QVQLVES-GGGVVQPGRSLRLSCAASG-FTFS | D------YGMH | WVRQAPGK GLEWVA | VIWYE---ENNKYYADS VKG | RFTISRDNSKNTFLQMNSL RAEDTAVYYCAR | EIGF--------SEDY | WGQGT LVTVS S |
| iPS:4 35407 | 21-225_150E7 | VH3/3-33/D7/7-27/RF1/JH4 | QVQLVES-GGGVVQPGRSLRLSCAASG-FTFS | D------YGMH | WVRQAEGK GLEWVA | VIWYE---ENNKYYADS VKG | RFTISRDNSKNTLYLQMNSL RAEDTAVYYCAR | EIGF--------SEDY | WGQGT LVTVS S |
| iPS:4 35609 | 21-225_161F7 | VH3/3-33/D7/7-27/RF1/JH4 | QVQLVES-GGGVVQPGRSLRLSCAASG-FTFS | D------FGLH | WVRQAPGQ GLEWVA | VIWFD---GSNKYYADS VKG | RFTIFRDNSKNTLYLQMNSL RAEDTAVYYCAR | EIGW--------LSDY | WGQGT LVTVS S |
| iPS:4 35613 | 21-225_161D11 | VH3/3-33/D7/7-27/RF1/JH4 | QVQLVES-GGGVVQPGRSLRLSCAASG-FTFS | D------FGLH | WVRQAPGK GLEWVA | VIWFD---GSNKYYADS VKG | RFTISRDNSKNTLYLQMNSL RVEDTAVYYCAR | EIGW--------LSDY | WGQGT LVTVS S |
| iPS:4 35791 | 21-225_180H7 | VH3/3-33/D7/7-27/RF1/JH4 | QVQLVES-GGGVVQPGRSLRLSCAASG-FTFS | D------YGMH | WVRQAPGK GLEWVA | VIWYD---ENNKHYADS AKG | RFTISRDNSKNTLYLQMNSL RAEDTAVYYCAR | EVGW--------SDDY | WGQGT LVTVS S |
| iPS:4 35805 | 21-225_181A8 | VH3/3-33/D7/7-27/RF1/JH4 | QVQLVES-GGGVVQPGRSLRLSCAASG-FTFS | D------YGMH | WVRQAPGK GLEWVA | VIWYD---ENNKHYGDS AKG | RFTISRDNSKNTLYLQMNSL RAEDTAVYYCAR | EVGW--------SDDY | WGQGT LVTVS S |
| iPS:4 35879 | 21-225_184H10 | VH3/3-33/D7/7-27/RF1/JH4 | QVQLVES-GGGVVQPGRSLRLSCAASG-FTFS | D------YGMH | WVRQAEGK GLEWVA | VIWYD---ETNKHYGDS VKG | RFTISRDNSKDTLYLQMNSL RAEDTAVYYCAR | EVGW--------HDDY | WGQGT LVTVS S |
| iPS:4 35881 | 21-225_184D11 | VH3/3-33/D7/7-27/RF1/JH4 | QVQLVES-GGGVVQPGRSLRLSCAASG-FTFS | D------YGMH | WVRQAEGK GLEWVA | VIWYD---ENNKHYGDS VKG | RFTISRDNSKDLYLQMNSL RAEDTAVYYCAR | EVGW--------HDDY | WGQGT LVTVS S |
| iPS:4 36350 | 21-225_210E4 | VH3/3-33/D7/7-27/RF1/JH4 | QVQLVES-GGGVVQPGRSLRLSCAASG-FTLI | N------YGMH | WVRQAPGK GLEWVA | VIWYD---ENNKYVDS VKG | RFTISRDDSKNTLYLQMNSL RAEDSAVYYCAR | ETGF--------LSDY | WGQGT LVTVS S |

Figure 51 (Continued)

| | | | | | | | | | |
|---|---|---|---|---|---|---|---|---|---|
| iPS:4 36576 | 21-225_225B6 | VH3/3-33/D7/7-27/RF1/JH4 | QVQLVES-GGGVVQPGRSLRLSCAASG-FTFS | D------YGMH | WVRQAPGK GLEWVA | VIWYD---ENNKYYADS VKG | RFTISRDNSKNTLYLQMNSL RAEDTAVYYCAR | EVGF--------- | ------TEDY | WGQGT LVTVS S |
| iPS:4 36578 | 21-225_225D6 | VH3/3-33/D7/7-27/RF1/JH4 | QVQLVES-GGGVVQPGRSLRLSCAASG-FTFS | N------YGMH | WVRQAPGK GLEWVA | VIWYD---ENNKYYADS VKG | RFTISRDNSQNTLYLQMTSL RAEDTAVYYCAR | EVGF--------- | ------TEDY | WGQGT LVTVS S |
| iPS:4 36582 | 21-225_225F8 | VH3/3-33/D7/7-27/RF1/JH4 | QVQLVES-GGGVVQPGRSLRLSCAASG-FTFS | S------YGMH | WVRQAPGK GLEWVA | VIWYD---ENNKYYVDS VKG | RFTISRDNSKNTLYLQMNSL RAEDTAVYYCAR | EVGF--------- | ------TEDY | WGQGT LVTVS S |
| iPS:4 36608 | 21-225_226A9 | VH3/3-33/D7/7-27/RF1/JH4 | QVQLVES-GGGVVQPGRSLRLSCAASG-FTFS | N------YGMH | WVRQAPGK GLEWVA | VIWYE---ESNKYYTDS VKG | RFTISRDNSKNTLFLQMNSL RAEDTAVYYCAR | EVGF--------- | ------TEDY | WGQGT LVTVS S |
| iPS:4 36630 | 21-225_227G3 | VH3/3-33/D7/7-27/RF1/JH4 | QVQLVES-GGGVVQPGRSLRLSCAASG-FTFS | S------YGMH | WVRQAEGK GLEWVA | VIWYV---GSNQYYADS VKG | RFTISRDNSKNTLYLQMSSL RAEDTAVYYCAR | EVGF--------- | ------TEDY | WGQGT LVTVS S |
| iPS:4 36634 | 21-225_227H5 | VH3/3-33/D7/7-27/RF1/JH4 | QVQLVES-GGGVVQPGRSLRLSCAASG-FTFS | N------YGMH | WVRQAPGK GLDWVA | VIWYE---ESNKYYADS VKG | RFTISRDNSKNTLYLQMNSL RAEDTAMYYCAR | EVGF--------- | ------TEDY | WGQGT LVTVS S |
| iPS:4 36650 | 21-225_227C12 | VH3/3-33/D7/7-27/RF1/JH4 | QVQLVES-GGGVVQPGRSLRLSCAASG-FTFS | N------YGMH | WVRQAPGK GLEWVA | VIWYI---GSNQYYADS VKG | RFTISRDNSKNTLYLQMSSL RAEDTAVYYCAR | EVGF--------- | ------TEDY | WGQGT LVTVS S |
| iPS:4 37280 | 21-225_203C10 | VH3/3-33/D7/7-27/RF1/JH4 | QVQLVES-GGGVVQPGRSLRLSCAASG-FTFS | D------YGMH | WVRQAPGK GLEWVA | VIWYD---GGNTHYTDS VKG | RFTISRDNSKNTLYLQMNSL RAEDTAVYYCAR | EVGW--------- | ------LDDY | WGQGT LVTVS S |
| iPS:3 92740 | 21-225_18H12 | VH3/3-33/D7/7-27/RF1/JH4 | QVQLVES-GGGVVQPGRSLRLSCAASG-FTFS | D------YGMH | WVRQAPGK GLEWMA | VIWYD---VTNKYYADS VKG | RFTISRDNSKNTLYLQMNSL RAEDTAVYYCAR | EVGW--------- | ------YEDY | WGQGT LVTVS S |
| iPS:3 92780 | 21-225_22B7 | VH3/3-33/D7/7-27/RF1/JH4 | QVQLVES-GGGVVQPGRSLRLSCAASG-FTFS | S------YGMH | WVRQAEGK GLEWVA | VIWYE---ENNQYYADS VKG | RFTISRDNSKNTLYLQMNSL RAEDTAVYYCAR | EVGF--------- | ------RSDY | WGQGT LVTVS S |
| iPS:3 92912 | 21-225_25A9 | VH3/3-33/D7/7-27/RF1/JH4 | QVQLVES-GGGVVQPGRSLRLSCAASG-FTFS | S------YGMH | WVRQAEGK GLEWVA | VIWYD---VTNKYYTGS VKG | RFTISRDNSKNTLYLQMNSL RAEDTAVYYCAR | EIGW--------- | ------LDDY | WGQGT LVTVS S |
| iPS:3 92940 | 21-225_29D9 | VH3/3-33/D7/7-27/RF1/JH4 | QVQLVES-GGGVVQPGRSLKLSCSASG-FTFS | D------YGIH | WVRQAPGK GLEWVA | VIWYD---ESNNYYADS VKG | RFTISRDNSKNTLYLQMNSL RAEDTAVYYCAR | EIGW--------- | ------LDDY | WGQGT QVTVS S |

Figure 51 (Continued)

| | | | | | | | | | |
|---|---|---|---|---|---|---|---|---|---|
| iPS:3 92948 | 21-225_25G5 | VH3j3-33/D7j7-27/RF1/JH4 | QVQLVES-GGGVVQPGRSLRL SCAASG-FTFS | D------YGIH | WVRQAPGK GLEWVA | VIWYD---GNNKYIADS VKG | RFTISRDNSKNTLYLQMNNL RAEDTAVYYCAR | EIGW----------- | ---------LDDY | WGQGT LVTVS S |
| iPS:3 92978 | 21-225_28B8 | VH3j3-33/D7j7-27/RF1/JH4 | QVQLVES-GGGVVQPGRSLRL SCAASG-FTFS | D------YGMH | WVRQAPGK GLEWVT | VIWYD---ANNKYYADS VKG | RFTISRDNFKNTVYLQMNSL RAEDTAVYYCAR | EIGW----------- | ---------LDDY | WGQGT LVTVS S |
| iPS:3 92998 | 21-225_28A9 | VH3j3-33/D7j7-27/RF1/JH4 | QVQLVES-GGGVVQPGRSLRL SCAASG-FTFS | S------YGIH | WVRQAPGK GLEWVA | VIWFD---GSNKYYADS VKG | RFTISRDNSKNTLFLQMNSL RVEDTAVYYCAR | EIGW----------- | ---------LDDY | WGQGT LVTVS S |
| iPS:3 93038 | 21-225_29D8 | VH3j3-33/D7j7-27/RF1/JH4 | QVQLVES-GGGVVQPGRSLRL SCAASG-FTFR | D------YGIH | WVRQAPGK GLEWVA | VIWFD---GTNKYYADS VKG | RFTISRDNSKNTLYLQMNSL RAEDTAVYYCGR | EIGW----------- | ---------LDDY | WGQGT LVTVS S |
| iPS:3 93056 | 21-225_30F3 | VH3j3-33/D7j7-27/RF1/JH4 | QVQLVES-GGGVVQPGRSLRL SCAASG-FTFS | S------YGMH | WVRQAPGK GLEWVA | VIWYD---VSNKYYADS VKG | RFTISRDNSKNTLYLQMNSL RPEDTAVYYCAR | EMGW----------- | ---------YDDY | WGQGT LVTVS S |
| iPS:3 93074 | 21-225_33B1 | VH3j3-33/D7j7-27/RF1/JH4 | QVQLVES-GGGVVQPGRSLRL SCAASG-FTFS | D------YGMH | WVRQAPGK GLEWVA | VIWFD---RNNKYYADS VKG | RFTISRDNSKNTLYLQMNSL RAEDTAVYYCAR | EMGW----------- | ---------YDDY | WGQGT LVTVS S |
| iPS:3 93822 | 21-225_15B11 | VH3j3-33/D7j7-27/RF1/JH4 | QVQLVES-GGGVVQPGRSLRL SCAASG-FTFS | N------YGMH | WVRQAPGK GLEWVA | VIWYE---ESNKYYTDS VKG | RFTISRDNSKNTLYLQMNSL RPEDTAVYYCAR | EVGF----------- | ---------TEDY | WGQGT LVTVS S |
| iPS:3 93856 | 21-225_14C2 | VH3j3-33/D7j7-27/RF1/JH4 | QVQLVES-GGGVVQPGRSLRL SCAASG-FTFS | D------YGMH | WVRQAPGK GLEWVA | VIWYD---ESNKYEDS VKG | RFTISRDNSKNTLYLQMKSL RAEDTAVYYCAR | EVGF----------- | ---------RSDY | WGQGT LVTVS S |
| iPS:3 93874 | 21-225_4C8 | VH3j3-33/D7j7-27/RF1/JH4 | QVQLVES-GGGVVQPGRSLRL SCAASG-FTFS | N------YGMH | WVRQAPGK GLEWVA | VIWYE---ENNQYYADS VKG | RFTISRDNSKNTLYLQMNSL TAEDTAVYYSPR | EMGF----------- | ---------LSDY | WGQGT LVTVS S |
| iPS:3 93884 | 21-225_4F12 | VH3j3-33/D7j7-27/RF1/JH4 | QVQLVES-GGGVVQPGRSLRL SCAASG-FTFS | S------YGMH | WVRQAPAK GLEWVA | VIWYD---VTNKYYADS VKG | RFTISRDNSKNTLYLQMNSL TPENTGGYENQR | EKGG----------- | ---------LFDY | WGQGT LVTVS S |
| iPS:3 94020 | 21-225_15H10 | VH3j3-33/D7j7-27/RF1/JH4 | QVQLVES-GGGVVQPGRSLRL SCAASG-FTFS | N------YGMH | WVRQAPGK GLEWVA | VIWYD---ESNKYEDS VKG | RFTISRDNSKNTLYLQMNSL RAEDTAVYYCVR | EVGF----------- | ---------LSDY | WGQGI LVTVS S |
| iPS:3 94095 | 21-225_16H4 | VH3j3-33/D7j7-27/RF1/JH4 | QVQLVES-GGGVVQPGRSLRL SCAASG-FTFS | N------YGMH | WVRQAPGK GLEWVA | VIWYD---VSNKYYADS VKG | RFTISRDNSKNMLYLQMNSL RAEDTAVYYCAR | EMGW----------- | ---------TDDC | WGQGT LVTVS S |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| | | VH1|1-08|D5|5-24|RF3|JH6 | QVQLVQS CAETKKPGASVKV SCKASG-YTFT | S------YDIN | WVRQATGQ GLEWMG | WMNPK--- SGGTNYAQK FQG | RVTMTRDTSISTAYMELSSL RSEDTAVYYCAR | EDLNYTF--AYWMDV | WGQGT LVTVS S |
| iPS:4 68818 | 21-225_190C8 | VH1|1-08|D5|5-24|RF3|JH6 | QVQLVQS- GAEVKKPGASVKV SCKASG-YTFT | S------YDIN | WVRQATGQ GLEWMG | WMNPK--- RGNTGYAQK FQG | RVTMTRDTSISTAYMELSSL RSEDTAVYYCAR | GDPYNWN-------SYAMDV | WGQGA TVTVS S |
| iPS:4 36023 | 21-225_193A5 | VH1|1-08|D5|5-24|RF3|JH6 | QVQLVQS- GAEVKKPGASVKV SCKASG-YTFI | S------YDIN | WVRQATGQ GLEWMG | WMNPK--- RGNTGYAQK FQG | RVTMTRDTSISTAYMELSSL RSEDTAVYYCAR | GDPYNWN-------SYAMDV | WGQGA TVTVS S |
| iPS:4 36132 | 21-225_196C12 | VH1|1-08|D5|5-24|RF3|JH6 | QVQLVQS- GAEVKKPGASVKV SCKASG-YTFI | S------YDIN | WVRQATGQ GLEWMG | WMNPK--- RGNTGYAQK FQG | RVTMTRDTSISTAYMELSSL RSEDTAVYYCAR | GDPYNWN-------SYAMDV | WGQGA TVTVS S |
| | | VH3|3-33/D3|2-8|RF3|JH5 | QVQLVES GGGVVQPGRSSRL SCAASG-FTFS | S------YGMH | WVRQAPGK GLEWVS | GSNKYYADS VKG | RFTISRDNSKNTLFLQMNSL RAEDTAVYYCAR | AIWWFDP | WGQGT LVTVS S |
| iPS:4 68828 | 21-225_162A10 | VH3|3-33/D2|2-8|RF3|JH5 | QVQLVES- GGGVVQPGRSLRL SCAASG-FTFS | S------CGMH | WVRQAPGK GLEWVA | AIWYD--- GSNKYYADS VKG | RFTISRDNSKNTLFLQMNSL RAEDTAVYYCAR | DKNIMG-------DTWFDF | WGQGT LVTVS S |
| | | VH1|1-02|D5|5-18|RF3|JH4 | QVQLVQS CAETKKPGASVKV SCKASG-YTFT | G------YYMH | WVRQAPGQ GLEWMG | WINPN--- SGGTNYAQK FQG | RVTMTRDTSISTAYMELSRL RSEDTAVYYCAR | GYSYG------YYFDY | WGQGT LVTVS S |
| iPS:4 68830 | 21-225_191G11 | VH1|1-02|D5|5-18|RF3|JH4 | QVQLVQS- GAEVKKPGASVKV SCKASG-YTFT | G------YYMH | WVRQAPGQ GLEWMG | WINPN--- SGGTNFAQK FQG | RVLIIRDTSINIAYMELSWL RSEDTAVYYCAR | GKNYG-------SYFDY | WGQGT LVTVS S |
| iPS:4 36896 | 21-225_67F10 | VH1|1-02|D5|5-18|RF3|JH4 | QVQLVQS- GAEVKKPGASVKV SCKASG-YTFT | G------YYMH | WVRQAPGQ GLEWMG | WINPN--- SGGTNYGQK FQG | RVTMTRDTSISTAYMELSRL RSEDTAVYYCAR | TYFYGSGS------YYNGFDY | WGQGT LVTVS S |
| iPS:3 93218 | 21-225_14G3 | VH1|1-02|D5|5-18|RF3|JH4 | QVQLVQS- GAEVKKPGASVKV SCKASG-YTFT | G------YYMY | WVRQAPGQ GLEWMG | WINPN--- SGGTNYAQK FQG | RVTMTRDTSISTAYMELSRL RSEDTAVYYCAR | SYFYGSGS------YYNEFDY | WGQGT LVTVS S |
| iPS:3 93565 | 21-225_34B11 | VH1|1-02|D5|5-18|RF3|JH4 | QVKLVQS- GAEVKKPGASVKV SCKASG-YTFT | G------YYMH | WVRQAPGQ GLEWMG | WINPN--- SGGTNYAQK FQG | RVTMTRDTSISTAYMELSRL RSEDTAVYYCAR | VYFYGSGS------YYNEFDY | WGQGT LVTVS S |
| iPS:3 98470 | 21-225_14B7 | VH1|1-02|D5|5-18|RF3|JH4 | QVQLVQS- GAEVKKPGASVKV SCKASG-YTFT | G------YYMH | WVRQAPGQ GLEWMG | WINPN--- SGGTNYVQK FQG | RVTMTRDTSISTACMELSRL KSEDTAVYFCAR | SPFYGSGS------YYNEFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3/3-30.3/D1/1-1/RF1/JH6 | | QVQLVES-GGGVVQPGRSLRL SCAASG-FTFS | S------YGMH | WVRQAPGK GLEWVA | VISYD------GGYKNYADS VKG | RFTISRDNSKNTLYLQMNSL RAEDTAVYYCAR | GTHGYY------YGVDV | WGQGT TVTVS S |
| iPS:4 68836 21-225_198E3 | VH3/3-30.3/D1/1-1/RF1/JH6 | QVQLVES-GGAVVQPGRSLRL SCAASG-FTFS | S------YGMH | WVRQAPGK GLEWVA | VISYD------GGYKNYADS VKG | RFTISRDNSKNTLYLQMNSL RAEDTAVYYCAR | GTHGYY------YGVDV | WGQGT TVTVS S |
| iPS:4 35831 21-225_190C12 | VH3/3-30.3/D1/1-1/RF1/JH6 | QVQLVES-GGAVVQPGRSLRL SCAASG-FTFS | S------YGMH | WVRQAPGK GLEWVA | VISYD------GGYKNYADS VKG | RFTISRDNSKNTLYLQMNSL RAEDTAVYYCAR | GTHGYY------YGVDV | WGQGT TVTVS S |
| iPS:4 35857 21-225_191A4 | VH3/3-30.3/D1/1-1/RF1/JH6 | QVQLVES-GGGVVQPGRSLRL SCAASG-FTFS | S------YGMH | WVRQAPGK GLEWVA | VISYD------GGYKNYADS VKG | RFTISRDNSKNTLYLQMNSL RAEDTAVYYCAR | GTHGYY------YGVDV | WGQGT TVTVS S |
| iPS:4 35907 21-225_190G3 | VH3/3-30.3/D1/1-1/RF1/JH6 | QVQLVES-GGGVVQPGRSLRL SCAASG-FTFS | S------YGMH | WVRQAPGK GLEWVA | VISYD------GGYKNYVDS VKG | RFTISRDNSKNTLYLQMNSL RAEDTAVYYCAR | GTHGYY------YGVDV | WGQGT TVTVS S |
| iPS:4 35919 21-225_190H5 | VH3/3-30.3/D1/1-1/RF1/JH6 | QVQLVES-GGGVVQPGRSLRL SCAASG-FTFS | S------YGMH | WVRQAPGK GLEWVA | VISYD------GGYKNYADS VKG | RFTISRDNSKNTLYLQMNSL RAEDTAVYYCAR | GTHGYY------YGVDV | WGQGT TVTVS S |
| iPS:4 35989 21-225_192F7 | VH3/3-30.3/D1/1-1/RF1/JH6 | QVQLVES-GGGVVQPGRSLRL SCAASG-FTFS | S------YGMH | WVRQAPGK GLEWVT | VISYD------GGYKNYADS VKG | RFTISRDNSKNTLYLQMNSL RAEDTAVYYCAR | GTHGYY------YGVDV | WGQGT TVTVS S |
| iPS:4 36222 21-225_200C9 | VH3/3-30.3/D1/1-1/RF1/JH6 | QVQLVES-GGGVVQPGRSLRL SCAASG-FTFS | S------YGMH | WVRQAPGK GLEWVA | VISYD------GGYKNYIDS VKG | RFTISRDNSKNTLYLQMNSL RAEDTAVYYCAR | GTHGYY------YGVDV | WGQGT TVTVS S |
| | Germline | H_FR1 | H_CDR1 | H_FR2 | H_CDR2 | H_FR3 | H_CDR3 | H_FR4 |
| VH4/4-30.1/D5/5-24/RF3/JH6 | | | | | | | | |
| iPS:4 68840 21-225_200H9 | VH4/4-30.1/D5/5-24/RF3/JH6 | QVQLQES-GPGLVKPSQTLSL TCTVSG-GSMR | SG---GDYWS | WIRQHPGK GLEWPG | YIYY------SGSTYNPS LKS | RVTLSVDTSKNQFSLKLSSV TAADTAVYYCAR | MDYSNY------YYGMDV | WGQGT SVTVS S |
| iPS:4 36096 21-225_195E10 | VH4/4-30.1/D5/5-24/RF3/JH6 | QVQLQES-GPGLVKPSQTLSL TCTVSG-GSIS | SG---GYYMS | WIRQHPGK GLEMIG | YIYY------SGSTYNPS LKS | RVTLSVDTSKNQFSLKLSSV AAADTAVYYCAR | GGYNWN------HGMDV | WGQGT TVTVS S |
| iPS:4 36120 21-225_196C10 | VH4/4-30.1/D5/5-24/RF3/JH6 | QVQLQES-GPGLVKPSQTLSL TCTVSG-GSMR | SG---GDYWS | WIRQHPGK GLEWPG | FIYY------SGSTYNPS LKS | RVTLSVDTSKNQFSLKLSSV TAADTAVYYCAR | MDYSNY------YYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36216 | 21-225_200B7 | VH4/4-30.1/D5/5-24/RF3/J H6 | QVQLQES-GPGLVKPSQTLSL TCTVSG-GSIS | SG---GYYWS | WIRQHPGK GLEWIG | YIFY----SGSTNYNPS LRS | RVTISVDTSKNQFSLKLSSV TAADTAVYYCAR | AGYNWN---------NGMDV | WGQGT TVTVS S |
| | | Germline | | | | | | | |
| | VH3/3-21/D6/6-6/RF2/JH4 | | | | | | | | |
| iPS:4 68844 | 21-225_48E10 | VH3/3-21/D6/6-6/RF2/JH 4 | EVQLVES-GGGLVKPGGSLRL SCAASG-FTFS | S------YNMN | WVRQAPGK GLEWVS | SISGS---SSYIYYADS VKG | RFTISRDNAKNSLYLQMNSL RAEDTAVYYCAR | SL-------------DL | WGQGT LVTVS S |
| iPS:4 35537 | 21-225_157H12 | VH3/3-21/D6/6-6/RF2/JH 4 | EVQLVES-GGGLVKPGGSLRL SCAASG-FTFS | S------YSMN | WVRQAPGK GLEWVS | SISGS---GSYIYYADS VKG | RFTISRDNAKTISLYLQVNGL RAEDTAVYYCAR | SKF------------DS | WGQGT LVTVS S |
| iPS:4 35539 | 21-225_158G1 | VH3/3-21/D6/6-6/RF2/JH 4 | EVQWVES-GGGLVKPGGSLRL SCAASG-FTFS | S------YGMN | WVRQAPGK GLEWIS | SISGS---GSYIYYADS VKG | RFTISRDNAKNSLYLQMNSL RAEDTAVYYCAI | SSG------------WS | WGQGT LVTVS S |
| iPS:4 35583 | 21-225_160F2 | VH3/3-21/D6/6-6/RF2/JH 4 | EVQLVES-GGGLVKPGGSLRL SCAASG-FTFS | S------YGMN | WVRQAPGK GLEWIS | SISGS---GSYIYYADS VKG | RFTISRDNAKNSLYLQMNSL RAEDTAVYYCAR | SSG------------WS | WGQGT LVTVS S |
| | | Germline | | | | | | | |
| | VH3/3-21/D11-1/RF2/JH5 | | | | | | | | |
| iPS:4 68846 | 21-225_53B10 | VH3/3-21/D1/1-1/RF2/JH 5 | EVQLVES-GGGLVKPGGSLRL SCAASG-FTFS | S------YSMN | WVRQAPGK GLEWVS | SISGS---SSYIYYVDS VKG | RFTISRDNAKNSLYLQMNSL RAEDTAVYYCAR | VNS------------FDS | WGQGT LVTVS S |
| iPS:4 34251 | 21-225_62G3 | VH3/3-21/D1/1-1/RF2/JH 5 | EVQLVES-GGGLVKPGGSLRL SCAASG-FTFS | S------YSMN | WVRQAPGK GLEWVS | SISSS---SSYIYYADS VKG | RFTISRDNAKNSLYLQMNSL RAEDTAVYYCAR | VNS------------FDS | WGQGT LVTVS S |
| iPS:4 34407 | 21-225_68G8 | VH3/3-21/D1/1-1/RF2/JH 5 | EVQLVES-GGGLVKPGGSLRL SCAASG-FTFS | S------YSMN | WVRQAPGK GLEWVS | SISGS---SSYIYYADS VMG | RFTISRDNAKNSLYLQMNSL RAEDTAVYYCAR | VNS------------FDS | WGQGT LVTVS S |
| iPS:4 35575 | 21-225_159H11 | VH3/3-21/D1/1-1/RF2/JH 5 | EVQLVES-GGGLVKPGGSLRL SCAASG-FTFS | S------YTMN | WVRQAPGK GLEWVS | SISGS---SSYIYYADS VKG | RFTISRDNAKNSLYLQMNSL RAEDTAVYYCAR | VSW------------ADC | WGQGT LVTVS S |
| | | Germline | | | | | | | |
| | VH3/3-23/D11-1/RF2/JH4 | | | | | | | | |

Figure 51 (Continued)

| | | | H FR1 | H CDR1 | H FR2 | H CDR2 | H FR3 | H CDR3 | H FR4 |
|---|---|---|---|---|---|---|---|---|---|
| iPS:4 68848 | 21-225_54B1 | VH3/3-23/D1/1-1/RF2/JH4 | EVQLLES-GGGLVQPGGSLRL SCAASG-FTFS | S-----YAMS | WVRQAPGK GLEWVS | VLSGS---GGSTFYADS VKG | RFTISRENSKNTLYLQMSSL RAEDTAVYYCAR | RGREYSG------YDYFDY | WGQGT LVTVS S |
| iPS:4 33993 | 21-225_47G7 | VH3/3-23/D1/1-1/RF2/JH4 | EVQLLES-GGGLVQPGGSLRL SCAASG-FTFS | S-----YAMS | WVRQAPGK GLEWVS | AISGR---GGNTFYAES VRG | RFTISRDNSKNTLYLQMNSL RAEDTAVYYCAR | IIREQ-------WAFDY | WGQGT LVTVS S |
| iPS:4 34007 | 21-225_48D7 | VH3/3-23/D1/1-1/RF2/JH4 | EVQLLES-GGGLVQPGGSLRL SCAASG-FTFR | N-----SAMN | WVRQAPGK GLEWVS | AISGS---GGTTFYADS VKG | RFTISRDNSKNTLYLQINSL RAEDTAVYYCAR | CGREQ-------WLDY | WGQGT LVTVS S |
| iPS:4 34115 | 21-225_53E4 | VH3/3-23/D1/1-1/RF2/JH4 | EVQLLES-GGGLVQPGGSLRL SCAASG-FTFS | S-----YVMS | WVRQAPGK GLEWVS | GISGS---GGRTYYADS VKG | RFNISRDNSKNTLYLQMNSL RAEDTAVYYCAR | VAL---------FDY | WGQGT LVTVS S |
| iPS:4 35679 | 21-225_169D10 | VH3/3-23/D1/1-1/RF2/JH4 | EVQLLES-GGGLVQSGGSLRL SCAASG-FTFS | S-----YVMS | WVRQAPGK GLEWVS | AISGS---GSRIYYADS VKG | RFTISRDNSKNTLYLQMNSL RAEDTALYYCAR | VAF---------FDY | WGQGT LVTVS S |
| iPS:4 35685 | 21-225_170E1 | VH3/3-23/D1/1-1/RF2/JH4 | EVQLLES-GGGLVQPGGSLRL SCAASG-FTFS | S-----YVMS | WVRQAPGK GLEWVS | AISGS---GNRIYYADS VKG | RFTISRDNSKNTLYLQMNSL RAEDTAVYYCAR | VAF---------FDY | WGQGT LVTVS S |
| iPS:4 36632 | 21-225_227E4 | VH3/3-23/D1/1-1/RF2/JH4 | EGQLLES-GGGLVQPGGSLRL SCTASG-FTFS | T-----FAMT | WVRQAFGR GLEWVS | VISGR---GGSSFYADS VKG | RFTISRDNTRNTLYLQMNSL RAEDTAVYYCAR | DQLW--------FDY | WGQGT LVTVS S |
| Germline | VH4/4-39/D4/4-11/RF2/JH5 | | QLQLQES-GPGLVKPSETLSL TCTVSG-GSIS | SS----SYWG | WIRQPPGK GLEWIG | SIYY----SGSTYYNPS LKS | RVTISVDTSKNQFSLKLSSV TAADTAVYYCAR | DYNT | WGQGT LVTVS S |
| iPS:4 68856 | 21-225_77C9 | VH4/4-39/D4/4-11/RF2/JH5 | QLQLQES-GPGLVTPSETLSL TCTVSG-GSIS | RS----SYYWG | WIRQPPGK GLEWIG | SIYY----SGSAYSNPS LKS | RVTISVDTSKNQFSLKLSSV TAADTALFYCAR | LDSNW-------GLDY | WGQGT LVTVS S |
| iPS:4 34489 | 21-225_74E4 | VH4/4-39/D4/4-11/RF2/JH5 | QLQLQES-GPGLVTPSETLSL TCTVSG-GSIS | SS----NYYWG | WIRQPEGK GLEWIG | SIYY----SGYTSYNPS LKS | RVTISVDSSKNHFSLRLSSV TAADTAVYYCAR | LDSNW-------GLDY | WGQGT LVTVS S |
| iPS:4 35251 | 21-225_96A3 | VH4/4-39/D4/4-11/RF2/JH5 | QLQLQES-GPGLVKPSETLSL TCTVSG-GSIS | SS----NYYWG | WIRQPPGK GLEWIG | SIYY----SGYTSYNPS LKS | RVTISVDSSKNHFSLRLSSV TAADTAVYYCAR | LDSNW-------GLDY | WGQGT LVTVS S |
| iPS:4 37346 | 21-225_75H7 | VH4/4-39/D4/4-11/RF2/JH5 | QLQLQES-GPGLVTPSETLSL TCTVSG-GSIS | RS----SYYWG | WIRQPPGK GLEWIG | SIYY----SGSAYSNPS LKS | RVTISVDSSKNQFSLKLSSV TAADTALFYCAR | LDSNW-------GLDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 93886 | 21-225_2G9 | VH4|4-39/D4|4-11|RF2/JH5 | QLQLQES-GPGLVKPSETLSLTCTVSG-GSIR | PN----YYWG | WIRQPPGK GLEWIG | SIYY----SGSTSYNPS LNS | RVTISVDTSKNQFSLKLNSV TAADTAVYYCAR | LSSNW----------DFDN | WGQGT LVTVS S |
| iPS:3 93928 | 21-225_4E10 | VH4|4-39/D4|4-11|RF2/JH5 | QLQLQES-GPGLVKPSETLSLTCTVSG-GSLS | RS---SYYWG | WIRQPPGK GLEWIG | SVYY----SGATSYNPS LKS | RVTISVDTSKNQFSLKLNSV TAADTALYCVR | LSSNW----------DFDY | WGQGT LFTVS S |
| | Germline | VH1|1-02/D6|6-6|RF1/JH6 | | | | | | | H_FR4 |
| iPS:4 68862 | 21-225_178H8 | VH1|1-02/D6|6-6|RF1/JH6 | QVQLVQS-GAEVRTPGASVKV SCKASG-YIFT | D------YMH | WVRQAPGQ GLEWMG | WINPN----RGGTNYAQK FQG | RVTMTRDTSISTAYMELSRL RSEDTAVYYCAR | EEDRSGNY---------YYYGMDV | WGQGT TVTVS S |
| iPS:4 51112 | 21-225_53D10 | VH1|1-02/D6|6-6|RF1/JH6 | QVQLVQS-GAEVKKPGASVKV SCKASG-YIFT | G------YVIH | WVRQAPGQ GLEWMG | WINPN----SGGTNYAQK FQG | RVTMTRDTSISTAYMELIRL RSEDTAVYYCAR | ENESLATRP---------FYDYGMDV | WGQGT TVTVS S |
| | Germline | VH2|2-05/D6|6-6|RF2/JH4 | | | | | | | H_FR4 |
| iPS:4 68864 | 21-225_60D6 | VH2|2-05/D6|6-6|RF2/JH4 | QITLKES-GPTLVKPTQTLTL TCTFSG-FSLS | TS----GVGVG | WIRQPPGK ALEWLA | LIYW----KDDERYSPS LKS | RLITTKDTSKNQVVLTMTNM DPVDTATYYCAH | AVAV----------SFDY | WGQGT LVTVS S |
| iPS:4 36850 | 21-225_57D9 | VH2|2-05/D6|6-6|RF2/JH4 | QITLKES-GPMLVKPTQTLTL TCTFSG-FSLS | TS----GVGVG | WIRQPPGK ALEWLA | LIYW----NDDKRYSPS LKS | RLITTKDTSKNQVVLTMTNM DPVDTATYYCAH | AVAV----------SFDY | WGQGT LVTVS S |
| iPS:4 36914 | 21-225_76B4 | VH2|2-05/D6|6-6|RF2/JH4 | QITLKES-GPTLVKPTQTLTL TCTFSG-FSLS | TG----GVGVG | WIRQPPGK ALEWLA | LIYW----DDDKRYSPS LKS | RLITTKDTPKNQVVLTMTNM DPVDTATYYCAH | LIAV----------AFDY | WGQGT LVTVS S |
| iPS:4 36918 | 21-225_77A2 | VH2|2-05/D6|6-6|RF2/JH4 | QITLKES-GPSLVKPTQTLTL TCTFSG-FSLS | TS----GVGVG | WIRQPPGK ALEWLV | FIYW----DDDKRYSPS LKS | RLITTKDTSKNQVVLTMTNM DPVDTATYYCAH | LIAV----------AFDY | WGQGT LVTVS S |
| iPS:4 36934 | 21-225_96B5 | VH2|2-05/D6|6-6|RF2/JH4 | QITLKES-GPTLVKPTQTLTL TCTFSG-FSLS | TG----GVGVG | WIRQPPGK ALEWLA | LIYW----DDDKRYSPS LKS | RLITTKDTPKNQVVLTMTNM DPVDTATYYCAH | LIAV----------ACDY | WGQGT LVTVS S |
| iPS:4 37334 | 21-225_75F11 | VH2|2-05/D6|6-6|RF2/JH4 | QITLKES-GPTLVKPTQTLTL TCTFSG-FSLS | TG----GVGVG | WIRQPPGK ALEWLA | LIYW----DDDKRYSPS LKS | RLITTKDTPKNQVVLTMTNM DPVDTATYYCAH | LIAV----------AFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 37377 | 21-225_74G9 | VH2J2-05/D6J6-6/RF2JH4 | QITLKES-GPTLVKPTQLTL TCTFSG-FSLS | TG---GVGVG | WIRQPPGK ALEWLA | LIYW----DDCKRYSPS LKS | RLIITKDTPKNQVVLTMTNM DPVDTATYYCAH | LIAV--------AFDY | WGQGT LVTVS S |
| iPS:3 92583 | 21-225_10B10 | VH2J2-05/D6J6-6/RF2JH4 | QITLKES-GPTLVKPTQLTL TCTFSG-FSLS | TG---GVGVG | WIRQPPGK ALEWLV | FIYW----SDDKRYSPS LKS | RLSITKDTSKNQVVLTMTNM DPVDTATYYCAR | IAAV--------AFDY | WGQGT LVTVS S |
| iPS:3 93184 | 21-225_15H11 | VH2J2-05/D6J6-6/RF2JH4 | QITLKES-GLTLMKPTQLTL TCTFSG-FSLS | TG---GVGVG | WIRQPPGK ALEWLA | LIYW----HDDKRYSPS LRS | RLIITKDTSKNQVVLTMTNM DPVDTATYYCAR | IVAV--------AFDY | WGQGT LITVS S |
| iPS:3 93212 | 21-225_30H6 | VH2J2-05/D6J6-6/RF2JH4 | QITLKES-GPTLVKPTQLTL TCTFSG-FSLS | TG---GVGVG | WIRQPPGK ALEWLA | LIYW----HDDKRYSPS LKS | RLAITKDTSKNQVVLTIINM DPVDTATYYCAH | LIAV--------AFDY | WGQGT LVTVS S |
| iPS:3 93222 | 21-225_17F5 | VH2J2-05/D6J6-6/RF2JH4 | QITLKES-GPSLVKPTQLTL TCTFSG-FSLS | TS---GVGVG | WIRQPPGK ALEWLA | LIYW----DDDKRYSPS LKS | RLIITKDTSKNQVVLTMTNM DPVDTATYYCAR | LIAV--------AFDY | WGQGT LVTVS S |
| iPS:3 93224 | 21-225_31C2 | VH2J2-05/D6J6-6/RF2JH4 | QITLKES-GPTLVKPTQLTL TCTFSG-FSLN | TG---GVGVG | WIRQPPGK ALEWLA | LIYW----NDCERYSPS LKS | RLIITKDTSKNQVVLTMTNM DPLDTASYYCAH | LIAV--------SFDY | WGQGA LVTVS S |
| | Germline | | | | | | | | |
| | VH1J1-02/D6J6-19/RF2JH6 | | | | | | | | |
| iPS:4 68866 | 21-225_190C1 | VH1J1-02/D6J6-19/RF2JH6 | QVQLVQS-GAEVKKPGASVKV SCKASG-YTFT | G-----YYMH | WVRQAPGQ GLEWMG | WINPY---SGGTNYAQK FQG | RVTMTRDTSISTAYMELSRL RSDDTAVYYCAR | DRAVAGNY--------FYYGMDV | WGQGT TVTVS S |
| iPS:4 36972 | 21-225_190C7 | VH1J1-02/D6J6-19/RF2JH6 | QVQLVQS-GAEVKKPGASVKV SCKASG-YTFT | G-----YYMH | WVRQAPGQ GLEWMG | WINPN---SGGTNYAQK FQG | RVTMTRDTSISTAYMELSRL RSDDTAVYYCAR | DRAVAGNY--------FYYGMDV | WGQGT TVTVS S |
| iPS:4 37020 | 21-225_193F11 | VH1J1-02/D6J6-19/RF2JH6 | QVQLVQS-GAEVKKPGASVKV SCKASG-YTFT | G-----YYMH | WVRQAPGQ GLEWMG | WINPY---SGGTNYAQK FQD | RVTMTRDTSITTAYMELSRL RSDDTAVYYCAR | DRAVAGNY--------FYYGMDV | WGQGT TVTVS S |
| iPS:4 37036 | 21-225_195H9 | VH1J1-02/D6J6-19/RF2JH6 | QVQLVQS-GAEVKKPGASVKV SCKASG-YTFT | G-----YYMH | WVRQAPGQ GLEWMG | WINPN---SGGTNYAQK FQD | RVTMTRDTSITTAYMELSRL RSDDTAVYYCAR | DRAVAGNY--------FYYGMDV | WGQGT TVTVS S |
| iPS:4 37042 | 21-225_197E8 | VH1J1-02/D6J6-19/RF2JH6 | QVQLLQS-GAEVRKPGASVRV SCKASG-YTFT | G-----YYIH | WVRQAPGQ GLEWMG | WINPN---SGGTNYAQR FQG | RVTMTRDTSITTAYMELSRL RSDDTAVYYCAR | EIAVAGNY--------FYYGMGV | WGQGT TVAVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4:4-39D1\|1-1\|RF2JH4 | | QLQLQES SGPGLVKPSETLSL TLSVTSG-GSIS | GS---SYYRG | WIRQPPGK GLEWIG | NIYY---- SGSTYHNPS LKS | RVTISVDTSKNQFSLKLTSV TAADTAVFYCAR | VQLER-------------HDLLW---------SLDF | WGQGT LVTVS S |
| iPS:4 68868 21-225_74A1 | VH4\|4-39D1\|1-1\|RF2JH4 | QLQLQES-GPGLVKPSETLSL TCTVSG-GSIS | GS---SYYRG | WIRQPPGK GLEWIG | NIYY---- SGSTYHNPS LKS | RVTISVDTSKNQFSLKLTSV TAADTAVFYCAR | HDLLW---------SLDF | WGQGT LVTVS S |
| | Germline | H_FR1 | H_CDR1 | H_FR2 | H_CDR2 | H_FR3 | H_CDR3 | H_FR4 |
| VH1\|1-02D3\|3-22\|RF2\|JH5 | | QVQLVQS- GAEVKKPGASVKV SCKASG-YTFT | G------YYMH | WVRQAPGQ GLEWMG | WINPN---- SGGTNYAQK FQG | RVTMTRDTSISTAYMELSRL RSDDTAVYYCAR | VSYASS--------YYNEFDP | WGQGT LVTVS S |
| iPS:4 72742 21-225_30D9_LC2 | VH1\|1-02D3\|3-22\|RF2\|JH5 | QVKLVQS- GAEVEKPGASVKV SCKASG-YTFT | G------YYLH | WVRQAPGQ GLEWMG | WINPN---- SGGTNYAQK FQG | RVTMTRDTSISTAYMELSRL RSDDTAVYYCAR | VYYYGSSG--------YYNEFDN | WGQGT LVTVS S |
| iPS:4 72741 21-225_30D9_LC1 | VH1\|1-02D3\|3-22\|RF2\|JH5 | QVKLVQS- GAEVKKPGASVKV SCKASG-YTFT | G------YYLH | WVRQAPGQ GLEWMG | WINPN---- SGGTNYAQK FQG | RVTMTRDTSISTAYMELSRL RSDDTAVYYCAR | VYYYGSSG--------YYNEFDN | WGQGT LVTVS S |
| iPS:4 37040 21-225_196E7 | VH1\|1-02D3\|3-22\|RF2\|JH5 | QVQLVQS- GAEVKKPGASVKV SCKVSG-YTFT | G------YNMH | WVRQAPGQ GLEWMG | WINPN---- SGGTNYAHK FQG | RVTMTRDTSISTAYMELSRL RSDDTAVYYCAR | DYYDTSG--------EGWFDP | WGQGT LVTVS S |
| iPS:4 37050 21-225_197C11 | VH1\|1-02D3\|3-22\|RF2\|JH5 | QVQLVQS- GAEVKKPGASVKV SCKVSG-YTFT | G------YNMH | WVRQAPGQ GLEWMG | WINPN---- SGGTNYAHK FQG | RVTMTRDTSISTAYMELSRL RSDDTAVYYCAR | DYYDSSG--------EGWFDP | WGQGT LVTVS S |
| iPS:3 93214 21-225_33A1 | VH1\|1-02D3\|3-22\|RF2\|JH5 | QVQLVQS- GAEVKKPGASVKV SCKASG-YTFS | G------YYMH | WVRQAPGQ GLEWMG | WINPN---- NGGTHYAQK FQG | RVTMTRDTSIRTASMELSRL RSDDTAVFYCAR | GYYYASSG--------YYNDLDP | WGQGT LVTVS S |
| | Germline | H_FR1 | H_CDR1 | H_FR2 | H_CDR2 | H_FR3 | H_CDR3 | H_FR4 |
| VH1\|1-02D3\|3-22\|RF2\|JH4 | | QVQLVQS- GAEVKKPGASVKV SCKASG-YTFT | G------YYMH | WVRQAPGQ GLEWMG | WINPN---- SGGTNYAQK FQG | RVTMTRDTSIRTASMELSRL RSDDTAVYYCAR | VSYASS--------YYYFDY | WGQGT LVTVS S |
| iPS:4 72743 21-225_68G6 | VH1\|1-02D3\|3-22\|RF2\|JH4 | QVQLVQF- GGEVKKPGSSVKV SCKASG-YTFT | G------YYMH | WVRQAPGQ GLEWMG | SIYRN---- SGGTNYAQK FQG | RVTMTRDKSISTAYMEKSRI RSDDTAVYYCAR | APYYGSGT--------YYNEFDY | WGQGT LVTVS S |
| iPS:4 36902 21-225_69B11 | VH1\|1-02D3\|3-22\|RF2\|JH4 | QVQLVQS- GAEVKKPGASVRV SCKASG-YTFT | G------YYMH | WVRQAPGQ GLEWMG | WINPN---- SGGTNYGQK FQD | RVTMTRDTSISTAFMELSRL RSDDTAAYYCAR | TYYYGSSG--------YYNGFDY | WGQGT LVTVS S |
| iPS:4 36904 21-225_71D4 | VH1\|1-02D3\|3-22\|RF2\|JH4 | QVQLVQS- GAEVKKPGASVKV SCKASG-YTFT | G------YCMH | WVRQAPGQ GLEWMG | WINPN---- SGGTNYAQK FQV | RVTMTRDISVSTVYMDLSRL RSDDTAVYYCAR | AYYYGSGT--------YHNEFDY | WGQGS LVTVS S |

Figure 51 (Continued)

| | | | | | | | | | |
|---|---|---|---|---|---|---|---|---|---|
| iPS:4 36906 | 21-225_72B4 | VH1j1-02jD3j3-22jRF2jJH4 | QVQLVQS-GAEVKKPGASVKVSCKASG-YTFT | G-----YYMH | WVRQAPGQGLEWMG | WINPN---SGGTNYGQKFQG | RVTMTRDISISTAYMELSRLRSDDTAVYYCAR | TYYYGSGT----YNGFDY | WGQGTLVTVSS |
| iPS:4 37034 | 21-225_195E9 | VH1j1-02jD3j3-22jRF2jJH4 | QVQVVQS-GAEVKKPGASVKVSCKASG-YTFT | G-----YYMH | WVRQAPGQGLEWMG | WINPN---SGATNYAQKFQG | RVTMTRDTSISTAYMELNRLRSDDTAVYYCAR | AYYYGSGT----YNEFDY | WGQGTLVTVSS |
| iPS:3 92598 | 21-225_18E10 | VH1j1-02jD3j3-22jRF2jJH4 | QVQLVQS-GAEVKKPGASVKVSCKASG-YTFT | G-----YYMH | WVRQAPGQGLEWMG | WINPN---SGGTNYAQKFQG | RVTMTRDISINTAYMELSRLRSDDTAVYYCAR | SYYYGSGT----YNEFDY | WGQGTLVTVSS |
| iPS:3 93182 | 21-225_4B3 | VH1j1-02jD3j3-22jRF2jJH4 | QVQLVQS-GAEVKKPGASVKVSCKASG-YTFT | G-----YYMH | WVRQAPGQGLEWMG | WINPN---SGGTNSAQKFQG | RVTMTRDISISTAYMELSRLRSDDTAVYYCAR | SYYYGSGT----YNEFDY | WGQGTLVTVSS |
| iPS:3 93200 | 21-225_35E1 | VH1j1-02jD3j3-22jRF2jJH4 | QVKLVQS-GAEVKKPGASVKVSCKASG-YTFT | G-----YYMH | WVRQAPGQGLEWMG | WINPK---SGGTNYAQKFQG | RVTMTRDISISTVYMEPSRLRSDDTAVYYCAR | VYYHGSGS----YNEFDY | WGQGTLVTVSS |
| iPS:3 93206 | 21-225_13F6 | VH1j1-02jD3j3-22jRF2jJH4 | QVQLVQS-GAEVKKPGASVKVSCKASG-YTFT | G-----YYMH | WVRQAPGQGLEWMG | WINPN---SGGANYAQKFQG | RVTMTRDISISTAYMELSRLRSDDTAVYYCAR | SFYYGSGT----YNEFDY | WGQGTLVTVSS |
| iPS:3 93208 | 21-225_16F3 | VH1j1-02jD3j3-22jRF2jJH4 | QVQLVQS-GAEVKKPGASVKVSCKASG-YTFT | G-----HYMH | WVRQAPGQGLEWMG | WINPN---SGGTNYAQKFQG | RVTMTRDISISTAYMELSRLRSDDTAVYYCAR | SYYYGSGT----YNEFDY | WGQGTLVTVSS |
| iPS:3 93210 | 21-225_17D3 | VH1j1-02jD3j3-22jRF2jJH4 | QVQLVQS-GAEVKKPGASVKVSCKASG-YTFT | G-----YYMH | WVRQAPGQGLEWMG | WINPN---SGGTDYAQKFQG | RVTMTRDISISTAYMELSRLRSDDTAVYYCAR | ANYYGSGS----YNDFDY | WGQGTLVTVSS |
| iPS:3 93226 | 21-225_33E6 | VH1j1-02jD3j3-22jRF2jJH4 | QVQLVQS-GAEVKKPGASVKVSCKASG-YTFT | G-----YYMH | WVRQAPGQGLEWMG | WINPN---SGGTNYAQKFQG | RVTMTRDISISTAYMELSRLRSDDTAVYYCAR | VYYYGSGS----YNEFDY | WGQGTLVTVSS |
| iPS:3 93230 | 21-225_9G9 | VH1j1-02jD3j3-22jRF2jJH4 | QVQLVQS-GAEVKKPGASVKVSCKASG-YTFT | G-----YYIH | WVRQAPGQGLEWMG | WINPN---SGGTDYAQKFQG | RVTMTRDISISTAYMELSRLRSDDTAVYYCAR | SYYYGSGT----YNEFDY | WGQGTLVTVSS |
| iPS:3 98490 | 21-225_21D12 | VH1j1-02jD3j3-22jRF2jJH4 | QVQLVQS-GAEVKKPGASVKVSCKASG-YTFT | D-----YYIH | WVRQAPGQGLEWMG | WINPN---SGGTNNAQKFQG | RVTMTRDISISTAYMELSRLRSDDTAVYYCAR | SYYYGSGT----YNEFDY | WGQGTLVTVSS |
| iPS:4 23018 | 21-225_31D12_LC2 | VH1j1-02jD3j3-22jRF2jJH4 | QVKLVQS-GAEVKKPGASVKVSCKASG-YTFT | G-----YYMH | WVRQAPGQGLEWMG | WINPN---SGGTNYVQKFQG | RVTMTRDISISTAYMELSRLRSDDTAVYYCAR | VYYYGSGS----YNEFDY | WGQGTLVTVSS |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 23019 | 21-225_31D12_L C1 | VH1|1-02|D3|3-22|RF2|J H4 | QVKLVQS-GAEVKKPGASVKV SCKAASG-YTFT | G------YYMH | WVRQAPGQ GLEWMG | WINPN---SGGTNIVQK FQG | RVTMTRDTSISTAYMELSRL RSEDTAVYYCAR | VYYYGGSS------------YYNEFDY | WGQGT LVTVS S |
| | | Germline | | | | | | | |
| | VH3|3-33|D7|7-27|RF2|JH4 | | QVQLVES-GGGVVQPGRSLRL SCAASG-FTFS | S------YGMH | WVRQAPGK GLEWVA | VIWYD---ESNKYYADS VKG | RFTISRDNSKNTLYLQMNSL RAEDTAVYYCAR | | WGQGT LVTVS S |
| iPS:3 92920 | 21-225_29G4 | VH3|3-33|D7|7-27|RF2|J H4 | QVQLVES-GGGVVQPGRSLRL TCAASG-FTFS | D------YGIH | WVRQAPGK GLEWVA | VIWYD---ESNKYYADS MKG | RFTISRDNSKNTLYLQMNSL RAEDTAVYYCAR | ELGM----------------TGDY | WGQGT LVTVS S |
| iPS:4 33899 | 21-225_43C3 | VH3|3-33|D7|7-27|RF2|J H4 | QVQLVES-GGGVVQPGRSLRL SCAASG-FTFS | S------YGIH | WVRQAPGK GLEWVA | VIWYD---ENNKYYADS VKG | RFTISRDNSKNTLYLQMNSL RAEDTAVYYCAR | ELGF----------------SNDY | WGQGT LVTVS S |
| iPS:4 33921 | 21-225_44C3 | VH3|3-33|D7|7-27|RF2|J H4 | QVQLVES-GGGVVQPGRSLRL SCAASG-FTFS | S------YGMH | WVRQAPGK GLEWVA | VIWFE---GSNKYYADS VKG | RFTISRDNSKNTLYLQMSSL RAEDTAVYYCVR | ELGF----------------STDY | WGQGT LVTVS S |
| iPS:4 33933 | 21-225_44C8 | VH3|3-33|D7|7-27|RF2|J H4 | QVQLVES-GGGVVQPGRSLRL SCAASG-FTFN | N------YGMH | WVRQAPGK GLEWVA | VIWYD---GSNKYYADS VKG | RFTISRDNSKNTLYLYQMNSL RAEDTAVYYCVR | ELGF----------------LSDY | WGQGT LVTVS S |
| iPS:4 33969 | 21-225_46F3 | VH3|3-33|D7|7-27|RF2|J H4 | QVQLVES-GGGVVQPGRSLRL SCAASG-FTFS | D------YGMH | WVRQAPGK GLEWVA | VIWFE---GSNKYYADS VKG | RFTISRDNSKNTLYLYQVNSL RAEDTAVYYCVR | ELGF----------------SNDY | WGQGT LVTVS S |
| iPS:4 33975 | 21-225_46C6 | VH3|3-33|D7|7-27|RF2|J H4 | QVQLVES-GGGVVQPGRSLRL SCAASG-FTFS | S------YGIH | WVRQAPGK GLEWVA | VIWYD---ENNKYYADS VKG | RFTISRDNSKNTLYLQMNSL RAEDTAVYYCAR | ELGF----------------SNDY | WGQGT LVTVS S |
| iPS:4 33977 | 21-225_46D8 | VH3|3-33|D7|7-27|RF2|J H4 | QVQLVES-GGGVVQPGRSLRL SCAASG-FTFS | D------YGIH | WVRQAPGK GLEWVA | VIWFE---GSNKYYADS VKG | RFTISRDNSKNTLYLYQVNSL RAEDTAVYYCVR | ELGF----------------SNDY | WGQGT LVTVS S |
| iPS:4 33983 | 21-225_47A1 | VH3|3-33|D7|7-27|RF2|J H4 | QVQLVES-GGGVVQPGRSLRL SCAASG-FTFS | D------YGMH | WVRQAPGK GLEWVA | VIWYD---DYNKKYADS VKG | RFTISRDNAKNTLYLQVNSL RVEDTAVYYCAT | ELGM----------------LFDY | WGQGT LVTVS S |
| iPS:4 33997 | 21-225_48C1 | VH3|3-33|D7|7-27|RF2|J H4 | QVQLVES-GGGVVQPGRSLRL SCAASG-FTFS | S------YGMH | WVRQAPGK GLEWVA | VVWYD---EINKKYYADS VKG | RVTISRDNSKNTLYLQMNSL RAEDTAMYYCAR | ELGW----------------EADY | WGQGT LVTVS S |
| iPS:4 34009 | 21-225_48A9 | VH3|3-33|D7|7-27|RF2|J H4 | QVQLVES-GGGVVQPGRSLRL SCAASG-FTFS | S------YGMH | WVRQAPGK GLEWVA | VIWYE---ENKKYYADS VKG | RFTISRDNSKNTLFLQMNSL RAEDTAMYFCAR | ELAW----------------YEDY | WGQGT LVTVS S |

Figure 51 (Continued)

| | | | | | | | | | |
|---|---|---|---|---|---|---|---|---|---|
| iPS:4 34013 | 21-225_48D12 | VH3J3-33/D7J7-27[RF2]JH4 | QVQLVES-GGGVVQPGRSLRL SCAASG-FTFS | D-----YGMH | WVRQAPGR GLEWVA | VIWYD---VSNKYYVDS VKG | RFTISRDNSKNTLYLQMNSL RAEDTAVYYCAR | ELGM-------RSDY | WGQGT LVTVS S |
| iPS:4 34019 | 21-225_49A1 | VH3J3-33/D7J7-27[RF2]JH4 | QVQLVES-GGGVVQPGRSLRL SCAASG-FTFS | D-----YGMH | WVRQAPGK GLEWVA | VIWYD---EDNKYYVDS VKG | RFTISRDNSKNTLYLQMNSL RAEDTAVYYCAR | ELGF-------LSDY | WGQGT LVTVS S |
| iPS:4 34029 | 21-225_49C6 | VH3J3-33/D7J7-27[RF2]JH4 | QVQLVES-GGGVVQPGRSLRL SCAASG-FTFS | N-----YGMH | WVRQAPGK GLEWVA | VIMFD---VSNKKYYVDS VKG | RFTISRDNSKNTLYLQMSSL RAEDTAVYYCAR | DLGM-------IEDY | WGQGT LVTVS S |
| iPS:4 34057 | 21-225_51E4 | VH3J3-33/D7J7-27[RF2]JH4 | QVQLVES-GGGVVQPGRSLRL SCAASG-FTFS | S-----YGMH | WVRQAPGK GLEWVA | VIWYD---ESNKYYADS VKG | RFTISRDNSKNTLYLQMNSL RAEDTAVYYCAR | ELGF-------LSDY | WGQGT LVTVS S |
| iPS:4 34071 | 21-225_51F9 | VH3J3-33/D7J7-27[RF2]JH4 | QVQLVES-GGGVVQPGRSLRL SCAASG-FTFS | D-----YGMH | WVRQAEGK GLEWVA | VIWFD---GNNKYYADS VKG | RFTISRDNSKNTLYLQMNSL SAEDTAVYYCAR | ELGF-------LSDY | WGQGT LVTVS S |
| iPS:4 34075 | 21-225_51B11 | VH3J3-33/D7J7-27[RF2]JH4 | QVQLVES-GGGVVQPGRSLRL SCAASG-FTFS | D-----YGMH | WVRQAPGK GLEWVA | VIMFG---GNNKYYGDS VKG | RFTISRDNSKNTLYLQMNSL SAEDTAVYYCAR | ELGF-------LSDY | WGQGT LVTVS S |
| iPS:4 34077 | 21-225_51F11 | VH3J3-33/D7J7-27[RF2]JH4 | QVQLVES-GGGVVQPGRSLRL SCAASG-FTFS | N-----FGMH | WVRQAPGK GLEWVA | VIWYE---ESNKYYADS VKG | RFTISRDNSKNTLYLQMNSL RAEDTAVYYCAR | ELGF-------LSDF | WGQGT LVTVS S |
| iPS:4 34081 | 21-225_52B2 | VH3J3-33/D7J7-27[RF2]JH4 | QVQLVES-GGGVVQPGRSLRL SCAASG-FTFS | N-----YGMH | WVRQAPGK GLEWVA | VTWFD---GSNQRYADS VKG | RFTISRDISKNTLYLQMNSL SAEDTAVYYCAR | DLGM-------IEDF | WGQGT LVTVS S |
| iPS:4 34091 | 21-225_52B9 | VH3J3-33/D7J7-27[RF2]JH4 | QVQLVES-GGGVVQPGRSLRL SCAASG-FTFS | D-----YGMH | WVRQAPGK GLEWVA | VIWFD---GNNKYYADS VKG | RFTISRDNSKNTLYLQMNSL SAEDTAVYYCAR | ELGF-------LSDY | WGQGT LVTVS S |
| iPS:4 34105 | 21-225_53D2 | VH3J3-33/D7J7-27[RF2]JH4 | QVQLVES-GGGVVQPGRSLRL SCAASG-FTFS | N-----YGMH | WVRQAPGK GLEWVT | VVWDD---GSNKYYADS VKG | RFTISRDNSKNTLYLQMNSL RAEDTAVYYCTR | GLGF-------TGDY | WGQGA LVTVS S |
| iPS:4 34119 | 21-225_53E6 | VH3J3-33/D7J7-27[RF2]JH4 | QVQLVES-GGGVVQPGRSLRL SCTISG-FTFS | D-----YGIH | WVRQAPGK GLEWVA | VIWYD---ESNKYYADS VKG | RPAISRDNSKNTLYLQMNSL RAEDTAVYYCVR | ELGM-------TSDY | WGQGT LVTVS S |
| iPS:4 34129 | 21-225_53B12 | VH3J3-33/D7J7-27[RF2]JH4 | QVQLVES-GGGVVQPGRSLRL SCAASG-FTFS | N-----FGMH | WVRQAPGK GLEWVA | VVWYD---GNNRYYADS VKG | RFTISRDNSKNTLYLQMHSL RAEDTAVYYCAR | ELGF-------LSDF | WGQGT LVTVS S |

Figure 51 (Continued)

| | | | | | | | | | |
|---|---|---|---|---|---|---|---|---|---|
| iPS:4 34131 | 21-225_54D3 | VH3]3-33/D7]7-27]RF2/J H4 | QVQLVES-GGGVVQPGRSLRL SCAASG-FTFS | N-----YGMH | WVRQAPGK GLEWVA | VIWFD---GNNNYYADS VKG | RFTISRDNSKNTLYLQMNSL RAEDTAVYYCAR | ELGF--------LSDY | WGQGT LVTVS S |
| iPS:4 34141 | 21-225_54C6 | VH3]3-33/D7]7-27]RF2/J H4 | QVQLVES-GGGVVQPGRSLRL SCTISG-FTFS | D-----YGIH | WVRQAPGK GLDWVA | VIWYD---ENNKYYADS VKG | RFAISRDNSKNTLYLQMNSL RAEDTAVYYCVR | ELGM--------TSDY | WGQGT LVTVS S |
| iPS:4 34143 | 21-225_54G7 | VH3]3-33/D7]7-27]RF2/J H4 | QVQLVES-GGGVVQPGRSLRL SCAASG-FTFS | N-----YGMH | WVRQAPGK GLEWVA | VIWYE---ESNKYYGDS VKG | RFTISRDNSKNTLYLQMNSL RAEDTAVYYCAR | ELGF--------LSDY | WGQGT LVTVS S |
| iPS:4 34155 | 21-225_55B3 | VH3]3-33/D7]7-27]RF2/J H4 | QVQLVES-GGGVVQPGRSLRL SCAASG-FTFS | S-----YGMH | WVRQAPGK GLEWVA | VIWFD---GNNKYYEDS VKG | RFTISRDNSKNTLYLQMNSL RAEDTAVYYCVR | ELGF--------LSDY | WGQGT LVTVS S |
| iPS:4 34199 | 21-225_59F11 | VH3]3-33/D7]7-27]RF2/J H4 | QVQLVES-GGGVVQPGRSLRL SCAASG-FTFS | N-----YGMH | WVRQAPGK GLEWVA | VIWYD---ESNKHYADS VKG | RFTISRDNSKTTLYLQMSSL RAEDTAVYYCSR | ELGM--------NGDY | WGQGT LVTVS S |
| iPS:4 34207 | 21-225_60A3 | VH3]3-33/D7]7-27]RF2/J H4 | QVQLVES-GGGVVQPGRSLRL SCAASG-FTFS | S-----YGMH | WVRQAPGK GLEWVA | VIWYE---ESNKYYADS VKG | RFTISRDNSKNTLYLQMNSL RAEDTAVYYCAR | ELGM--------TGDY | WGQGT LVTVS S |
| iPS:4 34253 | 21-225_62E4 | VH3]3-33/D7]7-27]RF2/J H4 | QVQLVES-GGGVVQPGRSLRL SCAASG-FTFS | D-----YGMH | WVRQAPGK GLEWVA | VIWYD---RSNKYYADS VKG | RFTISRDNSKNTLYLQMNSL RVEDTAVYHCAR | ELGF--------SSDY | WGQGT LVTVS S |
| iPS:4 34271 | 21-225_57A4 | VH3]3-33/D7]7-27]RF2/J H4 | QVQLVES-GGGVVQPGRSLRL SCAASG-FTFS | D-----YGMH | WVRQAPGK GLEWVA | VIWYA---GSNKYYVDS VKG | RFTISRDNSKNTLYLQMNSL RAEDTAVYYCAR | ELGM--------RSDY | WGQGT LVTVS S |
| iPS:4 34293 | 21-225_58F5 | VH3]3-33/D7]7-27]RF2/J H4 | QVQLVES-GGGVVQPGRSLRL SCVASG-FTFS | D-----YGMH | WVRQAPGK GLEWVA | VIWYA---GSNKYHVDS VKG | RFTISRDNSKNTLYLQMNSL RAEDTAVYYCAR | ELGM--------RSDY | WGQGT LVTVS S |
| iPS:4 34337 | 21-225_64E1 | VH3]3-33/D7]7-27]RF2/J H4 | QVQLVES-GGGVVQPGRSLRL SCAASG-FTFS | S-----YGMH | WVRQAPGK GLEWVA | VIWFD---ETNKYYGDS VKG | RFTISRDNSKNTLYLQMNSL RAEDTAVYYCAR | ELGF--------SSDY | WGQGT LVTVS S |
| iPS:4 34357 | 21-225_65C1 | VH3]3-33/D7]7-27]RF2/J H4 | QVQLVES-GGGVVQPGRSLRL SCAASG-FTFS | D-----YGMH | WVRQAPGK GLEWVA | VIWFE---GSNKHYTDS VKG | RFTISRDNSKNTLYLQMNSL RAEDTAVYYCAR | ELGF--------SSDY | WGQGT LVTVS S |
| iPS:4 34375 | 21-225_66C7 | VH3]3-33/D7]7-27]RF2/J H4 | QVQLVES-GGGVVQPGRSLRL SCVASG-FTFS | D-----YGMH | WVRQAPGK GLEWVA | VIWFE---GSHKYYTDS VKG | RFTISRDNSKNTLYLQMNSL RAEDTAVYYCAR | ELGF--------SSDY | WGQGT LVTVS S |

Figure 51 (Continued)

| | | | | | | | | |
|---|---|---|---|---|---|---|---|---|
| iPS:4 34411 | 21-225_68F11 | VH3/3-33/D7/7-27/RF2/J H4 | QVQLVES-GGGVVQPGRSLRL SCAASG-FTFS | D------YGMH | WVRQAPGK GLEWVA | VIWYD--- VSNKYYADS VKG | RFTISRDNSKNTLYLQMNSL RAEDTAVYYCAR | ELGM--------TSDC | WGQGT LVTVS S |
| iPS:4 34441 | 21-225_71A2 | VH3/3-33/D7/7-27/RF2/J H4 | QVQLVES-GGGVVQPGRSLRL SCAISG-FTFS | D------YGMH | WVRQAPGK GLEWVA | VIWYD--- ESNKYYADS VKG | RFTISRDNSKNTLYLQMNSL RAEDTAVYYCAR | ELGW--------QDDY | WGQGT LVTVS S |
| iPS:4 34447 | 21-225_71B6 | VH3/3-33/D7/7-27/RF2/J H4 | QVQLVES-GGGVVQPGRSLRL SCAASG-FTFS | N------YGMH | WVRQAPGK GLEWVA | VIWYD--- RTNKYYADS VKG | RFTISRDNSKNTLHLQMNSL RAEDTAVYYCAR | ELGM--------LSDY | WGQGT LVTVS S |
| iPS:4 34453 | 21-225_71B11 | VH3/3-33/D7/7-27/RF2/J H4 | QVQLVES-GGGVVQPGRSLRL SCAASG-FTFS | D------YGMH | WVRQAPGK GLEWVA | VIWYD--- RNNKYYGDS VKG | RFTISRDNSKNTLYLQMNSL RAEDTAVYYCAR | ELGM--------LSDY | WGQGT LVTVS S |
| iPS:4 34457 | 21-225_72G12 | VH3/3-33/D7/7-27/RF2/J H4 | QVQLVES-GGGVVQPGRSLRL SCAASG-FTFS | S------YGMH | WVRQAEDT GLEWVA | VIWFD--- ESNKYYADS VKG | RFTISRDNSKNTLYLQMNSL RAEDTAVYYCAR | ELGF--------SSDY | WGQGT LVTVS S |
| iPS:4 35311 | 21-225_146H9 | VH3/3-33/D7/7-27/RF2/J H4 | QVQLVES-GGGVVQPGRSLRL SCAASG-FSFS | S------YGMH | WVRQAPGK GLEWVA | VIWFD--- ESNKHYGDS VKG | RFTISRDNSKNTLYLQMNSL RAEDTAVYYCAR | ELGF--------LSDY | WGQGT LVTVS S |
| iPS:4 35511 | 21-225_157C3 | VH3/3-33/D7/7-27/RF2/J H4 | QVQLVES-GGGVVQPGRSLRL SCAASG-FTFS | T------YGMH | WVRQAPGK GLEWVA | VIWYD--- VNNKYYADS VKG | RFTISRDNSKNTLYLQMNSL RAEDTAVYYCAR | ELGF--------LSDY | WGQGT LVTVS S |
| iPS:4 35533 | 21-225_157H8 | VH3/3-33/D7/7-27/RF2/J H4 | QVQLVES-GGGVVQPGRSLRL SCAASG-FTFS | S------YGMH | WVRQAPGK GLEWVA | VIWYD--- VNNKYYADS VKG | RFTISRDNSKNTLYLQMNSL RAEDTAVYYCAR | ELGF--------LSDY | WGQGI LVTVS S |
| iPS:4 35551 | 21-225_158H6 | VH3/3-33/D7/7-27/RF2/J H4 | QVQLVES-GGGVVQPGRSLRL SCAVSG-FTFS | S------YGMH | WVRQAPGK GLEWVA | VIWYD--- VTNKYYADS VKG | RFTISRDNSKNTLYLQMNSL RQEDTAVYYCVR | ELGW--------AEDY | WGQGT LVTVS S |
| iPS:4 35569 | 21-225_159C5 | VH3/3-33/D7/7-27/RF2/J H4 | QVQLVES-GGGVVQPGRSLRL SCAASG-FTFS | S------YGIH | WVRQAPGK GLEWVA | VVWYD--- VNNKYYADS VKG | RFTISRDNSKNTLYLQMNSL RAEDTAVYYCAR | ELGF--------LSDY | WGQGT LVTVS S |
| iPS:4 36268 | 21-225_203B9 | VH3/3-33/D7/7-27/RF2/J H4 | QVQLVES-GGGVVQPGRSLRL SCAASG-FTLS | S------FGMH | WVRQAPGK GLEWVA | VIWYD--- VNNKYYADS VKG | RFTISRDNSKNTLYLQMNSL RPEDTAVYYCAR | ELGF--------LSDY | WGQGT LVTVS S |
| iPS:4 36328 | 21-225_207F12 | VH3/3-33/D7/7-27/RF2/J H4 | QVQLVES-GGGVVQPGRSLRL SCAASG-FTFS | N------YGMH | WVRQAPGK GLEWVA | VIWYD--- RNNKYYGDS VKG | RFTISRDNSKNTLYLQMNSL RAEDTAVYYCAR | ELGF--------LFDY | WGQGT LVTVS S |

Figure 51 (Continued)

| | | | | | | | | |
|---|---|---|---|---|---|---|---|---|
| iPS:4 336556 | 21-225_224D10 | VH3J3-33/D7J7-27/RF2J H4 | QVQLVES-GGGLVQPGKSLRL SCAASG-FTFS | S-----YGMH | WVRQAPGK GLEWVA | VIWYE---GSNKYYVDS VRG | RFTISRDNSKSTLYLQMNSL RAEDTAVYYCVR | ELGF--------QSDY | WGQGT PVTVS S |
| iPS:3 92618 | 21-225_16F10 | VH3J3-33/D7J7-27/RF2J H4 | QVQLVES-GGGVVQPGRSLRL SCAASG-FTFS | D-----YGMH | WVRQAPGK GLEWVA | VIWYD---GNNKYYVDS VKG | RFTISRDNSKNTLYLQMNSL RAEDTAVYYCAR | ELAW--------YEDY | WGQGT LVTVS S |
| iPS:3 92626 | 21-225_18A5 | VH3J3-33/D7J7-27/RF2J H4 | QVQLVES-GGGVVQPGRSLRL SYTASG-FTFS | D-----YGMH | WVRQAPGK GLEWVA | VIWFD---GSNKYYADS VKG | RFTISRDNSKNTLYLQMNSL RAEDTAVYYCAR | DLGW--------TEEY | WGQGT LVTVS S |
| iPS:3 92630 | 21-225_20E5 | VH3J3-33/D7J7-27/RF2J H4 | QVQLVES-GGGVVQPGRSLRL SCAASG-FTFS | D-----YGMH | WVRQAPGK GLEWVA | VIWYE---ENNQYYADS VKG | RFTISRDNSKNTLYLQMNSL RAEDTAVYYCAR | ELGF--------RSDY | WGQGT LVTVS S |
| iPS:3 92640 | 21-225_18A1 | VH3J3-33/D7J7-27/RF2J H4 | QVQLVES-GGGVVQPGRSLRL SCAASG-FTFS | S-----YGMH | WVRQAPGK GLEWVA | VIWYE---ENNKYYVDS VKG | RFTISRDNSKSTLYLQMNSL RAEDTAVYYCVR | ELGF--------QSDY | WGQGT PVTVS S |
| iPS:3 92644 | 21-225_19E1 | VH3J3-33/D7J7-27/RF2J H4 | QVQLVES-GGGVVQPGRSLRL SCAVSG-FTFS | N-----YGMH | WVRQAPGK GLEWVA | VIWYE---ENNKYYADS VKG | RFTISRDNSKNTLYLQMNSL RAEDTAVYYCAR | ELGF--------RSDY | WGQGT LVTVS S |
| iPS:3 92654 | 21-225_17A10 | VH3J3-33/D7J7-27/RF2J H4 | QVQLVES-GGGVVQPGRSLRL SCAASG-FTFS | N-----YGMH | WVRQAPAK GLEWMA | VIWYD---ENNQYYADS VKG | RFTISRDNSKNTLYLQMNSL RAEDTAVYYCAR | ELGF--------RSDY | WGQGT LVTVS S |
| iPS:3 92658 | 21-225_18E8 | VH3J3-33/D7J7-27/RF2J H4 | QVQLVES-GGGVVQPGRSLRL SCAASG-FTFS | N-----YGMH | WVRQAPGK GLEWVA | VIWYE---VTNKYYADS VKG | RFTVSRDNSKNTLFLQMNSL RAEDTAVYYCAR | ELGF--------RSDY | WGQGT LVTVS S |
| iPS:3 92666 | 21-225_16F11 | VH3J3-33/D7J7-27/RF2J H4 | QVQMVES-GGGVVQPGRSLRL SCEASG-FTFS | S-----YGMH | WVRQAPGK GLEWVA | VIWYE---ENNQYYVDS VKG | RFTISRDNSKSTLYLQMNSL RAEDTAVYYCVR | ELGF--------QSDY | WGQGT PVTVS S |
| iPS:3 92674 | 21-225_18C2 | VH3J3-33/D7J7-27/RF2J H4 | QVQLVES-GGGVVQPGRSLRL SCAASG-FTFS | D-----YGMH | WVRQAPGK GLEWMA | VIWYE---VTNKYYADS VKG | RFTISRDNSKNTLYLQMNSL SAEDTAVYYCAR | ELGW--------YEDY | WGQGT LVTVS S |
| iPS:3 92680 | 21-225_20A7 | VH3J3-33/D7J7-27/RF2J H4 | QVQLVES-GGGVVQPGRSLRL SCAASG-FTFS | N-----YGMH | WVRQAPGK GLEWVA | VIWYE---ENNQYYADS VKG | RFTISRDNSKNTLYLQMNSL RAEDTAIYYCAR | ELGF--------RSDY | WGQGT LVTVS S |
| iPS:3 92686 | 21-225_17C7 | VH3J3-33/D7J7-27/RF2J H4 | QVQLVES-GGGVVQPGKSLRL SCAASG-FTFS | D-----YGMH | WVRQAPGK GLEWVA | VIWFD---GSNKYYADS VKG | RFTISRDNSKNTLYLQMNSL RAEGTAVYYCAR | DLGW--------TEEY | WGQGT LVTVS S |

Figure 51 (Continued)

| | | | | | | | | | |
|---|---|---|---|---|---|---|---|---|---|
| iPS:3 92690 | 21-225_18F2 | VH3]3-33/D7[7-27[RF2/J H4 | QVQLVES-GGGVVQPGRSLRL SCAASG-FTFS | D-----YGMH | WVRQAPGK GLEWVA | VIWFD---GSNKYVDS VKG | RFTISRDNSKNTLYLQMNSL RVEDTAVYYCAR | DLGW------------ | ------TEEY | WGQGT LVTVS S |
| iPS:3 92716 | 21-225_17B5 | VH3]3-33/D7[7-27[RF2/J H4 | QVQLVES-GGGVVQPGRSLRL SCAASG-FTFS | D-----YGMH | WVRQAPGK GLEWVA | VIWYD---ESNKHYIDS VKG | RFTISRDNSKNTLYLQMNSL RAEDTAVYYCVR | ELGF------------ | ------RFDY | WGQGT LVTVS S |
| iPS:3 92732 | 21-225_17E5 | VH3]3-33/D7[7-27[RF2/J H4 | QVQLVES-GGGVVQPGRSLRL SCAASG-FTFS | D-----YGMH | WVRQAPGK GLEWVA | LIWYD---VTNKYYGDS VKG | RFTISRDNSQNTLYLQLNSL RAEDTAVYYCAR | ELGW------------ | ------YEDY | WGQGT LVTVS S |
| iPS:3 92744 | 21-225_20D5 | VH3]3-33/D7[7-27[RF2/J H4 | QVQLVES-GGGVVQPGRSLRL SCAASG-FTFS | S-----YGMH | WVRQAPGK GLEWVA | VIWYE---ENNQYYADS VKG | RFTISRDNSKNTLYLQMNSL RAEDTAVYYCAR | ELGF------------ | ------RSDY | WGQGT LVTVS S |
| iPS:3 92758 | 21-225_21G11 | VH3]3-33/D7[7-27[RF2/J H4 | QVQLVES-GGGVVQPGRSLRL SCAASG-FTFS | D-----YGMH | WVRQAPGK GLEWMA | VIWYD---VTNEYYADS VKG | RFTISRDNSKNTLYLQMNSL RAEDTAVYYCAR | ELGW------------ | ------YEDY | WGQGT LVTVS S |
| iPS:3 92772 | 21-225_20E12 | VH3]3-33/D7[7-27[RF2/J H4 | QVQLVES-GGGVVQPGRSLRL SCAASG-FTFS | S-----YGMH | WVRQAPGK GLEWVA | VMWYD---ESNKHYADS VKG | RFTISRDNSKNTLYLQMNSL RAEDTAVYYCAR | ELGF------------ | ------RFDY | WGQGT LVTVS S |
| iPS:3 92790 | 21-225_20D10 | VH3]3-33/D7[7-27[RF2/J H4 | QVQLVES-GGGVVQPGRSLRL SCAASG-FTFS | D-----YGMH | WVRQAPGK GLEWVA | VIWFD---GSNKYVDS VKG | RFTISRDNSKNTLYLQMNSL RVEDTAVYYCAR | DLGW------------ | ------TEEY | WGQGT LVTVS S |
| iPS:3 92796 | 21-225_22A4 | VH3]3-33/D7[7-27[RF2/J H4 | QVQLVES-GGGVVQPGRSLRL SCAASG-FTFS | D-----YGIH | WVRQAPGK GLEWVA | VIWYD---GSNKYVDS VKG | RFTISRDNSKNTLYLQMNSL RAEDTAVYYCAR | DLGW------------ | ------TEEY | WGQGT LVTVS S |
| iPS:3 92810 | 21-225_20H12 | VH3]3-33/D7[7-27[RF2/J H4 | QVQLVES-GGGVVQPGRSLRL SCAASG-FTFS | N-----YGMH | WVRQAPGK GLEWVA | VIWYD---ENNKYVDS VKG | RFTISRDNSKNTLYLQMNSL RAEDTAVYYCAR | ELGF------------ | ------RSDY | WGQGT LVTVS S |
| iPS:3 92832 | 21-225_21H8 | VH3]3-33/D7[7-27[RF2/J H4 | QVQLVES-GGGVVQPGRSLRL SCAASG-FTFS | D-----YGMH | WVRQAPGK GLEWVA | VIWFD---GSNKYVDS VKG | RFTISRDNSKNTLYLQMNSL RAEDTAVYYCAR | DLGW------------ | ------TEEY | WGQGT LVTVS S |
| iPS:3 92854 | 21-225_21E5 | VH3]3-33/D7[7-27[RF2/J H4 | QVQLVES-GGGVVQPGRSLRL SCSASG-FTFS | D-----YGMH | WVRQAPGK GLEWVA | VIWYD---ESNKYADS VKG | RITISRDNSKNTLYLQMNSL RAEDTAMYCTR | ELGF------------ | ------RSDY | WGQGT LVTVS S |
| iPS:3 92860 | 21-225_22H8 | VH3]3-33/D7[7-27[RF2/J H4 | QVQLVES-GGGVVQPGRSLRL SCAASG-FTFS | S-----YGMH | WVRQAPGK GLEWVA | VIWYD---GNNKYADS VKG | RFTISRDNSKNTLYLQMNSL RAEDTAVYYCAR | ELAW------------ | ------YEDY | WGQGT LVTVS S |

Figure 51 (Continued)

| | | | | | | | | |
|---|---|---|---|---|---|---|---|---|
| iPS:3 92866 | 21-225_23H11 | VH3J3-33/D7J7-27JRF2/J H4 | QEQLVES-GGGVVQPGRSLRL SCAASG-FTFS | S-----YGMH | WVRQAPGK GLEWVA | VIWYD---ENNKYVDS VKG | RFTISRDNSKNTLYLQMNSL RAEDTAVYYCAR | ELGF--------RSDY | WGQGT LVTVS S |
| iPS:3 92876 | 21-225_21F7 | VH3J3-33/D7J7-27JRF2/J H4 | QVQLVES-GGGVVQPGRSLRL SCAASG-FTFS | D-----YGMH | WVRQAPGK GLEWVA | VIWFD---GNNKYVDS VKG | RFTISRDNSKNLYLQMNSL RAEDTAVYYCVR | DLGW--------TEEY | WGQGT LVTVS S |
| iPS:3 92880 | 21-225_22F9 | VH3J3-33/D7J7-27JRF2/J H4 | QVQMVES-GGGVVQPGRSLRL SCAASG-FTFS | S-----YGMH | WVRQAPGK GLEWVA | VIWYD---ENNKDYVDS VKG | RFTISRDNSKSTYLQMNSL RAEDTAVYYCAR | ELGF--------QSDY | WGQGT PVTVS S |
| iPS:3 92894 | 21-225_21G2 | VH3J3-33/D7J7-27JRF2/J H4 | QVQLVES-GGGVVQPGRSLRL SCAASG-FTFS | D-----YGMH | WVRQAPGK GLEWMA | VIWYD---VTNKYYADS VKG | RFTISRDNSKNTLYLEMNSL RAEDTAVYYCAR | ELGW--------YEDY | WGQGT LVTVS S |
| iPS:3 92900 | 21-225_22F2 | VH3J3-33/D7J7-27JRF2/J H4 | QVQLVES-GGGVVQPGRSLRL SCAASG-FTFS | D-----YGMH | WVRQAEGK GLEWVA | VIWYE---GSNKYYVDS VRG | RFTISRDNSKSTLYLQMNSL RAEDTAVYYCVR | ELGF--------QSDY | WGQGT PVTVS S |
| iPS:3 92908 | 21-225_23F12 | VH3J3-33/D7J7-27JRF2/J H4 | QVQLVES-GGGVVQPGRSLRL SCVASG-FTFS | S-----YGMH | WVRQAPGK GLEWVA | VIWYD---ETNKYYADS VKG | RFTISRDNSKNTLYLQMNSL RAEDTAIYYCAR | ELAW--------YEDY | WGQGS LVTVS S |
| iPS:3 92918 | 21-225_28F5 | VH3J3-33/D7J7-27JRF2/J H4 | QVQLVES-GGGVVQPGRSLRL SCAASG-FTFS | S-----YGMH | WVRQAPGK GLEWVA | VIWYD---ENNKYYADS VKG | RFTISRDNSKNNLYLQMNSL RGEDTALYYCAR | ELGF--------YDDY | WGQGT LVTVS S |
| iPS:3 92934 | 21-225_27D5 | VH3J3-33/D7J7-27JRF2/J H4 | QVQLVES-GGGVVQPGRSLRL SCAASG-FTFS | S-----YGMH | WVRQAPGK GLEWVA | VIWYE---ESNKYYGDS VKG | RFTISRDNSKNLYLQMNSL RAEDTAVYYCAR | ELGW--------LSDY | WGQGT LVTVS S |
| iPS:3 92958 | 21-225_28C7 | VH3J3-33/D7J7-27JRF2/J H4 | QVQLVES-GGGVVQPGRSLRL SCAASG-FTFS | S-----YGMH | WVRQAPGK GLEWVA | VIWYE---ESNKYYADS VKG | RFTISRDNSKNTLYLQMNSL RAEDTAVYYCAR | ELGW--------YDDY | WGQGT LVTVS S |
| iPS:3 92968 | 21-225_25B6 | VH3J3-33/D7J7-27JRF2/J H4 | QVQLVES-GGGVVQPGRSLRV SCTASG-FTLR | N-----YGMH | WVRQAPGK GLEWVA | VIWYE---ESNKYYTES VKG | RFTISRDNSKNTLYLQMNSL RAEDTAVYYCAR | ELGF--------LSDY | WGQGT LVTVS S |
| iPS:3 92972 | 21-225_26A2 | VH3J3-33/D7J7-27JRF2/J H4 | QVQLVES-GGGVVQPGRSLRL SCAASG-FTFS | S-----YGMH | WVRQAPGK GLEWVT | VIWYD---GSNKYYADS VKG | RFTISRDNSKNLYLQMNSL RAEDTAVYYCAR | ELGW--------YDDY | WGQGT LVTVS S |
| iPS:3 92980 | 21-225_29H6 | VH3J3-33/D7J7-27JRF2/J H4 | QVQLVES-GGGVVQPGRSLRL SCAASG-FTFS | D-----YGMH | WVRQAPGK GLEWVA | VIWYN---ENNKYYADS VKG | RFTISRDNSKNTLYLQMNSL RAEDTAVYYCAR | ELGM--------TGDS | WGQGT LVTVS S |

Figure 51 (Continued)

| | | | | | | | | |
|---|---|---|---|---|---|---|---|---|
| iPS:3 92988 | 21-225_25E6 | VH3]3-33|D7|7-27|RF2|J H4 | QVQLVES-GGGVVQPGRSLRL SCAASG-FTFS | D------YGMH | WVRQAPGK GLEWVA | VIWYD---ENNKYYADS VKG | RFTISRDNSKNTLYLQMNSL RAEDTALYYCAI | ELGM--------TGDS | WGQGT LVTVS S |
| iPS:3 92990 | 21-225_25H10 | VH3]3-33|D7|7-27|RF2|J H4 | QVQLVES-GGGVVQPGRSLRL SCAASG-FTFS | D------YGMH | WVRQAPGK GLEWVA | VIWYD---ESNKYYADS MKG | RFTISRDNSKNTLYLQMNSL RAEDTAVYYCAR | ELGM--------TGDY | WGQGT LVTVS S |
| iPS:3 93000 | 21-225_29D7 | VH3]3-33|D7|7-27|RF2|J H4 | QVQLVES-GGGVVQPGRSLRL SCAASG-FTFS | S------YGMH | WVRQAPGK GLEWVA | VIWYD---ESNKYYGDS VKG | RFTISRDNSKNTLYLQMNSL RGEDTALYYCAR | ELGF--------LSDY | WGQGT LVTVS S |
| iPS:3 93018 | 21-225_29B8 | VH3]3-33|D7|7-27|RF2|J H4 | QVQLVES-GGGVVQPGRSLRL SCAASG-FTFS | D------YGMH | WVRQAPGK GLEWVA | VIWYD---ENNKYYADS VKG | RFTISRDNSKNTLYLQMNSL RAEDTAVYYCAR | ELGM--------TGDS | WGQGT LVTVS S |
| iPS:3 93030 | 21-225_25H11 | VH3]3-33|D7|7-27|RF2|J H4 | QVQLVES-GGGVVQPGRSLRL SCAASG-FTFS | D------YGMH | WVRQAPGK GLEWVA | VIWYD---ENNEYYADS VKG | RFTISRDNSKNTLYLQMNSL RAEDTAVYYCAR | ELGM--------TGDS | WGQGT LVTVS S |
| iPS:3 93034 | 21-225_27F2 | VH3]3-33|D7|7-27|RF2|J H4 | QEQLVES-GGGVVQPGRSLRL SCAASG-FTFS | D------YGMH | WVRQAPGK GLEWVA | VIWYD---ENNKYYVDS VRG | RFTISRDNSKNTLYLQMNSL RAEDTAVYYCAR | ELGM--------TGDS | WGQGT LVTVS S |
| iPS:3 93048 | 21-225_27C3 | VH3]3-33|D7|7-27|RF2|J H4 | QVQLVES-GGGVVQPGRSLRL SCAASG-FTFS | D------YGMH | WVRQAPGK GLEWVA | VIWYD---ENNKYYADS VKG | RFTISRDNSKNTLYLQMNSL RAEDTAVYYCAR | ELGM--------TGDS | WGQGT LVTVS S |
| iPS:3 93054 | 21-225_29G8 | VH3]3-33|D7|7-27|RF2|J H4 | QVQLVES-GGGVVQPGRSLRL SCAASG-FTFS | D------YGMH | WVRQAPGK GLEWVA | VIWYD---ETNKYYADS VKG | RFTISRDNSKNTLYLQMNSL RAEDTAVYYCAR | ELGM--------TSDY | WGQGT LVTVS S |
| iPS:3 93812 | 21-225_6A11 | VH3]3-33|D7|7-27|RF2|J H4 | QVQLVES-GGGVVQPGRSLRL SCAASG-FTFS | D------YGMH | WVRQAPGK GLEWVA | VIWFD---GSNKYYADS VKG | RFTISRDNSKNTLYLQMNSL RAEDTAVYDCAR | DLGW--------TEEY | WGQGT LVTVS S |
| iPS:3 93818 | 21-225_6G12 | VH3]3-33|D7|7-27|RF2|J H4 | QVQLVES-GGGVVQPGRSLRL SCAASG-FTFS | S------YGMH | WVRQAFGK GLEWVA | VIWYD---RSNNYYADS VKG | RFTISRDNSKNTLYLQMNSL RAEDTAVYYCAR | ELGF--------RSDY | WGQGT LVTVS S |
| iPS:3 93820 | 21-225_8H7 | VH3]3-33|D7|7-27|RF2|J H4 | QVQLVES-GGGVVQPGRSLRL SCPASG-FTFS | D------FGMH | WVRQAPGK GLEWVA | VIWYE---ENNQYYADS VKG | RFTISRDNSKNTLYLQMNSL RAEDTAVYYCAR | ELGF--------RSDY | WGQGT LVTVS S |
| iPS:3 93826 | 21-225_10G5 | VH3]3-33|D7|7-27|RF2|J H4 | QVQLVES-GGGVVQPGRSLRL SCAASG-FTFS | N------YGMH | WVRQAPGK GLEWVA | VIWYE---ENNQYYADS VKG | RFTISRDNSKNTLYLQMNSL RAEDTAVYYCTR | ELGF--------RSDY | WGQGT LVTVS S |

Figure 51 (Continued)

| | | | | | | | | |
|---|---|---|---|---|---|---|---|---|
| iPS:3 93828 | 21-225_10H12 | VH3\|3-33\|D7\|7-27\|RF2\|J H4 | QVQLVES-GGGVVQPGRSLRL SCAASG-FTFS | D-----YGMH | WVRQAPGK GLEWVA | VIWYD---DNNQYIADS VKG | RFTISRDNSKNTLYLQMNSL RAEDTAVYYCAR | ELGF------------RSDY | WGQGT LVTVS S |
| iPS:3 93830 | 21-225_12A1 | VH3\|3-33\|D7\|7-27\|RF2\|J H4 | QVQLVES-GGGVVQPGRSLRL SCAASG-FTFS | S-----YGMH | WVRQAPGK GLEWVA | VIWYE---ENNQYYADS VKG | RFTISRDNSKNTLYLQMNSL RAEDTAVYYCAR | ELGF------------RSDY | WGQGT LVTVS S |
| iPS:3 93838 | 21-225_6G2 | VH3\|3-33\|D7\|7-27\|RF2\|J H4 | LVQLVES-GGGVVQPGKSLRL SCAASG-FTFS | D-----YGIH | WVRQAPGK GLEWVA | VIWFD---GSNKYYADS VKG | RFTISSDNSKNTLYLQMNSL RAEDTAVYYCAR | DLGW------------TEEY | WGQGT LVTVS S |
| iPS:3 93854 | 21-225_7H11 | VH3\|3-33\|D7\|7-27\|RF2\|J H4 | QVQLVES-GGGVVQPGRSLRL SCSASG-FTFS | D-----YGMH | WVRQAPGK GLEWVA | VIWYD---ENNKYYADS VKG | RFTISRDNSKNTLYLQMNSL RAEDTAVYYCAR | ELGF------------RSDY | WGQGT LVTVS S |
| iPS:3 93866 | 21-225_14E3 | VH3\|3-33\|D7\|7-27\|RF2\|J H4 | QVQLVES-GGGVVQPGRSLRL SCAASG-FTFS | D-----FGMH | WVRQAPGK GLEWVA | VIWYE---ENNQYYADS VKG | RFTISRDNSKNTLYLQMNSL RAEDTAFYYCAR | ELGF------------RSDY | WGQGT LVTVS S |
| iPS:3 93876 | 21-225_9A1 | VH3\|3-33\|D7\|7-27\|RF2\|J H4 | QVQVVES-GGGVVQPGRSLRL SCAASG-FTFS | D-----YGMH | WVRQAPGK GLEWVA | VIWFD---GSNKYYADS VKG | RFTISRDNSKNTLYLQMNSL RAEDTAVYYCAR | DLGW------------TEEY | WGQGT PVTVS S |
| iPS:3 93882 | 21-225_15E3 | VH3\|3-33\|D7\|7-27\|RF2\|J H4 | QVQLVES-GGTVVQPGRSLRL SCAASG-FTFS | S-----YGMH | WVRQAPGK GLEWVA | VIWYE---ENNKHYADS VKG | RFTISRDNSKNTVYLQMNSL RAEDTAVYYCAR | ELGF------------RSDY | WGQGT LVTVS S |
| iPS:3 93884 | 21-225_16F4 | VH3\|3-33\|D7\|7-27\|RF2\|J H4 | QVQLVES-GGGVVQPGRSLRL SCAASG-FTFS | N-----YGMH | WVRQAPGK GLEWVA | VIWYD---GSNQYYGDS VKG | RFTISRDNSKNTVYLQMHSL RAEDTAVYYCAR | ELGF------------LSDY | WGQGT LVTVS S |
| iPS:3 93912 | 21-225_16F6 | VH3\|3-33\|D7\|7-27\|RF2\|J H4 | QVQLVES-GGGVVQPGRSLRL SCAASG-FTFS | N-----YGMH | RVRQAPGK GLEWVA | VIWYE---GSNQYYGDS VKG | RFTISRDNSKNTLYLQMNSL RAEDTAVYYCAR | ELGF------------LSDY | WGQGT LVTVS S |
| iPS:3 93922 | 21-225_2B2 | VH3\|3-33\|D7\|7-27\|RF2\|J H4 | QVQLVES-GGGVVQPGRSLRL SCAASG-FTFS | S-----YGMH | WVRQAPGK GLEWVA | VIWYE---ENNKYVDS VKG | RFTISRDNSKSTLYLQMNSL RAEDTAVYYCVR | ELGF------------QSDY | WGQGT PVTVS S |
| iPS:3 93934 | 21-225_13E6 | VH3\|3-33\|D7\|7-27\|RF2\|J H4 | QVQLVES-GGGVVQPGRSLRL SCAASG-FTFS | N-----YGMH | WVRQAPGK GLEWVA | VIWYD---ENNKYVDS VKG | RFTISRDNSKNTLYLQMNSL RAEDTAVYYCAR | ELGF------------RSDY | WGQGT LVTVS S |
| iPS:3 93948 | 21-225_16A5 | VH3\|3-33\|D7\|7-27\|RF2\|J H4 | QVQLVES-GGGVVQPGRSLRL SCAASG-FTFS | D-----YGMH | WVRQAPGK GLEWVA | VIWFD---GSNKYVDS VKG | RFTISRDNSKNTLYLQMSSL RAEDTAVYYCAR | DLGW------------TEEY | WGQGT LVTVS S |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:3 93960 | 21-225_7G2 | VH3-33/D7|7-27/RF2/JH4 | QVQLVES-GGGVVQPGRSLRLSCAASG-FTFS | D-----YGMH | WVRQAPGK GLEWMA | VIWYD---VTNKYADS VKG | RFTISRDNSKNTLYLQLNSL RAEDTAVYYCAR | ELGW--------YEDY | WGQGT LVTVS S |
| iPS:3 93974 | 21-225_7C4 | VH3-33/D7|7-27/RF2/JH4 | QVQLVES-GGGVVQPGKSLRLSCAASG-FTFS | N-----YGMH | WVRQAPGK GLEWVA | VIWYE---ENNQYYADS VKG | RFTISRDNSKNTLYLQMNSL RAEDTAVYYCAR | ELGF--------RSDY | WGQGT LVTVS S |
| iPS:3 93976 | 21-225_7E9 | VH3-33/D7|7-27/RF2/JH4 | QVQLVES-GGGVVQPGRSLRLSCAASG-FTFS | D-----YGMH | WVRQAPGK GLEWVA | VIWYD---ENNKYYVDS VKG | RFTISRDNSKNTLYLQMNSL RAEDTAVYYCAR | ELGF--------RSDY | WGQGT LVTVS S |
| iPS:3 93994 | 21-225_8C9 | VH3-33/D7|7-27/RF2/JH4 | QVQLVES-GGGVVQPGRSLRLSCAASG-FTFS | S-----YGMH | WVRQAPGK GLEWVA | VIWYD---ENNKYYVDS VKG | RFTISRDNSKNTLYLQMNSL RAEDTAVYYCAR | ELGF--------RSDY | WGQGT LVTVS S |
| iPS:3 93998 | 21-225_12B12 | VH3-33/D7|7-27/RF2/JH4 | QVQLVES-GGGVVQPGRSLRLSCAASG-FTFS | D-----YGMH | WVRQAPGK GLEWMA | VIWYD---VTNKYADS VKG | RFTISRDNSKNTLYLQMNSL RAEDTAVYYCAR | ELGW--------YEDY | WGQGT LVTVS S |
| iPS:3 94024 | 21-225_16B7 | VH3-33/D7|7-27/RF2/JH4 | QVQLVES-GGGVVQPGRSLRLSCAASG-FTFS | S-----YGMH | WVRQAPGK GLEWVA | VIWYD---ESNKYYADS VKG | RFTISRDNSKNTLYLQMNSL RAEDTAVYYCAR | ELGF--------LSDY | WGQGT LVTVS S |
| iPS:3 94059 | 21-225_9E8 | VH3-33/D7|7-27/RF2/JH4 | QVQLVES-GGGVVQPGRSLRLSCEASG-FTFS | S-----YGMH | WVRQAPGK GLEWVA | VIWYE---ENNQYYADS VKG | RFTISRDNSKNTLYLQMNSL RAEDTAVYYCAR | ELGF--------RSDY | WGQGT LVTVS S |
| iPS:3 94067 | 21-225_12F2 | VH3-33/D7|7-27/RF2/JH4 | QVQLVES-GGGVVQPGRSLRLSCAASG-FTFS | D-----YGMH | WVRQAPGK GLEWVA | VIWFD---GNNKYYVDS VKG | RFTISRDNSKNTLFLQMNSL RAEDTAVYYCVR | ELAW--------SEDY | WGQGT LVTVS S |
| iPS:3 94089 | 21-225_12E6 | VH3-33/D7|7-27/RF2/JH4 | QVQLVES-GGGVVQPGRSLRLSCAASG-FTFS | D-----YGMH | WVRQAPGK GLEWVI | VIWYD---ESNKYYADS VKG | RFTISHDDSKNTLYLQMNSL RAEDTAVYYCAR | ELAW--------YEDY | WGQGT LVTVS S |
| iPS:3 94097 | 21-225_16G7 | VH3-33/D7|7-27/RF2/JH4 | QVQLVES-GGGVVQPGRSLRLSCAASG-FTFT | D-----YGMH | WVRQAEGK GLEWVA | VIWYD---ENNEYYADS VKG | RFTISRANSKNTLYLQMNSL RAEDTAVYYCAR | ELAW--------YEDY | WGQGT LVTVS S |
| iPS:4 02219 | 21-225_1C12 | VH3-33/D7|7-27/RF2/JH4 | QVQLVES-GGGVVQPGRSLRLSCAASG-FTFS | N-----YGMH | WVRQAPGK GLEWVA | VIWYD---ENNKYYVDS VKG | RFTISRDNSKNTLYLQMNSL RAEDTAVYYCAR | ELGF--------RSDY | WGQGT LVTVS S |
| VH3-21/D4-11/RF2/JH4 | | | | | | | | | | |

Figure 51 (Continued)

| | | | | | | | | |
|---|---|---|---|---|---|---|---|---|
| iPS:4 33895 | 21-225_43E1 | VH3J3-21/D4J4-11/RF2/JH4 | EVQLVES-GGGLVKPGGSLRLSCAASG-FTFS | S------YSMN | WVRQAPGK GLEWVS | AISGN----STYIYYADS LKG | RFTISRDNAKNSLFQLNSL RAEDTAVYYCAR | DRG----------SE | WGQGT LVTVS S |
| iPS:4 34103 | 21-225_53G1 | VH3J3-21/D4J4-11/RF2/JH4 | EVQLVES-GGGLVKPGESLRLSCAASG-FTFS | S------YSMN | WVRQAPGK GLEWVS | SISGS----SSYIYYADS VKG | RFTISRDNAKNSLYLQMNSL RAEDTAVYYCAR | DRG----------ST | WGQGT LVTVS S |
| iPS:4 34179 | 21-225_56F1 | VH3J3-21/D4J4-11/RF2/JH4 | EVQLVES-GGGLVKFGGSLRLSCAASG-FTFS | S------YSMN | WVRQAPGK GLEWVS | SISIYYGDS STYIYYGDS VKG | RFTISRDNAKNSLYLQMNSL RAEDTAVYYCAR | DRG----------SS | WGQGT LVTVS S |
| iPS:4 34263 | 21-225_56H7 | VH3J3-21/D4J4-11/RF2/JH4 | EVQLVES-GGGLVKPGGSLRLSCAASG-FSFS | S------YSMN | WVRQAPGK GLEWVS | SISSS----STYIYYGDS VKG | RFTISRDNAKNSLYLQMNSL RAEDTAVYYCAR | DRG----------SS | WGQGT LVTVS S |
| iPS:4 35521 | 21-225_157H4 | VH3J3-21/D4J4-11/RF2/JH4 | EVQLVES-GGGLVKPGGSLRLSCAASG-FTFS | S------YSMN | WVRQAPGK GLEWVS | SISSS----STYIYYADS VKG | RFTISRDNAKNSLYLQMNSL RAEDTAVYYCAR | DRG----------SI | WGQGT LVTVS S |
| iPS:4 35527 | 21-225_157G7 | VH3J3-21/D4J4-11/RF2/JH4 | EVQLVES-GGGLVKPGGSLRFSCAASG-FTFS | S------YSMN | WVRQAPGK GLEWVS | SISGS----STYIYYADS VKG | RFTISRDNAKNSLYLQMNSL RAEDTAVYYCAR | DRG----------SS | WGQGT LVTVS S |
| iPS:4 35529 | 21-225_157H7 | VH3J3-21/D4J4-11/RF2/JH4 | EVQLVES-GGGLVKPGGSLRLSCAASG-FTFS | S------YSMN | WVRQAPGK GLEWVS | CISGS----SSYIYYADS VKG | RFTMSRDNAKNSLYLQMNSL RAEDTAVYYCVR | DRG----------GY | WGQGT LVTVS S |
| iPS:4 35547 | 21-225_158F5 | VH3J3-21/D4J4-11/RF2/JH4 | EVQLVES-GGGLVKPGGSLRLSCAASG-FTFS | S------YSMN | WVRQAPGK GLEWVS | SISGS----STYIYYADS VKG | RFTISRDNAKNSLYLQMNSL RAEDTAVYYCAR | DRG----------SS | WGQGT LVTVS S |
| iPS:4 35549 | 21-225_158H5 | VH3J3-21/D4J4-11/RF2/JH4 | EVQLVES-GGGLVKPGGSLRLSCAASG-FTFS | S------YSMN | WVRQAPGK GLEWVS | SISGS----STYIYYADS VKG | RFTISRDNAKNSLHLQMNSL RAEDTAVYYCAR | DRG----------SS | WGQGT LVTVS S |
| iPS:4 35553 | 21-225_158G8 | VH3J3-21/D4J4-11/RF2/JH4 | EVQLVES-GGGLVTPGGSLRLSCAASG-FTFS | S------YTMN | WVRQAEGK GLEWVS | LISGS----SSYIYYADS VKG | RFTISRDNAKNSLYLQMNSL RAEDTAVYYCAR | DRG----------SL | WGQGT LVTVS S |
| iPS:4 35581 | 21-225_160H1 | VH3J3-21/D4J4-11/RF2/JH4 | EVQLVES-GGGLVKPGGSLRLSCAASG-FTFS | S------YRMN | WVRQAPGK GLEWVS | SISSS----TGYMYYADS VKG | RFTISRDNAKNSLYLQMNSL RAEDTAVYFCAR | DK-----------DY | WGQGT LVTVS S |
| iPS:4 35593 | 21-225_160F4 | VH3J3-21/D4J4-11/RF2/JH4 | EVQLVES-GGGLVKPGGSLRFSCAASG-FTFS | S------YSMN | WVRQAPGK GLEWVS | SISGS----STYIYYADS VKG | RFTISRDNAKNSLYLQMNSL RAEDTAVYYCAR | DRG----------SS | WGQGT LVTVS S |

Figure 51 (Continued)

| | | | | | | | | |
|---|---|---|---|---|---|---|---|---|
| iPS:4 35617 | 21-225_162F2 | VH3J3-21/D4/4-11/RF2/J H4 | EVQLVES-GGGLVKPGGSLRF SCAASG-FTFS | S-----YSMN | WVRQAPGK GLEWVS | SISGS---STYIYADS VKG | RFTISRDNAKNSLYLQMNSL RAEDTAVYYCAR | DRG---------- | ----------SS | WGQGT LVTVS S |
| iPS:4 35621 | 21-225_162H3 | VH3J3-21/D4/4-11/RF2/J H4 | EVQLVES-GGGLVKPGGSLRL SCAASG-FTFS | S-----YSMN | RVRQAPGK GLEWVS | SISGS---STYIYADS VKG | RFTISRDNAKNSLYLQMNSL RAEDTAVYYCAR | DRG---------- | ----------SS | WGQGT LVTVS S |
| iPS:4 35641 | 21-225_163F9 | VH3J3-21/D4/4-11/RF2/J H4 | EVQLVES-GGGLVQPGGSLRL SCAASG-FTFS | S-----YSMN | WVRQAPGK GLEWVS | SISGS---STYIYADS VKG | RFTISRDNAKNSLYLQMNSL RAEDTAVYYCAR | DRG---------- | ----------SL | WGQGT LVTVS S |
| iPS:4 35719 | 21-225_171A11 | VH3J3-21/D4/4-11/RF2/J H4 | EVQLVES-GGGLVKPGGSLRL SCAASG-FTFS | S-----YSMN | WVRQAPGK GLEWVS | SISGS---SSYIYADS VKG | RFTISRDNAKNSLYLQMNSL RAEDTAVYYCAR | DRG---------- | ----------SS | WGQGT LVTVS S |
| iPS:4 36856 | 21-225_58C5 | VH3J3-21/D4/4-11/RF2/J H4 | EVQLVES-GGGLVKPGGSLRL SCAASG-FTFN | S-----YSMN | WVRQAPGK GLEWIS | SISSS---SYYLYADS VKG | RFTISRDSAKNSLYLQMNSL RAEDTAVYYCAR | TYSG---------- | ----------SFDY | WGQGT LVTVS S |
| iPS:4 48904 | 21-225_65C12 | VH3J3-21/D4/4-11/RF2/J H4 | EVQLVES-GGGLVKPGGSLRL SCAASG-FTFR | S-----FSLN | WVRQAPGK GLEWVS | SISGS---SSYIYADS VKG | RFTISRDNAKNSLYLQMNSL RAEDTAVYYCAR | DAY---------- | ----------SHY | WGQGT LVTVS S |
| iPS:4 72730 | 21-225_14B1_LC1 | VH3J3-21/D4/4-11/RF2/J H4 | EVQLVES-GGGLVKPGGSLRL SCAASG-FTFS | S-----YTMN | WVRQAPGK GLEWVS | SISGS---SSYLYPDS VKG | RFTISRDNAKNSLYLQMNSL RAEDTAVYYCAR | DRG---------- | ----------SS | WGQGT LVTVS S |
| iPS:4 72731 | 21-225_14B1_LC2 | VH3J3-21/D4/4-11/RF2/J H4 | EVQLVES-GGGLVKPGGSLRL SCAASG-FTFS | S-----YTMN | WVRQAPGK GLEWVS | SISGS---SSYLYPDS VKG | RFTISRDNAKNSLYLQMNSL RAEDTAVYYCAR | DRG---------- | ----------SS | WGQGT LVTVS S |
| iPS:3 92726 | 21-225_20B5 | VH3J3-21/D4/4-11/RF2/J H4 | EVQLVEA-GGGLVKPGGSLRL SCAASG-FTFT | S-----YSMN | WVRQAEGK GLEWVS | SISGS---GSHIYADS VKG | RFTISRDNAKNSLYLQMNSL RAEDTAVYYCAR | DRG---------- | ----------SY | WGQGT LVTVS S |
| iPS:3 92734 | 21-225_17D8 | VH3J3-21/D4/4-11/RF2/J H4 | EVQLVES-GGGLVKPGGSLRL SCAASG-FTFS | S-----YGLN | WVRQAPGK GLEWVS | SISGS---GSHISYADS VKG | RFTISRDNAKNSLYLQLNSL RAEDTAVYYCAR | DRG---------- | ----------SG | WGQGT LVTVS S |
| iPS:3 92768 | 21-225_20B8 | VH3J3-21/D4/4-11/RF2/J H4 | EVQLVES-GGGLVKPGGSLRL SCAASG-FTFS | S-----YSMN | WVRQAPGK GLEWVS | SISGS---SSYIYADS VKG | RFTISRDNAKNSLYLQMNSL RAEDTAVYYCAR | DRG---------- | ----------SG | WGQGT LVTVS S |
| iPS:3 92778 | 21-225_22H3 | VH3J3-21/D4/4-11/RF2/J H4 | AVQLVES-GGGLVKPGGSLRL SCAASG-FTFS | S-----YSMN | WVRQAPGK GLEWVS | SISSS---SSYIYADS VKG | RFTISRDNAKNSLYLQMNSL RAEDTAVFYCAR | DRG---------- | ----------SL | WGQGT LVTVS S |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:3 92788 | 21-225_20C8 | VH3/3-21|D4|4-11|RF2|JH4 | EVQLVES-GGGLVKPGGSLRLSCAASG-FTFS | S-----YSMN | WVRQAPGK GLEWVS | SISGS---SSYIYYADS VKA | RFTISRDNAKNSLYLQMNSL RAEDTAVYYCAR | DRG----------SL | WGQGT LVTVS S |
| iPS:3 92792 | 21-225_20G12 | VH3/3-21|D4|4-11|RF2|JH4 | EVQLVES-GGGLVKPGGSLRLSCAASG-FTFS | S-----YSMN | WVRQAPGK GLEWVS | SISGS---SSYIYYADS LKG | RFTISRDNAKNSLYLQMNSL RAEDTAVYYCAR | DRG----------SY | WGQGT LVTVS S |
| iPS:3 92844 | 21-225_23E11 | VH3/3-21|D4|4-11|RF2|JH4 | EVQLVES-GGGLVKPGGSLRLSCAASG-FTFS | S-----YTMN | WVRQAPGK GLEWVS | SISGS---SSYIWYVDS VKG | RFTISRDNAKNSLYLQMNSL RAEDTAVYYCAR | DRG----------SL | WGQGT LVTVS S |
| iPS:3 92848 | 21-225_20F9 | VH3/3-21|D4|4-11|RF2|JH4 | EVQLVES-GGGLVKPGGSLRLSCAASG-FTFS | S-----YSMN | WVRQAPGK GLEWVS | SISSS---SSYIYYADS VKG | RFTISRDNAKNSLYLQMNSL RAEDTAVYYCAR | DRG----------SC | WGQGT LVTIS S |
| iPS:3 92850 | 21-225_20H10 | VH3/3-21|D4|4-11|RF2|JH4 | EVQLVES-GGGLVKPGGSLRLSCAASG-FTFS | T-----YSMN | WVRQAPGK GLEWVS | SISSS---SSYIYYADS VKG | RFTISRDNAKNSLYLQMNSL RAEDTAIFYCAR | DRG----------SL | WGQGT LVTVS S |
| iPS:3 93006 | 21-225_31G9 | VH3/3-21|D4|4-11|RF2|JH4 | EVQLVES-GGGLVKPGGSLRLSCAASG-FTFS | S-----YSMN | WVRQAPGK GLEWVS | SISSS---SSYIYYADS VKG | RFTISRDNAKNSLYLQMNSL RAEDTAVYYCAR | DRG----------SS | WGQGT LVTVS S |
| iPS:3 93022 | 21-225_30H11 | VH3/3-21|D4|4-11|RF2|JH4 | EVQLVES-GGGLVKPGGSLRLSCAASG-FTFS | S-----YSMN | WVRQAPGK GLEWVS | SISGS---SSYIYYADS VKG | RFTISRDNAKNSLYLQMNSL RAEDTAVYYCAR | DRG----------SL | WGQGT LVTVS S |
| iPS:3 93130 | 21-225_33C2 | VH3/3-21|D4|4-11|RF2|JH4 | EVQLVES-GGGLVKPGGSLRLSCAASG-FTFS | S-----YTMN | WVRQAPGK GLQWVS | SISSS---SSYIYYADS VKG | RFTISRDNAKNSLFLQMNSL RAEDTAVYYCAR | DRG----------GT | WGQGT LVTVS S |
| iPS:3 93906 | 21-225_13D3 | VH3/3-21|D4|4-11|RF2|JH4 | EVQLVES-GGGLVKPGGSLRLSCAASG-FTFS | S-----YTMN | WVRQAPGK GLDWVS | SISGS---SSYIYYADS VKG | RFTISRDNAKNSLYLQMNSL RAEDTAVYYCAR | DRG----------SG | WGQGT LVTVS S |
| iPS:3 93982 | 21-225_6C12 | VH3/3-21|D4|4-11|RF2|JH4 | EVQLVES-GGGLVKPGGSLRLSCAASG-FTFS | S-----YSMN | WVRQAPGK GLEWVS | SISSS---SSYIYYADS VKG | RFTISRDNAKNSLYLQMNSL RAEDTAVYYCAR | DRG----------SL | WGQGT LVTVS S |
| iPS:3 98478 | 21-225_17C10 | VH3/3-21|D4|4-11|RF2|JH4 | EVQLVES-GGGLVKPGGSLRLSCAASG-FTFS | S-----YSMN | WVRQAPGK GLEWVS | SISGS---SSYMYYADS VKG | RFTISRDNAKNSLYLQMNSL RAEDTALYYCAR | DRG----------SS | WGQGT LVTVS S |
| VH3/3-23|D6|6-6|RF1|JH4 | | | | | | | | | |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:4 33897 | 21-225_43C2 | VH3/3-23/D6/6-6]RF1/JH4 | EVQLLES-GGGLVQPGGSLRLSCAASG-FTFS | S-----YAMS | WVRQAPGK GLEWVS | AISGR---GVNTFDADS VKG | RFTISRDNSKNTLYLQMNSL RAEDTAVYYCAK | ERSGS---------YFDY | WGQGT LVTVS S |
| iPS:4 33903 | 21-225_43H4 | VH3/3-23/D6/6-6]RF1/JH4 | EVQLLES-GGGLVQPGGSLRLSCAASG-FTFS | S-----YAMS | WVRQAPGK GLEWVS | AISGR---GINTFDADS VKG | RFTISRDNSKNTLYLQMNSL RAEDTAVYYCAK | ERSGS---------YFDY | WGQGT LVTVS S |
| iPS:4 33911 | 21-225_43E8 | VH3/3-23/D6/6-6]RF1/JH4 | EVQLLES-GGGLVQPGGSLRLSCAASG-FTFS | S-----YAMS | WVRQAPGK GLEWVS | AISGR---GINTFDADS VKG | RFTISRDNSKNTLYLQMNSL RAEDTAVYYCAK | ERSGS---------YFDY | WGQGT LVTVS S |
| iPS:4 33941 | 21-225_44D10 | VH3/3-23/D6/6-6]RF1/JH4 | EVQLLES-GGGLVQPGGSLRLSCAASG-FTFS | S-----YAMS | WVRQAPGK GLEWVS | AISGR---GVNTFDADS VKG | RFTISRDNSKNTLYLQMNSL RAEDTAVYYCAK | ERSGS---------YFDY | WGQGT LVTVS S |
| iPS:4 33957 | 21-225_45F8 | VH3/3-23/D6/6-6]RF1/JH4 | EVQLLES-GGGLVQPGGSLRLSCAASG-FTFS | S-----YAMS | WVRQAPGK GLEWVS | AISGR---GVNTFDADS VKG | RFTISRDNSKNTLYLQMNSL RAEDTAVYYCAK | ERSGS---------YFDY | WGQGT LVTVS S |
| iPS:4 33973 | 21-225_46A6 | VH3/3-23/D6/6-6]RF1/JH4 | EVQLLES-GGGLVQPGGSLRLSCAASG-FTFS | S-----YAMS | WVRQAPGK GLEWVS | AISGR---GINTFDADS VKG | RFTISRDNSKNTLYLQMNSL RAEDTAVYYCAK | ERSGS---------YFDY | WGQGT LVTVS S |
| iPS:4 35715 | 21-225_171A8 | VH3/3-23/D6/6-6]RF1/JH4 | EVQLLES-GGGLVQPGGSLRLSCAASG-PTFR | S-----SAMS | WVRQAPGK GLEWVS | VISGS---GGSTFYTDS VKG | RFTISRDNSKNTLYLQMNSL RAEDTAVYYCAK | SNSSG---------WFDY | WGQGT LVTVS S |
| iPS:4 35739 | 21-225_174G7 | VH3/3-23/D6/6-6]RF1/JH4 | EVQLLES-GGGLVQPGGSLRLSCAASG-FTFR | S-----SAMS | WVRQAPGK GLEWVS | VISGS---GGSTFYTDS VKG | RFTISRDNSKNTLYLQMNSL RAEDTAVYYCAK | SNSSG---------WFDY | WGQGT LVTVS S |
| iPS:4 35749 | 21-225_175C10 | VH3/3-23/D6/6-6]RF1/JH4 | EVQLLES-GGGLVQPGGSLRLSCAASG-FTFS | S-----YAMS | WVRQAPGK GLEWVS | SISGR---GGSTFYADS VKG | RFTVSHDNSKNTLYLQMNSL RAEDTAVYYCAK | SNSSG---------WFDY | WGQGT LVTVS S |
| | VH3/3-21/D7/7-27]RF1/JH4 | Germline | EVQLVES-GGGLVKPGGSLRLSCAASG-FTFS | S-----YTMN | WVRQVPGK GLEWVS | SISGS---STYIYYADS VKG | RFTISRDDAQMSLYLQMNSL RGEDTAVYYCAR | VTS------------FDY | WGQGA LVTVS S |
| iPS:4 33901 | 21-225_43A4 | VH3/3-21/D7/7-27]RF1/JH4 | EVQLVES-GGGLVKPGGSLRLSCAASG-FTFS | S-----YTMN | WVRQVPGK GLEWVS | SISGS---STYIYYADS VKG | RFTISRDDAQMSLYLQMNSL RGEDTAVYYCAR | VTS------------FDY | WGQGA LVTVS S |
| iPS:4 33961 | 21-225_45D9 | VH3/3-21/D7/7-27]RF1/JH4 | EVQLVES-GGGLVKPGGSLRLSCAASG-FTFS | S-----YTMN | WVRQVPGK GLEWVS | SISGS---STYIYYADS VKG | RFTISRDDAQMSLYLQMNSL RGEDTAVYYCAR | VTS------------FDY | WGQGA LVTVS S |

Figure 51 (Continued)

| | | | | | | | | | |
|---|---|---|---|---|---|---|---|---|---|
| iPS:4 34135 | 21-225_54H3 | VH3j3-21jD7j7-27jRF1jJ H4 | EVQLVES-GGGLVKPGGSLRL SCAASG-FTFS | S-----YSMI | WVRQAPGK GLEWVS | SISGT----SSYIYYADS VKG | RFTISRDNAKNSLYLQMNSL RAEDTAVYYCAG | MTT----------------VI | WGQGT LVTVS S |
| iPS:4 34331 | 21-225_63H8 | VH3j3-21jD7j7-27jRF1jJ H4 | EVQLVES-GGGLVKPGGSLRL SCAASG-FTFS | S-----YNMN | WVRQAPGK GLEWVS | SISGS----STYMNYTDS VKG | RFTISRDNAKNSLYLQMNSL RAEDTAVYYCAR | LRN---------------FDY | WGQGT LVTVS S |
| iPS:4 35421 | 21-225_151F1 | VH3j3-21jD7j7-27jRF1jJ H4 | EVQLVES-GGGLVKPGGSLRL SCAASG-YIFR | S-----FSMN | WVRQAPGK GLEWVS | SISSS----SYIYYADS VKG | RFTISRDNAKNSLYLQMNSL RAEDTAVYYCAR | DIP---------------LVY | WGQGT LVTVS S |
| iPS:4 35653 | 21-225_166H12 | VH3j3-21jD7j7-27jRF1jJ H4 | EVQLVES-GGALVKPGGSLRL SCAASG-FTFS | S-----YSMS | WVRQAPGK GLGWVS | SISGS----SSYSYYADS VKG | RFTISRDNAKNSLYLQMNSL RAEDTAVYYCAR | LTG---------------FDY | WGQGT LVTVS S |
| iPS:4 36648 | 21-225_227F11 | VH3j3-21jD7j7-27jRF1jJ H4 | EVQLVES-GGGLVKPGGSLRL SCAASG-FTFS | T-----YSMN | WVRQAPGK GLEWVS | SISSS----INYMYYADS VKG | RFTISRDNAKNSLYLQMNSL RAEDSAVYYCAR | LG----------------VY | WGQGT LVTVS S |
| iPS:3 92952 | 21-225_26G1 | VH3j3-21jD7j7-27jRF1jJ H4 | EVQLVES-GGGLVKPGGSLRL SCAASG-FTFS | S-----YGMN | WVRQAPGK GLEWVS | SISGS----SSYIYYADS VKG | RFTISRDNAKNSLYLQMNSL RAEDTAVYYCAR | LTT---------------FDF | WGQGT LVTVS S |
| iPS:3 93082 | 21-225_34C11 | VH3j3-21jD7j7-27jRF1jJ H4 | EVQLVES-GGGLVKPGGSLRL SCAASG-FTFS | S-----YTKS | WVRQAPGK GLEWVS | SISGS----SNYIYYADS VKG | RFTISRDNAKNSLYLQMNSL RAEDTAVYYCAR | LTG---------------FDY | WGQGT LVTVS S |
| iPS:3 94061 | 21-225_12D2 | VH3j3-21jD7j7-27jRF1jJ H4 | EVQLVES-GGGLVKPGGSLRL SCAASG-FTFS | S-----YSMN | WVRQAPGK GLEWVS | SISSS----SSYIYYADS VKG | RFTISRDNAKNSLYLQMNSL RAEDTAVYYCAR | LG----------------DY | WGQGT LVAVS S |
| iPS:3 94071 | 21-225_10C7 | VH3j3-21jD7j7-27jRF1jJ H4 | EVQLVES-GGGLVKPGGSLRL SCAASG-FTFS | S-----YSMN | WVRQAPGK GLEWVS | SISSS----NNYIYYADS VKG | RFTISRDNAKNSLYLQMNSL RAEDSAVYYCAR | LG----------------VY | WGQGT LVTVS S |
| iPS:3 98532 | 21-225_33B7 | VH3j3-21jD7j7-27jRF1jJ H4 | EVQLVES-GGGLVKPGGSLRL SCAASG-FTFS | S-----YNMN | WVRQAPGK GLEWVS | SISGS----SSYIYYADS VKG | RFTISRDNAKNSLYLQMNSL RAEDTAVYYCAR | LNG---------------FDY | WGQGT LVTVS S |
| iPS:4 02225 | 21-225_2B1 | VH3j3-21jD7j7-27jRF1jJ H4 | EVQLVES-GGGLVKPGGSLRL SCAASG-FTFS | S-----YSMN | WVRQAPGK GLEWVS | SISSS----SSYIYYADS VKG | RFTISRDNAKNSLYLQMNSL RAEDTAVYYCAR | LG----------------NY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 04090 | 21-225_8D8 | VH3J3-21/D7/7-27/RF1/JH4 | EVQLVES-GGGLVKPGGSLRL SCAASG-FTFS | S-----YSMN | WVRQAPGK GLEWVS | SISSS---SSYIYIADS VKG | RFTISRDNAKNSLYLQMNSL RAEDTAVYYCAR | LG---------NY | WGQGT LVTVS S |
| | VH3J3-11/D4/4-11/RF2/JH4 | Germline | | | | | | | |
| iPS:4 33905 | 21-225_43E5 | VH3J3-11/D4/4-11/RF2/JH4 | QVQLVES-GGGLVKPGGSLRL SCAASG-FTFS | D-----YYMI | WIRQAPGK GLEWVS | YISSS---GITKYYADS MKG | RFTISRDNAKNSLYLQMNSL RAEDTAVYYCAA | DT---------IY | WGQGT LVTVS S |
| iPS:4 33913 | 21-225_43H8 | VH3J3-11/D4/4-11/RF2/JH4 | QVQLVES-GGGLVKPGGSLRL SCAASG-ITFS | D-----YYMN | WIRQAPGK GLEWVS | YISSS---GRIFYYADS LKG | RFTISRDNAKNSLYLQMNSL RAEDTAVYYCAA | DT---------IY | WGQGT LVTVS S |
| iPS:4 33949 | 21-225_45H2 | VH3J3-11/D4/4-11/RF2/JH4 | QVQLVES-GGGLVKPGGSLRL SCAASG-FTFS | D-----YYMN | WIRQAPGK GLEWVS | YISSS---GITKYYADS VKG | RFTISRDNAKNSLYLQMNSL RAEDTAVYYCAA | DT---------IY | WGQGT LVTVS S |
| iPS:4 33981 | 21-225_46E9 | VH3J3-11/D4/4-11/RF2/JH4 | QVQLVES-GGGLVKPGGSLRL SCAASG-FTFS | D-----YYMN | WIRQAPGK GLEWVS | YINSN---GFTKYYADS VKG | RFTISRDNAKNSLYLQMNSL RAEDTAVYYCAA | DT---------IY | WGQGT LVTVS S |
| iPS:4 33995 | 21-225_47H7 | VH3J3-11/D4/4-11/RF2/JH4 | QVQLVES-GGGLVKPGGSLRL SCAASG-FTFS | D-----YYMI | WIRQAPGK GLEWVS | YINSN---GFTKYYADS VKG | RFTISRDNAKNSLYLQMNSL RAEDTAVYYCAA | DT---------VY | WGQGT LVTVS S |
| iPS:4 34039 | 21-225_43B1 | VH3J3-11/D4/4-11/RF2/JH4 | QVQLVES-GGGLVKPGGSLRL SCAASG-FTFS | D-----YYMN | WIRQAPGK GLEWVS | YINSN---GFTIYYADS VKG | RFTISRDNAKNSLYLQMNSL RAEDTAVYYCAA | DT---------IY | WGQGT RVTVS S |
| iPS:4 34275 | 21-225_57F4 | VH3J3-11/D4/4-11/RF2/JH4 | QVQLVES-GGGLVKPGGSLRL SCAASG-FTFS | D-----YYMN | WIRQAPGK GLEWVS | YISSS---GSTIYYADS VKG | RFTISRDNAKNSLYLQMNSL RAEDTAVYYCAR | DM---------IT | WGQGT LVTVS S |
| | | Germline | H_FR1 | H_CDR1 | H_FR2 | H_CDR2 | H_FR3 | H_CDR3 | H_FR4 |
| VH3J3-23/D7/7-27/RF1/JH3 | | | | | | | | | |
| iPS:4 33915 | 21-225_43H9 | VH3J3-23/D7/7-27/RF1/JH3 | EVQLLES-GGGLVQPGGGSLRL SCAASG-FTFS | S-----YAMS | WVRQAPGM GLEWVS | AISGS---GSNTFYYADS VKG | RFTISRDNSKNTLYLHMNSL RAEDTAVYFCAK | RTPSD-------VFDI | WGQGT MVTVS S |
| iPS:4 33925 | 21-225_44F3 | VH3J3-23/D7/7-27/RF1/JH3 | EVHLLES-GGGLVQPGGGSLRL SCAASG-FTFS | S-----YAMS | WVRQAPGK GLEWVS | ILSGG---GKTYYIADS VKG | RFTISRDNSKNTLFLQMNSL RAEDTAVYYCAK | RTPSD-------AFDI | WGQGT MVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 33953 | 21-225_45H4 | VH3\|3-23\|D7\|7-27\|RF1\|JH3 | EVQLLES-GGGLVQPGGSLRLSCAASG-FTFS | S-----YAMS | WVRQAPGM GLEWVS | AISGS---GSNTFYADS VKG | RFTISRDNSKNTLYLHMNSL RAEDTAVYFCAK | RTPSD-------VFDI | WGQGT MVTVS S |
| iPS:4 33959 | 21-225_45C9 | VH3\|3-23\|D7\|7-27\|RF1\|JH3 | EVQLLES-GGGLVQPGGSLRLSCAASG-FTFN | S-----YAMS | WVRQAPGK GLEWVS | VISGR---GGTTYYADS VKG | RFTISRDNSKNTLYLQMNSL RAEDTAVYYCAK | RTPSD-------AFDI | WGQGT MVTVS S |
| iPS:4 35379 | 21-225_149B6 | VH3\|3-23\|D7\|7-27\|RF1\|JH3 | EVQLLES-GGGLVQPGGSLRLSCAASG-FTFS | S-----YAMS | WVRQAPGK GLEWVS | VISGS---GGSTFYADS VKG | RFTISRDNSKNTLFLQMNSL RAEDTAVYYCAK | RTPED-------VFDI | WGQGT MVTVS S |
| iPS:4 35787 | 21-225_180A3 | VH3\|3-23\|D7\|7-27\|RF1\|JH3 | EVQLLES-GGGLEQPGGSLRLSCAASG-FTFS | S-----FAMN | WVRQAPGK GLEWVS | VISGR---GGNTFYADS VKG | RFTISRDNSKNTLFLQMNSL RAEDTAVYFCAK | RTGDD-------VFDV | WGQGT MVTVS S |
| iPS:4 35809 | 21-225_182H5 | VH3\|3-23\|D7\|7-27\|RF1\|JH3 | EVQLLES-GGGLVQPGGSLRLSCAASG-FTFS | S-----YAMS | WVRQAPGK GLEWVS | VISGR---GGTTFYADS VKG | RFTISRDNSKNTLYLQMNSL RAEDTAVYYCAK | RTGDD-------VFDI | WGQGT MVTVS S |
| iPS:4 35889 | 21-225_186A11 | VH3\|3-23\|D7\|7-27\|RF1\|JH3 | EVQLLES-GGGLVQPGGSLRLSCAASG-FTFS | S-----YAMS | WVRQAPGK GLEWVS | VISGR---GGTTFYADS VKG | RFTISRDNSKNTLYLQMNSL RAEDTAVYYCAK | RTGDD-------VFDI | WGQGT MVTVS S |
| | Germline | | H_FR1 | H_CDR1 | H_FR2 | H_CDR2 | H_FR3 | H_CDR3 | H_FR4 |
| | VH4\|4-59\|D6\|6-13\|RF2\|JH4 | | | | | | | | |
| iPS:4 33931 | 21-225_44F6 | VH4\|4-59\|D6\|6-13\|RF2\|JH4 | QVHLQES-GEGLVKPSETLSLTCTVSG-GSIS | S-----YYWS | WIRQPPGK GLEWIG | YIYY----SGNTNYNPS LKS | RVIISVDTSKNQFSLKLSSV TAADTAVYYCVR | GVAI--------KNY | WGQGT LVTVS S |
| | Germline | | H_FR1 | H_CDR1 | H_FR2 | H_CDR2 | H_FR3 | H_CDR3 | H_FR4 |
| | VH3\|3-23\|D4\|4-17\|RF2\|JH6 | | | | | | | | |
| iPS:4 33943 | 21-225_44E10 | VH3\|3-23\|D4\|4-17\|RF2\|JH6 | EVQLLES-GGGLVQSGGSLRLSCAASG-FTFS | S-----YAMN | WVRQAPGK GLEWVS | GVVGS---GGRTYYADS VKG | RFTISRDNSKNTLYLQMNSL RAEDTAVYYCAK | DRGQWL-------LGGMDV | WGQGT TVTVS S |
| iPS:4 33989 | 21-225_47C7 | VH3\|3-23\|D4\|4-17\|RF2\|JH6 | EVQLLES-GGGLVQPGGSLRLSCAASG-FTFS | N-----YAMS | WVRQAPGK GLEWVS | GISGS---GSRTYYADS VKG | RFTISRDNSKNTLYLQMNSL RAEDTAVYYCAK | DRGQWL-------IGGMDV | WGQGT TVTVS S |
| iPS:4 34133 | 21-225_54G3 | VH3\|3-23\|D4\|4-17\|RF2\|JH6 | EVQLLES-GGGLVQPGGSLRLSCAASG-FTFS | T-----YAMS | WVRQAPGK GLEWVS | AISGS---GVNTFYADS VKG | RFTISRDNSKNTLFLQMNSL RAEDTAVYYCAK | LGKDYY-------YYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34221 | 21-225_60A11 | VH3/3-23/D4/4-17/RF2/J H6 | EVQLLES-GGGLVQPGGSLRL SCAASG-FTFS | N-----YAMT | WVRQAPGK GLEWVS | AISGS---GGNTFYADS VTG | RVTISRDNSKNTLYLQMNSL RAEDTAVYYCAK | LGKDYH------YYGMDV | WGQGT TVTVS S |
| iPS:4 34257 | 21-225_62F7 | VH3/3-23/D4/4-17/RF2/J H6 | EVQLLES-GGGLVQPGGSLRL SCAASG-FTFS | S-----YVMS | WVRQAPGK GLEWVS | GISGS---GAKTYYADS VKG | RFTISRDNSKNTLYLQMNSL RAEDTAVYYCAE | LGIDYY------YGMDV | WGQGT TVTVS S |
| iPS:4 34283 | 21-225_57F8 | VH3/3-23/D4/4-17/RF2/J H6 | EVQLLES-GGGLVQPGGSLRL SCVVSG-FTFS | N-----YAMS | WVRQAPGK GLEWVS | ASSGS---GGNTFYADS VTG | RVTISRDNSKNTLYLQMNSL RAEDTAVYYCAE | LGKDYH------YYGMDV | WGQGT TVTVS S |
| iPS:4 34385 | 21-225_66C10 | VH3/3-23/D4/4-17/RF2/J H6 | EVQLLES-GGGLVQPGGSLRL SCAASG-FTFS | S-----YVMS | WVRQAPGK GLEWVS | GISGS---GARTYYADS VKG | RFTISRDNSKNTLYLQMNSL RAEDTAVYYCAE | LGIDYY------YGMDV | WGQGT TVTVS S |
| iPS:4 35717 | 21-225_171A9 | VH3/3-23/D4/4-17/RF2/J H6 | EVQLLES-GGGLAQPGGSLRL SCAASG-FTFS | S-----YAMT | WVRQAPGK GLEWVS | AISGS---GGNTFNADS VKG | RFTISRDNSKNTLYLQMNSL RAEDTAVYYCAK | LGIDYY------YYGMDV | WGQGT TVTVS S |
| iPS:4 36528 | 21-225_224B1 | VH3/3-23/D4/4-17/RF2/J H6 | EVQLLES-GGGLVQPGGSLRL SCAASG-FTFS | S-----YAMS | WVRQAPGK GLEWVS | AISGS---GGNTFYADS VKG | RFTISRDNSKNTLYLHMNSL RAEDTAVYYCAG | EGGYYY------YYGVDV | WGQGT TVTVS S |
| iPS:3 93810 | 21-225_5A4 | VH3/3-23/D4/4-17/RF2/J H6 | EVQVLES-GGGLVQPGGSLRL SCAASG-LITFS | S-----SAMS | WVRQAPGK GLEWVS | AISGR---GGNTFYTDS VKG | RFTISRDNSKNTLYLQMNSL RAEDTAVYYTDS | LGKDYY------YYGMDV | WGQGT TVTVS S |
| Germline | | | H_FR1 | H_CDR1 | H_FR2 | H_CDR2 | H_FR3 | H_CDR3 | H_FR4 |
| VH3/3-48/D3/5-24/RF3/J H6 | | | | | | | | | |
| iPS:4 33945 | 21-225_44C12 | VH3/3-48/D5/5-24/RF3/J H6 | EVQLVES-GGGLVQPGGSLRL SCAASG-FTFS | S-----YSVN | WVRQAPGK GLEWVS | YISSS---SSTIYYADS VKG | RFTISRDNAKNSLYLQMNSL RDEDTAVYYCAR | SGYSYAYY------YYGMDV | WGQGT TVTVS S |
| Germline | | | H_FR1 | H_CDR1 | H_FR2 | H_CDR2 | H_FR3 | H_CDR3 | H_FR4 |
| VH3/3-33/D6/6-13/RF2/J H4 | | | | | | | | | |
| iPS:4 33947 | 21-225_44E12 | VH3/3-33/D6/6-13/RF2/J H4 | QVHLAES-GGGVVQPGRSLRL SCEASG-FTLS | S-----DDTH | WVRQPPGK GLEWVA | VIWFD---EYNKYYADS VKG | RFTISRDNSKNTLYLQMNSL RAEDAAVYYCAR | DLIAAA------GTGDY | WGQGI LVTVS S |
| iPS:4 33963 | 21-225_46B1 | VH3/3-33/D6/6-13/RF2/J H4 | QVHLAES-GGGVVQPGRSLRL SCEASG-FTLS | S-----DDSH | WVRQPPGK GLEWVA | VIWFD---EYTKYYADS VKG | RFTISRDNSKNTLYLQMNNL RAEDAAVYYCAR | DLIAAT------GTGDY | WGQGI LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 33987 | 21-225_47A5 | VH3/3-33/D6/6-13/RF2/JH4 | QVQLVES-GGGVVQPGRSLRL SCAASG-FTFS | D-----DDIH | WVRQAPGK GLEWVA | VIWFD---GSNKYYADS VKG | RFTISRDNSKNTLYLQMNSL SAEDTAVYYCAR | DLIAAA-------GTVDY | WGQGT LVTVS S |
| iPS:4 36258 | 21-225_202F12 | VH3/3-33/D6/6-13/RF2/JH4 | QVQLVES-GGGVVQPGRSLRL SCEASG-FTFS | Y-----YGMH | WVRQAPGK GLEWVA | IIWYD---GSNKYYADS VKG | RFTISRDSSKNTLYLQMNSL RAEDTAVYYCAS | NIAAAA-------PYFDY | WGQGT LVTVS S |
| iPS:3 92646 | 21-225_20G2 | VH3/3-33/D6/6-13/RF2/JH4 | QVQLVES-GGGVVQPGRSLRL SCAASG-FTLS | S-----DDMH | WVRQEPGK GLEWVA | VIWFD---GSNKYYADS VKG | RFIMSRDNSKNTLYLQMNSL RAGDTAVYYCAR | DLIAAA-------GTVDY | WGQGT LVTVS S |
| iPS:3 92750 | 21-225_20A10 | VH3/3-33/D6/6-13/RF2/JH4 | QVQLVES-GGGVVQPGRSLRL SCAASG-FTLS | S-----DDMH | WVRQAPGK GLEWVA | VIWFD---GSNKYYADS VKG | RFTISRDNSKNTLYLQMNSL RAEDTAMYYCAR | DLIAAA-------GTVDY | WGQGT LVTVS S |
| | Germline VH3/3-23/D6/6-19/RF2/JH3 | | | | | | | | |
| iPS:4 33999 | 21-225_48D1 | VH3/3-23/D6/6-19/RF2/JH3 | EVQLLES-GGGLVQPGGSLRL SCAASR-FTFS | S-----YAMS | WVRQAPGK GLEWVS | VISGR---GGSTFYADS VKG | RFTISRDNSKNTLYLQMNSL RAEDTAVYYCAR | RIAVAG-------NEAFDI | WGQGT MVTVS S |
| iPS:4 34003 | 21-225_48C3 | VH3/3-23/D6/6-19/RF2/JH3 | EVQLLES-GGGLVQPGGSLRL SCAASR-FTFS | S-----YAMS | WVRQAPGK GLEWVS | VISGR---GGSTFYADS VKG | RFTISRDNSKNTLYLQMNSL RAEDTAVYYCAR | RIAVAG-------NEAFDI | WGQGT MVTVS S |
| iPS:4 34037 | 21-225_49G12 | VH3/3-23/D6/6-19/RF2/JH3 | EVQLLES-GGGLVQPGGSLRL SCTASG-FTFS | S-----YAMS | WVRQAPGK GLEWVS | VISGS---GGTFYADS VKG | RLTISRDNSKNTLYLQMNSL RAEDTAVYYCAR | RIAVAG-------NDAFDI | WGQGT MVTVS S |
| iPS:4 34041 | 21-225_50H8 | VH3/3-23/D6/6-19/RF2/JH3 | EVQLLES-GGGLVQPGGSLRL SCAASR-FTFS | S-----YAMS | WVRQAPGK GLEWVS | VISGR---GGTFYADS VKG | RFTISRDNSKNTLYLQMNSL RAEDTAVYYCAR | RIAVAG-------NEAFDI | WGQGT MVTVS S |
| iPS:4 34045 | 21-225_50H10 | VH3/3-23/D6/6-19/RF2/JH3 | EQQLLES-GGGLVQPGGSLRL SCAASR-FTFS | S-----YAMS | WVRQAEGK GLEWVS | VISGR---GGTFYADS VKG | RFTISRDNSKNTLYLQMNSL RAEDTAVYYCAR | RIAVAG-------NEAFDI | WGQGT MVTVS S |
| iPS:4 34073 | 21-225_51H10 | VH3/3-23/D6/6-19/RF2/JH3 | EVQLLES-GGGLVQPGGSLRL SCTASG-FTFS | S-----YAMS | WVRQAPGK GLEWVS | VISGS---GGTFYADS VKG | RLTISRDNSKNTLYLQMNSL RAEDTAVYYCAR | RIAVAG-------NDAFDI | WGQGT MVTVS S |
| iPS:4 36212 | 21-225_200G1 | VH3/3-23/D6/6-19/RF2/JH3 | EVQLLES-GGGLVQPGGSLRL SCAASG-FTFS | S-----YAMS | WVRQAPGK GLEWVS | AISGR---GGNTFYADS VRG | RFTISRDNSKNTLYLQMNSL RAEDTAVYYCAR | RIAVDG-------YDAFDV | WGQGT MVTVS S |

Figure 51 (Continued)

| | | | | | | | | | |
|---|---|---|---|---|---|---|---|---|---|
| iPS:3 92652 | 21-225_17C6 | VH3/3-23\|D6\|6-19\|RF2\|J H3 | EVQLLES-GGGLVQPGGSLRL SCAASE-FTFS | S-----YAMN | WVRQAPGK GLEWVS | VISGR----GGNTFYADS VKG | RFTISRDNSKNTLFLQMNSL RAEDTAVYYCAS | RLAVAG--------SEAFDI | WGQGT MVTVS S |
| iPS:3 92668 | 21-225_17B4 | VH3/3-23\|D6\|6-19\|RF2\|J H3 | EVQLLES-GGGLVQPGGSLRL SCAASE-FTFS | S-----YAMN | WVRQAPGK GLEWVS | VISGR----GGNTFYADS VKG | RFTISRDNSKNTLYLQMNSL RAEDTAVYYCAS | RLAVAG--------SEAFDI | WGQGT MVTVS S |
| iPS:3 92696 | 21-225_20A4 | VH3/3-23\|D6\|6-19\|RF2\|J H3 | EVQLLES-GGGLVQPGGSLRL SCAASE-FTFS | S-----YAMT | WVRQGPGM GLEWVS | VISGS----GGYTYNADS VKG | RFTISRDNSKNTLYLQMNSL RVEDTAVYYCAS | RIAVAG--------SEAFDI | WGQGT MVTVS S |
| iPS:3 92702 | 21-225_17F7 | VH3/3-23\|D6\|6-19\|RF2\|J H3 | EVQLLES-GGGLVQPGGSLRL SCAASE-FTFS | S-----YAMN | WVRQAPGK GLEWVS | IISGR----GGNTFYADS VKG | RFTISRDNSKNTLYLQMNSL RAEDTAVYYCAS | RLAVAG--------SEAFDI | WGQGT MVTVS S |
| iPS:3 92704 | 21-225_17F11 | VH3/3-23\|D6\|6-19\|RF2\|J H3 | EAQLLES-GGGLEQPGGSLRL SCAASG-FTFS | S-----YAMS | WVRQAPGK GLEWVS | VISGR----GGNTFYADS VKG | RFTISRDNSKNTLYLQMNSL RAEDTAVYYCAS | RLAVAG--------SEAFHI | WGQGT MVTVS S |
| iPS:3 92720 | 21-225_17A12 | VH3/3-23\|D6\|6-19\|RF2\|J H3 | EVQLLES-GGGLVQPGGSLRL SCAASE-FTFS | S-----YAMS | WVRQDPGK GLEWVS | IISGR----GGNAFYADS VKG | RFTISRDNSKNTLYLQMNSL RAEDTAVYYCAS | RIAVAG--------SEAFDI | WGQGT MVTVS S |
| iPS:3 92722 | 21-225_18E12 | VH3/3-23\|D6\|6-19\|RF2\|J H3 | EVQLLES-GGGLVQPGGSLRL SCAASE-FTFS | S-----YAMS | WVRQAPGT GLEWVS | IISGR----GGNTFYADS VKG | RFTISRDNSKNTLYLQMNSL RAEDTAVYYCAS | RLAVAG--------SEAFDI | WGQGT MVTVS S |
| iPS:3 92760 | 21-225_22G3 | VH3/3-23\|D6\|6-19\|RF2\|J H3 | EVQLLES-GGGLVQPGGSLRL SCAASE-FTFS | S-----YAMN | WVRQAPGK GLEWVS | VISGR----GGNTFYADS VKG | RFTISRDNSKNTLYLQMNSL RAEDTAVYYCAS | RLAVAG--------SEAFDI | WGQGT MVTVS S |
| iPS:3 92764 | 21-225_22G10 | VH3/3-23\|D6\|6-19\|RF2\|J H3 | EVQLLES-GGDLVQPGGSLRL SCTASG-FTFS | S-----YAMN | WVRQAPGK GLEWVS | VISGS----GGNTFYADS VKG | RFTISRDNSKNTLFLHMNSL RAEDTAVYYCAS | RMAVAG--------SEAFDI | WGQGT MVTVS S |
| iPS:3 92812 | 21-225_21F4 | VH3/3-23\|D6\|6-19\|RF2\|J H3 | EVQLLES-GGGLVQPGGSLRL SCAASE-FTFS | S-----YAMN | WVRQAPGK GLEWVS | VISGR----GGNTFYADS VKG | RFTISRDNSKNTLYLQMNSL RAEDTAVYYCAS | RLAVAG--------SEAFDI | WGQGT MVTVS S |
| iPS:3 92816 | 21-225_22E4 | VH3/3-23\|D6\|6-19\|RF2\|J H3 | EVQLLES-GGGLVQPGGSLRL SCAASE-FTFS | S-----YAMS | WVRQAPGK GLEWIS | IISGR----GINTFYADS VKG | RFTISRVNSKNTLYLQMNSL RAEDTAVYYCAS | RIAVAG--------SEAFDI | WGQGT MVTVS S |
| iPS:3 92852 | 21-225_21A2 | VH3/3-23\|D6\|6-19\|RF2\|J H3 | EVQLLES-GGGLVQPGGSLRL SCAASK-FTFS | S-----YAMN | WVRQAPGK GLEWVS | IISGR----GGNTFYADS VKG | RFTISRDNSKNTLYLQMNSL RAEDTAVYYCAS | RLAVAG--------SEAFDI | WGQGT MVTVS S |

Figure 51 (Continued)

| | | | | | | | | | |
|---|---|---|---|---|---|---|---|---|---|
| iPS:3 92878 | 21-225_22C5 | VH3j3-23jD6j6-19jRF2/J H3 | EVQLLES-GGGLVQVGGSLRL SCAASG-FTFS | S-----YAMS | WVRQAPGM GLEWVS | IISGS---GGYTYADS VKG | RFTISRDNSKNTLYLQMNSL RAEDTAVYYCAS | RIAVAG---------SEAFDI | WGQGT MVTVS S |
| iPS:3 92902 | 21-225_22D5 | VH3j3-23jD6j6-19jRF2/J H3 | EVQLLES-GGGLVQPGGSLRL SCAASE-FTFS | S-----YAMS | WVRQAPGK GLEWVS | VISGR---GGNTFYADS VKG | RFTISRDNSKNTLYLQMNSL RAEDTAVYYCAS | RIAVAG---------SEAFDI | WGQGT MVTVS S |
| iPS:3 93824 | 21-225_10F12 | VH3j3-23jD6j6-19jRF2/J H3 | EVQLLES-GGGLVQPGGSLRL SCAASE-FTFS | S-----YAMS | WVRQAPGM GLEWVS | IISGR---GGNTFYADS VKG | RFTISRDNSKNTLYLQMNSL RAEDTAVYYCAS | RVAVAG---------SEAFAI | WGQGT MVTVS S |
| iPS:3 93848 | 21-225_4H2 | VH3j3-23jD6j6-19jRF2/J H3 | EVQLLES-GGGLVQPGGSLRL SCAASG-FTFS | G-----YAMN | WVRQAPGM GLEWVS | VISRS---GGYTYADS VKG | RFTISRDNSKNTLYLQMNSL RAEDTAVYYCAS | RLAVAG---------SEAFDI | WGQGT MVTVS S |
| iPS:3 93862 | 21-225_5G2 | VH3j3-23jD6j6-19jRF2/J H3 | EVQLLES-GGGLVQPGGSLRL SCAASE-FTFS | S-----YAMS | WVRQAPGK GLEWVS | VISGR---GVNTFYADS VKG | RFTISRDNSKNTLYLQMNSL RAEDTAVYYCAS | RIAVAG---------SEAFDI | WGQGT MVTVS S |
| iPS:3 93888 | 21-225_3E3 | VH3j3-23jD6j6-19jRF2/J H3 | EVQLLES-GGTLVQPGGSLRL SCAASE-FTFS | S-----YVMS | WVRQAPGK GLEWVS | IISGR---GGNTFYADS VKG | RFTISRDNSKNTLYLQMNSL RAEDTALYYCAS | RLAVAG---------SEAFDI | WGQGT MVTVS S |
| iPS:3 93898 | 21-225_5F7 | VH3j3-23jD6j6-19jRF2/J H3 | EVQLLES-GGGLVQPGGSLRL SCAASE-FTFS | S-----YAMS | WVRQAPGK GLEWVS | IISGR---GGNTFYADS VKG | RFTISRDNSKNTLYLQMNSL RAEDTAVYYCAS | RIAVAG---------SEAFDI | WGQGT MVTVS S |
| iPS:3 93980 | 21-225_6D3 | VH3j3-23jD6j6-19jRF2/J H3 | EVQLLES-GGGLVQPGGSLRL SCAASE-FTFS | S-----YAMN | WVRQAPGK GLEWVS | VISGR---GGYTYADS VKG | RFTISRDNSKNTLYLQMNSL RAEDTAVYYCAS | RLAVAG---------SEAFDI | WGQGT MVTVS S |
| iPS:3 94014 | 21-225_8G6 | VH3j3-23jD6j6-19jRF2/J H3 | EVQLLES-GGGLVQPGGSLRL SCVASE-FTFS | S-----YVMN | WVRQAPGK GLEWVS | VISGR---GGNTFYADS VKG | RFTISRDNSKNTLYLQMNSL RAEDTAVYYCAS | RLAVAG---------SEAFDI | WGQGT MVSVS S |
| iPS:3 94022 | 21-225_16H6 | VH3j3-23jD6j6-19jRF2/J H3 | EVQLLES-GGGLVQPGGSLRL SCAASE-FTFS | S-----YAMN | WVRQAPGM GLEWVS | VISRS---GGYTYADS VKG | RFTISRDNSKNTLYLQMNSL RAEDTAVYYCAS | RLAVAG---------SEAFDI | WGQGT MVTVS S |
| iPS:3 94043 | 21-225_3B1 | VH3j3-23jD6j6-19jRF2/J H3 | EVQLLES-GGGLVQPGGSLRL SCAASE-FTFS | S-----YAMN | WVRQAPGK GLEWVS | VISGR---GINTFYADS VKG | RFTISRDNSKNTLYLQMNSL RAEDTAVYYCAS | RLAVAG---------SEAFDI | WGQGT MVTVS S |
| iPS:3 94077 | 21-225_8E12 | VH3j3-23jD6j6-19jRF2/J H3 | EVQLLES-GGGLVQPGGSLRL SCAASE-FTFS | S-----YAMS | WVRQAPGK GLEWVS | IISGR---GGNTFYADS VKG | RFTISRDNSKNTLYLQMNSL RAEDTAVYYCAS | RMAVAG---------SEAFDI | WGQGT MVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 94087 | 21-225_11A5 | VH3/3-23|D6|6-19|RF2/JH3 | EVQLLES-GGDLVQPGGSLRLSCAASE-FTFS | S-----YAMS | WVRQAPGK GLEWIS | VISGR---GVNTFYADS VKG | RFTISRDNSKNTLYLQMNSL RAEDTAVYYCAS | RIAVAG--------SEAFDI | WGQGT MVTVS S |
| | Germline | VH3/3-11|D6|6-6|RF2/JH3 | EVQLVES-GGGLVKPGGSLRL SCAASG-FTFS | -------YAMS | WIRQAPGK GLEWVS | YISSA---GSTYYADS VKG | RFTISRDNAKNSLYLQMNSL RAEDTAVYYCAR | AVAAP---------GAFDI | WGQGT MVTVS S |
| | | | H_FR1 | H_CDR1 | H_FR2 | H_CDR2 | H_FR3 | H_CDR3 | H_FR4 |
| iPS:4 34011 | 21-225_48B10 | VH3/3-11|D6|6-6|RF2/JH3 | QVQLVES-GGGLVKPGGSLRL SCAASG-FTFS | D-----YFMT | WIRQAPGQ GLEWVS | YISSA---GGAIYYADS VKG | RFTISRDNAKNSLYLQMNSL RAEDTAVYYCAI | AVAAP---------GVFDI | WGQGT MVTVS S |
| | Germline | VH3/3-11|D6|6-6|RF2/JH4 | QVQLVES-GGGLVKPGGSLRL SCAASG-FTFS | -------YMS | WIRQAPGK GLEWVS | YISSS---GSTYYADS VKG | RFTISRDNAKNSLYLQMNSL RAEDTAVYYCAK | AVAAP---------YFDY | WGQGT LVTVS S |
| iPS:4 34015 | 21-225_48F12 | VH3/3-11|D6|6-6|RF2/JH4 | QVQLVES-GGGLVKPGGSLRL SCAASG-FTFS | D-----YFMT | WIRQAPGQ GLEWVS | YISSA---GGAIYYADS VKG | RFTISRDNAKNSLFLQMNSL RAEDTAVYYCAI | AVAAP---------GAFDI | WGQGT LVTVS S |
| iPS:4 34017 | 21-225_48G12 | VH3/3-11|D6|6-6|RF2/JH4 | QVQLVES-GGGLVKPGGSLRL SCAASG-FTFS | D-----YFMT | WIRQAPGQ GLEWVS | YISSA---GGAIYYADS VKG | RFTISRDNAKNSLFLQMNSL RAEDTAVYYCAI | AVAAP---------GAFDI | WGQGT LVTVS S |
| | Germline | VH3/3-23|D6|6-13|RF2/JH4 | EVQLLES-GGGLVQPGGSLRL SCAASG-FTFS | -------YAMS | WVRQAPGK GLEWVS | AISGS---GSTYYADS VKG | RFTISRDNSKNTLYLQMNSL RAEDTAVYYCAK | GGAAP---------YFDY | WGQGT LVTVS S |
| iPS:4 34023 | 21-225_49F1 | VH3/3-23|D6|6-13|RF2/JH4 | EVQLLES-GGGLVQPGGSLRL SCAASG-FTFS | S-----YAMS | WVRQAPGK GLEWVS | VISGS---GGSTFYADS VKG | RFTISRDNSKSTLYLQMNSL RAEDTAVYYCAS | AIAAAG--------AHYFDY | WGQGT LVTVS S |
| iPS:4 36246 | 21-225_201G6 | VH3/3-23|D6|6-13|RF2/JH4 | EVQLLES-GGGLVQPGGSLRL SCAASG-FTFS | S-----YAMS | WVRQAPGK GLEWVS | TISGS---GVRTYYADS VKG | RFTISRDNSKNTLFLQMNSL RAEDTAVYYCAK | GGARSSG--------WFHFDY | WGQGT LVTVS S |
| iPS:4 36254 | 21-225_202C12 | VH3/3-23|D6|6-13|RF2/JH4 | EVQLLES-GGGLVQPGGSLRL SCAASG-FTFS | S-----YAMS | WVRQAPGK GLEWVS | TISGS---GVRTYYADS VKG | RSTISRDNSKNTLFLQMNSL RAEDTAVYYCAK | GGARSSG--------WFHFDY | WGQGT LVTVS S |
| iPS:4 36304 | 21-225_201F3 | VH3/3-23|D6|6-13|RF2/JH4 | EVQLLES-GGGLVQPGGSLRL SCAASG-FTFS | S-----YAMS | WVRQAPGK GLEWVS | TISGS---GVRTYYADS VKG | RFTISRDNSKNTLFLQMNSL RAEDTAVYYCAK | GGARSSG--------WFHFDY | WGQGT LVTVS S |
| iPS:4 36334 | 21-225_208G3 | VH3/3-23|D6|6-13|RF2/JH4 | EVQLLES-GGGLVQPGGSLRL SCAASG-FTFS | S-----YAMS | WVRQAPGK GLEWVS | TISGS---GVRTYYADS VKG | RSTISRDNSKNTLFLQMNSL RAEDKAVYYCAK | GGARSSG--------WFHFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3J3-23D6J6-19RF2JH5 | | EVQLLES GGGLVQPGGSLRL SCAASG-FTFS | S-----YAMS | WVRQAPGK GLEWVS | AISGS--- GSTTYADS VKG | RFTISRDNSKNTLYLQMNSL RAEDTAVYYCAK | GIAVAG--------NHFDP | WGQGT LVTVS S |
| iPS:4 34027 | 21-225_49H5 | VH3J3-23D6J6-19RF2JH5 | EVQLLES- GGGLVQPGGSLRL SCAASG-FTFS | S-----YAMT | WVRQTPGK GLEWVS | AISGS--- GGNSFYADS VKG | RFTISRDNSENTFYLQMNSL RAEDTAVYYCAK | ARAVAG--------SHWFDP | WGQGT LVTVS S |
| iPS:4 34061 | 21-225_51C7 | VH3J3-23D6J6-19RF2JH5 | EVQLLES- GGGLVQPGGSLRL SCAASG-FTIS | N-----YAMT | WVRQTPGK GLEWVS | VISAS--- GGNSFYADS VKG | RFTISRDNSENIFYLQMNSL RAEDTAVYYCAK | ARAVAG--------SHWFDP | WGQGT LVTVS S |
| iPS:4 34167 | 21-225_50F3 | VH3J3-23D6J6-19RF2JH5 | EVQLLES- GGGLVQPGGSLRL SCAASG-FTFR | T-----YAMT | WVRQAPGK GLEWVS | AISGS--- GVNSFYADS VKG | RFTISRDNSENTLYLQMNSL RAEDTAVYYCAK | ARAVAG--------SHWFDP | WGQGT LVTVS S |
| iPS:4 34455 | 21-225_72F5 | VH3J3-23D6J6-19RF2JH5 | EVQLLES- GGGLVQPGGSLRL SCAASG-FTFS | S-----YAMI | WVRQAPGK GLEWVS | TISGS--- GGYTYADS VKG | RFTISRDNSKNTLYLQMNSL RAEDTAVYYCAK | RIAVTG--------TEWYDP | WGQGT LVTVS S |
| iPS:4 37232 | 21-225_63E1 | VH3J3-23D6J6-19RF2JH5 | EVQMLES- GGGLGQSGGGSLRL SCTASG-FTFT | T-----SAMS | WVRQAPGK GLEWVS | AISGS--- GANTFYADS VKG | RFTVIRDNSKNTLYLYQMNSL TAEDTAVYYCVK | VIAVAG--------GHFFDP | WGQGT LVTVS S |
| VH3J3-21D1J1-1RF2JH4 | | EVQLVES GGGLVKPGGSLRL SCAASG-FTFS | S-----YSMN | WVRQAPGK GLEWVS | SISSS--- VKG | RFTISRDNAKNSLYLQMNSL AKDTAVYYCAR | VGIER | H_FR4 |
| iPS:4 34043 | 21-225_50G10 | VH3J3-21D1J1-1RF2JH4 | EVQLVES- GGGLVKPGGSLRL SCAASG-FTFS | S-----YSMN | WVRQAPGK GLEWVS | SISGS--- SSIYYADS VKG | RFTISRDNAKNSLYLQMNSL RAEDTAVYYCAR | VAT-------------FDY | WGQGT LVTVS S |
| iPS:4 34085 | 21-225_52E3 | VH3J3-21D1J1-1RF2JH4 | EVQLVES- GGGLVKPGGSLRL SCAASG-FTFS | S-----YKMN | WVRQAPGK GLEWVS | SISGS--- NSSIYYADS VKG | RFTISRDNAENSLYLQMNSL RAEDTAVYYCAR | VSS-------------NDY | WGQGT LVTVS S |
| iPS:4 34101 | 21-225_52H12 | VH3J3-21D1J1-1RF2JH4 | EVQLVES- GGGLVKPGGSLRL SCAASG-FTFS | S-----YSMN | WVRQAPGK GLEWVS | SISGS--- STYIYADS VKG | RFTISRDNAKNSLYQVNSL RAEDTAVYYCAR | VNS-------------FDY | WGQGT LVTVS S |
| iPS:4 34187 | 21-225_56A5 | VH3J3-21D1J1-1RF2JH4 | EVQLVES- GGGLVKPGGSLRL SCAASG-FTFS | S-----YSMN | WVRQAPGK GLEWVS | SISGS--- SSIYYADS VKG | RFTISRDNAKNSLYLQMNSL RAEDTAVYYCAR | VAT-------------FDY | WGQGT LVTVS S |
| iPS:4 34265 | 21-225_57B2 | VH3J3-21D1J1-1RF2JH4 | EVQLVES- GGGLVKPGGSLRL SCAASG-FTFS | S-----YSMN | WVRQAPGK GLEWVS | SISGS--- SSINYIDS VKG | RFTISRDNAKNSLYLQMNSL RAEDTAVYYCAR | VAG-------------FDY | WGQGT LVTVS S |

Figure 51 (Continued)

| | | | | | | | | | |
|---|---|---|---|---|---|---|---|---|---|
| iPS:4 34439 | 21-225_70E12 | VH3J3-21JD1J1-1JRF2/JH4 | EVQLVES-GGGLVKPGGSLRL SCAASG-FTFS | S-----YSMN | WVRQAPGK GLEWVS | SISGN---STYIYTDS VKG | RFTISRDNAKNSLYLQMDSL TAEDTAVYYCAR | VAA--------- | ----FDC | WGQGT LVTVS S |
| iPS:4 35515 | 21-225_157E4 | VH3J3-21JD1J1-1JRF2/JH4 | EVQLVES-GGGLVKPGGSLRL SCAASG-FTFS | S-----YTMN | WVRQAPGK GLEWVS | SISGS---SSYIYYADS VKG | RFTISRDNAKNSLYLQMNSL KAEDTAVYYCAR | VAT--------- | ----FDY | WGQGT LVTVS S |
| iPS:4 35535 | 21-225_157H10 | VH3J3-21JD1J1-1JRF2/JH4 | EVQLVES-GGGLVKPGGSLRL SCAASG-FTFS | S-----YTMN | WVRQAPGK GLEWVS | SISGS---SSYINYADS VKG | RFTISRDNAKNSLYLQMNSL RAEDTAVYYCAR | VAH--------- | ----FDY | WGQGT LVTVS S |
| iPS:4 37224 | 21-225_56H1 | VH3J3-21JD1J1-1JRF2/JH4 | EVQLVES-GGGLVKPGGSLRL SCAASG-FTFS | N-----YRMN | WVRQGPGK GLEWIS | SISGS---STDIYYADS VKG | RFTISRDNAKNSLYLQMNSL RAEDTAVYYCAR | VAS--------- | ----FDY | WGQGT LVTVS S |
| iPS:3 92620 | 21-225_17H5 | VH3J3-21JD1J1-1JRF2/JH4 | EVQLVES-GGGLVKPGGSLRL SCAASG-FTFS | S-----YSMN | WVRQAPGK GLEWVS | SISSS---STYIYYADS VKG | RFTISRDNAKNSLYLQMNSL RAEDTAVYYCAR | VAS--------- | ----FDY | WGQGT LVTVS S |
| iPS:3 92632 | 21-225_16A11 | VH3J3-21JD1J1-1JRF2/JH4 | EVQLVES-GGGLVKPGGSLRL SCAASG-FTFS | S-----YTMN | WVRQAPGK GLEWVS | SISGS---SSLIYYADS VKG | RFTISRDNAKNSLYLQMNSL RAEDTAVYYCAR | VAA--------- | ----FDY | WGQGT LVTVS S |
| iPS:3 92746 | 21-225_20H7 | VH3J3-21JD1J1-1JRF2/JH4 | EVHLVES-GGGLVKPGGSLRL SCAASG-FTFS | S-----YSMN | WVRQAPGK GLEWVS | SISGS---SSFIYYADS VKG | RFTISRDNAKNSLYLQMNSL RAEDTAVYYCAR | VAA--------- | ----LDY | WGQGT LVTVS S |
| iPS:3 92782 | 21-225_22B12 | VH3J3-21JD1J1-1JRF2/JH4 | EVQLVES-GGGLVKPGGSLRL SCAASG-FTFS | S-----YSMN | WVRQAPGK GLEWVS | SISGS---SSYTYYADS VKG | RFTISRDNAKNSLYLQMNSL RAEDTAVYYCAR | VAA--------- | ----LDS | WGQGT LVTVS S |
| iPS:3 92916 | 21-225_27C5 | VH3J3-21JD1J1-1JRF2/JH4 | EVQLVES-GGGLVKPGGSLRL SCAASG-FTFS | S-----YSMN | WVRQAPGK GLEWVS | STSSS---DSYIYYADS VKG | RFTISRDNAKNSLYLQMNSL RAEDTAVYYCAR | VAS--------- | ----FDC | WGQGT LVTVS S |
| iPS:3 92976 | 21-225_27H12 | VH3J3-21JD1J1-1JRF2/JH4 | EVQLVES-GGGLVKPGGSLRL SCAASG-FTFS | S-----YSLN | WVRQAPGK GLEWVS | SISGS---SSNIYYADS VKG | RFTISRDNAKNSLFLQMNSL RAEDTAVYYCAR | VAS--------- | ----FDY | WGQGT LVTVS S |
| iPS:3 93120 | 21-225_35H8 | VH3J3-21JD1J1-1JRF2/JH4 | EVQLVES-GGGLVKPGGSLRL SCAASG-FTFS | S-----YSMN | WVRQAPGK GLEWVS | SISGT---GSFIYYADS VKG | RFTISRDNAKKSVYLQMNSL RAEDTAVYYCAR | VSG--------- | ----FDY | WGQGT LVTVS S |
| iPS:3 93836 | 21-225_15A2 | VH3J3-21JD1J1-1JRF2/JH4 | EVQLVES-GGGLVKPGGSLRL SCAASG-FTFS | S-----YTMN | WVRQAPGK GLEWVS | SISGS---GSYIYYADS VKG | RFTISRDNAKNSLYLQMNAL RAEDTAVYYCAR | VAS--------- | ----FDY | WGQGT LVTVS S |

Figure 51 (Continued)

| | | | | | | | | | |
|---|---|---|---|---|---|---|---|---|---|
| iPS:3 93894 | 21-225_5E11 | VH3|3-21|D1|1-1|RF2|JH4 | EVQLVES-GGGLVKPGGSLRL SCAASG-FTFS | S------YSMN | WVRQAPGK GLEWVS | SISGS---STYIYYADS VKG | RFTISRDNAKNSLYLQMNSL RAEDTAVYYCAR | VAS----------- | ----------FDY | WGQGT LVTVS S |
| iPS:3 93896 | 21-225_2A4 | VH3|3-21|D1|1-1|RF2|JH4 | EVQLVES-GGGLVKPGGSLRL SCAASG-FTFS | S------YSMN | WVRQAPGK GLEWVS | SISGS---STYIYYADS VKG | RIAISRDNAKNSLYLQMNSL RAEDTAVYYCAR | VAS----------- | ----------FDY | WGQGT LVTVS S |
| iPS:3 93914 | 21-225_16B8 | VH3|3-21|D1|1-1|RF2|JH4 | EVQLVES-GGGLVKPGGSLRL SCAASG-FTFS | S------YSMN | WVRQAPGK GLEWIS | SISGS---STYIYYADS VKG | RFTISRDNAKNSLYLQMNSL RAEDTAVYYCAR | VAS----------- | ----------FDY | WGQGT LVTVS S |
| iPS:3 93944 | 21-225_14D6 | VH3|3-21|D1|1-1|RF2|JH4 | EVQLVES-GGGLVKPGGSLRL SCAASG-FTFS | S------YTMN | WVRQAPGK GLEWVS | SISGS---GSYIYYADS VKG | RFTMSRDNAKNSLYLQMNSL RAEDTAVYYCAR | VAA----------- | ----------FDS | WGQGT LVSVS S |
| iPS:3 93952 | 21-225_1F1 | VH3|3-21|D1|1-1|RF2|JH4 | EVQLVES-GGGLVKPGGSLRL SCAASG-FTFS | S------YNMN | WVRQAPGK GLEWVS | SISSS---SSYIYYADS VKG | RFTISRDNAKNSLYLQMNSL RAEDTAVYYCAR | VNL----------- | ----------FDY | WGQGT LVTVS S |
| iPS:3 94033 | 21-225_5F4 | VH3|3-21|D1|1-1|RF2|JH4 | EVQLVES-GGGLVKPGGSLRL SCVASG-FTFS | S------YSMN | WVRQAPGK GLEWVS | SISGS---SSYIYYADS VKG | RFTISRDNAKNSLYLQMNSL RAEDTAVYYCAR | VNN----------- | ----------FDY | WGQGT LVTVS S |
| iPS:3 94069 | 21-225_16H1 | VH3|3-21|D1|1-1|RF2|JH4 | EVQLVES-GGGLVKPGGSLRL SCAASG-FTFS | S------YSMN | WVRQAPGK GLEWVS | SISGS---STYIYYADS VKG | RFTISRDNAKNSLYLQMNSL RAEDTAVYYCAR | VAA----------- | ----------FDY | WGQGT LVTVS S |
| iPS:3 98482 | 21-225_17H6 | VH3|3-21|D1|1-1|RF2|JH4 | EVQLVES-GGGLVKPGGSLRL SCAASG-FTFS | S------YSMN | WVRQAPGK GLEWVS | SISGS---STYIYYADS VKG | RFTIFRDNAKNSLYLQMNSL RAEDTAVYYCAR | VAS----------- | ----------FDY | WGQGT LVTVS S |
| iPS:3 98492 | 21-225_21F12 | VH3|3-21|D1|1-1|RF2|JH4 | EVQLVES-GGGLVKPGGSLRL SCAASG-FTFS | S------YRMN | WVRQAPGK GLEWVS | SINSY---SSYIYYADS VKG | RFTISRDNAKNSLYLQMNSL RAEDTAVYYCAR | VAS----------- | ----------FDY | WGQGT LVTVS S |
| iPS:3 98500 | 21-225_23A11 | VH3|3-21|D1|1-1|RF2|JH4 | EVQLVES-GGGLVKPGGSLRL SCAASG-FTFS | S------YSMN | WIRQAEGK GLEWVS | SISGS---STYIYYADS VKG | RIAISRDNAKNSLYLQMNSL RAEDTAVYYCAR | VAS----------- | ----------FDY | WGQGT LVTVS S |
| iPS:3 98526 | 21-225_32B3 | VH3|3-21|D1|1-1|RF2|JH4 | EVQLVES-GGGLVKPGGSLRL SCAASG-FTFS | S------YSMN | WVRQAPGK GLEWVS | SISGS---STYIYYADS VKG | RFTISRDNAKNSLYLQMNSL RAEDTAVYYCAR | VAG----------- | ----------FDY | WGQGT LVTVS S |
| iPS:4 02221 | 21-225_2C12 | VH3|3-21|D1|1-1|RF2|JH4 | EVQLVES-GGGLVKPGGSLRL SCAASG-FTFS | S------YSMN | WVRQAPGK GLEWVS | SISGS---SSYMYYADS VKG | RFTISRDNAKDSLYLQMNSL RAEDTAVYYCAR | VNL----------- | ----------FDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH1|1-02|D2|2-15|RF2|JH6 | | EVQLVQS GGGLVKPGGSLRL SCAASG-YTFT | YYMH | WVRQAPGQ GLEWMG | WINP SGGTNSAQK FQG | RVTMTRDTSISTAYMELSRL RSEDTAVYYCAR | GYLSGSYS YYYYGMDV | WGQGT TVTVS S |
| iPS:4 34047 | 21-225_50A12 | VH1|1-02|D2|2-15|RF2|JH6 | QVQLVQS- GAEVKKPGASVKV SCKASG-YTFT | G-----HYIN | WVRQAPGQ GFEWMA | WVNPN--- SGGTNSAQK FQG | RVTMTRDTSISTVYMELSRL RSEDTAVYYCAR | GGQLGGFN--------- ------YYYYGMDV | WGQGT TVTVS S |
| iPS:4 34067 | 21-225_51H8 | VH1|1-02|D2|2-15|RF2|JH6 | QVQLVQS- GAEVKKPGASVKV SCKASG-YTFT | G-----HYMN | WVRQAPGQ GLEWMG | WVNPN--- SGGSNSAQQ FQG | RVTMIKDTSISTVYMELSRL SSDDTAVYYCAR | GGQLGGFN--------- ------FYYYGMDV | WGQGT TVTVS S |
| iPS:4 34197 | 21-225_56C7 | VH1|1-02|D2|2-15|RF2|JH6 | QVQLVQS- GAEVKKPGASVKV SCKASG-YTFT | G-----HYIN | WVRQAPGQ GLEWMA | WVNPN--- SGGTNSAQK FQG | RVTMTRDTSISTVYMELSRL RSEDTAVYYCAR | GGQLGGFN--------- ------YYYYGMDV | WGQGT TVTVS S |
| VH3|3-21|D|2-15|RF3|JH6 | | EVQLVES GGGLVKPGGSLRL SCAASG-FTFS | YSMN | WVRQAPGKG GLEWVS | SISSSS SSTYYYADS VKG | RFTISRDNAKNSLYLQMNSL RAEDTAVYYCAR | DYYYYAAY --YYYYGMDV | WGQGT TVTVS S |
| iPS:4 34049 | 21-225_50B12 | VH3|3-21|D|2-15|RF3|JH6 | EVQLVES- GGGLVKPGGSLRL SCAASG-FTFS | S-----HSMN | WVRQAPGK GLEWVS | SISSSS--- SNYIYYADS VKG | RFTISRDYAKNSLYLQMNSL RAEDTAVYYCAR | DRSIVVAGP------ ------MDYYGMDV | WGQGT MVTVS S |
| VH3|3-23|D11-20|RF1|JH3 | | EVQLLES GGGLVQPGGSLRL SCAASG-FTFS | YAMS | WVRQAPGK GLEWVS | AISGS GGSTYYADS VKG | RFTISRDNSKNTLYLQMNSL RAEDTAVYYCAK | GETDI -----DAFDI | WGQGT MVTVS S |
| iPS:4 34055 | 21-225_51B4 | VH3|3-23|D1|1-20|RF1|JH3 | EVQLLES- GGGLVQPGGSLRL SCAASG-FTFR | S-----YVMS | WVRQAPGK GLEWVS | AISGR--- GSNTFYTDS VKG | RFTISRDNSKNTLYLQMNSL RAEDTAVYYCAK | GITGSH--------- -----GAFDI | WGQGT MVTVS S |
| VH3|3-23|D7|7-27|RF1|JH4 | | EVQLLES GGGLVQPGGSLRL SCAASG-FTFS | YAMS | WVRQAPGK GLEWVS | AISGS GGSTYYADS VKG | RFTISRDNSKNTLYLQMNSL RAEDTAVYYCAK | LGTDI ------FDY | WGQGT LVTVS S |
| iPS:4 34059 | 21-225_51C5 | VH3|3-23|D7|7-27|RF1|JH4 | EVQLLES- GGGLVQPGGSLRL SCAASG-FTFS | S-----YVMS | WVRQTPGK GLEWVS | TMSGS--- GGRTYYADS VNG | RFTVSRDNSKNTLYLQMSSL RAEDTAVYYCAR | VTA------------ ------FDY | WGQGT LVTVS S |
| iPS:4 34213 | 21-225_60A4 | VH3|3-23|D7|7-27|RF1|JH4 | EVQLLES- GGGLVQPGGSLRL SCAASG-FTFS | S-----YVMS | WVRQAPGK GLEWVS | SISGS--- GGWTNYADS VKG | RFTISRDNSKNTLYLQMNSL RAEDTAVYYCAR | LTG------------ ------FDY | WGQGT LVTVS S |
| iPS:4 34215 | 21-225_60F7 | VH3|3-23|D7|7-27|RF1|JH4 | EVQLLES- GGGLVQPGGSLRL SCAASG-FTFS | S-----YVMS | WVRQAPGK GLEWVS | GISGS--- GNRTYYADS VKG | RFTISRDNSKNTLYLQMNSL RAEDSAVYYCGS | LG------------- --------ID | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 34241 | 21-225_61E6 VH3]3-23]D7]7-27]RF1]JH4 | EVQLLES-GGGLVQPGGSLRL SCAASG-FTFR | S-----YAMS | WVRQAPGK GLEWVS | ATSGS---GVNTFYADS VKG | RFTISRDNSKNTLYLQMNSL RAEDTAVYYCAK | LELG----------IFDY | WGQGT LVTVS S |
| iPS:4 34281 | 21-225_57B8 VH3]3-23]D7]7-27]RF1]JH4 | EVQLLES-CGGLVQPGGSLRL SCAASG-FTFR | S-----YAMS | WVRQAPGK GLEWVS | AISGS---GGNTFYADS VKG | RFTISRDNSKNTLYLQMNSL RAEDTAVYYCAK | LELG----------IFDY | WGQGT LVTVS S |
| iPS:4 34301 | 21-225_58F11 VH3]3-23]D7]7-27]RF1]JH4 | EVQLLES-CGGLVQPGGSLRL SCAASG-FTFS | S-----YAMS | WVRQAPGK GLEWVS | AISGS---GGNTFYADS VKG | RFTISRYNSKNTLYLQMNSL RAEDTAVYYCAK | FFGMVG--------AGFFDY | WGQGT LVTVS S |
| iPS:4 35523 | 21-225_157G5 VH3]3-23]D7]7-27]RF1]JH4 | EVQLLES-GGGLVQPGGSLRL SCAASG-FTFS | S-----YVMS | WVRQAPGK GLDWVS | AMSGS---GGRTYYADS VKG | RFTISRDNSKNTLYLQMNSL RAEDTAVYYCAK | YTW-----------NGY | WGQGT LVTVS S |
| iPS:4 35659 | 21-225_167D12 VH3]3-23]D7]7-27]RF1]JH4 | EVQLLES-GGGLVQFGGSLRL SCAASG-FTFS | S-----YVMS | WVRQAPGK GLEWVS | AMSGS---GGRTYYADS VKG | RFTISRDNSKNTLYLQMNSL RAEDTAVYYCAK | YTW-----------NGY | WGQGT LVTVS S |
| iPS:4 35765 | 21-225_177D3 VH3]3-23]D7]7-27]RF1]JH4 | EVQLLES-CGGLVQPGGSLRL SCAASG-FTFS | S-----YVMN | WVRQAPGK GLEWVS | GMSGS---GGRTYYADS VKD | RFTISRDNSKNTLSLQMNSL RAEDTAVYYCAK | VTF-----------FDY | WGQGT LVTVS S |
| iPS:4 37216 | 21-225_51D5 VH3]3-23]D7]7-27]RF1]JH4 | EVQLLES-GGGLVQPGGSLRL SCAASG-FTFS | S-----YVMS | WVRQTPGK GLEWVS | IMSGS---GGRTYYADS VNG | RFTVSRDNSKNTLYLQMSSL RAEDTAVYYCAR | VTA-----------FDY | WGQGT LVTVS S |
| | Germline | H_FR1 | H_CDR1 | H_FR2 | H_CDR2 | H_FR3 | H_CDR3 | H_FR4 |
| VH3]3-21]D5]5-24]RF2]JH4 | | EVQLLES-CGGLVKPGGSLRL SCAASG-FTFS | S-----YSMN | WVRQAPGK GLEWVS | SISSS---SSYIYYADS VKG | RFTISRDNAKNSLYLQMNSL RAEDTAVYYCAR | ARL-----------DY | WGQGT LVTVS S |
| iPS:4 34063 | 21-225_51G7 | | | | | | | |
| | Germline | H_FR1 | H_CDR1 | H_FR2 | H_CDR2 | H_FR3 | H_CDR3 | H_FR4 |
| VH3]3-23]D7]7-27]RF3]JH4 | | EVQLLES-CGGLVQPGGSLRL SCAASG-FTFS | R-----NAMS | WVRQAPGM GLEWVS | AISGR---GGNTFYADS VKG | RFTVSRDNSKNTLFLQMNSL RAEDTAVYYCAK | NGREQ---------WLDY | WGQGT LVTVS S |
| iPS:4 34083 | 21-225_52H2 | | | | | | | |
| | Germline | H_FR1 | H_CDR1 | H_FR2 | H_CDR2 | H_FR3 | H_CDR3 | H_FR4 |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34087 | 21-225_52F6 | VH3|3-30.3|D6|6-6|RF2|JH6 | QVQLVES-GGGVVQPGRSLRL SCAASG-FTFS | S-----YGMH | WVRQAPGK GLEWVA | IISYG---GSNKYIADS VKG | RFTISRDNSKNTLYLQMNSL RADDTAVYYCAR | RSAARP-------GYGMDV | WGQGT TVTVS S |
| iPS:4 34111 | 21-225_53H2 | VH3|3-30.3|D6|6-6|RF2|JH6 | QVQLVES-GGGVVQPGRSLRL SCAASG-FTFS | S-----YGMH | WVRQAPGK GFEWVA | VISYG---GSNKYHADS VKG | RFTISRDNSKNTLYLQMNSL RAEDTAVYYCAR | RGAARP-------GYGMDV | WGQGT TVTVS S |
| iPS:4 34121 | 21-225_53F6 | VH3|3-30.3|D6|6-6|RF2|JH6 | QVQLVES-GGGVVQPGRSLRL SCAASG-FTFS | S-----YGMH | WVRQAPGK GLEWVA | VISYG---GSNKYDADS VKG | RFTISRDNSKNTLYLQMISL RAEDTAVYYCAR | RRAARP-------GYGMDV | WGQGT TVTVS S |
| iPS:4 34163 | 21-225_50H1 | VH3|3-30.3|D6|6-6|RF2|JH6 | QVQLVES-GGGVVQPGRSLRL SCAASG-FTFS | S-----YGMH | WVRQAPGK GLEWVS | IISYG---GSNKYDADS VKG | RFTISRDNSKNTLYLQMISL RAEDTAVYYCAR | RRAARP-------GYGMDV | WGQGT TVTVS S |
| iPS:3 94035 | 21-225_5G9 | VH3|3-30.3|D6|6-6|RF2|JH6 | QVQLVES-GGGVVQPGRSLRL SCAASG-FTFS | N-----YGMH | WVRQAPGK GLEWVA | IISYA---GSNKYADS VKG | RFTISRDNSKNTLYLQMNSL RAEDTAVYYCVR | RITARL-------YYGMDV | WGQGT TVTVS S |
| VH3|3-33|D2|2-8|RF1|JH4 | | Germline | | | | | | | |
| iPS:4 34095 | 21-225_52F10 | VH3|3-33|D2|2-8|RF1|JH4 | QVQLVES-GGGVVQPGRSLRL SCAASG-FTFS | F-----YGMH | WVRQAPGK GLEWVA | VINDD---GSNKYADS VKG | RFTISRDNSKNTLFLQMSL RAEDTAVYYCAR | DSLYSS-------SWLFDY | WGQGT LVTVS S |
| VH3|3-23|D4|4-23|RF3|JH4 | | Germline | | | | | | | |
| iPS:4 34107 | 21-225_53E2 | VH3|3-23|D4|4-23|RF3|JH4 | EVQLLES-GGGLIQPGGSLRL SCAASG-FTFR | S-----YAMS | WVRQAPGK GLEWVS | AISGS---GGNTFYADS VKG | RFTISRDNSKNTLYLQMNTL RAEDTAVYYCAK | KVVDTA-------MALDY | WGQGT LVTVS S |
| iPS:4 34181 | 21-225_56B2 | VH3|3-23|D4|4-23|RF3|JH4 | EVQLLES-GGGLIQPGGSLRL SCAASG-FTFR | S-----YAMS | WVRQAEGK GLEWVS | AISGS---GGNTFYADS VKG | RFTISRDNSKNTLYLQMNTL RADDTAVYYCAK | KVVDTA-------MALDY | WGQGT LVTVS S |
| VH3|3-23|D1|1-26|RF1|JH3 | | Germline | | | | | | | |
| iPS:4 34117 | 21-225_53C6 | VH3|3-23|D1|1-26|RF1|JH3 | EVQLLES-GGGLVQPGGSLRL SCAASG-FTFS | S-----YAMN | WVRQAPGK GLEWVS | AISGS---GGATYYADS VKG | RFTISRDNSKNTLYLQMNSL RAEDTAVYYCAK | PLVGAH-------DAFEI | WGQGT MVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 92984 | 21-225_30E11 | VH3J3-23|D1|1-26|RF1/JH3 | EVQLLES-GGDMVQPGGSLRLSCAASG-FTFS | I-----YAMS | WVRQAPGK GLEWVS | VISGS---GGSSFYADS VKG | RFTISRDNSKNTLYLQMNSL RAEDTAVYYCTK | DRVKAH------DGFDI | WGQGT MVTVS S |
| iPS:3 93114 | 21-225_33G12 | VH3J3-23|D1|1-26|RF1/JH3 | EVQLLES-GGDMVQPGGSLRLSCAASG-FTFS | S-----YAMS | WVRQAPGK GLEWVS | VISGS---GGSSFYADS VKG | RFTISRDNSKNTLYLQMNSL RAEDTAVYYCAK | DRVRAH------DGFDI | WGQGT MVTVS S |
| | Germline | | H_FR1 | H_CDR1 | H_FR2 | H_CDR2 | H_FR3 | H_CDR3 | H_FR4 |
| VH3J3-33|D3|5-24|RF2/JH4 | | | | | | | | | | |
| iPS:3 34127 | 21-225_53H8 | VH3J3-33|D5|5-24|RF2/JH4 | QVQLVES-GGGLVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | ARIG---------YFDS | WGQGT LVTVS S |
| | Germline | | H_FR1 | H_CDR1 | H_FR2 | H_CDR2 | H_FR3 | H_CDR3 | H_FR4 |
| VH3J3-23/D4|4-17|RF2/JH4 | | | | | | | | | | |
| iPS:4 34147 | 21-225_55E1 | VH3J3-23|D4|4-17|RF2/JH4 | EVQLLES-GGGLVQPGGSLRLSCAASG-FTFS | S-----YAMS | WVRQAPGK GLEWVS | AISGR---GSSTFYADS VKG | RFTISRDNSKNTLYLQMNSL RAEDTAVFYCAK | DHG1VG------TIYFDY | WGQGT LVTVS S |
| iPS:4 35303 | 21-225_146A6 | VH3J3-23|D4|4-17|RF2/JH4 | EVQLLES-GGGLVQPGGSLRLSCAASG-PTFN | S-----YAMN | WVRQAPGK GLEWVS | AISGS---GGNTFYADS VKG | RFTISRDNSKNTLYLQMNSL RAEDTAVYYCAK | KDNDYVW------GSPYFDY | WGQGT LVTVS S |
| iPS:4 35335 | 21-225_147D10 | VH3J3-23|D4|4-17|RF2/JH4 | EVQLLES-GGGLVQPGGSLRLSCAASG-FTFS | S-----YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |
| iPS:4 35339 | 21-225_147D12 | VH3J3-23|D4|4-17|RF2/JH4 | EVQLLES-GGGLVQSGGSLRLSCAASG-FTFS | S-----YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |
| iPS:4 35343 | 21-225_148E2 | VH3J3-23|D4|4-17|RF2/JH4 | EVQLLES-GGGLVQPGGSLRLSCAASG-FTFS | S-----YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |
| iPS:4 35381 | 21-225_149C6 | VH3J3-23|D4|4-17|RF2/JH4 | EVQLLES-GGGLVQPGGSLRLSCAASG-FTFS | S-----YAMS | WVRQAPGK GLEWVS | AISGS---GGNTFYADS VKG | RFTISRDNSKNTLYLHMNSL RAEDTAVYYCAK | KDYDYVW------GSPYFDY | WGQGT LVTVS S |
| iPS:4 35391 | 21-225_149F8 | VH3J3-23|D4|4-17|RF2/JH4 | EVQLLES-GGGLVQPGGSLRLSCAASG-FTFS | S-----YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 35395 | 21-225_149D11 | VH3/3-23/D4/4-17/RF2/JH4 | EVQLLES-GGGLVQPGGSLRLSCAASG-FTFS | S------YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |
| iPS:4 35403 | 21-225_150C5 | VH3/3-23/D4/4-17/RF2/JH4 | EVQLLES-GGGLVQPGGSLRLSCAASG-FTFS | S------YAMS | WVRQAPGK GLEWVS | AISGS---GGNTFYADS VKG | RFTISRDNSKNTLYLQMNSL RAEDTAVYYCAK | KDYDYVW------GSPYFDY | WGQGT LVTVS S |
| iPS:4 35447 | 21-225_152H7 | VH3/3-23/D4/4-17/RF2/JH4 | EVQLLES-GGGLVQPGGSLRLSCAASG-FTFS | S------YAMN | WVRQAPGK GLEWVS | AISGS---GGNTFYADS VKG | RFTISRDNSKNTLYLQMNSL RAEDTAVYYCAK | KDNDYVW------GSPYFDY | WGQGT LVTVS S |
| iPS:4 35453 | 21-225_152G10 | VH3/3-23/D4/4-17/RF2/JH4 | EVQLLES-GGGLVQPGGSLRLSCAASG-FTFS | S------YAMS | WVRQAPGK GLEWVS | AISGR---GGNTFYADS VKG | RFTISRDNSKNTLYLQMNSL RAEDTAVYYCAK | KDYDYVW------GSPYFDY | WGQGT LVTVS S |
| iPS:4 35483 | 21-225_155A4 | VH3/3-23/D4/4-17/RF2/JH4 | EVQLLES-GGGLVQPGGSLRLSCAASG-FTFS | S------YAMS | WVRQAPGK GLEWVS | AISGS---GGNTFYADS VKG | RFTISRDNSKNTLYLQMNSL RAEDTAVYYCAK | KDYDYVW------GSPYFDY | WGQGT LVTVS S |
| iPS:4 35485 | 21-225_155B4 | VH3/3-23/D4/4-17/RF2/JH4 | EVQLLES-GGGLVQPGGSLRLSCAASG-FTFS | S------YAMS | WVRQAPGK GLEWVS | AISGS---GGNTFYADS VKG | RFTISRDNSKNTLYLQMNSL RAEDTAVYYCAK | KDYDYVW------GSPYFDY | WGQGT LVTVS S |
| iPS:4 35777 | 21-225_178F7 | VH3/3-23/D4/4-17/RF2/JH4 | EVHLLES-GGGLVQPGGSLRLSCAASG-FTFS | S------YAMT | WVRQAPGK GLEWVS | VISGS---GGNTFYADS VKG | RFTISRDNSKNTLYLQMNSL RAEDTAVYYCAR | RYGD---------YFDY | WGQGT LVTVS S |
| iPS:4 35783 | 21-225_179G1 | VH3/3-23/D4/4-17/RF2/JH4 | EVHLLES-GGGLVQTGGSLRLSCAASG-FTFS | S------YAMT | WVRQAPGK GLEWVS | VISGF---GGNTFYADS VKG | RFTISRDNSKNTLYLQMNSL RAEDTAVYYCAR | RYGD---------YFDY | WGQGT LVTVS S |
| iPS:4 35833 | 21-225_190D12 | VH3/3-23/D4/4-17/RF2/JH4 | EVQLLES-GGGLVQPGGSLRLSCAASG-FTFS | S------YAMS | WVRQAPGK GLEWDS | AIIGN---GGRTYYADS VKG | RFTISRDNSKNTLYLQMNSL RAEDTAVYYCAK | DMGRYS------YGFFDY | WGQGT LVTVS S |
| iPS:4 36156 | 21-225_197C8 | VH3/3-23/D4/4-17/RF2/JH4 | EVQLLES-GGGLVQPGGSLRLSCAASG-FTFS | S------SAMT | WVRQAPGK GLEWVS | AIIGN---GGRAYYADS VKG | RFTISRDNSKNTLYLQMNSL RIEDTAVYYCAK | DRGYSRIA------VAGIFDY | WGQGT LVTVS S |
| | Germline | VH3/3-21/D1/11-1/RF1/JH4 | EVQLVES-GGGLVKPGGSLRLSCAASG-FTFN | S------YRMN | WVRQAPGK GLEWVS | SISSS---SNHIDYADS VKG | RFTISRDNAKNSLYLQMNSL RAEDTALYYCAR | GT----------DY | WGQGT LVSVS S |
| iPS:4 34157 | 21-225_55D4 | VH3/3-21/D1/11-1/RF1/JH4 | EVQLVES-GGGLVKPGGSLRLSCAASG-FTFN | S------YRMN | WVRQAPGK GLEWVS | SISSS---SNHIDYADS VKG | RFTISRDNAKNSLYLQMNSL RAEDTALYYCAR | GT----------DY | WGQGT LVSVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS.4 34243 | 21-225_62C1 | VH3/3-21/D1[1-1]/RF1/JH4 | EVQLVES-GGGLVKPGGSLRL SCAASG-FTFS | S-----YSMN | WVRQAPGK GLEWVS | SISSS---SSYIYYADS VKG | RFTISRDNAKNSLYLQMNSL RAEDTAVYYCAI | FG---------VD | WGQGT LVTVS S |
| iPS.4 35505 | 21-225_157C1 | VH3/3-21/D1[1-1]/RF1/JH4 | EVQLVES-GGGLVKPGGSLRL SCAASG-FTFS | S-----YRMN | WVRQAPGK GLEWVS | SMSNS---SSSIYYADS VKG | RFTISRDNAKNSLYLQMNSL RAEDTAVYYCAR | QAA--------QDY | WGQGT LVTVS S |
| iPS.3 92966 | 21-225_32G3 | VH3/3-21/D1[1-1]/RF1/JH4 | EVQLVES-GGGLVKPGGSLRL SCAASG-FTFS | S-----YSMN | WVRQAPGK GLEWVS | SISGS---SSYIYYADS VKG | RFTISRDNAKNSLYLQINSL RAEDTAVYYCAR | GNIA-------RDY | WGQGT LVTVS S |
| Germline | | | H_FR1 | H_CDR1 | H_FR2 | H_CDR2 | H_FR3 | H_CDR3 | H_FR4 |
| VH3/3-33/D7[7-27]/RF3/JH4 | | | | | | | | | |
| iPS.4 34159 | 21-225_55B8 | VH3/3-33/D7[7-27]/RF3/JH4 | QVQLVES-GGGVVQPGRSLRL SCAASG-FTFS | D-----YGMH | WVRQAPGK GLEWVA | VIWYD---ENNKYYADS VKG | RFTISRDNSKNTLYLQMNSL RAEDTAVYYCTR | EWF--------DY | WGQGT LVTVS S |
| iPS.3 93026 | 21-225_32B6 | VH3/3-33/D7[7-27]/RF3/JH4 | QVQLVES-GGGVVQPGRSLRL SCAASG-FTFS | D-----YGMH | WVRQAPGK GLEWVA | VIWHD---ENTKYYADS VKG | RFTISRDNSKNTLYLQMNSL RAEDTAVYYCAR | EWG--------DY | WGQGT LVTVS S |
| Germline | | | H_FR1 | H_CDR1 | H_FR2 | H_CDR2 | H_FR3 | H_CDR3 | H_FR4 |
| VH3/3-33/D6[6-6]/RF3/JH4 | | | | | | | | | |
| iPS.4 34165 | 21-225_50F2 | VH3/3-33/D6[6-6]/RF3/JH4 | QVQLVES-GGGVVQPGRSLRL SCAASA-FTFS | S-----YGMH | WVRQTPGK GLEWVA | VIWHD---GSNKYYADS VKG | RFTISRDNSKNTLYLQMNSL RAEDTAVYYCAR | DEQLG------TFDY | WGQGT LVTVS S |
| iPS.4 34191 | 21-225_56B6 | VH3/3-33/D6[6-6]/RF3/JH4 | QVQLVES-GGGVVQPGRSLRL SCAASG-FTFS | S-----YGMH | WVRQAPGK GLEWVG | VIWHD---GSNKYVDS VKG | RFTISRDNSKNTLYLQMNSL RAEDTAVYYCAR | DEQLG------TFDY | WGQGT LVTVS S |
| Germline | | | H_FR1 | H_CDR1 | H_FR2 | H_CDR2 | H_FR3 | H_CDR3 | H_FR4 |
| VH1/1-46/D4[4-17]/RF2/JH6 | | | | | | | | | |
| iPS.4 34171 | 21-225_50G4 | VH1/1-46/D4[4-17]/RF2/JH6 | QVQLVQS-GAEVKEPGASVKV SCKASG-YIFT | S-----YYIH | WVRQAPGQ GLEWMG | VINPS---NGRTSYAQK FQG | RVTMTRDTSTVYMELSSL RSEDTAVYYCAR | DRGDGYY----FYGMDV | WGQGT TVTVS S |
| Germline | | | H_FR1 | H_CDR1 | H_FR2 | H_CDR2 | H_FR3 | H_CDR3 | H_FR4 |
| VH3/3-30.3/D4[4-17]/RF2/JH3 | | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34175 | 21-225_55A11 | VH3/3-30.3/D4/4-17/RF2/J H3 | QVQLVES-GGGVVQPGRSLRL SCAASG-FTFS | S------YGMH | WVRQTPGK GLEWVA | VISYV---GSIKYYADS VRG | RFTISRDNSKNTLYLQMNSL RTEDTAVYYCAR | GRGRIYSDY-------------GHDAFDI | WGQGT MVTVS S |
| | Germline | VH1/1-02/D1/1-1/RF1/JH2 | | | | | | | |
| iPS:4 34193 | 21-225_56C6 | VH1/1-02/D1/1-1/RF1/JH 2 | QVQLVQS-GAEVKKPGASVKV SCKASG-YTFT | D------YHMH | WVRQAPGQ GLEWMG | WINPN----RGGTNYVQK FQG | RVAMINDTSISTAYMELSGL RSDDTAVYYCAR | DGIS--------------SPDY | WGRGI LVTVS S |
| | Germline | VH1/1-02/D5/5-24/RF1/JH4 | | | | | | | |
| iPS:4 34195 | 21-225_56F6 | VH1/1-02/D5/5-24/RF1/J H4 | QVQLVQS-GAEVKKPGASVKV SCKASG-FTFT | D------YYMH | WVRQAPGK GLEWMG | WINPN----SGGTNYAQR FQG | RVTMTRDTSISTAYMELSRL RSDDTAVYYCTR | EGATRP--------------TGFDY | WGQGT LVTVS S |
| | Germline | VH3/3-33/D1/1-1/RF2/JH4 | | | | | | | |
| iPS:4 34203 | 21-225_60E2 | VH3/3-33/D1/1-1/RF2/JH 4 | QVQLVES-GGGVVQPGRSLRL SCAASG-FTFN | D------YGMH | WVRQAPGK GLEWVA | IIWYD----ENNKYYADS VKG | RFTISRDNSKNTLYLQMSSL RAEDTAVYYCAR | DVLD---------------PFDY | WGQGT LVTVS S |
| iPS:4 34229 | 21-225_61H1 | VH3/3-33/D1/1-1/RF2/JH 4 | QVQLVES-GGGVVQPGRSLRL SCAASG-FTFN | D------YGMH | WVRQAPGK GLEWMG | IIWYD----ESNKYYADS VKG | RFTISRDNSKNTLYLQMNSL RAEDTAVYYCAR | DVLD---------------PFDY | WGQGT LVTVS S |
| | Germline | VH1/1-02/D5/5-18/RF3/JH6 | | | | | | | |
| iPS:4 34209 | 21-225_60C3 | VH1/1-02/D5/5-18/RF3/J H6 | QVQLVQS-GAEVKKPGASVKV SCKASG-YSFT | G------HYIH | WVRQAPGQ GLEYMG | WINPN----SGGTNYVQK FQG | RVTMTRDTSISTAYMELSRL RSDDTAIYYCAR | GGLLGATN----------YYYYGMDV | WGQGT TVTVS S |
| iPS:4 34315 | 21-225_59G7 | VH1/1-02/D5/5-18/RF3/J H6 | QVQLVQS-GAEVKKPGASVKV SCKASG-YSFT | G------HYIH | WVRQAPGQ GLEYMG | WINPN----SGGTNYVQK FQG | RVTMTRDTSISTAYMELSRL RSDDTAIYYCSR | GGLLGATN----------YYYYGMDV | WGQGT TVTVI S |
| iPS:4 34319 | 21-225_59B9 | VH1/1-02/D5/5-18/RF3/J H6 | QVQLVQS-GPEVKKPGASVKV SCKASG-YIFT | G------NYIH | WVRQAPGQ GLEYMG | WINPN----SGGTNYVQK FQG | RVTMTRDISISTANMELISL RSDDTAVYYCSR | GGLLGATY----------YYYYGMDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 43003 | 21-225_43F11_LC 2 | VH1|1-02/D5|5-18|RF3/J H6 | QVQLVQS-GAEVKKPGASVKV SCKASG-YIFT | G------YYIH | WVRQAPGQ GLEWMG | WINPN--- SGGTNYAQK FQG | GVTMTRLTSINTAYMDLSRL RSDDTAVYYCAR | GGNYFY------NHVMDV | WGQGT PVTVS S |
| iPS:4 43005 | 21-225_43F11_LC 1 | VH1|1-02/D5|5-18|RF3/J H6 | QVQLVQS-GAEVKKPGASVKV SCKASG-YIFT | G------YYIH | WVRQAPGQ GLEWMG | WINPN--- SGGTNYAQK FQG | GVTMTRLTSINTAYMDLSRL RSDDTAVYYCAR | GGNYFY------NHVMDV | WGQGT PVTVS S |
| | Germline | | | | | | | | |
| | VH4|4-30.4|D5|5-12|RF3|JH4 | | | | | | | |
| iPS:4 34217 | 21-225_60E8 | VH4|4-30.4/D5|5-12|RF3/J H4 | QVQLQES-GPGLVRPSATLSL TCIVSG-GSIS | RS---SYYWG | WIRQPGK GLEWIG | SIYY----- SGSASYNPS LKS | RVTISVDTSENQFSLRLSSV TAADTAVYYCAR | LDSGW------SFDY | WGQGT LVTVS S |
| | Germline | | | | | | | | |
| | VH3|3-23/D3|3-22|RF3/JH4 | | | | | | | |
| iPS:4 34219 | 21-225_60E9 | VH3|3-23/D3|3-22|RF3/J H4 | EVQLLES-GGGLVQPGGSLRL SCAASG-FTFS | S------YAMS | WVRQAPGK GLEWVS | AISGS---- GGNTFYADS VKG | RFTISRDNSKNTLFLQMNSL RAEDTAVYYCAK | FFGIVG------AGYFDY | WGQGT LVTVS S |
| iPS:4 34289 | 21-225_57H12 | VH3|3-23/D3|3-22|RF3/J H4 | EVQLLES-GGGLVQPGGSLRL SCAASG-LIFS | S------YAMS | WVRQDPGK GLEWVS | AISGS---- GGNTFYGDS VKG | RFTISRDNSKTLYLQMNSL RAEDTAVYYCAK | FFGIVG------AGYFDY | WGQGT LVTVS S |
| iPS:4 34297 | 21-225_58A10 | VH3|3-23/D3|3-22|RF3/J H4 | EVQLLES-GGGLVQPGGSLRL SCAASG-FTFR | S------YAMS | WVRQAPGK GLEWVS | AISGS---- GGNTFYADS VKG | RFTISRDNSKNTLFLQMNSL RAEDTAVYYCAK | FFGIVG------AGYFDY | WGQGT LVTVS S |
| iPS:3 92996 | 21-225_28B1 | VH3|3-23/D3|3-22|RF3/J H4 | EVQLLES-GGGLVQPGGSLRL SCAASG-FIFS | S------YAMS | WVRQAPGK GLEWVS | AISGS---- GGNTFYADS VKG | RFTISRDNSKNTLYLQMNSL RAEDTAVYYCAK | LGRIAVT------GPYFDY | WGQGT LVTVS S |
| | Germline | | | | | | | | |
| | VH4|4-59/D4|4-11|RF3/JH4 | | | | | | | |
| iPS:4 34225 | 21-225_60E12 | VH4|4-59/D4|4-11|RF3/J H4 | QVQLQES-GPGLVKPSETLSL TCTVSG-GSIS | S------YFMS | WIRQPAGK GLEMIG | RIYT----- RGSTNYNPS LKS | RVTMSVDTSKNQFSLKLSSV IAADTAVYYCAR | EGKTGG------VSYFDY | WGQGT LVTVS S |
| iPS:4 34227 | 21-225_61A1 | VH4|4-59/D4|4-11|RF3/J H4 | QVQLQES-GPGLVKPSETLSL TCIVSG-GSIS | S------HFWS | WIRQPAGK GLEWIG | RIYI----- RGSTNYNPS LKS | RVTMSVDTSKNQFSLKLSSV TAADTAVYYCAR | EGKIGG------VSYFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34267 | 21-225_57F2 | VH4/4-59/D4/4-11/RF3/JH4 | QVQLQES-GPGLVKPSETLSL TCTVSG-GSIS | S-----YYWS | WIRQPAG GLEWIG | RIYT----RGSTNYNPS LKS | RVTMSIDTSKNQFSLKLSSV TAADTAVYYCAR | EGKTGG----------VSYFDY | WGQGT LVTVS S |
| | Germline | VH3/3-23/D5/5-18/RF3/JH3 | EVQLLES-GGGLVQPGGSLRL | ----YAMS | WVRQAPGK GLEWVS | ASSR----GSSTYYADS VKG | RFTISRDNSKNTLYLQMNSL RAEDTAVYYCAK | VSYSY----------DAFDI | WGQGT MVTVS S |
| iPS:4 34239 | 21-225_58F1 | VH3/3-23/D5/5-18/RF3/JH3 | EVQLLES-GGGLVQPGGSLRL SCAASG-FTFS | S-----YAMS | WVRQAPGK GLEWVS | AISTG----GGNTYYADS VKG | RFTISRDNSKNTLYLQMNSL RAEDTAVYYCAK | RGVYGD----------FDAFDI | WGQGT MVTVS S |
| iPS:4 34309 | 21-225_59B5 | VH3/3-23/D5/5-18/RF3/JH3 | EVQLLES-GGGLVQPGGSLRE SCAASG-FTFS | S-----YAMN | WVRQAPGK GLEWVS | AISGS----GGNTYYADS VKG | RFTISRDNSKNTLYLQMNSL RAEDTAVYYCAK | RGVYGD----------YEAFDI | WGQGT MVTVS S |
| | Germline | VH3/3-33/D5/5-18/RF1/JH4 | QVQLVES-GGGVVQPGRSLRL SCAASG-FTFS | ----YGMH | WVRQAPGK GLEWVA | VISYD----GSNKYYADS VKG | RFTISRDNSKNTLYLQMNSL RAEDTAVYYCAR | VSTAM----------YFDY | WGQGT LVTVS S |
| iPS:4 34245 | 21-225_62H1 | VH3/3-33/D5/5-18/RF1/JH4 | QVQLVES-GGGVVQPGRSLRL SCAASG-FTFS | S-----YGMH | WVRQAPGQ GLEWMA | IIWYD----GSNKYYADS VKG | RFTISRDNSKNTLYLQINSL RAEDTAVYYCAR | EDPRT----------SCSDY | WGQGT LVTVS S |
| iPS:4 34323 | 21-225_62H8 | VH3/3-33/D5/5-18/RF1/JH4 | QVQLVES-GGGVVQPGRSLRL SCAASG-FTFS | T-----YGMH | WVRQAPGK GLEWVA | VIWHD----GSDKYYVDS VKG | RFTISRDNSKNTLYLQMNSL RAEDTAVYYCAR | EDPRT----------SCSDY | WGQGT LVTVS S |
| iPS:4 34379 | 21-225_66A9 | VH3/3-33/D5/5-18/RF1/JH4 | QVQLVES-GGGVVQPGRSLRL SCAASG-FTFS | S-----YGMN | WVRQAPGK GLEWVA | VIWHD----GSDKYYADS VKG | RFTISRDNSKNTLYLQMNSL RAEDTAVYYCAR | EDPRT----------SCSDY | WGQGT LVTVS S |
| | Germline | VH3/3-33/D1/1-1/RF3/JH4 | QVQLVES-GGGVVQPGRSLRL SCAASG-FTFS | ----YGMH | WVRQAPGK GLEWVA | VIWYD----GSNKYYADS VKG | RFTISRDNSKNTLYLQMNSL RAEDTAVYYCAR | SHSHS----------YFDY | WGQGT LVTVS S |
| iPS:4 34247 | 21-225_62D2 | VH3/3-33/D1/1-1/RF3/JH4 | QVYLVES-GGGVVQPGRSLRL SCAASG-FTFS | S-----YGMH | WVRQAPGK GLEWVA | VINYD----GSNKYSADS VKG | RFTISRDNSKNTLDLQMNSL RAEDTAVYYCAR | DNGNW----------NYLDY | WGQGT LVTVS S |
| iPS:4 36838 | 21-225_52H4 | VH3/3-33/D1/1-1/RF3/JH4 | QVQLVES-GGGVVQPGRSLRL SCAASG-FTFS | H-----FGMH | WVRQAPGK GLKWVA | VINYD----GSNKYYADS VKG | RFTISRDNSKNTLYLQMNSL RAEDTAVYYCAR | GDWNY----------EGFDY | WGQGT LVTVS S |
| iPS:4 36948 | 21-225_183F5 | VH3/3-33/D1/1-1/RF3/JH4 | QVQLVES-GGGVVQPGRSLRL SCAASG-FTFS | S-----YGML | WVRQAPGK GLEWVT | VIWYD----GSGKYYADS VKG | RFTISRDNSKNTLYLQMNSL RAEDTAVYYCAR | ENFW----------SGDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4/4-39|D5|5-12|RF3|JH4 | | QIQLQES-GPGLVKPSETLSL TCTVSG-GSIS | RS---SYYWG | WIRQPPGK GLEWIG | SIYY---- SGSTSYNPS LKS | RVTISVDTSKNQFSLKLSSV TAADTAVYYCAR | QQSGID ----FDY | WGQGT LVTVS S |
| iPS:4 34249 | VH4|4-39|D5|5-12|RF3|JH4 | QIQLQES-GPGLVKPSETLSL TCIVSG-GSIS | RS---SYYWG | WIRQPPGK GLEWIG | SIYY---- SGIASYNPS LKS | RVTISVDTSKNQFSLKLNSV IATDTAVYYCAR | LSSGW------- ----SFDY | WGQGT LVTVS S |
| iPS:4 34353 | VH4|4-39|D5|5-12|RF3|JH4 | QIQLQES-GPGLVKPSETLSL TCTVSG-VSIS | RS---SYYWG | WIRQPPGK GLEWIG | SIYY---- SGSTSYNPS LKS | RVTISVDTSKNQFSLKLSSV TAADTAVYYCAR | LDSGW------- ----SFDY | WGQGT LVTVS S |
| iPS:3 94073 | VH4|4-39|D5|5-12|RF3|JH4 | QIQLQES-GPGLVKPSETLSL TCTVSG-GSIS | RS---SYYWG | WIRQPPGK GLEWIG | NIYY---- SGSTYNNPS LKS | RVTISVDTSKNQFSLKLSSV TAADTAVYYCAR | QGSGW------- ----EVDY | WGQGT LVTVS S |
| | Germline | H_FR1 | H_CDR1 | H_FR2 | H_CDR2 | H_FR3 | H_CDR3 | H_FR4 |
| VH1|1-02|D7|7-27|RF1|JH4 | | QVQLVQS-GAEVKKPGASVKV SCKASG-YTFT | G------YYMH | WVRQAPGQ GLEWMG | WINPK--- SGGTNSAQK FQG | RVTMTRDTSISTAYMELSSL RSDDTAVYYCAR |  ----FDY | WGQGT LVTVS S |
| iPS:4 34259 | VH1|1-02|D7|7-27|RF1|JH4 | QVQLVQS-GAEVKKPGASVKV SCKASG-YTFT | G------YYMH | WVRQAPGQ GLEWMG | WIKPK--- SGGTNQAQK FQG | RVTMTRDTSISTAYMELSSL RSDDTAVYYCAR | APGIAAAG---- ----TWGIAAAG | WGQGT LVTVS S |
| iPS:4 34347 | VH1|1-02|D7|7-27|RF1|JH4 | QVQLVQS-GAEVKKPGASVKV SCKASG-YTFT | G------YYMH | WVRQAPGQ GLEWMG | WIKPN--- SGGTNQAQK FQG | RVTMTRDTSISTAYMELSGL RSDDTAVYYCAR | APGTAATG---- ----TWGYFDY | WGQGT LVTVS S |
| iPS:4 34359 | VH1|1-02|D7|7-27|RF1|JH4 | QVQLVQS-GAEVKKPGASVKV SCKASG-YTFT | G------YYIH | WVRQAPGQ GLEWMG | WINPN--- SGGTNSAQK FQG | RVTMTRDTSISTAYMELSRL RSDDTAVYYCAR | APGKAAAG---- ----TWGYFDY | WGQGT LVTVS S |
| iPS:4 34369 | VH1|1-02|D7|7-27|RF1|JH4 | QVQLVQS-GAEVKKPGASVKV SCKASG-YTFT | G------YYMH | WVRQAPGQ GLEWMG | WINPN--- SGGTNNAQK FQG | RVTMTRDTSISTAYMELSRL RSDDTAVYYCAR | APGTAAAG---- ----TWGYFDY | WGQGT LVTVS S |
| iPS:4 34373 | VH1|1-02|D7|7-27|RF1|JH4 | QVQLVQS-GAEVKKPGASVKV SCKASG-YTFT | G------YYMH | WVRQAPGQ GLEWMG | WIKPN--- SGGTNQAQK FQG | RVTMTRDTSISTAYMELSRL RSDDTAVYYCAR | APGTVAAG---- ----TWGYFDY | WGQGT LVTVS S |
| iPS:4 34397 | VH1|1-02|D7|7-27|RF1|JH4 | QVQLVQS-GAEVKKPGASVKV SCKASG-YTFT | G------YYMH | WVRQAPGQ GLEWMG | WIKPN--- SGGTNQAQK FQG | RVTMTRDTSISTAYMELSGL RSDDTAVYYCAR | APGTAATG---- ----TWGYFDY | WGQGT LVTVS S |
| iPS:4 34427 | VH1|1-02|D7|7-27|RF1|JH4 | QVQLVQS-GAEVKKPGASVKV SCKASG-YTFT | G------YYMH | WVRQAPGQ GLEWMG | WINPK--- SGGTNSAQK FQG | RVSMTRDTSIGTAYMELRGL RSDDTAEYYCAR | APGKAAAG---- ----TWGFFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34435 | 21-225_70G9 | VH1|1-02|D7|7-27|RF1|JH4 | QVQLVQS-GAEVKKPGASVKVSCKASG-YTFT | G------YYMH | WVRQAPGQGLEWMG | WIKPN---SGGTNQAQKFQG | RVTMTRDTSISTAYMELSSLRSDDTAVYYCAR | APGIAAAG-------TWGYFDY | WGQGTLVTVSS |
| iPS:4 34437 | 21-225_70A12 | VH1|1-02|D7|7-27|RF1|JH4 | QVQLVQS-GAEVKKPGASVKVSCKASG-YTFT | G------YYMH | WVRQAPGQGLEWMG | WIKPN---SGGTNQAQKFQG | RVTMTRDTSISTAYMELSGLRSDDTAVYYCAR | APGTAAIG-------TWGYFDY | WGQGTLVTVSS |
| iPS:4 34451 | 21-225_71B7 | VH1|1-02|D7|7-27|RF1|JH4 | QVQLVQS-GAEVKKPGASVKVSCKASG-YIFT | G------YYMH | WVRQAPGQGLEWMG | WIKPN---SGGTNSAQKFQG | RVTMTRDTSIGTAYMELSSLRSDDTAVYYCAR | APGKRAAG-------TWGFFDY | WGQGTLVTVSS |
| iPS:4 34459 | 21-225_71A7 | VH1|1-02|D7|7-27|RF1|JH4 | QVQLVQS-GAEVKKPGASVKVSCKASG-YIFT | G------YYMH | WVRQAPGQGLEWMG | WINPK---SGGTNHVYQKFQG | RVTMTRDTSISTAYMELSSLRSDDTAVYYCAR | APGTAPAG-------SWGYFDY | WGQGTLVTVSS |
| iPS:4 34461 | 21-225_73A3 | VH1|1-02|D7|7-27|RF1|JH4 | QVQLVQS-GAEVKKPGASVKVSCKASG-YTFT | G------YYMH | WVRQAPGQGLDWMG | WINPK---SGGTNHVQKFQG | RVAMTRDTSISTAYMELSSLRSDDTAVYYCAR | APGTAAAG-------SWGCFDY | WGQGTLVTVSS |
| | Germline | | H_FR1 | H_CDR1 | H_FR2 | H_CDR2 | H_FR3 | H_CDR3 | H_FR4 |
| | VH3|3-23|D4|4-11|RF3|JH4 | | EVQLLES-GGGLVQPGGSLRLSCAASG-FTFS | S------YAMS | WVRQAPGKGLEWVS | AISGS---GGSTYYADSVKG | RFTISRDNSKNTLYLQMNSLRAEDTAVYYCAR | | WGQGTLVTVSS |
| iPS:4 34261 | 21-225_56F7 | VH3|3-23|D4|4-11|RF3|JH4 | EVQLLES-GGGLVQPGGSLRLSCAASG-FTFS | S------YVLN | WVRQAPGKGLEWVS | AMSGS---GGRTYYADSVKG | RFTISRDNSKNTLYLQMNSLRAEDTAVYFCAM | TTH-----------FDY | WGQGTLVTVSS |
| iPS:4 35461 | 21-225_153A1 | VH3|3-23|D4|4-11|RF3|JH4 | EVQLLES-GGGLVQPGGSLRLSCAASG-FSFS | S------YVMS | WVRQGPGKGLEWVS | AISGS---GDRTYYADSVKG | RFTISRDNSKNTLYLQMNSLRAEDTAVYYCAK | TAT-----------KDY | WGQGTLVTVSS |
| iPS:4 35509 | 21-225_157H1 | VH3|3-23|D4|4-11|RF3|JH4 | EVQLLES-GGGLVQPGGSLRLSCAASG-FTFS | S------YAMR | WIRQAPGKGLQWVS | DISGS---GGTTYYADSVKG | RFTISRDNSKNTLYLQMNSLRAEDTAVYYCAK | TY------------L | WGQGTLVTVSS |
| iPS:4 35747 | 21-225_175C4 | VH3|3-23|D4|4-11|RF3|JH4 | EVQLLES-GGGLVQPGGSLRLSCAASA-FTFS | S------YVMS | WVRQAPGKGLEWVS | AISGS---GDRTYYADSVKG | RFTISRDDSNTTLYLQMNSLRAEDTAVYYCAR | TAG-----------FDY | WGQGTLVTVSS |
| iPS:3 92784 | 21-225_23C7 | VH3|3-23|D4|4-11|RF3|JH4 | EVQLLES-GGGLVQPGGSLRLSCAASG-FTFS | S------YVMS | WVRQAPGKGLEWVS | AMSGS---GGSTYYVDSVKG | RFTISRDNSKNTLYLQMNSLRAEDTAVYYCAR | TGV-----------FDY | WGQGTLVIVSS |
| iPS:3 92802 | 21-225_23E7 | VH3|3-23|D4|4-11|RF3|JH4 | EVQLLES-GGGLVQPGGSLRLSCTASG-FTFS | S------YAMN | WVRQAPGKGLEWVS | AISGS---GGFTYYADSVKG | RFTISRDNSKNTLYLQMNSLRAEDTAVYYCAR | TSG-----------FDY | WGQGTLVTVSS |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 92962 | 21-225_30A1 | VH3\|3-23\|D4\|4-11\|RF3\|JH4 | EVQLLES-GGGLVQPGGSLRL SCAASG-FTFS | S-----YVMN | WVRQAPGK GLEWVS | AISGS---GGSTYYADS VKG | RFTISRNNSKNTLYLQMNSL RAEDTAVYYCAR | TGV-----------FDY | WGQGT LVTVS S |
| iPS:3 93090 | 21-225_33A5 | VH3\|3-23\|D4\|4-11\|RF3\|JH4 | EVQLLES-GGGLVQPGGSLRL SCAASG-FTFS | S-----YVIN | WVRQAPGK GLEWVS | AISGS---GVSTYYADS VKG | RFTISRDNSKNTLYLQMNSL RAEDTAVYYCAR | TSL-----------FDY | WGQGT LVTVS S |
| | Germline VH3\|3-23\|D1\|1-1\|RF3\|JH4 | | | H_CDR1 | H_FR2 | H_CDR2 | H_FR3 | H_CDR3 | H_FR4 |
| iPS:4 34273 | 21-225_57E4 | VH3\|3-23\|D1\|1-1\|RF3\|JH4 | EVQLLES-GGGLVQPGGSLRL SCAASG-FTFS | S-----YAMS | WVRQAPGK GLEWVS | VISGS---GGSTYYADS VKG | RFTISRDNSKTTLYLQMNSL RAEDTAVYYCAR | RDWND---------VFDY | WGQGT LVTVS S |
| | Germline VH3\|3-23\|D3\|3-3\|RF3\|JH1 | | | H_CDR1 | H_FR2 | H_CDR2 | H_FR3 | H_CDR3 | H_FR4 |
| iPS:4 34279 | 21-225_57F7 | VH3\|3-23\|D3\|3-3\|RF3\|JH4 | EVQLLES-GGGLVQPGGSLRL SCAASG-FTFS | S-----YAMS | WVRQAPGK GLEWVS | AISGS---GGNTFYADS VKG | RFTISRDNSKNTLYLQMNSL RAEDTAVYYCAR | FFGVVG--------VGCFDY | WGQGT LVTVS S |
| iPS:4 37228 | 21-225_60C11 | VH3\|3-23\|D3\|3-3\|RF3\|JH4 | EVQLLES-GGGLVQPGGSLRL SCAASG-FTFS | S-----YAMS | WVRQAPGK GLEWVS | AISGS---GGNTFYADS VKG | RFTISRDNSKNTLYLQMNSL RAEDTAVYYCAR | FFGVVG--------VGCFDY | WGQGT LVTVS S |
| | Germline VH3\|3-23\|D3\|3-22\|RF3\|JH1 | | | H_CDR1 | H_FR2 | H_CDR2 | H_FR3 | H_CDR3 | H_FR4 |
| iPS:4 34291 | 21-225_58A4 | VH3\|3-23\|D3\|3-22\|RF3\|JH4 | EVQLLES-GGGLVQPGGSLRL SCAASG-LTFS | S-----YAMS | WVRQDPGK GLEWVS | AISGS---GGNTFYGDS VKG | RFTISRDNSKNTLYLQMNSL RAEDTAVYYCAR | FFGIVG--------AGFFDS | WGQGT LVTVS S |
| | Germline VH3\|3-33\|D2\|2-15\|RF3\|JH4 | | | H_CDR1 | H_FR2 | H_CDR2 | H_FR3 | H_CDR3 | H_FR4 |
| iPS:4 34299 | 21-225_58D11 | VH3\|3-33\|D2\|2-15\|RF3\|JH4 | QVQLVES-GGGVVQPGRSLRL SCAASG-FTFS | D-----YDIH | WVRQSPGK GLEWVA | VIWYD---GSKKYYADS VKG | RFTISRDNSKKTLYLQMNSL RAEDTALYYCAR | DRVT----------FDY | WGQGT LVTVS S |
| iPS:4 34871 | 21-225_85H1 | VH3\|3-33\|D2\|2-15\|RF3\|JH4 | QVQLVES-GGGVVQPGRSLRL SCAASG-FTFS | S-----YGIH | WVRQAPGK GLEWVA | VIWYD---GSNKYYADS VKG | RFTISRDNSKNTLYLQMNSL RAEDTAVYYCAR | DPFIVG--------ATYFDY | WGQGT LVTVS S |

Figure 51 (Continued)

| | | | | | | | | | |
|---|---|---|---|---|---|---|---|---|---|
| iPS:4 35109 | 21-225_92H5 | VH3-33/D2|2-15|RF3/JH4 | QVQLVES-GGGVVQPGRSLRL SCAASG-FTFS | S-----YGMH | WVRQAPGK GLEWVA | VIWYD----GSNKYYADS VKG | RFTISRDNSKNTLYLQMNSL RAEDTAVYYCAR | DPFIVG----------ATYFDY | WGQGT LVTVS S |
| iPS:4 36434 | 21-225_216B10 | VH3-33/D2|2-15|RF3/JH4 | QVQLVES-GGGVVQPGRSLRL SCAASG-FTFS | S-----YGMH | WVRQAPGK GLEWVA | AIWYD----GSNKYYADS VKG | RFTISRDNSKRTLYLQMNSL RAEDTAVYYCAR | DPNIVG----------ATWFDY | WGQGT LVTVS S |
| | Germline | | H_FR1 | H_CDR1 | H_FR2 | H_CDR2 | H_FR3 | H_CDR3 | H_FR4 |
| | VH1|1-02/D4|4-17|RF2/JH4 | | | | | | | | |
| iPS:4 34307 | 21-225_59B2 | VH1|1-02/D4|4-17|RF2/JH4 | QVQLVQS-GAEVKKPGASVKV SCKASG-YTFA | G-----YYIH | WVRQAPGQ GLEWLG | WINPN----SGGTNYAQK FQG | RVTMTRDTSISTAYMELSRL RPEDTAVYYCAR | DPGP-----------FDY | WGQGT LVTVS S |
| | Germline | | H_FR1 | H_CDR1 | H_FR2 | H_CDR2 | H_FR3 | H_CDR3 | H_FR4 |
| iPS:4 34311 | 21-225_59H5 | VH3-33/D3|3-22|RF3/JH6 | QVQLVES-GGGVVQPGRSLRL SCAASG-FTFS | S-----YGMH | WVRQAPGK GLEWVA | VIWYD----GSNKYYADS VKG | RFTISRDNSKNTLYLQMNSL RAEDTAVYYCAR | ERGIAVG---------YYGMDV | WGQGT TVTVS S |
| | Germline | | H_FR1 | H_CDR1 | H_FR2 | H_CDR2 | H_FR3 | H_CDR3 | H_FR4 |
| | VH4|4-39/D1|1-26|RF3/JH4 | | | | | | | | |
| iPS:4 34313 | 21-225_59E6 | VH4|4-39/D1|1-26|RF3/JH4 | QIQLQES-GPGLVKPSETLSL TCTVSG-GSIS | RS----SYYWG | WIRQPPGK GLEWIG | NIYY-----SGSTYYNPS LKS | RVIISVDTSKNQFSLKLSSV TAADTALYYCAR | HSSSW-----------SLDY | WGQGT LVTVS S |
| iPS:4 34413 | 21-225_68D12 | VH4|4-39/D1|1-26|RF3/JH4 | QIQLQES-GPGLVKPSETLSL TCTVSG-GSIS | RS----SYYWG | WIRQPPGK GLEWIG | NIYY-----SGSTYYIPS LKS | RVIISVDTSKNQFSLKLISV TAADTAVYYCAR | HSTSW-----------SIDY | WGQGT LVTVS S |
| iPS:3 92628 | 21-225_20C2 | VH4|4-39/D1|1-26|RF3/JH4 | QIQLQES-GPGLVKPSETLSL TCTVSG-GSIS | RS----SYYWG | WIRQPPGK GLEWIG | NIYY-----SGIAYCNSS LKS | RVIISVDTSKNQFSLKLSSV TAIDTAVYYCAR | HSSSW-----------SLDN | WGQGT LVTVS S |
| iPS:3 92642 | 21-225_18C6 | VH4|4-39/D1|1-26|RF3/JH4 | QIQLQES-GPGLVKPSETLSL TCTVSG-GSIS | RS----SYYWG | WIRQPPGK GLEWIG | NIYY-----SGYTYYNPS LKS | RVIISVDTSKNQFSLKLSSV TAADTALYYCAR | HSSSW-----------SLDD | WGQGT LVTVS S |
| iPS:3 92706 | 21-225_18A3 | VH4|4-39/D1|1-26|RF3/JH4 | QIQLQES-GPGLVKFSETLSL TCTVSG-GSIS | RS----SYYWG | WIRQPPGK GLEWIG | NIYY-----SGYTYIPS LKS | RVIISVDTSKNQFSLKLSSV TAADTAVYYCAR | HSTSW-----------SLDY | WGQGT LVTVS S |

Figure 51 (Continued)

| | | | | | | | | | |
|---|---|---|---|---|---|---|---|---|---|
| iPS:3 92800 | 21-225_22D12 | VH4|4-39/D1|1-26|RF3/JH4 | QLQLQES-GPGLVKPSETLSL TCTVSG-GSIS | RS---SYYWG | WIRQPPGK GLEWIG | NIYY----SGTTSYNPS LKS | RVTISVDISRNQFSLKLSSV TAADTAVFYCAR | LSSSW-------------- | ---SVDY | WGQGT LVTVS S |
| iPS:3 92820 | 21-225_23D1 | VH4|4-39/D1|1-26|RF3/JH4 | QLQLQES-GPGLVKPSETLSL TCTVSG-GSIS | RS---SYYWG | WIRQPPGK GLEWIG | SIYY----SGSAQYNPS LKS | RVTISVDTSKNQFSLTLSSV TAADTALYYCAR | LSSSW-------------- | ---SFDY | WGQGT LVTVS S |
| iPS:3 92824 | 21-225_24E5 | VH4|4-39/D1|1-26|RF3/JH4 | QLQLQES-GPGLVKPSETLSL TCTVSG-GAIS | RS---SYYWG | WIRQPPGK GLEWIG | SIYY----SGSANYNPS LKS | RVTISVDISKNQFSLKLSSV TAADTAVYYCAR | LSSSW-------------- | ---SIDN | WGQGT LVTVS S |
| iPS:3 92834 | 21-225_22C1 | VH4|4-39/D1|1-26|RF3/JH4 | QLQLQES-GPGLVKPSETLSL TCTVSG-GSIN | RS---SYYWG | WIRQPPGK GLEWIG | NIYY----SGATYYNPS LKS | RVTISVDTSTNQFSLKLSSV TAADTAVYYCAR | HSGSW-------------- | ---SLDY | WGQGT LVTVS S |
| iPS:3 92870 | 21-225_20G9 | VH4|4-39/D1|1-26|RF3/JH4 | QLQLQES-GPGLVKPSETLSL TCTVSG-GSIS | RS---SYYWG | WIRQPPGK GLEWIG | SIYY----SGSASYNPS LKS | RVTISVDTSRNQFSLKLSSV TAADTAAYYCAR | LSSSW-------------- | ---SFDY | WGQGT LVTVS S |
| iPS:3 92896 | 21-225_21G7 | VH4|4-39/D1|1-26|RF3/JH4 | QLQLQES-GPGLVKPSETLSL TCTVSG-GSIS | RS---SYYWG | WIRQPPGK GQEWIG | SIYY----SGYSYNPS LKS | RVTISVDISKNQFSLKLSSV TAADTAVYYCAR | HSTSW-------------- | ---SLDY | WGQGT LVTVS S |
| iPS:3 92904 | 21-225_22G9 | VH4|4-39/D1|1-26|RF3/JH4 | QLQLQES-GPGLVKPSETLSL TCTVSG-GAIS | GS---NYYWG | WIRQPPGK ELEWIG | NIYY----SGSTYNPS LKS | RVTISVDISKNQVSLKLSSV TAADTAVYYCAR | HSSSW-------------- | ---SFDY | WGQGT LVTVS S |
| iPS:3 93094 | 21-225_34C4 | VH4|4-39/D1|1-26|RF3/JH4 | QLQLQES-GPGLVKPSETLSL TCTVSG-GSIS | RS---SYYWG | WIRQSPGK GLEWIG | SIYY----SGSTAYNPS LKS | RVNISVDISKNQFSLKLNSV TAADTAVYYCAR | LSSSW-------------- | ---SLDY | WGQGT LVTVS S |
| iPS:3 93806 | 21-225_6A6 | VH4|4-39/D1|1-26|RF3/JH4 | QLQLQES-GPGLVKPSETLSL TCTVSG-GSIS | RS---SYYWG | WIRQPPGK GLEWIG | NIYY----SGIPYYNPS LKS | RVTISVDTSTNQFSLKLSSV TAADTAVYYCAR | HSSSW-------------- | ---SLDY | WGQGT LVTVS S |
| iPS:3 93814 | 21-225_7F4 | VH4|4-39/D1|1-26|RF3/JH4 | QLQLQES-GPGLVKPSETLSL TCTVSG-GSIS | RS---SYYWG | WIRQPPGK GLEWIG | NIYY----SGATYYNPS LKS | RVTISVDTSTNQFSLKLSSV TAADTAVYYCAR | HSGSW-------------- | ---SLDY | WGQGT LVTVS S |
| iPS:3 93816 | 21-225_6D4 | VH4|4-39/D1|1-26|RF3/JH4 | QLQLQES-GPGLVKPSETLSL TCTVSG-GSIS | RS---SSYWG | WIRQPPGK GLEWIG | SIYY----SGSAYYIPS LKS | RVTISVAISKNQFSLNLISV TAADTAVYYCAR | HSSSW-------------- | ---SLDC | WGQGT LVTVS S |
| iPS:3 93880 | 21-225_15A1 | VH4|4-39/D1|1-26|RF3/JH4 | QLHLQES-GPGLVKPSETLSL TCTVSG-GSIS | RS---SYYWG | WIRQPPGK GLEWIG | SIYY----SGSAQYNPS LKS | RVTISVDITRNQFSLTLSSV TAADTAVYYCAR | LSSSW-------------- | ---SFDY | WGQGT LVTVS S |

Figure 51 (Continued)

| | | | | H_FR1 | H_CDR1 | H_FR2 | H_CDR2 | H_FR3 | H_CDR3 | H_FR4 |
|---|---|---|---|---|---|---|---|---|---|---|
| iPS:394002 | 21-225_15G7 | VH4J4-39/D1|1-26|RF3/JH4 | | QIQLQES-GPGLVKPSETLSLTCTVSG-GSIS | RS---SSYWG | WIRQPPGKGLEWIG | SIYY----SGYTYTPSLKS | RVTISVDTSKNQFSLRLSSVTAADTASYYCAR | LSSSW--------SFDF | WGQGTLVTVSS |
| iPS:394053 | 21-225_11F10 | VH4J4-39/D1|1-26|RF3/JH4 | | QLHLQES-GPGLVKPSETLSLTCTVSG-ASIS | RS---SYYWG | WIRQPPGKGLEWIG | SIYY----SGSAQYNPSLKS | RVTISVDTSKNQFSLFLSSVTAADTAVYYCAR | LSSSW--------SFDY | WGQGTLVTVSS |
| iPS:394057 | 21-225_15H1 | VH4J4-39/D1|1-26|RF3/JH4 | | QIQLQES-GPGLVKFSETLSLTCTVSG-GSIS | RS---SYYWG | WIRQPPGKGLEWIG | NIYY----SGYPYNPSLKS | RVTISVDTSKNQFSLKLSSVTAADTAVYYCAR | HSTSW--------SLDY | WGQGTLVTVSS |
| iPS:394063 | 21-225_16A1 | VH4J4-39/D1|1-26|RF3/JH4 | | QIQLQES-GPGLVKPSETLSLICTVSG-GSID | RS---SYYWG | WIRQPPGKGLEWIG | SIYY----SGSAYHNPSLKS | RGTISVDTSKNQFSLKLSSVTAADTAAYYCAR | LSSSW--------SFDY | WGQGTLVTVSS |
| iPS:394075 | 21-225_8D12 | VH4J4-39/D1|1-26|RF3/JH4 | | QIQLQES-GPGLVKFSETLSLTCTVSG-GSIS | RS---SYYWG | WIRQPPGKGLEWIG | NIYY----SGYPYNPSLKS | RVTISIDTSKNQFSLKLSSVTAADTAVYYCAR | HSTSW--------SLDY | WGQGTLVTVSS |
| | Germline | | | H_FR1 | H_CDR1 | H_FR2 | H_CDR2 | H_FR3 | H_CDR3 | H_FR4 |
| | VH3J3-48|D7|7-27|RF3/JH4 | | | EVQLVES-GGGLVQPGGSLRLSCAASG-FTFS | YSMH | WVRQAPGKGLGWVS | YISSS---SGTIYYADSVKG | RFTISRDNARNSLYLQMNSLRDEDTAVYYCAR | EWGMAV-------AGPFDY | WGQGTLVTVSS |
| iPS:434317 | 21-225_59E8 | VH3J3-48|D7|7-27|RF3/JH4 | | EVQLVES-GGGLVQPGGSLRLSCAASG-FTFS | S------YSMN | WVRQAPGKGLGWVS | YISSS---SGTIYYADSVKG | RFTISRDNARNSLYLQMNSLRDEDTAVYYCAR | EWGMAV-------AGPFDY | WGQGTLVTVSS |
| | Germline | | | H_FR1 | H_CDR1 | H_FR2 | H_CDR2 | H_FR3 | H_CDR3 | H_FR4 |
| | VH3J3-33|D1|1-26|RF3/JH4 | | | QVQLVES-GGGVVQPGRSLRLSCAASG-FTFS | YGMH | WVRQAPGKGLEWVS | VIWYD---GSNKYYADSVKG | RFTISRDNSKNTLYLQMNSLRAEDTAVYYCAR | YSSY---------YFDY | WGQGTLVTVSS |
| iPS:434327 | 21-225_63G6 | VH3J3-33|D1|1-26|RF3/JH4 | | QVQLVES-GGGVVQPGRSLRLSCAASG-FTFS | S------YGMH | WVRQAPGKGLEWVI | VIWYD---GSNKYYADSVKG | RFTISRDNSKNTLYLQMNSLRAEDTAVYYCAR | DSLSGI-------AAAFDY | WGQGTLVTVSS |
| iPS:437084 | 21-225_206B5 | VH3J3-33|D1|1-26|RF3/JH4 | | QVQLVES-GGGVVQPGRSLRLSCAASG-FTFS | S------YGMH | WVRQAPGKGLEWVA | VIWYD---GSNKYYADSVKG | RFTISRDNSKNTLYLQMNSLRAEDTAVYNCAR | EGGSY--------HLDY | WGQGTLVTVSS |
| iPS:437088 | 21-225_209H10 | VH3J3-33|D1|1-26|RF3/JH4 | | QVQLVES-GGGVVQPGRSLRLSCAASG-FTFS | S------YGMH | WVRQAPGKGLEWVA | VIWYD---GSNKYYADSVKG | RFTISRDNSKNTLYLQMNSLRAEDTAVYNCAR | EGGSY--------HLDY | WGQGTLVTVSS |
| iPS:392684 | 21-225_17F4 | VH3J3-33|D1|1-26|RF3/JH4 | | QVQLVES-GGGVVQPGRSLRLSCAASG-FTFS | N------YGMN | WVRQAPGKGLEWVA | VIWYD---GNNKHIADSVKG | RFTISRDNSKNTLYLQMNSLRAEDTAVYYCAS | SGSY---------FFDY | WGQGTLVTVSS |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH1I1-02/D6|6-19|RF2|JH4 | | QVQLVQS CAEVKKPGASVKV SCKASG-YTFT | G------YYMH | WVRQAPGQ GLEWMG | WINPN---SGGTNFAQK FQG | RVTMTRDASINTAYMELRSL ISDDTAVYYCAR | APGVAAAG------SWGYFDY | WGQGT LVTVS S |
| iPS:4 34333 | VH1|1-02/D6|6-19|RF2|JH4 | | | | | | | |
| | Germline | H_FR1 | H_CDR1 | H_FR2 | H_CDR2 | H_FR3 | H_CDR3 | H_FR4 |
| VH3|3-33/D4|4-11|RF2|JH4 | | | | | | | | |
| iPS:4 34335 | VH3|3-33/D4|4-11|RF2|JH4 | QVQLVES-GGGVVQPGRSLRL SCAASG-FTFS | S------YGMH | WVRQAPGK GLDWVA | VIWYD---GSNKYYADS VKG | RFTISRDNSKNTLYLQMNSL RAEDTAVYYCAR | DDPRS------SAGDY | WGQGT LVTVS S |
| iPS:4 34429 | VH3|3-33/D4|4-11|RF2|JH4 | QVQLVES-GGGVVQPGRSLRL SCAASG-FTFS | S------YGMH | WVRQTPGK GLGWVA | VIWHD---GSNKYYADS VKG | RFTISRDNSKNTLYLQMNSL RAEDTAVYYCAR | DDPRS------SAGDY | WGQGT LVTVS S |
| iPS:4 34569 | VH3|3-33/D4|4-11|RF2|JH4 | QVQLVES-GGGVVQPGRSLRL SCAASG-FTFS | N------YGMH | WVRQAPGK GLEWVA | VIWYD---GRNKYYADS VKG | RFTISRDNSKNTLYLQMNSL RAEDTALYYCAR | DRSILG------ATFFDY | WGQGT LVTVS S |
| iPS:4 34629 | VH3|3-33/D4|4-11|RF2|JH4 | QVQLVES-GGGVVQPGRSLRL SCAASG-FTFS | S------FGMH | WARQAPGK GLEWVA | AIWYD---GSNKYCADS VKG | RFTISRDNSKNTLSLQMNSL RAEDSAVYYCAR | DRSILG------AAFFDY | WGQGT LVTVS S |
| iPS:4 35793 | VH3|3-33/D4|4-11|RF2|JH4 | QVQLVES-GGGVVQPGRSLRL SCAASG-FTFS | S------YGMH | WVRQAPGK GLEWVS | VIWYD---GSDKYYEDS VKG | RFTISRDNSKNTLYLQMNSL RAEDTAVYYCAR | DHPRW------SYGDY | WGQGT LVTVS S |
| iPS:4 36382 | 21-225_212C10 VH3|3-33/D4|4-11|RF2|JH4 | QVQLVES-GGGVVQPGRSLRL SCAASG-FTFS | S------YGMH | WVRQAPGK GLEWVT | AIWYD---GSHKYYTDS VKG | RFTISRDNSKNTLYLQMNSL RAEDTAVYYCAR | DRSIVG------ATYFDY | WGQGT LVTVS S |
| iPS:3 92660 | VH3|3-33/D4|4-11|RF2|JH4 | QVQLVES-GGGVVQPGRSLRL SCAASG-FTFS | S------YDMH | WVRQAPGK GLEWVA | VIWYD---GSDKYYADS VKG | RFTISRDNSKNTLFLQMNSL RAEDTAVYYCAR | DRAYS------SSSDY | WGQGT LVTVS S |
| iPS:3 93804 | VH3|3-33/D4|4-11|RF2|JH4 | QVQLVES-GGGVVQPGRSLRL SCAASG-FTFS | T------YNMH | WVRQAPGK GLEWVA | VIWYD---GSDRYSADS VKG | RFTISRDNSKNTLYLQMNSL RAEDTAVYYCAR | DRAYS------SSSDF | WGQGT LVTVS S |
| | Germline | H_FR1 | H_CDR1 | H_FR2 | H_CDR2 | H_FR3 | H_CDR3 | H_FR4 |
| VH4|4-59/D4|4-11|RF2|JH4 | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34341 | 21-225_64F7 | VH4/4-59/D4/4-11/RF2/JH4 | QVQLQES-GPGLVKPSETLSL TCTVSG-GSIS | S-----YFWS | WIRQPAGK GLEWIG | RIYT----SGISNINPS LKS | RVTMSVDTSKNQFSLKLSSV TAADTAVYYCAR | FSSG------------FFDY | WGQGT LVTVS S |
| | | Germline | | | | | | | |
| | VH3/3-33/D7/7-27/RF2/JH1 | | | | | | | | |
| iPS:4 34351 | 21-225_64A12 | VH3/3-33/D7/7-27/RF2/JH1 | QVQLVES-GGGVVQPGRSLRL SCAASG-FTFS | S-----YGMH | WVRQAPGK GLEWVA | VIWYD---ESNKYYVDS VKG | RFTISRDNSKNILYLQMNSL RAEDTAVYYCAR | ELGF------------LSDH | WGQGT LVTVS S |
| iPS:3 92700 | 21-225_16E12 | VH3/3-33/D7/7-27/RF2/JH1 | QVQLVES-GGGLVQPGRSLRL SCAASG-FTFS | N-----YGMH | WVRQAPGK GLEWVA | VIWYE---GSNKYYVDS VRG | RFTISRDNSKSTLYLQMNSL RAEDTAVYYCVR | ELGF------------QSDH | WGQGT PVTVS S |
| iPS:3 92710 | 21-225_19A10 | VH3/3-33/D7/7-27/RF2/JH1 | QVQLVES-GGGVVQPGRSLRL SCAASG-FTFS | S-----YGMH | WVRQAPGK GLEWVA | VIWYD---ESNKYYADS VKG | RFTISRDNSKNTLYLQMNSL RAEDTAVYYCAR | ELAW------------YEDS | WGQGT LVTVS S |
| iPS:3 94093 | 21-225_9D12 | VH3/3-33/D7/7-27/RF2/JH1 | QVQLVES-GGGVVQPGRSLRL SCAASG-FTFS | D-----YGMH | WVRQAPGK GLEWVA | VIWYD---GNNNYYADS VKG | RFTISRDNSKNTLYLQMNSL RAEDTAVYYCAR | ELAW------------YEDF | WGQGT LVTVS S |
| | | Germline | | | | | | | |
| | VH3/3-23/D3/3-22/RF2/JH3 | | | | | | | | |
| iPS:4 34355 | 21-225_64G12 | VH3/3-23/D3/3-22/RF2/JH3 | EVQLLES-GGGLVQPGGSLRL SCAASG-FTFS | S-----NAMS | WVRQAPGK GLEWVS | VISGS---GGSTYYADS VKG | RFTISRDNSKNILYLQMNSL RAEDTALYYCAK | RNYDD-----------AFDI | WGQGT MVTVS S |
| | | Germline | | | | | | | |
| | VH3/3-21/D4/4-11/RF3/JH4 | | | | | | | | |
| iPS:4 34367 | 21-225_65H11 | VH3/3-21/D4/4-11/RF3/JH4 | EVQLVES-GGGLVKPGGSLRL SCAASG-FTFS | S-----YRMN | WVRQAPGK GLEWVS | SISSS---NSSIYYADS VKG | RFTISRDNAKNSLYLQMNSL RAEDTAVYYCTS | TS--------------GS | WGQGT LVTVS S |
| iPS:4 37220 | 21-225_55H6 | VH3/3-21/D4/4-11/RF3/JH4 | EVHLVES-GGGLVKPGGSLRL SCAASG-FTFS | S-----YSMN | WVRQAPGK GLEWVS | SISGS---STYIYYADS VKG | RFTISRDNAKNSLYLQMNSL RAEDTAVYYCAR | TGV-------------FDY | WGQGT LVTVS S |
| iPS:4 02237 | 21-225_23D11 | VH3/3-21/D4/4-11/RF3/JH4 | EVQLVES-GGGLVKPGGSLRL SCAASG-FTFS | S-----YNIN | WVRQAPGK GLEWVS | SISGN---SGYIYYADS VKG | RFTISRDNAKNSLYLQMNSL RAEDTAVYYCAR | TNL-------------FDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3J3-21|D4|4-11|RF3|JH3 | | EVQLVES-CGGLVKPGGSLRL SCAASG-FTFS | S-----YSMN | WVRQAPGK GLEWVS | SISGT--- SSYIYYADS VKG | RFTISRDNAKNSLYLQMNGL RAEDTAVYFCAR | TNA-------------TYTD | WGQGT MVTVS S |
| iPS:4 34383 | 21-225_66F9 | VH3J3-21|D4|4-11|RF3|JH3 | EVQLVES-CGGLVKPGGSLRL SCAASG-FTFS | S-----YSMN | WVRQAPGK GLEWVS | SISGT--- SSYIYYADS VKG | RFTISRDNAKNSLYLQMNGL RAEDTAVYFCAR | TNA-------------FDI | WGQGT MVTVS S |
| iPS:4 34449 | 21-225_71H6 | VH3J3-21|D4|4-11|RF3|JH3 | EVQLVES-CGGLVKPGGSLRL SCAASG-FTFS | S-----YSMN | WVRQAPGK GLEWVS | SISGT--- SSYIYYADS VKG | RFTISRDNAKNSLYLQMNGL RAEDTAVYFCAR | TNA-------------FDI | WGQGT MVTVS S |
| | Germline | H_FR1 | H_CDR1 | H_FR2 | H_CDR2 | H_FR3 | H_CDR3 | H_FR4 |
| VH3J3-33|D6|6-6|RF2|JH4 | | QVQLVES-GGGVVQFGRSLRL SCAASG-FTFS | | WVRQAPGK GLEWVA | GSKKYYADS VKG | RFTISRDNSKNTLYLQMNSL RAEDTAVYYCAR | SIPE-------------VFDY | WGQGT LVTVS S |
| iPS:4 34399 | 21-225_67B7 | VH3J3-33|D6|6-6|RF2|JH4 | QVQLVES-GGGVVQFGRSLRL SCAASG-FTFS | N-----YGMH | WVRQAPGK GLEWVA | VILYD--- GSKKYYADS VKG | RFTISRDNSKNTLYLQMNSL RAEDTAVYYCAR | SIPE-------------FDY | WGQGT LVTVS S |
| iPS:4 34463 | 21-225_73A6 | VH3J3-33|D6|6-6|RF2|JH4 | QVQLVES-CGGVVQPGRSLRL SCAASG-FTFS | Y-----YGMH | WVRQAPGK GLEWVA | VILYD--- GSKKYAAS VKG | RFTISRDNSKNTLYLQMNSL RAEDTAVYYCAR | SIPD-------------FDY | WGQGT LVTVS S |
| | Germline | H_FR1 | H_CDR1 | H_FR2 | H_CDR2 | H_FR3 | H_CDR3 | H_FR4 |
| VH3J3-21|D1|1-26|RF3|JH4 | | EVQLVES-CGGLVKPGGSLRL SCAASG-FTFS | | WVRQAPGK GLEWVS | SISSS--- | RFTISRDNAKNSLYLQMNSL RAEDTAVYYCAR | SSGS-------------VFDY | WGQGT LVTVS S |
| iPS:4 34405 | 21-225_68E6 | VH3J3-21|D1|1-26|RF3|JH4 | EVQLVES-GGGLVKPGGSLRL SCAASG-FILS | S-----FGMN | WVRQAPGK GLEWVS | YISRS--- SSHIYYADS VKG | RFTISRDNAKNSLYLQMNSL RAEDTAVYYCAR | SSGS-------------FFDY | WGQGT LVTVS S |
| iPS:4 35595 | 21-225_160H4 | VH3J3-21|D1|1-26|RF3|JH4 | EVQLVES-CGGLVKSGCSLRL SCAASG-FTFS | S-----YRMN | WVRQAPGK GLEWVS | SISGS--- SSYIDYADS VKG | RFTISRDNAKNSLYLQMNSL RAEDTAVYYCAR | KSW-------------FDY | WGQGT LVTVS S |
| iPS:4 35635 | 21-225_163F1 | VH3J3-21|D1|1-26|RF3|JH4 | EVQLVDS-CGGLVKPGGSLRL SCAASG-FTFS | S-----YSMN | WVRQAPGK GLEWVS | SISGS--- GSYIYYADS VKG | RFTISRDNAKNSLYLQMNSL SAEDTAVYYCTL | YSS-------------SHY | WGQGT LVTVS S |
| | Germline | H_FR1 | H_CDR1 | H_FR2 | H_CDR2 | H_FR3 | H_CDR3 | H_FR4 |
| VH3J3-30.3|D2|2-15|RF3|JH4 | | QVQLVES-CGGVVQPCRSSLRL SCAASG-FTFS | | WVRQAPGK GLEWVA | | RFTISRDNSKNTLYLQMISL RAEDTAVYYCAR | DIPSN-------------XTFFDY | WGQGT LVTVS S |
| iPS:4 34417 | 21-225_69C8 | VH3J3-30.3|D2|2-15|RF3|JH4 | QVQLVES-CGGVVQPGRSLRL SCAASG-FTFS | N-----YAMH | WVRQAPGK GLEWVA | VIWYD--- GSDKYYADS VKG | RFTISRDNSKNTLYLQMISL RAEDTAVYYCAR | DIPSN-------------SAGDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3|3-33|D3|3-10|RF1|JH4 | | QVQLVES-GGGVVQPGRSLRLSCAASG-FTFS | S-----YGMH | WVRQAPGK GLEWVA | IINYD---ESNKYYADS VKG | RFTISRDNSKNTLYLQMNSL RAEDTAVYYCAR | DLLD-------PRDY | WGQGT LVTVS S |
| iPS:4 34433 | VH3|3-33|D3|3-10|RF1|JH4 | QVQLVES-GGGVVQPGRSLRLSCAASG-FTFS | S-----YGMH | WVRQAPGK GLEWVA | IINYD---ESNKYYADS VKG | RFTISRDNSKNTLYLQMNSL RAEDTAVYYCAR | DLLD-------PRDY | WGQGT LVTVS S |
| VH3|3-23|D6|6-13|RF1|JH4 | Germline | | | | | | | |
| iPS:4 34467 | VH3|3-23|D6|6-13|RF1|JH4 | EVQLLES-GGGVVQSGGGSLRLSCAASG-FTFS | S-----NAMS | WVRQAPGK GLEWVS | DISRS---GGTFYYADS VKG | RFTISRDNSKNTLYLQMNSL RAEDTAVYYCAR | WDSSSWY-------OVTPFDY | WGQGT LVTVS S |
| VH4|4-34|D4|4-17|RF2|JH4 | Germline | | | | | | | |
| iPS:4 34471 | 21-225_75G3 VH4|4-34|D4|4-17|RF2|JH4 | QVQLQQW-GAGLLKPSETLSLTCAVYG-GSLS | G-----SYWS | WIRQPPGK GLEWIG | EINL-----SGSTNYNPS LKS | RVTISVDTSKSQFSLTLRSV TAADTAVYYCAR | DYGG-------LDY | WGQGT LVTVS S |
| iPS:4 34517 | 21-225_76A7 VH4|4-34|D4|4-17|RF2|JH4 | QVQLQQW-GAGLLKPSETLSLTCAVYG-GSFS | G-----CYWS | WIRQPPGK GLEWIG | EINH-----SGRTNYNPS LKS | RVTISVDTSENQFSLKLSSV TAADTAVYYCAR | DYGG-------LDY | WGQGT LVTVS S |
| iPS:4 34519 | 21-225_74C7 VH4|4-34|D4|4-17|RF2|JH4 | QVQLQQW-GAGLLKPSETLSLTCAVYG-GSLS | G-----SYWS | WIRQPPGK GLEWIG | EINL-----SGSTNYNPS LKS | RVTISVDTSENQFSLTLRSV TAADTAVYYCAR | DYGG-------LDY | WGQGT LVTVS S |
| iPS:4 34571 | 21-225_74D2 VH4|4-34|D4|4-17|RF2|JH4 | QVQLQQW-GAGLLKPSETLSLTCAVYG-GSFS | G-----CYWS | WIRQPPGK GLEWIG | EINH-----SGRTNYNPS LKS | RVTISVDTSENQFSLKLSSV TAADTAVYYCAR | DYGG-------LDY | WGQGT LVTVS S |
| iPS:4 34637 | 21-225_78E7 VH4|4-34|D4|4-17|RF2|JH4 | QVQLQQW-GAGLLKPSETLSLTCAVYG-GSLS | G-----SYWS | WIRQPPGK GLEWIG | EINL-----SGSTNYNPS LKS | RVTISVDTSKSQFSLTLRSV TAADTAVYYCAR | DYGG-------LDY | WGQGT LVTVS S |
| iPS:4 34717 | 21-225_80A6 VH4|4-34|D4|4-17|RF2|JH4 | QVQLQQW-GAGLLKPSETLSLTCAVYG-GSFS | G-----CYWS | WIRQPPGK GLEWIG | EINH-----SGRTNYNPS LKS | RVTISVDTSEKQFSLKLSSV TAADTAVYYCAR | DYGG-------LDY | WGQGA LVTVS S |
| iPS:4 34735 | 21-225_80B10 VH4|4-34|D4|4-17|RF2|JH4 | QVQLQQW-GAGLLKPSETLSLTCAVYG-GSFS | G-----CYWS | WIRQPPGK GLEWIG | EINH-----SGSTNYNPS LKS | RVTISVDTSKNQFSLKLSSV TAADTAVYYCAR | DYGG-------LDY | WGQGT LVTVS S |

Figure 51 (Continued)

| | | | | | | | | |
|---|---|---|---|---|---|---|---|---|
| iPS:4 34835 | 21-225_83B6 | VH4|4-34|D4|4-17|RF2|J H4 | QVQLQQW-GAGLLKPSETLSL TCAVYG-GSFS | G-----CYWS | WIRQPPGK GLEWIG | EINH----SGRTNYNPS LKS | RVTISVDISENQFSLKLSSV TAADTAVYYCAR | DYGG------- | ------LDY | WGQGT LVTVS S |
| iPS:4 34849 | 21-225_83C10 | VH4|4-34|D4|4-17|RF2|J H4 | QVQLQQW-GAGLLKPSETLSL TCTVYG-GSFS | G-----YYWS | WIRQPPGK GLEWIG | EINH----SGSTNFNPS LKS | RVTISVDTSKNQFSLKLSSV TAADTAVFYCAR | DYGG------- | ------LDY | WGQGT LVTVS S |
| iPS:4 34891 | 21-225_85G6 | VH4|4-34|D4|4-17|RF2|J H4 | QVQLQQW-GAGLLKPSETLSL TCAVYG-GSFS | D-----CYWS | WIRQPPGK GLEWIG | EINH----SGRTNYNPS LKS | RVTISVDISENKFSLKLSSV TAADTAVYYCAR | DYGG------- | ------LDY | WGQGT LVTVS S |
| iPS:4 35183 | 21-225_93E9 | VH4|4-34|D4|4-17|RF2|J H4 | QVQLQQW-GAGLLKPSETLSL TCAVYG-GSFS | G-----CYWS | WIRQPPGK GLEWIG | EINH----SGRTNYNPS LKS | RVTISVDTSENKFSLKLSSV TAADTAVYYCAR | DYGG------- | ------LDY | WGQGT LVTVS S |
| iPS:4 35331 | 21-225_147G8 | VH4|4-34|D4|4-17|RF2|J H4 | QVQLQQW-GAGLLKPSETLSL TCAVYG-GSFS | A-----YYWS | WIRQPPGK GLEWIG | EINH----SGSTNYKPS LKS | RVTISVDTSKNQFSLKLSSV TAADTAVYYCAR | DYGV------- | ------FDY | WGQGT LVTVS S |
| iPS:4 35995 | 21-225_192F8 | VH4|4-34|D4|4-17|RF2|J H4 | QVQLQQW-GAGLLKPSETLSL TCAVYG-GSFS | G-----CYWS | WIRQPPGK GLEWIG | EINQ----SGRSNYNPS LKS | RVTISVDTSTNQFSLKLRSV TAADTAVYYCAR | DYGV------- | ------FDY | WGQGT LVTVS S |
| iPS:4 36027 | 21-225_193E6 | VH4|4-34|D4|4-17|RF2|J H4 | QVQLQQW-GAGLLKPSETLSL TCAVYG-GSFS | G-----PYWS | WIRQPPGK GLEWIG | ESNH----SGRTNYNPS LKS | RVTISVDTSKNQFSLRLSSV TAADTAVYYCAR | DYGG------- | ------LDY | WGQGT LVTVS S |
| iPS:4 36080 | 21-225_195B1 | VH4|4-34|D4|4-17|RF2|J H4 | QVQLQQW-GAGLLKPSETLSL TCAVSG-GSFR | Y-----YFWS | WIRQSPGK GLEWFG | EINH----SGSTNYNPS LKS | RVTISVDISKNQFSLKLRSV TAADTAVYYCAR | DYGA------- | ------FDI | WGQGT LVTVS S |
| iPS:4 36232 | 21-225_201E1 | VH4|4-34|D4|4-17|RF2|J H4 | QVQLQQW-GAGLLKPSETLSL TCAVFD-GSFS | P-----YYWS | WIRQPPGK GLEWIG | EVNH----SGRSNYNPS LKS | RVTISVDISKNQFSLKLSSV TAADTAVYYCAR | DYGG------- | ------LDY | WGQGA LVTVS S |
| iPS:4 36238 | 21-225_201B2 | VH4|4-34|D4|4-17|RF2|J H4 | QVQLQQW-GAGLLKPSETLSL TCAVYG-GSIS | V-----YYWT | WIRQPPGK GLEWIG | EINH----SGRTNYNPS LKS | RVTISVDTSKNQFSLKLSSV TAADTAVYYCAR | DYGV------- | ------FDY | WGQGT LVTVS S |
| iPS:4 36256 | 21-225_202D9 | VH4|4-34|D4|4-17|RF2|J H4 | QVQLQQW-GAGLLKPSETLSL TCAVFG-GSFS | F-----YYWS | WIRQPPGK GLEWIG | EINH----SGSTNYNPS LKS | RVTISVDTSKNQFSLKLSSV TAADTAVYYCAR | DYGG------- | ------LDY | WGQGT LVTVS S |
| iPS:4 36302 | 21-225_205G7 | VH4|4-34|D4|4-17|RF2|J H4 | QVQLQQW-GAGLLKPSETLSL TCAVYG-GSFS | V-----YYWS | WIRQPPGK GLEWIG | ESNQ----SGRTYNPS LKS | RVTISVDTSKNQFSLNLISV TAADTAVYYCAR | DYGV------- | ------FDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36310 | 21-225_202D11 | VH4|4-34|D4|4-17|RF2|JH4 | QVQLQQR-GAGLLKPSETLSLTCAAYG-GSFS | G-----PYWS | WIRQPPGK GLEWIG | EINH----SGSTNYNPS LKS | RVTISVDTSKNQFSLKLSSV TAADTAVYYCAR | DYGV--------LDY | WGQGT LVTVS S |
| iPS:4 36336 | 21-225_208B5 | VH4|4-34|D4|4-17|RF2|JH4 | QVQLQQW-GAGLLKPSETLSLTCAVFG-GS1S | V-----YYWT | WIRQPPGK GLEWIG | EINH----SGSTNYNPS LKS | RVTISVDTSKNQFSLKLSSV TIAADTAVYYCAR | DYGV--------FDY | WGQGT LVTVS S |
| iPS:4 36340 | 21-225_208A9 | VH4|4-34|D4|4-17|RF2|JH4 | QVQLQQW-GAGLLKPSEPLSLTCAVYG-GSFS | V-----SYWS | WIRQPPGK GLEWIG | EINH----SGRANYNPS LKS | RVTISIDTSKNQFSLKLSSV TAADTAVYYCAR | DYGV--------LDY | WGQGT LVTVS S |
| iPS:4 37340 | 21-225_75G9 | VH4|4-34|D4|4-17|RF2|JH4 | QVQLQQW-GAGLLKPSETLSLTCAVYG-GSFS | G-----CYWS | WIRQPPGK GLEWIG | EINH----SGRTNYNPS LKS | RVTISVDTSENQFSLKLSSV TAADTAVYYCAR | DYGG--------LDY | WGQGT LVTVS S |
| iPS:4 51122 | 21-225_200A1 | VH4|4-34|D4|4-17|RF2|JH4 | QVQLQQW-GAGLLKPSETLSLTCAVYG-GSFS | V-----YYWS | WIRQPPGK GLEWIG | EINH----SGSTNYNPS LKS | RVTISLDTSKNQFSLKLSSV TAADTAVYYCAR | DYGV--------FDY | WGQGT LVTVS S |
| | Germline | H_FR1 | H_CDR1 | H_FR2 | H_CDR2 | H_FR3 | H_CDR3 | H_FR4 |
| VH3|3-33|D2|2-15|RF3|JH1 | | QVQLVES-GGGVVQPGRSLRLSCAASG-FTFS | S-----YGMH | WVRQAPGK GLEWVA | VIWYD---GSNKYYADS VKG | RFTISRDNSKMTLFLQMNSL RAEDTAVYYCAR | RNIYFA | WGQGT LVTVS S |
| iPS:4 34485 | 21-225_76D2 | VH3|3-33|D2|2-15|RF3|JH1 | QVQLVES-GGGVVQPGRSLRLSCAASG-FTFS | S-----YGMH | WVRQAPGK GLEWVA | VIWYD---GSNKYYADS VKG | RFTISRDNSKNTLFLQMNSL RAEDTAVYYCAS | DRNIVG-----ATYFES | WGQGT LVTVS S |
| iPS:4 34537 | 21-225_74E11 | VH3|3-33|D2|2-15|RF3|JH1 | QVQLVES-GGGVVQPGRSLRLSCAASG-FTFS | S-----YGMH | WVRQAPGK GLEWVA | VIWYD---GSNKYYADS VKG | RFTISRDNSKNTLFLQMNSL RAEDTAVYYCAS | DRNIVG-----ATYFES | WGQGT LVTVS S |
| iPS:4 34673 | 21-225_74E3 | VH3|3-33|D2|2-15|RF3|JH1 | QVQLVES-GGGVVQPGRSLRLSCTASG-FTFS | S-----YGMH | WVRQAPGK GLEWVA | VIWYD---GSNKYYADS VKG | RFTISRDNSKNTLFLQMNSL RAEDTAVYYCAS | DRNIVG-----ATYFES | WGQGT LVTVS S |
| iPS:4 35221 | 21-225_95G2 | VH3|3-33|D2|2-15|RF3|JH1 | QVQLVES-GGGVVQPGRSLRLSCTASG-FTFS | S-----YGMH | WVRQAPGK GLEWVA | VIWYD---GSNKYYADS VKG | RFTISRDNSKNTLFLQMNSL RAEDTAVYYCAS | DRNIVG-----ATYFES | WGQGT LVTVS S |
| | Germline | H_FR1 | H_CDR1 | H_FR2 | H_CDR2 | H_FR3 | H_CDR3 | H_FR4 |
| VH4|4-34|D7|7-27|RF1|JH5 | | QLQLQES-GPGLVKPSETLSLTCSVSG-GSIF | RS----SYYWG | WIRQPPGK GLEWIG | GIYY----SGSTSNPS LKS | RVTISVDTSKNQFSLKLSSV TAADTAVYYCAR | TR--------AFDP | WGQGT LVTVS S |
| iPS:4 34503 | 21-225_74D7 | VH4|4-39|D7|7-27|RF1|JH5 | QLQLQES-GPGLVKPSETLSLTCSVSG-GSIF | RS----SYYWG | WIRQPPGK GLEWIG | GIYY----SGSTSNPS LKS | RVTISVDISENQFSLKLSSV TAADTAVYYCAR | LRPNW------DFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3|3-15|D1|1-1|RF2|JH4 | | EVQLVES-GGGLVKPGGSLRL SCAASG-FTFS | N------AWMN | WVRQAPGK GLEWVS | RIKSKT DGGTTDYAA PVKG | RFTISRDDSKNTLYLQMNSL KTEDTAVYYCTI | VQLER------TDY | WGQGT LVTVS S |
| iPS:4 34531 | 21-225_76C9 | VH3|3-15|D1|1-1|RF2|JH4 | EVQLVES-GGGLVKPGGSLRL SCAASG-FSFS | N------AWMN | WVRQAPGK GLEWVG | RIKNKA-DGGTTDFAA PVKG | RFTISRDDSKNTLYLQMNSL KTEDTAVYYCTI | VGPT------TDY | WGQGT LVTVS S |
| iPS:4 34633 | 21-225_74G8 | VH3|3-15|D1|1-1|RF2|JH4 | EVQLVES-GGGLVKPGGSLRL SCAASG-FTFS | N------AWMN | WVRQAPGK GLEWVG | RIKNKA-DGGTTDYAA PVKG | RFTISRDDSKNTLYLQMNSL KTEDTAVYYCTI | VGAT------TDY | WGQGT LVTVS S |
| iPS:4 34671 | 21-225_74F4 | VH3|3-15|D1|1-1|RF2|JH4 | EVQLVES-GGGLVKPGGSLRL SCAASG-FTFS | N------AWMN | WVRQAPGK GLEWVG | RIKNKI-DGGTTDYAA PVKG | RFTISRDDSKNTLYLQMNSL KTEDTAVYYCTI | VGAT------TDY | WGQGT LVTVS S |
| iPS:4 37383 | 21-225_74H8 | VH3|3-15|D1|1-1|RF2|JH4 | EVHLVES-GGGLVKPGGSLRL SCAASG-FTFS | N------AWMN | WVRQAPGK GLEWVG | RIKSKT DGGTTDYAA PVKG | RFTISRDDSKNTLYLQMNSL KTEDTAVYYCTI | VGAT------TDY | WGQGT LVTVS S |
| VH3|3-33|D5|5-18|RF3|JH4 | | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | GXYG------FFDY | WGQGT LVTVS S |
| iPS:4 34535 | 21-225_74C8 | VH3|3-33|D5|5-18|RF3|JH4 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DGSYGY------DGLDY | WGQGT LVTVS S |
| iPS:4 34573 | 21-225_77E6 | VH3|3-33|D5|5-18|RF3|JH4 | QVQLVES-GGGVVQSGRSLRL SCAASG-FTFS | S------YGMH | WVRQAPGK GLEWVA | VIWYD---GSNQNVADS VKG | RFTISRDNSKNTLFLQMNSL RAEDTAVYYCAR | DGSYGY------DGLDY | WGQGT LVTVS S |
| iPS:4 34615 | 21-225_76C5 | VH3|3-33|D5|5-18|RF3|JH4 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DGSYGY------DGLDY | WGQGT LVTVS S |
| iPS:4 34669 | 21-225_79F4 | VH3|3-33|D5|5-18|RF3|JH4 | QVQLVES-GGGVVQPGRSLRL SCAASG-FTFS | N------YGMH | WVRQAPGK GLEWVA | VIWYD---GSNQNVADS VKG | RFTISRDNSKNTLFLQMNSL RAEDTAVYYCAR | DGSYGY------DGLDY | WGQGT LVTVS S |
| iPS:4 34737 | 21-225_74G6 | VH3|3-33|D5|5-18|RF3|JH4 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DGSYGY------DGLDY | WGQGT LVTVS S |
| iPS:4 34741 | 21-225_80C11 | VH3|3-33|D5|5-18|RF3|JH4 | QVQLVES-GGGVVQPGRSLRL SCAASG-FTFS | S------YGMH | WVRQAPGK GLEWVA | VIWYD---GSNKNYADS VKG | RFTISRDNSKNTLSLQMNSL RAEDTAVYYCAR | DGSYGY------DGLDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34867 | 21-225_79A12 | VH3/3-33|D5/5-18|RF3/JH4 | EVQLVES-GGGVVQPGKSRLR-LSCAASG-FTFS | S-----YGMH | WVRQAPGK GLEWVA | VINYD----GSNKNIADS VKG | RFTISRDNSKNTLYLQMNSL RAEDTAVYYCAR | DGSYGY--------DGLDY | WGQGT LVAVS S |
| | VH4|4-34D3|3-10|RF2|JH6 | Germline | | | | | | | |
| iPS:4 34539 | 21-225_74A2 | VH4|4-34|D3|3-10|RF2|J H6 | QVQLQQW-GAGLLKPSETLSL TCAVYG-GSFT | D-----YYWS | WIRQPPGK GLEWIG | EINH----SGDTNYNPS LKS | RVTISVDTSKNQFSLKLSSV TAADTAVYYCAR | EFPYSGSY--------LYYYGMDV | WGQGT TVTVS S |
| iPS:4 37248 | 21-225_97H3 | VH4|4-34|D3|3-10|RF2|J H6 | QVQLQQW-GAGLLKPSETLSL TCAVYG-GSFT | D-----YYWS | WIRQPPGK GLEWIG | EINH----SGDTNYNPS LKS | RVTISVDTSKNQFSLKLSSV TAADTAVYYCAR | EFPYSGSY--------LYYYGMDV | WGQGT TVTVS S |
| iPS:4 37320 | 21-225_75A1 | VH4|4-34|D3|3-10|RF2|J H6 | QVQLQQW-GAGLLKHSETLSL TCAVYG-GSFT | D-----YYWS | WIRQPPGK GLEWIG | EINH----SGDTNYNPS LKS | RVTISVDTSKNQFSLKLSSV TAADTAVYYCAR | EFPYSGSY--------LYYYGMDV | WGQGT TVTVS S |
| | VH3|3-13D3|3-9|RF1|JH6 | Germline | | | | | | | |
| iPS:4 34563 | 21-225_75D8 | VH3|3-13|D3|3-9|RF1|JH 6 | EVQLVES-GGGLVQPGGSLRL SCAASG-FTFS | N-----YDMH | WVRQATGK GLEWVS | AIGT----AGDTYYPGS VKG | RFTISRENAKNSLYLQMNSL RAGDTAVYYCAR | VLDYGDSLG------YYYYGMDV | WGQGT TVTVS S |
| iPS:4 35009 | 21-225_89G4 | VH3|3-13|D3|3-9|RF1|JH 6 | EVQLVES-GGGLVQPGGSLRL SCAASG-FTFS | S-----YDMH | WVRQATGK GLEWVS | AIGT----AGDTYYPGS VKG | RFTISRENAKNSLYLQMNSL RAGDTAVYYCAR | ALDYGDSLG------YYYYGMDV | WGQGT TVTVS S |
| iPS:4 35059 | 21-225_90C11 | VH3|3-13|D3|3-9|RF1|JH 6 | EVQLVES-GGGLVQPGGSLRL SCAASG-FTFS | N-----YDMH | WVRQATGK GLEWVS | AIGT----AGDTYYPGS VKG | RFTISRENAKNSLYLQMNSL RAGDTAVYYCAR | VLDYGDSLG------YYYYGMDV | WGQGT TVTVS S |
| iPS:4 35103 | 21-225_92B2 | VH3|3-13|D3|3-9|RF1|JH 6 | EVQLVES-GGGLVQPGGSLRL SCAASG-FTFS | N-----YDMH | WVRQATGK GLEWVS | AIGT----AGDTYYPGS VKG | RFTISRENAKNSLYFCAR | ALDYGDSLG------YYYYGMDV | WGQGT TVTVS S |
| iPS:4 37371 | 21-225_74D8 | VH3|3-13|D3|3-9|RF1|JH 6 | EVQLVES-GGGLVQPGGSLRL SCAASG-FTFS | N-----YDMH | WVRQATGK GLEWVS | AIGT----AGDTYYPGS VKG | RFTISRENAKNSLYLQMNSL RAGDTAVYFCAR | VLDYGDSLG------YYYYGMDV | WGQGT TVTVS S |
| | VH1|1-08|D1|1-26|RF3|JH4 | Germline | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 34711 | 21-225_80H3 | VH1|1-08/D1|1-26|RF3/J H4 | QVQLVQS-GAEVKKPGASVKV SCKASG-YTLT | N------YDIN | WVRQATGQ GLEWMG | WMNPN---SGNTGYAQK FQG | RVTMTRNTSISTAYMELSSL RSEDTAVYYCGS | TSGWN------FFDY | WGQGT LVTVS S |
| iPS:4 34901 | 21-225_85H9 | VH1|1-08/D1|1-26|RF3/J H4 | QVQLVQS-GAEVKKPGASVKV SCKASG-YTLT | N------YDIN | WVRQATGQ GLEWMG | WMNPN---SGNTGYAQK FQG | RVTMTRNTSISTAYMELSSL RSEDTAVYYRGS | TSGWN------FFDY | WGQGT LVTVS S |
| iPS:4 35167 | 21-225_92F12 | VH1|1-08/D1|1-26|RF3/J H4 | QVQLVQS-GAEVKKPGASVKV SCKASG-YTLT | N------YDIN | WVRQATGQ GLEWMG | WMNPN---SGNTGYAQK FQG | RVTMTRNTSISTAYMELSSL RSEDTAVYYRGS | TSGGK------FFDY | WGQGT LVTVS S |
| iPS:4 35215 | 21-225_94E12 | VH1|1-08/D1|1-26|RF3/J H4 | QVQLVQS-GAEVKKPGASVKV SCKASG-YTLT | N------YDIN | WVRQATGQ GLEWMG | WMNPN---SGNTGYAQK FQG | RVTMTRNTSISTAYMELSSL RSEDTAVYYRGS | TSGWK------FFDY | WGQGT LVTVS S |
| iPS:4 37356 | 21-225_74B1 | VH1|1-08/D1|1-26|RF3/J H4 | QVQLVQS-GAEVKKPGASVKV SCKASG-YTLT | N------YDIN | WVRQATGQ GLEWMG | WMNPN---SGNTGYAQK FQG | RVTMTRNTSISTAYMELSSL RSEDTAVYYCGS | TSGWN------FFDY | WGQGT LVTVS S |
| | Germline VH1|1-08/D1|1-1|RF1/JH6 | | | | | | | | |
| iPS:4 34815 | 21-225_74A11 | VH1|1-08/D1|1-1|RF1/JH 6 | QVQLVQS-GAEVKKPGASVKV SCKASG-YTFT | S------YDIN | WVRQATGQ GLEWMG | WMNPN---SGNTGYAQK FQG | RVTMWNTSKSTAYMELSSL RSEDTAVYYCAR | GFYDFLTGS------GYYYVMDV | WGQGT TVTVS S |
| iPS:4 35253 | 21-225_96A4 | VH1|1-08/D1|1-1|RF1/JH 6 | QVQLVQS-GAEVKKPGASVKV SCKASG-YTFT | S------YDIN | WVRQATGH GLEWMG | WMNPN---SGNTGYAQK FQG | RVTMIWNTSIRTAYMELSSL RSEDTAVYYCAR | GFYDFLTGS------GYYYVMDV | WGQGT TVTVS S |
| | Germline VH1|1-08/D3|3-22|RF2/JH6 | | | | | | | | |
| iPS:4 34977 | 21-225_88A5 | VH1|1-08/D3|3-22|RF2/J H6 | QVQLVQS-GAEVKKPGASVKV SCKASG-YTFT | S------YDIN | WVRQATGQ GLEWMG | WMNPN---SGNTGYAQK FQG | RVTMIWNTSIRTAYMELSSL RSEDTAVYYCAR | GFYDFLTGYS----PTYYYDMDV | WGQGT TVTVS S |
| iPS:4 35259 | 21-225_96C6 | VH1|1-08/D3|3-22|RF2/J H6 | QVQLVQS-GAEVKKPGASVKV SCKASG-YTFT | S------YDIN | WVRQATGQ GLEWMG | WMNPN---SRNTGYAQK FQG | RVTMIWNTSISTAYMELSSL RSEDTAVYYCAR | GGYDVLPGN------NYYYDMDV | WGQGT TVTVS S |
| | Germline VH3|3-33|D2|2-15|RF3/JH3 | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35291 | 21-225_146E1 | VH3/3-33/D2/2-15/RF3/JH3 | QVQLVES-GGGVVQPGRSLRL SCEASG-FTFS | S-----YGMH | WVRQAPGK GLEWVA | IIWYD----GSNKYADS VKG | RFTISRDNSKNTLFLQMNSL RAEDTAVYYCAR | DRLVGAT------ADAFDI | WGQGT MVTVS S |
| iPS:4 36360 | 21-225_210H11 | VH3/3-33/D2/2-15/RF3/JH3 | QVQLVES-GGGVVQPGRSLRL SCAASG-FTFS | S-----HGMH | WVRQAPGK GLEWVA | VTWYD----GSDKYADS VKG | RFTISRDNSKNTLYLQMNSL RAEDTAVYYCAR | DRLVGAT------TDAFDI | WGQGT MVTVS S |
| iPS:4 36370 | 21-225_211A6 | VH3/3-33/D2/2-15/RF3/JH3 | QVQLVES-GGGVVQPGRSLRL SCAASG-FTFS | S-----YGMH | WVRQAPGK GLEWVA | VIWYD----GSNKNYADS VKG | RFTISRDNSKNTLYLQMNSL RAEDTAVYYCAR | DRTVGY--------DGFDI | WGQGT MVTVS S |
| iPS:4 36392 | 21-225_213B3 | VH3/3-33/D2/2-15/RF3/JH3 | QVQLVES-GGGVVQPGRSLRL SCAASG-FTFS | S-----YGMH | WVRQAPGK GLEWVA | VIWYD----GSNKNYADS VKG | RFTISRDNSKNTLYLQMNSL RAEDTAVYYCAR | DRTVGY--------DGFDI | WGQGT MVTVS S |
| iPS:4 36406 | 21-225_214E4 | VH3/3-33/D2/2-15/RF3/JH3 | QVQLVES-GGGVVQPGRSLRL SCAASG-FTFS | S-----YGMH | WVRQAPGK GLEWVA | VIWYD----GSNENYADS VKG | RITISRDNSKNTLYLQMNSL RAEDTAVYYCAR | DRTVGY--------DGCDI | WGQGA MVTVS S |
| iPS:4 37326 | 21-225_75C10 | VH3/3-33/D2/2-15/RF3/JH3 | QVQLVES-GGGVVQPGRSLRL SCAASG-FTFS | S-----YGMH | WVRQAPGK GLEWVA | VIWYD----GSCKYADS VKG | RFTISRDNSKNTLYLQMNSL RAEDTAVYYCAR | DRLVGAT------VDAFDI | WGQGT MVTVS S |
| | Germline | | H_FR1 | H_CDR1 | H_FR2 | H_CDR2 | H_FR3 | H_CDR3 | H_FR4 |
| | VH4/4-39/D7/7-27/RF1/JH4 | | QLQLQES-GPGLVKPSETLSL TCTVSG-GSIS | RS----SYYWG | WIRQPPGK GLEWIG | SIYY-----SGSTSYNPS LKS | RVTISVDTSKNQFSLKLSSV TAADTAVYYCAR | | WGQGT LVTVS S |
| iPS:4 35293 | 21-225_146F1 | VH4/4-39/D7/7-27/RF1/JH4 | QLQLQES-GPGLVKPSETLSL TCTVSG-GSIS | RS----SYYWG | WIRQPPGK GLEWIG | SIYY-----SGSTSYNPS LKS | RVTISVDTSKNQFSLKLSSV TAADTAVYYCAR | LDLLW---------SFDY | WGQGT LVTVS S |
| iPS:4 35361 | 21-225_148E11 | VH4/4-39/D7/7-27/RF1/JH4 | QLQLQES-GPGLVKPSETLSL TCTVSG-VSIS | RS----SYYWG | WIRQPPGK GLEWIG | SIYY-----SGSTSYNPS LKS | RVTISVDTSKNQFSLKLSSV TAADTAVFYCAR | LDPQW---------SFDY | WGQGT LVTVS S |
| iPS:4 35449 | 21-225_152H9 | VH4/4-39/D7/7-27/RF1/JH4 | QLQLQES-GPGLVKPSETLSL TCTVSG-GSIS | RS----SYYWG | WIRQPPGK GLEWIG | SIYY-----SGSASYNPS LKS | RVTISVDTSKNQFSLKLSSV TAADTAVFYCAR | LDLQW---------SFDF | WGQGT LVTVS S |
| iPS:4 35499 | 21-225_156G1 | VH4/4-39/D7/7-27/RF1/JH4 | QLQLQES-GPGLVKPSETLSL TCTVSG-GSIS | RS----SYYWG | WIRQPPGK GLEWIG | SIYY-----SGSASYNPS LKS | RVTISVDTSKNQFSLKLSSV TAADTAVFYCAR | LDLQW---------SFDF | WGQGT LVTVS S |
| iPS:4 35587 | 21-225_160H3 | VH4/4-39/D7/7-27/RF1/JH4 | QLQLQES-GPGLVKPSETLSL TCTVSG-GSIS | RS----SYYWG | WIRQPPGK GLEWIG | SIYY-----SGSTSYNPS LES | RVTISVDTSKNQFSLKLSSV TAADTAVFYCAR | LSQRW---------DFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 03868 | 21-225_19D11 | VH4‑4‑39/D7/7‑27/RF1/JH4 Germline | QLQLQES‑GPGLVKPSETLSLTCTVSG‑GSIS | RS‑‑‑SYYWG | WIRQPPGKGLDWIG | SIYY‑‑‑‑SGSANYNPSLKS | RVTISVDTSKNQFSLKLSSVTAADAAVYYCAR | LDRGW‑‑‑‑‑‑‑‑‑‑SFDY | WGQGTLVTVSS |
| | | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKNTLYLQMNSLRAEDTAVYYCAK | DYYDY‑‑‑‑‑‑‑‑‑‑NDWFDP | WGQGTLVTVSS |
| iPS:4 35295 | 21-225_146H1 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKNTLYLQMNSLRAEDTAVYYCAK | RVTDYGG‑‑‑‑‑‑‑NDWFDP | WGQGTLVTVSS |
| iPS:4 35307 | 21-225_146E9 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKKTLYLQMNSLRAEDTAVYYCAK | RVTDYGG‑‑‑‑‑‑‑NDWFDP | WGQGTLVTVSS |
| iPS:4 35347 | 21-225_148C4 | VH3/3‑23/D4/4‑17/RF2/JH5 | EVQLLES‑GGGLVQPGGSLRLSCAASG‑FTFS | S‑‑‑‑‑YAMN | WVRQAPGKGLEWVS | AISGS‑‑‑‑GGNTFYADSVKG | RFTISRDNSKNTLYLQMNSLRAEDTAVYYCAK | RVTDYGG‑‑‑‑‑‑‑NDWFDP | WGQGTLVTVSS |
| iPS:4 35355 | 21-225_148H9 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKNTLYLQMNSLRAEDTAVYYCAK | RVTDYGG‑‑‑‑‑‑‑NDWFDP | WGQGTLVTVSS |
| iPS:4 35371 | 21-225_149A3 | VH3/3‑23/D4/4‑17/RF2/JH5 | EVQLLES‑GGGLVQPGGSLRLSCAASG‑FTFS | N‑‑‑‑‑YAMT | WVRQAPGKGLEWVS | AISGR‑‑‑‑GGNTFYADSVKG | RFTISRDNSKNTLYLQMNSLRAEDTAVYYCTK | RVTDYGG‑‑‑‑‑‑‑NDWFDP | WGQGTLVTVSS |
| iPS:4 35415 | 21-225_150C11 | VH3/3‑23/D4/4‑17/RF2/JH5 | EVQLLES‑GGGLVQPGGSLRLSCAASG‑FTFS | S‑‑‑‑‑YAMN | WVRQAPGKGLEWVS | AISGS‑‑‑‑GGNTFYADSVKG | RFTISRDNSKNTLNLQMSSLRAEDTAVYYCAK | RVTDYGG‑‑‑‑‑‑‑NDWFDP | WGQGTLVTVSS |
| iPS:4 35419 | 21-225_150C12 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKNTLYLQMNSLRAEDTAVYYCAK | RVTDYGG‑‑‑‑‑‑‑NDWFDP | WGQGTLVTVSS |
| iPS:4 35425 | 21-225_151B12 | VH3/3‑23/D4/4‑17/RF2/JH5 | EVQLLES‑GGGLVQPGGSLRLSCAASG‑FTFS | S‑‑‑‑‑YAMN | WVRHAEGKGLEWVS | AISGS‑‑‑‑GKNTFYADSVKG | RFTISRDNSKNTLYLQMNSLRAEDTAVYYCAK | RVTDYGG‑‑‑‑‑‑‑NDWFDP | WGQGTLVTVSS |
| iPS:4 35431 | 21-225_152D2 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKKTLYLQMNSLRAEDTAVYYCAK | RVTDYGG‑‑‑‑‑‑‑NDWFDP | WGQGTLVTVSS |
| iPS:4 35439 | 21-225_152G4 | VH3/3‑23/D4/4‑17/RF2/JH5 | EVQLLES‑GGGLVQPGGSLRLSCAASG‑FTFS | S‑‑‑‑‑YAMS | WVRQAPGKGLEWVS | AISGR‑‑‑‑GGNTFYADSVKG | RFTISRDNSKNTLYLQMNSLRAEDTAVYYCAK | RVTDYGG‑‑‑‑‑‑‑NDWFDP | WGQGTLVTVSS |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 35455 | 21-225_152B11 | VH3l3-23lD4l4-17lRF2lJH5 | EVQLLES-GGGLVQPGGSLRL SCAASG-FTFS | S-----YAMN | WVRQAPGK GLEWVS | AISGR---GGNTFYADS VKG | RFTISRDNSKNTLYLQMNSL RAEDTAVYYCAK | RVTDYGG-------NDWFDP | WGQGT LVTVS S |
| iPS:4 35487 | 21-225_155C4 | VH3l3-23lD4l4-17lRF2lJH5 | EVQLLES-GGGLVQPGGSLRL SCAASG-FTFS | S-----YAMS | WVRQAPGK GLEWVS | AISGR---GGNTFYADS VKG | RFTISRDNSKNILYLQMNSL RAEDTAVYYCAK | RVTDYGG-------NDWFDP | WGQGT LVTVS S |
| iPS:4 35503 | 21-225_156E4 | VH3l3-23lD4l4-17lRF2lJH5 | EVQLLES-GGGLVQPGGSLRL SCAASG-FTFS | S-----YAMS | WVRQAPGK GLEWVS | AISGR---GGNTFYADS VKG | RFTISRDNSKNILYLQMNSL RAEDTAVYYCAK | RVTDYGG-------NDWFDP | WGQGT LVTVS S |
| | Germline | H_FR1 | H_CDR1 | H_FR2 | H_CDR2 | H_FR3 | H_CDR3 | H_FR4 |
| | VH3l3-30lD3l3-22lRF3lJH6 | | | | | | | |
| iPS:4 35297 | 21-225_146B3 | VH3l3-30lD3l3-22lRF3lJH6 | QVQLVES-GGGVVQPGRSLRL SCAASG-FTFS | S-----YGMH | WVRQAPGK GLEWVA | VIWYD---GSYKYYADS VKG | RFTISRDNSKNTLDLQMNSL RAEDTAVYYCVK | MGIEVAVD-------YYYGMDV | WGQGT TVTVS S |
| | Germline | H_FR1 | H_CDR1 | H_FR2 | H_CDR2 | H_FR3 | H_CDR3 | H_FR4 |
| | VH4l4-30.1lD1l1-1lRF1lJH3 | | | | | | | |
| iPS:4 35301 | 21-225_146G4 | VH4l4-30.1lD1l1-1lRF1lJH3 | QVQLQES-GPGLVKPSQTLSL NCTVSG-GSIS | NS---GYYWS | WIRQHPGK GLEWIG | YSYY---SGSTYYNPS LKS | RITISVDTSNQFSLKLTSV TAADTAVYYCAR | GKYNWN-------HAFDI | WGQGT MVTVS S |
| | Germline | H_FR1 | H_CDR1 | H_FR2 | H_CDR2 | H_FR3 | H_CDR3 | H_FR4 |
| | VH3l3-21lD6l6-13lRF1lJH4 | | | | | | | |
| iPS:4 35313 | 21-225_146G11 | VH3l3-21lD6l6-13lRF1lJH4 | EVQLVES-GGGLVKPGGSLRL SCAASG-FTFS | S-----YSMN | WVRQAPGK GLEWVS | SISGS---GSTYYADS VKG | RFTISRDNAKMSLYLQMNSL RAEDTAVYYCAR | GSSSS-------GFDY | WGQGT LVTVS S |
| iPS:3 93808 | 21-225_1A2 | VH3l3-21lD6l6-13lRF1lJH4 | EVQLVES-GGGLVKPGGSLRL SCAASG-FTFS | S-----YTMN | WVRQAPGK GLEWVS | SISGS---GSYIYYADS VKG | RFTISRDNAKNSLYLQMNSL RAEDTAVYYCAR | GSSSS-------GFDY | WGQGT LVTVS S |
| iPS:3 93958 | 21-225_5H2 | VH3l3-21lD6l6-13lRF1lJH4 | EVQLVES-GGGLVKPGGSLRL SCAASG-FTFS | S-----YTMN | WVRQAPGK GLEWVS | SISGS---SSYIYYADS VKG | RFTISRANAKMSLYLQMNSL RAEDTAVYYCAR | GSSSS-------GFDY | WGQGT LVTVS S |
| | Germline | H_FR1 | H_CDR1 | H_FR2 | H_CDR2 | H_FR3 | H_CDR3 | H_FR4 |
| | VH4l4-30.4lD5l5-18lRF3lJH6 | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 35317 | 21-225_147D2 VH4/4-30.4/D5/5-18/RF3/J H6 | QVLLQES-GPGLVKPSQTLSL TCAVSG-GFIS | SG---DYYWN | WIRQRPGK GLEWIG | FIYY----TGSTYNPS LKS | RVSISEDTSENQFSLNLSSV TAADTAVYYCAR | GGAYYS--------YYGMDV | WGQGT TVTVS S |
| | Germline VH4/4-30.1/D5/5-24/RF3/JH3 | QVQLQES-GPGLVKPSQTLSL NCTVSG-GSIS | SG---GYYWS | WIRQHPGK GLEWIG | YIYY----SGSTYNPS LKS | RVTISVDTSKNQFSLKLSSV TAADTAVYYCAR | DAFDI | WGQGT MVTVS S |
| iPS:4 35319 | 21-225_147E3 VH4/4-30.1/D5/5-24/RF3/J H3 | QVQLQES-GPGLVKPSQTLSL TCTVSG-GSIT | NS---GYYYS | WIRQHPGK GLEWIG | YIYY----SGSTYNPS LKS | RITISVDTSNNQFSLKLSSV TAADTAVYYCAR | GGYNWN--------HAFDF | WGQGT MVTVS S |
| iPS:4 35383 | 21-225_149D7 VH4/4-30.1/D5/5-24/RF3/J H3 | QVQLQES-GPGLVKPSQTLSL NCTVSG-GSIS | NS---GYYWS | WIRQHPGK GLEWIG | YIYY----SGSTYNPS LKS | RITISVDTSNNQFSLKLSSV TAADTAVYYCAR | GGYNWN--------HAFDI | WGQGT MVTVS S |
| iPS:4 35443 | 21-225_152E7 VH4/4-30.1/D5/5-24/RF3/J H3 | QVQLQES-GPGLVKPSQTLSL NCTVSG-GSIS | NS---GYYWS | WIRQHPGK GLEWIG | YSYY----SGSTYNPS LKS | RITISVDTSNNQFSLKLSSV TAADTAVYYCAR | GGYNWN--------HAFDI | WGQGT MVTVS S |
| iPS:4 35465 | 21-225_153A6 VH4/4-30.1/D5/5-24/RF3/J H3 | QVQLQES-GPGLVKPSQTLSL NCTVSG-GSIS | NS---GYYWS | WIRQHPGK GLEWIG | YSYY----SGSTYNPS LKS | RITISVDTSNNQFSLKLSSV TAADTAVYYCAR | GGYNWN--------HAFDI | WGQGT MVTVS S |
| iPS:4 42568 | 21-225_149D8 VH4/4-30.1/D5/5-24/RF3/J H3 | QVQLQES-GPGLVKPSQTLSL NCTVSG-GSIS | NS---GYYWS | WIRQHPGK GLEWIG | YSYY----SGSTYNPS LKS | RITISVDTSNNQFSLKLSSV TAADTAVYYCAR | GGYNWN--------HAFDI | WGQGT MVTVS S |
| | Germline VH3/3-48/D4/4-11/RF2/JH4 | EVQLVES-GGGLVQPGGSLRL SCAASG-FTFS | S-----YSMN | WVRQAPGK GLEWVS | SISSS--SSSYIYYA DSVKG | RFTISRDNAKNSLYLQMNSL RAEDTAVYYCAR | DTYYYYA-------YFDY | WGQGT LVTVS S |
| iPS:4 35333 | 21-225_147E9 VH3/3-48/D4/4-11/RF2/J H4 | EVQLVES-GGGLVQPGGSLRL SCAASG-FTFS | S-----YSMN | WVRQAPGK GLEWVS | SISGR--NTTIYYADS VKG | RFTISRDNAKNSLYLQMNSL RQEDTAVYYCSR | DRG-----------SC | WGQGT LVTVS S |
| iPS:4 35637 | 21-225_163E2 VH3/3-48/D4/4-11/RF2/J H4 | EVQLVES-GGGLVQPGGSLRL SCAASG-FTFS | S-----YSMN | WVRQAEGK GLEWVS | STSGS--STYIYADS VKG | RFTISRQNAKNLVYLQMNSL RPEDIAVYYCAR | DRG-----------SL | WGQGT LVTVS S |
| | Germline VH1/1-02/D3/3-42/15/RF3/JH4 | QVQLVQS-GAEVKKPGASVKV SCKASG-YTFT | G-----YYMH | WVRQAPGQ GLEWMG | WINPN--SGGTNYAQT FQG | RVTMTRDTSISTVYMELSRL RSEDTAVYYCAR | DIYYYYA-------ATFDY | WGQGT LVTVS S |
| iPS:4 35351 | 21-225_148B6 VH1/1-02/D2/2-15/RF3/J H4 | QVQLVQS-CAEVKKPGASVKV SCKASG-YIFT | G-----YYMH | WVRQAPGQ GLEWMG | WIHPN--NGGTNYAQT FQG | RVIMTRDTSISTVYMELSRL RSDDTAVYYCAR | DPVVVP--------AAPFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH4/4-30.1/D5/5-12/RF3/JH6 | QVQLQES-GPGLVKPSQTLSL TCTVSG-GSIS | SG---GYYWS | WIRQHPGK GLEWIG | YIYY------SGSTYYNPS LKS | RVTISVDTSKDQFSLRLSSV TAADTAVYYCAR | GYSGYLY -------YYGMDV | WGQGT TVTVS S |
| iPS:4 35363 | 21-225_148F12 | QVQLQES-GPGLVKPSQTLSL TCTVSG-GSIS | NG---GYYWN | WIRQHPGK GLEWIG | YIYY------SGSTYYNPS LKS | QITISVDISKDQFSLRLSSV TAADTAVYYCAR | YSTYDY -------YYGMDV | WGQGT TVTVS S |
| iPS:4 35377 | 21-225_149G5 | QVQLQES-GPGLVKPSQTLSL TCTVSG-GSIS | NG---GYYWN | WIRQHPGK GLEWIG | YIYY------SGSTYYNPS LKS | RVTISVDISKDQFSLRLSSV TAADTAVYYCAR | YSTYDY -------YYGMDV | WGQGT TVTVS S |
| | H_FR1 | H_CDR1 | H_FR2 | H_CDR2 | H_FR3 | H_CDR3 | H_FR4 | |
| | VH3/3-48/D6/6-5/RF2/JH4 | EVQLVES-GGGLVQPGGSLRL SCAASG-FTFS | S---YSMT | WVRQAPGK GLDWVS | VISRS------SSTIYYADS VKG | RFSISRDNAKNSLYLQMNSL RDEDTALYYCAR | STAAS -------YFDY | WGQGT LVTVS S |
| iPS:4 35409 | 21-225_150G8 | EVQLVES-GGGLVQPGGSLRL SCAASG-FTFS | T---YSMT | WVRQAPGK GLDWVS | VISRS------SSTIYYADS VKG | RFSISRDNAKNSLYLQMNSL RDEDTALYYCAR | SAFS------PFDY | WGQGT LVTVS S |
| | H_FR1 | H_CDR1 | H_FR2 | H_CDR2 | H_FR3 | H_CDR3 | H_FR4 | |
| | VH3/3-30.3/D5/5-18/RF2/JH5 | QVQLVES-GGGVVQPGRSLRL SCAASG-FTFS | S---YGMH | WVRQAPGK GLEWVA | VISYD------GSNKYYADS VKG | RFTISRDNSKNTLYLQMNSL RAEDTAVYYCAR | WIQWL -------NWFDP | WGQGT LVTVS S |
| iPS:4 35427 | 21-225_151C9 | QVQLVES-GGGVVQPGRSLRL SCAASG-FTFS | S---YGMH | WVRQAPGK GLEWVA | VISYD------GSNKYYADS VKG | RFTISRDNSKNTLYLQMNSL RAEDTAVYYCAR | GVLIWFGH -------LEDDWFDP | WGQGT LVTVS S |
| | H_FR1 | H_CDR1 | H_FR2 | H_CDR2 | H_FR3 | H_CDR3 | H_FR4 | |
| | VH3/3-33/D3/3-22/RF2/JH4 | QVQLVES-GGGVVQPGRSLRL SCAASG-FTFS | S---YGMH | WVRQAPGK GLEWVA | IIWYD------GSNKYYADS VKG | RFTISRDNSKNTLYLQMNSL RAEDTAVYYCAR | GYSGYLY -------YYFDY | WGQGT LVTVS S |
| iPS:4 35441 | 21-225_152F6 | QVQLVES-GGGVVQPGRSLRL SCAASG-FTFS | S---YGMH | WVRQAPGK GLEWVA | IIWYD------GSYKYYADS VKG | RFTISRDNSKNTLYLQMNSL RAEDTAVYYCAR | EGYDFW------SGYLGY | WGQGT LVTVS S |
| iPS:4 35457 | 21-225_152C11 | QVQLVES-GGGVVQPGRSLRL SCAASG-FTFR | N---YGMH | WVRQAPGK GLEWVA | IIWYD------GSNKYYADS VKG | RFTISRDNSKNTLYLQMNSL RAEDTAVYYCAR | EAYDFW------SGYFDY | WGQGT LVTVS S |
| iPS:4 35463 | 21-225_153D2 | QVQLVES-GGGVVQPGRSLRL SCAASG-FTFS | S---YGMH | WVRQAPGK GLEWVA | IIWYD------GSYKYYADS VKG | RFTISRDNSKNTVYLQMNSL RAEDTAVYYCAR | EGYDFW------SGYLGY | WGQGT LVTVS S |
| iPS:4 35531 | 21-225_157G8 | QVQLVES-GGGVVQPGRSLRL SCAASG-FTFS | N---YGMH | WVRQAPGK GLEWVA | IIWYD------GSYKYYADS VKG | RFTVSRDNSKNILYLQMNSL RAEDTAVYYCAR | EGYDFW------SGFFDS | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35577 | 21-225_160B1 | VH3J3-33/D3J3-22/RF2/JH4 | QVQLVES-GGGVVQPGRSLRL SCAASG-FTFS | S-----YGMH | WVRQAPGK GLEWVA | VIWYD----GSYKYYADS VKG | RFTISRDNSKNTLYLQMNSL RAEDTAVYYCAR | EAYDFW------SGYYDY | WGQGT LVTVS S |
| iPS:4 35723 | 21-225_172B7 | VH3J3-33/D3J3-22/RF2/JH4 | QVQLVES-GGGVVQPGRSLRL SCAASG-FTFS | N-----YGMH | WVRQAPGK GLEWVA | IIWYD----GSNKYYYDS VKG | RFTISRDNSKNTLYLQMNSL RAEDTAVYYCAR | EAYDFW------SGYWDY | WGQGT LVTVS S |
| iPS:4 35731 | 21-225_173A11 | VH3J3-33/D3J3-22/RF2/JH4 | QVQLVES-GGGVVQPGRSLRL SCAASG-FTFS | S-----YGMH | WVRQAPGK GLEWVA | IIWYD----GSNKYYADS VKG | RFTISRDNSKNTLYLQMNSL RAEDTAVYYCAR | EAYDFW------SGFFDS | WGQGT LVTVS S |
| iPS:4 35781 | 21-225_178G10 | VH3J3-33/D3J3-22/RF2/JH4 | QVQLVES-GGGVVQPGRSLRL SCAASG-FTFS | T-----YGMH | WVRQAPGK GLEWVA | VIWYD----GSNKYYADS VKG | RFTISRDNFKNTLYLQMNSL RAEDTAVYYCAR | ERYDFW------SGHFDY | WGQGT LVTVS S |
| iPS:4 35899 | 21-225_188G11 | VH3J3-33/D3J3-22/RF2/JH4 | QVQLVES-GGGVVQPGRSLRL SCAASG-FTFS | S-----YGMH | WVRQAPGK GLEWVI | IIWYD----GSYKYYADS VKG | RFTISRDNSKNTLFLQMNSL RAEDTAVYYCAR | ERYDFW------SGHFDY | WGQGT LVTVS S |
| iPS:4 36602 | 21-225_226E7 | VH3J3-33/D3J3-22/RF2/JH4 | QVQLVES-GGGVVQPGRSLRL SCAASG-FTFS | T-----YGMH | WVRQAPGK GLEWVA | IIWYD----GSNKYYADS VKG | RFTISRDNFKNTLYLQMNSL RAEDTAVYYCAR | ENYDFW------SGYYGY | WGQGT LVTVS S |
| iPS:3 92930 | 21-225_25H9 | VH3J3-33/D3J3-22/RF2/JH4 | QVQLVES-GGGVVQPGRSLRL SCAASG-FFFN | N-----YGMH | WVRQAPGK GLEWVS | IIWYD----GSYKYYADS VKG | RFTISRDNSKNTLYLQMNSL RAEDTAVYYCAR | EGYDFW------SGFFDS | WGQGT LVTVS S |
| Germline | | | H_FR1 | H_CDR1 | H_FR2 | H_CDR2 | H_FR3 | H_CDR3 | H_FR4 |
| VH3J3-23/D1J1-26/RF2/JH4 | | | EVQLLES-GGGLVQPGGSLRL SCAASG-FTFS | | | | | | |
| iPS:4 35479 | 21-225_154E9 | VH3J3-23/D1J1-26/RF2/JH4 | EVKLLES-GGGLVQPGGSLRL SCAASG-FTFS | S-----YAMS | WVRQAPGK GLEWVS | AISGR----GGNTYYADS VKG | RFTISRDNSKNTLFLQMNSL RAEDTAVYYCAR | RGFRFLE----WLGGFDY | WGQGT LVTVS S |
| Germline | | | H_FR1 | H_CDR1 | H_FR2 | H_CDR2 | H_FR3 | H_CDR3 | H_FR4 |
| VH3J3-23/D5J5-18/RF3/JH4 | | | EVQLLES-GGGLVQPGGSLRL SCAASG-FTFS | | | | | | |
| iPS:4 35497 | 21-225_155H9 | VH3J3-23/D5J5-18/RF3/JH4 | EVQLLES-GGGLVQPGGSLRL SCAASG-FTFS | S-----YAMN | WVRQAPGK GLEWVS | TISGR----GLGTYYADS VKG | RFTISRDNSKNTLYLQMNSL RAEDTAVYYCAR | DHDYGDY----NIYFDY | WGQGT LVTVS S |
| Germline | | | H_FR1 | H_CDR1 | H_FR2 | H_CDR2 | H_FR3 | H_CDR3 | H_FR4 |
| VH3J3-23/D6J6-19/RF1/JH3 | | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35513 | 21-225_157F3 | VH3j3-23/D6j6-19jRF1/JH3 | EVQLLES-GGGLVQPGGSLRL SCAASE-FTFS | T------YAMS | WVRQAPGK GLEWVS | VISGS---GGSTYYADS VKG | RFTISRDNSKNTLYLQMNSL RAEDTAVYYCAK | RSSGWY------EDALDI | WGQGT MVTVS S |
| iPS:3 92766 | 21-225_23H4 | VH3j3-23/D6j6-19jRF1/JH3 | EVQLLES-GGGLVQPGGSLRL SCAASG-FTFS | S------YAMN | WVRQAPGK GLEWVS | VISGS---GGTYPADS VKG | RFTISRDNSKNTLYLQMNSL RAEDTAVYYCAK | RNSSGW------HDVPDI | WGQGT KVTVS S |
| iPS:3 92808 | 21-225_20F8 | VH3j3-23/D6j6-19jRF1/JH3 | EVQLLES-GGGLVQPGGSLRL SCAASG-FTFR | S------YAMS | WIRQAPGK GLEWSS | VISGS---GGSTYYADS VKG | RFTISRDNSKNTLYLQMSSL RAEDTAVYYCAK | RYNSGW------HDVPDI | WGQGT MVTVS S |
| | Germline | VH4j4-39jD2j2-21jRF3/JH4 | QVQLQES-GGGLVKPSETLSL KCTASG-GSIS | SS---SYWG | WIRQPPG-GLEWIG | SIYY----SGSTYYNPS LKS | RVTISVDTSKNQFSLRLSSV TAADTAAVYYCAR | RIVYY------AITYDY | WGQGT LVTVS S |
| iPS:4 35525 | 21-225_157E7 | VH4j4-39jD2j2-21jRF3/JH4 | QLHLQES-GPGLVKPSETLSL TCTVSG-GSIS | SG-----SYYWG | WIRQPPG-GLEWIG | SIYY----SGSTYYNPS LKS | RVTISVDTSKNQFSLNLSSV TAADTAVYYCAR | HKVAG------PFDY | WGQGT LVTVS S |
| | Germline | VH3j3-33jD3j3-10jRF2/JH6 | QVQLVES-GGGVVQPGRSLRL SCAASG-FTFS | ------YGMH | WVRQAPGK GLEWVS | VIWYD---GSNKYYADS VKG | RFTISRDNSKNTLYLQMNSL RAEDTAVYYCAR | YYYSSGW------WYYGMDV | WGQGT TVTVS S |
| iPS:4 35543 | 21-225_158D4 | VH3j3-33jD3j3-10jRF2/JH6 | QVQLVES-GGGVVQPGRSLRL SCAASG-FTFS | D------YVMH | WVRQAPGK GLEWVS | VIWYD---GSNKYYADS VKG | RFTISRDNSKNTLYLQMNSL RAEDTAVYYCAR | EPYTSGW------YDYGMDV | WGQGT TVTVS S |
| iPS:4 35571 | 21-225_159C8 | VH3j3-33jD3j3-10jRF2/JH6 | QVQLVES-GGGVVQPGRSLRL SCAASG-FTFS | D------YVMQ | WVRQAPGK GLEWVA | VIWYD---GSNKYYADS VKG | RFTISRDNSKNTLYLQMNSL RAEDTAVYYCAR | EPYNSGW------YDYGMDV | WGQGT TVTVS S |
| iPS:4 35591 | 21-225_160C4 | VH3j3-33jD3j3-10jRF2/JH6 | QVQLVES-GGGVVQPGRSLRL SCAASG-FTFS | D------YVMQ | WVRQAPGK GLEWVA | VIWYD---GSNKYYADS VKG | RFTISRDNSKNTLYLQMNSL RAEDTAVYYCAR | EPYNSGW------YDYGMDV | WGQGT TVTVS S |
| iPS:4 35615 | 21-225_161G12 | VH3j3-33jD3j3-10jRF2/JH6 | QVQLVES-GGGVVQPGRSLRL SCAASG-FTFS | D------YVMQ | WVRQAPGK GLEWVA | VIWYD---GSNKYYADS VKG | RFTISRDNSKNTLYLQMNSL RAEDTAVYYCAR | EPYNSGW------YDYGMDV | WGQGT TVTVS S |
| iPS:4 36604 | 21-225_226F7 | VH3j3-33jD3j3-10jRF2/JH6 | QVQLVES-GGGVVQPGRSLRL SCAASG-FTFS | S------YGMH | WVRQAPGK GLEWVA | IIWYD---GSNKYYADS VKG | RFTISRDNSKNTLYLQMNSL RAEDTAVYYCAR | ERYNSGW------YDYGLDV | WGQGT TVTVS S |
| iPS:4 51114 | 21-225_159A3 | VH3j3-33jD3j3-10jRF2/JH6 | QVQLVES-GGGVVQPGRSLRL SCAASG-FTFS | D------YVMQ | WVRQAPGK GLEWVA | VIWYD---GSNKYYADS VKG | RFTISRDISKNTLYLQMNSL RAEDTAVYYCAR | EPYNSGW------YDYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 72732 | 21-225_2B10_LC1 | VH3)3-33/D3)3-10|RF2/JH6 | QVQLVES-GGGVVQPGRSLRLSCAASG-FTFS | S-----YVMH | WVRQAPGK GLEWVA | VINYD---GSNKYYADSVKV | RFTVSRDNSKNTLSLQMNSL RAEDTAVYYCAR | ERYTSGW------YDYGMDV | WGQGT TVTVS S |
| iPS:4 72733 | 21-225_2B10_LC2 | VH3)3-33/D3)3-10|RF2/JH6 | QVQLVES-GGGVVQPGRSLRLSCAASG-FTFS | S-----YVMH | WVRQAPGK GLEWVA | VINYD---GSNKYYADSVKV | RFTVSRDNSKNTLSLQMNSL RAEDTAVYYCAR | ERYTSGW------YDYGMDV | WGQGT TVTVS S |
| iPS:3 92872 | 21-225_20B11 | VH3)3-33/D3)3-10|RF2/JH6 | QVQLVES-GGGVVQPGRSLRLSCAASG-FTFS | S-----YVMH | WVRQAPGK GLEWVA | VINYD---GSNKYYADSVKV | RFTVSRDNSKNTLSLQMNSL RAEDTAVYYCAR | ERYTSGW------YDYGMDV | WGQGT TVTVS S |
| iPS:3 93966 | 21-225_7F8 | VH3)3-33/D3)3-10|RF2/JH6 | QVQLVES-GGGVVQPGRSLRLSCAASG-FTFS | S-----CVMH | WVRQAPGK GLEWVA | VINYD---GSNKYYADSVKG | RFTISRDNSNTLYLQMNSL RAEDTAVYYCAR | ERYTSGW------HDYGMDV | WGQGT TVTVS S |
| | Germline | | H_FR1 | H_CDR1 | H_FR2 | H_CDR2 | H_FR3 | H_CDR3 | H_FR4 |
| | VH3)3-23/D1)1-1|RF1/JH6 | | | | | | | | |
| iPS:4 35559 | 21-225_158H12 | VH3)3-23/D1)1-1|RF1/JH6 | EVQLVES-GGGLVQPGGSLRLSCAASG-FTFS | S-----YVMS | WVRQAPGK GLEWVS | AISGS---GGRTDYADSVKG | RFTISRDNSKNTLYLQMNSL RAEDTAVYYCAR | GGW---------NHD | WGQGT TVTVS S |
| | Germline | | H_FR1 | H_CDR1 | H_FR2 | H_CDR2 | H_FR3 | H_CDR3 | H_FR4 |
| | VH3)3-21/D1)1-1|RF1/JH6 | | | | | | | | |
| iPS:4 35561 | 21-225_159F1 | VH3)3-21/D1)1-1|RF1/JH6 | EVQLVES-GGGLVKPGGSLRLSCAASG-FTFS | S-----YRMN | WVRQAPGK GLEWVS | SISGS---GNYIDYADSVKG | RFTISRDNAKNSLYLQMNSL RAEDTAVYYCAR | GW-----------DV | WGQGT TVTVS S |
| | Germline | | H_FR1 | H_CDR1 | H_FR2 | H_CDR2 | H_FR3 | H_CDR3 | H_FR4 |
| | VH1)1-08/D1)1-1|RF1/JH4 | | | | | | | | |
| iPS:4 35563 | 21-225_159H2 | VH1)1-08/D1)1-1|RF1/JH4 | QVQLVQS-GAEVKKPGASVKVSCKASG-YTFT | S-----YDIN | WVRQATGQ GLEWMG | WMNPN---SGNTGYVQKFQG | RVTMTRNTSISTAYMELSSL RSEDTAVYYCAR | KKT---------GDY | WGQGT LVTVS S |
| iPS:3 92718 | 21-225_17B8 | VH1)1-08/D1)1-1|RF1/JH4 | QVQLVQS-GAEVKKPGASVKVSCKASG-YTFT | S-----YAIN | WVRQATGQ GLEWMG | WMNPN---TGNTGYAQKFQG | RVTMTRNTSISTAYMELSSL RSEDTAVYFCTR | KAG---------FDY | WGQGT LVTVS S |
| iPS:3 93064 | 21-225_33A9 | VH1)1-08/D1)1-1|RF1/JH4 | QVQLVQS-GAEVKKPGASVKVSCKASG-YTFT | S-----YDIN | WVRQATGQ GLEWMG | WMNPN---SGNTGYAQKFQG | RVTMTRNTSISTAYMELSSL GSEDTAVYYCAR | KKA---------NDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 93148 | 21-225_35E5 | VH1|1-08/D1|1-1|RF1/JH4 | QVQLVQS-GAEVKKPGASVKV SCKASG-YIFT | S-----YDIN | WVRQATGQ GLEWMG | WMNPN---SGNTGYAQK FQG | RVTMTRNTSISTAYMELSSL RSEDTAVYYCAR | KKS------------NDY | WGQGT LVTVS S |
| iPS:3 98530 | 21-225_32G4 | VH1|1-08/D1|1-1|RF1/JH4 | QVQLVQS-GAEVKKPGASVKV SCKASG-YIFT | S-----YDIN | WVRQATGQ GLEWMG | WMNPN---SGNTGYAQK FQG | RVTMTRNTSISTAYMELSSL RSEDTAVYYCAR | KKA------------NDY | WGQGT LVTVS S |
| | Germline | VH3|3-30.3|D1|1-26|RF3|JH6 | | | | | | |
| iPS:4 35565 | 21-225_159C4 | VH3|3-30.3|D1|1-26|RF3/JH6 | QVQLVES-GGGVVQPGRSLRL SCAASG-FTFS | N-----YGMH | WVRQAPGK GLEWVA | VISYS---GNNKYYADS VKG | RFTISRDNSKNTLYLQLNSL RAEDMAVYYCAR | RSSSWG------GYGMDV | WGHGT TVTVS S |
| iPS:3 93892 | 21-225_6G7 | VH3|3-30.3|D1|1-26|RF3/JH6 | QVQLVES-GGGVVQPGRSLRL SCAASG-FTFS | S-----YGMH | WVRQTPGK GLEWVA | IISYV---GKNKYYADS VKG | RFTISRDNSKNTLYLQMNSL RAEDTAVYYCAR | RGNSYG------GYGMDV | WGQGT TVTVS S |
| | Germline | VH3|3-23|D2|2-21|RF3|JH4 | | | | | | |
| iPS:4 35579 | 21-225_160G1 | VH3|3-23|D2|2-21|RF3/JH4 | EVQLLES-GGGLVQPGGSLRL SCAASG-FTFS | S-----YVMS | WVRQAPGK GLEWIG | AMSGS---GGHTYYADS VKG | RFTISRDNSKNTLYLQMNSL RAEDTAVYYCVR | HG------------YS | WGQGT LVTVS S |
| iPS:4 35585 | 21-225_160G3 | VH3|3-23|D2|2-21|RF3/JH4 | EVQLLES-GGGLVQPGGSLRL SCAASG-FTFS | S-----YVMS | WVRQTPGK GLEWVS | AMSGS---GGHTYYADS VKG | RFTISRDNSKNTLYLQMNSL RAEDTAIYYCVR | HG------------YS | WGQGT LVTVS S |
| | Germline | VH4|4-39|D1|1-1|RF3|JH5 | | | | | | |
| iPS:4 35599 | 21-225_160B10 | VH4|4-39|D1|1-1|RF3/JH5 | QLQLQES-GPGLVKPSETLSL TCTVSG-GSIS | RS----SYYWG | WIRQTPGK GLEWIG | NIYY----SGSAYHIPS LKS | RVTISVDTSKNQFSLKLNSV TAADIAVYYCVR | HDPNW-------GVDY | WGQGT LVTVS S |
| | Germline | VH3|3-33|D1|1-1|RF2|JH6 | | | | | | |
| iPS:4 35601 | 21-225_160G10 | VH3|3-33|D1|1-1|RF2/JH6 | QVQLVES-CGGVVQPGRSLRL SCAASG-FTFS | S-----FGMH | WVRQAPGK GLEWVA | VIWYD---GSYKYYADS VKG | RFTISRDNSKNTLYLQMNSL RAEDTAVYYCAR | VGIEVAGD----YYFGMEV | WGQGT TVTVS S |

Figure 51 (Continued)

| | | | | H_CDR1 | | | | | |
|---|---|---|---|---|---|---|---|---|---|
| iPS:4 35655 | 21-225_167E2 | VH3|3-33|D1|1-1|RF2|JH6 | QVQLVES-GGGVVQPGRSLRL SCAASG-FTFS | S-----FGMH | WVRQAPGK GLEWVA | VIWYD---GTYKYYADS VKG | RFTISRDNSKNTLYLQMNSL RAEDTAVYYCAR | VGIEVAGD------YYYGMEV | WGQGT TVTVS S |
| iPS:4 35657 | 21-225_167H10 | VH3|3-33|D1|1-1|RF2|JH6 | QVQLVES-GGGVVQPGRSQRL SCAASG-FTFS | S-----FGMH | WVRQAPGK GLEWVA | VIWYD---GSYKYHADS VKG | RFTISRDNSKNTLYLQMNSL RAEDTAVYYCAR | VGIEVAGD------YYYGMEV | WGQGT TVTVS S |
| | Germline | VH3|3-53|D7|7-27|RF3|JH4 | | H_CDR1 | | | H_FR3 | H_CDR3 | H_FR4 |
| iPS:4 35605 | 21-225_161A4 | VH3|3-53|D7|7-27|RF3|JH4 | EVQLVES-GGGLIQPGGSLRL SCAASG-FTVS | S-----NYMS | WVRQAPGK GLEWVS | VIYT----GGSTYNADS VKG | RFTISRDNSKNTLYLQMNSL RAEDTAVYYCAR | NWGMA-------GPFDY | WGQGT LVTVS S |
| | Germline | VH3|3-30.3|D6|6-6|RF1|JH6 | QVQLVES-GGGVVQPGRSLRL SCAASG-FTFS | H_CDR1 | | | H_FR3 | H_CDR3 | H_FR4 |
| iPS:4 35607 | 21-225_161G4 | VH3|3-30.3|D6|6-6|RF1|JH6 | QVQLVES-GGGVVQPGRSLRL SCAASG-FTFS | S-----YGMH | WVRQAPGK GLEWVA | VISYG---GSNKYHADS VKG | RFTISRDNSKNTLYLQMNSL RAEDTAVYYCVR | RSSSSG------GYGMDV | WGQGT TVTVS S |
| iPS:4 93020 | 21-225_30E2 | VH3|3-30.3|D6|6-6|RF1|JH6 | QVQLVES-GGGVVQPGRSLRL SCAASG-FTFS | S-----YGMH | WVRQAPGK GLEWVA | VISYG---GSNKFYAVS VKG | RFTISRDNSKNTLYLQMNSL RAEDTAVYYCVR | RGYSSG------GYGMDV | WGQGT TVTVS S |
| iPS:3 93062 | 21-225_33H3 | VH3|3-30.3|D6|6-6|RF1|JH6 | QVQLVES-GGGVVQPGRSLRL SCAASG-FTFS | S-----YGMH | WVRRAPGK GLEWVA | IISYG---GSNNFYADS VKG | RFTISRDNSKNTLYLQMNSL RAEDTAVYYCAR | RGYSSG------GYGMDV | WGQGT TVTVS S |
| iPS:3 93138 | 21-225_35E3 | VH3|3-30.3|D6|6-6|RF1|JH6 | QVQLVES-GGGVVQPGRSLRL SCAASG-FTFS | S-----YGMH | WVRQAPGK GLEWVA | VISYG---GSNKYYADS VKG | RFTISRDNSKNTLYLQMNSL RAEDTAVYYCAR | RGYSSG------GYGMDV | WGQGT TVTVS S |
| | Germline | VH3|3-30.3|D6|6-13|RF1|JH6 | | H_CDR1 | | | H_FR3 | H_CDR3 | H_FR4 |
| iPS:4 35611 | 21-225_161F10 | VH3|3-30.3|D6|6-13|RF2|JH6 | QVQLVES-GGGVVQPGRSLRL SCAASG-FTFS | S-----YGMH | WVRQAPGK GLEWVA | IISYS---GRNDFYADS VKG | RFTISRDNSKNTLYLQMNSL RAEDTAVYYCAR | RIAAAG------HYGMDV | WGQGT TVTVS S |
| | Germline | VH3|3-33|D6|5-18|RF1|JH6 | | H_CDR1 | | | H_FR3 | H_CDR3 | H_FR4 |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35629 | 21-225_162H6 | VH3/3-33/D5/5-18/RF1/JH6 | QVQLVES-GGGVVQPGRSLRLSCAASG-FTFN | N-----YGMH | WVRQAPGK GLEWVA | VIWYD----GSNKYYADS VKG | RFTISRDNSKNTLYLQMNSL RAEDTAVYYCAR | KGIAAVGD--------YYYGMDV | WGQGT TVTVS S |
| | | Germline | EVQLVES-GGGLVKPGGSLRL SCAASG-FTFS | -------YGMH | WVRQAPGK GLEWVS | SISSS---SSYIYADS VKG | RFTISRDNAKNSLYLQMNSL RAEDTAVYYCAR | AKLLLLLL--------YYYGMDV | WGQGT TVTVS S |
| iPS:4 35639 | 21-225_163G6 | VH3/3-21/D7/7-27/RF1/JH6 | EVQLVES-GGGLVKPGGSLRL SCAASG-FTFS | S-----YSMS | WVRQAPGK GLEWVS | SISGS---SAYIYADS VKG | RFTISRDNAKNSLYLQLMNSL RAEDTAVYYCAR | LSG--------------MDV | WGQGT TVTVS S |
| | | Germline | EVQLVES-GGGLVKPGGSLRL SCAASG-FTFS | -------YGMH | WVRQAPGK GLEWVS | SISSS---SSYIYADS VKG | RFTISRDNAKNSLYLQMNSL RAEDTAVYYCAR | AKLLLLLL--------YYYGMDV | WGQGT TVTVS S |
| iPS:4 35643 | 21-225_163G10 | VH3/3-21/D5/5-24/RF2/JH6 | EVQLVES-GGGLVKPGGSLRL SCAASG-FTFS | S-----YSMN | WVRQAPGK GLEWVS | SISGS---STYIYADS VKG | RFTISRDNAKNSLYLQMNSL RAEDTAVYYCAR | ARM---------------DV | WGQGT TVTVS S |
| | | Germline | EVQLVES-GGGLVKPGGSLRL SCAASG-FTFS | -------YGMH | WVRQAPGK GLEWVA | VIWYD----GTNKYIADS VKG | RFTISRDNSKNTLYLQMNSL RAEDTAVYYCAR | AKDTIIS---------YYNFDY | WGQGT LVTVS S |
| iPS:4 35663 | 21-225_169B1 | VH3/3-33/D3/3-9/RF2/JH4 | QVQLVES-GGGVVQPGRSLRL SCAASG-FTFS | S-----YGMH | WVRQAPGK GLEWVA | VIWYD----GSNKYYADS VRG | RFTISRDNSKNTLYLQMNSL RAEDTAVYYCAR | DPLRGYN----------DPVMDY | WGQGT LVTVS S |
| iPS:4 35669 | 21-225_169F9 | VH3/3-33/D3/3-9/RF2/JH4 | QVQLVES-GGGVVQPGRSLRL SCAASG-FTFS | T-----YGMH | WVRQAPGK GLEWVS | IIWYD----GTNKYYADS VKG | RFTISRDNSKNTLYLQMNSL RAEDTAVYYCAR | DPLRGYN----------DPVMDY | WGQGT LVTVS S |
| iPS:4 35693 | 21-225_170G4 | VH3/3-33/D3/3-9/RF2/JH4 | QVQLVES-GGGVVQPGRSLRL SCAASG-FTFS | T-----YGMH | WVRQAPGK GLEWVS | IIWYD----GTNKYYADS VKG | RFTISRDNSKNTLFLQLNSL RAEDTAMYYCAR | DPLRGYN----------DPVMDY | WGQGT LVTVS S |
| iPS:4 35695 | 21-225_170D5 | VH3/3-33/D3/3-9/RF2/JH4 | QVQLVES-GGGVVQPGRSLRL SCAASG-FTFS | S-----YGMH | WVRQAPGK GLEWVA | IIWYD----GTNKYYADS VKG | RFTISRDNSKNTLYLQLNSL RAEDTAVYYCAR | DPLRGYN----------DPVMDY | WGQGT LVTVS S |
| iPS:4 35697 | 21-225_170G5 | VH3/3-33/D3/3-9/RF2/JH4 | QVQLVES-GGGVVQPGRSLRL SCAASG-FTFS | T-----YGMH | WVRQAPGK GLEWVI | IIWYD----GTNKYYADS VKG | RFTISRDNSKSTLYLQLNSL RAEDTAVYFCAR | DPLRGYN----------DPVMDY | WGQGT LVTVS S |
| iPS:4 35703 | 21-225_170D11 | VH3/3-33/D3/3-9/RF2/JH4 | QVQLVES-GGGVVQPGRSLRL SCVASG-FTFS | S-----YGMH | WVRQAPGK GLEWVA | IIWYD----GTNKYYADS VKG | RFTISRDNSKNTLYLQLNSL RAEDTAVYYCAR | DPLRGYN----------DPVMDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35705 | 21-225_171C3 | VH3\|3-33/D3\|3-9\|RF2\|JH4 | QVQLVES-GGGVVQPGGSLRLSCAASG-FTFS | T------YGMH | WVRQAPGK GLEWVT | IIWYD---GTNKYYADS VKG | RFTISRDNSKNTLYLQMNSL RAEDTAVYYCAR | DPLRGYN------DPVMDY | WGQGT LVTVS S |
| iPS:4 35709 | 21-225_171A4 | VH3\|3-33/D3\|3-9\|RF2\|JH4 | QVQLVES-GGGVVQPGGSLRLSCAASG-FTFS | T------YGMH | WVRQAPGK GLEWVA | IIWYD---GSNKYYADS VKG | RFTISRDNSKNTLYLQMNSL RAEDTAVYYCAR | DPLRGYN------DPVMDY | WGQGT LVTVS S |
| iPS:4 35721 | 21-225_172B3 | VH3\|3-33/D3\|3-9\|RF2\|JH4 | QVQLVES-GGGVVQPGRPLRLSCAASG-FTFS | T------YGMH | WVRQAPGK GLEWVA | VIWYD---GSNKYYADS VKG | RFTISRDNSKNTLYLQMNSL RAEDTAVYYCAR | DPLRGYN------DPVMDY | WGQGT LVTVS S |
| iPS:4 35725 | 21-225_172G8 | VH3\|3-33/D3\|3-9\|RF2\|JH4 | QVQMVES-GGGVVQPGRSLRLSCAASG-FTFS | T------YGMH | WVRQAPGK GLEWMA | IIWYD---GTNKYYADS VKG | RFTISRDNSKNTLYLQLNSL RAEDTAVYYCAR | DPLRGYN------DPVMDY | WGQGT LVTVS S |
| iPS:4 35735 | 21-225_173H12 | VH3\|3-33/D3\|3-9\|RF2\|JH4 | QVQLVES-GGGVVQPGRSLRLSCAASG-FTFS | S------YGMH | WVRQAPGK GLEWVA | IIWYD---GTNKYYADS VKG | RFTISRDNSKNTLYLQLNSL RAEDTAVYYCAR | DPLRGYN------DPVMDY | WGQGT LVTVS S |
| iPS:4 35743 | 21-225_175G1 | VH3\|3-33/D3\|3-9\|RF2\|JH4 | QVQLVES-GGGVVQPGGSLRLSCAASG-FTFS | T------YGMH | WVRQAPGK GLEWVS | VIWYD---GSNKYYADS VKG | RFTISRDNSKNTLYLQMNSL RAEDTAVYYCAR | DPLRGYN------DPVMDY | WGQGT LVTVS S |
| iPS:4 35761 | 21-225_176B11 | VH3\|3-33/D3\|3-9\|RF2\|JH4 | QVQLVES-GGGVVQPGRSLRLSCAASG-FTFS | T------YGMH | WVRQAPGK GLEWVS | IIWYD---GTNKYYADS VKG | RFTISRDNSKNTLFLQLNSL RAEDTAVYYCAR | DPLRGYN------DPVLDY | WGQGT LVTVS S |
| iPS:4 35779 | 21-225_178B10 | VH3\|3-33/D3\|3-9\|RF2\|JH4 | QVQLVES-GGGVVQPGRSLRLSCVASG-FTSS | T------YGMH | WVRQAPGK GLEWMA | IIWYD---GTNKYYADS VKG | RFTISRDNSKNTLYLQLNSL RAEDTAVYYCAR | DPLRGYN------DPVMDY | WGQGT LVTVS S |
| | Germline | | | | | | | | |
| | VH3\|3-48D2\|2-15\|RF3\|JH6 | | | | | | | | |
| iPS:4 35667 | 21-225_169E3 | VH3\|3-48D2\|2-15\|RF3\|JH6 | EVQLVES-GGGLVQPGGSLRLSCAASG-FTFS | G------HSMN | WVRQAPGK GLEWVA | YISLS---GSTIKYADS VKG | RFTISRDNARDSLYLQMNSL RDEDTAVYYCAR | RGITVVR------NEDGLDV | WGQGT TVTVS S |
| iPS:4 35673 | 21-225_169E6 | VH3\|3-48D2\|2-15\|RF3\|JH6 | EVQLVES-GGGLVQPGGSLRLSCAASG-FTFS | G------HSMN | WVRQAPGK GLEWVA | YISIS---SSTIKYADS VKG | RFTISRDNARDSLYLQMNSL RDEDTAVYYCAR | RGITVVR------NEDGLDV | WGQGT TVTVS S |
| iPS:4 35759 | 21-225_176E6 | VH3\|3-48D2\|2-15\|RF3\|JH6 | EVQLVES-GGGLVQPGGSLRLSCAASG-FTFS | G------HSMN | WVRQAPGK GLEWVA | YISIS---GSTIKYADS VKG | RFTISRDNARDSLYLQMNSL RDEDTAVYYCAR | RGITVVR------NEDGLDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH4/4-59/D3/3-9/RF1/JH6 | | | | | | | |
| iPS:4 35675 | 21-225_169D7 | VH4/4-59/D3/3-9/RF1/JH6 | QVQLQES-GPGLVKPSETLSLTCTVSG-GSIS | S-----YYWT | WIRQPAGKGLEWIG | RIYT----SGSTNYNPSLKS | RVTMSVDTSKNQFSLKLSSVTAADTAVYFCAK | VGRYY---------YGMDV | WGQGTTVTVSS |
| iPS:4 35687 | 21-225_170H1 | VH4/4-59/D3/3-9/RF1/JH6 | QVQLQES-GPGLVKPSETLSLTCTVSG-GSIS | S-----YYMS | WIRQPAGKGLEWIG | RIYT----SGSTNYNPSLKS | RVTMSVDTSKNQFSLKLSSVTAADTAVYFCAK | VGRYY---------YGMDV | WGQGTTVTVSS |
| | Germline | H_FR1 | H_CDR1 | H_FR2 | H_CDR2 | H_FR3 | H_CDR3 | H_FR4 |
| | VH3/3-23/D4/4-23/RF2/JH4 | | | | | | | |
| iPS:4 35711 | 21-225_171G4 | VH3/3-23/D4/4-23/RF2/JH4 | EVQLLES-GGGLVQPGGSLRLSCAASG-FTFS | S-----CAMT | WVRQAPGKGLEWVS | AISGR---GGTFYADSVRG | RFTISRDNSKNTLFLQMNSLRAEDTAVYSCAK | DLIGGA--------TYFDY | WGQGTLVTVSS |
| iPS:4 35875 | 21-225_190B9 | VH3/3-23/D4/4-23/RF2/JH4 | EVQLLES-GGGLVQPGGSLRLSCAASG-FTFS | T-----YAMS | WVRQAPGKGLEWVS | AISRS---GGNTYYADSVKG | RFTISRDNSKNTLYLQMNSLRAEDTAVYSCAK | DGFGGS--------SYFDY | WGQGTLVTVSS |
| iPS:4 35909 | 21-225_190H3 | VH3/3-23/D4/4-23/RF2/JH4 | EVQLLES-GGGLVQPGGSLRLSCAASG-FTFS | S-----YAMS | WVRQAPGKGLEWVS | AISGR---GGNTYYADSVKG | RFTISRDNSKNTLYLQMNSLRAEDTAVYSCAK | DGFGGS--------SYFDY | WGQGTLVTVSS |
| iPS:4 36013 | 21-225_193F2 | VH3/3-23/D4/4-23/RF2/JH4 | EVQLLES-GGGLVQPGGSLRLSCAASG-FTFS | T-----FAMS | WVRQAPGKGLEWVS | AISRS---GGNTYYADSVKG | RFTISRDNSKNTLYLQMNSLRAEDTAVYSCAK | DGFGGS--------SYFDY | WGQGTLVTVSS |
| iPS:4 36100 | 21-225_195G12 | VH3/3-23/D4/4-23/RF2/JH4 | EVQLLES-GGGLVQPGGSLRLSCAASG-FTFS | T-----YAMS | WVRQAPGKGLEWVS | AISRS---GGNTYYADSVKG | RFTISRDNSKNTLYLQMNSLRAEDTAVYSCAK | DGFGGS--------SYFDY | WGQGTLVTVSS |
| | Germline | H_FR1 | H_CDR1 | H_FR2 | H_CDR2 | H_FR3 | H_CDR3 | H_FR4 |
| | VH3/3-30.3/D1/1-7/RF2/JH6 | | | | | | | |
| iPS:4 35713 | 21-225_171D7 | VH3/3-30.3/D1/1-7/RF2/JH6 | QVQLVES-RGGVVQPGRSLRLSCAASG-FTFS | S-----YGMH | WVRQAPGKGLEWVA | VISYD---GNNRHYADSVQG | RFTISRDNSKNTLSLQMNSLGAEDTAVYYCAR | DRHRLD--------YYALDV | WGQGTTVTVSS |
| | VH3/3-23/D4/5-24/RF3/JH3 | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35729 | 21-225_173E7 | VH3/3-23/D5/5-24/RF3/JH3 | EVQLLES-GGGSVQPGGSLRL SCAASG-FTFS | S------YAMS | WVRQAPGK GLEWVS | FISGS---GGNTYFADS VKG | RFTISRDNSKNTLYLQMNSL QAEDTAVYYCTK | RDTYNG----------WDAFDI | WGQGT MVTVS S |
| iPS:4 35753 | 21-225_175G10 | VH3/3-23/D5/5-24/RF3/JH3 | EVQLLES-GGGLVQPGGSLRL SCAASG-FTFS | S------YAMS | WVRQTPGK GLEWVS | IISGS---GGNTYYADS VKG | RFTISRDNSKNTLYLQMNSL RAEDTAVYYCAK | RDTWNG----------WDAFDI | WGQGT MVTVS L |
| iPS:3 93024 | 21-225_31H9 | VH3/3-23/D5/5-24/RF3/JH3 | EVQLLES-GGGLVQPGGSLRL SCAASG-FTFS | S------CAMN | WVRQAPGK GLEWVS | AISGS---GGSSFYADS VKG | RFTISRDNSKNTLYLQMNSL RAEDTAVYYCAK | RTPYD-----------VFDI | WGQGT MVTVS S |
| iPS:3 98474 | 21-225_17B10 | VH3/3-23/D5/5-24/RF3/JH3 | EVQLLES-GGGLVQPGGSLRL SCAASG-FTFR | S------YAMS | WVRQAPGK GLEWVS | VISGS---GGNTYFADS VKG | RFTISRDNSKNTLYLQMDSL RAEDTAVYYCAK | RGIPEA----------DAFDI | WGQGT MVTVS S |
| | Germline | VH1/1-02/D1/1-1/RF1/JH3 | | | | | | | H_FR4 |
| iPS:4 35745 | 21-225_175G3 | VH1/1-02/D1/1-1/RF1/JH3 | QVQVVQS-GAEVKKPGASVKV SCKASG-YTFT | G------YFMH | WVRQAPGQ GLEWMG | WIKPK---SGGTNCAQR FQG | RVTMTRDTSITTAYMELSRL RSDDTAVYYCVR | GGTIVTT---------NGVFDY | WGQGT MVTVS S |
| iPS:4 37270 | 21-225_178H4 | VH1/1-02/D1/1-1/RF1/JH3 | QVQLVQS-GAEVKKPGASVKV SCKASG-YTFT | G------YFMH | WVRQAPGQ GLEWMG | WIKPK---SGGTNCAQK FQG | RVTMTRCTSISTAYMELSRL RSDDTAVYYCVR | GGTIVTT---------NGVFDY | WGQGT MVTVS S |
| | Germline | VH3/3-23/D3/3-22/RF2/JH4 | | | | | | H_CDR3 | H_FR4 |
| iPS:4 35769 | 21-225_177B6 | VH3/3-23/D3/3-22/RF2/JH4 | EVQLLES-GGGLVQPGGSRRL SCEASG-FTFS | S------YAMS | WVRQAPGK GLEWVS | VISGS---GSNTYYVDS VKG | RFTISRDNSKNTLNLQMNSL RAEDSAVYYCTK | GYYDSSG---------YYYPFDF | WGQGT LVTVS S |
| | Germline | VH3/3-33/D3/3-22/RF2/JH1 | | | | | | H_CDR3 | H_FR4 |
| iPS:4 35771 | 21-225_177B11 | VH3/3-33/D3/3-22/RF2/JH1 | QVQLVES-GGGVVQPGRSLRL TCAASG-FTFS | S------YGMH | WVRQAPGK GLEWVA | IIWYD---GSYKYTDS VKG | RPTISRDNSKNTLYLQMNSL RAEDTAVYYCAR | ETYDFW----------SGYFVF | WGQGT LVTVS S |
| | Germline | VH3/3-23/D5/5-24/RF3/JH4 | H_FR1 | H_CDR1 | H_FR2 | H_CDR2 | H_FR3 | H_CDR3 | H_FR4 |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 35775 | 21-225_178A5 | VH3|3-23|D5|5-24|RF3|JH4 | EVHLLES-GGGLVQTGGSLRL SCAASG-FTFS | S-----YAMT | WVRQAPGK GLEWVS | VISGS---GGNTYADS VKG | RFTISRDNSKNTLYLQMNSL RAEDTAVYYCAR | RDGD----------YFDY | WGQGT LVTVS S |
| iPS:4 37214 | 21-225_48B12 | VH3|3-23|D5|5-24|RF3|JH4 | EVQLLES-GGGLVQPGGSLRL SCAASG-FTFS | S-----YAMN | WVRQAPGK GLEWVS | AISGR---GGNTFYADS VKG | RFTISRDNSKNTLYLQMNSL RAEDTAVYYCAK | RETYNWN--------YEGFDY | WGQGT LVTVS S |
| iPS:3 93028 | 21-225_25D7 | VH3|3-23|D5|5-24|RF3|JH4 | EVQLLES-GGGLVQPGGSLRL SCAASG-FTFS | S-----YAMS | WVRQTPGQ GLEWVS | AISGR---GGTFFYADS VKG | RFTISRDNSKNTLYLQMNSL RAEDTAVYYCAK | DGYGGN---------SFFDY | WGQGT LVTVS S |
| | VH3|3-23|D4|4-11|RF3|JH6 Germline | | | H_CDR1 | H_FR2 | H_CDR2 | H_FR3 | H_CDR3 | H_FR4 |
| iPS:4 35789 | 21-225_180C4 | VH3|3-33|D4|4-11|RF3|JH6 | QVQLVES-GGGLVQPGRSLRL SCAASG-FTFS | A------YGMH | WVRQAPGK GLEMVI | IIWYD---GSYKYADS VKG | RFAISRDNSKNTLYLQMNSL RAEDTAVYYCAR | TGVDPWD---------YYNGMDV | WGQGT TVTVS S |
| | VH3|3-23|D2|2-8|RF1|JH3 Germline | | | H_CDR1 | H_FR2 | H_CDR2 | H_FR3 | H_CDR3 | H_FR4 |
| iPS:4 35799 | 21-225_181G3 | VH3|3-23|D2|2-8|RF1|JH3 | EVQLLES-GGGLVQPGGSLRL SCAASG-FTFS | S------YAMS | WVRQAPGK GLEWVS | VISGS---GGNTFYGDS VKG | RFTISRDNSKNTLYLQMNSL RAEDTAVYYCAK | RETYDWG---------SDAFDI | WGQGT MVTVS S |
| | VH3|3-30.3|D5|5-18|RF2|JH3 | | | H_CDR1 | H_FR2 | H_CDR2 | H_FR3 | H_CDR3 | H_FR4 |
| iPS:4 35811 | 21-225_183H6 | VH3|3-30.3|D5|5-18|RF2|JH6 | QVQLVES-GGGVVQPGRSLRL SCAASG-FTFS | S------YGMH | WVRQAPGK GLEWVA | IISYA---GSTKFYADS VKG | RFTISRDNSKNIYLQMNSL RAEDTAVYYCVR | RPPQWLV---------EGYGMDV | WGQGT TVTVS S |
| iPS:4 36754 | 21-225_155G3 | VH3|3-30.3|D5|5-18|RF2|JH6 | QVQLVES-GGGVVQPGRSLRL SCTASG-FTFS | S------YGMH | WVRQAPGK GLEWVA | VISYD---GSNKYADS VKG | RFTISRDNSKNTLYLQMNSL RAEDTAVYYCAK | DTERWLP---------YSYGMDV | WGQGT TVTVS S |
| iPS:4 48908 | 21-225_50G9 | VH3|3-30.3|D5|5-18|RF2|JH6 | QVQLVES-GGGVVQPGRSLRL SCAASG-FIFS | S------YGMH | WVRQAPGK GLEWVA | VISQD---GIIRYADS VKG | RFTISRDNSKNTLYLQMNSL RAEDTAVYYCAK | DVKQWLV---------RTYGMDV | WGQGT TVTVS S |
| | VH3|3-30.3|D5|5-19|RF1|JH5 Germline | | | H_CDR1 | H_FR2 | H_CDR2 | H_FR3 | H_CDR3 | H_FR4 |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 35813 | 21-225_183A12 | VH3J3-30.3/D6|6-19|RF1/JH5 | QVQLVES-GGGVVQPGRSLRL SCAASG-FTFS | S-----YGMH | WVRQAPGK GLEWVA | VISSA----GSNKYIADS VKG | RFTISRDNSKNTLYLQMNSL RAEDTAVYYCAR | RYSSGW------DWFDP | WGQGT LVTVS S |
| | | Germline | H_FR1 | H_CDR1 | H_FR2 | H_CDR2 | H_FR3 | H_CDR3 | H_FR4 |
| | VH3J3-21/D3J3-10|RF3/JH4 | | | | | | | |
| iPS:4 35815 | 21-225_190G10 | VH3J3-21/D3J3-10|RF3/JH4 | EVQLVES-GGGLVKPGGSLRL SCAASG-FTFR | D-----YSMN | WVRQAPGK GLEWVS | SISSG----SGYIHYADS VKG | RFTISRDNAKNSLYLQMNSL RAEDTAVYYCAR | ATMA---------LDY | WGQGT LVTVS S |
| iPS:4 35865 | 21-225_191A5 | VH3J3-21/D3J3-10|RF3/JH4 | EIQVVES-GGGLVKPGGSLRL SCAASG-FTFR | D-----YSMN | WVRQAPGK GLEWVS | SISSG----SGYIYYADS VKG | RFTISRDNAKNSLYLQMNSL RAEDTAVYYCAR | ATMA---------LDY | WGQGA LVTVS S |
| iPS:4 36047 | 21-225_193B10 | VH3J3-21/D3J3-10|RF3/JH4 | EVQLVES-GGGLVKPGGSLRL SCAASG-FTFR | D-----YSMN | WVRQAPGK GLEWVS | SISSA----GGYIYYADS LKG | RFTISRDNAKNSLYLQMNSL RAEDTAVYYCAR | ATMA---------LDY | WGQGT LVTVS S |
| iPS:4 36122 | 21-225_196G10 | VH3J3-21/D3J3-10|RF3/JH4 | EVQLVES-GGGLVKPGGSLRL SCAASG-FTFR | D-----YSMN | WVRQAPGK GLEWVS | SISSG----SGYIHYADS VKG | RFTISRDNAKNSLYLQMNSL RAEDTAVYYCAR | ATMA---------LDY | WGQGT LVTVS S |
| | | Germline | H_FR1 | H_CDR1 | H_FR2 | H_CDR2 | H_FR3 | H_CDR3 | H_FR4 |
| | VH4J4-59/D4J4-17|RF2/JH6 | | | | | | | |
| iPS:4 35817 | 21-225_190B11 | VH4J4-59/D4J4-17|RF2/JH6 | QVQLQES-GPGLVKPSETLSL TCTVSG-GSIN | N-----YYWS | WIRQPAGK GLEWIG | RIYT----SGSTNYNPS LKS | RVTMSVDTSKNQFSLKLSSV TAADTAVHYCAR | DRGYYG------YYGMDV | WGQGT TVTVS S |
| iPS:4 35917 | 21-225_190D5 | VH4J4-59/D4J4-17|RF2/JH6 | QVQLQES-GPGLVKPSETLSL TCTVSG-GSIN | N-----YYWS | WIRQPAGK GLEWIG | RIYA----SGSTNYNPS LKS | RVTMSIDTSKNQFSLKLSSV TAADTAVYYCAR | DRGYYG------YYGMDV | WGQGT TVTIS S |
| iPS:4 36056 | 21-225_194C3 | VH4J4-59/D4J4-17|RF2/JH6 | QVQLQES-GPGLVKPSETLSL TCTVSG-GSIN | N-----YYWS | WIRQPAGK GLEWIG | RIYA----SGSTNYNPS LKS | RVTMSIDTSKNQFSLKLSSV TAADTAVHYCAR | DRGYYG------YYGMDV | WGQGT TVTIS S |
| iPS:4 36220 | 21-225_200F8 | VH4J4-59/D4J4-17|RF2/JH6 | QVQLQES-GPGLVKPSETLSL TCTVSG-GSIN | N-----YYWS | WIRQPAGK GLEWIG | RIYT----SGSTNYNPS LKS | RVTMSVDTSKNQFSLKLSSV TAADTAVHYCAR | DRGYYG------YYGMDV | WGQGT TVTVS S |
| | | Germline | H_FR1 | H_CDR1 | H_FR2 | H_CDR2 | H_FR3 | H_CDR3 | H_FR4 |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35821 | 21-225_190E11 | VH3/3-30/D4/4-17/RF2/JH6 | QVQLVES-GGGVVQPGRSLRL SCTASG-FTFS | N-----YGMH | WVRQAPGK GLEWVA | IINFD---GSNKYIADS VKG | RFTISRDNSKNTLYLQMNSL RAEDTAVYYCAK | AQGVIY------YVMDV | WGQGT TVTVS S |
| | | Germline | | | | | | | |
| | VH3/3-23/D5/5-12/RF3/JH5 | | | | | | | | H_FR4 |
| iPS:4 35823 | 21-225_190F11 | VH3/3-23/D5/5-12/RF3/JH5 | EVQLLDS-GGGLGQPGGSLRL SCAASG-FTFD | S-----YAMN | WVRQAPGK GLEWVS | TISGT---GRRTYYADS VKG | RFTISRDNSKNTLYLQMNSL RAEDTAVYYCAK | EEDYDS------SGPGFDP | WGQGT LVTVS S |
| iPS:4 35867 | 21-225_191E5 | VH3/3-23/D5/5-12/RF3/JH5 | EVQLLDS-GGGLGQPGGSLRL SCAASG-FTFD | S-----YAMN | WVRQAPGK GLEWVS | TISGT---GRRTYYADS VKG | RFTISRDNSKNTLYLQMNSL RAEDTAVYYCAK | EEDYDS------SGPGFDP | WGQGT LVTVS S |
| iPS:4 35929 | 21-225_190D9 | VH3/3-23/D5/5-12/RF3/JH5 | EVQLLDS-GGGLGQPGGSLRL SCAASG-FTFD | S-----YAMS | WVRQAPGK GLEWVS | TISGT---GRRTYYADS VKG | RFTISRDNSKNTLYLQMNSL RAEDTAVYYCAK | EEDYDS------SGPGFDP | WGQGT LVTVS S |
| iPS:4 35935 | 21-225_190H8 | VH3/3-23/D5/5-12/RF3/JH5 | GVQLLDS-GGGLGQPGGSLRL SCAASG-FTFD | S-----YAMS | WVRQAPGK GLEWVS | TISGT---GRRTYYADS VKG | RFTISRDNSKNTLYLQMNSL RAEDTAVYYCAK | EEDYDS------SGPGFDP | WGQGT LVTVS S |
| | | Germline | H_FR1 | H_CDR1 | H_FR2 | H_CDR2 | H_FR3 | H_CDR3 | H_FR4 |
| | VH4/4-39/D3/3-9/RF1/JH4 | | | | | | | | |
| iPS:4 35827 | 21-225_190H11 | VH4/4-39/D3/3-9/RF1/JH4 | QLQLQES-GPGLVKPSETLSL TCTVSG-GSIR | S-----YHWS | WIRQPAGK GLEWIG | LIYT----SRSTYNPS LKS | RVILSVDTSKNQFSLKLSSV TAADTAVYYCAR | LRYNWN------EPYFDY | WGQGT LVTVS S |
| iPS:4 35853 | 21-225_191E3 | VH4/4-39/D3/3-9/RF1/JH4 | QLQLQES-GPGLVKPSETLSL TCTVSG-GSIR | S-----YHWS | WIRQPAGK GLEWIG | LIYT----SRSTYNPS LKS | RVTMSVDTSKNQFSLKLSSV TAADTAVYYCAR | LRYNWN------EPYFDY | WGQGT LVTVS S |
| iPS:4 35871 | 21-225_191E6 | VH4/4-39/D3/3-9/RF1/JH4 | QLQLQES-GPGLVKPSETLSL TCTVSG-GSIR | S-----YHWS | WIRQPAGK GLEWIG | LIYT----SRSTYNPS LKS | RVTMSVDTSKNQFSLKLSSV TAADTAVYYCAR | LRYNWN------EPYFDF | WGQGT LVTVS S |
| iPS:4 35927 | 21-225_190E7 | VH4/4-39/D3/3-9/RF1/JH4 | QLQLQES-GPGLVKPSETLSL TCTVSG-GSIR | S-----YHWS | WIRQPAGK GLEWIG | HIYT----SRSTYNPS LKS | RVTISVDTSKNQFSLKLSSV TAIDTAVYYCAR | LRYNWN------EPYFDY | WGQGT LVTVS S |
| iPS:4 35999 | 21-225_192F9 | VH4/4-39/D3/3-9/RF1/JH4 | QLQLQES-GPGLVKPSETLSL TCTVSG-GSIR | S-----YHWS | WIRQPAGK GLEWIG | LIYT----SRSTYNPS LKS | RVTMSVDTSKNQFSLKLNSV TAADTAVYYCAR | LRYNWN------EPYFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36060 | 21-225_194F4 | VH4/4-39/D3/3-9/RF1/JH4 | QLQLQES-GPGLVKPSETLSL TCIVSG-GSIS | S-----YHWS | WIRQPAGK GLEWIG | LIYT----SRSTNINPS LKS | RVTMSVDRSKSQFSLKLSSV TAADTAVYYCAR | LRYNWN--------FPYFDY | WGQGT LVTVS S |
| iPS:4 36193 | 21-225_198A10 | VH4/4-39/D3/3-9/RF1/JH4 | QLQLQES-GPGLVKPSETLSL TCIVSG-GSIR | S-----YHWS | WIRQPAGK GLEWIG | HIYT----SRSTNINPS LKS | RVTISVDTSKNQFSLKLSSV IATDTAVYYCAR | LRYNWN--------FPYFDY | WGQGT LVTVS S |
| | Germline | | | | | | | | |
| | VH4/4-30.1/D5/5-24/RF3/JH2 | | | | | | | | |
| iPS:4 35829 | 21-225_190B12 | VH4/4-30.1/D5/5-24/RF3/J H2 | QVQLQES-GPGLVKPSQTLSL TCIVSG-GSIS | SG---GYYWN | WIRQHPGK GLEWIG | YIYY----SGSTYINPS LKS | RVTISVDTSKNQFFLKLNSV TAADTAVYYCAR | SGYNWD--------AGVDP | WGRGT LVTVS S |
| | Germline | | | | | | | | |
| | VH3/3-33/D4/4-11/RF2/JH6 | | | | | | | | |
| iPS:4 35835 | 21-225_190F12 | VH3/3-33/D4/4-11/RF2/J H6 | QVQLVES-GGGVVQPGRSLRL SCAASG-FTFR | N-----YGMH | WVRQAPGK GLEWVA | VIWFD----GSNDYYADS VKG | RFTISRDNSKNTLSLQMNSL RAEDTAVYYCAR | DRSVGY--------DGLDV | WGQGT TVTVS S |
| iPS:4 35861 | 21-225_190A5 | VH3/3-33/D4/4-11/RF2/J H6 | QVQLVES-GGGVVQPGRSLRL SCAASG-FTFS | S-----YGMH | WVRQAPGK GLEWVA | VIWYD----GSNKNYADS VKG | RFTISRDNSKNTLYLQMNSL RAEDTAVYYCAR | DFSVGY--------DGMDV | WGQGT TVTVS S |
| iPS:4 35937 | 21-225_190H9 | VH3/3-33/D4/4-11/RF2/J H6 | QVQLVES-GGGVVQPGRSLRL SCAASG-FTFS | N-----YGMH | WVRQAPGK GLEWVA | VIWYD----GSNKNYVQS VKG | RFTISRDNSKNTLYLQMNSL RAEDTAVYYCAR | DRSVGY--------DGLDV | WGQGT TVTVS S |
| iPS:4 35977 | 21-225_192E4 | VH3/3-33/D4/4-11/RF2/J H6 | QVQLVES-GGGVVQPGRSLRL SCAASG-FTFR | S-----YGMH | WVRQAPGK GLKWVA | VIWYD----GSNKNYVQS VRG | RFTISRDNSKNTLYLQMNSL RAEDTAVYYCAR | DRSVGY--------DGMDV | WGQGT TVTVS S |
| iPS:4 36001 | 21-225_192C10 | VH3/3-33/D4/4-11/RF2/J H6 | QVQLVES-GGGVVQPGRSLRL SCAASG-FTFS | N-----YGMH | WVRQAPGK GLEWVA | VIWYD----GSNDYYADS VKG | RFTISRDNSKNTLYLQMNSL RAEDTAVYYCAR | DRSVGY--------DGLDV | WGQGT TVTVS S |
| iPS:4 36066 | 21-225_194B7 | VH3/3-33/D4/4-11/RF2/J H6 | QVQLVES-GGGVVQFGRSLRL SCASSG-FTFS | S-----YGMH | WVRQAPGK GLEWVA | VIWYD----GSNKNYADS VKG | RFTISRDNSKNTLYLQMNSL RAEDTAVYYCAR | DRSKGY--------DGMDV | WGQGT TVTVS S |
| iPS:4 36078 | 21-225_194H12 | VH3/3-33/D4/4-11/RF2/J H6 | QVQLVES-CGGVVQPGRSLRL SCAASG-FTFR | N-----YGMH | WVRQAPGK GLEWVA | VIWFD----GSNDYYADS VKG | RFTISRDNSKNTLSLQMNSL RAEDTAVYYCAR | DRSVGY--------DGLDV | WGQGT TVTVS S |

Figure 51 (Continued)

| | | | | | | | | |
|---|---|---|---|---|---|---|---|---|
| iPS:4 36140 | 21-225_197G3 | VH3J3-33/D4J4-11/RF2/J H6 | QVQLVES-GGGVVQPGRSLRL SCVASG-FTFS | S------HGMH | WVRQAPGK GLEWVA | VIWYD---GSNKNIADS VKG | RFTISRDNSKNTLYLQMNSL RAEDTAVYYCAR | DPSVGY------EGMDV | WGQGT TVTVS S |
| iPS:4 36167 | 21-225_197E11 | VH3J3-33/D4J4-11/RF2/J H6 | QVQLVES-GGGVVQPGRSLRL SCAASG-FTFR | N------YGMH | WVRQAPGK GLEWVA | VIWFD---GSNDYYADS VKG | RFTISRDNSKNTLSLQMNSL RAEDTAVYYCAR | DRSVGY------DGLDV | WGQGT TVTVS S |
| iPS:4 36292 | 21-225_205H3 | VH3J3-33/D4J4-11/RF2/J H6 | QVQLVES-GGGVVQPGRSLRL SCAASG-FTFS | S------YGMH | WVRQAPGK GLEWVA | VIWYD---GSNKYYADS VKG | RFTISRDNSKNTLYLQMNSL RAEDTAVYYCAR | DRSVGY------DGTDV | WGQGT TVTVS S |
| iPS:4 36802 | 21-225_171E12 | VH3J3-33/D4J4-11/RF2/J H6 | QVQLVES-GGGVVQPGRSLRL SCAASG-FTFS | S------YGMH | WVRQAPGK GLEWVA | VIWND---GGNKYNGDS VKG | RFTISRDNSKNTLYLQMNSL RAEDTAVYYCAR | DRTYYSGSGSP------PIYYYYGMDV | WGQGT TVTVS S |
| iPS:4 36816 | 21-225_179H5 | VH3J3-33/D4J4-11/RF2/J H6 | QVQLVES-GGGVVQPGRSLRL SCAASG-FTFS | S------YGMH | WVRQAPGK GLEWVA | VIWYD---GSNEYYADS VKG | RFTISRDNSKNTLYLQMNSL RAEDTAVYYCAR | DIRNYY------YGLDV | WGQGT TVTVS S |
| iPS:4 36960 | 21-225_198D2 | VH3J3-33/D4J4-11/RF2/J H6 | QVQLVES-GGGVVQPGRSLRL SCAASG-FTFR | S------YGMH | WVRQAPGK GLEWVA | VIIYD---GSYKYYADS VKG | RFTISRDNSKNTLYLQMNSL RAEDTAVYYCAR | TYSG------GMDV | WGQGT TVTVS S |
| iPS:4 36974 | 21-225_190H7 | VH3J3-33/D4J4-11/RF2/J H6 | QVQLVES-GGGVVQPGRSLRL SCAASG-FNFR | S------YGMH | WVRQAPGK GLEWVA | VIIYD---GSYKYYADS VKG | RFTISRDNSKNTLYLQMNSL RAEDTAVYYCAR | TYSG------GMDV | WGQGT TVTVS S |
| iPS:4 36982 | 21-225_190D10 | VH3J3-33/D4J4-11/RF2/J H6 | QVQLVES-GGGVVQPGRSLRL SCAASG-FTFR | S------YGMH | WVRQAPGK GLEWVA | VIIYD---GSYKYYADS VKG | RFTISRDNSKNTLYLQMNSL RAEDTAVYYCAR | TYSG------GMDV | WGQGT TVTVS S |
| iPS:4 37274 | 21-225_196D4 | VH3J3-33/D4J4-11/RF2/J H6 | QVQVVES-GGGVVQPGRSLRL SCAASG-FTFS | S------YGMH | WVRQAPGK GLEWVA | VIWYD---GSNRNYADS VKG | RFTISRDNSKNTLYLQMNSL RVEDTAVYYCAR | DRSKGY------EGMDV | WGQGT TVTVS S |
| iPS:3 92664 | 21-225_20F6 | VH3J3-33/D4J4-11/RF2/J H6 | QVQLVES-GGGVVQPGRSLRL SCAASG-FTFS | S------YGMH | WVRQAEGK GLEWGA | VIWHD---GSNKYYADS VKG | RFTISRDNAKNTLYLQMNSL RAEDTAVYYCAR | DLSMG------GMDV | WGQGT TVTVS S |
| iPS:3 92738 | 21-225_18G4 | VH3J3-33/D4J4-11/RF2/J H6 | QVQLVES-GGGVVQPGRSLRL SCAASG-FTFS | S------YGMH | WVRQAEGK GLEWGA | IIWYD---GSNKYYADS VKG | RFTISRDNSKNTLYLQMNSL RAEDTAVYYCAR | DLSMG------GMDV | WGQGT TVTVS S |
| iPS:3 92798 | 21-225_22C7 | VH3J3-33/D4J4-11/RF2/J H6 | QVQLVES-GGGVVQPGRSLRL SCAASG-FTFS | S------YGMH | WVRQAPGK GLEWVA | VIWHD---GSNKYYADS VKG | RFTISRDNAKNTLYLQMNSL RAEDTAVYYCAR | DLSMG------GMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 92956 | 21-225_27A11 | VH3|3-33|D4|4-11|RF2|JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYHCAR | DSSPY------------GMDV | WGQGT TVTVS S |
| iPS:3 92994 | 21-225_26G11 | VH3|3-33|D4|4-11|RF2|JH6 | QVQLVES-GGGVVQPGRSLRLSCAASG-FTFS | S-----YGMH | WVRQAPGK GLEWVA | VIWYD---GSNKYYADS VKG | RFTISRDNSKNTLYLQMNSL RAEDTAVYYCAR | RYSNSW-------SGGMDV | WGQGT TVTVS S |
| iPS:3 93014 | 21-225_26D12 | VH3|3-33|D4|4-11|RF2|JH6 | QVQLVES-GGGVVQPGRSLRLSCAASG-FTFS | S-----YGMH | WVRQAPGK GLEWVA | VIWYD---GSNEYYADS VKG | RFTISRDNSKNTLYLQMNSL RAADTAVYYCAR | DSSPY------------GMDV | WGQGT TVTVS S |
| iPS:3 93152 | 21-225_25B3 | VH3|3-33|D4|4-11|RF2|JH6 | QVQLVES-GGGVVQPGRSLRLSCAASG-FTFS | S-----YGMH | WVRQAPGK GLEWGA | VIWYD---GSNKYYADS VKG | RFTISRDNSKNTLYLQMNSL RAEDTAVYYCAR | DSSPY------------GMDV | WGQGT TVTVS S |
| iPS:3 93840 | 21-225_3F8 | VH3|3-33|D4|4-11|RF2|JH6 | QVQLVES-GGGVVQPGRSLRLSCAASG-FTFS | S-----YGMH | WVRQAPGK GLEWVA | VIWHD---GSNKYYADS VKG | RFTISRDNAKNTLYLQMNSL RAEDTAVYYCAR | DLSMG------------GMDV | WGQGT TVTVS S |
| iPS:3 93930 | 21-225_7E11 | VH3|3-33|D4|4-11|RF2|JH6 | QVQLVES-GGGVVQPGRSLRLSCAASG-FTFS | S-----FGMH | WVRQAPGK GLEWVA | IIWHD---GSNKYYADS VKG | RFTISRDNSKNTLYLQMNSL RAEDTAVYYCAR | DLSMG------------GMDV | WGQGT TVTVS S |
| iPS:3 93964 | 21-225_6G1 | VH3|3-33|D4|4-11|RF2|JH6 | QVQLVES-GGGVVQPGRSLRLSCAASG-PIFS | S-----YGMH | WVRQAPGK GLEWVA | IIWYD---GSNKYYADS VKG | RFTISRDNSKNTLYLQMNSL RAEDTAMYYCAR | DLSMG------------GMDV | WGQGT TVTVS S |
| iPS:3 94012 | 21-225_15A3 | VH3|3-33|D4|4-11|RF2|JH6 | QVQLVES-GGGVVQPGRSLRLSCAASG-FTFS | S-----YGIH | WVRQAPGK GLEWVA | VIWHD---GSNKYYADS VKG | RFTISRDNSKNTLYLQMNSL RAEDTAVYYCAR | DLSMG------------GMDV | WGQGT TVTVS S |
| iPS:3 94016 | 21-225_13D4 | VH3|3-33|D4|4-11|RF2|JH6 | QVQLVES-GGGVVQPGRSLRLSCAASG-FTFS | S-----YGMH | WVRQAPGK GLEWVA | VIWHD---GSNKYYVDS VKG | RFTISRDNSKNTLYLQMNSL RAEDTAVYYCAR | DLSMG------------GMDV | WGQGT TVTVS S |
| iPS:3 94083 | 21-225_16E6 | VH3|3-33|D4|4-11|RF2|JH6 | QVQLVES-GGGVVQPGRSLRLSCAASG-FTFS | S-----YGMH | WVRQAPGK GLEWVA | VIWHD---GSNKYYADS VKG | RFTISRDNSKNTLNLQMNSL RAEDTAVYYCAR | DLSMG------------GMDV | WGQGT TVTVS S |
| VH4|4-59|D3|3-9|RF1|JH4 | | Germline | | | | | | | |
| iPS:4 35839 | 21-225_191B1 | VH4|4-59|D3|3-9|RF1|JH4 | QVQLQES-GPGLVKPSETLSLTCTVSG-GSIS | S-----YHWS | WIRQPAGK GLEWIG | HIYT----SGSTKYNPS LKS | RVTMSVDISKNQFSLKLSSV TAADTAVYYCAR | LRYNWN---------FPFFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36158 | 21-225_197G8 | VH4J4-59/D3J3-9|RF1/JH4 | QVHLQES-GPGLVKPSETLSL TCIVSG-GSIS | A-----YSWS | WIRQPAGK GLEWIG | RLSP----GGSTNFNPS LKS | RVTMSVDTSKNQFSLRLSSV TAADTAVYYCAR | LRYNWN------FPYFDY | WGQGA LVTVS S |
| | | Germline | | | | | | | H_FR4 |
| iPS:4 35843 | 21-225_191F1 | VH4J4-30.1/D3J3-22|RF2/J H6 | QVQLQES-GPGLVKPSQTLSL TCTVSG-GSIN | SG----GYYWN | WIRQHPGK GLEWIG | YIFY----SGSTYYNPS LKS | RVTISVDTSKNQFSLKLSSV TAADTAVYYCAR | GDYDGSGSY------HYYYGMDV | WGQGT TVTVS S |
| iPS:4 35847 | 21-225_191A3 | VH4J4-30.1/D3J3-22|RF2/J H6 | QVQLQES-GPGLVKPSQTLSL TCTVSG-GSIN | SG----DYYWN | WIRQHPGK GLEWIG | YIFY----SGSTYYNPS LKS | RVTISVDTSKNQFSLKLSSV TAADTAVYYCAR | GDYDGSGSY------HYYYGMDV | WGQGT TVTVS S |
| iPS:4 35851 | 21-225_191D3 | VH4J4-30.1/D3J3-22|RF2/J H6 | QVQLKES-GPGLVKPSQTLSL TCTVSG-GSIN | SG----DYYWN | WIRQHPGK GLEWIG | YIFY----SGSTYYNPS LKS | RVTISVDTSKNQFSLKLSSV TAADTAVYYCAR | GDYDGSGSY------HYYYGMDV | WGQGT TVTVS S |
| iPS:4 35905 | 21-225_190A3 | VH4J4-30.1/D3J3-22|RF2/J H6 | QVQLQES-GPGLVKPSQTLSL TCTVSG-GSIS | SG----GYYWN | WIRQHPGK GLEWIG | FIFY----SGSTYYNPS LKS | RVTISVDTSKNQFSLKLSNV TAADTAVYYCAR | GDYDGSGSY------HYYYGMDV | WGQGT TVTVS S |
| iPS:4 35911 | 21-225_190B4 | VH4J4-30.1/D3J3-22|RF2/J H6 | QVQLQES-GPGLVKPSQTLSL TCTVSG-GSIS | SG----DYYWN | WIRQHPGK GLEWIG | YIFY----SGSTYYNPS LKS | RITISVDTSKNQFSLKLSSV TAADTAVYYCAR | GDYDGSGSY------HYYYGMDV | WGQGT TVTVS S |
| iPS:4 35913 | 21-225_190A7 | VH4J4-30.1/D3J3-22|RF2/J H6 | QVQLQES-GPGLVNPSQTLSL TCTVSG-GSIS | SG----VYYWS | WIRQHPGK GLEWIG | NIYY----SGSTYYNPS LKS | RVTISVDTSKNQFSLKLSSV IVADTAVYYCAR | GDYDGSGSY------HYYGLDV | WGQGT TVTVS S |
| iPS:4 35939 | 21-225_191H7 | VH4J4-30.1/D3J3-22|RF2/J H6 | QVQLQES-GPGLVKPSQTLSL TCTVSG-GSIN | SG----DYYWN | WIRQHPGK GLEWIG | YIFY----SGSTYYNPS LKS | RVTISVDTSKNQFSLKLSSV TAADTAVYYCAR | GDYDGSGSY------HYYYGMDV | WGQGT TVTVS S |
| iPS:4 35967 | 21-225_192B3 | VH4J4-30.1/D3J3-22|RF2/J H6 | QVQLQES-GPGLVKPSQTLSL TCTVSG-GSIS | SG----DYYWN | WIRQHPGK GLEWIG | FIFY----SGSTYYNPS LKS | RVTISVDTSKNQFSLKLSSV TVADTAVYYCAR | GDYDGSGSY------HHYYGMDV | WGQGT TVTVS S |
| iPS:4 35973 | 21-225_192H3 | VH4J4-30.1/D3J3-22|RF2/J H6 | QVQLQES-GPGLVKPSQTLSL TCTVSG-GSIS | SV----SYYWS | WIRQHPGK GLEWIG | NLYY----SGSTYYNPS LRS | RATISVDTSKNQFSLKLSSV TAADTAVYYCTR | GDYDGSGSY------HYYHGMDV | WGQGT TVTVS S |
| iPS:4 36007 | 21-225_192G12 | VH4J4-30.1/D3J3-22|RF2/J H6 | QVQLQES-GPGLVKPSQTLSL TCTVSG-GSIS | SG----VYHWS | WIRQHPGK GLEWIG | NIHY----SGSTYYNPS LKS | RVTISVDTSKNQFSLKLSSV TAADTAVYYCAR | GDYDGSGSY------HYYYGMDV | WGQGT TVTVS S |

Figure 51 (Continued)

| | | | | | | | | |
|---|---|---|---|---|---|---|---|---|
| iPS:4 36009 | 21-225_193A1 | VH4|4-30.1|D3|3-22|RF2|J H6 | QVQLQES-GPGLVKPSQTLSL TCTVSG-GSIS | SG---VYYWS | WIRQHPGK GLEWIG | NIYY----SGSTYNNPS LKS | RLTISADISKNQFSLKLSSV TAADTAVYYCAR | GDYDGSGSY-------HYYYGMDV | WGQGT TVTVS S |
| iPS:4 36011 | 21-225_193B1 | VH4|4-30.1|D3|3-22|RF2|J H6 | QVQLQES-GPGLVKPSQTLSL TCTVSG-GSIS | SG---VYYWS | WIRQHPGK GLEWIG | NIYY----SGSTYNNPS LKS | RVTISVDTSKNQFSLKLSSV TAADTAVYYCAR | GDYDGSGSY-------HYYYGMDV | WGQGT TVTVS S |
| iPS:4 36017 | 21-225_193F3 | VH4|4-30.1|D3|3-22|RF2|J H6 | QVQLQES-GPGLVKPSQTLSL TCTVSG-GSIN | SG---DYYWN | WIRQHPGK GLEWIG | YIFY----SGSTYYNPS LKS | RVTISVDTSKNQFSLKLSSV TAADTAVYYCAR | GDYDGSGSY-------HYYYGMDV | WGQGT TVTVS S |
| iPS:4 36029 | 21-225_193H6 | VH4|4-30.1|D3|3-22|RF2|J H6 | QVQLQES-GPGLVKPSQTLSL TCTVSG-GSIN | SG---DYYWN | WIRQHPGK GLEWIG | YIFY----SGSTYYNPS LKS | RVSISVDTSKNQFSLKLSSV TAADTAVYYCAR | GDYDGSGSY-------HYYYGMDV | WGQGT TVTVS S |
| iPS:4 36035 | 21-225_193C8 | VH4|4-30.1|D3|3-22|RF2|J H6 | QVQLQES-GPGLVKPSQTLSL TCTVSG-GSIS | SG---GYYWN | WIRQHPGK GLEWIG | YIFY----SGSTYYNPS LKS | RVTISVDTSKNQFSLKLSSV TAADTAVYYCAR | GDYDGSGSY-------HYYYGMDV | WGQGT TVTVS S |
| iPS:4 36037 | 21-225_193D8 | VH4|4-30.1|D3|3-22|RF2|J H6 | QVQLQES-GPGLVKPSQTLSL TCTVSG-GSIN | SG---GYYWN | WIRQHPGK GLEWIG | FIFY----SGSTYYNPS LKS | RVTISVDTSKNQFSLKLSSV TAADTAVYYCAR | GDYDGSGSY-------HYYYGMDV | WGQGT TVTVS S |
| iPS:4 36041 | 21-225_193G8 | VH4|4-30.1|D3|3-22|RF2|J H6 | QVQLQEK-GPGLVKPSQTLSL TCTVSG-GSVS | SG---VYYWS | WIRQHPGK GLEWIG | NIYY----SGSTYNNPS LKS | RVTISVDTSKNQFSLKLNSV TAADTAVYYCAR | GDYDGSGSY-------HFYYGLDV | WGHGT TVTVS S |
| iPS:4 36062 | 21-225_194E5 | VH4|4-30.1|D3|3-22|RF2|J H6 | QVQLQES-GPGLVKPSQTLSL TCTVSG-GSIN | SG---DYYWN | WIRHHPGK GLEWIG | YIFY----SGSTYYNPS LKS | RVTISVDTSKNQFSLKLSSV TAADTAVYYCAR | GDYDGSGSY-------HYYYGMDV | WGQGT TVTVS S |
| iPS:4 36064 | 21-225_194E6 | VH4|4-30.1|D3|3-22|RF2|J H6 | QVQLQES-GPGLVKPSQTLSL TCTVSG-DSIN | SG---DYYWN | WIRQHPGK GLEWIG | FIFY----SGSTYYNPS LKS | RVTISIDISKNQFSLKLSSV NVADTAVYYCAR | GDYDGSGSY-------HYYYGMDV | WGQGT TVTVS S |
| iPS:4 36134 | 21-225_196H12 | VH4|4-30.1|D3|3-22|RF2|J H6 | QVQLQES-GPGLVKPSQTLSL TCTVSG-GSIS | SG---VYYWS | WIRQHPGK GLEWIG | NIYY----SGSTYNNPS LKS | RITISVDTSKNQFSLKLSSV TAADTAVYYCAR | GDYDGSGSY-------HYYYGLDV | WGQGT TVTVS S |
| iPS:4 36146 | 21-225_197F4 | VH4|4-30.1|D3|3-22|RF2|J H6 | QVQLQES-GPGLVKPSQTLSL TCTVSG-GSIS | SG---DYYWN | WIRQHPGK GLEWIG | YIFY----SGSTYYNPS LKS | RITISVDISKNQFSLKLSSV TAADTAVYYCAR | GDYDGSGSY-------HYYYGLDV | WGQGT TVTVS S |
| iPS:4 36177 | 21-225_198B1 | VH4|4-30.1|D3|3-22|RF2|J H6 | QVQLKES-GPGLVKPSQTLSL TCTVSG-GSIN | SG---DYYWN | WFRQHPGK GLEWIG | YIFH----SGSTYYNPS LKS | RVTVSVDTSKNQFSLKLSSV TAADTAVYYCAR | GDYDGSGSY-------HYYYGMDV | WGRGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36179 | 21-225_198E1 | VH4/4-30.1/D3/3-22/RF2/J H6 | QVQLQES-GPGLVKPSQTLSL TCTVSG-GSIN | SG---GYYWN | WIRQHPGK GLEWIG | FIFY----SGSTYYNPS LKS | RLSISVDTSKNQFSLKLSSV TAADTAVYYCAR | GDYDGGSSY------HYYYGMDV | WGQGT TVTVS S |
| iPS:4 36197 | 21-225_199C2 | VH4/4-30.1/D3/3-22/RF2/J H6 | QVQLQES-GPGLVKPSQTLSL TCTVSG-GSIS | SG---DYYWN | WLRQHPEK GLEWIG | YIFY----SGSTYYNPS LKS | RVTISVDTSMTQFSLKLISV TAADTAVYYCAR | GDYDGSSY------HYYYGMDV | WGQGT TVTVS S |
| iPS:4 36207 | 21-225_199C7 | VH4/4-30.1/D3/3-22/RF2/J H6 | QVQLQES-GPGLVKPSQTLSL TCTVSG-GSIN | SG---GYYWN | WIRQHPGK GLEWIG | FIFY----SGSTYYNPS LKS | RVSISVDTSKNQFSLKLSSV TAADTAVYYCAR | GDYDGSSY------HYYYGMDV | WGQGT TVTVS S |
| iPS:4 36226 | 21-225_200F10 | VH4/4-30.1/D3/3-22/RF2/J H6 | QVQLQES-GPGLVKPSQTLSL TCTVSG-GSIS | SG---DYYWN | WLRQHPEK GLEWIG | YIFY----SGSTYYNPS LKS | RLTISVDTSMTQFSLKLISV TAADTAVYYCAR | GDYDGSSY------HYYYGMDV | WGQGT TVTVS S |
| | Germline | VH4/4-30.4/D3/3-22/RF2/J H6 | H_FR1 | H_CDR1 | H_FR2 | H_CDR2 | H_FR3 | H_CDR3 | H_FR4 |
| iPS:4 35849 | 21-225_191C3 | VH4/4-30.4/D3/3-22/RF2/J H6 | QVQLQES-GPGLVKPSQTLSL TCTVSG-GSIS | SG---DYYWN | WIRQLPGK GLEWIG | YIFY----SGSTYYNPS LKS | RLTISVDTSKNQFSLKLNSV TAADTAVYYCAR | GDYDGSSY------HFYYGMDV | WGQGT TVTVS S |
| iPS:4 36015 | 21-225_193D3 | VH4/4-30.4/D3/3-22/RF2/J H6 | QVQLQES-GPGLVKPSQTLSL TCTVSG-GSIS | SG---DYYWN | WIRQLPGK GLEWIG | YIFY----SGSTYYNPS LKS | RLTISVDTSKNQFSLKLSSV TAADTAVYYCTR | GDYDGSSY------HFYYGMDV | WGQGT TVTVS S |
| iPS:4 36049 | 21-225_193B12 | VH4/4-30.4/D3/3-22/RF2/J H6 | QVQLQES-GPGLVKPSQTLSL TCTVSG-GSIS | SA---DYYWN | WIRQLPGK GLEWIG | YIFY----SGSTYYNPS LKS | RLTISVDTSKNQFSLKLSSV IAADTAVYYCAR | GDYDGSSY------HFYYGMDV | WGQGT TVTVS S |
| iPS:4 36088 | 21-225_195C8 | VH4/4-30.4/D3/3-22/RF2/J H6 | QVQLQES-GPGLVKPSQTLSL TCTVSG-GSIS | SG---DYYWN | WIRQLPGK GLEWIG | YIFY----SGSTYYNPS LKS | RLTISVDTSKNQFSLKLSSV TAADTAVYYCAR | GDYDGSSY------HFYYGMDV | WGQGT TVTVS S |
| iPS:4 36195 | 21-225_198G10 | VH4/4-30.4/D3/3-22/RF2/J H6 | QVQLQES-GPGLVKPSQTLSL TCTVSG-GSIS | SG---GYYWN | WIRQLPGK GLEWIG | YIFY----SGSTYYNPS LKS | RLTISVDTSKNQFSLKLSSV TAADTAVYYCAR | GDYDGSSY------HFYYGMDV | WGQGT TVTVS S |
| | Germline | VH4/4-30.1/D5/5-24/RF3/J H5 | H_FR1 | H_CDR1 | H_FR2 | H_CDR2 | H_FR3 | H_CDR3 | H_FR4 |
| iPS:4 35863 | 21-225_191H4 | VH4/4-30.1/D5/5-24/RF3/J H5 | QVQLQES-GPGLVKPSQTLSL TCTVSG-GSIS | SG---GYYWN | WIRQHPGK GLEWIG | YIFY----SGSTYYNPS LRS | RLTISIDTSKNQFSLKLISV TAADTAVYYCGR | SGYNWD------NGVDP | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35943 | 21-225_191C9 | VH4/4-30.1/D5/5-24/RF3/JH5 | QVQLQES-GPGLVKPSQTLSL TCIVSG-GSIS | SG---GYYWN | WIRQHPGK GLDWIG | YIYY----SGSTYYNPS LKS | RVTISVDTSKNQFSLKLNSV TAADTAVYYCAR | SGYNWD-------AGVDP | WGQGT LVTVS S |
| iPS:4 36094 | 21-225_195B10 | VH4/4-30.1/D5/5-24/RF3/JH5 | QVQLQES-GPGLVKPSQTLSL TCIVSG-GSIS | NS---GYYWS | WIRQHPGK GLEWIG | YMYY----SGSTYYNPS LKS | RVTISVDTSKNQFYLKLSAV TAADTAVYYCAK | GGYNWN-------NGFDC | WGQGT LVTVS S |
| | Germline | | H_FR1 | H_CDR1 | H_FR2 | H_CDR2 | H_FR3 | H_CDR3 | H_FR4 |
| | VH3/3-33/D2/2-15/RF3/JH6 | | | | | | | | |
| iPS:4 35869 | 21-225_190B1 | VH3/3-33/D2/2-15/RF3/JH6 | QVQLVES-GGGVVQPGRSLRL SCATSG-FTFS | S------YGMH | WVRQAPGK GLEWVA | VIWYD---GSNKHYADS VKG | RFTISRDNSKNTLYLQMNSL RAEDTAVYYCAR | DRTVGY-------SGMDV | WGQGT TVTVS S |
| iPS:4 36260 | 21-225_203H1 | VH3/3-33/D2/2-15/RF3/JH6 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DRTVGY-------NGMDV | WGQGT TVTVS S |
| iPS:4 36490 | 21-225_221F6 | VH3/3-33/D2/2-15/RF3/JH6 | QVQLVES-GGGVVQPGRSLRL SCAASG-FTFS | S------NGMH | WVRQAPGK GLEWVA | VIWYD---GSNENYADS VKG | RFTISRDNSKNTLYLQMNSL RAEDTAVYYCAR | DRTVGY-------NGMDV | WGQGT TVTVS S |
| iPS:4 36502 | 21-225_222A11 | VH3/3-33/D2/2-15/RF3/JH6 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DRDVGY-------NGMDV | WGQGT TVTVS S |
| iPS:4 36514 | 21-225_222D10 | VH3/3-33/D2/2-15/RF3/JH6 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DRDVGY-------NGMDV | WGQGT TVTVS S |
| iPS:4 36522 | 21-225_223H10 | VH3/3-33/D2/2-15/RF3/JH6 | QVQLVES-GGGVVQPGRSLRL SCAASG-FTFS | S------YGMH | WVRQAPGK GLEWVA | VIWYD---GSNKNYADS VKG | RFTISRDNSKNTLYLQMNSL RAEDTAVYYCAR | DRDVGY-------NGMDV | WGQGT TVTVS S |
| | Germline | | H_FR1 | H_CDR1 | H_FR2 | H_CDR2 | H_FR3 | H_CDR3 | H_FR4 |
| | VH3/3-21/D1/1-1/RF3/JH5 | | | | | | | | |
| iPS:4 35883 | 21-225_185A1 | VH3/3-21/D1/1-1/RF3/JH5 | EVQLVES-GGGLVKPGGSLRL SCAASG-FTFN | S------YSMN | WVRQAPGK GLEWVS | SISSS---GSYIYYADS VKG | RPTISRDNAKNSLYLQMHSL RAEDTAVYYCAR | SNL----------FDC | WGQGT PVTVS S |
| | Germline | | H_FR1 | H_CDR1 | H_FR2 | H_CDR2 | H_FR3 | H_CDR3 | H_FR4 |
| | VH3/3-23/D1/1-1/RF1/JH3 | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 35895 | 21-225_188E8 | VH3/3-23/D1/1-1|RF1/JH3 | EVQLLES-GGGLVQPGGSLRLSCAASG-FTFS | S-----SAMN | WVRQAPGK GLEWVS | VISGS----GGYTYIADS VKG | RFTISRDNSKNTLYLQMNSL RAEDTAVYFCAK | RNTDD----------AFDI | WGQGT MVTVS S |
| | | Germline | | | | | | | |
| | VH3|3-11|D7|7-27|RF3|JH4 | | | | | | | | |
| iPS:4 35903 | 21-225_190E2 | VH3/3-11/D7/7-27|RF3/JH4 | QVQLVES-GGGLVKPGGSLRLSCAASG-FTFS | D-----YYMS | WIRQAPGK GLEWLS | YISSS----GTTVFYADS VKG | RFTISRDNAKNSLYLQMNSL RAEDTAVYYCAR | EWVG-----------ADY | WGQGT LVTVS S |
| iPS:4 35923 | 21-225_190H6 | VH3/3-11/D7/7-27|RF3/JH4 | QVQLVES-GGGLVKPGGSLRLSCAASG-FTFS | D-----YYMS | WIRQAPGK GLEWLS | YISSS----GTTVFYADS VKG | RFTISRDNAKNSLYLQMNSL RAEDTAVYYCAR | EWVG-----------ADY | WGQGT LVTVS S |
| iPS:4 35953 | 21-225_191B12 | VH3/3-11/D7/7-27|RF3/JH4 | QVQLVES-GGGLVKPGGSLRLSCAASG-FTFS | D-----YYMS | WIRQAPGK GLEWLS | YISSS----GTTVFYADS VKG | RFTISRDNAKNSLYLQMNSL RAEDTAVYYCAR | EWVG-----------ADY | WGQGT LVTVS S |
| iPS:4 36098 | 21-225_195G11 | VH3/3-11/D7/7-27|RF3/JH4 | QVQLVES-GGGLVKPGGSLRLSCAASG-FTFS | D-----YYMS | WIRQAPGK GLEWLS | YISSS----GITMYYADS VKG | RFTISRDNAKNSLYLQMNSL RAEDTAVYYCAR | EWVG-----------ADY | WGQGT LVTVS S |
| iPS:4 36102 | 21-225_196B1 | VH3/3-11/D7/7-27|RF3/JH4 | QVQLVES-GGGLVKPGGSLRLSCAASG-FTFS | D-----YYMS | WIRQAPGK GLEWLS | YISSS----GTTVFYADS VKG | RFTISRDNAKNSLYLQMNSL RAEDTAVYYCAR | EWVG-----------ADY | WGQGT LVTVS S |
| iPS:4 36104 | 21-225_196C1 | VH3/3-11/D7/7-27|RF3/JH4 | QVQLVES-GGGLVKPGGSLRLSCAASG-FTFS | D-----YYMS | WIRQAPGK GLEWLS | VISGR----GGNTYYADS VKG | RFTISRDNAKNSLYLQMNSL RAEDTAVYYCAR | EWVG-----------ADY | WGQGT LVTVS S |
| | | H_FR1 | H_CDR1 | H_FR2 | H_CDR2 | H_FR3 | H_CDR3 | H_FR4 | | |
| | | Germline | | | | | | | |
| | VH3|3-23|D6|6-19|RF2|JH4 | | | | | | | | |
| iPS:4 35965 | 21-225_192H2 | VH3/3-23/D6/6-19|RF2/JH4 | EVQLLES-GGDLIQPGGSLRLSCAASG-FTFS | S-----SAMS | WVRQAPGK GLEWVS | AISGS----GGNTFYADS VKG | RFTISRDNSKNTLYLQMNSL RAEDTAVYYCAK | LIAVVG---------SHYFDY | WGQGT LVTVS S |
| iPS:4 36160 | 21-225_197C9 | VH3/3-23/D6/6-19|RF2/JH4 | EVQLLES-GGGLAQPGGSLRLSCAASG-FTFR | S-----YAMS | WVRQAPGK GLEWVS | VISGR----GGNTYYADS VKG | RFTISRDNSKNTLYLQMNSL RAEDTAVYYCAK | GIAVAG---------SHYFDY | WGQGT LVTVS S |
| iPS:3 92954 | 21-225_26A10 | VH3/3-23/D6/6-19|RF2/JH4 | EVQLLES-GGGLVQPGGSLRLSCAASG-FTFS | S-----YAMS | WVRQAPGK GLEWVS | VISGS----GVNTFYADS VKG | RFTISRDNSKNTLYLLMNSL RAEDTAVYYCAK | KIAVAG---------THYFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH4/4-30.1/D5/5-24/RF3/JH4 | QVQLQES-GPGLVKPSQTLSL TCTVSG-GSIS | SG----GYYWS | WIRQHPGK GLEWIG | YIYY----SGSTYNPS LKS | RVTISVDTSKNQFSLKLSSV TAADTAVYYCAR | RGYY-------YFDY | WGQGT LVTVS S |
| iPS:4 35983 | 21-225_192E5 | VH4/4-30.1/D5/5-24/RF3/JH4 | QVQLQES-GPGLVKPSQILSL TCTVSG-DSIN | NG----GYYWS | WIRQHPGK GLEWIG | YIFY----SGSTYNPS LKS | RVTISVDTSKNQFSLKLNSV TAADTAVYFCAR | AGYNWD-------NGFDY | WGQGT LVTVS S |
| iPS:4 36043 | 21-225_193G9 | VH4/4-30.1/D5/5-24/RF3/JH4 | QVQLQES-GPGLVKPSQILSL TCTVSG-DSIN | NG----GYYWS | WIRQHPGK GLEWIG | YIFY----SGSTYNPS LKS | RVTISVDTSKNQFSLKLNSV TAADTAVYFCAR | AGYNWD-------NGFDY | WGQGT LVTVS S |
| iPS:4 36084 | 21-225_195F2 | VH4/4-30.1/D5/5-24/RF3/JH4 | QVQLQES-GPGLVKPSQILSL TCTVSG-DSIS | SG----GYYWS | WIRQHPGK GLEWIG | YSYY----SGSTYNPS LKS | RVTISVDMSKNQFSLKLSSV TDADTAVYYCAR | GGYNWN-------NGFDY | WGQGA LVTVS S |
| iPS:4 37138 | 21-225_214D8 | VH4/4-30.1/D5/5-24/RF3/JH4 | QVQLQES-GPGLVKPSQILSL TCTVSG-GSIS | TA----FYYWS | WIRQHPGK GLEWIG | YIYF----SGSTYNPS LKS | RVTISVDTSKNQFSLNLSSV TAADTAVYYCAR | ARGYHY-------SIFDY | WGQGT LVTVS S |
| | Germline | H_FR1 | H_CDR1 | H_FR2 | H_CDR2 | H_FR3 | H_CDR3 | H_FR4 |
| | VH3/3-23/D3/3-16/RF1/JH3 | | | | | | | |
| iPS:4 36003 | 21-225_192G10 | VH3/3-23/D3/3-16/RF1/JH3 | EVQLLES-GGGLVQPGGSLRL SCSASG-FTFS | S-----YAMS | WVRQAPGK GLEWVS | AISGR---GGSTFYADS VKG | RFTISRDNSKNTLYLQMNSL RAEDTAVYYCAR | RLALDG-------YDAFDI | WGQGT MVTVS S |
| | Germline | H_FR1 | H_CDR1 | H_FR2 | H_CDR2 | H_FR3 | H_CDR3 | H_FR4 |
| | VH3/3-23/D7/7-27/RF2/JH4 | | | | | | | |
| iPS:4 36019 | 21-225_193C4 | VH3/3-23/D7/7-27/RF2/JH4 | EVQLLES-GGGLAQPGGSLRL SCAASG-FTFS | S-----YAMN | WVRQAPGK GLEWVS | AIIGN---GGRTFYADS VKG | RFSISRDNSKNTLFLQMNSL RAEDTAVYYCAK | DLGRYS-------YGFFDY | WGQGT LVTVS S |
| | Germline | H_FR1 | H_CDR1 | H_FR2 | H_CDR2 | H_FR3 | H_CDR3 | H_FR4 |
| | VH4/4-30.1/D1/1-1/RF1/JH6 | | | | | | | |
| iPS:4 36025 | 21-225_193B5 | VH4/4-30.1/D1/1-1/RF1/JH6 | QVQLQES-GPGLVKPSQILSL TCTVSG-GSIS | SG----GYYWS | WIRQHPGK GLEWIG | YIYY----SGSTYNPS LKS | RVTISVDTSKNQFSLKLSSV AAADTAVYYCAR | GEYNWN-------HGMDV | WGQGT TVTVS S |
| | Germline | H_FR1 | H_CDR1 | H_FR2 | H_CDR2 | H_FR3 | H_CDR3 | H_FR4 |
| | VH4/4-34/D4/4-11/RF1/JH4 | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36033 | 21-225_193E7 | VH4/4-34/D4/4-11/RF2/JH4 | QVQLQQW-GAGLLKPSETLSLTCAVYG-GSFS | G------YFWT | WIRQPPGKGLEWIG | EINH----SGSTNYNPSLKS | RVTISVDTSKNQFSLKLSSVTAADTAVYYCAR | DYG----------ADY | WGQGTLVAVSA |
| iPS:4 36199 | 21-225_199E3 | VH4/4-34/D4/4-11/RF2/JH4 | QVQLQQW-GAGLLKPSETLSLTCAVYG-GSFS | G------YFWT | WIRQPPGKGLEWIG | EINH----SGSTNYNPSLKS | RVTISVDTSKNQFSLKLSSVTAADTAVYYCAR | DYG----------ADY | WGQGTLVAVSA |
| iPS:4 36228 | 21-225_200F12 | VH4/4-34/D4/4-11/RF2/JH4 | QVQLQQW-GAGLLKPSETLSLTCAVYG-GSFS | G------YFWT | WIRQPPGKGLEWIG | EINH----SGSTNYNPSLKS | RVTISVDTSKNQFSLKVSSVTAADTAVYYCAR | DYG----------ADY | WGQGTLVTVSS |
| iPS:4 36230 | 21-225_201A1 | VH4/4-34/D4/4-11/RF2/JH4 | QVQLQQW-GAGLLKPSETLSLTCAVYG-GSFS | G------YFWT | WIRQPPGKGLEWIG | EISH----SGSTNYNPSLKS | RVTISGDTSKNQFSLKLSSVTAADTAVYYCAR | DYG----------ADY | WGQGTLVTVSS |
| iPS:4 36242 | 21-225_201A10 | VH4/4-34/D4/4-11/RF2/JH4 | QVQLQQW-GAGLLKPSETLSLTCAVYG-GSFS | G------YFWT | WIRQPPGKGLEWIG | EISH----SGRTNYNPSLKS | RVTISVDTSKNQFSLKVNSVTAADTAVYYCAR | DYG----------ADY | WGQGTLVTVSS |
| iPS:4 36286 | 21-225_204H8 | VH4/4-34/D4/4-11/RF2/JH4 | QVQLQQW-GAGLLKPSETLFLTCAVYG-GSFS | G------YFWT | WVRQPPGKGLEWIG | EISH----SGSTNYNPSLKS | RVTISVDKSKNQFSLKLSSVTAADTAVYYCAR | DYG----------ADY | WGQGTLVTVSS |
| iPS:4 36308 | 21-225_205H8 | VH4/4-34/D4/4-11/RF2/JH4 | QVQLQQW-GAGLLKPSETLSLTCAVYG-GSFS | G------YFWS | WIRQPPGKGLEWIG | EISH----SGRTNYNPSLKS | RVTISVDTSKNQFSLKVSSVTAADTAVYYCAR | DYG----------ADY | WGQGTLVTVSS |
| | Germline | | | | | | | | |
| | VH3/3-30.3/D1/1-1/RF1/JH4 | | | | | | | | |
| iPS:4 36051 | 21-225_193G12 | VH3/3-30.3/D1/1-1/RF1/JH4 | QVQLVES-GGGVVQPGRSLRLSCGASG-FTFS | S------YAMH | WVRQAPGKGLEWVA | VIWYD---GTNKYYGDSVKG | RFTISRDNSKNTLMLQMNSLRAEDTAVYYCAR | DETIIG------ATYFDY | WGQGTLVTVSS |
| | Germline | | | | | | | | |
| | VH3/3-33/D7/7-27/RF3/JH6 | | | | | | | | |
| iPS:4 36054 | 21-225_194C1 | VH3/3-33/D7/7-27/RF3/JH6 | QVQLVES-GGGVVQFGRSLRLSCAASG-FTFS | S------YGMH | WVRQAPGKGLEWVA | VIWYD---GSNEHYADSVKG | RFTISRDNSKNTLYLQMNSLRAEDTAVYYCAR | NRGVGY-------YGLDV | WGQGTTVTVSS |
| | Germline | | | | | | | | |
| | VH1/1-02/D5/5-18/RF3/JH1 | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36058 | 21-225_194A4 | VH1|1-02|D5|5-18|RF3/JH1 | QVQLVQS-GIEVKKPGASLKV SCKASG-YTFT | V------YYLN | WVRQAPGQ GLEWMG | WINPN---SGGTNYAQK FQG | RVTMTRDTSISTAYMELSRL RSDDTAVYYCAR | GYDI------------LIG | WGQGT LVTVS S |
| | VH1|1-02|D5|5-26|RF3/JH6 | Germline | QVQLVQS-GIEVKKPGASVKV SCKASG-YTFT | ------YYMH | WVRQAPGQ GLEWMG | WINPN---SGGTNYAQK FQG | RVTMTRDTSISTAYMELSRL RSDDTAVYYCAR | ----------DAFDI | WGQGT MVTVS S |
| iPS:4 36068 | 21-225_194F7 | VH1|1-02|D1|1-26|RF3/JH6 | QVQLVQS-GAEVKKPGASVKV SCKASG-YTFT | D------YYIH | WVRQAPGQ GLEWMG | WINPN---NGGTNYAQK FQG | RVTMIKDTSISTAYMELSRL RSDDTAVYYCAR | EPLGYIGSG----SYGAYGMDV | WGQGT TVTVS S |
| | VH4|4-34|D4|4-17|RF2/JH3 | Germline | QVQLQQW-GAGLLKPSEILSL TCAVYG-GSFS | ------YWS | WIRQPPSGK GLEWIG | EINH----SGSTNYNPS LKS | RVTISVDTSKNQFSLKLSSV TAADTAVYYCAR | ----DAFDI | WGQGT MVTVS S |
| iPS:4 36072 | 21-225_194C10 | VH4|4-34|D4|4-17|RF2/JH3 | QVQLQQW-GAGLLKPSEILSL TCAVSG-GSFR | Y------YWS | WIRQPPGK GLEWFG | EINH----SGSTNYNPS LKS | RVTISIDTSKNQFSLKLRSV TAADTAVYYCAR | ----FDI | WGQGT MVTVS S |
| iPS:4 36506 | 21-225_222C7 | VH4|4-34|D4|4-17|RF2/JH3 | QVQLQQW-GAGLLKPSEILSL TCAVYG-GSFS | G------RYWS | WIRQPPGK GLEWIG | EINH----SGSANYNPS LKS | RVTISVDTSKNQFSLKLSSV TAADTAVYYCAR | ----LDF | WGQGT MVTVS S |
| | VH3|3-33|D5|5-24|RF2/JH6 | Germline | QVQLVES-GGGVVQPGRSLRL SCAASG-FTFS | ------YGMH | WVRQAPGK GLEWVA | VIWYD---GSNKYYADS VKG | RFTISRDNSKNTLYLQMNSL RAEDTAVYYCAR | ----YYGMDV | WGQGT TVTVS S |
| iPS:4 36092 | 21-225_195B9 | VH3|3-33|D5|5-24|RF2/JH6 | QVQLVES-GGGVVQPGRSLRL SCAASG-FTFS | S------YGMH | WVRQAPGK GLEWVA | VIWYD---GSNKYYADS VKG | RFTISRDNSKNTLYLQMNSL RAEDTAVYYCAR | EWLQFRY-------YYGMDV | WGQGT TVTVS S |
| iPS:4 36164 | 21-225_197G10 | VH3|3-33|D5|5-24|RF2/JH6 | QVQLVES-GGGVVQPGRSLRL SCVASG-FTFS | S------YGMH | WVRQAPGK GLEWVA | VTWYD---GSNKYYADS VKG | RFTISRDNSKNTLYLQMNSL RAEDTAVYYCAR | EWLQFRY-------YYGIDV | WGQGT TVTVS S |
| iPS:4 36191 | 21-225_198B9 | VH3|3-33|D5|5-24|RF2/JH6 | QVQLVES-GGGVVQPGRSLRL SCAASG-FTFS | N------YGMH | WVRQAPGK GLEWVA | IIWFD---GSNKYYVDS VKG | RFTISRDNSKNTLFLQMSSL RAEDTAVYYCAR | EWLQFRY-------YYGMDV | WGQGT TVTVS S |
| iPS:4 36205 | 21-225_199A7 | VH3|3-33|D5|5-24|RF2/JH6 | QVQLVES-GGGVVQPGRSLRL SCAASG-FTFS | N------YGMH | WVRQAPGK GLEWVA | IIWFD---GSNKYYVDS VKG | RFTISRDNSKNTLFLQMSSL RAEDTAVYYCAR | EWLQFRY-------YYGMDV | WGQGT TVTVS S |
| iPS:4 36214 | 21-225_200F6 | VH3|3-33|D5|5-24|RF2/JH6 | QVQLVES-GGGVVQPGRSLRL SCAASG-FTFS | S------YGMH | WVRQAPGK GLEWVA | VIWYD---GSNKYYADS VKG | RFTISRDNSKNTLYLQMNSL RAEDTAVYYCTR | EWLQFRY-------YYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3/3-33|D6|6-19|RF3|JH6 | | QVQLVES- | S | WVRQAPGK | VILND | RFTISRDNSKNTLYLQMNSL | V*DRLYY | WGQGT |
| iPS:4 36106 | 21-225_196F2 | VH3|3-33/D6|6-19|RF3|JH6 | QVQLVES-GGGVVQPGRSLRL SCAASG-FTFS | S------FGMH | WVRQAPGK GLEWVA | VILND---GSNKKCADS VKG | RCTISRDNSKNTLYLQMNSL RAEDTAVYYCAR | GQQWLV-------NGVDV | WGQGT TVTVS S |
| VH3|3-23|D6|6-6|RF3|JH6 | Germline | | | | | | | |
| iPS:4 36110 | 21-225_196F4 | VH3|3-23/D6|6-6|RF3|JH 6 | EVQLLES-GGGLVQPGGSLRF SCAASG-FTFS | S------CAMT | WVRQAPGK GLEWVS | AISGS---GGSTYYADS VKG | RFTISRDNSKNTLYLQMNSL RAEDTAVYYCAR | VGGLIGSY-------YYYGMDV | WGQGT TVTVS S |
| VH1|1-08|D2|2-21|RF1|JH5 | Germline | | | | | | | |
| iPS:4 36114 | 21-225_196G8 | VH1|1-08|D2|2-21|RF1|J H5 | QVQLVQS-GAEVKKPGASVKV SCKASG-YIFT | N------YDIN | WMRQATGQ GLEWMG | WMHLN---SGNTGYAPK FQG | RVIMTRDTSISTAFMELSSL RSEDTAVYYCAY | SGGWY-------VFDP | WGQGT LVTVS S |
| iPS:4 36218 | 21-225_200G7 | VH1|1-08|D2|2-21|RF1|J H5 | QVQLVQS-GAEVKKPGASVKV SCKASG-YIFT | N------YDIN | WMRQATGQ GLEWMG | WMHLN---SGNTGYAPK FQG | RVIMTRDTSISTAFMELSSL RSEDTAVYYCAY | SGGWY-------VFDP | WGQGT LVTVS S |
| VH1|1-02|D3|3-10|RF3|JH6 | Germline | | | | | | | |
| iPS:4 36116 | 21-225_196B9 | VH1|1-02|D3|3-10|RF3|J H6 | QVQLVQS-GAEVKKPGASMKV SCKASG-YIFT | G------YYMH | WVRQAPGQ GLEWMG | WINPN---SGGTNFAQK FRG | RVIMTRDTSISTAYMELSRL SSDDTAVYYCAR | GGVRGVPN-----YYYVMDV | WGQGT TVTVS S |
| VH4|4-30.1|D5|5-18|RF3|JH6 | Germline | | | | | | | |
| iPS:4 36181 | 21-225_198C2 | VH4|4-30.1|D5|5-18|RF3|J H6 | QVQLQES-GPGLVKPSQTLSL TCTVSG-GSIS | SG---GYYWS | WIRQHPGK GLEWIG | NIYY----SGSTYYNPS LKS | RVTISVDTSKNQFSLKLSSV TAADTAVYYCAR | GDYYGSGSY-------HNYYGLDV | WGQGT TVTVS S |
| iPS:4 36210 | 21-225_199G11 | VH4|4-30.1|D5|5-18|RF3|J H6 | QVQLQES-GPGLVKPSQTLSL TCTVSG-GSIS | SG---GYYWS | WIRQHPGK GLEWIG | NIYY----SGSTYYNPS LKS | RVTISVDTSKNQFSLKLSSV TAADTAVYYCAR | GDYYGSGSY-------HNYYGLDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH1|1-18|D3|3-3|RF2|JH6 | | | | | | | | |
| iPS:4 36234 | 21-225_51E3 | VH1|1-18|D3|3-3|RF2|JH6 | QVQLVQS-GAEVKKPGASVKV SCKASG-YTFN | S-----YGIS | WVRLAPGQ GLEWMG | WISAY---NGNTKNAQK FQG | RVTMTTDTSTSTAYMELRSL RSDDTAVYYCAR | HDFWSGY-------YKGMDV | WGQGT TVTVS S |
| iPS:4 36830 | 21-225_51F4 | VH1|1-18|D3|3-3|RF2|JH6 | QVQLVQS-GAEVKKPGASVKV SCKASG-YTFN | S-----YGIS | WVRQAPGQ GLEWMG | WISAY---NGNTKYAQK LQG | RVTMTTDTSTSTAYMELRSL RSDDTAVYYCAR | HDFWSGY-------YKGMDV | WGQGT TVTVS S |
| iPS:4 36834 | 21-225_52F1 | VH1|1-18|D3|3-3|RF2|JH6 | QVQLVQS-GAEVKKPGASVKV SCKASG-YTFN | S-----YGVS | WVRQAPGQ GLEWMG | WISAY---NGNRKYAQK LQG | RVSMTTDTSTSTAYMELRSL RSDDTAVYYCAR | HDFWSGY-------YKGMDV | WGQGT TVTVS S |
| iPS:4 36842 | 21-225_54E9 | VH1|1-18|D3|3-3|RF2|JH6 | QVQLVQS-GAEVKKPGASVKV SCKASG-YTFN | S-----YGIS | WVRLAPGQ GLEWMG | WISAY---NGNTKNAQK FQG | RVTMTTDTSTSTAYMELRSL RSDDTAVYYCAR | HDFWSGY-------YKGMDV | WGQGT TVTVS S |
| iPS:4 36844 | 21-225_56G1 | VH1|1-18|D3|3-3|RF2|JH6 | QVQLVQS-GAEVKKPGASVKV SCKASG-YTFN | S-----YGIS | WVRQAPGQ GLEWMG | WISAY---NGNTKYAQK LQG | RVTMTTDTSTSTAYMELRSL RSDDTAVYYCAR | HDFWSGY-------YKGMDV | WGQGT TVTVS S |
| iPS:4 36846 | 21-225_56E3 | VH1|1-18|D3|3-3|RF2|JH6 | QVQLVQS-GAEVKKPGASVKV SCKASG-YTFN | S-----YGFS | WVRQAPGQ GLEWMG | WISAY---NGNTKEAQK FQG | RVTMTTDTSTSTAYMELRSL RADDTAVYYCAR | HDFWSGY-------YKGMDV | WGQGT TVTVS S |
| iPS:4 51104 | 21-225_49C5 | VH1|1-18|D3|3-3|RF2|JH6 | QVQLVQS-GAEVKKPGASVKV SCKASG-YTFN | S-----YGIS | WVRQAPGQ GLEWMG | WISAY---NGNTKYAQK LQG | RVTMTTDTSTSTAYMELRSL RSDDTAVYYCAR | HDFWSGY-------YKGMDV | WGQGT TVTVS S |
| iPS:4 51106 | 21-225_49D10 | VH1|1-18|D3|3-3|RF2|JH6 | QVQLVQS-GAEVKKPGASVKV SCKASG-YTFN | S-----YGIS | WVRLAPGQ GFEWMG | WISAY---NGNTKNAQK LQG | RVTMTTDTSTSTAYMELRSL RSDDTAVYYCAR | HDFWSGY-------YKGMDV | WGQGT TVTVS S |
| iPS:4 51108 | 21-225_53E8 | VH1|1-18|D3|3-3|RF2|JH6 | QVQLVQS-GAEVKKPGASVKV SCKASG-YTFN | S-----YGIS | WVRQAPGQ GLEWMG | WISAY---NGNTKFAQK LQG | RVTMTTDTSTSTAYMELRSL RSDDTAVYYCAR | HDFWSGY-------YKGMDV | WGQGT TVTVS S |

| | Germline | H_FR1 | H_CDR1 | H_FR2 | H_CDR2 | H_FR3 | H_CDR3 | H_FR4 |
|---|---|---|---|---|---|---|---|---|
| VH6|6-01|D3|3-9|RF1|JH6 | | | | | | | | |
| iPS:4 36236 | 21-225_201F7 | VH6|6-01|D3|3-9|RF1|JH6 | QVQLQQS-GPGLVKPSQTLSL TCAISG-DSVS | SN---SAAWN | WIRQSPSR GLEWLG | RTYYR---SKWINYYEV SVRS | RITINPDISKNQFSLQLNSV TPEDTAVYFCAR | DQRYY--------GMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36250 | 21-225_201A4 | VH6[6-01]D3[3-9]RF1/JH6 | QVQLQQS-GPGLVKPSQTLSLTCAISG-DSVS | SN---SAAWN | WIRQSPSR GLEWLG | RTYYR---SKWYNYYEV SVRS | RITINPDTSKNQFSLQLNSV TPEDTAVYFCAR | DQRYY-------GMDV | WGQGT TVTVS S |
| iPS:4 36252 | 21-225_202A8 | VH6[6-01]D3[3-9]RF1/JH6 | QVQLQQS-GPGLVKPSQTLSLTCAISG-DSVS | SN---SAAWN | WIRQSPSR GLEWLG | RTYYR---SKWYNEYAV SVRS | RITINPDTSKNQFSLQLNSV TPEDTALYYCTR | DQRYY-------GMDV | WGQGT PVTVS S |
| iPS:4 36278 | 21-225_201F2 | VH6[6-01]D3[3-9]RF1/JH6 | QVQLQQS-GPGLVKPSQTLSLTCAISG-DSVS | SN---SAAWN | WIRQSPSR GLEWLG | RTYYR---SKWYNYYEV SVRS | RVTINPDTSKNQFSLQLNSV TPEDTAVYFCAR | DQRYY-------GMDV | WGQGT TVTVS S |
| iPS:4 36294 | 21-225_205G4 | VH6[6-01]D3[3-9]RF1/JH6 | QVQLQQS-GPGLVKPSQTLSLTCAISG-DSVS | SN---SAAWN | WIRQSPSR GLEWLG | RTYYR---SKWYNYYEV SVRS | RITINPDTSKNQFSLLLNSV TPEDTAVYFCAR | DQRYY-------GMDV | WGQGT TVTVS S |
| iPS:4 36356 | 21-225_210H10 | VH6[6-01]D3[3-9]RF1/JH6 | QVQLQQS-GPGLVKPSQTLSLTCAISG-DSVS | SN---SAAWN | WIRQSPSR GLEWLG | RTYYR---SKWYNYYPV SVRS | RITIMPDTSKNQFSLLLNSV TPEDTAVYFCAR | DQRYY-------GMDV | WGQGT TVTVS S |
| | Germline | VH1[1-02]D4[4-23]RF2/JH4 | QVQLVQS-GAEVKKPGASVKVSCKASG-YTFT | G------YYMH | WVRQAPGQ GLEWMG | WINPN---SGGTNYAQK FQG | RVTMTRDTSISTAYMELSRL RSDDTAVYYCAR | | H_FR4 |
| iPS:4 36240 | 21-225_201E8 | VH1[1-02]D4[4-23]RF2/JH4 | QVQLVQS-GAEVKKPGASVKVSCKASG-YTFT | G------YYMH | WVRQAPGQ GLEWMG | WIDPN---SGGTNYPQK FQG | RVTMTRDTSISTAYMELSRL RSDDTAVFYCAK | DQGYNW-----NSFDY | WGQGT LVTVS S |
| iPS:4 36314 | 21-225_206G4 | VH1[1-02]D4[4-23]RF2/JH4 | QVQLVQS-GAEVKKPGASVKVSCKASG-YTFT | G------YYIH | WVRQAPGQ GLEWMG | WIDPN---SGGTNYAQK FQG | RITMTRDTSISTAYMELSRL RSDDTAVFYCAK | DQGYNW-----NSFDY | WGQGT LVTVS S |
| | Germline | VH1[1-02]D5[5-18]RF3/JH5 | QVQLVQS-GAEVKKPGASVKVSCKASG-YTFT | G------YYIH | WVRQAPGQ GLEWMA | WINPN---SGGTNYAQK FQG | RVTMTRDTSITTAYMELSRL RSDDTAVYYCAR | | H_FR4 |
| iPS:4 36244 | 21-225_201H10 | VH1[1-02]D5[5-18]RF3/JH5 | QVQLVQS-GAEVKKPGASVKVSCKASG-YTFT | G------YYIH | WVRQAPGQ GLEWMA | WINPN---SGGTNYAQK FQG | RVTMTRDTSITTTYMELSRL RSDDTAVYYCAR | GYSYGY-----NWFDP | WGQGT LVTVS S |
| iPS:4 36262 | 21-225_203E3 | VH1[1-02]D5[5-18]RF3/JH5 | QVQLVQS-GAEVKKPGASVKVSCKASG-YTFT | G------YYIH | WVRQAPGQ GLEWMA | WINPN---SGGTNYAQK FQG | RITMTRDTSITTAYMELSRL RSDDTAVYYCAR | GYSYGY-----NWFDP | WGQGT LVTVS S |
| iPS:4 36276 | 21-225_204H4 | VH1[1-02]D5[5-18]RF3/JH5 | QVQLVQS-GAEVKKPGASVKVSCKASG-YTFT | G------YYIH | WVRQAPGQ GLEWMA | WINPN---SGGTNYAQK FQG | RVTMTRDTSITTAYMELSRL RSDDTAVYYCAR | GYSYGY-----NWFDP | WGQGT LVTVS S |

Figure 51 (Continued)

| | | | | | | | | |
|---|---|---|---|---|---|---|---|---|
| iPS:4 36312 | 21-225_206A4 | VH1|1-02|D5|5-18|RF3|JH5 | QVQLVQS-GAEVKKPGASVKVSCKASG-YTFT | G------YYIH | WVRQAPGQGLEWMA | WINPN---SGGTNYAQKFQG | RVTMTRDTSITTAYMELSRLRSDDTAVYYCAR | GYSYGY------NWFDP | WGQGTLVTVSS |
| iPS:4 36316 | 21-225_206A5 | VH1|1-02|D5|5-18|RF3|JH5 | QVQLVQS-GAEVKKPGASVKVSCKASG-YTFT | G------YYIH | WVRQAPGQGLEWMA | WINPN---SGGTNYAQKFQG | RVTMTRDTSITTAYMELSRLRSDDTAVYYCAR | GYSYGY------NWFDP | WGQGTLVTVSS |
| iPS:4 36338 | 21-225_208E8 | VH1|1-02|D5|5-18|RF3|JH5 | QVQLVQS-GAEVKKPGASVKVSCKASG-YTFT | G------YYIH | WVRQAPGQGLEWMA | WINPN---SGGTNYAQKFQG | RVTMTRDTSITTAYMELSRLRSDDTAVYYCAR | GYSYGY------NWFDP | WGQGTLVTVSS |
| iPS:4 36344 | 21-225_208B11 | VH1|1-02|D5|5-18|RF3|JH5 | QVQLVQS-GAEVKKPGASVKVSCKASG-YTFT | G------YYIH | WVRQAPGQGLEWMA | WINPN---SGGTNYAQKFQG | RVTMTRDTSITTAYMELSRLRSDDTAVYYCAR | GYSYGY------NWFDP | WGQGTLVTVSS |
| iPS:4 36358 | 21-225_210D11 | VH1|1-02|D5|5-18|RF3|JH5 | QVQLVQS-GAEVKKPGASVKVSCKASG-YTFT | G------YYIH | WVRQAPGQGLEWMA | WINPN---SGGTNYAQKFQG | RVTMTRDTSITTAYMELSRLRSDDTAVYYCAR | GYSYGY------NWFDP | WGQGTLVTVSS |
| iPS:4 36408 | 21-225_214H8 | VH1|1-02|D5|5-18|RF3|JH5 | QVQLVQS-GAEVKKPGASVKVSCKASG-YTFT | G------HYIH | WVRQAPGQGLEWMG | WINSN---NGGTNYAQKFQG | RVTMTRDTSISTAYMELSRLRSDDTAVYYCAK | DGRYSYG------YDWFDP | WGQGTLVTVSS |
| iPS:4 36424 | 21-225_215H6 | VH1|1-02|D5|5-18|RF3|JH5 | QVQLVQS-GAEVKKPGASVKVSCKASG-YTFT | G------HYIH | WVRQAPGQGLEWMG | WINSN---SGGTNYAEKFQG | RVTMTRDTSISTAYMELSRLRSDDTAVYYCAK | DGRYSYG------HDWFDP | WGQGTLVTVSS |
| iPS:4 37092 | 21-225_210B12 | VH1|1-02|D5|5-18|RF3|JH5 | QVQLVQS-GAEVKKPGASVKISCKASG-FTFT | D------YYMN | WVRQAPGQGLEWMG | WINPN---SGGTNYAQKFQG | RVTMTRDTSISTAYMELSRLRSDDTAVYYCAK | GYDS------FAP | WGQGTLVTVSS |
| iPS:4 37134 | 21-225_213A7 | VH1|1-02|D5|5-18|RF3|JH5 | QVQLVQS-GAEVKKPGASVKISCKASG-FTFT | D------YYMN | WVRQAPGQGLEWMG | WINPK---NGGTNYAQKFQD | RVTMTRDISLSRAYMELSRLRSDDTAVYYCAK | GYDS------FAP | WGQGTLVTVSS |
| iPS:4 37194 | 21-225_226B2 | VH1|1-02|D5|5-18|RF3|JH5 | QVQLVQS-GAEVKKPGASVKVSCKASG-YTFT | G------YFMH | WVRQAPGQGLEWMG | WINPN---SGDTNYAQKFQG | RVTMTRDTSLNTAYMELSRLRSDDTAIYYCAR | GTYYGSGS------YFNELDS | WGQGTLVTVSS |
| iPS:4 37196 | 21-225_226B7 | VH1|1-02|D5|5-18|RF3|JH5 | QVQLVQS-GAEVKKPGASVKVSCKASG-YTFT | G------YFMH | WVRQAPGQGLEWMG | WINPN---SGGTNYAQKFQG | RVTMTRDTSISTAHMELSRLRSDDTAVYYCAR | GYYYGSGS------YYNWFDS | WGQGTLVTVSS |
| iPS:4 37200 | 21-225_226A10 | VH1|1-02|D5|5-18|RF3|JH5 | QVQLVQS-GAEVKKPGASVKVSCKASG-YTFT | G------YFMH | WVRQAPGQGLEWMG | WINPN---SGGTNYAQKFQG | RVTMTRDISLSTAYMELSRLRSDDTAIYYCAR | GTYYGSGS------YFNELDS | WGQGTLVTVSS |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:3 93168 | 21-225_32B11 | VH1[1-02]D5[5-18]RF3/JH5 | QVQLVQS-GAEVKKPGASVKV SCKASG-YTFT | G------YYMH | WVRQAPGQ GLEWMG | WINPN---SDGTNYAQK FQG | RVTMTRDTSISTAYMELRRL RSEDTAVYYCAR | GFYYGSGS---------YYNDLDP | WGQGT LVTVS S |
| iPS:3 93178 | 21-225_34D7 | VH1[1-02]D5[5-18]RF3/JH5 | QVQLVQS-GAEVKKPGASVKV SCKASG-YTFT | G------YYMH | WVRQAPGQ GLEWMG | WINPN---SGGTNYAQK FQG | RVTMTRDTSISTAYMELSRL RSEDTAVYYCAR | GYYYGSGS---------YYNDLDP | WGQGT LVTVS S |
| iPS:3 98480 | 21-225_17G4 | VH1[1-02]D5[5-18]RF3/JH5 | QVQLVQS-GAEVKKPGASVKV SCKISG-YTFT | D------YYMH | WVRQAPGQ GLEWMG | WINPN---SGGTNYFQK FQG | RVTMTRDTSISTAYMELSRL RSEDTAVYYCAS | GYSYGY---------NWFDP | WGQGT LVTVS S |
| iPS:3 98486 | 21-225_19A1 | VH1[1-02]D5[5-18]RF3/JH5 | QVQLVQS-GAEVKKPGASVKV SCKASG-YTFT | G------YYMH | WVRQAPGQ GLEWMG | WINPN---SGGTNYAQK FQG | RVTMTRDTSISTAYMELSRL RSEDTAVYYCAS | GYSYGY---------NWFDP | WGQGT LVTVS S |
| | Germline | VH1[1-02]D5[5-18]RF3/JH6 | | | | | | | |
| iPS:4 36248 | 21-225_202A3 | VH1[1-08]D6[6-13]RF1/JH6 | QVQLEQS-GAEVKKPGASVKV SCKASG-YTFT | S------YDIN | WVRQATGQ GLEWLG | WMNPK---RGNTGYAQK FQG | RVTMTRNTSISTAHMELSSL RSEDTAVYYCAR | GRYSREDY---------YYYYDMDV | WGQGT TVTVS S |
| | Germline | | | | | | | | |
| iPS:4 36270 | 21-225_203F10 | VH3[3-11]D4[4-17]RF2/JH6 | QVQLVES-GGGLVKPGGSLRL SCAASG-FTFS | D------YYMS | WIRQAPGK GLEWVL | YISGS---GTTIYADS VKG | RFTISRDNAKNSLYLQMNSL RAEDTAVYYCAR | DRGG---------LDV | WGQGT TVTVS S |
| iPS:4 36280 | 21-225_204D6 | VH3[3-23]D11[1-20]RF1/JH6 | EVQVLES-GGGLVQPGGSLRL SCAASG-FTFS | T------YAMS | WVRQAPGK GLEWVS | AISGS---GGSTYYADS VKG | RFTISRDNSKNTLYLQMDSL RAEDTAVYYCAK | GISGTGSY---------YYYGVDV | WGQGT TVTVS S |
| | Germline | | | | | | | | |
| iPS:4 36284 | 21-225_204G8 | VH3[3-33]D7[7-27]RF2/JH6 | QVQLVES-GGDVVQPGRSLRL SCAASG-FTFS | S------YGMH | WGRQAPGK GLEWVA | VIWYD---GSNENYVAS VKG | RFTIFRDNSKNTLYLQMNSL RAEDTAVYYCAR | DLGIGY---------YGMDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36968 | 21-225_190B10 | VH3|3-33/D7|7-27/RF2/JH6 | QVQLVES-GGGVVQPGRSLRL SCVASG-FTFS | S-----YGMH | WVRQAPGK GLEWVA | VIWND---GSKKYHVDS VKG | RFTISRDNSKNTLYLQMNSL RAEDTALYYCAR | DLDKRNFPY------YYYYGMDV | WGQGT TVTVS S |
| iPS:4 37006 | 21-225_192G2 | VH3|3-33/D7|7-27/RF2/JH6 | QVQLVES-GGGVVQPGRSLRL SCAASG-FTFS | S-----YGMH | WVRQAPGK GLEWVT | VIWND---GSNKYYADS VKG | RFTISRDNSKNTLYLQMNSL RAEDTALYYCAR | DLDKRNFPY------YYYYGMDV | WGQGT TVTVS S |
| iPS:4 37024 | 21-225_194F11 | VH3|3-33/D7|7-27/RF2/JH6 | QVQLVES-GGGVVQPGRSLRL SCAASG-FTFS | S-----YGMH | WVRQAPGK GLEWVA | VIWND---GSKKYHVDS VKG | RFTISRDNSKNTLYLQMNSL RAEDTALYYCAR | DLDKRNFPY------YYYYGMDV | WGQGT TVTVS S |
| iPS:4 37028 | 21-225_194G12 | VH3|3-33/D7|7-27/RF2/JH6 | QVQLVES-GGGVVQPGRSLRL SCAASG-FTFS | S-----YGMH | WVRQAPGK GLEWVT | VIWND---GSNKYYADS VKG | RFTISRDNSKNTLYLQMNSL RAEDTALYYCAR | DLDKRNFPY------YYYYGMDV | WGQGT TVTVS S |
| | Germline VH4|4-34/D6|6-19/RF3/JH3 | | | | | | | |
| iPS:4 36290 | 21-225_205G3 | VH4|4-34/D6|6-19/RF3/JH3 | QVQLQQW-GAGLLKPSETLSL TCAVFG-GSFS | G-----MYWS | WIRQPGK GLEWIG | EMYH----FGKTNINPS LKS | RVTMSVDTSKKQFSLKLSSV TAADTAVYYCAR | VGQWL---------AFDI | WGQGT MVTVS S |
| | Germline VH3|3-30.3/D4|4-17/RF2/JH1 | | | | | | | |
| iPS:4 36306 | 21-225_201H4 | VH3|3-30.3/D4|4-17/RF2/JH1 | QVQLVES-GGGVVQPGRSLRL SCAASG-FTFS | S-----YAMH | WVRQAPGK GLEWVA | AIWYD---GSNKYNADS VKG | RFTISRDNSKNTLYMQMNSL RAEDTAVYYCAR | DVGTVG--------ATYFDC | WGPGT LVTVS S |
| | Germline VH1|1-18/D1|1-1/RF1/JH6 | | | | | | | |
| iPS:4 36362 | 21-225_210C12 | VH1|1-18/D1|1-1/RF1/JH6 | QVQLVQS-GAEVKKPGASVKV SCKASG-YTFT | N-----NGIS | WVRQAPGQ GLEWMG | WINAY---NGHTNYAQK FQG | RVTMTTDTSTSTAYMELRSL RSDDTAVYYCAR | DPTVTHY------YYYGMDV | WGQGT TVTVS S |
| iPS:4 36374 | 21-225_211C10 | VH1|1-18/D1|1-1/RF1/JH6 | QVQLVQS-GAEVKKPGASVKV SCKASG-YTFT | R-----HGIS | WVRLAPGQ GLEWMG | WISAY---NGLTNYAQK FQG | RVTMTTDTSTSTGYMELRSL RSDDTAVYYCAR | DPTVTHY------YYYGMDV | WGQGT TVTVS S |
| | Germline VH3|3-33/D3|5-18/RF3/JH6 | | | | | | | |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:4 36366 | 21-225_211A3 | VH3/3-33/D5/5-18/RF3/J H6 | QVQLVES-GGGVVQPGRSLRL SCAVSG-ITFS | S-----YGMH | WARQAPGK GLEWVA | VIWYD---GSNKNYEDS VKG | RFTISRDNSKNTLYLQMNSL RAEDTAVYYCAR | DGSYGY-----------DGMDV | WGQGT TVTVS S |
| iPS:4 36388 | 21-225_212H11 | VH3/3-33/D5/5-18/RF3/J H6 | QVQLVES-GGGVVQPGRSLRL SCAVSG-ITFS | S-----YGMH | WARQAPGK GLEWVA | VIWYD---GSNKNYEDS VKG | RFTISRDNSKNTLYLQMNSL RAEDTAVYYCAR | DGSYGY-----------DGMDV | WGQGT TVTVS S |
| iPS:4 36396 | 21-225_213E5 | VH3/3-33/D5/5-18/RF3/J H6 | QVQLVES-GGGVVQPGRSLRL SCAVSG-ITFS | S-----YGMH | WARQAPGK GLEWVA | VIWYD---GSNKNYEDS VKG | RFTISRDNSKNTLYLQMNSL RAEDTAVYYCAR | DGSYGY-----------DGMDV | WGQGT TVTVS S |
| iPS:4 36454 | 21-225_217B10 | VH3/3-33/D5/5-18/RF3/J H6 | QVQLVES-GGGVVQPGRSLRL SCAVSG-ITFS | S-----YGMH | WARQAPGK GLEWVA | VIWYD---GSNKNYEDS VKG | RFTISRDNSKNTLYLQMNSL RAEDTAVYYCAR | DGSYGY-----------DGMDV | WGQGT TVTVS S |
| iPS:4 36668 | 21-225_147B9 | VH3/3-33/D5/5-18/RF3/J H6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | DRDYGDPPY-----YYYYGMDV | WGQGT TVTVS S |
| iPS:4 36688 | 21-225_148C8 | VH3/3-33/D5/5-18/RF3/J H6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | DRDYGDPPY-----YYYYGMDV | WGQGT TVTVS S |
| iPS:4 36706 | 21-225_149A11 | VH3/3-33/D5/5-18/RF3/J H6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | DRDYGDPPY-----YYYYGMDV | WGQGT TVTVS S |
| iPS:4 36760 | 21-225_155E10 | VH3/3-33/D5/5-18/RF3/J H6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | DRDYGDPPY-----YYYYGMDV | WGQGT TVTVS S |
| iPS:4 36966 | 21-225_190C3 | VH3/3-33/D5/5-18/RF3/J H6 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAN | WYYYY-----------YGMDV | WGQGT TVTVS S |
| iPS:4 36976 | 21-225_190D8 | VH3/3-33/D5/5-18/RF3/J H6 | QVQLVES-GGDVVQPGRSLRL SCEASG-FTFS | S-----YGLH | WVRQAPGK GLEWVA | VIWYD---GSNKYYADS VKG | RFTISRDNSKNTLYLQMNSL RAEDTAVYYCAN | WYYYY-----------YGMDV | WGQGT TVTVS S |
| iPS:4 37168 | 21-225_218G4 | VH3/3-33/D5/5-18/RF3/J H6 | QVQLVES-GGGVVQPGRSLRL SCAASG-FTFS | S-----YGLH | WVRQAPGK GLEWVA | VIWYD---GSNKYYADS VKG | RFTISRDNSKNTLYLQMNSL NVEDTAVYYCAN | WYYYY-----------YGMDV | WGQGT TVTVS S |
| VH3/3-33/D5/5-18/RF3/JH6 | | | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36368 | 21-225_211G3 | VH3/3-33/D5/5-24/RF3/JH5 | QVQLVES-GGGVVQPGRSLRL SCAASG-FTFS | N-----YGMH | WVRQAPGK GLEWVA | VIWHD---GSNKYYADS VKG | RFTISRDNSKNTLYLQMNSL RAEDTAVYYCAR | LDYSNY------GWFDP | WGQGT LVTVS S |
| iPS:4 36426 | 21-225_215C7 | VH3/3-33/D5/5-24/RF3/JH5 | QVQLVES-GGGVVQPGRSLRL SCAASG-FTFS | Y-----YGMH | WVRQAPGK GLEWVA | VIWHD---GSNKYYADS VKG | RFTISRDNSKNTLYLQMNSL RAEDTAVYYCAR | LDYSNY------GWFDP | WGQGT LVTVS S |
| iPS:4 36432 | 21-225_215H12 | VH3/3-33/D5/5-24/RF3/JH5 | QVQLVES-GGGVVQPGRSLRL SCAASG-FTFS | N-----YGMH | WVRQAPGK GLEWVA | VIWHD---GSNKYYADS VKG | RFTISRDNSKNTLYLQMNSL RAEDTAVYYCAR | LDYSNY------GWFDP | WGQGT LVTVS S |
| | Germline | H_FR1 | H_CDR1 | H_FR2 | H_CDR2 | H_FR3 | H_CDR3 | H_FR4 |
| | VH1/1-18/D4/4-11/RF2/JH6 | | | | | | | |
| iPS:4 36402 | 21-225_213H12 | VH1/1-18/D4/4-11/RF2/JH6 | QVQLVQS-GAEVKKPGASVKV SCKASG-FTFT | S-----YGIN | WVRQAPGQ GLEWMG | WISVH---NGNTDYAQK FQG | RVIMTDTSTAYMELRSL RSDDTAVYYCAR | DYYY------GMDV | WGQGT KVTVS S |
| iPS:4 36500 | 21-225_222H3 | VH1/1-18/D4/4-11/RF2/JH6 | QVQLVQS-GAEVKKPGASVKV SCKASG-FTFT | S-----YGIN | WVRQAPGQ GLEWMG | WISVI---NGNTNYAQK LQG | RVIMTDTSTAYMELRSL RSDDTAVYYCAR | DYYY------GFDV | WGQGT TVTVS S |
| iPS:4 36520 | 21-225_223G10 | VH1/1-18/D4/4-11/RF2/JH6 | QVQLVQS-GAEVKKPGASVKV SCKASG-FTFT | S-----YGIN | WVRQAPGQ GLEWMG | WISVY---SGNTNYAQK LQG | RVIMTDTSTAYMELRSL RSDDTAVYYCAR | DYYY------GMDV | WGQGT TVTVS S |
| | Germline | H_FR1 | H_CDR1 | H_FR2 | H_CDR2 | H_FR3 | H_CDR3 | H_FR4 |
| | VH3/3-48/D2/2-21/RF1/JH4 | | | | | | | |
| iPS:4 36436 | 21-225_216F10 | VH3/3-48/D2/2-21/RF1/JH4 | EVQLVES-GGGLVQPGGSLRL SCAASG-FSFR | S-----YSMN | WVRQAPGK GLEWVS | YITGS---SSTIYYADS VKG | RFTISRDNAKNSLYLQMNSL RDEDTAVYYCAR | SGLA------VEDY | WGQGT LVTVS S |
| | Germline | H_FR1 | H_CDR1 | H_FR2 | H_CDR2 | H_FR3 | H_CDR3 | H_FR4 |
| | VH3/3-48/D6/6-6/RF1/JH4 | | | | | | | |
| iPS:4 36448 | 21-225_217A3 | VH3/3-48/D6/6-6/RF1/JH4 | EVQLVES-GGGLVQPGGSLRL SCAASG-FTFS | S-----YNMN | WVRQAPGK GLEWVS | YISSS---RMIIYYADS VKG | RFTISRENAKNSLSLQMDSL RDEDTAVYYCAR | DGSYSSG------WYWGFDY | WGQGT LVTVS S |
| | Germline | H_FR1 | H_CDR1 | H_FR2 | H_CDR2 | H_FR3 | H_CDR3 | H_FR4 |
| | VH4/4-39/D6/6-19/RF1/JH6 | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36472 | 21-225_220E1 | VH4/4-59/D6/6-19/RF3/J H6 | QVQLQES-GPGLVKPSETLSL TCTVSG-GSIS | T------YYWS | WIRQPPGK GLEWIG | YIYY----SGTYNPS LKS | RVTISVDTSKNQFSLKLSSV TAADTAVYYCAR | DQQWLVRGR------DNYYGMDV | WGQGT TVTVS S |
| | | Germline | | | | | | | |
| | VH3/3-23/D2/2-15/RF3/JH4 | | | | | | | | |
| iPS:4 36504 | 21-225_222H4 | VH3/3-23/D2/2-15/RF3/J H4 | EVQLLES-GGGLVQPGGSLRL SCAASG-FTFS | N------FAMS | WVRQAPGK GLEWVS | SIVGS---GGRTYYADS VKG | RFTISRDNSKNTLYLQMNSL RAEDTAVYYCAK | DPYRVAV------AGAFDY | WGQGT LITVS S |
| iPS:4 36510 | 21-225_222H8 | VH3/3-23/D2/2-15/RF3/J H4 | EVQLLES-GGGLVQPGGSLRL SCAASG-FTFS | N------FAMS | WVRQAPGK GLEWVS | SIVGS---GGRTYYADS VKG | RFTISRDNSKNTLYLQMNSL RAEDTAVYYCAK | DPYRVAV------AGAFDY | WGQGT LITVS S |
| | | Germline | | | | | | | |
| | VH3/3-23/D3/3-22/RF2/JH1 | | | | | | | | |
| iPS:4 36526 | 21-225_224A1 | VH3/3-23/D3/3-22/RF2/J H1 | EVQVLES-GGGLVQPGGSLRL SCAASG-FTFS | S------YAMS | WVRQAPGK GLEWVS | AISGR---GGSTYYADA VKG | RFTISRDNSKNTLYLQMNSL RAEDTAVYYCAK | GSYDSSG------YYHYLDR | WGQGT LVTVS S |
| | | Germline | | | | | | | |
| | VH1/1-02/D4/4-23/RF2/JH6 | | | | | | | | |
| iPS:4 36536 | 21-225_224G1 | VH1/1-02/D4/4-23/RF2/J H6 | QVQLVQS-GAEVKKPGASVKV SCKASG-YTFT | G------YYIH | WVRQAPGQ GLEWMG | WINPY---SGDTNYAQK FQG | RVTMTRDTSISTAYMELSRL REDDTAVFYCAR | DWGGYSS------YYYGMDV | WGQGT TVTVS S |
| iPS:4 36548 | 21-225_224A7 | VH1/1-02/D4/4-23/RF2/J H6 | QVQLVQS-GAEVKKPGASVKV SCKASG-YTFT | G------YYIH | WVRQAPGQ GLEWMG | WINPY---SGDTNYAQK FQG | RVTMTRDTSITTAYMELSRL REDDTAVFYCAR | DWGGYSS------YYYGMDV | WGQGT TVTVS S |
| iPS:4 36558 | 21-225_224C11 | VH1/1-02/D4/4-23/RF2/J H6 | QVQLVQS-GAEVKKPGASVKV SCKASG-YTFT | G------YYIH | WVRQAPGQ GLEWMG | WINPY---SGDTNYAQK FQG | RVTMTRDTSISTAYMELRRL REDDTAVFYCAR | DWGGYSS------YYFGMDV | WGQGT TVTVS S |
| iPS:4 36562 | 21-225_224H11 | VH1/1-02/D4/4-23/RF2/J H6 | QVQLVQS-GAEVKKPGASVKV SCKASG-YTFT | G------YYIH | WVRQTPGQ GLEWMG | WINPY---SGDTNYAQK FQG | RVTMTRDTSISTAYMELRRL REDDTAVFYCAR | DWGGYSS------YYYGMDV | WGQGT TVTVS S |
| iPS:4 36572 | 21-225_225G4 | VH1/1-02/D4/4-23/RF2/J H6 | QVQLVQS-GAEVKKPGASVKV SCKASG-YTFT | G------YYIH | WVRQAPGK GLEWMG | WINPY---SGDTNYAQK FQG | RVTMTRDTSISTAYMELRRL REDDTAVFYCAR | DWGGYSS------YYYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36606 | 21-225_226G8 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTYKYAQK FQG | RVTMTRDTSISTAYMELSRL REDDTAVFYCAR | DWGGYSS------ ------YYYGMDV | WGQGT TVTVS S |
| iPS:4 36610 | 21-225_226F9 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTYKYAQK FQG | RVTMTRATSISTAYMELSRL REDDTAVFYCAR | DWGGYSS------ ------YYYGMDV | WGQGT TVTVS S |
| iPS:4 36612 | 21-225_226H9 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTNSAQK FQG | RVTMTRDTSISTAYMELSRL REDDTAVFYCAR | DWGGYSS------ ------YYYGMDV | WGQGT TVTVS S |
| iPS:4 36614 | 21-225_226F10 | VH1|1-02|D4|4-23|RF2|JH6 | QVQLVQS-GGEVKKLRASVKV SCKASG-YTFT | G------YYIH | WVRQAPGQ GLEWMG | WINPY---- SGDTNYAQK FQG | RVTMTRDTSISTAYMELSRL RLDDTAVFYCAR | DWGGYSS------ ------YYYGMDV | WGQGT PVTVS S |
| iPS:4 36618 | 21-225_226E11 | VH1|1-02|D4|4-23|RF2|JH6 | QVQLVQS-GAEVKKFGASVKV SCKASG-YTFT | G------YYIH | WVRQAPGQ GLEWMG | WINPY---- SGDTNYAQK FQG | RVTMTRATSISTAYMELSRL REDDTAVFYCAR | DWGGYSS------ ------YYYGMDV | WGQGT TVTVS S |
| iPS:4 36624 | 21-225_226H12 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTNYAQK FQG | RVTMTRDTSISTAYMELRRL REDDTAVFYCAR | DWGGYSS------ ------YYYGMDV | WGQGT TVTVS S |
| iPS:4 36626 | 21-225_227C1 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTNYAQK FQG | RVTMTRDTSISTAYMELSRL RFDDTAVFYCAR | DWGGYSS------ ------YYYGMDV | WGQGT TVTVS S |
| iPS:4 36628 | 21-225_227F2 | VH1|1-02|D4|4-23|RF2|JH6 | QVHLVQS-GAEVKKPGASVKV SCKASG-YTFT | G------YYIH | WVRQAPGQ GLEWMG | WINPY---- SGDTNYAQK FQG | RVTMTRDTSVSTAYMELSRL REDDTAVFYCAR | DWGGYSS------ ------YYYGMDV | WGQGT TVTVS S |
| iPS:4 36640 | 21-225_227A8 | VH1|1-02|D4|4-23|RF2|JH6 | QVQLVQS-GAEVKKPGASVKV SCKASG-YTFT | G------YYIH | WVRQAPGQ GLEWMG | WINPY---- SGDTNYAQK FQG | RVTMTRDTSVSTAYMELSRL REDDTAVFYCAR | DWGGYSS------ ------YYYGMDV | WGQGT TVTVS S |
| | Germline VH4|4-39|D4|4-17|RF1|JH4 | | | | | | | H_CDR3 | H_FR4 |
| iPS:4 36538 | 21-225_224C3 | VH4|4-39|D4|4-17|RF1|JH4 | QLQLQES-GPGLVKSSETLSL TCTVSG-GSIS | RS---SYYWG | WIRQPPGK GLEMIG | NIYY----- SGSTYYNPS LKS | RVTISVDTSKNQFSLKLSSV TAADTAVYYCAR | QGRDW------ ----------GVDY | GGQGT LVTVS S |
| | Germline VH3|3-23|D4|4-11|RF2|JH5 | | H_FR1 | H_CDR1 | H_FR2 | H_CDR2 | H_FR3 | H_CDR3 | H_FR4 |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36546 | 21-225_224D6 | VH3J3-23/D4/4-11/RF2/JH5 | EVQVLES-GGGLVQPGGSLRL SCAASG-SIFS | S-----DAMS | WVRQAPGK GLEWVS | AISGS---GDNTYIADS VKG | RFTISRDNSKNTLYLQMNSL RAEDTAVYYCAK | VYSAYD------SHWFDP | WGQGT LVTVS S |
| | | Germline | VH1/1-46/D6/6-6/RF2/JH6 | | | | | | |
| iPS:4 36568 | 21-225_225B3 | VH1/1-46/D6/6-6/RF2/JH6 | QVQLVQS-GAEVKKPGASVKV SCKASG-YTFT | S-----YYMH | WVRQAPGQ GLEWMG | IINPS---GGSTYAQK FQG | RVTMTRDTSISTVYMELSSL RSADTAVYYCAR | DLAARSIY------YYFGMDV | WGQGA TVTVS S |
| | | Germline | | | | | | | |
| iPS:4 36580 | 21-225_225E7 | VH4/4-30.1/D4/4-17/RF2/JH6 | QVQLQES-CPGLVKPSQTLSL TCTVSG-NSIS | SG---HYYWS | WIRQHPGK GLEWIG | FIYY----TGSTYNPS LKS | RVTISVDTSKNQFSLKLSSV TAADTAVYYCAR | EAGDYG------YYGMDV | WGQGT TVTVS S |
| iPS:4 36926 | 21-225_78D10 | VH4/4-30.1/D4/4-17/RF2/JH6 | QVQLQES-CPGLVKPSQTLSL TCTVSG-GSIS | SG---GYYWS | WIRQHPGK GLEWIG | YIYY----IGSVYNPS LKS | RVTISVDTSKNQFSLKLSSV TAADTAVYYCAR | DAPDF------GMDV | WGQGT TVTVS S |
| | | Germline | | | | | | | |
| iPS:4 36592 | 21-225_226B1 | VH3/3-33/D4/4-17/RF2/JH1 | EVQLVES-GGGVVQFGRSLRL SCAASG-FTFS | T-----YGMH | WVRQAPGK GLEWVA | IIWYD---GGYKYYADS VKG | RFTISRDNSKNTLFLQMNSL RAEDTAVYYCAR | DHYDFW------SGYLTH | WGQGT LVTVS S |
| | | Germline | VH3/3-33/D4/4-17/RF1/JH6 | | | | | | |
| iPS:4 36652 | 21-225_146B11 | VH3/3-23/D7/7-27/RF1/JH6 | EVQLLES-GGGLVQPGGSLRL SCAASG-FTFS | S-----YAMS | WVRQAPGK GLEWVS | VISGG---GSSTYYADS VKG | RFTISRDNSKNTLYLQMNSL RAEDIAVYYCAK | WRGNPT------DYGMDV | WGQGT TVTVS S |
| iPS:4 36654 | 21-225_146C11 | VH3/3-23/D7/7-27/RF1/JH6 | EVQLLES-GGGLVQFGGSLRL SCAASG-IIFS | S-----YAMS | WVRQAPGK GLEWVS | VISGG---GSSTYYADS VKG | RFTISRDNSKNTLYLQMNSL RAEDTAVYYCAR | WRGNPT------DYGMDV | WGQGT TVTVS S |
| iPS:4 36658 | 21-225_146A2 | VH3/3-23/D7/7-27/RF1/JH6 | EVQLLES-CGGLVQPGGSLRL SCAASG-FTFS | S-----YAMS | WVRQAPGK GLEWVS | VISGG---GSSTYYADS VKG | RFTISRDNSKNTLHLQMNSL RAEDTAVYYCAR | WRGNPT------DYGMDV | WGQGT TVTVS S |

Figure 51 (Continued)

| | | | | | | | | | |
|---|---|---|---|---|---|---|---|---|---|
| iPS:4 36664 | 21-225_147E7 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36676 | 21-225_147E11 | VH3/3-23/D7/7-27/RF1/JH6 | EVQLLES-GGGLVQPGGSLRLSCAASG-FTFS | N-----YVMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36678 | 21-225_147B12 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36686 | 21-225_148G6 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNMHLQMNSL RAEDTAVYYCAK | WRGNPT------DYGMDV | WGQGT TVTVS S |
| iPS:4 36694 | 21-225_148G11 | VH3/3-23/D7/7-27/RF1/JH6 | EVQLLES-GGGLVQPGGSLRLSCAASG-FTFS | S-----YPMS | WVRQAPGK GLEWVS | VISGG---GSSAYYADS VKG | RFTISRDNSKNTLYLQMNSL RAEDTAVYYCAK | WRGNPT------DYGMDV | WGQGT TVTVS S |
| iPS:4 36700 | 21-225_149C7 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36704 | 21-225_149C10 | VH3/3-23/D7/7-27/RF1/JH6 | EVQLLES-GGGLVQPGGSLRFSCAASG-FTFS | S-----HAMS | WVRQAPGK GLEWVS | IISGG---GSSTYYADS VKG | RFTISRDNSKNTLYLQMNSL RAEDTAVYYCAK | WRGNPT------DYGMDV | WGQGT TVTVS S |
| iPS:4 36710 | 21-225_150F6 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36714 | 21-225_150H11 | VH3/3-23/D7/7-27/RF1/JH6 | EVQLLES-GGGLVQPGGSLRLSCAASG-FTFS | T-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36718 | 21-225_151H5 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36722 | 21-225_151H7 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |
| iPS:4 36724 | 21-225_151B9 | VH3/3-23/D7/7-27/RF1/JH6 | EVQLLES-GGGLVQPGGSLRLSCAASG-FTFS | S-----YAMS | WVRQAPGK GLEWVS | VISGG---GSSTYYADS VKG | RFTISRDNSKNTLYLQMNSL RAEDTAVYYCAK | WRGNPT------DYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36728 | 21-225_152G6 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 36730 | 21-225_152D7 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DSGMDV | WGQGT TVTVS S |
| iPS:4 36742 | 21-225_154C4 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 36746 | 21-225_154E10 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 36758 | 21-225_155C10 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 36938 | 21-225_146A3 | VH3J3-23/D7J7-27/RF1/JH6 | EVQLLES-GGGLVQPGGSLRLSCAASG-FTFS | S-----YAMS | WVRQAPGK GLEWVS | VISGG----GTTTYYADS VKG | RFTISRDNSKNTLYLQMNSL RAEDTAVYYCAK | WRGNPT---------DYGMDV | WGQGT TVTVS S |
| iPS:4 37250 | 21-225_148C6 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 37252 | 21-225_148H11 | VH3J3-23/D7J7-27/RF1/JH6 | EVQLLES-GGGLVQPGGSLRLSCAASG-FTFS | S-----YAMS | WVRQAPGK GLEWVS | VISGG----GSSTYYADS VKG | RFTISRDNSKNTLYLQMNSL RAEDTAVYYCAK | WRGNPT---------DYGMDV | WGQGT TVTVS S |
| iPS:4 37282 | 21-225_207C9 | VH3J3-23/D7J7-27/RF1/JH6 | EVQLLES-GGGLVQPGGSLRLSCAASG-FTFS | S-----YAMS | WVRQAPGK GLEWVS | AISGS----GGSTYYADS VKG | RFTISRDNSKNTLYLQMNSL RAEDTAVYYCAK | AGGTTGSY-------YNGMDV | WGQGT TVTVS S |
| Germline | VH3J3-48/D4J4-11/RF2/JH6 | | EVQLVES-GGGLVQPGGSLRLSCAASG-FTFS | N-----YNMN | WVRQAPGK GLEWVS | YISSS----SSTYYADS VKG | RFTISRDNAKNSLYLQMNSL RDEDTAVYYCAR | DYSNYY---------YYGMDV | WGQGT TVTVS S |
| iPS:4 36660 | 21-225_146D8 | VH3J3-48/D4J4-11/RF2/JH6 | EVQLVES-GGGLVQPGGSLRLSCAASG-FTFS | N-----YNMN | WVRQAPGK GLEWVS | YISRS----SNIKYVDS VKG | RFTISRDNAKNSLYLQMNSL RDEDTAVYYCAR | DRSGSYGY-------FYYYGLDV | WGQGT TVTVS S |
| iPS:4 36682 | 21-225_146A8 | VH3J3-48/D4J4-11/RF2/JH6 | EVKLVES-GGGLVQPGESLRLSCVASG-FTFS | N-----YNMN | WVRQAPGK GLEWVS | YISRS----SNIKYYADS VRG | RFTISRDNAKNSLYLQMNSL RDEDTAVYYCAR | DRSGSYGY-------FYYYGLDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36684 | 21-225_146B6 | VH3/3-48/D4/4-11/RF2/JH6 | EVQLVES-GGGLVQPGGSLRL SCAASG-FTFS | S-----YNMN | WVRQAPGK GLEWVS | YISRS---SNIKHYADS VKG | RFTISRDNAKNSLYLQMDSL RDEDTAVYYCAR | DRSGSYGY------FYYYGLDV | WGQGT TVTVS S |
| iPS:4 36696 | 21-225_149A1 | VH3/3-48/D4/4-11/RF2/JH6 | EVQLVES-GGGLVQPGGSLRL SCAASG-FTFS | S-----YNMN | WVRQAPGK GLEWVS | YISRS---SNIKHYADS VKG | RFTISRDNAKNSLYLQMNSL RDEDTAVYYCAR | DRSGSYGY------FYYYGLDV | WGQGT TVTVS S |
| iPS:4 36712 | 21-225_150F9 | VH3/3-48/D4/4-11/RF2/JH6 | EMQLVES-GGGLVQPGGSLRL SCAASG-FTFS | S-----YNMN | WVRQVPGK GLEWVS | YISRS---SNIKHYADS VKG | RFTISRDNAKNSLYLQMNSL RDEDTAVYYCAR | DRSGSYGY------FYYYGLDV | WGQGT TVTVS S |
| iPS:4 36762 | 21-225_156H2 | VH3/3-48/D4/4-11/RF2/JH6 | EVQLVES-GGGLIQPGGSLRL SCAASG-FTFS | N-----YNMN | WVRQAPGK GLEWVS | YISRS---SNIKYYADS VKG | RFTISRDNAKNSLYLQMNSL RDEDTAVYYCAR | DRSGSYGY------FYYYGMDV | WGQGT TVTVS S |
| iPS:4 36820 | 21-225_179D10 | VH3/3-48/D4/4-11/RF2/JH6 | EVQLVES-GGGLVQPGGSLRF SCAASG-FTFS | S-----YSMN | WVRQAPGK GLEWVA | YISSS---GSITYYADS VQG | RFTISRDNAKNSLYLQMNSL RDEDTAVYRCAR | DSRKGF------YYYGLDV | WGQGT TVTVS S |
| iPS:4 37262 | 21-225_170E4 | VH3/3-48/D4/4-11/RF2/JH6 | EVQLVES-GGGSVQPGGSLRL SCAASG-FTFS | S-----YSMN | WVRQAPGK GLEWVS | YISSS---GSIKYIADS VEG | RFTISRDNAKNSLDLQMNSL RDEDTAVYRCAR | DSRKGF------YYGLDV | WGQGT TVTVS S |
| | Germline | VH1/1-08/D5/5-12/RF1/JH6 | | | | | | | |
| iPS:4 36662 | 21-225_147D7 | VH1/1-08/D5/5-12/RF1/JH6 | QVQLVQS-GAEVKKPGASVKV SCKASG-YTFT | S-----YDIN | WVRQATGQ GLEWMG | MMNPN---SGNTGYAQK FQG | RVTMTRNTSISTAYMELRSL RSEDTAVYYCAR | ADIVLVEAAI---FYNYFAMDV | WGQGT TVTVS S |
| | Germline | VH1/1-02/D3/3-3/RF2/JH6 | | | | | | | |
| iPS:4 36666 | 21-225_147B8 | VH1/1-02/D3/3-3/RF2/JH6 | QVQLVQS-GAEVKKPGASVKV SCKASG-YTFT | D-----YYLH | WVRQAPGQ GLEWMG | WINPN---SGDTNVAQK FQG | RVTMTRDTSISTAYMELSRL RSEDTAVYYCAR | DRDSGSSYP---YYYYGMDV | WGQGT TVTVS S |
| | Germline | VH3/3-33/D3/3-3/RF2/JH6 | | | | | | | |
| iPS:4 36672 | 21-225_147F9 | VH3/3-33/D3/3-3/RF2/JH6 | QVQLVES-GGGVVQPGRSLRL SCAASG-FTFS | T-----YGMH | WVRQAPGK GLEWVA | VIWYG---GSDKDIADS VKG | RFTISRDISKNTLYLQMNSL RAEDTAVYYCAR | DRDYCSGGIC------FYYYYGMDV | WGQGT TVTVS S |

Figure 51 (Continued)

| | | | | | | | | | |
|---|---|---|---|---|---|---|---|---|---|
| iPS:4 36674 | 21-225_147G9 | VH3J3-33/D3J3-3\|RF2/JH6 | QVQLVES-GGGVVQPGRSLRL SCAASG-FTFS | T------YGMH | WVRQAPGK GLEWVA | VIWYG---GSDKDYADS VKG | RFTISRDISKNTLYLQMNSL RAEDTAVYYCAR | DRDYCSGGSC----------PYYYYYGMDV | WGQGT TVTVS S |
| iPS:4 36690 | 21-225_148A9 | VH3J3-33/D3J3-3\|RF2/JH6 | QVQLVES-GGGVVQPGRSLRL SCAASG-FTFS | T------YGMH | WVRQAPGK GLEWVA | VIWYG---GSDKDYADS VKG | RFTISRDISKNTLYLQMNSL RAEDTAVYYCAR | DRDYCSGTC----------PYYYYYGMDV | WGQGT TVTVS S |
| iPS:4 36708 | 21-225_150D3 | VH3J3-33/D3J3-3\|RF2/JH6 | QVQLVES-GGGVVQPGRSLRL SCAASG-FTFS | T------YGMH | WVRQAPGK GLEWVA | VIWYG---GSNKDYADS VKG | RFTISRDNSKNTLYLQMNSL RAEDTAVYYCAR | DRDYCSGTC----------PYYYYYGMDV | WGQGT TVTVS S |
| iPS:4 36716 | 21-225_151F3 | VH3J3-33/D3J3-3\|RF2/JH6 | QVQLVES-GGGVVQPGRSLRL SCAASG-FTFS | T------YGMH | WVRQAPGK GLEWVA | VIWYG---GSNTDYADS VKG | RFTISRDISKNTLYLQMNSL RAEDTAVYYCAR | DRDYCSGGSC----------PYYYYYGMDV | WGQGT TVTVS S |
| iPS:4 36738 | 21-225_153D9 | VH3J3-33/D3J3-3\|RF2/JH6 | QVQLVES-GGGVVQPGRSLRL SCAASG-FTFS | T------YGMH | WVRQAPGK GLEWVA | VIWYG---GSNKDYADS VKG | RFTISRDISKNTLYLQMNSL RAEDTAVYYCAR | DRDYCSGGSC----------PYYYYYGMDV | WGQGT TVTVS S |
| iPS:4 36740 | 21-225_154C3 | VH3J3-33/D3J3-3\|RF2/JH6 | QVQLVES-GGGVVQPGRSLRL SCTASG-FTFS | T------YGMH | WVRQAPGK GLEWVA | VVWYG---GNNKDYADS VKG | RFTISRDNSKNTLYLQMNSL RAEDTAVYYCAR | DRDYCSGGSC----------PYYYYYGMDV | WGQGT TVTVS S |
| iPS:4 36748 | 21-225_154D11 | VH3J3-33/D3J3-3\|RF2/JH6 | QVQLVES-GGGVVQPGRSLRL SCAASG-FNVS | T------YGMH | WVRQAPGK GLEWVA | VIWYG---GSNKDYADS VKG | RFTISRDISKNTLYLQMNSL RAEDTAVYYCAR | DRVFCSGTSC----------PYYYYYGMDV | WGQGT TVTVS S |
| iPS:4 36764 | 21-225_158E9 | VH3J3-33/D3J3-3\|RF2/JH6 | QVQLVES-GGGVVQPGRSLRL SCAASG-FTFS | S------YGMH | WVRQAPGK GLEWVA | VIWYD---GSSKYADS VKG | RFTISRDNSKNTLYLQMNSL RAEDTAVYYCAR | DRVFCSGTSC----------PYYYYYGMDV | WGQGT TVTVS S |
| iPS:4 36774 | 21-225_161E10 | VH3J3-33/D3J3-3\|RF2/JH6 | QVQLVES-GGGVVQPGRSLRL SCAASG-FTFS | S------YGMH | WVRQAPGK GLEWVA | VIWYD---GSNKYVDS VKG | RFTISRDNSKNTLYLQMNSL RAEDTAVYYCAR | DRVFCSGTSC----------PYYYYYGMDV | WGQGT TVTVS S |
| iPS:4 36916 | 21-225_74A9 | VH3J3-33/D3J3-3\|RF2/JH6 | QVQLVES-GGGVVQPGRSLRL SCAASG-FTFS | S------YGMH | WVRQAEGK GLEWVA | VIWYG---GNNKSYADS VKG | RFTISRDISKNTLFLQMNSL RAEDTAVYYCAR | DRDYCSGTSC----------PYYYYYGMDV | WGQGT TVTVS S |
| iPS:4 36940 | 21-225_146B8 | VH3J3-33/D3J3-3\|RF2/JH6 | QVQLVES-GGGVVQPGRSLRL SCAASG-FTFS | T------YGMH | WVRQAEGK GLEWVA | VVWYG---GNDKDFADS VTG | RFTISRDISKNTLYLQMNSL RAEDTAVYYCAR | DRDYCSGSC----------PYYYYYGMDV | WGQGT TVTVS S |
| iPS:4 37258 | 21-225_153F9 | VH3J3-33/D3J3-3\|RF2/JH6 | QVHLVES-GGGVVQPGRSLRL SCAASG-FTIS | T------YGMH | WVRQGPGK GLEWVA | VIWYG---GSDTDYADS VKG | RFTISRDISKNTLYLQMNSL RAEDTAVYYCAR | DRDYCSGGNC----------PYYYYYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4-30.1/D7/7-27/RF3/JH5 | | QVQLQES-GPGLVKPSQTLSL TCTVSG-GSIS | SG YHWS | WIRQHPGK GLEWIG | YIYY SGSTYYNPS LKS | RVTISVDTSKNQFSLKLTSV TAADTAVYYCAR | NKCK---------NKDP | WGQGT LVTVS S |
| iPS:4 36680 | VH4-30.1/D7/7-27/RF3/JH5 | QVQLQES-GPGLVNPSQTLSL TCAVSG-GSIS | SG---YHWS | WIRQHPGK GLEWIG | YIYY---SGSTYYNPS LKS | RVTISVDTSKNQFSLKLTSV TAADTAVYYCAR | DWGGYDS------SGWFDP | WGQGT LVTVS S |
| iPS:4 36750 | VH4-30.1/D7/7-27/RF3/JH5 | QVQLQES-GPGLVNPSQTLSL TCGVSG-GSIS | SG---YYYWS | WIRQHPGK GLEWIG | YIYY---SGSTYYNPS LKS | RVSISLDTPKNQFSLKLTSV TAADTAVYYCAR | DWGGYDS------SGWFDP | WGQGT LVTVS S |
| | Germline | H_FR1 | H_CDR1 | H_FR2 | H_CDR2 | H_FR3 | H_CDR3 | H_FR4 |
| VH3-07/D6/6-13/RF1/JH4 | | EVQLVES-GGGLVQPGGSLRL SCAASG-FTFS | S YMNS | WVRQAPGK GLEWVA | NIKQD---GSEKYYVDS VKG | RFTISRDNAKNSLYLQMNSL RAEDTAVYYCAR | GYSSSW---------YFDY | WGQGT LVTVS S |
| iPS:4 36698 | VH3-07/D6/6-13/RF1/JH4 | EVQLVES-GGGLVQPGGSLRL SCAASG-FTFS | G-----YWMN | WVRQAPGK GLEWVA | NIKQD---GSEKYYVDS VKG | RFTISRDNAKNSLYLQMNSL RAEDTAVYYCAR | GMYSSG---------WYIFDY | WGQGT LVTVS S |
| | Germline | H_FR1 | H_CDR1 | H_FR2 | H_CDR2 | H_FR3 | H_CDR3 | H_FR4 |
| VH3-21/D6/6-19/RF2/JH5 | | EVQLVES-GGGLVKPGGSLRL SCAASG-FTFS | S YSMN | WVRQAPGK GLEWVS | SISSS---GSTIYYADS VKG | RFTISRDNAKNSLYLQMNSL RAEDTAVYYCAR | GIAVAG---------SWFDP | WGQGT LVTVS S |
| iPS:4 36702 | VH3-21/D6/6-19/RF2/JH5 | EVQLVES-GGGLVKPGGSLRL SCAASG-FTFS | S-----YSMN | WVRRAPGK GLEWVS | AISSI---GSYIYYADS VKG | RFTISRDNAKNSLYLQMNSL RAEDTAVYYCAR | TAVAGI---------GWFDP | WGQGT LVTVS S |
| | Germline | H_FR1 | H_CDR1 | H_FR2 | H_CDR2 | H_FR3 | H_CDR3 | H_FR4 |
| VH5-51/D3/3-22/RF2/JH6 | | EVQLVQS-GAEVKKPGESLKI SCTGS-YSFT | S YWIG | WVRQMPGK GLEWMG | IIYPG---DSDTRYSPS FQG | QVTISADKSISTAYLQWSSL KASDTAMYYCAR | YYYDSSGYYY------YYYGMDV | WGQGT TVTVS S |
| iPS:4 36752 | VH5-51/D3/3-22/RF2/JH6 | EVQLVQS-GAEVKPGESLKI SCKGSG-YSFT | S-----YWIG | WVRQMPGK GLEWMG | LIYPG---ASDTRYSPS FQG | QVTISADKSISTAYLQWSSL KASDTAMYYCAR | QAIASKGR------YYYYGMDV | WGQGT TVTVS S |
| | Germline | H_FR1 | H_CDR1 | H_FR2 | H_CDR2 | H_FR3 | H_CDR3 | H_FR4 |
| VH3-33/D6/6-19/RF1/JH4 | | QVQLVES-GGGVVQPGRSLRL SCAASG-FTFS | S YGMH | WVRQAPGK GLEWVA | VIWYD---GSNKYYADS VKG | RFTISRDNSKNTLYLQMNSL RAEDTAVYYCAR | GYSSGW---------YFDY | WGQGT LVTVS S |
| iPS:4 36772 | VH3-33/D6/6-19/RF1/JH4 | QVQLVES-GGGVVQPGRSLRL SCAASG-FTFS | S-----YGMH | WVRQAPGK GLEWVA | VIWYD---GSNKYYADS VKG | RFTISRDNSKNTLYLQMNSL RAEDTAVYYCAR | VGYSGG---------WYIFDY | WGQGT LVTVS S |
| | Germline | H_FR1 | H_CDR1 | H_FR2 | H_CDR2 | H_FR3 | H_CDR3 | H_FR4 |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| | VH4/4-30.1/D2/2-2/RF2/JH6 | QVQLQES-GGLVKPSQTLSL TCTVSG-GSIS | SG---GYYW | WIRQHPGK GLEWIG | YIYY----SGSPYYNPS LKS | RFTISIDTSKNQFSLKLNSV TAADTAVYYCAR | GYSSTHCYT-------VYYYGMDV | WGRGT TVTVS S |
| iPS:4 36776 | 21-225_161F12 | QVQLQES-GPGLVKPSQTLSL TCTVSG-GSIS | SG---GYYWS | WIRQHPGK GLEWIG | YIYY----SGSPYYNPS LKS | RITISIDTSKNQFSLKLNSV TAADTAVYYCAR | SNCSSANCYT-------VGFYYYGLDV | WGRGT TVTVS S |
| iPS:4 36780 | 21-225_165H3 | QVQLQES-GPGLVKPSQTLSL TCTVSG-GSIS | SG---GYYWS | WIRQHPGK GLEWIG | YIYY----SGSPYYNPS LKS | RITISIDTSKNQFSLKLNSV TAADTAVYYCAR | SNCSSANCYT-------VGFYYYGMDV | WGQGT TVTVS S |
| | Germline | H_FR1 | H_CDR1 | H_FR2 | H_CDR2 | H_FR3 | H_CDR3 | H_FR4 |
| | VH3/3-33/D5/5-24/RF3/JH6 | EVQLVES-GGGVVQPGRSLRL SCAASG-FTFS | S-----YGMH | MVRQAPGK GLEWVA | VIWYD---GSNKYYADS VKG | RFTISRDNSKNTLYLQMNSL RAEDTAVYYCAR | VDTAMV--------YYYGMDV | WGQGT TVTVS S |
| iPS:4 36784 | 21-225_169C1 | QVQLVES-GGGVVQPGRSLRL SCAASG-FTLS | S-----NGMH | MVRQAPGK GLEWVA | VIWYD---GSNKYYADS VKG | RFTISRDTSKNTLYLQMNSL RAEDTAVYYCAR | DQYNRNDGPP-------AYYYYGLDV | WGQGT TVTVS S |
| iPS:4 36786 | 21-225_169A6 | QVQLVES-GGGVVQPGRSLRL SCAASG-FTLS | S-----NGMH | MVRQAPGK GLEWVA | VIWYD---GSNKYYADS VKG | RFTISRDNSKNTLSLQMNSL RAEDTAVYYCAR | DQYNRNDGPP-------AYYYYGMDV | WGQGT TVTVS S |
| iPS:4 36796 | 21-225_170A5 | QVQLVES-GGGVVQPGRSLRL SCAASG-LTFS | N-----CGMH | MVRQAPGK GLEWVA | IIWYD---GSNKYYADS VKG | RFTISRDNSKNTLDLQMNSL RAEDTAVYYCAR | DQYNRNDGPP-------AYYYYGLDV | WGQGT TVTVS S |
| iPS:4 36812 | 21-225_175C6 | QVQLVES-GGGVVQPGRSLRL SCAASG-LTFS | N-----CGMH | MVRQAPGK GLEWVA | IIWYD---GSNKYYADS VKG | RFTVSRDNSKNTLDLQMNSL RAEDTAVYYCAR | DQYNRNDGPP-------AYYYYGLDV | WGQGT TVTVS S |
| | Germline | H_FR1 | H_CDR1 | H_FR2 | H_CDR2 | H_FR3 | H_CDR3 | H_FR4 |
| | VH3/3-48/D5/5-18/RF1/JH6 | EVQLVES-GGGLVQPGGSLRL SCAASG-FTFS | S-----YSMN | MVRQAPGK GLEWVS | YISSS---SSTIFYADS VKS | RFTISRDNAKNSLYLQMNSL RDEDTAVYYCAR | VDTAMV--------YYYGMDV | WGQGT TVTVS S |
| iPS:4 36788 | 21-225_169B7 | EVQLVES-GGGLVQPGGSLRL SCAASG-FTFS | S-----YSLN | MVRQAPGK GLEWVS | YIGSS---GSTIFYADS VKG | RFTISRDNAKNSLYLQMNSL RDEDTAVYYCAR | GDTAGVT-------YYYYGMDV | WGQGT TVTVS S |
| iPS:4 36798 | 21-225_171F5 | EVQLVES-GGGLVQPGGSLRL SCAASG-FTFS | S-----YSLN | MVRQAPGK GLEWVS | YIGSS---GSTIFYADS VKG | RFTISRDNAKNSLYLQMNSL RDEDTAVYYCAR | GDTAGVT-------YYYYGMDV | WGQGT TVTVS S |
| iPS:4 36864 | 21-225_58G11 | EVQLVES-GGGLVQPGGSLRL SCAASG-FTFS | S-----YSMN | MVRQAPGK GLEWIS | YISTS---SSTIFYADS VKG | RFTISRDSAKNSLYLQMNSL RDEDTAVYYCAR | GDTAMVL-------YYYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36866 | 21-225_59F2 | VH3J3-48|D5|5-18|RF1|JH6 | EVQLVES-GGGLVQPGGSLRL SCGASG-FTFS | S-----YSMN | WVRQAPGK GLEWVS | YISGS---SNIYYTDS VKG | RFTIISRDNAKNSLYLQMNSL RDEDTAVYYCAR | ADTPMVL-------YFYGMDV | WGQGT TVTVS S |
| iPS:4 36872 | 21-225_60D2 | VH3J3-48|D5|5-18|RF1|JH6 | EVQLVES-GGGLVQPGGSLRL SCGASG-FTFS | S-----YSMN | WVRQAPGK GLEWVS | YISES---SNIYYTDS VKG | RFTIISRDNAMNSLYLQMNSL RDEDTAVYYCAR | ADTPMVL-------YFYGMDV | WGQGT TVTVS S |
| | | Germline | H_FR1 | H_CDR1 | H_FR2 | H_CDR2 | H_FR3 | H_CDR3 | H_FR4 |
| | VH3J3-33D5|5-24|RF1|JH6 | | | | | | | | |
| iPS:4 36790 | 21-225_169G11 | VH3J3-33|D5|5-24|RF1|JH6 | QVQLVES-GGGVVQPGRSLRL SCAASG-FTFS | S-----YGMH | WVRQAPGK GLEWVA | IIWYD---GSNKYYADS VKG | RFTIISRDNSKNTLYLQMNSL RAEDTAVYYCAR | EGATYYHGSGS----YYPATNYGMDV | WGQGT TVTVS S |
| | | VH3J3-33|D3|3-10|RF1|JH6 | | | | | | | |
| iPS:4 36792 | 21-225_169D12 | VH3J3-33|D3|3-10|RF1|JH6 | QVQLVES-GGGVVQPGRSLRL SCAASG-FTFS | S-----YGMH | WVRQAPGK GLEWVA | VINYD---GSNKYYADS VKG | RFTIISRDNSKNTLYLQMNSL RAEDTAVYYCAR | PLYDMGL-------YYDMDV | WGQGT TVTVS S |
| | | Germline | H_FR1 | H_CDR1 | H_FR2 | H_CDR2 | H_FR3 | H_CDR3 | H_FR4 |
| | VH1J1-46|D7|7-27|RF3|JH4 | | | | | | | | |
| iPS:4 36800 | 21-225_171D12 | VH1J1-46|D7|7-27|RF3|JH4 | QVQLVQS-GAEVKKPGASVKV SCKASG-YTFN | S-----YYMY | WVRQAPGQ GLEWMG | IINPS----GGSTNYAQK FQG | RVTMTRDTSTSTLYMELNSL RSEDTAVYYCAS | GWE-----LNY | WGQGT LVTVS S |
| iPS:4 36804 | 21-225_172C3 | VH1J1-46|D7|7-27|RF3|JH4 | QVQLVQS-GAEVKKPGASVKV SCKASG-YTFR | S-----YYMY | WVRQAPGQ GLEWVG | TINPS----GGSTNYAQK FQG | RVTMTRDTSTSTLYMELNSL RSEDTAVYYCAS | GWE-----LNY | WGQGT LVTVS S |
| iPS:4 36806 | 21-225_172B12 | VH1J1-46|D7|7-27|RF3|JH4 | QVQLVQS-GAEVKKPGASVKV SCKASG-YTFR | S-----YYMY | WVRQAPGQ GLEWVG | TINPS----GGSTDYAQK FQG | RVTMTRDTSTSTLYMELNSL RSEDTAVYYCAS | GWE-----LNY | WGQGT LVTVS S |
| | | Germline | H_FR1 | H_CDR1 | H_FR2 | H_CDR2 | H_FR3 | H_CDR3 | H_FR4 |
| | VH3J3-30.3|D4|4-23|RF1|JH6 | | | | | | | | |
| iPS:4 36808 | 21-225_173F8 | VH3J3-30.3|D4|4-23|RF1|JH6 | QVQLVES-CGGVVQPGRSLRL SCAASG-FTFS | S-----YGMH | WVRQAPGK GLEWVA | VISYD---GSPKYCADS VKG | RFTIISRDSKNTLFLQMNSL RAEDTAVYYCAR | DERQMLP-------APYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH6|6-01|D6|6-6|RF2|JH6 | QVQLQQS-GPGLVKPSQTLSL TCTVSG-GSVS | SN---SAAWN | WIRQSPSR GLEWLG | RTYYR-SKWYNDYA SMES | RITINPDTSKNQFSLQLNSF TPEDTAVYYCAR | DKAAGT---FYYGMDV | WGQGT TVTVS S |
| iPS:4 36810 | 21-225_175F4 | VH6|6-01|D6|6-6|RF2|JH6 | QVQLQQS-GPGLVKPSQTLSL TCAISG-DSVS | SN---SAAWN | WIRQSPSR GLEWLG | RTYYR-SKWYNAYPV SMES | RISINPDTSKNQFSLQLNSV TPEDTAVYYCAR | DKAAGRND------FYYYGMDV | WGQGT TVTVS S |
| iPS:4 36814 | 21-225_178H10 | VH6|6-01|D6|6-6|RF2|JH6 | QVQLQQS-GPGLVKPSQTLSL TCAISG-DSVS | SN---SAAWN | WIRQSPSR GLEWLG | RTYYR-SKWYSAYPV SMES | RVSINPDTSKNQFSLQLNSV TPEDTAVYYCAR | DKAAGRND------FYYYGMDV | WGQGT TVTVS S |
| | Germline | H_FR1 | H_CDR1 | H_FR2 | H_CDR2 | H_FR3 | H_CDR3 | H_FR4 |
| | VH3|3-33D1|1-1|RF3|JH6 | QVQLVES-GGGVVQPGRSLRL SCAASG-FTFS | S------YGMH | WVRQAPGK GLEWVA | VIWYD---GSNKYYADS VKG | RFTISRDNSKNTLYLQMNSL RAEDTAVYYCAR | GDWNP----------YYYGMDV | WGQGT TVTVS S |
| iPS:4 36818 | 21-225_179C7 | VH3|3-33D1|1-1|RF3|JH6 | QAQLVES-GGGVVQPGRSLRL SCAASG-FTFS | N------SGMH | WVRQPGK GLEWVA | IIIYYD--GSYKINADS VKG | RFTISRDNSKNTLYLQMNSL RAEDTAVYYCAR | DRHYDFHVP------YYYYGMDV | WGQGT TVTVS S |
| iPS:4 37094 | 21-225_210D12 | VH3|3-33D1|1-1|RF3|JH6 | QVQLVES-GGGVVQPGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGLDV | WGQGT TVTVS S |
| iPS:4 37096 | 21-225_210E12 | VH3|3-33D1|1-1|RF3|JH6 | QVHLVES-GGGVVQPGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGMDV | WGQGT TVTVS S |
| iPS:4 37098 | 21-225_211C1 | VH3|3-33D1|1-1|RF3|JH6 | QVQLVES-GGGVVQPGRSLRL SCAASG-FTFS | H------YGMH | WVRQAPGK GLEWVA | VIWYD---GSNKYYADS VKG | RFTISRDNSKNTLYLQMNTL RAEDTAIYYCAR | GDWNP----------EGLDV | WGQGT TVTVS S |
| iPS:4 37104 | 21-225_211G5 | VH3|3-33D1|1-1|RF3|JH6 | QVQLVES-GGGVVQPGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGLDV | WGQGT TVTVS S |
| iPS:4 37112 | 21-225_212C2 | VH3|3-33D1|1-1|RF3|JH6 | QVQLVES-GGGVVQPGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGMDV | WGQGT SVTVS S |
| iPS:4 37114 | 21-225_212A4 | VH3|3-33D1|1-1|RF3|JH6 | QVQLVES-GGGVVQAGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGMDV | WGQGT TVTVS S |
| iPS:4 37116 | 21-225_212F6 | VH3|3-33D1|1-1|RF3|JH6 | QVQLVES-GGGVVQPGRSLRL SCAASG-FTFS | H------YGMH | WVRQAPGK GLEWVA | VIWYD---GSNKYYADS VKG | RFTISRDNSKNTLYLQMNSL RAEDTAVYYCAR | GDWNP----------EGLDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 37118 | 21-225_212G7 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYCADS VKG | RFTISRDNSTNTLYLQMNSL RAEDTAVYYCAR | GDWNP------EGLDV | WGQGT TVTVS S |
| iPS:4 37128 | 21-225_213G3 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYYADS VKG | RFTISRDNSKNTLHLQMNSL RAEDTAVYYCAR | GDWNP------EGMDV | WGQGT SVTVS S |
| iPS:4 37130 | 21-225_213D5 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYYADS VKG | RFTISRDNSKNTLFLQMNSL RVEDTAVYYCAR | GDWNP------EGMDV | WGQGT TVTVS S |
| iPS:4 37146 | 21-225_215D3 | VH3|3-33|D1|1-1|RF1|3|JH6 | QIQLVES-GGGVVQPGRSLRLSCAASG-FTFS | H------YGMH | WVRQAPGK GLEWVA | VIWYD---GSNRYYADS VKG | RFTISRDNSKNTLYLQMNSL RAEDTAVYYCAR | GDWNP------EGMDV | WGQGT TVTVS S |
| iPS:4 37150 | 21-225_216A3 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYYADS VKG | RFTISRDNSKNTLYLQMNSL RAEDTAVYYCAR | GDWNP------EGLDV | WGQGT TVTVS S |
| iPS:4 37162 | 21-225_217B2 | VH3|3-33|D1|1-1|RF1|3|JH6 | QVHLVES-GGGVVQPGRSLRLSCAASG-FTFS | N------YGMH | WVRQAPGK GLEWVA | VIWYD---GSNKYYADS VKG | RFTISRDNSKNTLYLQMNSL RAEDTAVYYCAR | GDWNP------EGMDV | WGQGT TVTVS S |
| iPS:4 37172 | 21-225_219A7 | VH3|3-33|D1|1-1|RF1|3|JH6 | QVQLVES-GGGVVQPGRSLRLSCPASG-FTFS | H------YGMH | WVRQAPGK GLEWVA | IIWYD---GSDKYYADS VKG | RFTISRDNSKNMLYLQMNSL RAEDTAVYYCAR | GDWNP------EGMDV | WGQGT SVTVS S |
| iPS:4 37182 | 21-225_221H2 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYYADS VKG | RFTISRDNSKNTLHLQMNSL RAEDTAVYYCAR | GDWNP------EGMDV | WGQGT TVTVS S |
| iPS:4 37184 | 21-225_221G4 | VH3|3-33|D1|1-1|RF1|3|JH6 | QVQLVES-GGGVVQPGRSLRLSCAASG-FTFS | H------YGMH | WVRQAPGK GLEWVA | VIWYD---GSNKYYADS VKG | RFTISRDNSKNTLHLQMNSL RAEDTAVYYCAR | GDWNP------EGMDV | WGQGT TVTVS S |
| iPS:4 38664 | 21-225_216G1 | VH3|3-33|D1|1-1|RF1|3|JH6 | QVHLVES-GGGVVQPGRSLRLSCAASG-FTFS | N------FGMH | WVRQAPGK GLEWVA | VIWYD---GSDKYYADS VKG | RFTISRDNSKNTLYLQMNTL RAEDTAVYFCAR | GDWNP------EGMDV | WGQGT TVTVS S |
| Germline | VH3|3-33|D1|1-1|RF1|JH4 | | QVQLVES-GGGVVQPGRSLRLSCAASG-FTFS | S------YGMH | WVRQAPGK GLEWVA | VIWYD---GSNKYYADS VKG | RFTISRDNSKNTLYLQMNSL RAEDTAVYYCAR | | YFDY | WGQGT LVTVS S |
| iPS:4 36822 | 21-225_180D4 | VH3|3-33|D1|1-1|RF1|JH4 | QVQLVES-GGGVVQPGRSLRLSCAASG-FTFS | N------FGMH | WVRQAEGK GLEWVA | IINWYD---GSDKYYADS VKG | RFTISRDNSKNTLYLQMNTL RAEDTAVYFCAR | GGPFSI------VTMYFDY | WGQGT LVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36828 | 21-225_181H1 | VH3-33/D1(1-1)RF2/JH4 | QVQLVES-GGGVVQPGRSLRL SCAASG-FTFS | N-----YGMH | WVRQAPGK GLEWVA | IINWD---GSDKYYADS VKG | RFTISRDNSKNTLYLQMNTL RAEDTAVYFCAR | GGPFFST------VTMYFDY | WGQGT LVTVS S |
| iPS:4 36950 | 21-225_184G4 | VH3-33/D1(1-1)RF1/JH4 | QVQLVES-GGGVVQPGRSLRL SCAVSG-FTFS | S-----YGMH | WVRQAPGK GLEWVA | IINWD---GSNKYYADS VKG | RFTISRDNSKNTLYLQMNSL RAEDTAVYYCAR | GGPFFST------VTMYFDY | WGQGT LVTVS S |
| iPS:4 36952 | 21-225_185D2 | VH3-33/D1(1-1)RF1/JH4 | QVQLVES-GGGVVQPGRSLRL SCAASG-FTFS | N-----YGMH | WVRQAPGK GLEWVA | IINWD---GSDKYYADS VKG | RFTISRDNSKNTLYLQMNTL RAEDTAVYFCAR | GGPFFST------VTMYFDY | WGQGT LVTVS S |
| | Germline | | H_FR1 | H_CDR1 | H_FR2 | H_CDR2 | H_FR3 | H_CDR3 | H_FR4 |
| | VH2(2-05/D6(6-6)RF2/JH3 | | | | | | | | |
| iPS:4 36824 | 21-225_180C5 | VH2(2-05/D6(6-6)RF2/JH3 | QITLKES-GPTLVKPTQTLTL TCTFSG-FSLS | TS----GVGVG | WIRQPPGK ALEWLG | FISW---NDDKRYSPS LKS | SLITKDTSKNQVVLIMTNM DEVDTATYYCAR | KAAAV------AFDI | WGQGT MVTVS S |
| iPS:4 36956 | 21-225_186H6 | VH2(2-05/D6(6-6)RF2/JH3 | QITLKES-GPTLVKPTQTLTL TCTFSG-FSLS | TS----GVGVG | WIRQPPGK ALEWLG | FISW---NDCKRYSPS LKS | SLITKDTSKNQVVLIMTNM DEVDTATYYCAR | KAAAV------AFDI | WGQGT MVTVS S |
| | Germline | | H_FR1 | H_CDR1 | H_FR2 | H_CDR2 | H_FR3 | H_CDR3 | H_FR4 |
| | VH1(1-08/D5(5-18)RF3/JH6 | | | | | | | | |
| iPS:4 36826 | 21-225_180G5 | VH1(1-08/D5(5-18)RF3/JH6 | QVQLVQS-GAEVKKPGASVKV SCKASG-YTFT | S-----YDIN | WVRQATGQ GLEWMG | MMNPN---SGNTGYAQK FQG | RVIMTRNTSISTAYMELSSL RSEDTAVYYCAR | GFYYYGSGSHV------PYHYYGLDV | WGQGT TVTVS S |
| | Germline | | H_FR1 | H_CDR1 | H_FR2 | H_CDR2 | H_FR3 | H_CDR3 | H_FR4 |
| | VH6(6-01/D5(5-24)RF3/JH2 | | | | | | | | |
| iPS:4 36832 | 21-225_51D8 | VH6(6-01/D5(5-24)RF3/JH2 | QVQLQQS-GPGLVKPSQTLSL TCAISG-DSVS | SN----SAARN | WIRQSFSR GLEWLG | RTYYR---SKWNDYAV SVKS | RITFNPDTSKNQFSLRLNSV TPEDTAVYCAR | DRYNWNY------PYWYFDL | WGRGT LVTVS S |
| | Germline | | H_FR1 | H_CDR1 | H_FR2 | H_CDR2 | H_FR3 | H_CDR3 | H_FR4 |
| | VH1(1-02/D5(5-24)RF3/JH5 | | | | | | | | |
| iPS:4 36840 | 21-225_53E9 | VH1(1-02/D5(5-24)RF3/JH5 | QVQLVQS-GAEVKKPGASVKV SCKASG-NIFT | G-----YYMH | WVRQAPGQ GLEWMG | WIIPN---SGDTNIAQK FQG | RVIMTRDISISTAYMELSRL RSDDTAVYYCAR | DGYSSGW------ENWFDP | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH2|2-05|D7|7-27|RF1|JH4 | | QITLKES-GPTLVKPTQTLTLTCTFSG-FSLS | TS---GVGVG | WIRQPPGK ALEWLA | LIYW------HEDKRYSPS LKS | RLIITEDTSKNQVDLTMTNM APVDTATYYCAH | VTGI--------------- | WGQGT LVTVS S |
| iPS:4 36848 | VH2|2-05|D7|7-27|RF1|JH4 | QITLKES-GPTLVKPTQTLTLTCTFSG-FSLS | TS---GVGVG | WIRQPPGK ALEWLA | LIYW------HEDKRYSPS LKS | RLIITEDTSKNQVDLTMTNM APVDTATYYCAH | VTGI-----------AAPY | WGQGT LVTVS S |
| iPS:4 36852 | VH2|2-05|D7|7-27|RF1|JH4 | QITLKES-GPTLVKPTQTLTLTCTFSG-FSLT | TS---GVGVG | WIRQPPGK ALEWLA | LIYW------HEDRRYSPS LKS | RLIITEDTSKNQVDLTMTNM APVDTATYYCAH | VTGI-----------AAPY | WGQGT LVTVS S |
| iPS:4 36870 | VH2|2-05|D7|7-27|RF1|JH4 | QITLKES-GPTLVKPTQTLTLTCTFSG-FSLS | TS---GVGVG | WIRQPPGK ALEWLA | LIYW------HEDKRYSPS LKS | RLIITEDTSKNQVDLTMTNM APVDTATYYCAH | VTYI-----------AAPY | WGQGT LVTVS S |
| iPS:4 36876 | VH2|2-05|D7|7-27|RF1|JH4 | QITLKES-GPTLVKPTQTLTLTCTFSG-FSLS | TS---GLGVG | WIRQPPGK ALEWLA | LIYS------HEDKRYSPS LKS | RLIITEDTSKNQVDLTMTNM APVDTATYYCAH | VTGI-----------AAPY | WGQGT LVTVS S |
| iPS:3 92593 | VH2|2-05|D7|7-27|RF1|JH4 | QITLKES-GPTLVKPTQTLTLTCTFSG-FSLN | TG---GVGVG | WIRQPPGK ALEWLA | LIYW------NDDKRHSPS LKS | RLIITKDTSKNQVVLTMTHM APVDTATYYCAH | LIEV-----------AFDY | WGQGT LVTVS S |
| | Germline | H_FR1 | H_CDR1 | H_FR2 | H_CDR2 | H_FR3 | H_CDR3 | H_FR4 |
| VH2|2-05|D6|6-6|RF2|JH1 | | | | | | | | |
| iPS:4 36854 | VH2|2-05|D6|6-6|RF2|JH1 | QITLKES-GPTLVKPTQTLTLTCTFSG-FSLS | TS---GVGVG | WIRQPPGK ALEWLA | LIYW------DDDKRYSPS LKS | RLIITEDTSKNQVVLTMTRM DPVDTATYYCAH | LIAV-----------AFDS | WGQGT LVTVS S |
| iPS:4 36874 | VH2|2-05|D6|6-6|RF2|JH1 | QITLKES-GPTLVKPTQTLTLTCTFSG-FSLS | TS---GVGVG | WIRQPPGK ALEWLA | LIYW------DDDKRYSPS LKS | RLIITEDTSKNQVVLTMTRM DPVDTATYYCAH | LIAV-----------AFDS | WGQGT LVTVS S |
| iPS:4 36954 | VH2|2-05|D6|6-6|RF2|JH1 | QITLKES-GPTLVKPTQTLTLTCTFSG-FSLT | TG---GVGVG | WIRQPPGK ALEWLA | LIYW------NDDERYSPS LKS | RGIITKDTSKNQVVLTMTRM DPVDTATYYCAH | LIAV-----------AFQH | WGQGT LVTVS S |
| iPS:3 93188 | VH2|2-05|D6|6-6|RF2|JH1 | QITLRES-GPTLVKPTQTLTLTCTFSG-FSLS | TS---GVGVG | WIRQPPGK ALEWLA | LIYW------NDDKRISPS LKS | RLIITKDTSKNQVVLTMTNM DPVDTATYYCAH | LIAV-----------TFDS | WGQGS LVTVS S |
| | Germline | H_FR1 | H_CDR1 | H_FR2 | H_CDR2 | H_FR3 | H_CDR3 | H_FR4 |
| VH3|3-30.3|D3|3-10|RF2|JH6 | | | | | | | | |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36858 | 21-225_58E7 | VH3J3-30.3/D3J3-10[RF3]JH6 | QVQLVES-GGGVVQPGRSLRL SCAASG-FTFS | F-----YGMH | WVRQAPGK GLEWVA | VTSYD---GSDKYYADS VKG | RFSISRDNSKNTLYLQMSSL RAEDTAMYYCAR | DDYGSGSP------LYYGMDV | WGQGT TVTVS S |
| | | Germline | | | | | | | |
| | | VH3J3-30.3/D4J4-12[RF3]JH6 | | | | | | | |
| iPS:4 36860 | 21-225_58F7 | VH3J3-07/D5J5-12[RF3J]JH6 | EVQLVES-GGGLVQPGGSLRL SCAASG-FTFS | S-----FWMS | WVRQAPGK GLEWVA | HIKQD---GSEKYYVDS VKG | RFTISRDNAKNSLYLQMNSL RAEDTAVYYCAR | GDLPYSG-------YYYGMDV | WGQGT TVTVS S |
| | | Germline | | | | | | | |
| | | VH3J3-30.3/D4J4-17[RF2]JH6 | | | | | | | |
| iPS:4 36862 | 21-225_58F8 | VH3J3-30.3/D4J4-17[RF2]JH6 | QVQLVES-GGGVVQPGRSLRL SCAASG-FTFS | S-----YGMH | WVRQAPGK GLEWVA | VISYD---GSNKYYADS VKG | RFTISRDNSKNTLYLQMNSL RAEDTAVYYCAR | DEGRGYGGYER----GYYYYYGMDV | WGQGT TVTVS S |
| | | Germline | | | | | | | |
| | | VH3J3-33/D3J3-16[RF2]JH6 | | | | | | | |
| iPS:4 36868 | 21-225_59B11 | VH3J3-33/D3J3-16[RF2]JH6 | QVQLVES-GGGVVQPGRSLRL SCAASG-FTFS | S-----YGVH | WVRQAPGK GLEWVA | AIWYD---GSNKYYADS VKG | RFTISRDNSKNTLYLLMNSL RAEDTAVYYCAR | DRDYCSSSC----PYYYYYGMDV | WGQGT TVTVS S |
| | | Germline | | | | | | | |
| | | VH2J2-05/D1J1-1[RF1]JH3 | | | | | | | |
| iPS:4 36878 | 21-225_62E3 | VH2J2-05/D1J1-1[RF1]JH3 | QITLKES-GPTLVKPTQTLTL TCTFSG-FSLS | TS---GVGVG | WIRQPPGK ALEWLA | LINW-----NDDKRYSPS LKS | RFTITRDTSKDQVVLTMTNM DPVDTATYYCAH | KATWV--------AFDI | WGQGT MVTVS S |
| iPS:4 36880 | 21-225_62E8 | VH2J2-05/D1J1-1[RF1]JH3 | QITLKES-GPTLVKPTQTLTL TCTFSG-FSLS | TS---GVGVG | WIRQPPGK ALEWLA | LINW-----NDDKRYSPS LKS | RFTITRDTSKDQVVLTMTNM DPVDIATYYCAH | KATWV--------AFDI | WGQGT MVTVS S |
| iPS:4 36882 | 21-225_62D10 | VH2J2-05/D1J1-1[RF1]JH3 | QITLKES-GPTLVKSTQTLTL TCTFSG-FSLS | TS---GVGVG | WIRQPPGK ALEWLA | LINW-----NDDKRYSPS LKS | RFTITRDTSKDQVVLTMTNM DPVDTATYYCAH | KATWV--------AFDI | WGQGT MVTVS S |
| iPS:4 36884 | 21-225_62A12 | VH2J2-05/D1J1-1[RF1]JH3 | QITLKES-GPTLVKPTQTLTL TCTFSG-FSLS | TS---GVGVG | WIRQPPGK ALEWLA | LINW-----NDDKRYSPS LKS | RFTITRDTSKDQVVLTMTNM DPLDTATYYCAH | KITWV--------AFDI | WGQGT MVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36886 | 21-225_62B12 | VH2/2-05/D1/1-1/RF1/JH3 | QITLKES-GPTLVKPTQTLTL TCTFSG-FSLN | TS---GVGVG | WIRQPPGK ALEWLA | LINW----NDCKRYSPS LKS | RFTITRDTSKDQVVLTMTNM DPVDTATYYCAH | KATWV------AFDI | WGQGT MVTVS S |
| iPS:4 36894 | 21-225_66G9 | VH2/2-05/D1/1-1/RF1/JH3 | QITLKES-GPTLVKPTQTLTL TCTFSG-FSLS | TS---GVGVG | WIRQPPGK ALEWLA | LINW----NDDKRFSPS LKS | RFTITRDTSKDQVVLTMTNM DPVDTATYYCAH | KATWV------AFDI | WGQGT MVTVS S |
| iPS:4 36908 | 21-225_72D5 | VH2/2-05/D1/1-1/RF1/JH3 | QITLKES-GPTLVKPTQTLTL TCTFSG-FSLS | TS---GVGVG | WIRQPPGK ALEWLA | LINW----NDDKRYSPS LKS | RFTITRDTSKDQVVFTMTNM DPVDTGTYYCAH | KATWV------AFDI | WGQGT MVTVS S |
| iPS:4 36912 | 21-225_73C4 | VH2/2-05/D1/1-1/RF1/JH3 | QITLKES-GPTLVKPIQTLTL TCTFSG-FSLS | TS---GVGVG | WIRQPPGK ALEWLA | LINW----NDCKRYSPS LKS | RFTITRDTSKDQVVLTMTNM DPVDTATYYCAH | KITWV------AFDI | WGQGT MVTVS S |
| | Germline | | H_FR1 | H_CDR1 | H_FR2 | H_CDR2 | H_FR3 | H_CDR3 | H_FR4 |
| | VH3/3-48/D4/4-11/RF2/JH3 | | | | | | | | |
| iPS:4 36888 | 21-225_63G7 | VH3/3-48/D4/4-11/RF2/JH3 | EVQLVES-GGGLVQPGGSLRL SCAASG-FTFS | S------YSMN | WVRQAPGK GLEWVS | YISSS----TSTIYYAAS VKG | RFTISRDNAKMSLYLQMNSL RDEDTAVYYCAR | DHRYDSSG------YYSDAFDI | WGQGT MVTVS S |
| iPS:4 36890 | 21-225_63A10 | VH3/3-48/D4/4-11/RF2/JH3 | EVQLVES-GGGLVQPGGSLRL SCAASG-FTFS | S------YSMN | WVRQAPGK GLEWVS | YISSS----TSTIYYAAS VKG | RFTISRDNARNSLYLQMNSL RDEDTAVYYCAR | DHRYDSSG------YYSDAFDI | WGQGT MVTVS S |
| | Germline | | H_FR1 | H_CDR1 | H_FR2 | H_CDR2 | H_FR3 | H_CDR3 | H_FR4 |
| | VH1/1-02/D3/3-22/RF2/JH3 | | | | | | | | |
| iPS:4 36892 | 21-225_65E9 | VH1/1-02/D3/3-22/RF2/JH3 | QVQLVQS-GAEVKKPGASVKV SCKASG-YTFT | G------YYMH | WVRQAPGQ GLEWMG | WINPN----SGGTNYAQK FQG | RVTMTRDTSISTAYMELSRL RSDDTAVYYCAR | AYYYGSGS------YNEFDM | WGQGT MVTVS S |
| iPS:4 36900 | 21-225_69B9 | VH1/1-02/D3/3-22/RF2/JH3 | QVQMVQS-GDEVKKPGASVKV SCKASG-YTFT | G------YHMH | WVRQAPGQ GLEWMG | WINPN----SGGTNYAQK FQG | RVTMTRDTSISTAYMELSRM RSDDTAVYYCAR | AYYYGSGS------YNESDM | WGQGT MVTVS S |
| | Germline | | H_FR1 | H_CDR1 | H_FR2 | H_CDR2 | H_FR3 | H_CDR3 | H_FR4 |
| | VH6/6-01/D4/4-17/RF2/JH6 | | | SN---SAAWN | | | | | |
| iPS:4 36898 | 21-225_68D8 | VH6/6-01/D4/4-17/RF2/JH6 | QVQLQQS-GPGLVKPSQTLSL TCAISG-DSVS | SN---SAAWN | WIRQSPSR GLEWLG | RTYYR----SECINDYAV SVQS | RITINPDISKNQFSLHLNSV TPEDTAVYFCAR | DRGHRG------FYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | | | | | | | | |
| iPS:4 36910 | VH3/3-33/D7/7-27/RF1/JH3 | QVQLVES-GGGVVQPGRSLRL SCAGTG-TFFS | Y-------YGMH | WVRQAPGK GLEWVA | VTTYD----GSNKYYADS VKG | RFTSSRDNSKNTLYLQMNSL RAEDTAVYHCAR | EIGTW----------AFDI | WGQGT MVTVS L |
| | | | H_FR1 | H_CDR1 | H_FR2 | H_CDR2 | H_FR3 | H_CDR3 | H_FR4 |
| iPS:4 36920 | VH4/4-30.1/D2/2-15/RF3/J H4 | QVQLQES-GPGLVKPSQTLSL TCTVSG-GSIR | SG----GYYWS | WIRQHPGK GLEWIG | YIYY------SGSTYYNPS LRS | RASISVDTSKNQFSLKLSSV TAADTAVYYCAR | DSPVA-----------GTDY | WGQGT LVTVS S |
| iPS:4 37012 | VH4/4-30.1/D2/2-15/RF3/J H4 | QVQLQES-GPGLVKPSQTLSL TCTVSG-GSIS | SG----GYYWS | WIRQHPGK GLEWIG | YIYY------RGSTYYNPS LKS | RVTISVDTSKNQFSLKLNSV TAADTAVYYCAR | DSPVT-----------GFDY | WGQGI LVTVS S |
| | Germline | H_FR1 | H_CDR1 | H_FR2 | H_CDR2 | H_FR3 | H_CDR3 | H_FR4 |
| iPS:4 36942 | VH1/1-08/D5/5-12/RF3/J H6 | QVQLVQS-GAEVKKPGASVKV SCKASG-YTFI | S------YDIN | WVRQATGQ GLEWMG | WMNPN----SGNTGYAQK FQG | RVTMTRNTSKSTAYMELSSL RSEDTAVYYCAR | GDYYYDSSGHQ----PYYYYYGMDV | WGQGT TVTVS S |
| | | | H_FR1 | H_CDR1 | H_FR2 | H_CDR2 | H_FR3 | H_CDR3 | H_FR4 |
| iPS:4 36944 | VH2/2-05/D6/6-6/RF3/JH 4 | 21-225_182D12 QIILKES-GPTLVKPTQPLTL TCTFSG-FSLS | IT----GVGVG | WIRQPPGK ALEWLG | ILFW------NDDERYSPS LKS | RLTITKDISKNQVVLTMTNM DFVDTATYYCAR | KSQLV----------YFDY | WGQGT LVTVS S |
| | Germline | H_FR1 | H_CDR1 | H_FR2 | H_CDR2 | H_FR3 | H_CDR3 | H_FR4 |
| iPS:4 36958 | VH4/4-30.1/D2/2-8/RF3/JH 4 | 21-225_190D1 QVQLQES-GPGLVKPSQTLSL TCTVSG-GSIS | SG----GYYWS | WIRQHPGK GLEWIG | YIYY------SGSTYYNPS LKS | RVTISVDTSKNQFSLKLSSV TAADTAVYYCAR | DSPLR-----------GFDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| VH6|6-01|D4|4-17|RF2|JH4 | | QVQLQQS-GPGLVKPSQTLSLTCAISG-DSVS | SGSAAWN | WIRQSPSRGLEWLG | RTYYR-SKWYNDYAVSVKS | RITINPDTSKNQFSLQLNSVTPEDTAVYYCAR | YFDY | WGQGTLVTVSS |
| iPS:4 36962 | 21-225_190H1 | VH6|6-01|D4|4-17|RF2|JH4 | QVQLQQS-GPGLVKPSQTLSLTCDISG-DSVS | RK---SATWN | WIRQSPSRGLEWLG | RTYYR-SKWYNDYAVSVKS | RITINPDTSKNQFSLQLNSVTPEDTAVYYCAR | DPGG------------LFDY | WGQGTLVTVSS |
| iPS:4 36978 | 21-225_190G9 | VH6|6-01|D4|4-17|RF2|JH4 | QVQLQQS-GPGLVKPSQTLSLTCAISG-DSVS | RK---SATWN | WIRQSPSRGLEWLG | RTYYR-SKWYNDYAVSVKS | RITINPDTSKNQFSLQLNSVTPEDTAVYYCAR | DPGG------------LFDY | WGQGTLVTVSS |
| iPS:4 37070 | 21-225_201G11 | VH6|6-01|D4|4-17|RF2|JH4 | QVQLQQS-GPGLVKPSQTLSLTCAISG-DSVS | RI----NPTWN | WIRQSPSRGLEWLG | RTYYR-SKWYHVYAVSVKS | RITINPDTSKNQFSLQLNSVTPEDTAVYYCAR | DPGG------------LFDY | WGQGTLVTVSS |
| iPS:4 37076 | 21-225_203G6 | VH6|6-01|D4|4-17|RF2|JH4 | QVQLQQS-GPGLVKPSQTLSLTCAISG-DSVS | RT----NPTWN | WIRQSPSRGLEWLG | RTYYR-SKWYHVYALSVKS | RITIPDISKNQFSLQLNSVTPEDTAVYYCAR | DPGG------------LFDY | WGQGTLVTVSS |
| | Germline | H_FR1 | H_CDR1 | H_FR2 | H_CDR2 | H_FR3 | H_CDR3 | H_FR4 |
| VH3|3-33|D1|1-7|RF3|JH6 | | QVQLVES-GGGVVQPGRSLRLSCAASG-FTFS | SGYYMH | WVRQAPGKGLEWVA | VIWYD-GSNKYYADSLRS | RFTISRDNSKNTLYLQMNSLRAEDTAVYYCAR | YYYGMDV | WGQGTTVTVSS |
| iPS:4 36964 | 21-225_190B3 | VH3|3-33|D1|1-7|RF3|JH6 | QVQLVES-GGGVVQPGRSLRLSCAASG-FTFN | N------YGIH | MVRQAPGKGLEWVA | VIWFD---GDNKYYADSVKG | RFTISRDNSKNTLYLQMNSLRAEDTAVYYCAR | DMWNYGDH-----YYYFGMDV | WGQGTTVTVSS |
| iPS:4 36970 | 21-225_190B8 | VH3|3-33|D1|1-7|RF3|JH6 | QVQLVES-GGGVVQPGRSLRLSCAASG-FTFS | S------YGMH | MVRQAPGKGLEWVA | VIWFD---GSNKYYTDSVKG | RFTISRDNSKNTLYLQMNSLRAEDTAVFYCAR | DMWNYGDY-----YYYYGMDV | WGQGTTVTVSS |
| iPS:4 36980 | 21-225_190C10 | VH3|3-33|D1|1-7|RF3|JH6 | QVQLVES-GGGVVQPGRSLRLSCAASG-FTLS | N------YGMH | MVRQAPGKGLEWVA | VIWFG---GDNKYYADSVRG | RFTISRDNSKNTLYLQMNSLRAEDTAVFYCAR | DMWNYGDH-----YYYYGMDV | WGQGTTVTVSS |
| iPS:4 36992 | 21-225_191B8 | VH3|3-33|D1|1-7|RF3|JH6 | QVQLVES-GGGVVQPGRSLRLSCAASG-FTLS | S------YGMH | MVRQAPGKGLEWVA | VIWFG---GDNKYYADSVKG | RFTISRDNSKNTLYLQMNSLRAEDTAVFYCAR | DMWNYGDH-----YYYYGMDV | WGQGTTVTVSS |
| iPS:4 36994 | 21-225_191A9 | VH3|3-33|D1|1-7|RF3|JH6 | QVQLVES-GGGVVQPGRSLRLSCAASG-FTLS | N------YGMH | MVRQAPGKGLEWVA | VIWFG---GDNKYYADSVKG | RFTISRDNSKNTLYLQMNSLRAEDTAVFYCAR | DMWNYGDH-----YYYYGMDV | WGQGTTVTVSS |
| | Germline | H_FR1 | H_CDR1 | H_FR2 | H_CDR2 | H_FR3 | H_CDR3 | H_FR4 |
| VH4|4-30.1|D4|4-11|RF2|JH6 | | QVQLQES-GPGLVKPSQTLSLTCVSG-GSIS | SG--GYYWS | WIRQHPGKGLEWIG | SISYSGSTTYNPSLRS | RVTISVDTSKNQFSLKLSSVTAADTAVYYCAR | YYYGMDV | WGQGTTVTVSS |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 36984 | 21-225_190F10 | VH4|4-30.1/D4|4-11|RF2/J H6 | QVQLQES-GPGLVKPSQTLSL TCTVSG-GSIR | SG---GDYWS | WIRQHPGE GLEWIG | YIYY---- SGITYNPS LKS | RVTISVDTSKNQFSLKLSSV TAADTAVYYCAR | DSSSR-------GMDV | WGQGT TVTVS S |
| iPS:4 36988 | 21-225_191A2 | VH4|4-30.1/D4|4-11|RF2/J H6 | QVQLQES-GPGLVKPSQTLSL TCTVSG-GSIS | SG---GDYWS | WIRQHPGE GLEWIG | YIYY---- SGITYNPS LKS | RVTISVDTSKNQFSLKLSSV TAADTAVYYCAR | DSSSR-------GMDV | WGQGT TVTVS S |
| iPS:4 37014 | 21-225_192H8 | VH4|4-30.1/D4|4-11|RF2/J H6 | QVQLQES-GPGLVKPSQTLSL TCTVSG-GSIS | SG---GDYWS | WIRQHPGK GLEWIG | YIYY---- SGPTYNPS LKS | RLIMSADTSKNQFSLKLSSV TAADTAVYYCAR | DSSLY-------GMDV | WGQGT TVTVS S |
| iPS:4 37022 | 21-225_194G5 | VH4|4-30.1/D4|4-11|RF2/J H6 | QVQLQES-GPGLVKPSQTLSL TCTVSG-GSIR | SG---GDYWS | WIRQHPGK GLEWIG | YIYY---- SGSTYNPS LKS | RVTISVDTSKNQFSLKLSSV TAADTAVYYCAR | DHSLY-------GMDV | WGQGT TVTVS S |
| iPS:4 37026 | 21-225_194D12 | VH4|4-30.1/D4|4-11|RF2/J H6 | QVQLQES-GPGLVKPSQTLSL TCTVSG-GSIS | SG---GDYWS | WIRQHPGE GLEWIG | YIYY---- SGSTYYNPS LKS | RVTISVDTSKNQFSLKLSSV TAADTAVYYCAR | DGARH-------GMDV | WGQGT TVTVS S |
| iPS:4 37056 | 21-225_198B8 | VH4|4-30.1/D4|4-11|RF2/J H6 | QVQLQES-GPGLVKPSQTLSL TCTVSG-GSIS | SG---GDYWS | WIRQHPGE GLEWIG | YIYY---- SGSTYYNPS LKS | RVTISVDTSKNQFSLKLSSV TAADTAVYYCAR | DSSSR-------GMDV | WGQGT TVTVS S |
| iPS:4 37124 | 21-225_212H12 | VH4|4-30.1/D4|4-11|RF2/J H6 | QVQLQES-GPGLVKPSQTLSL TCTVSG-GSIR | SG---GDYWS | WIRQHPGK GLEWIG | YIYY---- SGSTYYNPS LKS | RVTISGDTSKNQFSLKLSSV TAADTAVYYCAR | DSSSY-------GMDV | WGQGT TVTVS S |
| iPS:4 37136 | 21-225_214H3 | VH4|4-30.1/D4|4-11|RF2/J H6 | QVQLQES-GPGLVKPSQTLSL TCTVSG-GSIR | SG---GDYWS | WIRQPPGK GLEWIG | YIYY---- SGSTYYNPS LKS | RVTISVDTSKNQFSLKLSSV TAADTAVYYCAR | DSSSY-------GMDV | WGQGT TVTVS S |
| VH4|4-59|D1|1-26|RF1/JH4 | | Germline | QVQLQES-GPGLVKPSETLSL TCTVSG-GSIS | S------YWS | WIRQPPGK GLEWIG | YIYY---- SGSTYNPS VRG | RVTISBDTSKNYLQLNSL RSVTAADTA VYYCAR | YYCAR | WGQGT LVTVS S |
| iPS:4 36986 | 21-225_191A1 | VH4|4-59|D1|1-26|RF1/J H4 | QVQLQES-GPGLVKPSETLSL TCTVSG-GSIR | S------YYWI | WIRQPPGK GLEWIG | YIYY---- SGSTKYNPS LKS | RVTISVDTSKNQFSLKLSSV TAADTAVYYCAR | KGVGT--------IHFDY | WGQGT LVTVS S |
| iPS:4 37064 | 21-225_200G8 | VH4|4-59|D1|1-26|RF1/J H4 | QVQLQES-GPGLVKPSETLSL TCTVSG-GSIR | S------YYMS | WIRQPPGK GLEWIG | YIYY---- SGSTKYNPS LKS | RVTISVDTSKNQFSLKLSSV TAADTAVYYCAR | KGVGT--------IHFDY | WGQGT LVTVS S |
| VH3|3-30|D6|6-RF1|JH4 | | Germline | QVQLVES-GGGTVQPGGSL RLSCAASG-FTFS | S------YGMH | WVRQAPGK GLEWVA | VISY---- DGSNKYYAD SVKG | RFTISRDNSKNTLYLQMNSL RAEDTAVYYCAR | EGSSS--------SFDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 36996 | 21-225_191B9 | VH3J3-30/D6J6-6|RF1/JH4 | QVQLVES-GGGVVQPGRSLRL SCAASG-FTFS | F------HGMH | WVRQAPGK GLEWVA | VINYD---GSKKYYADS VKG | RFTISRDNSKNTLHLQMNSL RAEDTAVYYCAK | EGYSSGF------YRGFDN | WGQGT LVTVS S |
| iPS:4 37054 | 21-225_194G3 | VH3J3-30/D6J6-6|RF1/JH4 | QVQLVES-GGGVVQPGRSLRL SCAASG-FTFS | F------HGMH | WVRQAPGK GLEWVA | VINYD---GSKKYYADS VKG | RFTISRDNSKNTLHLQMNSL RAEDTAVYYCAK | EGFSSGF------YRGFDN | WGQGT LVTVS S |
| | Germline VH3J3-33D11J-26|RF1/JH6 | | | | | | | | |
| | | H_FR1 | H_CDR1 | H_FR2 | H_CDR2 | H_FR3 | H_CDR3 | H_FR4 |
| iPS:4 37000 | 21-225_191G9 | VH3J3-33/D1J1-26|RF1/JH6 | QVQLVES-GGGVVQPGRSLRL SCAASG-FTFS | I------YGMH | WVRQAPGK GLEWVT | LIWFD---GSNKYYADS VKG | RFTISRDNSKNTLYLQMNSL RAEDTAVYYCAR | DRVGGTSPF------YYYYGMDV | WGQGT TVTVS S |
| iPS:3 93192 | 21-225_12B1 | VH3J3-33D11J-26|RF1/JH6 | QVQLVES-GGGVVQFGRSLRL SCAASG-FTFS | S------YGMH | WVRQAPGK GLEWVA | VIWND---GSNKYYADS VKG | RFTISRDNSKNTLYLQMNSL RAEDTAVYYCAR | DRVAAAGTP------YYYYGMDV | WGQGT TVTVS S |
| | Germline VH1J1-02/D3J3-10|RF2/JH5 | | | | | | | | |
| | | H_FR1 | H_CDR1 | H_FR2 | H_CDR2 | H_FR3 | H_CDR3 | H_FR4 |
| iPS:4 37002 | 21-225_191H9 | VH1J1-02/D3J3-10|RF2/JH5 | QVQLVQS-GAEVKKPGASVKV SCKVSG-YTFT | G------YNMH | WVRQAPGQ GLEWMG | WINPN---SGGTNYAHK FQG | RVTMTRDTSTAYMELSRL RSDDTAVYYCAR | DFYDSGG------EGWFDP | WGQGT LVTVS S |
| | Germline VH4J4-30.4|D2J2-8|RF3/JH6 | | | | | | | | |
| | | H_FR1 | H_CDR1 | H_FR2 | H_CDR2 | H_FR3 | H_CDR3 | H_FR4 |
| iPS:4 37008 | 21-225_192E3 | VH4J4-30.4/D2J2-8|RF3/JH6 | QVQLQES-GPGLVKPSQTLSL TCTVSG-GSIS | SG---GYYWS | WIRQPPGK GLEWIG | YIYY---TGSTYNPS LKS | RVTISVDTSKNQFSLKLSSV TAADTAVYYCAR | DDPLY------GMDV | WGQGT TVTVS S |
| iPS:4 37048 | 21-225_197B11 | VH4J4-30.4/D2J2-8|RF3/JH6 | QVQLQES-GPGLVKPSQTLSL TCTVSG-GSIS | SG---GYYWS | WIRQPPGK GLEWIG | YIYY---TGSTYNPS LKS | RVTISVDTSKNQFSLKLSSV TAADTAVYYCAR | DDPLY------GMDV | WGQGT TVTVS S |
| | Germline VH4J4-59|D7J7-27|RF3/JH4 | | | | | | | | |
| | | H_FR1 | H_CDR1 | H_FR2 | H_CDR2 | H_FR3 | H_CDR3 | H_FR4 |
| iPS:4 37010 | 21-225_192G3 | VH4J4-59/D7J7-27|RF3/JH4 | QVQLQES-CPGLVKPSETLSL TCTVSG-GSIS | N------YYWS | WIRQPAGK GLEWIG | RIYS---SGSTNYNPS LKS | RVTMSVDTSKNQFSLKLNSV TAADTAVYYCAR | GME------LNY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 37016 | 21-225_193A6 | QVQLQES-GPGLVKPSETLSL TCTVSG-GSIS | S------YYWS | WIRQPPGK GLEWIG | YIYY----SGSTNYNPS LKS | RVTISVDTSKNQFSLKLSSV TAADTAVYYCAG | GWE-----------LNY | WGQGT LVTVS S |
| | VH4/4-59/D7/7-27/RF3/JH4 Germline | | | | | | | |
| | VH3/3-15/D4/4-17/RF2/JH4 | | | | | | | |
| iPS:4 37018 | 21-225_193H5 | EVQLVES-GGGLVMPGGGLSL SCAASG-FTFS | N------AYMT | WVRQAPGK GLEWVG | RIKSKT-DGGTIDYAA PVKG | RFTISRDDSKNTLYLQMNSL KTEDTAVYYCTT | DPGG-----------IFDY | WGQGT LVTVS S |
| iPS:4 37144 | 21-225_215B3 | EVQLVES-GGGLVKPGGSLRL SCAASG-FTFS | N------AWMH | WVRQAPGK GLEWVG | RIKSKT-NGGTIDYAA PVKG | RFTISRDDSKNTLYLQMNSL KTEDTAVYYCTT | DPGG-----------IFDY | WGQGT LVTVS S |
| | VH3/3-15/D4/4-17/RF2/JH4 Germline | | | | | | | |
| | VH3/3-11/D3/3-9/RF1/JH4 | | | | | | | |
| iPS:4 37030 | 21-225_195E3 | QVQLVES-GGGLVKPGGSLRL SCAASG-FTFS | D------YYMS | WIRQAPGK GLEWVS | YITSS---GNTIYYADS VKG | RFTISRDNAKNSLYLQMNSL RAEDTAVYYCAR | DSRYF-----------DWFDY | WGQGT LVTVS S |
| | VH4/4-59/D7/7-27/RF3/JH1 Germline | | | | | | | |
| iPS:4 37032 | 21-225_195H6 | QVQLQES-GPGLVKPSETLSL TCTVSG-GSIR | N------YYWS | WIRQPAGK GLEWIG | RIYS----SGSTNYNPS LKS | RVSMSVDTSKNQFSLKLSSV TAADTAVYYCTR | GWE-----------LNN | WGQGT LVTVS S |
| | VH4/4-59/D6/6-6/RF1/JH6 Germline | | | | | | | |
| iPS:4 37044 | 21-225_197F9 | QVQLQES-GPGLVKPSETLSL TCTVSG-GSIR | I------YYWS | WIRQPPGK GLEWIG | YVYY----SGSTTYNPS LKS | RVTISVDTSKNQFSLKLNSV TAADTAVYYCVR | ERGSSHRM---GDYYGMDV | WGRGT TVTVS S |
| iPS:4 37060 | 21-225_199C3 | QVQLQES-GPGLVKPSETLSL TCTVSG-GSIR | I------YYWS | WIRQTPGK GLEWIG | YIYY----SGSTTYNPS LKS | RVTISVDTSKNQFSLKLNSV TAADTAVYYCVR | ERGSSHRM---GDYYGMDV | WGRGT TVTVS S |
| | VH3/3-30/D6/6-6/RF1/JH1 Germline | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 37058 | 21-225_199F3 | VH3J3-30/D6|6-6|RF1/JH1 | QVQLVES-GGGVVQPGRSLRL SCAASG-FTFS | F-----YGMH | WVRQAPGK GLEWVA | VINYD---GSSKYIADS VKG | RFTVSRDNSKNTLYLQMNSL RAEDTAVYYCAR | EGYSSGF------YRGFAN | WGQGT LVTVS S |
| | Germline | VH4J4-30.1|D6|6-6|RF2|JH6 | QVQLQES-GPGLVKPSQTLSL TCTVSG-GSIS | SG----GDYWS | WIRQHPGK GLEWIG | YIYY----SGSTYNPS LKS | RVTISVDTSKNQFSLKLNSV TAADTAVYYCAR | STAAHYF------YYGMDV | WGQGT TVTVS S |
| iPS:4 37062 | 21-225_200H1 | VH4J4-30.1|D6|6-6|RF2|JH6 | QVQLQES-GPGLVKPSQTLSL TCTVSG-GSIS | SG----GDYWS | WIRQHPGK GLEWIG | YIYY----SGSTYNPS LKS | RVTISVDTSKNQFSLKLNSV TAADTAVYYCAR | DGAAL----------GMDV | WGQGT TVTVS S |
| iPS:4 37066 | 21-225_200G9 | VH4J4-30.1|D6|6-6|RF2|JH6 | QVQLQES-GPGLVKPSQTLSL TCTVSG-GSIS | SG----GDYWS | WIRQHPGK GLEWIG | YIYY----SGSTYNPS LKS | RVTISVDTSKNQFSLKLNSV TAADTAVYYCAR | DGAAL----------GMDV | WGQGT TVTVS S |
| iPS:4 37068 | 21-225_200A11 | VH4J4-30.1|D6|6-6|RF2|JH6 | QVQLQES-GPGLVKPSQTLSL TCTVSG-GSIS | SG----GDYWS | WIRQHPGK GLEWIG | YIYY----RGSTYNPS LKS | RVTISVDTSKNQFSLKLSSV TAADTAVYYCAR | DAAAH----------GMDV | WGQGT TVTVS S |
| iPS:4 37140 | 21-225_214E12 | VH4J4-30.1|D6|6-6|RF2|JH6 | QVQLQES-GPGLVKPSQTLSL TCTVSG-GSIS | SG----GDYWS | WIRQHPGK GLEWIG | YIYY----SGPTYNPS LKS | RVTISVDTSKNQFSLKLSSV TAADTAVYYCAR | DGAAE----------GMDV | WGQGT TVTVS S |
| iPS:4 37158 | 21-225_216H11 | VH4J4-30.1|D6|6-6|RF2|JH6 | QVQLQES-GPGLVKPSQTLSL TCTVSG-GSIS | SG----GDYWS | WIRQHPGK GLEWIG | YIYY----SGPTYNPS LKS | RVTISVDTSKNQFSLKLSSV TAADTAVYYCAR | DGAAE----------GLDV | WGQGT TVTVS S |
| | Germline | VH3J3-33D1|1-26|RF3|JH3 | QVQLVES-GGGVVQPGGSLRL SCAASG-FTFS | S-----YSMN | WVRQAPGK GLEWVS | YISSS----SSIIYADS VKG | RFTISRDNAKNSLYLQMRSL RDEDTAVYYCAR | DYFDY------DAFDI | WGQGT MVTVS S |
| iPS:4 37074 | 21-225_203B2 | VH3J3-33|D1|1-26|RF3|JH3 | QVQLVES-GGGVVQPGRSLRL SCAASG-FTFS | N-----YGMH | WVRQAPGK GLEWVA | IIWFD---GSNEYYADS VKG | RFTISRDNSMSTLYLQMNSL RAEDTAVYYCAR | ESGSY----------ALYI | WGQGT MVTVS S |
| iPS:4 37082 | 21-225_205E12 | VH3J3-33|D1|1-26|RF3|JH3 | QVQLVES-GGGVVQPGRSLRL SCAASG-FTFS | N-----YGMH | WVRQAPGK GLEWVA | IIWFD---GSNEYYADS VKG | RFTISRDNSMSTLYLQMNSL RAEDTAVYYCAR | ESGSY----------ALYI | WGQGT MVTVS S |
| | Germline | VH3J3-48|D4|4-17|RF2|JH4 | EVQLVES-CGGLVQPGGSLRL SCAASG-FTFR | S-----YSMN | WVRQAPGK GLEWVS | YISSS----SSIIYADS VKG | RFTISRDNAKNSLYLQMNSL RDEDTAVYYCAR | DYFDY------YFDY | WGQGT LVTVS S |
| iPS:4 37086 | 21-225_209A8 | VH3J3-48|D4|4-17|RF2|JH4 | EVQLVES-CGGLVQPGGSLRL SCAASG-FTFR | S-----YSMN | WVRQAPGK GLEWVL | YISSS----SSIKKIADS VKG | RFTISRDNAKNSLYLQMNSL RDEDTAVYYCVR | DDGSY----------YFDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4-30.1|D2|2-8|RF3|JH6 | Germline | QVQLQES-GPGLVKPSQTLSL TCTVSG-GSIS | SG----GSYWS | WIRQHPGK GLEWIG | YIYY----SGSTYYNPS LKS | RVTISVDTSKNQFSLKLSSV TAADTAVYYCAR | DIYLGYAL-----YYYGMDV | WGQGT TVTVS S |
| iPS:4 37090 21-225_210F11 | VH4-30.1/D2/2-8|RF3/JH6 | QVQLQES-GPGLVKPSQTLSL TCTVSG-GSIS | SG----GSYWS | WIRQHPGK GLEWIG | YIYY----IGTTYYNPS LKS | RVTISVDTSTNHFSLKLSSV TAADTAVYYCAR | DEPLT-----GMDV | WGQGT TVTVS S |
| iPS:4 37106 21-225_211H7 | VH4-30.1/D2/2-8|RF3/JH6 | QVQLQES-GPGLVKPSQTLSL TCTVSG-GSIS | SG----GYYWS | WIRQHPGK GLEWIG | YIYY----VGSTYYNPS LKS | RVTISVDTSKNQFSLKLSSV TAADTAVYYCAR | DGPLS-----GMDV | WGQGT TVTVS S |
| VH3-30.3|D4|4-17|RF2|JH5 | Germline | QVQLVES-GGGVVQPGRSLRL SCAASG-FTFS | S-----YAMH | WVRQAPGK GLEWVA | VIWYD----GSNKYYADS VKG | RFTISRDNSKNTLYLQMNSL RAEDTAVYYCAR | PYSEY-----NWFDP | WGQGT LVTVS S |
| iPS:4 37100 21-225_211H2 | VH3-30.3D4/4-17|RF2/JH5 | QVQLVES-GGGVVQPGRSLRL SCAASG-FTFS | S-----YAMH | WVRQAPGK GLEWVA | VIWYD----GSNKYYADS VKG | RFTIARDNSKNTLYLQMNSL RAEDTAVYYCAR | DPGSY------GFDF | WGQGT LVTVS S |
| VH3-33|D5|5-12|RF3|JH6 | Germline | QVQLVES-GGGVVQPGRSLRL SCAASG-FTFS | S-----YGMH | WVRQAPGK GLEWVS | VIYY----SGSKYYADS VKG | RFTISRDNSKNTLYLQMNSL RAEDTAVYYCAR | GSSGWYY-----YYYGMDV | WGQGT TVTVS S |
| iPS:4 37102 21-225_211E5 | VH3-33/D5|5-12|RF3/JH6 | QVQLVES-GGGVVQPGRSLRL SCAASG-FTFR | N-----YGMH | WVRQAPGK GLEWVS | IIWFD----GSDQYYADS VKG | RFTISRDNSKNTLYLQMNSL RAEDTAVYYCAR | GLSVYY-----YGMDV | WGQGT TVTVS S |
| iPS:4 37164 21-225_217C6 | VH3-33/D5|5-12|RF3/JH6 | QVQLVES-GGGVVQPGRSLRL SCAASG-FTFS | N-----YGMH | WVRQAPGK GLEWMA | IIWFD----GSDEYYADS VKG | RFTISRDNSKNTLYLQMNSL RAEDTAVYYCAR | GLSVYY-----YGMDV | WGQGT TVTVS S |
| iPS:4 37166 21-225_217G11 | VH3-33/D5|5-12|RF3/JH6 | QVQLVES-GGGVVQPGRSLRL SCAASG-FTFR | N-----YGMH | WVRQAPGK GLEWVS | IIWFD----GSDQYYADS VKG | RFTISRDNSKNTLYLQMNSL RAEDTAVYYCAR | GLSVYY-----YGMDV | WGQGT TVTVS S |
| iPS:4 37170 21-225_218E5 | VH3-33/D5|5-12|RF3/JH6 | QVQLVES-GGGVVQPGRSLRL SCAASG-FTFS | N-----YGMH | WVRQAPGK GLEWMA | IIWFD----GSDEYYADS VKG | RFTISRDNSKNTLYLQMNSL RAEDTAVYYCAR | GLSVYY-----YGMDV | WGQGT TVTVS S |
| VH4-30.1|D6|6-19|RF2|JH6 | Germline | QVQLQES-GPGLVKPSQTLSL TCTVSG-GSIS | SG----GSYWS | WIRQHPGK GLEWIG | YIYY----SGSTYYNPS LKS | RVTISVDTSKNQFSLKLSSV TAADTAVYYCAR | GIAVAGY-----YYYGMDV | WGQGT TVTVS S |

Figure 51 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:4 37108 | 21-225_211C9 | VH4J4-30.1/D6J6-19JRF2/J H6 | QVQLQES-GPGLVKPSQTLSL TCIVSG-GSIR | SG---GDYWS | WIRQHPGK GLEWIG | YIYY---- SGSTYYNPS LKS | RVTILLDTSKNQFSLKLSSV TVADTAVYYCAR | DSAVY----------NMDV | WGQGT TVTVS S |
| iPS:4 37110 | 21-225_211E9 | VH4J4-30.1/D6J6-19JRF2/J H6 | QVQLQES-GPGLVKPSQTLSL TCTVSG-GSIS | SG---GDYWS | WIRQHPGK GLEWIG | YIYY---- TGSNYNPS LKS | RVTISVDTSKNQFSLNLISV IAADTAVYYCAR | DSAVY----------GMDV | WGQGT TVTVS S |
| iPS:4 37120 | 21-225_212A9 | VH4J4-30.1/D6J6-19JRF2/J H6 | QVQLQES-GPGLVKPSQTLSL TCSVSG-GSIR | SG---GDYWS | WIRQHPGK GLEWIG | YMYY---- SGSTYYNPS LKS | RVTISVDTSKNQFSLKLSSV TVADTAVYYCAR | DSAVY----------GMDV | WGQGT TVTVS S |
| iPS:4 37132 | 21-225_213F5 | VH4J4-30.1/D6J6-19JRF2/J H6 | QVQLQES-GPGLVKPSQTLSL TCSVSG-GSIR | SG---GDYWS | WIRQHPGK GLEWIG | YIYY---- SGSTYYNPS LKS | RVTISLDTSKNQFSLKLSSV TVADTAVYYCAR | DSAVY----------NMDV | WGQGT TVTVS S |
| iPS:4 37142 | 21-225_215A3 | VH4J4-30.1/D6J6-19JRF2/J H6 | QVQLQES-GPGLVKPSQTLSL TCTVSG-GSIS | SG---GDYWS | WIRQHPGK GLEWIG | YIYY---- TGSNYNPS LKS | RVTISVDTSKNQFSLKVISV IAADTAVYYCAR | DSAVY----------GMDV | WGQGT TVTVS S |
| iPS:4 37148 | 21-225_215H3 | VH4J4-30.1/D6J6-19JRF2/J H6 | QVQLQES-GPGLVKPSQTLSL TCSVSG-GSIR | SG---GDYWS | WIRQHPGK GLEWIG | YMYY---- SGSTYYNPS LKS | RVTISVDTSKNQFSLKLSSV TVADTAVYYCAR | DSAVY----------GMDV | WGQGT TVTVS S |
| iPS:4 37154 | 21-225_216A7 | VH4J4-30.1/D6J6-19JRF2/J H6 | QVQLQES-GPGLVKPSQTLSL TCSVSG-GSIR | SG---GDYWS | WIRQHPGK GLEWIG | YMYY---- SGSTYYNPS LKS | RVTISVDTSKNQFSLKLSSV TVADTAVYYCAR | DSAVY----------GMDV | WGQGT TVTVS S |
| | Germline | | | | | | | | |
| | VH3J3-30.3D7/7-27JRF2/JH4 | | | | | | | | |
| iPS:4 37160 | 21-225_216B12 | VH3J3-30.3/D7J7-27JRF2/J H4 | QVQLVES-GGGVVQPGRSLRL SCAASG-FIFS | S-----YAMH | WVRQAPGK GLEWVA | VIWYD-- GSNKYYADS VKG | RFIISRDNSKNTLYLQMNSL RAEDTAVYYCAR | DLGLG---------YFFDY | WGQGT LVTVS S |
| | Germline | | | | | | | | |
| | VH6J6-01/6D2/2-21JRF2JH5 | | | | | | | | |
| iPS:4 37186 | 21-225_224H2 | VH6J6-01/D2J2-21JRF2/J H5 | QVQLQQS-GPGLVKPSQTLSL TCDISG-DSVS | SN---SAAWN | WIRQSPSR GLEMLG | RTYYR-- SKWYNDYAV SVKS | RVTINPDTSKNQFSLQLNSV IPEDTAVYYCAR | EGGLGYCSST-----SCYGGWFDF | WGQGT LVTVS S |
| | Germline | | | | | | | | |
| | VH1J1-02/D4J4-17JRF2JH6 | | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 37188 | 21-225_224B11 | VH1|1-02/D4|4-17|RF2|JH6 | QVHLVQS-GAEVKKPGASVKV SCKASG-YTFT | G-----YYIH | WVRQAPGQ GLEWMG | WINPK---NGGTNYAQK FQG | RVTMTRDASISTTYMELSRL RSDDTAVYYCAR | GAFDYFY-------YYAMDV | WGHGT TVTVS S |
| iPS:4 37198 | 21-225_226F8 | VH1|1-02/D4|4-17|RF2|JH6 | QVQLVQS-GAEVKKPGASVKV SCKASG-YTFT | G-----YYIH | WVRQAPGQ GLEWMG | WINPN---SGGTNYARK FQG | RVTMTRDTSISTAYMELSRL RSDDTAVYYCAR | GAFDYYY-------YYALDV | WGQGT TVTVS S |
| iPS:4 37202 | 21-225_227D3 | VH1|1-02/D4|4-17|RF2|JH6 | QVQLVQS-GAEVKKPGASVKV SCKASG-YTFT | G-----YYMH | WVRQAPGQ GLERMG | WINPK---SGGTNFAQR FQG | RVTMTRDTSISTAYMELSRL RSDDTAVYYCAR | GAFDYFY-------YYGMDV | WGQGT TVTVS S |
| iPS:4 37208 | 21-225_227C10 | VH1|1-02/D4|4-17|RF2|JH6 | QVQLVQS-GAEVKKPGASVKV SCKASG-YTFT | G-----YYMH | WVRQAPGQ GLERMG | WINPK---SGGTNYAQK FQG | RVTMTRDTSISTAYMELSRL RSDDTAVYYCAR | GAFDYFY-------YYGMDV | WGQGT TVTVS S |
| | Germline VH3|3-33/D2|2-2|RF2|JH6 | | | | | | | |
| iPS:4 37192 | 21-225_225E9 | VH3|3-33/D2|2-2|RF2|JH6 | QVQLVES-GGGVVQPGRSLRL SCEASG-FTFS | S-----YGMH | WVRQAPGK GLEWVA | VMWYD---GGNKDYADS VKG | RFTISRDNSKNTLYLQMNSL RAEDTAVYYCAR | DREYCTSTSC-----PYYYYGMDV | WGQGT TVTVS S |
| | Germline VH3|3-23/D2|2-21|RF2|JH6 | | | | | | | |
| iPS:4 37204 | 21-225_227E5 | VH3|3-23/D2|2-21|RF2|JH6 | EVQLLES-GGGLVQPEGSLRL SCAASG-FTFS | S-----YAMS | WVRQAPGK GLEWVS | AISGS---GGSTYYADS VKG | RFTISRDNSKNTLCLEMNSL RAEDTAVYYCAK | EYCGGDCYSF-----YYYYGMDV | WGQGT TVTVS S |
| iPS:3 93196 | 21-225_16G8 | VH3|3-23/D2|2-21|RF2|JH6 | EVQLLES-GGGLVQPEGSLRL SCAASG-FTFS | S-----YAMS | WVRQAPGK GLEWVS | GISGS---GGSTYYADS VKG | RFTISRDNSKNTLCLEMNSL RAEDTAVYYCAK | EYCGGDCYSP-----YYYYGMDV | WGQGT TVTVS S |
| iPS:3 93202 | 21-225_6B4 | VH3|3-23/D2|2-21|RF2|JH6 | EVQLLES-GGGLVQPEGSLRL SCAASG-FTFS | S-----YAMS | WVRQAPGK GLEWVS | AISGS---GGSTYYADS VKG | RFTISRDNSKNTLCLQMNSL RAEDTAVYYCAK | EYCGGDCYSP-----YYYYGMDV | WGQGT TVTVS S |
| iPS:3 93345 | 21-225_5G7 | VH3|3-23/D2|2-21|RF2|JH6 | EVQLLES-GGGLVQPEGSLRL SCAASG-FTFS | S-----YAMS | WVRQAPGK GLEWVS | AISGS---GGSTYYADS VKG | RFTISRDNSKNTLCLQMNSL RAEDTAVYYCAK | EYCGGDCYSP-----YYYYGMDV | WGQGT TVTVS S |
| | Germline VH2|2-05/D6|6-13|RF3|JH4 | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:4 37210 | 21-225_227E12 | VH2/2-05/D6/6-13/RF3/J H4 | QITLKES-GPTLVKPTQLTL TCTFSG-FSLS | TS---GVGVG | WIRQPPGK ALECLS | LIYW----NDDKVISPS LKS | RLTITKYTSKNQVVLTMTNM DPVDTATYYCAH | RGQQL---------ALDY | WGQGT LVTVS S |
| iPS:3 92587 | 21-225_18G5 | VH2/2-05/D6/6-13/RF3/J H4 | QITLKES-GPTLVKPTQLTL TCTFSG-FSLS | TS---GVGVG | WIRQPPGK ALECLS | LIYW----NDDKVISPS LKS | RLTITKYTSKNQVVLTMTNM DPVDTATYYCAH | RGQQL---------ALDY | WGQGT LVTVS S |
| iPS:3 98504 | 21-225_23D7 | VH2/2-05/D6/6-13/RF3/J H4 | QITLKES-GPTLVKPTQLTL TCTFSG-FSLS | TS---GVGVG | WIRQPPGK ALECLS | LIYW----NNDKVISPS LKS | RLTITKYTSKNQVVLIMSNM DPVDTATYYCAH | RGQQL---------ALDY | WGQGT LVTVS S |
| | Germline | VH3/3-21/D4/4-11/RF2/JH6 | EVQLVES-GGGLVKPGGSLRL SCAASG-FTFS | S------YSMN | WVRQAPGK GLEWVS | SISSSS--SSYIYYADS VKG | RFTISRDNAKNSLYLQMNSL RAEDTAVYYCAR | DSNMY---------YYGMDV | WGQGT LVTVS S |
| iPS:4 37226 | 21-225_57C2 | VH3/3-21/D4/4-11/RF2/J H6 | EVQLVES-GGGLVKPGGSLRL SCAASG-FTFS | S------FGMN | WVRQAPGK GLEWVS | SISSS---TGYIYNADS VKG | RFTISRDNAKNSLYLQMNSL RAEDTAVYYCAR | TYSG----------SLDV | WGQGT TVTVS S |
| | Germline | VH3/3-21/D5/5-18/RF3/JH5 | EVQLVES-GGGLVKPGGSLRL SCAASG-FTFS | S------YSMN | WVRQAPGK GLEWVS | SISSSS--SSYIYYADS VKG | RFTISRDNAKNSLYLQMNSL RAEDTAVYYCAR | GSRGY---------NWFDP | WGQGT LVTVS S |
| iPS:4 37230 | 21-225_62H10 | VH3/3-21/D5/5-18/RF3/J H5 | EVQLVES-GGGLVKPGGSLRL SCAASG-FTFS | S------YSMN | WVRQAPGK GLEWVS | SISSS---SSYIYYADS VKG | RFTISRDNAKNSLYLQMNSL RAEDTAVYYCAR | GGSR----------GFDP | WGQGT LVTVS S |
| iPS:4 48906 | 21-225_72G9 | VH3/3-21/D5/5-18/RF3/J H5 | EVQLVES-GGGLVKPGGSLRL SCAASG-FTFS | S------YSMN | WVRQAPGK GLEWVS | SISGS---SSYIYYADS VKG | RFTISRDNAKNSLYFCAR | GGSR----------GFDP | WGQGT LVTVS S |
| | Germline | VH1/1-02/D1/1-26/RF1/JH4 | QVQLVQS-GAEVKKPGASVKV SCKASG-YTFT | G------YFMH | WVRQAPGQ GLEWMG | WINPN---SGGTNQA FQG | RVTMTRDTSISTAYMELSRL TSEDTAVYYCAR | GGATYY---------YYFDY | WGQGT LVTVS S |
| iPS:4 37260 | 21-225_170D1 | VH1/1-02/D1/1-26/RF1/J H4 | QVQLVQS-GAEVKKPGASVKV SCKASG-YTFT | G------YFMH | WVRQAPGQ GLEWMG | WIKPK---SGGTNCAQK FQG | RVTMTRDTSSTAYMELSRL TSDDTAVYYCAR | GGATYY---------MGVFDY | WGQGT LVTVS S |
| | Germline | VH3/3-33/D2/2-21/RF2/JH6 | QVQLVES-GGGVVQPGRSLRL SCAASG-FTFS | S------YGMH | WVRQAPGK GLEWVA | VIWYD---GSNKYYADS VKG | RFTISRDNSKNTLYLQMNSL RAEDTAVYYCAR | AYCGGDCYFP---YYYGMDV | WGQGT LVTVS S |
| iPS:4 37268 | 21-225_177D2 | VH3/3-33/D2/2-21/RF2/J H6 | QVQLVES-GGGVVQPGRSLRL SCAASG-FTFS | S------YGMD | WVRQAPGK GLEWVA | IIWFD---GSNKYYADS VKG | RFTISRDNSKNTLYLQMNSL RAEDTAVYYCAR | AYCGGDCYFP---HLHYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4/4-30.1/D4/4-17/RF2/JH4 | | QVQLQES--------GPGLVKPQSLSL TCTVSG-GSIS | SG----GYYWS | WIRQHPGK GLEWIG | YIYY----SGSTYNPS LKS | RVTISVDTSKNQFSLKLSSV TAADTAVYFCAR | DSPDR----GFDY | WGQGT LVTVS S |
| iPS:4 37294 | 21-225_216D5 | VH4/4-30.1/D4/4-17/RF2/H4 | QVQLQES--------GPGLVKPSQTLSL TCTVSG-GSIS | SG----GYYWS | WIRQHPGK GLEWIG | YIYY----SGSTYNPS LKS | RVTISVDTSKNQFSLKLNSV TAADTAVYFCAR | DSPDR----GFDY | WGQGT LVTVS S |
| | Germline | | | | | | | |
| VH3/3-30.3/D5/5-24/RF3/JH6 | | QVQLVES--------GGGVVQPGRSLRL SCAASG-FTFS | S------YGMH | WVRQAPGK GLEWVS | VISYD----GSNKYADS VKG | RFTISRDNSKNTLYLQMNSL RAEDTAVYYCAR | RGYSYG-------GYGMDV | WGQGT TVTVS S |
| iPS:4 37302 | 21-225_225B11 | VH3/3-30.3/D5/5-24/RF3/JH6 | QVQLVES--------GGGVVQPGRSLRL SCAASG-FTFS | S------YGMH | WVRQAPGK GLEWVT | IISYS----GSNKYADS VKG | RFTISRDNSKNTLYLQMNSL RAEDTAVYYCAR | RGYSYG-------GYGMDV | WGQGT TVTVS S |
| iPS:4 51102 | 21-225_45F6 | VH3/3-30.3/D5/5-24/RF3/JH6 | QVQLVES--------GGGVVQPGRSLRL SCAASG-FTFS | Y------YGLH | WVRQAPGK GLEWVA | VISID----GSNKYADS VKG | RFTISRDNSKNTLYLQMNNL RAEDTAVFYCAR | EDRYCSGTSC----PYYYYGMDV | WGQGT TVTVS S |
| iPS:3 92868 | 21-225_24D6 | VH3/3-30.3/D5/5-24/RF3/JH6 | QVQLVES--------GGGVVQPGRSLRL SCAASG-FTFS | S------YGMH | WVRQVPGK GLEWVA | IISYA----GSNKYADS VKG | RFTISRDNSKNTLYLQMNSL RAEDTAVYYCVR | RGYSYG-------GYGMDV | WGQGA TVTVS S |
| iPS:3 93910 | 21-225_15F10 | VH3/3-30.3/D5/5-24/RF3/JH6 | QVQLVES--------GGGVVQPGRSLRL SCAASG-FTFS | S------YGMH | WVRQAPGK GLEWVS | VISYG----GSNNYADS VKG | RFTISRDNSKNTLYLQMNSL RAEDTAVYYCVR | RGYSYG-------GYGMDV | WGQGT TVTVS S |
| iPS:3 94000 | 21-225_11A2 | VH3/3-30.3/D5/5-24/RF3/JH6 | QVQLVES--------GGGVVQPGRSLRL SCAASG-FTFS | S------YGMH | WVRQAPGK GLEWVA | VISIG----GSNKDSADE VKG | RFTISRDNSKNTLYLQMNSL RAEDTAVYYCVR | RGYSYG-------GYGMDV | WGQGT TVTVS S |
| iPS:3 94004 | 21-225_13A1 | VH3/3-30.3/D5/5-24/RF3/JH6 | QVQLVES--------GGGVVQPGRSLRL SCAASG-FTFS | S------YGMH | WVRQAPGK GLEWVA | VISYA----GTNQYYADS VKG | RFTISRDNSKNTLYLQMNSL RAEDTAVYYCVR | RGYSYG-------GYGMDV | WGQGT TVTVS S |
| iPS:3 94006 | 21-225_15C2 | VH3/3-30.3/D5/5-24/RF3/JH6 | QVQLVES--------GGGVVQPGRSLRL SCAASG-FTFS | S------YGMH | WVRQAPGK GLEWVS | IISYG----GRNNHYADS VKG | RFTISRDNSKNTLYLQMNSL RAEDTAVYYCAR | RGYSYG-------GYGMDV | WGQGT TVTVS S |
| iPS:3 94029 | 21-225_1B12 | VH3/3-30.3/D5/5-24/RF3/JH6 | QVQLVES--------GGGVVQPGRSLRL SCAASG-FTFS | S------YGMH | WVRQAPGK GLEWVA | IISYA----GSNKSYADS VKG | RFTISRDNSKNMLYLQMNSL RAEDTAVYYCVR | RGYSYG-------GYGMDV | WGQGA TVTVS S |
| iPS:3 94047 | 21-225_5E6 | VH3/3-30.3/D5/5-24/RF3/JH6 | QVQLVES--------GGGVVQPGRSLRL SCAASG-FTFS | S------YGMH | WVRQAPGK GLEWVA | IISYV----GNKKYYADS VKG | RFTISRDNSKNTLYLQMNSL RVEDTAVYYCAR | RGYSYG-------GYGMDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 94081 | 21-225_16B3 | VH3J3-30.3/D5J5-24/RF3/JH6 | QVQLVES-GGGVVQPGRSLRL SCVASG-FTFS | S-----YGMH | WVRQAPGK GLEWVA | VISYA---GINKSIADS VKG | RFTISRDNSKNTLYLQMNSL RAEDTAVYYCVR | RGYSYG-------GYGMDV | WGQGA TVTVS S |
| | | Germline | | | | | | | |
| | VH4J4-61/D3J3-9/RF1/JH4 | | | | | | | | |
| iPS:4 51118 | 21-225_191C8 | VH4J4-61/D3J3-9/RF1/JH4 | QVQLQES-GPGLVKPSETLSL TCTVSS-GSVS | SG---GYYWS | WIRQPPGK GLEWIG | YIYY-----SGTTYNPS LKS | RVTISVDTSKNQFSLKLISV TVADTAVYYCAR | DTPCFDG-------CGYFFDS | WGQGT LVTVS S |
| | | Germline | | | | | | | |
| | VH2J2-05/D4J4-11/RF3/JH4 | | | | | | | | |
| iPS:3 92573 | 21-225_15G2 | VH2J2-05D4J4-11/RF3/JH4 | QITLKES-GPTIVKPTQTLTL TCTFSG-FSLS | TS---GVGVG | WIRQPPGK ALEWLA | LIIW----NDDKRYSPS LKS | RLIITKDTSKNQVVLTMTNM DEVDTATYYCAD | TGVSC--------CYFHY | WGQGT LVTVS S |
| | | Germline | | | | | | | |
| | VH1J1-02/D2J2-2/RF2/JH6 | | | | | | | | |
| iPS:3 92585 | 21-225_14H11 | VH1J1-02D2J2-2/RF2/JH6 | QVQLVQS-GAEVKKPGASVKV SCQGSG-YTFT | G---HYMC | WVRQAPGQ GLEWMG | WINPN----SGGTNYAQK FQG | RVTMTRDISISTAYMELSRL RSDDTAVYYCAA | GYCSSSCYL----QPGYYGMDV | WGQGT TVTVS S |
| iPS:3 93186 | 21-225_27D9 | VH1J1-02D2J2-2/RF2/JH6 | QVQLVQS-GAEVKKPGASVKV SCKASG-YTFT | G---YYMH | WVRQAPGQ GLEWMG | MINPN----SGGTKYAQK FQG | RVTMTRDISISTAYMELNRL RSDDTAVYYCAR | ERCSTTSCYL----GTGYYGMDV | WGQGT TVTVS S |
| iPS:3 93234 | 21-225_26C10 | VH1J1-02D2J2-2/RF2/JH6 | QVQLVQS-GAEVKKPGASVKV SCKASG-YTFT | G---YYVH | WVRQAPGK GLEWVS | WINPN----SGGTNYAQK FQG | RVTMTRDISISTAYMELSRL RSDDTAVYYCAR | ERCSTTSCYL----GTGYYGMDV | WGQGT TVTVS S |
| | | Germline | | | | | | | |
| | VH3J3-23/D5J5-12/RF3/JH6 | | | | | | | | |
| iPS:3 92596 | 21-225_12D8 | VH3J3-23D5J5-12/RF3/JH6 | EVQLLES-GGGLVQPGGSLRL SCAASG-FTFS | S-----YVMS | WVRQAPGK GLEWVS | IISVG----GGSTYYADS VKG | RFTISRDNSKTLYLQMNSL RAEDTAVYYCAK | WGRGYSYE-------YYYGMDV | WGQGT TVTVS S |
| iPS:3 92942 | 21-225_30E9 | VH3J3-23D5J5-12/RF3/JH6 | EVQLLES-GGGLVQPGGSLRL SCAASG-FTFS | S-----CAMN | WVRQAPGK GLEWVS | AISGR----GGSTFYADS VKG | RFTISRDNSKNTLYLQMNSL RAEDTAVYYCAK | GELLEDY-------YYYGMDV | WGQGT TVTVS S |

Figure 51 (Continued)

| | | | | | | | | |
|---|---|---|---|---|---|---|---|---|
| iPS:3 92944 | 21-225_31H5 | VH3J3-23lD5l5-12lRF3lJ H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQMNSL RAEDTAVYYCVK | GELLEDY------YFYGMDV | WGQGT TVTVS S |
| iPS:3 92964 | 21-225_31A8 | VH3J3-23lD5l5-12lRF3lJ H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQMNSL RDEDTAVYYCVK | GELLEDY------YFYGMDV | WGQGT TVTVS S |
| iPS:3 92982 | 21-225_30D1 | VH3J3-23lD5l5-12lRF3lJ H6 | EVQVLES-GGGLVQPGGSLRL SCAASG-FTFS | S-----YAMS | WVRQAPGK GLEWVS | AISGR---GGSTFHADS VKG | RFTISRDNSKNTLYLQMNSL RAEDTAVYYCVK | GELLEDY------YFYGLDV | WGQGT TVTVS S |
| iPS:3 92986 | 21-225_31B8 | VH3J3-23lD5l5-12lRF3lJ H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQMNSL RAEDTAVYYCVK | GELLEDY------YFYGMDV | WGQGT TVTVS S |
| iPS:3 93004 | 21-225_30G11 | VH3J3-23lD5l5-12lRF3lJ H6 | EVQLLES-GGGLVQPGGSLRL SCAASG-FTFS | S-----YAMS | WVRQAPGK GLEWVS | AISGR---GGSTFHADS VKG | RFTISRDNSKTTLYLQMNSL RAEDTAVYYCVK | GELLEDY------YFYGMDV | WGQGT TVTVS S |
| iPS:3 93040 | 21-225_30E3 | VH3J3-23lD5l5-12lRF3lJ H6 | EVQLLES-GGGLVQPGGSLRL SCAASG-FTFS | S-----YAMN | WVRQAPGK GLEWVS | AISGR---GGSTFYADS EKG | RFTISRDNSKNTLYLQMNSL RAEDTALYYCAK | GELLEDY------YYYGMDV | WGQGT TVTVS S |
| iPS:3 93058 | 21-225_31H3 | VH3J3-23lD5l5-12lRF3lJ H6 | EVQVLES-GGGLVQPGGSLRL SCAASG-FTFS | S-----YAMN | WVRQAPGK GLEWVS | AISGR---GGNTFYADS VKG | RFTISRDNSKNTLYLQMNSL RAEDTAVYYCVK | GELLEDY------YYYGMDV | WGQGT TVTVS S |
| iPS:3 93060 | 21-225_32G12 | VH3J3-23lD5l5-12lRF3lJ H6 | EVQLLES-GGGLVQPGGSLRL SCAASG-FTFS | S-----YAMS | WVRQVEGK GLEWVS | SISGR---GGSTFYADS VKG | RFTISRDNSKNTLYLQMNSL RAEDTAVYYCVK | GELLEDY------YFYGMDV | WGQGT TVTVS S |
| iPS:3 93068 | 21-225_34G9 | VH3J3-23lD5l5-12lRF3lJ H6 | EVQLLES-GGGLVQPGGSLRL SCAASG-FTFN | S-----YAMS | WVRQAPGK GLEWVS | AISGR---GGSTFYADS VKG | RFTISRDNSKNTLYLQMNSL RAEDTAVYYCVK | GELLEDY------YFYGMDV | WGQGT TVTVS S |
| iPS:3 93072 | 21-225_36C5 | VH3J3-23lD5l5-12lRF3lJ H6 | EVQLVES-GGGLVQPGGSLRL SCAASG-FTFS | S-----YAMN | WVRQAPGK GLEWVS | AISRR---GGSTFYADS VKG | RFTISRDNSKNTLYLQMNSL RAEDTAVYYCVK | GELLEDY------YFYGMDV | WGQGT TVTVS S |
| iPS:3 93076 | 21-225_33A4 | VH3J3-23lD5l5-12lRF3lJ H6 | EVQLLES-GGGLVQSGGSLRL SCEASG-FTFS | S-----YAMN | WVRQVEGK GLEWVS | AISGR---GGSTFYADS VKG | RFTISRDNSKNTLYLQMNSL RAEDTAVYFCAK | GELLEDY------SYYGIDV | WGQGT TVTVS S |
| iPS:3 93102 | 21-225_33F1 | VH3J3-23lD5l5-12lRF3lJ H6 | EVQLLES-GGGLLQPGGSLRL SCAASG-FTFS | S-----YAMS | WVRQAPGK GLEWVS | SISGR---GGSTFHADS VKG | RFTISRDNSKNTLYLQMNSL RAEDTAVYYCVK | GELLEDY------YFYGMDV | WGQGT TVTVS S |

Figure 51 (Continued)

| | | | | | | | | |
|---|---|---|---|---|---|---|---|---|
| iPS:3 93104 | 21-225_33A7 | VH3J3-23JD5J5-12JRF3JJ H6 | EVQLLES-GGGLVQPGGSLRL SCAASG-FTFS | S-----CAMS | WVRQAPGK GLEWVS | AISGR---GGSTFHADS VKG | RFTISRDNSKNTLYLQMNSL RAEDTAVYYCVK | GELLEDY-------YFYGMDV | WGQGT TVTVS S |
| iPS:3 93106 | 21-225_34A6 | VH3J3-23JD5J5-12JRF3JJ H6 | EVQLLES-GGGLVQPGGSLRL SCAASG-FTFN | N-----YAMN | WVRQAPGK GLEWVS | AISRR---GGSTFYADS VKG | RFTISRDNSKNTLYLQMNSL RAEDTAVYYCAK | GELLEDY-------YYFAMDV | WGQGT TVTVS S |
| iPS:3 93110 | 21-225_35B7 | VH3J3-23JD5J5-12JRF3JJ H6 | EVQLLES-GGGLVQPGGSLRL SCAASG-FTFS | S-----YAMS | WVRQAPGK GLEWVS | AISGR---GGSTFYADS VKG | RFTISRDNSKNTLYLQMNSL RAEDTAVYYCAK | GELLEDY-------YFYGMDV | WGQGA TVTVS S |
| iPS:3 93118 | 21-225_34H11 | VH3J3-23JD5J5-12JRF3JJ H6 | EVQLLES-GGGLVQPGGSLRL SCAASG-FTFS | S-----YAMN | WVRQAPGE GLEWVS | AISGR---GGSTFHADS VKG | RFTISRDNSKNTLFLQMNSL RAEDTAVYYCVK | GELLEDY-------YYYGMDV | WGQGT TVTVS S |
| iPS:3 93124 | 21-225_33G7 | VH3J3-23JD5J5-12JRF3JJ H6 | EVQLLES-GGGLVQPGGSLRL SCAASG-FTFN | N-----YAMS | WVRQAPGK GLEWVS | AISRR---GGSTFYADS VKG | QFTISRDNSKNTLYLQMNSL RAEDTAVYYCAK | GELLEDY-------SYYGMDV | WGQGT TVTVS S |
| iPS:3 93126 | 21-225_35D1 | VH3J3-23JD5J5-12JRF3JJ H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQMNSL RAEDTAVYYCAK | GELLEDY-------YFYGMDV | WGQGA TVTVS S |
| iPS:3 93128 | 21-225_35F11 | VH3J3-23JD5J5-12JRF3JJ H6 | EVQLLES-GGGLVQPGGSLRL SCAASG-FTFS | S-----YAMS | WVRQAPGK GLEWVS | AISGR---GGSTFHADS MKG | RFTISRDNSKNTLYLQMNSL RAEDTAVYYCVK | GELLEDY-------YFYGMDV | WGQGT TVTVS S |
| iPS:3 93146 | 21-225_34G8 | VH3J3-23JD5J5-12JRF3JJ H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQINSL RAEDTAVYYCVK | GELLEDY-------YFYGMDV | WGQGT TVTVS S |
| iPS:3 93150 | 21-225_36A5 | VH3J3-23JD5J5-12JRF3JJ H6 | EVQLLES-GGGLVQPGGSLRL SCAASG-FTFN | N-----YAMN | WVRQAPGK GLEWVS | AISGR---GGNTFYADS VKG | RFTISRDNSKNTLYLQMNSL RAEDTAVYYCAK | GELLEDY-------YYAMDV | WGQGT TVTVS S |
| iPS:3 93180 | 21-225_4G12 | VH3J3-23JD5J5-12JRF3JJ H6 | EVQLLES-GGGLVQPGGSLRL SCAASG-FTFS | S-----YAMS | WVRQAPGK GLEWVS | TLSGR---GGSTYYADS VKG | RSTISRDNSKNTLYLQMSSL RAEDTAVYYCAK | WGRGYSYE------YYYGMDV | WGQGT TVTVS S |
| iPS:3 93232 | 21-225_17F12 | VH3J3-23JD5J5-12JRF3JJ H6 | EVQLLES-GGGLVQPGGSLRL SCAASG-FTFS | S-----YAMS | WVRQAPGK GLEWVS | AISGG---GGSTYYADS VKG | RVTISRDNSKNTLYLQMNSL RAEDTAVYYCAK | WGRGYNYE------YYYGMDV | WGQGT TVTVS S |
| iPS:3 98494 | 21-225_21H4 | VH3J3-23JD5J5-12JRF3JJ H6 | EVQLLES-GGGLVQPGGSLRL SCAASG-FTFS | S-----YAMS | WVRQAPGK GLEWVS | ALSGR---GGSTYYADS VKG | RFTISRDNSKNTLYLQMNSL RAEDTAVYYCAK | WGRGYSYE------YYYGMDV | WGQGT TVTVS S |

Figure 51 (Continued)

| | | | H FR1 | H CDR1 | H FR2 | H CDR2 | H FR3 | H CDR3 | H FR4 |
|---|---|---|---|---|---|---|---|---|---|
| iPS:3 98508 | 21-225_24B1 | VH3J3-23|D5|5-12|RF3|J H6 | EVQLLES-GGGLVQPGGSLRL SCAASG-FTFS | S-----YAMS | WVRQAPGK GLEWVS | AISGR---GGSTYHADS VKG | RFTISRDNSKNTLYLQMNSL RAEDTAVYYCAK | WGRGYSYE------------YYYGMDV | WGQGT TVTVS S |
| iPS:3 98528 | 21-225_32G1 | VH3J3-23|D5|5-12|RF3|J H6 | EVQLLES-GGGLAQPGGSLRL SCAASG-FTFS | S-----YAMS | WVRQAPGK GLEWVS | AISGR---GGSTFHADS VKG | RFTISRDNSKNTLYLQMNSL RAEDTAVYYCVK | GELLEDY-------------YFYGMDV | WGQGT TVTVS S |
| iPS:3 98534 | 21-225_33B8 | VH3J3-23|D5|5-12|RF3|J H6 | EVQLLES-GGGLVQPGGSLRL SCAASG-FTFS | S-----YAMS | WVRQAPGK GLEWVS | AISGR---GGSTFHADS VKG | RFTISRDNSKNTLYLQMNSL RAEDTAVYYCVK | GELLEDY-------------YFYGMDV | WGQGT TVTVS S |
| iPS:3 98540 | 21-225_35A6 | VH3J3-23|D5|5-12|RF3|J H6 | EVQLLES-GGGLVQPGGSLRL SCAASG-FTFS | S-----YAMS | WVRQAPGK GLEWVS | TISGR---GGSTFHADS VKG | RFTISRDNSKNTLYLQMNSL RAEDTAVYYCVK | GELLEDY-------------YFYGMDV | WGQGT TVTVS S |
| | Germline | | H FR1 | H CDR1 | H FR2 | H CDR2 | H FR3 | H CDR3 | H FR4 |
| | VH4|4-39|D4|4-17|RF2|H4 | | QLQLQES-GPGLVKPSETLSL TCTVSG-GSIS | RS----SYYWG | WIRQPPGK GLEWIG | SIYYS---SGSTYYNPS LKS | RVTISVDTSKNQFSLKLSS TAADTAVYYCAR | TFDY | WGQGT LVTVS S |
| iPS:3 92622 | 21-225_17H8 | VH4|4-39|D4|4-17|RF2|J H4 | QLQLQES-GPGLVKPSETLSL TCTVSG-GSIS | RS----SYYWG | WIRQPPGK GLEWIG | NIYY----GGNTYNPS LKS | RVTISVDTSKNQFSLKLSSV TAADTAVYYCAR | HGKDW---------------GLDY | WGQGT LVTVS S |
| iPS:3 92638 | 21-225_17F9 | VH4|4-39|D4|4-17|RF2|J H4 | QLQLQES-GPGLVKPSETLSL TCTVSG-GSIS | RS----SYYWG | WIRQPPGK GLEWIG | NIYY----SGSTYNPS LKS | RVTISVDSSKNQFSLNLNSV TAADTAVYSCAR | HGKDW---------------GLDY | WGQGT LVTVS S |
| iPS:3 92656 | 21-225_1F2 | VH4|4-39|D4|4-17|RF2|J H4 | QLQLQES-GPGLVKPSETLSL TCTVSG-GSIS | RS----SYYWG | WIRQPPGK GLEWIG | NIYY----SGSAYNNPS LKG | RVTISVDTSKNQFSLKLNSV TAADTAVYYCGR | HGKDW---------------GLDY | WGQGT LVTVS S |
| iPS:3 92794 | 21-225_21H3 | VH4|4-39|D4|4-17|RF2|J H4 | QLQLQES-GPGLVKPSETLSL TCTVSG-GSIS | RS----SYYWG | WIRQPPGK GLEWIG | NIYY----SGSTDNPS LKS | RVTISVDTSKNQFSLKLSSV TAADTAVYYCGR | HGKDW---------------GLDY | WGQGT LVTVS S |
| iPS:3 92822 | 21-225_23C8 | VH4|4-39|D4|4-17|RF2|J H4 | QLQLQES-GPGLVKPSETLSL TCTVSG-GSIS | RS----SYYWG | WIRQPEGK GLEWIG | NIYY----SGTTYNPS LKS | RVTISVDTSKNHFSLKLSSV TAADTAVYYCGR | HGKDW---------------GLDY | WGQGT LVTVS S |
| iPS:3 92838 | 21-225_22G8 | VH4|4-39|D4|4-17|RF2|J H4 | QLQLQES-GPGLVKPSETLSL TCTVSG-GSIN | RS----SYYWG | WIRQPPGK GLDWIG | NIYY----SGSTYNPS VKS | RFTISVDTSKNQFSLKLSSV TAADTAVYYCAR | HGKDW---------------GLDY | WGQGT LVTVS S |
| iPS:3 92858 | 21-225_22H4 | VH4|4-39|D4|4-17|RF2|J H4 | QLQLQES-GPGLVKPSETLSL TCTVSG-GSIS | RS----SYYWG | WIRQPPGK GLEWIG | NIYY----SGSTYHNPS LKS | RVTISVDISMNQFSLKLISV TAADTAVYFCGR | HGKDW---------------GLDY | WGQGT LVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 92882 | 21-225_23A3 | VH4|4-39/D4|4-17|RF2/JH4 | QLQLQES-GPGLVKPSETLSL TCTVSG-GSIS | RS---SYYWG | WIRQPPGQ GLEWIG | NIYY----SGSTYNNPSLKS | RVSISVDTSKNQFSLNLSSV TAADTAVYYCAR | HGKDW------GLDF | WGQGT LVTVS S |
| iPS:3 93804 | 21-225_5H7 | VH4|4-39/D4|4-17|RF2/JH4 | QLQLQES-GPGLVKPSETLSL TCTVSG-GSIN | RS---SYYWG | WIRQPPGK GLEWIG | NIYY----SGTTYNPSLKS | RVTISVDTSKNQFSLNLSSV TTAADTAVYSCAR | HGKDW------GLDY | WGQGT LVTVS S |
| iPS:3 93832 | 21-225_14B2 | VH4|4-39/D4|4-17|RF2/JH4 | QLQLQES-GPGLVKPSETLSL TCTVSG-GSIN | RS---SYYWG | WIRQPPGK GLEWIG | NIYY----SGTTYNPSLKS | RVTISVDTSKNQFSLNLSSV TAADTAVYSCAR | HGKDW------GLDY | WGQGA LVTVS S |
| iPS:3 94037 | 21-225_4F4 | VH4|4-39/D4|4-17|RF2/JH4 | QLQLQES-GPGLVRPSETLSL TCTVSG-GSIS | RS---SYYWG | WIRQPPGK GLEWIG | NIYY----SGSTYDNPSLKS | RVTISVDTSKNQFSLKLSSV TAADTAVYYCGR | HGKDW------GLDY | WGQGT LVTVS S |
| iPS:3 94045 | 21-225_4H4 | VH4|4-39/D4|4-17|RF2/JH4 | QLQLQES-GPGLVKPSETLSL TCTVSG-GSIS | RS---SYYWG | WIRQPPGM GLEWIG | NIYY----SGNTYNNPSLKS | RVTISVDTSKNQFSLKLNSV TTAADTAVYYCGR | HGKDW------GLDY | WGQGT LVTVS S |
| iPS:3 94079 | 21-225_11F5 | VH4|4-39/D4|4-17|RF2/JH4 | QLQLQES-GPGLVKPSETLSL TCTVSG-GSIS | RS---SYYWG | WIRQPPGK GLEWIG | NIYY----SGSTYNPSLKS | RVTISVDTSKNHFSLKLSSV TAADTAVYYCGR | HGKDW------GLDN | WGQGT LVTVS S |
| VH3|3-21/D4|4-11|RF2/JH3 | Germline | EVQLVES-GGGLVKPGGSLRL SCAASG-FTFS | S------YSMN | WVRQAPGK GLEWVS | SISGS---SSYIYADSVKG | RFTISRDNAKNSLYLQMNSL DYNY | | | |
| iPS:3 92624 | 21-225_17H12 | VH3|3-21/D4|4-11|RF2/JH3 | EVQLVES-GGGLVKPGGSLRL SCAASG-FTFS | S------YTMN | WVRQAPGK GLEWVS | SISGS---SSYIYADSVKG | RFTISRDNAKNSLYLQMNSL RAEDTAVYYCAR | DRG---------SI | WGQGT MVTVS S |
| iPS:3 93946 | 21-225_16A4 | VH3|3-21/D4|4-11|RF2/JH3 | EVQLVES-GGGLVKPGGSLRL SCAASG-FTFS | S------YSMN | WVRQAPGK GLEWVS | SISGS---STYKYYADSVKG | RFTISRDNAKNSLYLQMNSL RTEDTAVYYCAR | DRG---------SY | WGQGT QVTVS S |
| iPS:3 94008 | 21-225_15H8 | VH3|3-21/D4|4-11|RF2/JH3 | EVQLVES-GGGLVKPGGSLRL SCAASG-FTFS | S------YVMN | WVRQAEGK GLEWVS | SISGS---STYIYCADSIKG | RFTISRDNAKNSLYLQMNSL RADDTAVYYCAR | DRG---------SI | WGQGT MVTVS S |
| VH6|6-01/D6|6-19|RF1/JH6 | Germline | QVQLQQS-GPGLVKPSQTLSL TCAISG-DSVS | RN---TAAWS | WIRQSPSR GLEWLG | RTYYR----SKWYNDYAVSVKS | RVTINPDISKNQFSLQLNSV TPEDTAVYYCAR | VSSGWSHH------YYYYGMDV | WGQGT TVTVS S |
| iPS:3 92636 | 21-225_17A6 | VH6|6-01/D6|6-19|RF1/JH6 | QVQLQQS-GPGLVKPSQTLSL TCAISG-DSVS | RN---TAAWS | WIRQSPSR GLEWLG | RTYYR----SKWYNDYAVSVKS | RVTINPDISKNQFSLQLNSV TPEDTAVYYCAR | VSSGWSHH------YYYYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH6/6-01/D2/2-15/RF2/JH6 | | | | | | | | |
| iPS:3 92648 | VH6/6-01/D2/2-15/RF2/JH6 | QVQLQQS-GPGLVKPSQTLSL TCAISG-DSVS | RN---TAAWS | WIRQSPSR GLEWLG | RTYYR--SKWYNDYAV SVKS | RITINPDTSKNQFSLQLNSV TPEDTAVYYCAR | VNSGWHH-------YYYGMDV | WGQGT TVTVS S |
| VH3/3-11/D1/1-1/RF3/JH2 | | | | | | | | |
| iPS:3 92650 | VH3/3-11/D1/1-1/RF3/JH2 | QVQLVES-GGGLVKPGGSLRL SCAASG-FTFS | D------YYMS | WIRQAPGK GLEWVS | HISSS---GSTIYYADS VKG | RFTISRDNAKNSLYLQMNSL RAEDTAVYYCAR | YRNNR--------GYFDL | WGRGT LVTVS S |
| iPS:3 92728 | VH3/3-11/D1/1-1/RF3/JH2 | QVQLVES-GGGLVKPGGSLRL SCAASG-FTFS | D------YYMS | WIRQAPGK GLEWVS | HISSS---GSTIYYADS VKG | RFTISRDNGENSLYLQMNSL RAEDTAVYYCAR | YRNNR--------GYFDL | WGRGS LVTVS S |
| VH4/4-59/D1/1-26/RF3/JH4 | | | | | | | | |
| iPS:3 92676 | VH4/4-59/D1/1-26/RF3/JH4 | QVQLQES-GPGLVKPSETLSL TCTVSG-GAIS | GS---SYYWG | WIRQPPGK QLEWIG | NIYY---SGSTYNPS FKS | RVTISVDTSKNQFSLKLSSV TAEDTAVYYCAR | HSSSW-------SLDY | WGQGT LVTVS S |
| VH3/3-23/D6/6-13/RF2/JH2 | | | | | | | | |
| iPS:3 92678 | VH3/3-23/D6/6-13/RF2/JH2 | EVQLLES-GGGLVQPGGSLRL SCAASG-FTFS | S------YAMN | WVRQAPGK GLEWVS | VISGS---GGSTYYADS VKG | RFTISRDNSKNTLYLQMNSL RAEDTAVYYCAR | RIAAAG-----TEYFDL | WGRGT LVTVS S |
| VH3/3-21/D5/5-24/RF3/JH4 | | | | | | | | |
| iPS:3 92682 | VH3/3-21/D5/5-24/RF3/JH4 | EVQLVES-GGGLVKPGGSLRL SCAASG-FTFS | S------YRMN | WFRQAPGK GLEWVS | SISGS---STDIYYADS VKG | RFTISRDNAENSLYLQMNSL RAEDTAVYYCAR | RD-------------F | WGQGT LVTVS S |
| VH3/3-48/D7/7-27/RF1/JH4 | | | | | | | | |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 92692 | 21-225_18G10 | VH3J3-48/D7/7-27/RF1/JH4 | EVQLVES-GGGLVQPGGSLRL LCAASG-IIFS | T-----YSMN | WVRQAPGK GLEWVS | YISRS---SSTIYADS VKG | RFTIISRDNAKNSLYLQMNSL RDEDTAVYYCAR | GGGS------PFDY | WGQGT LVTVS S |
| iPS:3 92708 | 21-225_18D11 | VH3J3-48/D7/7-27/RF1/JH4 | EVQLVES-GGGLVQPGGSLRL SCAASG-FTFR | S-----YSMN | WVRQAPGK GLEWLS | YISSS---SGTIYYADS VKG | RFTIISRDNARNSLNLQMNSL RDEDTAVYYCAR | GGGS------PFDY | WGQGT LVTVS S |
| iPS:3 93992 | 21-225_14H8 | VH3J3-48/D7/7-27/RF1/JH4 | EVQLVES-GGGLVQPGGSLRL SCAASG-FTFS | S-----NSMN | WVRQAPGK GLEWVS | YISSS---SSTIYYADS VKG | RFTIARDNAKNSLYLQMNSL RDEDTAVYYCAR | GGGS------PFDY | WGQGT LVTVS S |
| iPS:3 94055 | 21-225_9C8 | VH3J3-48/D7/7-27/RF1/JH4 | EVQLVES-GGGLVQPGGSLRL SCVVSG-FTFS | S-----QSMN | WVRQAPGK GLEWVS | YISI----SSTIYYADS VKG | RFTIISRDNHAKNSLYLQMNSL RDEDTAVYYCAR | GGGS--------PFDS | WGQGT LVTVS S |
| | Germline VH3J3-30.3/D4/4-11/RF2/JH4 | EVQLVES-GGGLVQPGRSLRL SCAASG-FTFS | S-----YAMS | WVRQAPGK GLEWVS | YISYD---GSNTYADS VKG | RFTIISRDNSKNTLYLQMNSL RAEDTAVYYCAR | YSSNY | H_FR4 |
| iPS:3 92694 | 21-225_19A5 | VH3J3-30.3/D4/4-11/RF2/JH4 | QVQLVES-GGGLVQPGRSLRL SCAASG-FTFS | S-----YAMH | WVRQAPGK GLEWVA | VIWFD---GSDKYYADS VKG | RFTIISRDNSKNTLYLQMNSL RAEDTAVYYCAR | DRAYS------SSSDY | WGQGT LVTVS S |
| | Germline VH3J3-23/D1/1-1/RF1/JH4 | EVQLLES-GGGLVQPGGSLRL SCAASG-FTFS | S-----YAMS | WVRQAPGK GLEWVS | AISGS---GGSTYYADS VKG | RFTIISRDNSKNTLYLQMNSL RAEDTAVYYCAK | GYYDY | H_FR4 |
| iPS:3 92714 | 21-225_16G12 | VH3J3-23/D1/1-1/RF1/JH4 | EVQLLES-GGGLVQPGGSLRL SCAASG-FSFS | S-----YAMT | WVRQAPGK GLEWVS | TISGR---GGHTYYADS VRG | RFAISRDSSKNTLYLQMNSL RAEDTAVYYCAK | QD----------C | WGQGT LVTVS S |
| iPS:3 92890 | 21-225_20H9 | VH3J3-23/D1/1-1/RF1/JH4 | EVQLLES-GGGLVQPGGSLRL SCAASG-FTFS | S-----YAMS | WVRQAPGK GLEWVS | AISGS---GGYTYYADS VKG | RFTIISRDNSENTLYLQMNSL RAEDTAVYYCAK | GGS---------LFY | WGQGT LVTVS S |
| iPS:3 92892 | 21-225_20C11 | VH3J3-23/D1/1-1/RF1/JH4 | EVQLLES-GGGLVQPGGSLRL SCAASG-FSFS | S-----YAMS | WVRQAPGK GLEWVS | TISGR---GGHTYYADS VKG | RFAISRDSSKNTLYLQMNSL RAEDTAVYYCAK | QD----------C | WGQGT LVTVS S |
| iPS:3 93968 | 21-225_5A5 | VH3J3-23/D1/1-1/RF1/JH4 | EVQLWES-GGGLVQPGGSLRL SCAASG-FTFS | S-----YAMN | WVRQAPGK GLEWVS | AISGS---GGYTYYADS VKG | RFTIISRDNSKNTLYLQMNSL RAEDTAVYYCAK | GGS---------LFY | WGQGT LVTVS S |
| | Germline VH3J3-23/D6/6-6/RF1/JH3 | EVQLLES-GGGLVQPGGSLRL SCAASG-FTFS | S-----YAMS | WVRQAPGK GLEWVS | AISGS---GGSTYYADS VKG | RFTIISRDNSKNTLYLQMNSL RAEDTAVYYCAK | YYGSS | DAFDI | WGQGT MTTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 92730 | 21-225_17A1 | VH3/3-23/D6[6-6]/RF1/JH3 | EVQLLES-GGGLVQPGGSLRL SCAASG-FTFS | S-----YAMN | WVRQAPGK GLEWVS | VISGS---GSNTYYADS VKG | RFTIISRDNSKNTLYLQMNSL RAEDTAVYYCAK | RYTSDW----------HDAFDI | WGQGT MVTVS S |
| iPS:3 92736 | 21-225_17B12 | VH3/3-23/D6[6-6]/RF1/JH3 | EVQLLES-CGGLVQPGGSLRL SCVASG-FTFS | S-----YAMN | WVRQAPGK GLEWVS | VISGS---GGSTYYADS VKG | RFTIISRDNSKNTLYLQMNTL RAEDTAVYYCAK | RYTSDW----------HDAFDI | WGQGT MVTVS S |
| iPS:3 92770 | 21-225_20C10 | VH3/3-23/D6[6-6]/RF1/JH3 | EVQLLES-CGGLVQPGGSLRL SCAASG-FTFS | S-----YAMN | WVRQAPGK GLEWVS | VISGS---GGTTYYADS VKG | RFTIISRDNSKNTLYLQMNTL RAEDTAVYYCAK | RYTSDW----------HDAFDI | WGQGT MVTVS S |
| iPS:3 93878 | 21-225_7G12 | VH3/3-23/D6[6-6]/RF1/JH3 | EVQLLES-GGGLVQPGGSLRL SCAASG-FTFS | S-----YAMN | WVRQAPGK GLEWVS | VISGS---GGSTYYADS VKG | RFTIISRDNSKNTLYLQMNTL RAEDTAVYYCAK | RYTSDW----------HDAFDI | WGQGT MVTVS S |
| | Germline | H_FR1 | H_CDR1 | H_FR2 | H_CDR2 | H_FR3 | H_CDR3 | H_FR4 |
| | VH3/3-21/D7[7-27]/RF3/JH5 | EVQLVES-GGGLVKPGGSLRL SCVASG-FTFS | S-----YSVN | WVRRAPGK GLEWVS | SISSS---SSFLYYADS VKG | RFTIISRDNAKNSVYLQMNSL RAEDTAVYYCAR | NW--------------DY | WGQGT LVTVS S |
| iPS:3 92748 | 21-225_20A8 | VH3/3-21/D7[7-27]/RF3/JH5 | EVQLVES-GGGLVKPGGSLRL SCVASG-FTFS | S-----YSVN | WVRQAPGK GLEWVT | VISYD---GSNKYYADS VKG | RFTIISRDNSKNTLYLQMNSL RAEDTAVYYCAR | NW--------------DY | WGQGT LVTVS S |
| | Germline | H_FR1 | H_CDR1 | H_FR2 | H_CDR2 | H_FR3 | H_CDR3 | H_FR4 |
| | VH3/3-30.3/D1[1-1]/RF1/JH5 | | | | | | | |
| iPS:3 92754 | 21-225_21D3 | VH3/3-30.3/D1[1-1]/RF1/JH5 | EVQLLES-GGGLVQPGGRSLRL SCVASG-FTFS | S-----YGMH | WVRQAPGK GLEWVT | VISYD---GSNKYYADS VKG | RFTIISRDNSKNTLYLQMNSL RAEDTAVYYCAR | GVWF------------GDL | WGQGT LVTVS S |
| iPS:3 92818 | 21-225_22D8 | VH3/3-30.3/D1[1-1]/RF1/JH5 | QVQLVES-GGGVVQPGRSLRL SCVASG-FTFR | S-----YGMH | WVRQAPGK GLEWVT | IISYD---GSNKYYADS VKG | RFTIISRDNSKNTLYLQMNSL RAEDTAVYFCAR | GVWF------------GDF | WGQGT LVTVS S |
| | Germline | H_FR1 | H_CDR1 | H_FR2 | H_CDR2 | H_FR3 | H_CDR3 | H_FR4 |
| | VH3/3-23/D6[6-19]/RF2/JH1 | | | | | | | |
| iPS:3 92762 | 21-225_22G5 | VH3/3-23/D6[6-19]/RF2/JH1 | EVQLLES-GGGLVQPGGSLRL SCAASG-FTFS | S-----YAMN | WVRQAPGM GLEWVS | VISRS---GGTTYYADS VKG | RFTIISRDNSKNTLYLQMNSL RAEDTAVYYCAS | RLAVAG----------SEAFDI | WGQGT LVTVS S |
| iPS:3 94051 | 21-225_9E5 | VH3/3-23/D6[6-19]/RF2/JH1 | EVQLLES-CGGLVQPGGSLRL SCAASG-FTFS | N-----YAMN | WVRQAPGK GLEWVS | AISGG---GGNTFYADS VKG | RFTIISRDNSKNTLYLQMNGL RAEDTAVYYCAS | RIAVAG----------SEAFAI | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4/4-39/D1|1-26|RF3/JH1 | | QLQLQES-GPGLVKPSETLSL TCTVSG-GSIS | SS----SYYWG | WIRQPPGK GLEWIG | SIYY----SGSTYYNPS LKS | RVTISVDTSKNQFSLKLSSV TAADTAVYYCAS | LSSSW----DFQH | WGQGT LVTVS S |
| iPS:3 92774 | VH4|4-39/D1|1-26|RF3/JH1 | QLQLQES-GPGLVKPAETLSL TCIVSG-GSIS | RS----SYYWG | WIRQPPGK VLEWIG | SIYY----SGSTYYNPS LKS | RVTISVDTSKNQFSLKLSSV TAADTAEYYCAS | LSSSW----DFQH | WGQGT LVTVS S |
| iPS:3 93862 | VH4|4-39/D1|1-26|RF3/JH1 | QLQLQES-GPGLVKPSETLSL TCTVSG-GSIS | RS----SYYWG | WIRQPPGK GLEWIG | NIYY----SGSTYYIPS LKS | RVTISVDTSKNQFSLKLSSV TAADTAVYYCAR | HSTSW----SLDH | WGQGT LVTVS S |
| iPS:3 94049 | VH4|4-39/D1|1-26|RF3/JH1 | QLQLQES-GPGLVKPAETLSL TCTVSG-GSIS | RS----SYYWG | WIRQPPGK GLEWIG | SIYY----SGSTYYNPS LKS | RVTISVDTSKNQFSLKLSSV TAADTAVYYCAS | LSSSW----DFQH | WGQGT LVTVS S |
| VH3|3-21/D2|2-21|RF2/JH4 | Germline | EVQLVES-GGGLVQPGGSLRL SCAASG-FTFS | S----YSMN | WVRQAPGK GLEWVS | SSIYYADS VKG | RFTISRDNAKNSLYLQMNSL RAEDTAVYYCAR | KSYYDY | WGQGT LVTVS S |
| iPS:3 92776 | VH3|3-21/D2|2-21|RF2/JH4 | EVQLVES-GGGLVKPGGSLRL SCAASG-FTFN | S----YSMN | WVRQAPGK GLEWVS | SISGS----VKG | RFTISRDNAKNSLYLQMNSL RAEDTAVYYCAR | AAG----FDY | WGQGT LVTVS S |
| VH3|3-33/D6|6-19|RF2/JH6 | Germline | EVQLVES-GGGLVQPGRSLRL SCAASG-FTFS | S----YGMH | WVRQAPGK GLEWVA | VIWYD----VKG | RFTISRDNSKNTLYLQMNSL RAEDTAVYYCAR | NTYGMDV | WGQGT TVTVS S |
| iPS:3 92806 | VH3|3-33/D6|6-19|RF2/JH6 | QVQLVES-GGGVVQPGRSLRL SCGASG-FTFS | S----YGMH | WVRQAPGK GLEWVA | VIWYD----GSNKYYADS VKG | RFTISRDNSKNTLYLQMNSL RAEDTAVYYCAR | VAVAG----GMDV | WGQGT TVTVS S |
| VH3|3-48/D7|7-27|RF2/JH4 | Germline | EVQLVES-GGGLVQPGGSLRL SCAASG-FTFS | S----YSMN | WVRQAPGK GLEWVS | YISSS----VKG | RFTISRDNAKNSLYLQMNSL RDEDTAVYYCAR | LGT----FDY | WGQGT LVTVS S |
| iPS:3 92826 | VH3|3-48/D7|7-27|RF2/JH4 | EVQLVES-GGGLVQPGGSLRL SCAASG-FTFS | S----YSMN | WVRQAPGK GLEWVS | YISSS----SSTIYYADS VKG | RFTISRDNAKNSLYLQMNSL RDEDTAVYYCAR | SLWS----PFDY | WGQGT LVTVS S |
| VH4|4-59/D1|1-1|RF1/JH5 | Germline | QVQLQES-GPGLVKPSETLSL TCTVSG-GSIS | S----YYWS | WIRQPPGK GLEWIG | YIYY----SGSTNYNPS LKS | RVIMSVDTSKNQFSLKLSSV TAADTAVYYCAR | GTTGT----NWFDP | WGQGT LVTVS S |
| iPS:3 92830 | VH4|4-59/D1|1-1|RF1/JH5 | QVQLQES-GPGLVKPSETLSL TCTVSG-GSIS | S----YFWS | WIRQPAGK GLEWIG | RIYT----SGITNYNPS LKS | RVIMSVDTSKNQFSLKLSSV TAADTAIYYCAR | GPTSG----WFDP | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3J3-23|D6|6|RF2|JH4 | | EVQLLES- GGGLVQPGGSLRL SCAASG-FTFS | S-----YAMS | WVRQAPGK GLEWVS | AISGS--- GGSTYYADS VKG | RFTISRDNSKNTLYLQMNSL RAEDTAVYYCAR | SSAAR | WGQGT LTVTV S |
| iPS.3 92840 | 21-225_23G1 | EVQLLES- GGGLVQPGGSLRL SCAASG-FTFS | S-----YAMS | WVRQAPGK GLEWVS | VISGS--- GGTTYNTDS VKG | RFTISRDNSKNTLYLQMNSL RAEDTAVYYCAR | SSL---------------FDY | WGQGT LVTVS S |
| iPS.3 94018 | 21-225_15B1 | VH3J3-23|D6|6-6|RF2|JH 4 | EVQLLES- GGGLVQPGGSLRL SCATSG-FTFS | S-----YVMS | WVRQAPGK GLEWVS | GISGS--- GGSTNNADS VKG | RFTISRDNSKNTLYLQVNSL RAEDTAVYYCAR | SSL---------------FDY | WGQGT LVTVS S |
| iPS.3 94026 | 21-225_16C7 | VH3J3-23|D6|6-6|RF2|JH 4 | EVQLLES- GGGLVQPGGSLRL SCAASG-FTFS | S-----YVWT | WVRQAPGK GLEWVS | TISGS--- GGMTYYADS VKG | RFTISRDNSKNTLYLQMNSL RAEDTAEYYCAR | SSL---------------FDY | WGQGT LVTVS S |
| VH3J3-23|D6|6-6|RF2|JH5 | Germline | EVQLLES- GGGLVQPGGSLRL SCAASG-FTFS | S-----YAMS | WVRQAPGK GLEWVS | AISGS--- GGSTYYADS VKG | RFTISRDNSKNTLYLQMNSL RAEDTAVYYCAK | STAAR------------WFDP | WGQGT LVTVS S |
| iPS.3 92842 | 21-225_23G8 | VH3J3-23|D6|6-6|RF2|JH 5 | EVQLLES- GGGLVQPGGSLRL SCAASG-FTFS | S-----YAMS | WVRQAPGK GLEWVS | AISGS--- GGSTYYADS VKG | RFTISRDNSKNTLYLQMNSL RAEDTAVYYCAV | SSG---------------WFA | WGQGT LVTVS S |
| VH3J3-23|D11-1|RF2|JH2 | Germline | EVQLLES- GGGLVQPGGSLRL SCAASG-FTFS | S-----YAMS | WVRQAPGK GLEWVS | AISGS--- GGSTYYADS VKG | RFTISRDNSKNTLYLQMNSL RAEDTAVYYCAK | VDLERY | WGQGT LVTVS S |
| iPS.3 92856 | 21-225_22A2 | VH3J3-23|D11-1|RF2|JH 2 | EVQLLES- GGGLVQPGGSLRL SCAASG-FTFS | S-----YAMS | WVRQAPGK GLEWVS | GISGS--- GGNTPYADS VKG | RFTISRDNSKNTLYLQMNSL RAEDTAVYYCAR | VVG---------------AVH | WGRGT LVTVS S |
| iPS.3 92864 | 21-225_23B9 | VH4J4-30.1|D5|5-18|RF1|J H6 | QVQLQAS- GPGLVRPSQTLSL TCTVSD-GSIS | SG---GYYWS | WIRQHPGK GLEWIG | YIYY---- SGSTYNPS LKS | RVTISVDTSRNQFSLKLSSV TAADIAVYYCAR | EDGAFG-----------YYGMDV | WGQGT TVTVS S |
| VH3J3-23|D2|2-2|RF2|JH3 | Germline | EVQLLES- GGGLVQPGGSLRL SCAASG-FTFS | S-----YAMS | WVRQAPGK GLEWVS | AISGS--- GGSTYYADS VKG | RFTISRDNSKNTLYLQMNSL RAEDTAVYYCAK | GYCSSSS----------YDAFDI | WGQGT MVTVS S |
| iPS.3 92874 | 21-225_21D2 | VH3J3-23|D2|2-2|RF2|JH 3 | EVKLLES- GGGLVQPGGSLRL SCAASG-FTFN | N-----YAMS | WVRQAPGK GLEWVS | VLSGS--- GGSTFYADS VKG | RFTISRDNSKNTLYLQMSSL RAGDTAVYFCAR | YCSSARC----------PYDAFDI | WGQGT MVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS:3 93940 | 21-225_16B2 | VH3J3-23|D2|2-2|RF2|JH3 | EVQLLES-GGGLVQPGGSLRL SCAASG-FTFS | S-----YAMT | WVRQAPGK GFEWVS | VISGS---GGSTFYADS VKG | RFTISRDNSKNTLYLQMSSL RAEDTAVYFCAR | YCSSTRC--------PYDAFDI | WGQGT MVTVS S |
| iPS:3 93956 | 21-225_4D7 | VH3J3-23|D2|2-2|RF2|JH3 | EVKLLES-GGGLVQPGGSLRL SCAASG-FTFS | S-----YAMS | WVRQAPGK GLEWVS | VLSGS---GGSTFYADS VKG | RFTISRDNSKNTLYLQMSSL RAGDTAVYFCAR | YCSSARC--------PYDAFDI | WGQGT MVTVS S |
| iPS:3 98476 | 21-225_17C1 | VH3J3-23|D2|2-2|RF2|JH3 | EVQLLES-GGGLEQPGGSLRL SCAASG-FTFS | S-----YAMS | WVRQAPGK GLEWVS | VISGS---GGSTFYADS VKG | RFTISRDNSKNTLYLQMSSL RAEDTAVYFCAR | YCSSTRC--------PYDAFDI | WGQGT MVTVS S |
| | Germline VH3|3-15|D1|1-1|RF3|JH4 | | EVQLVES-GGGLVQPGGSLRL SCAASG-FTFS | | WVRQAPGK GLEWVS | RIKSKT---DGGTTDYAA KTEDTAVYYCTT | RFTISRDNSKNTLYLQMNSL | | WGQGT LVTVS S |
| iPS:3 92898 | 21-225_21H10 | VH3J3-15|D1|1-1|RF3|JH4 | EVQLVES-GGGLVKPGGSLRL SCAASG-FTFS | N-----AWMN | WVRQAPGK GLEWVG | RIKSKT---DGGTIDYAA KTEDTAVYYCTT | RFTISRDDSKNTLYLQMNSL | EGWN---------TDY | WGQGT LVTVS S |
| iPS:3 93802 | 21-225_3D12 | VH3J3-15|D1|1-1|RF3|JH4 | EVQLVES-GGGLVKPGGSLRL SCAASG-VTFS | T-----AWMN | WVRQAPGK GLEWVG | RIKNKI---DGGTIDYVA PVKG | RFTISRDDSKNTLYLQMNSL KTEDTAVYYCTT | EGWN---------TDY | WGQGT LVTVS S |
| | Germline VH3|3-48|D4|4-11|RF3|JH4 | | EVQLVES-GGGLVQPGGSLRL SCAASG-FTFS | | WVRQAPGK GLEWVS | SISSS---SSTIYYADS VKG | RFTISRDNAKNSLYLQMNSL | | WGQGT LVTVS S |
| iPS:3 92950 | 21-225_25C10 | VH3J3-48|D4|4-11|RF3|JH4 | EVQLVES-GGGLVQPGGSLRL SCAASG-FTFS | S-----YRMN | WVRQAPGK GLEWVS | SISSS---SSTIYYADS VKG | RFTISRDNAKNSLYLQMNSL RDEDTAVYYCAR | TAG--------FDY | WGQGT LVTVS S |
| | Germline VH3|3-23|D1|1-26|RF3|JH4 | | EVQLLES-GGGLVQPGGSLRL SCAASG-FTFS | | WVRQAPGK GLEWVS | VISGS---GGSTYYADS | RFTISRDNSKNTLYLQMNSL | | WGQGT LVTVS S |
| iPS:3 93010 | 21-225_25E11 | VH3J3-23|D1|1-26|RF3|JH4 | EVQLLES-GGGLVQPGGSLRL SCAASG-FTFS | S-----YAMS | WVRQAPGK GLEWVS | VISGG---GGSTYYADS VKG | RFTISRDNSKNTLYLQMNSL RAEDTAVYYCAK | RGYSGYE-------DLLYFDC | WGQGT LVTVS S |
| | Germline VH3|3-23|D3|3-3|RF3|JH3 | | EVQLLES-GGGLVQPGGSLRL SCAASG-FTFS | S-----YAMS | WVRQAPGK GLEWVS | VISGS---GGSTYYADS | RFTISRDNSKNTLYLQMNSL RAEDTAVYYCAK | | WGQGT MVTVS S |
| iPS:3 93016 | 21-225_28F11 | VH3J3-23|D3|3-3|RF3|JH3 | EVQLVQPGGSLRL SCAASG-FIFS | S-----YAMS | WVRQAPGK GLEWVS | VTSGS---GGTTFYADS VKG | RFTISRDNSKNTLYLQMNSL RAEDTAVYYCAR | RIQFD---------DFDI | WGQGT MVTVS S |

Figure 51 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| | VH3-33/D3/3-22/RF2/JH6 | | | | | | | | |
| iPS:3 93032 | 21-225_26F8 | VH3-33/D3/3-22/RF2/JH6 | QVQLVES-GGGVVQPGRSLRL SCAASG-FTFS | G-----YGMH | WVRQAPGK GLEWVA | IIWYD--GSNKYYADS VKG | RFTISRDNSKNTLYLQMNSL RAEDTAVYYCAR | ERYDFW------SGCMDV | WGQGT TVTVS S |
| | | Germline | | | | | | | |
| iPS:3 93042 | 21-225_31F1 | VH1/1-02/D4/4-11/RF2/JH6 | QVQLVQS-GAEVKKPGASVKV SCKASG-YTFT | D-----YYMH | WVRQAPGQ GLEWMG | WINPN--SGGTNYAQK FQG | RVTMTRDTSIMTAYMELSRL RSDDTAVYYCAR | DSSNFSNW------YDYGMDV | WGQGT TVTVS S |
| iPS:3 93108 | 21-225_34G11 | VH1/1-02/D4/4-11/RF2/JH6 | QVQLVQS-GAEVKKPGASVKV SCKASG-YTFT | G-----YYMH | WVRQAPGQ GLEWMG | WINPN--SGGTNYAQK FQG | RVTIMRDTSTAYMELSRL RSDDTAVYYCAR | DISNFSSW------YDYYAMDV | WGQGT TVTVS S |
| | | Germline | | | | | | | |
| iPS:3 93044 | 21-225_25B8 | VH1/1-18/D5/5-12/RF3/JH4 | QVQLVQS-GAEVKKPGASVKV SCKASG-YTFT | S-----YGIS | WVRQAPGQ GLEWMG | WISAY--NGNTTYAQK LRG | RVTMTDTSTAYMDLRSL RSDDIAVYYCAR | TAAGYS------SSWFDY | WGQGT LVTVS S |
| iPS:3 93050 | 21-225_28C5 | VH1/1-18/D5/5-12/RF3/JH4 | QVQLVQS-GAEVKKPGASVKV SCKASD-YTFT | S-----YGIS | WVRQAPGQ GLEWMG | WISAY--NGNTTYAQK LRG | RVTMTDTSTAYMDLRSL RSDDTAVYYCAR | TAAGYS------SSWFDY | WGQGT LVTVS S |
| | | Germline | | | | | | | |
| iPS:3 93046 | 21-225_25A12 | VH3-33/D6/6-6/RF1/JH3 | QVQLVES-GGGVVQPGRSLRL SCAASG-FTFS | N-----CVMH | WVRQAEGK GLEWVA | VIWYD--GSNKYYADS VKG | RFTISRDNSKNTLYLQMNSL RAEDTAVYYCAR | EEYSSGW------YDYGMDV | WGQGT MVTVS S |
| | | Germline | | | | | | | |
| iPS:3 93078 | 21-225_33H11 | VH3-21/D4/4-11/RF3/JH6 | EVQLVES-GGGLVKPGGSLRL SCAASG-FTFS | S-----YSMN | WVRQAPGK GLEWVS | SISGS--SSYIYYADS VKG | RFTISRDNAKNSLYLQMSSL RAEDTAVYYCAR | TNG------MDV | WGQGT TVTVS S |

Figure 51 (Continued)

| | | H_FR1 | H_CDR1 | H_FR2 | H_CDR2 | H_FR3 | H_CDR3 | H_FR4 |
|---|---|---|---|---|---|---|---|---|
| iPS.3 93142 | 21-225_33A3 | VH3/3-21/D4/4-11/RF3/JH6 | EVQLVES-GGGLVKPGGSLRL SCAASG-FTFS | S------YGMN | WVRQAPGK GLEWVS | SISGS---STYIYYADS VKG | RFTISRDNAMNSLYLQMNSL RAEDTAVYYCAR | TNG--------------MDV | WGQGT TVTVS S |
| | VH3/3-23/D4/4-19/RF2/JH6 | Germline | EVQLVES-GGGLVKPGGSLRL SCAASG-FTFS | S------YAMS | WVRQAPGK GLEWVS | AISGS---GGSTYYADS VKG | RFTISRDNSKNTLYLQMNSL RAEDTAVYYCAK | GIAVNGY--------YYYGMDV | WGQGT TVTVS S |
| iPS.3 93096 | 21-225_34D11 | VH3/3-23/D6/6-19/RF2/JH6 | EVQLSES-GGGLVQPGGSLRL SCAASG-FTFS | S------YAMN | WVRQAPGK GLEWVS | AISGR---GGSTFHADS VKG | RFTISRDNSKNTLYLQMNSL RAEDTAVYYCVK | GELVEDY--------YFYGMDV | WGQGT TVTVS S |
| | VH3/3-30.3/D4/4-23/RF2/JH3 | Germline | EVQLVES-GGGLVQPGGSLRL SCAASG-FTFS | S------YAMH | WVRQAPGK GLEWVA | VISYD---GSNKYYADS VKG | RFTISRDNSKNTLYLQMNSL RAEDTAVYYCAR | DYGNS----------DAFDI | WGQGT MVTVS S |
| iPS.3 93172 | 21-225_3B12 | VH3/3-30.3/D4/4-23/RF2/JH3 | QVHLVES-GGGLVQPGRSLRL SCAASG-FTFS | Y------YGMH | WVRQAPGK GLEWVA | VISYD---GSNKYYADS VKG | RFTISRDNSKNTLHLQMNSL RAEDTAVYYCAR | DRAGGYG-----------VPDAFDI | WGQGT MVTVS S |
| | VH3/3-30.3/D4/4-23/RF2/JH6 | Germline | QVQLVES-GGGLVQPTGRSLRL SCAASG-FTFS | S------YAMH | WVRQAPGK GLEWVA | VISYD---GSNKYYADS VKG | RFTISRDNSKNTLYLQMNSL RAEDTAVYYCAR | DYGNSY---------YYYGMDV | WGQGT TVTVS S |
| iPS.3 93174 | 21-225_15D8 | VH3/3-30.3/D4/4-23/RF2/JH6 | QVQLVES-GGGLVQPTGRSLRL SCAASG-FTFS | G------YGMH | WVRQAPGK GLEWVS | VISYD---GSNKYYADS VKG | RFTISRDNSKNTLYLQMNSL RAEDTAVYYCAR | DRVYCSSTSCV---PYYDYYGMDV | WGQGT TVTVS S |
| | VH3/3-15/D7/7-27/RF1/JH6 | Germline | EVQLVES-GGGLVKPGGSLRL SCAASG-FTFS | N------AMMN | WVRQAPGK GLEWVG | RIKSKT---DGGTTDYAA PVKG | RFTISRDDSKNTLYLQMNSL KIEDTAVYYCTT | DYGNSY---------YYYGMDV | WGQGT TVTVS S |
| iPS.3 93194 | 21-225_16D2 | VH3/3-15/D7/7-27/RF1/JH6 | EVQLVES-GGGLVKPGGSLRL SCAASG-FTFS | N------AMMN | WVRQAPGK GLEWVG | RIKSKT---DGGTTDYAA PVKG | RFTISRDDSKNTLYLQMNSL KIEDTAVYYCTI | DTGPIAARLA--------YYYYAMDV | WGQGT TVTVS S |
| iPS.3 98488 | 21-225_19F6 | VH3/3-15/D7/7-27/RF1/JH6 | EVQLVES-GGGLVKPGGSLRL SCAASG-FTFS | N------AMMN | WVRQAPGK GLEWVG | RIKSKT---DGGTTDYAA PVKG | RFTISRDSKNTLYLQMNSL KIEDTAVYYCTT | DTGPIAARLA--------YYYYAMDV | WGHGT TVTVS S |
| iPS.3 98544 | 21-225_7C8 | VH3/3-15/D7/7-27/RF1/JH6 | EVQLVES-GGGLVKPGGSLRL SCAASG-FTFS | N------AMMN | WVRLAPGK GLEWVG | RIKSKT---DGGTTDYAA PVKG | RFTISRDESENTLYLQMNSL KIEDTGVYYCSI | DTGPIAARLA--------YYYYAMDV | WGQGT TVTVS S |
| iPS.4 02231 | 21-225_6D9 | VH3/3-15/D7/7-27/RF1/JH6 | EVQLVES-GGGLVKPGGSLRL SCAASG-FTFS | N------AMMN | WVRLAPGK GLEWVG | RIKSKT---DGGTTDYAA PVKG | RFTISRDESENILYLQMNSL KIEDTAVYYCSI | DTGPIAARLA--------YYYYAMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3/3-23/D4/4-11/RF2/JH4 | | | | | | | | |
| iPS.3 93870 21-225_7B1 | VH3/3-23/D4/4-11/RF2/JH4 | EVQLLES-GGGLVQPGGSLRL SCAASG-FTFS | S-----YDMS | WVRQAPGK GLEWVS | TISGS---GGITYYADS VKG | RFTISRDNSKNTLYLQMNSL RAEDTAVYFCAR | DRG----------SV | WGQGT LVTVS S |
| VH4/4-39/D4/4-17/RF2/JH1 | | | | | | | | |
| iPS.3 93872 21-225_2A11 | VH4/4-39/D4/4-17/RF2/JH1 | QLQLQES-GPGLVKPSETLSL TCTVSG-GSIS | RS---SYYWG | WIRQPPGK GLEWIG | NIYY---SGSTYYNPS VKS | RVTISVDTSKNQFSLKLSTV TAADTAVYYCAR | HGKDW---------GLED | WGQGT LVTVS S |
| VH4/4-59/D6/6-6/RF1/JH4 | | | | | | | | |
| iPS.3 93890 21-225_4B1 | VH4/4-59/D6/6-6/RF1/JH4 | QVQLQES-GPGLVKPSETLSL TCSVSG-DSIS | S-----YSWS | WIRQPAGK GLEWIG | RIYT----SGSTNYIPS LKS | RETIMSVDTSKKQFSLKLSSV TAADTAVYYCAR | DLKSSG-------CLFFDY | WGQGT TVTVS S |
| VH3/3-33/D4/4-17/RF1/JH6 | | | | | | | | |
| iPS.3 93926 21-225_4G4 | VH3/3-33/D4/4-17/RF1/JH6 | QVQLVES-GGGVVQPGRSLRL SCAASG-FTFS | S-----YGMH | WVRQAPGK GLEWGA | VINHD---GSNKYYADS VKG | RFTISRDNAKNTLYLQMNSL RAEDTAVYYCAR | DLRMG----------GMDV | WGQGT TVTVS S |
| VH3/3-23/D6/6-6/RF2/JH2 | | | | | | | | |
| iPS.3 93936 21-225_14A11 | VH3/3-23/D6/6-6/RF2/JH2 | EVQLLES-GGGLVQPGGSLRL SCAASG-FTFS | S-----YAMN | WVRQAPGK GLEWVS | VISGR---GGSTYYADS VKG | RFTISRDNSKNTLYLQMNSL RAEDTAVYYCAR | RIAAGM--------EYFDL | WGRGT LVTVS S |
| VH3/3-21/D1/1-1/RF3/JH4 | | | | | | | | |
| iPS.3 93968 21-225_7F10 | VH3/3-21/D1/1-1/RF3/JH4 | EVQLVES-GGGLVKPGGSLRL SCAASG-FTFS | S-----YSMN | WVRQAPGK GLEWVS | SISSS---SSYIYYADS VKG | RFTISRDNAKNSLYLQMNSL RIEDTAVYYCAR | ANL-----------FDY | WGQGT LVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4/4-39/D6/6-6|RF1/JH4 | | | | | | | | |
| iPS:3 93990 21-225_11G7 | VH4/4-39/D6/6-6|RF1/JH4 | QLQLQES-CPGLVKPSETLSL TCIVSG-GFIS | RS----TYYWG | WIRQPPGK GLEWIG | SIYY----SGSTSYSPS LKS | RVTISVDTSKNQFSLKLSSV TAADTAVYYCAR | LNSSW-------SFDY | WGQGT LVTVS S |
| VH3|3-30.3|D2|2-15|RF3|JH6 | | | | | | | | |
| iPS:3 94010 21-225_12G5 | VH3|3-30.3|D2|2-15|RF3|J H6 | QVQLVES-GGGVVQPGRSLRL SCAASG-FIFS | N------YGIY | WVRQAPGK GLEWVA | VISYD----GSNKYYADS VKG | RFTISRDNSKNTLYLQMNSL RAEDTAVYYCAR | DKGAVAAY-----YYYGIDV | WGQGT TVTVS S |
| VH1|1-08|D2|2-21|RF1|JH4 | | | | | | | | |
| iPS:3 94065 21-225_11E2 | VH1|1-08|D2|2-21|RF1|J H4 | QVQVVQS-GAEVKKPGASVKV SCKASG-YIFT | N------YDIN | WVRQATGQ GLEWMG | WMNTN----SGNTGYAQK FQG | RVTMTRNTISTAYMDLSSL RSEDTAVYYCAY | SHGWF-------LFDY | WGQGI LVTVS S |
| iPS:3 98506 21-225_23G12 | VH1|1-08|D2|2-21|RF1|J H4 | QVQLLQS-GAEVKKPGASVKV SCKASG-YIFT | N------YDIN | WVRQAPGK GLEWMG | WMYFN----SGNTGYAQK FQG | RVTMTNTISTAYMELSSL RSEDTAVYYCAI | SGGWY-------YFDY | WGQGT LVTVS S |
| iPS:3 98512 21-225_25E12 | VH1|1-08|D2|2-21|RF1|J H4 | QVQLVQS-GAEVKKPGASVKV SCKASG-YIFT | N------YDIN | WVRQAPGK GLEWMG | WMKPN----SGNTGYAQK FQG | RVTMIRNTISTAYLELSSL RSEDTAVYYCAG | SNGWY-------YFDY | WGQGT LVTVS S |
| VH3|3-33|D7|7-27|RF2|JH3 | | | | | | | | |
| iPS:3 94091 21-225_13H3 | VH3|3-33|D7|7-27|RF2|J H3 | QVQLVES-GGGLVQPGRSLRL SCAASG-FTFS | S------YGMH | WVRQAPGK GLEWVA | VIWYE----ESNKYYVDS VRG | RFTISRDNSKSTLYLQMNSL RAEDTAVYYCVR | ELGF--------QSDF | WGQGT PVTVS S |
| VH3|3-23|D4|4-23|RF2|JH6 | | | | | | | | |
| iPS:3 98472 21-225_16E4 | VH3|3-23|D4|4-23|RF2|J H6 | EVQLLES-CGGLIQPGGSLRL SCAASG-FTFS | S------YVMS | WVRQAPGK GLEWVS | TISVG----GGTTYYADS VKG | RFTISRDNSKNTLYLQMNSL RAEDTAVYYCAK | WGRGNSYE----YYYGMDV | WGQGT TVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH2|2-05|D6|6-19|RF2|JH4 | QITLKES- GPTLVKPTQTLTL TCTFSG-FSLS | IS---GVGVG | WIRQPPGK ALEWLA | LIYW---- NDDKRYSPS LKS | RLTITKDTSKNQVVLTMTNM DFVDTATYCAR | GFAVR-------- ---------GFDY | WGQGT LVTVS S |
| iPS:3 98498 | VH2|2-05|D6|6-19|RF2|JH4 | QITLKES- GPTLVKPTQTLTL TCTFSG-FSLS | IG---GVGVG | WIRQPPGK ALEWLA | LIYW---- NDDKRYSPS LKS | RLTITKDTSKNQVVLTMTNM DFVDTATYCAR | TIAVR------ ---------GFDY | WGQGT LVTVS S |
| | Germline | | | | | | | H_FR4 |
| | VH1|1-08|D5|5-24|RF2|JH4 | QVQLVQS- GAEVKKPGASVKV SCKASG-YTFT | | | | | | |
| iPS:3 98536 | VH1|1-08|D5|5-24|RF2|JH4 | QVQLVQS- GAEVKKPGASVKV SCKASG-YTFT | S------YDIS | WVRLATGQ GLEWMG | WMNPN--- SGNTGYAQK FQG | RVTMTRNTSISTAYMELSSL RSEDTAVYYCAR | KRA--------- ---------NDY | WGQGT LVTVS S |
| | Germline | | | | | | | H_FR4 |
| iPS:3 98546 | VH2|2-05|D6|6-6|RF1|JH4 | QITLKES- GPTLVKPTQTLTL TCTFSG-FSLS | IS---GVGVG | WIRQPPGK ALEWLA | LIYW---- SDDKRYSPS LKS | RLTITKDTSKNQVVLTMTNM APVDTATYCAR | TGSSC------- ---------CYFDY | WGQGT LVTVS S |
| | Germline | | | | | | | H_FR4 |
| iPS:4 02229 | VH3|3-21|D1|1-1|RF2|JH6 | EVQLVES- GGGLVKPGGSLRL SCAASG-FTFS | S------YSMN | WVRQAPGK GLEWVS | SISGS--- SSYIYADS VKG | RFTISRDNAKNSLYLQMNSL RAEDTAVYYCAR | VNG--------- ---------MDV | WGQGT TVTVS S |
| | Germline | | | | | | | H_FR4 |
| iPS:4 02233 | VH3|3-21|D4|4-11|RF3|JH5 | EVQLVES- GGGLVKPGGSLRL SCAASG-FTFS | I------YNLN | WVRQAPGK GLEWVS | SISGG--- AGHIYSDS VKG | RFTISRDNAKNSLYLQMNSL RAEDTAVYYCAR | TNG--------- ---------FDF | WGQGT LVTVS S |
| | Germline | | | | | | | H_FR4 |
| iPS:4 02235 | VH3|3-21|D1|1-1|RF1|JH3 | EVQLVES- GGGLVKPGGSLRL SCAASG-FTFS | S------YSMN | WVRQAPGK GLEWVS | SIST---- STFIYYADS VKG | RFTISRDNAKNSLYLQMNSL RAEDTAVYYCAR | KAG--------- ---------LDI | WGQGT MVTVS S |

Figure 51 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH3|3-23|D5|5-12|RF1|JH3 | EVQLLES | S-----YAMS | WVRQAPGK GLEWVS | AISGS--- GGSTYYADS VKG | RFTISRDNSKNTLYLQMNSL RAEDTAVYYCAK | RGIVAT | WGQGT MVTVS S |
| iPS:4 03870 | 21-225_23G4 VH3|3-23|D5|5-12|RF1|JH3 | EVQLLES-CGGLVQPGGSLRL SCAASG-FTFS | S-----YAMS | WVRQAPGK GLEWVS | VISGR---GGSTYYADS VKG | RFTISRDNSKNTLYLQMNSL RAEDTAVYYCAK | RGIVGA------TEAFDI | WGQGT MVTVS S |
| | Germline VH4|4-39|D4|4-11|RF1|JH4 | | | | | | YFDY | WGQGT LVTVS S |
| iPS:4 03872 | 21-225_8F11 VH4|4-39|D4|4-11|RF1|JH4 | QLQLQES-GPGLVQPSETLSL TCTVSG-VSIS | RT----SYYWG | WLRQPGK GLEWIG | NIYY----SGSAYNNPS LKS | RVTISVDTSKNQFSLKLSSV TAADTAVYYCGR | HGQDW------GLDY | WGQGT LVTVS S |
| | Germline VH1|1-08|D3|3-9|RF2|JH6 | | | | | | YYYYYDMDV | WGQGT TVTVS S |
| iPS:4 37240 | 21-225_84H12 VH1|1-08|D3|3-9|RF2|JH6 | QVQLVQS-GAEVKKPGASVKV SCKASG-YTFT | S-----YDIN | WVRQATGQ GLEWMG | WLNPH---SGNTGYAQK FQG | RITIMTWNTSIRTAYMELSSL RSEDTAVYYCAR | GFYDILTGYS-----PTYYYYDMDV | WGQGT TVTVS S |
| iPS:4 34577 | 21-225_75C11 VH1|1-08|D3|3-9|RF2|JH6 | QVQLVQS-GAEVKKPGASVKV SCKASG-YTFT | S-----YDIN | WVRQATGQ GLEWMG | WLNFH---SGNTGYAQK FQG | RITMTWNTSIRTAYMELSSL RSEDTAVYYCAR | GFYDILTGYS-----PTYYYYDMDV | WGQGT TVTVS S |
| iPS:4 34553 | 21-225_76H12 VH1|1-08|D3|3-9|RF2|JH6 | QVQLVQS-GAEVKKPGASVKV SCKASG-YTFT | S-----YDIN | WVRQATGQ GLEWMG | WLNPH---SGNTGYAQK FQG | RITMTWNTSIRTAYMELSSL RSEDTAVYYCAR | GFYDILTGYS-----PTYYYYDMDV | WGQGT TVTVS S |
| iPS:4 34927 | 21-225_86E5 VH1|1-08|D3|3-9|RF2|JH6 | QVQLVQS-GAEVKKPGASVKV SCKASG-YTFT | S-----YDIN | WVRQATGQ GLEWMG | WMNPN---SGNTGYAQK FQG | RVTIMTWNTSIRTAYMELSSL RSEDTAVYYCAR | GFYDILTGYS-----PTYYYYDMDV | WGQGT TVTVS S |
| | Germline VH3|3-23|D6|6-19|RF2|JH4 | | | | | | GIAVA | |
| iPS:4 35477 | 21-225_154E8 VH3|3-23|D6|6-19|RF2|JH4 | EVQLLES-GGGLVQPGGSLRL SCAASG-FTFS | S-----YAMS | WVRQAPGR GLEWVS | AISGS---GGNTFYADS VKG | RFTISRDNSKNTLYLQMNSL RAEDTAVYYCAI | HGIAVAGT------GAHYFDY | WGQGT LATVS S |
| iPS:4 35385 | 21-225_149G7 VH3|3-23|D6|6-19|RF2|JH4 | EVQLLES-CGGLVQPGGSLRL SCAASG-FTFS | S-----YAMS | WVRQAPGR GLEWVS | AISGS---GGNTFYADS VKG | RFTISRDNSKNTLYLQMNSL RAEDTAVYYCAI | HGIAVAGT------GAHYFDY | WGQGT LATVS S |

Figure 52 - Table 5
Standard IgG Antibody Variable Region Consensus Protein Alignment
CDRs defined by Kabat
Alignment numbering defined by Amgen Reference (AHo)

| KAPPA_VARIABLE | | Germline | K_FR1 | K_CDR1 | K_FR2 | K_CDR2 | K_FR3 | K_CDR3 | K_FR4 |
|---|---|---|---|---|---|---|---|---|---|
| | VK4|B3|JK3 | | DIVMTQSPDSLA VSLGERATINC | KSS QSVLYSSNNKN YLA | WYQQKPGQ PKLLIY | WAS TRES | GVPDRFSGSGSG TDFTLTISSLQAEDVAV YYC | QQYYS TPFT | FGQGTK VEIK |
| iPS:42 6126 | 21-225_6G6 | VK4|B3/J K3 | . . . . . . . . . . . . . . . . . . . . . . . . | . . . . Y . . . . . . . . . . . . . EN | . . N . F | . . . . . | . . . . . N . . . . . . . . . . . . . . . . . . F . . . . . . . . . . . | . . D . . . . . | . . H . . |
| iPS:41 2232 | 21-225_4A2 | VK4|B3/J K3 | . . . . . . . . . . . . . . . . . . . . . . . . | . . . . . . . I . H . . . . . . . . . | . F . . L . | . . . . . | . . . . . . . . . . . . . . . . . P . . . . . . . . . . . . . . . . . | . . N . . . . . | . V . . . . . G . . . |
| iPS:45 1141 | 21-225_164B11 | VK4|B3/J K3 | . . . . . . . . . . . . . . . . . . . . . . . . | . . . . . L . K . . . . . . . S . . . | S . L . . . | . . . S . | . . . . . . . . . . . . . . . . . L . . . . . . . . . . . . . . . . . | . . . . . . . . | . I . P . . . H . N . . T |
| iPS:42 3314 | 21-225_12F11 | VK4|B3/J K3 | . . . . . . . . . . . . . . . . . . . . . . . . | . . . . Y . . . . . . . . . . . . . H | . . N . F | . . . . . | . . . . . N . . . . . . . . . . . . . . . . . . F . . . . . . . . . . . | . . D . . . . . | . . . . . |
| iPS:43 5327 | 21-225_147G6 | VK4|B3/J K3 | . . . . . . . . . . . . . . . . . . . . . . . . | . . SN . . . . . . . . . . . . . . . | . . . . . | . . . A . | . . . . . . . . . . . . . . . . . . . . . . . . . . . . . . . . . . . | . . T . . . . . | . . . . . |
| iPS:43 5345 | 21-225_148G3 | VK4|B3/J K3 | . . . . . . . H . . . . . . . . . . . . . . . . | . . . R . H . . . . Y . . . . . . . . | . . . . . | . . D . . | . . . . . . . . . . . . . . . . . A . . . . . . . . . . . . . . L . . | . . . . . . . . | . . . . . |
| iPS:43 5405 | 21-225_150B7 | VK4|B3/J K3 | . . . . . . . . . . . . . . . . . . . . . . . . | . . . N . . . . . . . . . . . . . H . N | . . . . . | . . . K . | . . . . . T . . . . . . . . . . . . . . . . . . . . . . . . . . . . . | . . . . . . . . | . . . . . |
| iPS:43 5433 | 21-225_152E3 | VK4|B3/J K3 | . . . . . . . . . . . . . . . . . . . . . . . . | . . . . Y . . V . . . . . . . . . . . H | G . R . . | . . . . . | S . . . . . . . . . . . . . . . . . . . . . . . . . . . . . . . . . . | . . . . . . . . | . . . . . |
| iPS:43 5437 | 21-225_152F4 | VK4|B3/J K3 | . . . . . . . . . . . . . . . . . . . . . . . . | . . . . Y . . . . . . . . . . . . . . | . . . . . | . . . K . | . . . . . V . . . . . . . . . . . . . . . . . . . . . . . . . . . . . | . . . . . . . . | . P . . . |
| iPS:43 5649 | 21-225_165H2 | VK4|B3/J K3 | . T . . . . . . . . . P . . . . . . . . . . . . | . . . . . . . . . . . . . . . . . H . T | . . . . . | . . . . . | . . . . . V . . M . DD . . . . . . . . . . . . . . . . . . . . . . R | . S . . . . . . | . I . P . . . N |
| iPS:43 5855 | 21-225_191G3 | VK4|B3/J K3 | . . . . . . . . . . . . . . . . . . . . . . . . | . . . . . . . . . . . . . . . . . . H | . L . . . | . . . . . | . . . . . . . . . . . . . . . . . . . . . . . . . . . . . . . . . . F | . . . . . . . . | . S . P . . . M . . |
| iPS:43 5903 | 21-225_190E2 | VK4|B3/J K3 | AN . . . . . . . . . . . . . . . . . . . . . . . | . . . SY . . . . . . . . . . . . . FN | . . N . . | . . . . . | . . . . . . . . . . . . . . . . . . M . . . . . . . . . . . . . . . . . | . FN . . . . . | . L . . . . . R |
| iPS:43 5915 | 21-225_190H4 | VK4|B3/J K3 | . . . . . . . . . . . . . . . . . . . . . . . . | . . . . . Y . . . . . . . . . . . . H | . R . . . | . . . . . | . . . . . . . . . . . . . . . . . . . . . . . . . . . . . . . . . . . | . S . . . . . . | . I . P . . . |
| iPS:43 5923 | 21-225_190H6 | VK4|B3/J K3 | . . . . . . . . . . . . . . . . . . . . . . . . | . . . . . . . . . . . . . . . . . . FN | . . N . . | . . . . . | . . . . . . . . . . . . . . . . . . . . . . . . . . . . . . . . . . C | . C . . . . . . | . L . . . . . R |
| iPS:43 5953 | 21-225_191B12 | VK4|B3/J K3 | . . . . . . . . . . . . . . . . . . . . . . . . | . . . . . . . . . . . . . . . . . . FN | . . . . . | . . . . . | . . . . . N . . . . . . . . . . . . . . . . . . . . . . . . . . . I . | . S . . . . . . | . L . . . . . |
| iPS:43 6098 | 21-225_195G11 | VK4|B3/J K3 | . D . . . . . . . . . . . . . . . . . . . . . . | . . . . . . . . . . . . . . . . . . FN | . . N . . | . . L . . | . . . . . M . . . . . . . . . . . . . . . . . . . . . . . . . . . . C | . C . . . . . . | . F . . . . . R |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 6102 | 21-225_196B1 | VK4|B3/JK3 | .......F........ | .......I.F. | ........... | ........... | ........... | ...S....... | ........ |
| iPS:43 6104 | 21-225_196C1 | VK4|B3/JK3 | ........ | ....R....FN | L.N....... | ........ | ........M..C | ...C....L. | ........ |
| iPS:43 6156 | 21-225_197C8 | VK4|B3/JK3 | ........ | ......P. | ........ | ........ | ........ | ..S.T....F. | ........ |
| iPS:43 6270 | 21-225_203F10 | VK4|B3/JK3 | ........ | .....FFH | ........ | ........ | ......S... | ........I | ......N |
| iPS:43 6570 | 21-225_225F4 | VK4|B3/JK3 | ........ | ........ | ........ | ........ | ......T... | ....F....L. | .......T |
| iPS:43 4065 | 21-225_11E2 | VK4|B3/JK3 | ........ | ....N..R..S. | .....R. | ......I. | ...CV.P... | H..HN...S.P. | H..E |
| iPS:39 | | VK4|B3/JK3 | ....H.. | ........ | ........ | ........ | ........ | ....F....... | ....R |
| | Germline | | K_FR1 DIQMTQSPSSLS ASVGDRVTITC | K_CDR1 RAS QGIS NDLG | K_FR2 WYQQKPGK APKLLIY | K_CDR2 AASSLQS | K_FR3 GVPSRFSGSGSG TDFTLTISSLQPEDFAT YYC | K_CDR3 LQHNS YPLT | K_FR4 FGGGTK LEIK |
| iPS:47 3253 | 21-225_7C3_LC5 | VK1|A30/JK5 | ........ | .......S.... | ........N.V. | ........ | ........V..... | ........ | ........ |
| iPS:47 3256 | 21-225_9F12_LC2 | VK1|A30/JK5 | ........ | ........ | ........V. | ........L. | ........ | ........YL.. | ........ |
| iPS:45 3449 | 21-225_208A2 | VK1|A30/JK5 | ........ | ........T... | ........Q. | ........ | ........ | ........ | ........ |
| iPS:43 4467 | 21-225_73H8 | VK1|A30/JK5 | .......Y ......R | ........D.. | ....L..V. | ........ | ........S..... | ......I..G | ....P. |
| iPS:43 5045 | 21-225_90H5 | VK1|A30/JK5 | ........ | ........ | ........ | ........I | ........R....D. | ........YP. | ........V |
| iPS:43 5561 | 21-225_159F1 | VK1|A30/JK5 | ........ | ......RV.. | ........A.D. ....I.F | ....D..N. | ........ | ....H.... | ........ |
| iPS:43 6328 | 21-225_207F12 | VK1|A30/JK5 | ........ | ........ | ........ | ........ | ........F.. | ........L. | ........ |
| iPS:43 6354 | 21-225_210G10 | VK1|A30/JK5 | .......F | ........T... | ........Q. ....T..M. | ........ | ........R....D. | ....Y....P. | ........ |
| iPS:39 3094 | 21-225_34C4 | VK1|A30/JK5 | ........ | ........ | ........ | ........ | ........ | ...S.......... | ........ |
| iPS:39 8484 | 21-225_18D4 | VK1|A30/JK5 | ........ | ........ | ....T..... | .......N. | ........V..... | ........YL.. | ........ |
| ........ | ....E. | ....T... | ....E. | ........ | .H..N......... | ........ |
| | Germline | | K_FR1 DIQMTQSPSSVS ASVGDRVTITC | K_CDR1 RAS QGIS SWLA | K_FR2 WYQQKPGK APKLLIY | K_CDR2 AASSLQS | K_FR3 GVPSRFSGSGSG TDFTLTISSLQPEDFAT YYC | K_CDR3 QQANS FPFT | K_FR4 FGPGTK VDIK |
| VK1|L5|JK3 | | | | | | | | | |

| | | | | | | | | | |
|---|---|---|---|---|---|---|---|---|---|
| iPS:43 4167 | 21-225_50F3 | VK1|L5/J K3 | . . . . . . . . . . . | . . . . D . . . . . | . . . . . F . . . . | . . . . . . . . . N | . . . . . . . . . . | . . . . . . . . . T | . . . . . . . . . . |
| iPS:43 4189 | 21-225_56E5 | VK1|L5/J K3 | . . . . . . . . . . . | . . . . . R . . . . | . . . . . . . . . . | . . . . . . . . . . | . . . . . . . . . . | . . . . . . . . . . | . . . . . . . . . . |
| iPS:43 4193 | 21-225_56C6 | VK1|L5/J K3 | . . . . . . . . . . . | . . . K . . . . . . | . . . . S . N . . . | . . . . . R . . . . | . I . . . S . . . Y | . . . . . . . . . . | . . . . . . . . . . |
| iPS:43 4195 | 21-225_56F6 | VK1|L5/J K3 | . . . Y . . . . . . . | . V . . . D . . . . | . F . . . . . . . V | . . . . . . . . . . | . F . . . . . . . . | . . . . . . . . . . | . . . . . . . . . . |
| iPS:43 4273 | 21-225_57E4 | VK1|L5/J K3 | . . . . . C . . . . . | . . K . . . . . . . | . . . . . . . . . . | . . . . . . . G . . | . . . . . S . . . . | . . . . . . . . G . | . . . . . . . . . . |
| iPS:43 4277 | 21-225_57A7 | VK1|L5/J K3 | . . . . . . . S . . . | . . . N . . . . . . | . . . . . . . . . . | . . . . . . . . . . | . . . . . . . . . . | . . . . . . . . . . | . . . . . . . . . . |
| iPS:43 4355 | 21-225_64G12 | VK1|L5/J K3 | . . . . . . . . . . . | . . . R . . . . . . | . . . . . . . . . N | . . . . . . . . . . | . . . . . . . . . . | . . . . . . . . . . | . . . . . . . . L . |
| iPS:43 4389 | 21-225_66F11 | VK1|L5/J K3 | . . . . . C . . . . . | . . . N . T . . . . | . . . . . S . . . . | . . . . . . . . . . | . . . . . . . . . I | . . . . . . . . . . | . . . . . . . . . . |
| iPS:43 4423 | 21-225_70D1 | VK1|L5/J K3 | . . . . . . . . . . . | . E . . . . I . . . | . . . . . . . . . . | . . . . . . . . . . | . . . . . . . Y . . | . . . . . . . . . . | . . . . . . . . . . |
| iPS:43 5291 | 21-225_146E1 | VK1|L5/J K3 | . . . . . . . . . . . | . . . . . V . . . . | . . . . . . . . . . | . . . . . . . . . . | . V . . . . . . . . | . . . . . . . . . . | . . . . . . . . . . |
| iPS:43 5303 | 21-225_146A6 | VK1|L5/J K3 | . . . . . . . K . . . | . . . N . . . . . . | . . . . . . . . . . | . . . . . . . . . . | . . . . . S . . . R | . . . . . . . . . . | . . . . . . . . . . |
| iPS:43 5335 | 21-225_147D10 | VK1|L5/J K3 | . . . . . A . . . . . | . . . N . V . . . . | . . . . . . . . . . | . . . . . . . . . . | . . . . . S . . . . | . . . . . . . . T D | . . . . . . . . . . |
| iPS:43 5339 | 21-225_147D12 | VK1|L5/J K3 | . . . . . A . . . . . | . . . N . . . . . . | . . . . . . . . . . | . . . . . . . . . . | . . . . . S . . . . | . . . . . . . . T D | . . . . . . . . . V |
| iPS:43 5343 | 21-225_148E2 | VK1|L5/J K3 | . . . . . A . . . . . | . . . N . . . . . . | . . . . . . E . . . | . . . . . . . . . . | . . . . . S . . . N E | . . . . . . . . T D | . . . . . . . . . V |
| iPS:43 5379 | 21-225_149B6 | VK1|L5/J K3 | . . . . . . . . . . . | . . . . . I . . . . | . . . . . . . . . R | . . . . . . . . . . | . . . . . . . . . . | . . . . . . . . G . | . . . . . . . . . . |
| iPS:43 5381 | 21-225_149C6 | VK1|L5/J K3 | . . . . . A . . . . . | . . . N . . . . . . | . . . . . . . . . . | . . . . . . . . . . | . . . . . S . . . Y | . . . . . . . . T D | . . . . . . . . . V |
| iPS:43 5391 | 21-225_149F8 | VK1|L5/J K3 | . . . . . A . . . . . | . . . N . T . . . . | . . . . . . . . . . | . . . . . . . . . . | . . . . . S . . . N E | . . . . . . . . T D | . . . . . . . . . . |
| iPS:43 5395 | 21-225_149D11 | VK1|L5/J K3 | . . . . . A . . . . . | . . . N . . . . . . | . . . . . . . . . . | . . . . . . . . . . | . . . . . S . . . I | . . . . . . . . T D | . . . . . . . . . V |
| iPS:43 5403 | 21-225_150C5 | VK1|L5/J K3 | . . . . . G . . . . . | . . . N . . . . . . | . . . . . . . . . . | . . . . . . . . G . | . . . . . S . . . . | . . . . . . . . G . | . . . . . . . . . . |
| iPS:43 5447 | 21-225_152H7 | VK1|L5/J K3 | . . . . . A . . . . . | . . . . . D . . . . | . . . . . . . . . . | . . . . . . . . . . | . . . . . S . T . . | . . . . . . . . T D | . . . . . . . . . V |
| iPS:43 5453 | 21-225_152G10 | VK1|L5/J K3 | . . . . . A . . . . . | . . . N . . . . . . | . . . . . S . . . . | . . . . . . . . G . | . . . . . S . . . N E | . . . . . . . . T D | . . . . . . . . . V |

Figure 52 (Continued)

| | | | | | | | | | | |
|---|---|---|---|---|---|---|---|---|---|---|
| iPS:43 5483 | 21-225_155A4 | VK1|L5/J K3 | . . . . . . . . . . A . . . | . . . . . . . . . . . . . | . . . . . . . . . . . . . | . . . . . . H . . . . . . | . . . . . . . . . . . . . | . . . . . . . . . . . S . | . . . . . . . . . . . . . | H.TD. . . . . . . . . . | . . . . . . . . . . . . . |
| iPS:43 5485 | 21-225_155B4 | VK1|L5/J K3 | . . . . . . . . . . A . . . | . . . . . N . . . . D . . | . . . . . . . . . . . . . | . . . . . . . . . . . . G | . . . . . . . . . . . . . | . . . . . . N . . . . . . | . . . . . . . . . . . . . | H.TD. . . . . . . . . . | . . . . . . . . . . . . . |
| iPS:43 5787 | 21-225_180A3 | VK1|L5/J K3 | . . . . . . . . . . . . . | . . . . . N . . . . D.T . | . . . . . . . . . . . . . | . . . . . . . . . . . . . | . . . . . . . . . . . . . | . . . I . . . . . . F H . | . . . . . . . . . . . I . | . . . . . . . . . . . . . | . . . . . . . . . . . N . |
| iPS:43 5809 | 21-225_182H5 | VK1|L5/J K3 | . . . . . . . . . . . . Y | . . . . . . . . . . D.T . | . . . . . . . . . . . . . | . . . . . . . . . . . . . | . . . . . . . . . . . . . | . . I . T V . D . . . . . | . . . . . . . . . . V . . | . . . . . . . . . . . V . | . . . . . . . . . . . H . |
| iPS:43 5889 | 21-225_186A11 | VK1|L5/J K3 | . . . . . . . . . . . . . | . . . . . . . . . . D.T . | . . . . . . . . . . . . . | . . . . . . . . . . . . G | . . . . . . . . . . . . . | . . I . T V . D . . . . . | . . . . . . . . . . . . . | . . . . . . . . . . . . . | . . . . . . . . . . . H . |
| iPS:43 5965 | 21-225_192H2 | VK1|L5/J K3 | . . . . . . . . . . . . . | . . . . . . . . . . . I . | . . . . . . . . . . . . . | . . . . . . . . . . . . . | . . . . . . . . . . . . . | . . . . . . . . . . . . . | . . . . . . . . . . . S . | . . . . . . . . . . . . . | . . . . . . . . . . . V . |
| iPS:43 6106 | 21-225_196F2 | VK1|L5/J K3 | . . . . . . . . . . . . . | . . . . . . . . . . . . . | . . . . . . . . . . . . . | . . . . . . . . . . . . . | . . . . . . . . . . . N . | . . . . . . . . . . . . . | . . . . . . . . . . . . . | . . . . . . . . . . . T . | . . . . . . . . . . . . . |
| iPS:43 6360 | 21-225_210H11 | VK1|L5/J K3 | . . . . . . . . . . . . . | . . . . . . . . . . . I . | . . . . . . . . . . . N . | . . . . . . . . . . . . . | . . . . . . . . . . . . . | . . . . . . . . . . . . R | . . . . . . . . . . . . . | . . . . . . . . . . . K . | . . . . . . . . . . . . . |
| iPS:43 6488 | 21-225_221A6 | VK1|L5/J K3 | . . . . . . . . . . . . . | . . . . . . . . . . . . . | . . . . . . . . . . . . . | . . . . . . . . . . . T . | . . . . . . . . . . . N . | . . . . . . . . . . . . . | . . . . . . . . . . . . R | . . . . . . . . . . . . . | . . . . . . . . . . . R . |
| iPS:43 6494 | 21-225_221F12 | VK1|L5/J K3 | . . . . . . . . . . . . . | . . . . . . . . . . . . . | . . . . . . . . . . . . . | . . . . . . . . . . . T . | . . . . . . . . . . . N . | . . . . . . . . . . . . . | . . . . . . . . . . . . . | . . . . . . . . . . . . . | . . . . . . . . . . . . . |
| iPS:43 6496 | 21-225_222E1 | VK1|L5/J K3 | . . . . . . . . . . . . . | . . . . . . . . . . . . . | . . . . L . V . . . . . . | . . . . . . . . . . . T . | . . . . . . . . . . . N . | . . . . . . . . . . . . . | . . . . . . . . . . . . . | . . . . . . . . . . . . . | . . . . . . . . . . . . . |
| iPS:43 6508 | 21-225_222F7 | VK1|L5/J K3 | . . . . . . . . . . . . . | . . . . . . . . . . . . . | . . . . . . . . . . . . . | . . . . . . . . . . . . . | . . . . . . . . . . . . . | . . . . . . . . . . . . . | . . . . . . . . . . . V . | . . . . . . . . . . . . . | . . . . . . . . . . . . . |
| iPS:43 6516 | 21-225_222C12 | VK1|L5/J K3 | . . . . . . . . C . . . . | . . . . . R . . . . . . . | . . . . . . . . . . . . . | . . . . . . . . . . . . . | . . . . . . . . . . . . . | . . . . . . . . . . . . . | . . . . . . . . . . V . R | . . . . . . . . . . . D . | . . . . . . . . . . . R . |
| iPS:43 7234 | 21-225_64E2 | VK1|L5/J K3 | . . . . . . . . . . . . . | . . . . . . . . . A.N . . | . . . . . . . . . . . . . | . . . . . . . . . . . . . | . . . . . . . . . . . F . | . . . . . . . . . . . . . | . . . . . . . . . . . . . | . . . . . . . . . . . . . | . . . . . . . . . . . . . |
| iPS:39 2996 | 21-225_28B1 | VK1|L5/J K3 | . . . . . . . . . . . . . | . . . . . . . . . . D . . | . . . . . . . . . . . . . | . . . . . . . . . . . . . | . . . . . . . . . . . . . | . . . . . . . . . . . . . | . . . . . . . . . . . . . | . . . . . . . . . . . . . | . . . . . . . . . . . . . |
| iPS:39 3010 | 21-225_25E11 | VK1|L5/J K3 | . . . . . . . . . . . . . | . . . . . . . . . . . N . | . . . . . . . . . . . . . | . . . . . . . . . . . . G | . . . . . . . . . . . . . | . . . . . . . . . . . . . | . . . . . . . . . . . . . | . . . . . . . . . . . I . | . . . . . . . . . . . . . |
| iPS:39 3016 | 21-225_28F11 | VK1|L5/J K3 | . . . . . . . . . . . . . | . . . . . . . . . . . N . | . . . . . S . . . . . . . | . . . . . . . . . . . . . | . . . . . . . . . . . N . | . . . . I S . . . . . C . | . . . . . . . . . . . . R | . . . . . . . . . . . . . | . . . . . . . . . . . . . |
| iPS:39 3024 | 21-225_31H9 | VK1|L5/J K3 | . . . . . . . . . . . . . | . . . . . . . . . . . T . | . . . . . R . . . . . . . | . . . . . . . . . . . D . | . . . . . . . . . . . . . | . . . . . . T . . . . . . | . . . . . . . . . . . . R | . . . . . . . . . . . L . | . . . . . . . . . . . . . |
| iPS:39 3080 | 21-225_34F3 | VK1|L5/J K3 | . . . . . T . . . . . . . | . . . . . . . . . . . T . | . . . . . . . . . . . . . | . . . . . . . . . . . F . | . . . . . . . . . . . . . | . . I F . . . . . . . . . | . . . . . . . . . . . . . | . . . . . . . . . . . . . | . . . . . . . . . . . R . |
| iPS:39 3084 | 21-225_35C6 | VK1|L5/J K3 | . . . . . . . S . . . . . | . . . . K . . . . . . . . | . . . . . P . . . . . . . | . . . . . . . . . . . . . | . . . . . . . . . . . . . | . . . . . . . T . . . . . | . . . . . . . . . . . S . | . . . . . . . . . . . G . | . . . . . . . . . . . . . |
| iPS:39 3086 | 21-225_36H5 | VK1|L5/J K3 | . . . . . . . . . . . . . | . . . . . K . . . . R . . | . . . . . E . . . . . . . | . . . . . . . . . . . R . | . . . . . . . . . . . . . | . . . . . I . . . . . T . | . . . . . . . . . . . . . | . . . . . . . . . . . . . | . . . . . . . . . . . Q . |

Figure 52 (Continued)

| | | | | | | | | | |
|---|---|---|---|---|---|---|---|---|---|
| iPS:39 3098 | 21-225_35G6 | VK1|L5/J K3 | | | .R. | | .V. | | .G. | A. | | ...L |
| iPS:39 3112 | 21-225_33G1 | VK1|L5/J K3 | V | .L. | | | .V. | .R. | | | |
| iPS:39 3116 | 21-225_34G7 | VK1|L5/J K3 | | | .L. | | | G. .Y. | | | |
| iPS:39 3132 | 21-225_33H7 | VK1|L5/J K3 | | | .K. | | .V. | | | .T. | |
| iPS:39 3140 | 21-225_35H12 | VK1|L5/J K3 | | | .R. | | | | .I. | | |
| iPS:39 3954 | 21-225_4H6 | VK1|L5/J K3 | | | .R. .E. | | | .R. | | .G. | ...L |
| iPS:39 8502 | 21-225_23B11 | VK1|L5/J K3 | | | .R. T. | | .V. | G. | | .t. | |
| iPS:39 8520 | 21-225_31C4 | VK1|L5/J K3 | | | .K. | | | .R. | .R. | .R. | |
| iPS:40 2223 | 21-225_30A11 | VK1|L5/J K3 | | | .K. | | .P. | | .T. | .I. | |
| | | Germline | K_FR1 | | K_CDR1 | | K_FR2 | .R. .E. | K_CDR2 | K_FR3 | ...N |
| | | | DIVMTQSPDSLA VSLGERATINC | | KSS QSVLYSSNNKN YLA | | WYQQKPGQ PPKLLIY | WASTRES | GVPDRFSGSGS GTDFTLTISSLQAEDVAVY YC | K_CDR3 | K_FR4 FGQGTK VEIK |
| VK4|B3/JK1 | | | | | | | | | | |
| iPS:42 6112 | 21-225_12F12 | VK4|B3/J K1 | | | | | | | | | |
| iPS:45 1137 | 21-225_74A7 | VK4|B3/J K1 | | | .NH. T. .F. | | ..N. | .A. | | .H. | S. | ...T |
| iPS:43 3909 | 21-225_43D8 | VK4|B3/J K1 | | | .Y. F. | | ..N. | | .A. | | .S.P. | .Q. |
| iPS:43 4177 | 21-225_56A1 | VK4|B3/J K1 | | | .D. .MT | | .R. | | .G. | | .P. | |
| iPS:43 4237 | 21-225_61B5 | VK4|B3/J K1 | | | ..T | | .R. | | .G. | | .P. | |
| iPS:43 4285 | 21-225_57A11 | VK4|B3/J K1 | T | | .N.S.T .H. | | .L. .N. | | | | | ...S |
| iPS:43 4295 | 21-225_58B9 | VK4|B3/J K1 | | | .Y. .H. | | .R. .K. | | .M. | | .P. | |
| iPS:43 4321 | 21-225_59F10 | VK4|B3/J K1 | F | | .G. .I. | | .K. | .A. | .A. | .F. | .P. | ...F |
| iPS:43 4431 | 21-225_70E7 | VK4|B3/J K1 | | | .N. .T. .R | | | .D. | | .N. | .I.P. | |
| iPS:43 4475 | 21-225_74F9 | VK4|B3/J K1 | L | | .Y. | | .K. | .A. | .S. | | .S.P. | ...S |

| | | | | | | | | | | | |
|---|---|---|---|---|---|---|---|---|---|---|---|
| iPS:43 4707 | 21-225_80D3 | VK4[B3/J K1 | . . . . . . . C . . | . . . . . . . . T | . . . . N . . . | . . . . . . . . | . . . . . . . . | . . . . . . . . | . . . . . . . . | . H . NE . . . | V . V . . |
| iPS:43 4711 | 21-225_80H3 | VK4[B3/J K1 | . . . . . . . . . | . . . . . . HR | . . . . Y . . . | . . . . . . . . | . . . . . . . . | . . . . . . . . | . . . . . . . . | . . . . . . . . | . . T . . |
| iPS:43 4731 | 21-225_80E9 | VK4[B3/J K1 | . . . . . . . C . | . . . . . . . T | . . . . . . . . | . . . . . . . . | . . . . . . . . | . . . . . . . . | . . . . . . . . | . . . . N . . | . . V . . |
| iPS:43 4761 | 21-225_81E5 | VK4[B3/J K1 | . . . . . . . C . | . . . . . . F . | . . . . N . . . | . . . . . . . . | . . . . . . . . | . . . . . . . . | . . . . . . . . | . . . . . . . . | . . . . T |
| iPS:43 4771 | 21-225_81F9 | VK4[B3/J K1 | . . . . . . . C . | . . . . . . . T | . . . . Y . . . | . . . R . . . . | . . . . . . . . | . . . . . . . . | . . . . . . . . | . S . L . . . | . Q . . . |
| iPS:43 4827 | 21-225_83F3 | VK4[B3/J K1 | . . . . . . . C . | . . . . . . . T | . . . . N . . . | . . . . . . . . | . . . . . . . . | . . . . . . . R | . H . ND . . . | . . . . GK | V . IM |
| iPS:43 4829 | 21-225_83G3 | VK4[B3/J K1 | . . . . . . . C . | . . . . . . . T | . . . . N . . . | . . . . . . . . | . . . . . . . . | . . . . . . . . | . H . ND . . . | . . . . GK | . . T . . |
| iPS:43 4841 | 21-225_83G7 | VK4[B3/J K1 | . . . . . . . . . | . . . . . T . H . | . . . . Y . . . | . . . . . . . . | . . . . . . . . | . . . . . . . . | . H . N . . . . | . . . . K . | V . I . . |
| iPS:43 4863 | 21-225_84G7 | VK4[B3/J K1 | . . . . . . . P . | . . . . . T . H . | . . . . Y . . . | . . . V . . . . | . F . . . . . . . | . . . . . . . . | . . F . . . . | . S . L . . . | . . . . . |
| iPS:43 4877 | 21-225_85H2 | VK4[B3/J K1 | . . . SM . . . . . | . . . . . . H . | . . . . Y . . . | . . . V . . . . | . F . . . . . . . | . . . . . . . . | . . F . . . . | . S . P . . . | V . . . . |
| iPS:43 4901 | 21-225_85H9 | VK4[B3/J K1 | . . . . . . . . . | . . . . . . HR | . . . . K . . . | . . . . . . . . | . . . . . . . . | . . . . . . . . | . . R . . . . | . . . . . . . | . . . . . |
| iPS:43 4935 | 21-225_86E9 | VK4[B3/J K1 | . . . . . . . C . | . . . P . . . . | . . . . Y . . . | . . . . . . . . | . . . . . . . . | . . . A . . . . | . . . . . . . . | . . . . . . . | . . . . . |
| iPS:43 4965 | 21-225_88A1 | VK4[B3/J K1 | N . . . . . . . . | . A . . . . . . | . . . . Y . . . | . . . N . . . . | . . . . . . . . | . . . . . . . . | . H . . . . . . | . . . . . . . | . . T . . |
| iPS:43 4971 | 21-225_88G2 | VK4[B3/J K1 | . . . . . . . . . | . . . . . . . T | . . . . . . . . | . . . . . . . L | . . . . . . . . | . . . . . . . . | . . . . . . . . | . . . . . . . | . . . . . |
| iPS:43 4973 | 21-225_88B4 | VK4[B3/J K1 | . . . . . . . C . | . . . . . . . H . | . . . . W . . . | . . . . . . . H | . . . . . . . . | . A . . . . . . | . . R . . . . | . A . P . . . | . . . . . |
| iPS:43 4997 | 21-225_88C10 | VK4[B3/J K1 | . . . . . . . . . | . . . . . . HN | . . . . N . . . | . . . . . . . . | . F . K . . . . | . . . . . . . . | . L . . . . . . | . S . L . . . | V . . . . |
| iPS:43 5051 | 21-225_90D9 | VK4[B3/J K1 | . . . . . . . P . | . . . . . T . H . | . . . . Y . . . | . . . V . . . . | . F . . . . . . . | . G . N . . . . | . . . . . . . . | . S . P . . . | . . . . . |
| iPS:43 5053 | 21-225_75F9 | VK4[B3/J K1 | . . . . . . . V . | . . . . . . . T | . . . . . . . . | . . . . . . . . | . . . . . . . . | . . . . . . . . | . . . . . . . . | . . . . . . . | . . . . . |
| iPS:43 5071 | 21-225_91F1 | VK4[B3/J K1 | . . . . . . . C . | . . . . . . . . | . . . . N . . . | . . . . . . . . | . . . . . . . . | . . . . . . . . | . H . N . . . . | . . . . K . | V . . . . |
| iPS:43 5087 | 21-225_91G8 | VK4[B3/J K1 | . . . . . . . . . | . . . . . . . T | . . . . . . . . | . . . I . . . . | . . . . . . . . | . . . . . . . . | . . T . . . . | . . . . . . . | . . . . . |
| iPS:43 5113 | 21-225_92E6 | VK4[B3/J K1 | . A . . . . . . . | . . . NI . S . | . . . . . T . . | . . . . . . . T | . . . . . . . . | . . . F . . . . | . . F . . . . | . V . P . . . | . . . . . |

Figure 52 (Continued)

| ID1 | ID2 | Framework | Col1 | Col2 | Col3 | Col4 | Col5 | Col6 | Col7 |
|---|---|---|---|---|---|---|---|---|---|
| iPS:43 5167 | 21-225_92F12 | VK4\|B3/JK1 | ........ | ........ | ........ | ........ | ........ | ........ | ........ |
| iPS:43 5203 | 21-225_75A7 | VK4\|B3/JK1 | ........ | ...Y.... | ....T.H. | ........ | ........ | .....P. | ........ |
| iPS:43 5209 | 21-225_75A10 | VK4\|B3/JK1 | N...A... | ........ | HN | ...V.... | ........F | ........ | ........ |
| iPS:43 5211 | 21-225_94E11 | VK4\|B3/JK1 | ........ | ...Y.... | ....T | ......L. | .......K | ........ | ...S.P. | ........ |
| iPS:43 5215 | 21-225_94E12 | VK4\|B3/JK1 | ........ | ...Y.... | ........F. | ....N... | ........ | ........ | ........ |
| iPS:43 5227 | 21-225_95G4 | VK4\|B3/JK1 | ....T... | ...Y.... | HR | ......R. | ........ | ........A. | ....H... | ...S.L. | ......Q. |
| iPS:43 5245 | 21-225_95E12 | VK4\|B3/JK1 | ....C... | ....Y... | ....FR | HN | ........ | ........ | ....H... | .....P. | ........ |
| iPS:43 5249 | 21-225_96E2 | VK4\|B3/JK1 | ........ | ...A.... | ........ | N.F. | ........ | ........ | ........ | ........ | ........ |
| iPS:43 5255 | 21-225_96D5 | VK4\|B3/JK1 | .S...... | ...K.... | ....H... | ........ | W........ | ........ | ........ | ........ |
| iPS:43 5257 | 21-225_96H5 | VK4\|B3/JK1 | ........ | ....Y... | ........ | ....N... | ........ | ....Y.A. | ....H... | ...S.L. | ......Q. |
| iPS:43 5267 | 21-225_96D10 | VK4\|B3/JK1 | ........ | ...SH... | NI.S. | ......I. | .......I | ...S..M..F | ........ | ....CS | ........ |
| iPS:43 5279 | 21-225_97H4 | VK4\|B3/JK1 | ........ | ........ | .....T | ......T. | ........ | ........ | ........ | .....P. | ........ |
| iPS:43 5321 | 21-225_147E4 | VK4\|B3/JK1 | ........ | ...Y.... | ....H.. | ....L.R. | ........ | ........ | ........ | ...V.P. | ........ |
| iPS:43 5353 | 21-225_148F8 | VK4\|B3/JK1 | ....L... | ...Y.... | .A.H.. | ........ | ........ | ........R | ........ | ........ | ...V.T |
| iPS:43 5369 | 21-225_149A2 | VK4\|B3/JK1 | ........ | P.N..... | ........ | ........ | .......K | ........ | ........ | ......K | ......P. |
| iPS:43 5373 | 21-225_149E3 | VK4\|B3/JK1 | .....S.. | ......Y. | .H.F... | ........ | ........ | ........ | ........ | ....S.. | ........ |
| iPS:43 5375 | 21-225_149H4 | VK4\|B3/JK1 | ........ | .....GN. | .T..HN | ........ | ......LR | ........ | ......H. | ....I.P. | ........ |
| iPS:43 5481 | 21-225_154A11 | VK4\|B3/JK1 | ........ | ........ | .N..H. | ........R. | ........ | ........ | ........ | ........ | ........ |
| iPS:43 5557 | 21-225_158B12 | VK4\|B3/JK1 | .....P.. | .....N.. | .N..T | ........ | ........ | ........ | ........ | ......E. | ........ |
| iPS:43 5627 | 21-225_162F6 | VK4\|B3/JK1 | ........ | ........ | ........ | ......R. | .......K.D | ........ | ........E | ....S.R. | ........ |
| iPS:43 5701 | 21-225_170F6 | VK4\|B3/JK1 | ....A... | ...Y.... | ....H.. | ...V..H | ........ | ....N... | ........V | ........ | .....P. |

Figure 52 (Continued)

| | | | | | | | | | | | |
|---|---|---|---|---|---|---|---|---|---|---|---|
| iPS:43_5737 | 21-225_174G5 | VK4|B3/J K1 | . . . . . . . . . . . A . . . . | . . . . . Y . . T | . . . . . . H . | . . . . . . . . . | . . . . . . . . . | . . . . . . . . . | . . . . . . . . . | . . . R . . . . . | . . . . . . . . . |
| iPS:43_5751 | 21-225_175D10 | VK4|B3/J K1 | . . . . . . . . . . . . . . . . | . . . . . N . . . | . . . . . . . T | . . . . . . . . N | . . . . . . . . . | . . . . . . . . . | . . . . . . . . . | . . . . . . . P . | . . . . . . . . . |
| iPS:43_5773 | 21-225_177B12 | VK4|B3/J K1 | . . . . . . . . . . . . . . . V | . . . . . N . . . | . . . . . . . T | . . . . . . . . . | . . . . . . . . . | . . . . . . . . . | . . . . . . . . . | . S . . . . . P . | . . . . . . . . . |
| iPS:43_5801 | 21-225_181E5 | VK4|B3/J K1 | . . . . . . . . . . . . . . . . | . . . . . Y . . . | . . . . . . H . | . . . . . . . . . | . . . . . . . . . | . . . . . . . . . | . . . . . . . . . | H . F I . . . . . | . . . L . . . . . |
| iPS:43_5841 | 21-225_191D8 | VK4|B3/J K1 | . . . . . . M . . . . I . S . . | . R . . . . . . . | . . . . . . . H | . . . . . . . . . | . . . . . . . . . | . . . . . . . . . | . . . . . . . . . | . . . . . . . . . | . . . . . . . . . |
| iPS:43_5925 | 21-225_190D7 | VK4|B3/J K1 | . . . . . . . . . . . . . . . . | . . . . . Y . . . | . . . . . . . S | . . . . . . . . . | . . . . . . . . K | . . . . . . . . . | . . . . . . . . . | . . . R . . . . . | . . . . . . . . . |
| iPS:43_6021 | 21-225_193G4 | VK4|B3/J K1 | . . . . . . . . . . . . . . . . | . . . . . Y . . . | . . . . . . . V | . . . . . . . . . | . . . . . . . . . | . . . . . . . . D | . . . . . . . . . | . . . I . . . . . | . . . . . . . . . |
| iPS:43_6114 | 21-225_196G8 | VK4|B3/J K1 | . . . . . . . . . . . . . . . . | . . . . . Y . . . | . . . . . . . T | . . . . . . . . . | . . . . . . . . K | . . . . . . . . D | . . . . . . . . . | . . . N . . . . . | . . D . . . . . . |
| iPS:43_6150 | 21-225_197H4 | VK4|B3/J K1 | . . . . . . . . . . . . . . . T . . . . . . . V | . . . . . . N . | . . . . . . . . . | . . . . . . . . . | . . . . . . . . . | . . . . . . . . A | . . . . . . . . . | . . . . . . . . . | . . . . . . . . . |
| iPS:43_6154 | 21-225_197C6 | VK4|B3/J K1 | . . . . . . M . . S . . . T . . . I . S . . . . | . R . . . . . . . | . . . . . A . H | . . . . . . . . . | . . . . . . . . . | . . . . . . . . P | . . . . . . . . . | . . . . . . . P . | . . . L . . . . . |
| iPS:43_6218 | 21-225_200G7 | VK4|B3/J K1 | . . . . . . M . . . . . . I . S . . . . . . . . | . F . . Y . . . . | . . . . . . . H | . . . . . . . N . | . . . . . . . . . | . . . . . . . . . | . . . . . . . . . | . . . . . . . P . | . . . L . . . . . |
| iPS:43_6272 | 21-225_201F5 | VK4|B3/J K1 | . A . . . . . . . . . . V K . . | . . . . . . N . . | . . . . . . . . | . . . . . . . . . | . . . . . . . . . | . . . . . . . . A | . . . . . . . . . | . . . N . . . P . | . . . . . . . . . |
| iPS:43_6400 | 21-225_213H7 | VK4|B3/J K1 | . . . . . . . . . . . . . . . E | . . . . . . . . . | . . . . . . . V | . . . . . . F . . | . . . . . . . . . | . . . . . . . . . | . . . . . . . . . | . . . . . . . . . | . . . . . . . . . |
| iPS:43_6402 | 21-225_213H12 | VK4|B3/J K1 | . . . . . . . . . . . . . . . . | . . . . . . N . DI | . . N . . . S . G | . . . . . . . . N | . . . . . . . . . | . . . . . . . T . | . . . . . . . . . | . . . N . . . I . P | . . . R . . . . . |
| iPS:43_6500 | 21-225_222H3 | VK4|B3/J K1 | . . . . . . . . . . . . . . . T | . . . . . . N . . KT | . . . . . . K . | . . . . . . . Q . | . . . . . . . . . | . . . . . . . . . | . . . . . . . . H | . . . . . . . I . | . . . . . . . . . |
| iPS:43_6520 | 21-225_223G10 | VK4|B3/J K1 | . . . . . . . . . . . . . . . . | . . . HR . . . . . | . . . . . . . . | . . . . . . . H . | . . . . . . . . . | . . . . . . . . . | . . S . . . . S . S | . . . S . . . . . | . . . . . . . . N |
| iPS:43_6544 | 21-225_224H5 | VK4|B3/J K1 | . . . . . . . . . . . . . . . . | . . . . . F . . T | . . . . . . I . L | . . . . . . . . . | . . . . . . . . . | . . . . . . . . N | . . . . . . . . . | . L . F . . . . . | . . . . . . . . . |
| iPS:43_6550 | 21-225_224D8 | VK4|B3/J K1 | . . . . . . . . . . A . . . . . | . . . . . . N . . | . . . . . . . . | . . . . . . . . . | . S . . . . . . K | . . . . . . . . . | . . . . . . . . . | . . . F . . . . . | . . . . . . . . . |
| iPS:43_6574 | 21-225_225F5 | VK4|B3/J K1 | . . . . . . . . . . . . . . . . | . . . . . Y . . . | . . . . . . . . | . . . . . . . N . | . . . . . . . . . | . . . . . . . . . | . . . . . . . . F | . . . T . . . S . P | . . . N . . . . . |
| iPS:43_6586 | 21-225_225F11 | VK4|B3/J K1 | . . . . . . . . . . . . . . . . | . . . . . Y . . . | . . . . . . . I | . . . . . . . . . | . . . . . . . . . | . . . . . . . . . | . . . . . . . . P | . . . T . . . . . P | . . . . . . . . . |
| iPS:43_6600 | 21-225_226F6 | VK4|B3/J K1 | . . . . . . . . . . . . . . . . | . . . . . Y . . . | . . . . . . . I | . . . . . . . R . | . . . . . . . . . | . . . . . . . . . | . . . . . . . . P | . . . . . . . P . | . . . . . . . . . |

Figure 52 (Continued)

| | Germline | K_FR1 | K_CDR1 | K_FR2 | K_CDR2 | K_FR3 | K_CDR3 | K_FR4 |
|---|---|---|---|---|---|---|---|---|
| iPS:43 6616 | 21-225_226D11 | VK4|B3|J K1 | ........... | ....N..H. .SN...V | ......... | ......... | ..........R............. | ....K. | ........ |
| iPS:43 6622 | 21-225_226A12 | VK4|B3|J K1 | ........... | ....N..... .....T.F. | ......... | ....K. | ......................... | ....... | ........ |
| iPS:43 6638 | 21-225_227C7 | VK4|B3|J K1 | ........... | R....I..SD ....N..... | ...N..... | ......... | ......................... | ......S.P. | ........ |
| iPS:43 7356 | 21-225_74B1 | VK4|B3|J K1 | .....F..... | ........HR ......... | ......... | ......... | ..........F.............. | ......S.P. | ........ |
| iPS:43 7361 | 21-225_74C1 | VK4|B3|J K1 | ...C...P. ......S. | ........Y. ......... | ......... | ......... | .........................Y | ........P. | ........ |
| iPS:43 7379 | 21-225_74H2 | VK4|B3|J K1 | ........... | ........I.H ........H. | ........H. | ......... | ......................... | ........ | ........ |
| iPS:44 6094 | 21-225_77E1 | VK4|B3|J K1 | ........... | ....T..H. .....Y..... | ......V.. | ......... | S.......H................. | ..H.L... | ........ |
| iPS:45 1116 | 21-225_164A4 | VK4|B3|J K1 | .....Y..R. ......K. | ........T. ......... | ........F. | ........T. | ............C.............. | ....F... | ......H. |
| iPS:45 1124 | 21-225_74F6 | VK4|B3|J K1 | ........... | ......NI.S ........T. | ......I.. | ........T. | ............V.............. | ....F... | ......Q. |
| iPS:45 1127 | 21-225_164A7 | VK4|B3|J K1 | .....C..... | ........H. ......... | ......H. | ......... | S........A...Y............ | ........V.L | ........ |
| iPS:45 1129 | 21-225_94D2 | VK4|B3|J K1 | ........... | ........H. ......... | ......... | ......... | S.....G..H................ | ..H...L.L. | ........ |
| iPS:45 1133 | 21-225_95H4 | VK4|B3|J K1 | .....C..... | ........F. .H.NY.T | ..HN..... | ......... | ..........A............... | ..H.....P. | ........ |
| iPS:39 2786 | 21-225_24E1 | VK4|B3|J K1 | ........... | ........N..T | R.N..... | ......... | ......................... | ....F... | ........ |
| iPS:39 2886 | 21-225_23A12 | VK4|B3|J K1 | ........... | ........Y. ......... | ......... | ......... | ......................... | ......... | ........ |
| iPS:39 2928 | 21-225_25A4 | VK4|B3|J K1 | .....F..... | ........N. .H.NY.T | ..H..L. | ......S. | ..........E.............. | ......... | ........ |
| iPS:39 2960 | 21-225_29E6 | VK4|B3|J K1 | .....F..... | ........Y. ......... | ......... | ......... | ..........E.............. | ....D.... | ........ |
| iPS:39 2992 | 21-225_26C4 | VK4|B3|J K1 | ........... | ........R ......... | ........H | ......... | ......................... | ......... | ........ |
| iPS:39 3368 | 21-225_29H8 | VK4|B3|J K1 | ........... | R....TI.H. .....Y..... | ......... | ......... | ......................N. | ......L.L. | ........ |
| iPS:39 3942 | 21-225_11E5 | VK4|B3|J K1 | .....L..... | ........N..T ........ | ......... | ......... | ......................... | ....C....P. | ........ |
| iPS:39 8506 | 21-225_23G12 | VK4|B3|J K1 | ........... | ........N ....I.F. | ..R..... | ......... | ......................F. | ....S.....P. | ......F. |

| ID | Chain | | | | | | | |
|---|---|---|---|---|---|---|---|---|
| iPS:43 4335 | 21-225_63C10 | VK1|O12/JK4 | ....T.... | .......F.. | ......... | ......... | T........ | ......... |
| iPS:43 4341 | 21-225_64F7 | VK1|O12/JK4 | ......... | ....H..... | ......S.. | ......... | ...P..... | ...L..... |
| iPS:43 5295 | 21-225_146H1 | VK1|O12/JK4 | ......... | ...N.K.... | ...F..G.. | ......... | ..N...ISF | ......... |
| iPS:43 5307 | 21-225_146E9 | VK1|O12/JK4 | ......... | ...K...... | ...V..T.. | ....A.... | ...--..... | ......... |
| iPS:43 5347 | 21-225_148C4 | VK1|O12/JK4 | ......... | ...D...... | ...L..T.. | ......... | ...-.STP. | ......... |
| iPS:43 5355 | 21-225_148H9 | VK1|O12/JK4 | ......... | ...D...... | ...V..T.. | ...F..... | ...-.STP. | ...E..... |
| iPS:43 5371 | 21-225_149A3 | VK1|O12/JK4 | ......... | ...N...... | ...V..... | ...I..... | ...-.STP. | ......... |
| iPS:43 5415 | 21-225_150C11 | VK1|O12/JK4 | ......... | ...N...... | ...V..T.. | ......... | ...-.STP. | ......... |
| iPS:43 5419 | 21-225_150C12 | VK1|O12/JK4 | ......... | ........... | ..VM..T.. | ......... | ...-.STP. | ......... |
| iPS:43 5425 | 21-225_151B12 | VK1|O12/JK4 | ......... | ........... | ...V..... | ....N..... | ...-.SIY. | ....S.... |
| iPS:43 5431 | 21-225_152D2 | VK1|O12/JK4 | ......... | ...D...... | ...V..T.. | ......... | ...F-.STP. | ......... |
| iPS:43 5439 | 21-225_152G4 | VK1|O12/JK4 | ......... | ...D...... | ...V..T.. | ......... | ...-.STP. | ......... |
| iPS:43 5455 | 21-225_152B11 | VK1|O12/JK4 | ....L.... | ..NF...... | ...V..T..E | .......E. | ...-.STP. | ....R.... |
| iPS:43 5487 | 21-225_155C4 | VK1|O12/JK4 | ......... | ...D...... | ...L..T.. | ...F..... | ...-.STP. | ......... |
| iPS:43 5503 | 21-225_156E4 | VK1|O12/JK4 | ......... | ...D...... | ...V..T.. | ...F..... | ...-.STP. | ......... |
| | | | | | ...V,F..T.. | ...F..... | ...-.STP. | ....R.... |
| | | | | | ...V....T.. | ......... | ...-.SAP. | ......... |

Figure 52 (Continued)

| | | | | | | | | | | | | |
|---|---|---|---|---|---|---|---|---|---|---|---|---|
| iPS:43 5563 | 21-225_159H2 | VK1[O12]/JK4 | ....L..... | .......... | ....K..... | ....E..... | ..T.N....G | .....T.... | .......V.. | .......... | ....L.V... | .......... |
| iPS:43 6110 | 21-225_196F4 | VK1[O12]/JK4 | .F..I..... | .......... | .....R.H.. | .......... | .......... | .......... | .......... | ........G. | .......S.. | .......... |
| iPS:43 6244 | 21-225_201H10 | VK1[O12]/JK4 | .......... | ....P..... | ....HN.N.. | ....S..... | .......... | .F........ | .......... | .......... | ....F..... | ....MR.... |
| iPS:43 6262 | 21-225_203E3 | VK1[O12]/JK4 | .......... | ....P....R | ....HN.N.. | ....S..... | .......... | .F........ | .......... | .......... | ....F..... | ....MR.... |
| iPS:43 6276 | 21-225_204H4 | VK1[O12]/JK4 | ....L..... | ....P..... | ....HN.N.. | .......... | .......... | .F........ | .......... | .......... | ....F..... | .......... |
| iPS:43 6280 | 21-225_204D6 | VK1[O12]/JK4 | .S........ | .......... | ....R.VH.. | ....V..... | ........G. | .......... | .......V.. | .......... | ....S..... | ....Q..... |
| iPS:43 6312 | 21-225_206A4 | VK1[O12]/JK4 | ....L..... | ....P..... | ....HN.N.. | ....S..... | ........R. | .F........ | .......... | .......... | ....F..... | ....MR.... |
| iPS:43 6316 | 21-225_206A5 | VK1[O12]/JK4 | .F........ | ....P....R | ....HN.N.. | ....S....C | .......... | .F........ | .......... | .......... | ....F..... | .......... |
| iPS:43 6338 | 21-225_208E8 | VK1[O12]/JK4 | .......... | ....P..... | ....HN.N.. | ....S....C | .......... | .F........ | .......... | .......... | ....F..... | ....MR.... |
| iPS:43 6344 | 21-225_208B11 | VK1[O12]/JK4 | .F........ | ....P....R | ....HN.N.. | ....S..... | .......... | .F........ | .......... | .......... | ....F..... | .......... |
| iPS:43 6358 | 21-225_210D11 | VK1[O12]/JK4 | .......... | ....P..... | ....HN.N.. | .......... | .......... | .F........ | .......... | .......... | ....F..... | ....MR.... |
| iPS:43 7282 | 21-225_207C9 | VK1[O12]/JK4 | .N........ | .......... | ....RF.... | ....H..... | .......... | .F..A.V... | .......... | .......... | ....T..... | .......... |
| iPS:39 2636 | 21-225_17A6 | VK1[O12]/JK4 | .......... | .......... | .N........ | ....H..... | .......... | .......... | .......... | ....HT.... | ....S..... | .......... |
| iPS:39 2648 | 21-225_16D11 | VK1[O12]/JK4 | .......... | .......... | .N....T... | ....H..... | .......... | .......... | .......... | ....H..... | .......... | .......... |
| iPS:39 2664 | 21-225_20F6 | VK1[O12]/JK4 | .......... | .......... | .....I..T. | ....V..H.. | ....T..... | .......... | .......... | ....T..... | .......... | .......... |
| iPS:39 2738 | 21-225_18G4 | VK1[O12]/JK4 | .H........ | .......... | .....I.... | ....V..... | .F........ | .......G.. | .......... | ....T..... | ....P..... | .......... |
| iPS:39 2798 | 21-225_22C7 | VK1[O12]/JK4 | .......... | .......... | ....N.I... | ....E..H.. | .H........ | .......... | .......... | ....T..... | ....P..... | .......... |
| iPS:39 2922 | 21-225_30G4 | VK1[O12]/JK4 | .......... | ....P..... | ....N.F... | ....H..... | .T......G. | .I.M...... | .......... | ....L..... | .......S.. | .......... |
| iPS:39 3002 | 21-225_30G1 | VK1[O12]/JK4 | T......... | .......... | .......... | ....D..... | .......H.. | .......... | .......... | .......... | .......... | .......... |
| iPS:39 3042 | 21-225_31F1 | VK1[O12]/JK4 | .......... | .......... | .....R.... | .......... | .......S.. | .......... | .......... | ....I..... | ....P.Y... | .......... |
| iPS:39 3066 | 21-225_34D3 | VK1[O12]/JK4 | .......... | .......... | ....N.Y... | ....D..... | .......H.. | .......... | .......F.. | .......... | .......... | ....T....R |

Figure 52 (Continued)

| | | K_FR1 | K_CDR1 | K_FR2 | K_CDR2 | K_FR3 | | | K_CDR3 | K_FR4 |
|---|---|---|---|---|---|---|---|---|---|---|
| | Germline | | | | | | | | | |
| iPS:39 3082 | 21-225_34C11 | VK1|O12/ JK4 | T........ | ......N.R.. | ......D..Q.. | ....E.G...T. | | ......F.... | ...TC....... | ........... |
| iPS:39 3092 | 21-225_33C12 | VK1|O12/ JK4 | T........ | ......NF... | ............ | ............G | | ....K....... | ............ | ........... |
| iPS:39 3100 | 21-225_36B8 | VK1|O12/ JK4 | .T....... | .........I. | ............ | ....V....... | | .N.......... | ............ | .......M... |
| iPS:39 3108 | 21-225_34G11 | VK1|O12/ JK4 | ......... | ....N.N.... | ............ | ............ | | ............ | ...Y........ | ........... |
| iPS:39 3122 | 21-225_33B2 | VK1|O12/ JK4 | T...K.... | .....R..... | ............ | ....G....... | | ..T......... | ...I........ | ........... |
| iPS:39 3134 | 21-225_34C2 | VK1|O12/ JK4 | .F....... | ......R.I.. | ...F........ | ....V....... | | .........Y.. | ...Y........ | ........... |
| iPS:39 3136 | 21-225_34D8 | VK1|O12/ JK4 | TF....... | ....I.I.I.. | ............ | ....V....... | | ............ | ............ | .......M... |
| iPS:39 3840 | 21-225_3F8 | VK1|O12/ JK4 | .F....... | .........L. | ....R....R.. | ....RT...T.. | | ......V..... | ...T........ | ....R....... |
| | | | | | ...QV..H.... | | | | | |
| iPS:39 3844 | 21-225_3G7 | VK1|O12/ JK4 | ........ | ......R..... | ..GR..R..... | ..V....S.... | | .......A.... | ...P.F...... | ....A...... |
| | | | | | ......M..... | | | | | .D......... |
| iPS:39 3852 | 21-225_12A10 | VK1|O12/ JK4 | V........ | ...........Y | ...V..H..... | ....R....... | | .N...G...... | ...P........ | ........... |
| iPS:39 3900 | 21-225_10E12 | VK1|O12/ JK4 | .A....... | ....N..Y.... | ..E....R.... | ....R....... | | .....G...... | ...N........ | .......E... |
| iPS:39 3920 | 21-225_1H12 | VK1|O12/ JK4 | ......... | ....N..Y.... | ..E....R.... | ...T..N.T... | | ............ | ...PH....... | ........... |
| | | | | | ..R......... | | | | | |
| iPS:39 3926 | 21-225_4G4 | VK1|O12/ JK4 | ......A.. | .....T.I.... | ........H... | ....T....... | | .........D.. | ...T........ | ........... |
| iPS:39 3930 | 21-225_7E11 | VK1|O12/ JK4 | .....A... | ....N..I.... | ...F........ | ....T....... | | ............ | ...T........ | ........... |
| iPS:39 3932 | 21-225_10F5 | VK1|O12/ JK4 | ......... | ....N..Y.... | ..E....R.... | ....T....... | | .........D.. | ...P........ | ........... |
| | | | | | ..R......... | | | | | |
| iPS:39 3964 | 21-225_6G1 | VK1|O12/ JK4 | ......... | ....N..I.... | ...V........ | ....T....... | | ......I..... | ...P........ | ........... |
| | | | | | ..T......... | | | | | |
| iPS:39 4012 | 21-225_15A3 | VK1|O12/ JK4 | ......... | .........I.. | ..L......... | ....T....... | | .....G...... | ...P........ | ........... |
| | | | | | ..F......... | | | | | |
| iPS:39 4016 | 21-225_13D4 | VK1|O12/ JK4 | L........ | .........F.. | .........C.. | ....T....... | | ............ | ...T........ | ........... |
| iPS:39 4083 | 21-225_16E6 | VK1|O12/ JK4 | ......... | .........I.. | ...F........ | ....T....... | | ............ | ...L........ | ........... |
| | | | | | | ..T......... | | | | |
| iPS:39 8480 | 21-225_17G4 | VK1|O12/ JK4 | .A....... | .T...N...... | ............ | ....V....... | | ............ | ...NF....... | ....I...... |
| | | | | | | ..F?........ | | | | |
| iPS:39 8486 | 21-225_19A1 | VK1|O12/ JK4 | ......... | ....HT.T.... | ...F........ | ...T.N...... | | .F......I... | ...N.F...... | ........... |
| | | | K_FR1 | K_CDR1 | K_FR2 | K_CDR2 | K_FR3 | | | K_CDR3 | K_FR4 |

Figure 52 (Continued)

| VK2fA18/JK4 | | DIVMTQTPLSL SVTPGQPASIC | RSS QSLLHSD GNTYLN | WYLQKPGQ SPQLLIY | LGSNRAS | GVPDRFSGS GSGTDFTL | KISRVEAEDV GVYYC | MQAIH ------LPT | FGGGTK VEIK |
|---|---|---|---|---|---|---|---|---|---|
| iPS:45 1139 | 21-225_71A6 | VK2|A18/JK4 | | ..R. | | | .S. | ..SKQ | .F. |
| iPS:43 3937 | 21-225_44B10 | VK2|A18/JK4 | H | ..H.... | .P. | ..N. | | ..S.. | .F. |
| iPS:43 3979 | 21-225_46B9 | VK2|A18/JK4 | | E.R.... | .P. | .I.H. | ..M.. | .HS.Q | ..Q |
| iPS:43 4201 | 21-225_59A12 | VK2|A18/JK4 | | E....Q.G | .P. | ..Y. | | .STQ. | |
| iPS:43 4205 | 21-225_60G2 | VK2|A18/JK4 | ..S. | E...... | .V. | ..Y. | ..V.. | ..S.Q | .Y. |
| iPS:43 4223 | 21-225_60C12 | VK2|A18/JK4 | | E...... | .P. | ..N. | | ..S.K | .Y. |
| iPS:43 4233 | 21-225_61B3 | VK2|A18/JK4 | | ...... | .P.F. | ..N.I. | ..I.. | ..S.Q | |
| iPS:43 4303 | 21-225_58H11 | VK2|A18/JK4 | | E...... | .V. | ..Y. | | ..S.Q | .Y. |
| iPS:43 5349 | 21-225_148F5 | VK2|A18/JK4 | | E...... | .P. | ..Y.V. | ..F.. | ..S.Q | |
| iPS:43 5359 | 21-225_148H10 | VK2|A18/JK4 | | E...... | .P. | ..Y.V. | | ..S.Q | |
| iPS:43 5417 | 21-225_150D11 | VK2|A18/JK4 | F | ...H.N | .P. | ..Y. | | ..Q. | |
| iPS:43 5469 | 21-225_153G9 | VK2|A18/JK4 | | E..F. | .P.F. | ..N. | .D. | ..N.K | .Y. |
| iPS:43 5733 | 21-225_173C11 | VK2|A18/JK4 | | ...... | .P. | ..H. | | ..S.- | |
| iPS:43 5785 | 21-225_179C2 | VK2|A18/JK4 | | ...... | .P. | | .L.... | ..S.-- ..QL. | |
| iPS:39 2618 | 21-225_16F10 | VK2|A18/JK4 | | ...... | .P. | ..Y. | .E...A. ..V. | F.S.Q ..QV. | |
| iPS:39 2860 | 21-225_22H8 | VK2|A18/JK4 | I | ...... | .P.H | | | | |
| iPS:39 2888 | 21-225_25A2 | VK2|A18/JK4 | N | ...... | .P. | ..N. | .A.L. ..i.. | ..S.Q | .S. |
| iPS:39 2938 | 21-225_29H4 | VK2|A18/JK4 | G | ...... | .P.G | .I.N. | | .STQ. | .F. |
| iPS:39 2994 | 21-225_26G11 | VK2|A18/JK4 | | E...T..G | .P. | ..H. | ..I.. | ..S.Q | .H.F. |
| | | | | | .P.H. | ..N. | | ..S.K | ..R .N. |

Figure 52 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:39 3012 | 21-225_26G7 | VK2|A18/ JK4 | ...L....... | ........E | ........P.F.. | ......H.L | .......... | ..S.Q...... | ........ |
| iPS:39 3144 | 21-225_34D2 | VK2|A18/ JK4 | .......... | .......... | ........P... | ......N... | .......... | ..SK- | ....R... |
| | | Germline | DIQMTQSPSS ASVSDRVTITC | RAS QSIS NYLA | WYQQKPGK APKLLIY | AASSLQS | GVPSRFSGSG SGTDFTLTIS SLQPEDFAT YYC | QQYNS ----QLPP LT | FGGGTKV EIK |
| | VK1|L1|JK3 | | | | | | | |
| iPS:45 1143 | 21-225_66H11 | VK1|L1/JK3 | ...F...... | .......... | .......... | .G........ | .......K.. | ...SC...... | ...H.... |
| iPS:46 8814 | 21-225_223D11 | VK1|L1/JK3 | .......... | .......... | .......... | .FN.H..... | .N.N...... | ...SG....F. | ....T... |
| iPS:43 3901 | 21-225_43A4 | VK1|L1/JK3 | .......... | .......N.. | .......... | .......T.. | .......K.. | ....Y...... | ........ |
| iPS:43 3961 | 21-225_45D9 | VK1|L1/JK3 | .......... | .......N.. | .......N.. | .......... | .A........ | .H.Y....... | ....R... |
| iPS:43 4059 | 21-225_51C5 | VK1|L1/JK3 | .......... | .......... | .......E.. | .......R.. | ..Q...I... | ....Y....... | ........ |
| iPS:43 4085 | 21-225_52E3 | VK1|L1/JK3 | .......... | .......... | .......N.. | .......... | .......K.. | .......... F | ........ |
| iPS:43 4115 | 21-225_53E4 | VK1|L1/JK3 | .......... | ....V..... | .......S.. | .......... | .......... | ....H...... | ....R... |
| iPS:43 4213 | 21-225_60A4 | VK1|L1/JK3 | .......... | .......... | ...V...... | .......... | .......K..S | ....K...... | ........ |
| iPS:43 4215 | 21-225_60F7 | VK1|L1/JK3 | ...S...... | ...V.K...V | .......... | .......... | .......T.. | .L.FH....... | ...M... |
| iPS:43 4261 | 21-225_56F7 | VK1|L1/JK3 | ...L...... | ...T...... | .......T.T | .......G.. | .......K.. | ....H....F.K | ....R..T |
| iPS:43 4331 | 21-225_63H8 | VK1|L1/JK3 | .......... | .......... | ...H...... | .......... | ..Q.A....Q | PL.K........ | ....R... |
| iPS:43 4361 | 21-225_65D5 | VK1|L1/JK3 | .......... | ...D.N.... | ...R...... | .......... | .......K..N | ....H........ | ........ |
| iPS:43 4405 | 21-225_68E6 | VK1|L1/JK3 | .......... | ....Y..... | ...R.V..... | .......RV. | .......K.. | ....D......L | ........ |
| iPS:43 5259 | 21-225_96C6 | VK1|L1/JK3 | .......... | ...K...... | .......... | .......... | .......N.. | H..D....... | ........ |
| iPS:43 5351 | 21-225_148B6 | VK1|L1/JK3 | ...S...... | ...V...... | .......F.. | .......... | .......K... I | ....H.....F. | ....F... |
| iPS:43 5461 | 21-225_153A1 | VK1|L1/JK3 | .......... | ...D...... | ...R...... | .......... | .......... | ....H....... | ....F... |
| iPS:43 5509 | 21-225_157H1 | VK1|L1/JK3 | .......... | ....V...... | ...R...... | ......R... | .......K.. | ...H........ | ........ |

Figure 52 (Continued)

| ID | Germline | | | | | | | | | |
|---|---|---|---|---|---|---|---|---|---|---|
| iPS:43_5515 | 21-225_157E4 | VK1|L1/J K3 | . . . . . . . . . . | . . . . . . . . . . | . . . . . . . . . . | . . . . . . . . . . | Q . . N . . . . . | . . . . . . . . . . | . H . . . . . . . . | . . . . . . . . . . |
| iPS:43_5523 | 21-225_157G5 | VK1|L1/J K3 | . . . . . . F . . | . . . . N . . . | . . . . . . . . | . . . . . R . | Q . . . . . . . | . . . . . . . . | . . . . . . . . | . . . . . . . . |
| iPS:43_5535 | 21-225_157H10 | VK1|L1/J K3 | . . . . . . . . | . . . . T . . . | . E . . . . . . | . . . . . . . . | . K . . . . . . | . . . . . . . . | . H . . . . . . | . . . . . . . . |
| iPS:43_5559 | 21-225_158H12 | VK1|L1/J K3 | . . . . . . . . | . . . . N . . . | . . . . . N . . | . . . . . . . . | . K . . . . . . | . . . . . . . . | . H . . . . . . | . . . . . . . . |
| iPS:43_5575 | 21-225_159H11 | VK1|L1/J K3 | . . . . . . . . | . K . V . . . . | . . . . . S . . | . . . . . . . . | . K . . . S . . | . . . . . . . . | . . . . . . . . | . . . . . . . . |
| iPS:43_5579 | 21-225_160G1 | VK1|L1/J K3 | . . . . . . . . | . D . N . . . . | . T . . . . . . | . . S . . . . . | . K . . . . . . | . . . . . . . . | . H . . . . . . | . R . . . . . . |
| iPS:43_5585 | 21-225_160G3 | VK1|L1/J K3 | . . . . . . . . | . D . N . . . . | . T . . . R . . | . . S . . . . . | . K . . . . . . | . . . . . . . . | . H . . . . . . | . . . . . . . . |
| iPS:43_5635 | 21-225_163F1 | VK1|L1/J K3 | . . . . . . . . | . . . D . . . . | . . . . . . . . | . . . . . . . . | . K . . . A . . | . . . . . . . . | . . . . . . . . | . AQ . . . . . . |
| iPS:43_5659 | 21-225_167D12 | VK1|L1/J K3 | . . . . . . . . | . . . N . . . . | . E . . . . . . | . . . . . . . . | . K . . . . F . | . . . . . . . . | . H . . . . . . | . . . . . . . . |
| iPS:43_5679 | 21-225_169D10 | VK1|L1/J K3 | . . . . . . . . | . . . D . . . . | . . . . . . . . | . . . . . . . . | . K . . . . . . | . . . . . . . . | . . . . . . . . | . . . . . . . . |
| iPS:43_5685 | 21-225_170E1 | VK1|L1/J K3 | . . . E . . . . | . . . . . . . . | . . . . . . . . | . . G . . . . . | . . . . . . . . | . . . . . . . . | . Y . . . . . . | . . . . . . . . |
| iPS:43_5747 | 21-225_175C4 | VK1|L1/J K3 | . . . . E . . . | . . G . . . . . | . I . . . . T . | . . . . . . . . | . F . K . . . . | . . . . . . . . | . . . . . . . . | . . . . . . . . |
| iPS:43_5765 | 21-225_177D3 | VK1|L1/J K3 | . . . . . . . . | . . T . . . . . | . . . . . . . . | . . . . . . . . | . S . . . . F . | . . . . . . . . | . R . DT . . . . | . . . . . . . . |
| iPS:43_5797 | 21-225_181G2 | VK1|L1/J K3 | . . . . . . . . | . . K . . . . . | . . . . . . . . | . . . . . . . . | . K . . . D . . | . . . . . . . . | . . . . . . . . | . . . . . . . . |
| iPS:43_5835 | 21-225_190F12 | VK1|L1/J K3 | . . . . . . . . | . . G . . . . . | . . . . . . . . | . . . . . . . . | . K . . . . . . | . . . . . . . . | . SN . . . . . . | . . . . . . . . |
| iPS:43_5861 | 21-225_190A5 | VK1|L1/J K3 | . . . . . . . . | . . H . . . . . | . . . . . H . . | . V . . . . . . | . K . . . E . . | V . . . . . . . | . IN . . . . . . | . . . . . . . . |
| iPS:43_5869 | 21-225_190B1 | VK1|L1/J K3 | . . . . . . . . | . . R . . . . . | . . . . . . . . | . . . . . E . . | . K . . . G . . | . . . . . . . . | . G . . . . . . | . . . . . . . . |
| iPS:43_5877 | 21-225_184E7 | VK1|L1/J K3 | . . . . E . . R | . . . . . . . . | . I . . . . T . | . . . . . . . . | . S . . . . F . | . . . . . . . . | . G . . . . . . | . R . . . . . . |
| iPS:43_5883 | 21-225_185A1 | VK1|L1/J K3 | . . . . H . . . | . . . . . . . . | . . T . . . S . | . . V . . . . . | . I . . V . R . | . . . . . . . . | . R . H . . . . | . H . . . . . . |
| iPS:43_5885 | 21-225_185E10 | VK1|L1/J K3 | . . . . E . . R | . . . . . . . . | . I . . . . T . | . . . . . . . . | . S . . . . F . | . . . . . . . . | . G . . . . . . | . . . . . . . . |
| iPS:43_5891 | 21-225_188H5 | VK1|L1/J K3 | . . . . E . . . | . . . . . . . . | . L . . . . T . | . . . . . . . . | . S . . . . F . | . . . . . . . . | . . . . . . . . | . . . . . . . . |

Figure 52 (Continued)

| | | | | | | | | | |
|---|---|---|---|---|---|---|---|---|---|
| iPS:43 5897 | 21-225_188B9 | VK1|L1/J K3 | . . . . . . . . | . . . . . . . . | . . . . . . . . | . . . . . . . . | . . S . . . . F | . . . . . . . . | . . . . . . . . |
| iPS:43 5937 | 21-225_190H9 | VK1|L1/J K3 | . . . . . E . . | . . . . . . . . | . . . G . . . . | . L . . . . . . | . . K . . . . . | . . . . . D . . | . . . . . . . . |
| iPS:43 5961 | 21-225_192A2 | VK1|L1/J K3 | . . . . . . . . | . . . . . . . . | . N . . . N . . | . . . . . . . . | . . K . . . . . | . R . D T . . . | . . . . . . . . |
| iPS:43 5977 | 21-225_192E4 | VK1|L1/J K3 | . . . . . . . . | . . . . . . . . | . . . G . . . . | . . . . . . . . | . . K . . . . . | . R . D T . . . | . . . . V . . . |
| iPS:43 6001 | 21-225_192C10 | VK1|L1/J K3 | . . . . . . . . | . . . . . . . . | . . K . . . . . | . . . . V . . . | . . K . . . . . | . R . D T . . . | . . . . . . . . |
| iPS:43 6039 | 21-225_193F8 | VK1|L1/J K3 | . . . . . . L . | . . . . . . . . | . . . V . . . . | . . . . . R . . | . . K . . . A . | . R . D T . . . | . . . . . . . . |
| iPS:43 6078 | 21-225_194H12 | VK1|L1/J K3 | . . . . . . . . | . . . . . . R . | . . . G . . . . | . L . . . . . . | . . K . . . D . | . R . D T . . . | . . . . . . . . |
| iPS:43 6140 | 21-225_197G3 | VK1|L1/J K3 | . . . . . . . . | . . . . . . . . | . . . G . . . . | . . . . . . . . | . S K . R . . . | . . S N . . . . | . . . . V . . . |
| iPS:43 6167 | 21-225_197E11 | VK1|L1/J K3 | . . . . . . . . | . . . . . . . . | . . K . S . . . | . . . . . V . . | . . K . . R D . G | . R . D T . . . | . . . . . . . . |
| iPS:43 6370 | 21-225_211A6 | VK1|L1/J K3 | . . . . . . . . | . . . . S . . . | . . . G . . . . | . . . . . . L . | . . K . . . . . | . K . D T . . . | . . . . . I . . |
| iPS:43 6392 | 21-225_213B3 | VK1|L1/J K3 | . . . . . . . . | . . . . . . . . | . . . G . . . . | . . . . . V L . | . . K . . . . . | . K . D T . . . | . . . . . . . . |
| iPS:43 6404 | 21-225_214C3 | VK1|L1/J K3 | . . . . . . . . | . . . . . . . . | . . N . . . . . | . . . . E . . . | . . K . . T . . | . . M T . . . . | . . . . . . . . |
| iPS:43 6406 | 21-225_214E4 | VK1|L1/J K3 | . . . . . . . . | . . . . . . . . | . Y . . . . . . | V . . . . . R . | . . K . . . . . | . . L T . . . . | . . . . . L . . |
| iPS:43 7216 | 21-225_51D5 | VK1|L1/J K3 | . . . . . . . . | . . . . . . . . | . . . . . N . . | . Q . M S . . . | . I . Q . . . . | . . . Y . . . . | . . . . . . . . |
| iPS:43 7224 | 21-225_56H1 | VK1|L1/J K3 | . . . . . . . . | . . . . . . . . | . H . . . . . . | . . . . . . G . | . . K . . . F . | . . Q N . . . . | . . . . . . . . |
| iPS:39 2620 | 21-225_17H5 | VK1|L1/J K3 | . . . . . . . . | . . . . . . . . | . . . . . N . . | . . . . . . . . | . . K . . . . . | . . H . . . . . | . . . . . . . . |
| iPS:39 2692 | 21-225_18G10 | VK1|L1/J K3 | . . . . . . . . | . . . . . . . . | . . . D . . . . | V . . . . . . . | . . K . G . F . | L . . . . . . . | . . . . . . . . |
| iPS:39 2708 | 21-225_18D11 | VK1|L1/J K3 | . . . . . F . . | . . . . F . . . | . . Y . . . . . | V . . . . . . . | . . K . . . F . | . . T . . . . . | . . . . . T . . |
| iPS:39 2714 | 21-225_16G12 | VK1|L1/J K3 | . . . . . . . . | . . . . . . . . | . . Y . . D . . | . . . . . . . . | . . K R . . . S | . . H . . . F . | . . . . . . . . |
| iPS:39 2746 | 21-225_20H7 | VK1|L1/J K3 | . . . . . . . . | . T . . . . . . | . . . . . N . . | . R . . . . . . | . . K . N . . . | . . . Y . . . . | M . F . . . . . |
| iPS:39 2782 | 21-225_22B12 | VK1|L1/J K3 | . . . . . . . . | . . . . . . . . | . . . . V . . . | . H . . E . G R | N . K . . . L . | . . H . . . . . | . . . F . . . . |

Figure 52 (Continued)

| ID | Name | Framework | | | | | | | |
|---|---|---|---|---|---|---|---|---|---|
| iPS:39 2784 | 21-225_23C7 | VK1|L1/J K3 | . . . . . . . . . | . . . . . . . . . | . . . . . . . . . | . . . . . . . . . | K . . . . . . . . | . . . . . . . . . | . . . . . . . . . |
| iPS:39 2802 | 21-225_23E7 | VK1|L1/J K3 | . . . . . . . . . | . . . . . . G . . | . . . . . . I . . | . . . . . . . . . | . K . . . . . . . | . . . . . . . F Y | . . . . . . . . N |
| iPS:39 2826 | 21-225_20B9 | VK1|L1/J K3 | . . . . . . . . . | . . . . . . . . . | . . . . . . . . . | . . . . . . . V . | . K . . . . . . . | . . . . . . . . T | . . . . . . . . . |
| iPS:39 2840 | 21-225_23G1 | VK1|L1/J K3 | . . . . . . . . . | . . . . . . . . . | . . . . . . . S . | . . . . . . . . . | . . . . . . . Q . | . . . . . . . . . | . . . . . . . . . |
| iPS:39 2842 | 21-225_23G8 | VK1|L1/J K3 | . . . . . . . . . | . . . . . . R . . | . . . . . . . . . | . . . . . . . . . | . . . . . . . F . | . . . . . . . . . | . . . . . . . . . |
| iPS:39 2880 | 21-225_20H9 | VK1|L1/J K3 | . . . . . . . . . | . . . . . . . . . | . . . . . . . S . | . . . . . . . . . | . N . . . . . . . | . . . . . . . . . | . . . . . . . . . |
| iPS:39 2892 | 21-225_20C11 | VK1|L1/J K3 | . . . . . . . . . | . . . . . . D . . | . . . . . . . . . | . . . . . . . . . | . K . R . . . . . | . . . . . . . H . | . . . . . . . . . |
| iPS:39 2950 | 21-225_25C10 | VK1|L1/J K3 | . . . . . . . . . | . . . . . . . . . | . . . . . . . . . | . . . . . . . . . | F . K . . . . . . | . . . . . . . F . | . . . . . . . . . |
| iPS:39 2952 | 21-225_26G1 | VK1|L1/J K3 | . . . . . . . . . | . . . . . . D . . | . . . . . . . . R | . . . . . . . . . | . N . . . . . N . | . . . . . . . H . | . . . . . . . . . |
| iPS:39 2962 | 21-225_30A1 | VK1|L1/J K3 | . . . . . . . . . | . . . . . . . . . | . . . . . . . . T | . . . . . . . . . | . K . . . . . . . | . . . . . . . H . | . . . . . . . . . |
| iPS:39 2976 | 21-225_27H12 | VK1|L1/J K3 | . . . . . F H . . | . . . . . . A . . | . . . . . . S . . | . . . . . . G . . | . K . . . . . . . | . . . . . . . Y . | . . . . . . . . . |
| iPS:39 3090 | 21-225_33A5 | VK1|L1/J K3 | . . . . . . . . . | . . . . . . . . . | . . . . . . . . . | . . . . . . G . . | . K . . . . . . . | . . . . . . . . . | . . . . . . N . N |
| iPS:39 3120 | 21-225_35H8 | VK1|L1/J K3 | . . . . . F . . . | . . . . . . D . . | . . . . . . F . . | . . . . . . . G . | . K . . . . . F . | . . . . . . . . . | . . . . . . . . . |
| iPS:39 3836 | 21-225_15A2 | VK1|L1/J K3 | . . . . . . . . . | . . . . . . H V . | . . . . . . F . . | . . . . . . . . . | F P . . . . . N . | . . . . . . . Y . | . . . . . . E . . |
| iPS:39 3870 | 21-225_7B1 | VK1|L1/J K3 | . . . . . A . . . | . . . . . . . . . | . . . . . . . . . | . . . . . . . . . | . Q . . . . . . . | H . . . . . . . . | . . . . . . . Q . |
| iPS:39 3894 | 21-225_5E11 | VK1|L1/J K3 | V . . . . . . . . | . . . . . . . . . | . . . . . . N . . | . . . . . . . . . | . i . . . . . . . | H . . . . . . H . | . . . . . . . V . |
| iPS:39 3896 | 21-225_2A4 | VK1|L1/J K3 | . . . . . . . . . | . . . . . . . . . | . . . . . . R . . | . . . . . . . T . | . K . N . . . . . | . . . . . . . . . | . . . . . . . F . |
| iPS:39 3914 | 21-225_16B8 | VK1|L1/J K3 | . . . . . . . . . | . . . . . . N . . | . . . . . . L . N | . . . . . . . V . | . K . . . . . . . | . . . . . . . . . | . . . . . . . . . |
| iPS:39 3968 | 21-225_5A5 | VK1|L1/J K3 | . . . . . . . . . | . . . . . . . . . | . . . . . . . . . | . . . . . . . V . | . K . . . . . . . | . . . . . . H . H | . . . . . . . V . |
| iPS:39 3992 | 21-225_14H8 | VK1|L1/J K3 | . . . . . . . . . | . . . . . Y . . . | . . . . . . . S . | . . . . . . . . . | . K . . . . . . . | . . . . . . . . . | . . . . . . . . . |
| iPS:39 4018 | 21-225_15B1 | VK1|L1/J K3 | . . . . . . . . . | . . . . . . . . . | . . . . . . . S . | . . . . . . . . . | . N . . . . . . . | . . . . . . . H . | . . . . . . . . N |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:39 4026 | 21-225_16C7 | VK1|L1/J K3 | | | | | | |
| iPS:39 4055 | 21-225_9C8 | VK1|L1/J K3 | ......Y... | ...S... | ...V... | ...K... | ...D... | ... |
| iPS:39 8482 | 21-225_17H6 | VK1|L1/J K3 | ......RD... | ...T... | ...K... | ...I... | ...H... | ...Q |
| iPS:39 8492 | 21-225_21F12 | VK1|L1/J K3 | ......R... | ...S... | ...K... | ...F... | ... | ... |
| iPS:39 8500 | 21-225_23A11 | VK1|L1/J K3 | T...D... | ...R... | ...F... | ...K... | ... | ... |
| iPS:39 8526 | 21-225_32B3 | VK1|L1/J K3 | | ... | ...R... | ... | ...T... | ...F... | ...L |
| iPS:40 2235 | 21-225_20F10 | VK1|L1/J K3 | L... | ...N... | ...R... | ... | ...F... | ...F... | ...N |
| | Germline | K_FR1 | K_CDR1 EIVLTQSPGTL SLSPGERATLSC | K_FR2 RAS QSVSS SYLA | K_CDR2 WYQQKPG QAPRLLIY GASSRAT | K_FR3 GIPDRFSGSGSG TDFTLTISRLEPEDFAVY YC | K_CDR3 QQYGS | K_FR4 SPXT FGGGTK VEIK |
| | VK3|A27|JK1 | | | | | | | |
| iPS:46 8810 | 21-225_74D5 | VK3|A27| JK1 | ...N... | ...R... | | I I I | ...E... | ... |
| iPS:46 8834 | 21-225_94G10 | VK3|A27| JK1 | ...N... | ...R... | | I I I | ...E... | ... |
| iPS:46 8838 | 21-225_80E12 | VK3|A27| JK1 | C... V. | ...N... | ...R...D. | | I I I | ...E... | ... |
| iPS:46 8820 | 21-225_76E10 | VK3|A27| JK1 | ...N... | ...R... | | I I I | ...E... | ... |
| iPS:43 3931 | 21-225_44F6 | VK3|A27| JK1 | ...G... | ...E... | | | ...E... | ... |
| iPS:43 4307 | 21-225_59B2 | VK3|A27| JK1 | W...Y... F... | ...F...S... | | | ...T... F... | ... |
| iPS:43 4471 | 21-225_75G3 | VK3|A27| JK1 | R...N.D. | | | | ...ER... F... | ... |
| iPS:43 4473 | 21-225_76D1 | VK3|A27| JK1 | ...NIY... N... | | | ...V... | ...E... | ... |
| iPS:43 4495 | 21-225_74B2 | VK3|A27| JK1 | ...NIY... | | | ...C... | ...E... | ... |
| iPS:43 4497 | 21-225_76A4 | VK3|A27| JK1 | Y...Y... | | | A... | .HSDN... | ... |
| iPS:43 4501 | 21-225_76G4 | VK3|A27| JK1 | | | | A...C... | .HSDN... | ... |
| iPS:43 4507 | 21-225_74C5 | VK3|A27| JK1 | ...N... | ...F... | | N.I ...V... | ...E... | ... |

Figure 52 (Continued)

| | | | | | | | | | | |
|---|---|---|---|---|---|---|---|---|---|---|
| iPS:43 4517 | 21-225_76A7 | VK3\|A27/ JK1 | .A...... | ...... | ....P..D.. | .....R. | ....... | ....... | ....... | ....E.. | ...... |
| iPS:43 4519 | 21-225_74C7 | VK3\|A27/ JK1 | ........ | ...... | .T...PN.D. | ....... | ....... | ....... | ....F.. | ...ER.. | ...... |
| iPS:43 4523 | 21-225_75C3 | VK3\|A27/ JK1 | ...Q.... | ...... | ......R... | ....... | ....... | ....... | ....... | ..H.D.. | ...... |
| iPS:43 4531 | 21-225_76C9 | VK3\|A27/ JK1 | ........ | ...... | ........S. | ....... | ....... | ....... | ....... | ....-.. | ..RSR. |
| iPS:43 4533 | 21-225_85F7 | VK3\|A27/ JK1 | .P...... | ...... | .....NIY.. | ....... | ....... | ....... | ....C.. | ....E.. | ...... |
| iPS:43 4547 | 21-225_74H5 | VK3\|A27/ JK1 | ........ | ...... | ......N... | ...R... | ....... | .I.I.. | ....... | ....E.. | ...... |
| iPS:43 4559 | 21-225_74D11 | VK3\|A27/ JK1 | ........ | ...... | ......N... | ....... | ....... | A...... | ....... | ..H.DN. | ...... |
| iPS:43 4561 | 21-225_77G1 | VK3\|A27/ JK1 | ........ | ...Y.. | ......Y... | ....... | ....... | A...... | ....C.. | ..H.DN. | ...... |
| iPS:43 4565 | 21-225_75B10 | VK3\|A27/ JK1 | ........ | ...... | .....P.N.. | ....... | ....... | ....... | ....F.. | ...ED.. | ...... |
| iPS:43 4571 | 21-225_74D2 | VK3\|A27/ JK1 | ........ | ...... | .....Y.D.. | ....... | ...P... | ....N.. | ....F.. | ....E.. | ...... |
| iPS:43 4579 | 21-225_77F7 | VK3\|A27/ JK1 | ........ | ...Y.. | ......Y... | .....I. | ....... | A...V.H.C. | ....... | ..H.DN. | ...... |
| iPS:43 4581 | 21-225_74B12 | VK3\|A27/ JK1 | ........ | ...Y.. | ......Y... | ....... | ...S... | A...... | ....... | ..H.DN. | ...... |
| iPS:43 4585 | 21-225_75A12 | VK3\|A27/ JK1 | ........ | ...... | ......R... | ....... | ....... | ....... | ....A.. | ..H.D.. | ...... |
| iPS:43 4595 | 21-225_77A10 | VK3\|A27/ JK1 | ........ | ...... | ......R..H. | ..K..F | ....... | ....... | ....... | ..H.D.. | ...... |
| iPS:43 4611 | 21-225_77C12 | VK3\|A27/ JK1 | ........ | ...... | ......R..D.. | ...R... | ....... | ....... | ....... | ....E.. | ...... |
| iPS:43 4633 | 21-225_74G8 | VK3\|A27/ JK1 | ........ | ...... | ........F.. | ...A... | .T..... | ....G.. | ....... | ....-.. | ..NSR. |
| iPS:43 4637 | 21-225_78E7 | VK3\|A27/ JK1 | ........ | ...... | ......N.D.. | ....... | ....... | ....... | ....F.. | ...ER.. | ...... |
| iPS:43 4657 | 21-225_79G1 | VK3\|A27/ JK1 | ...S.... | ...Y.. | ......Y... | ...A... | ...S... | A...... | ....... | ..H.DN. | ...... |
| iPS:43 4663 | 21-225_79F3 | VK3\|A27/ JK1 | ........ | ...Y.. | ......Y... | ...A... | ...S... | A...... | ....... | ..H.DN. | ...... |
| iPS:43 4671 | 21-225_74F4 | VK3\|A27/ JK1 | ........ | ...... | .....IF... | ..S.... | ....... | ....... | ....... | ....-.. | ...SR. |

Figure 52 (Continued)

| | | | | | | | | | |
|---|---|---|---|---|---|---|---|---|---|
| iPS:43 4687 | 21-225_75A5 | VK3JA27/ JK1 | . . . . . . . . . . . . . . . . . . . Y | . . . . . . . . . . . . . . . . . Y . . | . . . . . . . . . . . | . . . . . . . . . . | A . . . . . . . . . . . | . . . . . . . . . . . . | H . DN . . . . . . . | . . . . . . . . . . |
| iPS:43 4691 | 21-225_75G7 | VK3JA27/ JK1 | . . . . . . . . . . . . . . . . . . . . | . . R . . . . . . . D . . | . . . . . . . . . . . | . . . . . . . . . . | . . . . . . . . . . . . | . . . . . . . . . . . . | . . E . . . . . . . . | . . . . . . . . . . |
| iPS:43 4693 | 21-225_79F11 | VK3JA27/ JK1 | . . . . . . . . . . . . . . . . . . . Y | . . . . . . . . . . . . . Y . . | . . . . . . . . . . . | . . . . . . . . . . | A . . . . . . . . . . . | . . . . . . . . . . . . | . HSDN . . . . . . . | . . . . . . . . . . |
| iPS:43 4699 | 21-225_79G12 | VK3JA27/ JK1 | . . . . . . . . . . . . . . . . . . . Y | . . . . . . . . . . . . . Y . . | . . . . . . . . . . . | . . . . . . . . . . | A . . . . . . . . . . . | . . . . . . . . . . . . | . HSDN . . . . . . . | . . . . . . . . . . |
| iPS:43 4701 | 21-225_80A1 | VK3JA27/ JK1 | . . . . . . . . . . . . . . . . . RY | . . . . . . . . . . . . . Y . . | . . . . . . . . . . . | . . . . . . . S . . | A . . . . . V . . . C | . . . . . . . . . . . . | . HSDN . . . . . . . | . . . . . . . . . . |
| iPS:43 4703 | 21-225_80C1 | VK3JA27/ JK1 | . . . . . . . . . . . . . . . . . . . Y | . . . . . . . . . . . . . Y . . | . . . . . . . . . . . | . . . . . . . S . . | A . . . . . V . . . C | . . . . . . . . . . . . | . HSDN . . . . . . . | . . . . . . . . . . |
| iPS:43 4709 | 21-225_80E3 | VK3JA27/ JK1 | . . . . . . . . . . . . S . . . . . . . | . . . . . . . . . . . . . Y . . | . . . . . . . . . . . | . . . . . . . S . . | A . . . . . V . . . . | . . . . . . . . . . . . | . HSDN . . . . . . . | . . . . . . . . . . |
| iPS:43 4715 | 21-225_80D5 | VK3JA27/ JK1 | . L . . . . . . . . . K . V . . . . . . | . . . . . . . . . NIY . . | . . . . . . . . . . . | . . . . . . . . . . | . . . . . . T . . . . | . . . . . . . . . . . . | . . E . . . . . . . . | . . . . . . . . . . |
| iPS:43 4717 | 21-225_80A6 | VK3JA27/ JK1 | . . . . . . . . . . . IP . . . . . . . | . . G . . . . . . . D . . | . . . . . . . . . . . | . . . . . . . P . . | . . . . . . . . . . . . | . . . . . . . . . . . . | . . E . . . . . . . . | . . . . . . . . . . |
| iPS:43 4725 | 21-225_80H7 | VK3JA27/ JK1 | . . . . . . . . . . . . . . . . . . . . | . N . . . . . . . . IN . | . . . . . . . . . . . | . . . . . . . . . . | . . . . . . . . . . F | . . . . . . . . . . . . | . HSDN . . . . . . . | . . . . . . . . . . |
| iPS:43 4735 | 21-225_80B10 | VK3JA27/ JK1 | . . . . . . . . . . . . . . . . . . . . | . . . . . . . . . . . . . D . . | . . . . . . . . . . . | . . . . . . . P . . | . . . . . . . . . . . . | . . . . . . . . . . . . | . . E . . . . . . . . | . . . . . . . . . . |
| iPS:43 4743 | 21-225_74A4 | VK3JA27/ JK1 | . . . . . . . . . . . . . . . . . . . Y | . . . . . . . . . . . . . Y . . | . . . . . . . . . . . | . . . . . . . S . . | A . . . . . . . . . C | . . . . . . . . . . . . | . HSDN . . . . . . . | . . . . . . . . . . |
| iPS:43 4751 | 21-225_80H12 | VK3JA27/ JK1 | . . . . . . . . . S . . . . . . . . . . | . . . . . . . . . . . . . Y . . | . . . . . . . . . . . | . . . . . . . S . . | A . . . . . V . . . C | . . . . . . . . . . . . | . HSDN . . . . . . . | . . . . . . . . . . |
| iPS:43 4759 | 21-225_81C5 | VK3JA27/ JK1 | . . . . . . . . . . . . . . . . . . . Y | . . . . . . . . . . . . . Y . . | . . . . . . R . . . . | . . . . . . . S . . | A . . . . . V . . . C | . . . . . . . . . . . . | . . E . . . . . . . . | . . . . . . . . . . |
| iPS:43 4773 | 21-225_75D9 | VK3JA27/ JK1 | . . . . . . . . . V . . . . . . . RY | . . . . . . . . . . . . . Y . . | . . . . . . . . . . . | . . . . . . . . . . | . . . . . . . . . . C | . . . . . . . . . . . . | . HSDN . . . . . . . | . . . . . . . . . . |
| iPS:43 4777 | 21-225_81C11 | VK3JA27/ JK1 | . . . . . . . . . . . . . . . . . . . Y | . . . . . . . . . . . . . Y . . | . . . . . . . . . . . | . . . . . . . S . . | . L . . . . V . . . C | . . . . . . . . . . . . | . HSDN . . . . . . . | . . . . . . . . . . |
| iPS:43 4809 | 21-225_74F5 | VK3JA27/ JK1 | . . . . . . . . . . . . . . . . . . . Y | . . . . . . . . . . . . . Y . . | . . . . . . . . . . . | . . . . . . . S . . | A . . . . . . . . . . | . . . . . . . . . . . . | . HSDN . . . . . . . | . . . . . . . . . . |
| iPS:43 4821 | 21-225_83G1 | VK3JA27/ JK1 | . . . . . . . . . . . . . . . . . RY | . . . . . . . . . . . . . Y . . | . . . . . . . . . . . | . . . . . . . S . . | VL . . . . . V . . . C | . . . . . . . . . . . . | . HSDN . . . . . . . | . . . . . . . . . . |
| iPS:43 4835 | 21-225_83B6 | VK3JA27/ JK1 | . . . . . . . . . . . . . . . . . . . . | . . G . . . . . . . D . . | . . . . . . . . . . . | . . . . . . . TP . | A . . . . . . . . . . | . . . . . . . . . . . . | . . E . . . . . . . . | . . . . . . . . . . |
| iPS:43 4839 | 21-225_83B7 | VK3JA27/ JK1 | . . . . . . . . . SV . . . . . . . RY | . . . . . . . . . . . . . Y . . | . . . . . . . . . . . | . . . . . . . S . . | A . . . . . . . . . C | . . . . . . . . . . . . | . HSDN . . . . . . . | . . . . . . . . . . |
| iPS:43 4849 | 21-225_83C10 | VK3JA27/ JK1 | . . . . . . . . . . . . . . . . . . . . | . N . . . . . . . . P . H | . . . . . . . . . . . | . . . . . . . . . . | I . . . . . . . . . . | . . . . . . . . . . . . | . . E . . . . . . . . | . . . . . . . . . . |

Figure 52 (Continued)

| | | | | | | | | | | | | |
|---|---|---|---|---|---|---|---|---|---|---|---|---|
| iPS:43 4869 | 21-225_84E12 | VK3|A27/JK1 | . . . . . | . . . . . | . I N . . | . . . . . | . . . . . | . . . . . | . . . . . | . D . . F | . . E . . | . . . . . |
| iPS:43 4879 | 21-225_85A3 | VK3|A27/JK1 | . . . . F | . . . . . | . . N . . | . . . . A | . . . . . | . . . . A | . . . . . | . . . . . | . H . DN | . . . . . |
| iPS:43 4881 | 21-225_85B4 | VK3|A27/JK1 | . . . . F | . . . . Y | . . . . . | . . . . . | . . . . . | . . . . A | . . . . . | . . . . . | . H . DN | . . . . . |
| iPS:43 4887 | 21-225_85D6 | VK3|A27/JK1 | . . Q . . | . . . . F | . . . . . | . . . . . | . . . . . | . . . . A | . . . . . | . . . . . | . R . D . | . . . . . |
| iPS:43 4891 | 21-225_85G6 | VK3|A27/JK1 | . A . . . | . . . . . | . R . . . | . P . D . | . . . . . | . A . P | . . . . . | . . . . . | . . E . . | . . . . . |
| iPS:43 4895 | 21-225_74H7 | VK3|A27/JK1 | . L . . . | . . . . . | . . . . . | . N I Y . | . . . . . | . . . . . | . I I . . | . . V . . | . . E . . | . . . . . |
| iPS:43 4899 | 21-225_85B9 | VK3|A27/JK1 | . . . . . | . . . . F | . . . . . | . . N . . | . R . . . | . . . . . | . . . . . | . . . . C | . . E . . | . . . . . |
| iPS:43 4907 | 21-225_85G10 | VK3|A27/JK1 | . . . . . | . . . . S | . . G . . | . . W . . | . . . . . | . . . . . | . . . . . | . . . . F | . . E . . | . . . . . |
| iPS:43 4913 | 21-225_86C1 | VK3|A27/JK1 | . . . . . | . . . . Y | . . . . . | . . Y . . | . . . . A | . . . . . | . A . . . | . . . . C | . H . DN | . . . . . |
| iPS:43 4921 | 21-225_86E4 | VK3|A27/JK1 | . . . . . | . . . . RY | . . . . . | . . . . . | . . . . . | . . . . . | . A . . . | . . . . C | . HSDN | . . . . . |
| iPS:43 4939 | 21-225_86C11 | VK3|A27/JK1 | . . . . . | . . . . Y | . . . . . | . . Y . . | . . . . . | . . A . T | . L . . . | . . . . C | . HSDN | . . . . . |
| iPS:43 4943 | 21-225_87H1 | VK3|A27/JK1 | . . . . . | . . . . . | . . N . . | . . D . . | . . . . . | . . . . . | . A . . . | . . . . S | . . E . . | . . . . . |
| iPS:43 4945 | 21-225_87E5 | VK3|A27/JK1 | . F . . . | . . . . Y | . . . . . | . . Y . . | . . . . . | . . . . S | . . . . . | . V . . C | . HSDN | . . . . . |
| iPS:43 4955 | 21-225_87C9 | VK3|A27/JK1 | . . V . . | . . . . RY | . . . . . | . . Y . . | . . . . . | . . . . S | . A . . . | . V . . C | . HSDN | . . . . . |
| iPS:43 4961 | 21-225_87A12 | VK3|A27/JK1 | . . . . . | . . . . Y | . . . . . | . . Y . . | . . . . . | . . . . S | . V . . . | . . . . C | . HSDN | . . . . . |
| iPS:43 4969 | 21-225_88H1 | VK3|A27/JK1 | . . . . . | . . . . Y | . . . . . | . . Y . . | . . . . . | . . . . S | . V . . . | . V . . C | . HSDN | . . . . . |
| iPS:43 4981 | 21-225_88E7 | VK3|A27/JK1 | . . . . . | . . . . Y | . . . . . | . . Y . . | . . . . . | . . . . S | . A . . . | . V . . C | . HSDN | . . . . . |
| iPS:43 4983 | 21-225_88F7 | VK3|A27/JK1 | . . . . . | . . . . . | . . . . . | . . Y . . | . . . . . | . . . . S | . A . . . | . . . . C | . HSDN | . . . . . |
| iPS:43 4995 | 21-225_88G9 | VK3|A27/JK1 | . . . . . | . . . . RY | . . . . . | . . Y . . | . . . . . | . . . . S | . A . . . | . V . . C | . HSDN | . . . . . |
| iPS:43 4999 | 21-225_75A8 | VK3|A27/JK1 | . . . . . | . . . . Y | . . . . . | . . Y . . | . . . . . | . . . . S | . A . . . | . . . . C | . HSDN | . . . . . |
| iPS:43 5013 | 21-225_89D5 | VK3|A27/JK1 | . . . . S | . . . . Y | . . . . . | . . Y . . | . . . . . | . . . . S | . A . . . | . . . . . | . H . DN | . . . . . |

Figure 52 (Continued)

| | | | | | | | | | | |
|---|---|---|---|---|---|---|---|---|---|---|
| iPS:43 5015 | 21-225_89H5 | VK3JA27/ JK1 | . . . . . . . . . . | . . . . . . . . . . | . N . . . . . . . . | . . . . . . . . . . | . . . . . . . . . . | . . . . . . . . . . | . N . I . . . . . V | . . . . . . . . . . V . . | . E . . . . . . . . | . . . . . . . . . . |
| iPS:43 5025 | 21-225_89E10 | VK3JA27/ JK1 | . . S . . . . . . Y | . . . . . . . . . . | . . . . . . . . . . | . . . . . . . . . . | . . . . . . . . . . | V . . . . . . . . . A . . | . . . . . . . . . V | . HSDN . . . . . . | . . . . . . . . . . |
| iPS:43 5029 | 21-225_89A11 | VK3JA27/ JK1 | . . . . . . . . . . | . . . . . . . NF . | . . . . . . . . . D | . . . . . . . . . . | . . A . T . . . . . | . . . . . . . . . . | . . . . . . . . . . | . . EI . . . . . . | . . . . . . . . . . |
| iPS:43 5039 | 21-225_90G4 | VK3JA27/ JK1 | . . . . . . . . . Y | . . . . . . . . . . | . . . . . . . . . Y | . . . . . . . . . . | . . . . . . . . . S | V . . . . . . . . . A . . | . . . . . . . . . S | . HSDN . . . . . . | . . . . . . . . . . |
| iPS:43 5041 | 21-225_90A5 | VK3JA27/ JK1 | . . . . . . . . . Y | . . . . . . . . . . | . . . . . . . . . Y | . . . . . . . . . . | . . . . . . . . . . | . . . . . . . . . . A . . | . . . . . . V . H . | . H . DN . . . . . . | . . . . . . . . . . |
| iPS:43 5043 | 21-225_90G5 | VK3JA27/ JK1 | . . . . . . . . . Y | . . . . . . . . . . | . . . . . . . . . Y | . . . . . . . . . T | . . . . . . . . . . | . . . . . . . . . . A . . | . . . . . . V . H . | . H . DN . . . . . . | . . . . . . . . . . |
| iPS:43 5055 | 21-225_90F10 | VK3JA27/ JK1 | . . . . . . . . . Y | . . . . . . . . . . | . . . . . . . . . Y | . . . . . . . . . . | . . . . . . . . . S | . . . . . . . . . . A . . | . . . . . . . . . C | . H . DN . . . . . . | . . . . . . . . . . |
| iPS:43 5073 | 21-225_91B2 | VK3JA27/ JK1 | . . . . . . . . . Y | . . . . . . . . . . | . . . . . . . . . Y | . . . . . . . . . . | . . . . . . . . . S | . . . . . . . . . . A . . | . . . . . . V . . C | . H . DN . . . . . . | . . . . . . . . . . |
| iPS:43 5075 | 21-225_91B3 | VK3JA27/ JK1 | . . . . . . . . . Y | . . . . . . . . . . | . . . . . . . . . Y | . . . . . . . . . . | . . . . . . . . . S | . . . . . . . . . . A . . | . . . . . . V . H . C | . H . DN . . . . . . | . . . . . . . . . . |
| iPS:43 5077 | 21-225_91F3 | VK3JA27/ JK1 | . . . . . . . . . Y | . . . . . . . . . . | . . . . . . . . . Y | . . . . . . . . . A | . . . . . . . . . S | . . . . . . . . . . A . . | . . . . . . V . . C | . HSDN . . . . . . | . . . . . . . . . . |
| iPS:43 5079 | 21-225_91B4 | VK3JA27/ JK1 | . . . . . . . . . Y | . . . . . . . . . . | . . . . . . . . . Y | . . . . . . . . . T | . . . . . . . . . . | . . . . . . . . . . A . . | . . . . . . V . . C | . H . DN . . . . . . | . . . . . . . . . . |
| iPS:43 5089 | 21-225_91E9 | VK3JA27/ JK1 | . . . . . . . . . Y | . . . . . . . . . . | . . . . . . . . . Y | . . . . . . . . . . | . . . . . . . . . . | . . . . . . . . . . A . . | . . . . . . V . H . C | . HSDN . . . . . . | . . . . . . . . . . |
| iPS:43 5097 | 21-225_92B1 | VK3JA27/ JK1 | . . . . . . . . . . | . . . . . . . . . R | . . . . . . . . . G | . . . . . . . . . R | . . . . . . . . . . | D . . . . . . . . . | . . . . . . . . . . C | . HSDN . . . . . . | . . . . . . . . . . |
| iPS:43 5111 | 21-225_92D6 | VK3JA27/ JK1 | . . . . . . . . . Y | . . . . . . . . . N | . . . . . . . . . Y | . . . . . . . . . . | . . . . . . . . . . | V . . . . . . . . . | . . . . . . . . . . C | . E . . . . . . . . | . . . . . . . . . . |
| iPS:43 5115 | 21-225_77C5 | VK3JA27/ JK1 | . . . . . . . . . Y | . . . . . . . . . . | . . . . . . . . . Y | . . . . . . . . . . | . . . . . . . . . S | . . . . . . . . . . A . . | . . . . . . . . . . | . H . DN . . . . . . | . . . . . . . . . . |
| iPS:43 5171 | 21-225_93C2 | VK3JA27/ JK1 | . . . . . . . . . Y | . . . . . . . . . . | . . . . . . . . . Y | . . . . . . . . . . | . . . . . . . . . . | . . . . . . . . . . A . . | . . . . . . . H . C | . H . DN . . . . . . | . . . . . . . . . . |
| iPS:43 5177 | 21-225_93E4 | VK3JA27/ JK1 | . . . . . . . . . Y | . . . . . . . . . . | . . . . . . . . . Y | . . . . . . . . . . | . . . . . . . . . . | . . . . . . . . . . A . . | . . . . . . V . . C | . HSDN . . . . . . | . . . . . . . . . . |
| iPS:43 5183 | 21-225_93E9 | VK3JA27/ JK1 | . . . . . . . . . . | . . . . . . . . . . | . . . . . . . . . D | . . . . . . . . . T | . . . . . . . . . P | . . . . . . . . . . | . . . . . . . . . . | . E . . . . . . . . | . . . . . . . . . . |
| iPS:43 5195 | 21-225_94D3 | VK3JA27/ JK1 | . . Q . . . . . . . | . . . . . . . . . . | . . . . . . . . . . | . . . . . . . . . . | . . . . . . . . . . | . . . . . . . . . . | . . . . . . . . . . | . H . D . . . . . . | . . . . . . . . NQ |
| iPS:43 5217 | 21-225_94F12 | VK3JA27/ JK1 | . . . . . . . . . F | . . . . . . . . . . | . . . . . . . . . Y | . . . . . . . . . . | . . . . . . . . . S | . . . . . . . . . . A . . | . . . . . . . . . . | . H . DN . . . . . . | . . . . . . . . . . |
| iPS:43 5219 | 21-225_95D2 | VK3JA27/ JK1 | . . . . . . . . . . | . . . . . . . . . . | . . . . . . . . . Y | . . . . . . . . . . | . . . . . . . . . . | . . . . . . . . . . A . . | . . . . . . . . . C | . H . DN . . . . . . | . . . . . . . . . . |

Figure 52 (Continued)

| | | | | | | | | | |
|---|---|---|---|---|---|---|---|---|---|
| iPS:43 5235 | 21-225_95F9 | VK3|A27/ JK1 | . . . . . . . . . . . | . . Y . . . | . . . . . Y . . | . . . . . . . . . . | . . . . . A . . . . | . . . . . . C . . . | . H.DN . . . . | . . . . |
| iPS:43 5237 | 21-225_95G9 | VK3|A27/ JK1 | . . S . . . . . . . | . . . . . Y | . . . . . . . . . . | . . . S . . . . | . . . . . A . . . . | . . . . . . C . . . | . H.DN . . . . | . . . . |
| iPS:43 5239 | 21-225_95H10 | VK3|A27/ JK1 | . . . . S . . I . Y | . . . . . . . | . . . . . . . . . . | . . . . . . . . | . . . . . A . . V.H.C | . . . . . . . . . . | . H.DN . . . . | . . . . |
| iPS:43 5273 | 21-225_97A2 | VK3|A27/ JK1 | . . . S . . . . . . | . . . . . Y . . | . . . . . . . . . . | . . . . . . . | . . . . . A . . . . | . . . . . . C . . . | . HSDN . . . . | . . . . |
| iPS:43 5281 | 21-225_97E5 | VK3|A27/ JK1 | . . . S . . . . . . | . . . . . Y . . | . . . . . . . . . . | . . . S . . . | . . . . . A . . V . C | . . . . . . . . . . | . HSDN . . . . | . . . . |
| iPS:43 5331 | 21-225_147G8 | VK3|A27/ JK1 | Q . . . . . . . . . | . RIF . . . . N . . | . . . . . . . . . . | . . . . . . . | . . . I . . . T . . | . . . . . . . . . . | . . D . . . . . | . . N . |
| iPS:43 5815 | 21-225_190G10 | VK3|A27/ JK1 | . . . . . . . . . . | . . P . . . RF . . | . . . . . . . . . . | . . . . . . . | . . . . . . . N . . | . . . . . . . . . . | . . . . . . SP . . | . . . . |
| iPS:43 5843 | 21-225_191F1 | VK3|A27/ JK1 | . A . . . . . . . . | . . I.L . . NF . . | . . . . . . . . . . | . . . . . . . | . . . . . . . N . . | . . . . . . . . . . | . R . . . . . . | . . . . |
| iPS:43 5847 | 21-225_191A3 | VK3|A27/ JK1 | . . . . . . . . . . | . IR . . . F . . | . . . . . . . . . . | . . . . . . . | . . . . . . . . . . | . . . . . . . . . . | . N . . . . . A | . . . . |
| iPS:43 5849 | 21-225_191C3 | VK3|A27/ JK1 | . . . . . . . . . . | . IR . . . F . . | . . . . . . . . . . | . . . . . . . | . . . . . . . . . . | . . . . . . . . . . | . N . . . . . A | . . . . |
| iPS:43 5851 | 21-225_191D3 | VK3|A27/ JK1 | . . . . . . . . . . | . G . . IRT . NF . | . . . Q . . . . . . | . . . . . . . | . . . . . . . N . . | . . . . . . . . . . | . . . . . . . . | . . . . |
| iPS:43 5865 | 21-225_191A5 | VK3|A27/ JK1 | . . . S . . . . . . | . . . . . R . . NF . | . . . . . . . . . . | . . . N . . . | . . . . . . . . . . | . . . . . . . . . . | . G . . . . . . | V . . . |
| iPS:43 5905 | 21-225_190A3 | VK3|A27/ JK1 | . . . M . . . . . . | . . . NIR . . NF . | . . . . . . . . . . | . . . . . . . | . . . . . . . N . V | . . . . . . . . . . | . N . . . . SP . . | . . . . |
| iPS:43 5911 | 21-225_190B4 | VK3|A27/ JK1 | . . . . . . . . . . | . . . IR . . . F . | . . H . . . . . . . | . YR . . . . | . . . . . . . N . . | . . . . . . . . . . | . N . . . . . A | . . . . |
| iPS:43 5913 | 21-225_190A7 | VK3|A27/ JK1 | . . . . . . . . . . | . . . . R . . NF . | . . . Q . . . . . . | . . P . . . . | . . . . . . . N . . | . . . . . . . F . | . N . . . . . . | . . N . |
| iPS:43 5939 | 21-225_191H7 | VK3|A27/ JK1 | . . S . . . . . . . | . G . . IRT . DF . | . . . . . . . . . . | . . . . . . . | . . . . . . . N . . | . . . . . . . . . . | . N . . . . . . | . . . . |
| iPS:43 5967 | 21-225_192B3 | VK3|A27/ JK1 | . . . . . . . . . . | . . . . . R . . F . | . . . . . F . . . . | . . . . . . . | . . . . . A . . . . | . . . . . . . . . . | . N . . . . . A | . . . . |
| iPS:43 5973 | 21-225_192H3 | VK3|A27/ JK1 | . . . . . . . . . . | . . . . I . . NF . | . L . . . . . . . . | . . . . . . . | . . . . . . . N . . | . . . . . . . . . . | . I . . . . . . | . . . . |
| iPS:43 5995 | 21-225_192F8 | VK3|A27/ JK1 | . . . . . . . . . . | . . . . . R . . DF . | . H . . . . . . . . | . V.R . . . | . . . . . . . N . . | . . . . . . . . . . | . E . . . . . . | . . . . |
| iPS:43 6007 | 21-225_192G12 | VK3|A27/ JK1 | . . . . . . . . . . | . . . . . R . . NF . | . . . . . F . . . . | . . R . . . . | . . . . . . . N . . | . . . . . . . . . . | . N . . . . . . | . . . . |
| iPS:43 6009 | 21-225_193A1 | VK3|A27/ JK1 | . . . . . . . . . . | . . . . . R . . NF . | . . . . . . . . . . | . . . . . . . | . . . . . . . N . . | . . . . . . . . . . | . N . . . . . . | . . . . |

Figure 52 (Continued)

| | | | | | | | | | | |
|---|---|---|---|---|---|---|---|---|---|---|
| iPS:43 6011 | 21-225_193B1 | VK3JA27/ JK1 | . . . . . . . . . . | . . . . D . . . . . | . . . . . R . . . | . H . . . . . . . . | . . . . . . . . . . | . . . N . . . . . . | . . . N . . . . . . | . . . . . . . . . . |
| iPS:43 6015 | 21-225_193D3 | VK3JA27/ JK1 | . . . . . . . . . . | . . . NF . . . . . | . . . . . . . . . | . . . . . . . . . . | . . . . . . . . . . | . . . . . . . F . | . . . . . . . . . . | . . . . . . . . . . |
| iPS:43 6017 | 21-225_193F3 | VK3JA27/ JK1 | . . . . . . . . . . | . . . IR . . . . . | . . . . . . . . . | . . . . . . . . . | . . F . E . . . . | . . . . . . . . . | . . . . . . . A . . | . . . . N . . . . . |
| iPS:43 6027 | 21-225_193E6 | VK3JA27/ JK1 | . . . . . . . . . . | . . G . . . IRT . . . . . DF . V | . . . . . . . . . | . Q . . . . . . . | . . . N . . . . . . | . . G . . . . . . | . . . . . . . . . . | . . . . . . . . . . |
| iPS:43 6029 | 21-225_193H6 | VK3JA27/ JK1 | . . . . A . . . . . | . . . . . R . . . | . . . . . . . . . | . . . . . . . . . | . . . . . G . . . . | . . . . . . . . . | . . E . . . . . . . | . . . . . . . . . . |
| iPS:43 6035 | 21-225_193C8 | VK3JA27/ JK1 | . . . . . F . . . . | . . . . S . . . IRT . . NF . . . . . | . . . . . . . . . | . Q . . . . . . . | . . . . . . . . . | . . . N . . . . . | . . . N . . . . . . | . . . N . . . . . . |
| iPS:43 6037 | 21-225_193D8 | VK3JA27/ JK1 | . . . F . . . . . . | . . . . . . . . . IR . . F . . . . | . . . . . . . . . | . . . . . . . . . | . . . . . . . . . | . . . . . . . . . | . . . N . . . . . . | . . . . . . . . . . |
| iPS:43 6041 | 21-225_193G8 | VK3JA27/ JK1 | . . . K . . . . . . | . . . . . . . . . . . . IRT . . | . H . . . . . . . | . . . . . . . . . | . . . . . . . . . | . . . . . . . . . | . . . N . . . . . . | . . . . . . . . . . |
| iPS:43 6047 | 21-225_193B10 | VK3JA27/ JK1 | . . . . . . . . . . | . . . . . . . . . . . . RT . . . . NF . . . . . | . . . . . . . . | . . . . . . . . . | . . . . . . . . . | . . . N . . . L . . | . . . N . . . . . . | . . . . . . . . . . |
| iPS:43 6049 | 21-225_193B12 | VK3JA27/ JK1 | . . . . . . . . . . | . . . . . . . . . | . . . P . . . . . | . . . . V . . . . | . . . . . . . . . | . . . . R . . . . | . . . . SP . . . . | . . . . . . . . . . |
| iPS:43 6062 | 21-225_194E5 | VK3JA27/ JK1 | . . . . S . . . . . | . . . G . . IRT . | . . . . . . . . . | . D . . . . . . . | . . . . . . . . . | . . . . . . . . . | . . . N . . . A . . | . . . . . . . . . . |
| iPS:43 6064 | 21-225_194E6 | VK3JA27/ JK1 | . . . . . . . . . . | . . . . . . . . . IR . . NF . . . . | . . . . . . . . . | . . . . . . . . . | . . . . . . . . . | . . . N . . K . . | . . . . . . . . . . | . . . . . . . . . . |
| iPS:43 6072 | 21-225_194C10 | VK3JA27/ JK1 | . . . L . . . . . . | . . . . P . N . . . . . . G . . . . | . T . . . . . . . | . . . . . . . . . | . . . . . . . . . | . . . . . V . . . | . . A . . . . A . . | . . . . . . . . . . |
| iPS:43 6080 | 21-225_195B1 | VK3JA27/ JK1 | . . . . . . . . . . | . . . P . N . . . . . . . N . . . . | . T . . . . . . . | . . . N . . . . . | . . . . . . . . . | . V . . R . . . . | . . A . . . . . F . | . . . . . . . . . . |
| iPS:43 6088 | 21-225_195C8 | VK3JA27/ JK1 | . . . . . . . F . . | . . . . . . . . . | . . . . . . . . . | . F . . . . . . . | . . . . . . . . . | . . . . . . . . . | . . E . . . . F . | . . . . . . . . . . |
| iPS:43 6122 | 21-225_196G10 | VK3JA27/ JK1 | . . . . . . . . . . | . . . . P . . . N . | . . . . . YR . . | . . . . . . . . . | . . . . . N . . . | . . . . . . . . . | . . . . . . . . . . | . . . . . . . . . . |
| iPS:43 6134 | 21-225_196H12 | VK3JA27/ JK1 | . . . . . . . F . . | . . . . . R . . . | . H . . . . . . . | . . . . . . . . . | . . . N . . . . . | . . . . . . . . . | . . . N . . . A . . | . . . . . . . . . . |
| iPS:43 6146 | 21-225_197F4 | VK3JA27/ JK1 | . . . . . G . . . . | . . . . . . . . . IR . . F . . . . | . L . . . . . . . | . . . . . . . . . | . . . . . . . . . | . . . . . . . . . | . . . . SP . . . . | . . . L . . . . . . |
| iPS:43 6177 | 21-225_198B1 | VK3JA27/ JK1 | . . . . S . . . . . | . . G . . . IRT . . . . NF . . . . | . . . . . . . . . | . Q . . . . . . . | . . . . . F . . . | . . . . . . . . . | . . . . . . . . . . | . . . . . . . . . . |
| iPS:43 6179 | 21-225_198E1 | VK3JA27/ JK1 | . . . . . . . . . . | . . . . . . . . . IR . . . . . . . | . . . . . . . . . | . . . . . . . . . | . . . . . . . . . | . . . . . . . . . | . . . N . . . . . . | . . . . . . . . . . |
| iPS:43 6181 | 21-225_198C2 | VK3JA27/ JK1 | . V . . . . . . L . YSE . . S . . . | . . . . . . R . . | . . . . . . . . C | . . E . . . . . S | . . . . . . . . . | . . . . . . . . . | . . . N . . . . . . | L . HA . . |

Figure 52 (Continued)

| ID | | | | | | | | | | | |
|---|---|---|---|---|---|---|---|---|---|---|---|
| iPS:43 6195 | 21-225_198G10 | VK3jA27/JK1 | ..... | ..IR.. | ..... | ..... | ..... | ..... | ..N.. | ..A.. | ..... |
| iPS:43 6197 | 21-225_199C2 | VK3jA27/JK1 | ..... | ..IR.. F.. | ..... | ..... | ..... | ..... | ..N.. | ..... | ..... |
| iPS:43 6207 | 21-225_199C7 | VK3jA27/JK1 | ..... | ..IRT. NF.. | ..... | ..... | ..... | ..... | ..N.. | ..A.. | ..... |
| iPS:43 6210 | 21-225_199G11 | VK3jA27/JK1 | ...V. | ..R.. | ..... | ..... | ..... | ..... | ..... | ..... | ..... |
| iPS:43 6226 | 21-225_200F10 | VK3jA27/JK1 | ..... | ..NIR. F.. | ..... | F.. | ..... | ..... | ..N.. | ..A.. | ..... |
| iPS:43 6232 | 21-225_201E1 | VK3jA27/JK1 | ..D.. | ..P.IN.. GF.. | ..... | ..... | ..N.. | ..... | H.ET. | ..... | ..... |
| iPS:43 6238 | 21-225_201B2 | VK3jA27/JK1 | ..... | ..R | ..... | ..... | ..... | MFH. | ..... | ..... | ..... |
| iPS:43 6256 | 21-225_202D9 | VK3jA27/JK1 | ..... | ..N.. G.. | S | ..... | ..... | F | ..EN. | ..... | ..... |
| iPS:43 6302 | 21-225_205G7 | VK3jA27/JK1 | ..... | ..F.. N.. | ..... | A | ..... | H | ..ET. | ..... | ..... |
| iPS:43 6310 | 21-225_202D11 | VK3jA27/JK1 | ..... | ..IN.. N.. | ..R.. ..V. | ..... | ..... | ..... | ..E.. | ..... | ..... |
| iPS:43 6336 | 21-225_208B5 | VK3jA27/JK1 | ..... | ..N.. | ..R.. | ..... | ..N.. | F | ..EN. | ..... | ..... |
| iPS:43 6340 | 21-225_208A9 | VK3jA27/JK1 | ..... | ..N.. | ..V.. | ..... | ..... | ..... | H.EN. | ..... | ..... |
| iPS:43 6472 | 21-225_220E1 | VK3jA27/JK1 | ..... | ..I.R. H.V | ..N.V. ..L..T. | ..... | ..... | ..... | H.H. | ..... | ..... |
| iPS:43 6506 | 21-225_220E1 | VK3jA27/JK1 | ..... | ..Y.. N.. | ..... | ..... | ..RS. | M | ..ED. | ..... | ..... |
| iPS:43 6580 | 21-225_222C7 | VK3jA27/JK1 | ..RY | ..Y.. | ..... | ..... | ..G. | TI | ..T.. | ..R.. | ..R.. |
| iPS:43 6506 | 21-225_225E7 | VK3jA27/JK1 | ..Y. | ..Y.. | ..... | ..... | A.... | C | H.DN. | ..... | ..... |
| iPS:43 7324 | 21-225_75C2 | VK3jA27/JK1 | ..... | ..Y.. | ..... | ..... | A.... | V.H.C | H.DN. | ..... | ..... |
| iPS:43 7328 | 21-225_75D3 | VK3jA27/JK1 | ..... | ..Y.. | ..... | S | A.... | H | ..E.. | ..... | ..... |
| iPS:43 7332 | 21-225_75F3 | VK3jA27/JK1 | A.... | ..P.D. | ..... | P | ..... | ..... | H.DN. | ..... | ..... |
| iPS:43 7340 | 21-225_75G9 | VK3jA27/JK1 | ..... | ..Y.. | ..... | ..... | A...V. | C | H.DN. | ..... | ..... |
| iPS:43 7344 | 21-225_75G12 | VK3jA27/JK1 | ..... | ..Y.. | S | ..... | A.... | ..... | HSDN. | ..... | H.. |
| iPS:43 7350 | 21-225_74A3 | VK3jA27/JK1 | | | | | | | | | |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 7369 | 21-225_74D6 | VK3/A27/ JK1 | ........Y. | ........ | ........ | ........ | A....... | .H.DN... | ........ |
| iPS:43 7383 | 21-225_74H8 | VK3/A27/ JK1 | ......F. | ........ | ........ | ........ | ........ | ........ | ........ |
| iPS:45 1122 | 21-225_200A1 | VK3/A27/ JK1 | ..Y.....I | ....N... | ....R... | ........ | C.L..... | ....EI.. | ........ |
| iPS:39 2864 | 21-225_23B9 | VK3/A27/ JK1 | ........ | N..N.Y.. | ...S.... | ........ | ........C. | ........ | ....S... |
| | Germline | | K_FR1 | K_CDR1 | K_FR2 | K_CDR2 | K_FR3 | K_CDR3 | K_FR4 |
| | VK1/A30/JK4 | | DIQMTQSPSS LSASVGDRVTITC | RAS QSI ....SNLA | WYQQKPG KAPKLLIY | AASSLQS | GVPSRFSGSG SGTDFTLTIS SLQPEDFATYYC | QQSYSTPPT | FGGGTK VEIK |
| iPS:46 8812 | 21-225_48H4 | VK1/A30/ JK4 | ......F. | .RD..... | ........ | ........ | ........ | ....Y... | ........ |
| iPS:46 8824 | 21-225_73G6 | VK1/A30/ JK4 | ........ | ........ | ........ | ........ | ........ | ........ | ........ |
| iPS:46 8818 | 21-225_190C8 | VK1/A30/ JK4 | ........ | ........ | ........ | ........ | ......E. | ....D... | ........ |
| iPS:46 8840 | 21-225_200H9 | VK1/A30/ JK4 | ........ | ........ | ........ | ........ | ...I.... | ........ | ........ |
| iPS:46 8868 | 21-225_74A1 | VK1/A30/ JK4 | ........ | ........ | ........ | ........ | ........ | ....D... | ......A. |
| iPS:39 2920 | 21-225_29G4 | VK1/A30/ JK4 | ........ | ........ | ........ | ...G.... | ........ | ........ | ........ |
| iPS:43 3899 | 21-225_43C3 | VK1/A30/ JK4 | ........ | ........ | ........ | ........ | ........ | ........ | ......T. |
| iPS:43 3921 | 21-225_44C3 | VK1/A30/ JK4 | ........ | ........ | ........ | ........ | ....G... | ....S... | .....G.T |
| iPS:43 3947 | 21-225_44E12 | VK1/A30/ JK4 | ........ | T....... | ........ | ........ | S....... | ........ | ........ |
| iPS:43 3963 | 21-225_46B1 | VK1/A30/ JK4 | ........ | ........ | ........ | ........ | ........ | ........ | ........ |
| iPS:43 3969 | 21-225_46F3 | VK1/A30/ JK4 | ........ | ...K.... | ........ | ........ | S....... | ........ | ........ |
| iPS:43 3975 | 21-225_46C6 | VK1/A30/ JK4 | ........ | ........ | ........ | ........ | ........ | ....R... | ........ |
| iPS:43 3977 | 21-225_46D8 | VK1/A30/ JK4 | ........ | ...K.... | ........ | ....F... | ........ | ........ | ......T. |
| iPS:43 3983 | 21-225_47A1 | VK1/A30/ JK4 | ........ | ....D... | ........ | ........ | .....R.. | ........ | ........ |
| iPS:43 3987 | 21-225_47A5 | VK1/A30/ JK4 | ........ | ........ | ........ | ........ | ........ | ........ | ........ |

Figure 52 (Continued)

| | | | | | | | | | |
|---|---|---|---|---|---|---|---|---|---|
| iPS:43 4013 | 21-225_48D12 | VK1|A30/JK4 | . . . | . . . | . . . | . . . | . . . | . . . | . . . |
| iPS:43 4019 | 21-225_49A1 | VK1|A30/JK4 | . . . D | . . . | . . . | . . . | . . . | . . . | . . . |
| iPS:43 4029 | 21-225_49C6 | VK1|A30/JK4 | . . . | . . . | . . . | . F . | . . . | . . . | . . . |
| iPS:43 4043 | 21-225_50G10 | VK1|A30/JK4 | . . . N | . V . | . . . | . . . | . Y . | . . . | . . . |
| iPS:43 4077 | 21-225_51F11 | VK1|A30/JK4 | A . . | . . . | . T . | . . . | . . . | . F . | . S . |
| iPS:43 4081 | 21-225_52B2 | VK1|A30/JK4 | . . . | . R . | . T . | . . . | . R . | . . . | . . . |
| iPS:43 4105 | 21-225_53D2 | VK1|A30/JK4 | . . . | . . . | . . . | . . . | . . . | . . . | . . . |
| iPS:43 4119 | 21-225_53E6 | VK1|A30/JK4 | A . . | . N . | . N . | . . . | . R . | . F . | . . . |
| iPS:43 4141 | 21-225_54C6 | VK1|A30/JK4 | A . . | . N . | . N . | . . . | . R . | . . . | . . . |
| iPS:43 4159 | 21-225_55B8 | VK1|A30/JK4 | S . . A | . H . | . ER . | . . . | . . . | . . . | . G . |
| iPS:43 4179 | 21-225_56F1 | VK1|A30/JK4 | . D . | . N . | . . . | . . . | . D . | . H . F | . . . |
| iPS:43 4217 | 21-225_60E8 | VK1|A30/JK4 | F . . | . F . | . . . | . . . | . . . | . . . | . . . |
| iPS:43 4249 | 21-225_62E2 | VK1|A30/JK4 | . . . | . . . | . R . | . . . | . S . | . . . | . R . |
| iPS:43 4253 | 21-225_62E4 | VK1|A30/JK4 | . . . | . . . | . F . | . . . | . SN . | . . . | . . . |
| iPS:43 4313 | 21-225_59E6 | VK1|A30/JK4 | . . . | . . . | . . . | S . . K . L | . . . | . . . | . . . |
| iPS:43 4337 | 21-225_64E1 | VK1|A30/JK4 | . . . | . . . | . . . | . P . | . . . | . . . | . . . |
| iPS:43 4411 | 21-225_68F11 | VK1|A30/JK4 | . . . | . . . | . . . | . . . | . ST . | . F . | . . . |
| iPS:43 4413 | 21-225_68D12 | VK1|A30/JK4 | K . . | . . . | . . . | . . . | . R . | . . . | . . . |
| iPS:43 4433 | 21-225_70E8 | VK1|A30/JK4 | T . . | . . . | . . . | . . . | . . . | . . . | . . . |
| iPS:43 4439 | 21-225_70E12 | VK1|A30/JK4 | . N . N . N | . . . | . F . | . . . | . . . | . . . | . . . |
| iPS:43 4489 | 21-225_74E4 | VK1|A30/JK4 | . . . | . . . | . T . | . G . H | . SN . | . . . | . S . |

| ID | V/J | | | | | | | | | | |
|---|---|---|---|---|---|---|---|---|---|---|---|
| iPS:43 5703 | 21-225_170D11 | VK1|A30/ JK4 | . . . . . | . . . . . | . . . . . | . . . . . | . . . . . | . . . . . | . . . Y . | . . . . . | . . . . |
| iPS:43 5705 | 21-225_171C3 | VK1|A30/ JK4 | . . . . . | . . . . . | . . H . . | . . . T . | . . . . . | . . . . . | . . . Y . | . . F . . | . . R |
| iPS:43 5709 | 21-225_171A4 | VK1|A30/ JK4 | . . . . . | . . . . . | . . F . . | . . . T . | . . . . . | . . . . . | . . . Y . | . . . . . | . . . . |
| iPS:43 5721 | 21-225_172B3 | VK1|A30/ JK4 | . . . . . | . . . . . | . . . . . | . . . . . | . . . . . | . . . . . | . . . Y . | . . . . . | . . . . |
| iPS:43 5725 | 21-225_172G8 | VK1|A30/ JK4 | . . . . . | . . V . . | . . G . E | . . . . . | . . . . G | . . . . . | . . H Y . | . . F . . | . . . . |
| iPS:43 5735 | 21-225_173H12 | VK1|A30/ JK4 | . . . . . | . . . . . | . . . T . | . . . . . | . . . . . | . . . . . | . . . Y . | . F . N | . . . . |
| iPS:43 5743 | 21-225_175G1 | VK1|A30/ JK4 | . . . . . | . . . T . | . . F . . | . . . . . | . . . . . | . . . . . | . . . Y . | . . . . . | . . . . |
| iPS:43 5761 | 21-225_176B11 | VK1|A30/ JK4 | . . . . . | . . . . . | . . . . . | . . . . . | . . . . . | . . . . S | . . . Y . | . . . . . | . . . . |
| iPS:43 5779 | 21-225_178B10 | VK1|A30/ JK4 | . . . . . | . . . . . | . . H . . | . . . . N | . . L . . | . . . . . | . . R Y . | . . F . . | . . . . |
| iPS:43 6023 | 21-225_193A5 | VK1|A30/ JK4 | . . F . . | . . . . . | . . V . . | . . . . . | . . . . . | . . . F . | . . . D . | . . . . . | . . . . |
| iPS:43 6033 | 21-225_193E7 | VK1|A30/ JK4 | . . I . S | . . . . . | . . . . . | . . . . . | . . i . V | . . . . E | . . . . . | . . F . F | . . . . |
| iPS:43 6120 | 21-225_196C10 | VK1|A30/ JK4 | . . . . . | . . . . . | . . . S . | . . . . R | . . . . . | . . . . . | . . K R . | . . . . . | . . . . |
| iPS:43 6199 | 21-225_199E3 | VK1|A30/ JK4 | . . . . . | . . . . . | . . . S . | . . . . R | . . . . . | . . . . . | . . . Y . | . . . . . | . . . . |
| iPS:43 6228 | 21-225_200F12 | VK1|A30/ JK4 | . . . . . | . . . . . | . . . R S | . . H T | . . . . . | . . . . . | . . K R . | . . . . . | . . . . |
| iPS:43 6230 | 21-225_201A1 | VK1|A30/ JK4 | . . . . . | . . . . . | . . . S . | . . i . R | . . . . . | . . . . . | . . . K . | . . . . . | . . . . |
| iPS:43 6242 | 21-225_201A10 | VK1|A30/ JK4 | . . . . . | . . E . . | . . . R S | . . i . H | . . . . . | . . . . . | . . . K . | . . . . . | . . . V |
| iPS:43 6286 | 21-225_204H8 | VK1|A30/ JK4 | . . . . . | . . S . . | . . . S . | . . . . . | . . . V . | . . . . R | . . . . . | . . . . . | . . . . |
| iPS:43 6308 | 21-225_205H8 | VK1|A30/ JK4 | . . . . . | . . . . . | . . L Q . | . . F . R | . . . . . | . . . S A | . . . . . | . . . . . | . . T . . |
| iPS:43 6526 | 21-225_224A1 | VK1|A30/ JK4 | . . . . . | . . . . . | . . . . . | . . . . . | . . . . . | . . . . . | . . . . . | . . . . . | . . K . . |
| iPS:43 6528 | 21-225_224B1 | VK1|A30/ JK4 | . . . . . | . . D . . | . . . . . | . . . . . | . . . . . | . . . H . | . . . . . | . . P . . | . . . . |
| iPS:43 6538 | 21-225_224C3 | VK1|A30/ JK4 | . . . . . | . . . . . | . . . T . | . . . . . | . . . . . | . . . . . | . . . . . | . . . . . | . . . . |

Figure 52 (Continued)

| | | | | | | | | | |
|---|---|---|---|---|---|---|---|---|---|
| iPS:43 6356 | 21-225_224D10 | VK1|A30/ JK4 | .L...... | ........ | ........ | ........ | ........ | ........ | ........ |
| iPS:43 7220 | 21-225_55H6 | VK1|A30/ JK4 | ........ | ........ | ........ | ........ | ........ | ..RD.... | ......F. |
| iPS:43 7346 | 21-225_75H7 | VK1|A30/ JK4 | ......RY ..NS | ........ | S.Q..... | G....... | ........ | T.SN.... | ........ |
| iPS:47 2730 | 21-225_14B1_L C1 | VK1|A30/ JK4 | ......Y. ..DN.. | ........ | ........ | D....... | ....V... ...GV.. | ...YN... | ........ |
| iPS:39 2622 | 21-225_17H8 | VK1|A30/ JK4 | ........ | ........ | ........ | T.....Y. | ........ | ........ | ........ |
| iPS:39 2624 | 21-225_17H12 | VK1|A30/ JK4 | ........ | ........ | A... ..M | G....... | .....T.. | ..Y..... | ........ |
| iPS:39 2628 | 21-225_20C2 | VK1|A30/ JK4 | ....Q... | ........ | ...F.... | ........ | ...I.... ..TG... | ........ | ...MF... |
| iPS:39 2630 | 21-225_20E5 | VK1|A30/ JK4 | ........ | ........ | ........ | ........ | ........ | ..A..... | ........ |
| iPS:39 2638 | 21-225_17F9 | VK1|A30/ JK4 | ........ | ....V... | ........ | V....... | ...N.... | ........ | ........ |
| iPS:39 2640 | 21-225_18A1 | VK1|A30/ JK4 | ........ | ........ | ........ | ........ | ........ | ........ | ........ |
| iPS:39 2642 | 21-225_18C6 | VK1|A30/ JK4 | ....T... | ........ | ........ | ........ | ........ | ..S..... | ........ |
| iPS:39 2644 | 21-225_19E1 | VK1|A30/ JK4 | ........ | ........ | ........ | N....... | ........ | ........ | ........ |
| iPS:39 2646 | 21-225_20G2 | VK1|A30/ JK4 | ........ | ........ | ........ | V....... | ....S... | ...F.... | ........ |
| iPS:39 2654 | 21-225_17A10 | VK1|A30/ JK4 | ........ | ........ | ........ | ........ | ........ | ........ | ........ |
| iPS:39 2656 | 21-225_1F2 | VK1|A30/ JK4 | ........ | ........ | ........ | V....... | ...I.... | ........ | ........ |
| iPS:39 2658 | 21-225_18E8 | VK1|A30/ JK4 | ....A... | ........ | ........ | ........ | ........ | ........ | ........ |
| iPS:39 2666 | 21-225_16F11 | VK1|A30/ JK4 | ........ | ........ | ........ | ........ | ........ | ........ | ........ |
| iPS:39 2676 | 21-225_19F3 | VK1|A30/ JK4 | ....R... | ........ | ........ | V....... | ........ | ..A..... | ........ |
| iPS:39 2680 | 21-225_20A7 | VK1|A30/ JK4 | ........ | ........ | ........ | ........ | ...S.... | ........ | ........ |
| iPS:39 2700 | 21-225_16E12 | VK1|A30/ JK4 | ........ | ........ | ........ | ........ | ...N.... | ........ | ........ |
| iPS:39 2706 | 21-225_18A3 | VK1|A30/ JK4 | ........ | ........ | ........ | V....... | ........ | ..S..... | ........ |

Figure 52 (Continued)

| | | | | | | | | | |
|---|---|---|---|---|---|---|---|---|---|
| iPS:39 2716 | 21-225_17B5 | VK1｜A30/ JK4 | | | | | SF. | | |
| iPS:39 2744 | 21-225_20D5 | VK1｜A30/ JK4 | | | | | | | |
| iPS:39 2750 | 21-225_20A10 | VK1｜A30/ JK4 | | | Q.. | | | ..R | |
| iPS:39 2772 | 21-225_20E12 | VK1｜A30/ JK4 | | | F. | | | | |
| iPS:39 2774 | 21-225_21F3 | VK1｜A30/ JK4 | | | | | I | ..S | F. |
| iPS:39 2780 | 21-225_22B7 | VK1｜A30/ JK4 | | | | T. | | ..T | |
| iPS:39 2788 | 21-225_20C8 | VK1｜A30/ JK4 | | | K..N | | | ..D. | F. |
| iPS:39 2794 | 21-225_21H3 | VK1｜A30/ JK4 | | | | V.T | A.L.I | ..ST | |
| iPS:39 2800 | 21-225_22D12 | VK1｜A30/ JK4 | | ..D | | | D | | |
| iPS:39 2810 | 21-225_20H12 | VK1｜A30/ JK4 | | | | | | | |
| iPS:39 2820 | 21-225_23D1 | VK1｜A30/ JK4 | ..R | ..D | .RG | | V | ..S | |
| iPS:39 2822 | 21-225_23C8 | VK1｜A30/ JK4 | F | T | N | V | VI | | |
| iPS:39 2824 | 21-225_24E5 | VK1｜A30/ JK4 | | ..K.. | | | | ..SN | |
| iPS:39 2834 | 21-225_22C1 | VK1｜A30/ JK4 | G | ..N | G.C | | | ..ST | |
| iPS:39 2838 | 21-225_22G8 | VK1｜A30/ JK4 | | | | | ..K ..S | | |
| iPS:39 2850 | 21-225_20H10 | VK1｜A30/ JK4 | | | | T. | | | |
| iPS:39 2854 | 21-225_21E5 | VK1｜A30/ JK4 | | D | | V. | L | | |
| iPS:39 2858 | 21-225_22H4 | VK1｜A30/ JK4 | | | | | | | |
| iPS:39 2866 | 21-225_23H11 | VK1｜A30/ JK4 | | | | | | ..R | |
| iPS:39 2870 | 21-225_20G9 | VK1｜A30/ JK4 | | | | | | ..ST | T. |
| iPS:39 2880 | 21-225_22F9 | VK1｜A30/ JK4 | | | | | | | |

Figure 52 (Continued)

| | | | | | | | | | |
|---|---|---|---|---|---|---|---|---|---|
| iPS:39 2882 | 21-225_23A3 | VK1JA30/ JK4 | . | . | . | . | . | . | . |
| iPS:39 2896 | 21-225_21G7 | VK1JA30/ JK4 | . | V. | .Q. | . | .N. | .iF | .S. |
| iPS:39 2900 | 21-225_22F2 | VK1JA30/ JK4 | . | . | . | . | . | . | . |
| iPS:39 2904 | 21-225_22G9 | VK1JA30/ JK4 | . | .D. | . | . | . | . | .A. |
| iPS:39 2942 | 21-225_30E9 | VK1JA30/ JK4 | . | .D | .R. | G.F. | . | . | . |
| iPS:39 2944 | 21-225_31H5 | VK1JA30/ JK4 | F.SF | .D.S. | H.T. | . | F..M.D.SN. | . | .T. ..P. |
| iPS:39 2964 | 21-225_31A8 | VK1JA30/ JK4 | . | .D.S. | . | V. | . | . | I..II ..P. |
| iPS:39 2980 | 21-225_29H6 | VK1JA30/ JK4 | . | . | .S.T. | . | . | . | . |
| iPS:39 2982 | 21-225_30D1 | VK1JA30/ JK4 | . | .D.S. | .E. | . | . | .T. | .TI ..P. |
| iPS:39 2986 | 21-225_31B8 | VK1JA30/ JK4 | .I. | .D.S. | . | G. | . | . | .TI ..P. |
| iPS:39 2988 | 21-225_25E6 | VK1JA30/ JK4 | . | .R. | .R. | . | ..R.N. | . | . |
| iPS:39 2990 | 21-225_25H10 | VK1JA30/ JK4 | . | .D. | . | .F. | . | . | . |
| iPS:39 3004 | 21-225_30G11 | VK1JA30/ JK4 | . | .D.S. | . | G. | . | .R. | . |
| iPS:39 3018 | 21-225_29B8 | VK1JA30/ JK4 | . | . | . | . | . | . | . |
| iPS:39 3030 | 21-225_25H11 | VK1JA30/ JK4 | . | .T. | . | . | . | . | . |
| iPS:39 3034 | 21-225_27F2 | VK1JA30/ JK4 | . | . | . | V. | . | . | . |
| iPS:39 3040 | 21-225_30E3 | VK1JA30/ JK4 | . | .D. | .R. | . | . | .F. | .T. ..P. |
| iPS:39 3048 | 21-225_27C3 | VK1JA30/ JK4 | . | .D. | .L. | . | . | . | . |
| iPS:39 3054 | 21-225_29G8 | VK1JA30/ JK4 | . | . | . | . | . | .N. | .R. |
| iPS:39 3056 | 21-225_30F3 | VK1JA30/ JK4 | . | . | . | H. | . | .D.S | . ..F. |
| iPS:39 3058 | 21-225_31H3 | VK1JA30/ JK4 | . | .D. | .R. | .F. | . | . | .T. ..P. |

Figure 52 (Continued)

| ID | Name | Type | | | | | | | | | | |
|---|---|---|---|---|---|---|---|---|---|---|---|---|
| iPS:39 3060 | 21-225_32G12 | VK1|A30/ JK4 | . . . . . . . . . . | . . . . D . . . . S . . | . . . . R . . . . . . . | . . . . . . . . . . . . | . . . . . . . . . . . . | . . . . . . . . . . . . | . TI . . . . . . . . | . . . . . . . . . . . . |
| iPS:39 3068 | 21-225_34G9 | VK1|A30/ JK4 | . . . . . . . . . . | . . . . D . . . . S . . | . . . . . . . . . . . . | . . . . . . . . . . . . | . . . . T . . . . . . . | . . . . P . . . . . . . | . TI . . . . . . . . | . W . . . . . . . . . . |
| iPS:39 3072 | 21-225_36C5 | VK1|A30/ JK4 | . . . . . . . . . . | . . . . D . . . . S . . | . . . . . . . . . . . . | . . . . . . . . . . . . | . . . . T . A . I . . . | . H . PI . . . . . . . | . . . . . . . . . . . . | . W . . . . . . . . . . |
| iPS:39 3074 | 21-225_33B1 | VK1|A30/ JK4 | . . . . . . . . . . | . F . . . . . . . . . . | . . . . F . . . . . . . | . . . . . . . . . . . . | . . . . V . . . . . . . | . . . . P . . . . . . . | . . . . . . . . . . . . | . . . . . . . . . . . . |
| iPS:39 3076 | 21-225_33A4 | VK1|A30/ JK4 | . . . . . . . . . . | . . . . D . . . . V . . | . . . . . . . . . . R . | . . . . . . . . . . . . | . . . . . . . . . . . . | . Y . . . . . . . . . . | . . . . . . . . . . . . | . V . . . . . . . . . . |
| iPS:39 3096 | 21-225_34D11 | VK1|A30/ JK4 | . . . . . . . . . . | . . . . . . . . . . . . | . E . . . . . . . . . . | . . . . . . . . . . . . | . . . . . . . . . . . . | . TI . . . . . . . . | . . . . P . . . . . . . | . . . . . . . . . . . . |
| iPS:39 3102 | 21-225_33F1 | VK1|A30/ JK4 | . . . . . . . . . . | . F . . . D . . . . S . | . . . . . . . . . . . . | . . . . . . . . . . . . | . VT . . . . . . . . | . TI . . . . . . . . | . . . . P . . . . . . . | . G . . . . . . . . . . |
| iPS:39 3104 | 21-225_33A7 | VK1|A30/ JK4 | . . . . . . . . . . | . . . . D . . . . S . . | . V . . . . . . . . . . | . . . . . . . . . . . . | . . . . . . . . . I . . | . TI . . . . . . . . | . . . . P . . . . . . . | . . . . . . . . . . . . |
| iPS:39 3106 | 21-225_34A6 | VK1|A30/ JK4 | . . . . . . . . . . | . F . . . D . . . . S . | . . . . . . . . . . . . | . . . . . . . . . . . . | . V . . . . . . . . . A | . . . . . . . . . . . . | . . . . P . . . . . . . | . . . . . . . . . . . . |
| iPS:39 3110 | 21-225_35B7 | VK1|A30/ JK4 | . . . . . . . . . . | . . . . D . . . . S . . | . E . . . . . . . . . . | . . . . . . . . . . . . | . . . . . . . . . . . . | . . . . . . . . . . . . | . TI . . . . . . . . | . . . . . . . . . . . . |
| iPS:39 3118 | 21-225_34H11 | VK1|A30/ JK4 | . . . . . . . I . . | . . . . D . . . . S . . | . . . . . . . . . . . . | . . . . H . . . . . . . | . . . . . . . . . . . . | . . . . . . . . . . . . | . . . . P . . . . . . . | . . . . . . . . . . . . |
| iPS:39 3124 | 21-225_33G7 | VK1|A30/ JK4 | . . . . . . . . . . | . . . . D . . . . . . . | . . . . . . . . . . . . | . . . . . . . . . . . . | . . . . . . . . . . . . | . . . . . . . . . . . . | . . . . P . . . . . . . | . . . . . . . . . . . . |
| iPS:39 3126 | 21-225_35D1 | VK1|A30/ JK4 | . . . . . . . . . . | . . . . D . . . . S . . | . . . . F . . . . . . . | . . . . . . . . . . . . | . . . . . . . . . . . . | . Y . . . . . . . . . . | . . . . P . . . . . . . | . . . . . . . . . . . . |
| iPS:39 3128 | 21-225_35F11 | VK1|A30/ JK4 | . . . . . . . . . . | . . . . . . . . . . . . | . . . . . . . . . . . . | . V . . . . . G . . . . | . . . . . . . . . . . . | . TV . . . . . . . . | . . . . P . . . . . . . | . . . . . . . . . . . . |
| iPS:39 3146 | 21-225_34G8 | VK1|A30/ JK4 | . . . . . . . . . . | . . . . D . . . . S . . | . . . . . . . . . . . . | . . . . . . . . . . . . | . . . . . . . . . . . . | . TI . . . . . . . . | . . . . P . . . . . . . | . . . . . . . . . . . . |
| iPS:39 3150 | 21-225_36A5 | VK1|A30/ JK4 | . . . . . . . . . . | . T . . . D . . . . . . | . . . . . . . . . . . . | . . . . . . . . N . . . | . . . . . . . . . . . . | . H . . . . . . . . . . | . . . . PK . . . . . | . I . . T . . . . . . . |
| iPS:39 3804 | 21-225_5H7 | VK1|A30/ JK4 | . . . . . . . . . . | . . . . . . . . . . . . | . . . . . . . . . . . . | . . . . . . . . . . . . | . . . . . . . . . . . . | . . . . . . . . . . . . | . . . . . . . . . . . . | . . . . . . . . . . . . |
| iPS:39 3806 | 21-225_6A6 | VK1|A30/ JK4 | . . . . . . . . . . | . . . . . . . . . . . . | . . . . . . . . . . . . | . . . . . . . . . . . . | . . . . . . . . . . . . | . S . . . . . . . . . . | . . . . . . . . . . . . | . . . . . . . . . . . . |
| iPS:39 3808 | 21-225_1A2 | VK1|A30/ JK4 | . . . . . . . . . . | . . . . . . . . . . . . | . . . . . . . . . . . . | . . . . . . . . . . . . | . . . . . . . . . . . . | . . . . . H . . . . . . | . . . . . . . . . . . . | . . . . . . . . . . . . |
| iPS:39 3814 | 21-225_7F4 | VK1|A30/ JK4 | . . . . . . . . . . | . . . . A . . . . . . . | . . . . . . . . . . . . | . . . . . . . . . . . . | . . . . . . . . . . . . | . SA . . . . . . . . | . . . . . . . . . . . . | . . . . . . . . . . . . |
| iPS:39 3816 | 21-225_6D4 | VK1|A30/ JK4 | . . . . . . . . . . | . . . . . . . . . . . . | . . . . . . . . . . . . | . . . . . . . . . . . . | . . . . . . . . . . . . | . S . . . . . . . . . . | . . . . . . . . . . . . | . . . . . . . . . . . . |

| | | | F | | | E.T | | | | | | M |
|---|---|---|---|---|---|---|---|---|---|---|---|---|
| iPS:39 3976 | 21-225_7E9 | VK1|A30/ JK4 | . . . . . . | . . . . . . | . . . . . . | . . . . . . | . . . . . . | . . . . . . | . . . . . . | . . . . . . | . . . . . . |
| iPS:39 3982 | 21-225_6C12 | VK1|A30/ JK4 | . . . . . . | . . . SN . . | . . . . . . | . . . . . . | . . . . . . | . . . . . . | . . . . . . | . . . D . . | . . . . . . |
| iPS:39 3984 | 21-225_4F12 | VK1|A30/ JK4 | . . . . . . | . . . . G . | . . . . . . | . . . . E . | . . . G . . | . . F . I . | . . . . . . | . . . . F . | . . . . . . |
| iPS:39 3990 | 21-225_11G7 | VK1|A30/ JK4 | . . . . . . | . . . . . . | . . A . . . | . . . . . . | . . . . . . | . . . . . . | . . . . . . | . . SN . A . | . . . . M.R |
| iPS:39 3994 | 21-225_8C9 | VK1|A30/ JK4 | . . . . . . | . . . . . . | . . . D . . | . . . . . . | . . . . . . | . . . . . . | . . . . . . | . . . . . . | . . . . . . |
| iPS:39 4002 | 21-225_15G7 | VK1|A30/ JK4 | . . . . . . | . . . . . . | . . . . . . | . . . . . . | . . . T . . | . . . I . . | . . . . . . | . . . SN . . | . . . . . R |
| iPS:39 4008 | 21-225_15H8 | VK1|A30/ JK4 | . . . . . . | . . . . . . | . . . F . . | . . . . . . | . . . . . . | . . F . F . | . . . . . . | . . . . . . | . . . . . N |
| iPS:39 4020 | 21-225_15H10 | VK1|A30/ JK4 | . . . . . . | . . . . . . | . . . . . . | . . . . . . | . . . . S . | . . . . S . | . . . . . . | . . . . . . | . . . . FN |
| iPS:39 4024 | 21-225_16B7 | VK1|A30/ JK4 | . . . . . . | . . . . . . | . . . . . . | . . V.T . . | . . . . . . | . . . . I . | . . . . . . | . . . . . . | . . . . . . |
| iPS:39 4037 | 21-225_4F4 | VK1|A30/ JK4 | . . . . . . | . . . . . . | . . . . . . | . . . V . . | . . I . . . | . . . . . . | . . . . . . | . . . . . . | . . . . . . |
| iPS:39 4045 | 21-225_4H4 | VK1|A30/ JK4 | . . . . . . | . . . . . . | . . . . . . | . . . . . . | . . . . T . | . . . . . . | . . . . . . | . . . . . . | . . . . . . |
| iPS:39 4049 | 21-225_13H5 | VK1|A30/ JK4 | . . . . . . | . . . . . . | . . . . . . | . . . . . . | . . . . . N | . . . V . . | . . . . . . | . . . S . . | . . . . . . |
| iPS:39 4053 | 21-225_11F10 | VK1|A30/ JK4 | . . . . . . | . . . . . . | . . . . . . | . . . . T . | . . . . . . | . . . . . . | . . . . . . | . . . S . . | . . . . . . |
| iPS:39 4057 | 21-225_15H1 | VK1|A30/ JK4 | . . . . . . | . . . . . . | . . . . . . | . . . . . . | . . . . . . | . . . . I . | . . . . . . | . . . . . . | . . . . . . |
| iPS:39 4059 | 21-225_9E8 | VK1|A30/ JK4 | . . . F . . | . . . . . . | . . . . . . | . . . . . . | . . . . . . | . . . . . . | . . . . . . | . H.SN . . | . . . . . . |
| iPS:39 4063 | 21-225_16A1 | VK1|A30/ JK4 | . . . . . . | . . . . . . | . . . . . . | . . . . . . | . . . . . . | . . . . . . | . . . . . . | . . T . . . | . . . E . . |
| iPS:39 4073 | 21-225_15C9 | VK1|A30/ JK4 | . . . . . . | . . . . . . | . . . . . . | . . V . . . | . . . . N . | . . . . . . | . . . . . . | . . . S . . | . . . . . . |
| iPS:39 4075 | 21-225_8D12 | VK1|A30/ JK4 | . . . . . . | . . . . . . | . . . . . . | . . . . . . | . . . . . . | . . . . I . | . . . . . . | . . . . . . | . . . . . . |
| iPS:39 4079 | 21-225_11F5 | VK1|A30/ JK4 | . . . . . . | . . . . . . | . . . . . . | . . . . . . | . . . . . . | . . . . . . | . . . . . . | . . . . . . | . . . . . . |
| iPS:39 4091 | 21-225_13H3 | VK1|A30/ JK4 | . . . . . . | . . . . . . | . . . DM . . | . . . . . . | . . . . . . | . . . . . . | . . . . . . | . . . TI . . | . . . . . . |
| iPS:39 8528 | 21-225_32G1 | VK1|A30/ JK4 | . . . . . . | . . . . . . | . . . . S . | . . . . . . | . . . . . . | . . . . . . | . . . . . . | . . . . S.P. | . . . . . . |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:39 8534 | 21-225_33B8 | VK1|A30/ JK4 | .................... | ......D..... | ............ | ............ | .................... | ...TI...... | ..... |
| iPS:39 8540 | 21-225_35A6 | VK1|A30/ JK4 | .................... | ......S..D.. | ............ | ....T....... | .................... | ...TI...P.. | ..... |
| iPS:40 2219 | 21-225_1C12 | VK1|A30/ JK4 | .................... | ......S..... | ............ | ............ | .................... | ............ | ..A.. |
| iPS:40 3868 | 21-225_19D11 | VK1|A30/ JK4 | .................... | ............ | ............ | ....T....... | ............E....... | ...YY....... | ..... |
| iPS:40 3872 | 21-225_8F11 | VK1|A30/ JK4 | .................... | ......S..... | ...F........ | ...D....V... | .................... | ...YT....... | ...E. |
| Germline | VK2|A18|JK 5 | K_FR1 DIVMTQTPLSLS VTPGQPASIS | K_CDR1 CRSSQSLLHSD GNTYLN | K_FR2 WYLQKPGQSPQ LLIY | K_CDR2 LGS---NRA | K_FR3 SGVPDRFSGSGS GTDFTLKISRVEAEDVGV YYC | K_CDR3 MQALQ-------TPYT | K_FR4 FGQGTK LEIK |
| iPS:46 8816 | 21-225_52G8 | VK2|A18/ JK5 | ...................M. | ............ | ............ | ....K.L..... | ............M....... | ...SMQ....I. | ..... |
| iPS:43 4021 | 21-225_49C1 | VK2|A18/ JK5 | .................... | ......E..... | ...P.H...... | ......H..... | .................... | ...S.Q....I. | ..L.. |
| iPS:43 4025 | 21-225_49G3 | VK2|A18/ JK5 | ...................M. | ......E..... | ...A.F..F... | ....T........ | ............M....... | ...SMQ....... | ..... |
| iPS:43 4031 | 21-225_49E7 | VK2|A18/ JK5 | .................FM. | ............ | ...P.H...... | ....K.L..... | ............M.F..... | ...SMQ....I. | ..... |
| iPS:43 4033 | 21-225_49F9 | VK2|A18/ JK5 | .................... | ...N....V.N. | ...P........ | ......N...... | .................... | ...S.Q....Y. | ..... |
| iPS:43 4093 | 21-225_52D10 | VK2|A18/ JK5 | .................... | ............ | ...P........ | ....N.V...... | ............R....... | ...S.Q....Y. | ..... |
| iPS:43 4151 | 21-225_55C2 | VK2|A18/ JK5 | ....VM..I......... | ............ | ...P....F... | ....N.V...... | ............R....... | ...S.L....Y. | ..... |
| iPS:43 4161 | 21-225_55F9 | VK2|A18/ JK5 | ....VM..I........S. | ......V..... | ...P....F... | ......N...... | ............I.S..... | I.S.Q........ | ..... |
| iPS:43 5329 | 21-225_147A8 | VK2|A18/ JK5 | .................... | ...T....E... | ...P........ | ............ | .................... | ...S.---....QL... | ..... |
| iPS:43 2924 | 21-225_32H2 | VK2|A18/ JK5 | .................... | ......R..... | ...P........ | ....A.N...... | .................... | L.S.Q....Y. | ..... |
| Germline | VK2|A18|JK 1 | K_FR1 DIVMTQTPLSLS VTPGQPASIS | K_CDR1 CRSSQSLLHS QGILAST GNTYLN | K_FR2 WYLQKPGQ SPQLLIY | K_CDR2 LGS VSSRFS | K_FR3 GVPDRFSGSGS GTDFTLKISRVEAEDVGV YYC | K_CDR3 MQALQ-------LPWT | K_FR4 FGQGTK VEIK |
| iPS:46 8822 | 21-225_147E10 | VK2|A18/ JK1 | A................... | ......R...G. | ...P.H...S.. | ......N..... | .................... | ...S.Q....V. | ..... |
| iPS:43 3917 | 21-225_43E11 | VK2|A18/ JK1 | .................... | ......R..... | ...P........ | ......N..... | .................... | ...S.Q....Y. | ..... |

Figure 52 (Continued)

| | | | | T | | | G | P.V. | N | L | | S.Q | . |
|---|---|---|---|---|---|---|---|---|---|---|---|---|---|
| iPS:43 3965 | 21-225_46F2 | VK2|A18/ JK1 | . | . | . | . | . | P.V. | .N. | . | . | ..S.Q... | . |
| iPS:43 3985 | 21-225_47C1 | VK2|A18/ JK1 | . | F. E. | . | . | . | . | . | . | F. | ..S.Q... | . |
| iPS:43 3991 | 21-225_47E7 | VK2|A18/ JK1 | . | . | . | .R. | . | .P. | . | . | . | ..STQ... | A. |
| iPS:43 4345 | 21-225_64H9 | VK2|A18/ JK1 | E. | . | . | . | F. | . | . | A. | . | ..S.Q..V | . |
| iPS:43 5297 | 21-225_146B3 | VK2|A18/ JK1 | . | . | . | . | . | .P. | .N.LC | S. | L.H | ..S.Q... | .T |
| iPS:43 5341 | 21-225_148B2 | VK2|A18/ JK1 | A. | . | . | . | F. | .P. | .N. | . | . | ..S.Q..I | . |
| iPS:43 5357 | 21-225_148G10 | VK2|A18/ JK1 | . | . | . | . | . | .P. .R | .H. | . | . | ..S.Q... | . |
| iPS:43 5365 | 21-225_149F1 | VK2|A18/ JK1 | . | S...F Y | . | . | F. | .P. | .N. | . | . | ..S.Q..I | . |
| iPS:43 5413 | 21-225_150B11 | VK2|A18/ JK1 | . | . | . | .R. | V.G | .P. .R | .H. | . | . | ..S.Q... | . |
| iPS:43 5423 | 21-225_151G5 | VK2|A18/ JK1 | . | . | A. | . | .G | .P. L | . | . | . | ..S.Q..V | . |
| iPS:43 5429 | 21-225_151A10 | VK2|A18/ JK1 | . | . | . | . | .G | .P. .R | .N. | .N | . | ..S.Q..I | . |
| iPS:43 5441 | 21-225_152F6 | VK2|A18/ JK1 | . | . | . | . | R.G T | P.V.H | .I.K.T | .N | F. | ..S.Q..V | . |
| iPS:43 5457 | 21-225_152C11 | VK2|A18/ JK1 | . | . | . | . | .G | .P. L | . | . | F.F | ..S.Q..I | D. |
| iPS:43 5463 | 21-225_153D2 | VK2|A18/ JK1 | . | . | . | . | R.G T | .P. .R | .K.T | .N | F. | ..S.Q..V | . |
| iPS:43 5489 | 21-225_155A5 | VK2|A18/ JK1 | . | . | . | . | .G | .P. | .N. | . | F. | ..S.Q..V | . |
| iPS:43 5531 | 21-225_157G8 | VK2|A18/ JK1 | . | . | . | . | . | . | .I.K | SE | . | ..S.Q..V | . |
| iPS:43 5577 | 21-225_160B1 | VK2|A18/ JK1 | . | . | . | . | .G | P.V. | .K. | . | L. | ..S.Q..I | . |
| iPS:43 5601 | 21-225_160G10 | VK2|A18/ JK1 | A. | . | . | . | F. | .P.H | .K. | E. | . | ..S.Q... | .V |
| iPS:43 5629 | 21-225_162H6 | VK2|A18/ JK1 | . | . | T. | . | . | .P. | .K. | . | . | .K.S.Q... | .T |
| iPS:43 5655 | 21-225_167E2 | VK2|A18/ JK1 | . | . | . | . | .G | P.H | .K. | . | L.H | ..S.Q... | . |
| iPS:43 5657 | 21-225_167H10 | VK2|A18/ JK1 | . | . | . | . | .G | P.H | .K. | . | L.H | ..S.Q... | . |

Figure 52 (Continued)

| | | | | | | | | | | | |
|---|---|---|---|---|---|---|---|---|---|---|---|
| iPS:43 5683 | 21-225_170A1 | VK2|A18/ JK1 | E....... | ........ | ........ | ....G | ........ | ........ | ........ | ........ | ........ |
| iPS:43 5723 | 21-225_172B7 | VK2|A18/ JK1 | ........ | ........F.. | ....F.. | ....G | P..V.. | ........ | ....G | ..S.Q.... | ....F.. D |
| iPS:43 5731 | 21-225_173A11 | VK2|A18/ JK1 | ........ | ........ | ........ | ....G | P...... | ........ | ........ | ..S.Q.... | ....V.. |
| iPS:43 5755 | 21-225_176H4 | VK2|A18/ JK1 | ........ | ........ | ........ | ....G | P...... | ....N.. | ....FF.. | ..S.Q.... | ....I.. R |
| iPS:43 5771 | 21-225_177B11 | VK2|A18/ JK1 | ........ | ........ | ....R... | ....G | P...... | ........ | ....E.. | ..S.Q.... | ........ |
| iPS:43 5781 | 21-225_178G10 | VK2|A18/ JK1 | H....... | ........ | ........ | ....G | P..V.LF | ....N.. | ..L.G... | ..S.Q.... | ....I.. |
| iPS:43 5789 | 21-225_180C4 | VK2|A18/ JK1 | ........ | ........ | ........ | ....G | P...... | ....N.. | ....I... | ..S.Q.... | ....V.. |
| iPS:43 5795 | 21-225_181C2 | VK2|A18/ JK1 | E....... | ........ | ........ | ....G | P...... | A.N.P.. | ..S..... | ..S.Q.... | ....V.. |
| iPS:43 5807 | 21-225_181C10 | VK2|A18/ JK1 | ........ | ........ | ........ | ........ | P...... | ....N.. | ........ | ..S.Q.... | ....I.. |
| iPS:43 5827 | 21-225_190H11 | VK2|A18/ JK1 | ........ | ........ | ..R..... | ........ | P....C. | ....N.A | ..T..... | ..S.Q.... | ........ |
| iPS:43 5839 | 21-225_191B1 | VK2|A18/ JK1 | ........ | ........ | R...F... | ........ | P..V... | L.N.... | ....H... | ..SFQ.... | ....F.. |
| iPS:43 5853 | 21-225_191E3 | VK2|A18/ JK1 | ........ | ........ | ..R..... | ........ | P....C. | ....N.A | ..T..... | ..S.Q.... | ........ |
| iPS:43 5871 | 21-225_191E6 | VK2|A18/ JK1 | ........ | ........ | ..R..... | ........ | P....C. | ....N.A | ..T..G.. | ..S.Q.... | ........ |
| iPS:43 5887 | 21-225_186F7 | VK2|A18/ JK1 | .V.A.... | ........ | M....... | ........ | P...... | ....K.. | ..S..G.. | ..S.Q.... | ....V.. |
| iPS:43 5899 | 21-225_188G11 | VK2|A18/ JK1 | ........ | ........ | ..R..... | ....G | P...... | ....N.. | ..T..G.. | ..S.Q.... | ....I.. |
| iPS:43 5901 | 21-225_189G2 | VK2|A18/ JK1 | ........ | ........ | ....F... | ....G | P...... | ........ | ....G.. | ..S.Q.... | ....I.. |
| iPS:43 5927 | 21-225_190E7 | VK2|A18/ JK1 | ....L... | ........ | ........ | ........ | ........ | ........ | ....G.. | ..S.Q.... | ........ |
| iPS:43 5999 | 21-225_192F9 | VK2|A18/ JK1 | ........ | ........ | ..R..... | ........ | ..R..... | ....N.. | ....G.. | ..S.Q.... | ........ |
| iPS:43 6060 | 21-225_194F4 | VK2|A18/ JK1 | ....I... | ........ | ..R..N.. | ........ | P...... | ........ | ....S.. | ..S.Q.... | ........ |
| iPS:43 6158 | 21-225_197G8 | VK2|A18/ JK1 | ....L... | ........ | ..R..Y.. | ........ | P..V... | ....N.. | ....G.. | ..S.Q.... | ....A.S |
| iPS:43 6193 | 21-225_198A10 | VK2|A18/ JK1 | ........ | ........ | ........ | ........ | P..V.C. | ....N.. | ....G.. | ..S.Q.... | ........ |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 6536 | 21-225_224G1 | VK2A18/JK1 | ...G...... | ....F.S | P........ | .I.N... | ......... | ..STQ...... | ......... |
| iPS:43 6548 | 21-225_224A7 | VK2A18/JK1 | ......... | .....F.. | ..F.P.... | .I.N... | ......... | ..STQ...R. | ......... |
| iPS:43 6558 | 21-225_224C11 | VK2A18/JK1 | .F....... | .....F.. | ....P.... | .I.N... | ......... | ..STQ...R. | ......... |
| iPS:43 6562 | 21-225_224H11 | VK2A18/JK1 | ......... | .....F.. | ....P.... | .I.N... | ......... | ..STQ...R. | ......... |
| iPS:43 6572 | 21-225_225G4 | VK2A18/JK1 | ......... | .....F.. | ....P.... | .I.N... | ......... | ..STQ...R. | ......... |
| iPS:43 6592 | 21-225_226B1 | VK2A18/JK1 | ......... | ......G. | ....P...R | ....N.. | ......... | ..S.Q...I. | ......... |
| iPS:43 6594 | 21-225_226A5 | VK2A18/JK1 | ......... | ......G. | ....P.... | ....N.. | ......... | ..S.Q...I. | ....D.... |
| iPS:43 6602 | 21-225_226E7 | VK2A18/JK1 | ......... | ......G. | ..P.I.... | ....N.. | ......... | ..S.Q...V. | ......... |
| iPS:43 6606 | 21-225_226G8 | VK2A18/JK1 | ......... | ......... | ....P.... | .I.N... | ......... | ..STQ...R. | ......... |
| iPS:43 6610 | 21-225_226F9 | VK2A18/JK1 | ......... | ......... | ....P.... | .I.N... | ......... | ..STQ...R. | ......... |
| iPS:43 6612 | 21-225_226H9 | VK2A18/JK1 | .I....... | .....F.. | ....P...R | .I.N... | ......... | ..STQ...R. | ......... |
| iPS:43 6614 | 21-225_226F10 | VK2A18/JK1 | ......... | .....F.. | ....P.... | .I.N... | ......... | ..STQ...R. | ......... |
| iPS:43 6618 | 21-225_226E11 | VK2A18/JK1 | ......... | .....F.. | ..P.H.... | .I.N... | ......... | ..STQ...R. | ......... |
| iPS:43 6624 | 21-225_226H12 | VK2A18/JK1 | ......... | ....KT.. | ..P.H.... | .I.N... | ......... | ..STQ...R. | ......... |
| iPS:43 6626 | 21-225_227C1 | VK2A18/JK1 | ......... | .....F.. | ....P.F.. | .I.N... | ......... | ..STQ...R. | ......... |
| iPS:43 6628 | 21-225_227F2 | VK2A18/JK1 | ......... | .....F.. | ....P.... | .I.N... | ......... | ..STQ...R. | ......... |
| iPS:43 6640 | 21-225_227A8 | VK2A18/JK1 | ......... | .....F.. | ....P.... | .I.N... | ......... | ..STQ...R. | ....R.... |
| iPS:39 2814 | 21-225_22A1 | VK2A18/JK1 | ......... | G........ | ....P.... | ....N.. | .L....A.. | ..STQ...R. | ......... |
| iPS:39 2930 | 21-225_25H9 | VK2A18/JK1 | ......... | ......G. | ....P.... | ....N.. | ......... | ..TL...... | ......... |
| iPS:39 3032 | 21-225_26F8 | VK2A18/JK1 | ......... | .....F.. | ....P.... | ....N.. | ......... | ..S.Q...I. | ......... |
| iPS:39 3036 | 21-225_28G3 | VK2A18/JK1 | E........ | ......... | ....P.... | ...N... | ....E.... | ..S.Q...I. | ......... |

Figure 52 (Continued)

| VK1JA30/JK | | | | | | | | |
|---|---|---|---|---|---|---|---|---|
| | | LIGWQSPSSL AVSVGDRVTI | RAS QCIR ---- NDIC | NYLAWYQQK lFKLLI | -ASSLQS | GVPSRFSGSGS GTEFTLTISS LQPEDFAT | YYC | LQHN -------- YPWT | FGQGTK VEIK |
| iPS:46 8826 | 21-225_201C5 | VK1|A30/JK1 | . . . . . . . . . . . . . . . . . . . . | . . . . . . . . . . H . . . | . . . . . . . . . . | . . . . . . . | . . . . . . . . . . . . . . . . . . . . | . . . . Y . | . . . . . . . . | . . . |
| iPS:46 8842 | 21-225_50H4 | VK1|A30/JK1 | . . . . . . . . . . . . . . . . . . . . | . . . . . . . . . . . . . . . | . . . . . . . . . . | . . . . . . . | . . . . . . . . . . . . . . . . . . . . | . . . . Y . | . F . R . . . | . . . |
| iPS:46 8858 | 21-225_148C9 | VK1|A30/JK1 | . . . . . . . . . . . . . . . . . . . . | . . . . . . . . . . R . . . | . . . . . . . . . . | . . . . . . . | . . . . . . . . . . . . . . . . . . . . | . . . . Y . | . . . . . R . | . . . |
| iPS:46 8860 | 21-225_224E7 | VK1|A30/JK1 | . . . . . . . . . . . . . . . . . . . . | . . . . . . . . . . D . . . | . . . . . . . . . . T | . . . . . . . | . . . . . . . . . . . . . . . . . . . . | . . . . Y . | . . . . . . . | . . . |
| iPS:43 3919 | 21-225_44B3 | VK1|A30/JK1 | . . . . . . . . . . . . . . . . . . . . | . . . . . . . . . . . . . . . | . . . . . . . . . . | . . . . . . . | . . . . . . . . . . . . . . . . . . . . | . L . YN . | . . . . . R . | . . . |
| iPS:43 3923 | 21-225_44D3 | VK1|A30/JK1 | . . . . . . . . . F . . . . . . . . . . | . . . . . . . . . . D . . . | . . . . . . . . . . | . . . . . . . | . . . . . . . . . . . . . R . . . R . . | . . . . Y . | . . . . . R . | . . . |
| iPS:43 3929 | 21-225_44D5 | VK1|A30/JK1 | . . . . . . . . . . . . . . . . . . . . | . . . . . . . . . . D . . . | . . . . . . . . . . | . . . . . . . | . . . . . . . . . . . . . . . . . . . . | . . . . Y . | . . . . F . . | . . . |
| iPS:43 3935 | 21-225_44F9 | VK1|A30/JK1 | . . . V . . . . . . . . . . . . . . . . | . . . . . . . . . . K . . . | . . . . . . . . . . | . . . . T . E | . . . . . . . . . . . . . . . . . . . . | . H . YN . | . . . . . R . | . . . T |
| iPS:43 3939 | 21-225_44C10 | VK1|A30/JK1 | . . . . . . . . . . . . . . . . . . . . | . . . . . . . . . . D . . . | . . . . . . . . . . | . . . . . . T | . . . . . . . . . . . . . . . . . . . . | . . . . Y . | . . . . . R . | . . . |
| iPS:43 3951 | 21-225_45B4 | VK1|A30/JK1 | . . . . . . . . . . . . . . . . . . . . | . . . . . . . . . . D . . . | . . . . . . . . . . | . . . . . . . | . . . . . . . . . . . . . . . . . . . . | . . . . Y . | . . . . . . . | . . . |
| iPS:43 3955 | 21-225_45B8 | VK1|A30/JK1 | . . . . . . . . . F . . . . . . . . . . | . . . . . . . . . . D . . . | . . . . . . . . . . | . . . . . . . | . . . . . . . . . . . . . . . . . . . . | . . . YN . | . . . . . R . | . . . |
| iPS:43 3967 | 21-225_46C3 | VK1|A30/JK1 | . . . . . . . . . . . . . . . . . . . . | . . . . . . . . . . D . . . | . . . . . . . . . . | . . . . . . . | . . . . . . . . . . . . . R . . . . . . | . . . . Y . | . . . . . . . | . . . |
| iPS:43 3971 | 21-225_46D4 | VK1|A30/JK1 | . . . . . . . . . F . . . . . . . . . . | . . . . T . . . . . D . . . | . . . . . . V . . . | . . . . . . . | . . . . . . . . . . . . . . . . . . . . | . . . . Y . | . . . . . R . | . . . |
| iPS:43 3997 | 21-225_48C1 | VK1|A30/JK1 | . . . . . . . . . . . . . . . . . . . . | . . . . T . . . . . . . . . | . . . . . . . . . . | . . . . R . . | . . . . . . . . . A . . . . . . . . . . | . . . . Y . | . . . . F . . | . . . |
| iPS:43 4001 | 21-225_48F2 | VK1|A30/JK1 | . . . . . . . . . . . . . . . . . . . . | . . . . . . . . . . R . . . | . . . . . . . . . . | . . . . . . . | . . . . . . . . . . . . . . . . . . . . | . . . . Y . | . . . . . R . | . . . |
| iPS:43 4009 | 21-225_48A9 | VK1|A30/JK1 | . . . . . . . . . . . . . . . . . . . . | . . . . . . . . . . D . . . | . . . . . . . . P . | . . . . . . I | . . . . . . . . . N . . . S . L . . . . | . . . . QY . | . . . . . . . | . . . |
| iPS:43 4047 | 21-225_50A12 | VK1|A30/JK1 | . . . . . . . . . . . . . . . . . . . . | . . . . . . . . . . . . . . . | . . . . . . . . . . | . . . . . . . | . . . . . . . . . G . . . G . . . I . . | . . . . R . | . . . . . . . | . . . |
| iPS:43 4067 | 21-225_51H8 | VK1|A30/JK1 | . . . . . . . . . . . . . . . . . . . . | . . . . . . . . . . . . . . . | . . . . . . . . . . | . . . . . . . | . . . . . . . . . . . . . . G . . . H . | . . . . Y . | . . . . F . . | . . . |
| iPS:43 4135 | 21-225_54H3 | VK1|A30/JK1 | . . . . . . . . . . . . . . . . . . . . | . . . . . . . . . . D . . . | . . . . . . . . . . | . . . . . . N | . . . . . . . . . . . . . . . . . . . . | . . . . V . | . . . . . . . | . . . |
| iPS:43 4197 | 21-225_56C7 | VK1|A30/JK1 | . . . . . . . . . . . . . . . . . . . . | . . . . . . . . . . I . . . | . . . . . . . . . . | . . . . T . N | . . . . . . . . . . . . . . . . . . . . | . . . . . . | . . . . . . . | . . . |

Figure 52 (Continued)

| ID | Name | V/J | | | | | | | | |
|---|---|---|---|---|---|---|---|---|---|---|
| iPS:43 4203 | 21-225_60E2 | VK1JA30/JK1 | ..... | ..... | ..... | ..... | ..... | ..... | ..... | ..... |
| iPS:43 4209 | 21-225_60C3 | VK1JA30/JK1 | ..... | ....K..... | ..... | S..... | ..... | ..... | ..... | ..... |
| iPS:43 4229 | 21-225_61H1 | VK1JA30/JK1 | ..... | ....K..... | ..... | ..... | ..... | ..... | ..... | ...L.. |
| iPS:43 4241 | 21-225_61E6 | VK1JA30/JK1 | ....I.... | ....A..... | ...E..... | ..... | ..... | ....Y..... | FP..... | ..... |
| iPS:43 4257 | 21-225_62F7 | VK1JA30/JK1 | ..... | ..... | ...P..... | ..... | ..... | ..... | YP..... | ..S.. |
| iPS:43 4281 | 21-225_57B8 | VK1JA30/JK1 | ....T.... | ....G..... | ...E..... | .R..... | ..... | ..... | FP..... | ..... |
| iPS:43 4315 | 21-225_59G7 | VK1JA30/JK1 | ..... | ..... | ..... | ..... | ..... | ..... | ..... | ..... |
| iPS:43 4319 | 21-225_59B9 | VK1JA30/JK1 | ..... | ....D..... | ...H..... | ..... | TR..... | ..... | ..... | ..... |
| iPS:43 4339 | 21-225_64A4 | VK1JA30/JK1 | ..... | ..... | ..... | ..... | .L..... | ....Y..... | .R..... | ..... |
| iPS:43 4343 | 21-225_64C8 | VK1JA30/JK1 | .A..... | ....A..... | ...C..... | .C..... | ..... | ...H.Y..... | .R..... | ..... |
| iPS:43 4385 | 21-225_66C10 | VK1JA30/JK1 | ..... | ..... | ...P..... | ..... | ..... | ....Y..... | YP..... | ..S.. |
| iPS:43 4387 | 21-225_66D11 | VK1JA30/JK1 | ...F..Q.. | ....H..... | .H..... | ...C..... | IS..M.R..C | IV..... | ..... | ..... |
| iPS:43 4441 | 21-225_71A2 | VK1JA30/JK1 | ...R.. | ..... | H..... | ER..I.. | TH..... | ..... | ..... | ..... |
| iPS:43 4469 | 21-225_73C9 | VK1JA30/JK1 | ..... | ..... | ..... | ..... | ..... | ....Y..... | .R..... | ..... |
| iPS:43 5197 | 21-225_94F3 | VK1JA30/JK1 | ..... | ....A.D.. | ...Q..F.. | ..... | ..V..C.. | ..... | .R..... | .R.A.. |
| iPS:43 5325 | 21-225_147H5 | VK1JA30/JK1 | ..... | .R..D.. | ..... | ..... | .F..... | ..... | .R..... | ..... |
| iPS:43 5393 | 21-225_149D10 | VK1JA30/JK1 | ..... | ...R..D.. | ...N..... | ...N..... | .F..... | ....Y..... | .R..... | ..... |
| iPS:43 5539 | 21-225_158G1 | VK1JA30/JK1 | ..... | ....D..K.. | ..... | ..... | ..... | ....Y..... | .R..... | ..... |
| iPS:43 5543 | 21-225_158D4 | VK1JA30/JK1 | ..... | ..... | ..... | ..... | ..... | ...H..... | .R..... | ..... |
| iPS:43 5571 | 21-225_159C8 | VK1JA30/JK1 | ..... | ....K..... | ..... | ..... | ..... | ..... | ..... | ..... |
| iPS:43 5573 | 21-225_159D8 | VK1JA30/JK1 | ..... | RD.G..... | ..S..... | ..... | .F..... | ....Y..... | .R..... | ..... |

Figure 52 (Continued)

| | | | | | | | | | | |
|---|---|---|---|---|---|---|---|---|---|---|
| iPS:43 5581 | 21-225_160H1 | VK1|A30/JK1 | . . . . . | . . . . . | D . . . . | . . . . . | . . . . . | . . . . . | . F . . . | . . . . . |
| iPS:43 5583 | 21-225_160F2 | VK1|A30/JK1 | . . . . . | . . . . . | . . . . . | T . . . . N | . . . . . | . T . . . | . . . . . | . . . . . |
| iPS:43 5591 | 21-225_160C4 | VK1|A30/JK1 | . . . . . | . . . . . | D . . . . | . . . . N . | . . . . . | V . . . . | . R . . . | Y . . . . |
| iPS:43 5615 | 21-225_161G12 | VK1|A30/JK1 | . . . . R | . . . . . | . K . . . | . . . . N . | . . . . . | F . . . . | . R . . . | H . . . . |
| iPS:43 5675 | 21-225_169D7 | VK1|A30/JK1 | . . . . . | . . . . . | . K . . . | . . . . . | . . . . . | F . . . . | . C . . . | H . . . . |
| iPS:43 5681 | 21-225_169D11 | VK1|A30/JK1 | . . . . . | . . . . . | D . . . . | V . . . . | . . . . . | . . . . . | . R . . . | Y . . . . |
| iPS:43 5687 | 21-225_170H1 | VK1|A30/JK1 | . . . . . | . . . . . | . . . . . | . . . . T . | . . . . . | . . . . . | . N . . . | S . . . . . S . |
| iPS:43 5689 | 21-225_170F3 | VK1|A30/JK1 | . . . . Q | . . . . . | R . . . . | . . . . . | N . . . . | . . . . . | . R . . . | Y . . . . |
| iPS:43 5741 | 21-225_174G10 | VK1|A30/JK1 | . . . . . | . . . . . | D . . . . | V . . . . H | . . . . . | L . . . . | . R . . . | H . . . . |
| iPS:43 5831 | 21-225_190C12 | VK1|A30/JK1 | . . . . . | . . . . . | . K . . . | . . . . . H | . . . . T . N | L . . . . | . . . . . | . . . . . |
| iPS:43 5857 | 21-225_191A4 | VK1|A30/JK1 | . . . . R | . . . . . | . K . . . | . . . . . H | . . . . T . | L . . . . | . . . . . | . . . . . |
| iPS:43 5907 | 21-225_190G3 | VK1|A30/JK1 | . . . . . | . . . . . | . K . . . | . . . . T . | . . . . . | L . . . . | . . . . . C . | . . . . . |
| iPS:43 5919 | 21-225_190H5 | VK1|A30/JK1 | . . . . . | . . . . . | . H . . . | L . . . . | . . . . T . | L . . . . | . . . . V . N | N . . . . |
| iPS:43 5989 | 21-225_192F7 | VK1|A30/JK1 | L . . . F C . . I | . . . . . | . K . . . | EL . . . . | . . . . . A . . G | L . . . . | . . . . E | T . . . . |
| iPS:43 6132 | 21-225_196C12 | VK1|A30/JK1 | . . . . . | . . . . . | . K . . . | S . N . . | . . . . . | I . . . . | . . . . E | D . . . . | F . F . . |
| iPS:43 6222 | 21-225_200C9 | VK1|A30/JK1 | . . . . . | . . . . . RF | . K . . . | . . . . . | . . . . . | . . . . . | . . . . . | . . . . . | . . . . . |
| iPS:43 6264 | 21-225_203F7 | VK1|A30/JK1 | . . . . . | . . . . . | . H . . . | . . . . . | . . . . . | . . . . . | . . . . . | Y . . . . | . F . R . |
| iPS:43 6274 | 21-225_204H3 | VK1|A30/JK1 | . . . . . | . . . . . | . H . . . | . . . . . | . . . . . | G . . . . | . . . . . | Y . . . . | . R . . . |
| iPS:43 6332 | 21-225_208B2 | VK1|A30/JK1 | . . . . . | . . . . . P | . . . . . | . . . . . | . . . . . | G . . . . | . . . . . | . Y . . . | . R . . . |
| iPS:43 6352 | 21-225_210G5 | VK1|A30/JK1 | . . . . . | . . . . . | . . . . . | . . . . . | . . . . . | . . . . . | . . . . . | . H . Y . | . R . . . |
| iPS:43 6388 | 21-225_212B11 | VK1|A30/JK1 | . . . . . | . . . . . | . . . . . | . . . . . | I . . . . | . . . . . | . . . . . | . L . Y . | . L Q . . |

Figure 52 (Continued)

| ID | | Chain | | | | | | | | |
|---|---|---|---|---|---|---|---|---|---|---|
| iPS:43 6412 | 21-225_214H9 | VK1jA30/JK1 | ........... | ........... | ........... | ........... | ........... | ........... | Y........... | ........... |
| iPS:43 6414 | 21-225_214G10 | VK1jA30/JK1 | ....LC...PP | ........... | ........... | ........... | ........... | ....L...... | ........... | ...R....... |
| iPS:43 6416 | 21-225_214G12 | VK1jA30/JK1 | .........PP | ........... | ........... | ........... | ........... | I.......... | VM.Y....... | ...R....... |
| iPS:43 6418 | 21-225_215E3 | VK1jA30/JK1 | .........PP | ........... | ........... | ........... | ........... | I.......... | VM......... | ...R....... |
| iPS:43 6428 | 21-225_215E11 | VK1jA30/JK1 | ......C..PP | ........... | ........... | ........... | ........... | I....V.R... | VM.Y....... | ...R....... |
| iPS:43 6438 | 21-225_216E8 | VK1jA30/JK1 | .........P. | ........... | ........... | ........... | ........... | I.......... | .M.Y....... | ...R....... |
| iPS:43 6440 | 21-225_216H12 | VK1jA30/JK1 | ....L....P. | ........... | ........... | G.......... | ........... | I.......... | VM......... | ...R....... |
| iPS:43 6450 | 21-225_217E5 | VK1jA30/JK1 | ......C..PP | .F......... | ........... | ........... | ........... | I.......... | VM......... | ...R....... |
| iPS:43 6456 | 21-225_217G10 | VK1jA30/JK1 | .........PP | ........... | ........... | ........... | ........... | ........... | ........... | ...R....... |
| iPS:43 6458 | 21-225_217H12 | VK1jA30/JK1 | ......C..PP | ........... | ........... | G.......... | ........... | I.......... | .M.Y....... | ...R....... |
| iPS:43 6462 | 21-225_218C4 | VK1jA30/JK1 | .F....L..PP | ........... | ........... | ........... | ........... | I....V.R... | VM.Y....... | ...R....... |
| iPS:43 6480 | 21-225_220F8 | VK1jA30/JK1 | .F.......PP.R | ........... | ........... | ........... | ........... | I......R... | VM......... | ...R....... |
| iPS:43 6534 | 21-225_224F1 | VK1jA30/JK1 | A.......... | ........... | ........... | ........... | ........... | ....I...... | ........... | ...R....... |
| iPS:43 6540 | 21-225_224F3 | VK1jA30/JK1 | ........... | ........... | ........... | ........... | ........... | ........... | ........... | ...R....... |
| iPS:43 6564 | 21-225_225A1 | VK1jA30/JK1 | ........... | .....E...... | ........... | ........... | ........... | ........... | ..YN....... | ...RA...... |
| iPS:43 6596 | 21-225_225C6 | VK1jA30/JK1 | .L......... | ........... | ........... | ........... | ........... | .L.N....... | ..Y........ | ...RA...... |
| iPS:43 6604 | 21-225_226F7 | VK1jA30/JK1 | ........... | ........G.. | ........... | ........... | ........... | I...N.V... | ..YN....... | ...R....... |
| iPS:43 6620 | 21-225_226H11 | VK1jA30/JK1 | ........... | ........... | ........... | ........... | ........... | .........D. | .H.Y........ | ...R.....Q. |
| iPS:43 7262 | 21-225_170E4 | VK1jA30/JK1 | ........... | ....T....... | ........... | ...Y......V..G | ........... | ........... | ..Y......... | .YP......... |
| iPS:43 7280 | 21-225_203C10 | VK1jA30/JK1 | ........... | .....D...A.. | ........... | ........R... | ........... | ........A.. | ........... | ...R.....D. |
| iPS:43 7286 | 21-225_208F1 | VK1jA30/JK1 | ........... | .....H....F. | ........... | ........... | ........... | ........... | ..Y........ | .F.R........ |

Figure 52 (Continued)

| | | | RF | | | | S | V.R..C...N | V..Y | |
|---|---|---|---|---|---|---|---|---|---|---|
| iPS:43 7290 | 21-225_210G6 | VK1|A30/JK1 | | | | | | | V..Y.....F.R. | .L..V. |
| iPS:45 1114 | 21-225_159A3 | VK1|A30/JK1 | .F. | .D.K. | .N.. | | | | .H......R. | |
| iPS:39 2626 | 21-225_18A5 | VK1|A30/JK1 | | | | | | | | |
| iPS:39 2634 | 21-225_17H3 | VK1|A30/JK1 | .F. | .S. | | | | | | |
| iPS:39 2674 | 21-225_18C2 | VK1|A30/JK1 | | | | .T. | F | | .QY.......R. | |
| iPS:39 2686 | 21-225_17C7 | VK1|A30/JK1 | | | | | | | | |
| iPS:39 2690 | 21-225_18F2 | VK1|A30/JK1 | | | .R. | | | | | |
| iPS:39 2710 | 21-225_19A10 | VK1|A30/JK1 | | .T. | | .T. | .R. | | .G. | |
| iPS:39 2740 | 21-225_18H12 | VK1|A30/JK1 | | | | | | | .N. | .L..V. |
| iPS:39 2742 | 21-225_20B2 | VK1|A30/JK1 | .N. | .D. | | .T. | | | .YN.......RA | .D..V. |
| iPS:39 2758 | 21-225_21G11 | VK1|A30/JK1 | | | | .V. | R | | .N. | .L..V. |
| iPS:39 2790 | 21-225_20D10 | VK1|A30/JK1 | | .V. | | .Y. | | Y | .I.Q. | |
| iPS:39 2796 | 21-225_22A4 | VK1|A30/JK1 | | .D. | | | | | | |
| iPS:39 2832 | 21-225_21H8 | VK1|A30/JK1 | | | | | R | | | |
| iPS:39 2836 | 21-225_22F4 | VK1|A30/JK1 | | | | .P. | | R....D. | .H.Y. | |
| iPS:39 2844 | 21-225_23E11 | VK1|A30/JK1 | .I. | .G. | | .H. | T | | .Y. | .V. |
| iPS:39 2846 | 21-225_24B6 | VK1|A30/JK1 | | .D. | | .H. | | | | .R. |
| iPS:39 2872 | 21-225_20B11 | VK1|A30/JK1 | | | | E | | | .Y. | .R. |
| iPS:39 2876 | 21-225_21F7 | VK1|A30/JK1 | | .D. | | .NF. | | | .N. | |
| iPS:39 2884 | 21-225_23A10 | VK1|A30/JK1 | | | | | G | | .Y. | .L..V. |
| iPS:39 2894 | 21-225_21G2 | VK1|A30/JK1 | | | | .S. | | | | .L..V. |

Figure 52 (Continued)

| | | | | | | | | |
|---|---|---|---|---|---|---|---|---|
| iPS:39_2908 | 21-225_23F12 | VK1|A30/JK1 | . . . . . . . . . . | . . . . . . . . . . | . . . . . . . . . . | . . . . . . . . . . | . . . . . . . . . . | . . . . . . . . . . |
| iPS:39_2914 | 21-225_25D12 | VK1|A30/JK1 | . . . . . . . . . . | . . . T . . . . . . | . . . . . . . . . . | . . . . . S . . . . | . . . Y . . . . . . | . . . . . . . . . . |
| iPS:39_2918 | 21-225_28F5 | VK1|A30/JK1 | . . . . . . . . . . | . . . . . . . . . . | . . . F . . . . . . | . . . . . . . . . . | . T . . . . . . . . | . . F.R. . . . . . |
| iPS:39_2958 | 21-225_28C7 | VK1|A30/JK1 | . . . . . . . . . . | . . . . . . . . . . | . . . F . . . . . . | . . . . . . . . . . | . T . . . . . . . . | . . . . . . . . .V. |
| iPS:39_2972 | 21-225_26A2 | VK1|A30/JK1 | . . . . . . . . . . | . . . . S . . . . . | . . . F . . . . . . | . . . . F . . . . . | . R . . . . . . . . | . . . . . . . . . . |
| iPS:39_3026 | 21-225_32B6 | VK1|A30/JK1 | . . . . . . . . . . | . . . . . . . . . . | . V . . . . . . . . | . . . . . . . . . . | . . . . . . . . . . | . . . . . . . . . . |
| iPS:39_3130 | 21-225_33C2 | VK1|A30/JK1 | . . . . . . . . . . | . . . . . . . . . . | . . . P . . . . . . | . . . H . . . . . . | . . . . . . . . . . | . . . . . . . . . . |
| iPS:39_3812 | 21-225_6A11 | VK1|A30/JK1 | . . . . . . . . . . | . . . . . . . . . . | . . . . . . . . . . | . . . . . . . . . . | . . . . . . . . . . | . . . . . . . . . . |
| iPS:39_3838 | 21-225_6G2 | VK1|A30/JK1 | . F . . R. . . . Y | . . . . . . . . . . | . . Q . . . . . . . | . . . NI . . . . . . | I . . . Y . . . . . | . . L. . . . . T |
| iPS:39_3864 | 21-225_4C5 | VK1|A30/JK1 | . . H. HL. . . . . | . . . R. . . . . G. | . . R . . . . . . N | . . . . G . . . . . | . . Y . . . . . . . | . . R. . . . . . |
| iPS:39_3868 | 21-225_9C11 | VK1|A30/JK1 | . . . . . . . . . . | . . . N. . . Y.N | . . S.R.V . . . . L | . . . . N . . . . . | H.S. . . . . . . . | . T.L. . . . . . |
| iPS:39_3876 | 21-225_9A1 | VK1|A30/JK1 | . F . . R. . . . . | . . . . . . . . . . | . R. . . . . . . T | . . . . . . . . I H | I . . . . . . . . . | . . L . . . . . . |
| iPS:39_3902 | 21-225_14E10 | VK1|A30/JK1 | . . . . . . . . . . | . . T . . . . . . . | . H . . Q . . . . . | . . . . Y . . . N Y | . . . . . . . . . . | . . . R. . . . . . |
| iPS:39_3908 | 21-225_10E9 | VK1|A30/JK1 | . . . . . . . . . . | . . . D. . . . . . | . T . F . . . . . . | . . . . TA. . . . . | . . . Y . . . . . . | . . R. . . . . . |
| iPS:39_3916 | 21-225_2G4 | VK1|A30/JK1 | . . . . . . . . . . | . . . . . . . . . . | . T . . . . . . . . | . . . . . . . . N . | . . . Y . . . . . . | . . . . . . . . . R. |
| iPS:39_3948 | 21-225_16A5 | VK1|A30/JK1 | . . . . . . . . . . | . . . . . . . . . . | . C . . . . . . . . | . . . . L . . . . . | . . . Y . . . . . . | . F.R. . . . . . |
| iPS:39_3960 | 21-225_7G2 | VK1|A30/JK1 | . . . . . . . . . . | . . . G . . . . . . | . . . . . . . . . . | . . P . V . . . . . | . . YT . . . . . . | . . R. . . . . . |
| iPS:39_3966 | 21-225_7F8 | VK1|A30/JK1 | . . . . . . . . . . | . . . . . . . . . . | . T . . . . . . . . | . . . . L . . . . . | . . LY . . . . . . | . . L. . . . . V |
| iPS:39_3972 | 21-225_7C9 | VK1|A30/JK1 | . . . . . G . . . . | . . . . . . . . . . | . . . . . . . . . . | . . . . . . . . . . | . . Y . . . . . . . | . . R. . . . . D. |
| iPS:39_3978 | 21-225_4C12 | VK1|A30/JK1 | . . . . . . . . . . | . . . . . . . . . . | . T. R. . . . . . . | . . . H . . . . . . | . . Y . . . . . . . | . F.R. . . . . . |
| iPS:39_3986 | 21-225_7G4 | VK1|A30/JK1 | . . . . . . . . . . | . . . . . . . . . . | . . . . . . . . . . | . . . . S . . . . . | . HQY. . . . . . . | . . R. . . . . . |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:39 3996 | 21-225_15C11 | VK1|A30/JK1 | . . . . . . . | . . . . . . . | . . . . . . . | . . . . . . . | . . . . . . . | . . . . . . . | . . L . Y . . . | . . R . . . |
| iPS:39 3998 | 21-225_12B12 | VK1|A30/JK1 | . . . . . . . | . . . . . . . | . . . . . . . | . . . . . . . | . . . . . . . | . . . . R . | . . L . . |
| iPS:39 4041 | 21-225_5E5 | VK1|A30/JK1 | . . . . . . . | . . . T . | . . . . . . . | . . . . . . . | . . . . . . . | . . . . . . . | . . V . . |
| iPS:39 4067 | 21-225_12F2 | VK1|A30/JK1 | . . . . . . . | . . . . . . . | . . . . . . . | . . . . . . . | . . . . . . . | . . Y . . . | . . V . . |
| iPS:39 4089 | 21-225_12E6 | VK1|A30/JK1 | . . . . . . . | . . S . . . | . . . . . . . | . . . . . . . | . . . V . . . | . . . . . . . | . . . . . . . |
| iPS:39 4093 | 21-225_9D12 | VK1|A30/JK1 | . . . . . . . | . . . . . . . | . . . . . . . | . . . . . . . | . . . . . . . | . . . . . . . | . . . . . . . |
| iPS:39 4095 | 21-225_16H4 | VK1|A30/JK1 | . . . . . . . | . . . . . . . | . . . T . . | . . . . . . . | . . . . . . . | . . . . . . . | . . . . . . . |
| iPS:39 4097 | 21-225_16G7 | VK1|A30/JK1 | . . . . . . . | . . . . . . . | . . . . . . . | . . . . . . . | . . . . . . . | . . . . . . . | . . . . . . . |
| | Germline | K_FR1 | K_CDR1 | K_FR2 | K_CDR2 | K_FR3 | K_CDR3 | K_FR4 |
| VK3|L2|K2 | | EIVMTQSPATLS VSPGERATISC | RAS QSVS SYLA | WYQQKPGQ APRLLIY | GAS TRAT | GIPARFSGSGS GTEFTLTISSLQSEDFAV YYC | QQYN NWPPIT | FGQGTKVEIK |
| iPS:46 8828 | 21-225_162A10 | VK3|L2|JK2 | . . . . . . . | . . . T . N . | . . . S . . | . . . . . . . | V . . . . I N . . . . R . . | . . D . . . . . . . . . . . | . . . . . . . |
| iPS:43 4255 | 21-225_62E6 | VK3|L2|JK2 | . . . . . . . | . . . . N . . | . . . F . . | . . . V . . | . . . . . N . . . . . . . F | . . D . . . . . . . C S | . . . . . . . |
| iPS:43 4269 | 21-225_57H3 | VK3|L2|JK2 | . . . . . . . | . . . . . S . | . . . S . . | . . . . . . . | . . F . . N . . . M . . . I | . . D . . . . . . . C S | . . . . . . . |
| iPS:43 4363 | 21-225_65A6 | VK3|L2|JK2 | . . . V . F | . . . . . N . | . . . . . . | . . . . . . . | . . . . . N . . . . . I | . . D . . . . . . . C S | . . L E . . |
| iPS:43 4393 | 21-225_67C3 | VK3|L2|JK2 | . . . . . . . | . . . . . N . | . . . S . . | . . . H . . | . . . . . . . . . . . . . | . . D . . . . . . . C S | . . . . . . . |
| iPS:43 4425 | 21-225_70A5 | VK3|L2|JK2 | . . . . . . . | . . . V . V . | . . L . . | . . . T . . | . . P . . N . . . . . V . . | . . D . . . . . . . C S | . . . . . . . |
| iPS:43 4485 | 21-225_76D2 | VK3|L2|JK2 | . . . P . . | . . N S . . | . . . H . . | . . . T . . | . . . . . . . . . . . . I | . . D . . . . . . . C S | . . . . . . . |
| iPS:43 4537 | 21-225_74E11 | VK3|L2|JK2 | . . . . . . . | . . . L . V . | . . . L . . | . . . . . . . | . . . . . . . . . . . . . I | . . D . . . . . . . C S | . . . S . . |
| iPS:43 4569 | 21-225_77H5 | VK3|L2|JK2 | . . V . . | . . N S . . | . . . . . . | . . . . . . . | . . S F . . . . . . . . . F | . . D . . . . . . . C S | . . . Q . . |
| iPS:43 4629 | 21-225_74C3 | VK3|L2|JK2 | . . . . . . . | . . . S . A . | . . . . . . | . . . F . T . | . . . . . . . I . . . . . | . . D . . . . . . . C S | . . L . . |
| iPS:43 4673 | 21-225_74E3 | VK3|L2|JK2 | . . L . . | . . L . V . | . . . . . . | . . . . . . . | . . . . . . . . . . . . . | . . D . . . . . . . C S | . . . . . . . |

| | | K_FR1 | K_CDR1 | K_FR2 | K_CDR2 | K_FR3 | K_CDR3 | K_FR4 |
|---|---|---|---|---|---|---|---|---|
| iPS:43 6203 | 21-225_199A6 | VK3|L2/J K4 | D..... | P....F. ..R. | | | ..EC. | | |
| iPS:43 7334 | 21-225_75F11 | VK3|L2/J K4 | .........F | ..R. | F. ..I | | .Y..Y | | WP. |
| iPS:44 8904 | 21-225_65C12 | VK3|L2/J K4 | .F...G.... | ....I | | | ..NA..N ..S.... | ..T | |
| VK1|A30|JK 3 | | Germline K_FR1 | K_CDR1 | K_FR2 WYQQKPGK AKRLLIY | K_CDR2 AASSLQS | K_FR3 GVPSRFSGSGSGT DFTLTISSLQPEDFAT YYC | K_CDR3 LQHNS YPLT | K_FR4 FGQGTK VDIK |
| iPS:46 8832 | 21-225_76H10 | VK1|A30/ JK3 | ...A..... | | | | | ...Y | |
| iPS:46 8836 | 21-225_198E3 | VK1|A30/ JK3 | | | F. | G. | | .YR. | F. |
| iPS:46 8844 | 21-225_48E10 | VK1|A30/ JK3 | | ....K | | | ..V. | | |
| iPS:46 8846 | 21-225_53B10 | VK1|A30/ JK3 | | ....S | | T. | | ...Y. | |
| iPS:43 3895 | 21-225_43E1 | VK1|A30/ JK3 | ...A..... | ...D. ...Y. | | G. | | ...Y. | F. |
| iPS:43 3905 | 21-225_43E5 | VK1|A30/ JK3 | | | ..K.. .N | | | | |
| iPS:43 3913 | 21-225_43H8 | VK1|A30/ JK3 | | | ...H | | ...V. | ...T. | F. |
| iPS:43 3933 | 21-225_44C8 | VK1|A30/ JK3 | | | | ....N | ...S. | | |
| iPS:43 3949 | 21-225_45H2 | VK1|A30/ JK3 | | | | G. ...N | ...V. | ...T. | F. |
| iPS:43 3981 | 21-225_46E9 | VK1|A30/ JK3 | | | ....K | G. | ...V. | | F. |
| iPS:43 3995 | 21-225_47H7 | VK1|A30/ JK3 | | ...T | | | ...V. ..F. | ...T. | F. |
| iPS:43 4039 | 21-225_43B1 | VK1|A30/ JK3 | | | | | ...V. ..F. | ...T. | F. |
| iPS:43 4057 | 21-225_51E4 | VK1|A30/ JK3 | | | ...Q. | | ....A | | |
| iPS:43 4071 | 21-225_51F9 | VK1|A30/ JK3 | | | ...Q. .R. | | ....D | | |
| iPS:43 4075 | 21-225_51B11 | VK1|A30/ JK3 | A........ | | ....R. | ....R | ....S | | |
| iPS:43 4091 | 21-225_52B9 | VK1|A30/ JK3 | A........ | | ....R. | | .L... ..R. | | |

Figure 52 (Continued)

| | | | | | | | | | |
|---|---|---|---|---|---|---|---|---|---|
| iPS:43 4101 | 21-225_52H12 | VK1jA30/JK3 | . | . | . | . | . | . | . |
| iPS:43 4103 | 21-225_53G1 | VK1jA30/JK3 | . | . | . | . | D. | . | . |
| iPS:43 4129 | 21-225_53B12 | VK1jA30/JK3 | . | . | . | S. | . | . | . |
| iPS:43 4131 | 21-225_54D3 | VK1jA30/JK3 | . | . | . | . | . | . | . |
| iPS:43 4143 | 21-225_54G7 | VK1jA30/JK3 | . | . | . | . | H.T | . | . |
| iPS:43 4155 | 21-225_55B3 | VK1jA30/JK3 | . | . | . | . | . | R..S. | . |
| iPS:43 4169 | 21-225_50C4 | VK1jA30/JK3 | .L. | . | .T | . | R. | . | . |
| iPS:43 4187 | 21-225_56A5 | VK1jA30/JK3 | . | D...L. | . | . | Y. | . | ..R |
| iPS:43 4199 | 21-225_59F11 | VK1jA30/JK3 | . | . | . | . | R. | . | F. |
| iPS:43 4207 | 21-225_60A3 | VK1jA30/JK3 | . | . | . | . | . | . | . |
| iPS:43 4251 | 21-225_62G3 | VK1jA30/JK3 | .H. | D...N. | .F. | . | Y. | . | . |
| iPS:43 4263 | 21-225_56H7 | VK1jA30/JK3 | .L. | D. | .R..P | . | D. | . | .S. |
| iPS:43 4265 | 21-225_57B2 | VK1jA30/JK3 | .V. | A. | .L. | . | . | . | . |
| iPS:43 4271 | 21-225_57A4 | VK1jA30/JK3 | . | V. | .L. | . | . | . | . |
| iPS:43 4275 | 21-225_57F4 | VK1jA30/JK3 | . | . | FL.T | . | YG. | .H. | . |
| iPS:43 4293 | 21-225_58F5 | VK1jA30/JK3 | . | . | .L. | . | . | . | .E. |
| iPS:43 4299 | 21-225_58D11 | VK1jA30/JK3 | . | S..D | .T. | A..R. | N. F. | . | . |
| iPS:43 4351 | 21-225_64A12 | VK1jA30/JK3 | . | D. | .T. | G. | G. | . | . |
| iPS:43 4383 | 21-225_66F9 | VK1jA30/JK3 | . | V. | .F. | G. | Y. | . | . |
| iPS:43 4399 | 21-225_67B7 | VK1jA30/JK3 | . | . | .R... | S. | H. K | . | . |
| iPS:43 4407 | 21-225_68G8 | VK1jA30/JK3 | . | N. | V. | . | Y. | . | . |

Figure 52 (Continued)

| | | | | | | | | | | | |
|---|---|---|---|---|---|---|---|---|---|---|---|
| iPS:43 4447 | 21-225_71B6 | VK1|A30/ JK3 | P. | . . . . . . . . . . | . . D . . . . . . . | . . Q . . . . . . . | . . . . . . . . . . | . . . . . . . . . . | . . . . . . . . . . D . | . . . . . . . . . . Y . | . . . . . . . . . . |
| iPS:43 4449 | 21-225_71H6 | VK1|A30/ JK3 | . . . . . . . . . . | . . . . . . . . . V . | . . . . . . . . . . | . . . . . . . . . . | . . . . . . . . . . | . . . . . . . . . . | . . . . . . . . . . | . . . . . . . . . V . |
| iPS:43 4453 | 21-225_71B11 | VK1|A30/ JK3 | . . . . . . . . . . | . . . . . . . . . D . | . . . . . . . . t . | . . . . . . . . . . | . . . . . . . . . G . | . . . . . . . . . . | . . . . . . . . . T . | . . . . . . . . . . |
| iPS:43 4463 | 21-225_73A6 | VK1|A30/ JK3 | . . . . . . . . . . | . . . . . . . . . D . | . . . . . . . . F . | . . . . . . . . N . | . . . . . . . . . S . | . . . . . . . . . T . | . . . . . . . . . . | . . . . . . . . . . |
| iPS:43 4815 | 21-225_74A11 | VK1|A30/ JK3 | . . . . . . . . . . | . . . . . . . . . D . | . . . . . . . . C . | . . . . . . . . . . | . . . . . . . . . . | . . . . . . . . . . | . . . . . . . . . D . | . . . . . . . . . . |
| iPS:43 4977 | 21-225_88A5 | VK1|A30/ JK3 | . . . . . . . . . . | . . . . . . . . . . | . . . . . . . . . . | . . . . . . . . . . | . . . . . . . . . . | . . . . . . . . . F . | . . . . . . . . . D . | . . . . . . . . . E . |
| iPS:43 5253 | 21-225_96A4 | VK1|A30/ JK3 | . . . . . . . . . . | . . . . . . . . . D . | . . . . . . . . . . | . . . . . . . . . G V . | . . . . . . . . . . | . . . . . . . . . R . | . . . . . . . . . . | . . . . . . . . . . |
| iPS:43 5511 | 21-225_157C3 | VK1|A30/ JK3 | . . . . . . . . . . | . . . . . . . . . . | . . . . . . . . . . | . . . . . . . . . . | . . . . . . . . . . | . . . . . . . . . D . | . . . . . . . . . D . | . . . . . . . . . . |
| iPS:43 5521 | 21-225_157H4 | VK1|A30/ JK3 | . . . . . . . . . . | . . . . . . . . . . | . . . . . . . . R . | . . . . . . . . . P . | . . . . . . . . . . | . . . . . . . . . . | . . . . . . . . . D . | . . . . . . . . . . |
| iPS:43 5527 | 21-225_157G7 | VK1|A30/ JK3 | . . . . . . . . . C . | . . . . . . . . . . | . . . . . . . C . H . | . . . . . . . . . V . | . . . . . . . . . . | . . . . . . . . . V . R . | . . . . . . . . . I . D . | . . . . . . . . . E . |
| iPS:43 5533 | 21-225_157H8 | VK1|A30/ JK3 | . . . . . . . . . . | . . . . . . . . . . | . . . . . . . . N . | . . . . . . . . . . | . . . . . . . . . . | . . . . . . . . . . | . . . . . . . . . . | . . . . . . . . . . |
| iPS:43 5537 | 21-225_157H12 | VK1|A30/ JK3 | . . . . . . . . . . | . . . . . . . . . . | . . . . . . . . . . | . . . . . . . . . T . | . . . . . . . . . . | . . . . . . . . . D . | . . . . . . . . . . | . . . . . . . . . . |
| iPS:43 5547 | 21-225_158F5 | VK1|A30/ JK3 | . . . . . . . . . . | . . . . . . . . . F . | . . . . . . . . . . | . . . . . . . . . . | . . . . . . . . . . | . . . . . . . . . . | . . . . . . . . . Y . | . . . . . . . . . . |
| iPS:43 5551 | 21-225_158H6 | VK1|A30/ JK3 | . . . . . . . . . . | . . . . . . . . . . | . . . . . . . . . M . | . . . . . . . . . . | . . . . . . . . . . | . . . . . . . . . . I D . | . . . . . . . . . . | . . . . . . . . . . |
| iPS:43 5553 | 21-225_158G8 | VK1|A30/ JK3 | . . . . . . . . . P . | . . . . . . . . . . | . . . . . . . . N . | . . . . . . . . . V . | . . . . . . . . . . | . . . . . . . . . V . | . . . . . . . . . D . | . . . . . . . . . H . |
| iPS:43 5569 | 21-225_159C5 | VK1|A30/ JK3 | . . . . . . . . . . | . . . . . . . . . . | . . . . . . . . E . | . . . . . . . . . . t . | . . . . . . . . . E . | . . . . . . . . . . | . . . . . . . . . . | . . . . . . . . . . |
| iPS:43 5593 | 21-225_160F4 | VK1|A30/ JK3 | . . . . . . . . . . | . . . . . . . . . . | . . . . . . . . . . | . . . . . . . . . . | . . . . . . . . . . | . . . . . . . . V . G . V . R . . A . . | . . . . . . . . I . D . | . . . . . . . . . E . |
| iPS:43 5609 | 21-225_161F7 | VK1|A30/ JK3 | . . . . . . . . . . | . . . . . . . . . . | . . . . . . . . . . | . . . . . . . . . . | . . . . . . . . . t . | . . . . . . . . G . V . R . . . . G | . L Y I R . . | . . . . . . . . . R . |
| iPS:43 5613 | 21-225_161D11 | VK1|A30/ JK3 | . . . . . . . . . . | . . . . . . . . . . | . . . . . . . . . . | . . . . . . . . . . | . . . . . . . . . t . | . . . . . . . . G . V . R . . . . G | . . Y . R . . | . . . . . . . . . R . |
| iPS:43 5617 | 21-225_162F2 | VK1|A30/ JK3 | . . . . . . . . . C . | . . . . . . . . . . | . . . . . . . . N . | . . . . . . . . . . | . . . . . . . . . . | . . . . . . . . . V . | . . . . . . . . I . D . . H . | . . . . . . . . . E . |
| iPS:43 5621 | 21-225_162H3 | VK1|A30/ JK3 | . . . . . . . . . . | . . . . . . . . . . | . . . . . . . . N . | . . . . . . . . . . | . . . . . . . . . . | . . . . . . . . . . | . . . . . . . . . D . . H . | . . . . . . . . . E . |

Figure 52 (Continued)

| ID | Clone | V/J |   |   |   |   |   |   |   |   |   |
|---|---|---|---|---|---|---|---|---|---|---|---|
| iPS:43 5637 | 21-225_163E2 | VK1|A30/JK3 | ..... | ...D..... | ...T..... | ...P..... | ....... | ...S..... | ....... | ...H... | ....... |
| iPS:43 5641 | 21-225_163F9 | VK1|A30/JK3 | ....... | ...D..... | ....... | ...P..... | ....... | ....... | ...D... | ....... | ....... |
| iPS:43 5643 | 21-225_163G10 | VK1|A30/JK3 | ....... | ...D...N. | ....... | ...P..... | ....... | ...A... | ...DY. | ....... | ...F. |
| iPS:43 5719 | 21-225_171A11 | VK1|A30/JK3 | ....... | ...N..... | ....... | ....... | ....... | ....... | ...DH. | ....... | ...F. |
| iPS:43 5769 | 21-225_177B6 | VK1|A30/JK3 | ....... | ...D.S... | ....... | ....... | ...N... | ....... | ...L... | ....... | ....... |
| iPS:43 5791 | 21-225_180H7 | VK1|A30/JK3 | ....... | ....... | ...T... | ....... | ....... | ....... | ....... | ....... | ....... |
| iPS:43 5805 | 21-225_181A8 | VK1|A30/JK3 | ....... | ....... | ...T... | ....... | ....... | ...S... | ....... | ....... | ....... |
| iPS:43 5879 | 21-225_184H10 | VK1|A30/JK3 | ....... | ....... | ...T... | ....... | ....... | ...S..D | ....... | ....... | ....... |
| iPS:43 5881 | 21-225_184D11 | VK1|A30/JK3 | ....... | ...K... | ...L... | ....... | ....... | ....... | ....... | ....... | ....... |
| iPS:43 5921 | 21-225_190D6 | VK1|A30/JK3 | ....... | ...K... | ...L... | ....... | ....... | ...P... | ...Y... | ....... | ....... |
| iPS:43 5985 | 21-225_192F6 | VK1|A30/JK3 | ....... | ...K... | ...L... | ....... | ....... | ...P... | ...Y... | ...F... | ....... |
| iPS:43 6074 | 21-225_194F10 | VK1|A30/JK3 | ....... | ...D... | ....... | ....... | ....... | ...P... | ...Y... | ...F... | ....... |
| iPS:43 6092 | 21-225_195B9 | VK1|A30/JK3 | ....... | ....... | ...D... | ...G... | ....... | ...C... | ...YR | ....... | ....... |
| iPS:43 6164 | 21-225_197G10 | VK1|A30/JK3 | ....... | ....... | ....... | ....... | ....... | ....... | ...YR | ...F... | ....... |
| iPS:43 6191 | 21-225_198B9 | VK1|A30/JK3 | ...S... | ....... | ....... | ....... | ....... | ...V... | ...YR | ....... | ....... |
| iPS:43 6205 | 21-225_199A7 | VK1|A30/JK3 | ....... | ....... | ....... | ....... | ....... | ...V... | ...YR | ....... | ....... |
| iPS:43 6214 | 21-225_200F6 | VK1|A30/JK3 | ....... | ...D... | ....... | ....... | ....... | ...H... | ...YR | ....... | ....... |
| iPS:43 6248 | 21-225_202A3 | VK1|A30/JK3 | ....... | ....... | ...R... | ...C... | ....... | ...I... | ...HD | ....... | ....... |
| iPS:43 6268 | 21-225_203B9 | VK1|A30/JK3 | ....... | ....... | R...V.N | ....... | ....... | ...H... | ....... | ....... | ....... |
| iPS:43 6350 | 21-225_210E4 | VK1|A30/JK3 | ....... | ....... | ....... | ....... | ....... | ....... | ....... | ....... | ....... |
| iPS:43 6576 | 21-225_225B6 | VK1|A30/JK3 | ...I... | ...M...K. | ...T... | ....... | ....... | ....... | ....... | ....... | ....... |

| | Germline | K_FR1 | K_CDR1 | K_FR2 | K_CDR2 | K_FR3 | K_CDR3 | K_FR4 |
|---|---|---|---|---|---|---|---|---|
| iPS:39_3822 | 21-225_15B11 | VK1|A30/JK3 | ........................ | ........... | ........... | ........ | ........................ | ........... | ........ |
| iPS:39_3944 | 21-225_14D6 | VK1|A30/JK3 | ........................ | ....D...... | ....H...... | ........ | ........................ | ....Y...... | ....N... |
| iPS:39_4033 | 21-225_5F4 | VK1|A30/JK3 | ......S................. | ....H...... | ........... | ........ | ........................ | ....Y.G.... | ........ |
| iPS:39_4069 | 21-225_16H1 | VK1|A30/JK3 | ........................ | ....DI..... | ........... | ....N... | ....V.................... | ....YH..... | ....V... |
| iPS:40_2229 | 21-225_16H9 | VK1|A30/JK3 | ........................ | ....Y...... | ....F...... | ....G... | ....I.................... | ....YH...L. | ........ |
| VK1|O12/JK1 | Germline | K_FR1<br>DIQMTQSPSSLS<br>ASVGDRVTITC | K_CDR1<br>RAS_QSIS<br>____SYLN | K_FR2<br>WYQQKPGK<br>APKLLIY | K_CDR2<br>A___<br>ASSLQS | K_FR3<br>GVPSRFSGSGSG<br>TDFTLTISSLQPEDFAT<br>YYC | K_CDR3<br>QQSYS<br>____ | K_FR4<br>TPGQGTK<br>VEIK |
| iPS:46_8848 | 21-225_54B1 | VK1|O12/JK1 | ........L.............. | ....N...... | ....F...... | ........ | ....P.................... | ....R...TPL. | ........ |
| iPS:43_4239 | 21-225_58F1 | VK1|O12/JK1 | ........................ | ....T...NF. | ....F...... | ........ | ....I...I................ | ....I.....I. | ........ |
| iPS:43_5513 | 21-225_157F3 | VK1|O12/JK1 | ........................ | ....N...... | ....L...... | ....t... | ........................ | ....N...TPT. | ........ |
| iPS:43_5729 | 21-225_173E7 | VK1|O12/JK1 | ....CT...A..Y........... | ....T...N.. | ........... | ....I... | ........................ | ....R...TPQ. | ........ |
| iPS:43_5753 | 21-225_175G10 | VK1|O12/JK1 | ........................ | ....T.G.... | ....R...... | ........ | ....G.....V.............. | ....R...TPQ. | ........ |
| iPS:43_5799 | 21-225_181G3 | VK1|O12/JK1 | ........................ | ....N...... | ....A...... | ....t... | ........................F | ........... | ........ |
| iPS:43_5813 | 21-225_183A12 | VK1|O12/JK1 | ......N................. | ....RN..... | ....N...... | ....TLN.<br>V...V | ........................F | ........... | ....D.R |
| iPS:43_6003 | 21-225_192G10 | VK1|O12/JK1 | ........................ | ....N...... | ....F...... | ....E... | ........................S | ....SP..... | ........ |
| iPS:43_6212 | 21-225_200G1 | VK1|O12/JK1 | ........................ | ....N.N.... | ....G.V..F. | ....T... | ........................S | ....SP..... | ....F.. |
| iPS:39_2730 | 21-225_17A1 | VK1|O12/JK1 | ........................ | ....N.N.... | ....G.V..L. | ....t.t | ........................ | ....SP..... | ........ |
| iPS:39_2736 | 21-225_17B12 | VK1|O12/JK1 | ......S................. | ....N...... | ........... | ....T.. | ........................ | ....T.T.TPT. | ........ |
| iPS:39_2766 | 21-225_23H4 | VK1|O12/JK1 | ........................ | ....R...... | ....R..S..C | ....S...T | ........................ | ........... | ........ |
| iPS:39_2770 | 21-225_20C10 | VK1|O12/JK1 | ......H.....K.S......... | ....HH..... | ........... | ....T... | ........................ | ....T...TPT. | ....R.. |
| iPS:39_2808 | 21-225_20F8 | VK1|O12/JK1 | ........................ | ....R...... | ....E...... | ........ | ....I.................... | ....N...TPT. | ........ |

| | | | | | | | | | |
|---|---|---|---|---|---|---|---|---|---|
| iPS:43 5309 | 21-225_146F9 | VK4|B3/J K2 | ........ | ....NI.H. | ....Y... | ........ | ....T... | ........ | ........ |
| iPS:43 5323 | 21-225_147D5 | VK4|B3/J K2 | ........ | ......N.. | ........ | ........ | ......S. | ....H... | .....CS |
| iPS:43 5399 | 21-225_150D2 | VK4|B3/J K2 | ........ | ....R.... | ........ | ........ | ........ | ........ | ......R. |
| iPS:43 5435 | 21-225_152H3 | VK4|B3/J K2 | ......K. | ...S.K.T. | ....F... | ........ | ........ | ....F... | .....CS |
| iPS:43 5451 | 21-225_152D10 | VK4|B3/J K2 | ........ | ....Y..T. | ........ | ....K... | ....N... | ........ | .....N.. |
| iPS:43 5459 | 21-225_152E12 | VK4|B3/J K2 | G.....A.D | ........ | ........ | ....K... | ....Y... | ........ | ....RSPS |
| iPS:43 5467 | 21-225_153B9 | VK4|B3/J K2 | AV...... | T....I.H. | ........ | ........ | ........ | ........ | .G.CS |
| iPS:43 5471 | 21-225_153F11 | VK4|B3/J K2 | G...F... | ......Y.. | ....H... | ....F... | ....Y.V.C | ........ | ....N- |
| iPS:43 5475 | 21-225_154H6 | VK4|B3/J K2 | ........ | ....YK..H | ....N... | ....K... | ........ | ........ | ....RSLS |
| iPS:43 5491 | 21-225_155E5 | VK4|B3/J K2 | ........ | ......Y.. | ........ | ........ | ....S... | ....H... | .....CS |
| iPS:43 5495 | 21-225_155B6 | VK4|B3/J K2 | ........ | ......N.. | ........ | ....T... | ........ | ........ | .....CS |
| iPS:43 5501 | 21-225_156H1 | VK4|B3/J K2 | ........ | ......Y.H | ........ | ....K... | ....A... | ....H... | .....CS |
| iPS:43 5589 | 21-225_160A4 | VK4|B3/J K2 | ........ | ......N.H | ........ | ....T... | ........ | ........ | ....N... |
| iPS:43 5727 | 21-225_172E11 | VK4|B3/J K2 | ........ | ......N.H | ........ | ........ | ....I.G. | ........ | .....S.CS |
| iPS:43 6560 | 21-225_224F11 | VK4|B3/J K2 | N.....D. | ....H..S. | ....M... | ........ | ........ | ....FT. | .....CS |
| iPS:43 6584 | 21-225_225B9 | VK4|B3/J K2 | ........ | ......N.. | ........ | ........ | ........ | ....T... | .....CS |
| iPS:43 6588 | 21-225_225F12 | VK4|B3/J K2 | ........ | ......Q.. | ....R... | ....T... | ........ | ....HSK | ....I.GK |
| iPS:43 6590 | 21-225_225H12 | VK4|B3/J K2 | ........ | ......N.. | ....N... | ........ | ....N... | ....I... | .....CS |
| iPS:43 6598 | 21-225_226D6 | VK4|B3/J K2 | ........ | R....I..I | ....M... | ........ | ........ | ....I... | .....I..Q |
| iPS:43 6636 | 21-225_227E6 | VK4|B3/J K2 | ....F... | ....D.... | ....M... | ........ | ........ | ....I... | .....S.CS |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 6644 | 21-225_227G9 | VK4|B3/JK2 | ...... | ....H. | ...... | ...G... | ...... | ...... | ...... |
| iPS:43 6646 | 21-225_227D11 | VK4|B3/JK2 | ...... | ..N... | ...... | ...... | ...I.. | ..N... | ...A.S |
| iPS:43 7363 | 21-225_74C10 | VK4|B3/JK2 | ...D.. | ..N... | ...... | ...... | ...... | ...... | ....CS |
| iPS:45 1131 | 21-225_160A7 | VK4|B3/JK2 | ...L..P. | ...A.. | ..N... | ...... | ...... | ...Y.. | ....CS |
| iPS:39 3088 | 21-225_33D1 | VK4|B3/JK2 | ......S | ..H.N.. | ..R..H..F | ...... | .L...I..C | ...... | ....CS |
| iPS:39 4085 | 21-225_8B11 | VK4|B3/JK2 | ...... | ..I.... | .R..T. | ...... | ...... | ...T.. | ..S.CS |
| iPS:39 8496 | 21-225_22D2 | VK4|B3/JK2 | ....T. | ..N... | .N..N. | ...... | ...... | ...... | ....CS |
| iPS:39 8512 | 21-225_25E12 | VK4|B3/JK2 | ..L..F.M. | ..N... | ..H... | ...K.. | ...L..L | ...F.. | ...... |
| iPS:39 8522 | 21-225_32A1 | VK4|B3/JK2 | ...... | ..Y... | ...... | ...... | ...... | ...Y.. | ..S.CS |
| iPS:39 8524 | 21-225_32A5 | VK4|B3/JK2 | ...... | ...... | ..H... | ...K.. | ...A..T..L | ...T.. | ..S.CS |
| iPS:39 8538 | 21-225_34H7 | VK4|B3/JK2 | ...... | ..Y... | ..L... | ...K.. | .....L.H | ...T.. | ..S.CS |
| Germline | | | K_FR1 DIVMTQSPLSLP...VSLGERATINC | K_CDR1 RSSQSLVYS... GNTYLN | K_FR2 WFQQRPGQS PRRLIY | K_CDR2 KVSNRDS | K_FR3 GVPDRFSGSGS GTDFTLKISRVEAEDVGV YYC | K_CDR3 MQGTH...KPLT | K_FR4 FGGGT KVEIK |
| VK2|A17|JK4 | | | | | | | | | |
| iPS:46 8854 | 21-225_72C4 | VK2|A17/JK4 | ...... | ...G.. | ...... | .E..KW. | ...... | ...N..F. | ...... |
| iPS:43 7250 | 21-225_148C6 | VK2|A17/JK4 | ...... | ...... | ...... | ....W.. | ...... | ......S. | ...... |
| iPS:43 7252 | 21-225_148H11 | VK2|A17/JK4 | ...... | ...S.. | ...... | ....W.. | ...... | ......L. | ...... |
| iPS:43 7254 | 21-225_149F2 | VK2|A17/JK4 | ...... | ...S.. | ...... | ....W.. | ..V... | ...... | ......F. |
| iPS:43 7256 | 21-225_150F11 | VK2|A17/JK4 | ...S.Y....F. | ...... | .Y.... | ...W.Y. | ..V... | ...I.. | ......P. |
| iPS:43 7268 | 21-225_177D2 | VK2|A17/JK4 | ...... | ...... | ...... | ....W.. | ...... | ...I.. | ......P. |
| iPS:44 3005 | 21-225_43F11_LC1 | VK2|A17/JK4 | ......S | ...... | ...... | ...... | ...... | ...... | ...... |
| iPS:39 8530 | 21-225_32G4 | VK2|A17/JK4 | ...... | ...... | ...... | ...... | ...... | .I-....HW.. | ...... |

| | | | | | | | | | | |
|---|---|---|---|---|---|---|---|---|---|---|
| iPS:43 3973 | 21-225_46A6 | VK1|L5/J K1 | ..N...... | ........ | ........ | ........ | .N...... | ........ | .T...... | ........ |
| iPS:43 3993 | 21-225_47G7 | VK1|L5/J K1 | ..N...... | ........ | ........ | .V...... | ........ | .A...C.. | .V...... | ........ |
| iPS:43 4007 | 21-225_48D7 | VK1|L5/J K1 | ........ | .N...... | ........ | ..F..N.. | ...S.... | ........ | ........ | ........ |
| iPS:43 4063 | 21-225_51G7 | VK1|L5/J K1 | ........ | ..D..... | .V...... | ........ | A....... | ...V..C. | .H...... | ........ |
| iPS:43 4083 | 21-225_52H2 | VK1|L5/J K1 | ........ | .N...... | .F....R. | ..F.N... | ........ | ........ | .T...... | ..H..... |
| iPS:43 4133 | 21-225_54G3 | VK1|L5/J K1 | ........ | ........ | ........ | ..D..... | ........ | ....E... | ........ | ..V..... |
| iPS:43 4221 | 21-225_60A11 | VK1|L5/J K1 | ........ | .V...... | .L...... | ..T..... | ........ | .NE..... | ........ | ........ |
| iPS:43 4283 | 21-225_57F8 | VK1|L5/J K1 | ........ | .N...... | ........ | ..T..... | ........ | .NE..... | ..T..... | ........ |
| iPS:43 5711 | 21-225_171G4 | VK1|L5/J K1 | ........ | .VN..... | ..R..... | ..R.D... | ........ | ........ | ........ | ........ |
| iPS:43 5715 | 21-225_171A8 | VK1|L5/J K1 | A....... | ..D..... | .N.M.H.. | ........ | A....... | ........ | L..T.... | ........ |
| iPS:43 5717 | 21-225_171A9 | VK1|L5/J K1 | ........ | ..D.T... | ........ | ..D..... | ........ | ........ | ........ | ........ |
| iPS:43 5739 | 21-225_174G7 | VK1|L5/J K1 | A....... | ..T..... | .N...H.. | ..F..G.. | ...V.... | ........ | ..T..... | ........ |
| iPS:43 5749 | 21-225_175C10 | VK1|L5/J K1 | ........ | ........ | .N...... | ..F..G.. | ........ | ..F.D... | ........ | ........ |
| iPS:43 5775 | 21-225_178A5 | VK1|L5/J K1 | ........ | ..T..... | ........ | ........ | ........ | ..N..... | ..T..... | ........ |
| iPS:43 5777 | 21-225_178F7 | VK1|L5/J K1 | ........ | ..D.T... | ...S.... | ........ | A....... | ........ | ..L..... | ........ |
| iPS:43 5783 | 21-225_179G1 | VK1|L5/J K1 | ........ | ..D..... | ..S..... | ..V..... | ........ | ........ | ........ | ........ |
| iPS:43 5875 | 21-225_190B9 | VK1|L5/J K1 | ........ | .N...... | ........ | .G...... | ...G.... | ..G...C. | ........ | ........ |
| iPS:43 5895 | 21-225_188E8 | VK1|L5/J K1 | ........ | .N...D.. | ...L.... | ........ | ........ | ........ | ..L..... | ...R.... |
| iPS:43 5909 | 21-225_190H3 | VK1|L5/J K1 | ........ | ..LN.... | ........ | ..V..... | ........ | ........SE | ........ | ........ |
| iPS:43 6013 | 21-225_193F2 | VK1|L5/J K1 | ........ | .N...... | ........ | .G...... | ........ | ........H | ........ | ........ |
| iPS:43 6068 | 21-225_194F7 | VK1|L5/J K1 | ........ | ..R..... | ..F..T.. | ..V..... | ........ | ........S | ........ | ...R.... |

| | | | | | | | | | |
|---|---|---|---|---|---|---|---|---|---|
| iPS:43 4037 | 21-225_49G12 | VK1|O12/ JK3 | . . . . . . . . . . | S . . . . . T . . M | . . . . . . . . . . | . . . . . . . . . . | E . . A . . . . . . | . . . . . . . . . . | . . . . . . . . . . |
| iPS:43 4041 | 21-225_50H8 | VK1|O12/ JK3 | . . . . . N . . . . | . . . . . . . . . I | . . . . . . . . . . | . . . . . . . . . . | . . . . . A . . . S | N . . . . . . . . . | . . . . . . . . . I |
| iPS:43 4045 | 21-225_50H10 | VK1|O12/ JK3 | . . . . . N . . . . | . . . . Y . . . . I | . . . . . . . . . . | . . . . . . . . . . | . . . . . A . . . S | N . . . . . . . . . | . . . . . . . . . L |
| iPS:43 4049 | 21-225_50B12 | VK1|O12/ JK3 | . . . . . . . . . . | . . . . . . . . . . | . . . . . H . . . . | . . . . . . . . . . | . . . . . E . . . T | T . . . . . . . . . | . . . . . . . . . I |
| iPS:43 4073 | 21-225_51H10 | VK1|O12/ JK3 | . . . . . . . . . . | . T . . . . . T . M | . . . . . R . . . . | . . . . . . . . . I | I . . . . E . A . . | . . . . . . . . . . | . . . . . . . . . A |
| iPS:43 4107 | 21-225_53E2 | VK1|O12/ JK3 | . . . . . . . . . . | . . . . . F . . . . | . . . . N . F . . . | . . . . . V . . . . | . . . . P . . . S . | F . . . . . . . . . | . . . . . . . . . I |
| iPS:43 4181 | 21-225_56B2 | VK1|O12/ JK3 | . . . . . . . . . . | . . . . . F . . . . | . . . . N . F . . . | . . . . . V . . . . | . . . . . . . . I F | . . . . . . . . . . | . . . . . . . . . . |
| iPS:43 4225 | 21-225_60E12 | VK1|O12/ JK3 | . . . . Y . . . . . | . . . . . . . . . . | . . . . . . . . . . | . . . . . . . . . . | . . . . . . . . I F | . . . . . . . . . . | . . . . . . . . . . |
| iPS:43 4227 | 21-225_61A1 | VK1|O12/ JK3 | . . . . . . . . . . | . . . . . F . . . . | . . . . . . . . . . | . . . . . VF . . . | . . . . . . . . . P | N . . . . . . . . . | . . . . . . . . . . |
| iPS:43 4245 | 21-225_62H1 | VK1|O12/ JK3 | . . . . . . . . . . | . . . . N . F . . . | . . . . . N . . . . | . . . . . . . . . . | . . . . . . . . . P | N . . . . . . . . . | . . . . . . . . . . |
| iPS:43 4267 | 21-225_57F2 | VK1|O12/ JK3 | . . . . . . . . . . | . . . . . F . . . . | . . . . . . . . . . | . . . . . . . . . S | I . . . . L . N . . | . . . . . . . . . . | . . . . . . . . . . |
| iPS:43 4323 | 21-225_62H8 | VK1|O12/ JK3 | . . . . . . . . . . | . . . . . . . . . . | . . . . . . . . F . | . . . . . . . . . . | . . . . . . . . . . | . . . . . . . . . . | . . . . . . . . . . |
| iPS:43 4379 | 21-225_66A9 | VK1|O12/ JK3 | . . . . . . . . . . | . . . G . . T Y . . | . . . . F L . . . . | . . . . . V . . . . | . . . . . . . . . . | T . . . . . . . . . | . . . . . . . . . V |
| iPS:43 4417 | 21-225_69C8 | VK1|O12/ JK3 | . . . . . F . . . P | . . . . . N . R . . | . . . . . . . . . . | . . . . . T . . . T | . . . . . . . . . . | . . . . . . . . . . | . . . . . . . . . . |
| iPS:43 5545 | 21-225_158F4 | VK1|O12/ JK3 | . . . . . . . . . . | . . . . K . . H . . | . . . . . . . . . . | . . . . . . . . . G | S . . . . . . . . . | . . . . . . . . . . | . . . . . . . . . R |
| iPS:43 5793 | 21-225_180F8 | VK1|O12/ JK3 | . . . . . . . . . G | . . . . . T . L . . | . . . . . . . . . . | . . . . . . . . . V | . . . . . . . . . . | . . . . . . . . . . | . . . . . . . . . . |
| iPS:43 6504 | 21-225_222H4 | VK1|O12/ JK3 | . . . . . . . . . H | . . . . . . . . . N | . . . . . F . . . . | . . . . . T . . . . | . S . . . VHRD . . | . Y . F . . . . . . | . . . . . . . . . . |
| iPS:43 6510 | 21-225_222H8 | VK1|O12/ JK3 | . . . . . . . . . H | . . . . . . . . N V | . . . . . . . . . . | . . . . . I . . . . | . S . . . VHRD . I | . Y . F . . . . . . | . . . . . . . . . . |
| iPS:43 7230 | 21-225_62H10 | VK1|O12/ JK3 | . . . . . . . . . . | . . . . . . . . N V | . . . . . . . . . . | . . . . . T . . . . | . . . . . . . . . . | . H . . . . . . . . | . . . . . . . . . F |
| iPS:44 8906 | 21-225_72G9 | VK1|O12/ JK3 | . . . . . . . . . . | . . . . . . . . . . | . . . . . . . . . . | . . . . . T . . . . | . . . . . . . . . . | . H . . . . . . . . | . . . . . . . . . F |
| iPS:39 2652 | 21-225_17C6 | VK1|O12/ JK3 | . . . . . . . . . . | . . . . N . . . . . | . . . . . . . . . . | . . . . . T . . . . | . . . . . . . . . F | . . . . R . . . . . | . . . . . . . TPF |

Figure 52 (Continued)

| | | | | | | | | | | |
|---|---|---|---|---|---|---|---|---|---|---|
| iPS:39_2660 | 21-225_19B3 | VK1|O12/JK3 | . . . . . . . . . . | .G..N.I.. ..N.... | . . . . . . .N. . . | . . . . .V. . . . | .N. . . . . . . . | . . . . . . . . . | . . . . . . . . . | . . . . . . . . . |
| iPS:39_2668 | 21-225_17B4 | VK1|O12/JK3 | . . . . . . . . . .I | . . . . . . . .N. . | . . . . . . .N. . . | . . . .G. . . .T | . . . . . . . . F. | . . . . . . . . .R | . . . . . . .TPF. | . . . . . . . . . |
| iPS:39_2678 | 21-225_20F3 | VK1|O12/JK3 | . . . . . . . . . . | . . . . . . . . . .Y | . . . . . . . . . . | . . . . . . . . F. | . . . . . . . . . | . . . . . . . .N. | . . . . . . . AP. | . . . . . . . . . |
| iPS:39_2694 | 21-225_19A5 | VK1|O12/JK3 | . . . . . . . . . S. | . . . . . . . .N.I. | . . . . . . . .N. . | . . . . .V. . . .D | . . . . . . . . . | . . . . . . . . . | . . . . . . . . . | . . . . . . . . . |
| iPS:39_2696 | 21-225_20A4 | VK1|O12/JK3 | .P . . . . . . . . . | . . . . . . . . .I. | . . . . . . . .N. . | . . . . . .R. . . | . . . . . . . . . | . . . . . . . . .R | . . . . . . .TPL. | . . . . . . . F. |
| iPS:39_2702 | 21-225_17F7 | VK1|O12/JK3 | . . . . . . . . .A. | . . . . . . . .N. . | . . . . . . .S. . . | . . . . . . . . .H | . . . . . . . . . | . . . . . . . . .R | . . . . . . .TPF. | . . . . . . . . . |
| iPS:39_2704 | 21-225_17F11 | VK1|O12/JK3 | . . . . . . . . . . | . . . . . . . .T. . | . . . . . . .F. . . | . . . . . . . . . | . . . . . . . . . | . . . . . . . . .T | . . . . . . . . . | . . . . . . . . . |
| iPS:39_2720 | 21-225_17A12 | VK1|O12/JK3 | . . . . . . . . . S. | . . . . . . RT.N.. | . . . . . . . .N. . | . . . . . . . F. | . . . . . . . . . | . . . . . . . . . | . . . . . .TPL.A | . . . . . . . . . |
| iPS:39_2722 | 21-225_18E12 | VK1|O12/JK3 | . . . . . . . . . . | . . . . . . . . . . | . . . . . . . H. . . | . . . . .T. . . . | . . . . . . . . . | . . . . . . . .N. | . . . . . . .TPL. | . . . . . . . . . |
| iPS:39_2760 | 21-225_22G3 | VK1|O12/JK3 | . . . . . . . . . . | . . . . . . . . . . | . . . . . . . . . . | . . . . .T. . . . | . . . . . . . . . | . . . . . . . .R. | . . . . . . .TPF. | . . . . . . . . . |
| iPS:39_2762 | 21-225_22G5 | VK1|O12/JK3 | . . . . . . . . . . | . . . . . . . .N. . | . . . . . . . .Q. . | . . . . . . . . .N | . . . . . . . . . | . . . . . . . . .R | . . . . . . .TPL. | . . . . . . . F. |
| iPS:39_2764 | 21-225_22G10 | VK1|O12/JK3 | . . . . . . . . . . | . . . . . . . .F. . | . . . . . . .F. . . | . . . . . . . . . | . . . . . . . . .G | . . . . . . . . F. | . . . . . . .TPL. | . . . . . . . F. |
| iPS:39_2812 | 21-225_21F4 | VK1|O12/JK3 | . . . . . . . . . . | . . . . . . . N.G. | . . . . . . . . . . | . . . . . . . . F. | . . . . . . . . . | . . . . . . . .FR. | . . . . . . .TPF. | . . . . . . . . . |
| iPS:39_2816 | 21-225_22E4 | VK1|O12/JK3 | . . . . . . . . . C. | . . . . . . . . . . | . . . . . . . . . . | . . . . . . . . . | . . . . . . . . . | . . . . . . . . .R | . . . . . . .TPL. | . . . . . . . . . |
| iPS:39_2830 | 21-225_21A5 | VK1|O12/JK3 | . . . . . . . . . . | . . . . . . . .T. . | . . . . . . . .R. . | . . . . . . . . . | . . . . . . . . . | . . . . . . . . FF. | . . . . . . .TPF. | . . . . . . . F. |
| iPS:39_2852 | 21-225_21A2 | VK1|O12/JK3 | . . . . . . . . . . | . . . . . . . . .H. | . . . . . . . . . . | . . . . . . . . . | . . . . . . . . . | . . . . . . . . F. | . . . . . . . . IS. | . . . . . . . . . |
| iPS:39_2878 | 21-225_22C5 | VK1|O12/JK3 | . . . . . . . . .A. | . . . . . . . .N. . | . . . . . . . . . . | . . . . . . . . . | . . . . . . . .V. | . . . . . . . . .V | . . . . . . .TPL. | . . . . . . . . . |
| iPS:39_2902 | 21-225_22D5 | VK1|O12/JK3 | . . . . . . . . . . | . . . . . . . NF.. | . . . . . . . . .H. | . . . . . . . .V.H | . . . . . . . . I . | . . . . . . . . .R | . . . . . . .TPL. | . . . . . . . . . |
| iPS:39_2984 | 21-225_30E11 | VK1|O12/JK3 | . . . . . . . . . . | . . . . . . . .N. . | . . . . . . .QT. . | . . . . . . . . . | . . . . . . . . . | . . . . . . . . . | . . . . . . . . . | . . . . . . . . . |
| iPS:39_3114 | 21-225_33G12 | VK1|O12/JK3 | . . . . . . . . . . | . . . . . . . .N. . | . . . . . . . F. . . | . . . . . . . . . | . . . . . . . . . | . . . . . . . . . | . . . . . . . . . | . . . . . . . . . |
| iPS:39_3824 | 21-225_10F12 | VK1|O12/JK3 | . . . . . . . . . . | . . . . . . . .N. . | . . . . . . .QT. . | . . . . . . . . . | . . . . . . . . . | . . . . . . . .N. | . . . . . . .TPF. | . . . . . . . F. |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:39 3848 | 21-225_4H2 | VK1\|O12/ JK3 | . . . . . . . . . . . . . . . . . . L . . . . . . . . | . . . . . . . . . . . I . . . N . . . | . . . . . . . . . . . . . . . V . . | . . . . . . . . . . | . . . . . . . . . . . GCV.R. . . . . . . . . . R. . . | . . . . . . . . . . . R. . . | . . . . . . . . . . . . . . . . |
| iPS:39 3862 | 21-225_5G2 | VK1\|O12/ JK3 | . . . . . . . . . . . . . . . . . . . . . . . . . . . . | . . . . . . . . . . . . . . . N.I. . | . . . . . . . . . . . . . . . . . . | . . . . . . . G. . | . . . . . . . . . . . . N.R. . . . . . . . | . . . . . . . . . . . . . . . . | . . . . . . . TPL. . |
| iPS:39 3888 | 21-225_3E3 | VK1\|O12/ JK3 | . . . . . . . . . . . . . . . . . . P. . . . . . . . F | . . . . . . . . . . . . . . . . . R. . | . . . . . . . . . . . . . . R.V. . | . . . . . . . G. . | . . . . . . . . . . . . . . . . . . . . . . . . | . . . . . . . . . . . . . . . . | . . . . . . . TPL. . |
| iPS:39 3890 | 21-225_4B1 | VK1\|O12/ JK3 | . . . . . . . . . . . . . . . . . . P. . . . . . . . F | . . . . . . . . . . . HT.R. . . T. . | . . . . . . . . . . . . . . H.V. . | . . . . . . . . .T | . . . . . . . . . . . . . . IN . . . . TN . . . . | . . . . . . . . . . . N. . . | . . . . . . . . IS . . |
| iPS:39 3898 | 21-225_5F7 | VK1\|O12/ JK3 | . . . . . . . . . . . . . . . . . . P. . . . . . . . F | . . . . . . . . . . . . . . . T . . . T | . . . . . . . . . . . . . . . . . . | . . . . . . . . . . | . . . . . . . . . . . . . . . . . . . . . . . . | . . . . . . . . . . . N. . . | . . . . . . . TPL. . |
| iPS:39 3904 | 21-225_8H11 | VK1\|O12/ JK3 | . . . . . . . . . . . . . . . . . . . . . . . . . . . . | . . . . . . . . . . . . . . . N.I. . | . . . . . . . . . . . . . . . . . . S | . . . . . . . . V . T. . . H. . | . . . . . . . . . . . . . . . . . . . . . . . . . S | . . . . . . . . . . . . . . . T . | . . . . . . . SP. . . . . . . . . V . . . . . . . . A. |
| iPS:39 3936 | 21-225_14A11 | VK1\|O12/ JK3 | . . . . . . . F. . . . . . . . . I . . . . . . . . . | . . . . . . . . . . . T . . . . . T . | . . . . . . . . . . . . . . . . . . | . . . . . . . . . . N | . . . . . . . . . . . . . . . . . . . . . . . . | . . . . . . . . . . . . . . . . | . . . . . . . . . . . |
| iPS:39 3980 | 21-225_6D3 | VK1\|O12/ JK3 | . . . . . . . . . . . . . . . . . . . . . . . . . . . . | . . . . . . . . . . . . . . . . . . | . . . . . . . . . . . . . . . . . . | . . . . . . . . . . | . . . . . . . . . . . . . . . . . . . . . . . F. | . . . . . . . . . . . R. . . | . . . . . . . TPF. . |
| iPS:39 4014 | 21-225_8G6 | VK1\|O12/ JK3 | . . . . . . . . . . . . . . . . . . . . . . . . . . . . | . . . . . . . . . . . . . . . . . . | . . . . . . . . . . . . . . . . . . | . . . . . . . . . . | . . . . . . . . . . . . . . . . . . . . . . . F. | . . . . . . . . . . . R. . . | . . . . . . . TPF. . |
| iPS:39 4022 | 21-225_16H6 | VK1\|O12/ JK3 | . . . . . . . . . . . . . . . . . . . . . . . . . . . . | . . . . . . . . . . . . . . . . N . . | . . . . . . . . . . . . . . . . . . | . . . . . . . . . . | . . . . . . . . . . . . . . . . . . . . . . . . | . . . . . . . . . . . R. . . | . . . . . . . TPL. . |
| iPS:39 4043 | 21-225_3B1 | VK1\|O12/ JK3 | . . . . . . . . . . . . . . . . . . . . . . . . . . . . | . . . . . . . . . . . . . . . . . . | . . . . . . . . . . . . . . . . . . | . . . . . . . . .T | . . . . . . . . . . . . . . . . . . . . . . . . | . . . . . . . . . . . . . . . . | . . . . . . . . . . . F. |
| iPS:39 4051 | 21-225_9E5 | VK1\|O12/ JK3 | . . . . . . . . . . . . . . . . . . . . . . . . . . Q. | . . . . . . . . . . . . . . . . A. . | . . . . . . . . . . . . . . . . . . | . . . . . . . G. . | . . . . . . . . . . . . . . . . . . . . . . . . | . . . . . . . . . . . . . . . . | . . . . . . . TPL.S |
| iPS:39 4077 | 21-225_8E12 | VK1\|O12/ JK3 | . . . . . . . . . . . . . . . . . . . . . . . . . . . . | . . . . . . . . . . . . . . . N . . . | . . . . . . . . . . . . . . . . . . | . . . . . . . . . . | . . . . . . . . . . . . . . . . . . . . . . . . | . . . . . . . . . . . R. . . | . . . . . . . TPF. . |
| iPS:39 4087 | 21-225_11A5 | VK1\|O12/ JK3 | . . . . . . . . . . . . . . . . . . . . . . . . . . . . | . . . . . . . . . . . . . . . N.Y. . | . . . . . . . . . . . . . . . . . . | . . . . . . . . . . | . . . . . . . . . . . . . . . . . . . . . . . . | . . . . . . . . . . . N. . . | . . . . . . . TPL. . |
| | Germline | K_FR1 | K_CDR1 | K_FR2 | K_CDR2 | K_FR3 | K_CDR3 | K_FR4 |
| VK2\|A18\|JK 3 | | DVVMTQTPLSLS VPGQPASISC | KSS QSLLHSD GKTYLY | WYLQKPGQ SPQLLIY | EVS NRFS | GVPDRFSGSGSG TDFTLKISRVEAEDVGV YYC | MQG... LOFFT | FGPGTK VDIK |
| iPS:43 4053 | 21-225_51E1 | VK2\|A18/ JK3 | . . . . . . . . . . . . . . . . . . M. . . . . . . . . | . . . . . . . . . . . . . . . . E. . | . . . . . . . . . . . . . . . R. . . P.F.F | . . . . . . . N . . | . . . . . . . . . . . . . . . . . . . . . . . E. | . . . . . . . . . . . S.Q. . | . . . . . . . . . . . |
| iPS:43 4137 | 21-225_54D4 | VK2\|A18/ JK3 | . . . . . . . . . . . . . . . . . . M. . . . . . . . . | . . . . . . . . . . . . . . . . E. . | . . . . . . . . . . . . . . . R. . . P.F.F | . . . . . . . N . . | . . . . . . . . . . . . . . . . . . . . . . . E. . . I . . . . | . . . . . . . S.Q. . | . . . . . . . . . . . F. |
| iPS:43 4149 | 21-225_55H1 | VK2\|A18/ JK3 | . . . . . . . . . . . . . . . . . . . . . . . . . . . . | . . . . . . . . . . . . . . . . E. . | . . . . . . . . . . . . . . . . . . P.F.F | . . . . . . . . .H | . . . . . . . . . . . . . . . . . . . . . . . . | . . . . . . . S.Q. . | . . . . . . . . . . . |
| iPS:43 5315 | 21-225_147B2 | VK2\|A18/ JK3 | . . . . . . . . . . . . . . . . . . . . . . . . . . . . | . . . . . . . . . . . . . . . . . . | . . . . . . . . . . . . . . . . . . P. . | . . . . . . . H.V. | . . . . . . . . . . . . . . . . . . . . . . V . | . . . . . . . STQ. . | . . . . . . . F.P. |
| | Germline | K_FR1 | K_CDR1 | K_FR2 | K_CDR2 | K_FR3 | K_CDR3 | K_FR4 |

Figure 52 (Continued)

| | | K_FR1 DIQMTQSPSSL SASVGDRVTITC | K_CDR1 RASQSIS SYLN | K_FR2 WYQQKPGK APKLLIY | K_CDR2 AASSLQS | K_FR3 GVPSRFSGSGSGTDFTLTISSLQPEDFATYYC | K_CDR3 QQSYS TPIT | K_FR4 FGQGTK VEIK |
|---|---|---|---|---|---|---|---|---|
| | VK1|O18/JK3 | | | | | | | |
| iPS:43 4055 | 21-225_51B4 | ........................ | ....R.T... .F | ................ | ............. | ...................... ...CVH..................... | .Q.YDN ----IPLT | .....T |
| | Germline | K_FR1 | K_CDR1 | K_FR2 | K_CDR2 | K_FR3 | K_CDR3 | K_FR4 |
| | VK1|O18/JK4 | DIQMTQSPSSL SASVGDRVTITC | QAS QDIS NYLA | WYQQKPGK APKLLIY | D ASNLET | GVPSRFSGSGSGTDFTLTISSLQPEDFATYYC | QQYDN ----LPTT | FGQGTK VEIK |
| iPS:43 4087 | 21-225_52F6 | ........................ | ..........H | ................ | ............ | .............L............E | ....C.... | ....... |
| iPS:43 4111 | 21-225_53H2 | ........................ | ..........H ...Q | ................ | ....T.G | .............N............S | ..H....... | ....... |
| iPS:43 4121 | 21-225_53F6 | ........................ | ..........T. ..D | ................ | ............ | .............T............ | ....C.... | ....... |
| iPS:43 4163 | 21-225_50H1 | .........P.............. | ..........D | ................ | .......G | A........................... | ....C.... | ....... |
| iPS:43 5611 | 21-225_161F10 | ........................ | ..........Y. .H.S | .........W.... | ............ | .............G............F | ....E.... | ....... |
| iPS:43 5811 | 21-225_183H6 | ............A........... | ........... | ..........T ..V | ............ | .............A............ | ...... | .....D. |
| iPS:43 4035 | 21-225_5G9 | ........................ | ..........G. ..S | ................ | ............ | .............A............ | .......... | ....... |
| | Germline | K_FR1 DIQMTQSPSSL SASVGDRVTITC | K_CDR1 RAS QSIS SYLA | K_FR2 WYQQKPGK APKLLIY | K_CDR2 A ASSLQS | K_FR3 GVPSRFSGSGSGTDFTLTISSLQPEDFATYYC | K_CDR3 QQYNS ----LPTT | K_FR4 FGQGTK VEIK |
| | VK1|L1/JK1 | | | | | | | |
| iPS:43 4095 | 21-225_52F10 | V....................... | .........G. | ................ | ............ | .............K............ | .......P. | ....... |
| iPS:39 2848 | 21-225_20F9 | ....................T... | ............ | ................ | ............ | ........................... | .......... | ....... |
| iPS:39 3078 | 21-225_33H11 | .F...................... | W.......S. ..N | .......R...... | ............ | .............K............ | .H.....L | ....... |
| iPS:39 3142 | 21-225_33A3 | ........................ | ............ ..N | ................ | ............ | I............K............R | .F........ | ....... |
| iPS:39 3946 | 21-225_16A4 | ........................ | .........D | ................ | .......G | .............K............ | .F.....P. | ....... |
| | Germline | K_FR1 DIQMTQSPSSL SASVGDRVTITC | K_CDR1 RAS QSIS SYLN | K_FR2 WYQQKPGK APKLLIY | K_CDR2 A ASSLQS | K_FR3 GVPSRFSGSGSGTDFTLTISSLQPEDFATYYC | K_CDR3 QQSYS ----LPTT | K_FR4 FGQGTP LEIK |
| | VK1|O12/JK5 | | | | | | | |
| iPS:43 4117 | 21-225_53C6 | ........................ | ...YS..... ..D | ..........V.F | ...K........ | .............E............ | .......F. | .....N. |

| ID | Name | Germline | | | | | | | | | | |
|---|---|---|---|---|---|---|---|---|---|---|---|---|
| iPS:43 4367 | 21-225_65H11 | VK1|L1/J K4 | .......... | .......... | .......... | .......... | .......... | ..K....... | .......... | .......... | .......... | .......... |
| iPS:43 4429 | 21-225_70H6 | VK1|L1/J K4 | ......L... | T...S.F. | ..R.... | .......... | ..I....... | .......... | ...SY..... | ...F...... | .......... |
| iPS:43 4535 | 21-225_74C8 | VK1|L1/J K4 | .......... | .......G. | ..V.... | .......... | .A.K..... | .......... | ...SN..... | ...I...... | .......... |
| iPS:43 4573 | 21-225_77E6 | VK1|L1/J K4 | .......... | ....K..... | T.N... | .......G | .A.K..... | ...Y...... | ...SN..... | .......... | ....N..... |
| iPS:43 4615 | 21-225_76C5 | VK1|L1/J K4 | .......... | ....K..V. | .......... | .......... | .A.K..... | .......... | ...SN..... | .......... | ....R..... |
| iPS:43 4669 | 21-225_79F4 | VK1|L1/J K4 | .......... | ....K..G. | ..T.... | .......G | .A.K..... | ...Y...... | ...SN..... | .......... | ....R..... |
| iPS:43 4737 | 21-225_74G6 | VK1|L1/J K4 | .......... | ....K..G. | ..T.N.. | .......... | .A.K..... | .......... | ...SN..... | .......... | ....N..... |
| iPS:43 4741 | 21-225_80C11 | VK1|L1/J K4 | .......... | ....R..V. | ..R.T.. | .......... | ...K..... | .......... | ...SN..... | .......... | .......... |
| iPS:43 4867 | 21-225_79A12 | VK1|L1/J K4 | .......... | ....K..D.N | .......... | .......... | ...K..... | .......... | .......... | .......... | .......... |
| iPS:43 5333 | 21-225_147E9 | VK1|L1/J K4 | .......... | .......... | ..V.... | .......... | ...K..... | .......... | ....N..... | .......... | .......... |
| iPS:43 5409 | 21-225_150G8 | VK1|L1/J K4 | .......... | .......H. | .......... | ....N.. | ...K..... | .......... | .......... | .......... | .......... |
| iPS:43 5505 | 21-225_157C1 | VK1|L1/J K4 | T..I.L. | .......R. | .......... | ....L.. | ...K..... | .......... | .......... | ...F.F.... | ...L...... |
| iPS:43 5595 | 21-225_160H4 | VK1|L1/J K4 | .......... | .......D. | ..L.... | ....L.. | .......... | .......... | .......... | .......... | .......... |
| iPS:43 5639 | 21-225_163G6 | VK1|L1/J K4 | .......... | .......D..V | ..V.... | .......... | ...K..... | .......... | ....H..... | .......... | ...A...... |
| iPS:43 5653 | 21-225_166H12 | VK1|L1/J K4 | .......... | .......D. | ..S.... | .......... | ...K..... | .......... | ....SD.... | ...F...... | .......... |
| iPS:43 5677 | 21-225_169C10 | VK1|L1/J K4 | .......... | .......D. | ..S.... | .......... | N..K..... | .......... | ....SD.... | .......... | .......... |
| iPS:43 5699 | 21-225_170D6 | VK1|L1/J K4 | .......A. | ...D.G.C. | ..S.F.. | .......... | ...K..... | .......... | ....SD.... | .......... | .......... |
| iPS:43 5745 | 21-225_175G3 | VK1|L1/J K4 | .......... | .......D. | ...D.. | .......... | ...K..... | .......... | .......... | .......... | .......... |
| iPS:43 5819 | 21-225_190C11 | VK1|L1/J K4 | ...t...... | T......G. | ..K.T.. | .......... | ...K..... | .......... | ....MT.... | ...F...... | ...T...... |
| iPS:43 5825 | 21-225_190G11 | VK1|L1/J K4 | .......... | T......G. | ..K.L.. | .......... | ...K..... | .......... | ....MT.... | .......... | .......... |
| iPS:43 5837 | 21-225_198G3 | VK1|L1/J K4 | ...A...... | ..K....G. | ..L.... | .......G | ...K..... | .......... | ....MT.... | .......... | .......... |

Figure 52 (Continued)

| ID1 | ID2 | Type | | | | | | | | | |
|---|---|---|---|---|---|---|---|---|---|---|---|
| iPS:43 5845 | 21-225_191G1 | VK1|L1/J K4 | .... | .... | .... | .... | .... | K.... | .... | H.LT.... | .... |
| iPS:43 5859 | 21-225_190E6 | VK1|L1/J K4 | .... | T....G... | .... | K.... | .... | K.... | .... | ...MT.... | .... |
| iPS:43 5873 | 21-225_190G4 | VK1|L1/J K4 | .... | ....D.G... | .... | .... | .... | K.... | ...N | ...ST.... | .... |
| iPS:43 5933 | 21-225_190F8 | VK1|L1/J K4 | .... | ....R.... | ...L | K.... | .... | K.... | .... | ...MT.... | .... |
| iPS:43 5945 | 21-225_191A10 | VK1|L1/J K4 | .... | T....G... | .... | .... | .... | K.... | ...Y N.I | ...ST.... | .... |
| iPS:43 5947 | 21-225_191E10 | VK1|L1/J K4 | .... | ....K.... | ...L | .... | .... | K.... | ...N | ...ST.... | .... |
| iPS:43 5957 | 21-225_191G12 | VK1|L1/J K4 | .... | ....K.... | .... | K.... | .... | K.... | .... | ...IT.... | ...S. |
| iPS:43 5963 | 21-225_192D2 | VK1|L1/J K4 | ...I | T....G... | ...L | .... | .... | K.... | .... | H.VT....N | .... |
| iPS:43 5971 | 21-225_192D3 | VK1|L1/J K4 | .... | .... | .... | .... | .... | K.... | .... | LH.LT.... | .... |
| iPS:43 5979 | 21-225_192H4 | VK1|L1/J K4 | .... | ....D.... | ...S | .... | .... | K....R | ...G | LH.LN.... | ..R |
| iPS:43 5987 | 21-225_192G6 | VK1|L1/J K4 | ..K. | T....G... | ...L | K.... | .... | K.... | .... | ...MT.... | .... |
| iPS:43 5993 | 21-225_192C8 | VK1|L1/J K4 | .... | T....G... | ...L | K.... | .... | K.... | .... | H.LT.... | .... |
| iPS:43 5997 | 21-225_192G8 | VK1|L1/J K4 | .... | ....G... | .... | .... | .... | K.... | .... | ...IT.... | .... |
| iPS:43 6005 | 21-225_192H10 | VK1|L1/J K4 | .... | ....K.... | .... | .... | .... | K....Y | .... | ...ST.... | .... |
| iPS:43 6031 | 21-225_193C7 | VK1|L1/J K4 | .... | ....G... | .... | .... | .... | K....N | .... | ...ST.... | .... |
| iPS:43 6045 | 21-225_193A10 | VK1|L1/J K4 | .... | .... | .... | .... | .... | K.... | ...F | H.LT.... | .... |
| iPS:43 6054 | 21-225_194C1 | VK1|L1/J K4 | .... | .... | .... | .... | .... | K.... | .... | LH.LT.... | .... |
| iPS:43 6076 | 21-225_194H11 | VK1|L1/J K4 | .... | T....K... | ...L | K....V | .... | K.... | .... | ...MT.... | .... |
| iPS:43 6086 | 21-225_191G10 | VK1|L1/J K4 | .... | .... | .... | .... | .... | K.... | .... | H.LT.... | .... |
| iPS:43 6090 | 21-225_195A9 | VK1|L1/J K4 | .... | ..N..A.... | .... | .... | .... | K.... | .... | H.LT.... | .... |
| iPS:43 6112 | 21-225_196C7 | VK1|L1/J K4 | .... | .... | .... | .... | .... | K.... | .... | H.LT.... | .... |

Figure 52 (Continued)

| | | | | | | | | |
|---|---|---|---|---|---|---|---|---|
| iPS:43 6138 | 21-225_197F2 | VK1|L1/J K4 | ....L.... | ....G.. | ....K.. | ....K.... | ........ | ...IT | .... |
| iPS:43 6152 | 21-225_197B6 | VK1|L1/J K4 | ........ | ...K.... | ........ | ....K....N | ....F... | ...ST | .... |
| iPS:43 6173 | 21-225_197G12 | VK1|L1/J K4 | ....L.... | ....G.. | ...K....L | .F.K.... | ....F... | ...MT | .... |
| iPS:43 6189 | 21-225_198B6 | VK1|L1/J K4 | ........ | ...K.... | ........ | ....K...NR | ........ | ...ST | .... |
| iPS:43 6201 | 21-225_199C5 | VK1|L1/J K4 | ........ | ........ | ........ | ....K.... | ........A | ...LT | .... |
| iPS:43 6260 | 21-225_203H1 | VK1|L1/J K4 | ........ | ...K.... | ...V....R | ....K....T.D | ........S | .R.HT | .... |
| iPS:43 6282 | 21-225_204G6 | VK1|L1/J K4 | ..R..... | ...T....I | ........ | ........ | ........ | H.L.. | .... |
| iPS:43 6284 | 21-225_204G8 | VK1|L1/J K4 | ........ | ..H..... | .....F.. | ....Q....V | ....E... | ...SN | .... |
| iPS:43 6292 | 21-225_205H3 | VK1|L1/J K4 | ..P..... | ..A..... | ...L.... | ....K....R | ........S | ...SN | .... |
| iPS:43 6296 | 21-225_205F5 | VK1|L1/J K4 | ........ | ..H....G | ........ | ....K.... | ........T | ...SN | .... |
| iPS:43 6324 | 21-225_207G6 | VK1|L1/J K4 | ........ | ....R... | ...L.... | ....K...NR | ........ | ...SN | D.R |
| iPS:43 6364 | 21-225_211A11 | VK1|L1/J K4 | ..E....P | ....G... | ..R..... | ....K....R..G | ........ | .H.MT | A.. |
| iPS:43 6366 | 21-225_211A3 | VK1|L1/J K4 | ........ | ........ | .V..R... | ....K...NN..V | ........ | ...SN | .... |
| iPS:43 6372 | 21-225_211A8 | VK1|L1/J K4 | ........ | ........ | ........Q | ........S | ........L | LR.DT | .... |
| iPS:43 6376 | 21-225_212E6 | VK1|L1/J K4 | ........ | ...R.... | .....H.. | ........ | ........ | ...VT | I.. |
| iPS:43 6378 | 21-225_212D7 | VK1|L1/J K4 | ..E..... | ..S..... | .....L..S..N | ....K....R | ........ | ...SN | .... |
| iPS:43 6380 | 21-225_212H9 | VK1|L1/J K4 | ........ | ..A.G... | .....R.. | ....K...NR | ........ | LR.DT | .... |
| iPS:43 6384 | 21-225_212F10 | VK1|L1/J K4 | ..R..... | ..KH.... | ........R | ....K.... | ........L | .H.SN | .... |
| iPS:43 6388 | 21-225_212H11 | VK1|L1/J K4 | ........ | ..H..... | .....H.. | ....K...NR..V | ........ | .H.SN | V.. |
| iPS:43 6390 | 21-225_213D2 | VK1|L1/J K4 | ........ | ..A.R... | ..C..T.. | ....NN.. | ........ | H..SN | ..T |
| iPS:43 6394 | 21-225_213C4 | VK1|L1/J K4 | ..H..... | ........ | ........ | ....K.... | ........ | ...SN | .... |

Figure 52 (Continued)

| ID | Gene | | | | | | | | |
|---|---|---|---|---|---|---|---|---|---|
| iPS:43 6396 | 21-225_213E5 | VK1|L1/J K4 | ....R... | ........ | ...R... | ........ | K...... | ........ | .H.SN... | ........ |
| iPS:43 6398 | 21-225_213B8 | VK1|L1/J K4 | ........ | ...KH... | ........ | ........ | K...... | ........ | ...SN... | ........ |
| iPS:43 6410 | 21-225_212E10 | VK1|L1/J K4 | ........ | ...H.... | ........ | ........ | K...... | ........ | ...SN... | ........ |
| iPS:43 6420 | 21-225_215B5 | VK1|L1/J K4 | ........ | ...H.... | ...H.... | ........ | K..NR.. | ........ | ...IN... | ........ |
| iPS:43 6422 | 21-225_215D6 | VK1|L1/J K4 | ........ | ...H.... | ........ | ........ | NN..... | V...... | ...VT... | ........ |
| iPS:43 6430 | 21-225_215A12 | VK1|L1/J K4 | ....T... | F..D.G.. | ........ | ........ | K...R.. | ........ | ...VT... | ........ |
| iPS:43 6452 | 21-225_217G5 | VK1|L1/J K4 | ....L... | ...G.... | ...R.... | ........ | K...R.. | .S...... | ...VN... | ........ |
| iPS:43 6454 | 21-225_217B10 | VK1|L1/J K4 | ....R... | ...KH... | ........ | ...R.... | K...TR. | .D...... | .HTSK... | LV...... |
| iPS:43 6464 | 21-225_219H1 | VK1|L1/J K4 | ....Q... | ...D.... | ........ | ..S..... | K...V.. | .L....R | .H.SN... | .S.VQ... |
| iPS:43 6490 | 21-225_221F6 | VK1|L1/J K4 | G....... | ........ | ........ | ..N..... | K...... | ........ | ...MT... | .......T |
| iPS:43 6502 | 21-225_222A11 | VK1|L1/J K4 | ........ | ........ | ........ | ........ | K...R.. | ........ | LY.LN... | ......R |
| iPS:43 6514 | 21-225_222D10 | VK1|L1/J K4 | ........ | ........ | ........ | ........ | K...... | ........ | LH.LN... | ......R |
| iPS:43 6522 | 21-225_223H10 | VK1|L1/J K4 | ........ | ........ | ........ | ..N..... | K...... | ........ | LH.LN... | ........ |
| iPS:43 7258 | 21-225_153F9 | VK1|L1/J K4 | ...A.... | ........ | ........ | ........ | K...... | ........ | ...S.... | ........ |
| iPS:43 7260 | 21-225_170D1 | VK1|L1/J K4 | ........ | ...D.... | ........ | ..S..... | ........ | ........ | ...CD... | ........ |
| iPS:43 7264 | 21-225_171H12 | VK1|L1/J K4 | ........ | ...D.... | ..F..... | ........ | ........ | ........ | ...SD..F | ........ |
| iPS:43 7266 | 21-225_177A5 | VK1|L1/J K4 | ........ | ...D.... | ........ | ..S..... | K...... | ........ | ...SD... | ........ |
| iPS:43 7270 | 21-225_178H4 | VK1|L1/J K4 | ........ | ...D.... | ..L..... | ........ | K...... | ........ | ...S.... | ........ |
| iPS:43 8664 | 21-225_216G1 | VK1|L1/J K4 | ....E... | ..S..... | ........ | ........ | K...N.. | ........ | LR.DT... | ........ |
| iPS:45 1120 | 21-225_197D3 | VK1|L1/J K4 | ........ | ....R... | ........ | ........ | K...... | ........ | .H.LT... | ........ |
| iPS:39 2682 | 21-225_16A12 | VK1|L1/J K4 | ........ | ...A.N.. | ........ | ..S..... | K...... | E...... | ...Y.... | ........ |

| | | K_FR1 | K_CDR1 | K_FR2 | K_CDR2 | K_FR3 | K_CDR3 | K_FR4 |
|---|---|---|---|---|---|---|---|---|
| iPS:39 4029 | 21-225_1B12 | VK1|O18/ JK5 | ........................ | ........N.. | ............ | ............ | ............................................ | ......E...... | ............ |
| iPS:39 4047 | 21-225_5E6 | VK1|O18/ JK5 | ........................ | ............ | .....C...... | ............ | ............................................ | ............. | ............ |
| iPS:39 4081 | 21-225_16B3 | VK1|O18/ JK5 | ........................ | ........N... | ............ | .........R.. | ............................................ | ............. | ............ |
| | Germline | | K_FR1 DIVMTQSPATLS VSPGERATLSC | K_CDR1 RAS QSVS SYLA | K_FR2 WYQQKPGQ APRLLIY | K_CDR2 GASTRAT | K_FR3 GIPARFSGSGSGS GTEFTLTISSLQSEDFAV YYC | K_CDR3 QQYNN WPLT | K_FR4 FGQGTR VDIK |
| VK3L2JK3 | | | | | | | | | |
| iPS:43 4219 | 21-225_60E9 | VK3|L2/J K3 | ........................ | ........S... | ........R... | ............ | ..............T............................. | .......S...... | ......I..... |
| iPS:43 4279 | 21-225_57F7 | VK3|L2/J K3 | .....T...........F...... | ........D... | ............ | ............ | ..M.......................G.................C | .......F...... | ............ |
| iPS:43 4289 | 21-225_57H12 | VK3|L2/J K3 | ........................ | ........D... | ............ | ......A..... | .........................H................... | .......D...... | ............ |
| iPS:43 4291 | 21-225_58A4 | VK3|L2/J K3 | ........................ | ........D... | .....R...... | ......A..... | ............................................ | .......F...... | ............ |
| iPS:43 4297 | 21-225_58A10 | VK3|L2/J K3 | .....C.................. | ........S... | ............ | ............ | ............................................ | ............. | ............ |
| iPS:43 4301 | 21-225_58F11 | VK3|L2/J K3 | ........................ | ........D.V. | ............ | .......V.... | .........................A.......G........H.. | .......S...... | ......N..... |
| iPS:43 7228 | 21-225_60C11 | VK3|L2/J K3 | ........................ | .......ND... | ............ | ............ | ............................................ | ............. | ............ |
| | Germline | | K_FR1 DIVMTQSPLSLP VTPGEPASISC | K_CDR1 RSS QSLLHSN GYNYLD | K_FR2 WYLQKPGQ SPQLLIY | K_CDR2 LGSNRAS | K_FR3 GVPDRFSGSGSG TDFTLKISRVEAEDVGV YYC | K_CDR3 MQALQ TPLT | K_FR4 FGQGTK LEIK |
| VK2JA19JK 5 | | | | | | | | | |
| iPS:43 4243 | 21-225_62C1 | VK2|A19/ JK5 | ........................ | ............ | ............ | .......V.... | .....................................F........ | ........L..... | ............ |
| iPS:43 6648 | 21-225_227F11 | VK2|A19/ JK5 | ........V............... | .....W...... | ....V....... | ............ | ............................................ | ........L..... | ............ |
| iPS:43 4061 | 21-225_12D2 | VK2|A19/ JK5 | ........................ | ............ | ....V....... | ............ | .......................................G...... | ............. | ............ |
| iPS:39 4071 | 21-225_10C7 | VK2|A19/ JK5 | ........................ | ....K....... | ....V....... | ............ | ............................................ | ........L..... | ............ |
| | Germline | | K_FR1 DIQMTQSPSSVS ASVGDRVTITC | K_CDR1 RAS QGIS SWLA | K_FR2 WYQQKPGK APKLLIY | K_CDR2 AASSLQS | K_FR3 GVPSRFSGSGSG TDFTLTISSLQPEDFAT YYC | K_CDR3 QQANS FPLT | K_FR4 FGQGTK VEIK |
| VK1L5JK4 | | | | | | | | | |
| iPS:43 4259 | 21-225_62G7 | VK1|L5/J K4 | ........F............... | ....D....... | ............ | ............ | ...........................N.................. | ........T..... | ............ |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 4333 | 21-225_63C9 | VK1|L5/J K4 | . . . . . . . . . . . . . . . . . . . . . . | . . . . . . . . | . . N . . | . . . . . . . | . . . . . . . . . . . . . . . . . . . . . . . | . . I . . . | . . A . . |
| iPS:43 4347 | 21-225_64H10 | VK1|L5/J K4 | . . . . . . . . . . . . . . . . . . . . . . | . . . . L . . . | . . . . . | . . . . . . . | . . . . . . . . . . . . . . . . . . . . . . . | . . I . . . F | . . . . . |
| iPS:43 4359 | 21-225_65G3 | VK1|L5/J K4 | . . . . . . . . . . . . . . . . . . . . . . | . . . . . . . . | . . . . . | . . . . . . . | . . . . . . . G . . . . . . . . . . . . . . . | . . V . . . | . . . . . |
| iPS:43 4369 | 21-225_66B1 | VK1|L5/J K4 | . . . . . . . . . . . . . . . . . . . . . . | . . . . L . . . | . . . . . | . . . . . . . | . . . . . . . . . . . . . . . . . . . . F . . | . . T . . . | . . . . . |
| iPS:43 4373 | 21-225_66A7 | VK1|L5/J K4 | . . . . . . . . . . . . . . . . . . . . . . | . . . . . . . . | . . . . . | . . . . . . . | . . . . . . . . . . . . . . . . . . . . . . . | . . I . . . | . . . . . |
| iPS:43 4397 | 21-225_67H4 | VK1|L5/J K4 | . . . . . . . . . . . . . . . . . . . . . . | . . . . K . . . | . . N . . | . . . . . . . | . . . . . . . . . . . . . . . . . . N . . . . | . . I . . . | . . . . . |
| iPS:43 4427 | 21-225_70D6 | VK1|L5/J K4 | . . . . . . . . . . . . . . . . . . . . . . | . . . . D . . . | . . N . . F | . . . . . . . | . . . . . . . . . . . . . . . . . . . . . . . | . . T . . . | . . . . . |
| iPS:43 4435 | 21-225_70G9 | VK1|L5/J K4 | . . . . . . . . . . . . . . . . . . . . . . | . . . . . . . . | . . . . . | . . . . . . . | . . . . . . . . . . . . . . . . . . . . . . . | . . T . . . | . . . . . |
| iPS:43 4437 | 21-225_70A12 | VK1|L5/J K4 | . . . . . . . . . . . . . . . . . . . . . . | . . . . . . . . | . . L . . | . . . . . . . | . . . . . . . V . . . . . . . . . . . . . . . | . . T . . . | . . . . . |
| iPS:43 4451 | 21-225_71B7 | VK1|L5/J K4 | . . . . . . . . . . . . . . . . . . . . . . | . . . . . . . . | . . N . . E | . . . . G . . | . . . . . . . . . . . . . . . . . . . . . . . | . . T . . . | . . . . . |
| iPS:43 4459 | 21-225_71A7 | VK1|L5/J K4 | . . . . . . . . . . . . . . . . . . . . . . | . . . . . . . . | . . . . . | . . . . . . . | . . . . . . . V . . . . . . . . . . . N . . . | . . V . . . | . L . . . |
| iPS:43 4461 | 21-225_73A3 | VK1|L5/J K4 | . . . . . . . . . . . . . . . . . . . . I . | . . . . N . . . | . . . . . | . . . . . . . | . . . . . . . . . . . . . . . . . . . . E . . | . . V . . . | . . . . . |
| iPS:43 5479 | 21-225_154E9 | VK1|L5/J K4 | . . . . . . . L . . . . . . . . . . . Y . . | . . . . D . . . | . . R . . | . . . . . . . | . . . . . . . . . . . . . . . . . . . . . . . | . . G . . . | . . D . . |
| iPS:43 7232 | 21-225_63E1 | VK1|L5/J K4 | . . . . . . . . . . . . . . . . . . . Y . . | . . . . N . . . | . . V . . | . . . . . . . | . . . . . . . . . . . . . . . . . . . . . . . | . . V . . . | . . . . . |
| iPS:43 7326 | 21-225_75C10 | VK1|L5/J K4 | . . . . . . . . . . . . . . . . . . . . I . | . . . . . . . . | . . . . . | . . . . . . . | . . . L . . . . . . . . . . . . . . . . . . . | . . K . . . | . . . . . |
| VK1|O12|JK2 | | Germline | DIQM QSPSSLS ASVGDRVTITC | RAS QSIS SYLN | WYQQKPGK APKLLIY | AASSLQS | GVPSR FSGSGS GTDFTLTISSLQPEDFAT YYC | QQSYS TPYT | FGQGTK LEIK |
| iPS:43 4309 | 21-225_59B5 | VK1|O12/ JK2 | . . . . . . . . . . . . . . . . . . . I . . | . . . . . . . . | . . . . . | . . G . . . . | . . . . . . . . . . . . . . . . . . . . . . . | . . . . . TPMFS | . . . . . |
| iPS:39 2874 | 21-225_21D2 | VK1|O12/ JK2 | . . . . . . . . . . . . . . . . . . . F . . | . . . . . . . . | . . R . . | . R D . . . . | . . . . . . . . . . . . . . . . . . . . . . . | . T . NI . . . LPERS | . R . . . |
| iPS:39 3940 | 21-225_16B2 | VK1|O12/ JK2 | GV . . . . . . . . . . . . . . . . . . . . . | . . . . G . . . | . . . . . | . . . T . . . | . . . . . . . . . . . . . . . . . . . G . . . | . T . NT . . . PPERS | . . . . . |
| iPS:39 3956 | 21-225_4D7 | VK1|O12/ JK2 | . . . . . . . . . . . . . . . . . . . . . . | . . . . D . . . | . . . . . F | . D . . TT . . | . . . . . . . . . . . . . . . . . . N . . . . | . T . NT . . . PPERS | . . . . . |

Figure 52 (Continued)

[Table content too dense and low-resolution to transcribe reliably]

Figure 52 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:43_4457 | 21-225_72G12 | VK1jA20/JK4 | ....L............ | ...S...N | S......... | ....C..... G... | .........I.........A....E. | .QNYN... | ........ |
| | Germline | VK3jA27jJK4 | EIVLTQSPTTLS LSPGERATISC | RAS QSVSSS SYLA | WYQQKPGQ APRLLIY | GASSRAT | GIPDRFSGSGSG TDFTLTISSLEPEDFAV YYC | QQYGS SPLT | FGGGTK VEIK |
| iPS:43_4479 | 21-225_76H1 | VK3jA27/JK4 | .FM.........Y | .........V | | | .........Y........ | ....C... | ........ |
| iPS:43_4513 | 21-225_76A6 | VK3jA27/JK4 | W.........R. | | | ....T.... | .........Y........ | ....N... | ....T... |
| iPS:43_4515 | 21-225_74A5 | VK3jA27/JK4 | .FM......... | .........V | | ....T.... | .........Y........ | ....C... | ....T... |
| iPS:43_4529 | 21-225_76B9 | VK3jA27/JK4 | .FM......... | .........V | | ....T.... | .........Y........ | ....C... | ........ |
| iPS:43_4583 | 21-225_74B6 | VK3jA27/JK4 | .FM......... | .........V | | ....T.... | .........Y........ | ....N... | ....T... |
| iPS:43_4587 | 21-225_74G3 | VK3jA27/JK4 | .FM......C | .........V | | ....T.... | .........Y........ | ....C... | ....T... |
| iPS:43_4603 | 21-225_77D11 | VK3jA27/JK4 | W....I... | | | ....T.... | .........Y........ | ....C... | ........ |
| iPS:43_4705 | 21-225_80A2 | VK3jA27/JK4 | .FM......Y | .........V | | ....T.... | .........Y........ | ....C... | ....T... |
| iPS:43_4747 | 21-225_80C12 | VK3jA27/JK4 | .FM......Y | .........V | | ....T.... | .........Y........ | ....C... | ........ |
| iPS:43_4793 | 21-225_82A5 | VK3jA27/JK4 | W......... | | | ....T.... | .........Y........ | ....C... | ....T... |
| iPS:43_4797 | 21-225_82G5 | VK3jA27/JK4 | .FM......Y | ...E.....V | | ....T.... | .........Y........ | ....C... | ........ |
| iPS:43_4805 | 21-225_82D9 | VK3jA27/JK4 | .FM......S | ...E.....V | | ....T.... | .........Y........ | ....C... | ....T... |
| iPS:43_4813 | 21-225_82C12 | VK3jA27/JK4 | W......... | | | ....T.S.. | .........Y........ | ....N... | ....T... |
| iPS:43_4825 | 21-225_83C2 | VK3jA27/JK4 | .FM......C | ...E.....V | | ....T.... | .........Y........ | ....C... | ........ |
| iPS:43_4833 | 21-225_83C5 | VK3jA27/JK4 | W......C | | | ....T.... | .........Y........ | ....C... | ....T... |
| iPS:43_4883 | 21-225_85B5 | VK3jA27/JK4 | .FM......... | S........V | | ....T.... | .........Y........ | ....C... | ....T... |
| iPS:43_4911 | 21-225_85D11 | VK3jA27/JK4 | .FM.T......... | S........V | | ....T.... | .........Y........ | ....N... | ....T... |
| iPS:43_4957 | 21-225_87A10 | VK3jA27/JK4 | .F.........Y | .........V | | ...T.S.. | .........Y........ | ....N... | ....T... |

| | Germline | K_FR1 | K_CDR1 | K_FR2 | K_CDR2 | K_FR3 | K_CDR3 | K_FR4 |
|---|---|---|---|---|---|---|---|---|
| iPS:43 6246 | 21-225_201G6 | VK2|A19/JK4 | ........... | ....N ..R.H.. | ........ | ........ | ........ | -- | ........ |
| iPS:43 6254 | 21-225_202C12 | VK2|A19/JK4 | ...L....... | ....N ..K.H.. | ........ | ........ | ........ | ...QTP. | ........ |
| iPS:43 6304 | 21-225_201F3 | VK2|A19/JK4 | ........... | ....N ..R.H.. | ........ | ........ | ........ | -- | ........ |
| iPS:43 6334 | 21-225_208G3 | VK2|A19/JK4 | ...L....... | ....N ..K.H.. | ........ | ........ | ........ | ...QTP. | ........ |
| iPS:43 7248 | 21-225_97H3 | VK2|A19/JK4 | ...I....... | ....H..... | ....R... | ........ | ....E... | ...P.. | ........ |
| iPS:43 7320 | 21-225_75A1 | VK2|A19/JK4 | ........... | ....H..... | ....R... | ........ | ....E... | ...P..F. | ........ |
| iPS:43 7371 | 21-225_74D8 | VK2|A19/JK4 | ........S.. | ....V..S.. | ....V... | ........ | ........S | ...H.. | ........ |
| iPS:39 2718 | 21-225_17B8 | VK2|A19/JK4 | ........... | ....N.S.. | ........ | ....H.. | ....D...L | ...V..F. | ........ |
| | | K_FR1 | K_CDR1 | K_FR2 | K_CDR2 | K_FR3 | K_CDR3 | K_FR4 |
| | VK3|L2JK1 | EIVMTQSPATL... VSCRATISC | RAS QSVS SNLA | WYQQKPGQ APRLLIY | GASTRAT | GIPARFSGSG SGTDFTLTISSLQSEDFAV YYC | QQYNN WPLT | FGQGTK VEIK |
| iPS:43 4871 | 21-225_85H1 | VK3|L2/JK1 | ........... | ...D.I. TY. | ........ | ........ | ....V... | ..E..D...CS | ........ |
| iPS:43 5421 | 21-225_151F1 | VK3|L2/JK1 | .M......V.. | ...IN. I.I. | ........ | ........ | ........ | ...D...WP. | ........ |
| iPS:43 5497 | 21-225_155H9 | VK3|L2/JK1 | ........... | ........ | ........ | ....S.. | ........ | ...DD..WP. | ........ |
| iPS:43 5605 | 21-225_161A4 | VK3|L2/JK1 | ........S.. | ....S.. | ...R.. | ....I... | ....D...N | ........ | ...T |
| iPS:45 1118 | 21-225_191C8 | VK3|L2/JK1 | ........... | ........ | ...L.. | ........ | ........F | ...NW. | ........ |
| iPS:39 2734 | 21-225_17D8 | VK3|L2/JK1 | ........S.. | ...R.. | ....E.. | ........ | ........ | ...SFT...LR | ........ |
| iPS:39 2768 | 21-225_20B8 | VK3|L2/JK1 | ........S.. | ........ | ....F...N | ........ | ........ | ........L | ........ |
| iPS:39 3044 | 21-225_25B8 | VK3|L2/JK1 | ........V.. | ........ | ....F...N | ....S.. | ........ | ...C.L. | ........ |
| iPS:39 3050 | 21-225_28C5 | VK3|L2/JK1 | ........... | ....R.. | ....H.. | ....S.. | ........L | ...WP..P | ........ |

| | VK2|A19/JK | | | | K_CDR1 | K_FR2 | K_CDR2 | K_FR3 | K_CDR3 | K_FR4 |
|---|---|---|---|---|---|---|---|---|---|---|
| iPS:43 5667 | 21-225_169E3 | VK2|A19/ JK1 | | | ...K......N | .......... | .......... | ...........A. | ..V....... | ........ |
| iPS:43 5673 | 21-225_169E6 | VK2|A19/ JK1 | | | ...K......N | .......... | .......... | ...........A. | ..V....... | ........ |
| iPS:43 5759 | 21-225_176E6 | VK2|A19/ JK1 | | | ...K......N | .......... | .......... | ...........A. | ..V....... | ........ |
| | Germline | | | | K_CDR1 | K_FR2 | K_CDR2 | K_FR3 | K_CDR3 | K_FR4 |
| iPS:43 5817 | 21-225_190B11 | VK6|A26/ JK1 | .A....... | | ....N..... | .......... | ....S..... | ..........T.. | ..Q....... | ........ |
| iPS:43 5823 | 21-225_190F11 | VK6|A26/ JK1 | ....F..S. | | ....N..... | ..V....E.. | .......... | .............. | .......... | .F.R.... |
| iPS:43 5867 | 21-225_191E5 | VK6|A26/ JK1 | ....F..S. | | .......... | .......... | .......... | .............. | .......... | .F.R.... |
| iPS:43 5917 | 21-225_190D5 | VK6|A26/ JK1 | .A....... | | ....N..... | .......... | ....S..... | ..........T.. | ..Q....... | ........ |
| iPS:43 5929 | 21-225_190D9 | VK6|A26/ JK1 | ....F..S. | | .......... | .......... | .......... | .............. | .......... | .F.R.... |
| iPS:43 5935 | 21-225_190H8 | VK6|A26/ JK1 | .A....... | | ....N..... | .......... | ....S..... | ..........T.. | ..Q....... | ........ |
| iPS:43 6056 | 21-225_194C3 | VK6|A26/ JK1 | .A....... | | ....NT.... | .......... | .......... | .............I | ..Q....... | ........ |
| iPS:43 6216 | 21-225_200B7 | VK6|A26/ JK1 | .A....... | | ....N..... | .......... | ....S..... | ..........T.. | ...G...... | ........ |
| iPS:43 6220 | 21-225_200F8 | VK6|A26/ JK1 | .......... | | .......... | .......... | .......... | .............. | ..Q....... | ..Q..... |
| iPS:43 6448 | 21-225_217A3 | VK6|A26/ JK1 | ......K.. | | .......... | ......V... | .......... | ...........G. | ...R...... | ........ |
| | Germline | | | | K_CDR1 | K_FR2 | K_CDR2 | K_FR3 | K_CDR3 | K_FR4 |
| iPS:43 5829 | 21-225_190B12 | VK6|A26/ JK4 | .......... | | .......... | .......... | .......... | ...........D. | ..TR...... | ........ |
| iPS:43 5863 | 21-225_191H4 | VK6|A26/ JK4 | .......... | | ....N..... | .......... | ....L..... | ...........A.D | ..TGR...... | ........ |
| iPS:43 5943 | 21-225_191C9 | VK6|A26/ JK4 | .......... | | .......... | .......... | .......... | ...........D. | ..TR...... | ........ |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| iPS:43 5983 | 21-225_192E5 | VK6|A26/ JK4 | .......... | :::::::R. | .......... | .......... | .......... | .....R. | ..... |
| iPS:43 6043 | 21-225_193G9 | VK6|A26/ JK4 | .......... | .......R. | ......R... ..L... | .......... | .......... | .....R. | ..... |
| iPS:43 6084 | 21-225_195F2 | VK6|A26/ JK4 | .......... | .......... | .......... F. | .......... | .......... | ..RT | ..... |
| iPS:43 6094 | 21-225_195B10 | VK6|A26/ JK4 | .......... | .......... A. | .......... | .......... | A...S | .GR. | ..... |
| iPS:43 6240 | 21-225_201E8 | VK6|A26/ JK4 | .......... | ....N..... .....R... | .......... | .....N.... | .......... | .....R. | ...R |
| iPS:43 6314 | 21-225_206G4 | VK6|A26/ JK4 | .......... | .......R. | .......... | ....V..... | .......... | .....R. | ..... |
| VK6|A26|JK4 | | Germline | K_FR1 | K_CDR1 | K_FR2 | K_CDR2 | K_FR3 | K_CDR3 | K_FR4 |
| iPS:43 5833 | 21-225_190D12 | VK1|A20/ JK3 | .......... | .......... | .......... | ....V..... | .......... | .......... | ..... |
| iPS:43 6019 | 21-225_193C4 | VK1|A20/ JK3 | .......... | .P........ ......I... | .......N.. | .......... | .......... | .......... | ..... |
| iPS:39 4010 | 21-225_12G5 | VK1|A20/ JK3 | .......P. | .......D. | .......... | ..YI...... | .....A.... | .......D. | ..... |
| VK1|A20|JK3 | | Germline | K_FR1 | K_CDR1 | K_FR2 | K_CDR2 | K_FR3 | K_CDR3 | K_FR4 |
| iPS:43 6025 | 21-225_193B5 | VK6|A26/ JK3 | .......... | .......... | .......... | .......... | .......... | .....R. | ..... |
| iPS:43 6096 | 21-225_195E10 | VK6|A26/ JK3 | .......... | .......... | .......... | .......... | .......... | .....R. | ..... |
| iPS:43 6408 | 21-225_214H8 | VK6|A26/ JK3 | .......... | .......V. | ...Q...... | .......... | .S........ | .....R. | ...S |
| iPS:43 6424 | 21-225_215H6 | VK6|A26/ JK3 | .......... | .......V. | ...Q...... | .....L.... | .......I.. | .....R. | ...S |
| VK6|A26|JK3 | | Germline | K_FR1 | K_CDR1 | K_FR2 | K_CDR2 | K_FR3 | K_CDR3 | K_FR4 |
| iPS:43 6082 | 21-225_195D9 | VK1|L5/J K2 | .......Y.Y ......S... | .......... | ..A.F..... | ......LG.. | .......... | .....R. | ..... |
| iPS:43 6118 | 21-225_196A10 | VK1|L5/J K2 | .......... | .......R. | .......... | ......LG.. | ..S....... | .RD... | ..... |
| VK1|L5|K2 | | Germline | K_FR1 | K_CDR1 | K_FR2 | K_CDR2 | K_FR3 | K_CDR3 | K_FR4 |

Figure 52 (Continued)

| | | K_FR1 | K_CDR1 | K_FR2 | K_CDR2 | K_FR3 | K_CDR3 | K_FR4 |
|---|---|---|---|---|---|---|---|---|
| VK2lA19/JK2 | | DIVMTQSPLSLP VTPGEPASISC | RSS QSLLHSN GYNYLD | WYLQKPGQSP QRLIY | LGSNRAS | GVPDRFSGSGSG TDFTLKISRVEAEDVGV YYC | MQALQ TPYT | FGQGTK LEIK |
| iPS:43 6362 | 21-225_210C12 | VK2lA19/JK2 | .................... | ......H.F.......Y | ................ | ............V........ | .................... | .................... | .................... |
| iPS:43 6374 | 21-225_211C10 | VK2lA19/JK2 | .................... | .................... | .........L....... | .................... | .................... | ......L.....TPMCS | .................... |
| | Germline | K_FR1 | K_CDR1 | K_FR2 | K_CDR2 | K_FR3 | K_CDR3 | K_FR4 |
| VK2lA17/JK1 | | DVVMTQSPLSLP VTLGQPASISC | RSS QSLVYSD GNTYLN | WFQQRPGQ SPRRLIY | KVSNRDS | GVPDRFSGSGSG TDFTLKISRVEAEDVGV YYC | MQGTH MEWT | FGQGTP VEIK |
| iPS:43 7226 | 21-225_57C2 | VK2lA17/JK1 | .................... | .................... | .................... | ............E........ | .......N............ | ..........V........ | .................... |
| | Germline | K_FR1 | K_CDR1 | K_FR2 | K_CDR2 | K_FR3 | K_CDR3 | K_FR4 |
| VK1lA20/JK5 | | DIQMTQSPSSLS ASVGDRVTITC | RAS QGIS NYLA | WYQQKPGKA PKLLIY | AASTLQS | GVPSRFSGSGSG TDFTLTISSLQPEDFAT YYC | QQYNS APFT | FGQGTR LEIK |
| iPS:39 2726 | 21-225_20B5 | VK1lA20/JK5 | .................... | .........N....... | .........I....... | .................... | .................... | ..........AP..... | .................... |
| iPS:39 2792 | 21-225_20G12 | VK1lA20/JK5 | .................... | .................... | .........V....... | .............T........ | .................... | ..........AP..... | .................... |
| iPS:39 8478 | 21-225_17C10 | VK1lA20/JK5 | ............Q..... | .................... | .................... | .................... | ........D............ | ........AP.L. | .................... |
| | Germline | K_FR1 | K_CDR1 | K_FR2 | K_CDR2 | K_FR3 | K_CDR3 | K_FR4 |
| VK1lL1/JK2 | | DIQMTQSPSSLS ASVGDRVTITC | RAS QGIS NDLG | WYQQKPGKA PKLLIY | AASSLQS | GVPSRFSGSGSG TDFTLTISSLQPEDFAT YYC | QQYNS YPYT | FGQGTK LEIK |
| iPS:43 2776 | 21-225_21A12 | VK1lL1/JK2 | .................... | ...K................ | .................... | .................... | ......K............ | ............FR... | .................... |
| | Germline | K_FR1 | K_CDR1 | K_FR2 | K_CDR2 | K_FR3 | K_CDR3 | K_FR4 |
| VK1lA30/JK3 | | DIQMTQSPSSLS ASVGDRVTITC | RAS QGIS NDLG | WYQQKPGKA PKLLIY | AASSLQS | GVPSRFSGSGSG TDFTLTISSLQPEDFAT YYC | LQHNS YPFT | FGQGTK VEIK |
| iPS:43 7240 | 21-225_84H12 | VK1lA30/JK3 | ............YQ. | .................... | .........F....... | .................... | .................... | ....D............ | .................... |
| iPS:43 4577 | 21-225_75C11 | VK1lA30/JK3 | .................... | .................... | .........F....... | .................... | .................... | ....D............ | .................... |
| iPS:43 4553 | 21-225_76H12 | VK1lA30/JK3 | .................... | .................... | .................... | .................... | .................... | ....D............ | .................... |
| iPS:43 4927 | 21-225_86E5 | VK1lA30/JK3 | .................... | .................... | .................... | .............R........ | .............H........ | ....D............ | ...E................ |
| | Germline | K_FR1 | K_CDR1 | K_FR2 | K_CDR2 | K_FR3 | K_CDR3 | K_FR4 |

Figure 52 (Continued)

| VK1|L5|JK1 | | DIQMTQSPSSLS ASVGDRVTITC | RAS QGIS SWLA | WYQQKPG KAPKLLIY | AAS SLQS | GVPSRFSGSGSG TDFTLTISSLQPEDFAT YYC | QQANS FPWT | FGQGTK VEIK |
|---|---|---|---|---|---|---|---|---|
| iPS:43 5477 | 21-225_154E8 | VK1|L5|J K1 | ..I......... | F......... | ............ | .I........ | .......C.................... | ........... | ..FN |
| iPS:43 5385 | 21-225_149G7 | VK1|L5|J K1 | ............ | F......... | ............ | .......... | ............................ | ........... | ..N |
| LAMBDA_VARIABL E | | | | | | | | | |
| | | Germline | L_FR1 | L_CDR1 | L_FR2 | L_CDR2 | L_FR3 | L_CDR3 | L_FR4 |
| | | | SYELTQP PSVSVSPGQTAS ITC | SGD SLGD KYAC | WYQQKPG QSPVLVIY | QDSKRPS | GIPERFSGSNSG NTATLTISGTQAMDEAD YYC | QAWDS STAVV | FGGGTK LTVL |
| iPS:45 3445 | 21-225_148E10 | VL3|3r/JL 2 | ............ | ...V... | AA...R.H .I... | .......... | ............................ | ......R...... | ......... |
| iPS:47 2742 | 21-225_30D9_L_C2 | VL3|3r/JL 2 | ............ | ..VY... | .....F... | .......R.. | ..........L................. | ......N...-STA. | ......... |
| iPS:47 2743 | 21-225_68G6 | VL3|3r/JL 2 | ..V......... | ..TY... | ....A.... | .......... | .D........A.F............... | ......N...-STA. | ......... |
| iPS:43 6652 | 21-225_146B11 | VL3|3r/JL 2 | ............ | ..S.... | ......... | .......R.. | ..........I................. | ..........-ST.. | ......... |
| iPS:43 6654 | 21-225_146C11 | VL3|3r/JL 2 | ............ | ..S.... | ......... | .......... | ..........I................. | ..........-ST.. | ......... |
| iPS:43 6658 | 21-225_146A2 | VL3|3r/JL 2 | ............ | ..S.... | ......... | .......... | ..........I................. | ..........-ST.. | ......... |
| iPS:43 6664 | 21-225_147E7 | VL3|3r/JL 2 | ............ | ..V.... | ....E.... | .......R.. | ..........L.V............... | ......G...-ST.. | ......... |
| iPS:43 6666 | 21-225_147B8 | VL3|3r/JL 2 | ............ | ..VS... | ......... | .......R.. | ............................ | ......L....N... | ......... |
| iPS:43 6668 | 21-225_147B9 | VL3|3r/JL 2 | ............ | ..V..N. | ......... | .......... | ............................ | ..........-ST.. | ......... |
| iPS:43 6670 | 21-225_147D9 | VL3|3r/JL 2 | ............ | ..V.... | .....R... | .......... | ............................ | ......R...-N.Y. | ......... |
| iPS:43 6672 | 21-225_147F9 | VL3|3r/JL 2 | ............ | ..E..N. | ......... | .......... | ..........I................. | ......H...-ST.. | ......... |
| iPS:43 6674 | 21-225_147G9 | VL3|3r/JL 2 | ............ | ....... | ......... | .......... | ............................ | ..........F... | ......... |
| iPS:43 6676 | 21-225_147E11 | VL3|3r/JL 2 | ............ | ..S.... | ......... | .......... | ..........I..A.............. | ......R...-ST.. | ......... |
| iPS:43 6678 | 21-225_147B12 | VL3|3r/JL 2 | ............ | ..S.... | ......... | .......... | ..........I................. | ......H...-ST.. | ......... |
| iPS:43 6686 | 21-225_148G6 | VL3|3r/JL 2 | ............S | ..G.... | ......... | .......... | ..........I................. | ..........-ST.. | ......... |

Figure 52 (Continued)

| | | | | | | | | | | |
|---|---|---|---|---|---|---|---|---|---|---|
| iPS:43 6688 | 21-225_148C8 | VL3|3r/J|L 2 | | | | | T | | L | |
| iPS:43 6690 | 21-225_148A9 | VL3|3r/J|L 2 | | VS | I | R | | | H | F |
| iPS:43 6694 | 21-225_148G11 | VL3|3r/J|L 2 | | N V | | | | I | | -ST. |
| iPS:43 6698 | 21-225_149B5 | VL3|3r/J|L 2 | | F.S Y V | F | | | | | -ST. |
| iPS:43 6700 | 21-225_149C7 | VL3|3r/J|L 2 | | N | | NNQ | S | K I | | |
| iPS:43 6704 | 21-225_149C10 | VL3|3r/J|L 2 | | S | | N | | G.I | | -ST. |
| iPS:43 6706 | 21-225_149A11 | VL3|3r/J|L 2 | | N VS | | | | | L | F |
| iPS:43 6708 | 21-225_150D3 | VL3|3r/J|L 2 | | E.N S | | N | | I | S | -ST. |
| iPS:43 6710 | 21-225_150F6 | VL3|3r/J|L 2 | | S | C | | | I | C | -ST. |
| iPS:43 6714 | 21-225_150H11 | VL3|3r/J|L 2 | | S | | | | I | F | -ST. |
| iPS:43 6716 | 21-225_151F3 | VL3|3r/J|L 2 | | V | | R | | I | | H -ST. |
| iPS:43 6718 | 21-225_151H5 | VL3|3r/J|L 2 | A | S | | | | I | | -ST. |
| iPS:43 6722 | 21-225_151H7 | VL3|3r/J|L 2 | A D | S | | | | I | | -ST. |
| iPS:43 6724 | 21-225_151B9 | VL3|3r/J|L 2 | | N S | | | | I L | | N -ST. |
| iPS:43 6728 | 21-225_152G6 | VL3|3r/J|L 2 | | S | | | | I | | -ST. |
| iPS:43 6730 | 21-225_152D7 | VL3|3r/J|L 2 | | S N V | | | | T | G | H Y I |
| iPS:43 6736 | 21-225_153E8 | VL3|3r/J|L 2 | R | S V | R | R | | I | | -ST. V |
| iPS:43 6738 | 21-225_153D9 | VL3|3r/J|L 2 | | V | | R | | I | | H -ST. |
| iPS:43 6740 | 21-225_154C3 | VL3|3r/J|L 2 | | S | | | | I | | -ST. |
| iPS:43 6742 | 21-225_154C4 | VL3|3r/J|L 2 | | N | | | | I | | N -ST. |
| iPS:43 6744 | 21-225_154F4 | VL3|3r/J|L 2 | | V | E | K | | | G | -STL. |

Figure 52 (Continued)

| | | | | | | | |
|---|---|---|---|---|---|---|---|
| iPS:43 6746 | 21-225_154E10 | VL3｜3r/J｜L 2 | . | . | . | . | N | -ST |
| iPS:43 6748 | 21-225_154D11 | VL3｜3r/J｜L 2 | . | . | . | I | .H | -SI |
| iPS:43 6756 | 21-225_146A10 | VL3｜3r/J｜L 2 | . | V. | .F | K. | . | -ST.V |
| iPS:43 6758 | 21-225_155C10 | V | VS | . | . | . | -ST |
| iPS:43 6760 | 21-225_155E10 | . | VS | . | . | . | -ST |
| iPS:43 6764 | 21-225_158E9 | .D | V. | . | T. | L. | .F |
| iPS:43 6766 | 21-225_158D10 | T | V. | R. | L. | .GN | SF.L |
| iPS:43 6768 | 21-225_159H8 | . | V. | . | L. | .GN | SF |
| iPS:43 6770 | 21-225_160B12 | .D....S | V. | R. | L. | .GN | SF |
| iPS:43 6772 | 21-225_161H3 | . | R. V. | . | . | .VN | SF |
| iPS:43 6774 | 21-225_161E10 | .FD | V. | .N | L. | . | .N |
| iPS:43 6776 | 21-225_161F12 | . | . | T. | I. | T.N | SFAL |
| iPS:43 6780 | 21-225_165H3 | ....S | . | . | . | . | -TL |
| iPS:43 6782 | 21-225_166G11 | . | VH | . | . | . | -TL |
| iPS:43 6784 | 21-225_169C1 | . | V. | L. K. | . | .N | -STA |
| iPS:43 6786 | 21-225_169A6 | . | .R V. | . | . | T. | -NT.I |
| iPS:43 6788 | 21-225_169B7 | A.D | .G S | . | Y. | T. | -NT.L |
| iPS:43 6790 | 21-225_169G11 | . | . | R. | . | K. | -NT |
| iPS:43 6794 | 21-225_170F1 | . | . | . | . A | . | -STA |
| iPS:43 6796 | 21-225_170A5 | .D | .S | I. | Y. | .N | -NTA |
| iPS:43 6798 | 21-225_171F5 | A.D | .G S | .R | . | K. | -STM -NT.R |

Figure 52 (Continued)

| | | | | | | | | | | |
|---|---|---|---|---|---|---|---|---|---|---|
| iPS:43 6802 | 21-225_171E12 | VL3l3r/JL2 | . . . . | . . . . | . . . . | . . . . | . . . . | . . . . | I . . . | . . . . |
| iPS:43 6808 | 21-225_173F8 | VL3l3r/JL2 | . . . . | . . N . | . . . . | . R . . | . . . . | . . . . | . . Y . | . . . . |
| iPS:43 6812 | 21-225_175C6 | VL3l3r/JL2 | . . D . | . V . . | . R . S | . R . . | . . . . | . . . . | -FT . | . R . . |
| iPS:43 6818 | 21-225_179C7 | VL3l3r/JL2 | . . . . | . V . . | . I . . | . Y . . | . . . . | . . . . | -STM . | . . . . |
| iPS:43 6822 | 21-225_180D4 | VL3l3r/JL2 | . . T . | . R . . | . R . . | . E . . | . R . . | . . . . | . N . . | . . . . |
| iPS:43 6824 | 21-225_180C5 | VL3l3r/JL2 | . . . . | . E . . | . . . . | . R . . | . . . . | . G . . | . -RK . | . . . . |
| iPS:43 6826 | 21-225_180G5 | VL3l3r/JL2 | . Y . . | . VS . | . . . . | . . . . | . . . . | . . P . | -STA . | . . . . |
| iPS:43 6828 | 21-225_181H1 | VL3l3r/JL2 | . . T . | . . . . | . . . . | . E . . | . S . . | . . . . | . I . . | . . . . |
| iPS:43 6836 | 21-225_52H1 | VL3l3r/JL2 | . . F . S | . . . . | . . . . | . R . . | . . . . | . . . . | . -TA . | . . . . |
| iPS:43 6848 | 21-225_57F1 | VL3l3r/JL2 | . A . . | . E . . | . . . . | . R . . | . . . . | . . . . | -RK . | . . . . |
| iPS:43 6850 | 21-225_57D9 | VL3l3r/JL2 | . . . . | . E . E | . S . . | . R . . | . . . . | . . . . | . N . . | . . . . |
| iPS:43 6852 | 21-225_57H11 | VL3l3r/JL2 | . A . . | . F . . | . . . . | . R . . | . . . . | . . . . | -ST . | . . . . |
| iPS:43 6854 | 21-225_58C1 | VL3l3r/JL2 | . N . . | . E . . | . . . . | . R . . | . . . . | . . . . | -ST . | . . . . |
| iPS:43 6858 | 21-225_58E7 | VL3l3r/JL2 | . . . . | . N . . | . . . . | . R . . | . . . . | . . . . | -ST . | . . . . |
| iPS:43 6860 | 21-225_58F7 | VL3l3r/JL2 | . S . . | . . . . | . K . . | . N . . | . . . . | . . . . | -SSTA . | -SSTA . |
| iPS:43 6862 | 21-225_58F8 | VL3l3r/JL2 | . . . . | . T . . | . . . . | . R . . | . . . . | . F . . | NN -YT . | . . . . |
| iPS:43 6864 | 21-225_58G11 | VL3l3r/JL2 | . . . . | . S . . | . . . . | . . . . | . . . . | . . . . | . -ST . | . . . . |
| iPS:43 6866 | 21-225_59F2 | VL3l3r/JL2 | . . . . | . S . . | . R . . | . N . . | . . . . | . . . . | NN -NI.M | . . . . |
| iPS:43 6868 | 21-225_59B11 | VL3l3r/JL2 | . A . . | . E . . | . . . . | . N . . | . . . . | . L . . | . N . -NT . | . . . . |
| iPS:43 6870 | 21-225_60B1 | VL3l3r/JL2 | . . . . | . . . . | . . . . | . R . . | . . . . | . . . . | . . Y . | . A . . |
| iPS:43 6872 | 21-225_60D2 | VL3l3r/JL2 | . . . . | . N . S | . R . . | . N . . | . . . . | . f . . | . N . -NT . | . . . . |

Figure 52 (Continued)

| | | | | | N. | | | I | | | | | — |
|---|---|---|---|---|---|---|---|---|---|---|---|---|---|
| iPS:43 6874 | 21-225_60A12 | VL3j3r/jL2 | . | . | N. | . | . | . | . | . | . | . | ...-SSTA | . |
| iPS:43 6876 | 21-225_61F5 | VL3j3r/jL2 | . | . | . | . | . | .R. | . | . | . | . | ..-ST. | . |
| iPS:43 6878 | 21-225_62E3 | VL3j3r/jL2 | ..D | . | E. | . | . | . | . | . | . | . | ..-ST. | . |
| iPS:43 6880 | 21-225_62E8 | VL3j3r/jL2 | ..D | . | N. | V. | . | .R. | . | . | . | . | ..-STA | . |
| iPS:43 6882 | 21-225_62D10 | VL3j3r/jL2 | ..D | . | R..N..S | V. | . | .R. | . | . | . | . | ..-STA | . |
| iPS:43 6884 | 21-225_62A12 | VL3j3r/jL2 | ..D | . | N. | V. | . | .R. | . | . | . | . | ..-STA | . |
| iPS:43 6886 | 21-225_62B12 | VL3j3r/jL2 | ..D | . | N..T | V. | . | .R. | . | . | . | . | ..-STA | . |
| iPS:43 6892 | 21-225_65E9 | VL3j3r/jL2 | . | . | N..DY | . | . | .R. | . | . | N. | . | ..-ST. | . |
| iPS:43 6894 | 21-225_66G9 | VL3j3r/jL2 | ..D | F | N. | .V. | . | .R. | . | . | I. | . | ..-NTA | .R |
| iPS:43 6896 | 21-225_67F10 | VL3j3r/jL2 | . | . | Y..W | . | . | E..F | . | . | N. | . | ..-ST. | . |
| iPS:43 6898 | 21-225_68D8 | VL3j3r/jL2 | . | . | N. | . | . | .R. | . | . | N. | . | ..-ST. | . |
| iPS:43 6900 | 21-225_69B9 | VL3j3r/jL2 | ..D | . | N..DY | . | . | .R. | . | . | N. | . | ..-ST. | . |
| iPS:43 6902 | 21-225_69B11 | VL3j3r/jL2 | ..A | . | W | . | . | E..R. | . | . | VN. | . | ..-ST. | . |
| iPS:43 6904 | 21-225_71D4 | VL3j3r/jL2 | . | . | Y | V. | . | .R. | . | . | . | . | ..-ST. | . |
| iPS:43 6906 | 21-225_72B4 | VL3j3r/jL2 | . | . | W | R. | . | E..R. | . | . | . | . | ..-ST. | . |
| iPS:43 6908 | 21-225_72D5 | VL3j3r/jL2 | ..D | . | N..DY | V. | . | .R. | . | . | N. | . | ..-STA | . |
| iPS:43 6912 | 21-225_73C4 | VL3j3r/jL2 | ..D | . | N. | V. | . | .M. | . | . | . | . | ..-STA | . |
| iPS:43 6914 | 21-225_76B4 | VL3j3r/jL2 | P..N.T | . | R..T..F.. | . | . | . | . | . | . | . | ...-SST. | . |
| iPS:43 6916 | 21-225_74A9 | VL3j3r/jL2 | . | . | V | . | . | NR. | . | . | . | . | ..-SP.I | . |
| iPS:43 6918 | 21-225_77A2 | VL3j3r/jL2 | . | . | R. | . | . | .R. | . | . | . | . | ..-STA | . |

Figure 52 (Continued)

| | | | | | | | | | |
|---|---|---|---|---|---|---|---|---|---|
| iPS:43 6922 | 21-225_78E9 | VL3j3r/jL 2 | . . . . . . . . . . | . . . . . . . . . . | . . . . N . . . . . . . VS | . . . . NR . | . . . . . . . . . | . . . . S . . . . | . . . . . . . . . . | . . . . . -SP.i | . . . . . . . . . . |
| iPS:43 6924 | 21-225_74B3 | VL3j3r/jL 2 | . . . . . . . . . . | . . . . . E . . . . | . . . . . . . . . . | . . . . . . . . . | . . . . . . . . . | . . . . . . . . . | . . . . . . . . . . | . . . . . . . T . | . . . . . . . . . . |
| iPS:43 6928 | 21-225_79E7 | VL3j3r/jL 2 | . . . . . . . . . . | . . . . . . . . . . | . . . . N . . . . . . . VS | . . . . NR . | . . . . . . . . . | . . . . S . . . . | . . . . . . . . . . | . . . . . -SP.i | . . . . . . . . . . |
| iPS:43 6932 | 21-225_92A4 | VL3j3r/jL 2 | . . . . . . . . N . | . . . . . . . . . . | . . . . N . . . . . . . V | . . . . NR . | . . . . . . . . . | . . . . . . . . . | . . . . . . . . . . | . . . . . -SP.i | . . . . . . . . . . |
| iPS:43 6934 | 21-225_96B5 | VL3j3r/jL 2 | P . . . N . T . . . | . . . . . . . . . . | . . . . . . R . T . F . | . . . . . . . . . | . . . . . . . . . | . . . . . . . . . | . . . -SST. | . . . . . . . . . . | . . . . . . . . . . |
| iPS:43 6936 | 21-225_97E6 | VL3j3r/jL 2 | . . . . . . . . . . | . . . . . . . . . . | . . . . N . . . . . . . VS | . . . . NR . | . . . . . . . . . | . . . . S . . . . | . . . . . . . . . . | . . . . . .P.I | . . . . . . . . . . |
| iPS:43 6938 | 21-225_146A3 | VL3j3r/jL 2 | . . . . . . . . . . | . . . AM . . . . M . | . . . . N . . . . N . . R . | . . . . . . . . . | . . . . . . . . . | . . . . i . . . . | . . . . . . . . . . | . . . . . -ST . | . . . . . . . . . . |
| iPS:43 6940 | 21-225_146B8 | VL3j3r/jL 2 | . . . . . . . . . . | . . . . . V . . . . | . . . . . . . . V . | . . . . . R . | . . . . . . . . . | . . . . . . . . . | . . . . H . . . . | . . . . . -ST . | . . . . . . . . . . |
| iPS:43 6942 | 21-225_146H8 | VL3j3r/jL 2 | . . . . . . . . . . | . . . . . . . . . . | . . . . . . . . . . | . . . . . K . | . . . . V . . . | . . . . . . . . . | . . . . I . . . . | . . . . . -RT . | . . . . . . . . . . |
| iPS:43 6944 | 21-225_182D12 | VL3j3r/jL 2 | . . . . . . . . . . | . . . . . . . . . . | . . . . . . E . . | . . . . . R . | . . . . . S . . | . . . . . . . . . | . . . . . . . . . . | . . . . . -RTA . | . . . . . . . . . . |
| iPS:43 6946 | 21-225_183F4 | VL3j3r/jL 2 | . . . . . . . . . . | . . . . . . . . . . | . . . . . . . . . . | . . . . . K . | . . . . . . . . . | . . . . . D . . . | . . . . . N . . . | . . . . . -RK . | . . . . . . . . . . |
| iPS:43 6952 | 21-225_185D2 | VL3j3r/jL 2 | . . . . . . . . . . | . . . . . . . T . . | . . . . . . . . . . | . . . . E . R . | . . . . . . . . . | . . . . . . . . . | . . . . . . . . . . | . . . . . -RK . | . . . . . . . . . . |
| iPS:43 6954 | 21-225_185G7 | VL3j3r/jL 2 | . . . . . . . . . . | . . . . . . . . . . | . . . . . . . . . . | . . . . . R . | . . . . . . . . . | . . . . . . . . . | . . . -SST. | . . . . . . . . . . | . . . . . . . . . . |
| iPS:43 6956 | 21-225_186H6 | VL3j3r/jL 2 | . . . . . . . . . . | . . . . . . . . . . | . . . . . H . . . FV . | . . . . . R . | . . . . . . . . . | . . . . . . . . . | K . . . . . . . . . | . . . . . -STA . | . . . . . . . . . . |
| iPS:43 6962 | 21-225_190H1 | VL3j3r/jL 2 | . . . . . . . . . . | . . . . . . . . . . | . . . . . . M . E . | . . . . . R . | . . . . . . . . . | . . . . S . . . . | . . . . . . . . . . | . . . . . -ST . | . . . . . . . . . . |
| iPS:43 6978 | 21-225_190G9 | VL3j3r/jL 2 | . . . . . . . . . . | . . . . . . . . . . | . . . . . . . . RF.Y | . . . . . . . . . | . . . . . . . . . | . . . . . . . . . | . . . . . . . . . . | . . . . . -ST . | . . . . . R |
| iPS:43 7018 | 21-225_193H5 | VL3j3r/jL 2 | . . . . . . . . . . | . . . . . S . . . . | . . . . . . . . RF.Y | . . . . . N . | . . . . . . . . . | . . . . . . . . . | . . . . . . . . . . | . . . . . -STA . | . . . . . . . . . . |
| iPS:43 7030 | 21-225_195E3 | VL3j3r/jL 2 | . . . . . . . . . . | . . . . . . . . . . | . . . . . . . . RF . | . . . . E . . . . | . . . . . . . . . | . . . . . . . . . | . . . . . . . . . . | . . . . . -VT . | . . . . . . . . . . |
| iPS:43 7034 | 21-225_195E9 | VL3j3r/jL 2 | . . . . . . . . . . | . . . . . . . . . . | . . . . . . . RSV . | . . . . . R . | . . . . . G . . | . . . . . G . . . | . . . . . R . . . | . . . . . -GI . | . . . . . . . . . . |
| iPS:43 7070 | 21-225_201G11 | VL3j3r/jL 2 | . . . . . . . . . . | . . . . . . . . . . | . . . . . . . . RF . Y | . . . . . . . . . | . . . . . . . . . | . . . . . . . . . | . . . . . . . . . . | . . . . . -ST . | . . . . . I . |

Figure 52 (Continued)

| ID | Name | Type | | | | | | | | |
|---|---|---|---|---|---|---|---|---|---|---|
| iPS:43 7076 | 21-225_203G6 | VL3\|3r\|JL2 | ..... | ..... | ..... | ..... | ..... | ..... | ..... | ..... |
| iPS:43 7144 | 21-225_215B3 | VL3\|3r\|JL2 | ..... | ...RF.. | ..... | ..... | ..... | ..... | ...-ST. | ..... |
| iPS:43 7186 | 21-225_224H2 | VL3\|3r\|JL2 | ...S... | ..F..... | ..N.V..TY | ..... | ..... | ..... | ...-ST. | ..... |
| iPS:43 7192 | 21-225_225E9 | VL3\|3r\|JL2 | ..D..... | ..R..... | ..N..N.M | ..... | ..... | ..... | ...-ST. | ..... |
| iPS:43 7194 | 21-225_226B2 | VL3\|3r\|JL2 | ..... | ..... | ..T.G.W | ..R.. | ..... | ..N... | ..-G.A. | ..... |
| iPS:43 7200 | 21-225_226A10 | VL3\|3r\|JL2 | ..... | ..... | ..T.G.W | ..R.. | ..... | ..N... | ..-G.A. | ..... |
| iPS:43 7204 | 21-225_227E5 | VL3\|3r\|JL2 | ..S... | ..... | ..E.. | ..R.. | ..S.. | ..... | ..-NTMI | ..... |
| iPS:43 7210 | 21-225_227E12 | VL3\|3r\|JL2 | ..... | ..... | ..V.. | ..... | ..... | ..VN... | ..-SN.. | ..... |
| iPS:44 8908 | 21-225_50G9 | VL3\|3r\|JL2 | ..... | ..... | ..... | ..... | ..K.. | ..RN.. | ..-RRG. | ...R |
| iPS:45 1102 | 21-225_45F6 | VL3\|3r\|JL2 | ..... | ..... | ..... | ..... | ..R.E | ..N... | ..-RTM. | ..... |
| iPS:45 1110 | 21-225_74C9 | VL3\|3r\|JL2 | ..E... | ..S.VS | ..S.N. | ..NR.. | ..S.. | ..... | ...P.I | ..... |
| iPS:45 1112 | 21-225_53D10 | VL3\|3r\|JL2 | ..... | ..... | ..N.. | ..R.. | ..... | ..N... | ..-ST. | ..... |
| iPS:47 2731 | 21-225_14B1_LC2 | VL3\|3r\|JL2 | ..F.. | ..... | ..Y.. | ..R.. | ..... | ..... | ..-ST. | ..... |
| iPS:39 2583 | 21-225_10B10 | VL3\|3r\|JL2 | ..T.. | ..S.. | ..W.. | ..R.. | ..... | ..... | ..-ST. | ..... |
| iPS:39 2585 | 21-225_14H11 | VL3\|3r\|JL2 | ..T.. | ..... | ..V.. | ..T.. | ..T.. | ..... | ..-SSTI | ..... |
| iPS:39 2587 | 21-225_18G5 | VL3\|3r\|JL2 | ..... | ..E.. | ..... | ..... | ..... | ..N... | ..-SN.. | ..... |
| iPS:39 2589 | 21-225_27H2 | VL3\|3r\|JL2 | ..... | ..... | ..S.. | ..G.. | ..L.. | ..... | ..Y.. | ..... |
| iPS:39 2598 | 21-225_18E10 | VL3\|3r\|JL2 | ..... | ..R.. | ..... | ..R.. | ..... | ..... | ..-ST. | ..... |
| iPS:39 3166 | 21-225_27G6 | VL3\|3r\|JL2 | ..... | ..... | ..W.. | ..... | ..... | ..... | ..SY. | ..... |
| iPS:39 3168 | 21-225_32B11 | VL3\|3r\|JL2 | ..... | ..Y.. | ..... | ..S.. | ..K.. | ..N... | ..-ST. | ..... |
| iPS:39 3172 | 21-225_3B12 | VL3\|3r\|JL2 | ..S.. | ..E.. | ..... | ..R.. | ..... | ..VN.. | ..-NTMI | ..... |

Figure 52 (Continued)

| ID | Name | Region | | | | | | | |
|---|---|---|---|---|---|---|---|---|---|
| iPS:39 3176 | 21-225_27E7 | VL3j3r/JL2 | . . . . . | . . . . . N . | . . . . . | . . . . . | . . . . . | . . . . . -ST. | . . . |
| iPS:39 3178 | 21-225_34D7 | VL3j3r/JL2 | . . . . . | . . . . . E . | . . . . . | . . . . . T . | . . . . . N . | . . . . . -T. | . . . |
| iPS:39 3182 | 21-225_4B3 | VL3j3r/JL2 | . . R . . V | . . . . . Y | . . . . . | . . . . . | . . . . . N . | . . . . . -NT.I | . . . |
| iPS:39 3184 | 21-225_15H11 | VL3j3r/JL2 | . . . . . | . . . . . E . | . . . . . V | . . . . . R . | . . . . . | . . . . . -STA. | . . . |
| iPS:39 3186 | 21-225_27D9 | VL3j3r/JL2 | . . . . . M . | . . . . . Y | . . . . . F . | . . . . . | . . . . . V- | . . . . . | . . . |
| iPS:39 3188 | 21-225_34B9 | VL3j3r/JL2 | . . . . . A . | . . . . . VS | . . . . . E . | . . . . . R . | . . . . . | . . . . . -NMT. | . . . |
| iPS:39 3192 | 21-225_12B1 | VL3j3r/JL2 | . . R . . V | . . . . . | . . . . . | . . . . . | . . . . . | . . . . . -SST. | . . . |
| iPS:39 3194 | 21-225_16D2 | VL3j3r/JL2 | . . . . . | . . . . . | . . . . . | . . . . . | . . . . . N . | . . . . . -NT.I | . . . |
| iPS:39 3196 | 21-225_16G8 | VL3j3r/JL2 | . . . . . S . | . . . . . E . | . . . . . | . . . . . R . | . . . . . K . | . . . . . Y . | . . . |
| iPS:39 3198 | 21-225_28A11 | VL3j3r/JL2 | . . . . . | . . . . . | . . . . . F . | . . . . . R . | . . . . . VN . | . . . . . -NTMI | . . . |
| iPS:39 3200 | 21-225_35E1 | VL3j3r/JL2 | . . . . . | . . . . . Y | . . . . . I | . . . . . R . | . . . . . | . . . . . Y . | . . . |
| iPS:39 3202 | 21-225_6B4 | VL3j3r/JL2 | . . R . . V | . . . . . | . . . . . | . . . . . R . | . . . . . N . | . . . . . -STA. | . . . |
| iPS:39 3206 | 21-225_13F6 | VL3j3r/JL2 | . . . . . | . . . . . | . . . . . | . . . . . R . | . . . . . | . . . . . -NT.I | . . . |
| iPS:39 3210 | 21-225_17D3 | VL3j3r/JL2 | . . . . . S | . . . . . VY | . . . . . V . | . . . . . R . | . . . . . GN. | . . . . . | . . . |
| iPS:39 3212 | 21-225_30H6 | VL3j3r/JL2 | . . . . . | . . . . . N | . . . . . | . . . . . | . . . . . | . . . . . -ITA. | . . R |
| iPS:39 3214 | 21-225_33A1 | VL3j3r/JL2 | . . . . . | . . . . . FVY | . . . . . | . . . . . | . . . . . | . . . . . -SST. | . . . |
| iPS:39 3218 | 21-225_14G3 | VL3j3r/JL2 | . . . . . | . . . . . V . | . . . . . E . | . . . . . | . . . . . GN . | . . . . . .I | . . . |
| iPS:39 3222 | 21-225_17F5 | VL3j3r/JL2 | . . . . . | . . . . . E . | . . . . . | . . . . . R . | . . . . . | . . . . . -SST. | . . . |
| iPS:39 3224 | 21-225_31C2 | VL3j3r/JL2 | . . . . . | . . . . . N | . . . . . | . . . . . | . . . . . | . . . . . -SST. | . . . |

Figure 52 (Continued)

| | | L_FR1 | L_CDR1 | L_FR2 | L_CDR2 | L_FR3 | L_CDR3 | L_FR4 |
|---|---|---|---|---|---|---|---|---|
| iPS:39 3226 | 21-225_33E6 | VL3j3r/JL2 | . . . . . . . . . . . . . . . . . . . . . . . . . . . | . . . . . . . . . . . . . . . . . . . . Y | . . . . . . . . . . . . . . . . . . . . .F. . .I. | . . . . . . . . . . .R. | . . . . . . . . . . . . . . . . . . . . . . . . . . . . . . . . . . . . . . . | . . . . . .N. . . . . . . . . . . . . . . . . . . -STA. | . . . . . . . . . |
| iPS:39 3234 | 21-225_26C10 | VL3j3r/JL2 | . . . . . . . . .V. . . . . . . . . . . . . . . . | . . . . . . . . . . . . . . . . . . . . .V. | . . . . . . . . . . . . . . . . . . . . . | . . . . . . . . . . .R. | . . . . . . . . . . . . . . . . . . . . . . . . . . . . . . . . . . . . . . . | . . . . . .V-. . . . . . . . . . . . . . . . . . . -NNT. | . . . . . . . . . |
| iPS:39 3345 | 21-225_5G7 | VL3j3r/JL2 | . . . . . . . . . . . . . . . . .M. . . . . . . . | . . . . . . . . . . . . . . . . . . . . .N. .W | . . . . . . . . . . . . . . . . . . . . .F. | . . . . . . . . . . .R. | . . . . . . . . . . . . . . . . . . . . . . . . . . . . . . . . . . . . . . . | . . . . . .N. . . . . . . . . . . . . . . . . . . -ST. | . . . . . . . . . |
| iPS:39 3565 | 21-225_34B11 | VL3j3r/JL2 | . . . . . . . . . . . . . . . . . . . . . . . . . . . | . . . . . . . . . . . . . . . . . . . . . | . . . . . . . . . . . . . . . . . . . . .V. | . . . . . . . . . . .M. | . . . . . . . . . . . . . . . . . . . . . . . . . . . . . . . . . . . . . . . | . . . . . .N. . . . . . . . . . . . . . . . . . . -STA. | . . . . . . . . . |
| iPS:39 3950 | 21-225_3H10 | VL3j3r/JL2 | . . . . . . . . . . . . . . . . . . . . .S. . . . | . . . . . . . . . . . . . . . . . . . . .E. | . . . . . . . . . . . . . . . . . . . . . | . . . . . . . . . . .R. | . . . . . . . . . . . . . . . . . . . . . . . . . . . . . . . . . . .K. . . | . . . . . .VN. . . . . . . . . . . . . . . . . . . -N?M? | . . . . . . . . . |
| iPS:39 8470 | 21-225_14B7 | VL3j3r/JL2 | . . . . . . . . . . . . . . . . . . . . . . . . . . . | . . . . . . . . . . . . . . . . . . . . .N. | . . . . . . . . . . . . . . . . . . . . . | . . . . . . . . . . .R. | . . . . . . . . . . . . . . . . . . . . . . . . . . . . . . . . . . . . . . . | . . . . . .NN. . . . . . . . . . . . . . . . . . . -ST. | . . . . . . . . . |
| iPS:39 8472 | 21-225_16E4 | VL3j3r/JL2 | . . . . . . . .P. . . . . . . . . . . . . . . . . | . . . . . . . . . . . . . . . . . . . . .Y | . . . . . . . . . . . . . . . . . . . .S | . . . . . . . . . . . . . | . . . . . . . . . . . . . . . . . . . . . . . . . . . . . . . . .A. . . . . | . . . . . . . . . . . . . . . . . . . . . . . . . . | . . . . . . . . . |
| iPS:39 8488 | 21-225_19F6 | VL3j3r/JL2 | . . . . . . . . . . . . . . . . . . . . . . . . . . . | . . . . . . . . . . . . . . . . . . . . VY | . . . . . . . . . . . . . . . . . . . . . | . . . . . . . . . . . . . | . . . . . . . . . . . . . . . . . . . . . . . . . . . . . . . . . .T. . . . | . . . . . .N. . . . . . . . . . . . . . . . . . . -NT. | . . . .R. . . . . |
| iPS:39 8490 | 21-225_21D12 | VL3j3r/JL2 | . . . . . . . . . . . . . . . . . . . . . . . . . . . | . . . . . . . . . . . . . . . . . . . . .N. .Y | . . . . . . . . . . . . . . . . . . . . . | . . . . . . . . . . .R. | . . . . . . . . . . . . . . . . . . . . . . . . . . . . . . . . . . . . . . . | . . . . . .N. . . . . . . . . . . . . . . . . . . -ST. | . . . . . . . . . |
| iPS:39 8498 | 21-225_22E6 | VL3j3r/JL2 | . . . . . . . . . . . . . . . . . . . . . . . . . . . | . . . . . . . . . . . . . . . . . . . . .E. | . . . . . . . . . . . . . . . . . . . . . | . . . . . . . . . . .R. | . . . . . . . . . . . . . . . . . . . . . . . . . . . .Y. . . .T. . .F. . . | . . . . . .N. . . . . . . . . . . . . . . . . . . -ST. | . . . . . . . . . |
| iPS:39 8504 | 21-225_23D7 | VL3j3r/JL2 | . . . . . . . . . . . . . . . . . . . . . . . . . . . | . . . . . . . . . . . . . . . . . . . .E. .V. | . . . . . . . . . . . . . . . . . . . . . | . . . . . . . . . . . . . | . . . . . . . . . . . . . . . . . . . . . . . . . . . . . . . . . . . . . . . | . . . . . . . . . . . . . . . . . . . . . . . . . . | . . . . . . . . . |
| iPS:39 8546 | 21-225_9H10 | VL3j3r/JL2 | . . . . . . . . . . . . . . . . . . . . . . . . . . . | . . . . . . . . . . . . . . . . . . . . . | . . . . . . . . . . . . . . . . . . . . . | . . . . . . . . . . .R. | . . . . . . . . . . . . . . . . . . . . . . . . . . . . . . . . . . . . . . . | . . . . . .N. . . . . . . . . . . . . . . . . . . -SN. | . . . . . . . . . |
| iPS:40 2225 | 21-225_2B1 | VL3j3r/JL2 | . . . . . . . . . . . . . . . . . . . . . . . . . . . | . . . . . . . . . . . . . . . . . . . . .E. | . . . . . . . . . . . . . . . . . . . . . | . . . . . . . . . . .K. | . . . . . . . . . . . . . . . . . . . . . . . . . . . . . . . . . . . . . . . | . . . . . . . . . . . . . . . . . . . . . . . . .Y. | . . . . . . . . . |
| iPS:40 2231 | 21-225_6D9 | VL3j3r/JL2 | . . . . . . . . . . . . . . . . . . . . . . . . . . . | . . . . . . . . . . . . . . . . . . . . .Y | . . . . . . . . . . . . . . . . . . . . .V. | . . . . . . . . . . .R. | . . . . . . . . . . . . . . . . . . . . . . . . . . . . . . . . . . . .I. . | . . . . . .N. . . . . . . . . . . . . . . . . . . -NT. | . . . . . . . . . |
| iPS:40 4090 | 21-225_8D8 | VL3j3r/JL2 | . . . . . . . . . . . . . . . . . . . . . . . . . . . | . . . . . . . . . . . . . . . . . . . . .E. | . . . . . . . . . . . . . . . . . . . . .F. .I | . . . . . . . . . . .R. | . . . . . . . . . . . . . . . . . . . . . . . . . . . . . . . . . . . . . . . | . . . . . . . . . . . . . . . . . . . . . . . . -STA. | . . . . . . . . . |
| iPS:42 3018 | 21-225_31D12_LC2 | VL3j3r/JL2 | . . . . . . . . . . . . . . . . . . . . . . . . . . . | . . . . . . . . . . . . . . . . . . . . .Y | . . . . . . . . . . . . . . . . . . . . . | . . . . . . . . . . .R. | . . . . . . . . . . . . . . . . . . . . . . . . . . . . . . . . . . . . . . . | . . . . . .N. . . . . . . . . . . . . . . . . . . -STA. | . . . . . . . . . |
| | Germline | VL2j2a2/JL3b | QSALTQP ASVSGSPGQSI TSC | TGTS SDVGGY NYVS | WYQQHPGK APKLMIY | VSNRPS | GVSNRFSGSKSG NTASLTISGLQAEDEAD YYC | SSYTSS STWV | FGGGTK LTVL |
| iPS:46 8862 | 21-225_178H8 | VL2j2a2/JL3b | . . . . . . . . . . . . . . . . . . . . . . .S. . . | . . . . . . . . . . . . . . . . . . . . F. | . . . . . . . . . . . . . . . . . . . V.F. . | . . . . . . . . . . . . . | . . . . . . . . . . . . . . . . . . . . . . . . . . . . . . . . . .P. . . . . | . . . . . . . . . . . . . . . . . . . . . . . . -YI. . . | . . . . . . . . . |

Figure 52 (Continued)

| | | | | | | | |
|---|---|---|---|---|---|---|---|
| iPS:43 6838 | 21-225_52H4 | VL2J2a2/ JL3b | .......... | .......... | .......... | .......... | N...... -<br>......NIT.. |
| iPS:43 7094 | 21-225_210D12 | VL2J2a2/ JL3b | .......... | ....V.<br>....L. | .......... | .......... | N...... -<br>......IT.. |
| iPS:43 7096 | 21-225_210E12 | VL2J2a2/ JL3b | .......... | .......... | .......... | .......... | G..VK-<br>....GIT.. | S |
| iPS:43 7098 | 21-225_211C1 | VL2J2a2/ JL3b | .......S. | ....Y. | .......... | .......... | N...... -<br>......IT.. |
| iPS:43 7104 | 21-225_211G5 | VL2J2a2/ JL3b | .......... | .......... | .......... | .......... | N...R-<br>......IT.. |
| iPS:43 7112 | 21-225_212C2 | VL2J2a2/ JL3b | .......... | .......... | ......R. | .......... | N...R-<br>......IT.. |
| iPS:43 7114 | 21-225_212A4 | VL2J2a2/ JL3b | .......... | ....Y. | .......... | .......... | G..VK-<br>....GIT.. | S |
| iPS:43 7116 | 21-225_212F6 | VL2J2a2/ JL3b | .......... | T...... | .......... | .......... | N...... -<br>......IT.. |
| iPS:43 7118 | 21-225_212G7 | L......... | ......S. | ......R. | .......... | .......... | N...R-<br>......IT.. |
| iPS:43 7128 | 21-225_213G3 | VL2J2a2/ JL3b | .......... | ....V. | ......R. | .......... | N...R-<br>......IT.. |
| iPS:43 7130 | 21-225_213D5 | VL2J2a2/ JL3b | .......... | .......... | .......... | ....K. | C...R-<br>....RIT.. |
| iPS:43 7146 | 21-225_215D3 | VL2J2a2/ JL3b | .......I. | T...... | .......... | .......... | N..KR-<br>....GST.. |
| iPS:43 7150 | 21-225_216A3 | VL2J2a2/ JL3b | .......... | .......... | .......... | ......Y. | N...... -<br>......IT.. | V |
| iPS:43 7162 | 21-225_217B2 | VL2J2a2/ JL3b | .......... | ....L. | .......... | .......... | G..VK-<br>....GIT.. | S |

Figure 52 (Continued)

| | | L_FR1 | L_CDR1 | L_FR2 | L_CDR2 | L_FR3 | L_CDR3 | L_FR4 |
|---|---|---|---|---|---|---|---|---|
| iPS:43 7172 | 21-225_219A7 | VL2l2a2/ JL3b | L........ ........ | ........ ........ ........ | ........ | ........ | ........ | C....R— ........ | ........ ........ |
| iPS:43 7182 | 21-225_221H2 | VL2l2a2/ JL3b | ........ ........ | ........ ........ S....... | ........ | ..R..... | ........ | N...R— ...IT.. | ........ ........ |
| iPS:43 7184 | 21-225_221G4 | VL2l2a2/ JL3b | ........ ........ | ........ ........ ........ | ........ | ..R..... | ........ | N...R— ...IT.. | ........ ........ |
| VL2l2a2JL3b | Germline | L_FR1 DSVLTQP- PSASGTPGQRVT ISC | L_CDR1 SGSS SNIGS NTVN | L_FR2 WYQQLPGT APKLLIY | L_CDR2 NNQRPS | L_FR3 GVPDRFSGSKSG TSASLAISGLRSEDEAD YYC | L_CDR3 AAWDDS----- LNGVV | L_FR4 FGGGT LTVL |
| iPS:46 8864 | 21-225_60D6 | VL1l1c/J L2 | ........ ........ | ........ ........ | ........ | ........ | ........ | ........ ...SLNGP | V....... |
| iPS:43 6660 | 21-225_146D8 | VL1l1c/J L2 | ........ ........ | ......Y. ......D | ........ | ........ | ........ | ........ | ........ |
| iPS:43 6680 | 21-225_147H12 | VL1l1c/J L2 | T....... ........ | ...YA... ........ | ........ | ........ | ........ | E....... ........P. | ........ |
| iPS:43 6682 | 21-225_146A8 | VL1l1c/J L2 | ........ ........ | ...SI... ........ | ....R... | ........ | ........ | ........ | ........ |
| iPS:43 6684 | 21-225_146B6 | VL1l1c/J L2 | ........ ........ | ...A.... ........ | ........ | ..D..... | ........ | ........ | ........ |
| iPS:43 6696 | 21-225_149A1 | VL1l1c/J L2 | ........ ........ | ...A.... ........ | ........ | ........ | ........ | ........ | ........ |
| iPS:43 6712 | 21-225_150F9 | VL1l1c/J L2 | ........ ........ | ...A.S.. ........ | ........ | ..S..... | F....... | ........ .....K.P. | ........ |
| iPS:43 6750 | 21-225_154G12 | VL1l1c/J L2 | ........ ........ | ......N. ........ | ........ | ..DH.... | ........ | ........ | ........ |
| iPS:43 6762 | 21-225_156H2 | VL1l1c/J L2 | V....... ........ | ........ ........ | ........ | ..S..... | L....... | ........ | ........ |
| iPS:43 7044 | 21-225_197F9 | VL1l1c/J L2 | ........ ........ | ........ ........ | ........ | ........ | ........ | ........ .....M.P. | V....... |
| iPS:43 7060 | 21-225_199C3 | VL1l1c/J L2 | ........ ........ | ........ ........ | ........ | ..I..... | ........ | ........ ........P. | ........ |
| iPS:39 3180 | 21-225_4G12 | VL1l1c/J L2 | ...NM... ........ | ...TN... ..V..... | ........ | ..I..... | ........ | ........ LNGH. | ...R.... |
| iPS:39 3230 | 21-225_9G9 | VL1l1c/J L2 | ...NM... ........ | ...TN... ..V..... | ........ | ........ | ........ | ........ LNGH. | ...R.... |
| | Germline | L_FR1 | L_CDR1 | L_FR2 | L_CDR2 | L_FR3 | L_CDR3 | L_FR4 |

Figure 52 (Continued)

| | | L_FR1<br>SYELTQP<br>PSASGTPGQRVT<br>ISC | L_CDR1<br>SGD<br>ALPK | L_FR2<br>NYQQKSGQ<br>APVLVIY | L_CDR2<br>EDSKRPS | L_FR3<br>GIPERFSGSSSG<br>TMATLTISGAQIEDEAD<br>YYC | L_CDR3<br>YSTDSS<br>SGNR | L_FR4<br>FGGGTK<br>LTVL |
|---|---|---|---|---|---|---|---|---|
| VL3j3p/JL2 | | | | | | | | |
| iPS:46 8866 | 21-225_190C1 | VL3j3p/J L2 | T....M... | ...D... S | ........ | ........T..E. | N........ | ........ |
| iPS:43 7214 | 21-225_48B12 | VL3j3p/J L2 | ........ | ........ | ........ | P............. | N........SGNR. | ........ |
| | Germline | L_FR1 | L_CDR1 | L_FR2 | L_CDR2 | L_FR3 | L_CDR3 | L_FR4 |
| VL1j1c/JL3b | | QSVLTQP<br>PSASGTPGQRVT<br>ISC | SGSSSNIGS<br>NTVN | WYQQLPGT<br>APKLLIY | KNDQRPS | GVPDRFSGSKSG<br>TSASLAISGLRSEDEAD<br>YYC | AAWDDS<br>LNGWV | FGGGTK<br>LTVL |
| iPS:43 6234 | 21-225_51E3 | VL1j1c/J L3b | ....N... | ........ | ........ | ........ | T........ | ........T |
| iPS:43 6830 | 21-225_51F4 | VL1j1c/J L3b | ....I..T | ........ | ..D..... | ........T... | T........ | ........T |
| iPS:43 6834 | 21-225_52F1 | VL1j1c/J L3b | ....I..T | ........ | ..D..... | ........ | ........ | ........T |
| iPS:43 6842 | 21-225_54E9 | VL1j1c/J L3b | ....N..N.. | ........ | ..D..V... | ........ | V........ | ........T |
| iPS:43 6844 | 21-225_56G1 | VL1j1c/J L3b | ....HI.T | ........ | ..D..... | ........ | ......I.. | ........T |
| iPS:43 6846 | 21-225_56E3 | VL1j1c/J L3b | ....I..T | ........ | ........ | ......C... | ........ | ........ |
| iPS:43 7010 | 21-225_192G3 | VL1j1c/J L3b | ....H... | ...F.... | .G...... | ........ | ........ | ........T |
| iPS:43 7032 | 21-225_195H6 | VL1j1c/J L3b | ........M. | ........ | .N...K.. | ........ | .T....... | ........T |
| iPS:43 1104 | 21-225_49C5 | VL1j1c/J L3b | ....N... | ........ | ..V..... | ........ | T......SV. | ......V. |
| iPS:45 1106 | 21-225_49D10 | VL1j1c/J L3b | ....I..T | ........ | ..D..... | ........T... | T........ | ........T |
| iPS:45 1108 | 21-225_53E8 | VL1j1c/J L3b | ....C..I.T | ........ | ..D..... | ........ | T........D... | ........T |
| | Germline | L_FR1 | L_CDR1 | L_FR2 | L_CDR2 | L_FR3 | L_CDR3 | L_FR4 |
| VL3j3r/JL1 | | SYELTQP<br>PSVSVSPGQTAS | SGD<br>KLGD<br>KYAC | WYQQKPGQ<br>SPVLVIY | DSKRPS | GIPERFSGSNSG<br>NTATLTISGTQAMDEAD<br>YYC | QAWDS<br>STAYV | FGGGTK<br>LTVL |
| iPS:43 6662 | 21-225_147D7 | VL3j3r/JL 1 | ........ | ....F... | ........ | ....R... | ........ | R........-NTA. | ........ |
| iPS:43 6720 | 21-225_151H6 | VL3j3r/JL 1 | ........ | ........ | ........ | ....T... | ........ | ........-ST. | ........ |

| | | | L_FR1 | L_CDR1 | L_FR2 | L_CDR2 | L_FR3 | L_CDR3 | L_FR4 |
|---|---|---|---|---|---|---|---|---|---|
| iPS:43_6792 | 21-225_169D12 | VL6(6a)/JL3b | | ....TG. | ..H....N | ...KK. | | ...Y | |
| | VL3jll/JL2 | Germline | QPVLTQP-PSVSGAPGQRVT ISC | TGTS SDVGSY NLVS | WYQQLPGT APKLMIY | DVS KRPS | GVSNRFSGSKSG NTASLTITGLQAEDEAD YYC | CSYAGS STYVV | FGGGTK LTVL |
| iPS:43_6800 | 21-225_171D12 | VL3jll/JL2 | | | | | | | |
| iPS:43_6804 | 21-225_172C3 | VL3jll/JL2 | | ......N.. | .....I... | .A..... | | ......S.... | |
| iPS:43_6806 | 21-225_172B12 | VL3jll/JL2 | | ......N.. | .....I... | .T..S.. | ......T........ | | |
| iPS:43_6964 | 21-225_190B3 | VL3jll/JL2 | | ...K..T.. | .....V... | .T..S.. | ......T........ | ....GNHL.L | |
| iPS:43_6970 | 21-225_190B8 | VL3jll/JL2 | | ..T..E... | | | | ....GNHL... | |
| iPS:43_6980 | 21-225_190C10 | VL3jll/JL2 | | .....V... | | | ......E........ | ....GNHL... | |
| iPS:43_6992 | 21-225_191B8 | VL3jll/JL2 | | ..T..P... | .....P... | | ......S........ | ....GNHL... | |
| iPS:43_6994 | 21-225_191A9 | VL3jll/JL2 | | .......F. | | | ......E........ | ....C...... | |
| iPS:43_7016 | 21-225_193A6 | VL3jll/JL2 | | ..........N | .....F... | .A..... | ......N........ | ....GNHL... | |
| | VL2(2b2)/JL2 | Germline | L_FR1 | L_CDR1 | L_FR2 | L_CDR2 | L_FR3 | L_CDR3 | L_FR4 |
| | | | QSALTQP- ACVSGSPGQSITI SC | TGTS SDVGGY NYVS | WYQQHPGK APKLMII | EVS NRPS | GVSNRFSGSKSG NTASLTISGLRAEDEAD YYC | CSYAGS STYVV | FGGGTK LTVL |
| iPS:43_6810 | 21-225_175F4 | VL2(2b2)/JL2 | | ........RF | ........Y | | | ....Y...... | |
| iPS:43_6814 | 21-225_178H10 | VL2(2b2)/JL2 | | ........RF | ..H..N... | | ......R........ | | |
| | VL3jll/JL3b | Germline | L_FR1 | L_CDR1 | L_FR2 | L_CDR2 | L_FR3 | L_CDR3 | L_FR4 |
| | | | SSELTQD PAVSVALGQTVR ITC | QGD SLRS YYAS | WYQQKPGQ APVLVIY GKNNRPS | | GIPDRFSGSSSG NTASLTIT-GAQAEDEAD YYC | NSRDSS | FGGGTK LTVL |
| iPS:43_6816 | 21-225_179H5 | VL3jll/JL3b | | ........N. | | | | | |
| | VL1(1e)/JL1 | Germline | L_FR1 | L_CDR1 | L_FR2 | L_CDR2 | L_FR3 | L_CDR3 | L_FR4 |
| | | | QSVLTQP PSVSGAPGQRVTISC | SGS SSNIGSN- YDVH | WYQQLPGT APKLLIY NSNRPS | | GVPDRFSGSKSG TSASLAITGLQAEDEAD YYC | CSYDSS LSGYV | FGTGTK VTVL |

Figure 52 (Continued)

| | | | L_FR1 | L_CDR1 | L_FR2 | L_CDR2 | L_FR3 | L_CDR3 | | L_FR4 |
|---|---|---|---|---|---|---|---|---|---|---|
| iPS:43 6832 | 21-225_51D8 | VL1\|1e/J L1 | | | | | | | | |
| | VL1j1e/J7 | Germline | SYELTQP PSVSVSPGQTAS ITC | SGD KLGT RYAC | NYQQKPGQ SPVLVIY | -DSKRPS | GIPERFSGSNSG NTATLTISGTQAMDEAD YYC | QAWDS | STAAV | FGGGTQ LTVL |
| iPS:43 6840 | 21-225_53E9 | VL3j3r/JL 7 | | T | | N | | T | ST | T |
| iPS:43 6950 | 21-225_184G4 | VL3j3r/JL 7 | | F | | E.R | | | RTV | |
| | VL1j1bJL2 | Germline | QSVLTQP PSVSAAPGQKVT ISC | SGSS SNIGN NYVS | RYQQLPGT APKLLIY | -DNNKRPS | GIPDRFSGSKSG TSATLGITGLQTGDEAD YYC | GTWDSS | LSAVV | FGGGTK LTVL |
| iPS:43 6856 | 21-225_58C5 | VL1\|1b/J L2 | | | | | | I | VG | |
| iPS:43 6960 | 21-225_198D2 | VL1\|1b/J L2 | | S | V | | | R | NVG | |
| iPS:43 6966 | 21-225_190C3 | VL1\|1b/J L2 | | | L | S | G | | T | |
| iPS:43 6968 | 21-225_190B10 | VL1\|1b/J L2 | | H | H | | | GR | G | |
| iPS:43 6974 | 21-225_190H7 | VL1\|1b/J L2 | | S | V | | | | NVG | |
| iPS:43 6976 | 21-225_190D8 | VL1\|1b/J L2 | | | | SS | E | R | T | |
| iPS:43 6982 | 21-225_190D10 | VL1\|1b/J L2 | | V | V.V | | V | | NVG | |
| iPS:43 6986 | 21-225_191A1 | VL1\|1b/J L2 | | L.F | F | Y | | | G | |
| iPS:43 7006 | 21-225_192G2 | VL1\|1b/J L2 | R | | | | R | | NTG | |
| iPS:43 7024 | 21-225_194F11 | VL1\|1b/J L2 | | | F | | | | G | |
| iPS:43 7028 | 21-225_194G12 | VL1\|1b/J L2 | | | | | R.E | | VG | |
| iPS:43 7042 | 21-225_197E8 | VL1\|1b/J L2 | | K | F | | K | I.R | VM | |
| iPS:43 7064 | 21-225_200G8 | VL1\|1b/J L2 | R | F.L | | Y | L | | NTG | |
| iPS:43 7086 | 21-225_209A8 | VL1\|1b/J L2 | | FL.S | | | | | G | |

Figure 52 (Continued)

| | | | | L_CDR1 | | L_FR2 | L_CDR2 | L_FR3 | L_CDR3 | L_FR4 |
|---|---|---|---|---|---|---|---|---|---|---|
| iPS:43_7138 | 21-225_214D8 | VL1|1b/J L2 | | ........... | ..F.... ...H | ....... | ...S.. | ........ .A.... | .A............ .............. | I....S. ....... |
| iPS:43_7168 | 21-225_218G4 | VL1|1b/J L2 | | ........... | .....L. | ....... | ....... | .............. | ..............NT. | ....... |
| | | Germline | NFMLTQP PSVSESPGKTVT ISC | TRSSGSIAS ------NYVQ | L_FR1 | WYQQRPGS SPTTVIV | L_CDR2 EDNQRPS | CVPDRFSGSIDSSSNSA GLTIGLKTEDEADYYIC | L_CDR3 QSYTS------SNWV | L_FR4 FGGGTK LTVL |
| iPS:43_6888 | 21-225_63G7 | VL6|6a/J L2 | | .....N...V.. | ....... | ...M... | .SR.... | ........S..... | ....G......... I.... | ....... |
| iPS:43_6890 | 21-225_63A10 | VL6|6a/J L2 | | .....N...V.. | ....... | ....... | .KR.... | .............. | ............. I.... | ....... |
| | | Germline | QTVVTQE PSLVSGPGGTVT LTC | GLSS-- GSVSTS ----YYPS | L_FR1 | WYQQTPGQ APRLLIY | L_CDR2 NTRSS | GVPDRFSGSILG NKAALTITGAQADDESD YYC | L_CDR3 VLYMG------SSIWV | L_FR4 FGGGTK LTVL |
| iPS:43_6910 | 21-225_73G1 | VL8|8a/J L3b | | ........... | ....... | ....N.. | ....... | .............. | .......A...... | ....... |
| iPS:43_6948 | 21-225_183F5 | VL8|8a/J L3b | | .....F..... | ....... | ...T... | ....... | .............. | ............. | ....... |
| | | Germline | QTVVTQEP SITVSPGGTVT LTC | ASST GSVTSG ----NYPN | L_FR1 | WFQQRPGS APRTLIY | L_CDR2 STSNRKS | NTPARFSGSLLG GKAALTLSGVQPEDEAE YYC | L_CDR3 LLYC------GAQYY | L_FR4 FGGGTR LTVL |
| iPS:43_6920 | 21-225_74E5 | VL7|7a/J L2 | | .....ET | ....... | ....... | ....... | .....D........ | .............L. | ....... |
| iPS:43_6926 | 21-225_78D10 | VL7|7a/J L2 | | ......S | ....... | ....... | ....... | .............. | .............LM | ....... |
| iPS:43_6958 | 21-225_190D1 | VL7|7a/J L2 | | ......F | ....... | ....... | ....... | .............. | .............. | ....... |
| iPS:43_6984 | 21-225_190F10 | VL7|7a/J L2 | | VF......3.. | ....... | ....... | ....... | ...........D.. | .............A | ....... |
| iPS:43_6988 | 21-225_191A2 | VL7|7a/J L2 | | VL...SF... | ....... | ....... | ....... | ...........D.. | ...C.........L. | ....... |
| iPS:43_7002 | 21-225_191H9 | VL7|7a/J L2 | | ......SF... | ....... | .L..T.. | ....... | .............. | ...M.C........L. | ....... |
| iPS:43_7008 | 21-225_192E3 | VL7|7a/J L2 | | ......F...S | ....... | ....... | ....N.. | ..........R... | ...IF........VH.I | ....... |
| iPS:43_7012 | 21-225_192G7 | VL7|7a/J L2 | | .....N..Q | ....... | ....... | ..T.R.. | .............. | ...F.........I | ....... |
| iPS:43_7014 | 21-225_192H8 | VL7|7a/J L2 | | ......F..T | ....... | ....... | ....N..R | ...........M.D | .............LM | ....... |

Figure 52 (Continued)

| | | | | | | | | | |
|---|---|---|---|---|---|---|---|---|---|
| iPS:43 7022 | 21-225_194G5 | VL7|7a/J L2 | . . . . . . | . . . . . . | . . . T . . | . . . . . . | . S . . . . | . . . . G . | . I . . . . . . . . . . |
| iPS:43 7026 | 21-225_194D12 | VL7|7a/J L2 | . . . . . . | . . N . . . | . . . . . . | . . . . . . | . . . . . . | . . . . . . | . I . . . . . . . . LM |
| iPS:43 7040 | 21-225_196E7 | VL7|7a/J L2 | . . . . . . | . . SF.S | . . . . . A | . . . R . . | . . . . E . | . . . . . . | . . . . . . . . . . LA |
| iPS:43 7048 | 21-225_197B11 | VL7|7a/J L2 | . . . . . . | . F . . . . | . L . . . T | . . N . . . | . . . D . . | . . . . . . | . IF . . . . . . VH.I |
| iPS:43 7050 | 21-225_197C11 | VL7|7a/J L2 | . . . . . . | . . . S . . | . . . . . A | . . . . . . | . . . . . . | . . . . . . | . . . . . . . . . . L. |
| iPS:43 7056 | 21-225_198B8 | VL7|7a/J L2 | . . . . S . | . VL . . . . | . . . . . . | . . . . . . | . . . D . . | . . . . . . | . IF . . . . . . VH.I |
| iPS:43 7062 | 21-225_200H1 | VL7|7a/J L2 | . . . . . . | . . . SF . . | . L . . . . | . H . N . . | . . . . . . | . . . D.F | M.S . . . . . . . M. |
| iPS:43 7066 | 21-225_200G9 | VL7|7a/J L2 | . . . . . . | . . N . . . | . . . L . . | . H . D . . | . . . A . . | . . . . . . | . I . . . . . . . . L. |
| iPS:43 7068 | 21-225_200A11 | VL7|7a/J L2 | . . . . . . | . . N . . . | . V . . . . | . . . N . . | . . . . . . | . . . . . . | . I . . . . . . . . L. |
| iPS:43 7090 | 21-225_210F11 | VL7|7a/J L2 | . . . . . . | . F . N . . | . . . . . . | . . . . . . | . . . . . . | . . . . . . | . . . . . . . . . HLA |
| iPS:43 7106 | 21-225_210H7 | VL7|7a/J L2 | . . . . . . | . F . N . S | . V . . . . | . . . R . . | . . . . . . | . . . . . . | . . . . . . . . . . L. |
| iPS:43 7108 | 21-225_211C9 | VL7|7a/J L2 | . . . . . . | G . . . . . | . . . . . . | . . . P . . | . . . D . . | . . . D . . | . . . . . . . . . . LA |
| iPS:43 7110 | 21-225_211E9 | VL7|7a/J L2 | . . . . . . | . . . F . . | . . . . . . | . . . N . . | . . . . T.F | . . . . . . | . . . . . . . . . . LA |
| iPS:43 7120 | 21-225_212A9 | VL7|7a/J L2 | . . . . . . | . . . . . . | . . . . . . | . . . N . . | . G . . . . | . . . D . . | . . . . . . . . . . G. |
| iPS:43 7124 | 21-225_212H12 | VL7|7a/J L2 | . . . . . . | G . . . . . | . . . . . . | . . . . . . | . . . D . . | . . . . T . | . . . . . . . . . . H. |
| iPS:43 7132 | 21-225_213F5 | VL7|7a/J L2 | . . . . . . | . . . S . . | . T . P . . | . . . . . . | . . . . . . | . . . . . . | . F . . . . . . . . LA |
| iPS:43 7136 | 21-225_214H3 | VL7|7a/J L2 | . . . . . . | . . . F . . | . . . . . . | . . . . . . | . . . . . . | . . . . . . | . . . CD . . . . . H. |
| iPS:43 7140 | 21-225_214E12 | VL7|7a/J L2 | . . . . . . | . . . . . . | . . . . . . | . . . . . . | . G . . T . | . . . D . . | . . . . . . . . . . L. |
| iPS:43 7142 | 21-225_215A3 | VL7|7a/J L2 | . . . . . . | . . E . . . | . . . . . . | . . . . . . | . CG . . . . | . . . D . D | . . . . . . . . . . LA . . . . . . A. |
| iPS:43 7148 | 21-225_215H3 | VL7|7a/J L2 | . . . . . . | . . N . S | . . . . . . | . . N . . . | . C . . . . | . . . D . D | . . . . . . . . . . G. |
| iPS:43 7154 | 21-225_216A7 | VL7|7a/J L2 | . . . . . . | . . . . . . | . . . . . . | . . N . . . | . . . . . . | . . . . . . | . . . . . . . . . . G. |

Figure 52 (Continued)

[Figure showing antibody sequence alignment table with columns for L_FR1, L_CDR1, L_FR2, L_CDR2, L_FR3, L_CDR3, and L_FR4 regions across multiple antibody clones including iPS:43 21-225_216H11, 190C7, 193F11, 195H9, 191B9, 194G3, 199F3, 191G9, 203B2, 205E12, 206B5, 209H10, and 211H2, organized by germline groupings VL1j1b/JL3b, VL1j1b/JL1, VL5j5c/JL2, and VL3j3j/JL2.]

Figure 52 (Continued)

| | | L_FR1 | L_CDR1 | L_FR2 | L_CDR2 | L_FR3 | L_CDR3 | L_FR4 |
|---|---|---|---|---|---|---|---|---|
| iPS:43 7160 | 21-225_216B12 | VL3|3j/JL2 | ..........................  | .D....RR. | ............................ | .........S. | ...........................................IE......P. | .........-STG. | ............ |
| iPS:39 2593 | 21-225_3E10 | VL3|3j/JL2 | ......TA.M....H..... | ....R..... | .D........................ | ............ | ...........................................IE......P. | .......DH... | ............ |
| iPS:39 3204 | 21-225_8C12 | VL3|3j/JL2 | ......TA.M....H..... | ....A..... | .D........................ | ............ | ...........................................IE......P. | .......DH... | ............ |
| | Germline | L_FR1 | L_CDR1 | L_FR2 | L_CDR2 | L_FR3 | L_CDR3 | L_FR4 |
| VL2|2a2/JL2 | | QSALTQP ASVSGSPGQSIT ISC | TGTS SDVGGY NYVS | WYQQHPG KAPKLMIY | EVSNRPS | GVSNRFSGSKSG NTASLTISGLQAEDEAD YYC | SSYTTS STLVV | FGGGTK LTVL |
| iPS:43 7092 | 21-225_210B12 | VL2|2a2/JL2 | ............................ | ............ | ....F........... | ..R....... | ............................................ | .......RTL.. | ............ |
| iPS:43 7134 | 21-225_213A7 | VL2|2a2/JL2 | ............................ | ....F........... | ............ | ..R....... | ............................................ | .......RTL.. | ............ |
| iPS:47 2733 | 21-225_2B10_LC2 | VL2|2a2/JL2 | ............................ | ............ | ......D........... | ............ | ............................................ | T......TGT.. | ............ |
| iPS:39 2573 | 21-225_15G2 | VL2|2a2/JL2 | ............................ | ............ | ............ | ............ | ............................................ | T......TST.. | ............ |
| iPS:39 3232 | 21-225_17F12 | VL2|2a2/JL2 | ............................ | ..A.....D. ...S...... | ............ | ............ | ............................................ | .......IT... | ............ |
| iPS:39 8494 | 21-225_21H4 | VL2|2a2/JL2 | ............................ | ...S...... | ......D........... | ............ | ............................................ | ..R-...ST... | ............ |
| | Germline | L_FR1 | L_CDR1 | L_FR2 | L_CDR2 | L_FR3 | L_CDR3 | L_FR4 |
| VL3|3m/JL1 | | SYELMQPP PSVSVSPGQTAR ITC | SGD ALPK QKYAY | WYQQKPG QAPVLVIY | KDSERPS | GIPERFSGSSSG TTVTLTISGVQAEDEAD YYC | QSADSS GTYYV | FGTGTK VTVL |
| iPS:43 7102 | 21-225_211E5 | VL3|3m/JL1 | ......T............. | ............ | ............ | .......A.. | ..........V................................. | LVY.-...L... | ............M |
| iPS:43 7164 | 21-225_217C6 | VL3|3m/JL1 | ......T............. | ............ | ............ | ............ | ..........R................................. | ...SDT..... | ............ |
| iPS:43 7166 | 21-225_217G11 | VL3|3m/JL1 | ......T............. | ............ | ............ | ............ | ..........V................................. | LIV.-....... | ............ |
| iPS:43 7170 | 21-225_218E5 | VL3|3m/JL1 | ......T............. | .R.V....... | ............ | ............ | ..........R................................. | LVY.-...SDT.. | ............ |

Figure 52 (Continued)

| | | L_FR1 | L_CDR1 | L_FR2 | L_CDR2 | L_FR3 | L_CDR3 | L_FR4 |
|---|---|---|---|---|---|---|---|---|
| iPS:43 7196 | 21-225_226B7 | VL3|3m/J L1 | F..T...... | .....R. ......H.V. | ......N. | | .......SGT. | |
| | VL4|c/JL2 | Germline | L_FR1 SYVLTQP PSASALLGASIK LTC | L_CDR1 TLSS EHSTY TIE | L_FR2 WYQLRPGR VKS SPQIMK | L_CDR2 | L_FR3 GIPDRFMGSSSG BCSHSEGD ADVYLTFSALQSDDEAE FYC | L_CDR3 GESHTID SQWGWV | L_FR4 FGGGTK LTVL |
| iPS:39 2596 | 21-225_12D8 | VL4|c/J L2 | | | | | .............D........... | | |
| iPS:39 3174 | 21-225_15D8 | VL4|c/J L2 | | | | .........I. | ............E.......... | | |
| iPS:39 8544 | 21-225_7C8 | VL4|c/J L2 | | | | | .............D...G....... | ....P. | |
| | VL3|3h/JL2 | Germline | L_FR1 SYVLTQP PSSVSPGKTAR LTC | L_CDR1 GGN NIGS KSVH | L_FR2 WYQCKPGQ APVLVIY | L_CDR2 DSERPS | L_FR3 GIPERFSGSNSG NTATLTISRVEAGDEAD YYC | L_CDR3 QVWDSS SDRVV | L_FR4 FGGGTK LTVL |
| iPS:39 3208 | 21-225_16F3 | VL3|3h/J L2 | ......Q. | | ......V... | ..D......I..... | | | |
| HEAVY_VARIABLE | | | | | | | | | |
| | VH1|1-08|D6|6-19|RF1/JH4 | Germline | H_FR1 QVQLVQS GAEVKKPGASVK VSCKASG IYTF | H_CDR1 S......VDIN | H_FR2 WVRQAIGQ GLEWMG | H_CDR2 WMNH- SGNTGYAQ KFQG | H_FR3 RVTMTRTSISTAYMEL SSLRSEDTAVYYCAR | H_CDR3 CVSSGW- YYFDY | H_FR4 WGQGT VTVSS |
| iPS:42 6126 | 21-225_6G6 | VH1|1-08|D6|6-19|RF1/J H4 | .........R. | N.............. | ...P............ | .......H. ..........K. | .............A....V... .................L.... | SSGWY- | |
| iPS:41 2232 | 21-225_4A2 | VH1|1-08|D6|6-19|RF1/J H4 | | N.............T. | | .......H. | ...................... ..................S... | SSGWY- .....-. | |
| iPS:42 6112 | 21-225_12F12 | VH1|1-08|D6|6-19|RF1/J H4 | | N............... | | .......Y. | .........M............ ...................... | SSGWY- ....-M. | |
| iPS:45 1141 | 21-225_164B11 | VH1|1-08|D6|6-19|RF1/J H4 | | N............... | | .......T. | .........M........SY.. ...................... | SSGWY- .....-. | |
| iPS:46 8850 | 21-225_63F4 | VH1|1-08|D6|6-19|RF1/J H4 | | N............V. | | .......H. ..........R. | .............L....V... ...................Y.. | SSGWY- ....-V. | |

Figure 52 (Continued)

| | | | | | | | | | |
|---|---|---|---|---|---|---|---|---|---|
| iPS:46 8852 | 21-225_71F3 | VH1\|1-08/D6\|6-19\|RF1/J H4 | .......... | ....V. | .......... | .......... | .......... | .......... | SSGWY--- .......... |
| iPS:46 8854 | 21-225_72C4 | VH1\|1-08/D6\|6-19\|RF1/J H4 | .......... | N........ | .......... | .......... | .N....... | ......Y... | SSGWY--- .-V..S |
| iPS:46 8870 | 21-225_74A8 | VH1\|1-08/D6\|6-19\|RF1/J H4 | .......... | N........ | ....V..... | .H........ | .......... | ......SH.. | SSGWY--- .-L.... |
| iPS:42 3314 | 21-225_12F11 | VH1\|1-08/D6\|6-19\|RF1/J H4 | .......... | N........ | ...S...... | .H........ | ....S..... | ......Y... | SSGWY--- .-K.... |
| iPS:43 3909 | 21-225_43D8 | VH1\|1-08/D6\|6-19\|RF1/J H4 | .......... | N........ | ..P....... | .H......K. | ....A...V. | ......L... | SSGWY--- .-..... |
| iPS:43 4177 | 21-225_56A1 | VH1\|1-08/D6\|6-19\|RF1/J H4 | .......... | N........ | .......... | .H........ | ....T..... | ......H... | SSGWT--- .....A |
| iPS:43 4211 | 21-225_60F3 | VH1\|1-08/D6\|6-19\|RF1/J H4 | .......... | N........ | ...L...... | .H........ | .......... | ......Y... | SSGWY--- .-L.... |
| iPS:43 4235 | 21-225_61E3 | VH1\|1-08/D6\|6-19\|RF1/J H4 | .....L.... | N........ | .......... | .T........ | ....K..... | ......Y... | SSGWY--- .-V.... |
| iPS:43 4237 | 21-225_61B5 | VH1\|1-08/D6\|6-19\|RF1/J H4 | .......... | N........ | .......... | .H....S... | .......... | ......Y... | SSGWY--- .-F.... |
| iPS:43 4295 | 21-225_58B9 | VH1\|1-08/D6\|6-19\|RF1/J H4 | .......... | N........ | .......... | ....S..... | .......... | ......Y... | SSGWY--- .-R.... |
| iPS:43 4305 | 21-225_59E1 | VH1\|1-08/D6\|6-19\|RF1/J H4 | .......... | N........ | .......... | .T........ | ....T..... | ......F... | SSGWY--- .-..... |
| iPS:43 4321 | 21-225_59F10 | VH1\|1-08/D6\|6-19\|RF1/J H4 | .......... | N........ | .......... | .......... | .......... | ....N.V... | SSGWY--- .-F.... |

Figure 52 (Continued)

| | | | | | | | | |
|---|---|---|---|---|---|---|---|---|
| iPS:43 4431 | 21-225_70E7 | VH1j1-08jD6j6-19jRF1/J H4 | .... | N.... | .... H.... .... | .... .... .... | .... .Y. .... | SSGWY- .-V.. | .... .... .... |
| iPS:43 4443 | 21-225_71G3 | VH1j1-08jD6j6-19jRF1/J H4 | .... | N.... | .... H.... ..S. | .... .... .... | ..D.V .... ...Y | SSGWY- ..... .-... | .... .... .... |
| iPS:43 4475 | 21-225_74F9 | VH1j1-08jD6j6-19jRF1/J H4 | .... | N.... | .... .... ..C. | .... .... .... | .... .... ...S | SSGWN- ..... .-F.. | .... .... .... |
| iPS:43 4477 | 21-225_74A6 | VH1j1-08jD6j6-19jRF1/J H4 | .... | N.... | .... H.... ..R. | W... .... .... | .... .... ...S | SSGWY- ..... .-... | .... .... .... |
| iPS:43 4487 | 21-225_76G2 | VH1j1-08jD6j6-19jRF1/J H4 | .... | N.... | .... .... .... | .... .... .... | ...G .... .Y. | SSGWY- ..... .-M.. | .... .... .... |
| iPS:43 4511 | 21-225_74B11 | VH1j1-08jD6j6-19jRF1/J H4 | ..R. | N.... | .... H.... .... | .... .... .... | .... .... .Y. | SSGWY- ..... .-... | .... .... .... |
| iPS:43 4549 | 21-225_76E11 | VH1j1-08jD6j6-19jRF1/J H4 | .... | N.... | .... .... .... | .L.. .... .... | ...F .... ...Y | SSGWY- ..... .-... | .... .... .... |
| iPS:43 4551 | 21-225_75C4 | VH1j1-08jD6j6-19jRF1/J H4 | .... | N.... | .... H.... .... | .... .... .... | .... .... ...S | SSGWY- ..... .-... | .... .... .... |
| iPS:43 4635 | 21-225_78E6 | VH1j1-08jD6j6-19jRF1/J H4 | .... | N.... | .S.. H.... .... | .... .... .... | ...S .... ...Y | SSGWY- ..... .-... | ..S. .... .... |
| iPS:43 4649 | 21-225_78E11 | VH1j1-08jD6j6-19jRF1/J H4 | .... | N.... | .... .... ..C. | .... .... .... | .R.. .... ...S | SSGWN- ..... .-K.. | .... .... .... |
| iPS:43 4665 | 21-225_74G4 | VH1j1-08jD6j6-19jRF1/J H4 | .... | N..V. | .... H.... .... | .... .... .... | ...S .... ...S | SSGWY- ..... .-F.. | .... .... .... |
| iPS:43 4679 | 21-225_79G7 | VH1j1-08jD6j6-19jRF1/J H4 | .... | N.... | .... H.... .... | .... .... .... | ...S .... .Y. | SSGWY- ..... .-K.. | ..S. .... .... |

Figure 52 (Continued)

| | | | | | | | | | |
|---|---|---|---|---|---|---|---|---|---|
| iPS:43 4685 | 21-225_79E9 | VH1\|1-08/D6\|6-19\|RF1/J H4 | ..... | N.... | ..... | ..... | ..... | SSGWY- | ..... |
| iPS:43 4697 | 21-225_79F12 | VH1\|1-08/D6\|6-19\|RF1/J H4 | ..... | N.... | ..... | ..... | ....S | SSGWY- -.F.. | ..L.. |
| iPS:43 4729 | 21-225_80B12 | VH1\|1-08/D6\|6-19\|RF1/J H4 | ..... | N.... | ..... | ...V | ..Y.. | SSGWY- -.I.. | ..... |
| iPS:43 4851 | 21-225_75A6 | VH1\|1-08/D6\|6-19\|RF1/J H4 | ..... | N.... | ..... | ..... | ..Y.. | SSGWY- -.I.. | ..... |
| iPS:43 4909 | 21-225_85C11 | VH1\|1-08/D6\|6-19\|RF1/J H4 | ..... | N.... | S.... | ..H.. | ..Y..S | SSGWY- -.K.. | ..S.. |
| iPS:43 4959 | 21-225_87E10 | VH1\|1-08/D6\|6-19\|RF1/J H4 | ..... | N.... | ..... | ..... | ..Y.. | SSGWY- -.F.. | ..... |
| iPS:43 4965 | 21-225_88A1 | VH1\|1-08/D6\|6-19\|RF1/J H4 | ..... | ..... | ..... | ..... | S...T.SY | SSGWY- ..... | ..... |
| iPS:43 4973 | 21-225_88B4 | VH1\|1-08/D6\|6-19\|RF1/J H4 | ..... | ..... | ..... | ..D.. | ..S.. | SSGWY- ..... | ..... |
| iPS:43 4997 | 21-225_88C10 | VH1\|1-08/D6\|6-19\|RF1/J H4 | ..R.. ...S | ..... | ..... | ..T.. | ..Y.. | SSGWY- ..... | ..L.. |
| iPS:43 5053 | 21-225_75F9 | VH1\|1-08/D6\|6-19\|RF1/J H4 | ..R.. | ..... | ..... | ..H.. | ..M.... H | SSGWY- -.I.. | ..... |
| iPS:43 5113 | 21-225_92E6 | VH1\|1-08/D6\|6-19\|RF1/J H4 | ..... | ..... | ..... | ..H.. | ..Y.. | SSGWY- -.F.. | ..... |
| iPS:43 5209 | 21-225_75A10 | VH1\|1-08/D6\|6-19\|RF1/J H4 | ..... | N.... | ..... | ..... | ..Y.. | SSGWY- ..... | ..... |

Figure 52 (Continued)

| ID | Construct | | | | | | | | |
|---|---|---|---|---|---|---|---|---|---|
| iPS:43 5257 | 21-225_96H5 | VH1J1-08/D6J6-19JRF1/JH4 | .... | .... | N... | .....S..... | ....H.... | .........S....... | SSGWY-- | .S... |
| iPS:43 5267 | 21-225_96D10 | VH1J1-08/D6J6-19JRF1/JH4 | ...R | .... | N... | .... | ....H.... | .....M.......H | SSGWY-- | .-K... |
| iPS:43 5299 | 21-225_146D4 | VH1J1-08/D6J6-19JRF1/JH4 | .... | .... | N... | .... | .VH.. | .........G.... | SSGWY-- | .-F... |
| iPS:43 5305 | 21-225_146C9 | VH1J1-08/D6J6-19JRF1/JH4 | .... | .... | N... | .... | ....H.... | ....W.......A...Y | SSGWY-- | .-... |
| iPS:43 5309 | 21-225_146F9 | VH1J1-08/D6J6-19JRF1/JH4 | .... | .... | N... | .... | ....H.... | .........S....... | SSGWY-- | .-S... |
| iPS:43 5321 | 21-225_147E4 | VH1J1-08/D6J6-19JRF1/JH4 | .... | .... | N... | .... | .... | .........S....... | SSGWY-- | .-F... |
| iPS:43 5323 | 21-225_147D5 | VH1J1-08/D6J6-19JRF1/JH4 | .... | .... | N... | ....S..... | .VH.. | .....G...G....... | SSGWY-- | .-... |
| iPS:43 5345 | 21-225_148G3 | VH1J1-08/D6J6-19JRF1/JH4 | .... | .... | N... | .... | ....H....N | .........S....... | SSGWY-- | .-F... |
| iPS:43 5353 | 21-225_148F8 | VH1J1-08/D6J6-19JRF1/JH4 | .... | .... | N... | .... | .... | .........S....... | SSGWY-- | .-... |
| iPS:43 5369 | 21-225_149A2 | VH1J1-08/D6J6-19JRF1/JH4 | .... | .... | N... | .... | .VH.. | .........G....... | SSGWY-- | .-... |
| iPS:43 5373 | 21-225_149E3 | VH1J1-08/D6J6-19JRF1/JH4 | .... | .... | N... | .... | ....H.... | ....T........Y... | SSGWY-- | .-W... |
| iPS:43 5375 | 21-225_149H4 | VH1J1-08/D6J6-19JRF1/JH4 | .... | .... | N... | .... | ....H....D | .........T.V.....TF | SSGWY-- | .-... |

Figure 52 (Continued)

| | | | | | | | | |
|---|---|---|---|---|---|---|---|---|
| iPS:43 5399 | 21-225_150D2 | VH1\|1-08\|D6\|6-19\|RF1/JH4 | .......... | N......... | .......... | .......... | SSGWY- | ..... |
| iPS:43 5405 | 21-225_150B7 | VH1\|1-08\|D6\|6-19\|RF1/JH4 | ....T..FP.. | N......... | ..H....... | ....Y..... | SSGWY- .-F.... | ..... |
| iPS:43 5433 | 21-225_152E3 | VH1\|1-08\|D6\|6-19\|RF1/JH4 | .......... | N......... | ..H....... | L...S..... | SSGWY- .-F.... | ..... |
| iPS:43 5435 | 21-225_152H3 | VH1\|1-08\|D6\|6-19\|RF1/JH4 | ......P... | N......... | ..H....... | ....S..... | SSGWY- .-W.... | ..... |
| iPS:43 5459 | 21-225_152E12 | VH1\|1-08\|D6\|6-19\|RF1/JH4 | .......... | N......... | .......... | ....Y..... | SSGWY- ...... | ..... |
| iPS:43 5471 | 21-225_153F11 | VH1\|1-08\|D6\|6-19\|RF1/JH4 | ..E....... | N......... | ..H....... | N...Y..... | SSGWY- .-F..N | ..... |
| iPS:43 5475 | 21-225_154H6 | VH1\|1-08\|D6\|6-19\|RF1/JH4 | .......... | N......... | .......... | ....Y..... | SSGWY- .-I... | ..... |
| iPS:43 5481 | 21-225_154A11 | VH1\|1-08\|D6\|6-19\|RF1/JH4 | .......... | N......... | .......... | ....S..... | SSGWY- ...... | ..... |
| iPS:43 5491 | 21-225_155E5 | VH1\|1-08\|D6\|6-19\|RF1/JH4 | .......... | N......... | ..H..S..R. | ....F..... | SSGWY- .-.... | ..... |
| iPS:43 5495 | 21-225_155B6 | VH1\|1-08\|D6\|6-19\|RF1/JH4 | .......... | N......... | .......... | ....Y..... | SSGWY- .-.... | ..... |
| iPS:43 5501 | 21-225_156H1 | VH1\|1-08\|D6\|6-19\|RF1/JH4 | .......... | N......... | .VH....... | ....G....F | SSGWY- .-.... | ..... |
| iPS:43 5557 | 21-225_158B12 | VH1\|1-08\|D6\|6-19\|RF1/JH4 | .R........ | N......... | ..H....... | ....Y..... | SSGWY- .-R... | ..... |

Figure 52 (Continued)

| | | | | | | | | |
|---|---|---|---|---|---|---|---|---|
| iPS:43 5589 | 21-225_160A4 | VH1\|1-08/D6\|6-19\|RF1/J H4 | ....... | .T..... | ....N.. | .P..... | ....... | ....... | SSGWY-- |
| | | | | | | | | ....Y.. | ....... |
| iPS:43 5623 | 21-225_162D5 | VH1\|1-08/D6\|6-19\|RF1/J H4 | ....... | ...S... | ....N.. | ....... | ....H.. | ....S.. | SSGWY-- |
| | | | | | | | | ...D... | .-I.... |
| iPS:43 5627 | 21-225_162F6 | VH1\|1-08/D6\|6-19\|RF1/J H4 | ..R.... | ....... | ....N.. | ....... | ....H.. | .F..F.. | SSGWY-- |
| | | | | | | | | ....... | .-F.... |
| iPS:43 5649 | 21-225_165H2 | VH1\|1-08/D6\|6-19\|RF1/J H4 | ....... | ....... | ....H.. | ...V... | ..HK... | .F..... | SSGWY-- |
| | | | | | | | | ....Y.. | .-R.... |
| iPS:43 5727 | 21-225_172E11 | VH1\|1-08/D6\|6-19\|RF1/J H4 | ....... | ....M.. | ....N.. | ....... | ....H.. | ...N... | SSGWY-- |
| | | | | | | | | ....Y.. | .-M.... |
| iPS:43 5751 | 21-225_175D10 | VH1\|1-08/D6\|6-19\|RF1/J H4 | ....... | ....... | ....N.L | ....... | ....H.. | ...V... | SSGWY-- |
| | | | | | | | | ....Y.. | .-R.... |
| iPS:43 5773 | 21-225_177B12 | VH1\|1-08/D6\|6-19\|RF1/J H4 | ....... | ....... | ....N.. | ....... | ....H.. | ....... | SSGWY-- |
| | | | | | | | | ....Y.. | .....F. |
| iPS:43 5801 | 21-225_181E5 | VH1\|1-08/D6\|6-19\|RF1/J H4 | ....... | ....... | ....N.. | ....... | ....H.. | ....... | SSGWY-- |
| | | | | | | | | ....S.. | .-I.... |
| iPS:43 5841 | 21-225_191D8 | VH1\|1-08/D6\|6-19\|RF1/J H4 | ....... | ....... | ....N.. | ....... | ..R.... | ....... | SSGWY-- |
| | | | | | | | | ....H.. | ....... |
| iPS:43 5855 | 21-225_191G3 | VH1\|1-08/D6\|6-19\|RF1/J H4 | ....... | ....... | ....N.. | ....... | ....... | ....... | SSGWY-- |
| | | | | | | | | ....H.. | .-I.... |
| iPS:43 5915 | 21-225_190H4 | VH1\|1-08/D6\|6-19\|RF1/J H4 | ....... | ....... | ....N.. | ....... | ....... | ....... | SSGWY-- |
| | | | | | | | | ....H.. | .-I.... |
| iPS:43 5925 | 21-225_190D7 | VH1\|1-08/D6\|6-19\|RF1/J H4 | ....... | ...N... | ....N.. | ....... | ....... | ....... | SSGWY-- |
| | | | | | | | | ....S.. | .-F.... |

Figure 52 (Continued)

| | | | | | | | | |
|---|---|---|---|---|---|---|---|---|
| iPS:43 6021 | 21-225_193G4 | VH1|1-08/D6|6-19|RF1/J H4 | . . . . . . . . . . . . | N . . . . . . . . . . | . . . . . . . . . . | . . . . . . . . . . | . R . . . . . . . . S | SSGWY— .-F... |
| iPS:43 6150 | 21-225_197H4 | VH1|1-08/D6|6-19|RF1/J H4 | . . . . . . . . . . . . | N . . . . . . . . . . | . H . . . . | . . . . . . . . . . | . . . . . . . . H | SSGWY— .-... |
| iPS:43 6154 | 21-225_197C6 | VH1|1-08/D6|6-19|RF1/J H4 | . . . . . . . . . . . . | N . . . . . . . . . . | . H . . . . | . . . . . . . . . . | . . . . . . . . H | SSGWY— .-... |
| iPS:43 6272 | 21-225_201F5 | VH1|1-08/D6|6-19|RF1/J H4 | . . . . . . . A . . . | N . . . . . . . . . . | . H . . . . | . . . . . . . . . . | . . . . . . . . Y | SSGWY— .-... |
| iPS:43 6550 | 21-225_224D8 | VH1|1-08/D6|6-19|RF1/J H4 | . . . . . . . . . . . . | N . . . . . . . . . . | LY. . . . . | . . . . . . . . . . | . . . . . . . . Y | SSGWY— .-... |
| iPS:43 6554 | 21-225_224C10 | VH1|1-08/D6|6-19|RF1/J H4 | . . . . . . . S . . . | N . . . . . . . . . . | . . . . . . | . . . . . . . . . . | . . . . . . . . Y | SSGWY— .-K... |
| iPS:43 6560 | 21-225_224F11 | VH1|1-08/D6|6-19|RF1/J H4 | . R . . . . . H . . | N . . . . . . . . . . | . H . . F . | . R . . . . . . . . | . . . . . . . . Y | SSGWY— .-K... |
| iPS:43 6574 | 21-225_225F5 | VH1|1-08/D6|6-19|RF1/J H4 | . R . . . . . . . . | N . . . . . . . . . . | . . . . . . | . . . . . . . . . . | . N . . . . . . Y | SSGWT— .-R... |
| iPS:43 6584 | 21-225_225B9 | VH1|1-08/D6|6-19|RF1/J H4 | . . . . . . . . . . . . | N . . . . . . . . . . | . H . . . . .R. | . . . . . . . . . . | . N . . . . . . Y | SSGWY— .-R... |
| iPS:43 6586 | 21-225_225F11 | VH1|1-08/D6|6-19|RF1/J H4 | . . . . . . . . . . . . | H . . . . . . . . . . | . H . . . . | . . . . . . . . . . | . . . A . . . . Y | SSGWY— .-L... |
| iPS:43 6588 | 21-225_225F12 | VH1|1-08/D6|6-19|RF1/J H4 | . . . . . . . . . . . . | N . . . . . . . . . . | . H . . . . | . . . . . . . . . . | . . . . . . . . Y | SSGWY— .-R... |
| iPS:43 6590 | 21-225_225H12 | VH1|1-08/D6|6-19|RF1/J H4 | . . . . . . . . . . . . | N . . . . . . . . . . | . H . . . . | . . . . . . . . . . | . . . . . . . . Y | SSGWY— .-K... |

Figure 52 (Continued)

| ID | Clone | V(D)J | | | | | | | |
|---|---|---|---|---|---|---|---|---|---|
| iPS:43 6598 | 21-225_226D6 | VH1\|1-08/D6\|6-19\|RF1/JH4 | ......... | N........ | ......... | .H...... | ......... | .......Y | SSGWY-- .-K... |
| iPS:43 6600 | 21-225_226F6 | VH1\|1-08/D6\|6-19\|RF1/JH4 | ......... | N........ | ......... | .H...... | ......N. | .......Y | SSGWY-- .-R... |
| iPS:43 6616 | 21-225_226D11 | VH1\|1-08/D6\|6-19\|RF1/JH4 | .....S... | N........ | ......... | .H...... | ......... | .......Y | SSGWY-- .-..... |
| iPS:43 6622 | 21-225_226A12 | VH1\|1-08/D6\|6-19\|RF1/JH4 | ......... | N........ | ......... | .H...... | ......... | .......Y | SSGWY-- .-..... |
| iPS:43 6636 | 21-225_227E6 | VH1\|1-08/D6\|6-19\|RF1/JH4 | ......... | N........ | ......... | .H...... | ......... | .......Y | SSGWY-- .-K... |
| iPS:43 6638 | 21-225_227C7 | VH1\|1-08/D6\|6-19\|RF1/JH4 | ...R..H.. | N........ | ......... | .H...... | ......... | .......Y | SSGWY-- .-R... |
| iPS:43 6646 | 21-225_227D11 | VH1\|1-08/D6\|6-19\|RF1/JH4 | ......... | N........ | ......... | .H...... | ......... | .......Y | SSGWY-- .-..... |
| iPS:44 6086 | 21-225_94D8 | VH1\|1-08/D6\|6-19\|RF1/JH4 | ...T..... | N........ | ......... | ...V.... | ......... | .......V Y | SSGWY-- .-I... |
| iPS:45 1116 | 21-225_164A4 | VH1\|1-08/D6\|6-19\|RF1/JH4 | ...F..P.. | N........ | ......... | .H...... | ...M..... | .......S | SSGWY-- .-..... |
| iPS:45 1124 | 21-225_74F6 | VH1\|1-08/D6\|6-19\|RF1/JH4 | ...R..... | N........ | ......... | .H...... | ...T..S. | .......S H | SSGWY-- .-F... |
| iPS:45 1127 | 21-225_164A7 | VH1\|1-08/D6\|6-19\|RF1/JH4 | ......... | N.....V.. | ......... | .H...... | ......N. | .......H | SSGWY-- .-L... |
| iPS:45 1131 | 21-225_160A7 | VH1\|1-08/D6\|6-19\|RF1/JH4 | ......... | N........ | ......... | .H.H.... | ......... | .......H | SSGWY-- .-..... |

Figure 52 (Continued)

| | | | | | | | |
|---|---|---|---|---|---|---|---|
| iPS:39 2786 | 21-225_24E1 | VH1\|1-08\|D6\|6-19\|RF1/J H4 | ... | ... | ... H ... | ... ... ... | SSGWE- ...-V... |
| iPS:39 2886 | 21-225_23A12 | VH1\|1-08\|D6\|6-19\|RF1/J H4 | ......P... | N....... | ......R.... | ...N... ... | SSGWY- ...-... |
| iPS:39 2928 | 21-225_25A4 | VH1\|1-08\|D6\|6-19\|RF1/J H4 | ...L... ....R... | N....... | ...Y.... | ... ... | SSGWY- ...-... |
| iPS:39 2936 | 21-225_28B6 | VH1\|1-08\|D6\|6-19\|RF1/J H4 | ...L... ....R... | N....... | ...H.D... | ...S... ... | SSGWY- ...-... |
| iPS:39 2960 | 21-225_29E6 | VH1\|1-08\|D6\|6-19\|RF1/J H4 | ...L... ....R... | N....... | ...H.... | ...N...S ... | SSGWY- ...-... |
| iPS:39 2992 | 21-225_26C4 | VH1\|1-08\|D6\|6-19\|RF1/J H4 | ......... | N....... | ......R.... | ...S... ... | SSGWY- ...-F... |
| iPS:39 3088 | 21-225_33D1 | VH1\|1-08\|D6\|6-19\|RF1/J H4 | ......... | N....... | ...H...F .T.F. ....R. | ...L...S ... | SSGWY- ...-... |
| iPS:39 3144 | 21-225_34D2 | VH1\|1-08\|D6\|6-19\|RF1/J H4 | ......... | N....... | ...V... ...R. | ...A...S ... | SSGWY- ...-F... |
| iPS:39 3368 | 21-225_29H8 | VH1\|1-08\|D6\|6-19\|RF1/J H4 | ...Q... ... | N....... | ...A... ....R. | ... ... | SSGWY- ...-... |
| iPS:39 3942 | 21-225_11E5 | VH1\|1-08\|D6\|6-19\|RF1/J H4 | ...P... ... | N....... | ...H.A... | ...T... ... | SSGWE- ...-V... |
| iPS:39 4085 | 21-225_8B11 | VH1\|1-08\|D6\|6-19\|RF1/J H4 | ......... | N....... | ...H.... | ...R...Y ... | SSGWY- ...-F... |
| iPS:39 8496 | 21-225_22D2 | VH1\|1-08\|D6\|6-19\|RF1/J H4 | ......I | N....... | ...H.D... | ...Y... ... | SSGWY- ...-... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 8522 | 21-225_32A1 | VH1\|1-08/D6\|6-19\|RF1/JH4 | . . . . . . . . . . . . . . . . . . . . . . . . . . . . . . | N . . . . . . . . | . . . . . . . . . . . . . . . . . . . . . | . . . . . . . . . | . . . . . . . . . . . . . . . . . . . . . . . . S | SSGWY- . . . . . -F . . . | . . . . . . . . |
| iPS:39 8524 | 21-225_32A5 | VH1\|1-08/D6\|6-19\|RF1/JH4 | . . . . . . . . . . . . . . . . . . . . . . . . . . . . . . | N . . . . . . . . | . . . . . . . . . . . . . . . . . . . . . | H . . . . . . F . . R . | . . . . . . . . . . . . . . . . . . . . . . SS | SSGWY- . . . . . -F . . . | . . . . . . . . |
| iPS:39 8538 | 21-225_34H7 | VH1\|1-08/D6\|6-19\|RF1/JH4 | . . . . . . . . . . . . . . . . . . . . . . . . . . . . . . | N . . . . . . . . | . . . . . . . . . . . . . . . . . . . . . | . . . . . . . . . | N . . . . . . . . . . . . . . . . . . . . . . . S | SSGWY- . . . . . -F . . . | . . . . . . . . |
| | Germline | | H_FR1 | H_CDR1 | H_FR2 | H_CDR2 | H_FR3 | H_CDR3 | H_FR4 |
| | VH1\|1-02/D1\|1-1\|RF1/JH4 | QVQLQES GGGLVKPGGSVK VSCEASG-YTFT | -YYMH | WVRQAPGQ WLEWMG GLEWMG | SGGTNYAQ SGGTNYAQ KFQG | RVTMTRDTSISTAYMEL SRLRSEDTAVYYCAR | SFTGT YFDY | WGQGTL VTVSS |
| iPS:47 3253 | 21-225_7C3_LC_1 | VH1\|1-02/D1\|1-1\|RF1/JH4 | . . . . . . . . . . . . . . . . . . . . . . . . . N | D . . . . . . L . | . . . . . . . . . . . . . . . . . . . . . | . . . . . . . . H | . . . . . . . . . . . . . . . . . . . . . . . S . | DG.S- . . . S . . . | . . . . . . . . |
| iPS:47 3254 | 21-225_7C3_LC_2 | VH1\|1-02/D1\|1-1\|RF1/JH4 | . . . . . . . . . . . . . . . . . . . . . . . . . N | D . . . . . . L . | . . . . . . . . . . . . . . . . . . . . . | . . . . . . . . H | . . . . . . . . . . . . . . . . . . . . . . . S . | DG.S- . . . S . . . | . . . . . . . . |
| iPS:47 3255 | 21-225_9F12_L_C1 | VH1\|1-02/D1\|1-1\|RF1/JH4 | . . . . . . . . . . . . . . . . . . . . . . . . . A | D . . . . . . L . | . . . . . . . . . . . . . . . . . . . . . | . . . . . . . . H . . . . . . . F . | . . . . . . . . . . . . . . . . . . . F . . . L . | DG.S- . . . S . . . | . . . . . . . . |
| iPS:47 3256 | 21-225_9F12_L_C2 | VH1\|1-02/D1\|1-1\|RF1/JH4 | . . . . . . . . . . . . . . . . . . . . . . . . . A | D . . . . . . L . | . . . . . . . . . . . . . . . . . . . . . | . . . . . . . . H . . . . . . . F . | . . . . . . . . . . . . . . . . . . . F . . . L . | DG.S- . . . S . . . | . . . . . . . . |
| iPS:42 6108 | 21-225_10G6 | VH1\|1-02/D1\|1-1\|RF1/JH4 | . . . . . . . . . . . . . . . . . . . . . . . . . . | A . . . . . . H . | . . . . . . . . . . . . . . . . . . . . . | NN . . . . . . . | . . . . . . . . . . . . . . . . . . . . . . G . . | DV.S- . . . S . . . | . . . . . . . . |
| iPS:42 6110 | 21-225_12E9 | VH1\|1-02/D1\|1-1\|RF1/JH4 | . . . . . . . . . . . . . . . . . . . . . . . . . . | D . . . . . . L . | . . . . . . . . . . . . . . . . . . . . . | VH . . . . . F . . . . D | . . . . . . . . . . . . . . . . . . . S . I.S . | DG.S- . . . S . . . | . . . . . . . . |
| iPS:45 3451 | 21-225_52G11 | VH1\|1-02/D1\|1-1\|RF1/JH4 | . . . . . . . . . . . . . . . . . . . . . . . . . . | . . . . . . . . . | . . . . . . . . . . . . . . . . . . . . . | . . . . . . . . . RN . . . . . . | . . . . . . . . . . . . . . . . . . . . . . . F . | DG.S- . . . S . . . | . . . . . . . . |

Figure 52 (Continued)

| | | | | | | | | |
|---|---|---|---|---|---|---|---|---|
| iPS:45 3453 | 21-225_53F2 | VH1\|1-02/D1\|1-1\|RF1/JH4 | .... | L.. | .... | RN.... N.... | ...K..... | DG.S— ...S... |
| iPS:43 4035 | 21-225_49F10 | VH1\|1-02/D1\|1-1\|RF1/JH4 | .... | H.. | .... | NNA.... N... | ...L..... | DG.S— ...S..F |
| iPS:43 4065 | 21-225_50D4 | VH1\|1-02/D1\|1-1\|RF1/JH4 | .... | H.. | .... | NNA.... S... | ...L..... | DG.S— ...S..F |
| iPS:43 4069 | 21-225_51E9 | VH1\|1-02/D1\|1-1\|RF1/JH4 | ..R. | HI. | .... | TN..Q... .... | ......... | DG.S— ...S... |
| iPS:43 4079 | 21-225_52B1 | VH1\|1-02/D1\|1-1\|RF1/JH4 | .... | H.Q | .... | ..A.... N... | .......LD. | DG.S— ...S... |
| iPS:43 4097 | 21-225_52H10 | VH1\|1-02/D1\|1-1\|RF1/JH4 | .... | H.Q | .... | ...N..Q .... | ......... | DG.S— ...S... |
| iPS:43 4123 | 21-225_53F7 | VH1\|1-02/D1\|1-1\|RF1/JH4 | .... | H.. | .... | NN.... .... | ..N.T.... | DG.S— ...S... |
| iPS:43 4189 | 21-225_56E5 | VH1\|1-02/D1\|1-1\|RF1/JH4 | ....Q | H.. | .... | NNA.... .... | ...R..... | DG.S— ...S... |
| iPS:43 5677 | 21-225_169C10 | VH1\|1-02/D1\|1-1\|RF1/JH4 | ....R | F.. | .... | ..K.K... R... | ...N..... | G.TVAT.. .....WGV. |
| iPS:43 5699 | 21-225_170D6 | VH1\|1-02/D1\|1-1\|RF1/JH4 | ....R | FI. | .... | ..K.... R... | ...N..... | G.TVAT.. .....WGV. |
| iPS:43 5797 | 21-225_181G2 | VH1\|1-02/D1\|1-1\|RF1/JH4 | ..T.. | .N. | V... | N.S.T .... | ......... | KF——— ....--GD |
| iPS:43 5877 | 21-225_184E7 | VH1\|1-02/D1\|1-1\|RF1/JH4 | ..T.. | .N. | V... | N.S.T .... | ......... | KF——— ....--GD |

Figure 52 (Continued)

| | | | | | | | | |
|---|---|---|---|---|---|---|---|---|
| iPS:43 5885 | 21-225_185E10 | VH1J1-02/D1J1-1JRF1/JH4 | ......T... | S......N.. | ....V... | N.S.T... | ........ | KF------...----GD | ... |
| iPS:43 5891 | 21-225_188H5 | VH1J1-02/D1J1-1JRF1/JH4 | ......T... | S......N.. | ....V... | ...S.T... | ....I... | KF------...----GD | ... |
| iPS:43 5897 | 21-225_188B9 | VH1J1-02/D1J1-1JRF1/JH4 | ......T... | S......N.. | ....V... | ...S.T... | ........ | KF------...----GD | ... |
| iPS:43 6400 | 21-225_213H7 | VH1J1-02/D1J1-1JRF1/JH4 | ........ | ......H.. | ........ | ..D.K... | ........ | EKP.S......YK. | ... |
| iPS:43 6488 | 21-225_221A6 | VH1J1-02/D1J1-1JRF1/JH4 | ......T... | ........ | ........ | .H...... | ...L..D. | DG.S-......S... | ... |
| iPS:43 6496 | 21-225_222E1 | VH1J1-02/D1J1-1JRF1/JH4 | ......T... | ........ | ........ | .H...... | ...L..D. | DG.S-......S... | ... |
| iPS:43 6508 | 21-225_222F7 | VH1J1-02/D1J1-1JRF1/JH4 | ......T... | ........ | ........ | .H...... | ...L..D. | DG.S-......S... | ... |
| iPS:43 6516 | 21-225_222C12 | VH1J1-02/D1J1-1JRF1/JH4 | ......T... | ........ | ........ | .H...... | ...L..D. | DG.S-......S... | ... |
| iPS:43 7264 | 21-225_171H12 | VH1J1-02/D1J1-1JRF1/JH4 | ......R... | ...F.... | ........ | .K.K...S..R. | ...N.... | G.TVAT.......WGV.... | ... |
| iPS:43 7266 | 21-225_177A5 | VH1J1-02/D1J1-1JRF1/JH4 | ......R... | ...F.... | ........ | .K.K...S..R. | ...NW... | G.TVAT.......WGV.... | ... |
| iPS:39 3080 | 21-225_34F3 | VH1J1-02/D1J1-1JRF1/JH4 | ........ | ...H.... | ..D..... | ........ | ........ | DG.S-......S... | ... |
| iPS:39 3084 | 21-225_35C6 | VH1J1-02/D1J1-1JRF1/JH4 | ......T... | ..D..... | ........ | .S.K...N... | ...N.... | DG..-......S... | ... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| Germline | | | | | | | | |
| iPS:39 3086 | 21-225_36H5 | VH1|1-02/D1|1-1|RF1/JH4 | M... | D......H... | ...... | R.... ...D | ...... ...F.. | DG..- ...S... | ...... |
| iPS:39 3098 | 21-225_35G6 | VH1|1-02/D1|1-1|RF1/JH4 | ....D | D......HI. | ...... | N...H... E... | ...S...... | DG..- ...S... | ...... |
| iPS:39 3112 | 21-225_33G1 | VH1|1-02/D1|1-1|RF1/JH4 | ..A.. | .......... | ...... | ..S...... | ...... | DG..- ...S... | ...... |
| iPS:39 3116 | 21-225_34G7 | VH1|1-02/D1|1-1|RF1/JH4 | ....R | D......HI. | ...... | N...H... | ...... | DG..- ...S... | ...... |
| iPS:39 3132 | 21-225_33H7 | VH1|1-02/D1|1-1|RF1/JH4 | ....D | D......HI. | ...... | N...H... E... | ..S...... | DG..- ...S... | N..... |
| iPS:39 3140 | 21-225_35H12 | VH1|1-02/D1|1-1|RF1/JH4 | ...... | D......I.. | ...... | R.... | ...... | DG..- ...S... | ...... |
| iPS:39 3954 | 21-225_4H6 | VH1|1-02/D1|1-1|RF1/JH4 | ...... | D......L.. | ...... | ..H... | ..S...G.. | DG.S- ...S... | ...... |
| iPS:39 8484 | 21-225_18D4 | VH1|1-02/D1|1-1|RF1/JH4 | ...... | .......L.. | ..L... | .N..IS.. | ...I...... | DG.S- ...SL.. | ...... |
| iPS:39 8502 | 21-225_23B11 | VH1|1-02/D1|1-1|RF1/JH4 | ...... | .......L.. | ...... | NN.... | ...... | DG.S- ...S... | ...... |
| iPS:39 8520 | 21-225_31C4 | VH1|1-02/D1|1-1|RF1/JH4 | ..T... | ....D... | ...... | ..S.K... N... | ...N...V. | DG..- ...S... | ...... |
| iPS:40 2223 | 21-225_30A11 | VH1|1-02/D1|1-1|RF1/JH4 | ...... | D......H.. | ...... | R.... ...D | ...... ...F.. | DG..- ...S... | ...... |

Figure 52 (Continued)

| VH3|3-33|D6|6-6|RF1|JH6 | | LQLKS TGGVQPGRSLR LSCAASGFTFS | SYAM NWVRQAPGKG LEWVS | AIGTGGGTYYA DSVKG | RFTISRDNSKNTLYLQM NSLRAEDTAVYYCAR | ETVSSSYY YYGMDV | WGQGTT VTVSS |
|---|---|---|---|---|---|---|---|---|
| iPS:42 6114 | 21-225_28H2 | VH3|3-33|D6|6-6|RF1|JH6 | .......... | N......V.. | .......... | .......... | .EY.GW-.....D. | ........ |
| iPS:42 6116 | 21-225_29E2 | VH3|3-33|D6|6-6|RF1|JH6 | .......... | N.....CV.. | .......... | ......V... | .EY.GW-.....D. | ........ |
| iPS:46 8812 | 21-225_48H4 | VH3|3-33|D6|6-6|RF1|JH6 | .......... | D.....SL.. | ........T | ......I... | .NY.GW-.....G. | ........ |
| iPS:46 8816 | 21-225_52G8 | VH3|3-33|D6|6-6|RF1|JH6 | .......... | .......... | .......... | ......L... | R....W--...- SG... | ........ |
| iPS:46 8826 | 21-225_201C5 | VH3|3-33|D6|6-6|RF1|JH6 | .......... | D......V.. | ........V | ......R... | .RY.GL-.....D. | ........ |
| iPS:46 8842 | 21-225_50H4 | VH3|3-33|D6|6-6|RF1|JH6 | .......... | .......V.. | .......... | ......D... | .LY.NW-....... | ........ |
| iPS:46 8858 | 21-225_148C9 | VH3|3-33|D6|6-6|RF1|JH6 | A......... | D.......... | A......... | ......L... | .RY.GW-.....D. ..L.. | ........ |
| iPS:46 8860 | 21-225_224E7 | VH3|3-33|D6|6-6|RF1|JH6 | .......S.. | .......V.. | .......... | ......L... | .QY..W--.....DF ..L.. | ........ |
| iPS:43 3917 | 21-225_43E11 | VH3|3-33|D6|6-6|RF1|JH6 | .......... | D.......... | .......... | .......... | R.VR.W--...- VG... | ........ |
| iPS:43 3919 | 21-225_44B3 | VH3|3-33|D6|6-6|RF1|JH6 | ......T... | .......... | .......... | .......... | .RY.GW-.....D. | ........ |
| iPS:43 3923 | 21-225_44D3 | VH3|3-33|D6|6-6|RF1|JH6 | .......... | .......V.. | .......... | .......... | .RY.GL-.....D. | ........ |

Figure 52 (Continued)

| | | | | | | | |
|---|---|---|---|---|---|---|---|
| iPS:43 3929 | 21-225_44D5 | VH3j3-33/D6j6-6jRF1/JH6 | . . . | . . . V . | . . . | . . . | VPY . . . W- . . . . . . . . . . . . | . D . . . . . . . . . . . . . |
| iPS:43 3935 | 21-225_44F9 | VH3j3-33/D6j6-6jRF1/JH6 | . . . | . . . V . | . . . | . . . | . PY . . . W- . . . . . . . . . . . | . D . . . . . . . . . . . . . G . . |
| iPS:43 3937 | 21-225_44B10 | VH3j3-33/D6j6-6jRF1/JH6 | . . . V | . . . . . | . . . | . . . | R . . . . . W- . . . . . . . . . . . | . . . . . . . . . . . . . . . |
| iPS:43 3939 | 21-225_44C10 | VH3j3-33/D6j6-6jRF1/JH6 | . . . | D . . . . CV . | . . . | . . . | VG . . . . . . . . . . | . D . . . . . . . . . . . . . |
| iPS:43 3951 | 21-225_45B4 | VH3j3-33/D6j6-6jRF1/JH6 | . . . | D . . . . CV . | . . . | . . . | RY . . GL- . . . . . . . . . . | . D . . . . . . . . . . . . . |
| iPS:43 3955 | 21-225_45B8 | VH3j3-33/D6j6-6jRF1/JH6 | . . . | . . . V . | . . . | . . . | RY . . GL- . . . . . . . . . . | . D . . . . . . . . . . . . . |
| iPS:43 3967 | 21-225_46C3 | VH3j3-33/D6j6-6jRF1/JH6 | . . . | . . . V . | . . . | . . . | RY . . GL- . . . . . . . . . . | . D . . . . . . . . . . . . . |
| iPS:43 3971 | 21-225_46D4 | VH3j3-33/D6j6-6jRF1/JH6 | . . . | . . . . . | . . . | . . . | VPY . . . W- . . . . . . . . . . . | . D . . . . . . . . . . . . . |
| iPS:43 3979 | 21-225_46B9 | VH3j3-33/D6j6-6jRF1/JH6 | . . . S | D . . . . . | . R . | T . . . | R . . . . . W- . . . . . . MG . . . . . | . . . . . . . . . . . . . . . |
| iPS:43 3985 | 21-225_47C1 | VH3j3-33/D6j6-6jRF1/JH6 | . . . | D . . . . . | . . . | . . . F . | R . R . W- . . . . . . . . . . . | . D . . . . . . . . . . . . . |
| iPS:43 3991 | 21-225_47E7 | VH3j3-33/D6j6-6jRF1/JH6 | . . . | I . . . . . | . . . | . . . | R . R . W- . . . . . . VG . . . . . | . . . . . . . . . . . . . . . |
| iPS:43 4001 | 21-225_48F2 | VH3j3-33/D6j6-6jRF1/JH6 | . . . | N . . . V . | . . . | . . . | RY . . . W- . . . . . . . L . . | . D . . . . . . . . . . . . . |

Figure 52 (Continued)

| | | | | | | | |
|---|---|---|---|---|---|---|---|
| iPS:43 4021 | 21-225_49C1 | VH3\|3-33/D6\|6-6\|RF1/JH 6 | . . . . . . . . . . T . . . | . . . . . . . . . . . . . . . | . . . . . . . . . . . . . . . | . . . . . . . . . . . . . . . | R . . . . W . . . . . . . . . SG . . . . . |
| iPS:43 4025 | 21-225_49G3 | VH3\|3-33/D6\|6-6\|RF1/JH 6 | . . . . . . . . . . . . . . . | . . . . . . . . . . . . . . . | . . . . . . . . . . . . . . . | . . . . . . . . . . . . . . . | R . . . . W . . . . . . . . . SG . . . . . |
| iPS:43 4031 | 21-225_49E7 | VH3\|3-33/D6\|6-6\|RF1/JH 6 | . . . . . . . . . . . . . . . | . . . . . . . . . . . . . . . | . . . . . . . . . . . . . . . | . . . . L . . . . . . . . . . | R . . . . W . . . . . . . . . SG . . . . . |
| iPS:43 4033 | 21-225_49F9 | VH3\|3-33/D6\|6-6\|RF1/JH 6 | . . . . . . . . . . . . . . . | . . . . . L . . . . . . . . . .R . . . | . . . . . . . . . . . . . . . | . . . . P . . . . . . H . . . | R . . . . W . . . . . . . . . SG . . . . . |
| iPS:43 4053 | 21-225_51E1 | VH3\|3-33/D6\|6-6\|RF1/JH 6 | . . . . . . . . . . . . . . . | . . . . . . . . . . . . . . . S . . . | . . . . . . . . . . . . . . . | . . . . . . . . . . . . . . . | R . . . . W . . . . . . . . . SG . . . . . |
| iPS:43 4093 | 21-225_52D10 | VH3\|3-33/D6\|6-6\|RF1/JH 6 | . . . . . . . . . . . . . . . | . . . . . L . . . . . . . H . . | . . . . . . . . . . . . . . . | . . . . . . . . . . . . . . . | R . . . . W . . . . . . . . . SG . . . . . |
| iPS:43 4137 | 21-225_54D4 | VH3\|3-33/D6\|6-6\|RF1/JH 6 | . . . . . . . . . . . . . . . | . . . . . . . . . . . . . . . | . . . . . . . . . . . . . . . | . . . . . . . . . . . . . . . | R . . . . W . . . . . . . . . SG . . . . . |
| iPS:43 4149 | 21-225_55H1 | VH3\|3-33/D6\|6-6\|RF1/JH 5 | . . . . . . . . . . . . . . . | . . . . . L . . . . . . . H . . | . . . . . . . . . . . . . . . | . . . . . . . . . . . . . . . | R . . . . W . . . . . . . . . SG . . . . . |
| iPS:43 4151 | 21-225_55C2 | VH3\|3-33/D6\|6-6\|RF1/JH 6 | . . . . . . . . . . . . . . . | . . . . . . . NG . . . . . . . | . . . . . . . . . . . . . . . | . . . . . . . . . . . . . . . | R . . . . W . . . . . . . . . SG . . . . . |
| iPS:43 4161 | 21-225_55F9 | VH3\|3-33/D6\|6-6\|RF1/JH 6 | . . . . . . . . . . . . . . . | . . . . . . . . . . . . . . . | . . . . . . . . . . . . . . . | . . . . . . . . . . . . . . . | R . . . . W . . . . . . . . . SG . . . . . |
| iPS:43 4201 | 21-225_59A12 | VH3\|3-33/D6\|6-6\|RF1/JH 6 | . . . . . . . . . . . . . . . | . . . . . . . . . . . . . . . | . . . . . . . . . . . . . . . | . . . . . . . . . . . . . . . | R . . . . W . . . . . . . . . DG . . . . . |
| iPS:43 4205 | 21-225_60G2 | VH3\|3-33/D6\|6-6\|RF1/JH 6 | . . . . . . . . . . . . . . . | . . . . . . . . . . . . . . . | . . . . . . . . . . . . . . . | . . . . . . . . . . . . . . . | R . . R . W . . . . . . . . . TG . . . . . |

Figure 52 (Continued)

| | | | | | | | | |
|---|---|---|---|---|---|---|---|---|
| iPS:43 4223 | 21-225_60C12 | VH3j3-33/D6j6-6jRF1/JH6 | . . . | . . . | . . . | . . . | . . . | R..R.W--- |
| iPS:43 4231 | 21-225_61F2 | VH3j3-33/D6j6-6jRF1/JH6 | . . . | . . . | ...V. | . . . | . . . | TG.....................D. |
| iPS:43 4233 | 21-225_61B3 | VH3j3-33/D6j6-6jRF1/JH6 | . . . | . . . | . . . | . . . | . . . | .RY..GW--- |
| iPS:43 4303 | 21-225_58H11 | VH3j3-33/D6j6-6jRF1/JH6 | . . . | . . . | ...H. | . . . | . . . | R..R.W--- AG..... |
| iPS:43 4339 | 21-225_64A4 | VH3j3-33/D6j6-6jRF1/JH6 | . . . | D....V. | . . . | . . . Q | . . . | R...W--- DG..... |
| iPS:43 4343 | 21-225_64C8 | VH3j3-33/D6j6-6jRF1/JH6 | . . . | D....V. | ...M. | . . . | . . . | .RY...W---.................D. |
| iPS:43 4387 | 21-225_66D11 | VH3j3-33/D6j6-6jRF1/JH6 | . . . | N....V. | . . . | . . . | . . . | .RY..GW--- |
| iPS:43 4469 | 21-225_73C9 | VH3j3-33/D6j6-6jRF1/JH6 | . . . | N...DI. | . . . | . . . S | . . . | MY..NW---...L. |
| iPS:43 5197 | 21-225_94F3 | VH3j3-33/D6j6-6jRF1/JH6 | . . . | D.... | . . . | . . . F.. | . . . I | .RY...W---.................FD. |
| iPS:43 5315 | 21-225_147B2 | VH3j3-33/D6j6-6jRF1/JH6 | . . . | . . . | . . . | . . . | . . . | .KY..GW---.................D. |
| iPS:43 5325 | 21-225_147H5 | VH3j3-33/D6j6-6jRF1/JH6 | ...A. | . . . | . . . | ...L...S | . . . | R....W--- SG..... |
| iPS:43 5329 | 21-225_147A8 | VH3j3-33/D6j6-6jRF1/JH6 | . . . | . . . | . . . | . . . | . . . | .RY..GW---...L. |
| | | | | | | | | R....W--- TG..... |

Figure 52 (Continued)

| ID | | | | | | | | | |
|---|---|---|---|---|---|---|---|---|---|
| iPS:43 5349 | 21-225_148F5 | VH3J3-33/D6J6-6JRF1/JH6 | . . . | . . . | . . . | . . . | . . . | R....W--- | . . . |
| iPS:43 5359 | 21-225_148H10 | VH3J3-33/D6J6-6JRF1/JH6 | . . . | . . . | . . . | . . . | . . . | R....W---  SG.... | . . . |
| iPS:43 5393 | 21-225_149D10 | VH3J3-33/D6J6-6JRF1/JH6 | . . A . . | D..... | . . . | . . L . | . . . | .RY..GW- .......D | . . . |
| iPS:43 5401 | 21-225_150E2 | VH3J3-33/D6J6-6JRF1/JH6 | . . . | . . . V | . . . | . . . | . . . | .EY...W-  .......G | . . . |
| iPS:43 5417 | 21-225_150D11 | VH3J3-33/D6J6-6JRF1/JH6 | . . . | . . . | . F . H . | . . . T | . . . | RF....W---  SG.... | . . . |
| iPS:43 5445 | 21-225_152F7 | VH3J3-33/D6J6-6JRF1/JH6 | . . . | . . . I | . . . | . . . | . . . | .EY...W- | . . . |
| iPS:43 5469 | 21-225_153G9 | VH3J3-33/D6J6-6JRF1/JH6 | . . . | . . . | L.F . . | . . . I . F | . C . | R..R.W---  AG..... | . . A |
| iPS:43 5573 | 21-225_159D8 | VH3J3-33/D6J6-6JRF1/JH6 | . . . | N......V | . . . | . . . L | . . . | .PY..GW- .......D | . . . |
| iPS:43 5681 | 21-225_169D11 | VH3J3-33/D6J6-6JRF1/JH6 | . . . | D......V | . . . | . . . | . . . | .RY..GW- .......D | . . . |
| iPS:43 5689 | 21-225_170F3 | VH3J3-33/D6J6-6JRF1/JH6 | ..S.. | D......V | . . E . | . . . | . . . | .TY...W- | . . . |
| iPS:43 5733 | 21-225_173C11 | VH3J3-33/D6J6-6JRF1/JH6 | . . . | . . . I | L.F . . | . . S . . H . | . . . | R....W---  SG.... | . . . |
| iPS:43 5741 | 21-225_174G10 | VH3J3-33/D6J6-6JRF1/JH6 | . . . | D......V | . . . | . . L | . . . | .RY..GW- .......D | . . . |

Figure 52 (Continued)

| ID | V/D/J | | | | | | | |
|---|---|---|---|---|---|---|---|---|
| iPS:43 5763 | 21-225_176H12 | VH3J3-33/D6J6-6JRF1/JH6 | ..... | D......V... | ..... | ..... | ..... | KY..NW-...D..... |
| iPS:43 5767 | 21-225_177B4 | VH3J3-33/D6J6-6JRF1/JH6 | ..... | D......V... | ..... | ..... | .IV. | KY...W-...D..... .L.. |
| iPS:43 5785 | 21-225_179C2 | VH3J3-33/D6J6-6JRF1/JH6 | ..... | ..... | ..L.F..... | ..... | ...F. | R..G.W-- SG..... |
| iPS:43 5921 | 21-225_190D6 | VH3J3-33/D6J6-6JRF1/JH6 | ..... | ....FI... | ..R. | ..... | ..... | .EY..GW-......FG. |
| iPS:43 5961 | 21-225_192A2 | VH3J3-33/D6J6-6JRF1/JH6 | ..... | ..... | ...L..Y. | ..... | ..... | D.PY.G.A........ ..LD.F..... |
| iPS:43 5985 | 21-225_192F6 | VH3J3-33/D6J6-6JRF1/JH6 | ..... | ....FI... | ..R. | ...V. | ..... | EY..GW-......FG. |
| iPS:43 6039 | 21-225_193F8 | VH3J3-33/D6J6-6JRF1/JH6 | ..... | I......D | ...Y. | ..... | ..... | D.PY.G.G........ ...LD........ |
| iPS:43 6074 | 21-225_194F10 | VH3J3-33/D6J6-6JRF1/JH6 | ..... | ....FI... | ..R. | ..... | ..... | EY..GW-......FG. |
| iPS:43 6264 | 21-225_203F7 | VH3J3-33/D6J6-6JRF1/JH6 | ..... | D......V... | ..... | ...V. | ...E. ..R. | EY..GW-...D..... |
| iPS:43 6274 | 21-225_204H3 | VH3J3-33/D6J6-6JRF1/JH6 | G....T | ..... | ..... | ..N. | ..R. | RY..GL-...D..... .L.. |
| iPS:43 6332 | 21-225_208B2 | VH3J3-33/D6J6-6JRF1/JH6 | ..... | D......CV.. | ..... | ...V. | ..... | PY...W-.S.....FG. |
| iPS:43 6352 | 21-225_210G5 | VH3J3-33/D6J6-6JRF1/JH6 | ..... | D......CV.. | ..... | ...V. | ..R. | RY..GL-...D..... .L.. |

Figure 52 (Continued)

| | | | | | | | |
|---|---|---|---|---|---|---|---|
| iPS:43 6386 | 21-225_212B11 | VH3J3-33/D6J6-6JRF1/JH6 | | D......V... | | | RY..GW-......D.... |
| iPS:43 6412 | 21-225_214H9 | VH3J3-33/D6J6-6JRF1/JH6 | | ......V... | ...T... | | RYT.W-......D.... |
| iPS:43 6414 | 21-225_214G10 | VH3J3-33/D6J6-6JRF1/JH6 | | D......V... | ...T... | | RY..GW-......D.... |
| iPS:43 6416 | 21-225_214G12 | VH3J3-33/D6J6-6JRF1/JH6 | | D......V... | ...T... | ...F... | RY..GW-......D.... |
| iPS:43 6418 | 21-225_215E3 | VH3J3-33/D6J6-6JRF1/JH6 | | D......VI... | ...T... | | RY..GW-......D.... |
| iPS:43 6428 | 21-225_215E11 | VH3J3-33/D6J6-6JRF1/JH6 | | D......V... | ...T... | ...V... | RY..GW-......D.... |
| iPS:43 6438 | 21-225_216E8 | VH3J3-33/D6J6-6JRF1/JH6 | | D......V... | ...T... | | RY..GW-......D.... |
| iPS:43 6440 | 21-225_216H12 | VH3J3-33/D6J6-6JRF1/JH6 | | D......V... | ...T... | | RY..GW-......D.... |
| iPS:43 6450 | 21-225_217E5 | VH3J3-33/D6J6-6JRF1/JH6 | | D......V... | ...T... | | RY..GW-......D.... |
| iPS:43 6456 | 21-225_217G10 | VH3J3-33/D6J6-6JRF1/JH6 | | D......V... | ...T... | | RY..GW-......D.... |
| iPS:43 6458 | 21-225_217H12 | VH3J3-33/D6J6-6JRF1/JH6 | | D......V... | ...T... | | RY..GW-......D.... |
| iPS:43 6462 | 21-225_218C4 | VH3J3-33/D6J6-6JRF1/JH6 | | D......V... | ...T... | | RY..GW-......D.... |

Figure 52 (Continued)

| | | | | | | | | |
|---|---|---|---|---|---|---|---|---|
| iPS:43 6480 | 21-225_220F8 | VH3\|3-33/D6\|6-6\|RF1/JH6 | ........... | D......V... | ....:T | ........... | ........... | RY..GW-......D..... |
| iPS:43 6534 | 21-225_224F1 | VH3\|3-33/D6\|6-6\|RF1/JH6 | ........... | ......I.... | ........... | ........... | ........... | RY..NW-......D..... |
| iPS:43 6540 | 21-225_224F3 | VH3\|3-33/D6\|6-6\|RF1/JH6 | .......S... | ........... | ........... | ........... | ........... | RY...W-......D..... |
| iPS:43 6564 | 21-225_225A1 | VH3\|3-33/D6\|6-6\|RF1/JH6 | ........... | D......VI.. | ........... | ........... | ........... | RY..GW-......D..... |
| iPS:43 6596 | 21-225_226C6 | VH3\|3-33/D6\|6-6\|RF1/JH6 | ........... | D........ | ........... | ...T...... | ........... | RY...W-......D..... |
| iPS:43 6620 | 21-225_226H11 | VH3\|3-33/D6\|6-6\|RF1/JH6 | ........... | N......C... | ....:T | ........... | ........... | LY...W-...L........ |
| iPS:43 6744 | 21-225_154F4 | VH3\|3-33/D6\|6-6\|RF1/JH6 | ........... | ........... | ........... | ........... | ........... | D.YC.GTSC........PYY........ |
| iPS:43 6946 | 21-225_183F4 | VH3\|3-33/D6\|6-6\|RF1/JH6 | .......R... | D......V... | ........V. | .......R.. | ........... | RTYC.GTTC......PYY....LG..... |
| iPS:43 7286 | 21-225_208F1 | VH3\|3-33/D6\|6-6\|RF1/JH6 | ........... | D......V... | ........V. | .......R.. | ........... | RY..GL-......D..... |
| iPS:43 7290 | 21-225_210G6 | VH3\|3-33/D6\|6-6\|RF1/JH6 | ........... | N......CV.. | ........... | ........... | ........... | RY..GL-............. |
| iPS:39 2634 | 21-225_17H3 | VH3\|3-33/D6\|6-6\|RF1/JH6 | ........... | N......VI.. | ........... | ........S. | ........... | KY...W-......D..... |
| iPS:39 2742 | 21-225_20B2 | VH3\|3-33/D6\|6-6\|RF1/JH6 | ........... | ........... | ........... | ........... | ........... | KY...W-......D..... |

Figure 52 (Continued)

| | | | | | | | | |
|---|---|---|---|---|---|---|---|---|
| iPS:39 2836 | 21-225_22F4 | VH3\|3-33/D6\|6-6\|RF1/JH6 | . . . | D . . . . . . | . . . . V . | . . . | . . . | KY...W-- | . . D | . . . |
| iPS:39 2846 | 21-225_24B6 | VH3\|3-33/D6\|6-6\|RF1/JH6 | . . P . . . I . . | N . . . . V . | . . . | . . . | . . . | .EY.GW-- | . . D | . . . |
| iPS:39 2884 | 21-225_23A10 | VH3\|3-33/D6\|6-6\|RF1/JH6 | . . . | . . . | . . . | . . . | . . . | .RY.GW-- <br> . . . | HD . . | . . . |
| iPS:39 2888 | 21-225_25A2 | VH3\|3-33/D6\|6-6\|RF1/JH6 | . . . | . . . | . . . | . . . | . . . | R. . . W-- <br> SG . . . | -- | . . . |
| iPS:39 2914 | 21-225_25D12 | VH3\|3-33/D6\|6-6\|RF1/JH6 | . . . | . . D . | . . . | . . . | . . . | .RY...W-- <br> . . . | . . D | . . . |
| iPS:39 2924 | 21-225_32H2 | VH3\|3-33/D6\|6-6\|RF1/JH6 | . . . | . . . | . . . | . . . | . . G . . | R. . . W-- <br> TG . . . | -- | . . . |
| iPS:39 2938 | 21-225_29H4 | VH3\|3-33/D6\|6-6\|RF1/JH6 | . . . | N . . . CV . | . . . | . . . | . N . . | R. . . W-- <br> SG . . . | -- | . . . |
| iPS:39 2974 | 21-225_26A11 | VH3\|3-33/D6\|6-6\|RF1/JH6 | . . . | . . . | . . . | . . . | . . . | .EY.GW-- | . . D | . . . |
| iPS:39 3012 | 21-225_26G7 | VH3\|3-33/D6\|6-6\|RF1/JH6 | . . . | . . . | . . . | . . . | . N . . | R. . . W-- <br> SG . . . | -- | . . . |
| iPS:39 3176 | 21-225_27E7 | VH3\|3-33/D6\|6-6\|RF1/JH6 | . . . | . VL . | . . . | . . . | . . . | .D.YC.STSC <br> . .PYY . . . | . . . | . . . |
| iPS:39 3664 | 21-225_4C5 | VH3\|3-33/D6\|6-6\|RF1/JH6 | . . . | . . . | . . . | . . . | . . . | .KYT..W-- | . . D | . . . |
| iPS:39 3902 | 21-225_14E10 | VH3\|3-33/D6\|6-6\|RF1/JH6 | . . . | D . . . | . . . | . . . | . . . | .KY...W-- | . . D | . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| Germline | VH3-33/D2/2-8/RF3/JH4 | QVQLVES-GGGVVQPGRSLR LSCAASG-FTFS | S------VGMH | WVRQAPGK GLEWVA | VIWYD-GSNKYYAD SVKG | RFTISRDNSKNTLYLQM NSLRAEDTAVYYCAR | DIVLMYY------ALYFDY | WGQGTL VTVSS |
| iPS:39 3908 | 21-225_10E9 | VH3-33/D6/6-6/RF1/JH6 | . . . . . . . . . . | N . . . . . VI. | . . . . . . . | . . . . . . . | . . . . . . . | .KY...W- ......D. | . . . . . . |
| iPS:39 3916 | 21-225_2G4 | VH3-33/D6/6-6/RF1/JH6 | . . . . . . . . | . . . . . V . . | . . . . . . . | . . . . . . . | . . . . . . . | .KY...W- ......D. ..H. | . . . . . . |
| iPS:39 3950 | 21-225_3H10 | VH3-33/D6/6-6/RF1/JH6 | . . . . . . . . | . . . . . V . . | . . . . . . . | . . . . . . . | . . . . . . . | .RY..GW- ......D. .L. | . . . . . . |
| iPS:39 3972 | 21-225_7C9 | VH3-33/D6/6-6/RF1/JH6 | . . . . . . . . .L | . . . . . V . . | . . . . . . . | . . . . . . . | . . . . . . . | .KY...W- ......D. | . . . . . . |
| iPS:39 3978 | 21-225_4C12 | VH3-33/D6/6-6/RF1/JH6 | . . . . . . . . | N . . . . . V . . | . . . . . . . | . . . . . . . | . . . . . . . | .KY...W- ......D. ..H. | . . . . . . |
| iPS:39 3986 | 21-225_7G4 | VH3-33/D6/6-6/RF1/JH6 | . . . . . . . . .N | . . . . . V . . | . . . . . . . | . . . . . . . | T . . . . . . | .KY..NW- ......D. | . . . . . . |
| iPS:39 3996 | 21-225_15C11 | VH3-33/D6/6-6/RF1/JH6 | . . . . . . . . | D . . . . . V . . | . . . . . . . | . . . . . . . | . . . . . . . | .KY...W- ......D. .L. | . . . . . . |
| iPS:39 4041 | 21-225_5E5 | VH3-33/D6/6-6/RF1/JH6 | . . . . . . . . | N . . . . . V . . | . . . . . . . | . . . . . . . | . . . . . T . | .VY..GW- ......D. | . . . . . . |
| iPS:42 6118 | 21-225_7A10 | VH3-33/D2/2-8/RF3/JH4 | . . . . . . . . | . . . . . . . | . . . . .M. | . . . .H. . . | . . . .H. . . | .ER.G--- ------I---- | . . . . . . |
| iPS:39 3844 | 21-225_3G7 | VH3-33/D2/2-8/RF3/JH4 | . . . . . . . . | . . . . . . . | . . . . . . . | . . . .H. .V. | . . . . V . . . | .ER.G--- ------I---- | . . . . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 3852 | 21-225_12A10 | VH3\|3-33\|D2\|2-8\|RF3/JH4 | ........ | ........ | ........ | ..H..T.E.. | ........ | .ER.G--- -I.... | ........ |
| iPS:39 3868 | 21-225_9C11 | VH3\|3-33\|D2\|2-8\|RF3/JH4 | ........ | ........ | ........ | ..H...ET. | .....S.. | .ER.G--- -I.... | ........ |
| iPS:39 3900 | 21-225_10E12 | VH3\|3-33\|D2\|2-8\|RF3/JH4 | ....N... | ........ | ....V... | ..H...V. | .....S..C | .ER.G--- -I.... | ........ |
| iPS:39 3920 | 21-225_1H12 | VH3\|3-33\|D2\|2-8\|RF3/JH4 | ..S..... | ........ | ........ | .IH...V. | ........ | .ER.G--- -I.... | ........ |
| iPS:39 3932 | 21-225_10F5 | VH3\|3-33\|D2\|2-8\|RF3/JH4 | ...N.... | ........ | .....S.. | .IH...V. | ........ | .ER.G--- -I.... | ........ |
| Germline | VH3\|3-33\|D6\|6\|RF1/JH4 | QVQLVES GGGVVQPGRSLR LSCAASG_FTFS | YDMH | WVRQAPGK GLEWVA | VIWYD GSNKYYAD SVKG | RFTISRDNSKNTLYLQM NSLRAEDTAVYYCAR | EVSSS _____ GYFDY | WGQGTL VTVSS |
| iPS:42 6124 | 21-225_32D6 | VH3\|3-33\|D6\|6\|RF1/JH4 | ........ | ........ | .......T | ..A..... | ........ | N....... -Y.... | ........ |
| iPS:39 2922 | 21-225_30G4 | VH3\|3-33\|D6\|6\|RF1/JH4 | ........ | ........ | .......R | ..TD..V. | .......S | ........ | ........ |
| iPS:39 3002 | 21-225_30G1 | VH3\|3-33\|D6\|6\|RF1/JH4 | ........ | Y....... | ........ | ..H...V. | ........ | N....... -Y.... | ........ |
| iPS:39 3066 | 21-225_34D3 | VH3\|3-33\|D6\|6\|RF1/JH4 | ........ | Y....... | ........ | ..H...V. | ........ | N....... -F.... | ........ |
| iPS:39 3092 | 21-225_33C12 | VH3\|3-33\|D6\|6\|RF1/JH4 | ........ | H....... | ........ | ........ | ........ | N....... -Y.... | ........ |

| | | | | | | | | |
|---|---|---|---|---|---|---|---|---|
| iPS:43 4481 | 21-225_74B10 | VH1j1-08jD6j6-19jRF1/J H5 | . . . . . . . . . . . . . . | N . . . . . . | . . . . . . . H . . F | . . . . . . . . | . . . . . . . V | SSGWY--- . . . . . . . |
| iPS:43 4483 | 21-225_74C12 | VH1j1-08jD6j6-19jRF1/J H5 | . . . F . . . | N . . . . . . | . . . . . . . . | . . . . . . . . | . . . . . . . I | SSGWY--- . . . . . . . |
| iPS:43 4493 | 21-225_76F3 | VH1j1-08jD6j6-19jRF1/J H5 | . . . . . . . | N . . . . . . | . . . . . . . . | . . . . T . . . H . . V | . . . . . . . . | SSGWN--- . . . . . . . |
| iPS:43 4509 | 21-225_76F5 | VH1j1-08jD6j6-19jRF1/J H5 | . . . . . . . | N . . . . . . | . . . . . . . . | . . . . . . . S | . . . . . . . . | SSGWY--- . . . . . . . |
| iPS:43 4513 | 21-225_76A6 | VH1j1-08jD6j6-19jRF1/J H5 | . . . . . . . | N . . . . . . | . . . . . H . . N . . . | . . . . . . . . | . . . . . . . I | SSGWY--- . . . L . . . |
| iPS:43 4515 | 21-225_74A5 | VH1j1-08jD6j6-19jRF1/J H5 | . . . . . . . | N . . . . . . | . . . VP . H . . . | . . . . . . . . | . . . . . . . . | SSGWY--- . . . . . . . |
| iPS:43 4525 | 21-225_76E8 | VH1j1-08jD6j6-19jRF1/J H5 | . . . P . . . | N . . . . . . | . . . VP . . . . | . . . . . . . . | . . . . . . . V | SSGWY--- . . . A . . . |
| iPS:43 4529 | 21-225_76B9 | VH1j1-08jD6j6-19jRF1/J H5 | . . . P . . . | N . . . . . . | . . . . . . . . | . . . . . . . . | . . . . . . . I | SSGWH--- . . . . . . . |
| iPS:43 4575 | 21-225_77C7 | VH1j1-08jD6j6-19jRF1/J H5 | . . . . . . . | N . . . . . . | . . . . . H . . . | . . . . . . . . | . . . . . . . V | SSGWH--- . . . A . . . |
| iPS:43 4583 | 21-225_74B6 | VH1j1-08jD6j6-19jRF1/J H5 | . . . . . . . | N . . . . . . | . . . . . H . . N . . . | . . . . . . . . | . . . . . . . I | SSGWY--- . . . . . . . |
| iPS:43 4587 | 21-225_74G3 | VH1j1-08jD6j6-19jRF1/J H5 | . . . . . . . | N . . . . . . | . . . . . H . . . | . . . . . . . . | . . . . . . . . | SSGWY--- . . . L . . . |
| iPS:43 4597 | 21-225_77C10 | VH1j1-08jD6j6-19jRF1/J H5 | . . . . . . . | N . . . . . . | . . . . . H . . . | . . . . . . . . | . . . . . . . I | SSGWY--- . . . . . . . |

Figure 52 (Continued)

| | | | | | | | | |
|---|---|---|---|---|---|---|---|---|
| iPS:43 4603 | 21-225_77D11 | VH1j1-08/D6j6-19jRF1/JH5 | ..... | N..... | ..VP....H... | ........ | ........ | SSGWY-... |
| iPS:43 4613 | 21-225_77D12 | VH1j1-08/D6j6-19jRF1/JH5 | ..... | N..... | ........ | ........N... | ......I.. | SSGWY-... |
| iPS:43 4617 | 21-225_74B8 | VH1j1-08/D6j6-19jRF1/JH5 | ..... | N..... | ..H..... | ....L........V | ......I.. | SSGWY-... |
| iPS:43 4619 | 21-225_78C1 | VH1j1-08/D6j6-19jRF1/JH5 | ..... | N..... | ..H..... | ........I... | ........ | SSGWY-... |
| iPS:43 4639 | 21-225_74B7 | VH1j1-08/D6j6-19jRF1/JH5 | ....P | N..... | ........ | ........V | ........A | SSGWH-... |
| iPS:43 4653 | 21-225_74B5 | VH1j1-08/D6j6-19jRF1/JH5 | ..... | N..... | ........ | ....T...H...V | ........ | SSGWN-... |
| iPS:43 4655 | 21-225_78H12 | VH1j1-08/D6j6-19jRF1/JH5 | ....P | N..... | ..H.F... | ........V | ........A | SSGWH-... |
| iPS:43 4675 | 21-225_79G6 | VH1j1-08/D6j6-19jRF1/JH5 | ..... | N..... | ........ | ........V | ........ | SSGWY-... |
| iPS:43 4689 | 21-225_79G10 | VH1j1-08/D6j6-19jRF1/JH5 | ..F.. | N..... | ..VP.... | ....T...H...V | ........ | SSGWN-... |
| iPS:43 4705 | 21-225_80A2 | VH1j1-08/D6j6-19jRF1/JH5 | ..... | N..... | ..H..... | ......I.. | ........ | SSGWY-... |
| iPS:43 4707 | 21-225_80D3 | VH1j1-08/D6j6-19jRF1/JH5 | ..... | N..... | ..H..... | ........ | ........ | SSGWY-... |
| iPS:43 4731 | 21-225_80E9 | VH1j1-08/D6j6-19jRF1/JH5 | ..... | N..... | ..H..... | ......I.. | ........ | SSGWY-... |

Figure 52 (Continued)

| | | | | | | | | | |
|---|---|---|---|---|---|---|---|---|---|
| iPS:43 4747 | 21-225_80C12 | VH1j1-08/D6j6-19jRF1/JH5 | . . . . . . . . . . . | N . . . . . . . . . . | . . . . . . . . . . | . . . . . . . . . . | N . . . . . . . . . . | SSGWY- . . . . . . . . . . --- | . . . . . . . . . . L |
| iPS:43 4761 | 21-225_81E5 | VH1j1-08/D6j6-19jRF1/JH5 | . . . . . . . . . . . | N . . . . . . . . . . | . . . . . . . . . . | . . . . . . . . . . | . T . H . . . . . . V | SSGWN- . . . . . . . . . . --- | . . . . . . . . . . |
| iPS:43 4771 | 21-225_81F9 | VH1j1-08/D6j6-19jRF1/JH5 | . . . . . . . . . . . | N . . . . . . . . . . | . . . . . . . . . . | H . . . . . . . . . | . . . . . . . . . . I | SSGWY- . . . . . . . . . . --- | . . . . . . . . . . |
| iPS:43 4793 | 21-225_82A5 | VH1j1-08/D6j6-19jRF1/JH5 | . . . . . . . . . . . | N . . . . . . . . . . | . . . . . . . . . . | . . H . . . . . . . N | . . . . . . . . . . | SSGWY- . . . . . . . . . . --- | . . . . . . . . . . L |
| iPS:43 4797 | 21-225_82G5 | VH1j1-08/D6j6-19jRF1/JH5 | . . . . . . . . . . . | N . . . . . . . . . . | VP . . . . . . . . . | . H . . . . . . . . | . . . . . . . . . . I | SSGWY- . . . . . . . . . . --- | . . . . . . . . . . |
| iPS:43 4805 | 21-225_82D9 | VH1j1-08/D6j6-19jRF1/JH5 | . . . . . . . . . . . | N . . . . . . . . . . | VP . . . . . . . . . | . H . . . . . . . . | . . . . . . . . . . I | SSGWY- . . . . . . . . . . --- | . . . . . . . . . . |
| iPS:43 4813 | 21-225_82C12 | VH1j1-08/D6j6-19jRF1/JH5 | . . . . . . . . . . . | N . . . . . . . . . . | VP . . . . . . . . . | . H . . . . . . . . | . N . . . . . . . . I | SSGWY- . . . . . . . . . . --- | . . . . . . . . . . L |
| iPS:43 4825 | 21-225_83C2 | VH1j1-08/D6j6-19jRF1/JH5 | . . . . . . . . . . . | N . . . . . . . . . . | . . . . . . . . . . | . H . . . . . . . . | . . . . . . . . . . I | SSGWY- . . . . . . . . . . --- | . . . . . . . . . . |
| iPS:43 4827 | 21-225_83F3 | VH1j1-08/D6j6-19jRF1/JH5 | . . . . . . . . . . . | N . . . . . . . . . . | VP . . . . . . . . . | . H . . . . . . . . | . . . . . . . . . . I | SSGWY- . . . . . . . . . . --- | . . . . . . . . . . |
| iPS:43 4829 | 21-225_83G3 | VH1j1-08/D6j6-19jRF1/JH5 | . . . . . . . . . . . | N . . . . . . . . . . | . . . . . . . . . . | . H . . . . . . . . | . . . . . . . . . . I | SSGWY- . . . . . . . . . . --- | . . . . . . . . . . L |
| iPS:43 4833 | 21-225_83C5 | VH1j1-08/D6j6-19jRF1/JH5 | . . . . . . . . . . . | N . . . . . . . . . . | . . . . . . . . . . | . H . . . . . . . . | . . . . . . . . . . I | SSGWY- . . . . . . . . . . --- | . . . . . . . . . . |
| iPS:43 4841 | 21-225_83G7 | VH1j1-08/D6j6-19jRF1/JH5 | . . . . . . . . . P | N . . . . . . . . . . | . . . . . . . . . . | . . . . . . . . . . | . . . . . . . . . . V | SSGWH- . . . . . . . . . . --- | . . . . . . . . . . A |

Figure 52 (Continued)

| | | | | | | | | | |
|---|---|---|---|---|---|---|---|---|---|
| iPS:43 4863 | 21-225_84G7 | VH1|1-08/D6|6-19|RF1/J H5 | . . . . . . . . . . | N . . . . . . . . . | . . . . . . . . . . | . . . D . . . . . . | . . . . . . . . . . | SSGWH- . . . . . --- | . . . A . . . . . . |
| iPS:43 4877 | 21-225_85H2 | VH1|1-08/D6|6-19|RF1/J H5 | . . . . . P . . . . | N . . . . . . . . . | . . . . . . . . . . | . . . . . . . . . . | . . . . . L . . . V | SSGWY- . . . . . --- | . . . . . . . . . . |
| iPS:43 4883 | 21-225_85B5 | VH1|1-08/D6|6-19|RF1/J H5 | . . . . . . . . . . | N . . . . . . . . . | . . . . . . . . . . | . . V P . . . . H . | . . . . . . . . . I | SSGWY- . . . . . --- | . . . . . . . . . . |
| iPS:43 4911 | 21-225_85D11 | VH1|1-08/D6|6-19|RF1/J H5 | . . . . . . . . . . | N . . . . . . . . . | . . . . . . . . . . | . . V P . . . . H . | . . . . . . . . . I | SSGWY- . . . . . --- | . . . . . . . . . . |
| iPS:43 4935 | 21-225_86E9 | VH1|1-08/D6|6-19|RF1/J H5 | . . . . . . . . . . | N . . . . . . . . . | . . . . . . . . . . | . . . . . . . . H . | . . S . T . . H . V | SSGWS- . . . . . --- | . . . . . . . . . . |
| iPS:43 4957 | 21-225_87A10 | VH1|1-08/D6|6-19|RF1/J H5 | . . . . . . . . . . | N . . . . . . . . . | . . . . . . . . . . | . . . . . . . . . N | . . . . . . . . . . | SSGWY- . . . . . --- | . . . L . . . . . . |
| iPS:43 4971 | 21-225_88G2 | VH1|1-08/D6|6-19|RF1/J H5 | . . . . . . . . . . | N . . . . . . . . . | . . . . . . . . . . | . . . . . . . . H . | . . . . . . . . . I | SSGWY- . . . . . --- | . . . . . . . . . . |
| iPS:43 5051 | 21-225_90D9 | VH1|1-08/D6|6-19|RF1/J H5 | . . . . . P . . . . | N . . . . . . . . . | . . . . . . . . . . | . . . . . . . . . . | . . . . . . . . . I | SSGWH- . . . . . --- | . . . A . . . . . . |
| iPS:43 5071 | 21-225_91F1 | VH1|1-08/D6|6-19|RF1/J H5 | . . . . . . . . . . | N . . . . . . . . . | . . . . . . . . . . | . . . . . . . . H . | . . . . . . . . . V | SSGWY- . . . . . --- | . . . . . . . . . . |
| iPS:43 5087 | 21-225_91G8 | VH1|1-08/D6|6-19|RF1/J H5 | . . . . . . . . . . | N . . . . . . . . . | . . . . . . . . . . | . . . . . . . . H . | . . . . . . . . . I | SSGWY- . . . . . --- | . . . . . . . . . . |
| iPS:43 5203 | 21-225_75A7 | VH1|1-08/D6|6-19|RF1/J H5 | . . . . . P . . . . | N . . . . . . . . . | . . . . . . . . . . | . . . . . . . . D . | . . . . . . . . . V | SSGWH- . . . . . --- | . . . A . . . . . . |
| iPS:43 5211 | 21-225_94E11 | VH1|1-08/D6|6-19|RF1/J H5 | . . . . . . . . . . | N . . . . . . . . . | . . . . . . . . . . | . . . . . . . . . . | . . . . . T . H . V | SSGWK- . . . . . --- | . . . . . . . . . . |

Figure 52 (Continued)

| ID | Gene | | | | | | | |
|---|---|---|---|---|---|---|---|---|
| iPS:43 5227 | VH1j1-08/D6j6-19jRF1/JH5 | . . . . . . . . . . | N . . . . . . . . | . . . . . . . . . . | . . . . . . . . . . | . . . . T . . H . . . V | SSGWN- . . . . . — — | . . . . . . . . . . |
| iPS:43 5245 | 21-225_95E12 | . . . . . . . . . . | N . . . . . . . . | . . . . . . . . . . | . . . . . . . . . . | . . . . . . . . . . I | SSGWY- . . . . . — — | . . . . . . . . . . |
| iPS:43 5247 | 21-225_96G1 | . . . . . . . . . . | N . . . . . . . . | . . . H . . . . . . | . . . N . . . . . . | . . . . . . . . . . I | SSGWY- . . . . . — — | . . . . L . . . . . |
| iPS:43 5249 | 21-225_96E2 | . . . . . . . . . . | N . . . . . . . . | . . . . H . . . . . | . . . . . . . . . . | . . . L . . . . . . V | SSGWY- . . . . . — — | . . . . . . . . . . |
| iPS:43 5255 | 21-225_96D5 | . . . . . . . . . . | N . . . . . . . . | . . . . . . . . . . | . . . . . . . . . . | . . . . S . T . . H . V | SSGWS- . . . . . — — | . . . . . . . . . . |
| iPS:43 5279 | 21-225_97H4 | . . . . . . . . . . | N . . . . . . . . | . . . . H . . . . . | . . . . . . . . . . | . . . . . . . . . . I | SSGWY- . . . . . — — | . . . . . . . . . . |
| iPS:43 5327 | 21-225_147G6 | . . . . . . . . . . | N . . . . . . . . | . . . H . . . . . . | . . . . . . . . . . | . . . . . . . . . . Y | SSGWY- . . . . . — — | . . . . . . . . . . |
| iPS:43 5437 | 21-225_152F4 | . . . . . . . . . . | N . . . . . . . . | . . . H . . D . . . | . . . . . . . . . . | . . . . . . D . . . Y | SSGWY- . . . . . — — | . . . . . . . . . . |
| iPS:43 5701 | 21-225_170F6 | . . . . . . . . . . | N . . . . . . . . | . . . . . . . . . . | . . . . . . . . . . | . . . . . . . H . . I | SSGWY- . . . . . — — | . . . . . . . . . . |
| iPS:43 5737 | 21-225_174G5 | . . . . . . . . . . | N . . . . . . . . | . . . H . . . . . . | . . . . . . . . . . | . . . . . . . . . . V | SSGWY- . . . . . — — | . . . . . . . . . . |
| iPS:43 6544 | 21-225_224H5 | . . . . . . . . . . | N . . . . . . . . | . . . . . S . . . . | . . . . . . . . . . | . . . . . . . . . . S | SSGWN- . . . . . — — | . . . . . . . . . . |
| iPS:43 6570 | 21-225_225F4 | . . . . . . . . . . | N . . . . . . . . | . . . H . S . . . . | . . . L . . . . . . | . . . N . . . . . V . S | SSGWY- . . . . . — — | . . . . . . . . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6644 | 21-225_227G9 | VH1J1-08/D6[6-19]RF1/JH5 | .................................. | N............ | .................................... | ....K..Y....... | ................................................................... | SSGWY-......L.... | ........... |
| iPS:43 7322 | 21-225_75B1 | VH1J1-08/D6[6-19]RF1/JH5 | .....................R............ | ............ | ..VP................................ | ...H........... | ................................................................... | SSGWY-......I.... | ........... |
| iPS:43 7361 | 21-225_74C1 | VH1J1-08/D6[6-19]RF1/JH5 | .................................. | N............ | .................................... | ...D........... | .........................................................V......... | SSGWY-........... | ........... |
| iPS:43 7363 | 21-225_74C10 | VH1J1-08/D6[6-19]RF1/JH5 | .................................. | N............ | .................................... | ...F........... | ................................................................I.. | SSGWY-........... | ........... |
| iPS:43 7379 | 21-225_74H2 | VH1J1-08/D6[6-19]RF1/JH5 | ...............F.................. | N............ | .................................... | ...H..F........ | .........................................................V......... | SSGWY-........... | ........... |
| iPS:44 6094 | 21-225_77E1 | VH1J1-08/D6[6-19]RF1/JH5 | .............P.................... | ............ | .................................... | ............... | .........................................................V......... | SSGWH-........A.. | ........... |
| iPS:45 1129 | 21-225_94D2 | VH1J1-08/D6[6-19]RF1/JH5 | ...............F.................. | ............ | .................................... | ...H..F........ | .........................................................V......... | SSGWY-........... | ........... |
| iPS:45 1133 | 21-225_95H4 | VH1J1-08/D6[6-19]RF1/JH5 | .............I.................... | ............ | .................................... | ............... | ..........................................T.....H........V......... | SSGWN-........... | ........... |
| iPS:39 8510 | 21-225_25A3 | VH1J1-08/D6[6-19]RF1/JH5 | .................................. | N............ | .................................... | ...H........... | ....................................W......................N......S | SSGWY-........... | ........... |
| iPS:39 8516 | 21-225_26A9 | VH1J1-08/D6[6-19]RF1/JH5 | .................................. | N............ | .................................... | ...H..C........ | ....................................W.M....................S | SSGWY-........... | ........... |
| Germline VH3J3-30.3/D5[5-18]RF3/JH4 | | QVQLVES-GGGVVQPGRSLR LSCAASG-FTFS | S-------YAMH | WVRQAPGK VSID- GLRWVA | GSNKYYAD SVKG | RFTISRDNSKNTLYLQM NSLRAEDTAVYYCAR | GYSYG----------YFDY | WGQGTL VTVSS |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:45_1139 | VH3j3-30.3/D5j5-18jRF3/J H4 | . . . . . . . . . . . . . . . . . . . . . . . . . . . . . . . . . . . . . . . . . . . . . . . . . | N . . . . . . . G . . . | . . . . . . . . . . . . . . . . . . . . . . | . . . . . E . . . . . . | . . . . . . . . . . . . . . . . . . . . . . . . . . . . . . . . . . . . . . . . . . . . . . . . . . . . . | DHR.V . . . . . . . . . . . . . . . . RGG . . . | . . . . . . . . . . . . . |
| VH1j1-18jD6j6-19jRF2jJH5 | Germline | QVQLVQS GAEVKKPGASVK VSCKASG YTFT | S . . . . . . . YGIS | WVRQAPGQ GLEWMG | WISAY NGNTNYAQ KLQG | RVTMTTDTSTSTAYMEL RSLRSDDTAVYYCAR | GLAYAG . . WFDP | WGQGTL VTVSS |
| iPS:45_1143 | VH1j1-18jD6j6-19jRF2jJ H5 | . . . . . . . . . . . . . . . . . . . . . . . . . . . . . . . . . . . . . . . . . | T . . . . . . . . . . . . | . . . . . . . . . . . . . . . . . . . . . . | . . . . . . . . . . . . . . . . . . | . . . . . . . . . . . . . . . . . . . . . . . . . . . . . . . . . . . . . . . . . . | .E . . . — . . . . . -V . . . | . . . . . . . . . . . . . |
| iPS:43_4361 | VH1j1-18jD6j6-19jRF2jJ H5 | . . . . . . . . . . . . . . . . . . . . . . . . A . . . . . . . . . . . P . . . . . | . . . . . . . . . . . . . . . | . . . . . . . . . . . . . . . . . . . . . . | . . . . . . . . . . . . . . S . . . . | . . . . . . . . . . . . . F . . . . . . . . . . . . . . . . . . . . . . . . . . . . | .E . . . — . . . . . -V . . . | . . . . . . . . . . . . . |
| VH3j3-33jD4j4-23jRF2jJH6 | Germline | QVQLVES GGGLVQPGRSLR LSCAASG FTFS | S . . . . . . . YGMH | KVRQAPGK GLEWVA | VIWYD GSNKYYAD SVKG | RFTISRDNSKNTLYLQM NSLRAEDTAVYYCAR | DYGNSYY . . YYGMDV | WGQGTT VTVSS |
| iPS:45_3445 | VH3j3-33jD4j4-23jRF2jJ H6 | . . . . . . . . . . . . . . . . . . . . . . . . . . . . . . . . . . . . . . . . . | . . . . . . . . . . . . . . . | . . . . . . . . . . . . . . . . . . . . . . | F . . . . . V . . D . . | . . . . . . . . . . . . . . . . . . . . . . . . . . . . . . . . . . . . . . . . . | .RVEG.GTP . . . . . . . . . . . . Y . . . | . . . . . . . . . . . . . |
| iPS:43_6082 | VH3j3-33jD4j4-23jRF2jJ H6 | . . . . . . . . . . . . . . . . . . . . . . . . . . . . . . . . . . . . . . . . . | H . . . . . . V . . | . . . . . . . . . . . . . . . . . . . . . . | . . . . . T . . . . . | . . . . . . . . . . . . . . . . . . . . . . . . . . . . . . . . . . . . . . . . . | .WF.EGN— . . . . . . . . . . . | . . . . . . . . . . . . . |
| iPS:43_6118 | VH3j3-33jD4j4-23jRF2jJ H6 | . . . . . . . . . . . . . . . . . . . . . . . . . . . . . . . . . . . . . . . . . | H . . . . . . V . . | . . . . . . . . . . . . . . . . . . . . . . | . . . . . T . . . . . | . . . . . . . . . . . . . . . . . . . . . . . . . . . . . . . . . . . . . . . . . | .WF.EGN— . . . . . . . . . . . | . . . . . . . . . . . . . |
| iPS:43_6670 | VH3j3-33jD4j4-23jRF2jJ H6 | . . . . . . . . . . . . . . . . . . . . . . . . . . . . . . . . . . . . . . . . . | . . . . . . . . . . . . . . . | . . . . . . . . . . . . . . . . . . . . . . | D..F . . . V . . D . . | . . . . . . . . . . . . . . . . . . . . . . . . . . . . . . . . . . . . . . . . . | .RVEG.GTP . . . . . . . . . . . . Y . . . | . . . . . . . . . . . . . |
| iPS:43_6720 | VH3j3-33jD4j4-23jRF2jJ H6 | . . . . . . . . . . . . . . . . . . . . . . . . . . . . . . . . . . . . . . . . . | D . . . . . . . . . . . | . . . . . . . . . . . . . . . . . . . . . . | L . . . . . . . . . . | . . . . . . . . . . . . . . . . . . . . . . . . . . . . . . . . . . . . . . . . . | .DRSC.RTSC . . . . . .PYY . . . .L . . . | . . . . . I . . . |
| iPS:43_6726 | VH3j3-33jD4j4-23jRF2jJ H6 | . . . . . . . . . . . . . . . . . . . . . . . . . . . . . . . . . . . . . . . . . | D . . . . . . . . . . . | . . . . . . . . . . . . . . . . . . . . . . | L . . . . . . . . . . | . . . . . . . . . . . . . . . . . . . . . . . . . . . . . . . . . . . . . . . . . | .DRSC.RTSC . . . . . . .FYY . . . .L . . . | . . . . . I . . . |

Figure 52 (Continued)

| | | | | | | | |
|---|---|---|---|---|---|---|---|
| iPS:43 6732 | 21-225_152B12 | VH3|3-33|D4|4-23|RF2|J H6 | ..V............ | D............. | ............... | ............... | DRSC.STSC......... ..PYY.....L.... | ............... |
| iPS:43 6734 | 21-225_153A8 | VH3|3-33|D4|4-23|RF2|J H6 | ..M............ | ............... | L.............. | ............... | DRSC.RTSC......... ..PYY.....L.... | ............T. |
| iPS:43 6736 | 21-225_153E8 | VH3|3-33|D4|4-23|RF2|J H6 | ............L.. | ............... | ....F......V... ........D...... | ............... | RVEG.GTP.......... ............Y. | ............... |
| iPS:43 6756 | 21-225_146A10 | VH3|3-33|D4|4-23|RF2|J H6 | ..E............ | G............. | ...MT.......... | L.R........... ..D.N.......... | ............... | RVFC.STSCL........ ..SYY.......... | ............... |
| iPS:43 6766 | 21-225_158D10 | VH3|3-33|D4|4-23|RF2|J H6 | ............... | ............... | ............... | ............... | ............... | RVSC.STSC......... ..PYY.......... | ............... |
| iPS:43 6768 | 21-225_159H8 | VH3|3-33|D4|4-23|RF2|J H6 | ............... | T............. | ............... | ............... | ............... | RVSC.STSC......... ..PYY.......... | ............... |
| iPS:43 6770 | 21-225_160B12 | VH3|3-33|D4|4-23|RF2|J H6 | ............... | ............... | ............... | ............... | ............... | RVSC.STSC......... ..PYY.......... | ............... |
| iPS:43 6782 | 21-225_166G11 | VH3|3-33|D4|4-23|RF2|J H6 | ............N.. | G............. | ............... | ............... | ............T. ............F. | DRYC.SPTCH........ ..PYY.....L.... | ............... |
| iPS:43 6794 | 21-225_170F1 | VH3|3-33|D4|4-23|RF2|J H6 | ............... | G............. | ............N.. | ....I.......... ....N.......... | ............... | RVIC.STSCR........ ..PYY......A... | ............... |
| iPS:43 6836 | 21-225_52H1 | VH3|3-33|D4|4-23|RF2|J H6 | ............... | ............... | ............... | ............... | ............... | RVVC.SSSCS........ ...YYY......... | ............... |
| iPS:43 6922 | 21-225_78E9 | VH3|3-33|D4|4-23|RF2|J H6 | ............... | ............... | ............... | ....N..S....... ............... | ............... ............I. | RDYC.STSC......... ..PYY.......... | ............... |
| iPS:43 6924 | 21-225_74B3 | VH3|3-33|D4|4-23|RF2|J H6 | ............... | R............. | ............... | ....F......D... ............... | ............... | RDYC.STSC......... ..PYY.......... | ............... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6928 | 21-225_79E7 VH3\|3-33\|D4\|4-23\|RF2/J H6 | ................ | ............ | ............ | ............ | ..............I........ | .RDYC.STSC........ ..PYY............ | ............ |
| iPS:43 6932 | 21-225_92A4 VH3\|3-33\|D4\|4-23\|RF2/J H6 | ................ | ............ | ............ | ..N..S....... | ..........Y...I........ | .RDYC.STSC........ ..PYY............ | ............ |
| iPS:43 6936 | 21-225_97E6 VH3\|3-33\|D4\|4-23\|RF2/J H6 | ................ | ............ | ............ | ..N..S....... | ..............I........ | .RDYC.STSC........ ..PYY............ | ............ |
| iPS:43 7190 | 21-225_225A9 VH3\|3-33\|D4\|4-23\|RF2/J H6 | .......G........ | ....T....... | ........L... | ............ | ..............I..Q..... | .NHYC.STSCS....... ..PYY..F......... | ............ |
| iPS:43 7254 | 21-225_149F2 VH3\|3-33\|D4\|4-23\|RF2/J H6 | ....G.A......... | ....R....... | ............ | F.......EN... | ..........V...R........ | .RVEG.GTP......... .....Y........... | ............ |
| iPS:43 7256 | 21-225_150F11 VH3\|3-33\|D4\|4-23\|RF2/J H6 | ....G.A......... | ....R....... | ............ | F.......EN... | ..........V...R........ | .RVEG.GTP......... .....Y........... | ............ |
| iPS:45 1110 | 21-225_74C9 VH3\|3-33\|D4\|4-23\|RF2/J H6 | ................ | ....G....... | ............ | ..N..S....... | ..............I........ | .RDYC.STSC........ ..PYY............ | ............ |
| iPS:39 2589 | 21-225_27H2 VH3\|3-33\|D4\|4-23\|RF2/J H6 | ................ | ....G....... | ............ | ............ | ......................F | .RVYC.STSCS....... ..PYY............ | ............ |
| iPS:39 3166 | 21-225_27G6 VH3\|3-33\|D4\|4-23\|RF2/J H6 | ................ | ....G....... | ........L... | I.......K..N. | ............ | .RVYC.STSCS....... ..PYY............ | ............ |
| iPS:39 3198 | 21-225_28A11 VH3\|3-33\|D4\|4-23\|RF2/J H6 | ................ | ............ | ............ | L.......N..T. | ............ | .RVSC.STSCS....... ..PYY............ | ............ |
| iPS:39 3204 | 21-225_8C12 VH3\|3-33\|D4\|4-23\|RF2/J H6 | ..............G. | ............ | ............ | L............ | ............ | .RVSC.SSSCY....... ..PYY............ | ............ |
| Germline | | | | | | | | |

Figure 52 (Continued)

| | Germline | H_FR1 QVQLVQS GAEVKKPGASVK VSCKASG.YTFT | H_CDR1 .YMH | H_FR2 WVRQAPG QGLEWMG | H_CDR2 IINPS GGSTYAQ KFQG | H_FR3 RVTMTRDTSISTAYMEL SSLRSEDTAVYYCAR | H_CDR3 DYSNY........YFDY | H_FR4 WGQGT LVTVSS |
|---|---|---|---|---|---|---|---|---|
| iPS:45 3447 | 21-225_65F10 | VH1\|1-02\|D4\|4-11\|RF2\|JH4 | ........................ | .H. | ........ | N...S ....D | N........................ | .SRS-........YFDV | ........ |
| iPS:43 4145 | 21-225_55B1 | VH1\|1-02\|D4\|4-11\|RF2\|JH4 | ........................ | ....F. | ........ | .H. NNA. | ........................K | .GRS-.....SW. | ........ |
| iPS:43 4277 | 21-225_57A7 | VH1\|1-02\|D4\|4-11\|RF2\|JH4 | ........................ | .HI | D..... | NN. | ........................ | .GRS-.....S. | ........ |
| iPS:43 4389 | 21-225_66F11 | VH1\|1-02\|D4\|4-11\|RF2\|JH4 | ........................ | .H. | ........ | N...H ....D | W........................ | .SRS-.....G. | ........ |
| iPS:43 4423 | 21-225_70D1 | VH1\|1-02\|D4\|4-11\|RF2\|JH4 | ........................ | .H. | ........ | .NA. | ........................ | .SIS-.....SW. | ........ |
| iPS:43 7234 | 21-225_64E2 | VH1\|1-02\|D4\|4-11\|RF2\|JH4 | ........................ | ........ | ........ | NN. | ........................ | .G.S-.....G. | ........ |

| | Germline | H_FR1 QVQLQES GPGLVKPSETLS LTCTVSGGSIS .SYYWS | H_CDR1 .SYYWS | H_FR2 WIRQPPG KGLEWIG | H_CDR2 YIYY SGSTNYNP SLKS | H_FR3 RVTISVDTSKNQFSLK LSSVTAADTAVYYCAR | H_CDR3 HEY........FDI | H_FR4 WGQGT MVTVSS |
|---|---|---|---|---|---|---|---|---|
| iPS:45 3449 | 21-225_208A2 | VH4\|4-59\|D7\|7-27\|RF1\|JH4 | ........N. ....R | ........ | ....A.. | R..T. ...D. | ..I..M. | GF.D.........W. | ........ |
| iPS:43 5451 | 21-225_152D10 | VH4\|4-59\|D7\|7-27\|RF1\|JH4 | ........................ | N....... | ....A.. | R.DT. ...I. | ....M. T........ | EG.LGA.......TF. | ........ |
| iPS:43 5467 | 21-225_153B9 | VH4\|4-59\|D7\|7-27\|RF1\|JH4 | ........................ | ........ | ....A.. | R.DT. ...I. | ....M. T........ | EG.VGA.......TY. | ........ |
| iPS:43 5545 | 21-225_158F4 | VH4\|4-59\|D7\|7-27\|RF1\|JH4 | ........................ | .HF. | ....A.. | R..T. ...T...T | ....M. | .SSG.........W. | ........ |

| | | | | | | | | |
|---|---|---|---|---|---|---|---|---|
| iPS:43 4497 | 21-225_76A4 | VH4|4-34|D4|4-17|RF2/J H6 | ........ | .C. | ........ | ........ | ........ | ...G---- |
| iPS:43 4501 | 21-225_76G4 | VH4|4-34|D4|4-17|RF2/J H6 | .H...... | .C. | ........ | ........ | ........ | ...G---- |
| iPS:43 4507 | 21-225_74C5 | VH4|4-34|D4|4-17|RF2/J H6 | .H...... | .C. | ..C..F.. | ........ | ........ | ...G---- |
| iPS:43 4523 | 21-225_75C3 | VH4|4-34|D4|4-17|RF2/J H6 | ....G... | .C. | ..Y...R. | ........ | ........ | ...G---- |
| iPS:43 4533 | 21-225_85F7 | VH4|4-34|D4|4-17|RF2/J H6 | .....P.. | .P. | ........ | ..T..... | ........ | ...G---- ---L.. |
| iPS:43 4547 | 21-225_74H5 | VH4|4-34|D4|4-17|RF2/J H6 | .N.P.... | .C. | ..R..F.. | ........ | ........ | ...G---- |
| iPS:43 4559 | 21-225_74D11 | VH4|4-34|D4|4-17|RF2/J H6 | .H...... | .C. | ........ | ........ | ........ | ...G---- |
| iPS:43 4561 | 21-225_77G1 | VH4|4-34|D4|4-17|RF2/J H6 | .H...... | ... | ........ | ........ | ........ | ...G---- |
| iPS:43 4565 | 21-225_75B10 | VH4|4-34|D4|4-17|RF2/J H6 | ......K.D | .C. | ........ | ........ | ........ | ...G---- ---L.. |
| iPS:43 4579 | 21-225_77F7 | VH4|4-34|D4|4-17|RF2/J H6 | .H...... | .C. | ........ | ........ | ........ | ...G---- |
| iPS:43 4581 | 21-225_74B12 | VH4|4-34|D4|4-17|RF2/J H6 | ....G..P | .C. | ........ | ........ | ........ | ...G---- |
| iPS:43 4585 | 21-225_75A12 | VH4|4-34|D4|4-17|RF2/J H6 | ........ | .C. | ..Y...R. | ........ | ........ | ...G---- |

Figure 52 (Continued)

| | | | | | | | | |
|---|---|---|---|---|---|---|---|---|
| iPS:43 4595 | 21-225_77A10 | VH4\|4-34\|D4\|4-17\|RF2/JH6 | ........G..P.. :::::::: | ....C... :::::::: | ........Y. ...R...... :::::::: | :::::::: | :::::::: | ...G----- :::::::: |
| iPS:43 4611 | 21-225_77C12 | VH4\|4-34\|D4\|4-17\|RF2/JH6 | :::::::: ......A. | ....S... :::::::: | .....S.. :::::::: ...R...... | :::::::N :::::::: | :::::::: | ...G---- :::::::: ---- |
| iPS:43 4657 | 21-225_79G1 | VH4\|4-34\|D4\|4-17\|RF2/JH6 | :::::::: .H...... | ....C... :::::::: | ........Y. ...R...... :::::::: | :::::::: | :::::::: | ...G---- :::::::: |
| iPS:43 4663 | 21-225_79F3 | VH4\|4-34\|D4\|4-17\|RF2/JH6 | :::::::: .H...... | ....C... :::::::: | :::::::: | :::::::: | :::::::: | ...G---- :::::::: |
| iPS:43 4687 | 21-225_75A5 | VH4\|4-34\|D4\|4-17\|RF2/JH6 | :::::::: .H...... | ....C... :::::::: | .....S.. :::::::: | :::::::: | :::::::: | ...G---- :::::::: |
| iPS:43 4691 | 21-225_75G7 | VH4\|4-34\|D4\|4-17\|RF2/JH6 | :::::::T ......A. | ....S... :::::::: | :::::::: ...R...... :::::::: | :::::::N :::::::: | :::::::: | ...G---- :::::::: |
| iPS:43 4693 | 21-225_79F11 | VH4\|4-34\|D4\|4-17\|RF2/JH6 | :::::::: .H...... | ....C... :::::::: | :::::::: | :::::::: | :::::::: | ...G---- :::::::: |
| iPS:43 4699 | 21-225_79G12 | VH4\|4-34\|D4\|4-17\|RF2/JH6 | :::::::: .H...... | ....C... :::::::: | :::::::: | :::::::: | :::::::: | ...G---- :::::::: |
| iPS:43 4701 | 21-225_80A1 | VH4\|4-34\|D4\|4-17\|RF2/JH6 | :::::::: .H...... | ....C... :::::::: | :::::::: | :::::::: | :::::::: | ...G---- :::::::: |
| iPS:43 4703 | 21-225_80C1 | VH4\|4-34\|D4\|4-17\|RF2/JH6 | :::::::: .H...... | ....C... :::::::: | :::::::: | :::::::: | :::::::: | ...G---- :::::::: |
| iPS:43 4709 | 21-225_80E3 | VH4\|4-34\|D4\|4-17\|RF2/JH6 | :::::::: .H...... | ....P... :::::::: | :::::::: | .T....... :::::::: | ........M. :::::::: | ...G---- :::::::: |
| iPS:43 4715 | 21-225_80D5 | VH4\|4-34\|D4\|4-17\|RF2/JH6 | :::::::: ...P.... | :::::::: | :::::::: | :::::::: | :::::::: | ...G---- ---L... |

Figure 52 (Continued)

| | | | | | | | |
|---|---|---|---|---|---|---|---|
| iPS:43 4725 | 21-225_80H7 | VH4\|4-34\|D4\|4-17\|RF2/J H6 | ........ | ....S... | .....Q .....R ... | ........ | ...G--- ---- .... |
| iPS:43 4743 | 21-225_74A4 | VH4\|4-34\|D4\|4-17\|RF2/J H6 | ...V.... | ........ | ........ | ........ | ...G--- ----I.. |
| iPS:43 4751 | 21-225_80H12 | VH4\|4-34\|D4\|4-17\|RF2/J H6 | .H...... | ...C.... | ........ | ........ | ...G--- ---- .... |
| iPS:43 4759 | 21-225_81C5 | VH4\|4-34\|D4\|4-17\|RF2/J H6 | .H...... | ...C.... | ........ | ........ | ...G--- ---- .... |
| iPS:43 4773 | 21-225_75D9 | VH4\|4-34\|D4\|4-17\|RF2/J H6 | ........ | ...P.... | ...Y .R.. | ....N... | ...G--- ---- .... |
| iPS:43 4777 | 21-225_81C11 | VH4\|4-34\|D4\|4-17\|RF2/J H6 | .H...... | ...C.... | ........ | ........ | ...G--- ---- .... |
| iPS:43 4809 | 21-225_74F5 | VH4\|4-34\|D4\|4-17\|RF2/J H6 | ........ | ...C.... | ........ | ........ | ...G--- ---- .... |
| iPS:43 4821 | 21-225_83G1 | VH4\|4-34\|D4\|4-17\|RF2/J H6 | .H...... | ...C.... | ........ | ........ | ...G--- ---- .... |
| iPS:43 4839 | 21-225_83B7 | VH4\|4-34\|D4\|4-17\|RF2/J H6 | .H...... | ........ | ........ | ........ | ...G--- ---- .... |
| iPS:43 4869 | 21-225_84E12 | VH4\|4-34\|D4\|4-17\|RF2/J H6 | ........ | ...S.... | ...Q .R.. | ........ | ...G--- ---- .... |
| iPS:43 4879 | 21-225_85A3 | VH4\|4-34\|D4\|4-17\|RF2/J H6 | .H...... | ...C.... | ........ | ........ | ...G--- ---- .... |
| iPS:43 4881 | 21-225_85B4 | VH4\|4-34\|D4\|4-17\|RF2/J H6 | .H...... | ...C.... | ........ | ........ | ...G--- ----I.. |

Figure 52 (Continued)

| | | | | | | | |
|---|---|---|---|---|---|---|---|
| iPS:43 4887 | 21-225_85D6 | VH4|4-34|D4|4-17|RF2|JH6 | ..........G..P | ....C... | ....Y.... | | ...G---- |
| iPS:43 4895 | 21-225_74H7 | VH4|4-34|D4|4-17|RF2|JH6 | ...........P... | ....P... | ....R.... | ....T.... | ...G----<br>---L... |
| iPS:43 4899 | 21-225_85B9 | VH4|4-34|D4|4-17|RF2|JH6 | ....N...P... | ....C... | ....R..F. | | ...G---- |
| iPS:43 4907 | 21-225_85G10 | VH4|4-34|D4|4-17|RF2|JH6 | ............R.. | ....C... | ....I.... | ....T.... | ...G----<br>---L... |
| iPS:43 4913 | 21-225_86C1 | VH4|4-34|D4|4-17|RF2|JH6 | ............H.. | ....C... | ......... | | ...G---- |
| iPS:43 4921 | 21-225_86E4 | VH4|4-34|D4|4-17|RF2|JH6 | ............H.. | ....C... | ......... | | ...G----<br>---L... |
| iPS:43 4939 | 21-225_86C11 | VH4|4-34|D4|4-17|RF2|JH6 | ............H.. | ....C... | ......... | | ...G---- |
| iPS:43 4943 | 21-225_87H1 | VH4|4-34|D4|4-17|RF2|JH6 | ...........P... | ....C... | ....R.... | ....D.... | ...G---- |
| iPS:43 4945 | 21-225_87E5 | VH4|4-34|D4|4-17|RF2|JH6 | ............H.. | ....C... | ......... | | ...G---- |
| iPS:43 4955 | 21-225_87C9 | VH4|4-34|D4|4-17|RF2|JH6 | ............H.. | ....C... | ......... | | ...G---- |
| iPS:43 4961 | 21-225_87A12 | VH4|4-34|D4|4-17|RF2|JH6 | ............H.. | ....C... | ......... | | ...G---- |
| iPS:43 4969 | 21-225_88H1 | VH4|4-34|D4|4-17|RF2|JH6 | ............H.. | | ......... | | ...G---- |

Figure 52 (Continued)

| | | | | | | | |
|---|---|---|---|---|---|---|---|
| iPS:43 4981 | 21-225_88E7 | VH4|4-34|D4|4-17|RF2|J H6 | ..H...... | ...C........ | ........ | ........ | ...G---- |
| iPS:43 4983 | 21-225_88F7 | VH4|4-34|D4|4-17|RF2|J H6 | ..H...... | ...C........ | ........ | ........ | ...G---- |
| iPS:43 4995 | 21-225_88G9 | VH4|4-34|D4|4-17|RF2|J H6 | ..H...... | ...C........ | ........ | ........ | ...G---- |
| iPS:43 4999 | 21-225_75A8 | VH4|4-34|D4|4-17|RF2|J H6 | ..H...... | ...C........ | ........ | ........ | ...G---- |
| iPS:43 5013 | 21-225_89D5 | VH4|4-34|D4|4-17|RF2|J H6 | ..H...... | ...C........ | ...Y.F.. | ........ | ...G---- |
| iPS:43 5015 | 21-225_89H5 | VH4|4-34|D4|4-17|RF2|J H6 | ..H...... | ...C........ | ........ | ...A.... | ...G---- |
| iPS:43 5025 | 21-225_89E10 | VH4|4-34|D4|4-17|RF2|J H6 | ..P...... | ...C........ | ...R.S.. | ........ | ...G---- |
| iPS:43 5029 | 21-225_89A11 | VH4|4-34|D4|4-17|RF2|J H6 | ..H...... | ...C........ | ........ | ........ | ...G---- -L.. |
| iPS:43 5039 | 21-225_90G4 | VH4|4-34|D4|4-17|RF2|J H6 | .......... | ...C........ | ........ | ........ | ...G---- |
| iPS:43 5041 | 21-225_90A5 | VH4|4-34|D4|4-17|RF2|J H6 | ..H...... | ...C........ | ........ | ........ | ...G---- |
| iPS:43 5043 | 21-225_90G5 | VH4|4-34|D4|4-17|RF2|J H6 | ..H...... | ...C........ | ........ | ........ | ...G---- |
| iPS:43 5055 | 21-225_90F10 | VH4|4-34|D4|4-17|RF2|J H6 | ..H...... | ............ | ........ | ........ | ...G---- |

Figure 52 (Continued)

| | | | | | | | | |
|---|---|---|---|---|---|---|---|---|
| iPS:43 5073 | 21-225_91B2 | VH4|4-34|D4|4-17|RF2|J H6 | .H...... | ...C.. | : : : | : : : | ...G---- | : : : |
| iPS:43 5075 | 21-225_91B3 | VH4|4-34|D4|4-17|RF2|J H6 | ........ | ...C.. | : : : | : : : | ...G---- | : : : |
| iPS:43 5077 | 21-225_91F3 | VH4|4-34|D4|4-17|RF2|J H6 | .H...... | ...C.. | : : : | : : : | ...G---- | : : : |
| iPS:43 5079 | 21-225_91B4 | VH4|4-34|D4|4-17|RF2|J H6 | .H...... | ...C.. | : : : | : : : | ...G---- | : : : |
| iPS:43 5089 | 21-225_91E9 | VH4|4-34|D4|4-17|RF2|J H6 | .H...... | ...C.. | : : : | : : : | ...G---- | : : : |
| iPS:43 5097 | 21-225_92B1 | VH4|4-34|D4|4-17|RF2|J H6 | ........ | ...S.. | ...Y..R. | ...A...N..T | ...G---- ---L.. | : : : |
| iPS:43 5111 | 21-225_92D6 | VH4|4-34|D4|4-17|RF2|J H6 | .H...... | ...C.. | : : : | : : : | ...G---- | : : : |
| iPS:43 5115 | 21-225_77C5 | VH4|4-34|D4|4-17|RF2|J H6 | ........ | ...C.. | : : : | : : : | ...G---- | : : : |
| iPS:43 5171 | 21-225_93C2 | VH4|4-34|D4|4-17|RF2|J H6 | .H...... | ...C.. | : : : | : : : | ...G---- | : : : |
| iPS:43 5177 | 21-225_93E4 | VH4|4-34|D4|4-17|RF2|J H6 | ...G....P | ...C.. | ...Y..R. | : : : | ...G---- | : : : |
| iPS:43 5195 | 21-225_94D3 | VH4|4-34|D4|4-17|RF2|J H6 | .H...... | ...C.. | : : : | : : : | ...G---- | : : : |
| iPS:43 5217 | 21-225_94F12 | VH4|4-34|D4|4-17|RF2|J H6 | .H...... | ...C.. | : : : | : : : | ...G---- | : : : |

Figure 52 (Continued)

| | | | | | | |
|---|---|---|---|---|---|---|
| iPS:43 5219 | 21-225_95D2 | VH4|4-34|D4|4-17|RF2|J H6 | ........ ........ ........ | :C. ... ... | ... ... ... | ...G---- ... ... --- |
| iPS:43 5235 | 21-225_95F9 | VH4|4-34|D4|4-17|RF2|J H6 | ........ .H...... ........ | :C. ... ... | ... ... ... | ...G---- ... ... --- |
| iPS:43 5237 | 21-225_95G9 | VH4|4-34|D4|4-17|RF2|J H6 | ........ .H...... ........ | :C. ... ... | ... ... ... | ...G---- ... ... --- |
| iPS:43 5239 | 21-225_95H10 | VH4|4-34|D4|4-17|RF2|J H6 | ........ .H...... ........ | :C. ... ... | ... ... ... | ...G---- ... ... --- |
| iPS:43 5273 | 21-225_97A2 | VH4|4-34|D4|4-17|RF2|J H6 | ........ .H...... ........ | :C. ... ... | ... ... ... | ...G---- ... ... --- |
| iPS:43 5281 | 21-225_97E5 | VH4|4-34|D4|4-17|RF2|J H6 | ........ .H...... ........ | :C. ... ... | ... ... ... | ...G---- ... ... --- |
| iPS:43 7324 | 21-225_75C2 | VH4|4-34|D4|4-17|RF2|J H6 | ........ .H...... ........ | :C. ... ... | ... ... ... | ...G---- ... ... --- |
| iPS:43 7328 | 21-225_75D3 | VH4|4-34|D4|4-17|RF2|J H6 | ........ .H...... ........ | :C. ... ... | ... ... ... | ...G---- ... ... --- |
| iPS:43 7332 | 21-225_75F3 | VH4|4-34|D4|4-17|RF2|J H6 | ........ .H...... ........ | :C. ... ... | ... ... ... | ...G---- ... ... --- |
| iPS:43 7344 | 21-225_75G12 | VH4|4-34|D4|4-17|RF2|J H6 | ........ .H...... ........ | :C. ... ... | ... ... ... | ...G---- ... ... --- |
| iPS:43 7350 | 21-225_74A3 | VH4|4-34|D4|4-17|RF2|J H6 | ........ .H...... ........ | :C. ... ... | ... ... ... | ...G---- ... ... --- |
| iPS:43 7369 | 21-225_74D6 | VH4|4-34|D4|4-17|RF2|J H6 | ........ .H...... ........ | :C. ... ... | ... ... ... | ...G---- ... ... --- |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3)3-33D4)4-17)RF2/JH6 | | QVQLVES-SGGTVQPGRSLR LSCAASG FTFS | S-----YGMH | WVRQAPGK GLEWVA | ISNPYTAD SVKG | RF ISRDNSKNTVYLQM NSLRAEDTAVYYCAR | AYGSFY-------TYYGMDV | WGQGT TVTSS |
| iPS:46 8814 | 21-225_223D11 | VH3J3-33D4J4-17JRF2/J H6 | N....... .D | | .D. | | .R.IG.- ND... | |
| iPS:43 4621 | 21-225_74D1 | VH3J3-33D4J4-17JRF2/J H6 | | | .H. | .M. | E.FGEFD. ...Y.N.. | |
| iPS:43 4947 | 21-225_87B7 | VH3J3-33D4J4-17JRF2/J H6 | | | .N. | | .F.VG.- | |
| iPS:43 5819 | 21-225_190C11 | VH3J3-33D4J4-17JRF2/J H6 | | | .N. | | .Q.VG.- D.L.. | |
| iPS:43 5825 | 21-225_190G11 | VH3J3-33D4J4-17JRF2/J H6 | I....... | | .N. | | .Q.VG.- D.L.. | |
| iPS:43 5837 | 21-225_198G3 | VH3J3-33D4J4-17JRF2/J H6 | T....... ...K... | | .T.N. | .C. | .Q.VG.- D.L.. | |
| iPS:43 5845 | 21-225_191G1 | VH3J3-33D4J4-17JRF2/J H6 | | | .EH. | | .R.VG.- ..L.. | |
| iPS:43 5859 | 21-225_190E6 | VH3J3-33D4J4-17JRF2/J H6 | | | .N. | | .Q.VG.- D.L.. | |
| iPS:43 5873 | 21-225_190G4 | VH3J3-33D4J4-17JRF2/J H6 | | | .N. | .M. | .Q.VG.- D.L.. | S |
| iPS:43 5933 | 21-225_190F8 | VH3J3-33D4J4-17JRF2/J H6 | T....... | | .N. | | .Q.VG.- D.... | |

Figure 52 (Continued)

| | | | | | | | | |
|---|---|---|---|---|---|---|---|---|
| iPS:43 5941 | 21-225_191E8 | VH3\|3-33\|D4\|4-17\|RF2/J H6 | . . . . . . | N . . . . . | . . . . . . | I . F . . Q | L . . . . . | AH.V... .A... |  . . . . . |
| iPS:43 5945 | 21-225_191A10 | VH3\|3-33\|D4\|4-17\|RF2/J H6 | . . . . . . | . . . . . . | . . . . . . | . N . . . . | . . . . . . | .Q.VG.- D.L.. | S . . . . |
| iPS:43 5947 | 21-225_191E10 | VH3\|3-33\|D4\|4-17\|RF2/J H6 | . . . . . . | . . . . . . | . . . . . . | . N . . . . | . M . . . . | .Q.VG.- D.L.. | S . . . . |
| iPS:43 5957 | 21-225_191G12 | VH3\|3-33\|D4\|4-17\|RF2/J H6 | . . . . . . | . . . . . . | . . . . . . | . N . . . . | . M . . . . | .Q.VG.- D.L.. |  . . . . . |
| iPS:43 5963 | 21-225_192D2 | VH3\|3-33\|D4\|4-17\|RF2/J H6 | . . . . . . | . . . . . . | . . . . . . | . N . . . . | . M . . . . E | .R.VG.- . . . . . |  . . . . . |
| iPS:43 5971 | 21-225_192D3 | VH3\|3-33\|D4\|4-17\|RF2/J H6 | . . . . . . | . . . . . . | . . . . . . | . EH . . . . | . . . . . . | .R.VG.- . L . . |  . . . . . |
| iPS:43 5979 | 21-225_192H4 | VH3\|3-33\|D4\|4-17\|RF2/J H6 | . . . . . . | . . . . . . | . . . . . . | . N . . . . | . . . . . . | .Q.VG.- . . . . . |  . . . . . |
| iPS:43 5987 | 21-225_192G6 | VH3\|3-33\|D4\|4-17\|RF2/J H6 | . . . . . . | . . . . . . | . . . . . . | . L . . . . T . N | . M . . . . | .Q.VG.- D.L.. |  . . . . . |
| iPS:43 5993 | 21-225_192C8 | VH3\|3-33\|D4\|4-17\|RF2/J H6 | . . . . . . | . . . . . . | . . . . . . | . EH . . . . | . . . . . . | .R.VG.- . . . . . |  . . . . . |
| iPS:43 5997 | 21-225_192G8 | VH3\|3-33\|D4\|4-17\|RF2/J H6 | . . . . . . | . . . . . . | . . . . . . | . N . . . . | . . . . . . | .Q.VG.- . . . . . |  . . . . . |
| iPS:43 6005 | 21-225_192H10 | VH3\|3-33\|D4\|4-17\|RF2/J H6 | . . . . . . | . . . . . . | . . . . . . | . N . . . . | . M . . . . | .Q.VG.- D.L.. | S . . . . |
| iPS:43 6031 | 21-225_193C7 | VH3\|3-33\|D4\|4-17\|RF2/J H6 | . . . . . . | . . . . . . | . . . . . . | . N . . . . | . M . . . . | .Q.VG.- D.L.. | S . . . . |

Figure 52 (Continued)

| | | | | | | | | |
|---|---|---|---|---|---|---|---|---|
| iPS:43 6045 | 21-225_193A10 | VH3\|3-33\|D4\|4-17\|RF2/J H6 | ... | ... | ... | ... | R.VG.- | ... |
| iPS:43 6076 | 21-225_194H11 | VH3\|3-33\|D4\|4-17\|RF2/J H6 | ... | ... | .EH | S | ..L.. | ... |
| iPS:43 6086 | 21-225_191G10 | VH3\|3-33\|D4\|4-17\|RF2/J H6 | ... | ... | .EH | ... | Q.VG.- D.L.. | ... |
| iPS:43 6090 | 21-225_195A9 | VH3\|3-33\|D4\|4-17\|RF2/J H6 | ... | ..Q | .N | ... | R.VG.- ..L.. | ... |
| iPS:43 6112 | 21-225_196C7 | VH3\|3-33\|D4\|4-17\|RF2/J H6 | ... | ... | .EH | ... | R.VG.- ..L.. | ... |
| iPS:43 6138 | 21-225_197F2 | VH3\|3-33\|D4\|4-17\|RF2/J H6 | ... | ... | .N | ... | Q.VG.- D.L.. | ... |
| iPS:43 6152 | 21-225_197B6 | VH3\|3-33\|D4\|4-17\|RF2/J H6 | ... | ... | .N | .M. .M. | Q.VG.- D.L.. | ... |
| iPS:43 6173 | 21-225_197G12 | VH3\|3-33\|D4\|4-17\|RF2/J H6 | ... | ... | .H | ... | Q.VG.- D.L.. | ... |
| iPS:43 6189 | 21-225_198B6 | VH3\|3-33\|D4\|4-17\|RF2/J H6 | ... | ... | .N | ... | Q.VG.- ... | ... |
| iPS:43 6201 | 21-225_199C5 | VH3\|3-33\|D4\|4-17\|RF2/J H6 | ... | .N | I.F. .Q | ... | Q.VG.- ... | ... |
| iPS:43 6203 | 21-225_199A6 | VH3\|3-33\|D4\|4-17\|RF2/J H6 | ... | ... | ... | ..L | AH.V.- .A... | ... |
| iPS:43 6282 | 21-225_204G6 | VH3\|3-33\|D4\|4-17\|RF2/J H6 | ..T | ... | .N | ... | R.VG.- ..D.. | ... |

Figure 52 (Continued)

| | | | | | | | | |
|---|---|---|---|---|---|---|---|---|
| iPS:43 6296 | 21-225_205F5 | VH3\|3-33\|D4\|4-17\|RF2/J H6 | ........ | R........ | ....... | ...EN.V. .... | .......T.KM.F ....TD........ | M.IG.— ....... |
| iPS:43 6324 | 21-225_207G6 | VH3\|3-33\|D4\|4-17\|RF2/J H6 | ........ | ........ | ....... | ....N..E .... | ............ | A.IG.— ..I.... |
| iPS:43 6364 | 21-225_211A11 | VH3\|3-33\|D4\|4-17\|RF2/J H6 | ......G. | ........ | ....... | ...L.F. .RN. | ............ | R.VG.— ..T.... |
| iPS:43 6372 | 21-225_211A8 | VH3\|3-33\|D4\|4-17\|RF2/J H6 | ........ | ........ | ....... | ....EH. .... | ........K.... | H.VG.— ....... |
| iPS:43 6376 | 21-225_212E6 | VH3\|3-33\|D4\|4-17\|RF2/J H6 | ........ | ........ | ....... | ....N.V. .... | ............ | ...VG.— ..T.... |
| iPS:43 6378 | 21-225_212D7 | VH3\|3-33\|D4\|4-17\|RF2/J H6 | ........ | ........ | ....... | ....N... .... | .........S.... | ...VG.— ..T.... |
| iPS:43 6380 | 21-225_212H9 | VH3\|3-33\|D4\|4-17\|RF2/J H6 | ........ | ........ | ....... | ....EH. .... | ........K.... | H.VG.— ....... |
| iPS:43 6384 | 21-225_212F10 | VH3\|3-33\|D4\|4-17\|RF2/J H6 | ........ | R........ | ....... | ....H.. .... | ......G....... | R.VG.— N...... |
| iPS:43 6390 | 21-225_213D2 | VH3\|3-33\|D4\|4-17\|RF2/J H6 | ........ | ........ | ....... | ....N... .... | .........S.... | ...VG.— ....... |
| iPS:43 6394 | 21-225_213C4 | VH3\|3-33\|D4\|4-17\|RF2/J H6 | ....T... | ........ | ....... | ....H.. .... | ............ | ...VG.— D...... |
| iPS:43 6398 | 21-225_213B8 | VH3\|3-33\|D4\|4-17\|RF2/J H6 | ........ | ........ | ....... | ....H.. .... | ............ | ...VG.— ..T.... |
| iPS:43 6404 | 21-225_214C3 | VH3\|3-33\|D4\|4-17\|RF2/J H6 | ......E. | ........ | ....... | ....N.G .... | ............ | R.VG.— D...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| VH3/3-33/D4/4-17/RF2/JH4 | Germline | QVQLVES-GGGVVQPGRSLR LSCAASG-FTFS | S------YGMH | WVRQAPGK GLEWVA | VIWYD--GSNKYYAD SVKG | RFTISRDNSKNTLYLQM NSLRAEDTAVYYCAR | DYGDY------IFDY | WGQGTL VTVSS |
| iPS:43 6410 | 21-225_212E10 | VH3/3-33/D4/4-17/RF2/JH6 | . . . . . . . . . . . . . . . . . . . . . . . | . . . . . . . . . . . | . . . . . . . . | . . . . . . . . . . . . | . . . . . . S . . . . . . . . . . . . . . . | . . . VG.-. . . . . T . . | . . . . . |
| iPS:43 6420 | 21-225_215B5 | VH3/3-33/D4/4-17/RF2/JH6 | . . . . . . . . . K . . . . . . . . . . . . | . . . . . . . . . . . | . . . . . . . . | . . . . . . . N . . . . | . . . . . . S . . . . . . . . . . . . . . . | . . . VG.-. . . . . T . . | . . . . . |
| iPS:43 6422 | 21-225_215D6 | VH3/3-33/D4/4-17/RF2/JH6 | . . . . . . . . . . . . . . . . . . . . . . . | . . . . . . . . . . . | . . . . . . . . | . . . . . . . N . . . . | . . . . . . . . . . . . . . . . . . . . . . | . . C . VG.-. . . . . T . . | . . . . . |
| iPS:43 6430 | 21-225_215A12 | VH3/3-33/D4/4-17/RF2/JH6 | . . . . . . . . . . . . . . . . L . . . . . | . . . . . N . . . . . | . . . . . . . . | . . . . . . . EH . . . | . . . . . . . . . . . . . . . . . . . . . . | . . R . VG.-. . . . . L . . | . . . . . |
| iPS:43 6452 | 21-225_217G5 | VH3/3-33/D4/4-17/RF2/JH6 | . . . . . . . . R . . . . . . . . . . . . . | . . . . . . . . . . . | . . . . . . . . | . . . . . . . . H . . . | . . . . . . . . . . . . . . . . . . . . . . | . . . VG.-. . . . . . . . | . . . . . |
| iPS:43 6464 | 21-225_219H1 | VH3/3-33/D4/4-17/RF2/JH6 | . . . . . . . . . . . . . . . . . . . . . . . | . . . . . . . . . . . | . . . . . . . . | . . . . . . . . . . . . | . . . . . . . . . . . . G . . . . . . . . . | . . R . VG.-. . . . N . . . | . . . . . |
| iPS:45 1120 | 21-225_197D3 | VH3/3-33/D4/4-17/RF2/JH6 | . . . . . . . . . I . . . . . . . . . . . . | . . . . . . . H . . . | . . . . . . . . | . . . . . . . EH . . . | . . . . . . . . . . . . . . . . . . . . . . | . . Q . VG.-. . . . . . . . | . . . . . |
| iPS:46 8822 | 21-225_147E10 | VH3/3-33/D4/4-17/RF2/JH4 | . . . . . . . . . . . . . . . . . . . . . . . | N . . . . . . L . . . | . . . . . . . . | I . . . . . . . . . . . | . . . . . . . . . . . . . . . . . . . . . . | . HY.FW. . . . . . . . SGH . . | . . . . . |
| iPS:43 3965 | 21-225_46F2 | VH3/3-33/D4/4-17/RF2/JH4 | . . . . . . . . . . . . . . . . . . . . . . . | . . . . . . . . . . . | . . . . . . . . | I . . . . . . . . V . . | . . . . . . . . . . . . . . . . . . . . . . | . RY.FW. . . . . . . . SG . . | . . . . . |
| iPS:43 4255 | 21-225_62E6 | VH3/3-33/D4/4-17/RF2/JH4 | . . . . . . . . . . . . . . . . . . . . . . . | . . . . . . . . . . . | . . . . . . . . | A . . . . . . . . G . . | . . . . . V . . . . . . . . . . . . S . H . . | . Q . IVG . . . . . . . ATW . . | . . . . . |

Figure 52 (Continued)

| | | | | | | | | |
|---|---|---|---|---|---|---|---|---|
| iPS:43_4269 | 21-225_57H3 | VH3\|3-33/D4\|4-17\|RF2/JH4 | ... | ... | ... | A... | ... | .IVG......AT... |
| iPS:43_4345 | 21-225_64H9 | VH3\|3-33/D4\|4-17\|RF2/JH4 | ...I | ... | ... | ... | ... | TY.FW......SG.LG. |
| iPS:43_4363 | 21-225_65A6 | VH3\|3-33/D4\|4-17\|RF2/JH4 | ...N | ... | ...G. | I... | ... | Q.IVG......ATW... |
| iPS:43_4393 | 21-225_67C3 | VH3\|3-33/D4\|4-17\|RF2/JH4 | ... | ... | ...G. | A... | .V....S.H. | Q.IVG......ATW... |
| iPS:43_4425 | 21-225_70A5 | VH3\|3-33/D4\|4-17\|RF2/JH4 | ... | ... | ... | ... | ...S...... | Q.IVG......ATW... |
| iPS:43_5341 | 21-225_148B2 | VH3\|3-33/D4\|4-17\|RF2/JH4 | ... | ... | ...Y. | I... | ...S...... | HF.FW......SGH... |
| iPS:43_5357 | 21-225_148G10 | VH3\|3-33/D4\|4-17\|RF2/JH4 | ... | ... | ... | I... | ... | RY.FW......SGH... |
| iPS:43_5365 | 21-225_149F1 | VH3\|3-33/D4\|4-17\|RF2/JH4 | ... | ... | ...Y. | I... | ...S...... | HF.FW......SGH... |
| iPS:43_5413 | 21-225_150B11 | VH3\|3-33/D4\|4-17\|RF2/JH4 | ...M | ...I | ... | I... | ... | RY.FW......SGH... |
| iPS:43_5423 | 21-225_151G5 | VH3\|3-33/D4\|4-17\|RF2/JH4 | ... | ...N | ... | I... | ... | RY.FW......SGH... |
| iPS:43_5429 | 21-225_151A10 | VH3\|3-33/D4\|4-17\|RF2/JH4 | ... | ...L | ... | I... | ... | HY.FW......SGH... |
| iPS:43_5489 | 21-225_155A5 | VH3\|3-33/D4\|4-17\|RF2/JH4 | ...D | ... | ...S. | I... | ...H. | RY.FW......SGH... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5683 | 21-225_170A1 | VH3J3-33/D4J4-17JRF2/J H4 | | | | ...I... ..Y... | | ...AH.FW... .....SG...S | ...A |
| iPS:43 5755 | 21-225_176H4 | VH3J3-33/D4J4-17JRF2/J H4 | | | | ...I... ..Y... | ...S......... | ...AH.FW... .....SG...A | |
| iPS:43 5795 | 21-225_181C2 | VH3J3-33/D4J4-17JRF2/J H4 | | | ...T... | ...I... ..Y... | | ...HY.FW... .....SGH..F | |
| iPS:43 5807 | 21-225_181C10 | VH3J3-33/D4J4-17JRF2/J H4 | | | ...M... | ...I... ..Y... | | ...HY.FW... .....SGH... | |
| iPS:43 5887 | 21-225_186F7 | VH3J3-33/D4J4-17JRF2/J H4 | | ...T... | | ...I... ..Y... | | ...HY.FW... .....SGH... | |
| iPS:43 5901 | 21-225_189G2 | VH3J3-33/D4J4-17JRF2/J H4 | | ...N... | | ...I... ..Y... | | ...RF.FW... .....SG...S | |
| iPS:43 6594 | 21-225_226A5 | VH3J3-33/D4J4-17JRF2/J H4 | | ...N... | | ...I.T. ..T... | | ...EGH.FW... .....SGF.C | |
| iPS:39 2814 | 21-225_22A1 | VH3J3-33/D4J4-17JRF2/J H4 | | ...T... | | ...M... | | ...G.FL... .....EWL... | |
| iPS:39 3036 | 21-225_28G3 | VH3J3-33/D4J4-17JRF2/J H4 | ...I... | | | | | ...RY.FW... .....SG... | |
| Germline | VH3J3-33/D7J7-27JRF1/JH4 | QVQLVES GGGVVQPGRSLR LSCAASG-FTFS | ...YGMH | WVRQAPGK GLEWVA | VIWYD-GSNKYYAD SVKG | RFTISRDNSKNTILYLQM NSLRAEDTAVYYCAR | EGY-----------------FDY | WGQGTL VTVSS |
| iPS:46 8824 | 21-225_73G6 | VH3J3-33/D7J7-27JRF1/JH4 | | | | ...V......G | | ...EV.M....TS... | |

Figure 52 (Continued)

| | | | | | | | |
|---|---|---|---|---|---|---|---|
| iPS:43 4169 | 21-225_50C4 | VH3j3-33/D7j7-27jRF1/J H4 | ........D... | ........... | ........E... ET... | ........... | EV.F......LN | ....I.... |
| iPS:43 5045 | 21-225_90H5 | VH3j3-33/D7j7-27jRF1/J H4 | ........D... | ......S.... | ........E... ....T | ......V.... | EM.W......LD | ......... |
| iPS:43 5367 | 21-225_149G1 | VH3j3-33/D7j7-27jRF1/J H4 | ........D... | ........... | ........E... | ......M.... | EI.F......SE | ......... |
| iPS:43 5397 | 21-225_149F12 | VH3j3-33/D7j7-27jRF1/J H4 | ........D... | ........... | EN......E... | ......F.... | EI.F......SE | ......... |
| iPS:43 5407 | 21-225_150E7 | VH3j3-33/D7j7-27jRF1/J H4 | ........D... | ........... | EN......E... | ...F....... | EI.F......SE | ......... |
| iPS:43 5609 | 21-225_161F7 | VH3j3-33/D7j7-27jRF1/J H4 | ........D.F.L | ......Q.... | ........F... | ...F....... | EI.W......LS | ......... |
| iPS:43 5613 | 21-225_161D11 | VH3j3-33/D7j7-27jRF1/J H4 | ........D.F.L | ......Q.... | ........F... | ......V.... | EI.W......LS | ......... |
| iPS:43 5791 | 21-225_180H7 | VH3j3-33/D7j7-27jRF1/J H4 | ........D... | ........... | EN...H...A.. | ........... | EV.W......SD | ......... |
| iPS:43 5805 | 21-225_181A8 | VH3j3-33/D7j7-27jRF1/J H4 | ........D..V | ........... | EN...H...A.. | ......D.... | EV.W......SD | ....I.... |
| iPS:43 5879 | 21-225_184H10 | VH3j3-33/D7j7-27jRF1/J H4 | ........D... | ........... | ET...H.G.... | ......D.... | EV.W......HD | ......... |
| iPS:43 5881 | 21-225_184D11 | VH3j3-33/D7j7-27jRF1/J H4 | ........D... | ........... | ET...H.G.... | ......D.S.. | EV.W......HD | ......... |
| iPS:43 6350 | 21-225_210E4 | VH3j3-33/D7j7-27jRF1/J H4 | ........N.LI | ........... | EN.....V.... | ........... | EI.F......LS | ......... |

Figure 52 (Continued)

| | | | | | | | | |
|---|---|---|---|---|---|---|---|---|
| iPS:43 6576 | 21-225_225B6 | VH3j3-33/D7j7-27jRF1/J H4 | .R........ | D......... | .......... | EN....... | .......... | EV.F.....TE. | .......... |
| iPS:43 6578 | 21-225_225D6 | VH3j3-33/D7j7-27jRF1/J H4 | .......... | N......... | .......T.. | EN....... | ....Q..... | EV.F.....TE. | .......... |
| iPS:43 6582 | 21-225_225F8 | VH3j3-33/D7j7-27jRF1/J H4 | .......... | .......... | .......... | EN.....V. | .......... | EV.F.....TE. | .......... |
| iPS:43 6608 | 21-225_226A9 | VH3j3-33/D7j7-27jRF1/J H4 | .......... | N......... | .......... | E...E...T. | .....F.... | EV.F.....TE. | .......... |
| iPS:43 6630 | 21-225_227G3 | VH3j3-33/D7j7-27jRF1/J H4 | .......... | .......... | .......... | ....V....Q. | .....S.... | EV.F.....TE. | .......... |
| iPS:43 6634 | 21-225_227H5 | VH3j3-33/D7j7-27jRF1/J H4 | ....K..... | N......... | ...D...... | ...E...... | .....M.... | EV.F.....TE. | .......... |
| iPS:43 6650 | 21-225_227C12 | VH3j3-33/D7j7-27jRF1/J H4 | .......... | D......... | .......... | ...I...Q.. | .....S.... | EV.W.....LD. | .......... |
| iPS:43 7280 | 21-225_203C10 | VH3j3-33/D7j7-27jRF1/J H4 | .......... | .......... | .....M.... | .G.TH.T... | .......... | EV.W.....YE. | .......... |
| iPS:39 2740 | 21-225_18H12 | VH3j3-33/D7j7-27jRF1/J H4 | .......... | .......... | .......... | VT........ | .......... | EV.F.....RS. | .......... |
| iPS:39 2780 | 21-225_22B7 | VH3j3-33/D7j7-27jRF1/J H4 | .......... | .......... | .......... | EN.Q...... | .......... | EI.W.....LD. | .......... |
| iPS:39 2912 | 21-225_25A9 | VH3j3-33/D7j7-27jRF1/J H4 | .......... | .......... | .......... | VT.....TG. | .......... | EI.W.....LD. | .......... |
| iPS:39 2940 | 21-225_29D9 | VH3j3-33/D7j7-27jRF1/J H4 | ....K....S | D........I | .......... | E..N...... | .......... | EI.W.....LD. | ....Q..... |

Figure 52 (Continued)

| | | | | | | | | |
|---|---|---|---|---|---|---|---|---|
| iPS:39 2948 | 21-225_25G5 | VH3\|3-33/D7\|7-27\|RF1/J H4 | . . . | D . . . . . I . | . . . . . . . . . N . . . . | . . . . . . . . . N . . . . | . . . . . . . . . . . . . . | EI.W . . . . . LD . . . . |
| iPS:39 2978 | 21-225_28B8 | VH3\|3-33/D7\|7-27\|RF1/J H4 | . . . | D . . . . . . . | . . . T . . . AN . . . . | . . . . . . . . . . . . | . . . . . . . . . . . . . . | EI.W . . . . . LD . . . . |
| iPS:39 2998 | 21-225_28A9 | VH3\|3-33/D7\|7-27\|RF1/J H4 | . . . | . . . . . . I . | . . . . . . . F . . . . | . . . . . . . . V . . . | . . . . . . . F . . V . . | EI.W . . . . . LD . . . . |
| iPS:39 3038 | 21-225_29D8 | VH3\|3-33/D7\|7-27\|RF1/J H4 | . . . . . . K | D . . . . . I . | . . . T . . . F . . . . | . . . . . . . . . . . . | . . . . . . . . F . . . . | EI.W . . . . . LD . . . . |
| iPS:39 3056 | 21-225_30F3 | VH3\|3-33/D7\|7-27\|RF1/J H4 | . . . | . . . . . . . . | . . . . . V . . . . . . | . . . . . . . . . . . . | . . . . . . . . . G . . . | EM.W . . . . . YD . . . . |
| iPS:39 3074 | 21-225_33B1 | VH3\|3-33/D7\|7-27\|RF1/J H4 | . . . | D . . . . . . A | . . . . . RN . . . . . | . . . . . . . . . . . . | . . . . . . . . . . . . . . | EM.W . . . . . YD . . . . |
| iPS:39 3822 | 21-225_15B11 | VH3\|3-33/D7\|7-27\|RF1/J H4 | . . . | N . . . . . . . | . . . E . . . . T . . . | K . . . . . . . . . . . | . . . . . . . . . P . . . | EV.F . . . . . TE . . . . |
| iPS:39 3856 | 21-225_14C2 | VH3\|3-33/D7\|7-27\|RF1/J H4 | . . . | D . . . . . . . | . . . E . . . . E . . . | . . . . . . . . . T . . | . . . . . . . . . . G . . | EV.F . . . . . RS . . . . |
| iPS:39 3874 | 21-225_4C8 | VH3\|3-33/D7\|7-27\|RF1/J H4 | . . . | . . . . . . . . | . . EN.Q . . . . . . | . . . TF.N.GG.ENQ | . . . . . . . . . SP . . | EM.F . . . . . LS . . . . |
| iPS:39 3984 | 21-225_4F12 | VH3\|3-33/D7\|7-27\|RF1/J H4 | . . . | . . . . . . . . | . . VT.K . . . . . . | . . . . . . . . . . . . | . . . . . . . . . . . . . . | EK.G . . . . . L . . . . |
| iPS:39 4020 | 21-225_15H10 | VH3\|3-33/D7\|7-27\|RF1/J H4 | . . . | N . . . . . . . | . . . E . . . . E . . . | . . . . . . . . . . . . | . . . . . . . . . V . . . | EV.F . . . . . LS . . . . I . . . |
| iPS:39 4095 | 21-225_16H4 | VH3\|3-33/D7\|7-27\|RF1/J H4 | . . . | N . . . . . . . | . . . V . . . . . . . . | . . . . . . . . . . . . | . . . . . . . . . M . . . | EM.W . . . . . TD.C |

| | | H_FR1 | H_CDR1 | H_FR2 | H_CDR2 | H_FR3 | H_CDR3 | H_FR4 |
|---|---|---|---|---|---|---|---|---|
| | Germline | VH1|1-02/D5|5-18|RF3/JH4 | | | | ..........V. | ...........C. .........F..... | SFF...SGS........YNE.... | |
| iPS:39 8470 | 21-225_14B7 | .................. | S.....YAFH | .NYRQAPGK WISVA | GSNKYTAQ SVKG | ..K.............. | | |
| | VH3|3-30.3/D1|1-1|RF1/JH6 | CVQLVES-GGGVVQPGRSLR LSCAASG FTFS | S.....YGMH | .NWVRQAPGK GLEWVA | VISYD-GSNKYYAD SVKG | RFTISRDNSKNTLYLQM NSLRAEDTAVYYCAR | GTTCYY...YYYGMDV | WGQGTT VTVSS |
| iPS:46 8836 | 21-225_198E3 | ................ | .......G. | ................ | .GY.N... | ................ | ..H.Y.-.......... ....V.. | --- |
| iPS:43 5831 | 21-225_190C12 | .........A...... | .......G. | ................ | .GY.N.V. | ................ | ..H.Y.-.......... ....V.. | --- |
| iPS:43 5857 | 21-225_191A4 | ................ | .......G. | ................ | .GY.N... | ................ | ..H.Y.-.......... ....V.. | --- |
| iPS:43 5907 | 21-225_190G3 | ................ | .......G. | ................ | .GY.N.V. | ................ | ..H.Y.-.......... ....V.. | --- |
| iPS:43 5919 | 21-225_190H5 | ................ | .......G. | ..........T..... | .GY.N... | ................ | ..H.Y.-.......... ....V.. | --- |
| iPS:43 5989 | 21-225_192F7 | ................ | .......G. | ................ | .GY.N... | ................ | ..H.Y.-.......... ....V.. | --- |
| iPS:43 6222 | 21-225_200C9 | ................ | .......G. | ................ | .GY.N.I. | ..............F.. | ..H.Y.-.......... ....V.. | --- |
| | Germline | H_FR1 | H_CDR1 | H_FR2 | H_CDR2 | H_FR3 | H_CDR3 | H_FR4 |
| | VH4|4-30.1/D5|5-24|RF3/JH6 | CVQLQES GPGLVKPSQTLS LTCTVSG GSIS | SS....GYYWS | .WIRQPPGK GLEWIG | YIYY...SGSTYYNP SLKS | RVTISVDTSKNQFSLRL RSVTAADTAVYYCAR | GTYCNYYY...YYYGMDV | WGQGTT VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS-46 8840 | 21-225_200H9 | VH4|4-30.1/D5|5-24|RF3/JH6 | ........I ......MR | .........D.. | ......F. | | .....L... | M.YS.-- | .....S |
| iPS-43 6096 | 21-225_195E10 | VH4|4-30.1/D5|5-24|RF3/JH6 | | | | | ....A... | GGYNWN-- ...H.... | |
| iPS-43 6120 | 21-225_196C10 | VH4|4-30.1/D5|5-24|RF3/JH6 | ........W ......MR | .........D.. | ......F. | | .....L... | M.YS.-- | |
| iPS-43 6216 | 21-225_200B7 | VH4|4-30.1/D5|5-24|RF3/JH6 | | | | ...F..N... ....R... | | AGYNWN-- ...N.... | |
| VH3|3-21|D6|6-6|RF2/JH4 | | EVQLVES GGGLVKPGGSLR LSCAASG-FTFS | S....YSMN | WVRQAPGK GLEWVS | SISSS SSIYYAD SVKG | RFTISRDNAKNSLY LQM NSLRAEDTAVYYCAR | STXAR------YFDY | WGQGTL VTVSS |
| iPS-46 8844 | 21-225_48E10 | VH3|3-21/D6|6-6|RF2/JH4 | ........N... | | ...G... | | .L---- | |
| iPS-43 5537 | 21-225_157H12 | VH3|3-21/D6|6-6|RF2/JH4 | ........W | | ...G...N... | .........T....V | ....L | |
| iPS-43 5539 | 21-225_158G1 | VH3|3-21/D6|6-6|RF2/JH4 | ...G.... | | ...G... | .........I | KF---- ....S | |
| iPS-43 5583 | 21-225_160F2 | VH3|3-21/D6|6-6|RF2/JH4 | ...G.... | | ...G... | .........I | SG--- ....WS | |
| | Germline | H_FR1 | H_CDR1 | H_FR2 | H_CDR2 | H_FR3 | H_CDR3 | H_FR4 |
| VH3|3-21|D1|1-1|RF2/JH5 | | EVQLVES GGGLVKPGGSLR LSCAASG-FTFS | S....SMN | WVRQAPGK GLEWVS | SISSS SSIYYAD SVKG | RFTISRDNAKNSLY LQM NSLRAEDTAVYYCAR | VGLER------NWFDP | WGQGTL VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:46 8846 | 21-225_53B10 | VH3|3-21|D1|1-1|RF2/JH5 | ........... ........... ........... | ....... | ........... ........... ........... | G.....V ....... ....... | ........... ........... ........... | .NS-- ......S ......S |
| iPS:43 4251 | 21-225_62G3 | VH3|3-21|D1|1-1|RF2/JH5 | ........... ........... ........... | ....... | ........... ........... ........... | ....... ....... ....... | ........... ........... ........... | .NS-- ......S ......S |
| iPS:43 4407 | 21-225_68G8 | VH3|3-21|D1|1-1|RF2/JH5 | ........... ........... ........... | ....... | ........... ........... ........... | G..... ..M... ....... | ........... ........... ........... | .NS-- ......S ......S |
| iPS:43 5575 | 21-225_159H11 | VH3|3-21|D1|1-1|RF2/JH5 | ........... ........... ........... | ...T... | ........... ........... ........... | G..... ....... ....... | ........... ........... ........... | .SW-- --A.C ....... |
| Germline | | H_FR1 EVQLLES- CGGGLVQPGGSLR LSCAASG-FTFS | H_CDR1 S-------YAMS | H_FR2 WVRQAPGK GLEWVS | H_CDR2 AISGS GGSTYYAD SVKG | H_FR3 RFTISRDNSKNTLYLQM NSLRAEDTAVYYCAR | H_CDR3 -------- YFDY | H_FR4 WGQGTL VTVSS |
| iPS:46 8848 | 21-225_54B1 | VH3|3-23|D1|1-1|RF2/JH4 | ........... ........... ........... | ....... | ........... ........... ........... | VL.... ...F... ....... | ...........E ...S....R ........... | RGR.YSG ....YD. ....... |
| iPS:43 3993 | 21-225_47G7 | VH3|3-23|D1|1-1|RF2/JH4 | ...D....... ........... ........... | ....... | ........... ........... ........... | ...R... .N.F..E ..R.... | ........... ........... ........... | IIR.Q.. ....WA. ....... |
| iPS:43 4007 | 21-225_48D7 | VH3|3-23|D1|1-1|RF2/JH4 | ........... ........... ........R.. | N....S..N | ........... ........... ........... | ..T.F.. ....... ....... | ...........I ........... ........... | CGR.Q.. ....WL. ....... |
| iPS:43 4115 | 21-225_53E4 | VH3|3-23|D1|1-1|RF2/JH4 | ........... ........... ........... | ...V... | ........... ........... ........... | G...... ....R.. ....... | ...N....... ........... ........... | .A.--- ....... ....... |
| iPS:43 5679 | 21-225_169D10 | VH3|3-23|D1|1-1|RF2/JH4 | ....S...... ........... ........... | ...V... | ........... ........... ........... | .SRI... ....... ....... | ........... ........L..R ........... | .AF--- ....... ....... |
| iPS:43 5685 | 21-225_170E1 | VH3|3-23|D1|1-1|RF2/JH4 | ........... ........... ........... | ...V... | ........... ........... ........... | .NRI... ....... ....... | ........... ........L..R ........... | .AF--- ....... ....... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:43 6632 | 21-225_227E4 | VH3J3-23/D1|1-1|RF2/JH4 | .G........... | T......F..T | ....RV...R... ...SF... | ........T...... | D..W— ...—..... | |
| | VH4|4-39/D4|4-11|RF2/JH5 | Germline | QVQLQES-GPGLVKPSETLS LTCTVSG-GSIS | H_FR1 | SS--SYYWG H_CDR1 | WIRQPPGK GLEWIG H_FR2 | SIYYSGSTYYNPSLKS H_CDR2 | RVTISVDTSKNQFSLKL SSVTAADTAVYYCAR H_FR3 | DYSNY------NWFDP H_CDR3 | WGQGT LVTVSS H_FR4 |
| iPS:46 8856 | 21-225_77C9 | VH4|4-39/D4|4-11|RF2/JH5 | ..T.......... | .R.......... | ............... | ...A.S......... | ............LF.... | LD.W.........—GL.Y | |
| iPS:43 4489 | 21-225_74E4 | VH4|4-39/D4|4-11|RF2/JH5 | ......I..... | ...N........ | ............... | ...Y.S......... | .........S....H...R | LD.W.........—GL.Y | |
| iPS:43 5251 | 21-225_96A3 | VH4|4-39/D4|4-11|RF2/JH5 | ......I..... | ...N........ | ............... | ...Y.S......... | .........S....H...R | LD.W.........—GL.Y | |
| iPS:43 7346 | 21-225_75H7 | VH4|4-39/D4|4-11|RF2/JH5 | ..T.......... | .R.......... | ............... | ...A.S......... | ............LF.... | LD.W.........—GL.Y | |
| iPS:39 3886 | 21-225_2G9 | VH4|4-39/D4|4-11|RF2/JH5 | .............R | PN...-....... | ............... | ....S.... ..N. | N............... | LS.W........—D..N | |
| iPS:39 3928 | 21-225_4E10 | VH4|4-39/D4|4-11|RF2/JH5 | ............ | .R.......... | ............... | ..V....A.S..... | N..........L..V. | LS.W........—D..Y | F..... |
| | VH1|1-02/D6|6-6|RF1/JH6 | Germline | QVQLVQS-GAEVKKPGASVK VSCKASG-YTFT | H_FR1 | G.......SYYMH H_CDR1 | WVRQAPGQ GLEWMG H_FR2 | WINPN--SGGTNYAQ KFQG H_CDR2 | RVTMTRDTSISTAYMEL SRLRSDDTAVYYCAR H_FR3 | EIGSSSWY------YFFGMDV H_CDR3 | WGQG TVTVSS H_FR4 |
| iPS:46 8862 | 21-225_178H8 | VH1|1-02/D6|6-6|RF1/JH6 | RT.......... | ...D........ | ............... | ......R........ | ............... | .EDR.GW........... | |
| iPS:45 1112 | 21-225_53D10 | VH1|1-02/D6|6-6|RF1/JH6 | ......I...... | ........I... | ............... | ............... | I............... | .NE.LATRP .....FYD.......... | |
| | | H_FR1 | H_CDR1 | H_FR2 | H_CDR2 | H_FR3 | H_CDR3 | H_FR4 |

Figure 52 (Continued)

| VH2\|2-05\|D6\|6-6\|RF2\|JH4 | | LFLLHS GFLVRFIQIII ICIGSG-FSHS | GVQPG | NRGGFT ALEWLA | LLVN MDLRRVSP SLKS | RLTISRDNSKNTVYL QMSSL | RAED TAATYYCAR | YFDY | WGQGTL VTVSS |
|---|---|---|---|---|---|---|---|---|---|
| iPS:46 8864 | 21-225_60D6 | VH2\|2-05\|D6\|6-6\|RF2\|JH4 | ........ | ........ | ........ | ........ | AV.V- ...S... | ........ | ........ |
| iPS:43 6850 | 21-225_57D9 | VH2\|2-05\|D6\|6-6\|RF2\|JH4 | ....M... | ........ | K.E..... | ....E... | AV.V- ...S... | ........ | ........ |
| iPS:43 6914 | 21-225_76B4 | VH2\|2-05\|D6\|6-6\|RF2\|JH4 | ........ | .G...... | ...D.... | ....P... | L..V- ...A... | ........ | ........ |
| iPS:43 6918 | 21-225_77A2 | VH2\|2-05\|D6\|6-6\|RF2\|JH4 | ....S... | ........ | ..V..... | F.D..... | ........ | L..V- ...A... | ........ | ........ |
| iPS:43 6934 | 21-225_96B5 | VH2\|2-05\|D6\|6-6\|RF2\|JH4 | ........ | .G...... | ...D.... | ....P... | L..V- ...AC.. | ........ | ........ |
| iPS:43 7334 | 21-225_75F11 | VH2\|2-05\|D6\|6-6\|RF2\|JH4 | ........ | .G...... | ...D.... | ....P... | L..V- ...A... | ........ | ........ |
| iPS:43 7377 | 21-225_74G9 | VH2\|2-05\|D6\|6-6\|RF2\|JH4 | ........ | .G...... | ...D.... | ........ | L..V- ...A... | ........ | ........ |
| iPS:39 2583 | 21-225_10B10 | VH2\|2-05\|D6\|6-6\|RF2\|JH4 | ........ | .G...... | F.S..... | ..S..... | ........R | IA.V- ...A... | ........ | ........ |
| iPS:39 3184 | 21-225_15H11 | VH2\|2-05\|D6\|6-6\|RF2\|JH4 | ....M... | .G...... | ..V..... | ..H....R | ........R | IV.V- ...A... | ........I | ........ |
| iPS:39 3212 | 21-225_30H6 | VH2\|2-05\|D6\|6-6\|RF2\|JH4 | ........ | ........ | ..H..... | ..A..... | ........ | L..V- ...A... | ........ | ........ |
| iPS:39 3222 | 21-225_17F5 | VH2\|2-05\|D6\|6-6\|RF2\|JH4 | ....S... | ........ | ...D.... | ........ | ....S... | I..V- ...A... | ........ | ........ |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 3224 | 21-225_31C2 | VH2|2-05|D6|6-6|RF2/JH4 | ......... | .G...... | ......... | ....E... | .....L..S........T....... | L..V—...S.... | ....A. |
| | Germline | | H_FR1 QVQLVQS GAEVKKPGASVK VSCKASG-YTFT | H_CDR1 G------YMH | H_FR2 WVRQAPGQ GLEWMG | H_CDR2 WINPN SGGTNYAQ KFQG | H_FR3 RVTMTRDTSISTAYMEL SRLRSDDTAVYYCAR | H_CDR3 GTAVAGYY ------YYYGMDV | H_FR4 WGQGTT VTVSS |
| iPS:46 8866 | 21-225_190C1 | VH1|1-02|D6|6-19|RF2/JH6 | ......... | ......... | ......... | ....Y.... | ......... | DR.....N.. ...........F... | ...... |
| iPS:43 6972 | 21-225_190C7 | VH1|1-02|D6|6-19|RF2/JH6 | ......... | ......... | ......... | ......... | ......... | DR.....N.. ...........F... | ...... |
| iPS:43 7020 | 21-225_193F11 | VH1|1-02|D6|6-19|RF2/JH6 | ......... | ......... | ......... | ....Y.... | ......... | DR.....N.. ...........F... | ...... |
| iPS:43 7036 | 21-225_195H9 | VH1|1-02|D6|6-19|RF2/JH6 | ......... | ......... | ......... | .....D... | .....T... | DR.....N.. ...........F... | ...... |
| iPS:43 7042 | 21-225_197E8 | VH1|1-02|D6|6-19|RF2/JH6 | ......L.. R.......R. | ...I..... | ......... | R........ | ......... | E......N.. ...F......G. | ..A... |
| | Germline | | H_FR1 QVQLQES GPGLVKPSETLS LTCTVSG-GSIS | H_CDR1 SS---STYWG | H_FR2 WIRQPPGK GLEWIG | H_CDR2 SIYY SGSTNYNP SLKS | H_FR3 RVTISVDTSKNQFS LKLSSVTAADTAVYYCAR | H_CDR3 VGIER -------YFDY | H_FR4 WGQGTL VTVSS |
| iPS:46 8868 | 21-225_74A1 | VH4|4-39|D1|1-1|RF2/JH4 | ......... | G........ | ......... | ....N..H. | .....T... | HD.LW......SL.F | ....I. |
| | Germline | | H_FR1 QVQLVQS GAEVKKPGASVK VSCKASG-YTFT | H_CDR1 G------YMH | H_FR2 WVRQAPGQ GLEWMG | H_CDR2 WINPN SGGTNYAQ KFQG | H_FR3 RVTMTRDTSISTAYMEL SRLRSDDTAVYYCAR | H_CDR3 YYYDSSGT -------YRNWFDP | H_FR4 WGQGTT VTVSS |
| iPS:47 2742 | 21-225_30D9_L C2 | VH1|1-02|D3|3-22|RF2/JH5 | .K....... E........ | ......L.. | ......... | ......... | ......... | V...YG..S. .......E..N | ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:47 2741 | 21-225_30D9_L_C1 | VH1 1-02/D3 3-22/RF2/J H5 | ..K........E........ | ....L... | ........ | ........ | ........ | V..YG...S........E..N | ........ |
| iPS:43 7040 | 21-225_196E7 | VH1 1-02/D3 3-22/RF2/J H5 | ............V...... | ....N... | ........ | .....H.. | ........ | D....T..- .......EG... | ........ |
| iPS:43 7050 | 21-225_197C11 | VH1 1-02/D3 3-22/RF2/J H5 | ............V...... | ....N... | ........ | .....H.. | ........ | D........- .......EG... | ........ |
| iPS:39 3214 | 21-225_33A1 | VH1 1-02/D3 3-22/RF2/J H5 | ..............S..... | ........ | ........ | N..H.... | R..S.... ...F..... | G..YA...S.......DL... | ........ |
| VH1 1-02/D3 3-22/RF2/JH4 | Germline | H_FR1 CVQLVQS– GAEVKKPGASVK VSCKASGYTFT | H_CDR1 G——YYMH | H_FR2 WVRQAPGQ GLEWMG | H_CDR2 WINPN SGGTNYAQ KFQG | H_FR3 RVTMTRDTS ISTAYMEL SRLRSEDTAVYYCAR | H_CDR3 YYYYSSG– ———YYYFDV | H_FR4 WGQGTL VTVSS |
| iPS:47 2743 | 21-225_68G6 | VH1 1-02/D3 3-22/RF2/J H4 | ......F..G........ ........S........ | ........ | ........ | S.YR.... KFQG | ...I........ ........K | AF.YG..T...........NE... | ........ |
| iPS:43 6902 | 21-225_69B11 | VH1 1-02/D3 3-22/RF2/J H4 | ..............R..... | ........ | ........ | ......G. | ........F...A........ | ...YG..S...........NG... | ........ |
| iPS:43 6904 | 21-225_71D4 | VH1 1-02/D3 3-22/RF2/J H4 | ........ | ....C... | ........ | ...D.... | ........V..V..D. | T..YG..T...........HNE... | ...S.... |
| iPS:43 6906 | 21-225_72B4 | VH1 1-02/D3 3-22/RF2/J H4 | ........ | ........ | ........ | ...V.... | ........ | A..YG..T...........NG... | ........ |
| iPS:43 7034 | 21-225_195E9 | VH1 1-02/D3 3-22/RF2/J H4 | ..........V........ | ........ | ........ | ...A.... | ....N........ | A..YG..T...........NE... | ........ |
| iPS:39 2598 | 21-225_18E10 | VH1 1-02/D3 3-22/RF2/J H4 | ........ | ........ | ........ | ........ | ........S..N.... | S..YG..S...........NE... | ........ |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:39 3182 | 21-225_4B3 | VH1J1-02/D3J3-22/RF2/JH4 | . . . . . . . . . . . . . . . . | . . . . . . . . . . | . . . . . . . . . . | S . . | . . . . . . . . . . . . . . . . . . . . . . . . . . . . . . . . | S . . YG . . S . . . . . . . . . . . . NE . . . . | . . . . |
| iPS:39 3200 | 21-225_35E1 | VH1J1-02/D3J3-22/RF2/JH4 | . . K . . . . . . . . . . . . . | . . . . . . . . . . | . . . . . . . . . . | . . K . | . . . . . . . . . . . . . . . . . . . . . . . V . . . P | V . . HG . . S . . . . . . . . . . . NE . . . | . . . . |
| iPS:39 3206 | 21-225_13F6 | VH1J1-02/D3J3-22/RF2/JH4 | . . . . . . . . . . . . . . . . | . . . . . H . . . | . . . . . . . . . . | . . A . | . . . . . . . . . . . . . . . . . . . . . . . . F . . . | SF . YG . . T . . . . . . . . . . . NE . . . | . . . . |
| iPS:39 3208 | 21-225_16F3 | VH1J1-02/D3J3-22/RF2/JH4 | . . . . . . . . . . . . . . . . | . . . . . . . . . . | . . . . . . . . . . | . . . . | . . . . . . . . . . . . . . . . . . . . . . . . . . . . | S . . YG . . T . . . . . . . . . . . NE . . . | . . . . |
| iPS:39 3210 | 21-225_17D3 | VH1J1-02/D3J3-22/RF2/JH4 | . . . . . . . . . . . . . . . . | . . . . . . . . . . | . . . . . . . . . . | . . . . | . . . . . . . . . . . . . . . . . . . . . . . . . . . . | AN . YG . . S . . . . . . . . . . . ND . . . | . . . . |
| iPS:39 3226 | 21-225_33E6 | VH1J1-02/D3J3-22/RF2/JH4 | . . K . . . . . . . . . . . . . | . . . . . . I . . | . . . . . . . . . . | . . . . | . . . . . . . . . . . . . . . . . . . . . . . . . . . . | V . . YG . . S . . . . . . . . . . . NE . . . | . . . . |
| iPS:39 3230 | 21-225_9G9 | VH1J1-02/D3J3-22/RF2/JH4 | . . . . . . . . . . . . . . . . | D . . . . . I . . | . . . . . . . . . . | . . D . | . . . . . . . . . . . . . . . . . . . . . . . . S . . . | S . . YG . . T . . . . . . . . . . . NE . . . | . . . . |
| iPS:39 8490 | 21-225_21D12 | VH1J1-02/D3J3-22/RF2/JH4 | . . K . . . . . . . . . . . . . | . . . . . . . . . . | . . . . . . . . . . | . . N . | . . . . . . . . . . . . . . . . . . . . . . . . . . . . | S . . YG . . T . . . . . . . . . . . NE . . . | . . . . |
| iPS:42 3018 | 21-225_31D12_LC2 | VH1J1-02/D3J3-22/RF2/JH4 | . . K . . . . . . . . . . . . . | . . . . . . . . . . | . . . . . . . . . . | . . V . | . . . . . . . . . . . . . . . . . . . . . . . . . . . . | V . . YG . . S . . . . . . . . . . . NE . . . | . . . . |
| iPS:42 3019 | 21-225_31D12_LC1 | VH1J1-02/D3J3-22/RF2/JH4 | . . K . . . . . . . . . . . . . | . . . . . . . . . . | . . . . . . . . . . | . . V . | . . . . . . . . . . . . . . . . . . . . . . . . . . . . | V . . YG . . S . . . . . . . . . . . NE . . . | . . . . |
| VH3J3-33/D7J7-27/RF2/JH4 | Germline | QVQLVES-GGGVVQPGRSLR-SCAASG-FTFS | S------YGMH | WVRQAPGK-GLEWVA | VIWYD---GSNKYYAD-SVKG | RFTISRDNSKNTLYLQM-NSLRAEDTAVYYCAR | -EY---------FDY | WGQGTL-VTVSS |

Figure 52 (Continued)

| | | | | | | | |
|---|---|---|---|---|---|---|---|
| iPS:39_2920 | 21-225_29G4 | VH3|3-33/D7|7-27|RF2/JH4 | ... | D........I | .....E.. .M.. | ........ | E..M........TG.. |
| iPS:43_3899 | 21-225_43C3 | VH3|3-33/D7|7-27|RF2/JH4 | ....T.. | ........ | EN...... | ........ | E..F........SN.. |
| iPS:43_3921 | 21-225_44C3 | VH3|3-33/D7|7-27|RF2/JH4 | ........ | ........I | .FE..... | ....S... | E..F........ST.. |
| iPS:43_3933 | 21-225_44C8 | VH3|3-33/D7|7-27|RF2/JH4 | ......N. | N....... | .E...... | .....V.. | E..F........LS.. |
| iPS:43_3969 | 21-225_46F3 | VH3|3-33/D7|7-27|RF2/JH4 | ........ | D....... | .FE..... | .....V.. | E..F........SN.. |
| iPS:43_3975 | 21-225_46C6 | VH3|3-33/D7|7-27|RF2/JH4 | ........ | ........I | EN...... | .V...V.. | E..F........SN.. |
| iPS:43_3977 | 21-225_46D8 | VH3|3-33/D7|7-27|RF2/JH4 | ........ | D....... | .FE..... | .....V..T | E..F........SN.. |
| iPS:43_3983 | 21-225_47A1 | VH3|3-33/D7|7-27|RF2/JH4 | ........ | D....... | DY..K... | .V..A...T | E..M........L... |
| iPS:43_3997 | 21-225_48C1 | VH3|3-33/D7|7-27|RF2/JH4 | ........ | ........ | EI..K... | .....M.. | E..W........EA.. |
| iPS:43_4009 | 21-225_48A9 | VH3|3-33/D7|7-27|RF2/JH4 | ........ | D....... | ENK..... | ....M.F. | E..AW.......YE.. |
| iPS:43_4013 | 21-225_48D12 | VH3|3-33/D7|7-27|RF2/JH4 | ........ | ........ | .....R. .V.....V | ........ | E..M........RS.. |
| iPS:43_4019 | 21-225_49A1 | VH3|3-33/D7|7-27|RF2/JH4 | ........ | D....... | ED...V | ........ | E..F........LS.. |

Figure 52 (Continued)

| | | | | | | | | |
|---|---|---|---|---|---|---|---|---|
| iPS:43 4029 | 21-225_49C6 | VH3J3-33/D7|7-27|RF2/J H4 | . . . | . . . | N . . . | . . . | V . . . K.V . . . | S . . . | . . . | D.M . . . . . . IE . . . | . . . |
| iPS:43 4057 | 21-225_51E4 | VH3J3-33/D7|7-27|RF2/J H4 | . . . | . . . | . . . | . . . | . . . E . . . | . . . | . . . | E.F . . . . . . LS . . . | . . . |
| iPS:43 4071 | 21-225_51F9 | VH3J3-33/D7|7-27|RF2/J H4 | . . . | . . . | D . . . | . . . | . . . F . . N . . . | . . . S . . . | . . . | E.F . . . . . . LS . . . | . . . |
| iPS:43 4075 | 21-225_51B11 | VH3J3-33/D7|7-27|RF2/J H4 | . . . | . . . | D . . . | . . . | . . . FG . . N . . . G | . . . S . . . | . . . | E.F . . . . . . LS . . . | . . . |
| iPS:43 4077 | 21-225_51F11 | VH3J3-33/D7|7-27|RF2/J H4 | . . . | . . . | N . . . . F | . . . | . . . E . . . E . . . | . . . | . . . | E.F . . . . . . LS.F | . . . |
| iPS:43 4081 | 21-225_52B2 | VH3J3-33/D7|7-27|RF2/J H4 | . . . | . . . | N . . . | . . . | T.F . . . QR . . . | . . . S . . . | . . . T . . . | D.M . . . . . . IE.F | . . . |
| iPS:43 4091 | 21-225_52B9 | VH3J3-33/D7|7-27|RF2/J H4 | . . . | . . . | D . . . | . . . | . . . F . . N . . . | . . . S . . . | . . . | E.F . . . . . . LS . . . | . . . |
| iPS:43 4105 | 21-225_53D2 | VH3J3-33/D7|7-27|RF2/J H4 | . . . T | . . . T | D . . . I | . . . | V.D . . . . . . . . . | . . . A . . . | . . . V . . . | G.F . . . . . . TG . . . | A . . . |
| iPS:43 4119 | 21-225_53E6 | VH3J3-33/D7|7-27|RF2/J H4 | . . . | . . . | N . . . . F | . . . | . . . E . . . G | . . . H . . . | . . . | E.M . . . . . . TS . . . | . . . |
| iPS:43 4129 | 21-225_53B12 | VH3J3-33/D7|7-27|RF2/J H4 | . . . | . . . | N . . . | . . . | V . . . N.R . . . | . . . | . . . | E.F . . . . . . LS.F | . . . |
| iPS:43 4131 | 21-225_54D3 | VH3J3-33/D7|7-27|RF2/J H4 | . . . | . . . | . . . | . . . | T.F . . . N.N . . . | . . . | . . . | E.F . . . . . . LS . . . | . . . |
| iPS:43 4141 | 21-225_54C6 | VH3J3-33/D7|7-27|RF2/J H4 | . . . T | . . . T | D . . . I | . . D . . . | EN . . . . . . . . . | . . . A . . . | . . . V . . . | E.M . . . . . . TS . . . | . . . |

Figure 52 (Continued)

| | | | | | | | | |
|---|---|---|---|---|---|---|---|---|
| iPS:43 4143 | 21-225_54G7 | VH3\|3-33\|D7\|7-27\|RF2\|J H4 | . . . . | N . . . . | . . . . | E . . G E . . . . | . . . . | E.F.....LS... |
| iPS:43 4155 | 21-225_55B3 | VH3\|3-33\|D7\|7-27\|RF2\|J H4 | . . . . | . . . . | . . . . | . F . . . N . . E. | . . . . | E.F.....LS... |
| iPS:43 4199 | 21-225_59F11 | VH3\|3-33\|D7\|7-27\|RF2\|J H4 | . . . . | N . . . . | . . . . | . . . . . . . . | . . S . T . . S | E.M.....NG... |
| iPS:43 4207 | 21-225_60A3 | VH3\|3-33\|D7\|7-27\|RF2\|J H4 | . . . V | . . . . | . . . . | E . . H . . E . . | . . . . | E.M.....TG... |
| iPS:43 4253 | 21-225_62E4 | VH3\|3-33\|D7\|7-27\|RF2\|J H4 | . . . V | D . . . . | . . . . | . . E . . . . . | . . . V . . H . | E.F.....SS... |
| iPS:43 4271 | 21-225_57A4 | VH3\|3-33\|D7\|7-27\|RF2\|J H4 | . . . V | D . . . . | . . . . | R . . . A . . V | . . . . | E.M.....RS... |
| iPS:43 4293 | 21-225_58F5 | VH3\|3-33\|D7\|7-27\|RF2\|J H4 | . . . V | D . . . . | . . . . | . . . . A . HV . | . . . . | E.M.....RS... |
| iPS:43 4337 | 21-225_64E1 | VH3\|3-33\|D7\|7-27\|RF2\|J H4 | . . . . | D . . . . | . . . . | . F . . G ET . . . | . . . . | E.F.....SS... |
| iPS:43 4357 | 21-225_65C1 | VH3\|3-33\|D7\|7-27\|RF2\|J H4 | . . . . | D . . . . | . . . . | FE . . . H . T | . . . . | E.F.....SS... |
| iPS:43 4375 | 21-225_66C7 | VH3\|3-33\|D7\|7-27\|RF2\|J H4 | . . . . | D . . . . | . . . . | FE . . . H . T | . . . . | E.F.....SS... |
| iPS:43 4411 | 21-225_68F11 | VH3\|3-33\|D7\|7-27\|RF2\|J H4 | . . . . | D . . . . | . . . . | . . . . V . . . | . . . V . | E.M.....TS.C |
| iPS:43 4441 | 21-225_71A2 | VH3\|3-33\|D7\|7-27\|RF2\|J H4 | . . . T | D . . . . | . . . . | E . . . . . . . | . . . . | E.W.....QD... |

Figure 52 (Continued)

| | | | | | | | | |
|---|---|---|---|---|---|---|---|---|
| iPS:43 4447 | 21-225_71B6 | VH3\|3-33/D7\|7-27\|RF2/J H4 | . . . . . . . . . . | N . . . . . . . . | . . . . . . . . . . | . . . . . . . . . . RT . . . . . . | . . . . . . . . . H . . . . . . . . . | E . . M . . . . . . . . LS . . . | . . . . . . . . . . |
| iPS:43 4453 | 21-225_71B11 | VH3\|3-33/D7\|7-27\|RF2/J H4 | . . . . . . . . . . | D . . . . . . . . | . . . . . . . . . . | . RN . . . . . G . . . . . . | . . . . . . . . . . . . . . . . | E . . M . . . . . . . . LS . . . | . . . . . . . . . . |
| iPS:43 4457 | 21-225_72G12 | VH3\|3-33/D7\|7-27\|RF2/J H4 | . . . . . . . . . . | . . . . . . . . . | . . . . . . . . . . . . . . ET | . . . . . . . F . . . E . . . . . . | . . . . . . . . . . . . . . . . | E . . F . . . . . . . . SS . . . | . . . . . . . . . . |
| iPS:43 5311 | 21-225_146H9 | VH3\|3-33/D7\|7-27\|RF2/J H4 | . . . . . . . S . . | . . . . . . . . . | . . . . . . . . . . | . . . . . . . F . . . E . . . H . G . . . | . . . . . . . . . . . . . . . . | E . . F . . . . . . . . LS . . . | . . . . . . . . . . |
| iPS:43 5511 | 21-225_157C3 | VH3\|3-33/D7\|7-27\|RF2/J H4 | . . . . . . . . V . | T . . . . . . . . | . . . . . . . . . . | . VN . . . . . . . . . . . . | . . . . . . . . . . . . . . . . | E . . F . . . . . . . . LS . . . | . . . . . . . . . . |
| iPS:43 5533 | 21-225_157H8 | VH3\|3-33/D7\|7-27\|RF2/J H4 | . . . . . . . . . . | . . . . . . . . . | . . . . . . . . . . | . VN . . . . . . . . . . . . | . . . . . . . . . . . . . . . . | E . . F . . . . . . . . LS . . . | . . . . . . . . . . |
| iPS:43 5551 | 21-225_158H6 | VH3\|3-33/D7\|7-27\|RF2/J H4 | . . . . . . . . . . | . . . . . . . . . | . . . . . . I . . . | . VT . . . . . . . . . . . . | . . . . . . . D . . V . . . . . . | E . . W . . . . . . . . AE . . . | . . . . . . . . . . |
| iPS:43 5569 | 21-225_159C5 | VH3\|3-33/D7\|7-27\|RF2/J H4 | . . . . . . . . . . | . . . . . . . . . | . . . . . . F . . . | . V . . . . . . . . VN . . . . . . . | . . . . . . . P . . . . . . . . | E . . F . . . . . . . . LS . . . | . . . . . . . . . . |
| iPS:43 6268 | 21-225_203B9 | VH3\|3-33/D7\|7-27\|RF2/J H4 | . . . . . . . . . L | . . . . . . . . . | . . . . . . . . . . | . VN . . . . . . . . . . . . | . . . . . . . . . . . . . . . . | E . . F . . . . . . . . LS . . . | . . . . . . . . I . |
| iPS:43 6328 | 21-225_207F12 | VH3\|3-33/D7\|7-27\|RF2/J H4 | . . . . . . . . . . | N . . . . . . . . | . . . . . . . . . . | . RN . . . . . G . . . . . . | . . . . . . . . . . S . . . V . . | E . . F . . . . . . . . L . . . | . . . . . . . . . . |
| iPS:43 6556 | 21-225_224D10 | VH3\|3-33/D7\|7-27\|RF2/J H4 | . . . . . . . K . . | . . . . . . . . . | . . . . . . . . . . | . E . . . . . V . . . . . R . . | . . . . . . . . . . . . . . . . | E . . F . . . . . . . . QS . . . | . . . . . . . . P . |
| iPS:39 2618 | 21-225_16F10 | VH3\|3-33/D7\|7-27\|RF2/J H4 | . . . . . . . . . . | D . . . . . . . . | . . . . . . . . . . | . . . . . . . N . . . V . . . . | . . . . . . . . . . . . . . . . | E . AW . . . . . . . . YE . . . | . . . . . . . . . . |

Figure 52 (Continued)

| | | | | | | | | |
|---|---|---|---|---|---|---|---|---|
| iPS:39 2626 | 21-225_18A5 | VH3J3-33/D7J7-27JRF2/J H4 | ....YT | D...... | ........ | ....... | ....... | D.W....TEE. | ....... |
| iPS:39 2630 | 21-225_20E5 | VH3J3-33/D7J7-27JRF2/J H4 | ........ | D...... | ........ | F...... | ....... | E.F....RS. | ....... |
| iPS:39 2640 | 21-225_18A1 | VH3J3-33/D7J7-27JRF2/J H4 | V....... | ........ | ........ | EN.Q.E. | ...S... | E.F....QS. | ....P.. |
| iPS:39 2644 | 21-225_19E1 | VH3J3-33/D7J7-27JRF2/J H4 | ........ | N...... | ........ | EN.Q.E.V | ...V... | E.F....RS. | ....... |
| iPS:39 2654 | 21-225_17A10 | VH3J3-33/D7J7-27JRF2/J H4 | ........ | N...... | ...A... | ..E.... | V...... | E.F....RS. | ....... |
| iPS:39 2658 | 21-225_18E8 | VH3J3-33/D7J7-27JRF2/J H4 | ........ | ........ | ........ | EN.Q.E. | ...F... | E.F....RS. | ....... |
| iPS:39 2666 | 21-225_16F11 | VH3J3-33/D7J7-27JRF2/J H4 | M...E.. | ........ | ........ | EN.Q.E.V | ...S..V | E.F....QS. | ....P.. |
| iPS:39 2674 | 21-225_18C2 | VH3J3-33/D7J7-27JRF2/J H4 | ....V.. | D...... | ....M.. | VT.E.. | ...T... | E.F....... | ....... |
| iPS:39 2680 | 21-225_20A7 | VH3J3-33/D7J7-27JRF2/J H4 | ........ | N...... | ........ | EN.Q.E. | ...S... | E.W....YE. | ....... |
| iPS:39 2686 | 21-225_17C7 | VH3J3-33/D7J7-27JRF2/J H4 | ....K.. | D...... | ........ | ..E.... | ...G... | E.F....RS. | ....... |
| iPS:39 2690 | 21-225_18F2 | VH3J3-33/D7J7-27JRF2/J H4 | ........ | D...... | ........ | ..F..V | ...V... | D.W....TEE. | ....... |
| iPS:39 2716 | 21-225_17B5 | VH3J3-33/D7J7-27JRF2/J H4 | ........ | D...... | ........ | E..H.I | ...V... | E.F....R.. | ....... |

Figure 52 (Continued)

| | | | | | | | |
|---|---|---|---|---|---|---|---|
| iPS:39 2732 | 21-225_17E5 | VH3j3-33/D7j7-27jRF2/J H4 | ........ | D....... | L....... VT.....G. | .Q...L.E. | L.W....... ...YE... |
| iPS:39 2744 | 21-225_20D5 | VH3j3-33/D7j7-27jRF2/J H4 | ........ | ........ | EN.Q.... | ......D. | E.F....... ...RS... |
| iPS:39 2758 | 21-225_21G11 | VH3j3-33/D7j7-27jRF2/J H4 | ........ | D....... | ..M..... VT.E.... | ........ | E.W....... ...YE... |
| iPS:39 2772 | 21-225_20E12 | VH3j3-33/D7j7-27jRF2/J H4 | ........ | ........ | .M...... E...H.. | ...R.... | E.F....... ....R... |
| iPS:39 2790 | 21-225_20D10 | VH3j3-33/D7j7-27jRF2/J H4 | ........ | D....... | ..F..... ........ | I....D.. | D.W....... ..TEE... |
| iPS:39 2796 | 21-225_22A4 | VH3j3-33/D7j7-27jRF2/J H4 | ........ | D....I.. | ..F..... ......V. | ........ | D.W....... ..TEE... |
| iPS:39 2810 | 21-225_20H12 | VH3j3-33/D7j7-27jRF2/J H4 | ........ | N....... | EN....V. | ........ | E.F....... ...RS... |
| iPS:39 2832 | 21-225_21H8 | VH3j3-33/D7j7-27jRF2/J H4 | ........ | D....... | ..F..... ........ | ........ | D.W....... ..TEE... |
| iPS:39 2854 | 21-225_21E5 | VH3j3-33/D7j7-27jRF2/J H4 | ...S.... | ........ | .E...... ........ | ...M..T. | E.F....... ...RS... |
| iPS:39 2860 | 21-225_22H8 | VH3j3-33/D7j7-27jRF2/J H4 | ........ | ........ | .N...... ........ | ........ | E.AW...... ...YE... |
| iPS:39 2866 | 21-225_23H11 | VH3j3-33/D7j7-27jRF2/J H4 | ..E..... | ........ | EN....V. | ........ | E.F....... ...RS... |
| iPS:39 2876 | 21-225_21F7 | VH3j3-33/D7j7-27jRF2/J H4 | ........ | D....... | ..F..... .N....V. | ........ | D.W....... ..TEE... |

Figure 52 (Continued)

| | | | | | | | | |
|---|---|---|---|---|---|---|---|---|
| iPS:39 2880 | 21-225_22F9 | VH3\|3-33/D7\|7-27\|RF2/J H4 | . . . M . . . | . . . . . . . | . . . . . . . | . . . . . . . | E . . . B . V . EN . . . . . . | . . . S . . . V |  E . . F . . . . . . . . . QS . . | . . . P . . . |
| iPS:39 2894 | 21-225_21G2 | VH3\|3-33/D7\|7-27\|RF2/J H4 | . . . . . . . | . . D . . . . | . . . M . . . | . . . . . . . | . . . . . . . VT . . . . . . | . . . . . E . . . . . . . | E . . W . . . . . . . . . YE . . | . . . . . . . |
| iPS:39 2900 | 21-225_22F2 | VH3\|3-33/D7\|7-27\|RF2/J H4 | . . . . . . . | . . D . . . . | . . . . . . . | . . . . . . . | . . . . . E . V . . . . . . . R . | . . . S . . . V | E . . F . . . . . . . . . QS . . | . . . P . . . |
| iPS:39 2908 | 21-225_23F12 | VH3\|3-33/D7\|7-27\|RF2/J H4 | . . . . . V . | . . . . . . . | . . . . . . . | . . . . . . . | . . . . . ET . | . . . . I . . | E . AW . . . . . . . . YE . . | . . . S . . . |
| iPS:39 2918 | 21-225_28F5 | VH3\|3-33/D7\|7-27\|RF2/J H4 | . . . . . . . | . . . . . . . | . . . . . . . | . . . . . . . | . . . . . EN . . | . . . . . . M . . | E . . W . . . . . . . . . YD . . | . . . . . . . |
| iPS:39 2934 | 21-225_27D5 | VH3\|3-33/D7\|7-27\|RF2/J H4 | . . . . . . . | . . . . . . . | . . . . . . . | . . . . . . . | . . . . . E . . . G . | . . . G . . . L . | E . . F . . . . . . . . . LS . . | . . . . . . . |
| iPS:39 2958 | 21-225_28C7 | VH3\|3-33/D7\|7-27\|RF2/J H4 | . . . . . . . | . . . . . . . | . . . . . . . | . . . . . . . | . . . . . E . . | . . . . . . . | E . . W . . . . . . . . . YD . . | . . . . . . . |
| iPS:39 2968 | 21-225_25B6 | VH3\|3-33/D7\|7-27\|RF2/J H4 | . . . . V . I . LR | . . N . . . . | . . . . . . . | . . . . . . . | . . . . . E . TE | . . . . . . . | E . . F . . . . . . . . . LS . . | . . . . . . . |
| iPS:39 2972 | 21-225_26A2 | VH3\|3-33/D7\|7-27\|RF2/J H4 | . . . . . . . | . . D . . . . | . . . . . . . | . . . . . . . | . . . . . . . V . | . . . . . . . | E . . W . . . . . . . . . YD . . | . . . . . . . |
| iPS:39 2980 | 21-225_29H6 | VH3\|3-33/D7\|7-27\|RF2/J H4 | . . . . . . . | . . . . . . . | . . . . . . T | . . . . . . . | . . . . . N . . EN . . | . . . . . . . | E . . M . . . . . . . . . TG . S | . . . . . . . |
| iPS:39 2988 | 21-225_25E6 | VH3\|3-33/D7\|7-27\|RF2/J H4 | . . . . . . . | . . . . . . . | . . . . . . . | . . . . . . . | . . . . . EN . . | . . . . . T . | E . . M . . . . . . . . . TG . S | . . . . . . . |
| iPS:39 2990 | 21-225_25H10 | VH3\|3-33/D7\|7-27\|RF2/J H4 | . . . . . . . | . . D . . . . | . . . . . . . | . . . . . . . | . . . . . E . . . M . . | . . . . . . . | E . . M . . . . . . . . . TG . . | . . . . . . . |

Figure 52 (Continued)

| | | | | | | | |
|---|---|---|---|---|---|---|---|
| iPS:39 3000 | 21-225_29D7 | VH3\|3-33/D7\|7-27\|RF2/J H4 | ... | ... | E......G. ........ | ......G... .L...... | E..F..... ...LS... | ... |
| iPS:39 3018 | 21-225_29B8 | VH3\|3-33/D7\|7-27\|RF2/J H4 | ...D.... | ... | EN...... ........ | ........ ........ | E..M..... ...TG.S.. | ... |
| iPS:39 3030 | 21-225_25H11 | VH3\|3-33/D7\|7-27\|RF2/J H4 | ...D.... | ... | EN.E.... ........ | ........ ........ | E..M..... ...TG.S.. | ... |
| iPS:39 3034 | 21-225_27F2 | VH3\|3-33/D7\|7-27\|RF2/J H4 | E....... ...I... | ... | EN...V. ..R..... | ........ ........ | E..M..... ...TG.S.. | ... |
| iPS:39 3048 | 21-225_27C3 | VH3\|3-33/D7\|7-27\|RF2/J H4 | ...D.... | ... | EN..S... ........ | ........ ........ | E..M..... ...TG.S.. | ... |
| iPS:39 3054 | 21-225_29G8 | VH3\|3-33/D7\|7-27\|RF2/J H4 | ...D.... | ... | ET...... ........ | ........ ........ | E..M..... ...TS... | ... |
| iPS:39 3812 | 21-225_6A11 | VH3\|3-33/D7\|7-27\|RF2/J H4 | ...D.... | ...F.... | ..F..... ........ | ....D... ........ | D..W..... ..TEE... | ... |
| iPS:39 3818 | 21-225_6G12 | VH3\|3-33/D7\|7-27\|RF2/J H4 | ...D..F. | ........ | R..N.... ........ | ........ ........ | E..F..... ...RS... | ... |
| iPS:39 3820 | 21-225_8H7 | VH3\|3-33/D7\|7-27\|RF2/J H4 | ..N..... | ........ | EN.Q.... ........ | .......T ........ | E..F..... ...RS... | ... |
| iPS:39 3826 | 21-225_10G5 | VH3\|3-33/D7\|7-27\|RF2/J H4 | ...D.... | ........ | EN.Q.... ........ | ........ ........ | E..F..... ...RS... | ... |
| iPS:39 3828 | 21-225_10H12 | VH3\|3-33/D7\|7-27\|RF2/J H4 | ........ | ........ | DN.Q.... ........ | ........ ........ | E..F..... ...RS... | ... |
| iPS:39 3830 | 21-225_12A1 | VH3\|3-33/D7\|7-27\|RF2/J H4 | ........ | ........ | EN.Q.... ........ | ........ ........ | E..F..... ...RS... | ... |

Figure 52 (Continued)

| | | | | | | | | | |
|---|---|---|---|---|---|---|---|---|---|
| iPS:39 3838 | 21-225_6G2 | VH3j3-33/D7j7-27jRF2/J H4 | L......... | D......I. | ...F | ... | ...S..... | D.W.....TEE. | ... |
| iPS:39 3854 | 21-225_7H11 | VH3j3-33/D7j7-27jRF2/J H4 | ........K.....S | D........ | EN....... | ... | ......... | E.F.....RS. | ... |
| iPS:39 3866 | 21-225_14E3 | VH3j3-33/D7j7-27jRF2/J H4 | ......... | D.....F.. | EN.Q..... | ... | ....F.... | E.F.....RS. | ... |
| iPS:39 3876 | 21-225_9A1 | VH3j3-33/D7j7-27jRF2/J H4 | ...V..... | D........ | ...F..... | ... | ......... | D.W.....TEE. | ... |
| iPS:39 3882 | 21-225_15E3 | VH3j3-33/D7j7-27jRF2/J H4 | ......T.. | N........ | EN...E... | ... | ......... | E.F.....LS. | ... |
| iPS:39 3884 | 21-225_16F4 | VH3j3-33/D7j7-27jRF2/J H4 | ......... | ......... | ...E..H.. | R.. | .....H... | E.F.....LS. | ... |
| iPS:39 3912 | 21-225_16F6 | VH3j3-33/D7j7-27jRF2/J H4 | ......... | N........ | ...Q..G.. | ... | .....H.V. | E.F.....LS. | P. |
| iPS:39 3922 | 21-225_2B2 | VH3j3-33/D7j7-27jRF2/J H4 | ......... | N........ | ...E..G.. | ... | ......V. | E.F.....QS. | ... |
| iPS:39 3934 | 21-225_13E6 | VH3j3-33/D7j7-27jRF2/J H4 | ......... | ......... | EN...E... | ... | ......... | E.F.....RS. | ... |
| iPS:39 3948 | 21-225_16A5 | VH3j3-33/D7j7-27jRF2/J H4 | ......... | D........ | EN....I.. | ... | .....S.V. | D.W.....TEE. | ... |
| iPS:39 3960 | 21-225_7G2 | VH3j3-33/D7j7-27jRF2/J H4 | ......... | D........ | ...F..V.. | .M. | ......L.. | E.W.....YE. | ... |
| iPS:39 3974 | 21-225_7C4 | VH3j3-33/D7j7-27jRF2/J H4 | ......K.. | N........ | ...VT.... | ... | ......... | E.F.....RS. | ... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| Germline | VH3|3-33|D7|7-27|RF2|JH4 | EVQLVEST GGGLVKPGGSL RLSCAASG-FTFS | -TSMH | WVRQAPGK GLEWVS | SISSS- SSSTIYAD SVKG | RFTISRDNAKNSLYLQM NSLRAEDTAVYYCAR | DKSIY---TFDI | WGQGTL VTVSS |
| iPS:39 3976 | 21-225_7E9 | VH3|3-33|D7|7-27|RF2|JH4 | . . . . . . . . . . . . . . . . . . . . . . . . . . . . . | D . . . . . | . . . . . . . . . . . . . . . . | EN . . . . V . | . . . . . . . . . . . . . . . . . . . . . . . . . . . | E.F. . . . . . . . RS. . . | . . . . |
| iPS:39 3994 | 21-225_8C9 | VH3|3-33|D7|7-27|RF2|JH4 | . . . . . . . . . . . . . . . . . . . . . . . . . . . . . | . . . . . . | . . . . . . . . . . . . . . . . | EN . . . . V . | . . . . . . . . . . . . . . . . . . . . . . . . . . . | E.F. . . . . . . . RS. . . | . . . . |
| iPS:39 3998 | 21-225_12B12 | VH3|3-33|D7|7-27|RF2|JH4 | . . . . . . . . . . . . . . . . . . . . . . . . . . . . . | D . . . . . | . . M . . . . . . . . . . . . . | . VT . . . . | . . . . . . . . . . . . . . . . . . . . . . . . . . . | E.W. . . . . . . . YE. . . | . . . . |
| iPS:39 4024 | 21-225_16B7 | VH3|3-33|D7|7-27|RF2|JH4 | . . . . . . . . . . . . . . . . . . . . . . . . . . . . . | . . . . . . | . . . . . . . . . . . . . . . . | . E . . . . | . . . . . . . . . . . . . . . . . . . . . . . . . . . | E.F. . . . . . . . LS. . . | . . . . |
| iPS:39 4059 | 21-225_9E8 | VH3|3-33|D7|7-27|RF2|JH4 | . . . . . . . . . . . . . . . . . . . . . . . E . . . . . | . . . . . . | . . . . . . . . . . . . . . . . | EN . Q . . | . . . . . . . . . . . . . . . . . . . . . . . . . . . | E.F. . . . . . . . RS. . . | . . . . |
| iPS:39 4067 | 21-225_12F2 | VH3|3-33|D7|7-27|RF2|JH4 | . . . . . . . . . . . . . . . . . . . . . . . . . . . . . | D . . . . . | . . . . . . . . . . . . . . . . | . . N . . . V . | . . . . . . . . . F . . V . . . . . . . . . . . . . | E.F. . . . . . . . SE. . . | . . . . |
| iPS:39 4089 | 21-225_12E6 | VH3|3-33|D7|7-27|RF2|JH4 | . . . . . . . . . . . . . . . . . . . . . . . . . . . . . | D . . . . . | . . . . T . . . . . . . . . . . | . E . . . | . . . . . . . . . . . . . D . . . . . . . . . . . . . | E.AW. . . . . . . . YE. . . | . . . . |
| iPS:39 4097 | 21-225_16G7 | VH3|3-33|D7|7-27|RF2|JH4 | . . . . . . . . . . . . . . . . . . . . . . . . . . . . . | D . . . . . | . . . . . . . . . . . . . . . . | EN . E . . | . . . . . . . . . . . . . A . . . . . . . . . . . . . | E.AW. . . . . . . . YE. . . | . . . . |
| iPS:40 2219 | 21-225_1C12 | VH3|3-33|D7|7-27|RF2|JH4 | . . . . . . . . . . . . . . . . . . . T . . . . . . . . . | N . . . . . | . . . . . . . . . . . . . . . . | EN . . . V . | . . . . . . . . . . . . . . . . . . . . . . . . . . . | E.F. . . . . . . . RS. . . | . . . . |
| VH3|3-21|D4|4-11|RF2|JH4 | | H_FR1 | H_CDR1 | H_FR2 | H_CDR2 | H_FR3 | H_CDR3 | H_FR4 |
| iPS:43 3895 | 21-225_43E1 | VH3|3-21|D4|4-11|RF2|JH4 | . . . . . . . . . . . . . . . . . . . . . . . . . . . . . | . . . . . . | . . . . . . . . . . . . . . . . | A . GN . . . . T . . . . . L . . . | . . . . . . . . . . . . . . . . . . . . . . . F . L . | . RG-- . . . . --SE | . . . . |

Figure 52 (Continued)

| | | | | | | |
|---|---|---|---|---|---|---|
| iPS:43 4103 | 21-225_53G1 | VH3\|3-21\|D4\|4-11\|RF2/J H4 | .....E........ | ............ | .....G..... | ............ | RG---- |
| iPS:43 4179 | 21-225_56F1 | VH3\|3-21\|D4\|4-11\|RF2/J H4 | ....F........ | ............ | ..T...G..... | ............ | ....—ST |
| iPS:43 4263 | 21-225_56H7 | VH3\|3-21\|D4\|4-11\|RF2/J H4 | ....S........ | ............ | ..T...G..... | ............ | ....—SS |
| iPS:43 5521 | 21-225_157H4 | VH3\|3-21\|D4\|4-11\|RF2/J H4 | ............ | ............ | ..T........ | ............ | RG---- |
| iPS:43 5527 | 21-225_157G7 | VH3\|3-21\|D4\|4-11\|RF2/J H4 | ....F........ | ............ | .....G..... | ............ | ....—SI |
| iPS:43 5529 | 21-225_157H7 | VH3\|3-21\|D4\|4-11\|RF2/J H4 | ............ | ............ | ..T........ | ............ | RG---- |
| iPS:43 5547 | 21-225_158F5 | VH3\|3-21\|D4\|4-11\|RF2/J H4 | ....F........ | ............ | C..G....... | ....M....V | ....—SS |
| iPS:43 5549 | 21-225_158H5 | VH3\|3-21\|D4\|4-11\|RF2/J H4 | ....T........ | ............ | .....G..... | ............ | RG---- |
| iPS:43 5553 | 21-225_158G8 | VH3\|3-21\|D4\|4-11\|RF2/J H4 | ....R........ | ............ | ..T........ | ............ | ....—G. |
| iPS:43 5581 | 21-225_160H1 | VH3\|3-21\|D4\|4-11\|RF2/J H4 | ............ | ............ | ..L..G..... | ............ | RG---- |
| iPS:43 5593 | 21-225_160F4 | VH3\|3-21\|D4\|4-11\|RF2/J H4 | ............ | ............ | TG.M....... | ....H...... | ....—SS |
| iPS:43 5617 | 21-225_162F2 | VH3\|3-21\|D4\|4-11\|RF2/J H4 | ....F........ | ............ | .....G..... | .....F..... | K---- |

Figure 52 (Continued)

| | | | | | | | | |
|---|---|---|---|---|---|---|---|---|
| iPS:43 5621 | 21-225_162H3 | VH3\|3-21\|D4\|4-11\|RF2/J H4 | ........ | ........ | R....... | ....G.. ...T... | ........ | .RG--- ...--SS |
| iPS:43 5641 | 21-225_163F9 | VH3\|3-21\|D4\|4-11\|RF2/J H4 | ...F.... ...Q.... | ........ | ........ | ....G.. ...T... | ........ | .RG--- ...--SL |
| iPS:43 5719 | 21-225_171A11 | VH3\|3-21\|D4\|4-11\|RF2/J H4 | ........ ...N.... | ........ | ........ | ....G.. | ........ | .RG--- ...--SS ...--I |
| iPS:43 6856 | 21-225_58C5 | VH3\|3-21\|D4\|4-11\|RF2/J H4 | ........ | ........ | ....I... | ..Y.L.. | ...S... | T..G- ...S... |
| iPS:44 8904 | 21-225_65C12 | VH3\|3-21\|D4\|4-11\|RF2/J H4 | ........ ...R.... | ..F..L.. | ........ | ........ | ........ | .AY-- ...--SH |
| iPS:47 2730 | 21-225_14B1_L C1 | VH3\|3-21\|D4\|4-11\|RF2/J H4 | ........ | ...T.... | ........ | ....G.. ...L..P | ........ | .RG--- ...--SS |
| iPS:47 2731 | 21-225_14B1_L C2 | VH3\|3-21\|D4\|4-11\|RF2/J H4 | ........ | ...T.... | ........ | ....G.. ...L..P | ........ | .RG--- ...--SS |
| iPS:39 2726 | 21-225_20B5 | VH3\|3-21\|D4\|4-11\|RF2/J H4 | ...A.... ...T.... | ..G.L.. | ........ | ....G.. | ........ | .RG--- ...--S. |
| iPS:39 2734 | 21-225_17D8 | VH3\|3-21\|D4\|4-11\|RF2/J H4 | ........ | ........ | ........ | ...G.H.S | .....L.. | .RG--- ...--SG |
| iPS:39 2768 | 21-225_20B8 | VH3\|3-21\|D4\|4-11\|RF2/J H4 | ........ | ........ | ........ | ...G.H.. | .....F.. | .RG--- ...--SG |
| iPS:39 2778 | 21-225_22H3 | VH3\|3-21\|D4\|4-11\|RF2/J H4 | ...A.... | ........ | ........ | ........ | ........ | .RG--- ...--SL |
| iPS:39 2788 | 21-225_20C8 | VH3\|3-21\|D4\|4-11\|RF2/J H4 | ........ | ........ | ........ | ....G.. ...A.. | ........ | .RG--- ...--SL |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:39_2792 | VH3}3-21/D4|4-11|RF2/JH4 | ..................... | ............ | ................. | ....G...... .L........ | ............................................ | .RG---.......---S. | ............ |
| iPS:39_2844 | VH3}3-21/D4|4-11|RF2/JH4 | ..................... | ........T... | ................. | ....G...... .W.V...... | ............................................ | .RG---.......---SL | ............ |
| iPS:39_23E11 | | | | | | | | |
| iPS:39_2848 | VH3}3-21/D4|4-11|RF2/JH4 | ..................... | ...T........ | ................. | ................... | ............................................ | .RG---.......---SC | ......I..... |
| iPS:39_20F9 | | | | | | | | |
| iPS:39_2850 | VH3}3-21/D4|4-11|RF2/JH4 | ..................... | ............ | ................. | ................... | ..............I............................. | .RG---.......---SL | ............ |
| iPS:39_20H10 | | | | | | | | |
| iPS:39_3006 | VH3}3-21/D4|4-11|RF2/JH4 | ..................... | ............ | ................. | ....G............... | ............................................ | .RG---.......---SS | ............ |
| iPS:39_31G9 | | | | | | | | |
| iPS:39_3022 | VH3}3-21/D4|4-11|RF2/JH4 | ..................... | ...T........ | ................. | ....G............... | ............................................ | .RG---.......---SL | ............ |
| iPS:39_30H11 | | | | | | | | |
| iPS:39_3130 | VH3}3-21/D4|4-11|RF2/JH4 | ..................... | ...T........ | .........Q....... | ....G............... | ............................IF...F........... | .RG---.......---GT | ............ |
| iPS:39_33C2 | | | | | | | | |
| iPS:39_3906 | VH3}3-21/D4|4-11|RF2/JH4 | ..................... | ............ | .........D....... | ....G............... | ............................................ | .RG---.......---SG | ............ |
| iPS:39_13D3 | | | | | | | | |
| iPS:39_3982 | VH3}3-21/D4|4-11|RF2/JH4 | ..................... | ............ | ................. | ....G...... ...M...... | ............................................ | .RG---.......---SL | ............ |
| iPS:39_6C12 | | | | | | | | |
| iPS:39_8478 | VH3}3-21/D4|4-11|RF2/JH4 | ..................... | ............ | ................. | ................... | ..............................L.............. | .RG---.......---SS | ............ |
| iPS:39_17C10 | | | | | | | | |
| VH3}3-23|D6|6-6|RF1|JH4 | Germline | EVQLLES-GGGLVQPGGSLR SCAASG-FTFS | S------YAMS | WVRQAPGK GLEWVS | AISGSS--- GGSTYYAD SVKG | RFTISRDNSKNTLYLQM NSLRAEDIAVYYCAK | ETSSSS-----------SPDY | WGQGTL VTVSS |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:43_3897 | VH3\|3-23\|D6\|6-6\|RF1/JH4 | .......... | .......... | .......... | ....R...VN.FD.. | .......... | .R.G...... | .......... |
| iPS:43_3903 | VH3\|3-23\|D6\|6-6\|RF1/JH4 | .......... | .......... | .......... | ....R...IN.FD.. | .......... | .R.G...... | .......... |
| iPS:43_3911 | VH3\|3-23\|D6\|6-6\|RF1/JH4 | .......... | .......... | .......... | ....R...IN.FD.. | .......... | .R.G...... | .......... |
| iPS:43_3941 | VH3\|3-23\|D6\|6-6\|RF1/JH4 | .......... | .......... | .......... | ....R...VN.FD.. | .......... | .R.G...... | .......... |
| iPS:43_3957 | VH3\|3-23\|D6\|6-6\|RF1/JH4 | .......... | .......... | .......... | ....R...VN.FD.. | .......... | .R.G...... | .......... |
| iPS:43_3973 | VH3\|3-23\|D6\|6-6\|RF1/JH4 | .......... | .......... | .......... | ....R...IN.FD.. | .......... | .R.G...... | .......... |
| iPS:43_5715 | VH3\|3-23\|D6\|6-6\|RF1/JH4 | .........R | ......S... | .......V.. | V.......F.T... | .......... | SN..G....-W | .......... |
| iPS:43_5739 | VH3\|3-23\|D6\|6-6\|RF1/JH4 | .........R | ......S... | .......... | V.......F.T... | .......... | SN..G....-W | .......... |
| iPS:43_5749 | VH3\|3-23\|D6\|6-6\|RF1/JH4 | .......... | .......... | .......... | S...R...F..... | ...V...... | SN..G....-W | .......... |
| VH3\|3-21\|D7\|7-27\|RF1/JH4 | | EVQLVEST GGGLVQPGGSL RLSCAASG-FTFS | TSMR | WVRQAPGK GLEWVS | SISSSSSYIYYAD SVKG | RFTISRDNAKNSLYLQM NSLRAEDTAVYYCAR | | WGQGTL VTVSS |
| iPS:43_3901 | VH3\|3-21\|D7\|7-27\|RF1/JH4 | .......... | ........T.. | .......... | .....G....T..... | ........D.Q....G... | V.S-..... | .....A. |

Figure 52 (Continued)

| | | | | | | | | |
|---|---|---|---|---|---|---|---|---|
| iPS:43 3961 | 21-225_45D9 | VH3\|3-21/D7\|7-27\|RF1/J H4 | . . . . . . . . . . . . | . . . T . . . | . . . V . . . | . . . . G . . . | . . . . . . D.Q . . . | V.S-- . . . . . . . A . |
| iPS:43 4135 | 21-225_54H3 | VH3\|3-21/D7\|7-27\|RF1/J H4 | . . . . . . . . . . . . | . . . . I . . | . . . . . . . | . . . T . . . | . . . . . . . G . . . | M.T-- . . . . . . . . |
| iPS:43 4331 | 21-225_63H8 | VH3\|3-21/D7\|7-27\|RF1/J H4 | . . . . . . . . . . . . | . . . N . . . | . . . . . . . | . . . GT . . | . . . . . . . . . . . | . . . . . -VI |
| iPS:43 5421 | 21-225_151F1 | VH3\|3-21/D7\|7-27\|RF1/J H4 | . . . Y . . K . . . . . | . . . F . . . | . . . . . . . | . T MN.T . . | . . . . . . . . . . . | RN-- . . . . . . . . |
| iPS:43 5653 | 21-225_166H12 | VH3\|3-21/D7\|7-27\|RF1/J H4 | . . . . . . . A . . . . | . . . . . S . | . . . . Y . . | . . . . . . . | . . . . . . . . . . . | D.P-- . . . LV . |
| iPS:43 6648 | 21-225_227F11 | VH3\|3-21/D7\|7-27\|RF1/J H4 | . . . V . . . . . . . . | . . T . . . . | . . . . . G . | . . . G . . S | . . . . . . . . . . . | . . -- . . . . . . . . |
| iPS:39 2952 | 21-225_26G1 | VH3\|3-21/D7\|7-27\|RF1/J H4 | . . . . . . . . . . . . | . . . . . . . | . . . . . . . | IN.M. . . . | . . . . . . . . . . . | .G-- . . . . -V . |
| iPS:39 3082 | 21-225_34C11 | VH3\|3-21/D7\|7-27\|RF1/J H4 | . . . . . . . . . . . . | . . . G . . . | . . . . . . . | . . . G . . . | . . . . . . . . . . . | . T-- . . . . F . |
| iPS:39 4061 | 21-225_12D2 | VH3\|3-21/D7\|7-27\|RF1/J H4 | . . . . . . . . . . . . | . . T.S . . . | . . . . . . . | . . . N . . . | . . . . . . . . . . . | . -- . . . . . . . . |
| iPS:39 4071 | 21-225_10C7 | VH3\|3-21/D7\|7-27\|RF1/J H4 | . . . . . . . . . . . . | . . . . . . . | . . . . . . . | NN . . . . . | . . . . . . . S . . . | .G-- . . . . . A . |
| iPS:39 8532 | 21-225_33B7 | VH3\|3-21/D7\|7-27\|RF1/J H4 | . . . . . . . . . . . . | . . . N . . . | . . . . . . . | . . . G . . . | . . . . . . . . . . . | .G-- . . . . -V . |
| iPS:40 2225 | 21-225_2B1 | VH3\|3-21/D7\|7-27\|RF1/J H4 | . . . . . . . . . . . . | . . . . . . . | . . . . . . . | . . . . . . . | . . . . . . . . . . . | .G-- . . . . -N . |

| | | H_FR1 | H_CDR1 | H_FR2 | H_CDR2 | H_FR3 | H_CDR3 | H_FR4 |
|---|---|---|---|---|---|---|---|---|
| iPS:43 3925 | 21-225_44F3 | VH3\|3-23\|D7\|7-27\|RF1\|J H3 | ..H............. | ................ | ............. | IL..G... .KT... ... | ............. .............. | R.PSD....... ............. | ...... ...... |
| iPS:43 3953 | 21-225_45H4 | VH3\|3-23\|D7\|7-27\|RF1\|J H3 | ................ | ................ | ............M | .SN.F... | ........H. ....F..... | R.PSD....V. ............. | ...... ...... |
| iPS:43 3959 | 21-225_45C9 | VH3\|3-23\|D7\|7-27\|RF1\|J H3 | ..........N..... | ................ | ............. | V...R... ....T... | ............. ............. | R.PSD....... ............. | ...... ...... |
| iPS:43 5379 | 21-225_149B6 | VH3\|3-23\|D7\|7-27\|RF1\|J H3 | ................ | ................ | ............. | V...... ....F... | ............F ............. | R.PED....V. ............. | ...... ...... |
| iPS:43 5787 | 21-225_180A3 | VH3\|3-23\|D7\|7-27\|RF1\|J H3 | ..E............. | ......F..N..... | ............. | V...R... ....N.F... | ............F ............. | R....D..V..V ............. | ...... ...... |
| iPS:43 5809 | 21-225_182H5 | VH3\|3-23\|D7\|7-27\|RF1\|J H3 | ................ | ................ | ............. | V...R... ...T.F... | ............F ............. | R....D.....V ............. | ...... ...... |
| iPS:43 5889 | 21-225_186A11 | VH3\|3-23\|D7\|7-27\|RF1\|J H3 | ................ | ................ | ............. | V...R... ...T.F... | ............. ............. | R....D.....V ............. | ...... ...... |
| | VH4\|4-59\|D6\|6-13\|RF2\|JH4 | Germline | H_FR1 CVQLQES GPGLVKPSETLS LTCTVSC GSIS | H_CDR1 SYYS | H_FR2 WIRQPPGK GLEWIG | H_CDR2 SCSTYYNP SSLKS | H_FR3 RV TISVDTSKNQFSLKL SSVTAADTAVYYCAR | H_CDR3 GXAA —————— GYFDY | H_FR4 WGQGTL VTVSS |
| iPS:43 3931 | 21-225_44F6 | VH4\|4-59\|D6\|6-13\|RF2\|J H4 | ......H......... | ................ | ............. | ......N... ............ | .........I..... ............V. | ...V.I-.......GYFDY ............--KN. | ......I ...... |
| | VH3\|3-23\|D4\|4-17\|RF2\|JH6 | Germline | H_FR1 EVQLLES GGGLVQPGGSLR LSCAASG FTFS | H_CDR1 SYAMS | H_FR2 WVRQAPGK GLEWVS | H_CDR2 AISGS GGSTYYA DSVKG | H_FR3 RFTISRDNSKNTLYLQMN SLRAEDTAVYYCAR | H_CDR3 DYGDYY —————— YYYGMDV | H_FR4 WGQGTT VTVSS |
| iPS:43 3943 | 21-225_44E10 | VH3\|3-23\|D4\|4-17\|RF2\|J H6 | ..S............. | ................ | ............. | GVV.... ....R... | ............. ............. | R.QWL....... LG........... | ...... ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 3989 | 21-225_47C7 | VH3|3-23/D4|4-17|RF2/J H6 | ........................ N............. | ................ | ........G... .SR.... ..... | ...................................... | .R.QWL- ..IG.... | ........ |
| iPS:43 4133 | 21-225_54G3 | VH3|3-23/D4|4-17|RF2/J H6 | ........................ T............. | ................ | ........F... VN.F.... ..... | ...................................... | LGK.... -..... | ........ |
| iPS:43 4221 | 21-225_60A11 | VH3|3-23/D4|4-17|RF2/J H6 | .......T................ N............. | ................ | ............ ..N.F... ..T.. | ...................................... | LGK..H- ...... | ........ |
| iPS:43 4257 | 21-225_62F7 | VH3|3-23/D4|4-17|RF2/J H6 | ........................ ....V........ | ................ | ........E... ......G ...AK.. | ...................V.................. | LGI...- ...... | ........ |
| iPS:43 4283 | 21-225_57F8 | VH3|3-23/D4|4-17|RF2/J H6 | ........V............... ................ | ................ | ............ ....S... ..N.F.. ..T.. | ...................V.................. | LGK..H- ...... | ........ |
| iPS:43 4385 | 21-225_66C10 | VH3|3-23/D4|4-17|RF2/J H6 | ........................ ....V........ | ................ | ........E... ......G ...AR.. | ...................................... | LGI...- ...... | ........ |
| iPS:43 5717 | 21-225_171A9 | VH3|3-23/D4|4-17|RF2/J H6 | .......A................ ....T........ | ................ | ............ .....N.FN... | ...................................... | LGI...- ...... | ........ |
| iPS:43 6528 | 21-225_224B1 | VH3|3-23/D4|4-17|RF2/J H6 | ........V............... ................ | ................ | ........H... ......G ....N... | ...................................... | EG.Y..- ...V.. | ........ |
| iPS:39 3810 | 21-225_5A4 | VH3|3-23/D4|4-17|RF2/J H6 | ........V............... .L..S........ | ................ | ............ ...R.. ..N.F.T ..... | ...................................... | LGK...- ...... | ........ |
| | Germline | H_FR1 | H_CDR1 | H_FR2 | H_CDR2 | H_FR3 | H_CDR3 | H_FR4 |
| VH3|3-48|D5|5-24|RF3/JH6 | | EVQLVES GGGLVQPGGSLR LSCAASG-FTFS | S YSMN | WVRQAPGK GLEWVS | SISSS SSIYYAD SVKG | RFTISRDNAKNSLY LQM NSLRDEDTAVYYCAR | RDGYNYY --YYYGMDV | WGQGT TVTVSS |
| iPS:43 3945 | 21-225_44C12 | VH3|3-48|D5|5-24|RF3/J H6 | ................ ................ | ........V..... | ............ ............. | ...................................... | SGYSYA ...... | ........ |
| | Germline | H_FR1 | H_CDR1 | H_FR2 | H_CDR2 | H_FR3 | H_CDR3 | H_FR4 |

Figure 52 (Continued)

| | | QVQLVES...GGSVVQPGRSLR LSCAASG.FTFS | S...YGMH | WVRQAPGK...GLEWVA VISYDGSNK.YYAD | SVKG | RFTISRDNSKNTLYLQM NSLRAEDTAVYYCAR | GIAVAG...........GLFDY | WGQGTLVTVSS |
|---|---|---|---|---|---|---|---|---|
| | Germline | H_FR1 | H_CDR1 | H_FR2 | H_CDR2 | H_FR3 | H_CDR3 | H_FR4 |
| iPS:43 3947 | VH3-33/D6-13/JRF2JH4 | ....H.A.........E ..........L. | ......DDT. | ..........P. | .....F...... EY........ | ...................A........... | DLI..A.....TG... | ........... |
| iPS:43 3963 | VH3-33/D6-13/JRF2JH4 | ....H.A.........E ..........L. | ......DDS. | ..........P. | .....F...... EYT....... | .N...........A........... | DLI..T......TG... | ........... |
| iPS:43 3987 | VH3-33/D6-13/JRF2JH4 | ..................E ............ | D.....DDT. | .............. | .....F...... .......... | ........S............... | DLI..A.....TV... | ........... |
| iPS:43 6258 | VH3-33/D6-13/JRF2JH4 | ..................E ............ | V......... | .............. | .I.......... .F........ | ...................S........... | N....A......P... | ........... |
| iPS:39 2646 | VH3-33/D6-13/JRF2JH4 | .................. ..........L. | ......DD.. | ..........E. | .....F...... .F........ | .IM..........G........... | DLI..A.....TV... | ........... |
| iPS:39 2750 | VH3-33/D6-13/JRF2JH4 | .................. ..........L. | ......DD.. | ..........E. | .....F...... .F........ | .I...........M........... | DLI..A.....TV... | ........... |
| | Germline | H_FR1 | H_CDR1 | H_FR2 | H_CDR2 | H_FR3 | H_CDR3 | H_FR4 |
| | VH3-23/D6-19/JRF2JH3 | QVQLLES...GGGLVQPGGSLR LSCAASG.FTFS | S...YAMS | WVRQAPGK...GLEWVS AISGS..GGSTYYAD | SVKG | RFTISRDNSKNTLYLQM NSLRAEDTAVYYCAK | GLAVAG...........DAFDI | WGQGTMVTVSS |
| iPS:43 3999 | VH3-23/D6-19/JRF2JH3 | ...................... ..........R. | .......... | .............. | V....R...... .F........ | ................................ | R......NE... | ........... |
| iPS:43 4003 | VH3-23/D6-19/JRF2JH3 | ...................... ..........R. | .......... | .............. | V....R...... .F........ | ................R............... | R......NE... | ........... |
| iPS:43 4037 | VH3-23/D6-19/JRF2JH3 | ...................... ...........T | .......... | .............. | V....R...... ..F....... | ......L..........R............... | R......N.... | ........... |
| iPS:43 4041 | VH3-23/D6-19/JRF2JH3 | ...................... ..........R. | .......... | .............. | V....R...... ..F....... | ................R............... | R......NE... | ........... |

Figure 52 (Continued)

| | | | | | | | | | |
|---|---|---|---|---|---|---|---|---|---|
| iPS:43 4045 | 21-225_50H10 | VH3\|3-23\|D6\|6-19\|RF2/J H3 | .G.......... | ............ | ............ | V...R. ..F... | ............ | .R.......... | R.....NE.... |
| iPS:43 4073 | 21-225_51H10 | VH3\|3-23\|D6\|6-19\|RF2/J H3 | ...R......T | ............ | ............ | V..... .T.F.. | ..L......... | .R.......... | R......N.... |
| iPS:43 6212 | 21-225_200G1 | VH3\|3-23\|D6\|6-19\|RF2/J H3 | ............ | ............ | .......N.... | ...R. .N.F.. ..R. | ............ | .K.......... | R...D..Y...V |
| iPS:39 2652 | 21-225_17C6 | VH3\|3-23\|D6\|6-19\|RF2/J H3 | ..E......... | ............ | .......N.... | V...R. ..N.F. | ............ | F........S.. | RL......SE... |
| iPS:39 2668 | 21-225_17B4 | VH3\|3-23\|D6\|6-19\|RF2/J H3 | ..E......... | ...G..M...... | .......T.... | ............ | ............ | ........S.. | RL......SE... |
| iPS:39 2696 | 21-225_20A4 | VH3\|3-23\|D6\|6-19\|RF2/J H3 | ..E......... | ............ | .......N.... | V.....  ..Y..N. | ...V........ | ........S.. | R.......SE... |
| iPS:39 2702 | 21-225_17F7 | VH3\|3-23\|D6\|6-19\|RF2/J H3 | ..E......... | ............ | ............ | I...R. ..N.F. | ............ | ........S.. | RL......SE... |
| iPS:39 2704 | 21-225_17F11 | VH3\|3-23\|D6\|6-19\|RF2/J H3 | .A.......... | ............ | ............ | V...R. ..N..S | ............ | ........S.. | RL......SE..H. |
| iPS:39 2720 | 21-225_17A12 | VH3\|3-23\|D6\|6-19\|RF2/J H3 | .I......... ..E......... | ...D........ | ............ | I...R. .NAF.. | ............ | ........S.. | R.......SE... |
| iPS:39 2722 | 21-225_18E12 | VH3\|3-23\|D6\|6-19\|RF2/J H3 | ............ | ...T........ | ............ | I...R. ..N.F. | ............ | ........S.. | RL......SE... |
| iPS:39 2760 | 21-225_22G3 | VH3\|3-23\|D6\|6-19\|RF2/J H3 | ..E......... | ............ | .......N.... | I..... VN.F.. | ............ | F.H...... S | RL......SE... |
| iPS:39 2764 | 21-225_22G10 | VH3\|3-23\|D6\|6-19\|RF2/J H3 | ...D......T | ............ | .......N.... | V...... ..N.F. | ............ | ........S.. | RM......SE... |

Figure 52 (Continued)

| | | | | | | | |
|---|---|---|---|---|---|---|---|
| iPS:39 2812 | 21-225_21F4 | VH3\|3-23\|D6\|6-19\|RF2/J H3 | . . . . . . . . . . . . . . . . . E . . . | . . . . . . . . . . N | . . . . . . . . . . . . . . . . . . . . . . | V . . R . . . . . N . F . . . . . . . | . . . . . . . . . . . . . . . . . . . . V | RL . . . . . . . . SE . C . . |
| iPS:39 2816 | 21-225_22E4 | VH3\|3-23\|D6\|6-19\|RF2/J H3 | . . . . . . . . . . . . . . . . . E . . . | . . . . . . . . . . . | . . . . . . . . . . . . . . I . . . . . . | I . . R . . . . TN . F . . . . . . . | . . . . . . . . . . . . . . . . . . . S . | R . . . . . . . . . SE . . . . |
| iPS:39 2852 | 21-225_21A2 | VH3\|3-23\|D6\|6-19\|RF2/J H3 | . . . . . . . . . . . . . . . . . K . . . | . . . . . . . . . . N | . . . . . . . . . . . . . . . . . . . . . | I . . R . . . . . N . F . . . . . . . | . . . . . . . . . . . . . . . . . . . S . | RL . . . . . . . . SE . . . . |
| iPS:39 2878 | 21-225_22C5 | VH3\|3-23\|D6\|6-19\|RF2/J H3 | . . . . . . . . . . . . . . . . . V . . . | . . . . . . . . . . . | . . . . . . . . . . . . . . . M . . . . . | . . . I . . . . . . . Y . . . . . . . | . . . . . . . . . . . . . . . . . . . S . | R . . . . . . . . . SE . . . . |
| iPS:39 2902 | 21-225_22D5 | VH3\|3-23\|D6\|6-19\|RF2/J H3 | . . . . . . . . . . . . . . . . . E . . . | . . . . . . . . . . . | . . . . . . . . . . . . . . . . . . . . . | V . . R . . . . . N . F . . . . . . . | . . . . . . . . . . . . . . . . . . . S . | R . . . . . . . . . SE . . . . |
| iPS:39 3824 | 21-225_10F12 | VH3\|3-23\|D6\|6-19\|RF2/J H3 | . . . . . . . . . . . . . . . . . E . . . | . . . . . . . . . . . | . . . . . . . . . . . . . . . . . . . . . | I . . R . . . . . N . F . . . . . . . | . . . . . . . . . . . . . . . . . . . S . | RV . . . . . . . . SE . A . . |
| iPS:39 3848 | 21-225_4H2 | VH3\|3-23\|D6\|6-19\|RF2/J H3 | . . . . . . . . . . . . . . . . . . . . . | . . . . . . . . . . G | . . . . . . . . . . . . . . . . . . . . . | M V . . R . . . . . . Y . . . . . . . | . . . . . . . . . . . . . . . . . . . S . | RL . . . . . . . . SE . . . . |
| iPS:39 3862 | 21-225_5G2 | VH3\|3-23\|D6\|6-19\|RF2/J H3 | . . . . . . . . . . . . . . . . . T . . . | . . . . . . . . . . . | . . . . . . . . . . . . . . . . . . . . . | V . . R . . . . VN . F . . . . . . . | . . . . . . . . . . . . . . . . . . . S . | R . . . . . . . . . SE . . . . |
| iPS:39 3888 | 21-225_3E3 | VH3\|3-23\|D6\|6-19\|RF2/J H3 | . . . . . . . . . . . . . . . . . E . . . | . . . . . . . . . V . | . . . . . . . . . . . . . . . . . . . . . | I . . R . . . . . N . F . . . . . . . | . . . . . . . . . . . . . . . . . L . S . | RL . . . . . . . . SE . . . . |
| iPS:39 3898 | 21-225_5F7 | VH3\|3-23\|D6\|6-19\|RF2/J H3 | . . . . . . . . . . . . . . . . . E . . . | . . . . . . . . . . . | . . . . . . . . . . . . . . . . . . . . . | I . . R . . . . . N . F . . . . . . . | . . . . . . . . . . . . . . . . F . . S . | R . . . . . . . . . SE . A . . |
| iPS:39 3980 | 21-225_6D3 | VH3\|3-23\|D6\|6-19\|RF2/J H3 | . . . . . . . . . . . . . . . . . E . . . | . . . . . . . . . . N | . . . . . . . . . . . . . . . . . . . . . | V . . R . . . . . N . F . . . . . . . | . . . . . . . . . . . . . . . . . . . S . | RL . . . . . . . . SE . . . . |
| iPS:39 4014 | 21-225_8G6 | VH3\|3-23\|D6\|6-19\|RF2/J H3 | . . . . . . . . . . . . . . . . . E . . . | . . . . . . . . V . N | . . . . . . . . . . . . . . . . . . . . . | V . . R . . . . . N . F . . . . . . . | . . . . . . . . . . . . . . . . . . . S . | RL . . . . . . . . SE . . . . . S . . . |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:39 4022 | 21-225_16H6 | VH3\|3-23\|D6\|6-19\|RF2\|JH3 | ........... | ...N...... | ....M.V..R. ...........Y.. | ........... | RL.......SE..... | ........... |
| iPS:39 4043 | 21-225_3B1 | VH3\|3-23\|D6\|6-19\|RF2\|JH3 | .....E..... | ...N...... | ....V...R. ...IN.F...... | ........S. | RL.......SE..... | ........... |
| iPS:39 4077 | 21-225_8E12 | VH3\|3-23\|D6\|6-19\|RF2\|JH3 | .....E..... | ........... | ....I...R. ...N.F....... | ........S. | RM.......SE..... | ........... |
| iPS:39 4087 | 21-225_11A5 | VH3\|3-23\|D6\|6-19\|RF2\|JH3 | .....E...D. | ........... | ....V...R. ...VN.F....... | ........S. | R........SE..... | ........... |
| VH3\|3-11\|D6\|6-6\|RF2\|JH3 | Germline | H_FR1 EVQLLES GGGLVQPGGSLR LSCAASG-FTFS | H_CDR1 YYMS | H_FR2 WVRQAPGK GLEWVS | H_CDR2 YISSS GSTIYAD SVKG | H_FR3 RFTISRDNAKNSLY LQM | H_CDR3 STARR--------DADI | H_FR4 WGQGTM VTVSS |
| iPS:43 4011 | 21-225_48B10 | VH3\|3-11\|D6\|6-6\|RF2\|JH3 | ........... | ....F.T... | ....Q...... | ......A... ..GA... ...... | ........I.. | AV..P......GV.. | ........... |
| VH3\|3-11\|D6\|6-6\|RF2\|JH4 | Germline | H_FR1 EVQLLES GGGLVQPGGSLR LSCAASG-FTFS | H_CDR1 YYMS | H_FR2 WVRQAPGK GLEWVS | H_CDR2 YISSS GSTIYAD SVKG | H_FR3 RFTISRDNAKNSLY LQM | H_CDR3 STARR--------YFDI | H_FR4 WGQGTL VTVSS |
| iPS:43 4015 | 21-225_48F12 | VH3\|3-11\|D6\|6-6\|RF2\|JH4 | ........... | ....F.T... | ....Q...... | ......A... ..GA... | ........I..F. | AV..P......GA..I | ........... |
| iPS:43 4017 | 21-225_48G12 | VH3\|3-11\|D6\|6-6\|RF2\|JH4 | ........... | ....F.T... | ....Q...... | ......A... ..GA... | ........I..F. | AV..P......GA..I | ........... |
| VH3\|3-23\|D6\|6-13\|RF2\|JH4 | Germline | H_FR1 EVQLLES GGGLVQPGGSLR LSCAASG-FTFS | H_CDR1 SYAMS | H_FR2 WVRQAPGK GLEWVS | H_CDR2 AISGS GSTIYAD SVKG | H_FR3 RFTISRDNSKNTLY LQM | H_CDR3 GTAAA--------GIFDI | H_FR4 WGQGTI VTVSS |
| iPS:43 4023 | 21-225_49F1 | VH3\|3-23\|D6\|6-13\|RF2\|JH4 | ........... | ........... | ....D...... | ......V... ....F.. | ........S.. | A........G.....AH | ........... |

| | | | | | | | | |
|---|---|---|---|---|---|---|---|---|
| iPS:43 4043 | 21-225_50G10 | VH3J3-21/D1J1-1JRF2/JH4 | . . . . . . . | . . . . . . . | . . . . . . . | . G . . . . | . . . . . . | . . . . . . | AT--- . . . . . |
| iPS:43 4085 | 21-225_52E3 | VH3J3-21/D1J1-1JRF2/JH4 | . . . . . . . | . . . K . . | . . . . . . . | . . G . . . N.S . | . . . E . . | . . . . . . | SS--- . . . . . -N . . |
| iPS:43 4101 | 21-225_52H12 | VH3J3-21/D1J1-1JRF2/JH4 | . . . . . . . | . . . . . . . | . . . . . . . | . . G . . . T . | . . . V . . | . . . . . . | NS--- . . . . . |
| iPS:43 4187 | 21-225_56A5 | VH3J3-21/D1J1-1JRF2/JH4 | . . . . . . . | . . . . . . . | . . . . . . . | . . G . . . | . . . . . . | . . . . . . | AT--- . . . . . |
| iPS:43 4265 | 21-225_57B2 | VH3J3-21/D1J1-1JRF2/JH4 | . . . . . . . | . . . . . . . | . . . . . . . | . . G . . . N T | . . . . . . | . . . . . . | AG--- . . . . . |
| iPS:43 4439 | 21-225_70E12 | VH3J3-21/D1J1-1JRF2/JH4 | . . . . . . . | . . . . . . . | . . . . . . . | . GN . . . T . T | . . . . . . D . T | . . . . . . | AA--- . . . . . . . . C |
| iPS:43 5515 | 21-225_157E4 | VH3J3-21/D1J1-1JRF2/JH4 | . . . . . . . | . . . . . . . | . . . . . . . | . . G . . . | . . . K . . | . . . . . . | AT--- . . . . . |
| iPS:43 5535 | 21-225_157H10 | VH3J3-21/D1J1-1JRF2/JH4 | . . . . . . . | N . . . R . . | . . . . . . . | . . G . . . N | . . . . . . | . . . . . . | AH--- . . . . . |
| iPS:43 7224 | 21-225_56H1 | VH3J3-21/D1J1-1JRF2/JH4 | . . . . . . . | . . . . . . . | . G . . . I | . . G . . . TD . | . . . . . . | . . . . . . | AS--- . . . . . |
| iPS:39 2620 | 21-225_17H5 | VH3J3-21/D1J1-1JRF2/JH4 | . . . . . . . | . . . . . . . | . . . . . . . | . . G . . . T . | . . . . . . | . . . . . . | AS--- . . . . . |
| iPS:39 2632 | 21-225_16A11 | VH3J3-21/D1J1-1JRF2/JH4 | . . . . . . . | . . . . . . . | . . . . . . . | . . G . . . L . | . . . . . . | . . . . . . | AA--- . . . . . |
| iPS:39 2746 | 21-225_20H7 | VH3J3-21/D1J1-1JRF2/JH4 | . . . . . . . H | . . . . . . . | . . . . . . . | . . G . . . F . | . . . . . . | . . . . . . | AA--- . . . . . -L . . |

Figure 52 (Continued)

| | | | | | | | |
|---|---|---|---|---|---|---|---|
| iPS:39 2782 | 21-225_22B12 | VH3}3-21/D1{1-1}RF2/JH4 | | | .G.<br>.T. | | AA---<br>...- |
| iPS:39 2916 | 21-225_27C5 | VH3}3-21/D1{1-1}RF2/JH4 | | | .T.<br>D | | AS---<br>..-L.S |
| iPS:39 2976 | 21-225_27H12 | VH3}3-21/D1{1-1}RF2/JH4 | | .L | | F | AS---<br>...-.C |
| iPS:39 3120 | 21-225_35H8 | VH3}3-21/D1{1-1}RF2/JH4 | | | .G.<br>.N...T | K.V | AS---<br>... |
| iPS:39 3836 | 21-225_15A2 | VH3}3-21/D1{1-1}RF2/JH4 | | .T | ...GT<br>G.F. | .A | .SG---<br>..-I |
| iPS:39 3894 | 21-225_5E11 | VH3}3-21/D1{1-1}RF2/JH4 | | | .G.<br>G | | AS---<br>... |
| iPS:39 3896 | 21-225_2A4 | VH3}3-21/D1{1-1}RF2/JH4 | | | .G.<br>.T | .F | AS---<br>... |
| iPS:39 3914 | 21-225_16B8 | VH3}3-21/D1{1-1}RF2/JH4 | | .T | .G.<br>.T | .IA. | AS---<br>... |
| iPS:39 3944 | 21-225_14D6 | VH3}3-21/D1{1-1}RF2/JH4 | | .N | .G.<br>G | .M | AS---<br>... |
| iPS:39 3952 | 21-225_1F1 | VH3}3-21/D1{1-1}RF2/JH4 | | | .G. | | AA---<br>...-.S |
| iPS:39 4033 | 21-225_5F4 | VH3}3-21/D1{1-1}RF2/JH4 | .V | | .G. | F | N.---<br>... |
| iPS:39 4069 | 21-225_16H1 | VH3}3-21/D1{1-1}RF2/JH4 | | | .G.<br>.T | | NN---<br>... |
| | | | | | | | AA---<br>...-.S |

| | | Germline | H_FR1 | H_CDR1 | H_FR2 | H_CDR2 | H_FR3 | H_CDR3 | H_FR4 |
|---|---|---|---|---|---|---|---|---|---|
| iPS:43 4055 | 21-225_51B4 | VH3\|3-23/D1\|1-20\|RF1/J H3 | ........S.... ..........R | ........V.. | ........ | .....R. .SN.F.T. ..... | .......V...... S............. | ...SH... ......G.... | ........ ........ |
| | VH3\|3-23\|D7\|7-27\|RF1/JH4 | | EVQLLES GGGVVQPGGSLR LSCAASG_FTFS | S---- YAMS | WVRQAPGK GLEWVS | AISGS GGSTYYAD SVKG | RFTISRDNSKNTLYLQM NSLRAEDTAVYYCAR | ITTY -------FDY | WGQGTL VTVSS |
| iPS:43 4059 | 21-225_51C5 | VH3\|3-23/D7\|7-27\|RF1/J H4 | | ........V. | ........T | ..TM..... ...R..... ...N..... | ........V..... S............R | V.A- .......... | ........ ........ |
| iPS:43 4213 | 21-225_60A4 | VH3\|3-23/D7\|7-27\|RF1/J H4 | | ........V. | | ...S..... ...W.N... ........ | ........T..... .............R | ......-I.. .......... | ........ ........ |
| iPS:43 4215 | 21-225_60F7 | VH3\|3-23/D7\|7-27\|RF1/J H4 | | ........V. | | ...G..... ...NR.... ........ | ........S.....GS ............. | .G---..... .....-ID.. | ........ ........ |
| iPS:43 4241 | 21-225_61E6 | VH3\|3-23/D7\|7-27\|RF1/J H4 | | | | ...T..... ..VN.F... ........ | ............. ............. | ELG....... ........I. | ........ ........ |
| iPS:43 4281 | 21-225_57B8 | VH3\|3-23/D7\|7-27\|RF1/J H4 | ........R | | | ........ ..N.F.... ........ | ............. ............. | ELG....... ........I. | ........ ........ |
| iPS:43 4301 | 21-225_58F11 | VH3\|3-23/D7\|7-27\|RF1/J H4 | ........R | | | ........ ..N.F.... ........ | ........Y..... ............. | FF.MVG.... ......AGF. | ........ ........ |
| iPS:43 5523 | 21-225_157G5 | VH3\|3-23/D7\|7-27\|RF1/J H4 | | ........V. | ..D..... | ..M...... ...R..... ........ | ............. ............. | Y.W-...... .....NG... | ........ ........ |
| iPS:43 5659 | 21-225_167D12 | VH3\|3-23/D7\|7-27\|RF1/J H4 | | ........V. | | ..M...... ...R..... ........ | ............. ............. | Y.W-...... .....NG... | ........ ........ |
| iPS:43 5765 | 21-225_177D3 | VH3\|3-23/D7\|7-27\|RF1/J H4 | | ......V.N | | ..GM..... ...R..... ...D..... | ........S..... ............R | V.F-...... .......... | ........ ........ |

Figure 52 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:43 7216 | 21-225_51D5 | VH3\|3-23\|D7\|7-27\|RF1\|JH4 | ................ ................ ................ | ........V... | ......T.... | ...TM. ..R.... ..N. | ...V............ S............R | V.A-............ ................ | ................ |
| | | VH3\|3-21\|D5\|5-24\|RF2\|JH4 | EVOLVES GGGLVKPGGSLR LSCAASG-FTFS | S.....YSM H | WVRQAPGK GLEWVS | SISSS SSTIYAD SVKG | RFTISRDNAKNSLYLQM NSLRAEDTAVYYCAR | PWLQ LFPDI | WGQGTL VTVSS |
| iPS:43 4063 | 21-225_51G7 | VH3\|3-21\|D5\|5-24\|RF2\|JH4 | ................ ................ ................ | ................ | ................ | ................ | ................ | A.L-............ | ................ |
| | | Germline | H_FR1 | H_CDR1 | H_FR2 | H_CDR2 | H_FR3 | H_CDR3 | H_FR4 |
| | | VH3\|3-23\|D7\|7-27\|RF3\|JH4 | EVOLVES GGGLVQPGGSLR LSCAASG-FTFS | S.....YAMS | WVRQAPGK GLEWVS | AISGS GGSTYAD SVKG | RFTISRDNSKNTLYLQM NSLRAEDTAVYYCAK | NMCY FDI | WGQGTL VTVSS |
| iPS:43 4083 | 21-225_52H2 | VH3\|3-23\|D7\|7-27\|RF3\|JH4 | ................ ................ ................ | R....N.... | ................ | ...M.... N.F. | ...V............ ................ .F...... | .GREQ...WL. ................ | ................ |
| | | Germline | H_FR1 | H_CDR1 | H_FR2 | H_CDR2 | H_FR3 | H_CDR3 | H_FR4 |
| | | VH3\|3-30.3\|D6\|6-6\|RF2\|JH6 | QVQLVES GGGVVQPGRSLR LSCAASG-FTFS | S.....YAMH | WVRQAPGK GLEWVA | VISYD-GSNKYYAD SVKG | RFTISRDNSKNTLYLQM NSLRAEDTAVYYCAR | STANYY YYYGMDV | WGQGTT VTVSS |
| iPS:43 4087 | 21-225_52F6 | VH3\|3-30.3\|D6\|6-6\|RF2\|JH6 | ................ ................ ................ | ......G... | ................ | ...I....G. ................ | ................ ........D....... | RS...P-......... G............... | ................ |
| iPS:43 4111 | 21-225_53H2 | VH3\|3-30.3\|D6\|6-6\|RF2\|JH6 | ................ ................ ................ | ......G... | ........P. | ........G. ........H. | ................ | RG...P-......... G............... | ................ |
| iPS:43 4121 | 21-225_53F6 | VH3\|3-30.3\|D6\|6-6\|RF2\|JH6 | ................ ................ ................ | ......G... | ................ | ........G. ........D. | ................ ........T....... | RR...P-......... G............... | ................ |
| iPS:43 4163 | 21-225_50H1 | VH3\|3-30.3\|D6\|6-6\|RF2\|JH6 | ................ ................ ................ | ......G... | .......S.. | ...I....G. ........D. | ................ ........T....... | RR...P-......... G............... | I............... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:39 4035 | 21-225_5G9 | VH3|3-30.3/D6|6-6|RF2/JH6 | N.......G... | | I....A. ....V. | | R.T.L- | |
| VH3|3-33|D2|2-8|RF1/JH4 | Germline | EVOLVES-GGGVVQPGRSLR LSCAASG-FTFS | H_FR1 | S VGMH | H_CDR1 | WVRQAPGK VKYD- GSNKYYAD SVKG | H_FR2 | RFTISRDNSKNTLYLQM NSLRAEDTAVYYCAR | H_FR3 | **RTIY*RC -SLYFDI | H_CDR3 | WGQGTL VTVSS | H_FR4** |
| iPS:43 4095 | 21-225_52F10 | VH3|3-33|D2|2-8|RF1/JH4 | | F..... | | .....D. | | M..... | | DS...SS-SWL.... | |
| VH3|3-23|D4|4-23|RF3/JH4 | Germline | EVQLLES-GGGLVQPGGSLR LSCAASG-FTFS | | S---YAMS | | WVRQAPGK GLEWVS AISGS---- GGSTYYAD SVKG | | RFTISRDNSKNTLYLQM NSLRAEDTAVYYCAK | | TIVVT --YFDY | | WGQGTL VTVSS | |
| iPS:43 4107 | 21-225_53E2 | VH3|3-23|D4|4-23|RF3/JH4 | I........R | | | ....N.F... | | ....T...D. | | KV.D.A....MAL.. | |
| iPS:43 4181 | 21-225_56B2 | VH3|3-23|D4|4-23|RF3/JH4 | I........R | | | ....N.F... | | ....T...D. | | KV.D.A....MAL.. | |
| VH3|3-23|D1|1-26|RF1/JH3 | Germline | EVQLLES-GGGLVQPGGSLR LSCAASG-FTFS | | S YAMS | | WVRQAPEK GLEWVS AISSS---- GGSTYYAD SVKG | | RFTISRDNSKNTLYLQM NSLRAEDTAVYYCAK | | GIVGAT -YAFDI | | WGQGIM VTVSS | |
| iPS:43 4117 | 21-225_53C6 | VH3|3-23|D1|1-26|RF1/JH3 | .........N | | | ......A.. | | | | PL....H....E... | |
| iPS:39 2984 | 21-225_30E11 | VH3|3-23|D1|1-26|RF1/JH3 | DM | I | | V..... | | | | DR.K.H......G.. | |
| iPS:39 3114 | 21-225_33G12 | VH3|3-23|D1|1-26|RF1/JH3 | DM | | | V...SF | | ....T..... | | DR.R.H......G.. | |
| VH3|3-33|D5|5-24|RF2/JH4 | Germline | EVQLVES GGGVVQPGRSLR LSCAASG-FTFS | | S VGMH | | WVRQAPGK GLEWVA VINKD GSNKYYAD SVKG | | RFTISRDNSKNTLYLQM NSLRAEDTAVYYCAR | | TRLQ -LYFDY | | WGQGTL VTVSS | |

Figure 52 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:43 4127 | 21-225_53H8 | VH3|3-33/D5|5-24|RF2/JH4 | ................ ................ ................ | ...... | ................ ...... | ...... ...... | ................ ................ | A.IG- ........ ...-..S | ...... ...... |
| | VH3|3-23|D4|4-17|RF2|JH4 | | EVQLLES GGGLVQPGGSLR LSCAASG FTFS | S...... YAMS | WVRQAPGK GLEWVS | AISGS GGSTYYAD SVKG | RFTISRDNSKNTLYLQM NSLRAEDTAVYYCAR | DYGIY..... .....YFDY | WGQGTL VTVSS |
| iPS:43 4147 | 21-225_55E1 | VH3|3-23|D4|4-17|RF2/JH4 | ...... | ...... | ...... | ..S..F. | ............F........ | .H.IVG......TI... | ...... |
| iPS:43 5303 | 21-225_146A6 | VH3|3-23|D4|4-17|RF2/JH4 | ....N........ | ...N.. | ...... | ..N.F. | ...................... | KDN..VW......GSP. | ...... |
| iPS:43 5335 | 21-225_147D10 | VH3|3-23|D4|4-17|RF2/JH4 | ...... | ...... | ...... | ..R.F. N.F. | ...................... | KDY..VW......GSP. | ...... |
| iPS:43 5339 | 21-225_147D12 | VH3|3-23|D4|4-17|RF2/JH4 | ..S... | ...... | ...... | ..R.F. N.F. | ...................... | KDY..VW......GSP. | ...... |
| iPS:43 5343 | 21-225_148E2 | VH3|3-23|D4|4-17|RF2/JH4 | ...... | ...... | ...... | ..R.F. N.F. | ...................... | KDY..VW......GSP. | ...... |
| iPS:43 5381 | 21-225_149C6 | VH3|3-23|D4|4-17|RF2/JH4 | ...... | ...... | ...... | ..R.F. N.F. | ............H........ | KDY..VW......GSP. | ...... |
| iPS:43 5391 | 21-225_149F8 | VH3|3-23|D4|4-17|RF2/JH4 | ...... | ...... | ...... | ..R.F. N.F. | ...................... | KDY..VW......GSP. | ...... |
| iPS:43 5395 | 21-225_149D11 | VH3|3-23|D4|4-17|RF2/JH4 | ...... | ...... | ...... | ..R.F. N.F. | ...............R...... | KDY..VW......GSP. | ...... |
| iPS:43 5403 | 21-225_150C5 | VH3|3-23|D4|4-17|RF2/JH4 | ...... | ...... | ...... | ..N.F. | ...................... | KDY..VW......GSP. | ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5447 | 21-225_152H7 | VH3\|3-23\|D4\|4-17\|RF2/JH4 | ........................ .N | ........... | ..N.F... | ............ | KDN..VW... ....GSP.... | ..... |
| iPS:43 5453 | 21-225_152G10 | VH3\|3-23\|D4\|4-17\|RF2/JH4 | ..............N......... | ........... | ..N.F... | ............ | KDY..VW... ....GSP.... | ..... |
| iPS:43 5483 | 21-225_155A4 | VH3\|3-23\|D4\|4-17\|RF2/JH4 | ..............N......... | ........... | ..R...... ..N.F... | ............ | KDY..VW... ....GSP.... | ..... |
| iPS:43 5485 | 21-225_155B4 | VH3\|3-23\|D4\|4-17\|RF2/JH4 | ........................ | ........... | ..N.F... | ............ | KDY..VW... ....GSP.... | ..... |
| iPS:43 5777 | 21-225_178F7 | VH3\|3-23\|D4\|4-17\|RF2/JH4 | .....H.. .....T.. | .....T..... | V......... ..N.F... | ........R... | R........ ............ | ..... |
| iPS:43 5783 | 21-225_179G1 | VH3\|3-23\|D4\|4-17\|RF2/JH4 | .....H.. .....T.. | .....T..... | V...F... ..N.F... | ........R... | R........ ............ | ..... |
| iPS:43 5833 | 21-225_190D12 | VH3\|3-23\|D4\|4-17\|RF2/JH4 | ........................ | .........D. | ..I.N... ...R.... | ............ | M.R.S.... ....YGF.... | ..... |
| iPS:43 6156 | 21-225_197C8 | VH3\|3-23\|D4\|4-17\|RF2/JH4 | ........................ | .....S..T.. | ..I.N... ..RA.... | .....T...... | R.YSRIA... ....VAGT.... | ..... |
| VH3\|3-21\|D1\|1-1\|RF1\|JH4 | | Germline EVQLVES- GGGLVKPGGSLR LSCAASG-FTFS | S-----VSMN | WVRQAPGK GLEWVS | SISSS- SSIYYAD SVKG | RFTISRDNAKNSLYLQM NSLRAEDTAVYYCAR | GTIGT --- YFDY | WGQGTL VTVSS |
| iPS:43 4157 | 21-225_55D4 | VH3\|3-21\|D1\|1-1\|RF1\|JH4 | ........................ | ........R.. | ........ .NH.D... | .....L...... | ........... ........... | .S... |
| iPS:43 4243 | 21-225_62C1 | VH3\|3-21\|D1\|1-1\|RF1\|JH4 | ........................ | ........... | ........ ........ | .........I.. | FG----- ---VD | ..... |

| | | H_FR1 | H_CDR1 | H_FR2 | H_CDR2 | H_FR3 | H_CDR3 | H_FR4 |
|---|---|---|---|---|---|---|---|---|
| iPS:43-4175 | 21-225_55A11 | VH3\|3-30.3/D4\|4-17\|RF2/JH3 | .......... | ......G... | ......T.. ......R. | ..........V. | ..........T. | GR.R.SDY..... .....GH...... | ........ ........ |
| | Germline | H_FR1 | H_CDR1 | H_FR2 | H_CDR2 | H_FR3 | H_CDR3 | H_FR4 |
| | VH1\|1-02/D1\|1-1\|RF1\|JH2 | QVQLVQS-GAEVKKPGASVK VSCKASG-YTFT | G------YMH | WVRQAPGQ GLEWMG | WINPN--- SGGTNYAQ KFQG | RVTMTRDTSISTAYMEL SRLRSDDTAVYYCAR | GTTGTY... ........... | WGQGTL VTVSS |
| iPS:43-4193 | 21-225_56C6 | VH1\|1-02/D1\|1-1\|RF1/JH2 | ............ | D.........H... | ............ | R......V. | ...A..N... ...G........ | DG.S--.... .-S..Y..... | ........ |
| | Germline | H_FR1 | H_CDR1 | H_FR2 | H_CDR2 | H_FR3 | H_CDR3 | H_FR4 |
| iPS:43-4195 | 21-225_56F6 | VH1\|1-02/D5\|5-24\|RF1/JH4 | GAEVKKPGASVK VSCKASG-YTFT ........F... | G------YTH D........... | WVRQAPGQ GLEWMG ............ | WINPN--- SGGSNYAQ KFQG R........ | RVTMTRDTSISTAYMEL SRLRSDDTAVYYCAR ..........T. | EGATRP.TG... .............. | WGQGTL VTVSS ........ |
| | Germline | H_FR1 | H_CDR1 | H_FR2 | H_CDR2 | H_FR3 | H_CDR3 | H_FR4 |
| | VH3\|3-33/D1\|1-1\|RF2\|JH4 | QVQLVES- GGGLVQPGRSLR LSCAASG-FTFS | S------YGMH | MVRQAPGK GLEWVA | VIWYD- GSNKYYAD SVKG | RFTISRDNSKNTLYLQM NSLRAEDTAVYYCAR | VQLEF........ ............... | WGQGTL VTVSS |
| iPS:43-4203 | 21-225_60E2 | VH3\|3-33/D11\|1-1\|RF2/JH4 | ..........N... | D........... | ............ | I...... EN........ | ....S.......... | DV.D--.... ...P....... | ........ |
| iPS:43-4229 | 21-225_61H1 | VH3\|3-33/D11\|1-1\|RF2/JH4 | ..........N... | D........... | ............ | I...... E........ | ....S.......... | DV.D--.... ...P....... | ........ |
| | Germline | H_FR1 | H_CDR1 | H_FR2 | H_CDR2 | H_FR3 | H_CDR3 | H_FR4 |
| | VH1\|1-02/D5\|5-18\|RF3\|JH6 | QVQLVQS- GAEVKKPGASVK VSCKASG-YTFT | G------YYMH | WVRQAPGQ GLEWMG | WINPN--- SGGTNYAQ KFQG | RVTMTRDTSISTAYMEL SRLRSDDTAVYYCAR | GVSVGYY.... ....YYYGMDV | WGQGTT VTVSS |
| iPS:43-4209 | 21-225_60C3 | VH1\|1-02/D5\|5-18\|RF3/JH6 | ..........S... | ....H.I...... | .......Y... | ............V. | ........I...S.... | GLL.ATN..... .....Y....... | ........ |
| iPS:43-4315 | 21-225_59G7 | VH1\|1-02/D5\|5-18\|RF3/JH6 | ..........S... | ....H.I...... | .......Y... | ............V. | ........I...S.... | GLL.ATN..... .....Y....... | ...T.... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 4319 | VH1|1-02|D5|5-18|RF3/J H6 | ..........P.. | ....N.I. | | | ....TS......... | .GLL.AT....... | .... |
| iPS:44 3003 | VH1|1-02|D5|5-18|RF3/J H6 | ..........I... | .....I.. | ......Y... | | G......L...N....D. | .GN.F.-- | ....P |
| iPS:44 3005 | VH1|1-02|D5|5-18|RF3/J H6 | .............. | .....I.. | | | G......L...N....D. | .GN.F.-- | ....P |
| Germline | | H_FR1 QVQLQES- GGGLVQPGGSLR LSCAASG FTFS | H_CDR1 SG---DYKS | H_FR2 WFRQAPGK GLEWIG | H_CDR2 S--------------- SLKS | H_FR3 RVTISVDTSKNQFSL KL SSVTAADTAVYYCAR | H_CDR3 GSSSD --------VEDY | H_FR4 WGQGTL VTVSS |
| iPS:43 4217 | VH4|4-30.4|D5|5-12|RF3/J H4 | .R.A......... | RS...S...G | | ...AS | .......E......R. | LD..W- | .... |
| Germline | | H_FR1 QVQLLES GGGLVQPGGSLR LSCAASG FTFS | H_CDR1 S | H_FR2 YAMS WFRQAPGK GLRWVS | H_CDR2 AISGS GGSTYYAD SVKG | H_FR3 RFTISRDNSKNTLYLQM NSLRAEDTAVYYCAK | H_CDR3 ---------- LDBX | H_FR4 WGQGTL VTVSS |
| iPS:43 4219 | VH3|3-23|D3|3-22|RF3/J H4 | .............. | .... | | ...N.F. | .......F....... | FFG..G- ......A | .... |
| iPS:43 4289 | VH3|3-23|D3|3-22|RF3/J H4 | .......L..... | .... | ......D.. | ...N.F.G. | ........K...... | G..... | .... |
| iPS:43 4297 | VH3|3-23|D3|3-22|RF3/J H4 | .............. | .... | | ...N.F. | .......F....... | FFG..G- ......A | .... |
| iPS:39 2996 | VH3|3-23|D3|3-22|RF3/J H4 | .........R... | .... | | ...N.F. | ............... | LGR.A.T.......GP | .... |
| Germline | VH4|4-59|D4|4-11|RF3/J H4 | H_FR1 QVQLQES GPGLVKPSETLS LTCTVSG-GSIS | H_CDR1 S YWS | H_FR2 WIRQPPGK GLEWIG | H_CDR2 YISGSTYYNP SLKS | H_FR3 RVTISVDTSKNQFSLKL SSVTAADTAVYYCAR | H_CDR3 ----------VEDY | H_FR4 WGQGTL VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 4225 | 21-225_60E12 | VH4|4-59/D4|4-11|RF3|JH4 | ........ | ....F... | ........ | ....A.. | R..T... | ...M.... | EGK.GG... | .... |
| | | | | | | | | ......VS.... | |
| iPS:43 4227 | 21-225_61A1 | VH4|4-59/D4|4-11|RF3|JH4 | ........ | ....HF.. | ........ | ....A.. | R..I... | ...M.... | EGK.GG... | .... |
| | | | | | | | R...... | | ......VS.... | |
| iPS:43 4267 | 21-225_57F2 | VH4|4-59/D4|4-11|RF3|JH4 | ........ | ........ | ........ | ........ | R..T... | ...M.I.. | EGK.GG... | .... |
| | | | | | | | R...... | | ......VS.... | |
| Germline | VH3|3-23|D5|5-18|RF3|JH3 | H_FR1 EVQLLES GGGLVQPGGSLR LSCAASG.FTFS | H_CDR1 .YAMS | H_FR2 WVRQAPGK GLEWVS | H_CDR2 AISGS GGSTYYAD SVKG | H_FR3 RFTISRDNSKNTLYLQM NSLRAEDTAVYYCAR | H_CDR3 GYSYGY DAFDI | H_FR4 WGQGTM VTVSS |
| iPS:43 4239 | 21-225_58F1 | VH3|3-23|D5|5-18|RF3|JH3 | ........ | ........ | ........ | ....TG. | ........ | RGV..D.. | .... |
| | | | | | | N...... | | | |
| iPS:43 4309 | 21-225_59B5 | VH3|3-23|D5|5-18|RF3|JH3 | ........ | ......N. | ........ | ..N.F.. | ........ | RGV..D.. | .... |
| | | | | | | | | ......YE. | |
| Germline | VH3|3-33|D5|5-18|RF1|JH4 | H_FR1 EVQLVES GGGVVQPGRSLR LSCAASG.FTFS | H_CDR1 .YGMH | H_FR2 WVRQAPGK GLEWVA | H_CDR2 VIWYD GSNKYYAD SVKG | H_FR3 RFTISRDNSKNTLYLQM NSLRAEDTAVYYCAR | H_CDR3 VDTHP VFDI | H_FR4 WGQGTL VTVSS |
| iPS:43 4245 | 21-225_62H1 | VH3|3-33|D5|5-18|RF1|JH4 | ........ | ....T... | ...Q.... | ....... | ...I.... | E.PRT... | .... |
| | | | | | | .M..... | | ......SCS.. | |
| iPS:43 4323 | 21-225_62H8 | VH3|3-33|D5|5-18|RF1|JH4 | ........ | ...T.... | ........ | ....H.. | ........ | E.PRT... | .... |
| | | | | | | .D..V.. | | ......SCS.. | |
| iPS:43 4379 | 21-225_66A9 | VH3|3-33|D5|5-18|RF1|JH4 | ........ | ........ | ........ | ....H.. | ........ | E.PRT... | .... |
| | | | | | | .D..... | | ......SCS.. | |
| Germline | VH3|3-33|D11-11|RF3|JH4 | H_FR1 EVQLVES GGGVVQPGRSLR LSCAASG.FTFS | H_CDR1 .YGMH | H_FR2 WVRQAPGK GLEWVA | H_CDR2 VIWYD GSNKYYAD SVKG | H_FR3 RFTISRDNSKNTLYLQM NSLRAEDTAVYYCAR | H_CDR3 YNWND VFDY | H_FR4 WGQGTL VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 4247 | 21-225_62D2 | VH3/3-33/D1|1-1|RF3/JH4 | ..........Y... | ................. | ................. | ................. | .................. | D.G.W........ ...N.L....... | ............. |
| iPS:43 6838 | 21-225_52H4 | VH3/3-33/D1|1-1|RF3/JH4 | ................ | .......H......F... | .........K....... | ................. | .................. | GD..Y........ .......EG..... | ............. |
| iPS:43 6948 | 21-225_183F5 | VH3/3-33/D1|1-1|RF3/JH4 | ................ | ..............L.. | ................. | .........G....... | .................. | E.FW-........ .....SG....... | ............. |
| Germline | | H_FR1 QLQLQES GPGLVKPSETLS LTCTVSG GSIS | H_CDR1 SS SYWG | H_FR2 WIRQPPGK GLEWIG | H_CDR2 SIYY SGSTYYNP SLKS | H_FR3 RVTISVDTSKNQFSLKL SSVTAADTAVYYCAR | H_CDR3 CVSGYD ---------YYFDY | H_FR4 WGQGTL VTVSS |
| iPS:43 4249 | 21-225_62E2 | VH4/4-39/D5|5-12|RF3/JH4 | ................ | .......R......... | ................. | .......IAS....... | .................. | LS...W- .....-S....... | ............. |
| iPS:43 4353 | 21-225_64B12 | VH4/4-39/D5|5-12|RF3/JH4 | .........V..... | .......R......... | ................. | .........S....... | ..............T... | LD...W- .....-S....... | ............. |
| iPS:39 4073 | 21-225_15C9 | VH4/4-39/D5|5-12|RF3/JH4 | ................ | .......R......... | ................. | .......N.....N... | .................. | QG..W- .....-EV...... | ............. |
| Germline | | H_FR1 CVQLVQSG AEVKKPGASVK VSCKASG YTFT | H_CDR1 G YYMH | H_FR2 WVRQAPGQ GLEWMG | H_CDR2 WINPN SGGTNYAQ KFQG | H_FR3 RVTMTRDTSISTAYMEL SRLRSDDTAVYYCAR | H_CDR3 LLGY ----------FDY | H_FR4 WGQGTL VTVSS |
| iPS:43 4259 | 21-225_62G7 | VH1|1-02/D7|7-27|RF1/JH4 | ................ | ................. | ................. | .......K.K....... | .................. | AP.IAAAG..... .....TWGY..... | ............. |
| iPS:43 4347 | 21-225_64H10 | VH1|1-02/D7|7-27|RF1/JH4 | ................ | ................. | ................. | .......K......Q.. | ..............S... | AP.TAATG..... .....TWGY..... | ............. |
| iPS:43 4359 | 21-225_65G3 | VH1|1-02/D7|7-27|RF1/JH4 | ................ | .........I....... | ................. | ...............S. | ..............G... | AP.KAAAG..... .....TWGY..... | ............. |

Figure 52 (Continued)

| | Germline | H_FR1 | H_CDR1 | H_FR2 | H_CDR2 | H_FR3 | | H_CDR3 | | H_FR4 |
|---|---|---|---|---|---|---|---|---|---|---|
| iPS:43_4369 | VH1\|1-02\|D7\|7-27\|RF1/JH4 | ................ | ........ | ...... | .N... | ........ | .A.... | AP.TAAAG. .....TWGY... | | ..... |
| iPS:43_4373 | VH1\|1-02\|D7\|7-27\|RF1/JH4 | ................ | ........ | ...... | .K... .Q. | ........ | ...... G. | AP.TVAAG. .....TWGY... | | ..... |
| iPS:43_4397 | VH1\|1-02\|D7\|7-27\|RF1/JH4 | ................ | ........ | ...... | .K... .Q. | ........ G. | ...... | AP.TAATG. .....TWGY... | | ..... |
| iPS:43_4427 | VH1\|1-02\|D7\|7-27\|RF1/JH4 | ......I.. | ........ | ...... | .K... .S. | ...S.... RG. | .....G. ....E. | AP.KAAAG. .....TWGF... | | ..... |
| iPS:43_4435 | VH1\|1-02\|D7\|7-27\|RF1/JH4 | ................ | ........ | ...... | .K... .Q. | ...S.... | ...... | AP.IAAAG. .....TWGY... | | ..... |
| iPS:43_4437 | VH1\|1-02\|D7\|7-27\|RF1/JH4 | ................ | ........ | ...... | .K... | ........ G. | .....G. | AP.TAATG. .....TWGY... | | ..... |
| iPS:43_4451 | VH1\|1-02\|D7\|7-27\|RF1/JH4 | ......I.. | ........ | ...... | .S... | ........ G. | ...... | AP.KAAAG. .....TWGF... | | ..... |
| iPS:43_4459 | VH1\|1-02\|D7\|7-27\|RF1/JH4 | ................ | ........ | ...... | .K... .V. | ........ .S. | ...... | AP.TAPAG. .....SWGY... | | ..... |
| iPS:43_4461 | VH1\|1-02\|D7\|7-27\|RF1/JH4 | ................ | ........ | ..D... | .HV. | ..A..... .S. | ...... | AP.TAAAG. .....SWGC... | | ..... |
| | | H_FR1 EVQLLES GGGLVQPGGSLR LSCAASG-FTFS | H_CDR1 YAMS ........VLN | H_FR2 WVRQAPGK GLEWVS | H_CDR2 AISGS GGSTYYAD SVKG ..M.. ..R.. | H_FR3 RFTISRDNSKNTLYLQM NSLRAEDTAVYYCAK | | H_CDR3 TYYY———————YFDY ..H— | | H_FR4 WGQGTL VTVSS ..... |
| iPS:43_4261 | VH3\|3-23\|D4\|4-11\|RF3/JH4 | ................ | ........ | ...... | ...... | ........ | F..M | ...... | | ..... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5461 | VH3\|3-23\|D4\|4-11\|RF3\|JH4 | ........ | .V... | .....G. | ....DR.... | ............. | .AT- ....-K... | ........ |
| iPS:43 5509 | VH3\|3-23\|D4\|4-11\|RF3\|JH4 | ....S... | ....R | .H..... .Q.... | ....D.. ...T. | ...........R. | ....Y--- ....--L | ........ |
| iPS:43 5747 | VH3\|3-23\|D4\|4-11\|RF3\|JH4 | .....A... | .V... | ........ | ....DR.... | ....D.NT....R. | .AG- ....-- | ........ |
| iPS:39 2784 | VH3\|3-23\|D4\|4-11\|RF3\|JH4 | ........ | .V... | ........ | ....M..... ......V | ..........R. | .G.- ....-- | .....T.. |
| iPS:39 2802 | VH3\|3-23\|D4\|4-11\|RF3\|JH4 | ......T. | ........ | ........ | ....F..... | .R.........R. | ........ | ........ |
| iPS:39 2962 | VH3\|3-23\|D4\|4-11\|RF3\|JH4 | ........ | .V.N | ........ | ........ | ....N......R. | .G.- ........ | ........ |
| iPS:39 3090 | VH3\|3-23\|D4\|4-11\|RF3\|JH4 | ........ | .VIN | ........ | ....V..... | ...........R. | .SL- ........ | ........ |
| VH3\|3-23\|D1\|1-11\|RF3\|JH4 | Germline | EVQLLES GGGLVQPGGSLR LSCAASG FTFS | YAMS | WVRQAPG KGLEWVS | AISGS GGSTYYAD SVKG | RFTISRDNSKNTLYLQM NSLRAEDTAVYYCAK | VSHD ---------YFDY | WGQGTL VTVSS |
| iPS:43 4273 | VH3\|3-23\|D1\|1-11\|RF3\|JH4 | ........ | ........ | ........ | ......V.. ......F | ........T.... | RD.. ......V. | ........ |
| VH3\|3-23\|D3\|3-3\|RF3\|JH4 | Germline | EVQLLES GGGLVQPGGSLR LSCAASG FTFS | S | WVRQAPG KGLEWVS | AISGS GGSTYYAD SVKG | RFTISRDNSKNTLYLQM NSLRAEDTAVYYCAK | LLFGVV ---------YFDY | WGQGTL VTVSS |
| iPS:43 4279 | VH3\|3-23\|D3\|3-3\|RF3\|JH4 | ........ | ........ | ........ | ...N.F.... | ........ | FFGVVG- GC...... | .....V.. |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 7228 | 21-225_60C11 | VH3｜3-23｜D3｜3-22｜RF3｜JH4 | | | | | FFGVVG----------V | |
| | | | | | ..N.F. | | .........GC... | |
| Germline | | H_FR1 EVQLLES CGGGVVQPGGSLR LSCAASG-FTFS | H_CDR1 ....YAMS | H_FR2 WVRQAPGK GLEWVS | H_CDR2 AISGS GGSTYYAD SVKG | H_FR3 RFTISRDNSKNTLYLQM NSLRAEDTAVYYCAR | H_CDR3 ITMIVYT--------TAEHGH | H_FR4 WGQGT VTVSS |
| iPS:43 4291 | 21-225_58A44 | VH3｜3-23｜D3｜3-22｜RF3｜JH1 | | ....D... | ..N.F.G. | ........K........ | FFG...G---................ .GF.DS | |
| Germline | | H_FR1 QVQLVES CGGGVVQPGRSLR LSCAASG-FTFS | H_CDR1 S......YSMH | H_FR2 WVRQAPGK GLEWVA | H_CDR2 VIWYD GSNKYYAD SVKG | H_FR3 RFTISRDNSKNTLYLQM NSLRAEDTAVYYCAR | H_CDR3 DYYYA---------ATEDY | H_FR4 WGQGT VTVSS |
| iPS:43 4299 | 21-225_58D11 | VH3｜3-33｜D2｜2-15｜RF3｜JH4 | D.....DI. | ....S... | ..K. | ............L.... | .R.T----.......... | |
| iPS:43 4871 | 21-225_85H1 | VH3｜3-33｜D2｜2-15｜RF3｜JH4 | ......I. | | | | --.-............ | |
| iPS:43 5109 | 21-225_92H5 | VH3｜3-33｜D2｜2-15｜RF3｜JH4 | | | | | .PFI.G-..................... | |
| iPS:43 6434 | 21-225_216B10 | VH3｜3-33｜D2｜2-15｜RF3｜JH4 | | | ....A... | ........R........ | .PFI.G-..................... | |
| | | | | | | | .PNI.G-..................... .W.... | |
| Germline | | H_FR1 QVQLVQS GAEVKKPGASVK VSCKASG-YTFT | H_CDR1 S.......YGMH | H_FR2 WVRQAPGQ GLEWMG | H_CDR2 WINPN-- SGNTNYAQ KFQG | H_FR3 RVTMTRDTSISTAYMEL SRLRSDDTAVYYCAR | H_CDR3 DWGIY---------YFDY | H_FR4 WGQGT VTVSS |
| iPS:43 4307 | 21-225_59B2 | VH1｜1-02｜D4｜4-17｜RF2｜JH4 | ........A | ......I. | ....L... | | | .P.P-........... |
| Germline | | H_FR1 QVQLVES GGGVVQPGRSLR LSCAASG-FTFS | H_CDR1 S......YGMH | H_FR2 WVRQAPGK GLEWVA | H_CDR2 VIWYD GSNKYYAD SVKG | H_FR3 RFTISRDNSKNTLYLQM NSLRAEDTAVYYCAR | H_CDR3 ITMIVYT--------YYYYGMTV | H_FR4 WGQGT VTVSS |
| | | VH3｜3-33｜D3｜3-22｜RF3｜JH6 | | | | | | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 4311 | VH3|3-33/D3|3-22|RF3/J H6 Germline | QVQLQES GPGLVKPSETLS LTCTVSG GSIS | SSS SYYWG | WIRQPPG KGLEWIG | SIYY SGSTYYNP SLKS | RVTISVDTSKNQFSLKL SSVTAADTAVYYCAR | ERG.A.G------VSGSY YYFDY | WGQGTL VTVSS H_FR4 |
| | VH4|4-39/D1|1-26|RF3/JH4 | | | | | | | |
| iPS:43 4313 | VH4|4-39/D1|1-26|RF3/J H4 | . . . . . . . . . . . . . . . . . . . . . . . . . . . . . . . . . . . | R . . . . . | . . . . . . . . . . . . . . . | N . . . . . . . . . . . . . . . . . | . . . . . . . . . . . . . . . . . . . . . . . . . . . . . L . . . . . . . . . . . . . . . . | H.S.W. . . . . . . . . . -SL. . . | . . . . . . |
| iPS:43 4413 | VH4|4-39/D1|1-26|RF3/J H4 | . . . . . . . . . . . . . . . . . . . . . . . . . . . . . . . . . . . | R . . . . . | . . . . . . . . . . . . . . . | N . . . . . I . . . . . . . . . . | . . . . . . . . . . . T . . . . . . . . . . . . . . . . . . . . . . . . . . . . . . . . | H.T.W. . . . . . . . . . -SI. . . | . . . . . . |
| iPS:39 2628 | VH4|4-39/D1|1-26|RF3/J H4 | . . . . . . . . . . . . . . . . . . . . . . . . . . . . . . . . . . . | R . . . . . | . . . . . . . . . . . . . . . | N . . . . TA.C.S . . . | . . . I . . . . . . . . . . . . . . . . . . . . . . . . . . . . . . . . . . . . . . . | H.S.W. . . . . . . . . -SI.N | . . . . . . |
| iPS:39 2642 | VH4|4-39/D1|1-26|RF3/J H4 | . . . . . . . . . . . . . . . . . . . . . . . . . . . . . . . . . . . | R . . . . . | . . . . . . . . . . . . . . . | N . . . . . . . . . . . . . . . . . | . . . I . . . . . T . . . . . . . . . . . . . . . . . . . . . . . . . . . . . . . . | H.S.W. . . . . . . . . -SL.D | . . . . . . |
| iPS:39 2706 | VH4|4-39/D1|1-26|RF3/J H4 | . . . . . F . . . . . . . . . . . . . . . . . . . . . . . . . . . . . | R . . . . . | . . . . . . . . . . . . . . . | N . . Y . . . T . . . . . . . . | . . . . . . . . . . . . . . . . . . . . . . . . . . . . . L . . . . . . . . . . . . . | H.T.W. . . . . . . . . . -SL. . . | . . . . . . |
| iPS:39 2800 | VH4|4-39/D1|1-26|RF3/J H4 | . . . . . . . . . . . . . . . . . . . . . . . . . . . . . . . . . . . | R . . . . . | . . . . . . . . . . . . . . . | N . . . T.S . . . . . . . . . | . . . . . . . . . . . . . . . . . . . . . . . . . . . . . R . . . . . . . . . . F . . . | L.S.W. . . . . . . . . . -SV. . . | . . . . . . |
| iPS:39 2820 | VH4|4-39/D1|1-26|RF3/J H4 | . . . . . . . . . . . . . . . . . . . . . . . . . . . . . A . . . . . | R . . . . . | . . . . . . . . . . . . . . . | . . . AQ . . . . . . . . . . | . . . . . . . . . . . . . . . . . . . . . . . . . . . . . . . . . . . . L . . . . . . . | L.S.W. . . . . . . . . -S. . . | . . . . . . |
| iPS:39 2824 | VH4|4-39/D1|1-26|RF3/J H4 | . . . . . . . . . . . . . . . . . . . . . . . . . . . . . . . . . . . | R . . . . . | . . . . . . . . . . . . . . . | . . . AN . . . . . . . . . . | . . . . . . . . . . . . . . . . . . . . . . . . . . . . . T . . . . . . . . . . . . . | L.S.W. . . . . . . . . . -S. . . | . . . . . . |
| iPS:39 2834 | VH4|4-39/D1|1-26|RF3/J H4 | . . . . . . . . . . . . . . . . . . . . . . . . . . . . . . . N . . . | R . . . . . | . . . . . . . . . . . . . . . | M . . . . . . . A . . . . S | . . . . . . . . . . . . . . . . . . . . . . . . . . . . . T . . . . . . . . . . . . . | H. . .W. . . . . . . . . -SL. . . | . . . . . . |

Figure 52 (Continued)

| | | | | | | | | |
|---|---|---|---|---|---|---|---|---|
| iPS:39 2870 | 21-225_20G9 | VH4|4-39/D1|1-26|RF3/J H4 | . . . . . . . . . . | . . . . . . . . . . | . . . . . . . . . . | . . . . . . . . . . | . . . R . . . . . . | L.S.W . . . . . . . -S . . . |
| iPS:39 2896 | 21-225_21G7 | VH4|4-39/D1|1-26|RF3/J H4 | . . . . F . . . . . | R . . . . . . . . . | . . . . . . . . . . | . Q . . . . . . . . | . . . A . . . . . . | H.T.W . . . . . . . -SL . . |
| iPS:39 2904 | 21-225_22G9 | VH4|4-39/D1|1-26|RF3/J H4 | . . . . A . . . . . | G . . . . N . . . . | . . . . . . . . . . | E . . . . . . . . . | R . . . E . . . . . | H.S.W . . . . . . . -SL . . |
| iPS:39 3094 | 21-225_34C4 | VH4|4-39/D1|1-26|RF3/J H4 | . . . . . . . . . . | R . . . . . . . . . | . . . . A . . . . . | . . . S . . . . . . | . . . . V . . . . . | L.S.W . . . . . . . -S . . . |
| iPS:39 3806 | 21-225_6A6 | VH4|4-39/D1|1-26|RF3/J H4 | . . . . . . . . . . | R . . . . . . . . . | N . . . IP . . . . | . . . . . . . . . . | . N . . . . . . . . | H.S.W . . . . . . . -SL . . |
| iPS:39 3814 | 21-225_7F4 | VH4|4-39/D1|1-26|RF3/J H4 | . . . . . . . . . . | R . . . . . . . . . | N . . . A . . . . . | . . . . . . . . . . | . T . . . . . . . . | H . W . . . . . . . -SL . . |
| iPS:39 3816 | 21-225_6D4 | VH4|4-39/D1|1-26|RF3/J H4 | . . . . . . . . . . | R . . . . S . . . . | . . . . . . . . . . | . . . . . . . . . . | . . . . A . . . . N | H.S.W . . . . . . . -SL.C |
| iPS:39 3880 | 21-225_15A1 | VH4|4-39/D1|1-26|RF3/J H4 | . . . . H . . . . . | R . . . . S . . . . | . . . . AQ . . . . | . . . . . . . . . . | . T . . . T . . . . T | L.S.W . . . . . . . -S . . . |
| iPS:39 4002 | 21-225_15G7 | VH4|4-39/D1|1-26|RF3/J H4 | . . . . . . . . . . | R . . . . . . . . . | . . . . Y . . . T . | . . . . . . . . . . | . . . . S . . . . R | L.S.W . . . . . . . -S . . . |
| iPS:39 4053 | 21-225_11F10 | VH4|4-39/D1|1-26|RF3/J H4 | . . . . H . . . . . | R . . . . . . . . . | . . . . AQ . . . . | . . . . . . . . . . | . . . . . . . . . T | L.S.W . . . . . . . -S . F . |
| iPS:39 4057 | 21-225_15H1 | VH4|4-39/D1|1-26|RF3/J H4 | . . . . F . . . . . | R . . . . . . . . . | N . . . YP . . . . | . . . . . . . . . . | . . . . . . . . . . | H.T.W . . . . . . . -SL . . |
| iPS:39 4063 | 21-225_16A1 | VH4|4-39/D1|1-26|RF3/J H4 | . . . . I . . . . D | R . . . . . . . . . | . . . . A.H . . . | . . . . . . . . . . | . G . . . A . . . . | L.S.W . . . . . . . -S . . . |

| | | H_FR1 | H_CDR1 | H_FR2 | H_CDR2 | H_FR3 | H_CDR3 | H_FR4 |
|---|---|---|---|---|---|---|---|---|
| iPS:43 4335 | 21-225_63C10 | VH3\|3-33/D4\|4-11\|RF2\|JH4 | ................ | ........ | ....D... | ........ | ........ | DPRS....SAG... | ........ |
| iPS:43 4429 | 21-225_70H6 | VH3\|3-33/D4\|4-11\|RF2\|JH4 | ................ | ........ | ...T....D... | ....H... | ........ | DPRS....SAG... | ........ |
| iPS:43 4569 | 21-225_77H5 | VH3\|3-33/D4\|4-11\|RF2\|JH4 | ................ | ...N.... | ........ | ...R.... | ........L....... | R.ILG....ATF... | ........ |
| iPS:43 4629 | 21-225_74C3 | VH3\|3-33/D4\|4-11\|RF2\|JH4 | ................ | ....F... | ....A... | ....A...C... | ........ | R.ILG....AAF... | ........ |
| iPS:43 5793 | 21-225_180F8 | VH3\|3-33/D4\|4-11\|RF2\|JH4 | ................ | ........ | ........ | ....D.E. | ....S... | HPRW....S.G... | ........ |
| iPS:43 6382 | 21-225_212C10 | VH3\|3-33/D4\|4-11\|RF2\|JH4 | ................ | ........ | ....T... | ..H..T. | ........ | R.IVG....AT... | ........ |
| iPS:39 2660 | 21-225_19B3 | VH3\|3-33/D4\|4-11\|RF2\|JH4 | ................ | ....D... | ........ | ...D.... | ........F....... | RAYS....SSS... | ........ |
| iPS:39 3904 | 21-225_8H11 | VH3\|3-33/D4\|4-11\|RF2\|JH4 | ....T.....N.. | ........ | ........ | .DR.S... | ........ | RAYS....SSS.F | ........ |
| Germline | VH4\|4-59\|D4\|4-11\|RF2\|JH4 | CVQLQES GPGLVKPSETLS LTCTVSG-GSIS | S....YWS | WIRQPPG KGLEWIG | YIYY SGSTNYNP SLKS | RVTISVDTSKNQFSLKL SSVTAADTAVYYCAR | DPSNY YFDY | WGQGTL VTVSS |
| iPS:43 4341 | 21-225_64F7 | VH4\|4-59/D4\|4-11\|RF2\|JH4 | ........F... | ........ | ........ | ..R..T. ..IS... | ........M... | FS.G-..F... | ........ |
| Germline | VH3\|3-33/D7\|7-27\|RF2\|JH1 | CVQLVES GGGVVQPGRSLR LSCAASG-FTFS | S.....YGMH | WVRQAPG KGLEWVA | VIWYD GSNKYYAD SVKG | RFTISRDNSKNTLYLQM NSLRAEDTAVYYCAR | VLGAE VFDH | WGQG VTVSS |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:43 4351 | VH3\|3-33\|D7\|7-27\|RF2\|JH1 | .................... | .................... | .................... | E....V. | .................... | E..F- | .................... |
| iPS:39 2700 | VH3\|3-33\|D7\|7-27\|RF2\|JH1 | ............L....... | ..N................. | .................... | E....V. ..R. | ........S........... | E..F- ...QSD. | .................P. ...LSD. |
| iPS:39 2710 | VH3\|3-33\|D7\|7-27\|RF2\|JH1 | .................... | .................... | .................... | E...... | .................... | E.AW- ....EDS | .................... |
| iPS:39 4093 | VH3\|3-33\|D7\|7-27\|RF2\|JH1 | .................... | D................... | .................... | .N.N... | .................... | E.AW- ....EDZ | .................... |
| | Germline | H_FR1 EVQLLES GGGLVQPGGSLR LSCAASG-FTFS | H_CDR1 SYAMS | H_FR2 WVRQAPGK GLEWVS | H_CDR2 AISGS GGSTYYAD SVKG | H_FR3 RFTISRDNSKNTLY LQM NSLRAEDTAVYYCAR | H_CDR3 VYYESSGY ---YYDARDI | H_FR4 WGQGTL VTVSS |
| VH3\|3-23\|D3\|3-22\|RF2\|JH3 | | | | | | | | |
| iPS:43 4355 | VH3\|3-23\|D3\|3-22\|RF2\|JH3 | .................... | .................... | .................... | .V..... | ...........L........ | RN..D---- | .................... |
| | Germline | H_FR1 EVQLVES GGGLVKPGGSLR LSCAASG-FTFS | H_CDR1 -SMN | H_FR2 WVRQAPGK GLEWVS | H_CDR2 SISSS SSIYYAD SVKG | H_FR3 RFTISRDNAKNSLY LQM NSLRAEDTAVYYCAR | H_CDR3 TYVT | H_FR4 WGQGTL VTVSS |
| VH3\|3-21\|D4\|4-11\|RF3\|JH4 | | | | | | | | |
| iPS:43 4367 | VH3\|3-21\|D4\|4-11\|RF3\|JH4 | .................... | ..R................. | .................... | N.S.... | ...........T........ | S-- | .................... |
| iPS:43 7220 | VH3\|3-21\|D4\|4-11\|RF3\|JH4 | .................... | .................... | .................... | ..G.... | ..................TS | ....-GS | .................... |
| iPS:40 2237 | VH3\|3-21\|D4\|4-11\|RF3\|JH4 | ..H................. | .................... | .................... | ...GN.. ...G... | .................... | G.- | .................... |
| iPS:43 7225 23D11 | VH3\|3-21\|D4\|4-11\|RF3\|JH4 | .................... | ..NI................ | .................... | | .................... | .NL- | .................... |
| | Germline | H_FR1 EVQLVES GGGLVKPGGSLR LSCAASG-FTFS | H_CDR1 -SMN | H_FR2 WVRQAPGK GLEWVS | H_CDR2 SISSS SSIYYAD SVKG | H_FR3 RFTISRDNAKNSLY LQM NSLRAEDTAVYYCAR | H_CDR3 TYVTD ------ARDI | H_FR4 WGQGTL VTVSS |
| VH3\|3-21\|D4\|4-11\|RF3\|JH3 | | | | | | | | |

| | | | | | | | | | |
|---|---|---|---|---|---|---|---|---|---|
| | | QVQLVES GGGVVQPGRSLR LSCAASG-FTFS | ----YGMH | WVRQAPGK GLEWVA | VIWYDGSN KYYAD SVKG | RFTISRDNSKNTLYLQM NSLRAEDTAVYYCAR | VLWFGE LL*YFIIV | WGQGTL VTVSS |
| VH3\|3-33\|D3\|3-10\|RF1\|JH4 | | | | | | | | | |
| iPS:43 4433 | 21-225_70E8 | ................. | ........L | ........ | .....I... E..... | ................. | D...D--- -PR.. | ..... |
| | Germline | H_FR1 | H_CDR1 | H_FR2 | H_CDR2 | H_FR3 | H_CDR3 | H_FR4 |
| VH3\|3-23\|D6\|6-13\|RF1\|JH4 | | EVQLLES GGGLVQPGGSLR LSCAASG-FTFS | ----YAMS | WVRQAPGK GLEWVS | AISGS GGSTYYAD SVRG | RFTISRDNSKNTLYLQM NSLRAEDTAVYYCAK | GYSSSW ----YFDY | WGQGTL VTVSS |
| iPS:43 4467 | 21-225_73H8 | ...S........... | .......N... | ........ | ..D..R.... ..T.F..... | ................. | WD......Y. .....DVTP.... | ..... |
| | Germline | H_FR1 | H_CDR1 | H_FR2 | H_CDR2 | H_FR3 | H_CDR3 | H_FR4 |
| VH4\|4-34\|D4\|4-17\|RF2\|JH4 | | QVQLQES GAGLLKPSETLS LTCTVSG GSFS | G----YYWS | WIRQPPG KGLEWIG | EINH SGSTNYNP SLKS | RVTISVDTSKNQFSLKL SSVTAADTAVYYCAR | DYGDY ----YFDY | WGQGTL VTVSS |
| iPS:43 4471 | 21-225_75G3 | ................. | .....S..... | ........ | .....L........ | .................S...T... | ...G-- --L.. | ..... |
| iPS:43 4517 | 21-225_76A7 | .......L........ | .....C..... | ........ | .....R........ | ..R................... | ...G-- --L.. | ..A.. |
| iPS:43 4519 | 21-225_74C7 | ................. | .....S..... | ........ | .....L........ | .................S...T... | ...G-- --L.. | ..... |
| iPS:43 4571 | 21-225_74D2 | .......L........ | .....C..... | ........ | .....R........ | ..R..........E........ | ...G-- --L.. | ..... |
| iPS:43 4637 | 21-225_78E7 | ................. | .....S..... | ........ | .....L........ | .................S...T... | ...G-- --L.. | ..... |
| iPS:43 4717 | 21-225_80A6 | ................. | .....C..... | ........ | .....R........ | ..R............EK..... | ...G-- --L.. | ..... |
| iPS:43 4735 | 21-225_80B10 | ................. | .....C..... | ........ | ............. | ..................... | ...G-- --L.. | ..... |

| | Germline | H_FR1 | H_CDR1 | H_FR2 | H_CDR2 | H_FR3 | H_CDR3 | H_FR4 |
|---|---|---|---|---|---|---|---|---|
| iPS:43 4503 | VH4/4-39/D7/7-27/RF1/JH5 | ..........S | R...... | | G...... | ..........E | RP.W......D.Y | ..... |
| VH3/3-15/D1/1-1/RF2/JH4 | Germline | EVOLVES GGGLVQPGGSLR LSCAASG-FTFS | ----AWMS | WVRQAPGK GLEWVG | RIKSKT DGGTTYA AZVKG | RFTISRDDSKNTLYLQM NSLKTEDTAVYYCTT | VGLER-------YFDX | WGQGTL VTVSS |
| iPS:43 4531 | VH3/3-15/D1/1-1/RF2/JH4 | .......S.. | ......N | | ...N.A... | | .GPT------T... | |
| iPS:43 4633 | VH3/3-15/D1/1-1/RF2/JH4 | | ......N | | .....F... | | .GAT------T... | |
| iPS:43 4671 | VH3/3-15/D1/1-1/RF2/JH4 | | ......N | | ...N.I... | | .GAT------T... | |
| iPS:43 7383 | VH3/3-15/D1/1-1/RF2/JH4 | ...H...... | | | | | .GAT------T... | |
| VH3/3-33/D5/5-18/RF3/JH4 | Germline | EVOLVES GGGVVQPGRSLR LSCAASG-FTFS | ----YGMH | WVRQAPGK GLEWVA | VIWYD- GSNKYYAD SVKG | RFTISRDNSKNTLYLQM NSLRAEDTAVYYCAR | GXYVG------YFDX | WGQGTL VTVSS |
| iPS:43 4535 | VH3/3-33/D5/5-18/RF3/JH4 | | | | .....N... | | DG...Y.....DGL... | |
| iPS:43 4573 | VH3/3-33/D5/5-18/RF3/JH4 | .......S.. | | | ....QN... | | DG...Y.....DGL... | |
| iPS:43 4615 | VH3/3-33/D5/5-18/RF3/JH4 | | | | .....N... | ......F........... | DG...Y.....DGL... | |
| iPS:43 4669 | VH3/3-33/D5/5-18/RF3/JH4 | .......S.. | ......N | | ....QN... | ......F........... | DG...Y.....DGL... | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 4737 | VH3|3-33|D5|5-18|RF3|JH4 | .................... | ........ | ................ | ........... N...... | .................................. | DG...Y......DGL... | .... |
| iPS:43 4741 | VH3|3-33|D5|5-18|RF3|JH4 | .................... | ........ | ................ | ........... N...... | .................................S | DG...Y......DGL... | .... |
| iPS:43 4867 | VH3|3-33|D5|5-18|RF3|JH4 | .................... | ........ | ................ | ........... N...... | .................................. | DG...Y......DGL...A | .... |
| Germline | | H_FR1 EVQLQQSG GGLVQPGGSLR LSCAASG_FTFS | H_CDR1 G YMS | H_FR2 WVRQAPGK GLEWVS | H_CDR2 RINH SGSTNYNP SLKS | H_FR3 RVTISVDTSKNQFSLKL SSVTAADTAVYYCAR | H_CDR3 VYYGSGSYYN ---YYYGMDV | H_FR4 WGQGTT VTVSS |
| VH4|4-34|D3|3-10|RF2|JH6 | | | | | | | | |
| iPS:43 4539 | VH4|4-34|D3|3-10|RF2|JH6 | .........V......... | D....... | ................ | ......D............ | .................................. | EFPY....--------- | .... |
| iPS:43 7248 | VH4|4-34|D3|3-10|RF2|JH6 | .........V...F..... | D....... | ................ | ......D............ | .................................. | EFPY....L--------- | .... |
| iPS:43 7320 | VH4|4-34|D3|3-10|RF2|JH6 | .....H...V...F..... | D....... | ................ | ......D............ | .................................. | EFPY....L--------- | .... |
| Germline | | H_FR1 EVQLVES GGGLVQPGGSLR LSCAASG_FTFS | H_CDR1 S YDMH | H_FR2 WVRQATGK GLEWVS | H_CDR2 AIGT AGDTYYPG SVKG | H_FR3 RFTISRENAKNSLYLQM NSLRAGDTAVYYCAR | H_CDR3 VLRYFDLL*--VLYYGMDV | H_FR4 WGQGTT VTVSS |
| VH3|3-13|D3|3-9|RF1|JH6 | | | | | | | | |
| iPS:43 4563 | VH3|3-13|D3|3-9|RF1|JH6 | .................... | N....... | ................ | ................... | .................................. | ..D.G.S.G-........ | .... |
| iPS:43 5009 | VH3|3-13|D3|3-9|RF1|JH6 | .................... | ........ | ................ | ................F.. | .................................. | A.D.G.S.G-........ | .... |
| iPS:43 5059 | VH3|3-13|D3|3-9|RF1|JH6 | .................... | N....... | ................ | ................... | .................................. | ..D.G.S.G-........ | .... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:43 5103 | 21-225_92B2 | VH3/3-13/D3/3-9/RF1/JH6 | | N........ | | | A.D.G.S.G- ........ -.... | ... ... ... |
| iPS:43 7371 | 21-225_74D8 | VH3/3-13/D3/3-9/RF1/JH6 | | N........ | | ........F | ..D.G.S.G- ........ -.... | ... ... ... |
| | Germline | H_FR1 | H_CDR1 | H_FR2 | H_CDR2 | H_FR3 | H_CDR3 | H_FR4 |
| VH1/1-08/D1/1-26/RF3/JH4 | | QVQLVQS.. GAEVKKPGASVK VSCKASG.YTFT | S.... YDIN | WVRQATGQ GLEWMG | WMNPN SGNTGYAQ KFQG | RVTMTRDTSISTAYMEL SSLRSEDTAVYYCAR | IGSSY...... -YFDY | WGQGTL VTVSS |
| iPS:43 4711 | 21-225_80H3 | VH1/1-08/D1/1-26/RF3/JH4 | .......... ........L. | N........ | | ........GS | T.WN..... ........-F.... | ... ... ... |
| iPS:43 4901 | 21-225_85H9 | VH1/1-08/D1/1-26/RF3/JH4 | .......... ........L. | N........ | | ........RGS | T.WN..... ........-F.... | ... ... ... |
| iPS:43 5167 | 21-225_92F12 | VH1/1-08/D1/1-26/RF3/JH4 | .......... ........L. | N........ | | ........RGS | T.GK..... ........-F.... | ... ... ... |
| iPS:43 5215 | 21-225_94E12 | VH1/1-08/D1/1-26/RF3/JH4 | .......... ........L. | N........ | | ........RGS | T.WK..... ........-F.... | ... ... ... |
| iPS:43 7356 | 21-225_74B1 | VH1/1-08/D1/1-26/RF3/JH4 | .......... ........L. | N........ | | ........GS | T.WN..... ........-F.... | ... ... ... |
| | Germline | H_FR1 | H_CDR1 | H_FR2 | H_CDR2 | H_FR3 | H_CDR3 | H_FR4 |
| VH1/1-08/D1/1-1/RF1/JH6 | | QVQLVQS.. GAEVKKPGASVK VSCKASG.YTFI | .......... | WVRQATGQ GLEWMG | WMNN SGNTGYAQ KFQG | RVTMTRNTSISTAYMEL SSLRSEDTAVYYCAR | FYD.LIGS ........ -YYYGMDV | WGQGT LVTVSS |
| iPS:43 4815 | 21-225_74A11 | VH1/1-08/D1/1-1/RF1/JH6 | .......... | .......... | | ........W..K | .FYD.LIGS ....G...V.... | ... ... ... |
| iPS:43 5253 | 21-225_96A4 | VH1/1-08/D1/1-1/RF1/JH6 | .......... | ........H | | ........W..K | .FYD.LIGS ....G...V.... | ... ... ... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| | VH1|1-08/D3|3-22|RF2/JH6 | QVQLVQSG AEVKKPGASVK VSCKASG-YTFT | ...KDSY | WVRQATGQ GLEWMG | ...KDSN...MNPN SGNTGYAQ NFQG | RVTMTRNTSISTAYME LSSLRSEDTAVYYCAR | MVYDSSGYYY YYYYYGMDV | WGQGTT VTVSS |
| iPS:43 4977 | 21-225_88A5 VH1|1-08/D3|3-22|RF2/JH6 | ........ ........ ........ | ...... | ...... | ...... | ...W....R...... ........ | GF..FLTG.S..... .PT....D... | ...... |
| iPS:43 5259 | 21-225_96C6 VH1|1-08/D3|3-22|RF2/JH6 | ........ ........ ........ | ...... | ...... | ..R......... ...... | ...W........... ........ | GG..VLPGN- .......-- N...D..... | ...... |
| | Germline | H_FR1 | H_CDR1 | H_FR2 | H_CDR2 | H_FR3 | H_CDR3 | H_FR4 |
| | VH3|3-33/D2|2-15|RF3/JH3 | QVQLEES GGGVVQPGRSLR LSCAASG-FTFS | VGMH | WVRQAPGKG LEWVA | ..LID GSNKYYAD NSLPAEDTAVYYCAR SVKG | RFTISRDNSKNTLLLQM NSLPAEDTAVYYCAR | DTVWVA ..A.DAFDI | WGQGTM VTVSS |
| iPS:43 5291 | 21-225_146E1 VH3|3-33/D2|2-15|RF3/JH3 | ........E. ........ ........ | ...... | ...... | ...I......... ...... | ........F....... ........ | .RL.GAT........ ......-A-..... | ...... |
| iPS:43 6360 | 21-225_210H11 VH3|3-33/D2|2-15|RF3/JH3 | ........ ........ ........ | H..... | ...... | ...T......... ...D......... | ............... ........ | .RL.GAT........ ......-....... | ...... |
| iPS:43 6370 | 21-225_211A6 VH3|3-33/D2|2-15|RF3/JH3 | ........ ........ ........ | ...... | ...... | ...N......... ...... | ............F... ........ | .RT.GY-........ ......G....... | ...... |
| iPS:43 6392 | 21-225_213B3 VH3|3-33/D2|2-15|RF3/JH3 | ........ ........ ........ | ...... | ...... | ...N......... ...... | ............... ........ | .RT.GY-........ ......G....... | ...... |
| iPS:43 6406 | 21-225_214E4 VH3|3-33/D2|2-15|RF3/JH3 | ........ ........ ........ | ...... | ...... | ...EN........ ...... | ..T............ ........ | .RT.GY-........ ......GC...... | ..A... |
| iPS:43 7326 | 21-225_75C10 VH3|3-33/D2|2-15|RF3/JH3 | ........ ........ ........ | ...... | ...... | ...D......... ...... | ............... ........ | .RL.GAT........ ......-V...... | ...... |
| | Germline | H_FR1 | H_CDR1 | H_FR2 | H_CDR2 | H_FR3 | H_CDR3 | H_FR4 |
| | VH4|4-39/D7|7-27|RF1/JH4 | QVQLQES GPGLVKPSETLS LTCTVSG GSIS | SS..SYYWG | WIRQPPG KGLEWIG | ..SIY YSGSTYYNP SLKS | RVTISVDTSKNQFSLKL SSVTAADTAVYYCAR | ITGY ......FDI | WGQGTL VTVSS |
| iPS:43 5293 | 21-225_146F1 VH4|4-39/D7|7-27|RF1/JH4 | ........ ........ ........ | R..... | ...... | ......S...... ...... | ............... ........ | DLLW......S.... ........ | ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5361 | 21-225_148E11 | VH4|4-39/D7|7-27|RF1/JH4 | ...... | ...... | ...... | ......R........ | ...... | .DPQW...... | ....I. |
| iPS:43 5449 | 21-225_152H9 | VH4|4-39/D7|7-27|RF1/JH4 | ..........V.. | ...... | ...... | ......R......S... | .........F.. | .DLQW......S..F | ...... |
| iPS:43 5499 | 21-225_156G1 | VH4|4-39/D7|7-27|RF1/JH4 | ...... | ...... | ...... | ......R.....AS... | .........F.. | .DLQW......S..F | ...... |
| iPS:43 5587 | 21-225_160H3 | VH4|4-39/D7|7-27|RF1/JH4 | ...... | ...... | ...... | ......R.....AS...E.. | .........F.. | .SQRW......D... | ...... |
| iPS:40 3868 | 21-225_19D11 | VH4|4-39/D7|7-27|RF1/JH4 | ...... | ...... | ....D... | ......R.....AN... | .........A.. | .DRGW......S... | ...... |
| Germline | VH3|3-23|D4|4-17|RF2/JH5 | EVQLLES GGGLVQPGGSLR LSCAASG_FTFS | YAMS | WVRQAPGK GLEWVS | AISGS GGSTYYAD SVKG | RFTISRDNSKNTLYLQM NSLRAEDTAVYYCAR | DYDY_____NWFDP | WGQGTL VTVSS |
| iPS:43 5295 | 21-225_146H1 | VH3|3-23|D4|4-17|RF2/JH5 | ...... | ...... | ...... | ....R. ..N.F. | ...... | RVT..GG......ND... | ...... |
| iPS:43 5307 | 21-225_146E9 | VH3|3-23|D4|4-17|RF2/JH5 | ...... | ...... | ...... | ....R. ..N.F. | .........K.. | RVT..GG......ND... | ...... |
| iPS:43 5347 | 21-225_148C4 | VH3|3-23|D4|4-17|RF2/JH5 | ...... | ..N... | ...... | ....R. ..N.F. | ...... | RVT..GG......ND... | ...... |
| iPS:43 5355 | 21-225_148H9 | VH3|3-23|D4|4-17|RF2/JH5 | ...... | ...... | ...... | ....R. ..N.F. | ...... | RVT..GG......ND... | ...... |
| iPS:43 5371 | 21-225_149A3 | VH3|3-23|D4|4-17|RF2/JH5 | ...... | ..N....T | ...... | ....R. ..N.F. | ............T. | RVT..GG......ND... | ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5415 | VH3|3-23/D4|4-17|RF2/J H5 | ........ | ........N... | ........ | ....R..N.F.. | ........S........ | RVT..GG.....ND... | ........ |
| iPS:43 5419 | VH3|3-23/D4|4-17|RF2/J H5 | ........ | ........ | ........ | ....R..N.F.. | ................. | RVT..GG.....ND... | ........ |
| iPS:43 5425 | VH3|3-23/D4|4-17|RF2/J H5 | ........ | ........N... | ......H. | .KN.F.. | ................. | RVT..GG.....ND... | ........ |
| iPS:43 5431 | VH3|3-23/D4|4-17|RF2/J H5 | ........ | ........ | ........ | ....R..N.F.. | ................. | RVT..GG.....ND... | ........ |
| iPS:43 5439 | VH3|3-23/D4|4-17|RF2/J H5 | ........ | ........N... | ........ | ....R..N.F.. | .........K....... | RVT..GG.....ND... | ........ |
| iPS:43 5455 | VH3|3-23/D4|4-17|RF2/J H5 | ........ | ........ | ........ | ....R..N.F.. | ................. | RVT..GG.....ND... | ........ |
| iPS:43 5487 | VH3|3-23/D4|4-17|RF2/J H5 | ........ | ........ | ........ | ....R..N.F.. | ................. | RVT..GG.....ND... | ........ |
| iPS:43 5503 | VH3|3-23/D4|4-17|RF2/J H5 | ........ | ........ | ........ | ....R..N.F.. | ................. | RVT..GG.....ND... | ........ |
| Germline VH3|3-30|D3|3-22|RF3|JH6 | | CVQLQES GGGVVQPGRSLR LSCAASG-FTFS | SG- GYYWS | WIRQAPGK GLEWVA | YIYYD GSNKYYAD SVKG | RFTISRDNSKNTLYLQM NSLRAEDTAVYYCAR | TMGYYYIT --YYYYGMDV | WGQGTTV TVSS |
| iPS:43 5297 | VH3|3-30/D3|3-22|RF3/J H6 | ........ | ........ | ........ | .W.. ...Y.. | .......D... ..V.... | MGIE.A.D- ........ | ........ |
| Germline VH4|4-30.1|D1|1-1|RF1|JH3 | | CVQLQES GPGLVKPSQTLS LTC-VSG-GSIS | ........ | WIRQHPGK GLEWIG | YIYY SGSTYYNP SLKS | RVTISVDTSKNQFSLKL SSVTAADTAVYYCAR | ETTGT DAFDI | WGQGTM VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5301 | 21-225_146G4 | VH4J4-30.1/D1[1-1]RF1/JH3 | ........N.... | NS...... | ............ | ........S.... | ........I....N.... | .KYNWN...H........ | ........ |
| | Germline | H_FR1 FVIVES GGGLVKPGGSLR LSCAASG FTFS | H_CDR1 S..... YSTN | H_FR2 WVRQAPGK GLEWVS | H_CDR2 SISSS SSYIYYAD SVKG | H_FR3 RFTISRDNAKNSLYLQM NSLRAEDTAVYYCAR | H_CDR3 GYSSSW........YFDY | H_FR4 WGQGTLVTVSS |
| iPS:43 5313 | 21-225_146G11 | VH3J3-21/D6[6-13]RF1/JH4 | .............. | .............. | .............. | ..G....G.T.... | .............. | S....-....-G.... | ........ |
| iPS:39 3808 | 21-225_1A2 | VH3J3-21/D6[6-13]RF1/JH4 | .............. | .......T...... | .............. | ..G............ | .............. | S....-....-G.... | ........ |
| iPS:39 3958 | 21-225_5H2 | VH3J3-21/D6[6-13]RF1/JH4 | .............. | .......T...... | .............. | ..G............ | ........A.... | S....-....-G.... | ........ |
| | Germline | H_FR1 QVQLQES GPGLVKPSQTLS LTCTVSG-GSIS | H_CDR1 SG-- YYWS | H_FR2 WIRQHPGK GLEWIG | H_CDR2 YIYY SGSIYYNP SLKS | H_FR3 RVTISVDTSKNQFSLKL SSVTAADTAVYYCAR | H_CDR3 GVSYGYYY......YYYGMDV | H_FR4 WGQGTT VTVSS |
| iPS:43 5317 | 21-225_147D2 | VH4J4-30.4/D5[5-18]RF3/JH6 | .....L...... ......P... | .....N.... | .....R...... | .....F........T.... | .....S..E..E.....N.... | .GA.YS---........ | ........ |
| | Germline | H_FR1 QVQLQES GPGLVKPSQTLS LTCTVSG-GSIS | H_CDR1 SG-- GYYWS | H_FR2 WIRQHPGK GLEWIG | H_CDR2 YIYY SGSIYYNP SLKS | H_FR3 RVTISVDTSKNQFSLKL SSVTAADTAVYYCAR | H_CDR3 RDGYYY........DAFDI | H_FR4 WGQGTM VTVSS |
| iPS:43 5319 | 21-225_147E3 | VH4J4-30.1/D5[5-24]RF3/JH3 | .............. | NS......Y.... | .............. | ..G............ | ........I....N.... | GGYNWN...H...F | ........ |
| iPS:43 5383 | 21-225_149D7 | VH4J4-30.1/D5[5-24]RF3/JH3 | ........N.... | NS...... | .............. | ..S............ | ........I....N.... | GGYNWN...H.... | ......I |

Figure 52 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:43 5443 | 21-225_152E7 | VH4|4-30.1/D5|5-24|RF3/JH3 | .........N...... | NS........ | ............ | ........S... | ........I......N.... | GGYNWN........ | |
| iPS:43 5465 | 21-225_153A6 | VH4|4-30.1/D5|5-24|RF3/JH3 | .........N...... | NS........ | ............ | ........S... | ........I......N.... | GGYNWN........H.... | |
| iPS:44 2568 | 21-225_149D8 | VH4|4-30.1/D5|5-24|RF3/JH3 | .........N...... | NS........ | ............ | ........S... | ........I......N.... | GGYNWN........H.... | |
| | | Germline | H_FR1 | H_CDR1 | H_FR2 | H_CDR2 | H_FR3 | H_CDR3 | H_FR4 |
| VH3|3-48|D4|4-11|RF2/JH4 | | | EVQLVES GGGLVQPGGSLR LSCAASG-FTFS | ----YSYN | WVRQAPGK GLEWVS | SSIYYAD SVKG | RFTISRDNSKNTLYLQMN SLRAEDTAVYYCAR | DVSNY----VFDY | WGQGTL VTVSS |
| iPS:43 5333 | 21-225_147E9 | VH3|3-48|D4|4-11|RF2/JH4 | ............ | .......... | ............ | S..GR.... NT.... STSG | ..........S..... | .RG---------SC | |
| iPS:43 5637 | 21-225_163E2 | VH3|3-48|D4|4-11|RF2/JH4 | ............ | .......... | ............ | ST.G.... .TY..... | ..........LV.... .P | .RG---------SL | |
| | | Germline | H_FR1 | H_CDR1 | H_FR2 | H_CDR2 | H_FR3 | H_CDR3 | H_FR4 |
| VH1|1-02/D2|2-15|RF3/JH4 | | | QVQLVQS GAEVKKPGASVK VSCKASG-YTFT | ----SYWMH | WVRQAPGQ GLEWMG | IINPN-SGGTNYAQ KFQG | RVTMTRDTS ISTAYMEL SRLRSDDTAVYYCAR | DIVVVA----ATYFDY | WGQGTL VTVSS |
| iPS:43 5351 | 21-225_148B6 | VH1|1-02/D2|2-15|RF3/JH4 | ............ | ........ | ............ | ..H..... N..... T.... | ...........V.... | .P...P- AP..... | |
| | | Germline | H_FR1 | H_CDR1 | H_FR2 | H_CDR2 | H_FR3 | H_CDR3 | H_FR4 |
| VH4|4-30.1/D5|5-12|RF3/JH6 | | | QVQLQES GPGLVKPSQTLS LTCTVSG-GSIS | SS-GYYWS | WIRQHPGK GLEWIG | YIYY-SGSTYYNP SLKS | RVTISVDTSKNQFSLKL SSVTAADTAVYYCAR | GVSGYDY----YYYYGMDV | WGQGTT VTVSS |
| iPS:43 5363 | 21-225_148F12 | VH4|4-30.1/D5|5-12|RF3/JH6 | ............ | N......... | ............ | ........ | QI.........D....R. | YSTYDY--- | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5377 | 21- 225_149G5 | VH4/4-30.1/D5|5-12|RF3/JH6 | N........ | N......... | | | .....D....R.. | YSTYDY--- | |
| | | Germline | QVQLQ... CCLVKPGGSLR LSCAASG-FTFS | S....VSMN | WVRQAPGK GLEWVS | SSIIYAD SVKG | RFTISRDNAKNTLYLQM NSLRAEDTAVYYCAR | STAAR.........TFDY | WGQGT LVTVSS |
| iPS:43 5409 | 21- 225_150G8 | VH3|3-48/D6|6-6|RF2/JH4 | .......... | T........ | ...D..... | .....R... | ....S...........L | .AFS-............P.. | .... |
| | | Germline | QVQLV... CCSVKPGRSLR LSCAASG-FTFS | S....YAMH | WVRQAPGK GLEWVA | TISY GSNKYYAD SVKG | RTISRDNSKNTLYLQM NSLRAEDTAVYYCAR | VIVNL.........NWDP | WGQGT LVTVSS |
| iPS:43 5427 | 21- 225_151C9 | VH3|3-30.3/D5|5-18|RF2/JH5 | .......... | .....G... | | | | GVL..FGE....LEDD... | .... |
| | | Germline | QVQLV... CCAVKPGGSLR LSCAASG-FTFS | S....YGMH | WVRQAPGK GLEWVA | VIWYD GSNKYYAD SVKG | RTISRDNSKNTLYLQM NSLRAEDTAVYYCAR | YYIDSSG-.......YYYEDI | WGQGT LVTVSS |
| iPS:43 5441 | 21- 225_152F6 | VH3|3-33/D3|3-22|RF2/JH4 | .......... | .......... | | I....Y... | | EG..FW-............ | .... |
| iPS:43 5457 | 21- 225_152C11 | VH3|3-33/D3|3-22|RF2/JH4 | .......R | N......... | | I........ | | SG.LG............. | I... |
| iPS:43 5463 | 21- 225_153D2 | VH3|3-33/D3|3-22|RF2/JH4 | .......... | N......... | | I....Y... | | EA..FW-............SG.... | .... |
| iPS:43 5531 | 21- 225_157G8 | VH3|3-33/D3|3-22|RF2/JH4 | .......... | .......... | | I....Y... | ....V..... | EG..FW-............SG.LG | .... |
| iPS:43 5577 | 21- 225_160B1 | VH3|3-33/D3|3-22|RF2/JH4 | .......... | .......... | | .....Y... | | EA..FW-............SG.Y.. | .... |

| | | H_FR1 | H_CDR1 | H_FR2 | H_CDR2 | H_FR3 | H_CDR3 | H_FR4 |
|---|---|---|---|---|---|---|---|---|
| iPS:43 5513 | 21-225_157F3 | VH3J3-23/D6[6-19]RF1/JH3 | ....E.... | ......F...... | ......V..... | ........... | ........... | RS.GWY......E..L.... | ........... |
| iPS:39 2766 | 21-225_23H4 | VH3J3-23/D6[6-19]RF1/JH3 | ........... | ........N... | ........V... | ......T..F... | ........... | RN..........H..V.... | ........K... |
| iPS:39 2808 | 21-225_20F8 | VH3J3-23/D6[6-19]RF1/JH3 | ......R... | ........... | ...I........S. | ......R..V... | .....S..... | R..N........H..V.... | ........... |
| Germline | | H_FR1 QVQLVES GGGLVKPSETLS LTCTVSG GSIS | H_CDR1 SS SYWG | H_FR2 WIRQPPGK GLEWIG | H_CDR2 SIYY SGSTYYNP SLKS | H_FR3 RVTISVDTSKNQFSLKL SSVTAADTAVYYCAR | H_CDR3 HYWYT ——————RIYFDY | H_FR4 WGQGTL VTVSS |
| VH4J4-39/D2[2-21]RF3/JH4 | | | | | | | | | |
| iPS:43 5525 | 21-225_157E7 | VH4J4-39/D2[2-21]RF3/JH4 | .H......... | ...G........ | ........... | ........... | .......N..... | .K.AG-......—P... | ........... |
| Germline | | H_FR1 QVQLVES GGGVVQPGRSLR LSCAASG FTFS | H_CDR1 ——— YSMH | H_FR2 WVRQAPGK GLEWVA | H_CDR2 VISYD GSNKYYAD SVKG | H_FR3 RFTISRDNSKNTLYLQM NSLRAEDTAVYYCAR | H_CDR3 YPYSSGSYYN ——————YYYGMDV | H_FR4 WGQGTT VTVSS |
| VH3J3-33/D3[3-10]RF2/JH6 | | | | | | | | | |
| iPS:43 5543 | 21-225_158D4 | VH3J3-33/D3[3-10]RF2/JH6 | ........... | D........V... | ......S..... | ........... | ........... | EP.T..W———..D...... | ........... |
| iPS:43 5571 | 21-225_159C8 | VH3J3-33/D3[3-10]RF2/JH6 | ........... | D........V.Q | ........... | ........... | ........... | EP.N..W———..D...... | ........... |
| iPS:43 5591 | 21-225_160C4 | VH3J3-33/D3[3-10]RF2/JH6 | ........... | D........V.Q | ........... | ........... | ........... | EP.N..W———..D...... | ........... |
| iPS:43 5615 | 21-225_161G12 | VH3J3-33/D3[3-10]RF2/JH6 | ........... | D........V.Q | ........... | ........... | ........... | EP.N..W———..D...... | ........... |
| iPS:43 6604 | 21-225_226F7 | VH3J3-33/D3[3-10]RF2/JH6 | ........... | ........... | ......I..... | ........... | ........... | ER.N..W———..D..L... | ........... |

Figure 52 (Continued)

| | | H_FR1 | H_CDR1 | H_FR2 | H_CDR2 | H_FR3 | | H_CDR3 | H_FR4 |
|---|---|---|---|---|---|---|---|---|---|
| iPS:45 1114 | 21-225_159A3 | VH3\|3-33/D3\|3-10\|RF2/JH6 | ........ ........ ........ | D......V.Q | ........ ........ | ........ | ........ | I | EP.N..W--- ........ | ........ ........ |
| iPS:47 2732 | 21-225_2B10_L C1 | VH3\|3-33/D3\|3-10\|RF2/JH6 | ........ ........ ........ | ...V... | ........ ........ | ...V | ........ | ...V... | ER.T..W--- .D..... | ........ ........ |
| iPS:47 2733 | 21-225_2B10_L C2 | VH3\|3-33/D3\|3-10\|RF2/JH6 | ........ ........ ........ | ...V... | ........ ........ | ...V | ........ | ...S... | ER.T..W--- .D..... | ........ ........ |
| iPS:39 2872 | 21-225_20B11 | VH3\|3-33/D3\|3-10\|RF2/JH6 | ........ ........ ........ | ...V... | ........ ........ | ...V | ........ | ...S... | ER.T..W--- .D..... | ........ ........ |
| iPS:39 3966 | 21-225_7F8 | VH3\|3-33/D3\|3-10\|RF2/JH6 | ........ ........ ........ | ...CV... | ........ ........ | ........ | ........ | N...... | HD........ | ........ ........ |
| VH3\|3-23\|D1\|1-1\|RF1/JH6 | | Germline | EVQLVES GGGLVQPGGSLR LSCAASG-FTFS | S----YAMS | WVRQAPGK GLEWVS | SISSS-GGSTYAD SVKG | RFTISRDNSKNTLY LQMNSLRAEDTAVYYCAR | | GTTGTY------YYYGMDV | WGQGT VTVSS |
| iPS:43 5559 | 21-225_158H12 | VH3\|3-23\|D1\|1-1\|RF1/JH6 | ........ ........ ........ | ........ | ........ | .R.D... | ........ | ........ | .GW--- --NHD | ........ ........ |
| VH3\|3-21\|D1\|1-1\|RF1/JH6 | | Germline | EVQLVES GGGLVKPGGSLR LSCAASG-FTFS | S----YSMN | WVRQAPGK GLEWVS | SISSS-SSTYYAD SVKG | RFTISRDNANSL YLQMNSLRAEDTAVYYCAR | | GTTGTY------YYYGMDV | WGQGT VTVSS |
| iPS:43 5561 | 21-225_159F1 | VH3\|3-21\|D1\|1-1\|RF1/JH6 | ........ ........ ........ | ........ | ........ | GN..D... | ........ | ........ | .W--- ........ | ........ ........ |
| VH1\|1-08\|D1\|1-1\|RF1/JH4 | | Germline | QVQLVQS GAEVKKPGASVK VSCKASG-YTFT | S----YDIN | WVRQATGQ GLEWMG | WMNPN-SGNTGYAQ KFQG | RVTMTRNTSISTAYMEL SSLRSEDTAVYYCAR | | GTTGT-------YFDY | WGQGT LVTVSS |
| iPS:43 5563 | 21-225_159H2 | VH1\|1-08\|D1\|1-1\|RF1/JH4 | ........ ........ ........ | ........ | ........ | ...V... | ........ | ........ | KK.--- ...G--- | ........ ........ |

| | VH3|3-33|D3|3-9|RF2|JH4 | LQLKS SGGVQPGRSLR SCAASG-FTFS | S | YGMH WVRQAPGK GLEWVA | WYSGS CSIKTYAD SVKG | RFTISRDNSKNTLY LQMNSLRAEDTAVYYCAR | WLLTG VYNFDY | WGQGTL VTVSS |
|---|---|---|---|---|---|---|---|---|
| iPS:43 5663 | 21-225_169B1 | VH3|3-33|D3|3-9|RF2|JH4 | . . . . . . . . . . . . . . . . . . | . . . . . . . | . . . . . . . . . . . . . . . . . . | . . R . . . . . . . . . | . . . . . . . . . . . . . . . . . . . . . . . . . . . . . . . . . . . . . . . . . . . . . . . . . | DPLRGYN . . . . . . . -DPVM . . | . . . . . . . . . . |
| iPS:43 5669 | 21-225_169F9 | VH3|3-33|D3|3-9|RF2|JH4 | . . . . . . . . . . . . . . . . . . | T . . . . . . | . . . . . . S . . . . . . . . . . . | I . . . . . . T . . . . | . . . . . . . . . . . . . . . . . . . . . . . . . . . . . . . . . . L . . . . . . . . . . . . . . | DPLRGYN . . . . . . . -DPVM . . | . . . . . . . . . . |
| iPS:43 5693 | 21-225_170G4 | VH3|3-33|D3|3-9|RF2|JH4 | . . . . . . . . . . . . . . . T . . | T . . . . . . | . . . . . . S . . . . . . . . . . . | I . . . . . . T . . . . | . . . . . . . . . . . . . . . . . . . . . . M . . . . . F . . L . . . . . . . . . . . . . . . . . | DPLRGYN . . . . . . . -DPVM . . | . . . . . . . . . . |
| iPS:43 5695 | 21-225_170D5 | VH3|3-33|D3|3-9|RF2|JH4 | . . . . . . . . . . . . . . . . . . | . . . . . . . | . . . . . . . . . . . . . . . . . . | I . . . . . . T . . . . | . . . . . . . . . . . . . . . . . . . . . . . . . . . . . . . . . . L . . . . . . . . . . . . . . | DPLRGYN . . . . . . . -DPVM . . | . . . . . . . . . . |
| iPS:43 5697 | 21-225_170G5 | VH3|3-33|D3|3-9|RF2|JH4 | . . . . G . . . . . . . . . . . . . | T . . . . . . | . . . . . . T . . . . . . . . . . . | I . . . . . . T . . . . | . . . . . . . . . . . . . . . . . . . . . . S . . . . . F . . . . . . . . . . . . . . . . . . . . | DPLRGYN . . . . . . . -DPVM . . | . . . . . . . . . . |
| iPS:43 5703 | 21-225_170D11 | VH3|3-33|D3|3-9|RF2|JH4 | . . . . . . . . . . . V . . . . . . | . . . . . . . | . . . . . . . . . . . . . . . . . . | I . . . . . . T . . . . | . . . . . . . . . . . . . . . . . . . . . . . . . . . . . . . . . . . . . . . . . . . . . . . . . | DPLRGYN . . . . . . . -DPVM . . | . . . . . . . . . . |
| iPS:43 5705 | 21-225_171C3 | VH3|3-33|D3|3-9|RF2|JH4 | . . . . G . . . . . . . . . . . . . | T . . . . . . | . . . . . . T . . . . . . . . . . . | I . . . . . . T . . . . | . . . . . . . . . . . . . . . . . . . . . . . . . . . . . . . . . . L . . . . . . . . . . . . . . | DPLRGYN . . . . . . . -DPVM . . | . . . . . . . . . . |
| iPS:43 5709 | 21-225_171A4 | VH3|3-33|D3|3-9|RF2|JH4 | . . . . G . . . . . . . . . . . . . | T . . . . . . | . . . . . . . . . . . . . . . . . . | I . . . . . . T . . . . | . . . . . . . . . . . . . . . . . . . . . . . . . . . . . . . . . . . . . . . . . . . . . . . . . | DPLRGYN . . . . . . . -DPVM . . | . . . . . . . . . . |
| iPS:43 5721 | 21-225_172B3 | VH3|3-33|D3|3-9|RF2|JH4 | . . . . P . . . . . . . . . . . . . | T . . . . . . | . . . . . . . . . . . . . . . . . . | I . . . . . . T . . . . | . . . . . . . . . . . . . . . . . . . . . . . . . . . . . . . . . . . . . . . . . . . . . . . . . | DPLRGYN . . . . . . . -DPVM . . | . . . . . . . . . . |
| iPS:43 5725 | 21-225_172G8 | VH3|3-33|D3|3-9|RF2|JH4 | . . . . M . . . . . . . . . . . . . | . . . . . . . | . . . . . . M . . . . . . . . . . . | I . . . . . . T . . . . | . . . . . . . . . . . . . . . . . . . . . . . . . . . . . . . . . . L . . . . . . . . . . . . . . | DPLRGYN . . . . . . . -DPVM . . | . . . . . . . . . . |
| iPS:43 5735 | 21-225_173H12 | VH3|3-33|D3|3-9|RF2|JH4 | . . . . . . . . . . . . . . . . . . | . . . . . . . | . . . . . . . . . . . . . . . . . . | I . . . . . . T . . . . | . . . . . . . . . . . . . . . . . . . . . . . . . . . . . . . . . . L . . . . . . . . . . . . . . | DPLRGYN . . . . . . . -DPVM . . | . . . . . . . . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5743 | 21- 225_175G1 | VH3\|3-33/D3\|3-9\|RF2/JH4 | .........G.. | .........T.. | ............ | ............ | ............ | ......V..DPLRGYN......-DPVM. | ......... |
| iPS:43 5761 | 21- 225_176B11 | VH3\|3-33/D3\|3-9\|RF2/JH4 | ............ | ............ | ........S... | ....I....T.. | ............ | ......F..L.DPLRGYN......-DPVL. | ......... |
| iPS:43 5779 | 21- 225_178B10 | VH3\|3-33/D3\|3-9\|RF2/JH4 | ........V..S. | ............ | .......M.... | ....I....T.. | ............ | .........L.DPLRGYN......-DPVM. | ......... |
| Germline | VH3\|3-48/D2\|2-15\|RF3/JH6 | EVQLVES GGGLVQPGGSLR LSCAASG-FTFS | ..YSMN | WVRQAPGK GLEWVS | VISSS SSTIYYAD SVKG | RFTISRDNAKNSLYLQM NSLRPEDTAVYYCAR | DIVVYAAT YYYYYGMDV | WGQGT VTVSS |
| iPS:43 5667 | 21- 225_169E3 | VH3\|3-48/D2\|2-15\|RF3/JH6 | .........G.. | ......H..... | ........A... | ......L..K.. | ............RD..... | RGIT..R--- NED.L... | ......... |
| iPS:43 5673 | 21- 225_169E6 | VH3\|3-48/D2\|2-15\|RF3/JH6 | .........G.. | ......H..... | ........A... | ......I..K.. | ............RD..... | RGIT..R--- NED.L... | ......... |
| iPS:43 5759 | 21- 225_176E6 | VH3\|3-48/D2\|2-15\|RF3/JH6 | .........G.. | ......H..... | ........A... | ......I..K.. | ......I.....RD..... | RGIT..R--- NED.L... | ......... |
| Germline | VH4\|4-59/D3\|3-9\|RF1/JH6 | EVQLLES GPGLVKPSETLS LTCTVSG-GSIS | ....YWS | WIRQPPGK GLEWIG | YIYY SSTNYNP SLKS | RVTISVDTSKNQFS.KL SSVTAADTAVYYCAR | VLRYFDWLL- -YYYYGMDV | WGQGT VTVSS |
| iPS:43 5675 | 21- 225_169D7 | VH4\|4-59/D3\|3-9\|RF1/JH6 | ............ | ............T | ........A..T | ......R..T.. | ......M............ | .G..Y------ | ......... |
| iPS:43 5687 | 21- 225_170H1 | VH4\|4-59/D3\|3-9\|RF1/JH6 | ............ | ............ | ........A... | ......R..T.. | ......M..F..K...... | .G..Y------ | ......... |
| Germline | VH3\|3-23/D4\|4-23\|RF2/JH4 | EVQLLES GGGLVQPGGSLR LSCAASG-FTFS | ....YAMS | WVRQAPGK GLEWVS | AISGS GGSTYYAD SVKG | RFTISRDNSKNTLYLQM NSLRAEDTAVYYCAR | DYGGN-------SLFDY | WGQGTL VTVSS |

Figure 52 (Continued)

| | | | | | | | | | |
|---|---|---|---|---|---|---|---|---|---|
| iPS:43 5711 | 21-225_171G4 | VH3|3-23|D4|4-23|RF2|JH4 | ........D... | ........C..T | ........ | ......R. ..T.F. ...R.. | ........ | ........F | .L.I.GA..... .......T..... |
| iPS:43 5875 | 21-225_190B9 | VH3|3-23|D4|4-23|RF2|JH4 | ........ | T....... | ........ | ......R. ...N.H. | ........ | .....S.. | .GF.GS...... |
| iPS:43 5909 | 21-225_190H3 | VH3|3-23|D4|4-23|RF2|JH4 | ........ | ........ | ........ | ......R. ...N... | ........ | ........ | .GF.GS...... |
| iPS:43 6013 | 21-225_193F2 | VH3|3-23|D4|4-23|RF2|JH4 | ........ | T...F... | ........ | ......R. ...N.H. | ........ | .....S.. | .GF.GS...... |
| iPS:43 6100 | 21-225_195G12 | VH3|3-23|D4|4-23|RF2|JH4 | ........ | T....... | ........ | ......R. ...N.H. | ........ | .....S.. | .GF.GS...... |
| Germline | | | H_FR1 EVQLLES GGGLVQPGGSLR LSCAASG-FTFS | H_CDR1 S----YAMS | H_FR2 WVRQAPGK GLEWVS | H_CDR2 -VISH- SGSNKYYAD SVKG | H_FR3 RFTISRDNSKNTLYLQM NSLRAEDTAVYYCAR | H_CDR3 VX-ELYY -----YYYGMDV | H_FR4 WGQGTT VTVSS |
| iPS:43 5713 | 21-225_171D7 | VH3|3-30.3|D1|1-7|RF2|JH6 | .........R..... | ......G. | ........ | ..N.RH.. ..Q..... | ........G...... ................. | DRHR.D- ...AL.. | ........ |
| Germline | | | H_FR1 EVQLVES GGGLVQPGGSLR LSCAASG-FTFS | H_CDR1 S----YAMS | H_FR2 WVRQAPGK GLEWVS | H_CDR2 AISGS GGSTYYAD SVKG | H_FR3 RFTISRDNSKNTLYLQM NSLRAEDTAVYYCAK | H_CDR3 RDINY -----DAFDI | H_FR4 WGQGTM VTVSS |
| iPS:43 5729 | 21-225_173E7 | VH3|3-23|D5|5-24|RF3|JH3 | ........ | ........ | F....... | ...N.F.. ........ | .....Q.......... ................. | ..T.G.. ....... | ........ |
| iPS:43 5753 | 21-225_175G10 | VH3|3-23|D5|5-24|RF3|JH3 | ......S. | ........ | ........ | ...I.... ........ | ........T....... ................. | ..W.... ....... | ........ |
| iPS:39 3024 | 21-225_31H9 | VH3|3-23|D5|5-24|RF3|JH3 | ........ | .....C..N | ........ | .....SF. ........ | ................. ................. | TW.G... ..W.... | ........L |
| | | | | | | | | TP.D-.. ..-V... | |

Figure 52 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:39 8474 | 21-225_17B10 | VH3|3-23|D5|5-24|RF3|J H3 | ..........................R | .................. | .................. | ......V........N.F... | .................D....... | .GIPEA............ | ............... |
| | | Germline | EVQLLES CGTTKPGASVK VSCAASG-YTFT | -------YIMH | WVRQAPGQ GLEWMG | WINPN SGGTNYAQ KFQG | RVTMTRDTSISTAYMEL SRLRSEDTAVYYCAR | GTTGT DAFDI | WGQGTL VTVSS |
| iPS:43 5745 | 21-225_175G3 | VH1|1-02|D1|1-1|RF1|JH 3 | ........V......... ................ | ............F... | .................. | .....K.K........C... R...... | ................T.... .............V...... | .G.TVTT....... ......WGV..Y | ............... |
| iPS:43 7270 | 21-225_178H4 | VH1|1-02|D1|1-1|RF1|JH 3 | .................. ................ | ............F... | .................. | .....K.K........C... ...... | ..................... .............V...... | .G.TVTT....... ......WGV..Y | ............... |
| | | Germline | EVQLLES CGTTKPGGSLR LSCAASG-FTFS | S-----YAMS | WVRQAPGK GLEWVS | AISGS CGSTYYAD SVKG | RFTISRDNSKNTLYLQM NSLRAEDTAVYYCAR | YIIDSSG YYYYFDY | WGQGTL VTVSS |
| iPS:43 5769 | 21-225_177B6 | VH3|3-23|D3|3-22|RF2|JH4 | ........R....E... ................ | .................. | .................. | .V................ .SN...V.......... | ................N.... ................T... | G.............. ........P..F | ............... |
| | | Germline | EVQLVES CGTTKPGESLR LSCAASG-FTFS | S-----YGMH | WVRQAPGK GLEWVA | VIWYD GSNKYYAD SVKG | RFTISRDNSKNTLYLQM NSLRAEDTAVYYCAR | YIIDSSG YYYYFDY | WGQGTL VTVSS |
| iPS:43 5771 | 21-225_177B11 | VH3|3-33|D3|3-22|RF2|JH 1 | ...........T.... ................ | .................. | .................. | .....Y....T........ | ..................... ..................... | ET..FW-- SG...VF | ............... |
| | | Germline | EVQLVES CGTTKPGGSLR LSCAASG-FTFS | S-----YAMS | WVRQAPGK GLEWVS | AISGS GGSTYYAD SVKG | RFTISRDNSKNTLYLQM NSLRAEDTAVYYCAR | RDGYN YYPFDY | WGQGTL VTVSS |
| iPS:43 5775 | 21-225_178A5 | VH3|3-23|D5|5-24|RF3|J H4 | .....H............ .T................ | .................T | .................. | .V................ ....N.F............. | .....................R .................... | ....D-........ ............... | ............... |
| iPS:43 7214 | 21-225_48B12 | VH3|3-23|D5|5-24|RF3|J H4 | .................. ................ | .................N | .................. | .....R............ ....N.F............. | ..................... .................... | .ET..WN.... ........YEG... | ............... |

| | | H_FR1 | H_CDR1 | H_FR2 | H_CDR2 | H_FR3 | H_CDR3 | H_FR4 |
|---|---|---|---|---|---|---|---|---|
| iPS:43 5813 | 21-225_183A12 | VH3J3-30.3/D6j6-19|RF1/JH5 | ........G.. | | ...SA... | | R..........-D-- | |
| | | Germline | EVOLVES- GGGLVKPGGSLR LSCAASG-FTFS | YMS | WVRQAPGK GLEWVS | SISSS--SSIYYAD STKG | RFTISRDNAKNSLYLQM NSLRAEDTAVYYCAR | ITAVRGV- -IYFDY | WGQGT LVTVSS |
| iPS:43 5815 | 21-225_190G10 | VH3J3-21|D3J3-10|RF3/JH4 | ............R | D...... | | .G..H.. | ....M..... | A..A--- --L.. | |
| iPS:43 5865 | 21-225_191A5 | VH3J3-21|D3J3-10|RF3/JH4 | ..I.V....R | D...... | | .G..... | ....M..... | A..A--- --L.. | A. |
| iPS:43 6047 | 21-225_193B10 | VH3J3-21|D3J3-10|RF3/JH4 | ............R | D...... | | ..A...GG..L.. | ....M..... | A..A--- ..L.. | |
| iPS:43 6122 | 21-225_196G10 | VH3J3-21|D3J3-10|RF3/JH4 | ............R | D...... | | .G..H.. | ....M..... | A..A--- --L.. | |
| | | H_FR1 | H_CDR1 | H_FR2 | H_CDR2 | H_FR3 | H_CDR3 | H_FR4 |
| | | Germline | CVQLQES- GPGLVKPSETLS LTCTVSG-GSIS | YYWS | WIRQPPGK GLEWIG | YIYY-SGSTRYNP SLKS | RVTISIDRSKNQLSLC LSSVTAADTAVYYCAR | DYGDYY -YYGMDY | WGQGT LVTVSS |
| iPS:43 5817 | 21-225_190B11 | VH4J4-59|D4J4-17|RF2/JH6 | ............N | N...... | A...... | R..T... | ...M..... | R.Y.G- | |
| iPS:43 5917 | 21-225_190D5 | VH4J4-59|D4J4-17|RF2/JH6 | ............N | N...... | A...... | R..A... | ...M.I...H.... | R.Y.G- | ..I |
| iPS:43 6056 | 21-225_194C3 | VH4J4-59|D4J4-17|RF2/JH6 | ............N | N...... | A...... | R..A... | ...M.I...H.... | R.Y.G- | ..I |
| iPS:43 6220 | 21-225_200F8 | VH4J4-59|D4J4-17|RF2/JH6 | ............N | N...... | A...... | R..T... | ...M..... | R.Y.G- | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| VH3|3-30|D4|4-17|RF2|JH6 | | QVQLVES GGGVVQPGRSLR LSCAASG-FTFS | YGMH | WVRQAPGKGLEWVA VISYDG-SNKYYA | DSVKG RFTISRDNSKNTLYLQMNSLRAEDTAVYYCAK | DYGDYYY-YYGMDV | WGQGT TVTVSS |
| iPS:43 21-225_190E11 5821 | VH3|3-30|D4|4-17|RF2|JH6 | .......... ........-.... | N........ | .......... ...... I.WF. | .......N... ...................... | AQ.V.------- ------ | ...... |
| | Germline | H_FR1 | H_CDR1 | H_FR2 | H_CDR2 | H_FR3 | H_CDR3 | H_FR4 |
| VH3|3-23|D5|5-12|RF3|JH5 | | EVQLLES GGGLVQPGGSLR LSCAASG-FTFS | SYAMS | WVRQAPGKGLEWVS AISGS-GGSTYYA | DSVKG RFTISRDNSKNTLYLQMNSLRAEDTAVYYCAR | ----------- --NFFDP | WGQGT LVTVSS |
| iPS:43 21-225_190F11 5823 | VH3|3-23|D5|5-12|RF3|JH5 | ......D..... G......-.... | ........N | .......... ...... T..T.. | ........... ...................... | EEDY..S..... ......SGPG | ...... |
| iPS:43 21-225_191E5 5867 | VH3|3-23|D5|5-12|RF3|JH5 | ......D..... G......-.... | ........N | .......... ...... T..T.. | ........... ...................... | EEDY..S..... ......SGPG | ...... |
| iPS:43 21-225_190D9 5929 | VH3|3-23|D5|5-12|RF3|JH5 | ......D..... G......-.... | ......... | .......... ...... T..T.. | ........... ...................... | EEDY..S..... ......SGPG | ...... |
| iPS:43 21-225_190H8 5935 | VH3|3-23|D5|5-12|RF3|JH5 | ......D..... G......-.... | ......... | .......... ...... T..T.. | ........... ...................... | EEDY..S..... ......SGPG | ...... |
| | Germline | H_FR1 | H_CDR1 | H_FR2 | H_CDR2 | H_FR3 | H_CDR3 | H_FR4 |
| VH4|4-39|D3|3-9|RF1|JH4 | | QLQLQES GPGLVKPSETLS LTCTVSG-GSIS | SSSYYWG | WIRQPPGKGLEWIG SIYYS- GSTYYNP | SLKS RVTISVDTSKNQFSLKL SSVTAADTAVYYCAR | VLRYDW---- ---LL-VFDY | WGQGT LVTVSS |
| iPS:43 21-225_190H11 5827 | VH4|4-39|D3|3-9|RF1|JH4 | ........... .........R | ..-......H.S | .......... A..... L..T.. .R..I. | ........L.. ...................... | LRYNWN----- ---FP..... | ...... |
| iPS:43 21-225_191E3 5853 | VH4|4-39|D3|3-9|RF1|JH4 | ........... .........R | ..-......H.S | .......... A..... L..T.. .R..N. | ........M.. .........N............ | LRYNWN----- ---FP..... | ...... |
| iPS:43 21-225_191E6 5871 | VH4|4-39|D3|3-9|RF1|JH4 | ........... .........R | ..-......H.S | .......... A..... L..T.. .R..N. | ........M.. ...................... | LRYNWN----- ---FP..F.. | ...... |
| iPS:43 21-225_190E7 5927 | VH4|4-39|D3|3-9|RF1|JH4 | ........... .........R | ..-......H.S | .......... A..... H..T.. .R..N. | ........T.. ...................... | LRYNWN----- ---FP..... | ...... |

Figure 52 (Continued)

| | | | H_CDR1 | | H_FR2 | H_CDR2 | H_FR3 | H_CDR3 | H_FR4 |
|---|---|---|---|---|---|---|---|---|---|
| iPS:43-5999 | 21-225_192F9 | VH4|4-39/D3|3-9|RF1/JH4 | ......... | ----.H.S | ....A.. | L..T... | ...M........ | LRYNWN- | .... |
| | | | | | | .R..N.. | | .N........ | FP.... | .... |
| iPS:43-6060 | 21-225_194F4 | VH4|4-39/D3|3-9|RF1/JH4 | .........R | ----.H.S | ....A.. | L..T... | ...M...R..S. | LRYNWN- | .... |
| | | | | | | .R..N.. | | | FP.... | .... |
| iPS:43-6193 | 21-225_198A10 | VH4|4-39/D3|3-9|RF1/JH4 | ......... | ----.H.S | ....A.. | H..T... | .....T...... | LRYNWN- | .... |
| | | | | | | .R..N.. | | | FP.... | .... |
| VH4|4-30.1|D5|5-24|RF3/JH2 | | Germline | H_FR1 | H_CDR1 | H_FR2 | H_CDR2 | H_FR3 | H_CDR3 | H_FR4 |
| | | | QVQLQES-GPGLVKPSETLS LTCTVSG-GSIS | SG----GYYWS | WIRQHPGK GLEWIG | YIYY- SGSTYYNP SLKS | RVTISVDTSKNQFSLKL SSVTAADTAVYYCAR | FGGHY- LWFFDL | WGRGTL VTVSS |
| iPS:43-5829 | 21-225_190B12 | VH4|4-30.1/D5|5-24|RF3/J H2 | ......... | ........N | ........ | ........ | ....F....... | SGYNWD -AGV.P | .... |
| VH3|3-33/D4|4-11|RF2/JH6 | | Germline | H_FR1 | H_CDR1 | H_FR2 | H_CDR2 | H_FR3 | H_CDR3 | H_FR4 |
| | | | QVQLVES-GGGVVQPGRSLR LSCAASGFTFS | SY----YGMH | WVRQAPGK GLEWVA | VISYD GSNKYYAD SVKG | RFTISRDNSKNTLYLQM NSLRAEDTAVYYCAR | DYNFF- LVYGMDV | WGQGTT VTVSS |
| iPS:43-5835 | 21-225_190F12 | VH3|3-33/D4|4-11|RF2/J H6 | .........N | ......... | ........ | ....F... | .........S.. | .R.VG.- D..... | .... |
| iPS:43-5861 | 21-225_190A5 | VH3|3-33/D4|4-11|RF2/J H6 | ........G | ......... | ........ | ....D... | ............ | F.VG.- D..... | .... |
| iPS:43-5937 | 21-225_190H9 | VH3|3-33/D4|4-11|RF2/J H6 | .........N | ......... | ........ | ....N... | .........S.. | .R.VG.- D.L... | .... |
| iPS:43-5977 | 21-225_192E4 | VH3|3-33/D4|4-11|RF2/J H6 | .........N | ......... | ........ | ....F... | ............ | .R.VG.- D..... | .... |
| | | | | | | ...N.V.. | | | | |
| | | | | | | ...R... | | | | |
| iPS:43-6001 | 21-225_192C10 | VH3|3-33/D4|4-11|RF2/J H6 | .........R | ......... | .....K.. | ....F... | .........S.. | .R.VG.- D.L... | .... |
| | | | .....S.. | | | ....D... | | | |

Figure 52 (Continued)

| | | | | | | | |
|---|---|---|---|---|---|---|---|
| iPS:43 6066 | 21-225_194B7 | VH3\|3-33/D4\|4-11\|RF2/J H6 | . . . . . . . . . . . . | . . . . . . . . . . . . | . . . . . . . . . . . . | . . . . . . . . . . . . | .R.KG.-. . . . . . . . . . . . . . |
| iPS:43 6078 | 21-225_194H12 | VH3\|3-33/D4\|4-11\|RF2/J H6 | . . . . . . . . . R . | N . . . . . . . . . . . | . . . . . . . . . . . . | . . . . S . . . . . . . . . . | .R.VG.-. . . . . . . . . . . . D.L. . . |
| iPS:43 6140 | 21-225_197G3 | VH3\|3-33/D4\|4-11\|RF2/J H6 | . . . . . . . V . . . | . . . . H . . . . | . . . . . . . . N . . . | . . . . . . . . . . . . | .P.VG.-. . . . . . . . . . . . D . . . |
| iPS:43 6167 | 21-225_197E11 | VH3\|3-33/D4\|4-11\|RF2/J H6 | . . . . . . . . . R . | N . . . . . . . . | . . . . . . . . F . D . | . . . . S . . . . . . . . . . | .R.VG.-. . . . . . . . . . . . D.L. . . |
| iPS:43 6292 | 21-225_205H3 | VH3\|3-33/D4\|4-11\|RF2/J H6 | . . . . . . . . . . . . | . . . . . . . . . . . . | . . . . . . . . . . . . | . . . . . . . . . . . . | .R.VG.-. . . . . . . . . . . . D.T. . . |
| iPS:43 6802 | 21-225_171E12 | VH3\|3-33/D4\|4-11\|RF2/J H6 | . . . . . . . . . . . . | . . . . . . . . . . . . | . . . . . . . . N . . . G . . . NG . | . . . . . . . . . . . . | RTY.SGSGSP. . . . . . .PYY. . . . . |
| iPS:43 6816 | 21-225_179H5 | VH3\|3-33/D4\|4-11\|RF2/J H6 | . . . . . . . . . . . . | . . . . . . . . . . . . | . . . . . . . . E . . . | . . . . . . . . . . . . | IR . . . - . . . . . . . |
| iPS:43 6960 | 21-225_198D2 | VH3\|3-33/D4\|4-11\|RF2/J H6 | . . . . . . . . . R . | . . . . . . . . . . . . | . . . . . . . . I . . . Y . . . | . . . . . . . . . . . . | . . . L . . . - . . . . . . . |
| iPS:43 6974 | 21-225_190H7 | VH3\|3-33/D4\|4-11\|RF2/J H6 | . . . . . . . . . N . R | . . . . . . . . . . . . | . . . . . . . . I . . . Y . . . | . . . . . . . . . . . . | T. .G . . .- . . . . . . . |
| iPS:43 6982 | 21-225_190D10 | VH3\|3-33/D4\|4-11\|RF2/J H6 | . . . . . . . . . R . | . . . . . . . . . . . . | . . . . . . . . I . . . Y . . . | . . . . . . . . . . . . | T. .G . . .- . . . . . . . |
| iPS:43 7274 | 21-225_196D4 | VH3\|3-33/D4\|4-11\|RF2/J H6 | . . . . . . . V . . . | . . . . . . . . . . . . | . . . . . . . . RN . . | . . . . V . . . . . . . . . . | .R.KG.-. . . . . . . . . . . . D . . . |
| iPS:39 2664 | 21-225_20F6 | VH3\|3-33/D4\|4-11\|RF2/J H6 | . . . . . . . . . V . | . . . . . . . . . . . . | . . . . . . . . H . . . . . G . | . . . . A . . . . . . . . . . | .L.MG.-. . . . . . . . . . . . - . . . |

Figure 52 (Continued)

| | | | | | | |
|---|---|---|---|---|---|---|
| iPS:39 2738 | 21-225_18G4 | VH3\|3-33/D4\|4-11\|RF2/J H6 | . . . . . . . . . . . . . . . | . . . . . . . . . . . . . . . | . . . . . . . . . . . . . . . | L.MG--- . . . . . --- |
| iPS:39 2798 | 21-225_22C7 | VH3\|3-33/D4\|4-11\|RF2/J H6 | . . . . . . . . . . . . . . . | . . . G . . . . . . H . . . | . . . . . . . . . . A . . . . | L.MG--- . . . . . --- |
| iPS:39 2956 | 21-225_27A11 | VH3\|3-33/D4\|4-11\|RF2/J H6 | . . . . . . . . . . . . . . . | . . . . . . . . . . . . . . . | . . . . . . . . H . . . . . . | S.P.--- . . . . . --- |
| iPS:39 2994 | 21-225_26G11 | VH3\|3-33/D4\|4-11\|RF2/J H6 | . . . . . . . . . . . . . . . | . . . . . . . . . . . . . . . | . . . . . . . . . . . . . . . | R...SW- SG.... |
| iPS:39 3014 | 21-225_26D12 | VH3\|3-33/D4\|4-11\|RF2/J H6 | . . . . . . . . . . . . . . . | . . . . . . . . . . F . . . | . . . . . . . . . . A . . . . | S.P.--- . . . . . --- |
| iPS:39 3152 | 21-225_25B3 | VH3\|3-33/D4\|4-11\|RF2/J H6 | . . . . . . . . . . . . . . . | . . . G . . . . . . H . . . | . . . . . . . . . . . . . . . | . . . . . . |
| iPS:39 3840 | 21-225_3F8 | VH3\|3-33/D4\|4-11\|RF2/J H6 | . . . . . . . . . . F . . . | . . . . . . . . . . . . . . . | . . . . . . . . . . A . . . . | S.P.--- . . . . . --- |
| iPS:39 3930 | 21-225_7E11 | VH3\|3-33/D4\|4-11\|RF2/J H6 | . . . . . . . . . . . . . . . | . . . . . I . . H . . . . . | . . S . . . . . . . . . . . . | L.MG--- . . . . . --- |
| iPS:39 3964 | 21-225_6G1 | VH3\|3-33/D4\|4-11\|RF2/J H6 | . . . . . F . . . . . . . . | . . . . . I . . . . . . . . | . . . . . . . . . . N . . . . | L.MG--- . . . . . --- |
| iPS:39 4012 | 21-225_15A3 | VH3\|3-33/D4\|4-11\|RF2/J H6 | . . . . . . . . . . . . . . . | . . . . . . . H . . . . . . | . . . . . . . . M . . . . . . | L.MG--- . . . . . --- |
| iPS:39 4016 | 21-225_13D4 | VH3\|3-33/D4\|4-11\|RF2/J H6 | . . . . . . . . . . . . . . . | . . . . . . . H . . . . . . | . . . . . . . . . . . . . . . | L.MG--- . . . . . --- |
| iPS:39 4083 | 21-225_16E6 | VH3\|3-33/D4\|4-11\|RF2/J H6 | . . . . . . . . . . . . . . . | . . . . . . . H . . V . . . | . . . . . . . . N . . . . . . | L.MG--- . . . . . --- |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4|4-59|D3|3-9|RF1|JH4 | | QVQLQES GPGLVKPSETLS LTCTVSG-CSIS | YYWS | WIRQPPGK GLEWIG | YIYY SGSTNYNP SLKS | RVTISVDTSKNQFSLK LSSVTAADTAVYYCAR | VTRYDW----LL*VEDY | WGQGTT VTVSS |
| iPS:43_5839 | 21-225_191B1 | VH4|4-59|D3|3-9|RF1|JH4 | .......H. | ......A. | ..H.T. ....K. ..... | .........M......... ................ | LRYNWN- FPF... | ... ... ... |
| iPS:43_6158 | 21-225_197G8 | VH4|4-59|D3|3-9|RF1|JH4 | .......H. | A.......S. | ......A. RLSP.. G...F. | .........M......... ..............R. | LRYNWN- FP..... | ...A. ... ... |
| | Germline | H_FR1 | H_CDR1 | H_FR2 | H_CDR2 | H_FR3 | H_CDR3 | H_FR4 |
| VH4|4-30.1|D3|3-22|RF2|JH6 | | QVQLQES GPGLVKPSQTLS LTCTVSG-GSIS | SGGYYWS | WIRQHPGK GLEWIG | YIYY SGSTYYNP SLKS | RVTISVDTSKNQFSLKL SSVTAADTAVYYCAR | YYYDSSGYYY----YYYYYGMDV | WGQGTT VTVSS |
| iPS:43_5843 | 21-225_191F1 | VH4|4-30.1|D3|3- 22|RF2|JH6 | .........N | ........N | .............F. | ........................ | GD..G...S.- H........ | ... ... ... |
| iPS:43_5847 | 21-225_191A3 | VH4|4-30.1|D3|3- 22|RF2|JH6 | ................. | ....D....N | ............. | .............F. | ........................ | GD..G...S.- H........ | ... ... ... |
| iPS:43_5851 | 21-225_191D3 | VH4|4-30.1|D3|3- 22|RF2|JH6 | ....K...... .......N | ....D....N | ....D. | .............F. | ........................ | GD..G...S.- H........ | ... ... ... |
| iPS:43_5905 | 21-225_190A3 | VH4|4-30.1|D3|3- 22|RF2|JH6 | ...........N | ....D....N | ............. | ..F.F. | ........N............... | GD..G...S.- H........ | ... ... ... |
| iPS:43_5911 | 21-225_190B4 | VH4|4-30.1|D3|3- 22|RF2|JH6 | ................. | ............. | ............. | .............F. | ........................ | GD..G...S.- H........ | ... ... ... |
| iPS:43_5913 | 21-225_190A7 | VH4|4-30.1|D3|3- 22|RF2|JH6 | .......N......... | .....V....... | ............. | ..N.....N. | ..II.................... | GD..G...S.- H....L.. | ... ... ... |

Figure 52 (Continued)

| | | | | | | | | |
|---|---|---|---|---|---|---|---|---|
| iPS-43 5939 | 21-225_191H7 | VH4J4-30.1/D3J3-22|RF2/JH6 | ... | ...D...N | ... | ...F... | ... | GD..G..S.- ...H....... |
| iPS-43 5967 | 21-225_192B3 | VH4J4-30.1/D3J3-22|RF2/JH6 | ....N | ...D...N | ... | F.F.... | ...V.. | GD..G..S.- ...HH...... |
| iPS-43 5973 | 21-225_192H3 | VH4J4-30.1/D3J3-22|RF2/JH6 | ... | V..S.... | .R..... | ... | .A..... | GD..G..S.- ...H....... |
| iPS-43 6007 | 21-225_192G12 | VH4J4-30.1/D3J3-22|RF2/JH6 | ... | V.H... | ... | NL.....N | ....T.. | GD..G..S.- .H.H....... |
| iPS-43 6009 | 21-225_193A1 | VH4J4-30.1/D3J3-22|RF2/JH6 | ... | ...V... | ... | N.H....N | ... | GD..G..S.- ...H....... |
| iPS-43 6011 | 21-225_193B1 | VH4J4-30.1/D3J3-22|RF2/JH6 | ... | ...V... | ... | N......N | .L..A.. | GD..G..S.- ...H....... |
| iPS-43 6017 | 21-225_193F3 | VH4J4-30.1/D3J3-22|RF2/JH6 | ....N | ...D...N | ... | ...F... | ... | GD..G..S.- ...H....... |
| iPS-43 6029 | 21-225_193H6 | VH4J4-30.1/D3J3-22|RF2/JH6 | ....N | ...D...N | ... | ...F... | ... | GD..G..S.- ...H....... |
| iPS-43 6035 | 21-225_193C8 | VH4J4-30.1/D3J3-22|RF2/JH6 | ... | ...D...N | ... | ...F... | ... | GD..G..S.- ...H....... |

Figure 52 (Continued)

| | | | | | | | | | |
|---|---|---|---|---|---|---|---|---|---|
| iPS-43 6037 | 21-225_193D8 | VH4\|4-30.1/D3\|3-22\|RF2/J H6 | . . . . . . . . . . . . . . . | . . . . . . . . . . . . . . . N | . . . . . . . . . . . . . . . | . . . . . F.F. . . . . . . . | . . . S . . . . . . . . . . . | GD..G..S.- . . . . . . . . . . . . . . . H. . . . . . . . . | . . . . . . . . . . . . . . . |
| iPS-43 6041 | 21-225_193G8 | VH4\|4-30.1/D3\|3-22\|RF2/J H6 | . . . . . K . . . . . . . . N . . . . . . . . V . | . . . V . . . . . . . . . . . | . . . . . . . . . . . . . . . | . . . . . . N . . . . . . . . | . . . . . N . . . . . . . . . | GD..G..S.- . . . . . . . . . . . . HF. . . . L. . . | . . . . . H . . . . . . . . . |
| iPS-43 6062 | 21-225_194E5 | VH4\|4-30.1/D3\|3-22\|RF2/J H6 | . . . . . . . . . . . . . . . | . . . D . . . N | . . . H . . . . . . . . . . . | . . . . . F . . . . . . . . . | . . . . . . . . . . . . . . . | GD..G..S.- . . . . . . . . . . . . H. . . . . . . . . | . . . . . . . . . . . . . . . |
| iPS-43 6064 | 21-225_194E6 | VH4\|4-30.1/D3\|3-22\|RF2/J H6 | . . . . . . . . . . D . . N | . . . D . . . N | . . . . . . . . . . . . . . . | . . . . . F.F . . . . . . . . | . . . . . . . . . . I . NV . . | GD..G..S.- . . . . . . . . . . . . H. . . . . . . . . | . . . . . . . . . . . . . . . |
| iPS-43 6134 | 21-225_196H12 | VH4\|4-30.1/D3\|3-22\|RF2/J H6 | . . N . . . . . . . . . . . . | . . . V . . . . . . . . . . . | . . . . . . . . . . . . . . . | . . . . . N . . . . . N . . . | . . . II . . . . . . . . . . . | GD..G..S.- . . . . . . . . . . . . H. . . . . . . . . | . . . . . . . . . . . . . . . |
| iPS-43 6146 | 21-225_197F4 | VH4\|4-30.1/D3\|3-22\|RF2/J H6 | . . . . . . . . . . . . . . . | . . . D . . . N | . . . F . . . . . . . . . . . | . . . . . F . . . . . . . . . | . . . I . . . . . . . . . . . | GD..G..S.- . . . . . . . . . . . . H. . . . L . . . . | . . . . . . . . . . . . . . . |
| iPS-43 6177 | 21-225_198B1 | VH4\|4-30.1/D3\|3-22\|RF2/J H6 | . . . K . . . . . . . . . . N | . . . . . . . . . . . . . . . | . . . . . . . . . . . . . . . | . . . . . FH . . . . . . . . . | . . . V . . . . . . . . . . . | GD..G..S.- . . . . . . . . . . . . H. . . . . . . . . | . . . R . . . . . . . . . . . |
| iPS-43 6179 | 21-225_198E1 | VH4\|4-30.1/D3\|3-22\|RF2/J H6 | . . . . . . . . . . . . . . N | . . . . . . . . . . . . . . . | . . . L . . . E . . . . . . . | . . . . . F.F . . . . . . . . | . . . LS . . . . . . . . . . . | GD..G..S.- . . . . . . . . . . . . H. . . . L . . . . | . . . . . . . . . . . . . . . |
| iPS-43 6197 | 21-225_199C2 | VH4\|4-30.1/D3\|3-22\|RF2/J H6 | . . . . . . . . . . . . . . . | . . . D . . . N | . . . . . . . . . . . . . . . | . . . . . F . . . . . . . . . | . . . T . . . . . . . . . MT . | GD..G..S.- . . . . . . . . . . . . H. . . . . . . . . | . . . . . . . . . . . . . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6207 | 21-225_199C7 | VH4|4-30.1/D3|3-22|RF2/JH6 | ........................ | ..........N............. | ........................ | ....F.F................ | ...........S............ ........................ | GD..G..S.- .H...........- | ........................ |
| iPS:43 6226 | 21-225_200F10 | VH4|4-30.1/D3|3-22|RF2/JH6 | ........................ ........N............... | ........D...N........... | .......L......E......... | ......F................. | ..I..........MT......... .T...................... | GD..G..S.- .H...........- | ........................ |
| VH4|4-30.4/D3|3-22|RF2/JH6 | | Germline QVQLQES---GPGLVKPSQTLS LTCTVSG-GSIS | H_FR1 SG---GYYWS | H_CDR1 WIRQHPGK GLEWIG | H_FR2 YIY---- SGSTYYNP SLKS | H_CDR2 RVTISVDTSKNQFSLKL SSVTAADTAVYYCAR | H_FR3 YYVDSSGYYY ----YYYYGMDV | H_CDR3 WGQGTT VTVSS | H_FR4 |
| iPS:43 5849 | 21-225_191C3 | VH4|4-30.4/D3|3-22|RF2/JH6 | ........................ | ..........N............. | ........................ | .......F................ | ...L.................... .N...................... | GD..G..S.- HF...........- | ........................ |
| iPS:43 6015 | 21-225_193D3 | VH4|4-30.4/D3|3-22|RF2/JH6 | ........................ | ..........N............. | ........................ | .......F................ | ...L.................... ...................T.... | GD..G..S.- HF...........- | ........................ |
| iPS:43 6049 | 21-225_193B12 | VH4|4-30.4/D3|3-22|RF2/JH6 | ........................ | .A........N............. | ........................ | .......F................ | ...L.................... ........................ | GD..G..S.- HF...........- | ........................ |
| iPS:43 6088 | 21-225_195C8 | VH4|4-30.4/D3|3-22|RF2/JH6 | ........................ | ..........N............. | ........................ | .......F................ | ...L.................... ........................ | GD..G..S.- HF...........- | ........................ |
| iPS:43 6195 | 21-225_198G10 | VH4|4-30.4/D3|3-22|RF2/JH6 | ........................ | ..........N............. | ........................ | .......F................ | ...L.................... ........................ | GD..G..S.- HF...........- | ........................ |
| VH4|4-30.1/D5|5-24|RF3/JH5 | | Germline QVQLQES---GPGLVRPSQTLS LTCTVSG-GSIS | H_FR1 SG---GIYWS | H_CDR1 | H_FR2 WIRQHPGK GLEWIG | H_CDR2 YIY---- SGSTYYNP SLKS | H_FR3 RVTISVDTSKNQFSLKL SSVTAADTAVYYCAR | H_CDR3 RDGYNY------NWFDP | H_FR4 WGQGTL VTVSS |

Figure 52 (Continued)

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| | VH3|3-21|D1|1-1|RF3/JH5 | ................................... | ........ | ............... | ........G....... | ..............................H........ | S.L---........---..C | ........P. |
| iPS:43 5883 | 21-225_185A1 | | | | | | | |
| Germline | | H_FR1 EVQLLES GGGLVQPGGSLR LSCAASG-FTFS | H_CDR1 ----YAMS | H_FR2 WVRQAPGK GLEWVS | H_CDR2 AISGS- GGSTYYAD SVKG | H_FR3 RFTISRDNSKNTLYLQM NSLRAEDTAVYYCAR | H_CDR3 ----------DAFDI | H_FR4 WGQGTM VTVSS |
| iPS:43 5895 | VH3|3-23|D1|1-1|RF1/JH3 21-225_188E8 | ..............N......... | ....S..N | | ......Y......... | ..................F..................... | RN.DD....---...... | |
| Germline | | H_FR1 | H_CDR1 D----YMS | H_FR2 WVRQAPGK GLEWVS | H_CDR2 YISSS- GSTIYYAD SVKG | H_FR3 RFTISRDNAKNSLYLQM NSLRAEDTAVYYCAR | H_CDR3 NWGY----------FDY | H_FR4 WGQGTL VTVSS |
| | VH3|3-11|D7|7-27|RF3/JH4 | | | | | | | |
| iPS:43 5903 | 21-225_190E2 | ....................... | ........ | .....L......... | .T.VF........... | ....................................... | E.VG............A.... | ........ |
| iPS:43 5923 | VH3|3-11|D7|7-27|RF3/JH4 21-225_190H6 | ....................... | ........ | .....L......... | .T.VF........... | ....................................... | E.VG............A.... | ........ |
| iPS:43 5953 | VH3|3-11|D7|7-27|RF3/JH4 21-225_191B12 | ....................... | ........ | .....L......... | .T.VF........... | ....................................... | E.VG............A.... | ........ |
| iPS:43 6098 | VH3|3-11|D7|7-27|RF3/JH4 21-225_195G11 | ....................... | ........ | .....I......... | .I.M............ | ....................................... | E.VG............A.... | ........ |
| iPS:43 6102 | VH3|3-11|D7|7-27|RF3/JH4 21-225_196B1 | ....................... | ........ | .....L......... | .T.VF........... | ....................................... | E.VG............A.... | ........ |
| iPS:43 6104 | VH3|3-11|D7|7-27|RF3/JH4 21-225_196C1 | ....................... | ........ | .....L......... | .T.VF........... | ....................................... | E.VG............A.... | ........ |
| Germline | | H_FR1 EVQLLES GGGLVQPGGSLR LSCAASG-FTFS | H_CDR1 ----YAMS | H_FR2 WVRQAPGK GLEWVS | H_CDR2 AISGS- GGSTYYAD SVKG | H_FR3 RFTISRDNSKNTLYLQM NSLRAEDTAVYYCAR | H_CDR3 GIRVA----------GYFDY | H_FR4 WGQGTL VTVSS |
| | VH3|3-23|D6|6-19|RF2/JH4 | | | | | | | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 5965 | 21-225_192H2 | VH3J3-23/D6[6-19]RF2/JH4 | ........I......D..... | .........S...... | ................ | ...N.F.......... | ................................ | L...VG...... | ...... |
| iPS:43 6160 | 21-225_197C9 | VH3J3-23/D6[6-19]RF2/JH4 | ........A...........R | ................ | ................ | V...R........N.. | ................................ | .....G...SH... | ...... |
| iPS:39 2954 | 21-225_26A10 | VH3J3-23/D6[6-19]RF2/JH4 | ..................... | ................ | ................ | V....VN.F....... | .........................L...... | K....G...TH... | ...... |
| Germline | | H_FR1 | H_CDR1 | H_FR2 | H_CDR2 | H_FR3 | H_CDR3 | H_FR4 |
| VH4J4-30.1D5[5-24]RF3.JH4 | | QVQLQES-GPGLVKPSQTLS LTCTVSG GSIS | SG--YYWS | WIRQHPGK GLEWIG | YIYY SGSTYYNP SLKS | RVTISVDTSKNQFSLKL SSVTAADTAVYYCAR | AGYNWD -------------YFDY | WGQGTL VTVSS |
| iPS:43 5983 | 21-225_192E5 | VH4J4-30.1D5[5-24]RF3/J H4 | N........D..N | ................ | ................ | .F.............. | ...N.............F.............. | AGYNWD...NG.... | ...... |
| iPS:43 6043 | 21-225_193G9 | VH4J4-30.1D5[5-24]RF3/J H4 | N........D..N | ................ | ................ | .F.............. | ...N.............F.............. | AGYNWD...NG.... | ...... |
| iPS:43 6084 | 21-225_195F2 | VH4J4-30.1D5[5-24]RF3/J H4 | .........D...... | ................ | ................ | S...N........... | .........M...D.................. | GGYNWN...NG.... | ...A.. |
| iPS:43 7138 | 21-225_214D8 | VH4J4-30.1D5[5-24]RF3/J H4 | ..................... | TA..F........... | ................ | .F.............. | .........................N...... | AR..HY....SI.. | ...... |
| Germline | | H_FR1 | H_CDR1 | H_FR2 | H_CDR2 | H_FR3 | H_CDR3 | H_FR4 |
| VH3J3-23/D3[3-16]RF1/JH3 | | EVQLLES-GGGLVQPGGSLR LSCAASG-FTFS | S----YAMS | WVRQAPGK GLEWVS | AISGS GGSTYYAD SVKG | RFTISRDNSKNTLYLQM NSLRAEDTAVYYCAK | VLYLRGTL------SLYDAFDI | WGQGTM VTVSS |
| iPS:43 6003 | 21-225_192G10 | VH3J3-23/D3[3-16]RF1/JH3 | ...................S | ................ | ................ | ......R......... | ................................R | R.A.DG--- | ...... |
| | | H_FR1 | H_CDR1 | H_FR2 | H_CDR2 | H_FR3 | H_CDR3 | H_FR4 |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| | VH3|3-23|D7|7-27|RF2|JH4 | EVQLLES GGGLVQPGGSLR LSCAASG FTFS | S....YAMS | WVRQAPGK GLEWVS | AISG..SGGSTYYAD SVKG | RFTISRDNSKNTLYLQM NSLRAEDTAVYYCAR | *LGY----------FDY | WGQGT LVTVSS |
| iPS:43 6019 | 21- 225_193C4 | .............A.. | .......N.. | ........ | .I.N........R...... | ....................S...........F... | D..RYS.....YGF... | ........ |
| | Germline | H_FR1 | H_CDR1 | H_FR2 | H_CDR2 | H_FR3 | H_CDR3 | H_FR4 |
| | VH4|4-30.1|D1|1-1|RF1|JH6 | QVQLQES GPGLVKPSETLS LTCTVSG GSIS | SS..GYYWS | WIRQHPGK GLEWIG | YIY...SGSTYYNP SLKS | RVTISVDTSKNQFSLKL SSVTAADTAVYYCAR | GIIGTII YYYGMDV | WGQGT TVTVSS |
| iPS:43 6025 | 21- 225_193B5 | ................ | ........ | ........ | ........ | ..................A............... | .EYNWN-H.... | -------- |
| | Germline | H_FR1 | H_CDR1 | H_FR2 | H_CDR2 | H_FR3 | H_CDR3 | H_FR4 |
| | VH4|4-34|D4|4-11|RF2|JH4 | QVQLQQW GAGLLKPSETLS LTCAVYG GSFS | G....YYWS | WIRQPPGK GLEWIG | EINH..SGSTNYNPS LKS | RVTISVDTSKNQFSLKL SSVTAADTAVYYCAR | LYSRY-------YFDY | WGQGT LVTVSS |
| iPS:43 6033 | 21- 225_193E7 | ................ | .....F.T | ........ | ........ | ..................... | ..G----.-A.. | ..A..A |
| iPS:43 6199 | 21- 225_199E3 | ................ | .....F.T | ........ | ........ | ..................... | ..G----.-A.. | ........ |
| iPS:43 6228 | 21- 225_200F12 | ................ | .....F.T | ........ | ....S... | ................V... | ..G----.-A.. | ..A..A |
| iPS:43 6230 | 21- 225_201A1 | ................ | .....F.T | ........ | ....S...R | ......G.............. | ..G----.-A.. | ........ |
| iPS:43 6242 | 21- 225_201A10 | ................ | .....F.T | ........ | ....S... | .........N..........V.. | ..G----.-A.. | ........ |
| iPS:43 6286 | 21- 225_204H8 | ............F... | .....F.T | ....V... | ....S...S | ....................K.... | ..G----.-A.. | ........ |

Figure 52 (Continued)

Illegible table image.

| | | | | | | | | | |
|---|---|---|---|---|---|---|---|---|---|
| VH1\|1-08\|D2\|2-21\|RF1/JH5 | QVQLVQS GAEVKKPGASVK VSCKASG-YTFT | S YDIN | WVRQATGQ GLEWMG | WMNPN SGNTGYAQ KFQG | RVTMTRTS TSTAYME SSLRSEDTAVYYCAR | STLMWFL ---LRWWFDP | WGQGTT VTVSS |
| iPS:43 6114 | 21-225_196G8 | VH1\|1-08\|D2\|2-21\|RF1/JH5 | . . . . . . . . . . . . . . . . . . . . . . . . . . . . | N . . . . | M . . . . . . . . . | . .HL . . . . .P . . . . . . . | . . . . . . . . . .D . . . .F . . . . . . . . . . . . .Y | .GG.Y---------V. . . . | . . . . . . . . . . |
| iPS:43 6218 | 21-225_200G7 | VH1\|1-08\|D2\|2-21\|RF1/JH5 | . . . . . . . . . . . . . . . . . . . . . . . . . . . . | N . . . . | M . . . . . . . . . | . .HL . . . . .P . . . . . . . | . . . . . . . . . .D . . . .F . . . . . . . . . . . . .Y | .GG.Y---------V. . . . | . . . . . . . . . . |
| Germline | | H_FR1 | H_CDR1 | H_FR2 | H_CDR2 | H_FR3 | H_CDR3 | H_FR4 |
| VH1\|1-02\|D3\|3-10\|RF3/JH6 | QVQLVQS GAEVKKPGASVK VSCKASG-YTFT | G . . .YMH | WVRQAPGQ GLEWMG | WINPN SGGTNYAQ KFQG | RVTMTRDTS TSTAYME SSLRSEDTAVYYCAR | TYVRGVI YYYYGMDV | WGQGTT VTVSS |
| iPS:43 6116 | 21-225_196B9 | VH1\|1-02\|D3\|3-10\|RF3/JH6 | . . . . . . . . . . .M . . . . . . . . . . . . . . . . | . . . . | . . . . . . . . . | . . . . .F . . .R . . . . . | . . . . . . . . . . . . . . .S . . . . . . . . . . . . . . | GGVRGVPN-. . . . . .V. . . | . . . . . . . . . . |
| Germline | | H_FR1 | H_CDR1 | H_FR2 | H_CDR2 | H_FR3 | H_CDR3 | H_FR4 |
| VH4\|4-30.1\|D5\|5-18\|RF3/JH6 | QVQLQES GPGLVKPSGTLS LTCTVSG GSIS | SG---GYYWS | WIRQHPGK GLEWIG | YIYY SGSTYYNP SLKS | RVTISVDTSKNQFSLK LSSVTAADTAVYYCAR | GYSIGYII ---YYYGMDV | WGQGTT VTVSS |
| iPS:43 6181 | 21-225_198C2 | VH4\|4-30.1/D5\|5-18\|RF3/JH6 | . . . . . . . . . . . . . . . . . . . . . . . . . . . . | . . . . . . . . | . . . . . . . . . | N . . . . . . . . . . . . | . . . . . . . . . . . . . . . . . . . . . . . . . . | .DY.SGSY . . . . . . . . . .HN . . .L . . . | . . . . . . . . . . |
| iPS:43 6210 | 21-225_199G11 | VH4\|4-30.1/D5\|5-18\|RF3/JH6 | . . . . . . . . . . . . . . . . . . . . . . . . . . . . | . . . . . . . . | . . . . . . . . . | N . . . . . . . . . . . . | . . . . . . . . . . . . . . . . . . . . . . . . . . | .DY.SGSY . . . . . . . . . .HN . . .L . . . | . . . . . . . . . . |
| Germline | | H_FR1 | H_CDR1 | H_FR2 | H_CDR2 | H_FR3 | H_CDR3 | H_FR4 |
| VH1\|1-18\|D3\|3-3\|RF2/JH6 | QVQLVQS GAEVKKPGASVK VSCKASG-YTFT | S . . .YGIS | WVRQAPGQ GLEWMG | WISAY NGNTNYAQ KLQG | RVTMTTDTS TSTAYME LSSLRSDDTAVYYCAR | VYDEWSGLLT ---YYYGMDV | WGQGTT VTVSS |
| iPS:43 6234 | 21-225_51E3 | VH1\|1-18\|D3\|3-3\|RF2/JH6 | . . . . . . . . . . . . . . . . . . . . . . . . . N | . . . . | . . . .L . . . . | . . . KN . . .RF . . . | . . . . . . . . . . . . . . . . . . . . . . . . . . | HDEWSGY---. . . .K . . . | . . . . . . . . . . |
| iPS:43 6830 | 21-225_51F4 | VH1\|1-18\|D3\|3-3\|RF2/JH6 | . . . . . . . . . . . . . . . . . . . . . . . . . N | . . . . | . . . . . . . . . | . . .K . . . . . . . . | | HDEWSGY---. . . .K . . . | . . . . . . . . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6834 | 21-225_52F1 | VH1|1-18|D3|3-3|RF2|JH6 | ........N | .......V. | ........ | ....RK... | ........S. | HDFWSGY----- ...K.... | ....... |
| iPS:43 6842 | 21-225_54E9 | VH1|1-18|D3|3-3|RF2|JH6 | ........N | ........ | ...L.... | ....KN... | ........ | HDFWSGY----- ...K.... | ....... |
| iPS:43 6844 | 21-225_56G1 | VH1|1-18|D3|3-3|RF2|JH6 | ........N | ........ | ........ | ....K.... ..F... | ........ | HDFWSGY----- ...K.... | ....... |
| iPS:43 6846 | 21-225_56E3 | VH1|1-18|D3|3-3|RF2|JH6 | ........N | ......F. | ........ | ....KE... ..F... | ......A. | HDFWSGY----- ...K.... | ....... |
| iPS:45 1104 | 21-225_49C5 | VH1|1-18|D3|3-3|RF2|JH6 | ........N | ........ | ........ | ....K.... | ........ | HDFWSGY----- ...K.... | ....... |
| iPS:45 1106 | 21-225_49D10 | VH1|1-18|D3|3-3|RF2|JH6 | ........N | ........ | ...L.... ..F... | ....KN... | ........ | HDFWSGY----- ...K.... | ....... |
| iPS:45 1108 | 21-225_53E8 | VH1|1-18|D3|3-3|RF2|JH6 | ........N | ........ | ........ | ....KF... | ........ | HDFWSGY----- ...K.... | ....... |
| VH6|6-01|D3|3-9|RF1|JH6 | Germline | | QVQLQQS--GPGLVKPSQTLS LTCAISG--DSVS | SN----SAAWN | WIROSPSR RLYYR--GLEWLG | RTYYR SAYYNDYA VSVKS | RITINPDTSKNQFSLQL NSVTPEDTAVYYCAR | VLRYFDWLL*-- ---YYYYYGMDV | WGQGTT VTVSS |
| iPS:43 6236 | 21-225_201F7 | VH6|6-01|D3|3-9|RF1|JH6 | ........ | ........ | ........ | ....Y.E. | ........F. | DQ..Y------ ....... | ....... |
| iPS:43 6250 | 21-225_201A4 | VH6|6-01|D3|3-9|RF1|JH6 | ........ | ........ | ........ | ....Y.E. ..R. | ........F. | DQ..Y------ ....... | ....... |
| iPS:43 6252 | 21-225_202A8 | VH6|6-01|D3|3-9|RF1|JH6 | ........ | ........ | ........ | ....E... ..R. | ......L...T. | DQ..Y------ ....... | ....P. |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6278 | 21-225_201F2 | VH6|6-01/D3|3-9|RF1/JH6 | .................... | ........ | ........ | ........ | .....V.......... ....F.......... | DQ..Y----- ........... | ........ |
| iPS:43 6294 | 21-225_205G4 | VH6|6-01/D3|3-9|RF1/JH6 | .................... | ........ | ........ | ....Y.E. ..R..... | ................ ....F.......... | DQ..Y----- ........... | ........ |
| iPS:43 6356 | 21-225_210H10 | VH6|6-01/D3|3-9|RF1/JH6 | .................... | ........ | ........ | ....Y.P. ..R..... | ................L ................ | DQ..Y----- ........... | ........ |
| Germline | | H_FR1 | H_CDR1 | H_FR2 | H_CDR2 | H_FR3 | H_CDR3 | H_FR4 |
| VH1|1-02|D4|4-23|RF2/JH4 | | QVQLVQS GAEVKKPGASVK VSCKASG_YTFT | G____YMH | WVRQAPGQ GLEWMG | WINPN SGGTNYAQ KFQG | RVTMTRDTS ISTAYMEL SRLRSDDTAVYYCAR | DVGGN ----------SYFDY | WGQGTL VTVSS |
| iPS:43 6240 | 21-225_201E8 | VH1|1-02/D4|4-23|RF2/JH4 | ........ | ........ | ....D... ........ | ........ ........ | ....F..K | Q.Y.W. ......NS... | ........ |
| iPS:43 6314 | 21-225_206G4 | VH1|1-02/D4|4-23|RF2/JH4 | ........ | ....I... | ........ | ....D... ........ | ....I........... ....F..K | Q.Y.W. ......NS... | ........ |
| Germline | | H_FR1 | H_CDR1 | H_FR2 | H_CDR2 | H_FR3 | H_CDR3 | H_FR4 |
| VH1|1-02|D5|5-18|RF3/JH5 | | QVQLVQS GAEVKKPGASVK VSCKASG_YTFT | G____YMH | WVRQAPGQ GLEWMG | WINPN SGGTNYAQ KFQG | RVTMTRDTS ISTAYMEL SRLRSDDTAVYYCAR | CYSYGY ----NWFDP | WGQGTL VTVSS |
| iPS:43 6244 | 21-225_201H10 | VH1|1-02/D5|5-18|RF3/JH5 | ........ | ....I... | ....A... | ........ | ........T......T ................ | ........ | ........ |
| iPS:43 6262 | 21-225_203E3 | VH1|1-02/D5|5-18|RF3/JH5 | ........ | ....I... | ....A... | ........ | ................ ........T....... | ........ | ........ |
| iPS:43 6276 | 21-225_204H4 | VH1|1-02/D5|5-18|RF3/JH5 | ........ | ....I... | ....A... | ........ | ................ ........T....... | ........ | ........ |
| iPS:43 6312 | 21-225_206A4 | VH1|1-02/D5|5-18|RF3/JH5 | ........ | ........ | ....A... | ........ | ................ ........T....... | ........ | ........ |

Figure 52 (Continued)

| | | | | | | | |
|---|---|---|---|---|---|---|---|
| iPS:43 6316 | 21-225_206A5 | VH1j1-02/D5j5-18jRF3/JH5 | ........ | ..I..... | ....A... | ........ | .T...... | ........ |
| iPS:43 6338 | 21-225_208E8 | VH1j1-02/D5j5-18jRF3/JH5 | ........ | ..I..... | ....A... | ........ | .T...... | ........ |
| iPS:43 6344 | 21-225_208B11 | VH1j1-02/D5j5-18jRF3/JH5 | ........ | ..I..... | ....A... | ........ | .T...... | ........ |
| iPS:43 6358 | 21-225_210D11 | VH1j1-02/D5j5-18jRF3/JH5 | ........ | ..I..... | ....A... | ........ | .T...... | ........ |
| iPS:43 6408 | 21-225_214H8 | VH1j1-02/D5j5-18jRF3/JH5 | ........ | .H.I.... | ........ | .S...... | ....K... | DGR.S.G....YD.... |
| iPS:43 6424 | 21-225_215H6 | VH1j1-02/D5j5-18jRF3/JH5 | ........ | .H.I.... | ........ | .S..E... | ....K... | DGR.S.G....HD.... |
| iPS:43 7092 | 21-225_210B12 | VH1j1-02/D5j5-18jRF3/JH5 | D.....N. | ........ | ........ | ........ | ........ | .DS--.......A.... |
| iPS:43 7134 | 21-225_213A7 | VH1j1-02/D5j5-18jRF3/JH5 | D.....N. | ....I..R | ........ | ........ | .L.R..K. | .DS--.......A.... |
| iPS:43 7194 | 21-225_226B2 | VH1j1-02/D5j5-18jRF3/JH5 | ....F... | ........ | ........ | ..K..... | .L.N..I. | .TY..SGS...YF.EL.S |
| iPS:43 7196 | 21-225_226B7 | VH1j1-02/D5j5-18jRF3/JH5 | ....F... | ........ | ........ | ..D..... | ....H... | .Y...SGS....YY.....S |
| iPS:43 7200 | 21-225_226A10 | VH1j1-02/D5j5-18jRF3/JH5 | ........ | ........ | ........ | ..D..... | .L....I. | .TY..SGS...YF.EL.S |
| iPS:39 3168 | 21-225_32B11 | VH1j1-02/D5j5-18jRF3/JH5 | ........ | ........ | ......N. | ..D..... | ........ | .FY..SGS....YY.DL. |

| | | H_FR1 | H_CDR1 | H_FR2 | H_CDR2 | H_FR3 | H_CDR3 | H_FR4 |
|---|---|---|---|---|---|---|---|---|
| iPS:43 6968 | 21-225_190B10 | VH3J3-33|D7|7-27|RF2|J H6 | ........V........ | ......... | ......... | .N...........K..HV..... | ..........L.......... | D.DKRNFPY..........YY...... | ......... |
| iPS:43 7006 | 21-225_192G2 | VH3J3-33|D7|7-27|RF2|J H6 | ......... | ......... | ........T........ | .N........... | ..........L.......... | D.DKRNFPY..........YY...... | ......... |
| iPS:43 7024 | 21-225_194F11 | VH3J3-33|D7|7-27|RF2|J H6 | ......... | ......... | ......... | .N...........K..HV..... | ..........L.......... | D.DKRNFPY..........YY...... | ......... |
| iPS:43 7028 | 21-225_194G12 | VH3J3-33|D7|7-27|RF2|J H6 | ......... | ......... | ........T........ | .N........... | ..........L.......... | D.DKRNFPY..........YY...... | ......... |
| Germline VH4|4-34|D6|6-19|RF2|JH3 | | H_FR1 CVQLQW... QXLLKESGPGL VKPSQTLSLTC TVSGGSIS | H_CDR1 ......YYWS | H_FR2 WIRQPPGK GLEWIG | H_CDR2 YIYYSGSTNYNP SLKS | H_FR3 RVTISVDTSKNQFSLKL SSVTAADTAVYYCAR | H_CDR3 YYYDWLV......DAFDI | H_FR4 WGQGTM VTVSS |
| iPS:43 6290 | 21-225_205G3 | VH4|4-34|D6|6-19|RF3|J H3 | ..F........ | ....H..... | ......... | .MY........F..N...... | ...M........K........ | .G.......-.......... | ......... |
| Germline VH3|3-30.3|D4|4-17|RF2|JH1 | | H_FR1 CVQLVES GGGVVQPGRSLR LSCAASGFTFS | H_CDR1 S.....YAMH | H_FR2 WVRQAPGK GLEWVA | H_CDR2 VISYD GSNKYYAD SVKG | H_FR3 RFTISRDNSKNTLYLQ MNSLRAEDTAVYYCAR | H_CDR3 DYGDYA......EYFQH | H_FR4 WGQGTL VTVSS |
| iPS:43 6306 | 21-225_201H4 | VH3J3-30.3|D4|4-17|RF2|J H1 | ......... | ......... | ......L.. | A.W........N...... | ...M.......... | .V.TVG.........AT..DC | ...P..... |
| Germline VH1|1-18|D1|1-1|RF1|JH6 | | H_FR1 CVQLVQS GAEVKKPGASVK VSCKASGYTFT | H_CDR1 S.....IGIS | H_FR2 WVRQAPGQ GLEWMG | H_CDR2 WISAY NGNTNYAQ KLQG | H_FR3 RVTMTTDTSTSTAYMEL RSLRSEDTAVYYCAR | H_CDR3 GTTGTD......YYYGMDV | H_FR4 WGQGTT VTVSS |
| iPS:43 6362 | 21-225_210C12 | VH1|1-18|D1|1-1|RF1|JH 6 | ........T........ | N........ | ......... | .N.......H.F... | ......... | DP.V.H........... | ......... |
| iPS:43 6374 | 21-225_211C10 | VH1|1-18|D1|1-1|RF1|JH 6 | ......... | R......H. | ......L.. | .L......F... | .......G......... | DP.V.H........... | ......... |
| | | H_FR1 | H_CDR1 | H_FR2 | H_CDR2 | H_FR3 | H_CDR3 | H_FR4 |

Figure 52 (Continued)

| VH3[3-33]D5[5-18]RF3[J]H6 | | LCLIES TGGVYDFSSLS LCLASC-FTFS | VSH S | MYGIRM GLEWV | VSG CSKETAD SVKG | FTISRDNSKNTLQM NSLRAEDTAVYYCAR | GIYKY VYGMDV | WGQGTT VTVSS |
|---|---|---|---|---|---|---|---|---|
| iPS:43 6366 | 21-225_211A3 | VH3[3-33]D5[5-18]RF3[J]H6 | . . . . . . . . . . . . . . . . | . . . . . . | A . . . . . | . . . . . . N.E. . . . | . . . . . . . . . . . . | DG . . . . . . . . . . . . . . . . | . . . |
| iPS:43 6388 | 21-225_212H11 | VH3[3-33]D5[5-18]RF3[J]H6 | V . . . I . . . | . . . . . . | . . . . . . | . . . . . . | . . . . . . . . . . . . | D . . . . . . . . . . . . . — | . . . |
| iPS:43 6396 | 21-225_213E5 | VH3[3-33]D5[5-18]RF3[J]H6 | V . . . I . . . | . . . . . . | A . . . . . | . . . . . . N.E. . . . | . . . . . . . . . . . . | DG . . . . . . . . . . . . . . . . | . . . |
| iPS:43 6454 | 21-225_217B10 | VH3[3-33]D5[5-18]RF3[J]H6 | V . . . I . . . | . . . . . . | A . . . . . | . . . . . . N.E. . . . | . . . . . . . . . . . . | D . . . . . . . . . . . . . — | . . . |
| iPS:43 6668 | 21-225_147B9 | VH3[3-33]D5[5-18]RF3[J]H6 | . . . . . . . . | . . . . . . | . . . . . . | . . . . . . | . . . . . . . . . . . . | DRD . DPPY . . . . . . . . . | . . . |
| iPS:43 6688 | 21-225_148C8 | VH3[3-33]D5[5-18]RF3[J]H6 | . . . . . . . . | . . . . . . | . . . . . . | . . . . . . | . . . . . . . . . . . . | . . Y . . . . . . . . . . . . . | . . . |
| iPS:43 6706 | 21-225_149A11 | VH3[3-33]D5[5-18]RF3[J]H6 | . . . . . . . . | . . . . . . | . . . . . . | . . . . . . | . . . . . . . . . . . . | DRD . DPPY . . . . . . . . . | . . . |
| iPS:43 6760 | 21-225_155E10 | VH3[3-33]D5[5-18]RF3[J]H6 | . . . . . . . . | L . . . . | . . . . . . | . . . . . . | . . . . . . . . . . . . | . . Y . . . . . . . . . . . . . | . . . |
| iPS:43 6966 | 21-225_190C3 | VH3[3-33]D5[5-18]RF3[J]H6 | . . . . . . . . | L . . . . | . . . . . . | . . . . . . | . . . . . . . . . N . . | DRD . DPPY . . . . . . . . . | . . . |
| iPS:43 6976 | 21-225_190D8 | VH3[3-33]D5[5-18]RF3[J]H6 | . . D . . . E . | . . . . . . | . . . . . . | . . . . . . | . . . . . . . . . N . . | W . Y . Y — — — | . . . |
| iPS:43 7168 | 21-225_218G4 | VH3[3-33]D5[5-18]RF3[J]H6 | . . . . . . . . | . . . . . . | . . . . . . | . . . . . . | . . . V . . . . . N . . | W . Y . Y — — — | . . . |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3/3-33|D5|5-24|RF3/JH5 | | QVQLVES GGGVQPGGSLR LSCAASG-FTFS | S------YSMH | WVRQAPGK GLEWVA | VISYD GSNKYYAD SVKG | RFTISRDNSKNTLYLQM NSLRAEDTAVYYCAR | RDGYNY -------NWFDP | WGQGT VTVSS |
| iPS:43 6368 | VH3/3-33|D5|5-24|RF3/JH5 | ...... | N...... | ...... | ..H... | ...... | L.YS......G.... | ...... |
| iPS:43 6426 | VH3/3-33|D5|5-24|RF3/JH5 | ...... | Y...... | ...... | ..H... | ...... | L.YS......G.... | ...... |
| iPS:43 6432 | VH3/3-33|D5|5-24|RF3/JH5 | ...... | N...... | ...... | ..H... | ...... | L.YS......G.... | ...... |
| | Germline | H_FR1 | H_CDR1 | H_FR2 | H_CDR2 | H_FR3 | H_CDR3 | H_FR4 |
| VH1|1-18|D4|4-11|RF2/JH6 | | QVQLVQS GAEVKKPGASVK VSCKASG-YTFT | S------YGIS | WVRQAPGQ GLEWMG | WISAY NGNTNYAQ KLQG | RVTMTTDTSTSTAYMEL RSLRSDDTAVYYCAR | DFSNYYY-------YYGMDV | WGQGT VTVSS |
| iPS:43 6402 | VH1|1-18|D4|4-11|RF2/JH6 | ...... | .N..... | ...... | ..VH...D...F...... | ...... | ..YY---- | ......K |
| iPS:43 6500 | VH1|1-18|D4|4-11|RF2/JH6 | .....F. | ...... | ...... | ..V........ | ...... | ..YY---- -.F.. | ...... |
| iPS:43 6520 | VH1|1-18|D4|4-11|RF2/JH6 | .....F. | .N..... | ...... | ..V...S...... | ...... | ..YY---- ..... | ...... |
| | Germline | H_FR1 | H_CDR1 | H_FR2 | H_CDR2 | H_FR3 | H_CDR3 | H_FR4 |
| VH3/3-48|D2|2-21|RF1/JH4 | | EVQLVES GGGLVQPGGSLR LSCAASG-FTFS | S------YSMN | WVRQAPGK GLEWVS | YISSS-- SSTIYYAD SVKG | RFTISRDNAKNSLYLQM NSLRAEDTAVYYCAR | SLWW*L -LYFDY | WGQGT VTVSS |
| iPS:43 6436 | VH3/3-48|D2|2-21|RF1/JH4 | ......S.R | ...... | ...... | ..TG... | ...... | .G.A---- -VE.. | ...... |
| | Germline | H_FR1 | H_CDR1 | H_FR2 | H_CDR2 | H_FR3 | H_CDR3 | H_FR4 |
| VH3/3-48|D6|6-6|RF1/JH4 | | EVQLVES GGGLVQPGGSLR LSCAASG-FTFS | S------YSMN | WVRQAPGK GLEWVS | YISSS-- SSTIYYAD SVKG | RFTISRDNAKNSLYLQM NSLRAEDTAVYYCAR | EVSSS -SYFDY | WGQGT VTVSS |

Figure 52 (Continued)

Figure 52 (Continued)

| | | | | | | | | | |
|---|---|---|---|---|---|---|---|---|---|
| iPS:43 6558 | 21-225_224C11 | VH1|1-02|D4|4-23|RF2|J H6 | . . . . . | . . . . I . | . . . . . . . Y . . . . . . . | . . . R . F . . . . F . . . . | . W . . Y . S . . . . . . . |
| iPS:43 6562 | 21-225_224H11 | VH1|1-02|D4|4-23|RF2|J H6 | . . . . . | I . . . . . . . . . | . . . T . . . . . . . Y . D . . | . . . . . . F . . . . | . W . . Y . S . . . . . . . |
| iPS:43 6572 | 21-225_225G4 | VH1|1-02|D4|4-23|RF2|J H6 | . . . . . | I . . . . . | . . . . . . . . Y . D . . . | . . . R . F . . . . F . . . . | . W . . Y . S . . . . . . . |
| iPS:43 6606 | 21-225_226G8 | VH1|1-02|D4|4-23|RF2|J H6 | . . . . . | I . . . . . | . . . . . . . . Y . D . K . . | . . . . . . F . . . . | . W . . Y . S . . . . . . . |
| iPS:43 6610 | 21-225_226F9 | VH1|1-02|D4|4-23|RF2|J H6 | . . . . . | I . . . . . | . . . . . . . . Y . D . K . . | . . . A . . . . . F . . . . | . W . . Y . S . . . . . . . |
| iPS:43 6612 | 21-225_226H9 | VH1|1-02|D4|4-23|RF2|J H6 | . . . . . | I . . . . . | . . . . . . . . Y . D . . S . | . . . . . . L . . . . F . . . . | . W . . Y . S . . . . . . . |
| iPS:43 6614 | 21-225_226F10 | VH1|1-02|D4|4-23|RF2|J H6 | . . . . . L R . . . G . . . . | I . . . . . | . . . . . . . . Y . D . . . | . . . . . . . V . . . . F . . . . | . W . . Y . S . . . . . . P |
| iPS:43 6618 | 21-225_226E11 | VH1|1-02|D4|4-23|RF2|J H6 | . . . . . | I . . . . . | . . . . . . . . Y . D . . . | . . . . . . F . . . . | . W . . Y . S . . . . . . . |
| iPS:43 6624 | 21-225_226H12 | VH1|1-02|D4|4-23|RF2|J H6 | . . . . . | I . . . . . | . . . . . . . . Y . D . . . | . . . R . . . . . F . . . . | . W . . Y . S . . . . . . . |
| iPS:43 6626 | 21-225_227C1 | VH1|1-02|D4|4-23|RF2|J H6 | . . . . . | I . . . . . | . . . . . . . . Y . . . . . . | . . . . . . F . . . . | . W . . Y . S . . . . . . . |
| iPS:43 6628 | 21-225_227F2 | VH1|1-02|D4|4-23|RF2|J H6 | . . . H . . . . . | I . . . . . | . . . . . . . . Y . D . K . . | . . . . . . F . . . . | . W . . Y . S . . . . . . . |
| iPS:43 6640 | 21-225_227A8 | VH1|1-02|D4|4-23|RF2|J H6 | . . . . . | . . . . . . . . . . | . . . . . . . . Y . D . . . | . . . . . . . V . . . . F . . . . | . W . . Y . S . . . . . . . |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH4/4-39/D4/4-17/RF1/JH4 | | QLQLQES GPGLVKPSETLS LTCTVSG GSIS | SG SYYWG | WIRQHPG KGLEWIG | SIYY SGSTYYNP SLKS | RVTISVDTSKNQFSLKL SSVTAADTAVYYCAR | YYR*L VYFDY | WGQGTL VTVSS |
| iPS:43 6638 | 21-225_224C3 | ..S.......... | .R.... | ........ | .N.... | .................. | QG.DW...GV... | G..... |
| VH3/3-23/D4/4-11/RF2/JH5 | | EVQLLES GGGLVQPGGSLR LSCAASG FTFS | S.....YAMH | WVRQAPGK GLEWVS | LISGS GGSTYYAD SVKG | RFTISRDNSKNTLYLQM NSLRAEDTAVYYCAR | EYSNY RWFDP | WGQGTL VTVSS |
| iPS:43 6546 | 21-225_224D6 | ...V.......... | ........D.... | ........ | ..DN.F... | .................. | V.A.D....SH.... | ....... |
| VH1/1-46/D6/6-6/RF2/JH6 | | QVQLVQS GAEVKKPGASV KVSCKASG YTFT | S......YAMH | WVRQAPGQ GLEWMG | IINPS GGSTSYA QKFQG | RVTMTRDTSISTAYMEL SSLRSEDTAVYYCAR | STAARII YYYGMDV | WGQGTT VTVSS |
| iPS:43 6568 | 21-225_225B3 | .............. | ............ | ........ | ......A.. | .................. | DL...S.Y... .....F.... | .A. ..... |
| VH4/4-30.1/D4/4-17/RF2/JH6 | | QVQLQES GPGLVKPSQTLS LTCTVSG GSIS | SG CYYWG | WIRQPPG KGLEWIG | YIYY SGSTYYNP SLKS | RVTISVDTSKNQFSLKL SSVTAADTAVYYCAR | PYGDYYY YYYGMDV | WGQGTT VTVSS |
| iPS:43 6580 | 21-225_225E7 | ..........N... | | ........ | F..... | .................. | EA....G-- .......... | ....... |
| iPS:43 6926 | 21-225_78D10 VH4/4-30.1/D4/4-17/RF2/JH6 | ............. | | ........ | I..V... | .................. | AP.F---- ......... | ....... |
| VH3/3-33/D4/4-17/RF2/JH1 | | QVQLVES GGGVVQPGRSLR LSCAASG FTFS | S.....YAMH | WVRQAPGK GLEWVA | VIWYD GSNKYYA DSVKG | RFTISRDNSKNTLYLQM NSLRAEDTAVYYCAR | DYGDYA EYYDH | WGQGTT VTVSS |
| iPS:43 6592 | 21-225_226B1 | ..............T | | ........ | I..GY... | .............F.... | .HY.FW......SG.LT. | ....... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH3\|3-23\|D7\|7-27\|RF1/JH6 | | EVQLLES...GGLVQPGGSLR LSCAASG FTFS | S....YAMS | WVRQAPK GKGLEWVS | AISG...SGSTYYAD SVKG | RFTISRDNSKNTLYLQM NSLRAEDTAVYYCAR | IGVYY..-YYGMDV | WGQGT TVTVSS |
| iPS:43 6652 | 21- 225_146B11 | VH3\|3- 23\|D7\|7- 27\|RF1/J H6 | ................ ................ ................ | ........ | ........ | V...G... .S...... | ........................ ........................ | WR.NPT... ......D.. | .... .... |
| iPS:43 6654 | 21- 225_146C11 | VH3\|3- 23\|D7\|7- 27\|RF1/J H6 | ................ ................ .I.............. | ........ | ........ | V...G... .S...... | ........................ ........................ | WR.NPT... ......D.. | .... .... |
| iPS:43 6658 | 21- 225_146A2 | VH3\|3- 23\|D7\|7- 27\|RF1/J H6 | ................ ................ ................ | ........ | ........ | V...G... .S...... | ........................ ...............H........ | WR.NPT... ......D.. | .... .... |
| iPS:43 6664 | 21- 225_147E7 | VH3\|3- 23\|D7\|7- 27\|RF1/J H6 | ................ ................ ................ | ........ | ........ | V...G... .S...... | .....L.................. ........................F | WR.NPT... ......D.. | .... .... |
| iPS:43 6676 | 21- 225_147E11 | VH3\|3- 23\|D7\|7- 27\|RF1/J H6 | ................ ................ ................ | N.....V. | ........ | V...G... .S...... | ........................ ........................ | WR.NPT... ......D.. | .... .... |
| iPS:43 6678 | 21- 225_147B12 | VH3\|3- 23\|D7\|7- 27\|RF1/J H6 | ................ ................ ................ | ........ | ........ | V...G... .S...... | ........................ ....................M.H. | WR.NPT... ......D.. | .... .... |
| iPS:43 6686 | 21- 225_148G6 | VH3\|3- 23\|D7\|7- 27\|RF1/J H6 | ................ ................ ................ | ......P. | ........ | V...G... .S...... | ........................ ........................ | WR.NPT... ......D.. | .... .... |
| iPS:43 6694 | 21- 225_148G11 | VH3\|3- 23\|D7\|7- 27\|RF1/J H6 | ................ ................ ................ | .....H.. | ........ | V...G... .S.A.... | ........................ ........................ | WR.NPT... ......D.. | .... .... |
| iPS:43 6700 | 21- 225_149C7 | VH3\|3- 23\|D7\|7- 27\|RF1/J H6 | ................ ................ ................ | ........ | ........ | V...G... .S...... | ........................ ........................ | WR.NPT... ......D.. | .... .... |
| iPS:43 6704 | 21- 225_149C10 | VH3\|3- 23\|D7\|7- 27\|RF1/J H6 | ................ ................ ........F....... | ........ | ........ | V...G... .S...... | ........................ ........................ | WR.NPT... ......D.. | .... .... |

Figure 52 (Continued)

| | | | | | | |
|---|---|---|---|---|---|---|
| iPS:43 6710 | 21-225_150F6 | VH3j3-23jD7j7-27jRF1/J H6 | ... | ... V...G... .S... | ... | WR.NPT... .....D.... |
| iPS:43 6714 | 21-225_150H11 | VH3j3-23jD7j7-27jRF1/J H6 | ...I... | ... I...G... .S... | ... | WR.NPT... .....D.... |
| iPS:43 6718 | 21-225_151H5 | VH3j3-23jD7j7-27jRF1/J H6 | ... | ... V...G... .S... | ... | WR.NPT... .....D.... |
| iPS:43 6722 | 21-225_151H7 | VH3j3-23jD7j7-27jRF1/J H6 | ... | ... V...G... .S... | ... | WR.NPT... .....D.... |
| iPS:43 6724 | 21-225_151B9 | VH3j3-23jD7j7-27jRF1/J H6 | ... | ... V...G... .S... | ... | WR.NPT... .....D.... |
| iPS:43 6728 | 21-225_152G6 | VH3j3-23jD7j7-27jRF1/J H6 | ... | ... V...G... .S... | ... | WR.NPT... .....D.... |
| iPS:43 6730 | 21-225_152D7 | VH3j3-23jD7j7-27jRF1/J H6 | ... | ... V...G... .S... | ... | WR.NPT... .....DS... |
| iPS:43 6742 | 21-225_154C4 | VH3j3-23jD7j7-27jRF1/J H6 | ...I... | ... V...G... .S... | ... | WR.NPT... .....D.... |
| iPS:43 6746 | 21-225_154E10 | VH3j3-23jD7j7-27jRF1/J H6 | ... | ... V...G... .S... | ... | WR.NPT... .....D.... |
| iPS:43 6758 | 21-225_155C10 | VH3j3-23jD7j7-27jRF1/J H6 | ... | ... V...G... .S... | ... | WR.NPT... .....D.... |
| iPS:43 6938 | 21-225_146A3 | VH3j3-23jD7j7-27jRF1/J H6 | ... | ... V...G... .TT... | ... | WR.NPT... .....D.... |
| iPS:43 7250 | 21-225_148C6 | VH3j3-23jD7j7-27jRF1/J H6 | ... | ... V...G... .S... | ... | WR.NPT... .....D.... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43-7252 | 21-225_148H11 | VH3|3-23|D7|7-27|RF1/J H6 | ................ | ........ | ........ | V...G. .S. | ................ | WR.NPT........... | ........ |
| iPS:43-7282 | 21-225_207C9 | VH3|3-23|D7|7-27|RF1/J H6 | ................ | ........ | ........ | ........ | ................ | AG.TTGSY......... ....Y.N....... | ........ |
| | Germline | | H_FR1 | H_CDR1 | H_FR2 | H_CDR2 | H_FR3 | H_CDR3 | H_FR4 |
| | VH3|3-48|D4|4-11|RF2/JH6 | | EVQLVES GGLVQPGGSLR LSCAASG FTFS | S....YSMN | WVRQAPGK GLEWVS | SISSS SSYIYYAD SVKG | RFTISRDNAKNSLYLQM NSLRDEDTAVYYCAR | DPSNYYY--------YYYGMDV | WGQGTT VTVSS |
| iPS:43-6660 | 21-225_146D8 | VH3|3-48|D4|4-11|RF2/J H6 | ................ | N....... | ........ | ...R.... .N.K..V | ................ | .R.GS.GY......... ...F....L........ | ........ |
| iPS:43-6682 | 21-225_146A8 | VH3|3-48|D4|4-11|RF2/J H6 | ...K..... ..E.....V | N....... | ........ | ...R.... .N.K... ..R. | ................ | .R.GS.GY......... ...F....L........ | ........ |
| iPS:43-6684 | 21-225_146B6 | VH3|3-48|D4|4-11|RF2/J H6 | ................ | ........ | ........ | ...R.... .N.KH... | ........D....... | .R.GS.GY......... ...F....L........ | ........ |
| iPS:43-6696 | 21-225_149A1 | VH3|3-48|D4|4-11|RF2/J H6 | ................ | N....... | ........ | ...R.... .N.KH... | ................ | .R.GS.GY......... ...F....L........ | ........ |
| iPS:43-6712 | 21-225_150F9 | VH3|3-48|D4|4-11|RF2/J H6 | .M.............. | ........ | ....V... | ...R.... .N.K... | ................ | .R.GS.GY......... ...F....L........ | ........ |
| iPS:43-6762 | 21-225_156H2 | VH3|3-48|D4|4-11|RF2/J H6 | ...I............ | N....... | ........ | ...R.... .N.K... | ................ | .R.GS.GY......... ...F............. | ........ |
| iPS:43-6820 | 21-225_179D10 | VH3|3-48|D4|4-11|RF2/J H6 | .......F........ | ........ | ....A... | ...G..T. ...Q... | ................R | .SRKGF-.......... .......L........ | .....I.. |
| iPS:43-7262 | 21-225_170E4 | VH3|3-48|D4|4-11|RF2/J H6 | .......S........ | ........ | ........ | ...G..K. ...E... | ................R | .SRKGF-.......... .......L........ | ........ |
| | Germline | | H_FR1 | H_CDR1 | H_FR2 | H_CDR2 | H_FR3 | H_CDR3 | H_FR4 |

Figure 52 (Continued)

| | | QVQLVQSGA<br>GAEVKKPGASVK<br>VSCKASG-YTFT | S-----KDYH<br>..... | WVRQATGQ<br>GLEWMG | WMNPN<br>SGNTGYAQ<br>KFQG | RVTMTRNTSISTAYMEL<br>SSLRSEDTAVYYCAR | DIVATV<br>YYYGMDV | WGQGTT<br>VTVSS |
|---|---|---|---|---|---|---|---|---|
| | VH1\|1-<br>08/D5\|5-<br>12\|RF1/J<br>H6 | | | | | | A....LVPAAI<br>.PYN..FA... | ... |
| iPS:43<br>6662 | 21-<br>225_147D7 | | | | | R............... | | |
| | Germline | H_FR1 | H_CDR1 | H_FR2 | H_CDR2 | H_FR3 | H_CDR3 | H_FR4 |
| | | QVQLVQSGA<br>EVKKPGASVK<br>VSCKASG-YTFT | S-----YGMH | WVRQAPGK<br>GLEWVA | VIWYD<br>GSNKYYAD<br>SVKG | RFTISRDNSKNTLYLQM<br>NSLRAEDTAVYYCAR | VYYDWSGYYY<br>------YYYGMDV | WGQGTT<br>VTVSS |
| iPS:43<br>6666 | VH1\|1-<br>02/D3\|3-<br>3\|RF2/JH<br>6 | | D........L | | ..D........ | | DR.SG..S.P.<br>........... | ... |
| | Germline | H_FR1 | H_CDR1 | H_FR2 | H_CDR2 | H_FR3 | H_CDR3 | H_FR4 |
| | VH3\|3-<br>33/D3\|3-<br>3\|RF2/JH6 | | | | | | | |
| iPS:43<br>6672 | 21-<br>225_147F9 | | T......... | | ..G...<br>..D.D. | ...........I......... | DR.YC..GTC.<br>..P........ | ... |
| iPS:43<br>6674 | 21-<br>225_147G9 | | T......... | | ..G...<br>..D.D. | ...........I......... | DR.YC..GSC.<br>..P........ | ... |
| iPS:43<br>6690 | 21-<br>225_148A9 | | T......... | | ..G...<br>..D.D. | ...........I......... | DR.YC..GTC.<br>..P........ | ... |
| iPS:43<br>6708 | 21-<br>225_150D3 | | T......... | | ..G...<br>..D... | ...........I......... | DR.YC..GTC.<br>..P........ | ... |
| iPS:43<br>6716 | 21-<br>225_151F3 | | T......... | | ..G...<br>..TD.. | ...........I......... | DR.YC..TSC.<br>..P........ | ... |
| iPS:43<br>6738 | 21-<br>225_153D9 | | T......... | | ..G...<br>..D... | ...........I......... | DR.YC..GSC.<br>..P........ | ... |
| iPS:43<br>6740 | 21-<br>225_154C3 | .......V.. | T........T | | V..G..<br>.N.D.. | ...........I......... | DR.YC..GSC.<br>..P........ | ... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43_6748 | 21-225_154D11 | VH3\|3-33\|D3\|3-3\|RF2/JH6 | ................................ | I........ | ................ | ..........G......D... | ..................S........... | DR.YC..GSC........P............ | ........ |
| iPS:43_6764 | 21-225_158E9 | VH3\|3-33\|D3\|3-3\|RF2/JH6 | .......NV. | .......... | ................ | ................. | ................................ | DRV.C..TSC.......P............ | ........ |
| iPS:43_6774 | 21-225_161E10 | VH3\|3-33\|D3\|3-3\|RF2/JH6 | .......... | .......... | ................ | ...........S..... | ................................ | DR.YC..TSC.......P............ | ........ |
| iPS:43_6916 | 21-225_74A9 | VH3\|3-33\|D3\|3-3\|RF2/JH6 | .......... | .......... | ................ | ..........V...... | ...........I......F............ | DR.YC..TSC.......P............ | ........ |
| iPS:43_6940 | 21-225_146B8 | VH3\|3-33\|D3\|3-3\|RF2/JH6 | .......... | T......... | ................ | ...N..S.......... | ...........I................... | DR.YC..GSC.......P............ | ........ |
| iPS:43_7258 | 21-225_153F9 | VH3\|3-33\|D3\|3-3\|RF2/JH6 | .......... | T......... | ..............G. | ..V.G.ND.DF....T. | ...........I................... | DR.YC..GNC.......P............ | ........ |
| | | | | | | ...........G.DTD....R........... | | |
| Germline | | H_FR1 EVQLVES SGGLVKPGGSLR LSCAASG FTFS | H_CDR1 SG_____SYWS | H_FR2 WVRQAPGKG LEWVA | H_CDR2 NIKQD_____ GSEKYYVD SVKG | H_FR3 RFTISRDNAKNSLYLQM NSLRAEDTAVYYCAR | H_CDR3 MY.G............W.V.... | H_FR4 WGQGTLVTVSS |
| iPS:43_6680 | 21-225_147H12 | VH4\|4-30.1/D7\|7-27\|RF3/JH5 | ......N... | ........Y.H.. | ...............A | .................. | .....T.......................... | D..GYDS................SG..... | ........ |
| iPS:43_6750 | 21-225_154G12 | VH4\|4-30.1/D7\|7-27\|RF3/JH5 | ......N... | ........Y... | ..............G. | .................. | ......T......................... | D..GYDS................SG..... | ........ |
| Germline | | H_FR1 EVQLVES GGGLVQPGGSLR LSCAASG FTFS | H_CDR1 S_____YYMS | H_FR2 WIRQAPGKG LEWVA | H_CDR2 YISSSGSTIYYA DSVKG | H_FR3 RFTISRDNAKNSLYLQM NSLRAEDTAVYYCAR | H_CDR3 GSSSW_____WFDP | H_FR4 WGQGTLVTVSS |
| iPS:43_6698 | 21-225_149B5 | VH3\|3-07/D6\|6-13\|RF1/JH4 | .......... | G..........N | ................ | .................. | ................................ | MY.G............W.V.... | ........ |
| | | H_FR1 | H_CDR1 | H_FR2 | H_CDR2 | H_FR3 | H_CDR3 | H_FR4 |

Figure 52 (Continued)

| | | | H_CDR1 | H_FR2 | H_CDR2 | H_FR3 | H_CDR3 | H_FR4 |
|---|---|---|---|---|---|---|---|---|
| | VH3J3-21|D6|6-19|RF2|JH5 | | S.......YSMN | ......R..... | ......A...T.SS.SS......SSYIYYAD......SVKG | ...........RFTISRDNAKNSLYLQM NSLRAEDTAVYYCAR | STAVAGT-----UWFDP | WGQGT VTVSS |
| iPS:43 6702 | 21-225_149E8 | VH3J3-21|D6|6-19|RF2|JH5 | .............. | .............. | ...........G... | .............. | TAVAGT..........G... | .............. |
| | | Germline | H_FR1 | H_FR2 | H_CDR2 | H_FR3 | H_CDR3 | H_FR4 |
| | VH5|5-51|D3|3-22|RF2|JH6 | | S........YWIG | ...QPPG......GLEWMG | IIYPG---DSDTRYSP SFQG | QVTISADKSISTAYLQW SSLRASDTAMYYCAR | YYYDSSGYYY-------YYYYGMDV | WGQGT VTVSS |
| iPS:43 6752 | 21-225_155H1 | VH5|5-51|D3|3-22|RF2|JH6 | .............. | .............. | ..L......A........ | .............. | QAIA.R.R-- | .............. |
| | | Germline | H_FR1 | H_FR2 | H_CDR2 | H_FR3 | H_CDR3 | H_FR4 |
| | VH3J3-33|D6|6-19|RF1|JH4 | | S.........YAMH | ...QAPGK......GLEWVA | VIWY---GSNKYYAD SVKG | RFTISRDNSKNTLYLQM NSLRAEDTAVYYCAR | GYSSSW-------YFFDY | WGQGT VTVSS |
| iPS:43 6772 | 21-225_161H3 | VH3J3-33|D6|6-19|RF1|JH4 | .............. | .............. | .............. | .............. | VGY...G........W.I... | .............. |
| | | Germline | H_FR1 | H_FR2 | H_CDR2 | H_FR3 | H_CDR3 | H_FR4 |
| | VH4|4-30.1|D2|2-2|RF2|JH6 | | S........SGY-------GYVWS | ..IRQPPG......GLEWIG | YIYY---SGSTNNP STKS | RVTISVDTSKNQFSLKL SCVTAADTAVYYCAR | GYCSSTSCY-------YYYYGMDV | WGQGT VTVSS |
| iPS:43 6776 | 21-225_161F12 | VH4|4-30.1|D2|2-2|RF2|JH6 | .............. | .............. | ......P..... | ........I...I...N.. | SN...AN......VGF.....L... | ....R.. |
| iPS:43 6780 | 21-225_165H3 | VH4|4-30.1|D2|2-2|RF2|JH6 | .............. | .............. | ......P..... | ........I...I...N.. | SN...AN......VGF.. | .............. |
| | | Germline | H_FR1 | H_FR2 | H_CDR2 | H_FR3 | H_CDR3 | H_FR4 |
| | VH3J3-33|D5|5-24|RF3|JH6 | | S........YAMH | ...QAPGK......GLEWVA | VIWY---GSNKYYAD SVKG | RFTISRDNSKNTLYLQM NSLRAEDTAVYYCAR | RGCYYYY-------YYYGMDV | WGQGT VTVSS |
| iPS:43 6784 | 21-225_169C1 | VH3J3-33|D5|5-24|RF3|JH6 | .......N..... | .............. | .............. | ......T............ | DQYNRNDGPP......AYY....L... | .............. |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6786 | 21-225_169A6 | VH3/3-33/D5/5-24/RF3/JH6 | .................... | N..... | .................... | ............ | .................S........ | DQYNRNDGPP...AYY..... | .......... |
| iPS:43 6796 | 21-225_170A5 | VH3/3-33/D5/5-24/RF3/JH6 | ...........L........ | N.....C. | .................... | ....I....... | .................D........ | DQYNRNDGPP...AYY....L. | .......... |
| iPS:43 6812 | 21-225_175C6 | VH3/3-33/D5/5-24/RF3/JH6 | ...........L........ | N.....C. | .................... | ....I....... | .........V.......D........ | DQYNRNDGPP...AYY..... | .......... |
| Germline | | H_FR1 EVQLVES...GGGLVQPGGSLR LSCAASG-FTFS | H_CDR1 S------YSMN | H_FR2 WVRQAPGK GLEWVS | H_CDR2 SSS------SSYIYAD SVKG | H_FR3 RFTISRDNAKNSLYLQM NSLRAEDTAVYYCAR | H_CDR3 VDTAYYY------YYGMDV | H_FR4 WGQGT TVTVSS |
| iPS:43 6788 | 21-225_169B7 | VH3/3-48/D5/5-18/RF1/JH6 | .................... | .......L | .................... | ...G. G.I.F. | .................... | G...G.T-........ | .......... |
| iPS:43 6798 | 21-225_171F5 | VH3/3-48/D5/5-18/RF1/JH6 | .................... | .......L | .................... | ...G. G.I.F. | .................... | G...G.T-........ | .......... |
| iPS:43 6864 | 21-225_58G11 | VH3/3-48/D5/5-18/RF1/JH6 | .................... | ........ | .........I.......... | ....T. F..... | .................S........ | G......L-........ | .......... |
| iPS:43 6866 | 21-225_59F2 | VH3/3-48/D5/5-18/RF1/JH6 | ................G... | ........ | .................... | ...G. NI...T. | .................M........ | A..P..L-.......F. | .......... |
| iPS:43 6872 | 21-225_60D2 | VH3/3-48/D5/5-18/RF1/JH6 | ................G... | ........ | .................... | ....E. NI...T. | ..................G...... | A..P..L-.......F. | .......... |
| Germline | | H_FR1 QVQLVES...GGGVVQPGRSLR LSCAASG-FTFS | H_CDR1 S------YGMH | H_FR2 WVRQAPGK GLEWVA | H_CDR2 VIWYD GSNKYYAD SVKG | H_FR3 RFTISRDNSKNTLYLQM NSLRAEDTAVYYCAR | H_CDR3 VEMATYY------YYGMDV | H_FR4 WGQGT TVTVSS |
| iPS:43 6790 | 21-225_169G11 | VH3/3-33/D5/5-24/RF1/JH6 | .................... | ........ | .................... | ....I....... | .................G........ | EGATYYHGSGS .YYPAYN..... | .......... |
| | | H_FR1 | H_CDR1 | H_FR2 | H_CDR2 | H_FR3 | H_CDR3 | H_FR4 |

Figure 52 (Continued)

[Table content too dense and small to reliably transcribe]

Figure 52 (Continued)

| VH3/3-33/D1/1-1/RF3/JH6 | | LVQES GGVQESLR SCAASG.FTFS | S | YGMH WVRQAP GKGLEWV | AVIWYD GSNKYYA DSVKG | RFTISRDNSKNT LYLQMNSLRAEDTAVYYCAR | TRDDY VYCMDV | WGQGTT VTVSS |
|---|---|---|---|---|---|---|---|---|
| iPS:43 6818 | 21-225_179C7 | VH3/3-33/D1/1-1/RF3/JH6 | .A........ | N......S... | ....G... | I.Y..<br>.Y.N. | ......... | DRHY.FHVP<br>..YY | ..... |
| iPS:43 7094 | 21-225_210D12 | VH3/3-33/D1/1-1/RF3/JH6 | .......... | H........ | ........ | ....... | ......... | GD..P---<br>........ | ..... |
| iPS:43 7096 | 21-225_210E12 | VH3/3-33/D1/1-1/RF3/JH6 | ..H....... | N........ | ........ | ....... | ......... | GD..P---<br>E..L.. | ..I.. |
| iPS:43 7098 | 21-225_211C1 | VH3/3-33/D1/1-1/RF3/JH6 | .......... | H........ | ........ | ....... | T....I.. | GD..P---<br>E..L.. | ..... |
| iPS:43 7104 | 21-225_211G5 | VH3/3-33/D1/1-1/RF3/JH6 | .......... | H........ | ........ | ....... | ......... | GD..P---<br>E....... | ..... |
| iPS:43 7112 | 21-225_212C2 | VH3/3-33/D1/1-1/RF3/JH6 | .......... | H........ | ........ | ..C.... | ......... | GD..P---<br>E..L.. | ...S. |
| iPS:43 7114 | 21-225_212A4 | VH3/3-33/D1/1-1/RF3/JH6 | ..H...A... | N........ | ........ | ....... | ......... | GD..P---<br>E....... | ..I.. |
| iPS:43 7116 | 21-225_212F6 | VH3/3-33/D1/1-1/RF3/JH6 | .......... | H........ | ........ | ....... | ......T.. | GD..P---<br>E....... | ..... |
| iPS:43 7118 | 21-225_212G7 | VH3/3-33/D1/1-1/RF3/JH6 | .......... | H........ | ........ | ....... | ......... | GD..P---<br>E..L.. | ..... |
| iPS:43 7128 | 21-225_213G3 | VH3/3-33/D1/1-1/RF3/JH6 | .......... | H........ | ........ | ....... | ......H.. | GD..P---<br>E....... | ...S. |
| iPS:43 7130 | 21-225_213D5 | VH3/3-33/D1/1-1/RF3/JH6 | .......... | H........ | ........ | ....... | ...V..F.. | GD..P---<br>E....... | ..... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| | Germline | QVQLVES-GGGVVQPGRSLR LSCAASG-FTFS | S------YGMH | WVRQAPGK GLEWVA | VIWYD-GSNKYYAD SVKG | RFTISRDNSKNTLYLQM NSLRAEDTAVYYCAR | GD..P---GTGT-------IFDY | WGQGTL VTVSS |
| iPS:43 7146 | 21-225_215D3 | VH3\|3-33/D\|1-1\|RF3/JH 6 | T.............H........ | ..................... | ...........E.... | ................................ | GD..P---........E.... | ..... |
| iPS:43 7150 | 21-225_216A3 | VH3\|3-33/D\|1-1\|RF3/JH 6 | ...............H........ | ..................... | ................ | ................................ | GD..P---........E.L.. | ..... |
| iPS:43 7162 | 21-225_217B2 | VH3\|3-33/D\|1-1\|RF3/JH 6 | ..H.............N........ | ..................... | ................ | ................................ | GD..P---........E.... | ..... |
| iPS:43 7172 | 21-225_219A7 | VH3\|3-33/D\|1-1\|RF3/JH 6 | ......P.........H........ | ..................... | ................ | ...........M.................... | GD..P---........E.... | ..... |
| iPS:43 7182 | 21-225_221H2 | VH3\|3-33/D\|1-1\|RF3/JH 6 | .................H........ | ..................... | ................ | ...........H.................... | GD..P---........E.... | ..... |
| iPS:43 7184 | 21-225_221G4 | VH3\|3-33/D\|1-1\|RF3/JH 6 | .................N........ | ..................... | ................ | ...........H.................... | GD..P---........E....S | ..... |
| iPS:43 8664 | 21-225_216G1 | VH3\|3-33/D\|1-1\|RF3/JH 6 | ..H.............. | ..................... | ................ | ................................ | GD..P---........E.... | ....I |
| VH3\|3-33/D\|1-1\|RF1/JH4 | | QVQLVES-GGGVVQPGRSLR LSCAASG-FTES | S------YGMH | WVRQAPGK GLEWVA | VIWYD-GSNKYYAD SVKG | RFTISRDNSKNTLYLQM NSLRAEDTAVYYCAR | .GPFFST.........IFDV | WGQGTL VTVSS |
| iPS:43 6822 | 21-225_180D4 | VH3\|3-33/D\|1-1\|RF1/JH 4 | ..................N........ | .....F................ | ................ | ...........I.................F.. | .GPFFST.........VTM.. | ..... |
| iPS:43 6828 | 21-225_181H1 | VH3\|3-33/D\|1-1\|RF1/JH 4 | ..................N........ | ..................... | .....I....D..... | ...........I.................F.. | .GPFFST.........VTM.. | ..... |
| iPS:43 6950 | 21-225_184G4 | VH3\|3-33/D\|1-1\|RF1/JH 4 | V.................... | ..................... | .....I....D..... | ................................ | .GPFFST.........VTM.. | ..... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43_6952 | 21-225_185D2 | VH3J3-33/D1J1-11/RF1/JH4 | | | N....... | .....I..... ..T........ ...........F | .GPPFST..... .....VTM..... | ........ ........ |
| | Germline | | QITLKES--GPTLVKPICTLT LTCTFSG-FSLS | TS--GVGVG | WIRQPPGK ALEWLA | RLTITKDTSKNQVVLTM TNMDPVDTAIYYCAH | STARR DARDI | WGQGT VTVSS |
| iPS:43_6824 | 21-225_180C5 | VH2J2-05/D6J6-6/RF2/JH3 | | | | ........ ........S.. | KA..V..... | ........ ........ |
| iPS:43_6956 | 21-225_186H6 | VH2J2-05/D6J6-6/RF2/JH3 | | | ......G | ........ ........S.. | KA..V..... | ........ ........ |
| | Germline | | CVQLQES-GPGLVKPSGTLS LTCAVSG-GSVS | S----ISN | WIRQATGQ GLEWMG | RVTMRNLTSISTAYMEL SSLRSEDTAVYYCAR | CYSICYY VYYGMDV | WGQGT VTVSS |
| iPS:43_6826 | 21-225_180G5 | VH1J1-08/D5J5-18/RF3/JH6 | | | | | FY.YGSGSHV ..FYH.....L.. | ........ |
| | Germline | | CVQLQQS-GPGLVKPSQTLS LTCAISG-DSVS | SN---SAAWN | WIRQSPSR GLEWLG | RITINPDTSKNQFSLQL NSVTPEDTAVYYCAR | RGHSYY ....VYREDI | WGRGT VTVSS |
| iPS:43_6832 | 21-225_51D8 | VH6J6-01/D5J5-24/RF3/JH2 | | | | .....I ........D.... | DRYNWNY .....P..... | ........ ........ |
| | Germline | | CVQLVQS-GAEVKKPGASVK VSCKASG-YTFT | S----TYTH | WIRQAPGQ GLEWMG | RVTMTRDTSISTAYMEL SPLRSDDTAVYYCAR | RGHNY SWYDP | WGQGT VTVSS |
| iPS:43_6840 | 21-225_53E9 | VH1J1-02/D5J5-24/RF3/JH5 | | | | | DGYSSGW ........F.... | ........ |
| | Germline | | QITLKES-GPILVKPTCTLT LTCTFSG-FSLS | TSGVGVG | WIRQPPGK ALEWLA | RLTITKDTSKNQVVLTM TNMDPVDTAIYYCAH | LTCV EDY | WGQGT VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6848 | 21-225_57F1 | VH2|2-05/D7|7-27|RF1/JH4 | ........... | ........ | ....HE. | ....E...D | V..I....AAP. | .... |
| iPS:43 6852 | 21-225_57H11 | VH2|2-05/D7|7-27|RF1/JH4 | ........T | ........ | ....HE.R. | ....A...D | V..I....AAP. | .... |
| iPS:43 6870 | 21-225_60B1 | VH2|2-05/D7|7-27|RF1/JH4 | ........... | ........ | ....HE. | ....A...D | V.YI....AAP. | .... |
| iPS:43 6876 | 21-225_61F5 | VH2|2-05/D7|7-27|RF1/JH4 | ........... | .....L.. | ....HE..S | ....A...D | V..I....AAP. | .... |
| iPS:39 2593 | 21-225_3E10 | VH2|2-05/D7|7-27|RF1/JH4 | .....N.... | .G...... | .......H. | .H.A....D | IEV.....A... | .... |
| Germline | | | H_FR1 CQVQLVESG GGGVVQPGRSLR LSCAASG-FTFS | H_CDR1 S---YAMH | H_FR2 WVRQAPGK GLEWVA | H_CDR2 VISYD GSNKYYAD SVKG | H_FR3 RFTISRDNSKNTLYLQM NSLRAEDTAVYYCAR | H_CDR3 VVYGSSTTH YYYYGMDV | H_FR4 WGQGTT VTVSS |
| iPS:43 6854 | 21-225_58C1 | VH2|2-05/D6|6-6|RF2/JH1 | ........... | ........ | ........ | ....D....E. | L..V---.-A.DS | .... |
| iPS:43 6874 | 21-225_60A12 | VH2|2-05/D6|6-6|RF2/JH1 | ........T | .G...... | ........ | ....D....E. | L..V---.-A.DS | .... |
| iPS:43 6954 | 21-225_185G7 | VH2|2-05/D6|6-6|RF2/JH1 | ........... | ........ | .......E. | ....E... | I..V---.-A... | .... |
| iPS:39 3188 | 21-225_34B9 | VH2|2-05/D6|6-6|RF2/JH1 | .....R.... | ........ | ........ | ........ | L..V---.-T.DS | ...S |
| Germline | VH3|3-30.3|D3|3-10|RF2/JH6 | | H_FR1 CVQLVESG GGVVQPGRSLR SCAASG-FTFS | H_CDR1 S---YAMH | H_FR2 WVRQAPGK GLEWVA | H_CDR2 VISYD GSNKYYAD SVKG | H_FR3 RFTISRDNSKNTLYLQM NSLRAEDTAVYYCAR | H_CDR3 VVYGSSTTH YYYYGMDV | H_FR4 WGQGTT VTVSS |

Figure 52 (Continued)

| | | | | | | | | | |
|---|---|---|---|---|---|---|---|---|---|
| | | | F......G.. | | .S........ | T...... | .S........ | DD......P--- | ...... |
| | VH3|3-30.3/D3|3-10|RF2/JH6 | | | | .D...... | .M...... | L........ | ...... |
| iPS:43 6858 | 21-225_58E7 | Germline | H_CDR1 | H_FR2 | H_CDR2 | H_FR3 | H_CDR3 | H_FR4 |
| VH3|3-07|D5|5-12|RF3|JH6 | | EVQLVES- GGGLVQPGGSLR LSCAASG-FTFS | S------YAMS | WVRQAPGK GLEWVA | AISGSGGSTYYAD SVKG | RFTISRDNSKNTLYLQM NSLRAEDTAVYYCAR | CSSIDI- -----KFYGMDV | WGQGTT VTVSS |
| iPS:43 6860 | 21-225_58F7 | VH3|3-07|D5|5-12|RF3|JH6 | ........F.... | | | H..... | | .DIP.SSG. ------ | ...... |
| | | Germline | H_CDR1 | H_FR2 | H_CDR2 | H_FR3 | H_CDR3 | H_FR4 |
| VH3|3-30.3/D4|4-17|RF2/JH6 | | QVQLVES GGGVVQPGRSLR LSCAASG-FTFS | ----YAMH | WVRQAPGK GLEWVA | VISYDGSNK YYADSVKG | RFTISRDNSKNTLYLQM NSLRAEDTAVYYCAR | DVGGY- ----YYGMDV | WGQGTT VTVSS |
| iPS:43 6862 | 21-225_58F8 | VH3|3-30.3/D4|4-17|RF2/JH6 | ........G... | | | | .E.RG.GGYER. .GYYY......... | ...... |
| | | Germline | H_CDR1 | H_FR2 | H_CDR2 | H_FR3 | H_CDR3 | H_FR4 |
| VH3|3-33|D3|3-16|RF2|JH6 | | QVQLVES GGGVVQPGRSLR LSCAASG-FTFS | ----YGMH | WVRQAPGK GLEWVA | VISYDGSNK YYADSVKG | RFTISRDNSKNTLYLQM NSLRAEDTAVYYCAR | DRVNGXRY- ----YYGMDV | WGQGTT VTVSS |
| iPS:43 6868 | 21-225_59B11 | VH3|3-33|D3|3-16|RF2|JH6 | .......V... | | A..... | ........L..... | DR.CSS.SC- .........P. | ...... |
| | | Germline | H_CDR1 | H_FR2 | H_CDR2 | H_FR3 | H_CDR3 | H_FR4 |
| VH2|2-05|D1|1-1|RF1|JH3 | | QITLKES GPTLVKPTQTL TLTCTFSG-FSLS | TS GYGVG | WIROPPGK ALEWLA | LIY WDDKRYSP SLKS | RLTITKDTSKNQVVLTM TNMDPVDTATYYCAH | GTYSI- ----DAFDI | WGQGTM VTVSS |
| iPS:43 6878 | 21-225_62E3 | VH2|2-05|D1|1-1|RF1|JH3 | | | N..... | .F......R.....D. | KA.WV......... | ...... |
| iPS:43 6880 | 21-225_62E8 | VH2|2-05|D1|1-1|RF1|JH3 | | | N..... | .F......R.....D. | KA.WV......... | ...... |
| iPS:43 6882 | 21-225_62D10 | VH2|2-05|D1|1-1|RF1|JH3 | ......S... | | N..... | .F......R.....D. | KA.WV......... | ...... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 6884 | 21-225_62A12 | VH2[2-05/D1[1-1]RF1/JH3 | ........... | ........... | ........... | .....N....... | .F...R....D....... | K..WV........ | ........... |
| iPS:43 6886 | 21-225_62B12 | VH2[2-05/D1[1-1]RF1/JH3 | ..........N | ........... | ........... | .....N....... | .F...R....D...L... | KA.WV........ | ........... |
| iPS:43 6894 | 21-225_66G9 | VH2[2-05/D1[1-1]RF1/JH3 | ........... | ........... | ........... | .....N...F... | .F...R....D....... | KA.WV........ | ........... |
| iPS:43 6908 | 21-225_72D5 | VH2[2-05/D1[1-1]RF1/JH3 | ........... | ........... | ........... | .....N....... | .F...R.G.D....F... | KA.WV........ | ........... |
| iPS:43 6912 | 21-225_73C4 | VH2[2-05/D1[1-1]RF1/JH3 | ........... | ........... | ........... | .....N....... | .F...R....D....... | K..WV........ | ........... |
| | Germline | VH3[3-48[D4[4-11]RF2/JH3 | EVQLVES-GGGLVQPGGSLR LSCAASG.FTFS | .YSMN | WVRQAPGK.GLEWVS | SISSS-SSTIYYAD.SVKG | RFTISRDNAKNSLYLQM NSLRAEDTAVYYCAR | HRY.DSSG-YYIDSSY VYIDAFDI | WGQGTM VTVSS |
| iPS:43 6888 | 21-225_63G7 | VH3[3-48/D4[4-11]RF2/JH3 | ........... | ........... | ........... | .T.......A... | ........... | .HRY.DSSG....YYS.... | ........... |
| iPS:43 6890 | 21-225_63A10 | VH3[3-48/D4[4-11]RF2/JH3 | ........... | ........... | ........... | .T.......A... | ........... | .HRY.DSSG....YYS.... | ........... |
| | Germline | VH1[1-02/D3[3-22]RF2/JH3 | QVQLVQS-GAEVKKPGASVK VSCKASG-YTFT | G.YMH | WVRQAPGQ.GLEWMG | WINPN.SGGTNTAQ.KFQG | RVTMTRDTSISTAYMEL SRLRSDDTAVYYCAR | A..YG..S--YYIDAFDI | WGQGTM VTVSS |
| iPS:43 6892 | 21-225_65E9 | VH1[1-02/D3[3-22]RF2/JH3 | ........... | ........... | ........... | ........... | ........... | A..YG..S....NE..M | ........... |
| iPS:43 6900 | 21-225_69B9 | VH1[1-02/D3[3-22]RF2/JH3 | ..M.....D.. | .H.. | ........... | ........... | .....M..... | A..YG..S....NES.M | ........... |
| | | H_FR1 | H_CDR1 | H_FR2 | H_CDR2 | H_FR3 | H_CDR3 | H_FR4 |

| | | H_FR1 | H_CDR1 | H_FR2 | H_CDR2 | H_FR3 | H_CDR3 | H_FR4 |
|---|---|---|---|---|---|---|---|---|
| VH4|4-30.1|D2|2-8|RF3|JH4 | | QVQLQES GPGLVKPSQTLS LTCTVSG GSTS | SG GYYWS | WIRQHPGK GLEWIG | YIYY SGSTYYNPSLKS | RVTISVDTSKNQFSLKL SSVTAADTAVYYCAR | EIVLNYY SAYFDY | WGQGTL VTVSS |
| iPS:43 6958 | 21-225_190D1 | | | | | | SP.R--........-...-G. | |
| | Germline | H_FR1 | H_CDR1 | H_FR2 | H_CDR2 | H_FR3 | H_CDR3 | H_FR4 |
| VH6|6-01|D4|4-17|RF2|JH4 | | QVQLQQS GPGLVKPSCILS LTCAISG DSVS | SN SAAWN | WIRQSPSR GLEWLG | RTYY RSKWYNDYA VSVKS | RITINPDTSKNQFSLQL NSVTPEDTAVYYCAR | DYGLY YFDY | WGQGTL VTVSS |
| iPS:43 6962 | VH6|6-01|D4|4-17|RF2|JH4 | .................D | RK....T.. | ............ | ....K.................... | ............................ | P.G-.........L... | |
| iPS:43 6978 | VH6|6-01|D4|4-17|RF2|JH4 | ............... | RK....T.. | ............ | ............................ | ........I................... | P.G-.........L... | |
| iPS:43 7070 | VH6|6-01|D4|4-17|RF2|JH4 | ............... | RI...NPT.. | ............ | ....HV................ | ............................ | P.G-.........L... | |
| iPS:43 7076 | VH6|6-01|D4|4-17|RF2|JH4 | ............... | RT...NPT.. | ............ | ....HV..L............ | ........T................... | P.G-.........L... | |
| | Germline | H_FR1 | H_CDR1 | H_FR2 | H_CDR2 | H_FR3 | H_CDR3 | H_FR4 |
| VH3|3-33|D1|1-7|RF3|JH6 | | QVQLVES GGGVVQPGRSLR LSCAASG FTFS | S YGMH | VVRQAPGK GLEWVA | VIWYD GSNKYYAD SVKG | RFTISRDNSKNTLYLQM NSLRAEDTAVYYCAR | VMNYYY YYYGMDV | WGQGTT VTVSS |
| iPS:43 6964 | VH3|3-33|D1|1-7|RF3|JH6 | .........N.... | N.......I. | ............ | ......F.....D................ | ............................ | D.....GDH......Y..F. | |
| iPS:43 6970 | VH3|3-33|D1|1-7|RF3|JH6 | ............... | .......... | ............ | ......F.....T................ | ............................ | D.....GDY......Y.... | |
| iPS:43 6980 | VH3|3-33|D1|1-7|RF3|JH6 | ..........L..... | N.......... | ............ | .....FG....D...R........ | ......................F..... | D.....GDH......Y.... | |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43-6992 | 21-225_191B8 | VH3J3-33JD1J1-7JRF3/JH6 | ........L. | ......... | ......... | ....F.... | ......... | D...GDH.. ...Y..... | ......... |
| iPS:43-6994 | 21-225_191A9 | VH3J3-33JD1J1-7JRF3/JH6 | ........L. | N........ | ......... | ..FG..... ...D..... | ......F.. | D...GDH.. ...Y..... | ......... |
| | Germline | H_FR1 | H_CDR1 | H_FR2 | H_CDR2 | H_FR3 | H_CDR3 | H_FR4 |
| VH4J4-30.1JD4J4-11JRF2JH6 | | QVQLQES GGGLVKPSQTLS LTCTVSG-GSIS | SGGYYWS | WIRQHPGK GLEWIG | YIYY SGSTYYNP SLKS | RVTISVDTSKNQFSLKL SSVTAADTAVYYCAR | DYSRYY YYYGMDV | WGQGTT VTVSS |
| iPS:43-6984 | 21-225_190F10 | VH4J4-30.1JD4J4-11JRF2/JH6 | .........R | ......D.. | ....E.... | ...I..... | ......... | .S.SR---- | ......... |
| iPS:43-6988 | 21-225_191A2 | VH4J4-30.1JD4J4-11JRF2/JH6 | .......V. ........R | ......D.. | ....E.... | ...I..... | ......... | .S.SR---- | ......... |
| iPS:43-7014 | 21-225_192H8 | VH4J4-30.1JD4J4-11JRF2/JH6 | .....I... | ......D.. | ......... | ...P..... | .L.M.A... | .S.L.---- | ......... |
| iPS:43-7022 | 21-225_194G5 | VH4J4-30.1JD4J4-11JRF2/JH6 | .........R | ......D.. | ......... | ......... | ......... | .H.L.---- | ......... |
| iPS:43-7026 | 21-225_194D12 | VH4J4-30.1JD4J4-11JRF2/JH6 | ......... | ......D.. | ......... | ......... | ......... | .GARH---- | ......... |
| iPS:43-7056 | 21-225_198B8 | VH4J4-30.1JD4J4-11JRF2/JH6 | .........R | ......D.. | ....E.... | ...I..... | ......G.. | .S.SR---- | ......... |
| iPS:43-7124 | 21-225_212H12 | VH4J4-30.1JD4J4-11JRF2/JH6 | .........R | ......D.. | ......... | ......... | ......... | .S.S.---- | ......... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43_7136 | VH4|4-30.1/D4|4-11|RF2/J H6 Germline | ........ | ........D.... | ........ | ........ | ........G........ | .S.S.— ...... | ........ |
| VH4|4-59|D1|1-26|RF1/JH4 | | CVQLQES-CPGLVKPSETLS LICTVSG-GSIS | S——-—YWS | WIRQPPGK GLEWIG | YIYY-SGSTNYNP SLKS | RVTISVDTSKNQFSLKL SSVTAADDAVYYCAR | GTVGA-—————YFDI | WGQGTL VTVSS |
| iPS:43_6986 | VH4|4-59|D1|1-26|RF1/J H4 | ........R | ........i | ........ | .K...... | ........ | KG.T........IH.. | ........ |
| iPS:43_7064 | VH4|4-59|D1|1-26|RF1/J H4 | ........R | ........ | ........ | .K...... | ........ | KG.T........IH.. | ........ |
| | Germline | H_FR1 | H_CDR1 | H_FR2 | H_CDR2 | H_FR3 | H_CDR3 | H_FR4 |
| VH3|3-30|D6|6-6|RF1/JH4 | | CVQLVES-GGGVVQPGRSLR LSCAASG-FTFS | S————YGMH | WVRQAPGK GLEWVA | VISYD——GSNKYYAD SVKG | RFTISRDNSKNTLYLQM NSLRAEDTAVYYCAR | EISSS-—————STFDI | WGQGTL VTVSS |
| iPS:43_6996 | VH3|3-30|D6|6-6|RF1/JH 4 | ........ | F...H... | ........ | .W...... .K...... | ........H........ | .GY..GF......YRG..N | ........ |
| iPS:43_7054 | VH3|3-30|D6|6-6|RF1/JH 4 | ........ | F...H... | ........ | .W...... .K...... | ........H........ | .GF..GF......YRG..N | ........ |
| | Germline | H_FR1 | H_CDR1 | H_FR2 | H_CDR2 | H_FR3 | H_CDR3 | H_FR4 |
| VH3|3-33|D1|1-26|RF1/JH6 | | CVQLVES-GGGVVQPGRSLR LSCAASG-FTFS | S————YGMH | WVRQAPGK GLEWVA | VIWY-DGSNKYYAD SVKG | RFTISRDNSKNTLYLQM NSLRAEDTAVYYCAR | GIVGATYY-YYYGMDV | WGQGTL VTVSS |
| iPS:43_7000 | VH3|3-33/D1|1-26|RF1/J H6 | ........ | T....... | ........T | .L..F... | ........ | DR.G.SPP........YY | ........ |
| iPS:39_3192 | 21-225_12B1 VH3|3-33/D1|1-26|RF1/J H6 | ........ | ........ | ........ | ..N..... | ........ | DR.A.AGTP........Y | ........ |
| VH1|1-02|D3|3-10|RF2/JH5 | Germline | CVQLVQS-GAEVKKPGASVK VSCKASG-YTFT | G———YYMH | WVRQAPGQ GLEWMG | WINPN-SGGTNYAQ KFQG | RVTMTRDTSISTAYMEL SRLRSEDTAVYYCAR | YYYGSSY-————YNWFDP | WGQGTL VTVSS |
| | | H_FR1 | H_CDR1 | H_FR2 | H_CDR2 | H_FR3 | H_CDR3 | H_FR4 |

Figure 52 (Continued)

The content of this page is a complex sequence alignment table that is too low-resolution to transcribe accurately.

Figure 52 (Continued)

| | | | | H_CDR1 | H_FR2 | H_CDR2 | H_FR3 | H_CDR3 | H_FR4 |
|---|---|---|---|---|---|---|---|---|---|
| iPS:43-7030 | 21-225_195E3 | VH3|3-11/D3|3-9|RF1/JH4 | ......... | ......... | ......... | ......... | ...T.... N..... | DS...---  DW.... | ......... |
| | | Germline | H_FR1 QVQLQES.. GPGLVKPSETLS LTCTVSG.GSIS | H_CDR1 S...CYWS | H_FR2 WIRQPPGK GLEWIG | H_CDR2 SIYY. SGSTNYNP SLKS | H_FR3 RVTISIDTSKNQFSLKL SSVTAADTAVYYCAR | H_CDR3 WGQGT | H_FR4 WGQGT VTVSS |
| iPS:43-7032 | 21-225_195H6 | VH4|4-59/D7|7-27|RF3/JH1 | ............R | N......... | .........A.. | ...R..S.. | ...SM.......... | G..E-- ....LNN | ......... |
| | | Germline | H_FR1 QVQLQES.. GPGLVKPSETLS LTCTVSG.GSIS | H_CDR1 S...YYWS | H_FR2 WIRQPPGK GLEWIG | H_CDR2 YIYY. SGSTNYNP SLKS | H_FR3 RVTISIDTSKNQFSLKT SSVTAADTAVYYCAR | H_CDR3 RYSSSSY YYYGMDV | H_FR4 WGQGT VTVSS |
| iPS:43-7044 | 21-225_197F9 | VH4|4-59/D6|6-6|RF1/JH6 | ............R | I......... | ......... | ...V.T... | .........N.... | .RG..HRW ......GD.... | ..R...... |
| iPS:43-7060 | 21-225_199C3 | VH4|4-59/D6|6-6|RF1/JH6 | ............R | I......... | ......T.. | ...T.. | .........N....V.. | .RG..HRW ......GD.... | ..R...... |
| | | Germline | H_FR1 EVQLVES.. GGGVVQPGRSLR LSCAASGFTFS | H_CDR1 S...YGMH | H_FR2 WVRQAPGK GLEWVA | H_CDR2 VIS.. GSNKYYAD SVKG | H_FR3 RFTISRDNSKNTLYLQM NSLRAEDTAVYYCAR | H_CDR3 EYSSSS LRTGH | H_FR4 WGQGT VTVSS |
| iPS:43-7058 | 21-225_199F3 | VH3|3-30/D6|6-6|RF1/JH1 | ......... | F......... | ......... | ...W...S.. | ......... | .GY.GF.. ......YRG.AN | ......... |
| iPS:43-7062 | 21-225_200H1 | VH4|4-30.1/D6|6-6|RF2/JH6 | ......... | .....D... | ......... | ......... | ...N............ | DG..L-- ---- | ......... |
| | | Germline | H_FR1 QVQLQES.. GPGLVKPSGTLS LTCAVSG.GSIS | H_CDR1 S...CYWS | H_FR2 WIRQPPGK GLEWIG | H_CDR2 YIYY. SGSTYYNP SLKS | H_FR3 RVTISVDTSKNQFSLKLS SVTAADTAVYYCAR | H_CDR3 SRASSY YYYGMDV | H_FR4 WGQGT VTVSS |
| iPS:43-7066 | 21-225_200G9 | VH4|4-30.1/D6|6-6|RF2/JH6 | ......... | .....D... | ......... | ......... | ...N............ | DG..L-- ---- | ......... |

Figure 52 (Continued)

| | | Germline | H_FR1 | H_CDR1 | H_FR2 | H_CDR2 | H_FR3 | H_CDR3 | H_FR4 |
|---|---|---|---|---|---|---|---|---|---|
| iPS:43 7068 | 21-225_200A11 | VH4|4-30.1|D6|6-|RF2|JH6 | . . . | . . . | . . . | . . . D . . . | . . . | . . . R . . . | . . . | DA . . H--- . . . . . . | . . . |
| iPS:43 7140 | 21-225_214E12 | VH4|4-30.1|D6|6-|RF2|JH6 | . . . | . . . | . . . | . . . D . . . | . . . P . . . | . . . | DG . . E--- . . . . . . | . . . |
| iPS:43 7158 | 21-225_216H11 | VH4|4-30.1|D6|6-|RF2|JH6 | . . . | . . . | . . . | . . . D . . . | . . . P . . . | . . . | DG . . E--- . . L . . . | . . . |
| | | Germline | H_FR1 | H_CDR1 | H_FR2 | H_CDR2 | H_FR3 | H_CDR3 | H_FR4 |
| VH3|3-33|D1|1-26|RF3|JH3 | | | QVQLVES GGGLVKPGGSLR LSCAASG-FTFS | S----YSMH | WVRQAPGK GLEWVA | VISYDGSNK YYADSVKG | RFTISRDNSKNTLYLQM NSLRAEDTAVYYCAR | VSSNY-----DAFDI | WGQGTM VTVSS |
| iPS:43 7074 | 21-225_203B2 | VH3|3-33|D1|1-26|RF3|JH3 | . . . | N . . . | . . . | I . F . . . . . . | . . . MS . . . | E . . . . . | . . . |
| iPS:43 7082 | 21-225_205E12 | VH3|3-33|D1|1-26|RF3|JH3 | . . . | N . . . | . . . | I . F . . . E . . | . . . MS . . . | E . . . -LY . | . . . |
| | | Germline | H_FR1 | H_CDR1 | H_FR2 | H_CDR2 | H_FR3 | H_CDR3 | H_FR4 |
| VH3|3-48|D4|4-17|RF2|JH4 | | | EVQLVES GGGLVQPGGSLR LSCAASG-FTFS | S------YSMN | WVRQAPGK GLEWVS | SISSS--- SSIYYAD SVKG | RFTISRDNAKNSLYLQM NSLRAEDTAVYYCAR | DYGDY---- --YFDY | WGQGTL VTVSS |
| iPS:43 7086 | 21-225_209A8 | VH3|3-48|D4|4-17|RF2|JH4 | . . . . R | . . . | . . . L . . . | . . . IKK . . . | . . . V . . . | . . . D . S . . . | . . . |
| | | Germline | H_FR1 | H_CDR1 | H_FR2 | H_CDR2 | H_FR3 | H_CDR3 | H_FR4 |
| VH4|4-30.1|D2|2-8|RF3|JH6 | | | QVQLQES GPGLVKPSGTLS LTCTVSG-GSIS | SG---SYYWS | WIRQHPGK GLEWIG | YIYY-- SGSTYYNP SLKS | RVTISVDTSKNQFSLKL SSVTAADTAVYYCAR | DVILWVYAI ----YYYYGMDV | WGQGTT VTVSS |
| iPS:43 7090 | 21-225_210F11 | VH4|4-30.1|D2|2-8|RF3|JH6 | . . . | . . . S . . . | . . . | . . I . T . . . | . . . T . H . . . | EP . T---- . . . . . . | . . . |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 7106 | VH4\|4-30.1/D2\|2-8\|RF3/JH6 | ........... | ........... | ....T....V...... | ........... | ........... | .GP.S---- | ........... |
| | Germline VH3\|3-30.3/D4\|4-17\|RF2/JH5 | QVQLVES-GGGVVQPGRSLR LSCAASG-FTFS | S-----IAMH | WVRQAPGK GLEWVA | VISID--SSNKIYAD SVKG | RFTISRDNSKNTLYLQM NSLRAEDTAVYYCAR | DIGDY------SWELF | WGQGTL VTVSS |
| iPS:43 7100 | VH3\|3-30.3/D4\|4-17\|RF2/JH5 | ........... | ........... | ........... | .....M..... | .......A........ | ....P.S........G.... | ........... |
| | Germline VH3\|3-33/D5\|5-12\|RF3/JH6 | QVQLVES-GGGVVQPGRSLR LSCAASG-FTFS | S-----YGMH | WVRQAPGK GLEWVA | VIWYD--GSNKYYAD SVKG | RFTISRDNSKNTLYLQM NSLRAEDTAVYYCAR | GYSGYDYY-----YYYGMDV | WGQGTT VTVSS |
| iPS:43 7102 | VH3\|3-33/D5\|5-12\|RF3/JH6 | ............R | N........... | .....S..... | .I..F.....DQ... | ........... | .L.V.Y--- | ........... |
| iPS:43 7164 | VH3\|3-33/D5\|5-12\|RF3/JH6 | ........... | N........... | .....M..... | .I..F.....DE... | ........M....... | ....G...... | ........... |
| iPS:43 7166 | VH3\|3-33/D5\|5-12\|RF3/JH6 | ............R | N........... | .....S..... | .I..F.....DQ... | ........... | .L.V.Y--- | ........... |
| iPS:43 7170 | VH3\|3-33/D5\|5-12\|RF3/JH6 | ........... | N........... | .....M..... | .I..F.....DE... | ........... | .L.V.Y--- | ........... |
| | Germline VH4\|4-30.1/D6\|6-19\|RF2/JH6 | QVQLQES-GPGLVKPSQTLS LTCTVSG-GSIS | SG---GYYWS | WIRQHPGK GLEWIG | YIYY--SGSTYYNP SLKS | RVTISVDTSKNQFSLKL SSVTAADTAVYYCAR | GIAVAGYY-----YYYGMDV | WGQGTT VTVSS |
| iPS:43 7108 | VH4\|4-30.1/D6\|6-19\|RF2/JH6 | ........... | ......D.... | ........... | ........... | ........LL.....V. | DS...Y---N.... | ........... |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:43 21-225_211E9 | VH4|4-30.1/D6|6-19|RF2|JH6 | | | | ....T..N.... | ....I........ | DS..Y---- | |
| iPS:43 21-225_212A9 | VH4|4-30.1/D6|6-19|RF2|JH6 | ........S ........R | | | ....M........ | ....V........ | DS..Y---- | |
| iPS:43 21-225_213F5 | VH4|4-30.1/D6|6-19|RF2|JH6 | ........R | ....D.... | | | ....L....V.... | DS..Y---- N... | |
| iPS:43 21-225_215A3 | VH4|4-30.1/D6|6-19|RF2|JH6 | | ....D.... | | ....T..N.... | ....I........V.... | DS..Y---- | |
| iPS:43 21-225_215H3 | VH4|4-30.1/D6|6-19|RF2|JH6 | ........S ........R | ....D.... | | ....M........ | ....V........ | DS..Y---- | |
| iPS:43 21-225_216A7 | VH4|4-30.1/D6|6-19|RF2|JH6 | ........S ........R | ....D.... | | ....M........ | ....V........ | DS..Y---- | |
| VH3|3-30.3/D7|7-27|RF2|JH4 | Germline | CVQLQES-GPGLVKPSQTLS LTCAISG-DSVS | SNN---SAIHN | WFGQAPGK GLEWLG | RTIYR-GSNKYYAD SVKG | RITIRDTSKNQFSLQL NSLRAEDTAVYYCAR | AKGSDG ------FDY | WGQG TLVTVSS |
| iPS:43 21-225_216B12 | VH3|3-30.3/D7|7-27|RF2|JH4 | | | ........W | | ........V........ | D..LG......YF... | |
| VH6|6-01/D2|2-21|RF2|JH5 | Germline | QVQLQES-CPGLVKPSQTLS LTCAISS-DSVS ........D | SNN---SAIHN | WFGQAPGK GLEWLG | RTIYR-SKWYNDYA VSVKS | RITIRDTSKNQFSLQL DSVTPEDTAVYYCAR ........V........ | AKGSDG------TSNWFDP | WGQG TLVTVSS |
| iPS:43 21-225_224H2 | VH6|6-01/D2|2-21|RF2|JH5 | | | | | ........V........ | EGGL.Y.SST... ...SC.GG.... | |

Figure 52 (Continued)

| | Germline | H_FR1 | H_CDR1 | H_FR2 | H_CDR2 | H_FR3 | H_CDR3 | H_FR4 |
|---|---|---|---|---|---|---|---|---|
| VH1\|1-02\|D4\|4-17\|RF2\|JH6 | | QVQLVQS GAEVKKPGASVK VSCKASG-YTFT | G YYMH | WVRQAPGQ GLEWMG | WINPN SGGTNYAQ KFQG | RVTITRDTSISTAYMEL SSLRSEDTAVYYCAR | GAF.F.DYSDYYY YYYGMDV | WGQGT TVTSS |
| iPS:43 21-225_224B11 | VH1\|1-02\|D4\|4-17\|RF2\|JH6 | .......H........ ................ ............... | .I.. | ........ ....... | .K..... N...... .... | ..............A..T. ................ | GAF.F..........A... ............ | .H. ... |
| iPS:43 21-225_226F8 | VH1\|1-02\|D4\|4-17\|RF2\|JH6 | ................ ................ ............... | .I.. | ........ ....... | ........ ....... .... | ................... ................ | GAF...........AL... ............ | ... ... |
| iPS:43 21-225_227D3 | VH1\|1-02\|D4\|4-17\|RF2\|JH6 | ................ ................ ............... | .... | ........ ...R... | .K..... .F...... .... | ................... ................ | GAF.F.............. ............ | ... ... |
| iPS:43 21-225_227C10 | VH1\|1-02\|D4\|4-17\|RF2\|JH6 | ................ ................ ............... | .... | ........ ...R... | .K..... ....... .... | ................... ................ | GAF.F.............. ............ | ... ... |
| VH3\|3-33\|D2\|2-21\|RF2\|JH6 | | EVQLLES GGGLVQPGGSLR LSCAASG-FTFS | S YGMH | WVRQAPGK GLEWVA | VIWYD GSNKYYAD SVKG | RFTISRDNSKNTLYLQM NSLRAEDTAVYYCAR | GYCSSTSCYT.......... YYYYYGMDV | WGQGT TVTSS |
| iPS:43 21-225_225E9 | VH3\|3-33\|D2\|2-21\|RF2\|JH 6 | ................ ................E ......I........ | .... | ........ ....... | ...M... .G.D... .... | ................... ................ | DREYC.TSC.......... ..P......... | ... ... |
| VH3\|3-23\|D2\|2-21\|RF2\|JH6 | | EVQLLES GGGLVQPGGSLR LSCAASG-FTFS | S YAMS | WVRQAPGK GLEWVS | AISGS GGSTYYAD SVKG | RFTISRDNSKNTLYLQM NSLRAEDTAVYYCAR | AYCGGDCYS........... VYYYYGMDV | WGQGT TVTSS |
| iPS:43 21-225_227E5 | VH3\|3-23\|D2\|2-21\|RF2\|JH6 | ................ ...............E ............... | .... | ........ ....... | ........ ....... .... | ...............C... ................ | ..E............P... ............ | ... ... |
| iPS:39 21-225_16G8 3196 | VH3\|3-23\|D2\|2-21\|RF2\|JH6 | ................ ...............E ............... | .... | ........ ....... | ...G... ....... .... | ..............C.H.. ................ | ..E............P... ............ | ... ... |
| iPS:39 21-225_6B4 3202 | VH3\|3-23\|D2\|2-21\|RF2\|JH6 | ................ ...............E ............... | .... | ........ ....... | ...S... ....... .... | ...............C... ................ | ..E............P... ............ | ... ... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 3345 | VH3\|3-23\|D2\|2-21\|RF2\|JH6 | .........E...... | ................ | ................ | ................ | ................C... | ....E........P.. | ................ |
| | Germline VH2\|2-05\|D6\|6-13\|RF3\|JH4 | QITLKES GPGILKPTQTLT LTCTFSG FSLS | TS GVSVG | MTRQFPGK ALWLA | SISSS NDEDKYSP SVKG | RLTIKDTSKQYVLTM TNMDPVDTATYYCAR | WGQL VFDY | WGQGT VTVSS |
| iPS:43 7210 | 21-225_227E12 | ................ | ................ | ...C.S.......... | .........V...... | ................Y.......... | RG............-AL.. | ................ |
| iPS:39 2587 | 21-225_18G5 VH2\|2-05\|D6\|6-13\|RF3\|JH4 | ................ | ................ | ...C.S.......... | .........V...... | ................Y.......... | RG............-AL.. | ................ |
| iPS:39 8504 | 21-225_23D7 VH2\|2-05\|D6\|6-13\|RF3\|JH4 | ................ | ................ | ...C.S.......... | .N.V............ | S...............Y.......... | RG............-AL.. | ................ |
| | Germline VH3\|3-21\|D4\|4-11\|RF2\|JH6 | EVQLVES-- GGG.VKPGGSLR LSCAASG.FTFS | S----YSMN | WVRQAPGK GLEWVS | SISSS-- SSIYYAD SVKG | RFTISRDNAKNSLYLQM NSLRAEDTAVYYCAR | DYSNYY- YYYGMDV | WGQGT VTVSS |
| iPS:43 7226 | 21-225_57C2 VH3\|3-21\|D4\|4-11\|RF2\|JH6 | ................ | ......FG.. | ................ | ....TG...N....... | ................ | T..G----SL.. | ................ |
| | Germline VH3\|3-21\|D5\|5-18\|RF3\|JH5 | EVQLVES-- GGG.VKPGGSLR LCAASG.FTFS | S----YSMN | WVRQAPGK GLEWVS | SISSS-- SSIYYAD SVKG | RFTISRDNAKNSLYLQM NSLRAEDTAVYYCAR | GYSYGY- NWFDP | H_FR4 |
| iPS:43 7230 | 21-225_62H10 VH3\|3-21\|D5\|5-18\|RF3\|JH5 | ................ | ................ | ................ | .........G...... | ................ | .G.R---.G... | ................ |
| iPS:44 8906 | 21-225_72G9 VH3\|3-21\|D5\|5-18\|RF3\|JH5 | ................ | ................ | ................ | ................ | .........F...... | .G.R---.G... | ................ |
| | Germline VH1\|1-02\|D1\|1-26\|RF1\|JH4 | QVQLVQS- GAEVKPGASVK VSCKASG.YTFT | G----YYMH | WVRQAPGQ GLEWMG | WINPN-- SGSTNYAQ KFQG | RVTMTRDTSISTAYMEL SRLRSDDTAVYYCAR | GVGA- YFDY | WGQGT VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:43 7260 | VH1|1-02|D1|1-26|RF1/J H4 | | | | ....K.K.....C.... | .........T........ | .GATVTT..... .......WGV... | |
| | Germline | QVQLVES— GGGVQPGRSLR LSCAASG-FTFS | S------YGMH | MVRQAPGK GLEWVA | VIWYD— GSNKYYAD SVKG | RFTISRDNSKNTLYLQM NSLRAEDTAVYYCAR | AVGGDVGS VTYYGMDV | WGQGTT VTVSS |
| iPS:43 7268 | VH3|3-33|D2|2-21|RF2/J H6 | | .........D....... | | ..I..F..... | | ...HLH...FP...... | |
| | Germline | QVQLQES— GPGLVKPSQTLS LTCTVSG-GSIS | SGT------GYYWS | WIRQHPGK GLEWIG | YIY— SGSTYYNP SLKS | RVTISVDTSKNQFSLKL SSVTAADTAVYYCAR | DVGDY ---------VFDY | WGQGTL VTVSS |
| iPS:43 7294 | VH4|4-30.1|D4|4-17|RF2/J H4 | | | | ...........N..... | ...........F..... | ...SP.R......G.... | |
| | Germline | QVQLVES— GGGVQPGRSLR LSCAASG-FTFS | S------YAMH | WVRQAPGK GLEWVA | VISYD— GSNKYYAD SVKG | RFTISRDNSKNTLYLQM NSLRAEDTAVYYCAR | RGGNYYY FDGMDV | WGQGTT VTVSS |
| iPS:43 7302 | VH3|3-30.3|D5|5-24|RF3/J H6 | | ...........G... | ..........T...... | ......I....S..... | | .GYSYG------ .........G..... | |
| iPS:45 1102 | VH3|3-30.3|D5|5-24|RF3/J H6 | | Y........GL. | | | ...........F..... | E.R.CSGTSC..... ..PYY.......... | |
| iPS:39 2868 | VH3|3-30.3|D5|5-24|RF3/J H6 | | ...........G... | ...........V..... | ......I..A...S... | ............V.... | .GYSYG------ .........G..... | |
| iPS:39 3910 | VH3|3-30.3|D5|5-24|RF3/J H6 | | ...........G... | ...........S..... | ......G....N..... | ............V.... | .GYSYG------ .........G..... | ....A... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 4000 | 21-225_11A2 | VH3\|3-30.3/D5\|5-24\|RF3/J H6 | ........G... | ................ | .....G... ..DS... | ...I............ | .GYSYG---G...... | ........ |
| iPS:39 4004 | 21-225_13A1 | VH3\|3-30.3/D5\|5-24\|RF3/J H6 | ........G... | ................ | ......A... .T.Q... | ............V... | .GYSYG---G...... | ........ |
| iPS:39 4006 | 21-225_15C2 | VH3\|3-30.3/D5\|5-24\|RF3/J H6 | ........G... | ...............S | ...I....G... .R.NH... | ............V... | .GYSYG---G...... | ........ |
| iPS:39 4029 | 21-225_1B12 | VH3\|3-30.3/D5\|5-24\|RF3/J H6 | ........G... | ................ | ...I....A... .......S... | ........M... .......V... | .GYSYG---G...... | ....A... |
| iPS:39 4047 | 21-225_5E6 | VH3\|3-30.3/D5\|5-24\|RF3/J H6 | ........G... | ................ | ...I...V... ........N... | ................V... | .GYSYG---G...... | ........ |
| iPS:39 4081 | 21-225_16B3 | VH3\|3-30.3/D5\|5-24\|RF3/J H6 | ..........V | ................ | ......A... .I....S... | ........N... .......V... | .GYSYG---G...... | ....A... |
| VH4\|4-61\|D3\|3-9\|RF1\|JH4 | | Germline | H_FR1 | H_CDR1 | H_FR2 | H_CDR2 | H_FR3 | H_CDR3 | H_FR4 |
| iPS:45 1118 | 21-225_191C8 | VH4\|4-61/D3\|3-9\|RF1/JH 4 | ...........S...... | ........G....... | ................ | ....T.T...... | ................T....V...... | DTFC..G.... ......CGYF...S | ........ |
| VH2\|2-05\|D4\|4-11\|RF3\|JH4 | | Germline | H_FR1 | H_CDR1 | H_FR2 | H_CDR2 | H_FR3 | H_CDR3 | H_FR4 |
| iPS:39 2573 | 21-225_15G2 | VH2\|2-05/D4\|4-11\|RF3/J H4 | ................ | ................ | ................ | ................ | ................D...... | G..SC... ......C..H. | ........ |

Figure 52 (Continued)

| | | | H_CDR1 | H_FR2 | H_CDR2 | H_FR3 | H_CDR3 | |
|---|---|---|---|---|---|---|---|---|
| | VH1\|1-02\|D2\|2-2\|RF2\|JH6 | QVQLVQS GAEVKKPGASVK VSCKASG.YTFT | .....G.....S MH | WVRQAPGQ GLEWMG | WINPN SGGTNYAQ KFQG | RVTMTRDTSISTAYMEL SSLRSEDTAVYYCAR | DYCSSTSCYY -----YYYYGMDV | WGQGTT VTVSS |
| iPS:39 2585 | 21-225_14H11 | .....Q G........ | ....H.C | | | .....A | ....S..L.. ...QPG..... | .... |
| iPS:39 3186 | 21-225_27D9 | .......... .......... | .......... | | ....K.. | .....N........ | ER..T....L.. ..GITG..... | .... |
| iPS:39 3234 | 21-225_26C10 | .......... .......... | ....V. | | | ............ | ER..T....L.. ..GITG..... | .... |
| Germline | | H_FR1 | H_CDR1 | H_FR2 | H_CDR2 | H_FR3 | H_CDR3 | H_FR4 |
| | VH3\|3-23\|D5\|5-12\|RF3\|JH6 | EVQLLES GGGLVQPGGSLR LSCAASG.FTFS | .....S YAMS | WVRQAPGK GLEWVS | AISGS GGSTYYAD SVKG | FTISRDNSKNTLYLQM NSLRAEDTAVYYCAK | DYSGSYDYY YYYYGMDV | WGQGTT VTVSS |
| iPS:39 2596 | 21-225_12D8 | .......... .......... | ....V. | | ..T..VG... | ........T... | WGR..S..E.. ---........ | .... |
| iPS:39 2942 | 21-225_30E9 | ....V..... .......... | ...C..N | | ..R.... ..... | ............ | .ELLE....- .......... | .... |
| iPS:39 2944 | 21-225_31H5 | .......... .......... | .......... | | ..R.... ..IFH.. | ......V....... | .ELLE....- ...F...... | .... |
| iPS:39 2964 | 21-225_31A8 | .......... .......... | .......... | | ..R.... ..FH... | .....D..V....... | .ELLE....- ...F...... | .... |
| iPS:39 2982 | 21-225_30D1 | ....V..... .......... | .......... | | ..R.... ..FH... | ......V....... | .ELLE....- ...F...... | .... |
| iPS:39 2986 | 21-225_31B8 | .......... .......... | .......... | | ..R.... ..FH... | .....D..V....... | .ELLE....- ...F.L.... | .... |
| iPS:39 3004 | 21-225_30G11 | .......... .......... | .......... | | ..R.... ..FN... | ........T..V.....L | .ELLE....- ...F...... | .... |

Figure 52 (Continued)

| | | | | | | | | |
|---|---|---|---|---|---|---|---|---|
| iPS:39 3040 | 21-225_30E3 | VH3j3-23jD5j5-12jRF3/J H6 | .V....... | ........N | .......... | ....R.... .F... .E. | ......L... | .ELLE..- ...... ...... | .......... .......... |
| iPS:39 3058 | 21-225_31H3 | VH3j3-23jD5j5-12jRF3/J H6 | .V....... | ........N | .......... | ....R... .F... .N.F.. | .......... | .ELLE..- ...F.. ...... | .......... .......... |
| iPS:39 3060 | 21-225_32G12 | VH3j3-23jD5j5-12jRF3/J H6 | .......... .L...... ...N | .......... | .......... | S...R.... .FH.. | ......R.. ......V | .ELLE..- ...F.. ...... | .......... .......... |
| iPS:39 3068 | 21-225_34G9 | VH3j3-23jD5j5-12jRF3/J H6 | .V....... | .......... | .......... | ....R.... .FH.. | ......V | .ELLE..- ...F.. ...... | .......... .......... |
| iPS:39 3072 | 21-225_36C5 | VH3j3-23jD5j5-12jRF3/J H6 | .V....... | ........N | .......V.. | ....R.... .FH.. | ......V | .ELLE..- ...F.. ...... | .......... .......... |
| iPS:39 3076 | 21-225_33A4 | VH3j3-23jD5j5-12jRF3/J H6 | .......... ..S..E .I | ........N | .......... | ...RR.... .F... | ......F.. | .ELLE..- ...... .S.I.. | .......... .......... |
| iPS:39 3102 | 21-225_33F1 | VH3j3-23jD5j5-12jRF3/J H6 | .......... .L...... | .......... | ....C..... | S...R.... .FH.. | ......V | .ELLE..- ...F.. ...... | .......... .......... |
| iPS:39 3104 | 21-225_33A7 | VH3j3-23jD5j5-12jRF3/J H6 | .......... | ........N | .......... | ...RR.... .F... | ......V | .ELLE..- ...F.. ...... | .......... .......... |
| iPS:39 3106 | 21-225_34A6 | VH3j3-23jD5j5-12jRF3/J H6 | .......... | .......... | .N........ | ....R.... .FH.. | ......V | .ELLE..- ...... .FA... | .......... .......... |
| iPS:39 3110 | 21-225_35B7 | VH3j3-23jD5j5-12jRF3/J H6 | .......... | .......... | .......H.. | ....R.... .F... | ......Q.. ......F | .ELLE..- ...F.. ...... | ....A..... .......... |
| iPS:39 3118 | 21-225_34H11 | VH3j3-23jD5j5-12jRF3/J H6 | .......... | ........N | .......... | ...RR.... .F... | .......... | .ELLE..- ...F.. ...... | .......... .......... |
| iPS:39 3124 | 21-225_33G7 | VH3j3-23jD5j5-12jRF3/J H6 | .......... | .N........ | .......... | ...RR.... .F... | .......... | .ELLE..- ...... .S.... | .......... .......... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 3126 | 21-225_35D1 | VH3\|3-23\|D5\|5-12\|RF3\|JH6 | ........ | ........ | ........ | ....R... .FH..... | ....N...V | .ELLE...— ........ ....F.... | ...A. .... .... |
| iPS:39 3128 | 21-225_35F11 | VH3\|3-23\|D5\|5-12\|RF3\|JH6 | ........ | ........ | ........ | ....R... .FH..... .M...... | .......V | .ELLE...— ........ ....F.... | .... .... .... |
| iPS:39 3146 | 21-225_34G8 | VH3\|3-23\|D5\|5-12\|RF3\|JH6 | ........ | ........ | ........ | ....R... .FH..... | .......I .......V | .ELLE...— ........ ....F.... | .... .... .... |
| iPS:39 3150 | 21-225_36A5 | VH3\|3-23\|D5\|5-12\|RF3\|JH6 | .......N | N....... | ........ | ...RR... ..N.F... | ........ | .ELLE...— ........ ....A.... | .... .... .... |
| iPS:39 3180 | 21-225_4G12 | VH3\|3-23\|D5\|5-12\|RF3\|JH6 | ........ | ........ | ........ | .TL..R.. ........ | .S...... .S...... | WGR..S.E. ........ ........— | .... .... .... |
| iPS:39 3232 | 21-225_17F12 | VH3\|3-23\|D5\|5-12\|RF3\|JH6 | ........ | ........ | ........ | ....G... ........ | .V...... | WGR..N.E. ........ ........ | .... .... .... |
| iPS:39 8494 | 21-225_21H4 | VH3\|3-23\|D5\|5-12\|RF3\|JH6 | ........ | ........ | ........ | ..L..R.. ........ | ........ | WGR..S.E. ........ ........— | .... .... .... |
| iPS:39 8508 | 21-225_24B1 | VH3\|3-23\|D5\|5-12\|RF3\|JH6 | ........ | ........ | ........ | ....R... ........ | ........ | .ELLE...— ........ ....F.... | .... .... .... |
| iPS:39 8528 | 21-225_32G1 | VH3\|3-23\|D5\|5-12\|RF3\|JH6 | A....... | ........ | ........ | ....R... .FH..... | ....V... | .ELLE...— ........ ....F.... | .... .... .... |
| iPS:39 8534 | 21-225_33B8 | VH3\|3-23\|D5\|5-12\|RF3\|JH6 | ........ | ........ | ........ | ....R... .FH..... | ....V... | .ELLE...— ........ ....F.... | .... .... .... |
| iPS:39 8540 | 21-225_35A6 | VH3\|3-23\|D5\|5-12\|RF3\|JH6 | ........ | ........ | ........ | ..T..R.. ..FH.... | ....V... | .ELLE...— ........ ....F.... | .... .... .... |
| | Germline | | | | | | | | |

Figure 52 (Continued)

| VH4|4-39|D4|4-17|RF2|JH4 | | U.QLGES FGLVKPSETLS LCTVSGGSIS | SGYYWG | SYYWG | WIRQHPGKGL EWIG | SIYYSGSTYY NPSLKS | RVTISVDRSKN QFSLKLSSVT AADTAVYYCAR | DYGDY | WGQGTL VTVSS |
|---|---|---|---|---|---|---|---|---|---|
| iPS:39 2622 | 21-225_17H8 | VH4|4-39|D4|4-17|RF2|JH4 | .......... .......... .......... | R......... | .......... .... | .R........ .G.N...... ...... | .......... .......... | HGK.W..... ....GL | .......... ..... |
| iPS:39 2638 | 21-225_17F9 | VH4|4-39|D4|4-17|RF2|JH4 | .......... .......... .......... | R......... | .......... .... | N......... .......... ...... | .......... ..S....N. | HGK.W..... ....GL | .......... ..... |
| iPS:39 2656 | 21-225_1F2 | VH4|4-39|D4|4-17|RF2|JH4 | .......... .......... .......... | R......... | .......... .... | N......... ..A.N..... ...G.. | .......... ......G. | HGK.W..... ....GL | .......... ..... |
| iPS:39 2794 | 21-225_21H3 | VH4|4-39|D4|4-17|RF2|JH4 | .......... .......... .......... | R......... | .......... .... | .......... .D........ ...... | .......... ......G. | HGK.W..... ....GL | .......... ..... |
| iPS:39 2822 | 21-225_23C8 | VH4|4-39|D4|4-17|RF2|JH4 | .......... .......... .......... | R......... | ..D....... .... | N......... ..T..N..... ...... | .......... .H....G. | HGK.W..... ....GL | .......... ..... |
| iPS:39 2838 | 21-225_22G8 | VH4|4-39|D4|4-17|RF2|JH4 | .......... .......... ........N. | R......... | .......... .... | N......... .......... .V.... | F......... .M....F.G. | HGK.W..... ....GL | .......... ..... |
| iPS:39 2858 | 21-225_22H4 | VH4|4-39|D4|4-17|RF2|JH4 | .......... .......... .......... | R......... | .......... .... | N......... ..T....H.... ...... | T......... .......... | HGK.W..... ....GL | .......... ..... |
| iPS:39 2882 | 21-225_23A3 | VH4|4-39|D4|4-17|RF2|JH4 | .......... .......... .......... | R......... | .......... .... | Q......... .......... ...... | S......... .......N. ..G.... | HGK.W..... ....GL.F | .......... ..... |
| iPS:39 3804 | 21-225_5H7 | VH4|4-39|D4|4-17|RF2|JH4 | .......... .......... ........N. | R......... | .......... .... | N......... ..T....... ...... | .......... ..S....N. | HGK.W..... ....GL | .......... ..... |
| iPS:39 3832 | 21-225_14B2 | VH4|4-39|D4|4-17|RF2|JH4 | .......... .......... .......... | R......... | .......... .... | N......... ..T....... ...... | .......... ..S....N. | HGK.W..... ....GL | A......... ..... |
| iPS:39 4037 | 21-225_4F4 | VH4|4-39|D4|4-17|RF2|JH4 | .......... .......... ....R..... | R......... | .......... .... | N......... ..D....... ...... | .......... ......G. | HGK.W..... ....GL | .......... ..... |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS.39 4045 | 21-225_4H4 | VH4|4-39/D4|4-17|RF2/J H4 | ........... | R........... | .......M N........ | N........... | HGK.W......GL... | ....I |
| iPS.39 4079 | 21-225_11F5 | VH4|4-39/D4|4-17|RF2/J H4 | ........... | R........... | ......N........T... | N........... | HGK.W......GL.N | ....  |
| | Germline | H_FR1 | H_CDR1 | H_FR2 | H_CDR2 | H_FR3 | H_CDR3 | H_FR4 |
| | VH3|3-21|D4|4-11|RF2|JH3 | EVQLVES GGG.VKPGGSLR LSCAASG-FTFS | ...S YSMN | WIRQAPGK GLEWVS | SISSS SSTIYYAD SVKG | RFTISRDNAK NSLRAED TAVYYCAR | DISNY | WGQGTM VTVSS |
| iPS.39 2624 | 21-225_17H12 | VH3|3-21/D4|4-11|RF2/J H3 | ........... | ......T...... | ........... | ......G...... | ........... | .RG--- | ........... |
| iPS.39 3946 | 21-225_16A4 | VH3|3-21/D4|4-11|RF2/J H3 | ........... | ........... | ........... | ......G T.K... | ......T...... | .RG--- ---S. | ......Q |
| iPS.39 4008 | 21-225_15H8 | VH3|3-21/D4|4-11|RF2/J H3 | ........... | ....V....... | ........... | ......G T...C. .I.... | ......D...... | .RG--- ---SY ---S. | ........... |
| | Germline | H_FR1 | H_CDR1 | H_FR2 | H_CDR2 | H_FR3 | H_CDR3 | H_FR4 |
| | VH6|6-01/D6|6-19|RF1/JH6 | QVQLQQS GPG.VKPSQTLS LTCAISG-DSVS | SN---SAAWN | WIRQSPSR GLEWLG | RIIYY--- SRWNDYA VSVKS | RTINPDTSKNQFSLQL NSVTEEDTAVYYCAR | GYSSGWYY YYYYGMDV | WGQGTT VTVSS |
| iPS.39 2636 | 21-225_17A6 | VH6|6-01/D6|6-19|RF1/J H6 | ........... | R......T.....S | ........... | ........... | ......V...... | VS.GWSHH | ........... |
| | Germline | H_FR1 | H_CDR1 | H_FR2 | H_CDR2 | H_FR3 | H_CDR3 | H_FR4 |
| | VH6|6-01/D2|2-15|RF2|JH6 | QVQLQQS GPG.VKPSQTLS LTCAISG-DSVS | SN---SAAWN | WIRQSPSR GLEWLG | RIIYY--- SRWNDYA VSVKS | RTINPDTSKNQFSLQL NSVTEEDTAVYYCAR | CVCSGGSCVS YYYYGMDV | WGQGTT VTVSS |
| iPS.39 2648 | 21-225_16D11 | VH6|6-01/D2|2-15|RF2/J H6 | ........... | R......T.....S | ........... | ........... | ........... | VNSGWSHH-- | ........... |
| | Germline | H_FR1 | H_CDR1 | H_FR2 | H_CDR2 | H_FR3 | H_CDR3 | H_FR4 |
| | VH3|3-11|D11-11|RF3|JH2 | QVQLVES GGG.VKPGGSLR LSCAASG-FTFS | D---VTMS | WVRQAPGK GLEWVS | YISSS--- GSTIYYAD SVKG | RFTISRDNAKNSLYLQM NSLRAEDTAVYYCAR | VNWNDY --WYFDL | WGRGTI VTVSS |

| | | H_FR1 | H_CDR1 | H_FR2 | H_CDR2 | H_FR3 | H_CDR3 | H_FR4 |
|---|---|---|---|---|---|---|---|---|
| iPS:39 3992 | 21-225_14H8 | VH3|3-48|D7|7-27|RF1/JH4 | .........N... | ........... | ........... | ........A.. | GG.S........P... | ........ |
| iPS:39 4055 | 21-225_9C8 | VH3|3-48|D7|7-27|RF1/JH4 | ...........V | .....Q..... | ........... | ........... | GG.S........P..S | ........ |
| | Germline | VH3|3-30.3|D4|4-11|RF2/JH4 | EVQLVES... GGGLVQPGGSLR LSCAASG-FTFS | S-----YAMS | WVRQAPGK GLEWVA | AISGS GGSTYYAD SVKG | RFTISRDNSKNTLYLQM NSLRAEDTAVYYCAR | VYDY | WGQGT LVTVSS |
| iPS:39 2694 | 21-225_19A5 | VH3|3-30.3|D4|4-11|RF2/JH4 | ............ | ............ | ..WF........ | ...D........ | ............ | RAYS........SSS. | ........ |
| | Germline | VH3|3-23|D1|1-1|RF1/JH4 | EVQLLES... GGGLVQPGGSLR LSCAASG-FTFS | S-----YAMS | WVRQAPGK GLEWVS | AISGS GGSTYYAD SVKG | RFTISRDNSKNTLYLQM NSLRAEDTAVYYCAK | GTYGY-YFDY | WGQGT LVTVSS |
| iPS:39 2714 | 21-225_16G12 | VH3|3-23|D1|1-1|RF1/JH4 | ........... | .T.......... | ..H......... | ..R....A.... | ........S.. | QD----------C | ........ |
| iPS:39 2890 | 21-225_20H9 | VH3|3-23|D1|1-1|RF1/JH4 | .S.......... | ............ | ..Y......... | ........E... | ............ | .GS--.....-LF. | ........ |
| iPS:39 2892 | 21-225_20C11 | VH3|3-23|D1|1-1|RF1/JH4 | .S.......... | .T.......... | ..H......... | ..R....A.... | ........S.. | QD----------C | ........ |
| iPS:39 3968 | 21-225_5A5 | VH3|3-23|D1|1-1|RF1/JH4 | ...M......... | ............ | ..Y......... | ............ | ............ | .GS--.....-LF. | ........ |
| | Germline | VH3|3-23|D6|6-6|RF1/JH3 | EVQLLES... GGGLVQPGGSLR LSCAASG-FTFS | S-----YAMS | WVRQAPGK GLEWVS | AISST GGSTYYAD SVKG | RFTISRDNSKNTLYLQM NSLRAEDTAVYYCAR | EISSSS---DAFDI | WGQGTM VTVSS |
| iPS:39 2730 | 21-225_17A1 | VH3|3-23|D6|6-6|RF1/JH3 | ..........N. | ............ | V........... | .SN......... | ............ | R.T.DW......H... | ........ |

| | Germline | H_FR1 | H_CDR1 | H_FR2 | H_CDR2 | H_FR3 | H_CDR3 | H_FR4 |
|---|---|---|---|---|---|---|---|---|
| VH4/4-39|D1|1-26|RF3|JH1 | | QVQLQES GPGLVKPSETLS LTCTVSG-GSIS | SSYWG | WIRQPPGK GLEWIG | SIYY SGSTYYNP SLKS | RVTISVDTSKNQFSLKL SSVTAADTAVYYCAR | YSSSYY ---ABYFDH | WGQGTL VTVSS |
| iPS:39 2774 | 21-225_21F3 | VH4|4-39|D1|1-26|RF3|JH1 | .........A........ ............ | R........ | ........ ........ | .................. .................. | L.S.W— ---------- | .... .... |
| iPS:39 3962 | 21-225_7H7 | VH4|4-39|D1|1-26|RF3|JH1 | .................. ............ | R........ | .....V.. ........ | N....... ...I.... | .........E........ .................. | H.T.W— ---SLD. | .... .... |
| iPS:39 4049 | 21-225_13H5 | VH4|4-39|D1|1-26|RF3|JH1 | .........A........ ............ | R........ | ........ ........ | ........ ........ | .........S........ .................. | L.S.W— ---D.... | .... .... |
| | Germline | H_FR1 | H_CDR1 | H_FR2 | H_CDR2 | H_FR3 | H_CDR3 | H_FR4 |
| VH3|3-21|D2|2-21|RF2|JH4 | | EVQLVES GGGLVKPGGSLR LSCAASG-FTFS | S---YSMN | WVRQAPGK GLEWVS | SISS- SSSYIYYAD SVKG | RFTISRDNAKNSLYLQM NSLRAEDTAVYYCAR | AGGEDC ---YSNFDY | WGQGTL VTVSS |
| iPS:39 2776 | 21-225_21A12 | VH3|3-21|D2|2-21|RF2|JH4 | .................N............ | ........ | ........ ........ | ...G.... ........ | ..................L.................. | .AG--- ------ | .... .... |
| | Germline | H_FR1 | H_CDR1 | H_FR2 | H_CDR2 | H_FR3 | H_CDR3 | H_FR4 |
| VH3|3-33|D6|6-19|RF2|JH6 | | QVQLVES GGGLVQPGRSLR LSCAASG-FTFG | S---YGMH | WVRQAPGK GLEWVA | VIWYD GSNKYYAD SVKG | RFTISRDNSKNTLYLQM NSLRAEDTAVYYCAR | GIAVAGXY ---YYYGMDV | WGQGTT VTVSS |
| iPS:39 2806 | 21-225_24H3 | VH3|3-33|D6|6-19|RF2|JH6 | ............G.............. | ........ | ........ ........ | ........ ........ | .................. .................. | VAVAG- ........ | .... .... |
| | Germline | H_FR1 | H_CDR1 | H_FR2 | H_CDR2 | H_FR3 | H_CDR3 | H_FR4 |
| VH3|3-48|D7|7-27|RF2|JH4 | | EVQLVES GGGLVQPGGSLR LSCAASG-FTFS | S---YSMN | WVRQAPGK GLEWVS | YISSS SSTYYYAD SVRG | RFTISRDNAKNSLYLQM NSLRDEDTAVYYCAR | YLGY ---FDY | WGQGTL VTVSS |
| iPS:39 2826 | 21-225_20B9 | VH3|3-48|D7|7-27|RF2|JH4 | ................................ | ........ | ........ ........ | ........ ........ | .................. .................. | S.WS... ---P... | .... .... |
| | Germline | H_FR1 | H_CDR1 | H_FR2 | H_CDR2 | H_FR3 | H_CDR3 | H_FR4 |
| VH4|4-59|D1|1-1|RF1|JH5 | | QVQLQES GPGLVKPSETLS LTCTVSG-GSIS | S---YYWS | WIRQPPGK GLEWIG | YIYYS SGSTKYNP SLKS | RVTISVDTSKNQFSLR1 SSVTAADTAVYYCAR | GTYY ---NWFDP | WGQGTL VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 2830 | 21-225_21A5 | VH4|4-59/D1|1-1|RF1/JH5 | ........F. | ....A..R.T. ....I...... | ....M....... | .P.SG....... | .......... |
| | Germline | H_FR1 EVQLLES GGGLVQPGGSLR LSCAASGFTFS | H_CDR1 .....YAMS | H_FR2 WVRQAPGK GLEWVS | H_CDR2 AISGS GGSTYYAD SVKG | H_FR3 RFTISRDNSKNTLYLQM NSLRAEDTAVYYCAK | H_CDR3 SIAAR ....SFDY | H_FR4 WGQGTL VTVSS |
| iPS:39 2840 | 21-225_23G1 | VH3|3-23/D6|6-6|RF2/JH4 | | .....R.. | | ....R..V.. ..T..NT..... | ....R....... | .SL-- | |
| iPS:39 4018 | 21-225_15B1 | VH3|3-23/D6|6-6|RF2/JH4 | .....V.. | | | G..... ....NN..... | ........V ....R..... | .SL-- | |
| iPS:39 4026 | 21-225_16C7 | VH3|3-23/D6|6-6|RF2/JH4 | .....V.T | | | T..... ....W..... | ....E...R..... | .SL-- | |
| | Germline | H_FR1 EVQLLES GGGLVQPGGSLR LSCAASGFTFS | H_CDR1 .....YAMS | H_FR2 WVRQAPGK GLEWVS | H_CDR2 AISGS GGSTYYAD SVKG | H_FR3 RFTISRDNSKNTLYLQM NSLRAEDTAVYYCAK | H_CDR3 SIAAR ....NWFDP | H_FR4 WGQGTL VTVSS |
| iPS:39 2842 | 21-225_23G8 | VH3|3-23/D6|6-6|RF2/JH5 | | | | | .........V | .SG--- ...WFA | |
| | Germline | H_FR1 EVQLLES GGGLVQPGGSLR LSCAASGFTFS | H_CDR1 .....YAMS | H_FR2 WVRQAPGK GLEWVS | H_CDR2 AISGS GGSTYYAD SVKG | H_FR3 RFTISRDNSKNTLYLQM NSLRAEDTAVYYCAK | H_CDR3 VDLEY ....WFDL | H_FR4 WGQGTL VTVSS |
| iPS:39 2856 | 21-225_22A2 | VH3|3-23/D1|1-1|RF1/JH2 | | | | G..... ....N.P..... | ....I........ | .VG--- | |
| | Germline | H_FR1 QVQLQES GPGLVKPSQTLS LTCTVSG GSIS | H_CDR1 SG .GYYWS | H_FR2 WIRQHPGK GLEWIG | H_CDR2 YIYY SGSTYYNP SLKS | H_FR3 RVTISVDTSKNQFSLKL SSVTAADTAVYYCAR | H_CDR3 VDTAWYYY YYGMDV | H_FR4 WGQGTT VTVSS |
| iPS:39 2864 | 21-225_23B9 | VH4|4-30.1/D5|5-18|RF1/JH6 | .....A... ...D....... | | | | | E.G.FG--- | |

Figure 52 (Continued)

| | | H_FR1 EVQLLES GGGLVQPGGSLR LSCAASG-FTFS | H_CDR1 .YAMS | H_FR2 WVRQAPGK GLEWVS | H_CDR2 AISGS GGSTYYAD SVKG | H_FR3 RFTISRDNSKNTLYLQM NSLRAEDTAVYYCAK | H_CDR3 DYSSSSC----------- YTDAFDI | H_FR4 WGQGT VTVSS |
|---|---|---|---|---|---|---|---|---|
| iPS:39 2874 | 21-225_21D2 | VH3|3-23|D2|2-2|RF2|JH 3 | ..K........N | ..........N | VL...F... | S....G....F..R | YCS.ARC-..........PY. | .......... |
| iPS:39 3940 | 21-225_16B2 | VH3|3-23|D2|2-2|RF2|JH 3 | ...............N | ........T | ....P.... V.....F... | S....G....F..R | YCS.TRC-..........PY. | .......... |
| iPS:39 3956 | 21-225_4D7 | VH3|3-23|D2|2-2|RF2|JH 3 | ..K............ | ............ | VL...F... | S....G....F..R | YCS.ARC-..........PY. | .......... |
| iPS:39 8476 | 21-225_17C1 | VH3|3-23|D2|2-2|RF2|JH 3 | .E............. | ............ | V....T.F... | S.........F..R | YCS.TRC-..........PY. | .......... |
| | Germline | H_FR1 | H_CDR1 | H_FR2 | H_CDR2 | H_FR3 | H_CDR3 | H_FR4 |
| | | EVQLVES GGGLVKPGGSLR LSCAASG-FTFS | .N.AMS | WVRQAPGK GLEWVS | RIKSKT DGGTTDYA APVKG | RFTISRDDSKNTLYLQM NSLKTEDTAVYYCTT | YNFWD--------- YFDY | WGQGT VTVSS |
| iPS:39 2898 | 21-225_21H10 | VH3|3-15|D1|1-1|RF3|JH 4 | ............... | ............ | ............ | ............ | EG.-..........-T... | .......... |
| iPS:39 3802 | 21-225_3D12 | VH3|3-15|D1|1-1|RF3|J H4 | ...V........ | .T........ | ............ | ..N.I..... V | ............ | EG.-..........-T... | .......... |
| | Germline | H_FR1 | H_CDR1 | H_FR2 | H_CDR2 | H_FR3 | H_CDR3 | H_FR4 |
| | | EVQLLES GGGLVQPGSSLR LSCAASG-FTFS | .S.YSMN | WVRQAPGK GLEWVS | YISSS SSTIYYAD SVKG | RFTISRDEDNSKNTLYLQM NSLRAEDTAVYYCAR | TTVT .......... | WGQGT VTVSS |
| iPS:39 2950 | 21-225_25C10 | VH3|3-48|D4|4-11|RF3|J H4 | ............... | .......R.. | ............ | ....S....... | ............ | .AG-.......... | .......... |
| | Germline | H_FR1 | H_CDR1 | H_FR2 | H_CDR2 | H_FR3 | H_CDR3 | H_FR4 |
| | | EVQLLES GGGLVQPGGSLR LSCAASG-FTFS | .YAMS | WVRQAPGH GLEWVS | | RFTISRENSKDTLYLQM NSLRAEDTAVYYCAR | YSSSSY--------- YFFDY | WGQGT VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:39 3010 | 21-225_25E11 | VH3|3-23|D3|1-26|RF3|JH4 | .......... | .......... | ..........V...G | ..........<br>..... | .......... | RGY.GYE..........<br>.....DLL....C | .......... |
| | Germline VH3|3-23|D3|3-3|RF3|JH3 | EVQLLES-<br>GGGLVQPGGSLR<br>LSCAASG-FTFS | S----YAMS | WVRQAPGK<br>GLEWVS | AISGSGGST<br>YYADSVKG | RFTISRDNSKNTLYLQM<br>NSLRAEDTAVYYCAR | LIIGWV-----<br>----IDAFDI | WGQGT<br>VTVSS |
| iPS:39 3016 | 21-225_28F11 | VH3|3-23|D3|3-3|RF3|JH3 | .......I... | .......... | .......... | .VI......<br>.T.F... | .......... | R.Q.D---<br>-D.... | .......... |
| | | H_FR1 | H_CDR1 | H_FR2 | H_CDR2 | H_FR3 | H_CDR3 | H_FR4 |
| | Germline VH3|3-33|D3|3-22|RF2|JH6 | CVQLVES-<br>GGSVVQPGRSLR<br>LSCAASG-FTFS | S-----YGMH | WVRQAPGK<br>GLEWVA | VIWY---<br>GSNKYYAD<br>SVKG | RFTISRDNSKNTLYLQM<br>NSLRAEDTAVYYCAR | YYYDSSGYYY-<br>-----YYYGMDV | WGQGT<br>TVTSS |
| iPS:39 3032 | 21-225_26F8 | VH3|3-33|D3|3-22|RF2|JH6 | .......G... | .......... | .......... | ........I | .......... | ER...FW-----<br>------<br>SGC.... | .......... |
| | | H_FR1 | H_CDR1 | H_FR2 | H_CDR2 | H_FR3 | H_CDR3 | H_FR4 |
| | Germline VH1|1-02|D4|4-11|RF2|JH6 | CVQLVQS<br>GAEVKKPGASVK<br>VSCKASG-YTFT | S-----YYMH | WVRQAPGQ<br>GLEWMG | WINPN-<br>SGGTNYAQ<br>KFQG | RVTMTRDTSISTAYMEL<br>SRLRSDDTAVYYCAR | DTSNYYY-----<br>------YYYGMDV | WGQGT<br>TVTSS |
| iPS:39 3042 | 21-225_31F1 | VH1|1-02|D4|4-11|RF2|JH6 | .......D... | .......... | .......... | .......... | ......M........... | ..S..FSNW.........<br>......YD... | .......... |
| iPS:39 3108 | 21-225_34G11 | VH1|1-02|D4|4-11|RF2|JH6 | .......... | .......... | .......... | ........I<br>........R. | .......... | ..I..FSSW.........<br>......YD..A. | .......... |
| | | H_FR1 | H_CDR1 | H_FR2 | H_CDR2 | H_FR3 | H_CDR3 | H_FR4 |
| | Germline VH1|1-18|D5|5-12|RF3|JH4 | CVQLVQS<br>GAEVKKPGASVK<br>VSCKASG-YTFT | S-----YGIS | WVRQAPGQ<br>GLEWMG | WISAY-<br>NGNTNYAQ<br>KLQG | RVTMTTSTSTAYMEL<br>RSLRSDDTAVYYCAR | GYSGYD---------<br>-----YFDY | WGQGT<br>LVTVSS |
| iPS:39 3044 | 21-225_25B8 | VH1|1-18|D5|5-12|RF3|JH4 | .......... | .......... | .......... | .......... | ...........D......... | TAA..S....SSW... | .......... |
| iPS:39 3050 | 21-225_28C5 | VH1|1-18|D5|5-12|RF3|JH4 | .......... | .......... | .......... | .......... | ...........D......... | TAA..S....SSW... | .......... |
| | | H_FR1 | H_CDR1 | H_FR2 | H_CDR2 | H_FR3 | H_CDR3 | H_FR4 |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| | VH3|3-33|D6|6-8|RF1|JH3 | QVQLVES GGGVVQPGRSLR LSCAASG FTFS | ....YGMH | WVRQAPGK GLEWVA | VISYD... GSNKYYADS VKG | RFTISRDNSKNTLYLQM NSLRAEDTAVYYCAR | EY..GW ————————DAFDI | WGQGTM VTVSS |
| iPS:39 3046 | 21-225_25A12 | | N......CV. | | | | .EY..GW....YDYGM.V | |
| | Germline | H_FR1 | H_CDR1 | H_FR2 | H_CDR2 | H_FR3 | H_CDR3 | H_FR4 |
| | VH3|3-21|D4|4-11|RF3|JH6 | EVQLVES GGGLVKPGGSLR LSCAASG FTFS | ....YSMN | WVRQAPGK GLEWVS | SISSS... SSYIYYAD SVKG | RFTISRDNAKNSLYLQM NSLRAEDTAVYYCAR | ——————— YYGMDV | WGQGTT VTVSS |
| iPS:39 3078 | 21-225_33H11 | | | | .....G.. | .....S........... | .NG———— | |
| iPS:39 3142 | 21-225_33A3 | | .........G | | ......G..T.. | | .NG———— | |
| | Germline | H_FR1 | H_CDR1 | H_FR2 | H_CDR2 | H_FR3 | H_CDR3 | H_FR4 |
| | VH3|3-23|D6|6-19|RF2|JH6 | EVQLLES GGGLVQPGGSLR LSCAASG FTFS | ....YAMS | WVRQAPGK GLEWVS | AISGS... GGSTYYAD SVKG | RFTISRDNSKNTLYLQM NSLRAEDTAVYYCAR | GLAVAGII————YYGMDV | WGQGTT VTVSS |
| iPS:39 3096 | 21-225_34D11 | ......S | .........N | | .....R..FH. | ................V. | .EL.ED.- | |
| | Germline | H_FR1 | H_CDR1 | H_FR2 | H_CDR2 | H_FR3 | H_CDR3 | H_FR4 |
| | VH3|3-30.3|D4|4-23|RF2|JH3 | QVQLVES GGGVVQPGRSLR LSCAASG FTFS | ....YAMH | WVRQAPGK GLEWVA | VISYD... GSNKYYADS VKG | RFTISRDNSKNTLYLQM NSLRAEDTAVYYCAR | DYGNS———— DAFDI | WGQGTM VTVSS |
| iPS:39 3172 | 21-225_3B12 | ......H | | ......S | | ................H. | .RR.GYG....VP.. | |
| | Germline | H_FR1 | H_CDR1 | H_FR2 | H_CDR2 | H_FR3 | H_CDR3 | H_FR4 |
| | VH3|3-30.3|D4|4-23|RF2|JH6 | QVQLVES GGGVVQPGRSLR LSCAASG FTFS | ....YAMH | WVRQAPGK GLEWVA | VISYD... GSNKYYADS VKG | RFTISRDNSKNTLYLQM NSLRAEDTAVYYCAR | DYGNSYY——— YYGMDV | WGQGTT VTVSS |
| iPS:39 3174 | 21-225_15D8 | ......T | .........G | | | | .RVYC.STSCV....PYYD...... | .....F.. |
| | Germline | H_FR1 | H_CDR1 | H_FR2 | H_CDR2 | H_FR3 | H_CDR3 | H_FR4 |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| VH3/3-15/D7/7-27/RF1/JH6 | | EVQLLES-GGGLVKPGGSLR LSCAASG-FTFS | N-------SMMS | WVRQAPGK RGLEWVG | N-SAPGK DGSTIYA RGSGG DGSTIYA EVRG | RFTISRDDSKNTLYLQM NSLKTEDTAVYYCTT | LIGYYY------- YYGMDV | WGQGTL VTVSS |
| iPS:39 3194 | 21-225_16D2 | VH3/3-15/D7/7-27/RF1/JH6 | .........N | ..................... | ..................... | H........... | D..PIAARLA ...YYY..A... | ..... |
| iPS:39 8488 | 21-225_19F6 | VH3/3-15/D7/7-27/RF1/JH6 | .........N | ..................... | ..................... | ..................... | D..PIAARLA ...YYY..A... | ....H |
| iPS:39 8544 | 21-225_7C8 | VH3/3-15/D7/7-27/RF1/JH6 | .........R.N | .......L........ | ..................... | ...E.E......... .....G.....S. | D..PIAARLA ...YYY..A... | ..... |
| iPS:40 2231 | 21-225_6D9 | VH3/3-15/D7/7-27/RF1/JH6 | .........N | .......L........ | ..................... | .......E......S. | D..PIAARLA ...YYY..A... | ..... |
| Germline | | H_FR1 | H_CDR1 | H_FR2 | H_CDR2 | H_FR3 | H_CDR3 | H_FR4 |
| VH3/3-23/D4/4-11/RF2/JH4 | | EVQLLES- GGGLVQPGGSLR LSCAASG-FTFS | S-------YAMS | WVRQAPGK GLEWVS | AISGS-- GGSTYYAD SVKG | RFTISRDNSKNTLYLQM NSLRAEDTAVYYCAR | DYSNY------- -----YFDY | WGQGTL VTVSS |
| iPS:39 3870 | 21-225_7B1 | VH3/3-23/D4/4-11/RF2/JH4 | ........D.. | ..................... | .........T..... | .........I..... | .......K....... F..R | .RG--....... ....-SV | ..... |
| Germline | | H_FR1 | H_CDR1 | H_FR2 | H_CDR2 | H_FR3 | H_CDR3 | H_FR4 |
| VH4/4-39/D4/4-17/RF2/JH1 | | QVQLQES- GPGLVKPSETLS LTCTVSG-GSIS | SST----SYYWG | WIRQPPGK GLEWIG | SIYY---- SGSTYYNP SLKS | RVTISVDTSKNQFSLKL SSVTAADTAVYYCAR | DYGKYA------- -----YFFDH | WGQGTL VTVSS |
| iPS:39 3872 | 21-225_2A11 | VH4/4-39/D4/4-17/RF2/JH1 | ................... | ..................... | ........A.... | ........N...... .....V... | ..................T..... | HGK.W-........ ...-GLED | ..... |
| Germline | | H_FR1 | H_CDR1 | H_FR2 | H_CDR2 | H_FR3 | H_CDR3 | H_FR4 |
| VH4/4-59/D6/6-6/RF1/JH4 | | QVQLQES- GPGLVKPSETLS LTCTVSG-GSIS | S-------YYWS | WIRQPPGK GLEWIG | YIYY---- SGSTNYNP SLKS | RVTISVDTSKNQFSLKL SSVTAADTAVYYCAR | EYSSS------- -----SYFDY | WGQGTL VTVSS |
| iPS:39 3890 | 21-225_4B1 | VH4/4-59/D6/6-6/RF1/JH4 | .....D... | .........S... | ..................... | ........R.T.... .........I...... | ..I.M......K...... ..... | DLK..G........ .....CLF... | ..... |
| Germline | | H_FR1 | H_CDR1 | H_FR2 | H_CDR2 | H_FR3 | H_CDR3 | H_FR4 |

| | | H_FR1 | H_CDR1 | H_FR2 | H_CDR2 | H_FR3 | H_CDR3 | H_FR4 |
|---|---|---|---|---|---|---|---|---|
| iPS:39_4065 | 21-225_11E2 | VH1\|1-08/D2\|2-21\|RF1/JH4 | .....V...... | N............ | ............ | ............ | ..........D. | .HG.F--- -L... | ....I. ..... |
| iPS:39_8506 | 21-225_23G12 | VH1\|1-08/D2\|2-21\|RF1/JH4 | ........L... | N............ | ............ | ......Y..... | ..........Y. | .GG.Y--- ---- | ..... ..... |
| iPS:39_8512 | 21-225_25E12 | VH1\|1-08/D2\|2-21\|RF1/JH4 | ............ | N............ | ............ | ......M..... | ............ | .NG.Y--- ---- | ..... ..... |
| | Germline | H_FR1 | H_CDR1 | H_FR2 | H_CDR2 | H_FR3 | H_CDR3 | H_FR4 |
| | VH3\|3-33/D7\|7-27\|RF2/JH3 | EVQLVES GGGVVQPGRSL RLSCAASG-FTFS | S......YGMH | WVRQAPGK GLEWVA | VIWYD GSNKYYAD SVKG | RFTISRDNSKNTLYLQM NSLRAEDTAVYYCAR | *LCD APDI | WGQGTT VTVSS |
| iPS:39_4091 | 21-225_13H3 | VH3\|3-33/D7\|7-27\|RF2/JH3 | ............ L. .......... | ............ | ............ | E........V. ...R. | ............S.......... | E..F...... QS.F | .....P ..... |
| | Germline | H_FR1 | H_CDR1 | H_FR2 | H_CDR2 | H_FR3 | H_CDR3 | H_FR4 |
| | VH3\|3-23/D4\|4-23\|RF2/JH6 | EVQLLES GGGLVQPGGSLR LSCAASG-FTFS | S......YAMS | WVRQAPGK GLEWVS | AISGS GGSTYYAD SVKG | RFTISRDNSKNTLYLQM NSLRAEDTAVYYCAR | DYGGNSYY YYYGMDV | WGQGTT VTVSS |
| iPS:39_8472 | 21-225_16E4 | VH3\|3-23/D4\|4-23\|RF2/JH6 | I........... | .....V...... | ............ | T..VG...T...... | ............ | WGR....E.... --------GYPDY | ..... ..... |
| | Germline | H_FR1 | H_CDR1 | H_FR2 | H_CDR2 | H_FR3 | H_CDR3 | H_FR4 |
| | VH2\|2-05/D6\|6-19\|RF2/JH4 | QITLKES GPTLVKPTQTL TLTCTFSG-FSLS | TS......GVGVG | WIRQPPGK ALEWL | ALIYW NDDKRYSP SLKS | RLTITKDTSKNQVVLTM TNMDPVDTATYYCAH | GTAVA -----GYFDY | WGQGTL VTVSS |
| iPS:39_8498 | 21-225_22E6 | VH2\|2-05/D6\|6-19\|RF2/JH4 | ............ | .G.......... | ............L. | ............ | ......R..... | T....R....... --------G--- | ..... ..... |
| | Germline | H_FR1 | H_CDR1 | H_FR2 | H_CDR2 | H_FR3 | H_CDR3 | H_FR4 |
| | VH1\|1-08/D5\|5-24\|RF2/JH4 | QVQLVQS GAEVKKPGASVK VSCKASG-YTFT | S......YDIN | WVRQATGQ GLEWMG | WMNPN SGNTGYAQ KFQG | RVTMTRNTSISTAYMEL SSLRSEDTAVYYCAR | *RLQ -----LYFDY | WGQGTL VTVSS |
| iPS:39_8536 | 21-225_33D12 | VH1\|1-08/D5\|5-24\|RF2/JH4 | ............ | ..........S. | ............ | ............ | ............ | K.A...... ---N... | ..... ..... |
| | Germline | H_FR1 | H_CDR1 | H_FR2 | H_CDR2 | H_FR3 | H_CDR3 | H_FR4 |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| | | QITLKES—GPTLVKPTQTLTLTCTFSG-FSLS | TS----SVGVG | WIRQPPGK ALEWLA | LI-----------NDDKRYSP SLKS | RLTITKDTSKNQVVLTM TNMDPVDTATYYCAR | ETSSS----------SYFDY | WGQGTL VTVSS |
| VH2\|2-05\|D6\|6-6\|RF1\|JH4 | iPS:39 8546 21-225_9H10 | ..........T.... | | | .....S..... | ........A..... | TG..C......C..... | |
| Germline | | H_FR1 | H_CDR1 | H_FR2 | H_CDR2 | H_FR3 | H_CDR3 | H_FR4 |
| | | EVQLVES-GGGLVKPGGSLR LSCAASG-FTFS | S------YSMN | WVRQAPGK GLEWVS | SISSS-----SSYIYYAD SVKG | RFTISRDNAKNSLYLQM NSLRAEDTAVYYCAR | VQIPATY----YYKGMDV | WGQGTT VTVSS |
| VH3\|3-21\|D1\|1-11\|RF2\|JH6 | iPS:40 2229 21-225_16H9 | | | | ..........G..... | | .....NG-------..... | |
| Germline | | H_FR1 | H_CDR1 | H_FR2 | H_CDR2 | H_FR3 | H_CDR3 | H_FR4 |
| | | EVQLVES-GGGLVKPGGSLR LSCAASG-FTFS | S------YSMN | WVRQAPGK GLEWVS | SISSS-----SSYIYYAD SVKG | RFTISRDNAKNSLYLQM NSLRAEDTAVYYCAR | TTVTR-----------WFDR | WGQGTL VTVSS |
| VH3\|3-21\|D4\|4-11\|RF3\|JH5 | iPS:40 2233 21-225_16D10 | ....T......NL.... | | | ......AGH...S..... | | .....NG-------.....F | |
| Germline | | H_FR1 | H_CDR1 | H_FR2 | H_CDR2 | H_FR3 | H_CDR3 | H_FR4 |
| | | EVQLVES-GGGLVQPGGSLR LSCAASG-FTFS | S------YSMN | WVRQAPGK GLEWVS | SISSS-----SSYIYYAD SVKG | RFTISRDNSKNTLYLQM NSLRAEDTAVYYCAR | GTTGI-----------DAFDI | WGQGTM VTVSS |
| VH3\|3-21\|D1\|1-11\|RF1\|JH3 | iPS:40 2235 21-225_20F10 | | | | .....T-.....TF... | | .....KAG-------.....IDAFDI | |
| Germline | | H_FR1 | H_CDR1 | H_FR2 | H_CDR2 | H_FR3 | H_CDR3 | H_FR4 |
| | | EVQLVES-GGGLVQPGGSLR LSCAASG-FTFS | S------YAMS | WVRQAPGK GLEWVS | AISGS-----GGSTYYAD SVKG | RFTISRDNSKNTLYLQM NSLRAEDTAVYYCAR | VDIVAT-----------IDAFDI | WGQGTM VTVSS |
| VH3\|3-23\|D5\|5-12\|RF1\|JH3 | iPS:40 3870 21-225_23G4 | | | | .....V..R..... | | .....-L...... | |
| Germline | | H_FR1 | H_CDR1 | H_FR2 | H_CDR2 | H_FR3 | H_CDR3 | H_FR4 |
| VH4\|4-39\|D4\|4-11\|RF1\|JH4 | | QVQLQES-GPGLVKPSETLS LTCTVSG-GSIS | SS-----SYWG | WIRQPPGK GLEWIG | SIYY-----SGSTYYNP SLKS | RVTISVDTSKNQFSLKL *LQ*L SSVTAADTAVYYCAR | RG..GA----------TE.....YPDY | WGQGTL VTVSS |

Figure 52 (Continued)

| | | H_FR1 | H_CDR1 | H_FR2 | H_CDR2 | H_FR3 | H_CDR3 | H_FR4 |
|---|---|---|---|---|---|---|---|---|
| iPS:40 3872 | 21-225_8F11 | VH4/4-39/D4/4-11\|RF1/JH4 | RT........ | ........ | L........ | ...N........ | ................G....... | HG.DW..........GL... | |
| | Germline | VH1\|1-08/D3\|3-9\|RF2/JH6 | EVQLVQS-GAEVKKPGASVK VSCKASG-YTFT | S----YDIN | WVRQATGQ GLEWMG | WMNPN-SGNTGYAQ KFQG | RVTMTRNTSISTAYMEL SSLRSEDTAVYYCAR | YYDILTGYYN-YYYYGMDV | WGQGTT VTVSS |
| iPS:43 7240 | 21-225_84H12 | VH1\|1-08/D3\|3-9\|RF2/JH6 | .................. | .................. | .................. | .................. | ..........R........ | GF..........S--..........PT.....D | .................. |
| iPS:43 4577 | 21-225_75C11 | VH1\|1-08/D3\|3-9\|RF2/JH6 | .................. | .................. | .................. | ...L..H........ | ........I...W..R........ | GF..........S--..........PT.....D | .................. |
| iPS:43 4553 | 21-225_76H12 | VH1\|1-08/D3\|3-9\|RF2/JH6 | .................. | .................. | .................. | ...L..H........ | ........I...W..R........ | GF..........S--..........PT.....D | .................. |
| iPS:43 4927 | 21-225_86E5 | VH1\|1-08/D3\|3-9\|RF2/JH6 | .................. | .................. | .................. | .................. | ............W..R........ | GF..........S--..........PT.....D | .................. |
| | | H_FR1 | H_CDR1 | H_FR2 | H_CDR2 | H_FR3 | H_CDR3 | H_FR4 |
| | Germline | VH3\|3-23/D6\|6-19\|RF2/JH4 | EVQLLES-GGGLVQPGGSLR LSCAASG-FTFS | S----YAMS | WVRQAPGK GLEWVS | AISGS-GGSTYYAD SVKG | RFTISRDNSKNTLYLQM NSLRAEDTAVYYCAK | GTAVA------GYFDY | WGQGTL VTVSS |
| iPS:43 5477 | 21-225_154E8 | VH3\|3-23/D6\|6-19\|RF2/JH4 | .................. | .................. | ......R........... | ....N.F........ | ..........I........ | H......GT.........GAH...... | A...... |
| iPS:43 5385 | 21-225_149G7 | VH3\|3-23/D6\|6-19\|RF2/JH4 | .................. | .................. | .................. | ....N.F........ | ..........I........ | H......GT.........GAH...... | A...... |

Figure 53 (Table 6)
Standard IgG Antibody Variable Region Protein Alignment
CDRs defined by Kabat
Alignment numbering defined by Amgen Reference (AHo)

| KAPPA_VARIABLE | Germline | K_FR1 | K_CDR1 | K_FR2 | K_CDR2 | K_FR3 | K_CDR3 | K_FR4 |
|---|---|---|---|---|---|---|---|---|
| VK4|B3/J K1 | | DIVMTQSPDSLAVSLG ERATINC | KSS QSVLYSSNNNY LA | WYQQKPGQPPK LLIY | W ASTRES | GVPDRFSGSGSG TEFTLTISSLQAEDVAVY YC | QQYYS TPPT | FGQGTK VEIK |
| iPS:39 2928 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:42 4419 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:44 1468 .001.001 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:44 1475 .001.002 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:44 1482 .001.003 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:44 1489 .001.004 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |
| iPS:44 1496 .001.005 | VK4|B3/J K1 | DIVMTQSFDSLAVSLG ERATIKC | KSS QSVLYSSHNNNY LA | WYQQKPGQPPK LLIY | W ASTRES | GVPDRFSGSGSG TEFTLTISSLQAEDVAVY YC | QQYYS TPPT | FGQGTK VEIK |
| iPS:44 1505 .001.006 | VK4|B3/J K1 | DIVMTQSPDSLAVSLG ERATIKC | KSS QSVLYSSHNNNY LA | WYQQKPGQPPK LLIY | W ASTRES | GVPDRFSGSGSG TEFTLTISSLQAEDVAVY YC | QQYYS TPPT | FGQGTK VEIK |
| iPS:44 1512 .001.007 | VK4|B3/J K1 | DIVMTQSPDSLAVSLG ERATIKC | KSS QSVLYSSHNNNY LA | WYQQKPGQPPK LLIY | W ASTRES | GVPDRFSGSGSG TEFTLTISSLQAEDVAVY YC | QQYYS TPPT | FGQGTK VEIK |
| iPS:44 1519 .001.008 | VK4|B3/J K1 | DIVMTQSPDSLAVSLG ERATIKC | KSS QSVLYSSHNNNY LA | WYQQKPGQPPK LLIY | W ASTRES | GVPDRFSGSGSG TEFTLTISSLQAEDVAVY YC | QQYYS TPPT | FGQGTK VEIK |
| iPS:44 1554 .001.013 | VK4|B3/J K1 | DIVMTQFPDSLAVSLG ERATIKC | KSS QSVLYSSHNNNY LA | WYQQKPGQPPK LLIY | W ASTRES | GVPDRFSGSGSG TEFTLTISSLQAEDVAVY YC | QQYYS TPPT | FGQGTK VEIK |
| iPS:44 1595 .001.019 | VK4|B3/J K1 | DIVMTQSPDSLAVSLG ERATINC | KSS QSVLYSSHNNNY LA | WYQQKPGQPPK LLIY | W ASTRES | GVPDRFSGSGSG TEFTLTISSLEAEDVAVY YC | QQYYS TPPT | FGQGTK VEIK |

Figure 53 (Continued)

| | | K_FR1 | K_CDR1 | K_FR2 | K_CDR2 | K_FR3 | K_CDR3 | K_FR4 |
|---|---|---|---|---|---|---|---|---|
| iPS:44 1604 | 21-225_25A4 .001.020 | VK4|B3|J K1 | DIVMTQSPDSLAVSLG ERATINC | KSS--- QSVLYSSHNNNY LA | WYQQKPGQPPK LLIY | W------ ASTRES | GVPDRFSGSGSG--- TEFTLTISSLQAEDVAVY YC | QQYYS------ ---------TPFT | FGQGTK VEIK |
| iPS:44 1613 | 21-225_25A4 .001.021 | VK4|B3|J K1 | DIVMTQSPDSLAVSLG ERATINC | KSS--- QSVLYSSHNNNY LA | WYQQKPGQPPK LLIY | W------ ASTRES | GVPDRFSGSGSG--- TEFTLTISSLQAEDVAVY YC | QQYYS------ ---------TPFT | FGQGTK VEIK |
| iPS:44 3006 | 21-225_25A4 .001.029 | VK4|B3|J K1 | DIVMTQFPDSLAVSLG ERATIKC | KSS--- QSVLYSSHNNNY LA | WYQQKPGQPPK LLIY | W------ ASTRES | GVPDRFSGSGSG--- TEFTLTISSLQAEDVAVY YC | QQYYS------ ---------TPPT | FGQGTK VEIK |
| iPS:44 1962 | 21-225_4A2 .001.023 | VK4|B3|J K1 | DIVMTQSPDSLAVSLG ERATINC | KSS--- QSIHSSNNNNY LA | WFQQKPGQPPK LLIY | W------ ASTRES | GVPDRFSGSGSG--- TDFTLTISSLQPEDVAVY YC | QQYYS------ ---------TPVI | FGQGTK VEIK |
| iPS:44 1999 | 21-225_4A2 .001.028 | VK4|B3|J K1 | DIVMTQSPDSLAVSLG ERATINC | KSS--- QSIHSSNNNNY LA | WFQQKPGQPPK LLIY | W------ ASTRES | GVPDRFSGSGSG--- TDFTLTISSLQPEDVAVY YC | QQYYS------ ---------TPVI | FGQGTK VEIK |
| iPS:44 2006 | 21-225_4A2 .001.029 | VK4|B3|J K1 | DIVMTQSPDSLAVSLG ERATINC | KSS--- QSIHSSNNNNY LA | WFQQKPGQPPK LLIY | W------ ASTRES | GVPDRFSGSGSG--- TDFTLTISSLQPEDVAVY YC | QQYYS------ ---------TPVI | FGQGTK VEIK |
| iPS:44 2020 | 21-225_4A2 .001.031 | VK4|B3|J K1 | DIVMTQSPDSLAVSLG ERATINC | KSS--- QSIHSSNNNNY LA | WFQQKPGQPPK LLIY | W------ ASTRES | GVPDRFSGSGSG--- TDFTLTISSLQPEDVAVY YC | QQYYN------ ---------TPVI | FGPGTK VEIK |
| Germline | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGPGTK VDIK |
| iPS:39 3954 | 21-225_4H6 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- IDFTLTISSLQPEDFAIY YC | QQANS------ ---------FPFT | FGPGTK VDIK |
| iPS:44 2050 | 21-225_4H6. 004 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGPGTK VDIK |
| iPS:44 2059 | 21-225_4H6. 005 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGQGTK VDIK |
| iPS:44 2065 | 21-225_4H6. 006 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGQGTK VDIK |
| iPS:44 2071 | 21-225_4H6. 007 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGPGTK VDIK |
| iPS:44 2078 | 21-225_4H6. 008 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGQGTK VDIK |
| iPS:44 2085 | 21-225_4H6. 009 | VK1|L5|J K3 | DIQMTQSPSSVSASVG DRVTITC | RAS---QGIS --- ----RWLA | WYQQKPGKAPK LLIY | G------ ASSLQS | GVPSRFSGSGSG--- TDFTLTISSLQPEDFAIY YC | QQANS------ ---------FPFT | FGQGTK VDIK |

Figure 53 (Continued)

| | | | K_FR1 | K_CDR1 | K_FR2 | K_CDR2 | K_FR3 | K_CDR3 | K_FR4 |
|---|---|---|---|---|---|---|---|---|---|
| iPS:44 2089 | 21- 225_4H6. 010 | VK1lL5J K3 | DIQMTQSPSSVSASVG DRVTIITC | RAS--QGIS---- ----RWLA | WYQQKPGKAPK LEIY | G-------- ASSLQS | GVPSRFSGSGSG-- TDFTLTISSLQPEDFAIY YC | QQANS------------- ----------FPFT | FGQGTK VDIK |
| iPS:44 2093 | 21- 225_4H6. 011 | VK1lL5J K3 | DIQMTQSPSSVSASVG DRVTIITC | RAS--QGIS---- ----RWLA | WYQQKPGKAPK LEIY | G-------- ASSLQS | GVPSRFSGSGSG-- TDFTLTISSLQPEDFAIY YC | QQANS------------- ----------FPFT | FGQGTK VDIK |
| iPS:44 3016 | 21- 225_4H6. 014 | VK1lL5J K3 | DIQMTQSPSSVSASVG DRVTIITC | RAS--QGIS---- ----RWLA | WYQQKPGKAPK LEIY | G-------- ASSLQS | GVPSRFSGSGSG-- TDFTLTISSLQPEDPATY YC | QQANS------------- ----------FPFT | FGPGTK VDIK |
| Germline | | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYS------------- ----------TPFT | FGPGTK VDIK |
| iPS:41 2232 | 21- 225_4A2 001 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------TPVT | FGPGTK VGIK |
| iPS:42 2894 | 21- 225_4A2. 001.001 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------TPVT | FGPGTK VGIK |
| iPS:44 1841 | 21- 225_4A2. 001.002 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYS------------- ----------TPVT | FGPGTK VGIK |
| iPS:44 1847 | 21- 225_4A2. 001.003 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYO------------- ----------APVT | FGPGTK VGIK |
| iPS:44 1853 | 21- 225_4A2. 001.004 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------TPVT | FGPGTK VGIK |
| iPS:44 1859 | 21- 225_4A2. 001.005 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------TPVT | FGPGTK VGIK |
| iPS:44 1866 | 21- 225_4A2. 001.006 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------TPVT | FGPGTK VGIK |
| iPS:44 1873 | 21- 225_4A2. 001.007 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYS------------- ----------TPVT | FGPGTK VGIK |
| iPS:44 1880 | 21- 225_4A2. 001.008 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYS------------- ----------TPVT | FGPGTK VGIK |
| iPS:44 1884 | 21- 225_4A2. 001.008 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------APVT | FGPGTK VGIK |
| iPS:44 1888 | 21- 225_4A2. 001.009 | VK4lB3J K3 | DIVMTQSPDSLAVSLG ERATINC | KSS--- QSILHSSNNNNY LA | WFQQKPGQPPK LLLY | W-------- ASTRES | GVPDRFSGSGSG-- TDFTLTISSLQPEDVAVY YC | QQYYN------------- ----------APVT | FGPGTK VGIK |

Figure 53 (Continued)

| | | K_FR1 | K_CDR1 | K_FR2 | K_CDR2 | K_FR3 | K_CDR3 | K_FR4 |
|---|---|---|---|---|---|---|---|---|
| iPS:44 1892 | VK4|B3/JK3 | DIVMTQSPDSLAVSLG ERATINC | KSS---QSILHSSNNNNY LA | WFQQKPGQPPK LLIY | W------ASTRES | GVPDRFSGSGSG---TDFTLTISSLQPEDVAVY YC | QQYYQ-------TPVT | FGPGTK VGIK |
| iPS:44 1896 | VK4|B3/JK3 | DIVMTQSPDSLAVSLG ERATINC | KSS---QSILHSSNNNNY LA | WFQQKPGQPPK LLIY | W------ASTRES | GVPDRFSGSGSG---TDFTLTISSLQPEDVAVY YC | QQYYQ-------TPVI | FGPGTK VGIK |
| iPS:44 1900 | VK4|B3/JK3 | DIVMTQSPDSLAVSLG ERATINC | KSS---QSILHSSNNNNY LA | WFQQKPGQPPK LLIY | W------ASTRES | GVPDRFSGSGSG---TDFTLTISSLQPEDVAVY YC | QQYYQ-------TPVT | FGPGTK VGIK |
| iPS:44 1955 | VK4|B3/JK3 | DIVMTQSPDSLAVSLG ERATINC | KSS---QSILHSSNNNNY LA | WFQQKPGQPPK LLIY | W------ASTRES | GVPDRFSGSGSG---TDFTLTISSLQPEDVAVY YC | QQYYS-------TPVI | FGPGTK VGIK |
| iPS:44 1971 | VK4|B3/JK3 | DIVMTQSPDSLAVSLG ERATINC | KSS---QSILHSSNNNNY LA | WFQQKPGQPPK LLIY | W------ASTRES | GVPDRFSGSGSG---TDFTLTISSLQPEDVAVY YC | QQYYS-------TPVT | FGPGTK VGIK |
| Germline VK1|A30/JK1 | | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEIK |
| iPS:39 4041 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2115 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2122 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2129 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2136 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2171 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2178 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2199 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |
| iPS:44 2206 | VK1|A30/JK1 | DIQMTQSPSSLSASVG DRVTITC | RAS---QGIR-----NDLG | WYQQKPGKAPK RLIY | A------ASSLQS | GVPSRFSGSGSG---TEFTLTISSLQPEDFATY YC | LQHYS-------YPRT | FGQGTK VEVK |

Figure 53 (Continued)

| | | | | K_FR1 | K_CDR1 | K_FR2 | K_CDR2 | K_FR3 | K_CDR3 | K_FR4 |
|---|---|---|---|---|---|---|---|---|---|---|
| iPS:44 2213 | 21-225_5E5. 017 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| iPS:44 2220 | 21-225_5E5. 018 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| iPS:44 2227 | 21-225_5E5. 019 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| iPS:44 2255 | 21-225_5E5. 023 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| iPS:44 2262 | 21-225_5E5. 024 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| iPS:44 2269 | 21-225_5E5. 025 | VK1|A30/ JK1 | | DIQMTQSPSSLSASVG DRVTITC | RAS---QGIR----NDLG | WYQQKPGKAPK RLIY | A------ASSLQS | GVPSRFSGSGSG--TEFTLTISSLQPEDFATY YC | LQHYS--------YPRT | FGQGTK VEVK |
| | | | Germline | DIQMTQSPSSLSASVG DRVTITC | RAS---QNII----SYLN | WYQQKPGKAPK LLIY | A------ASSLQS | GVPSRFSGSGSG--TDFTLTISSLQPEDFAIY YC | QQTYS--------TPLT | FGGGTK VEIK |
| | VK1|O12/ JK4 | | | DIQMTQSPSSLSASVG DRVTITC | RAS---QNII----SYLN | WYQQKPGKAPK LLIY | A------ASSLQS | GVPSRFSGSGSG--TDFTLTISSLQPEDFAIY YC | QQTYS--------TPLT | FGGGTK VEIK |
| iPS:39 3930 | 21-225_7E11 .001 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:42 4460 | 21-225_7E11 .001 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:44 2311 | 21-225_7E11 .001.001 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:44 2317 | 21-225_7E11 .001.002 | VK1|O12/ JK4 | | DIQMTQSPSSLSASVG DRVTIAC | RAS---QNII----SYLN | WYQQKPGKAPK LLIY | T------ASSLQS | GVPSRFSGSGSG--TDFTLTISSLQPEDFAIY YC | QQTYS--------TPLT | FGGGTK VEIK |
| iPS:44 2323 | 21-225_7E11 .001.003 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:44 2330 | 21-225_7E11 .001.004 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:44 2337 | 21-225_7E11 .001.005 | VK1|O12/ JK4 | | DIQMTQSPSSLSASVG DRVTIAC | RAS---QNII----SYLN | WYQQKPGKAPK FLIY | T------ASSLQS | GVPSRFSGSGSG--TDFTLTISSLQPEDFAIY YC | QQTYS--------TPLT | FGGGTK VEIK |
| iPS:44 2344 | 21-225_7E11 .001.006 | VK1|O12/ JK4 | | DIQMTQSPSSLSASVG DRVTIAC | RAS---QNII----SYLN | WYQQKPGKAPK FLIY | I------ASSLQS | GVPSRFSGSGSG--TDFTLTISSLQPEDFAIY YC | QQTYS--------TPLT | FGGGTK VEIK |

Figure 53 (Continued)

| | | | | | | | | | |
|---|---|---|---|---|---|---|---|---|---|
| iPS:44 2351 | 21-225_7E11 .001.007 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2358 | 21-225_7E11 .001.008 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2365 | 21-225_7E11 .001.009 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2372 | 21-225_7E11 .001.010 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2379 | 21-225_7E11 .001.011 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2386 | 21-225_7E11 .001.012 | VK1|O12/ JK4 | DIQMTQSPSSLSASVG DRVTITC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2390 | 21-225_7E11 .001.013 | VK1|O12/ JK4 | DIQMTQSPSSLSASVG DRVTITC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2394 | 21-225_7E11 .001.014 | VK1|O12/ JK4 | DIQMTQSPSSLSASVG DRVTITC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2398 | 21-225_7E11 .001.015 | VK1|O12/ JK4 | DIQMTQSPSSLSASVG DRVTITC | RAS--QNII-- ---SYLN | WYQQKPGKAPK LLIY | T------ ASSLQS | GVPSRFSGSGSG-- TDFTLTISSLQPEDFAIY YC | QQTYS--------- ------------TPLT | FGGGTK VEIK |
| iPS:44 2402 | 21-225_7E11 .001.016 | VK1|O12/ JK4 | DIQMTQSPSSLSASVG DRVTITC | RAS--QNII-- ---SYLN | WYQQKPGKAPK LLIY | T------ ASSLQS | GVPSRFSGSGSG-- TDFTLTISSLQPEDFAIY YC | QQTYS--------- ------------TPLT | FGGGTK VEIK |
| iPS:44 2406 | 21-225_7E11 .001.017 | VK1|O12/ JK4 | DIQMTQSPSSLSASVG DRVTITC | RAS--QNII-- ---SYLN | WYQQKPGKAPK LLIY | T------ ASSLQS | GVPSRFSGSGSG-- TDFTLTISSLQPEDFAIY YC | QQTYS--------- ------------TPLT | FGGGTK VEIK |
| iPS:44 2410 | 21-225_7E11 .001.018 | VK1|O12/ JK4 | DIQMTQSPSSLSASVG DRVTITC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2417 | 21-225_7E11 .001.019 | VK1|O12/ JK4 | DIQMTQSPSSLSASVG DRVTITC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2431 | 21-225_7E11 .001.021 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |
| iPS:44 2438 | 21-225_7E11 .001.022 | VK1|O12/ JK4 | DIQMTQSPSSLSASVG DRVTIAC | RAS--QNII-- ---SYLN | WYQQKPGKAPK FLIY | T------ ASSLQS | GVPSRFSGSGSG-- TDFTLTISSLQPEDFAIY YC | QQTYS--------- ------------TPLT | FGGGTK VEIK |

Figure 53 (Continued)

| | | | DIQMTQSPSSLSASVG DRVTIAC | RAS---QNI---SYLN | WYQQKPGKAPK FLIY | T---ASSLQS | GVPSRFSGSGSG TDFTLTISLQPEDFAIY YC | QQTYS---------TPLT | FGGGTK VEIK |
|---|---|---|---|---|---|---|---|---|---|
| iPS:44 3027 | 21-225_7E11 .001_023 | VK1|O12/ JK4 | | | | | | | |
| HEAVY_VARIABL E | | | | | | | | | |
| | | Germline | H_FR1 | H_CDR1 | H_FR2 | H_CDR2 | H_FR3 | H_CDR3 | H_FR4 |
| iPS:39 2928 | | VH1|1-08/D6|6-19|RF1/J H4 | QVQLVQS--- GAEVKKPGASVKVSCK ASG-YTFT | S-------YDIN | WVRQATGQGLE WMG | WMYPN--- SGNTGYAQK FQG | RVTMTRNTSISTAYMELS SLRSEDTAVYYCAS | SSGWY---------YFDY | WGQGTL VTVSS |
| iPS:42 4419 | 21-225_25A4 .001 | VH1|1-08/D6|6-19|RF1/J H4 | QVLLVQS--- GAEVKRPGASVKVSCK ASG-YTFT | N-------YDIN | WVRQATGQGLE WMG | WMYPN--- SGNTGYAQK FQG | RVTMTRDTSISTAYMELS SLRSEDTAVYYCAS | SSGWY---------YFDY | WGQGTL VTVSS |
| iPS:44 1468 | 21-225_25A4 .001.001 | VH1|1-08/D6|6-19|RF1/J H4 | QVLLVQS--- GAEVKRPGASVKVSCK ASG-YTFT | N-------YDIN | WVRQATGQGLE WMG | WMYPN--- SGSTGYAQK FQG | RVTMTRDTSISTAYMELS SLRSEDTAVYYCAS | SSGWY---------YFDY | WGQGTL VTVSS |
| iPS:44 1475 | 21-225_25A4 .001.002 | VH1|1-08/D6|6-19|RF1/J H4 | QVLLVQS--- GAEVKRPGASVKVSCK ASG-YTFT | N-------YDIN | WVRQATGQGLE WMG | WMYPN--- SGNAGYAQK FQG | RVTMTRDTSISTAYMELS SLRSEDTAVYYCAS | SSGWY---------YFDY | WGQGTL VTVSS |
| iPS:44 1482 | 21-225_25A4 .001.003 | VH1|1-08/D6|6-19|RF1/J H4 | QVLLVQS--- GAEVKRPGASVKVSCK ASG-YTFT | N-------YDIN | WVRQATGQGLE WMG | WMYPN--- SGNVGYAQK FQG | RVTMTRDTSISTAYMELS SLRSEDTAVYYCAS | SSGWY---------YFDY | WGQGTL VTVSS |
| iPS:44 1489 | 21-225_25A4 .001.004 | VH1|1-08/D6|6-19|RF1/J H4 | QVLLVQS--- GAEVKRPGASVKVSCK ASG-YTFT | N-------YDIN | WVRQATGQGLE WMG | WMYPN--- SGQTGYAQK FQG | RVTMTRDTSISTAYMELS SLRSEDTAVYYCAS | SSGWY---------YFDY | WGQGTL VTVSS |
| iPS:44 1496 | 21-225_25A4 .001.005 | VH1|1-08/D6|6-19|RF1/J H4 | QVQLVQS--- GAEVKRPGASVKVSCK ASG-YTFT | N-------YDIN | WVRQATGQGLE WMG | WMYPN--- SGSTGYAQK FQG | RVTMTRDTSISTAYMELS SLRSEDTAVYYCAS | SSGWY---------YFDY | WGQGTL VTVSS |
| iPS:44 1505 | 21-225_25A4 .001.006 | VH1|1-08/D6|6-19|RF1/J H4 | QVQLVQS--- GAEVKRPGASVKVSCK ASG-YTFT | N-------YDIN | WVRQATGQGLE WMG | WMYPN--- SGNAGYAQK FQG | RVTMTRDTSISTAYMELS SLRSEDTAVYYCAS | SSGWY---------YFDY | WGQGTL VTVSS |
| iPS:44 1512 | 21-225_25A4 .001.007 | VH1|1-08/D6|6-19|RF1/J H4 | QVQLVQS--- GAEVKRPGASVKVSCK ASG-YTFT | N-------YDIN | WVRQATGQGLE WMG | WMYPN--- SGNVGYAQK FQG | RVTMTRDTSISTAYMELS SLRSEDTAVYYCAS | SSGWY---------YFDY | WGQGTL VTVSS |

Figure 53 (Continued)

| | | | | | | | | |
|---|---|---|---|---|---|---|---|---|
| iPS:44 1519 | 21- 225_25A4 .001.008 | VH1\|1- 08\|D6\|6- 19\|RF1/J H4 | QVQLVQS- GAEVKRPGASVKVSCK ASG-YTFT | N-----YDIN | WVRQATGQGLE WMG | WMYPN---- SCQTGYAQK FQG | RVTMTRDISISTAYMELS SLRSEDTAVYYCAS | SSGWY--------- --------YFDY | WGQGTL VTVSS |
| iPS:44 1554 | 21- 225_25A4 .001.013 | VH1\|1- 08\|D6\|6- 19\|RF1/J H4 | QVLLVQS- GAEVKRPGASVKVSCK ASG-YTFT | N-----YDIN | WVRQATGQGLE WMG | WMYPN---- SGSTGYAQK FQG | RVTMTRDISISTAYMELS SLRSEDTAVYYCAS | SSGWY--------- --------YFDY | WGQGTL VTVSS |
| iPS:44 1595 | 21- 225_25A4 .001.019 | VH1\|1- 08\|D6\|6- 19\|RF1/J H4 | QVQLVQS- GAEVKRPGASVKVSCK ASG-YTFT | N-----YDIN | WVRQAPGQGLE WMG | WMYPN---- SGSTGYAQK FQG | RVTMTRDISISTAYMELS SLRSEDTAVYYCAS | SSGWY--------- --------YFDY | WGQGTL VTVSS |
| iPS:44 1604 | 21- 225_25A4 .001.020 | VH1\|1- 08\|D6\|6- 19\|RF1/J H4 | QVLLVQS- GAEVKRPGASVKVSCK ASG-YTFT | N-----YDIN | WVRQAPGQGLE WMG | WMYPN---- SCQTGYAQK FQG | RVTMTRDISISTAYMELS SLRSEDTAVYYCAS | SSGWY--------- --------YFDY | WGQGTL VTVSS |
| iPS:44 1613 | 21- 225_25A4 .001.021 | VH1\|1- 08\|D6\|6- 19\|RF1/J H4 | QVQLVQS- GAEVKRPGASVKVSCK ASG-YTFT | N-----YDIN | WVRQATGQGLE WMG | WMYPN---- SGNAGYAQK FQG | RVTMTRDISISTAYMELS SLRSEDTAVYYCAS | SSGWY--------- --------YFDY | WGQGTL VTVSS |
| iPS:44 3006 | 21- 225_25A4 .001.029 | VH1\|1- 08\|D6\|6- 19\|RF1/J H4 | QVLLVQS- GAEVKRPGASVKVSCK ASG-YTFT | N-----YDIN | WVRQATGQGLE WMG | WMYPN---- SGQTGYAQK FQG | RVTMTRDISISTAYMELS SLRSEDTAVYYCAS | SSGWY--------- --------YFDY | WGQGTL VTVSS |
| iPS:41 2232 | 21- 225_4A2 .001 | VH1\|1- 08\|D6\|6- 19\|RF1/J H4 | QVQLVQS- GTEVKKPGASVKVSCK ASG-YTFT | N-----YDIN | WVRQATGQGLE WMG | WMHPN---- SCNTGYAQK FQG | RVTLTRNISTAYMELS SLRSEDTAVYYCAS | SSGWY--------- --------YFDY | WGQGTL VTVSS |
| iPS:42 2894 | 21- 225_4A2 .001 | VH1\|1- 08\|D6\|6- 19\|RF1/J H4 | QVQLVQS- GTEVKKPGASVKVSCK ASG-YTFT | N-----YDIN | WVRQATGQGLE RMG | WMHPN---- SGNIGYAQK FQG | RVTLTRDISISTAYMELS SLRSEDTAVYYCAS | SSGWY--------- --------YFDY | WGQGTL VTVSS |
| iPS:44 1841 | 21- 225_4A2. 001.001 | VH1\|1- 08\|D6\|6- 19\|RF1/J H4 | QVQLVQS- GTEVKKPGASVKVSCK ASG-YTFT | N-----YDIN | WVRQATGQGLE WMG | WMHPN---- SGNTGYAQK FQG | RVTLTRDISISTAYMELS SLRSEDTAVYYCAS | SSGWY--------- --------YFDY | WGQGTL VTVSS |
| iPS:44 1847 | 21- 225_4A2. 001.002 | VH1\|1- 08\|D6\|6- 19\|RF1/J H4 | QVQLVQS- GTEVKKPGASVKVSCK ASG-YTFT | N-----YDIN | WVRQATGQGLE WMG | WMHPN---- SCNTGYAQK FQG | RVTLTRDISISTAYMELS SLRSEDTAVYYCAS | SSGWY--------- --------YFDY | WGQGTL VTVSS |
| iPS:44 1853 | 21- 225_4A2. 001.003 | VH1\|1- 08\|D6\|6- 19\|RF1/J H4 | QVQLVQS- GTEVKKPGASVKVSCK ASG-YTFT | N-----YDIN | WVRQATGQGLE WMG | WMHPN---- SGNIGYAQK FQG | RVTLTRDISISTAYMELS SLRSEDTAVYYCAS | SSGWY--------- --------YFDY | WGQGTL VTVSS |
| iPS:44 1859 | 21- 225_4A2. 001.004 | VH1\|1- 08\|D6\|6- 19\|RF1/J H4 | QVQLVQS- GTEVKKPGASVKVSCK ASG-YTFT | N-----YDIN | WVRQATGQGLE WMG | WMHPN---- SCNAGYAQK FQG | RVTLTRDISISTAYMELS SLRSEDTAVYYCAS | SSGWY--------- --------YFDY | WGQGTL VTVSS |

Figure 53 (Continued)

| | | | | | | | | | |
|---|---|---|---|---|---|---|---|---|---|
| iPS:44 1866 | 21- 225_4A2. 001.005 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGSTGYAQK FQG | RVTLTRDISISTAYMELS SLRSEDTAVYYCAS | SSGWY--------------YFDY | WGQGTL VTVSS |
| iPS:44 1873 | 21- 225_4A2. 001.006 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGQTGYAQK FQG | RVTLTRDISISTAYMELS SLRSEDTAVYYCAS | SSGWY--------------YFDY | WGQGTL VTVSS |
| iPS:44 1880 | 21- 225_4A2. 001.007 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGQTGYAQK FQG | RVTLTRDISISTAYMELS SLRSEDTAVYYCAS | SSGWY--------------YFDY | WGQGTL VTVSS |
| iPS:44 1884 | 21- 225_4A2. 001.008 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGNAGYAQK FQG | RVTLTRDISISTAYMELS SLRSEDTAVYYCAS | SSGWY--------------YFDY | WGQGTL VTVSS |
| iPS:44 1888 | 21- 225_4A2. 001.009 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGSIGYAQK FQG | RVTLTRDISISTAYMELS SLRSEDTAVYYCAS | SSGWY--------------YFDY | WGQGTL VTVSS |
| iPS:44 1892 | 21- 225_4A2. 001.010 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGQIGYAQK FQG | RVTLTRDISISTAYMELS SLRSEDTAVYYCAS | SSGWY--------------YFDY | WGQGTL VTVSS |
| iPS:44 1896 | 21- 225_4A2. 001.011 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGQTGYAQK FQG | RVTLTRDISISTAYMELS SLRSEDTAVYYCAS | SSGWY--------------YFDY | WGQGTL VTVSS |
| iPS:44 1900 | 21- 225_4A2. 001.012 | VH1j1- 08/D6j6- 19jRF1/J H4 | QVQLVQS- GTEVKKPGASVKVSCK ASG-YTFT | N-----YDIN | WVRQATGQGLE WMG | WMHPN---- SGQTGYAQK FQG | RVTLTRDISISTAYMELS SLRSEDTAVYYCAS | SSGWY--------------YFDY | WGQGTL VTVSS |
| iPS:44 1955 | 21- 225_4A2. 001.022 | VH1j1- 08/D6j6- 19jRF1/J H4 | QVQLVQS- GAEVKKPGASVKVSCK ASG-YTFT | N-----YDIN | WVRQAPGQGLE WMG | WMHPN---- SGNTGYAQK FQG | RVTLTRDISISTAYMELS SLRSEDTAVYYCAS | SSGWY--------------YFDY | WGQGTL VTVSS |
| iPS:44 1962 | 21- 225_4A2. 001.023 | VH1j1- 08/D6j6- 19jRF1/J H4 | QVQLVQS- GAEVKKPGASVKVSCK ASG-YTFT | N-----YDIN | WVRQAPGQGLE WMG | WMHPN---- SGQTGYAQK FQG | RVTLTRDISISTAYMELS SLRSEDTAVYYCAS | SSGWY--------------YFDY | WGQGTL VTVSS |
| iPS:44 1971 | 21- 225_4A2. 001.024 | VH1j1- 08/D6j6- 19jRF1/J H4 | QVQLVQS- GAEVKKPGASVKVSCK ASG-YTFT | N-----YDIN | WVRQAPGQGLE WMG | WMHPN---- SGQIGYAQK FQG | RVTLTRDISISTAYMELS SLRSEDTAVYYCAS | SSGWY--------------YFDY | WGQGTL VTVSS |
| iPS:44 1999 | 21- 225_4A2. 001.028 | VH1j1- 08/D6j6- 19jRF1/J H4 | QVQLVQS- GAEVKKPGASVKVSCK ASG-YTFT | N-----YDIN | WVRQAPGQGLE WMG | WMHPN---- SGQTGYAQK FQG | RVTLTRDISISTAYMELS SLRSEDTAVYYCAS | SSGWY--------------YFDY | WGQGTL VTVSS |

Figure 53 (Continued)

| | | H_FR1 | H_CDR1 | H_FR2 | H_CDR2 | H_FR3 | H_CDR3 | H_FR4 |
|---|---|---|---|---|---|---|---|---|
| iPS:44 2006 | 21-225_4A2. 001.029 | VH1∫1-08/D6∫6-19/RF1/J H4 | QVQLVQS-GAEVKKPGASVKVSCK ASG-YTFT | N------YDIN | WVRQAPGQGLE WMG | WMHPN----SGGTGYAQK FQG | RVTLTRDTSISTAYMELS SLRSEDTAVYYCAS | SSGWY-------YFDY | WGQGTL VTVSS |
| iPS:44 2020 | 21-225_4A2. 001.031 | VH1∫1-08/D6∫6-19/RF1/J H4 | QVQLVQS-GGEVKKPGASVKVSCK ASG-YTFT | N------YDIN | WVRQAEGQGLE WMG | WMHPN----SGNEGYAQK FQG | RVTLTRDTSISTAYMELS SLRSEDTAVYYCAS | SSGWY-------YFDY | WGQGTL VTVSS |
| | Germline | H_FR1 | H_CDR1 | H_FR2 | H_CDR2 | H_FR3 | H_CDR3 | H_FR4 |
| | VH1∫1-02/D1∫1-1/RF1/JH 4 | QVQLVQS-GAEVKKPGASVKVSCK ASG-YTFT | -------YYLH | WVRQAPGQGLE WMG | WIHPN----SGGTNYAQK FQG | RVTMTRDTSISTAYMELS SLRSEDTAVYYCAR | -------YFDY | WGQGTL VTVSS |
| iPS:39 3954 | 21-225_4H6 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DGTS-------SFDY | WGQGTL VTVSS |
| iPS:44 2050 | 21-225_4H6. 004 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DGTS-------SFDY | WGQGTL VTVSS |
| iPS:44 2059 | 21-225_4H6. 005 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DGTS-------SFDY | WGQGTL VTVSS |
| iPS:44 2065 | 21-225_4H6. 006 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DGTS-------SFDY | WGQGTL VTVSS |
| iPS:44 2071 | 21-225_4H6. 007 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DATS-------SFDY | WGQGTL VTVSS |
| iPS:44 2078 | 21-225_4H6. 008 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | SGTS-------SFDY | WGQGTL VTVSS |
| iPS:44 2085 | 21-225_4H6. 009 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | SGTS-------SFDY | WGQGTL VTVSS |
| iPS:44 2089 | 21-225_4H6. 010 | VH1∫1-02/D1∫1-1/RF1/JH 4 | QVQLVQS-GAEVKKPGASVKVSCK ASG-YTFT | D------YYLH | WVRQAPGQGLE WMG | WIHPN----SGGTNYAQK FQG | RVTMTRDTSISTAYMELS SLRSDDTAVYYCAR | DATS-------SFDY | WGQGTL VTVSS |

Figure 53 (Continued)

| | | | H_FR1 | H_CDR1 | H_FR2 | H_CDR2 | H_FR3 | H_CDR3 | H_FR4 |
|---|---|---|---|---|---|---|---|---|---|
| iPS:44 2093 | 21-225_4H6. 011 | VH1\|1-02/D1\|1-1\|RF1/JH4 | QVQLVQS-GAEVKKPGASVKVSCK ASG-YTFT | D------YYLH | WVRQAPGQGLE WMG | WIHPN---SGGTNYAQK FQG | RVTMTRDTSISTAYMELS SLRSDDTAVYYCAR | DATS------------SFDY | WGQGTL VTVSS |
| iPS:44 3016 | 21-225_4H6. 014 | VH1\|1-02/D1\|1-1\|RF1/JH4 | QVQLVQS-GAEVKKPGASVKVSCK ASG-YTFT | D------YYLH | WVRQAPGQGLE WMG | WIHPN---SGGTNYAQK FQG | RVTMTRDTSISTAMGLS SLRSDDTAVYYCAR | DATS------------SFDY | WGQGTL VTVSS |
| | | Germline | H_FR1 | H_CDR1 | H_FR2 | H_CDR2 | H_FR3 | H_CDR3 | H_FR4 |
| | VH3\|3-33/D6\|6-6\|RF1/JH6 | | QVQLVES-GGGVVQPGRSLRLSCA ASG-FTFS | S------YGMH | WVRQAPGKGLE WVA | VIWYD---GSNKYYADS VKG | RFTISRDNSKNTLYLQMN SLRAEDTAVYYCAR | EVYSSGY------------YDYGMDV | WGQGTT VTVSS |
| iPS:39 4041 | 21-225_5E5 | VH3\|3-33/D6\|6-6\|RF1/JH6 | QVQLVES-GGGVVQPGRSLRLSCA ASG-FTFS | N------YVMH | WVRQAPGKGLE WVA | VIWYD---GSNKYYADS VKG | RFTISRDNSKNTLYLQMN SLRAEDTAVYYCTR | EVYSSGW------------YDYGMDV | WGQGTT VTVSS |
| iPS:44 2115 | 21-225_5E5. 003 | VH3\|3-33/D6\|6-6\|RF1/JH6 | QVQLVES-GGGVVQPGRSLRLSCA ASG-FTFS | N------YVMH | WVRQAPGKGLE WVA | VIWYD---ASNKYYADS VKG | RFTISRDNSKNTLYLQMN SLRAEDTAVYYCTR | EVYSSGW------------YDYGMDV | WGQGTT VTVSS |
| iPS:44 2122 | 21-225_5E5. 004 | VH3\|3-33/D6\|6-6\|RF1/JH6 | QVQLVES-GGGVVQPGRSLRLSCA ASG-FTFS | N------YVMH | WVRQAPGKGLE WVA | VIWYD---GSNKYYAES VKG | RFTISRDNSKNTLYLQMN SLRAEDTAVYYCTR | EVYSSGW------------YDYGMDV | WGQGTT VTVSS |
| iPS:44 2129 | 21-225_5E5. 005 | VH3\|3-33/D6\|6-6\|RF1/JH6 | QVQLVES-GGGVVQPGRSLRLSCA ASG-FTFS | N------YVMH | WVRQAPGKGLE WVA | VIWYD---GSNKYYAGS VKG | RFTISRDNSKNTLYLQMN SLRAEDTAVYYCTR | EVYSSGW------------YDYGMDV | WGQGTT VTVSS |
| iPS:44 2136 | 21-225_5E5. 006 | VH3\|3-33/D6\|6-6\|RF1/JH6 | QVQLVES-GGGVVQPGRSLRLSCA ASG-FTFS | N------YVMH | WVRQAPGKGLE WVA | VIWYD---GSNKYYADA VKG | RFTISRDNSKNTLYLQMN SLRAEDTAVYYCTR | EVYSSGW------------YDYGMDV | WGQGTT VTVSS |
| iPS:44 2171 | 21-225_5E5. 011 | VH3\|3-33/D6\|6-6\|RF1/JH6 | QVQLVES-GGGVVQPGRSLRLSCA ASG-FTFS | N------YVMH | WVRQAPGKGLE WVA | VIWYD---ASNKYYAES VKG | RFTISRDNSKNTLYLQMN SLRAEDTAVYYCTR | EVYSSGW------------YDYGMDV | WGQGTT VTVSS |
| iPS:44 2178 | 21-225_5E5. 012 | VH3\|3-33/D6\|6-6\|RF1/JH6 | QVQLVES-GGGVVQPGRSLRLSCA ASG-FTFS | N------YVMH | WVRQAPGKGLE WVA | VIWYD---ASNKYYADA VKG | RFTISRDNSKNTLYLQMN SLRAEDTAVYYCTR | EVYSSGW------------YDYGMDV | WGQGTT VTVSS |
| iPS:44 2199 | 21-225_5E5. 015 | VH3\|3-33/D6\|6-6\|RF1/JH6 | QVQLVES-GGGVVQPGRSLRLSCA ASG-FTFS | N------YVMH | WVRQAPGKGLE WVA | VIWYD---ASNKYYADS VKG | RFTISRDNSKNTLYLQMN SLRAEDTAVYYCTR | EVYSSGY------------YDYGMDV | WGQGTT VTVSS |

Figure 53 (Continued)

| | | | | | | | | | |
|---|---|---|---|---|---|---|---|---|---|
| iPS:44 2206 | 21-225_5E5.016 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----ASNKYYADS VKG | RFTISRDNSKNTLYLQMN SLRAEDTAVYYCTR | EVYSSGF------YDYGMDV | WGQGTT VTVSS |
| iPS:44 2213 | 21-225_5E5.017 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----GSNKYYAES VKG | RFTISRDNSKNTLYLQMN SLRAEDTAVYYCTR | EVYSSGY------YDYGMDV | WGQGTT VTVSS |
| iPS:44 2220 | 21-225_5E5.018 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----GSNKYYADS VKG | RFTISRDNSKNTLYLQMN SLRAEDTAVYYCTR | EVYSSGY------YDYGMDV | WGQGTT VTVSS |
| iPS:44 2227 | 21-225_5E5.019 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----GSNKYYADS VKG | RFTISRDNSKNTLYLQMN SLRAEDTAVYYCTR | EVYSSGF------YDYGMDV | WGQGTT VTVSS |
| iPS:44 2255 | 21-225_5E5.023 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----ASNKYYAES VKG | RFTISRDNSKNTLYLQMN SLRAEDTAVYYCTR | EVYSSGY------YDYGMDV | WGQGTT VTVSS |
| iPS:44 2262 | 21-225_5E5.024 | VH3\|3-33\|D6\|6-6\|RF1/JH6 | QVQLVES-GGGVVQPGRSLRLSCA ASG-FTFS | N------YVMH | WVRQAPGKGLE WVA | VIWYD----ASNKYYAEA VKG | RFTISRDNSKNTLYLQMN SLRAEDTAVYYCTR | EVYSSGY------YDYGMDV | WGQGTT VTVSS |
| | VH3\|3-07\|D6\|6-6\|RF1/JH6 | Germline | H_FR1 | H_CDR1 | H_FR2 | H_CDR2 | H_FR3 | H_CDR3 | H_FR4 |
| iPS:44 2269 | 21-225_5E5.025 | VH3\|3-07\|D6\|6-6\|RF1/JH6 | EVQLVES-GGGVVQPGGSLRLSCA ASG-FTFS | N------YVMH | WVRQAPGKGLE WVA | VIWYD----GSNKYYAES VKG | RFTISRDNAKNTLYLQMN SLRAEDTAVYYCTR | EVYSSGW------YDYGMDV | WGQGTT VTVSS |
| | VH3\|3-33\|D4\|4-11\|RF2/JH6 | Germline | H_FR1 | H_CDR1 | H_FR2 | H_CDR2 | H_FR3 | H_CDR3 | H_FR4 |
| iPS:39 3930 | 21-225_7E11.001 | VH3\|3-33\|D4\|4-11\|RF2/JH6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:42 4460 | 21-225_7E11.001 | VH3\|3-33\|D4\|4-11\|RF2/JH6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |

Figure 53 (Continued)

| | | | | | | | | |
|---|---|---|---|---|---|---|---|---|
| iPS:44 2311 | 21-225_7E11 .001.001 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:44 2317 | 21-225_7E11 .001.002 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:44 2323 | 21-225_7E11 .001.003 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:44 2330 | 21-225_7E11 .001.004 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:44 2337 | 21-225_7E11 .001.005 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----ASNKYYADS VKG | RFTISRDNSKNTLYLQMS SLRAEDTAVYYCAR | DLSMG----------GMDV | WGQGTT VTVSS |
| iPS:44 2344 | 21-225_7E11 .001.006 | VH3\|3-33\|D4\|4-11\|RF2/J H6 | QVQLVES-GGGVVQPGRSLRLSCA ASG-FTFS | S------FGMH | WVRQAPGKGLE WVA | IIWHE----GSNKYYADA VKG | RFTISRDNSKNTLYLQMS SLRAEDTAVYYCAR | DLSMG----------GMDV | WGQGTT VTVSS |
| iPS:44 2351 | 21-225_7E11 .001.007 | VH3\|3-33\|D4\|4-11\|RF2/J H6 | QVQLVES-GGGVVQPGRSLRLSCA ASG-FTFS | S------FGMH | WVRQAPGKGLE WVA | IIWHD----GSNKYYADS VKG | RFTISRDNSKNTLYLQMS SLRAEDTAVYYCAR | DLSMG----------GMDV | WGQGTT VTVSS |
| iPS:44 2358 | 21-225_7E11 .001.008 | VH3\|3-33\|D4\|4-11\|RF2/J H6 | QVQLVES-GGGVVQPGRSLRLSCA ASG-FTFS | S------FGMH | WVRQAPGKGLE WVA | IIWHE----GSNKYYADA VKG | RFTISRDNSKNTLYLQMS SLRAEDTAVYYCAR | DLSMG----------GMDV | WGQGTT VTVSS |
| iPS:44 2365 | 21-225_7E11 .001.009 | VH3\|3-33\|D4\|4-11\|RF2/J H6 | QVQLVES-GGGVVQPGRSLRLSCA ASG-FTFS | S------FGMH | WVRQAPGKGLE WVA | IIWHE----GSNKYYAES VKG | RFTISRDNSKNTLYLQMS SLRAEDTAVYYCAR | DLSMG----------GMDV | WGQGTT VTVSS |
| iPS:44 2372 | 21-225_7E11 .001.010 | VH3\|3-33\|D4\|4-11\|RF2/J H6 | QVQLVES-GGGVVQPGRSLRLSCA ASG-FTFS | S------FGMH | WVRQAPGKGLE WVA | IIWHS----GSNKYYAES VKG | RFTISRDNSKNTLYLQMS SLRAEDTAVYYCAR | DLSMG----------GMDV | WGQGTT VTVSS |
| iPS:44 2379 | 21-225_7E11 .001.011 | VH3\|3-33\|D4\|4-11\|RF2/J H6 | QVQLVES-GGGVVQPGRSLRLSCA ASG-FTFS | S------FGMH | WVRQAPGKGLE WVA | IIWHS----GSNKYYADA VKG | RFTISRDNSKNTLYLQMS SLRAEDTAVYYCAR | DLSMG----------GMDV | WGQGTT VTVSS |
| iPS:44 2386 | 21-225_7E11 .001.012 | VH3\|3-33\|D4\|4-11\|RF2/J H6 | QVQLVES-GGGVVQPGRSLRLSCA ASG-FTFS | S------FGMH | WVRQAPGKGLE WVA | IIWHS----GSNKYYADS VKG | RFTISRDNSKNTLYLQMS SLRAEDTAVYYCAR | DLSMG----------GMDV | WGQGTT VTVSS |

Figure 53 (Continued)

| | | H FR1 | H CDR1 | H FR2 | H CDR2 | H FR3 | H CDR3 | H FR4 |
|---|---|---|---|---|---|---|---|---|
| iPS:44 2390 | 21-225_7E11 .001_013 | VH3/3-33/D4/4-11/RF2/J H6 | QVQLVES-GGGVVQPGRSLRLSCA ASG-FTFS | S------FGMH | WVRQAPGKGKGLE WVA | IIWHD------GSNKYYAES VKG | RFTISRDNSKNTLYLQMS SLRAEDTAVYYCAR | DLSMG------------GMDV | WGQGTT VTVSS |
| iPS:44 2394 | 21-225_7E11 .001_014 | VH3/3-33/D4/4-11/RF2/J H6 | QVQLVES-GGGVVQPGRSLRLSCA ASG-FTFS | S------FGMH | WVRQAPGKGKGLE WVA | IIWHS------GSNKYYAES VKG | RFTISRDNSKNTLYLQMS SLRAEDTAVYYCAR | DLSMG------------GMDV | WGQGTT VTVSS |
| iPS:44 2398 | 21-225_7E11 .001_015 | VH3/3-33/D4/4-11/RF2/J H6 | QVQLVES-GGGVVQPGRSLRLSCA ASG-FTFS | S------FGMH | WVRQAPGKGKGLE WVA | IIWHS------GSNKYYADS VKG | RFTISRDNSKNTLYLQMS SLRAEDTAVYYCAR | DLSMG------------GMDV | WGQGTT VTVSS |
| iPS:44 2402 | 21-225_7E11 .001_016 | VH3/3-33/D4/4-11/RF2/J H6 | QVQLVES-GGGVVQPGRSLRLSCA ASG-FTFS | S------FGMH | WVRQAPGKGKGLE WVA | IIWHS------GSNKYYAES VKG | RFTISRDNSKNTLYLQMS SLRAEDTAVYYCAR | DLSMG------------GMDV | WGQGTT VTVSS |
| iPS:44 2406 | 21-225_7E11 .001_017 | VH3/3-33/D4/4-11/RF2/J H6 | QVQLVES-GGGVVQPGRSLRLSCA ASG-FTFS | S------FGMH | WVRQAPGKGKGLE WVA | IIWHE------GSNKYYADA VKG | RFTISRDNSKNTLYLQMS SLRAEDTAVYYCAR | DLSMG------------GMDV | WGQGTT VTVSS |
| iPS:44 2410 | 21-225_7E11 .001_018 | VH3/3-33/D4/4-11/RF2/J H6 | QVQLVES-GGGVVQPGRSLRLSCA ASG-FTFS | S------FGMH | WVRQAPGKGKGLE WVA | IIWHS------ASNKYYAES VKG | RFTISRDNSKNTLYLQMS SLRAEDTAVYYCAR | DLSMG------------GMDV | WGQGTT VTVSS |
| iPS:44 3027 | 21-225_7E11 .001_023 | VH3/3-33/D4/4-11/RF2/J H6 | QVQLVES-GGGVVQPGRSLRLSCA ASG-FTFS | S------FGMH | WVRQAPGKGKGLE WVA | IIWHD------ASNKYYADA VKG | RFTISRDNSKNTLYLQMS SLRAEDTAVYYCAR | DLSMG------------GMDV | WGQGTT VTVSS |
| | Germline | VH3/3-07/D4/4-11/RF2/J H6 | EVQLVES-GGGVVQPGGSLRLSCA ASG-FTFS | S------YAMS | WVRQAPGKGLE WVS | NIKQ------DGSEKYYVDS VKG | RFTISRDNAKNSLYLQMN SLRAEDTAVYYCAR | DYSNYY------------YYYMDV | WGQGTT VTVSS |
| iPS:44 2417 | 21-225_7E11 .001_019 | VH3/3-07/D4/4-11/RF2/J H6 | EVQLVES-GGGVVQPGGSLRLSCA ASG-FTFS | S------FGMH | WVRQAPGKGLE WVA | IIWHD------GSNKYYAES VKG | RFTISRDNAKNTLYLQMS SLRAEDTAVYYCAR | DLSMG------------GMDV | WGQGTT VTVSS |
| iPS:44 2431 | 21-225_7E11 .001_021 | VH3/3-07/D4/4-11/RF2/J H6 | EVQLVES-GGGVVQPGGSLRLSCA ASG-FTFS | S------FGMH | WVRQAPGKGLE WVA | IIWHS------GSNKYYAES VKG | RFTISRDNAKNTLYLQMS SLRAEDTAVYYCAR | DLSMG------------GMDV | WGQGTT VTVSS |
| iPS:44 2438 | 21-225_7E11 .001_022 | VH3/3-07/D4/4-11/RF2/J H6 | EVQLVES-GGGVVQPGGSLRLSCA ASG-FTFS | S------FGMH | WVRQAPGKGLE WVA | IIWHE------GSNKYYAES VKG | RFTISRDNAKNTLYLQMS SLRAEDTAVYYCAR | DLSMG------------GMDV | WGQGTT VTVSS |

Figure 54 (Table 7)
Standard IgG Antibody Variable Region Consensus Protein Alignment
CDRs defined by Kabat
Alignment numbering defined by Amgen Reference (AHo)

| KAPPA_VARIABLE | Germline | K_FR1 | K_CDR1 | K_FR2 | K_CDR2 | K_FR3 | K_CDR3 | K_FR4 |
|---|---|---|---|---|---|---|---|---|
| VK4jB3J K1 | | FIVMTQSPDSL AVSLGERATINC | KSS QSVLYSSNNKNYLA | WYQQKPGQPPK LLIY | WASTRES | GVPDRFSGSGS GTDFTLTISSLQAEDVA VYYC | QQYYS TPYT | FGQGTKV EIK |
| iPS:39 2928 21-225_25A 4 | VK4jB3J K1 | ........F....... ........ | .N... | H. | ..L. | | | E. | ..P. | ... |
| iPS:42 4419 21-225_25A 4.001 | VK4jB3J K1 | ........F....... .....K.. | .N... | H. | ..L. | .....E........... | E. | ..P. | ... |
| iPS:44 1468 21-225_25A 4.001.001 | VK4jB3J K1 | ........F....... .....K.. | .N... | H. | ..L. | .....E........... | E. | ..P. | ... |
| iPS:44 1475 21-225_25A 4.001.002 | VK4jB3J K1 | ........F....... .....K.. | .N... | H. | ..L. | .....E........... | E. | ..P. | ... |
| iPS:44 1482 21-225_25A 4.001.003 | VK4jB3J K1 | ........F....... .....K.. | .N... | H. | ..L. | .....E........... | E. | ..P. | ... |
| iPS:44 1489 21-225_25A 4.001.004 | VK4jB3J K1 | ........F....... .....K.. | .N... | H. | ..L. | .....E........... | E. | ..P. | ... |
| iPS:44 1496 21-225_25A 4.001.005 | VK4jB3J K1 | ................ .....K.. | .N... | H. | ..L. | .....E........... | E. | ..P. | ... |
| iPS:44 1505 21-225_25A 4.001.006 | VK4jB3J K1 | ................ .....K.. | .N... | H. | ..L. | .....E........... | E. | ..P. | ... |
| iPS:44 1512 21-225_25A 4.001.007 | VK4jB3J K1 | ................ .....K.. | .N... | H. | ..L. | .....E........... | E. | ..P. | ... |
| iPS:44 1519 21-225_25A 4.001.008 | VK4jB3J K1 | ........F....... .....K.. | .N... | H. | ..L. | .................. | E. | ..P. | ... |
| iPS:44 1554 21-225_25A 4.001.013 | VK4jB3J K1 | ................ ........ | ..... | H. | ..L. | .....E........... | E. | ..P. | ... |
| iPS:44 1595 21-225_25A 4.001.019 | VK4jB3J K1 | ................ ........ | ..... | | ..L. | .................. | | ..P. | ... |

Figure 54 (Continued)

| | | K_FR1 | K_CDR1 | | K_FR2 | K_CDR2 | K_FR3 | | K_CDR3 | K_FR4 |
|---|---|---|---|---|---|---|---|---|---|---|
| iPS:44 1604 | 21- 225_25A 4.001.020 | VK4\|B3/J K1 | ........... | ....... | ..H... | .L... | ........... | ........... | ....... | ....... | ....... |
| iPS:44 1613 | 21- 225_25A 4.001.021 | VK4\|B3/J K1 | ........... | ..N... | ..H... | .L... | ........... | ........... | ....E.. | ....P.. | ....... |
| iPS:44 3006 | 21- 225_25A 4.001.029 | VK4\|B3/J K1 | ....F...... | ..N..K | ..H... | .L... | ........... | ........... | ....E.. | ....P.. | ....... |
| iPS:44 1962 | 21- 225_4A2. 001.023 | VK4\|B3/J K1 | ........... | ..N... | .I.H.. | .F.L. | ........... | ........P. | ....... | ....P.. | ....... |
| iPS:44 1999 | 21- 225_4A2. 001.028 | VK4\|B3/J K1 | ........... | ..N... | .I.H.. | .F.L. | ........... | ........P. | ....... | ....V.. | ....... |
| iPS:44 2006 | 21- 225_4A2. 001.029 | VK4\|B3/J K1 | ........... | ..N... | .I.H.. | .F.L. | ........... | ........P. | ....... | ....V.. | ....... |
| iPS:44 2020 | 21- 225_4A2. 001.031 | VK4\|B3/J K1 | ........... | ..N... | .I.H.. | .F.L. | ........... | ........P. | ....N.. | ....V.. | ....P.. |
| VK1\|L5/J K3 | Germline | K_FR1 | K_CDR1 | | K_FR2 | K_CDR2 | K_FR3 | | K_CDR3 | K_FR4 |
| iPS:39 3954 | 21- 225_4H6. 004 | VK1\|L5/J K3 | ........... | ..R... | ....... | ...... | ........... | ........I. | ....... | ....... | ....... |
| iPS:44 2050 | 21- 225_4H6. 005 | VK1\|L5/J K3 | ........... | ..R... | ....... | ...... | .....G..... | ........I. | ....... | ....... | ....... |
| iPS:44 2059 | 21- 225_4H6. 006 | VK1\|L5/J K3 | ........... | ..R... | ....... | ...... | .....G..... | ........I. | ....... | ....... | ....... |
| iPS:44 2065 | 21- 225_4H6. 007 | VK1\|L5/J K3 | ........... | ..R... | ....... | ...... | .....G..... | ........I. | ....... | ....... | ....Q.. |
| iPS:44 2071 | 21- 225_4H6. 008 | VK1\|L5/J K3 | ........... | ..R... | ....... | ...... | .....G..... | ........I. | ....... | ....... | ....Q.. |
| iPS:44 2078 | 21- 225_4H6. 008 | VK1\|L5/J K3 | ........... | ..R... | ....... | ...... | .....G..... | ........I. | ....... | ....... | ....... |
| iPS:44 2085 | 21- 225_4H6. 009 | VK1\|L5/J K3 | ........... | ..R... | ....... | ...... | .....G..... | ........I. | ....... | ....... | ....Q.. |

Figure 54 (Continued)

| | | K_FR1 | K_CDR1 | K_FR2 | K_CDR2 | K_FR3 | K_CDR3 | K_FR4 |
|---|---|---|---|---|---|---|---|---|
| iPS:44 2089 | VK1\|L5/J K3 | ........ | .....R.... | ........ | ........ | ........ | ........Q.. | ..... |
| iPS:44 2093 | VK1\|L5/J K3 | ........ | .....R.... | ........ | G........ | ........ | ........Q.. | ..... |
| iPS:44 3016 | VK1\|L5/J K3 | ........ | .....R.... | ........ | G........ | ........I. | ........ | ..... |
| Germline VK4\|B3/J K3 | | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | QQYYS TPYT | FGQGTKVEIK |
| iPS:41 2232 | VK4\|B3/J K3 | ........ | ......N... | .F...L... | ........ | ........P.... | ........N........V... | .....G... |
| iPS:42 2894 | VK4\|B3/J K3 | ........ | ...I.H...N... | .F...L... | ........ | ........P.... | ........N......A.V... | .....G... |
| iPS:44 1841 | VK4\|B3/J K3 | ........ | ...I.H...N... | .F...L... | ........ | ........P.... | ........N........V... | .....G... |
| iPS:44 1847 | VK4\|B3/J K3 | ........ | ...I.H...N... | .F...L... | ........ | ........P.... | ........Q........V... | .....G... |
| iPS:44 1853 | VK4\|B3/J K3 | ........ | ...I.H...N... | .F...L... | ........ | ........P.... | ........N........V... | .....G... |
| iPS:44 1859 | VK4\|B3/J K3 | ........ | ...I.H...N... | .F...L... | ........ | ........P.... | ........N........V... | .....G... |
| iPS:44 1866 | VK4\|B3/J K3 | ........ | ...I.H...N... | .F...L... | ........ | ........P.... | ........N........V... | .....G... |
| iPS:44 1873 | VK4\|B3/J K3 | ........ | ...I.H...N... | .F...L... | ........ | ........P.... | ........N........V... | .....G... |
| iPS:44 1880 | VK4\|B3/J K3 | ........ | ...I.H...N... | .F...L... | ........ | ........P.... | ........N........V... | .....G... |
| iPS:44 1884 | VK4\|B3/J K3 | ........ | ...I.H...N... | .F...L... | ........ | ........P.... | ........N........V... | .....G... |
| iPS:44 1888 | VK4\|B3/J K3 | ........ | ...I.H...N... | .F...L... | ........ | ........P.... | ........N......A.V... | .....G... |

Figure 54 (Continued)

| | | | | | | | | | | |
|---|---|---|---|---|---|---|---|---|---|---|
| iPS:44 1892 | 21-225_4A2. 001.010 | VK4|B3/J K3 | | | .F. ..L. | | | | .Q. | .V. | .G. |
| iPS:44 1896 | 21-225_4A2. 001.011 | VK4|B3/J K3 | .N... | .I.H... | .F. ..L. | | | .Q. | .V. | .G. |
| iPS:44 1900 | 21-225_4A2. 001.012 | VK4|B3/J K3 | .N... | .I.H... | .F. ..L. | | | .Q. | .V. | .G. |
| iPS:44 1955 | 21-225_4A2. 001.022 | VK4|B3/J K3 | .N... | .I.H... | .F. ..L. | | | .Q. | .V. | .G. |
| iPS:44 1971 | 21-225_4A2. 001.024 | VK4|B3/J K3 | .N... | .I.H... | .F. ..L. | | .P. | | .V. | .G. |
| Germline | VK1|A30/ JK1 | K_FR1 DIQMTQSPSSLSA SVGDRVTITC | K_CDR1 RAS-QSIS -NYLN | K_FR2 WYQQTPGKAPK LLIY | K_CDR2 AASSLQS | K_FR3 GVPSRFSGSGS GTDFTLTISSLQPEDFAT YYC | K_CDR3 QQSYS -----TPWT | K_FR4 FGQGT KVEIK |
| iPS:39 4041 | 21-225_5E5. 003 | VK1|A30/ JK1 | | | | | | .Y. | .R. | .V. |
| iPS:44 2115 | 21-225_5E5. 004 | VK1|A30/ JK1 | | | | | | .Y. | .R. | .V. |
| iPS:44 2122 | 21-225_5E5. 005 | VK1|A30/ JK1 | | | | | | .Y. | .R. | .V. |
| iPS:44 2129 | 21-225_5E5. 006 | VK1|A30/ JK1 | | | | | | .Y. | .R. | .V. |
| iPS:44 2136 | 21-225_5E5. 011 | VK1|A30/ JK1 | | | | | | .Y. | .R. | .V. |
| iPS:44 2171 | 21-225_5E5. 012 | VK1|A30/ JK1 | | | | | | .Y. | .R. | .V. |
| iPS:44 2178 | 21-225_5E5. 015 | VK1|A30/ JK1 | | | | | | .Y. | .R. | .V. |
| iPS:44 2199 | 21-225_5E5. 016 | VK1|A30/ JK1 | | | | | | .Y. | .R. | .V. |
| iPS:44 2206 | | VK1|A30/ JK1 | | | | | | | | |

| | | | | | | | | |
|---|---|---|---|---|---|---|---|---|
| iPS:44 2351 | VK1\|O12/ JK4 1.001.007 | . . . . . . . . . . | . . . . . . . . | . . . . . . . . . . | . F . . . | . . . . . . . . . . | . . . . . . . . | . . . . . . . . . . | . . . . |
| iPS:44 2358 | VK1\|O12/ JK4 1.001.008 | . . . . . A . | . N . I . . | . F . . . | . T . . . | . . . . . . . . . . | . . I . . | . T . . . | . . . . |
| iPS:44 2365 | VK1\|O12/ JK4 1.001.009 | . . . . . A . | . N . I . . | . F . . . | . T . . . | . . . . . . . . . . | . . I . . | . T . . . | . . . . |
| iPS:44 2372 | VK1\|O12/ JK4 1.001.010 | . . . . . A . | . N . I . . | . F . . . | . T . . . | . . . . . . . . . . | . . I . . | . T . . . | . . . . |
| iPS:44 2379 | VK1\|O12/ JK4 1.001.011 | . . . . . A . | . N . I . . | . F . . . | . T . . . | . . . . . . . . . . | . . I . . | . T . . . | . . . . |
| iPS:44 2386 | VK1\|O12/ JK4 1.001.012 | . . . . . . . . . . | . N . I . . | . F . . . | . T . . . | . . . . . . . . . . | . . I . . | . T . . . | . . . . |
| iPS:44 2390 | VK1\|O12/ JK4 1.001.013 | . . . . . . . . . . | . N . I . . | . F . . . | . T . . . | . . . . . . . . . . | . . I . . | . T . . . | . . . . |
| iPS:44 2394 | VK1\|O12/ JK4 1.001.014 | . . . . . . . . . . | . N . I . . | . F . . . | . T . . . | . . . . . . . . . . | . . I . . | . T . . . | . . . . |
| iPS:44 2398 | VK1\|O12/ JK4 1.001.015 | . . . . . . . . . . | . N . I . . | . F . . . | . T . . . | . . . . . . . . . . | . . I . . | . T . . . | . . . . |
| iPS:44 2402 | VK1\|O12/ JK4 1.001.016 | . . . . . . . . . . | . N . I . . | . F . . . | . T . . . | . . . . . . . . . . | . . I . . | . T . . . | . . . . |
| iPS:44 2406 | VK1\|O12/ JK4 1.001.017 | . . . . . . . . . . | . N . I . . | . F . . . | . T . . . | . . . . . . . . . . | . . I . . | . T . . . | . . . . |
| iPS:44 2410 | VK1\|O12/ JK4 1.001.018 | . . . . . . . . . . | . N . I . . | . F . . . | . T . . . | . . . . . . . . . . | . . I . . | . T . . . | . . . . |
| iPS:44 2417 | VK1\|O12/ JK4 1.001.019 | . . . . . A . | . N . I . . | . F . . . | . T . . . | . . . . . . . . . . | . . I . . | . T . . . | . . . . |
| iPS:44 2431 | VK1\|O12/ JK4 1.001.021 | . . . . . A . | . N . I . . | . F . . . | . T . . . | . . . . . . . . . . | . . I . . | . T . . . | . . . . |
| iPS:44 2438 | VK1\|O12/ JK4 1.001.022 | . . . . . . . . . . | . N . I . . | . F . . . | . T . . . | . . . . . . . . . . | . . I . . | . T . . . | . . . . |

Figure 54 (Continued)

| | | | | | | | | |
|---|---|---|---|---|---|---|---|---|
| iPS:44 3027 | 21- 225_7E1 1.001.023 | VK1O12/ JK4 | ........ | ........N.I...... | ........ | ......T. | ..........I.... | .T....... | ... |

| HEAVY_VARIABLE | | | H FR1 | H CDR1 | H FR2 | H CDR2 | H FR3 | H CDR3 | H FR4 |
|---|---|---|---|---|---|---|---|---|---|
| | Germline | | EVQLLES GGGLVQPGGSLRV SCAASG-YTFT | SYGIH | WVRQAPGKGLEW MGC | SGYSGNT NYAQKFQG | RVTMTRDTSISTAYM ELSRLRSDDTAVYYCAR | GISSSWYEDL | WGQGTLVTVSS |
| iPS:39 2928 | 21- 225_25A 4 | VH1|1- 08/D6|6- 19|RF1/J H4 | ..L... R...... | N........ | ........ | ..Y..... | ........ | SSGWY- | ... |
| iPS:42 4419 | 21- 225_25A 4.001 | VH1|1- 08/D6|6- 19|RF1/J H4 | ..L... R...... | N........ | ........ | ..Y..... | ........D........S | SSGWY- | ... |
| iPS:44 1468 | 21- 225_25A 4.001.001 | VH1|1- 08/D6|6- 19|RF1/J H4 | ..L... R...... | N........ | ........ | ..Y..... S | ........D........S | SSGWY- | ... |
| iPS:44 1475 | 21- 225_25A 4.001.002 | VH1|1- 08/D6|6- 19|RF1/J H4 | ..L... R...... | N........ | ........ | ..Y..... .A | ........D........S | SSGWY- | ... |
| iPS:44 1482 | 21- 225_25A 4.001.003 | VH1|1- 08/D6|6- 19|RF1/J H4 | ..L... R...... | N........ | ........ | ..Y..... .V | ........D........S | SSGWY- | ... |
| iPS:44 1489 | 21- 225_25A 4.001.004 | VH1|1- 08/D6|6- 19|RF1/J H4 | ..L... R...... | N........ | ........ | ..Y..... Q. | ........D........S | SSGWY- | ... |
| iPS:44 1496 | 21- 225_25A 4.001.005 | VH1|1- 08/D6|6- 19|RF1/J H4 | ...... R...... | N........ | ........ | ..Y..... S. | ........D........S | SSGWY- | ... |
| iPS:44 1505 | 21- 225_25A 4.001.006 | VH1|1- 08/D6|6- 19|RF1/J H4 | ...... R...... | N........ | ........ | ..Y..... .A | ........D........S | SSGWY- | ... |
| iPS:44 1512 | 21- 225_25A 4.001.007 | VH1|1- 08/D6|6- 19|RF1/J H4 | ...... R...... | N........ | ........ | ..Y..... .V | ........D........S | SSGWY- | ... |

Figure 54 (Continued)

| | | | | | | | | |
|---|---|---|---|---|---|---|---|---|
| iPS:44 1519 | 21-225_25A 4.001.008 | VH1|1-08/D6|6-19|RF1/J H4 | .........R....... | ............... | ............N............ | .................. | ....Y........ Q......... | .........D........ ...........S | SSGWY-- ...... ...... |
| iPS:44 1554 | 21-225_25A 4.001.013 | VH1|1-08/D6|6-19|RF1/J H4 | ........L....... | ............... | ............N............ | .................. | ....Y........ S......... | .........D........ ...........S | SSGWY-- ...... ...... |
| iPS:44 1595 | 21-225_25A 4.001.019 | VH1|1-08/D6|6-19|RF1/J H4 | .........R....... | ............... | ............N............ | ........P......... | ....Y........ S......... | .........D........ ...........S | SSGWY-- ...... ...... |
| iPS:44 1604 | 21-225_25A 4.001.020 | VH1|1-08/D6|6-19|RF1/J H4 | ........L....... | ............... | ............N............ | ........P......... | ....Y........ Q......... | .........D........ ...........S | SSGWY-- ...... ...... |
| iPS:44 1613 | 21-225_25A 4.001.021 | VH1|1-08/D6|6-19|RF1/J H4 | .........R....... | ............... | ............N............ | .................. | ....Y........ A......... | .........D........ ...........S | SSGWY-- ...... ...... |
| iPS:44 3006 | 21-225_25A 4.001.029 | VH1|1-08/D6|6-19|RF1/J H4 | ........L....... | ............... | ............N............ | .................. | ....Y........ Q......... | .........D........ ...........S | SSGWY-- ...... ...... |
| iPS:41 2232 | 21-225_4A2 | VH1|1-08/D6|6-19|RF1/J H4 | ............... | ........T...... | ............N............ | .................. | ....H......... | ....L....D........ ...........S | SSGWY-- ...... ...... |
| iPS:42 2894 | 21-225_4A2_ 001 | VH1|1-08/D6|6-19|RF1/J H4 | ............... | ........T...... | ............N............ | .................. | ....H......... | ....L....D........ ...........S | SSGWY-- ...... ...... |
| iPS:44 1841 | 21-225_4A2. 001.001 | VH1|1-08/D6|6-19|RF1/J H4 | ............... | ........T...... | ............N............ | .................. | ....H......... | ....L....D........ ...........S | SSGWY-- ...... ...... |
| iPS:44 1847 | 21-225_4A2. 001.002 | VH1|1-08/D6|6-19|RF1/J H4 | ............... | ............... | ............N............ | .................. | ....H......... | ....L....D........ ...........S | SSGWY-- ...... ...... |
| iPS:44 1853 | 21-225_4A2. 001.003 | VH1|1-08/D6|6-19|RF1/J H4 | ............... | ........T...... | ............N............ | .................. | ....H......... | ....L....D........ ...........S | SSGWY-- ...... ...... |
| iPS:44 1859 | 21-225_4A2. 001.004 | VH1|1-08/D6|6-19|RF1/J H4 | ............... | ........T...... | ............N............ | .................. | ....H........ A......... | ....L....D........ ...........S | SSGWY-- ...... ...... |

Figure 54 (Continued)

| | | | | | | | | | |
|---|---|---|---|---|---|---|---|---|---|
| iPS:44 1866 | 21-225_4A2. 001.005 | VH1\|1-08/D6\|6-19\|RF1/J H4 | .......... | .......... | ....N..... | .......... | ..H...... S........ | ...L..D... ..........S | SSGWY-.... .......... |
| iPS:44 1873 | 21-225_4A2. 001.006 | VH1\|1-08/D6\|6-19\|RF1/J H4 | ......T... | .......... | ....N..... | .......... | ..H...... Q........ | ...L..D... ..........S | SSGWY-.... .......... |
| iPS:44 1880 | 21-225_4A2. 001.007 | VH1\|1-08/D6\|6-19\|RF1/J H4 | ......T... | .......... | ....N..... | .......... | ..H...... Q........ | ...L..D... ..........S | SSGWY-.... .......... |
| iPS:44 1884 | 21-225_4A2. 001.008 | VH1\|1-08/D6\|6-19\|RF1/J H4 | ......T... | .......... | ....N..... | .......... | ..H...... A........ | ...L..D... ..........S | SSGWY-.... .......... |
| iPS:44 1888 | 21-225_4A2. 001.009 | VH1\|1-08/D6\|6-19\|RF1/J H4 | ......T... | .......... | ....N..... | .......... | ..H...... Q........ | ...L..D... ..........S | SSGWY-.... .......... |
| iPS:44 1892 | 21-225_4A2. 001.010 | VH1\|1-08/D6\|6-19\|RF1/J H4 | ......T... | .......... | ....N..... | .......... | ..H...... A........ | ...L..D... ..........S | SSGWY-.... .......... |
| iPS:44 1896 | 21-225_4A2. 001.011 | VH1\|1-08/D6\|6-19\|RF1/J H4 | ......T... | .......... | ....N..... | .......... | ..H...... Q........ | ...L..D... ..........S | SSGWY-.... .......... |
| iPS:44 1900 | 21-225_4A2. 001.012 | VH1\|1-08/D6\|6-19\|RF1/J H4 | .......... | .......... | ....N..... | .......... | ..H...... S........ | ...L..D... ..........S | SSGWY-.... .......... |
| iPS:44 1955 | 21-225_4A2. 001.022 | VH1\|1-08/D6\|6-19\|RF1/J H4 | .......... | ...P...... | .......... | .......... | ..H...... .......... | ...L..D... ..........S | SSGWY-.... .......... |
| iPS:44 1962 | 21-225_4A2. 001.023 | VH1\|1-08/D6\|6-19\|RF1/J H4 | .......... | ...P...... | .......... | .......... | ..H...... .......... | ...L..D... ..........S | SSGWY-.... .......... |
| iPS:44 1971 | 21-225_4A2. 001.024 | VH1\|1-08/D6\|6-19\|RF1/J H4 | .......... | .......... | ....N..... | .......... | ..H...... Q........ | ...L..D... ..........S | SSGWY-.... .......... |
| iPS:44 1999 | 21-225_4A2. 001.028 | VH1\|1-08/D6\|6-19\|RF1/J H4 | .......... | .......... | ....N..... | .......... | ..H...... Q........ | ...L..D... ..........S | SSGWY-.... .......... |

Figure 54 (Continued)

| | | H FR1 | H CDR1 | H FR2 | H CDR2 | H FR3 | H CDR3 | H FR4 |
|---|---|---|---|---|---|---|---|---|
| iPS:44-2006 | VH1¦1-08¦D6¦6-19¦RF1/JH4 | | N........ | ....F..... | ....H........ | ....L..D....... | SSGWY-.... | ..... |
| iPS:44-2020 | VH1¦1-08¦D6¦6-19¦RF1/JH4 | ........G... | N........ | ....E..... | ....H......... S | ....L..D...S... | SSGWY-.... | ..... |
| Germline | | H FR1 | H CDR1 | H FR2 | H CDR2 | H FR3 | H CDR3 | H FR4 |
| VH1¦1-02¦D1¦1-1¦RF1¦JH4 | | QVQLVQS-GAEVKKPGASVKV SCKASGYTFT | G------YYMH | WVRQAPGQGLEWMG | WINPNSGGTNYAQKFQG RVTMTRDTSISTAYMELS RLRSDDTAVYYCAR | | ----YFDY | WGQGTLVTVSS |
| iPS:39-3954 | VH1¦1-02¦D1¦1-1¦RF1¦JH4 | | D........L. | | ....H........ | ..........S.... | DG.S-..... | .....S.... |
| iPS:44-2050 | VH1¦1-02¦D1¦1-1¦RF1¦JH4 | | D........L. | | ....H........ | ..........S.... | DG.S-..... | .....S.... |
| iPS:44-2059 | VH1¦1-02¦D1¦1-1¦RF1¦JH4 | | D........L. | | ....H........ | ..........S.... | DG.S-..... | .....S.... |
| iPS:44-2065 | VH1¦1-02¦D1¦1-1¦RF1¦JH4 | | D........L. | | ....H........ | ..........S.... | DG.S-..... | .....S.... |
| iPS:44-2071 | VH1¦1-02¦D1¦1-1¦RF1¦JH4 | | D........L. | | ....H........ | ..........S.... | DA.S-..... | .....S.... |
| iPS:44-2078 | VH1¦1-02¦D1¦1-1¦RF1¦JH4 | | D........L. | | ....H........ | ..........S.... | SG.S-..... | .....S.... |
| iPS:44-2085 | VH1¦1-02¦D1¦1-1¦RF1¦JH4 | | D........L. | | ....H........ | ..........S.... | SG.S-..... | .....S.... |
| iPS:44-2089 | VH1¦1-02¦D1¦1-1¦RF1¦JH4 | | D........L. | | ....H........ | ..........S.... | DA.S-..... | .....S.... |

Figure 54 (Continued)

| | | H FR1 | H CDR1 | H FR2 | H CDR2 | H FR3 | H CDR3 | H FR4 |
|---|---|---|---|---|---|---|---|---|
| iPS:44-2093 | 21-225_4H6.011 | VH1|1-02/D1|1-1|RF1|JH4 | ......... | D........L. | ......... | .......H..... | ............. | DA.S- ...S.... | ......... |
| iPS:44-3016 | 21-225_4H6.014 | VH1|1-02/D1|1-1|RF1|JH4 | ......... | D........L. | ......... | .......H..... | ......S...... | DA.S- ...S.... | ......... |
| Germline | | H FR1 QVQLVES-CGVGSGLL SCAAGC-TYSS | H CDR1 S------XGNH | H FR2 WVRQAPGKGLE WVA | H CDR2 SSNYIADSV KG | H FR3 RFTISRDNSKNTLYLQMNS LRAEDTAVYYCAR | H CDR3 VH3|3-33|D6|6-6|RF1|JH EXPRESSIV YYYGMDV | H FR4 WGQGTTV TVSS |
| iPS:39-4041 | 21-225_5E5 | VH3|3-33|D6|6-6|RF1|JH6 | ......... | N........V.. | ......... | ............. | ..........T.. | .VY..GW- ............D. | ......... |
| iPS:44-2115 | 21-225_5E5.003 | VH3|3-33|D6|6-6|RF1|JH6 | ......... | N........V.. | ......... | ..........A.. | ..........T.. | .VY..GW- ............D. | ......... |
| iPS:44-2122 | 21-225_5E5.004 | VH3|3-33|D6|6-6|RF1|JH6 | ......... | N........V.. | ......... | .......E..... | ..........T.. | .VY..GW- ............D. | ......... |
| iPS:44-2129 | 21-225_5E5.005 | VH3|3-33|D6|6-6|RF1|JH6 | ......... | N........V.. | ......... | .......G..... | ..........T.. | .VY..GW- ............D. | ......... |
| iPS:44-2136 | 21-225_5E5.006 | VH3|3-33|D6|6-6|RF1|JH6 | ......... | N........V.. | ......... | ..........A.. | ..........T.. | .VY..GW- ............D. | ......... |
| iPS:44-2171 | 21-225_5E5.011 | VH3|3-33|D6|6-6|RF1|JH6 | ......... | N........V.. | ......... | .......E..A.. | ..........T.. | .VY..GW- ............D. | ......... |
| iPS:44-2178 | 21-225_5E5.012 | VH3|3-33|D6|6-6|RF1|JH6 | ......... | N........V.. | ......... | ..........A.. | ..........T.. | .VY..GW- ............D. | ......... |
| iPS:44-2199 | 21-225_5E5.015 | VH3|3-33|D6|6-6|RF1|JH6 | ......... | N........V.. | ......... | ..........A.. | ..........T.. | .VY..G.- ............D. | ......... |

Figure 54 (Continued)

| | | H_FR1 | H_CDR1 | H_FR2 | H_CDR2 | H_FR3 | | H_CDR3 | H_FR4 |
|---|---|---|---|---|---|---|---|---|---|
| iPS:44-2206 | 21-225_5E5.016 | VH3j3-33/D6j6-6jRF1/JH6 | | N......V... | | ..........A | | ........T.... | VY..GF-........D. | .... |
| iPS:44-2213 | 21-225_5E5.017 | VH3j3-33/D6j6-6jRF1/JH6 | | N......V... | | .......E. | | ........T.... | VY..G..........D. | .... |
| iPS:44-2220 | 21-225_5E5.018 | VH3j3-33/D6j6-6jRF1/JH6 | | N......V... | | | | ........T.... | VY..G..........D. | .... |
| iPS:44-2227 | 21-225_5E5.019 | VH3j3-33/D6j6-6jRF1/JH6 | | N......V... | | .......E. | | ........T.... | VY..GF-........D. | .... |
| iPS:44-2255 | 21-225_5E5.023 | VH3j3-33/D6j6-6jRF1/JH6 | | N......V... | | ..........A...  | | ........T.... | VY..G..........D. | .... |
| iPS:44-2262 | 21-225_5E5.024 | VH3j3-33/D6j6-6jRF1/JH6 | | N......V... | | ..........A... | | ........T.... | VY..G..........D. | .... |
| VH3j3-07/D6j6-6jRF1/JH6 | | Germline | H_FR1 EVQLVES-GGGLVQPGGSLR LSCAASG-FTFS | H_CDR1 SY...YMS--YCMH | H_FR2 WVRQAPGKGLEWVA | H_CDR2 GSIKYYGSSV KG | H_FR3 RFTISRDNSKNTLYLQM NSLRAEDTAVYYCAR | | H_CDR3 DYSNYY------YYGMDV | H_FR4 WGQGTTV TVSS |
| iPS:44-2269 | 21-225_5E5.025 | VH3j3-07/D6j6-6jRF1/JH6 | | N......V.H | | V..WY....N...AE... | | ........T.... | VY..GW-........D. | .... |
| VH3j3-33/D4j4-11jRF2/JH6 | | Germline | H_FR1 | H_CDR1 S...---YCMH | H_FR2 WVRQAPGKGLEWVA | H_CDR2 CSRIYADSV KG | H_FR3 RFTISRDNSKNTLYLQM NSLRAEDTAVYYCAR | | H_CDR3 DYSNYY------YYGMDV | H_FR4 WGQGTTV TVSS |
| iPS:39-3930 | 21-225_7E1.1 | VH3j3-33/D4j4-11jRF2/JH6 | | ......F... | | I..H........ | | ........N... | L.MG----........- | .... |
| iPS:42-4460 | 21-225_7E1.001 | VH3j3-33/D4j4-11jRF2/JH6 | | ......F... | | I..H........ | | ........S... | L.MG----........- | .... |

Figure 54 (Continued)

| | | | | | | |
|---|---|---|---|---|---|---|
| iPS:44 2311 | VH3\|3-33\|D4\|4-11\|RF2\|J H6 | | ....F.... | ........ | I..H........S...... | .L.MG--- |
| iPS:44 2317 | VH3\|3-33\|D4\|4-11\|RF2\|J H6 | | ....F.... | ........ | I..H........S...... | .L.MG--- |
| iPS:44 2323 | VH3\|3-33\|D4\|4-11\|RF2\|J H6 | | ....F.... | ........ | I..HS.......S...... | .L.MG--- |
| iPS:44 2330 | VH3\|3-33\|D4\|4-11\|RF2\|J H6 | | ....F.... | ........ | I..HE.......S...... | .L.MG--- |
| iPS:44 2337 | VH3\|3-33\|D4\|4-11\|RF2\|J H6 | | ....F.... | ........ | I..H....A...S...... | .L.MG--- |
| iPS:44 2344 | VH3\|3-33\|D4\|4-11\|RF2\|J H6 | | ....F.... | ........ | I..H...E....S...... | .L.MG--- |
| iPS:44 2351 | VH3\|3-33\|D4\|4-11\|RF2\|J H6 | | ....F.... | ........ | I..H....A...S...... | .L.MG--- |
| iPS:44 2358 | VH3\|3-33\|D4\|4-11\|RF2\|J H6 | | ....F.... | ........ | I..HE...A...S...... | .L.MG--- |
| iPS:44 2365 | VH3\|3-33\|D4\|4-11\|RF2\|J H6 | | ....F.... | ........ | I..HE..E....S...... | .L.MG--- |
| iPS:44 2372 | VH3\|3-33\|D4\|4-11\|RF2\|J H6 | | ....F.... | ........ | I..HS...E...S...... | .L.MG--- |
| iPS:44 2379 | VH3\|3-33\|D4\|4-11\|RF2\|J H6 | | ....F.... | ........ | I..HS...A...S...... | .L.MG--- |
| iPS:44 2386 | VH3\|3-33\|D4\|4-11\|RF2\|J H6 | | ....F.... | ........ | I..HS.......S...... | .L.MG--- |

Figure 54 (Continued)

| | Germline | H_FR1 | H_CDR1 | H_FR2 | H_CDR2 | H_FR3 | H_CDR3 | H_FR4 |
|---|---|---|---|---|---|---|---|---|
| iPS:44 2390 | VH3\|3-33\|D4\|4-11\|RF2\|J H6 | ........... | ....F... | ........... | I..H......E..... | .........S......... | .L.MG--- | ........ |
| iPS:44 2394 | VH3\|3-33\|D4\|4-11\|RF2\|J H6 | ........... | ....F... | ........... | I..HS.....E..... | .........S......... | .L.MG--- | ........ |
| iPS:44 2398 | VH3\|3-33\|D4\|4-11\|RF2\|J H6 | ........... | ....F... | ........... | I..HS.....E..... | .........S......... | .L.MG--- | ........ |
| iPS:44 2402 | VH3\|3-33\|D4\|4-11\|RF2\|J H6 | ........... | ....F... | ........... | I..HS.....E..... | .........S......... | .L.MG--- | ........ |
| iPS:44 2406 | VH3\|3-33\|D4\|4-11\|RF2\|J H6 | ........... | ....F... | ........... | I..HE....A..... | .........S......... | .L.MG--- | ........ |
| iPS:44 2410 | VH3\|3-33\|D4\|4-11\|RF2\|J H6 | ........... | ....F... | ........... | I..H....A..... | .........S......... | .L.MG--- | ........ |
| iPS:44 2414 | VH3\|3-33\|D4\|4-11\|RF2\|J H6 | ........... | ....F... | ........... | I..H....A..... | .........S......... | .L.MG--- | ........ |
| iPS:44 3027 | VH3\|3-33\|D4\|4-11\|RF2\|J H6 | ........... | ....F... | ........... | I..H....A..... | .........S......... | .L.MG--- | ........ |
| VH3\|3-07\|D4\|4-11\|RF2\|J H6 | | EVQLLES GGGVQPGGSLRL SCAASG-FTFS | WMS | WVRQAPGKGLE WVA | CDR2 SEQ GSEKYYVDSV KG | RFTISRDNSKNTLYL QMNSLRAEDTAVYYCAR | DY SKYY -----YYGMDV | WGQGTT VTVSS |
| iPS:44 2417 | VH3\|3-07\|D4\|4-11\|RF2\|J H6 | ........V.. | .FG.H | ........... | I..WH.....N...AE..... | .........T......... | .L.MG--- | ........ |
| iPS:44 2431 | VH3\|3-07\|D4\|4-11\|RF2\|J H6 | ........V.. | .FG.H | ........... | I..WHS....N...AE..... | .........T......... | .L.MG--- | ........ |
| iPS:44 2438 | VH3\|3-07\|D4\|4-11\|RF2\|J H6 | ........V.. | .FG.H | ........... | I..WHE....N...AE..... | .........T......... | .L.MG--- | ........ |

FIGURE 55

Table 19A

VARIABLE HEAVY CHAIN CONSENSUS SEQUENCES

| NAME (ORIGINAL AND PATENT) | Patent SEQ ID NO: | SEQUENCE |
|---|---|---|
| VH-Consensus 1 (Table 21) (generated from 13 heavy chain sequences) | SEQ ID NO: 50352 | QVQLVQSGAEVKKPGASVKVSCKASGYTFTDYYMH WVRQAPGQGLEWMGWINPENGGTNYAQKFQGRVT MTRDTSISTAYMELSRLRSDDTAVYYCARDGTGSFD YWGQGTLVTVSS |
| VH-Consensus 2 (Table 22) (generated from 11 heavy chain sequences) | SEQ ID NO: 50353 | QVQLVQSGAEVKKPGASVKVSCKASGYTFTGYYMH WVRQAPGQGLEWMGWINPNSGGTNYAQKFQGRVT MTRDTSISTAYMELSRLRSDDTAVYYCARSYYYGSG SYYNEFDYWGQGTLVTVSS |
| VH-Consensus 3 (Table 23) (generated from 15 heavy chain sequences) | SEQ ID NO: 50354 | QVQLVQSGAEVKKPGASVKV3CKASGYTFTNYDIN WVRQATGQGLEWMGWMHPNSGNTGYAQKFQGRV TMTRNTSISTAYMELSSLRSEDTAVYYCASSSGWYY FDYWGQGTLVTVSS |
| VH-Consensus 4 (Table 24) (generated from 23 heavy chain sequences) | SEQ ID NO: 50355 | EVQLVESGGGLVKPGGSLRLSCAASGFTFSSYSMNW VRQAPGKGLEWVSSISGSSSYITYADSVKGRFTISRD NAKNSLYLQMNSLRAEDTAVYYCARVAEFDYWGQ GTLVTVSS |
| VH-Consensus 5 | SEQ ID NO: 50356 | EVQLVESGGGLVKPGGSLRLSCAASGFTFSSYSMNW VRQAPGKGLEWVSSISGSSSYINYADSVKGRFTISRD NAKNSLYLQMNSLRAEDTAVYYCARDRGSLWGGQ TLVTVSS |
| VH-Consensus 6 (Table 26) (generated from 11 heavy chain sequences) | SEQ ID NO: 50357 | EVQLLESGGGLVQPGGSLRLSCAASGFTFSSYYMNW VRQAPGKGLEWVSAISGSGGSTYADSVKGRFTISR DNSKNTLYLQMNSLRAEDTAVYYCARTGTYFDYWG QGTLVTVSS |
| VH-Consensus 7 (Table 27) (generated from 30 heavy chain sequences) | SEQ ID NO: 50358 | EVQLLESGGGLVQPGGSLRLSCAASGFTFSSYAMSW VRQAPGKGLEWVSAISGRGGSTFHADSVKGRFTISR DNSKNTLYLQMNSLRAEDTAVYYCVKGELLEDYYF YGMDVWGQGTTVTVSS |
| VH-Consensus 8 (Table 28) (generated from 25 heavy chain sequences) | SEQ ID NO: 50359 | EVQLLESGGGLVQPGGSLRLSCAASEFTFSSYAMYW VRQAPGKGLEWVSVISGRGGNTFYADSVKGRFTISR DNSKNTLYLQMNSLRAEDTAVYYCASRLAVAGSEA FDIWGQGTMVTVSS |
| VH-Consensus 9 (Table 29) (generated from 14 heavy chain sequences) | SEQ ID NO: 50360 | QVQLVESGGGVVQPGRSLRLSCAASGFTFSSYGMH WVRQAPGKGLEWVAYIWYDGSNKYYADSVKGRFT ISRDNSKNTLYLQMNSLRAEDTAVYYCARDLSMGG MDVWGKGTTVTVSS |

FIGURE 55 (Continued)

| | SEQ ID NO: | Sequence |
|---|---|---|
| VH-Consensus 10 (Table 30) (generated from 22 heavy chain sequences) | SEQ ID NO: 50361 | QVQLVESGGGVVQPGRSLRLSCAASGFTFSSYYMH WVRQAPGKGLEWVAVIWYDGSNKYYADSVKGRFT ISRDNSKNTLYLQMNSLRAEDTAVYYCAREKYSSS WYDYGMDVWGQGTTVTVSS |
| VH-Consensus 11 (Table 31) (generated from 16 heavy chain sequences) | SEQ ID NO: 50362 | QVQLVESGGGVVQPGRSLRLSCAASGFTFSDYGMH WVRQAPGKGLEWVAYIWYDESNKYYADSVKGRFTI SRDNSKNTLYLQMNSLRAEDTAVYYCAREKGWLDD YWGQGTLVTVSS |
| VH-Consensus 12 (Table 32) (generated from 71 heavy chain sequences) | SEQ ID NO: 50363 | QVQLVESGGGVVQPGRSLRLSCAASGFTFSDYGMH WVRQAPGKGLEWVAVIWYDENNKYYADSVKGRFT ISRDNSKNTLYLQMNSLRAEDTAVYYCARELGFRSD YWGQGTLVTVSS |
| VH-Consensus 13 (Table 33) (generated from 21 heavy chain sequences) | SEQ ID NO: 50364 | QLQLQESGPGLVKPSETLSLTCTVSGGSISRSSYYWG WIRQPPGKGLEWIGNIYYSGSTYYNPSLKSRVTISVD TSKNQFSLKLSSVTAADTAVYYCARHSSSWSLDYW GQGTLVTVSS |
| VH-Consensus 14 (Table 34) (generated from 13 heavy chain sequences) | SEQ ID NO: 50365 | QLQLQESGPGLVKPSETLSLTCTVSGGSISRSSYYWG WIRQPPGKGLEWIGNIYYKGSTYYNPSLKSRVTISVD TSKNQFSLKLSSVTAADTAVYYCGRHGKDWGLDY WGQGTLVTVSS |
| VH-Consensus 15 (Table 49) (generated from 149 heavy chain sequences) | SEQ ID NO: 50266 | QVQLVQS-GAEVKKPGASVKVSCKASG-YTFTN--- YDINWVRQATGQGLEWMGWMHPN--- SGNTGYAQKFQGRVTMTRNTSISTAYMELSSLRSED TAVYYCASSSGWY--- YFDYWGQGTLVTVSS |
| VH-Consensus 16 (Table 50) (generated from 128 heavy chain sequences) | SEQ ID NO: 50267 | QVQLVES-GGGVVQPGRSLRLSCAASG-FTFSS--- YVMHWVRQAPGKGLEWVAVIWYD--- GSNKYYADSVKGRFTISRDNSKNTLYLQMNSLRAED TAVYYCAREKYSSG--- YDYGMDVWGQGTTVTVSS |
| VH-Consensus 17 (Table 51) (generated from 117 heavy chain sequences) | SEQ ID NO: 50268 | QVQLVES-GGGVVQPGRSLRLSCAASG-FTFSD--- YGMHWVRQAPGKGLEWVAVIWYD--- ENNKYYADSVKGRFTISRDNSKNTLYLQMNSLRAE DTAVYYCARELGF--- SDYWGQGTLVTVSS |
| VH-Consensus 18 (Table 52) (generated from 91 heavy chain sequences) | SEQ ID NO: 50269 | QVQLQQW-GAGLLKPSETLSLTCAVHG-GSFSG--- CYWSWIRQPPGKGLEWKGEINF--- SGSTNYNPSLKSRVTISVDTSKNQFSLKLSSVTAADT AVYYCARDYGG--- MDVWGQGTTVTVSS |

FIGURE 55
(Continued)

| | SEQ ID NO: | |
|---|---|---|
| VH-Consensus 19 (Table 53) (generated from 74 heavy chain sequences) | SEQ ID NO: 50270 | QVQLVQS-GAEVKKPGASVKVSCKASG-YTFTN---YDINWVRQATGQGLEWMGWMHPN---SGNTGYAQKFQGRVTMTRNTSISTAYMELSSLRSED TAVYYCAISSGWY---WFDFWGQGTLVTVSS |
| VH-Consensus 20 (Table 54) (generated from 53 heavy chain sequences) | SEQ ID NO: 50271 | QVQLVES-GGGVVQPGRSLRLSCAASG-FTFSS---YGMHWVRQAPGKGLEWVAYIWYD---GSNKNYADSVKGRFTISRDNSKNTLYLQMNSLRAED TAVYYCARDQGYGY---YGLDYWGQGTTVTVSS |
| VH-Consensus 21 (Table 55) (generated from 52 heavy chain sequences) | SEQ ID NO: 50272 | QVQLVQS-GAEVKKPGASVKVSCKASG-YTFTG---YYMHWVRQAPGQGLEWMGWINPN---SGGTNYAQKFQGRVTMTRDTSISTAYMELSRLRSDD TAVYYCARDGTS---SFDYWGQGTLVTVSS |
| VH-Consensus 22 (Table 56) (generated from 49 heavy chain sequences) | SEQ ID NO: 50273 | QVQLVES-GGGVVQPGRSLRLSCAASG-FTFSS---YGMHWVRQAPGKGLEWVAVIWHD---GSNKYYADSVKGRFTISRDNSKNTLYLQMNSLRAED TAVYYCARDLSMG---GMDVWGQGTTVTVSS |
| VH-Consensus 23 (Table 57) (generated from 37 heavy chain sequences) | SEQ ID NO: 50274 | QVQLVES-GGGVVQPGRSLRLSCAASG-FTFSD---YGMHWVRQAPGKGLEWVAVIWYD---FSNKYYADSVKGRFTISRDNSKNTLYLQMNSLRAED TAVYYCAREVGW---LDDYWGQGTLVTVSS |
| VH-Consensus 24 (Table 58) (generated from 35 heavy chain sequences) | SEQ ID NO: 50275 | EVQLVES-GGGLVKPGGSLRLSCAASG-FTFSS---YSMNWVRQAPGKGLEWVSSINGS---SSYIYYADSVKGRFTISRDNAKNSLYLQMNSLRAED TAVYYCARDRG---SSWGQGTLVTVSS |
| VH-Consensus 25 (Table 59) (generated from 32 heavy chain sequences) | SEQ ID NO: 50276 | EVQLLES-GGGLVQPGGSLRLSCAASE-FTFSS---YAMSWVRQAPGKGLEWVSVISGR---GGNTFYADSVKGRFTISRDNSKNTLYLQMNSLRAED TAVYYCASRIAVAG---SEAFDIWGQGTMVTVSS |
| VH-Consensus 26 (Table 60) (generated from 30 heavy chain sequences) | SEQ ID NO: 50277 | EVQLLES-GGGLVQPGGSLRLSCAASG-FTFSS---YAMSWVRQAPGKGLEWVSAISGR---GGSTEHADSVKGRFTISRDNSKNTLYLQMNSLRAED TAVYYCVKGELLEDY---YFYGMDVWGQGTTVTVSS |
| VH-Consensus 27 (Table 61) (generated | SEQ ID NO: 50278 | QVQLVES-GGGVVQPGRSLRLSCAASG-FTFSS---YGMHWVRQAPGKGLEWVAVIWYD--- |

FIGURE 55
(Continued)

| | | |
|---|---|---|
| from 29 heavy chain sequences) | | GSNKYYADSYKGRFTISRDNSKNTLYLQMNSLRAED TAVYYCARDRVYCSSTSC_____ PYYYYGMDYWGQGTTVTVSS |
| VH-Consensus 28 (Table 62) (generated from 28 heavy chain sequences) | SEQ ID NO: 50279 | EVQLVES-GGGLVKPGGSLRLSCAASG-FTFSS-___ YSMNWVRQAPGKGLEWVSSISGS-___ SSYIYYADSVKGRFTISRDMAKNSLYLQMNSLRAED TAVYYCARYAS-___ FDYWGQGTLVTVSS |
| VH-Consensus 29 (Table 63) (generated from 26 heavy chain sequences) | SEQ ID NO: 50280 | QVQLQES-GPGLVKPSQFLSLTCTVSG-GSISSG-___ DYYWNWIRQHPGKGLEWIGYIFY-___ SGSTYYNPSLKSRVTISVDTSKNQFSLKLSSVTAADT AVYYCARGDYDGSGSY-___ HYYYGMDVWGQGTTVTVSS |
| VH-Consensus 30 (Table 64) (generated from 24 heavy chain sequences) | SEQ ID NO: 50281 | EVQLLES-GGGLVQPGGSLRLSCAASG-FTFSS-___ YAMSWVRQAPGKGLEWVSYISGG-___ GSSTYYADSVKGRFTISRDNSKNTLYLQMNSLRAED TAVYYCAKWRGNPT-___ DYGMDVWGQGTTVTVSS |
| VH-Consensus 31 (Table 65) (generated from 24 heavy chain sequences) | SEQ ID NO: 50282 | QVQLVES-GGGVVQPGRSLRLSCAASG-FTFSS-___ YGMHWVRQAPGKGLEWVAHWYD-___ GSNKYYADSVKGRFTISRDNSKNTLYLQMNSLRAED TAVYYCARDHYDFW-___ SGHFDYWGQGTLVTVSS |
| VH-Consensus 32 (Table 66) (generated from 24 heavy chain sequences) | SEQ ID NO: 50283 | QVQLQQW-GAGLLKPSETLSLTCAVYG-GSFSG-___ YYWSWIRQPPGKGLEWIGEINH-___ SGRTNYNPSLKSRVTISVDTSKNQFSLKLSSVTAADT AVYYCARDYFG-___ LDYWGQGTLVTVSS |
| VH-Consensus 33 (Table 67) (generated from 22 heavy chain sequences) | SEQ ID NO: 50284 | QLQLQES-GPGLVKPSETLSLTCTVSG-GSISRS-___ SYYWGWIRQPPGKGLEWIGRIY-___ SGSTYYNPSLKSRVTISVDTSKNQFSLKLSSVTAADT AVYYCARHSSSW-___ SLDYWGQGTLVTVSS |
| VH-Consensus 34 (Table 68) (generated from 19 heavy chain sequences) | SEQ ID NO: 50285 | QVQLVQS-GAEVKKPGASVKVSCKASG-YTFTG-___ YYIHWVRQAPGQGLEWMGWINPN-___ SGGTNYAQKFQGRVTMTRDTSISTAYMELSRLRSDD TAVYYCARGYSYGY-___ NWFDFWGQGTLVTVSS |
| VH-Consensus 35 (Table 69) (generated from 18 heavy chain sequences) | SEQ ID NO: 50286 | QVQLVES-GGGVVQPGRSLRLSCAASG-FTFSH-___ YGMHWVRQAPGKGLEWVAVIWYD-___ GSNKYYADSVKGRFTISRDNSKNTLYLQMNSLRAED |

FIGURE 55
(Continued)

| | | TAVYYCARGDWNP-----EGMDVWGQGTTVTVSS |
|---|---|---|
| VH-Consensus 36 (Table 70) (generated from 17 heavy chain sequences) | SEQ ID NO: 50287 | EVQLLES-GGGLVQPGGSLRLSCAASG-FTFSS-----YAMSWVRQAPGKGLEWVSAISGS-----GGNTFYADSVKGRFTISRDNSKNTLYLQMNSLRAED TAVYYCAKKDYEYVW-----GSPYFDYWGQGTLVTVSS |
| VH-Consensus 37 (Table 71) (generated from 16 heavy chain sequences) | SEQ ID NO: 50288 | QVQLVQS-GAEVKKPGASVKVSCKASG-YTFTG-----YYMHWVRQAPGQGLEWMGWINPN-----SGGTNYAQKFQGRVTMTRDTSISTAYMELSRLRSDD TAVYYCARSYYYGSGS-----YYNFFDYWGQGTLVTVSS |
| VH-Consensus 38 (Table 72) (generated from 14 heavy chain sequences) | SEQ ID NO: 50289 | QVQLVQS-GAEVKKPGASVKVSCKASG-YTFTG-----YYIHWVRQAPGQGLEWMGWINPY-----SGDTNYAQKFQGRVTMTRDTSISTAYMELSRLRFDD TAVFYCARDWGGYSS-----YYYGMDVWGQGTTVTVSS |
| VH-Consensus 39 (Table 73) (generated from 14 heavy chain sequences) | SEQ ID NO: 50290 | EVQLVES-GGGLVKPGGSLRLSCAASG-FTFSL-----YSMHWVRQAPGKGLEWVSSISGS-----SSYTYYADSVKGRFTISRDNAKNSLYLQMNSLRAED TAVYYCARLL-----FDYWGQGTLVTVSS |
| VH-Consensus 40 (Table 74) (generated from 14 heavy chain sequences) | SEQ ID NO: 50291 | QVQLVES-GGGVVQPGRSLRLSCAASG-FTFST-----YGMHWVRQAPGKGLEWVAHWYD-----GTNKYYADSVKGRFTISRDMSKNTLYLQLNSLRAED TAVYYCARDPLRGYN-----DPVMDYWGQGTLVTVSS |
| VH-Consensus 41 (Table 75) (generated from 13 heavy chain sequences) | SEQ ID NO: 50292 | EVQLLES-GGGGLVQPGGSLRLSCAASG-FTFSS-----YAMSWVRQAPGKGLEWVSAISGR-----GGNTFYADSVKGRFTISRDNSKNTLYLQMNSLRAED TAVYYCAKRVTDYGG-----NDWFFPWGQGTLVTVSS |
| VH-Consensus 42 (Table 76) (generated from 13 heavy chain sequences) | SEQ ID NO: 50293 | QVQLVES-GGGVVQPGRSLRLSCAASG-FTFST-----XGMHWVRQAPGKGLEWVAYIWYG-----GNNKDYADSVKGRFTISRDISKNTLYLQMNSLRAED TAVYYCARDRDYCSGGSC-----PYYYYGMDYWGQGTTVTVSS |
| VH-Consensus 43 (Table 77) (generated from 13 heavy chain sequences) | SEQ ID NO: 50294 | QLQLQES-GPGLVKPSETLSLTCTVSG-GSISRS-----SYYWGWIRQPPGKGLEWIGNIYY-----SGSTYYNPSLKSRVTISVDTSKNQFSLKLSSVTAADT AVYYCGRHGRDW-----GLDYWGQGTLVTVSS |

FIGURE 55
(Continued)

| | SEQ ID NO: | |
|---|---|---|
| VH-Consensus 44 (Table 78) (generated from 12 heavy chain sequences) | SEQ ID NO: 50295 | QVQLVQS-GAEVKKPGASVKVSCKASG-YTFTG-----YYMHWVRQAPGQGLEWMGWIKPN----SGGTNQAQKFQGRVTMTRDTSISTAYMELSGLRSDDTAVYYCARAPGIAAAG----TWGYFDYWGQGTLVTVSS |
| VH-Consensus 45 (Table 79) (generated from 12 heavy chain sequences) | SEQ ID NO: 50296 | QITLKES-GPTLVKPTQTLTLTCTFSG-FSLSTG----GVGVGWIRQPPGKALEWLALIYW----DDDKRYSPSLKSRLTITKDTSKNQVVLTMTNMDPVDTATYYCAHLIAV----AFDYWGQGTLVTVSS |
| VH-Consensus 46 (Table 80) (generated from 11 heavy chain sequences) | SEQ ID NO: 50297 | QVQLVES-GGGVVQPGRSLRLSCAASG-FTFSS----YGMHWVRQAPGKGLEWVAHWYD----GSYKYYADSVKGRFTISRDNSKNTLYLQMNSLRAEDTAVYYCAREAYDFW----SGYFDYWGQGTLVTVSS |
| VH-Consensus 47 (Table 81) (generated from 11 heavy chain sequences) | SEQ ID NO: 50298 | QVQLVES-GGGVVQPGRSLRLSCAASG-FTFSS----YGMHWVRQAPGKGLEWVAYTWYD----GSNKYYADSVKGRFTISRDNSKNTLYLQMNSLRAEDTAVYYCARDEDYGD----YGMDVWGQGTTVTVSS |
| VH-Consensus 48 (Table 82) (generated from 10 heavy chain sequences) | SEQ ID NO: 50299 | EVQLLES-GGGLVQPGGSLRLSCAASG-FTFSS----YAMSWVRQAPGKGLEWVSAIHGS----GGNTFYADSVKGRFTISRDNSKNTLYLQMNSLRAEDTAVYYCAKLGKDYY----YYGMDVWGQGTTVTVSS |
| VH-Consensus 49 (Table 83) (generated from 10 heavy chain sequences) | SEQ ID NO: 50300 | EVQLLES-GGGLVQPGGSLRLSCAASG-FTFSS----YYMSWVRQAPGKGLEWVSAMSGS----GGRTYYADSVKGRFTISRDNSKNTLYLQMNSLRAEDTAVYYCAKLTA----FDYWGQGTLVTVSS |
| VH-Consensus 50 (Table 84) (generated from 10 heavy chain sequences) | SEQ ID NO: 50301 | QVQLVES-GGGVVQPGRSLRLSCAASG-FTFSS----YGMHWVRQAPGKGLEWVAHSYA----GSNKYYADSVKGRFTISRDNSKNTLYLQMNSLRAEDTAVYYCVRRGYSYG----GYGMDYWGQGTTVTVSS |
| VH-Consensus 51 (Table 85) (generated from 10 heavy chain sequences) | SEQ ID NO: 50302 | QVQLVES-GGGVVQPGRSLRLSCAASG-FTFSD----YYMHWVRQAPGKGLEWVAVIWYD----GSNKYYADSVKGRFTISRDNSKNTLYLQMNSLRAEDTAVYYCAREFYISW----YDYGMDVWGQGTTVTVSS |

FIGURE 55
(Continued)

| | SEQ ID NO: | |
|---|---|---|
| VH-Consensus 52 (Table 86) (generated from 9 heavy chain sequences) | SEQ ID NO: 50303 | QVQLVQS-GAEVKKPGASVKVSCKASG-YTFNS---YGISWVRQAPGQGLEWMGWISAY---NGNTKYAQKLQGRVTMTTDTSTSTAYMELRSLRSDDTAVYYCARHDFWSGY---YKGMDYWGQGTLVTVSS |
| VH-Consensus 53 (Table 87) (generated from 9 heavy chain sequences) | SEQ ID NO: 50304 | EVQLLES-GGGLVQPGGSLRLSCAASG-FTFSS---YAMSWVRQAPGKGLEWVSAISGR---GGNTFDADSVKGRFTISRDNSKNTLYLQMNSLRAEDTAVYYCAKERSGS---YFDYWGQGTLVTVSS |
| VH-Consensus 54 (Table 88) (generated from 9 heavy chain sequences) | SEQ ID NO: 50305 | QVQLVES-GGGVVQPGRSLRLSCAASG-FTFSN---YGMHWVRQAPGKGLEWVAVIWHD---GSNKYYADSVKGRFTISRDNSKNTILYLQMNSLRAEDTAVYYCARENSSS---YYFDYWGQGTLVTVSS |
| VH-Consensus 55 (Table 89) (generated from 8 heavy chain sequences) | SEQ ID NO: 50306 | QITLKES-GPTLVKPTQTLTLTCTFSG-FSLSTS---GVLVGWIRQPPGKALEWLALINW---NDDKRYSPSLKSRFTITRDTSKDQVVLTMTNMDPVDTATYYCAHKATWV---AEDIWGQGTMVTVSS |
| VH-Consensus 56 (Table 90) (generated from 8 heavy chain sequences) | SEQ ID NO: 50307 | EVQLLES-GGGLVQPGRLRLSCAASG-FTFSS---YYMNWVRQAPGKGLEWVSAISGS---GGRTYYADSVKGRFTISRDNSKNTLYLQMNSLRAEDTAVYYCARTAT---FDYWGQGTLVTVSS |
| VH-Consensus 57 (Table 91) (generated from 8 heavy chain sequences) | SEQ ID NO: 50308 | EVQLLES-GGGLVQPGGSLRLSCAASG-FTFSS---YAMSWVRQAPGKGLEWVSYISGR---GGITTYADSVKGRFTISRDNSKNTLYLQMNSLRAEDTAVYYCAKRTFSD---YFDIWGQGTMVTVSS |
| VH-Consensus 58 (Table 92) (generated from 8 heavy chain sequences) | SEQ ID NO: 50309 | QVQLVES-GGGVVQPGRSLRLSCAASG-FTFSS---YGMHWVRQAPGKGLEWVAVIWYD---GSNKYYADSVKGRFTISRDNSKNTLYLQMNSLRAEDTAVYYCARDRPRS---SAFDYWGQGTLVTVSS |
| VH-Consensus 59 (Table 93) (generated from 8 heavy chain sequences) | SEQ ID NO: 50310 | EVQLVES-GGGLVQPGGSLRLSCAASG-FTFSS---YNMNWVRQAPGKGLEWVSYISRS---SNTKYYADSVKGRFTISRDMAKNSLYLQMNSLRDEDTAVYYCARDRSGSYGY---FYYGLDVWGQGTTVTVSS |
| VH-Consensus 60 (Table 94) (generated | SEQ ID NO: 50311 | QVQLQES-GFGLVKPSQTLSLTCTVSG-GSIRSG---GDYWSWIRQHPGKGLEWIGYIYY--- |

FIGURE 55
(Continued)

| from 8 heavy chain sequences) | SGSTYYNPSLKSRVTISVDTSKNQFSLKLSSVTAADT AVYYCARDSSSY............ GMDVWGQGTTVTVSS |
| --- | --- |

FIGURE 55
(Continued)

Table 19B

VARIABLE HEAVY CDR CONSENSUS SEQUENCES I

| NAME (ORIGINAL AND PATENT) | Patent SEQ ID NO: | CDR | Sequence |
|---|---|---|---|
| VH-CONSENSUS-1 TABLE 21 | 50381 | VH1 | DYYMH |
| | 50382 | VH2 | WINPNNGGTNYAQKFQG |
| | 50383 | VH3 | DGTGSFDY |
| VH-CONSENSUS-2 TABLE 22 | 50384 | VH1 | GYYMH |
| | 50385 | VH2 | WINPNSGGTNYAQKFQG |
| | 50386 | VH3 | SYYYGSGSYYNEFDY |
| VH-CONSENSUS-3 TABLE 23 | 50387 | VH1 | NYDIN |
| | 50388 | VH2 | WMHPNSGNTGYAQKFQG |
| | 50389 | VH3 | SSGWYYFDY |
| VH-CONSENSUS-4 TABLE 24 | 50390 | VH1 | SYSMN |
| | 50391 | VH2 | SISGSSSYIYYADSVKG |
| | 50392 | VH3 | VASFDY |
| VH-CONSENSUS-5 TABLE 25 | 50393 | VH1 | SYSMN |
| | 50394 | VH2 | SISGSSSYIYYADSVKG |
| | 50395 | VH3 | DRGSL |
| VH-CONSENSUS-6 TABLE 26 | 50396 | VH1 | SYVMN |
| | 50397 | VH2 | AISGSGGSTYYADSVKG |
| | 50398 | VH3 | TGVFDY |
| VH-CONSENSUS-7 TABLE 27 | 50399 | VH1 | SYAMS |
| | 50400 | VH2 | AISGRGGSTFHAISVKG |
| | 50401 | VH3 | GELLEDYFYGMDV |
| VH-CONSENSUS-8 TABLE 28 | 50402 | VH1 | SYAMX |
| | 50403 | VH2 | VISGRGGNTFYADSVKG |
| | 50404 | VH3 | RLAVAGSEAFDI |
| VH-CONSENSUS-9 TABLE 29 | 50405 | VH1 | SYGMH |
| | 50406 | VH2 | VIWXDGSNKYYADSVKG |
| | 50407 | VH3 | DLSMGGMDV |
| VH-CONSENSUS-10 TABLE 30 | 50408 | VH1 | SYVMH |
| | 50409 | VH2 | VIWYDGSMKYYADSVKG |
| | 50410 | VH3 | EKYSSSWYDYGMDV |
| VH-CONSENSUS-11 TABLE 31 | 50411 | VH1 | DYGMH |
| | 50412 | VH2 | VIWYDESNKYYADSVKG |
| | 50413 | VH3 | EIGWLFDY |

FIGURE 55
(Continued)

| | | | |
|---|---|---|---|
| VH-CONSENSUS-12 TABLE 32 | 50414 | VH1 | DYGMH |
| | 50415 | VH2 | VIWYDENNKYYADSVKG |
| | 50416 | VH3 | ELGPRSDY |
| VH-CONSENSUS-13 TABLE 33 | 50417 | VH1 | RSSYYWG |
| | 50418 | VH2 | NIYYSGSTYYNPSLKS |
| | 50419 | VH3 | HSSSWSLDY |
| VH-CONSENSUS-14 TABLE 34 | 50420 | VH1 | RSSYYWG |
| | 50421 | VH2 | NIYYSGSTYYNPSLKS |
| | 50422 | VH3 | HGKDWGLDY |
| VH-CONSENSUS-15 TABLE 49 | 50468 | VH1 | NYDIN |
| | 50469 | VH2 | WMHPNSGNTGYAQKFQG |
| | 50470 | VH3 | SSGWYTPDY |
| VH-CONSENSUS-16 TABLE 50 | 50471 | VH1 | SYYMH |
| | 50472 | VH2 | VIWYDGSNKYYADSVKG |
| | 50473 | VH3 | ERYSSGWYDYGMDV |
| VH-CONSENSUS-17 TABLE 51 | 50474 | VH1 | DYGMH |
| | 50475 | VH2 | VIWYDENNKYYADSVKG |
| | 50476 | VH3 | ELGFSDY |
| VH-CONSENSUS-18 TABLE 52 | 50477 | VH1 | GCYWS |
| | 50478 | VH2 | EINHSGSTNYNPSLKS |
| | 50479 | VH3 | DYGGMDV |
| VH-CONSENSUS-19 TABLE 53 | 50480 | VH1 | NYDIN |
| | 50481 | VH2 | WMHPNSGNTGYAQKFQG |
| | 50482 | VH3 | SSGWYWFDP |
| VH-CONSENSUS-20 TABLE 54 | 50483 | VH1 | SYGMH |
| | 50484 | VH2 | VIWYDGSNKYYADSVKG |
| | 50485 | VH3 | DQGVGYYGDV |
| VH-CONSENSUS-21 TABLE 55 | 50486 | VH1 | GYYMH |
| | 50487 | VH2 | WINPNSGGTNYAQKFQG |
| | 50488 | VH3 | DGTSSFDY |
| VH-CONSENSUS-22 TABLE 56 | 50489 | VH1 | SYGMH |
| | 50490 | VH2 | VIWHDGSNKYYADSVKG |
| | 50491 | VH3 | DLSMGGMDV |
| VH-CONSENSUS-23 TABLE 57 | 50492 | VH1 | DYGMH |
| | 50493 | VH2 | VIWYDESNKYYADSVKG |
| | 50494 | VH3 | EVGWLDDY |

FIGURE 55
(Continued)

| | | | |
|---|---|---|---|
| VH-CONSENSUS-24 TABLE 58 | 50495 | VH1 | SYSMN |
| | 50496 | VH2 | SISGSSSYIYYADSVKG |
| | 50497 | VH3 | DRGSS |
| VH-CONSENSUS-25 TABLE 59 | 50498 | VH1 | SYAMS |
| | 50499 | VH2 | VISGRGGNTFYADSVKG |
| | 50500 | VH3 | RIAVAGSEAFDI |
| VH-CONSENSUS-26 TABLE 60 | 50501 | VH1 | SYAMS |
| | 50502 | VH2 | AISGRGGSTFHADSVKG |
| | 50503 | VH3 | GELLEDYYFYGMDY |
| VH-CONSENSUS-27 TABLE 61 | 50504 | VH1 | SYGMH |
| | 50505 | VH2 | VIWYDGSNKYYADSVKG |
| | 50506 | VH3 | DRVYCSSTSCPYYYYGMDV |
| VH-CONSENSUS-28 TABLE 62 | 50507 | VH1 | SYSMN |
| | 50508 | VH2 | SISGSSSYIYYADSVKG |
| | 50509 | VH3 | VASFDY |
| VH-CONSENSUS-29 TABLE 63 | 50510 | VH1 | SGDYYWN |
| | 50511 | VH2 | YIFYSGSTYYNPSLKS |
| | 50512 | VH3 | GDYDGSGSYHYYGMDV |
| VH-CONSENSUS-30 TABLE 64 | 50513 | VH1 | SYAMS |
| | 50514 | VH2 | VISGGGSSTYYADSVKG |
| | 50515 | VH3 | WRGNPTDYGMD |
| VH-CONSENSUS-31 TABLE 65 | 50516 | VH1 | SYGMH |
| | 50517 | VH2 | IIWYDGSNKYYADSVKG |
| | 50518 | VH3 | DHYDFWSGHFDY |
| VH-CONSENSUS-32 TABLE 66 | 50519 | VH1 | GYYWS |
| | 50520 | VH2 | EIHSGRTNYNPSLKS |
| | 50521 | VH3 | DYGGLDY |
| VH-CONSENSUS-33 TABLE 67 | 50522 | VH1 | RSSYYWG |
| | 50523 | VH2 | NIYYSGSTYYNPSLKS |
| | 50524 | VH3 | HSSSWSLDY |
| VH-CONSENSUS-34 TABLE 68 | 50525 | VH1 | GYYIH |
| | 50526 | VH2 | WINPNSGGTNYAQKFQG |
| | 50527 | VH3 | GVSYGYNWFDP |
| VH-CONSENSUS-35 TABLE 69 | 50528 | VH1 | HYGMH |
| | 50529 | VH2 | VIWYDGSNKYYADSVKG |
| | 50530 | VH3 | GDWNPEGMDV |

FIGURE 55
(Continued)

| | | | |
|---|---|---|---|
| VH-CONSENSUS-36 TABLE 70 | 50531 | VH1 | SYAMS |
| | 50532 | VH2 | AISGSGGNTFYADSVKG |
| | 50533 | VH3 | KDYDYVWGSPYFDY |
| VH-CONSENSUS-37 TABLE 71 | 50534 | VH1 | GYYMH |
| | 50535 | VH2 | WINPKSGGTNYAQKFQG |
| | 50536 | VH3 | SYYYGSGSYYNEFDY |
| VH-CONSENSUS-38 TABLE 72 | 50537 | VH1 | GYYIH |
| | 50538 | VH2 | WINPYSGFTNYAQKFQG |
| | 50539 | VH3 | DWGGYSSYYYGMDV |
| VH-CONSENSUS-39 TABLE 73 | 50540 | VH1 | SYSMN |
| | 50541 | VH2 | SISGSSSYIYYADSVKG |
| | 50542 | VH3 | LTFDY |
| VH-CONSENSUS-40 TABLE 74 | 50543 | VH1 | TYGMH |
| | 50544 | VH2 | HWYDGTNKYYADSVKG |
| | 50545 | VH3 | DPLRGYNDPVMDY |
| VH-CONSENSUS-41 TABLE 75 | 50546 | VH1 | SYAMS |
| | 50547 | VH2 | AISGRGGNTFYADSVKG |
| | 50548 | VH3 | RVTDYGGNDWFDP |
| VH-CONSENSUS-42 TABLE 76 | 50549 | VH1 | TYGMH |
| | 50550 | VH2 | VIWYGGSNKDYADSVKG |
| | 50551 | VH3 | DRDYCSGGSCPYYYYGMDV |
| VH-CONSENSUS-43 TABLE 77 | 50552 | VH1 | RSSYYWG |
| | 50553 | VH2 | NIYYSGSTYYNPSLKS |
| | 50554 | VH3 | HGKDWGLDY |
| VH-CONSENSUS-44 TABLE 78 | 50555 | VH1 | GYYMH |
| | 50556 | VH2 | WIKPKSGGTNQAQKFQG |
| | 50557 | VH3 | APGTAAAGTWGYFDY |
| VH-CONSENSUS-45 TABLE 79 | 50558 | VH1 | TGGVGVG |
| | 50559 | VH2 | LIYWDDDKRYSPSLKS |
| | 50560 | VH3 | LIAVAFDY |
| VH-CONSENSUS-46 TABLE 80 | 50561 | VH1 | SYGMH |
| | 50562 | VH2 | HWYDGSYKYYADSVKG |
| | 50563 | VH3 | EAYDFWSGYFDY |
| VH-CONSENSUS-47 TABLE 81 | 50564 | VH1 | SYGMH |
| | 50565 | VH2 | VIWYDGSNKYYADSVKG |
| | 50566 | VH3 | DRDYGDYGMDV |

FIGURE 55
(Continued)

| | | | | |
|---|---|---|---|---|
| VH-CONSENSUS-48 TABLE 82 | 50567 | VH1 | SYAMS | |
| | 50568 | VH2 | AISGSGGNTYYADSVKG | |
| | 50569 | VH3 | LGKDYYYYGMDV | |
| VH-CONSENSUS-49 TABLE 83 | 50570 | VH1 | SYVMS | |
| | 50571 | VH2 | AMSGSGGRTYYADSVKG | |
| | 50572 | VH3 | LTAFDY | |
| VH-CONSENSUS-50 TABLE 84 | 50573 | VH1 | SYGMH | |
| | 50574 | VH2 | IISYAGSNKYYADSVKG | |
| | 50575 | VH3 | RGYSYGGYGMDV | |
| VH-CONSENSUS-51 TABLE 85 | 50576 | VH1 | DYVMH | |
| | 50577 | VH2 | VIWYDGSNKYYADSVKG | |
| | 50578 | VH3 | EPYTSGWYDYGMDV | |
| VH-CONSENSUS-52 TABLE 86 | 50579 | VH1 | SYGIS | |
| | 50580 | VH2 | WISAYNGNTKYAQKLQG | |
| | 50581 | VH3 | HDFWSGYYKGMDV | |
| VH-CONSENSUS-53 TABLE 87 | 50582 | VH1 | SYAMS | |
| | 50583 | VH2 | AISGRGGNTFDADSVKG | |
| | 50584 | VH3 | ERSGSYFDY | |
| VH-CONSENSUS-54 TABLE 88 | 50585 | VH1 | NYGMH | |
| | 50586 | VH2 | VIWHDGSNKYYADSVKG | |
| | 50587 | VH3 | ENSSYYFDY | |
| VH-CONSENSUS-55 TABLE 89 | 50588 | VH1 | TSGVGVG | |
| | 50589 | VH2 | LINWNDDKRYSPSLKS | |
| | 50590 | VH3 | KATWVAFDI | |
| VH-CONSENSUS-56 TABLE 90 | 50591 | VH1 | SYVMN | |
| | 50592 | VH2 | AISGSGGRTYYADSVKG | |
| | 50593 | VH3 | TAFFDY | |
| VH-CONSENSUS-57 TABLE 91 | 50594 | VH1 | SYAMS | |
| | 50595 | VH2 | VISGRGGTIFYADSVKG | |
| | 50596 | VH3 | KRTPSDVFDI | |
| VH-CONSENSUS-58 TABLE 92 | 50597 | VH1 | SYGMH | |
| | 50598 | VH2 | VIWYDGSNKYYADSVKG | |
| | 50599 | VH3 | DRPSSAFDY | |
| VH-CONSENSUS-59 TABLE 93 | 50600 | VH1 | SYNMN | |
| | 50601 | VH2 | YISKSSNTKYYADSVKG | |
| | 50602 | VH3 | DRSGSYGYFYYGLDV | |
| VH-CONSENSUS-60 | 50603 | VH1 | SGGDYWS | |

FIGURE 55
(Continued)

| TABLE 94 | | | |
|---|---|---|---|
| | 50604 | VH2 | YIYYSGSTYYNPSLKS |
| | 50605 | VH3 | DSSSYGMDV |

FIGURE 55
(Continued)

Table 19C

VARIABLE HEAVY CDR CONSENSUS SEQUENCES II

| NAME (ORIGINAL AND PATENT) | Patent SEQ ID NO. | SEQ ID NO. | CDR | Sequence |
|---|---|---|---|---|
| VH-CONSENSUS-15 TABLE 49 | | SEQ ID NO: 50001 | VH1 | X1 Tyr Asp X2 Asn, wherein X1 = N or H or a conservative substitution thereof, X2 = I or V or L or a conservative substitution thereof. |
| | | SEQ ID NO: 50002 | VH2 | X1 X2 X3 Pro X4 Ser X5 X6 X7 X8 X9 X10 X11 X12 Phe X13 X14 wherein X1 = W or R or a conservative substitution thereof, X2 = M or V or L or a conservative substitution thereof, X3 = H or N or Y or T or a conservative substitution thereof, X4 = N or D or H or a conservative substitution thereof, X5 = G or H or a conservative substitution thereof, X6 = N or S or Q or A or D or K or T or a conservative substitution thereof, X7 = T or A or V or E or a conservative substitution thereof, X8 = G or D or a conservative substitution thereof, X9 = Y or F or C or a conservative substitution thereof, X10 = A or P or a conservative substitution thereof, X11 = Q or K or a conservative substitution thereof, X12 = K or R or N or a conservative substitution thereof, X13 = Q or R or a conservative substitution thereof, X14 = G or V or a conservative substitution thereof. |
| | | SEQ ID NO: 50003 | VH3 | Ser Ser Gly Trp X1 X2 Phe Asp X3, wherein X1 = Y or E or N or T or a conservative substitution thereof, X2 = Y or F or K or I or R or V or L or M or W or H or S or a conservative substitution thereof, X3 = Y or F or S or N or a conservative substitution thereof. |
| VH-CONSENSUS-16 TABLE 50 | | SEQ ID NO: 50004 | VH1 | X1 X2 X3 X4 X5, wherein X1 = S or D or N or I or a conservative substitution thereof, X2 = Y or C or F or D or S or a conservative substitution thereof, X3 = Y or G or I or L or a conservative substitution thereof, X4 = M or I or L or a conservative substitution thereof, X5 = H or D or a conservative substitution thereof. |
| | | SEQ ID NO: 50005 | VH2 | X1 Ile X2 Tyr Asp X3 X4 X5 Lys X6 X7 X8 X9 X10 X11 Lys Gly, wherein X1 = V or L or A or a conservative substitution thereof, X2 = W or F or a conservative substitution thereof, X3 = G or A or a conservative substitution thereof, X4 = S or R or N or a conservative substitution thereof, X5 = N or Y or G or S or a conservative substitution thereof, X6 = Y or H or a conservative substitution thereof, X7 = Y or H or N or a conservative substitution thereof, X8 = A or V or E or G or T or a conservative substitution thereof, X9 = D or E or G or a conservative substitution thereof, X10 = S or A or a conservative substitution thereof, X11 = Y or M or a conservative substitution thereof. |

FIGURE 55
(Continued)

| | | | |
|---|---|---|---|
| | SEQ ID NO: 50006 | VH3 | X1 X2 X3 X4 X5 X6 X7 X8 X9 X10 X11 X12 X13 X14 X15 X16 Gly X17 X18 Val, wherein X1 = E or R or V or a conservative substitution thereof, X2 = R or Y or K or V or E or P or D or L or F or M or N or Q or T or a conservative substitution thereof, X3 = Y or S or T or V or a conservative substitution thereof, X4 = S or R or Y or P or T or G or a conservative substitution thereof, X5 = S or C or Y or a conservative substitution thereof, X6 = G or W or S or N or a conservative substitution thereof, X7 = W or Absent or L or Y or G or F or S or a conservative substitution thereof, X8 = Absent or Y or a conservative substitution thereof, X9 = Absent or A or G or T or a conservative substitution thereof, X10 = Absent or C or a conservative substitution thereof, X11 = Absent or P or a conservative substitution thereof, X12 = Absent or Y or L or a conservative substitution thereof, X13 = Absent or Y or D or a conservative substitution thereof, X14 = Y or Absent or F or H or a conservative substitution thereof, X15 = D or S or G or T or V or Y or A or F or M or a conservative substitution thereof, X16 = Y or G or F or a conservative substitution thereof, X17 = M or L or a conservative substitution thereof, X18 = D or G or a conservative substitution thereof. |
| VH-CONSENSUS-17 TABLE 51 | SEQ ID NO: 50007 | VH1 | X1 X2 Gly X3 His, wherein X1 = D or S or N or T or a conservative substitution thereof, X2 = Y or F or a conservative substitution thereof, X3 = M or I or a conservative substitution thereof. |
| | SEQ ID NO: 50008 | VH2 | X1 X2 Trp X3 X4 X5 X6 X7 X8 X9 X10 X11 X12 Ser X13 X14 Gly, wherein X1 = V or L or a conservative substitution thereof, X2 = I or V or T or M or a conservative substitution thereof, X3 = Y or F or D or a conservative substitution thereof, X4 = D or E or A or G or N or a conservative substitution thereof, X5 = E or G or V or R or D or a conservative substitution thereof, X6 = N or S or T or D or I or Y or a conservative substitution thereof, X7 = N or H or K or a conservative substitution thereof, X8 = K or Q or E or N or R or a conservative substitution thereof, X9 = Y or H or K or D or R or S or a conservative substitution thereof, X10 = Y or H or a conservative substitution thereof, X11 = A or V or G or T or I or E or a conservative substitution thereof, X12 = D or E or a conservative substitution thereof, X13 = V or M or a conservative substitution thereof, X14 = K or R or a conservative substitution thereof. |
| | SEQ ID NO: 50009 | VH3 | X1 Leu X2 X3 X4 X5 X6 X7, wherein X1 = E or D or G or a conservative substitution thereof, X2 = G or A or a conservative substitution thereof, X3 = F or W or M or a conservative substitution thereof, X4 = L or R or T or Y or S or Q or I or A or E or N or a conservative substitution |

FIGURE 55
(Continued)

| | | | |
|---|---|---|---|
| VH-CONSENSUS-18 TABLE 52 | SEQ ID NO: 50010 | | thereof, X5 = S or E or G or D or F or N or A or T or a conservative substitution thereof, X6 = D or E or a conservative substitution thereof, X7 = Y or S or F or C or a conservative substitution thereof. |
| | SEQ ID NO: 50011 | VH1 | Gly X1 Tyr Trp Ser, wherein X1 = C or S or P or Y or a conservative substitution thereof. |
| | SEQ ID NO: 50011 | VH2 | Glu Ile Asn X1 X2 Gly X3 Thr X4 X5 Asn Pro Ser Leu X6 Ser, wherein X1 = H or Y or Q or a conservative substitution thereof; X2 = S or R or a conservative substitution thereof; X3 = S or R or C or I or a conservative substitution thereof; X4 = N or S or a conservative substitution thereof; X5 = Y or F or a conservative substitution thereof; X6 = K or T or a conservative substitution thereof. |
| | SEQ ID NO: 50012 | VH3 | Asp Tyr Gly Gly X1 Asp Val, wherein X1 = M or L or I or a conservative substitution thereof. |
| VH-CONSENSUS-19 TABLE 53 | SEQ ID NO: 50013 | VH1 | Asn Tyr Asp Ile Asn. |
| | SEQ ID NO: 50014 | VH2 | Trp Met X1 Pro X2 X3 X4 X5 X6 Gly X7 Ala Gln Lys Phe Gln X8, wherein X1 = H or N or Y or a conservative substitution thereof; X2 = N or D or a conservative substitution thereof; X3 = S or N or a conservative substitution thereof; X4 = G or V or a conservative substitution thereof; X5 = N or S or a conservative substitution thereof; X6 = T or I or a conservative substitution thereof; X7 = Y or F or C or a conservative substitution thereof; X8 = G or D or a conservative substitution thereof. |
| | SEQ ID NO: 50015 | VH3 | Ser Ser Gly Trp X1 X2 Phe Asp Pro, wherein X1 = Y or H or N or S or K or a conservative substitution thereof; X2 = W or R or a conservative substitution thereof. |
| VH-CONSENSUS-20 TABLE 54 | SEQ ID NO: 50016 | VH1 | X1 X2 Gly Met X3, wherein X1 = S or N or R or T or I or a conservative substitution thereof; X2 = Y or H or N or a conservative substitution thereof; X3 = H or D or a conservative substitution thereof. |
| | SEQ ID NO: 50017 | VH2 | X1 X2 Trp X3 Asp Gly X4 Asn X5 X6 X7 X8 X9 Ser Val Lys Gly, wherein X1 = V or I or a conservative substitution thereof; X2 = I or L or a conservative substitution thereof; X3 = Y or F or a conservative substitution thereof; X4 = S or T or a conservative substitution thereof; X5 = K or E or Q or D or R or a conservative substitution thereof; X6 = N or H or Y or a conservative substitution thereof; X7 = Y or H or a conservative substitution thereof; X8 = A or V or G or a conservative substitution thereof |

FIGURE 55
(Continued)

| | | | |
|---|---|---|---|
| VH-CONSENSUS-2 TABLE 55 | SEQ ID NO: 50018 | VH3 | or a conservative substitution thereof, X9 = D or E or a conservative substitution thereof. |
| | | | X1 X2 Gly X3 X4 X5 X6 X7 X8 X9 X10 X11 X12 X13 Asp Val, wherein X1 = D or A or a conservative substitution thereof, X2 = Q or R or Y or H or A or C or E or F or M or a conservative substitution thereof, X3 = V or I or F or a conservative substitution thereof, X4 = G or Y or a conservative substitution thereof, X5 = Y or E or a conservative substitution thereof, X6 = Absent or F or a conservative substitution thereof, X7 = Absent or D or a conservative substitution thereof, X8 = Absent or Y or a conservative substitution thereof, X9 = Absent or Y or a conservative substitution thereof, X10 = Absent or N or a conservative substitution thereof, X11 = Y or D or N or a conservative substitution thereof, X12 = G or A or D or a conservative substitution thereof, X13 = L or M or T or I or a conservative substitution thereof. |
| | SEQ ID NO: 50019 | VH1 | X1 X2 X3 X4 X5, wherein X1 = G or D or S or A or a conservative substitution thereof, X2 = Y or D or a conservative substitution thereof, X3 = Y or H or N or F or a conservative substitution thereof, X4 = M or L or I or a conservative substitution thereof, X5 = H or Q or a conservative substitution thereof. |
| | SEQ ID NO: 50020 | VH2 | Trp X1 X2 Pro X3 X4 X5 X6 X7 X8 X9 X10 X11 Phe Gln X12, wherein X1 = I or V or a conservative substitution thereof, X2 = N or H or K or S or a conservative substitution thereof, X3 = N or K or S or a conservative substitution thereof, X4 = S or N or R or T or a conservative substitution thereof, X5 = G or N or D or a conservative substitution thereof, X6 = G or A or a conservative substitution thereof, X7 = T or S or a conservative substitution thereof, X8 = N or H or Q or I or a conservative substitution thereof, X9 = Y or S or F or a conservative substitution thereof, X10 = A or T or a conservative substitution thereof, X11 = K or K or N or E or S or a conservative substitution thereof, X12 = G or D or a conservative substitution thereof. |
| | SEQ ID NO: 50021 | VH3 | X1 X2 X3 X4 X5 X6 X7 X8 X9 X10 X11 X12 X13, wherein X1 = D or K or G or S or E or a conservative substitution thereof, X2 = G or F or A or K or V or a conservative substitution thereof, X3 = T or Absent or P or a conservative substitution thereof, X4 = S or G or Absent or T or a conservative substitution thereof, X5 = Absent or V or S or a conservative substitution thereof, X6 = Absent or A or a conservative substitution thereof, X7 = Absent or T or a conservative substitution thereof, X8 = Absent or W or a conservative substitution thereof, X9 = Absent or G or a conservative substitution thereof, X10 = S or Absent or V or a conservative substitution thereof, X11 = F or |

FIGURE 55
(Continued)

| | | | |
|---|---|---|---|
| VH-CONSENSUS-22 TABLE 56 | SEQ ID NO: 50022 | VH1 | Absent or L or Y or a conservative substitution thereof, X12 = D or G or K or a conservative substitution thereof, X13 = Y or D or F or a conservative substitution thereof. |
| | SEQ ID NO: 50023 | VH2 | X1 X2 Gly X3 His, wherein X1 = S or N or a conservative substitution thereof, X2 = Y or F or H or a conservative substitution thereof, X3 = M or I or a conservative substitution thereof. |
| | SEQ ID NO: 50024 | VH3 | X1 Ile X2 X3 X4 X5 X6 X7 X8 X9 X10 X11 X12 X13 Val X14 Gly, wherein X1 = Y or I or a conservative substitution thereof, X2 = W or I or a conservative substitution thereof, X3 = H or Y or F or N or a conservative substitution thereof, X4 = D or S or E or a conservative substitution thereof, X5 = G or A or a conservative substitution thereof, X6 = S or G or a conservative substitution thereof, X7 = N or Y or a conservative substitution thereof, X8 = K or D or E or R or a conservative substitution thereof, X9 = Y or N or a conservative substitution thereof, X10 = Y or N or a conservative substitution thereof, X11 = A or V or G or a conservative substitution thereof, X12 = D or E or a conservative substitution thereof, X13 = S or A or a conservative substitution thereof, X14 = K or R or a conservative substitution thereof. |
| | | | X1 X2 X3 X4 X5 X6 X7 X8 X9 X10 X11 X12 X13 X14 X15 X16 X17 Gly X18 Asp Val, wherein X1 = D or T or R or a conservative substitution thereof, X2 = L or R or Y or S or F or I or P or a conservative substitution thereof, X3 = S or R or T or a conservative substitution thereof, X4 = M or V or G or P or K or M or Y or a conservative substitution thereof, X5 = G or Y or Absent or S or a conservative substitution thereof, X6 = Absent or Y or S or W or a conservative substitution thereof, X7 = Absent or G or a conservative substitution thereof, X8 = Absent or S or a conservative substitution thereof, X9 = Absent or G or a conservative substitution thereof, X10 = Absent or S or a conservative substitution thereof, X11 = Absent or P or a conservative substitution thereof, X12 = Absent or P or a conservative substitution thereof, X13 = Absent or Y or a conservative substitution thereof, X14 = Absent or Y or a conservative substitution thereof, X15 = Absent or Y or a conservative substitution thereof, X16 = Absent or S or Y or a conservative substitution thereof, X17 = Absent or D or Y or G or a conservative substitution thereof, X18 = M or L or T or a conservative substitution thereof. |
| VH-CONSENSUS-23 TABLE 57 | SEQ ID NO: 50025 | VH1 | X1 X2 Gly X3 His, wherein X1 = D or N or S or a conservative substitution thereof, X2 = Y or F or a conservative substitution thereof, X3 = M or I or L or a conservative substitution thereof. |

FIGURE 55
(Continued)

| | SEQ ID NO: 50026 | VH2 | Val Ile Trp X1 X2 X3 X4 Asn X5 X6 Tyr X7 X8 Ser X9 Lys Gly, wherein X1 = Y or F or a conservative substitution thereof, X2 = D or E or I or V or a conservative substitution thereof, X3 = E or G or V or A or R or a conservative substitution thereof, X4 = S or N or T or G or a conservative substitution thereof, X5 = K or Q or T or N or a conservative substitution thereof, X6 = Y or H or K or a conservative substitution thereof, X7 = A or T or G or E or V or a conservative substitution thereof, X8 = D or G or a conservative substitution thereof, X9 = V or A or a conservative substitution thereof. |
| | SEQ ID NO: 50027 | VH3 | Glu X1 Gly X2 X3 X4 Asp X5, wherein X1 = V or I or M or K or T or a conservative substitution thereof, X2 = W or F or G or M or a conservative substitution thereof, X3 = L or T or S or Y or H or R or a conservative substitution thereof, X4 = D or E or S or F or N or a conservative substitution thereof, X5 = Y or C or a conservative substitution thereof. |
| VH-CONSENSUS-24 TABLE 58 | SEQ ID NO: 50028 | VH1 | X1 X2 X3 X4 Asn, wherein X1 = S or T or a conservative substitution thereof, X2 = Y or F or a conservative substitution thereof, X3 = S or T or G or R or a conservative substitution thereof, X4 = M or L or a conservative substitution thereof. |
| | SEQ ID NO: 50029 | VH2 | X1 Ile Ser X2 Ser X3 X4 X5 X6 X7 Tyr X8 Asp Ser X9 Lys X10, wherein X1 = S or A or C or L or a conservative substitution thereof, X2 = G or S or a conservative substitution thereof, X3 = S or G or T or a conservative substitution thereof, X4 = S or T or G or Y or a conservative substitution thereof, X5 = Y or H or a conservative substitution thereof, X6 = I or L or M or a conservative substitution thereof, X7 = Y or S or W or a conservative substitution thereof, X8 = A or G or P or V or a conservative substitution thereof, X9 = V or L or a conservative substitution thereof, X10 = G or A or a conservative substitution thereof. |
| | SEQ ID NO: 50030 | VH3 | X1 Arg X2 X3 X4 X5 X6 X7, wherein X1 = D or T or a conservative substitution thereof, X2 = G or Absent or S or Y or a conservative substitution thereof, X3 = Absent or G or a conservative substitution thereof, X4 = Absent or S or a conservative substitution thereof, X5 = Absent or F or S or a conservative substitution thereof, X6 = S or D or G or H or a conservative substitution thereof, X7 = S or L or Y or G or T or C or E or I or a conservative substitution thereof. |
| VH-CONSENSUS-25 TABLE 59 | SEQ ID NO: 50031 | VH1 | X1 Tyr X2 Met X3, wherein X1 = S or G or a conservative substitution thereof, X2 = A or V or a conservative substitution thereof, X3 = S or N or T or a conservative substitution thereof. |

FIGURE 55
(Continued)

| | SEQ ID NO: 50032 | VH1 | X1 Ile Ser X2 X3 Gly X4 X5 X6 X7 X8 Ala Asp Ser Val X9 Gly, wherein X1 = V or I or A or a conservative substitution thereof, X2 = G or R or a conservative substitution thereof, X3 = R or S or a conservative substitution thereof, X4 = G or V or T or a conservative substitution thereof, X5 = N or Y or S or T or a conservative substitution thereof, X6 = T or A or a conservative substitution thereof, X7 = F or Y or a conservative substitution thereof, X8 = Y or N or S or a conservative substitution thereof, X9 = K or R or a conservative substitution thereof. |
|---|---|---|---|
| | SEQ ID NO: 50033 | VH3 | Arg X1 Ala Val X2 Gly X3 X4 Ala X5 X6 X7, wherein X1 = I or L or M or V or a conservative substitution thereof, X2 = A or D or a conservative substitution thereof, X3 = S or N or Y or a conservative substitution thereof, X4 = E or D or a conservative substitution thereof, X5 = F or C or a conservative substitution thereof, X6 = D or A or H or a conservative substitution thereof, X7 = I or V or a conservative substitution thereof. |
| VH-CONSENSUS-26 TABLE 60 | SEQ ID NO: 50034 | VH1 | X1 X2 X3 Met X4, wherein X1 = S or N or a conservative substitution thereof, X2 = Y or C or a conservative substitution thereof, X3 = A or V or a conservative substitution thereof, X4 = S or N or a conservative substitution thereof. |
| | SEQ ID NO: 50035 | VH2 | X1 X2 Ser X3 X4 Gly Gly X5 X6 X7 X8 Ala Asp Ser X9 Lys Gly, wherein X1 = A or T or S or a conservative substitution thereof, X2 = I or L or a conservative substitution thereof, X3 = G or R or V or a conservative substitution thereof, X4 = R or G or a conservative substitution thereof, X5 = S or N or a conservative substitution thereof, X6 = T or I or a conservative substitution thereof, X7 = F or Y or a conservative substitution thereof, X8 = H or Y or N or a conservative substitution thereof, X9 = V or E or M or a conservative substitution thereof. |
| | SEQ ID NO: 50036 | VH3 | X1 X2 Leu X3 X4 Tyr X5 X6 X7 X8 X9 X10 Asp Val, wherein X1 = G or W or a conservative substitution thereof, X2 = E or G or a conservative substitution thereof, X3 = E or Y or a conservative substitution thereof, X4 = D or S or N or a conservative substitution thereof, X5 = Absent or E or a conservative substitution thereof, X6 = Y or S or a conservative substitution thereof, X7 = F or Y or a conservative substitution thereof, X8 = Y or F or a conservative substitution thereof, X9 = G or A or a conservative substitution thereof, X10 = M or I or L or a conservative substitution thereof. |

FIGURE 55
(Continued)

| VH-CONSENSUS-27 TABLE 61 | SEQ ID NO: 50037 | VH1 | X1 Tyr X2 X3 X4, wherein X1 = S or G or D or R or H or T or N or a conservative substitution thereof, X2 = G or V or a conservative substitution thereof, X3 = M or L or a conservative substitution thereof, X4 = H or N or a conservative substitution thereof. |
|---|---|---|---|
| | SEQ ID NO: 50038 | VH2 | X1 X2 X3 X4 Asp Gly X5 X6 X7 X8 X9 X10 Asp Ser Val Lys X11, wherein X1 = Y or L or F or I or D or a conservative substitution thereof, X2 = I or F or a conservative substitution thereof, X3 = W or R or a conservative substitution thereof, X4 = Y or F or a conservative substitution thereof, X5 = S or N or T or a conservative substitution thereof, X6 = N or F or D or K or a conservative substitution thereof, X7 = K or N or T or a conservative substitution thereof, X8 = Y or S or D or N or a conservative substitution thereof, X9 = Y or N or a conservative substitution thereof, X10 = A or V or a conservative substitution thereof, X11 = G or D or a conservative substitution thereof. |
| | SEQ ID NO: 50039 | VH3 | Asp X1 X2 X3 X4 X5 X6 X7 X8 X9 X10 X11 X12 X13 X14 X15 Tyr X16 X17 Asp Val, wherein X1 = R or D or W or N or a conservative substitution thereof, X2 = V or D or R or F or H or a conservative substitution thereof, X3 = Y or S or E or G or F or a conservative substitution thereof, X4 = C or G or E or a conservative substitution thereof, X5 = S or G or a conservative substitution thereof, X6 = S or G or R or N or a conservative substitution thereof, X7 = T or Absent or S or P or a conservative substitution thereof, X8 = S or P or Absent or T or a conservative substitution thereof, X9 = C or Absent or T or a conservative substitution thereof, X10 = Absent or S or H or L or Y or a conservative substitution thereof, X11 = P or Absent or S or Y or a conservative substitution thereof, X12 = Y or Absent or a conservative substitution thereof, X13 = Y or Absent or a conservative substitution thereof, X14 = Y or Absent or a conservative substitution thereof, X15 = Y or F or a conservative substitution thereof, X16 = G or A or a conservative substitution thereof, X17 = M or L or a conservative substitution thereof. |
| VH-CONSENSUS-28 TABLE 62 | SEQ ID NO: 50040 | VH1 | X1 Tyr X2 X3 Asn, wherein X1 = S or N or a conservative substitution thereof, X2 = S or T or K or N or R or a conservative substitution thereof, X3 = M or L or a conservative substitution thereof. |
| | SEQ ID NO: 50041 | VH2 | Ser X1 Ser X2 X3 X4 X5 X6 X7 X8 Tyr X9 Asp Ser Val Lys Gly, wherein X1 = I or T or a conservative substitution thereof, X2 = G or S or a conservative substitution thereof, X3 = S or G or N or T or a conservative substitution thereof, X4 = S or G or D or N or a conservative substitution thereof, X5 = S or T or a conservative substitution thereof, X6 = Y or D or L or N or S or a conservative substitution thereof. |

FIGURE 55
(Continued)

| | | | |
|---|---|---|---|
| | SEQ ID NO: 50042 | VH3 | conservative substitution thereof; X7 = I or M or T or a conservative substitution thereof; X8 = Y or N or a conservative substitution thereof; X9 = A or T or a conservative substitution thereof. |
| | SEQ ID NO: 50042 | VH3 | Val X1 X2 X3 Asp X4, wherein X1 = A or N or S or a conservative substitution thereof; X2 = S or A or G or T or L or H or N or a conservative substitution thereof; X3 = F or L or N or a conservative substitution thereof; X4 = Y or C or S or a conservative substitution thereof. |
| VH-CONSENSUS-29 TABLE 63 | SEQ ID NO: 50230 | VH1 | Ser X1 X2 Tyr X3 Trp X4, wherein X1 = G or V or a conservative substitution thereof; X2 = D or V or G or S or a conservative substitution thereof; X3 = Y or H or a conservative substitution thereof; X4 = N or S or a conservative substitution thereof. |
| | SEQ ID NO: 50231 | VH2 | X1 X2 X3 X4 Ser Gly Ser Thr Tyr X5 Asn Pro Ser Leu X6 Ser, wherein X1 = Y or N or F or a conservative substitution thereof; X2 = I or L or a conservative substitution thereof; X3 = F or Y or H or a conservative substitution thereof; X4 = Y or H or a conservative substitution thereof; X5 = Y or N or a conservative substitution thereof; X6 = K or R or a conservative substitution thereof. |
| | SEQ ID NO: 50232 | VH3 | Gly Asp Tyr Asp Gly Ser Tyr His X1 Tyr X2 Gly X3 Asp Val, wherein X1 = Y or P or H or a conservative substitution thereof; X2 = Y or H or a conservative substitution thereof; X3 = M or L or a conservative substitution thereof. |
| VH-CONSENSUS-30 TABLE 64 | SEQ ID NO: 50043 | VH1 | X1 X2 X3 Met Ser, wherein X1 = S or N or T or a conservative substitution thereof; X2 = Y or H or a conservative substitution thereof; X3 = A or P or V or a conservative substitution thereof. |
| | SEQ ID NO: 50044 | VH2 | X1 Ile Ser Gly X2 Gly X3 X4 X5 Tyr Tyr Ala Asp Ser Val Lys Gly, wherein X1 = V or A or I or a conservative substitution thereof; X2 = G or S or a conservative substitution thereof; X3 = S or G or T or a conservative substitution thereof; X4 = S or T or a conservative substitution thereof; X5 = T or A or a conservative substitution thereof. |
| | SEQ ID NO: 50045 | VH3 | X1 X2 Gly X3 X4 X5 X6 X7 X8 X9 X10 Gly Met Asp, wherein X1 = W or A or a conservative substitution thereof; X2 = R or G or a conservative substitution thereof; X3 = N or T or a conservative substitution thereof; X4 = P or T or a conservative substitution thereof; X5 = T or G or a conservative substitution thereof; X6 = Absent or S or a conservative substitution thereof; X7 = Absent or Y or a conservative substitution thereof; X8 = Absent or Y or a conservative substitution thereof; X9 = D or Y or a conservative substitution thereof. |

FIGURE 55
(Continued)

| | | | |
|---|---|---|---|
| VH-CONSENSUS-31 TABLE 65 | SEQ ID NO: 50253 | VH1 | X1 Tyr Gly X2 His, wherein X1 = S or N or T or a conservative substitution thereof; X10 = Y or N or S or a conservative substitution thereof. |
| | SEQ ID NO: 50254 | VH2 | X1 X2 Trp Tyr Asp Gly X3 X4 Lys Tyr Tyr X5 Asp Ser Val Lys Gly, wherein X1 = I or V or A or a conservative substitution thereof; X2 = I or M or a conservative substitution thereof; X3 = S or T or a conservative substitution thereof; X4 = N or Y or S or a conservative substitution thereof; X5 = A or G or T or V or a conservative substitution thereof. |
| | SEQ ID NO: 50255 | VH3 | X1 X2 X3 X4 X5 X6 X7 X8 X9 X10 X11 X12, wherein X1 = D or E or a conservative substitution thereof; X2 = H or R or Q or A or G or T or Y or a conservative substitution thereof; X3 = Y or G or F or H or a conservative substitution thereof; X4 = D or I or F or a conservative substitution thereof; X5 = P or V or L or a conservative substitution thereof; X6 = W or G or Absent or a conservative substitution thereof; X7 = S or A or Absent or a conservative substitution thereof; X8 = G or T or E or a conservative substitution thereof; X9 = H or Y or W or F or a conservative substitution thereof; X10 = P or L or S or a conservative substitution thereof; X11 = D or A or C or G or a conservative substitution thereof; X12 = Y or F or S or a conservative substitution thereof. |
| VH-CONSENSUS-32 TABLE 66 | SEQ ID NO: 50233 | VH1 | X1 X2 X3 Trp Ser () wherein X1 = G or V or P or A or D or Y or a conservative substitution thereof; X2 = Y or C or S or P or a conservative substitution thereof; X3 = Y or F or a conservative substitution thereof. |
| | SEQ ID NO: 50234 | VH2 | Glu X1 Asn X2 Ser Gly X3 X4 X5 X6 Asn Pro Ser Leu Lys Ser, wherein X1 = I or S or V or a conservative substitution thereof; X2 = H or I or Q or a conservative substitution thereof; X3 = R or S or a conservative substitution thereof; X4 = T or A or S or a conservative substitution thereof; X5 = N or T or a conservative substitution thereof; X6 = Y or F or a conservative substitution thereof. |
| | SEQ ID NO: 50235 | VH3 | Asp Tyr Gly Leu Asp Tyr. |
| VH-CONSENSUS-33 TABLE 67 | SEQ ID NO: 50046 | VH1 | X1 Ser X2 X3 Tyr Trp Gly, wherein X1 = R or G or a conservative substitution thereof; X2 = S or N or a conservative substitution thereof; X3 = Y or S or a conservative substitution thereof. |
| | SEQ ID NO: 50047 | VH2 | X1 Ile Tyr Tyr Ser Gly X2 X3 X4 X5 X6 Pro Ser Leu Lys Ser, wherein X1 = N or S or a conservative substitution thereof; X2 = S or Y or A or T or I or a conservative substitution thereof. |

FIGURE 55
(Continued)

| | | | |
|---|---|---|---|
| | SEQ ID NO: 50048 | VH3 | substitution thereof, X3 = T or A or P or S or a conservative substitution thereof, X4 = Y or Q or S or A or N or a conservative substitution thereof, X5 = Y or C or H or a conservative substitution thereof, X6 = N or I or T or a conservative substitution thereof. |
| VH-CONSENSUS-34 TABLE 68 | SEQ ID NO: 50049 | VH1 | X1 Ser X2 Ser Trp Ser X3 Asp X4, wherein X1 = H or L or a conservative substitution thereof, X2 = S or T or G or a conservative substitution thereof, X3 = L or F or I or V or a conservative substitution thereof, X4 = Y or N or C or D or F or a conservative substitution thereof. |
| | SEQ ID NO: 50050 | VH2 | X1 X2 X3 X4 X5, wherein X1 = G or D or a conservative substitution thereof, X2 = Y or H or a conservative substitution thereof, X3 = Y or F or a conservative substitution thereof, X4 = I or M or a conservative substitution thereof, X5 = U or N or a conservative substitution thereof. |
| | SEQ ID NO: 50051 | VH3 | Trp Ile Asn X1 X2 X3 X4 X5 Thr Asn Tyr X6 X7 Lys Phe Gln X8, wherein X1 = P or S or a conservative substitution thereof, X2 = N or K or a conservative substitution thereof, X3 = S or N or a conservative substitution thereof, X4 = G or D or a conservative substitution thereof, X5 = G or D or a conservative substitution thereof, X6 = A or E or a conservative substitution thereof, X7 = Q or E or a conservative substitution thereof, X8 = G or D or a conservative substitution thereof. |
| | SEQ ID NO: 50051 | VH3 | X1 X2 X3 X4 X5 X6 X7 X8 X9 X10 X11 X12 X13 X14 X15, wherein X1 = G or D or a conservative substitution thereof, X2 = Y or G or T or F or a conservative substitution thereof, X3 = S or Y or D or R or a conservative substitution thereof, X4 = Y or S or a conservative substitution thereof, X5 = G or Absent or S or a conservative substitution thereof, X6 = Y or S or Absent or a conservative substitution thereof, X7 = Absent or G or a conservative substitution thereof, X8 = Absent or S or a conservative substitution thereof, X9 = Absent or Y or a conservative substitution thereof, X10 = Absent or Y or F or H or a conservative substitution thereof, X11 = N or Absent or D or a conservative substitution thereof, X12 = W or Absent or D or E or a conservative substitution thereof, X13 = F or L or a conservative substitution thereof, X14 = D or A or a conservative substitution thereof, X15 = P or S or a conservative substitution thereof. |
| VH-CONSENSUS-35 TABLE 69 | SEQ ID NO: 50052 | VH1 | X1 X2 Gly Met His, wherein X1 = H or N or a conservative substitution thereof, X2 = Y or S or a conservative substitution thereof. |
| | SEQ ID NO: 50053 | VH2 | X1 Ile X2 Tyr Asp Gly Ser X3 X4 X5 Tyr Ala Asp Ser Val Lys Gly, wherein X1 = V or I or a conservative substitution thereof, X2 = W or Y or a conservative substitution thereof. |

FIGURE 55
(Continued)

| | | | |
|---|---|---|---|
| | SEQ ID NO: 50054 | VH3 | X3 = N or Y or a conservative substitution thereof, X4 = K or E or a conservative substitution thereof, X5 = Y or C or N or a conservative substitution thereof. X1 X2 X3 X4 X5 X6 X7 X8 X9 X10 X11 X12 X13 X14 Gly X15 Asp Val, wherein X1 = G or D or a conservative substitution thereof, X2 = D or R or a conservative substitution thereof, X3 = W or H or a conservative substitution thereof, X4 = N or Y or a conservative substitution thereof, X5 = P or D or a conservative substitution thereof, X6 = Absent or F or a conservative substitution thereof, X7 = Absent or H or a conservative substitution thereof, X8 = Absent or V or a conservative substitution thereof, X9 = Absent or P or a conservative substitution thereof, X10 = Absent or Y or a conservative substitution thereof, X11 = Absent or Y or a conservative substitution thereof, X12 = Absent or Y or a conservative substitution thereof, X13 = Absent or Y or a conservative substitution thereof, X14 = E or Y or a conservative substitution thereof, X15 = M or L or a conservative substitution thereof. |
| VH-CONSENSUS-36 TABLE 70 | SEQ ID NO: 50055 | VH1 | Ser X1 Ala Met X2, wherein X1 = Y or S or a conservative substitution thereof, X2 = S or T or N or a conservative substitution thereof. |
| | SEQ ID NO: 50056 | VH2 | X1 Ile X2 Gly X3 Gly X4 X5 X6 X7 Tyr Ala Asp Ser Val Lys Gly, wherein X1 = A or V or a conservative substitution thereof, X2 = S or I or a conservative substitution thereof, X3 = S or R or N or F or a conservative substitution thereof, X4 = G or S or a conservative substitution thereof, X5 = N or R or S or a conservative substitution thereof, X6 = T or A or a conservative substitution thereof, X7 = F or Y or a conservative substitution thereof. |
| | SEQ ID NO: 50057 | VH3 | X1 X2 X3 X4 X5 X6 X7 X8 X9 X10 X11 X12 Phe Asp Tyr, wherein X1 = K or D or R or a conservative substitution thereof, X2 = D or Y or H or M or R or a conservative substitution thereof, X3 = Y or G or N or a conservative substitution thereof, X4 = D or I or R or Y or a conservative substitution thereof, X5 = Y or Absent or S or V or a conservative substitution thereof, X6 = V or Absent or G or R or S or a conservative substitution thereof, X7 = W or Absent or I or a conservative substitution thereof, X8 = Absent or A or a conservative substitution thereof, X9 = G or Absent or V or a conservative substitution thereof, X10 = S or Absent or A or T or Y or a conservative substitution thereof, X11 = P or Absent or G or I or a conservative substitution thereof, X12 = Y or F or T or a conservative substitution thereof. |

FIGURE 55
(Continued)

| VH-CONSENSUS-37 TABLE 71 | SEQ ID NO: 50058 | VH1 | X1 X2 X3 X4 His, wherein X1 = G or D or a conservative substitution thereof, X2 = Y or H or a conservative substitution thereof, X3 = Y or C or a conservative substitution thereof, X4 = M or I or a conservative substitution thereof. |
|---|---|---|---|
| | SEQ ID NO: 50059 | VH2 | X1 Ile X2 X3 X4 Ser Gly X5 X6 X7 X8 X9 Gln Lys Phe Gln X10, wherein X1 = W or S or a conservative substitution thereof, X2 = N or Y or a conservative substitution thereof, X3 = F or K or a conservative substitution thereof, X4 = N or K or a conservative substitution thereof, X5 = G or A or a conservative substitution thereof, X6 = T or A or a conservative substitution thereof, X7 = N or D or a conservative substitution thereof, X8 = Y or N or S or a conservative substitution thereof, X9 = A or G or V or a conservative substitution thereof, X10 = G or D or V or a conservative substitution thereof. |
| | SEQ ID NO: 50060 | VH3 | X1 X2 Tyr X3 Gly Ser Gly X4 Tyr X5 Asn X6 Phe Asp Tyr, wherein X1 = S or A or V or T or a conservative substitution thereof, X2 = Y or F or N or a conservative substitution thereof, X3 = Y or H or a conservative substitution thereof, X4 = S or T or a conservative substitution thereof, X5 = Y or H or a conservative substitution thereof, X6 = E or G or D or a conservative substitution thereof. |
| VH-CONSENSUS-38 TABLE 72 | SEQ ID NO: 50061 | VH1 | Gly Tyr Tyr X1 His, wherein X1 = I or T or a conservative substitution thereof. |
| | SEQ ID NO: 50062 | VH2 | Trp Ile Asn Pro Tyr Ser Gly X1 Thr X2 X3 Ala Gln Lys Phe Gln Gly, wherein X1 = D or G or a conservative substitution thereof, X2 = N or K or a conservative substitution thereof, X3 = Y or S or a conservative substitution thereof. |
| | SEQ ID NO: 50236 | VH3 | Asp Trp Gly Gly Tyr Ser Ser Tyr Tyr X1 Gly Met Asp Val, wherein X1 = Y or F or a conservative substitution thereof. |
| VH-CONSENSUS-39 TABLE 73 | SEQ ID NO: 50063 | VH1 | X1 X2 X3 Met X4, wherein X1 = S or T or a conservative substitution thereof, X2 = Y or F or a conservative substitution thereof, X3 = S or T or N or G or a conservative substitution thereof, X4 = N or S or I or a conservative substitution thereof. |
| | SEQ ID NO: 50064 | VH2 | Ser Ile Ser X1 X2 X3 X4 Tyr X5 X6 Tyr X7 Asp Ser Val Lys Gly, wherein X1 = G or S or a conservative substitution thereof, X2 = S or T or a conservative substitution thereof, X3 = S or T or N or G or a conservative substitution thereof, X4 = N or S or I or a conservative substitution thereof, X5 = S or N or T or Y or a conservative substitution thereof, X5 |

FIGURE 55
(Continued)

| | | | |
|---|---|---|---|
| | SEQ ID NO: 50065 | VH3 | = I or M or S or a conservative substitution thereof, X6 = Y or N or a conservative substitution thereof, X7 = A or T or a conservative substitution thereof. |
| | | | Leu Thr Phe Asp Tyr. |
| VH-CONSENSUS-40 TABLE 74 | SEQ ID NO: 50066 | VH1 | X1 Tyr Gly Met His, wherein X1 = T or S or a conservative substitution thereof. |
| | SEQ ID NO: 50067 | VH2 | X1 Ile Trp Tyr Asp Gly X2 Asn Lys Tyr Ala Asp Ser Val X3 Gly, wherein X1 = I or V or a conservative substitution thereof, X2 = T or S or a conservative substitution thereof, X3 = K or R or a conservative substitution thereof. |
| | SEQ ID NO: 50068 | VH3 | Asp Pro Leu Arg Gly Tyr Asn Asp Pro Val X1 Asp Tyr, wherein X1 = M or L or a conservative substitution thereof. |
| VH-CONSENSUS-41 TABLE 75 | SEQ ID NO: 50069 | VH1 | X1 Tyr Ala Met X2, wherein X1 = S or N or a conservative substitution thereof, X2 = S or N or T or a conservative substitution thereof. |
| | SEQ ID NO: 50070 | VH2 | Ala Ile Ser Gly X1 Gly X2 Asn Thr Phe Tyr Ala Asp Ser Val Lys Gly, wherein X1 = R or S or a conservative substitution thereof, X2 = G or K or a conservative substitution thereof. |
| | SEQ ID NO: 50071 | VH3 | Arg Val Thr Asp Tyr Gly Gly Asn Asp Trp Phe Asp Pro. |
| VH-CONSENSUS-42 TABLE 76 | SEQ ID NO: 50072 | VH1 | X1 Tyr Gly Met His, wherein X1 = T or S or a conservative substitution thereof. |
| | SEQ ID NO: 50073 | VH2 | Val X1 Trp Tyr X2 Gly X3 X4 X5 X6 X7 X8 Asp Ser Val X9 Gly, wherein X1 = I or V or a conservative substitution thereof, X2 = G or D or a conservative substitution thereof, X3 = S or N or a conservative substitution thereof, X4 = N or D or S or a conservative substitution thereof, X5 = K or T or a conservative substitution thereof, X6 = D or Y or S or a conservative substitution thereof, X7 = Y or F or a conservative substitution thereof, X8 = A or V or a conservative substitution thereof, X9 = K or R or T or a conservative substitution thereof. |
| | SEQ ID NO: 50074 | VH3 | Asp Arg X1 X2 Cys Ser Gly X3 X4 Cys Pro Tyr Tyr Tyr Tyr Gly Met Asp Val, wherein X1 = D or V or a conservative substitution thereof, X2 = Y or F or a conservative substitution thereof, X3 = G or T or a conservative substitution thereof, X4 = S or N or a conservative substitution thereof. |

FIGURE 55
(Continued)

| | | | |
|---|---|---|---|
| VH-CONSENSUS-43 TABLE 77 | SEQ ID NO: 50075 | VH1 | Arg Ser Ser Tyr Tyr Trp Gly |
| | SEQ ID NO: 50076 | VH2 | Asn Ile Tyr Tyr X1 Gly X2 X3 Tyr X4 Asn Pro Ser X5 Lys X6, wherein X1 = S or G or a conservative substitution thereof, X2 = S or T or N or a conservative substitution thereof, X3 = T or A or a conservative substitution thereof, X4 = Y or N or D or H or T or a conservative substitution thereof, X5 = L or V or a conservative substitution thereof, X6 = S or G or a conservative substitution thereof. |
| | SEQ ID NO: 50077 | VH3 | His Gly Lys Asp Trp Gly Leu Asp Tyr X1, wherein X1 = Y or F or N or a conservative substitution thereof. |
| VH-CONSENSUS-44 TABLE 78 | SEQ ID NO: 50078 | VH1 | Gly Tyr Tyr X1 His, wherein X1 = M or I or a conservative substitution thereof. |
| | SEQ ID NO: 50079 | VH2 | Trp Ile X1 Pro X2 Ser Gly Thr Asn X3 X4 Gln Lys Phe Gln Gly, wherein X1 = K or N or a conservative substitution thereof, X2 = N or K or a conservative substitution thereof, X3 = Q or S or H or N or Y or a conservative substitution thereof, X4 = A or V or a conservative substitution thereof. |
| | SEQ ID NO: 50080 | VH3 | Ala Pro Gly X1 X2 X3 X4 Gly X5 Trp Gly X6 Phe Asp Tyr, wherein X1 = T or K or F or a conservative substitution thereof, X2 = A or V or a conservative substitution thereof, X3 = A or P or a conservative substitution thereof, X4 = A or T or a conservative substitution thereof, X5 = T or S or a conservative substitution thereof, X6 = Y or F or C or a conservative substitution thereof. |
| VH-CONSENSUS-45 TABLE 79 | SEQ ID NO: 50081 | VH1 | Thr X1 Gly Val Gly Val Gly, wherein X1 = G or S or a conservative substitution thereof. |
| | SEQ ID NO: 50082 | VH2 | X1 Ile Tyr X2 Trp Asp Asp X3 Arg Tyr Ser Pro Ser Leu X4 Ser, wherein X1 = L or F or a conservative substitution thereof, X2 = D or H or N or K or S or a conservative substitution thereof, X3 = K or E or a conservative substitution thereof, X4 = K or R or a conservative substitution thereof. |
| | SEQ ID NO: 50083 | VH3 | X1 X2 Ala Val X3 X4 Asp Tyr, wherein X1 = L or I or A or a conservative substitution thereof, X2 = L or V or A or a conservative substitution thereof, X3 = A or S or a conservative substitution thereof, X4 = F or C or a conservative substitution thereof. |
| VH-CONSENSUS-46 TABLE 80 | SEQ ID NO: 50084 | VH1 | X1 Tyr Gly Met His () wherein X1 = S or N or T or a conservative substitution thereof. |

FIGURE 55
(Continued)

| | SEQ ID NO. | | Sequence |
|---|---|---|---|
| | SEQ ID NO. 50085 | VH2 | X1 Ile Trp Tyr Asp Gly Ser X2 Lys Tyr X3 Asp Ser Val Lys Gly, wherein X1 = I or V or a conservative substitution thereof, X2 = Y or N or a conservative substitution thereof, X3 = A or V or a conservative substitution thereof. |
| | SEQ ID NO. 50086 | VH3 | Glu X1 Tyr Asp Phe Trp Ser Gly X2 X3 X4 X5, wherein X1 = A or G or R or N or a conservative substitution thereof, X2 = Y or F or H or a conservative substitution thereof, X3 = F or L or Y or W or a conservative substitution thereof, X4 = D or G or a conservative substitution thereof, X5 = Y or S or a conservative substitution thereof. |
| VH-CONSENSUS-47 TABLE 81 | SEQ ID NO. 50087 | VH1 | Ser Tyr Gly X1 His, wherein X1 = M or L or a conservative substitution thereof. |
| | SEQ ID NO. 50088 | VH2 | Val Ile Trp Tyr Asp Gly Ser Asn Lys X1 Tyr X2 Asp Ser Val Lys Gly, wherein X1 = Y or N or a conservative substitution thereof, X2 = A or E or a conservative substitution thereof. |
| | SEQ ID NO. 50089 | VH3 | X1 X2 X3 Tyr X4 X5 X6 X7 X8 X9 X10 X11 X12 Gly Met Asp Val, wherein X1 = D or W or a conservative substitution thereof, X2 = R or G or Y or a conservative substitution thereof, X3 = D or S or Y or a conservative substitution thereof, X4 = G or Y or a conservative substitution thereof, X5 = D or Y or a conservative substitution thereof, X6 = Absent or P or a conservative substitution thereof, X7 = Absent or P or a conservative substitution thereof, X8 = Absent or Y or a conservative substitution thereof, X9 = Absent or Y or a conservative substitution thereof, X10 = Absent or Y or a conservative substitution thereof, X11 = Absent or Y or a conservative substitution thereof, X12 = Y or D or a conservative substitution thereof. |
| VH-CONSENSUS-48 TABLE 82 | | VH1 | X1 X2 X3 Met X4 (SEQ ID NO: 50090) wherein X1 = S or N or T or a conservative substitution thereof, X2 = Y or S or a conservative substitution thereof, X3 = A or V or a conservative substitution thereof, X4 = S or T or N or a conservative substitution thereof. |
| | | VH2 | X1 X2 X3 Gly X4 Gly X5 X6 Thr X7 X8 X9 Asp Ser Val X10 Gly (SEQ ID NO: 50091) wherein X1 = A or G or a conservative substitution thereof, X2 = I or S or V or a conservative substitution thereof, X3 = S or V or a conservative substitution thereof, X4 = S or R or a conservative substitution thereof, X5 = G or A or S or V or a conservative substitution thereof, X6 = N or R or K or a conservative substitution thereof, X7 = F or Y or a conservative substitution thereof, X8 = Y or N or a |

FIGURE 55
(Continued)

| | | |
|---|---|---|
| | VH3 | conservative substitution thereof, X9 = A or T or a conservative substitution thereof, X10 = K or T or a conservative substitution thereof |
| | VH3 | X1 X2 X3 X4 X5 X6 X7 X8 Gly X9 Asp Val (SEQ ID NO: 50092) wherein X1 = L or D or E or a conservative substitution thereof, X2 = G or R or a conservative substitution thereof, X3 = K or G or L or a conservative substitution thereof, X4 = D or Q or Y or a conservative substitution thereof, X5 = Y or W or a conservative substitution thereof, X6 = Y or H or L or a conservative substitution thereof, X7 = Y or Absent or L or a conservative substitution thereof, X8 = Y or G or a conservative substitution thereof, X9 = M or V or a conservative substitution thereof |
| VH-CONSENSUS-49 TABLE 83 | VH1 | Ser Tyr X1 Met X2 (SEQ ID NO: 50093) wherein X1 = V or A or a conservative substitution thereof, X2 = S or N or a conservative substitution thereof |
| | VH2 | X1 X2 Ser Gly X3 X4 Thr X5 Tyr Ala Asp Ser Val X6 X7 (SEQ ID NO: 50094) wherein X1 = A or G or T or S or a conservative substitution thereof, X2 = M or I or T or a conservative substitution thereof, X3 = G or N or V or a conservative substitution thereof, X4 = R or N or W or a conservative substitution thereof, X5 = Y or F or N or a conservative substitution thereof, X6 = K or N or a conservative substitution thereof, X7 = G or D or a conservative substitution thereof |
| | VH3 | X1 X2 X3 X4 X5 X6 X7 X8 X9 X10 X11 X12 (SEQ ID NO: 50095) wherein X1 = L or V or Y or F or a conservative substitution thereof, X2 = T or E or F or G or a conservative substitution thereof, X3 = A or G or L or W or Absent or F or a conservative substitution thereof, X4 = Absent or G or M or a conservative substitution thereof, X5 = Absent or G or a conservative substitution thereof, X6 = Absent or A or a conservative substitution thereof, X7 = Absent or G or a conservative substitution thereof, X8 = Absent or I or F or a conservative substitution thereof, X9 = Absent or N or Absent or a conservative substitution thereof, X10 = F or N or Absent or a conservative substitution thereof, X11 = D or G or I or a conservative substitution thereof, X12 = Y or D or a conservative substitution thereof |
| VH-CONSENSUS-50 TABLE 84 | VH1 | X1 Tyr Gly X2 His (SEQ ID NO: 50096) wherein X1 = S or Y or a conservative substitution thereof, X2 = M or L or a conservative substitution thereof |
| | VH2 | X1 Ile Ser Tyr X2 Gly X3 Asn X4 X5 X6 Ala Asp Ser Val Lys Gly (SEQ ID NO: 50097) wherein X1 = I or V or a conservative substitution thereof, X2 = A or G or D or S or V or a conservative substitution thereof, X3 = S or I or N or R or T or a conservative substitution thereof, X4 = K or N |

FIGURE 55
(Continued)

| | | | |
|---|---|---|---|
| | | VH3 | or Q or a conservative substitution thereof, X5 = Y or S or D or H or a conservative substitution thereof, X6 = Y or S or a conservative substitution thereof. |
| | | | X1 X2 X3 X4 X5 X6 X7 X8 X9 X10 X11 X12 X13 X14 X15 Tyr Gly Met Asp Val (SEQ ID NO: 50098) wherein X1 = R or E or a conservative substitution thereof, X2 = G or D or a conservative substitution thereof, X3 = Y or R or a conservative substitution thereof, X4 = S or Y or a conservative substitution thereof, X5 = Y or C or a conservative substitution thereof, X6 = G or S or a conservative substitution thereof, X7 = Absent or G or a conservative substitution thereof, X8 = Absent or T or a conservative substitution thereof, X9 = Absent or S or a conservative substitution thereof, X10 = Absent or C or a conservative substitution thereof, X11 = Absent or P or a conservative substitution thereof, X12 = Absent or Y or a conservative substitution thereof, X13 = Absent or Y or a conservative substitution thereof, X14 = Absent or Y or a conservative substitution thereof, X15 = G or Y or a conservative substitution thereof. |
| VH-CONSENSUS-51 TABLE 85 | | VH1 | X1 X2 X3 Met X4 (SEQ ID NO: 50099) wherein X1 = D or S or a conservative substitution thereof, X2 = Y or G or a conservative substitution thereof, X3 = V or G or a conservative substitution thereof, X4 = H or Q or a conservative substitution thereof. |
| | | VH2 | X1 Ile Trp Tyr Asp Gly Ser Asn Lys Tyr Tyr Ala Asp Ser Val Lys X2 (SEQ ID NO: 50100) wherein X1 = V or I or a conservative substitution thereof, X2 = G or V or a conservative substitution thereof. |
| | | VH3 | Gln X1 Tyr X2 Ser Gly Trp X3 Asp Tyr Gly X4 Asp Val (SEQ ID NO: 50101) wherein X1 = P or R or a conservative substitution thereof, X2 = T or N or a conservative substitution thereof, X3 = Y or H or a conservative substitution thereof, X4 = M or L or a conservative substitution thereof. |
| VH-CONSENSUS-52 TABLE 86 | | VH1 | Ser Tyr Gly X1 Ser (SEQ ID NO: 50102) wherein X1 = I or F or V or a conservative substitution thereof. |
| | | VH2 | Trp Ile Ser Ala Tyr Asn Gly Asn X1 Lys X2 Ala Gln X3 X4 Gln Gly (SEQ ID NO: 50103) wherein X1 = T or R or a conservative substitution thereof, X2 = Y or N or E or F or a conservative substitution thereof, X3 = K or R or a conservative substitution thereof, X4 = L or F or a conservative substitution thereof. |
| | | VH3 | His Asp Phe Trp Ser Gly Tyr Tyr Lys Gly Met Asp Val (SEQ ID NO: 50227). |

FIGURE 55
(Continued)

| | | |
|---|---|---|
| VH-CONSENSUS-53 TABLE 87 | VH1 | X1 Ser X2 Ala Met Ser (SEQ ID NO: 50104) wherein X1 = S or R or a conservative substitution thereof, X2 = Y or S or a conservative substitution thereof. |
| | VH2 | X1 Ile Ser Gly X2 Gly X3 X4 Thr Phe X5 X6 Asp Ser Val Lys Gly (SEQ ID NO: 50105) wherein X1 = A or V or S or a conservative substitution thereof, X2 = R or S or a conservative substitution thereof, X3 = G or I or V or a conservative substitution thereof, X4 = N or S or a conservative substitution thereof, X5 = D or Y or a conservative substitution thereof, X6 = A or T or a conservative substitution thereof. |
| | VH3 | X1 X2 Ser X3 X4 X5 Phe Asp Tyr (SEQ ID NO: 50106) wherein X1 = E or S or a conservative substitution thereof, X2 = R or N or a conservative substitution thereof, X3 = G or S or a conservative substitution thereof, X4 = S or G or a conservative substitution thereof, X5 = Y or W or a conservative substitution thereof. |
| VH-CONSENSUS-54 TABLE 88 | VH1 | X1 Tyr X2 Met His (SEQ ID NO: 50107) wherein X1 = S or N or Y or H or a conservative substitution thereof, X2 = V or G or a conservative substitution thereof. |
| | VH2 | X1 Ile Trp X2 Asp Gly X3 X4 X5 Tyr Tyr X6 Asp Ser Val Lys Gly (SEQ ID NO: 50108) wherein X1 = V or L or a conservative substitution thereof, X2 = H or Y or a conservative substitution thereof, X3 = S or T or a conservative substitution thereof, X4 = N or D or a conservative substitution thereof, X5 = K or A or a conservative substitution thereof, X6 = A or V or G or a conservative substitution thereof. |
| | VH3 | Glu Asn Ser Ser X1 Tyr Phe Asp Tyr Trp Gly Gln Gly Thr Leu Val Thr Val Ser Ser (SEQ ID NO: 50109) wherein X1 = Y or F or a conservative substitution thereof. |
| VH-CONSENSUS-55 TABLE 89 | VH1 | Thr Ser Gly Val Gly Val Gly (SEQ ID NO: 50110). |
| | VH2 | Leu Ile Asn Trp Asn Asp Asp Lys Arg X1 Ser Pro Ser Leu Lys Ser (SEQ ID NO: 50111) wherein X1 = Y or F or a conservative substitution thereof. |
| | VH3 | Lys X1 Thr Trp Val Ala Phe Asp Ile (SEQ ID NO: 50112) wherein X1 = A or T or a conservative substitution thereof. |
| VH-CONSENSUS-56 TABLE 90 | VH1 | Ser Tyr X1 X2 X3 (SEQ ID NO: 50113) wherein X1 = V or A or a conservative substitution thereof, X2 = M or I or L or a conservative substitution thereof, X3 = N or S or R or a conservative substitution thereof. |
| | VH2 | X1 X2 Ser Gly Ser Gly X3 X4 Thr Tyr X5 Asp Ser Val Lys Gly (SEQ ID NO: 50114) wherein X1 = A or D or a conservative substitution thereof, X2 = I or M or a conservative substitution thereof, X3 = G or D or V or a conservative substitution thereof, X4 = R or S or F or T or a conservative substitution thereof. |

FIGURE 55
(Continued)

| | | |
|---|---|---|
| | VH3 | conservative substitution thereof; X5 = A or V or a conservative substitution thereof. Thr X1 X2 X3 X4 X5 (SEQ ID NO: 50115) wherein X1 = A or G or S or T or Y or a conservative substitution thereof; X2 = T or V or Absent or H or L or G or a conservative substitution thereof; X3 = F or Absent or K or a conservative substitution thereof; X4 = D or Absent or a conservative substitution thereof; X5 = Y or L or a conservative substitution thereof. |
| VH-CONSENSUS-57 TABLE 91 | VH1 | Ser X1 Ala Met X2 (SEQ ID NO: 50116) wherein X1 = Y or F or a conservative substitution thereof; X2 = S or N or a conservative substitution thereof. |
| | VH2 | X1 X2 Ser Gly X3 Gly X4 X5 Thr X6 Tyr Ala Asp Ser Val Lys Gly (SEQ ID NO: 50117) wherein X1 = V or A or I or a conservative substitution thereof; X2 = I or L or a conservative substitution thereof; X3 = R or S or G or a conservative substitution thereof; X4 = G or S or K or a conservative substitution thereof; X5 = T or N or S or a conservative substitution thereof; X6 = F or Y or a conservative substitution thereof. |
| | VH3 | Lys Arg Thr X1 X2 Asp X3 Phe Asp X4 (SEQ ID NO: 50118) wherein X1 = P or G or a conservative substitution thereof; X2 = S or D or E or a conservative substitution thereof; X3 = V or A or a conservative substitution thereof; X4 = I or V or a conservative substitution thereof. |
| VH-CONSENSUS-58 TABLE 92 | VH1 | X1 X2 X3 Met His (SEQ ID NO: 50237) wherein X1 = S or N or T or a conservative substitution thereof; X2 = Y or F or a conservative substitution thereof; X3 = G or D or N or a conservative substitution thereof. |
| | VH2 | X1 Ile Trp X2 Asp Gly X3 X4 X5 Tyr X6 X7 Asp Ser Val Lys Gly (SEQ ID NO: 50238) wherein X1 = V or H or a conservative substitution thereof; X2 = Y or H or a conservative substitution thereof; X3 = S or R or a conservative substitution thereof; X4 = N or D or H or a conservative substitution thereof; X5 = K or R or a conservative substitution thereof; X6 = Y or C or S or a conservative substitution thereof; X7 = A or E or F or a conservative substitution thereof. |
| | VH3 | Asp X1 X2 X3 X4 X5 X6 X7 X8 X9 Asp X10 (SEQ ID NO: 50239) wherein X1 = R or D or H or a conservative substitution thereof; X2 = P or S or A or a conservative substitution thereof; X3 = I or R or Y or a conservative substitution thereof; X4 = S or L or V or W or a conservative substitution thereof; X5 = Absent or G or a conservative substitution thereof; X6 = Absent or A or a conservative substitution thereof; X7 = S or T or A or a conservative substitution thereof; X8 = A or F or S or Y or a conservative substitution thereof; X9 = F or G or S or a conservative substitution thereof. |

FIGURE 55
(Continued)

| | | |
|---|---|---|
| VH-CONSENSUS-59 TABLE 93 | | conservative substitution thereof, X10 = Y or F or a conservative substitution thereof. |
| | VH1 | X1 Tyr X2 Met Asn (SEQ ID NO: 50240) weherein X1 = S or N or a conservative substitution thereof, X2 = N or S or a conservative substitution thereof |
| | VH2 | Tyr Ile Ser X1 Ser X2 X3 Thr X4 X5 Tyr X6 Asp Ser Val X7 Gly (SEQ ID NO: 50241) wherein X1 = R or S or a conservative substitution thereof, X2 = S or G or a conservative substitution thereof, X3 = N or S or a conservative substitution thereof, X4 = K or T or a conservative substitution thereof, X5 = Y or H or a conservative substitution thereof, X6 = A or V or a conservative substitution thereof, X7 = K or R or E or Q or a conservative substitution thereof. |
| | VH3 | Asp X1 X2 X3 X4 X5 X6 X7 X8 X9 Tyr Tyr Gly X10 Asp Val (SEQ ID NO: 50242) wherein X1 = R or S or a conservative substitution thereof, X2 = S or R or a conservative substitution thereof, X3 = G or K or a conservative substitution thereof, X4 = S or G or a conservative substitution thereof, X5 = Y or F or a conservative substitution thereof, X6 = G or Absent or a conservative substitution thereof, X7 = Y or Absent or a conservative substitution thereof, X8 = F or Absent or a conservative substitution thereof, X9 = Y or Absent or a conservative substitution thereof, X10 = L or M or a conservative substitution thereof. |
| VH-CONSENSUS-60 TABLE 94 | VH1 | Ser Gly Gly Asp Tyr Tyr Trp Ser (SEQ ID NO: 50119) |
| | VH2 | Tyr Ile Tyr Tyr Ser Gly X1 Thr Tyr Tyr Asn Pro Ser Leu Lys Ser (SEQ ID NO: 50120) wherein X1 = S or I or P or a conservative substitution thereof. |
| | VH3 | Asp X1 X2 X3 X4 Gly Met Asp Val (SEQ ID NO: 50121) wherein X1 = S or G or H or a conservative substitution thereof, X2 = S or A or a conservative substitution thereof, X3 = S or L or R or a conservative substitution thereof, X4 = Y or R or H or a conservative substitution thereof. |

FIGURE 55
(Continued)

Table 20A

VARIABLE LIGHT CDR CONSENSUS SEQUENCES I

| NAME (ORIGINAL AND PATENT) | Patent SEQ ID NO: | SEQUENCE |
|---|---|---|
| VL-Consensus-1 (Table 35) (generated from 13 light chain sequences) | SEQ ID NO: 50366 | DIQMTQSPSSVSASVGDRVTITCRASQGISRWLAWY QQKPGKAPKLLIYAASSLQSGVPSRFSGSGSGTDFTL TISSLQPEDFATYYCQQANSFPFTFGPGTKVDIKR |
| VL-Consensus-2 (Table 36) (generated from 11 light chain sequences) | SEQ ID NO: 50367 | SYELTQPPSVSVSPGQTASITCSGDKLGDKYAYWYQ QKPGQSPVLVIYQDRKRPSGIPERFSGSNSGNFATLTI SGTQAMDEADYYCQAWDNSTVVFGGGTKLTVLGG |
| VL-Consensus-3 (Table 37) (generated from 15 light chain sequences) | SEQ ID NO: 50368 | DIVMTQSPDSLAVSLGERATINCKSSQSVLYSSNNNN YLAWYQQKPGQPPKLLIYWASTRESGVPDRFSGSGS GTDFTLTISSLQAEDVAVYYCQQYYSTPFTFGQGTK VEIKR |
| VL-Consensus-4 (Table 38) (generated from 23 light chain sequences) | SEQ ID NO: 50369 | DIQMTQSPSSLSASVGDRVTITCRASQGISNYLAWFQ QKPGKAPKSLIYAASSLQSGVPSKFSGSGSGTDFTLTI SSLQPEDFATYYCQQYNSYPFTFGPGTKVDIKR |
| VL-Consensus 5 (Table 39) (generated from 17 light chain sequences) | SEQ ID NO: 50370 | DIQMTQSPSSLSASVGDRVTITCRASQGIRNNLQWY QQKPGKAPKSLIEAASSLQSGVPSKFSGSGSGTEFTL TISSLQPEDFATYYCLQYNSYPFTFGQGTKVEIKR |
| VL-Consensus 6 (Table 40) (generated from 11 light chain sequences) | SEQ ID NO: 50371 | DIQMTQSPSSLSASVGDRVTITCRASQGISNYLAWFQ QKPGKAPKSLIYAASSLQSGVPSKFSGSGSGTDFTLTI SSLQPEDFATYYCQQYNSYPFTFGPGTKVDIKR |
| VL-Consensus 7 (kappa) (Table 41) (generated from 26 light chain sequences) | SEQ ID NO: 50372 | DIQMTQSPSSLSASVGDRVTITCRASQDIRSDLGWYQ QKPGKAPKRLIYAASSLQSGVPSRFSGSGSGTEFTLTI SSLQPEDFATYYCLQHTYPFTFGGGTKVEIKR |
| VL-Consensus-7 (lambda) (Table 41) (generated from 26 light chain sequences) | SEQ ID NO: 50373 | QSXLTQPXSXSGSPGQSITSCTGTSSDVGXXNXVSW YQQHPGKAPKLMIYEVSNRPSGVXXRFSGSKSGNTA SLTISGLQXEDEADYYCSSYTXSXTVVFGGGTKLTV LG |
| VL-Consensus-8 (Table 42) (generated from 25 light chain sequences) | SEQ ID NO: 50374 | DIQMTQSPSSLSASVGDRVTITCRASQSISSYLNWYQ QKPGKAPKLLIYAASSLQSGVPSRFSGSGSGTDFTLTI SSLQPEDFATYYCQQSYKTPLFTFGPGTKVDIKR |

FIGURE 55
(Continued)

| | | |
|---|---|---|
| VL-Consensus-9 (Table 43) (generated from 14 light chain sequences) | SEQ ID NO: 50375 | DIQMTQSPSSLSASVGDRVTITCRASQSHSYLNWYQQKPGKAPKLLIYTASSLQSGVPSRFSGSGSGTDFTLTISSLQPEDFATYYCQQTYSTPLTFGGGTKVEIKR |
| VL-Consensus-10 (Table 44) (generated from 22 light chain sequences) | SEQ ID NO: 50376 | DIQMTQSPSSLSASVGDRVTITCRASQGIRNDLGWYQQKPGKAPKRLIYAASSLQSGVPSRFSGSGSGTEFTLTISSLQPEDFATYYCLQHYSYPRLTFGQGTKVEIKR |
| VL-Consensus-11 (Table 45) (generated from 16 light chain sequences) | SEQ ID NO: 50377 | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPRLTFGXGTKVEIKR |
| VL-Consensus-12 (Table 46) (generated from 71 light chain sequences) | SEQ ID NO: 50378 | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPLITFGGGTKVEIKR |
| VL-Consensus-13 (Table 47) (generated from 21 light chain sequences) | SEQ ID NO: 50379 | DIQMTQSPSSLSASVGDRVTITCRASQGIRNDLGWYQQKPGKAPKRLIYAASSLQSGVPSRFSGSGSGTEFTLTISSLQPEDFATYYCLQHSSYPLTFGGGTKVEIKR |
| VL-Consensus-14 (Table 48) (generated from 13 light chain sequences) | SEQ ID NO: 50380 | DIQMTQSPSSLSASVGDRVTITCRASQGIRNDLGWYQQKPGKAPKRLIYAASSLQSGVPSRFSGSGSGTEFTLTISSLQPEDFATYYCLQHSSYPLITFGGGTKVEIKR |
| VL-Consensus-15 (Table 95) (generated from 209 light chain sequences) | SEQ ID NO: 50312 | DIQMTQSPSSLSASVGDRVTITCRASQGIRDLGWYQQKPGKAPKRLIYAASSLQSGVPSRFSGSGSGTEFTLTISSLQPEDFATYYCLQHNSYPLTFGGGTKVEIKR |
| VL-Consensus-16 (Table 96) (generated from 174 light chain sequences) | SEQ ID NO: 50313 | SYELTQPPSVSVSPGQTASITCSGDKLLGDKYACWYQQKPGQSPVLVIYQDKKRPSGIPERFSGSNSGNTATLTISGTQAMDEADYYCQAWDSSTVLFGGGTKLTVLG |
| VL-Consensus-17 (Table 97) (generated from 162 light chain sequences) | SEQ ID NO: 50314 | EIVLTQSPGTLSLSPGERATLSCRASQSVYSSYLAWYQQKPGQAPRLLIYGASSRATGIPDRFSGSGSGTDFTLTISRLEPEDFAVYYCQQYDNSPWTFGQGTKVEIKR |
| VL-Consensus-18 (Table 98) (generated from 147 light chain sequences) | SEQ ID NO: 50315 | DIQMTQSPSSLSASVGDRVTITCRASQGIRNDLGWYQQKPGKAPKRLIYAASSLQSGVPSRFSGSGSGTEFTLTISSLQPEDFATYYCLQHYSYPRLTFGQGTKVEIKR |

FIGURE 55
(Continued)

| | | |
|---|---|---|
| VL-Consensus 19 (Table 99) (generated from 132 light chain sequences) | SEQ ID NO: 50316 | DIVMTQSPDSLAVSLGERATINCKSSQSVLHSSNNEN YLAWYQQKPGQPPKLLIYWASTRESGVPDRFSGSGS GTDFTLTISSLQAEDVAVYYCQQYYSTPPTFGQGTK VEIKR |
| VL-Consensus 20 (Table 100) (generated from 109 light chain sequences) | SEQ ID NO: 50317 | DIQMTQSPSSLSASVGDRVTITCRASQGIRNDLGWY QQKPGKAPKRLIYAASSLQSGVPSRFSGSGSGTEFTLTI SSLQPEDFATYYCLQHNSYPFTFGPGTKVDIKR |
| VL-Consensus 21 (Table 101) (generated from 92 light chain sequences) | SEQ ID NO: 50318 | DIQMTQSPSSLSASVGDRVTITCRASQGISNYLAWFQ QKPGKAPKSLIYAASSLQSGVPSRFSGSGSGTDFTLTI SSLQPEDFATYYCQQYSTYPLTPGGGTKVEIKR |
| VL-Consensus 22 (Table 102) (generated from 89 light chain sequences) | SEQ ID NO: 50319 | DIQMTQSPSSLSASVGDRVTITCRASQNISYLNWYQ QKPGKAPKLLIYTASSLQSGVPSRFSGSGSGTDFTLTI SSLQPEDFATYYCQQYSTPLTFGGGTKVEIKR |
| VL-Consensus 23 (Table 103) (generated from 86 light chain sequences) | SEQ ID NO: 50320 | DIQMTQSPSSLSASVGDRVTITCRASQGISNYLAWFQ QKPGKAPKSLIYAASSLQSGVPSKFSGSGSGTDFTLTI SSLQPEDFATYYCQQYNSYPFTPGPGTKVDIKR |
| VL-Consensus 24 (Table 104) (generated from 81 light chain sequences) | SEQ ID NO: 50321 | SYELTQPPSVSVSPGQTASITCSGDKLGDKYACWYQ QKPGQSPVLVIYQDRKRPSGIPERFSGSNSGNTATLTI SGTQAMDEADYYCQAWDSSTYPGGGTKLTVLG |
| VL-Consensus 25 (Table 105) (generated from 65 light chain sequences) | SEQ ID NO: 50322 | DIVMTQTPLSLSVTPGQPASISCKSSQSLLHGD GKTYLYWYLQKPGQPPQLLIYEVSNRFSGVPDRFSG SGSGTDFTLKISRVEAEDVGVYYCMQSIQLPWTFGQ GTKVEIKR |
| VL-Consensus 26 (Table 106) (generated from 58 light chain sequences) | SEQ ID NO: 50323 | DIQMTQSPSSLSASVGDRVTITCRASQSISSYLNWYQ QKPGKAPKLLIYAASSLQSGVPSRFSGSGSGTDFTLTI SSLQPEDFATYYCQQSYSPFTFGPGTKVDIKR |
| VL-Consensus 27 (Table 107) (generated from 47 light chain sequences) | SEQ ID NO: 50324 | DIVMTQSPDSLAVSLGERATINCKSSQSVLYSSNNNN YLAWYQQKPGQPPKLLIYWASTRESGVPDRFSGSGS GTDFTLTISSLQAEDVAVYYCQQYYSTPRCSFGQGTK LEIKR |
| VL-Consensus 28 (Table 108) (generated from 42 light chain sequences) | SEQ ID NO: 50325 | DIQMTQSPSSVSASVGDRVTITCRASQGISNWLAWY QQKPGKAPKLLIYAASSLQSGVPSRFSGSGSGTDFTL TISSLQPEDFATYYCQQAFPWTFGQGTKVEIKR |

FIGURE 55
(Continued)

| | | |
|---|---|---|
| VL-Consensus 29 (Table 109) (generated from 37 light chain sequences) | SEQ ID NO: 50326 | DIVMTQSPDSLAVSLGERATINCKSSQSVLHSSNNEN YLAWYQQKPGQPPKLLIYWASTRESGVPDRFSGSGS GTDFTLTISSLQAEDVAVYYCQQYYSTPYTFGPGTK VDIKR |
| VL-Consensus 30 (Table 110) (generated from 31 light chain sequences) | SEQ ID NO: 50327 | QTVVTQEPSLTVSPGGTVTLTCASSTGAVTSG-YPNWFQQKPGQAPRALIYSTSNKHSWTPARFSGSL LGGKAALTLSGVQPEDEAEYYCLLYYGGAQLVPGG GTKLTVLG |
| VL-Consensus 31 (Table 111) (generated from 25 light chain sequences) | SEQ ID NO: 50328 | EIVMTQSPATLSVSPGERATLSCRASQSVNSNLAWY QQKPGQAPRLLIYGASTRATGIPARFSGSGSGTEFTL TISSLQSEDFAVYYCQQYNDWPCSFGQGTKLEIKR |
| VL-Consensus 32 (Table 112) (generated from 24 light chain sequences) | SEQ ID NO: 50329 | EFMLTQSPGTLSLSPGERATLSCRASQSVSSSYLVWY QQKPGQAPRLLIYGASTRATGIPDRFSGSGSGTDFTL TISSRLEPEYFAVYYCQQYGGSPLTPGGGTKVEITR |
| VL-Consensus-33 (Table 113) (generated from 21 light chain sequences) | SEQ ID NO: 50330 | DIVMTQTPLSLSVTPGQPASISCKSSQSLLHSEGKTYL YWYLQKPGQPPQLLIYEVSNRFSGVPDRFSGSGSGT DFTLKISRVEAEDVGVYYCMQSIQLPLTFGGGTKVEI KR |
| VL-Consensus 34 (Table 114) (generated from 18 light chain sequences) | SEQ ID NO: 50331 | QSALTQPASVSGSPGQSITSCTGTSSDVGGYNYVSW YQQHPGKAPKLMIYEVSNRPSGVSNRFSGSKSGNTA SLTISGLQAEDEADYCNSYTRSITWVFGGGTKLTV LG |
| VL-Consensus 35 (Table 115) (generated from 17 light chain sequences) | SEQ ID NO: 50332 | DIQMTQSPSSLSASVGDRVTITCRASQSISNYLNWYQ QKPGKAPKLLIYAASSLQSGVPSRFSGSGSGTDFTLTI SSLQPEDFATYYCQQSYSTPIWTFGQGTKVEIKR |
| VL-Consensus 36 (Table 116) (generated from 16 light chain sequences) | SEQ ID NO: 50333 | DIQMTQSPSSVSASVGDRVTITCRASQGISSWLAWY QQKPGKAPKLLIYAASSLQSGVPSRFSGSGSGTDFTL TISSLQPEDEFATYYCQQINSFPLTFGGGTKVEIKR |
| VL-Consensus 37 (Table 117) (generated from 16 light chain sequences) | SEQ ID NO: 50334 | DIQMTQSPSSLSASVGDRVTITCQASQDINNYLNWY QQKPGKAPKLLIYDASNLETGVPSRFSGSGSGTDFTF TISSLQPEDIATYYCQQYDNLPITFGQGTRLEIKR |
| VL-Consensus 38 (Table 118) (generated from 16 light chain sequences) | SEQ ID NO: 50335 | QSVLTQPPSVSAAPGQKVTISCSGSSSNIGNNYVSWY QQLPGTAPKLLIYDNKRPSGIPDRFSGSKSGTSATL GITGLQTGDEADYYCGTWDSSLSVGVFGGGTKLTV LG |

FIGURE 55
(Continued)

| | | |
|---|---|---|
| VL-Consensus 39 (Table 119) (generated from 14 light chain sequences) | SEQ ID NO: 50336 | DIVMTQSPLSLPVTPGEPASISCKSSQSLLHSNGYNYL DWYLQKPGQSPQLLIYLGSNRASGVPDRFSGSGSGT DFTLKISRVEAEDVGVYYCMQALHPPLTFGGGTKVE IKR |
| VL-Consensus 40 (Table 120) (generated from 13 light chain sequences) | SEQ ID NO: 50337 | QSVLTQPPSASGTPGQRVTISCSGSSSNIGSNTVNWY QQLPGTAPKLLIYSNNQRPSGVPDRFSGSKSGTSASL AISGLQSEDEADYYCAAWDDSLNGVYPGGGTKLTV LG |
| VL-Consensus 41 (Table 121) (generated from 11 light chain sequences) | SEQ ID NO: 50338 | QSVLTQPPSASGTPGQRVTISCSGSSSNIGSNIYTWYQ QLPGTAPKLLIYSNDQRPSGVPDRFSGSKSGTSASLAI SGLQSEDEADYYCAAWDDSLNGWVFGGGTTLTVL G |
| VL-Consensus 42 (Table 122) (generated from 10 light chain sequences) | SEQ ID NO: 50339 | DIQMTQSPSSLSASVGDRVTITCRASQGIRNDLGWY QQKPGKAPKRLIYAASSLQSGVPSRFSGSGSGTEFTL TISSLQPEDFATYYCLQHNSYPLIFGQGTRLEIKR |
| VL-Consensus 43 (Table 123) (generated from 10 light chain sequences) | SEQ ID NO: 50340 | DIQMTQSPSSLSASVGDRVTITCRASQSISSYLNWYQ QKPGKAPKLLIYAASSLQSGVPSRFSGSGSGTDFTLTI SSLQPEDFATYYCQQSYSIPITFGQGTRLEIKR |
| VL-Consensus 44 (Table 124) (generated from 10 light chain sequences) | SEQ ID NO: 50341 | DIVMTQTPLSLSVTPGQPASISCKSSQSLLHSEGKTYL YWYLQKPGQPPQLLIYEVSNRFSGVPDRFSGSGSGT DFTLKISRVEAEDVGVYYCMQSIQLPITFGQGTRLEI KR |
| VL-Consensus 45 (Table 125) (generated from 10 light chain sequences) | SEQ ID NO: 50342 | EIVLTQSPGTLSLSPGERATLSCRASQSVISSYLAWYQ QKPGQAPRLLIFGVSSRATGIPDRFSGSGSGTDFTLTI SRLEPEDFAVYYCQQYGRSPFNFGPGTKVDIKR |
| VL-Consensus 46 (Table 126) (generated from 10 light chain sequences) | SEQ ID NO: 50343 | EIVMTQSPATLSVSPGERATLSCRASQSVSSNLAWY QQKPGQAPRLLIYGASTRATGIPARFSGSGSGTEFTL TISSLQSEDFAVYYCQQYNDWPWTFGQGTKVEIKR |
| VL-Consensus 47 (Table 127) (generated from 10 light chain sequences) | SEQ ID NO: 50344 | EIVLTQSPDFQSVTPKEKVTITCRASQSIGSSLHWYQ QKPDQSPKLLIKYASQSFSGVPSRFSGSGSGTDFTLTI NSLEAEDAATYYCHQSSSLPWTFGQGTKVEIKR |
| VL-Consensus 48 (Table 128) (generated from 9 light chain sequences) | SEQ ID NO: 50345 | DIQMTQSPSSLSASVGDRVTITCRASQGIRNDLGWY QQKPGKAPKRLIYAASSLQSGVPSRFSGSGSGTEFTL TISSLQPEDFATYYCLQHYSYPRSFGQGTKLEIKR |

FIGURE 55
(Continued)

| | | |
|---|---|---|
| VL-Consensus 49 (Table 129) (generated from 9 light chain sequences) | SEQ ID NO: 50346 | DIQMTQSPSSLSASVGDRVTITCRASQGISNYLAWFQ QKPGKAPKSLIYAASSLQSGVPSKFSGSGSGTDFTLTI SSLQPEDFATYYCQQYLSYPITFGQGTRLEIKR |
| VL-Consensus 50 (Table 130) (generated from 9 light sequences) | SEQ ID NO: 50347 | EIVLTQSPDFQSVTPKEKVTITCRASQSIGSSLHWYQ QKPDQSPKLLIKYASQSFSGVPSRFSGSGSGTDFTLTI NSLEAEDAATYYCHQSRRLPLTFGGGTKVEIKR |
| VL-Consensus 51 (Table 131) (generated from 9 light chain sequences) | SEQ ID NO: 50348 | SSELTQDPAVSVALGQTVRITCQGDSLRPYYASWYQ QKPGQAPVLVIYGKNNRPSGIPDRFSGSSSGNTASLTI TGAQAEDEADYYCNSRDSSGNHLVVFGGGTKLTVL G |
| VL-Consensus 52 (Table 132) (generated from 8 light chain sequences) | SEQ ID NO: 50349 | DVVMTQSPLSLPVTLGQPASISCRSSQSLVYSDGNTY LNWFQQRPGQSPRRLIYKVSNWDSGVPDRFSGSGSG TDFTLKISRVEAEDVGVYYCMQGIHWPLTFGGGTK VEIKR |
| VL-Consensus 53 (Table 133) (generated from 8 light chain sequences) | SEQ ID NO: 50350 | EIVMTQSPATLSVSPGERATLSCRASQSVSRNLAWY QQKPGQAPRLLIYGASTRATGIPARFSGSGSGTEFTL TISSLQSEDFAVYYCQQYNNWPLTFGGGTKVEIKR |
| VL-Consensus 54 (Table 134) (generated from 8 light chain sequences) | SEQ ID NO: 50351 | SYELTQPLSVSVALGQTARITCGGNNIGRKNVHWYQ QKPGQAPVLVIYRDSDRPSGIPERFSGSNSGNTATLTI SRAQAGDEADYYCQVWDSSTVVFGGGTKLTVLG |

FIGURE 55
(Continued)

Table 20B

VARIABLE LIGHT CDR CONSENSUS SEQUENCES

| Name (original and patent) | Patent SEQ ID NO. | CDR | Sequence |
|---|---|---|---|
| VL-Consensus-1 (Table 35) | 50423 | VL1 | RASQGISRWLA |
| | 50424 | VL2 | AASSLQS |
| | 50425 | VL3 | QQAN5FPFT |
| VL-Consensus-2 (Table 36) | 50426 | VL1 | SGDKLGDKYAY |
| | 50427 | VL2 | QDRKRPS |
| | 50428 | VL3 | QAWENSTVV |
| VL-Consensus-3 (Table 37) | 50429 | VL1 | KSSQSVLYSSNNNNYLA |
| | 50430 | VL2 | WASTRES |
| | 50431 | VL3 | QQYYSTPPT |
| VL-Consensus-4 (Table 38) | 50432 | VL1 | RASQGISNYLA |
| | 50433 | VL2 | AASSLQS |
| | 50434 | VL3 | QQYNSYPFT |
| VL-Consensus-5 (Table 39) | 50435 | VL1 | RASQGIRNNLG |
| | 50436 | VL2 | AASSLQS |
| | 50437 | VL3 | LQYNSYPFT |
| VL-Consensus-6 (Table 40) | 50438 | VL1 | RASQGISNYLA |
| | 50439 | VL2 | AASSLQS |
| | 50440 | VL3 | QQYNSYPFT |
| VL-Consensus-7κ (Table 41) | 50441 | VL1 | RASQDIRSDLG |
| | 50442 | VL2 | AASSLQS |
| | 50443 | VL3 | LQHTYPFT |
| VL-Consensus-7λ (Table 41) | 50444 | VL1 | TGTSSDVGXXNXVS |
| | 50445 | VL2 | EVSNRPS |
| | 50446 | VL3 | SSYTXSYTVV |
| VL-Consensus-8 (Table 42) | 50447 | VL1 | RASQSISSYLN |
| | 50448 | VL2 | AASSLQS |
| | 50449 | VL3 | QQSYRTPLFT |
| VL-Consensus-9 (Table 43) | 50450 | VL1 | RASQSISYLN |
| | 50451 | VL2 | TASSLQS |
| | 50452 | VL3 | QQTYSTPLT |

FIGURE 55
(Continued)

| | | | |
|---|---|---|---|
| VL-Consensus-10 (Table 44) | 50453 | VL1 | RASQGIRNDLG |
| | 50454 | VL2 | AASSLQS |
| | 50455 | VL3 | LQHYSYPRT |
| VL-Consensus-11 (Table 45) | 50456 | VL1 | RASQGIRNDLG |
| | 50457 | VL2 | AASSLQS |
| | 50458 | VL3 | LQHNSYPFT |
| VL-Consensus-12 (Table 46) | 50459 | VL1 | RASQGIRNDLG |
| | 50460 | VL2 | AASSLQS |
| | 50461 | VL3 | LQHNSYPLT |
| VL-Consensus-13 (Table 47) | 50462 | VL1 | RASQGIRNDLG |
| | 50463 | VL2 | AASSLQS |
| | 50464 | VL3 | LQHSSYPLT |
| VL-Consensus-14 (Table 48) | 50465 | VL1 | RASQGIRNDLG |
| | 50466 | VL2 | AASSVQS |
| | 50467 | VL3 | LQHNSYPLT |
| VL-Consensus-15 (Table 95) | 50606 | VL1 | RASQGIRNDLG |
| | 50607 | VL2 | AASSLQS |
| | 50608 | VL3 | LQHNSYPLT |
| VL-Consensus-16 (Table 96) | 50609 | VL1 | SGDKLGDKYAC |
| | 50610 | VL2 | AASSLQS |
| | 50611 | VL3 | QAWDSSTVV |
| VL-Consensus-17 (Table 97) | 50612 | VL1 | RASQSVYSSYLA |
| | 50613 | VL2 | GASSRAT |
| | 50614 | VL3 | QQYDNSPWT |
| VL-Consensus-18 (Table 98) | 50615 | VL1 | RASQGIRNDLG |
| | 50616 | VL2 | AASSLQS |
| | 50617 | VL3 | LQUYSYPRT |
| VL-Consensus-19 (Table 99) | 50618 | VL1 | KSSQSVLHSSNNNNYLA |
| | 50619 | VL2 | WASTRES |
| | 50620 | VL3 | QQYSTPPT |
| VL-Consensus-20 (Table 100) | 50621 | VL1 | RASQGIRNDLG |
| | 50622 | VL2 | AASSLQS |
| | 50623 | VL3 | LQHNSYPFT |
| VL-Consensus-21 (Table 101) | 50624 | VL1 | RASQGISNYLA |
| | 50625 | VL2 | AASSLQS |
| | 50626 | VL3 | QQYSTYPLT |

FIGURE 55
(Continued)

| | | | |
|---|---|---|---|
| VL-Consensus-22 (Table 102) | 50627 | VL1 | RASQNISYLN |
| | 50628 | VL2 | TASSLQS |
| | 50629 | VL3 | QQSYSTPLT |
| VL-Consensus-23 (Table 103) | 50630 | VL1 | RASQGISNYLA |
| | 50631 | VL2 | AASSLQS |
| | 50632 | VL3 | QQYNSYPFT |
| VL-Consensus-24 (Table 104) | 50633 | VL1 | RASQGISRWLA |
| | 50634 | VL2 | AASSLQS |
| | 50635 | VL3 | QQANSFPFT |
| VL-Consensus-25 (Table 105) | 50636 | VL1 | KSSQSLLHGDGKTYLY |
| | 50637 | VL2 | EVSNRFS |
| | 50638 | VL3 | MQSIQLPWT |
| VL-Consensus-26 (Table 106) | 50639 | VL1 | RASQSISSYLN |
| | 50640 | VL2 | AASSLQS |
| | 50641 | VL3 | QQSYSPPT |
| VL-Consensus-27 (Table 107) | 50642 | VL1 | KSSQSVLYSSNNNNYLA |
| | 50643 | VL2 | WASTRES |
| | 50644 | VL3 | QQYYSTPCS |
| VL-Consensus-28 (Table 108) | 50645 | VL1 | RASQGISNWLA |
| | 50646 | VL2 | AASSLQS |
| | 50647 | VL3 | QQANSFPWT |
| VL-Consensus-29 (Table 109) | 50648 | VL1 | KSSQSVLHSSNNNNYLA |
| | 50649 | VL2 | WASTRES |
| | 50650 | VL3 | QQYYSTPVT |
| VL-Consensus-30 (Table 110) | 50651 | VL1 | ASSTGAVTSGYYPN |
| | 50652 | VL2 | STSNKHS |
| | 50653 | VL3 | LLYYGGAQLV |
| VL-Consensus-31 (Table 111) | 50654 | VL1 | RASQSVNSNLA |
| | 50655 | VL2 | GASTRAT |
| | 50656 | VL3 | QQYNDWPCS |

FIGURE 55
(Continued)

| | | | |
|---|---|---|---|
| VL-Consensus-32 (Table 112) | 50657 | VL1 | RASQSVSSSYLV |
| | 50658 | VL2 | GASTRAT |
| | 50659 | VL3 | QQYGCSPLT |
| VL-Consensus-33 (Table 113) | 50660 | VL1 | KSSQSLLHSEGKTYLY |
| | 50661 | VL2 | EVSNRFS |
| | 50662 | VL3 | MQSIQLPLT |
| VL-Consensus-34 (Table 114) | 50663 | VL1 | TGTSSDVGGYNYVS |
| | 50664 | VL2 | EVSNRPS |
| | 50665 | VL3 | NSYTRSITWV |
| VL-Consensus-35 (Table 115) | 50666 | VL1 | RASQSISNYLN |
| | 50667 | VL2 | AASSLQS |
| | 50668 | VL3 | QQSYSTPTWT |
| VL-Consensus-36 (Table 116) | 50669 | VL1 | RASQGISSWLA |
| | 50670 | VL2 | AASSLQS |
| | 50671 | VL3 | QQNSFPLT |
| VL-Consensus-37 (Table 117) | 50672 | VL1 | QASQDINNYLN |
| | 50673 | VL2 | DASNLET |
| | 50674 | VL3 | QQYDNLPIT |
| VL-Consensus-38 (Table 118) | 50675 | VL1 | SGSSSNIGNNYVS |
| | 50676 | VL2 | DNNKRP |
| | 50677 | VL3 | GTWDSSLSVGV |
| VL-Consensus-39 (Table 119) | 50678 | VL1 | RSSQSLLHSNGYNYLD |
| | 50679 | VL2 | LGSNRAS |
| | 50680 | VL3 | MQALPLT |
| VL-Consensus-40 (Table 120) | 50681 | VL1 | SGSSSNIGSNTVN |
| | 50682 | VL2 | SNNQRPS |
| | 50683 | VL3 | AAWDDSLNGVV |
| VL-Consensus-41 (Table 121) | 50684 | VL1 | SGSSSNIGSNIVT |
| | 50685 | VL2 | SNDQRPS |
| | 50686 | VL3 | AAWDDSLNGWV |

FIGURE 55
(Continued)

| | | |
|---|---|---|
| VL-Consensus-42 (Table 122) | VL1 | RASQGIRNDLG |
| | 50687 | |
| | VL2 | AASSLQS |
| | 50688 | |
| | VL3 | LQHNSYPIT |
| | 50689 | |
| VL-Consensus-43 (Table 123) | VL1 | RASQSISSYLN |
| | 50690 | |
| | VL2 | AASSLQS |
| | 50691 | |
| | VL3 | QQSYSIPIT |
| | 50692 | |
| VL-Consensus-44 (Table 124) | VL1 | KSSQSLLHSEGKTYLY |
| | 50693 | |
| | VL2 | EVSNRFS |
| | 50694 | |
| | VL3 | MQSIQPIT |
| | 50695 | |
| VL-Consensus-45 (Table 125) | VL1 | RASQSVISSYLA |
| | 50696 | |
| | VL2 | GVSSRAT |
| | 50697 | |
| | VL3 | QQYGRSPFN |
| | 50698 | |
| VL-Consensus-46 (Table 126) | VL1 | RASQSVSSNLA |
| | 50699 | |
| | VL2 | GASTRAT |
| | 50700 | |
| | VL3 | QQYNDWPWT |
| | 50701 | |
| VL-Consensus-47 (Table 127) | VL1 | RASQSIGSSLH |
| | 50702 | |
| | VL2 | YASQSFS |
| | 50703 | |
| | VL3 | HQSSSLPWT |
| | 50704 | |
| VL-Consensus-48 (Table 128) | VL1 | RASQGIRNDLG |
| | 50705 | |
| | VL2 | AASSLQS |
| | 50706 | |
| | VL3 | LQHYSYPRS |
| | 50707 | |
| VL-Consensus-49 (Table 129) | VL1 | RASQGISNVLA |
| | 50708 | |
| | VL2 | AASSLQS |
| | 50709 | |
| | VL3 | QQYLSYPIT |
| | 50710 | |
| VL-Consensus-50 (Table 130) | VL1 | RASQSIGSSLH |
| | 50711 | |
| | VL2 | YASQSFS |
| | 50712 | |
| | VL3 | HQSRRLPLT |
| | 50713 | |
| VL-Consensus-51 (Table 131) | VL1 | QGDSLRPYYAS |
| | 50714 | |
| | VL2 | GKNNRPS |
| | 50715 | |

FIGURE 55
(Continued)

|  |  |  |  |
|---|---|---|---|
|  | 50716 | VL3 | NSRDSSGNHLVV |
| VL-Consensus-52 (Table 132) | 50717 | VL1 | RSSQSLVYSDGNTYLN |
|  | 50718 | VL2 | KVSNWDS |
|  | 50719 | VL3 | MQGTHWPLT |
| VL-Consensus-53 (Table 133) | 50720 | VL1 | RASQSVSRNLA |
|  | 50721 | VL2 | GASTRAT |
|  | 50722 | VL3 | QQYNNWPLT |
| VL-Consensus-54 (Table 134) | 50723 | VL1 | GGNNIGRKNVH |
|  | 50724 | VL2 | RDSRPS |
|  | 50725 | VL3 | QVWDSSTVV |

FIGURE 55
(Continued)

Table 26C

VARIABLE LIGHT CDR CONSENSUS SEQUENCES II

| NAME (ORIGINAL AND PATENT) | Patent SEQ ID NO. | SEQ ID NO: | CDR | Sequence |
|---|---|---|---|---|
| VL-CONSENSUS-15 TABLE 95 | | SEQ ID NO: 50122 | VL1 | X1 X2 Ser X3 X4 X5 X6 X7 X8 X9 X10, wherein X1 = R or L or a conservative substitution thereof, X2 = A or T or a conservative substitution thereof, X3 = Q or R or a conservative substitution thereof, X4 = G or D or A or V or a conservative substitution thereof, X5 = I or M or V or a conservative substitution thereof, X6 = R or E or K or N or S or a conservative substitution thereof, X7 = N or S or D or T or K or I or a conservative substitution thereof, X8 = D or N or A or a conservative substitution thereof, X9 = L or F or V or a conservative substitution thereof, X10 = G or D or N or a conservative substitution thereof. |
| | | SEQ ID NO: 50123 | VL2 | X1 X2 X3 X4 X5 X6 X7, wherein X1 = A or T or S or V or G or D or R or a conservative substitution thereof, X2 = A or T or V or E or a conservative substitution thereof, X3 = S or F or C or Y or a conservative substitution thereof, X4 = S or N or T or F or R or I or a conservative substitution thereof, X5 = L or V or P or S or a conservative substitution thereof, X6 = Q or H or E or a conservative substitution thereof, X7 = S or R or N or T or G or a conservative substitution thereof. |
| | | SEQ ID NO: 50124 | VL3 | X1 X2 X3 X4 X5 X6 X7 X8 X9, wherein X1 = L or V or I or a conservative substitution thereof, X2 = Q or H or a conservative substitution thereof, X3 = H or D or Y or N or R or a conservative substitution thereof, X4 = N or S or Y or T or D or K or A or I or E or H or P or R or a conservative substitution thereof, X5 = S or I or N or R or T or D or A or L or V or a conservative substitution thereof, X6 = Y or F or H or S or a conservative substitution thereof, X7 = P or A or M or a conservative substitution thereof, X8 = L or P or F or N or V or a conservative substitution thereof, X9 = T or K or I or a conservative substitution thereof. |
| VL-CONSENSUS-16 TABLE 96 | | SEQ ID NO: 50125 | VL1 | Ser Gly X1 X2 X3 Gly X4 X5 X6 X7 X8, wherein X1 = D or N or E or Y or S or a conservative substitution thereof, X2 = K or R or N or E or T or a conservative substitution thereof, X3 = L or M or S or a conservative substitution thereof, X4 = D or N or E or G or Y or T or H or V or a conservative substitution thereof, X5 = K or R or a conservative substitution thereof, X6 = Y or F or S or a conservative substitution thereof, X7 = A or V or T or D or S or a conservative substitution thereof, X8 = C or S or Y or W or H or a conservative substitution thereof. |

FIGURE 55
(Continued)

| | SEQ ID NO: 50126 | VL2 | X1 X2 X3 X4 Arg X5 X6, wherein X1 = Q or E or K or a conservative substitution thereof, X2 = D or N or a conservative substitution thereof, X3 = R or S or N or K or Y or M or T or G or I or a conservative substitution thereof, X4 = K or R or Q or a conservative substitution thereof. |
|---|---|---|---|
| | SEQ ID NO: 50228 | VL3 | X1 X2 X3 X4 X5 X6 X7 X8 X9 X10, wherein X1 = Q or L or K or a conservative substitution thereof, X2 = A or T or a conservative substitution thereof, X3 = W or R or a conservative substitution thereof, X4 = D or H or Y or N or G or a conservative substitution thereof, X5 = S or N or Absent or I or R or K or T or a conservative substitution thereof, X6 = Absent or S or N or R or a conservative substitution thereof, X7 = S or T or N or R or G or P or I or V or Y or a conservative substitution thereof, X8 = T or S or Y or A or F or P or N or K or I or R or a conservative substitution thereof, X9 = V or A or T or M or L or G or a conservative substitution thereof, X10 = V or I or L or A or M. |
| VL-CONSENSUS-17 TABLE 97 | SEQ ID NO: 50127 | VL1 | X1 X2 X3 X4 X5 X6 X7 X8 X9 X10 Leu X11, wherein X1 = R or W or a conservative substitution thereof, X2 = A or T or a conservative substitution thereof, X3 = S or G or R or a conservative substitution thereof, X4 = Q or P or a conservative substitution thereof, X5 = S or N or I or R or a conservative substitution thereof, X6 = V or I or F or a conservative substitution thereof, X7 = Y or R or S or N or D or F or H or G or W or a conservative substitution thereof, X8 = S or T or N or G or L or R or a conservative substitution thereof, X9 = S or N or G or R or D or A or Y or a conservative substitution thereof, X10 = Y or F or H or a conservative substitution thereof, X11 = A or V or S or a conservative substitution thereof. |
| | SEQ ID NO: 50128 | VL2 | X1 X2 X3 X4 Arg X5 X6, wherein X1 = G or D or V or a conservative substitution thereof, X2 = A or T or P or V or a conservative substitution thereof, X3 = S or F or Y or A or T or a conservative substitution thereof, X4 = S or R or N or A or a conservative substitution thereof, X5 = A or S or T or a conservative substitution thereof, X6 = T or P or S or A or a conservative substitution thereof. |
| | SEQ ID NO: 50129 | VL3 | X1 X2 X3 X4 X5 X6 X7 X8 X9 X10, wherein X1 = Q or H or a conservative substitution thereof, X2 = Q or H or a conservative substitution thereof, X3 = Y or S or a conservative substitution thereof, X4 = D or E or G or H or a conservative substitution thereof, X5 = N or S or Absent or R or T or I or D or G or a conservative substitution thereof, X6 = Absent or S or a conservative substitution thereof, X7 = S or P or N or R or a conservative substitution thereof, X8 = P or S or V or a conservative substitution thereof. |

FIGURE 55
(Continued)

| | | | |
|---|---|---|---|
| VL-CONSENSUS-18 TABLE 98 | | | conservative substitution thereof, X9 = W or R or a conservative substitution thereof, X10 = T or A or a conservative substitution thereof. |
| | SEQ ID NO: 50130 | VL1 | Arg X1 X2 X3 X4 Ile X5 X6 X7 Leu X8, wherein X1 = A or T or a conservative substitution thereof, X2 = S or T or a conservative substitution thereof, X3 = Q or R or a conservative substitution thereof, X4 = G or D or A or N or V or a conservative substitution thereof, X5 = R or G or a conservative substitution thereof, X6 = N or K or D or H or S or G or T or a conservative substitution thereof, X7 = D or I or Y or a conservative substitution thereof, X8 = G or N or a conservative substitution thereof. |
| | SEQ ID NO: 50131 | VL2 | X1 X2 X3 X4 X5 X6 X7, wherein X1 = A or T or I or V or P or G or R or S or a conservative substitution thereof, X2 = A or T or S or a conservative substitution thereof, X3 = S or A or F or P or Y or a conservative substitution thereof, X4 = S or N or R or G or T or a conservative substitution thereof, X5 = L or C or F or S or a conservative substitution thereof, X6 = Q or H or P or a conservative substitution thereof, X7 = S or N or G or I or a conservative substitution thereof. |
| | SEQ ID NO: 50132 | VL3 | X1 X2 X3 X4 X5 X6 X7 X8 X9 Thr, wherein X1 = L or V or I or H or a conservative substitution thereof, X2 = Q or M or H or L or V or a conservative substitution thereof, X3 = H or Q or Y or L or S or a conservative substitution thereof, X4 = Y or N or H or S or T or a conservative substitution thereof, X5 = S or N or T or R or D or F or G or a conservative substitution thereof, X6 = Absent or Y or F or a conservative substitution thereof, X7 = Y or F or P or C or N or T or a conservative substitution thereof, X8 = P or L or a conservative substitution thereof, X9 = R or W or F or L or a conservative substitution thereof. |
| VL-CONSENSUS-19 TABLE 99 | SEQ ID NO: 50133 | VL1 | X1 X2 X3 Gln Ser X4 Leu X5 X6 X7 X8 X9 X10 X11 X12 X13 X14, wherein X1 = K or R or M or a conservative substitution thereof, X2 = S or G or R or a conservative substitution thereof, X3 = S or T or N or I or a conservative substitution thereof, X4 = V or I or A or a conservative substitution thereof, X5 = H or Y or F or S or K or D or L or M or a conservative substitution thereof, X6 = S or T or R or N or I or D or a conservative substitution thereof, X7 = S or F or P or a conservative substitution thereof, X8 = N or H or a conservative substitution thereof, X9 = N or K or S or D or H or a conservative substitution thereof, X10 = N or Y or K or H or R or A or F or W or a conservative substitution thereof, X11 = N or H or Y or a |

FIGURE 55
(Continued)

| | | | |
|---|---|---|---|
| | SEQ ID NO: 50259 | VL2 | conservative substitution thereof, X12 = Y or S or a conservative substitution thereof, X13 = L or F or a conservative substitution thereof, X14 = A or T or V or G or a conservative substitution thereof. |
| | SEQ ID NO: 50259 | VL3 | Trp X1 X2 X3 X4 X5 X6, wherein X1 = A or T or S or a conservative substitution thereof, X2 = S or F or a conservative substitution thereof, X3 = T or I or K or S or a conservative substitution thereof, X4 = R or W or L or a conservative substitution thereof, X5 = E or K or A or D or R or a conservative substitution thereof, X6 = S or T or a conservative substitution thereof. |
| | SEQ ID NO: 50134 | VL3 | X1 X2 X3 X4 X5 X6 Pro X7 X8, wherein X1 = Q or H or L or a conservative substitution thereof, X2 = Q or H or a conservative substitution thereof, X3 = Y or F or a conservative substitution thereof, X4 = Y or F or H or N or L or S or a conservative substitution thereof, X5 = S or N or R or D or I or T or C or E or K or a conservative substitution thereof, X6 = T or S or I or V or A or Y or a conservative substitution thereof, X7 = P or W or L or V or C or G or R or S or a conservative substitution thereof, X8 = T or K or S or a conservative substitution thereof. |
| VL-CONSENSUS-20 TABLE 100 | SEQ ID NO: 50135 | VL1 | Arg X1 Ser Gln X2 X3 X4 X5 X6 X7 X8, wherein X1 = A or T or a conservative substitution thereof, X2 = G or D or V or a conservative substitution thereof, X3 = I or M or a conservative substitution thereof, X4 = R or S or a conservative substitution thereof, X5 = N or K or S or D or T or a conservative substitution thereof, X6 = D or N or H or Y or V or A or I or L or a conservative substitution thereof, X7 = L or F or a conservative substitution thereof, X8 = G or D or a conservative substitution thereof. |
| | SEQ ID NO: 50136 | VL2 | X1 X2 X3 X4 X5 X6 X7, wherein X1 = A or P or T or G or I or R or V or a conservative substitution thereof, X2 = A or V or a conservative substitution thereof, X3 = S or F or T or a conservative substitution thereof, X4 = S or N or T or D or a conservative substitution thereof, X5 = L or V or a conservative substitution thereof, X6 = Q or L or a conservative substitution thereof, X7 = S or N or T or G or R or a conservative substitution thereof. |
| | SEQ ID NO: 50137 | VL3 | X1 X2 X3 X4 X5 X6 X7 X8 X9, wherein X1 = L or I or a conservative substitution thereof, X2 = Q or H or L or a conservative substitution thereof, X3 = H or Y or D or L or a conservative substitution thereof, X4 = N or Y or T or H or G or L or a conservative substitution thereof, X5 = S or R or D or T or G or N or a conservative substitution thereof, X6 = Y or F or H or a conservative substitution thereof, X7 = P or L or a conservative substitution thereof. |

FIGURE 55
(Continued)

| | SEQ ID NO: | | |
|---|---|---|---|
| VL-CONSENSUS-21 TABLE 101 | SEQ ID NO: 50138 | VL1 | Arg X1 X2 Gln X3 Ile X4 X5 X6 Leu X7, wherein X1 = A or T or a conservative substitution thereof, X2 = S or N or a conservative substitution thereof, X3 = G or D or A or V or S or a conservative substitution thereof, X4 = S or G or N or R or A or F or a conservative substitution thereof, X5 = N or K or R or H or S or T or I or a conservative substitution thereof, X6 = Y or H or C or D or a conservative substitution thereof, X7 = A or D or V or I or N or a conservative substitution thereof. |
| | SEQ ID NO: 50139 | VL2 | X1 X2 X3 X4 Leu X5 X6, wherein X1 = A or K or S or T or Y or D or G or a conservative substitution thereof, X2 = A or T or V or a conservative substitution thereof, X3 = S or P or a conservative substitution thereof, X4 = S or N or R or a conservative substitution thereof, X5 = Q or L or E or H or a conservative substitution thereof, X6 = S or G or N or T or a conservative substitution thereof. |
| | SEQ ID NO: 50140 | VL3 | X1 X2 X3 X4 X5 X6 Pro X7 X8, wherein X1 = Q or L or H or a conservative substitution thereof, X2 = Q or H or R or Y or a conservative substitution thereof, X3 = Y or S or C or T or a conservative substitution thereof, X4 = S or L or N or M or D or H or V or I or Y or a conservative substitution thereof, X5 = T or N or S or K or a conservative substitution thereof, X6 = V or F or I or S or a conservative substitution thereof, X7 = L or V or F or N or a conservative substitution thereof, X8 = T or I or Q or S or a conservative substitution thereof. |
| VL-CONSENSUS-22 TABLE 102 | SEQ ID NO: 50141 | VL1 | Arg X1 X2 X3 X4 X5 X6 X7 X8 Leu X9, wherein X1 = A or T or a conservative substitution thereof, X2 = S or T or a conservative substitution thereof, X3 = Q or H or R or a conservative substitution thereof, X4 = N or S or R or T or I or a conservative substitution thereof, X5 = I or V or F or I or a conservative substitution thereof, X6 = I or S or N or Y or F or R or H or L or K or T or a conservative substitution thereof, X7 = S or N or D or R or K or T or a conservative substitution thereof, X8 = Y or F or N or a conservative substitution thereof, X9 = N or H or a conservative substitution thereof. |
| | SEQ ID NO: 50142 | VL2 | X1 X2 Ser X3 X4 X5 X6, wherein X1 = T or A or V or G or I or S or a conservative substitution thereof, X2 = A or T or a conservative substitution thereof, X3 = S or N or R or T or a conservative substitution thereof, X4 = L or F or S or a conservative substitution thereof, X5 = Q or H or F or P or a conservative substitution thereof, |

FIGURE 55
(Continued)

| | | | |
|---|---|---|---|
| | SEQ ID NO: 50143 | VL3 | X6 = S or G or T or N or R or a conservative substitution thereof.<br>Gln X1 X2 X3 X4 X5 X6 X7 Thr, wherein X1 = Q or L or a conservative substitution thereof, X2 = S or T or N or P or a conservative substitution thereof, X3 = Y or H or C or D or F or N or a conservative substitution thereof, X4 = S or Absent or I or N or F or G or T or a conservative substitution thereof, X5 = T or S or P or F or N or I or L or a conservative substitution thereof, X6 = P or T or I or A or S or a conservative substitution thereof, X7 = L or P or Y or F or V or a conservative substitution thereof. |
| VL-CONSENSUS-23 TABLE 103 | SEQ ID NO: 50144 | VL1 | X1 X2 X3 X4 X5 X6 X7 X8 X9 Leu X10, wherein X1 = R or P or a conservative substitution thereof, X2 = A or T or a conservative substitution thereof, X3 = S or N or a conservative substitution thereof, X4 = Q or R or a conservative substitution thereof, X5 = G or D or V or A or a conservative substitution thereof, X6 = I or V or a conservative substitution thereof, X7 = S or N or G or R or T or K or a conservative substitution thereof, X8 = N or K or Y or H or I or T or a conservative substitution thereof, X9 = Y or H or a conservative substitution thereof, X10 = A or V or S or a conservative substitution thereof. |
| | SEQ ID NO: 50145 | VL2 | X1 X2 X3 X4 X5 X6 X7, wherein X1 = A or V or G or T or a conservative substitution thereof, X2 = A or S or V or a conservative substitution thereof, X3 = S or F or a conservative substitution thereof, X4 = S or G or N or T or a conservative substitution thereof, X5 = L or V or a conservative substitution thereof, X6 = Q or R or H or L or E or a conservative substitution thereof, X7 = S or G or T or a conservative substitution thereof. |
| | SEQ ID NO: 50146 | VL3 | X1 X2 X3 X4 X5 X6 Pro X7 X8, wherein X1 = Q or H or L or P or R or a conservative substitution thereof, X2 = Q or R or K or H or L or a conservative substitution thereof, X3 = Y or F or a conservative substitution thereof, X4 = N or H or D or Y or S or K or L or M or Q or a conservative substitution thereof, X5 = S or T or G or N or C or D or a conservative substitution thereof, X6 = Y or F or H or a conservative substitution thereof, X7 = F or V or L or I or a conservative substitution thereof, X8 = T or K or a conservative substitution thereof. |
| VL-CONSENSUS-24 TABLE 104 | SEQ ID NO: 50147 | VL1 | Arg X1 X2 X3 X4 X5 X6 X7 X8 X9 X10, wherein X1 = A or V or E or G or a conservative substitution thereof, X2 = S or G or a conservative substitution thereof, X3 = Q or R or a conservative substitution thereof, X4 = G or D or N or A or L or V or a |

FIGURE 55
(Continued)

| | | | |
|---|---|---|---|
| | SEQ ID NO: 50148 | VL2 | conservative substitution thereof, X5 = I or V or F or a conservative substitution thereof, X6 = S or N or T or R or I or a conservative substitution thereof, X7 = R or S or N or K or T or D or I or G or a conservative substitution thereof, X8 = W or Y or a conservative substitution thereof, X9 = L or I or a conservative substitution thereof, 10 = A or T or V or a conservative substitution thereof. |
| | SEQ ID NO: 50149 | VL2 | X1 X2 X3 X4 X5 X6 X7, wherein X1 = A or G or T or D or V or a conservative substitution thereof, X2 = A or T or V or a conservative substitution thereof, X3 = S or Y or a conservative substitution thereof, X4 = S or R or N or T or G or I or a conservative substitution thereof, X5 = L or F or a conservative substitution thereof, X6 = Q or E or a conservative substitution thereof, X7 = S or G or N or D or a conservative substitution thereof. |
| | SEQ ID NO: 50149 | VL3 | X1 Gln X2 X3 X4 X5 Pro X6 Thr, wherein X1 = Q or H or a conservative substitution thereof, X2 = A or T or G or S or V or D or a conservative substitution thereof, X3 = N or D or K or S or a conservative substitution thereof, X4 = S or I or a conservative substitution thereof, X5 = F or L or I or V or a conservative substitution thereof, X6 = F or I or a conservative substitution thereof. |
| VL-CONSENSUS-25 TABLE 105 | SEQ ID NO: 50150 | VL1 | X1 Ser X2 X3 X4 Leu X5 X6 X7 X8 Gly X9 Thr X10 X11 X12, wherein X1 = K or M or K or T or a conservative substitution thereof, X2 = S or G or T or a conservative substitution thereof, X3 = Q or K or a conservative substitution thereof, X4 = S or R or N or T or a conservative substitution thereof, X5 = L or R or V or a conservative substitution thereof, X6 = H or Y or a conservative substitution thereof, X7 = G or S or a conservative substitution thereof, X8 = D or E or G or a conservative substitution thereof, X9 = K or R or a conservative substitution thereof, X10 = Y or F or a conservative substitution thereof, X11 = L or F or a conservative substitution thereof, X12 = V or F or T or C or S or a conservative substitution thereof. |
| | SEQ ID NO: 50151 | VL2 | X1 X2 Ser X3 Arg X4 X5, wherein X1 = F or A or a conservative substitution thereof, X2 = V or I or L or T or I or S or a conservative substitution thereof, X3 = N or K or H or I or S or a conservative substitution thereof, X4 = F or L or a conservative substitution thereof, X5 = S or A or L or T or C or F or a conservative substitution thereof. |
| | SEQ ID NO: 50152 | VL3 | X1 Gln X2 X3 X4 X5 Pro X6 Thr, wherein X1 = M or K or a conservative substitution thereof, X2 = S or T or a conservative substitution thereof, X3 = I or T or F or a conservative substitution thereof, X4 = Q or H or L or a conservative substitution thereof, X5 = L or I or V or a conservative substitution thereof. |

FIGURE 55
(Continued)

| | | | |
|---|---|---|---|
| VL-CONSENSUS-26 TABLE 106 | SEQ ID NO: 50153 | VL1 | F or a conservative substitution thereof, X6 = W or R or a conservative substitution thereof. |
| | SEQ ID NO: 50154 | VL2 | Arg X1 X2 X3 X4 X5 X6 X7 X8 X9 X10, wherein X1 = A or S or T or a conservative substitution thereof, X2 = S or G or I or a conservative substitution thereof, X3 = Q or H or R or a conservative substitution thereof, X4 = S or N or T or a conservative substitution thereof, X5 = I or F or a conservative substitution thereof, X6 = S or I or L or N or R or Y or T or A or G or L or a conservative substitution thereof, X7 = S or N or T or H or K or a conservative substitution thereof, X8 = Y or F or H or a conservative substitution thereof, X9 = L or V or a conservative substitution thereof, X10 = N or I or M or H or Y or a conservative substitution thereof. |
| | SEQ ID NO: 50155 | VL3 | X1 X2 X3 X4 Leu X5 X6, wherein X1 = A or G or T or V or I or a conservative substitution thereof, X2 = A or T or V or S or a conservative substitution thereof, X3 = S or F or a conservative substitution thereof, X4 = S or N or T or V or a conservative substitution thereof, X5 = Q or H or a conservative substitution thereof, X6 = S or N or G or H or I or T or a conservative substitution thereof. |
| VL-CONSENSUS-27 TABLE 107 | SEQ ID NO: 50156 | VL1 | Gln Gln X1 X2 X3 X4 X5 X6 Phe X7, wherein X1 = S or T or Y or a conservative substitution thereof, X2 = Y or N or F or H or a conservative substitution thereof, X3 = S or R or N or F or I or a conservative substitution thereof, X4 = Absent or A or S or a conservative substitution thereof, X5 = P or T or I or F or A or L or V or a conservative substitution thereof, X6 = P or L or F or S or a conservative substitution thereof, X7 = T or A or S or a conservative substitution thereof. |
| | SEQ ID NO: 50157 | VL2 | X1 Ser X2 Gln X3 X4 Leu X5 X6 Ser X7 X8 X9 X10 X11 Leu X12, wherein X1 = K or R or T or a conservative substitution thereof, X2 = S or I or a conservative substitution thereof, X3 = S or N or a conservative substitution thereof, X4 = V or I or a conservative substitution thereof, X5 = Y or H or S or F or a conservative substitution thereof, X6 = S or N or I or R or H or a conservative substitution thereof, X7 = N or H or a conservative substitution thereof, X8 = N or S or D or a conservative substitution thereof, X9 = N or Y or K or H or A or M or Q or a conservative substitution thereof, X10 = N or K or a conservative substitution thereof, X11 = Y or F or a conservative substitution thereof, X12 = A or T or D or a conservative substitution thereof. |
| | SEQ ID NO: 50158 | VL3 | Trp X1 X2 X3 Arg X4 X5, wherein X1 = A or T or G or S or a conservative substitution thereof, X2 = S or F |

FIGURE 55
(Continued)

| | | | |
|---|---|---|---|
| | SEQ ID NO: 50158 | VL3 | or a conservative substitution thereof, X3 = T or I or a conservative substitution thereof, X4 = E or K or D or a conservative substitution thereof, X5 = S or F or a conservative substitution thereof. |
| VL-CONSENSUS-28 TABLE 108 | SEQ ID NO: 50159 | VL1 | X1 X2 X3 X4 X5 X6 X7 X8 X9, wherein X1 = Q or H or a conservative substitution thereof, X2 = Q or H or a conservative substitution thereof, X3 = Y or S or a conservative substitution thereof, X4 = Y or F or K or N or a conservative substitution thereof, X5 = S or T or I or Absent or N or a conservative substitution thereof, X6 = T or S or I or R or A or G or N or a conservative substitution thereof, X7 = P or S or a conservative substitution thereof, X8 = C or Y or G or L or P or a conservative substitution thereof, X9 = S or K or N or a conservative substitution thereof. |
| | SEQ ID NO: 50159 | VL1 | Arg Ala X1 Gln X2 X3 X4 X5 X6 Leu Ala, wherein X1 = S or N or a conservative substitution thereof, X2 = G or D or F or N or V or a conservative substitution thereof, X3 = I or L or V or a conservative substitution thereof, X4 = S or N or T or I or F or G or a conservative substitution thereof, X5 = N or S or D or T or R or a conservative substitution thereof, X6 = W or C or a conservative substitution thereof. |
| | SEQ ID NO: 50160 | VL2 | X1 X2 X3 X4 Leu Gln X5, wherein X1 = A or G or D or T or S or a conservative substitution thereof, X2 = A or V or P or T or a conservative substitution thereof, X3 = S or F or a conservative substitution thereof, X4 = S or N or a conservative substitution thereof, X5 = S or G or N or a conservative substitution thereof. |
| | SEQ ID NO: 50161 | VL3 | X1 Gln X2 X3 Ser X4 Pro X5 Thr, wherein X1 = Q or L or a conservative substitution thereof, X2 = A or T or S or G or V or Y or a conservative substitution thereof, X3 = N or D or H or Y or a conservative substitution thereof, X4 = F or L or a conservative substitution thereof, X5 = W or R or F or a conservative substitution thereof. |
| VL-CONSENSUS-29 TABLE 109 | SEQ ID NO: 50162 | VL1 | Lys Ser X1 Gln X2 X3 X4 X5 X6 Ser X7 X8 X9 X10 Tyr Leu X11, wherein X1 = S or N or a conservative substitution thereof, X2 = S or R or N or a conservative substitution thereof, X3 = V or I or L or a conservative substitution thereof, X4 = L or F or a conservative substitution thereof, X5 = H or F or Y or S or a conservative substitution thereof, X6 = S or N or H or a conservative substitution thereof, X7 = N or H or a conservative substitution thereof, X8 = N or S or a conservative substitution thereof, X9 = N or K or Y or H or a conservative substitution thereof, X10 = N or R |

FIGURE 55
(Continued)

| | | | |
|---|---|---|---|
| | SEQ ID NO: 50163 | VL2 | Trp Ala Ser X1 X2 X3 Ser, wherein X1 = T or A or I or S or a conservative substitution thereof, X2 = R or L or a conservative substitution thereof, X3 = E or K or D or a conservative substitution thereof. |
| | SEQ ID NO: 50164 | VL3 | X1 Gln X2 X3 X4 X5 Pro X6 Thr, wherein X1 = Q or H or a conservative substitution thereof, X2 = Y or S or a conservative substitution thereof, X3 = Y or C or F or S or H or a conservative substitution thereof, X4 = S or N or Q or D or T or a conservative substitution thereof, X5 = T or L or I or A or F or S or a conservative substitution thereof, X6 = V or F or P or a conservative substitution thereof. |
| VL-CONSENSUS-30 TABLE 110 | SEQ ID NO: 50165 | VL1 | X1 X2 X3 Thr X4 X5 Val Thr Ser X6 X7 X8 Pro X9, wherein X1 = A or V or G or a conservative substitution thereof, X2 = S or F or L or a conservative substitution thereof, X3 = S or N or a conservative substitution thereof, X4 = G or E or a conservative substitution thereof, X5 = A or S or T or a conservative substitution thereof, X6 = G or A or a conservative substitution thereof, X7 = Y or S or N or F or a conservative substitution thereof, X8 = Y or F or a conservative substitution thereof, X9 = N or S or Q or a conservative substitution thereof. |
| | SEQ ID NO: 50166 | VL2 | X1 Thr X2 Asn X3 His Ser, wherein X1 = S or H or N or a conservative substitution thereof, X2 = S or N or D or I or T or a conservative substitution thereof, X3 = K or R or a conservative substitution thereof. |
| | SEQ ID NO: 50167 | VL3 | X1 X2 X3 X4 X5 Gly X6 X7 X8 X9, wherein X1 = L or M or a conservative substitution thereof, X2 = L or I or F or a conservative substitution thereof, X3 = Y or F or a conservative substitution thereof, X4 = Y or C or F or S or a conservative substitution thereof, X5 = G or D or a conservative substitution thereof, X6 = A or V or a conservative substitution thereof, X7 = Q or H or a conservative substitution thereof, X8 = L or V or M or a conservative substitution thereof, X9 = V or A or L or G or M or a conservative substitution thereof. |
| VL-CONSENSUS-31 TABLE 111 | SEQ ID NO: 50168 | VL1 | Arg X1 Ser X2 X3 X4 X5 X6 X7 Leu Ala, wherein X1 = A or S or a conservative substitution thereof, X2 = Q or L or M or V or a conservative substitution thereof, X3 = S or N or D or R or T or a conservative substitution thereof, X4 = V or I or a conservative substitution thereof, X5 = N or K or S or V or A or I or L or a conservative substitution thereof, X6 = S or N or T or a conservative substitution thereof, X7 = N or S or Y or a conservative substitution thereof. |

FIGURE 55
(Continued)

| | | | |
|---|---|---|---|
| | SEQ ID NO: 50169 | VL2 | X1 X2 Ser X3 Arg Ala Thr, wherein X1 = G or I or F or V or a conservative substitution thereof, X2 = A or T or a conservative substitution thereof, X3 = T or I or a conservative substitution thereof. |
| | SEQ ID NO: 50170 | VL3 | Gln X1 X2 X3 X4 X5 X6 X7 Cys Ser, wherein X1 = Q or E or a conservative substitution thereof, X2 = Y or F or a conservative substitution thereof, X3 = N or Y or D or a conservative substitution thereof, X4 = D or N or a conservative substitution thereof, X5 = Absent or W or a conservative substitution thereof, X6 = W or P or a conservative substitution thereof, X7 = P or L or M or a conservative substitution thereof. |
| VL-CONSENSUS-32 TABLE 112 | SEQ ID NO: 50171 | VL1 | Arg X1 Ser X2 X3 X4 X5 X6 X7 X8 Leu X9, wherein X1 = A or S or a conservative substitution thereof, X2 = Q or E or a conservative substitution thereof, X3 = S or R or a conservative substitution thereof, X4 = V or I or a conservative substitution thereof, X5 = S or T or a conservative substitution thereof, X6 = S or T or a conservative substitution thereof, X7 = S or N or a conservative substitution thereof, X8 = Y or A or a conservative substitution thereof, X9 = Y or S or a conservative substitution thereof. |
| | SEQ ID NO: 50172 | VL2 | Gly Ala Ser X1 Arg Ala X2, wherein X1 = T or S or a conservative substitution thereof, X2 = T or S or I or a conservative substitution thereof. |
| | SEQ ID NO: 50173 | VL3 | Gln Gln Tyr X1 X2 Ser X3 Leu Thr, wherein X1 = G or V or a conservative substitution thereof, X2 = C or N or S or a conservative substitution thereof, X3 = P or L or a conservative substitution thereof. |
| VL-CONSENSUS-33 TABLE 113 | SEQ ID NO: 50174 | VL1 | Lys Ser Gln X1 Leu X2 X3 X4 X5 Gly X6 Thr X7 Leu X8, wherein X1 = S or T or a conservative substitution thereof, X2 = L or Q or a conservative substitution thereof, X3 = H or R or a conservative substitution thereof, X4 = S or G or a conservative substitution thereof, X5 = E or D or a conservative substitution thereof, X6 = K or R or a conservative substitution thereof, X7 = Y or H or F or a conservative substitution thereof, X8 = Y or N or a conservative substitution thereof. |
| | SEQ ID NO: 50175 | VL2 | Glu X1 Ser X2 Arg X3 Ser, wherein X1 = V or I or a conservative substitution thereof, X2 = N or Y or H or a conservative substitution thereof, X3 = F or I or V or L or a conservative substitution thereof. |
| | SEQ ID NO: 50176 | VL3 | X1 X2 X3 X4 X5 X6 X7 X8 X9, wherein X1 = M or F or a conservative substitution thereof, X2 = Q or H or a conservative substitution thereof, X3 = S or G or N or a conservative substitution thereof, X4 = I or K or T or a conservative substitution thereof, X5 = Q or Absent or |

FIGURE 55
(Continued)

| | | | |
|---|---|---|---|
| VL-CONSENSUS-34 TABLE 114 | SEQ ID NO: 50177 | VL1 | K or H or a conservative substitution thereof, X6 = L or Q or Y or F or H or a conservative substitution thereof, X7 = P or L or V or a conservative substitution thereof, X8 = L or F or P or a conservative substitution thereof, X9 = T or P or S or a conservative substitution thereof. |
| | SEQ ID NO: 50177 | VL1 | Thr Gly Thr Ser Asp X1 Gly X2 Tyr Asn X3 Val Ser, wherein X1 = V or I or a conservative substitution thereof, X2 = G or S or a conservative substitution thereof, X3 = Y or F or a conservative substitution thereof. |
| | SEQ ID NO: 50178 | VL2 | Gln Val X1 Asn Arg Pro Ser, wherein X1 = S or R or a conservative substitution thereof. |
| | SEQ ID NO: 50179 | VL3 | X1 Ser Tyr X2 X3 X4 X5 Thr Trp Val, wherein X1 = N or G or C or S or a conservative substitution thereof, X2 = T or V or K or a conservative substitution thereof, X3 = R or S or K or a conservative substitution thereof, X4 = S or G or N or R or a conservative substitution thereof, X5 = I or S or Y or a conservative substitution thereof. |
| VL-CONSENSUS-35 TABLE 115 | SEQ ID NO: 50180 | VL1 | Arg X1 Ser X2 X3 Ile X4 X5 X6 Leu Asn, wherein X1 = A or S or a conservative substitution thereof, X2 = Q or H or R or a conservative substitution thereof, X3 = S or N or T or H or a conservative substitution thereof, X4 = S or N or G or T or a conservative substitution thereof, X5 = N or S or R or a conservative substitution thereof, X6 = Y or F or a conservative substitution thereof. |
| | SEQ ID NO: 50181 | VL2 | X1 X2 X3 X4 Leu X5 X6, wherein X1 = A or T or S or V or a conservative substitution thereof, X2 = A or T or F or V or a conservative substitution thereof, X3 = S or L or V or a conservative substitution thereof, X4 = S or N or a conservative substitution thereof, X5 = Q or H or a conservative substitution thereof, X6 = S or L or a conservative substitution thereof. |
| | SEQ ID NO: 50182 | VL3 | Gln Gln X1 Tyr X2 X3 X4 X5 Trp Thr, wherein X1 = S or G or T or a conservative substitution thereof, X2 = S or T or N or R or a conservative substitution thereof, X3 = T or S or Absent or a conservative substitution thereof, X4 = P or I or a conservative substitution thereof, X5 = T or P or Q or L or a conservative substitution thereof. |
| VL-CONSENSUS-36 TABLE 116 | SEQ ID NO: 50183 | VL1 | Arg Ala Ser Gln X1 Ile Ser X2 X3 Leu Ala, wherein X11 = G or D or a conservative substitution thereof, X2 = S or N or I or K or a conservative substitution thereof, X3 = W or Y or a conservative substitution thereof. |
| | SEQ ID NO: 50184 | VL2 | Ala Ala Ser Ser Leu Gln X1, wherein X1 = S or G or a conservative substitution thereof. |

FIGURE 55
(Continued)

| | SEQ ID NO: 50185 | VL3 | Gln Gln X1 X2 Ser Phe Pro Leu Thr, wherein X1 = I or T or V or A or G or a conservative substitution thereof, X2 = N or K or a conservative substitution thereof. |
|---|---|---|---|
| VL-CONSENSUS-37 TABLE 117 | SEQ ID NO: 50186 | VL1 | Gln Ala X1 Gln X2 Ile X3 X4 X5 Leu Asn, wherein X1 = S or N or a conservative substitution thereof, X2 = D or Y or a conservative substitution thereof, X3 = N or S or T or F or Y or a conservative substitution thereof, X4 = N or D or a conservative substitution thereof, X5 = Y or F or a conservative substitution thereof. |
| | SEQ ID NO: 50187 | VL2 | Asp X1 Ser X2 Leu Glu Thr wherein X1 = A or G or a conservative substitution thereof, X2 = N or T or D or S or a conservative substitution thereof. |
| | SEQ ID NO: 50188 | VL3 | Gln Gln X1 X2 X3 X4 X5 Ile Thr, wherein X1 = Y or F or a conservative substitution thereof, X2 = D or E or a conservative substitution thereof, X3 = N or Absent or I or a conservative substitution thereof, X4 = L or N or V or a conservative substitution thereof, X5 = P or L or a conservative substitution thereof. |
| VL-CONSENSUS-38 TABLE 118 | SEQ ID NO: 50189 | VL1 | Ser Gly Ser Ser Asn X1 Gly X2 X3 X4 X5 Ser, wherein X1 = I or L or a conservative substitution thereof, X2 = N or S or a conservative substitution thereof, X3 = N or H or K or a conservative substitution thereof, X4 = Y or F or a conservative substitution thereof, X5 = V or L or a conservative substitution thereof. |
| | SEQ ID NO: 50190 | VL2 | Asp X1 X2 Lys Arg Pro Ser, wherein X1 = N or S or a conservative substitution thereof, X2 = N or Y or S or a conservative substitution thereof. |
| | SEQ ID NO: 50191 | VL3 | Gly X1 Trp Asp X2 X3 Leu X4 X5 X6 Val, wherein X1 = T or A or I or a conservative substitution thereof, X2 = S or G or i or R or a conservative substitution thereof, X3 = S or R or a conservative substitution thereof, X4 = S or N or a conservative substitution thereof, X5 = V or A or T or a conservative substitution thereof, X6 = G or V or M or a conservative substitution thereof. |
| VL-CONSENSUS-39 TABLE 119 | SEQ ID NO: 50243 | VL1 | Arg X1 Ser Gln Ser Leu X2 X3 X4 X5 X6 X7 Asn X8 Leu Asp, wherein X1 = S or Y or a conservative substitution thereof, X2 = L or V or a conservative substitution thereof, X3 = H or Y or a conservative substitution thereof, X4 = S or N or H or a conservative substitution thereof, X5 = N or S or a conservative substitution thereof, X6 = G or K or R or a conservative substitution thereof, X7 = Y or H or N or a conservative substitution thereof, X8 = Y or H or S or a conservative substitution thereof. |

FIGURE 55
(Continued)

| | SEQ ID NO: 50244 | VL2 | X1 Gly Ser X2 Arg Ala Ser, wherein X1 = L or V or a conservative substitution thereof, X2 = N or H or a conservative substitution thereof. |
|---|---|---|---|
| | SEQ ID NO: 50245 | VL3 | Met Gln X1 Leu X2 X3 X4 X5 X6 Thr, wherein X1 = A or P or T or V or a conservative substitution thereof, X2 = H or Q or Absent or a conservative substitution thereof, X3 = Absent or T or a conservative substitution thereof, X4 = P or Q or T or I or a conservative substitution thereof, X5 = P or F or a conservative substitution thereof, X6 = L or P or F or a conservative substitution thereof. |
| VL-CONSENSUS-40 TABLE 120 | SEQ ID NO: 50192 | VL1 | Ser Gly X1 X2 Ser X3 Ile Gly X4 X5 X6 X7 X8, wherein X1 = S or T or a conservative substitution thereof, X2 = S or N or a conservative substitution thereof, X3 = N or Y or a conservative substitution thereof, X4 = S or N or a conservative substitution thereof, X5 = N or Y or a conservative substitution thereof, X6 = T or A or S or a conservative substitution thereof, X7 = V or I or a conservative substitution thereof, X8 = N or D or S or a conservative substitution thereof. |
| | SEQ ID NO: 50193 | VL2 | X1 X2 X3 X4 Arg Pro Ser, wherein X1 = S or T or a conservative substitution thereof, X2 = N or S or a conservative substitution thereof, X3 = N or D or S or a conservative substitution thereof, X4 = Q or H or a conservative substitution thereof. |
| | SEQ ID NO: 50194 | VL3 | X1 Ala Trp Asp Asp X2 X3 X4 X5 X6 X7 X8, wherein X1 = A or E or a conservative substitution thereof, X2 = S or Absent or a conservative substitution thereof, X3 = Absent or L or a conservative substitution thereof, X4 = L or N or M or S or a conservative substitution thereof, X5 = N or G or K or L or a conservative substitution thereof, X6 = G or H or N or a conservative substitution thereof, X7 = V or P or G or a conservative substitution thereof, X8 = V or P or a conservative substitution thereof. |
| VL-CONSENSUS-41 TABLE 121 | SEQ ID NO: 50195 | VL1 | Ser Gly Ser X1 Ser Asn Ile Gly X2 X3 X4 Val X5, wherein X1 = S or N or C or a conservative substitution thereof, X2 = S or N or a conservative substitution thereof, X3 = N or H or a conservative substitution thereof, X4 = I or T or a conservative substitution thereof, X5 = T or N or a conservative substitution thereof. |
| | SEQ ID NO: 50196 | VL2 | X1 Asn X2 Gln Arg Pro Ser, wherein X1 = S or G or N or V or a conservative substitution thereof, X2 = D or K or N or Y or a conservative substitution thereof. |
| | SEQ ID NO: 50197 | VL3 | X1 X2 Trp Asp Asp Ser Leu X3 X4 Trp Val, wherein X1 = A or T or a conservative substitution thereof, X2 = |

FIGURE 55
(Continued)

| | | | |
|---|---|---|---|
| VL-CONSENSUS-42 TABLE 122 | SEQ ID NO: 50198 | VL1 | A or T or V or a conservative substitution thereof, X3 = N or I or S or a conservative substitution thereof, X4 = G or D or V or a conservative substitution thereof |
| | SEQ ID NO: 50198 | VL1 | Arg X1 Ser Gln X2 X3 Arg X4 Asp Leu Gly, wherein X1 = A or T or a conservative substitution thereof, X2 = G or D or R or a conservative substitution thereof, X3 = I or V or a conservative substitution thereof, X4 = N or S or a conservative substitution thereof |
| | SEQ ID NO: 50199 | VL2 | X1 Ala Ser X2 Leu X3 Ser, wherein X1 = A or D or I or T or a conservative substitution thereof, X2 = S or N or a conservative substitution thereof, X3 = Q or E or P or L or a conservative substitution thereof |
| | SEQ ID NO: 50200 | VL3 | X1 X2 X3 X4 X5 X6 X7 Pro X8 Thr wherein, X1 = L or I or a conservative substitution thereof, X2 = Q or H or a conservative substitution thereof, X3 = H or Y or a conservative substitution thereof, X4 = N or H or S or a conservative substitution thereof, X5 = S or N or a conservative substitution thereof, X6 = Absent or Y or a conservative substitution thereof, X7 = Y or L or F or P or a conservative substitution thereof, X8 = I or P or L or a conservative substitution thereof. |
| VL-CONSENSUS-43 TABLE 123 | SEQ ID NO: 50201 | VL1 | Arg X1 Ser Gln X2 X3 X4 X5 Tyr X6 X7, wherein X1 = A or T or a conservative substitution thereof, X2 = S or N or Y or a conservative substitution thereof, X3 = S or S or F or a conservative substitution thereof, X4 = S or F or N or R or T or a conservative substitution thereof, X5 = S or D or G or R or a conservative substitution thereof, X6 = L or S or a conservative substitution thereof, X7 = N or S or a conservative substitution thereof. |
| | SEQ ID NO: 50202 | VL2 | X1 X2 X3 X4 X5 X6 X7, wherein X1 = A or D or G or S or a conservative substitution thereof, X2 = A or T or a conservative substitution thereof, X3 = S or Y or a conservative substitution thereof, X4 = S or T or a conservative substitution thereof, X5 = L or F or a conservative substitution thereof, X6 = Q or E or K or a conservative substitution thereof, X7 = S or T or a conservative substitution thereof. |
| | SEQ ID NO: 50203 | VL3 | X1 X2 X3 X4 X5 X6 X7 X8 X9, wherein X1 = Q or H or a conservative substitution thereof, X2 = Q or E or a conservative substitution thereof, X3 = S or T or a conservative substitution thereof, X4 = Y or F or a conservative substitution thereof, X5 = S or G or N or a conservative substitution thereof, X6 = I or T or L or N or S or a conservative substitution thereof, X7 = P or S or R or T or a conservative substitution thereof, X8 = I or F or P or a conservative substitution thereof, X9 = T or A or a conservative substitution thereof. |

FIGURE 55
(Continued)

| | | | |
|---|---|---|---|
| VL-CONSENSUS-44 TABLE 124 | SEQ ID NO: 50204 | VL1 | X1 X2 X3 Gln X4 X5 X6 His X7 X8 Gly X9 Thr Tyr Leu Tyr, wherein X1 = K or R or a conservative substitution thereof, X2 = S or T or a conservative substitution thereof, X3 = S or N or a conservative substitution thereof, X4 = S or I or a conservative substitution thereof, X5 = L or F or a conservative substitution thereof, X6 = L or V or a conservative substitution thereof, X7 = S or N or R or a conservative substitution thereof, X8 = E or D or a conservative substitution thereof, X9 = K or R or a conservative substitution thereof. |
| | SEQ ID NO: 50205 | VL2 | Gln X1 Ser X2 Arg X3 Ser, wherein X1 = V or L or a conservative substitution thereof, X2 = N or K or H or a conservative substitution thereof, X3 = F or L or V or a conservative substitution thereof. |
| | SEQ ID NO: 50246 | VL3 | X1 Gln Ser X2 X3 X4 X5 Ile X6, wherein X1 = M or I or L or a conservative substitution thereof, X2 = I or M or a conservative substitution thereof, X3 = Q or Absent or L or a conservative substitution thereof, X4 = L or Y or I or Q or a conservative substitution thereof, X5 = P or L or a conservative substitution thereof, X6 = T or I or a conservative substitution thereof. |
| VL-CONSENSUS-45 TABLE 125 | SEQ ID NO: 50206 | VL1 | Arg Ala Ser X1 X2 X3 X4 X5 X6 X7 Leu Ala, wherein X1 = Q or R or a conservative substitution thereof, X2 = S or G or N or a conservative substitution thereof, X3 = V or I or a conservative substitution thereof, X4 = I or S or G or a conservative substitution thereof, X5 = S or N or a conservative substitution thereof, X6 = S or I or a conservative substitution thereof, X7 = Y or F or a conservative substitution thereof. |
| | SEQ ID NO: 50207 | VL2 | Gly X1 Ser X2 X3 Ala Thr, wherein X1 = V or A or T or a conservative substitution thereof, X2 = S or N or T or a conservative substitution thereof, X3 = R or W or a conservative substitution thereof. |
| | SEQ ID NO: 50208 | VL3 | X1 X2 X3 X4 X5 Ser X6 X7 Asn, wherein X1 = Q or H or a conservative substitution thereof, X2 = Q or H or a conservative substitution thereof, X3 = Y or N or a conservative substitution thereof, X4 = G or D or a conservative substitution thereof, X5 = R or Absent or N or Y or a conservative substitution thereof, X6 = P or L or M or a conservative substitution thereof, X7 = N or T or a conservative substitution thereof. |
| VL-CONSENSUS-46 TABLE 126 | SEQ ID NO: 50209 | VL1 | Arg X1 Ser Gln X2 X3 X4 X5 X6 X7 Ala, wherein X1 = A or S or a conservative substitution thereof, X2 = S or D or T or a conservative substitution thereof, X3 = V or I or a conservative substitution thereof, X4 = S or N or I or a conservative substitution thereof, X5 = S or R or I or a conservative substitution thereof. |

FIGURE 55
(Continued)

| | | | |
|---|---|---|---|
| | SEQ ID NO: 50210 | VL2 | or I or T or a conservative substitution thereof, X6 = N or Y or a conservative substitution thereof, X7 = L or I or a conservative substitution thereof. |
| | | | Gly Ala Ser Thr Arg Ala X1, wherein X1 = T or S or a conservative substitution thereof. |
| | SEQ ID NO: 50211 | VL3 | Gln X1 X2 X3 X4 X5 X6 X7 X8 X9, wherein X1 = Q or E or a conservative substitution thereof, X2 = Y or S or a conservative substitution thereof, X3 = N or D or P or H or a conservative substitution thereof, X4 = D or N or Absent or T or a conservative substitution thereof, X5 = Absent or W or a conservative substitution thereof, X6 = W or P or C or N or a conservative substitution thereof, X7 = P or L or W or a conservative substitution thereof, X8 = W or L or C or P or R or a conservative substitution thereof, X9 = T or P or S or a conservative substitution thereof. |
| VL-CONSENSUS-47 TABLE 127 | SEQ ID NO: 50256 | VL1 | Arg Ala Ser Gln X1 Ile Gly X2 X3 Leu His, wherein X1 = S or N or a conservative substitution thereof, X2 = S or N or a conservative substitution thereof, X3 = S or N or T or a conservative substitution thereof. |
| | SEQ ID NO: 50257 | VL2 | X1 Ala Ser Gln Ser Phe Ser, wherein X1 = Y or S or a conservative substitution thereof. |
| | SEQ ID NO: 50258 | VL3 | X1 Gln Ser X2 Ser X3 Pro X4 Thr, wherein X1 = H or Q or a conservative substitution thereof, X2 = S or G or R or a conservative substitution thereof, X3 = L or F or P or a conservative substitution thereof, X4 = W or R or Q or a conservative substitution thereof. |
| VL-CONSENSUS-48 TABLE 128 | SEQ ID NO: 50247 | VL1 | Arg Ala Ser Gln X1 Ile X2 X3 Asp Leu Gly, wherein X1 = G or A or a conservative substitution thereof, X2 = R or G or a conservative substitution thereof, X3 = N or D or a conservative substitution thereof. |
| | SEQ ID NO: 50248 | VL2 | Ala X1 Ser Ser Leu Gln Ser, wherein X1 = A or T or a conservative substitution thereof. |
| | SEQ ID NO: 50249 | VL3 | Leu Gln His X1 X2 X3 Pro X4 Ser, wherein X1 = Y or N or a conservative substitution thereof, X2 = S or N or a conservative substitution thereof, X3 = Y or F or a conservative substitution thereof, X4 = R or Y or a conservative substitution thereof. |
| VL-CONSENSUS-49 TABLE 129 | SEQ ID NO: 50212 | VL1 | X1 Ala Ser Gln X2 Ile X3 X4 X5 Leu X6, wherein X1 = R or Q or a conservative substitution thereof, X2 = G or D or a conservative substitution thereof, X3 = S or N or a conservative substitution thereof, X4 = N or K or a conservative substitution thereof, X5 = Y or F or a conservative substitution thereof, X6 = A or N or V or a conservative substitution thereof. |

FIGURE 55 (Continued)

| | | | |
|---|---|---|---|
| | SEQ ID NO: 50213 | VL2 | X1 Ala X2 X3 Leu X4 X5, wherein X1 = A or D or G or T or a conservative substitution thereof, X2 = S or T or a conservative substitution thereof, X3 = S or R or N or a conservative substitution thereof, X4 = Q or H or L or V or a conservative substitution thereof, X5 = S or T or a conservative substitution thereof. |
| | SEQ ID NO: 50214 | VL3 | X1 X2 Tyr X3 X4 X5 Pro X6 Thr, wherein X1 = Q or H or L or a conservative substitution thereof, X2 = Q or H or L or a conservative substitution thereof, X3 = L or H or D or K or N or Y or a conservative substitution thereof, X4 = S or N or H or T or a conservative substitution thereof, X5 = Y or L or a conservative substitution thereof, X6 = I or L or a conservative substitution thereof. |
| VL-CONSENSUS-50 TABLE 130 | SEQ ID NO: 50215 | VL1 | X1 Ala X2 Gln Ser X3 Gly Ser Ser Leu His, wherein X1 = S or N or a conservative substitution thereof, X2 = S or N or a conservative substitution thereof, X3 = S or R or a conservative substitution thereof. |
| | SEQ ID NO: 50216 | VL2 | Tyr Ala Ser Gln Ser X1 Ser, wherein X1 = F or L or a conservative substitution thereof. |
| | SEQ ID NO: 50217 | VL3 | His Gln X1 X2 X3 Leu Pro Leu Thr, wherein X1 = S or T or a conservative substitution thereof, X2 = R or G or S or a conservative substitution thereof, X3 = R or S or T or a conservative substitution thereof. |
| VL-CONSENSUS-51 TABLE 131 | SEQ ID NO: 50218 | VL1 | Gln Gly Asp X1 Leu Arg X2 Tyr Tyr X3 X4, wherein X1 = S or T or K or a conservative substitution thereof, X2 = P or N or S or T or a conservative substitution thereof, X3 = A or V or a conservative substitution thereof, X4 = S or N or a conservative substitution thereof. |
| | SEQ ID NO: 50219 | VL2 | X1 Lys Asn X2 Arg Pro Ser, wherein X1 = G or A or T or a conservative substitution thereof, X2 = N or S or a conservative substitution thereof. |
| | SEQ ID NO: 50220 | VL3 | Asn Ser Arg Asp Ser X1 X2 X3 X4 X5 X6 X7, wherein X1 = S or C or a conservative substitution thereof, X2 = G or Absent or a conservative substitution thereof, X3 = N or G or a conservative substitution thereof, X4 = H or N or S or a conservative substitution thereof, X5 = L or H or a conservative substitution thereof, X6 = V or L or a conservative substitution thereof, X7 = V or L or a conservative substitution thereof. |
| VL-CONSENSUS-52 TABLE 132 | SEQ ID NO: 50221 | VL1 | Arg Ser X1 Gln Ser Leu Val Tyr Ser Asp Gly Asn Thr X2 Leu Asn wherein X1 = S or G or a conservative substitution thereof, X2 = Y or S or a conservative substitution thereof. |
| | SEQ ID NO: 50222 | VL2 | X1 Val Ser X2 Trp Asp X3, wherein X1 = K or E or a conservative substitution thereof, X2 = N or S or a |

FIGURE 55
(Continued)

| | | | |
|---|---|---|---|
| | SEQ ID NO: 50223 | VL3 | conservative substitution thereof, X3 = S or Y or a conservative substitution thereof. |
| VL-CONSENSUS-53 TABLE 133 | SEQ ID NO: 50224 | VL1 | Met Gln Gly X1 X2 X3 X4 X5 Thr, wherein X1 = T or I or a conservative substitution thereof, X2 = H or Absent or a conservative substitution thereof, X3 = W or H or a conservative substitution thereof, X4 = P or L or S or W or a conservative substitution thereof, X5 = L or P or a conservative substitution thereof. |
| | SEQ ID NO: 50225 | VL2 | Arg X1 Ser Gln Ser X2 X3 X4 X5 X6 Ala, wherein X1 = A or P or T or a conservative substitution thereof, X2 = V or F or a conservative substitution thereof, X3 = S or R or W or a conservative substitution thereof, X4 = R or I or S or a conservative substitution thereof, X5 = N or D or S or a conservative substitution thereof, X6 = L or V or a conservative substitution thereof. |
| | SEQ ID NO: 50226 | VL3 | X1 Ala X2 X3 Arg Ala Thr, wherein X1 = G or D or a conservative substitution thereof, X2 = S or A or a conservative substitution thereof, X3 = T or I or A or a conservative substitution thereof. |
| VL-CONSENSUS-54 TABLE 134 | SEQ ID NO: 50250 | VL1 | Gln Gln Tyr X1 X2 X3 X4 Pro Leu Thr, wherein X1 = N or Y or a conservative substitution thereof, X2 = N or T or Y or a conservative substitution thereof, X3 = Absent or W or a conservative substitution thereof, X4 = W or P or a conservative substitution thereof. |
| | SEQ ID NO: 50251 | VL2 | Gly Gly X1 Asn Ile X2 X3 X4 X5 Val His, wherein X1 = N or D or a conservative substitution thereof, X2 = G or R or a conservative substitution thereof, X3 = R or S or a conservative substitution thereof, X4 = K or R or A or a conservative substitution thereof, X5 = N or A or a conservative substitution thereof. |
| | SEQ ID NO: 50252 | VL3 | X1 Asp X2 X3 Arg X4 Ser, wherein X1 = R or S or a conservative substitution thereof, X2 = S or R or a conservative substitution thereof, X3 = D or N or Y or a conservative substitution thereof, X4 = P or S or a conservative substitution thereof. |
| | | | Gln X1 Trp Asp Ser X2 X3 X4 X5 X6 Val, wherein X1 = V or D or a conservative substitution thereof, X2 = Absent or S or a conservative substitution thereof, X3 = Absent or S or a conservative substitution thereof, X4 = S or D or G or a conservative substitution thereof, X5 = T or H or a conservative substitution thereof, X6 = V or A or G or a conservative substitution thereof. |

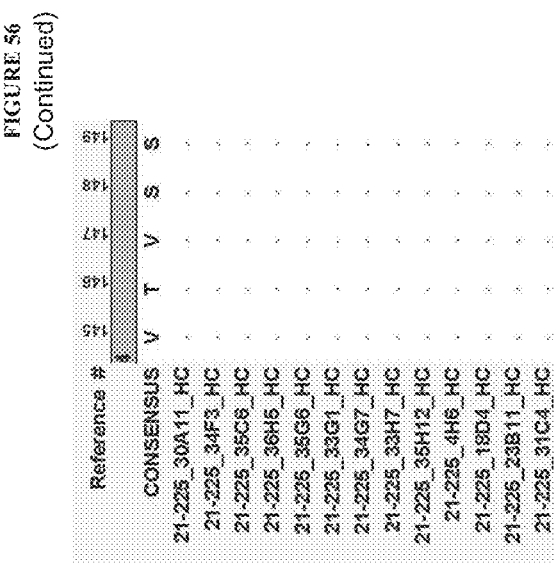

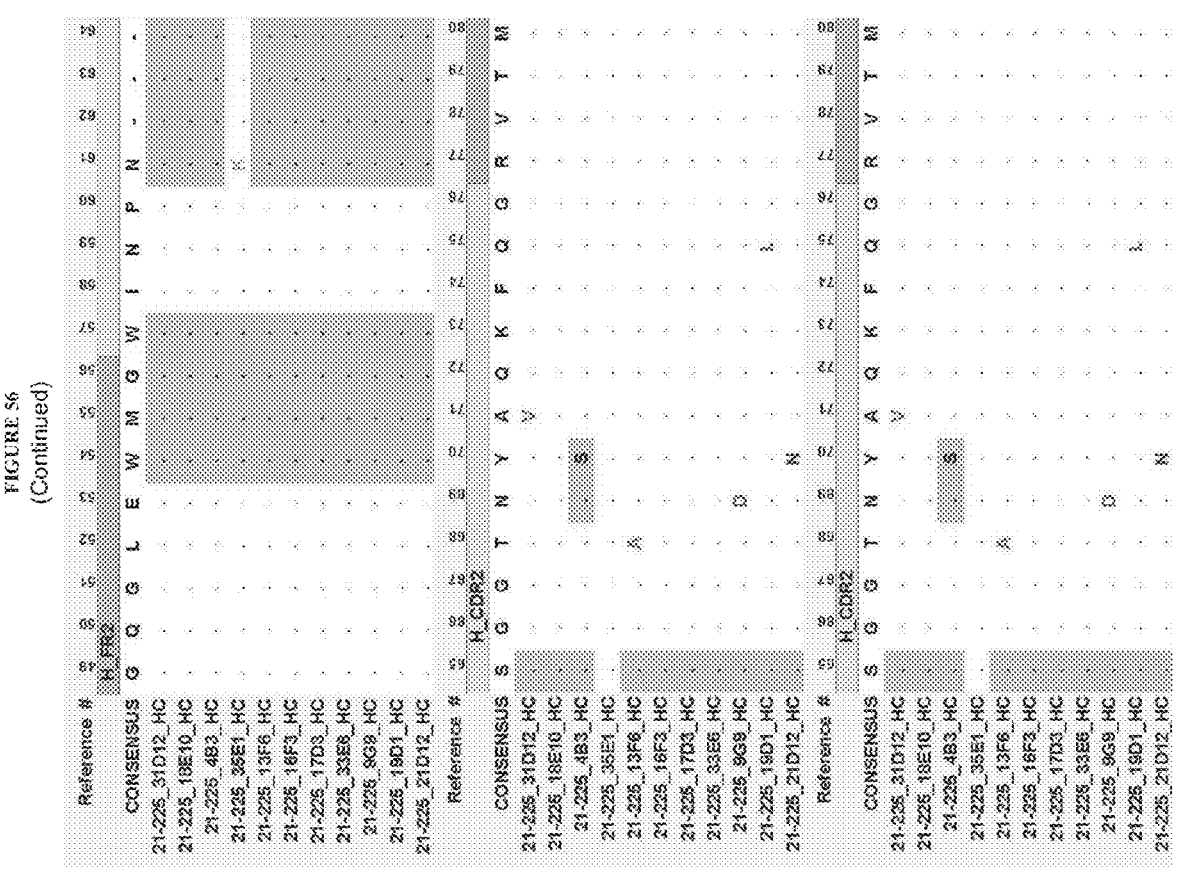
FIGURE S6 (Continued)

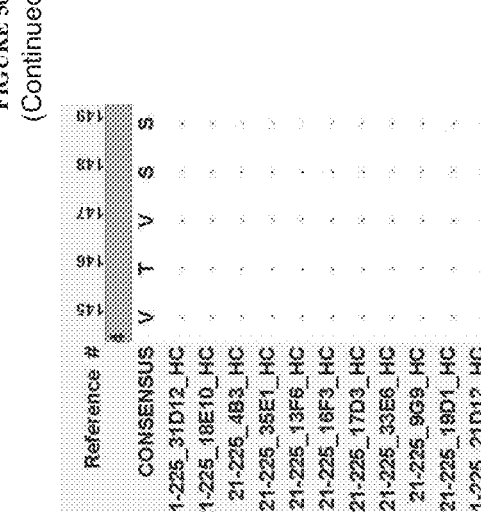

Table 28

FIGURE 56
(Continued)

Table 29

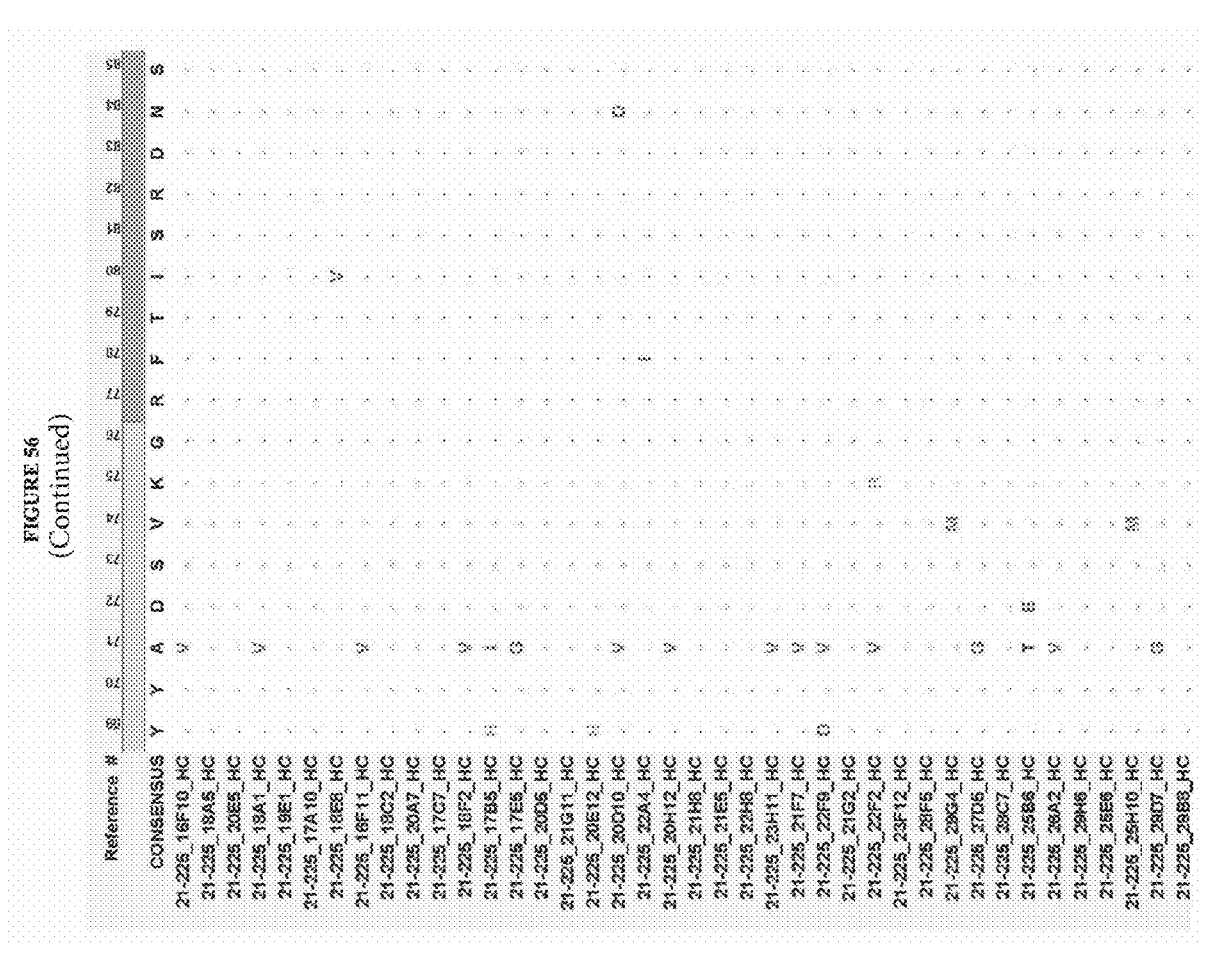

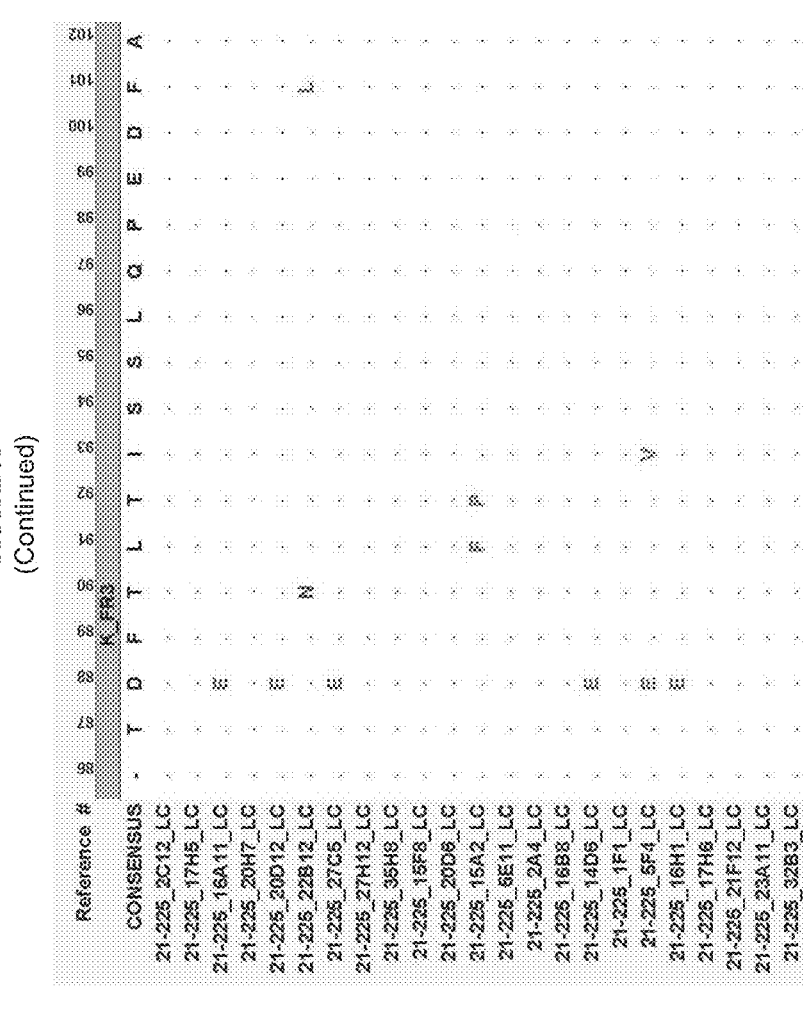

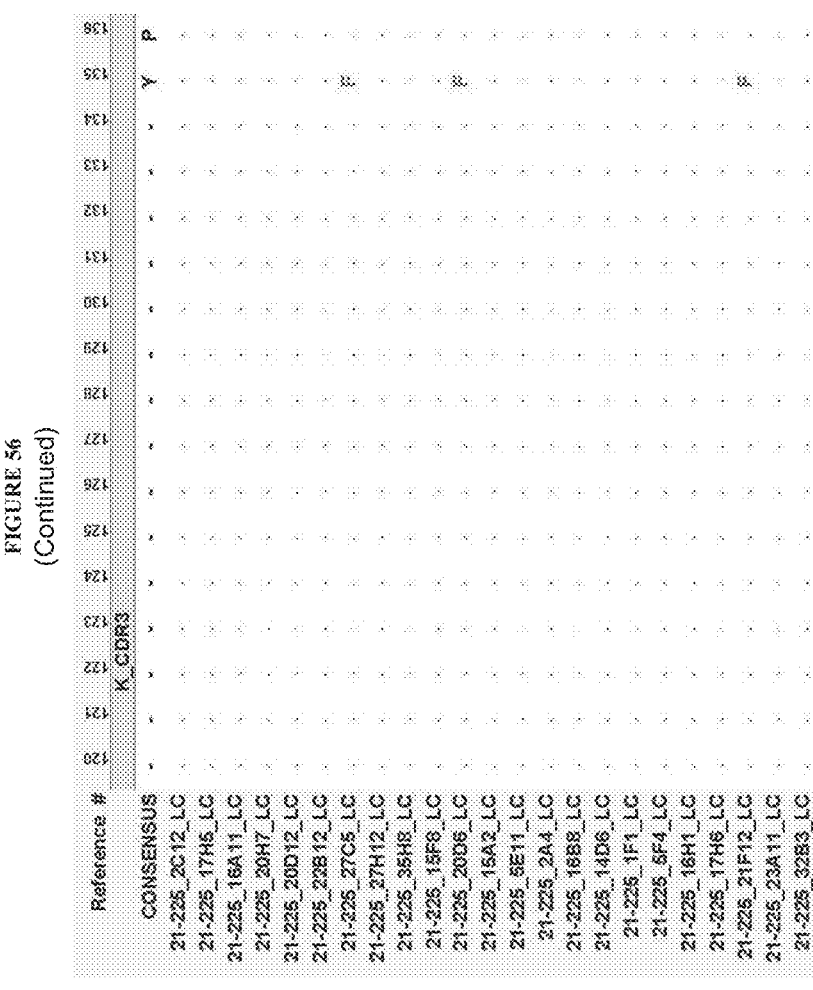

Table 42

Table 43

FIGURE 56
(Continued)

Table 46

FIGURE 56
(Continued)

Table 47

| Reference # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| CONSENSUS | D | I | Q | M | T | Q | S | P | S | S | L | S | A | S | V | G | D |
| 21-225_8D12_LC | | | | | | | | | | | | | | | | Q | |
| 21-225_20C2_LC | | | | | | | | | | | | | | | | | |
| 21-225_18C6_LC | | | | | | | | | | | | | | | | | |
| 21-225_18A3_LC | | | | | | | | | | | | | | | | | |
| 21-225_22D12_LC | | | | | | | | | | | | | | | | | |
| 21-225_23D1_LC | | | | | | | | | | | | | | | | | |
| 21-225_24E5_LC | | | | | | | | | | | | | | | | | |
| 21-225_22C1_LC | | | | | | | | | | | | | | | | | |
| 21-225_20G9_LC | | | | | | | | | | | | | | | | | |
| 21-225_21G7_LC | | | | | | | | | | | | | | | | | |
| 21-225_22G9_LC | | | | | | | | | | | | | | | | | |
| 21-225_34C4_LC | | | | | | | | | | | | | | | | | |
| 21-225_2F7_LC | | | | | | | | | | | | | | | | | |
| 21-225_3G4_LC | | | | | | | | | | | | | | | | | |
| 21-225_7F4_LC | | | | | | | | | | | | | | | | | |
| 21-225_6D4_LC | | | | | | | | | | | | | | | | | |
| 21-225_15A1_LC | | | | | | | | | | | | | | | | | |
| 21-225_16G7_LC | | | | | | | | | | | | | | | | | |
| 21-225_11F10_LC | | | | | | | | | | | | | | | | | |
| 21-225_16H1_LC | | | | | | | | | | | | | | | | | |
| 21-225_18A1_LC | | | | | | | | | | | | | | | | | |

Table 49: Consensus 15–VH1I1-08/D6i6-19iRF1/JH4 (SEQ ID NO: 50266):

QVQLVQS-GAEVKKPGASVKVSCKASG-YTFTN-----YDINWVRQATGQGLEWMGWMHPN---
SGNTGYAQKFQGRVTMTRNTSISTAYMELSSLRSEDTAVYYCASSSGWY............YFDYWGQGTLVTVSS wherein:

N at position 33 can be substituted with H

I at position 41 can be substituted with V or L

W at position 57 can be substituted with R

M at position 58 can be substituted with V or L

H at position 59 can be substituted with N, Y or T

N at position 61 can be substituted with D or H

G at position 66 can be substituted with H

N at position 67 can be substituted with S, Q, A, D, K or T

T at position 68 can be substituted with A, V or E

G at position 69 can be substituted with D

Y at position 70 can be substituted with F or C

A at position 71 can be substituted with P

Q at position 72 can be substituted with K

K at position 73 can be substituted with R or N

Q at position 75 can be substituted with R

G at position 76 can be substituted with V

Y at position 113 can be substituted with E, N or T

FIGURE 57
(Continued)

Y at position 135 can be substituted with F, K, I, R, V, L, M, W, H or S

Y at position 138 can be substituted with F, S or N

Xaa Tyr Asp Xaa Asn (SEQ ID NO: 50001)

Xaa Xaa Xaa Pro Xaa Ser Xaa Xaa Xaa Xaa Xaa Xaa Phe Xaa Xaa (SEQ ID NO: 50002)

Ser Ser Gly Trp Xaa Xaa Phe Asp Xaa (SEQ ID NO: 50003)

Asn Tyr Asp Ile Asn (SEQ ID NO: 50468)

Trp Met His Pro Asn Ser Gly Asn Thr Gly Tyr Ala Gln Lys Phe Gln Gly (SEQ ID NO: 50469)

Ser Ser Gly Trp Tyr Tyr Phe Asp Tyr (SEQ ID NO: 50470)

FIGURE 57
(Continued)

| Reference # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | | | | | | | | | | H_CDR1 | | | | | | | | | | | | | | H_FR2 | |
| CONSENSUS | S | G | . | Y | T | F | T | N | . | . | . | . | . | Y | D | I | N | W | V | R | Q | A | T | G | Q |
| 21-225_92E6_HC | . | . | . | . | . | . | . | . | . | . | . | . | . | . | . | . | . | . | . | . | . | . | . | . | . |
| 21-225_94D8_HC | . | . | . | . | . | . | . | . | . | . | . | . | . | . | . | . | . | . | . | . | . | . | . | . | . |
| 21-225_96D10_HC | . | . | . | . | . | . | . | . | . | . | . | . | . | . | . | . | . | . | . | . | . | . | . | . | . |
| 21-225_96H5_HC | . | . | . | . | . | . | . | . | . | . | . | . | . | . | . | . | . | . | . | . | . | . | S | . | . |

Table 50. Consensus 16- VH3|3-33/D6i6-6|RF1/JH6 (SEQ ID NO: 50267):

QVQLVES-GGGVVQPGRSLRLSCAASG-FTFSS-----YVMHWVRQAPGKGLEWVAVIWYD---GSNKYYADSVKGRFTISRDNSKNTLYLQMNSLRAEDTAVYYCARERYSSGW---------YDYGMDVWGQGTTVTVSS wherein:

S at position 33 can be substituted with D, N or I

Y at position 39 can be substituted with C, F, D or S

V at position 40 can be substituted with G, I or L

M at position 41 can be substituted with I or L

H at position 42 can be substituted with D

V at position 57 can be substituted with L or A

W at position 59 can be substituted with F

G at position 65 can be substituted with A

S at position 66 can be substituted with R or N

N at position 67 can be substituted with Y, G or S

Y at position 69 can be substituted with H

Y at position 70 can be substituted with H or N

A at position 71 can be substituted with V, E, G or T

D at position 72 can be substituted with E or G

S at position 73 can be substituted with A

V at position 74 can be substituted with M

E at position 109 can be substituted with R or V

FIGURE 57
(Continued)

R at position 110 can be substituted with Y, K, V, E, P, D, L, F, M, N, Q or T

Y at position 111 can be substituted with S, T or V

S at position 112 can be substituted with R, Y, P, T or G

S at position 113 can be substituted with C or Y

G at position 114 can be substituted with W, S or N

W at position 115 can be substituted with null (-), L, Y, G, F or S null (-) at position 116 can be substituted with Y null (-) at position 117 can be substituted with A, G or T null (-) at position 118 can be substituted with C null (-) at position 129 can be substituted with P null (-) at position 130 can be substituted with Y or L null (-) at position 131 can be substituted with Y or D Y at position 132 can be substituted with null (-), F or H D at position 133 can be substituted with S, G, T, V, Y, A, F or M Y at position 134 can be substituted with G or F M at position 136 can be substituted with L D at position 137 can be substituted with G Xaa Xaa Xaa Xaa (SEQ ID NO: 50004)

Xaa Ile Xaa Tyr Asp Xaa Xaa Xaa Xaa Lys Xaa Xaa Xaa Xaa Xaa Xaa Xaa Lys Gly (SEQ ID NO: 50005)

FIGURE 57
(Continued)

Xaa Xaa Xaa Xaa Xaa Xaa Xaa Xaa Xaa Xaa Xaa Xaa Gly Xaa Xaa Xaa Val (SEQ ID NO: 50006)

Ser Tyr Val Met His (SEQ ID NO: 50471)

Val Ile Trp Tyr Asp Gly Ser Asn Lys Tyr Tyr Ala Asp Ser Val Lys Gly (SEQ ID NO: 50472)

Glu Arg Tyr Ser Ser Gly Trp Tyr Asp Tyr Gly Met Asp Val (SEQ ID NO: 50473)

FIGURE 57
(Continued)

| Reference # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | | | | | | | | | | | H_CDR1 | | | | | | | | | | | | | H_FR2 | |
| CONSENSUS | S | G | . | F | T | S | S | . | . | . | . | . | Y | V | M | H | W | V | R | Q | A | P | G | K |
| 21-225_5E5.024_HC | | | | | | | N | | | | | | | | | | | | | | | | | | |
| 21-225_80C12_HC | | | | | | | | | | | | | | | O | | | | | | | | | | |
| 21-225_60G2_HC | | | | | | | | | | | | | | | O | | | | | | | | | | |
| 21-225_61B3_HC | | | | | | | | | | | | | | | O | | | | | | | | | | |
| 21-225_61F2_HC | | | | | | | | D | | | | | | | O | | | | | | | | | | |
| 21-225_64A4_HC | | | | | | | | D | | | | | | | | | | | | | | | | | |
| 21-225_64C8_HC | | | | | | | | | | | | | | | | | | | | | | | | | |
| 21-225_66D11_HC | | | | | | | | N | | | | | | | O | | | | | | | | | | |
| 21-225_73C9_HC | | | | L | | | N | N | | | | | | | | | | | | | | | | | |
| 21-225_7C9_HC | | | | | | | | N | | | | | | | | | | | | | | | | | |
| 21-225_7G4_HC | | | | | | | | N | | | | | | D | | | | | | | | | | | |
| 21-225_94F3_HC | | | | | | | | N | | | | | | | — | | | | | | | | | | |

FIGURE 57
(Continued)

|  | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| Reference # | | | | | | | | | | | | | | | | H_CDR2 | | | | | | | | | |
| CONSENSUS | G | L | E | W | V | A | V | I | W | Y | D | . | . | . | G | S | N | K | Y | Y | A | D | S | V | K |
| 21-225_5E5.024_HC | . | . | . | . | . | . | . | . | . | . | . | . | . | . | . | . | . | . | . | . | . | . | . | . | . |
| 21-225_80C12_HC | . | . | . | . | . | . | . | . | . | . | . | . | . | . | A | . | . | . | . | . | V | . | . | . | . |
| 21-225_60G2_HC | . | . | . | . | . | . | . | . | . | . | . | . | . | . | . | . | . | . | . | . | . | . | . | . | . |
| 21-225_61B3_HC | . | . | . | . | . | . | . | . | . | . | . | . | . | . | . | . | . | . | . | . | . | . | . | . | . |
| 21-225_61F2_HC | . | . | . | . | . | . | . | . | . | . | . | . | . | . | . | . | . | . | . | . | . | . | . | . | . |
| 21-225_64A4_HC | . | . | . | . | . | . | . | . | . | . | . | . | . | . | . | . | . | . | . | . | . | . | . | . | . |
| 21-225_64C8_HC | . | . | . | . | . | . | . | . | . | . | . | . | . | . | . | . | . | . | . | . | . | . | . | . | . |
| 21-225_66D11_HC | . | . | . | . | . | . | . | . | . | . | . | . | . | . | . | . | . | . | . | . | . | . | . | . | . |
| 21-225_73C9_HC | . | . | . | . | . | . | . | . | . | . | . | . | . | . | . | . | . | . | . | . | . | . | . | M | . |
| 21-225_7C9_HC | . | . | . | . | . | . | . | . | . | . | . | . | . | . | . | . | . | . | . | . | . | . | . | . | . |
| 21-225_7G4_HC | . | . | . | . | . | . | . | . | . | . | . | . | . | . | . | . | . | . | . | . | . | . | . | . | . |
| 21-225_94F3_HC | . | . | . | . | . | . | . | . | . | . | . | . | . | . | . | . | . | . | . | . | . | . | . | . | . |

FIGURE 57
(Continued)

| Reference # | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|---|---|---|
| | | | | | | | | | | | | | | | | | H_FR3 | | | | | | | | |
| CONSENSUS | G | R | F | T | I | S | R | D | N | S | K | N | T | L | Y | L | Q | M | N | S | L | R | A | E | D |
| 21-225_5E5.024_HC | . | . | . | . | . | . | . | . | . | . | . | . | . | . | . | . | . | . | . | . | . | . | . | . | . |
| 21-225_60C12_HC | . | . | . | . | . | . | . | . | . | . | . | . | . | . | . | . | . | . | . | . | . | . | . | . | . |
| 21-225_60G2_HC | . | . | . | . | . | . | . | . | . | . | . | . | . | . | . | . | . | . | . | . | . | . | . | . | . |
| 21-225_61B3_HC | . | . | . | . | . | . | . | . | . | . | . | . | . | . | . | . | . | . | . | . | . | . | . | . | . |
| 21-225_61F2_HC | . | . | . | . | . | . | . | . | . | . | . | . | . | . | . | . | . | . | . | . | . | . | . | . | . |
| 21-225_64A4_HC | . | . | . | . | . | . | . | . | . | . | Q | . | . | . | . | . | . | . | . | . | . | . | . | . | . |
| 21-225_64C8_HC | . | . | . | . | . | . | . | . | . | . | . | . | . | . | . | . | . | . | . | . | . | . | . | . | . |
| 21-225_88D11_HC | . | . | . | . | . | . | . | . | . | . | . | . | . | . | . | . | . | . | . | . | . | . | . | . | . |
| 21-225_73C9_HC | . | . | . | . | . | . | . | . | . | . | . | . | . | . | S | . | . | . | . | . | . | . | . | . | . |
| 21-225_7C9_HC | . | . | . | . | . | . | . | . | . | . | . | . | . | . | . | . | . | . | . | . | . | . | . | . | . |
| 21-225_7G4_HC | . | . | . | . | . | . | . | . | . | . | . | . | . | . | . | . | . | . | T | . | . | . | . | . | . |
| 21-225_94F3_HC | . | . | . | . | . | . | . | . | . | . | . | . | . | . | . | . | . | . | . | . | . | . | . | . | . |

FIGURE 57
(Continued)

| Reference # | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|---|
| | | | | | | | | | | | | | | | | | | | | | | | H_CDR3 | | |
| CONSENSUS | T | A | V | Y | Y | C | A | R | E | R | Y | S | S | G | W | | | | | | | | | | |
| 21-225_5E5.024_HC | . | . | . | . | . | . | . | . | . | V | . | . | . | W | Y | . | . | . | . | . | . | . | . | . | . |
| 21-225_60C12_HC | . | . | . | . | . | . | . | . | W | Y | S | W | . | W | . | . | . | . | . | . | . | . | . | . | . |
| 21-225_60G2_HC | . | . | . | . | . | . | . | . | W | Y | S | W | . | W | . | . | . | . | . | . | . | . | . | . | . |
| 21-225_61B3_HC | . | . | . | . | . | . | . | . | W | Y | S | W | . | W | . | . | . | . | . | . | . | . | . | . | . |
| 21-225_61F2_HC | . | . | . | . | . | . | . | . | . | . | . | . | . | . | . | . | . | . | . | . | . | . | . | . | . |
| 21-225_64A4_HC | . | . | . | . | . | . | . | . | . | . | . | . | . | S | . | . | . | . | . | . | . | . | . | . | . |
| 21-225_64C8_HC | . | . | . | . | . | . | . | . | . | . | . | . | . | . | . | . | . | . | . | . | . | . | . | . | . |
| 21-225_68D11_HC | . | . | L | . | . | . | . | . | . | W | . | . | . | N | . | . | . | . | . | . | . | . | . | . | . |
| 21-225_73C9_HC | . | . | . | . | . | . | . | . | . | . | . | . | . | S | . | . | . | . | . | . | . | . | . | . | . |
| 21-225_7C9_HC | . | . | . | . | . | . | . | . | . | W | . | . | . | S | . | . | . | . | . | . | . | . | . | . | . |
| 21-225_7G4_HC | . | . | . | . | . | . | . | . | . | W | . | . | . | N | . | . | . | . | . | . | . | . | . | . | . |
| 21-225_94F3_HC | . | . | . | . | W | . | . | . | . | W | . | . | . | . | . | . | . | . | . | . | . | . | . | . | . |

FIGURE 57
(Continued)

Table 51. Consensus 17 - VH3|3-33/D7|7-27|RF2/JH4 (SEQ ID NO: 50268):

QVQLVES-GGGVVQPGRSLRLSCAASG-FTFSD-----YGMHWVRQAPGKGLEWVAVIWYD---
ENNKYYADSVKGRFTISRDNSKNTLYLQMNSLRAEDTAVYYCARELGF..........SDYWGQGTLVTVSS wherein:

D at position 33 can be substituted with S, N or T

Y at position 39 can be substituted with F

M at position 41 can be substituted with I

V at position 57 can be substituted with L

I at position 58 can be substituted with V, T or M

Y at position 60 can be substituted with F or D

D at position 61 can be substituted with E, A, G or N

E at position 65 can be substituted with G, V, R or D

N at position 66 can be substituted with S, T, D, I or Y

N at position 67 can be substituted with H or K

K at position 68 can be substituted with Q, E, N or R

Y at position 69 can be substituted with H, K, D, R or S

Y at position 70 can be substituted with H

A at position 71 can be substituted with V, G, T, I or E

D at position 72 can be substituted with E

V at position 74 can be substituted with M

K at position 75 can be substituted with R

FIGURE 57
(Continued)

E at position 109 can be substituted with D or G

G at position 111 can be substituted with A

F at position 112 can be substituted with W or M

L at position 135 can be substituted with R, T, Y, S, Q, I, A, E or N

S at position 136 can be substituted with E, G, D, F, N, A or T

D at position 137 can be substituted with E

Y at position 138 can be substituted with S, F or C

Xaa Xaa Gly Xaa His (SEQ ID NO: 50007)

Xaa Xaa Trp Xaa Xaa Xaa Xaa Xaa Xaa Xaa Xaa Ser Xaa Xaa Gly (SEQ ID NO: 50008)

Xaa Leu Xaa Xaa Xaa Xaa Xaa (SEQ ID NO: 50009)

Asp Tyr Gly Met His (SEQ ID NO: 50474)

Val Ile Trp Tyr Asp Glu Asn Asn Lys Tyr Tyr Ala Asp Ser Val Lys Gly (SEQ ID NO: 50475)

Glu Leu Gly Phe Ser Asp Tyr (SEQ ID NO: 50476)

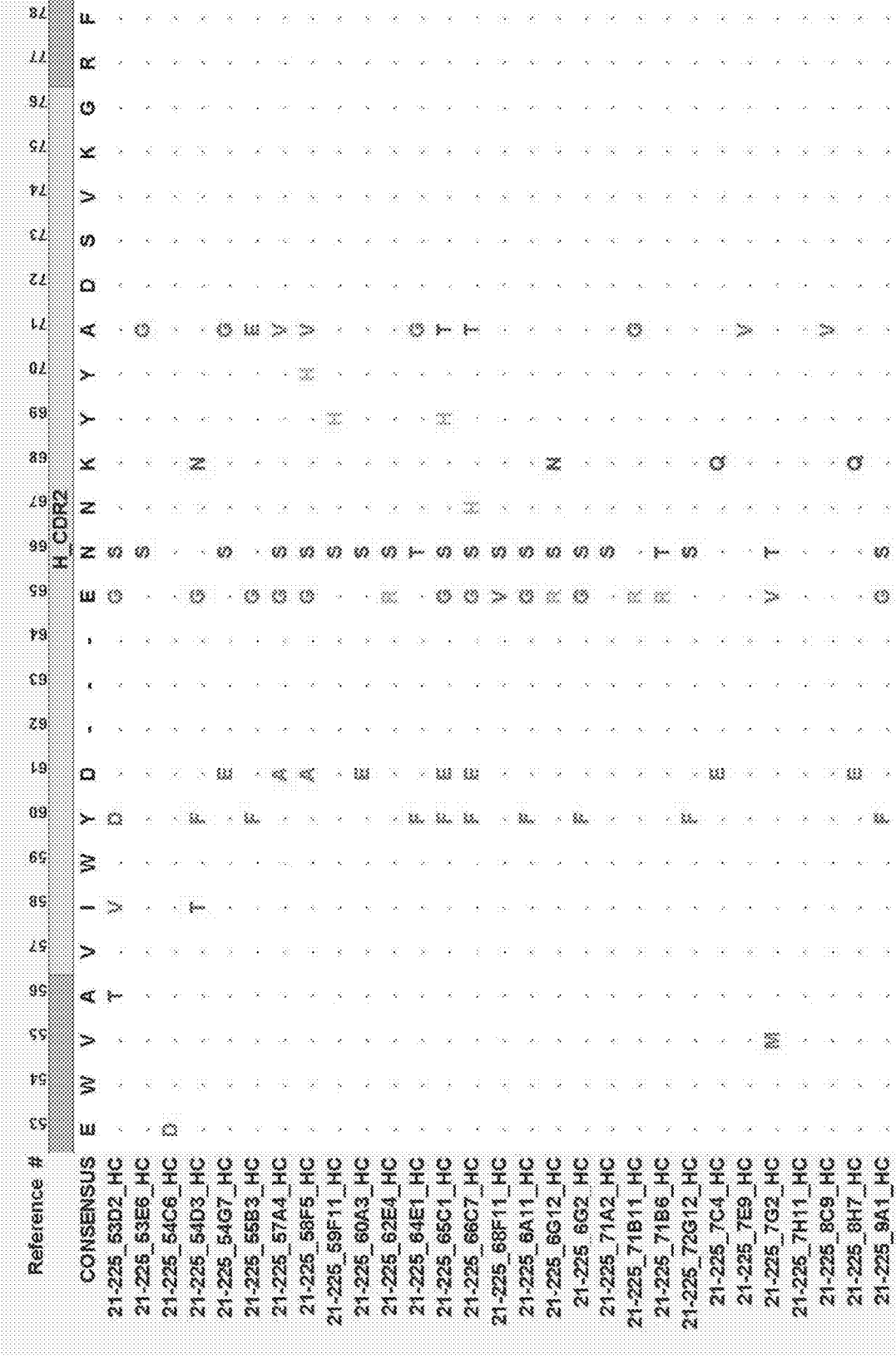

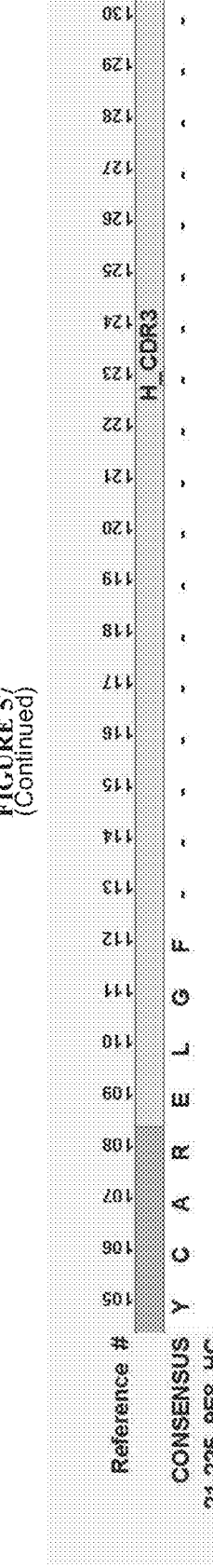

FIGURE 57
(Continued)

Table 52. Consensus 18 - VH4|4-34/D4|4-17/RF2/JH6 (SEQ ID NO: 50269):

QVQLQQW-GAGLLKPSETLSLTCAVHG-GSFSG------CYWSWIRQPPGKGLEWIGEINH----SGSTNYNPSLKSRVTISVDTSKNQFSLKLSSVTAADTAVYYCARDYGG----------MDVWGQGTTVTVSS wherein:

C at position 39 can be substituted with S, P or Y

H at position 60 can be substituted with Y or Q

S at position 65 can be substituted with R

S at position 67 can be substituted with R, C, or I

N at position 69 can be substituted with S

Y at position 70 can be substituted with F

K at position 75 can be substituted with T

M at position 136 can be substituted with L or I

Gly Xaa Tyr Trp Ser (SEQ ID NO: 50010)

Glu Ile Asn Xaa Xaa Gly Xaa Thr Xaa Xaa Asn Pro Ser Leu Xaa Ser (SEQ ID NO: 50011)

Asp Tyr Gly Gly Xaa Xaa Asp Val (SEQ ID NO: 50012)

Gly Cys Tyr Trp Ser (SEQ ID NO: 50477)

Glu Ile Asn His Ser Gly Ser Thr Asn Tyr Asn Pro Ser Leu Lys Ser (SEQ ID NO: 50478)

Asp Tyr Gly Gly Met Asp Val (SEQ ID NO: 50479)

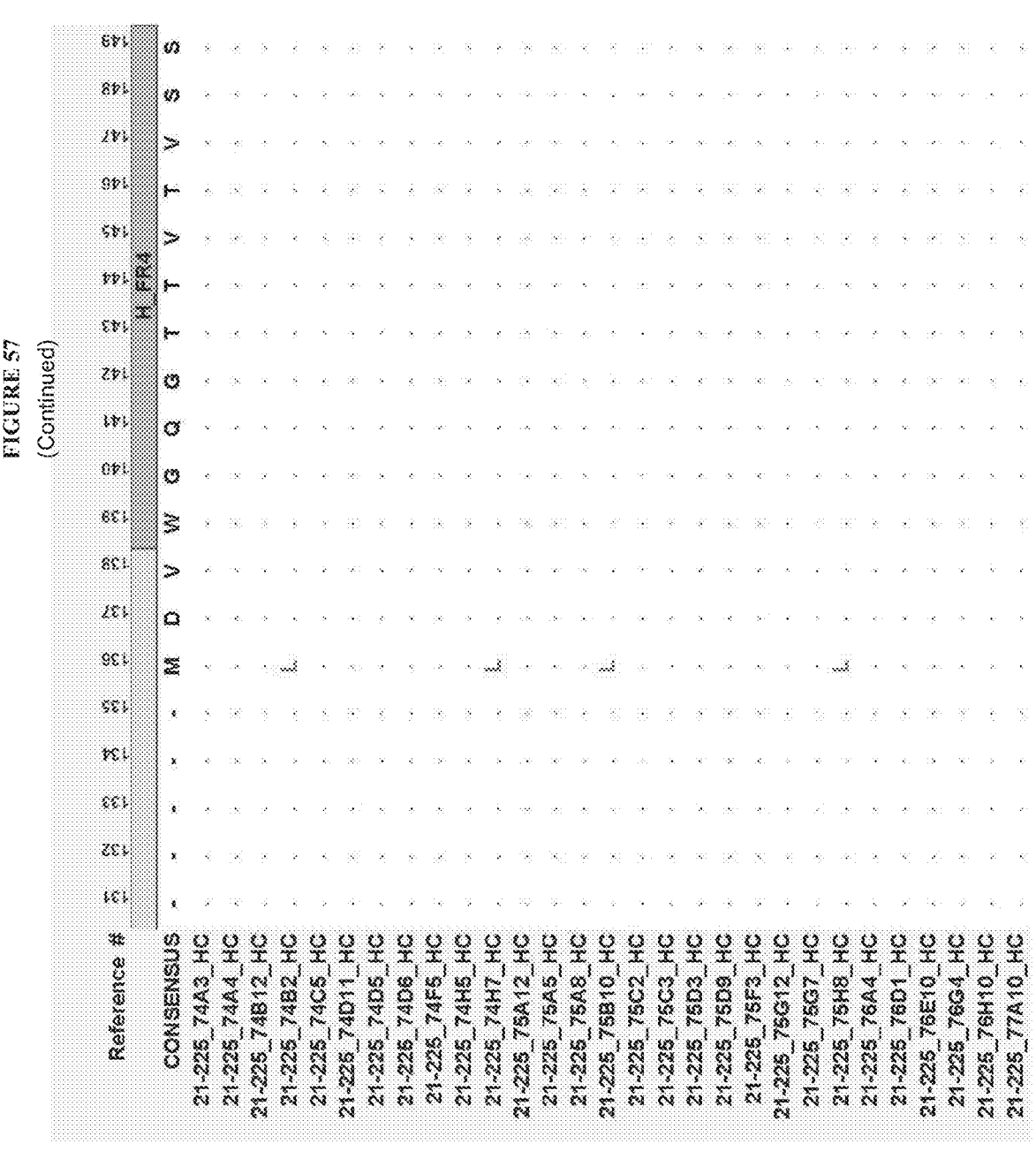

FIGURE 57
(Continued)

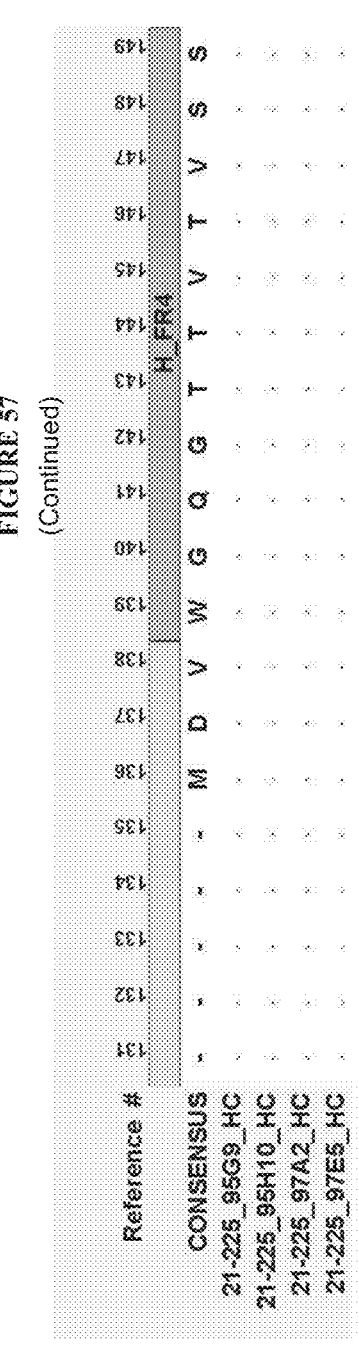

Table 53. Consensus 19-VH1|1-08/D6i6-19|RF1/JH5 (SEQ ID NO: 50270):

QVQLVQS-GAEVKKPGASVKVSCKASG-YTFTN----YDINWVRQATGQGLEWMGWMHPN---SGNTGYAQKFQGRVTMTRNTSISTAYMELSSLRSEDTAVYYCAISSGWY----------WFDPWGQGTLVTVSS wherein:

H at position 59 can be substituted with N, or Y

N at position 61 can be substituted with D

S at position 65 can be substituted with N

G at position 66 can be substituted with V

N at position 67 can be substituted with S

T at position 68 can be substituted with I

Y at position 70 can be substituted with F, or C

G at position 76 can be substituted with D

Y at position 113 can be substituted with H, N, S, or K

FIGURE 57
(Continued)

W at position 135 can be substituted with R

Asn Tyr Asp Ile Asn (SEQ ID NO: 50013)

Trp Met Xaa Pro Xaa Xaa Xaa Xaa Gly Xaa Xaa Ala Gln Lys Phe Gln Xaa (SEQ ID NO: 50014)

Ser Ser Gly Trp Xaa Xaa Phe Asp Pro (SEQ ID NO: 50015)

Asn Tyr Asp Ile Asn (SEQ ID NO: 50480)

Trp Met His Pro Asn Ser Gly Asn Thr Gly Tyr Ala Gln Lys Phe Gln Gly (SEQ ID NO: 50481)

Ser Ser Gly Trp Tyr Trp Phe Asp Pro (SEQ ID NO: 50482)

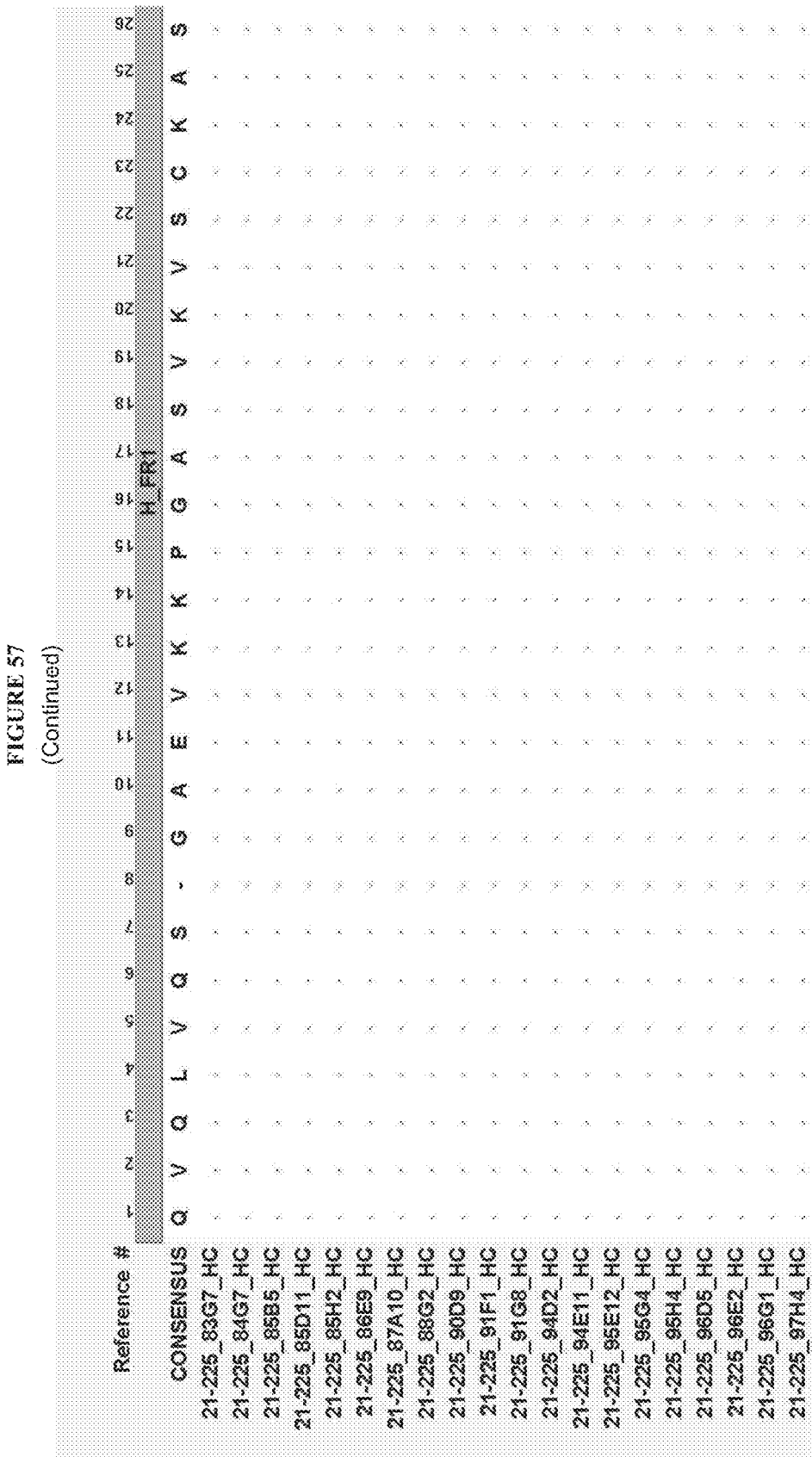

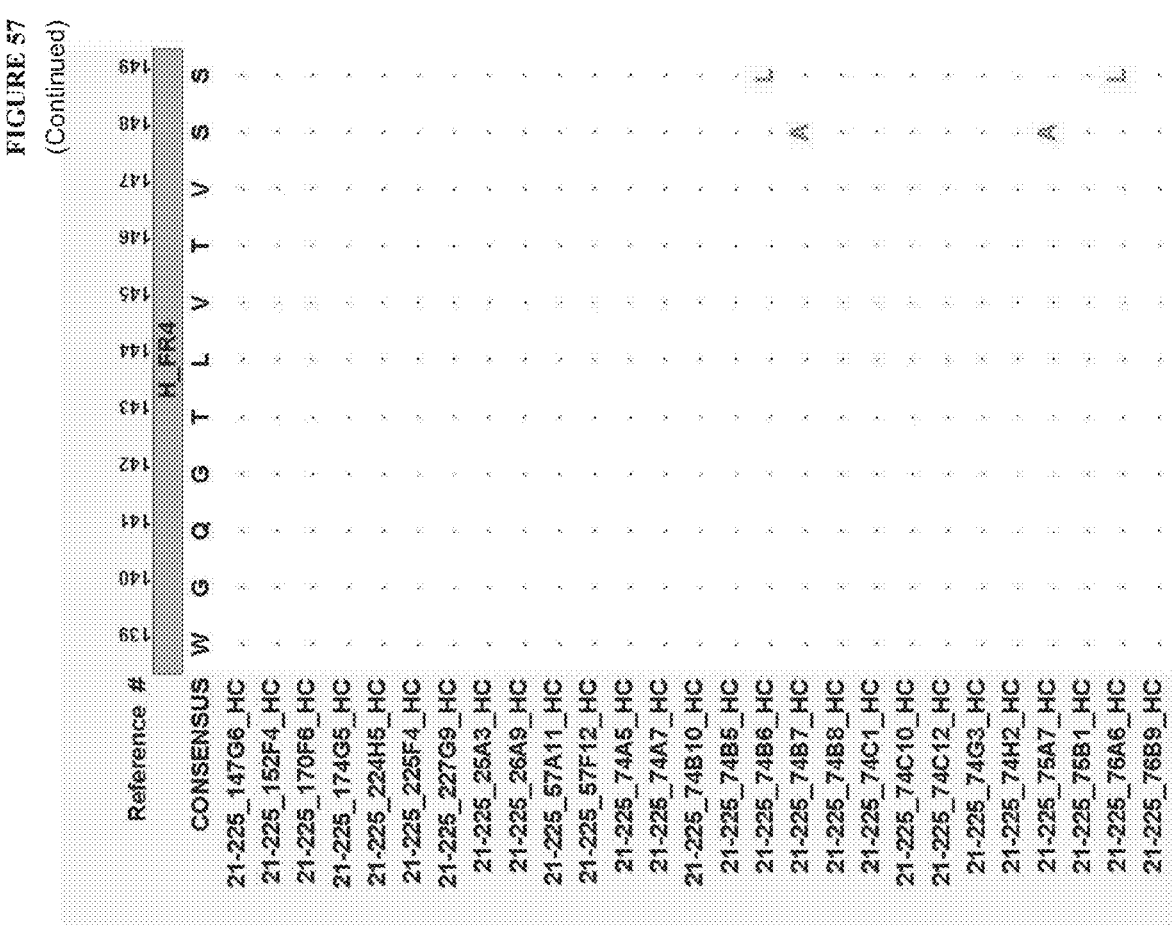

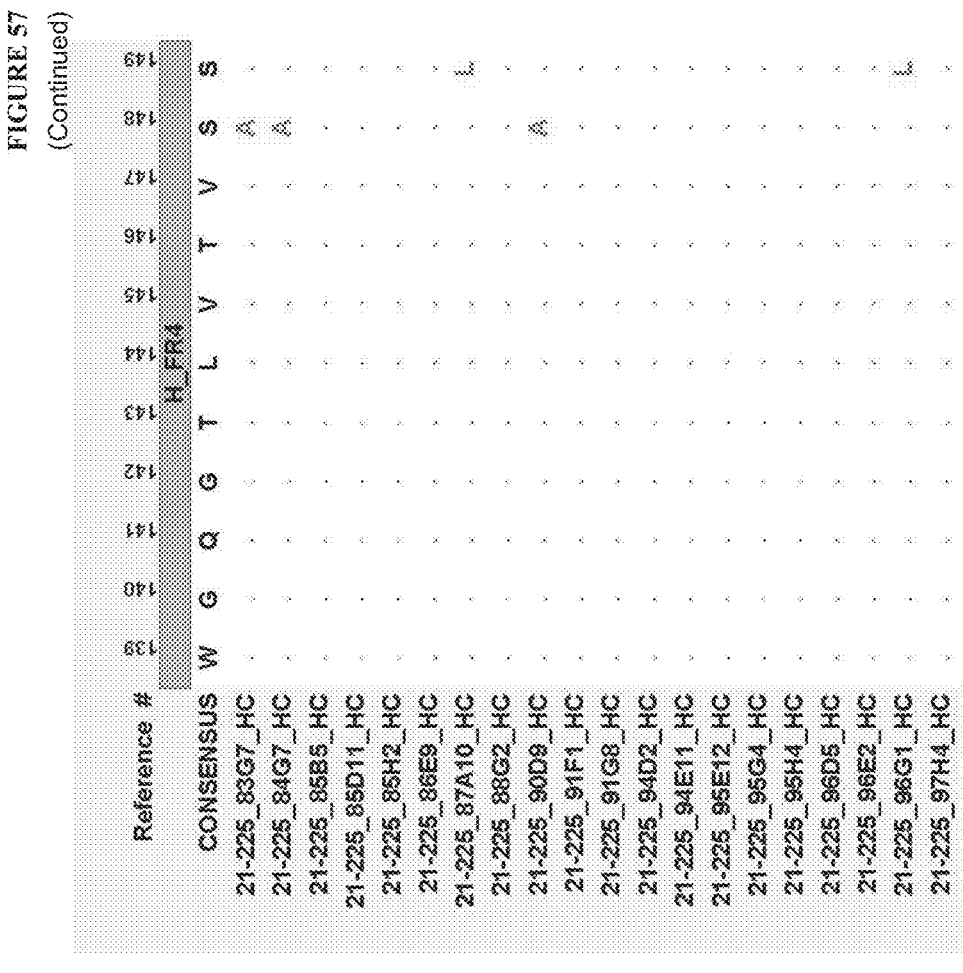

FIGURE 57
(Continued)

Table 54. Consensus 20- VH3|3-33/D4|4-17|RF2/JH6 (SEQ ID NO: 50271):

QVQLVES-GGGVVQPGRSLRLSCAASG-FTFSS-----YGMHWVRQAPGKGLEWVAVIWYD---
GSNKNYADSVKGRFTISRDNSKNTLYLQMNSLRAEDTAVYYCARDQGVGY----------YGLDVWGQGTTVTVSS wherein:

S at position 33 can be substituted with N, R, T or I

Y at position 39 can be substituted with H or N

H at position 42 can be substituted with D

V at position 57 can be substituted with I

I at position 58 can be substituted with L

Y at position 60 can be substituted with F

S at position 66 can be substituted with T

K at position 68 can be substituted with E, Q, D or R

N at position 69 can be substituted with H or Y

Y at position 70 can be substituted with H

A at position 71 can be substituted with V or G

D at position 72 can be substituted with E

D at position 109 can be substituted with A

Q at position 110 can be substituted with R, Y, H, A, C, E, F or M

V at position 112 can be substituted with I or F

G at position 113 can be substituted with Y

FIGURE 57
(Continued)

Y at position 114 can be substituted with E null (-) at position 115 can be substituted with F null (-) at position 116 can be substituted with D null (-) at position 131 can be substituted with Y null (-) at position 132 can be substituted with Y null (-) at position 133 can be substituted with N Y at position 134 can be substituted with D, or N G at position 135 can be substituted with A or D L at position 136 can be substituted with M, T or I Xaa Xaa Gly Met Xaa (SEQ ID NO: 50016)

Xaa Xaa Trp Xaa Asp Gly Xaa Asn Xaa Xaa Xaa Xaa Ser Val Lys Gly (SEQ ID NO: 50017)

Xaa Xaa Gly Xaa Xaa Xaa Xaa Xaa Xaa Xaa Xaa Xaa Asp Val (SEQ ID NO: 50018)

Ser Tyr Gly Met His (SEQ ID NO: 50483)

Val Ile Trp Tyr Asp Gly Ser Asn Lys Asn Tyr Ala Asp Ser Val Lys Gly (SEQ ID NO: 50484)

Asp Gln Gly Val Gly Tyr Tyr Gly Leu Asp Val (SEQ ID NO: 50485)

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | H_CDR1 | | | | | | | | | | | | H_FR2 | | | | | | | | |
| CONSENSUS | G | . | F | T | F | S | S | . | . | . | . | Y | G | M | H | W | V | R | Q | A | P | G | K | G | L |
| 21-225_199A6_HC | | | | | | | N | | | | | | | | | | | | | | | | | | | |
| 21-225_199C5_HC | | | | | | | | | | | | | | | | | | | | | | | | | | |
| 21-225_204G6_HC | | | | | | | G | | | | | | | | | | | | | | | | | | | |
| 21-225_205F5_HC | | | | | | | | | | | | | | | | | | | | | | | | | | |
| 21-225_207G6_HC | | | | | | | | | | | | | | | | | | | | | | | | | | |
| 21-225_211A11_HC | | | | | | | | | | | | | | | | | | | | | | | | | | |
| 21-225_211A8_HC | | | | | | | | | | | | | | | | | | | | | | | | | | |
| 21-225_212D7_HC | | | | | | | G | | | | | | | | | | | | | | | | | | | |
| 21-225_212E10_HC | | | | | | | | | | | | | | | | | | | | | | | | | | |
| 21-225_212E6_HC | | | | | | | | | | | | | | | | | | | | | | | | | | |
| 21-225_212F10_HC | | | | | | | | | | | | | | | | | | | | | | | | | | |
| 21-225_212H9_HC | | | | | | | | | | | | | | | | | | | | | | | | | | |
| 21-225_213B8_HC | | | | | | | | | | | | | | | | | | | | | | | | | | |
| 21-225_213C4_HC | | | | | | | | | | | | | | | | | | | | | | | | | | |
| 21-225_213D2_HC | | | | | | | | | | | | | | | | | | | | | | | | | | |
| 21-225_214C3_HC | | | | | | | | | | | | | | | | | | | | | | | | | | |
| 21-225_215A12_HC | | | L | | | | | | | | | | | | | | | | | | | | | | | |
| 21-225_215B5_HC | | | | | | | | | | | | | | | | | | | | | | | | | | |
| 21-225_215D6_HC | | | | | | | | | | | | | | | | | | | | | | | | | | |
| 21-225_217G5_HC | | | | | | | G | | | | | | | | | | | | | | | | | | | |
| 21-225_219H1_HC | | | | | | | N | | | | | N | | | | D | | | | | | | | | | |
| 21-225_223D11_HC | | | | | | | | | | | | | | | | | | | | | | | | | | |
| 21-225_74D1_HC | | | | | | | | | | | | | | | | | | | | | | | | | | |
| 21-225_87B7_HC | | | | | | | | | | | | | | | | | | | | | | | | | | |

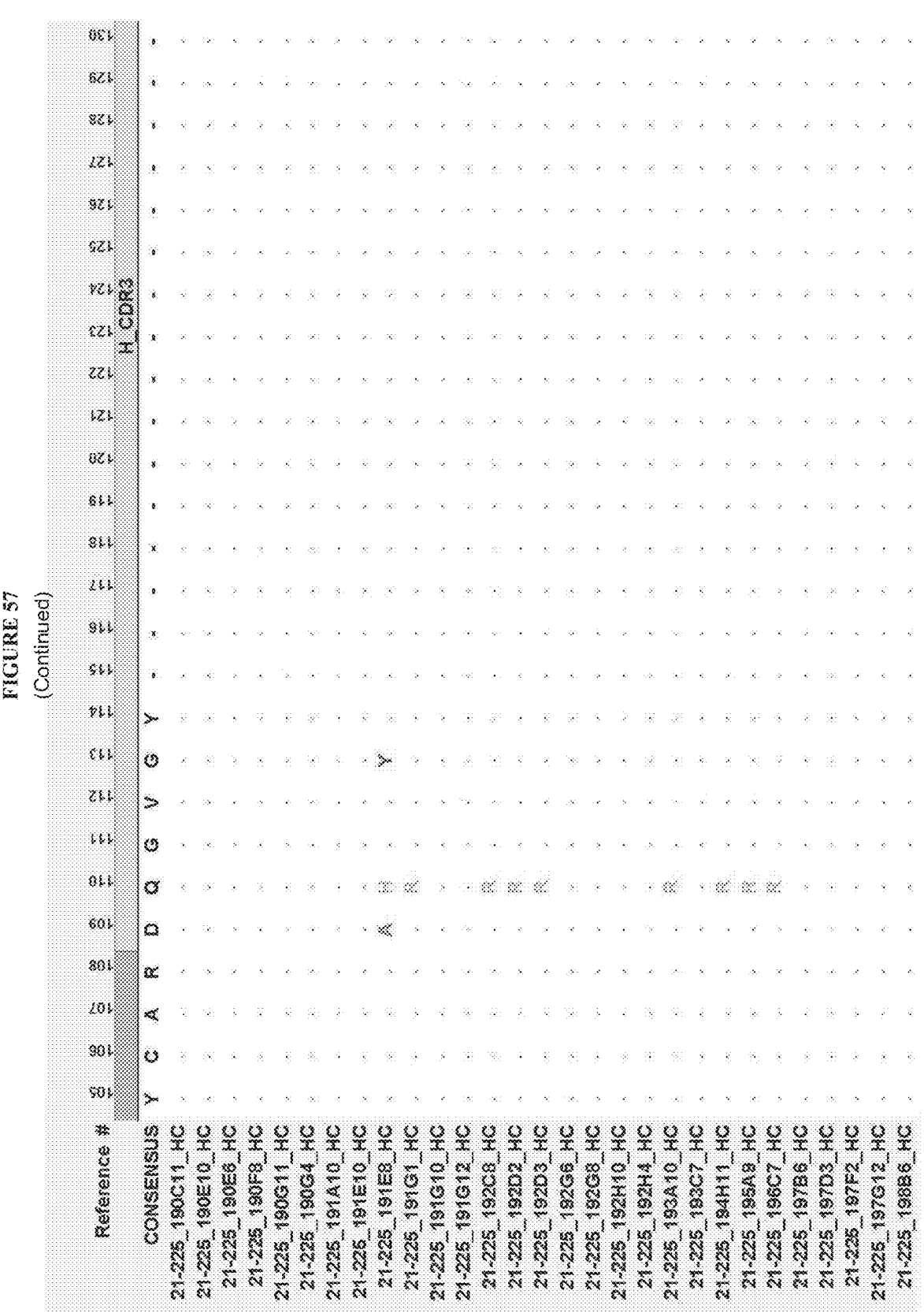

Table 55. Consensus 21- VH1I1-02/DI11-1|RF1/JH4 (SEQ ID NO: 50272):

QVQLVQS-GAEVKKPGASVKVSCKASG-YTFTG-----YYMHWVRQAPGQGLEWMGWINPN---SGGTNYAQKFQGRVTMTRDTSISTAYMELSRLRSDDTAVYYCARDGTS-----------SFDYWGQGTLVTVSS wherein:

G at position 33 can be substituted with D, S or A

Y at position 39 can be substituted with D

Y at position 40 can be substituted with H, N or F

M at position 41 can be substituted with L or I

H at position 42 can be substituted with Q

I at position 58 can be substituted with V

N at position 59 can be substituted with H, K or S

N at position 61 can be substituted with K

S at position 65 can be substituted with N, R or T

G at position 66 can be substituted with N or D

G at position 67 can be substituted with A

T at position 68 can be substituted with S

N at position 69 can be substituted with H, Q or I

Y at position 70 can be substituted with S or F

A at position 71 can be substituted with T

K at position 73 can be substituted with R, N, E or S

G at position 76 can be substituted with D

FIGURE 57
(Continued)

D at position 109 can be substituted with K, G, S or E

G at position 110 can be substituted with F, A, K or V

T at position 111 can be substituted with null (-) or P

S at position 112 can be substituted with G, null (-), or T null (-) at position 113 can be substituted with V or S null (-) at position 114 can be substituted with A null (-) at position 115 can be substituted with T null (-) at position 133 can be substituted with W null (-) at position 134 can be substituted with G S at position 135 can be substituted with null (-), V or Y F at position 136 can be substituted with null (-), L or Y D at position 137 can be substituted with G or K Y at position 138 can be substituted with D or F Xaa Xaa Xaa Xaa (SEQ ID NO: 50019)

Trp Xaa Xaa Pro Xaa Xaa Xaa Xaa Xaa Xaa Xaa Gln Xaa Xaa Phe Gln Xaa (SEQ ID NO: 50020)

Xaa Xaa Xaa Xaa Xaa Xaa Xaa Xaa Xaa Xaa Xaa Xaa Xaa (SEQ ID NO: 50021)

Gly Tyr Tyr Met His (SEQ ID NO: 50486)

Trp Ile Asn Pro Asn Ser Gly Gly Thr Asn Tyr Ala Gln Lys Phe Gln Gly (SEQ ID NO: 50487)

Asp Gly Thr Ser Ser Phe Asp Tyr (SEQ ID NO: 50488)

FIGURE 50

| | | | | |
|---|---|---|---|---|
| iPS:451141 | 21-225_164B11 | NA | GACATCGTGATGACCCAGTCTCCAGACTCCCT GGCTGTGTCTCTGGGCGAGAGGGCCACCATCA ACTGCAAGTCCAGCCAGAGTCTTTTAAAGAGC TCCAACAATAAGAGCTACTTAGCTTCGTACCA GCAGAAGCCAGGACAGCTTCCTAAACTGCTCA TTTACTGGGCATCTTCCGGGAATCCGGGGTC CCTGACCGATTCAGTGGCAGCGGGTCTGGGAC AGATTTCACTCTCACCATCAGCAGCCTGCAGG CTGAAGATGTGGCACTTTATTACTGTCAGCAA TATTATAGTATTCCTCCCACTTTCGGCCATGGG ACCAATGTGGATATCACG | CAGGTGCAGCTGGTGCAGTCTGGGGCTGAGGTG AAGAAGCCTGGGGCCTCAGTGAAGGTCTCCTGC AAGGCTTCTGGATACACCTTCACCAATTATGATA TCAACTGGGTGCGACAGGCCACTGGACAAGGGC TTGAGTGGATGGGATGGATGACCCCTAACAGTGG TAACACAGGCTATGCACAGAAGTTCCAGGGCAG AGTCACCATGACCAGGAACACTTCCATGAGCACC GCCTACATGGAGCTGAGCAGCCTGAGATCTGAG GACTCGGCCGTGTATTACTGTTCCTATAGCAGTG GCTGGTACATGTTTGACTACTGGGGCCAGGGAAC CCTGGTCACCGTCTCCTCA |
| | | | SEQ ID NO: 24117 | SEQ ID NO: 28123 |
| | | AA | DIVMTQSPDSLAVSLGERATINCKSSQSLLKSSN NKSYLASYQQKPGQLPKLLIYWASSRESGVPDR FSGSGSGTDFTLTISSLQAEDVALYYCQQYYSIPP TFGHGTNVDIT | QVQLVQSGAEVKKPGASVKVSCKASGYTFTNYDIN WVRQATGQGLEWMGWMTPNSGNTGYAQKFQGR VTMTRNTSMSTAYMELSSLRSEDSAVYYCSYSSG WYMFDYWGQGTLVTVSS |
| | | | SEQ ID NO: 24118 | SEQ ID NO: 28124 |
| iPS:451137 | 21-225_74A7 | NA | GACATCGTTATGACCCAGTCTCCAGACTCCCT GGCTGTGTCTCTGGGCGAGAGGGCCACCATCA ACTGCAAGTCCAGCCAGAGTGTTTTATTCAGC TCCAACAATTATAACTACTTAGCTTGGTACCA GCAGAGACCAGGACAGCCTCCTAACCTGCTCA TTTACTGGGCATCTACCCGGGAATCCGGGGTC CCTGACCGATTCAGTGGCAGCGGGTCTGGGAC AGATTTCACTCTCACCATCAGCAGCCTGCAGG CTGCTGATGTGGCAGTTTATTACTGTCAGCAA TATCATAGTTCTCCTCCGACGTTCGGCCAAGG GACCACGGTGCAAATCAAA | CAGGTGCAGTTGGTGCAGTCTGGGGCTGAGGTGA AGAAGCCTGGGGCCTCAGTGAAGGTCTCCTGCA AGGCTTCTGGATACACCTTCACCAATTATGATAT CAACTGGGTGCGACAGGCCACTGGACAAGGGCT TGAGTGGATGGGATGGATGAACCCTAACAGTGG TAACACAGGCTATGCACAGAAGTTCCAGGGCAG AGTCACCATGACCAGGAACACCTCCACAAGCAC AGCCTACATGGAGCTGAGCAGCCTGAGATCTGA GGACACGGCCGTGTATTACTGTGCGGTCTCCAGT GGCTGGAACTGGTTCGACCCCTGGGGCCAGGGA ACCCTGGTCACCGTCTCCTCA |
| | | | SEQ ID NO: 24119 | SEQ ID NO: 28125 |

FIGURE 57
(Continued)

Table 56. Consensus 22- VH3j3-33/D4j4-11|RF2/JH6 (SEQ ID NO: 50273):

QVQLVES-GGGVVQPGRSLRLSCAASG-FTFSS-----YGMHWVRQAPGKGLEWVAVIWHD---
GSNKYYADSVKGRFTISRDNSKNTLYLQMNSLRAEDTAVYYCARDLSMG--------------GMDVWGQGTTVTVSS wherein:

S at position 33 can be substituted with N

Y at position 39 can be substituted with F or H

M at position 41 can be substituted with I

V at position 57 can be substituted with I

W at position 59 can be substituted with I

H at position 60 can be substituted with Y, F or N

D at position 61 can be substituted with S or E

G at position 65 can be substituted with A

S at position 66 can be substituted with G

N at position 67 can be substituted with Y

K at position 68 can be substituted with D, E or R

Y at position 69 can be substituted with N

Y at position 70 can be substituted with N

A at position 71 can be substituted with V or G

D at position 72 can be substituted with E

S at position 73 can be substituted with A

K at position 75 can be substituted with R

FIGURE 57
(Continued)

D at position 109 can be substituted with T or R

L at position 110 can be substituted with R, Y, S, F, I or P S

S at position 111 can be substituted with R or T

M at position 112 can be substituted with V, G, P, K, N or Y

G at position 113 can be substituted with Y, null (-) or S null (-) at position 114 can be substituted with Y, S or W null (-) at position 115 can be substituted with G null (-) at position 116 can be substituted with S null (-) at position 117 can be substituted with G null (-) at position 118 can be substituted with S null (-) at position 119 can be substituted with P null (-) at position 129 can be substituted with P null (-) at position 130 can be substituted with Y null (-) at position 131 can be substituted with Y null (-) at position 132 can be substituted with Y null (-) at position 133 can be substituted with S or Y null (-) at position 134 can be substituted with D, Y or G M at position 136 can be substituted with L or T Xaa Xaa Gly Xaa His (SEQ ID NO: 50022)

FIGURE 57
(Continued)

Xaa Ile Xaa Xaa Xaa Xaa Xaa Xaa Xaa Xaa Xaa Val Xaa Gly (SEQ ID NO: 50023)

Xaa Xaa Xaa Xaa Xaa Xaa Xaa Xaa Xaa Xaa Xaa Xaa Gly Xaa Asp Val (SEQ ID NO: 50024)

Ser Tyr Gly Met His (SEQ ID NO: 50489)

Val Ile Trp His Asp Gly Ser Asn Lys Tyr Tyr Ala Asp Ser Val Lys Gly (SEQ ID NO: 50490)

Asp Leu Ser Met Gly Gly Met Asp Val (SEQ ID NO: 50491)

FIGURE 57
(Continued)

| Reference # | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|---|---|
| | | | | | | | | | | | | | | | | | | H_FR4 | | | | | | |
| CONSENSUS | . | . | . | . | . | . | . | . | . | G | M | D | V | W | G | Q | G | T | T | V | T | V | S | S |
| 21-225_7E11.001.001_HC | . | . | . | . | . | . | . | . | . | . | . | . | . | . | . | . | . | . | . | . | . | . | . | . |
| 21-225_7E11.001.002_HC | . | . | . | . | . | . | . | . | . | . | . | . | . | . | . | . | . | . | . | . | . | . | . | . |
| 21-225_7E11.001.003_HC | . | . | . | . | . | . | . | . | . | . | . | . | . | . | . | . | . | . | . | . | . | . | . | . |
| 21-225_7E11.001.004_HC | . | . | . | . | . | . | . | . | . | . | . | . | . | . | . | . | . | . | . | . | . | . | . | . |
| 21-225_7E11.001.005_HC | . | . | . | . | . | . | . | . | . | . | . | . | . | . | . | . | . | . | . | . | . | . | . | . |
| 21-225_7E11.001.006_HC | . | . | . | . | . | . | . | . | . | . | . | . | . | . | . | . | . | . | . | . | . | . | . | . |
| 21-225_7E11.001.007_HC | . | . | . | . | . | . | . | . | . | . | . | . | . | . | . | . | . | . | . | . | . | . | . | . |
| 21-225_7E11.001.008_HC | . | . | . | . | . | . | . | . | . | . | . | . | . | . | . | . | . | . | . | . | . | . | . | . |
| 21-225_7E11.001.009_HC | . | . | . | . | . | . | . | . | . | . | . | . | . | . | . | . | . | . | . | . | . | . | . | . |
| 21-225_7E11.001.010_HC | . | . | . | . | . | . | . | . | . | . | . | . | . | . | . | . | . | . | . | . | . | . | . | . |
| 21-225_7E11.001.011_HC | . | . | . | . | . | . | . | . | . | . | . | . | . | . | . | . | . | . | . | . | . | . | . | . |
| 21-225_7E11.001.012_HC | . | . | . | . | . | . | . | . | . | . | . | . | . | . | . | . | . | . | . | . | . | . | . | . |
| 21-225_7E11.001.013_HC | . | . | . | . | . | . | . | . | . | . | . | . | . | . | . | . | . | . | . | . | . | . | . | . |
| 21-225_7E11.001.014_HC | . | . | . | . | . | . | . | . | . | . | . | . | . | . | . | . | . | . | . | . | . | . | . | . |
| 21-225_7E11.001.015_HC | . | . | . | . | . | . | . | . | . | . | . | . | . | . | . | . | . | . | . | . | . | . | . | . |
| 21-225_7E11.001.016_HC | . | . | . | . | . | . | . | . | . | . | . | . | . | . | . | . | . | . | . | . | . | . | . | . |
| 21-225_7E11.001.017_HC | . | . | . | . | . | . | . | . | . | . | . | . | . | . | . | . | . | . | . | . | . | . | . | . |
| 21-225_7E11.001.018_HC | . | . | . | . | . | . | . | . | . | . | . | . | . | . | . | . | . | . | . | . | . | . | . | . |
| 21-225_7E11.001.023_HC | . | . | . | . | . | . | . | . | . | . | . | . | . | . | . | . | . | . | . | . | . | . | . | . |

Table 57. Consensus 23- VH3|3-33/D7|7-27|RF1/JH4 (SEQ ID NO: 50274):
QVQLVES-GGGVVQPGRSLRLSCAASG-FTFSD----YGMHWVRQAPGKGLEWVAVIWYD---
ESNKYYADSVKGRFTISRDNSKNTLYLQMNSLRAEDTAVYYCAREVGW----------LDDYWGQGTLVTVSS wherein:

FIGURE 57
(Continued)

D at position 33 can be substituted with N or S

Y at position 39 can be substituted with F

M at position 41 can be substituted with I or L

Y at position 60 can be substituted with F

D at position 61 can be substituted with E, I or V

E at position 65 can be substituted with G, V, A or R

S at position 66 can be substituted with N, T or G

K at position 68 can be substituted with Q, T or N

Y at position 69 can be substituted with H or K

A at position 71 can be substituted with T, G, E or V

D at position 72 can be substituted with G

V at position 74 can be substituted with A

V at position 110 can be substituted with I, M, K or T

W at position 112 can be substituted with F, G or M

L at position 135 can be substituted with T, S, Y, H or R

D at position 136 can be substituted with E, S, F or N

Y at position 138 can be substituted with C

Xaa Xaa Gly Xaa His (SEQ ID NO: 50025)

Val Ile Trp Xaa Xaa Xaa Xaa Asn Xaa Xaa Tyr Xaa Xaa Ser Xaa Lys Gly (SEQ ID NO: 50026)

FIGURE 57
(Continued)

Glu Xaa Gly Xaa Xaa Xaa Asp Xaa (SEQ ID NO: 50027)

Asp Tyr Gly Met His (SEQ ID NO: 50492)

Val Ile Trp Tyr Asp Gly Ser Asn Lys Tyr Tyr Ala Asp Ser Val Lys Gly (SEQ ID NO: 50493)

Glu Val Gly Trp Leu Asp Asp Tyr (SEQ ID NO: 50494)

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | | | | H_FR3 | | | | | | | | | | | |
| CONSENSUS | T | I | S | R | D | N | S | K | N | T | L | Y | L | Q | M | N | S | L | R | A | E | D | T | A | V | Y |
| 21-225_29D9_HC | . | . | . | . | . | . | . | . | . | . | . | . | . | . | . | . | . | . | . | . | . | . | . | . | . | . |
| 21-225_30F3_HC | . | . | . | . | . | . | . | . | . | . | . | . | . | . | . | . | . | . | . | . | . | . | . | . | . | . |
| 21-225_33B1_HC | . | . | . | . | . | . | . | . | . | . | . | . | . | . | . | . | . | . | T | . | . | . | . | . | . | . |
| 21-225_4C8_HC | . | . | . | . | . | . | . | . | . | . | . | . | . | . | . | . | . | . | . | . | . | . | . | . | . | . |
| 21-225_4F12_HC | . | . | . | . | . | . | . | . | . | . | . | . | . | . | . | . | . | . | T | P | . | N | . | G | G | . |
| 21-225_50C4_HC | . | . | . | . | . | . | . | . | . | . | . | . | . | . | . | . | . | . | . | G | . | . | . | . | . | . |
| 21-225_73G8_HC | . | . | . | . | . | . | . | . | . | . | . | . | . | . | . | . | . | . | . | . | . | . | . | . | . | . |
| 21-225_90H5_HC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | | H_CDR3 | | | | | | | |
| CONSENSUS | Y | C | A | R | E | V | G | W | . | . | . | . | . | . | . | . | . | . | . | . | . | . | . | . | . | . |
| 21-225_29D9_HC | . | . | . | . | . | − | . | . | . | . | . | . | . | . | . | . | . | . | . | . | . | . | . | . | . | . |
| 21-225_30F3_HC | . | . | . | . | . | M | . | . | . | . | . | . | . | . | . | . | . | . | . | . | . | . | . | . | . | . |
| 21-225_33B1_HC | . | S | P | . | . | M | . | F | . | . | . | . | . | . | . | . | . | . | . | . | . | . | . | . | . | . |
| 21-225_4C8_HC | E | N | Q | . | . | M | . | Q | . | . | . | . | . | . | . | . | . | . | . | . | . | . | . | . | . | . |
| 21-225_4F12_HC | . | . | . | . | . | M | . | F | . | . | . | . | . | . | . | . | . | . | . | . | . | . | . | . | . | . |
| 21-225_50C4_HC | . | . | . | . | . | . | . | M | . | . | . | . | . | . | . | . | . | . | . | . | . | . | . | . | . | . |
| 21-225_73G6_HC | . | . | V | . | . | M | . | . | . | . | . | . | . | . | . | . | . | . | . | . | . | . | . | . | . | . |
| 21-225_90H5_HC | . | . | . | . | . | . | . | . | . | . | . | . | . | . | . | . | . | . | . | . | . | . | . | . | . | . |

Table 58. Consensus 24-VH3l3-21/D4l4-11lRF2/JH4 (SEQ ID NO: 50275)

EVQLVES-GGGLVKPGGSLRLSCAASG-FTFSS-----YSMNWVRQAPGKGLEWVSSISGS---
SSYIYYADSVKGRFTISRDNAKNSLYLQMNSLRAEDTAVYYCARDRG..................SSWGQGTLVTVSS wherein:

S at position 33 can be substituted with T

Y at position 39 can be substituted with F

S at position 40 can be substituted with T, G or R

M at position 41 can be substituted with L

S at position 57 can be substituted with A, C or L

G at position 60 can be substituted with S

S at position 65 can be substituted with G or T

S at position 66 can be substituted with T, G or Y

Y at position 67 can be substituted with H

I at position 68 can be substituted with L or M

Y at position 69 can be substituted with S or W

A at position 71 can be substituted with G, P or V

V at position 74 can be substituted with L

G at position 76 can be substituted with A

D at position 109 can be substituted with T

G at position 111 can be substituted with null (-), S or Y null (-) at position 112 can be substituted with G FIGURE 57 (Continued)

null (-) at position 135 can be substituted with S null (-) at position 136 can be substituted with F or S S at position 137 can be substituted with D, G or H S at position 138 can be substituted with L, Y, G, T, C, E or I Xaa Xaa Xaa Xaa Asn (SEQ ID NO: 50028)

Xaa Ile Ser Xaa Ser Xaa Xaa Xaa Xaa Tyr Xaa Asp Ser Xaa Lys Xaa (SEQ ID NO: 50029)

Xaa Arg Xaa Xaa Xaa Xaa Xaa Xaa (SEQ ID NO: 50030)

Ser Tyr Ser Met Asn (SEQ ID NO: 50495)

Ser Ile Ser Gly Ser Ser Tyr Ile Tyr Tyr Ala Asp Ser Val Lys Gly (SEQ ID NO: 50496)

Asp Arg Gly Ser Ser (SEQ ID NO: 50497)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | | | | | H_FR1 | | | | | | | | | | |
| CONSENSUS | E | V | Q | L | V | E | S | - | G | G | G | L | V | K | P | G | G | S | L | R | L | S | C | A | A | S |
| 21-225_53G1_HC | . | . | . | . | . | . | . | . | . | . | . | . | . | . | . | . | E | . | . | . | . | . | . | . | . | . |
| 21-225_56F1_HC | . | . | . | . | . | . | . | . | . | . | . | . | . | . | R | . | . | . | . | . | . | . | . | . | . | . |
| 21-225_56H7_HC | . | . | . | . | . | . | . | . | . | . | . | . | . | . | . | . | . | . | . | . | . | . | . | . | . | . |
| 21-225_58C5_HC | . | . | . | . | . | . | . | . | . | . | . | . | . | . | . | . | . | . | . | . | . | . | . | . | . | . |
| 21-225_65C12_HC | . | . | . | . | . | . | . | . | . | . | . | . | . | . | . | . | . | . | . | . | . | . | . | . | . | . |
| 21-225_6C12_HC | . | . | . | . | . | . | . | . | . | . | . | . | . | . | . | . | . | . | . | . | . | . | . | . | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | | | | | | H_CDR1 | | | | | | | | | | | | | H_FR2 | | |
| CONSENSUS | G | . | F | T | F | S | S | . | . | . | . | . | Y | S | M | N | W | V | R | Q | A | P | G | K | G | L |
| 21-225_53G1_HC | . | . | . | . | . | . | . | . | . | . | . | . | . | . | . | . | . | . | . | . | . | . | . | . | . | . |
| 21-225_56F1_HC | . | . | . | . | . | . | . | . | . | . | . | . | . | . | . | . | . | . | . | . | . | . | . | . | . | . |
| 21-225_56H7_HC | . | . | . | S | . | . | . | . | . | . | . | . | . | . | . | . | . | . | . | . | . | . | . | . | . | . |
| 21-225_58C5_HC | . | . | . | . | . | N | . | . | . | . | . | . | . | . | . | . | . | . | . | . | . | . | . | . | . | . |
| 21-225_65C12_HC | . | . | . | . | . | . | . | . | . | . | . | . | R | . | L | . | . | . | . | . | . | . | . | . | . | . |
| 21-225_8C12_HC | . | . | . | . | . | . | . | . | . | . | . | . | . | . | . | . | . | . | . | . | . | . | . | . | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | | H_CDR2 | | | | | | | | | | | | |
| CONSENSUS | E | W | V | S | S | I | S | G | S | . | . | . | S | S | Y | I | Y | Y | A | D | S | V | K | G | R | F |
| 21-225_53G1_HC | . | . | . | . | . | . | . | . | . | . | . | . | . | . | . | . | . | . | . | . | . | . | . | . | . | . |
| 21-225_56F1_HC | . | . | . | . | . | . | . | G | . | . | . | . | . | T | . | . | . | . | G | . | . | . | . | . | . | . |
| 21-225_56H7_HC | . | . | . | . | . | . | . | G | . | . | . | . | . | T | . | . | . | . | G | . | . | . | . | . | . | . |
| 21-225_58C6_HC | . | . | . | . | . | . | . | G | . | . | . | . | . | Y | . | L | . | . | . | . | . | . | . | . | . | . |
| 21-225_65C12_HC | . | . | . | . | . | . | . | G | . | . | . | . | . | . | . | . | . | . | . | . | . | . | . | . | . | . |
| 21-225_6C12_HC | . | . | . | . | . | . | . | G | . | . | . | . | . | . | . | . | . | . | . | . | . | . | . | . | . | . |

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | | | | H_FR3 | | | | | | | | | | | |
| CONSENSUS | T | I | S | R | D | N | A | K | N | S | L | Y | L | Q | M | N | S | L | R | A | E | D | T | A | V | Y |
| 21-225_53G1_HC | . | . | . | . | . | . | . | . | . | . | . | . | . | . | . | . | . | . | . | . | . | . | . | . | . | . |
| 21-225_56F1_HC | . | . | . | . | . | . | . | . | . | . | . | . | . | . | . | . | . | . | . | . | . | . | . | . | . | . |
| 21-225_56H7_HC | . | . | . | . | . | S | . | . | . | . | . | . | . | . | . | . | . | . | . | . | . | . | . | . | . | . |
| 21-225_58C5_HC | . | . | . | . | . | . | . | . | . | . | . | . | . | . | . | . | . | . | . | . | . | . | . | . | . | . |
| 21-225_65C12_HC | . | . | . | . | . | . | . | . | . | . | . | . | . | . | . | . | . | . | . | . | . | . | . | . | . | . |
| 21-225_6C12_HC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | H_CDR3 | | | | | | | | | | | | | | | | | | | | | | |
| CONSENSUS | Y | C | A | R | D | R | G | . | . | . | . | . | . | . | . | . | . | . | . | . | . | . | . | . | . | . |
| 21-225_63G1_HC | . | . | . | . | . | . | . | . | . | . | . | . | . | . | . | . | . | . | . | . | . | . | . | . | . | . |
| 21-225_56F1_HC | . | . | . | . | . | . | . | . | . | . | . | . | . | . | . | . | . | . | . | . | . | . | . | . | . | . |
| 21-225_56H7_HC | . | . | . | . | T | Y | S | O | . | . | . | . | . | . | . | . | . | . | . | . | . | . | . | . | . | . |
| 21-225_58C5_HC | . | . | . | . | . | K | Y | . | . | . | . | . | . | . | . | . | . | . | . | . | . | . | . | . | . | . |
| 21-225_65C12_HC | . | . | . | . | . | . | . | . | . | . | . | . | . | . | . | . | . | . | . | . | . | . | . | . | . | . |
| 21-225_6C12_HC | . | . | . | . | . | . | . | . | . | . | . | . | . | . | . | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | H_FR4 | | | | | | |
| CONSENSUS | . | . | . | . | . | . | S | S | W | G | Q | G | T | L | V | T | V | S | S |
| 21-225_13D3_HC | . | . | . | . | . | . | . | G | . | . | . | . | . | . | . | . | . | . | . |
| 1-225_14B1_LC1_HC | . | . | . | . | . | . | . | . | . | . | . | . | . | . | . | . | . | . | . |
| 1-225_14B1_LC2_HC | . | . | . | . | . | . | . | . | . | . | . | . | . | . | . | . | . | . | . |
| 21-225_157G7_HC | . | . | . | . | . | . | . | I | . | . | . | . | . | . | . | . | . | . | . |
| 21-225_157H4_HC | . | . | . | . | . | . | G | Y | . | . | . | . | . | . | . | . | . | . | . |
| 21-225_157H7_HC | . | . | . | . | . | . | . | L | . | . | . | . | . | . | . | . | . | . | . |
| 21-225_158F6_HC | . | . | . | . | . | . | . | . | . | . | . | . | . | . | . | . | . | . | . |
| 21-225_158G8_HC | . | . | . | . | . | . | . | Y | . | . | . | . | . | . | . | . | . | . | . |
| 21-225_158H5_HC | . | . | . | . | . | . | . | . | . | . | . | . | . | . | . | . | . | . | . |
| 21-225_160F4_HC | . | . | . | . | . | . | D | L | . | . | . | . | . | . | . | . | . | . | . |
| 21-225_160H1_HC | . | . | . | . | . | . | . | . | . | . | . | . | . | . | . | . | . | . | . |
| 21-225_162F2_HC | . | . | . | . | . | . | . | G | . | . | . | . | . | . | . | . | . | . | . |
| 21-225_162H3_HC | . | . | . | . | . | . | . | Y | . | . | . | . | . | . | . | . | . | . | . |
| 21-225_163F9_HC | . | . | . | . | . | . | . | G | . | . | . | . | . | . | . | . | . | . | . |
| 21-225_171A11_HC | . | . | . | . | . | . | . | L | . | . | . | . | . | . | . | . | . | . | . |
| 21-225_17C10_HC | . | . | . | . | . | . | . | C | . | . | . | . | . | . | . | . | . | . | . |
| 21-225_17D8_HC | . | . | . | . | . | . | . | Y | . | . | . | . | . | . | . | . | . | . | . |
| 21-225_20B5_HC | . | . | . | . | . | . | . | L | . | . | . | . | . | . | . | . | . | . | . |
| 21-225_20B8_HC | . | . | . | . | . | . | . | L | . | . | . | . | . | . | . | . | . | . | . |
| 21-225_20C8_HC | . | . | . | . | . | . | . | L | . | . | . | . | . | . | . | . | . | . | . |
| 21-225_20F9_HC | . | . | . | . | . | . | . | . | . | . | . | . | . | . | . | . | . | . | . |
| 21-225_20G12_HC | . | . | . | . | . | . | . | . | . | . | . | . | . | . | . | . | . | . | . |
| 21-225_20H10_HC | . | . | . | . | . | . | . | . | . | . | . | . | . | . | . | . | . | . | . |
| 21-225_22H3_HC | . | . | . | . | . | . | . | . | . | . | . | . | . | . | . | . | . | . | . |
| 21-225_23E11_HC | . | . | . | . | . | . | . | . | . | . | . | . | . | . | . | . | . | . | . |
| 21-225_30H11_HC | . | . | . | . | . | . | . | . | . | . | . | . | . | . | . | . | . | . | . |
| 21-225_31G9_HC | . | . | . | . | . | . | G | T | . | . | . | . | . | . | . | . | . | . | . |
| 21-225_33C2_HC | . | . | . | . | . | . | . | T | . | . | . | . | . | . | . | . | . | . | . |
| 21-225_43E1_HC | . | . | . | . | . | . | . | E | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | H_FR4 | | | | | | |
| CONSENSUS | . | . | . | . | . | . | S | S | W | G | Q | G | T | L | V | T | V | S | S |
| 21-225_53G1_HC | . | . | . | . | . | . | . | T | . | . | . | . | . | . | . | . | . | . | . |
| 21-225_56F1_HC | . | . | . | . | . | . | . | . | . | . | . | . | . | . | . | . | . | . | . |
| 21-225_56H7_HC | . | . | . | . | . | F | D | Y | . | . | . | . | . | . | . | . | . | . | . |
| 21-225_58C5_HC | . | . | . | . | S | . | . | Y | . | . | . | . | . | . | . | . | . | . | . |
| 21-225_65C12_HC | . | . | . | . | . | . | H | Y | . | . | . | . | . | . | . | . | . | . | . |
| 21-225_6C12_HC | . | . | . | . | . | . | . | L | . | . | . | . | . | . | . | . | . | . | . |

FIGURE 57 (Continued)

Table 59. Consensus 25-VH3|3-23/D6i6-19|RF2/JH3 (SEQ ID NO: 50276)

EVQLLES-GGGLVQPGGSLRLSCAASE-FTFSS-----YAMSWVRQAPGKGLEWVSVISGR---
GGNTFYADSVKGRFTISRDNSKNTLYLQMNSLRAEDTAVYYCASRIAVAG........SEAFDIWGQGTMVTVSS wherein:

S at position 33 can be substituted with G

A at position 40 can be substituted with V

S at position 42 can be substituted with N or T

V at position 57 can be substituted with I or A

G at position 60 can be substituted with R

R at position 61 can be substituted with S

G at position 66 can be substituted with V, I or T

N at position 67 can be substituted with Y, S or T

T at position 68 can be substituted with A

F at position 69 can be substituted with Y

Y at position 70 can be substituted with N or S

K at position 75 can be substituted with R

I at position 110 can be substituted with L, M or V

A at position 113 can be substituted with D

S at position 133 can be substituted with N or Y

E at position 134 can be substituted with D

F at position 136 can be substituted with C

FIGURE 57 (Continued)

D at position 137 can be substituted with A or H

I at position 138 can be substituted with V

Xaa Tyr Xaa Met Xaa (SEQ ID NO: 50031)

Xaa Ile Ser Xaa Xaa Gly Xaa Xaa Xaa Xaa Ala Asp Ser Val Xaa Gly (SEQ ID NO: 50032)

Xaa Xaa Ala Val Xaa Gly Xaa Xaa Ala Xaa Xaa Xaa Xaa (SEQ ID NO: 50033)

Ser Tyr Ala Met Ser (SEQ ID NO: 50498)

Val Ile Ser Gly Arg Gly Gly Asn Thr Phe Tyr Ala Asp Ser Val Lys Gly (SEQ ID NO: 50499)

Arg Ile Ala Val Ala Gly Ser Glu Ala Phe Asp Ile (SEQ ID NO: 50500)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | | | | | H_FR1 | | | | | | | | | | |
| CONSENSUS | E | V | Q | L | L | E | S | - | G | G | G | L | V | Q | P | G | G | S | L | R | L | S | C | A | A | S |
| 21-225_8D3_HC | . | . | . | . | . | . | . | . | . | . | . | . | . | . | . | . | . | . | . | . | . | . | . | . | . | . |
| 21-225_8E12_HC | . | . | . | . | . | . | . | . | . | . | . | . | . | . | . | . | . | . | . | . | . | . | . | . | . | . |
| 21-225_8G6_HC | . | . | . | . | . | . | . | . | . | . | . | . | . | . | . | . | . | . | . | . | . | . | . | V | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | H_CDR1 | | | | | | | | | | | | | | H_FR2 | | | | | | | |
| CONSENSUS | E | . | F | T | F | S | S | . | . | . | . | . | Y | A | M | S | W | V | R | Q | A | P | G | K | G | L |
| 21-225_6D3_HC | . | . | . | . | . | . | . | . | . | . | . | . | . | . | . | N | . | . | . | . | . | . | . | . | . | . |
| 21-225_8E12_HC | . | . | . | . | . | . | . | . | . | . | . | . | . | . | . | . | . | . | . | . | . | . | . | . | . | . |
| 21-225_8G6_HC | . | . | . | . | . | . | . | . | . | . | . | . | . | V | . | N | . | . | . | . | . | . | . | . | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | | H_CDR2 | | | | | | | | | | | | |
| CONSENSUS | E | W | V | S | V | I | S | G | R | - | - | - | G | G | N | T | F | Y | A | D | S | V | K | G | R | F |
| 21-225_6D3_HC | . | . | . | . | . | . | . | . | . | . | . | . | . | . | . | . | . | . | . | . | . | . | . | . | . | . |
| 21-225_8E12_HC | . | . | . | . | — | . | . | . | . | . | . | . | . | . | . | . | . | . | . | . | . | . | . | . | . | . |
| 21-225_8G6_HC | . | . | . | . | . | . | . | . | . | . | . | . | . | . | . | . | . | . | . | . | . | . | . | . | . | . |

FIGURE 57 (Continued)

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | | | | H_FR3 | | | | | | | | | | | |
| CONSENSUS | T | I | S | R | D | N | S | K | N | T | L | Y | L | Q | M | N | S | L | R | A | E | D | T | A | V | Y |
| 21-225_6D3_HC | . | . | . | . | . | . | . | . | . | . | . | . | . | . | . | . | . | . | . | . | . | . | . | . | . | . |
| 21-225_8E12_HC | . | . | . | . | . | . | . | . | . | . | . | . | . | . | . | . | . | . | . | . | . | . | . | . | . | . |
| 21-225_8G6_HC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| CONSENSUS | Y | C | A | S | R | I | A | V | A | G | | | | | | | | | H_CDR3 | | | | | | | |
| 21-225_6D3_HC | F | . | . | . | . | L | . | . | . | . | . | . | . | . | . | . | . | . | . | . | . | . | . | . | . | . |
| 21-225_8E12_HC | . | . | . | . | . | X | . | . | . | . | . | . | . | . | . | . | . | . | . | . | . | . | . | . | . | . |
| 21-225_8G6_HC | . | . | . | . | . | L | . | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | HL_FR4 | | | | | |
| CONSENSUS | - | - | S | E | A | F | D | I | W | G | Q | G | T | M | V | T | V | S | S |
| 21-225_6D3_HC | . | . | . | . | . | . | . | . | . | . | . | . | . | . | . | . | . | . | . |
| 21-225_8E12_HC | . | . | . | . | . | . | . | . | . | . | . | . | . | . | . | S | . | . | . |
| 21-225_8G6_HC | . | . | . | . | . | . | . | . | . | . | . | . | . | . | . | . | . | . | . |

FIGURE 57 (Continued)

Table 60.   Consensus 26.- VH3j3-23/D5j5-12jRF3/JH6 (SEQ ID NO: 50277):

EVQLLES-GGGLVQPGGSLRLSCAASG-FTFSS-----YAMSWVRQAPGKGLEWVSAISGR---
GGSTFHADSVKGRFTISRDNSKNTLYLQMNSLRAEDTAVYYCVKGELLEDY...............YFYGMDVWGQGTTVTVSS wherein:

S at position 33 can be substituted with N

Y at position 39 can be substituted with C

A at position 40 can be substituted with V

S at position 42 can be substituted with N

A at position 57 can be substituted with T or S

I at position 58 can be substituted with L

G at position 60 can be substituted with R or V

R at position 61 can be substituted with G

S at position 67 can be substituted with N

T at position 68 can be substituted with I

F at position 69 can be substituted with Y

H at position 70 can be substituted with Y or N

V at position 74 can be substituted with E or M

G at position 109 can be substituted with W

E at position 110 can be substituted with G

E at position 113 can be substituted with Y

D at position 114 can be substituted with S or N

FIGURE 57 (Continued)

null (-) at position 116 can be substituted with E

Y at position 132 can be substituted with S

F at position 133 can be substituted with Y

Y at position 134 can be substituted with F

G at position 135 can be substituted with A

M at position 136 can be substituted with I or L

Xaa Xaa Xaa Met Xaa (SEQ ID NO: 50034)

Xaa Xaa Ser Xaa Xaa Gly Gly Xaa Xaa Xaa Xaa Ala Asp Ser Xaa Lys Gly (SEQ ID NO: 50035)

Xaa Xaa Leu Leu Xaa Xaa Tyr Xaa Xaa Xaa Xaa Xaa Xaa Asp Val (SEQ ID NO: 50036)

Ser Tyr Ala Met Ser (SEQ ID NO: 50501)

Ala Ile Ser Gly Arg Gly Gly Ser Thr Phe His Ala Asp Ser Val Lys Gly (SEQ ID NO: 50502)

Gly Glu Leu Leu Glu Asp Tyr Tyr Phe Tyr Gly Met Asp Val (SEQ ID NO: 50503)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | | H_CDR2 | | | | | | | | | | | | |
| CONSENSUS | E | W | V | S | A | I | S | G | R | . | . | . | G | S | T | T | Y | H | A | D | S | V | K | G | R | F |
| 21.225_4G12_HC | . | . | . | . | T | L | . | . | . | . | . | . | . | . | . | . | Y | Y | . | . | . | . | . | . | . | S |

Table 61. Consensus 27- VH3|3-33/D4|4-23|RF2/JH6 (SEQ ID NO: 50278):

QVQLVES-GGGVVQPGRSLRLSCAASG-FTFSS------YGMHWVRQAPGKGLEWVAVIWYD---
GSNKYYADSVKGRFTISRDNSKNTLYLQMNSLRAEDTAVYYCARDRVYCSSTSC---------PYYYYYGMDVWGQGTTVTVSS wherein:

S in position 33 can be substituted with G, D, R, H, T or N

G in position 40 can be substituted with V

M in position 41 can be substituted with L

H in position 42 can be substituted with N

V in position 57 can be substituted with L, F, I or D

I in position 58 can be substituted with F

W in position 59 can be substituted with R

Y in position 60 can be substituted with F

S in position 66 can be substituted with N or T

N in position 67 can be substituted with E, D or K

K in position 68 can be substituted with N or T

Y in position 69 can be substituted with S, D or N

Y in position 70 can be substituted with N

A in position 71 can be substituted with V

G in position 76 can be substituted with D

R in position 110 can be substituted with D, W or N

V in position 111 can be substituted with D, R, F or H

FIGURE 57 (Continued)

Y in position 112 can be substituted with S, E, G or F

C in position 113 can be substituted with G or E

S in position 114 can be substituted with G

S in position 115 can be substituted with G, R or N

T in position 116 can be substituted with null (-), S or P

S in position 117 can be substituted with P, null (-) or T

C in position 118 can be substituted with null (-)

null (-) in position 119 can be substituted with S, H, L or Y

P in position 129 can be substituted with null (-), S or Y

Y in position 130 can be substituted with null (-)

Y in position 131 can be substituted with null (-)

Y in position 132 can be substituted with null (-)

Y in position 134 can be substituted with F

G in position 135 can be substituted with A

M in position 136 can be substituted with L

Xaa Tyr Xaa Xaa (SEQ ID NO: 50037)

Xaa Xaa Xaa Asp Gly Xaa Xaa Xaa Xaa Xaa Asp Ser Val Lys Xaa (SEQ ID NO: 50038)

Asp Xaa Xaa Xaa Xaa Xaa Xaa Xaa Xaa Xaa Xaa Tyr Xaa Xaa Asp Val (SEQ ID NO: 50039)

Ser Tyr Gly Met His (SEQ ID NO: 50504)

FIGURE 57 (Continued)

Val Ile Trp Tyr Asp Gly Ser Asn Lys Tyr Tyr Ala Asp Ser Val Lys Gly (SEQ ID NO: 50505)

Asp Arg Val Tyr Cys Ser Ser Thr Ser Cys Pro Tyr Tyr Tyr Tyr Tyr Gly Met Asp Val (SEQ ID NO: 50506)

Table 62. Consensus 28- VH3|3-21/D|I1-1|RF2/JH4 (SEQ ID NO: 50279):

EVQLVES-GGGLVKPGGSLRLSCAASG-FTFSS------YSMNWVRQAPGKGLEWVSSISGS---
SSYIYYADSVKGRFTISRDNAKNSLYLQMNSLRAEDTAVYYCARVAS-------------FDYWGQGTLVTVSS wherein:

S at position 33 can be substituted with N

S at position 40 can be substituted with T, K, N or R

M at position 41 can be substituted with L

I at position 58 can be substituted with T

G at position 60 can be substituted with S

S at position 61 can be substituted with G, N or T

S at position 65 can be substituted with G, D or N

S at position 66 can be substituted with T

Y at position 67 can be substituted with F, D, L, N or S

I at position 68 can be substituted with M or T

Y at position 69 can be substituted with N

A at position 71 can be substituted with T

A at position 110 can be substituted with N or S

S at position 111 can be substituted with A, G, T, L, H or N

F at position 136 can be substituted with L or N

Y at position 138 can be substituted with C or S

Xaa Tyr Xaa Xaa Asn (SEQ ID NO: 50040)

FIGURE 57 (Continued)

Ser Xaa Ser Xaa Xaa Xaa Xaa Xaa Tyr Xaa Asp Ser Val Lys Gly (SEQ ID NO: 50041)

Val Xaa Xaa Xaa Asp Xaa (SEQ ID NO: 50042)

Ser Tyr Ser Met Asn (SEQ ID NO: 50507)

Ser Ile Ser Gly Ser Ser Ser Tyr Ile Tyr Tyr Ala Asp Ser Val Lys Gly (SEQ ID NO: 50508)

Val Ala Ser Phe Asp Tyr (SEQ ID NO: 50509)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | H_FR4 | | | | | |
| CONSENSUS | . | . | . | . | . | F | D | Y | W | G | Q | G | T | L | V | T | V | S | S |
| 21-225_14D6_HC | . | . | . | . | . | . | . | . | . | . | . | . | . | . | . | . | . | . | . |
| 21-225_157E4_HC | . | . | . | . | . | . | . | . | . | . | . | . | . | . | . | . | . | . | . |
| 21-225_157H10_HC | . | . | . | . | . | . | . | . | . | . | . | . | . | . | . | . | . | . | . |
| 21-225_15A2_HC | . | . | . | . | . | . | . | . | . | . | . | . | . | . | . | . | . | . | . |
| 21-225_16A11_HC | . | . | . | . | . | . | . | . | . | . | . | . | . | . | . | . | . | . | . |
| 21-225_16B8_HC | . | . | . | . | . | . | . | . | . | . | . | . | . | . | . | . | . | . | . |
| 21-225_16H1_HC | . | . | . | . | . | . | . | . | . | . | . | . | . | . | . | . | . | . | . |
| 21-225_17H5_HC | . | . | . | . | . | . | . | . | . | . | . | . | . | . | . | . | . | . | . |
| 21-225_17H8_HC | . | . | . | . | . | . | . | . | . | . | . | . | . | . | . | . | . | . | . |
| 21-225_1F1_HC | . | . | . | . | . | L | . | . | . | . | . | . | . | . | . | . | . | . | . |
| 21-225_20H7_HC | . | . | . | . | . | L | . | S | . | . | . | . | . | . | . | . | . | . | . |
| 21-225_22B12_HC | . | . | . | . | . | . | . | C | . | . | . | . | . | . | . | . | . | . | . |
| 21-225_23A11_HC | . | . | . | . | . | . | . | . | . | . | . | . | . | . | . | . | . | . | . |
| 21-225_27C5_HC | . | . | . | . | . | . | . | . | . | . | . | . | . | . | . | . | . | . | . |
| 21-225_27H12_HC | . | . | . | . | . | . | . | . | . | . | . | . | . | . | . | . | . | . | . |
| 21-225_2A4_HC | . | . | . | . | . | . | . | . | . | . | . | . | . | . | . | . | . | . | . |
| 21-225_2C12_HC | . | . | . | . | . | . | . | . | . | . | . | . | . | . | . | . | . | . | . |
| 21-225_32B3_HC | . | . | . | . | . | . | . | . | . | . | . | . | . | . | . | . | . | . | . |
| 21-225_35H8_HC | . | . | . | . | . | . | . | . | . | . | . | . | . | . | . | . | . | . | . |
| 21-225_50G10_HC | . | . | . | . | . | N | . | . | . | . | . | . | . | . | . | . | . | . | . |
| 21-225_52E3_HC | . | . | . | . | . | . | . | . | . | . | . | . | . | . | . | . | . | . | . |
| 21-225_52H12_HC | . | . | . | . | . | . | . | . | . | . | . | . | . | . | . | . | . | . | . |
| 21-225_56A5_HC | . | . | . | . | . | . | . | . | . | . | . | . | . | . | . | . | . | . | . |
| 21-225_56H1_HC | . | . | . | . | . | . | . | . | . | . | . | . | . | . | . | . | . | . | . |
| 21-225_57B2_HC | . | . | . | . | . | . | . | . | . | . | . | . | . | . | . | . | . | . | . |
| 21-225_5E11_HC | . | . | . | . | . | . | . | . | . | . | . | . | . | . | . | . | . | . | . |
| 21-225_5F4_HC | . | . | . | . | . | . | . | . | . | . | . | . | . | . | . | . | . | . | . |
| 21-225_70E12_HC | . | . | . | . | . | . | . | C | . | . | . | . | . | . | . | . | . | . | . |

FIGURE 57 (Continued)

Table 63. Consensus 29-VH4|4-30.1/D3|3-22|RF2/JH6 (SEQ ID NO: 50280):

QVQLQES-GPGLVKPSQTLSLTCTVSG-GSISSG---DYYWNWIRQHPGKGLEWIGYIFY----SGSTYYNPSLKSRVTISVDTSKNQFSLKLSSVTAADTAVYYCARGDYDGSGSY--------HYYYGMDVWGQGTTVTVSS wherein:

G at position 34 can be substituted with V

D at position 38 can be substituted with V, G or S

Y at position 40 can be substituted with H

N at position 42 can be substituted with S

Y at position 57 can be substituted with N or F

I at position 58 can be substituted with L

F at position 59 can be substituted with Y or H

Y at position 60 can be substituted with H

Y at position 70 can be substituted with N

K at position 75 can be substituted with R

Y at position 132 can be substituted with F or H

Y at position 134 can be substituted with H

M at position 136 can be substituted with L

Ser Xaa Xaa Tyr Xaa Trp Xaa (SEQ ID NO: 50230)

Xaa Xaa Xaa Ser Gly Ser Thr Tyr Xaa Asn Pro Ser Leu Xaa Ser (SEQ ID NO: 50231)

Gly Asp Tyr Asp Gly Ser Gly Ser Tyr His Xaa Tyr Xaa Gly Xaa Asp Val (SEQ ID NO: 50232)

Ser Gly Asp Tyr Tyr Trp Asn (SEQ ID NO: 50510)

FIGURE 57 (Continued)

Tyr Ile Phe Tyr Ser Gly Ser Thr Tyr Tyr Asn Pro Ser Leu Lys Ser (SEQ ID NO: 50511)

Gly Asp Tyr Asp Gly Ser Gly Ser Tyr His Tyr Tyr Tyr Gly Met Asp Val (SEQ ID NO: 50512)

Table 64. Consensus 30- VH3|3-23/D7|7-27|RF1/JH6 (SEQ ID NO: 50281):

EVQLLES-GGGLVQPGGSLRLSCAASG-FTFSS-----YAMSWVRQAPGKGLEWVSVISGG----GSSTYYADSVKGRFTISRDNSKNTLYLQMNSLRAEDTAVYYCAKWRGNPT............DYGMDVWGQGTTVTVSS wherein:

S at position 33 can be substituted with N or T

Y at position 39 can be substituted with H

A at position 40 can be substituted with P or V

V at position 57 can be substituted with A or I

G at position 61 can be substituted with S

S at position 66 can be substituted with G or T

S at position 67 can be substituted with T

T at position 68 can be substituted with A

W at position 109 can be substituted with A

R at position 110 can be substituted with G

N at position 112 can be substituted with T

P at position 113 can be substituted with T

T at position 114 can be substituted with G null (-) at position 115 can be substituted with S null (-) at position 116 can be substituted with Y null (-) at position 132 can be substituted with Y D at position 133 can be substituted with Y FIGURE 57 (Continued)

Y at position 134 can be substituted with N or S

Xaa Xaa Xaa Met Ser (SEQ ID NO: 50043)

Xaa Ile Ser Gly Xaa Gly Xaa Xaa Xaa Tyr Tyr Ala Asp Ser Val Lys Gly (SEQ ID NO: 50044)

Xaa Xaa Gly Xaa Xaa Xaa Xaa Xaa Xaa Gly Met Asp (SEQ ID NO: 50045)

Ser Tyr Ala Met Ser (SEQ ID NO: 50513)

Val Ile Ser Gly Gly Gly Ser Thr Tyr Tyr Ala Asp Ser Val Lys Gly (SEQ ID NO: 50514)

Trp Arg Gly Asn Pro Thr Asp Tyr Gly Met Asp (SEQ ID NO: 50515)

| Reference # | 105 Y | 106 C | 107 A | 108 K | 109 W | 110 R | 111 G | 112 N | 113 P | 114 T | 115 | 116 | 117 | 118 | 119 | 120 | 121 | 122 | 123 H_CDR3 | 124 | 125 | 126 | 127 | 128 | 129 | 130 |
|---|---|---|---|---|---|---|---|---|---|---|---|---|---|---|---|---|---|---|---|---|---|---|---|---|---|---|
| CONSENSUS | Y | C | A | K | W | R | G | N | P | T | | | | | | | | | | | | | | | | |
| 21-225_146A2_HC | . | . | . | . | . | . | . | . | . | . | . | . | . | . | . | . | . | . | . | . | . | . | . | . | . | . |
| 21-225_146A3_HC | . | . | . | . | . | . | . | . | . | . | . | . | . | . | . | . | . | . | . | . | . | . | . | . | . | . |
| 21-225_146B11_HC | . | . | . | . | . | . | . | . | . | . | . | . | . | . | . | . | . | . | . | . | . | . | . | . | . | . |
| 21-225_146C11_HC | . | . | . | . | . | . | . | . | . | . | . | . | . | . | . | . | . | . | . | . | . | . | . | . | . | . |
| 21-225_147B12_HC | . | . | . | . | . | . | . | . | . | . | . | . | . | . | . | . | . | . | . | . | . | . | . | . | . | . |
| 21-225_147E11_HC | . | . | . | . | . | . | . | . | . | . | . | . | . | . | . | . | . | . | . | . | . | . | . | . | . | . |
| 21-225_147E7_HC | . | . | . | . | . | . | . | . | . | . | . | . | . | . | . | . | . | . | . | . | . | . | . | . | . | . |
| 21-225_148C6_HC | . | . | . | . | . | . | . | . | . | . | . | . | . | . | . | . | . | . | . | . | . | . | . | . | . | . |
| 21-225_148G11_HC | . | . | . | . | . | . | . | . | . | . | . | . | . | . | . | . | . | . | . | . | . | . | . | . | . | . |
| 21-225_148G6_HC | . | . | . | . | . | . | . | . | . | . | . | . | . | . | . | . | . | . | . | . | . | . | . | . | . | . |
| 21-225_148H11_HC | . | . | . | . | . | . | . | . | . | . | . | . | . | . | . | . | . | . | . | . | . | . | . | . | . | . |
| 21-225_149C10_HC | . | . | . | . | . | . | . | . | . | . | . | . | . | . | . | . | . | . | . | . | . | . | . | . | . | . |
| 21-225_149C7_HC | . | . | . | . | . | . | . | . | . | . | . | . | . | . | . | . | . | . | . | . | . | . | . | . | . | . |
| 21-225_150F6_HC | . | . | . | . | . | . | . | . | . | . | . | . | . | . | . | . | . | . | . | . | . | . | . | . | . | . |
| 21-225_150H11_HC | . | . | . | . | . | . | . | . | . | . | . | . | . | . | . | . | . | . | . | . | . | . | . | . | . | . |
| 21-225_151B9_HC | . | . | . | . | . | . | . | . | . | . | . | . | . | . | . | . | . | . | . | . | . | . | . | . | . | . |
| 21-225_151H5_HC | . | . | . | . | . | . | . | . | . | . | . | . | . | . | . | . | . | . | . | . | . | . | . | . | . | . |
| 21-225_151H7_HC | . | . | . | . | . | . | . | . | . | . | . | . | . | . | . | . | . | . | . | . | . | . | . | . | . | . |
| 21-225_152D7_HC | . | . | . | . | . | . | . | . | . | . | . | . | . | . | . | . | . | . | . | . | . | . | . | . | . | . |
| 21-225_152G6_HC | . | . | . | . | . | . | . | . | . | . | . | . | . | . | . | . | . | . | . | . | . | . | . | . | . | . |
| 21-225_154C4_HC | . | . | . | . | . | . | . | . | . | . | . | . | . | . | . | . | . | . | . | . | . | . | . | . | . | . |
| 21-225_154E10_HC | . | . | . | . | . | . | . | . | . | . | . | . | . | . | . | . | . | . | . | . | . | . | . | . | . | . |
| 21-225_155C10_HC | . | . | . | . | . | . | . | . | . | . | . | . | . | . | . | . | . | . | . | . | . | . | . | . | . | . |
| 21-225_207C9_HC | . | . | . | K | W | G | . | T | T | Q | S | Y | . | . | . | . | . | . | . | . | . | . | . | . | . | . |

FIGURE 57 (Continued)

Table 65. Consensus 31-VH3j3-33/D4j4-17|RF2/JH4 (SEQ ID NO: 50282):

QVQLVES-GGGVVQPGRSLRLSCAASG-FTFSS-----YGMHWVRQAPGKGLEWVAIIWYD---
GSNKYYADSVKGRFTISRDNSKNTLYLQMNSLRAEDTAVYYCARDHYDFW----------SGHFDYWGQGTLVTVSS wherein:

S at position 33 can be substituted with N or T

M at position 41 can be substituted with L

I at position 57 can be substituted with V or A

I at position 58 can be substituted with M

S at position 66 can be substituted with T

N at position 67 can be substituted with Y or S

A at position 71 can be substituted with G, T or V

D at position 109 can be substituted with E

H at position 110 can be substituted with R, Q, A, G, T or Y

Y at position 111 can be substituted with G, F or H

D at position 112 can be substituted with I or F

F at position 113 can be substituted with V or L

W at position 114 can be substituted with G or null (-)

S at position 133 can be substituted with A or null (-)

G at position 134 can be substituted with T or E

H at position 135 can be substituted with Y, W or F

F at position 136 can be substituted with L or S

FIGURE 57 (Continued)

D at position 137 can be substituted with A, C or G

Y at position 138 can be substituted with F or S

Xaa Tyr Gly Xaa His (SEQ ID NO: 50253)

Xaa Xaa Trp Tyr Asp Gly Xaa Xaa Lys Tyr Tyr Xaa Asp Ser Val Lys Gly (SEQ ID NO: 50254)

Xaa Xaa Xaa Xaa Xaa Xaa Xaa Xaa Xaa Xaa Xaa (SEQ ID NO: 50255)

Ser Tyr Gly Met His (SEQ ID NO: 50516)

Ile Ile Trp Tyr Asp Gly Ser Asn Lys Tyr Tyr Ala Asp Ser Val Lys Gly (SEQ ID NO: 50517)

Asp His Tyr Asp Phe Trp Ser Gly His Phe Asp Tyr (SEQ ID NO: 50518)

Table 66. Consensus 32 - VH4|4-34/D4|4-17|RF2/JH4 (SEQ ID NO: 50283):

QVQLQQW-GAGLLKPSETLSLTCAVYG-GSFSG-----YYWSWIRQPPGKGLEWIGEINH-----
SGRTNYNPSLKSRVTISVDTSKNQFSLKLSSVTAADTAVYYCARDYGG------------LDYWGQGTLVTVSS wherein:

G at position 33 can be substituted with V, P, A, D or Y

Y at position 39 can be substituted with C, S or P

Y at position 40 can be substituted with F

I at position 58 can be substituted with S or V

H at position 60 can be substituted with I or Q

R at position 67 can be substituted with S

T at position 68 can be substituted with A or S

N at position 69 can be substituted with T

Y at position 70 can be substituted with F

Xaa Xaa Xaa Trp Ser (SEQ ID NO: 50233)

Glu Xaa Asn Xaa Ser Gly Xaa Xaa Xaa Xaa Asn Pro Ser Leu Lys Ser (SEQ ID NO: 50234)

Asp Tyr Gly Gly Leu Asp Tyr (SEQ ID NO: 50235)

Gly Tyr Tyr Trp Ser (SEQ ID NO: 50519)

Glu Ile Asn His Ser Gly Arg Thr Asn Tyr Asn Pro Ser Leu Lys Ser (SEQ ID NO: 50520)

Asp Tyr Gly Gly Leu Asp Tyr (SEQ ID NO: 50521)

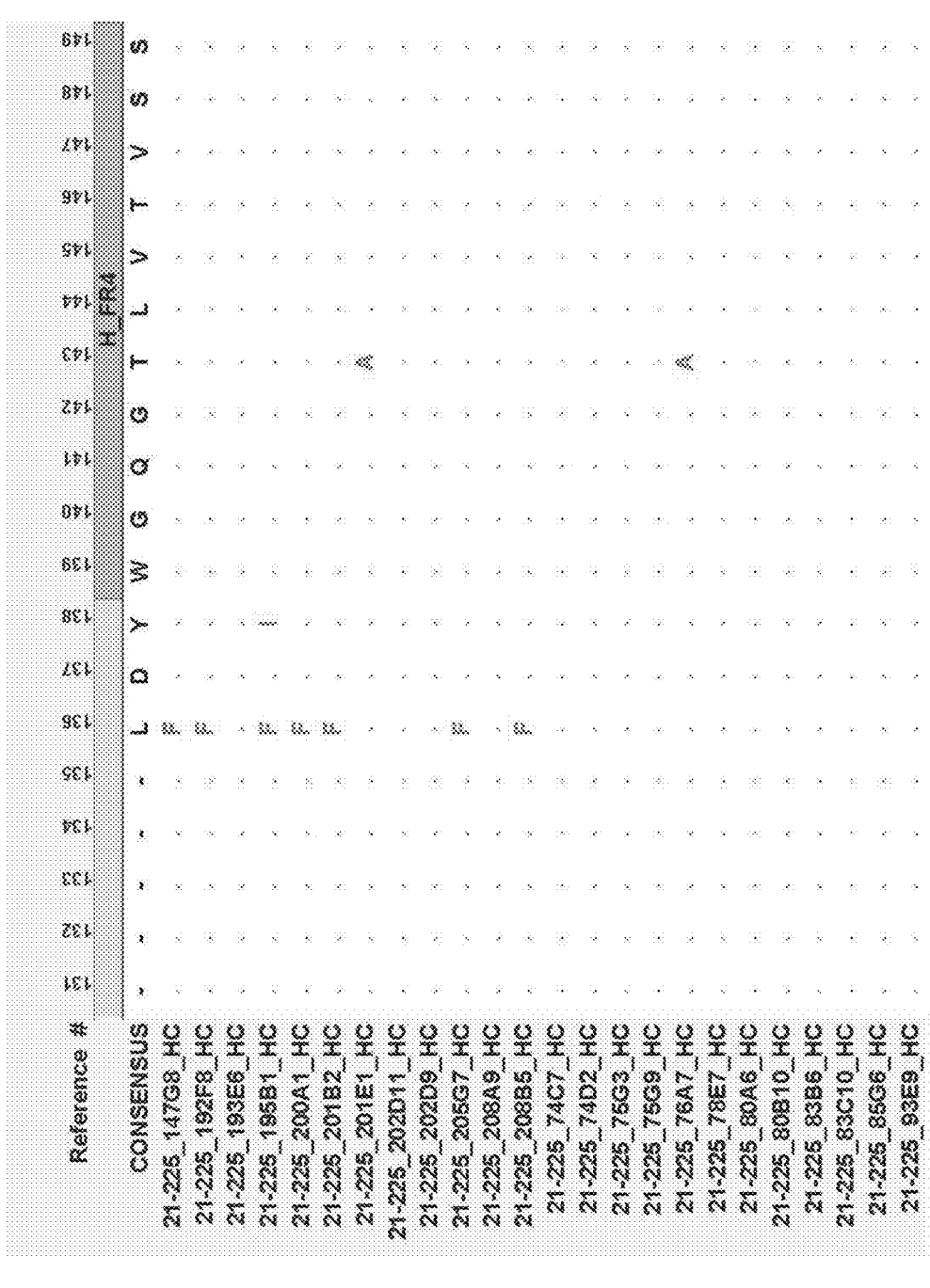

FIGURE 57 (Continued)

Table 67.    Consensus 33-VH4|4-39/D|1-26|RF3/JH4 (SEQ ID NO: 50284):

QLQLQES-GPGL VKPSETLSLTCTVSG-GSISRS---SYYWGWIRQPPGKGLEWIGNIYY----
SGSTYYNPSLKSRVTISVDTSKNQFSLKLSSVTAADTAVYYCARHSSSW----------SLDYWGQGTLVTVSS wherein:

R in position 33 can be substituted with G

S in position 38 can be substituted with N

Y in position 39 can be substituted with S

N in position 57 can be substituted with S

S in position 67 can be substituted with Y, A, T or I

T in position 68 can be substituted with A, P or S

Y in position 69 can be substituted with Q, S, A or N

Y in position 70 can be substituted with C or H

N in position 71 can be substituted with I or T

H in position 109 can be substituted with L

S in position 111 can be substituted with T or G

L in position 136 can be substituted with F, I or V

Y in position 138 can be substituted with N, C, D or F

Xaa Ser Xaa Xaa Tyr Trp Gly (SEQ ID NO: 50046)

Xaa Ile Tyr Tyr Ser Gly Xaa Xaa Xaa Xaa Pro Ser Leu Lys Ser (SEQ ID NO: 50047)

Xaa Ser Xaa Ser Trp Ser Xaa Asp Xaa (SEQ ID NO: 50048)

Arg Ser Ser Tyr Tyr Trp Gly (SEQ ID NO: 50522)

Asn Ile Tyr Tyr Ser Gly Ser Thr Tyr Tyr Asn Pro Ser Leu Lys Ser (SEQ ID NO: 50523)

His Ser Ser Ser Trp Ser Leu Asp Tyr (SEQ ID NO: 50524)

| Reference # | 105 | 106 | 107 | 108 | 109 | 110 | 111 | 112 | 113 | 114-130 (H_CDR3) |
|---|---|---|---|---|---|---|---|---|---|---|
| CONSENSUS | Y | C | A | R | H | S | S | S | W | |
| 21-225_11F10_HC | . | . | . | . | L | . | . | . | . | |
| 21-225_15A1_HC | . | . | . | . | L | . | . | . | . | |
| 21-225_15G7_HC | . | . | . | . | L | . | T | . | . | |
| 21-225_15H1_HC | . | . | . | . | . | . | T | . | . | |
| 21-225_16A1_HC | . | . | . | . | L | . | . | . | . | |
| 21-225_18A3_HC | . | . | . | . | . | . | T | . | . | |
| 21-225_18C6_HC | . | . | . | . | L | . | . | . | . | |
| 21-225_20C2_HC | . | . | . | . | . | . | . | . | . | |
| 21-225_20G9_HC | . | . | . | . | L | . | T | . | . | |
| 21-225_21G7_HC | . | . | . | . | . | . | Q | . | . | |
| 21-225_22C1_HC | . | . | . | . | . | . | . | . | . | |
| 21-225_22D12_HC | . | . | . | . | L | . | . | . | . | |
| 21-225_22G9_HC | . | . | . | . | L | . | . | . | . | |
| 21-225_23D1_HC | . | . | . | . | L | . | . | . | . | |
| 21-225_24E5_HC | . | . | . | . | . | . | . | . | . | |
| 21-225_34C4_HC | . | . | . | . | . | . | . | . | . | |
| 21-225_59E6_HC | . | . | . | . | . | . | T | . | . | |
| 21-225_68D12_HC | . | . | . | . | . | . | . | . | . | |
| 21-225_6A6_HC | . | . | . | . | . | . | . | . | . | |
| 21-225_6D4_HC | . | . | . | . | . | . | Q | . | . | |
| 21-225_7F4_HC | . | . | . | . | . | . | . | . | . | |
| 21-225_8D12_HC | . | . | . | . | . | . | T | . | . | |

FIGURE 57 (Continued)

| Reference # | 131 | 132 | 133 | 134 | 135 | 136 | 137 | 138 | 139 | 140 | 141 | 142 | 143 | 144 H_FR3 | 145 | 146 | 147 | 148 | 149 |
|---|---|---|---|---|---|---|---|---|---|---|---|---|---|---|---|---|---|---|---|
| CONSENSUS | | | | | S | L | D | Y | W | G | Q | G | T | L | V | T | V | S | S |
| 21-225_11F10_HC | | | | | | R | | | | | | | | | | | | | |
| 21-225_15A1_HC | | | | | | P | | F | | | | | | | | | | | |
| 21-225_15G7_HC | | | | | | P | | | | | | | | | | | | | |
| 21-225_15H1_HC | | | | | | P | | | | | | | | | | | | | |
| 21-225_16A1_HC | | | | | | | | | | | | | | | | | | | |
| 21-225_18A3_HC | | | | | | | | D | | | | | | | | | | | |
| 21-225_18C6_HC | | | | | | R | | N | | | | | | | | | | | |
| 21-225_20C2_HC | | | | | | | | | | | | | | | | | | | |
| 21-225_20G9_HC | | | | | | V | | | | | | | | | | | | | |
| 21-225_21G7_HC | | | | | | R | | | | | | | | | | | | | |
| 21-225_22C1_HC | | | | | | R | | N | | | | | | | | | | | |
| 21-225_22D12_HC | | | | | | — | | | | | | | | | | | | | |
| 21-225_22G9_HC | | | | | | R | | | | | | | | | | | | | |
| 21-225_23D1_HC | | | | | | | | | | | | | | | | | | | |
| 21-225_24E5_HC | | | | | | | | | | | | | | | | | | | |
| 21-225_34C4_HC | | | | | | | | | | | | | | | | | | | |
| 21-225_59E6_HC | | | | | | | | | | | | | | | | | | | |
| 21-225_68D12_HC | | | | | | | | Q | | | | | | | | | | | |
| 21-225_6A6_HC | | | | | | | | | | | | | | | | | | | |
| 21-225_6D4_HC | | | | | | | | | | | | | | | | | | | |
| 21-225_7F4_HC | | | | | | | | | | | | | | | | | | | |
| 21-225_8D12_HC | | | | | | | | | | | | | | | | | | | |

FIGURE 57 (Continued)

Table 68. Consensus 34-VH1j1-02/D5|5-18|RF3/JH5 (SEQ ID NO: 50285):

QVQLVQS-GAEVKKPGASVKVSCKASG-YTFTG-----YYIHWVRQAPGQGLEWMGWINPN---SGGTNYAQKFQGRVTMTRDTSISTAYMELSRLRSDDTAVYYCARGYSYGY----------NWFDPWGQGTLVTVSS wherein:

G in position 33 can be substituted with D

Y in position 39 can be substituted with H

Y in position 40 can be substituted with F

I in position 41 can be substituted with M

H in position 42 can be substituted with N

P in position 60 can be substituted with S

N in position 61 can be substituted with K

S in position 65 can be substituted with N

G in position 66 can be substituted with D

G in position 67 can be substituted with D

A in position 71 can be substituted with E

Q in position 72 can be substituted with E

G in position 76 can be substituted with D

G in position 109 can be substituted with D

Y in position 110 can be substituted with G, T or F

S in position 111 can be substituted with Y, D or R

Y in position 112 can be substituted with S

FIGURE 57 (Continued)

G in position 113 can be substituted with null (-) or S

Y in position 114 can be substituted with S or null (-)

null (-) in position 115 can be substituted with G null (-) in position 116 can be substituted with S null (-) in position 132 can be substituted with Y null (-) in position 133 can be substituted with Y, F or H N in position 134 can be substituted with null (-) or D W in position 135 can be substituted with null (-), D or E F in position 136 can be substituted with L D in position 137 can be substituted with A P in position 138 can be substituted with S Xaa Xaa Xaa Xaa (SEQ ID NO: 50049)

Trp Ile Asn Xaa Xaa Xaa Xaa Xaa Thr Asn Tyr Xaa Xaa Lys Phe Gln Xaa (SEQ ID NO: 50050)

Xaa Xaa Xaa Xaa Xaa Xaa Xaa Xaa Xaa Xaa Xaa Xaa Xaa Xaa Xaa (SEQ ID NO: 50051)

Gly Tyr Tyr Ile His (SEQ ID NO: 50525)

Trp Ile Asn Pro Asn Ser Gly Gly Thr Asn Tyr Ala Gln Lys Phe Gln Gly (SEQ ID NO: 50526)

Gly Tyr Ser Tyr Gly Tyr Asn Trp Phe Asp Pro (SEQ ID NO: 50527)

| Reference # | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|---|
| | | | | | | | | | | | | | | | | | | H_CDR3 | | | | | | | |
| CONSENSUS | T | A | V | Y | Y | C | A | R | G | Y | S | Y | G | Y | | | | | | | | | | | |
| 21-225_17G4_HC | . | . | . | . | . | . | . | S | . | . | . | . | . | . | . | . | . | . | . | . | . | . | . | . | . |
| 21-225_19A1_HC | . | . | . | . | . | . | . | S | . | . | . | . | . | . | . | . | . | . | . | . | . | . | . | . | . |
| 21-225_201H10_HC | . | . | . | . | . | . | . | . | . | . | . | . | . | . | . | . | . | . | . | . | . | . | . | . | . |
| 21-225_203E3_HC | . | . | . | . | . | . | . | . | . | . | . | . | . | . | . | . | . | . | . | . | . | . | . | . | . |
| 21-225_204H4_HC | . | . | . | . | . | . | . | . | . | . | . | . | . | . | . | . | . | . | . | . | . | . | . | . | . |
| 21-225_206A4_HC | . | . | . | . | . | . | . | . | . | . | . | . | . | . | . | . | . | . | . | . | . | . | . | . | . |
| 21-225_206A5_HC | . | . | . | . | . | . | . | . | . | . | . | . | . | . | . | . | . | . | . | . | . | . | . | . | . |
| 21-225_208B11_HC | . | . | . | . | . | . | . | . | . | . | . | . | . | . | . | . | . | . | . | . | . | . | . | . | . |
| 21-225_208E8_HC | . | . | . | . | . | . | . | . | . | . | . | . | . | . | . | . | . | . | . | . | . | . | . | . | . |
| 21-225_210B12_HC | . | . | . | . | . | . | . | . | D | G | D | S | . | . | . | . | . | . | . | . | . | . | . | . | . |
| 21-225_210D11_HC | . | . | . | . | . | . | . | . | . | G | . | S | S | . | . | . | . | . | . | . | . | . | . | . | . |
| 21-225_213A7_HC | . | . | . | . | . | . | . | . | D | G | D | . | . | . | . | . | . | . | . | . | . | . | . | . | . |
| 21-225_214H8_HC | . | . | . | . | . | . | . | K | . | T | E | . | . | S | S | S | . | . | . | . | . | . | . | . | . |
| 21-225_215H6_HC | . | . | . | . | . | . | . | K | . | T | Y | . | . | S | S | S | . | . | . | . | . | . | . | . | . |
| 21-225_226A10_HC | . | . | . | . | . | . | . | . | . | . | Y | . | . | S | S | S | . | . | . | . | . | . | . | . | . |
| 21-225_226B2_HC | . | . | . | . | . | . | . | . | . | . | Y | . | . | S | S | S | . | . | . | . | . | . | . | . | . |
| 21-225_226B7_HC | . | . | . | . | . | . | . | . | . | F | Y | . | . | S | S | S | . | . | . | . | . | . | . | . | . |
| 21-225_32B11_HC | . | . | . | . | . | . | . | . | . | . | Y | . | . | S | S | S | . | . | . | . | . | . | . | . | . |
| 21-225_34D7_HC | . | . | . | . | . | . | . | . | . | . | Y | . | . | S | S | S | . | . | . | . | . | . | . | . | . |

FIGURE 57 (Continued)

Table 69. Consensus 35- VH3|3-33/D1|1-1|RF3/JH6 (SEQ ID NO: 50286):

QVQLVES-GGGVVQPGRSLRLSCAASG-FTFSH......YGMHWVRQAPGKGLEWVAVIWYD-
GSNKYYADSVKGRFTISRDNSKNTLYLQMNSLRAEDTAVYYCARGDWNP............EGMDVWGQGTTVTVSS wherein:

H in position 33 can be substituted with N

Y in position 39 can be substituted with S

V in position 57 can be substituted with I

W in position 59 can be substituted with Y

N in position 67 can be substituted with Y

K in position 68 can be substituted with E

Y in position 70 can be substituted with C or N

G in position 109 can be substituted with D

D in position 110 can be substituted with R

W in position 111 can be substituted with H

N in position 112 can be substituted with Y

P in position 113 can be substituted with D null (-) in position 114 can be substituted with F null (-) in position 115 can be substituted with H null (-) in position 116 can be substituted with V null (-) in position 117 can be substituted with P FIGURE 57 (Continued)

null (-) in position 130 can be substituted with Y
null (-) in position 131 can be substituted with Y
null (-) in position 132 can be substituted with Y
null (-) in position 133 can be substituted with Y
E in position 134 can be substituted with Y
M in position 136 can be substituted with L
Xaa Xaa Gly Met His (SEQ ID NO: 50052)
Xaa Ile Xaa Tyr Asp Gly Ser Xaa Xaa Xaa Tyr Ala Asp Ser Val Lys Gly (SEQ ID NO: 50053)
Xaa Xaa Xaa Xaa Xaa Xaa Xaa Xaa Xaa Xaa Gly Xaa Xaa Asp Val (SEQ ID NO: 50054)
His Tyr Gly Met His (SEQ ID NO: 50528)
Val Ile Trp Tyr Asp Gly Ser Asn Lys Tyr Tyr Ala Asp Ser Val Lys Gly (SEQ ID NO: 50529)
Gly Asp Trp Asn Pro Glu Gly Met Asp Val (SEQ ID NO: 50530)

| Reference # | 26 | 27 | 28 | 29 | 30 | 31 | 32 | 33 | 34 | 35 | 36 | 37 H_CDR1 | 38 | 39 | 40 | 41 | 42 | 43 | 44 | 45 | 46 | 47 | 48 | 49 | 50 H_FR2 |
|---|---|---|---|---|---|---|---|---|---|---|---|---|---|---|---|---|---|---|---|---|---|---|---|---|---|
| CONSENSUS | S | G | . | F | T | F | S | H | . | . | . | . | Y | G | M | H | W | V | R | Q | A | P | G | K |
| 21-225_179C7_HC | | | | | | | N | | | | | | | | | | | | | | Q | | | |
| 21-225_210D12_HC | | | | | | | | | | | | | | | | | | | | | | | | |
| 21-225_210E12_HC | | | | | | | N | | | | | | | | | | | | | | | | | |
| 21-225_211C1_HC | | | | | | | | | | | | | | | | | | | | | | | | |
| 21-225_211G5_HC | | | | | | | N | | | | | | | | | | | | | | | | | |
| 21-225_212A4_HC | | | | | | | | | | | | | | | | | | | | | | | | |
| 21-225_212C2_HC | | | | | | | | | | | | | | | | | | | | | | | | |
| 21-225_212F6_HC | | | | | | | | | | | | | | | | | | | | | | | | |
| 21-225_212G7_HC | | | | | | | | | | | | | | | | | | | | | | | | |
| 21-225_213D5_HC | | | | | | | | | | | | | | | | | | | | | | | | |
| 21-225_213G3_HC | | | | | | | N | | | | | | | | | | | | | | | | | |
| 21-225_215D3_HC | | | | | | | N | | | | | | | | | | | | | | | | | |
| 21-225_216A3_HC | | | | | | | | | | | | | | | | | | | | | | | | |
| 21-225_216G1_HC | | | | | | | | | | | | | | | | | | | | | | | | |
| 21-225_217B2_HC | | | | | | | | | | | | | | | | | | | | | | | | |
| 21-225_219A7_HC | | | | | | | | | | | | | | | | | | | | | | | | |
| 21-225_221G4_HC | | | | | | | | | | | | | | | | | | | | | | | | |
| 21-225_221H2_HC | | | | | | | | | | | | | | | | | | | | | | | | |

| Reference # | 101 | 102 | 103 | 104 | 105 | 106 | 107 | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|---|---|---|---|---|---|---|
| | | | | | | | | | | | | | | | | | | | | | | | H_CDR3 | | |
| CONSENSUS | T | A | V | Y | Y | C | A | R | G | D | W | N | P | F | M | V | & | . | . | . | . | . | . | . | . |
| 21-225_179C7_HC | . | . | . | . | . | . | . | . | . | . | . | . | . | . | . | . | . | . | . | . | . | . | . | . | . |
| 21-225_210D12_HC | . | . | . | . | . | . | . | . | . | . | . | . | . | . | . | . | . | . | . | . | . | . | . | . | . |
| 21-225_210E12_HC | . | . | . | . | . | . | . | . | . | . | . | . | . | . | . | . | . | . | . | . | . | . | . | . | . |
| 21-225_211C1_HC | . | . | . | . | . | . | . | . | . | . | . | . | . | . | . | . | . | . | . | . | . | . | . | . | . |
| 21-225_211G5_HC | . | . | . | . | . | . | . | . | . | . | . | . | . | . | . | . | . | . | . | . | . | . | . | . | . |
| 21-225_212A4_HC | . | . | . | . | . | . | . | . | . | . | . | . | . | . | . | . | . | . | . | . | . | . | . | . | . |
| 21-225_212C2_HC | . | . | . | . | . | . | . | . | . | . | . | . | . | . | . | . | . | . | . | . | . | . | . | . | . |
| 21-225_212F6_HC | . | . | . | . | . | . | . | . | . | . | . | . | . | . | . | . | . | . | . | . | . | . | . | . | . |
| 21-225_212G7_HC | . | . | . | . | . | . | . | . | . | . | . | . | . | . | . | . | . | . | . | . | . | . | . | . | . |
| 21-225_213D5_HC | . | . | . | . | . | . | . | . | . | . | . | . | . | . | . | . | . | . | . | . | . | . | . | . | . |
| 21-225_213G3_HC | . | . | . | . | . | . | . | . | . | . | . | . | . | . | . | . | . | . | . | . | . | . | . | . | . |
| 21-225_215D3_HC | . | . | . | . | . | . | . | . | . | . | . | . | . | . | . | . | . | . | . | . | . | . | . | . | . |
| 21-225_216A3_HC | . | . | . | . | . | . | . | . | . | . | . | . | . | . | . | . | . | . | . | . | . | . | . | . | . |
| 21-225_216G1_HC | . | . | . | . | . | . | . | . | . | . | . | . | . | . | . | . | . | . | . | . | . | . | . | . | . |
| 21-225_217B2_HC | . | . | . | . | . | . | . | . | . | . | . | . | . | . | . | . | . | . | . | . | . | . | . | . | . |
| 21-225_219A7_HC | . | . | . | . | . | . | . | . | . | . | . | . | . | . | . | . | . | . | . | . | . | . | . | . | . |
| 21-225_221G4_HC | . | . | . | . | . | . | . | . | . | . | . | . | . | . | . | . | . | . | . | . | . | . | . | . | . |
| 21-225_221H2_HC | . | . | . | . | . | . | . | . | . | . | . | . | . | . | . | . | . | . | . | . | . | . | . | . | . |

Table 70. Consensus 36- VH3|3-23/D4|4-17|RF2/JH4 (SEQ ID NO: 50287):
EVQLLES-GGGLVQPGGSLRLSCAASG-FTFSS----YAMSWVRQAPGKGLEWVSAISGS---
GGNTFYADSVKGRFTISRDNSKNTLYLQMNSLRAEDTAVYYCAKKDYDYVW----------GSPYFDYWGQGTLVTVSS wherein:

Y in position 39 can be substituted with S

S in position 42 can be substituted with T or N

A in position 57 can be substituted with V

S in position 59 can be substituted with I

R in position 61 can be substituted with S, N or F

G in position 66 can be substituted with S

N in position 67 can be substituted with R or S

T in position 68 can be substituted with A

F in position 69 can be substituted with Y

K in position 109 can be substituted with D or R

D in position 110 can be substituted with Y, H, M or R

Y in position 111 can be substituted with G or N

D in position 112 can be substituted with I, R or Y

Y in position 113 can be substituted with null (-), S or V

V in position 114 can be substituted with null (-), G, R or S

W in position 115 can be substituted with null (-) or I null (-) in position 116 can be substituted with A FIGURE 57 (Continued)

G in position 132 can be substituted with null (-) or V

S in position 133 can be substituted with null (-), A, T or Y

P in position 134 can be substituted with null (-), G or I

Y in position 135 can be substituted with F or T

Ser Xaa Ala Met Xaa (SEQ ID NO: 50055)

Xaa Ile Xaa Gly Xaa Gly Xaa Xaa Xaa Xaa Tyr Ala Asp Ser Val Lys Gly (SEQ ID NO: 50056)

Xaa Xaa Xaa Xaa Xaa Xaa Xaa Xaa Xaa Xaa Xaa Xaa Phe Asp Tyr (SEQ ID NO: 50057)

Ser Tyr Ala Met Ser (SEQ ID NO: 50531)

Ala Ile Ser Gly Ser Gly Gly Asn Thr Phe Tyr Ala Asp Ser Val Lys Gly (SEQ ID NO: 50532)

Lys Asp Tyr Asp Tyr Val Trp Gly Ser Pro Tyr Phe Asp Tyr (SEQ ID NO: 50533)

FIGURE 57 (Continued)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| | | | | | | | | | | | | | | | | | H_FR1 | | | | | | | | |
| CONSENSUS | E | V | Q | L | L | E | S | - | G | G | G | L | V | Q | P | G | G | S | L | R | L | S | C | A | A |
| 21-225_146A6_HC | . | . | . | . | . | . | . | . | . | . | . | . | . | . | . | . | | . | . | . | . | . | . | . | . |
| 21-225_147D10_HC | . | . | . | . | . | . | . | . | . | . | . | . | . | . | S | . | | . | . | . | . | . | . | . | . |
| 21-225_147D12_HC | . | . | . | . | . | . | . | . | . | . | . | . | . | . | . | . | | . | . | . | . | . | . | . | . |
| 21-225_148E2_HC | . | . | . | . | . | . | . | . | . | . | . | . | . | . | . | . | | . | . | . | . | . | . | . | . |
| 21-225_149C6_HC | . | . | . | . | . | . | . | . | . | . | . | . | . | . | . | . | | . | . | . | . | . | . | . | . |
| 21-225_149D11_HC | . | . | . | . | . | . | . | . | . | . | . | . | . | . | . | . | | . | . | . | . | . | . | . | . |
| 21-225_149F8_HC | . | . | . | . | . | . | . | . | . | . | . | . | . | . | . | . | | . | . | . | . | . | . | . | . |
| 21-225_150C5_HC | . | . | . | . | . | . | . | . | . | . | . | . | . | . | . | . | | . | . | . | . | . | . | . | . |
| 21-225_152G10_HC | . | . | . | . | . | . | . | . | . | . | . | . | . | . | . | . | | . | . | . | . | . | . | . | . |
| 21-225_152H7_HC | . | . | . | . | . | . | . | . | . | . | . | . | . | . | . | . | | . | . | . | . | . | . | . | . |
| 21-225_155A4_HC | . | . | . | . | . | . | . | . | . | . | . | . | . | . | . | . | | . | . | . | . | . | . | . | . |
| 21-225_155B4_HC | . | . | . | . | . | . | . | . | . | . | . | . | . | . | T | . | | . | . | . | . | . | . | . | . |
| 21-225_178F7_HC | . | . | . | . | . | . | . | . | . | . | . | . | . | . | T | . | | . | . | . | . | . | . | . | . |
| 21-225_179G1_HC | . | . | . | . | . | . | . | . | . | . | . | . | . | . | . | . | | . | . | . | . | . | . | . | . |
| 21-225_190D12_HC | . | . | . | . | . | . | . | . | . | . | . | . | . | . | . | . | | . | . | . | . | . | . | . | . |
| 21-225_197C8_HC | . | . | . | . | . | . | . | . | . | . | . | . | . | . | . | . | | . | . | . | . | . | . | . | . |
| 21-225_55E1_HC | . | . | . | . | . | . | . | . | . | . | . | . | . | . | . | . | | . | . | . | . | . | . | . | . |

FIGURE 57 (Continued)

| Reference # | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 |
|---|---|---|---|---|---|---|---|---|---|---|---|---|---|---|---|---|---|---|---|---|---|---|---|---|---|
| | | | | | | | H_CDR1 | | | | | | | | | | | H_FR2 | | | | | | | |
| CONSENSUS | S | G | - | F | T | F | S | S | - | - | - | - | - | Y | A | M | S | W | V | R | Q | A | P | G | K |
| 21-225_146A6_HC | . | . | . | . | . | . | . | . | . | . | . | . | . | . | . | . | . | . | . | . | . | . | . | . | . |
| 21-225_147D10_HC | . | . | . | . | . | . | . | . | . | . | . | . | . | . | . | . | . | . | . | . | . | . | . | . | . |
| 21-225_147D12_HC | . | . | . | . | . | . | . | . | . | . | . | . | . | . | . | . | . | . | . | . | . | . | . | . | . |
| 21-225_148E2_HC | . | . | . | . | . | . | . | . | . | . | . | . | . | . | . | . | . | . | . | . | . | . | . | . | . |
| 21-225_149C8_HC | . | . | . | . | . | . | . | . | . | . | . | . | . | . | . | . | N | . | . | . | . | . | . | . | . |
| 21-225_149D11_HC | . | . | . | . | . | . | . | . | . | . | . | . | . | . | . | . | . | . | . | . | . | . | . | . | . |
| 21-225_149F8_HC | . | . | . | . | . | . | . | . | . | . | . | . | . | . | . | . | . | . | . | . | . | . | . | . | . |
| 21-225_150C5_HC | . | . | . | . | . | . | . | . | . | . | . | . | . | . | . | . | . | . | . | . | . | . | . | . | . |
| 21-225_152G10_HC | . | . | . | . | . | . | . | . | . | . | . | . | . | . | . | . | . | . | . | . | . | . | . | . | . |
| 21-225_152H7_HC | . | . | . | . | . | . | N | . | . | . | . | . | . | . | . | . | N | . | . | . | . | . | . | . | . |
| 21-225_155A4_HC | . | . | . | . | . | . | N | . | . | . | . | . | . | . | . | . | . | . | . | . | . | . | . | . | . |
| 21-225_155B4_HC | . | . | . | . | . | . | . | . | . | . | . | . | . | . | . | . | . | . | . | . | . | . | . | . | . |
| 21-225_178F7_HC | . | . | . | . | . | . | . | . | . | . | . | . | . | . | . | . | N | . | . | . | . | . | . | . | . |
| 21-225_179G1_HC | . | . | . | . | . | . | . | . | . | . | . | . | . | S | . | . | T | . | . | . | . | . | . | . | . |
| 21-225_190D12_HC | . | . | . | . | . | . | . | . | . | . | . | . | . | . | . | . | T | . | . | . | . | . | . | . | . |
| 21-225_197C8_HC | . | . | . | . | . | . | . | . | . | . | . | . | . | . | . | . | T | . | . | . | . | . | . | . | . |
| 21-225_55E1_HC | . | . | . | . | . | . | . | . | . | . | . | . | . | . | . | . | . | . | . | . | . | . | . | . | . |

FIGURE 57 (Continued)

H_CDR2 spans positions 56–67.

| Reference # | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|---|---|---|---|---|---|---|---|
| CONSENSUS | G | L | E | W | V | S | A | I | S | G | S | . | . | . | G | G | N | T | F | Y | A | D | S | V | K |
| 21-225_146A6_HC | . | . | . | . | . | . | . | . | . | . | S | . | . | . | . | . | . | . | . | . | . | . | . | . | . |
| 21-225_147D10_HC | . | . | . | . | . | . | . | . | . | . | K | . | . | . | . | . | . | . | . | . | . | . | . | . | . |
| 21-225_147D12_HC | . | . | . | . | . | . | . | . | . | . | K | . | . | . | . | . | . | . | . | . | . | . | . | . | . |
| 21-225_148E2_HC | . | . | . | . | . | . | . | . | . | . | S | . | . | . | . | . | . | . | . | . | . | . | . | . | . |
| 21-225_149C6_HC | . | . | . | . | . | . | . | . | . | . | K | . | . | . | . | . | . | . | . | . | . | . | . | . | . |
| 21-225_149D11_HC | . | . | . | . | . | . | . | . | . | . | K | . | . | . | . | . | . | . | . | . | . | . | . | . | . |
| 21-225_149F8_HC | . | . | . | . | . | . | . | . | . | . | S | . | . | . | . | . | . | . | . | . | . | . | . | . | . |
| 21-225_150C5_HC | . | . | . | . | . | . | . | . | . | . | K | . | . | . | . | . | . | . | . | . | . | . | . | . | . |
| 21-225_152G10_HC | . | . | . | . | . | . | . | . | . | . | S | . | . | . | . | . | . | . | . | . | . | . | . | . | . |
| 21-225_152H7_HC | . | . | . | . | . | . | V | . | . | . | S | . | . | . | . | . | . | . | . | . | . | . | . | . | . |
| 21-225_155A4_HC | . | . | . | . | . | . | V | . | . | . | S | . | . | . | . | . | . | . | . | . | . | . | . | . | . |
| 21-225_155B4_HC | . | . | . | . | . | . | . | . | . | . | S | . | . | . | . | . | . | . | . | . | . | . | . | . | . |
| 21-225_178F7_HC | . | . | . | . | . | . | . | . | . | . | F | . | . | . | . | . | . | . | . | . | . | . | . | . | . |
| 21-225_179G1_HC | . | . | . | . | D | . | . | . | - | . | N | . | . | . | . | . | K | . | Y | . | . | . | . | . | . |
| 21-225_190D12_HC | . | . | . | . | . | . | . | . | - | . | N | . | . | . | . | . | K | A | Y | . | . | . | . | . | . |
| 21-225_197C8_HC | . | . | . | . | . | . | . | . | . | . | K | . | . | . | . | S | S | . | . | . | . | . | . | . | . |
| 21-225_55E1_HC | . | . | . | . | . | . | . | . | . | . | . | . | . | . | . | . | . | . | . | . | . | . | . | . | . |

| Reference # | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|---|---|---|---|---|
| CONSENSUS | . | . | . | . | . | . | G | S | P | Y | F | D | Y | W | G | Q | G | T | L | V | T | V | S | S |
| 21-225_146A6_HC | . | . | . | . | . | . | . | . | . | . | . | . | . | . | . | . | . | . | . | . | . | . | . | . |
| 21-225_147D10_HC | . | . | . | . | . | . | . | . | . | . | . | . | . | . | . | . | . | . | . | . | . | . | . | . |
| 21-225_147D12_HC | . | . | . | . | . | . | . | . | . | . | . | . | . | . | . | . | . | . | . | . | . | . | . | . |
| 21-225_148E2_HC | . | . | . | . | . | . | . | . | . | . | . | . | . | . | . | . | . | . | . | . | . | . | . | . |
| 21-225_149C6_HC | . | . | . | . | . | . | . | . | . | . | . | . | . | . | . | . | . | . | . | . | . | . | . | . |
| 21-225_149D11_HC | . | . | . | . | . | . | . | . | . | . | . | . | . | . | . | . | . | . | . | . | . | . | . | . |
| 21-225_149F8_HC | . | . | . | . | . | . | . | . | . | . | . | . | . | . | . | . | . | . | . | . | . | . | . | . |
| 21-225_150C5_HC | . | . | . | . | . | . | . | . | . | . | . | . | . | . | . | . | . | . | . | . | . | . | . | . |
| 21-225_152G10_HC | . | . | . | . | . | . | . | . | . | . | . | . | . | . | . | . | . | . | . | . | . | . | . | . |
| 21-225_152H7_HC | . | . | . | . | . | . | . | . | . | . | . | . | . | . | . | . | . | . | . | . | . | . | . | . |
| 21-225_155A4_HC | . | . | . | . | . | . | . | . | . | . | . | . | . | . | . | . | . | . | . | . | . | . | . | . |
| 21-225_155B4_HC | . | . | . | . | . | . | . | . | . | . | . | . | . | . | . | . | . | . | . | . | . | . | . | . |
| 21-225_178F7_HC | . | . | . | . | . | . | . | . | . | . | . | . | . | . | . | . | . | . | . | . | . | . | . | . |
| 21-225_179G1_HC | . | . | . | . | . | . | . | . | . | & | . | . | . | . | . | . | . | . | . | . | . | . | . | . |
| 21-225_190D12_HC | . | . | . | . | . | . | . | Y | Q | . | . | . | . | . | . | . | . | . | . | . | . | . | . | . |
| 21-225_197C8_HC | . | . | . | . | . | . | V | A | Q | T | . | . | . | . | . | . | . | . | . | . | . | . | . | . |
| 21-225_65E1_HC | . | . | . | . | . | . | . | T | — | . | . | . | . | . | . | . | . | . | . | . | . | . | . | . |

FIGURE 57
(Continued)

Table 71. Consensus 37- VH1|1-02/D3|3-22|RF2/JH4 (SEQ ID NO: 50288):

QVQLVQS-GAEVKKPGASVKVSCKASG-YTFTG------YYMHWVRQAPGQGLEWMGWINPN---
SGGTNYAQKFQGRVTMTRDTSISTAYMELSRLRSDDTAVYYCARSYY--------YNEFDYWGQGTLVTVSS wherein:

G in position 33 can be substituted with D

Y in position 39 can be substituted with H

Y in position 40 can be substituted with C

M in position 41 can be substituted with I

W in position 57 can be substituted with S

N in position 59 can be substituted with Y

P in position 60 can be substituted with R

N in position 61 can be substituted with K

G in position 67 can be substituted with A

T in position 68 can be substituted with A

N in position 69 can be substituted with D

Y in position 70 can be substituted with N or S

A in position 71 can be substituted with G or V

G in position 76 can be substituted with D or V

S in position 109 can be substituted with A, V or T

Y in position 110 can be substituted with F or N

Y in position 112 can be substituted with H

FIGURE 57 (Continued)

S in position 116 can be substituted with T

Y in position 133 can be substituted with H

E in position 135 can be substituted with G or D

Xaa Xaa Xaa Xaa His (SEQ ID NO: 50058)

Xaa Ile Xaa Xaa Xaa Ser Gly Xaa Xaa Xaa Xaa Gln Lys Phe Gln Xaa (SEQ ID NO: 50059)

Xaa Xaa Tyr Xaa Gly Ser Gly Xaa Tyr Xaa Asn Xaa Phe Asp Tyr (SEQ ID NO: 50060)

Gly Tyr Tyr Met His (SEQ ID NO: 50534)

Trp Ile Asn Pro Asn Ser Gly Gly Thr Asn Tyr Ala Gln Lys Phe Gln Gly (SEQ ID NO: 50535)

Ser Tyr Tyr Tyr Gly Ser Gly Ser Tyr Tyr Asn Glu Phe Asp Tyr (SEQ ID NO: 50536)

Table 72. Consensus 38 – VH1|1-02/D4|4-23|RF2/JH6 (SEQ ID NO: 50289):

QVQLVQS-GAEVKKPGASVKVSCKASG-YTFTG-----YYIHWVRQAPGQGLEWMGWINPY---SGDTNYAQKFQGRVTMTRDTSISTAYMELSRLRFDDTAVFYCARDWGGYSS----------YYYGMDVWGQGTTVTVSS wherein:

I in position 41 can be substituted with T

D in position 67 can be substituted with G

N in position 69 can be substituted with K

Y in position 70 can be substituted with S

Y in position 134 can be substituted with F

Gly Tyr Tyr Xaa His (SEQ ID NO: 50061)

Trp Ile Asn Pro Tyr Ser Gly Xaa Thr Xaa Xaa Ala Gln Lys Phe Gln Gly (SEQ ID NO: 50062)

Asp Trp Gly Gly Tyr Ser Ser Tyr Tyr Xaa Gly Met Asp Val (SEQ ID NO: 50236)

Gly Tyr Tyr Ile His (SEQ ID NO: 50537)

Trp Ile Asn Pro Tyr Ser Gly Asp Thr Asn Tyr Ala Gln Lys Phe Gln Gly (SEQ ID NO: 50538)

Asp Trp Gly Gly Tyr Ser Ser Tyr Tyr Tyr Gly Met Asp Val (SEQ ID NO: 50539)

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | | | H_CDR1 | | | | | | | | | | | | H_FR2 | | | | | |
| CONSENSUS | G | . | Y | T | F | T | G | . | . | . | . | . | Y | Y | I | H | W | V | R | Q | A | P | G | Q | G | L |
| 21-225_224A7_HC | . | . | . | . | . | . | . | . | . | . | . | . | . | . | . | . | . | . | . | . | . | . | . | . | . | . |
| 21-225_224C11_HC | . | . | . | . | . | . | . | . | . | . | . | . | . | . | . | . | . | . | . | . | . | . | . | . | . | . |
| 21-225_224G1_HC | . | . | . | . | . | . | . | . | . | . | . | . | . | . | . | . | . | . | . | . | . | . | . | . | . | . |
| 21-225_224H11_HC | . | . | . | . | . | . | . | . | . | . | . | . | . | . | . | . | . | . | . | . | T | . | . | . | . | . |
| 21-225_225G4_HC | . | . | . | . | . | . | . | . | . | . | . | . | . | . | . | . | . | . | . | . | . | . | . | . | . | . |
| 21-225_226E11_HC | . | . | . | . | . | . | . | . | . | . | . | . | . | . | . | . | . | . | . | . | . | . | . | . | . | . |
| 21-225_226F10_HC | . | . | . | . | . | . | . | . | . | . | . | . | . | . | . | . | . | . | . | . | . | . | . | . | . | . |
| 21-225_226F9_HC | . | . | . | . | . | . | . | . | . | . | . | . | . | . | . | . | . | . | . | . | . | . | . | . | . | . |
| 21-225_226G8_HC | . | . | . | . | . | . | . | . | . | . | . | . | . | . | . | . | . | . | . | . | . | . | . | . | . | . |
| 21-225_226H12_HC | . | . | . | . | . | . | . | . | . | . | . | . | . | . | . | . | . | . | . | . | . | . | . | . | . | . |
| 21-225_226H9_HC | . | . | . | . | . | . | . | . | . | . | . | . | . | . | . | . | . | . | . | . | . | . | . | . | . | . |
| 21-225_227A8_HC | . | . | . | . | . | . | . | . | . | . | . | . | . | . | T | . | . | . | . | . | . | . | . | . | . | . |
| 21-225_227C1_HC | . | . | . | . | . | . | . | . | . | . | . | . | . | . | . | . | . | . | . | . | . | . | . | . | . | . |
| 21-225_227F2_HC | . | . | . | . | . | . | . | . | . | . | . | . | . | . | . | . | . | . | . | . | . | . | . | . | . | . |

FIGURE 57 (Continued)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | E | W | M | G | W | I | N | P | Y | - | - | - | S | G | D | T | N | Y | A | Q | K | F | Q | G | R | V |
| | | | | | | | | | | | | | | | H_CDR2 | | | | | | | | | | | |
| CONSENSUS | E | W | M | G | W | I | N | P | Y | - | - | - | S | G | D | T | N | Y | A | Q | K | F | Q | G | R | V |
| 21-225_224A7_HC | . | . | . | . | . | . | . | . | . | . | . | . | . | . | . | . | . | . | . | . | . | . | . | . | . | . |
| 21-225_224C11_HC | . | . | . | . | . | . | . | . | . | . | . | . | . | . | . | . | . | . | . | . | . | . | . | . | . | . |
| 21-225_224G1_HC | . | . | . | . | . | . | . | . | . | . | . | . | . | . | . | . | . | . | . | . | . | . | . | . | . | . |
| 21-225_224H11_HC | . | . | . | . | . | . | . | . | . | . | . | . | . | . | . | . | . | . | . | . | . | . | . | . | . | . |
| 21-225_225G4_HC | . | . | . | . | . | . | . | . | . | . | . | . | . | . | . | . | . | . | . | . | . | . | . | . | . | . |
| 21-225_225E11_HC | . | . | . | . | . | . | . | . | . | . | . | . | . | . | . | . | . | . | . | . | . | . | . | . | . | . |
| 21-225_226F10_HC | . | . | . | . | . | . | . | . | . | . | . | . | . | . | . | . | . | . | . | . | . | . | . | . | . | . |
| 21-225_226F9_HC | . | . | . | . | . | . | . | . | . | . | . | . | . | . | . | . | K | . | . | . | . | . | . | . | . | . |
| 21-225_226G8_HC | . | . | . | . | . | . | . | . | . | . | . | . | . | . | . | . | K | . | . | . | . | . | . | . | . | . |
| 21-225_226H12_HC | . | . | . | . | . | . | . | . | . | . | . | . | . | . | . | . | . | . | . | . | . | . | . | . | . | . |
| 21-225_226H9_HC | . | . | . | . | . | . | . | . | . | . | . | . | . | . | . | . | . | S | . | . | . | . | . | . | . | . |
| 21-225_227A8_HC | . | . | . | . | . | . | . | . | . | . | . | . | . | . | G | . | . | . | . | . | . | . | . | . | . | . |
| 21-225_227C1_HC | . | . | . | . | . | . | . | . | . | . | . | . | . | . | . | . | . | . | . | . | . | . | . | . | . | . |
| 21-225_227F2_HC | . | . | . | . | . | . | . | . | . | . | . | . | . | . | . | . | K | . | . | . | . | . | . | . | . | . |

Table 73. Consensus 39 – VH3[3-21/D7[7-27]RF1/JH4 (SEQ ID NO: 50290):

EVQLVES-GGGLVKPGGSLRLSCAASG-FTFSS-----YSMNWVRQAPGKGLEWVSSISGS---
SSYIYYADSVKGRFTISRDNAKNSLYLQMNSLRAEDTAVYYCARLI...............FDYWGQGTLVTVSS wherein:

S in position 33 can be substituted with T

Y in position 39 can be substituted with F

S in position 40 can be substituted with T, N or G

N in position 42 can be substituted with S or I

G in position 60 can be substituted with S

S in position 61 can be substituted with T

S in position 65 can be substituted with I or N

S in position 66 can be substituted with N, T or Y

I in position 68 can be substituted with M or S

Y in position 69 can be substituted with N

A in position 71 can be substituted with T

Xaa Xaa Xaa Met Xaa (SEQ ID NO: 50063)

Ser Ile Ser Xaa Xaa Xaa Xaa Tyr Xaa Xaa Tyr Xaa Asp Ser Val Lys Gly (SEQ ID NO: 50064)

Leu Thr Phe Asp Tyr (SEQ ID NO: 50065)

Ser Tyr Ser Met Asn (SEQ ID NO: 50540)

Ser Ile Ser Gly Ser Ser Ser Tyr Ile Tyr Tyr Ala Asp Ser Val Lys Gly (SEQ ID NO: 50541)

Leu Thr Phe Asp Tyr (SEQ ID NO: 50542)

|  |  |  |  |  |  |  |  |  |  |  |  |  |  |  | H_CDR2 |  |  |  |  |  |  |  |  |  |  |
|---|---|---|---|---|---|---|---|---|---|---|---|---|---|---|---|---|---|---|---|---|---|---|---|---|---|---|
| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
| CONSENSUS | E | W | V | S | S | I | S | G | S | - | - | - | S | S | Y | I | Y | Y | A | D | S | V | K | G | R | F |
| 21-225_10C7_HC | . | . | . | . | . | . | . | . | . | . | . | . | N | N | . | . | . | . | . | . | . | . | . | . | . | . |
| 21-225_12D2_HC | . | . | . | . | . | . | . | S | . | . | . | . | . | . | . | . | . | . | . | . | . | . | . | . | . | . |
| 21-225_151F1_HC | . | . | . | . | . | . | . | S | . | . | . | . | . | Y | . | . | . | . | . | . | . | . | . | . | . | . |
| 21-225_186H12_HC | G | . | . | . | . | . | . | . | . | . | . | . | . | . | . | . | . | . | . | . | . | . | . | . | . | . |
| 21-225_227F1_HC | . | . | . | . | . | . | . | S | . | . | . | . | . | N | . | S | . | . | . | . | . | . | . | . | . | . |
| 21-225_26G1_HC | . | . | . | . | . | . | . | S | . | . | . | . | . | . | . | M | . | . | . | . | . | . | . | . | . | . |
| 21-225_2B1_HC | . | . | . | . | . | . | . | . | . | . | . | . | . | . | . | . | . | . | . | . | . | . | . | . | . | . |
| 21-225_33B7_HC | . | . | . | . | . | . | . | . | . | . | . | . | . | N | . | . | . | . | . | . | . | . | . | . | . | . |
| 21-225_34C11_HC | . | . | . | . | . | . | . | . | . | . | . | . | . | T | . | . | . | . | . | . | . | . | . | . | . | . |
| 21-225_43A4_HC | . | . | . | . | . | . | . | . | . | . | . | . | . | T | . | . | . | . | . | . | . | . | . | . | . | . |
| 21-225_45D9_HC | . | . | . | . | . | . | . | . | T | . | . | . | . | . | . | . | . | . | . | . | . | . | . | . | . | . |
| 21-225_54H3_HC | . | . | . | . | . | . | . | . | . | . | . | . | . | . | . | . | . | . | . | . | . | . | . | . | . | . |
| 21-225_63H8_HC | . | . | . | . | . | . | . | . | . | . | . | . | . | T | . | M | N | . | T | . | . | . | . | . | . | . |
| 21-225_8D8_HC | . | . | . | . | . | . | . | S | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| CONSENSUS | Y | C | A | R | L | T | . | . | . | . | . | . | . | . | . | . | . | . | . | . | . | . | . | . | . | . |
| 21-225_10C7_HC | . | . | . | . | . | Q | . | . | . | . | . | . | . | . | . | . | . | . | . | . | . | . | . | . | . | . |
| 21-225_12D2_HC | . | . | . | . | . | Q | . | . | . | . | . | . | . | . | . | . | . | . | . | . | . | . | . | . | . | . |
| 21-225_151F1_HC | . | . | . | . | Q | . | P | . | . | . | . | . | . | . | . | . | . | . | . | . | . | . | . | . | . | . |
| 21-225_186H12_HC | . | . | . | . | . | . | Q | . | . | . | . | . | . | . | . | . | . | . | . | . | . | . | . | . | . | . |
| 21-225_227F1_HC | . | . | . | . | . | Q | . | . | . | . | . | . | . | . | . | . | . | . | . | . | . | . | . | . | . | . |
| 21-225_26G1_HC | . | . | . | . | . | Q | T | . | . | . | . | . | . | . | . | . | . | . | . | . | . | . | . | . | . | . |
| 21-225_2B1_HC | . | . | . | . | . | N | . | . | . | . | . | . | . | . | . | . | . | . | . | . | . | . | . | . | . | . |
| 21-225_33B7_HC | . | . | . | . | . | . | Q | . | . | . | . | . | . | . | . | . | . | . | . | . | . | . | . | . | . | . |
| 21-225_34C11_HC | . | . | . | . | V | . | S | . | . | . | . | . | . | . | . | . | . | . | . | . | . | . | . | . | . | . |
| 21-225_43A4_HC | . | . | . | . | V | . | S | . | . | . | . | . | . | . | . | . | . | . | . | . | . | . | . | . | . | . |
| 21-225_45D9_HC | . | . | . | G | M | . | . | . | . | . | . | . | . | . | . | . | . | . | . | . | . | . | . | . | . | . |
| 21-225_54H3_HC | . | . | . | . | . | . | T | . | . | . | . | . | . | . | . | . | . | . | . | . | . | . | . | . | . | . |
| 21-225_63H8_HC | . | . | . | . | . | . | N | . | . | . | . | . | . | . | . | . | . | . | . | . | . | . | . | . | . | . |
| 21-225_8D8_HC | . | . | . | . | . | Q | . | . | . | . | . | . | . | . | . | . | . | . | . | . | . | . | . | . | . | . |

H_CDR3

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
|  |  |  |  |  |  |  |  |  |  |  |  |  |  | H_FR4 |  |  |  |  |  |
| CONSENSUS |  |  |  |  |  | F | D | Y | W | G | Q | G | T | L | V | T | V | S | S |
| 21-225_10C7_HC |  |  |  |  |  |  | V |  |  |  |  |  |  |  |  | A |  |  |  |
| 21-225_12D2_HC |  |  |  |  |  |  |  |  |  |  |  |  |  |  |  |  |  |  |  |
| 21-225_151F1_HC |  |  |  |  |  | L | V |  |  |  |  |  |  |  |  |  |  |  |  |
| 21-225_166H12_HC |  |  |  |  |  |  | V |  |  |  |  |  |  |  |  |  |  |  |  |
| 21-225_227F1_HC |  |  |  |  |  |  | V | F |  |  |  |  |  |  |  |  |  |  |  |
| 21-225_26G1_HC |  |  |  |  |  |  | N |  |  |  |  |  |  |  |  |  |  |  |  |
| 21-225_2B1_HC |  |  |  |  |  |  |  |  |  |  |  |  |  |  |  |  |  |  |  |
| 21-225_33B7_HC |  |  |  |  |  |  |  |  |  |  |  |  |  |  |  |  |  |  |  |
| 21-225_34C11_HC |  |  |  |  |  |  |  |  |  |  |  |  | A |  |  |  |  |  |  |
| 21-225_43A4_HC |  |  |  |  |  |  |  |  |  |  |  |  | A |  |  |  |  |  |  |
| 21-225_45D9_HC |  |  |  |  |  |  |  | I |  |  |  |  |  |  |  |  |  |  |  |
| 21-225_54H3_HC |  |  |  |  |  |  | V |  |  |  |  |  |  |  |  |  |  |  |  |
| 21-225_63H8_HC |  |  |  |  |  |  |  |  |  |  |  |  |  |  |  |  |  |  |  |
| 21-225_8D8_HC |  |  |  |  |  |  | N |  |  |  |  |  |  |  |  |  |  |  |  |

FIGURE 57 (Continued)

Table 74. Consensus 40 – VH3|3-33/D3|3-9|RF2/JH4 (SEQ ID NO: 50291):

QVQLVES-GGGVVQPGRSLRLSCAASG-FTFST----YGMHWVRQAPGKGLEWVAIIWYD--
GTNKYYADSVKGRFTISRDNSKNTLYLQLNSLRAEDTAVYYCARDPLRGYN----------DPVMDYWGQGTLVTVSS wherein:

T in position 33 can be substituted with S

I in position 57 can be substituted with V

T in position 66 can be substituted with S

K in position 75 can be substituted with R

M in position 136 can be substituted with L

Xaa Tyr Gly Met His (SEQ ID NO: 50066)

Xaa Ile Trp Tyr Asp Gly Xaa Asn Lys Tyr Tyr Ala Asp Ser Val Xaa Gly (SEQ ID NO: 50067)

Asp Pro Leu Arg Gly Tyr Asn Asp Pro Val Xaa Asp Tyr (SEQ ID NO: 50068)

Thr Tyr Gly Met His (SEQ ID NO: 50543)

Ile Ile Trp Tyr Asp Gly Thr Asn Lys Tyr Tyr Ala Asp Ser Val Lys Gly (SEQ ID NO: 50544)

Asp Pro Leu Arg Gly Tyr Asn Asp Pro Val Met Asp Tyr (SEQ ID NO: 50545)

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | Y | C | A | R | D | P | L | R | G | Y | N | | | | | | | | | H_CDR3 | | | | | | |
| CONSENSUS | | | | | | | | | | | | | | | | | | | | | | | | | | |
| 21-225_169B1_HC | . | . | . | . | . | . | . | . | . | . | . | . | . | . | . | . | . | . | . | . | . | . | . | . | . | . |
| 21-225_169F9_HC | . | . | . | . | . | . | . | . | . | . | . | . | . | . | . | . | . | . | . | . | . | . | . | . | . | . |
| 21-225_170D11_HC | . | . | . | . | . | . | . | . | . | . | . | . | . | . | . | . | . | . | . | . | . | . | . | . | . | . |
| 21-225_170D5_HC | . | . | . | . | . | . | . | . | . | . | . | . | . | . | . | . | . | . | . | . | . | . | . | . | . | . |
| 21-225_170G4_HC | . | . | . | . | . | . | . | . | . | . | . | . | . | . | . | . | . | . | . | . | . | . | . | . | . | . |
| 21-225_170G5_HC | a | . | . | . | . | . | . | . | . | . | . | . | . | . | . | . | . | . | . | . | . | . | . | . | . | . |
| 21-225_171A4_HC | . | . | . | . | . | . | . | . | . | . | . | . | . | . | . | . | . | . | . | . | . | . | . | . | . | . |
| 21-225_171C3_HC | . | . | . | . | . | . | . | . | . | . | . | . | . | . | . | . | . | . | . | . | . | . | . | . | . | . |
| 21-225_172B3_HC | . | . | . | . | . | . | . | . | . | . | . | . | . | . | . | . | . | . | . | . | . | . | . | . | . | . |
| 21-225_172G8_HC | . | . | . | . | . | . | . | . | . | . | . | . | . | . | . | . | . | . | . | . | . | . | . | . | . | . |
| 21-225_173H12_HC | . | . | . | . | . | . | . | . | . | . | . | . | . | . | . | . | . | . | . | . | . | . | . | . | . | . |
| 21-225_175G1_HC | . | . | . | . | . | . | . | . | . | . | . | . | . | . | . | . | . | . | . | . | . | . | . | . | . | . |
| 21-225_176B11_HC | . | . | . | . | . | . | . | . | . | . | . | . | . | . | . | . | . | . | . | . | . | . | . | . | . | . |
| 21-225_178B10_HC | . | . | . | . | . | . | . | . | . | . | . | . | . | . | . | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | D | P | V | M | D | Y | W | G | Q | G | T | L | V | T | V | S | S |
| | | | | | | | | | | | | | | H_FR4 | | | | | |
| CONSENSUS | . | . | . | . | . | . | . | . | . | . | . | . | . | . | . | . | . | . | . |
| 21-225_169B1_HC | . | . | . | . | . | . | . | . | . | . | . | . | . | . | . | . | . | . | . |
| 21-225_169F9_HC | . | . | . | . | . | . | . | . | . | . | . | . | . | . | . | . | . | . | . |
| 21-225_170D11_HC | . | . | . | . | . | . | . | . | . | . | . | . | . | . | . | . | . | . | . |
| 21-225_170D5_HC | . | . | . | . | . | . | . | . | . | . | . | . | . | . | . | . | . | . | . |
| 21-225_170G4_HC | . | . | . | . | . | . | . | . | . | . | . | . | . | . | . | . | . | . | . |
| 21-225_170G5_HC | . | . | . | . | . | . | . | . | . | . | . | . | . | . | . | . | . | . | . |
| 21-225_171A4_HC | . | . | . | . | . | . | . | . | . | . | . | . | . | . | . | . | . | . | . |
| 21-225_171C3_HC | . | . | . | . | . | . | . | . | . | . | . | . | . | . | . | . | . | . | . |
| 21-225_172B3_HC | . | . | . | . | . | . | . | . | . | . | . | . | . | . | . | . | . | . | . |
| 21-225_172G8_HC | . | . | . | . | . | . | . | . | . | . | . | . | . | . | . | . | . | . | . |
| 21-225_173H12_HC | . | . | . | . | . | L | . | . | . | . | . | . | . | . | . | . | . | . | . |
| 21-225_175G1_HC | . | . | . | . | . | . | . | . | . | . | . | . | . | . | . | . | . | . | . |
| 21-225_176B11_HC | . | . | . | . | . | . | . | . | . | . | . | . | . | . | . | . | . | . | . |
| 21-225_178B10_HC | . | . | . | . | . | . | . | . | . | . | . | . | . | . | . | . | . | . | . |

FIGURE 57 (Continued)

Table 75. Consensus 41 - VH3|3-23/D4|4-17|RF2/JH5 (SEQ ID NO: 50292):

EVQLLES-GGGLVQPGGSLRLSCAASG-FTFSS-----YAMSWVRQAPGKGLEWVSAISGR---GGNTFYADSVKGRFTISRDNSKNTLYLQMNSLRAEDTAVYYCAKRVTDYGG----------NDWFDPWGQGTLVTVSS wherein:

S in position 33 can be substituted with N

S in position 42 can be substituted with N or T

R in position 61 can be substituted with S

G in position 66 can be substituted with K

Xaa Tyr Ala Met Xaa (SEQ ID NO: 50069)

Ala Ile Ser Gly Xaa Gly Xaa Asn Thr Phe Tyr Ala Asp Ser Val Lys Gly (SEQ ID NO: 50070)

Arg Val Thr Asp Tyr Gly Gly Asn Asp Trp Phe Asp Pro (SEQ ID NO: 50071)

Ser Tyr Ala Met Ser (SEQ ID NO: 50546)

Ala Ile Ser Gly Arg Gly Gly Asn Thr Phe Tyr Ala Asp Ser Val Lys Gly (SEQ ID NO: 50547)

Arg Val Thr Asp Tyr Gly Gly Asn Asp Trp Phe Asp Pro (SEQ ID NO: 50548)

FIGURE 57 (Continued)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | | | | | H_FR1 | | | | | | | | | | |
| CONSENSUS | E | V | Q | L | L | E | S | - | G | G | G | L | V | Q | P | G | G | S | L | R | L | S | C | A | A | S |
| 21-225_146E9_HC | . | . | . | . | . | . | . | . | . | . | . | . | . | . | . | . | . | . | . | . | . | . | . | . | . | . |
| 21-225_146H1_HC | . | . | . | . | . | . | . | . | . | . | . | . | . | . | . | . | . | . | . | . | . | . | . | . | . | . |
| 21-225_148C4_HC | . | . | . | . | . | . | . | . | . | . | . | . | . | . | . | . | . | . | . | . | . | . | . | . | . | . |
| 21-225_148H9_HC | . | . | . | . | . | . | . | . | . | . | . | . | . | . | . | . | . | . | . | . | . | . | . | . | . | . |
| 21-225_149A3_HC | . | . | . | . | . | . | . | . | . | . | . | . | . | . | . | . | . | . | . | . | . | . | . | . | . | . |
| 21-225_150C11_HC | . | . | . | . | . | . | . | . | . | . | . | . | . | . | . | . | . | . | . | . | . | . | . | . | . | . |
| 21-225_150C12_HC | . | . | . | . | . | . | . | . | . | . | . | . | . | . | . | . | . | . | . | . | . | . | . | . | . | . |
| 21-225_151B12_HC | . | . | . | . | . | . | . | . | . | . | . | . | . | . | . | . | . | . | . | . | . | . | . | . | . | . |
| 21-225_152B11_HC | . | . | . | . | . | . | . | . | . | . | . | . | . | . | . | . | . | . | . | . | . | . | . | . | . | . |
| 21-225_152D2_HC | . | . | . | . | . | . | . | . | . | . | . | . | . | . | . | . | . | . | . | . | . | . | . | . | . | . |
| 21-225_152G4_HC | . | . | . | . | . | . | . | . | . | . | . | . | . | . | . | . | . | . | . | . | . | . | . | . | . | . |
| 21-225_155C4_HC | . | . | . | . | . | . | . | . | . | . | . | . | . | . | . | . | . | . | . | . | . | . | . | . | . | . |
| 21-225_156E4_HC | . | . | . | . | . | . | . | . | . | . | . | . | . | . | . | . | . | . | . | . | . | . | . | . | . | . |

FIGURE 57 (Continued)

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | | | | | | | H_CDR1 | | | | | | | | H_FR2 | | | | | | |
| CONSENSUS | G | - | F | T | F | S | S | - | - | - | - | - | Y | A | M | S | W | V | R | Q | A | P | G | K | G | L |
| 21-225_146E9_HC | . | . | . | . | . | . | . | . | . | . | . | . | . | . | . | . | . | . | . | . | . | . | . | . | . | . |
| 21-225_146H1_HC | . | . | . | . | . | . | . | . | . | . | . | . | . | . | . | N | . | . | . | . | . | . | . | . | . | . |
| 21-225_148C4_HC | . | . | . | . | . | . | . | . | . | . | . | . | . | . | . | T | . | . | . | . | . | . | . | . | . | . |
| 21-225_148H9_HC | . | . | . | . | . | . | . | . | . | . | . | . | . | . | . | N | . | . | . | . | . | . | . | . | . | . |
| 21-225_149A3_HC | . | . | . | . | . | . | . | . | . | . | . | . | . | . | . | . | . | . | . | . | . | . | . | . | . | . |
| 21-225_150C11_HC | . | . | . | . | . | . | . | . | . | . | . | . | . | . | . | N | . | . | . | . | . | . | . | . | . | . |
| 21-225_150C12_HC | . | . | . | . | . | . | . | . | . | . | . | . | . | . | . | N | . | . | . | . | . | . | . | . | . | . |
| 21-225_151B12_HC | . | . | . | . | . | . | . | . | . | . | . | . | . | . | . | . | . | . | . | . | . | . | . | . | . | . |
| 21-225_152B11_HC | . | . | . | . | . | . | . | . | . | . | . | . | . | . | . | . | . | . | . | . | . | . | . | . | . | . |
| 21-225_152D2_HC | . | . | . | . | . | . | N | . | . | . | . | . | . | . | . | . | . | . | . | . | . | . | . | . | . | . |
| 21-225_152G4_HC | . | . | . | . | . | . | . | . | . | . | . | . | . | . | . | . | . | . | . | . | . | . | . | . | . | . |
| 21-225_155C4_HC | . | . | . | . | . | . | . | . | . | . | . | . | . | . | . | . | . | . | . | . | . | . | . | . | . | . |
| 21-225_156E4_HC | . | . | . | . | . | . | . | . | . | . | . | . | . | . | . | . | . | . | . | . | . | . | . | . | . | . |

FIGURE 57 (Continued)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | | H_CDR2 | | | | | | | | | | | | |
| CONSENSUS | E | W | V | S | A | I | S | G | R | - | - | - | G | G | N | T | F | Y | A | D | S | V | K | G | R | F |
| 21-225_146E9_HC | . | . | . | . | . | . | . | . | . | . | . | . | . | . | . | . | . | . | . | . | . | . | . | . | . | . |
| 21-225_146H1_HC | . | . | . | . | . | . | . | . | . | . | . | . | . | . | . | . | . | . | . | . | . | . | . | . | . | . |
| 21-225_148C4_HC | . | . | . | . | . | . | . | . | S | . | . | . | . | . | . | . | . | . | . | . | . | . | . | . | . | . |
| 21-225_148H9_HC | . | . | . | . | . | . | . | . | . | . | . | . | . | . | . | . | . | . | . | . | . | . | . | . | . | . |
| 21-225_149A3_HC | . | . | . | . | . | . | . | . | . | . | . | . | . | . | . | . | . | . | . | . | . | . | . | . | . | . |
| 21-225_150C11_HC | . | . | . | . | . | . | . | . | S | . | . | . | . | . | . | . | . | . | . | . | . | . | . | . | . | . |
| 21-225_150C12_HC | . | . | . | . | . | . | . | . | S | . | . | . | . | . | . | . | . | . | . | . | . | . | . | . | . | . |
| 21-225_151B12_HC | . | . | . | . | . | . | . | . | . | . | . | . | . | X | . | . | . | . | . | . | . | . | . | . | . | . |
| 21-225_152B11_HC | . | . | . | . | . | . | . | . | . | . | . | . | . | . | . | . | . | . | . | . | . | . | . | . | . | . |
| 21-225_152D2_HC | . | . | . | . | . | . | . | . | . | . | . | . | . | . | . | . | . | . | . | . | . | . | . | . | . | . |
| 21-225_152G4_HC | . | . | . | . | . | . | . | . | . | . | . | . | . | . | . | . | . | . | . | . | . | . | . | . | . | . |
| 21-225_155C4_HC | . | . | . | . | . | . | . | . | . | . | . | . | . | . | . | . | . | . | . | . | . | . | . | . | . | . |
| 21-225_156E4_HC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | H_CDR3 | | | | | | | | |
| CONSENSUS | Y | C | A | K | R | V | T | D | Y | G | G | . | . | . | . | . | . | . | . | . | . | . | . | . | . | . |
| 21-225_146E9_HC | . | . | . | . | . | . | . | . | . | . | . | . | . | . | . | . | . | . | . | . | . | . | . | . | . | . |
| 21-225_146H1_HC | . | . | . | . | . | . | . | . | . | . | . | . | . | . | . | . | . | . | . | . | . | . | . | . | . | . |
| 21-225_148C4_HC | . | . | . | . | . | . | . | . | . | . | . | . | . | . | . | . | . | . | . | . | . | . | . | . | . | . |
| 21-225_148H9_HC | . | . | T | . | . | . | . | . | . | . | . | . | . | . | . | . | . | . | . | . | . | . | . | . | . | . |
| 21-225_149A3_HC | . | . | . | . | . | . | . | . | . | . | . | . | . | . | . | . | . | . | . | . | . | . | . | . | . | . |
| 21-225_150C11_HC | . | . | . | . | . | . | . | . | . | . | . | . | . | . | . | . | . | . | . | . | . | . | . | . | . | . |
| 21-225_150C12_HC | . | . | . | . | . | . | . | . | . | . | . | . | . | . | . | . | . | . | . | . | . | . | . | . | . | . |
| 21-225_151B12_HC | . | . | . | . | . | . | . | . | . | . | . | . | . | . | . | . | . | . | . | . | . | . | . | . | . | . |
| 21-225_152B11_HC | . | . | . | . | . | . | . | . | . | . | . | . | . | . | . | . | . | . | . | . | . | . | . | . | . | . |
| 21-225_152D2_HC | . | . | . | . | . | . | . | . | . | . | . | . | . | . | . | . | . | . | . | . | . | . | . | . | . | . |
| 21-225_152G4_HC | . | . | . | . | . | . | . | . | . | . | . | . | . | . | . | . | . | . | . | . | . | . | . | . | . | . |
| 21-225_155C4_HC | . | . | . | . | . | . | . | . | . | . | . | . | . | . | . | . | . | . | . | . | . | . | . | . | . | . |
| 21-225_156E4_HC | . | . | . | . | . | . | . | . | . | . | . | . | . | . | . | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 H_FR3 | 145 | 146 | 147 | 148 | 149 |
|---|---|---|---|---|---|---|---|---|---|---|---|---|---|---|---|---|---|---|---|
| CONSENSUS | - | - | N | D | W | F | D | P | W | G | Q | G | T | L | V | T | V | S | S |
| 21-225_146E9_HC | . | . | . | . | . | . | . | . | . | . | . | . | . | . | . | . | . | . | . |
| 21-225_146H1_HC | . | . | . | . | . | . | . | . | . | . | . | . | . | . | . | . | . | . | . |
| 21-225_148C4_HC | . | . | . | . | . | . | . | . | . | . | . | . | . | . | . | . | . | . | . |
| 21-225_148H9_HC | . | . | . | . | . | . | . | . | . | . | . | . | . | . | . | . | . | . | . |
| 21-225_149A3_HC | . | . | . | . | . | . | . | . | . | . | . | . | . | . | . | . | . | . | . |
| 21-225_150C11_HC | . | . | . | . | . | . | . | . | . | . | . | . | . | . | . | . | . | . | . |
| 21-225_150C12_HC | . | . | . | . | . | . | . | . | . | . | . | . | . | . | . | . | . | . | . |
| 21-225_151B12_HC | . | . | . | . | . | . | . | . | . | . | . | . | . | . | . | . | . | . | . |
| 21-225_152B11_HC | . | . | . | . | . | . | . | . | . | . | . | . | . | . | . | . | . | . | . |
| 21-225_152D2_HC | . | . | . | . | . | . | . | . | . | . | . | . | . | . | . | . | . | . | . |
| 21-225_152G4_HC | . | . | . | . | . | . | . | . | . | . | . | . | . | . | . | . | . | . | . |
| 21-225_155C4_HC | . | . | . | . | . | . | . | . | . | . | . | . | . | . | . | . | . | . | . |
| 21-225_156E4_HC | . | . | . | . | . | . | . | . | . | . | . | . | . | . | . | . | . | . | . |

FIGURE 57 (Continued)

Table 76. Consensus 42 – VH3|3-33/D3|3-3|RF2/JH6 (SEQ ID NO: 50293):

QVQLVES-GGGVVQPGRSLRLSCAASG-FTFST----YGMHWVRQAPGKGLEWVAVIWYG---
GSNKDYADSVKGRFTISRDISKNTLYLQMNSLRAEDTAVYYCARDRDYCSGGSC-------PYYYYYGMDVWGQGTTVTVSS wherein:

T in position 33 can be substituted with S

I in position 58 can be substituted with V

G in position 61 can be substituted with D

S in position 66 can be substituted with N

N in position 67 can be substituted with D or S

K in position 68 can be substituted with T

D in position 69 can be substituted with Y or S

Y in position 70 can be substituted with F

A in position 71 can be substituted with V

K in position 75 can be substituted with R or T

D in position 111 can be substituted with V

Y in position 112 can be substituted with F

G in position 116 can be substituted with T

S in position 117 can be substituted with T or N

Xaa Tyr Gly Met His (SEQ ID NO: 50072)

Val Xaa Trp Tyr Xaa Gly Xaa Xaa Xaa Xaa Xaa Asp Ser Val Xaa Gly (SEQ ID NO: 50073)

Asp Arg Xaa Xaa Cys Ser Gly Xaa Xaa Xaa Cys Pro Tyr Tyr Tyr Tyr Tyr Gly Met Asp Val (SEQ ID NO: 50074)

FIGURE 57 (Continued)

Thr Tyr Gly Met His (SEQ ID NO: 50549)

Val Ile Trp Tyr Gly Gly Ser Asn Lys Asp Tyr Ala Asp Ser Val Lys Gly (SEQ ID NO: 50550)

Asp Arg Asp Tyr Cys Ser Gly Gly Ser Cys Pro Tyr Tyr Tyr Tyr Tyr Gly Met Asp Val (SEQ ID NO: 50551)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | | | | | H_FR1 | | | | | | | | | | |
| CONSENSUS | Q | V | Q | L | V | E | S | - | G | G | G | V | V | Q | P | G | R | S | L | R | L | S | C | A | A | S |
| 21-225_146B8_HC | . | . | . | . | . | . | . | . | . | . | . | . | . | . | . | . | . | . | . | . | . | . | . | . | . | . |
| 21-225_147F9_HC | . | . | . | . | . | . | . | . | . | . | . | . | . | . | . | . | . | . | . | . | . | . | . | . | . | . |
| 21-225_147G9_HC | . | . | . | . | . | . | . | . | . | . | . | . | . | . | . | . | . | . | . | . | . | . | . | . | . | . |
| 21-225_148A9_HC | . | . | . | . | . | . | . | . | . | . | . | . | . | . | . | . | . | . | . | . | . | . | . | . | . | . |
| 21-225_150D3_HC | . | . | . | . | . | . | . | . | . | . | . | . | . | . | . | . | . | . | . | . | . | . | . | . | . | . |
| 21-225_151F3_HC | . | . | H | . | . | . | . | . | . | . | . | . | . | . | . | . | . | . | . | . | . | . | . | . | . | . |
| 21-225_153D9_HC | . | . | . | . | . | . | . | . | . | . | . | . | . | . | . | . | . | . | . | . | . | . | . | . | . | . |
| 21-225_153F9_HC | . | . | . | . | . | . | . | . | . | . | . | . | . | . | . | . | . | . | . | . | . | . | . | . | . | . |
| 21-225_154C3_HC | . | . | . | . | . | . | . | . | . | . | . | . | . | . | . | . | . | . | . | . | . | . | . | T | . | . |
| 21-225_154D11_HC | . | . | . | . | . | . | . | . | . | . | . | . | . | . | . | . | . | . | . | . | . | . | . | . | . | . |
| 21-225_158E9_HC | . | . | . | . | . | . | . | . | . | . | . | . | . | . | . | . | . | . | . | . | . | . | . | . | . | . |
| 21-225_161E10_HC | . | . | . | . | . | . | . | . | . | . | . | . | . | . | . | . | . | . | . | . | . | . | . | . | . | . |
| 21-225_74A9_HC | . | . | . | . | . | . | . | . | . | . | . | . | . | . | . | . | . | . | . | . | . | . | . | . | . | . |

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | | | H_FR3 | | | | | | | | | | | | |
| CONSENSUS | T | L | S | R | D | I | S | K | N | T | L | Y | L | Q | M | N | S | L | R | A | E | D | T | A | V | Y |
| 21-225_146B8_HC | . | . | . | . | . | . | . | . | . | . | . | . | . | . | . | . | . | . | . | . | . | . | . | . | . | . |
| 21-225_147F9_HC | . | . | . | . | . | . | . | . | . | . | . | . | . | . | . | . | . | . | . | . | . | . | . | . | . | . |
| 21-225_147G9_HC | . | . | . | . | . | . | . | . | . | . | . | . | . | . | . | . | . | . | . | . | . | . | . | . | . | . |
| 21-225_148A9_HC | . | . | . | . | . | N | . | . | . | . | . | . | . | . | . | . | . | . | . | . | . | . | . | . | . | . |
| 21-225_150D3_HC | . | . | . | . | . | . | . | . | . | . | . | . | . | . | . | . | . | . | . | . | . | . | . | . | . | . |
| 21-225_151F3_HC | . | . | . | . | . | . | . | . | . | . | . | . | . | . | . | . | . | . | . | . | . | . | . | . | . | . |
| 21-225_153D8_HC | . | . | . | . | . | . | . | . | . | . | . | . | . | . | . | . | . | . | . | . | . | . | . | . | . | . |
| 21-225_153F9_HC | . | . | . | . | . | S | . | . | . | . | . | . | . | . | . | . | . | . | . | . | . | . | . | . | . | . |
| 21-225_154C3_HC | . | . | . | . | . | N | . | . | . | . | . | . | . | . | . | . | . | . | . | . | . | . | . | . | . | . |
| 21-225_154D11_HC | . | . | . | . | . | N | . | . | . | . | . | . | . | . | . | . | . | . | . | . | . | . | . | . | . | . |
| 21-225_158E9_HC | . | . | . | . | . | . | . | . | . | . | . | . | . | . | . | . | . | . | . | . | . | . | . | . | . | . |
| 21-225_161E10_HC | . | . | . | . | . | . | . | . | . | . | . | F | . | . | . | . | . | . | . | . | D | . | . | . | . | . |
| 21-225_74A9_HC | . | . | . | . | . | . | . | . | . | . | . | . | . | . | . | . | . | . | . | . | . | . | . | . | . | . |

FIGURE 57 (Continued)

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | H_CDR3 | | | | | | | | |
| CONSENSUS | Y | C | A | R | Q | R | D | Y | C | S | G | G | S | C | . | . | . | . | . | . | . | . | . | . | P | Y |
| 21-225_146B8_HC | . | . | . | . | . | . | . | . | . | . | . | . | . | . | . | . | . | . | . | . | . | . | . | . | . | . |
| 21-225_147F9_HC | . | . | . | . | . | . | . | . | . | . | . | . | T | . | . | . | . | . | . | . | . | . | . | . | . | . |
| 21-225_147G9_HC | . | . | . | . | . | . | . | . | . | . | . | . | . | . | . | . | . | . | . | . | . | . | . | . | . | . |
| 21-225_148A9_HC | . | . | . | . | . | . | . | . | . | . | . | . | T | . | . | . | . | . | . | . | . | . | . | . | . | . |
| 21-225_150D3_HC | . | . | . | . | . | . | . | . | . | . | . | T | T | . | . | . | . | . | . | . | . | . | . | . | . | . |
| 21-225_151F3_HC | . | . | . | . | . | . | . | . | . | . | . | . | . | . | . | . | . | . | . | . | . | . | . | . | . | . |
| 21-225_153D9_HC | . | . | . | . | . | . | . | . | . | . | . | . | . | . | . | . | . | . | . | . | . | . | . | . | . | . |
| 21-225_153F9_HC | . | . | . | . | . | . | . | . | . | . | . | . | N | . | . | . | . | . | . | . | . | . | . | . | . | . |
| 21-225_154C3_HC | . | . | . | . | . | . | . | . | . | . | . | . | . | . | . | . | . | . | . | . | . | . | . | . | . | . |
| 21-225_154D11_HC | . | . | . | . | . | . | . | . | . | . | . | . | . | . | . | . | . | . | . | . | . | . | . | . | . | . |
| 21-225_158E9_HC | . | . | . | . | . | . | V | F | . | . | . | T | . | . | . | . | . | . | . | . | . | . | . | . | . | . |
| 21-225_161E10_HC | . | . | . | . | . | . | V | F | . | . | . | T | . | . | . | . | . | . | . | . | . | . | . | . | . | . |
| 21-225_74A9_HC | . | . | . | . | . | . | . | . | . | . | . | T | . | . | . | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | H_FR4 | | | | | |
| CONSENSUS | Y | Y | Y | Y | G | M | D | V | W | G | Q | G | T | T | V | T | V | S | S |
| 21-225_146B8_HC | . | . | . | . | . | . | . | . | . | . | . | . | . | . | . | . | . | . | . |
| 21-225_147F9_HC | . | . | . | . | . | . | . | . | . | . | . | . | . | . | . | . | . | . | . |
| 21-225_147G9_HC | . | . | . | . | . | . | . | . | . | . | . | . | . | . | . | . | . | . | . |
| 21-225_148A9_HC | . | . | . | . | . | . | . | . | . | . | . | . | . | . | . | . | . | . | . |
| 21-225_150D3_HC | . | . | . | . | . | . | . | . | . | . | . | . | . | . | . | . | . | . | . |
| 21-225_151F3_HC | . | . | . | . | . | . | . | . | . | . | . | . | . | . | . | . | . | . | . |
| 21-225_153D9_HC | . | . | . | . | . | . | . | . | . | . | . | . | . | . | . | . | . | . | . |
| 21-225_153F9_HC | . | . | . | . | . | . | . | . | . | . | . | . | . | . | . | . | . | . | . |
| 21-225_154C3_HC | . | . | . | . | . | . | . | . | . | . | . | . | . | . | . | . | . | . | . |
| 21-225_154D11_HC | . | . | . | . | . | . | . | . | . | . | . | . | . | . | . | . | . | . | . |
| 21-225_158E9_HC | . | . | . | . | . | . | . | . | . | . | . | . | . | . | . | . | . | . | . |
| 21-225_161E10_HC | . | . | . | . | . | . | . | . | . | . | . | . | . | . | . | . | . | . | . |
| 21-225_74A9_HC | . | . | . | . | . | . | . | . | . | . | . | . | . | . | . | . | . | . | . |

FIGURE 57 (Continued)

Table 77. Consensus 43 – VH4|4-39/D4|4-17|RF2/JH4 (SEQ ID NO: 50294):

QLQLQES-GPGLVKPSETLSLTCTVSG-GSISRS---SYYWGWIRQPPGKGLEWIGNIYY---
SGSTYYNPSLKSRVTISVDTSKNQFSLKLSSVTAADTAVYYCGRHGKDW----------GLDYWGQGTLVTVSS wherein:

S in position 65 can be substituted with G

S in position 67 can be substituted with T or N

T in position 68 can be substituted with A

Y in position 70 can be substituted with N, D, H or T

L in position 74 can be substituted with V

S in position 76 can be substituted with G

Y in position 138 can be substituted with F or N

Arg Ser Tyr Tyr Trp Gly (SEQ ID NO: 50075)

Asn Ile Tyr Tyr Xaa Gly Xaa Xaa Tyr Xaa Asn Pro Ser Xaa Lys Xaa (SEQ ID NO: 50076)

His Gly Lys Asp Trp Gly Leu Asp Xaa (SEQ ID NO: 50077)

Arg Ser Tyr Tyr Trp Gly (SEQ ID NO: 50552)

Asn Ile Tyr Tyr Ser Gly Ser Thr Tyr Tyr Asn Pro Ser Leu Lys Ser (SEQ ID NO: 50553)

His Gly Lys Asp Trp Gly Leu Asp Tyr (SEQ ID NO: 50554)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | | | H_CDR2 | | | | | | | | | | | |
| CONSENSUS | E | W | I | G | N | I | Y | Y | . | . | . | . | S | G | S | T | Y | Y | N | P | S | L | K | S | R | V |
| 21-225_11F5_HC | . | . | . | . | . | . | . | . | . | . | . | . | . | . | . | . | . | . | . | . | . | . | . | . | . | . |
| 21-225_14B2_HC | . | . | . | . | . | . | . | . | . | . | . | . | . | . | . | . | . | . | . | . | . | . | . | . | . | . |
| 21-225_17F9_HC | . | . | . | . | . | . | . | . | . | . | . | . | . | . | . | . | . | . | . | . | . | . | . | . | . | . |
| 21-225_17H8_HC | Q | . | . | . | . | . | . | . | . | . | . | . | . | . | T | . | . | . | . | . | . | . | . | . | . | . |
| 21-225_1F2_HC | . | . | . | . | . | . | . | . | . | . | . | . | Q | . | N | . | . | N | . | . | . | . | . | . | . | . |
| 21-225_21H3_HC | . | . | . | . | . | . | . | . | . | . | . | . | . | . | . | A | . | Q | . | . | . | . | . | Q | . | A |
| 21-225_22G8_HC | . | . | . | . | . | . | . | . | . | . | . | . | . | . | . | . | . | . | . | . | . | . | . | . | . | . |
| 21-225_22H4_HC | . | . | . | . | . | . | . | . | . | . | . | . | . | . | . | . | . | N | . | . | . | V | . | . | . | . |
| 21-225_23A3_HC | . | . | . | . | . | . | . | . | . | . | . | . | . | . | T | . | . | N | . | . | . | . | . | . | . | . |
| 21-225_23C8_HC | . | . | . | . | . | . | . | . | . | . | . | . | . | . | . | . | . | Q | . | . | . | . | . | . | . | . |
| 21-225_4F4_HC | . | . | . | . | . | . | . | . | . | . | . | . | . | . | N | . | . | N | . | . | . | . | . | . | . | . |
| 21-225_4H4_HC | . | . | . | . | . | . | . | . | . | . | . | . | . | . | T | . | . | . | . | . | . | . | . | . | . | . |
| 21-225_5H7_HC | . | . | . | . | . | . | . | . | . | . | . | . | . | . | . | . | . | . | . | . | . | . | . | . | . | . |

Replacement Sheet

FIGURE 57 (Continued)

Table 78. Consensus 44 - VH1!1-02/D7![7-27]RF1/JH4 (SEQ ID NO: 50295):

QVQLVQS-GAEVKKPGASVKVSCKASG-YTFTG-----YYMHWVRQAPGQGLEWMGWIKPN---SGGTNQAQKFQGRVTMTRDTSISTAYMELSGLRSDDTAVYYCARAPGTAAAG---------TWGYFDYWGQGTLVTVSS wherein:

M at position 41 can be substituted with I

K in position 59 can be substituted with N

N in position 61 can be substituted with K

Q in position 70 can be substituted with S, H, N or Y

A in position 71 can be substituted with V

T in position 112 can be substituted with K or I

A in position 113 can be substituted with V

A in position 114 can be substituted with P

A in position 115 can be substituted with T

T in position 132 can be substituted with S

Y in position 135 can be substituted with F or C

Gly Tyr Tyr Xaa His (SEQ ID NO: 50078)

Trp Ile Xaa Pro Xaa Ser Gly Gly Thr Asn Xaa Xaa Gln Lys Phe Gln Gly (SEQ ID NO: 50079)

Ala Pro Gly Xaa Xaa Xaa Xaa Gly Xaa Trp Gly Xaa Phe Asp Tyr (SEQ ID NO: 50080)

Gly Tyr Tyr Met His (SEQ ID NO: 50555)

Trp Ile Lys Pro Asn Ser Gly Gly Thr Asn Gln Ala Gln Lys Phe Gln Gly (SEQ ID NO: 50556)

Ala Pro Gly Thr Ala Ala Ala Gly Trp Gly Tyr Phe Asp Tyr (SEQ ID NO: 50557)

Replacement Sheet

FIGURE 57 (Continued)

Table 79. Consensus 45 - VH2/2-05/JD6|6-6|RF2/JH4 (SEQ ID NO: 50296):

QITLKES-GPTLVKPTQTLTLTCTFSG-FSLSTG---GVGVGWIRQPPGKALEWLALIYW----
DDDKRYSPSLKSRLTITKDTSKNQVVLTMTNMDPVDTATYYCAHLIAV-----------AFDYWGQGTLVTVSS wherein:

G in position 34 can be substituted with S

L in position 57 can be substituted with F

D in position 65 can be substituted with H, N, K or S

K in position 68 can be substituted with E

K in position 75 can be substituted with R

L in position 109 can be substituted with I or A

I in position 110 can be substituted with V or A

A in position 135 can be substituted with S

F in position 136 can be substituted with C

Thr Xaa Gly Tyr Val Gly (SEQ ID NO: 50081)

Xaa Ile Tyr Trp Xaa Asp Asp Xaa Arg Tyr Ser Pro Ser Leu Xaa Ser (SEQ ID NO: 50082)

Xaa Xaa Ala Val Xaa Xaa Asp Tyr (SEQ ID NO: 50083)

Thr Gly Gly Val Gly Val Gly (SEQ ID NO: 50558)

Leu Ile Tyr Trp Asp Asp Lys Arg Tyr Ser Pro Ser Leu Lys Ser (SEQ ID NO: 50559)

Leu Ile Ala Val Ala Phe Asp Tyr (SEQ ID NO: 50560)

Replacement Sheet

FIGURE 57 (Continued)

Table 80. Consensus 46 - VH3:3-33/ID3|3-22|RF2/JH4 (SEQ ID NO: 50297):
QVQLVES-GGGVVQPGRSLRLSCAASG-FTPSS------YGMHWVRQAPGKGLEWVAIIWYD---GSYKYYADSVKGRFTISRDNSKNTLYLQMNSLRAEDTAVYYCAREAYDFW............SGYFDYWGQGTLVTVSS wherein:

S at position 33 can be substituted with N or T

I at position 57 can be substituted with V

Y at position 67 can be substituted with N

A at position 71 can be substituted with V

A at position 110 can be substituted with G, R, or N

Y at position 135 can be substituted with F or H

F at position 136 can be substituted with L, Y, or W

D at position 137 can be substituted with G

Y at position 138 can be substituted with S

Xaa Tyr Gly Met His (SEQ ID NO: 50084)

Xaa Ile Trp Tyr Asp Gly Ser Xaa Lys Tyr Tyr Xaa Asp Ser Val Lys Gly (SEQ ID NO: 50085)

Glu Xaa Tyr Asp Phe Trp Ser Gly Xaa Xaa Xaa Xaa (SEQ ID NO: 50086)

Ser Tyr Gly Met His (SEQ ID NO: 50561)

Ile Ile Trp Tyr Asp Gly Ser Tyr Lys Tyr Tyr Ala Asp Ser Val Lys Gly (SEQ ID NO: 50562)

Glu Ala Tyr Asp Phe Trp Ser Gly Tyr Phe Asp Tyr (SEQ ID NO: 50563)

FIGURE 57 (Continued)

Table 81. Consensus 47 - VH3|3-33/D5|5-18|RF3/JH6 (SEQ ID NO: 50298):

QVQLVES-GGGVVQPGRSLRLSCAASG-FTPSS------YGMHWVRQAPGKGLEWVAVIWYD---
GSNKYYADSVKGRFTISRDNSKNTLYLQMNSLRAEDTAVYYCARDRDYGD----------YGMDVWGQGTTVTVSS wherein, M at position 41 can be substituted with L
Y at position 69 can be substituted with N
A at position 71 can be substituted with E
D at position 109 can be substituted with W
R at position 110 can be substituted with R, G or Y
D at position 111 can be substituted with S or Y
G at position 113 can be substituted with Y
D at position 114 can be substituted with Y
null (-) at position 115 can be substituted with P
null (-) at position 116 can be substituted with P
null (-) at position 117 can be substituted with Y
null (-) at position 131 can be substituted with Y
null (-) at position 132 can be substituted with Y
null (-) at position 133 can be substituted with Y
Y at position 134 can be substituted with D
Ser Tyr Gly Xaa His (SEQ ID NO: 50087)
Val Ile Trp Tyr Asp Gly Ser Asn Lys Xaa Tyr Xaa Asp Ser Val Lys Gly (SEQ ID NO: 50088)

Replacement Sheet

FIGURE 57 (Continued)

Xaa Xaa Xaa Tyr Xaa Xaa Xaa Xaa Xaa Xaa Gly Met Asp Val (SEQ ID NO: 50089)

Ser Tyr Gly Met His (SEQ ID NO: 50564)

Val Ile Trp Tyr Asp Gly Ser Asn Lys Tyr Tyr Ala Asp Ser Val Lys Gly (SEQ ID NO: 50565)

Asp Arg Asp Tyr Gly Asp Tyr Gly Met Asp Val (SEQ ID NO: 50566)

Replacement Sheet

FIGURE 57 (Continued)

Table 82. Consensus 4S - VH3|3-23/D4-4-17|RF2/JH6 (SEQ ID NO: 50299):

EVQLLES-GGGLVQPGGSLRLSCAASG-FTFSS-----YAMSWVRQAPGKGLEWVSAISGS---
GGNTFYADSVKGRFTISRDNSKNTLYLQMNSLRAEDTAVYYCAKLGKDYY............YYGMDVWGQGTTVTVSS wherein:

S at position 33 can be substituted with N or T
Y at position 39 can be substituted with S
A at position 40 can be substituted with V
S at position 42 can be substituted with T or N
A at position 57 can be substituted with G
I at position 58 can be substituted with S or V
S at position 59 can be substituted with V
S at position 61 can be substituted with R
G at position 66 can be substituted with A, S or V
N at position 67 can be substituted with R or K
F at position 69 can be substituted with Y
Y at position 70 can be substituted with N
A at position 71 can be substituted with T
K at position 75 can be substituted with T
L at position 109 can be substituted with D or E
G at position 110 can be substituted with R
K at position 111 can be substituted with G or I Page 402 of 1000

Replacement Sheet

FIGURE 57 (Continued)

D at position 112 can be substituted with Q or Y

Y at position 113 can be substituted with W

Y at position 114 can be substituted with H or L

Y at position 133 can be substituted with null (-), I, or L

Y at position 134 can be substituted with G

M at position 136 can be substituted with V

Xaa Xaa Xaa Met Xaa (SEQ ID NO: 50090)

Xaa Xaa Xaa Gly Xaa Gly Xaa Xaa Thr Xaa Xaa Xaa Asp Ser Val Xaa Gly (SEQ ID NO: 50091)

Xaa Xaa Xaa Xaa Xaa Xaa Xaa Gly Xaa Gly Xaa Asp Val (SEQ ID NO: 50092)

Ser Tyr Ala Met Ser (SEQ ID NO: 50567)

Ala Ile Ser Gly Ser Gly Gly Asn Thr Phe Tyr Ala Asp Ser Val Lys Gly (SEQ ID NO: 50568)

Leu Gly Lys Asp Tyr Tyr Tyr Tyr Gly Met Asp Val (SEQ ID NO: 50569)

Page 403 of 1000

Replacement Sheet

FIGURE 57 (Continued)

Table 83. Consensus 49 - VH3|3-23/D7|7-27|RF1/JH4 (SEQ ID NO: 50300):
EVQLLES-GGGLVQPGGSLRLSCAASG-FTFSS----YVMSWVRQAPGKGLEWVSAMSGS---
GGRTYYADSVKGRFTISRDNSKNTLYLQMNSLRAEDTAVYYCAKLTA------------FDYWGQGTLVTVSS wherein:

V at position 40 can be substituted with A

S at position 42 can be substituted with N

A at position 57 can be substituted with G, T or S

M at position 58 can be substituted with I or T

G at position 66 can be substituted with N or V

R at position 67 can be substituted with N or W

Y at position 69 can be substituted with F or N

K at position 75 can be substituted with N

G at position 76 can be substituted with D

L at position 109 can be substituted with V, Y or F

T at position 110 can be substituted with E, F or G

A at position 111 can be substituted with G, L, W, null (-) or F null (-) at position 112 can be substituted with G or M null (-) at position 113 can be substituted with V null (-) at position 114 can be substituted with G null (-) at position 133 can be substituted with A null (-) at position 134 can be substituted with G Replacement Sheet FIGURE 57 (Continued)

null (-) at position 135 can be substituted with I or F

F at position 136 can be substituted with N or null (-)

D at position 137 can be substituted with G or I

Y at position 138 can be substituted with D

Ser Tyr Xaa Met Xaa (SEQ ID NO: 50093)

Xaa Xaa Ser Gly Ser Gly Xaa Xaa Thr Xaa Tyr Ala Asp Ser Val Xaa Xaa (SEQ ID NO: 50094)

Xaa Xaa Xaa Xaa Xaa Xaa Xaa Xaa Xaa Xaa Xaa Xaa Xaa (SEQ ID NO: 50095)

Ser Tyr Val Met Ser (SEQ ID NO: 50570)

Ala Met Ser Gly Ser Gly Gly Arg Thr Tyr Tyr Ala Asp Ser Val Lys Gly (SEQ ID NO: 50571)

Leu Thr Ala Phe Asp Tyr (SEQ ID NO: 50572)

FIGURE 57 (Continued)

| Reference # | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|
| | | | | | | | | | | | | | | | | | H_FR1 | | | | | | | | | | |
| CONSENSUS | | E | V | Q | L | L | E | S | - | G | G | L | V | Q | P | G | G | S | L | R | L | S | C | A | A | S |
| 21-225_157G5_HC | | . | . | . | . | . | . | . | . | . | . | . | . | . | . | . | . | . | . | . | . | . | . | . | . | . |
| 21-225_167D12_HC | | . | . | . | . | . | . | . | . | . | . | . | . | . | . | . | . | . | . | . | . | . | . | . | . | . |
| 21-225_177D3_HC | | . | . | . | . | . | . | . | . | . | . | . | . | . | . | . | . | . | . | . | . | . | . | . | . | . |
| 21-225_51C5_HC | | . | . | . | . | . | . | . | . | . | . | . | . | . | . | . | . | . | . | . | . | . | . | . | . | . |
| 21-225_51D5_HC | | . | . | . | . | . | . | . | . | . | . | . | . | . | . | . | . | . | . | . | . | . | . | . | . | . |
| 21-225_57B8_HC | | . | . | . | . | . | . | . | . | . | . | . | . | . | . | . | . | . | . | . | . | . | . | . | . | . |
| 21-225_58F11_HC | | . | . | . | . | . | . | . | . | . | . | . | . | . | . | . | . | . | . | . | . | . | . | . | . | . |
| 21-225_60A4_HC | | . | . | . | . | . | . | . | . | . | . | . | . | . | . | . | . | . | . | . | . | . | . | . | . | . |
| 21-225_60F7_HC | | . | . | . | . | . | . | . | . | . | . | . | . | . | . | . | . | . | . | . | . | . | . | . | . | . |
| 21-225_61E6_HC | | . | . | . | . | . | . | . | . | . | . | . | . | . | . | . | . | . | . | . | . | . | . | . | . | . |

| Reference # | | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|---|
| | | | | | | H_CDR1 | | | | | | | | | | | | | | | | H_FR2 | | | | | |
| CONSENSUS | | G | - | F | T | F | S | S | - | - | - | - | Y | V | M | S | W | V | R | Q | A | P | G | K | G | L | L |
| 21-225_157G5_HC | | . | . | . | . | . | . | . | . | . | . | . | . | . | . | . | . | . | . | . | . | . | . | . | . | . | . |
| 21-225_167D12_HC | | . | . | . | . | . | . | . | . | . | . | . | . | . | N | . | . | . | . | . | . | . | . | . | . | . | . |
| 21-225_177D3_HC | | . | . | . | . | . | . | . | . | . | . | . | . | . | . | . | . | . | . | . | . | . | . | . | . | . | . |
| 21-225_51C5_HC | | . | . | . | . | . | . | . | . | . | . | . | . | . | . | . | . | . | . | . | . | . | . | . | . | . | . |
| 21-225_51D5_HC | | . | . | . | . | . | S | . | . | . | . | . | . | A | . | . | . | . | . | . | . | T | . | . | . | . | . |
| 21-225_57B8_HC | | . | . | . | . | . | . | . | . | . | . | . | . | A | . | . | . | . | . | . | . | T | . | . | . | . | . |
| 21-225_58F11_HC | | . | . | . | . | . | . | . | . | . | . | . | . | . | . | . | . | . | . | . | . | . | . | . | . | . | . |
| 21-225_60A4_HC | | . | . | . | . | . | . | . | . | . | . | . | . | . | . | . | . | . | . | . | . | . | . | . | . | . | . |
| 21-225_60F7_HC | | . | . | . | . | . | . | . | . | . | . | . | . | . | . | . | . | . | . | . | . | . | . | . | . | . | . |
| 21-225_61E6_HC | | . | . | . | . | . | S | . | . | . | . | . | . | A | . | . | . | . | . | . | . | . | . | . | . | . | . |

Replacement Sheet

FIGURE 57 (Continued)

Table 84. Consensus 50 - VH3|3-30.3/D5|5-24|RF3/JH6 (SEQ ID NO: 50301):
QVQLVES-GGGVVQPGRSLRLSCAASG-FTPSS------YGMHWVRQAPGKGLEWVAIISYA---
GSNKYYADSVKGRFTISRDNSKNTLYLQMNSLRAEDTAVYYCVRRGYSYG----------GYGMDVWGQGTTVTVSS wherein:

S at position 33 can be substituted with Y

M at position 41 can be substituted with L

I at position 57 can be substituted with V

A at position 61 can be substituted with G, D, S or V

S at position 66 can be substituted with I, N, R or T

K at position 68 can be substituted with N or Q

Y at position 69 can be substituted with S, D or H

Y at position 70 can be substituted with S

R at position 109 can be substituted with E

G at position 110 can be substituted with D

Y at position 111 can be substituted with R

S at position 112 can be substituted with Y

Y at position 113 can be substituted with C

G at position 114 can be substituted with S null (-) at position 115 can be substituted with G null (-) at position 116 can be substituted with T null (-) at position 117 can be substituted with S Replacement Sheet FIGURE 57 (Continued)

null (-) at position 118 can be substituted with C null (-) at position 129 can be substituted with P null (-) at position 130 can be substituted with Y null (-) at position 131 can be substituted with Y null (-) at position 132 can be substituted with Y G at position 133 can be substituted with Y Xaa Tyr Gly Xaa His (SEQ ID NO: 50096)

Xaa Ile Ser Tyr Xaa Gly Xaa Asn Xaa Xaa Xaa Ala Asp Ser Val Lys Gly (SEQ ID NO: 50097)

Xaa Xaa Xaa Xaa Xaa Xaa Xaa Xaa Xaa Xaa Xaa Xaa Tyr Gly Met Asp Val (SEQ ID NO: 50098)

Ser Tyr Gly Met His (SEQ ID NO: 50573)

Ile Ile Ser Tyr Ala Gly Ser Asn Lys Tyr Tyr Ala Asp Ser Val Lys Gly (SEQ ID NO: 50574)

Arg Gly Tyr Ser Tyr Gly Gly Tyr Gly Met Asp Val (SEQ ID NO: 50575)

Replacement Sheet

FIGURE 57 (Continued)

Table 85. Consensus 51 - VH3|3-33/D3|3-10|RF2/JH6 (SEQ ID NO: 50302):

QVQLVES-GGGVVQPGRSLRLSCAASG-FTPSD------YVMHWVRQAPGKGLEWVAVIWYD---GSNKYYADSVKGRFTISRDNSKNTLYLQMNSLRAEDTAVYYCAREPYTSGW---------YDYGMDVWGQGTTVTVSS wherein:

D at position 33 can be substituted with S

Y at position 39 can be substituted with C

V at position 40 can be substituted with G

H at position 42 can be substituted with Q

V at position 57 can be substituted with I

G at position 76 can be substituted with V

P at position 110 can be substituted with R

T at position 112 can be substituted with N

Y at position 132 can be substituted with H

M at position 136 can be substituted with L

Xaa Xaa Xaa Met Xaa (SEQ ID NO: 50099)

Xaa Ile Trp Tyr Asp Gly Ser Asn Lys Tyr Ala Asp Ser Val Lys Xaa (SEQ ID NO: 50100)

Glu Xaa Tyr Xaa Ser Gly Trp Xaa Asp Tyr Gly Xaa Asp Val (SEQ ID NO: 50101)

Asp Tyr Val Met His (SEQ ID NO: 50576)

Val Ile Trp Tyr Asp Gly Ser Asn Lys Tyr Tyr Ala Asp Ser Val Lys Gly (SEQ ID NO: 50577)

Glu Pro Tyr Thr Ser Gly Trp Tyr Asp Tyr Gly Met Asp Val (SEQ ID NO: 50578)

FIGURE 57 (Continued)

Table 86. Consensus 52 - VH1|1-18/D3|3-3|RF2/JH6 (SEQ ID NO: 50303):

QVQLVQS-GAEVKKPGASVKVSCKASG-YTFNS------YGISWVRQAPGQGLEWMGWISAY---NGNTKYAQKLQGRVTMTIDTSTSTAYMELRSLRSDDTAVYYCARHDFWSGY---------YKGMDYWGQGTTVTVSS wherein:

I in position 41 can be substituted with F or V

T in position 68 can be substituted with R

Y in position 70 can be substituted with N, E or F

K in position 73 can be substituted with R

L in position 74 can be substituted with F

Ser Tyr Gly Xaa Ser (SEQ ID NO: 50102)

Trp Ile Ser Ala Tyr Asn Gly Asn Xaa Lys Xaa Ala Gln Xaa Xaa Gln Gly (SEQ ID NO: 50103)

His Asp Phe Trp Ser Gly Tyr Tyr Lys Gly Met Asp Val (SEQ ID NO: 50227)

Ser Tyr Gly Ile Ser (SEQ ID NO: 50579)

Trp Ile Ser Ala Tyr Asn Gly Asn Thr Lys Tyr Ala Gln Lys Tyr Ala Gln Lys Leu Gln Gly (SEQ ID NO: 50580)

His Asp Phe Trp Ser Gly Tyr Tyr Lys Gly Met Asp Val (SEQ ID NO: 50581)

Replacement Sheet

FIGURE 57 (Continued)

Table 87. Consensus 53 - VH3:3-23/D6|6-6|RF1/JH4 (SEQ ID NO: 50304):

EVQLLES-GGGLVQPGGSLRLSCAASG-FTFSS------YAMSWVRQAPGKGLEWVSAISGR----GG
NTFDADSVKGRFTISRDNSKNTLYLQMNSLRAEDTAVYYCAKERSGS................YFDYWGQGTLVTVSS wherein:

Y at position 39 can be substituted with S
A at position 57 can be substituted with V or S
R at position 61 can be substituted with S
G at position 66 can be substituted with I or V
N at position 67 can be substituted with S
D at position 70 can be substituted with Y
A at position 71 can be substituted with T
E at position 109 can be substituted with S
R at position 110 can be substituted with N
G at position 112 can be substituted with S
S at position 113 can be substituted with G
Y at position 135 can be substituted with W Xaa Xaa Ala Met Ser (SEQ ID NO: 50104)

Xaa Ile Ser Gly Xaa Gly Xaa Xaa Thr Phe Xaa Xaa Asp Ser Val Lys Gly (SEQ ID NO: 50105)

Xaa Xaa Ser Xaa Xaa Xaa Phe Asp Tyr (SEQ ID NO: 50106)

Ser Tyr Ala Met Ser (SEQ ID NO: 50582)

Ala Ile Ser Gly Arg Gly Asn Thr Phe Asp Ala Asp Ser Val Lys Gly (SEQ ID NO: 50583)

Replacement Sheet

FIGURE 57 (Continued)

Glu Arg Ser Gly Ser Tyr Phe Asp Tyr (SEQ ID NO: 50584)

FIGURE 57 (Continued)

Replacement Sheet

FIGURE 57 (Continued)

Table 88. Consensus 54 - VH3|3-33|/D6|6-6|RF1/JH4 (SEQ ID NO: 50305):

QVQLVES-GGGVVQPGRSLRLSCAASG-FTPSN----YGMHWVRQAPGKGLEWVAVIWHD---GSNKYYADSVKGRFTISRDNSKNTLYLQMNSLRAEDTAVYYCARENSSS---------YYFDYWGQGTLVTVSS, wherein:

N in position 33 can be substituted with S, Y or H

G in position 40 can be substituted with V

V in position 57 can be substituted with L

H in position 60 can be substituted with Y

S in position 66 can be substituted with T

N in position 67 can be substituted with D

K in position 68 can be substituted with A

A in position 71 can be substituted with V or G

Y in position 134 can be substituted with F

Xaa Tyr Xaa Met His (SEQ ID NO: 50107)

Xaa Ile Trp Xaa Asp Gly Xaa Xaa Xaa Tyr Tyr Xaa Asp Ser Val Lys Gly (SEQ ID NO: 50108)

Glu Asn Ser Ser Xaa Tyr Phe Asp Tyr Trp Gly Gln Gly Thr Leu Val Thr Val Ser Ser (SEQ ID NO: 50109)

Asn Tyr Gly Met His (SEQ ID NO: 50585)

Val Ile Trp His Asp Gly Ser Asn Lys Tyr Tyr Ala Asp Ser Val Lys Gly (SEQ ID NO: 50586)

Glu Asn Ser Ser Tyr Tyr Phe Asp Tyr Trp Gly Gln Gly Thr Leu Val Thr Val Ser Ser (SEQ ID NO: 50587)

Replacement Sheet

FIGURE 57 (Continued)

Table 89. Consensus 55 - VH2/2-05/D1|1-1|RF1/JH3 (SEQ ID NO: 50346):

QITLKES-GPTLVKPTQTLTLTCTFSG-FSLSTS---GVGVGWIRQPPGKALEWLALINW----NDDKRYSPSLKSRFTITRDTSKDQVVLTMTNMDPVDTATYYCAHKATWV---------AFDIWGQGTMVTVSS wherein:

Y in position 70 can be substituted with F

A in position 110 can be substituted with T

Thr Ser Gly Val Gly Val Gly (SEQ ID NO: 50110)

Leu Ile Asn Trp Asn Asp Asp Lys Arg Xaa Ser Pro Ser Leu Lys Ser (SEQ ID NO: 50111)

Lys Xaa Thr Trp Val Ala Phe Asp Ile (SEQ ID NO: 50112)

Thr Ser Gly Val Gly Val Gly (SEQ ID NO: 50588)

Leu Ile Asn Trp Asn Asp Asp Lys Arg Tyr Ser Pro Ser Leu Lys Ser (SEQ ID NO: 50589)

Lys Ala Thr Trp Val Ala Phe Asp Ile (SEQ ID NO: 50590)

Replacement Sheet

FIGURE 57 (Continued)

Table 90. Consensus 56 – VH3:3-23/D4|4-11|RF3/JH4 (SEQ ID NO: 50307):

EVQLLES-GGGLVQPGGSLRLSCAASG-FTFSS----YVMNWVRQAPGKGLEWVSAISGS---GGRTYYADSVKGRFTISRDNSKNTLYLQMNSLRAEDTAVYYCARTAT----------------FDYWGQGTLVTVSS wherein:

V at position 40 can be substituted with A

M at position 41 can be substituted with I or L

N at position 42 can be substituted with S or R

A at position 57 can be substituted with D

I at position 58 can be substituted with M

G at position 66 can be substituted with D or V

R at position 67 can be substituted with S, F or T

A at position 71 can be substituted with V

A at position 110 can be substituted with G, S, T or Y

T at position 111 can be substituted with V, null (-), H, L or G

F at position 136 can be substituted with null (-) or K

D at position 137 can be substituted with null (-)

Y at position 138 can be substituted with L

Ser Tyr Xaa Xaa Xaa (SEQ ID NO: 50113)

Xaa Xaa Ser Gly Ser Gly Xaa Xaa Thr Tyr Tyr Xaa Asp Ser Val Lys Gly (SEQ ID NO: 50114)

Thr Xaa Xaa Xaa Xaa Xaa (SEQ ID NO: 50115)

Ser Tyr Val Met Asn (SEQ ID NO: 50591)

Replacement Sheet

FIGURE 57 (Continued)

Ala Ile Ser Gly Ser Gly Gly Arg Thr Tyr Tyr Ala Asp Ser Val Lys Gly (SEQ ID NO: 50592)

Thr Ala Thr Phe Asp Tyr (SEQ ID NO: 50593)

Replacement Sheet

FIGURE 57 (Continued)

Table 91. Consensus 57 - VH3|3-23/D7|7-27|RF1/JH3 (SEQ ID NO: 50308):

EVQLLES-GGGLVQPGGSLRLSCAASG-FTFSS-----YAMSWVRQAPGKGLEWVSVISGR---
GGITFYADSVKGRFTISRDNSKNTLYLQMNSLRAEDTAVYYCAKRTPSD------------VFDIWGQGTMVTVSS wherein:

Y at position 39 can be substituted with F
S at position 42 can be substituted with N
V at position 57 can be substituted with A or I
I at position 58 can be substituted with L
R at position 61 can be substituted with S or G
G at position 66 can be substituted with S or K
T at position 67 can be substituted with N or S
F at position 69 can be substituted with Y
P at position 111 can be substituted with G
S at position 112 can be substituted with D or E
V at position 135 can be substituted with A
I at position 138 can be substituted with V Ser Xaa Ala Met Xaa (SEQ ID NO: 50116)
Xaa Xaa Ser Gly Xaa Gly Xaa Xaa Thr Xaa Tyr Ala Asp Ser Val Lys Gly (SEQ ID NO: 50117)
Lys Arg Thr Xaa Xaa Asp Xaa Xaa Phe Asp Xaa (SEQ ID NO: 50118)
Ser Tyr Ala Met Ser (SEQ ID NO: 50594)
Val Ile Ser Gly Arg Gly Gly Thr Phe Tyr Ala Asp Ser Val Lys Gly (SEQ ID NO: 50595)

FIGURE 57 (Continued)

Lys Arg Thr Pro Ser Asp Val Phe Asp Ile (SEQ ID NO: 50596)

Replacement Sheet

FIGURE 57 (Continued)

Table 92. Consensus 5S - VH3|3-33/D4|4-11|RF2/JH4 (SEQ ID NO: 50309):

QVQLVES-GGGVVQPGRSLRLSCAASG-FTPSS----YGMHWVRQAPGKGLEWVAVIWYD---GSNKYYADSVKGRFTISRDNSKNTLYLQMNSLRAEDTAVYYCARDRPRS--------SAF DYWGQGTLVTVSS wherein:

S at position 33 can be substituted with N or T

Y at position 39 can be substituted with F

G at position 40 can be substituted with D or N

V at position 57 can be substituted with A

Y at position 60 can be substituted with H

S at position 66 can be substituted with R

N at position 67 can be substituted with D or H

K at position 68 can be substituted with R

Y at position 70 can be substituted with C or S

A at position 71 can be substituted with E or T

R at position 110 can be substituted with D or H

P at position 111 can be substituted with S or A

I at position 112 can be substituted with R or Y

S at position 113 can be substituted with L, V or W

Null (-) at position 114 can be substituted with G

Replacement Sheet

FIGURE 57 (Continued)

Null (-) at position 133 can be substituted with A

S at position 134 can be substituted with T or A

A at position 135 can be substituted with F, S or Y

F at position 136 can be substituted with G or S

Y at position 138 can be substituted with F

Xaa Xaa Xaa Met His (SEQ ID NO: 50237)

Xaa Ile Trp Xaa Asp Gly Xaa Xaa Xaa Tyr Xaa Xaa Asp Ser Val Lys Gly (SEQ ID NO: 50238)

Asp Xaa Xaa Xaa Xaa Xaa Xaa Xaa Xaa Xaa Asp Xaa (SEQ ID NO: 50239)

Ser Tyr Gly Met His (SEQ ID NO: 50597)

Val Ile Trp Tyr Asp Gly Ser Asn Lys Tyr Tyr Ala Asp Ser Val Lys Gly (SEQ ID NO: 50598)

Asp Arg Pro Arg Ser Ser Ala Phe Asp Tyr (SEQ ID NO: 50599)

Replacement Sheet

FIGURE 57 (Continued)

Table 93. Consensus 59 – VH3:3-48/D4|4-11|RF2/JH6 (SEQ ID NO: 50310):

EVQLVES-GGGLVQPGGSLRLSCAASG-FTFSS-----YNMNWVRQAPGKGLEWVSYISRS---SNTKYYADSVKGRFTISRDNAKNSLYLQMNSLRDEDTAVYYCARDRSGSYGY-----------FYYYGLDVWGQGTTVTVSS wherein:

S at position 33 can be substituted with N

N at position 40 can be substituted with S

R at position 60 can be substituted with S

S at position 65 can be substituted with G

N at position 66 can be substituted with S

K at position 68 can be substituted with T

Y at position 69 can be substituted with H

A at position 71 can be substituted with V

K at position 75 can be substituted with R, E or Q

R at position 110 can be substituted with S

S at position 111 can be substituted with R

G at position 112 can be substituted with K

S at position 113 can be substituted with G

Y at position 114 can be substituted with F

G at position 115 can be substituted with null (-)

Y at position 116 can be substituted with null (-)

Replacement Sheet

FIGURE 57 (Continued)

F at position 131 can be substituted with null (-)

Y at position 132 can be substituted with null (-)

L at position 136 can be substituted with M

Xaa Tyr Xaa Met Asn (SEQ ID NO: 50240)

Tyr Ile Ser Xaa Ser Xaa Xaa Thr Xaa Xaa Tyr Xaa Asp Ser Val Xaa Gly (SEQ ID NO: 50241)

Asp Xaa Xaa Xaa Xaa Xaa Xaa Xaa Xaa Tyr Gly Xaa Asp Val (SEQ ID NO: 50242)

Ser Tyr Asn Met Asn (SEQ ID NO: 50600)

Tyr Ile Ser Arg Ser Ser Asn Thr Lys Tyr Tyr Ala Asp Ser Val Lys Gly (SEQ ID NO: 50601)

Asp Arg Ser Gly Ser Tyr Gly Tyr Phe Tyr Tyr Tyr Gly Leu Asp Val (SEQ ID NO: 50602)

FIGURE 57 (Continued)

Table 94. Consensus 60 - VH4-30.1/D4[4-11]RF2/JH6 (SEQ ID NO: 50311):

QVQLQES-GPGLVKPSQTLSLTCTVSG-GPSISG---GDYWSWIRQHPGKGLEWIGYIYY---SGSTYYNPSLKSRVTISVDTSKNQFSLKLSSVTAADTAVYYCARDSSSY----------GMDYWGQGTTVTVSS wherein:

S at position 67 can be substituted with I or P

S at position 110 can be substituted with G or H

S at position 111 can be substituted with A

S at position 112 can be substituted with L or R

Y at position 113 can be substituted with R or H

Ser Gly Asp Tyr Trp Ser (SEQ ID NO: 50119)

Tyr Ile Tyr Tyr Ser Gly Xaa Thr Tyr Tyr Asn Pro Ser Leu Lys Ser (SEQ ID NO: 50120)

Asp Xaa Xaa Xaa Xaa Gly Met Asp Val (SEQ ID NO: 50121)

Ser Gly Gly Asp Tyr Trp Ser (SEQ ID NO: 50603)

Tyr Ile Tyr Tyr Ser Gly Ser Thr Tyr Tyr Asn Pro Ser Leu Lys Ser (SEQ ID NO: 50604)

Asp Ser Ser Ser Tyr Gly Met Asp Val (SEQ ID NO: 50605)

Table 95. Consensus 15 - VK1|A30/JK4 (SEQ ID NO: 50312):

DIQMTQSPSSLSASVGDRVTITCRAS-QGIR-------NDLGWYQQKPGKAPKRLIYA--------ASSLQSGVPSRFSGSGSG-
TEFTLTISSLQPEDFATYYCLQHNS--------------YPLTFGGGTKVEIKR wherein:

R at position 24 can be substituted with L

A at position 25 can be substituted with T

Q at position 29 can be substituted with R

G at position 30 can be substituted with D, A or V

I at position 31 can be substituted with M or V

R at position 32 can be substituted with E, K, N or S

N at position 39 can be substituted with S, D, T, K or I

D at position 40 can be substituted with N or A

L at position 41 can be substituted with F or V

G at position 42 can be substituted with D or N

A at position 58 can be substituted with T, S, V, G, D or R

A at position 67 can be substituted with T, V or E

S at position 68 can be substituted with F, C or Y

S at position 69 can be substituted with N, T, F, R or I

L at position 70 can be substituted with V, F or S

Q at position 71 can be substituted with H or E

S at position 72 can be substituted with R, N, T or G

Replacement Sheet

FIGURE 57 (Continued)

L at position 107 can be substituted with V or I
Q at position 108 can be substituted with H
H at position 109 can be substituted with D, Y, N or R
N at position 110 can be substituted with S, Y, T, D, K, A, I, E, H, P or R
S at position 111 can be substituted with L, N, R, T, D, A, L or V
Y at position 135 can be substituted with F, H or S
P at position 136 can be substituted with A or M
L at position 137 can be substituted with P, F, N or V
T at position 138 can be substituted with K or I
Xaa Xaa Ser Xaa Xaa Xaa Xaa Xaa Xaa Xaa Xaa (SEQ ID NO: 50122)
Xaa Xaa Xaa Xaa Xaa Xaa Xaa Xaa (SEQ ID NO: 50123)
Xaa Xaa Xaa Xaa Xaa Xaa Xaa Xaa Xaa Xaa (SEQ ID NO: 50124)
Arg Ala Ser Gln Gly Ile Arg Asn Asp Leu Gly (SEQ ID NO: 50606)
Ala Ala Ser Ser Leu Gln Ser (SEQ ID NO: 50607)
Leu Gln His Asn Ser Tyr Pro Leu Thr (SEQ ID NO: 50608)

FIGURE 57 (Continued)

Table 96. Consensus 16 - VL3jr/fL2 (SEQ ID NO: 50313):

SYELTQP-PSVSVSPGQTASITCSGD---KLGD----KYACWYQQKPGQSPVLVIYQ--------DRKRPSGIPERFSGSNSG---NTATLTISGTQAMDEADYYCQAWDS----------------STVFGGGTKLTVLG wherein:

D at position 26 can be substituted with N, E, Y or S
K at position 30 can be substituted with R, N, E or T
L at position 31 can be substituted with M or S
D at position 33 can be substituted with N, E, G, Y, T, H or V
K at position 39 can be substituted with R
Y at position 40 can be substituted with F or S
A at position 41 can be substituted with V, T, D or S
C at position 42 can be substituted with S, Y, W or H
Q at position 58 can be substituted with E or K
D at position 67 can be substituted with N
R at position 68 can be substituted with S, N, K, Y, M, T, G or I
K at position 69 can be substituted with R or Q
P at position 71 can be substituted with S
S at position 72 can be substituted with L
Q at position 107 can be substituted with L or K
A at position 108 can be substituted with T Replacement Sheet FIGURE 57 (Continued)

W at position 109 can be substituted with R
D at position 110 can be substituted with H, V, N or G
S at position 111 can be substituted with N, null (-), I, R, K or T
null (-) at position 134 can be substituted with S, N or R
S at position 135 can be substituted with T, N, R, G, F, I V or Y
T at position 136 can be substituted with S, Y, A, F, P, N, K, I or R
V at position 137 can be substituted with A, T, M L or G
V at position 138 can be substituted with I, L, A or M
Ser Gly Xaa Xaa Xaa Gly Xaa Xaa Xaa Xaa Xaa (SEQ ID NO: 50125)
Xaa Xaa Xaa Xaa Arg Xaa Xaa (SEQ ID NO: 50126)
Xaa Xaa Xaa Xaa Xaa Xaa Xaa Xaa Xaa Xaa (SEQ ID NO: 50228)
Ser Gly Asp Lys Leu Gly Asp Lys Tyr Ala Cys (SEQ ID NO: 50609)
Gln Asp Arg Lys Arg Pro Ser (SEQ ID NO: 50610)
Gln Ala Trp Asp Ser Ser Thr Val (SEQ ID NO: 50611)

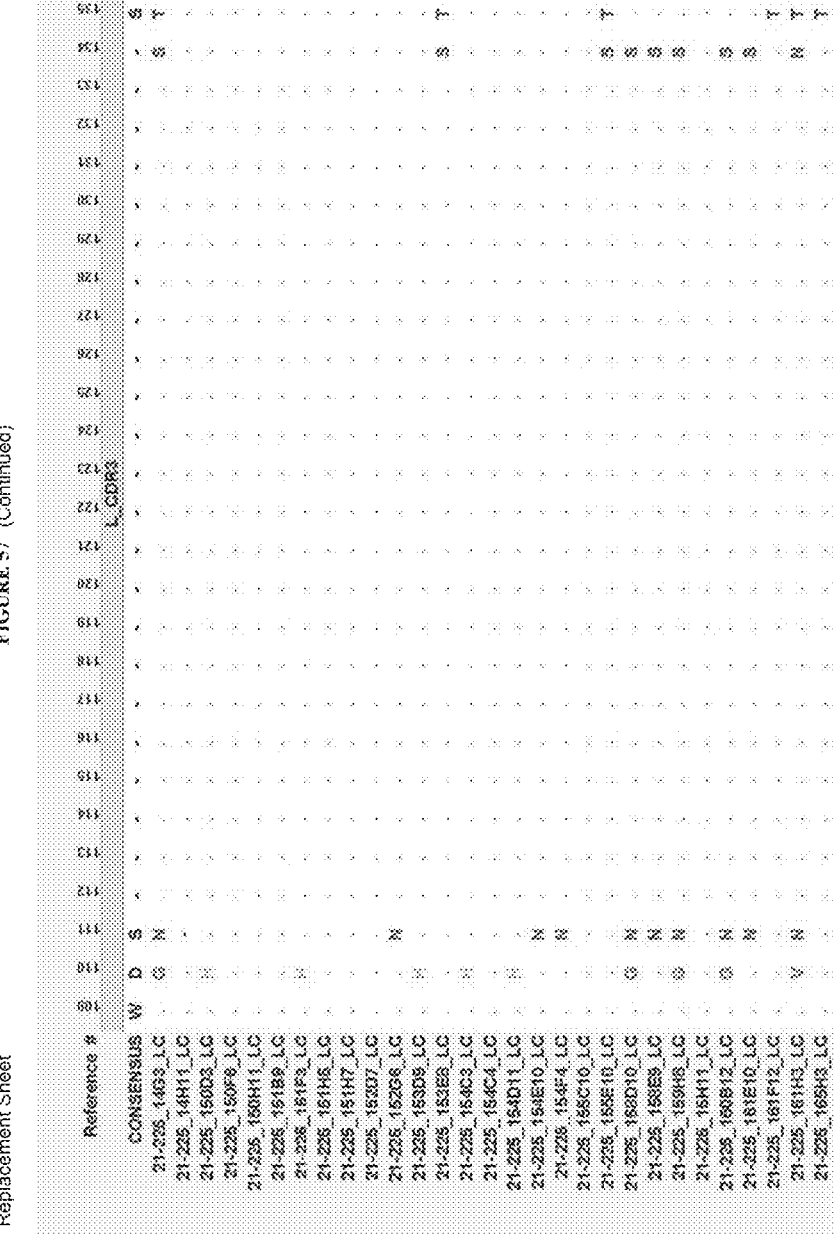

Replacement Sheet

FIGURE 57 (Continued)

Table 97. Consensus 17 - VK3/A27/JK1 (SEQ ID NO: 50314):

EIVLTQSPGTLSLSPGERATLSCRAS-QSVYS-----SYLAWYQQKPGQAPRLLIYG------ASSRATGIPDRFSGSGSG-TDFTLTISRLEPEDFAVYYCQQYDN------SPWTFGQGTKVEIKR wherein.

R at position 24 can be substituted with W

A at position 25 can be substituted with T

S at position 26 can be substituted with G or R

Q at position 29 can be substituted with P

S at position 30 can be substituted with N, I or R

V at position 31 can be substituted with I or F

Y at position 32 can be substituted with R, S, N, D, F, H, G or W

S at position 33 can be substituted with T, N, G, L or R

S at position 39 can be substituted with N, G, R, D, A or Y

Y at position 40 can be substituted with F or H

A at position 42 can be substituted with V or S

G at position 58 can be substituted with D or V

A at position 67 can be substituted with T, P or V

S at position 68 can be substituted with F, Y, A or T

S at position 69 can be substituted with R, N or A

A at position 71 can be substituted with S or T

T at position 72 can be substituted with P, S or A

FIGURE 57 (Continued)

Q at position 107 can be substituted with H
Q at position 108 can be substituted with H
Y at position 109 can be substituted with S
D at position 110 can be substituted with E, G or H
N at position 111 can be substituted with S, null (-), R, T, I, D or G
null (-) at position 134 can be substituted with S
S at position 135 can be substituted with P, N or R
P at position 136 can be substituted with S or V
W at position 137 can be substituted with R
T at position 138 can be substituted with A
Xaa Xaa Xaa Xaa Xaa Xaa Xaa Xaa Xaa Leu Xaa (SEQ ID NO: 50127)
Xaa Xaa Xaa Xaa Arg Xaa Xaa (SEQ ID NO: 50128)
Xaa Xaa Xaa Xaa Xaa Xaa Xaa Xaa Xaa Xaa (SEQ ID NO: 50129)
Arg Ala Ser Gln Ser Val Tyr Ser Ser Tyr Leu Ala (SEQ ID NO: 50612)
Gly Ala Ser Ser Arg Ala Thr (SEQ ID NO: 50613)
Gln Gln Tyr Asp Asn Ser Pro Trp Thr (SEQ ID NO: 50614)

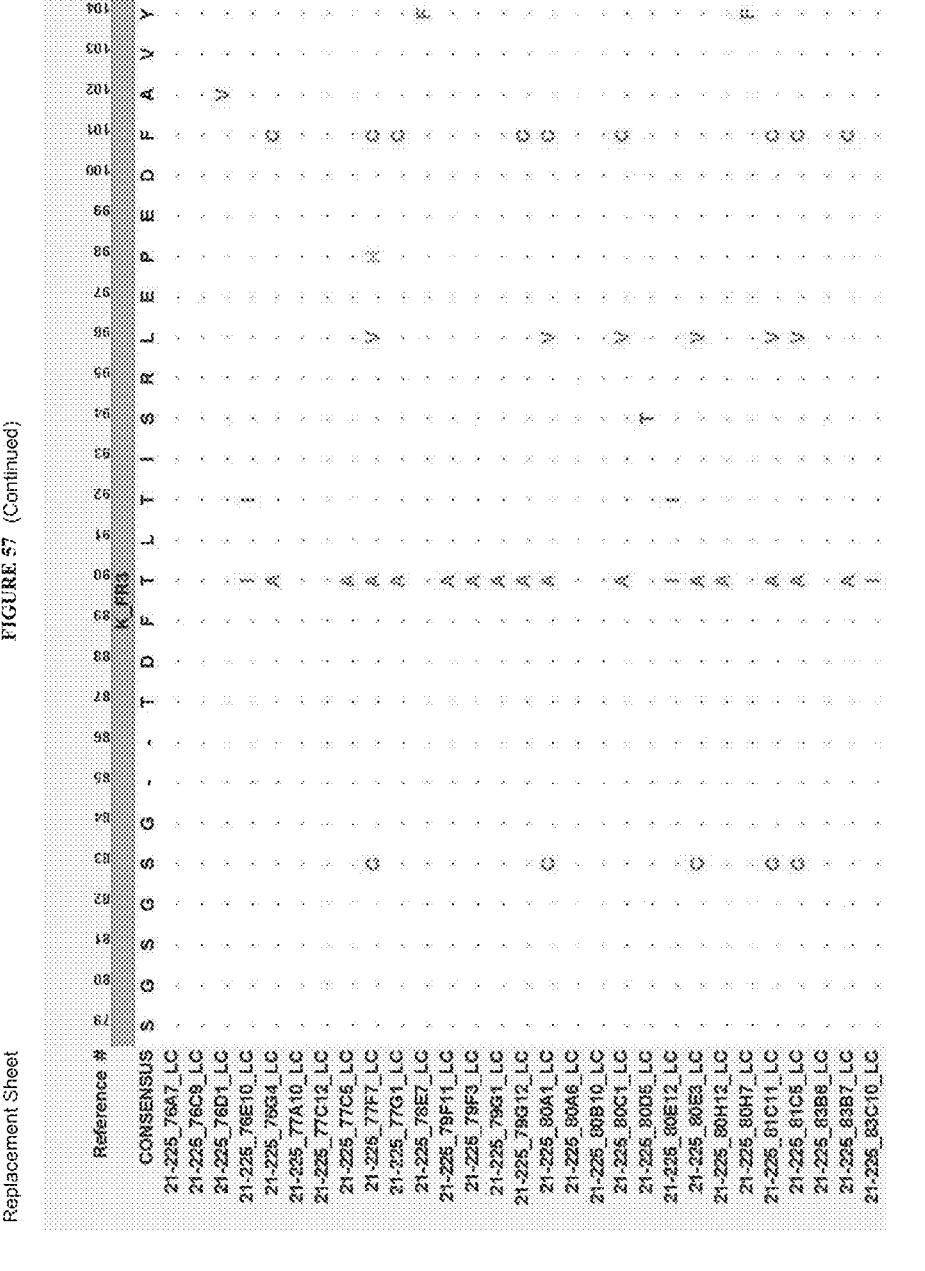

| Reference # | 131 | 132 | 133 | 134 | 135 S | 136 P | 137 W | 138 T | 139 F | 140 G | 141 Q | 142 G | 143 T | 144 K FR4 | 145 V | 146 E | 147 I | 148 K | 149 R |
|---|---|---|---|---|---|---|---|---|---|---|---|---|---|---|---|---|---|---|---|
| CONSENSUS | | | | | | | | | | | | | | | | | | | |
| 21-225_83G1_LC | | | | | | | | | | | | | | | | | | | |
| 21-225_84E12_LC | | | | | | | | | | | | | | | | | | | |
| 21-225_85A3_LC | | | | | | | | | | | | | | | | | | | |
| 21-225_85B4_LC | | | | | | | | | | | | | | | | | | | |
| 21-225_85B9_LC | | | | | | | | | | | | | | | | | | | |
| 21-225_85D6_LC | | | | | | | | | | | | | | | | | | | |
| 21-225_85G10_LC | | | | | | | | | | | | | | | | | | | |
| 21-225_85G8_LC | | | | | | | | | | | | | | | | | | | |
| 21-225_86C1_LC | | | | | | | | | | | | | | | | | | | |
| 21-225_86C11_LC | | | | | | | | | | | | | | | | | | | |
| 21-225_86E4_LC | | | | | | | | | | | | | | | | | | | |
| 21-225_87A12_LC | | | | | | | | | | | | | | | | | | | |
| 21-225_87C9_LC | | | | | | | | | | | | | | | | | | | |
| 21-225_87E5_LC | | | | | | | | | | | | | | | | | | | |
| 21-225_87H1_LC | | | | | | | | | | | | | | | | | | | |
| 21-225_88E7_LC | | | | | | | | | | | | | | | | | | | |
| 21-225_88F7_LC | | | | | | | | | | | | | | | | | | | |
| 21-225_88G9_LC | | | | | | | | | | | | | | | | | | | |
| 21-225_88H1_LC | | | | | | | | | | | | | | | | | | | |
| 21-225_89A11_LC | | | | | | | | | | | | | | | | | | | |
| 21-225_89D5_LC | | | | | | P | | | | | | | | | | | | | |
| 21-225_89E10_LC | | | | | | | | | | | | | | | | | | | |
| 21-225_89H5_LC | | | | | | | | | | | | | | | | | | | |
| 21-225_90A5_LC | | | | | | | | | | | | | | | | | | | |
| 21-225_90F10_LC | | | | | | | | | | | | | | | | | | | |
| 21-225_90G4_LC | | | | | | | | | | | | | | | | | | | |
| 21-225_90G5_LC | | | | | | | | | | | | | | | | | | | |
| 21-225_91B2_LC | | | | | | | | | | | | | | | | | | | |
| 21-225_91B3_LC | | | | | | | | | | | | | | | | | | | |

FIGURE 57 (Continued)

| Reference # | 131 | 132 | 133 | 134 | 135 | 136 | 137 | 138 | 139 | 140 | 141 | 142 | 143 | 144 KFR4 | 145 | 146 | 147 | 148 | 149 |
|---|---|---|---|---|---|---|---|---|---|---|---|---|---|---|---|---|---|---|---|
| CONSENSUS | . | . | . | . | S | P | W | T | F | G | Q | G | T | K | V | E | I | K | R |
| 21-225_91B4_LC | . | . | . | . | . | . | . | . | . | . | . | . | . | . | . | . | . | . | . |
| 21-225_91E9_LC | . | . | . | . | . | . | . | . | . | . | . | . | . | . | . | . | . | . | . |
| 21-225_91F3_LC | . | . | . | . | . | . | . | . | . | . | . | . | . | . | . | . | . | . | . |
| 21-225_92B1_LC | . | . | . | . | . | . | . | . | . | . | . | . | . | . | . | . | . | . | . |
| 21-225_92D6_LC | . | . | . | . | . | . | . | . | . | . | . | . | . | . | . | . | . | . | . |
| 21-225_93C2_LC | . | . | . | . | . | . | . | . | . | . | . | . | . | . | . | . | . | . | . |
| 21-225_93E4_LC | . | . | . | . | . | . | . | . | . | . | . | . | . | . | . | . | . | . | . |
| 21-225_93E9_LC | . | . | . | . | . | . | . | . | . | . | . | . | . | . | . | . | N | Q | N |
| 21-225_94D3_LC | . | . | . | . | . | . | . | . | . | . | . | . | . | . | . | . | . | . | . |
| 21-225_94F12_LC | . | . | . | . | . | . | . | . | . | . | . | . | . | . | . | . | . | . | . |
| 21-225_94G10_LC | . | . | . | . | . | . | . | . | . | . | . | . | . | . | . | . | . | . | . |
| 21-225_95D2_LC | . | . | . | . | . | . | . | . | . | . | . | . | . | . | . | . | . | . | . |
| 21-225_95F9_LC | . | . | . | . | . | . | . | . | . | . | . | . | . | . | . | . | . | . | . |
| 21-225_95G9_LC | . | . | . | . | . | . | . | . | . | . | . | . | . | . | . | . | . | . | . |
| 21-225_95H10_LC | . | . | . | . | . | . | . | . | . | . | . | . | . | . | . | . | . | . | . |
| 21-225_97A2_LC | . | . | . | . | . | . | . | . | . | . | . | . | . | . | . | . | . | . | . |
| 21-225_97E5_LC | . | . | . | . | . | . | . | . | . | . | . | . | . | . | . | . | . | . | . |

FIGURE 57 (Continued)

Table 98. Consensus 18 - VK1|A30/JK1 (SEQ ID NO: 50315):

DIQMTQSPSSLSASVGDRVTITCRAS--QGIR------NDLGWYQQKPGKAPKRLIYA------ASSLQSGVPSRFSGSGSG--
TEFTLTISSLQPEDFATYYCLQHYS................YPRTFGQGTKVEIKR wherein:

A at position 25 can be substituted with T

S at position 26 can be substituted with T

Q at position 29 can be substituted with R

G at position 30 can be substituted with D, A, N or V

R at position 32 can be substituted with G

N at position 39 can be substituted with K, D, H, S, G or T

D at position 40 can be substituted with I or Y

G at position 42 can be substituted with N

A at position 58 can be substituted with T, I, V, P, G, R or S

A at position 67 can be substituted with T or S

S at position 68 can be substituted with A, F, P or Y

S at position 69 can be substituted with N, R, G or T

L at position 70 can be substituted with C, F or S

Q at position 71 can be substituted with H or E

S at position 72 can be substituted with N, G or I

L at position 107 can be substituted with V, I or H

Q at position 108 can be substituted with M, H, L or V

FIGURE 57 (Continued)

H at position 109 can be substituted with Q, Y, L or S

Y at position 110 can be substituted with N, H, S or T

S at position 111 can be substituted with N, T, R, D, F or G null (-) at position 134 can be substituted with Y or F Y at position 135 can be substituted with F, P, C, N or T P at position 136 can be substituted with L R at position 137 can be substituted with W, F or L Arg Xaa Xaa Xaa Ile Xaa Xaa Xaa Leu Xaa (SEQ ID NO: 50130)

Xaa Xaa Xaa Xaa Xaa Xaa Xaa (SEQ ID NO: 50131)

Xaa Xaa Xaa Xaa Xaa Xaa Xaa Xaa Xaa Thr (SEQ ID NO: 50132)

Arg Ala Ser Gln Gly Ile Arg Asn Asp Leu Gly (SEQ ID NO: 50615)

Ala Ala Ser Ser Leu Gln Ser (SEQ ID NO: 50616)

Leu Gln His Tyr Ser Tyr Pro Arg Thr (SEQ ID NO: 50617)

FIGURE 57 (Continued)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | K_FR1 | | | | | | | | | | | | | | | |
| CONSENSUS | D | I | Q | M | T | Q | S | P | S | S | L | S | A | S | V | G | D | R | V | T | I | T | C | R | A | S |
| 21-225_9C11_LC | . | . | . | . | . | . | . | . | . | . | . | . | . | . | . | . | . | . | . | . | . | . | . | . | . | . |
| 21-225_9D12_LC | . | . | . | . | . | . | . | . | . | . | . | . | . | . | . | . | . | . | . | . | . | . | . | . | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| CONSENSUS | K | R | L | I | Y | A | | | | | | | K_CDR2 | | A | S | S | L | Q | S | G | V | P | S | R | F |
| 21-225_9C11_LC | . | L | . | . | . | V | . | . | . | . | . | . | | . | . | . | . | . | . | . | . | . | . | . | . | . |
| 21-225_9D12_LC | . | . | . | . | . | . | . | . | . | . | . | . | | . | . | . | . | . | . | . | . | . | . | . | . | . |

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | K_FR3 | | | | | | | | | | | | | | |
| CONSENSUS | S | G | S | G | S | G | x | x | T | E | F | T | L | T | I | S | S | L | Q | P | E | D | F | A | T | Y |
| 21-225_9C11_LC | . | . | . | . | . | . | . | . | . | . | . | . | . | . | . | N | . | . | . | . | . | . | . | . | - | . |
| 21-225_9D12_LC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | | K_CDR3 | | | | | | | |
| CONSENSUS | Y | C | L | Q | H | Y | S | . | . | . | . | . | . | . | . | . | . | . | . | . | . | . | . | . | . | . |
| 21-225_5E5.011_LC | . | . | . | . | . | . | . | . | . | . | . | . | . | . | . | . | . | . | . | . | . | . | . | . | . | . |
| 21-225_5E5.012_LC | . | . | . | . | . | . | . | . | . | . | . | . | . | . | . | . | . | . | . | . | . | . | . | . | . | . |
| 21-225_5E5.015_LC | . | . | . | . | . | . | . | . | . | . | . | . | . | . | . | . | . | . | . | . | . | . | . | . | . | . |
| 21-225_5E5.016_LC | . | . | . | . | . | . | . | . | . | . | . | . | . | . | . | . | . | . | . | . | . | . | . | . | . | . |
| 21-225_5E5.017_LC | . | . | . | . | . | . | . | . | . | . | . | . | . | . | . | . | . | . | . | . | . | . | . | . | . | . |
| 21-225_5E5.018_LC | . | . | . | . | . | . | . | . | . | . | . | . | . | . | . | . | . | . | . | . | . | . | . | . | . | . |
| 21-225_5E5.019_LC | . | . | . | . | . | . | . | . | . | . | . | . | . | . | . | . | . | . | . | . | . | . | . | . | . | . |
| 21-225_5E5.023_LC | . | . | . | . | . | . | . | . | . | . | . | . | . | . | . | . | . | . | . | . | . | . | . | . | . | . |
| 21-225_5E5.024_LC | . | . | . | . | . | . | . | . | . | . | . | . | . | . | . | . | . | . | . | . | . | . | . | . | . | . |
| 21-225_5E5.025_LC | . | . | . | . | . | . | . | . | . | . | . | . | . | . | . | . | . | . | . | . | . | . | . | . | . | . |
| 21-225_60C3_LC | . | . | . | . | . | N | . | . | . | . | . | . | . | . | . | . | . | . | . | . | . | . | . | . | . | . |
| 21-225_60E2_LC | . | . | . | . | . | N | . | . | . | . | . | . | . | . | . | . | . | . | . | . | . | . | . | . | . | . |
| 21-225_61E6_LC | . | . | . | . | Y | N | . | . | . | . | . | . | . | . | . | . | . | . | . | . | . | . | . | . | . | . |
| 21-225_61H1_LC | . | . | . | . | . | N | . | . | . | . | . | . | . | . | . | . | . | . | . | . | . | . | . | . | . | . |
| 21-225_82F7_LC | . | . | . | V | Y | N | . | . | . | . | . | . | . | . | . | . | . | . | . | . | . | . | . | . | . | . |
| 21-225_84A4_LC | . | . | . | V | . | . | . | . | . | . | . | . | . | . | . | . | . | . | . | . | . | . | . | . | . | . |
| 21-225_64C8_LC | . | . | . | . | . | . | . | . | . | . | . | . | . | . | . | . | . | . | . | . | . | . | . | . | . | . |
| 21-225_68C10_LC | . | . | . | . | . | N | . | . | . | . | . | . | . | . | . | . | . | . | . | . | . | . | . | . | . | . |
| 21-225_68D11_LC | . | . | . | . | . | N | . | . | . | . | . | . | . | . | . | . | . | . | . | . | . | . | . | . | . | . |
| 21-225_6A11_LC | . | . | . | . | . | N | . | . | . | . | . | . | . | . | . | . | . | . | . | . | . | . | . | . | . | . |
| 21-225_6G2_LC | . | . | . | . | . | . | . | . | . | . | . | . | . | . | . | . | . | . | . | . | . | . | . | . | . | . |
| 21-225_71A2_LC | . | . | . | . | . | . | . | . | . | . | . | . | . | . | . | . | . | . | . | . | . | . | . | . | . | . |
| 21-225_73C9_LC | . | . | — | . | . | . | . | . | . | . | . | . | . | . | . | . | . | . | . | . | . | . | . | . | . | . |
| 21-225_7C9_LC | . | . | . | . | L | . | . | . | . | . | . | . | . | . | . | . | . | . | . | . | . | . | . | . | . | . |
| 21-225_7F8_LC | . | . | — | . | . | . | . | . | . | . | . | . | . | . | . | . | . | . | . | . | . | . | . | . | . | . |
| 21-225_7G2_LC | . | . | . | . | Q | N | . | . | . | . | . | . | . | . | . | . | . | . | . | . | . | . | . | . | . | . |
| 21-225_7G4_LC | . | . | — | . | . | . | . | . | . | . | . | . | . | . | . | . | . | . | . | . | . | . | . | . | . | . |
| 21-225_94F3_LC | . | . | . | . | . | . | T | . | . | . | . | . | . | . | . | . | . | . | . | . | . | . | . | . | . | . |
| 21-225_9A1_LC | . | . | . | . | . | N | . | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | K_FR4 | | | | | |
| CONSENSUS | | | | | Y | P | R | T | F | G | Q | G | T | K | V | E | I | K | R |
| 21-225_9C11_LC | | | | | T | | L | | | | | | | | | | | | |
| 21-225_9D12_LC | | | | | | | W | | | | | | | | | | | | |

FIGURE 57 (Continued)

Table 99. Consensus 19 - VK4|B3/JK1 (SEQ ID NO: 50316):

DIVMTQSPDSLAVSLGERATINCKSS--QSVLHSSNNNNYLAWYQQKPGQPPKLLIYW--------ASTRESGVPDRFSGSGSG--TDFTLTISSLQAEDVAVYYCQQYYS----------TPPTFGQGTKVEIKR wherein:

K at position 24 can be substituted with R or M

S at position 26 can be substituted with G or R

S at position 30 can be substituted with T, N or I

V at position 31 can be substituted with I or A

H at position 33 can be substituted with Y, F, S, K, D, L or M

S at position 34 can be substituted with T, R, N, I or D

S at position 35 can be substituted with F or P

N at position 36 can be substituted with H

N at position 37 can be substituted with K, S, D or H

N at position 38 can be substituted with Y, K, H, R, A, F or W

N at position 39 can be substituted with H or Y

Y at position 40 can be substituted with S

L at position 41 can be substituted with F

A at position 42 can be substituted with T, V or G

A at position 67 can be substituted with T or S

S at position 68 can be substituted with F

T at position 69 can be substituted with I, K or S

FIGURE 57 (Continued)

R at position 70 can be substituted with W or L

E at position 71 can be substituted with K, A, D or R

S at position 72 can be substituted with T

Q at position 107 can be substituted with H or L

Q at position 108 can be substituted with H

Y at position 109 can be substituted with F

Y at position 110 can be substituted with F, H, N, L or S

S at position 111 can be substituted with N, R, D, I, T, C, E or K

T at position 135 can be substituted with S, I, V, A or Y

P at position 137 can be substituted with W, L, V, C, G, R or S

T at position 138 can be substituted with K or S

Xaa Xaa Xaa Gln Ser Xaa Leu Xaa Xaa Xaa Xaa Xaa Xaa Xaa Xaa Xaa Xaa (SEQ ID NO: 50133)

Trp Xaa Xaa Xaa Xaa Xaa Xaa (SEQ ID NO: 50229)

Xaa Xaa Xaa Xaa Xaa Xaa Pro Xaa Xaa (SEQ ID NO: 50134)

Lys Ser Ser Gln Ser Val Leu His Ser Ser Asn Asn Asn Asn Tyr Leu Ala (SEQ ID NO: 50618)

Trp Ala Ser Thr Arg Glu Ser (SEQ ID NO: 50619)

Gln Gln Tyr Tyr Ser Thr Pro Pro Thr (SEQ ID NO: 50620)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | K_CDR2 | | | | | | | | | | | | | | |
| CONSENSUS | K | L | L | I | Y | W | , | , | , | , | , | , | , | , | A | S | T | R | E | S | G | V | P | D | R | F |
| 21-225_224D8_LC | . | . | . | . | . | . | . | . | . | . | . | . | . | . | S | . | . | . | . | . | . | . | . | . | . | . |
| 21-225_224H5_LC | . | . | . | . | . | . | . | . | . | . | . | . | . | . | . | . | . | . | . | . | . | . | . | . | . | . |
| 21-225_225F11_LC | N | . | . | . | . | . | . | . | . | . | . | . | . | . | . | . | . | . | . | . | . | . | . | . | . | . |
| 21-225_225F5_LC | . | . | . | F | . | . | . | . | . | . | . | . | . | . | . | . | . | . | K | . | . | . | . | . | . | . |
| 21-225_226A12_LC | . | . | . | . | . | . | . | . | . | . | . | . | . | . | . | . | . | . | . | . | . | . | . | . | . | . |
| 21-225_226D11_LC | N | . | . | . | . | . | . | . | . | . | . | . | . | . | T | . | . | . | . | . | . | . | . | . | . | . |
| 21-225_226F6_LC | . | . | . | . | . | . | . | . | . | . | . | . | . | . | . | . | . | . | . | . | . | . | . | . | . | . |
| 21-225_227C7_LC | N | . | . | . | . | . | . | . | . | . | . | . | . | . | . | . | . | . | . | . | . | . | . | . | . | . |
| 21-225_23A12_LC | . | . | . | . | . | . | . | . | . | . | . | . | . | . | . | . | . | . | . | . | . | . | . | . | . | . |
| 21-225_23G12_LC | . | . | . | . | . | . | . | . | . | . | . | . | . | . | . | . | . | . | . | . | . | . | . | . | . | . |
| 21-225_24E1_LC | . | . | . | L | . | . | . | . | . | . | . | . | . | . | . | . | . | . | . | . | . | . | . | . | . | . |
| 21-225_25A4_LC | . | . | . | L | . | . | . | . | . | . | . | . | . | . | . | . | . | . | . | . | . | . | . | . | . | . |
| 21-225_25A4.001_LC | . | . | . | L | . | . | . | . | . | . | . | . | . | . | . | . | . | . | . | . | . | . | . | . | . | . |
| 21-225_25A4.001.001_LC | . | . | . | L | . | . | . | . | . | . | . | . | . | . | . | . | . | . | . | . | . | . | . | . | . | . |
| 21-225_25A4.001.002_LC | . | . | . | L | . | . | . | . | . | . | . | . | . | . | . | . | . | . | . | . | . | . | . | . | . | . |
| 21-225_25A4.001.003_LC | . | . | . | L | . | . | . | . | . | . | . | . | . | . | . | . | . | . | . | . | . | . | . | . | . | . |
| 21-225_25A4.001.004_LC | . | . | . | L | . | . | . | . | . | . | . | . | . | . | . | . | . | . | . | . | . | . | . | . | . | . |
| 21-225_25A4.001.005_LC | . | . | . | L | . | . | . | . | . | . | . | . | . | . | . | . | . | . | . | . | . | . | . | . | . | . |
| 21-225_25A4.001.006_LC | . | . | . | L | . | . | . | . | . | . | . | . | . | . | . | . | . | . | . | . | . | . | . | . | . | . |
| 21-225_25A4.001.007_LC | . | . | . | L | . | . | . | . | . | . | . | . | . | . | . | . | . | . | . | . | . | . | . | . | . | . |
| 21-225_25A4.001.008_LC | . | . | . | L | . | . | . | . | . | . | . | . | . | . | . | . | . | . | . | . | . | . | . | . | . | . |
| 21-225_25A4.001.013_LC | . | . | . | L | . | . | . | . | . | . | . | . | . | . | . | . | . | . | . | . | . | . | . | . | . | . |
| 21-225_25A4.001.019_LC | . | . | . | L | . | . | . | . | . | . | . | . | . | . | . | . | . | . | . | . | . | . | . | . | . | . |
| 21-225_25A4.001.020_LC | . | . | . | L | . | . | . | . | . | . | . | . | . | . | . | . | . | . | . | . | . | . | . | . | . | . |
| 21-225_25A4.001.021_LC | . | . | . | L | . | . | . | . | . | . | . | . | . | . | . | . | . | . | . | . | . | . | . | . | . | . |
| 21-225_25A4.001.029_LC | . | . | . | L | . | . | . | . | . | . | . | . | . | . | . | . | . | . | . | . | . | . | . | . | . | . |
| 21-225_28C4_LC | . | . | . | L | . | . | . | . | . | . | . | . | . | . | . | . | S | . | . | . | . | . | . | . | . | . |
| 21-225_29E6_LC | . | . | . | L | . | . | . | . | . | . | . | . | . | . | . | . | . | . | . | . | . | . | . | . | . | . |
| 21-225_29H8_LC | . | . | . | L | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | K_CDR3 | | | | | | | | |
| CONSENSUS | Y | C | Q | Q | Y | Y | S | | | | | | | | | | | | | | | | | | | |
| 21-225_11E5_LC | . | . | . | . | . | . | . | . | . | . | . | . | . | . | . | . | . | . | . | . | . | . | . | . | . | . |
| 21-225_12F12_LC | . | . | . | . | . | . | . | . | . | . | . | . | . | . | . | . | . | . | . | . | . | . | . | . | . | . |
| 21-225_147E4_LC | . | . | . | . | . | . | . | . | . | . | . | . | . | . | . | . | . | . | . | . | . | . | . | . | . | . |
| 21-225_148F8_LC | . | . | . | . | . | . | . | . | . | . | . | . | . | . | . | . | . | . | . | . | . | . | . | . | . | . |
| 21-225_149A2_LC | . | . | X | . | . | . | . | . | . | . | . | . | . | . | . | . | . | . | . | . | . | . | . | . | . | . |
| 21-225_149E3_LC | . | . | . | . | . | . | . | . | . | . | . | . | . | . | . | . | . | . | . | . | . | . | . | . | . | . |
| 21-225_149H4_LC | . | . | . | . | . | . | . | . | . | . | . | . | . | . | . | . | . | . | . | . | . | . | . | . | . | . |
| 21-225_154A11_LC | . | . | . | . | . | X | . | . | . | . | . | . | . | . | . | . | . | . | . | . | . | . | . | . | . | . |
| 21-225_158B12_LC | . | . | . | . | . | . | X | . | . | . | . | . | . | . | . | . | . | . | . | . | . | . | . | . | . | . |
| 21-225_162F6_LC | . | . | . | . | . | . | . | . | . | . | . | . | . | . | . | . | . | . | . | . | . | . | . | . | . | . |
| 21-225_164A4_LC | . | . | . | . | . | X | . | . | . | . | . | . | . | . | . | . | . | . | . | . | . | . | . | . | . | . |
| 21-225_164A7_LC | . | . | . | . | . | . | — | . | . | . | . | . | . | . | . | . | . | . | . | . | . | . | . | . | . | . |
| 21-225_170F6_LC | . | . | X | . | . | . | X | . | . | . | . | . | . | . | . | . | . | . | . | . | . | . | . | . | . | . |
| 21-225_174G5_LC | . | . | . | . | . | . | — | N | . | . | . | . | . | . | . | . | . | . | . | . | . | . | . | . | . | . |
| 21-225_175D10_LC | . | . | . | . | . | . | . | . | . | . | . | . | . | . | . | . | . | . | . | . | . | . | . | . | . | . |
| 21-225_177B12_LC | . | . | . | . | . | . | N | . | . | . | . | . | . | . | . | . | . | . | . | . | . | . | . | . | . | . |
| 21-225_181E5_LC | . | . | . | . | . | . | . | . | . | . | . | . | . | . | . | . | . | . | . | . | . | . | . | . | . | . |
| 21-225_190D7_LC | . | . | . | . | . | . | . | . | . | . | . | . | . | . | . | . | . | . | . | . | . | . | . | . | . | . |
| 21-225_191D8_LC | . | . | . | . | . | . | N | . | . | . | . | . | . | . | . | . | . | . | . | . | . | . | . | . | . | . |
| 21-225_193G4_LC | . | . | . | . | . | . | . | . | . | . | . | . | . | . | . | . | . | . | . | . | . | . | . | . | . | . |
| 21-225_196G8_LC | . | . | . | . | . | . | . | . | . | . | . | . | . | . | . | . | . | . | . | . | . | . | . | . | . | . |
| 21-225_197C6_LC | . | . | . | . | . | . | N | . | . | . | . | . | . | . | . | . | . | . | . | . | . | . | . | . | . | . |
| 21-225_197H4_LC | . | . | . | . | . | . | . | . | . | . | . | . | . | . | . | . | . | . | . | . | . | . | . | . | . | . |
| 21-225_200G7_LC | . | . | . | . | . | . | . | . | . | . | . | . | . | . | . | . | . | . | . | . | . | . | . | . | . | . |
| 21-225_201F5_LC | . | . | X | . | . | . | . | . | . | . | . | . | . | . | . | . | . | . | . | . | . | . | . | . | . | . |
| 21-225_213H12_LC | . | . | . | . | . | . | . | . | . | . | . | . | . | . | . | . | . | . | . | . | . | . | . | . | . | . |
| 21-225_213H7_LC | X | . | . | . | . | S | . | . | . | . | . | . | . | . | . | . | . | . | . | . | . | . | . | . | . | . |
| 21-225_222H3_LC | . | . | . | . | . | S | N | . | . | . | . | . | . | . | . | . | . | . | . | . | . | . | . | . | . | . |
| 21-225_223G10_LC | S | . | L | . | . | . | . | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | T | P | P | T | F | G | Q | G | T | K | V | E | L | K | R |
| | | | | | | | | | | | | | | L_FR4 | | | | | |
| CONSENSUS | | | | | T | P | P | T | F | G | Q | G | T | K | V | E | L | K | R |
| 21-225_224D8_LC | . | . | . | . | . | . | . | . | . | . | . | . | . | . | . | . | . | . | . |
| 21-225_224H5_LC | . | . | . | . | . | . | . | . | . | . | . | . | . | . | . | . | . | N | . |
| 21-225_225F11_LC | . | . | . | . | S | . | . | . | . | . | . | . | . | . | . | . | . | . | . |
| 21-225_225F5_LC | . | . | . | . | S | . | W | . | . | . | . | . | . | . | . | . | . | . | . |
| 21-225_226A12_LC | . | . | . | . | . | . | . | . | . | . | . | . | . | . | . | . | . | . | . |
| 21-225_226D11_LC | . | . | . | . | . | . | . | . | . | . | . | . | . | . | . | . | . | . | . |
| 21-225_226F8_LC | . | . | . | . | S | . | W | . | . | . | . | . | . | . | . | . | . | . | . |
| 21-225_227C7_LC | . | . | . | . | . | . | . | . | . | . | . | . | . | . | . | . | . | . | . |
| 21-225_23A12_LC | . | . | . | . | . | . | . | . | . | . | . | . | . | . | . | . | . | . | . |
| 21-225_23G12_LC | . | . | . | . | . | . | . | . | . | . | . | . | . | . | . | . | . | . | . |
| 21-225_24E1_LC | . | . | . | . | . | . | . | . | . | . | . | . | . | . | . | . | . | . | . |
| 21-225_25A4_LC | . | . | . | . | . | . | . | . | . | . | . | . | . | . | . | . | . | . | . |
| 21-225_25A4.001.001_LC | . | . | . | . | . | . | . | . | . | . | . | . | . | . | . | . | . | . | . |
| 21-225_25A4.001.002_LC | . | . | . | . | . | . | . | . | . | . | . | . | . | . | . | . | . | . | . |
| 21-225_25A4.001.003_LC | . | . | . | . | . | . | . | . | . | . | . | . | . | . | . | . | . | . | . |
| 21-225_25A4.001.004_LC | . | . | . | . | . | . | . | . | . | . | . | . | . | . | . | . | . | . | . |
| 21-225_25A4.001.005_LC | . | . | . | . | . | . | . | . | . | . | . | . | . | . | . | . | . | . | . |
| 21-225_25A4.001.006_LC | . | . | . | . | . | . | . | . | . | . | . | . | . | . | . | . | . | . | . |
| 21-225_25A4.001.007_LC | . | . | . | . | . | . | . | . | . | . | . | . | . | . | . | . | . | . | . |
| 21-225_25A4.001.008_LC | . | . | . | . | . | . | . | . | . | . | . | . | . | . | . | . | . | . | . |
| 21-225_25A4.001.013_LC | . | . | . | . | . | . | . | . | . | . | . | . | . | . | . | . | . | . | . |
| 21-225_25A4.001.019_LC | . | . | . | . | . | . | . | . | . | . | . | . | . | . | . | . | . | . | . |
| 21-225_25A4.001.020_LC | . | . | . | . | . | . | . | . | . | . | . | . | . | . | . | . | L | . | . |
| 21-225_25A4.001.021_LC | . | . | . | . | . | . | . | . | . | . | . | . | . | . | . | . | . | . | . |
| 21-225_25A4.001.029_LC | . | . | . | . | . | . | . | . | . | . | . | . | . | . | . | . | . | . | . |
| 21-225_26C4_LC | . | . | . | . | . | . | . | . | . | . | . | . | . | . | . | . | . | . | . |
| 21-225_29E6_LC | . | . | . | . | . | . | . | . | . | . | . | . | . | . | . | . | . | . | . |
| 21-225_29H8_LC | . | . | . | . | . | . | . | . | . | . | . | . | . | . | . | . | . | . | . |

Table 100. Consensus 20 - VK1|A30/JK3 (SEQ ID NO: 50317):

DIQMTQSPSSLSASVGDRVTITCRAS--QGIR------NDLGWYQQKPGKAPKRLIYA------ASSLQSGVPSRFSGSGSG--
TEFTLTISSLQPEDFATYYCLQHNS................YPFTFGPGTKVDIKR wherein:

A at position 25 can be substituted with T

G at position 30 can be substituted with D or V

I at position 31 can be substituted with M

R at position 32 can be substituted with S

N at position 39 can be substituted with K, S, D or T

D at position 40 can be substituted with N, H, Y, V, A, I or L

L at position 41 can be substituted with F

G at position 42 can be substituted with D

A at position 58 can be substituted with P, T, G, I, R or V

A at position 67 can be substituted with V

S at position 68 can be substituted with F or T

S at position 69 can be substituted with N, T, R or D

L at position 70 can be substituted with V

Q at position 71 can be substituted with L

S at position 72 can be substituted with N, T, G or R

L at position 107 can be substituted with I

Q at position 108 can be substituted with H or L

FIGURE 57 (Continued)

H at position 109 can be substituted with Y, D or L

N at position 110 can be substituted with Y, T, H, G or I

S at position 111 can be substituted with R, D, T, G or N

Y at position 135 can be substituted with F or H

P at position 136 can be substituted with L

F at position 137 can be substituted with L

T at position 138 can be substituted with K

Arg Xaa Ser Gln Xaa Xaa Xaa Xaa Xaa Xaa Xaa (SEQ ID NO: 50135)

Xaa Xaa Xaa Xaa Xaa Xaa Xaa Xaa (SEQ ID NO: 50136)

Xaa Xaa Xaa Xaa Xaa Xaa Xaa Xaa Xaa Xaa (SEQ ID NO: 50137)

Arg Ala Ser Gln Gly Ile Arg Asn Asp Leu Gly (SEQ ID NO: 50621)

Ala Ala Ser Ser Leu Gln Ser (SEQ ID NO: 50622)

Leu Gln His Asn Ser Tyr Pro Phe Thr (SEQ ID NO: 50623)

Table 101. Consensus 21 - VKIiL1/JK4 (SEQ ID NO: 50318):

DIQMTQSPSSLSASVGDRVTITCRAS--QGIS-----NYLAWFQQKPGKAPKSLIY A---------ASSLQSGVPSKFSGSGSG--
TDFTLTISSLQPEDFATYYCQQYST--------------YPLTFGGGTKVEIKR wherein:

A at position 25 can be substituted with T

S at position 26 can be substituted with N

G at position 30 can be substituted with D, A, V or S

S at position 32 can be substituted with G, N, R, A or F

N at position 39 can be substituted with K, R, H, S, T or I

Y at position 40 can be substituted with H, C or D

A at position 42 can be substituted with D, V, I or N

A at position 58 can be substituted with K, S, T, V, D or G

A at position 67 an be substituted with T or V

S at position 68 can be substituted with P

S at position 69 can be substituted with N or R

Q at position 71 can be substituted with L, E or H

S at position 72 can be substituted with G, N or T

Q at position 107 can be substituted with L or H

Q at position 108 can be substituted with H, R or Y

Y at position 109 can be substituted with S, C or T

S at position 110 can be substituted with L, N, M, D, H, V, I or Y

FIGURE 57 (Continued)

T at position 111 can be substituted with N, S or K

Y at position 135 can be substituted with F, I or S

L at position 137 can be substituted with V, F or N

T at position 138 can be substituted with I, Q or S

Arg Xaa Xaa Gln Xaa Ile Xaa Xaa Xaa Leu Xaa (SEQ ID NO: 50138)

Xaa Xaa Xaa Xaa Leu Xaa Xaa Xaa (SEQ ID NO: 50139)

Xaa Xaa Xaa Xaa Xaa Xaa Pro Xaa Xaa (SEQ ID NO: 50140)

Arg Ala Ser Gln Gly Ile Ser Asn Tyr Leu Ala (SEQ ID NO: 50624)

Ala Ala Ser Ser Leu Gln Ser (SEQ ID NO: 50625)

Gln Gln Tyr Ser Thr Tyr Pro Leu Thr (SEQ ID NO: 50626)

| Reference # | 1 | 2 | 3 | 4 | 5 | 6 | 7 | 8 | 9 | 10 | 11 | 12 K_FR1 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| CONSENSUS | D | I | Q | M | T | Q | S | P | S | S | L | S | A | S | V | G | D | R | V | T | I | T | C | R | A | S |
| 21-225_77E6_LC | . | . | . | . | . | . | . | . | . | . | . | . | . | . | . | . | . | . | . | . | . | . | . | . | . | . |
| 21-225_79A12_LC | . | . | . | . | . | . | . | . | . | . | . | . | . | . | . | . | . | . | . | . | . | . | . | . | . | . |
| 21-225_79F4_LC | . | . | . | . | . | . | . | . | . | A | . | . | . | . | . | . | . | . | . | . | . | . | . | . | . | . |
| 21-225_7F10_LC | . | . | . | . | . | . | . | . | . | . | . | . | . | . | . | . | . | . | . | . | . | . | . | . | . | . |
| 21-225_80C11_LC | . | . | . | . | . | . | . | . | . | . | . | . | . | . | . | . | . | . | . | . | . | . | . | . | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | K_CDR1 | | | | | | | | | | | | K_FR2 | | | | | | | | |
| CONSENSUS | . | - | Q | G | I | S | . | . | . | . | . | . | N | Y | L | A | W | F | Q | Q | K | P | G | K | A | P |
| 21-225_77E6_LC | . | . | . | . | . | . | . | . | . | . | . | . | . | . | . | . | . | . | . | . | . | . | . | . | . | . |
| 21-225_79A12_LC | . | . | . | V | . | . | . | . | . | . | . | . | K | . | . | . | . | . | . | . | . | . | . | . | . | . |
| 21-225_79F4_LC | . | . | . | D | . | S | . | . | . | . | . | . | K | . | . | . | . | . | . | . | . | . | . | . | . | . |
| 21-225_7F10_LC | . | . | . | . | . | G | . | . | . | . | . | . | . | . | . | . | . | . | . | . | . | . | . | . | . | . |
| 21-225_80C11_LC | . | . | . | . | . | . | . | . | . | . | . | . | K | . | . | . | . | . | . | . | . | . | . | K | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | K_CDR2 | | | | | | | | | | | | | | |
| CONSENSUS | K | S | L | I | Y | A | . | . | . | . | . | . | . | A | S | S | L | Q | S | G | V | P | S | K | F |
| 21-225_77E6_LC | . | . | . | . | . | . | . | . | . | . | . | . | . | . | . | . | . | . | . | . | A | . | . | . | . |
| 21-225_79A12_LC | . | . | . | . | S | V | . | . | . | . | . | . | . | . | . | . | . | . | Q | . | A | . | . | . | . |
| 21-225_79F4_LC | . | . | . | . | . | T | . | . | . | . | . | . | . | . | . | . | . | . | . | . | A | . | . | . | . |
| 21-225_7F10_LC | . | . | . | . | . | . | . | . | . | . | . | . | . | . | . | . | . | . | . | . | . | . | . | . | . |
| 21-225_80C11_LC | . | . | . | . | . | . | . | . | . | . | . | . | . | . | . | . | . | . | . | . | A | . | . | . | . |

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | K_FR3 | | | | | | | | | | | | | | | | |
| CONSENSUS | S | G | S | G | S | G | - | T | D | F | K | T | L | T | I | S | S | L | Q | P | E | D | F | A | T | Y |
| 21-225_77E6_LC | . | . | . | . | . | . | . | . | . | . | . | . | . | . | . | . | . | . | . | . | . | . | . | . | . | . |
| 21-225_79A12_LC | . | . | . | . | . | . | . | . | . | . | . | . | . | . | . | . | . | . | . | . | . | . | . | . | . | . |
| 21-225_79F4_LC | . | . | . | . | . | . | . | . | . | . | . | . | . | . | . | . | . | . | . | . | . | . | . | . | . | . |
| 21-225_7F10_LC | . | . | . | . | . | . | . | . | . | . | . | . | . | . | . | . | . | . | . | . | . | . | . | . | . | . |
| 21-225_80C11_LC | . | . | . | . | . | . | . | . | . | . | . | . | . | . | . | . | . | . | . | . | . | . | . | . | . | . |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | Y | C | Q | Q | Y | S | T | | | | | | | | | | K_CDR3 | | | | | | | | | |
| CONSENSUS | Y | C | Q | Q | Y | S | T | | | | | | | | | | | | | | | | | | | |
| 21-225_77E6_LC | . | . | . | . | . | . | N | . | . | . | . | . | . | . | . | . | . | . | . | . | . | . | . | . | . | . |
| 21-225_79A12_LC | . | . | . | . | . | . | N | . | . | . | . | . | . | . | . | . | . | . | . | . | . | . | . | . | . | . |
| 21-225_79F4_LC | . | . | . | . | . | N | N | . | . | . | . | . | . | . | . | . | . | . | . | . | . | . | . | . | . | . |
| 21-225_7F10_LC | . | . | . | . | . | . | S | . | . | . | . | . | . | . | . | . | . | . | . | . | . | . | . | . | . | . |
| 21-225_80C11_LC | . | . | . | . | . | . | N | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | K_FR4 | | | | | |
| CONSENSUS | ' | ' | ' | ' | Y | P | L | T | F | G | G | G | T | K | V | E | I | K | R |
| 21-225_77E6_LC | . | . | . | . | . | . | . | . | . | . | . | . | . | . | . | . | . | . | . |
| 21-225_79A12_LC | . | . | . | . | . | . | . | . | . | . | . | . | . | @ | . | . | . | . | . |
| 21-225_79F4_LC | . | . | . | . | . | . | . | . | . | . | . | . | . | @ | . | . | . | . | . |
| 21-225_7F10_LC | . | . | . | . | . | . | . | . | . | . | . | . | . | . | . | . | . | . | . |
| 21-225_80C11_LC | . | . | . | . | . | . | . | . | . | . | . | . | . | . | . | . | . | N | . |

FIGURE 57 (Continued)

Table 102. Consensus 22 - VK1IO12/JK4 (SEQ ID NO: 50319):

DIQMTQSPSSLSASVGDRVTITCRAS--QNII------SYLNWYQQKPGKAPKLLIYT------ASSLQSGVPSRFSGSGSG--
TDFTLTISSLQPEDFATYYCQQSYS---------------TPLTFGGGTKVEIKR wherein:

A at position 25 can be substituted with T
S at position 26 can be substituted with T
Q at position 29 can be substituted with H or R
N at position 30 can be substituted with S, R, T or I
I at position 31 can be substituted with V or F
I at position 32 can be substituted with S, N, Y, F, R, H, L, K or T
S at position 39 can be substituted with N, D, R, K or T
Y at position 40 can be substituted with F
N at position 42 an be substituted with H
T at position 58 can be substituted with A, V, G, I or S
A at position 67 can be substituted with T
S at position 69 can be substituted with N, R or T
L at position 70 can be substituted with F or S
Q at position 71 can be substituted with H, E or P
S at position 72 can be substituted with G, T, N or R
Q at position 108 can be substituted with L
S at position 109 can be substituted with T, N or P FIGURE 57 (Continued)

Y at position 110 can be substituted with H, C, D, F or N

S at position 111 can be substituted with null (-), I, N, F, G or T

T at position 135 can be substituted with S, P, F, N, I or L

P at position 136 can be substituted with T, I, A or S

L at position 137 can be substituted with P, Y, F or V

Arg Xaa Xaa Xaa Xaa Xaa Xaa Xaa Leu Xaa (SEQ ID NO: 50141)

Xaa Xaa Ser Xaa Xaa Xaa Xaa (SEQ ID NO: 50142)

Gln Xaa Xaa Xaa Xaa Xaa Xaa Xaa Xaa Thr (SEQ ID NO: 50143)

Arg Ala Ser Gln Asn Ile Ile Ser Tyr Leu Asn (SEQ ID NO: 50627)

Thr Ala Ser Ser Leu Gln Ser (SEQ ID NO: 50628)

Gln Gln Ser Tyr Ser Thr Pro Leu Thr (SEQ ID NO: 50629)

| Reference # | 131 | 132 | 133 | 134 | 135 T | 136 P | 137 L | 138 T | 139 F | 140 G | 141 G | 142 G | 143 T | 144 K FR4 | 145 V | 146 E | 147 I | 148 K | 149 R |
|---|---|---|---|---|---|---|---|---|---|---|---|---|---|---|---|---|---|---|---|
| CONSENSUS | . | . | . | . | . | . | . | . | . | . | . | . | . | . | . | . | . | . | . |
| 21-225_56B6_LC | . | . | . | . | P | . | . | . | . | . | . | . | . | . | . | . | . | . | . |
| 21-225_62D2_LC | . | . | . | . | P | . | . | . | . | . | . | . | . | . | . | . | . | . | . |
| 21-225_63C10_LC | . | . | . | . | P | . | . | . | . | . | . | . | . | . | . | . | . | . | . |
| 21-225_64A11_LC | . | . | . | . | L | S | . | . | . | . | . | . | . | . | . | . | L | . | . |
| 21-225_64F7_LC | . | . | . | . | P | . | F | . | . | . | . | . | . | . | . | . | . | . | . |
| 21-225_6G1_LC | . | . | . | . | P | . | . | . | . | . | . | . | . | . | . | . | . | . | . |
| 21-225_7A10_LC | . | . | . | . | . | . | . | . | . | . | . | . | . | . | . | . | . | X | . |
| 21-225_7E11_LC | . | . | . | . | . | . | . | . | . | . | . | . | . | . | . | . | . | . | . |
| 21-225_7E11.001.001_LC | . | . | . | . | . | . | . | . | . | . | . | . | . | . | . | . | . | . | . |
| 21-225_7E11.001.002_LC | . | . | . | . | . | . | . | . | . | . | . | . | . | . | . | . | . | . | . |
| 21-225_7E11.001.003_LC | . | . | . | . | . | . | . | . | . | . | . | . | . | . | . | . | . | . | . |
| 21-225_7E11.001.004_LC | . | . | . | . | . | . | . | . | . | . | . | . | . | . | . | . | . | . | . |
| 21-225_7E11.001.005_LC | . | . | . | . | . | . | . | . | . | . | . | . | . | . | . | . | . | . | . |
| 21-225_7E11.001.006_LC | . | . | . | . | . | . | . | . | . | . | . | . | . | . | . | . | . | . | . |
| 21-225_7E11.001.007_LC | . | . | . | . | . | . | . | . | . | . | . | . | . | . | . | . | . | . | . |
| 21-225_7E11.001.008_LC | . | . | . | . | . | . | . | . | . | . | . | . | . | . | . | . | . | . | . |
| 21-225_7E11.001.009_LC | . | . | . | . | . | . | . | . | . | . | . | . | . | . | . | . | . | . | . |
| 21-225_7E11.001.010_LC | . | . | . | . | . | . | . | . | . | . | . | . | . | . | . | . | . | . | . |
| 21-225_7E11.001.011_LC | . | . | . | . | . | . | . | . | . | . | . | . | . | . | . | . | . | . | . |
| 21-225_7E11.001.012_LC | . | . | . | . | . | . | . | . | . | . | . | . | . | . | . | . | . | . | . |
| 21-225_7E11.001.013_LC | . | . | . | . | . | . | . | . | . | . | . | . | . | . | . | . | . | . | . |
| 21-225_7E11.001.014_LC | . | . | . | . | . | . | . | . | . | . | . | . | . | . | . | . | . | . | . |
| 21-225_7E11.001.015_LC | . | . | . | . | . | . | . | . | . | . | . | . | . | . | . | . | . | . | . |
| 21-225_7E11.001.016_LC | . | . | . | . | . | . | . | . | . | . | . | . | . | . | . | . | . | . | . |
| 21-225_7E11.001.017_LC | . | . | . | . | . | . | . | . | . | . | . | . | . | . | . | . | . | . | . |
| 21-225_7E11.001.018_LC | . | . | . | . | . | . | . | . | . | . | . | . | . | . | . | . | . | . | . |
| 21-225_7E11.001.019_LC | . | . | . | . | . | . | . | . | . | . | . | . | . | . | . | . | . | . | . |
| 21-225_7E11.001.021_LC | . | . | . | . | . | . | . | . | . | . | . | . | . | . | . | . | . | . | . |

FIGURE 57 (Continued)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | K_FR4 | | | | | |
| CONSENSUS | - | - | - | - | T | P | L | T | F | G | G | G | T | K | V | E | I | K | R |
| 21-225_7E11.001.022_LC | . | . | . | . | . | . | . | . | . | . | . | . | . | . | . | . | . | . | . |
| 21-225_7E11.001.023_LC | . | . | . | . | . | . | . | . | . | . | . | . | . | . | . | . | . | . | . |

FIGURE 57 (Continued)

Table 103. Consensus 23 - VK1|L1/JK3 (SEQ ID NO: 50320):

DIQMTQSPSSLSASVGDRVTITCRAS--QGIS------NYLAWFQQKPGKAPKSLIYA-------ASSLQSGVPSKFSGSGSG---TDFTLTISSLQPEDFATYCQQYNS--------YPFTFGPGTKVDIKR wherein:

R at position 24 can be substituted with P

A at position 25 can be substituted with T

S at position 26 can be substituted with N

Q at position 29 can be substituted with R

G at position 30 can be substituted with D, V or A

I at position 31 can be substituted with V

S at position 32 can be substituted with N, G, R, T or K

N at position 39 can be substituted with K, Y, H, I or T

Y at position 40 can be substituted with H

A at position 42 can be substituted with V or S

A at position 58 can be substituted with V, G or T

A at position 67 can be substituted with S or V

S at position 68 can be substituted with F

S at position 69 can be substituted with G, N or T

L at position 70 can be substituted with V

Q at position 71 can be substituted with R, H, L or E

S at position 72 can be substituted with G or T

FIGURE 57 (Continued)

Q at position 107 can be substituted with H, L, P or R
Q at position 108 can be substituted with R, K, H or L
Y at position 109 can be substituted with F
N at position 110 can be substituted with H, D, Y, S, K, L, M or Q
S at position 111 can be substituted with T, G, N, C or D
Y at position 135 can be substituted with F or H
F at position 137 can be substituted with V, L or I
T at position 138 can be substituted with K
Xaa Xaa Xaa Xaa Xaa Xaa Xaa Xaa Leu Xaa (SEQ ID NO: 50144)
Xaa Xaa Xaa Xaa Xaa Xaa Xaa Xaa (SEQ ID NO: 50145)
Xaa Xaa Xaa Xaa Xaa Xaa Pro Xaa Xaa (SEQ ID NO: 50146)
Arg Ala Ser Gln Gly Ile Ser Asn Tyr Leu Ala (SEQ ID NO: 50630)
Ala Ala Ser Ser Leu Gln Ser (SEQ ID NO: 50631)
Gln Gln Tyr Asn Ser Tyr Pro Phe Thr (SEQ ID NO: 50632)

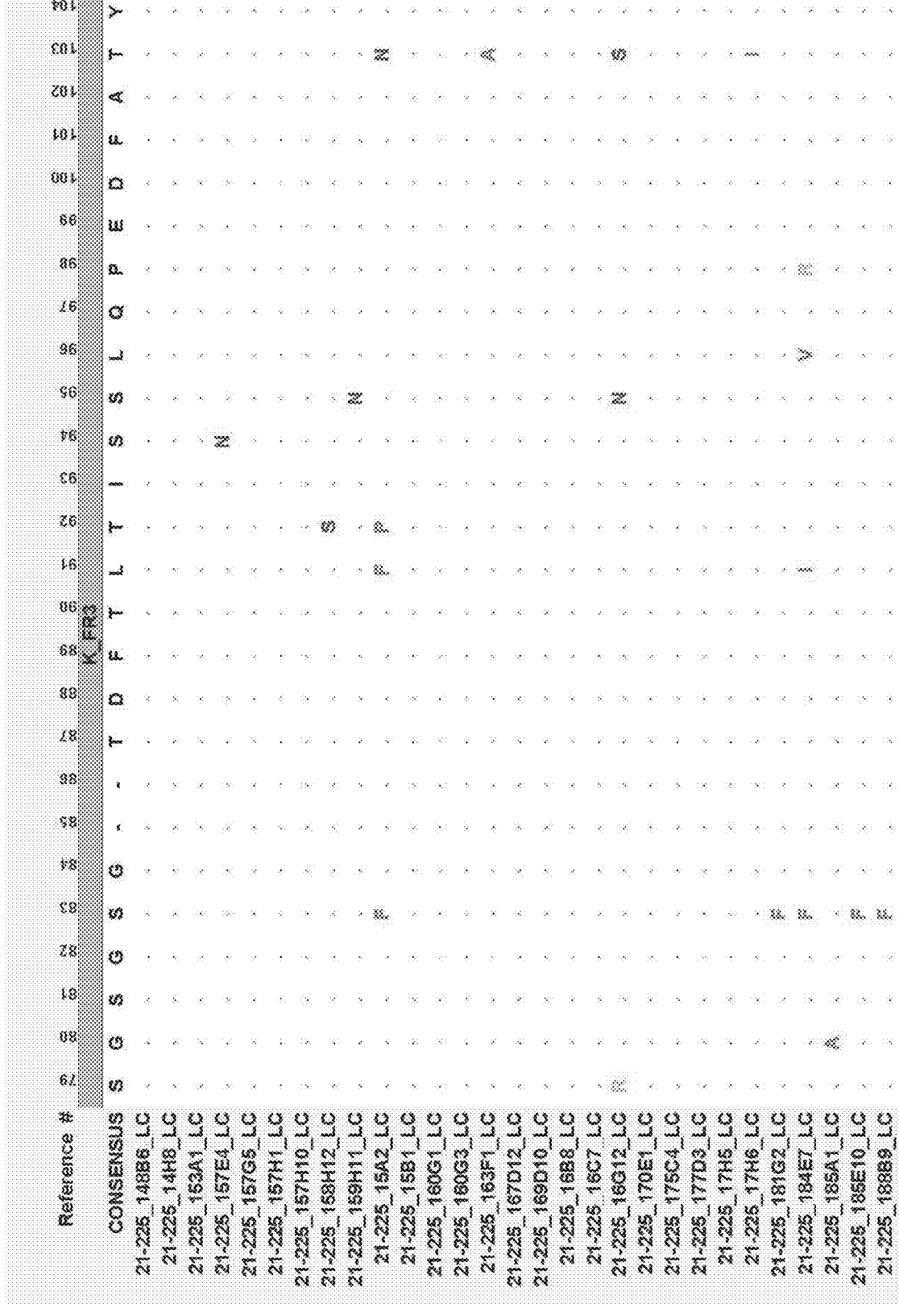

Table 104. Consensus 24 - VK1jL5/JK3 (SEQ ID NO: 50321):

DIQMTQSPSSVSASVGDRVTITCRAS--QGIS-------RWLAWYQQKPGKAPKLLIYA--------ASSLQSGVPSRFSGSGSG---
TDFTLTISSLQPEDFATYYCQQANS--------------FPFTFGPGTKVDIKR wherein:

A at position 25 can be substituted with V, E or G

S at position 26 can be substituted with G

Q at position 29 can be substituted with R

G at position 30 can be substituted with D, N, A, L or V

I at position 31 can be substituted with V or F

S at position 32 can be substituted with N, T, R or I

R at position 39 can be substituted with S, N, K, T, D, I or G

W at position 40 can be substituted with Y

L at position 41 can be substituted with I

A at position 42 can be substituted with T or V

A at position 58 can be substituted with G, T, D or V

A at position 67 can be substituted with T or V

S at position 68 can be substituted with Y

S at position 69 can be substituted with R, N, T, G or I

L at position 70 can be substituted with F

Q at position 71 can be substituted with E

FIGURE 57 (Continued)

S at position 72 can be substituted with G, N or D

Q at position 107 can be substituted with H

A at position 109 can be substituted with T, G, S, V or D

N at position 110 can be substituted with D, K or S

S at position 111 can be substituted with I

F at position 135 can be substituted with L, I or V

F at position 137 can be substituted with I

Arg Xaa Xaa Xaa Xaa Xaa Xaa Xaa Xaa Xaa (SEQ ID NO: 50147)

Xaa Xaa Xaa Xaa Xaa Xaa Xaa Xaa (SEQ ID NO: 50148)

Xaa Gln Xaa Xaa Xaa Xaa Pro Xaa Thr (SEQ ID NO: 50149)

Arg Ala Ser Gln Gly Ile Ser Arg Trp Leu Ala (SEQ ID NO: 50633)

Ala Ala Ser Ser Leu Gln Ser (SEQ ID NO: 50634)

Gln Gln Ala Asn Ser Phe Pro Phe Thr (SEQ ID NO: 50635)

FIGURE 57 (Continued)

| Reference # | 1 | 2 | 3 | 4 | 5 | 6 | 7 | 8 | 9 | 10 | 11 | 12 K_FR1 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| CONSENSUS | D | I | Q | M | T | Q | S | P | S | S | V | S | A | S | V | G | D | R | V | T | I | T | C | R | A | S |
| 21-225_4H6.014_LC | | | | | | | | | | | | | | | | | | | | | | | | | | |
| 21-225_50D4_LC | | | | | | | | | | | | | | | | | | | L | | | | | | | |
| 21-225_50F3_LC | | | | | | | | | | | | | | | | | | | | | | | | | | |
| 21-225_51C7_LC | | | | | | | | | | | | | | | | | | | | | | | | | | |
| 21-225_51E9_LC | | | | | | | | | | | | | | | | | | | R | | | | | | | |
| 21-225_52B1_LC | | | | | | | | | | | | | T | | | | | | | | | | | | | |
| 21-225_52G11_LC | | | | | S | | | | | | | | | P | | | | | | | | | | | | |
| 21-225_52H10_LC | | | | | | | | | | | | | | | | | | | | | | | | | | |
| 21-225_53F2_LC | | | | | | | | | | | | | | | | | | | | | | | | | | |
| 21-225_53F7_LC | | | | | | | | | | | | | | | | | | | | | | | | | | |
| 21-225_55B1_LC | | | | | | | | | | | | | | | | | | | | | | | | | | |
| 21-225_56C6_LC | | | | | | | | | | | | | | | | | | | | | | | | | | |
| 21-225_56E5_LC | | | | | | | | | | | | | | | | | | | | | | | | | | |
| 21-225_56F6_LC | | | | | | | | | | | | C | | Y | | | | | | | | | | | V | |
| 21-225_57A7_LC | | | | | | | | | | | | | | | | | | | | S | | | | | | Q |
| 21-225_57E4_LC | | | | | | | | | | | | | | | | | | | | | | | | | | |
| 21-225_64E2_LC | | | | | | | | | | | | | | | | | | | | | | | | | | |
| 21-225_64G12_LC | | | | | | | | | | | | | | | | | | | | | | | | | Q | Q |
| 21-225_65F10_LC | | | | | | | | | | | | C | | | | | | | | | | | | | E | |
| 21-225_66F11_LC | | | | | | | | | | | | | | | | | | | | | | | | | | |
| 21-225_70D1_LC | | | | | | | | | | | | | | | L | | | | | | | | | | | |
| 21-225_7C3_LC2_LC | | | | | | | | | | | | | | | | | | | | | | | | | | |
| 21-225_9F12_LC1_LC | | | | | | | | | | | | | | | | | | | | | | | | | | |

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | K_CDR3 | | | | | | | | |
| CONSENSUS | Y | C | Q | Q | A | N | S | | | | | | | | | | | | | | | | | | | |
| 21-225_2B1_LC | . | . | . | . | . | . | . | . | . | . | . | . | . | . | . | . | . | . | . | . | . | . | . | . | . | . |
| 21-225_28F11_LC | C | . | . | . | . | . | . | . | . | . | . | . | . | . | . | . | . | . | . | . | . | . | . | . | . | . |
| 21-225_30A11_LC | . | . | . | . | . | . | . | . | . | . | . | . | . | . | . | . | . | . | . | . | . | . | . | . | . | . |
| 21-225_31C4_LC | . | . | . | . | . | . | . | . | . | . | . | . | . | . | . | . | . | . | . | . | . | . | . | . | . | . |
| 21-225_31H9_LC | . | . | . | . | O | . | . | . | . | . | . | . | . | . | . | . | . | . | . | . | . | . | . | . | . | . |
| 21-225_33G1_LC | . | . | . | . | . | . | . | . | . | . | . | . | . | . | . | . | . | . | . | . | . | . | . | . | . | . |
| 21-225_33H7_LC | . | . | . | . | . | . | . | . | . | . | . | . | . | . | . | . | . | . | . | . | . | . | . | . | . | . |
| 21-225_34F3_LC | . | . | . | . | . | . | . | . | . | . | . | . | . | . | . | . | . | . | . | . | . | . | . | . | . | . |
| 21-225_34G7_LC | . | . | . | . | . | . | . | . | . | . | . | . | . | . | . | . | . | . | . | . | . | . | . | . | . | . |
| 21-225_35C6_LC | . | . | . | . | . | . | . | . | . | . | . | . | . | . | . | . | . | . | . | . | . | . | . | . | . | . |
| 21-225_35G6_LC | . | . | . | . | . | . | . | . | . | . | . | . | . | . | . | . | . | . | . | . | . | . | . | . | . | . |
| 21-225_35H12_LC | . | . | . | . | . | . | . | . | . | . | . | . | . | . | . | . | . | . | . | . | . | . | . | . | . | . |
| 21-225_36H5_LC | R | . | . | . | . | . | . | . | . | . | . | . | . | . | . | . | . | . | . | . | . | . | . | . | . | . |
| 21-225_43H9_LC | . | . | . | . | . | . | . | . | . | . | . | . | . | . | . | . | . | . | . | . | . | . | . | . | . | . |
| 21-225_44F3_LC | . | . | . | . | . | . | . | . | . | . | . | . | . | . | . | . | . | . | . | . | . | . | . | . | . | . |
| 21-225_45C9_LC | . | . | . | . | . | . | . | . | . | . | . | . | . | . | . | . | . | . | . | . | . | . | . | . | . | . |
| 21-225_45H4_LC | R | . | . | . | . | . | . | . | . | . | . | . | . | . | . | . | . | . | . | . | . | . | . | . | . | . |
| 21-225_49F1_LC | . | . | . | . | S | . | . | . | . | . | . | . | . | . | . | . | . | . | . | . | . | . | . | . | . | . |
| 21-225_49F10_LC | . | . | . | . | T | . | . | . | . | . | . | . | . | . | . | . | . | . | . | . | . | . | . | . | . | . |
| 21-225_49H5_LC | . | . | . | . | . | . | . | . | . | . | . | . | . | . | . | . | . | . | . | . | . | . | . | . | . | . |
| 21-225_4H6_LC | . | . | . | . | . | . | . | . | . | . | . | . | . | . | . | . | . | . | . | . | . | . | . | . | . | . |
| 21-225_4H6.004_LC | . | . | . | . | . | . | . | . | . | . | . | . | . | . | . | . | . | . | . | . | . | . | . | . | . | . |
| 21-225_4H6.005_LC | . | . | . | . | . | . | . | . | . | . | . | . | . | . | . | . | . | . | . | . | . | . | . | . | . | . |
| 21-225_4H6.006_LC | . | . | . | . | . | . | . | . | . | . | . | . | . | . | . | . | . | . | . | . | . | . | . | . | . | . |
| 21-225_4H6.007_LC | . | . | . | . | . | . | . | . | . | . | . | . | . | . | . | . | . | . | . | . | . | . | . | . | . | . |
| 21-225_4H6.008_LC | . | . | . | . | . | . | . | . | . | . | . | . | . | . | . | . | . | . | . | . | . | . | . | . | . | . |
| 21-225_4H6.009_LC | . | . | . | . | . | . | . | . | . | . | . | . | . | . | . | . | . | . | . | . | . | . | . | . | . | . |
| 21-225_4H6.010_LC | . | . | . | . | . | . | . | . | . | . | . | . | . | . | . | . | . | . | . | . | . | . | . | . | . | . |
| 21-225_4H6.011_LC | . | . | . | . | . | . | . | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | K_FR4 | | | | | | | |
| CONSENSUS | - | - | - | - | F | P | F | T | F | G | P | G | T | K | V | D | I | K | R |
| 21-225_4H6.014_LC | . | . | . | . | . | . | . | . | . | . | . | . | . | . | . | . | . | X | . |
| 21-225_50D4_LC | . | . | . | . | . | . | . | . | . | . | . | . | . | . | . | . | . | . | . |
| 21-225_50F3_LC | . | . | . | . | . | . | . | . | . | . | . | . | . | . | . | . | . | . | . |
| 21-225_51C7_LC | . | . | . | . | . | . | . | . | . | . | . | . | . | . | . | . | V | . | . |
| 21-225_51E9_LC | . | . | . | . | . | . | . | . | . | . | . | . | . | . | . | . | V | . | . |
| 21-225_52B1_LC | . | . | . | . | . | . | . | . | . | . | . | . | . | . | . | . | L | . | . |
| 21-225_52G11_LC | . | . | . | . | . | . | . | . | . | . | . | . | . | . | . | . | . | . | . |
| 21-225_52H10_LC | . | . | . | . | . | . | . | . | . | . | . | . | . | . | . | . | . | . | . |
| 21-225_53F2_LC | . | . | . | . | . | . | . | . | . | . | . | . | . | . | . | . | . | . | . |
| 21-225_53F7_LC | . | . | . | . | . | . | . | . | . | . | . | . | . | . | . | . | . | . | . |
| 21-225_55B1_LC | . | . | . | . | . | . | . | . | . | . | . | . | . | . | . | . | . | . | . |
| 21-225_56C6_LC | . | . | . | . | . | . | . | . | . | . | . | . | . | . | . | . | . | . | . |
| 21-225_56E5_LC | . | . | . | . | . | . | . | . | . | . | . | . | . | . | . | . | . | . | . |
| 21-225_56F8_LC | . | . | . | . | . | . | . | . | . | . | . | . | . | . | . | . | . | . | . |
| 21-225_57A7_LC | . | . | . | . | . | . | . | . | . | . | . | . | . | . | L | . | . | . | . |
| 21-225_57E4_LC | . | . | . | . | . | . | . | . | . | . | R | . | . | . | . | . | . | . | . |
| 21-225_64E2_LC | . | . | . | . | . | . | . | . | . | . | . | . | . | . | . | . | . | . | . |
| 21-225_64G12_LC | . | . | . | . | . | . | . | . | . | . | . | . | . | . | . | . | . | . | . |
| 21-225_65F10_LC | . | . | . | . | . | . | . | . | . | . | . | . | . | . | . | . | . | . | . |
| 21-225_68F11_LC | . | . | . | . | . | . | . | . | . | . | . | . | . | . | . | . | . | . | . |
| 21-225_70D1_LC | . | . | . | . | . | . | . | . | . | . | . | . | . | . | . | . | . | . | . |
| 21-225_7C3_LC2_LC | . | . | . | . | . | . | . | . | . | . | . | . | . | . | . | . | F | . | . |
| 21-225_9F12_LC1_LC | . | . | . | . | . | . | . | . | . | . | . | . | . | . | . | . | . | . | . |

FIGURE 57 (Continued)

Table 105. Consensus 25 - VK2|A18/JK1 (SEQ ID NO: 50322):

DIVMTQTPLSLSVTPGQPASISCKSS--QSLLHGD-GKTYLYWYLQKPGQPPQLLIYE--------VSNRFSGVPDRFSGSGSG--
TDFTLKISRVEAEDVGVYCMQSIQ----------------LPWTFGQGTKVEIKR wherein:

K at position 24 can be substituted with M, R or T

S at position 26 can be substituted with G or T

Q at position 29 can be substituted with K

S at position 30 can be substituted with R, N or T

L at position 32 can be substituted with R or V

H at position 33 can be substituted with Y

G at position 34 can be substituted with S

D at position 35 can be substituted with E or G

K at position 38 can be substituted with R

Y at position 40 can be substituted with F

L at position 41 can be substituted with F

Y at position 42 can be substituted with F, T, C or S

E at position 58 can be substituted with A

V at position 67 can be substituted with I, L or T

N at position 69 can be substituted with K, H, I or S

F at position 71 can be substituted with L

S at position 72 can be substituted with A, T, C or P

FIGURE 57 (Continued)

M at position 107 can be substituted with K

S at position 109 can be substituted with T

I at position 110 can be substituted with T, F or L

Q at position 111 can be substituted with H

L at position 135 can be substituted with I, V or F

W at position 137 can be substituted with R

Xaa Ser Xaa Xaa Leu Xaa Xaa Xaa Gly Xaa Thr Xaa Xaa Xaa (SEQ ID NO: 50150)

Xaa Xaa Ser Xaa Arg Xaa Xaa (SEQ ID NO: 50151)

Xaa Gln Xaa Xaa Xaa Pro Xaa Thr (SEQ ID NO: 50152)

Lys Ser Ser Gln Ser Leu Leu His Gly Asp Gly Lys Thr Tyr Leu Tyr (SEQ ID NO: 50636)

Glu Val Ser Asn Arg Phe Ser (SEQ ID NO: 50637)

Met Gln Ser Ile Gln Leu Pro Trp Thr (SEQ ID NO: 50638)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | K_FR1 | | | | | | | | | | | | | | | |
| CONSENSUS | D | I | V | M | T | Q | T | P | L | S | L | S | V | T | P | G | Q | P | A | S | I | S | C | K | S | S |
| 21-225_28F8_LC | E | . | . | . | . | . | . | . | . | . | . | . | . | . | . | . | . | . | . | . | . | . | . | . | . | . |
| 21-225_28G3_LC | . | . | . | . | . | . | . | . | . | . | . | . | . | . | . | . | . | . | . | . | . | . | . | . | . | . |
| 21-225_43E11_LC | . | . | . | . | . | . | . | . | . | . | . | T | . | . | . | . | . | . | . | . | . | . | . | . | . | . |
| 21-225_46F2_LC | . | . | . | . | . | . | . | . | . | . | . | . | . | . | . | . | . | . | . | . | . | . | . | . | . | . |
| 21-225_47C1_LC | . | . | . | . | . | . | . | . | . | . | . | . | . | . | . | . | . | . | . | . | . | . | . | T | . | . |
| 21-225_47E7_LC | . | . | . | . | . | . | . | . | . | . | . | . | . | . | . | . | . | . | . | . | . | . | . | . | . | . |
| 21-225_64H9_LC | E | . | . | . | . | . | . | . | . | . | . | . | . | . | . | . | . | . | . | . | . | . | . | . | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | K_CDR1 | | | | | | | | | | | | | | | | | K_FR2 | | | |
| CONSENSUS | - | - | Q | S | L | L | H | G | D | - | G | K | T | Y | L | Y | W | Y | L | Q | K | P | G | Q | P | P |
| 21-225_26F8_LC | . | . | . | . | . | . | . | . | . | . | . | . | . | . | . | . | . | . | . | . | . | . | . | . | . | . |
| 21-225_28G3_LC | . | . | . | . | . | . | . | S | . | . | . | . | . | . | . | . | . | . | . | . | . | . | . | . | . | . |
| 21-225_43E11_LC | . | . | . | . | . | . | . | . | . | . | . | R | . | . | . | . | . | . | . | . | . | . | . | . | . | . |
| 21-225_46F2_LC | . | . | . | . | . | . | . | . | E | . | . | . | . | . | . | . | . | . | . | . | . | . | . | . | . | . |
| 21-225_47C1_LC | . | . | . | . | . | . | . | S | . | . | . | . | . | . | . | . | . | . | . | . | . | . | . | . | . | . |
| 21-225_47E7_LC | . | . | . | . | . | . | . | S | . | . | . | R | . | . | . | R | . | . | . | . | . | . | . | . | . | . |
| 21-225_64H9_LC | . | . | . | . | . | . | . | . | . | . | . | . | . | . | . | . | . | . | . | . | . | . | . | . | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | Y | E | | | | | | K_CDR2 | | | | | | | | | | | | | | | |
| CONSENSUS | Q | L | L | I | Y | E | . | . | . | . | . | . | . | . | V | S | N | R | F | S | G | V | P | D | R | F |
| 21-225_26F8_LC | . | . | . | . | . | . | . | . | . | . | . | . | . | . | . | . | . | . | . | . | . | . | . | E | . | . |
| 21-225_28G3_LC | . | . | . | . | . | . | . | . | . | . | . | . | . | . | . | . | . | . | . | . | . | . | . | . | . | . |
| 21-225_43E11_LC | . | V | . | . | . | . | . | . | . | . | . | . | . | . | . | . | . | . | . | . | . | . | . | . | . | . |
| 21-225_46F2_LC | . | . | . | . | . | . | . | . | . | . | . | . | . | . | . | . | . | . | . | . | . | . | . | . | . | . |
| 21-225_47C1_LC | . | . | . | . | . | . | . | . | . | . | . | . | . | . | . | . | S | . | . | . | . | . | . | . | . | . |
| 21-225_47E7_LC | . | V | . | . | . | . | . | . | . | . | . | . | . | . | . | . | . | . | . | . | . | . | . | . | . | . |
| 21-225_64H9_LC | . | . | . | . | . | . | . | . | . | . | . | . | . | . | . | . | . | . | L | C | . | . | . | . | . | . |

| Reference # | 79 | 80 | 81 | 82 | 83 | 84 | 85 | 86 | 87 | 88 | 89 K FR3 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| CONSENSUS | S | G | S | G | S | G | . | T | D | F | T | T | L | K | I | S | R | V | E | A | E | D | V | G | V | Y |
| 21-225_26F8_LC | . | . | . | . | . | . | . | . | . | . | . | . | . | . | . | . | . | . | . | . | . | . | . | . | . | . |
| 21-225_28G3_LC | . | . | . | . | . | . | . | . | . | . | . | . | . | . | . | . | . | . | . | . | . | . | . | . | . | . |
| 21-225_43E11_LC | . | . | . | . | . | . | . | . | . | . | . | . | . | . | . | . | . | . | . | . | . | . | . | . | . | . |
| 21-225_46F2_LC | . | . | . | . | . | . | . | . | . | . | . | . | . | . | . | . | . | . | . | . | . | . | . | . | . | . |
| 21-225_47C1_LC | . | . | . | . | . | . | . | . | . | . | . | A | . | . | L | . | . | . | . | . | . | . | . | . | . | A |
| 21-225_47E7_LC | . | . | . | . | . | . | . | . | . | . | . | S | . | . | . | . | . | . | . | . | . | . | . | . | . | . |
| 21-225_64H9_LC | . | . | . | . | . | . | . | . | . | . | . | . | . | . | . | . | . | . | . | . | . | . | . | . | . | . |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | K_FR4 | | | | | |
| CONSENSUS | . | . | . | . | L | P | W | T | F | G | Q | G | T | K | V | E | I | K | R |
| 21-225_26F8_LC | . | . | . | . | . | . | . | . | . | . | . | . | . | . | . | . | . | . | . |
| 21-225_28G3_LC | . | . | . | . | I | . | . | . | . | . | . | . | . | . | . | . | . | . | . |
| 21-225_43E11_LC | . | . | . | . | . | . | . | . | . | . | . | . | . | . | . | . | . | . | . |
| 21-225_46F2_LC | . | . | . | . | . | . | . | . | . | . | . | . | . | . | . | . | . | . | . |
| 21-225_47C1_LC | . | . | . | . | . | . | . | . | . | . | . | . | . | . | A | . | . | . | . |
| 21-225_47E7_LC | . | . | . | . | V | . | . | . | . | . | . | . | . | . | . | . | . | T | . |
| 21-225_64H9_LC | . | . | . | . | . | . | . | . | . | . | . | . | . | . | . | . | . | . | . |

FIGURE 57 (Continued)

Table 106. Consensus 26 - VKIIO12/JK3 (SEQ ID NO: 50323):

DIQMTQSPSSLSASVGDRVTITCRAS--QSIS------SYLNWYQQKPGKAPKLLIYA------ASSLQSGVPSRFSGSGSG--TDFTLTISSLQPEDFATYYCQQSYS-----------PPFTFGPGTKVDIKR wherein:

A at position 25 can be substituted with S or T
S at position 26 can be substituted with G or I
Q at position 29 can be substituted with H or R
S at position 30 can be substituted with N or T
I at position 31 can be substituted with F
S at position 32 can be substituted with I, F, N, R, Y, T, A, G or L
S at position 39 can be substituted with N, T, H or K
Y at position 40 can be substituted with F or H
L at position 41 can be substituted with V
N at position 42 can be substituted with I, M, H or Y
A at position 58 can be substituted with G, T, V or I
A at position 67 can be substituted with T, V or S
S at position 68 can be substituted with F
S at position 69 can be substituted with N, T or V
Q at position 71 can be substituted with H
S at position 72 can be substituted with N, G, H, I or T
S at position 109 can be substituted with T or Y
Y at position 110 can be substituted with N, F or H FIGURE 57 (Continued)

S at position 111 can be substituted with R, N, F or I null (-) at position 134 can be substituted with A or S P at position 135 can be substituted with T, I, F, A, L or V P at position 136 can be substituted with L, F, or S T at position 138 can be substituted with A or S Arg Xaa Xaa Xaa Xaa Xaa Xaa Xaa Xaa Xaa (SEQ ID NO: 50153)

Xaa Xaa Xaa Xaa Leu Xaa Xaa (SEQ ID NO: 50154)

Gln Gln Xaa Xaa Xaa Xaa Xaa Xaa Phe Xaa (SEQ ID NO: 50155)

Arg Ala Ser Gln Ser Ile Ser Ser Tyr Leu Asn (SEQ ID NO: 50639)

Ala Ala Ser Ser Leu Gln Ser (SEQ ID NO: 50640)

Gln Gln Ser Tyr Ser Pro Pro Phe Thr (SEQ ID NO: 50641)

Table 107. Consensus 27 – VK4|B3/JK2 (SEQ ID NO: 50324):

DIVMTQSPDSLAVSLGERATINCKSS--QSVLYSSNNNNYLAWYQQKPGQPPKLLIYW--------ASTRESGVPDRFSGSGSG--TDFTLTISSLQAEDVAVYYCQQYYS----------------TPCSFGQGTKLEIKR wherein:

K at position 24 can be substituted with R or T
S at position 26 can be substituted with I
S at position 30 can be substituted with N
V at position 31 can be substituted with I
Y at position 33 can be substituted with H, S or F
S at position 34 can be substituted with N, I, R or H
N at position 36 can be substituted with H
N at position 37 can be substituted with S or D
N at position 38 can be substituted with Y, K, H, A, M or Q
N at position 39 can be substituted with K
Y at position 40 can be substituted with F
A at position 42 can be substituted with T or D
A at position 67 can be substituted with T, G or S
S at position 68 can be substituted with F
T at position 69 can be substituted with I
E at position 71 can be substituted with K or D
S at position 72 can be substituted with F
Q at position 107 can be substituted with H FIGURE 57 (Continued)

Q at position 108 can be substituted with H
Y at position 109 can be substituted with S
Y at position 110 can be substituted with F, K, or N
S at position 111 can be substituted with T, I, null (-) or N T at position 135 can be substituted with S, I, R, A, G or N P at position 136 can be substituted with S C at position 137 can be substituted with Y, G, L or P S at position 138 can be substituted with K or N Xaa Ser Xaa Gln Xaa Xaa Leu Xaa Xaa Ser Xaa Xaa Xaa Xaa Xaa Leu Xaa (SEQ ID NO: 50156)

Trp Xaa Xaa Xaa Arg Xaa Xaa (SEQ ID NO: 50157)

Xaa Xaa Xaa Xaa Xaa Xaa Xaa Xaa Xaa (SEQ ID NO: 50158)

Lys Ser Ser Gln Ser Val Leu Tyr Ser Ser Asn Asn Asn Asn Tyr Leu Ala (SEQ ID NO: 50642)

Trp Ala Ser Thr Arg Glu Ser (SEQ ID NO: 50643)

Gln Gln Tyr Tyr Ser Thr Pro Cys Ser (SEQ ID NO: 50644)

FIGURE 57 (Continued)

| Reference # | 131 | 132 | 133 | 134 | 135 | 136 | 137 | 138 | 139 | 140 | 141 | 142 | 143 | 144 K_FR4 | 145 | 146 | 147 | 148 | 149 |
|---|---|---|---|---|---|---|---|---|---|---|---|---|---|---|---|---|---|---|---|
| CONSENSUS | . | . | . | . | T | P | C | S | F | G | Q | G | T | K | L | E | I | K | R |
| 21-225_33D1_LC | | | | | S | | | | | | | | | | | | | | |
| 21-225_34H7_LC | | | | | S | | | | | | | | | | | | | | |
| 21-225_57F12_LC | | | | | N | | | | | | | | | | | | | | |
| 21-225_59E1_LC | | | | | I | | | | | | | | | | | | | | |
| 21-225_60F3_LC | | | | | X | | | | | | | | | | | | | N | |
| 21-225_61E3_LC | | | | | | | | | | | | | | | | | | | |
| 21-225_63F4_LC | | | | | | | | | | | | | | | | | | N | |
| 21-225_71F3_LC | | | | | | | | | | | | | | | | | | | |
| 21-225_71G3_LC | | | | | | | | | | | | | | | | | | | |
| 21-225_74A8_LC | | | | | | | | | | | | | | | | | | | |
| 21-225_74C10_LC | | | | | | | | | | | | | | | | | | | |
| 21-225_74C12_LC | | | | | | | | | | | | | | | | | | | |
| 21-225_77D12_LC | | | | | | | | | | | | | | | | | | | |
| 21-225_78E6_LC | | | | | | | | | | | | | | | | | | | |
| 21-225_79G7_LC | | | | | S | | | | | | | | | | | | | | |
| 21-225_85C11_LC | | | | | | | | | | | | | | | | | | | |
| 21-225_87E10_LC | | | | | | | | | | | | | | | X | | | | |
| 21-225_8B11_LC | | | | | | | | | | | | | | | | | | | |

FIGURE 57 (Continued)

Table 108. Consensus 28 - VK1jL5/JK1 (SEQ ID NO: 50325):

DIQMTQSPSSVSASVGDRVTITCRAS-QGIS-----NWLAWYQQKPGKAPKLLIYA-----ASSLQSGVPSRFSGSGSG--
TDFTLTISSLQPEDFATYYCQQANS------------FPWTFGQGTKVEIKR wherein:

S at position 26 can be substituted with N
G at position 30 can be substituted with D, F, N or V
I at position 31 can be substituted with L or V
S at position 32 can be substituted with N, T, I, F or G
N at position 39 can be substituted with S, D, T or R
W at position 40 can be substituted with C
A at position 58 can be substituted with G, D, T or S
A at position 67 can be substituted with V, P or T
S at position 68 can be substituted with F
S at position 69 can be substituted with N
S at position 72 can be substituted with G or N
Q at position 107 can be substituted with L
A at position 109 can be substituted with T, S, G, V or Y
A at position 110 can be substituted with D, H or Y
F at position 135 can be substituted with L
W at position 137 can be substituted with R or P Arg Ala Gln Xaa Xaa Xaa Xaa Leu Ala (SEQ ID NO: 50159)
Xaa Xaa Xaa Xaa Leu Gln Xaa (SEQ ID NO: 50160)

Xaa Gln Xaa Xaa Ser Xaa Pro Xaa Thr (SEQ ID NO: 50161)

Arg Ala Ser Gln Gly Ile Ser Asn Trp Leu Ala (SEQ ID NO: 50645)

Ala Ala Ser Ser Leu Gln Ser (SEQ ID NO: 50646)

Gln Gln Ala Asn Ser Phe Pro Trp Thr (SEQ ID NO: 50647)

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | K_CDR1 | | | | | | | | | | | | | | | K_FR2 | | | | | |
| CONSENSUS | | | Q | G | I | S | | | | | | N | W | L | A | W | Y | Q | Q | K | P | G | K | A | P |
| 21-225_43H4_LC | | | | | | | | | | | | | | | | | | | | | | | | | | |
| 21-225_44C12_LC | | | | | | | | | | | | D | | | | | | | | | | | | | | |
| 21-225_44D10_LC | | | | | | | | | | | | D | | | | | | | | | | | | | | |
| 21-225_45F8_LC | | | | | | T | | | | | | | | | | | | | | | | | | | | |
| 21-225_46A6_LC | | | | N | | | | | | | | S | | | | | | | | | | | | | | |
| 21-225_47G7_LC | | | | D | | | | | | | | S | | | | | | | | | | | | | | |
| 21-225_48D7_LC | | | | N | | T | | | | | | | | | | | | | | | | | | | | |
| 21-225_51G7_LC | | | | | | | | | | | | S | | | | | | | | | | | | | | |
| 21-225_52H2_LC | | | | | | | | | | | | | | | | | Y | | | K | | | | | | |
| 21-225_54G3_LC | | | | | | | | | | | | T | | | | | | | | | | | | | | |
| 21-225_57F8_LC | | | | | | | | | | | | | | | | | | | | | | | | | | |
| 21-225_5A4_LC | | | | | | | | | | | | | | | | | | | | | | | | | | |
| 21-225_60A11_LC | | | | V | | | | | | | | | | | | | | | L | | | | | | | |

Table 109. Consensus 29 - VK4|B3/JK3 (SEQ ID NO: 50326):

DIVMTQSPDSLAVSLGERATINCKSS--QSVLHSSNNNYLAWYQQKPGQPPKLLIYW--------ASTRESGVPDRFSGSGSG--TDFTLTISSLQAEDVAVYYCQQYYS--------------TPVTFGPGTKVDIKR wherein:

S at position 26 can be substituted with N
S at position 30 can be substituted with R or N
V at position 31 can be substituted with I or L
L at position 32 can be substituted with F
H at position 33 can be substituted with F, Y, K or S
S at position 34 can be substituted with N or H
N at position 36 can be substituted with H
N at position 37 can be substituted with S
N at position 38 can be substituted with K, Y or H
N at position 39 can be substituted with R or S
A at position 42 can be substituted with T or V
T at position 69 can be substituted with A, I or S
R at position 70 can be substituted with L
E at position 71 can be substituted with K or D
Q at position 107 can be substituted with H
Y at position 109 can be substituted with S
Y at position 110 can be substituted with C, F, S or H
S at position 111 can be substituted with N, Q, D or T FIGURE 57 (Continued)

T at position 135 can be substituted with L, I, A, F or S

V at position 137 can be substituted with F or P

Lys Ser Xaa Gln Xaa Xaa Xaa Xaa Ser Xaa Xaa Xaa Tyr Leu Xaa (SEQ ID NO: 50162)

Trp Ala Ser Xaa Xaa Xaa Xaa Ser (SEQ ID NO: 50163)

Xaa Gln Xaa Xaa Xaa Xaa Pro Xaa Thr (SEQ ID NO: 50164)

Lys Ser Ser Gln Ser Val Leu His Ser Ser Asn Asn Asn Tyr Leu Ala (SEQ ID NO: 50648)

Trp Ala Ser Thr Arg Glu Ser (SEQ ID NO: 50649)

Gln Gln Tyr Tyr Ser Thr Pro Val Thr (SEQ ID NO: 50650)

FIGURE 57 (Continued)

| Reference # | 1 D | 2 I | 3 V | 4 M | 5 T | 6 Q | 7 S | 8 P | 9 D | 10 S | 11 L | 12 A | 13 V | 14 S | 15 L | 16 G | 17 E | 18 R | 19 A | 20 T | 21 I | 22 N | 23 C | 24 K | 25 S | 26 S |
|---|---|---|---|---|---|---|---|---|---|---|---|---|---|---|---|---|---|---|---|---|---|---|---|---|---|---|
| CONSENSUS | D | I | V | M | T | Q | S | P | D | S | L | A | V | S | L | G | E | R | A | T | I | N | C | K | S | N |
| 21-225_11E2_LC | | | | | | | | | | | | | | | | | | | | | | | | | | |
| 21-225_12F11_LC | | | | | | | | | | | | | | | | | | | | | | | | | | |
| 21-225_147G6_LC | | | | | | | | | | | | | | | | | | | | | | | | | | |
| 21-225_148G3_LC | | | | | | | | | | | | | | | | | | | | | | X | | | | |
| 21-225_150B7_LC | | | | | | | | | | | | | | | | | | | | | | | | | | |
| 21-225_152E3_LC | | | | | | | | | | | | | | | | | | | | | | | | | | |
| 21-225_152F4_LC | | | | | | | | | | | | | | | | | | | | | | | | | | |
| 21-225_164B11_LC | | | | | | | | | | | | | | | | | | | | | | | | | | |
| 21-225_165H2_LC | | | | | | | | | | | | | | L | | | | | | | | | | | | |
| 21-225_190E2_LC | | | | | | | | | | | | F | | | | | | | T | | | | | | | |
| 21-225_190H4_LC | A | N | | | | | | | | | | | | | | | | | | | | | | | | |
| 21-225_190H6_LC | | | | | | | | | | | | | | | | | | | | | | | | | | |
| 21-225_191B12_LC | | | | | | | | | | | | | | | | | | | | | | | | | | |
| 21-225_191G3_LC | | | | | | | | | | | | | | | | | | | | | | | | | | |
| 21-225_195G11_LC | | | | | | | | | | | | | | | | | | | | | | | | | | |
| 21-225_198B1_LC | | | | | | | | | | | | | | | | | | | | | | | | | | |
| 21-225_196C1_LC | | | | | | A | | | | | | | | A | | | | | | | | D | | | | |
| 21-225_197C8_LC | | | | | | | | | | | | | | | | | | | | | | | | | | |
| 21-225_203F10_LC | | | | | | | | | | | | | | | | | | | | | | | | | | |
| 21-225_225F4_LC | | | | | | | | | | | | | | | | | | | | | | | | | | |
| 21-225_4A2_LC | | | | | | | | | | | | | | | | | | | | | | | | | | |
| 21-225_4A2.001.001_LC | | | | | | | | | | | | | | | | | | | | | | | | | | |
| 21-225_4A2.001.002_LC | | | | | | | | | | | | | | | | | | | | | | | | | | |
| 21-225_4A2.001.003_LC | | | | | | | | | | | | | | | | | | | | | | | | | | |
| 21-225_4A2.001.004_LC | | | | | | | | | | | | | | | | | | | | | | | | | | |
| 21-225_4A2.001.005_LC | | | | | | | | | | | | | | | | | | | | | | | | | | |
| 21-225_4A2.001.006_LC | | | | | | | | | | | | | | | | | | | | | | | | | | |
| 21-225_4A2.001.007_LC | | | | | | | | | | | | | | | | | | | | | | | | | | |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | K_CDR1 | | | | | | | | | | | | | | | | | K_FR2 | | | |
| CONSENSUS | . | . | Q | S | V | L | H | S | S | N | N | N | N | Y | L | A | W | Y | Q | Q | K | P | G | Q | P | P |
| 21-225_4A2.001.008_LC | | | | | — | | | | | | | | | | | | | R | | | | | | | | |
| 21-225_4A2.001.009_LC | | | | | — | | | | | | | | | | | | | R | | | | | | | | |
| 21-225_4A2.001.010_LC | | | | | — | | | | | | | | | | | | | R | | | | | | | | |
| 21-225_4A2.001.011_LC | | | | | — | | | | | | | | | | | | | R | | | | | | | | |
| 21-225_4A2.001.012_LC | | | | | — | | | | | | | | | | | | | R | | | | | | | | |
| 21-225_4A2.001.022_LC | | | | | — | | | | | | | | | | | | | R | | | | | | | | |
| 21-225_4A2.001.024_LC | | | | | — | | | N | | | | Y | | | | | | | | | | | | | | |
| 21-225_6G6_LC | | | | | | | | | | | | | | | | | | | | | | | | | | |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| CONSENSUS | K | L | L | I | Y | W | . | . | . | . | . | . | . | . | A | S | T | R | E | S | G | V | P | D | R | F |
| 21-225_4A2.001.008_LC | . | . | . | L | . | . | . | . | . | . | . | . | . | . | . | . | . | . | . | . | . | . | . | . | . | . |
| 21-225_4A2.001.009_LC | . | . | . | L | . | . | . | . | . | . | . | . | . | . | . | . | . | . | . | . | . | . | . | . | . | . |
| 21-225_4A2.001.010_LC | . | . | . | L | . | . | . | . | . | . | . | . | . | . | . | . | . | . | . | . | . | . | . | . | . | . |
| 21-225_4A2.001.011_LC | . | . | . | L | . | . | . | . | . | . | . | . | . | . | . | . | . | . | . | . | . | . | . | . | . | . |
| 21-225_4A2.001.012_LC | . | . | . | L | . | . | . | . | . | . | . | . | . | . | . | . | . | . | . | . | . | . | . | . | . | . |
| 21-225_4A2.001.022_LC | . | . | . | L | . | . | . | . | . | . | . | . | . | . | . | . | . | . | . | . | . | . | . | . | . | . |
| 21-225_4A2.001.024_LC | . | . | . | . | R | . | . | . | . | . | . | . | . | . | . | . | . | . | . | . | . | . | . | . | . | . |
| 21-225_6G6_LC | N | . | . | . | . | . | . | . | . | . | . | . | . | . | . | . | . | . | . | . | . | . | . | . | . | . |

FIGURE 57 (Continued)

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | | K_FR3 | | | | | | | | | | | | | | |
| CONSENSUS | S | G | S | G | S | G | - | - | T | D | F | T | L | T | I | S | S | L | Q | A | E | D | V | A | V | Y |
| 21-225_4A2.001.008_LC | | | | | | | | | | | | | | | | | | | | P | | | | | | |
| 21-225_4A2.001.009_LC | | | | | | | | | | | | | | | | | | | | P | | | | | | |
| 21-225_4A2.001.010_LC | | | | | | | | | | | | | | | | | | | | P | | | | | | |
| 21-225_4A2.001.011_LC | | | | | | | | | | | | | | | | | | | | P | | | | | | |
| 21-225_4A2.001.012_LC | | | | | | | | | | | | | | | | | | | | P | | | | | | |
| 21-225_4A2.001.022_LC | | | | | P | | | | | | | | | | | | | | | P | | | | | | |
| 21-225_4A2.001.024_LC | | | | | | | | | | | | | N | | | | | | | | | | | | | |
| 21-225_6G6_LC | | | | | | | | | | | | | | | | | | | | | | | | | | |

FIGURE 57 (Continued)

K_CDR3

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| CONSENSUS | Y | C | Q | Q | Y | Y | S | . | . | . | . | . | . | . | . | . | . | . | . | . | . | . | . | . | . | . |
| 21-225_11E2_LC | . | . | . | . | . | P | . | . | . | . | . | . | . | . | . | . | . | . | . | . | . | . | . | . | . | . |
| 21-225_12F11_LC | . | . | . | . | . | . | D | . | . | . | . | . | . | . | . | . | . | . | . | . | . | . | . | . | . | . |
| 21-225_147G6_LC | . | . | . | . | . | . | T | . | . | . | . | . | . | . | . | . | . | . | . | . | . | . | . | . | . | . |
| 21-225_148G3_LC | . | . | . | . | . | . | . | . | . | . | . | . | . | . | . | . | . | . | . | . | . | . | . | . | . | . |
| 21-225_150B7_LC | . | . | . | . | . | . | . | . | . | . | . | . | . | . | . | . | . | . | . | . | . | . | . | . | . | . |
| 21-225_152E3_LC | . | . | . | . | . | . | . | . | . | . | . | . | . | . | . | . | . | . | . | . | . | . | . | . | . | . |
| 21-225_152F4_LC | . | . | . | . | . | . | N | . | . | . | . | . | . | . | . | . | . | . | . | . | . | . | . | . | . | . |
| 21-225_164B11_LC | . | . | . | . | . | . | . | . | . | . | . | . | . | . | . | . | . | . | . | . | . | . | . | . | . | . |
| 21-225_165H2_LC | . | X | . | . | . | . | . | . | . | . | . | . | . | . | . | . | . | . | . | . | . | . | . | . | . | . |
| 21-225_190E2_LC | . | . | . | . | . | F | . | . | . | . | . | . | . | . | . | . | . | . | . | . | . | . | . | . | . | . |
| 21-225_190H4_LC | . | . | . | . | . | . | . | . | . | . | . | . | . | . | . | . | . | . | . | . | . | . | . | . | . | . |
| 21-225_190H6_LC | . | . | . | . | . | C | . | . | . | . | . | . | . | . | . | . | . | . | . | . | . | . | . | . | . | . |
| 21-225_191B12_LC | . | . | . | . | . | . | . | . | . | . | . | . | . | . | . | . | . | . | . | . | . | . | . | . | . | . |
| 21-225_191G3_LC | . | . | . | . | S | Q | S | . | . | . | . | . | . | . | . | . | . | . | . | . | . | . | . | . | . | . |
| 21-225_195G11_LC | . | . | . | . | . | . | . | . | . | . | . | . | . | . | . | . | . | . | . | . | . | . | . | . | . | . |
| 21-225_198B1_LC | . | . | . | . | . | C | S | . | . | . | . | . | . | . | . | . | . | . | . | . | . | . | . | . | . | . |
| 21-225_196C1_LC | . | . | . | . | S | Q | . | . | . | . | . | . | . | . | . | . | . | . | . | . | . | . | . | . | . | . |
| 21-225_197C8_LC | . | . | . | . | . | . | . | . | . | . | . | . | . | . | . | . | . | . | . | . | . | . | . | . | . | . |
| 21-225_203F10_LC | . | . | . | . | . | Q | . | . | . | . | . | . | . | . | . | . | . | . | . | . | . | . | . | . | . | . |
| 21-225_225F4_LC | . | . | X | . | . | F | T | . | . | . | . | . | . | . | . | . | . | . | . | . | . | . | . | . | . | . |
| 21-225_4A2_LC | . | . | . | . | . | H | N | . | . | . | . | . | . | . | . | . | . | . | . | . | . | . | . | . | . | . |
| 21-225_4A2.001_LC | . | . | . | . | . | . | N | . | . | . | . | . | . | . | . | . | . | . | . | . | . | . | . | . | . | . |
| 21-225_4A2.001.001_LC | . | . | . | . | . | . | N | . | . | . | . | . | . | . | . | . | . | . | . | . | . | . | . | . | . | . |
| 21-225_4A2.001.002_LC | . | . | . | . | . | . | . | . | . | . | . | . | . | . | . | . | . | . | . | . | . | . | . | . | . | . |
| 21-225_4A2.001.003_LC | . | . | . | . | . | . | N | . | . | . | . | . | . | . | . | . | . | . | . | . | . | . | . | . | . | . |
| 21-225_4A2.001.004_LC | . | . | . | . | . | . | Q | . | . | . | . | . | . | . | . | . | . | . | . | . | . | . | . | . | . | . |
| 21-225_4A2.001.005_LC | . | . | . | . | . | . | N | . | . | . | . | . | . | . | . | . | . | . | . | . | . | . | . | . | . | . |
| 21-225_4A2.001.006_LC | . | . | . | . | . | . | N | . | . | . | . | . | . | . | . | . | . | . | . | . | . | . | . | . | . | . |
| 21-225_4A2.001.007_LC | . | . | . | . | . | . | . | . | . | . | . | . | . | . | . | . | . | . | . | . | . | . | . | . | . | . |

Table 110. Consensus 30 - VL7j7a/JL2 (SEQ ID NO: 50327):

QTVVTQE-PSLTVSPGGTVTLTCASST-GAVTSG----YYPNWFQQKPGQAPRALIYS-------TSNKHSWTPARFSGSLLG--
GKAALTLSGVQPEDEAEYYCLLYYG---------GAQLVFGGGTKLTVLG wherein:

A at position 24 can be substituted with V or G
S at position 25 can be substituted with F or L
S at position 26 can be substituted with N
G at position 29 can be substituted with E
A at position 30 can be substituted with S or T
G at position 34 can be substituted with A
Y at position 39 can be substituted with S, N or F
Y at position 40 can be substituted with F
N at position 42 can be substituted with S or Q
S at position 58 can be substituted with H or N
S at position 68 can be substituted with N, D, I or T
K at position 70 can be substituted with R
L at position 107 can be substituted with M
L at position 108 can be substituted with I or F
Y at position 109 can be substituted with F
Y at position 110 can be substituted with C, F or S
G at position 111 can be substituted with D
A at position 135 can be substituted with V FIGURE 57 (Continued)

Q at position 136 can be substituted with H

L at position 137 can be substituted with V or M

V at position 138 can be substituted with A, I, G or M

Xaa Xaa Xaa Thr Xaa Xaa Val Thr Ser Xaa Xaa Xaa Pro Xaa (SEQ ID NO: 50165)

Xaa Thr Xaa Asn Xaa His Ser (SEQ ID NO: 50166)

Xaa Xaa Xaa Xaa Gly Xaa Xaa Xaa Xaa Xaa (SEQ ID NO: 50167)

Ala Ser Ser Thr Gly Ala Val Thr Ser Gly Tyr Tyr Pro Asn (SEQ ID NO: 50651)

Ser Thr Ser Asn Lys His Ser (SEQ ID NO: 50652)

Leu Leu Tyr Tyr Gly Gly Ala Gln Leu Val (SEQ ID NO: 50653)

FIGURE 57 (Continued)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | L_FR1 | | | | | | | | | | | | | | | |
| CONSENSUS | Q | T | V | V | T | Q | E | , | P | S | L | T | V | S | P | G | G | T | V | T | L | T | C | A | S | S |
| 21-225_74E5_LC | . | . | . | . | . | . | . | . | . | . | . | . | . | . | . | . | . | . | . | . | . | . | . | . | . | . |
| 21-225_78D10_LC | . | . | . | . | . | . | . | . | . | . | . | . | . | . | . | . | . | . | . | . | . | . | . | . | . | . |

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | L_CDR2 | | | | | | | | | | | | | |
| CONSENSUS_LC | R | A | L | I | Y | S | . | . | . | . | . | . | . | . | T | S | N | K | H | S | W | T | P | A | R | F |
| 21-225_74E5_LC | . | . | . | . | . | . | . | . | . | . | . | . | . | . | . | . | . | . | . | . | . | . | . | . | . | . |
| 21-225_78D10_LC | . | . | . | . | . | . | . | . | . | . | . | . | . | . | . | D | . | . | . | . | . | . | . | . | . | . |

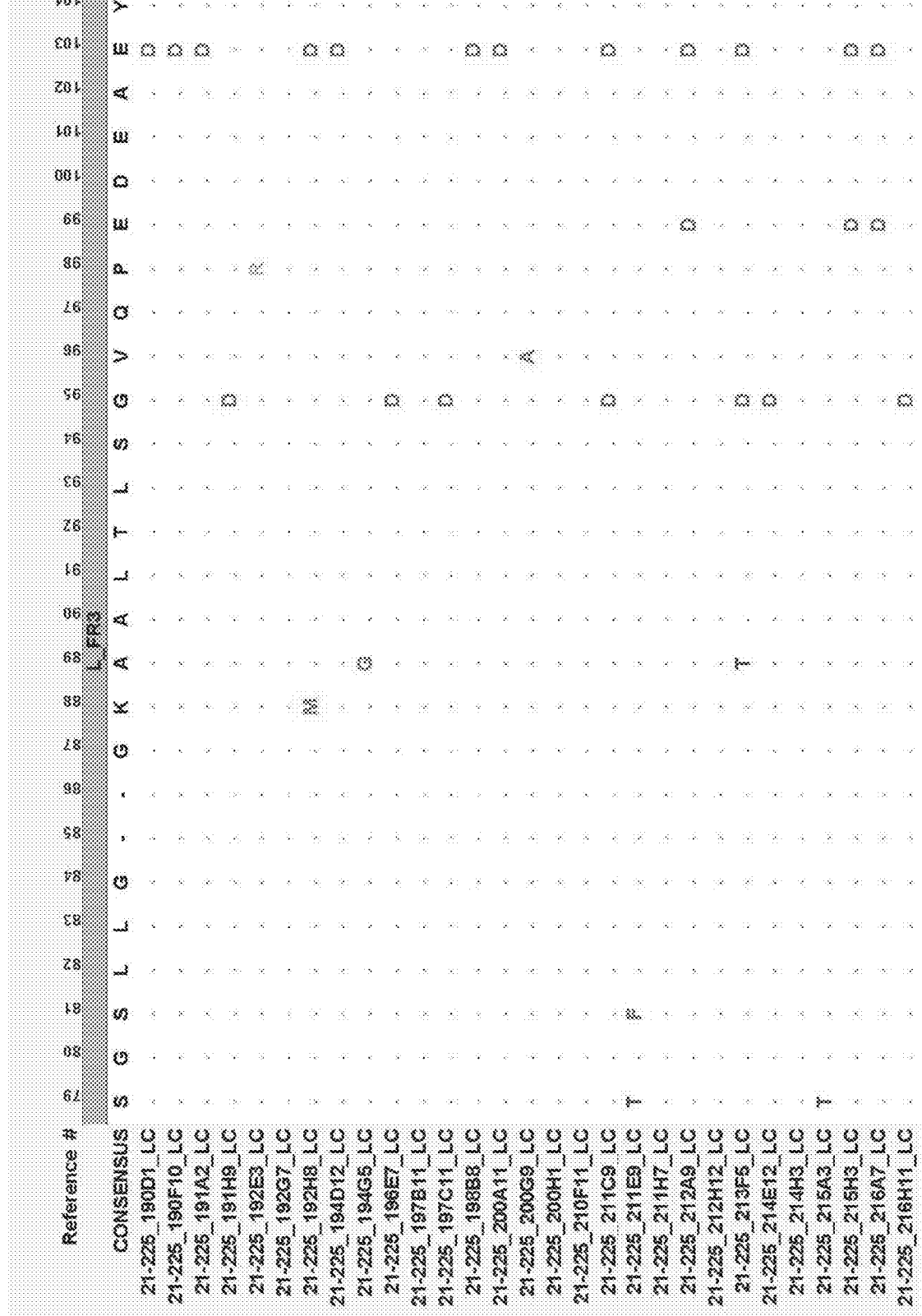

FIGURE 57 (Continued)

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | L_FR3 | | | | | | | | | | | | | | | | |
| CONSENSUS | S | G | S | L | L | G | - | - | G | K | A | A | L | T | L | S | G | V | Q | P | E | D | E | A | E | Y |
| 21-225_74E5_LC | . | . | . | . | . | . | . | . | . | . | . | . | . | . | . | . | D | . | . | . | . | . | . | . | . | . |
| 21-225_78D10_LC | . | . | . | . | . | . | . | . | . | . | . | . | . | . | . | . | . | . | . | . | . | . | . | . | . | . |

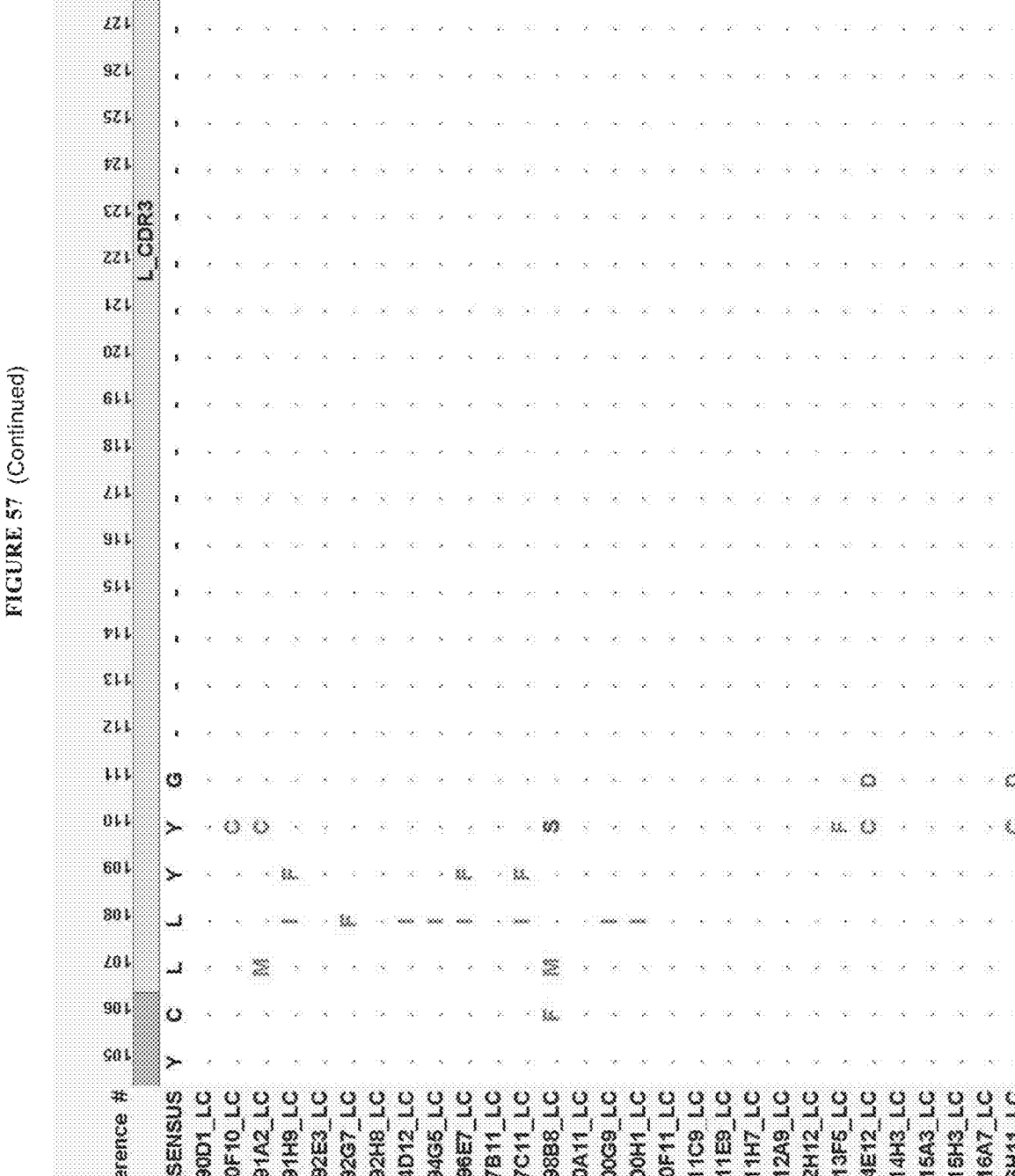

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | LFR4 | | | | | |
| CONSENSUS | - | - | - | G | A | Q | L | V | F | G | G | G | T | K | L | T | V | L | G |
| 21-225_74E5_LC | . | . | . | . | . | . | . | . | . | . | . | . | . | . | . | . | . | . | . |
| 21-225_78D10_LC | . | . | . | . | . | . | . | M | . | . | . | . | . | . | . | . | . | . | . |

FIGURE 57 (Continued)

Table 111. Consensus 31 - VK3jL2/JK2 (SEQ ID NO: 50328):

EIVMTQSPATLSVSPGERATLSCRAS--QSVN-------SNLAWYQQKPGQAPRLLIYG-------ASTRATGIPARFSGSGSG---
TEFTLTISSLQSEDFAVYYCQQYND---------------WPCSFGQGTKLEIKR wherein:

A at position 25 can be substituted with S

Q at position 29 can be substituted with L, M or V

S at position 30 can be substituted with N, D, R or T

V at position 31 can be substituted with I

N at position 32 can be substituted with K, S, V, A, I or L

S at position 39 can be substituted with N or T

N at position 40 can be substituted with S or Y

G at position 58 can be substituted with I, F or V

A at position 67 can be substituted with T

T at position 69 can be substituted with I

Q at position 108 can be substituted with E

Y at position 109 can be substituted with F

N at position 110 can be substituted with Y or D

D at position 111 can be substituted with N

Null (-) at position 134 can be substituted with W

W at position 135 can be substituted with P

P at position 136 can be substituted with L or M

Arg Xaa Ser Xaa Xaa Xaa Xaa Xaa Xaa Leu Ala (SEQ ID NO: 50168)

Xaa Xaa Ser Xaa Arg Ala Thr (SEQ ID NO: 50169)

Gln Xaa Xaa Xaa Xaa Xaa Xaa Xaa Cys Ser (SEQ ID NO: 50170)

Arg Ala Ser Gln Ser Val Asn Ser Asn Leu Ala (SEQ ID NO: 50654)

Gly Ala Ser Thr Arg Ala Thr (SEQ ID NO: 50655)

Gln Gln Tyr Asn Asp Trp Pro Cys Ser (SEQ ID NO: 50656)

| Reference # | K_CDR1 | | | | | | | | | | | | | | | | K_FR2 | | | | | | |
|---|---|---|---|---|---|---|---|---|---|---|---|---|---|---|---|---|---|---|---|---|---|---|---|---|
| | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
| CONSENSUS | . | . | Q | S | V | N | . | . | . | . | . | S | N | L | A | W | Y | Q | Q | K | P | G | Q | A | P |
| 21-225_162A10_LC | | | | T | | | | | | | | | | | | | | | | | | S | | | |
| 21-225_193G12_LC | | | | | | S | | | | | | | | | | | | | | | | | | | |
| 21-225_201A4_LC | | | | N | | K | | | | | | N | | | | | | | | | | | | | |
| 21-225_201F2_LC | | | | N | | K | | | | | | N | | Y | | | | | | | | | | | |
| 21-225_201F7_LC | | | | N | | K | | | | | | N | | | | | | | | | | | | | |
| 21-225_201H4_LC | | | | | | | | | | | | | | | | | | | | N | | | | | |
| 21-225_202A8_LC | | | | | | L | | | | | | | | | | | | | | R | | | | | |
| 21-225_202F12_LC | | | | N | | K | | | | | | N | | | | | | | | | | | | | |
| 21-225_205G4_LC | | | | | | A | | | | | | | | | | | | | | | | | | | |
| 21-225_210H10_LC | | | | | | | | | | | | | | S | | | | | | | | | | | |
| 21-225_212C10_LC | | | | | | S | | | | | | N | | S | | | | | R | | | | | | |
| 21-225_218B10_LC | | | | | | S | | | | | | | | | | | | | | | | | | | |
| 21-225_24H3_LC | | | | | | | | | | | | | | | | | | | | | | | | | |
| 21-225_57H3_LC | | | | | | | | | | | | | | | | | | | | | | | | | |
| 21-225_62E6_LC | | | | | | A | | | | | | | | | | | | | | | | | | | |
| 21-225_65A6_LC | | | | | | V | | | | | | N | | S | | | | | | | | | | | |
| 21-225_67C3_LC | | | L | | | V | | | | | | N | | S | | | | | | | | | | | |
| 21-225_70A5_LC | | | V | | | V | | | | | | N | | S | | | | | | | | | | | |
| 21-225_74C3_LC | | | | | | S | | | | | | | | S | | | | | | | | | | | |
| 21-225_74E3_LC | | | | | | | | | | | | | | | | | | | | | | | | | |
| 21-225_74E11_LC | | | | | | | | | | | | | | | | | | | | | | | | | |
| 21-225_76D2_LC | | | | O | | | | | | | | | | | | | | | | | | | | | |
| 21-225_77H5_LC | | | | | | | | | | | | T | | Y | | | | | | | | | | | |
| 21-225_82H5_LC | | | | | | | | | | | | | | | | | | | | | | | | | |
| 21-225_95G2_LC | | | R | | | V | | | | | | N | | S | | | | | | | | | | | |

Table 112. Consensus 32 – VK3|A27/JK4 (SEQ ID NO: 50329):

EFMLTQSPGTLSLSPGERATLSCRAS--QSVSS------SYLVWYQQKPGQAPRLLIYG------ASTRATGIPDRFSGSGSG--
TDFTLTISRLEPEYFAVYYCQQYGC------------------SPLTFGGGTKVEITR wherein:

A at position 25 can be substituted with S

Q at position 29 can be substituted with E

S at position 30 can be substituted with R

V at position 31 can be substituted with I

S at position 32 can be substituted with T

S at position 33 can be substituted with T

S at position 39 can be substituted with N

Y at position 40 can be substituted with A

V at position 42 can be substituted with S

T at position 69 can be substituted with S

T at position 72 can be substituted with S or I

G at position 110 can be substituted with V

C at position 111 can be substituted with N or S

P at position 136 can be substituted with L

Arg Xaa Ser Xaa Xaa Xaa Xaa Xaa Xaa Leu Xaa (SEQ ID NO: 50171)

Gly Ala Ser Xaa Arg Ala Xaa (SEQ ID NO: 50172)

Gln Gln Tyr Xaa Xaa Ser Xaa Leu Thr (SEQ ID NO: 50173)

Arg Ala Ser Gln Ser Val Ser Ser Ser Tyr Leu Val (SEQ ID NO: 50657)

Gly Ala Ser Thr Arg Ala Thr (SEQ ID NO: 50658)

Gln Gln Tyr Gly Cys Ser Pro Leu Thr (SEQ ID NO: 50659)

Table 113. Consensus 33 - VK2|A18/JK4 (SEQ ID NO: 50330):

DIVMTQTPLSLSVTPGQPASISCKSS-QSLLHSE-GKTYLYWYLQKPGQPPQLLIYE--------VSNRFSGVPDRFSGSGSG-
TDFTLKISRVEAEDVGVYYCMQSIQ---------------------LPLTFGGGTKVEIKR wherein:

S at position 30 can be substituted with T

L at position 32 can be substituted with Q

H at position 33 can be substituted with R

S at position 34 can be substituted with G

E at position 35 can be substituted with D

K at position 38 can be substituted with R

Y at position 40 can be substituted with H or F

Y at position 42 can be substituted with N

V at position 67 can be substituted with I

N at position 69 can be substituted with Y or H

F at position 71 can be substituted with L, V or L

M at position 107 can be substituted with F

Q at position 108 can be substituted with H

S at position 109 can be substituted with G or N

I at position 110 can be substituted with K or T

Q at position 111 can be substituted with null (-), K or H

FIGURE 57 (Continued)

L at position 135 can be substituted with Q, Y, F or H

P at position 136 can be substituted with L or V

L at position 137 can be substituted with F or P

T at position 138 can be substituted with P or S

Lys Ser Ser Gln Xaa Leu Xaa Xaa Xaa Gly Xaa Thr Xaa Leu Xaa (SEQ ID NO: 50174)

Glu Xaa Ser Xaa Arg Xaa Ser (SEQ ID NO: 50175)

Xaa Xaa Xaa Xaa Xaa Xaa Xaa Xaa (SEQ ID NO: 50176)

Lys Ser Ser Gln Ser Leu Leu His Ser Glu Gly Lys Thr Tyr Leu Tyr (SEQ ID NO: 50660)

Glu Val Ser Asn Arg Phe Ser (SEQ ID NO: 50661)

Met Gln Ser Ile Gln Leu Pro Leu Thr (SEQ ID NO: 50662)

Table 114. Consensus 34 - VL2|2a2/JL3b (SEQ ID NO: 50331):

QSALTQP-ASVSGSPGQSITISCTGTS-SDVGGY----NYVSWYQQHPGK-APKLMIYE--------VSNRPSGVSNRFSGSKSG--NTASLTISGLQAEDEADYYCNSYTR--------------SITWVFGGGTKLTVLG wherein:

V at position 31 can be substituted with I

G at position 33 can be substituted with S

Y at position 40 can be substituted with F

S at position 68 can be substituted with R

N at position 107 can be substituted with G, C or S

T at position 110 can be substituted with V or K

R at position 111 can be substituted with S or K

S at position 134 can be substituted with G, N or R

I at position 135 can be substituted with S or Y

Thr Gly Thr Ser Ser Asp Xaa Gly Xaa Tyr Asn Xaa Val Ser (SEQ ID NO: 50177)

Glu Val Xaa Asn Arg Pro Ser (SEQ ID NO: 50178)

Xaa Ser Tyr Xaa Xaa Xaa Xaa Thr Trp Val (SEQ ID NO: 50179)

Thr Gly Thr Ser Ser Asp Val Gly Gly Tyr Asn Tyr Val Ser (SEQ ID NO: 50663)

Glu Val Ser Asn Arg Pro Ser (SEQ ID NO: 50664)

Asn Ser Tyr Thr Arg Ser Ile Thr Trp Val (SEQ ID NO: 50665)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | LFR4 | | | | | |
| CONSENSUS | . | . | . | S | Y | T | W | V | F | G | G | G | T | K | L | T | V | L | G |
| 21-225_178H8_LC | . | . | . | . | . | . | . | . | . | . | . | . | . | . | . | . | . | . | . |
| 21-225_210D12_LC | . | . | . | G | . | . | . | . | . | . | . | . | . | . | . | . | . | . | . |
| 21-225_210E12_LC | . | . | . | . | . | . | . | . | . | . | . | . | . | . | . | . | . | . | . |
| 21-225_211C1_LC | . | . | . | G | . | . | . | . | . | . | . | . | . | S | . | . | . | . | . |
| 21-225_211G5_LC | . | . | . | . | . | . | . | . | . | . | . | . | . | . | . | . | . | . | . |
| 21-225_212A4_LC | . | . | . | G | . | . | . | . | . | . | . | . | . | S | . | . | . | . | . |
| 21-225_212C2_LC | . | . | . | . | . | . | . | . | . | . | . | . | . | . | . | . | . | . | . |
| 21-225_212F6_LC | . | . | . | . | . | . | . | . | . | . | . | . | . | . | . | . | . | . | . |
| 21-225_212G7_LC | . | . | . | G | . | . | . | . | . | . | . | . | . | . | . | . | . | . | . |
| 21-225_213D5_LC | . | . | . | G | S | . | . | . | . | . | . | . | . | . | V | . | . | . | S |
| 21-225_213G3_LC | . | . | . | G | . | . | . | . | . | . | . | . | . | . | . | . | . | . | . |
| 21-225_215D3_LC | . | . | . | G | . | . | . | . | . | . | . | . | . | S | . | . | . | . | . |
| 21-225_216A3_LC | . | . | . | . | . | . | . | . | . | . | . | . | . | . | . | . | . | . | . |
| 21-225_217B2_LC | . | . | . | . | . | . | . | . | . | . | . | . | . | . | . | . | . | . | . |
| 21-225_219A7_LC | . | . | . | . | . | . | . | . | . | . | . | . | . | . | . | . | . | . | . |
| 21-225_221G4_LC | . | . | . | N | . | . | . | . | . | . | . | . | . | . | . | . | . | . | . |
| 21-225_221H2_LC | . | . | . | . | . | . | . | . | . | . | . | . | . | . | . | . | . | . | . |
| 21-225_52H4_LC | . | . | . | . | . | . | . | . | . | . | . | . | . | . | . | . | . | . | . |

FIGURE 57 (Continued)

Table 115. Consensus 35 - VK1iO12/JK1 (SEQ ID NO: 50332):

DIQMTQSPSSLSASVGDRVTITCRAS--QSIS----NYLNWYQQKPGKAPKLLIYA-------ASSLQSGVPSRFSGSGSG--
TDFTLTISSLQPEDFATYCQQSYS.............TPTWTFGQGTKVEIKR wherein:

A at position 25 can be substituted with S

Q at position 29 can be substituted with H or R

S at position 30 can be substituted with N, T or H

S at position 32 can be substituted with N, G or T

N at position 39 can be substituted with S or R

Y at position 40 can be substituted with F

A at position 58 can be substituted with T, S or V

A at position 67 can be substituted with T, E or V

S at position 68 can be substituted with L

S at position 69 can be substituted with N

Q at position 71 can be substituted with H

S at position 72 can be substituted with I

S at position 109 can be substituted with G or T

S at position 111 can be substituted with T, N or R

T at position 134 can be substituted with S or null (-)

P at position 135 can be substituted with I

T at position 136 can be substituted with P, Q or L

Arg Xaa Ser Xaa Xaa Ile Xaa Xaa Xaa Xaa Leu Asn (SEQ ID NO: 50180)

Xaa Xaa Xaa Xaa Leu Xaa Xaa (SEQ ID NO: 50181)

Gln Gln Xaa Tyr Xaa Xaa Xaa Xaa Xaa Trp Thr (SEQ ID NO: 50182)

Arg Ala Ser Gln Ser Ile Ser Asn Tyr Leu Asn (SEQ ID NO: 50666)

Ala Ala Ser Ser Leu Gln Ser (SEQ ID NO: 50667)

Gln Gln Ser Tyr Ser Thr Pro Thr Trp Thr (SEQ ID NO: 50668)

Table 116. Consensus 36 – VK1iL5/JK4 (SEQ ID NO: 50333):

DIQMTQSPSSVSASVGDRVTITCRAS--QGIS------SWLAWYQQKPGKAPKLLIYA-------ASSLQSGVPSRFSGSGSG--
TDFTLTISSLQPEDFATYYCQQINS----------------FPLTFGGGTKVEIKR wherein:

G at position 30 can be substituted with D

S at position 39 can be substituted with N, I or K

W at position 40 can be substituted with Y

S at position 72 can be substituted with G

I at position 109 can be substituted with T, V, A or G

N at position 110 can be substituted with K

Arg Ala Ser Gln Xaa Ile Ser Xaa Xaa Leu Ala (SEQ ID NO: 50183)

Ala Ala Ser Ser Leu Gln Ser Xaa (SEQ ID NO: 50184)

Gln Gln Xaa Xaa Ser Phe Pro Leu Thr (SEQ ID NO: 50185)

Arg Ala Ser Gln Gly Ile Ser Ser Trp Leu Ala (SEQ ID NO: 50669)

Ala Ala Ser Ser Leu Gln Ser (SEQ ID NO: 50670)

Gln Gln Ile Asn Ser Phe Pro Leu Thr (SEQ ID NO: 50671)

Table 117. Consensus 37 - VK1jO18/JK5 (SEQ ID NO: 50334):

DIQMTQSPSSLSASVGDRVTITCQAS--QDIN------NYLNWYQQKPGKAPKLLIYD--------ASNLETGVPSRFSGSGSG--
TDFTFTISSLQPEDIATYCQQYDN------------LPITFGQGTRLEIKR wherein:

S at position 26 can be substituted with N

D at position 30 can be substituted with Y

N at position 32 can be substituted with S, T, F or Y

N at position 39 can be substituted with D

Y at position 40 can be substituted with F

A at position 67 can be substituted with G

N at position 69 can be substituted with T, D or S

Y at position 109 can be substituted with F

D at position 110 can be substituted with E

N at position 111 can be substituted with null (-) or I

L at position 135 can be substituted with N or V

P at position 136 can be substituted with L

Gln Ala Xaa Gln Xaa Ile Xaa Xaa Xaa Leu Asn (SEQ ID NO: 50186)

Asp Xaa Ser Xaa Leu Glu Thr (SEQ ID NO: 50187)

Gln Gln Xaa Xaa Xaa Xaa Xaa Ile Thr (SEQ ID NO: 50188)

Gln Ala Ser Gln Asp Ile Asn Asn Tyr Leu Asn (SEQ ID NO: 50672)

Asp Ala Ser Asn Leu Glu Thr (SEQ ID NO: 50673)

FIGURE 57 (Continued)

Gln Gln Tyr Asp Asn Leu Pro Ile Thr (SEQ ID NO: 50674)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | K_FR1 | | | | | | | | | | | | | | |
| CONSENSUS | D | I | Q | M | T | Q | S | P | S | S | L | S | A | S | V | G | D | R | V | T | I | T | C | Q | A | S |
| 21-225_11A2_LC | . | . | . | . | . | . | . | . | . | . | . | . | . | . | . | . | . | . | . | . | . | . | . | . | . | . |
| 21-225_13A1_LC | . | . | . | . | . | . | . | . | . | . | . | . | . | . | . | . | . | . | . | . | . | . | . | . | . | . |
| 21-225_159C4_LC | . | . | . | . | . | . | . | . | . | . | . | . | . | . | . | . | . | . | . | . | . | . | . | . | . | . |
| 21-225_15C2_LC | . | . | . | . | . | . | . | . | . | . | . | . | . | . | . | . | . | . | . | . | . | . | . | . | . | . |
| 21-225_15F10_LC | . | . | . | . | . | . | . | . | . | . | . | . | . | . | . | . | . | . | . | . | . | . | . | . | . | N |
| 21-225_161G4_LC | . | . | . | . | . | . | . | . | . | . | . | . | . | . | . | . | . | . | . | . | . | . | . | . | . | . |
| 21-225_16B3_LC | . | . | . | . | . | . | . | . | . | . | . | . | . | . | . | . | . | . | . | . | . | . | . | . | . | . |
| 21-225_16F6_LC | . | . | . | . | . | . | . | . | . | . | . | . | . | . | . | . | . | . | . | . | . | . | . | . | . | N |
| 21-225_1B12_LC | . | . | . | . | . | . | . | . | . | . | . | . | . | . | . | . | . | . | . | . | . | . | . | . | . | . |
| 21-225_225B11_LC | . | . | . | . | . | . | . | . | . | . | . | . | . | . | . | . | . | . | . | . | . | . | . | . | . | . |
| 21-225_24D6_LC | . | . | . | . | . | . | . | . | . | . | . | . | . | . | . | . | . | . | . | . | . | . | . | . | . | . |
| 21-225_30E2_LC | . | . | . | . | . | . | . | . | S | . | . | . | . | . | . | . | . | . | . | . | . | . | . | . | . | . |
| 21-225_35E3_LC | . | . | . | . | . | . | . | . | T | . | . | . | . | . | . | . | . | . | . | . | . | . | . | . | . | . |
| 21-225_50G4_LC | . | . | . | . | . | . | . | . | . | . | . | . | . | . | . | . | . | . | . | . | . | . | . | . | . | . |
| 21-225_5E6_LC | . | . | . | . | . | . | . | . | . | . | . | . | . | . | . | . | . | . | . | . | . | . | . | . | . | . |
| 21-225_6G7_LC | . | . | . | . | . | . | . | . | . | . | L | . | . | . | . | . | . | . | . | . | . | . | . | . | . | . |

Table 118. Consensus 38 - VL1|1b/JL2 (SEQ ID NO: 50335):

QSVLTQP-PSVSAAPGQKVTISCSGSS-SNIGN----NYVSWYQQLPGTAPKLLIYD----NNKRPSGIPDRFSGSKSG-
TSATLGITGLQTGDEADYYCGTWDSS----------LSVGVFGGGTKLTVLG wherein:

I at position 31 can be substituted with L

N at position 33 can be substituted with S

N at position 39 can be substituted with H or K

Y at position 40 can be substituted with F

V at position 41 can be substituted with L

N at position 67 can be substituted with S

N at position 68 can be substituted with Y or S

T at position 108 can be substituted with A or I

S at position 111 can be substituted with G, I or R

S at position 112 can be substituted with R

S at position 135 can be substituted with N

V at position 136 can be substituted with A or T

G at position 137 can be substituted with V or M

Ser Gly Ser Ser Asn Xaa Gly Xaa Xaa Xaa Xaa Ser (SEQ ID NO: 50189)

Asp Xaa Xaa Lys Arg Pro Ser (SEQ ID NO: 50190)

Gly Xaa Trp Asp Xaa Xaa Leu Xaa Xaa Xaa Val (SEQ ID NO: 50191)

Ser Gly Ser Ser Asn Ile Gly Asn Asn Tyr Val Ser (SEQ ID NO: 50675)

FIGURE 57 (Continued)

Asp Asn Asn Lys Arg Pro Ser (SEQ ID NO: 50676)

Gly Thr Trp Asp Ser Ser Leu Ser Val Gly Val (SEQ ID NO: 50677)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | LFR1 | | | | | | | | | | | | | | |
| CONSENSUS | Q | S | V | L | T | Q | P | - | P | S | V | S | A | A | P | G | Q | K | V | T | I | S | C | S | G | S |
| 21-225_190B10_LC | . | . | . | . | . | . | . | . | . | . | . | . | . | . | . | . | . | . | . | . | . | . | . | . | . | . |
| 21-225_190C3_LC | . | . | . | . | . | . | . | . | . | . | . | . | . | . | . | . | . | . | . | . | . | . | . | . | . | . |
| 21-225_190D10_LC | . | . | . | . | . | . | . | . | . | . | . | . | . | . | . | . | . | . | . | . | . | . | . | . | . | . |
| 21-225_190D8_LC | . | . | . | . | . | . | . | . | . | . | . | . | . | . | . | . | . | . | . | . | . | . | . | . | . | . |
| 21-225_190H7_LC | . | . | . | . | . | . | . | . | . | . | . | . | . | . | . | . | . | . | . | . | . | . | . | . | . | . |
| 21-225_191A1_LC | . | . | . | . | . | . | . | . | . | . | . | . | . | . | . | . | . | R | . | . | . | . | . | . | . | . |
| 21-225_192G2_LC | . | . | . | . | . | . | . | . | . | . | . | . | . | . | . | . | . | . | . | . | . | . | . | . | . | . |
| 21-225_194F11_LC | . | . | . | . | . | . | . | . | . | . | . | . | . | . | . | . | . | . | . | . | . | . | . | . | . | . |
| 21-225_194G12_LC | . | . | . | . | . | . | . | . | . | . | . | . | . | . | . | . | . | R | . | . | . | . | . | . | . | . |
| 21-225_197E8_LC | . | . | . | . | . | . | . | . | . | . | . | . | . | . | . | . | . | . | . | . | . | . | . | . | . | . |
| 21-225_198D2_LC | . | . | . | . | . | . | . | . | . | . | . | . | . | . | . | . | . | . | . | . | . | . | . | . | . | . |
| 21-225_200G8_LC | . | . | . | . | . | . | . | . | . | . | . | . | . | . | . | . | . | . | . | . | . | . | . | . | . | . |
| 21-225_209A8_LC | . | . | . | . | . | . | . | . | . | . | . | . | . | . | . | . | . | . | . | . | . | . | . | . | . | . |
| 21-225_214D8_LC | . | . | . | . | . | . | . | . | . | . | . | . | . | . | . | . | . | . | . | . | . | . | . | . | . | . |
| 21-225_218G4_LC | . | . | . | . | . | . | . | . | . | . | . | . | . | . | . | . | . | . | . | . | . | . | . | . | . | . |
| 21-225_58C5_LC | . | . | . | . | . | . | . | . | . | . | . | . | . | . | . | . | . | . | . | . | . | . | . | . | . | . |

Table 119. Consensus 39 - VK2|A19/JK4 (SEQ ID NO: 50336):

DIVMTQSPLSLPVTPGEPASISCRSS--QSLLHSN--GYNYLDWYLQKPGQSPQLLIYL--------GSNRASGVPDRFSGSGSG--
TDFTLKISRVEAEDVGVYYCMQALH--------------PPLTFGGGTKVEIKR wherein:

S at position 25 can be substituted with Y

L at position 32 can be substituted with V

H at position 33 can be substituted with Y

S at position 34 can be substituted with N or H

N at position 35 can be substituted with S

G at position 37 can be substituted with K or R

Y at position 38 can be substituted with H or N

Y at position 40 can be substituted with H or S

L at position 58 can be substituted with V

N at position 69 can be substituted with H

A at position 109 can be substituted with P, T or V

H at position 111 can be substituted with Q or null (-)

Null (-) at position 134 can be substituted with T

P at position 135 can be substituted with Q, T or I

P at position 136 can be substituted with T

L at position 137 can be substituted with P or F

Arg Xaa Ser Gln Ser Leu Xaa Xaa Xaa Xaa Xaa Asn Xaa Leu Asp (SEQ ID NO: 50243)

FIGURE 57 (Continued)

Xaa Gly Ser Xaa Arg Ala Ser (SEQ ID NO: 50244)

Met Gln Xaa Leu Xaa Xaa Xaa Xaa Xaa Thr (SEQ ID NO: 50245)

Arg Ser Ser Gln Ser Leu Leu His Ser Asn Gly Tyr Asn Tyr Leu Asp (SEQ ID NO: 50678)

Leu Gly Ser Asn Arg Ala Ser (SEQ ID NO: 50679)

Met Gln Ala Leu His Pro Pro Leu Thr (SEQ ID NO: 50680)

Table 120.   Consensus 40 - VL1|1c/JL2 (SEQ ID NO: 50337):

QSVLTQP-PSASGTPGQRVTISCSGSS-SNIGS------NTVNWYQQLPGTAPKLLIYS------NNQRPSGVPDRFSGSKSG--TSASLAISGLQSEDEADYYCAAWDDS------------LNGVFGGGTKLTVLG wherein:

S at position 26 can be substituted with T

S at position 27 can be substituted with N

N at position 30 can be substituted with Y

S at position 33 can be substituted with N

N at position 39 can be substituted with Y

T at position 40 can be substituted with A or S

V at position 41 can be substituted with I

N at position 42 can be substituted with D or S

S at position 58 can be substituted with I

N at position 67 can be substituted with S

N at position 68 can be substituted with D or S

Q at position 69 can be substituted with H

A at position 107 can be substituted with E

S at position 112 can be substituted with null (-)

null (-) at position 133 can be substituted with L

L at position 134 can be substituted with N, M or S

N at position 135 can be substituted with G, K or L

FIGURE 57 (Continued)

G at position 136 can be substituted with H or N

V at position 137 can be substituted with P or G

V at position 138 can be substituted with P

Ser Gly Xaa Xaa Ser Xaa Ile Gly Xaa Xaa Xaa Xaa Xaa (SEQ ID NO: 50192)

Xaa Xaa Xaa Xaa Arg Pro Ser (SEQ ID NO: 50193)

Xaa Ala Trp Asp Asp Xaa Xaa Xaa Xaa Xaa Xaa Xaa (SEQ ID NO: 50194)

Ser Gly Ser Ser Ser Asn Ile Gly Ser Asn Thr Val Asn (SEQ ID NO: 50681)

Ser Asn Asn Gln Arg Pro Ser (SEQ ID NO: 50682)

Ala Ala Trp Asp Asp Ser Leu Asn Gly Val Val (SEQ ID NO: 50683)

FIGURE 57 (Continued)

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
|  |  |  |  |  | L_CDR1 |  |  |  |  |  |  |  |  |  |  |  | L_FR2 |  |  |  |  |  |  |  |  |  |
| CONSENSUS | S | - | S | N | I | G | S | - | - | - | - | - | N | T | V | N | W | Y | Q | Q | L | P | G | T | A | P |
| 21-225_146A8_LC | . | . | . | . | . | . | . | . | . | . | . | . | . | . | . | . | . | . | . | . | . | . | . | . | . | . |
| 21-225_146B6_LC | . | . | . | . | . | . | . | . | . | . | . | . | . | . | . | . | . | . | . | . | . | . | . | . | . | . |
| 21-225_146D8_LC | . | . | . | Y | . | . | . | . | . | . | . | . | . | S | . | . | . | . | . | . | . | . | . | . | . | . |
| 21-225_147H12_LC | . | . | . | . | . | . | . | . | . | . | . | . | . | A | . | . | . | . | . | . | . | . | . | . | . | . |
| 21-225_149A1_LC | . | . | . | . | . | . | . | . | . | . | . | . | Y | A | . | D | . | . | . | . | . | . | . | . | . | . |
| 21-225_150F9_LC | . | . | . | . | . | . | . | . | . | . | . | . | . | A | . | . | . | . | . | . | . | . | . | . | . | . |
| 21-225_154G12_LC | . | . | . | . | . | . | N | . | . | . | . | . | . | . | . | . | . | . | . | . | . | . | . | . | . | . |
| 21-225_156H2_LC | . | . | . | . | . | . | . | . | . | . | . | . | . | A | . | . | . | . | . | . | . | . | . | . | . | . |
| 21-225_197F9_LC | . | . | . | . | . | . | . | . | . | . | . | . | . | . | . | . | . | . | . | . | . | . | . | . | . | . |
| 21-225_199C3_LC | . | . | . | . | . | . | . | . | . | . | . | . | . | . | . | S | . | . | . | . | . | . | . | . | . | . |
| 21-225_4G12_LC | N | . | . | . | . | . | . | . | . | . | . | . | Y | . | . | . | . | . | . | . | . | . | . | . | . | . |
| 21-225_60D6_LC | . | . | . | . | . | . | . | . | . | . | . | . | . | . | . | . | . | . | . | . | . | . | . | . | . | . |
| 21-225_9G9_LC | N | . | . | . | . | . | . | . | . | . | . | . | Y | . | . | . | . | . | . | . | . | . | . | . | . | . |

FIGURE 57 (Continued)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | | | | | | | | | | | L_CDR2 | | | | | | | | | | | | | |
| CONSENSUS | K | L | L | I | Y | S | . | . | . | . | . | . | . | . | N | N | Q | R | P | S | G | V | P | D | R | F |
| 21-225_146A8_LC | . | . | . | . | . | . | . | . | . | . | . | . | . | . | . | D | . | . | . | . | . | . | . | . | . | . |
| 21-225_146B8_LC | . | . | . | . | . | . | . | . | . | . | . | . | . | . | . | . | . | . | . | . | . | . | . | . | . | . |
| 21-225_146D8_LC | . | . | . | . | . | . | . | . | . | . | . | . | . | . | . | . | K | . | . | . | . | . | . | . | L | . |
| 21-225_147H12_LC | . | . | . | . | . | . | . | . | . | . | . | . | . | . | . | . | K | . | . | . | . | . | . | . | . | . |
| 21-225_149A1_LC | . | . | . | . | . | . | . | . | . | . | . | . | . | . | . | S | . | . | . | . | . | . | . | . | . | . |
| 21-225_150F9_LC | . | . | . | . | . | . | . | . | . | . | . | . | . | . | S | D | . | . | . | . | . | . | . | . | . | . |
| 21-225_154G12_LC | . | . | . | . | . | . | . | . | . | . | . | . | . | . | . | . | . | . | . | . | . | . | . | . | . | . |
| 21-225_158H2_LC | . | . | . | . | . | . | . | . | . | . | . | . | . | . | . | . | . | . | . | . | . | . | . | . | . | . |
| 21-225_197F9_LC | . | . | . | . | . | . | . | . | . | . | . | . | . | . | . | . | . | . | . | . | . | . | . | . | . | . |
| 21-225_199C3_LC | . | . | . | . | . | . | . | . | . | . | . | . | . | . | . | . | . | . | . | . | . | . | . | . | . | . |
| 21-225_4G12_LC | . | . | . | . | . | S | . | . | . | . | . | . | . | . | . | . | . | . | . | . | . | . | . | . | . | . |
| 21-225_60D6_LC | . | . | . | . | . | . | . | . | . | . | . | . | . | . | . | . | . | . | . | . | . | . | . | . | . | . |
| 21-225_9G9_LC | . | . | . | . | . | S | . | . | . | . | . | . | . | . | . | . | . | . | . | . | . | . | . | . | . | . |

Table 121. Consensus 41 - VL1i1c/JL3b (SEQ ID NO: 50338):

QSVLTQP-PSASGTPGQRVTISCSGSS-SNIGS------NIVTWYQQLPGTAPKLLIYS------NDQRPSGVPDRFSGSKSG-TSASLAISGLQSEDEADYYCAAWDDS----------LNGWFGGGTLTVLG wherein:

S at position 27 can be substituted with N or C

S at position 33 can be substituted with N

N at position 39 can be substituted with H

I at position 40 can be substituted with T

T at position 42 can be substituted with N

S at position 58 can be substituted with G, N or V

D at position 68 can be substituted with K, N or Y

A at position 107 can be substituted with T

A at position 108 can be substituted with T or V

N at position 135 can be substituted with I or S

G at position 136 can be substituted with D or V

Ser Gly Ser Xaa Ser Asn Ile Gly Xaa Xaa Xaa Val Xaa (SEQ ID NO: 50195)

Xaa Asn Xaa Gln Arg Pro Ser (SEQ ID NO: 50196)

Xaa Xaa Trp Asp Asp Ser Leu Xaa Xaa Trp Val (SEQ ID NO: 50197)

Ser Gly Ser Ser Ser Asn Ile Gly Ser Asn Ile Val Thr (SEQ ID NO: 50684)

Ser Asn Asp Gln Arg Pro Ser (SEQ ID NO: 50685)

Ala Ala Trp Asp Asp Ser Leu Asn Gly Trp Val (SEQ ID NO: 50686)

Table 122. Consensus 42 - VK1|A30/JK5 (SEQ ID NO: 50339):

DIQMTQSPSSLSASVGDRVTITCRAS--QGIR------NDLGWYQQKPGKAPKRLIYA--------ASSLQSGVPSRFSGSGSG--TEFTLTISSLQPEDFATYYCLQHNS-------------YPITFGQGTRLEIKR wherein:

A at position 25 can be substituted with T

G at position 30 can be substituted with D or R

I at position 31 can be substituted with V

N at position 39 can be substituted with S

A at position 58 can be substituted with D, I or T

S at position 69 can be substituted with N

Q at position 71 can be substituted with E, F or L

L at position 107 can be substituted with I

Q at position 108 can be substituted with H

H at position 109 can be substituted with Y

N a position 110 can be substituted with H or S

S at position 111 can be substituted with N null (-) at position 134 can be substituted with Y Y at position 135 can be substituted with L, F or P I at position 137 can be substituted with P or L Arg Xaa Ser Gln Xaa Xaa Arg Xaa Asp Leu Gly (SEQ ID NO: 50198)

Xaa Ala Ser Xaa Leu Xaa Ser (SEQ ID NO: 50199)

Xaa Xaa Xaa Xaa Xaa Xaa Pro Xaa Thr (SEQ ID NO: 50200)

Arg Ala Ser Gln Gly Ile Arg Asn Asp Leu Gly (SEQ ID NO: 50687)

Ala Ala Ser Ser Leu Gln Ser (SEQ ID NO: 50688)

Leu Gln His Asn Ser Tyr Pro Ile Thr (SEQ ID NO: 50689)

Table 123. Consensus 43 - VK1|O12/JK5 (SEQ ID NO: 50340):

FIGURE 57 (Continued)

DIQMTQSPSSLSASVGDRVTITCRAS--QSIS------SYLNWYQQKPGKAPKLLIYA--------ASSLQSGVPSRFSGSGSG--
TDFTLTISSLQPEDFATYCQQSYS--------------IPITFGQGTRLEIKR wherein:

A at position 25 can be substituted with T

S at position 30 can be substituted with N or Y

I at position 31 can be substituted with S or F

S at position 32 can be substituted with F, N, R or T

S at position 39 can be substituted with D, G or R

L at position 41 can be substituted with S

N at position 42 can be substituted with S

A at position 58 can be substituted with D, G or S

A at position 67 can be substituted with T

S at position 68 can be substituted with Y

S at position 69 can be substituted with T

L at position 70 can be substituted with F

Q at position 71 can be substituted with E or K

S at position 72 can be substituted with T

Q at position 107 can be substituted with H

Q at position 108 can be substituted with E

S at position 109 can be substituted with T

Y at position 110 can be substituted with F

FIGURE 57 (Continued)

S at position 111 can be substituted with G or N

I at position 135 can be substituted with T, L, N or S

P at position 136 can be substituted with S, R or T

I at position 137 can be substituted with F or P

T at position 138 can be substituted with A

Arg Xaa Ser Gln Xaa Xaa Xaa Xaa Tyr Xaa Xaa (SEQ ID NO: 50201)

Xaa Xaa Xaa Xaa Xaa Xaa Xaa Xaa (SEQ ID NO: 50202)

Xaa Xaa Xaa Xaa Xaa Xaa Xaa Xaa Xaa Xaa (SEQ ID NO: 50203)

Arg Ala Ser Gln Ser Ile Ser Ser Tyr Leu Asn (SEQ ID NO: 50690)

Ala Ala Ser Ser Leu Gln Ser (SEQ ID NO: 50691)

Gln Gln Ser Tyr Ser Ile Pro Ile Thr (SEQ ID NO: 50692)

Table 124. Consensus 44 - VK2iA18/JK5 (SEQ ID NO: 50341):

DIVMTQTPLSLSVTPGQPASISCKSS--QSLLHSE-GKTYLYWYLQKPGQPPQLLIYE--------VSNRFSGVPDRFSGSGSG--TDFTLKISRVEAEDVGVYYCMQSIQ--------LPITFGQGTRLEIKR wherein:

K at position 24 can be substituted with R

S at position 25 can be substituted with T

S at position 26 can be substituted with N

S at position 30 can be substituted with I

L at position 31 can be substituted with F

L at position 32 can be substituted with V

S at position 34 can be substituted with N or R

E at position 35 can be substituted with D

K at position 38 can be substituted with R

V at position 67 can be substituted with L

N at position 69 can be substituted with K or H

F at position 71 can be substituted with L or V

M at position 107 can be substituted with I or L

I at position 110 can be substituted with M

Q at position 111 can be substituted with null (-) or L

L at position 135 can be substituted with Y, I or Q

FIGURE 57 (Continued)

P at position 136 can be substituted with L

T at position 138 can be substituted with I

Xaa Xaa Xaa Gln Xaa Xaa His Xaa Xaa Gly Xaa Thr Tyr Leu Tyr (SEQ ID NO: 50204)

Glu Xaa Ser Xaa Arg Xaa Ser (SEQ ID NO: 50205)

Xaa Gln Ser Xaa Xaa Xaa Xaa Ile Xaa (SEQ ID NO: 50246)

Lys Ser Ser Gln Ser Leu Leu His Ser Glu Gly Lys Thr Tyr Leu Tyr (SEQ ID NO: 50693)

Glu Val Ser Asn Arg Phe Ser (SEQ ID NO: 50694)

Met Gln Ser Ile Gln Leu Pro Ile Thr (SEQ ID NO: 50695)

Table 125. Consensus 45 – VK3|A27/JK3 (SEQ ID NO: 50342):

EIVLTQSPGTLSLFPGERATLSCRAS--OSVIS-----SYLAWYQQKPGQAPRLLIFG------VSSRATGIPDRFSGSGSG--
TDFTLTISRLEPEDFAVYYCQQYGR----------SPFNFGPGTKVDIKR wherein:

Q at position 29 can be substituted with R.

S at position 30 can be substituted with G or N

V at position 31 can be substituted with I

I at position 32 can be substituted with S or G

S at position 33 can be substituted with N

S at position 39 can be substituted with I or N

Y at position 40 can be substituted with F

V at position 67 can be substituted with A or T

S at position 69 can be substituted with N or T

R at position 70 can be substituted with W

Q at position 107 can be substituted with H

Q at position 108 can be substituted with H

Y at position 109 can be substituted with N

G at position 110 can be substituted with D

R at position 111 can be substituted with null (-), N or Y

P at position 136 can be substituted with L or M

FIGURE 57 (Continued)

N at position 138 can be substituted with T

Arg Ala Ser Xaa Xaa Xaa Xaa Xaa Xaa Xaa Leu Ala (SEQ ID NO: 50206)

Gly Xaa Ser Xaa Xaa Ala Thr (SEQ ID NO: 50207)

Xaa Xaa Xaa Xaa Ser Xaa Xaa Xaa Asn (SEQ ID NO: 50208)

Arg Ala Ser Gln Ser Val Ile Ser Ser Tyr Leu Ala (SEQ ID NO: 50696)

Gly Val Ser Ser Arg Ala Thr (SEQ ID NO: 50697)

Gln Gln Tyr Gly Arg Ser Pro Phe Asn (SEQ ID NO: 50698)

Table 126. Consensus 46 - VK3jL2/JK1 (SEQ ID NO: 50343):

EIVMTQSPATLSVSPGERATLSCRAS--QSVS-----SNLAWYQQKPGQAPRLLIYG-----ASTRATGIPARFSGSGSG--
TEFTLTISSLQSEDFAVYYCQQYND-----------------WPWTFGQGTKVEIKR wherein:

A at position 25 can be substituted with S

S at position 30 can be substituted with D or T

V at position 31 can be substituted with I

S at position 32 can be substituted with N, R or I

S at position 39 can be substituted with I or T

N at position 40 can be substituted with Y

L at position 41 can be substituted with I

T at position 72 can be substituted with S

Q at position 108 can be substituted with E

Y at position 109 can be substituted with S

N at position 110 can be substituted with D, F or H

D at position 111 can be substituted with N, null (-) or T null (-) at position 134 can be substituted with W W at position 135 can be substituted with P, C or N P at position 136 can be substituted with L or W W at position 137 can be substituted with L, C, P or R FIGURE 57 (Continued)

T at position 138 can be substituted with P or S

Arg Xaa Ser Gln Xaa Xaa Xaa Xaa Xaa Xaa Ala (SEQ ID NO: 50209)

Gly Ala Ser Thr Arg Ala Xaa (SEQ ID NO: 50210)

Gln Xaa Xaa Xaa Xaa Xaa Xaa Xaa Xaa Xaa Xaa (SEQ ID NO: 50211)

Arg Ala Ser Gln Ser Val Ser Ser Asn Leu Ala (SEQ ID NO: 50699)

Gly Ala Ser Thr Arg Ala Thr (SEQ ID NO: 50700)

Gln Gln Tyr Asn Asp Trp Pro Trp Thr (SEQ ID NO: 50701)

Table 127. Consensus 47 – VK6/A26/JK1 (SEQ ID NO: 50344):

EIVLTQSPDFQSVTPKEKVTITCRAS--QSIG-----SSLHWYQQKPDQSPKLLIKY--------ASQSFSGVPSRFSGSGSG--
TDFTLTINSLEAEDAATYYCHQSSS------------LPWIFGQGTKVEIKR wherein:

S at position 30 can be substituted with N

S at position 39 can be substituted with N

S at position 40 can be substituted with N or T

Y at position 58 can be substituted with S

H at position 107 can be substituted with Q

S at position 110 can be substituted with G or R

L at position 135 can be substituted with F

W at position 137 can be substituted with R or Q

Arg Ala Ser Gln Xaa Ile Gly Xaa Xaa Leu His (SEQ ID NO: 50256)

Xaa Ala Ser Gln Ser Phe Ser (SEQ ID NO: 50257)

Xaa Gln Ser Xaa Ser Xaa Pro Xaa Thr (SEQ ID NO: 50258)

Arg Ala Ser Gln Ser Ile Gly Ser Ser Leu His (SEQ ID NO: 50702)

Tyr Ala Ser Gln Ser Phe Ser (SEQ ID NO: 50703)

His Gln Ser Ser Leu Pro Trp Thr (SEQ ID NO: 50704)

Table 128. Consensus 48 – VK1|A30/JK2 (SEQ ID NO: 50345):

DIQMTQSPSSLSASVGDRVTITCRAS--QGIR----NDLGWYQQKPGKAPKRLIYA--------ASSLQSGVPSRFSGSGSG--TEFTLTISSLQPEDFATYYCLQHYS----------------------YPRSFGQGTKLEIKR wherein:

G at position 30 can be substituted with A

R at position 32 can be substituted with G

N at position 39 can be substituted with D

A at position 67 can be substituted with T

Y at position 110 can be substituted with N

S at position 111 can be substituted with N

Y at position 135 can be substituted with F

R at position 137 can be substituted with Y

Arg Ala Ser Gln Xaa Ile Xaa Xaa Asp Leu Gly (SEQ ID NO: 50247)

Ala Xaa Ser Ser Leu Gln Ser (SEQ ID NO: 50248)

Leu Gln His Xaa Xaa Xaa Pro Xaa Ser (SEQ ID NO: 50249)

Arg Ala Ser Gln Gly Ile Arg Asn Asp Leu Gly (SEQ ID NO: 50705)

Ala Ala Ser Ser Leu Gln Ser (SEQ ID NO: 50706)

Leu Gln His Tyr Ser Tyr Pro Arg Ser (SEQ ID NO: 50707)

| Reference # | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|
| | | | K_CDR2 | | | | | | | | | | | | | | | | | | | | | | | |
| CONSENSUS | K | R | L | I | Y | A | - | - | - | - | - | - | - | - | A | S | S | L | Q | S | G | V | P | S | R | F |
| 21-225_150E2_LC | T | . | . | . | . | . | . | . | . | . | . | . | . | . | . | . | . | . | . | . | . | . | . | . | . | . |
| 21-225_152F7_LC | . | . | . | . | . | . | . | . | . | . | . | . | . | . | . | . | . | . | . | . | . | . | . | . | . | . |
| 21-225_176H12_LC | N | . | . | . | . | . | . | . | . | . | . | . | . | . | . | . | . | . | . | . | . | . | . | . | . | . |
| 21-225_177B4_LC | . | . | . | . | . | . | . | . | . | . | . | . | . | . | . | . | . | . | . | . | . | . | . | . | . | . |
| 21-225_25A12_LC | . | . | . | . | . | . | . | . | . | . | . | . | . | . | T | . | . | . | . | . | . | . | . | . | . | . |
| 21-225_26A11_LC | . | . | . | . | . | . | . | . | . | . | . | . | . | . | . | . | . | . | . | . | . | . | . | . | . | . |
| 21-225_28H2_LC | . | . | . | . | . | . | . | . | . | . | . | . | . | . | . | . | . | . | . | . | . | . | . | . | . | . |
| 21-225_29E2_LC | . | . | . | . | . | . | . | . | . | . | . | . | . | . | . | . | . | . | . | . | . | . | . | . | . | . |
| 21-225_61F2_LC | E | . | . | . | . | . | . | . | . | . | . | . | . | . | . | . | . | . | . | . | . | . | . | . | . | . |

| Reference # | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|
| | | | | | | | | | | | K_FR3 | | | | | | | | | | | | | | | |
| CONSENSUS | S | G | S | G | S | G | - | - | T | E | F | T | L | T | I | S | S | L | Q | P | E | D | F | A | T | Y |
| 21-225_150E2_LC | . | . | . | . | . | . | . | . | . | . | . | . | . | . | . | . | . | . | . | . | . | . | . | . | . | . |
| 21-225_152F7_LC | . | . | . | . | . | . | . | . | . | . | . | . | . | . | . | . | . | . | . | . | . | . | . | . | . | . |
| 21-225_176H12_LC | . | . | . | . | . | . | . | . | . | . | . | . | . | . | . | . | . | . | . | . | . | . | . | . | . | . |
| 21-225_177B4_LC | . | . | . | . | . | . | . | . | . | . | . | . | . | . | . | . | . | . | . | . | . | . | . | . | . | . |
| 21-225_25A12_LC | . | . | . | . | . | . | . | . | . | . | . | . | . | . | . | . | . | . | . | . | A | . | . | . | . | . |
| 21-225_26A11_LC | . | . | . | . | . | . | . | . | . | . | . | . | . | . | . | . | . | . | . | X | . | . | . | . | . | . |
| 21-225_28H2_LC | . | . | . | . | . | . | . | . | . | . | . | . | . | . | . | . | . | . | . | . | . | . | . | . | . | . |
| 21-225_29E2_LC | . | . | . | . | . | . | . | . | . | . | . | . | . | . | . | . | . | . | . | . | . | . | . | . | . | . |
| 21-225_61F2_LC | . | . | . | . | . | . | . | . | . | . | . | . | . | . | . | . | . | . | . | . | . | . | . | . | . | . |

Table 129. Consensus 49 – VK1|L1/JK5 (SEQ ID NO: 50346):

DIQMTQSPSSLSASVGDRVTITCRAS--QGIS-------NYLAWFQQKPGKAPKSLIYA--------ASSLQSGVPSKFSGSGSG--
TDFTLTISSLQPEDFATYCQQYLS----------------------YPHTFGQGTRLEIKR wherein:

R at position 24 can be substituted with Q

G at position 30 can be substituted with D

S at position 32 can be substituted with N

N at position 39 can be substituted with K

Y at position 40 can be substituted with F

A at position 42 can be substituted with N or V

A at position 58 can be substituted with D, G, or T

S at position 68 can be substituted with T

S at position 69 can be substituted with R or N

Q at position 71 can be substituted with H, L, or V

S at position 72 can be substituted with T

Q at position 107 can be substituted with H or L

Q at position 108 can be substituted with H or L

L at position 110 can be substituted with H, D, K, N, or Y

S at position 111 can be substituted with N, H, or T

Y at position 135 can be substituted with L

FIGURE 57 (Continued)

I at position 137 can be substituted with L

Xaa Ala Ser Gln Xaa Ile Xaa Xaa Xaa Leu Xaa (SEQ ID NO: 50212)

Xaa Ala Xaa Xaa Leu Xaa Xaa (SEQ ID NO: 50213)

Xaa Xaa Tyr Xaa Xaa Xaa Pro Xaa Thr (SEQ ID NO: 50214)

Arg Ala Ser Gln Gly Ile Ser Asn Tyr Leu Ala (SEQ ID NO: 50708)

Ala Ala Ser Ser Leu Gln Ser (SEQ ID NO: 50709)

Gln Gln Tyr Leu Ser Tyr Pro Ile Thr (SEQ ID NO: 50710)

Table 130. Consensus 50 - VK6/A26/JK4 (SEQ ID NO: 50347):

EIVLTQSPDFQSVTPKEKVTITCRAS--QSIG------SSLHWYQQKPDQSPKLLIKY--------ASQSFSGVPSRFSGSGSG--
TDFTLTINSLEAEDAATYYCHQSRR---------------------LPLTFGGGTKVEIKR wherein:

S at position 26 can be substituted with N
S at position 30 can be substituted with N
S at position 39 can be substituted with R
F at position 71 can be substituted with L
S at position 109 can be substituted with T
R at position 110 can be substituted with G or S
R at position 111 can be substituted with S or T
Xaa Ala Xaa Gln Ser Xaa Gly Ser Ser Leu His (SEQ ID NO: 50215)
Tyr Ala Ser Gln Ser Xaa Ser (SEQ ID NO: 50216)
His Gln Xaa Xaa Xaa Leu Pro Leu Thr (SEQ ID NO: 50217)
Arg Ala Ser Gln Ser Ile Gly Ser Ser Leu His (SEQ ID NO: 50711)
Tyr Ala Ser Gln Ser Phe Ser (SEQ ID NO: 50712)
His Gln Ser Arg Arg Leu Pro Leu Thr (SEQ ID NO: 50713)

Table 131.  Consensus 51 - VL3j3l/JL2 (SEQ ID NO: 50348):

SSELTQD-PAVSVALGQTVRITCQGD---SLRP------YYASWYQQKPGQAPVLVIYG--------KNNRPSGIPDRFSGSSSG--NTASLTITGAQAEDEADYYCNSRDSS-----------GNHLVVFGGGTKLTVLG wherein:

S at position 30 can be substituted with T or K

P at position 33 can be substituted with N, S, or T

A at position 41 can be substituted with V

S at position 42 can be substituted with N

G at position 58 can be substituted with A or T

N at position 69 can be substituted with S

S at position 112 can be substituted with C

G at position 133 can be substituted with null (-)

N at position 134 can be substituted with G

H at position 135 can be substituted with N or S

L at position 136 can be substituted with H

V at position 137 can be substituted with L

V at position 138 can be substituted with L

Gln Gly Asp Xaa Leu Arg Xaa Tyr Tyr Xaa Xaa (SEQ ID NO: 50218)

Xaa Lys Asn Xaa Arg Pro Ser (SEQ ID NO: 50219)

Asn Ser Arg Asp Ser Xaa Xaa Xaa Xaa Xaa Xaa Xaa (SEQ ID NO: 50220)

FIGURE 57 (Continued)

Gln Gly Asp Ser Leu Arg Pro Tyr Tyr Ala Ser (SEQ ID NO: 50714)

Gly Lys Asn Arg Pro Ser (SEQ ID NO: 50715)

Asn Ser Arg Asp Ser Ser Gly Asn His Leu Val Val (SEQ ID NO: 50716)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | | L_FR1 | | | | | | | | | | | | | | |
| CONSENSUS | S | S | E | L | T | Q | D | - | P | A | V | S | V | A | L | G | Q | T | V | R | I | T | C | Q | G | D |
| 21-225_171D12_LC | . | . | . | . | . | . | . | . | . | . | . | . | . | . | . | . | . | . | . | . | . | . | . | . | . | . |
| 21-225_172B12_LC | . | . | . | . | . | . | . | . | . | . | . | . | . | . | . | . | . | . | . | . | . | . | . | . | . | . |
| 21-225_172C3_LC | . | . | . | . | . | . | . | . | . | . | . | . | . | . | . | . | . | . | . | . | . | . | . | . | . | . |
| 21-225_190B3_LC | . | . | . | . | . | . | . | . | . | . | . | . | . | . | . | . | . | . | . | . | . | . | . | . | . | . |
| 21-225_190B8_LC | . | . | . | . | . | . | . | . | . | . | . | . | . | . | . | . | . | . | . | . | . | . | . | . | . | . |
| 21-225_190C10_LC | . | . | . | . | . | . | . | . | . | . | . | . | . | . | . | . | . | . | . | . | . | . | . | . | . | . |
| 21-225_191A9_LC | . | . | . | . | . | . | . | . | . | . | . | . | . | . | . | . | . | . | . | . | . | . | . | . | . | . |
| 21-225_191B8_LC | . | . | . | . | . | . | . | . | . | . | . | . | . | . | . | . | . | . | . | . | . | . | . | . | . | . |
| 21-225_193A6_LC | . | . | . | . | . | . | . | . | . | . | . | . | . | . | . | . | . | . | . | . | . | . | . | . | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | | | L_CDR1 | | | | | | | | | | | L_FR2 | | | | | | | | | |
| CONSENSUS | - | - | - | S | L | R | P | - | - | - | - | - | Y | Y | A | S | W | Y | Q | Q | K | P | G | Q | A | P |
| 21-225_171D12_LC | . | . | . | . | . | . | . | . | . | . | . | . | . | . | . | . | . | . | . | . | . | . | . | . | . | . |
| 21-225_172B12_LC | . | . | . | . | . | S | . | . | . | . | . | . | . | . | . | . | . | . | . | . | . | . | . | . | . | . |
| 21-225_172C3_LC | . | . | . | K | . | N | . | . | . | . | . | . | . | . | . | . | . | . | . | . | . | . | . | . | . | . |
| 21-225_190B3_LC | . | . | . | T | . | N | . | . | . | . | . | . | . | . | V | . | . | . | . | . | . | . | . | . | . | . |
| 21-225_190B8_LC | . | . | . | . | . | T | . | . | . | . | . | . | . | . | . | . | . | . | . | . | . | . | . | . | . | . |
| 21-225_190C10_LC | . | . | . | T | . | . | . | . | . | . | . | . | . | . | V | . | . | . | . | . | . | . | . | . | . | . |
| 21-225_191A9_LC | . | . | . | . | . | . | . | . | . | . | . | . | . | . | . | . | . | . | . | . | . | . | . | . | . | . |
| 21-225_191B8_LC | . | . | . | . | . | . | . | . | . | . | . | . | . | . | . | . | . | . | . | . | . | . | . | . | . | . |
| 21-225_193A6_LC | . | . | . | . | . | S | . | . | . | . | . | . | . | . | . | N | . | . | . | . | . | . | . | . | . | . |

Table 132. Consensus 52 - VK2/A17/JK4 (SEQ ID NO: 50349):

DVVMTQSPLSLPVTLGQPASISCRSS--QSLVYSD-GNTYLNWFQQRPGQSPRRLIYK------VSNWDSGVPDRFSGSGSG--TDFTLKISRVEAEDVGVYYCMQGTH----------WPLTFGGGTKVEIKR wherein:

S at position 26 can be substituted with G

Y at position 40 can be substituted with S

K at position 58 can be substituted with E

N at position 69 can be substituted with K

S at position 72 can be substituted with Y

T at position 110 can be substituted with I

H at position 111 can be substituted with null (-)

W at position 135 can be substituted with H

P at position 136 can be substituted with L, S or W

L at position 137 can be substituted with P

Arg Ser Xaa Gln Ser Leu Val Tyr Ser Asp Gly Asn Thr Xaa Leu Asn (SEQ ID NO: 50221)

Xaa Val Ser Xaa Trp Asp Ser Xaa (SEQ ID NO: 50222)

Met Gln Gly Xaa Xaa Xaa Xaa Xaa Thr (SEQ ID NO: 50223)

Arg Ser Gln Ser Leu Val Tyr Ser Asp Gly Asn Thr Tyr Leu Asn (SEQ ID NO: 50717)

Lys Val Ser Asn Trp Asp Ser (SEQ ID NO: 50718)

Met Gln Gly Thr His Trp Pro Leu Thr (SEQ ID NO: 50719)

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | L_FR4 | | | | | |
| CONSENSUS | . | . | . | . | W | P | L | T | F | G | G | G | T | K | V | E | I | K | R |
| 21-225_148C6_LC | . | . | . | . | . | S | . | . | . | . | . | . | . | . | . | . | . | . | . |
| 21-225_148H11_LC | . | . | . | . | . | L | . | . | . | . | . | . | . | . | . | . | . | . | . |
| 21-225_149F2_LC | . | . | . | . | . | . | P | . | . | . | . | . | . | . | . | . | . | . | T |
| 21-225_150F11_LC | . | . | . | . | . | . | R | . | . | . | . | . | . | . | . | . | . | . | . |
| 21-225_177D2_LC | . | . | . | . | T | W | . | . | . | . | . | . | . | . | . | . | . | . | . |
| 21-225_32G4_LC | . | . | . | . | . | . | . | . | . | . | . | . | . | . | . | . | . | . | . |
| 21-225_43F11_LC1_LC | . | . | . | . | . | . | . | . | . | . | . | . | . | . | . | . | . | . | . |
| 21-225_72C4_LC | . | . | . | . | . | . | . | . | . | . | . | . | . | . | . | . | . | . | . |

FIGURE 57
(Continued)

Table 133. Consensus 53 - VK3jL2/JK4 (SEQ ID NO: 50350):

EIVMTQSPATLSVSPGERATLSCRAS--QSVS------RNLAWYQQKPGQAPRLLIYG--------ASTRATGIPARFSGSGSG--
TEFTLTISSLQSEDFAVYYCQQYNN-------------WPLTFGGGTKVEIKR wherein:

A at position 25 can be substituted with P or T

V at position 31 can be substituted with F

S at position 32 can be substituted with R or W

R at position 39 can be substituted with I or S

N at position 40 can be substituted with D or S

L at position 41 can be substituted with V

G at position 58 can be substituted with D

S at position 68 can be substituted with A

T at position 69 can be substituted with I or A

N at position 110 can be substituted with Y

N at position 111 can be substituted with T or Y null (-) at position 134 can be substituted with W W at position 135 can be substituted with P Arg Xaa Ser Gln Ser Xaa Xaa Xaa Xaa Xaa Ala (SEQ ID NO: 50224)

Xaa Ala Xaa Xaa Arg Ala Thr (SEQ ID NO: 50225)

Gln Gln Tyr Xaa Xaa Xaa Pro Leu Thr (SEQ ID NO: 50226)

Arg Ala Ser Gln Ser Val Ser Arg Asn Leu Ala (SEQ ID NO: 50720)

FIGURE 57 (Continued)

Gly Ala Ser Thr Arg Ala Thr (SEQ ID NO: 50721)
Gln Gln Tyr Asn Asn Trp Pro Leu Thr (SEQ ID NO: 50722)

| Reference # | 105 | 106 | 107 | 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 |
|---|---|---|---|---|---|---|---|---|---|---|---|---|---|---|---|---|---|---|---|---|---|---|---|---|---|---|
| | | | | | | | | | | | | | | | | | | K_CDR3 | | | | | | | | |
| CONSENSUS | Y | C | Q | Q | Y | N | N | | | | | | | | | | | | | | | | | | | |
| 21-225_190E11_LC | . | . | . | . | . | . | . | . | | | | | | | | | | | | | | | | | | |
| 21-225_191E8_LC | . | . | . | . | . | . | . | . | | | | | | | | | | | | | | | | | | |
| 21-225_191G11_LC | . | . | . | . | . | Y | Y | . | | | | | | | | | | | | | | | | | | |
| 21-225_199A6_LC | . | . | . | . | . | . | . | . | | | | | | | | | | | | | | | | | | |
| 21-225_55E1_LC | . | . | . | . | . | . | . | . | | | | | | | | | | | | | | | | | | |
| 21-225_65C12_LC | . | . | . | . | . | . | T | . | | | | | | | | | | | | | | | | | | |
| 21-225_74D1_LC | . | . | . | . | . | . | . | . | | | | | | | | | | | | | | | | | | |
| 21-225_75F11_LC | . | . | . | . | . | . | . | . | | | | | | | | | | | | | | | | | | |

| Reference # | 131 | 132 | 133 | 134 | 135 | 136 | 137 | 138 | 139 | 140 | 141 | 142 | 143 | 144 | 145 | 146 | 147 | 148 | 149 |
|---|---|---|---|---|---|---|---|---|---|---|---|---|---|---|---|---|---|---|---|
| | | | | | | | | | | | | | | K_FR4 | | | | | |
| CONSENSUS | | | | | W | P | L | T | F | G | G | G | T | K | V | E | I | K | R |
| 21-225_190E11_LC | | | | | . | . | . | . | . | . | . | . | . | . | . | . | . | . | . |
| 21-225_191E8_LC | | | | | . | . | . | . | . | . | . | . | . | . | . | . | . | . | . |
| 21-225_191G11_LC | | | | | . | . | . | . | . | . | . | . | . | . | . | . | . | . | . |
| 21-225_199A6_LC | | | | | . | . | . | . | . | . | . | . | . | . | . | . | . | . | . |
| 21-225_55E1_LC | | | | | . | . | . | . | . | . | . | . | . | . | . | . | . | . | . |
| 21-225_65C12_LC | | | | | . | . | . | . | . | . | . | . | . | . | . | . | . | . | . |
| 21-225_74D1_LC | | | W | P | . | . | . | . | . | . | . | . | . | . | . | . | . | . | . |
| 21-225_75F11_LC | | | W | P | . | . | . | . | . | . | . | . | . | . | . | . | . | . | . |

FIGURE 57 (Continued)

Table 134.   Consensus 54 - VL3|3j/JL2 (SEQ ID NO: 50351):

SYELTQP-LSVSVALGQTARITCGGN---NIGR------KNVHWYQQKPGQAPVLVIYR-------DSDRPSGIPERFSGSNSG--
NTATLTISRAQAGDEADYYCQVWDS.................STVVFGGGTKLTVLG wherein:

N at position 26 can be substituted with D

G at position 32 can be substituted with R

R at position 33 can be substituted with S

K at position 39 can be substituted with R

N at position 40 can be substituted with A

R at position 58 can be substituted with S

S at position 68 can be substituted with R

D at position 69 can be substituted with N or Y

P at position 71 can be substituted with S

V at position 108 can be substituted with D null (-) at position 112 can be substituted with S null (-) at position 134 can be substituted with S S at position 135 can be substituted with D or G T at position 136 can be substituted with H V at position 137 can be substituted with A or G Gly Gly Asn Ile Xaa Xaa Xaa Xaa Val His (SEQ ID NO: 50250)

Xaa Asp Xaa Xaa Arg Xaa Ser (SEQ ID NO: 50251)

FIGURE 57 (Continued)

Gln Xaa Trp Asp Ser Xaa Xaa Xaa Xaa Xaa Val (SEQ ID NO: 50252)

Gly Gly Asn Asn Ile Gly Arg Lys Asn Val His (SEQ ID NO: 50723)

Arg Asp Ser Asp Arg Pro Ser (SEQ ID NO: 50724)

Gln Val Trp Asp Ser Ser Thr Val Val (SEQ ID NO: 50725)

| Reference # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | | | | | | | | | | | LFR1 | | | | | | | | | | | | | | | |
| CONSENSUS | S | Y | E | L | T | Q | P | . | L | S | V | S | V | A | L | G | Q | T | A | R | I | T | C | G | G | N |
| 21-225_203B2_LC | . | . | . | . | . | . | . | . | . | . | . | . | . | . | . | . | . | . | . | . | . | . | . | . | . | . |
| 21-225_205E12_LC | . | . | . | . | . | . | . | . | . | . | . | . | . | . | . | . | . | . | . | . | . | . | . | . | . | . |
| 21-225_206B5_LC | . | . | . | . | . | . | . | . | . | . | . | . | A | . | . | . | . | . | . | . | . | A | . | . | . | . |
| 21-225_209H10_LC | . | . | . | . | . | . | . | . | . | . | . | . | . | . | . | . | . | . | . | . | . | A | . | . | . | . |
| 21-225_211H2_LC | . | . | . | . | . | . | . | . | . | . | . | . | . | . | . | . | . | . | . | . | . | . | . | . | . | . |
| 21-225_216B12_LC | . | . | . | . | . | . | . | . | H | . | . | . | . | . | T | A | . | M | . | . | . | . | . | . | . | Q |
| 21-225_3E10_LC | . | . | . | . | . | . | . | . | H | . | . | . | . | . | T | A | . | M | . | . | . | . | . | . | . | . |
| 21-225_8C12_LC | . | . | . | . | . | . | . | . | . | . | . | . | . | . | . | . | . | . | . | . | . | . | . | . | . | . |

| Reference # | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|---|
| | | | | L_CDR1 | | | | | | | | | | | LFR2 | | | | | | | | | | | |
| CONSENSUS | . | . | . | N | I | G | R | . | . | . | . | K | N | V | H | W | Y | Q | Q | K | P | G | Q | A | P | P |
| 21-225_203B2_LC | . | . | . | . | . | . | . | . | . | . | . | . | . | . | . | . | . | . | . | . | . | . | . | . | S | . |
| 21-225_205E12_LC | . | . | . | . | . | . | . | . | . | . | . | . | . | . | . | . | . | . | . | . | . | . | . | . | S | . |
| 21-225_206B5_LC | . | . | . | . | . | . | . | . | . | . | . | . | . | . | . | . | . | . | . | . | . | . | . | . | . | . |
| 21-225_209H10_LC | . | . | . | . | . | . | . | . | . | . | . | R | . | . | . | . | . | . | . | . | . | . | L | . | . | . |
| 21-225_211H2_LC | . | . | . | . | . | . | . | . | . | . | . | R | . | . | . | . | . | . | . | . | . | . | L | . | . | . |
| 21-225_216B12_LC | . | . | . | . | . | S | . | . | . | . | . | . | A | . | . | . | . | . | . | . | . | . | . | . | . | . |
| 21-225_3E10_LC | . | . | . | . | . | S | . | . | . | . | . | . | A | . | . | . | . | . | . | . | . | . | . | . | Q | . |
| 21-225_8C12_LC | . | . | . | . | . | . | . | . | . | . | . | . | . | . | . | . | . | . | . | . | . | . | . | . | D | . |

Table 7.6. ASGR-1 residues identified as hits via Arg/Glu scanning mutagenesis:

| mAb | Relative Epitope Profiling Bin | ASGR1 CBD Mutations That Reduced Antibody Binding Signal (3xIQR Cutoff) | | | | | | | | | | | | | | | | | |
|---|---|---|---|---|---|---|---|---|---|---|---|---|---|---|---|---|---|---|---|
| 4A2 | A | W195 | | | | | | | | | | | | | | | | | |
| 7E11 | A | W195 | | | | | | | | | | | | | | | | | |
| 56E5 | A | W195 | | | | | | | | | | | | | | | | | |
| 7G4 | A | W195 | R263 | | | | | | | | | | | | | | | | |
| 53F7 | A | W195 | K199 | E196 | | | | | | | | | | | | | | | |
| 10G6 | A | W195 | E196 | | | | | | | | | | | | | | | | |
| 26C4 | A | W195 | P207 | | | | | | | | | | | | | | | | |
| 6G6 | A | | | | | | | | | | | | | | | | | | |
| 29H8 | A | W195 | P207 | | | | | | | | | | | | | | | | |
| 25A4 | A | | | | | | | | | | | | | | | | | | |
| 32D6 | A | W195 | K199 | | | | | | | | | | | | | | | | |
| 198D2 | unknown | W195 | E196 | H204 | | | | | | | | | | | | | | | |
| 4B3 | A | H203 | H204 | | | | | | | | | | | | | | | | |
| 50G9 | A | H203 | H204 | | | | | | | | | | | | | | | | |
| 60D2 | A | H203 | H204 | | | | | | | | | | | | | | | | |
| 59F2 | A | H203 | H204 | | | | | | | | | | | | | | | | |
| 60E8 | A | H203 | H204 | P220 | G251 | | | | | | | | | | | | | | |
| 65E9 | A.1 | H203 | H204 | | | | | | | | | | | | | | | | |
| 5E5 | A | K199 | W195 | R263 | | | | | | | | | | | | | | | |
| 29E2 | A | K199 | R263 | | | | | | | | | | | | | | | | |
| 45B4 | A | K199 | R263 | | | | | | | | | | | | | | | | |
| 6G7 | B | L184 | | | | | | | | | | | | | | | | | |
| 72F5 | B.1 | L184 | | | | | | | | | | | | | | | | | |
| 22G5 | B | L184 | N265 | P220 | H215 | G251 | G248 | R183 | G246 | | | | | | | | | | |
| 48B12 | B | L184 | | | | | | | | | | | | | | | | | |
| 151B9 | B | L184 | | | | | | | | | | | | | | | | | |
| 52H2 | B | L184 | P238 | H247 | G251 | P220 | | | | | | | | | | | | | |
| 149D11 | B | R170 | L184 | S171 | | | | | | | | | | | | | | | |
| 175F4 | B | R183 | | | | | | | | | | | | | | | | | |
| 147E9 | C | | P241 | D242 | G251 | E263 | Y245 | | | | | | | | | | | | |
| 61A1 | C | | P241 | Y245 | D242 | E263 | G251 | | | | | | | | | | | | |
| 184E7 | C | | E263 | P241 | | | | | | | | | | | | | | | |
| 72G9 | C | | Y245 | P241 | D242 | E263 | G251 | | | | | | | | | | | | |
| 194A4 | C | D260 | | | | | | | | | | | | | | | | | |
| 60C12 | E | R263 | D260 | R263 | | | | | | | | | | | | | | | |
| 173C11 | E | R237 | D260 | T259 | R263 | | | | | | | | | | | | | | |
| 56E3 | E.1 | R237 | T259 | R263 | N265 | D260 | P241 | R170 | | | | | | | | | | | |
| 54E9 | E.1 | R237 | T259 | N265 | R263 | D260 | P241 | E239 | | | | | | | | | | | |
| 65D5 | E | D260 | R237 | R263 | T259 | | | | | | | | | | | | | | |
| 190F8 | L | R271 | R274 | G172 | P272 | V208 | | | | | | | | | | | | | |
| 198G3 | L | R271 | R274 | G172 | | | | | | | | | | | | | | | |
| 191G10 | L | R271 | G172 | R274 | | | | | | | | | | | | | | | |
| 202A3 | unknown | R271 | G172 | N209 | | | | | | | | | | | | | | | |
| 194C1 | L | R274 | R271 | P272 | G172 | V208 | R170 | | | | | | | | | | | | |
| 176H4 | R | R271 | P272 | N265 | G172 | P241 | L249 | H247 | D242 | | | | | | | | | | |
| 197G3 | L | R271 | R274 | R170 | G172 | D243 | G248 | D216 | P272 | S171 | Q270 | L249 | E196 | D260 | H215 | D225 | D228 | G251 | E280 | P207 | H204 |
| 191G1 | L | R271 | R238 | R274 | P272 | G172 | V208 | | | | | | | | | | | | |
| 213B3 | L | R238 | R271 | R274 | P272 | G172 | | | | | | | | | | | | | |
| 218G4 | O | R274 | R238 | G172 | R271 | | | | | | | | | | | | | | |
| 75G3 | M | R238 | R170 | G172 | V208 | | | | | | | | | | | | | | |
| 194C10 | T | R238 | R170 | G172 | V208 | | | | | | | | | | | | | | |
| 85F7 | M.1 | R274 | R170 | V208 | G172 | | | | | | | | | | | | | | |
| 199A7 | N | H215 | R170 | R183 | Q270 | | | | | | | | | | | | | | | |
| 14B6 | P | T259 | N265 | P241 | | | | | | | | | | | | | | | | |
| 193E7 | Q | R263 | P207 | | | | | | | | | | | | | | | | |
| 65C12 | O | | | | | | | | | | | | | | | | | | |

ANTI-ASGR-1 MONOCLONAL INHIBITORY ANTIBODIES

CROSS REFERENCE TO RELATED APPLICATIONS

This application is a continuation of U.S. Non-Provisional application Ser. No. 16/230,356, filed Dec. 21, 2018, which is a divisional of U.S. Non-Provisional application Ser. No. 15/279,162, filed Sep. 28, 2016, now U.S. Pat. No. 10,358, 497, which claims priority to U.S. Provisional Patent Application No. 62/319,740, filed Apr. 7, 2016, U.S. Provisional Patent Application No. 62/259,553, filed Nov. 24, 2015, and U.S. Provisional Patent Application No. 62/234,546, filed Sep. 29, 2015, each of which is incorporated herein by reference in their entirety.

REFERENCE TO THE SEQUENCE LISTING AND TABLES IN ELECTRONIC FORMAT

This application contains a Sequence Listing which has been submitted electronically in ASCII format and is hereby incorporated by reference in its entirety. Said ASCII copy, created on Sep. 26, 2016, is named APMOL017ASEQUENCE.txt and is 14,772,816 bytes in size, and updated and replaced by a file entitled APMOL017C1SEQUENCEREPLACEMENT.txt, created on Nov. 6, 2020, which is 14,782,737 bytes in size. The present application is being filed along with a collection of Tables in electronic format. The collection of Tables is provided as four files entitled TABLE10A.txt, TABLE10B.txt, TABLE10C.txt, and TABLE10D.txt, created and last saved on Sep. 26, 2016, which are 88,431, 356,111, 699,631, and 688,275 bytes in size respectively. The information in the electronic format of the collection of Tables is incorporated herein by reference in its entirety.

FIELD

The field of this invention relates to compositions and methods related to ASGR inhibitors, including but not limited to anti-ASGR, anti-ASGR-1, and/or anti-ASGR-2 antigen binding proteins.

BACKGROUND OF VARIOUS EMBODIMENTS

Cardiovascular disease involving the heart or blood vessels remains a leading cause of global mortality. Cardiovascular disease includes coronary artery disease (CAD) which can lead to angina and myocardial infarction (MI), stroke, hypertensive heart disease, rheumatic heart disease, and other disorders of the cardiovascular system. Medicines for treating cardiovascular disease, and in particular coronary artery disease, have been introduced over the years (e.g., the small molecule class of drugs called statins and the recently approved Repatha®, an antibody targeting PCSK9).

SUMMARY OF VARIOUS EMBODIMENTS

In some aspects, the invention provides an isolated antigen binding protein that binds to human ASGR and inhibits ASGR function. In one embodiment, the invention comprises an isolated antigen binding protein that binds to human ASGR and inhibits ASGR binding to ligand. In another embodiment, the invention comprises an isolated antigen binding protein that binds to human ASGR-1 and inhibits ASGR-1 binding to ligand and/or ASGR-1 interaction with ASGR-2. In another embodiment, the invention comprises an isolated antigen binding protein that binds to human ASGR-2 and inhibits ASGR-2 binding to ligand and/or ASGR-2 interaction with ASGR-1. In yet another embodiment, the invention comprises an isolated antigen binding protein that binds to human ASGR-1 and human ASGR-2, and inhibits ASGR-1 and/or ASGR-2 binding to ligand. In some embodiments, the isolated binding protein binds specifically to human ASGR, ASGR-1 and/or ASGR-2.

In some aspects, the invention provides an isolated antigen binding protein, wherein the isolated antigen binding protein binds to human ASGR-1 and comprises one or more VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7. In some aspects, the invention comprises an isolated antigen binding protein, wherein the isolated antigen binding protein binds to human ASGR-1 and comprises one or more VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises one or more VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and one or more VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises one VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and one VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises two VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and two VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises the VH CDR1, VH CDR2 and VH CDR3 having an amino acid sequence identical to or comprising 1, 2, or 3 amino acid residue substitutions, deletions or insertions in each CDR relative to the VH of any of the sequences set forth in Tables 3-7, and the VL CDR1, VL CDR2 and VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises the VH CDR1, VH CDR2, VH CDR3, VL CDR1, VL CDR2, and VL CDR3 having an amino acid sequence identical to any of the sequences set forth in Tables 3-7. In some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE A. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE A. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE A, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in TABLE A. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE A. In some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE B. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE B. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE B, and the VL CDR1, VL CDR2 and VL CDR3 having an amino acid sequence identical to or comprising 1, 2, or 3 amino acid residue substitutions, deletions or insertions in each CDR relative to the VL of any of the sequences set forth in TABLE B. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE B. In still some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE C. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE C. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE C, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in TABLE C. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE C. In further embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in Table 6. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in Table 6. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in Table 6, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in Table 6. In some embodiments, the isolated antigen binding protein comprises the VH CDR1, VH CDR2, VH CDR3, VL CDR1, VL CDR2, and VL CDR3 having an amino acid sequence identical to any of the sequences set forth in Table 6.

In some aspects, the invention provides an isolated antigen binding protein, wherein the antigen binding protein specifically binds human ASGR-1 and comprises a heavy chain variable domain having at least 90% identity to any of the VH domain amino acid sequences set forth in Tables 3-7. In some aspects, the invention provides an isolated antigen binding protein, wherein the antigen binding protein specifically binds human ASGR-1 and comprises a light chain variable domain having at least 90% identity to any of the VL domain amino acid sequences set forth in Tables 3-7. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Tables 3-7, and a light chain variable domain having at least 90% identity to any of the VL domain amino acid sequences set forth in Tables 3-7. In some embodiments, the invention provides an isolated antigen binding protein, wherein the antigen binding protein specifically binds human ASGR-1 and comprises a heavy chain variable domain having any of the VH domain amino acid sequences set forth in Tables 3-7, and a light chain variable domain having any of the VL domain amino acid sequences set forth in Tables 3-7. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table A. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table A. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table A, and a light chain variable domain having at least 90% identity to any of the VL domain amino acid sequences set forth in Table A. In some embodiments, the invention provides an isolated antigen binding protein, wherein the antigen binding protein specifically binds human ASGR-1 and comprises a heavy chain variable domain having any of the VH domain amino acid sequences set forth in Table A, and a light chain variable domain having any of the VL domain amino acid sequences set forth in Table A. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table B. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table B. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table B, and a light chain variable domain having at least 90% identity to any of the VL domain amino acid sequences set forth in Table B. In some embodiments, the invention provides an isolated antigen binding protein, wherein the antigen binding protein specifically binds human ASGR-1 and comprises a heavy chain variable domain having any of the VH domain amino acid sequences set forth in Table B, and a light chain variable domain having any of the VL domain amino acid sequences set forth in Table B. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table C. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table C. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table C, and a light chain variable domain having at least 90% identity to any of the VL domain amino acid sequences set forth in Table C. In some embodiments, the invention provides an isolated antigen binding protein, wherein the antigen binding protein specifically binds human ASGR-1 and comprises a heavy chain variable domain having any of the VH domain amino acid sequences set forth in Table C, and a light chain variable domain having any of the VL domain amino acid sequences set forth in Table C. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table 6. In some embodiments, the invention provides an isolated anti-gen binding protein, wherein the antigen binding protein specifically binds human ASGR-1 and comprises a light chain variable domain having at least 90% identity to any of the VL domain amino acid sequences set forth in Table 6. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table 6, and a light chain variable domain having at least 90% identity to any of the VL domain amino acid sequences set forth in Table 6. In some embodiments, the invention provides an isolated antigen binding protein, wherein the antigen binding protein specifically binds human ASGR-1 and comprises a heavy chain variable domain having any of the VH domain amino acid sequences set forth in Table 6, and a light chain variable domain having any of the VL domain amino acid sequences set forth in Table 6.

In some aspects, the invention provides an isolated antigen binding protein, wherein the antigen binding protein binds human ASGR-1 and comprises one or more VH CDR1, VH CDR2 or VH CDR3 having an amino acid sequence identical to or comprising no more than 18 amino acid residue substitutions, insertions or deletions in each CDR relative to the VH of any of the sequences set forth in Table 19A as depicted in FIG. 55. In some embodiments, the invention provides an isolated antigen binding protein, wherein the antigen binding protein binds human ASGR-1 and comprises one or more VH CDR1, VH CDR2 or VH CDR3 having an amino acid sequence identical to or comprising a conservative substitution of any of the amino acid sequences set forth in Table 19B or 19C, as depicted in FIG. 55. In some aspects, the invention comprises an isolated antigen binding protein, wherein the isolated antigen binding protein binds to human ASGR-1 and comprises one or more VL CDR1, VL CDR2 or VL CDR3 having an amino acid sequence identical to or comprising no more than 14 amino acid residue substitutions, insertions or deletions in each CDR relative to the VL of any of the sequences set forth in Table 20A as depicted in FIG. 55. In some embodiments, the invention provides an isolated antigen binding protein, wherein the antigen binding protein binds human ASGR-1 and comprises one or more VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises one or more VH CDR1, VH CDR2 or VH CDR3 having an amino acid sequence identical to or comprising no more than 18 amino acid residue substitutions, insertions or deletions in each CDR relative to the VH of any of the sequences set forth in Table 19A, as depicted in FIG. 55, and one or more VL CDR1, VL CDR2 or VL CDR3 having an amino acid sequence identical to or comprising no more than 14 amino acid residue substitutions, insertions or deletions in each CDR relative to the VL of any of the sequences set forth in Table 20A as depicted in FIG. 55. In some embodiments, the invention provides an isolated antigen binding protein, wherein the antigen binding protein binds human ASGR-1 and comprises one or more VH CDR1, VH CDR2 or VH CDR3 having an amino acid sequence identical to or comprising a conservative substitution of any of the amino acid sequences set forth in Table 19B or 19C, as depicted in FIG. 55, and one or more VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises one VH CDR1, VH CDR2 or VH CDR3 having an amino acid sequence identical no more than 18 amino acid residue substitutions, insertions or deletions in each CDR relative to the VH of any of the sequences set forth in Table 19A, as depicted in FIG. 55, and one VL CDR1, VL CDR2 or VL CDR3 having an amino acid sequence identical to or comprising no more than 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises one VH CDR1, VH CDR2 or VH CDR3 having an amino acid sequence identical to or comprising a conservative substitution of any of the amino acid sequences set forth in Table 19B or 19C, as depicted in FIG. 55, and one VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises two VH CDR1, VH CDR2 or VH CDR3 having an amino acid sequence identical to or comprising up to 18 amino acid residue substitutions, insertions or deletions in each CDR relative to the VH of any of the sequences set forth in Table 19A, as depicted in FIG. 55, and two VL CDR1, VL CDR2 or VL CDR3 having an amino acid sequence identical to or comprising up to 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises two VH CDR1, VH CDR2 or VH CDR3 having an amino acid sequence identical to or comprising a conservative substitution of any of the amino acid sequences set forth in Table 19B or 19C, as depicted in FIG. 55, and two VL CDR1, VL CDR2 or VL CDR3 having an amino acid sequence identical to or comprising a conservative substitution of any of the amino acid sequences set forth in Tables 20B or 20C, as depicted in FIG. 55. In some embodiments, the isolated antigen binding protein comprises the VH CDR1, VH CDR2 and VH CDR3 having an amino acid sequence identical to or comprising up to 18 amino acid residue substitutions, insertions or deletions in each CDR relative to the VH of any of the sequences set forth in Table 19A, as depicted in FIG. 55, and the VL CDR1, VL CDR2 and VL CDR3 having an amino acid sequence identical to or comprising up to 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises the VH CDR1, VH CDR2 or VH CDR3 having an amino acid sequence identical to or comprising a conservative substitution of any of the amino acid sequences set forth in Table 19B or 19C, as depicted in FIG. 55, and the VL CDR1, VL CDR2 or VL CDR3 having an amino acid sequence identical to or comprising a conservative substitution of any of the amino acid sequences set forth in Table 20B or 20C, as depicted in FIG. 55.

In some aspects, the invention provides an isolated antigen binding protein, wherein the antigen binding protein specifically binds human ASGR-1 and comprises a heavy chain variable domain having at least 90% identity to any of the VH domain amino acid sequences set forth in Tables 19A, as depicted in FIG. 55 or in Tables 21-34 as depicted in FIG. 56 or in Tables 49-95 as depicted in FIG. 56. In some aspects, the invention provides an isolated antigen binding protein, wherein the antigen binding protein specifically binds human ASGR-1 and comprises a light chain variable domain having at least 90% identity to any of the VL domain amino acid sequences set forth in Table 20A, as depicted in FIG. 55, or in Tables 35-48, as depicted in FIG. 56 or in Tables 96-134 as depicted in FIG. 57. In some embodiments, the antigen binding protein comprises a heavy chain variable domain having at least 90% identity to any of the VH domain amino acid sequences set forth in Tables 19A as depicted in FIG. 55, or in Tables 21-34 as depicted in FIG. 56 or in Tables 49-95 as depicted in FIG. 57, and a light chain variable domain having at least 90% identity to any of the VL domain amino acid sequences set forth in Table 20A as depicted in FIG. 55 or in Tables 35-48 as depicted in FIG. 56 or in Tables 96-134 as depicted in FIG. 57. In some embodiments, the antigen binding protein comprises a heavy chain variable domain having any of the VH domain amino acid sequences set forth in Tables 19A as depicted in FIG. 55, or in Tables 21-34 as depicted in FIG. 56 or in Tables 49-95 as depicted in FIG. 57, and a light chain variable domain having any of the VL domain amino acid sequences set forth in Table 20A as depicted in FIG. 55 or in Tables 35-48 as depicted in FIG. 56 or in Tables 96-134 as depicted in FIG. 57.

In some aspects, the invention provides an antigen binding protein that specifically binds to human ASGR-1 at an epitope that is bound by any of the antigen binding proteins disclosed herein. In some embodiments, the invention provides an isolated antigen binding protein that specifically binds to human ASGR-1 at an epitope that is bound by at least one of the antigen binding proteins set forth in Tables 2-7. In some embodiments, the invention provides an isolated antigen binding protein that specifically binds to human ASGR-1 at an epitope that is bound by at least one of the antigen binding proteins set forth in Table A. In some embodiments, the invention provides an isolated antigen binding protein that specifically binds to human ASGR-1 at an epitope that is bound by at least one of the antigen binding proteins set forth in Table B. In some embodiments, the invention provides an isolated antigen binding protein that specifically binds to human ASGR-1 at an epitope that is bound by at least one of the antigen binding proteins set forth in Table C. In some embodiments, the invention provides an isolated antigen binding protein that specifically binds to human ASGR-1 at an epitope that is bound by at least one of the antigen binding proteins set forth in Table 6.

In some aspects, the invention provides an isolated antigen binding protein that competes for binding to human ASGR-1 with any of the antigen binding proteins disclosed herein. In some embodiments, the invention provides an isolated antigen binding protein that competes for binding with any of the antigen binding proteins set forth in Tables 2-7. In some embodiments, the invention provides an isolated antigen binding protein that competes for binding with any of the antigen binding proteins set forth in Table A. In some embodiments, the invention provides an isolated antigen binding protein that competes for binding with any of the antigen binding proteins set forth in Table B. In still some embodiments, the invention provides an isolated antigen binding protein that competes for binding with any of the antigen binding proteins set forth in Table C. In yet another embodiment, the invention provides an isolated antigen binding protein that competes for binding with any of the antigen binding proteins set forth in Table 6.

In some aspects, the invention provides an isolated antigen binding protein that binds to human ASGR-1 within the carbohydrate recognition domain ("CRD") (also known as the carbohydrate binding domain or "CBD") and inhibits human ASGR-1 binding to ligand. In some embodiments, the antigen binding protein binds to human ASGR-1 within residues 148-291, or 149-291, or 150-291, or 151-291, or 152-291, or 153-291, or 154-291, or 155-291 of SEQ ID NO:5. In some embodiments, the invention comprises an isolated antigen binding protein that binds to human ASGR-1 CBD within Helix α-1. In some embodiments, the invention comprises an isolated antigen binding protein that binds to human ASGR-1 within residues 174-186 of SEQ ID NO:5. In some embodiments, the invention comprises an isolated antigen binding protein that binds to human ASGR-1 CBD within Helix α-2. In some embodiments, the invention comprises an isolated antigen binding protein that binds to human ASGR-1 CBD within residues 194-206 of SEQ ID NO:5. In some embodiments, the invention comprises an isolated antigen binding protein that binds to human ASGR-1 within residues 237-273 or residues 240-267 of SEQ ID NO:5. In some embodiments, the antigen binding protein binds to ASGR-1 having an amino acid sequence that is at least 90% identical to SEQ ID NO:5. In some embodiments, the antigen binding protein is an antibody.

In some aspects, the invention provides an isolated antigen binding protein or an antibody that binds to human ASGR-1 and inhibits human ASGR-1 function. In some embodiments, the isolated antigen binding protein or an antibody binds to human ASGR-1 and inhibits human ASGR-1 from binding to a ligand. In some embodiments, the antigen binding protein or antibody or a paratope in an antibody binds to human ASGR-1 at an epitope comprising at least one of the following amino acid residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, R274 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, or Y273 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments when the antigen binding protein or antibody or paratope in an antibody binds to human ASGR-1 at an epitope comprising at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or paratope in an antibody binds to human ASGR-1 at an epitope comprising at least one of the following residues: H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, N157, R170, S171, G172, Q202, H203, H204, I205, G206, P207, V208, N209, T210, D260, R271, P272, Y273, or R274 (SEQ ID NO:5). In some embodiments, the antigen binding protein or antibody or a paratope in an antibody binds to human ASGR-1 at an epitope comprising at least one of the following amino acid residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5). In some embodiments, the antigen binding protein or antibody or a paratope in an antibody binds to human ASGR-1 at an epitope comprising at least one of the following amino acid residues: H161, E162, W195, E196, Q198, K199, F200, Q202, H203, H204, G232, F233, K234, N235, W236, R237, P238, D261, G262, or R263 (SEQ ID NO:5). In some embodiments, the antigen binding protein or antibody or a paratope in an antibody binds to human ASGR1 at an epitope comprising at least one of the following amino acid residues: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5). In some embodiments, the antigen binding protein or antibody or a paratope in an antibody binds to human ASGR-1 at an epitope comprising at least one of the following amino acid residues: W167, S171, G172, K173, A174, A176, D177, N180, Y181, R183, L184, E185, D186, Q270, P272, or W275 (SEQ ID NO:5). In some embodiments, the antigen binding protein or antibody or a paratope in an antibody binds to human ASGR-1 at an epitope comprising at least one of the following amino acid residues: R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, or W264 (SEQ ID NO:5). In some embodiments, the antigen binding protein or antibody or a paratope in an antibody binds to human ASGR-1 at an epitope comprising at least one of the following amino acid residues: R170, W195, E196, K199, Q202, H203, H204, I205, G206, P207, V208, F233, K234, N235, W236, P238, D260, D261, G262, R263, or R274 (SEQ ID NO:5). In some embodiments, the antigen binding protein or antibody or a paratope in an antibody binds to human ASGR-1 at an epitope comprising at least one of the following amino acid residues: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5). In some embodiments, the antigen binding protein or antibody or a paratope in an antibody binds to human ASGR-1 at an epitope comprising at least one of the following amino acid residues: H161, S194, W195, E196, Q198, K199, F200, Q202, H203, F233, K234, N235, W236, R237, P238, or R263 (SEQ ID NO:5). In some embodiments, the antigen binding protein or antibody or a paratope in an antibody binds to human ASGR-1 at an epitope comprising at least one of the following amino acid residues: H161, E162, T193, S194, W195, E196, K199, Q202, T231, G232, F233, K234, N235, P238, D261, R263, R163, V192, E197, Q198, H203, P207, D228, E230, W236, R237, D260, G262, or W264 (SEQ ID NO:5). In some embodiments, the antigen binding protein or antibody or a paratope in an antibody binds to human ASGR-1 at an epitope comprising at least one of the following amino acid residues: H161, E162, T193, S194, W195, E196, K199, Q202, T231, G232, F233, K234, N235, P238, D261, or R263 (SEQ ID NO:5). In some embodiments, the antigen binding protein or antibody or a paratope in an antibody binds to human ASGR-1 at an epitope comprising at least one of the following amino acid residues: T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, or W264 (SEQ ID NO:5). In some embodiments, the antigen binding protein or antibody or a paratope in an antibody binds to human ASGR-1 at an epitope comprising at least one of the following amino acid residues: T193, S194, W195, E196, P220, W221, G226, T227, D228, Y229, E230, T231, G232, F233, K234, N235, W236, R237, P238, E239, or G252 (SEQ ID NO:5). In some embodiments, the antigen binding protein or antibody or a paratope in an antibody binds to human ASGR-1 at an epitope comprising at least one of the following amino acid residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, or C269 (SEQ ID NO:5). In some embodiments, the antigen binding protein or antibody or a paratope in an antibody binds to human ASGR-1 at an epitope comprising at least one of the following amino acid residues: D216, Q217, N218, G219, P220, W221, Y229, E230, K234, W236, E239, Q240, P241, D242, D243, W244, Y245, G246, L249, G250, G251, G252, D254, or Q270 (SEQ ID NO:5). In some embodiments, the antigen binding protein or antibody or a paratope in an antibody binds to human ASGR-1 at an epitope comprising at least one of the following amino acid residues: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W195, N209, N235, R237, P238, E239, Q240, D242, H257, T259, D260, D261, R263, N265, D267, R271, or Y273 (SEQ ID NO:5). In some embodiments, the antigen binding protein or antibody or a paratope in an antibody binds to human ASGR-1 at an epitope comprising at least one of the following amino acid residues: N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or a paratope in an antibody binds to human ASGR-1 at an epitope comprising at least one of the following amino acid residues: N157, R170, S171, G172, Q202, H203, H204, I205, G206, P207, V208, N209, T210, D260, R271, P272, Y273, or R274 (SEQ ID NO:5). In some embodiments, the antigen binding protein or antibody or a paratope in an antibody binds to human ASGR-1 at an epitope comprising at least one of the following amino acid residues: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5). In some embodiments, the antigen binding protein or antibody or a paratope in an antibody binds to human ASGR-1 at an epitope comprising at least one of the following amino acid residues: R170, S171, G172, A174, H204, I205, G206, P207, V208, N209, H257, D260, N265, D267, Q270, R271, P272, Y273, or R274 (SEQ ID NO:5). In some embodiments, the antigen binding protein or antibody or a paratope in an antibody binds to human ASGR-1 at an epitope comprising at least one of the following amino acid residues: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or a paratope in an antibody binds to human ASGR-1 at an epitope comprising at least one of the following amino acid residues: R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5).

In some aspects, the invention provides an isolated antigen binding protein or an antibody or a paratope in an antibody that specifically binds to human ASGR-1 and inhibits human ASGR-1 function. In some embodiments, the isolated antigen binding protein or an antibody or a paratope in an antibody specifically binds to human ASGR-1 and inhibits human ASGR-1 from binding to a ligand. In some embodiments, the antigen binding protein or antibody or a paratope in an antibody specifically binds to human ASGR-1 within residues 148-291 of SEQ ID NO:5. In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5).

In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, or D267 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R237, Q240, D242, W244, E253, N265, D266, D267, N209, P238, E239, P241, D243, Y245, G246, H247, G252, C255, H257, T259, V268, R271, or Y273 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R237, Q240, D242, W244, E253, N265, D266, or D267 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: N209, R237, Q240, D242, W244, E253, H257, T259, N265, D266, D267, Y273, P238, E239, P241, D243, Y245, G246, H247, G252, C255, F258, D260, R263, W264, V268, or R271 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, or C269 (SEQ ID NO:5). In some embodiments when the antigen binding protein or antibody is bound to human ASGR-1, the antigen binding protein or antibody or a paratope in an antibody is positioned 5 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, or Q270 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W195, N209, N235, R237, P238, E239, Q240, D242, H257, T259, D260, D261, R263, N265, D267, R271, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R170, S171, G172, A174, H204, I205, G206, P207, V208, N209, H257, D260, N265, D267, Q270, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues of human ASGR-1 (SEQ ID NO:5): D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, N157, R170, S171, G172, Q202, H203, H204, I205, G206, P207, V208, N209, T210, D260, R271, P272, Y273, R274, V156, W158, V159, H161, W167, F168, S169, K173, (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues of human ASGR-1 (SEQ ID NO:5): H161, E162, W195, E196, Q198, K199, F200, Q202, H203, H204, G232, F233, K234, N235, W236, R237, P238, D261, G262, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W167, S171, G172, K173, A174, A176, D177, N180, Y181, R183, L184, E185, D186, Q270, P272, or W275 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, or W264 (SEQ ID NO:5). In some embodiments when the antigen binding protein or antibody or a paratope in an antibody is bound to human ASGR-1, the antigen binding protein or a paratope in an antibody is positioned 5 angstroms or less from at least one of the following residues: R170, W195, E196, K199, Q202, H203, H204, I205, G206, P207, V208, F233, K234, N235, W236, P238, D260, D261, G262, R263, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, S194, W195, E196, Q198, K199, F200, Q202, H203, F233, K234, N235, W236, R237, P238, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, T193, S194, W195, E196, K199, Q202, T231, G232, F233, K234, N235, P238, D261, R263, R163, V192, E197, Q198, H203, P207, D228, E230, W236, R237, D260, G262, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, E162, T193, S194, W195, E196, K199, Q202, T231, G232, F233, K234, N235, P238, D261, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: T193, S194, W195, E196, P220, W221, G226, T227, D228, Y229, E230, T231, G232, F233, K234, N235, W236, R237, P238, E239, or G252 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270 or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: N157, R170, S171, G172, Q202, H203, H204, I205, G206, P207, V208, N209, T210, D260, R271, P272, Y273 or R274 (SEQ ID NO:5).

In some aspects, the invention comprises an isolated antigen binding protein or antibody that specifically binds to human ASGR-1 and inhibits human ASGR-1 function. In some embodiments, the isolated antigen binding protein or antibody that specifically binds to human ASGR-1 inhibits binding of human ASGR-1 binding to a ligand. In some embodiments, the antigen binding protein or antibody specifically binds to human ASGR-1 at a location that overlaps with a location where a ligand binds to human ASGR-1. In some embodiments, the location where a ligand binds to ASGR-1 includes at least one amino acid residue selected from the group consisting of: N209, R237, Q240, D242, W244, E253, H257, T259, N265, D266, D267, Y273, P238, E239, P241, D243, Y245, G246, H247, G252, C255, F258, D260, R263, W264, V268, or R271 (SEQ ID NO:5). In some embodiments, an isolated antigen binding protein or an antibody specifically binds to human ASGR-1 at a location that overlaps with a location that a ligand binds to ASGR-1. In some embodiments, the location that a ligand binds to human ASGR-1 includes at least one amino acid residue selected from the group consisting of: N209, R237, Q240, D242, W244, E253, H257, T259, N265, D266, D267, and Y273 (SEQ ID NO:5).

In some aspects, the invention comprises an isolated antigen binding protein that binds to human ASGR-1 and inhibits human ASGR, ASGR-1 and/or ASGR-2 function, wherein the antigen binding protein does not bind to a variant ASGR-1 protein, and wherein said variant ASGR-1 protein comprises a single mutation of a residue selected the group consisting of: R170, S171, G172, R183, L184, W195, E196, K199, H203, H204, P207, V208, N209, H215, D216, P220, D225, D228, R237, P238, E239, P241, D242, D243, Y245, G246, H247, G248, L249, G251, E253, T259, D260, R263, N265, Q270, R271, P272, R274, and E280 as shown in SEQ ID NO:5. In some embodiments, an isolated antigen binding protein or an antibody is contemplated. An antigen binding protein "does not bind" to a variant ASGR-1 protein when the measured reduction in antibody binding signal to a variant ASGR-1 protein (compared to that determined for binding to wild type ASGR-1) is statistically significant as measured by any number of methods known to one skilled in the art, such as the method described in Example 7E below. In some embodiments, the variant ASGR-1 protein comprises a single mutation of a residue at a position selected from the group consisting of: W195, E196, K199, H203, H204, P207, P220, G251, and R263 as shown in SEQ ID NO:5. In some embodiments, the single mutation is selected from the group consisting of H203, H204, P220, and G251. In some embodiments, the single mutation is selected from the group consisting of W195, E196 and K199. In some embodiments, the single mutation is selected from the group consisting of W195, E196 and H204. In some embodiments, the single mutation is selected from the group consisting W195, K199, and R263. In some embodiments, the single mutation is selected from the group consisting of W195 and E196. In some embodiments, the single mutation is selected from the group consisting of W195 and K199. In some embodiments, the single mutation is selected from the group consisting of W195 or P207. In some embodiments, the single mutation is selected from the group consisting of W195 and R263. In some embodiments, the single mutation is selected from the group consisting of H203 and H204. In some embodiments, the single mutation is selected from the group consisting of K199 and R263. In some embodiments, the single mutation is a mutation of residue W195. In some embodiments, the variant ASGR-1 protein comprises a single mutation of a residue selected the group consisting of: R170, S171, R183, L184, H215, P220, P238, G246, H247, G248, G251, and N265 as shown in SEQ ID NO:5. In some embodiments, the single mutation is selected from the group consisting of R183, L184, H215, P220, G246, G248, G251, and N265. In some embodiments, the single mutation is selected from the group consisting of L184, P220, P238, H247, and G251. In some embodiments, the single mutation is selected from the group consisting of R170, S171, and L184. In some embodiments, the single mutation is a mutation of residue R183. In some embodiments, the single mutation is a mutation of residue L184. In some embodiments, the variant ASGR-1 protein comprises a single mutation of a residue at a position selected from the group consisting of: P241, D242, D243, Y245, G251, E253 and D260 as shown in SEQ ID NO:5. In some embodiments, the single mutation is selected from the group consisting of P241, D243, Y245, G251, E253 and D260. In some embodiments, the single mutation is selected from the group consisting of P241, D243, and E253. In some embodiments, the single mutation is a mutation of residue D260. In some embodiments, the variant ASGR-1 protein comprises a single mutation of a residue at a position selected from the group consisting or comprising: R170, R237, E239, P241, T259, D260, R263, and N265 as shown in SEQ ID NO:5. In some embodiments, the single mutation is selected from the group consisting of R237, D260 and R263. In some embodiments, the single mutation is selected from the group consisting of R237, T259, D260 and R263. In some embodiments, the single mutation is selected from the group consisting of R170, R237, P241, T259, D260, R263 and N265. In some embodiments, the single mutation is selected from the group consisting of R237, E239, P241, T259, D260, R263 and N265. In some embodiments, the variant ASGR-1 protein comprises a single mutation of a residue at a position selected from the group consisting or comprising: R170, S171, G172, E196, H204, P207, V208, N209, H215, D216, D225, D228, P238, P241, D242, D243, H247, G248, L249, G251, D260, R263, N265, Q270, R271, P272, R274 and E280 as shown in SEQ ID NO:5. In some embodiments, the single mutation is selected from the group consisting of R170, S171, G172, E196, H204, P207, V208, N209, H215, D216, D225, D228, P238, P241, D242, D243, H247, G248, L249, G251, D260, R263, N265, Q270, R271, P272, R274 and E280 as shown in SEQ ID NO:5. In some embodiments, the single mutation is selected from the group consisting of R170, S171, G172, E196, H204, P207, H215, D216, D225, D228, D243, G248, L249, G251, D260, Q270, R271, P272, R274 and E280. In some embodiments, the single mutation is selected from the group consisting of G172, V208, R271, P272 and R274. In some embodiments, the single mutation is selected from the group consisting of G172, R271 and R274. In some embodiments, the single mutation is selected from the group consisting of G172, N209, and R271. In some embodiments, the single mutation is selected from the group consisting of R170, G172, V208, R271 and P272. In some embodiments, the single mutation is selected from the group consisting of G172, V208, P238, R271, P272 and R274. In some embodiments, the single mutation is selected from the group consisting of G172, P238, R271, P272 and R274. In some embodiments, the variant ASGR-1 protein comprises a single mutation of a residue at a position selected from the group consisting or comprising: G172, P238, R271 and R274 as shown in SEQ ID NO:5. In some embodiments, the variant ASGR-1 protein comprises a single mutation of a residue at a position selected from the group consisting or comprising: R170, G172, V208 and R274 as shown in SEQ ID NO:5. In some embodiments, the variant ASGR-1 protein comprises a single mutation of a residue at a position selected from the group consisting or comprising: R170, R183, H215 and Q270 as shown in SEQ ID NO:5. In some embodiments, the variant ASGR-1 protein comprises a single mutation of a residue at a position selected from the group consisting or comprising: P241, T259, and N265 as shown in SEQ ID NO:5. In some embodiments, the variant ASGR-1 protein comprises a single mutation of a residue at a position selected from the group consisting or comprising: P207 and R263 as shown in SEQ ID NO:5. In some embodiments, the variant ASGR-1 protein comprises a single mutation of a residue at a position selected from the group consisting or comprising: G172, P241, D242, H247, L249, N265, R271 and P272 as shown in SEQ ID NO:5. In some embodiments, the antigen binding protein or antibody does not bind to two or more variant ASGR-1 proteins, wherein the variant ASGR-1 proteins comprise the single mutations of the group individually.

In some aspects, the invention comprises a vector comprising a nucleic acid molecule as described herein. In some embodiments, the invention comprises a host cell comprising a nucleic acid molecule as described herein.

In some aspects, the invention comprises a nucleic acid molecule encoding the antigen binding protein as described herein.

In some aspects, the invention comprises a pharmaceutical composition comprising at least one antigen binding protein described herein.

In some aspects, the invention provides a method of treating or preventing a cardiovascular disease comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the relative risk reduction of a cardiovascular event is at least about 5%, at least about 10%, at least about 15%, at least about 20%, at least about 25%, at least about 30%, at least about 35%, at least about 40%, at least about 45%, at least about 50%, at least about 55%, at least about 60% in the patient.

In some aspects, the invention provides a method of decreasing the risk of acquiring coronary artery disease or having a myocardial infarction (MI) comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the relative risk reduction of coronary artery disease or MI is at least about 5%, at least about 10%, at least about 15%, at least about 20%, at least about 25%, at least about 30%, at least about 35%, at least about 40%, at least about 45%, at least about 50%, at least about 55%, at least about 60% in the patient.

In other aspects, the invention provides a method of reducing blood LDL cholesterol levels in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, blood LDL cholesterol is reduced by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as compared to a predose level of blood LDL cholesterol in the patient.

In still other aspects, the invention provides a method of reducing non-HDL cholesterol levels in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, non-HDL cholesterol is reduced by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as compared to a predose level of non-HDL cholesterol in the patient.

In some aspects, the invention provides a method of increasing alkaline phosphatase ("ALP") levels in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, ALP levels are increased at least about 40%, at least about 45%, at least about 50%, at least about 55%, at least about 60%, at least about 65%, at least about 70%, at least about 75%, at least about 80%, at least about 85%, or at least about 90% as compared to a predose ALP level in the patient. In some embodiments, ALP levels are increased at least about 1.25×, 1.5×, 2×, 2.5×, 3×, 3.5×, 4×, 4.5×, and 5× over pretreatment.

In some aspects, the invention provides a method of antagonizing ASGR, ASGR-1 and/or ASGR-2 in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein.

BRIEF DESCRIPTION OF THE FIGURES

FIG. 1A. ASGR-1 sequence alignments of human (SEQ ID NO: 32699), cynomolgus monkey (cyno) (SEQ ID NO: 32700), dog (SEQ ID NO: 32701), pig (SEQ ID NO: 32702), rat (SEQ ID NO: 32703) and mouse ASGR-1 (SEQ ID NO: 32704). The boxed areas denoting different regions of ASGR-1 (i.e., cytoplasmic, transmembrane, and the carbohydrate binding domain (CBD; also called the carbohydrate recognition domain, or CRD) are representative of the approximate amino acid locations of these regions; the human Y273 amino acid is boxed.

FIG. 1B. Human ASGR-1 sequence alignments (SEQ ID NOS 32705-32710, respectively, in order of appearance).

FIG. 2. ASGR-2 sequence alignments of human (SEQ ID NO: 32713), cyno (SEQ ID NO: 32714), dog (SEQ ID NO: 32716), pig (SEQ ID NO: 32715), rat (SEQ ID NO: 32712) and mouse ASGR-2 (SEQ ID NO: 32711). The boxed areas denoting different regions of ASGR-2 (i.e., cytoplasmic, transmembrane, and the carbohydrate binding domain (CBD; also called the carbohydrate recognition domain, or CRD) are representative of the approximate amino acid locations of these regions.

FIG. 5. (A) The del12 variant was typed in the indicated populations a total of 41,648 CAD cases and 247,374 controls. For each cohort, the square (diamond in the case of the combined estimate) indicates the estimated odds ratio and the line shows the 95% confidence interval. There was no evidence of heterogeneity across the eight study populations (Phet=0.96). (B) Kaplan-Meier curves for survival to first myocardial infarction in carriers and non-carriers of del12 in ASGR-1 stratified by sex. The proportion of individuals that have not had a myocardial infarction is shown on the y-axis and plotted against age on the x-axis. Males and females are represented separately and a distinction is made between del12 carriers and non-carriers in each case.

FIG. 8. RNAi in vitro data in CHO cells transfected with hASGR-1 using construct S1662. Panel A is a western blot demonstrating reduction of expression of human ASGR-1. Panel B is a graphical representation of the relative reduction in expression of human ASGR-1. Panel C demonstrates that CHO cells receiving construct S1662 displays a dramatic reduction in internalization of ligand (β-GalNAc).

FIG. 9. RNAi in vitro data in CHO cells transfected with mASGR-1 using various constructs. Panel A is a western blot demonstrating reduction of expression of mouse ASGR-1. Panel B is a graphical representation of the relative reduction in expression of mouse ASGR-1. Panel C demonstrates that CHO cells receiving the various constructs display a dramatic reduction in internalization of ligand (β-GalNAc).

FIG. 10. RNAi in vitro data in HepG2 cells using construct S1662. Panel A is a western blot demonstrating reduction of expression of human ASGR-1. Panel B is a graphical representation of the relative reduction in expression of human ASGR-1.

FIG. 11. RNAi in vitro data in CHO cells transfected with hASGR-2 using various constructs. Panel A is a western blot demonstrating reduction of expression of human ASGR-2. Panel B is a graphical representation of the relative reduction in expression of human ASGR-2 by the various constructs.

FIG. 12. RNAi in vitro data in CHO cells transfected with mASGR-1 and mASGR-2 using various other constructs. Panel A is a western blot demonstrating reduction of expression of mouse ASGR-1 (anti-mouse ASGR-1 or anti-flag) or mouse ASGR-2 (anti-his). Panel B is a graphical representation of the relative reduction in expression of mouse ASGR-1 by the various constructs. Panel C is a graphical representation of the relative reduction in expression of mouse ASGR-2 by the various constructs.

FIG. 13. RNAi in vitro data in HepG2 cells using various constructs. Panel A is a western blot demonstrating reduction of expression of human ASGR-2. Panel B is a graphical representation of the relative reduction in expression of human ASGR-2 by the various constructs.

FIG. 14. RNAi in vivo data in in C57BL/6J mice using various constructs over the course of 7 days with three injections total, one injection at day 0, one injection at day 2 and one injection at day 4. Panel A is a graphical representation of quantitative per data showing the relative reduction in expression of mASGR-1 RNA in the liver. Panel B is a graphical representation of the relative reduction in expression of mASGR-2 RNA in the liver.

FIG. 15. RNAi in vivo data in in C57BL/6J mice using various constructs over the course of 7 days with three injections total, one injection at day 0, one injection at day 2, and one injection at day 4. Panel A is a western blot demonstrating reduction of expression of mouse ASGR-1 protein. Panel B is a graphical representation of the relative increase of serum ALP activity.

FIG. 16. RNAi in vivo data in C57BL/6J mice using various constructs over the course of 7 days with one injection at day 0. Panel A is a graphical representation of the relative reduction in expression of mASGR-2 in the liver. Panel B is a graphical representation of the relative reduction in expression of mASGR-1 in the liver.

FIG. 18. Panel A shows a computer representation of the crystal structure of the ASGR-1/lactose complex. Panel B is a computer representation of the observed electron density. Panel C is an enlarged view of the carbohydrate binding domain.

FIG. 19. Panel A shows a computer representation of the crystal structure of the ASGR-1/galactose complex. Panel B is a computer representation of the observed electron density. Panel C is an enlarged view of the carbohydrate binding domain.

FIG. 21. Panel A shows a computer representation of the crystal structure of the ASGR-1/GalNAc complex. Panel B is a computer representation of the observed electron density. Panel C is an enlarged view of the carbohydrate binding domain.

FIG. 22. Panel A shows a depiction of the structure of the ASGR-1 CBD and the 5E5 Fab. Panel B is an enlarged view of the ASGR-1 CBD and 5E5 Fab that represents a disordered carbohydrate binding loop with a dashed line and highlights the indirect inhibition of ASGR-1 CBD and the ligand (GalNAc) binding. Panel B also incorporates a double-headed arrow which represents a 5 angstrom distance from tip to tip.

FIG. 24. A depiction of the structure of the ASGR-1 CBD and the 4A2 Fab.

FIG. 35. A depiction of the structure of the ASGR-1 CBD and the 54E9 Fab.

FIG. 37. Panel A is a depiction of the structure of the ASGR-1 CBD and the 218G4 Fab; and Panel B is an enlarged view of the structure of the ASGR-1 CBD and the 218G4 Fab.

FIG. 48. A table presenting various protein sequences for human, mouse, rat, pig, dog and cynomolgus monkey ASGR, ASGR-1 and ASGR-2 (Table 1).

FIG. 49. Two tables presenting variable light and heavy chain CDR1, CDR2 and CDR3 amino acid sequences for certain antigen binding proteins of the present invention (Table 2A and Table 2B). Table 2A presents the Variable Light Chain CDR1, CDR2 and CDR3, while Table 2B presents the Variable Heavy Chain CDR1, CDR2, and CDR3. The CDR sequences in Tables 2A and 2B are wrapped due to space issues, and unless stated otherwise, should be understood to be a single amino acid sequence.

FIG. 50. A table presenting the amino acid sequences of the light and heavy chain variable domains for certain antigen binding proteins of the present invention are displayed in a table (Table 3). The amino acid sequences of the light and heavy chain variable domains in Table 3 are wrapped due to space issues, and unless stated otherwise, should be understood to be single amino acid sequences.

FIG. 51. A table presenting a protein alignment of light and heavy variable regions for certain antigen binding proteins of the present invention (Table 4). An asterisk "*" denotes a stop codon. Sequences containing a stop codon are represented as distinct sequences in the Sequence Listing, however, these sequences are related. Generally speaking, however, the amino acid sequences of the light and heavy chain variable domains in the protein alignment presented in Table 4 are wrapped due to space issues, and unless stated otherwise, like in the case of sequences with one or more stop codons, should be understood to be single amino acid sequences.

FIG. 52. A table presenting a consensus protein alignment of light and heavy variable regions for certain antigen binding proteins of the present invention (Table 5). An asterisk "*" denotes a stop codon. Sequences containing a stop codon are represented as distinct sequences in the Sequence Listing, however, these sequences are related. Generally speaking, however, the amino acid sequences of the light and heavy chain variable domains in the consensus protein alignment presented in Table 5 are wrapped due to space issues, and unless stated otherwise, like in the case of sequences with one or more stop codons, should be understood to be single amino acid sequences.

FIG. 53. A table presenting a protein alignment of light and heavy variable regions for certain optimized antigen binding proteins of the present invention (Table 6). The amino acid sequences of the light and heavy chain variable domains in the protein alignment presented in Table 6 are wrapped due to space issues, and unless stated otherwise, should be understood to be single amino acid sequences.

FIG. 54. A table presenting a consensus protein alignment of light and heavy variable regions for certain optimized antigen binding proteins of the present invention (Table 7). The amino acid sequences of the light and heavy chain variable domains in the consensus protein alignment presented in Table 7 are wrapped due to space issues, and unless stated otherwise, should be understood to be single amino acid sequences.

FIG. 55. A group of tables presenting the consensus sequences of various heavy and light chain variable regions (Tables 19A and 20A, respectively), as well as the consensus sequences of CDRs of various heavy and light chain variable regions (Tables 19B and C and Tables 20B and 20C, respectively) for certain antigen binding proteins of the present invention.

FIG. 60. A table presenting ASGR-1 residues identified as hits via Arg/Glu scanning mutagenesis.

DETAILED DESCRIPTION OF THE VARIOUS EMBODIMENTS

Figure 3:
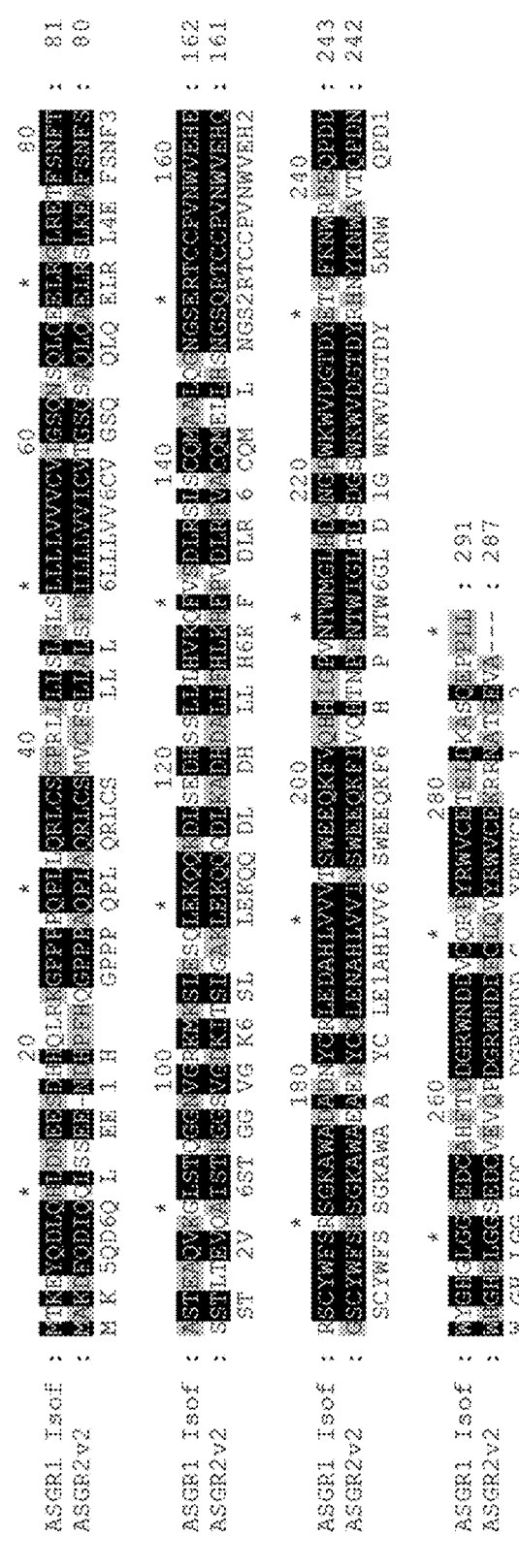
FIG. 3. Human ASGR-1 (SEQ ID NO: 32717) vs. human ASGR-2v2 (SEQ ID NO: 32718) alignments are provided.

As shown in Example 1 below, sequence variants in ASGR-1 (which resulted in either a faster degrading ASGR1 or a loss of function ASGR1 mutation) resulted in a lowering in the level of non-HDL cholesterol in humans. This in turn resulted in a decrease in the risk of coronary artery disease experienced by these people. As loss of function mutations in ASGR-1 resulted in both the lowering of non-HDL cholesterol and the lowering of coronary artery disease, antibodies and inhibitory RNA that effectively block ASGR can be used to lower the risk of coronary artery disease.

The present invention is directed to inhibitors of ASGR, ASGR-1 and/or ASGR-2. The present invention provides antigen binding proteins that specifically bind to human ASGR, ASGR-1 and/or ASGR-2 and inhibit human ASGR, ASGR-1 and/or ASGR-2 binding to a ligand. The present invention also provides antigen binding proteins that specifically bind to other species of ASGR, ASGR-1 and/or ASGR-2. The present invention is further directed to methods of treating or preventing cardiovascular disease in a human subject comprising administering an inhibitor of ASGR, ASGR-1 and/or ASGR-2, wherein the ASGR inhibitor an antigen binding protein and/or an interfering RNA (e.g., siRNA or shRNA).

The present invention further provides compositions, kits, and methods relating to antigen binding proteins that specifically bind to human ASGR, human ASGR-1, and/or human ASGR-2. Also provided are nucleic acid molecules comprising a sequence of polynucleotides that encode all or a portion of a polypeptide that specifically binds to human ASGR, human ASGR-1, and/or human ASGR-2. The present invention further provides vectors and plasmids comprising such nucleic acids, and cells or cell lines comprising such nucleic acids and/or vectors and plasmids. The provided methods further include, for example, methods of making, identifying, or isolating antigen binding proteins that bind to human ASGR, human ASGR-1, and/or human ASGR-2, methods of determining whether an antigen binding protein binds to human ASGR, human ASGR-1, and/or human ASGR-2, methods of making compositions, such as pharmaceutical compositions, comprising an antigen binding protein that binds to human ASGR, human ASGR-1, and/or human ASGR-2, and methods for administering an antigen binding protein that binds human ASGR, human ASGR-1, and/or human ASGR-2 to a human subject.

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 1 to 50, or by the actual residue at that site such as asparagine to proline. A particular polypeptide or polynucleotide sequence also can be described by explaining how it differs from a reference sequence.

The following terms, unless otherwise indicated, shall be understood to have the following meanings:

The term "inhibitor" as used herein, is a compound that decreases the magnitude of at least one activity or function of a molecule compared to the magnitude of the activity or function observed in the absence of the inhibitor. In some instances, an inhibitor will substantially decrease the magnitude of at least one activity or function of a molecule compared to the magnitude of the activity or function observed in the absence of the inhibitor. In some instances, an inhibitor will completely diminish the magnitude of at least one activity or function of a molecule compared to the magnitude of the activity or function observed in the absence of the inhibitor. Certain exemplary inhibitors include, but are not limited to, proteins, peptides, antibodies, peptibodies, aptamers, antisense oligonucleotides, interfering RNA, carbohydrates or small organic molecules.

The term "isolated molecule" (where the molecule is, for example, a polypeptide, a polynucleotide, antigen binding protein or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, CA and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

ASGR

Genomic database analysis is one manner that allows for the discovery of associations between disease states and particular targets and/or pathways. For example, genetic analysis of patients with familial hypercholesterolemia resulted in the discovery of proprotein convertase subtilisin/kexin type 9 (PCSK9) being involved with regulating serum LDL cholesterol levels and risk of developing coronary artery disease, and ultimately, in the development of the recently approved Repatha®, an anti-hPCSK9 antibody (see, e.g., Jackson et al., U.S. Pat. No. 8,030,457). Advances in DNA sequencing technology provide the means to sequence the genomes of large numbers of individuals allowing for discovery of rare variants. deCODE Genetics (an Amgen company) has previously reported methods to analyze whole genomes of large numbers of Icelanders in order to search for associations between genetic variants and traits of interest. (Gudbjartsson et al., Nature Genetics; Vol. 47 (5) May 2015; p. 435-444).

This methodology has now been applied in the search for novel genetic variants that affect cardiovascular disease, including cholesterol levels, and the risk for developing coronary artery disease and myocardial infarction (MI). The groundbreaking analysis performed has identified novel sequence variants of the Ashwell-Morell Receptor that are implicated in cardiovascular disease.

In the present invention, whole-genome sequencing of the Icelandic population discovered a rare, 12 base pair deletion ("del12") in intron 4 of the ASGR-1 gene that is also present in other European ancestry populations. This deletion leads to a frameshift predicted to generate a truncated ASGR-1 receptor subunit that is lacking both the oligomerization and extracellular carbohydrate recognition domains (also known as "CRD," "carbohydrate binding domain" or "CBD") or may generate an unstable and rapidly degraded transcript (and therefore no protein) due to nonsense mediated decay. In the present invention, whole-genome sequencing of the Icelandic population also discovered a second rare loss of function variant in the ASGR-1 gene; namely, a 4 base pair insertion in exon 7 (c. 469-472dupAACT or "W158X"). This 4 base pair insertion in exon 7 causes a frameshift and introduces a premature stop codon at amino acid 158 out of the 291 amino acid full length protein (NP_001662.1: p.W158X). This variant is predicted to encode a protein lacking the carbohydrate recognition domain of the receptor or may generate an unstable and rapidly degraded transcript (and therefore no protein) due to nonsense mediated decay. Furthermore, the W158X variant effects all reported refseq transcripts of ASGR-1 regardless of tissue or cell type of expression. Without wishing to be bound by any particular hypothesis, the analysis indicates that del12 and W158X results in lower non-HDL cholesterol levels, protection against CAD and MI, leading to prolonged life. Additionally, the analysis indicates that del12 and W158X also associates with increased levels of circulating ALP and vitamin B12. Supporting this del12 and W158X association with increased levels of ALP are data from mice having a Y272C variant in ASGR-1, showing that these mice exhibit a phenotype of increased plasma ALP (Sabrautzki et al., Mamm. Genome, 23, 416-430, 2012). The Y272 position in mouse ASGR-1 corresponds to the Y273 position in human ASGR-1 (see FIG. 1A).

The Ashwell-Morell Receptor (AMR), originally named the hepatic asialoglycoprotein receptor, was one of the first cellular receptors to be isolated and identified. (Grewal, Methods in Enzymology, Volume 479, Chapter 13, 2010, pp. 223-241). This receptor is also known as the Ashwell Receptor, the hepatic galactose/N-acetylgalactosamine (GalNAc) receptor, or the hepatic lectin receptor. However, this receptor is now more commonly known as "ASGPR," or simply "ASGR."

ASGR is a C-type lectin that is expressed on the surface of hepatocytes and is made up of 48 kDa major subunit(s) (ASGR-1) and 40 kDa minor subunit(s) (ASGR-2). (Roggenbuck et al., Autoimmune Highlights, 2012, 3:119-125). Functional variants of ASGR are formed by the oligomerization of the ASGR-1 and ASGR-2 subunits. (Grewal). The receptor complexes can comprise homo-oligomers and hetero-oligomers of the ASGR-1 and ASGR-2 subunits, with $(ASGR-1)_2\text{-}(ASGR-2)_1$ trimer being the most common form and having the highest affinity to substrate. (Grewal). Other identified forms of ASGR include $(ASGR-1)_2$, $(ASGR-1)_3$, $(ASGR-1)_2\text{-}(ASGR-2)_2$, $(ASGR-1)_3\text{-}(ASGR-2)_2$. (Grewal).

The polynucleotide and polypeptide sequences for several species of ASGR-1 and ASGR-2 are known. Table 1 presents sequences for human, mouse, rat, pig, dog and cynomolgus. FIGS. 1A, 1B and 2 present sequence alignments of various species of ASGR-1 and ASGR-2, and FIG. 3 presents a sequence alignment between human ASGR-1 and human ASGR-2.

ASGR-1 is a single pass transmembrane protein and is the major subunit of ASGR. The galactose (Gal) or N-acetylgalactosamine (GalNAc) residues of glycoproteins are exposed by removal of sialic acid by sialidases, hence the term asialoglycoprotein for the ligands of ASGR. Although ASGR expression is detected in other tissues, liver is the predominant site of expression. A circulating form of the receptor, generated from ASGR-1 transcripts lacking exon two, has also been reported. (Liu J, Hu B, Yang Y, et al. A new splice variant of the major subunit of human asialoglycoprotein receptor encodes a secreted form in hepatocytes. PloS one 2010; 5:e12934). The del12 and W158X variants are predicted to truncate both the membrane bound and the circulating form of the receptor, and as mentioned above, the W158X variant may generate an unstable and rapidly degraded transcript (and therefore no protein) due to nonsense mediated decay.

The primary reported function of ASGR is to bind and internalize glycoproteins in the circulation that contain terminal galactose or N-acetylgalactosamine residues (asialoglycoproteins), resulting in the clearance of these proteins from the circulation. (Roggenbuck). Reported endogenous ligands include components of the blood coagulation system, such as platelets and Von Willebrand Factor. (Grewal).

As used herein, the terms "ASGR, ASGR-1, and/or ASGR-2 function" or "ASGR, ASGR-1, and/or ASGR-2 activity" includes any biological effect of ASGR, ASGR-1 and/or ASGR-2. In certain embodiments, ASGR function or activity includes the ability of ASGR to interact or bind to a ligand. In some embodiments, ASGR function or activity is represented by the ability of ASGR to interact or bind to sugars including but not limited to lactose, galactose, and/or GalNAc or glycoproteins displaying such sugars including but not limited to fetuin, orosomucoid and/or alkaline phosphatase. In some embodiments, ASGR function or activity includes any biological activity resulting from ASGR response. Exemplary activities include, but are not limited to, clearance of asialoglycoproteins from the circulation; clearance of IgA from circulation; removal of apoptotic cells; clearance of low density lipoprotein (LDL) and/or the disposal of cellular fibronectin (Roggenbuck).

Given the location of ASGR on the surface of liver hepatocytes and its implication in hepatocyte entry by certain viruses (Roggenbuck), the receptor has become a target of convenience for therapeutics that require delivery to the liver and internalization into the cells. Examples of these uses include the targeted delivery of doxorubicin to hepatocellular carcinoma (Wei et al., Int J Nanomedicine, 2015, 10:5123-37), gene delivery to hepatocytes (D'Souza et al., J Control Release, 2015, 203:126-39), and targeted delivery of siRNA to hepatocytes (Rajeev et al., Chembiochem, 2015, 16(6):903-8).

Although the ASGR and its ability to mediate endocytosis and degradation of desialylated glycoproteins has been known for nearly 4 decades, the endogenous ligands and the physiological function of the receptor have been difficult to establish. (Weigel P H, Yik J H. Glycans as endocytosis signals: the cases of the asialoglycoprotein and hyaluronan/chondroitin sulfate receptors. Biochimica et biophysica acta 2002; 1572:341-63). It has been reported that ASGR-1-/- mice (lacking any ASGR activity) thrive normally and do not accumulate desialylated glycoproteins in their circulation although they are unable to clear exogenously added asialoglycoproteins, suggesting that under normal physiological condition ASGR is not essential for homeostasis of circulating asialoglycoproteins. (Tozawa R, Ishibashi S, Osuga J, et al. Asialoglycoprotein receptor deficiency in mice lacking the major receptor subunit. Its obligate requirement for the stable expression of oligomeric receptor. The Journal of Biological Chemistry 2001; 276:12624-8).

In contrast to the ASGR-1 knockout mice which lack an apparent phenotype, the present invention has established a clear physiological role for human ASGR-1 in cardiovascular disease, for example, but not limited to, the regulation of non-HDL levels and modulation of CAD and MI risk. The present invention has also demonstrated the association of del12 and W158X with increased levels of circulating ALP and vitamin B12. Furthermore, the present invention shows that disturbing one allele of ASGR-1 appears to have an overall beneficial effect as heterozygotes carriers of del12 live on average 1.5 years longer than non-carriers.

Surprisingly, the various embodiments provided herein demonstrate that the del12 variant and the W158 variant both have an effect on non-HDL levels that is opposite to their effect on ALP and vitamin B12 levels; decreasing non-HDL and increasing ALP and vitamin B12. While not wishing to be bound by any particular hypothesis, it is important to note that the common variant previously described that associates with ALP and LDL cholesterol also has opposing effects on these serum components; hence ASGR-1 may affect the level of these molecules through different mechanisms. It is unlikely that the ALP increase mediated by del12 or W158X reflects an underlying liver disease since other measures of liver function are not affected. Both ALP and the vitamin B12 transporter in the circulation, haptocorrin, are asialylated glycoproteins known to bind ASGR-1 and be cleared from the circulation by the receptor (Tuin A, Huizinga-Van der Vlag A, van Loenen-Weemaes A M, Meijer D K, Poelstra K. On the role and fate of LPS-dephosphorylating activity in the rat liver. American Journal of Physiology Gastrointestinal and Liver Physiology 2006; 290:G377-85; Furger E, Fedosov S N, Lildballe D L, et al. Comparison of recombinant human haptocorrin expressed in human embryonic kidney cells and native haptocorrin. PloS one 2012; 7:e37421; Burger R L, Schneider R J, Mehlman C S, Allen R H. Human plasma R-type vitamin B12-binding proteins. II. The role of transcobalamin I, transcobalamin III, and the normal granulocyte vitamin B12-binding protein in the plasma transport of vitamin B12. The Journal of Biological Chemistry 1975; 250:7707-13; Steirer L M, Park E I, Townsend R R, Baenziger J U. The asialoglycoprotein receptor regulates levels of plasma glycoproteins terminating with sialic acid alpha 2,6-galactose. The Journal of Biological Chemistry 2009; 284:3777-83). While not wishing to be bound by any particular hypothesis, the more likely reason for the increased levels of ALP and vitamin B12 in del12 carriers and in W158X carriers is decreased clearance of desialylated forms of these molecules from the circulation, due to reduced number of functional ASGR receptors in del12 carriers and in W158X carriers, suggesting a role for ASGR-1 in maintaining homeostasis of circulating ALP and vitamin B12.

While not wishing to be bound by any particular hypothesis, the decreased levels of non-HDL in del12 carriers and in W158X carriers in the face of reduced ASGR-1 function suggest that ASGR-1 affects non-HDL levels by mechanisms other than direct binding and endocytosis of cholesterol particles. In mice expressing a hypomorphic form of neuraminidase 1 (Neu1), a sialidase that cleaves the sialic acid residues thereby generating substrates for ASGR-1, the LDL receptor (LDLR) is sialylated and this form of the receptor was more stable and took up LDL cholesterol more avidly (LDL levels were decreased in these mice) than the asialylated form of the wild type LDLR (Yang A, Gyulay G, Mitchell M, White E, Trigatti B L Igdoura S A. Hypomorphic sialidase expression decreases serum cholesterol by downregulation of VLDL production in mice Journal of Lipid Research 2012; 53:2573-2585). Both ASGR and LDLR are located in clathrin-coated pits on hepatocytes and ASGR may be capable of interacting with the asialylated form of the LDLR and blocking its activity.

Two novel rare variants in ASGR-1 have been identified herein that play a role in cardiovascular disease, including, but not limited to, lowering non-HDL levels and protecting against CAD and MI. These variants disrupt ASGR-1 protein function. Accordingly, the present invention is further directed to methods of inhibiting ASGR function, methods of inhibiting ASGR-1 function and/or methods of inhibiting ASGR-2 function. The present invention is further directed to molecules (for example, but not limited to, antigen binding proteins or interfering RNA) that inhibit ASGR function, ASGR-1 function and/or ASGR-2 function.

Antigen Binding Proteins

In some embodiments, the invention comprises antigen binding proteins that bind to ASGR, ASGR-1, and/or ASGR-2 of different species, including, but not limited to, human, cynomolgus, porcine, canine, murine and rat. In some embodiments, the antigen binding proteins specifically bind to ASGR, ASGR-1, and/or ASGR-2 of different species, including, but not limited to, human, cynomolgus, porcine, canine, and murine and rat. Exemplary amino acid sequences of human, cyno, dog, pig, rat and mouse ASGR-1 and ASGR-2 are provided in FIGS. 1-3. In some embodiments, the antigen binding proteins further inhibit ASGR, ASGR-1 and/or ASGR-2 from binding to a ligand.

An "antigen binding protein" is a protein comprising an antigen binding fragment that binds to an antigen and, optionally, a scaffold or framework portion that allows the antigen binding fragment to adopt a conformation that promotes binding of the antigen binding protein to the antigen. In the instant application, the antigen is ASGR, ASGR-1 and/or ASGR-2 protein or a fragment thereof. In some embodiments, the antigen binding fragment comprises at least one CDR from an antibody that binds to the antigen, and in some embodiments comprises the heavy chain CDR3 from an antibody that binds to the antigen. In some embodiments, the antigen binding fragment comprises all three CDRs from the heavy chain of an antibody that binds to the antigen or from the light chain of an antibody that binds to the antigen. In still some embodiments, the antigen binding fragment comprises all six CDRs from an antibody that binds to the antigen (three from the heavy chain and three from the light chain). The antigen binding fragment in certain embodiments is an antibody fragment.

Nonlimiting examples of antigen binding proteins include antibodies, antibody fragments (e.g., an antigen binding fragment of an antibody), antibody derivatives, and antibody analogs. Further specific examples include, but are not limited to, a single-chain variable fragment (scFv), a nanobody (e.g. VH domain of camelid heavy chain antibodies; VHH fragment, see Cortez-Retamozo et al., Cancer Research, Vol. 64:2853-57, 2004), a Fab fragment, a Fab' fragment, a F(ab')2 fragment, a Fv fragment, a Fd fragment, and a complementarity determining region (CDR) fragment. These molecules can be derived from any mammalian source, such as human, mouse, rat, rabbit, or pig, dog, or camelid. Antibody fragments may compete for binding of a target antigen with an intact antibody and the fragments may be produced by the modification of intact antibodies (e.g. enzymatic or chemical cleavage) or synthesized de novo using recombinant DNA technologies or peptide synthesis. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129 (2003); Roque et al., Biotechnol. Prog. 20:639-654 (2004). In addition, peptide antibody mimetics ("PAMs") can be used, as well as scaffolds based on antibody mimetics utilizing fibronectin components as a scaffold.

An antigen binding protein can also include a protein comprising one or more antibody fragments incorporated into a single polypeptide chain or into multiple polypeptide chains. For instance, antigen binding proteins can include, but are not limited to, a diabody (see, e.g., EP 404,097; WO 93/11161; and Hollinger et al., Proc. Natl. Acad. Sci. USA, Vol. 90:6444-6448, 1993); an intrabody; a domain antibody (single VL or VH domain or two or more VH domains joined by a peptide linker; see Ward et al., Nature, Vol. 341:544-546, 1989); a maxibody (2 scFvs fused to Fc region, see Fredericks et al., Protein Engineering, Design & Selection, Vol. 17:95-106, 2004 and Powers et al., Journal of Immunological Methods, Vol. 251:123-135, 2001); a triabody; a tetrabody; a minibody (scFv fused to CH3 domain; see Olafsen et al., Protein Eng Des Sel., Vol. 17:315-23, 2004); a peptibody (one or more peptides attached to an Fc region, see WO 00/24782); a linear antibody (a pair of tandem Fd segments (VH-CH1-VH-CH1) which, together with complementary light chain polypeptides, form a pair of antigen binding regions, see Zapata et al., Protein Eng., Vol. 8:1057-1062, 1995); a small modular immunopharmaceutical (see U.S. Patent Publication No. 20030133939); and immunoglobulin fusion proteins (e.g. IgG-scFv, IgG-Fab, 2scFv-IgG, 4scFv-IgG, VH-IgG, IgG-VH, and Fab-scFv-Fc).

In certain embodiments, an antigen binding protein can have, for example, the structure of an immunoglobulin. An "immunoglobulin" is a tetrameric molecule, with each tetramer comprising two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Within light and heavy chains, the variable (V) and constant regions (C) are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

Human light chains are classified as kappa and lambda light chains. The term "light chain" refers to a polypeptide comprising, from amino terminus to carboxyl terminus, a single immunoglobulin light chain variable region (VL) and a single immunoglobulin light chain constant domain (CL). Heavy chains are classified as mu ($\mu$), delta ($\Delta$), gamma ($\gamma$), alpha ($\alpha$), and epsilon ($\epsilon$), and define the antibody's isotype as IgM, IgD, IgG, IgA, and IgE, respectively. The term "heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). The IgG-class is further divided into subclasses, namely, IgG1, IgG2, IgG3, and IgG4. The IgA-class is further divided into subclasses, namely IgA1 and IgA2. The IgM has subclasses including, but not limited to, IgM1 and IgM2. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the antibody heavy chains.

The term "antibody" refers to an intact immunoglobulin of any isotype, and includes, for instance, chimeric, humanized, human, and bispecific antibodies. An "antibody" is a species of an antigen binding protein. An intact antibody will generally comprise at least two full-length heavy chains and two full-length light chains. Antibody sequences can be derived solely from a single species, or can be "chimeric," that is, different portions of the antibody can be derived from two different species as described further below. Unless otherwise indicated, the term "antibody" also includes antibodies comprising two substantially full-length heavy chains and two substantially full-length light chains provided the antibodies retain the same or similar binding and/or function as the antibody comprised of two full length light and heavy chains. For example, antibodies having 1, 2, 3, 4, or 5 amino acid residue substitutions, insertions or deletions at the N-terminus and/or C-terminus of the heavy and/or light chains are included in the definition provided that the antibodies retain the same or similar binding and/or function as the antibodies comprising two full length heavy chains and two full length light chains. Furthermore, unless explicitly excluded, antibodies include, for example, monoclonal antibodies, polyclonal antibodies, chimeric antibodies, humanized antibodies, human antibodies, bispecific antibodies, and synthetic antibodies. In some sections of the present disclosure, examples of antigen binding proteins are described herein in terms of the hybridoma line number as "number/letter/number" (e.g., 25A4). In these cases, the exact name denotes a specific monoclonal antibody derived from a specific hybridoma having a specific light chain variable region and heavy chain variable region. In some sections of the present disclosure, examples of antigen binding proteins are described herein in terms of "number/letter/number/"dot"/number" (e.g., 25A4.001) or number/letter/number/"dot"/number/"dot"/number (e.g., 25A4.001.001). In these cases, the name denotes a variant of a specific antibody having a light chain variable region and a heavy chain variable region that is related to, but distinct from the antibody derived from a hybridoma. That is, for example, an antigen binding protein named 25A4 is not the same as an antibody named 25A4.001 or an antibody named 25A4.001.001.

A "polyclonal antibody" refers to a population of antibodies that are typically widely varied in composition and binding specificity. A "monoclonal antibody" ("mAb") as used herein refers to one or more of a population of antibodies having identical sequences. Monoclonal antibodies bind to the antigen at a particular epitope on the antigen.

In some embodiments, the antigen binding protein is a "fragment" or "antigen binding fragment" of an antibody. As used herein and unless otherwise specified, an "antibody fragment" refers to the Fab, Fab', F(ab')2, and Fv fragments that contain at least one CDR of an immunoglobulin that is sufficient to confer specific antigen binding to ASGR, ASGR-1 and/or ASGR-2. Antibody fragments may be produced by recombinant DNA techniques or by enzymatic or chemical cleavage of intact antibodies.

A Fab fragment is a monovalent fragment having the VL, VH, CL and CH1 domains; a F(ab')2 fragment is a bivalent fragment having two Fab fragments linked by a disulfide bridge at the hinge region; a Fd fragment has the VH and CH1 domains; an Fv fragment has the VL and VH domains of a single arm of an antibody; and a dAb fragment has a VH domain, a VL domain, or an antigen-binding fragment of a VH or VL domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)). In certain embodiments, these antibody fragments can be incorporated into single domain antibodies, single-chain antibodies, maxibodies, minibodies, intrabodies, diabodies, triabodies, tetrabodies, v-NAR and bis-scFv (see e.g., Hollinger and Hudson, 2005, Nature Biotechnology, 23, 9, 1126-1136). Other antigen binding proteins envisioned are antibody polypeptides such as those disclosed in U.S. Pat. No. 6,703,199, including fibronectin polypeptide monobodies, the polypeptides as disclosed in U.S. Patent Publication 2005/0238646. In some embodiments, the antibodies comprise at least one CDR set forth in Tables 2 or 6 herein.

A "single-chain variable fragment" ("scFv") is a fusion protein in which a VL and a VH region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). For the sake of clarity, a "single-chain variable fragment" is not an antibody or an antibody fragment as defined herein. Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The term "CDR" refers to the complementarity determining region (also termed "minimal recognition units" or "hypervariable region") within antibody variable sequences. The CDRs permit the antigen binding protein to specifically bind to a particular antigen of interest. There are three heavy chain variable region CDRs (CDRH1, CDRH2 and CDRH3) and three light chain variable region CDRs (CDRL1, CDRL2 and CDRL3). The CDRs in each of the two chains typically are aligned by the framework regions to form a structure that binds specifically to a specific epitope or domain on the target protein. From N-terminus to C-terminus, naturally-occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, J. Mol. Biol. 196:901-917; Chothia et al., 1989, Nature 342: 878-883. Complementarity determining regions (CDRs) and framework regions (FR) of a given antibody may be identified using this system. Other numbering systems for the amino acids in immunoglobulin chains include IMGT® (the international ImMunoGeneTics information system;

Lefranc et al, Dev. Comp. Immunol. 29:185-203; 2005) and AHo (Honegger and Pluckthun, J. Mol. Biol. 309(3):657-670; 2001). One or more CDRs may be incorporated into a molecule either covalently or noncovalently to make it an antigen binding protein.

In some embodiments, an antigen binding protein of the invention may incorporate the CDR(s) as part of a larger polypeptide chain, may covalently link the CDR(s) to another polypeptide chain, or may incorporate the CDR(s) noncovalently. The antigen binding molecules may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostatin, cytochrome b, CP1 zinc finger, PST1, coiled coil, LACI-D1, Z domain and tendamistat domains may be used (See e.g., Nygren and Uhlen, 1997, Current Opinion in Structural Biology, 7, 463-469).

An antigen binding protein may have one or more binding sites. If there is more than one binding site, the binding sites may be identical to one another or may be different. For example, an antibody typically has two identical binding sites, while a "bispecific" or "bifunctional" antibody has two different binding sites. The two binding sites of a bispecific antigen binding protein or antibody will bind to two different epitopes, which can reside on the same or different protein targets.

In some embodiments, the ASGR-1 antigen binding protein is a bispecific antibody. In certain embodiments, a bispecific antibody binds to ASGR, ASGR-1 or ASGR-2 and PCSK9. In some embodiments, a bispecific antibody will bind to the ASGR-1 CBD and will inhibit ASGR-1 function, in addition to binding to PCSK9 and inhibiting the binding of PCSK9 to the LDLR. Methods of making bispecific antibodies are known in the art. One such method of making a "bispecific," or "bifunctional" antigen binding protein or antibody involves the fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. Another method involves engineering the Fc portion of the heavy chains such as to create "knobs" and "holes" which facilitate heterodimer formation of the heavy chains when co-expressed in a cell. U.S. Pat. No. 7,695,963. Still another method also involves engineering the Fc portion of the heavy chain but uses electrostatic steering to encourage heterodimer formation while discouraging homodimer formation of the heavy chains when co-expressed in a cell. WO 09/089,004, which is incorporated herein by reference in its entirety.

The term "human antibody" includes antibodies having antibody regions such as variable and constant regions or domains which correspond substantially to human germline immunoglobulin sequences known in the art, including, for example, those described by Kabat et al. (1991) (loc. cit.). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, in CDR3. The human antibodies can have at least one, two, three, four, five, or more positions replaced with an amino acid residue that is not encoded by the human germline immunoglobulin sequence. The definition of human antibodies as used herein also contemplates fully human antibodies, which include only non-artificially and/or genetically altered human sequences of antibodies as those can be derived by using technologies or systems known in the art, such as for example, phage display technology or transgenic mouse technology, including but not limited to the Xenomouse.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-ASGR, ASGR-1 or ASGR-2 antibody. In another embodiment, all of the CDRs are derived from a human anti-ASGR, ASGR-1 or ASGR-2 antibody. In another embodiment, the CDRs from more than one human anti-ASGR, ASGR-1 or ASGR-2 antibodies are mixed and matched in a chimeric antibody. For instance, a chimeric antibody may comprise a CDR1 from the light chain of a first human anti-ASGR, ASGR-1 or ASGR-2 antibody, a CDR2 and a CDR3 from the light chain of a second human anti-ASGR, ASGR-1 or ASGR-2 antibody, and the CDRs from the heavy chain from a third anti-ASGR, ASGR-1 or ASGR-2 antibody. Further, the framework regions may be derived from one of the same anti-ASGR, ASGR-1 or ASGR-2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity.

A "neutralizing antigen binding protein" or "inhibitory antigen binding protein" or "antagonizing antigen binding protein" (e.g., "neutralizing antibody" or "inhibitory antibody" or "antagonizing antibody") refers to an antigen binding protein or antibody, respectively, that binds to a target molecule and reduces and/or prevents the biological effect of that target molecule. This can be done, for example, by directly blocking a site on the target molecule through which the target molecule interacts with other molecules (e.g. blocking a ligand binding site of a receptor) or by indirectly blocking a site on the target molecule through which the target molecule interacts with other molecules (such as structural or energetic alterations in the target molecule). In some embodiments, these terms can also denote an antigen binding protein or antibody that prevents the target molecule to which it is bound from performing a biological function. In assessing the binding and/or specificity of an antigen binding protein, e.g., an antibody or immunologically functional fragment thereof, an antibody or fragment can substantially inhibit binding of a target molecule to its binding partner when an excess of antibody reduces the quantity of binding partner bound to the target molecule by at least about 1-20, 20-30%, 30-40%, 40-50%, 50-60%, 60-70%, 70-80%, 80-85%, 85-90%, 90-95%, 95-97%, 97-98%, 98-99%, 99.5%, 99.9% and 100%. In some embodiments, inhibition is complete. The measurement of reduction of binding is done using various assays known to those skilled in the art, (e.g., an in vitro competitive binding assay) and performed using relevant control molecules so that actual inhibition is measured. For example, numerous competition assays are well known in the art, with nonlimiting examples being competition ELISA, use of the BiaCore® platform, the Kinexa® platform, or the like. Further examples include: solid phase direct or indirect radioimmunoassay (RA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:7-82). Typically, such an assay involves the use of purified antigen bound to a solid surface or cells bearing either of these, an unlabelled test antigen binding protein and a labeled reference antigen binding protein. In some embodiments, in the case of ASGR, ASGR-1 and/or ASGR-2, such a neutralizing antigen binding protein or antibody can diminish the ability of ASGR, ASGR-1 and/or ASGR-2 to bind to a ligand. In some embodiments, the neutralizing ability is characterized and/or described via a competition assay. In some embodiments, the neutralizing ability is described in terms of an IC50 or EC50 value. The antigen binding proteins in at least Table C are strong neutralizers. In some embodiments, the antibodies or antigen binding proteins neutralize by binding to ASGR, ASGR-1 and/or ASGR-2 and preventing ASGR, ASGR-1 and/or ASGR-2 from binding to a ligand, including sugars such as lactose, galactose, and/or GalNAc or glycoproteins displaying such sugars, such as fetuin, orosomucoid and/or alkaline phosphatase (or reducing the ability of ASGR, ASGR-1 and/or ASGR-2 to bind to ligand).

Competitive inhibition can be measured by determining the amount of labelled ligand bound to the solid surface or cells in the presence of the test antigen binding protein. Usually the test antigen binding protein is present in excess. Antigen binding proteins or antibodies identified by competition assay (competing antigen binding proteins or antibodies) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit (e.g., reduce) specific binding of a reference antigen binding protein to a target antigen by at least 40-45%, 45-50%, 50-55%, 55-60%, 60-65%, 65-70%, 70-75% or 75% or more. In some embodiments, binding is inhibited by at least 40%, 45%, 50%, 55%, 60%, 65%, 70%, 75%, 80%, 85%, 90%, or 95%. In some embodiments, binding is inhibited by at least 80-85%, 85-90%, 90-95%, 95-97%, or 97% or more, including up to 100% inhibition.

In some embodiments, a ligand binding assay is used where cells expressing the target protein (e.g., ASGR-1) are mixed with antigen binding proteins and incubated for a time period, then washed. These cells are then incubated with labelled ligand (e.g., β-GalNAc) for a time period and then washed and analyzed for ligand binding, where reduced ligand binding as compared to a relevant control antigen binding protein indicates inhibition of binding due to the antigen binding protein blocking or inhibiting this binding.

Another manner in which the reduction in binding can be measured is the half maximal inhibitory concentration (IC50). The IC50 measures the amount or concentration of antigen binding protein that is needed to inhibit a given attribute (e.g., ligand binding) by half. In certain embodiments, the antigen binding proteins (e.g., human antibodies) have an IC50 value of 90 nM or less, in another embodiment, an IC50 value of 80 nM or less, in another embodiment, 70 nM or less, in another embodiment, 60 nM or less, in another embodiment, 50 nM or less, in another embodiment, 40 nM or less, in another embodiment, 30 nM or less, in another embodiment 25 nM or less.

In certain embodiments, the antigen binding proteins of the invention bind to an ASGR-1 monomer. In some embodiments, the antigen binding proteins of the invention bind to an ASGR-1 oligomer. In further embodiments, the antigen binding proteins of the invention bind to an ASGR-2 monomer. In some embodiments, the antigen binding proteins of the invention bind to an ASGR-2 oligomer. In certain embodiments, the antigen binding proteins of the invention bind to both ASGR-1 monomers and ASGR-2 monomers. In certain embodiments, the antigen binding proteins of the invention bind to an ASGR oligomer comprising an $(ASGR-1)_2$-$(ASGR-2)_1$ trimer. In some embodiments, the antigen binding proteins of the invention bind to an ASGR oligomer comprising an $(ASGR-1)_2$ dimer. In further embodiments, the antigen binding proteins of the invention bind to an ASGR oligomer comprising an $(ASGR-1)_3$ trimer. In yet further embodiments, the antigen binding proteins of the invention bind to an ASGR oligomer comprising an $(ASGR-1)_2$-$(ASGR-2)_2$ tetramer. In further embodiments, the antigen binding proteins of the invention bind to an ASGR oligomer comprising an $(ASGR-1)_3$-$(ASGR-2)_2$ pentamer. In some embodiments, the antigen binding proteins of the invention bind to a multimeric complex comprising at least two subunits of ASGR-1 and/or ASGR-2.

In certain embodiments, the antigen binding proteins (e.g., antibodies, antibody fragments, etc.) bind to ASGR, ASGR-1 and/or ASGR-2 and inhibit ASGR, ASGR-1 and/or ASGR-2 from binding to a ligand, wherein the antigen binding proteins comprise specific amino acid residues at particular positons in the molecule (e.g., in the VH, VL or CDRs). These residues may be involved in the binding properties of desired molecules (e.g., part of the paratope). A "paratope" are used herein is the location in an antibody that binds to the antigen. The paratope can comprise several amino acid residues from the VH and/or VL CDRs, and also can comprise residues from the framework regions. The paratope binds to the antigen's epitope. Paratopes can be determined using methodologies similar to those described determining epitopes. Once the amino acid residues involved in the binding properties of desired molecules, are identified, this information can be used to design antigen binding proteins (e.g., antibodies, antibody fragments, etc.) that can bind to ASGR, ASGR-1 and/or ASGR-2 and inhibit ASGR function (e.g., inhibit ASGR, ASGR-1 and/or ASGR-2 from binding to ligand).

The binding site (or interface) between the representative antibodies and human ASGR-1 can be determined/defined a number of ways. For example, binding of representative antigen binding proteins (e.g., antibodies) to human ASGR-1 was analyzed in Example 10 using X-ray crystallography, and the binding site or interface was determined using distance. The crystal structure of the antibody/huASGR1 complex provides information as to which residues of representative antibodies form the interface with human ASGR-1. As mentioned above, one of ordinary skill in the art may use this information to design antigen binding proteins and antigen binding protein variants, including those that contain variable domains having 90% identity or greater, 95% identity or greater, 97% identity or greater, 99% identity or greater, or those antigen binding protein variants that contain variable domains having 20 or less, 15 or less, or 10 or less, or 5 or less insertions, deletions, and/or substitutions within the light chain and/or heavy chain variable domain of the antigen binding proteins disclosed herein. One may wish to maintain the amino acids within the interface while altering non-interface residues. Thus, in some embodiments, one may design and create antigen binding proteins and antigen binding protein variants of the antigen binding proteins disclosed herein having one or more amino acid additions, substitutions, and/or deletions within one or more CDRs that maintain binding to human ASGR-1 and inhibit ASGR, ASGR-1 and/or ASGR-2 function (e.g., inhibit ASGR, ASGR-1 and/or ASGR-2 from binding to ligand).

In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13 or all amino acid residues selected from the group consisting of Q27, R30, D32, H91, Y92, S93, Y94, I2, G28, I29, L33, Q90, P95, and R96 of SEQ ID NO:25010 and/or the heavy chain variable region comprises at least 1, 2, 3, 4, 5, 6, 7, 8, 9, 10, 11, 12, 13, 14, 15, 16, 17, 18, 19, 20, 21, 22, 23 or all amino acid residues selected from the group consisting of S30, N31, W52, Y53, D54, S56, N57, Y59, Y101, S102, S103, G104, W105, Y106, D107, Y32, V33, V50, G55, K58, N74, E99, V100, and Y108 of SEQ ID NO:29016. In some embodiments, the light chain variable region comprises at least 1, 2, 3, 4, 5, 6 or all amino acid residues selected from the group consisting of Q27, R30, D32, H91, Y92, S93, and Y94 of SEQ ID NO:25010 and/or the heavy chain variable region comprises at least 1, 2, 3, 4, 5, 6, 7, 8, 9, 10, 11, 12, 13, 14, or all amino acid residues selected from the group consisting of S30, N31, W52, Y53, D54, S56, N57, Y59, Y101, S102, S103, G104, W105, Y106, and D107 of SEQ ID NO:29016. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15 or all amino acid residues selected from the group consisting of H31, S33, N34, N36, Y38, W56, Y97, Y98, I29, S32, N35, N37, Y55, T59, Q96, N99, T100 of SEQ ID NO:25164 and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25, 26 or all amino acid residues selected from the group consisting of T28, F29, T30, N31, Y32, D33, W50, H52, S55, N57, S99, S100, G101, W102, Y103, Y27, I34, N35, W47, M51, P53, N54, G56, T58, G59, Y104, D106 of SEQ ID NO:29170. In some embodiments, the light chain variable region comprises at least 1, 2, 3, 4, 5, 6, 7 or all amino acid residues selected from the group consisting H31, S33, N34, N36, Y38, W56, Y97, Y98 of SEQ ID NO:25164 and/or the heavy chain variable region comprises at least 1, 2, 3, 4, 5, 6, 7, 8, 9, 10, 11, 12, 13, 14, or all amino acid residues selected from the group consisting of T28, F29, T30, N31, Y32, D33, W50, H52, S55, N57, S99, S100, G101, W102, Y103 of SEQ ID NO:29170. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17, 18 or all amino acid residues selected from the group consisting of I30, Y32, T91, Y92, S93, T94, I96, I2, Q27, N28, I29, S31, L33, N34, T50, S67, Q89, Q90, P95 of SEQ ID NO:24908 and/or the heavy chain variable region comprises at least 1, 2, 3, 4, 5, 6, 7, 8, 9, 10, 11, 12, 13, 14, 15, 16, 17, 18, 19, 20, 21, 22 or all amino acid residues selected from the group consisting of S30, S31, I50, W52, H53, S56, N57, Y59, S01, M102, G103, T28, F29, F32, G33, H35, W47, I51, D54, K58, D99, L100, G104 of SEQ ID NO:28914. In some embodiments, the light chain variable region comprises at least 1, 2, 3, 4, 5, 6 or all amino acid residues selected from the group consisting I30, Y32, T91, Y92, S93, T94, I96 of SEQ ID NO:24908 and/or the heavy chain variable region comprises at least 1, 2, 3, 4, 5, 6, 7, 8, 9, 10 or all amino acid residues selected from the group consisting of S30, S31, I50, W52, H53, S56, N57, Y59, S01, M102, G103 of SEQ ID NO:28914. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15 or all amino acid residues selected from the group consisting of Y32, S91, Y92, R93, Thr94, Pro95, F97, Ile2, Q27, N28, NAG100, Ile29, S30, S31, Q90, and L96 of SEQ ID NO:24362 and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25, 26, 27 or all amino acid residues selected from the group consisting of A33, Val50, Ile51, S52, R53, S54, G55, G56, Y57, Y59, R99, A101, A103, G104, E106, S30, S31, Y32, Met34, N35, W47, S49, Thr58, R72, N74, L100, Val102, and S105 of SEQ ID NO:28368. In some embodiments, the light chain variable region comprises at least 1, 2, 3, 4, 5, 6, or all amino acid residues selected from the group consisting of Y32, S91, Y92, R93, Thr94, Pro95, and F97 of SEQ ID NO:24362, and/or the heavy chain variable region comprises at least 1, 2, 3, 4, 5, 6, 7, 8, 9, 10, 11, 12, 13, 14, or all amino acid residues selected from the group consisting of A33, Val50, Ile51, S52, R53, S54, G55, G56, Y57, Y59, R99, A101, A103, G104, and E106 of SEQ ID NO:28368. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17 or all amino acid residues selected from the group consisting of Q27, W32, A91, N92, S93, F94, F96, D1, I2, G28, I29, S30, R31, Y49, G50, Q89, Q90, and P95 of SEQ ID NO:24930 and/or the heavy chain variable region comprises at least 1, 2, 3, 4, 5, 6, 7, 8, 9, 10, 11, 12, 13, 14, 15, 16, 17, 18, 19, 20, 21, 22 or all amino acid residues selected from the group consisting of Y33, H35, W50, H52, S55, G57, T58, N59, D99, G100, T101, S102, D31, Y32, L34, W47, I51, N54, G56, Y60, Q65, S103, and F104 of SEQ ID NO:28936. In some embodiments, the light chain variable region comprises at least 1, 2, 3, 4, 5, 6 or all amino acid residues selected from the group consisting of Q27, W32, A91, N92, S93, F94, and F96 of SEQ ID NO:24930 and/or the heavy chain variable region comprises at least 1, 2, 3, 4, 5, 6, 7, 8, 9, 10, 11 or all amino acid residues selected from the group consisting of Y33, H35, W50, H52, S55, G57, T58, N59, D99, G100, T101, and S102 of SEQ ID NO:28936. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17, 18, 19 or all amino acid residue selected from the group consisting of Y32, Y49, T50, Q55, S91, H92, S93, F94, F96, S28, I29, T30, N33, L46, S53, L54, S56, Q89, Q90, and P95 of SEQ ID NO:28074 and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25, 26, 27, 28 or all amino acid residues selected from the group consisting of G26, F27, T28, S30, S31, Y32, S33, S52, G53, S54, S56, Y57, Y59, R98, G100, S101, R102, V2, F29, N35, S50, T51, S55, I58, R72, G99, G103, F104 and D105 of SEQ ID NO:32080. In some embodiments, the light chain variable region comprises at least 1, 2, 3, 4, 5, 6, 7, 8 or all amino acid residues selected from the group consisting of Y32, Y49, T50, Q55, S91, H92, S93, F94, and F96 of SEQ ID NO:28074 and/or heavy chain variable region comprises at least 1, 2, 3, 4, 5, 6, 7, 8, 9, 10, 11, 12, 13, 14, 15, 16 or all amino acid residues selected from the group consisting of G26, F27, T28, S30, S31, Y32, S33, S52, G53, S54, S56, Y57, Y59, R98, G100, S101 and R102 of SEQ ID NO:32080. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17, 18, 19, 20, 21 or all amino acid residues selected from the group consisting of V29, S30, I32, Y33, L47, Y50, R55, A56, T57, Y94, G28, N31, L48, I49, G51, N54, G58, I59, S68, G69, D93, and S95 of SEQ ID NO:26814 and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25 or all amino acid residues selected from the group consisting of V31, Y32, Y33, W50, N52, S55, G57, R98, G99, Y100, D101, I102, T204, V2, Y27, T30, L34, N35, P53, N54, G56, T58, N59, A97, L103, and G105 of SEQ ID NO:30820. In some embodiments, the light chain variable region comprises at least 1, 2, 3, 4, 5, 6, 7, 8, 9, or all amino acid residues selected from the group consisting of V29, S30, I32, Y33, L47, Y50, R55, A56, T57, and Y94 of SEQ ID NO:26814 and/or heavy chain variable region comprises at least 1, 2, 3, 4, 5, 6, 7, 8, 9, 10, 11, 12 or all amino acid residues selected from the group consisting of V31, Y32, Y33, W50, N52, S55, G57, R98, G99, Y100, D101, I102, and T204 of SEQ ID NO:30820. In some embodiments, the antigen binding protein or the antibody comprises a light chain variable region and/or a heavy chain variable region, wherein the light chain variable region comprises at least 1, 2, 3 or all amino acid residues selected from the group consisting of N31, Y50, V51, Q54 SEQ ID NO:27482; and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25, 26, 27 or all amino acid residues selected from the group consisting of N30, S31, Y32, S52, Y54, N55, K59, R98, D100, F101, W102, S103, G104, Y105, K107, D110, V2, Y27, T28, F29, G33, W50, A53, G56, N57, H99, Y106, or G108 of SEQ ID NO:31488. In some embodiments, the antigen binding protein or the antibody comprises a light chain variable region and/or a heavy chain variable region, wherein the heavy chain variable region comprises at least 1, 2, 3, 4, 5, 6, 7, 8, 9, 10, 11, 12, 13, 14, 15, or all amino acid residues selected from the group consisting of N30, S31, Y32, S52, Y54, N55, K59, R98, D100, F101, W102, S103, G104, Y105, K107, and D110 of SEQ ID NO:31488. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, or all amino acid residues selected from the group consisting of Y33, Y50, D51, N53, K54, S57, V34, S52, R55, P56, G58, and G65 of SEQ ID NO:27780 and/or the heavy chain variable region comprises at least 1, 2, 3, 4, 5, 6, 7, 8, 9, 10, 11, 12, 13, 14, 15, 16, 17, 18, 19, 20, 21, 22, 23, 24, 25 or all amino acid residues selected from the group consisting of Q1, V2, F27, S30, S31, Y32, Y53, D54, W99, Y100, Y101, Y102, G26, T28, F29, G33, W52, G55, R72, N74, N98, Y103, Y104, D107, and V108 of SEQ ID NO:31786. In some embodiments, the light chain variable region comprises at least 1, 2, 3, 4, 5 or all amino acid residues selected from the group consisting of Y33, Y50, D51, N53, K54 and S57 of SEQ ID NO:27780 and/or heavy chain variable region comprises at least 1, 2, 3, 4, 5, 6, 7, 8, 9, 10, 11 or all amino acid residues selected from the group consisting of Q1, V2, F27, S30, S31, Y32, Y53, D54, W99, Y100, Y101, and Y102 of SEQ ID NO:31786. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17, 18, 19 or all amino acid residues selected from the group consisting of H31, G32, D33, G34, K35, Y37, I97, Q98, I99, I2, Q27, S28, L29, L30, T36, E55, Q95, S96, P100, and W101 of SEQ ID NO:26536 and/or the heavy chain variable region comprises at least 1, 2, 3, 4, 5, 6, 7, 8, 9, 10, 11, 12, 13, 14, 15, 16, 17, 18, 19, 20, 21, 22, 23 or all amino acid residues selected from the group consisting of S31, W52, Y53, D54, Y57, Y59, D102, F103, W104, T28, S30, Y32, G33, W47, I50, I51, S56, K58, Y60, K65, D99, H101, S105, and G106 of SEQ ID NO:30542. In some embodiments, the light chain variable region comprises at least 1, 2, 3, 4, 5, 6, 7, 8 or all amino acid residues selected from the group consisting of H31, G32, D33, G34, K35, Y37, I97, Q98, and I99 of SEQ ID NO:26536 and/or heavy chain variable region comprises at least 1, 2, 3, 4, 5, 6, 7, 8 or all amino acid residues selected from the group consisting of S31, W52, Y53, D54, Y57, Y59, D102, F103 and W104 of SEQ ID NO:30542. In some embodiments, the antigen binding protein or the antibody comprises a light chain variable region and/or a heavy chain variable region, wherein the light chain variable region comprises at least 1, 2, 3, 4, 5, 6, 7, 8, 9, 10, 11, 12, 13, 14, 15, 16, 17, 18, 19 or all amino acid residues selected from the group consisting of N30, S31, Y33, F50, S54, S68, Y92, E93, W97, S28, V29, G32, L47, G51, A52, S53, R55, A56, G69, Q90, Q91, S94, and S95 of SEQ ID NO:26826 and/or the heavy chain variable region comprises at least 1, 2, 3, 4, 5, 6, 7, 8, 9, 10, 11, 12, 13, 14, 15, 16, 17, 18, 19, 20, 21, 22, 23, 24 or all amino acid residues selected from the group consisting of R30, Y31, Y33, E50, S54, S56, N58, D98, Y99, G100, S28, Y32, W34, S35, W47, G49, I51, S52, H53, G55, T57, R97, A101, F102 and D103 of SEQ ID NO:30832. In some embodiments, the light chain variable region comprises at least 1, 2, 3, 4, 5, 6, 7, 8 or all amino acid residues selected from the group consisting of N30, S31, Y33, F50, S54, S68, Y92, E93, and W97 of SEQ ID NO:26826 and/or heavy chain variable region comprises at least 1, 2, 3, 4, 5, 6, 7, 8, 9 or all amino acid residues selected from the group consisting of R30, Y31, Y33, E50, S54, S56, N58, D98, Y99 and G100 of SEQ ID NO:30832.

In further embodiments, consensus sequences among the antigen binding proteins of the inventions are envisioned. For example, the variable heavy chain and variable light chain regions (VH and VL) and the CDRs (HCDR1/2/3 and LCDR1/2/3) of the invention include consensus sequences derived from groups of related monoclonal antibodies. In some embodiments, the antigen binding proteins (e.g., antibodies) may be related by both sequence homology and function. As described herein, a "consensus sequence" refers to amino acid sequences having conserved amino acids common among a number of sequences and amino acids that vary within given amino acid sequences at certain positions. In some embodiments, the varied amino acid at a certain position is a substitution. In some embodiments, the varied amino acid at a certain position is a deletion. In some embodiments, the varied amino acid at a certain position is an addition or insertion. These varied amino acids will be apparent to one of skill in the art when analyzing particular antibody VH, VL and/or CDR sequences.

For example, antibody sequences were analyzed using the following methodology. The Smith-Waterman algorithm was used to align amino acid sequences against translated IMGT germline V, D and J genes. The V gene was located first, then the J gene was located in the region downstream from located V gene, and finally the D gene was located in the region between V and J regions. Note, that since D gene is a relatively short sequence that is located in the hypervariable CDR3 region, a spurious match is possible and as such, was taken into consideration.

Sequences from each group were then subjected to sequence similarity alignment interrogation using a program that employs a standard ClustalW algorithm (see, Thompson et al., 1994, Nucleic Acids Res. 22:4673-4680). In some cases, the Biosum cost matrix was used with a gap creation penalty of 50 was employed along with a gap extension penalty of 0.1. The sequence logos were generated by Geneious (v8.1.7, Biomatters) once the alignments were made and then exported as PDF images. The consensus sequences were generated in Geneious (v8.1.7, Biomatters) with a 0% threshold and exported as FASTA files. Amino acids that varied within each group were noted with the notation X within each consensus sequence. See Table 19A VH Consensus 1-14 and Table 20A VL Consensus 1-14 in FIG. 55, and Tables 21-48 in FIG. 56 for the consensus sequences resulting from this analysis. In other cases, the consensus sequences were generated in Abinitio. See Table 19A VH Consensus-15-60 and Table 20A VL Consensus 15-54 in FIG. 55, and Tables 49-134 in FIG. 57 for the consensus sequences resulting from this analysis.

Alternatively, different methods of analysis readily available to one of skill in the art can be used. For example, consensus sequences can be determined using standard phylogenetic analyses of the CDRs corresponding to the VH (i.e., Variable Heavy, etc.) & VL (i.e., Variable Light, etc.) of antibodies. For example, amino acid sequences corresponding to the entire variable domains of either VH or VL can be converted to FASTA formatting for ease in processing comparative alignments and inferring phylogenies. Next, framework regions of these sequences can be replaced with an artificial linker sequence so that examination of the CDRs alone can be performed without introducing any amino acid position weighting bias due to coincident events (e.g., such as unrelated antibodies that serendipitously share a common germline framework heritage) while still keeping CDRs contiguous within the same sequence corresponding to a VH or VL. VH or VL sequences of this format can then be subjected to sequence similarity alignment interrogation using a program that employs a standard ClustalW-like algorithm (see, Thompson et al., 1994, Nucleic Acids Res. 22:4673-4680). A gap creation penalty of 8.0 can be employed along with a gap extension penalty of 2.0. This program likewise generated phylograms (phylogenetic tree illustrations) based on sequence similarity alignments using either UPGMA (unweighted pair group method using arithmetic averages) or Neighbor-Joining methods (see, Saitou and Nei, 1987, Molecular Biology and Evolution 4:406-425) to construct & illustrate similarity and distinction of sequence groups via branch length comparison and grouping. The original sequence alignments generated can be employed to empirically examine and document the occurrence of amino acids tolerated at each position with a consensus group. Consensus sequences for the groups of similar sequences within each CDR can then be prepared.

In another type of approach, CDR consensus sequences can be determined for each separate CDR, independently of their contiguous context within the same sequence corresponding to a VH or VL. In this approach the consensus sequences can be determined by aligning each H-CDR1, H-CDR2, H-CDR3, L-CDR1, L-CDR2, and L-CDR3 in groups, i.e., by aligning the individual H-CDR1 sequences of the antigen binding proteins to determine a H-CDR1 consensus sequence, by aligning the individual H-CDR2 sequences of the antigen binding proteins to determine a H-CDR2 consensus sequence, by aligning the individual H-CDR3 sequences of the antigen binding proteins to determine a H-CDR3 consensus sequence, by aligning the individual L-CDR1 sequences of the antigen binding proteins to determine a L-CDR1 consensus sequence, by aligning the individual L-CDR2 sequences of the antigen binding proteins to determine a L-CDR2 consensus sequence, and by aligning the individual L-CDR3 sequences of the antigen binding proteins to determine a L-CDR3 consensus sequence. Similarities between sequences within each individual CDR sequences can be identified. Consensus sequences for the groups of similar sequences within each CDR can then be prepared.

Various embodiments of Variable Heavy chain (VH) Consensus amino acid sequences of the present invention are set forth in Table 19A of FIG. 55 (CDRs are underlined, with the first being CDR1). Various embodiments of VH CDR Consensus amino acid sequences of the present invention are set forth in Tables 19B and 19C of FIG. 55. In some cases, an "X" is present in the amino acid sequences set forth in Tables 19A and 19B which signifies that more than one amino acid (or no amino acid) may be present at this location (see FIGS. 56 and 57 for details of the consensus protein alignment). In some cases a "-" is present in Table 19A (which is the result of the consensus alignment) and signifies that no amino acid is present at the location (see FIGS. 56 and 57 for details of the consensus protein alignment). The VH Consensus sequences and the VH CDR Consensus sequences are based on analysis of 8 or more aligned VH/VH CDR antibody sequences, as described above. In some cases, the VH/VH CDR Consensus sequence is based on analysis of 25 or more, 50 or more, 75 or more, or 100 or more aligned VH antibody sequences. In one case, the VH/VH CDR Consensus sequence is based on analysis of 149 aligned VH antibody sequences.

Various embodiments of Variable Light chain (VL) Consensus amino acid sequences of the present invention are set forth in Table 20A of FIG. 55 (CDRs are underlined, with the first being CDR1). Various embodiments of VL CDR Consensus amino acid sequences of the present invention are set forth in Tables 20B and 20C of FIG. 55. As mentioned above, in some cases, an "X" is present in the amino acid sequences set forth in Tables 20A and 20B which signifies that more than one amino acid (or no amino acid) may be present at this location (see FIGS. 56 and 57 for details of the consensus protein alignment). In some cases a "-" is present in Table 20A (which is the result of the consensus alignment) and signifies that no amino acid is present at the location (see FIGS. 56 and 57 for details of the consensus protein alignment). The VL Consensus sequences and the VL CDR Consensus sequences are based on analysis of 8 or more aligned VL/VL CDR antibody sequences, as described above. In some cases, the VL/VL CDR Consensus sequence is based on analysis of 25 or more, 50 or more, 75 or more, or 100 or more, 125 or more, or 150 or more aligned VL antibody sequences. In one case, the VL/VL CDR Consensus sequence is based on analysis of 209 aligned VL antibody sequences.

As discussed above, the consensus sequences in certain embodiments can comprise substitutions, deletions, or additions/insertions at different positions in the sequence. Specific examples of these substitutions, deletions, or additions/insertions can be found in Tables 19C and 20C of FIG. 55, as well as Tables 21-48 of FIG. 56 and Tables 49-134 of FIG. 57, all of which are included herein. However, in no way should the amino acid substitutions, deletions, or additions/insertions exemplified in Tables 19A-C and 20A-C in FIG. 55 or in Tables 21-48 in FIG. 56 or in Tables 49-134 in FIG. 57 be construed to limit the invention to only those amino acid substitutions, deletions, or additions at any position in the identified consensus sequences (VH, VL and/or CDRs) with any amino acid is contemplated herein.

In certain embodiments, the antigen binding proteins of the invention comprise 3 VH CDRs and 3 VL CDRs, wherein at least one VH CDR is a VH1 CDR selected from Table 19B or Table 19C as depicted in FIG. 55. In certain embodiments, the antigen binding proteins of the invention comprise 3 VH CDRs and 3 VL CDRs, wherein at least one VH CDR is a VH2 CDR selected from Table 19B or Table 19C as depicted in FIG. 55. In certain embodiments, the antigen binding proteins of the invention comprise 3 VH CDRs and 3 VL CDRs, wherein at least one VH CDR is a VH3 CDR selected from Table 19B or Table 19C as depicted in FIG. 55. In certain embodiments, the antigen binding proteins of the invention comprise 3 VH CDRs and 3 VL CDRs, wherein the VH1 CDR, the VH2 CDR and the VH3 CDR is selected from Table 19B or Table 19C as depicted in FIG. 55.

In certain embodiments, the antigen binding proteins of the invention comprise 3 VH CDRs and 3 VL CDRs, wherein at least one VL CDR is a VL1 CDR selected from Table 20B or Table 20C as depicted in FIG. 55. In certain embodiments, the antigen binding proteins of the invention comprise 3 VH CDRs and 3 VL CDRs, wherein at least one VL CDR is a VL2 CDR selected from Table 20B or Table 20C as depicted in FIG. 55. In certain embodiments, the antigen binding proteins of the invention comprise 3 VH CDRs and 3 VL CDRs, wherein at least one VL CDR is a VL3 CDR selected from Table 20B or Table 20C as depicted in FIG. 55. In certain embodiments, the antigen binding proteins of the invention comprise 3 VH CDRs and 3 VL CDRs, wherein the VL1 CDR, the VL2 CDR and the VL3 CDR is selected from Table 20B or Table 20C as depicted in FIG. 55.

In some embodiments, antigen binding proteins comprise no more than one, two, three, four, five, or six amino acid additions, deletions or substitutions of a VH. In some embodiments, antigen binding proteins comprise no more than one, two, three, four, five, or six amino acid additions, deletions or substitutions of a VL. In further embodiments, antigen binding proteins comprise no more than one, two, three, four, five, or six amino acid additions, deletions or substitutions within a VH1 CDR. In further embodiments, antigen binding proteins comprise no more than one, two, three, four, five, or six amino acid additions, deletions or substitutions within a VH2 CDR. In further embodiments, antigen binding proteins comprise no more than one, two, three, four, five, or six amino acid additions, deletions or substitutions within a VH3 CDR. In further embodiments, antigen binding proteins comprise no more than one, two, three, four, five, or six amino acid additions, deletions or substitutions within a VL1 CDR. In further embodiments, antigen binding proteins comprise no more than one, two, three, four, five, or six amino acid additions, deletions or substitutions within a VL2 CDR. In further embodiments, antigen binding proteins comprise no more than one, two, three, four, five, or six amino acid additions, deletions or substitutions within a VL3 CDR.

In some embodiments, antigen binding proteins comprise no more than one, two, three, four, five, or six amino acid additions, deletions or substitutions of a VH consensus sequence. In some embodiments, antigen binding proteins comprise no more than one, two, three, four, five, or six amino acid additions, deletions or substitutions of a VL consensus sequence. In further embodiments, antigen binding proteins comprise no more than one, two, three, four, five, or six amino acid additions, deletions or substitutions within a VH1 CDR Consensus sequence. In further embodiments, antigen binding proteins comprise no more than one, two, three, four, five, or six amino acid additions, deletions or substitutions within a VH2 CDR Consensus sequence. In further embodiments, antigen binding proteins comprise no more than one, two, three, four, five, or six amino acid additions, deletions or substitutions within a VH3 CDR Consensus sequence. In further embodiments, antigen binding proteins comprise no more than one, two, three, four, five, or six amino acid additions, deletions or substitutions within a VL1 CDR Consensus sequence. In further embodiments, antigen binding proteins comprise no more than one, two, three, four, five, or six amino acid additions, deletions or substitutions within a VL2 CDR Consensus sequence. In further embodiments, antigen binding proteins comprise no more than one, two, three, four, five, or six amino acid additions, deletions or substitutions within a VL3 CDR Consensus sequence.

In some embodiments, framework consensus sequences are encompassed by the present invention. Examples of these framework consensus sequences and additions, deletions or substitutions are shown in Tables 21-48 in FIG. 56 and Tables 49-134 in FIG. 57 herein.

In a further embodiment, the antigen binding proteins of the invention bind to ASGR of different species, including, but not limited to, human, cynomolgus, porcine, canine, murine and rat. In some embodiments, the antigen binding proteins of the invention bind to human. In some embodiments, the antigen binding proteins of the invention bind to cynomolgus ASGR. In some embodiments, the antigen binding proteins of the invention bind to porcine ASGR. In some embodiments, the antigen binding proteins of the invention bind to canine ASGR. In some embodiments, the antigen binding proteins of the invention bind to murine ASGR. In some embodiments, the antigen binding proteins of the invention bind to rat ASGR. In some embodiments, the antigen binding proteins specifically bind to ASGR of the different species.

In some embodiments, the antigen binding proteins of the invention bind to ASGR-1 of different species, including, but not limited to, human, cynomolgus, porcine, canine, murine and rat. In some embodiments, the antigen binding proteins of the invention bind to human ASGR-1. In some embodiments, the antigen binding proteins of the invention bind to cynomolgus ASGR-1. In some embodiments, the antigen binding proteins of the invention bind to porcine ASGR-1. In some embodiments, the antigen binding proteins of the invention bind to canine ASGR-1. In some embodiments, the antigen binding proteins of the invention bind to murine ASGR-1. In some embodiments, the antigen binding proteins of the invention bind to rat ASGR-1. In some embodiments, the antigen binding proteins specifically bind to ASGR-1 of the different species.

In some embodiments, the antigen binding proteins of the invention binds to ASGR-2 of different species, including, but not limited to, human, cynomolgus, porcine, canine, murine and rat. In some embodiments, the antigen binding proteins of the invention bind to human ASGR-2. In some embodiments, the antigen binding proteins of the invention bind to cynomolgus ASGR-2. In some embodiments, the antigen binding proteins of the invention bind to porcine ASGR-2. In some embodiments, the antigen binding proteins of the invention bind to canine ASGR-2. In some embodiments, the antigen binding proteins of the invention bind to murine ASGR-2. In some embodiments, the antigen binding proteins of the invention bind to rat ASGR-2. In some embodiments, the antigen binding proteins specifically bind to ASGR-2 of the different species.

In some embodiments, the antigen binding proteins of the invention bind to ASGR, ASGR-1 and/or ASGR-2 from two or more different species, and/or bind ASGR, ASGR-1 and/or ASGR-2 from the same species. For example, but not limited to: an antibody that binds human and cynomolgus ASGR-1; an antibody that binds to human, cynomolgus and porcine ASGR-1; an antibody that binds to human, cynomolgus, rat and murine ASGR-2; an antibody that binds human ASGR-1 and human ASGR-2; an antibody that binds human and cynomolgus ASGR-1 and ASGR-2. In some embodiments, the antigen binding proteins specifically bind to ASGR, ASGR-1 and/or ASGR-2 from two or more different species and/or specifically bind ASGR, ASGR-1 and/or ASGR-2 from the same species.

As discussed herein, the ASGR receptor, and ASGR-1 and/or ASGR-2 separately, internalize into the cell upon ligand binding. Accordingly, in certain embodiments, the invention provides antigen binding proteins that inhibit or reduce internalization of ASGR, ASGR-1 and/or ASGR-2. In certain embodiments, the antigen binding proteins of the invention reduce ligand binding and also inhibit internalization of ASGR, ASGR-1 and/or ASGR-2. In some embodiments, the antigen binding proteins of the invention inhibit internalization without necessarily inhibiting ligand binding.

In some embodiments, the antigen binding proteins (e.g., antibodies) of the invention are pH and/or calcium insensitive molecules, as well as binding to ASGR, ASGR-1 and/or ASGR-2 and inhibiting the binding to a ligand. It is envisioned that these properties are desired to reduce or prevent the molecule from disassociating from the receptor during the endocytotic process in order to extend the half-life of the molecule. In some embodiments, the antigen binding proteins (e.g., antibodies) with pH-independent binding to its antigen such that the affinity for the antigen binding at physiological pH (i.e., pH 7.4) is similar to that at endosomal pH (i.e., pH 5.5-6.0). In some embodiments, the antigen binding proteins (e.g., antibodies) with calcium-independent binding to its antigen such that the affinity for the antigen binding at assay conditions (i.e., 1 mM calcium) is similar to that in the absence of exogenously added calcium. In some embodiments, the antigen binding proteins with both pH- and calcium-independent binding to its antigen such that the affinity for the antigen binding at physiologic pH and in the presence of calcium is similar to that at endosomal pH (i.e., pH 5.5-6.0) and in the absence of calcium. Any number of methods known to one skilled in the art can be used to measure pH and/or calcium insensitivity, such as the method described in Example 7C below.

ASGR-1, an asialoglycoprotein receptor, contains an N-term cytosolic domain, a transmembrane domain, a stalk region and a carbohydrate recognition domain (CRD) (alternatively known as the carbohydrate binding domain, or "CBD"). The carbohydrate recognition domain ("CRD") structure of ASGR-1 is reported in literature (M. Meier et al, JMB (2000)300, 857-865). The structure of ASGR-1 at a higher resolution than reported, and also when bound to various ligands (e.g., sugars including but not limited to lactose, galactose, and/or GalNAc or glycoproteins displaying such sugars including but not limited to fetuin, orosomucoid and/or alkaline phosphatase) is provided herein (see Example 10 and FIGS. 18-21 herein). Given the importance of this domain to the function of ASGR-1, in some embodiments, it is desirable to target this domain with the antigen binding proteins of the present invention.

Accordingly, in some embodiments, the antigen binding proteins of the invention bind to the CBD of ASGR-1. In certain embodiments, the antigen binding proteins of the invention bind to the CBD of human ASGR-1. In certain embodiments, the antigen binding proteins of the invention bind to the CBD of SEQ ID NO:5. In some embodiments, the antigen binding proteins of the invention bind to amino acid residues selected from the group consisting of 148-291, 149-291, 150-291, 151-291, 152-291, 153-291, and 154-291 of SEQ ID NO:5. In some embodiments, the invention comprises an isolated antigen binding protein that binds to human ASGR-1 CBD within Helix α-1 or Helix α-2. In some embodiments, the invention comprises an isolated antigen binding protein that binds to human ASGR-1 CBD within residues 174-186 of SEQ ID NO:5. In some embodiments, the invention comprises an isolated antigen binding protein that binds to human ASGR-1 CBD within residues 194-206 of SEQ ID NO:5. In some embodiments, the invention comprises an isolated antigen binding protein that binds to human ASGR-1 CBD at the same or overlapping binding site as where a ligand binds (e.g., sugars including but not limited to lactose, galactose, and/or GalNAc or glycoproteins displaying such sugars including but not limited to fetuin, orosomucoid and/or alkaline phosphatase or other sugars and glycoproteins capable of binding to ASGR, ASGR-1, and/or ASGR-2). In some embodiments, the invention comprises an isolated antigen binding protein that binds to human ASGR-1 CBD within residues 237-273 or residues 240-267 of SEQ ID NO:5. In some embodiments, the antigen binding proteins of the invention bind to the CBD of cynomolgus ASGR-1. In some embodiments, the antigen binding proteins of the invention bind to the CBD of porcine ASGR-1. In some embodiments, the antigen binding proteins of the invention bind to the CBD of canine ASGR-1. In some embodiments, the antigen binding proteins of the invention bind to the CBD of murine ASGR-1. In yet some embodiments, the antigen binding proteins of the invention bind to the CBD of rat ASGR-1. In yet some embodiments, the antigen binding proteins of the invention bind to the CBD of two or more different ASGR-1 species, for example, but not limited to, human ASGR-1 and cynomolgus ASGR-1, or human ASGR-1, cynomolgus ASGR-1 and canine ASGR-1, or human ASGR-1 and murine ASGR-1.

In further embodiments, the antigen binding proteins of the invention bind to ASGR-1 and inhibit binding of ligand to ASGR-1. In a specific embodiment, the ligands that are inhibited include, but are not limited to, sugars including but not limited to lactose, galactose, and/or GalNAc or glycoproteins displaying such sugars including but not limited to fetuin, orosomucoid and/or alkaline phosphatase or other sugars and glycoproteins capable of binding to ASGR, ASGR-1, and/or ASGR-2.

The tyrosine at position 272 of murine ASGR-1 (position 273 of human ASGR-1 (SEQ ID NO:5)) appears to be important for protein stability, as it displays hydrogen bonding to D266 of murine ASGR-1 and several van der Waals contacts to other residues of murine ASGR-1 (N208, W210, H256, and R270). Additionally, by analogy with other lectins, Y272 of murine ASGR-1 may play a role in carbohydrate binding and function of ASGR-1. Accordingly, in some embodiments, the antigen binding proteins of the invention bind to or interact with Y273 of human ASGR-1. In some embodiments, the antigen binding proteins of the invention bind to ASGR-1 at an epitope that comprises Y273 of human ASGR-1. In some embodiments, the antigen binding proteins of the invention bind to ASGR-1 at an epitope that results in Y273 of human ASGR-1 being unable to take part in binding ligand.

Analysis of the crystal structure of hASGR-1 revealed specific amino acids that are involved in the interaction between hASGR-1 and the ligands (e.g., sugars including but not limited to lactose, galactose, and/or GalNAc or glycoproteins displaying such sugars including but not limited to fetuin, orosomucoid and/or alkaline phosphatase). Accordingly, in further embodiments, the antigen binding proteins of the invention bind to or interact with at least one of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least one of Q240, D242, W244, E253, N265, D266, D267, N209, R237, P238, E239, P241, D243, Y245, G246, H247, G252, C255, H257, T259, D260, V268, R271, Y273, F258, R263, or W264. In further embodiments, the antigen binding proteins of the invention bind to hASGR-1and block or reduce the binding or interaction of at least one of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., sugars including but not limited to lactose, galactose, and/or GalNAc or glycoproteins displaying such sugars including but not limited to fetuin, orosomucoid and/or alkaline phosphatase).

In further embodiments, the antigen binding proteins of the invention bind to or interact with at least one of Q240, D242, W244, E253, N265, D266, D267, R237, P238, H257, T259, or Y273. In some embodiments, the antigen binding proteins of the invention bind at an epitope comprising at least one of Q240, D242, W244, E253, N265, D266, D267, R237, P238, H257, T259, or Y273. In further embodiments, the antigen binding proteins of the invention bind to hASGR-1 and block or reduce the binding or interaction of at least one of Q240, D242, W244, E253, N265, D266, D267, R237, P238, H257, T259, or Y273 with a ligand (e.g., sugars including but not limited to lactose, galactose, and/or GalNAc or glycoproteins displaying such sugars including but not limited to fetuin, orosomucoid and/or alkaline phosphatase).

In some embodiments, the antigen binding proteins of the invention bind to or interact with at least two of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least three of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least four of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least five of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least six of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least seven of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least eight of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least nine of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least ten of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least eleven of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least twelve of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least thirteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least fourteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least fifteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least sixteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least seventeen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least eighteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least nineteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind to or interact with at least twenty of Q240, D242, W244, E253, N265, D266, D267, N209, R237, P238, E239, P241, D243, Y245, G246, H247, G252, C255, H257, T259, D260, V268, R271, Y273, F258, R263, or W264.

In some embodiments, the antigen binding proteins of the invention bind to or interact with at least two of Q240, D242, W244, E253, N265, D266, D267, R237, P238, H257, T259, or Y273. In some embodiments, the antigen binding proteins of the invention bind to or interact with at least three of Q240, D242, W244, E253, N265, D266, D267, R237, P238, H257, T259, or Y273. In some embodiments, the antigen binding proteins of the invention bind to or interact with at least four of Q240, D242, W244, E253, N265, D266, D267, R237, P238, H257, T259, or Y273. In some embodiments, the antigen binding proteins of the invention bind to or interact with at least five of Q240, D242, W244, E253, N265, D266, D267, R237, P238, H257, T259, or Y273. In some embodiments, the antigen binding proteins of the invention bind to or interact with at least six of Q240, D242, W244, E253, N265, D266, D267, R237, P238, H257, T259, or Y273. In some embodiments, the antigen binding proteins of the invention bind to or interact with at least seven of Q240, D242, W244, E253, N265, D266, D267, R237, P238, H257, T259, or Y273. In some embodiments, the antigen binding proteins of the invention bind to or interact with at least eight of Q240, D242, W244, E253, N265, D266, D267, R237, P238, H257, T259, or Y273. In some embodiments, the antigen binding proteins of the invention bind to or interact with at least nine of Q240, D242, W244, E253, N265, D266, D267, R237, P238, H257, T259, or Y273. In some embodiments, the antigen binding proteins of the invention bind to or interact with at least ten of Q240, D242, W244, E253, N265, D266, D267, R237, P238, H257, T259, or Y273. In some embodiments, the antigen binding proteins of the invention bind to or interact with at least eleven of Q240, D242, W244, E253, N265, D266, D267, R237, P238, H257, T259, or Y273. In some embodiments, the antigen binding proteins of the invention bind to or interact with at least all of Q240, D242, W244, E253, N265, D266, D267, R237, P238, H257, T259, or Y273.

In some embodiments, the antigen binding proteins of the invention bind at an epitope comprising at least two of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least three of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least four of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least five of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least six of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least seven of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least eight of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least nine of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least ten of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least eleven of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least twelve of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least thirteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least fourteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least fifteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least sixteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least seventeen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least eighteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least nineteen of Q240, D242, W244, E253, N265, D266, D267, N209, R237, P238, E239, P241, D243, Y245, G246, H247, G252, C255, H257, T259, D260, V268, R271, Y273, F258, R263, or W264. In some embodiments, the antigen binding proteins of the invention bind at an epitope comprising at least twenty of Q240, D242, W244, E253, N265, D266, D267, N209, R237, P238, E239, P241, D243, Y245, G246, H247, G252, C255, H257, T259, D260, V268, R271, Y273, F258, R263, or W264.

In some embodiments, the antigen binding proteins of the invention bind at an epitope comprising at least two of Q240, D242, W244, E253, N265, D266, D267, R237, P238, H257, T259, or Y273. In some embodiments, the antigen binding proteins of the invention bind at an epitope comprising at least three of Q240, D242, W244, E253, N265, D266, D267, R237, P238, H257, T259, or Y273. In some embodiments, the antigen binding proteins of the invention bind at an epitope comprising at least four of Q240, D242, W244, E253, N265, D266, D267, R237, P238, H257, T259, or Y273. In some embodiments, the antigen binding proteins of the invention bind at an epitope comprising at least five of Q240, D242, W244, E253, N265, D266, D267, R237, P238, H257, T259, or Y273. In some embodiments, the antigen binding proteins of the invention bind at an epitope comprising at least six of Q240, D242, W244, E253, N265, D266, D267, R237, P238, H257, T259, or Y273. In some embodiments, the antigen binding proteins of the invention bind at an epitope comprising at least seven of Q240, D242, W244, E253, N265, D266, D267, R237, P238, H257, T259, or Y273. In some embodiments, the antigen binding proteins of the invention bind at an epitope comprising at least eight of Q240, D242, W244, E253, N265, D266, D267, R237, P238, H257, T259, or Y273. In some embodiments, the antigen binding proteins of the invention bind at an epitope comprising at least nine of Q240, D242, W244, E253, N265, D266, D267, R237, P238, H257, T259, or Y273. In some embodiments, the antigen binding proteins of the invention bind at an epitope comprising at least ten of Q240, D242, W244, E253, N265, D266, D267, R237, P238, H257, T259, or Y273. In some embodiments, the antigen binding proteins of the invention bind at an epitope comprising at least eleven of Q240, D242, W244, E253, N265, D266, D267, R237, P238, H257, T259, or Y273. In some embodiments, the antigen binding proteins of the invention bind at an epitope comprising all of Q240, D242, W244, E253, N265, D266, D267, R237, P238, H257, T259, or Y273.

In further embodiments, the antigen binding proteins of the invention bind to hASGR-1 and block or reduce the binding or interaction of at least two of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least three of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least four of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g, sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least five of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g, sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least six of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g, sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least seven of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least eight of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g, sugars including but not limited to lactose, galactose, and/or GalNAc or glycoproteins displaying such sugars including but not limited to fetuin, orosomucoid and/or alkaline phosphatase). In further embodiments, the antigen binding proteins of the invention bind to hASGR-1 and block or reduce the binding or interaction of at least nine of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least ten of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least eleven of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least twelve of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least thirteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least fourteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least fifteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least sixteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least seventeen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least eighteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least nineteen of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc). In further embodiments, the antigen binding proteins of the invention bind to hASGR-1 and block or reduce the binding or interaction of at least twenty of Q240, D242, W244, E253, N265, D266, D267, N209, R237, P238, E239, P241, D243, Y245, G246, H247, G252, C255, H257, T259, D260, V268, R271, Y273, F258, R263, or W264 with a ligand (e.g., lactose, galactose and/or GalNAc).

In further embodiments, the antigen binding proteins of the invention bind to hASGR-1 and block or reduce the binding or interaction of at least two of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least three of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least four of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least five of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least six of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least seven of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least eight of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least nine of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least ten of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of at least eleven of Q240, D242, W244, E253, N265, D266, D267, R237, P238, H257, T259, or Y273 with a ligand (e.g., lactose, galactose and/or GalNAc). In further embodiments, the antigen binding proteins of the invention bind to hASGR-1 and block or reduce the binding or interaction of all of Q240, D242, W244, E253, N265, D266, D267, R237, P238, H257, T259, or Y273 with a ligand (e.g., lactose, galactose and/or GalNAc).

In order to relate unique antigen binding protein sequence features to specific functions or binding characteristics, sequences from antigen binding proteins of the invention from various characterization bins can be analyzed. For example, antigen binding proteins of the invention can be tested for their ability to bind a variety of binning probes (e.g., membrane preps from cells expressing ASGR-1 from different species or soluble huASGR-1). For each unique binding bin, the heavy and light chain sequences from each of the antigen binding proteins can be compared and claded based on, for example: 1. the unique VDJ and VJ rearrangements; 2. divergence from germline (ie. unique somatic hypermutation); and 3. relatedness to other antigen binding proteins of the same bin. Accordingly, in certain embodiments, the antigen binding proteins comprising the same or similar sequence features and patterns, will have substantially the same or similar binding characteristics. In specific embodiments, these antigen binding proteins can bind to the same or similar epitope with varying affinities.

The exemplary antigen binding proteins described herein have properties based on the epitope on ASGR, ASGR-1 and/or ASGR-2 that is bound by the antigen binding protein. The term "epitope" includes any determinant capable of being bound by an antigen binding protein, such as an antibody. An epitope is a region of an antigen that is bound by, or interacts with, an antigen binding protein that targets that antigen, and when the antigen is a protein, includes specific amino acids that directly contact, or interact with, the antigen binding protein. An epitope can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is a group of discontinuous amino acids (e.g., in a polypeptide, amino acid residues that are not contiguous in the polypeptide's primary sequence but that, in the context of the polypeptide's tertiary and quaternary structure, are near enough to each other to be bound by an antigen binding protein). Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins specific for a particular target molecule will preferentially recognize an epitope on the target molecule in a complex mixture of proteins and/or macromolecules.

Methods of characterizing the epitope bound by an antigen binding protein are well known in the art, including, but not limited to, binning (competition and/or cross-competition) (Miller et al "Epitope binning of murine monoclonal antibodies by a multiplexed pairing assay" *J Immunol Methods* (2011) 365, 118-25), peptide mapping (e.g., PEPSPOT™) (Albert et al "The B-cell Epitope of the Monoclonal Anti-Factor VIII Antibody ESH8 Characterized by Peptide Array Analysis" 2008 *Thromb Haemost* 99, 634-7), mutagenesis methods such as chimeras (Song et al "Epitope Mapping of Ibalizumab, a Humanized Anti-CD4 Monoclonal Antibody with Anti-HIV-1 Activity in Infected Patients" *J. Virol.* (2010) 84, 6935-6942), alanine scanning (Cunningham and Wells "High-resolution epitope mapping of HGH-receptor interactions by alanine-scanning mutagenesis" *Science* (1989) 244, 1081-1085), arginine scanning (Lim et al "A diversity of antibody epitopes can induce signaling through the erythropoietin receptor" *Biochemistry* (2010) 49, 3797-3804), HD exchange methods (Coates et al "Epitope mapping by amide hydrogen/deuterium exchange coupled with immobilization of antibody, on-line proteolysis, liquid chromatography and mass spectrometry" *Rapid Commun. Mass Spectrom.* (2009) 23 639-647), NMR cross saturation methods (Morgan et al "Precise epitope mapping of malaria parasite inhibitory antibodies by TROSY NMR cross-saturation" *Biochemistry* (2005) 44, 518-23), and crystallography (Gerhardt et al "Structure of IL-17A in complex with a potent, fully human neutralizing antibody" *J. Mol. Biol* (2009) 394, 905-21). The methods vary in the level of detail they provide as to the amino acids comprising the epitope.

Antigen binding proteins of the present invention include those that have an identical or overlapping epitope with an exemplary antigen binding protein described in Tables 2-7. In some embodiments, the antigen binding protein has an identical epitope as to the exemplary antigen binding proteins. In other embodiments, the antigen binding protein binds only a subset of the same amino acids as the exemplary antigen binding protein. In some embodiments, antigen binding proteins that might bind to any of the epitopes that are bound by the antibodies listed in Tables A, B, C or 6 are especially useful.

In certain embodiments, the antigen binding proteins of the present invention have an identical or overlapping epitope to the antigen binding proteins in Table 2-7 and comprise a) a light chain variable domain having at least 90% identity, at least 95% identity, or is identical to the amino acid sequence of the antigen binding proteins described in Tables 2-7; b) a heavy chain variable domain having at least 90% identity, at least 95% identity, or is identical to the amino acid sequence of the antigen binding proteins set forth in Tables 2-7; or c) the light chain variable domain of a) and the heavy chain variable domain of b).

In certain embodiments, the antigen binding protein of the present invention has an identical or overlapping epitope to the antigen binding proteins selected from the group consisting of 25A4, 4H6, 4A2, 5E5, 7E11, 54E9, 22G5, 194A4, 218G4, 176H4 and 194C10 wherein the antigen binding protein comprises a light chain variable domain having at least 90% identity, at least 95% identity, or is identical to the amino acid sequence of 25A4 and a heavy chain variable domain having at least 90% identity, at least 95% identity, or is identical to the amino acid sequence of 25A4; those comprising a light chain variable domain having at least 90% identity, at least 95% identity, or is identical to the amino acid sequence of 4H6 and a heavy chain variable domain having at least 90% identity, at least 95% identity, or is identical to the amino acid sequence of 4H6; those comprising a light chain variable domain having at least 90% identity, at least 95% identity, or is identical to the amino acid sequence of 4A2 and a heavy chain variable domain having at least 90% identity, at least 95% identity, or is identical to the amino acid sequence of 4A2; those comprising a light chain variable domain having at least 90% identity, at least 95% identity, or is identical to the amino acid sequence of 5E5 and a heavy chain variable domain having at least 90% identity, at least 95% identity, or is identical to the amino acid sequence of 5E5; those comprising a light chain variable domain having at least 90% identity, at least 95% identity, or is identical to the amino acid sequence of 7E11 and a heavy chain variable domain having at least 90% identity, at least 95% identity, or is identical to the amino acid sequence of 7E11; those comprising a light chain variable domain having at least 90% identity, at least 95% identity, or is identical to the amino acid sequence of 54E9 and a heavy chain variable domain having at least 90% identity, at least 95% identity, or is identical to the amino acid sequence of 54E9; those comprising a light chain variable domain having at least 90% identity, at least 95% identity, or is identical to the amino acid sequence of 22G5 and a heavy chain variable domain having at least 90% identity, at least 95% identity, or is identical to the amino acid sequence of 22G5; those comprising a light chain variable domain having at least 90% identity, at least 95% identity, or is identical to the amino acid sequence of 194A4 and a heavy chain variable domain having at least 90% identity, at least 95% identity, or is identical to the amino acid sequence of 194A4; those comprising a light chain variable domain having at least 90% identity, at least 95% identity, or is identical to the amino acid sequence of 218G4G4 and a heavy chain variable domain having at least 90% identity, at least 95% identity, or is identical to the amino acid sequence of 218G4; those comprising a light chain variable domain having at least 90% identity, at least 95% identity, or is identical to the amino acid sequence of 176H4 and a heavy chain variable domain having at least 90% identity, at least 95% identity, or is identical to the amino acid sequence of 176H4; those comprising a light chain variable domain having at least 90% identity, at least 95% identity, or is identical to the amino acid sequence of 194C10 and a heavy chain variable domain having at least 90% identity, at least 95% identity, or is identical to the amino acid sequence of 194C10.

In certain embodiments, the ASGR-1 antigen binding protein of the invention has an identical or overlapping epitope as the antibodies in Tables 2-7, and comprises a light chain variable domain comprising an LCDR1 having no more than three amino acid additions, deletions, or substitutions from the LCDR1 sequence set forth in Table 2; an LCDR2 having no more than three amino acid additions, deletions, or substitutions from the LCDR2 sequence set forth in Table 2; and an LCDR3 having no more than three amino acid additions, deletions, or substitutions from the LCDR3 sequence set forth in Table 2; and a heavy chain variable domain comprising a) an HCDR1 having no more than three amino acid additions, deletions, or substitutions from the HCDR1 sequence set forth in Table 2; an HCDR2 having no more than three amino acid additions, deletions, or substitutions from the HCDR2 sequence set forth in Table 2; and an HCDR3 having no more than three amino acid additions, deletions, or substitutions from the HCDR3 sequence set forth in Table 2.

In certain embodiments, the ASGR-1 antigen binding protein of the invention has an identical or overlapping epitope as the antibodies in Tables A, B, C or 6, and comprises a light chain variable domain comprising an LCDR1 having no more than three amino acid additions, deletions, or substitutions from the LCDR1 sequence set forth in Tables A, B, C or 6; an LCDR2 having no more than three amino acid additions, deletions, or substitutions from the LCDR2 sequence set forth in Tables A, B, C or 6; and an LCDR3 having no more than three amino acid additions, deletions, or substitutions from the LCDR3 sequence set forth in Tables A, B, C or 6; and a heavy chain variable domain comprising a) an HCDR1 having no more than three amino acid additions, deletions, or substitutions from the HCDR1 sequence set forth in Tables A, B, C or 6; an HCDR2 having no more than three amino acid additions, deletions, or substitutions from the HCDR2 sequence set forth in Tables A, B, C or 6; and an HCDR3 having no more than three amino acid additions, deletions, or substitutions from the HCDR3 sequence set forth in Tables A, B, C or 6.

In certain embodiments, the ASGR-1 antigen binding protein of the invention has an identical or overlapping epitope as the antibody, 25A4, and comprises a light chain variable domain comprising an LCDR1 having no more than three amino acid additions, deletions, or substitutions from the LCDR1 sequence set forth in SEQ ID NO:480; an LCDR2 having no more than three amino acid additions, deletions, or substitutions from the LCDR2 sequence set forth in SEQ ID NO:8492; and an LCDR3 having no more than three amino acid additions, deletions, or substitutions from the LCDR3 sequence set forth in SEQ ID NO:16504; and a heavy chain variable domain comprising an HCDR1 having no more than three amino acid additions, deletions, or substitutions from the HCDR1 sequence set forth in SEQ ID NO:4488; an HCDR2 having no more than three amino acid additions, deletions, or substitutions from the HCDR2 sequence set forth in SEQ ID NO:12500; and an HCDR3 having no more than three amino acid additions, deletions, or substitutions from the HCDR3 sequence set forth in SEQ ID NO:20512.

In certain embodiments, the ASGR-1 antigen binding protein of the invention has an identical or overlapping epitope as the antibody, 4H6, and comprises a light chain variable domain comprising an LCDR1 having no more than three amino acid additions, deletions, or substitutions from the LCDR1 sequence set forth in SEQ ID NO:894; an LCDR2 having no more than three amino acid additions, deletions, or substitutions from the LCDR2 sequence set forth in SEQ ID NO:8906; and an LCDR3 having no more than three amino acid additions, deletions, or substitutions from the LCDR3 sequence set forth in SEQ ID NO:16918; and a heavy chain variable domain comprising an HCDR1 having no more than three amino acid additions, deletions, or substitutions from the HCDR1 sequence set forth in SEQ ID NO:4902; an HCDR2 having no more than three amino acid additions, deletions, or substitutions from the HCDR2 sequence set forth in SEQ ID NO:12914; and an HCDR3 having no more than three amino acid additions, deletions, or substitutions from the HCDR3 sequence set forth in SEQ ID NO:20926.

In certain embodiments, the ASGR-1 antigen binding protein of the invention has an identical or overlapping epitope as the antibody, 4A2, and comprises a light chain variable domain comprising an LCDR1 having no more than three amino acid additions, deletions, or substitutions from the LCDR1 sequence set forth in SEQ ID NO:1130; an LCDR2 having no more than three amino acid additions, deletions, or substitutions from the LCDR2 sequence set forth in SEQ ID NO:9142; and an LCDR3 having no more than three amino acid additions, deletions, or substitutions from the LCDR3 sequence set forth in SEQ ID NO:17154; and a heavy chain variable domain comprising an HCDR1 having no more than three amino acid additions, deletions, or substitutions from the HCDR1 sequence set forth in SEQ ID NO:5136; an HCDR2 having no more than three amino acid additions, deletions, or substitutions from the HCDR2 sequence set forth in SEQ ID NO:13148; and an HCDR3 having no more than three amino acid additions, deletions, or substitutions from the HCDR3 sequence set forth in SEQ ID NO:21160.

In certain embodiments, the ASGR-1 antigen binding protein of the invention has an identical or overlapping epitope as the antibody, 5E5, and comprises a light chain variable domain comprising an LCDR1 having no more than three amino acid additions, deletions, or substitutions from the LCDR1 sequence set forth in SEQ ID NO:974; an LCDR2 having no more than three amino acid additions, deletions, or substitutions from the LCDR2 sequence set forth in SEQ ID NO:8986; and an LCDR3 having no more than three amino acid additions, deletions, or substitutions from the LCDR3 sequence set forth in SEQ ID NO:16998; and a heavy chain variable domain comprising an HCDR1 having no more than three amino acid additions, deletions, or substitutions from the HCDR1 sequence set forth in SEQ ID NO:4982; an HCDR2 having no more than three amino acid additions, deletions, or substitutions from the HCDR2 sequence set forth in SEQ ID NO:12994; and an HCDR3 having no more than three amino acid additions, deletions, or substitutions from the HCDR3 sequence set forth in SEQ ID NO:21006.

In certain embodiments, the ASGR-1 antigen binding protein of the invention has an identical or overlapping epitope as the antibody, 7E11, and comprises a light chain variable domain comprising an LCDR1 having no more than three amino acid additions, deletions, or substitutions from the LCDR1 sequence set forth in SEQ ID NO:872; an LCDR2 having no more than three amino acid additions, deletions, or substitutions from the LCDR2 sequence set forth in SEQ ID NO:8884; and an LCDR3 having no more than three amino acid additions, deletions, or substitutions from the LCDR3 sequence set forth in SEQ ID NO:16896; and a heavy chain variable domain comprising an HCDR1 having no more than three amino acid additions, deletions, or substitutions from the HCDR1 sequence set forth in SEQ ID NO:4880; an HCDR2 having no more than three amino acid additions, deletions, or substitutions from the HCDR2 sequence set forth in SEQ ID NO:12892; and an HCDR3 having no more than three amino acid additions, deletions, or substitutions from the HCDR3 sequence set forth in SEQ ID NO:20904.

In certain embodiments, the ASGR-1 antigen binding protein of the invention has an identical or overlapping epitope as the antibody, 54E9, and comprises a light chain variable domain comprising an LCDR1 having no more than three amino acid additions, deletions, or substitutions from the LCDR1 sequence set forth in SEQ ID NO:3448; an LCDR2 having no more than three amino acid additions, deletions, or substitutions from the LCDR2 sequence set forth in SEQ ID NO:11460; and an LCDR3 having no more than three amino acid additions, deletions, or substitutions from the LCDR3 sequence set forth in SEQ ID NO:19472; and a heavy chain variable domain comprising an HCDR1 having no more than three amino acid additions, deletions, or substitutions from the HCDR1 sequence set forth in SEQ ID NO:7452; an HCDR2 having no more than three amino acid additions, deletions, or substitutions from the HCDR2 sequence set forth in SEQ ID NO:15464; and an HCDR3 having no more than three amino acid additions, deletions, or substitutions from the HCDR3 sequence set forth in SEQ ID NO:23476.

In certain embodiments, the ASGR-1 antigen binding protein of the invention has an identical or overlapping epitope as the antibody, 22G5, and comprises a light chain variable domain comprising an LCDR1 having no more than three amino acid additions, deletions, or substitutions from the LCDR1 sequence set forth in SEQ ID NO:326; an LCDR2 having no more than three amino acid additions, deletions, or substitutions from the LCDR2 sequence set forth in SEQ ID NO:8338; and an LCDR3 having no more than three amino acid additions, deletions, or substitutions from the LCDR3 sequence set forth in SEQ ID NO:16350; and a heavy chain variable domain comprising an HCDR1 having no more than three amino acid additions, deletions, or substitutions from the HCDR1 sequence set forth in SEQ ID NO:4334; an HCDR2 having no more than three amino acid additions, deletions, or substitutions from the HCDR2 sequence set forth in SEQ ID NO:12346; and an HCDR3 having no more than three amino acid additions, deletions, or substitutions from the HCDR3 sequence set forth in SEQ ID NO:20358.

In certain embodiments, the ASGR-1 antigen binding protein of the invention has an identical or overlapping epitope as the antibody, 194A4, and comprises a light chain variable domain comprising an LCDR1 having no more than three amino acid additions, deletions, or substitutions from the LCDR1 sequence set forth in SEQ ID NO:2780; an LCDR2 having no more than three amino acid additions, deletions, or substitutions from the LCDR2 sequence set forth in SEQ ID NO:10792; and an LCDR3 having no more than three amino acid additions, deletions, or substitutions from the LCDR3 sequence set forth in SEQ ID NO:18804; and a heavy chain variable domain comprising an HCDR1 having no more than three amino acid additions, deletions, or substitutions from the HCDR1 sequence set forth in SEQ ID NO:6786; an HCDR2 having no more than three amino acid additions, deletions, or substitutions from the HCDR2 sequence set forth in SEQ ID NO:14798; and an HCDR3 having no more than three amino acid additions, deletions, or substitutions from the HCDR3 sequence set forth in SEQ ID NO:22810.

In certain embodiments, the ASGR-1 antigen binding protein of the invention has an identical or overlapping epitope as the antibody, 218G4, and comprises a light chain variable domain comprising an LCDR1 having no more than three amino acid additions, deletions, or substitutions from the LCDR1 sequence set forth in SEQ ID NO:3746; an LCDR2 having no more than three amino acid additions, deletions, or substitutions from the LCDR2 sequence set forth in SEQ ID NO:11758; and an LCDR3 having no more than three amino acid additions, deletions, or substitutions from the LCDR3 sequence set forth in SEQ ID NO:19770; and a heavy chain variable domain comprising an HCDR1 having no more than three amino acid additions, deletions, or substitutions from the HCDR1 sequence set forth in SEQ ID NO:7750; an HCDR2 having no more than three amino acid additions, deletions, or substitutions from the HCDR2 sequence set forth in SEQ ID NO:15762; and an HCDR3 having no more than three amino acid additions, deletions, or substitutions from the HCDR3 sequence set forth in SEQ ID NO:23774.

In certain embodiments, the ASGR-1 antigen binding protein of the invention has an identical or overlapping epitope as the antibody, 176H4, and comprises a light chain variable domain comprising an LCDR1 having no more than three amino acid additions, deletions, or substitutions from the LCDR1 sequence set forth in SEQ ID NO:2502; an LCDR2 having no more than three amino acid additions, deletions, or substitutions from the LCDR2 sequence set forth in SEQ ID NO:10514; and an LCDR3 having no more than three amino acid additions, deletions, or substitutions from the LCDR3 sequence set forth in SEQ ID NO:18526; and a heavy chain variable domain comprising an HCDR1 having no more than three amino acid additions, deletions, or substitutions from the HCDR1 sequence set forth in SEQ ID NO:6508; an HCDR2 having no more than three amino acid additions, deletions, or substitutions from the HCDR2 sequence set forth in SEQ ID NO:14520; and an HCDR3 having no more than three amino acid additions, deletions, or substitutions from the HCDR3 sequence set forth in SEQ ID NO:22532.

In certain embodiments, the ASGR-1 antigen binding protein of the invention has an identical or overlapping epitope as the antibody, 194C10, and comprises a light chain variable domain comprising an LCDR1 having no more than three amino acid additions, deletions, or substitutions from the LCDR1 sequence set forth in SEQ ID NO:2792; an LCDR2 having no more than three amino acid additions, deletions, or substitutions from the LCDR2 sequence set forth in SEQ ID NO:10804; and an LCDR3 having no more than three amino acid additions, deletions, or substitutions from the LCDR3 sequence set forth in SEQ ID NO:18816; and a heavy chain variable domain comprising an HCDR1 having no more than three amino acid additions, deletions, or substitutions from the HCDR1 sequence set forth in SEQ ID NO:6798; an HCDR2 having no more than three amino acid additions, deletions, or substitutions from the HCDR2 sequence set forth in SEQ ID NO:14810; and an HCDR3 having no more than three amino acid additions, deletions, or substitutions from the HCDR3 sequence set forth in SEQ ID NO:22822.

Antigen binding proteins that have an identical or overlapping epitope will often compete for binding to the antigen, ASGR, ASGR1 and/or ASGR2. Thus, in certain embodiments, an antigen binding protein (e.g., antibody or antibody fragment thereof) of the invention competes with the antigen binding proteins described in Tables 2-7. In some embodiments, an antigen binding protein (e.g., antibody or antibody fragment thereof) of the invention competes with the antigen binding proteins described in Tables A, B and C. In some embodiments, an antigen binding protein (e.g., antibody or antibody fragment thereof) of the invention competes with the antigen binding proteins described in Table 6. To "compete" or "competition" means the antigen binding proteins compete for the same epitope or binding site on a target. Such competition can be determined by an assay in which the reference antigen binding protein (e.g., antibody or antibody fragment thereof) prevents or inhibits specific binding of a test antigen binding protein. Numerous types of competitive binding assays can be used to determine if a test molecule competes with a reference molecule for binding. Examples of assays that can be employed include solid phase direct or indirect radioimmunoassay (RIA), solid phase direct or indirect enzyme immunoassay (EIA), sandwich competition assay (see, e.g., Stahli et al. (1983) *Methods in Enzymology* 9:242-253), solid phase direct biotin-avidin EIA (see, e.g., Kirkland et al., (1986) *J. Immunol.* 137:3614-3619), solid phase direct labeled assay, solid phase direct labeled sandwich assay, Luminex (Jia et al "A novel method of Multiplexed Competitive Antibody Binning for the characterization of monoclonal antibodies" *J. Immunological Methods* (2004) 288, 91-98) and surface plasmon resonance ((Song et al "Epitope Mapping of Ibalizumab, a Humanized Anti-CD4 Monoclonal Antibody with Anti-HIV-1 Activity in Infected Patients" *J. Virol.* (2010) 84, 6935-6942). An exemplary method of determining competition is described in Example 7D. Usually, when a competing antigen binding protein is present in excess, it will inhibit binding of a reference antigen binding protein to a common antigen by at least 50%, 55%, 60%, 65%, 70%, or 75%. In some instances, binding to ASGR-1 is inhibited by at least 80%, 85%, 90%, 95%, 96%, 97%, 98%, 99%, or more.

Besides competition, antigen binding proteins (e.g., antibodies or antibody fragments thereof) with identical, overlapping, or similar epitopes may be affected by mutagenesis of ASGR, ASGR-1 and/or ASGR-2 similarly. In brief, the domain(s)/region(s) containing residues that are in contact with or are buried by an antibody can be identified by mutating specific residues in ASGR, ASGR-1 and/or ASGR-2 (e.g., a wild-type antigen) and determining whether the antigen binding protein can bind the mutated or variant ASGR, ASGR-1 and/or ASGR-2 protein. By making a number of individual mutations, residues that play a direct role in binding or that are in sufficiently close proximity to the antibody such that a mutation can affect binding between the antigen binding protein and antigen can be identified. From the knowledge of these amino acids, the domain(s) or region(s) of the antigen that contain residues in contact with the antigen binding protein or covered by the antibody can be elucidated. Such a domain can include the binding epitope of an antigen binding protein. As mentioned above, one specific example of this general approach utilizes an arginine/glutamic acid scanning protocol (see, e.g., Nanevicz, T., et al., 1995, *J. Biol. Chem.,* 270:37, 21619-21625 and Zupnick, A., et al., 2006, *J. Biol. Chem.,* 281:29, 20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginine residues that exist in the wild-type antigen are replaced with glutamic acid. A variety of such individual mutants are obtained and the collected binding results analyzed to determine what residues affect binding. In Example 7E, scanning arginine/glutamic acid mutagenesis was performed using the human ASGR-1 CBD domain and the effect on exemplary antibodies was determined. Included with the scope of the invention are ASGR, ASGR-1 and/or ASGR-2 antigen binding proteins having characteristics such that they are affected in a similar way as an exemplary antibody to mutagenesis.

Example 7E describes one such arginine/glutamic acid scanning of ASGR-1 for ASGR-1 antigen binding proteins provided herein. A series of mutant ASGR-1 antigens were created, with each mutant antigen having a single mutation. Binding of each mutant ASGR-1 antigen with various ASGR-1 antigen binding proteins was measured and compared to the ability of the selected antigen binding proteins to bind to human ASGR-1 (SEQ ID NO:5). In certain embodiments, binding of an antigen binding protein of the present invention to ASGR-1 is inhibited by a single mutation in ASGR-1, wherein the single mutation is selected from the group consisting of R170, S171, G172, R183, L184, W195, E196, K199, H203, H204, P207, V208, N209, H215, D216, P220, D225, D228, R237, P238, E239, P241, D242, D243, Y245, G246, H247, G248, L249, G251, E253, T259, D260, R263, N265, Q270, R271, P272, R274, and E280 as shown in SEQ ID NO:5. In some embodiments, the ASGR-1 antigen binding proteins share the attributes of antibody 4A2 and their binding to ASGR-1 is inhibited a mutation of any of W195, E196, K199, H204, P207, and R263. In some embodiments, the ASGR-1 antigen binding proteins share the attributes of antibody 4B3 and their binding to ASGR-1 is inhibited by a mutation of any of H203, H204, P220, and G251. In some embodiments, the ASGR-1 antigen binding proteins share the attributes of antibody 5E5 and their binding to ASGR-1 is inhibited by a mutation of any of W195, K199, and R263. In some embodiments, the ASGR-1 antigen binding proteins share the attributes of antibody 6G7 and their binding to ASGR-1 is inhibited by a mutation of any of R183, L184, H215, P220, P238, G246, H247, G248, G251, and N265. In some embodiments, the ASGR-1 antigen binding proteins share the attributes of antibody 149D11 and their binding is inhibited by a mutation of any of R170, S171, and L184. In some embodiments, the ASGR-1 antigen binding proteins share the attributes of antibody 175F4 and their binding is inhibited by a mutation of R183. In some embodiments, the ASGR-1 antigen binding proteins share the attributes of antibody 17H6 and their binding is inhibited by a mutation of any of P241, D242, D243, Y245, G251, and E253. In some embodiments, the ASGR-1 antigen binding proteins share the attributes of antibody 194A4 and their binding is inhibited by a mutation of D260. In some embodiments, the ASGR-1 antigen binding proteins share the attributes of antibody 60C12 and their binding is inhibited by a mutation of any of R170, R237, E239, P241, T259, D260, R263, and N265. In some embodiments, the ASGR-1 antigen binding proteins share the attributes of antibody 65D5 and their binding is inhibited by a mutation of any of R237, T259, D260 and R263. In some embodiments, the ASGR-1 antigen binding proteins share the attributes of antibody 190F8 or 191G1 and their binding is inhibited by a mutation of any of R170, S171, G172, E196, H204, P207, V208, N209, H215, D216, D225, D228, P238, D243, G248, L249, G251, D260, Q270, R271, P272, R274 and E280. In some embodiments, the ASGR-1 antigen binding proteins share the attributes of antibody 199A7 and their binding is inhibited by a mutation of any of R170, R183, H215 and Q270. In some embodiments, the ASGR-1 antigen binding proteins share the attributes of antibody 146B6 and their binding is inhibited by a mutation of any of P241, T259, and N265. In some embodiments, the ASGR-1 antigen binding proteins share the attributes of antibody 193E7 and their binding is inhibited by a mutation of any of P207 and R263. In some embodiments, any of two or more, three or more, four or more, five or more, six or more, seven or more, eight or more nine or more, ten or more, or all of the single mutations of the aforementioned groups individually inhibit binding of the ASGR-1 antigen binding protein to ASGR-1.

Binding of various anti-ASGR-1 antigen binding proteins (e.g., antibodies 5E5, 22G5, 7E11, 4A2, 4H6, 72G9, 194A4, 54E9, 218G4, 176H4 and 194C10) were further analyzed using X-ray crystallography. The results from the X-ray crystallography were highly correlated with the results from the Arginine/Glutamic acid mutagenesis profiling described above and in Example 7E. The interface between an antigen binding protein and the antigen can be determined/defined a number of ways. In Examples 10B-L, the interface was determined by selecting interface residues having at least one atom within a predefined distance to its partner protein. In some embodiments, ASGR-1 residues that are within the interface with antibody, 5E5, as determined by distance of 8 Å or less are: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5). In some embodiments, ASGR-1 residues that are within the interface with antibody, 5E5, as determined by distance of 5 Å or less are: H161, E162, W195, E196, Q198, K199, F200, Q202, H203, H204, G232, F233, K234, N235, W236, R237, P238, D261, G262, or R263 (SEQ ID NO:5). In certain embodiments, the ASGR-1 antigen binding protein forms an interface with ASGR-1 that overlaps with that of antibody 5E5, including those wherein any of: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5) are within the interface. In certain embodiments, the ASGR-1 antigen binding protein forms an interface with ASGR-1 that overlaps with that of antibody 5E5, including those wherein any of: H161, E162, W195, E196, Q198, K199, F200, Q202, H203, H204, G232, F233, K234, N235, W236, R237, or P238 (SEQ ID NO:5) are within the interface.

In some embodiments, ASGR-1 residues that are within the interface with antibody, 22G5, as determined by distance of 8 Å or less are: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5). In some embodiments, ASGR-1 residues that are within the interface with antibody, 22G5, as determined by distance of 5 Å or less are: W167, S171, G172, K173, A174, A176, D177, N180, Y181, R183, L184, E185, D186, Q270, P272, or W275 (SEQ ID NO:5). In certain embodiments, the ASGR-1 antigen binding protein forms an interface with ASGR-1 that overlaps with that of antibody 5E5, including those wherein any of: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5) are within the interface. In certain embodiments, the ASGR-1 antigen binding protein forms an interface with ASGR-1 that overlaps with that of antibody 5E5, including those wherein any of: W167, S171, G172, K173, A174, A176, D177, N180, Y181, R183, L184, E185, D186, Q270, P272, or W275 (SEQ ID NO:5) are within the interface.

In some embodiments, ASGR-1 residues that are within the interface with antibody, 4A2, as determined by distance of 8 Å or less are: R170, W195, E196, K199, Q202, H203, H204, I205, G206, P207, V208, F233, K234, N235, W236, P238, D260, D261, G262, R263, R274, P155, N157, W158, F168, S169, R170, W175, A178, D179, C182, A187, W211, C269, R271, Y273, R274, C277, or T279 (SEQ ID NO:5). In some embodiments, ASGR-1 residues that are within the interface with antibody, 4A2, as determined by distance of 5 Å or less are: R170, W195, E196, K199, Q202, H203, H204, I205, G206, P207, V208, F233, K234, N235, W236, P238, D260, D261, G262, R263, or R274 (SEQ ID NO:5). In certain embodiments, the ASGR-1 antigen binding protein forms an interface with ASGR-1 that overlaps with that of antibody 4A2, including those wherein any of: R170, W195, E196, K199, Q202, H203, H204, I205, G206, P207, V208, F233, K234, N235, W236, P238, D260, D261, G262, R263, R274, P155, N157, W158, F168, S169, R170, W175, A178, D179, C182, A187, W211, C269, R271, Y273, R274, C277, or T279 (SEQ ID NO:5) are within the interface. In certain embodiments, the ASGR-1 antigen binding protein forms an interface with ASGR-1 that overlaps with that of antibody 4A2, including those wherein any of: R170, W195, E196, K199, Q202, H203, H204, I205, G206, P207, V208, F233, K234, N235, W236, P238, D260, D261, G262, R263, R274 (SEQ ID NO:5) are within the interface.

In some embodiments, ASGR-1 residues that are within the interface with antibody, 7E11, as determined by distance of 8 Å or less are: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5). In some embodiments, ASGR-1 residues that are within the interface with antibody, 7E11, as determined by distance of 5 Å or less are: H161, S194, W195, E196, Q198, K199, F200, Q202, H203, F233, K234, N235, W236, R237, P238, or R263 (SEQ ID NO:5). In certain embodiments, the ASGR-1 antigen binding protein forms an interface with ASGR-1 that overlaps with that of antibody 7E11, including those wherein any of: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5) are within the interface. In certain embodiments, the ASGR-1 antigen binding protein forms an interface with ASGR-1 that overlaps with that of antibody 7E11, including those wherein any of are within the surface: H161, S194, W195, E196, Q198, K199, F200, Q202, H203, F233, K234, N235, W236, R237, P238, or R263 (SEQ ID NO:5) are within the interface.

In some embodiments, ASGR-1 residues that are within the interface with antibody, 4H6, as determined by distance of 8 Å or less are: H161, E162, T193, S194, W195, E196, K199, Q202, T231, G232, F233, K234, N235, P238, D261, R263, R163, V192, E197, Q198, H203, P207, D228, E230, W236, R237, D260, G262, or W264 (S within the interface with antibody, 194C10, as determined by distance of 5 Å or less are: N157, R170, S171, G172, Q202, H203, H204, I205, G206, P207, V208, N209, T210, D260, R271, P272, Y273 or R274 (SEQ ID NO:5). In certain embodiments, the ASGR-1 antigen binding protein forms an interface with ASGR-1 that overlaps with that of antibody 194C10, including those wherein any of: N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5) are within the interface. In certain embodiments, the ASGR-1 antigen binding protein forms an interface with ASGR-1 that overlaps with that of antibody 194C10, including those wherein any of: N157, R170, S171, G172, Q202, H203, H204, I205, G206, P207, V208, N209, T210, D260, R271, P272, Y273, or R274 (SEQ ID NO:5) are within the interface.

In some embodiments, ASGR-1 residues that are within the interface with antibody, 54E9, as determined by distance of 8 Å or less are: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5). In some embodiments, ASGR-1 residues that are within the interface with antibody, 54E9, as determined by distance of 5 Å or less are: W195, N209, N235, R237, P238, E239, Q240, D242, H257, T259, D260, D261, R263, N265, D267, R271, or Y273 (SEQ ID NO:5). In certain embodiments, the ASGR-1 antigen binding protein forms an interface with ASGR-1 that overlaps with that of antibody 54E9, including those wherein any of: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5) are within the interface. In certain embodiments, the ASGR-1 antigen binding protein forms an interface with ASGR-1 that overlaps with that of antibody 54E9, including those wherein any of: W195, N209, N235, R237, P238, E239, Q240, D242, H257, T259, D260, D261, R263, N265, D267, R271, or Y273 (SEQ ID NO:5) are within the interface.

In some embodiments, ASGR-1 residues that are within the interface with antibody, 218G4, as determined by distance of 8 Å or less are: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5). In some embodiments, ASGR-1 residues that are within the interface with antibody, 218G4, as determined by distance of 5 Å or less are: R170, S171, G172, A174, H204, I205, G206, P207, V208, N209, H257, D260, N265, D267, Q270, R271, P272, Y273, or R274 (SEQ ID NO:5). In certain embodiments, the ASGR-1 antigen binding protein forms an interface with ASGR-1 that overlaps with that of antibody 218G4, including those wherein any of: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5) are within the interface. In certain embodiments, the ASGR-1 antigen binding protein forms an interface with ASGR-1 that overlaps with that of antibody 218G4, including those wherein any of: R170, S171, G172, K173, A174, D177, P207, V208, N209, R237, Q240, W244, G246, H247, G248, L249, E253, H257, T259, D260, N265, D267, Q270, R271, P272, Y273 or R274 (SEQ ID NO:5) are within the interface.

In some embodiments, ASGR-1 residues that are within the interface with antibody, 176H4, as determined by distance of 8 Å or less are: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, ASGR-1 residues that are within the interface with antibody, 176H4, as determined by distance of 5 Å or less are: R170, S171, G172, K173, A174, D177, P207, V208, N209, R237, Q240, W244, G246, H247, G248, L249, E253, H257, T259, D260, N265, D267, Q270, R271, P272, Y273 or R274 (SEQ ID NO:5). In certain embodiments, the ASGR-1 antigen binding protein forms an interface with ASGR-1 that overlaps with that of antibody 176H4, including those wherein any of: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275 (SEQ ID NO:5) are within the interface. In certain embodiments, the ASGR-1 antigen binding protein forms an interface with ASGR-1 that overlaps with that of antibody 176H4, including those wherein any of: R170, S171, G172, K173, A174, D177, P207, V208, N209, R237, Q240, W244, G246, H247, G248, L249, E253, H257, T259, D260, N265, D267, Q270, R271, P272, Y273, R274 (SEQ ID NO:5) are within the interface.

In some embodiments, the ASGR-1 residues that are involved in ligand binding are also in close proximity to the areas where antibodies 72G9, 54E9, 218G4 or 176H4 bind and can be useful for manipulating ASGR-1 binding to ligand. In some embodiments, the ASGR-1 antigen binding protein forms an interface with ASGR-1 that overlaps with that of antibody 72G9 and the ligand (e.g., GalNAc), including those wherein any of Q240, D242, W244, E239, P241, D243, Y245, G246, G252, R237, E253, P238, H247, C255, or V268 (SEQ ID NO:5) are within the interface. In some embodiments, the ASGR-1 antigen binding protein forms an interface with ASGR-1 that overlaps with that of antibody 72G9 and the ligand (e.g., GalNAc), including those wherein any of Q240, D242, or W244 (SEQ ID NO:5) are within the interface. In some embodiments, the ASGR-1 antigen binding protein forms an interface with ASGR-1 that overlaps with that of antibody 72G9 and the ligand (e.g., GalNAc), including those wherein any of Q240, D242, W244, E239, P241, D243, Y245, G246 or G252 (SEQ ID NO:5) are within the interface. In some embodiments, the ASGR-1 antigen binding protein forms an interface with ASGR-1 that overlaps with that of antibody 72G9 and the ligand (e.g., GalNAc), including those wherein any of Q240, D242, W244, R237 or E253 (SEQ ID NO:5) are within the interface. As noted in the examples below, the extent of inhibition resulting from 72G9 is lower than other direct blocking antibodies provided herein. While not intended to be limiting, this is understood to occur due to the nature of the relative orientations of the ASGR-1 protein and the antibody when bound to one another. For example, when the 72G9 antibody is bound to ASGR-1, there is still sufficient space for a ligand to reach the binding site, to some (although lesser) extent. In some embodiments, the ASGR-1 antigen binding protein forms an interface with ASGR-1 that overlaps with that of antibody 54E9 and the ligand (e.g., GalNAc), including those wherein any of N209, R237, Q240, D242, H257, T259, N265, D267, Y273, P238, E239, D260, R263, R271, E253, D266, D243, F258, or W264 (SEQ ID NO:5) are within the interface. In some embodiments, the ASGR-1 antigen binding protein forms an interface with ASGR-1 that overlaps with that of antibody 54E9 and the ligand (e.g., GalNAc), including those wherein any of N209, R237, Q240, D242, H257, T259, N265, D267, or Y273 (SEQ ID NO:5) are within the interface. In some embodiments, the ASGR-1 antigen binding protein forms an interface with ASGR-1 that overlaps with that of antibody 54E9 and the ligand (e.g., GalNAc), including those wherein any of N209, R237, Q240, D242, H257, T259, N265, D267, Y273, P238, E239, D260, R263, or R271 (SEQ ID NO:5) are within the interface. In some embodiments, the ASGR-1 antigen binding protein forms an interface with ASGR-1 that overlaps with that of antibody 54E9 and the ligand (e.g., GalNAc), including those wherein any of N209, R237, Q240, D242, H257, T259, N265, D267, Y273, E253 or D266 (SEQ ID NO:5) are within the interface. In some embodiments, the ASGR-1 antigen binding protein forms an interface with ASGR-1 that overlaps with that of antibody 218G4 and the ligand (e.g., GalNAc), including those wherein any of N209, H257, N265, D267, Y273, D260, R271, R237, T259, D266, F258 or V268 (SEQ ID NO:5) are within the interface. In some embodiments, the ASGR-1 antigen binding protein forms an interface with ASGR-1 that overlaps with that of antibody 218G4 and the ligand (e.g., GalNAc), including those wherein any of N209, H257, N265, D267, or Y273 (SEQ ID NO:5) are within the interface. In some embodiments, the ASGR-1 antigen binding protein forms an interface with ASGR-1 that overlaps with that of antibody 218G4 and the ligand (e.g., GalNAc), including those wherein any of N209, H257, N265, D267, Y273, D260 or R271 (SEQ ID NO:5) are within the interface. In some embodiments, the ASGR-1 antigen binding protein forms an interface with ASGR-1 that overlaps with that of antibody 218G4 and the ligand (e.g., GalNAc), including those wherein any of N209, H257, N265, D267, Y273. R237, T259 or D266 (SEQ ID NO:5) are within the interface. In some embodiments, the ASGR-1 antigen binding protein forms an interface with ASGR-1 that overlaps with that of antibody 176H4 and the ligand (e.g., GalNAc), including those wherein any of N209, R237, Q240, W244, E253, H257, T259, N265, D267, Y273, G246, H247, D260, R271, D266, P238, E239, Y245, F258, R263, W264, or V268 (SEQ ID NO:5) are within the interface. In some embodiments, the ASGR-1 antigen binding protein forms an interface with ASGR-1 that overlaps with that of antibody 176H4 and the ligand (e.g., GalNAc), including those wherein any of N209, R237, Q240, W244, E253, H257, T259, N265, D267, or Y273 (SEQ ID NO:5) are within the interface. In some embodiments, the ASGR-1 antigen binding protein forms an interface with ASGR-1 that overlaps with that of antibody 176H4 and the ligand (e.g., GalNAc), including those wherein any of N209, R237, Q240, W244, E253, H257, T259, N265, D267, Y273, G246, H247, D260, or R271 (SEQ ID NO:5) are within the interface. In some embodiments, the ASGR-1 antigen binding protein forms an interface with ASGR-1 that overlaps with that of antibody 176H4 and the ligand (e.g., GalNAc), including those wherein any of N209, R237, Q240, W244, E253, H257, T259, N265, D267, Y273, or D266 (SEQ ID NO:5) are within the interface.

As discussed above, the binding interaction between huASGR-1 and ligand (e.g., lactose, galactose, GalNAc), as well as the binding interaction between huASGR-1 and various embodiments of the antigen binding proteins (e.g., antibodies) of the present invention was evaluated using x-ray crystallography as described in Example 10. The binding interaction between huASGR-1 and various embodiments of the antigen binding proteins (e.g., antibodies) of the present invention was also evaluated using methodologies, including epitope binning as described in Example 7D, and arginine/glutamic acid mutational profiling as described in Example 7E. A summary of the data obtained through these methodologies is set forth in Table D below. This summary illustrates the various binding characteristics of representative antigen binding proteins (e.g., antibodies) of the present invention and their ability to directly and/or indirectly inhibit ligand binding to huASGR-1. In some embodiments, antibodies that interact with residues in common across different ligands can result in a similar form of inhibition (direct) across the various ligands. Examples of such residues are underlined and in bold in Table D.

TABLE D

Summary of Binding Characteristics of Representative Antigen Binding Proteins Derived from Examples 7 and 10.

| Ligand/<br>mAb<br>Name | mAb<br>Epitope<br>(bin) | Interaction Site<br>(crystal structure <5<br>angstroms) | Interaction Site<br>(crystal structure 5-8<br>angstroms) | R/E scan |
|---|---|---|---|---|
| Ligand/<br>Lactose | ND | Q240, D242, W244,<br>E253, N265, D266,<br>D267 | N209, R237, P238,<br>E239, P241, D243,<br>Y245, G246, H247,<br>G252, C255, H257,<br>T259, D260, V268,<br>R271, Y273 | ND |
| Ligand/<br>Galactose | ND | R237, D240, D242,<br>W244, E253, N265,<br>D266, D267 | N209, P238, E239,<br>P241, D243, Y245,<br>G246, H247, G252,<br>C255, H257, T259,<br>V268, R271, Y273 | ND |
| Ligand/<br>GalNAc | ND | N209, R237, D240,<br>D242, W244, E253,<br>H257, T259, N265,<br>D266, D267, Y273 | P238, E239, P241,<br>D243, Y245, G246,<br>H247, G252, C255,<br>F258, D260, R263,<br>W264, V268, R271 | ND |

TABLE D-continued

Summary of Binding Characteristics of Representative Antigen Binding Proteins Derived from Examples 7 and 10.

| Ligand/ mAb Name | mAb Epitope (bin) | Interaction Site (crystal structure <5 angstroms) | Interaction Site (crystal structure 5-8 angstroms) | R/E scan |
| --- | --- | --- | --- | --- |
| 5E5- Interaction is representative of indirect inhibition of ligand binding | A | H161, E162, W195, E196, Q198, K199, F200, Q202, H203, H204, G232, F233, K234, N235, W236, R237, P238, D261, G262, R263 | V159, E160, R163, T193, S194, E197, V201, I205, G206, P207, Y229, E230, T231, E239, F258, T259, D260, W264 | W195, K199 |
| 4A2- Interaction is representative of indirect inhibition of ligand binding | A | R170, W195, E196, K199, Q202, H203, H204, I205, G206, P207, V208, F233, K234, N235, W236, P238, D260, D261, G262, R263, R274 | N157, V159, F168, S169, S171, S194, Q198, F200, V201, T210, R237, E239, Q240, F258, T259, W264 | W195 |
| 7E11- Interaction is representative of indirect inhibition of ligand binding | A | H161, S194, W195, E196, Q198, K199, F200, Q202, H203, F233, K234, N235, W236, R237, P238, R263, | E160, E162, V192, T193, E197, V201, H204, Y229, E230, T231, G232, E239, Q240, P241, D261, G262, W264 | W195 |
| 4H6- Interaction is representative of indirect inhibition of ligand binding | A | H161, E162, T193, S194, W195, E196, K199, Q202, T231, G232, F233, K234, N235, P238, D261, R263 | R163, V192, E197, Q198, H203, P207, D228, E230, W236, R237, D260, G262, W264 | ND |
| 22G5- Interaction is representative of indirect inhibition of ligand binding | B | W167, S171, G172, K173, A174, A176, D177, N180, Y181, R183, L184, E185, D186, Q270, P272, W275 | P155, N157, W158, F168, S169, R170, W175, A178, D179, C182, A187, W211, C269, R271, Y273, R274, C277, T279 | R183, L184, H215, P220, G246, G248, G251, N265 |
| 194A4- Interaction is representative of indirect inhibition of ligand binding | C | T193, S194, W195, E196, P220, W221, G226, T227, D228, Y229, E230, T231, G232, F233, K234, N235, W236, R237, P238, E239, G252 | H161, E162, V191, V192, E197, Q198, D216, G219, K222, W223, D225, R263, W264 | D260 |
| 72G9- Interaction is representative of direct inhibition of ligand binding | C | D216, Q217, N218, G219, P220, W221, Y229, E230, K234, W236, E239, Q240, P241, D242, D243, W244, Y245, G246, L249, G250, G251, G252, D254, Q270 | H215, K222, T231, G232, R237, P238, H247, G248, E253, C255, D266, V268, C269 | P241, D242, D243, Y245, G251, E253 |
| 54E9- Interaction is representative of direct inhibition of ligand binding | E | W195, N209, N235, R237, P238, E239, Q240, D242, H257, T259, D260, D261, R263, N265, D267, R271, Y273 | Q198, Q202, P207, V208, F233, W236, D243, E253, F258, G262, W264, D266 | R237, E239, P241, T259, D260, R263, N265 |
| 218G4- Interaction is representative of direct inhibition of ligand binding | L/O | R170, S171, G172, A174, H204, I205, G206, P207, V208, N209, H257, D260, N265, D267, Q270, R271, P272, Y273, R274 | W167, F168, S169, K173, W175, D177, Y181, Q202, H203, T210, W211, R237, F258, T259, D261, D266, V268, C269, W275 | R171, G172, P238, R274 |
| 176H4- Interaction is representative of direct inhibition of ligand binding | L/R | R170, S171, G172, K173, A174, D177, P207, V208, N209, R237, Q240, W244, G246, H247, G248, L249, E253, H257, T259, D260, N265, D267, Q270, R271, P272, Y273, R274 | S169, W175, A176, A178, T210, W211, W236, P238, E239, D242, Y245, G250, G251, F258, D261, G262, R263, W264, D266, V268, C269, W275 | G172, P241, D242, H247, L249, N265, R271, P272 |
| 194C10- Interaction is representative of direct | L/T | N157, R170, S171, G172, Q202, H203, H204, I205, G206, P207, V208, N209, | V156, W158, V159, H161, W167, F168, S169, K173, K199, F200, V201, W211, | R170, G172, V208, R274 |

TABLE D-continued

Summary of Binding Characteristics of Representative Antigen Binding Proteins Derived from Examples 7 and 10.

| Ligand/<br>mAb<br>Name | mAb<br>Epitope<br>(bin) | Interaction Site<br>(crystal structure <5<br>angstroms) | Interaction Site<br>(crystal structure 5-8<br>angstroms) | R/E scan |
|---|---|---|---|---|
| and/or indirect<br>inhibition of<br>ligand binding | | T210, D260, R271,<br>P272, Y273, R274 | R237, H257, F258,<br>T259, D261, D267,<br>V268, Q270, W275 | |

In some embodiments, the antibody can directly inhibit ASGR-1 CBD/Ligand binding. While described herein in greater detail, and while not intended to be limiting by theory, such an interaction can denote that the antibody interacts with the section of ASGR-1 CBD that binds to its ligand directly, such that a paratope or other section of an antigen binding protein (e.g., antibody) directly obstructs the ligand's access to the binding site in ASGR1 CBD. An antigen binding protein or antibody can be designated as a direct inhibitor when it has one or more of the characteristics of the direct inhibitors provided herein, including the examples below (such as example 10, or the crystal structures referenced therein). Some examples of direct inhibition are shown by 72G9, 54E9, 218G4 and 176H4 and are indicated in Table D. In some embodiments, a direct inhibitor can bind to one or more of residues 237-273 or residues 240-267 of SEQ ID NO:5 of ASGR-1.

In some embodiments, the antigen binding protein or antibody can indirectly inhibit ASGR-1 CBD/Ligand binding. While described herein in greater detail, and while not intended to be limiting by theory, this denotes that the antigen binding protein or antibody binds to ASGR-1 CBD, but need not directly obstruct the ligand's access to the binding site in ASGR-1 CBD. An antigen binding protein or antibody can be designated as an indirect inhibitor when it has one or more of the characteristics of the indirect inhibitors provided herein, including the examples below (such as example 10 or the crystal structures provided therein). Some examples of indirect inhibition are shown by 5E5, 4A2, 7E11, 4H6, 22G5, 194A4, and are indicated in Table D. While not limiting, it is noted that indirect inhibition can occur from a variety of interactions or rearrangements. For example, indirect inhibition may occur from a conformational rearrangement of the carbohydrate binding loop occurs which could impair the carbohydrate binding loop from binding to/interacting with ligand (i.e., carbohydrates). In some embodiments, an indirect inhibitor can bind to one or more of the residues in ASGR-1 CBD helix alpha 1 and/or helix alpha 2. In some embodiments, the antibody binds to ASGR-1 and results in the disordering of the CBD.

In some embodiments, an antigen binding protein or antibody can have characteristics of both direct and indirect inhibition and/or bind to areas on ASGR-1 CBD that are common to both types of inhibition. Of course, such an embodiment may have sufficient inhibition capability through its direct, indirect, or both direct and indirect interactions.

In some embodiments, the distinction between direct and indirect inhibition need not be made. In some embodiments, denoting that an antigen binding protein or antibody provides direct or indirect inhibition means that it provides at least that form of inhibition (e.g., ASGR-1 CBD/Ligand blocking). In some embodiments, an antigen binding protein or antibody that provides direct inhibition, may also provide indirect aspects as well (such as other conformational changes). In addition, as shown in Table D, as the interation between ASGR-1 CBD and its ligands can vary for each of the noted three ligands, what may be a direct or indirect interaction for one ligand, need not be direct or indirect for another. While the antibodies provided herein that have the properties of direct and/or indirect inhibition will function accordingly, and the guidance provided herein allows for one to screen for and produce additional such antibodies, the fact that an antibody simply binds to ASGR-1 CBD does not necessarily mean that it will bind at the relevant locations on ASGR-1 to allow for direct or indirect inhibition.

In some embodiments, an isolated antigen binding protein that binds to human ASGR and inhibits ASGR function is provided. In one embodiment, the invention comprises an isolated antigen binding protein that binds to human ASGR and inhibits ASGR binding to ligand. In another embodiment, the invention comprises an isolated antigen binding protein that binds to human ASGR-1 and inhibits ASGR-1 binding to ligand and/or ASGR-1 interaction with ASGR-2. In another embodiment, the invention comprises an isolated antigen binding protein that binds to human ASGR-2 and inhibits ASGR-2 binding to ligand and/or ASGR-2 interaction with ASGR-1. In yet another embodiment, the invention comprises an isolated antigen binding protein that binds to human ASGR-1 and human ASGR-2, and inhibits ASGR-1 and/or ASGR-2 binding to ligand. In some embodiments, the isolated binding protein binds specifically to human ASGR, ASGR-1 and/or ASGR-2.

In some embodiments, an isolated antigen binding protein is provided, wherein the isolated antigen binding protein binds to human ASGR-1 and comprises one or more VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7. In some embodiments, the invention comprises an isolated antigen binding protein, wherein the isolated antigen binding protein binds to human ASGR-1 and comprises one or more VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises one or more VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and one or more VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises one VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and one VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises two VH CDR1, VH CDR2 or VH CDR3 having an amino acid sequence identical to or comprising 1, 2, or 3 amino acid residue substitutions, deletions or insertions in each CDR relative to the VH of any of the sequences set forth in Tables 3-7, and two VL CDR1, VL CDR2 or VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises the VH CDR1, VH CDR2 and VH CDR3 having an amino acid sequence identical to or comprising 1, 2, or 3 amino acid residue substitutions, deletions or insertions in each CDR relative to the VH of any of the sequences set forth in Tables 3-7, and the VL CDR1, VL CDR2 and VL CDR3 having an amino acid sequence identical to or comprising 1, 2, or 3 amino acid residue substitutions, deletions or insertions in each CDR relative to the VL of any of the sequences set forth in Tables 3-7. In some embodiments, the isolated antigen binding protein comprises the VH CDR1, VH CDR2, VH CDR3, VL CDR1, VL CDR2, and VL CDR3 having an amino acid sequence identical to any of the sequences set forth in Tables 3-7. In some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE A. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE A. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE A, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in TABLE A. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE A. In some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE B. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE B. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE B, and the VL CDR1, VL CDR2 and VL CDR3 having an amino acid sequence identical to or comprising 1, 2, or 3 amino acid residue substitutions, deletions or insertions in each CDR relative to the VL of any of the sequences set forth in TABLE B. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE B. In still some embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in TABLE C. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in TABLE C. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in TABLE C, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in TABLE C. In some embodiments, the isolated antigen binding protein comprises the VH CDR1, VH CDR2, VH CDR3, VL CDR1, VL CDR2, and VL CDR3 having an amino acid sequence identical to any of the sequences set forth in TABLE C. In further embodiments, the isolated antigen binding protein comprises the VH CDR1, VH CDR2 or VH CDR3 having an amino acid sequence identical to or comprising 1, 2, or 3 amino acid residue substitutions, deletions or insertions in each CDR relative to the VH of any of the sequences set forth in Table 6. In some embodiments, the isolated antigen binding protein comprises the VL CDR1, VL CDR2 or VL CDR3 having an amino acid sequence identical to or comprising 1, 2, or 3 amino acid residue substitutions, deletions or insertions in each CDR relative to the VL of any of the sequences set forth in Table 6. In some embodiments, the isolated antigen binding protein comprises the VH CDR1, VH CDR2, and VH CDR3 having an amino acid sequence identical to or comprising 1, 2, or 3 amino acid residue substitutions, deletions or insertions in each CDR relative to the VH of any of the sequences set forth in Table 6, and the VL CDR1, VL CDR2 and VL CDR3, having an amino acid sequence identical to or comprising 1, 2, or 3 amino acid residue substitutions, deletions or insertions in each CDR relative to the VL of any of the sequences set forth in Table 6. In some embodiments, the isolated antigen binding protein comprises the VH CDR1, VH CDR2, VH CDR3, VL CDR1, VL CDR2, and VL CDR3 having an amino acid sequence identical to any of the sequences set forth in Table 6.

In some embodiments, an isolated antigen binding protein is provided, wherein the antigen binding protein specifically binds human ASGR-1 and comprises a heavy chain variable domain having at least 90% identity to any of the VH domain amino acid sequences set forth in Tables 3-7. In some aspects, the invention provides an isolated antigen binding protein, wherein the antigen binding protein specifically binds human ASGR-1 and comprises a light chain variable domain having at least 90% identity to any of the VL domain amino acid sequences set forth in Tables 3-7. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Tables 3-7, and a light chain variable domain having at least 90% identity to any of the VL domain amino acid sequences set forth in Tables 3-7. In some embodiments, the invention provides an isolated antigen binding protein, wherein the antigen binding protein specifically binds human ASGR-1 and comprises a heavy chain variable domain having any of the VH domain amino acid sequences set forth in Tables 3-7, and a light chain variable domain having any of the VL domain amino acid sequences set forth in Tables 3-7. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table A. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table A. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table A, and a light chain variable domain having at least 90% identity to any of the VL domain amino acid sequences set forth in Table A. In some embodiments, the invention provides an isolated antigen binding protein, wherein the antigen binding protein specifically binds human ASGR-1 and comprises a heavy chain variable domain having any of the VH domain amino acid sequences set forth in Table A, and a light chain variable domain having any of the VL domain amino acid sequences set forth in Table A. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table B. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table B. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table B, and a light chain variable domain having at least 90% identity to any of the VL domain amino acid sequences set forth in Table B. In some embodiments, the invention provides an isolated antigen binding protein, wherein the antigen binding protein specifically binds human ASGR-1 and comprises a heavy chain variable domain having any of the VH domain amino acid sequences set forth in Table B, and a light chain variable domain having any of the VL domain amino acid sequences set forth in Table B. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table C. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table C. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table C, and a light chain variable domain having at least 90% identity to any of the VL domain amino acid sequences set forth in Table C. In some embodiments, the invention provides an isolated antigen binding protein, wherein the antigen binding protein specifically binds human ASGR-1 and comprises a heavy chain variable domain having any of the VH domain amino acid sequences set forth in Table C, and a light chain variable domain having any of the VL domain amino acid sequences set forth in Table C. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table 6. In some embodiments, the invention provides an isolated antigen binding protein, wherein the antigen binding protein specifically binds human ASGR-1 and comprises a light chain variable domain having at least 90% identity to any of the VL domain amino acid sequences set forth in Table 6. In some embodiments, the invention provides an isolated antigen binding protein, wherein the antigen binding protein specifically binds human ASGR-1 and comprises a heavy chain variable domain having at least 90% identity to any of the VH domain amino acid sequences set forth in Table 6, and a light chain variable domain having at least 90% identity to any of the VL domain amino acid sequences set forth in Table 6. In some embodiments, the invention provides an isolated antigen binding protein, wherein the antigen binding protein specifically binds human ASGR-1 and comprises a heavy chain variable domain having any of the VH domain amino acid sequences set forth in Table 6, and a light chain variable domain having any of the VL domain amino acid sequences set forth in Table 6.

In some embodiments, an isolated antigen binding protein is provided, wherein the antigen binding protein binds human ASGR-1 and comprises one or more VH CDR1, VH CDR2 or VH CDR3 having an amino acid sequence identical to or comprising no more than 18 amino acid residue substitutions, insertions or deletions in each CDR relative to the VH of any of the sequences set forth in Table 19A as depicted in FIG. 55. In some embodiments, the invention provides an isolated antigen binding protein, wherein the antigen binding protein binds human ASGR-1 and comprises one or more VH CDR1, VH CDR2 or VH CDR3 having an amino acid sequence identical to or comprising a conservative substitution of any of the amino acid sequences set forth in Table 19B or 19C, as depicted in FIG. 55. In some aspects, the invention comprises an isolated antigen binding protein, wherein the isolated antigen binding protein binds to human ASGR-1 and comprises one or more VL CDR1, VL CDR2 or VL CDR3 having an amino acid sequence identical to or comprising no more than 14 amino acid residue substitutions, insertions or deletions in each CDR relative to the VL of any of the sequences set forth in Table 20A as depicted in FIG. 55. In some embodiments, the invention provides an isolated antigen binding protein, wherein the antigen binding protein binds human ASGR-1 and comprises one or more VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises one or more VH CDR1, VH CDR2 or VH CDR3 having an amino acid sequence identical to or comprising no more than 18 amino acid residue substitutions, insertions or deletions in each CDR relative to the VH of any of the sequences set forth in Table 19A, as depicted in FIG. 55, and one or more VL CDR1, VL CDR2 or VL CDR3 having an amino acid sequence identical to or comprising no more than 14 amino acid residue substitutions, insertions or deletions in each CDR relative to the VL of any of the sequences set forth in Table 20A as depicted in FIG. 55. In some embodiments, the invention provides an isolated antigen binding protein, wherein the antigen binding protein binds human ASGR-1 and comprises one or more VH CDR1, VH CDR2 or VH CDR3 having an amino acid sequence identical to or comprising a conservative substitution of any of the amino acid sequences set forth in Table 19B or 19C, as depicted in FIG. 55, and one or more VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises one VH CDR1, VH CDR2 or VH CDR3 having an amino acid sequence identical no more than 18 amino acid residue substitutions, insertions or deletions in each CDR relative to the VH of any of the sequences set forth in Table 19A, as depicted in FIG. 55, and one VL CDR1, VL CDR2 or VL CDR3 having an amino acid sequence identical to or comprising no more than 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises one VH CDR1, VH CDR2 or VH CDR3 having an amino acid sequence identical to or comprising a conservative substitution of any of the amino acid sequences set forth in Table 19B or 19C, as depicted in FIG. 55, and one VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises two VH CDR1, VH CDR2 or VH CDR3 having an amino acid sequence identical to or comprising up to 18 amino acid residue substitutions, insertions or deletions in each CDR relative to the VH of any of the sequences set forth in Table 19A, as depicted in FIG. 55, and two VL CDR1, VL CDR2 or VL CDR3 having an amino acid sequence identical to or comprising up to 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises two VH CDR1, VH CDR2 or VH CDR3 having an amino acid sequence identical to or comprising a conservative substitution of any of the amino acid sequences set forth in Table 19B or 19C, as depicted in FIG. 55, and two VL CDR1, VL CDR2 or VL CDR3 having an amino acid sequence identical to or comprising a conservative substitution of any of the amino acid sequences set forth in Table 20B or 20C, as depicted in FIG. 55. In some embodiments, the isolated antigen binding protein comprises the VH CDR1, VH CDR2 and VH CDR3 having an amino acid sequence identical to or comprising up to 18 amino acid residue substitutions, insertions or deletions in each CDR relative to the VH of any of the sequences set forth in Table 19A, as depicted in FIG. 55, and the VL CDR1, VL CDR2 and VL CDR3 having an amino acid sequence identical to or comprising up to 14 amino acid residue substitutions, insertions or deletions in each CDR relative to the VL of any of the sequences set forth in Table 20A, as depicted in FIG. 55. In some embodiments, the invention provides an isolated antigen binding protein, wherein the antigen binding protein binds human ASGR-1 and comprises the VH CDR1, VH CDR2 or VH CDR3 having an amino acid sequence identical to or comprising a conservative substitution of any of the amino acid sequences set forth in Table 19B or 19C, as depicted in FIG. 55, and the VL CDR1, VL CDR2 or VL CDR3 having an amino acid sequence identical to or comprising a conservative substitution of any of the amino acid sequences set forth in Table 20B or 20C, as depicted in FIG. 55.

Figure 56:
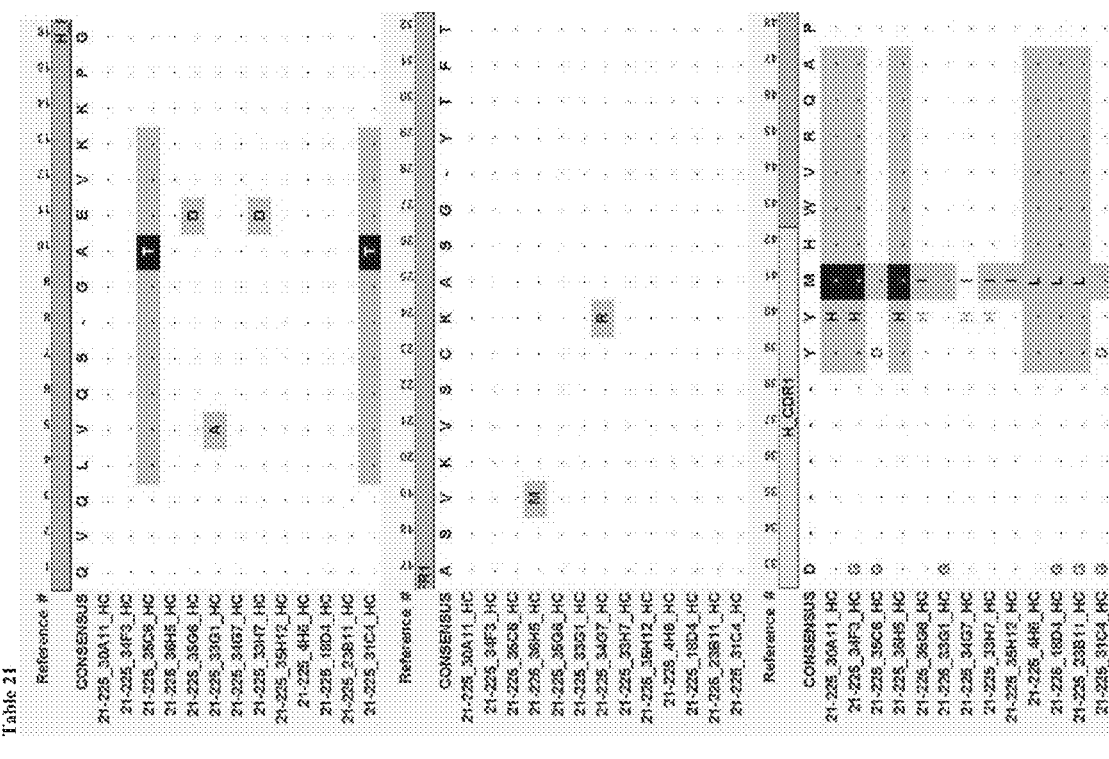
FIG. 56. A group of tables presenting the detailed consensus protein alignment of various light and heavy chain variable regions for certain antigen binding proteins of the present invention (Tables 21-48). The shading of amino acid residues in the consensus protein alignment presented in Tables 21-48 denote particular residues that one of ordinary skill in the art may wish to target for engineering.
Figure 56:
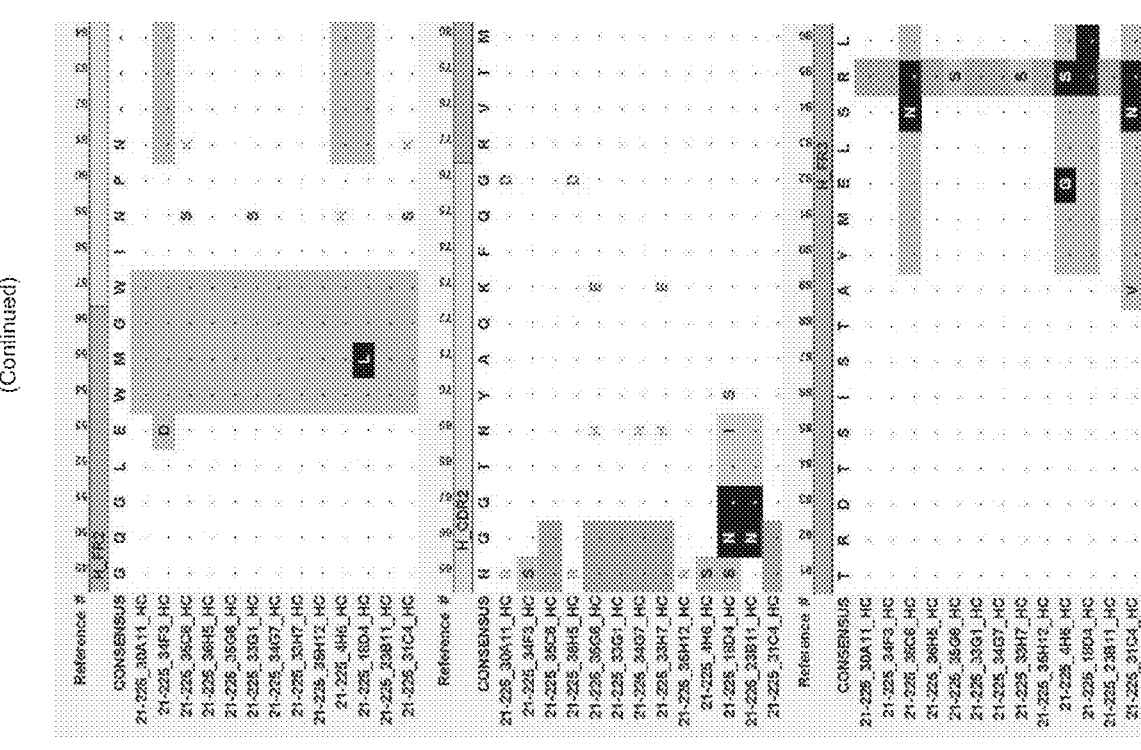
Figure 56:
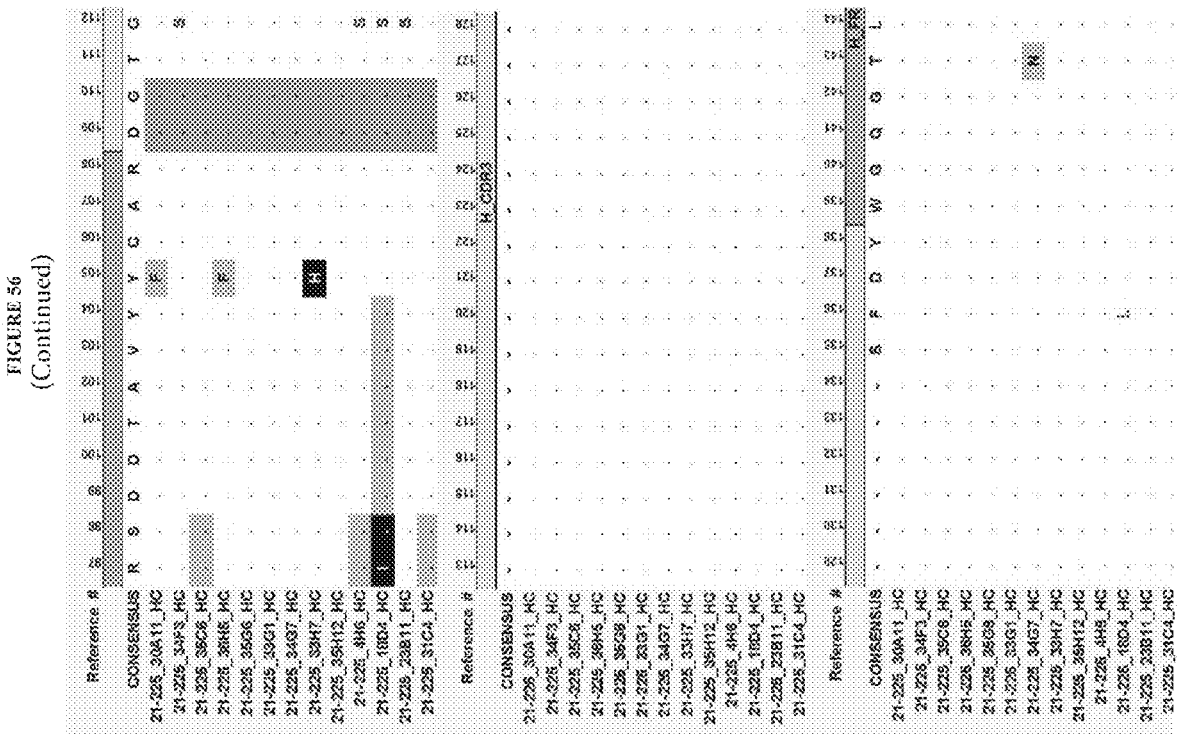
Figure 56:
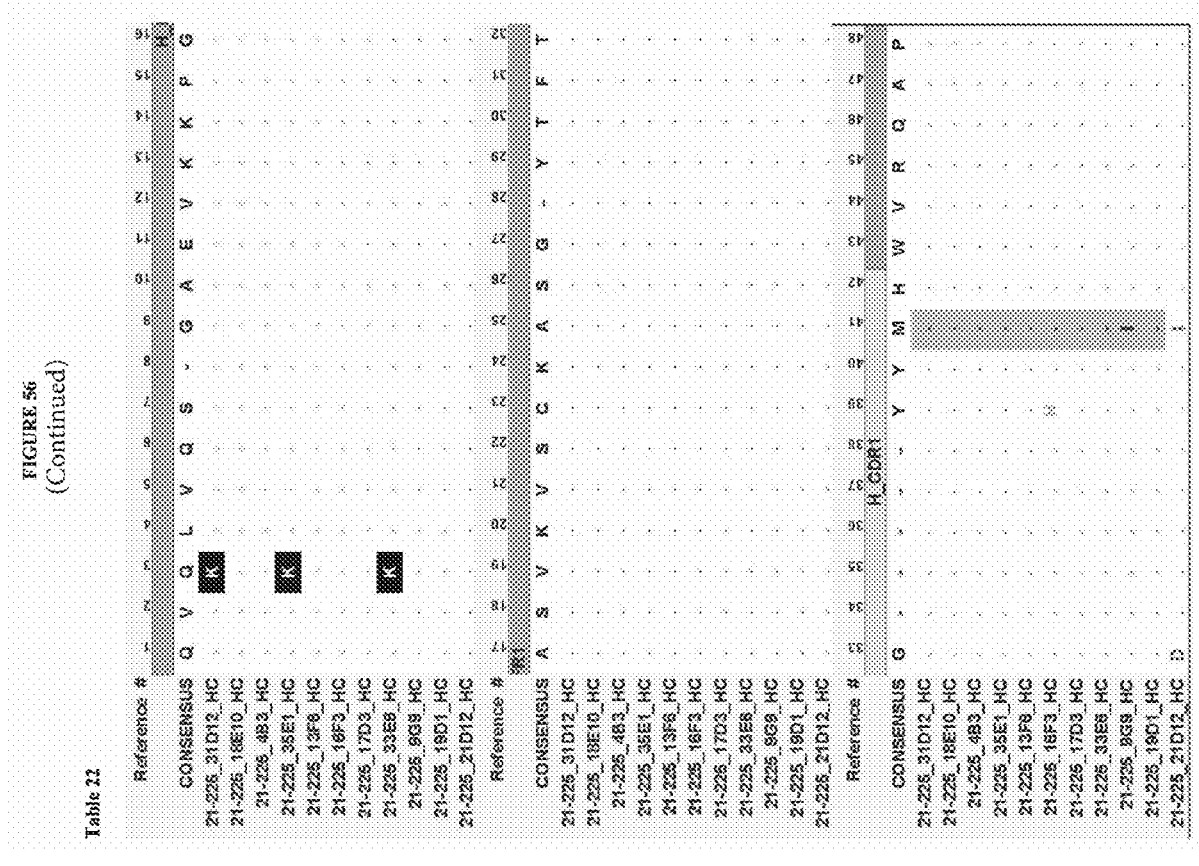
Figure 56:
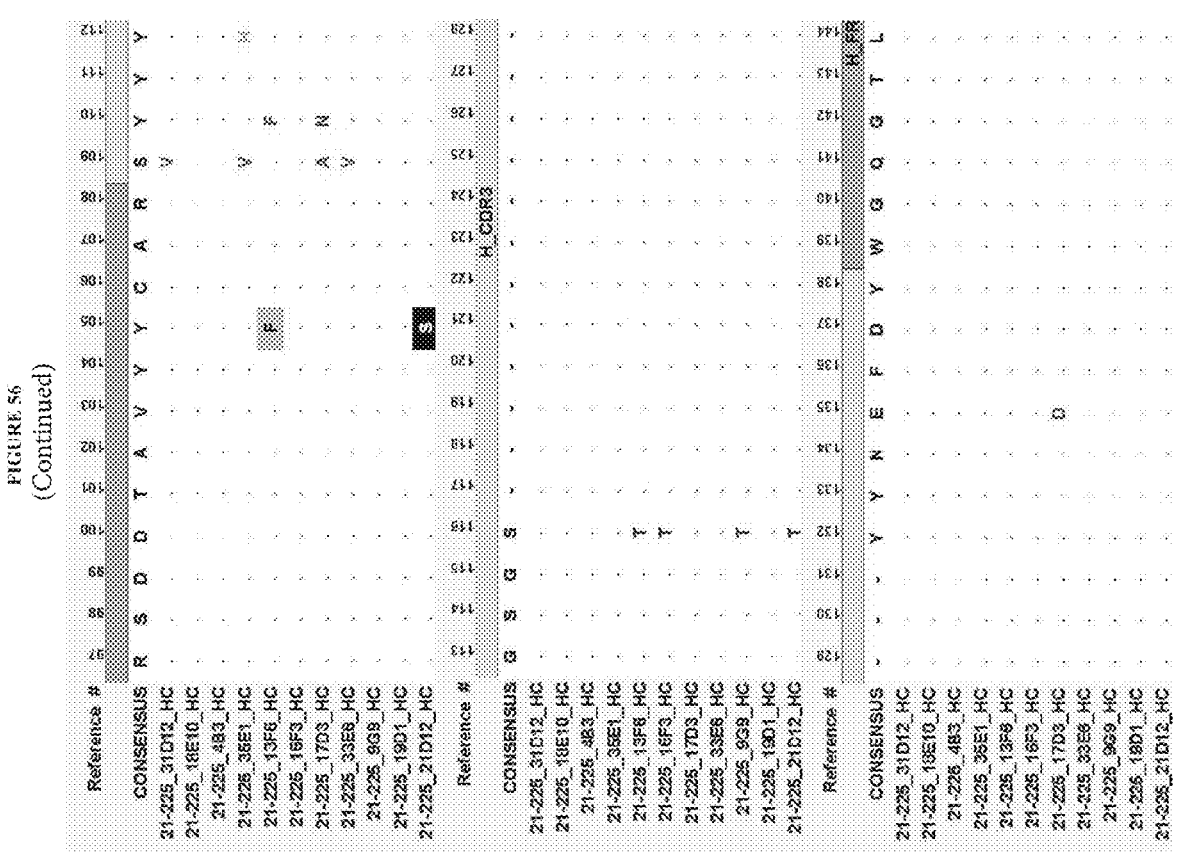
Figure 56:
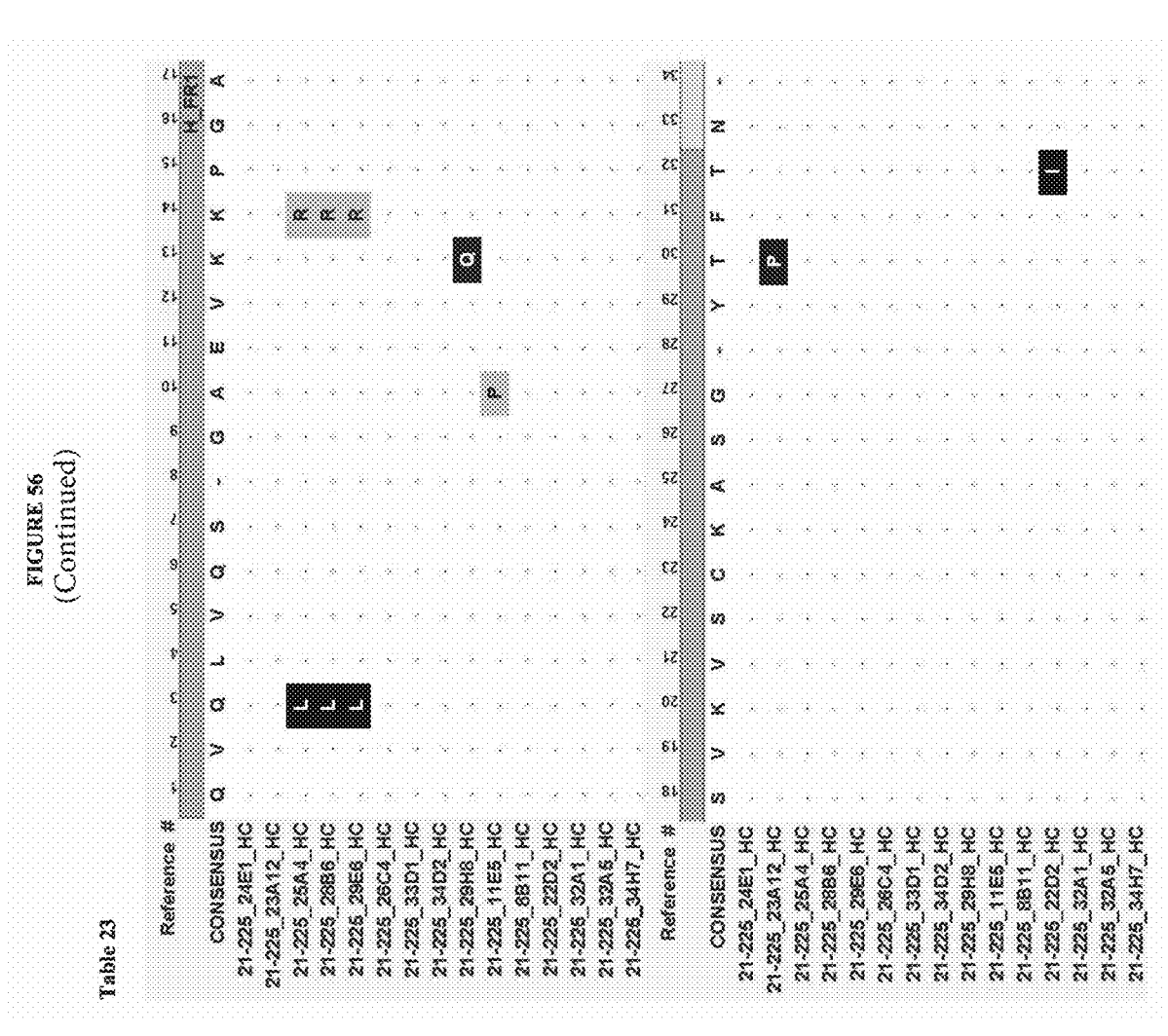
Figure 56:
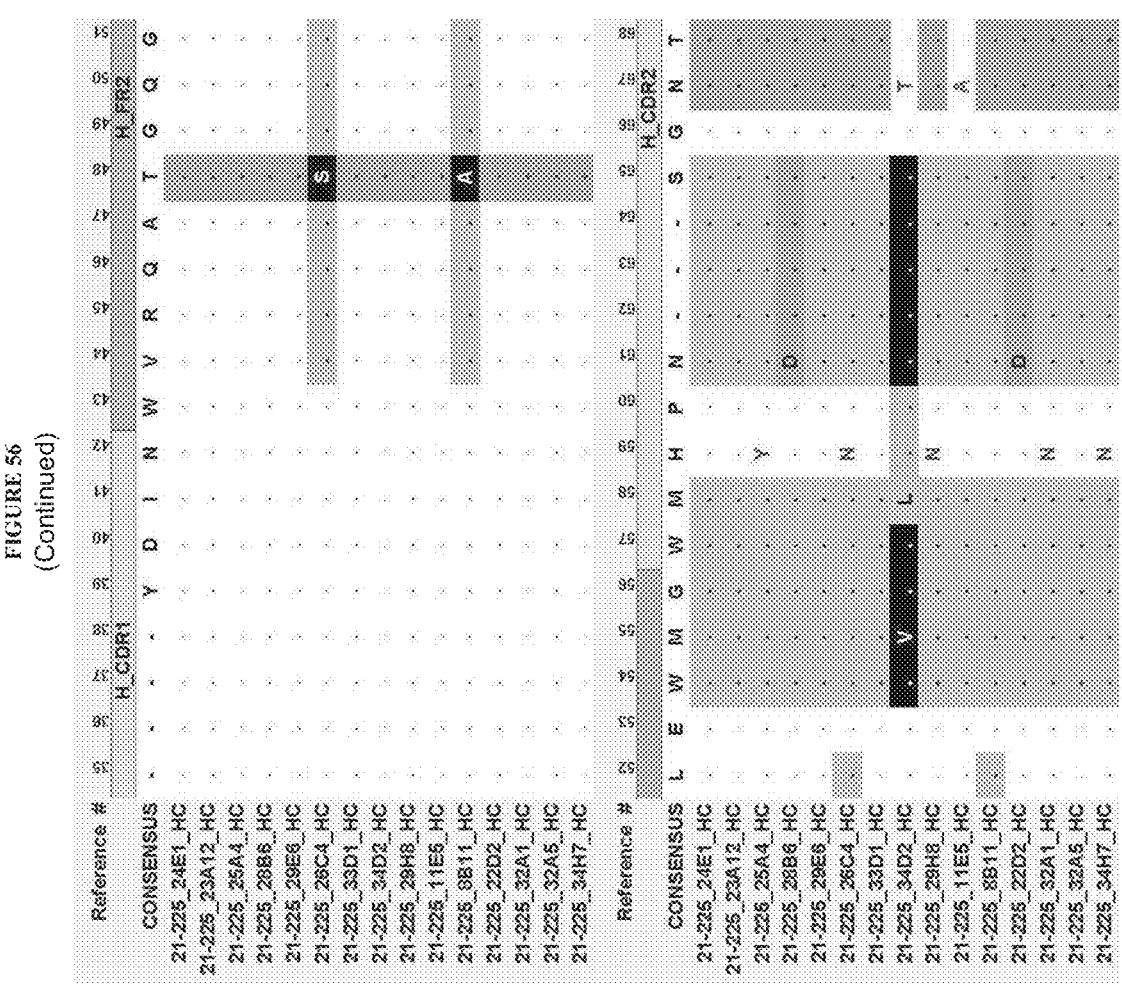
Figure 56:
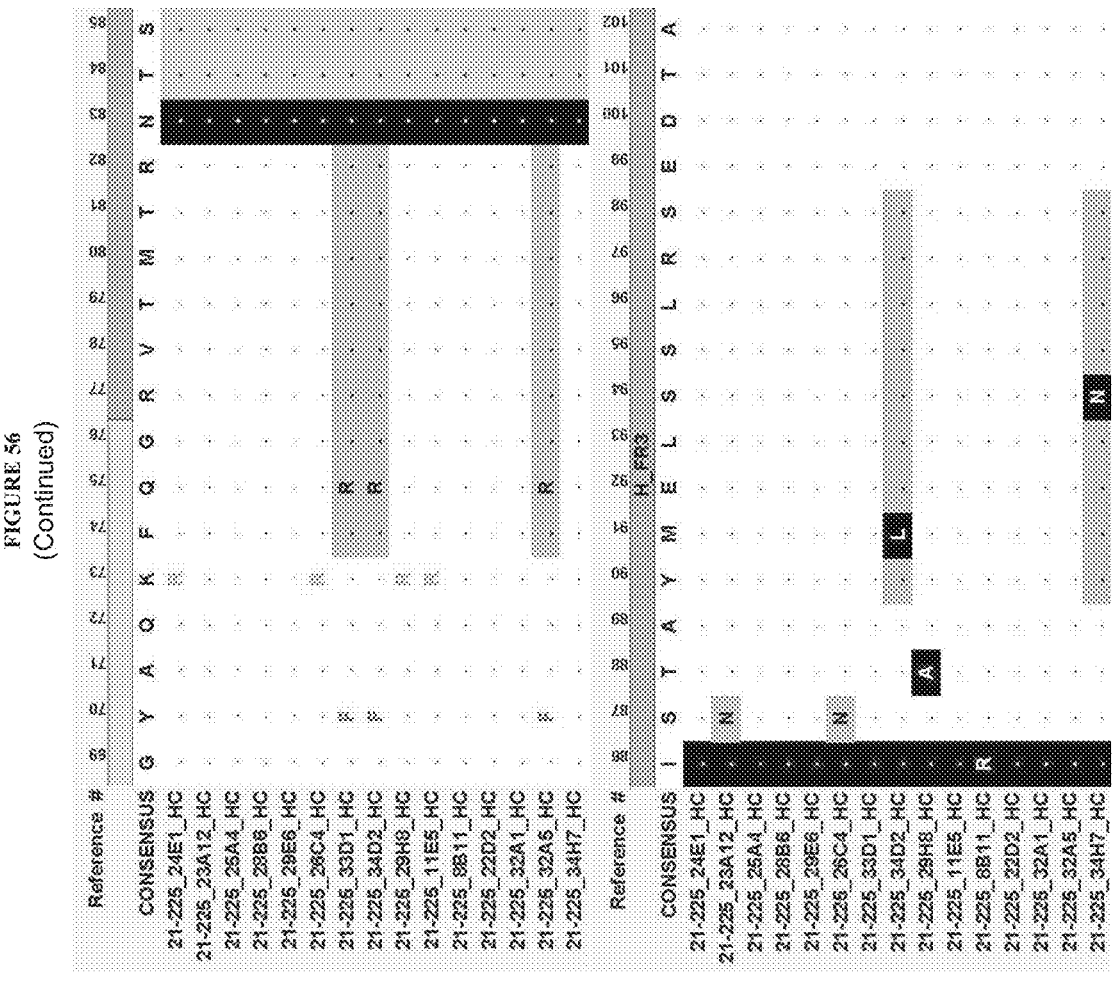
Figure 56:
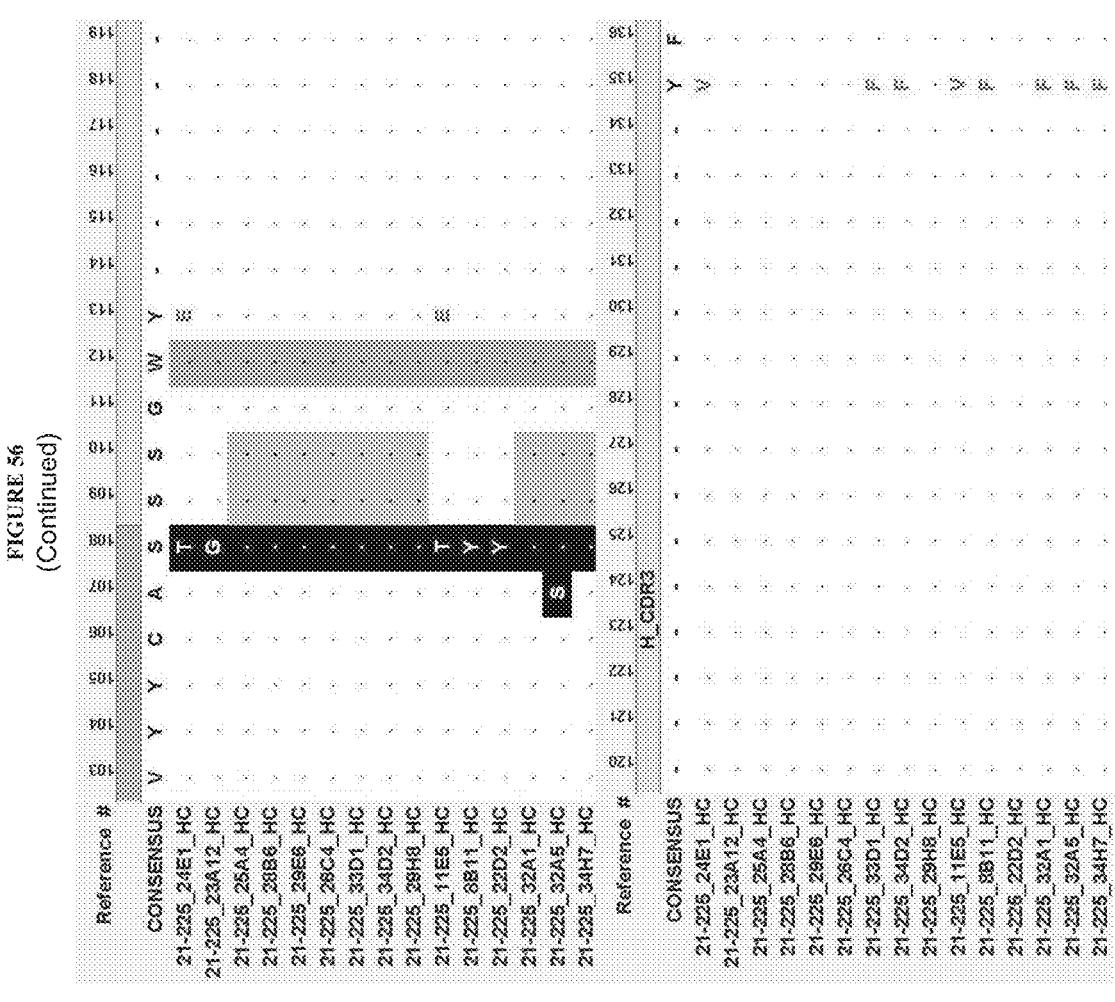
Figure 56:
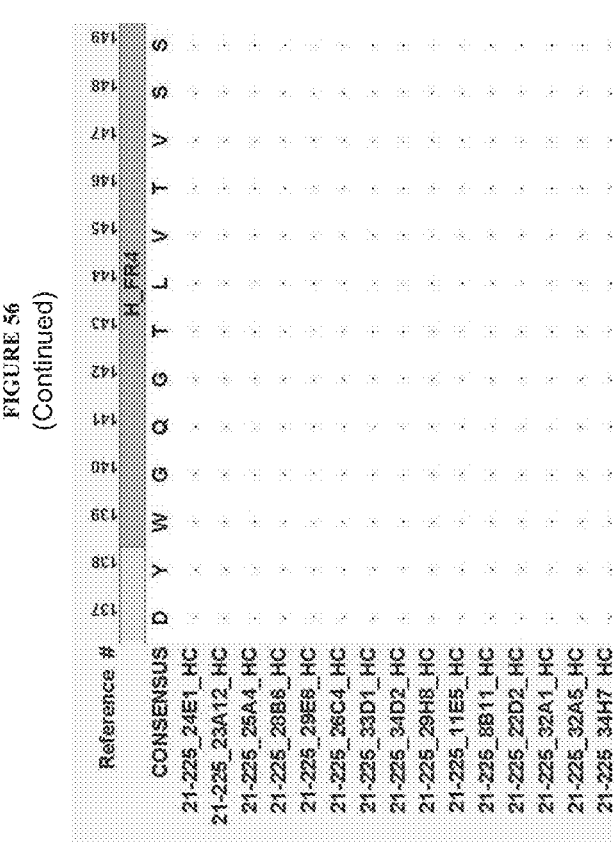
Figure 56:
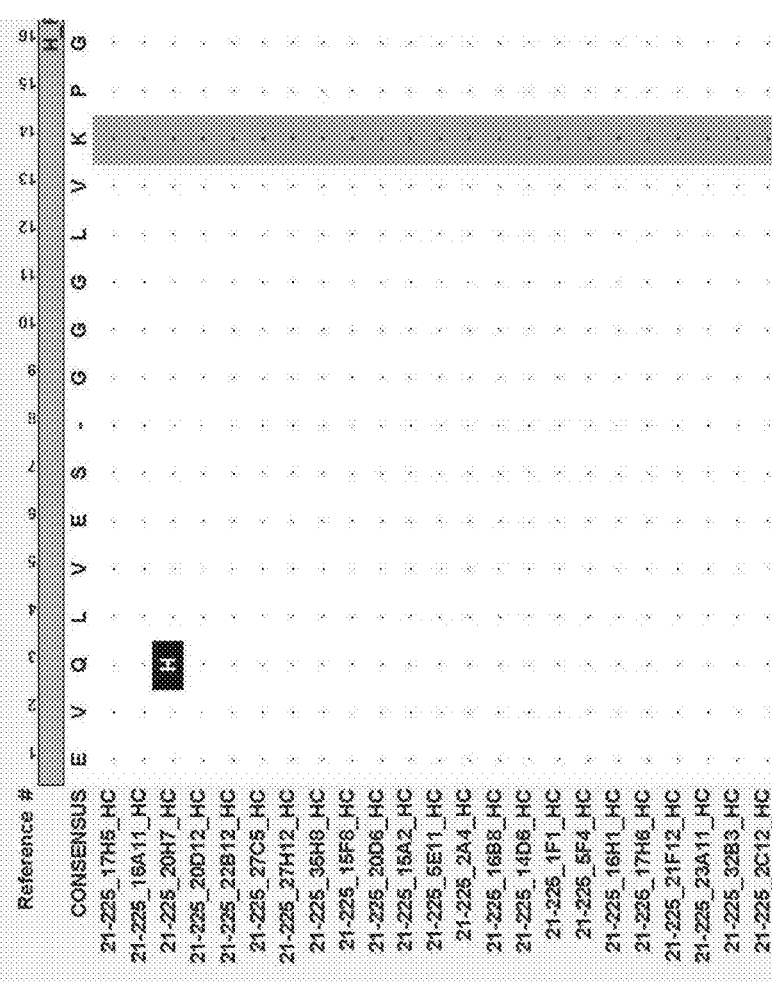
Figure 56:
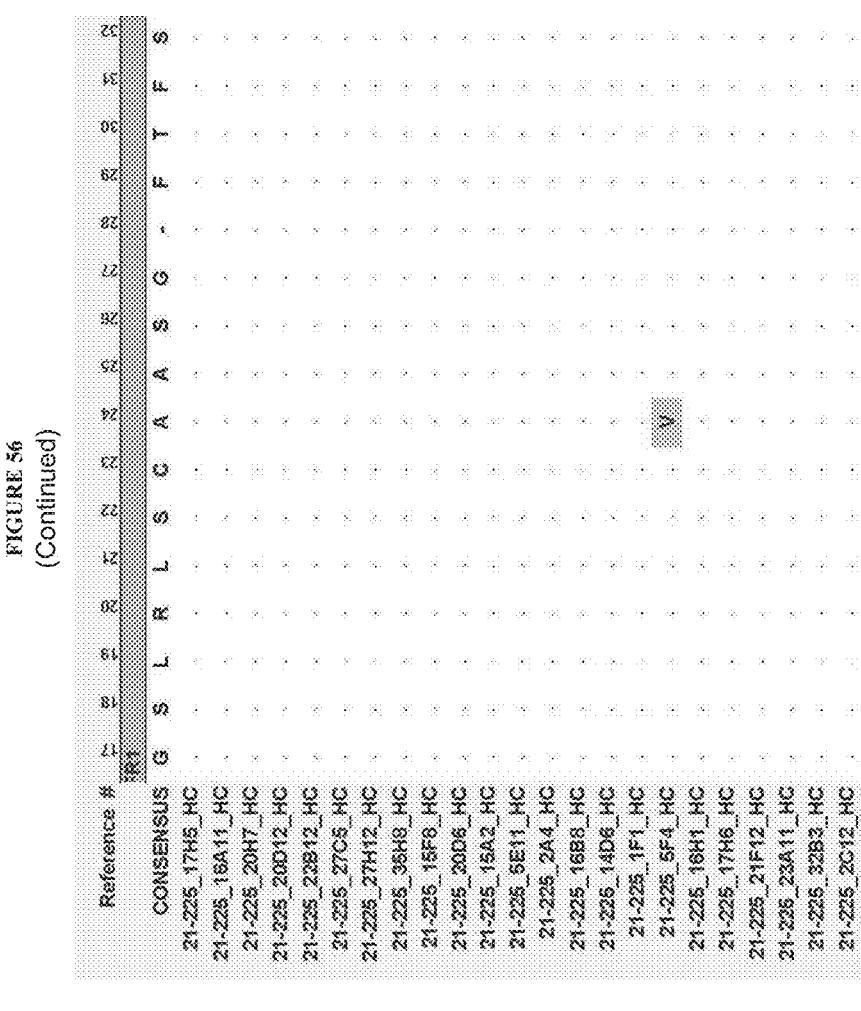
Figure 56:
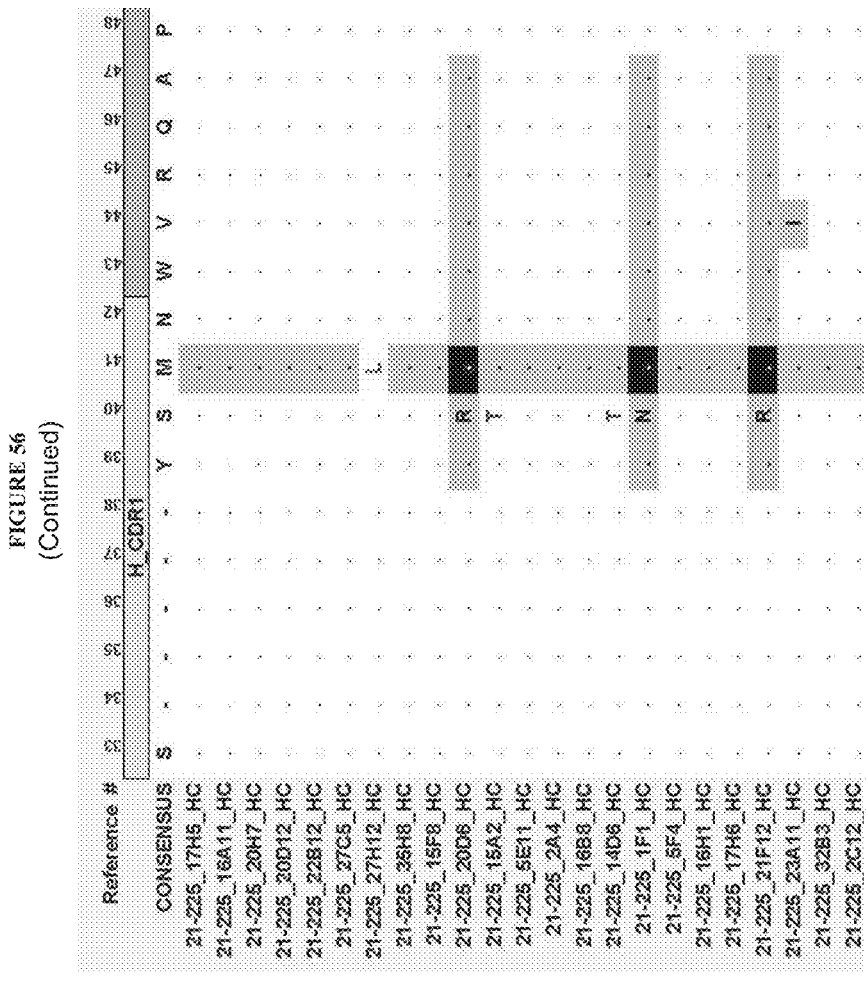
Figure 56:
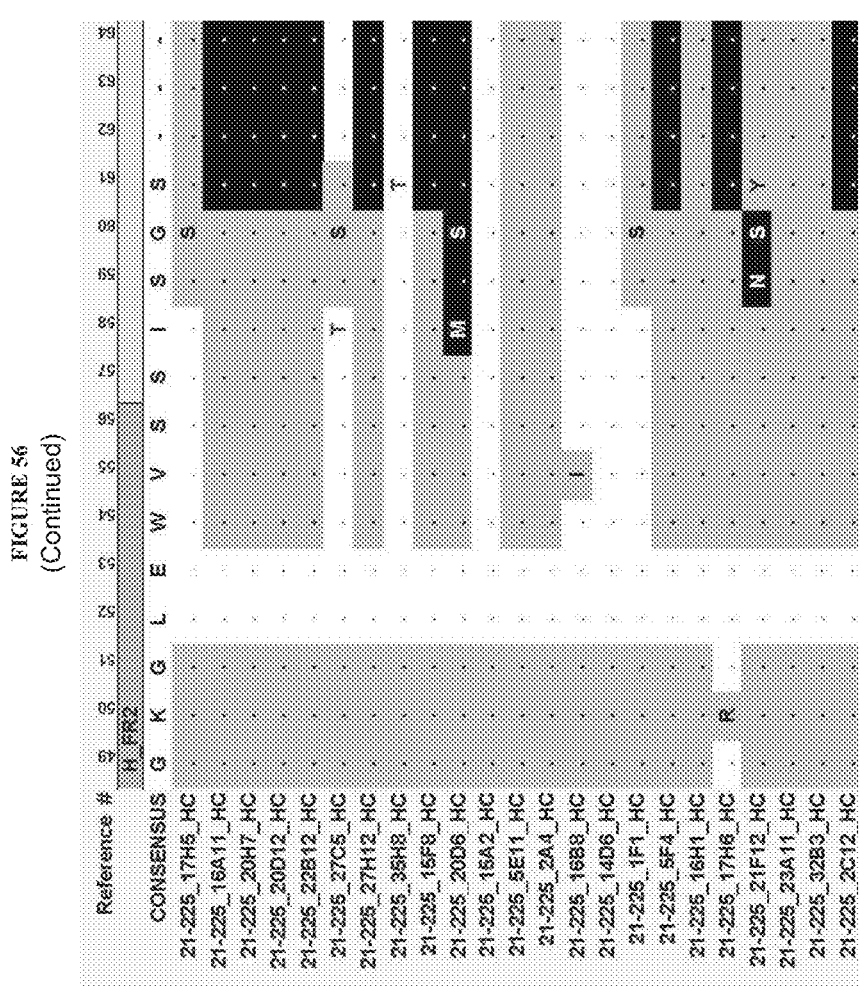
Figure 56:
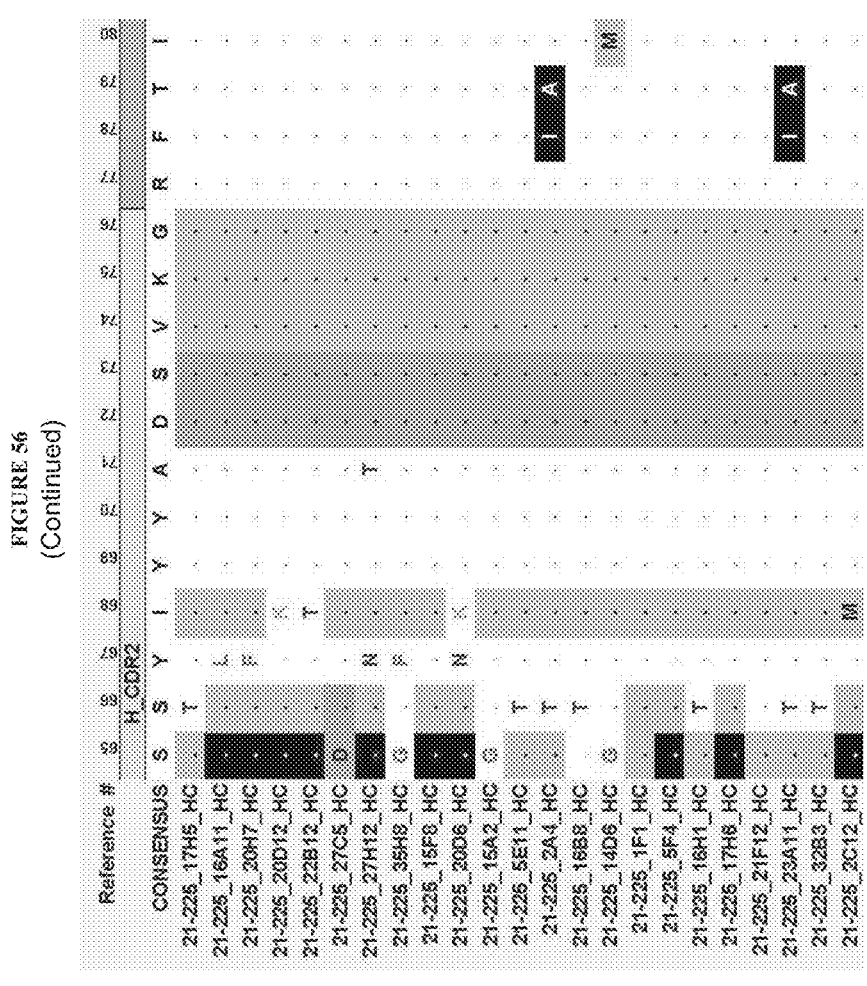
Figure 56:
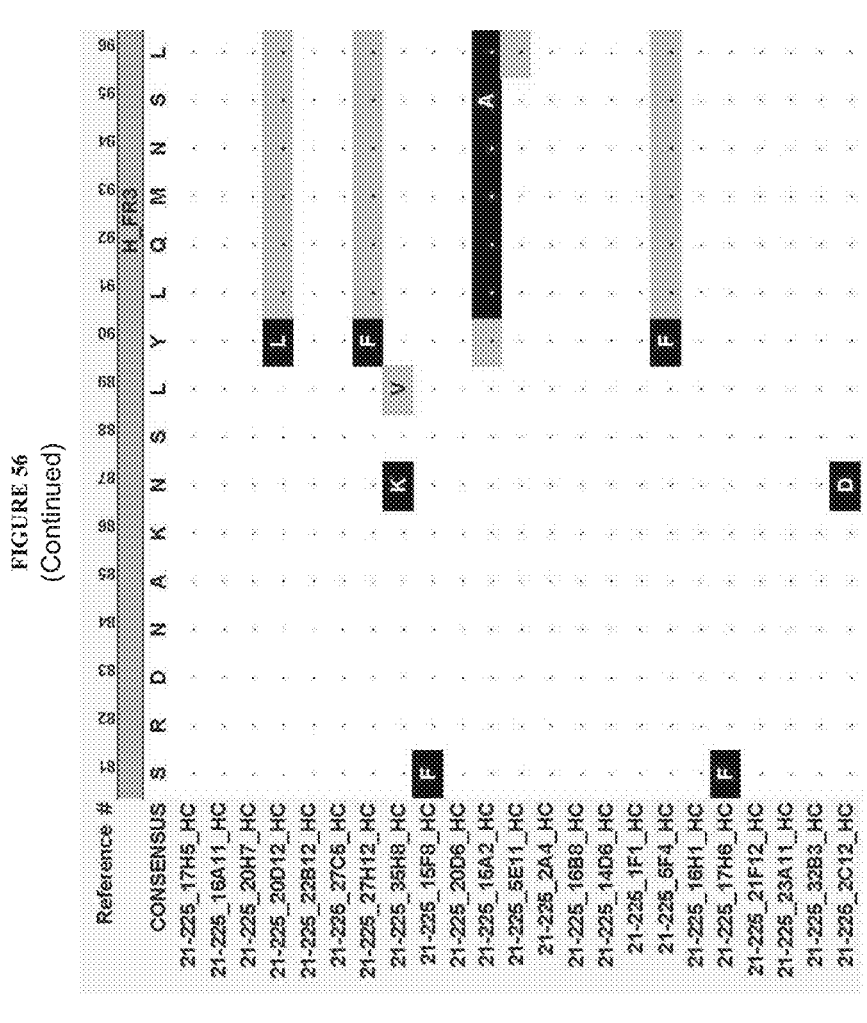
Figure 56:
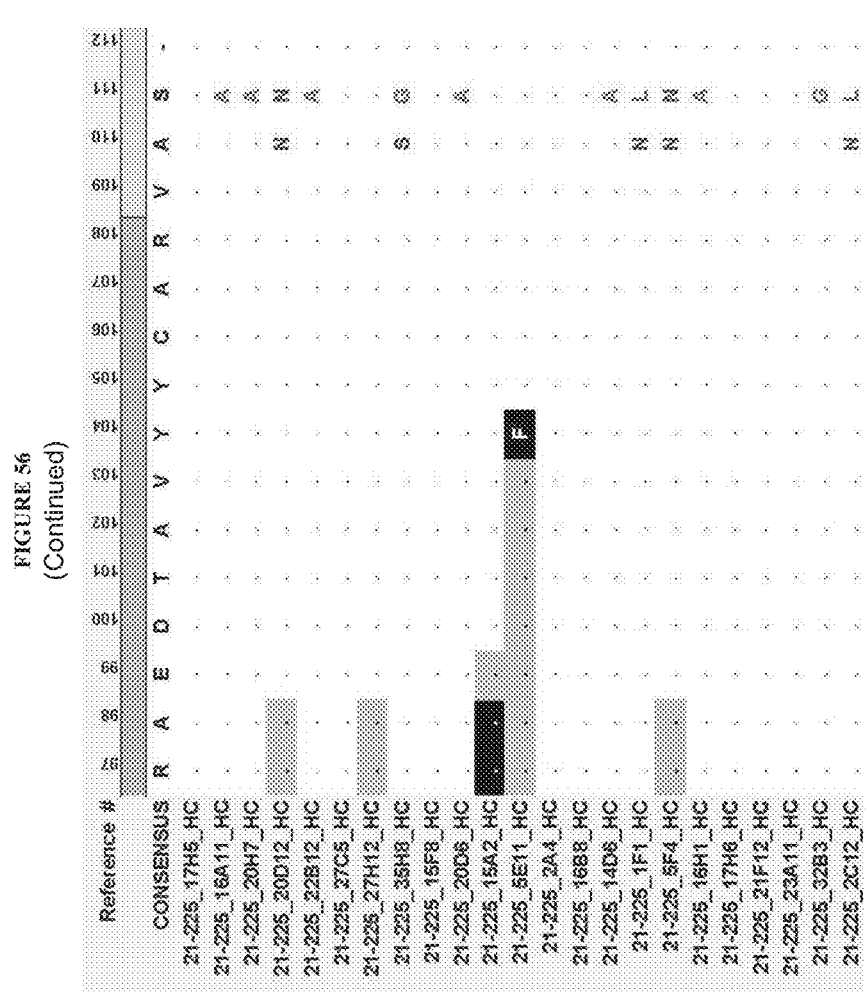
Figure 56:
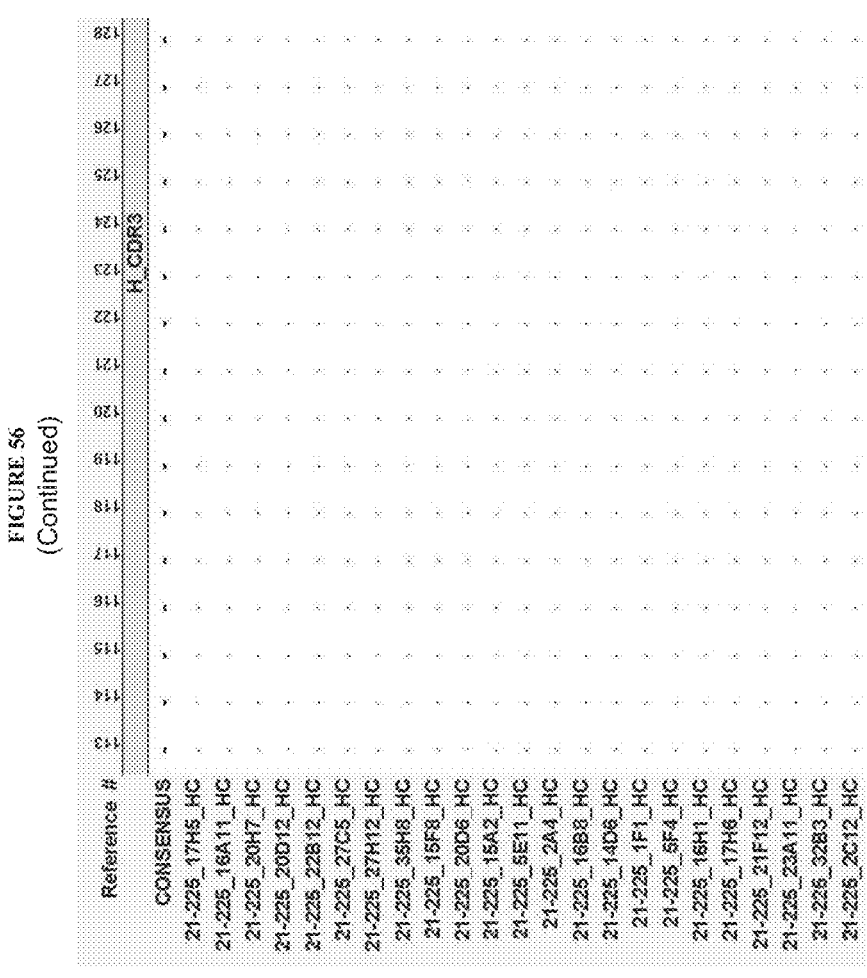
Figure 56:
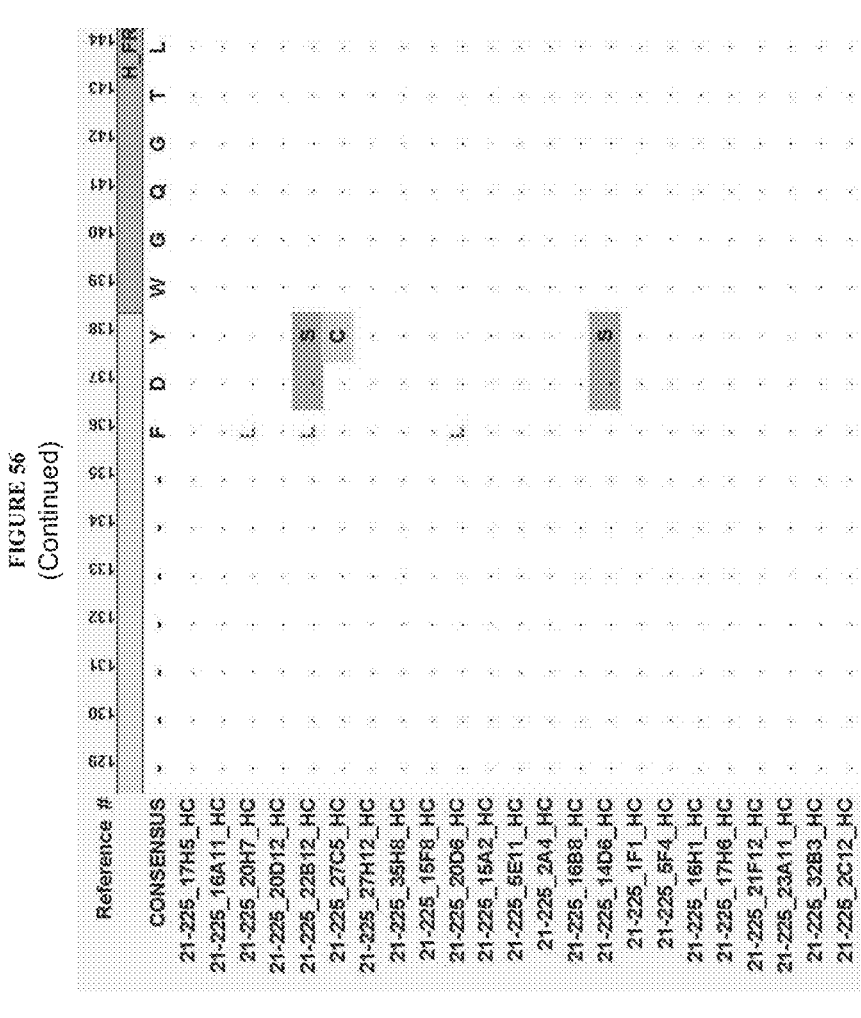
Figure 56:
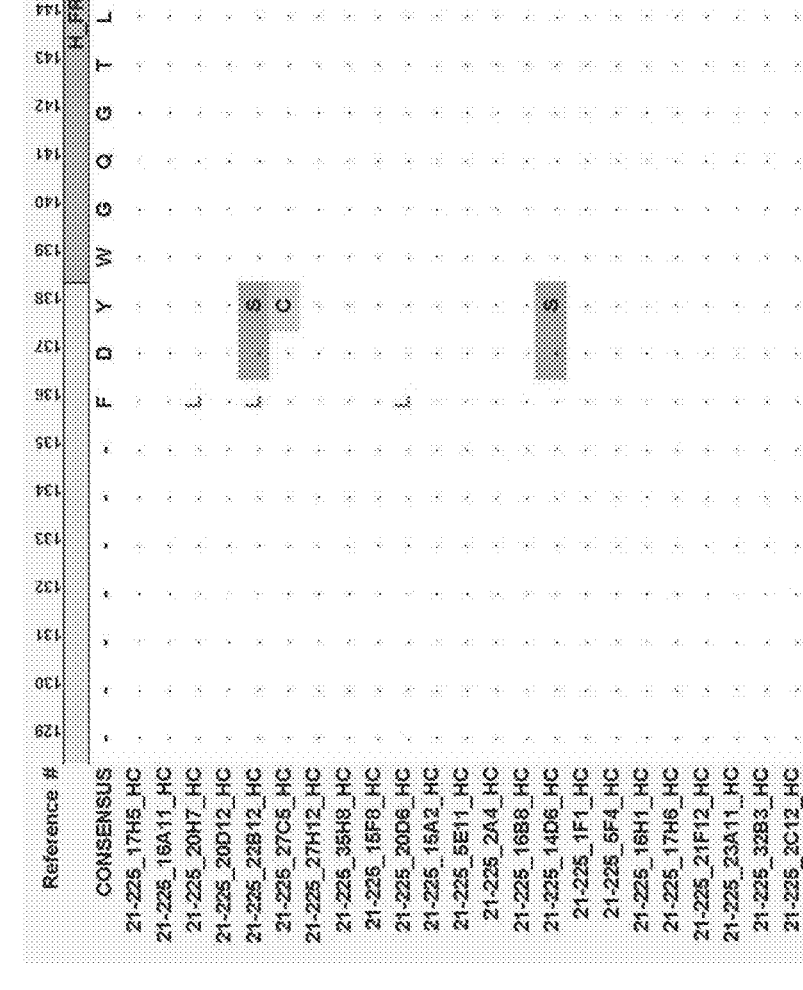
Figure 56:
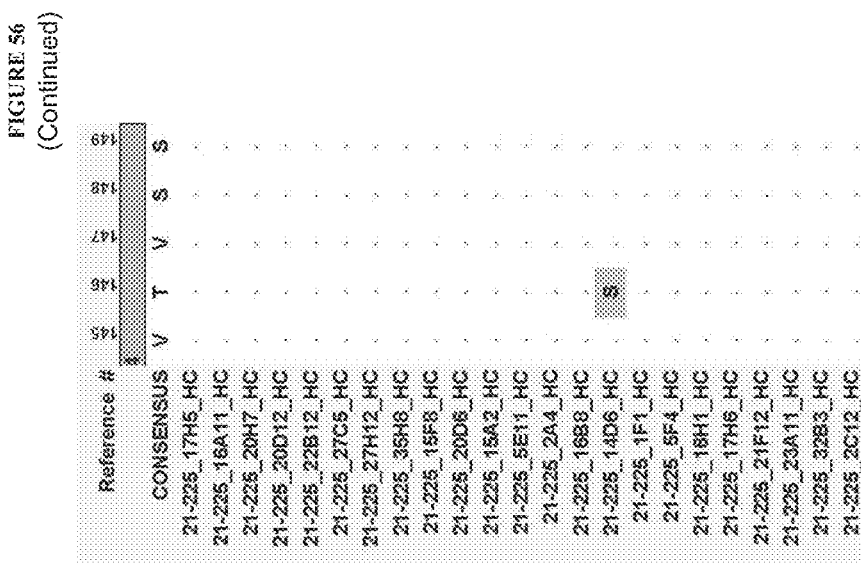
Figure 56:
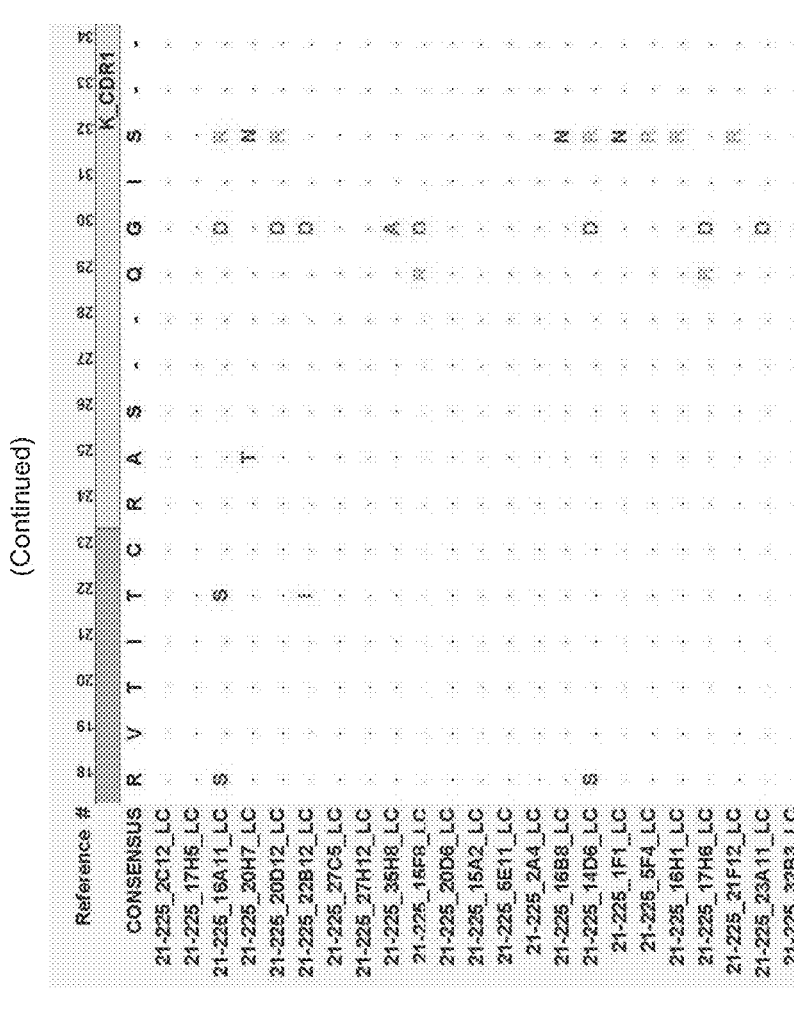
Figure 56:
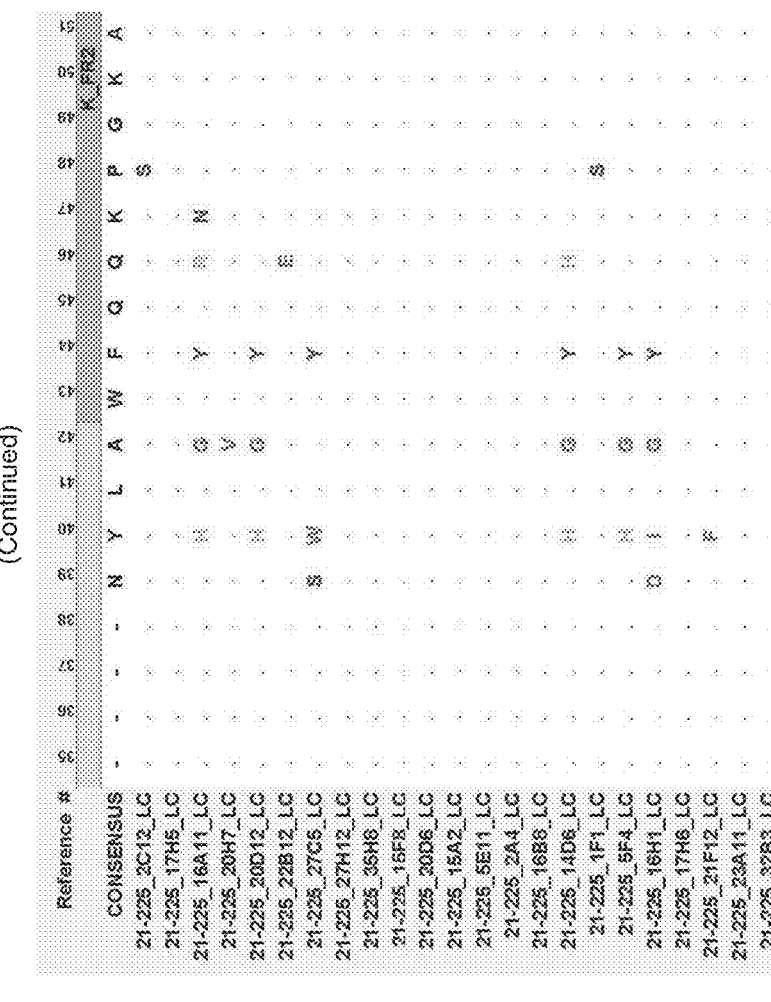
Figure 56:
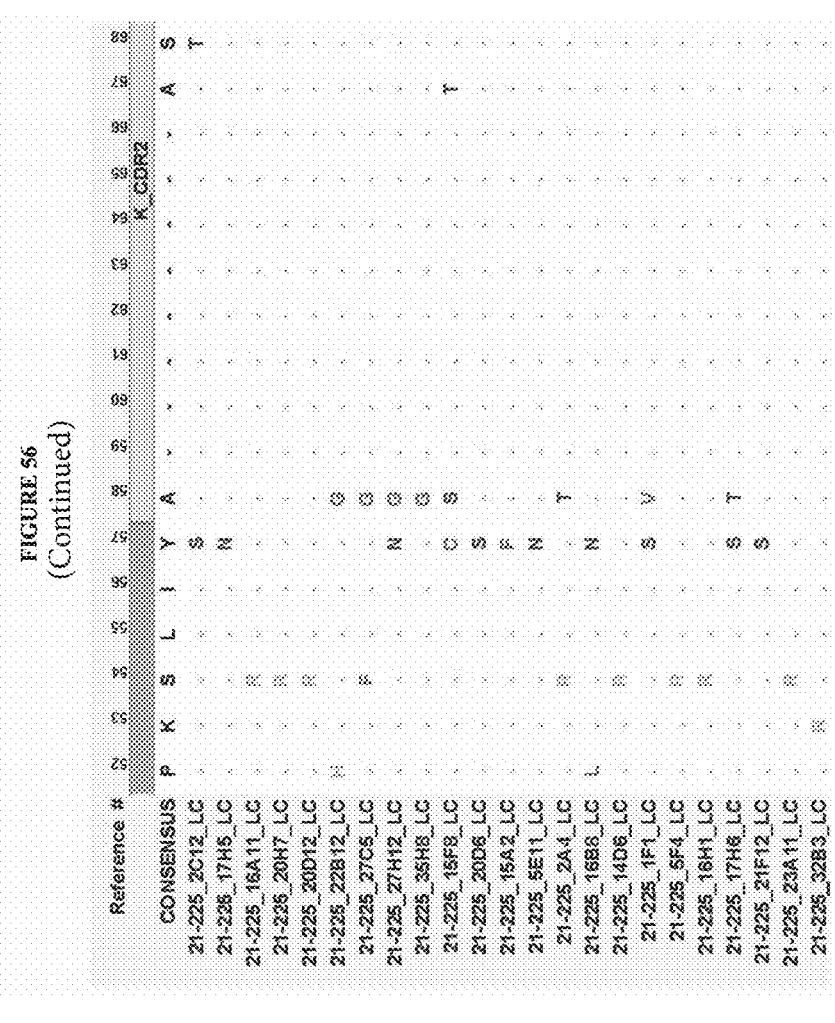
Figure 56:
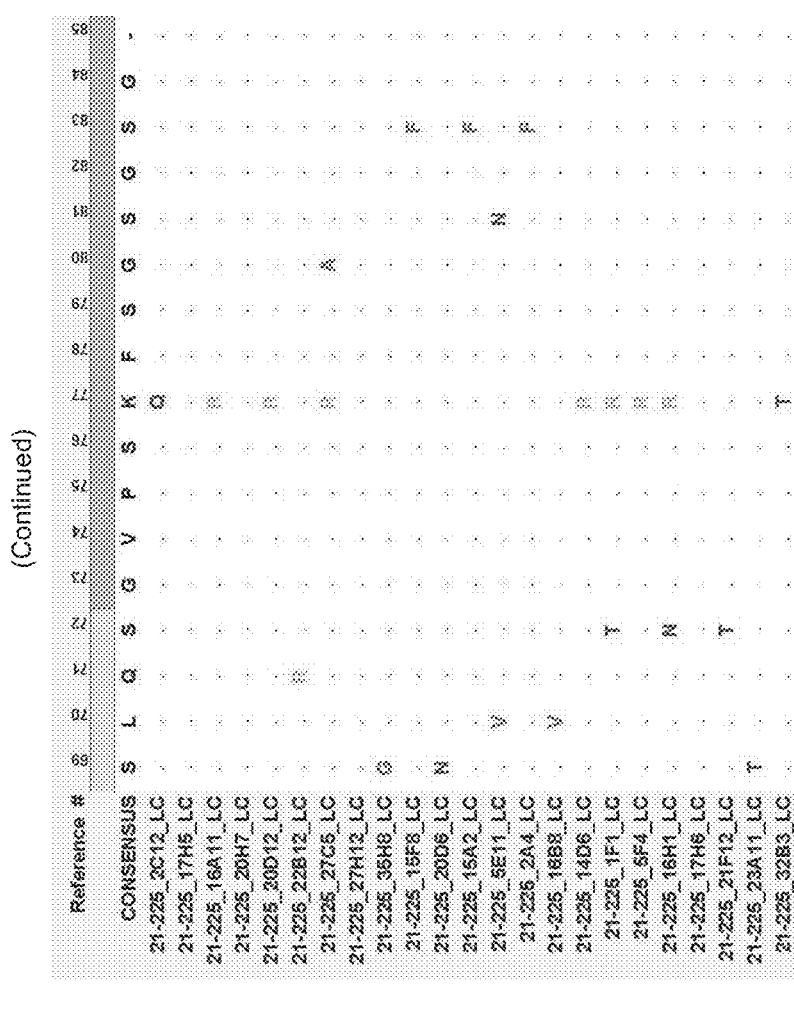
Figure 56:
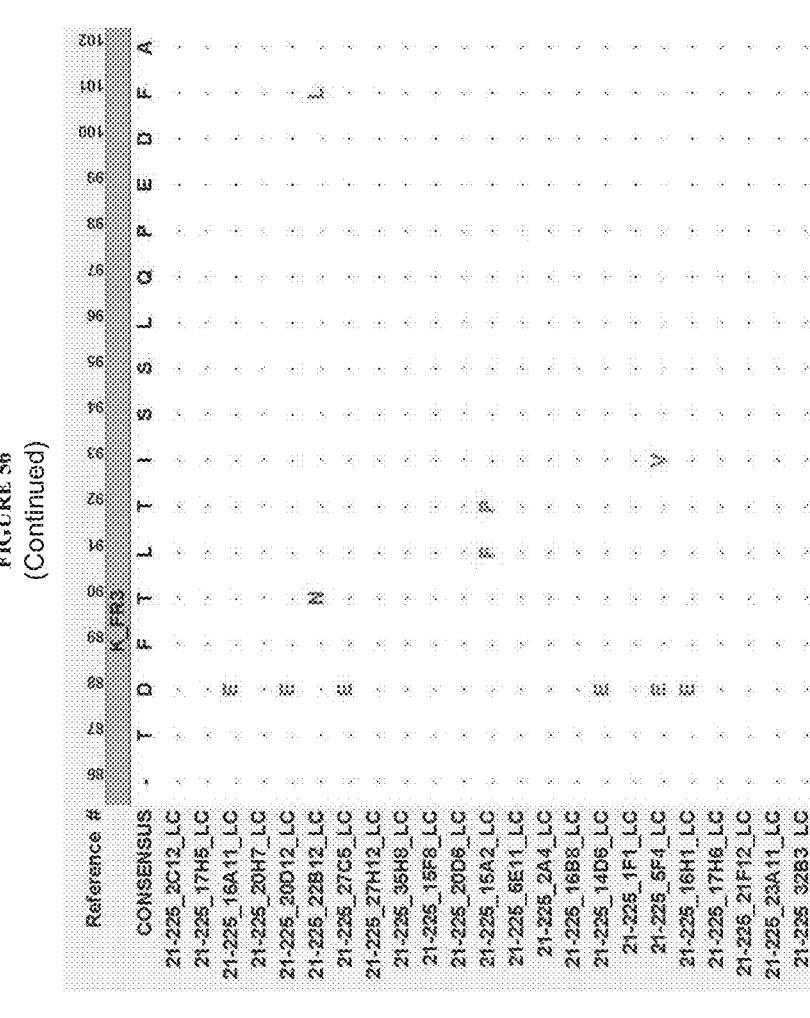
Figure 56:
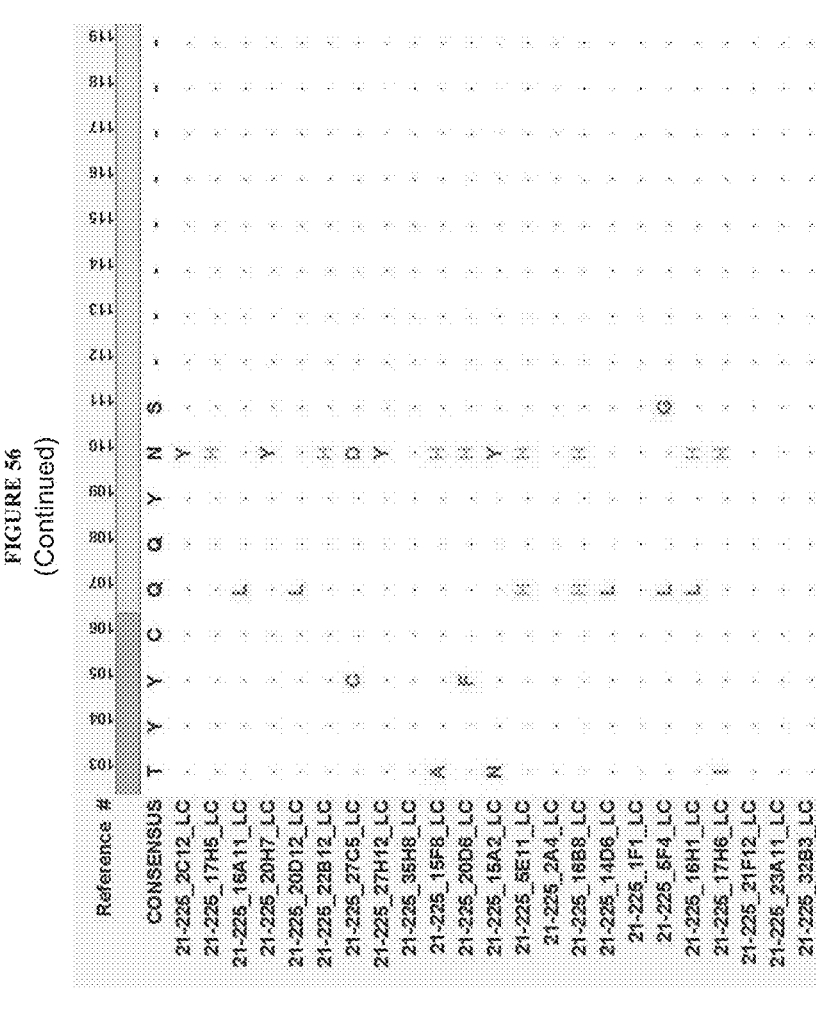
Figure 56:
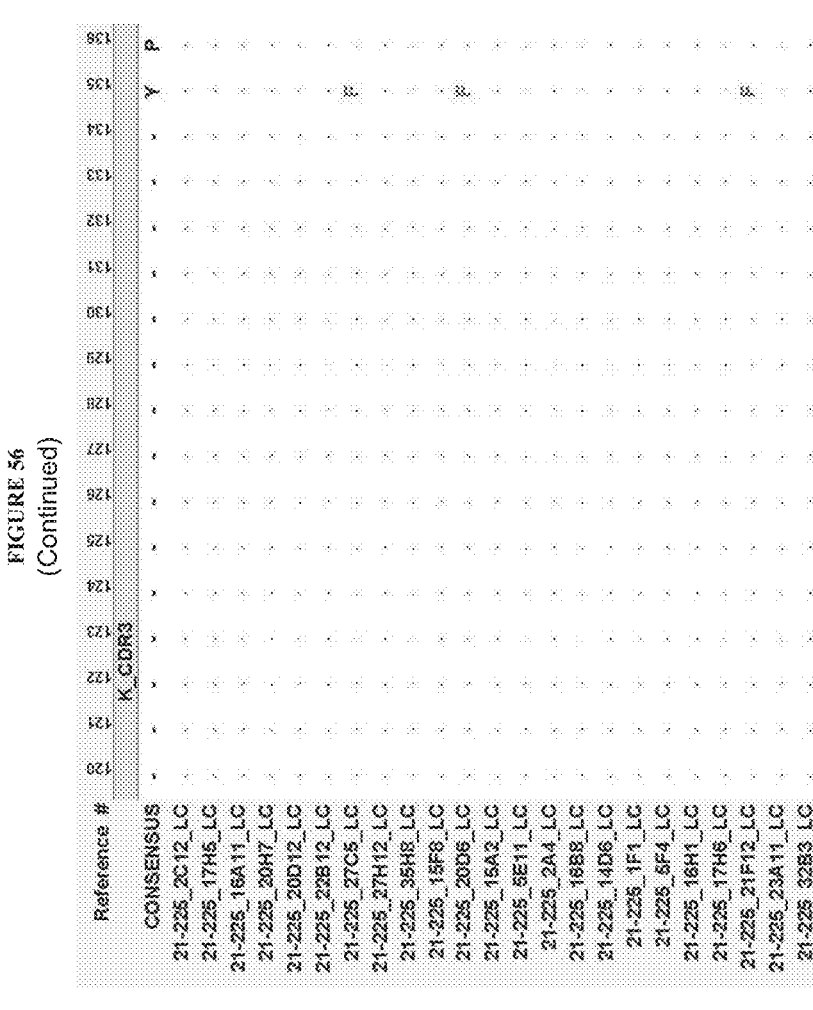
Figure 56:
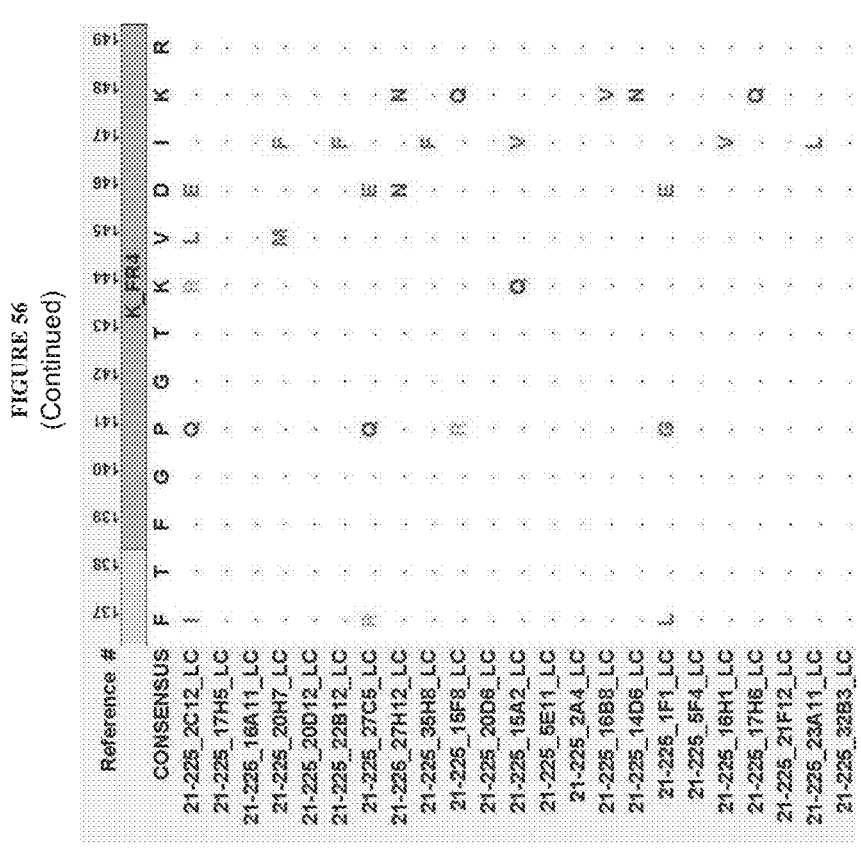
Figure 56:
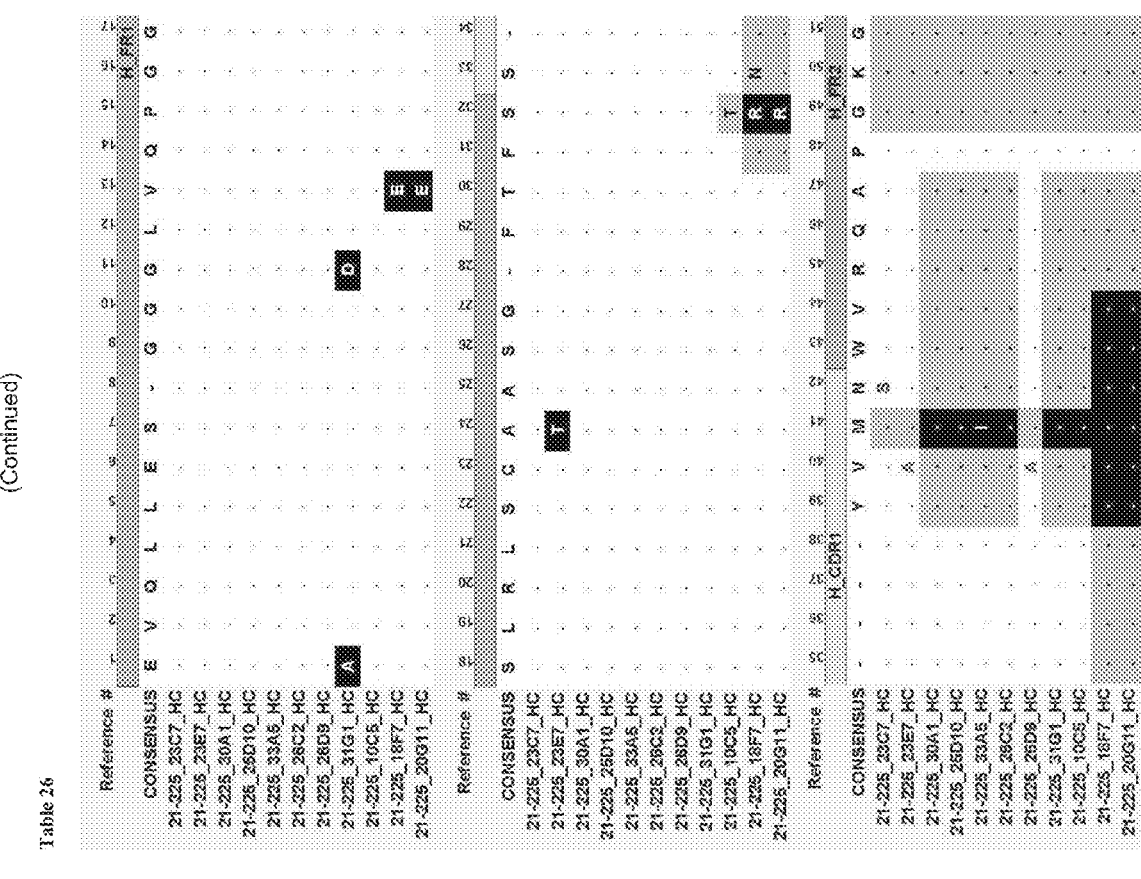
Figure 56:
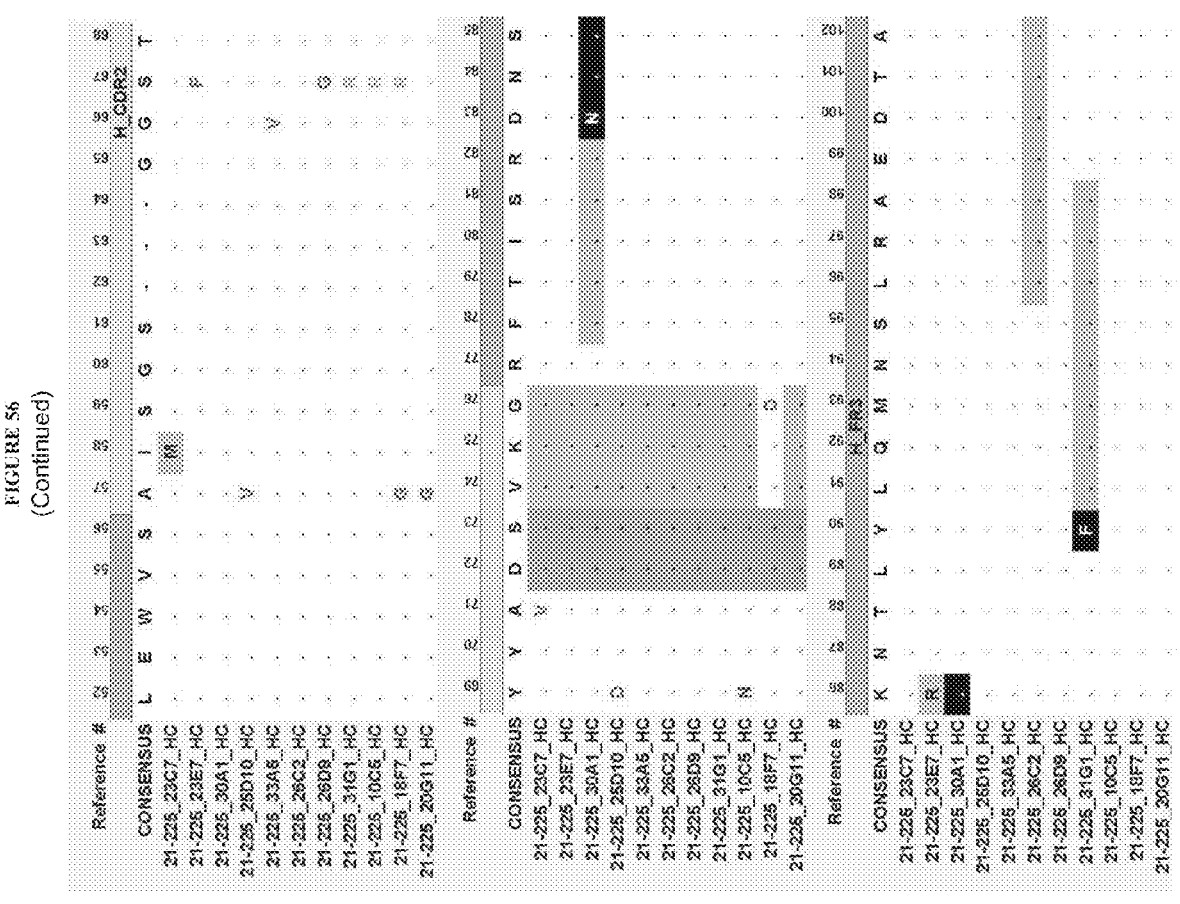
Figure 56:
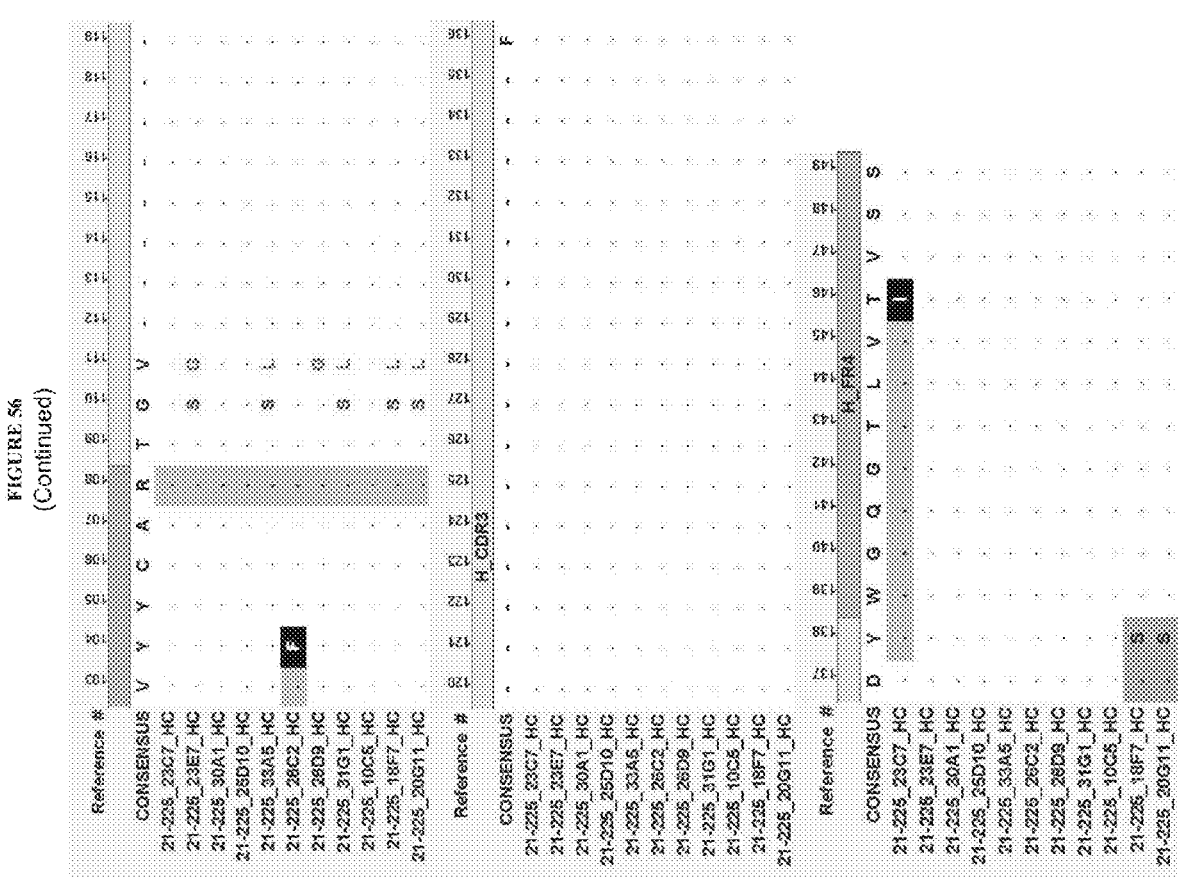
Figure 56:
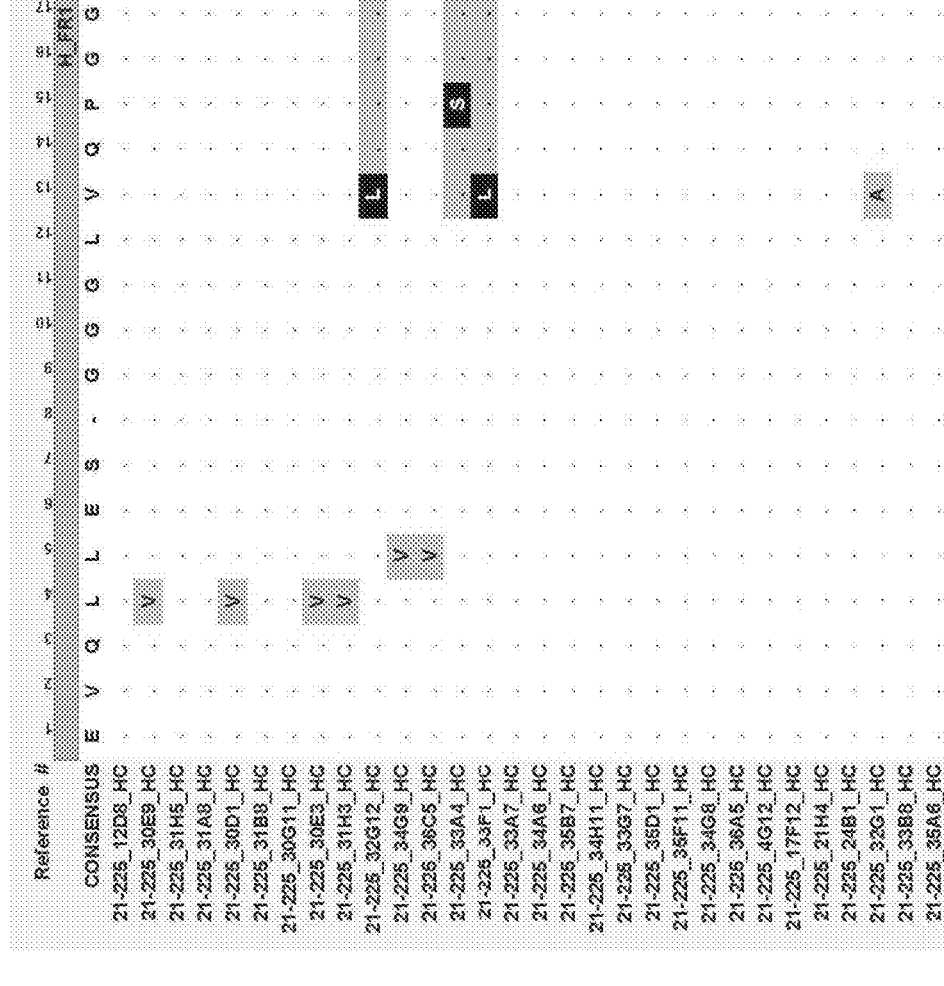
Figure 56:
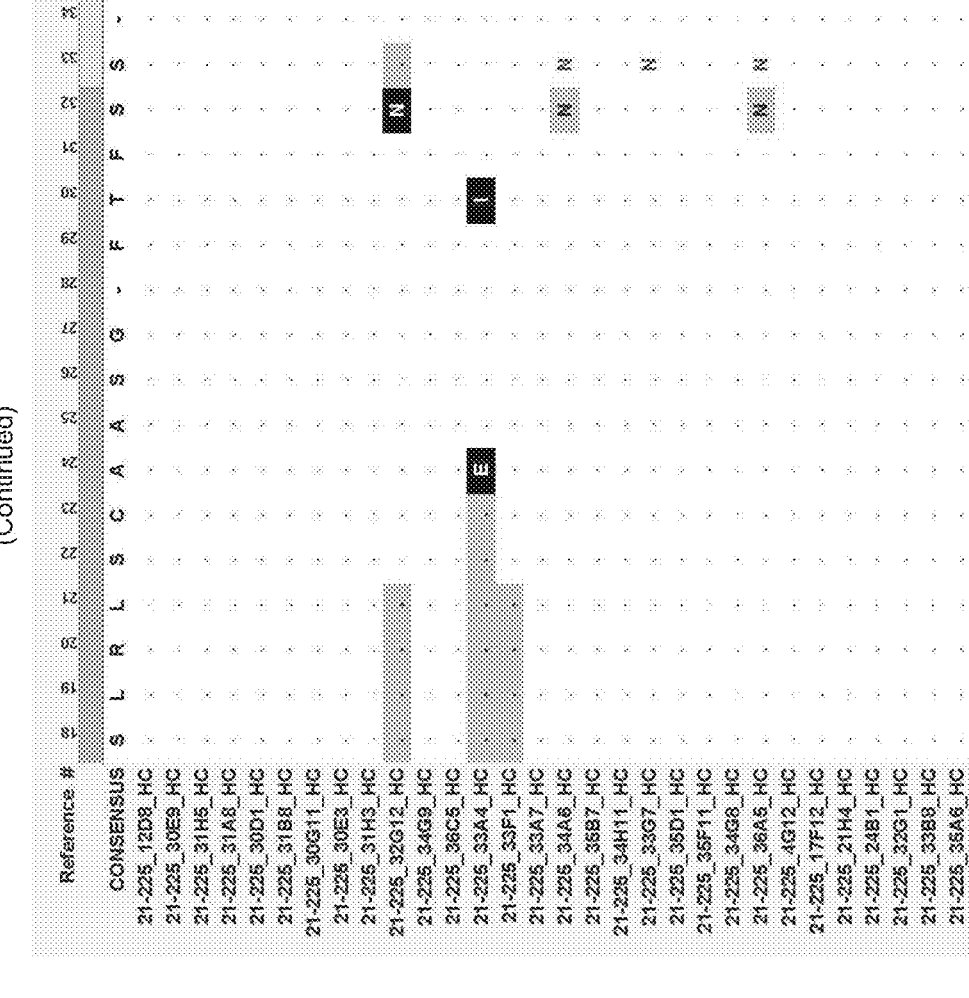
Figure 56:
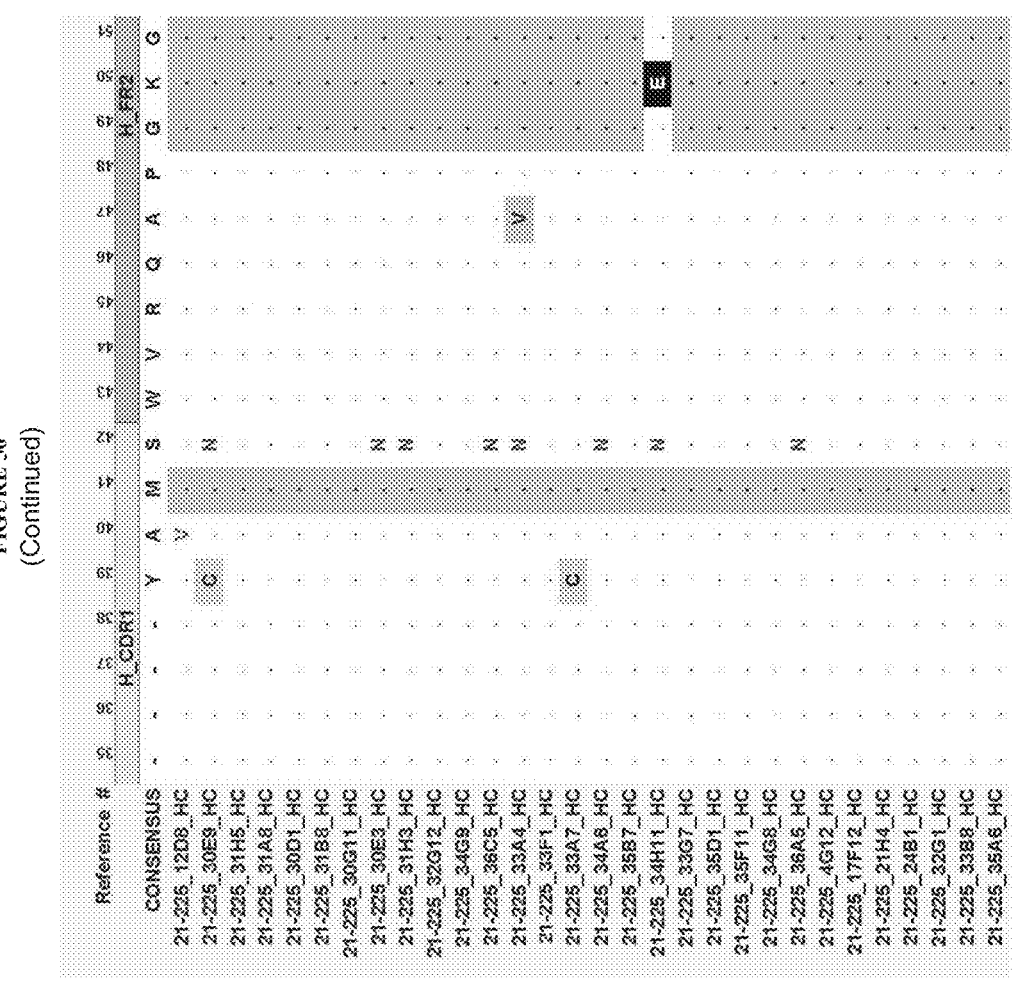
Figure 56:
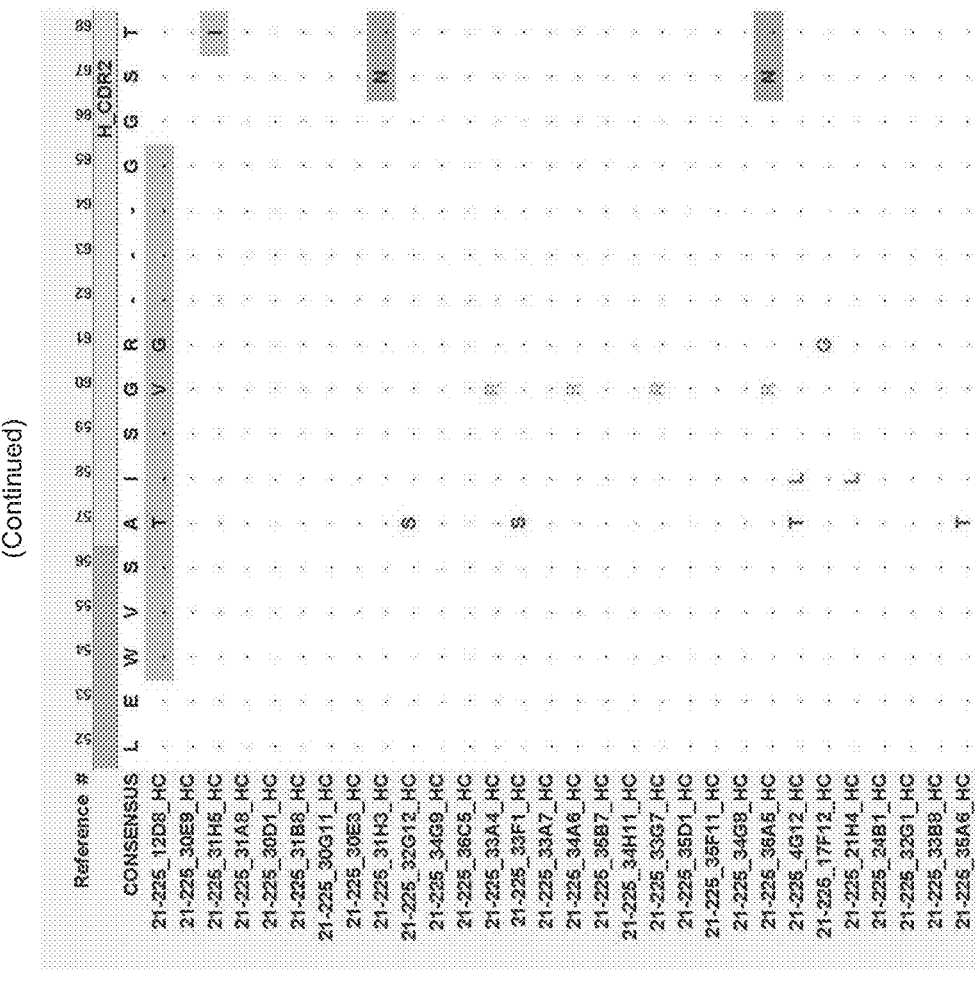
Figure 56:
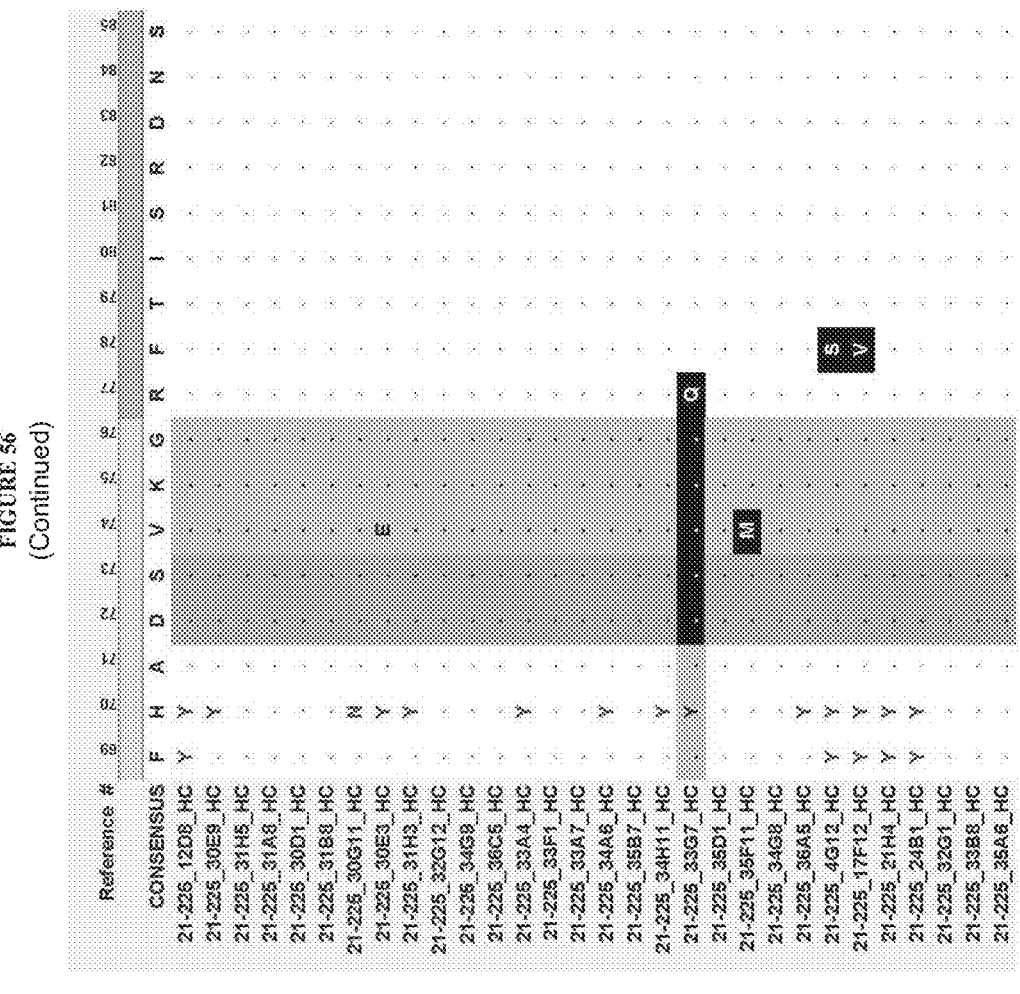
Figure 56:
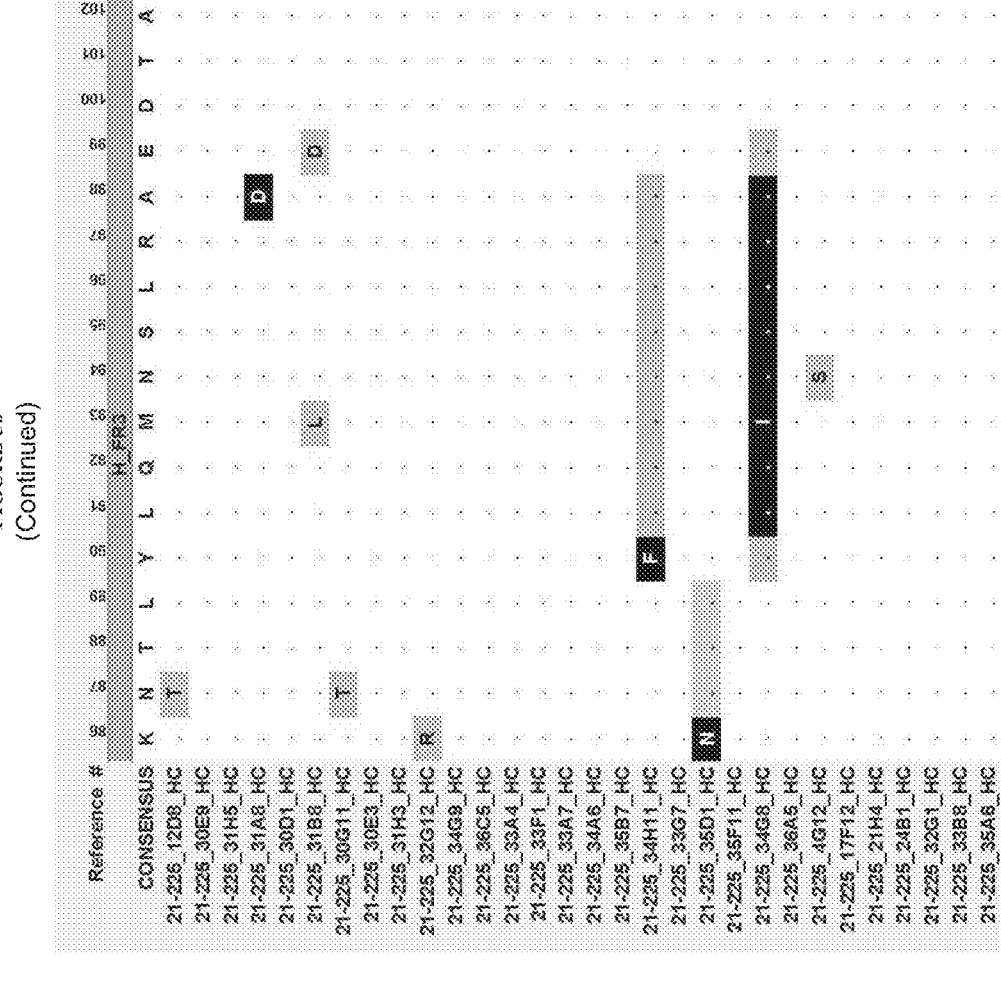
Figure 56:
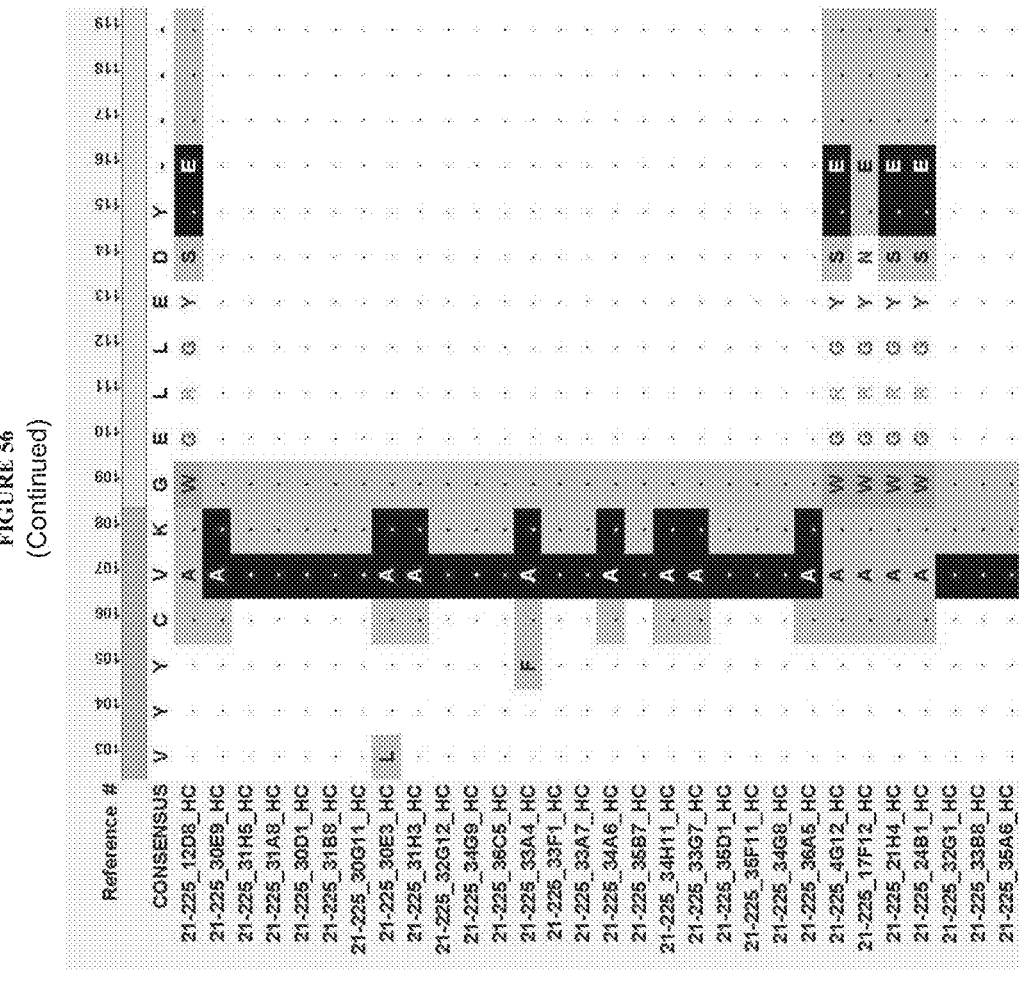
Figure 56:
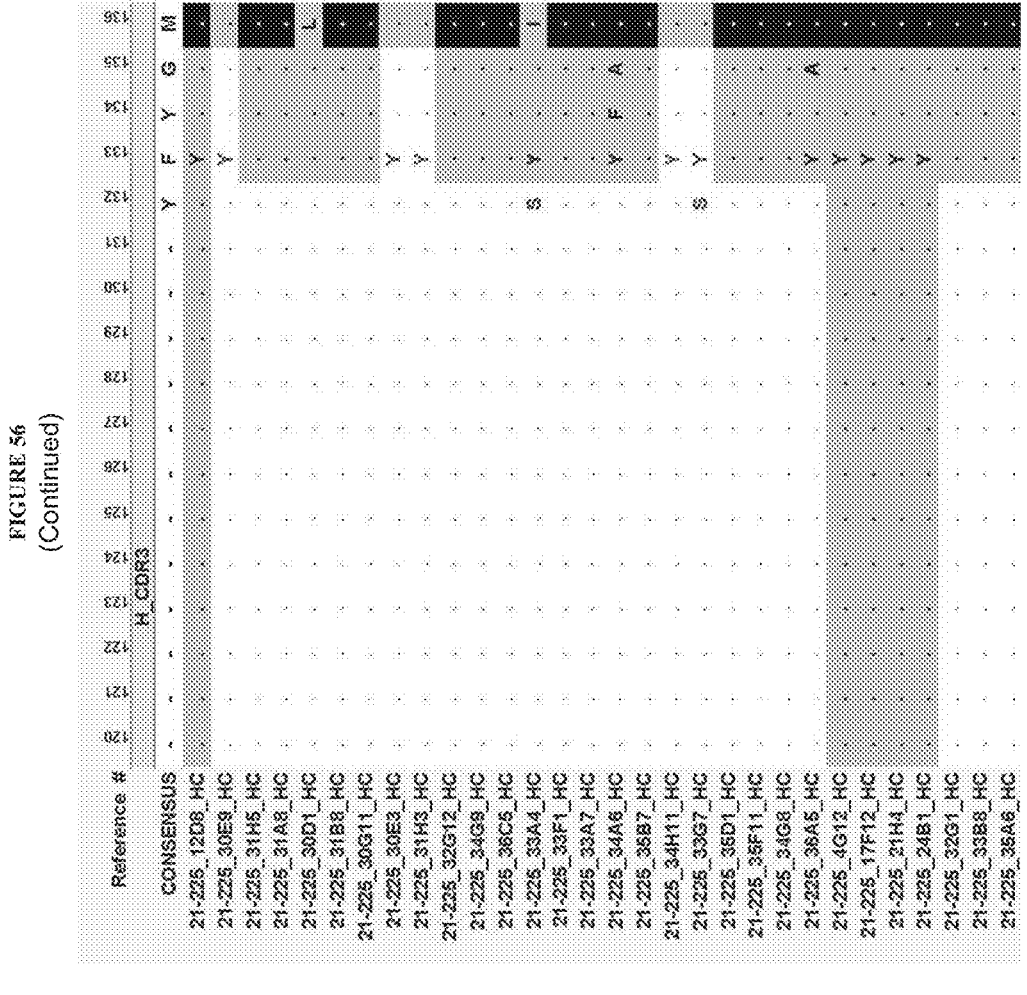
Figure 56:
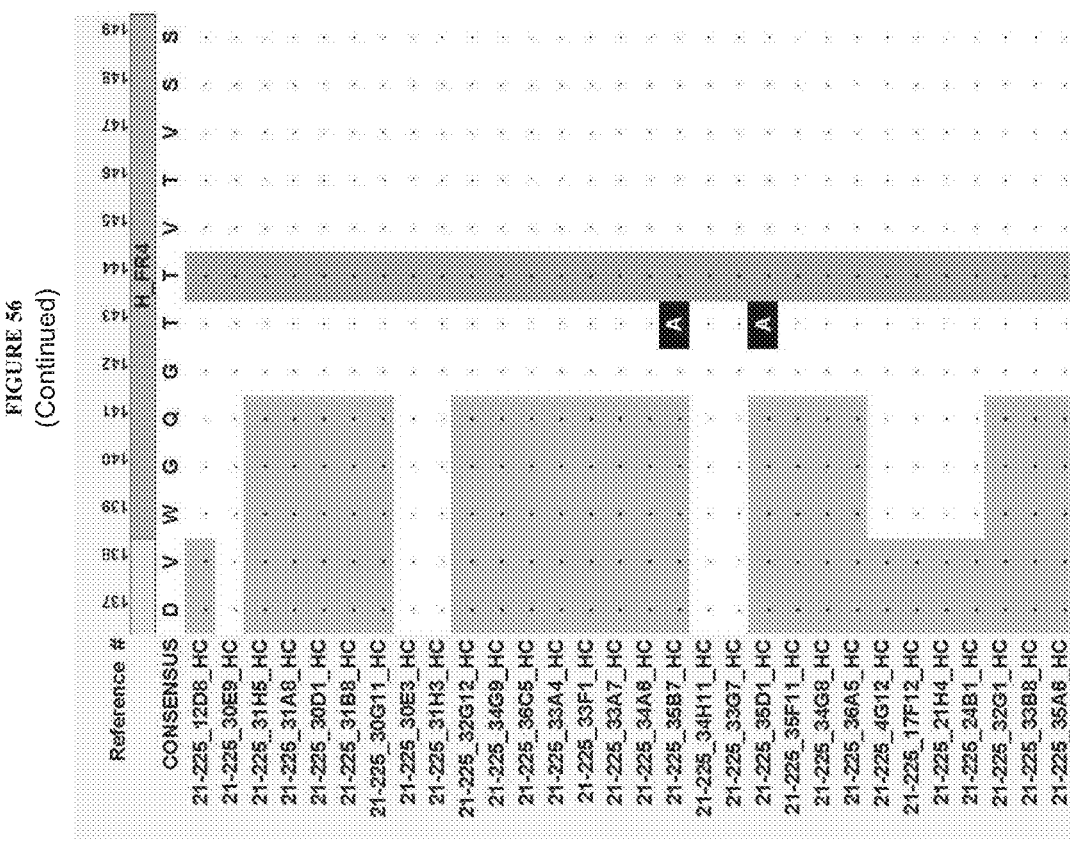
Figure 56:
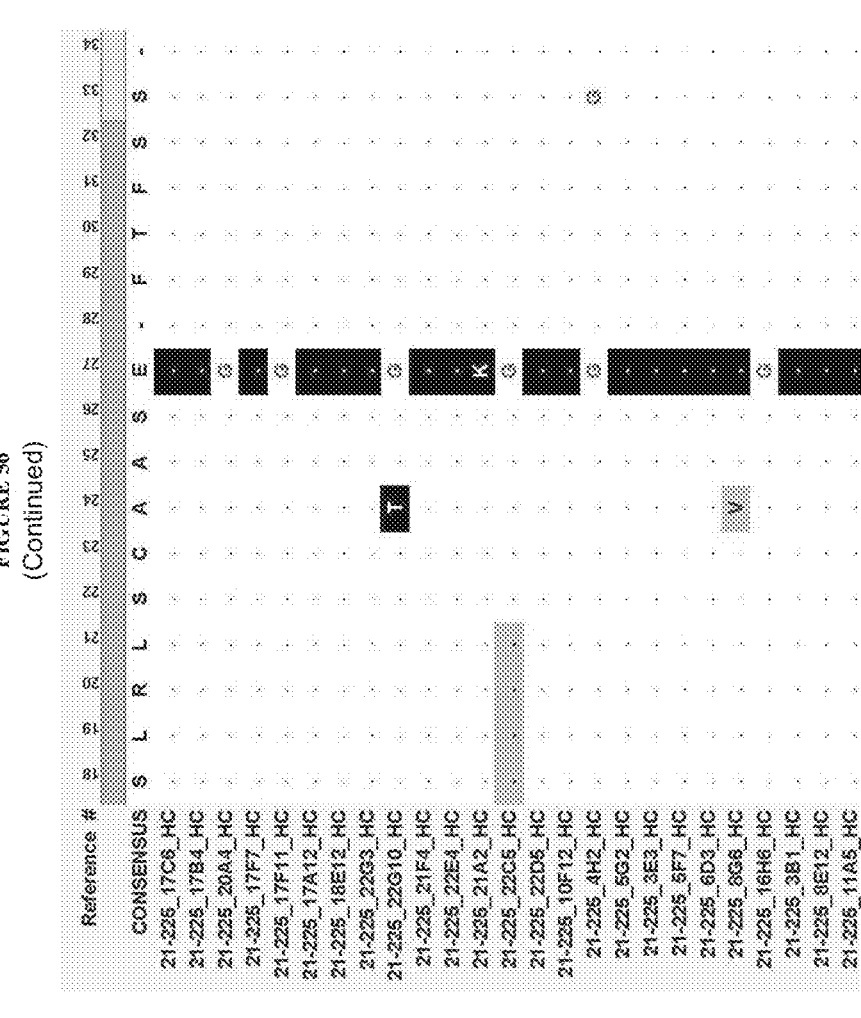
Figure 56:
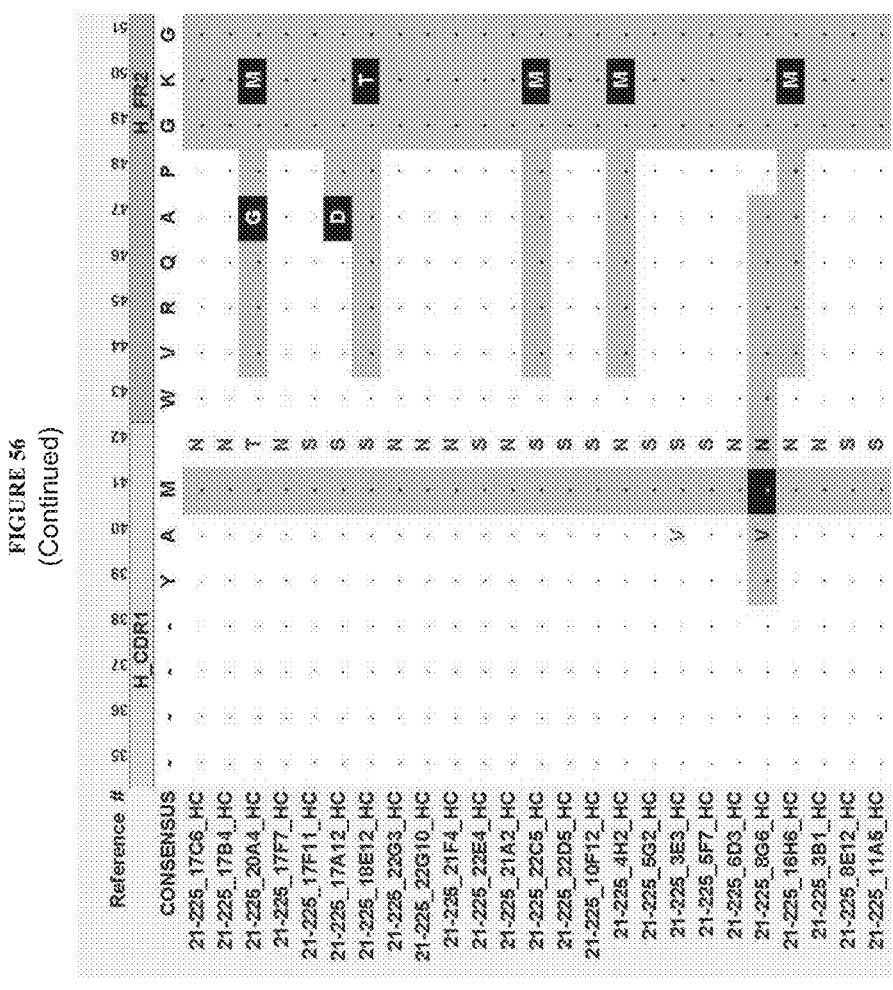
Figure 56:
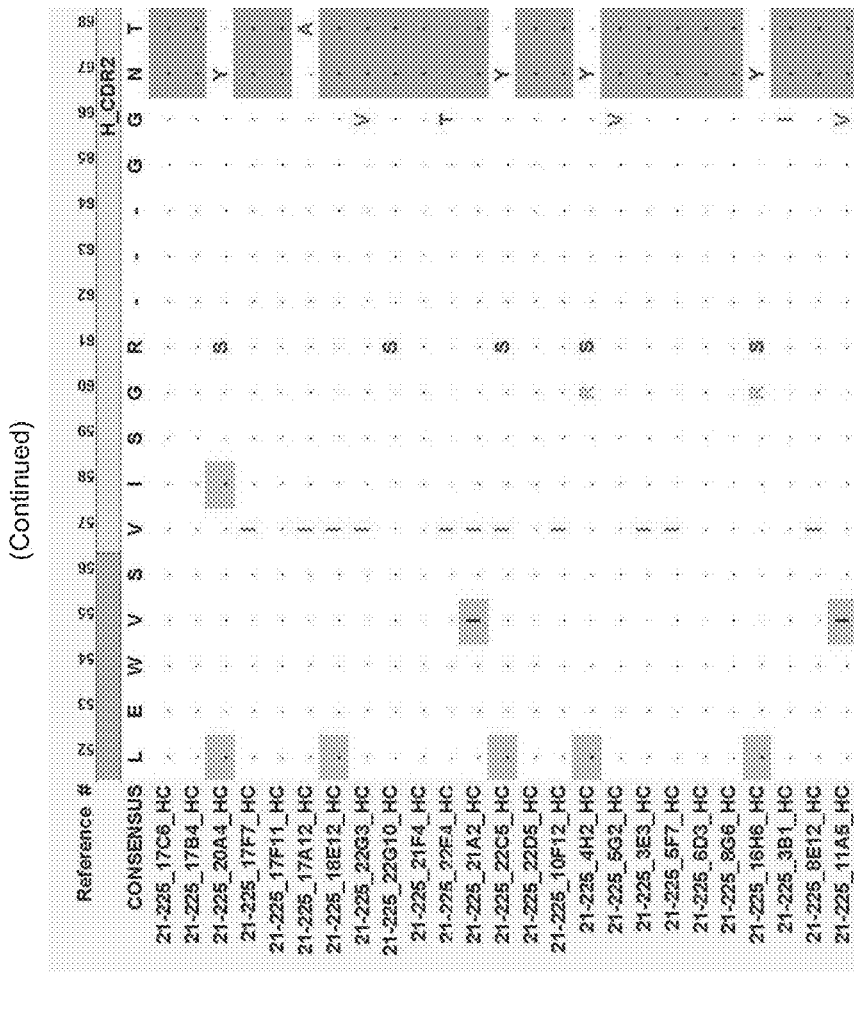
Figure 56:
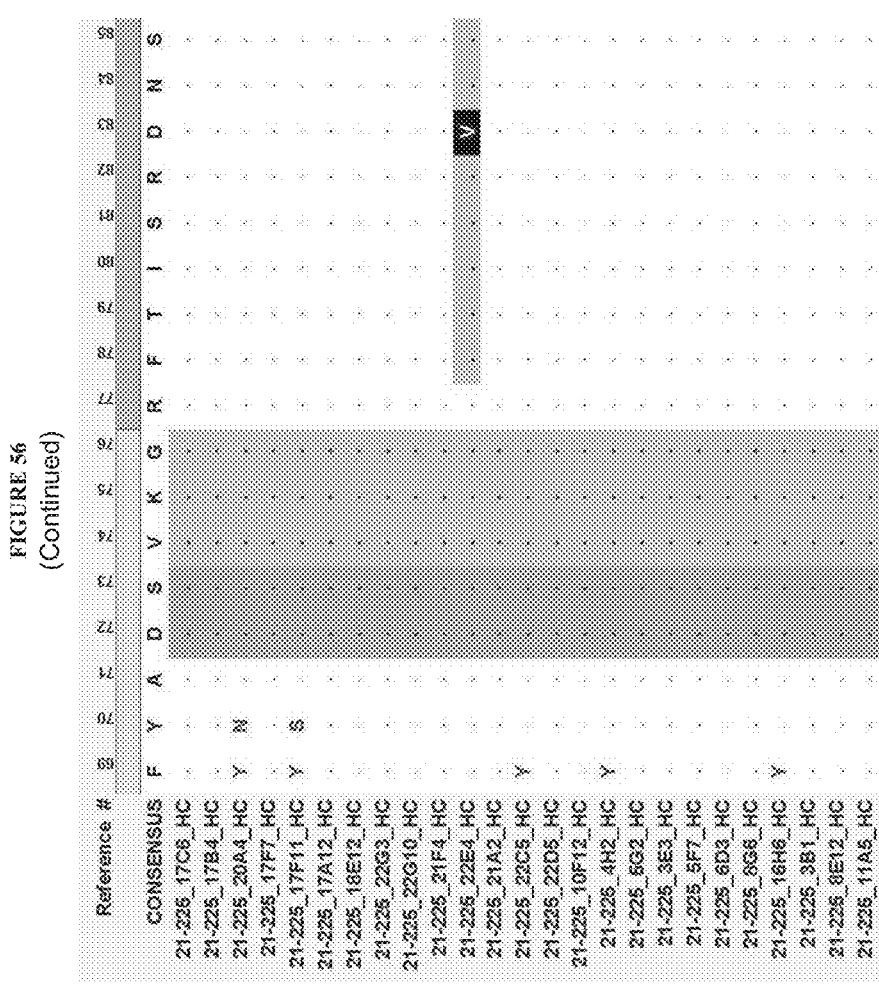
Figure 56:
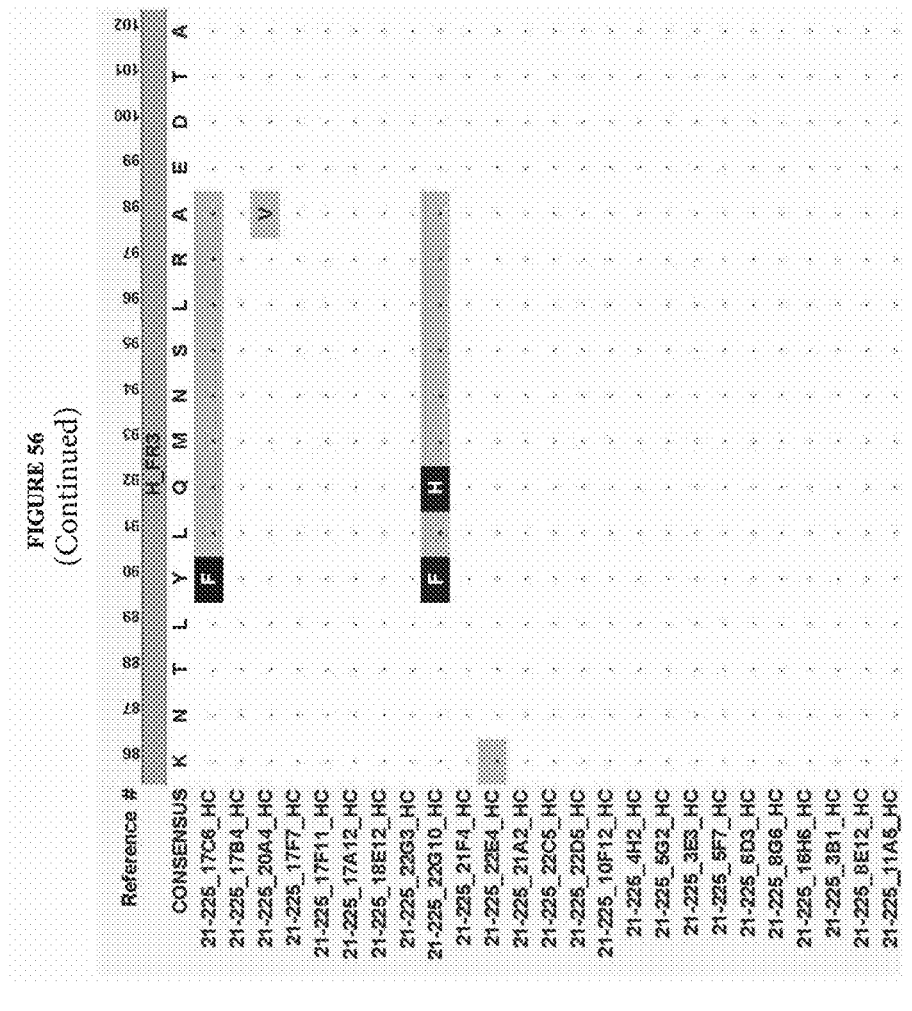
Figure 56:
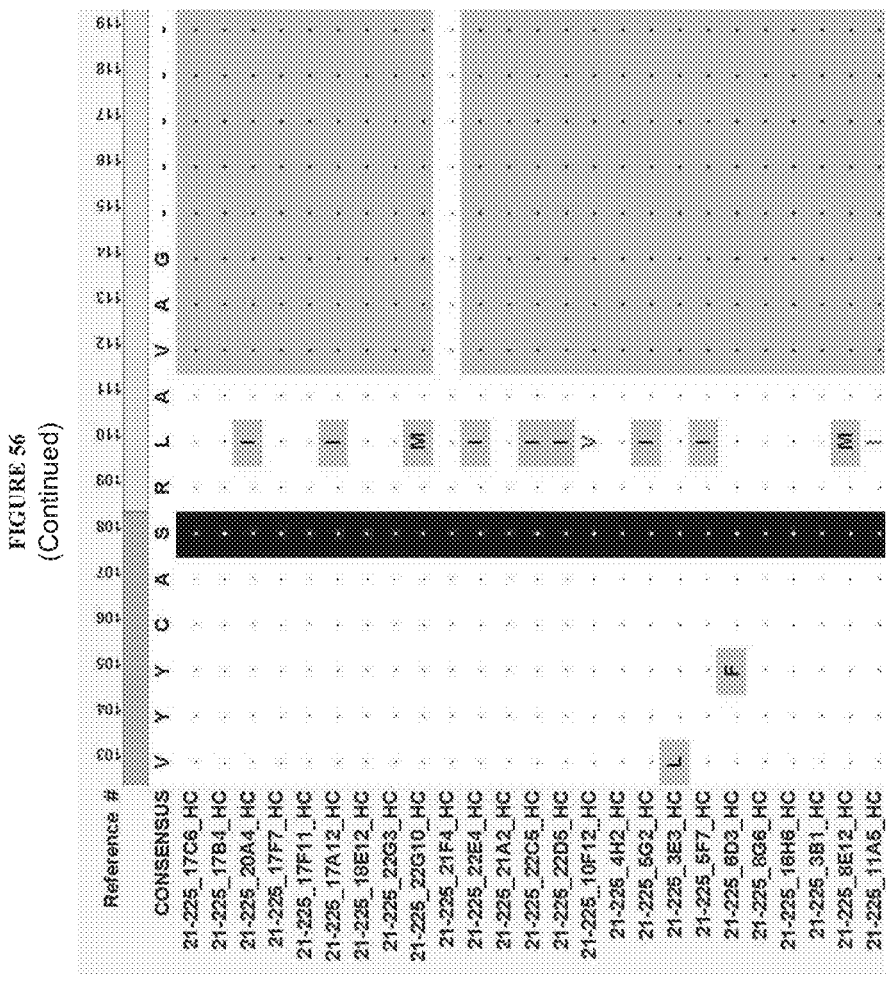
Figure 56:
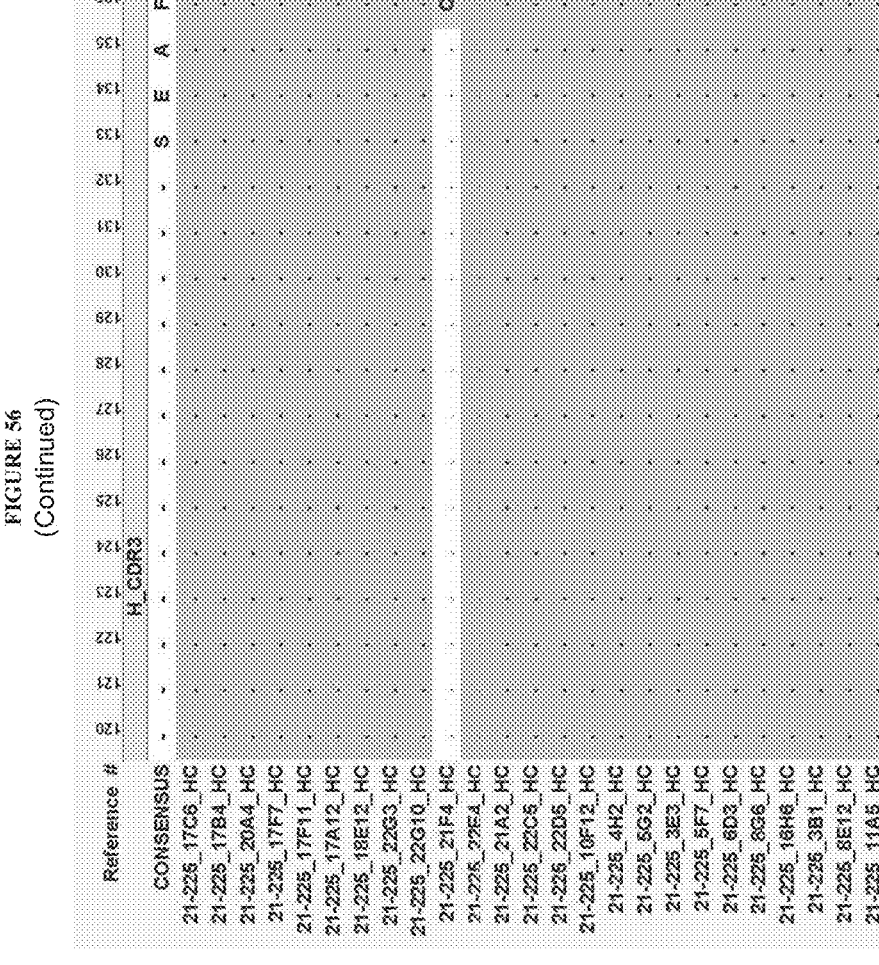
Figure 56:
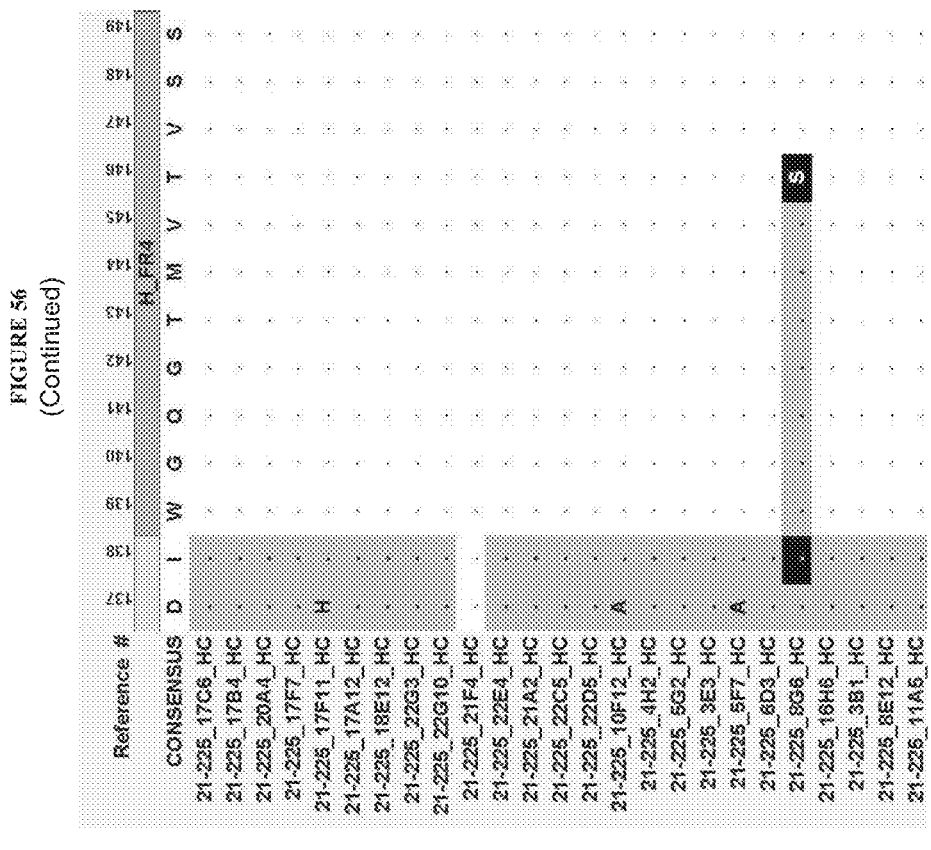
Figure 56:
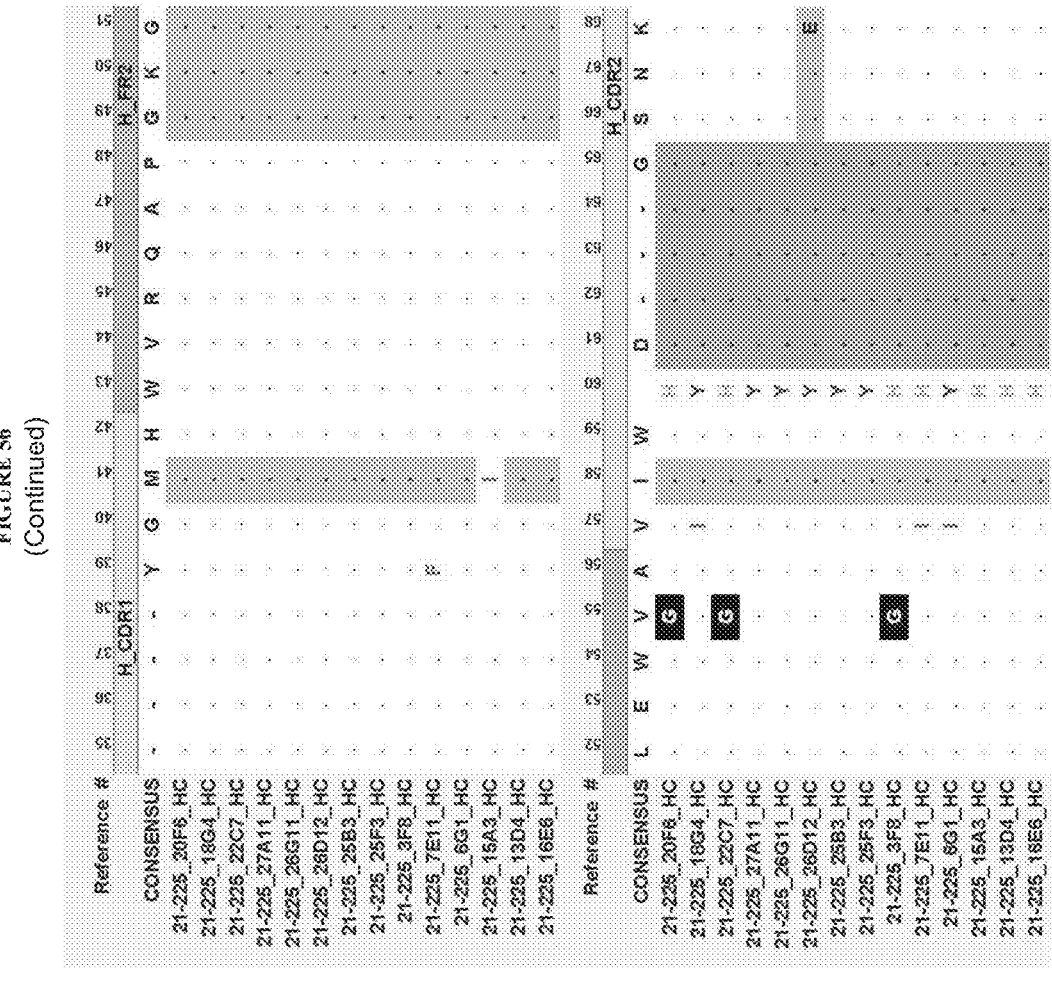
Figure 56:
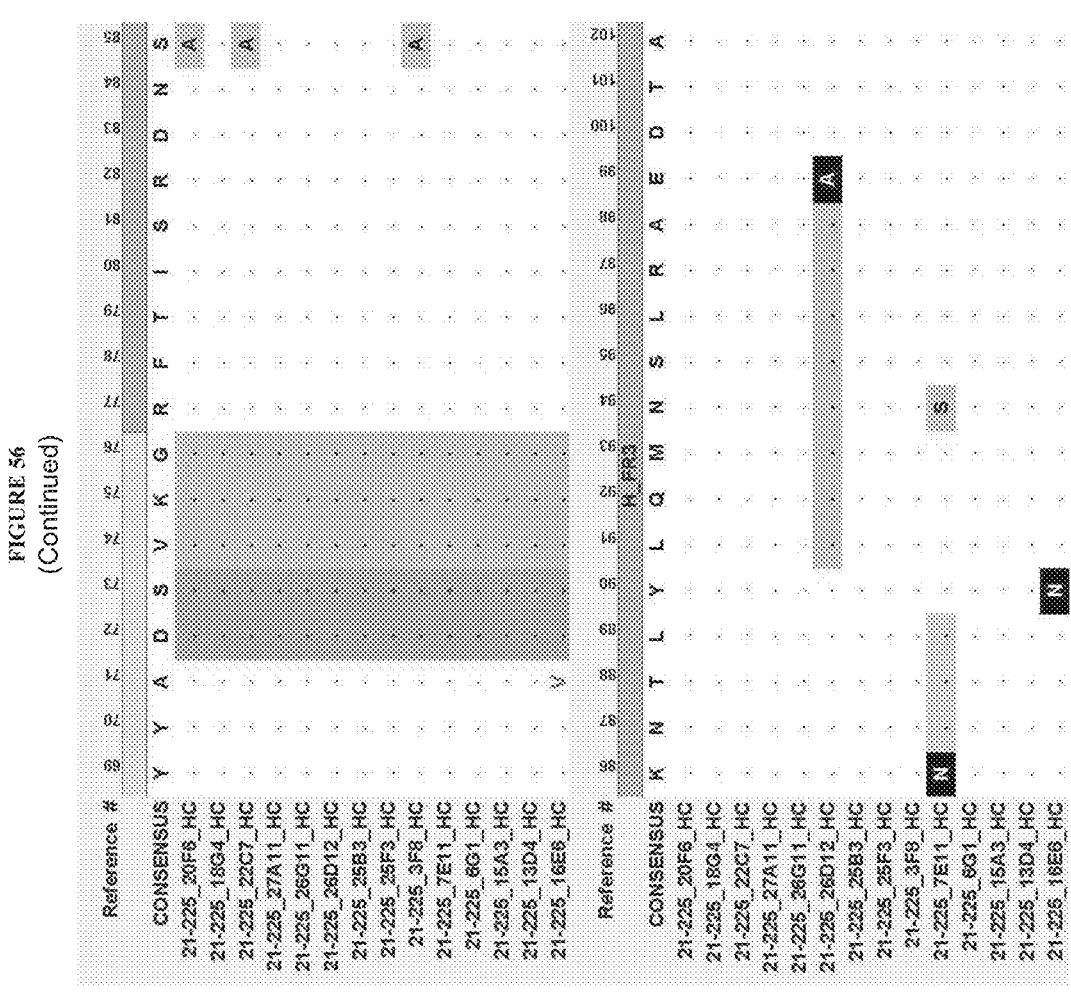
Figure 56:
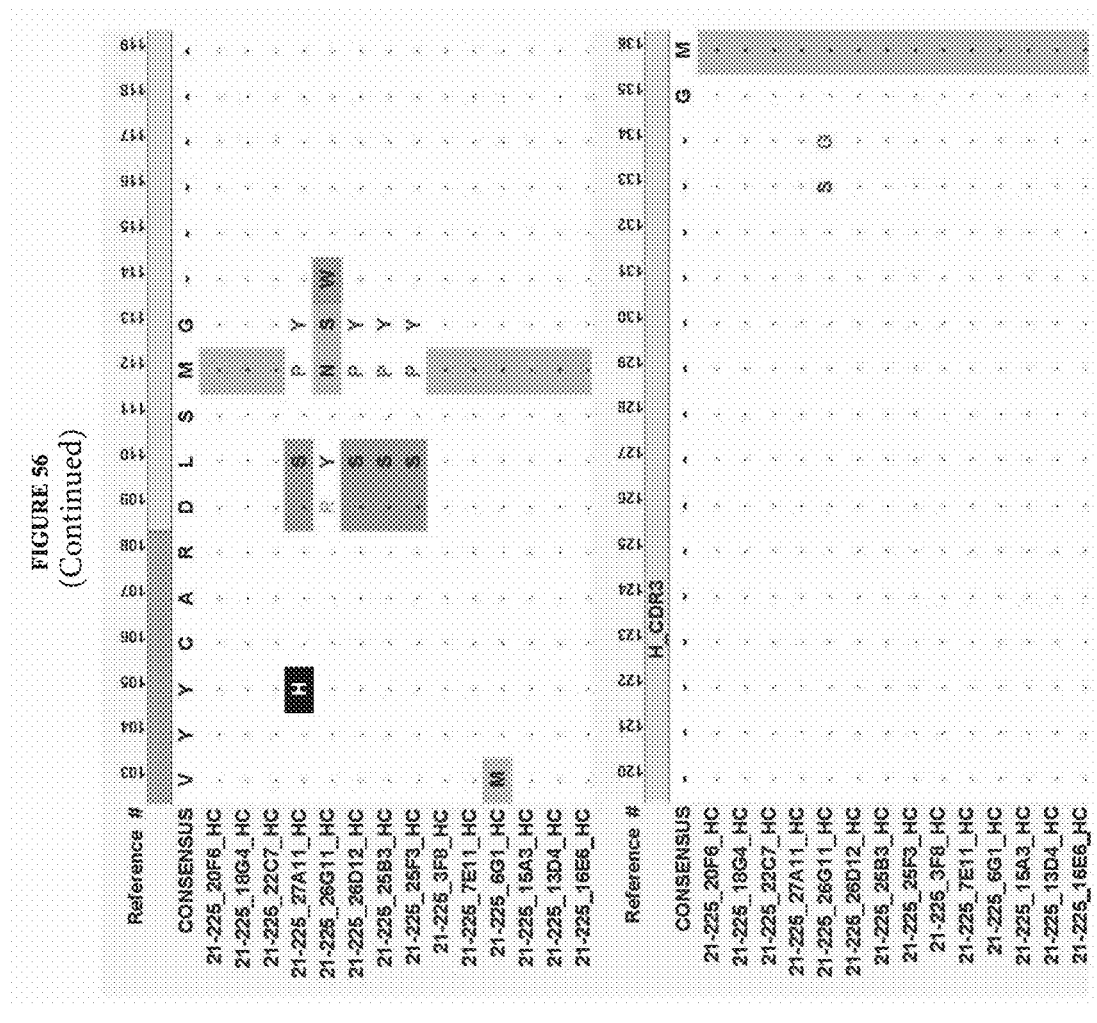
Figure 56:
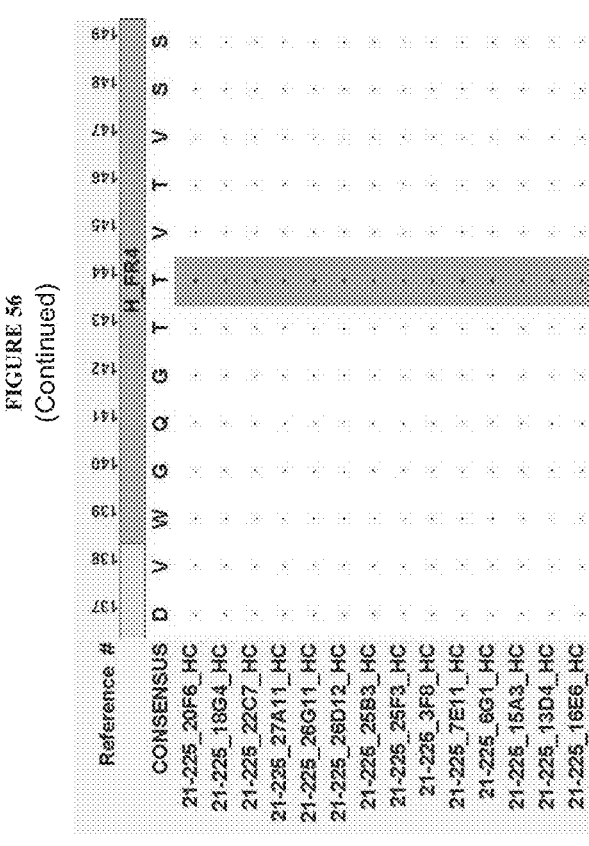
Figure 56:
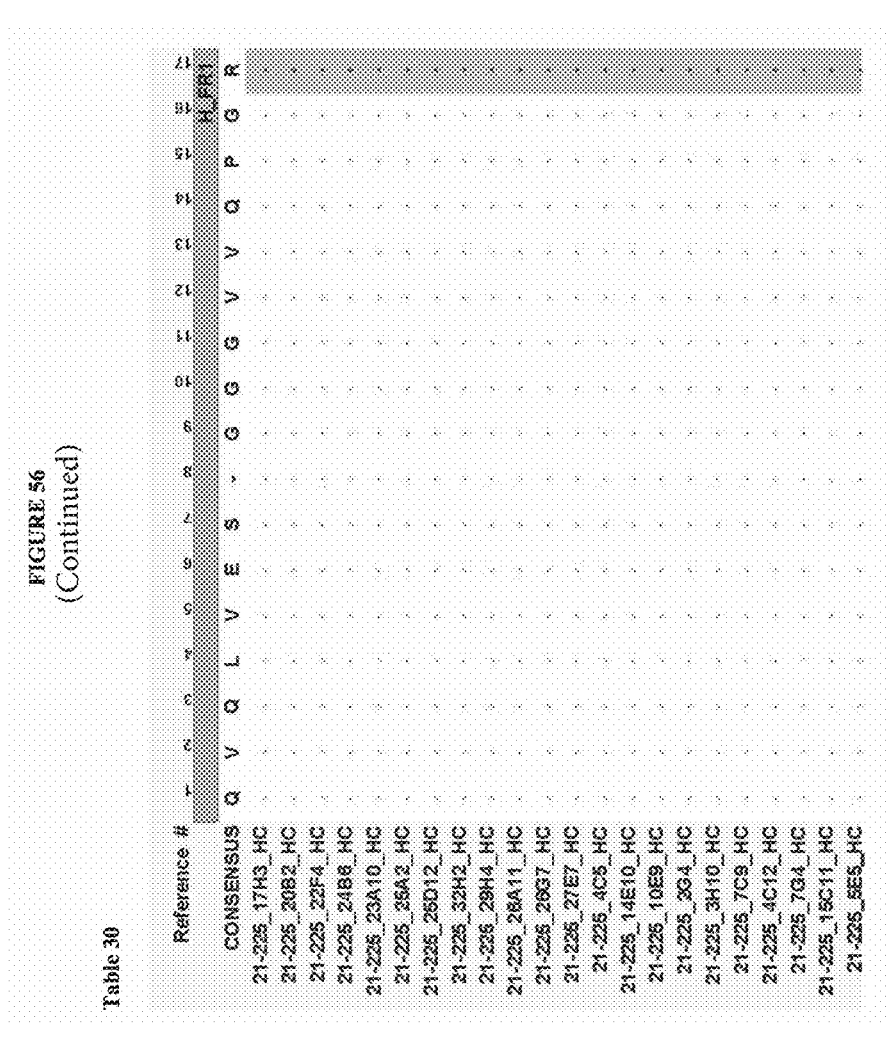
Figure 56:
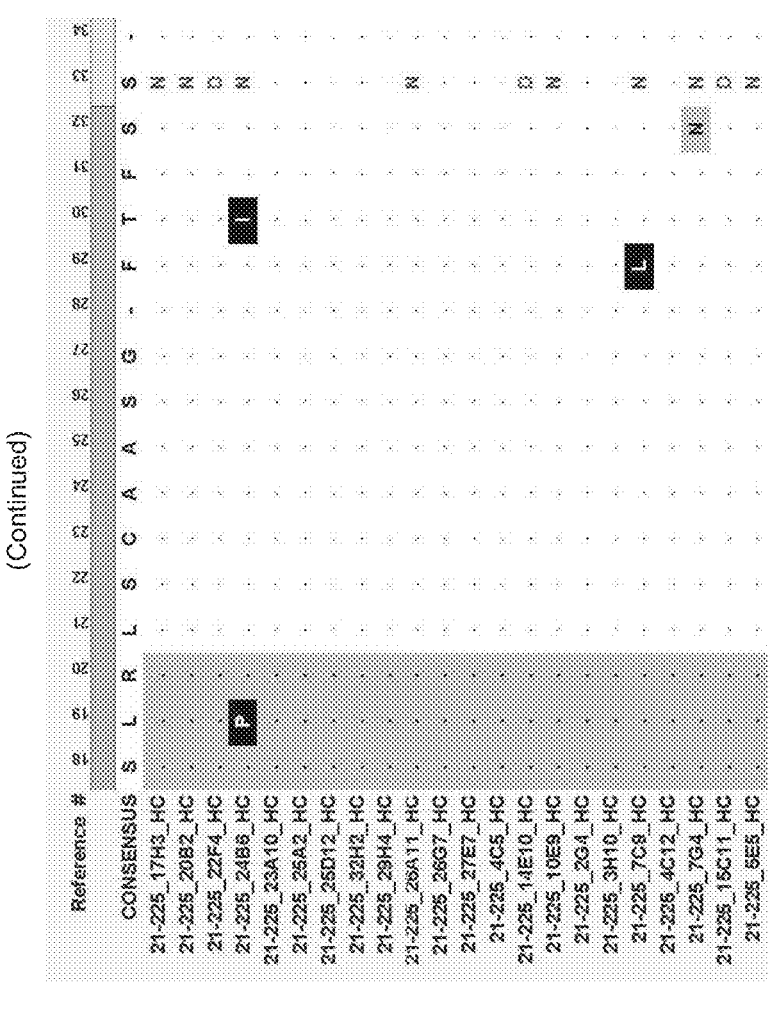
Figure 56:
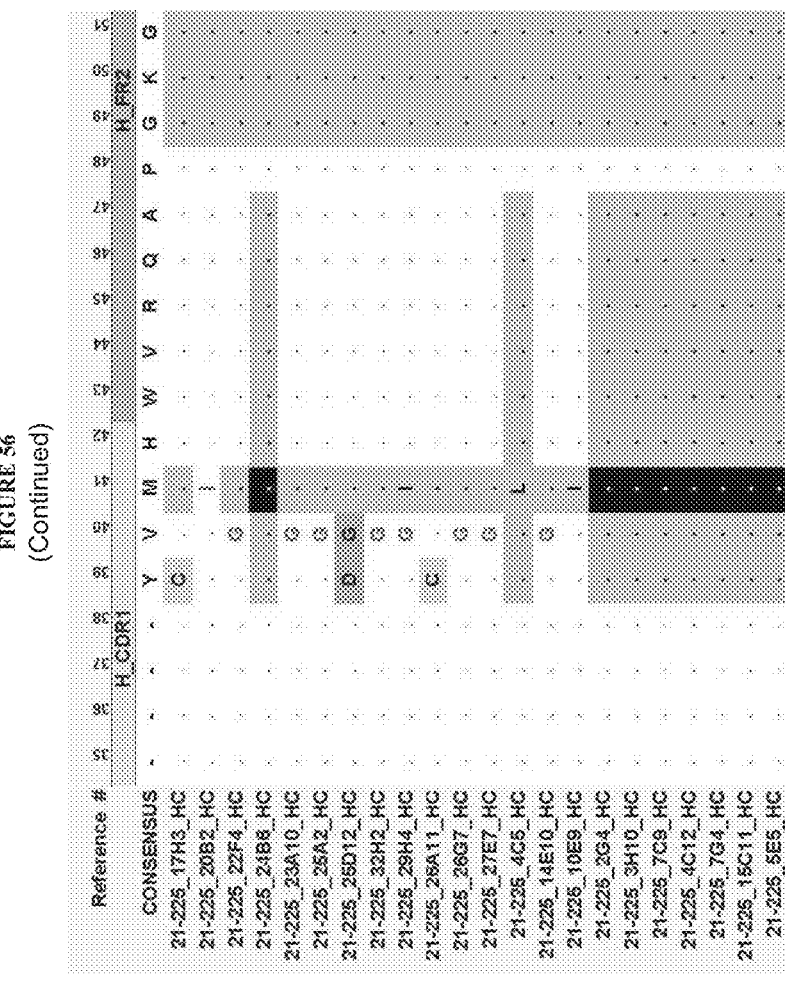
Figure 56:
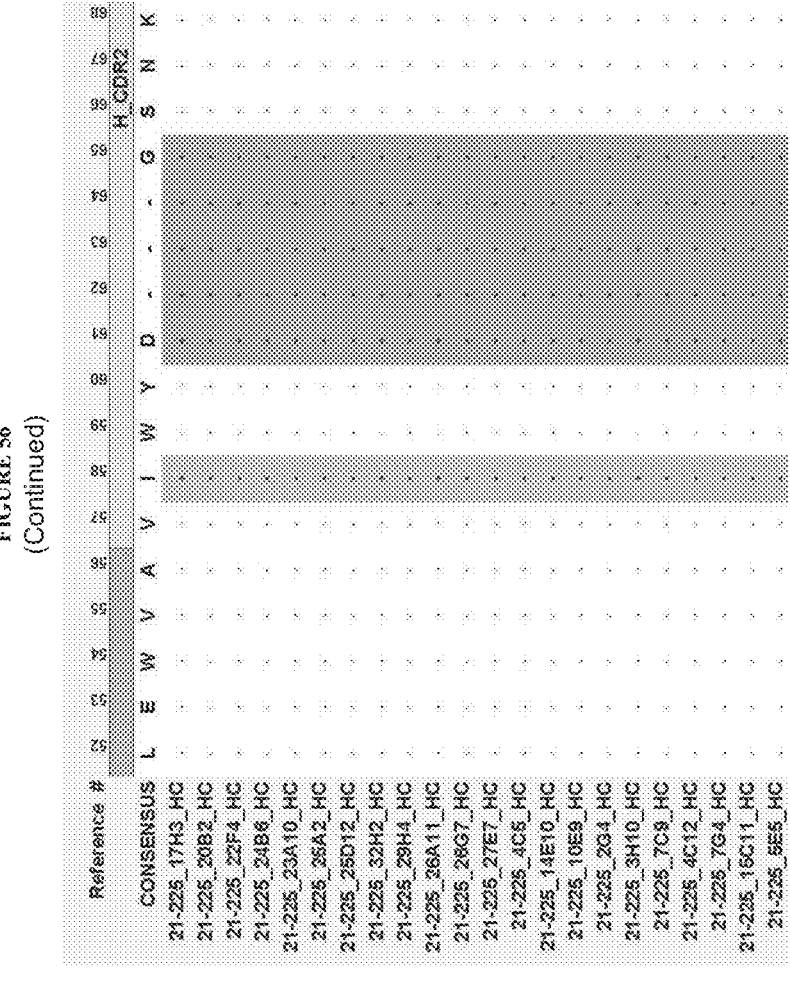
Figure 56:
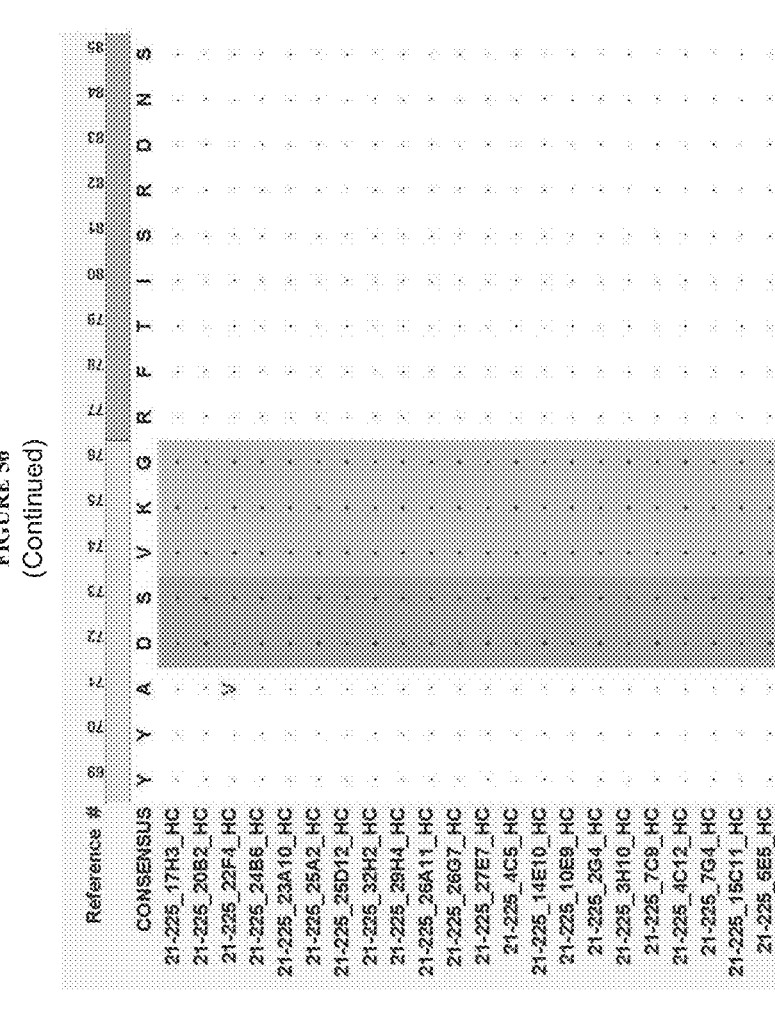
Figure 56:
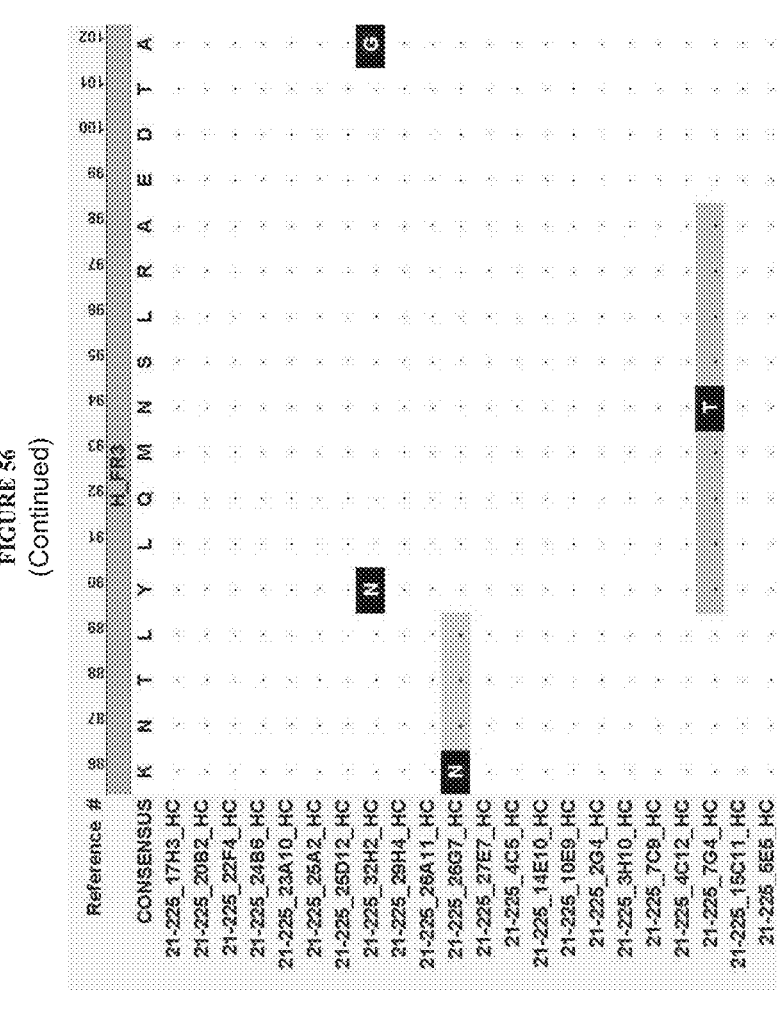
Figure 56:
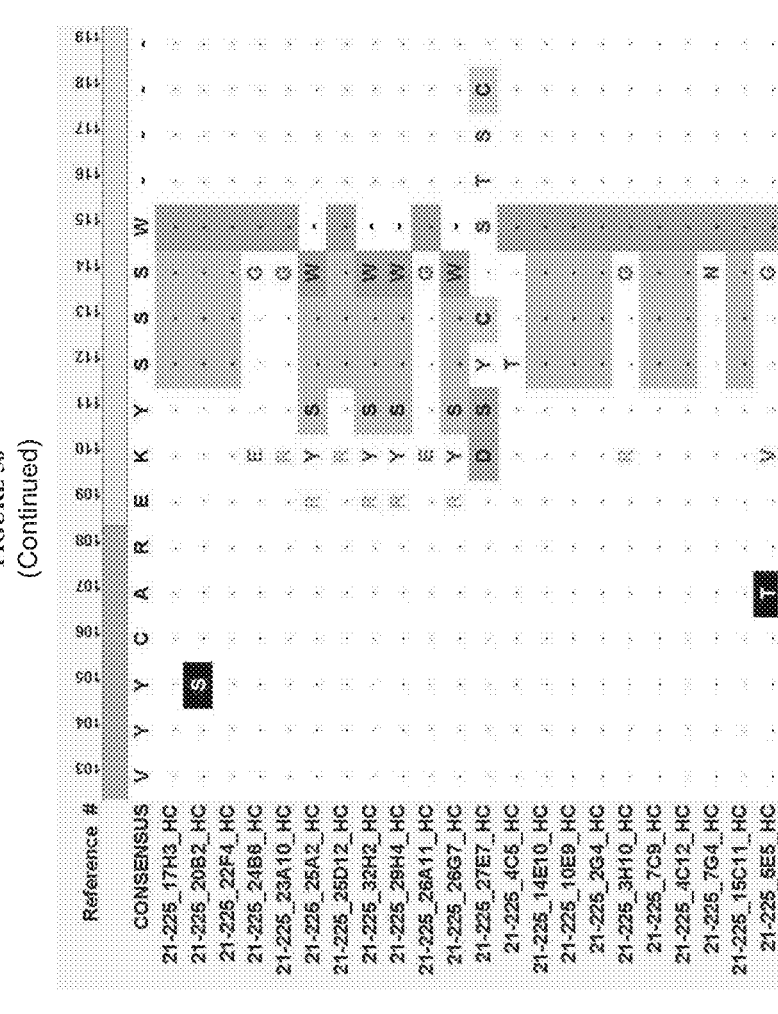
Figure 56:
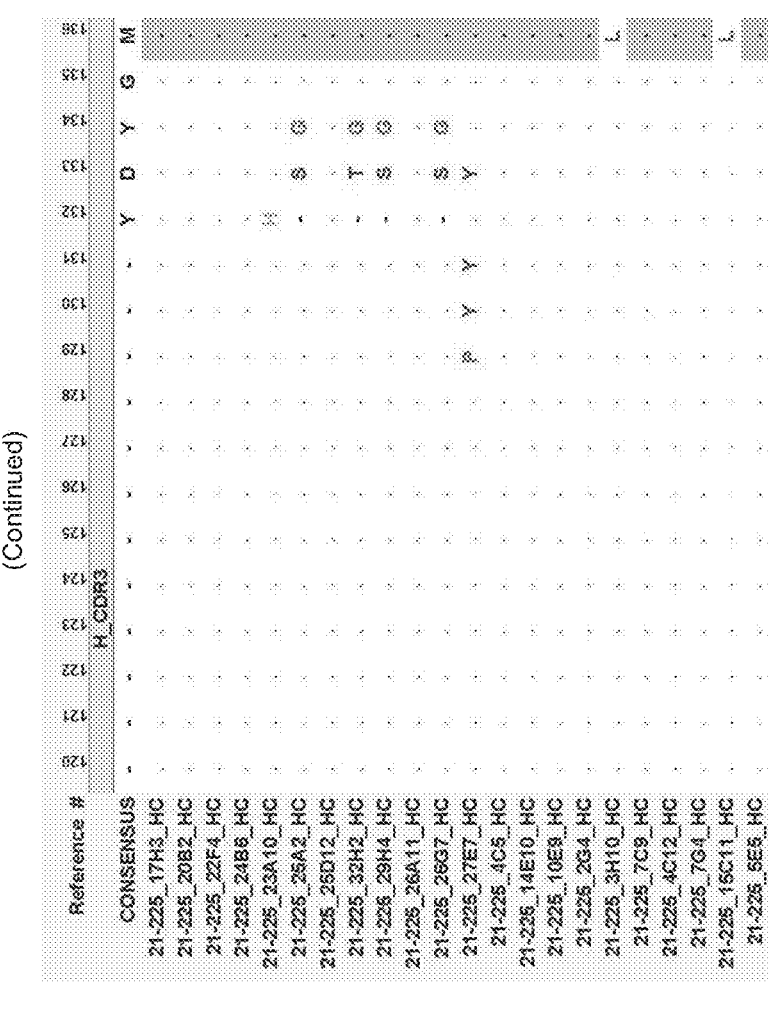
Figure 56:
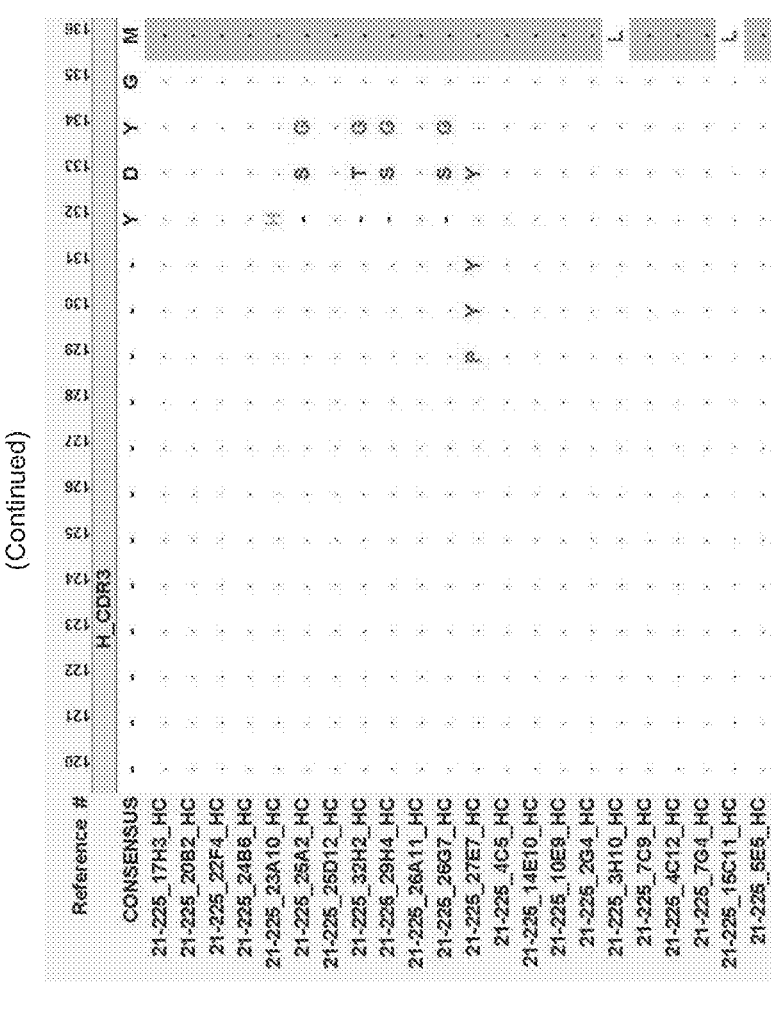
Figure 56:
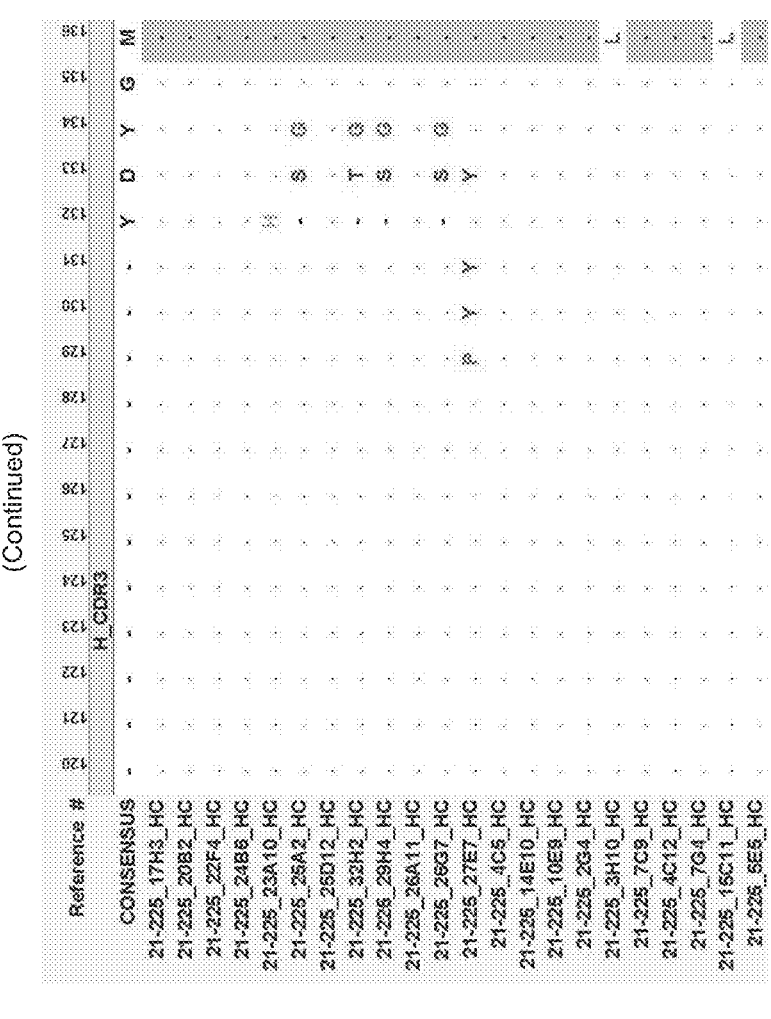
Figure 56:
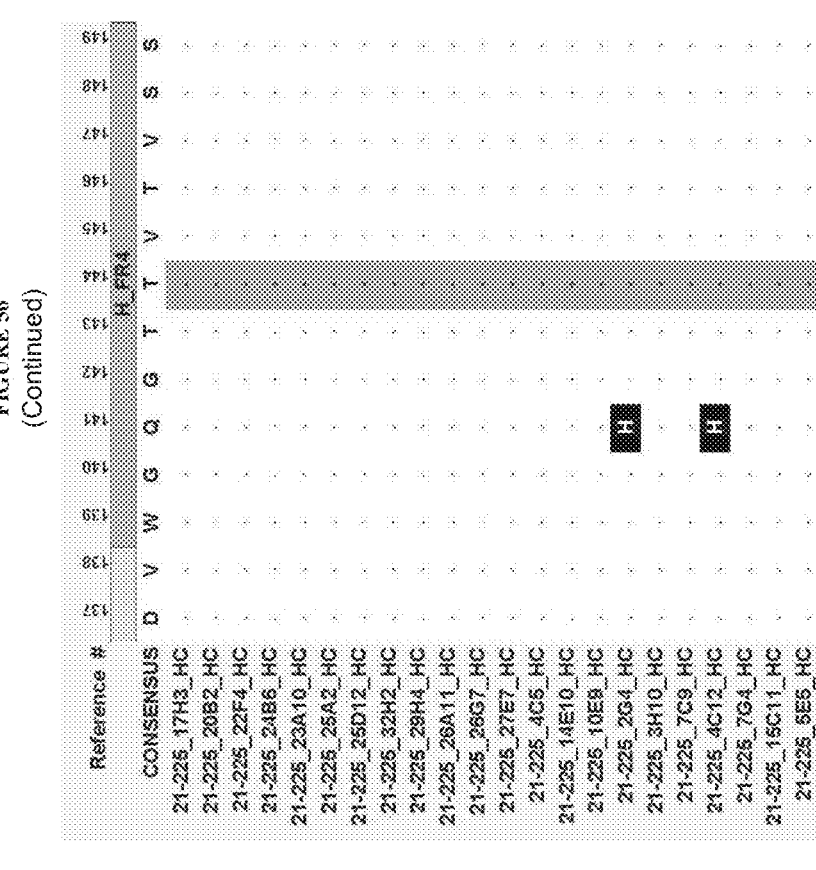
Figure 56:
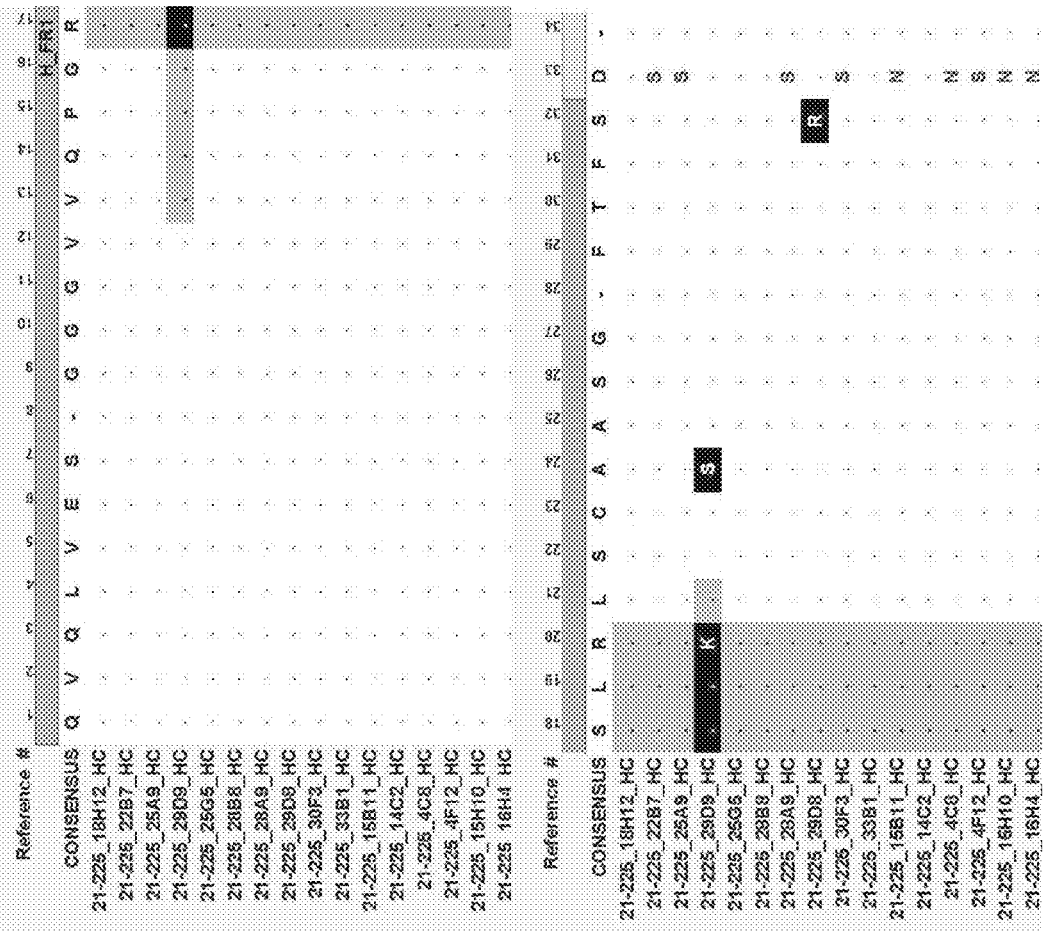
Figure 56:
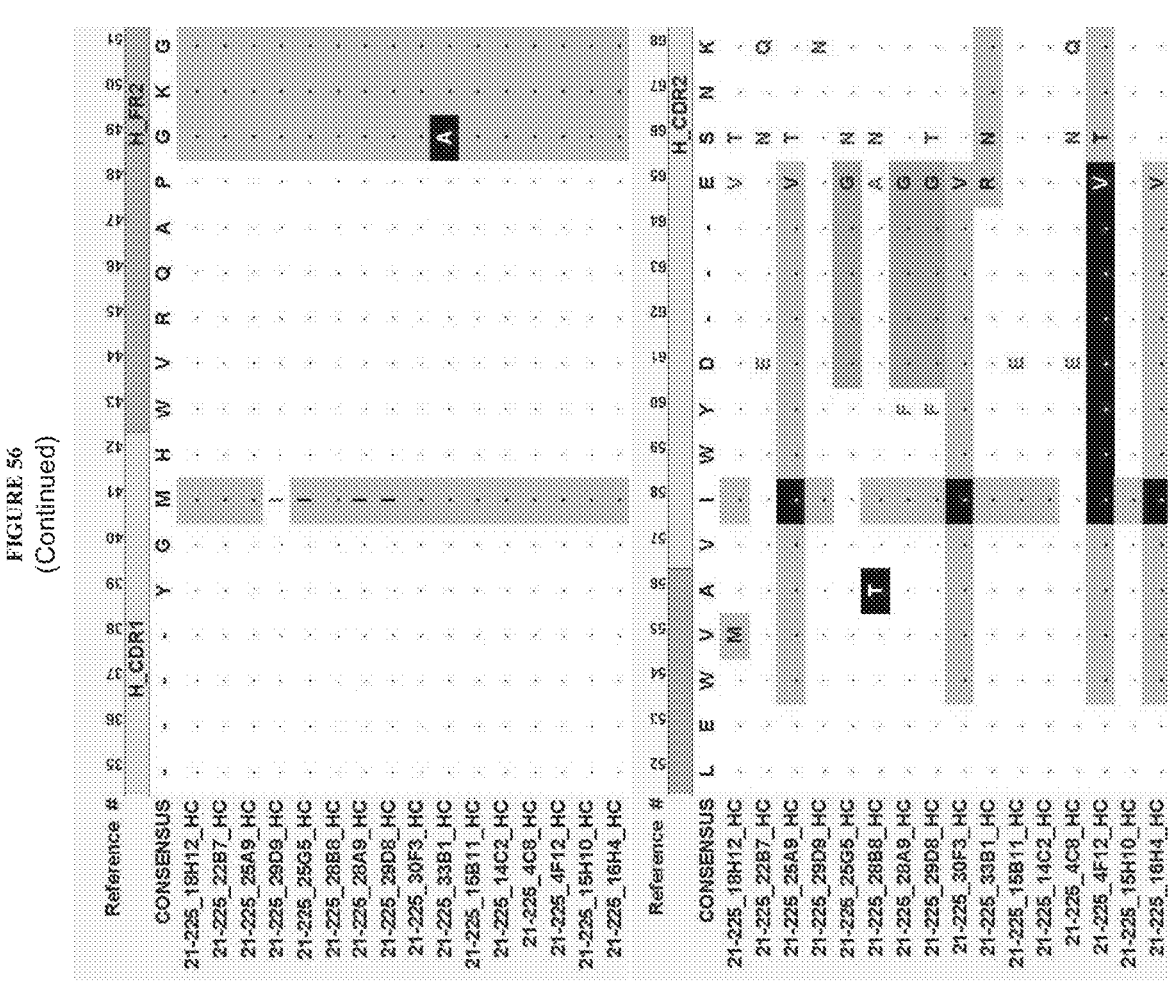
Figure 56:
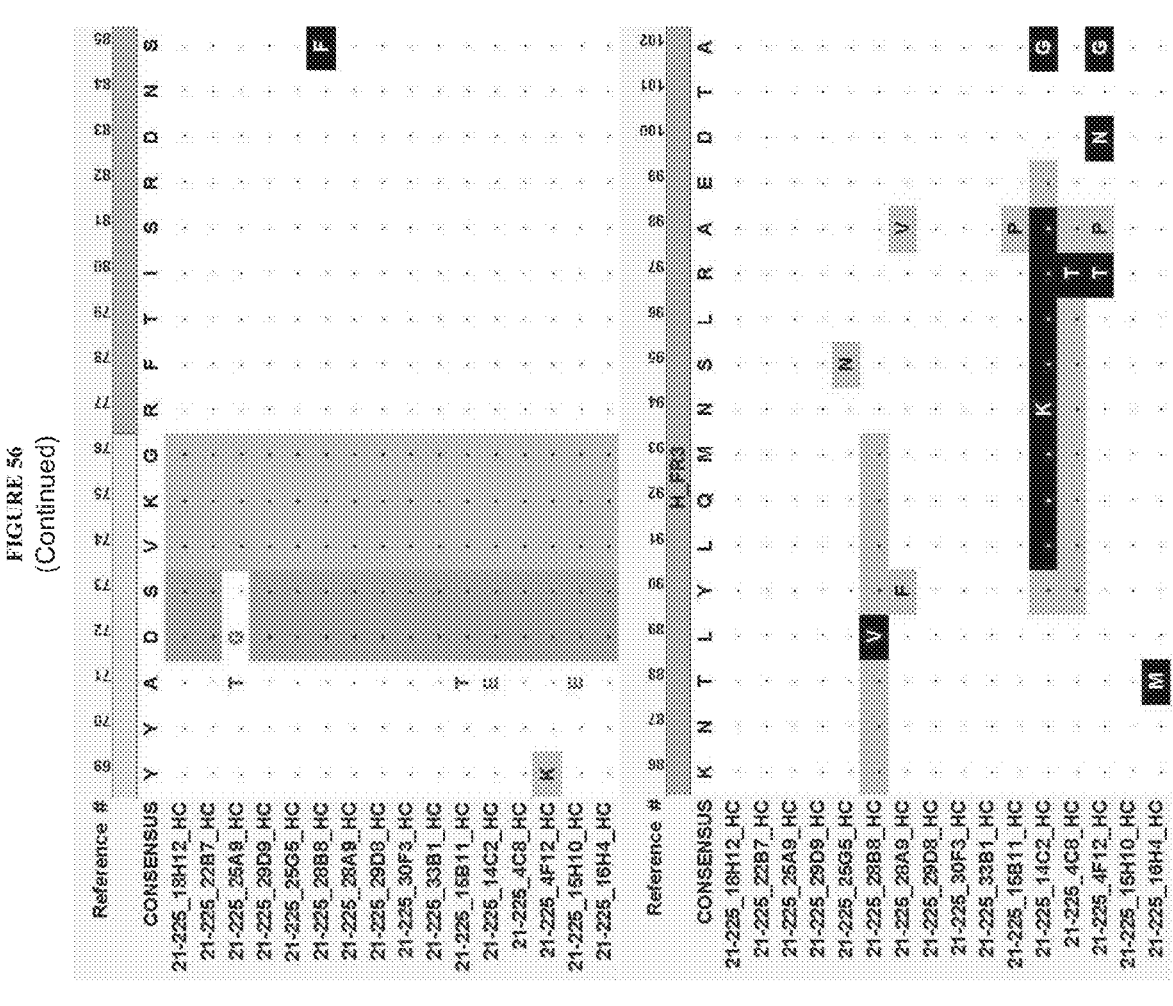
Figure 56:
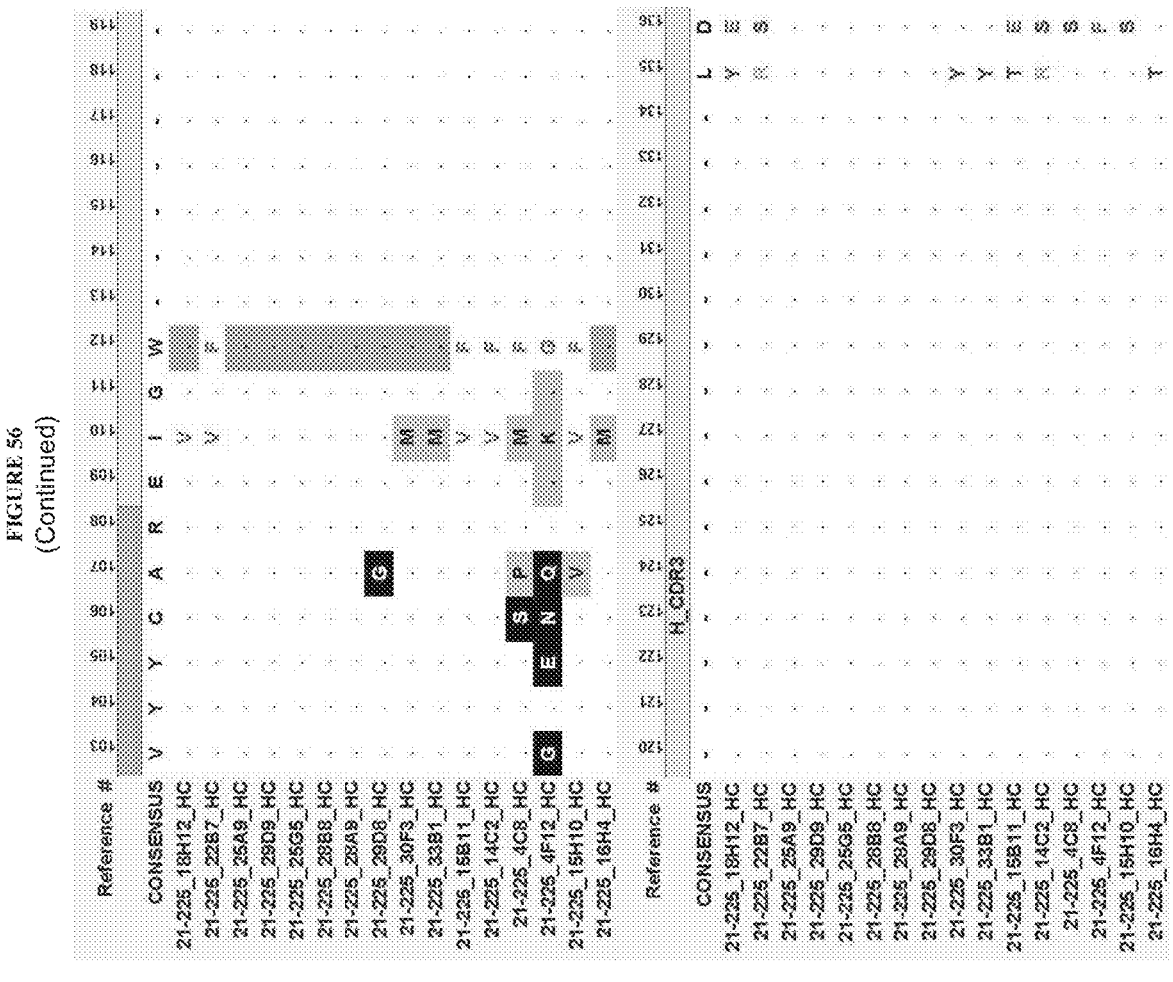
Figure 56:
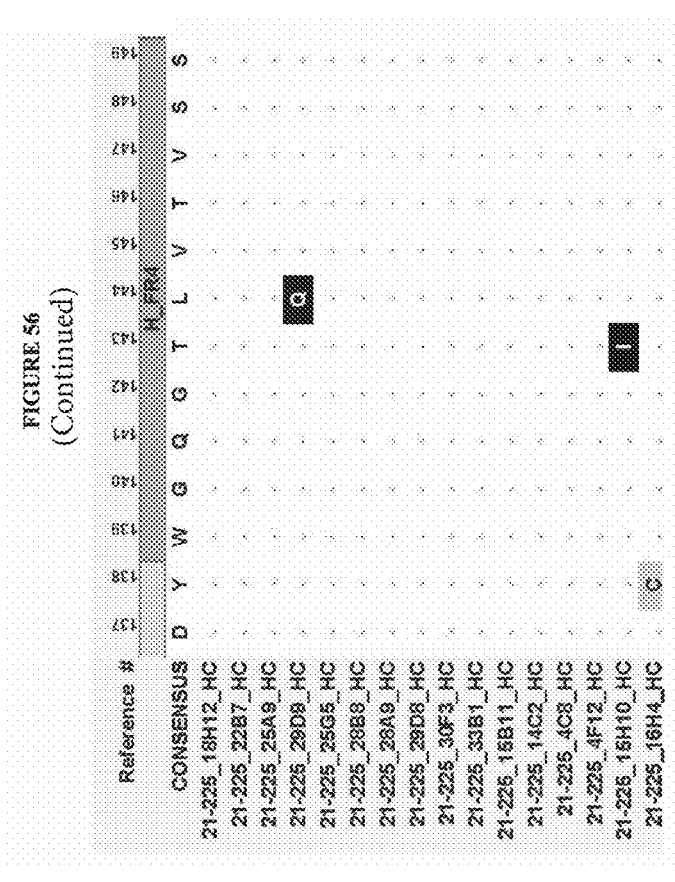
Figure 86:
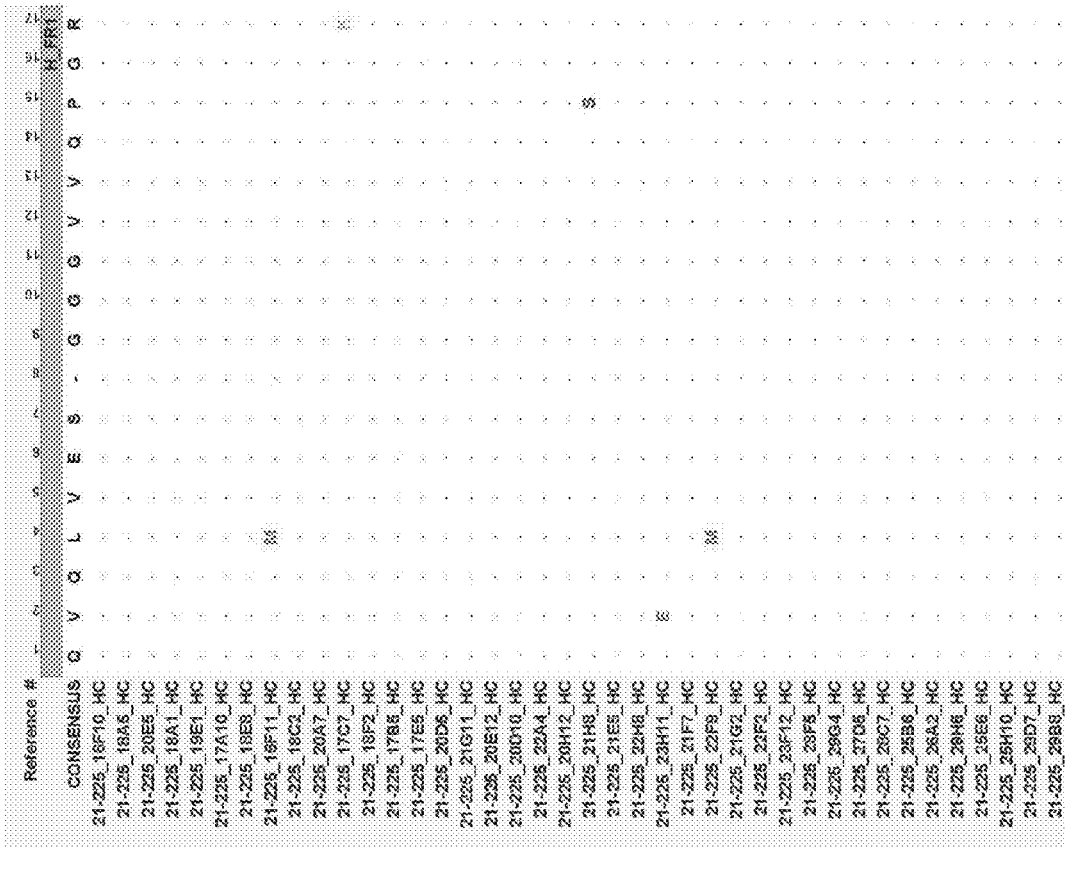
Figure 56:
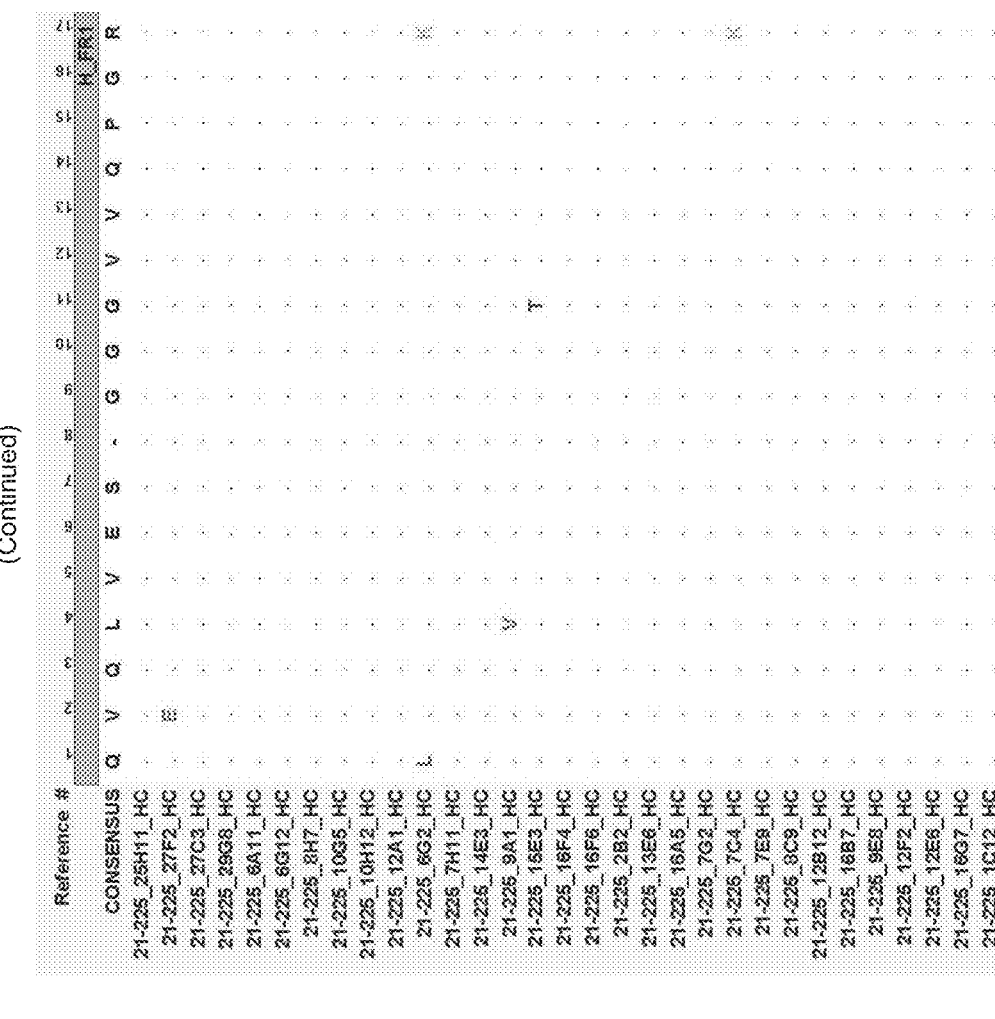
Figure 56:
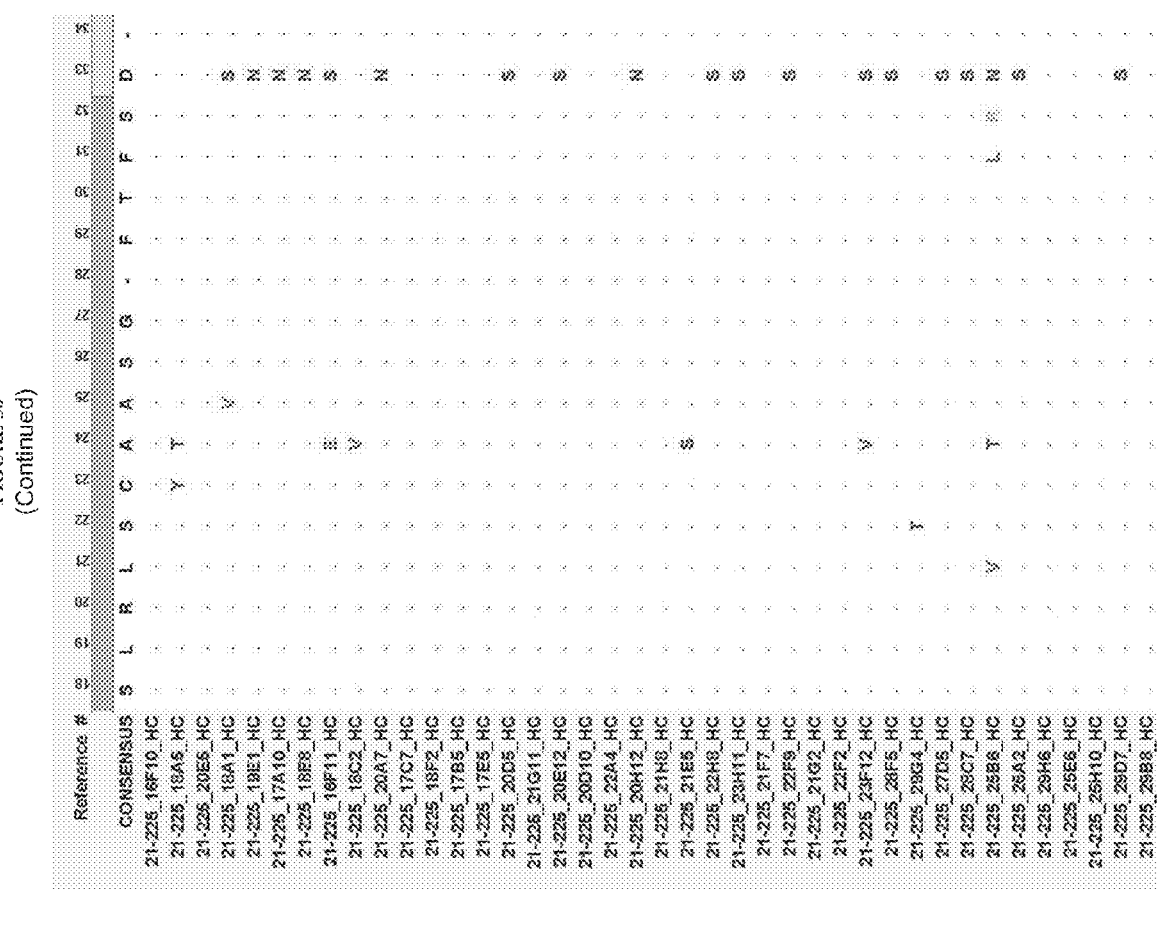
Figure 56:
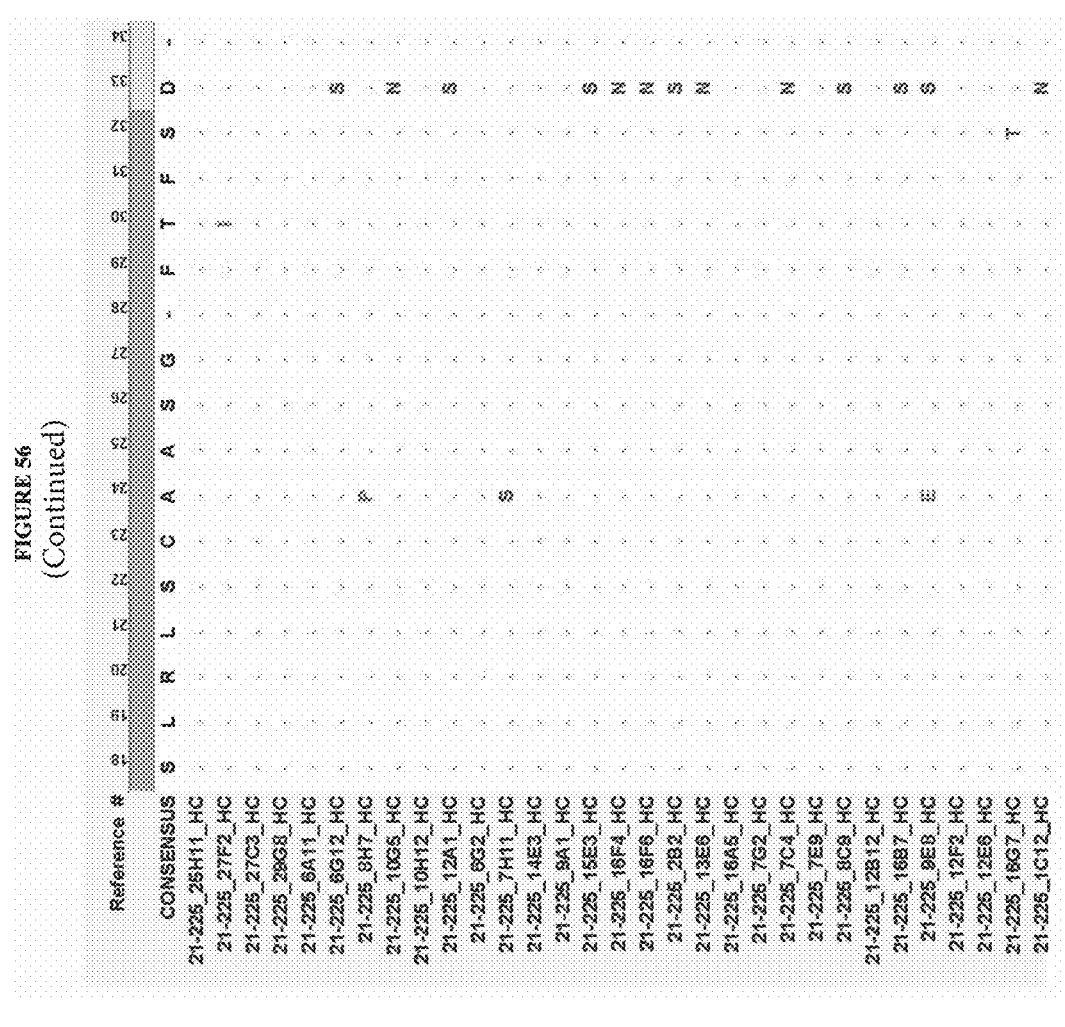
Figure 56:
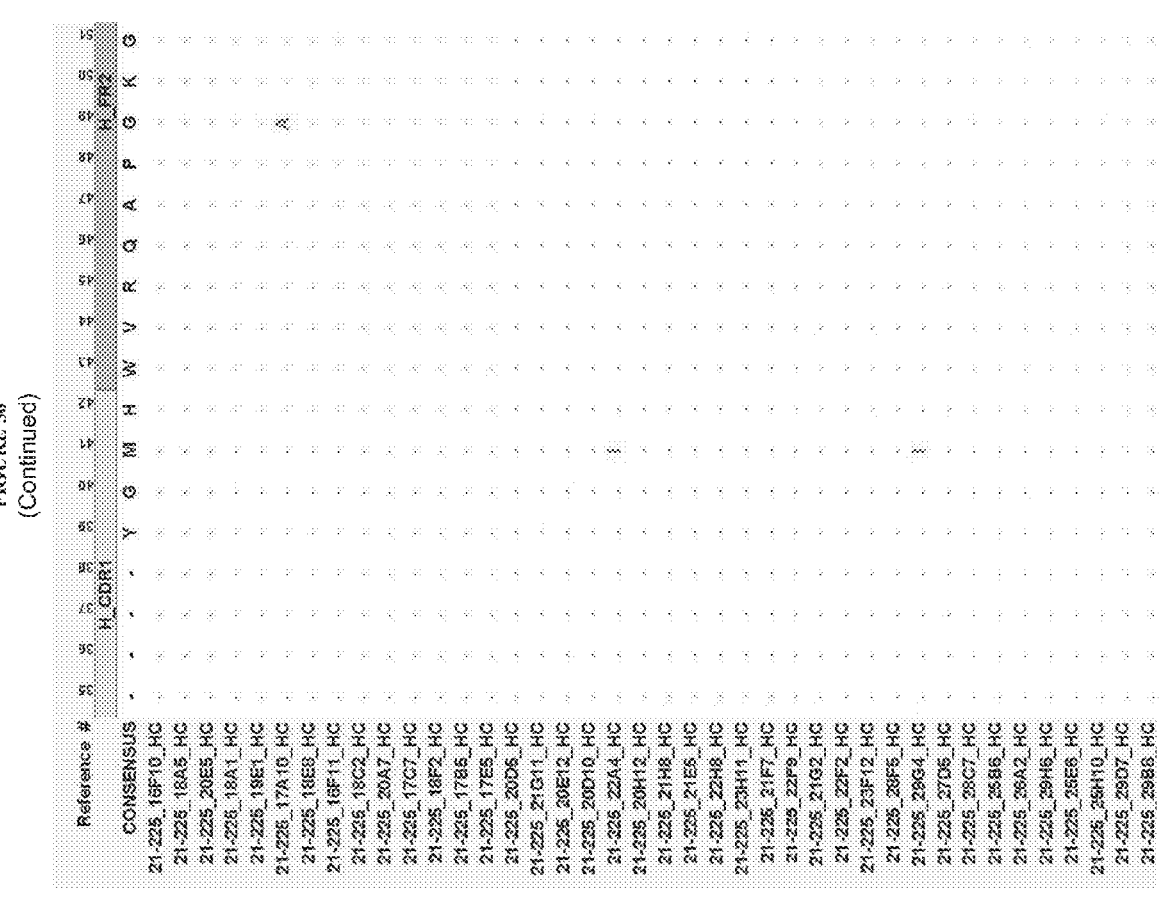
Figure 56:
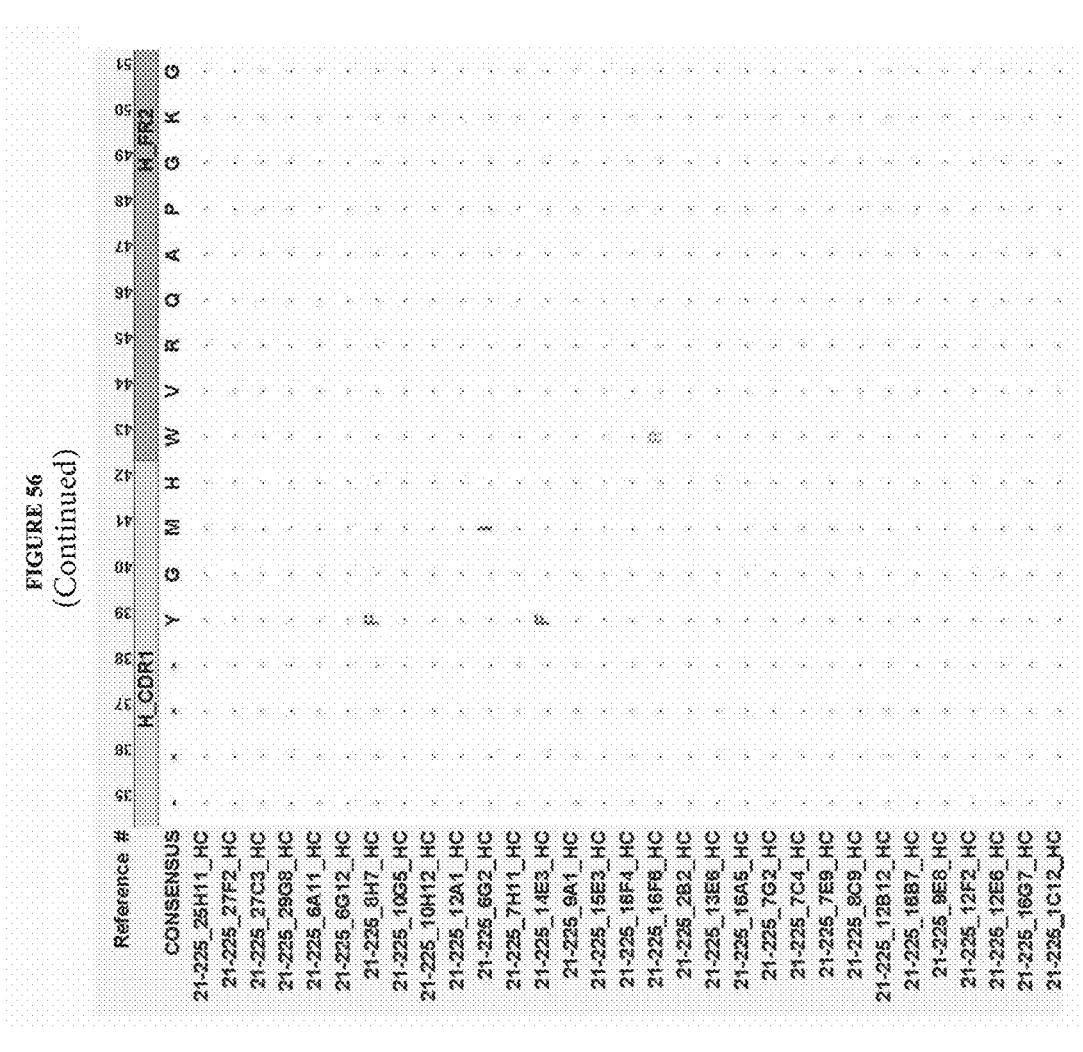
Figure 56:
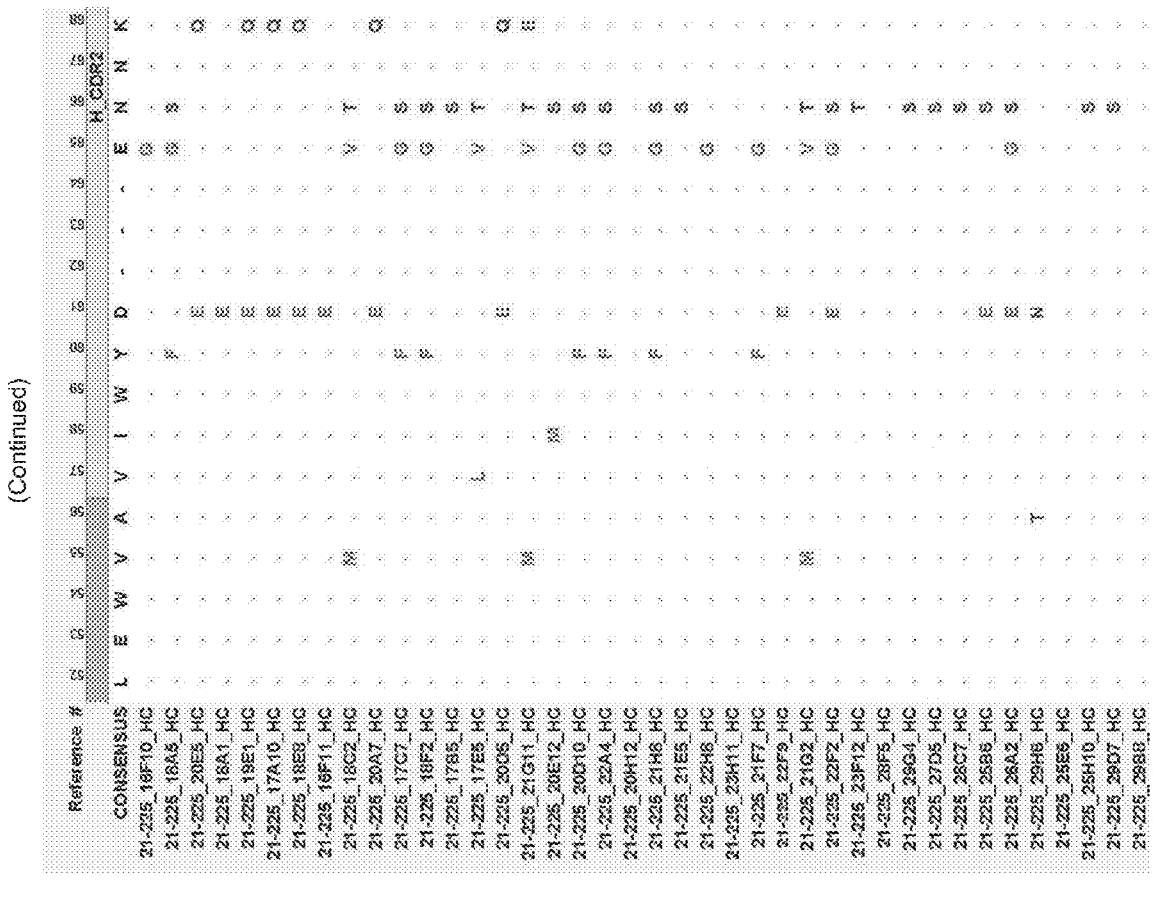
Figure 56:
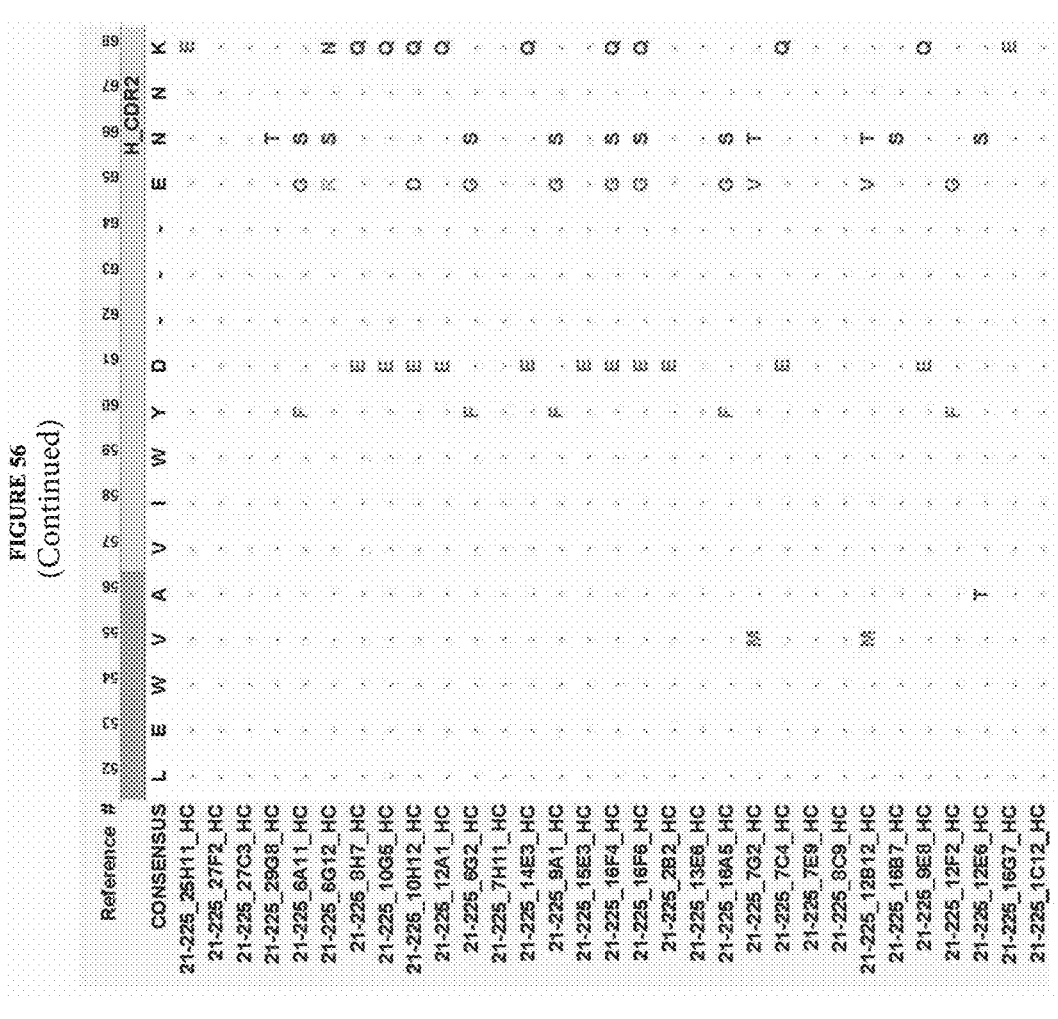
Figure 56:
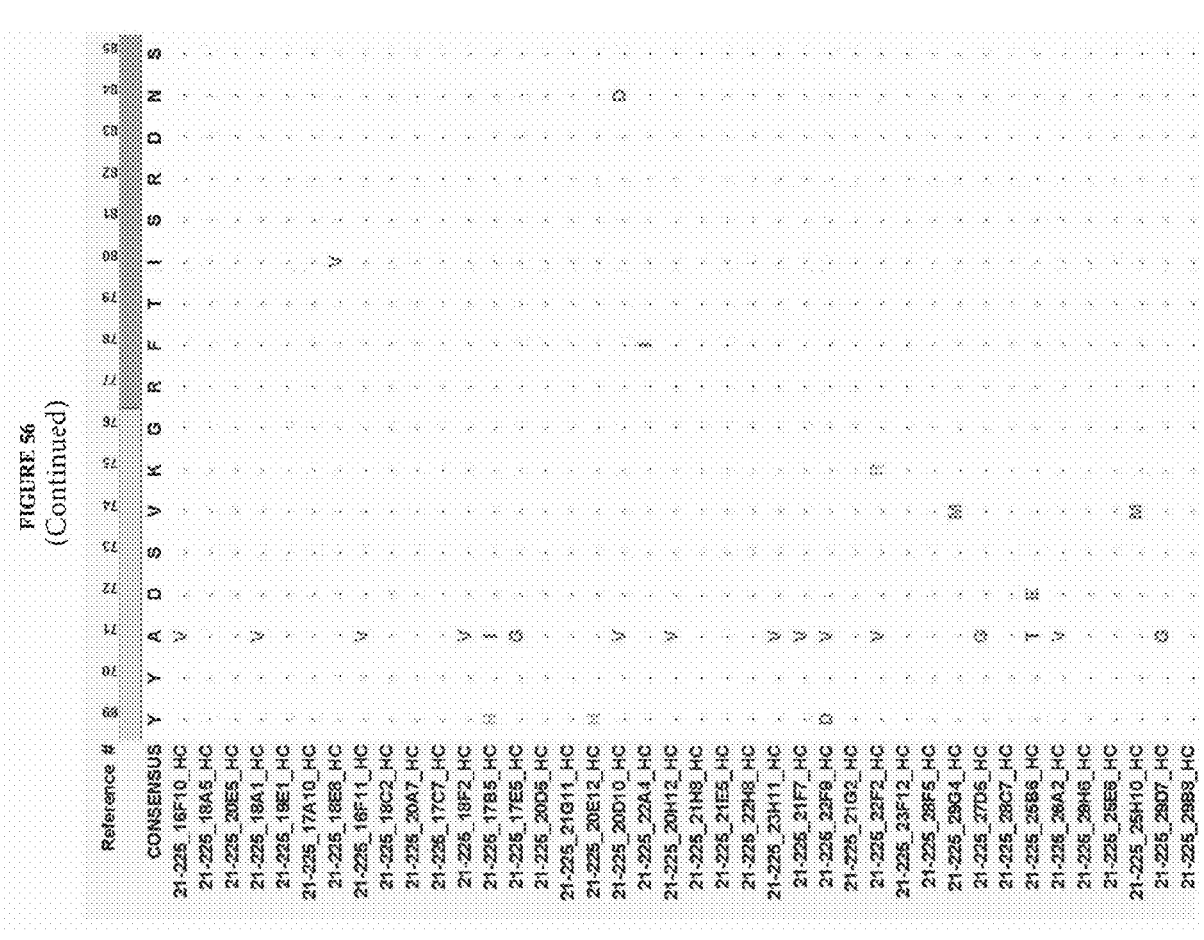
Figure 56:
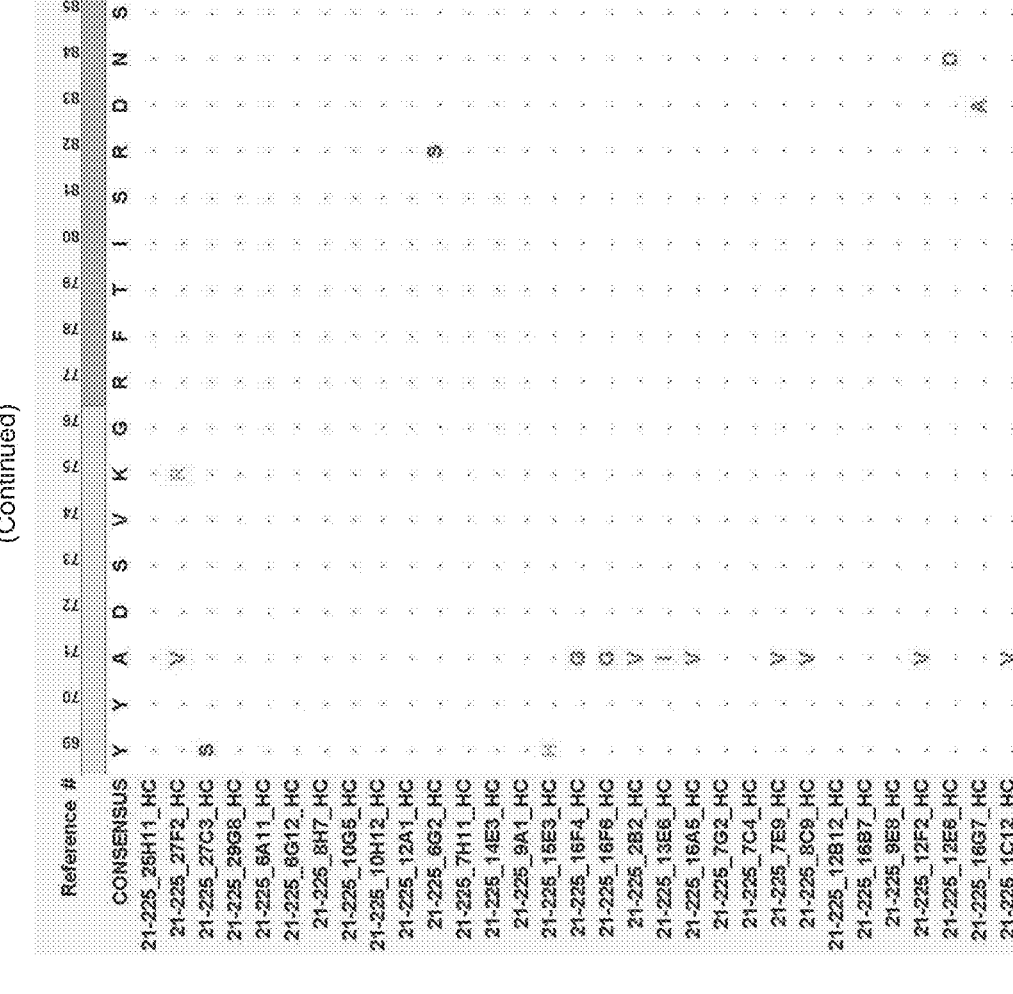
Figure 56:
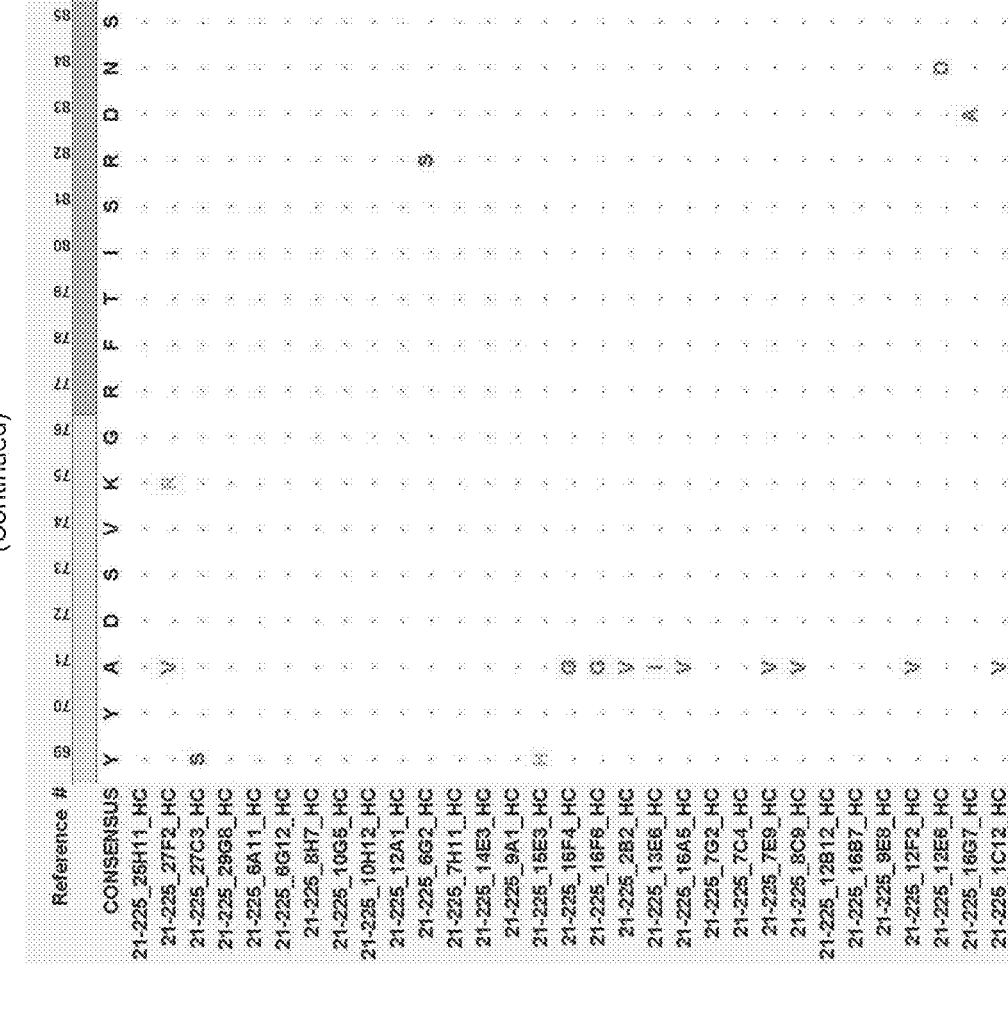
Figure 56:
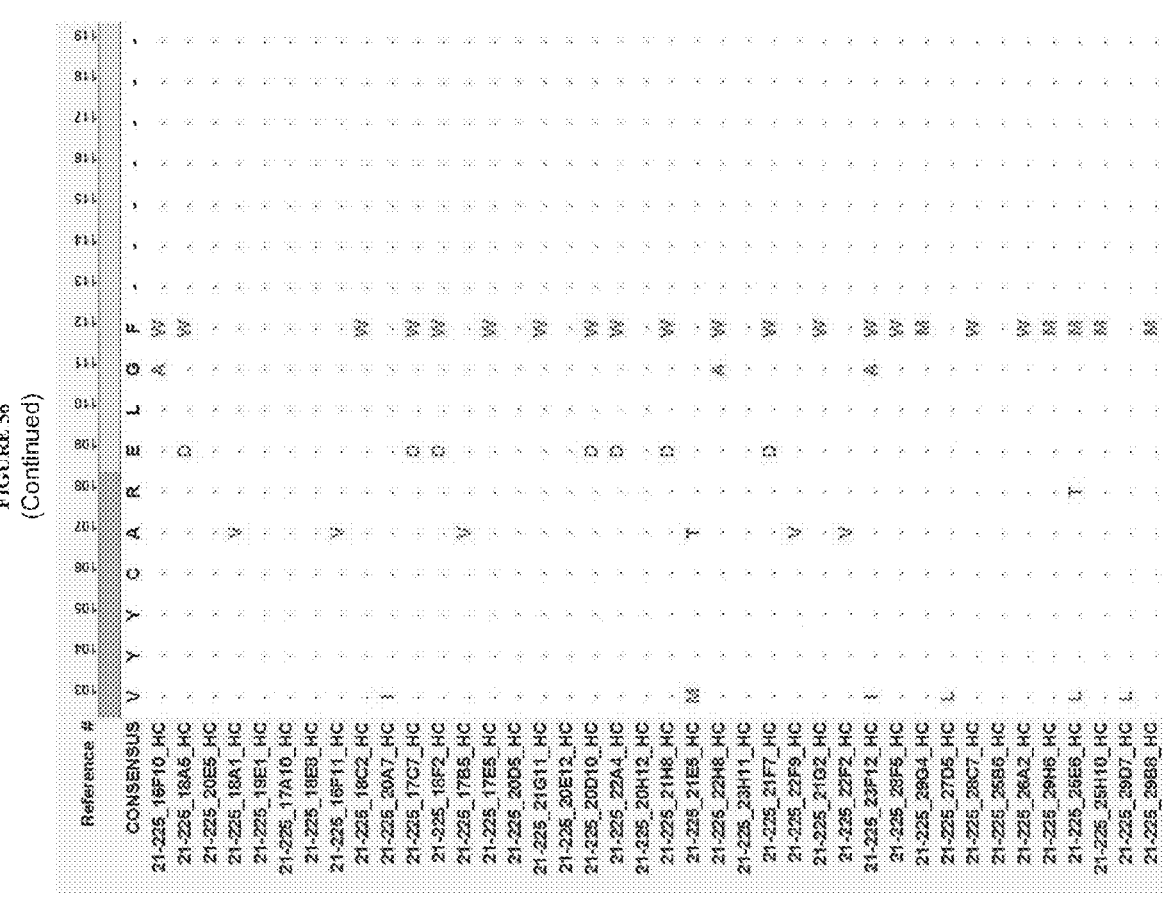
Figure 56:
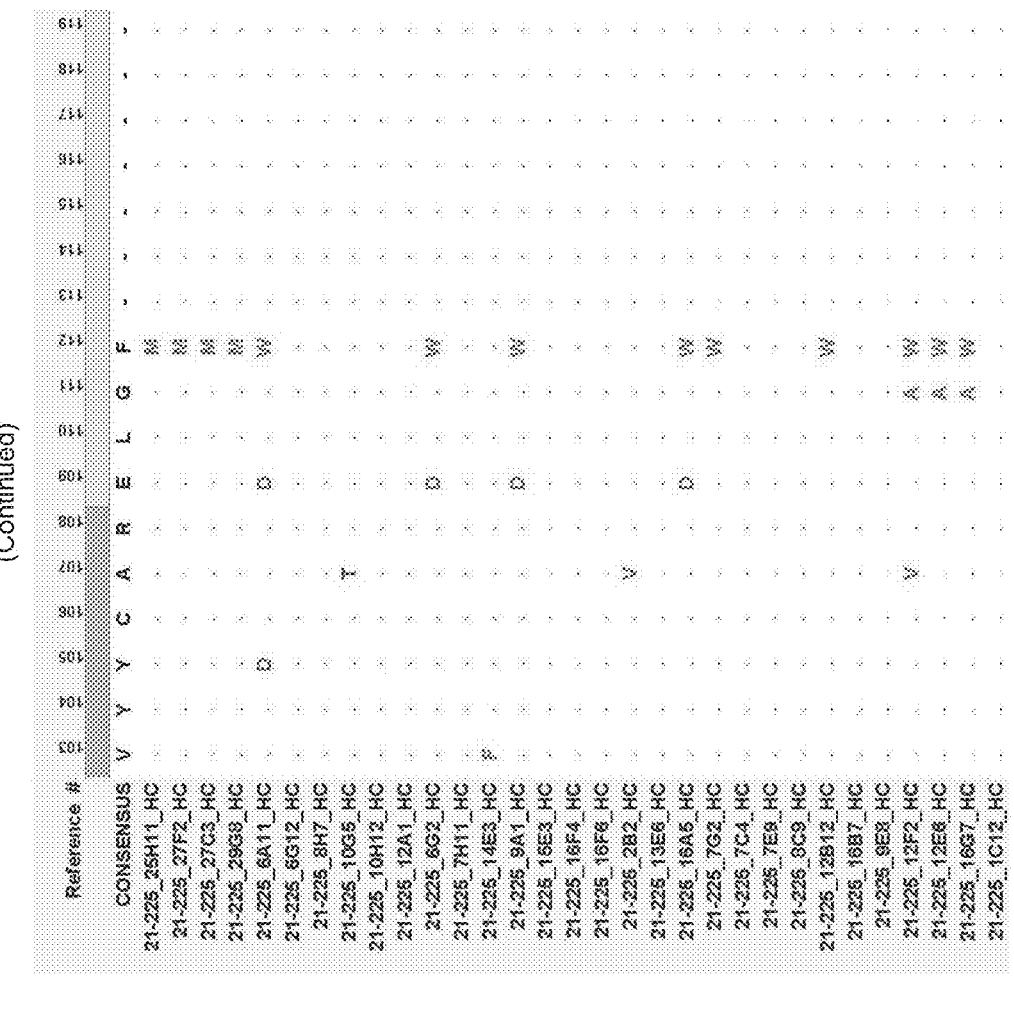
Figure 56:
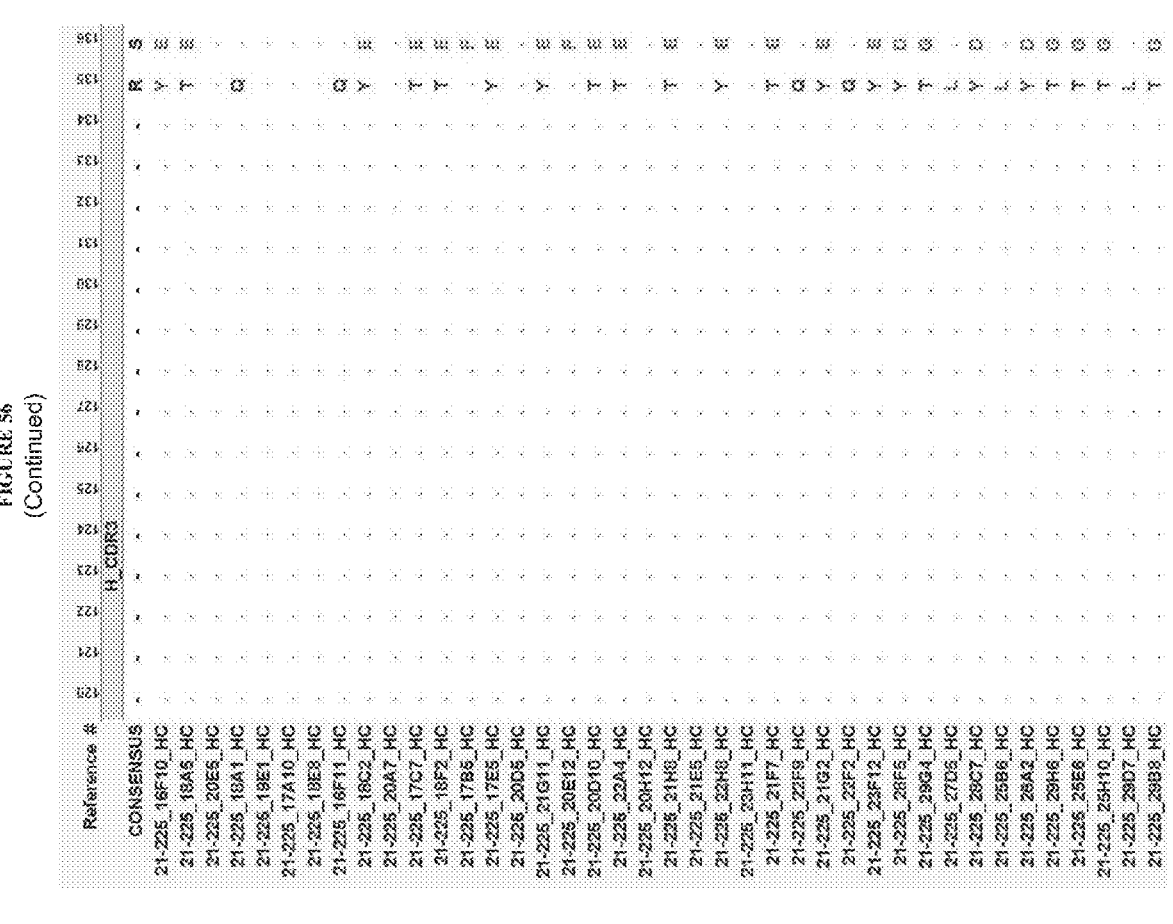
Figure 56:
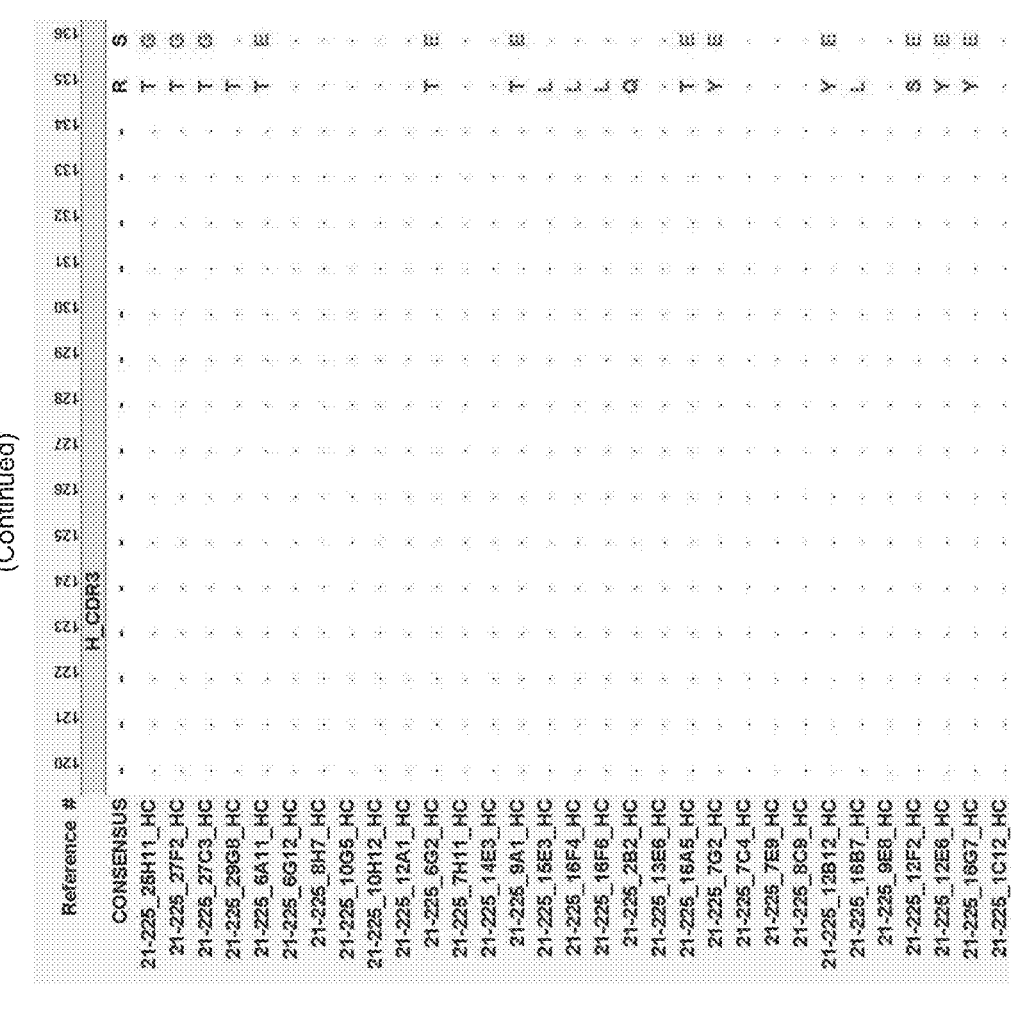
Figure 56:
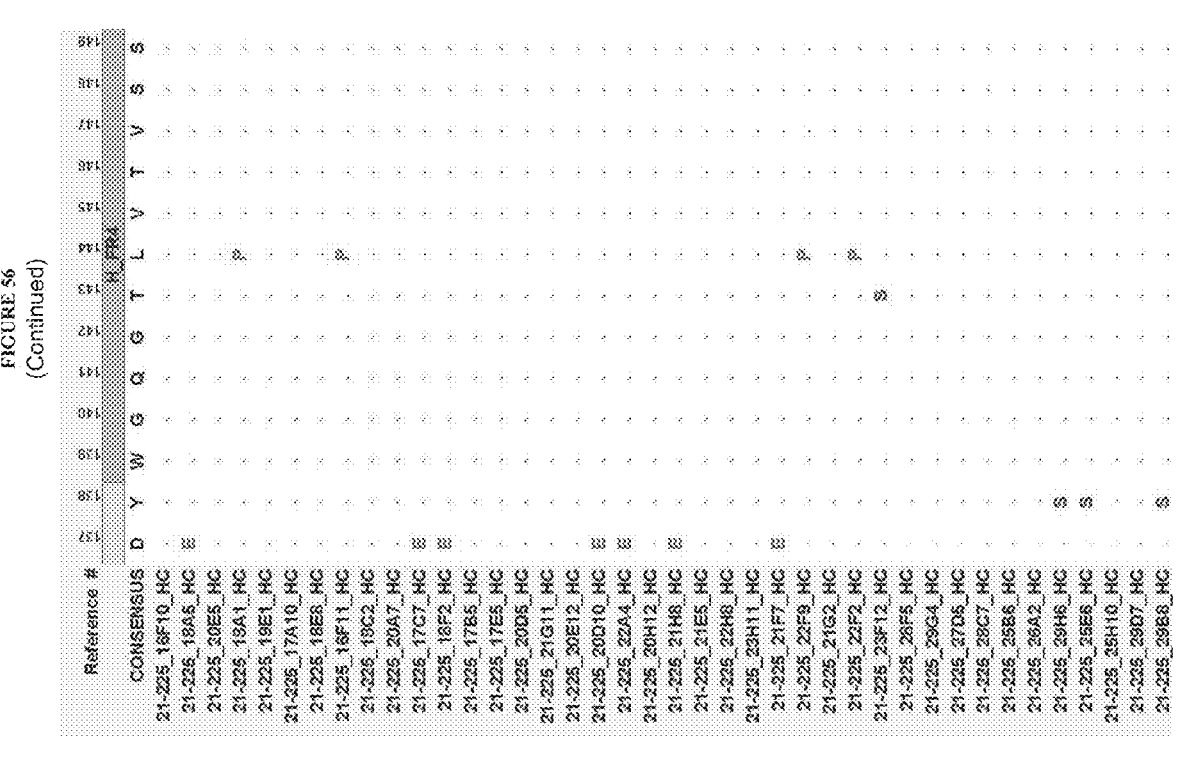
Figure 56:
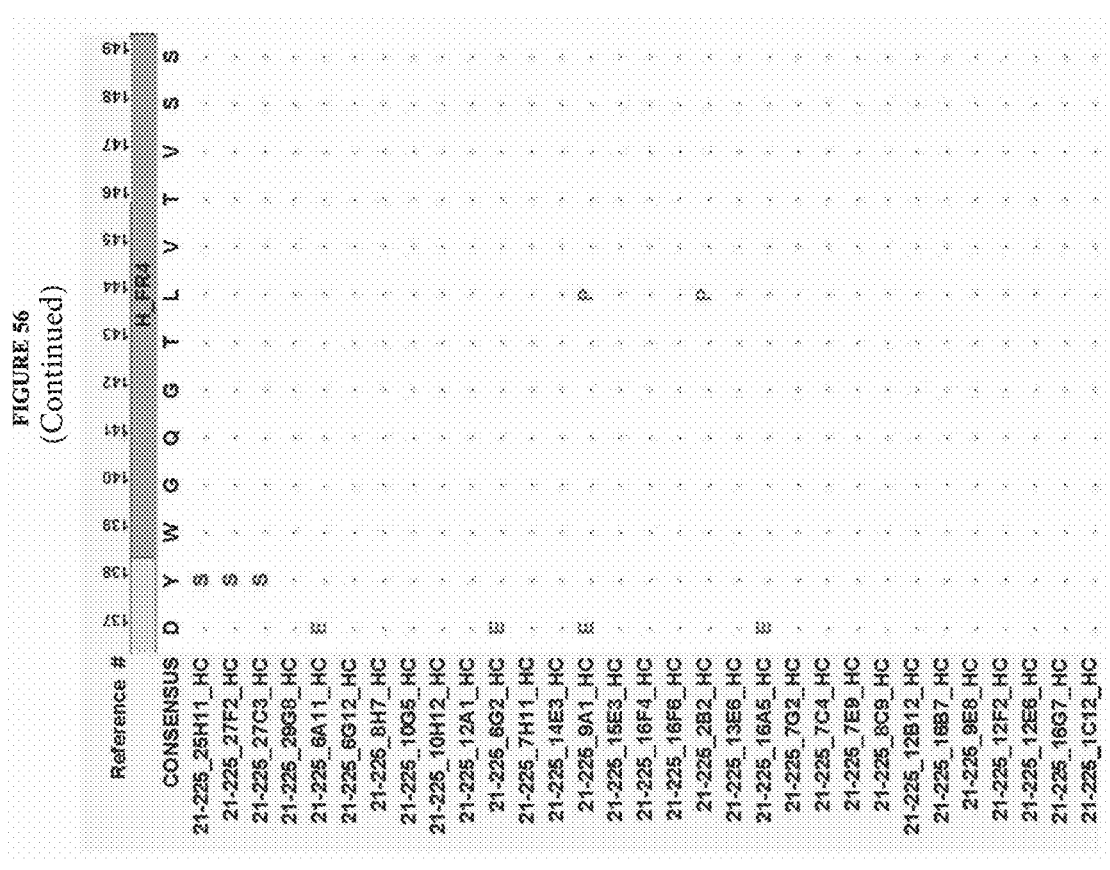
Figure 56:
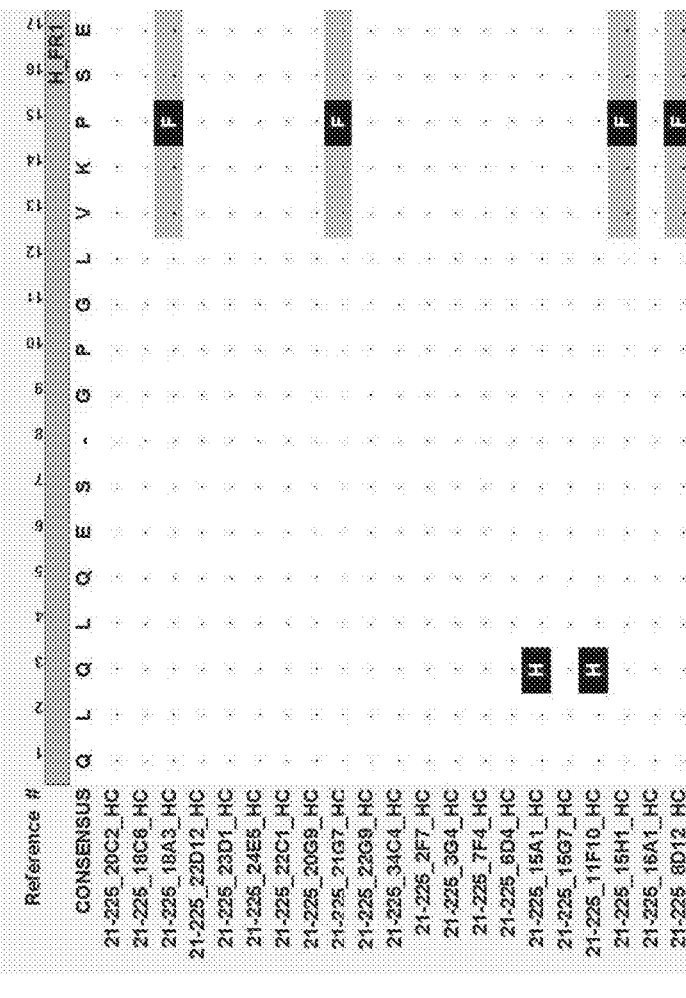
Figure 56:
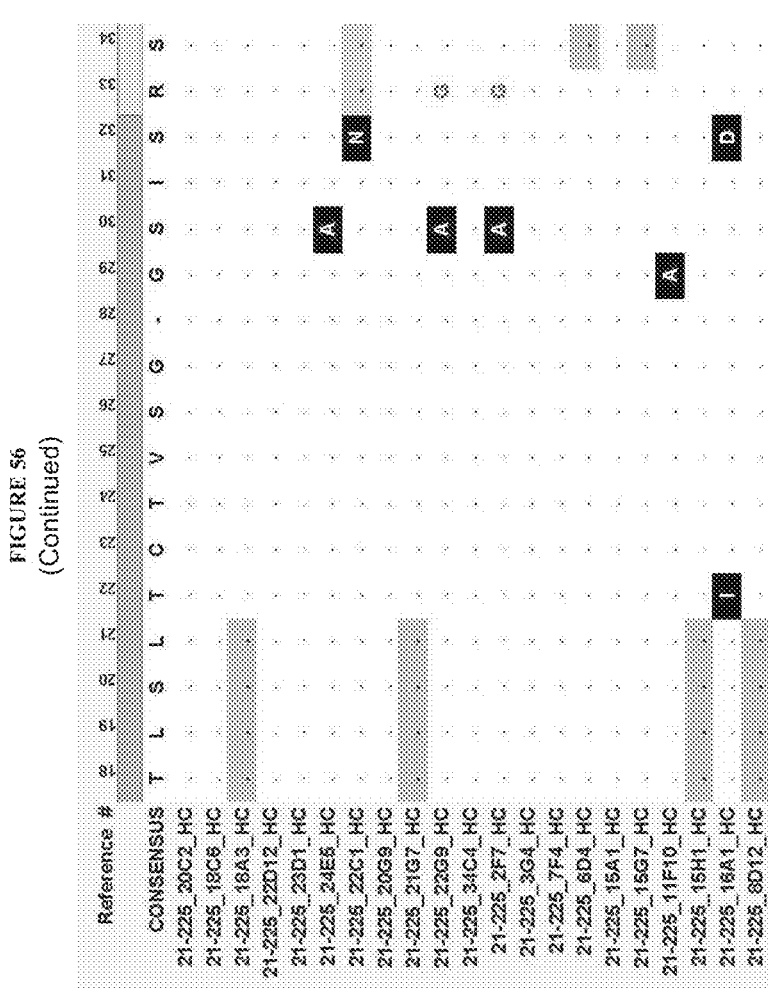
Figure 56:
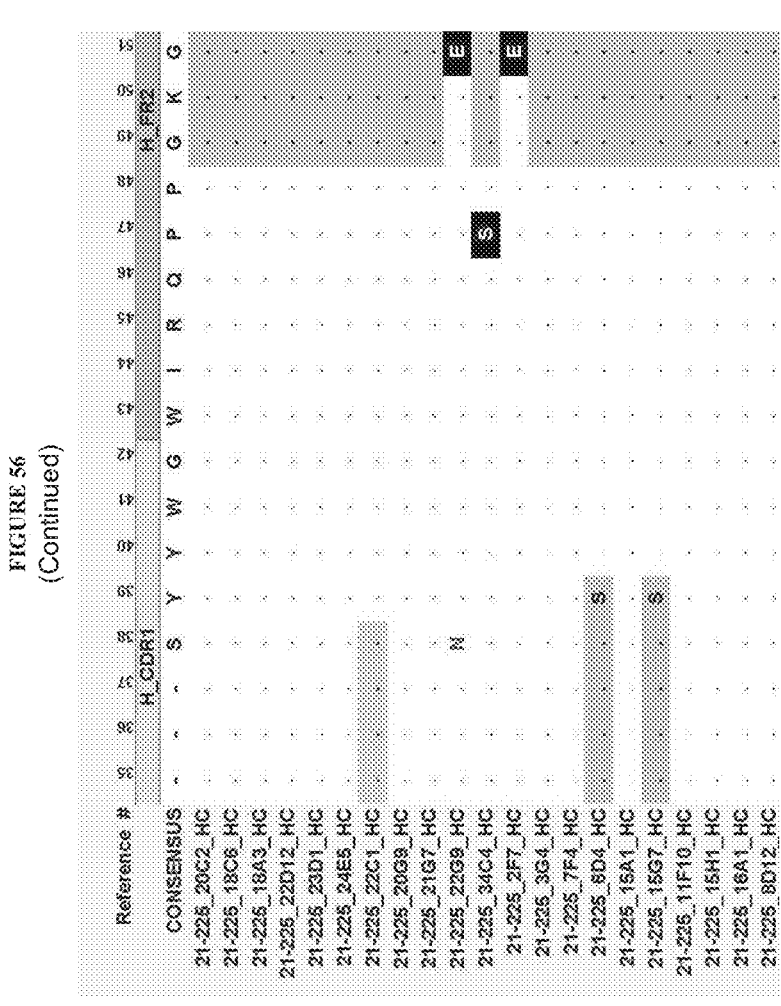
Figure 56:
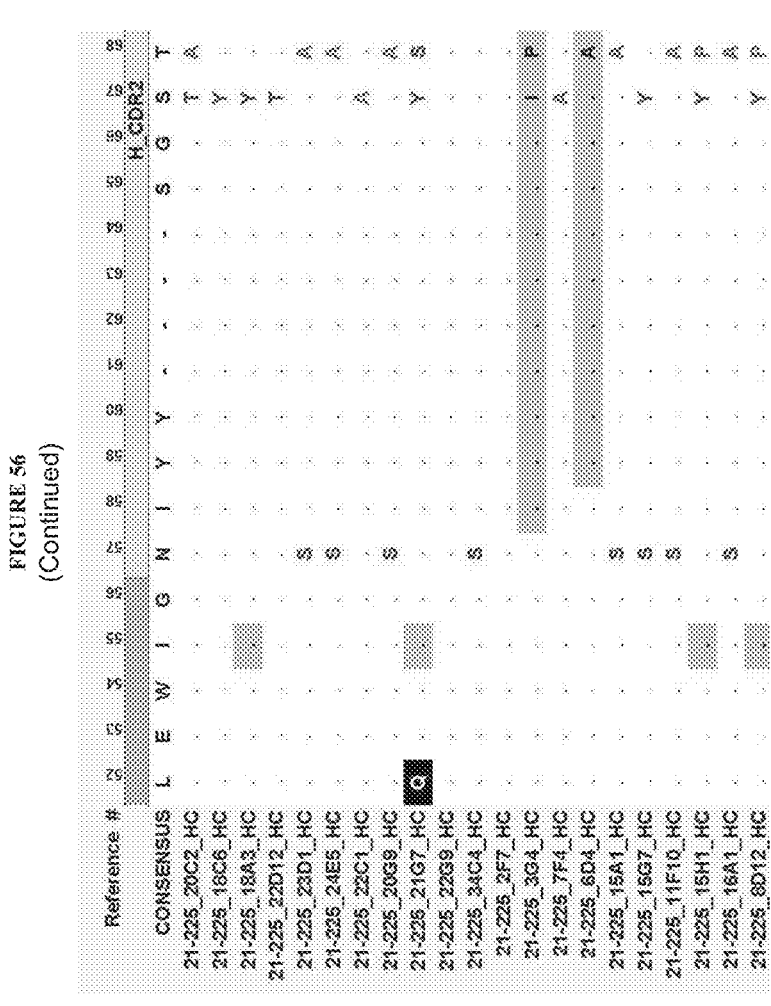
Figure 56:
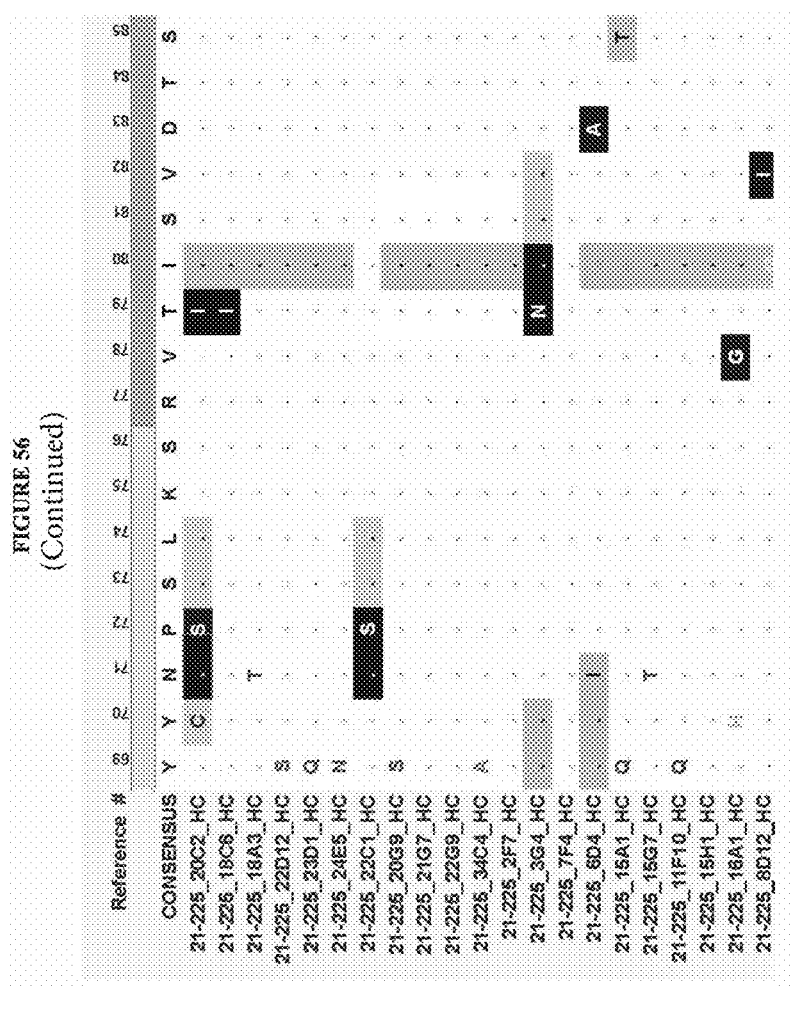
Figure 56:
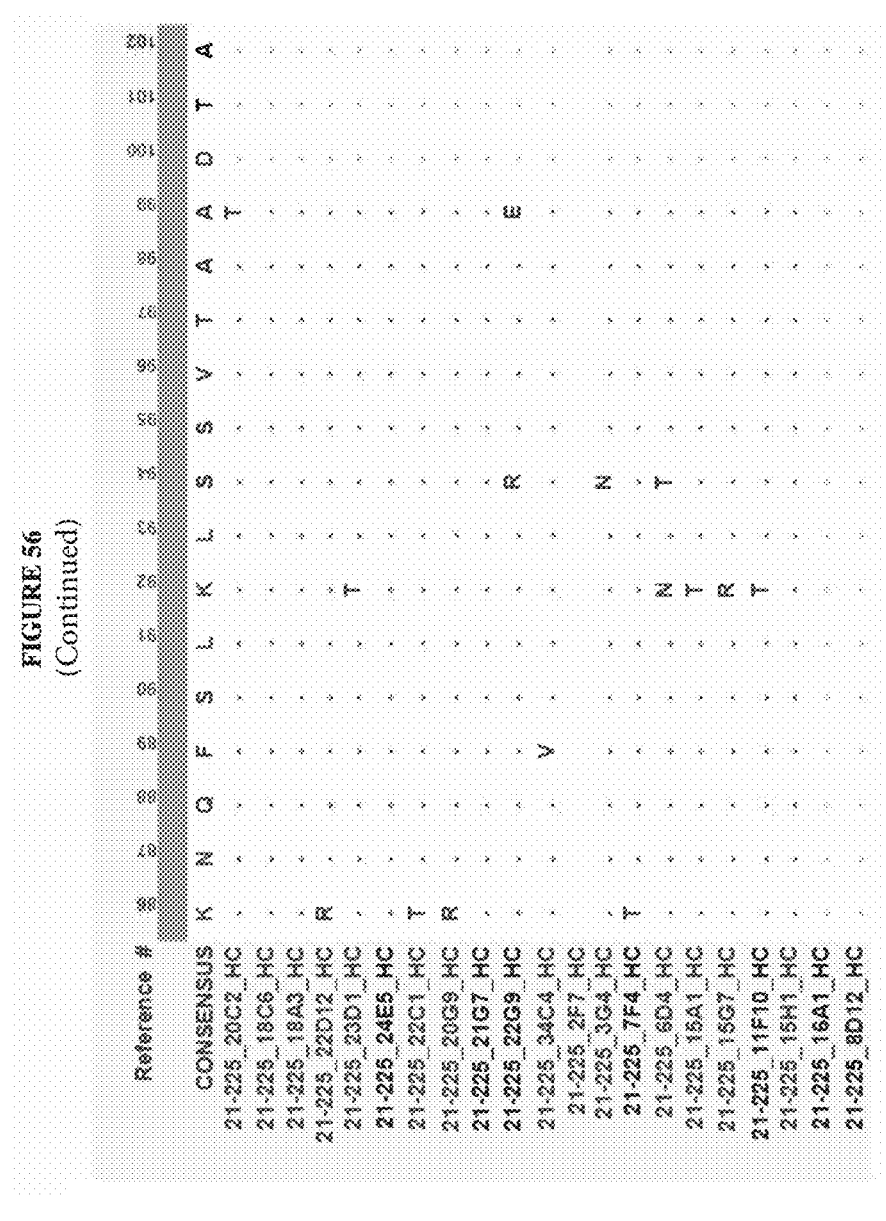
Figure 56:
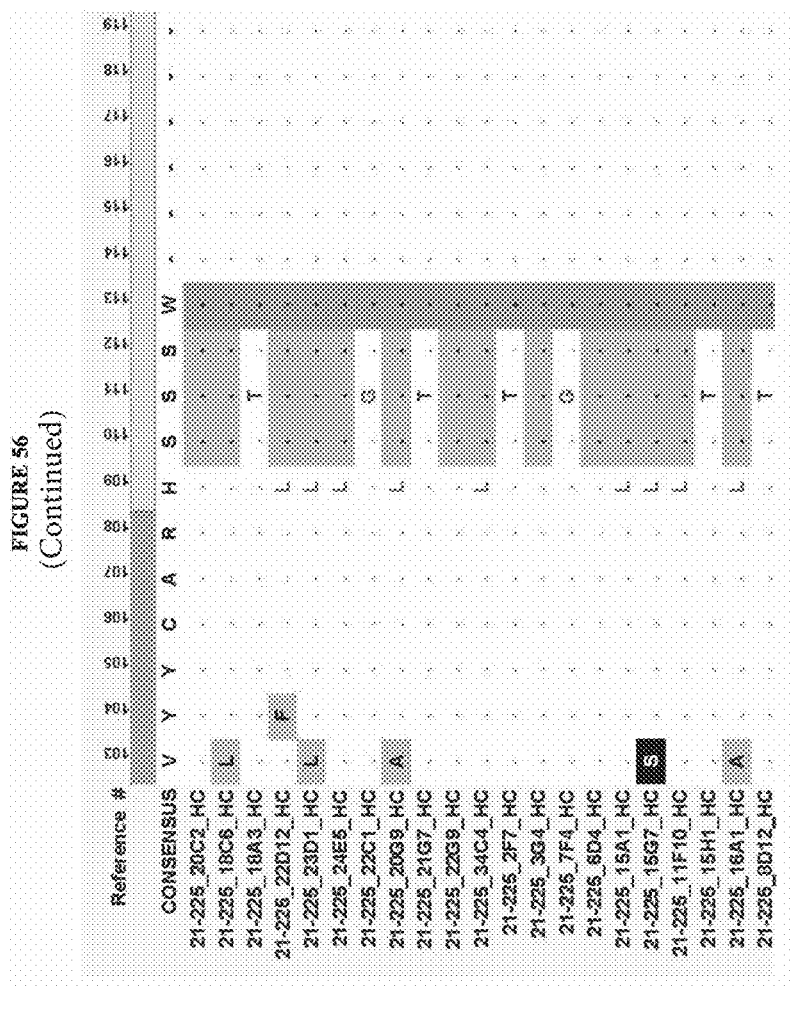
Figure 56:
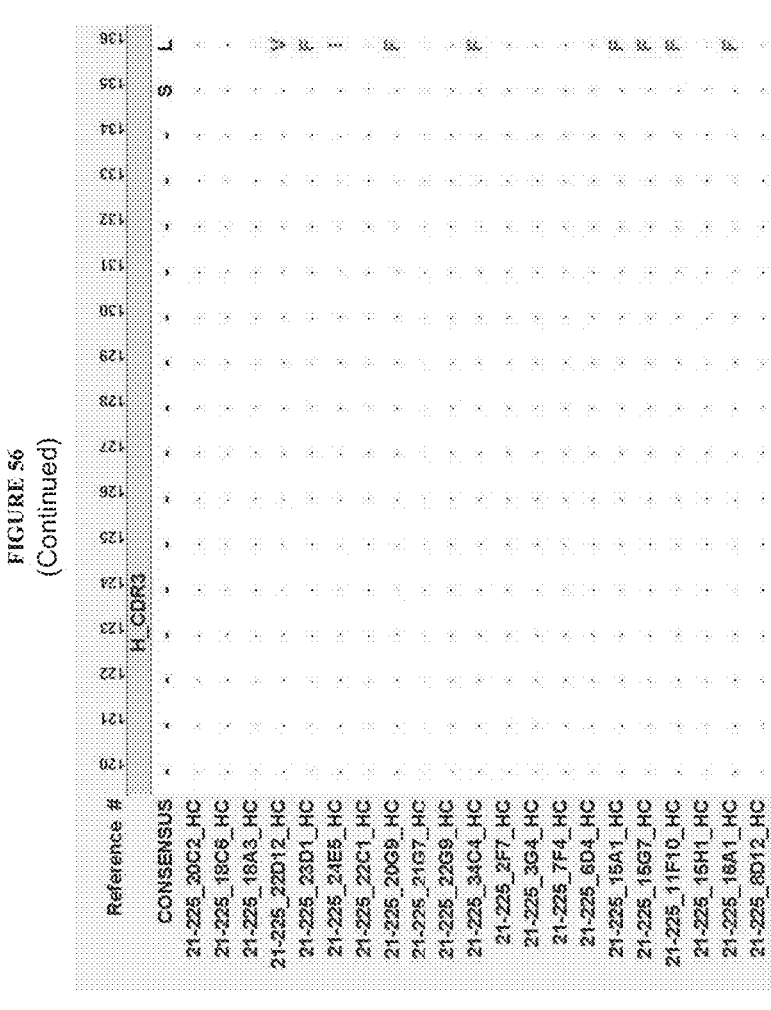
Figure 56:
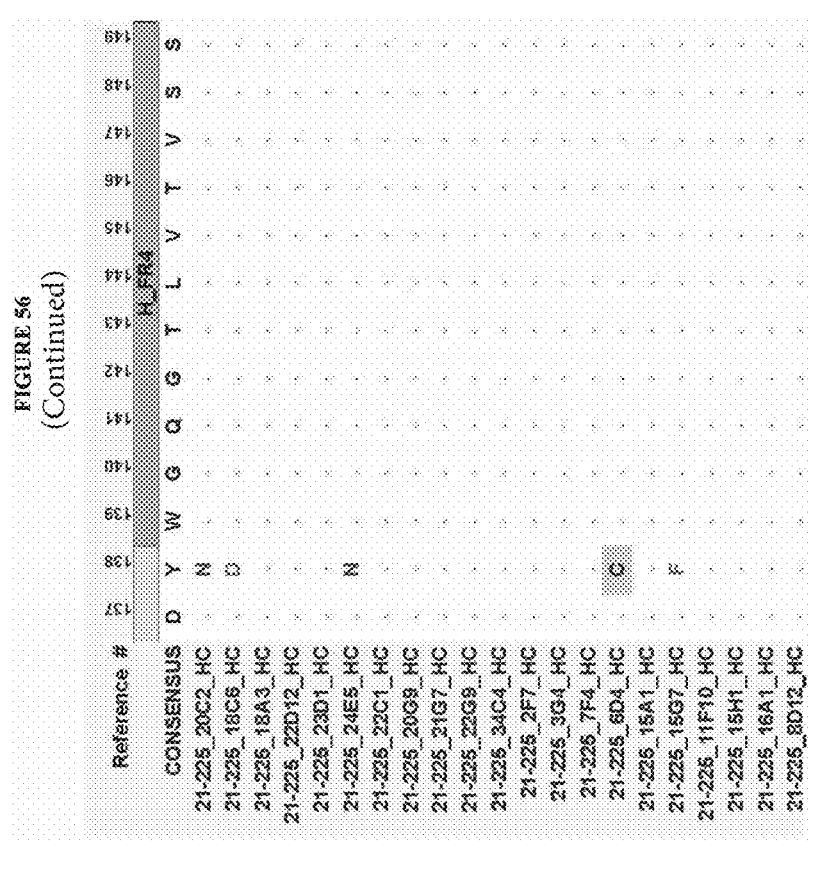
Figure 56:
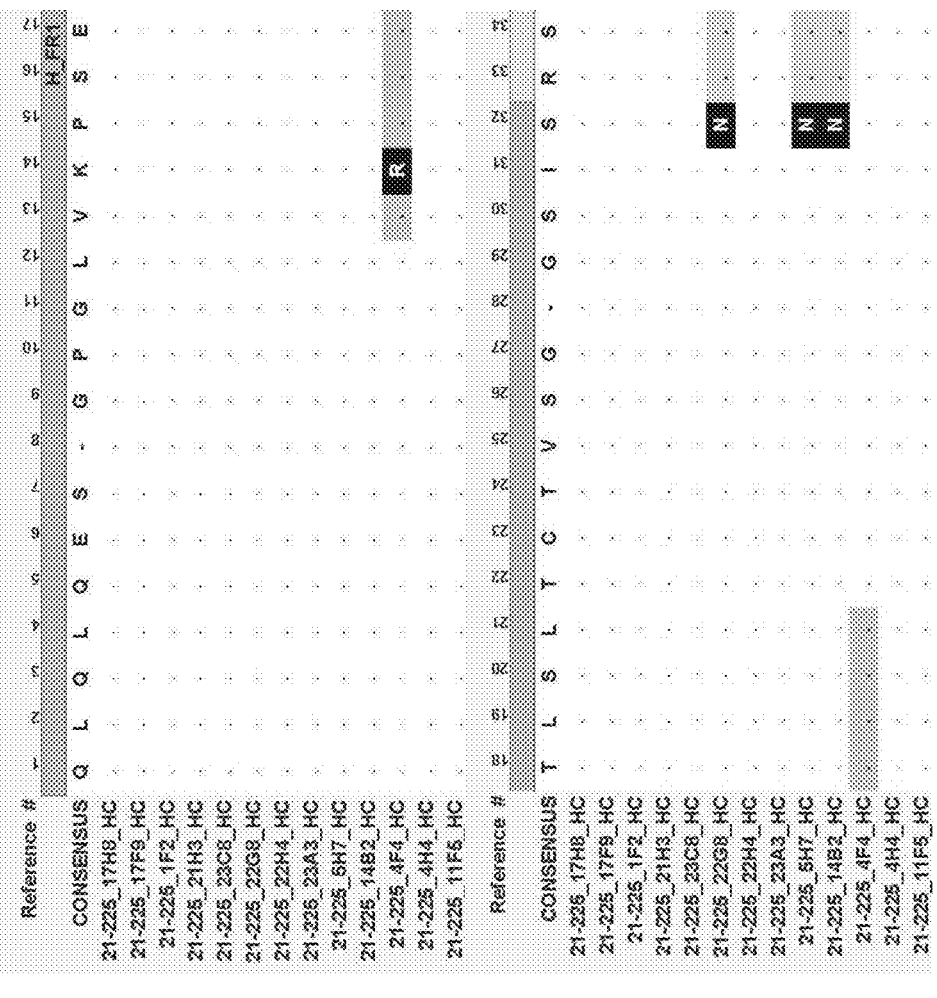
Figure 56:
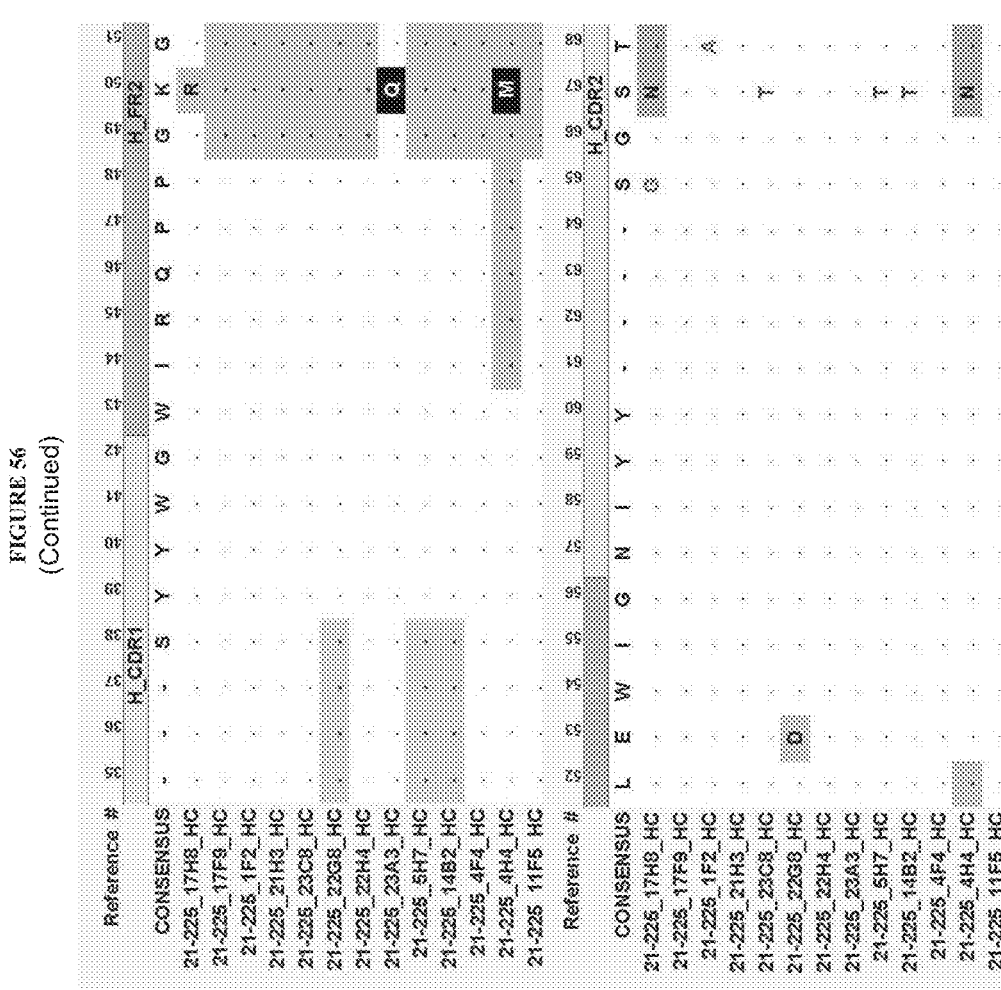
Figure 56:
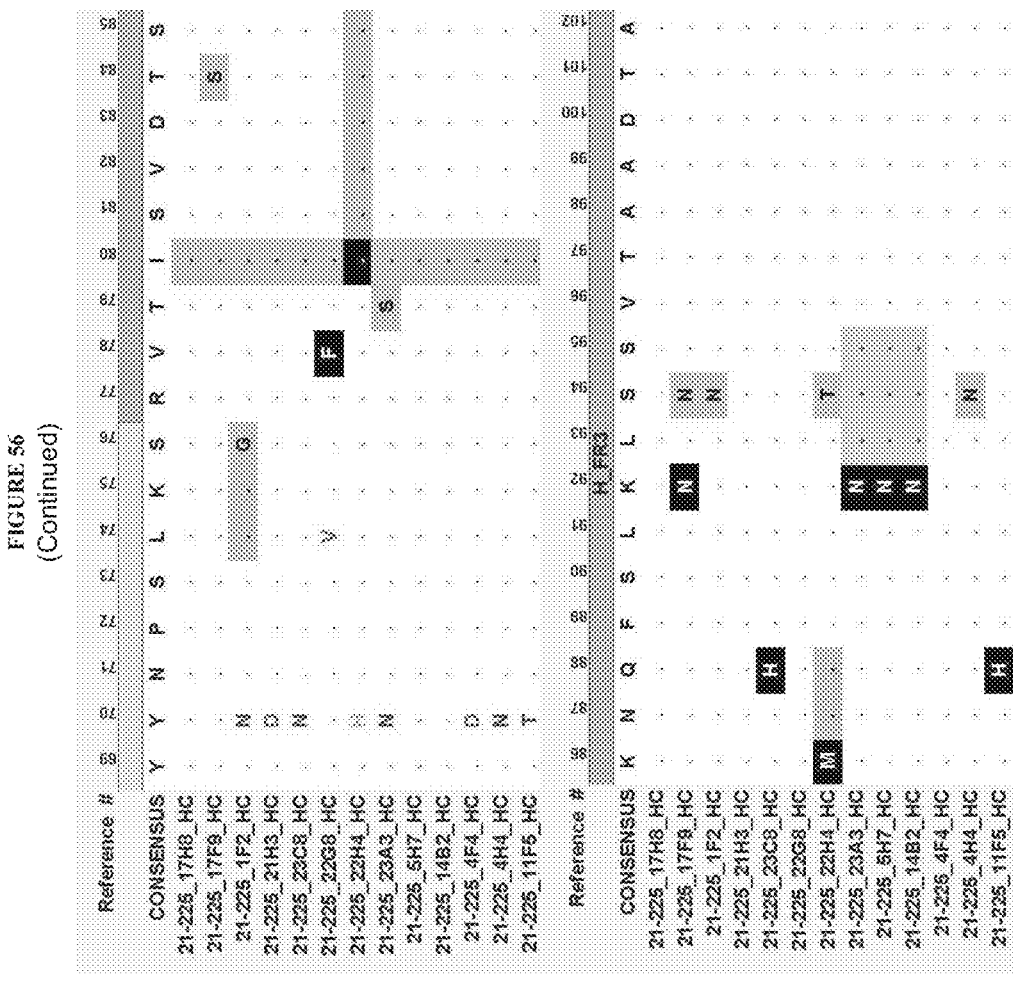
Figure 56:
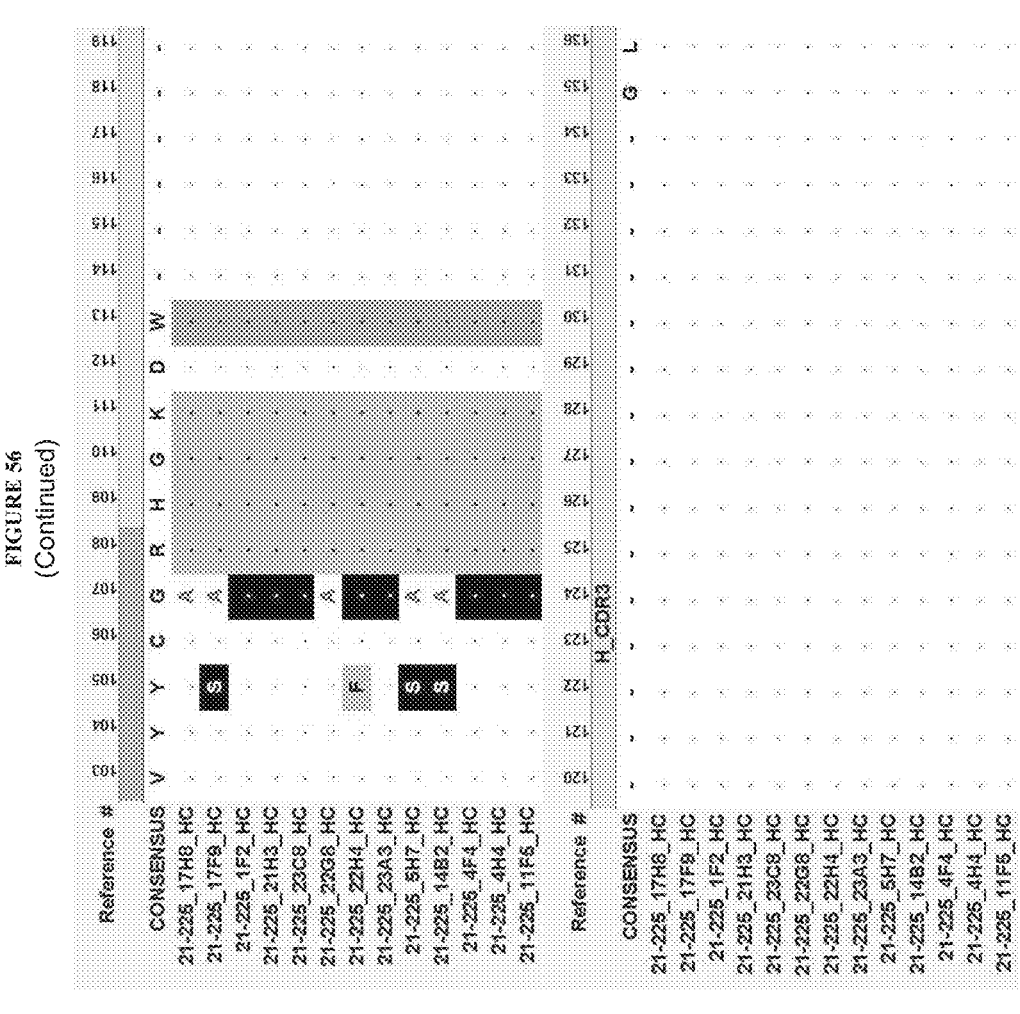
Figure 56:
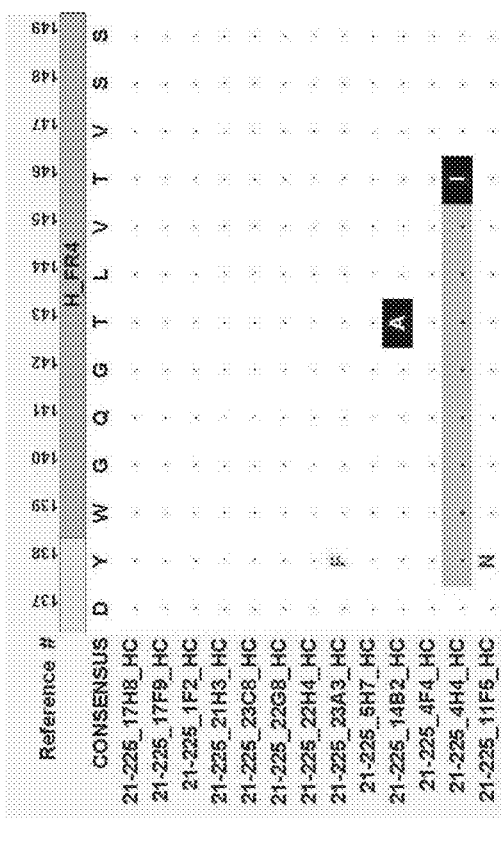
Figure 56:
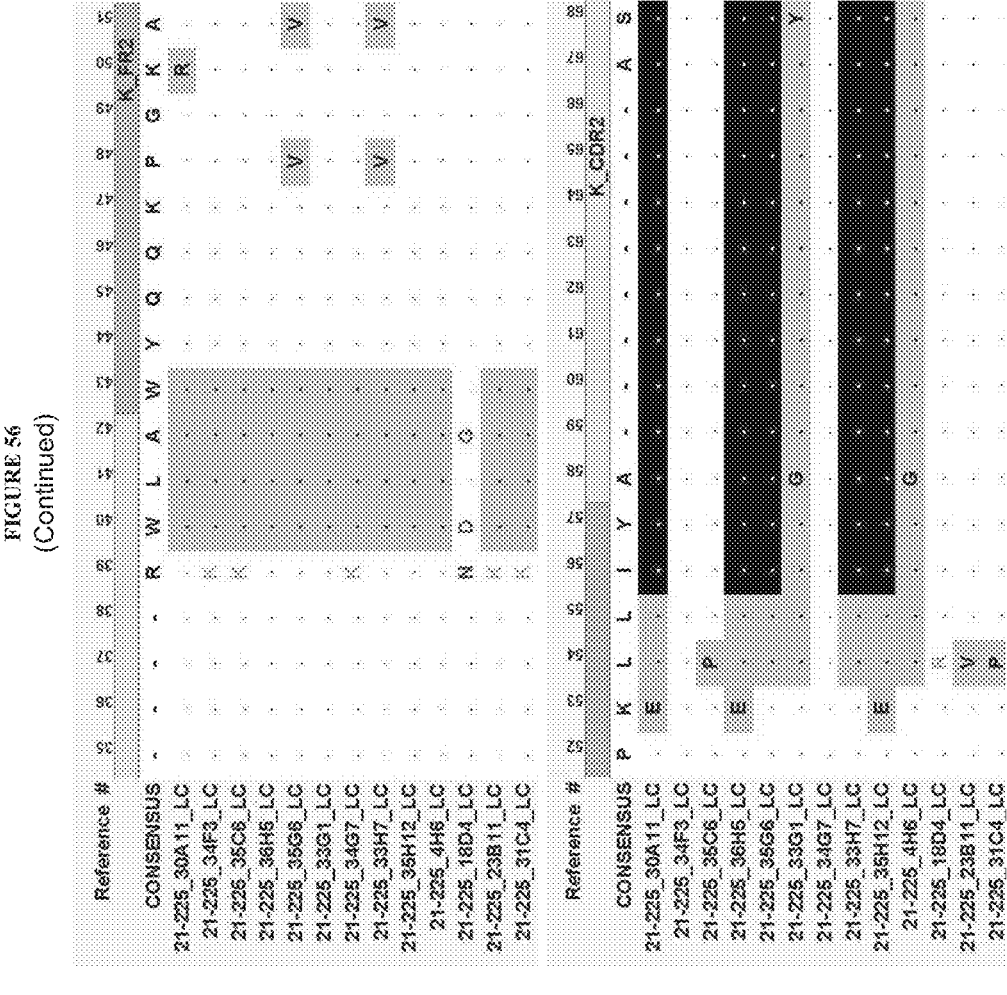
Figure 56:
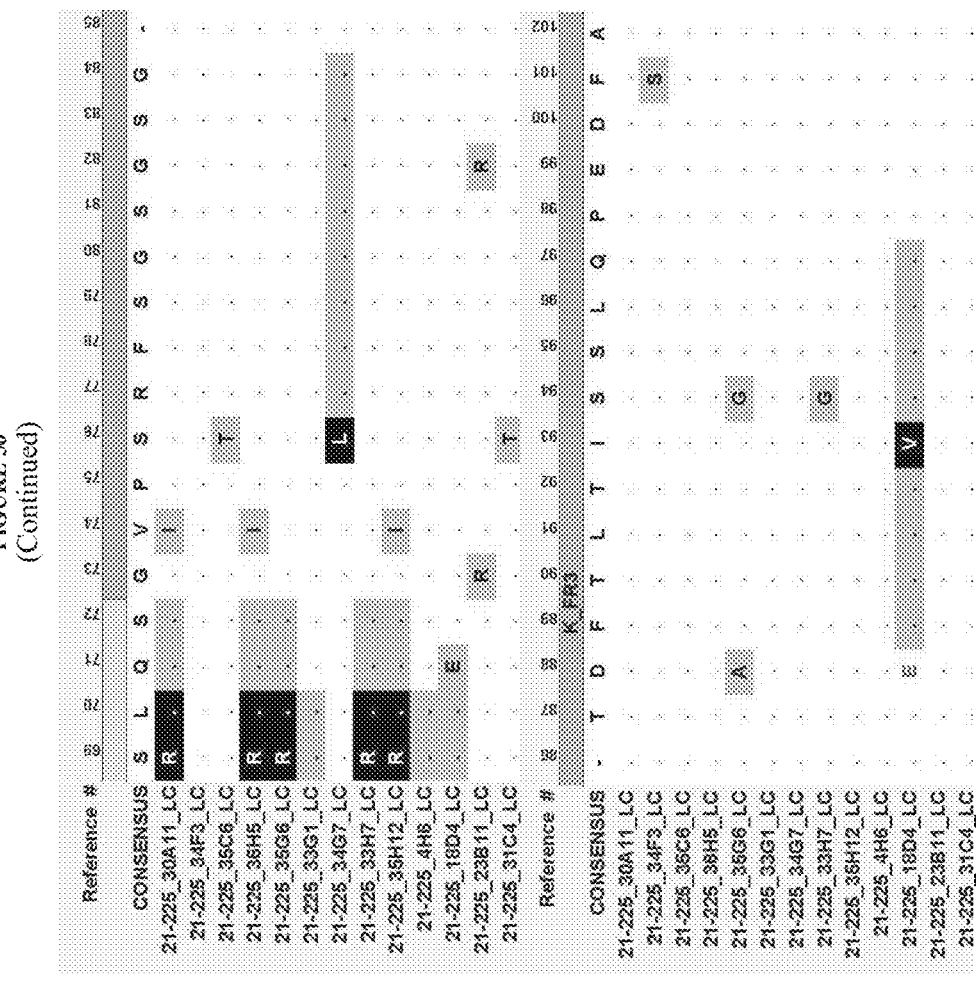
Figure 56:
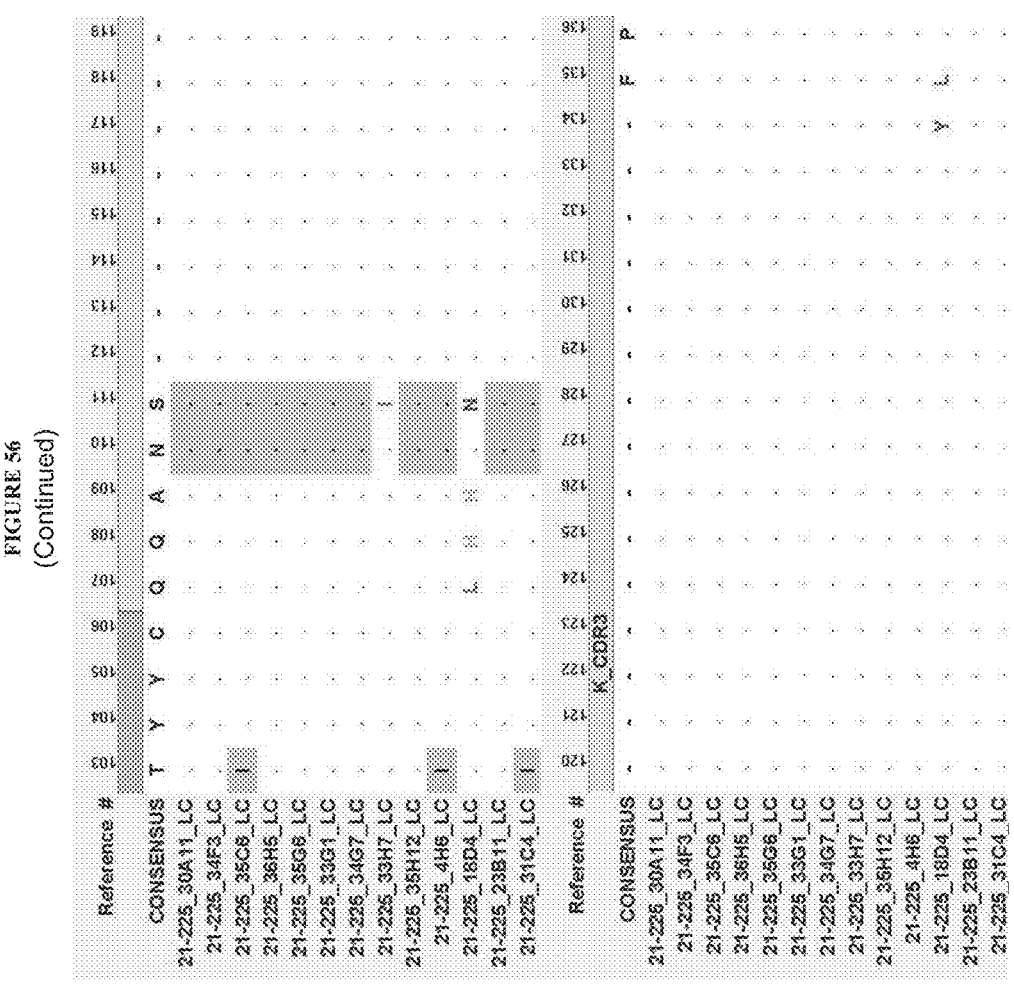
Figure 56:
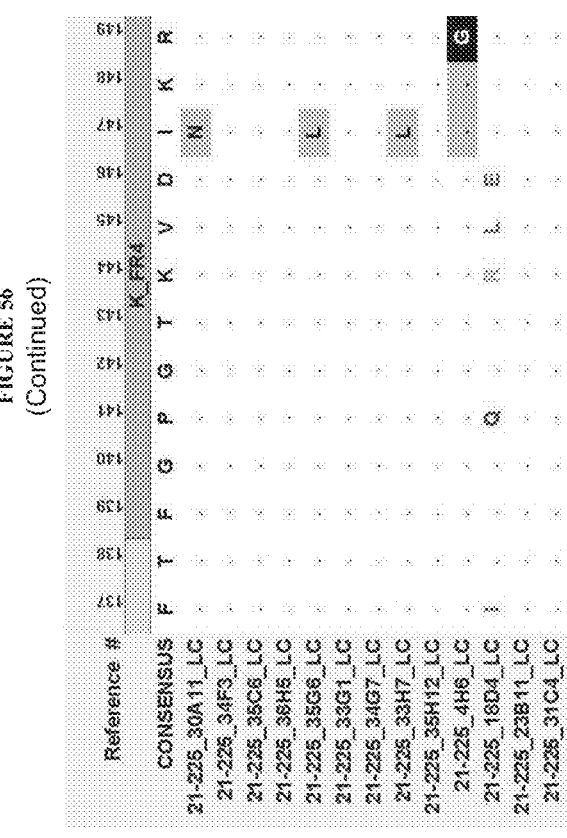
Figure 56:
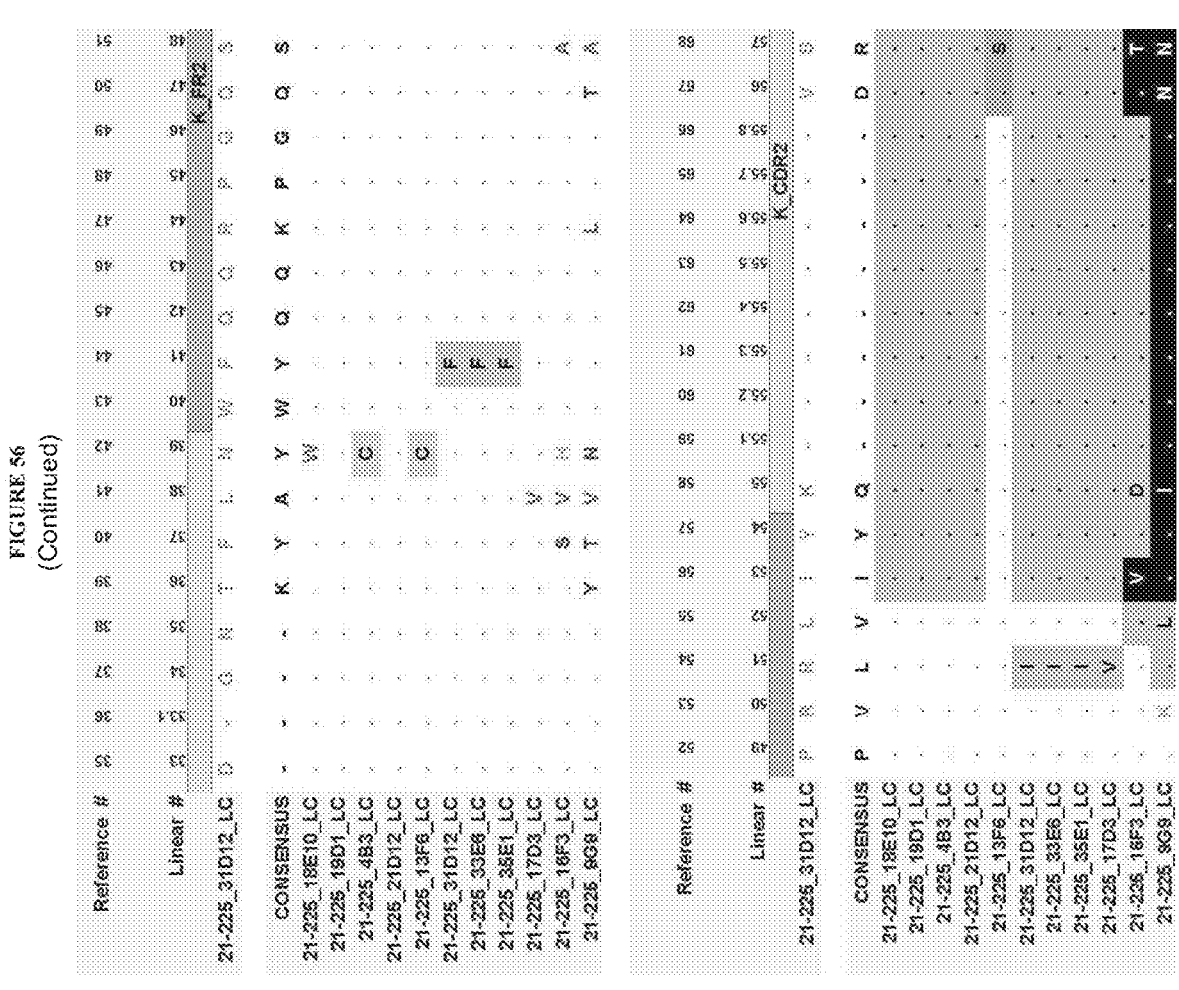
Figure 56:
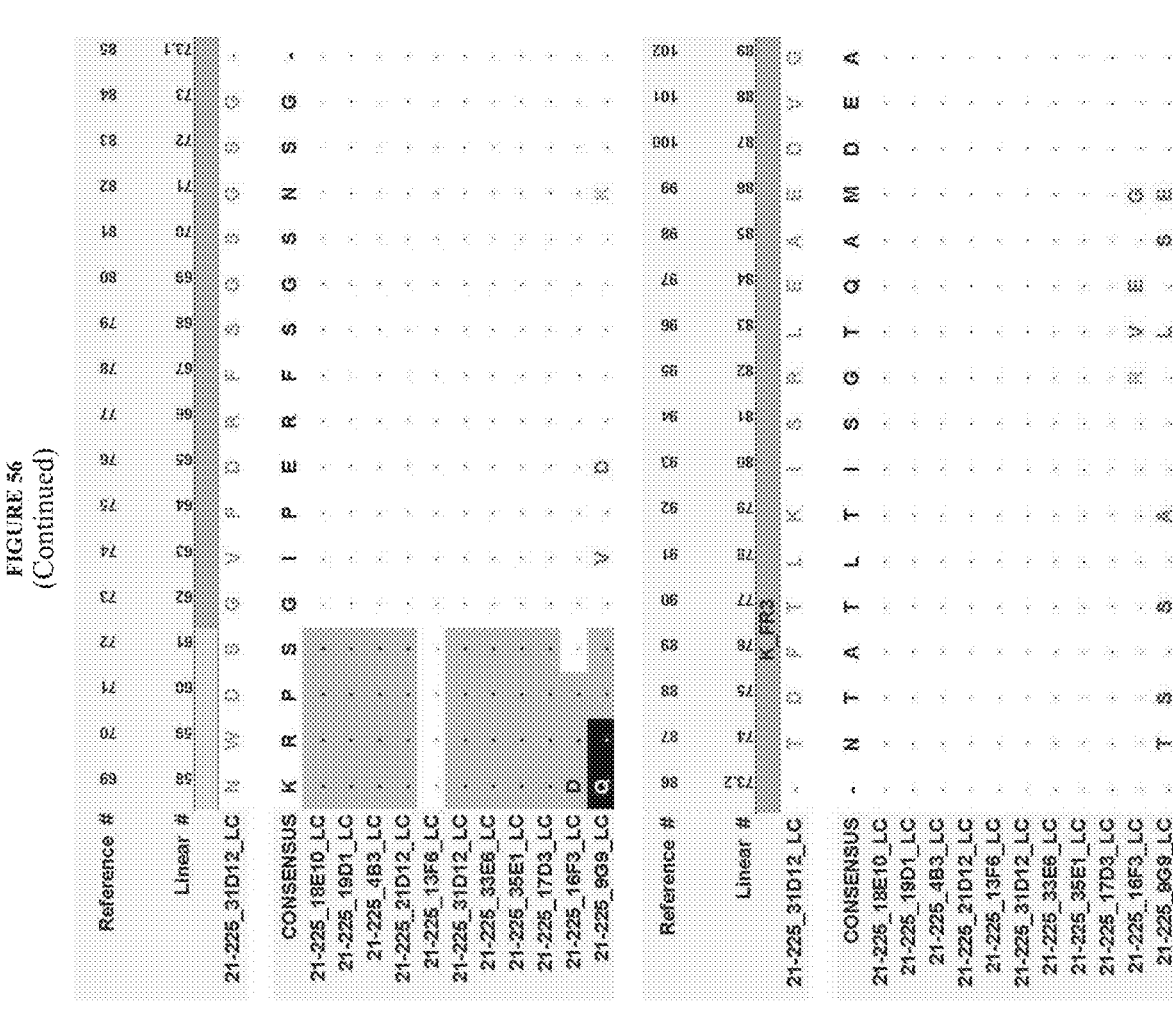
Figure 56:
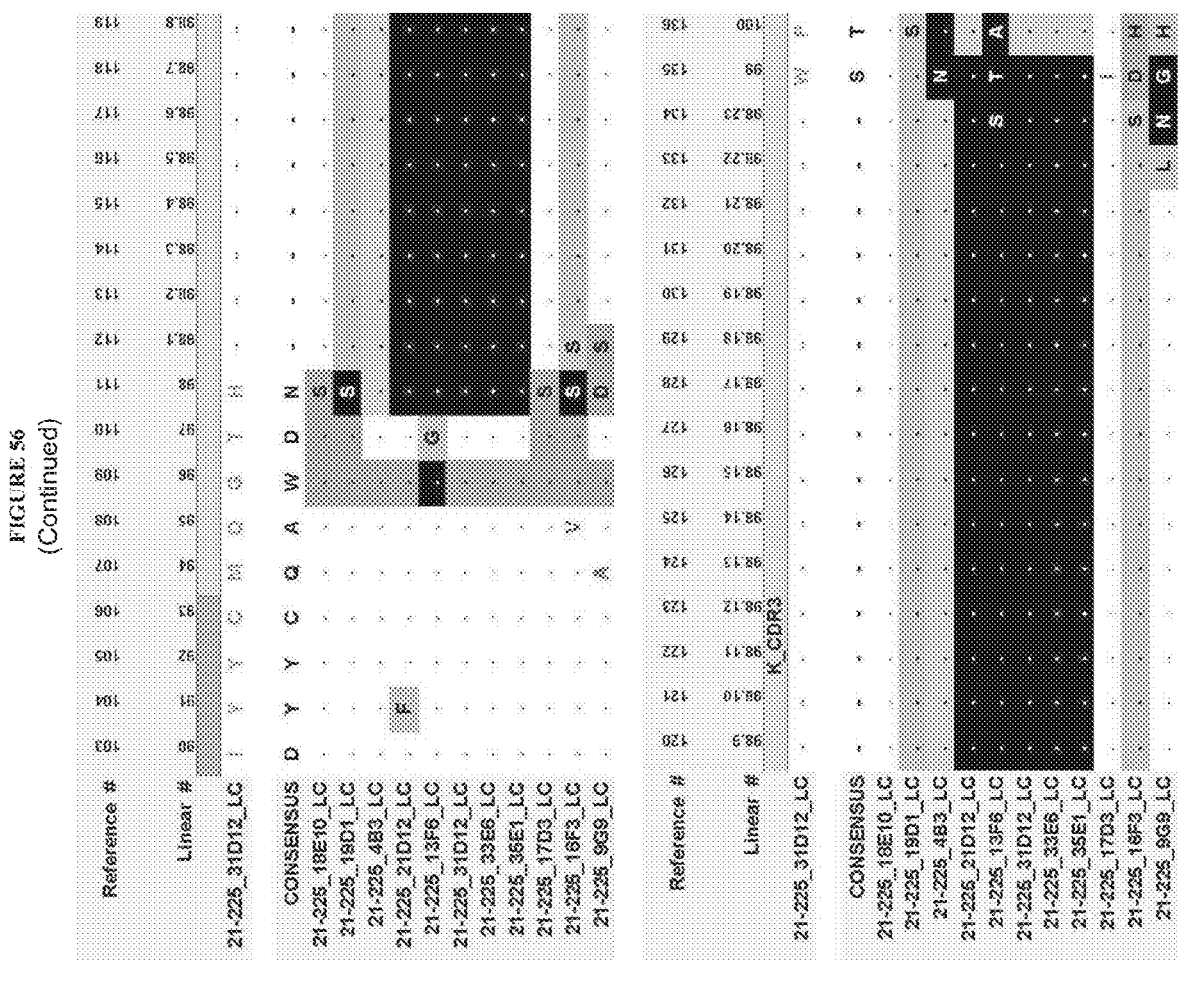
Figure 56:
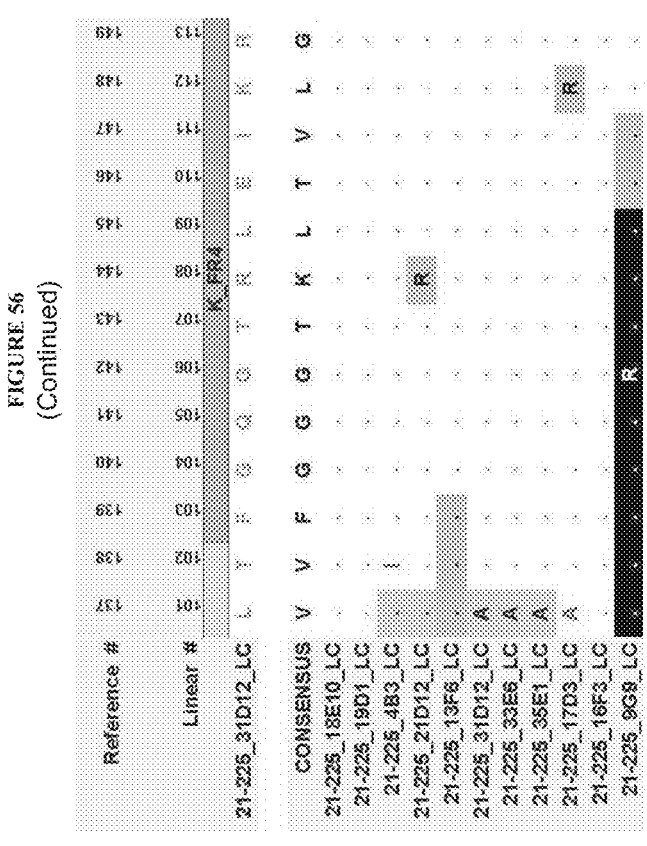
Figure 56:
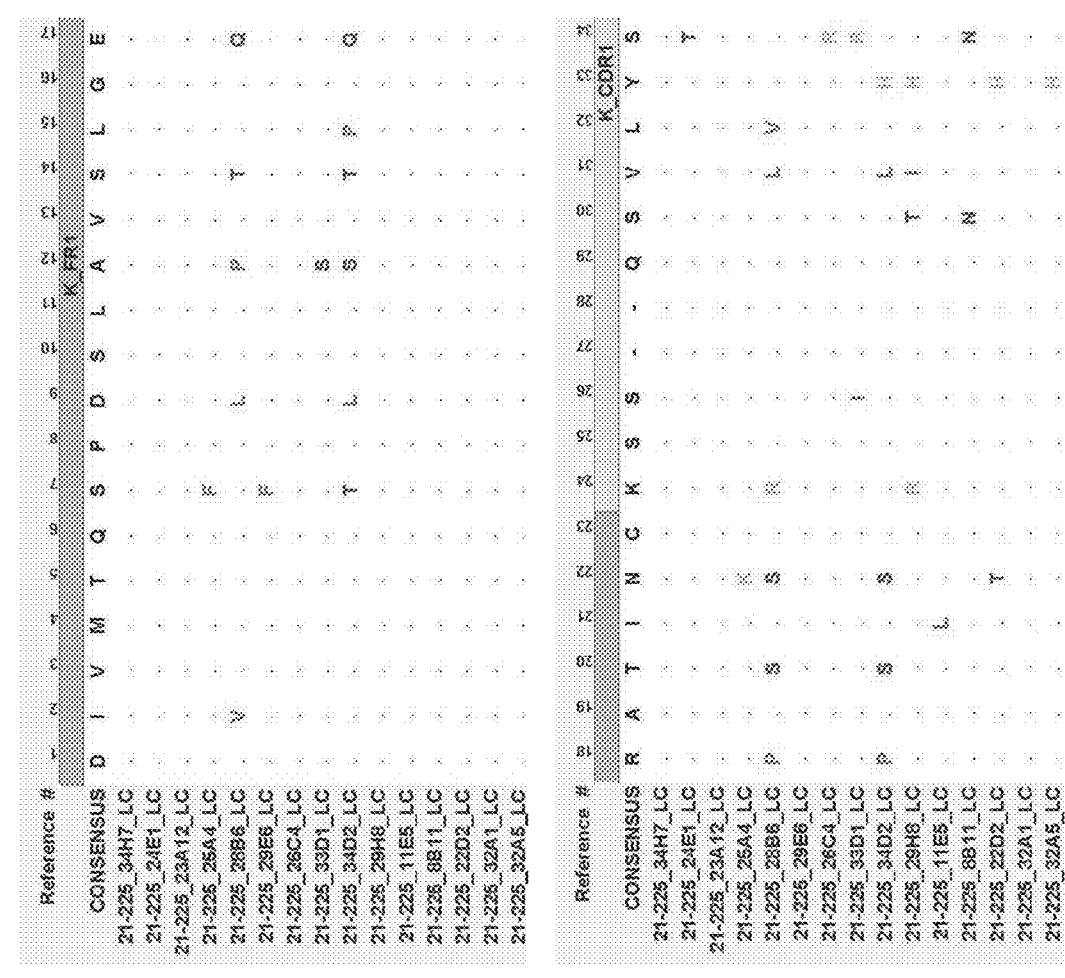
Figure 56:
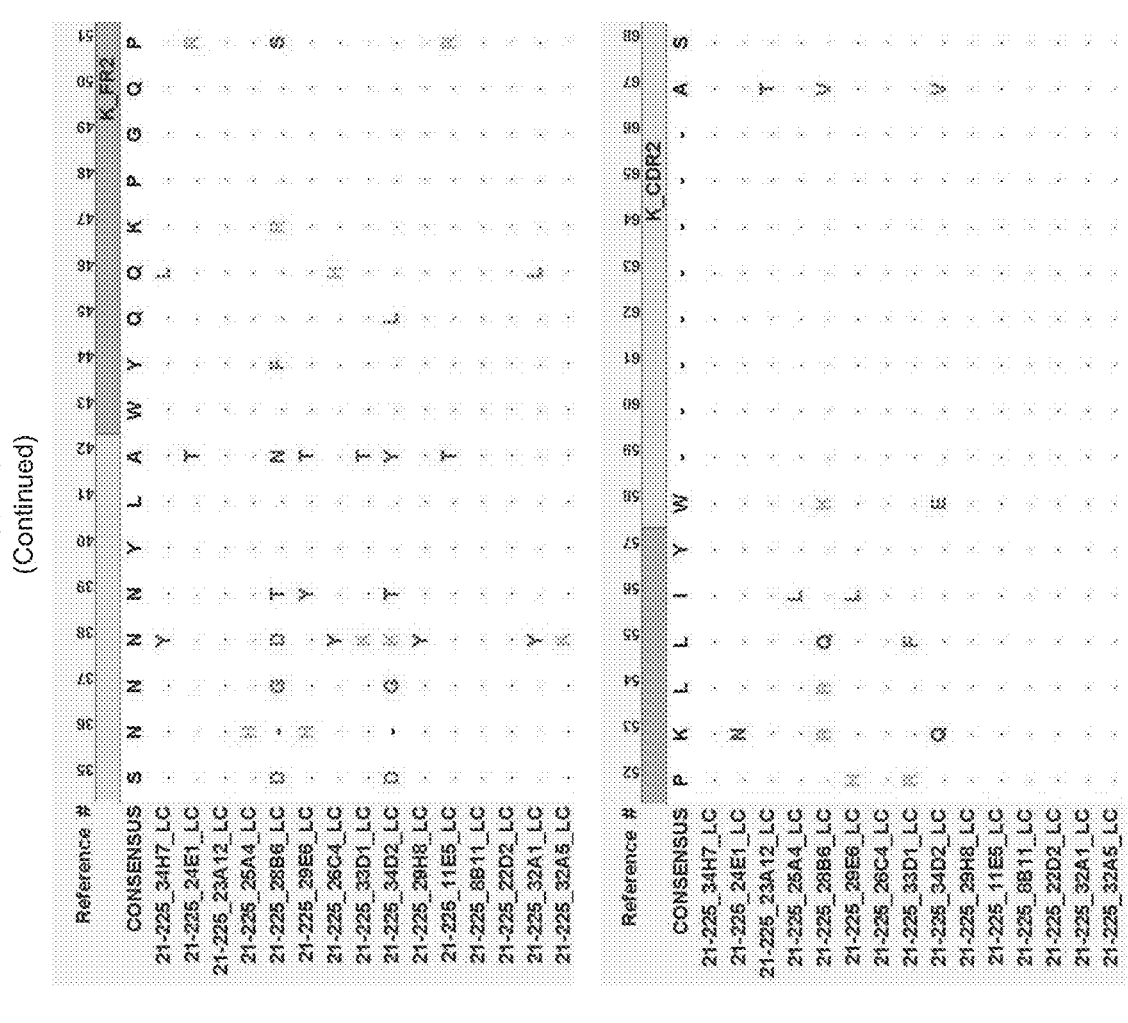
Figure 56:
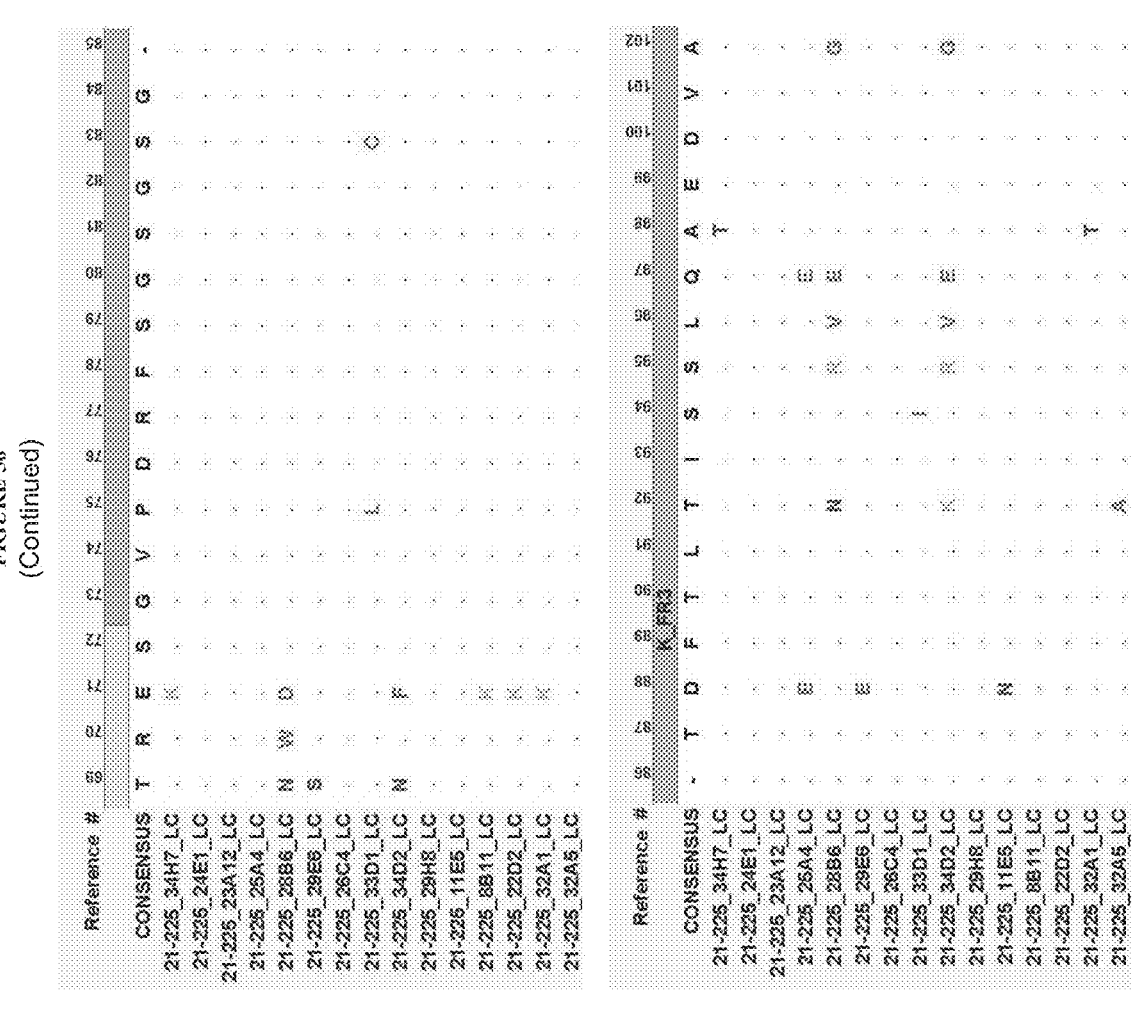
Figure 56:
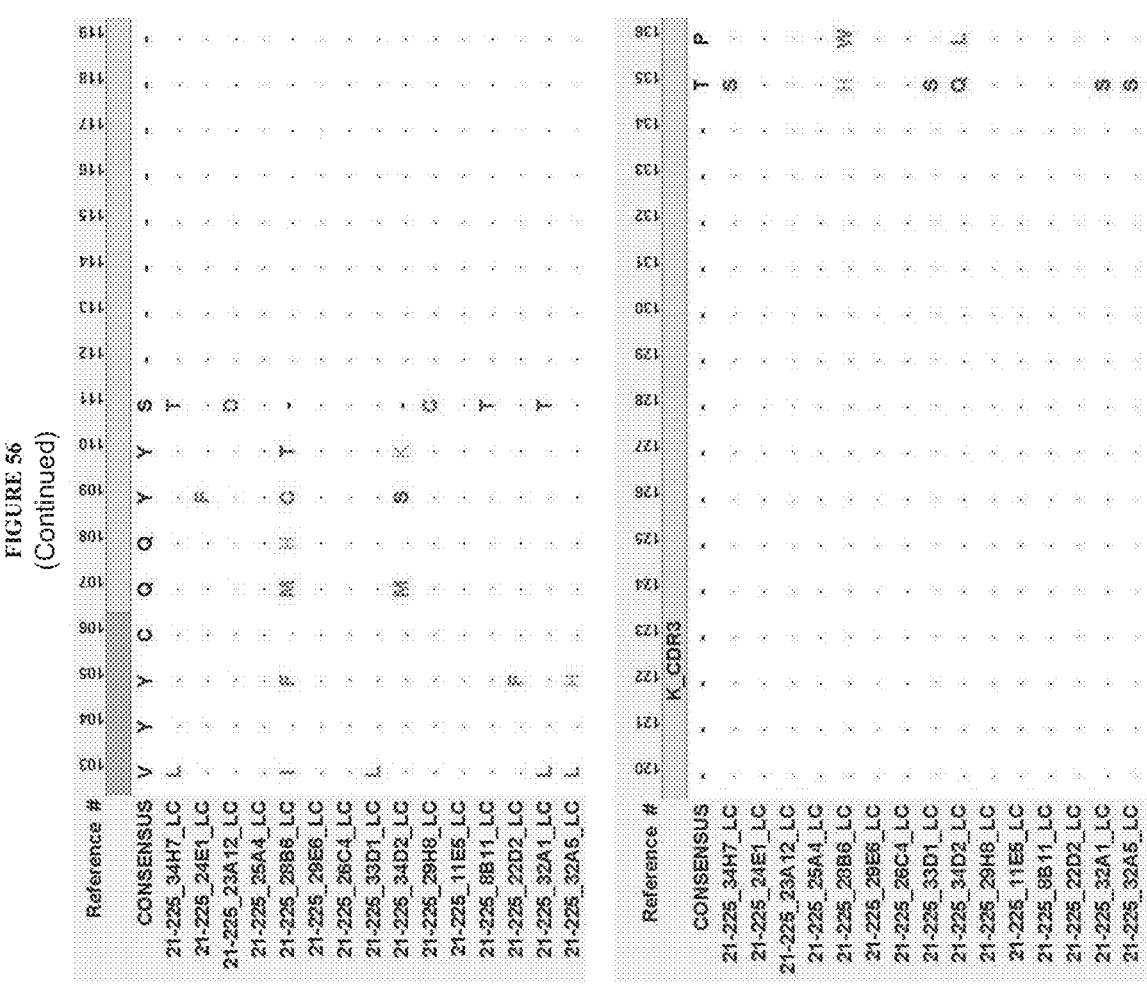
Figure 56:
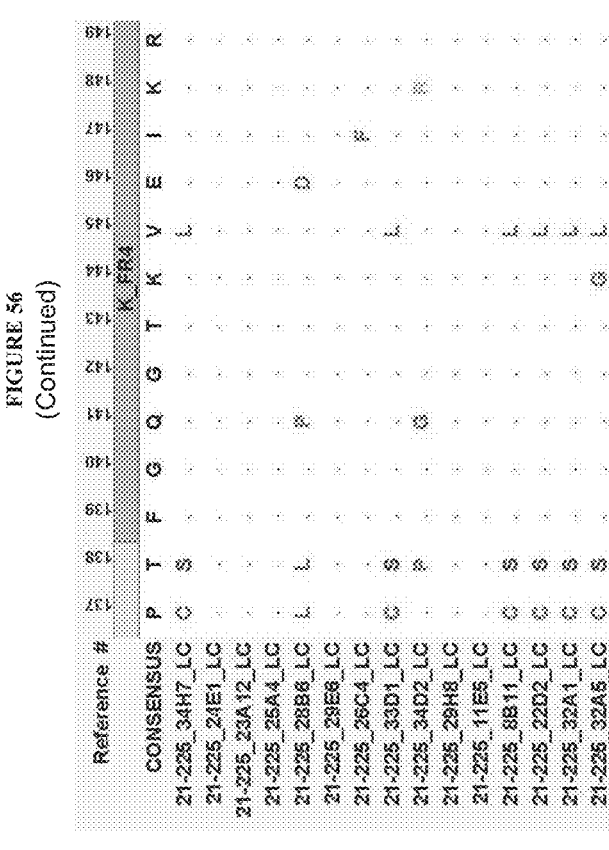
Figure 56:
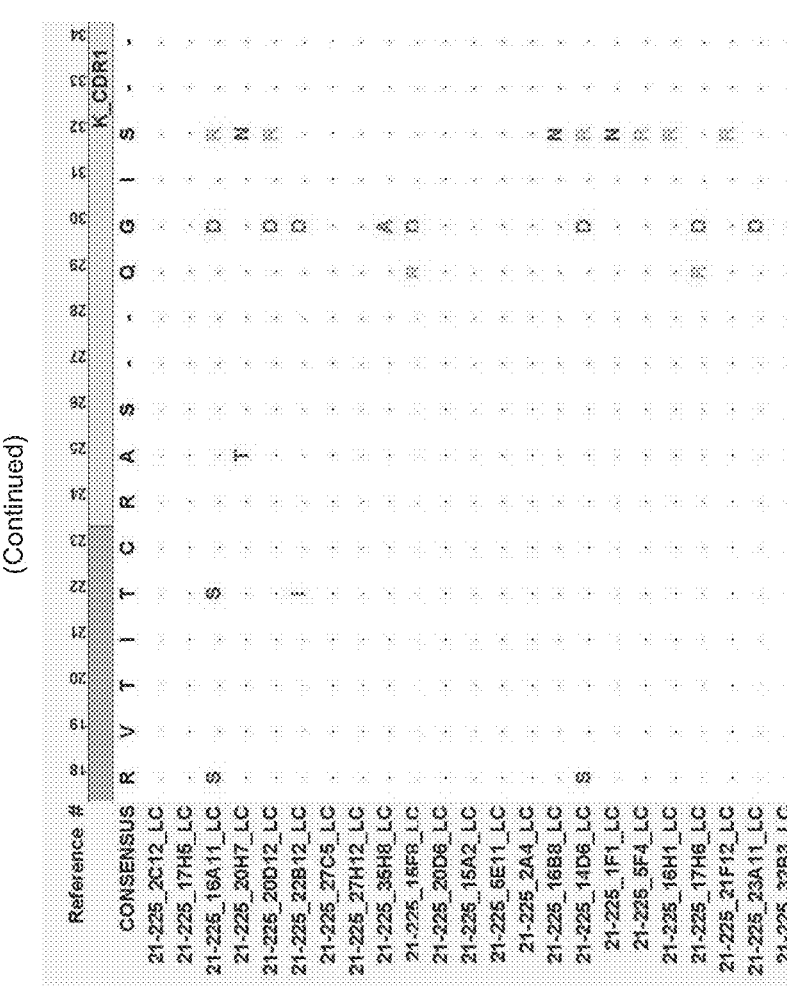
Figure 56:
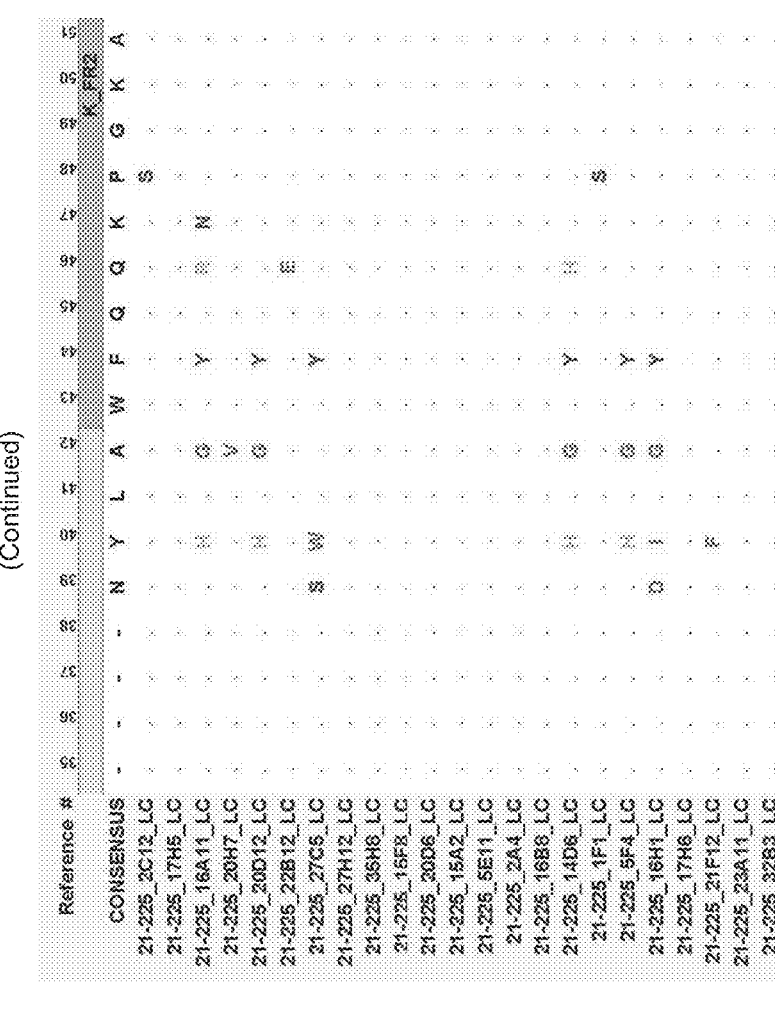
Figure 56:
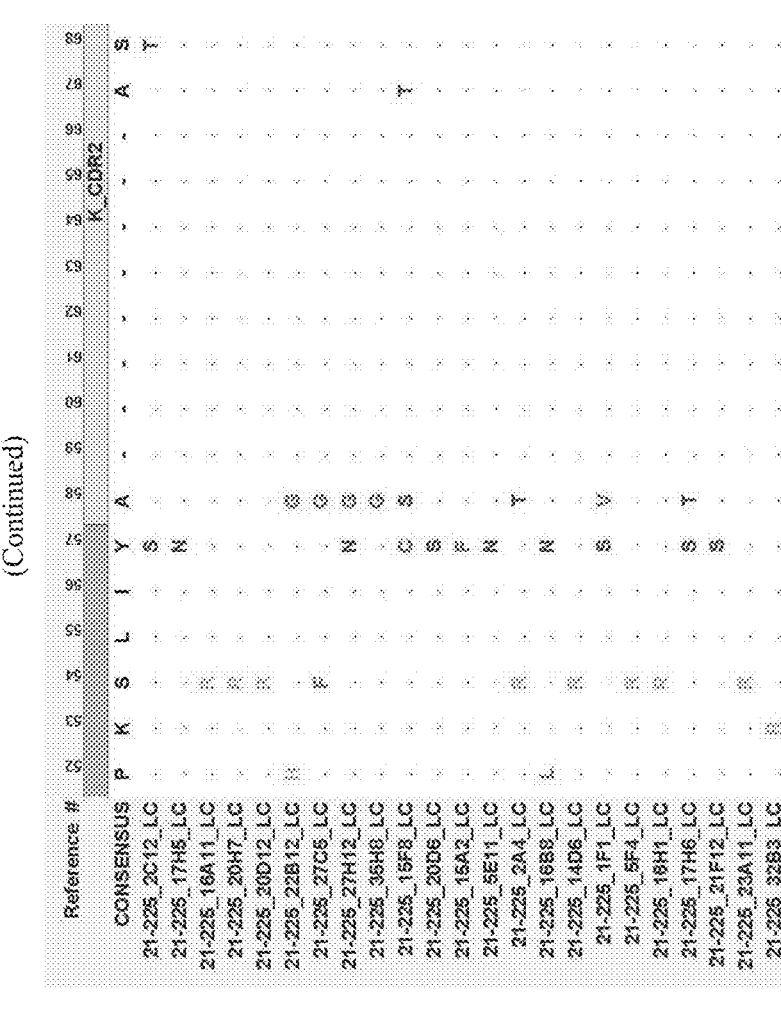
Figure 56:
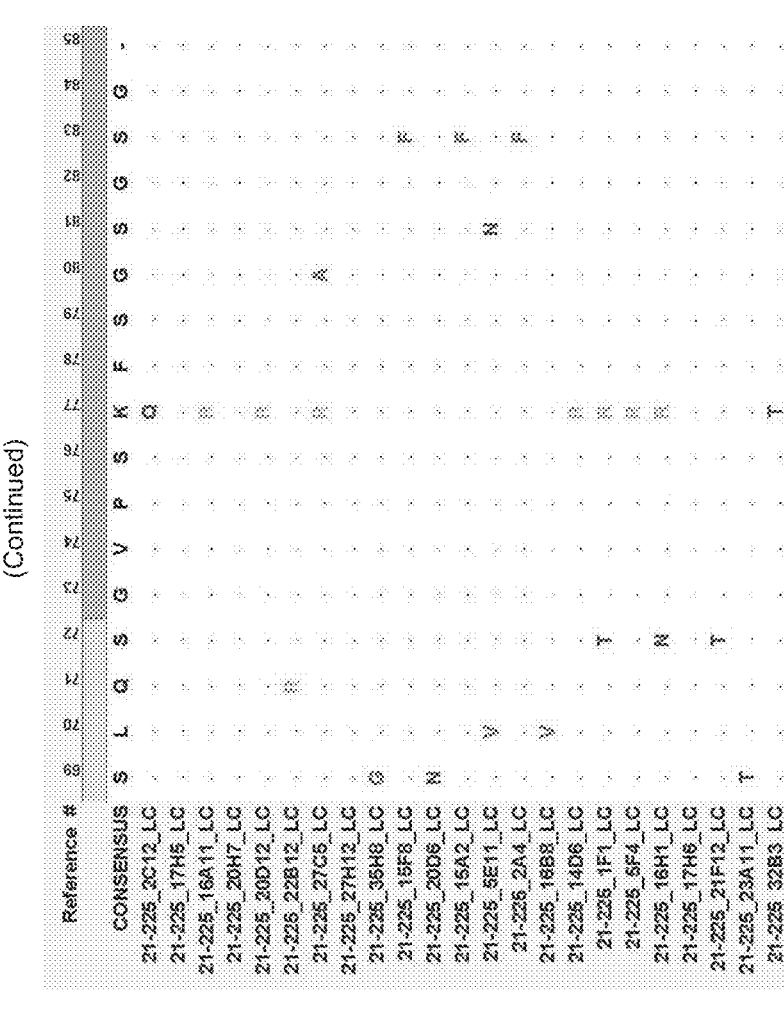
Figure 56:
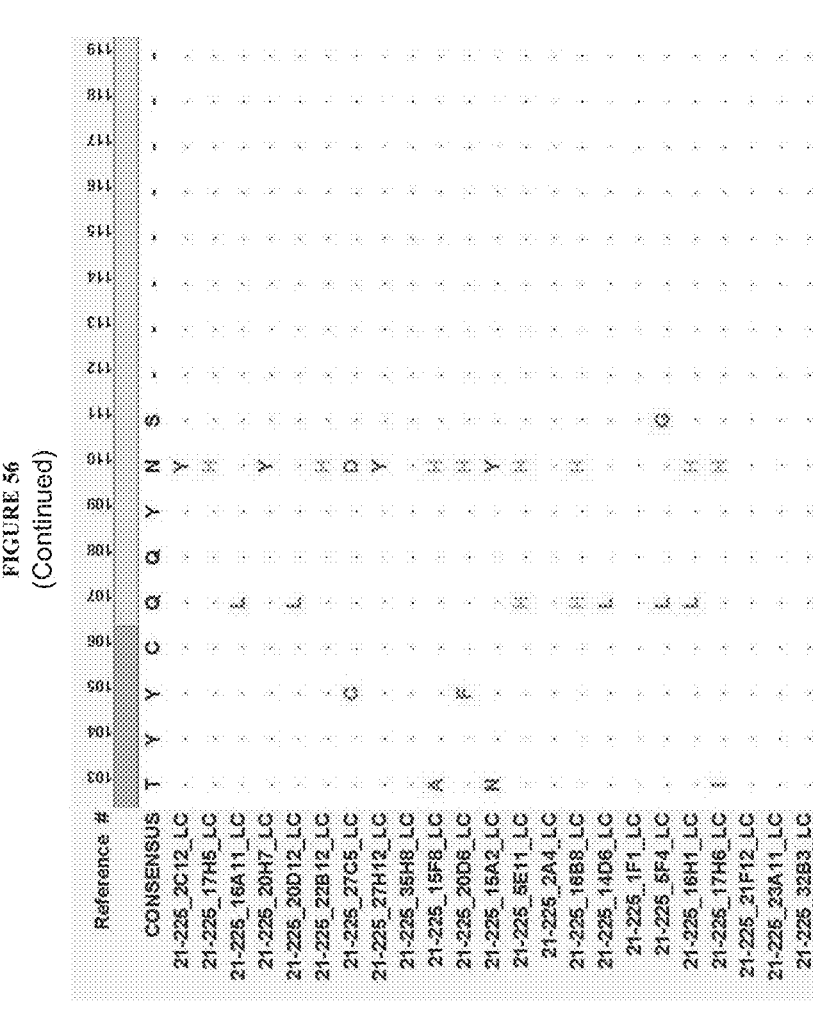
Figure 56:
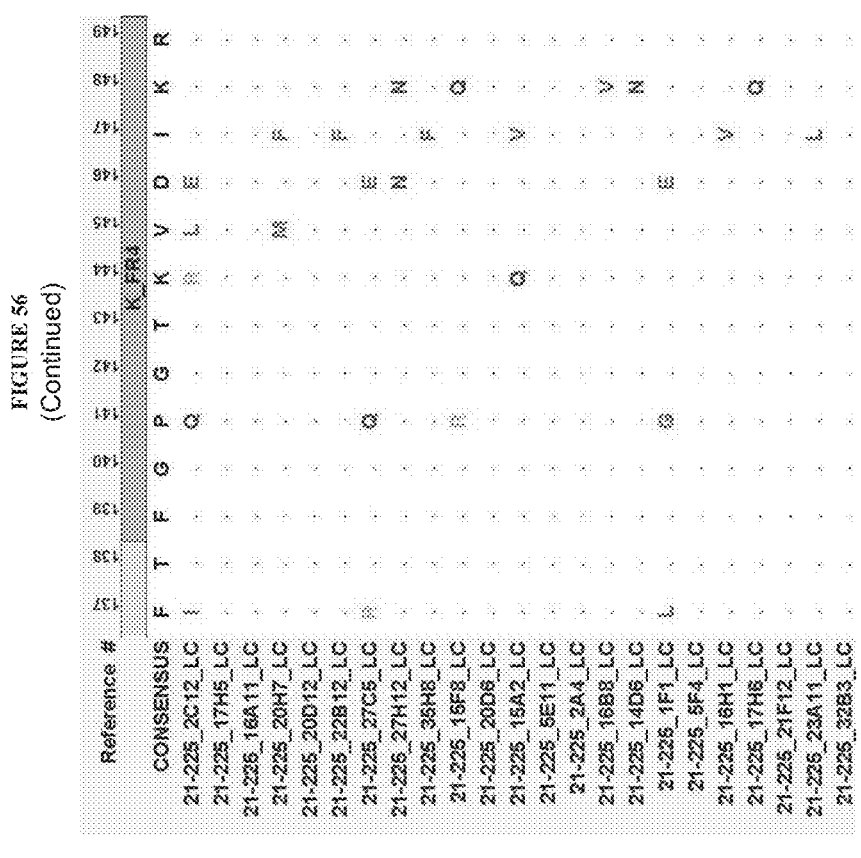
Figure 56:
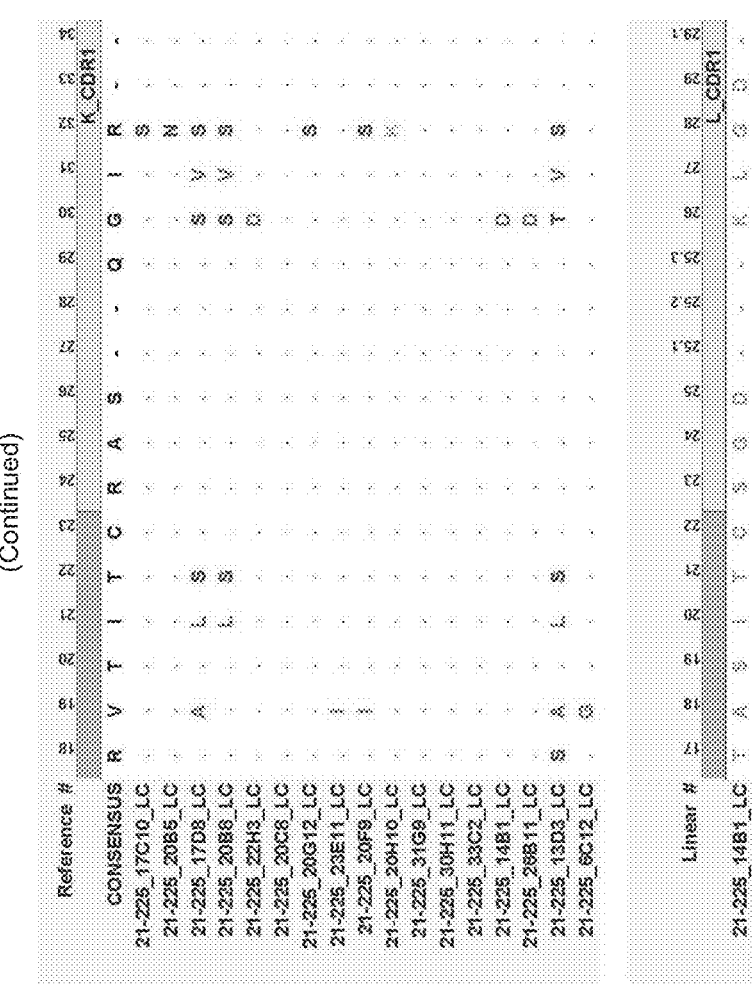
Figure 56:
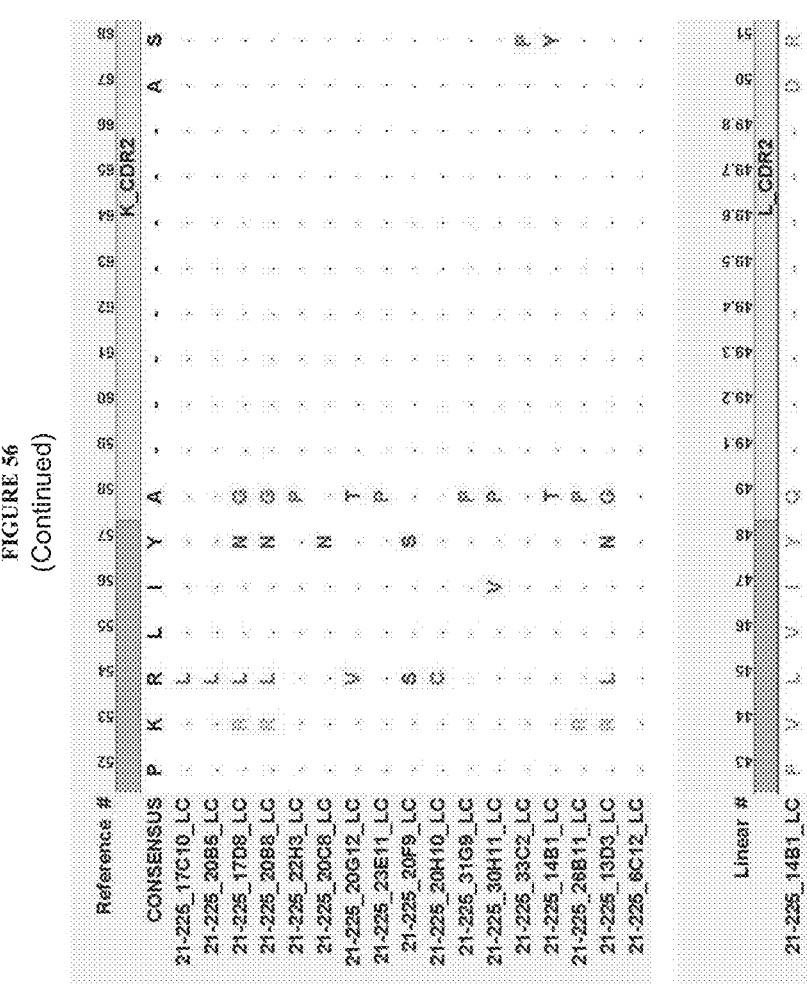
Figure 56:
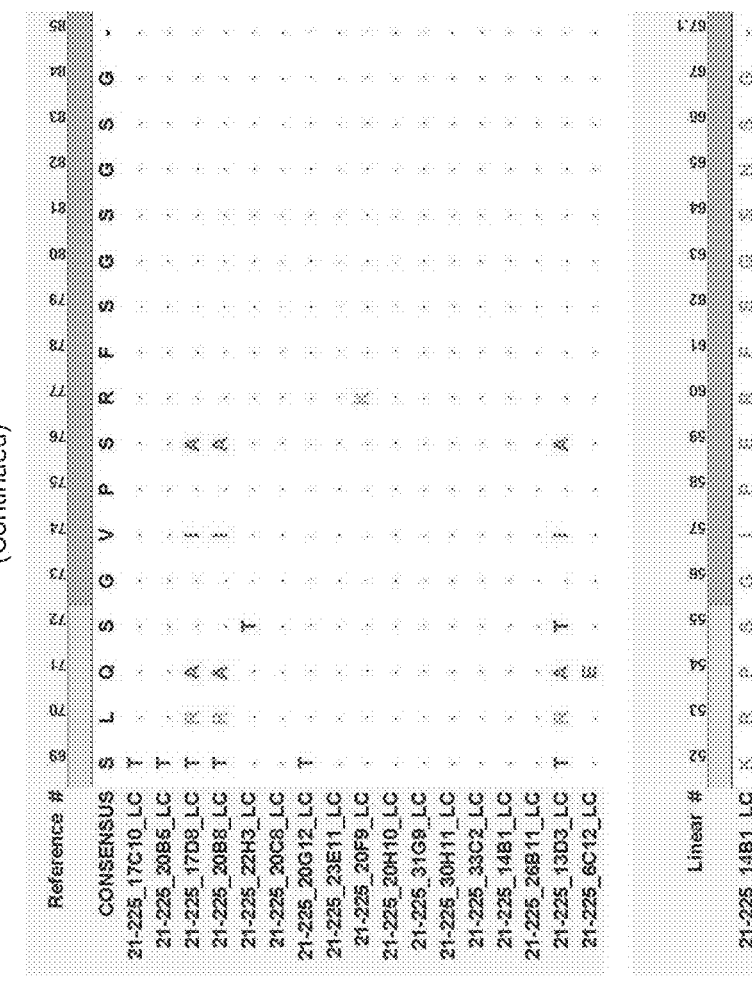
Figure 56:
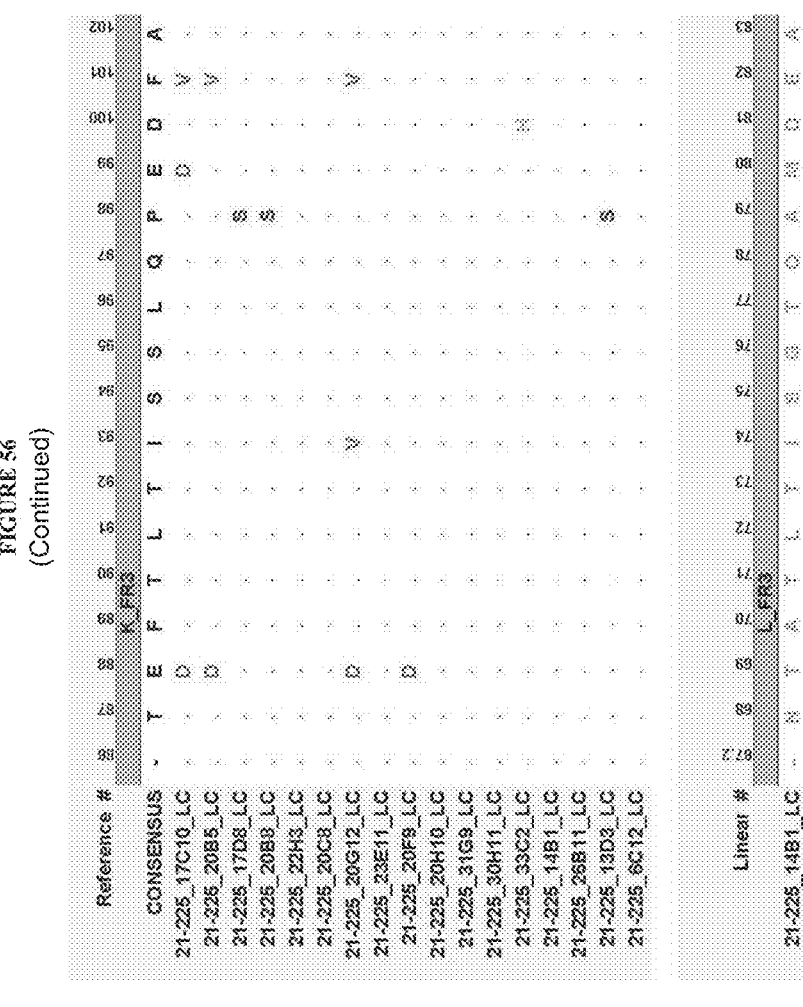
Figure 56:
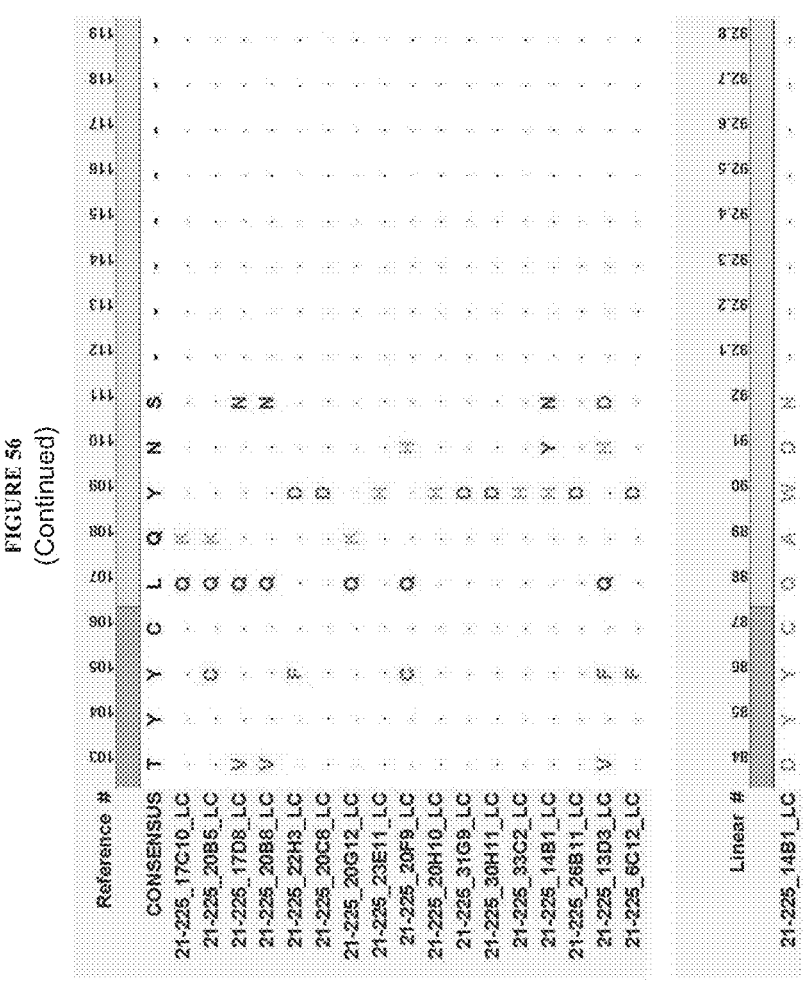
Figure 56:
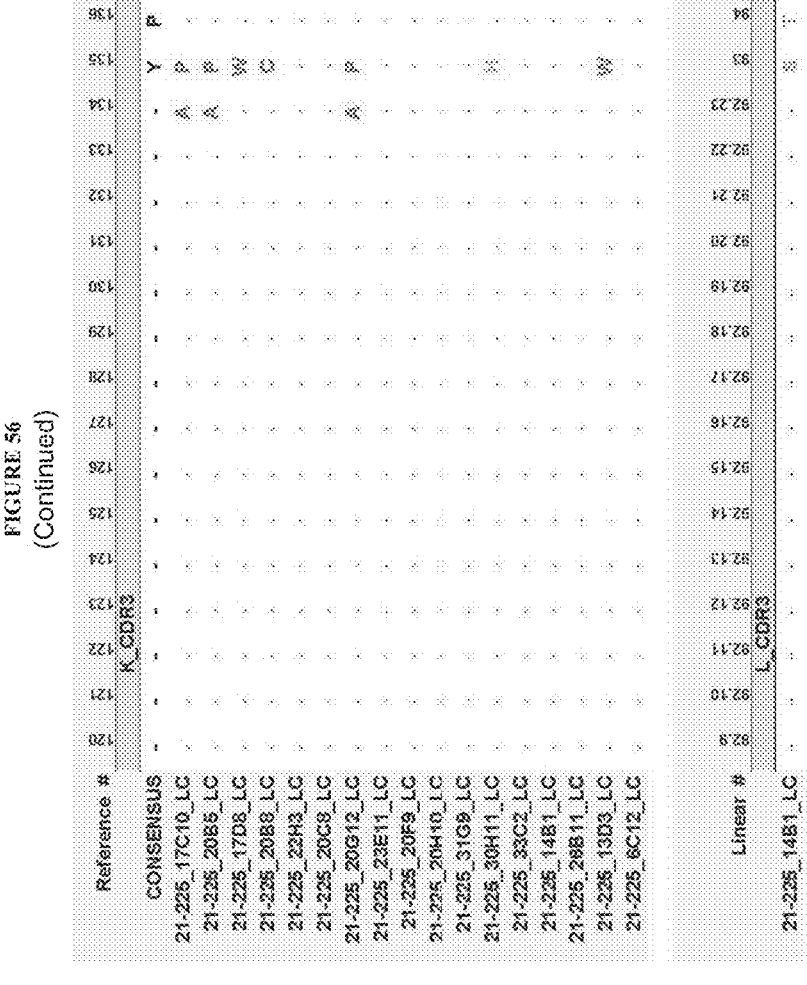
Figure 56:
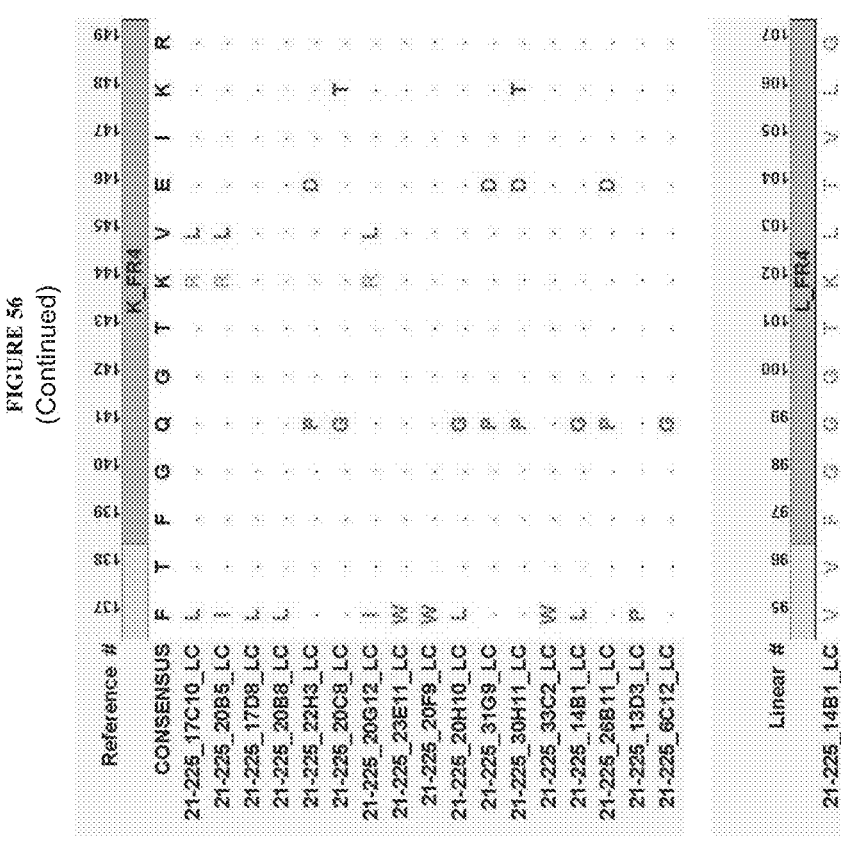
Figure 56:
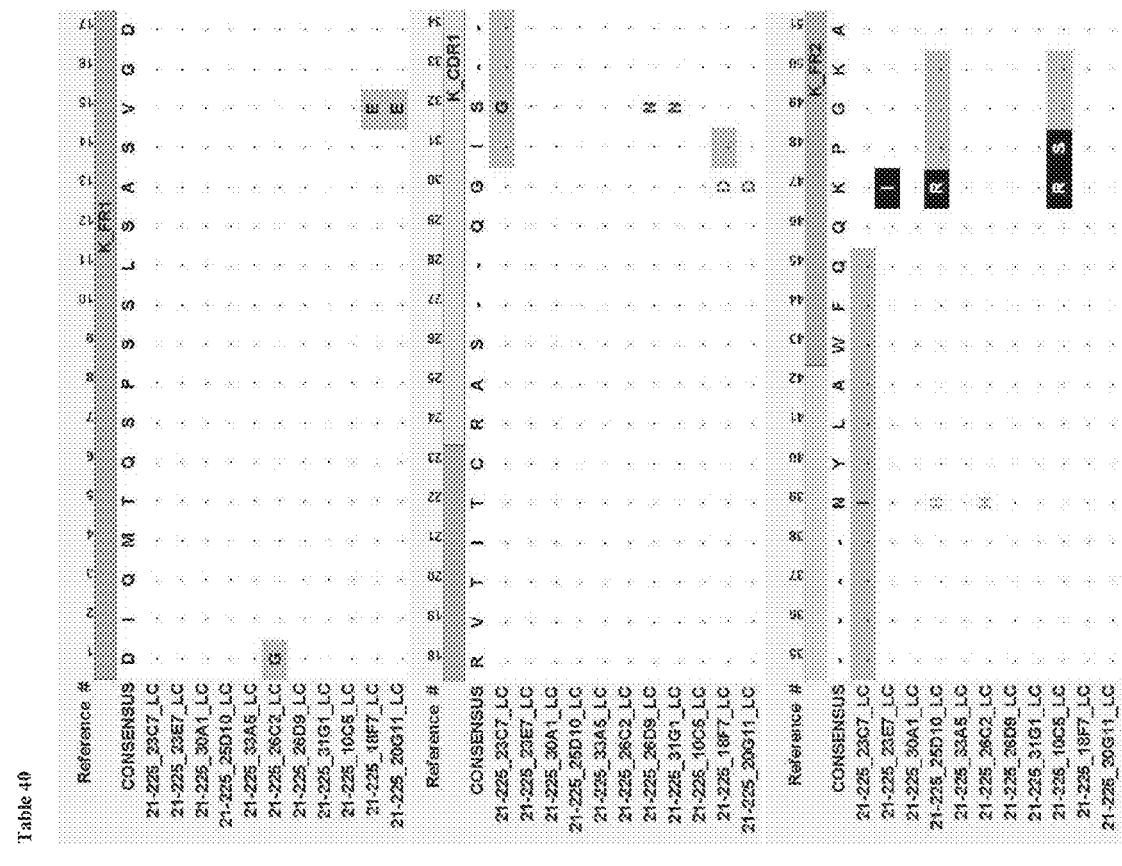
Figure 56:
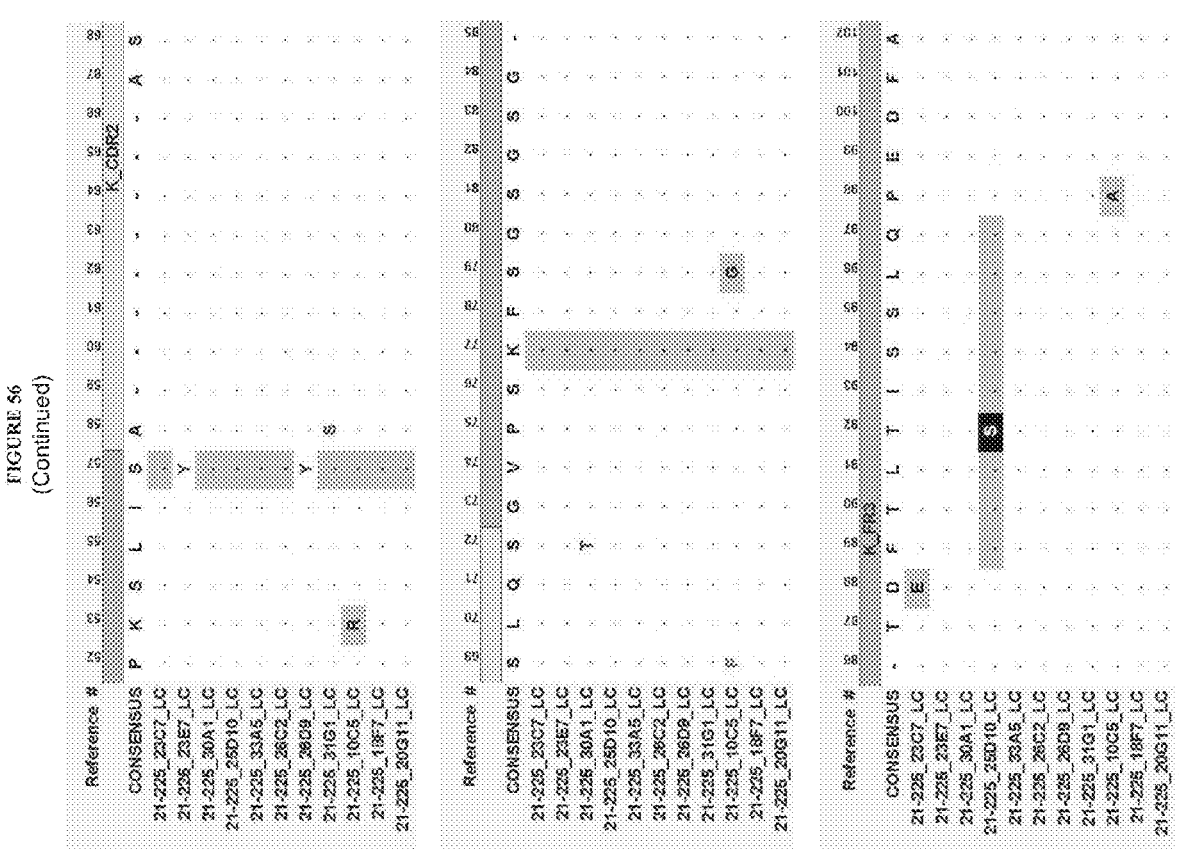
Figure 56:
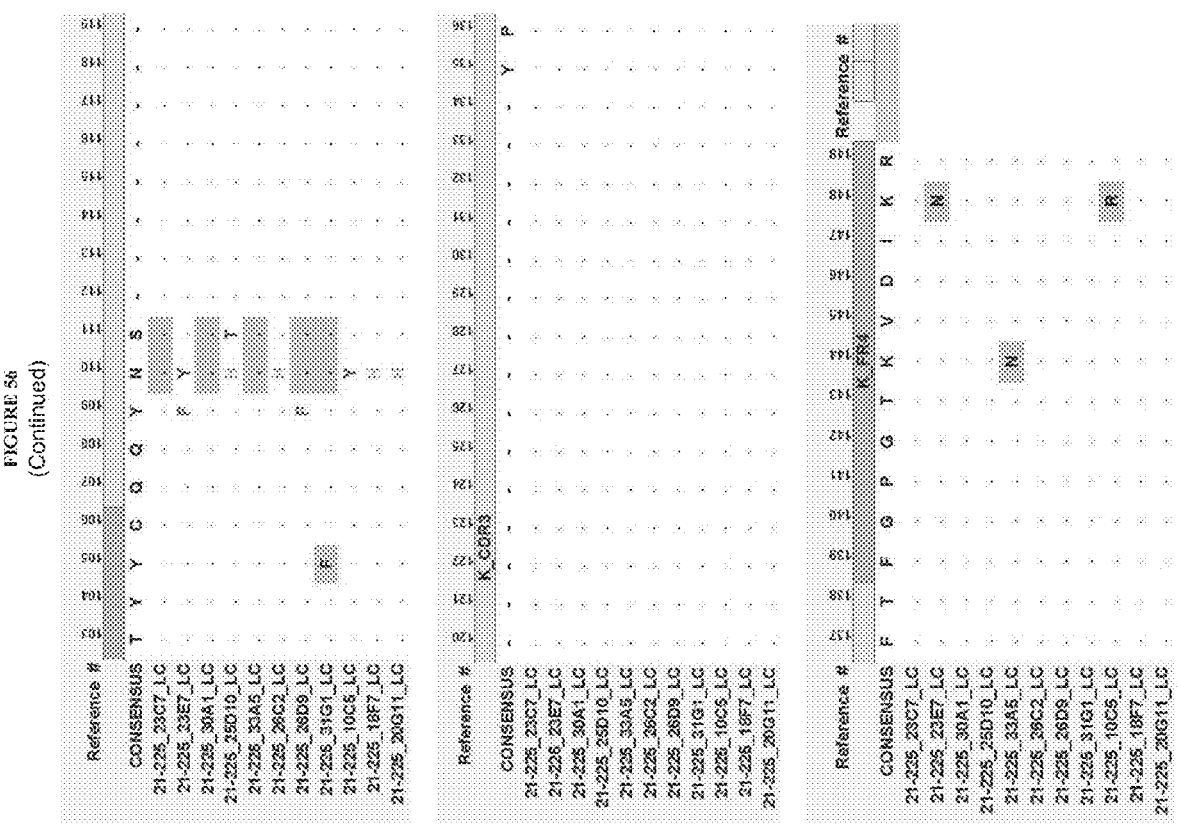
Figure 56:
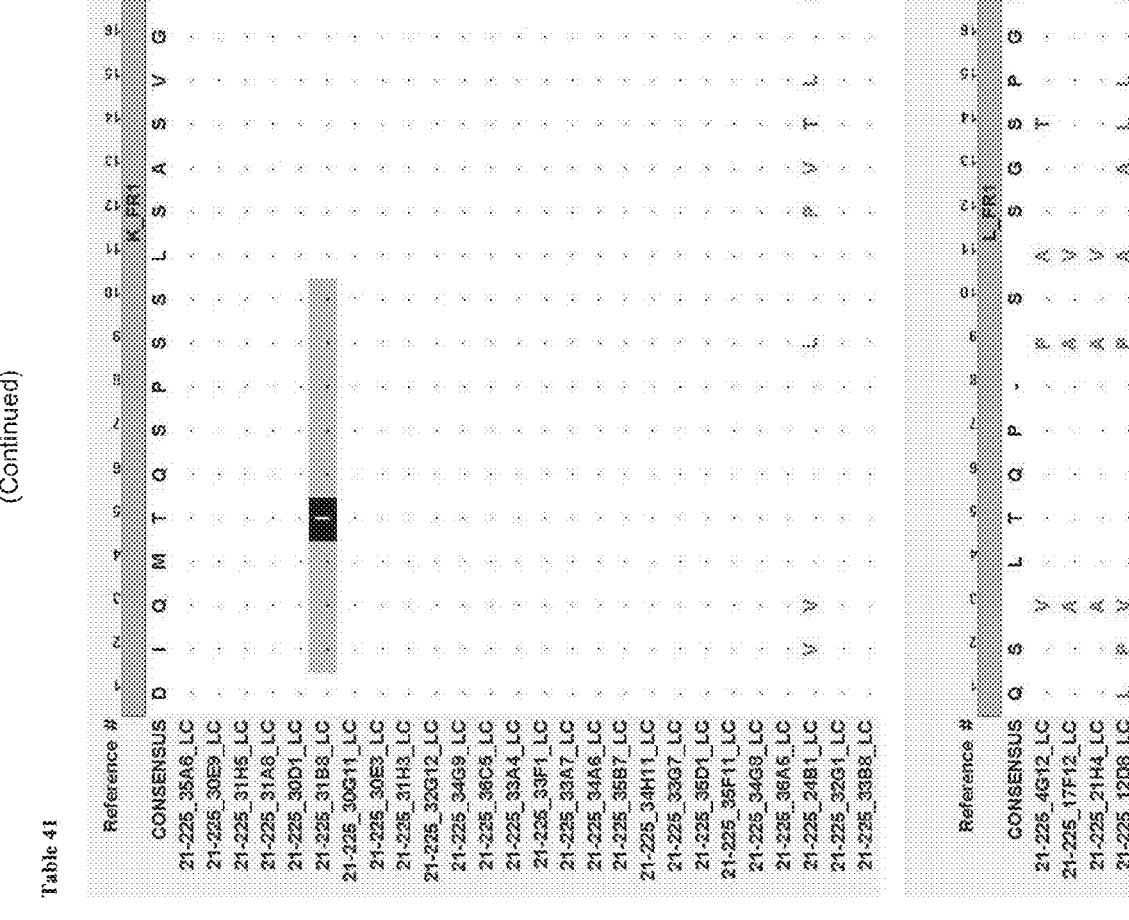
Figure 56:
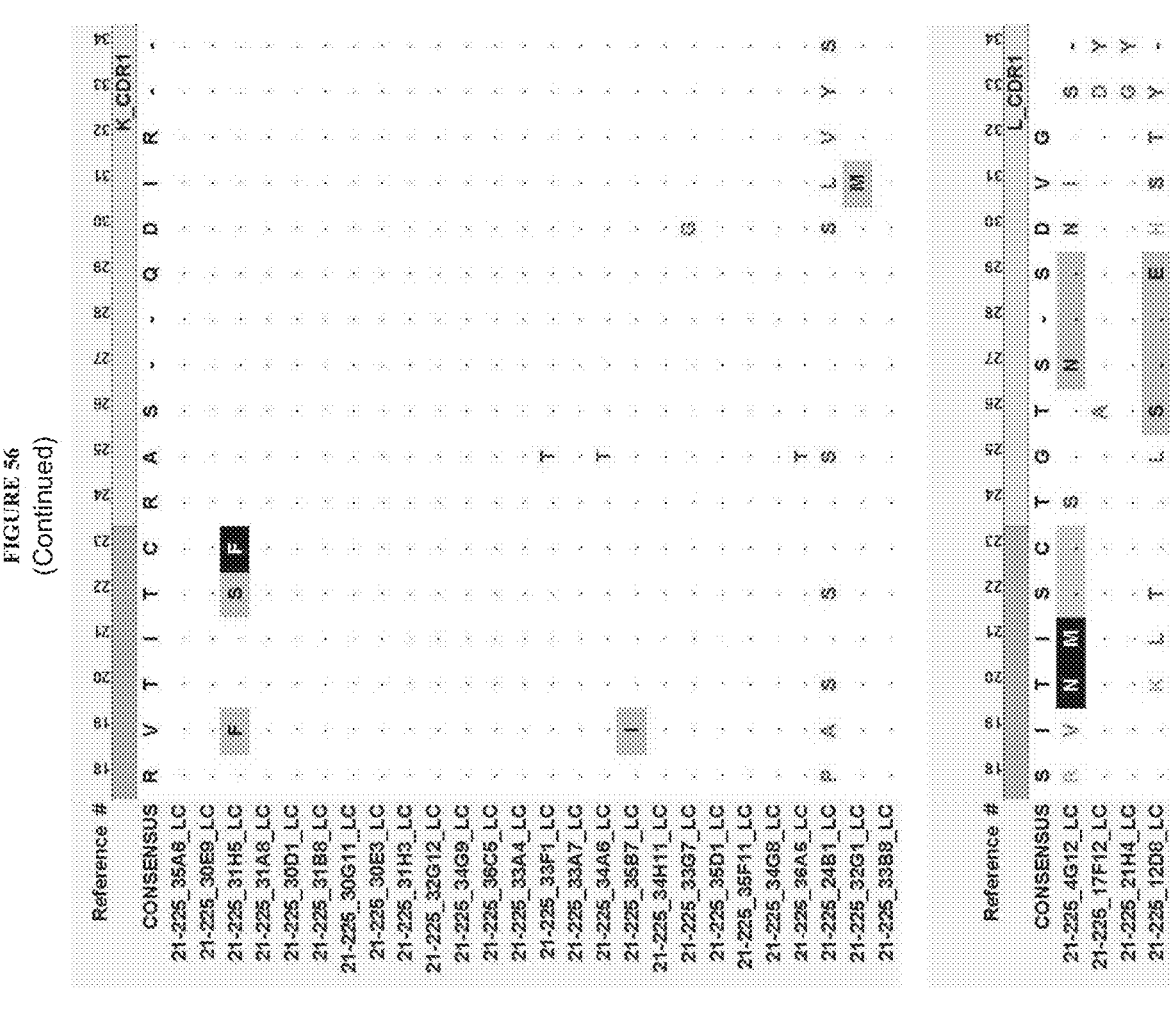
Figure 56:
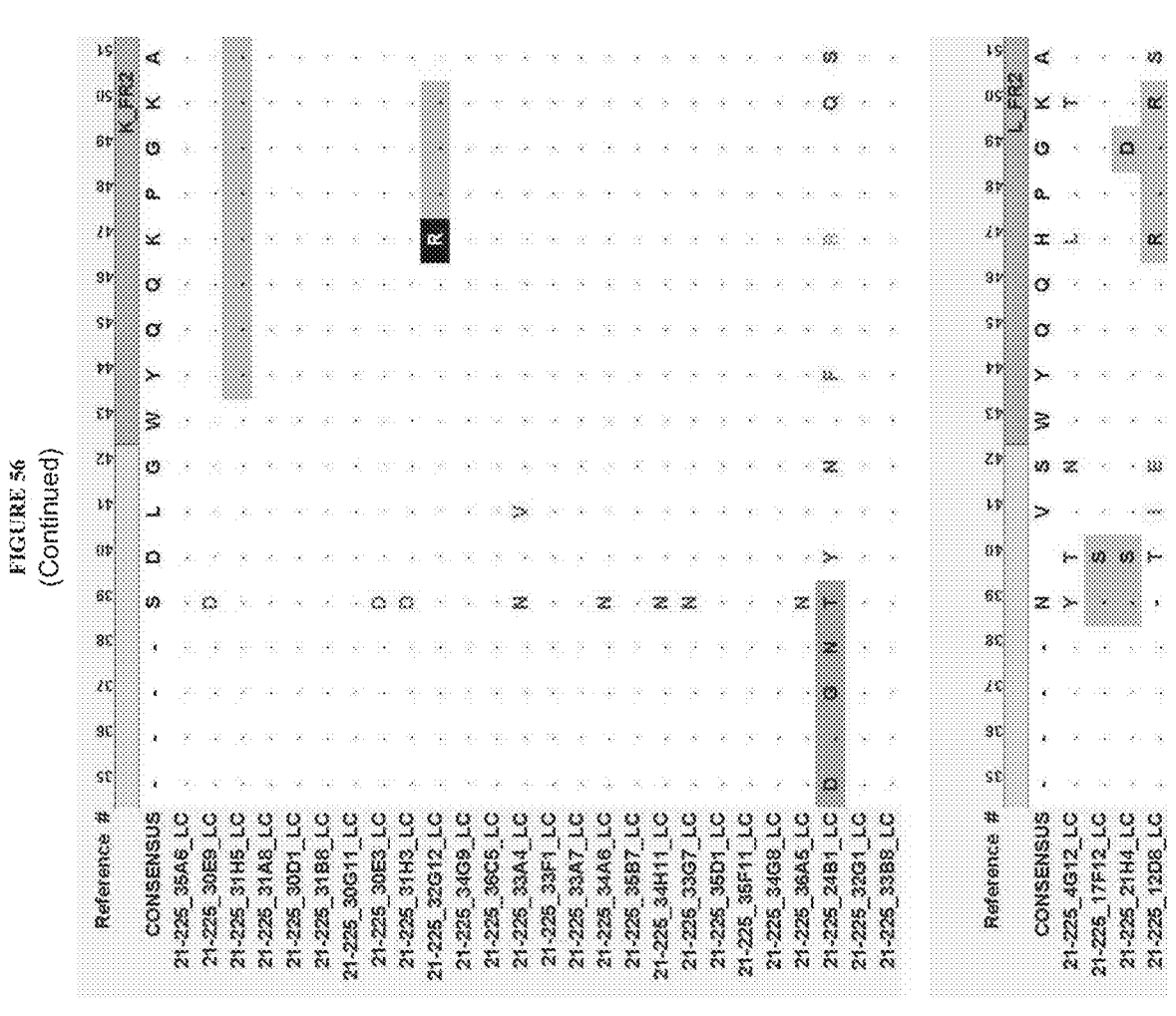
Figure 56:
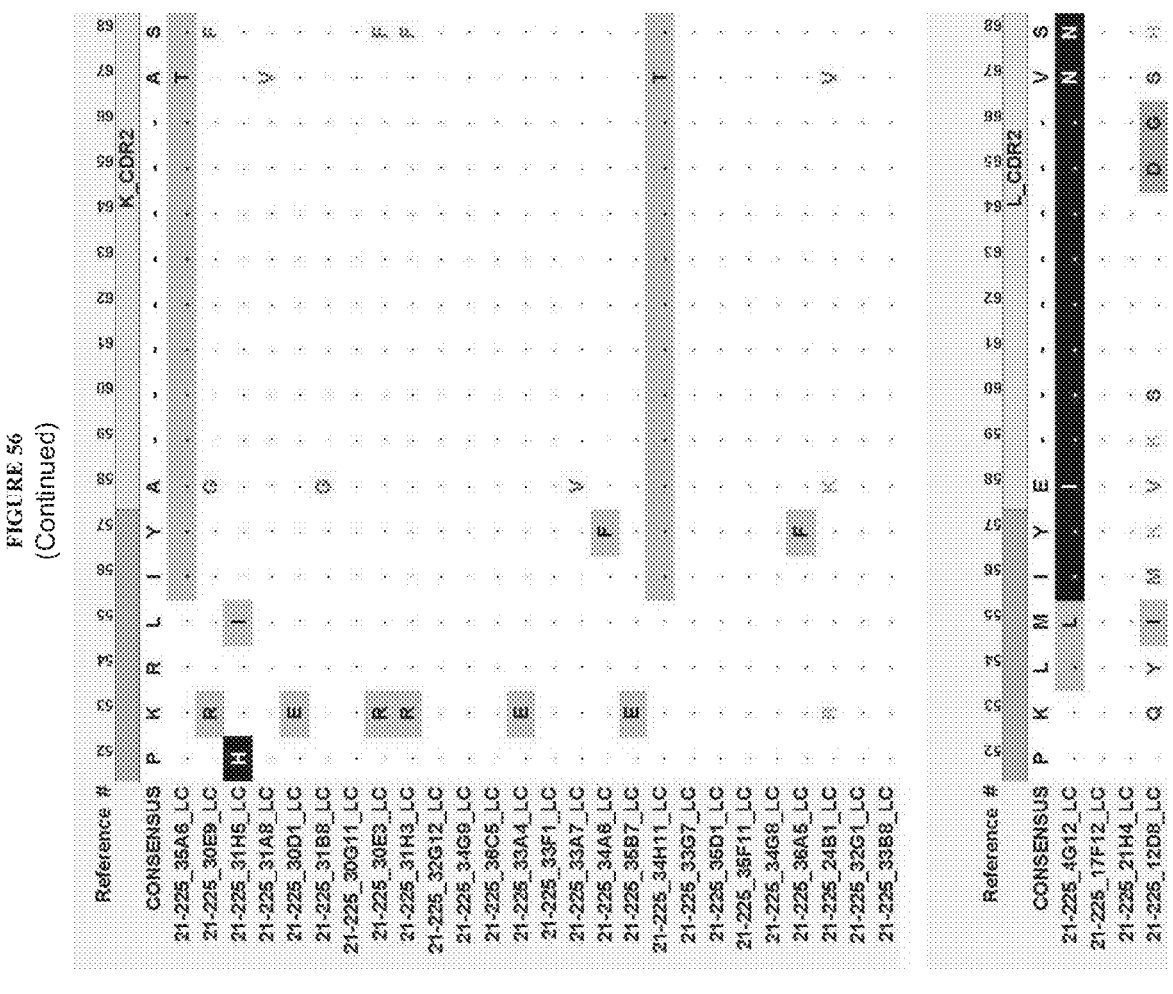
Figure 56:
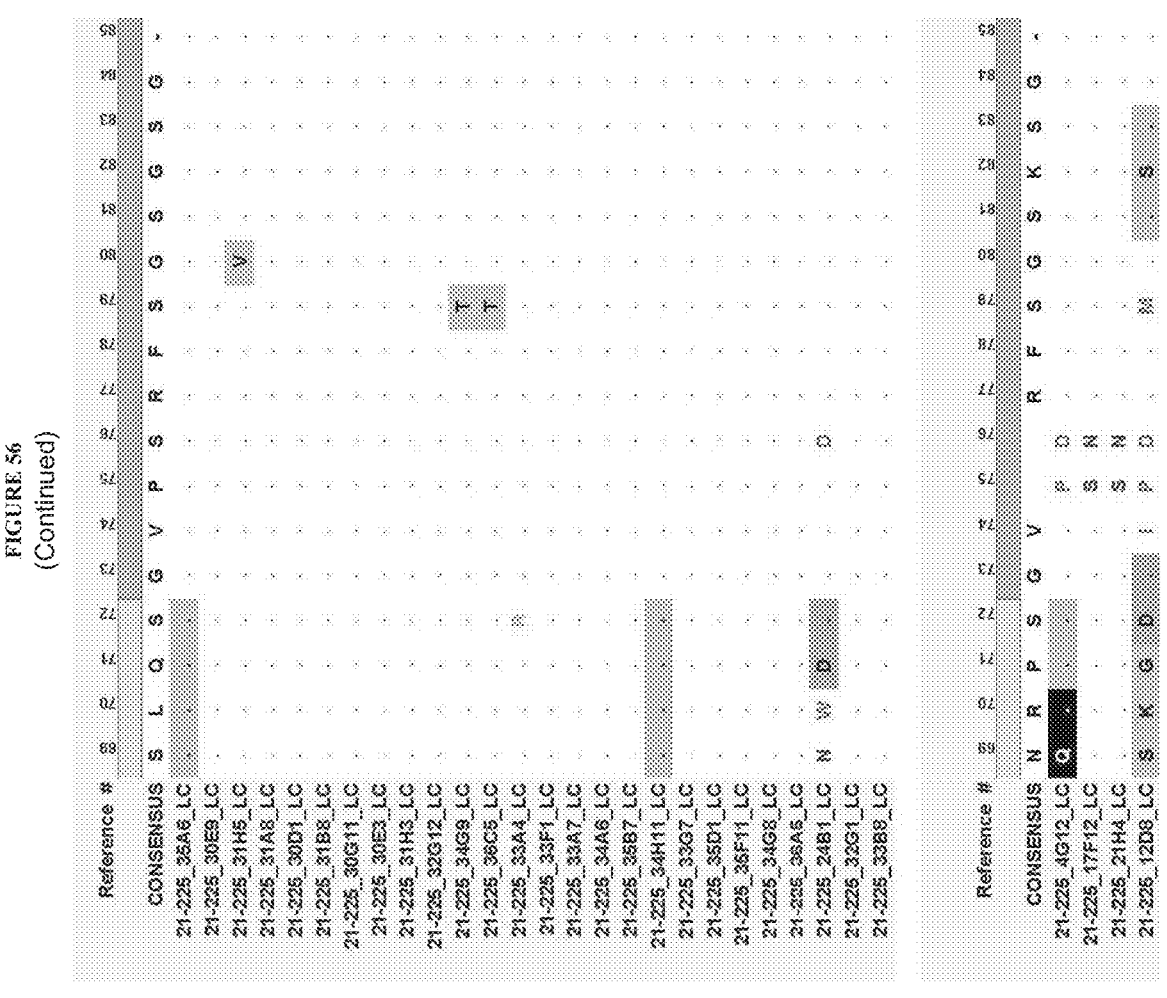
Figure 56:
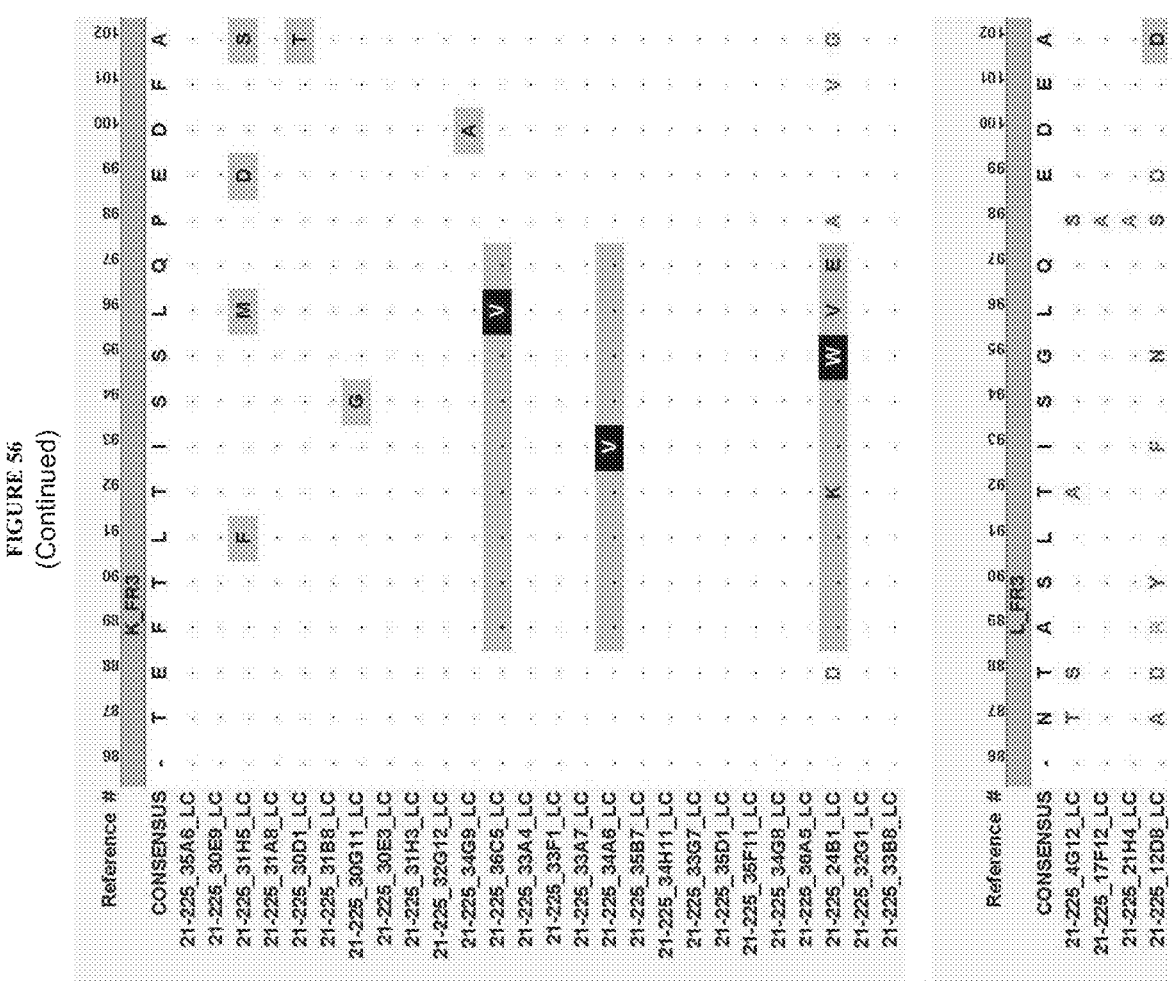
Figure 56:
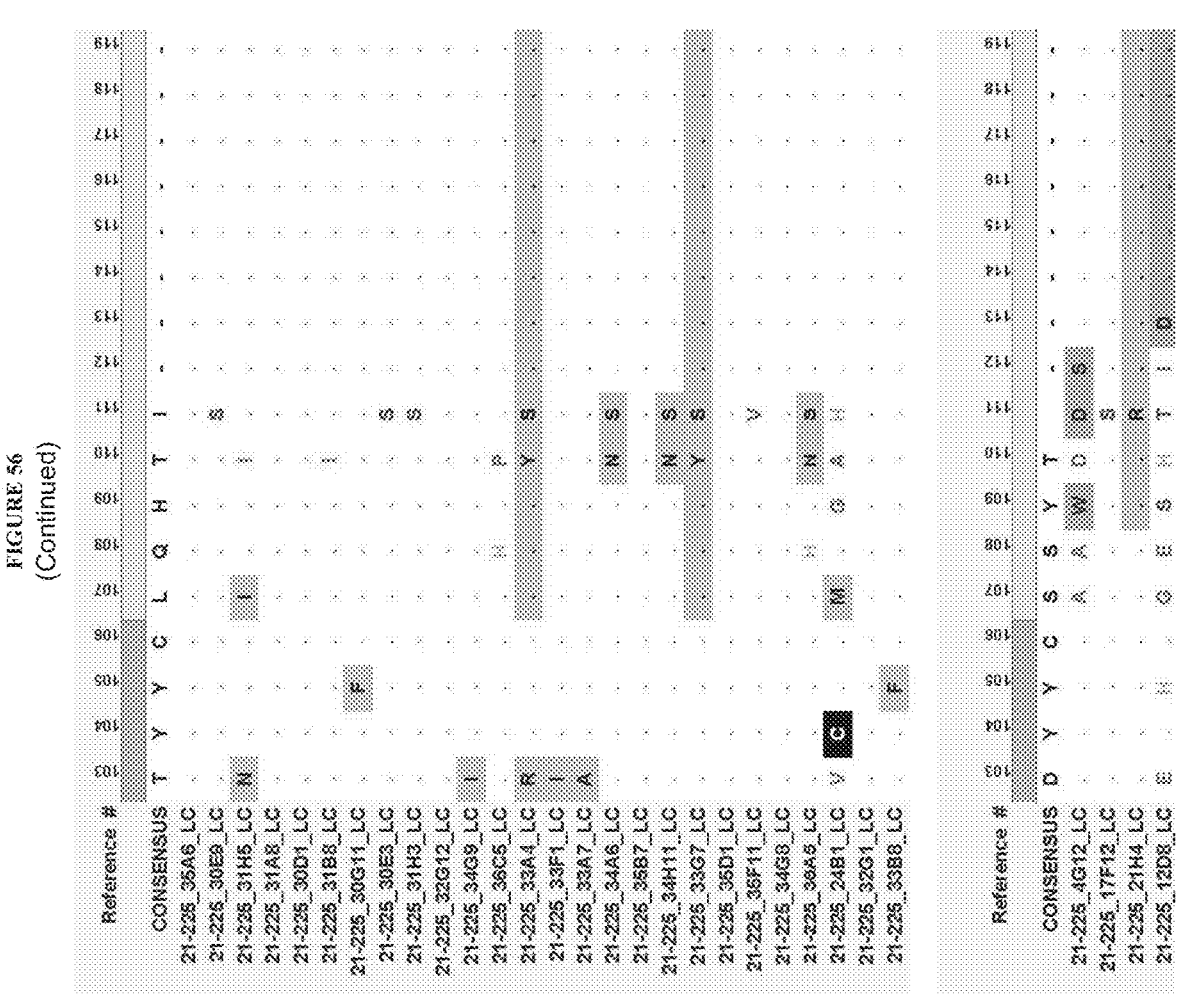
Figure 56:
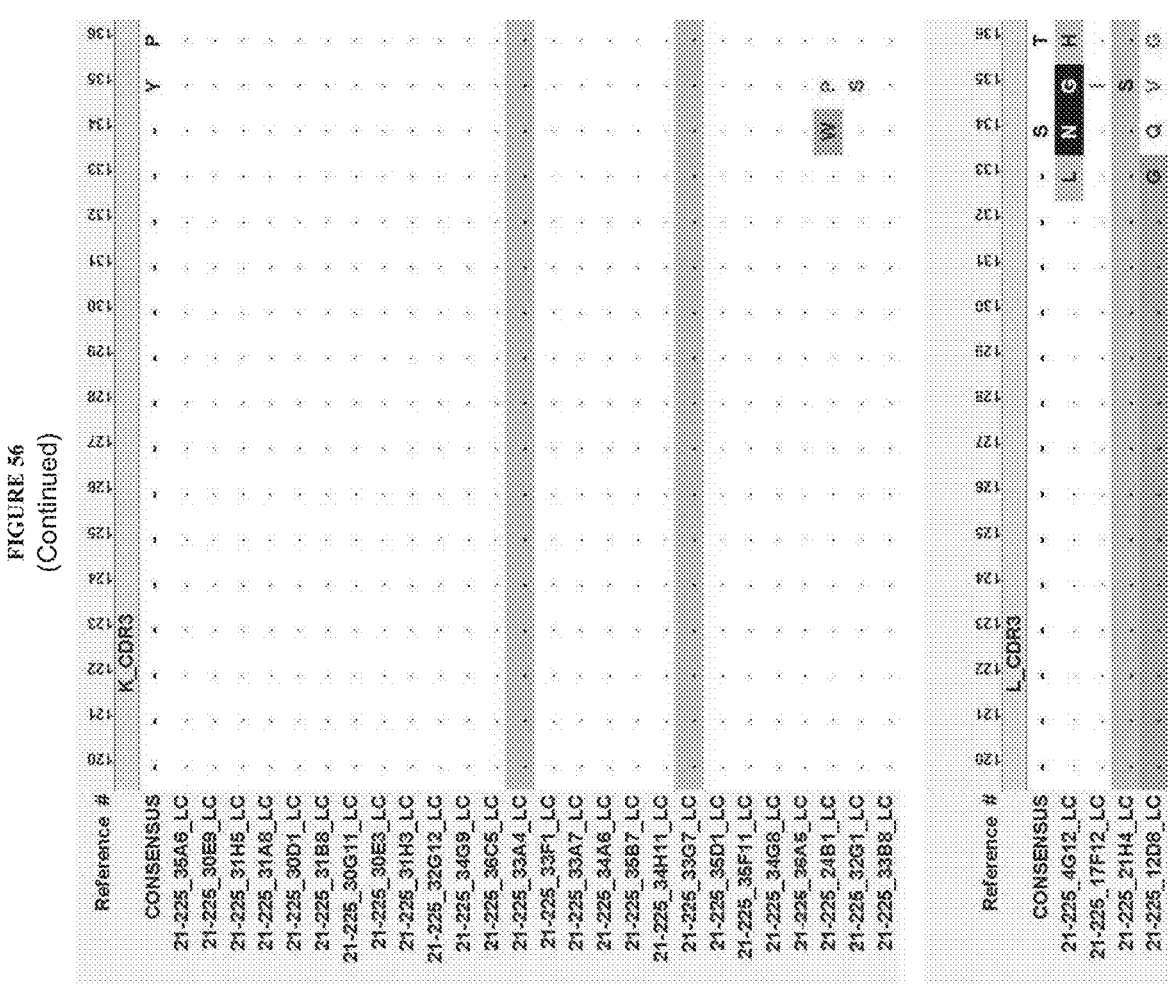
Figure 56:
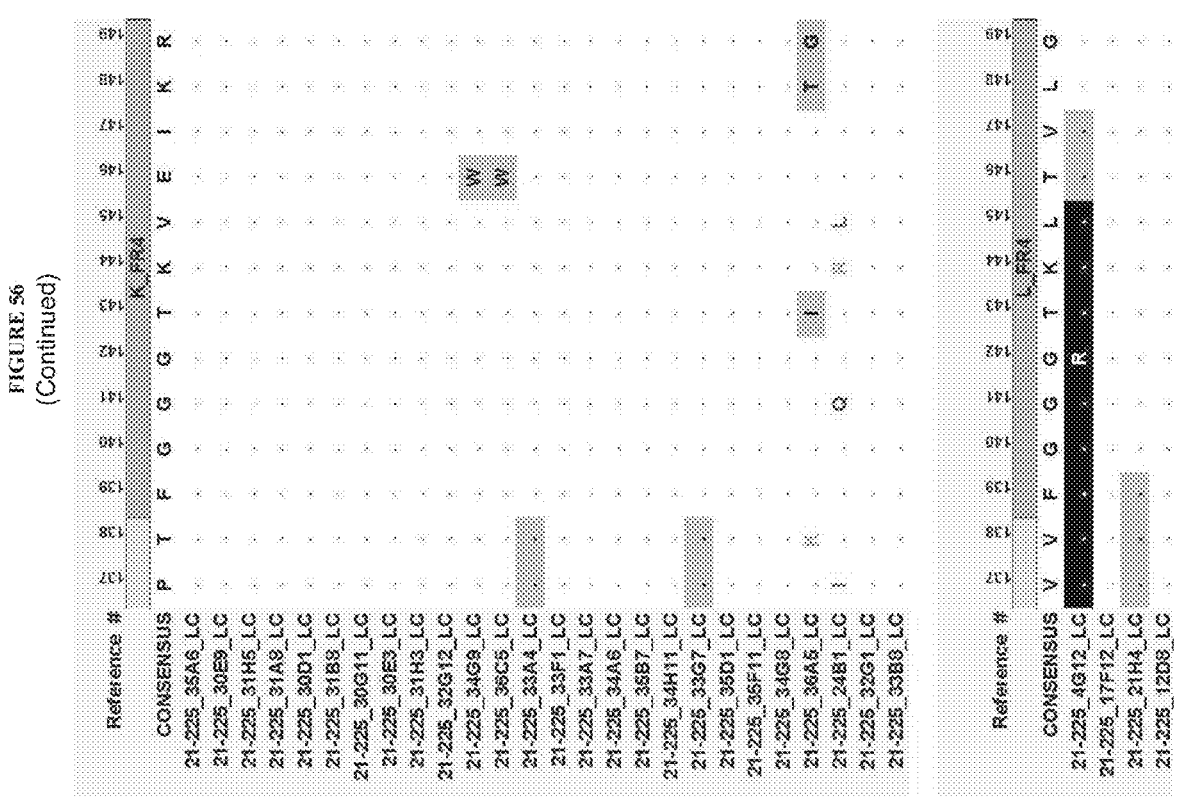
Figure 56:
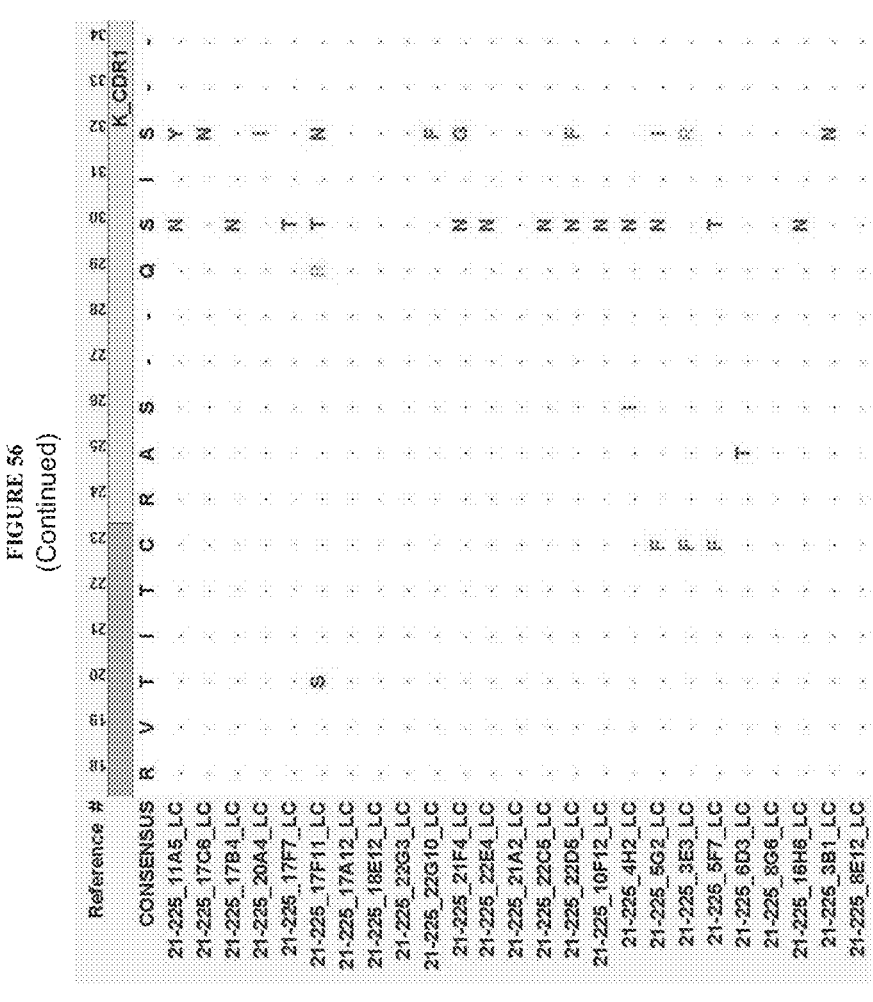
Figure 56:
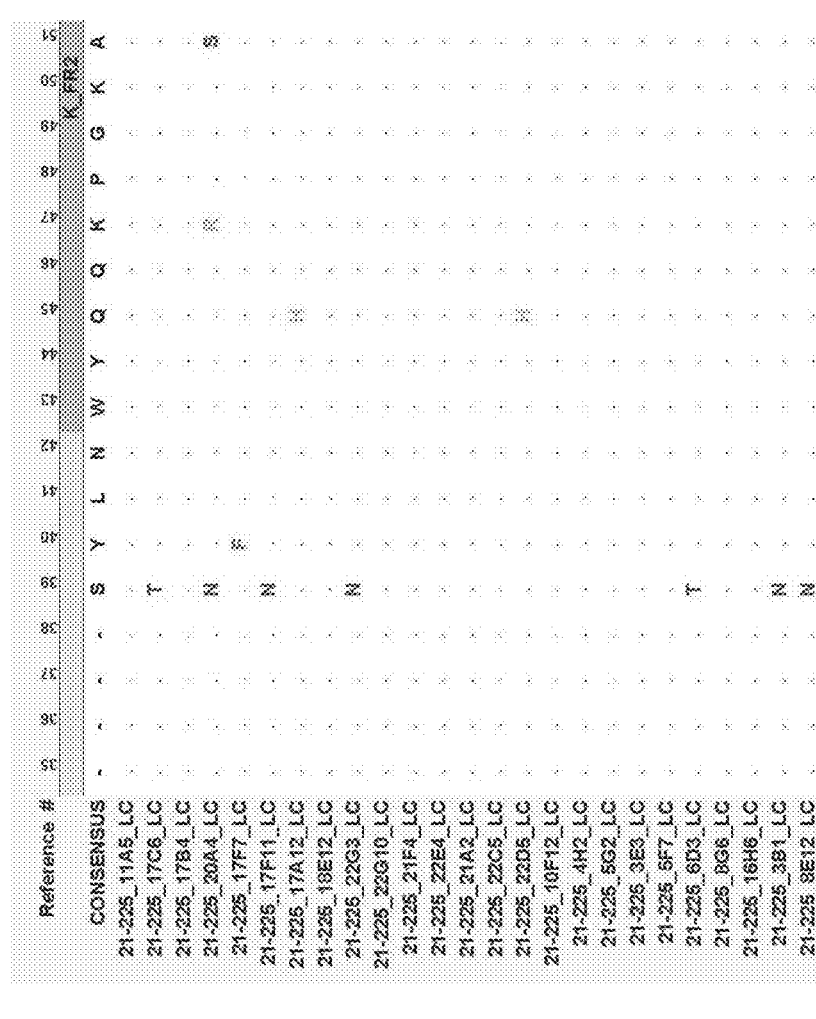
Figure 56:
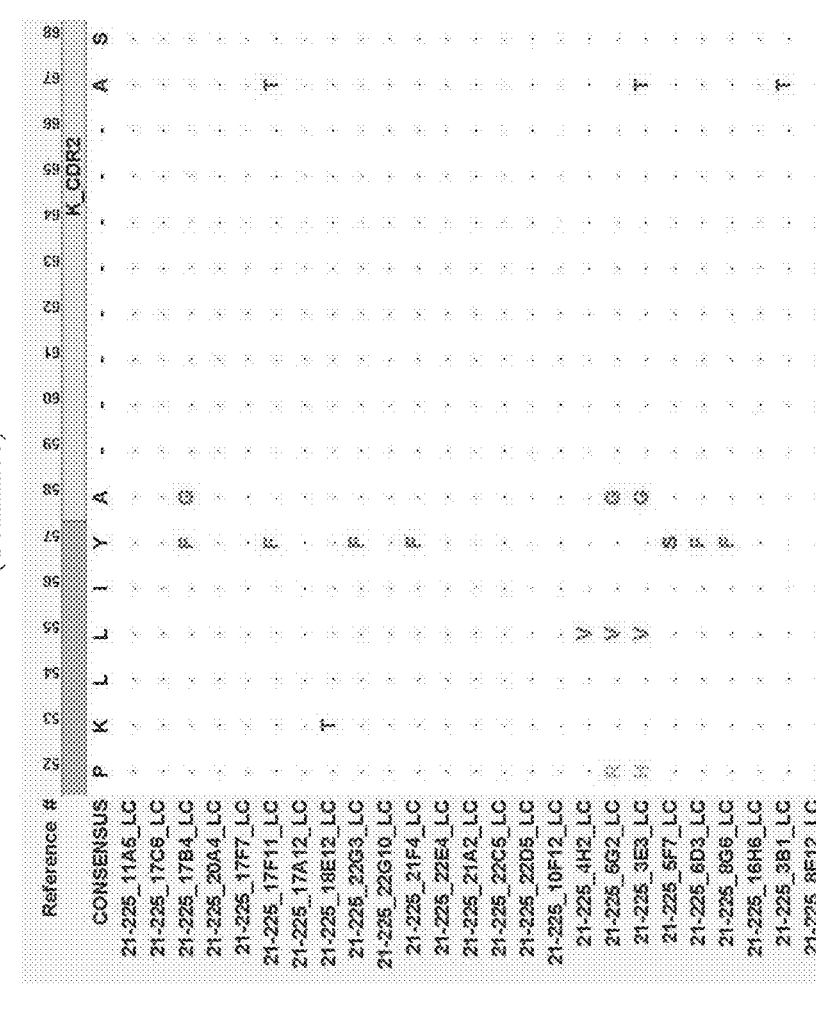
Figure 56:
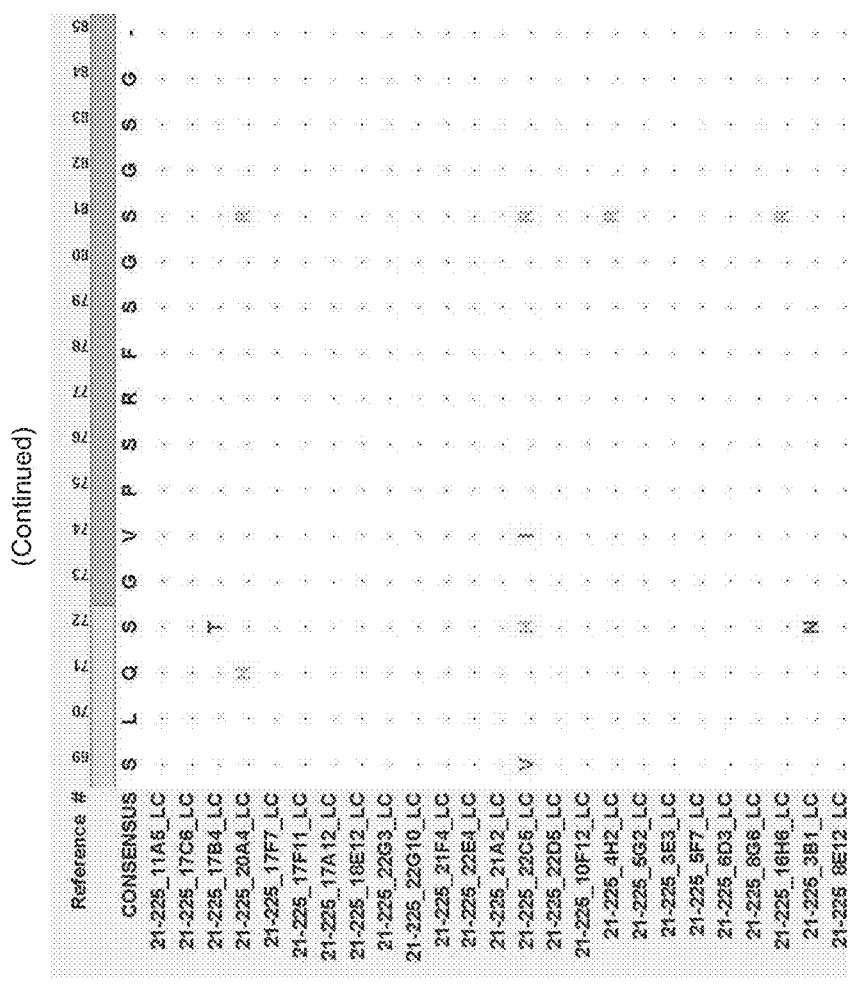
Figure 56:
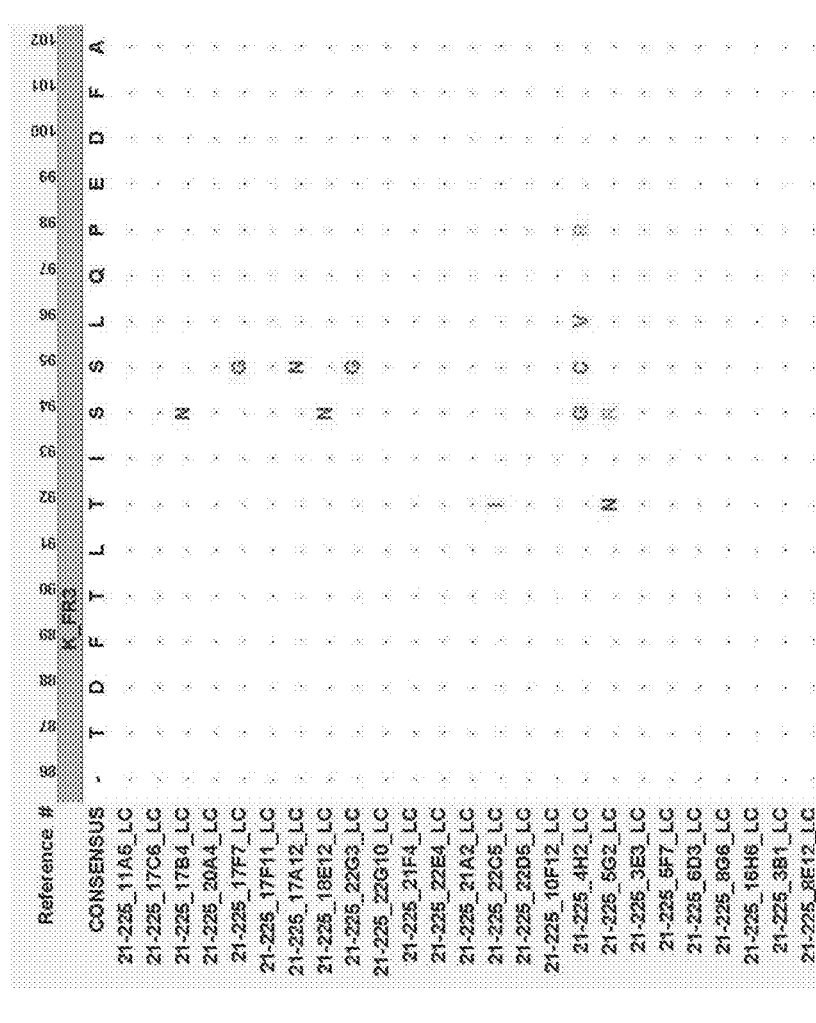
Figure 56:
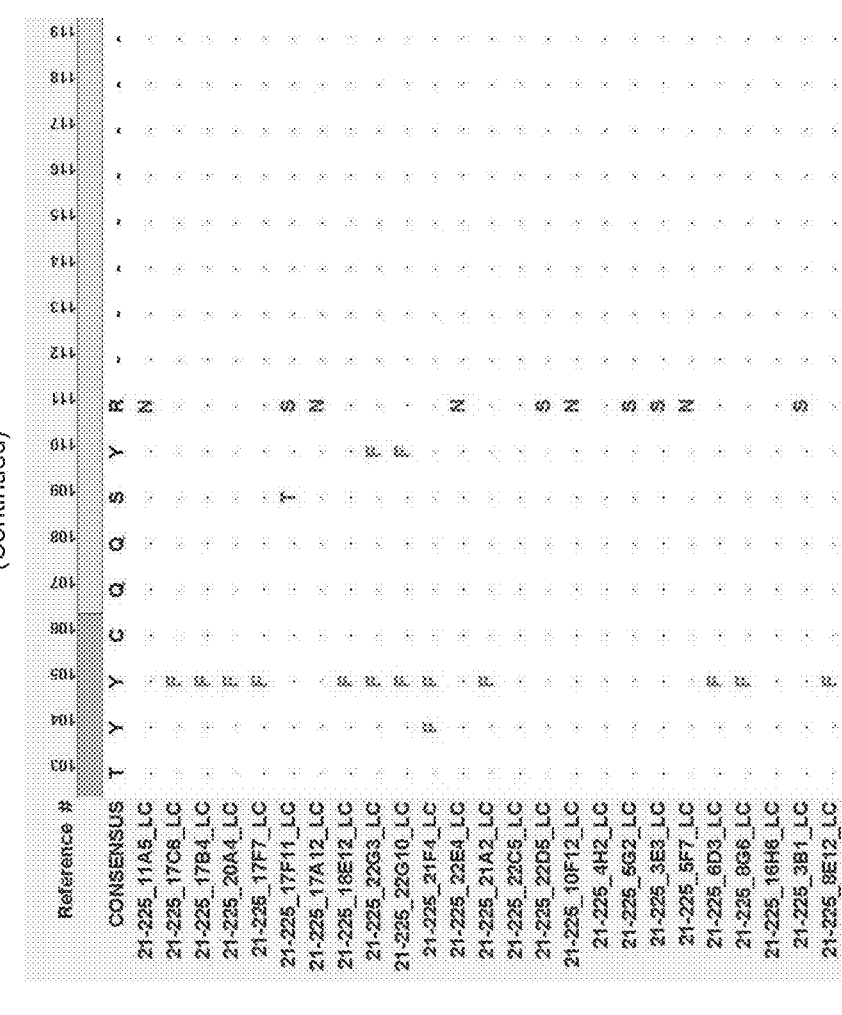
Figure 56:
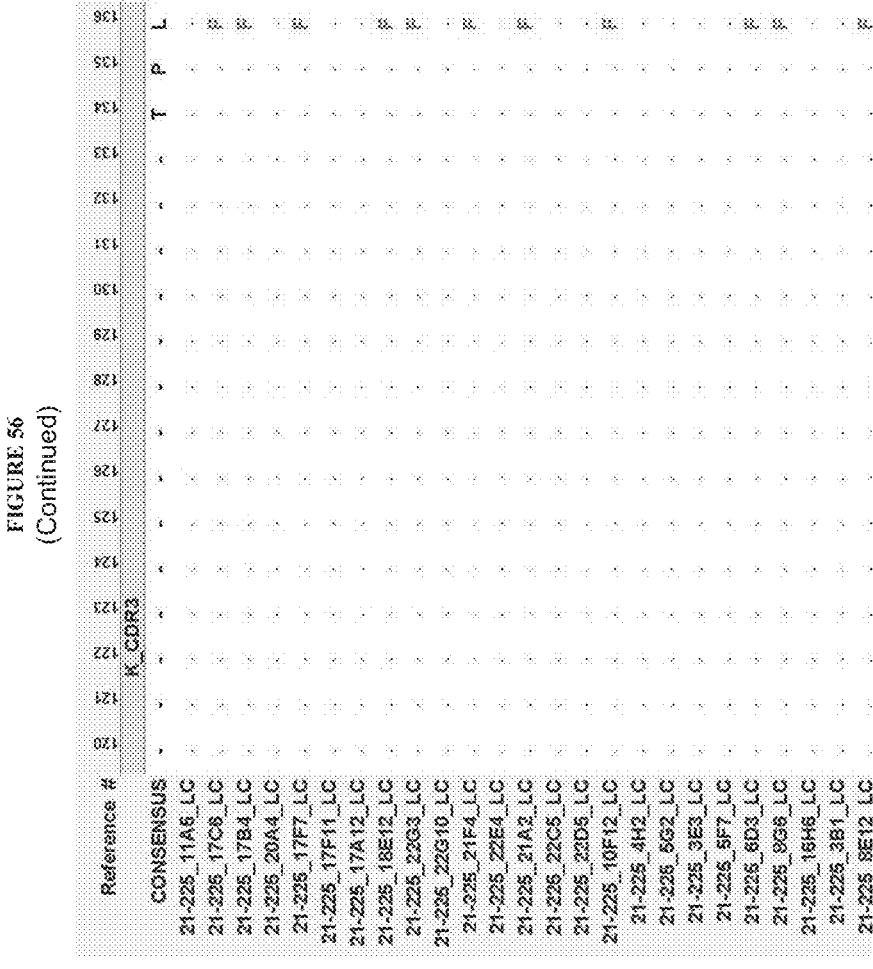
Figure 56:
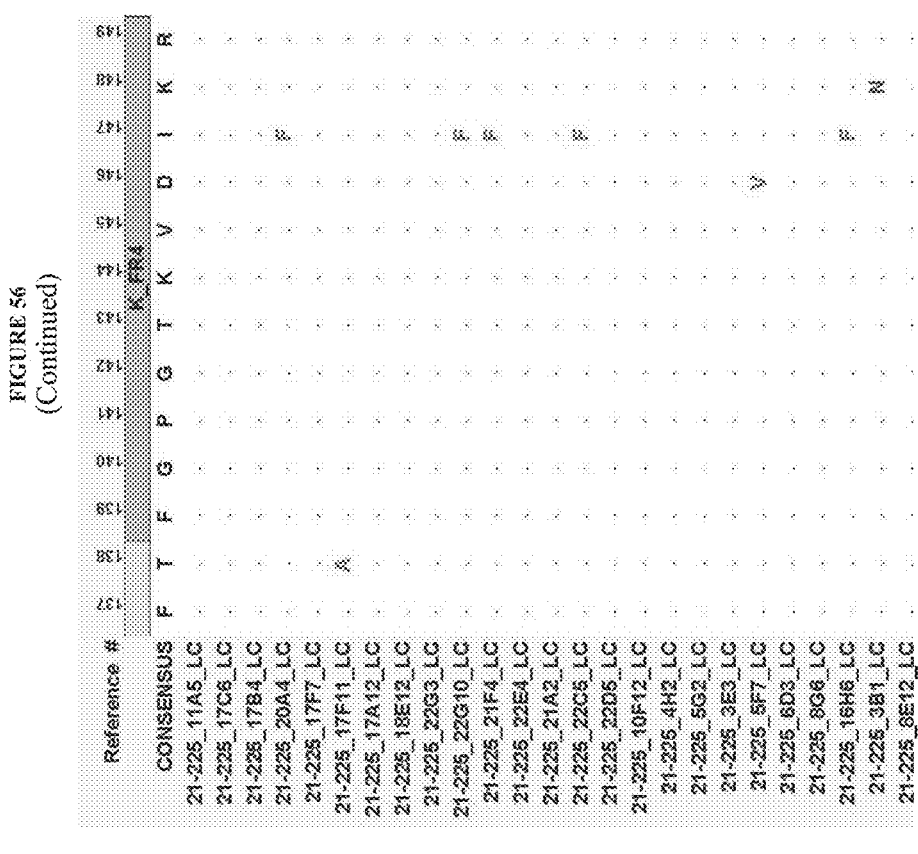
Figure 56:
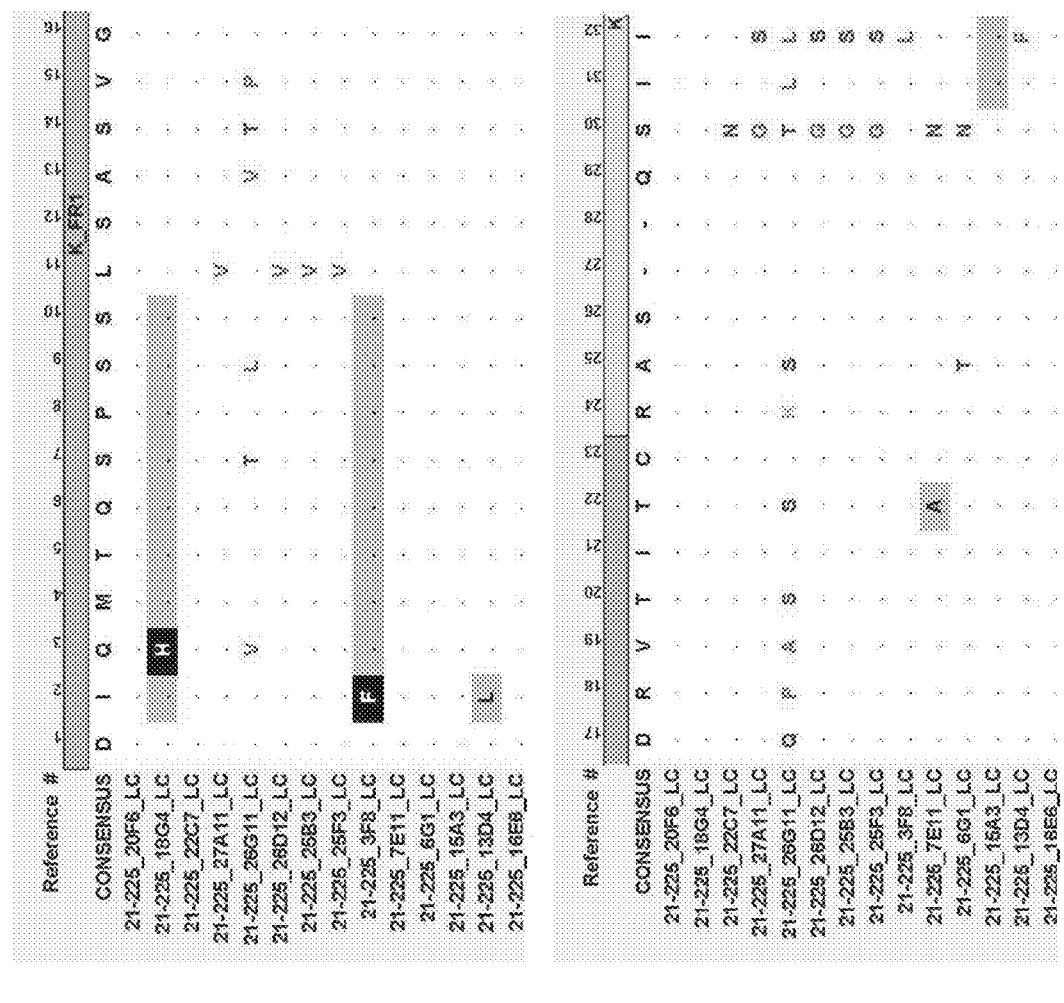
Figure 56:
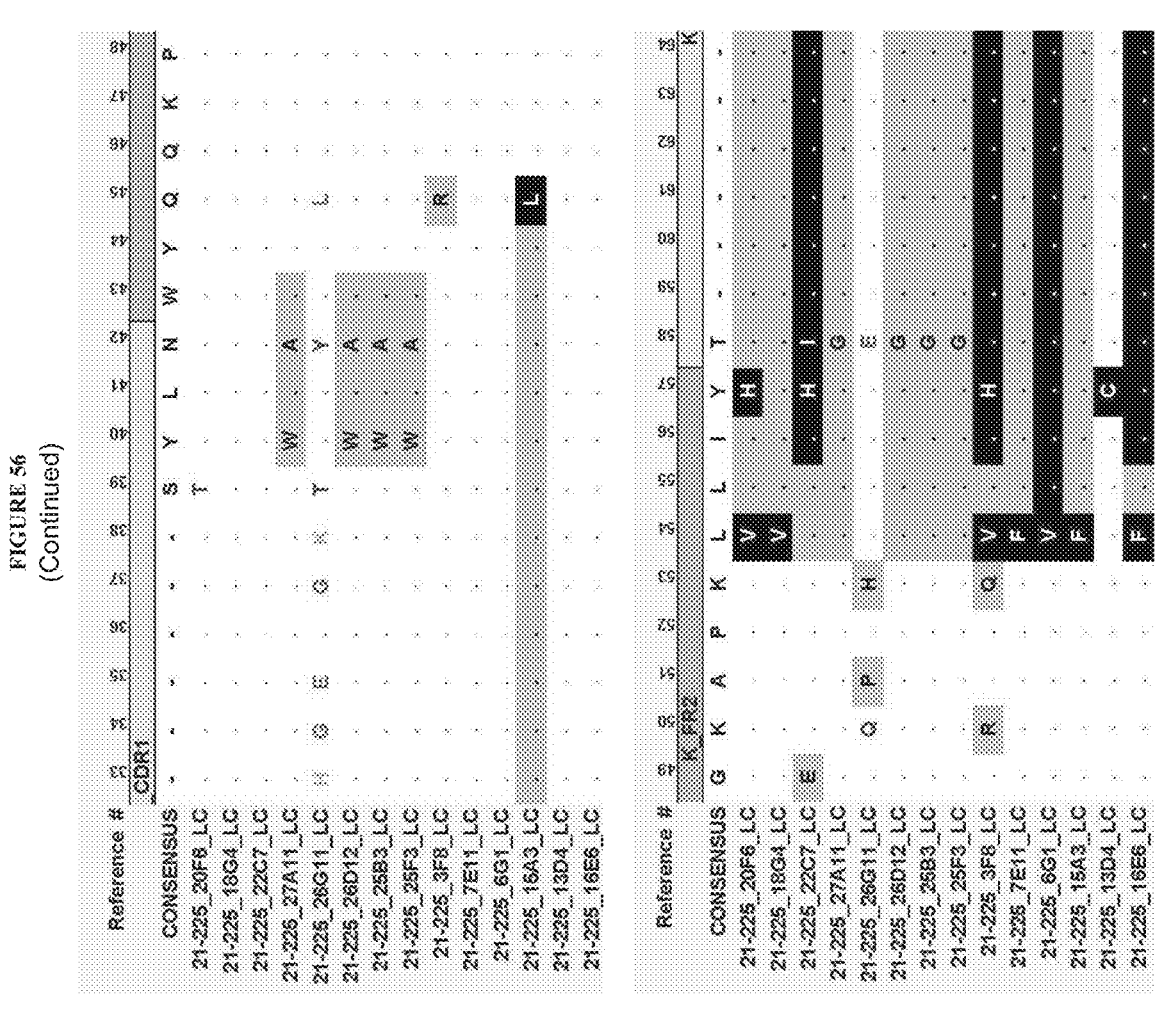
Figure 56:
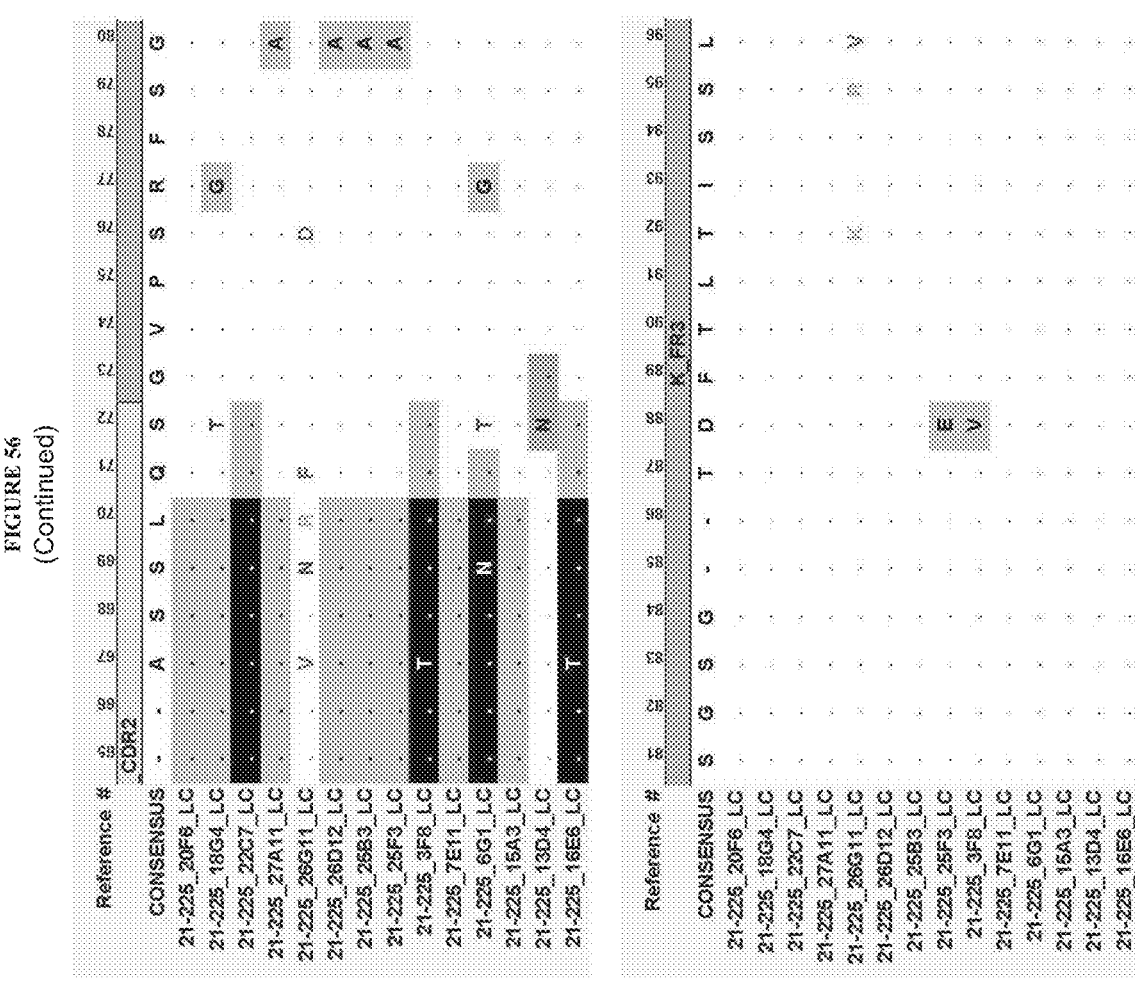
Figure 56:
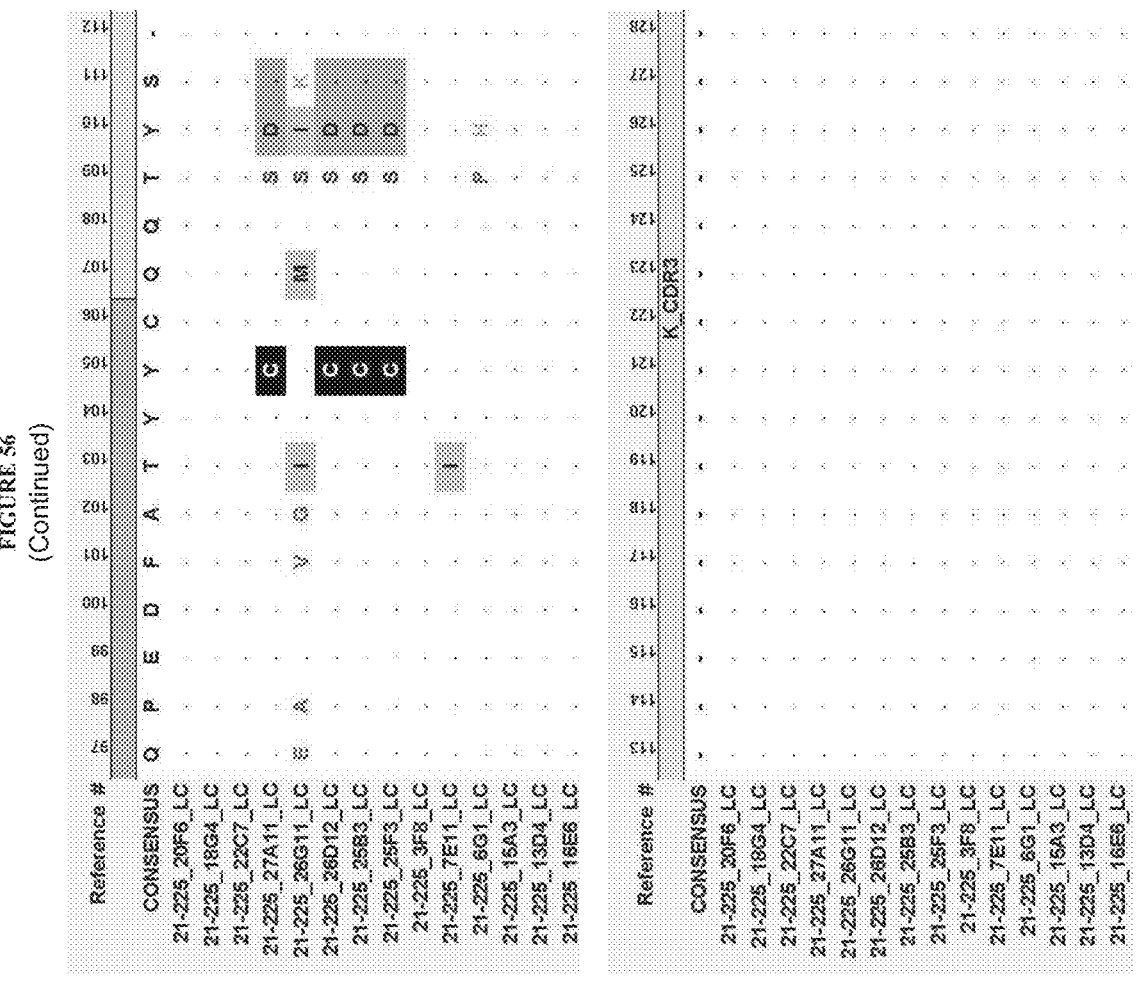
Figure 56:
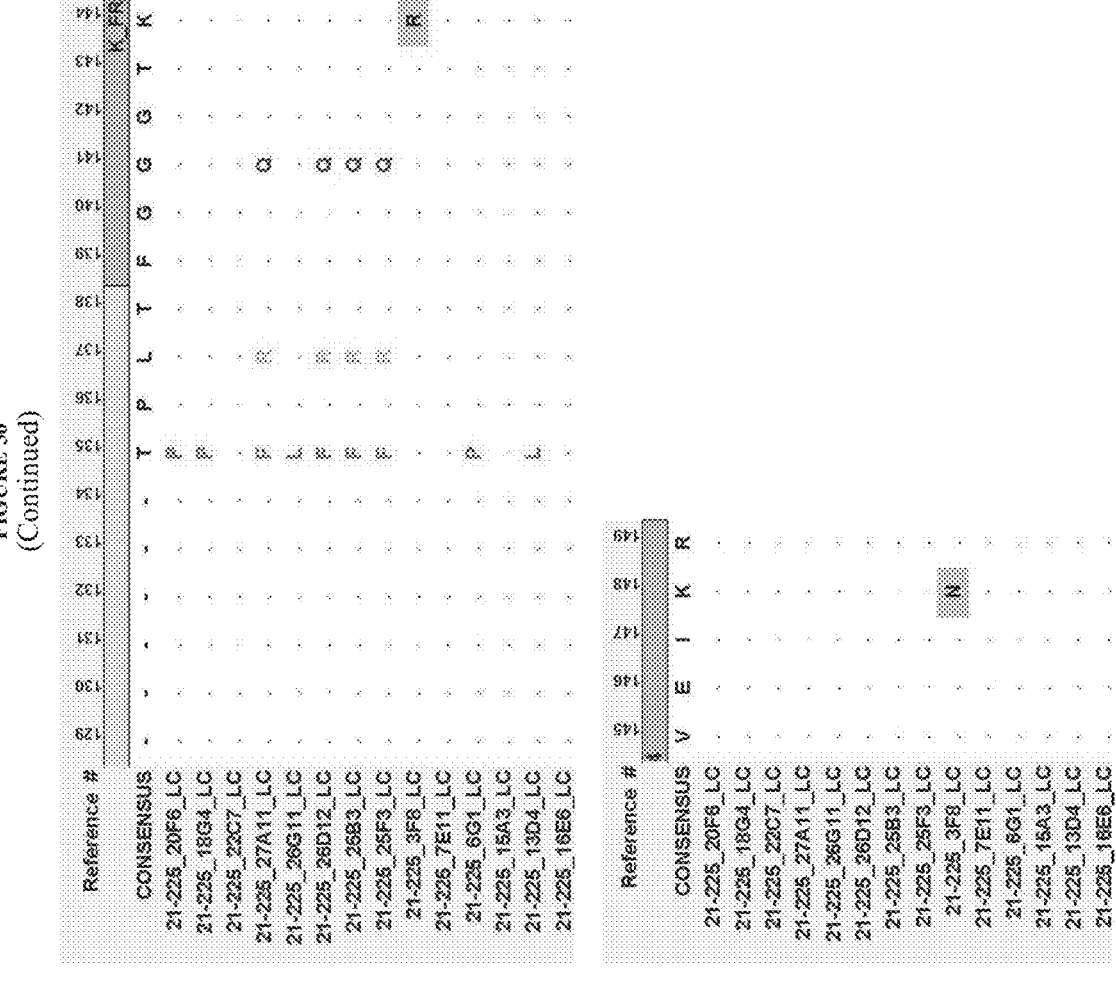
Figure 56:
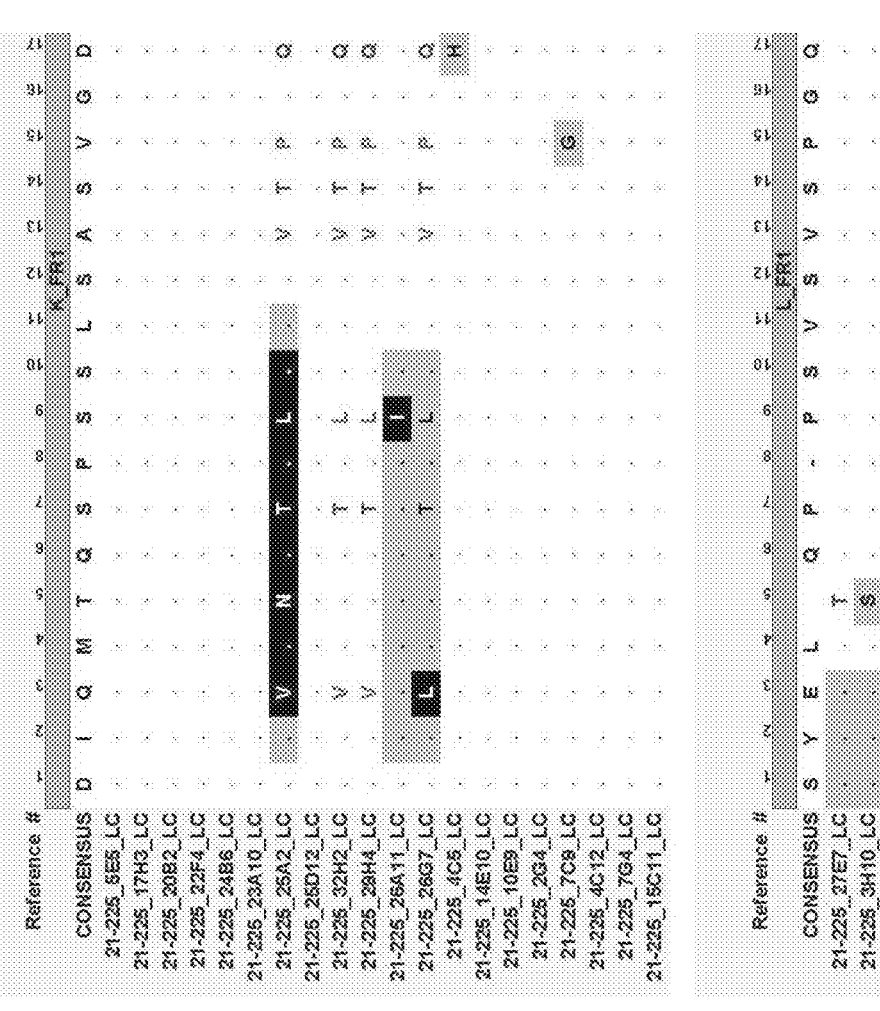
Figure 56:
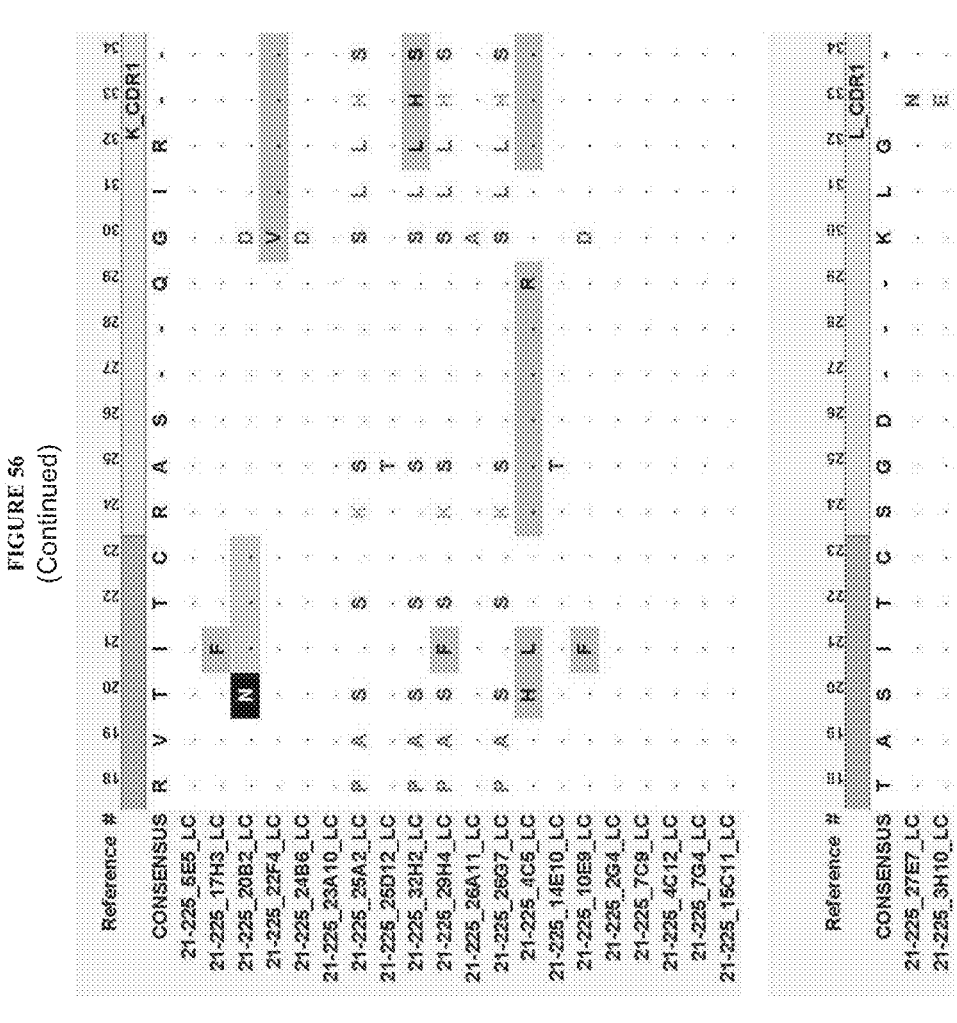
Figure 56:
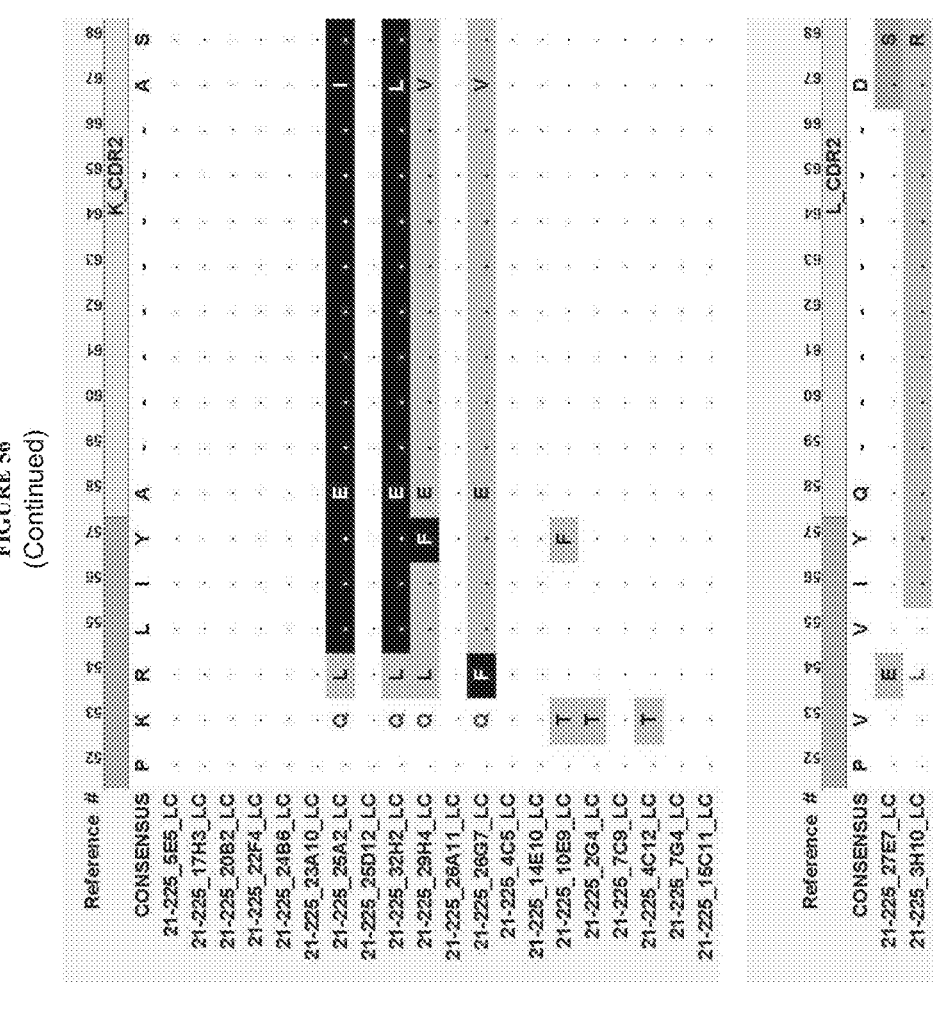
Figure 56:
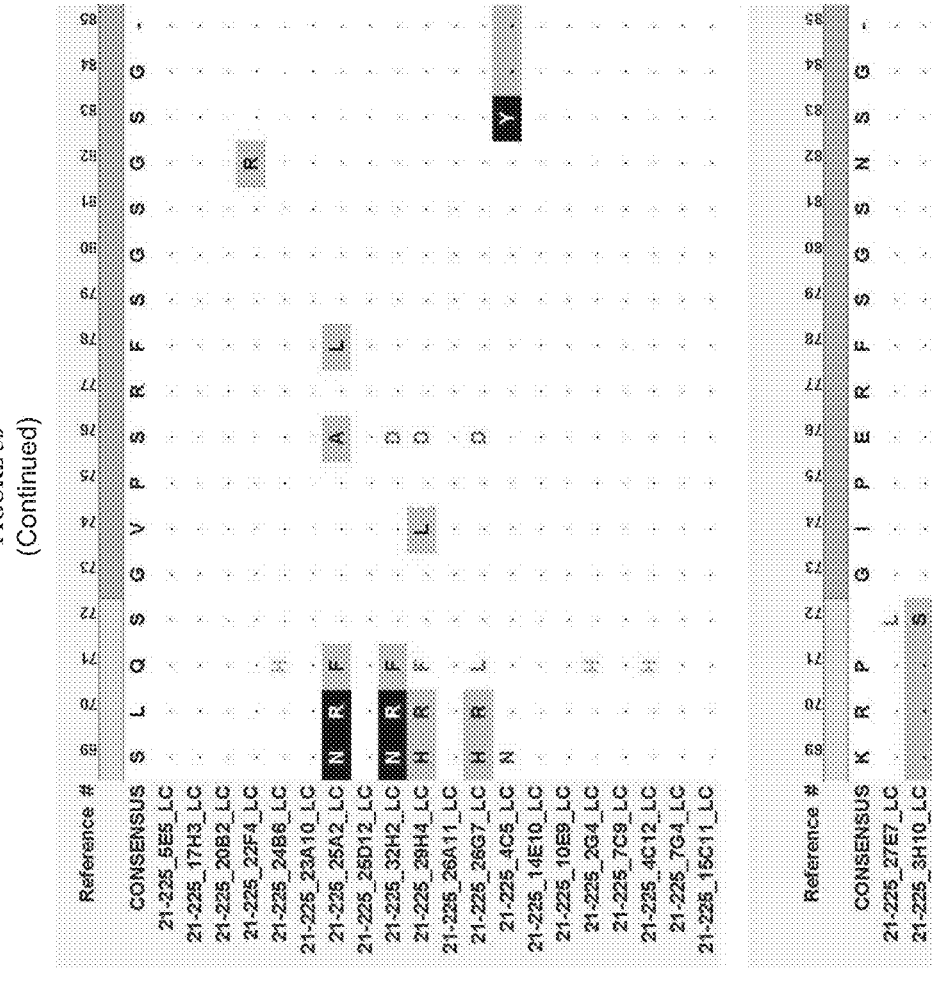
Figure 56:
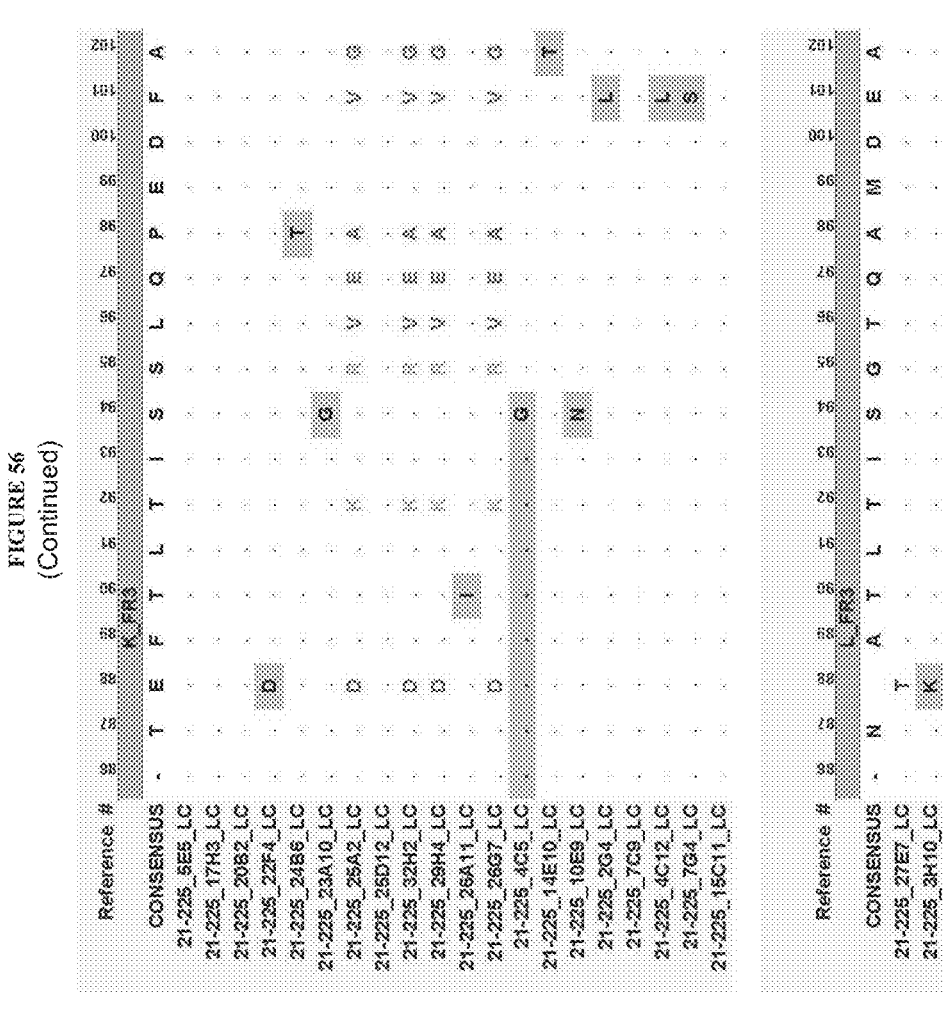
Figure 56:
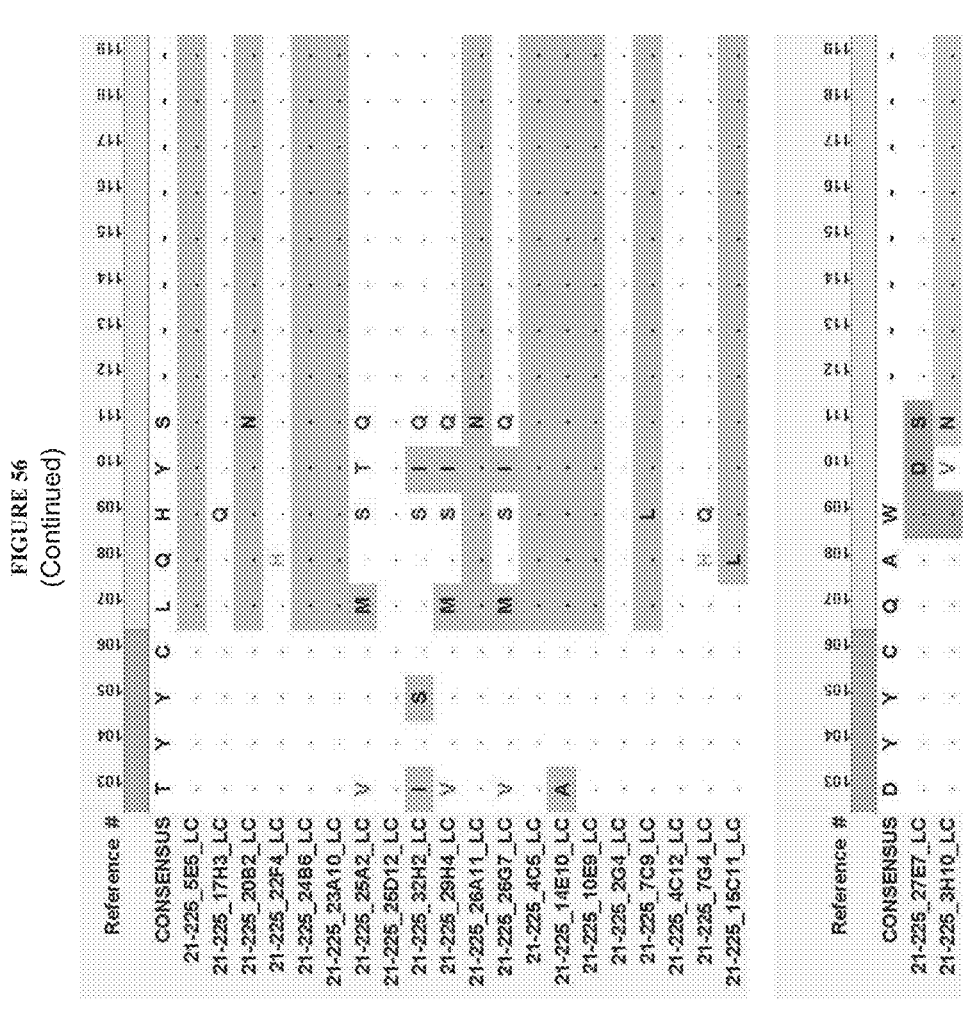
Figure 56:
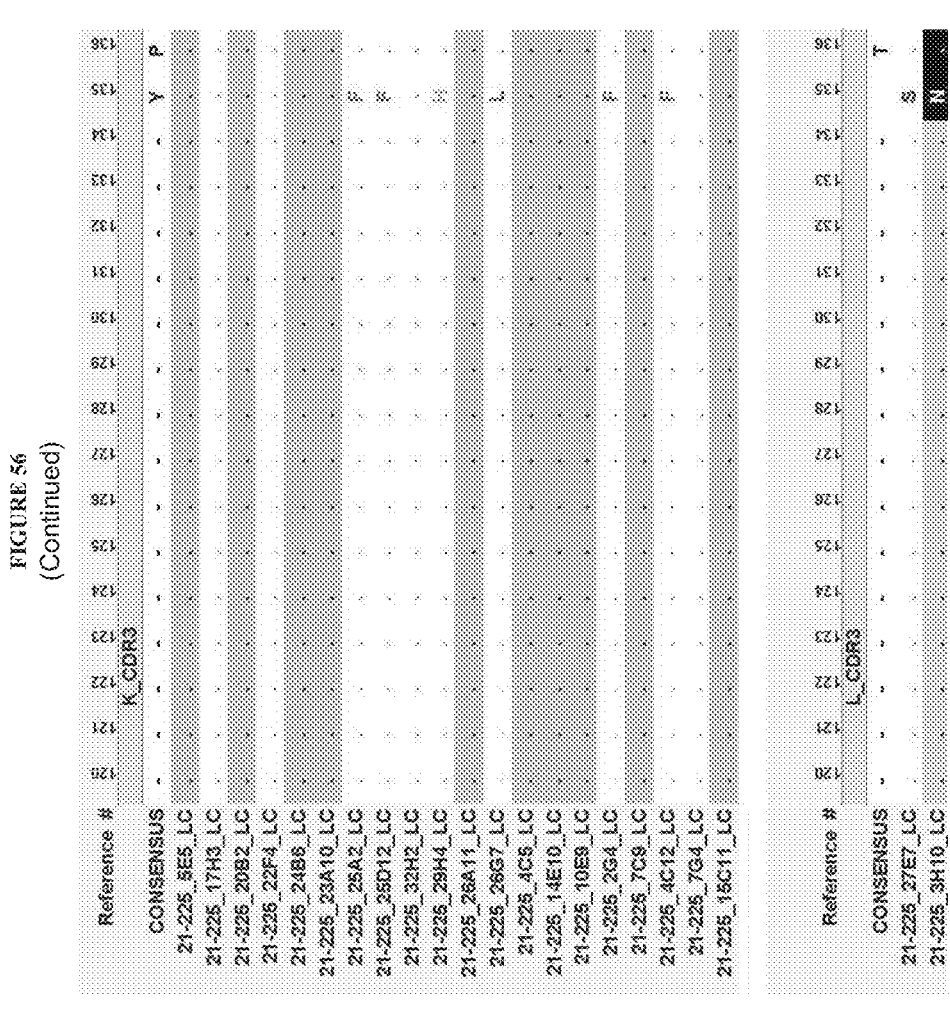
Figure 56:
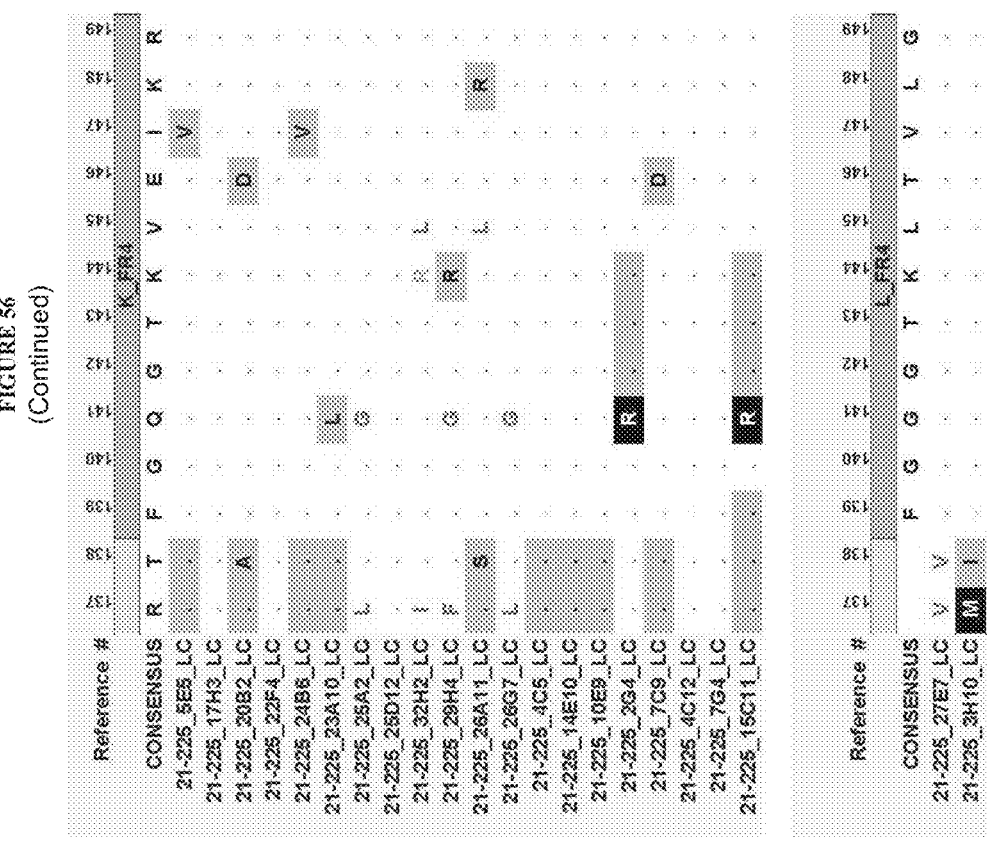
Figure 56:
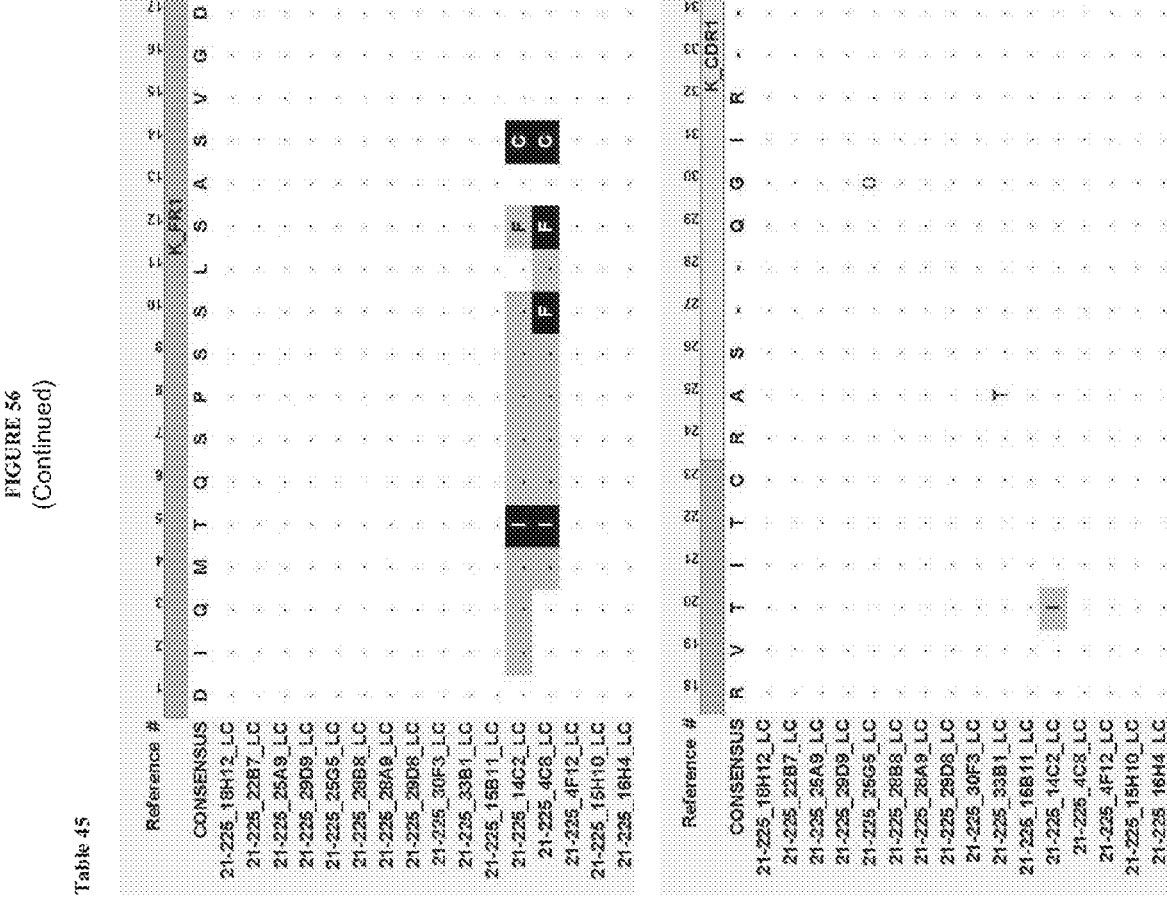
Figure 56:
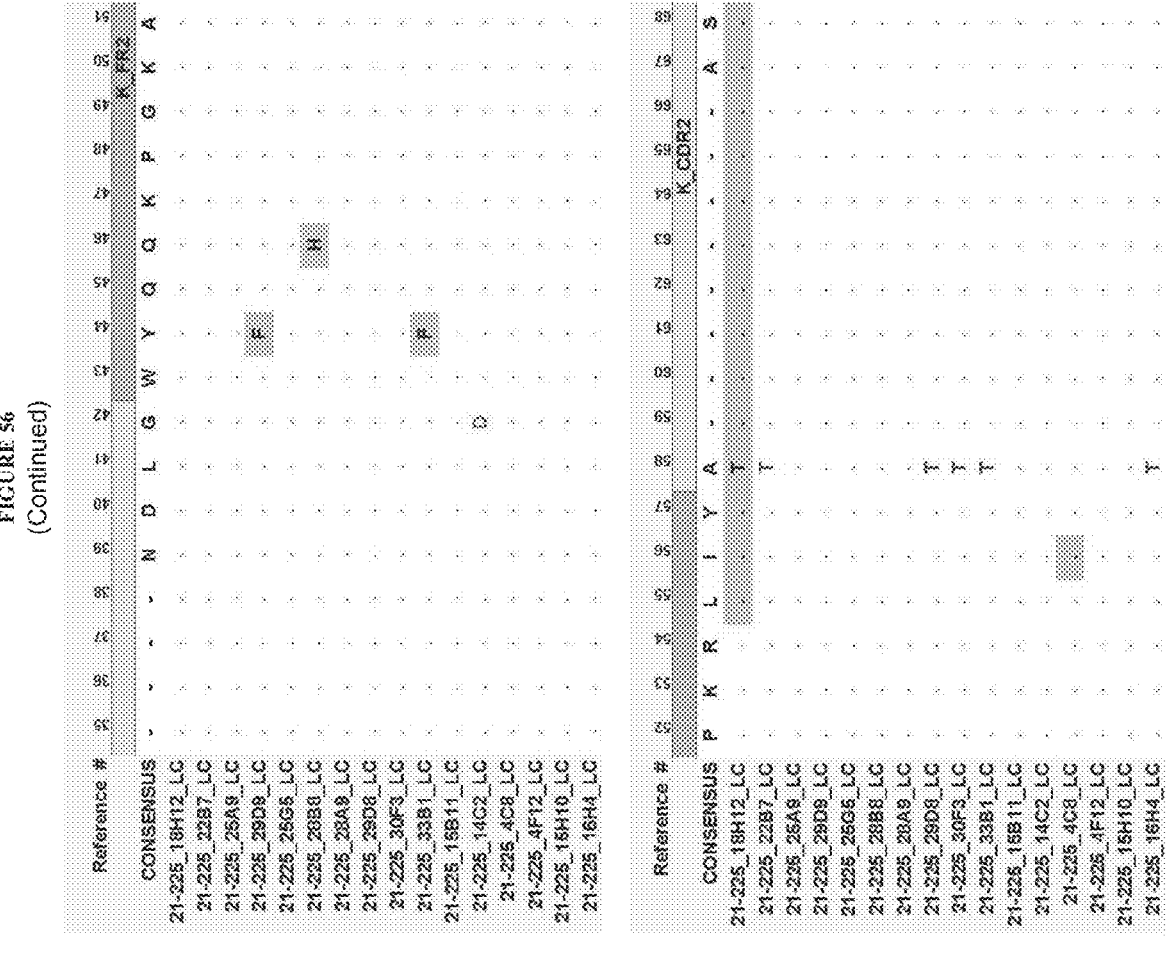
Figure 56:
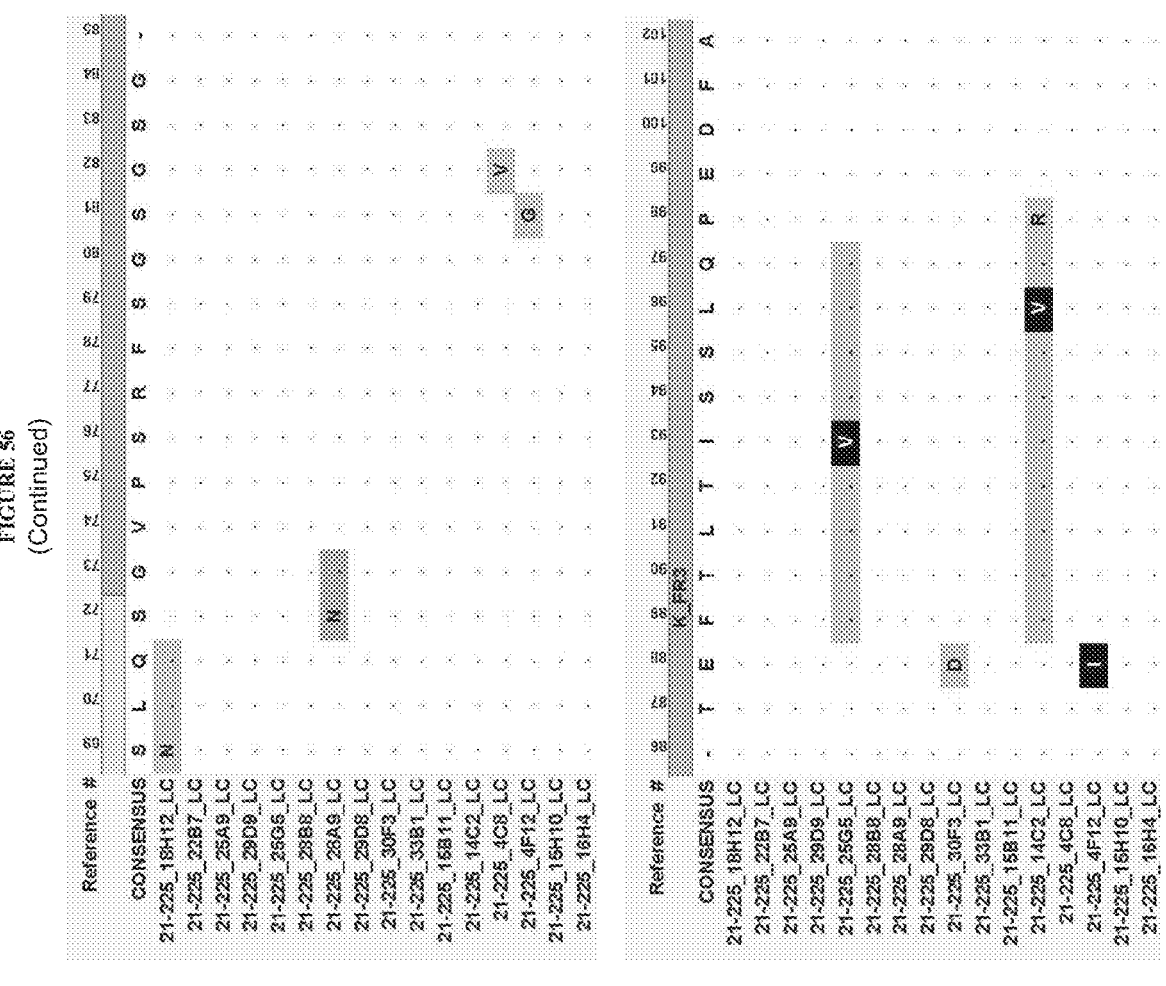
Figure 56:
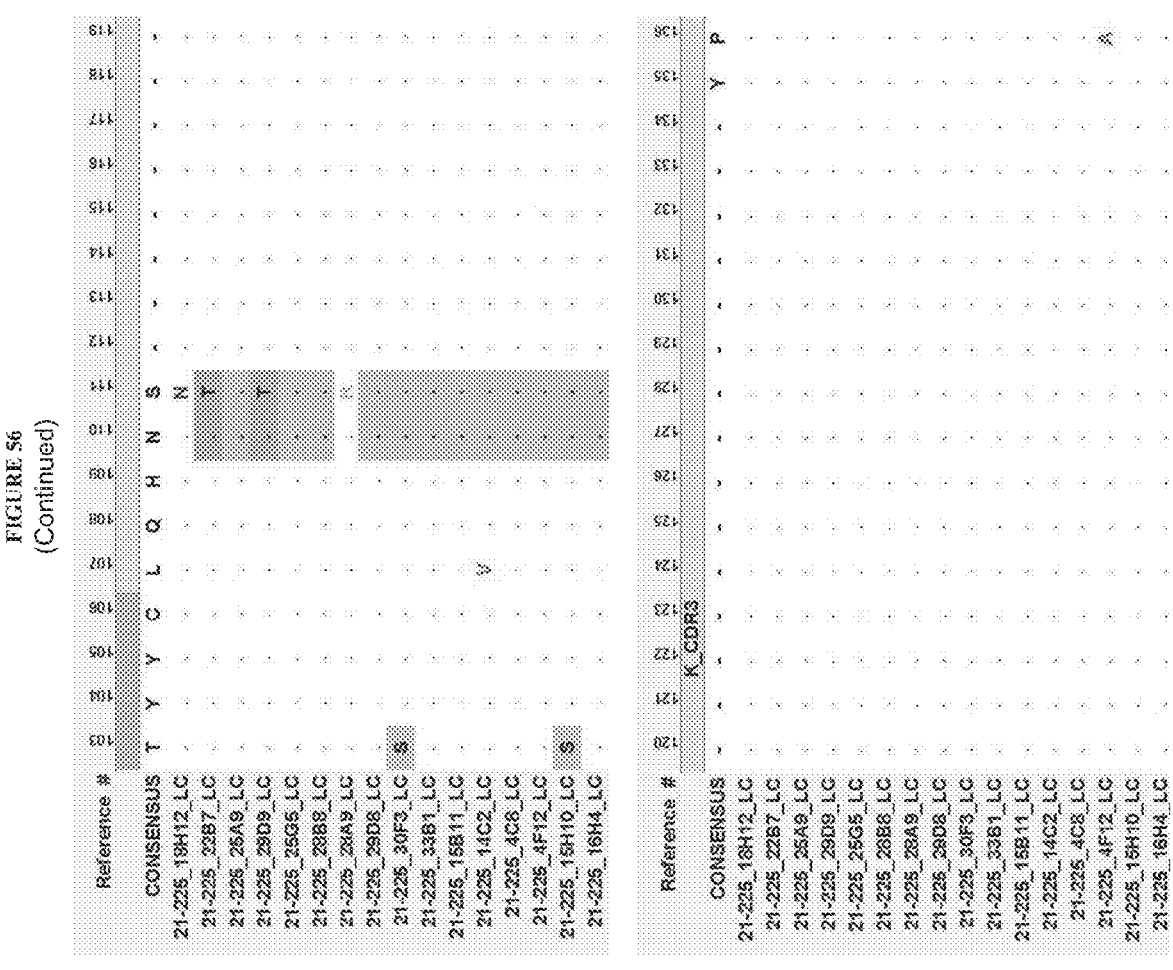
Figure 56:
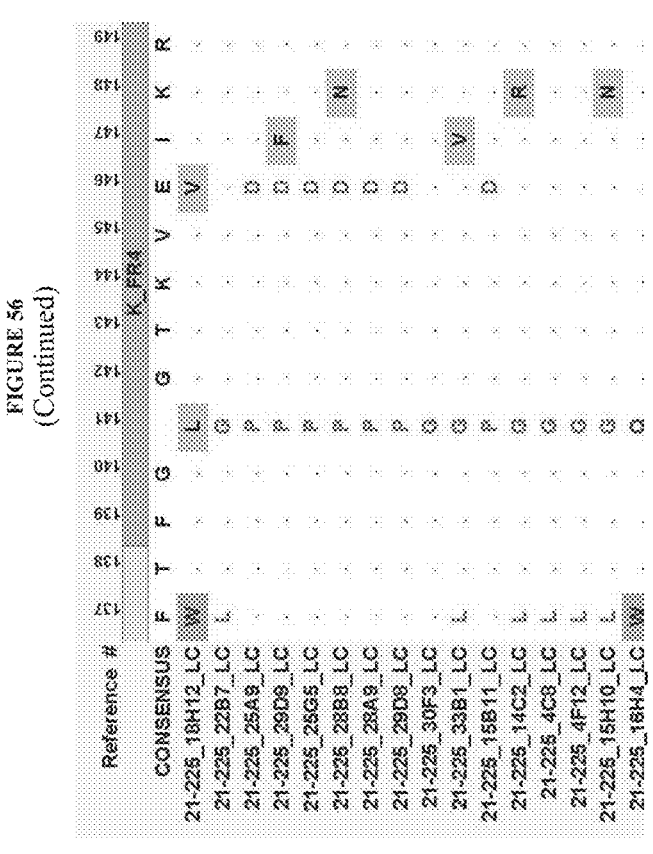
Figure 86:
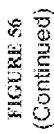
Figure 56:
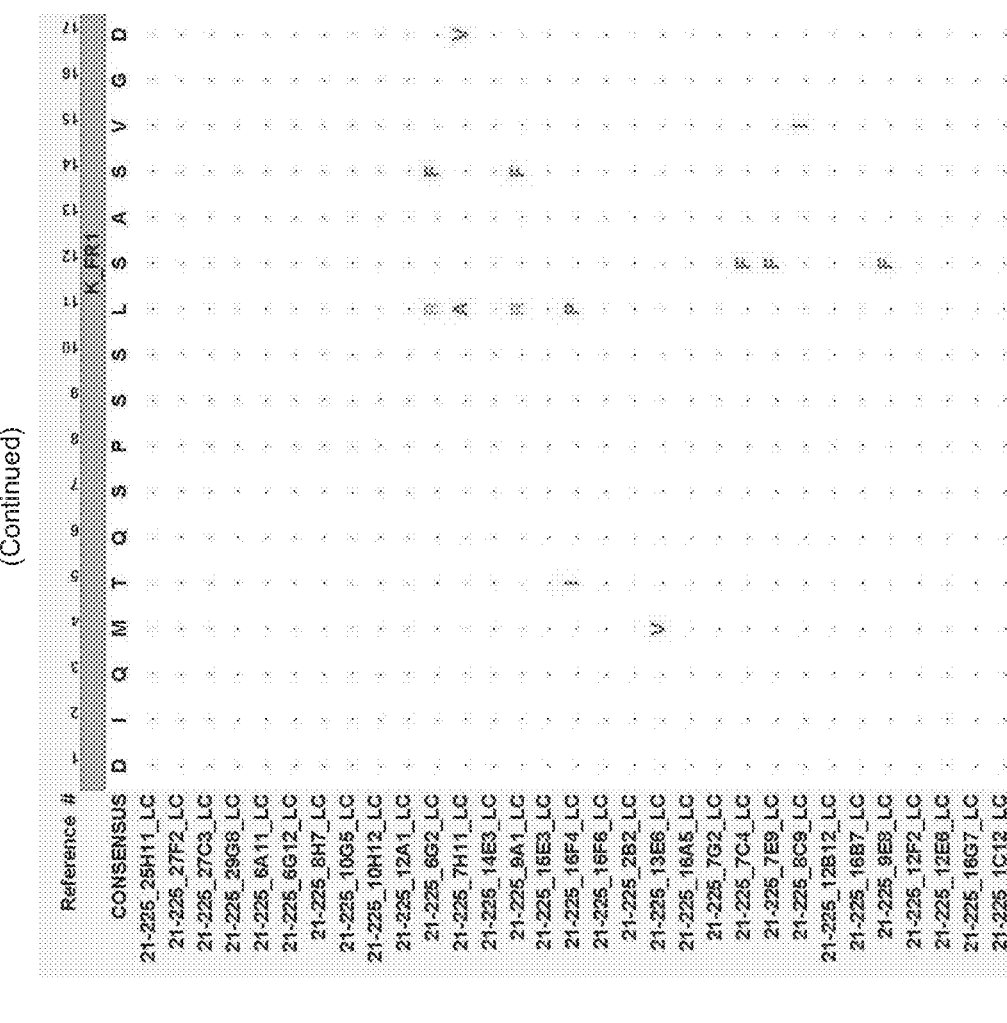
Figure 56:
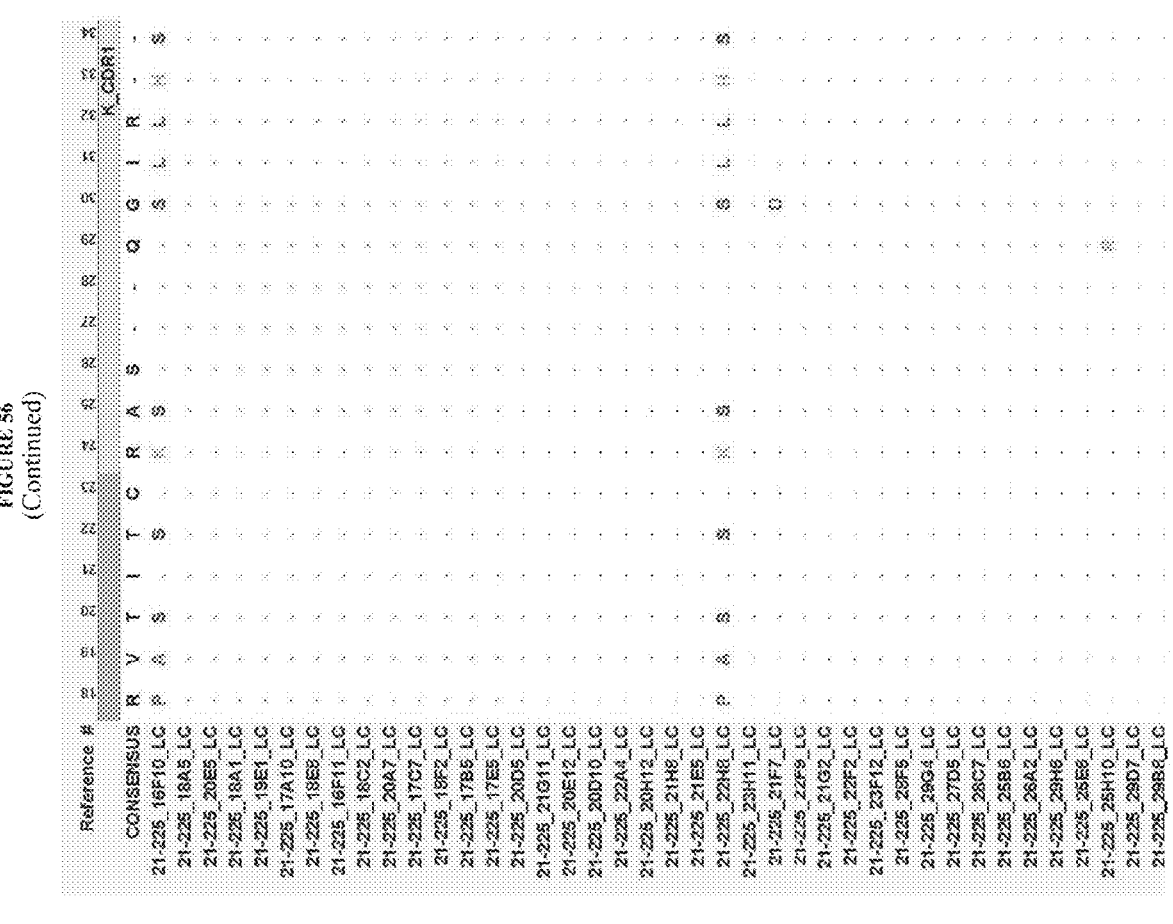
Figure 56:
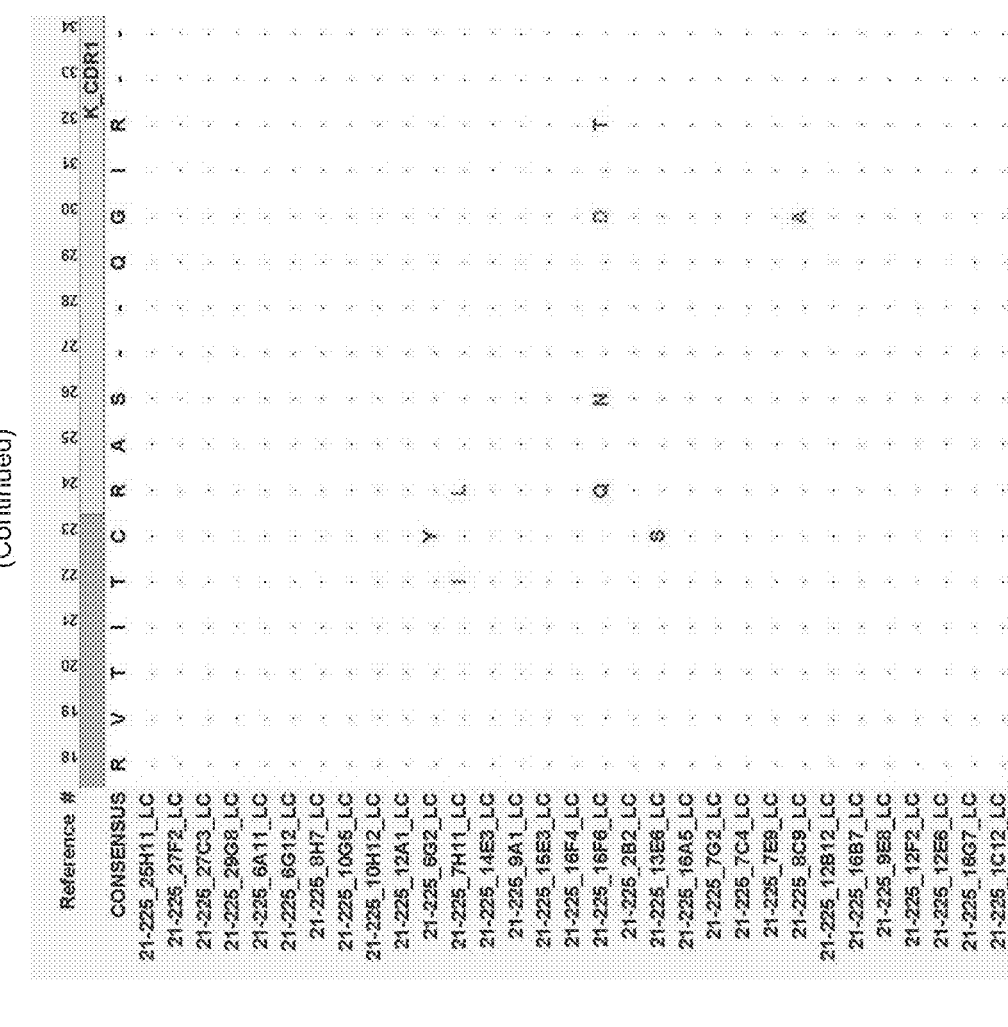
Figure 56:
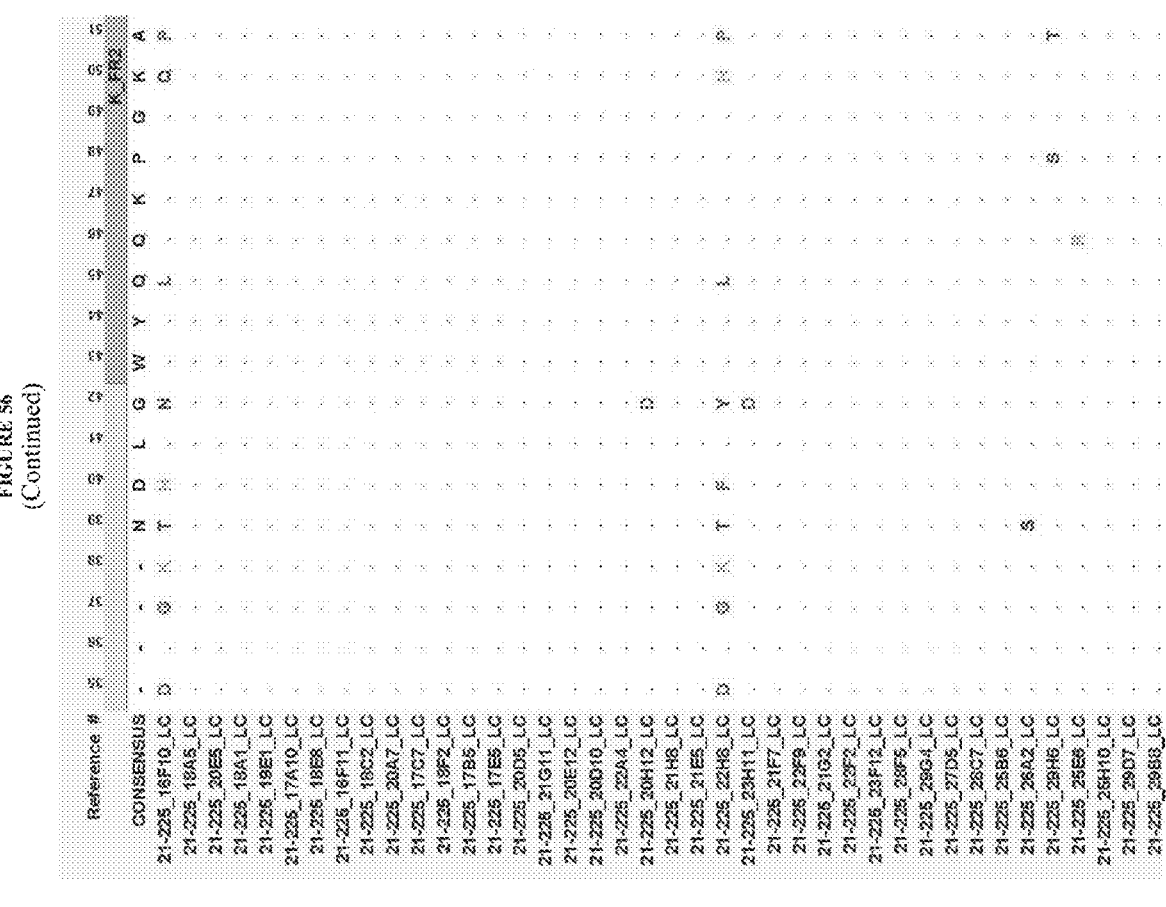
Figure 56:
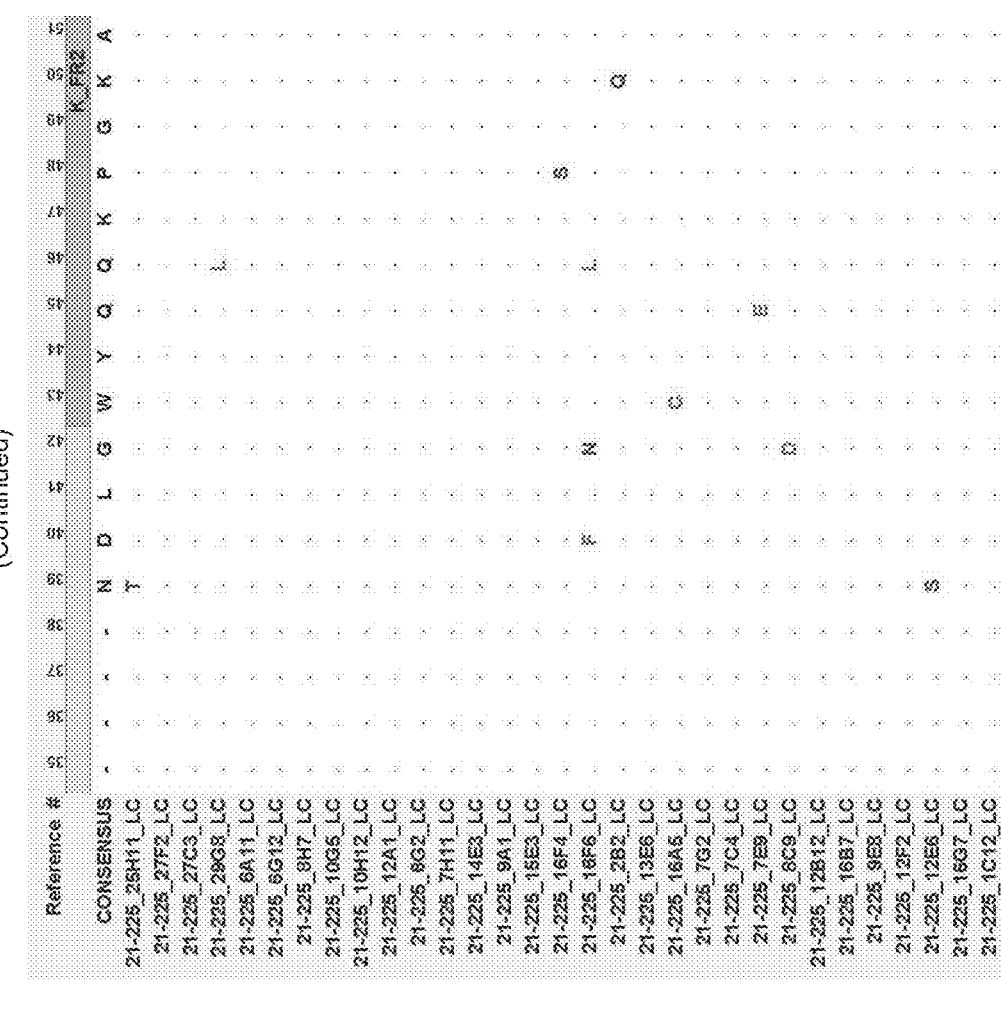
Figure 56:
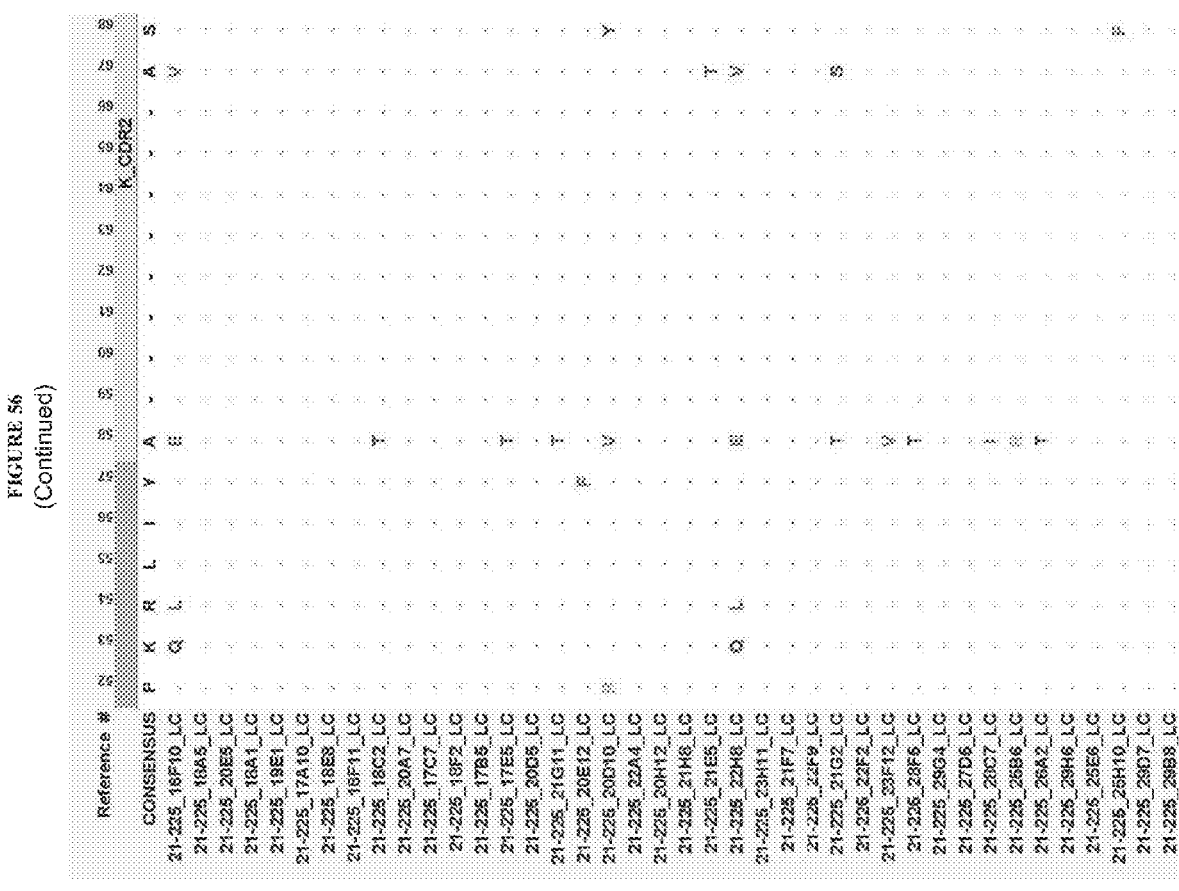
Figure 56:
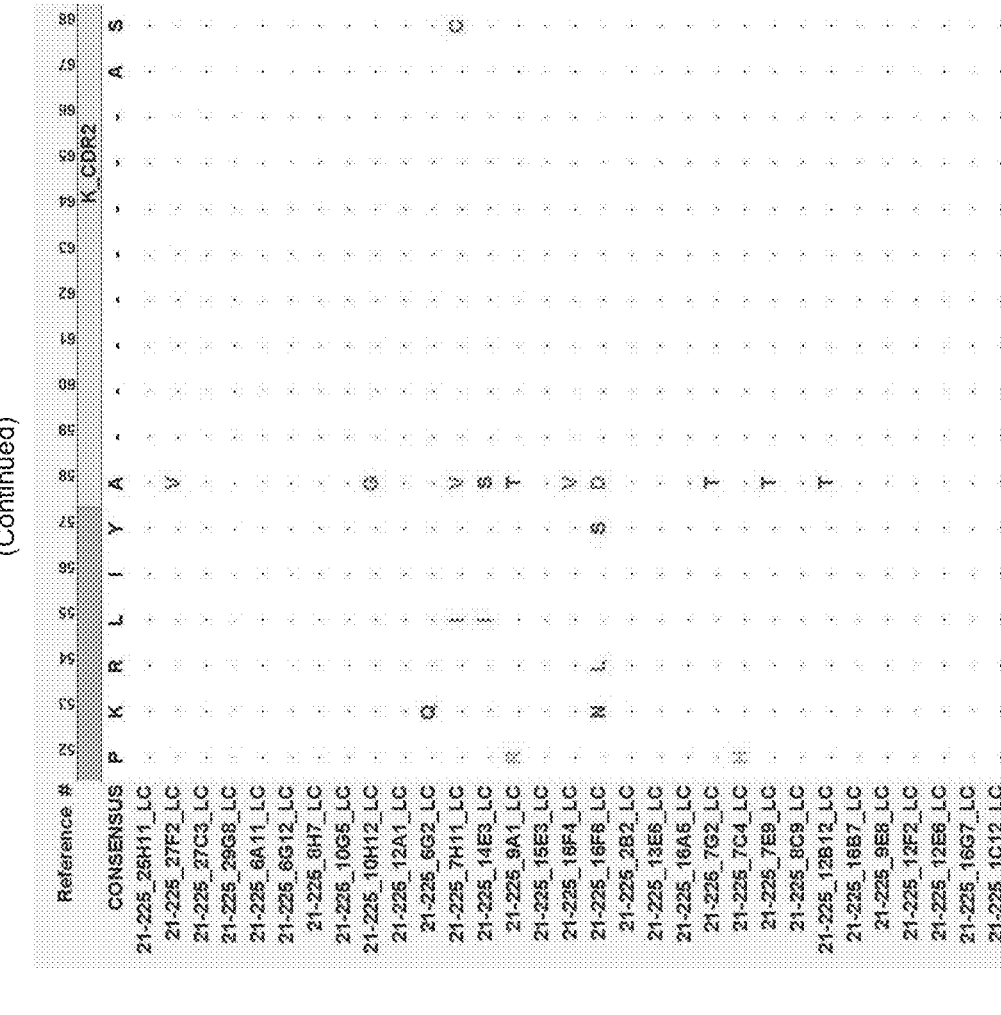
Figure 56:
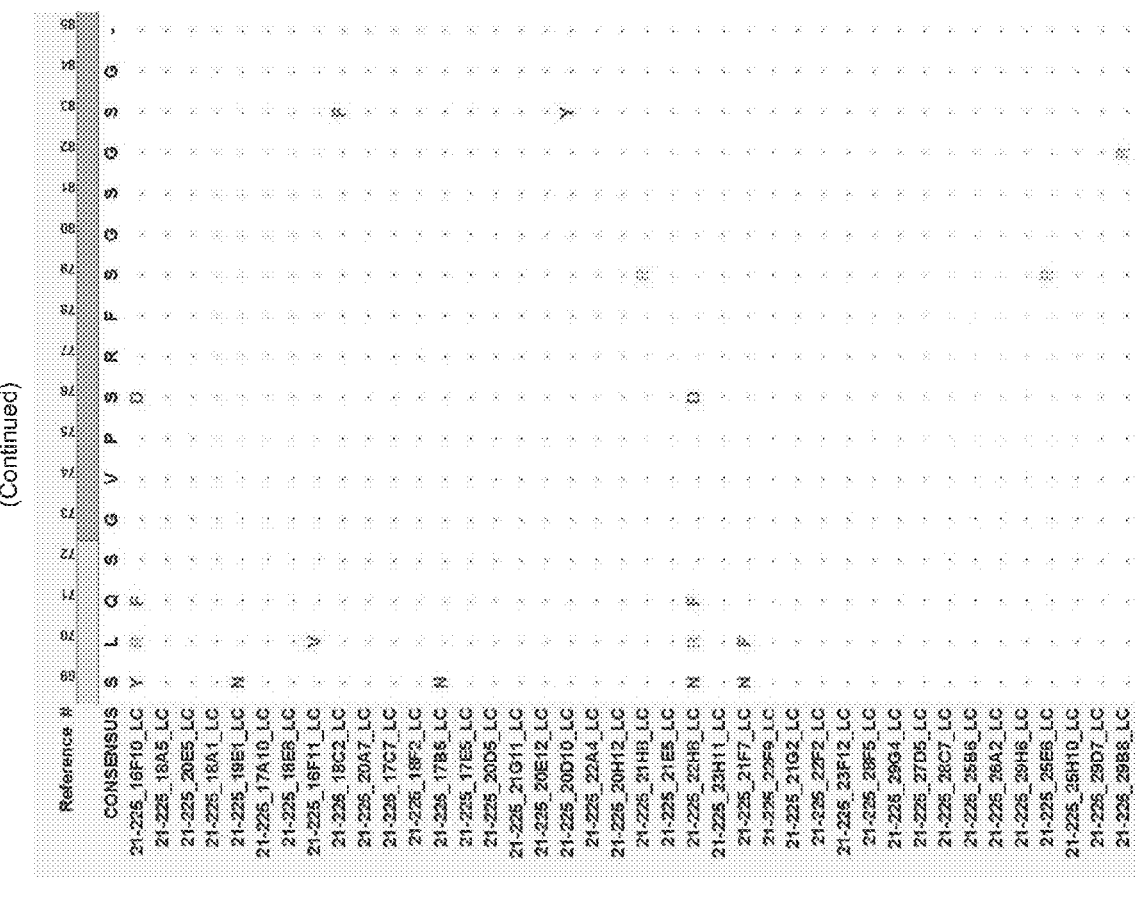
Figure 56:
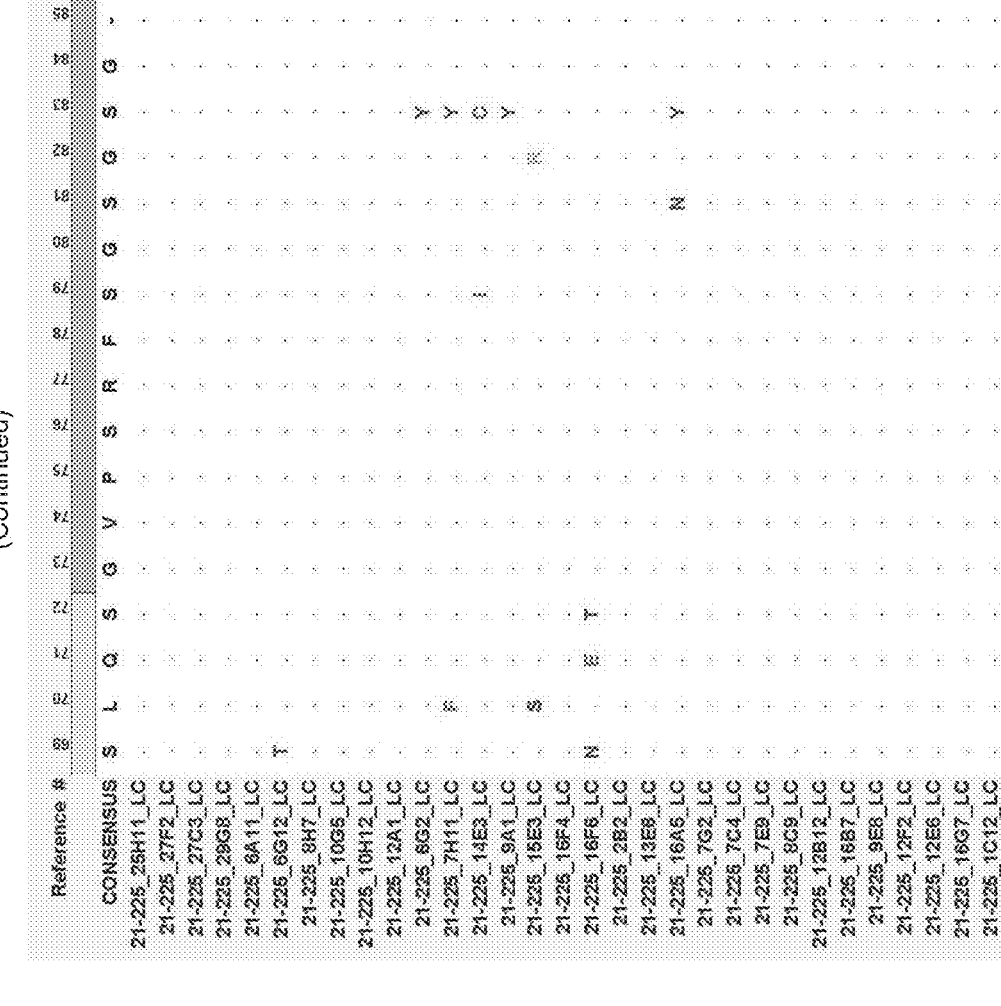
Figure 56:
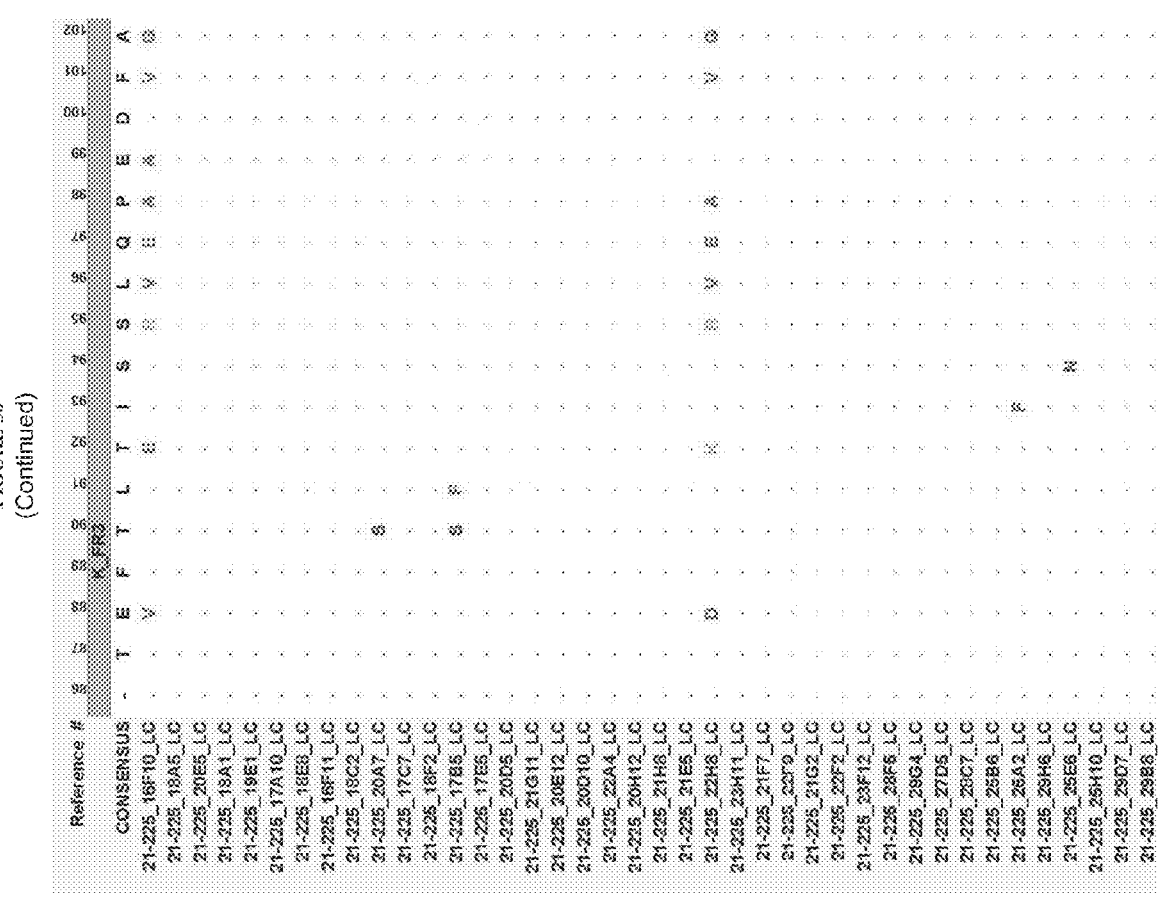
Figure 56:
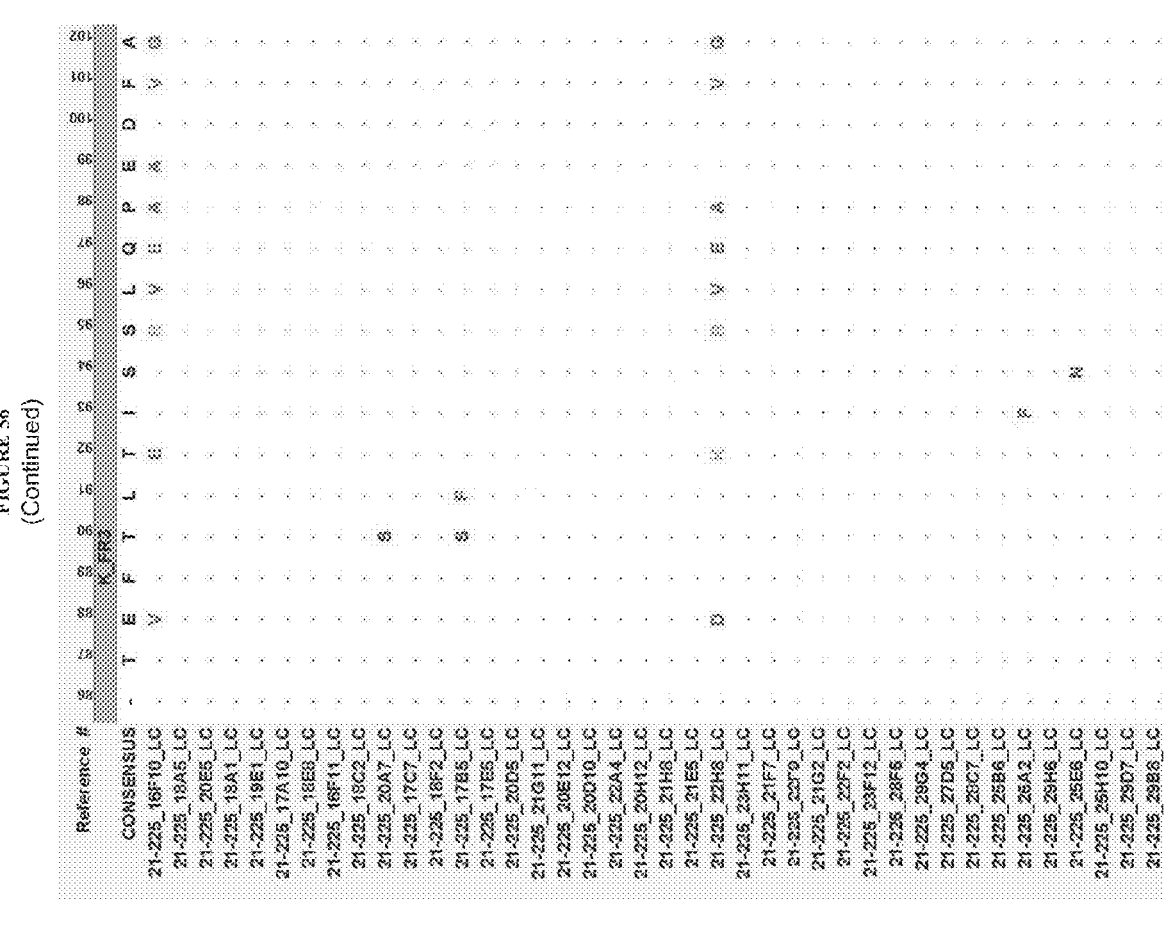
Figure 56:
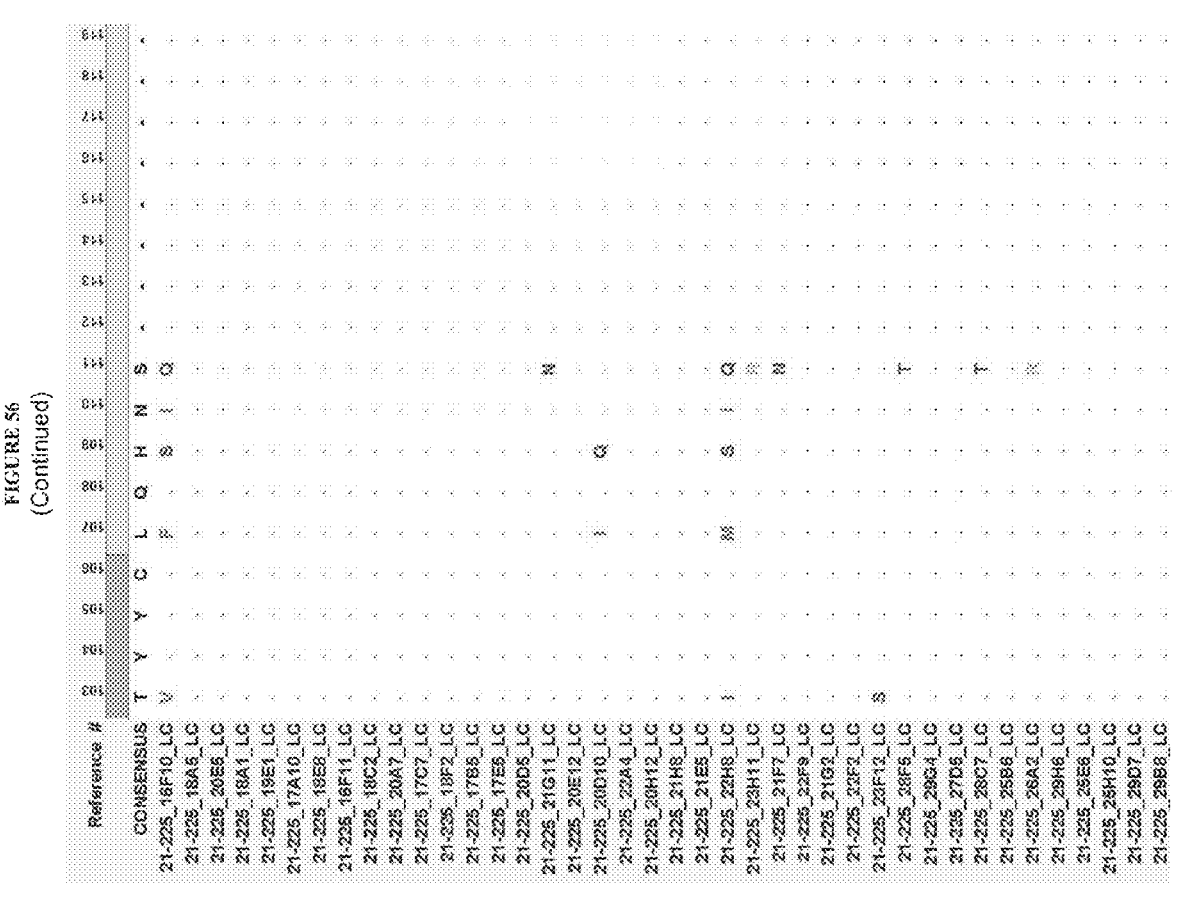
Figure 56:
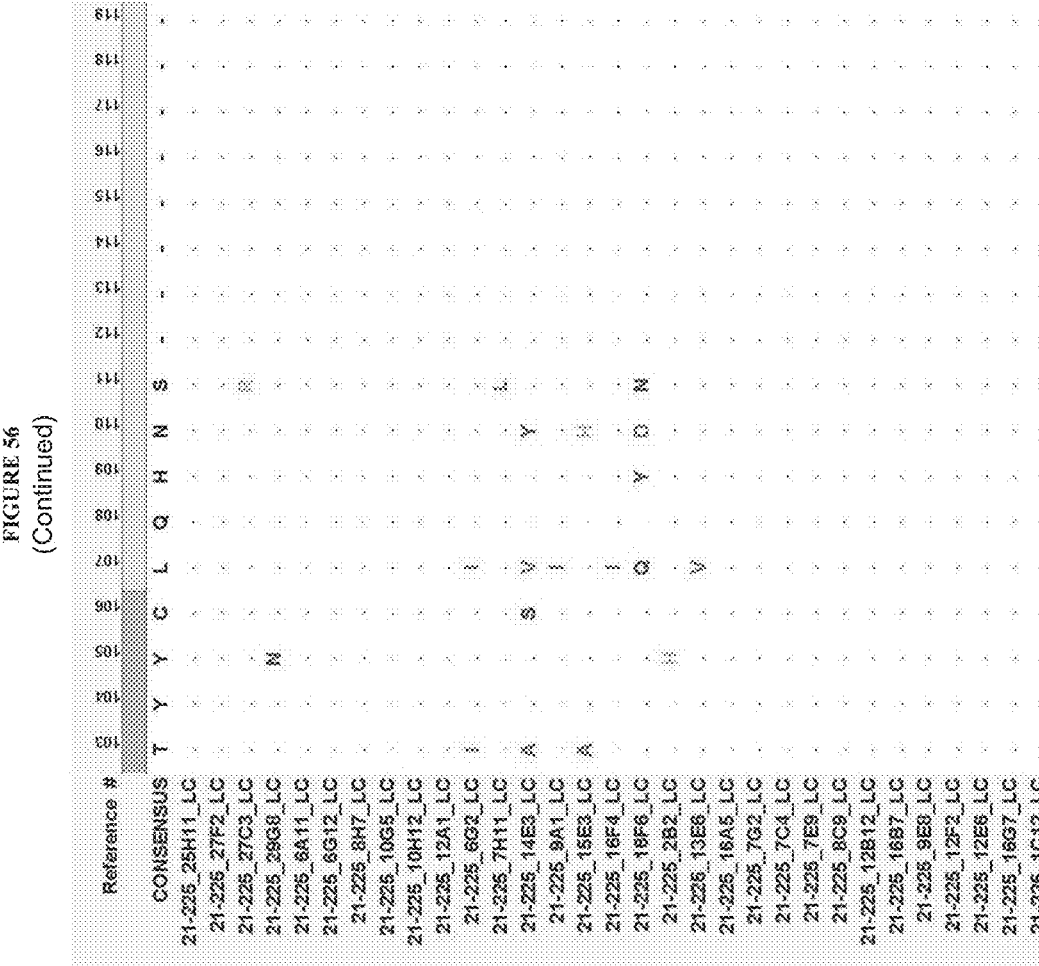
Figure 56:
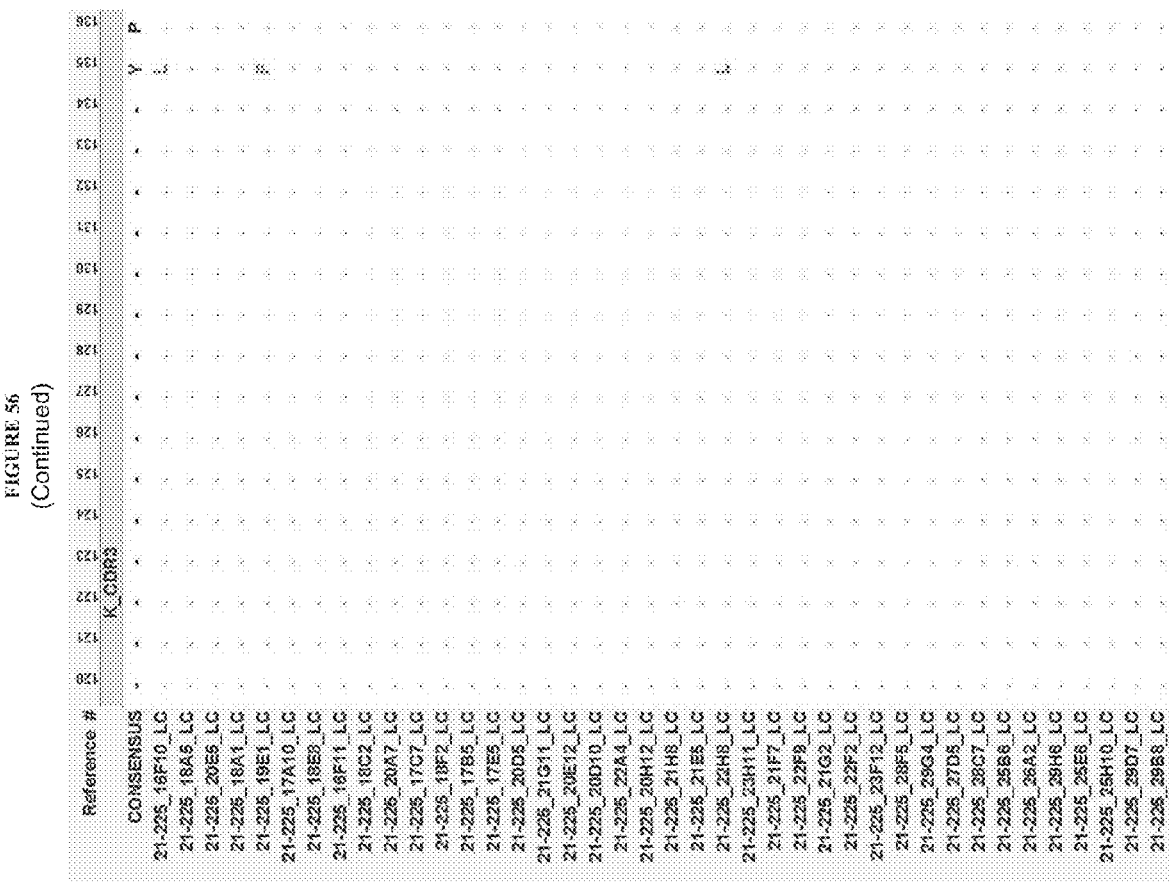
Figure 56:
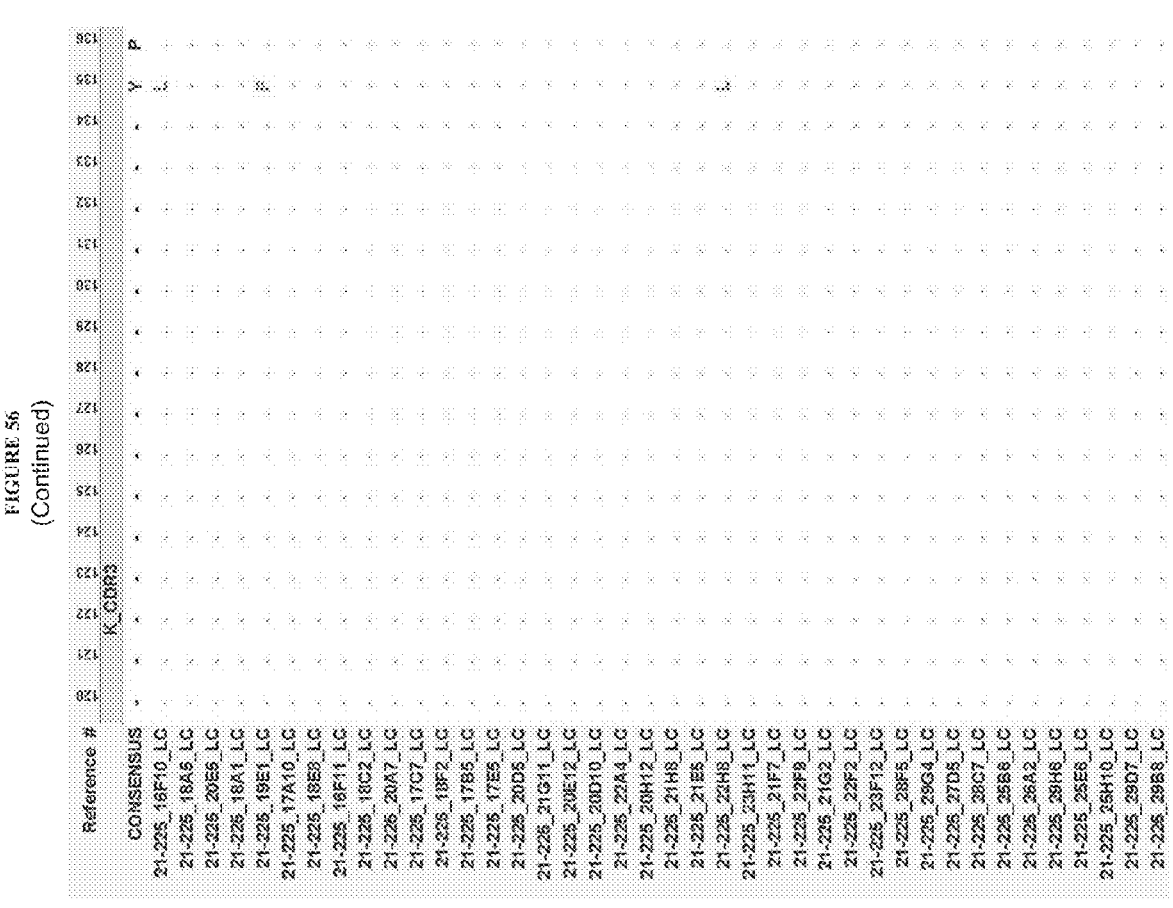
Figure 56:
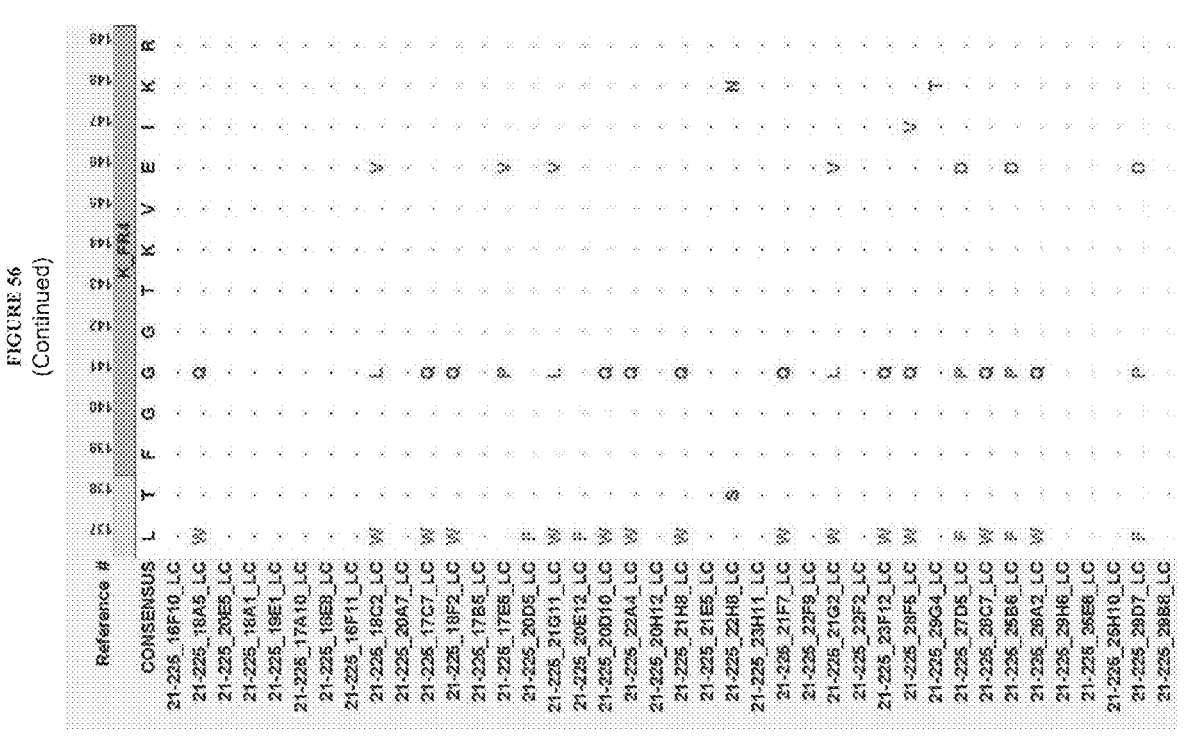
Figure 56:
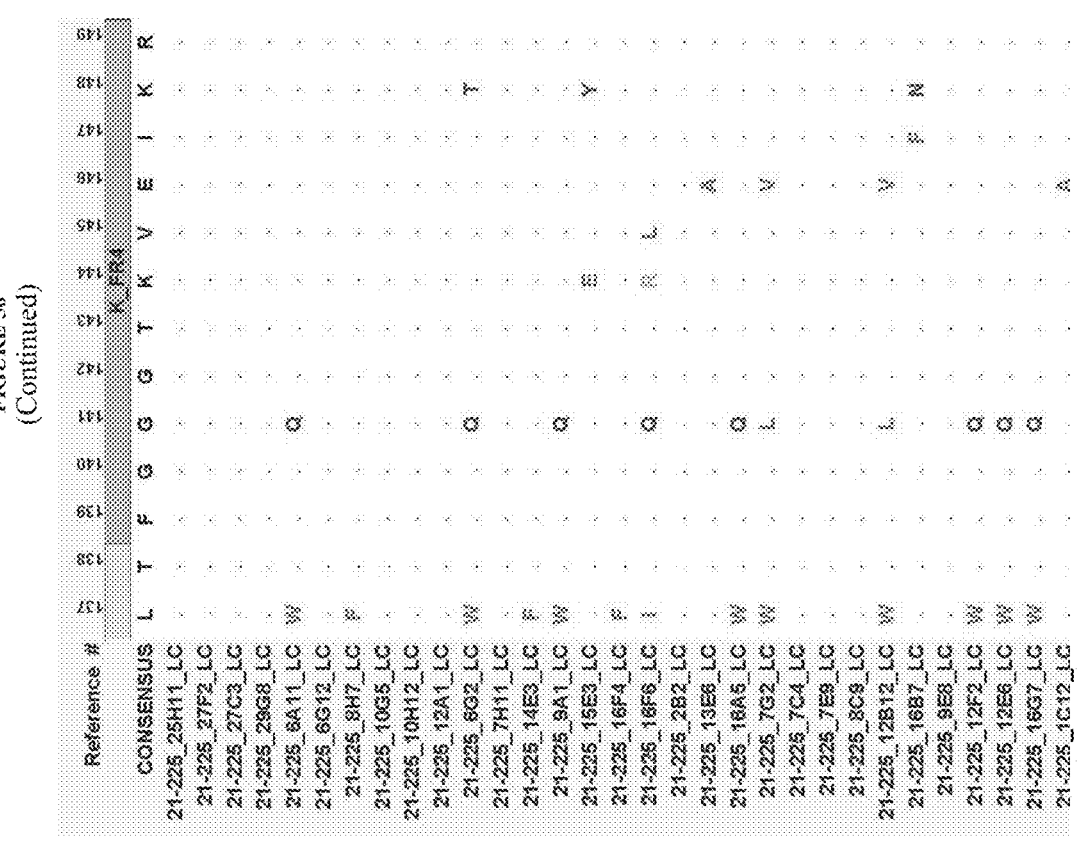
Figure 56:
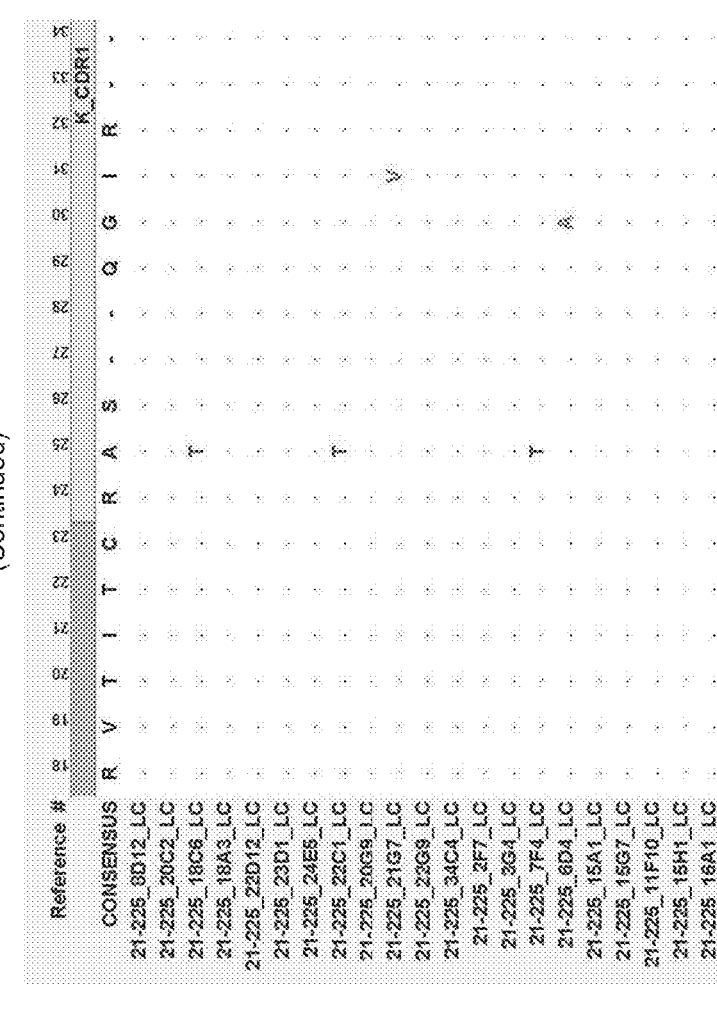
Figure 56:
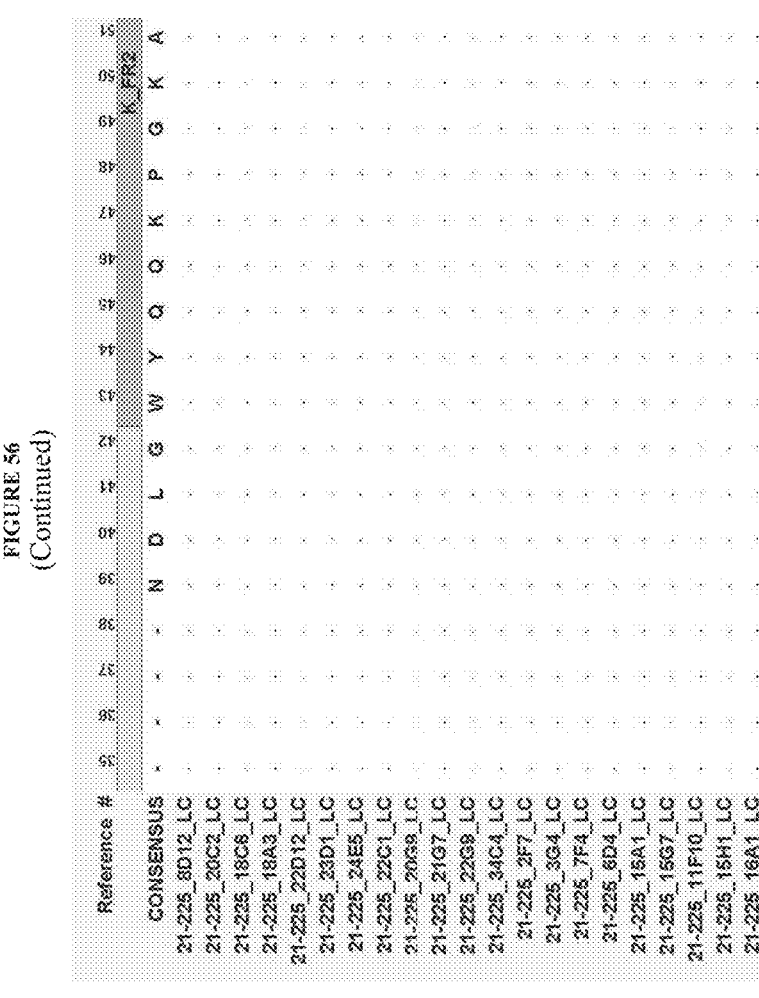
Figure 56:
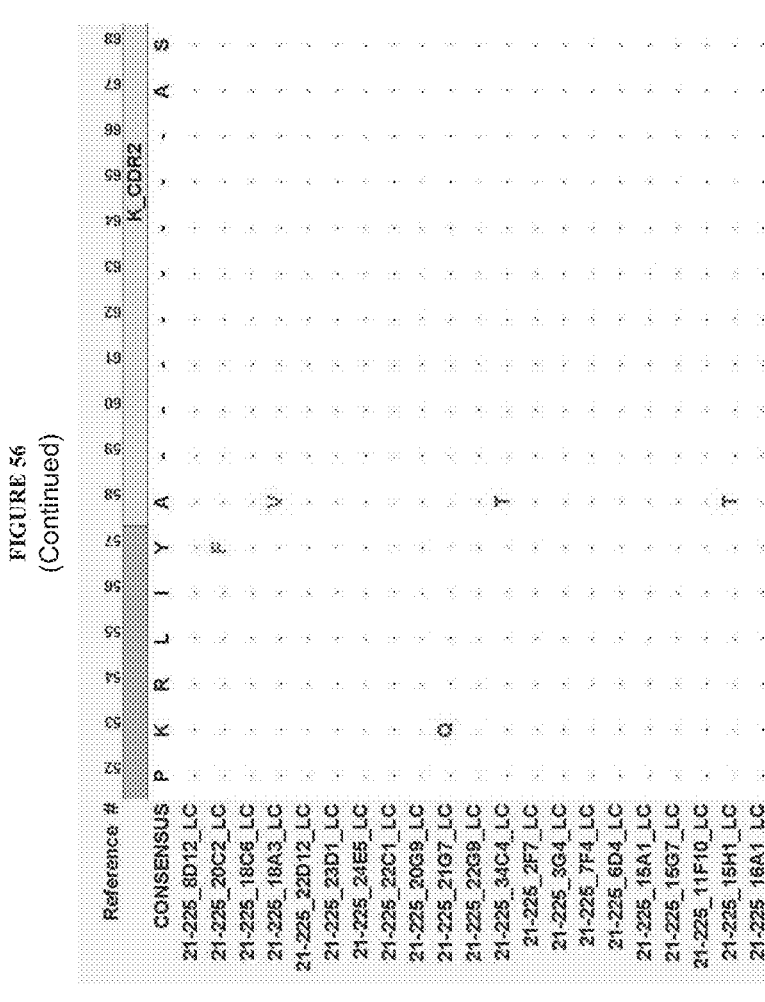
Figure 56:
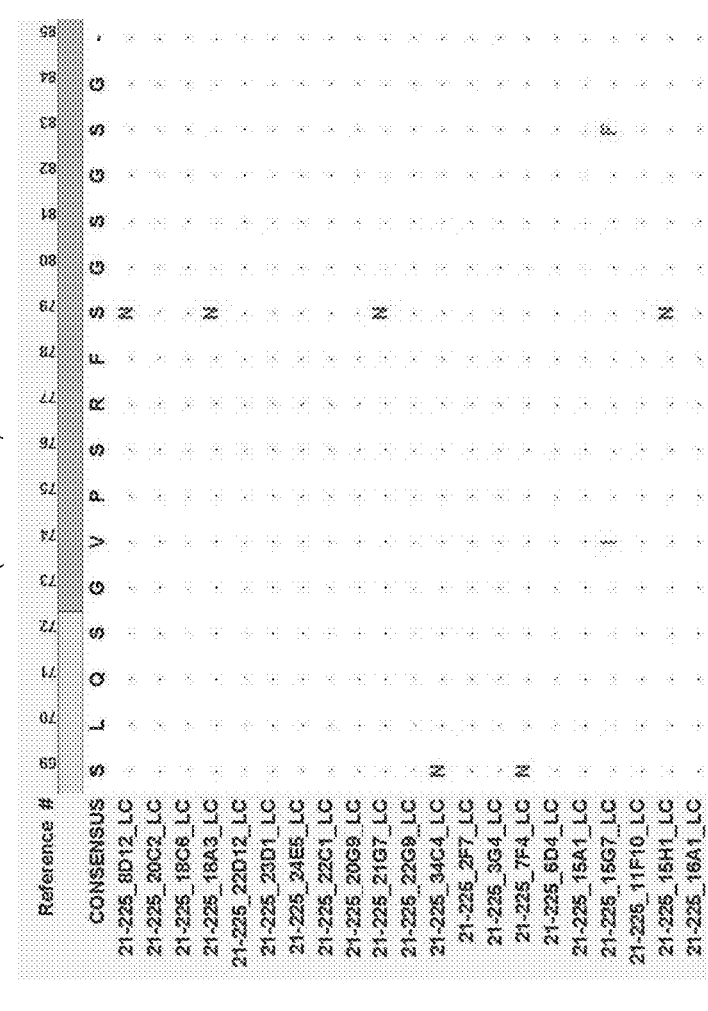
Figure 56:
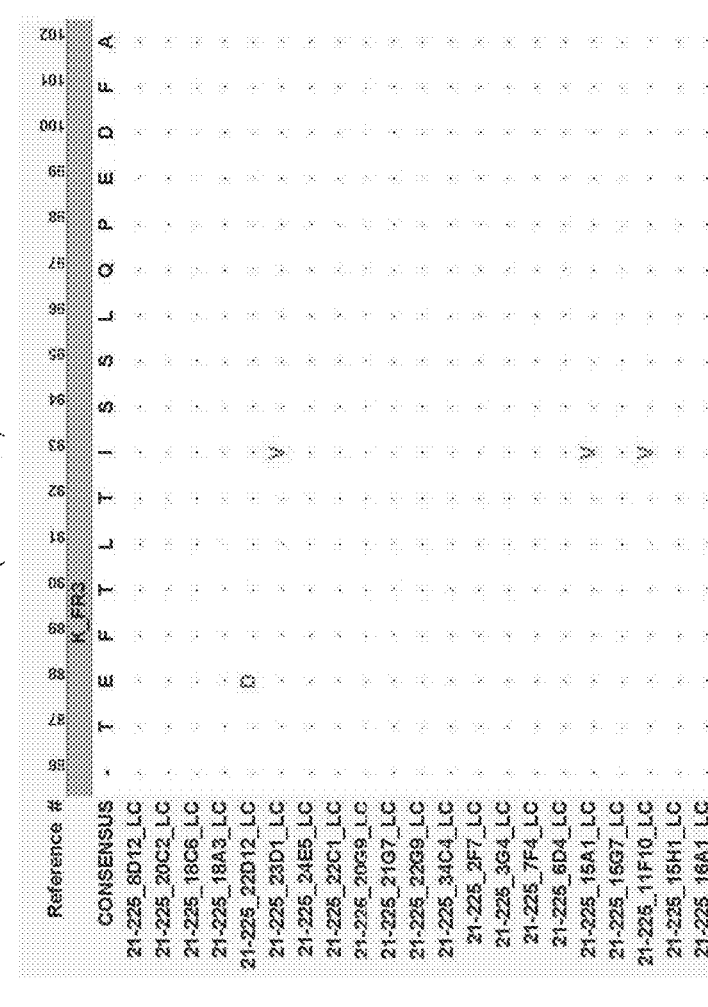
Figure 56:
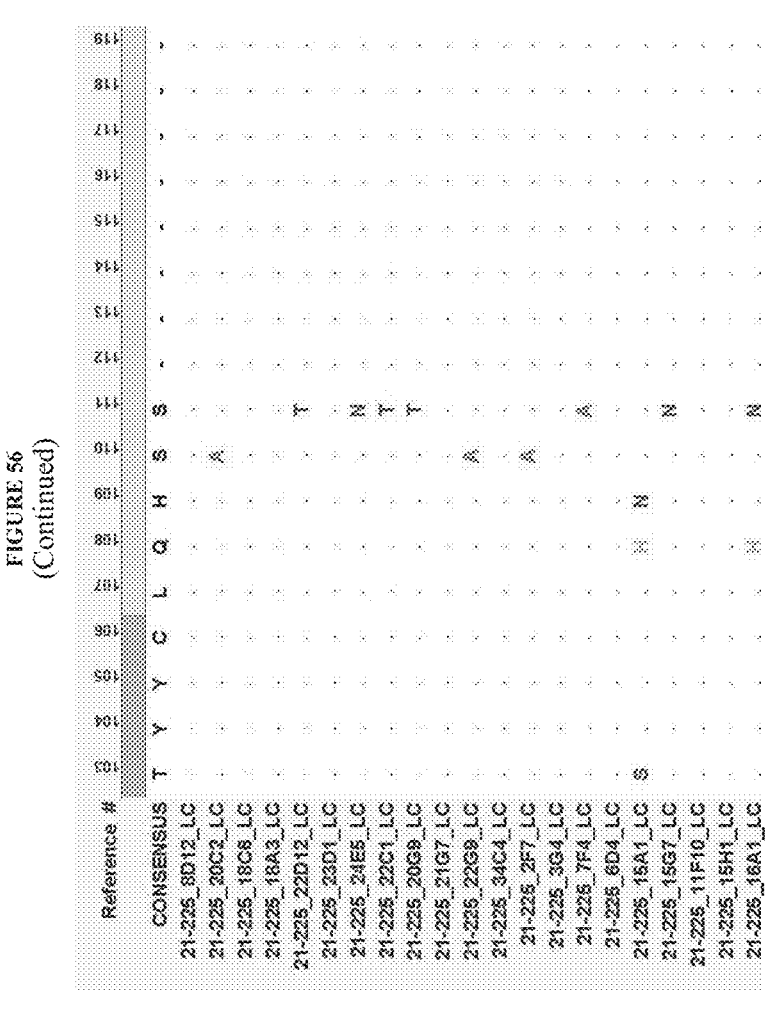
Figure 56:
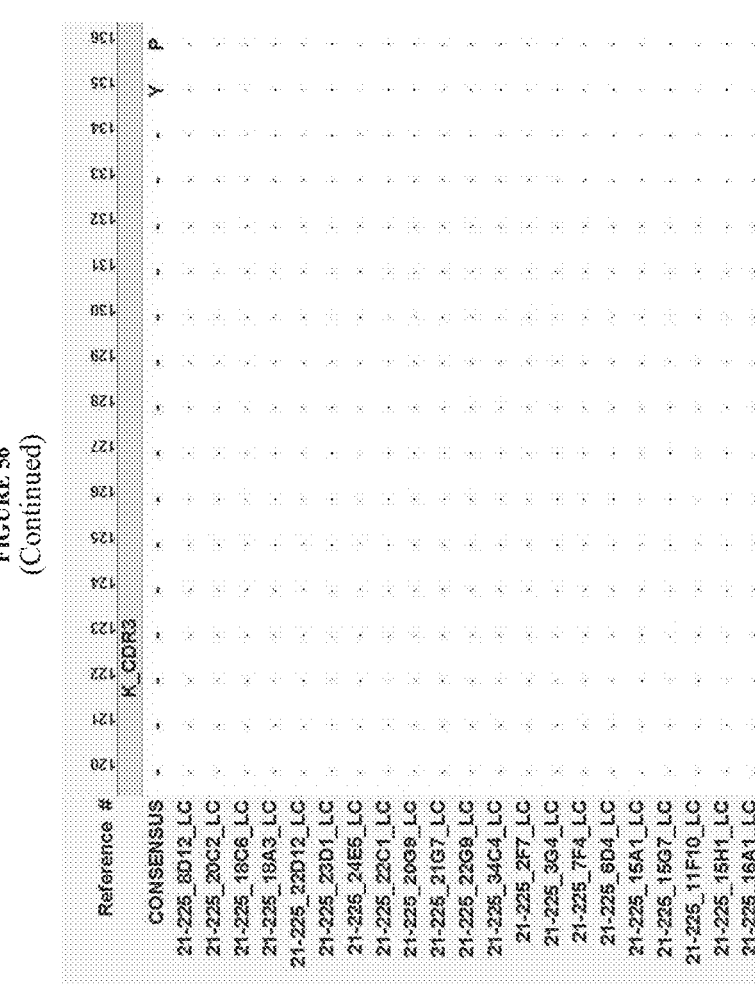
Figure 56:
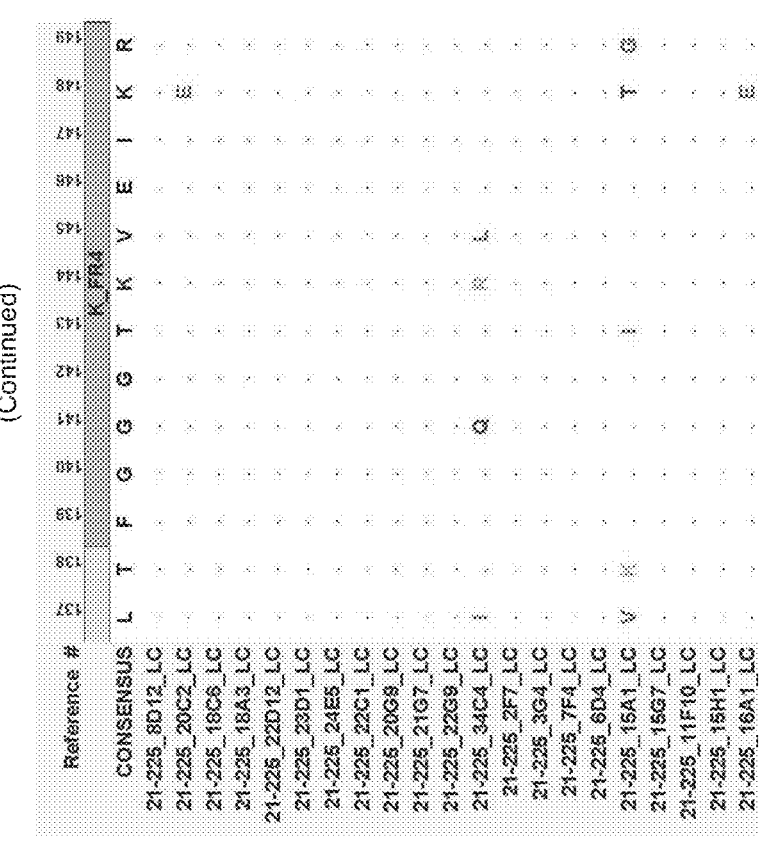
Figure 56:
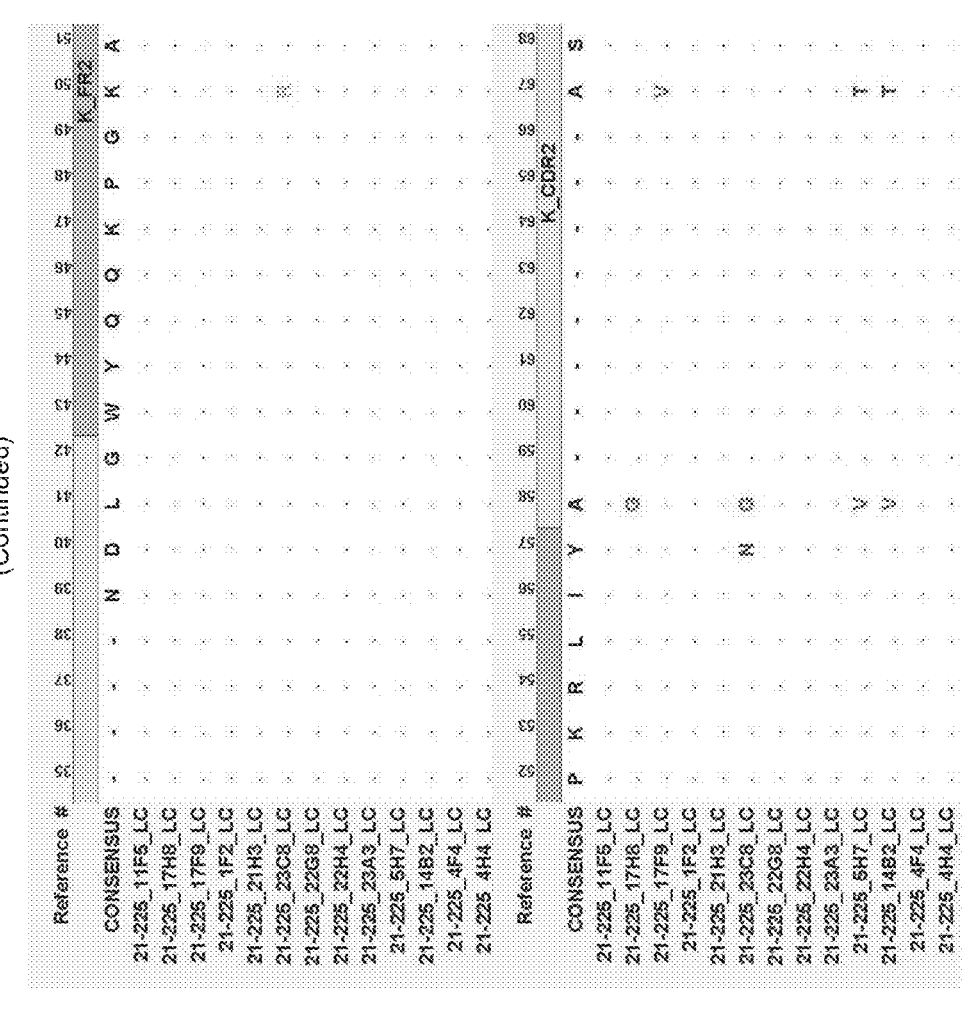
Figure 56:
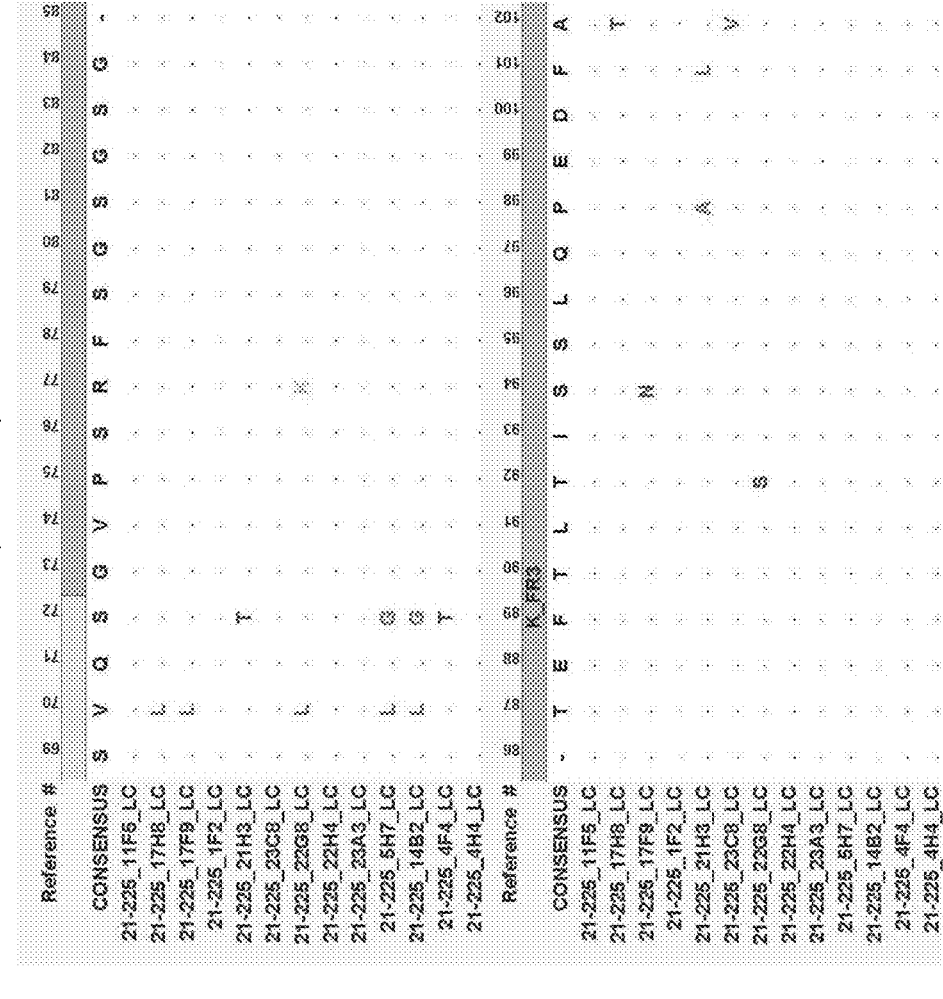
Figure 56:
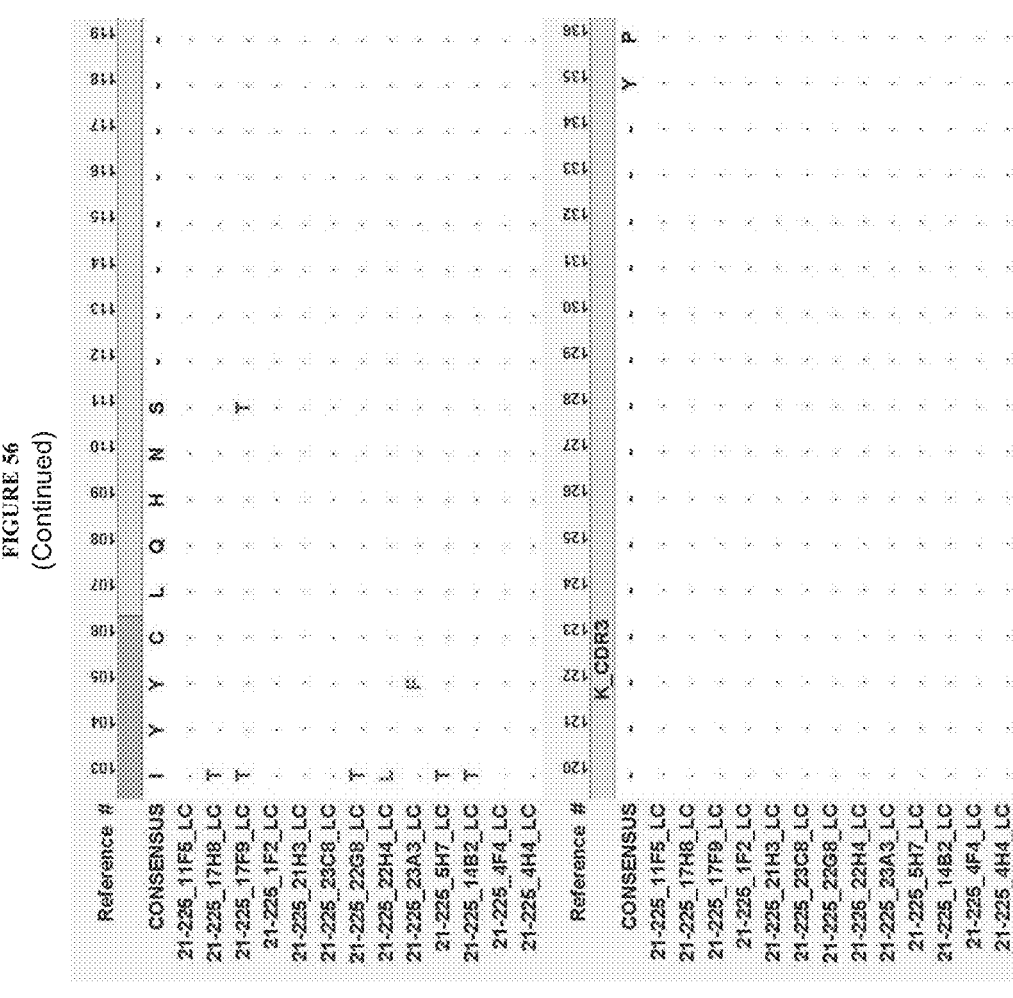
Figure 56:
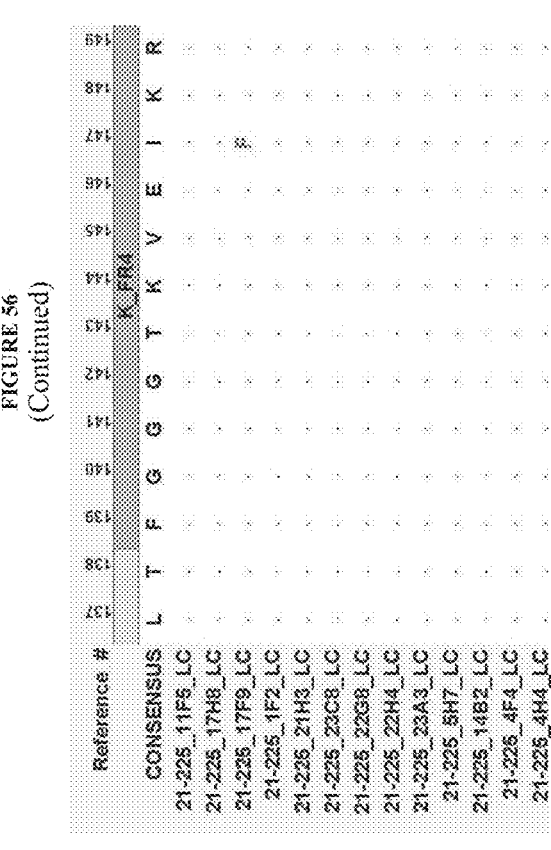
Figure 57:
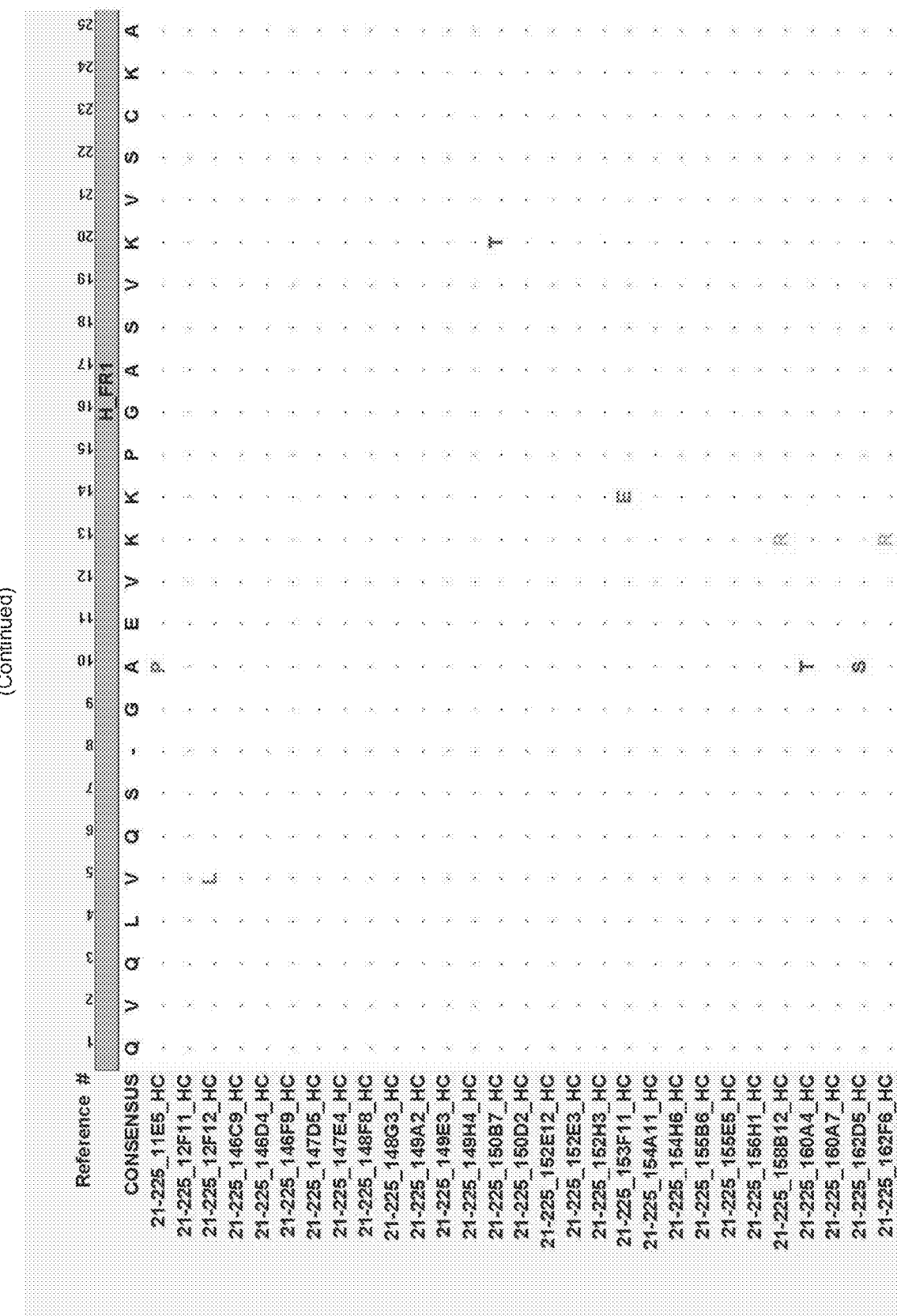
FIG. 57. A group of tables presenting the consensus protein alignment of various light and heavy chain variable regions for certain antigen binding proteins of the present invention (Tables 49-134).
Figure 57:
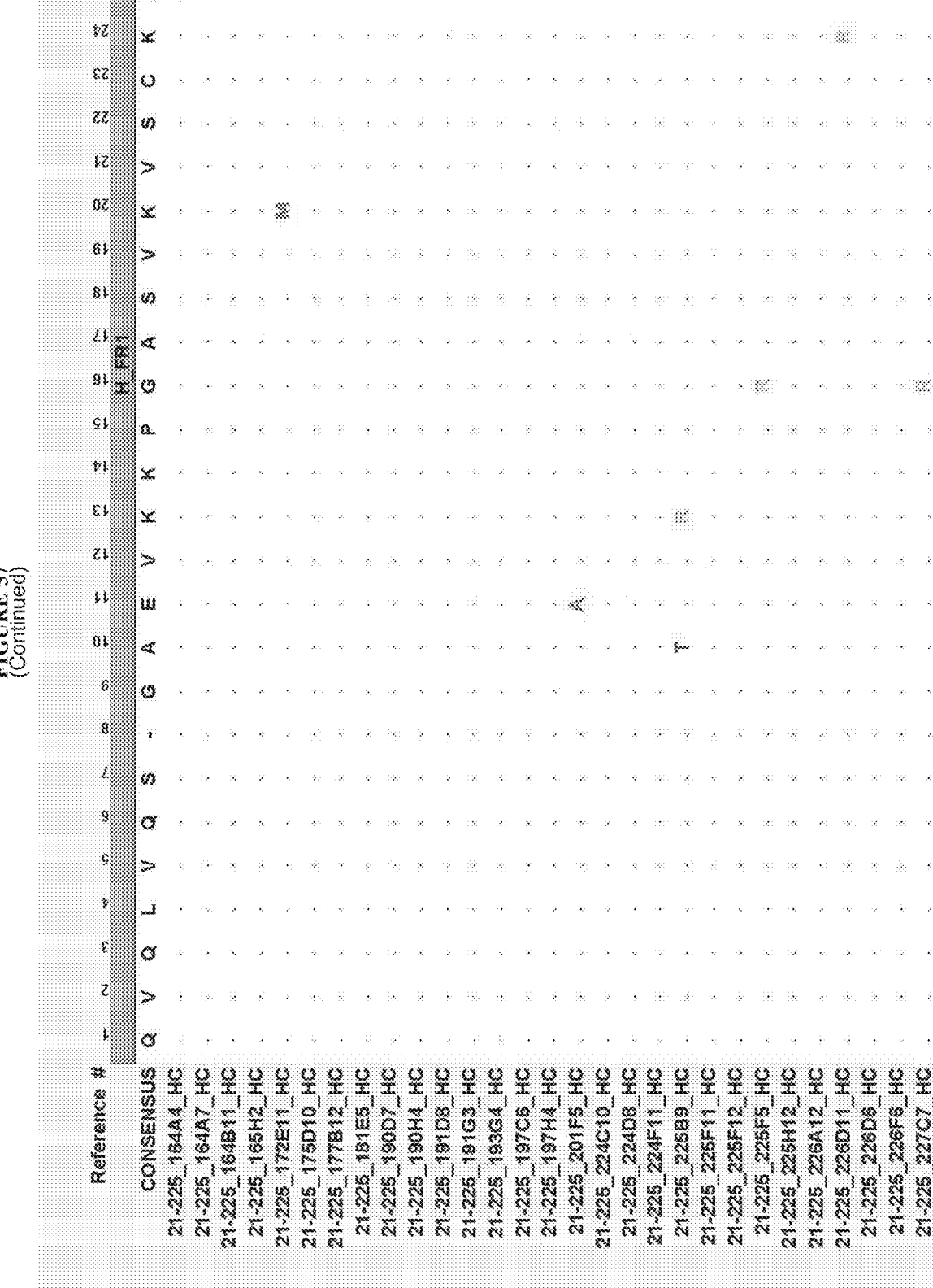
Figure 57:
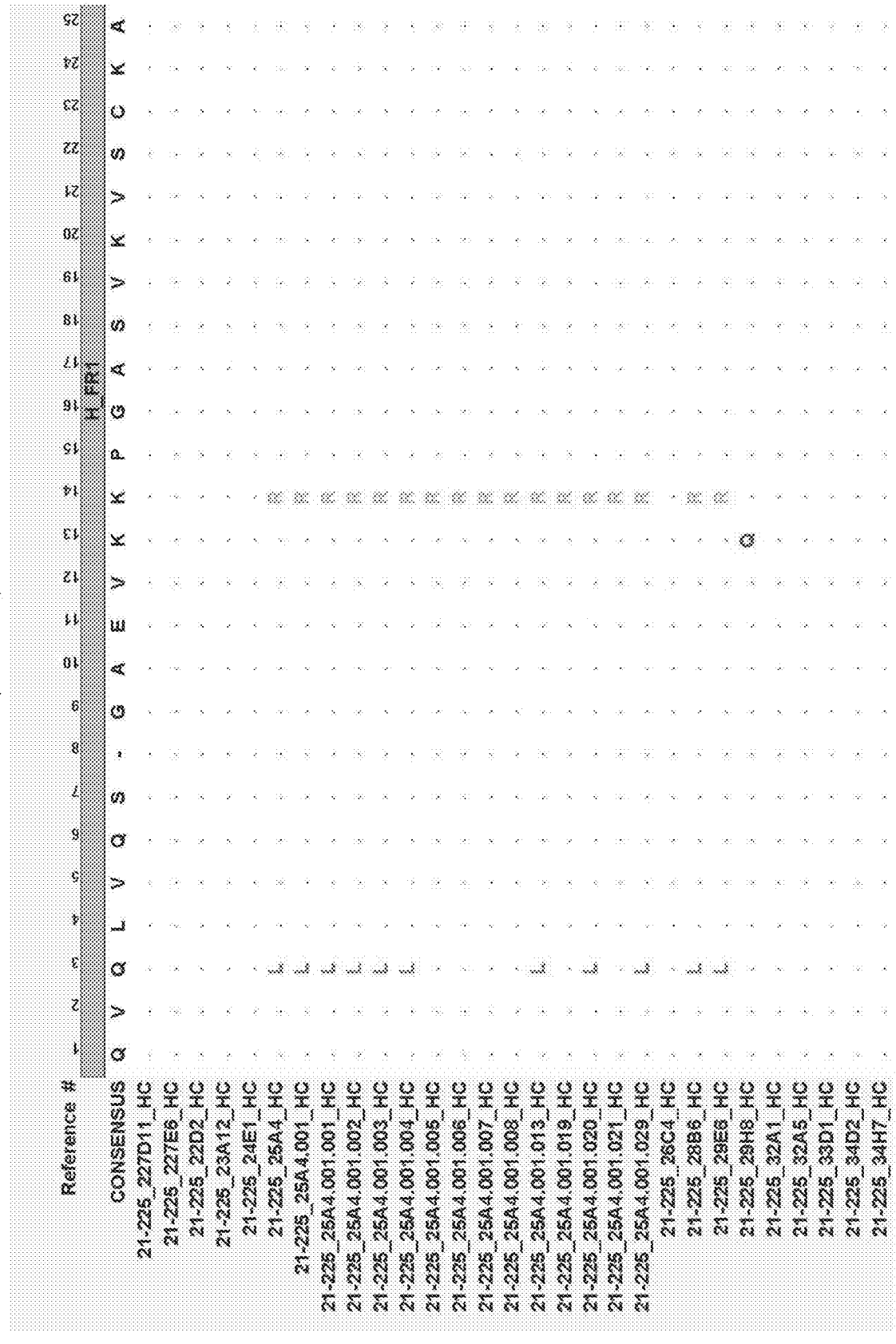
Figure 57:
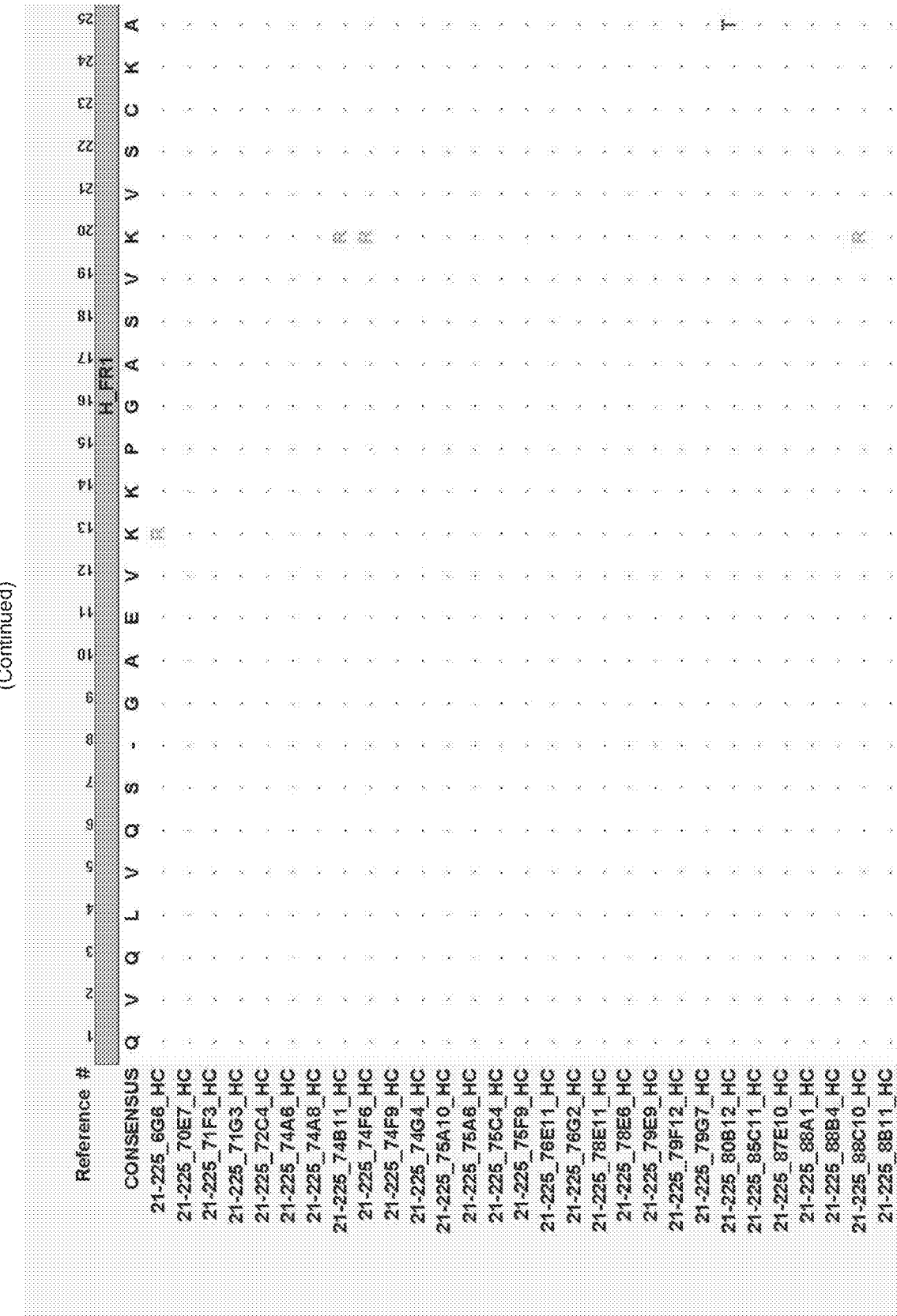
Figure 57:
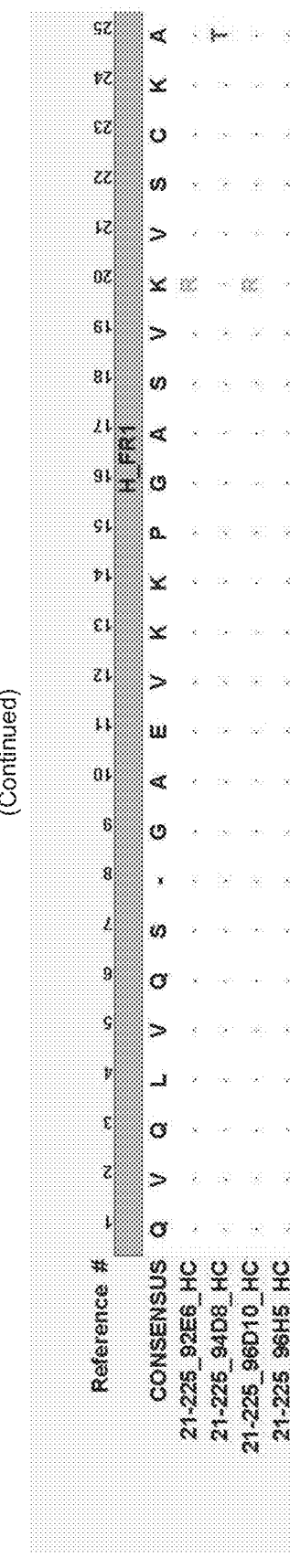
Figure 57:
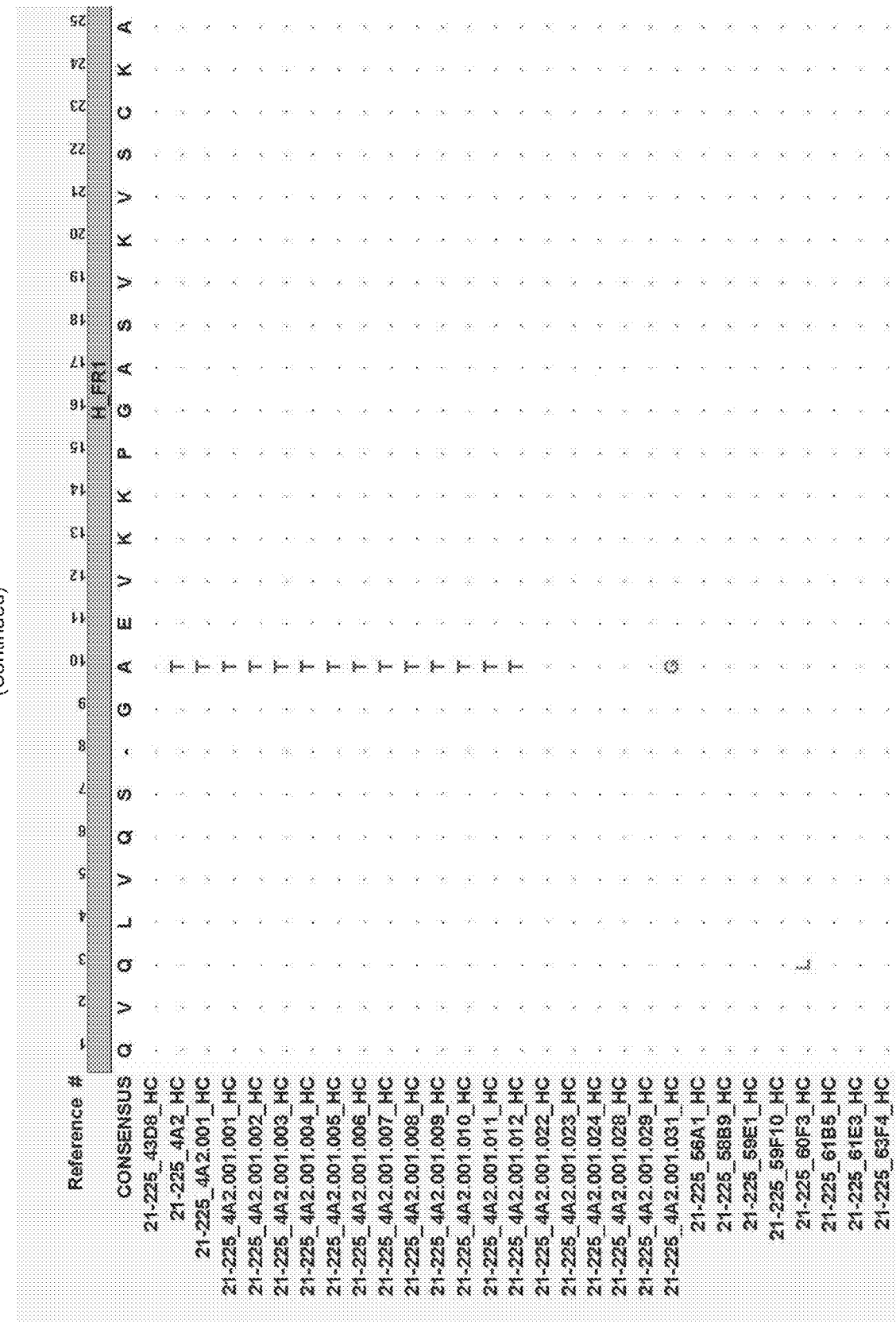
Figure 57:
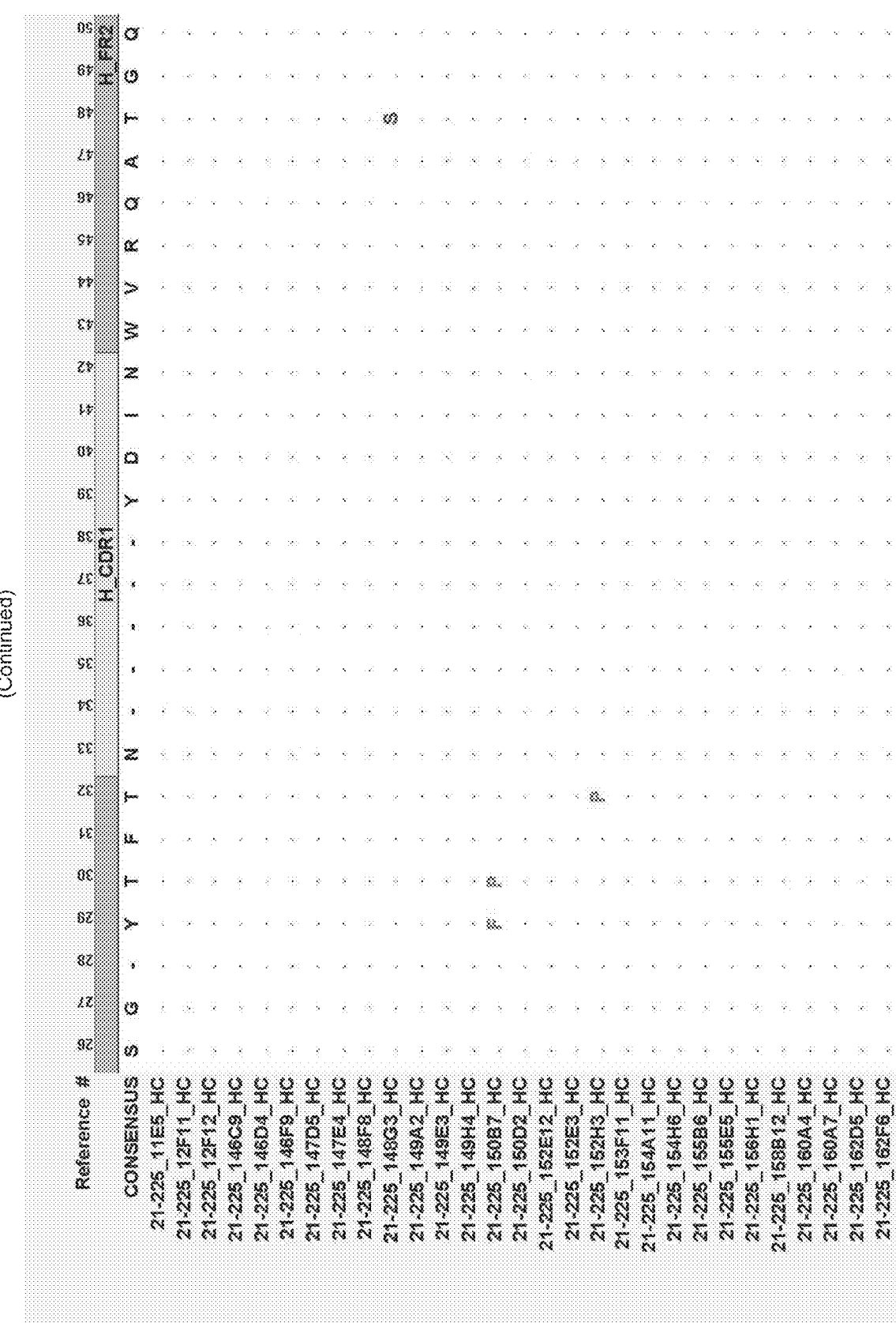
Figure 57:
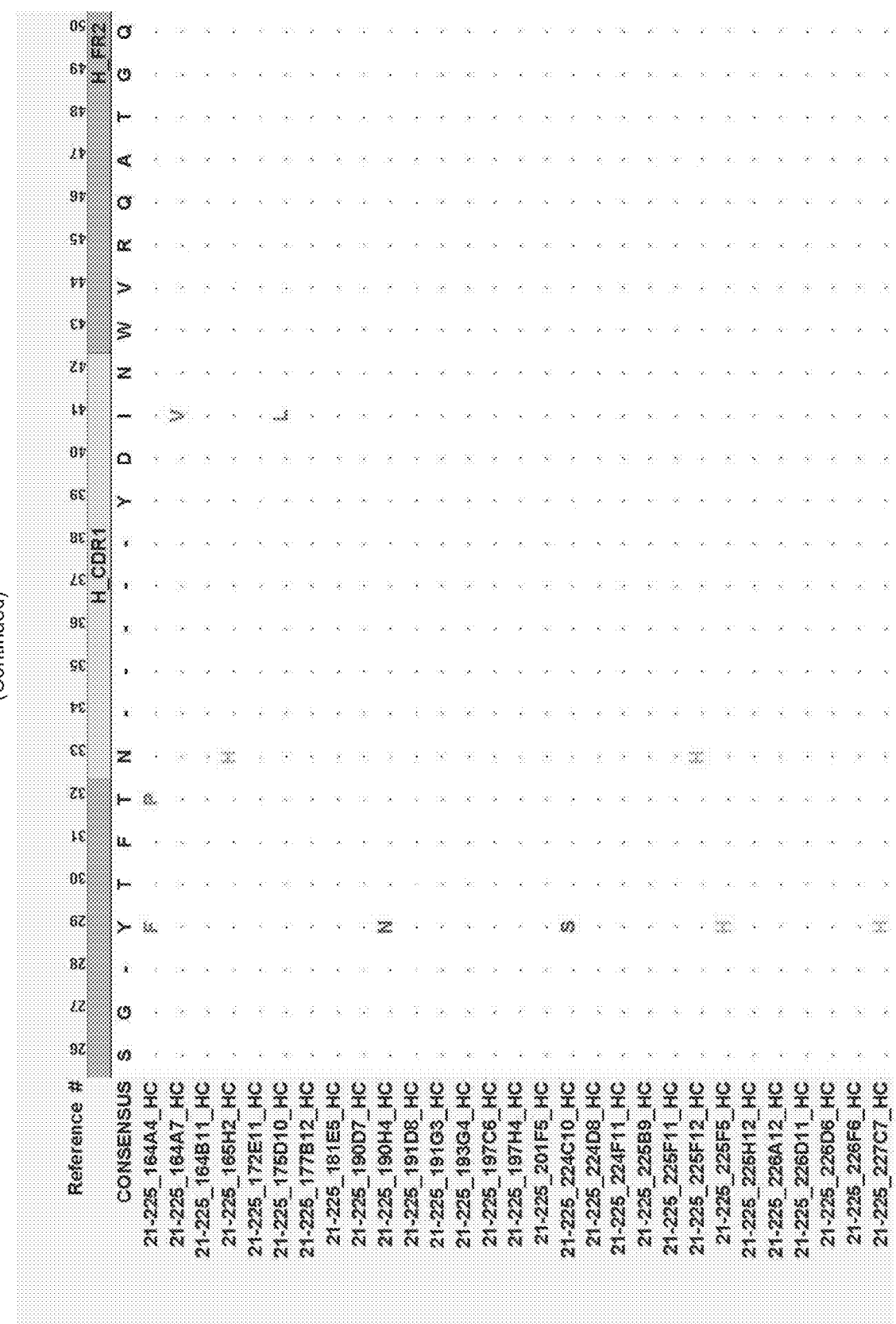
Figure 57:
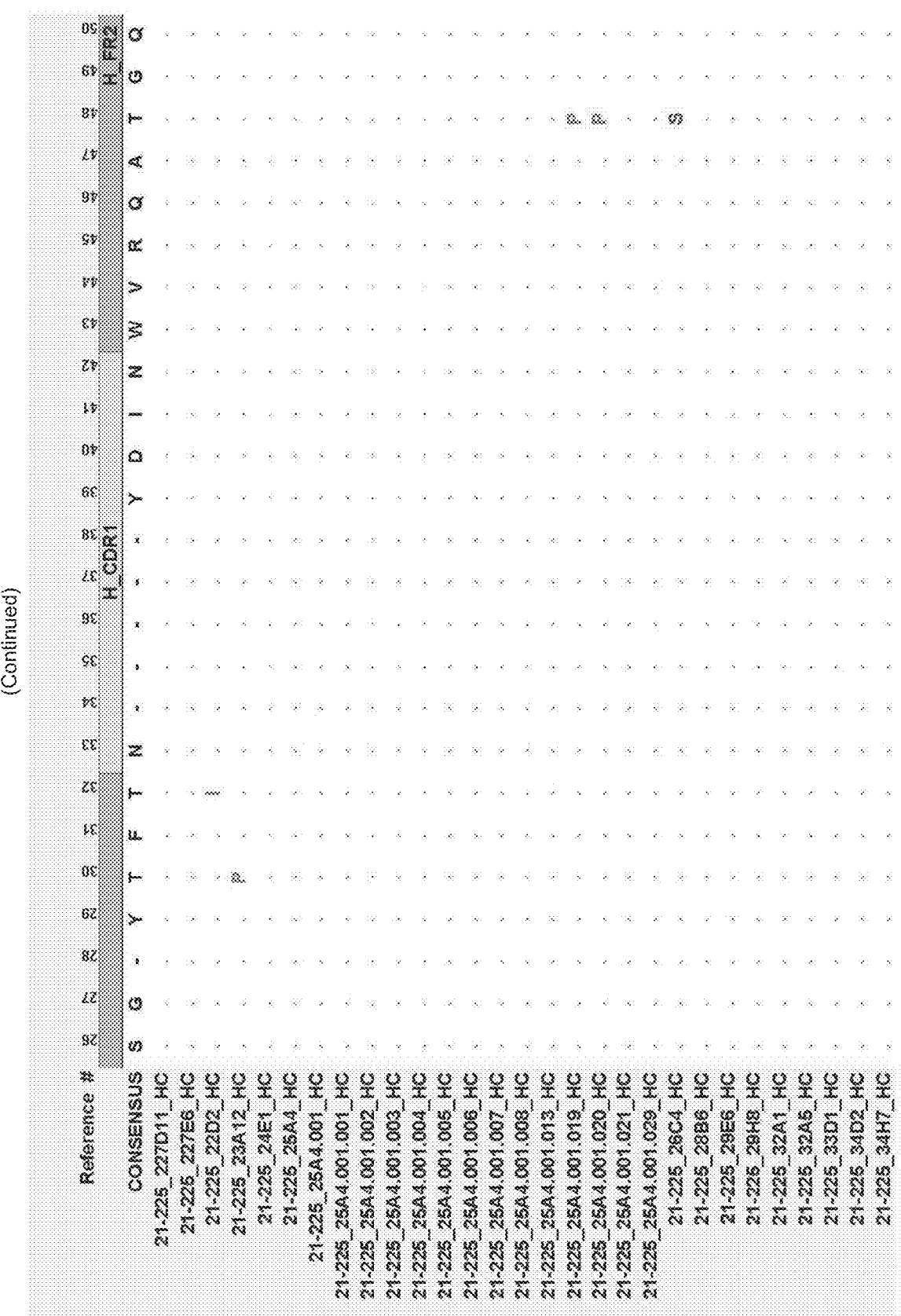
Figure 57:
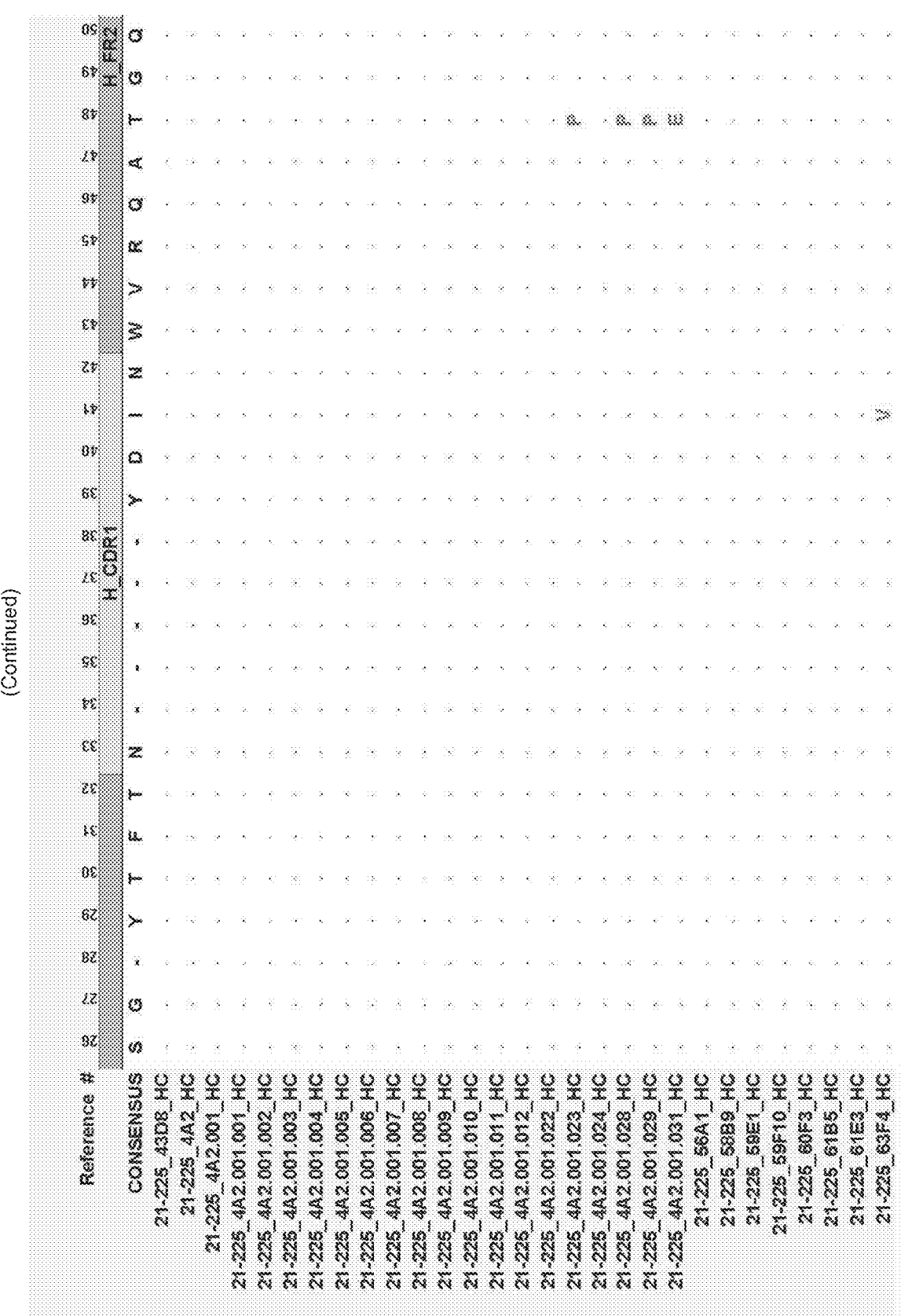
Figure 57:
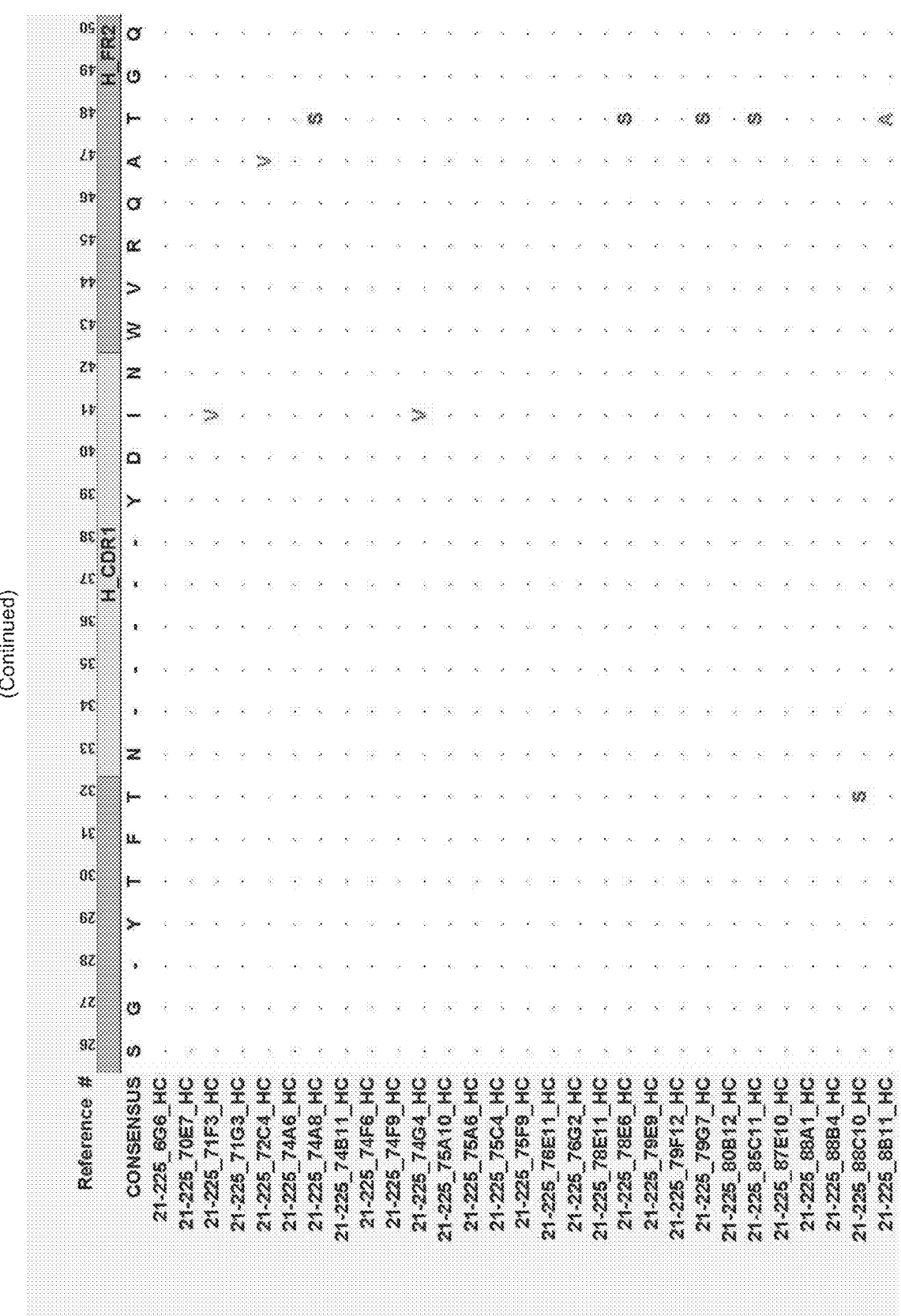
Figure 57:
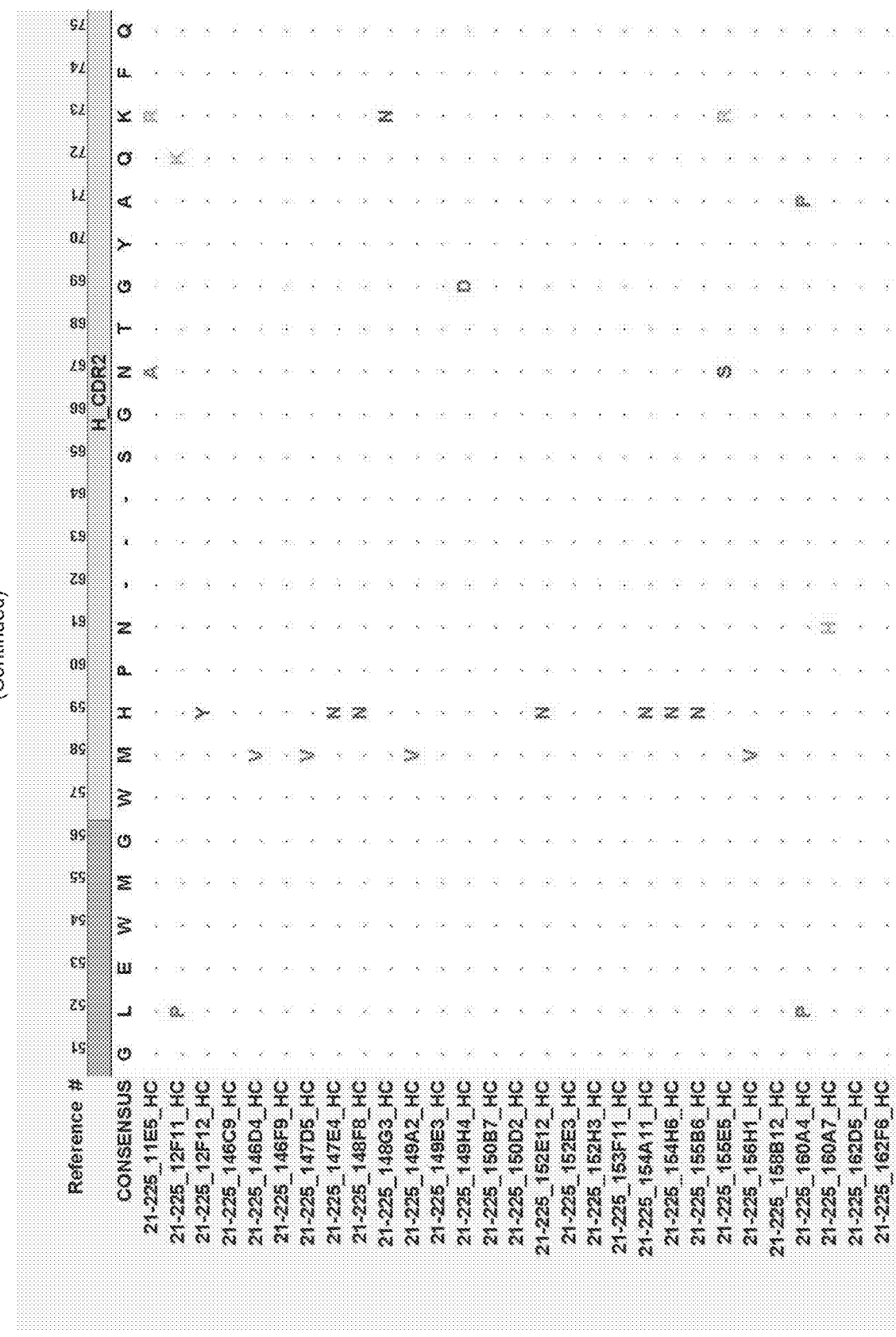
Figure 57:
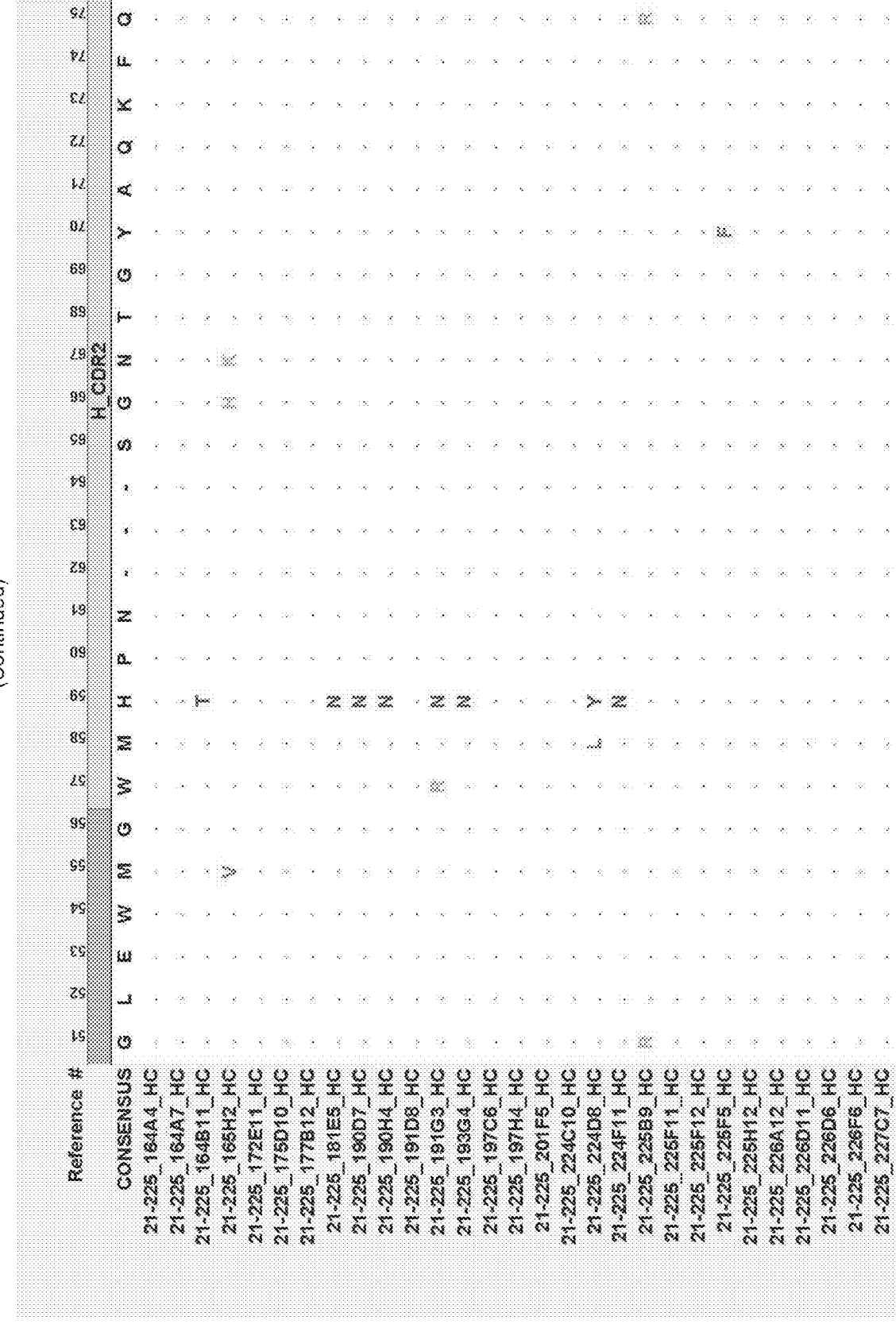
Figure 57:
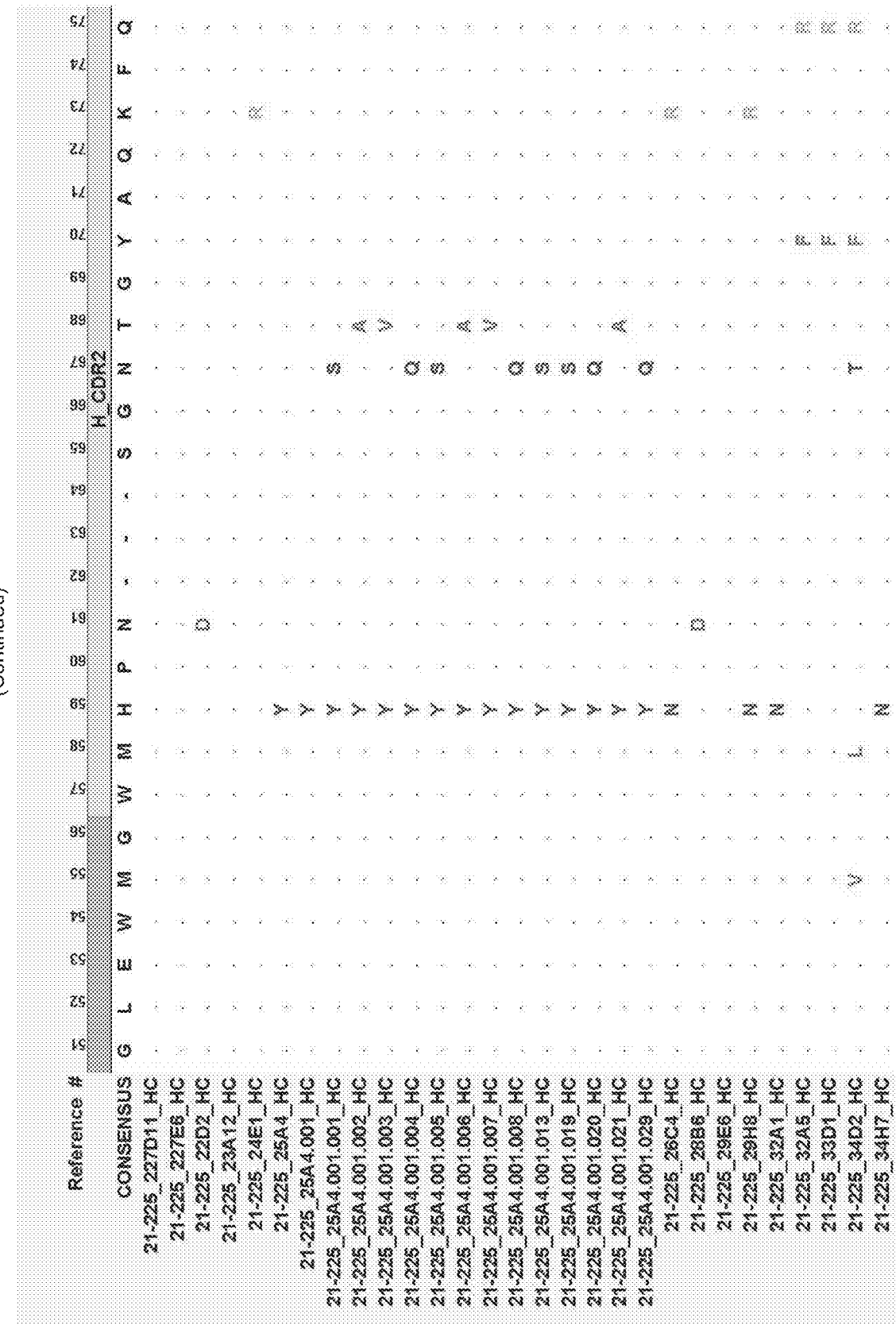
Figure 57:
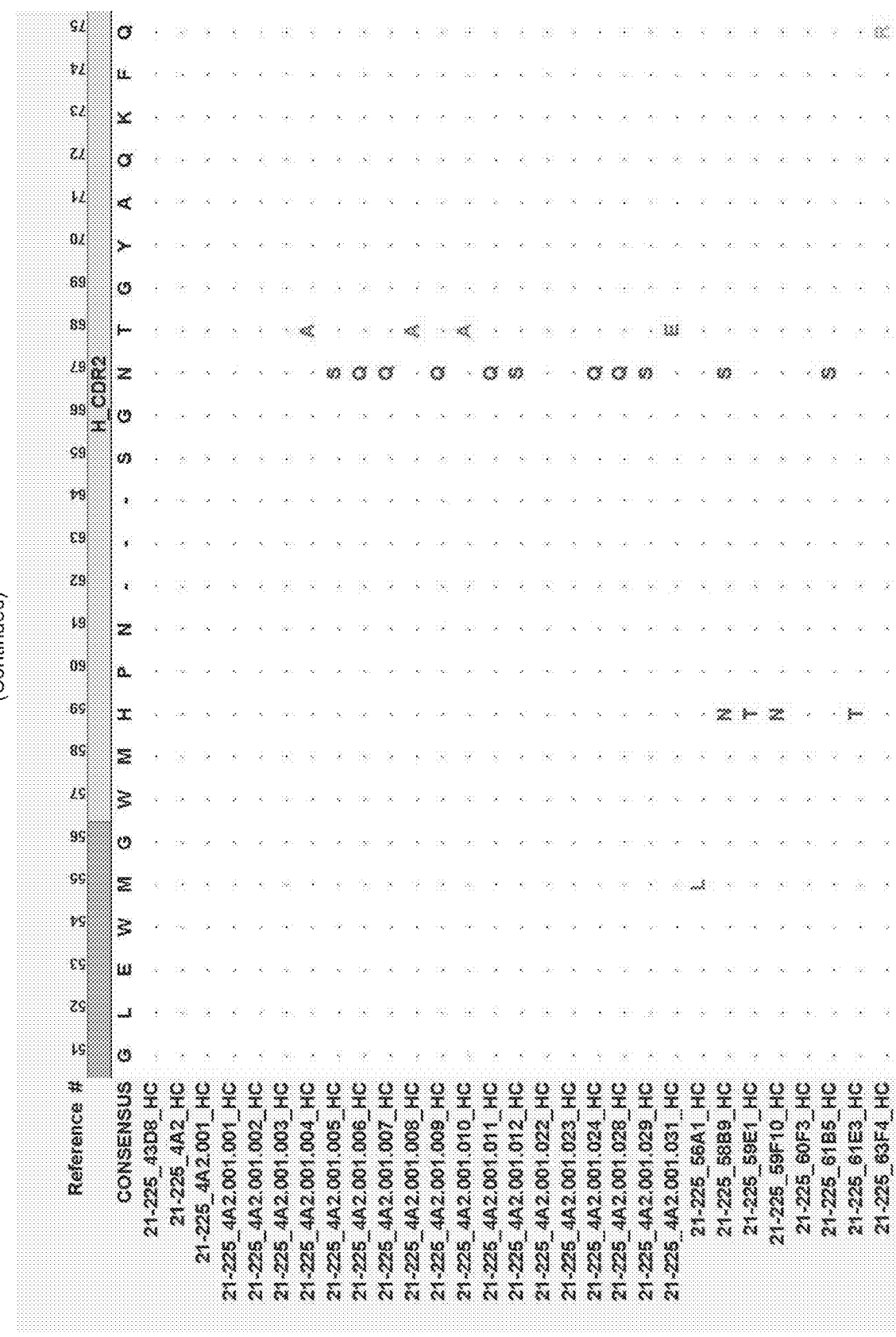
Figure 57:
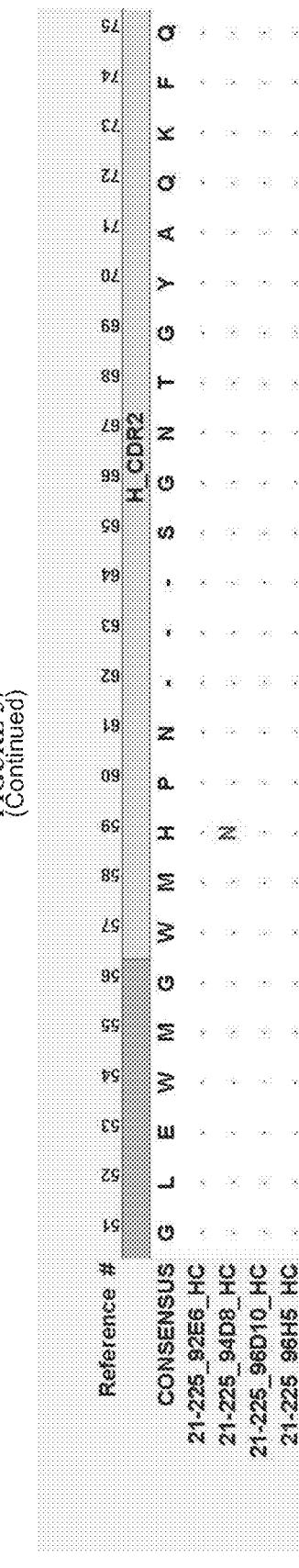
Figure 57:
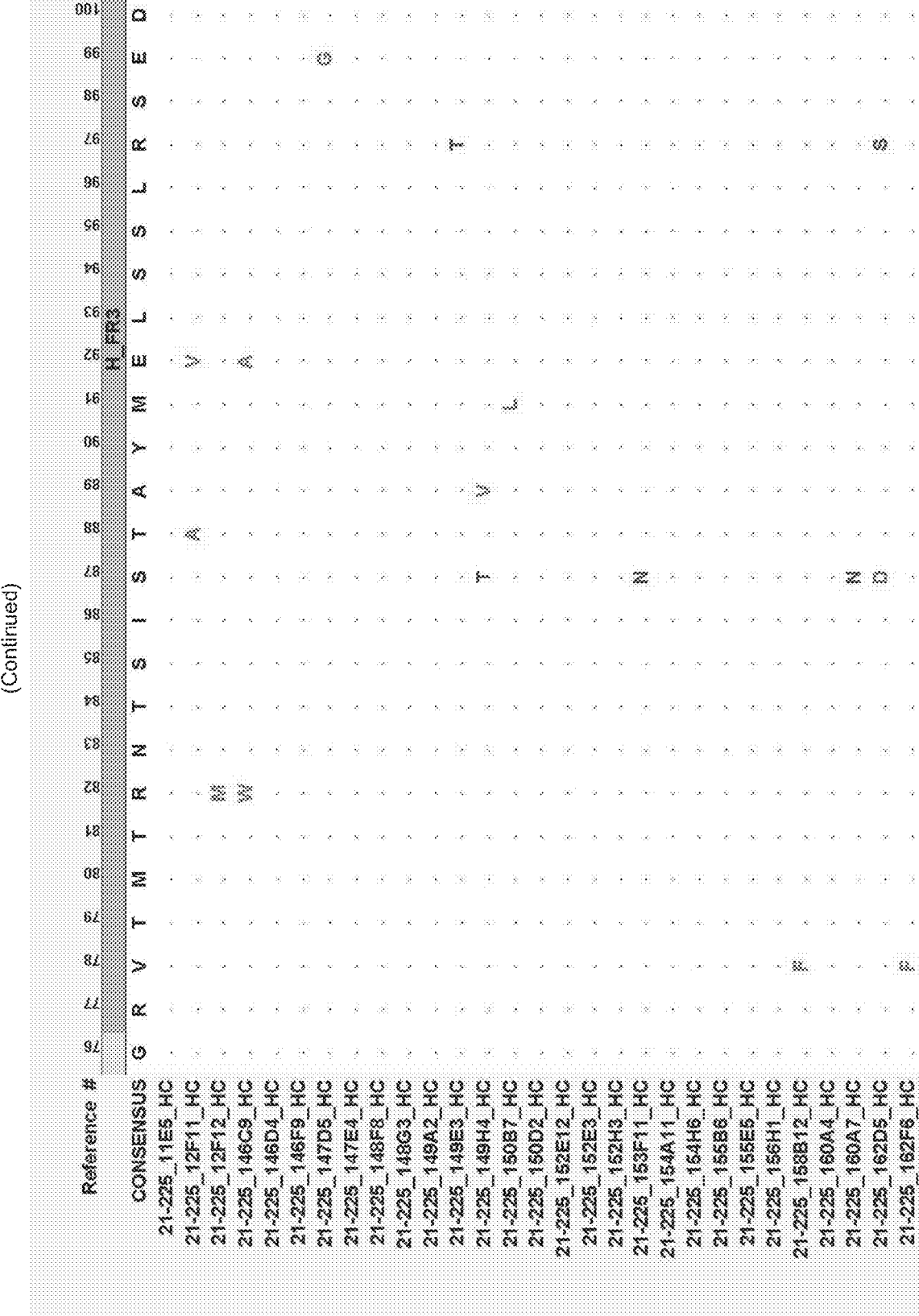
Figure 57:
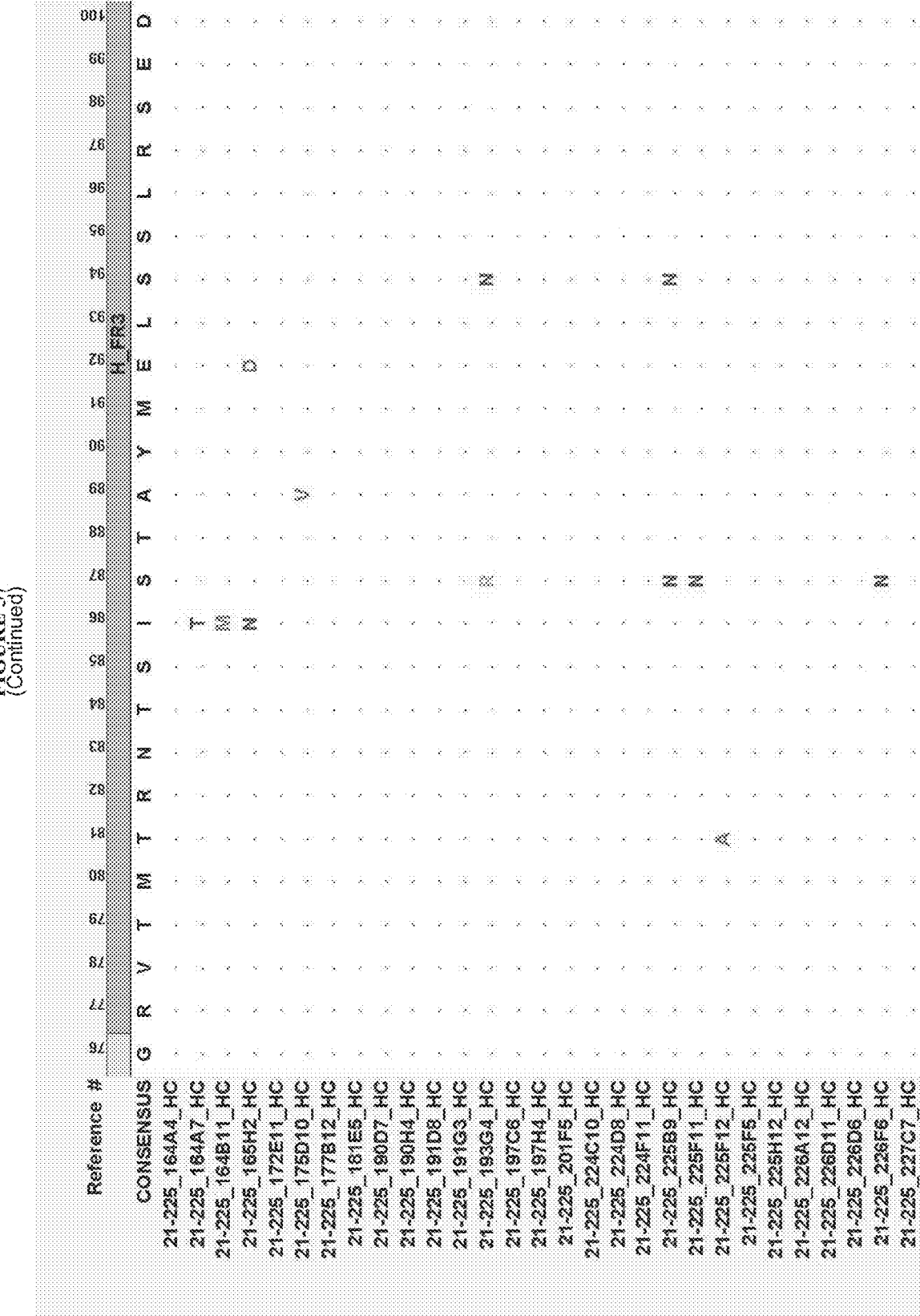
Figure 57:
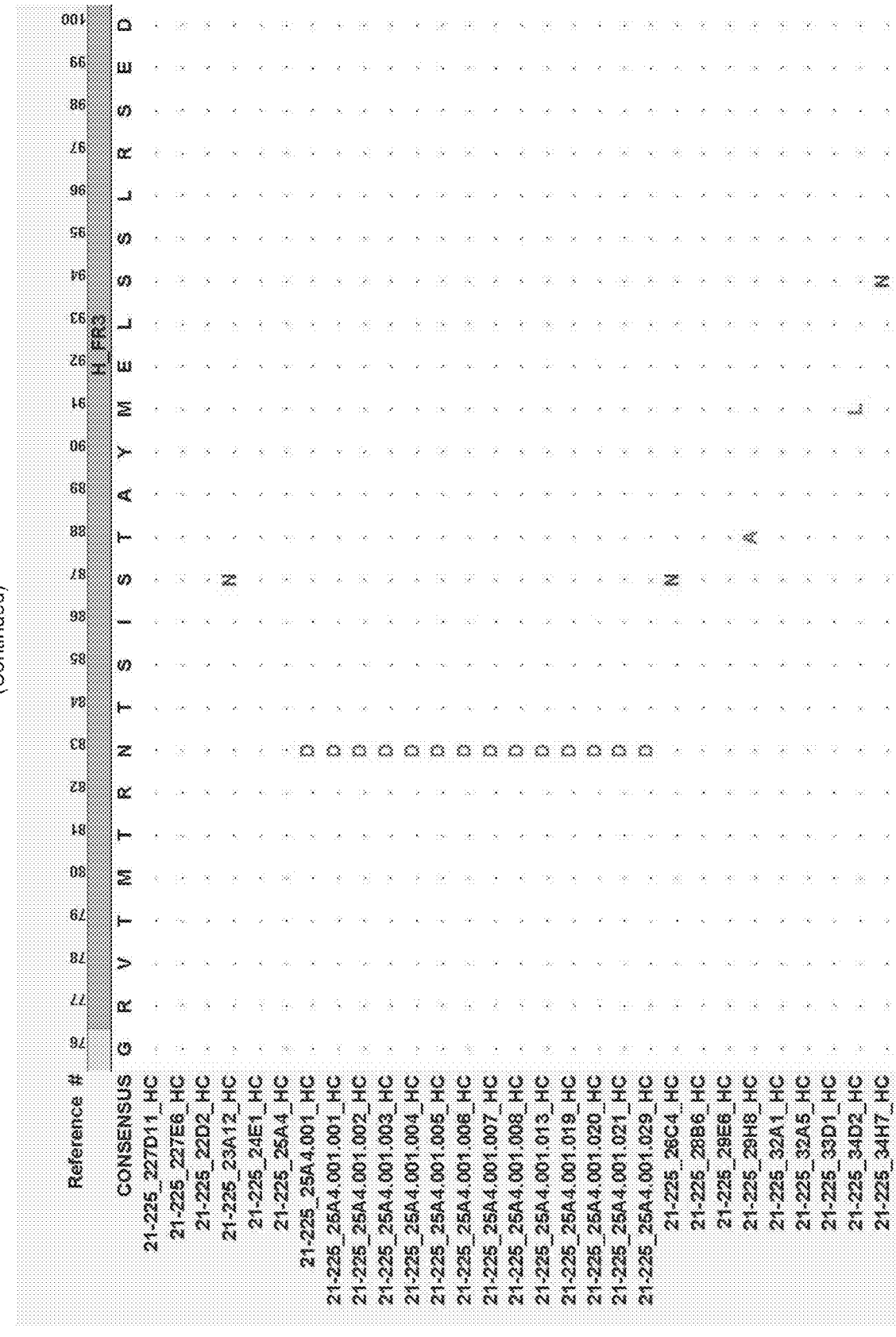
Figure 57:
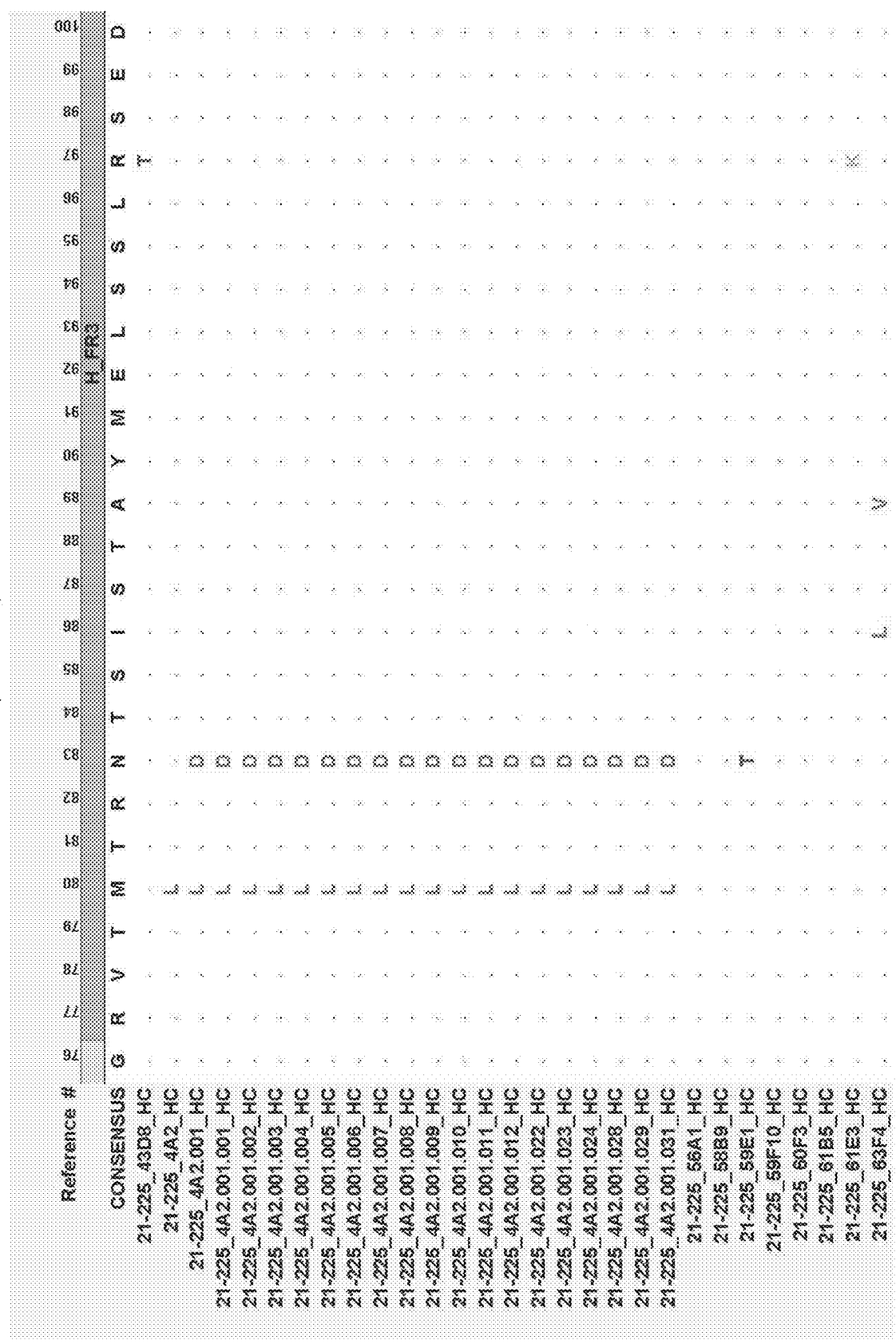
Figure 57:
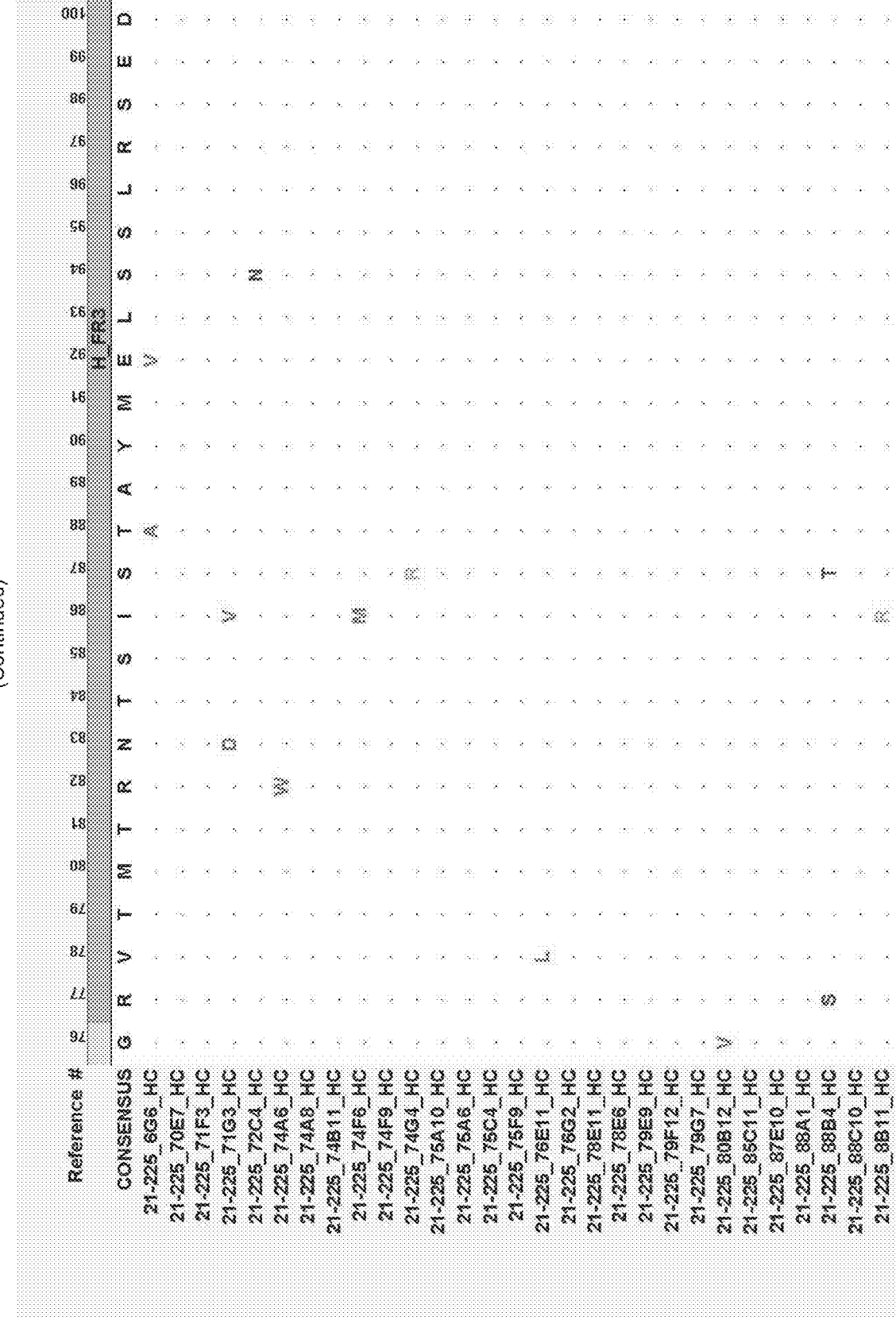
Figure 57:
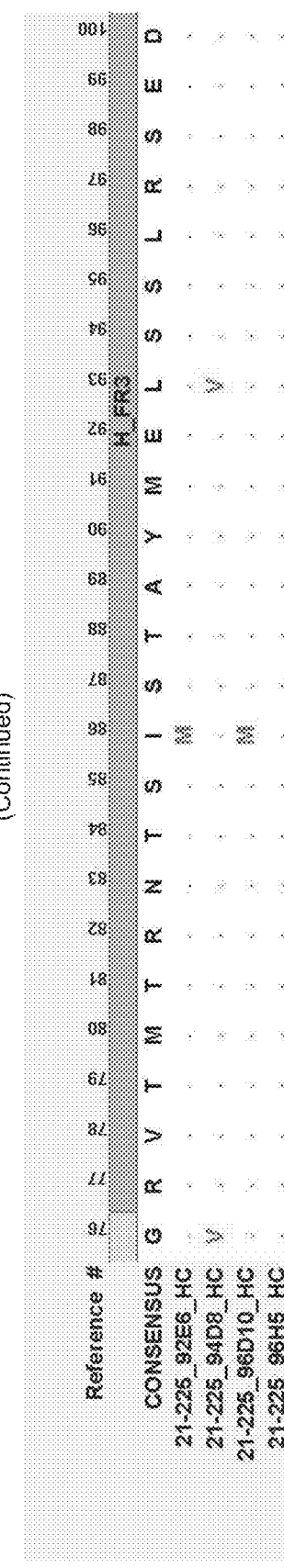
Figure 57:
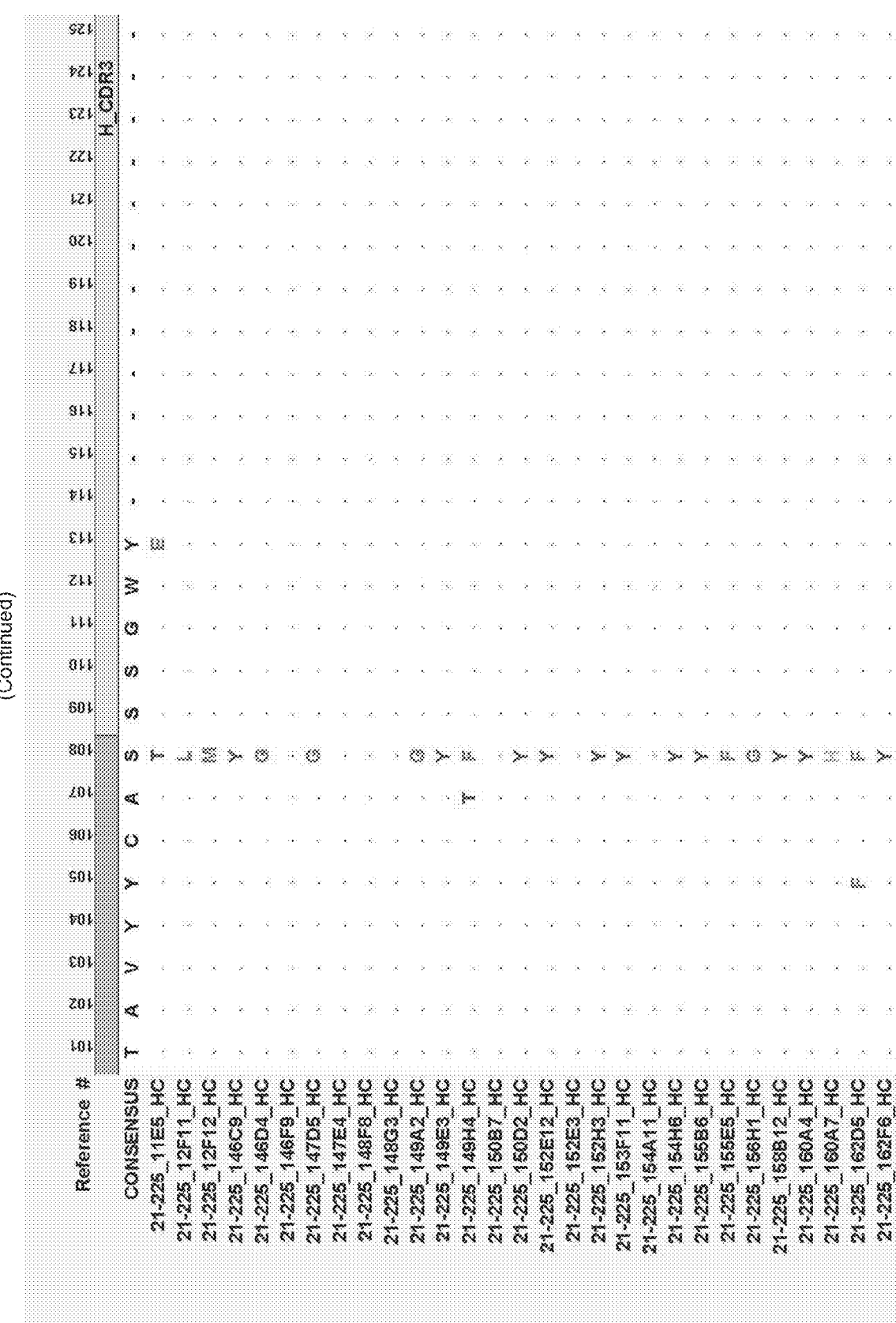
Figure 57:
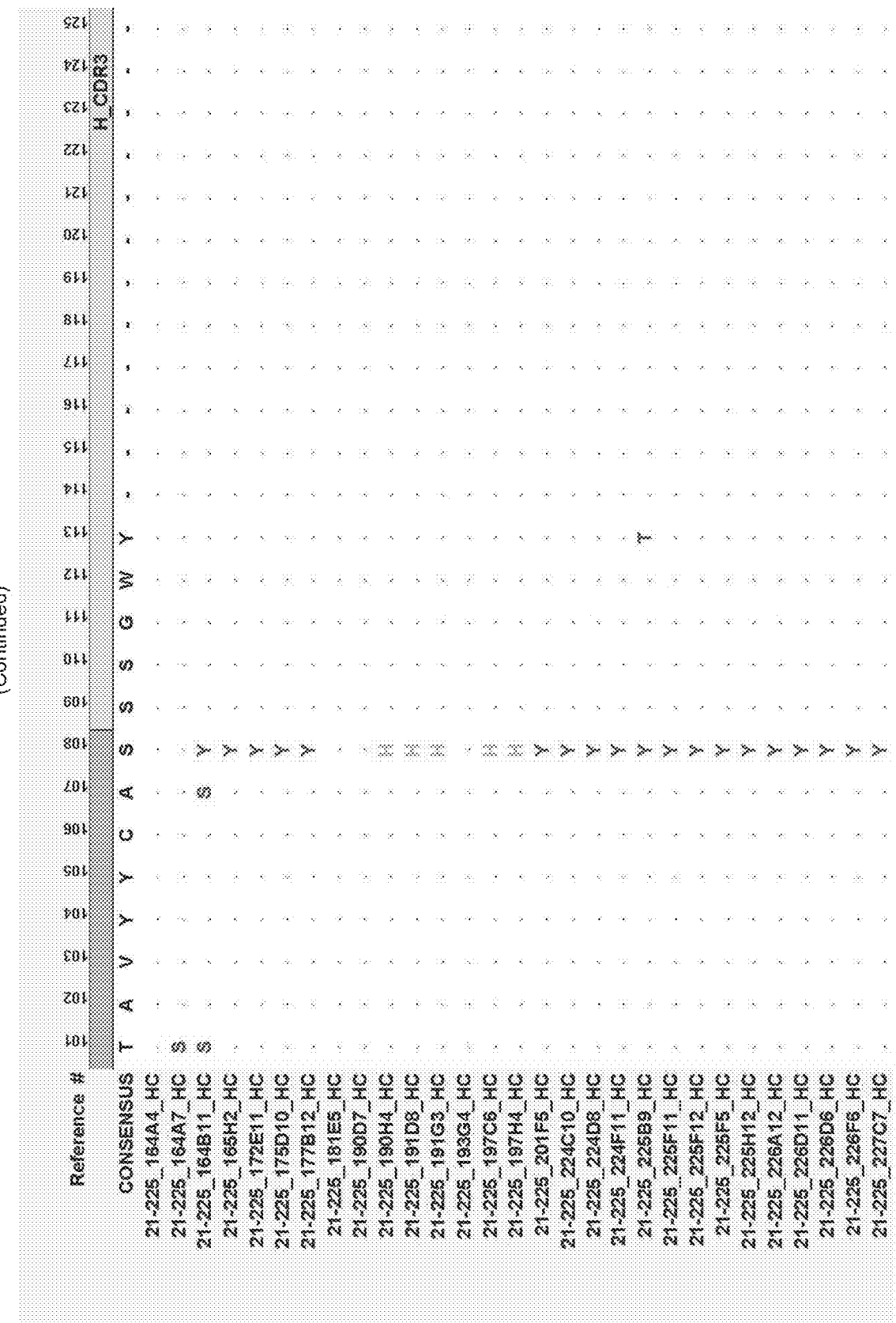
Figure 57:
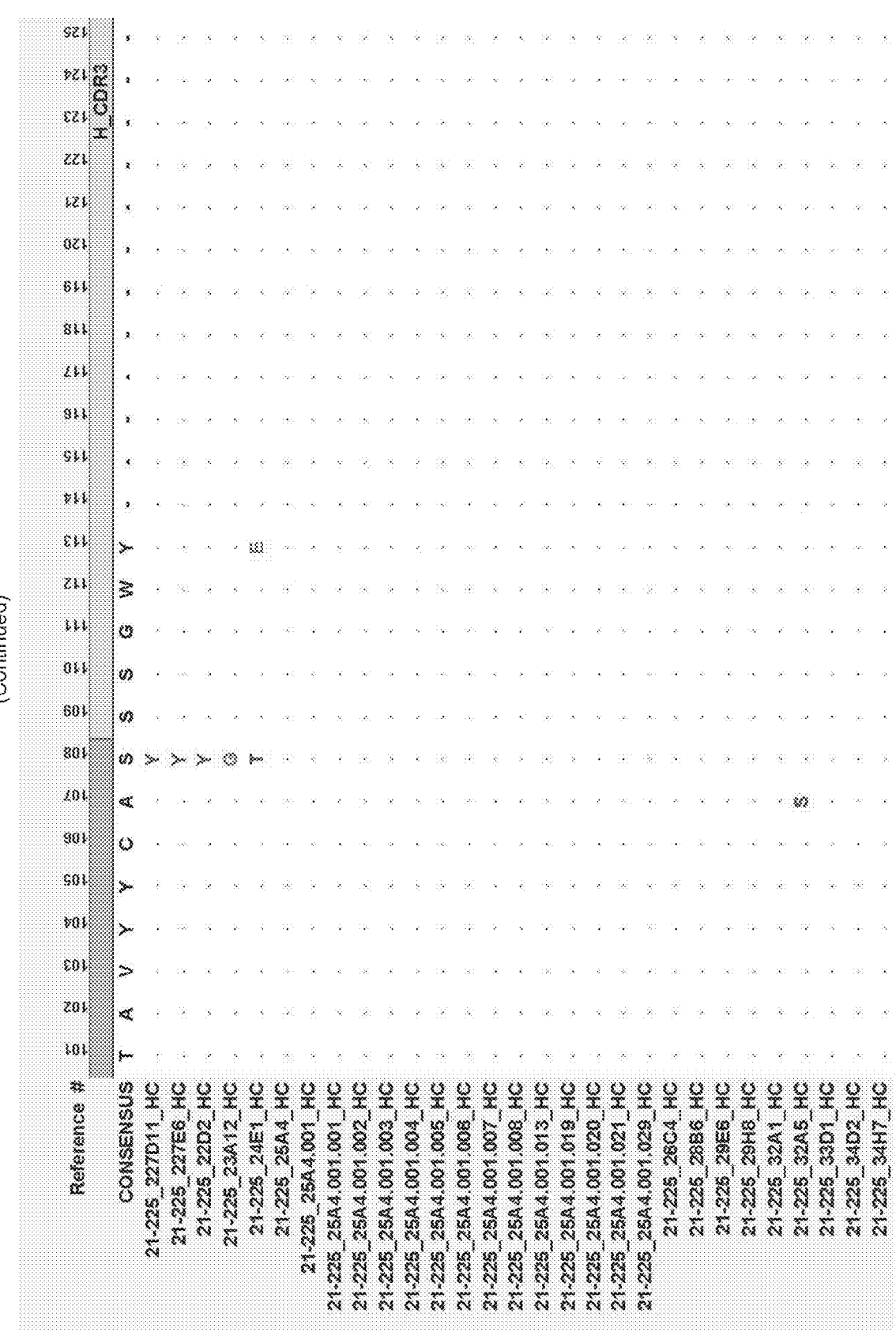
Figure 57:
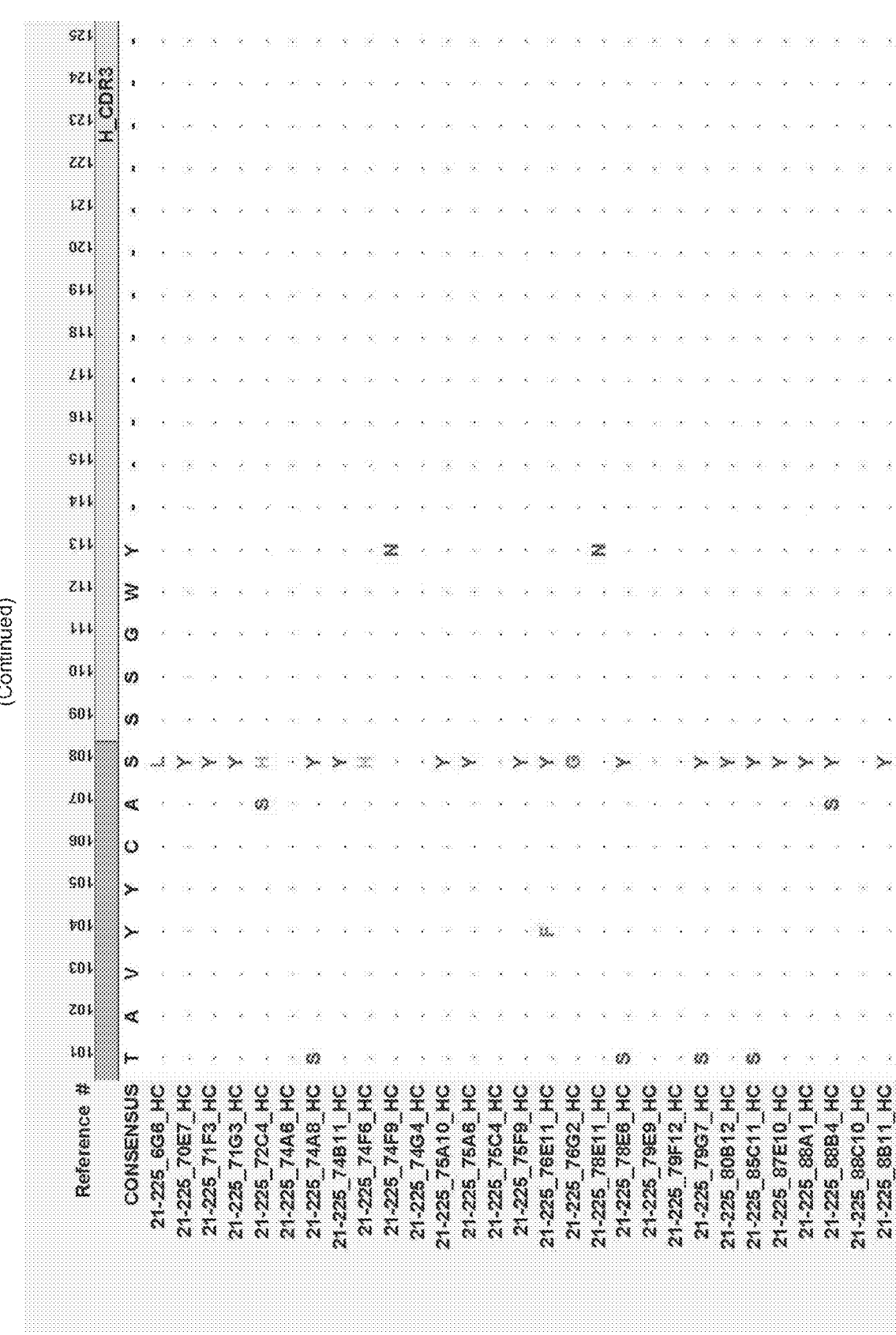
Figure 57:
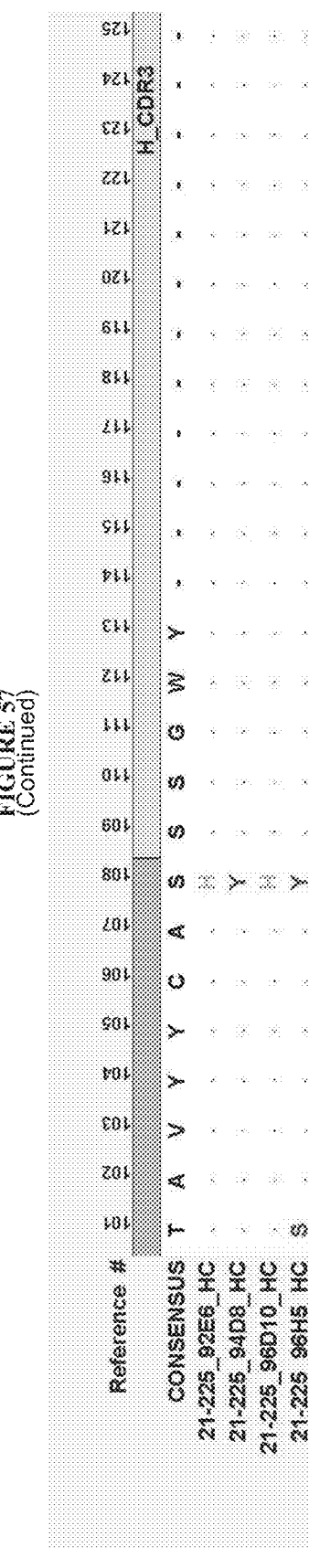
Figure 57:
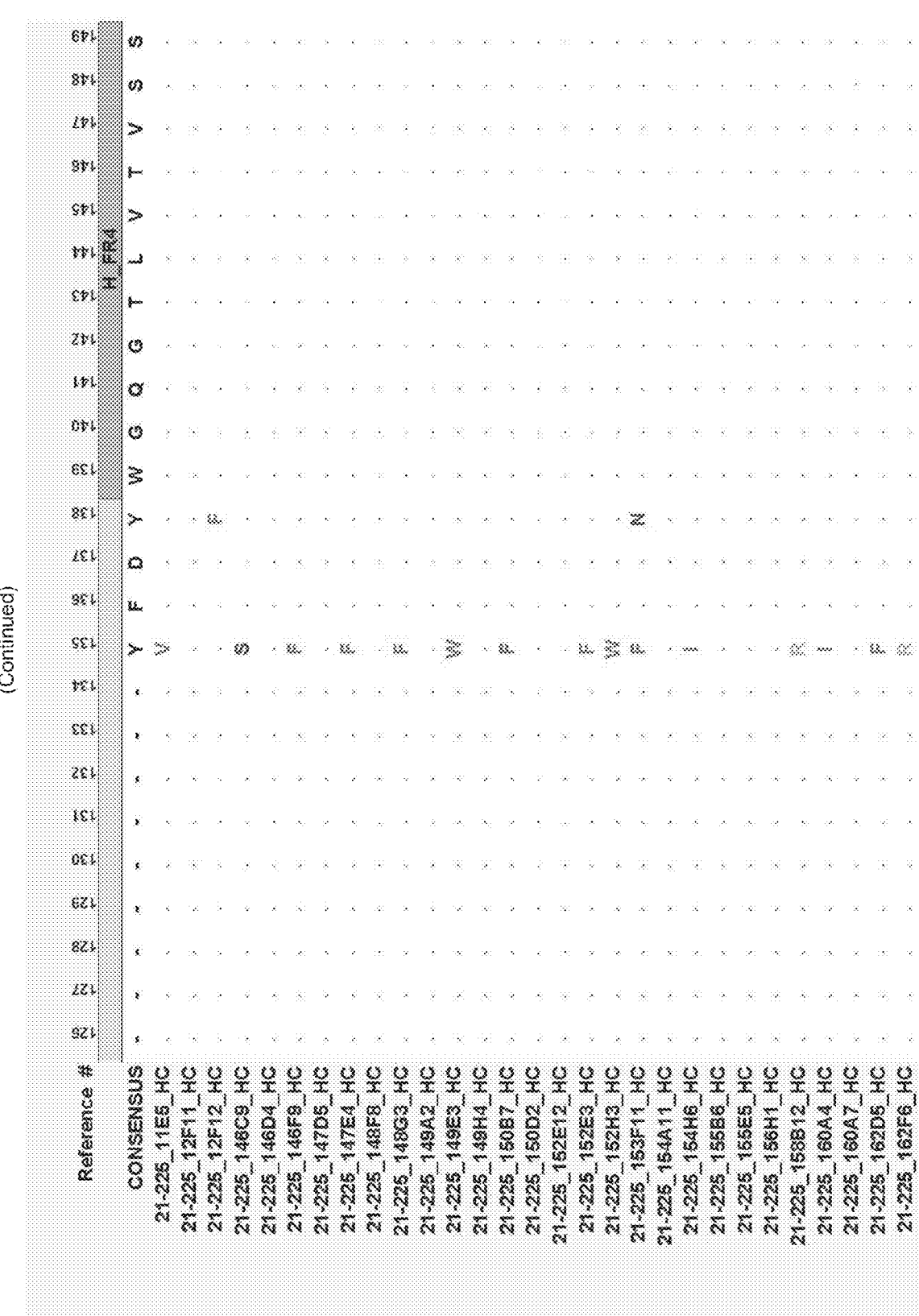
Figure 57:
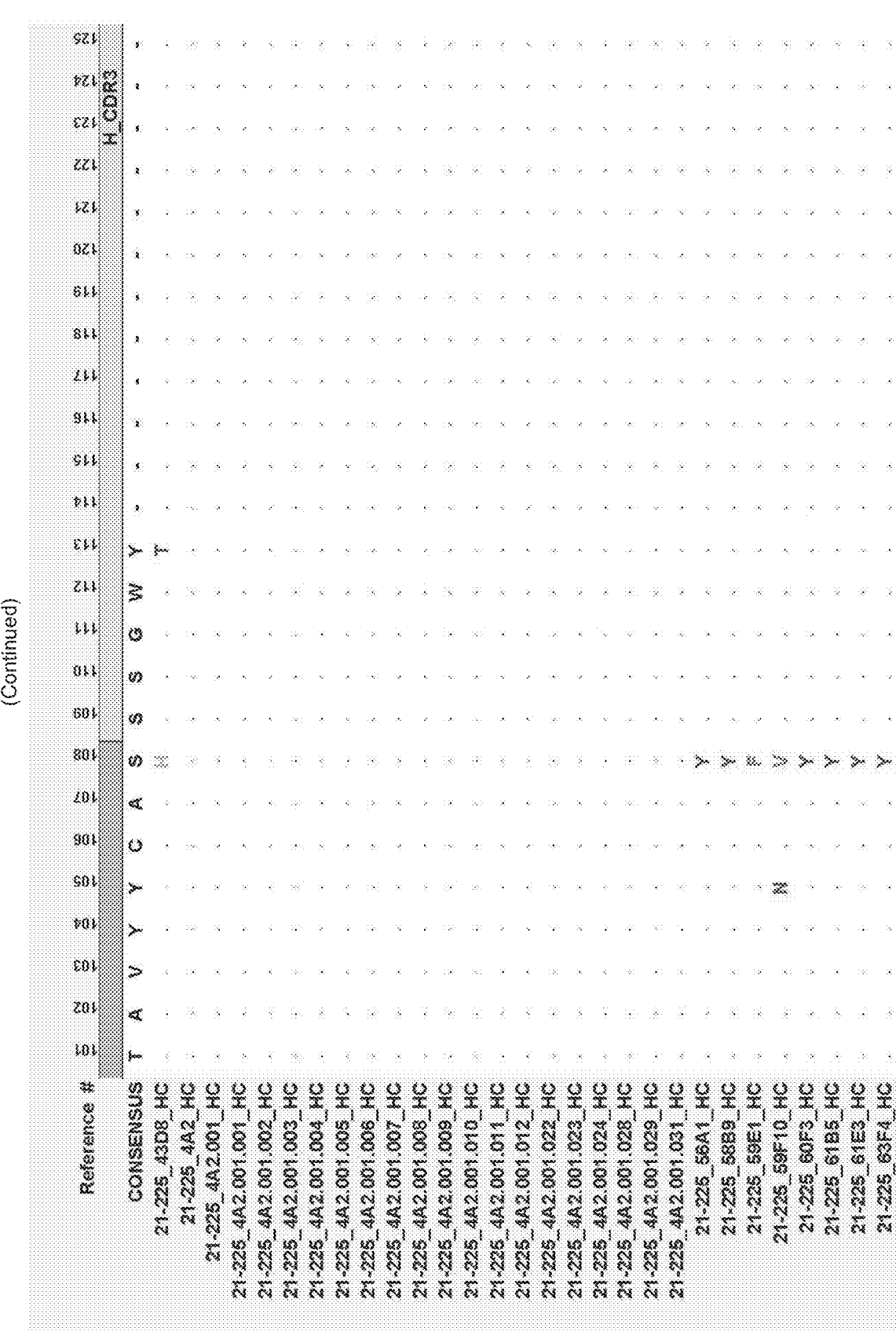
Figure 57:
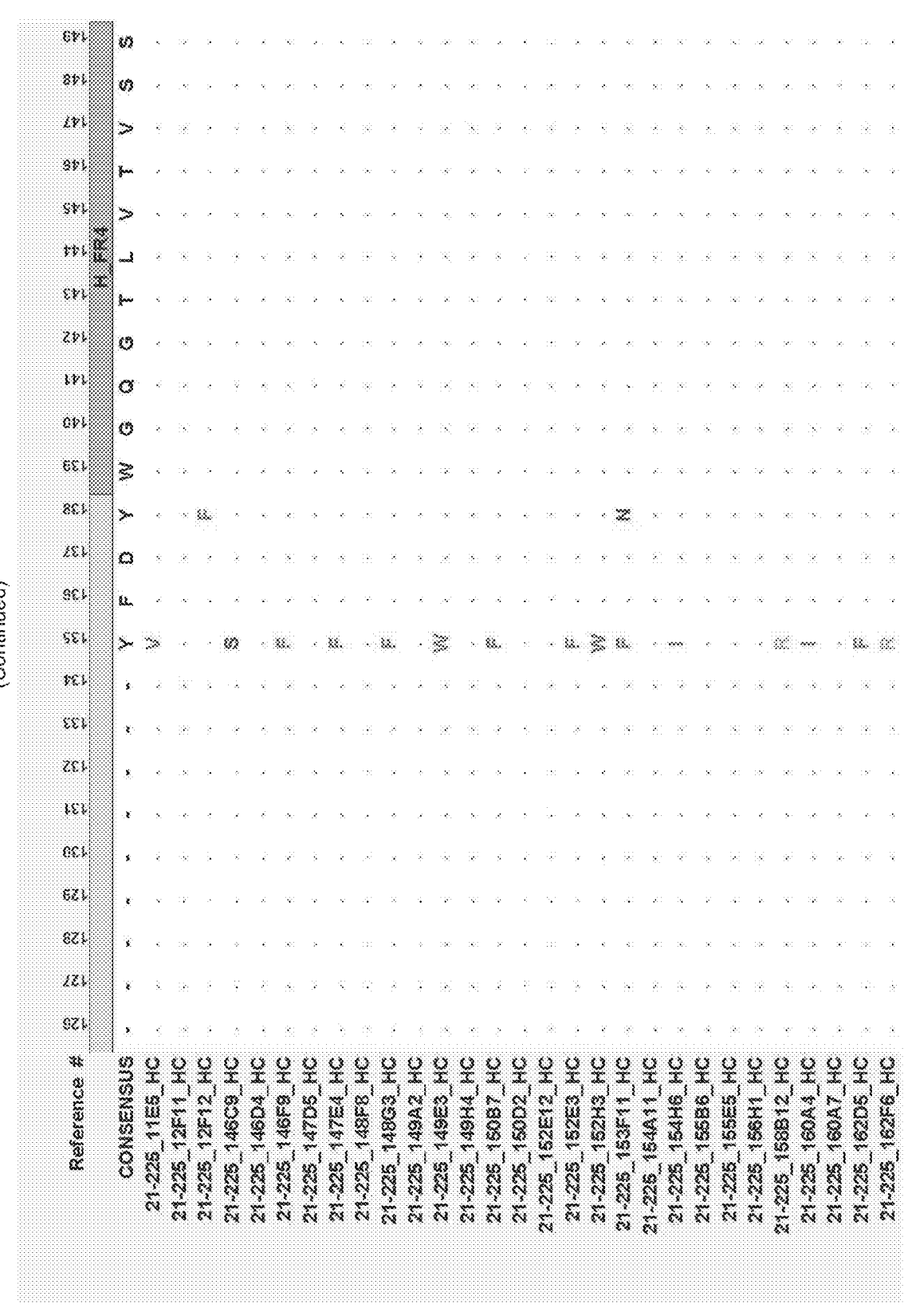
Figure 57:
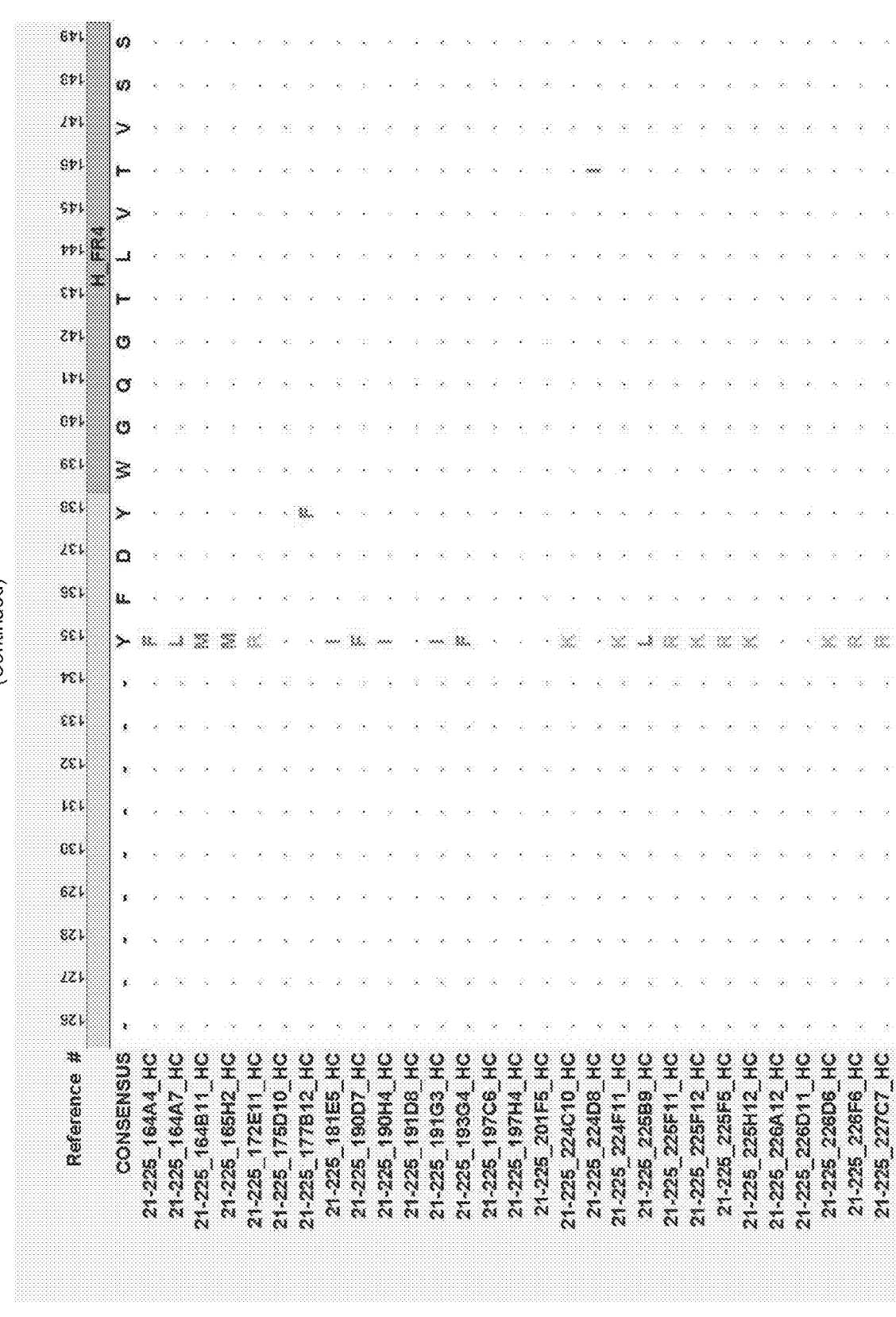
Figure 57:
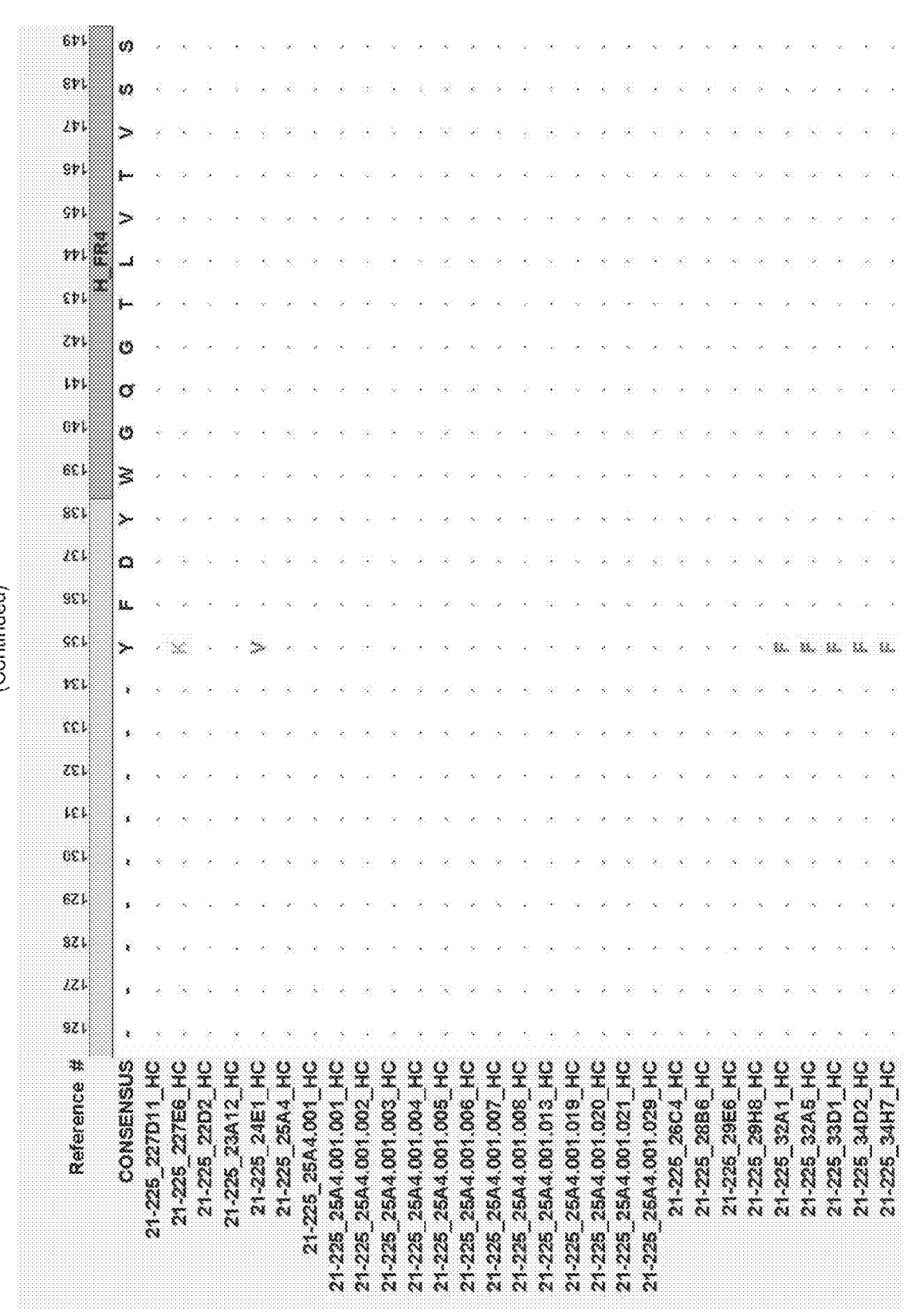
Figure 57:
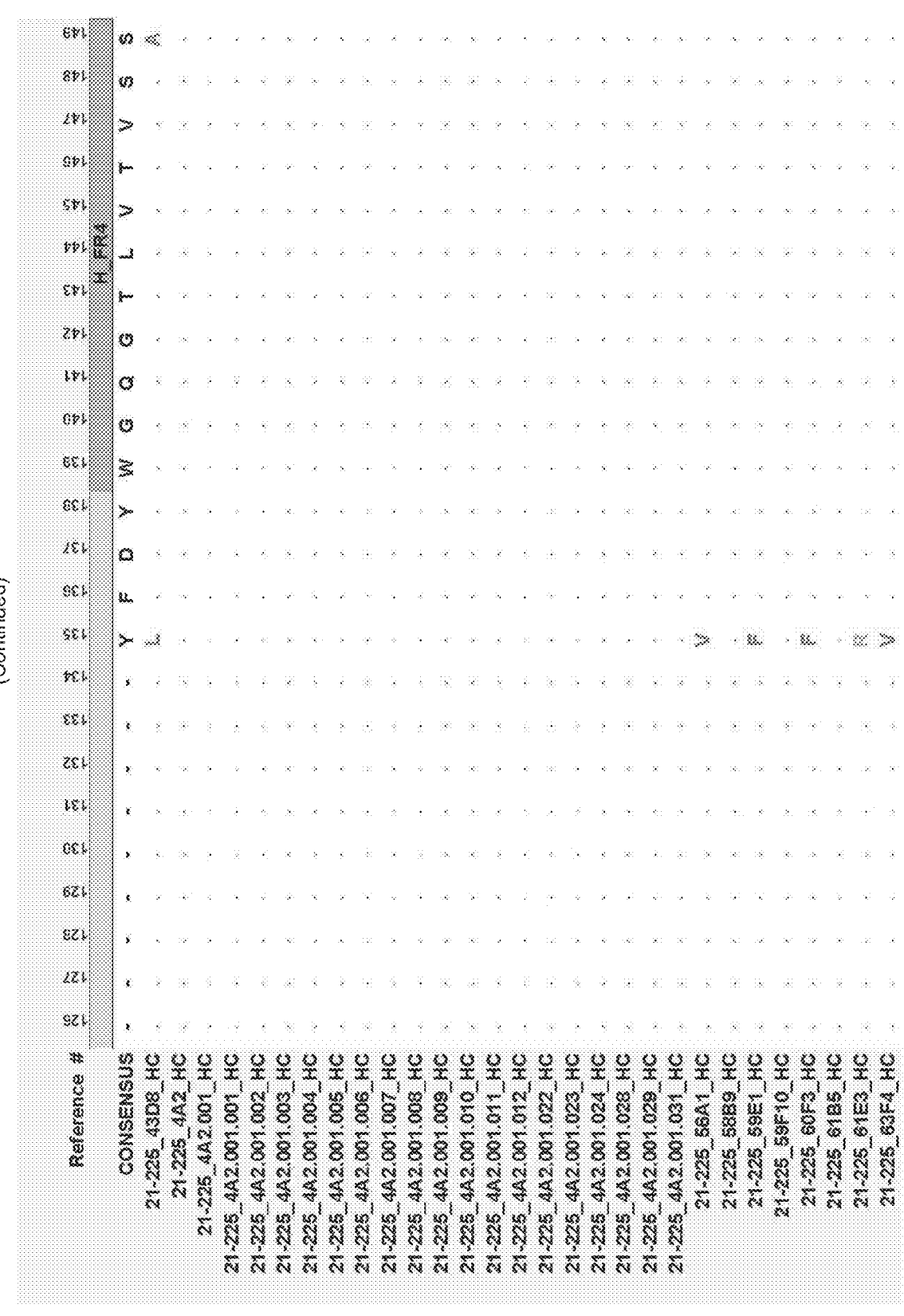
Figure 57:
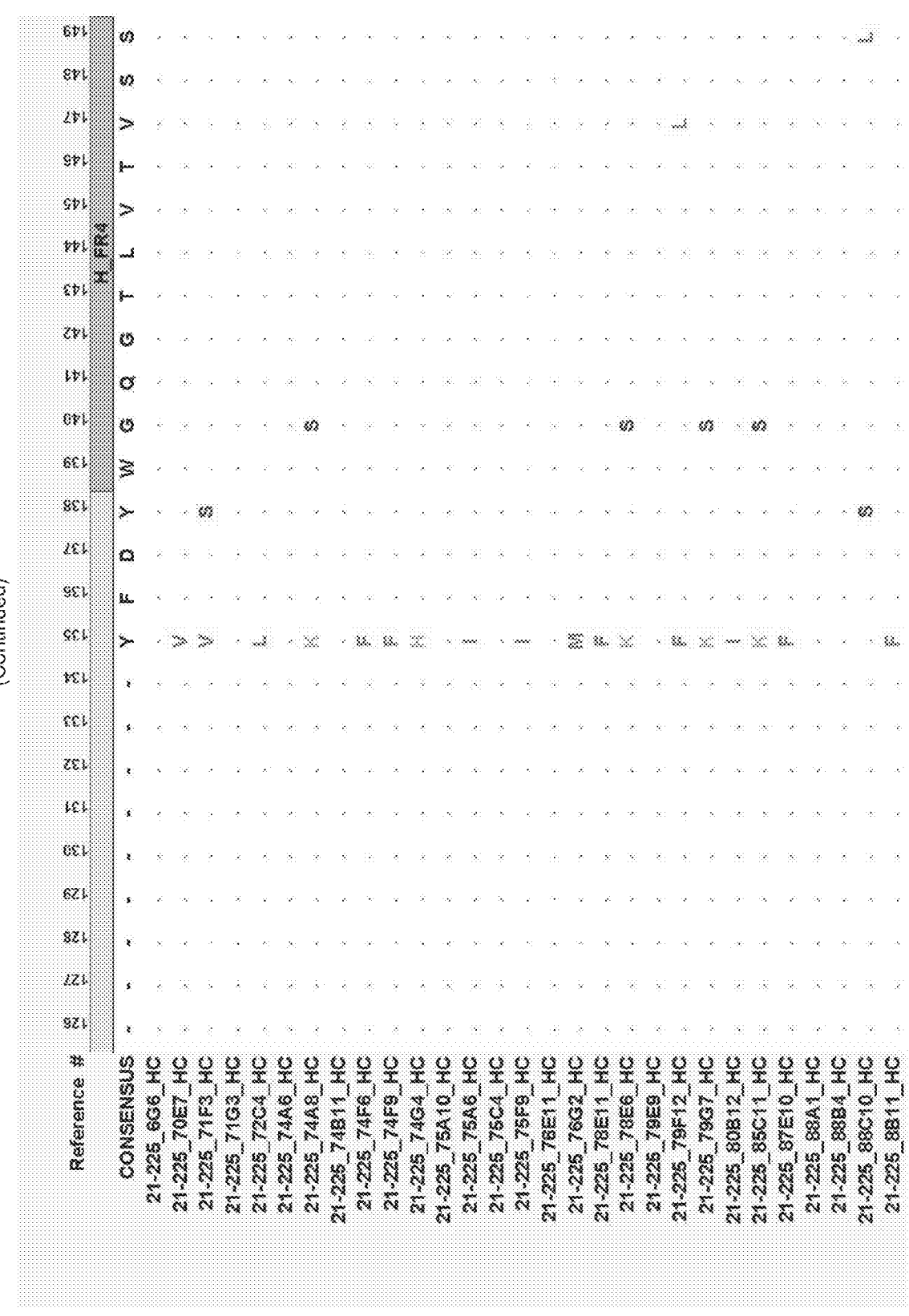
Figure 57:
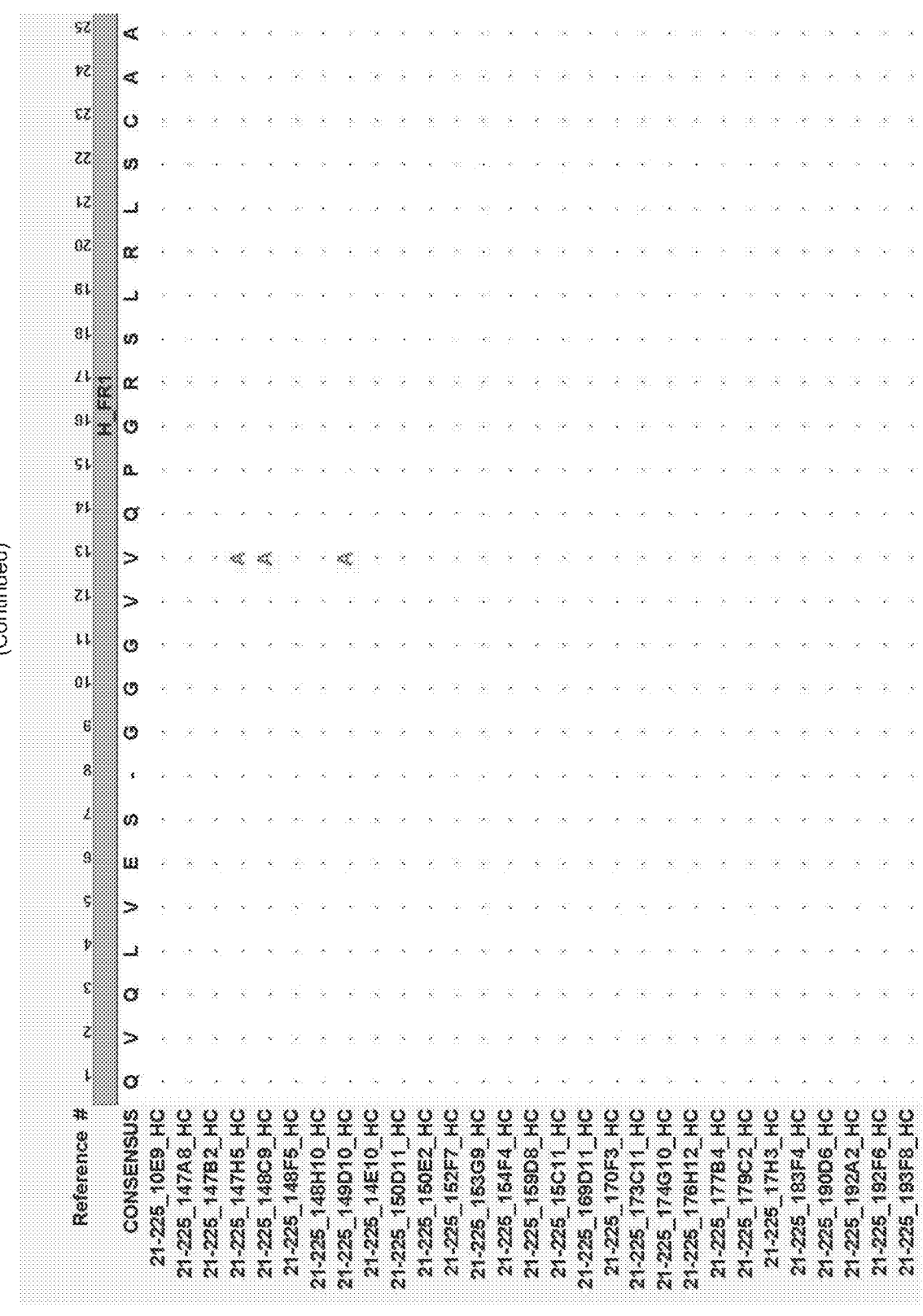
Figure 57:
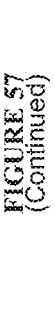
Figure 57:
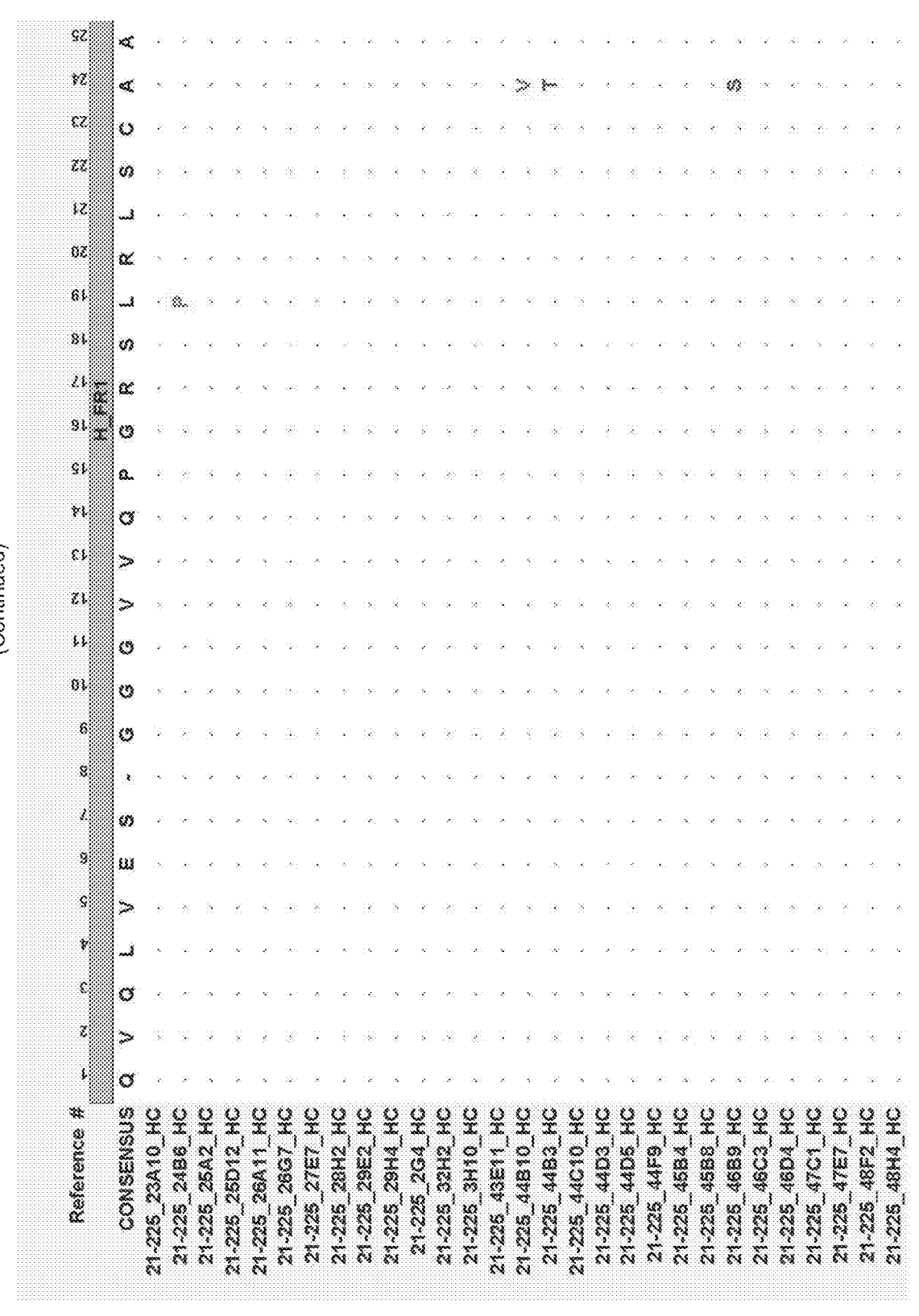
Figure 57:
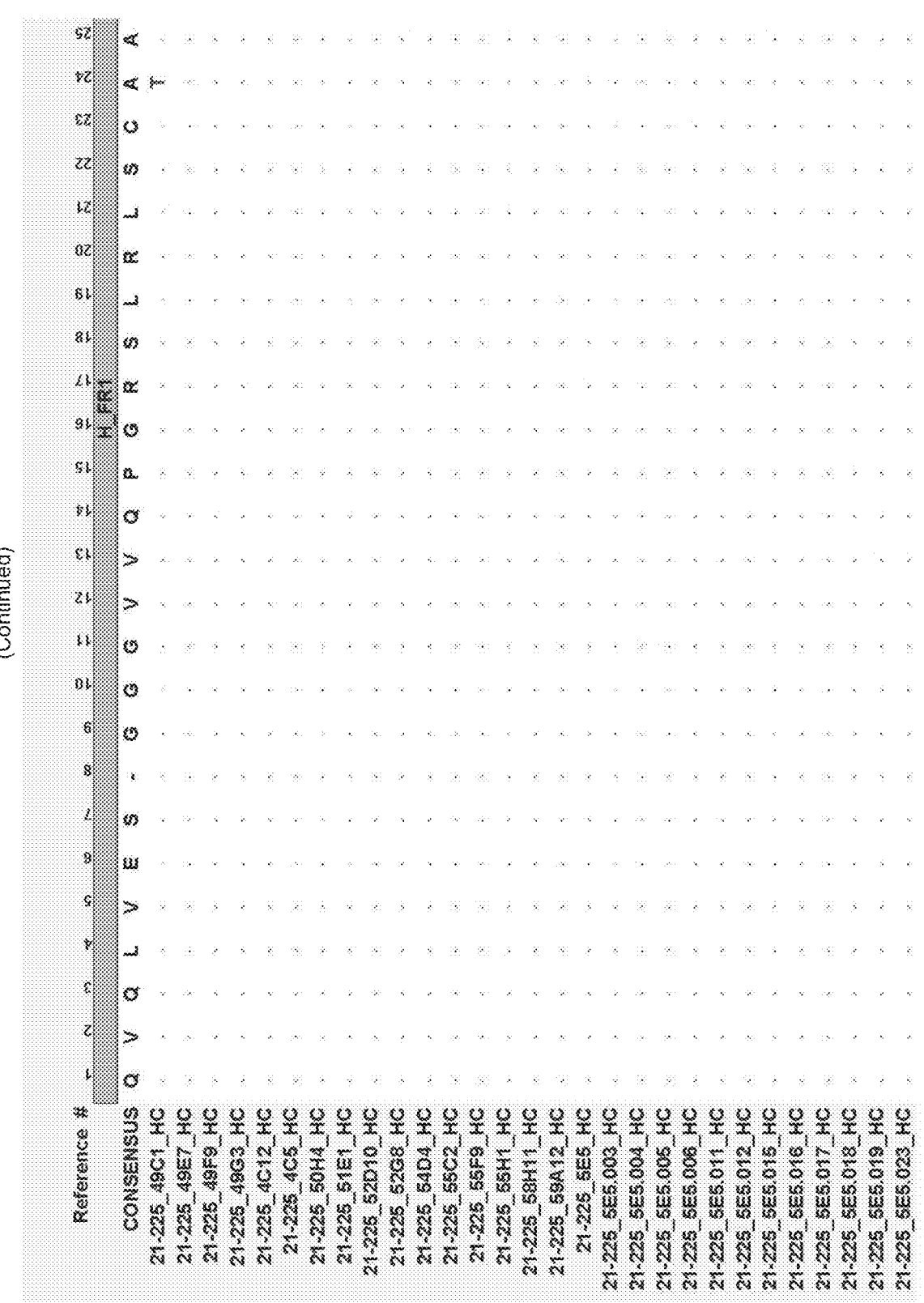
Figure 57:
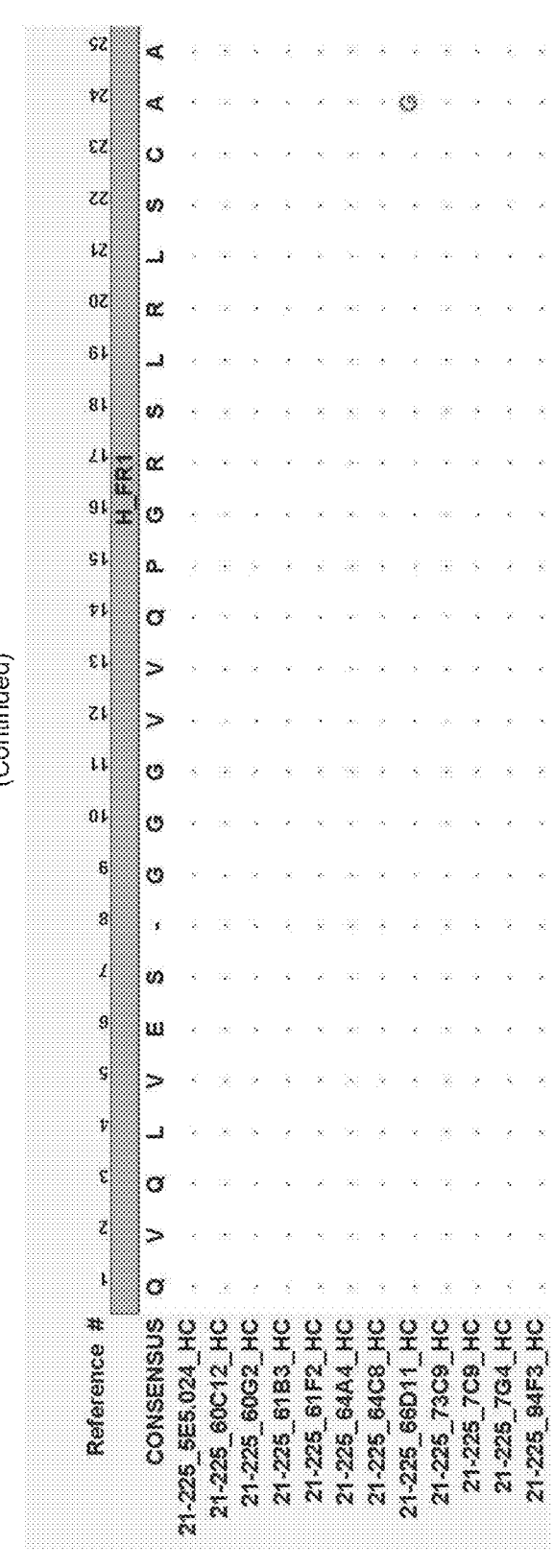
Figure 57:
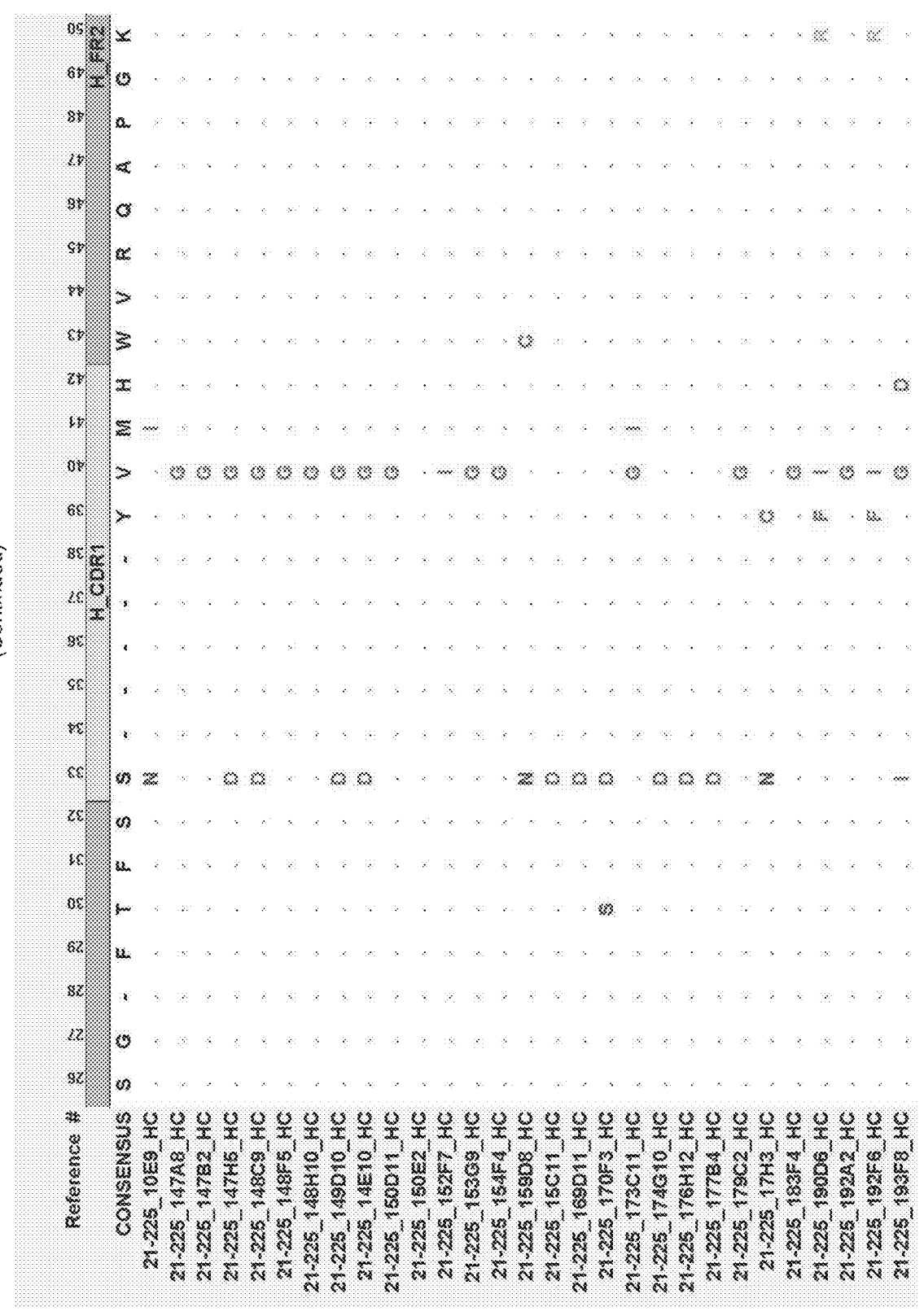
Figure 57:
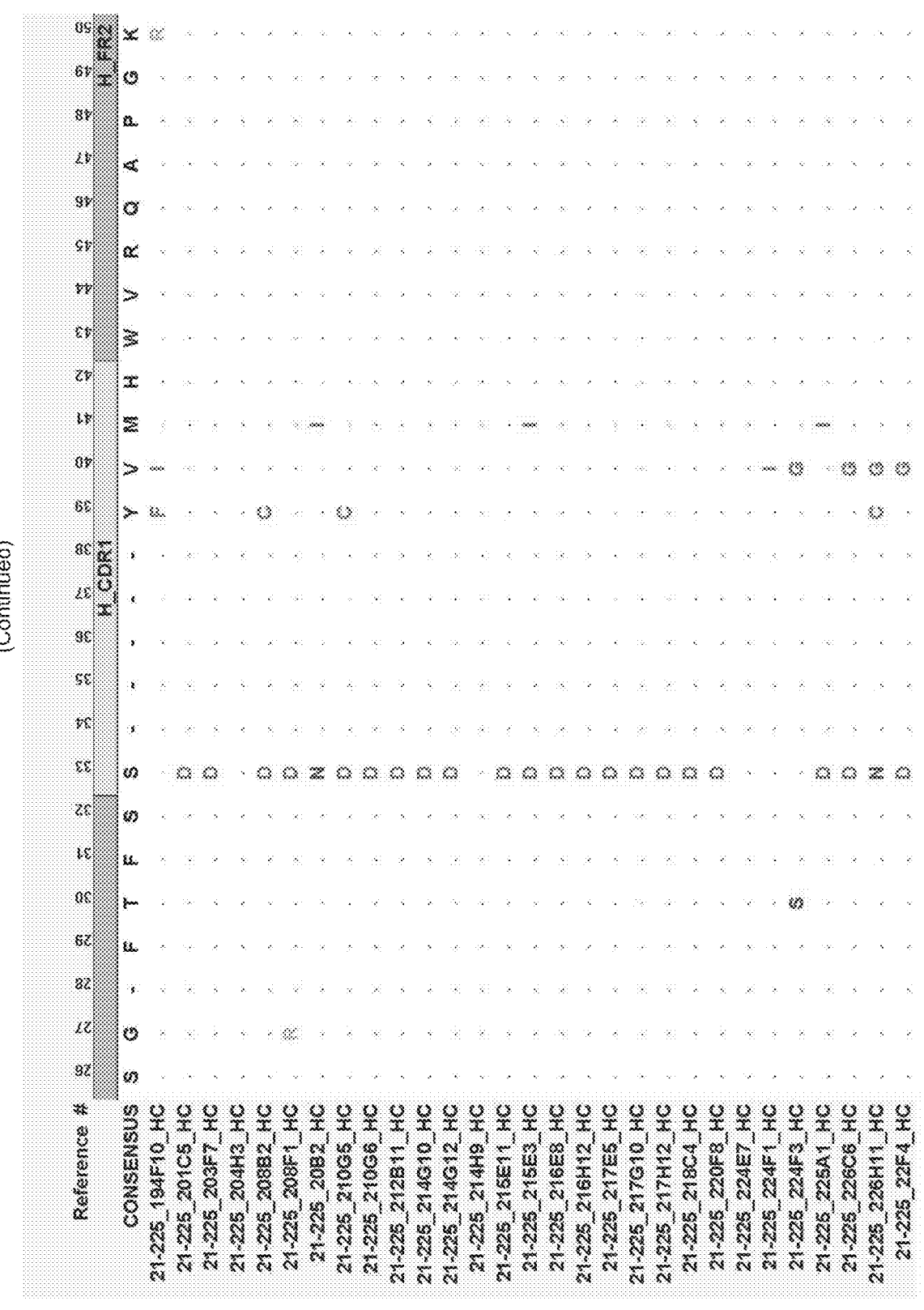
Figure 57:
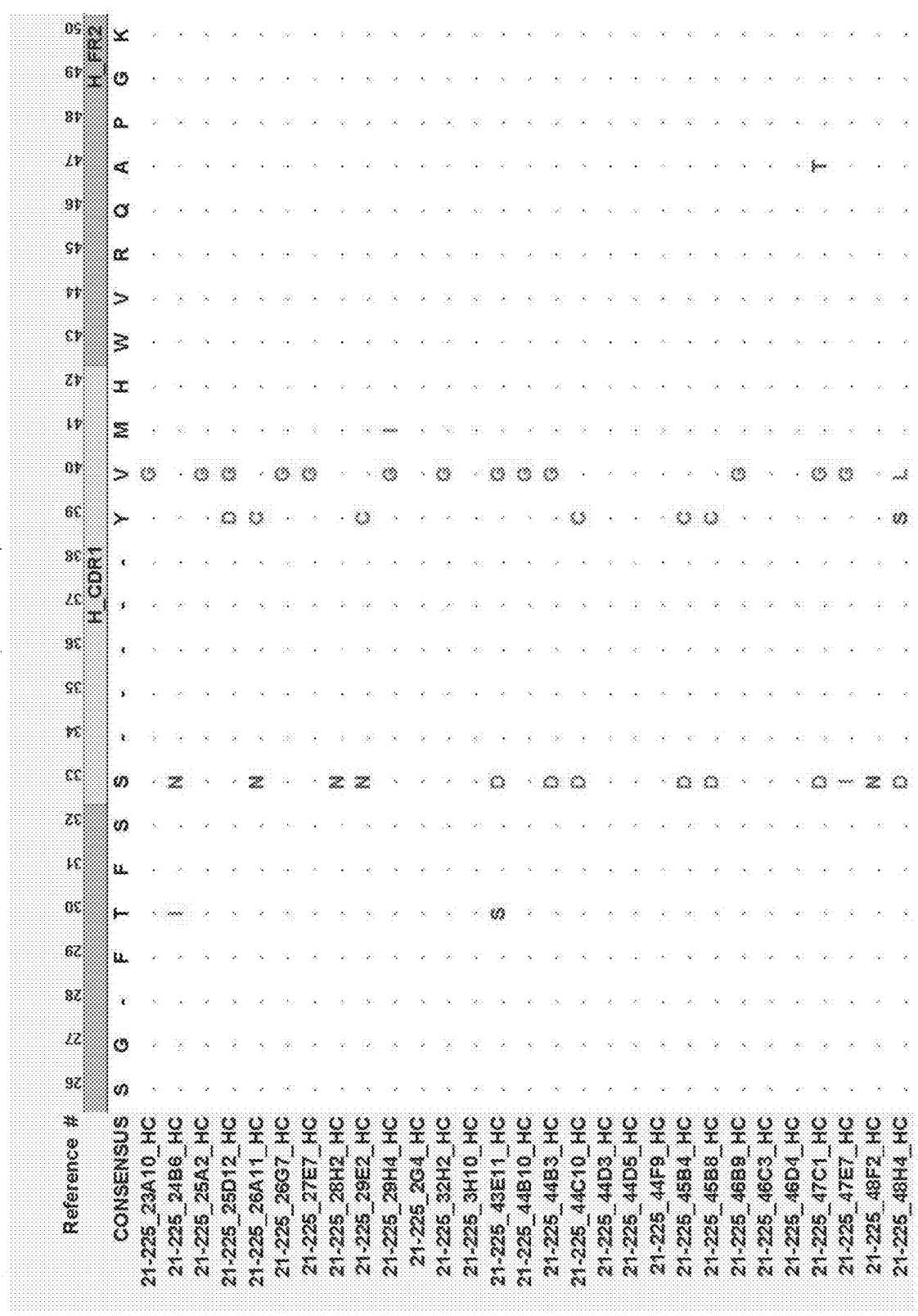
Figure 57:
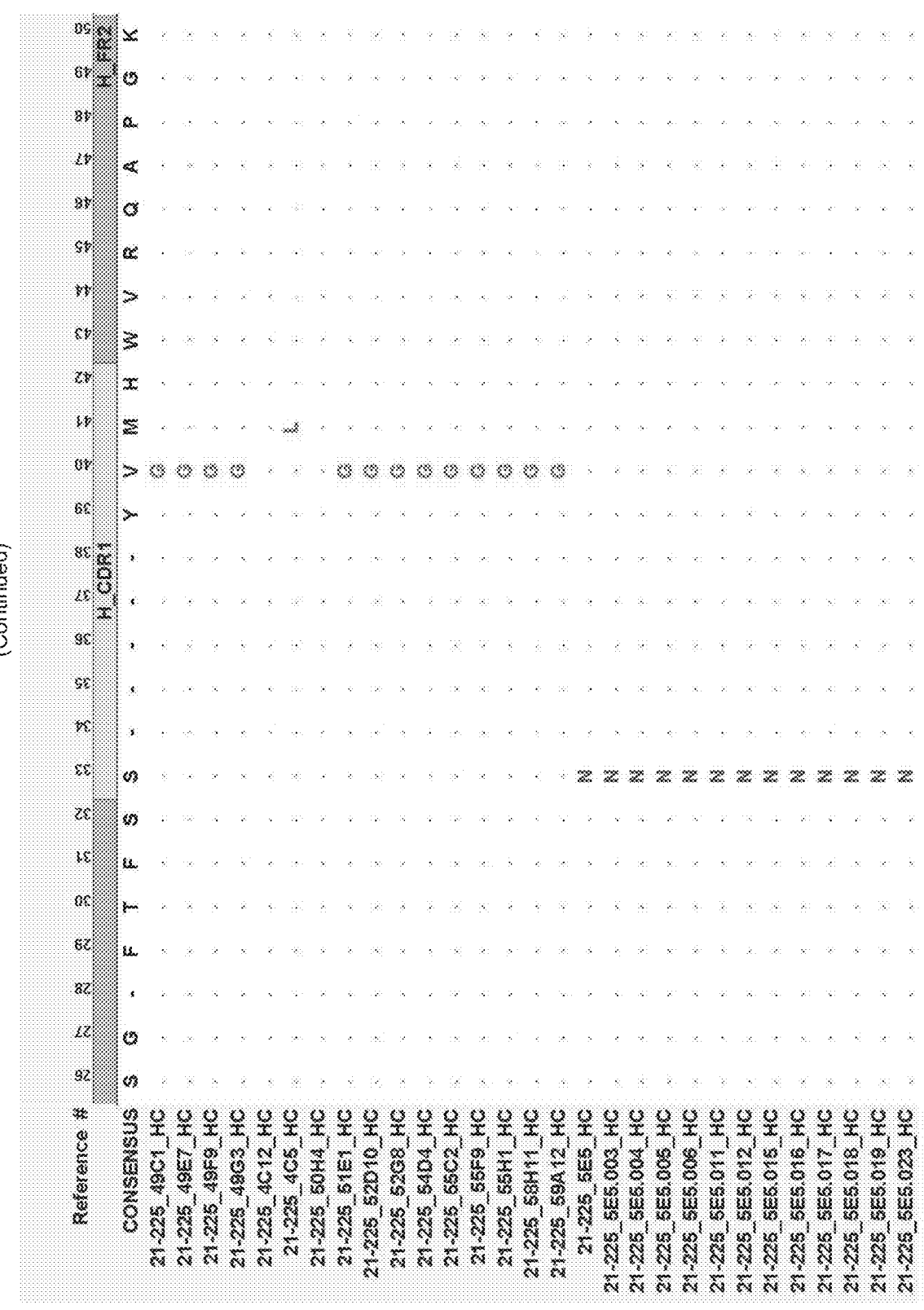
Figure 57:
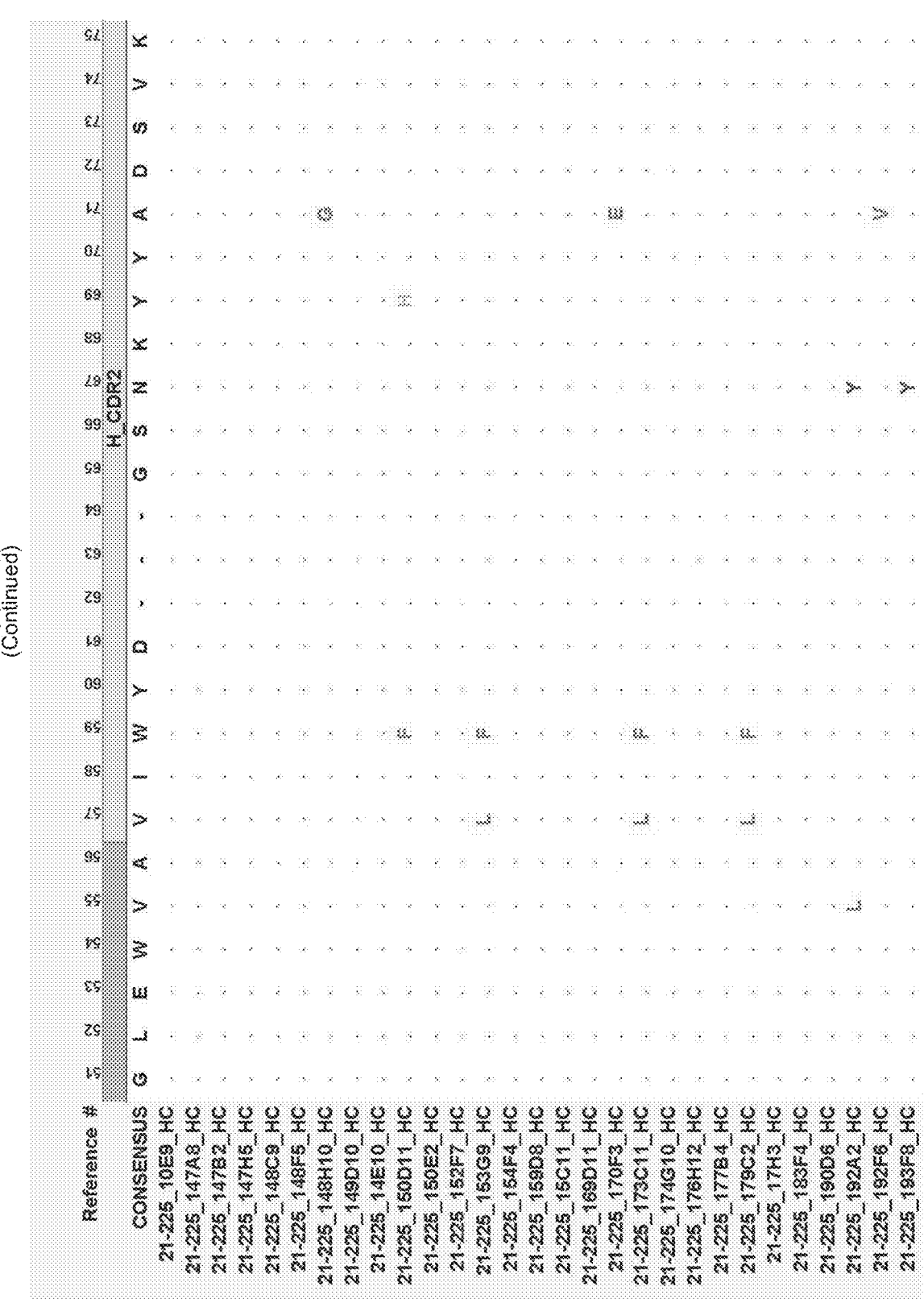
Figure 57:
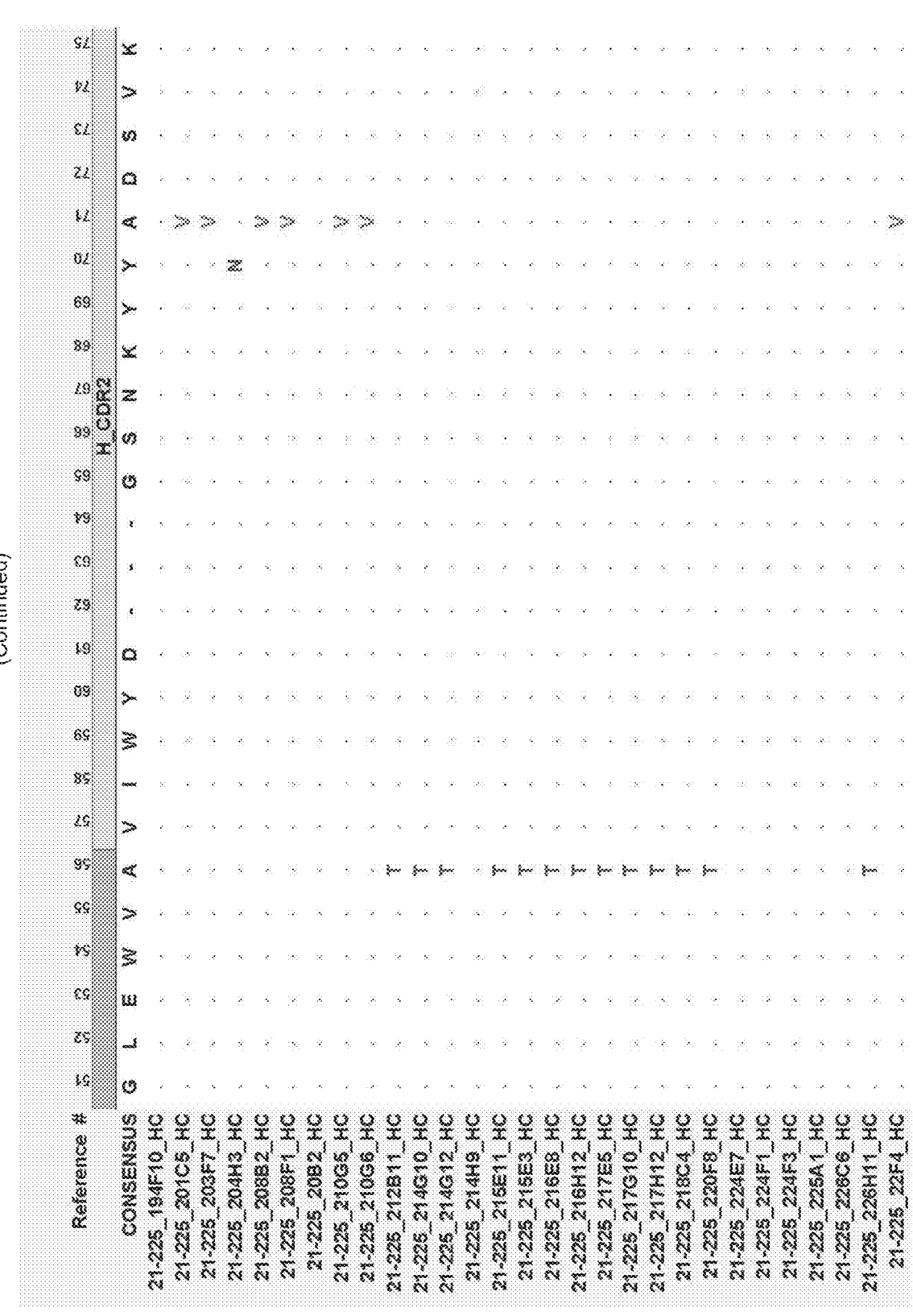
Figure 57:
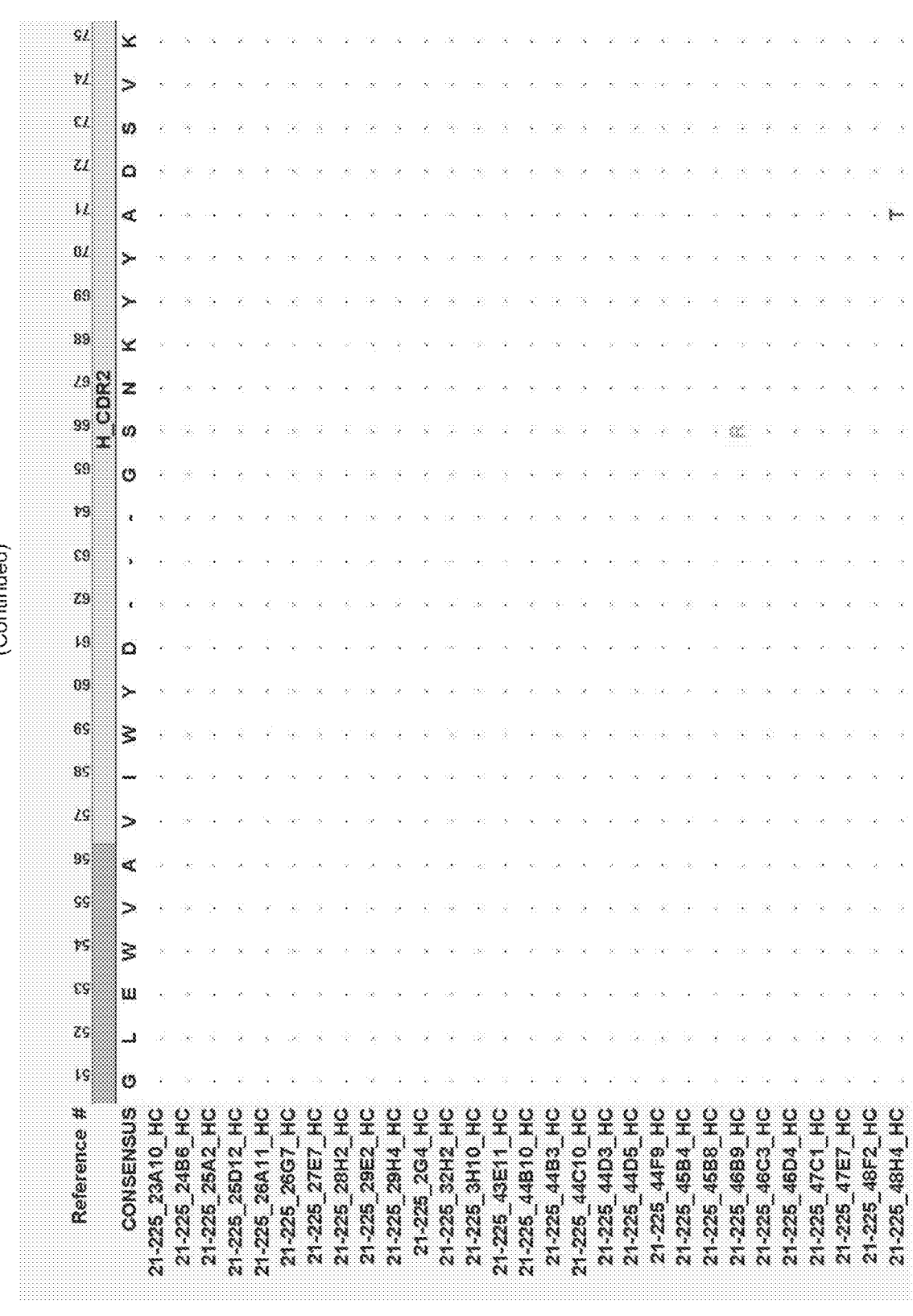
Figure 57:
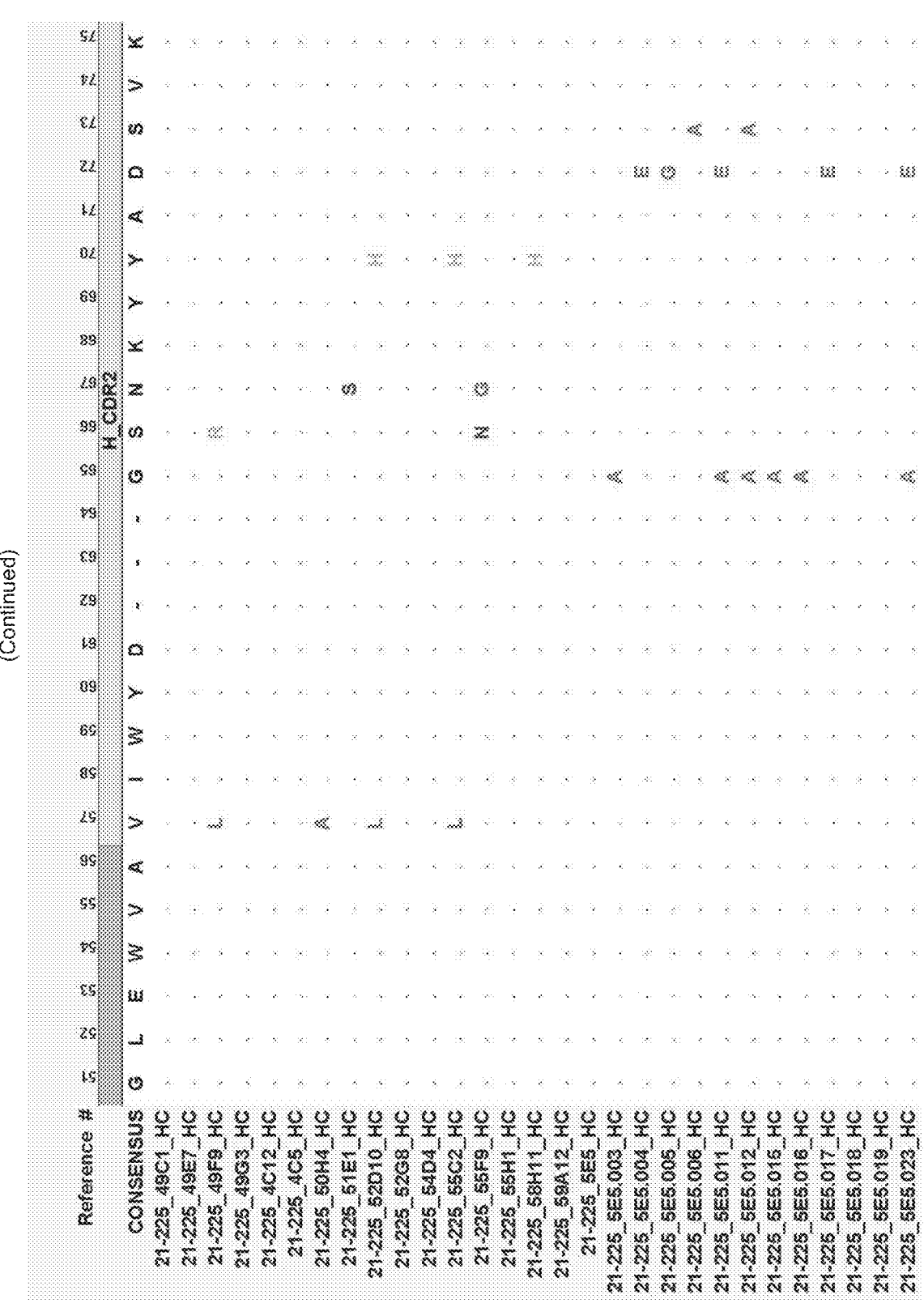
Figure 57:
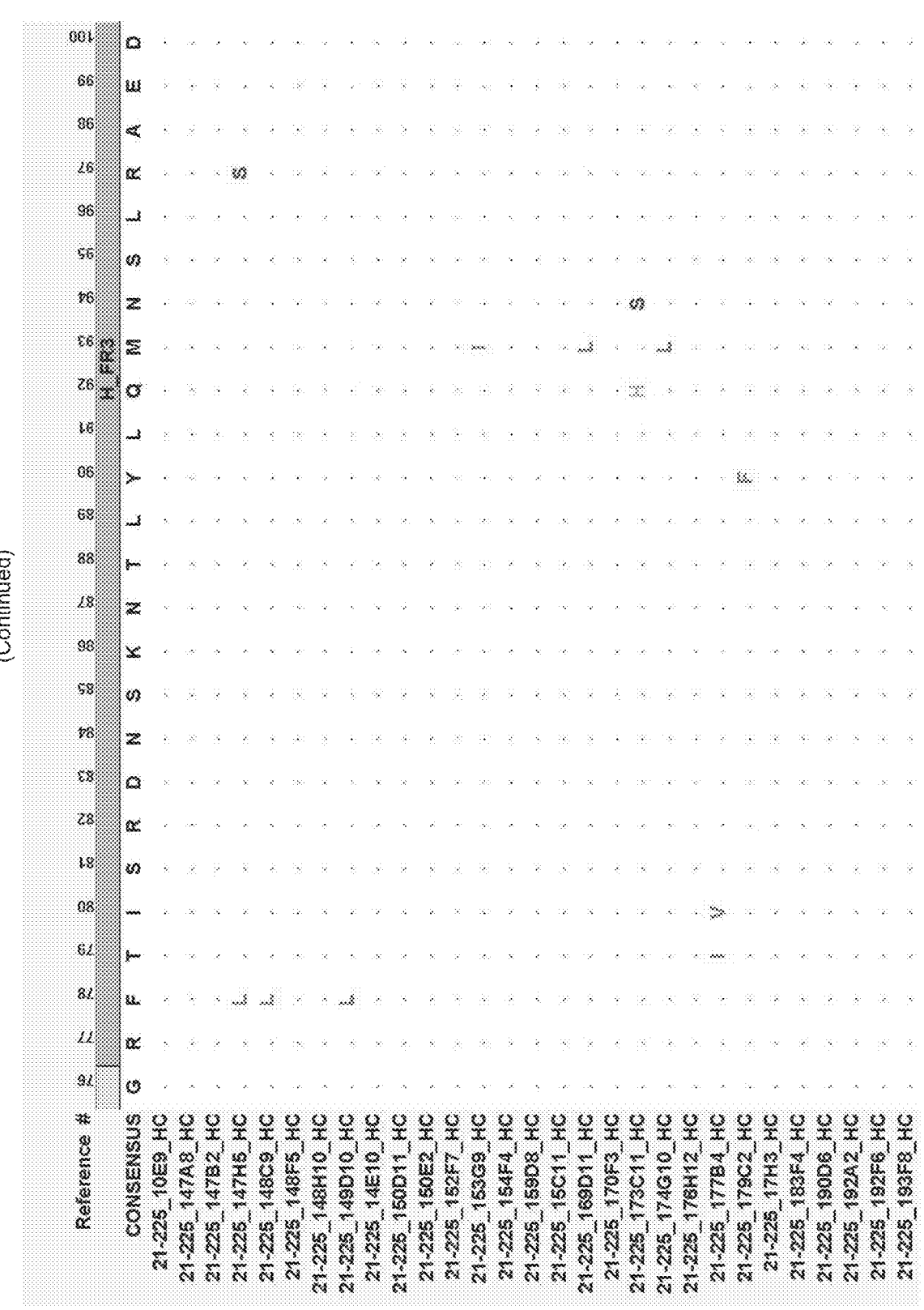
Figure 57:
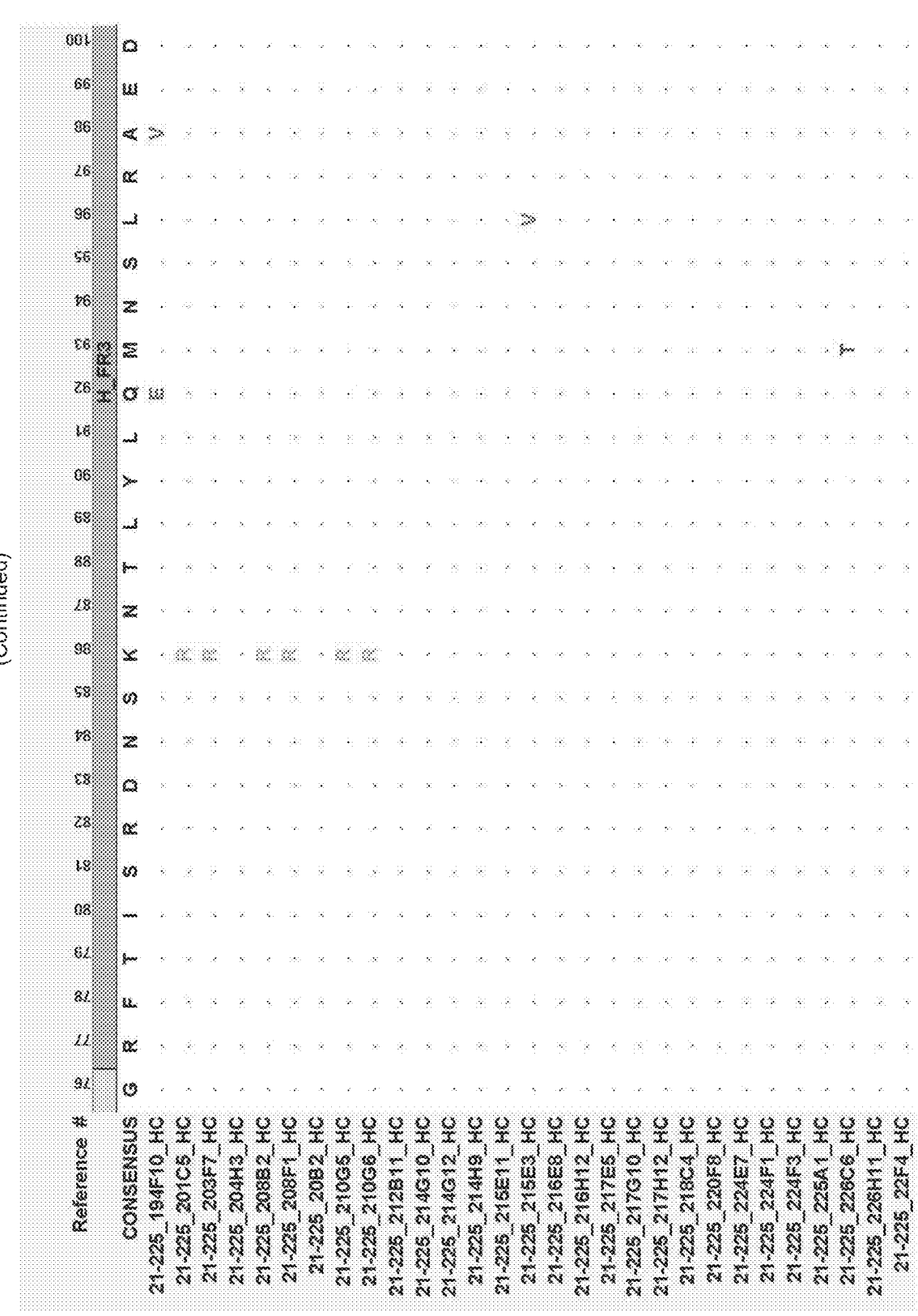
Figure 57:
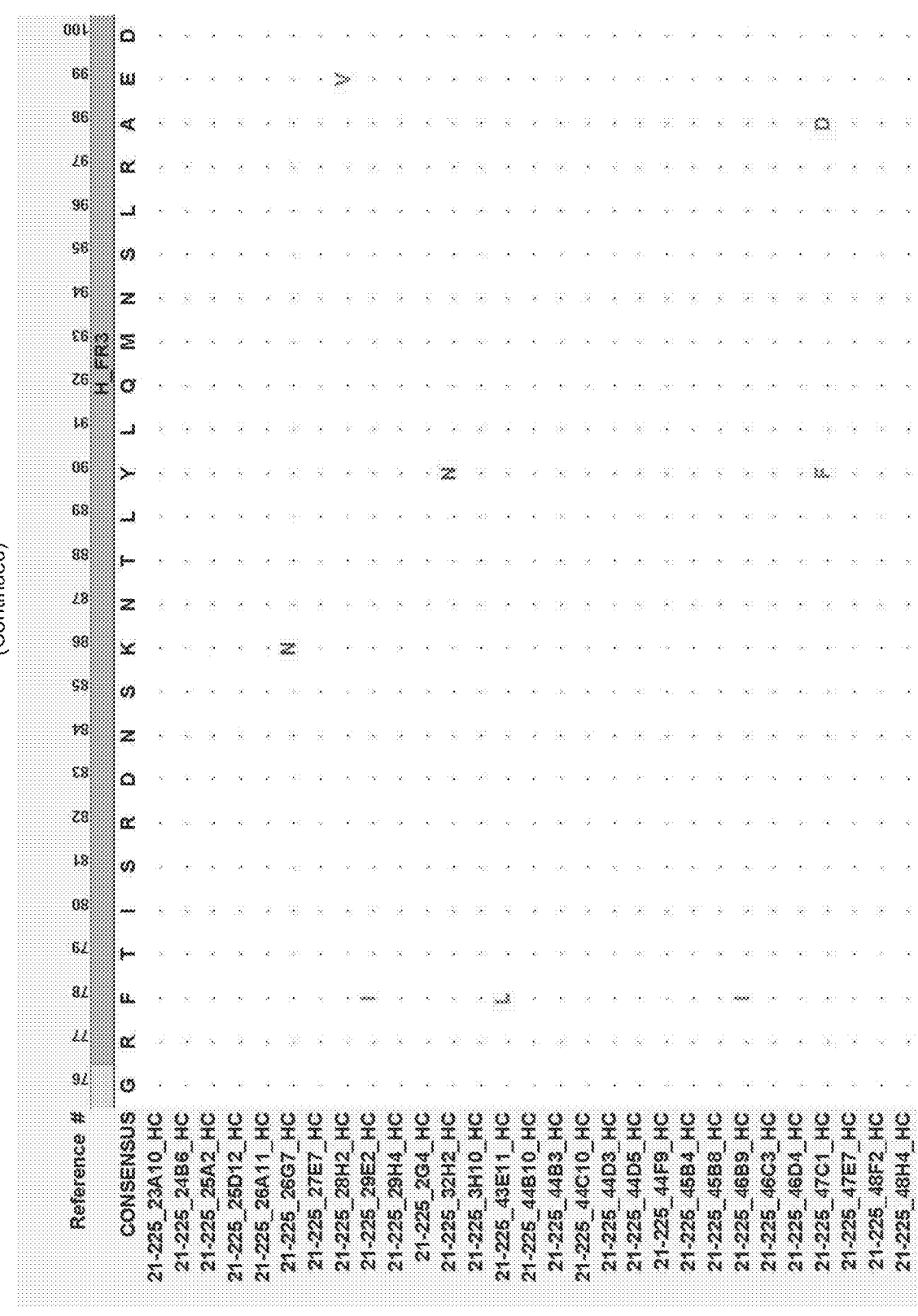
Figure 57:
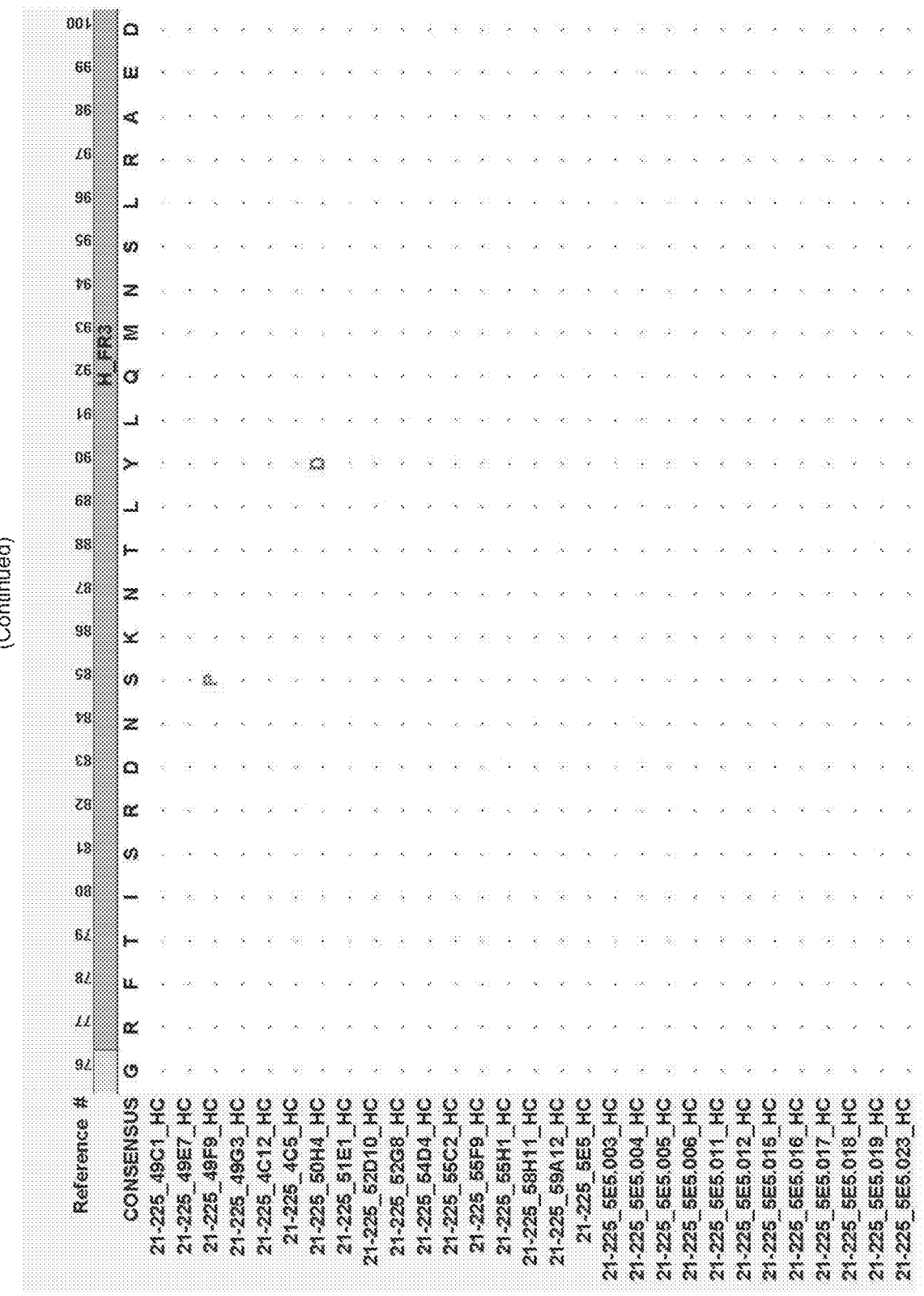
Figure 57:
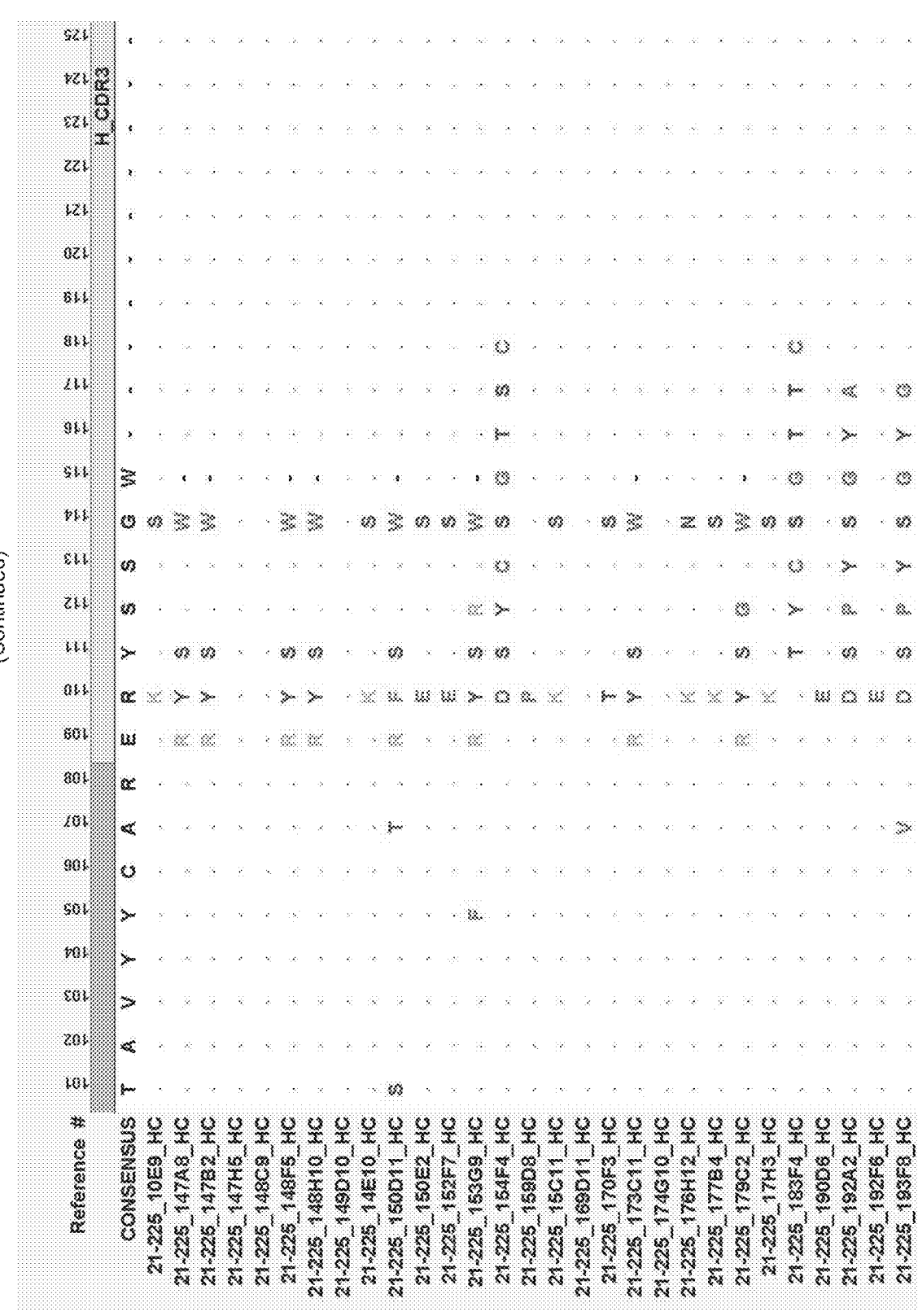
Figure 57:
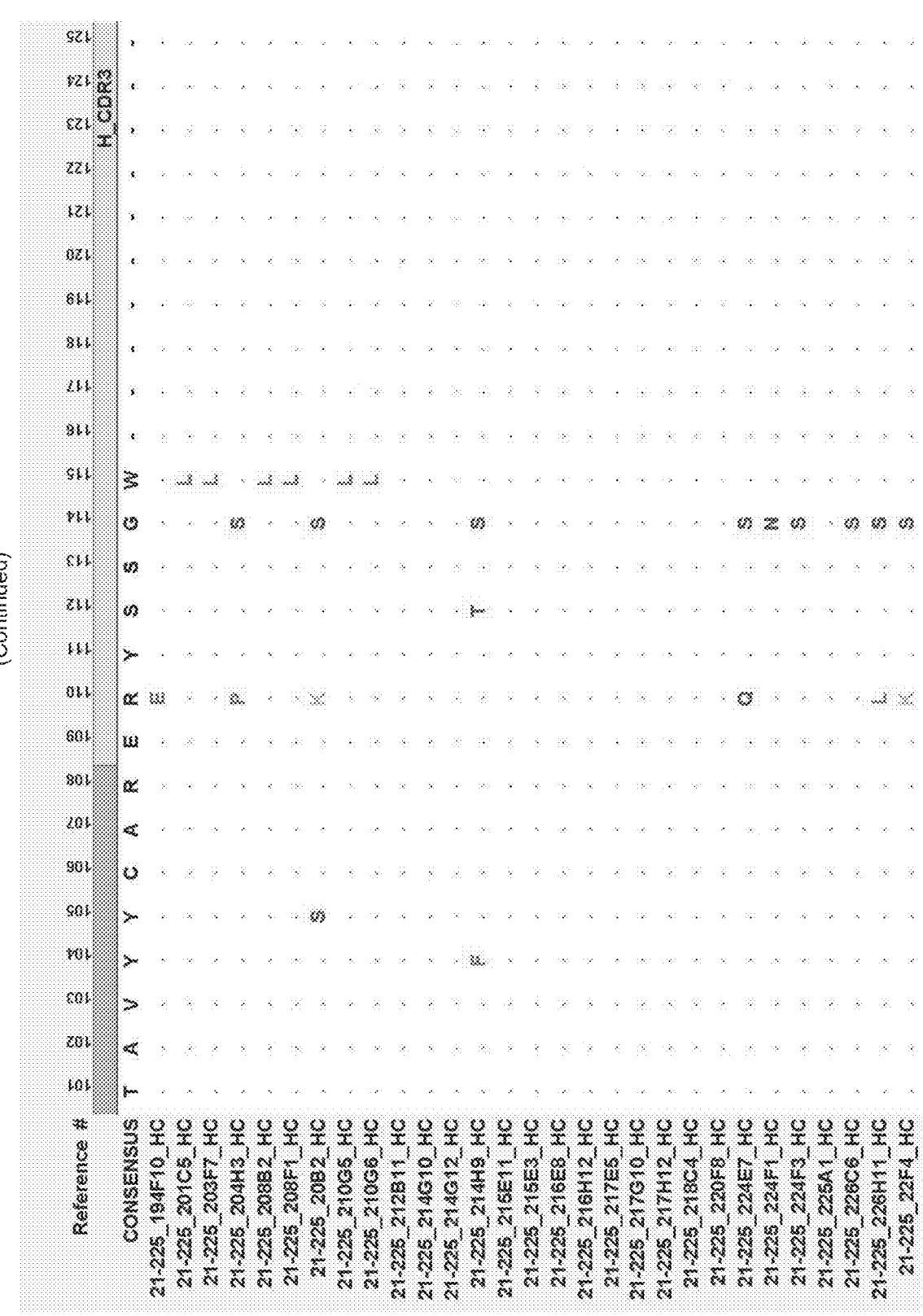
Figure 57:
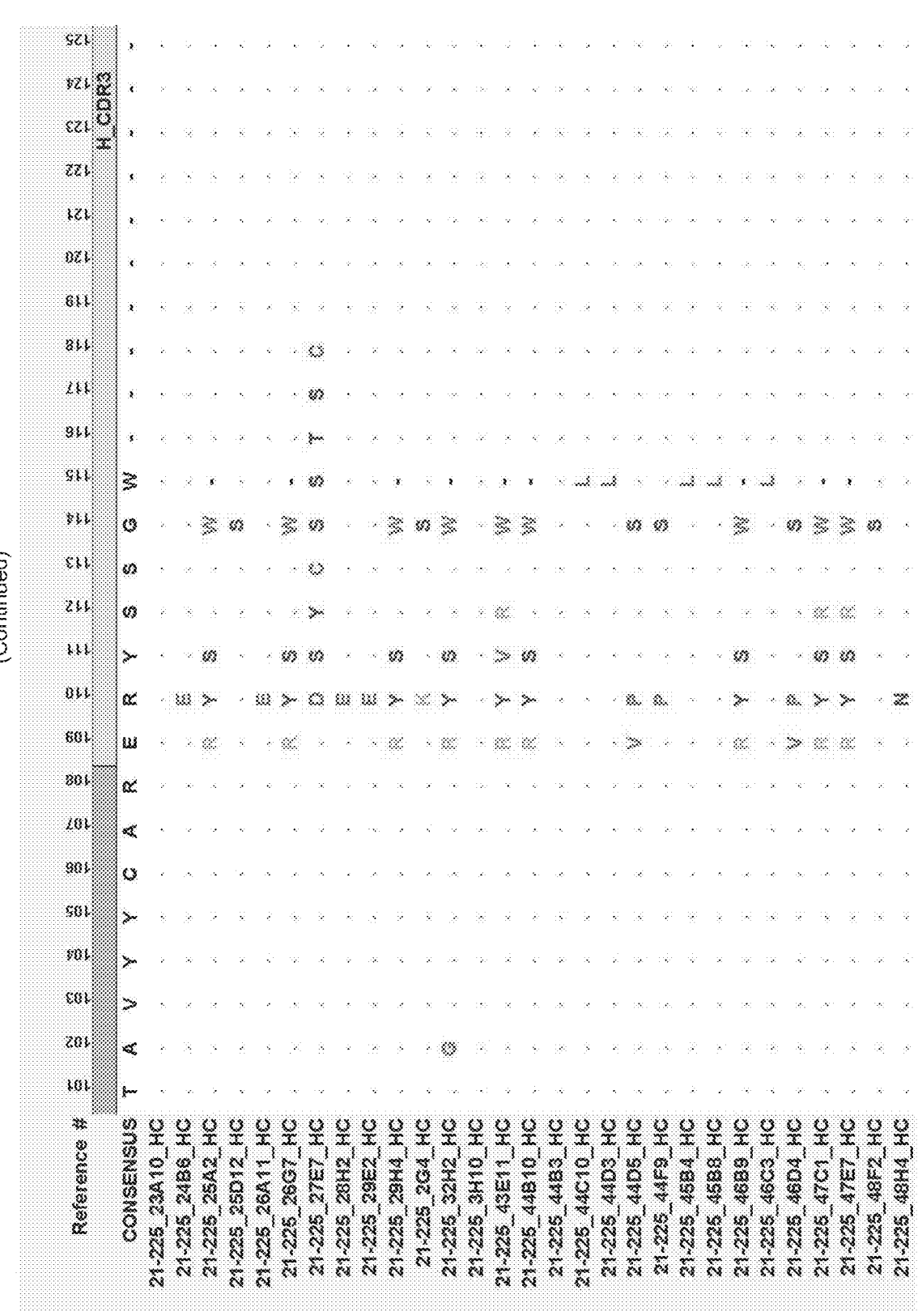
Figure 57:
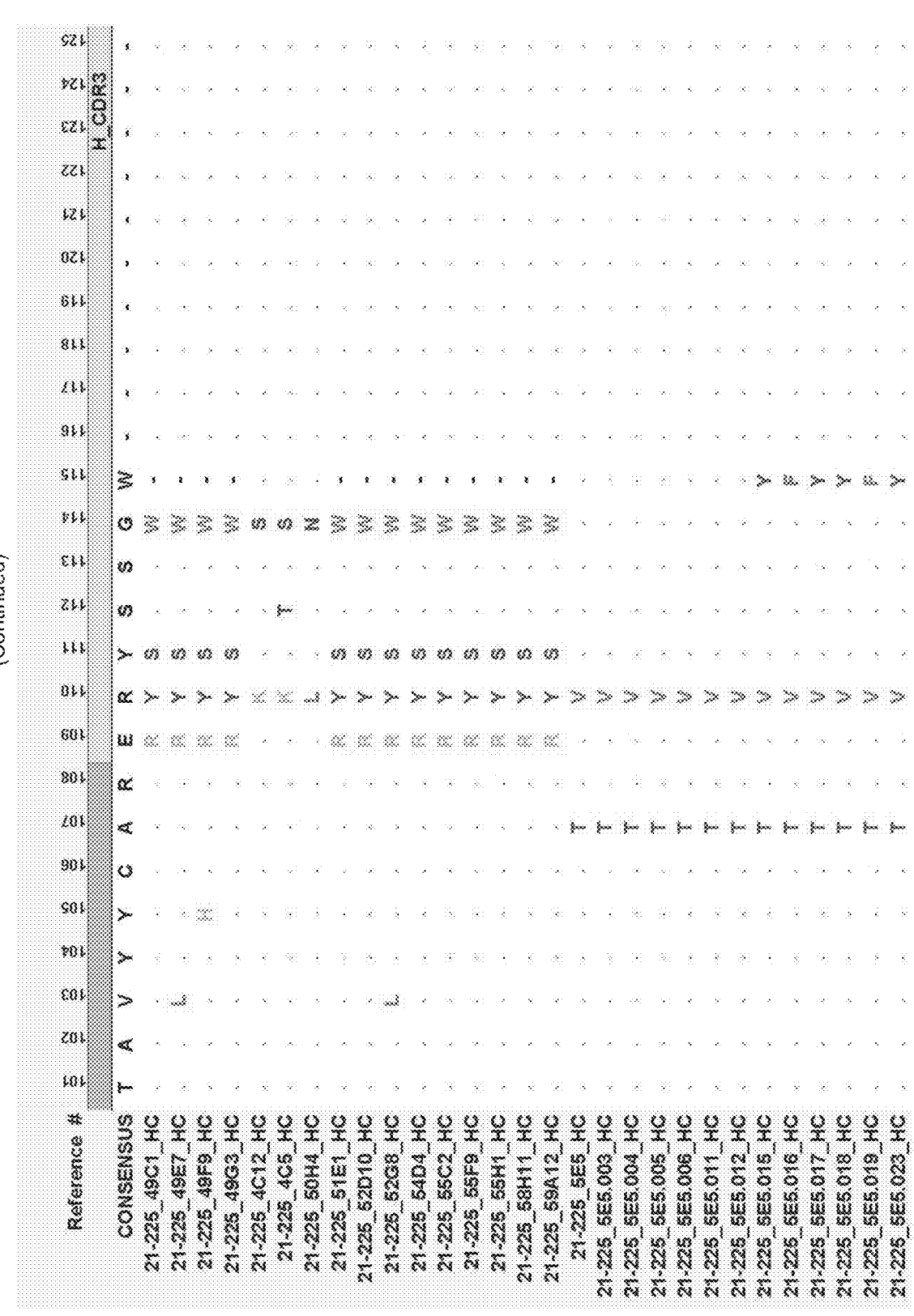
Figure 57:
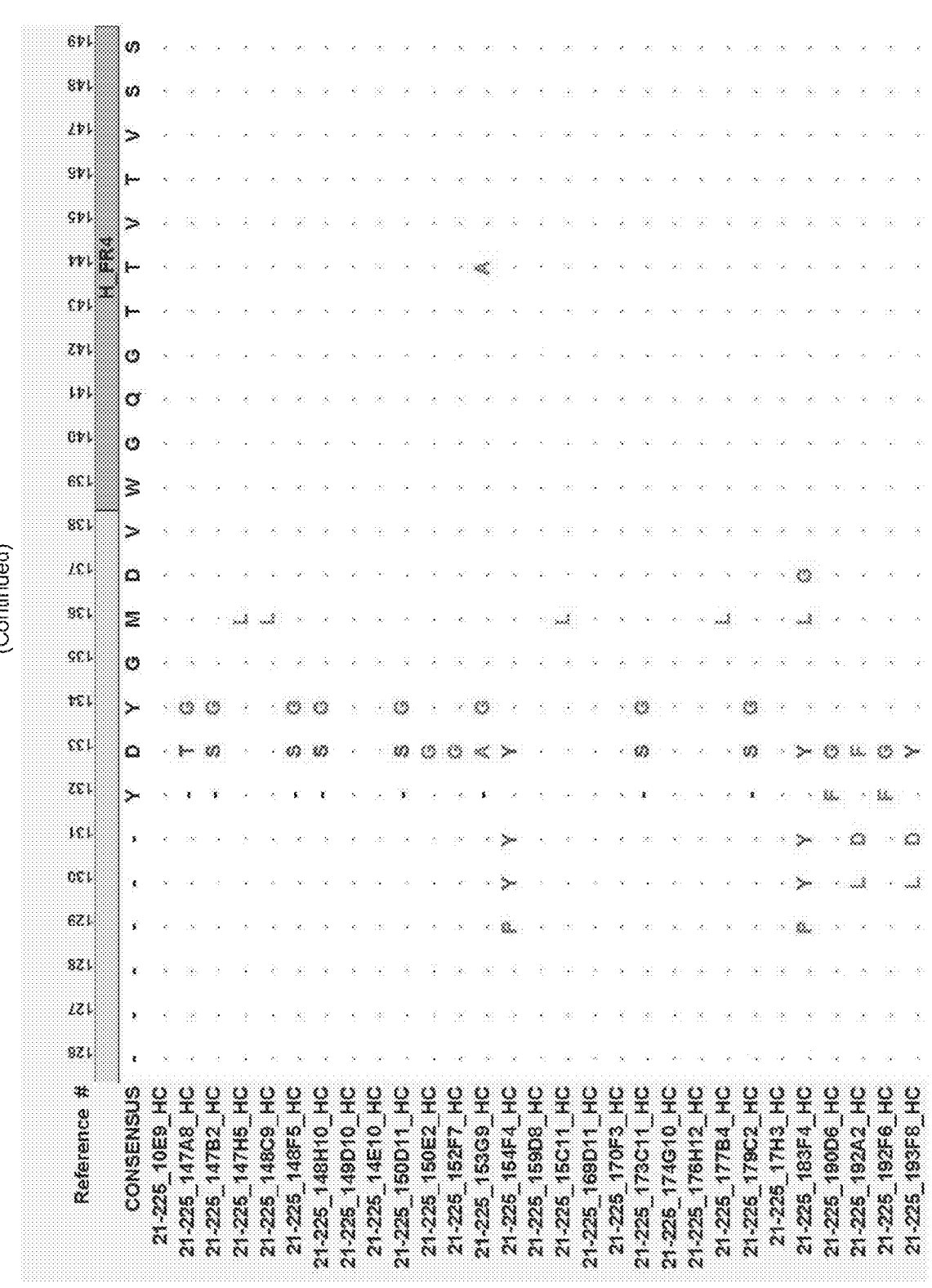
Figure 57:
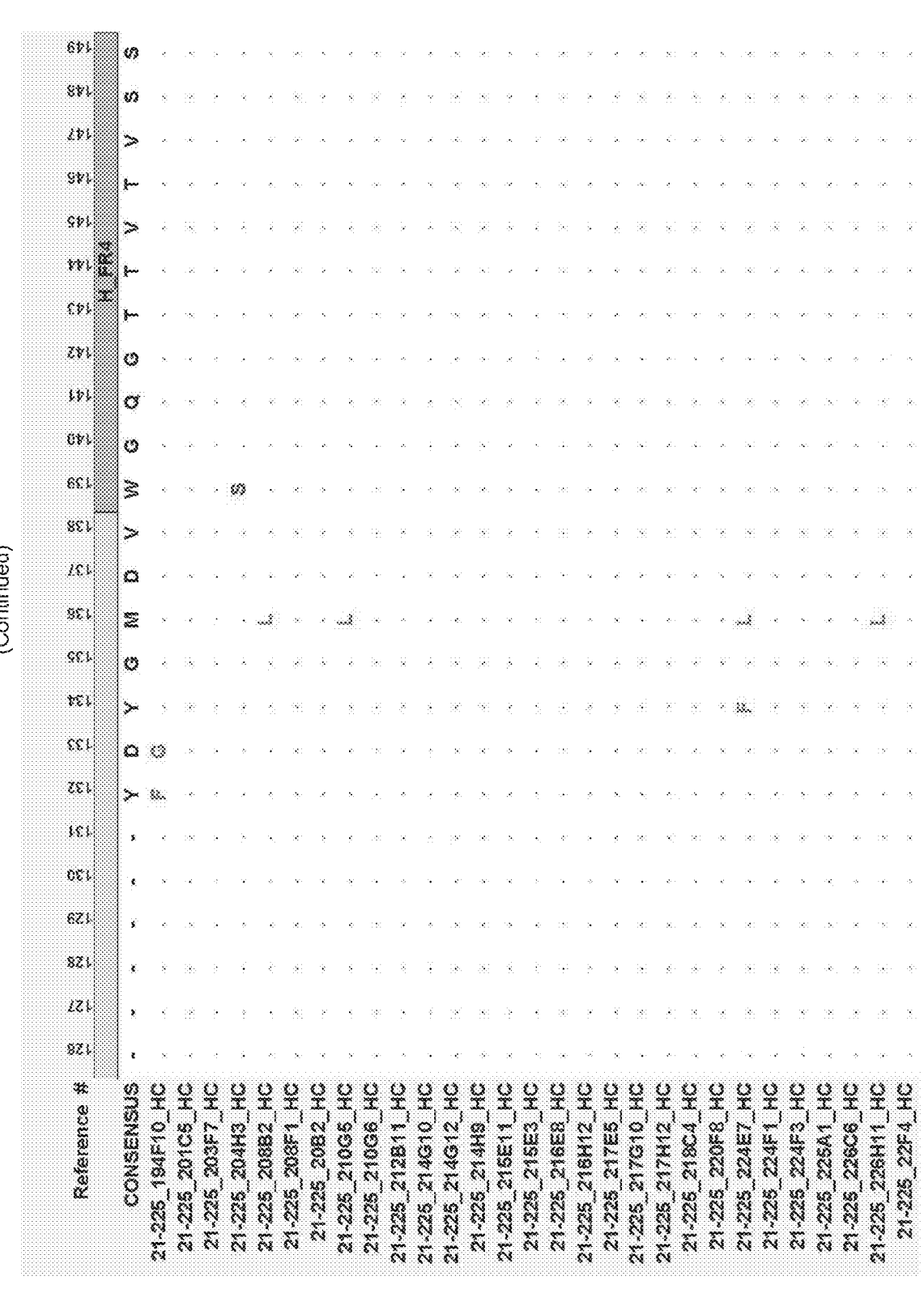
Figure 57:
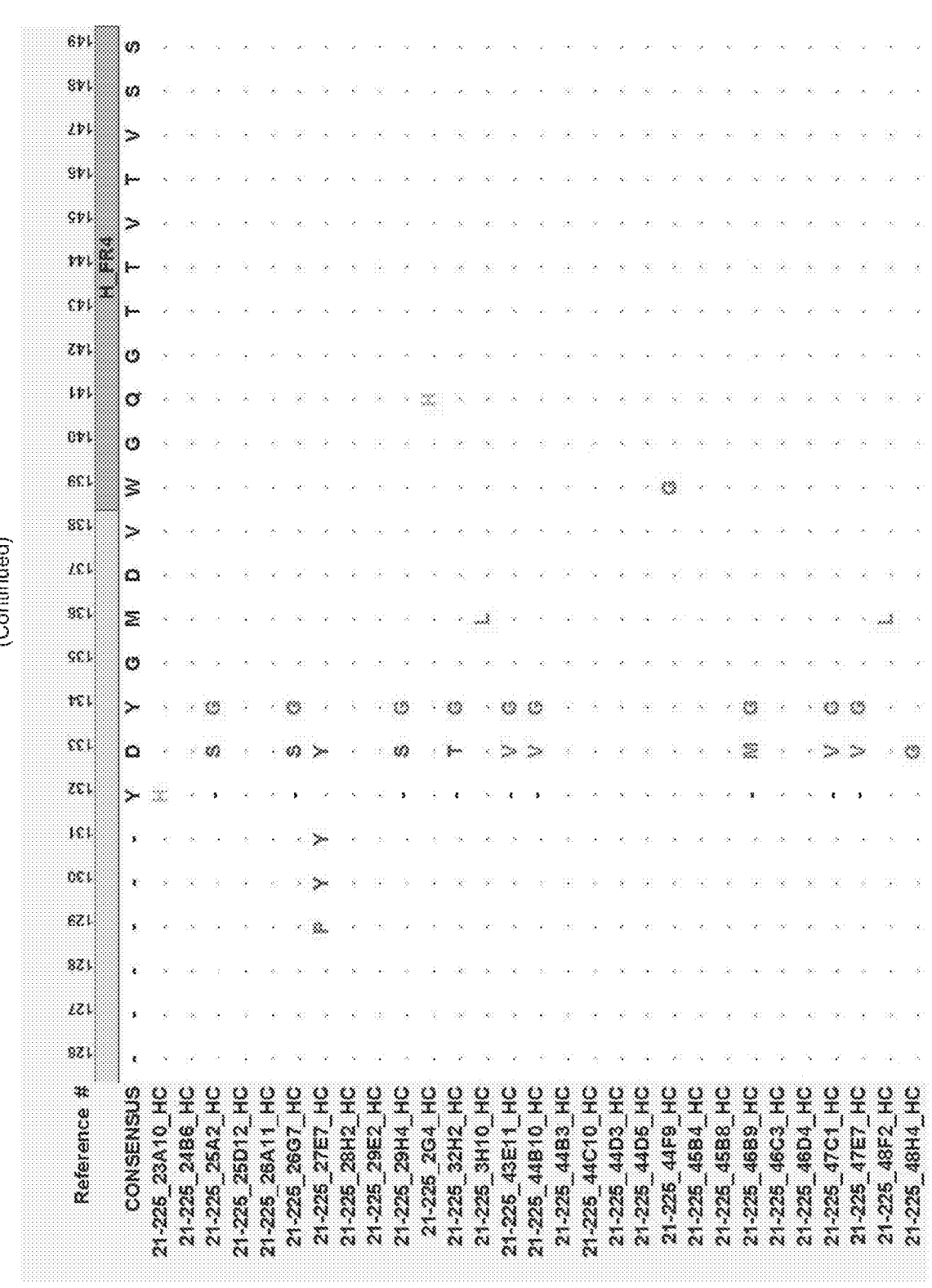
Figure 57:
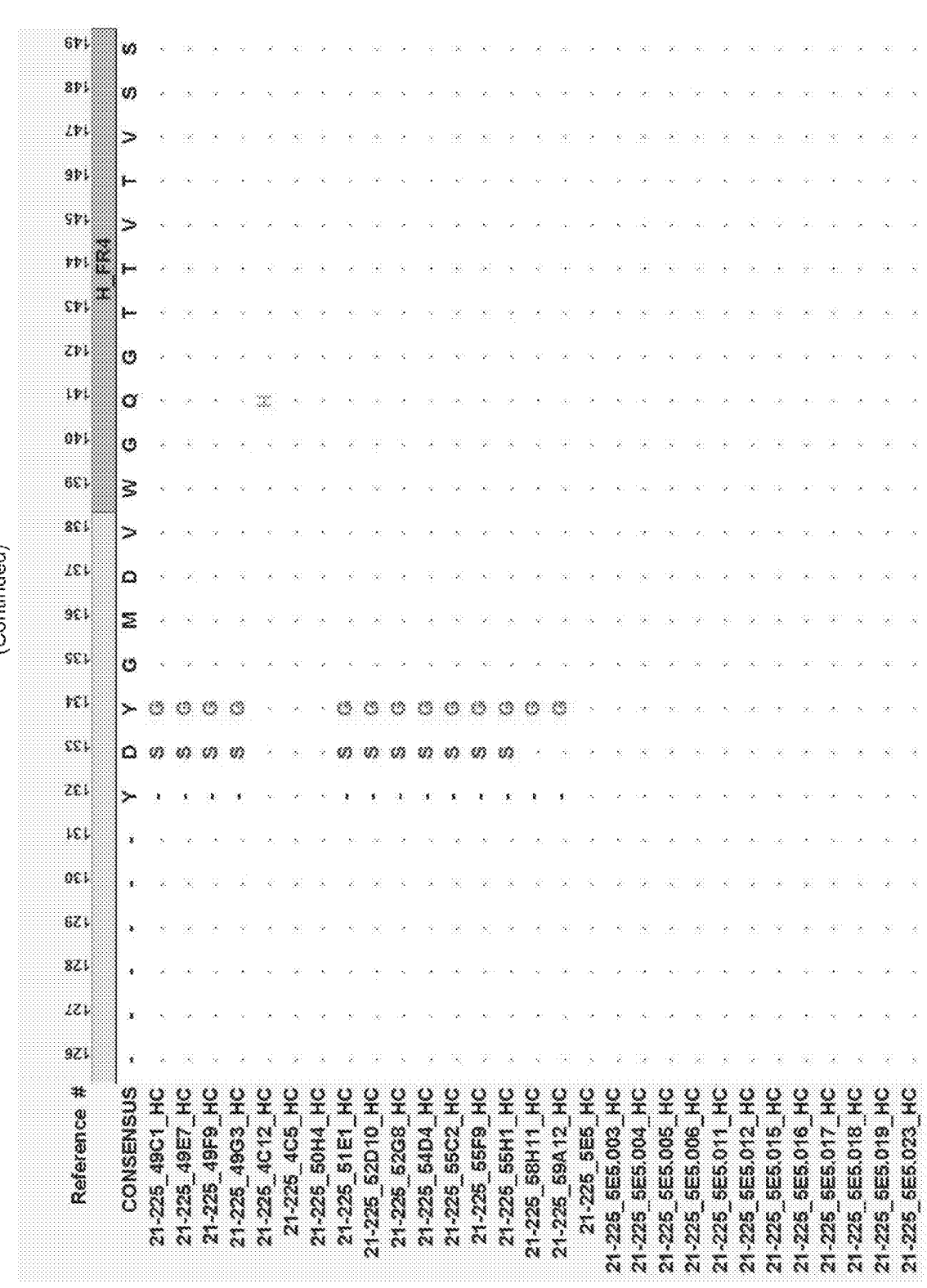
Figure 57:
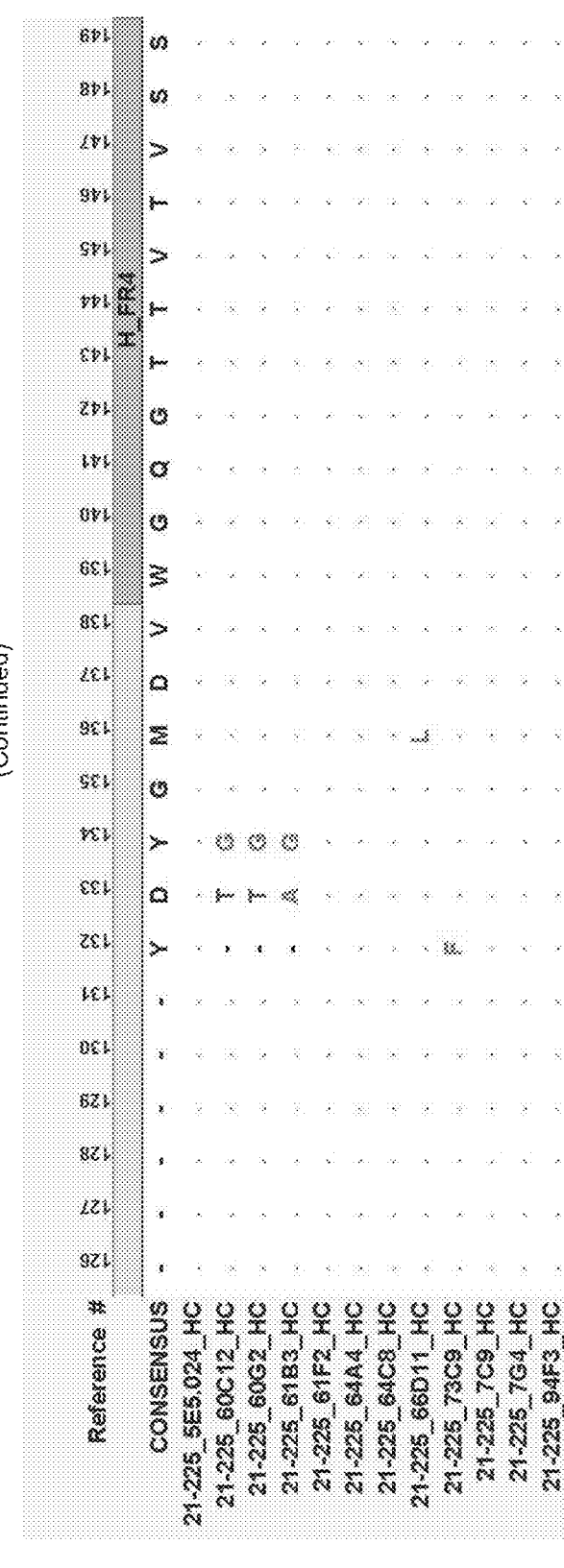
Figure 57:
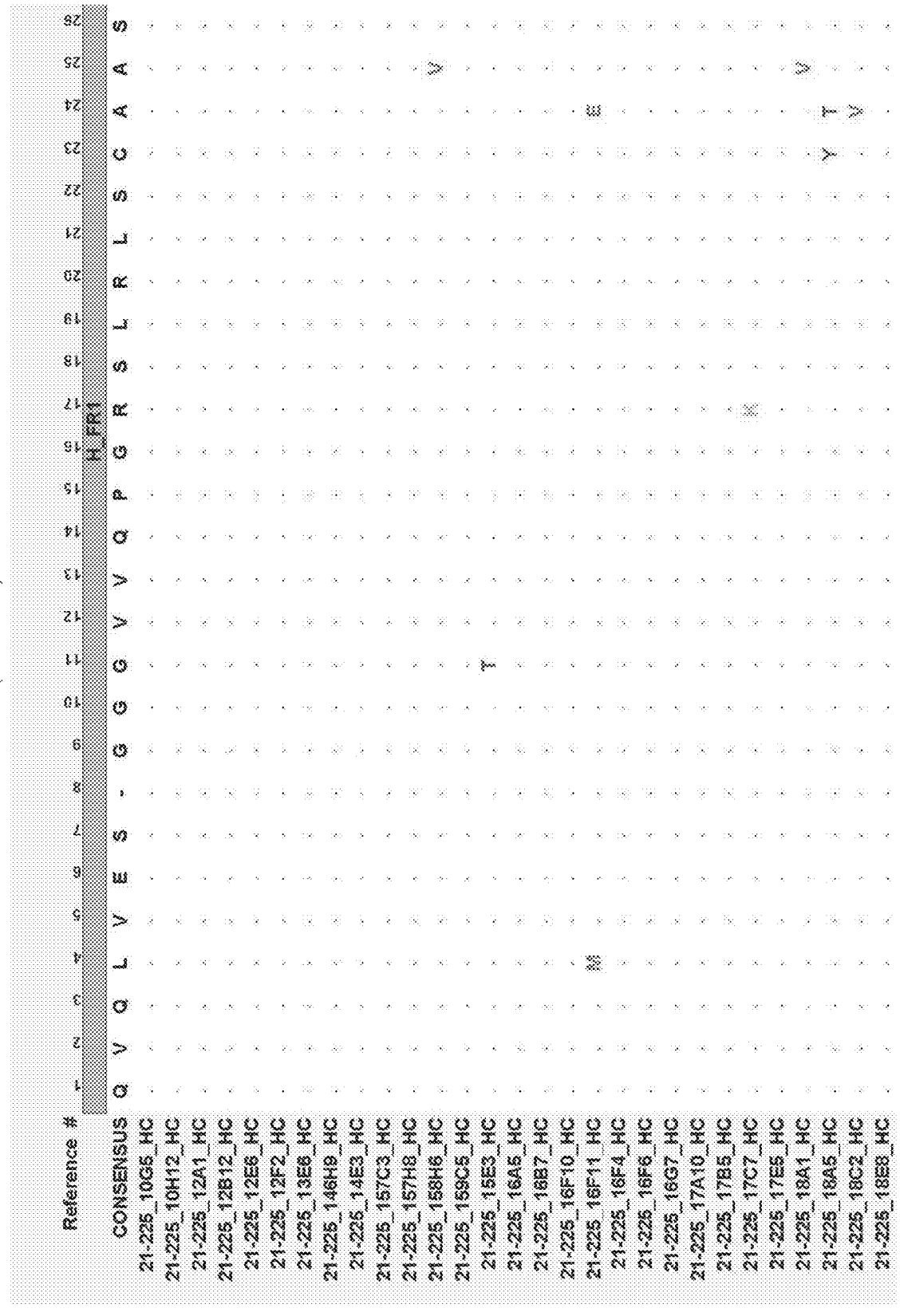
Figure 57:
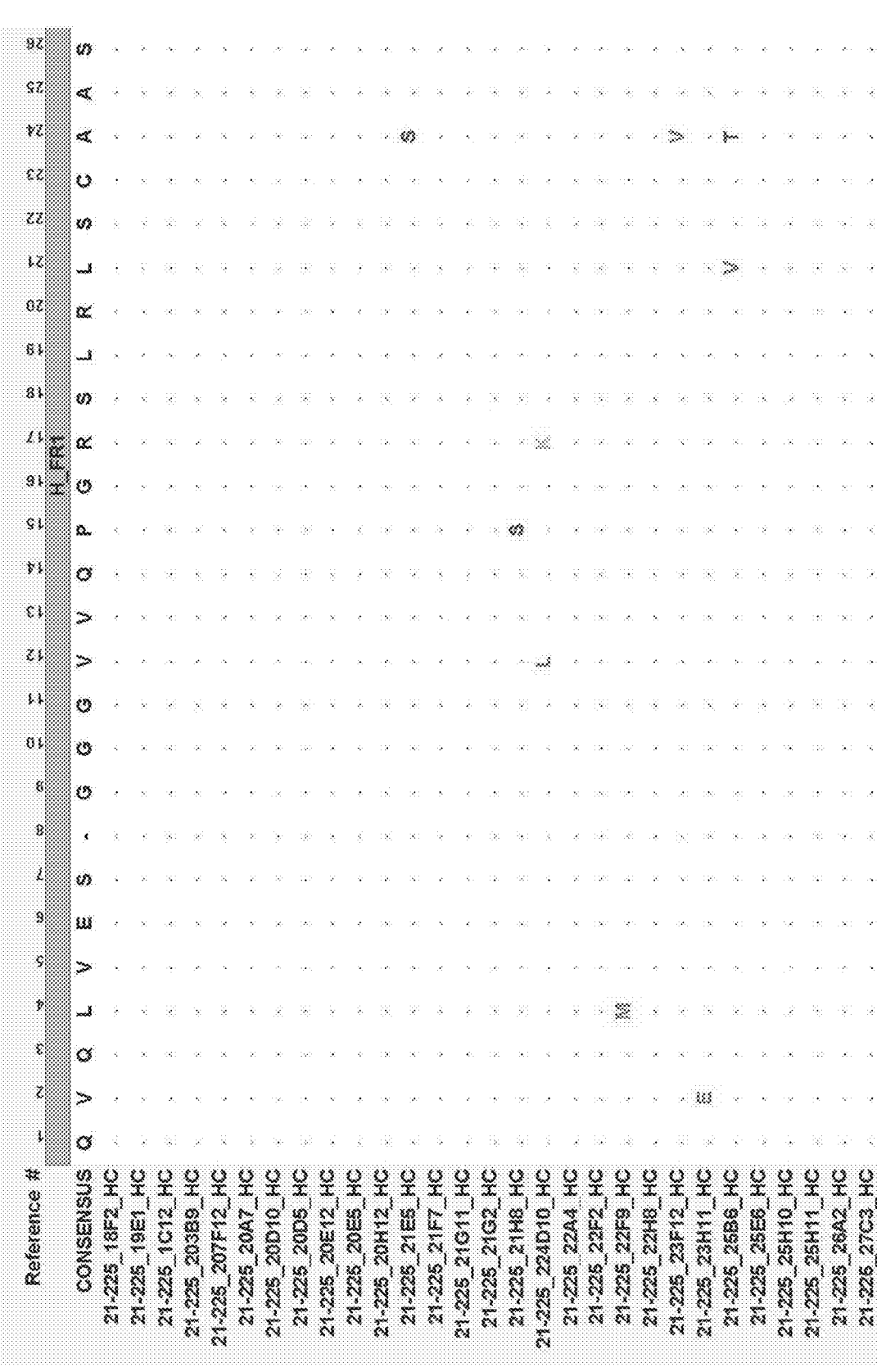
Figure 57:
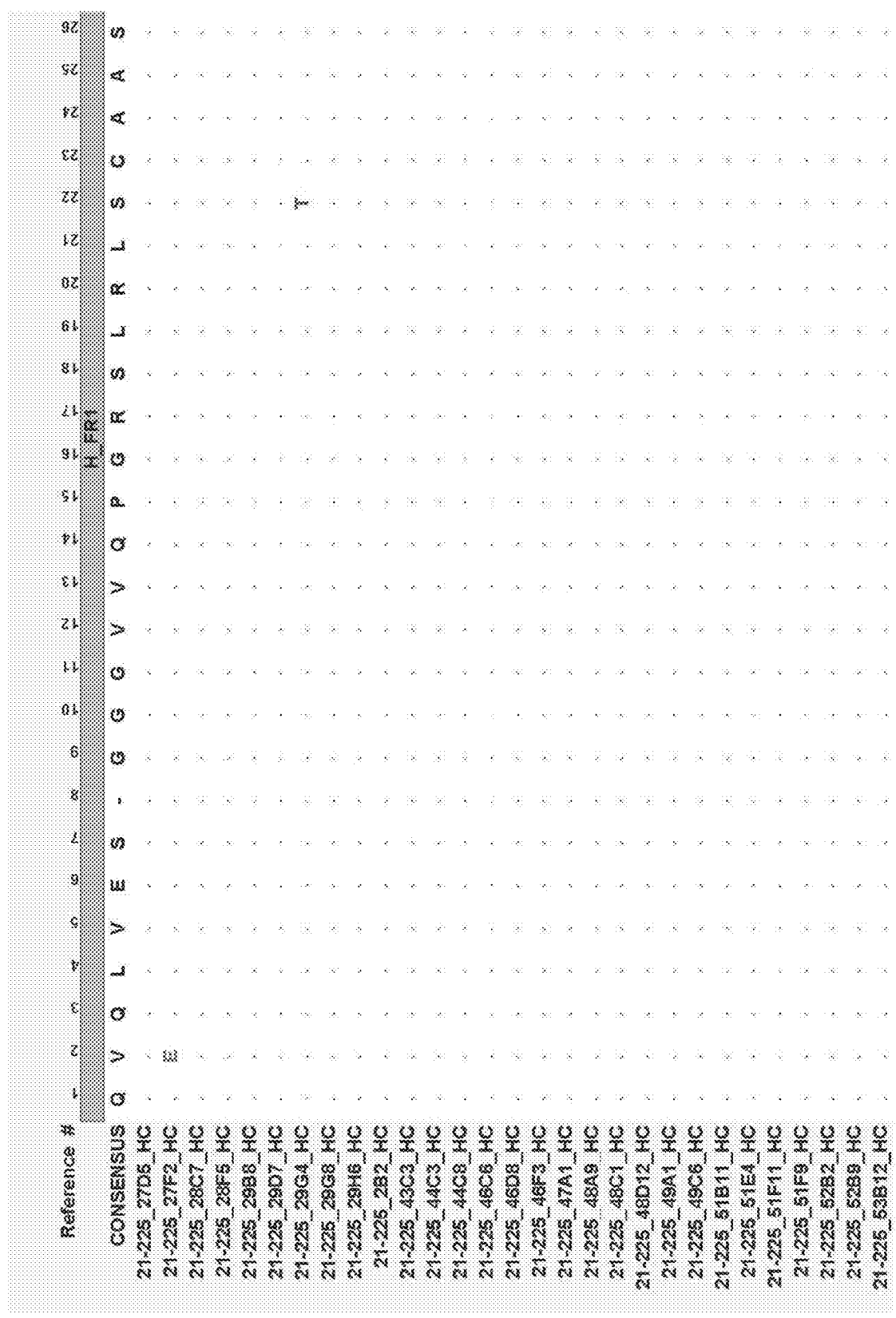
Figure 57:
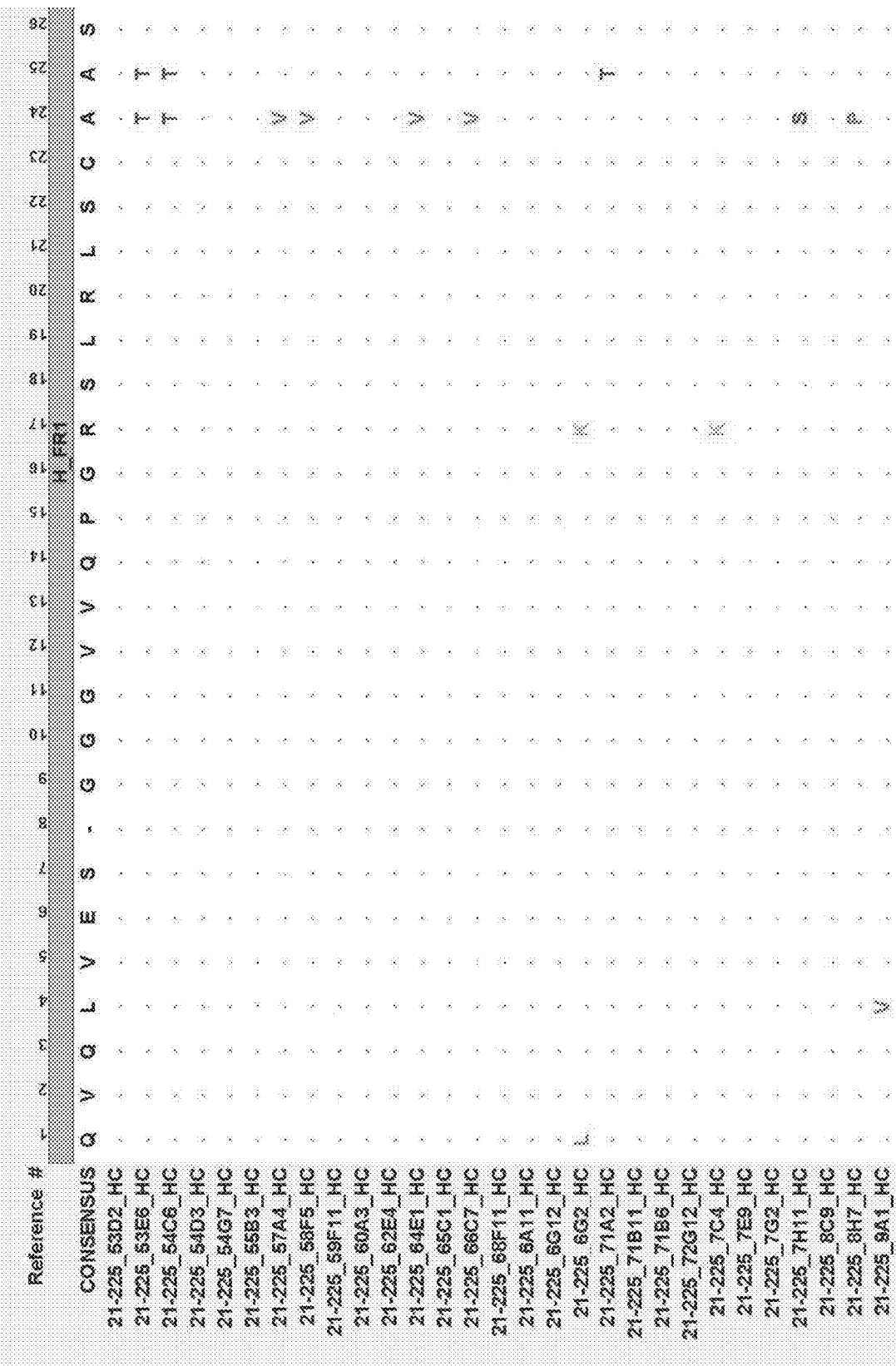
Figure 57:
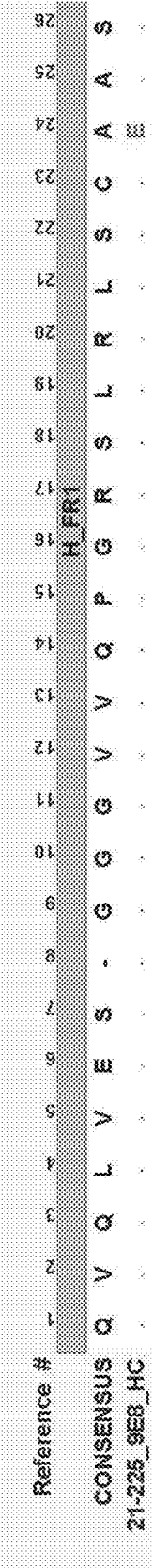
Figure 57:
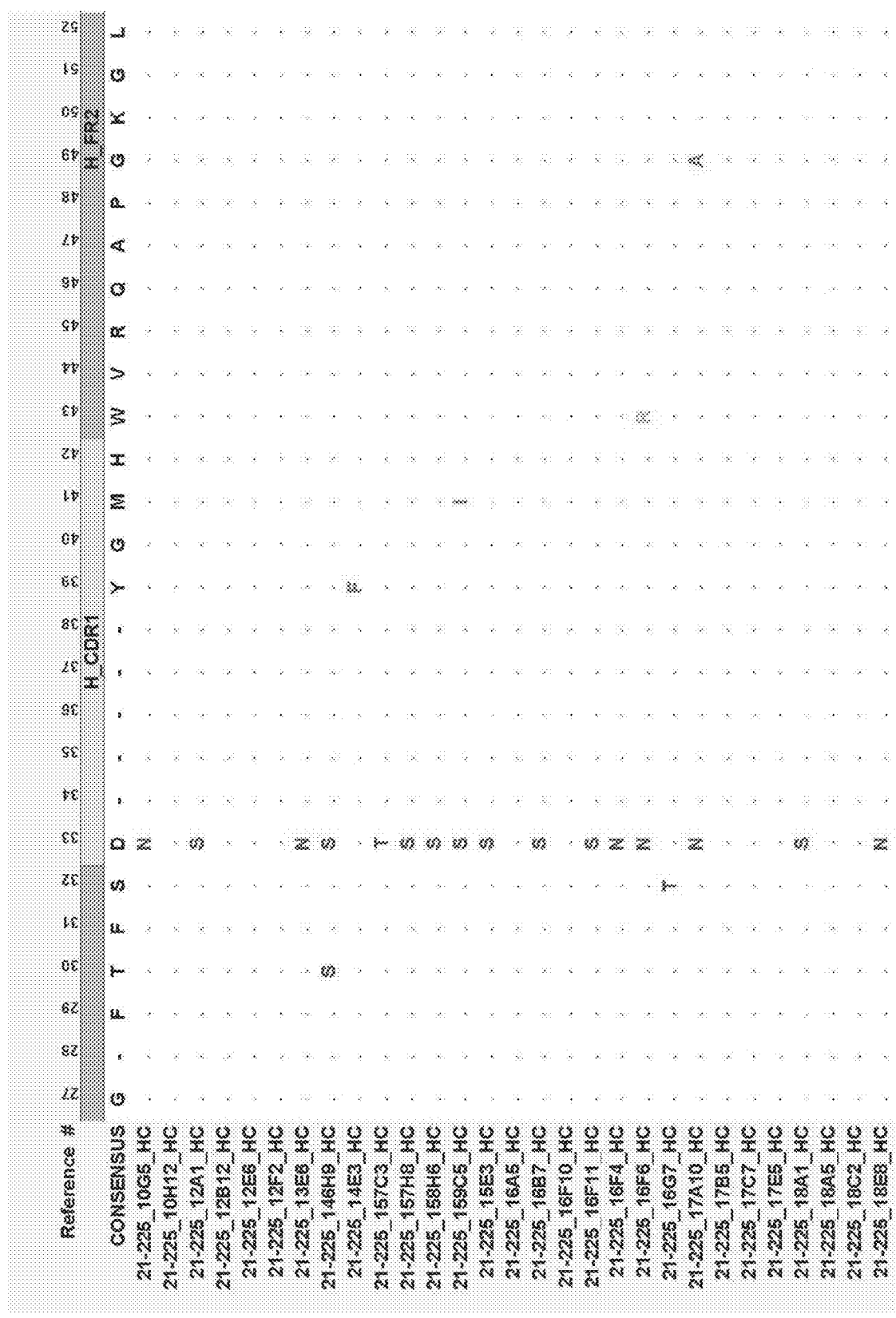
Figure 57:
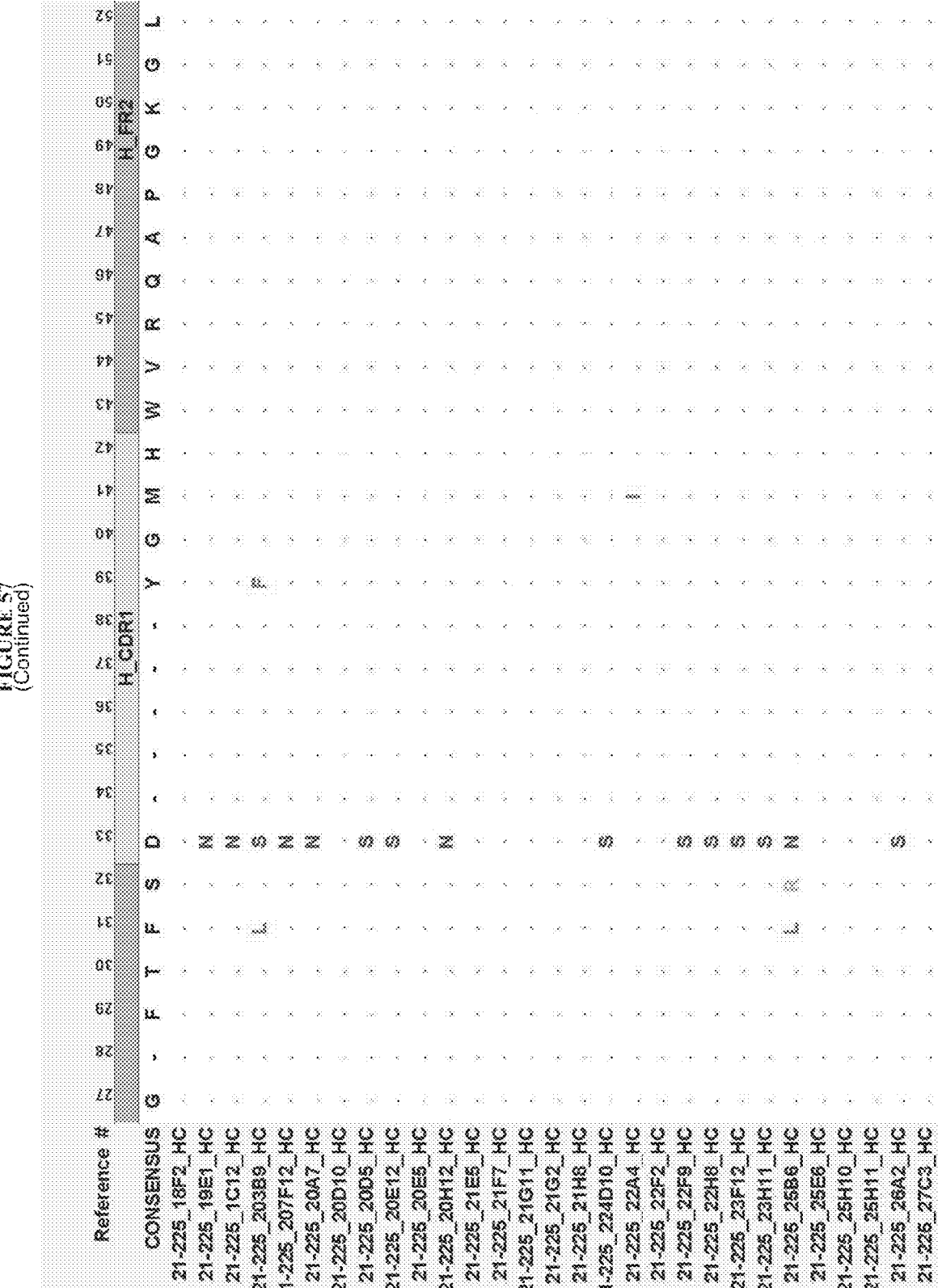
Figure 57:
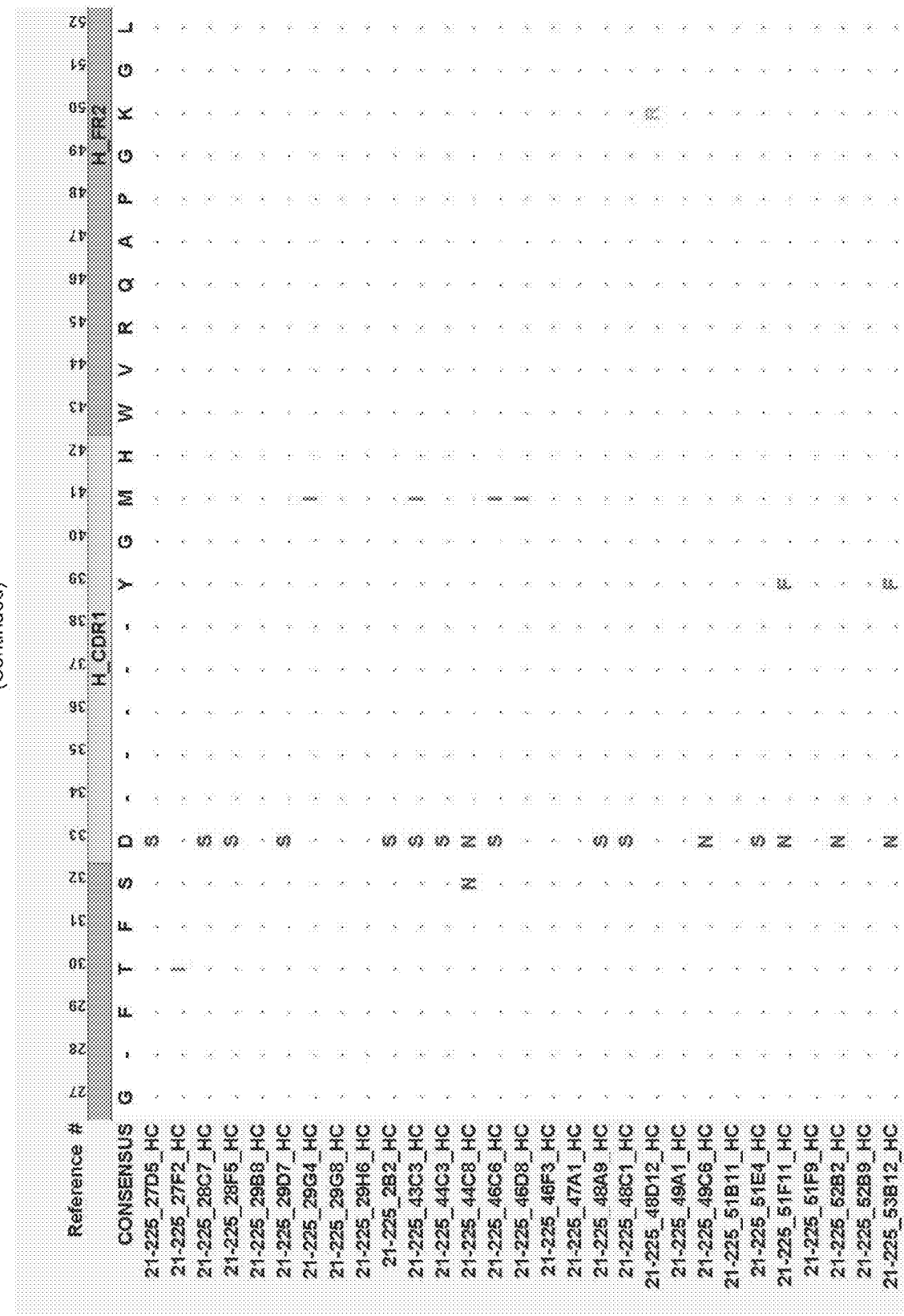
Figure 57:
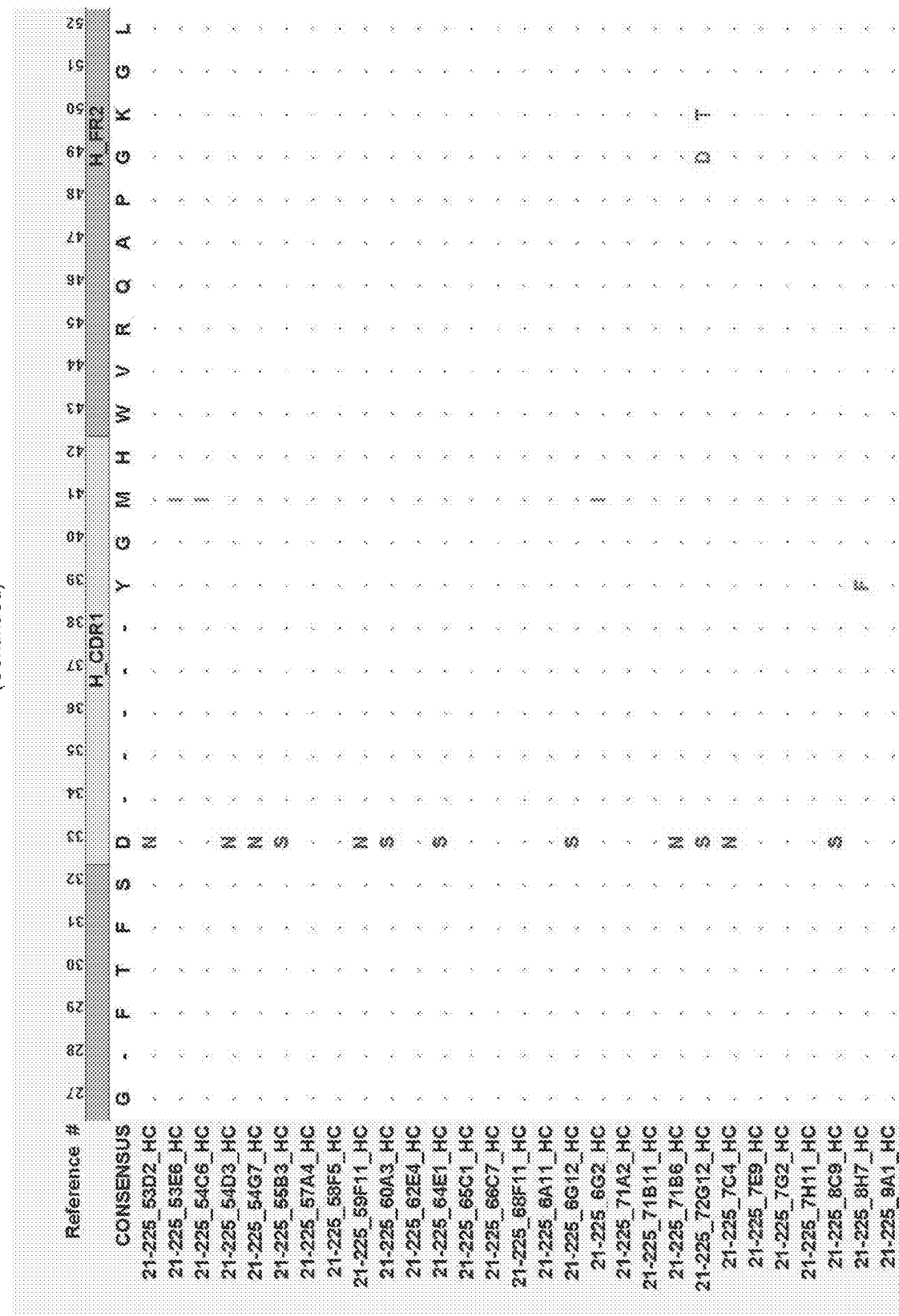
Figure 57:
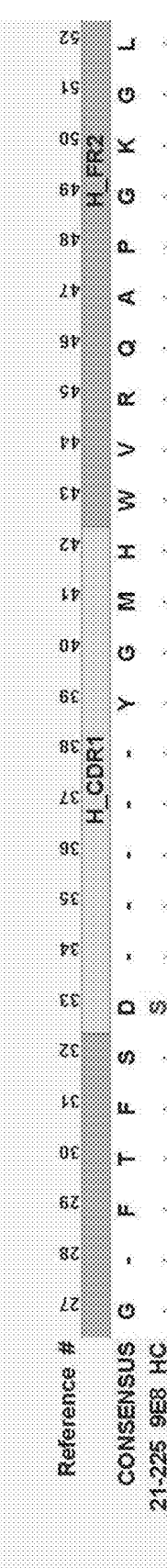
Figure 57:
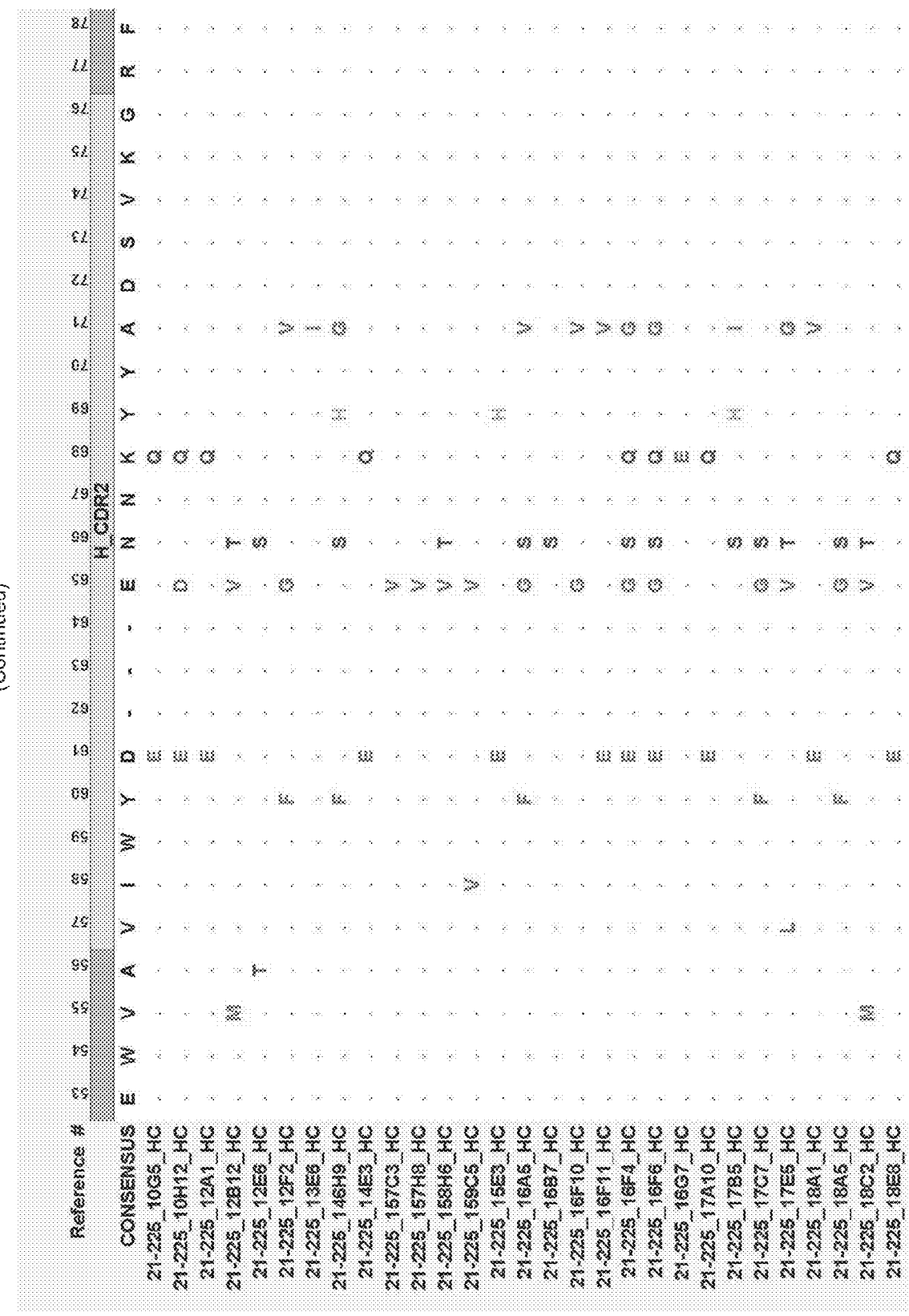
Figure 57:
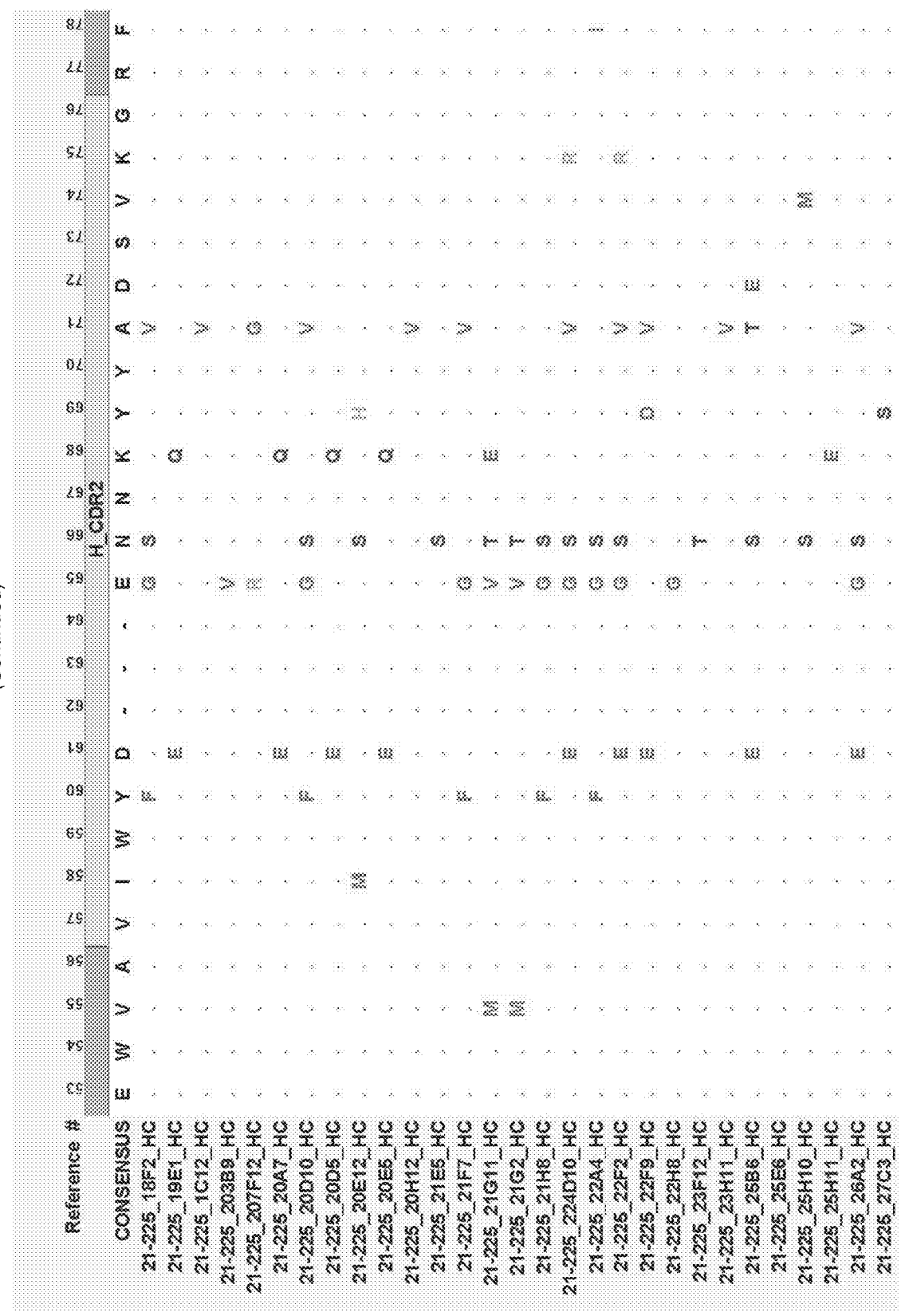
Figure 57:
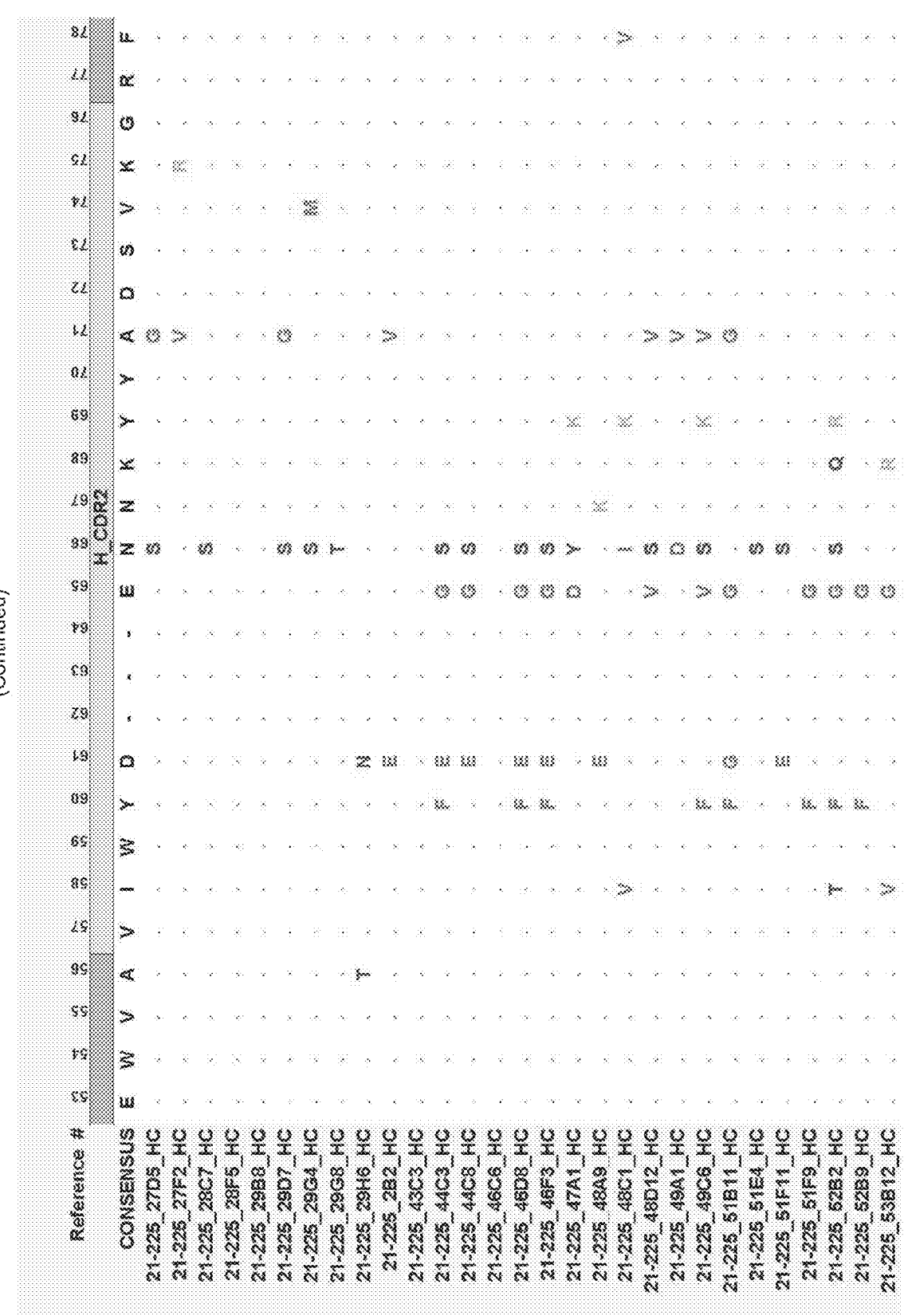
Figure 57:
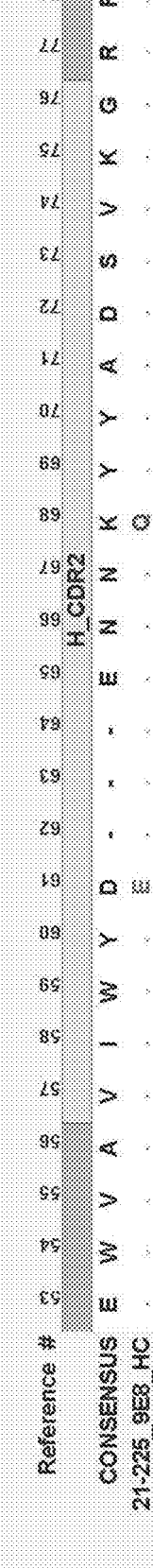
Figure 57:
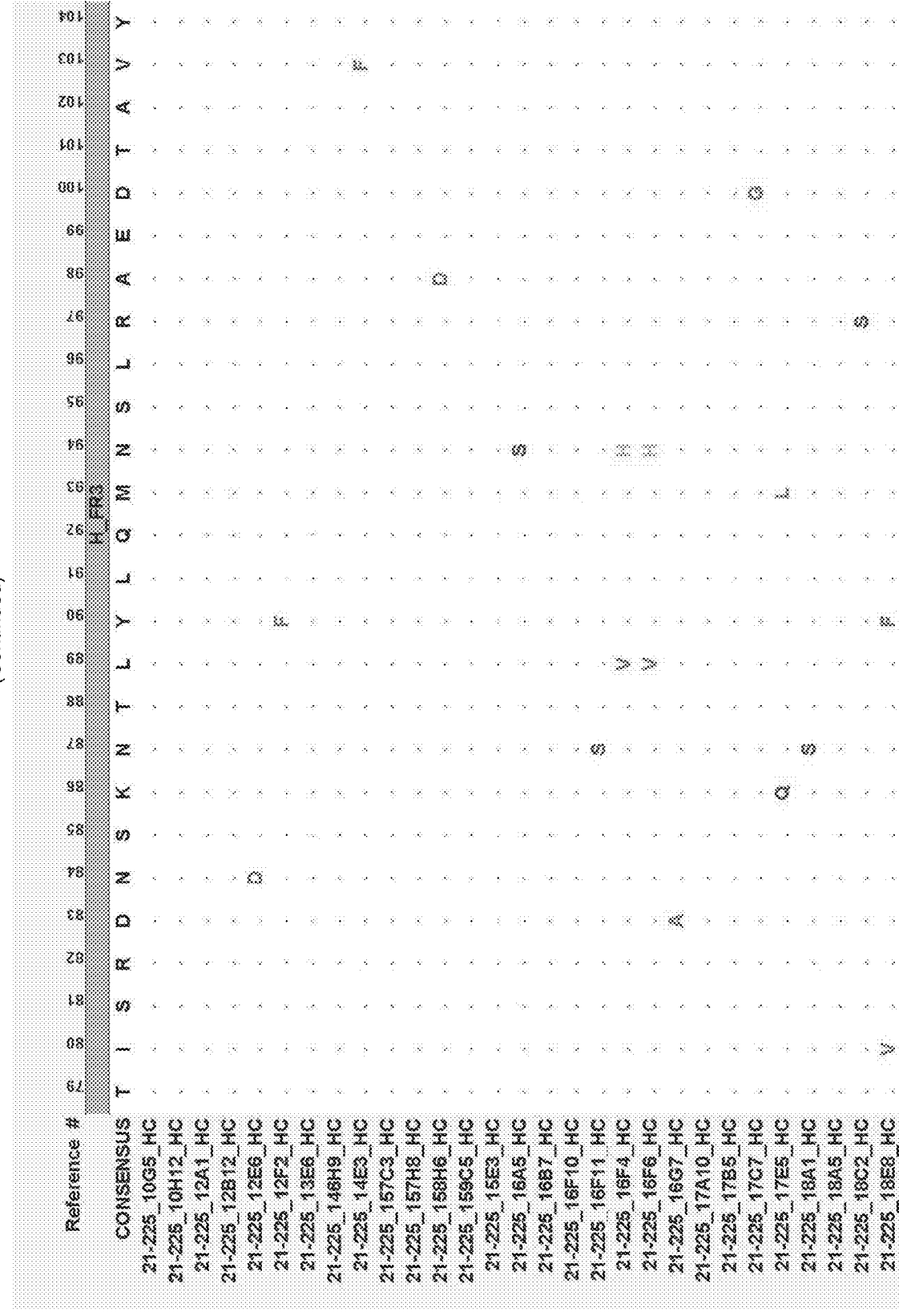
Figure 57:
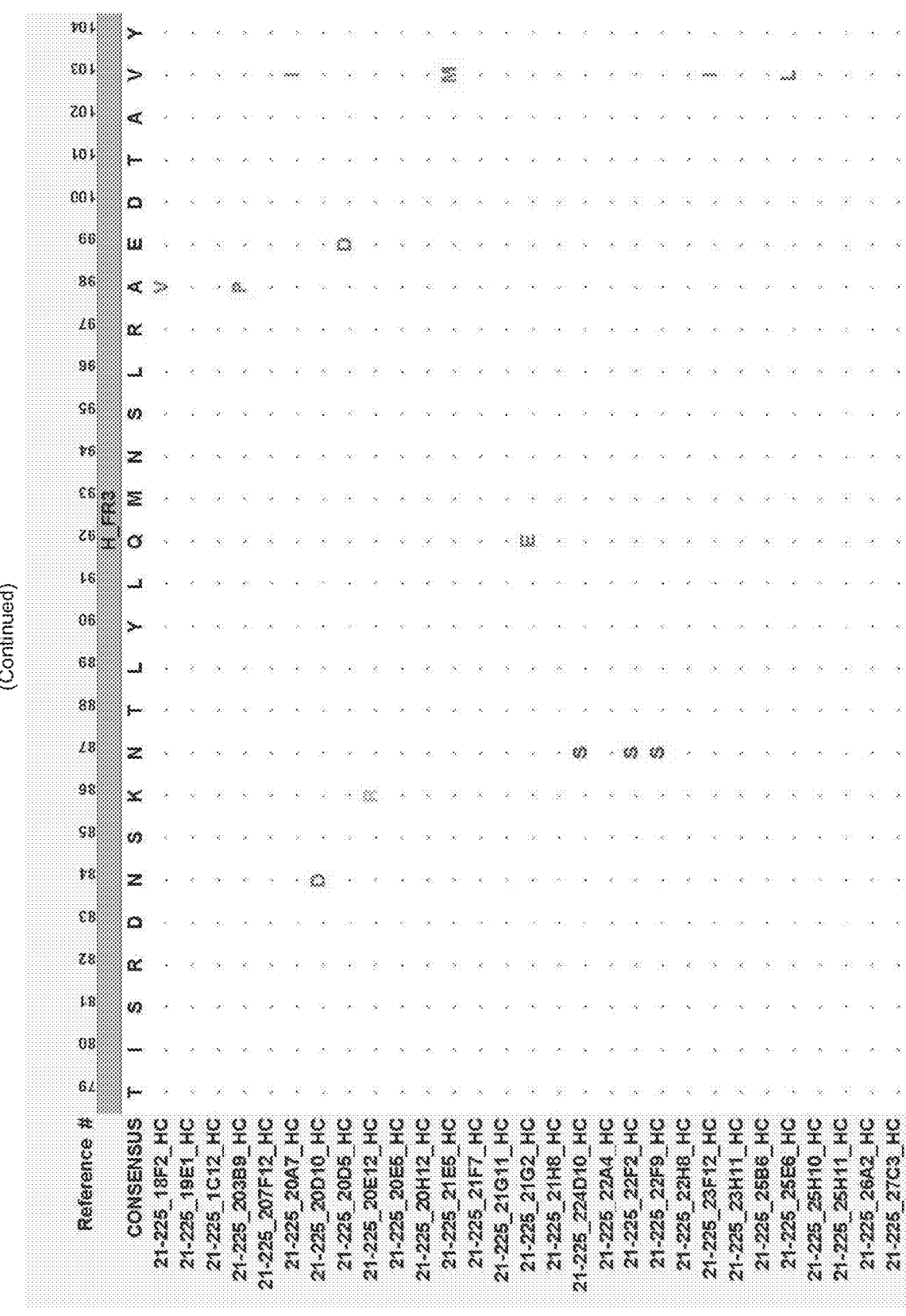
Figure 57:
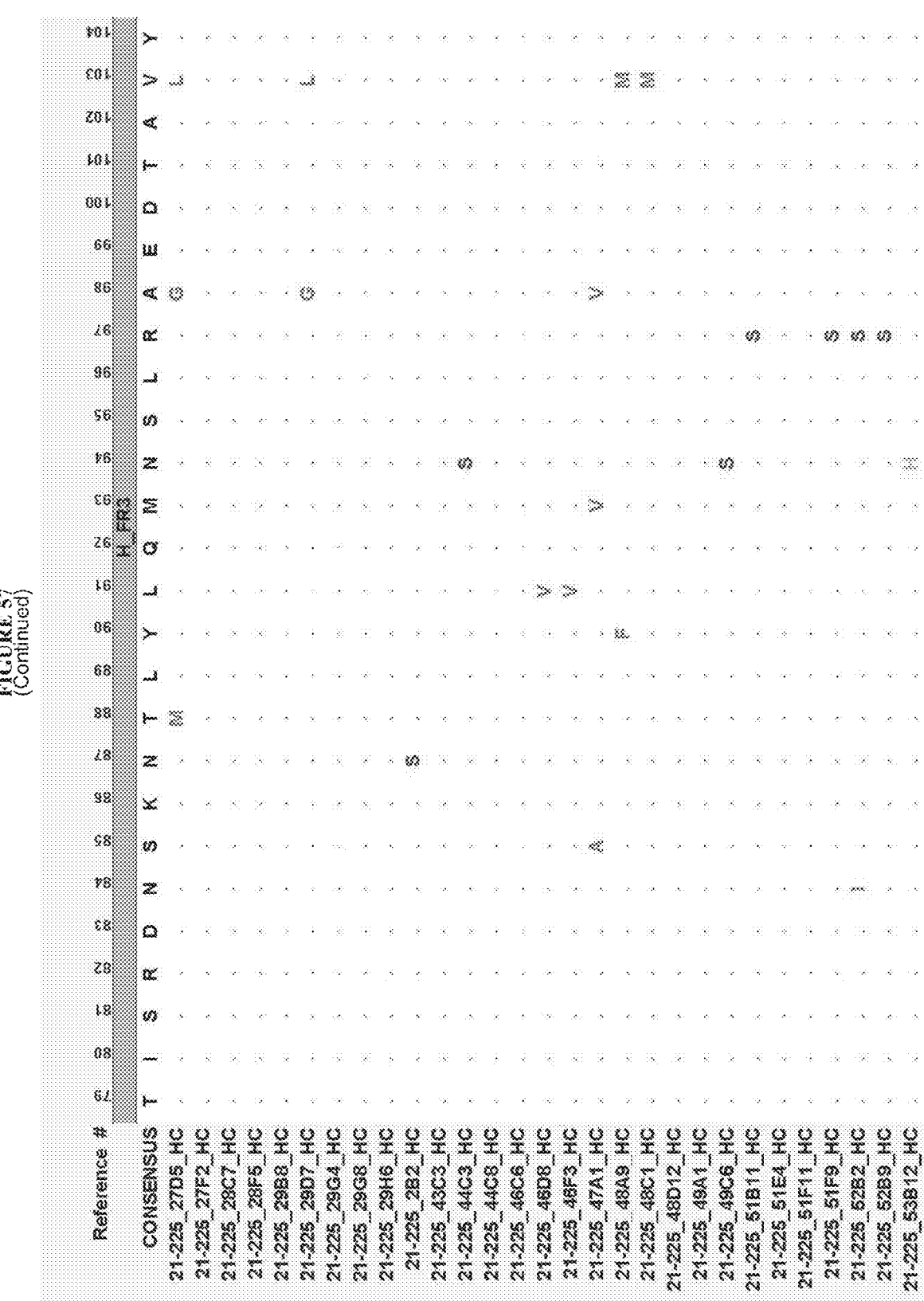
Figure 57:
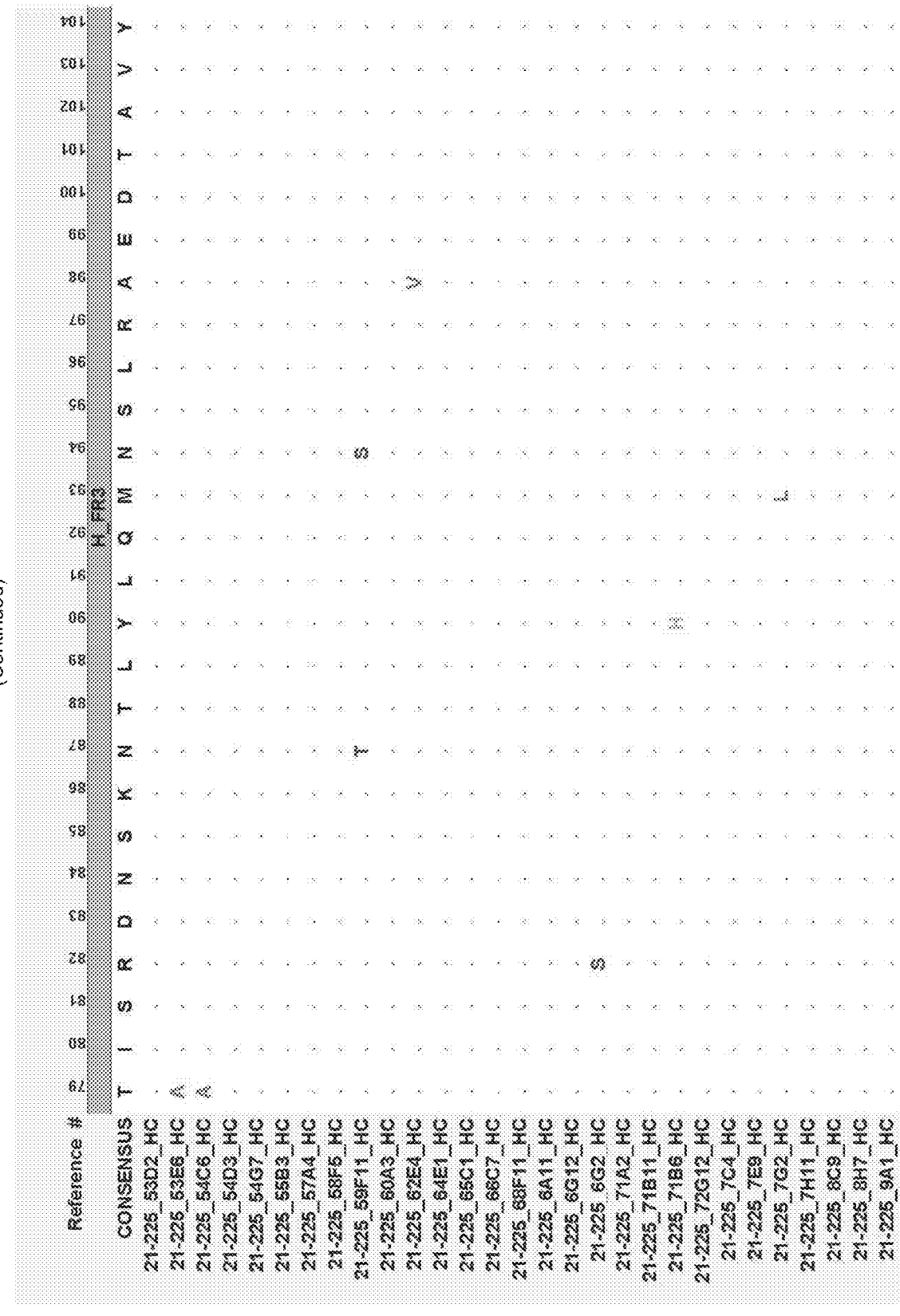
Figure 57:
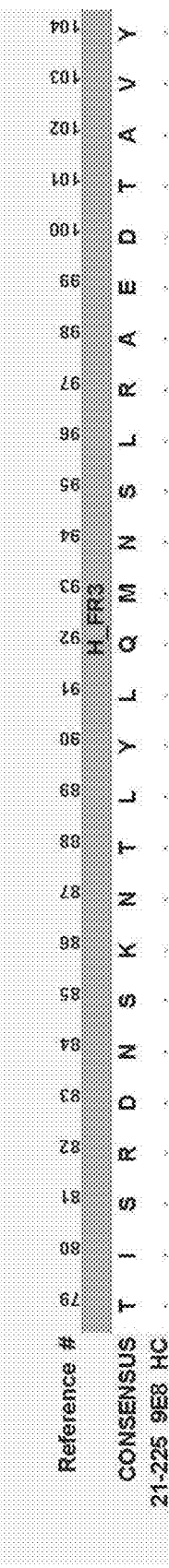
Figure 57:
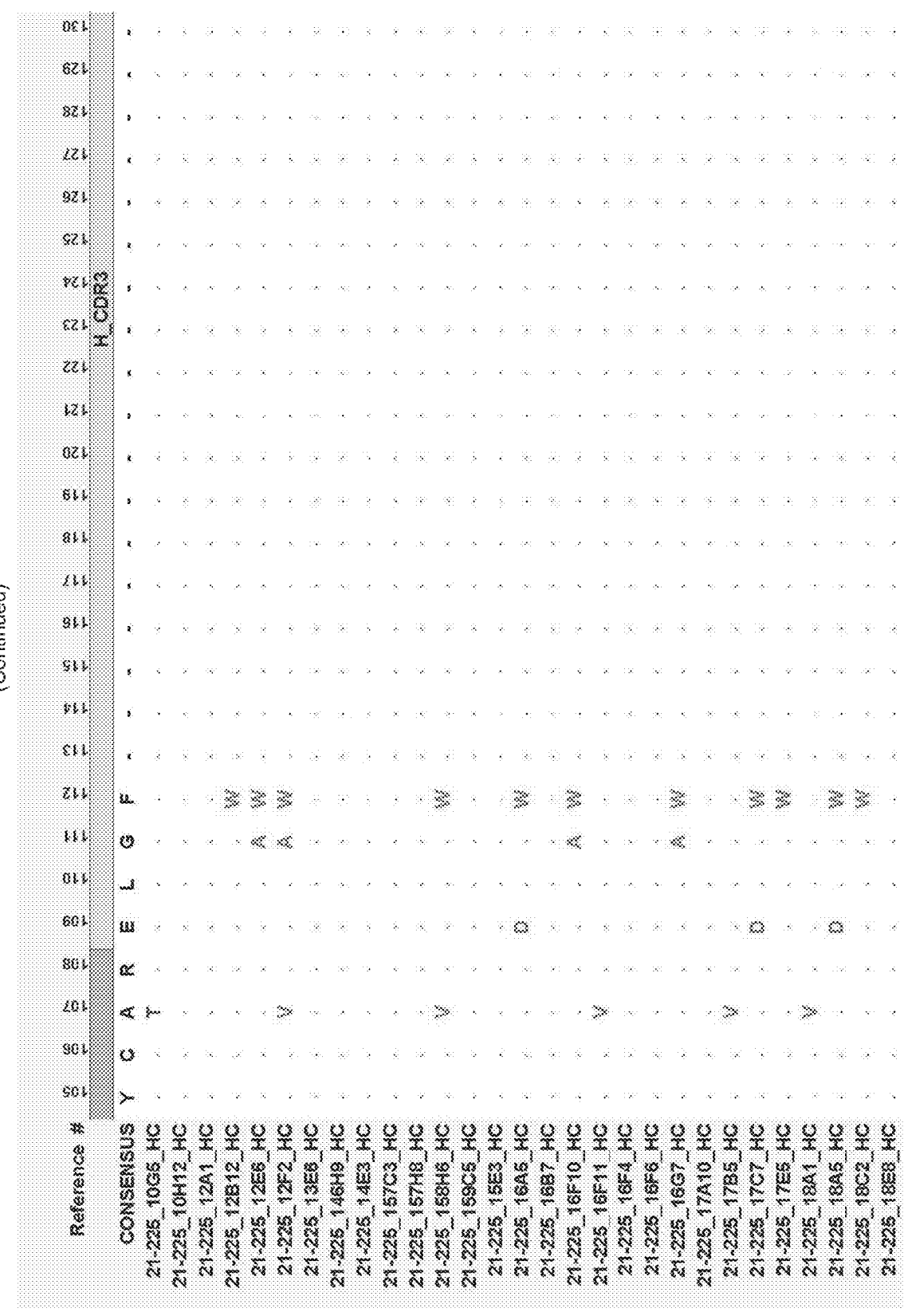
Figure 57:
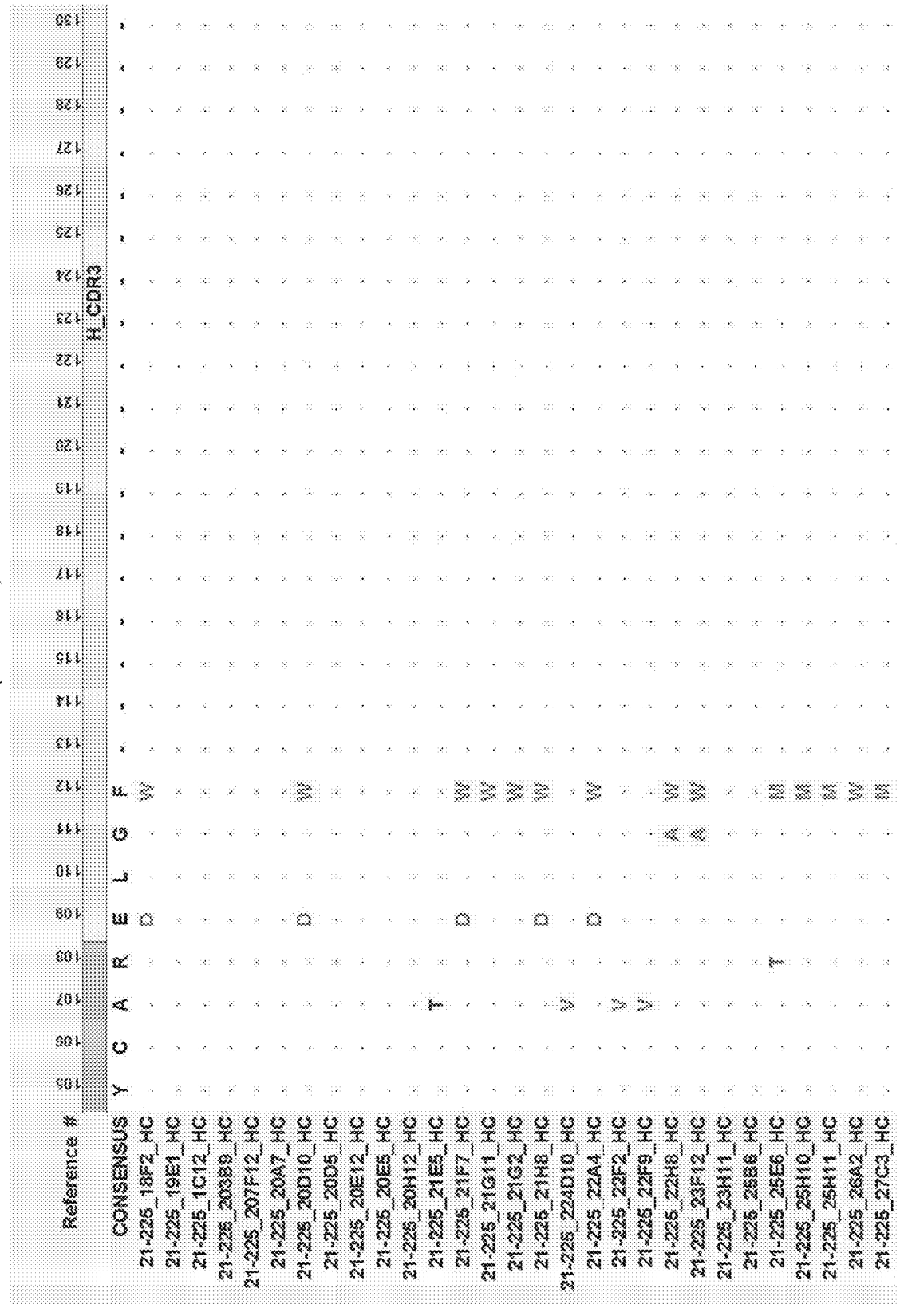
Figure 57:
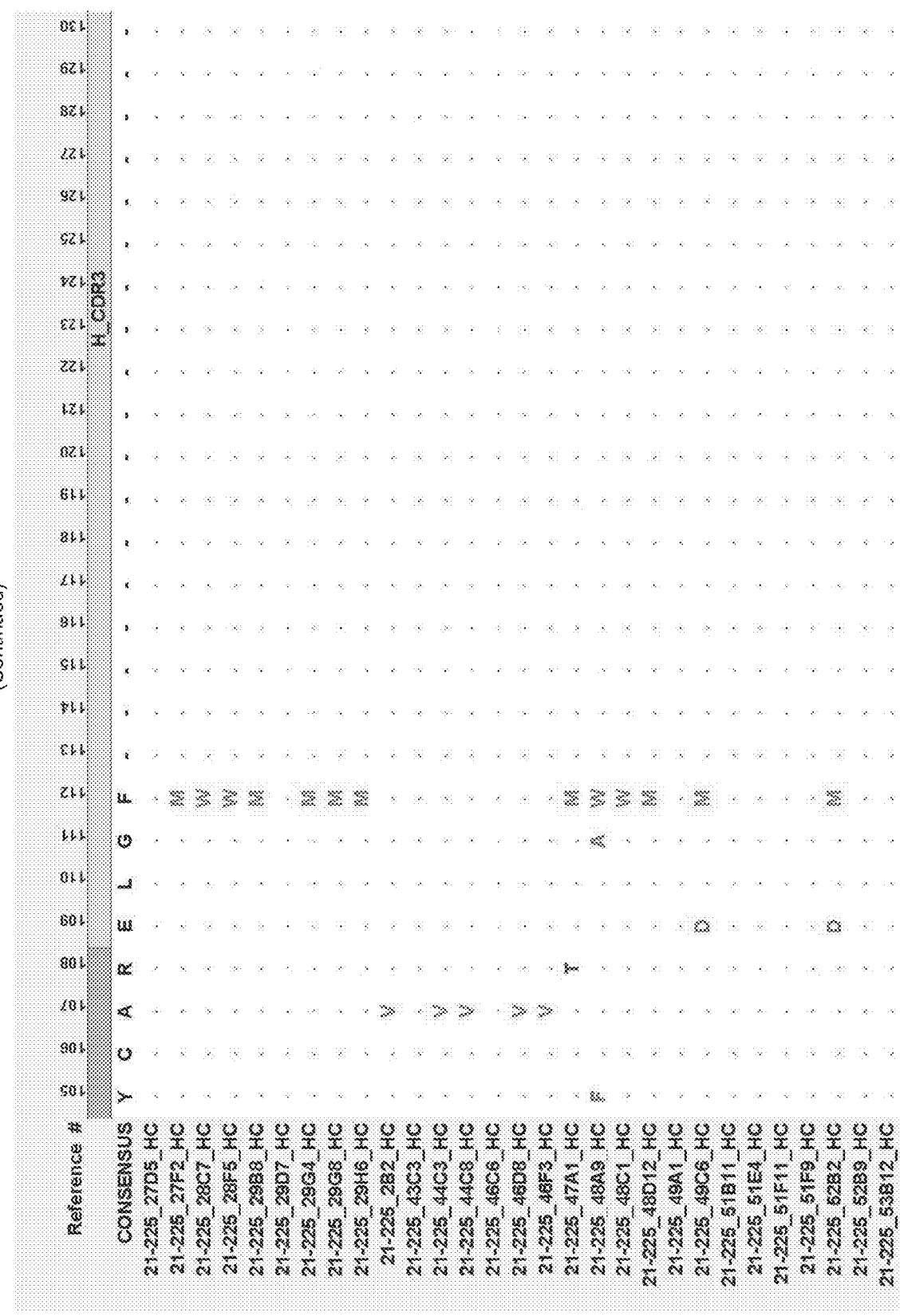
Figure 57:
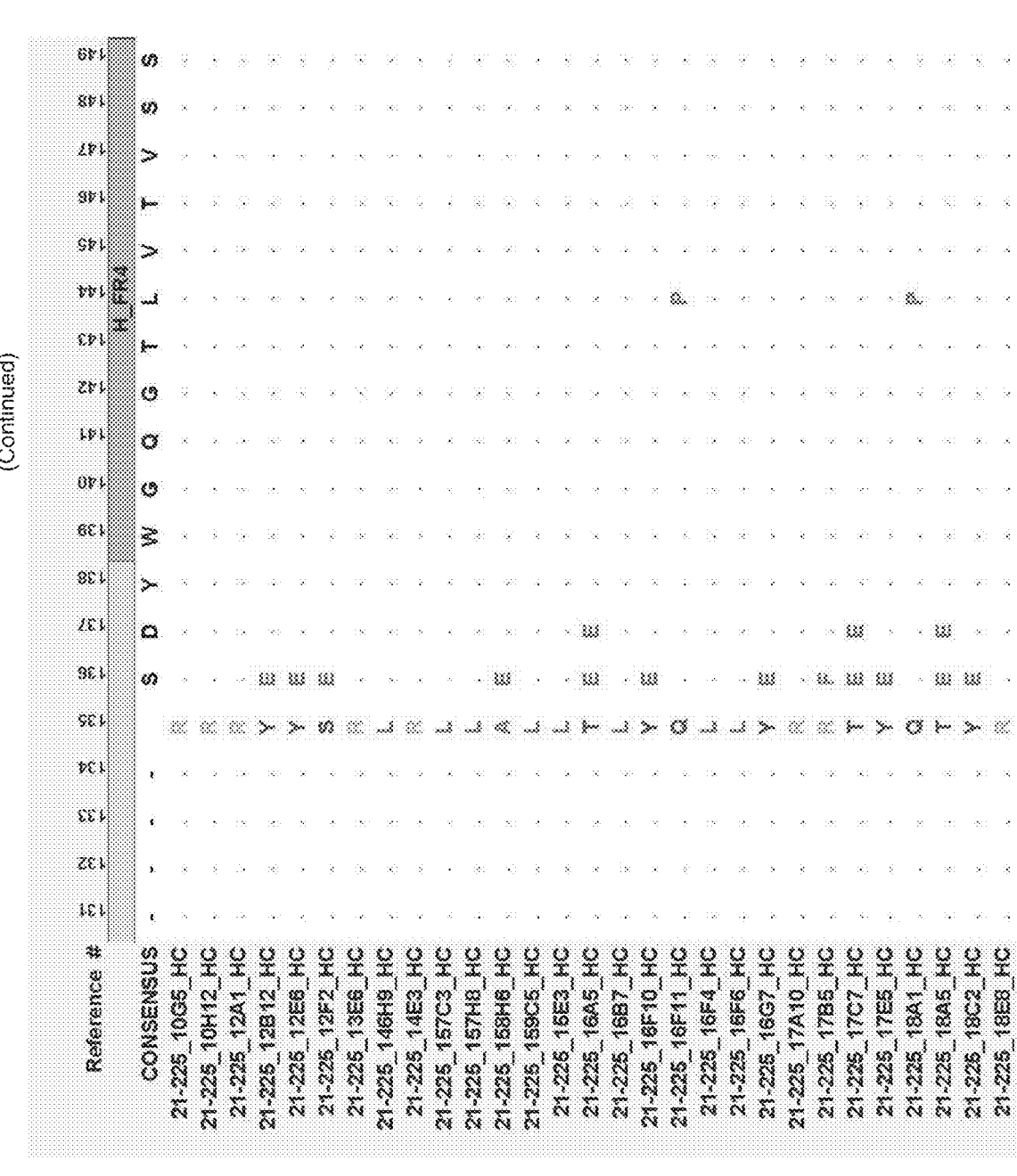
Figure 57:
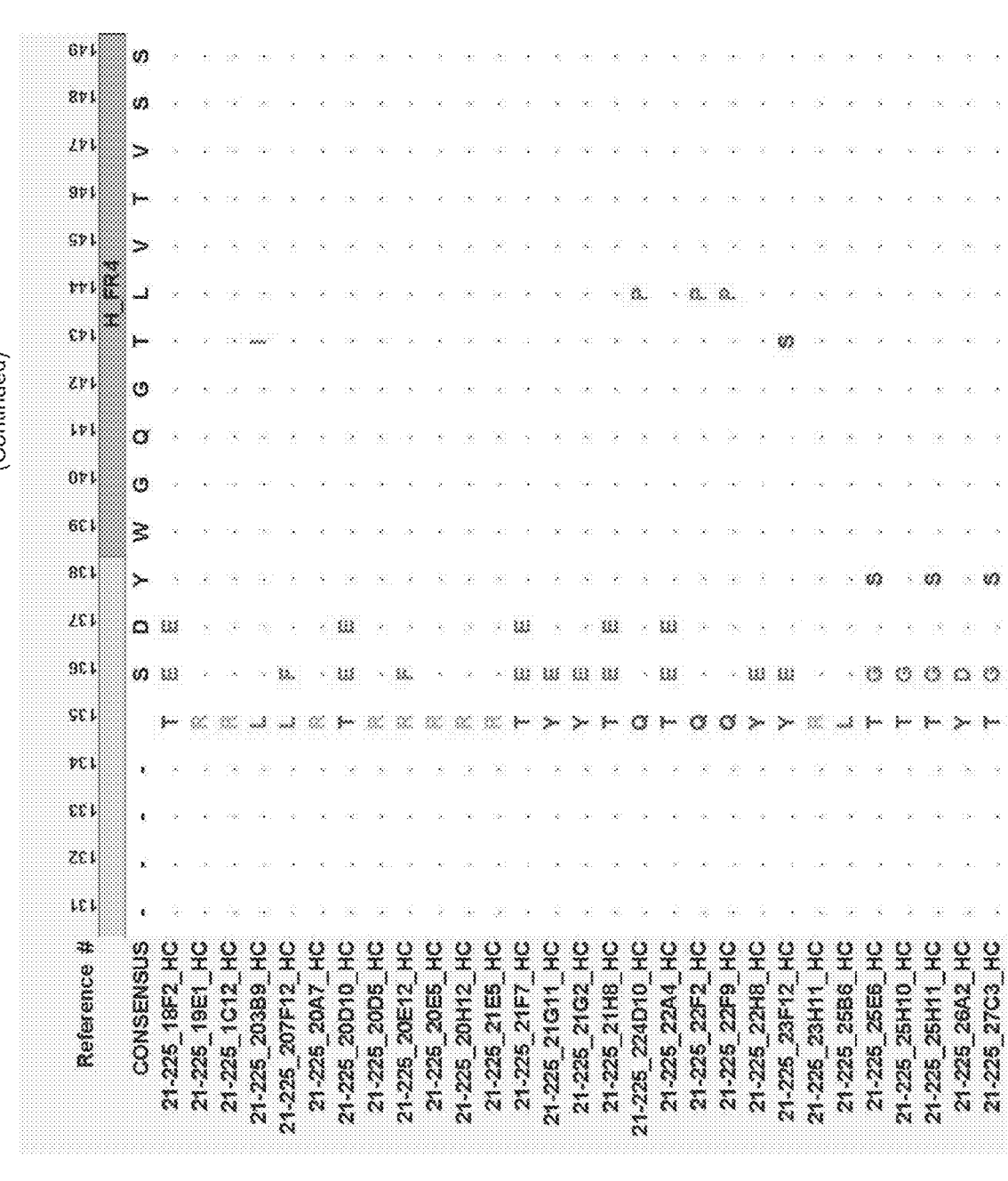
Figure 57:
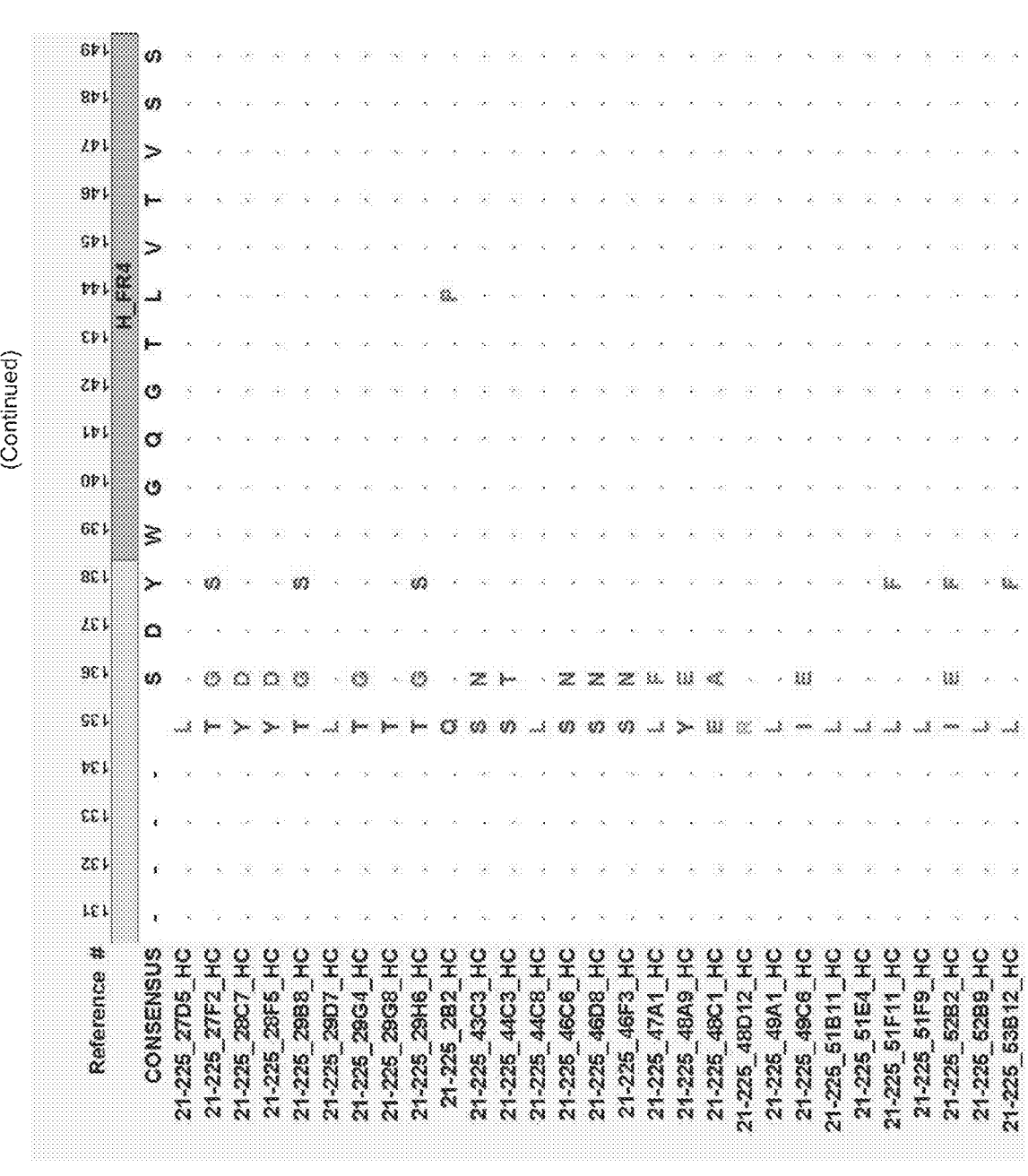
Figure 57:
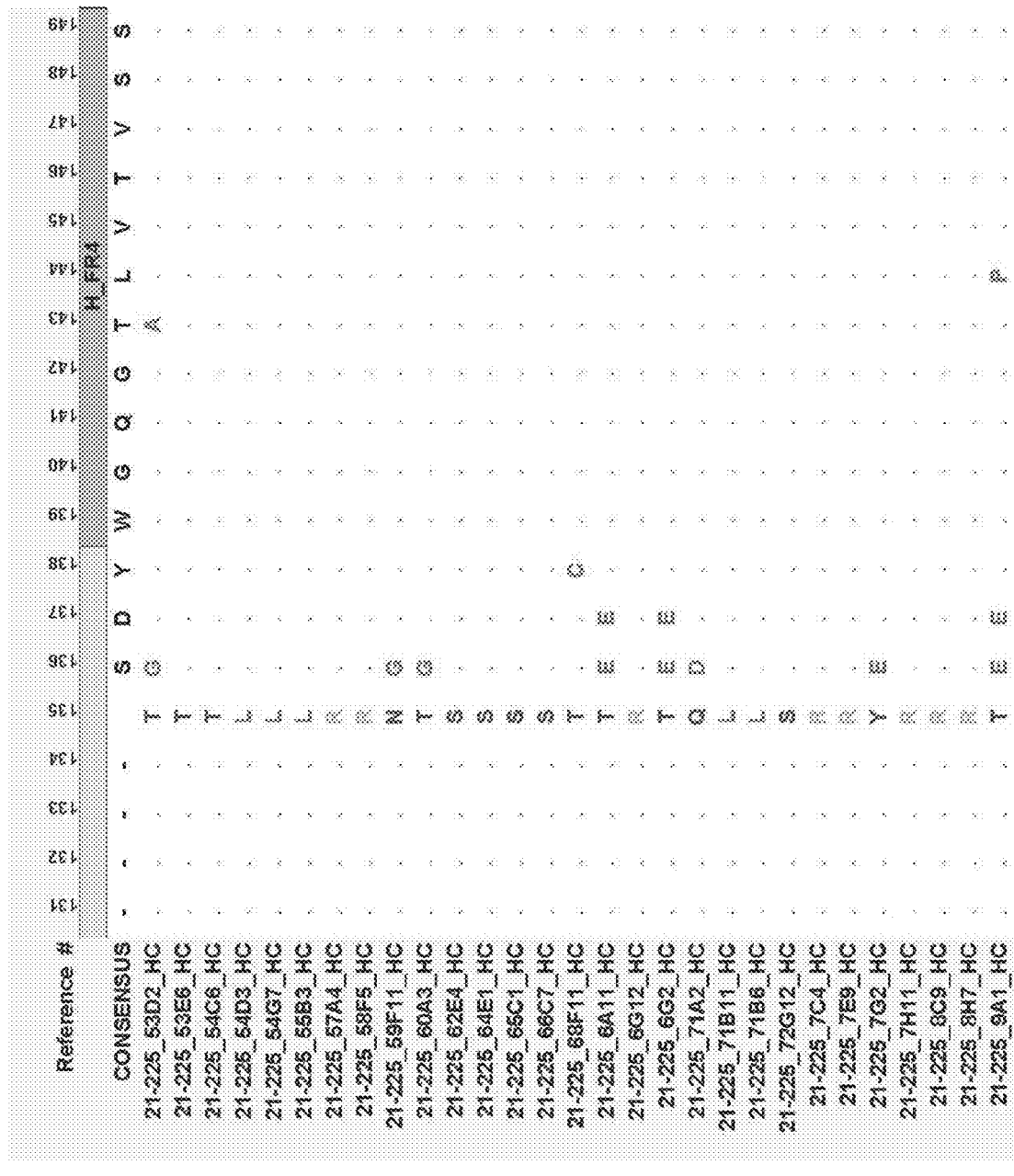
Figure 57:
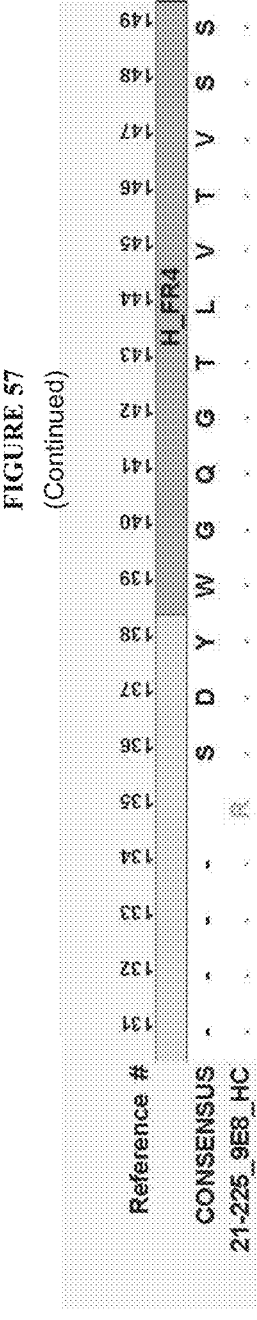
Figure 57:
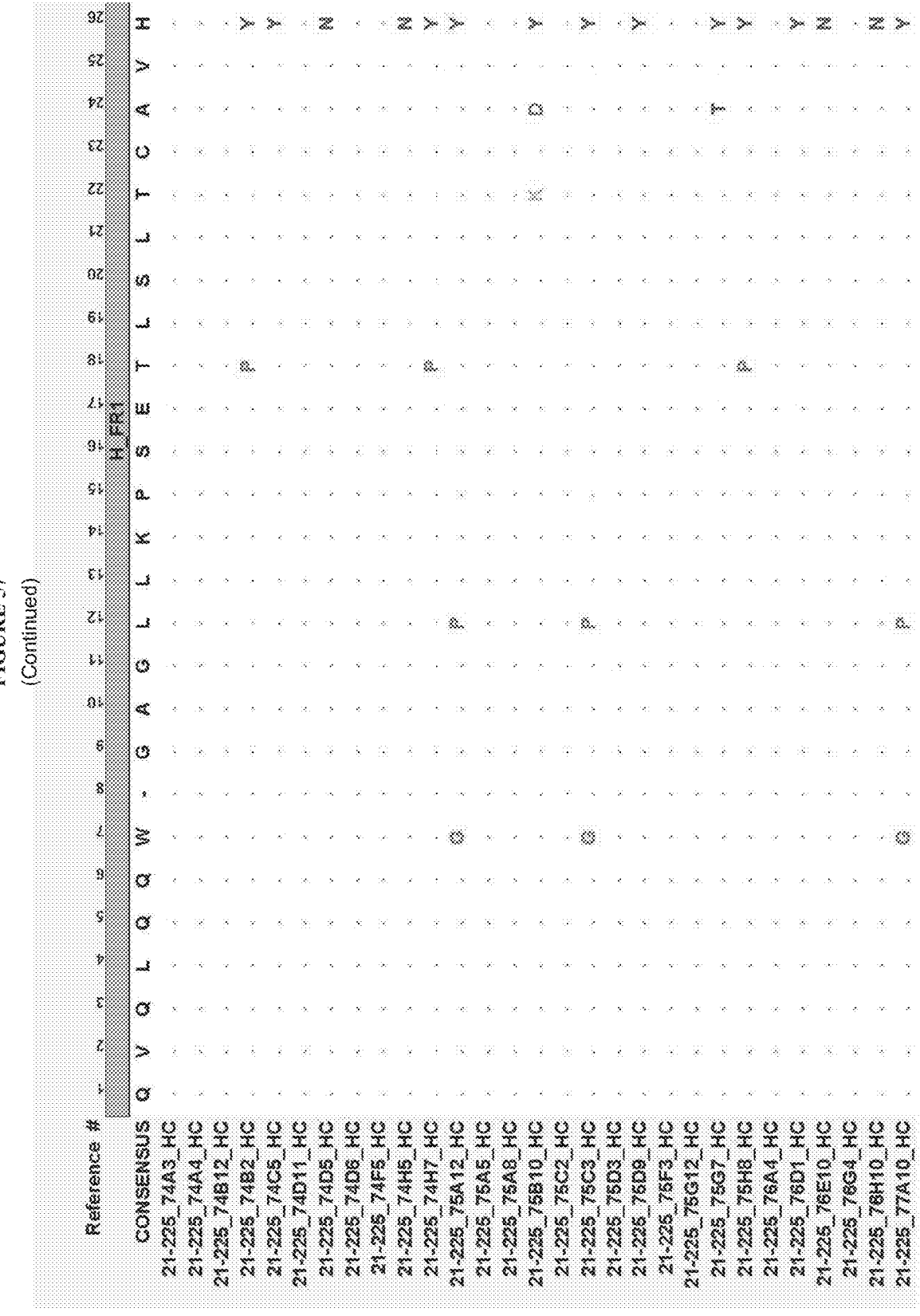
Figure 57:
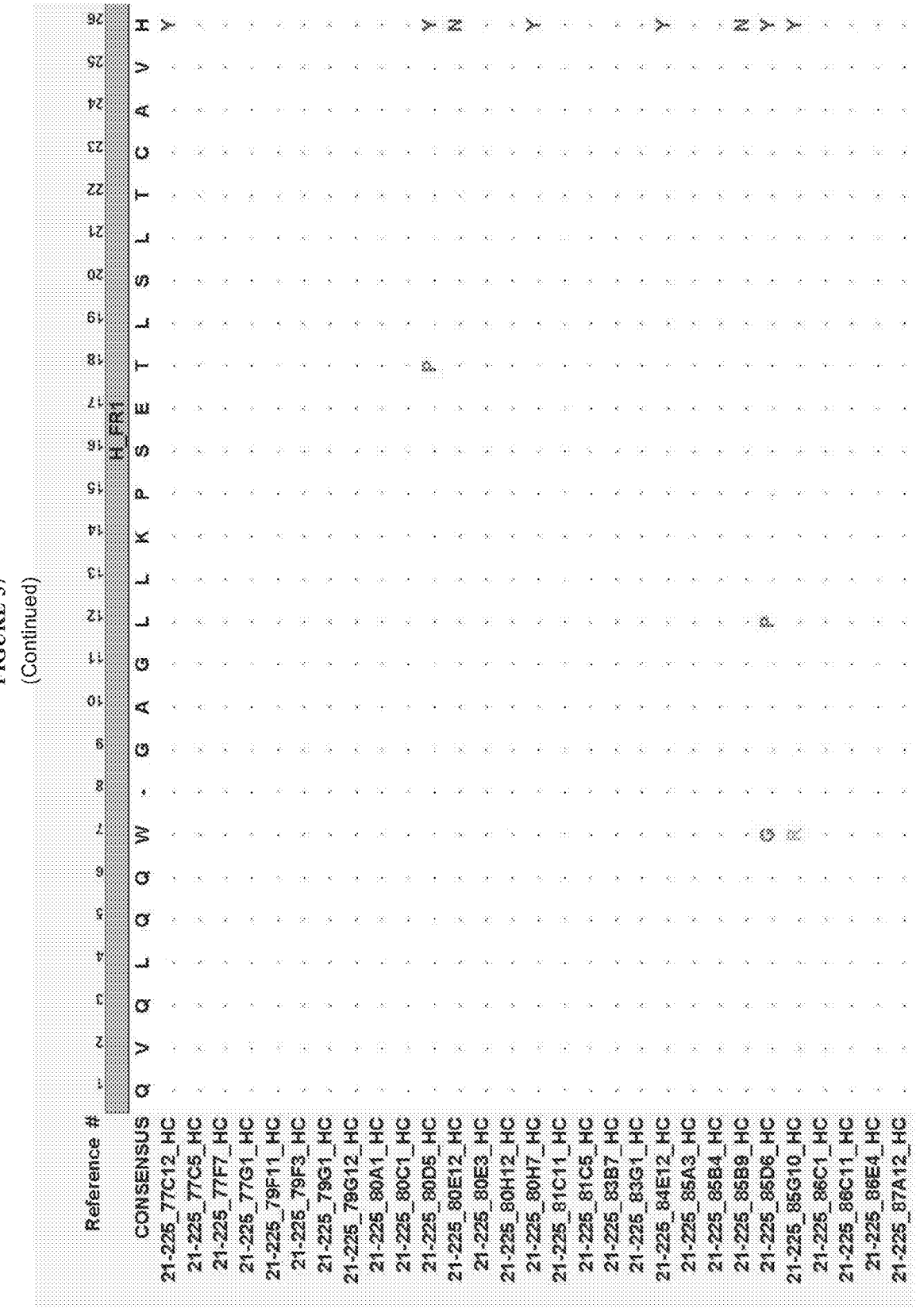
Figure 57:
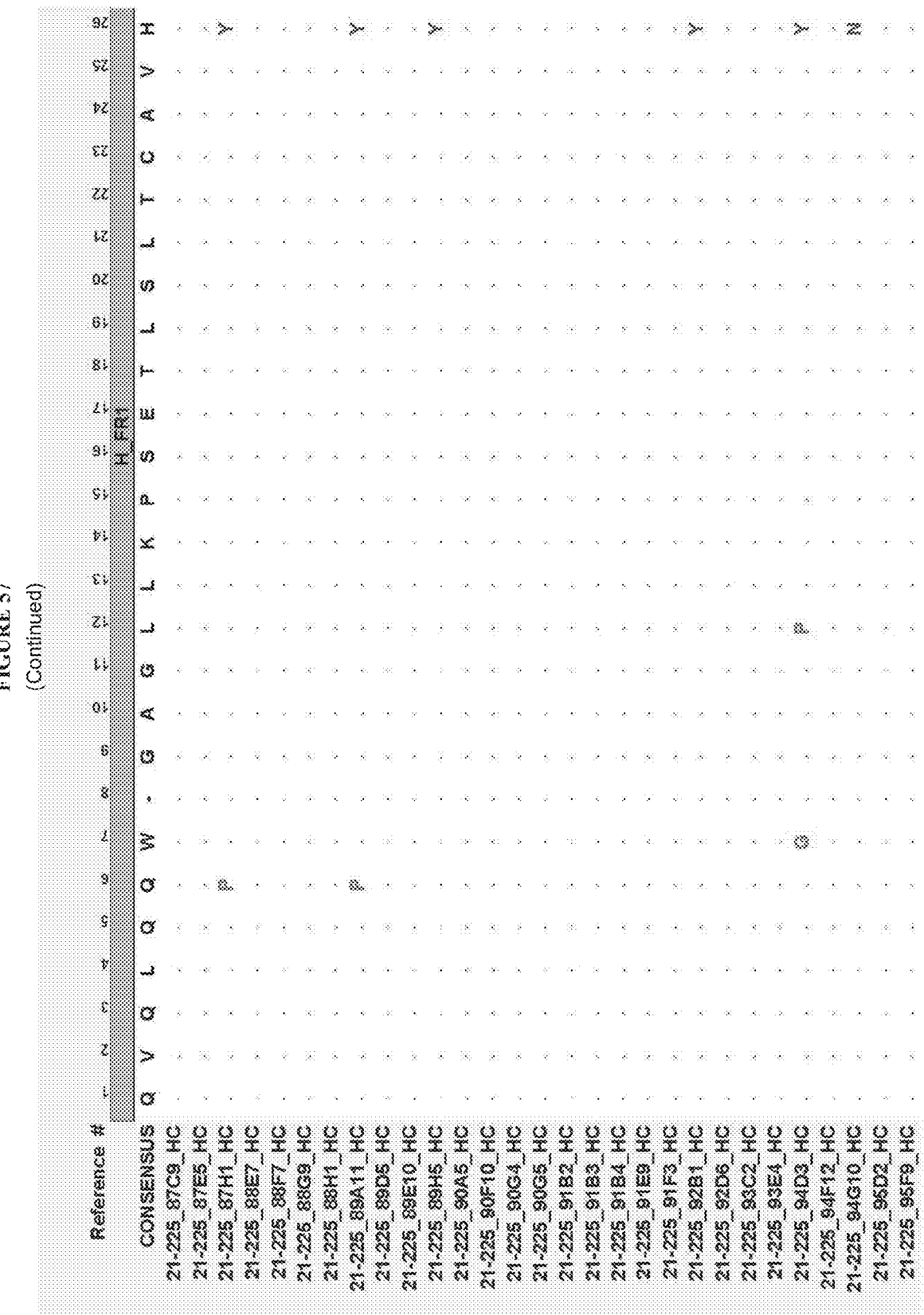
Figure 57:
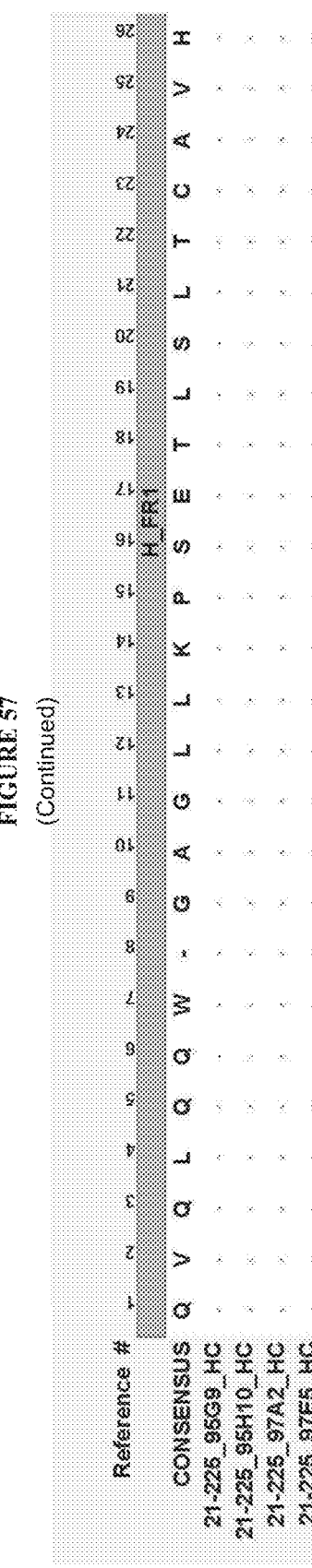
Figure 57:
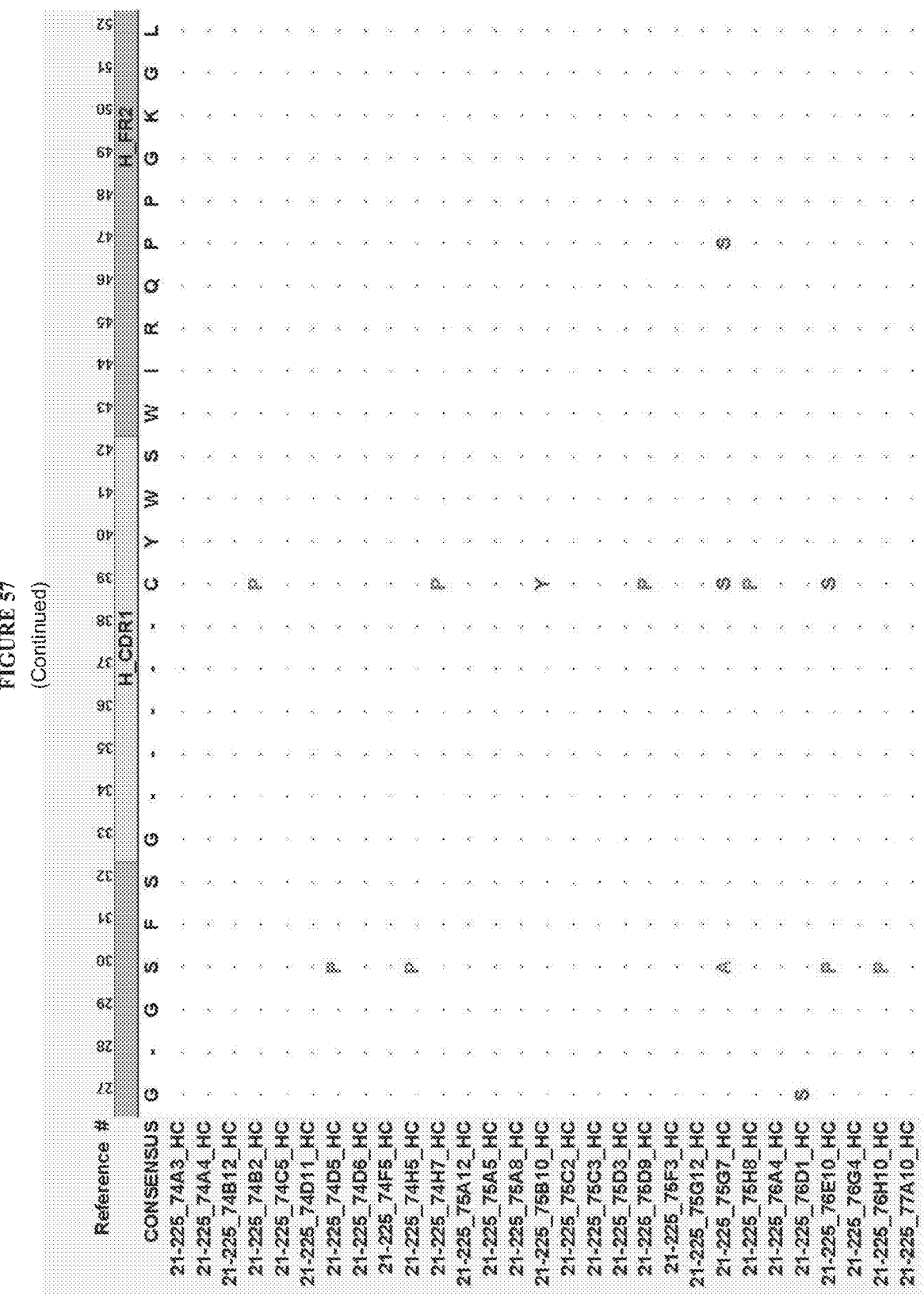
Figure 57:
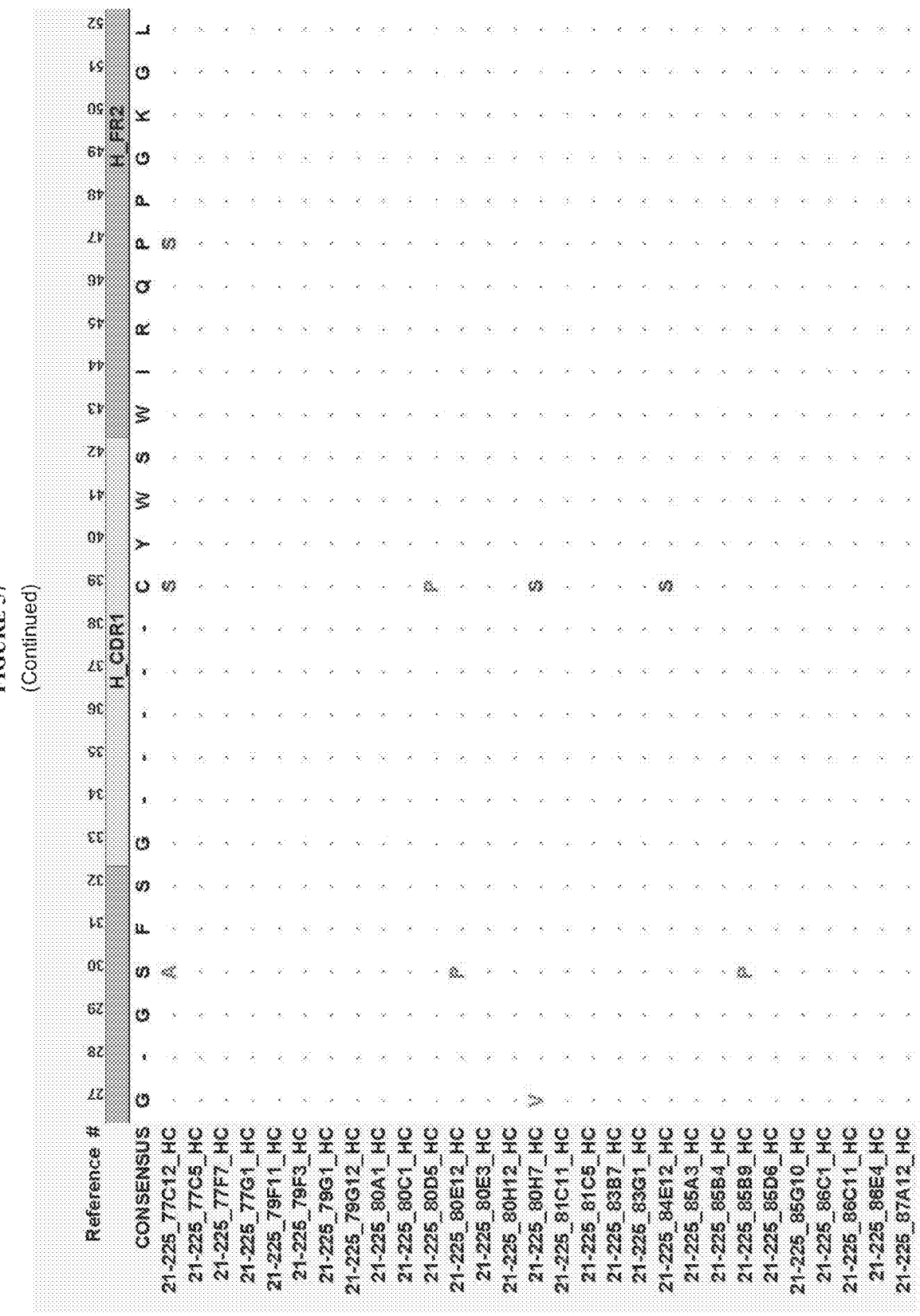
Figure 57:
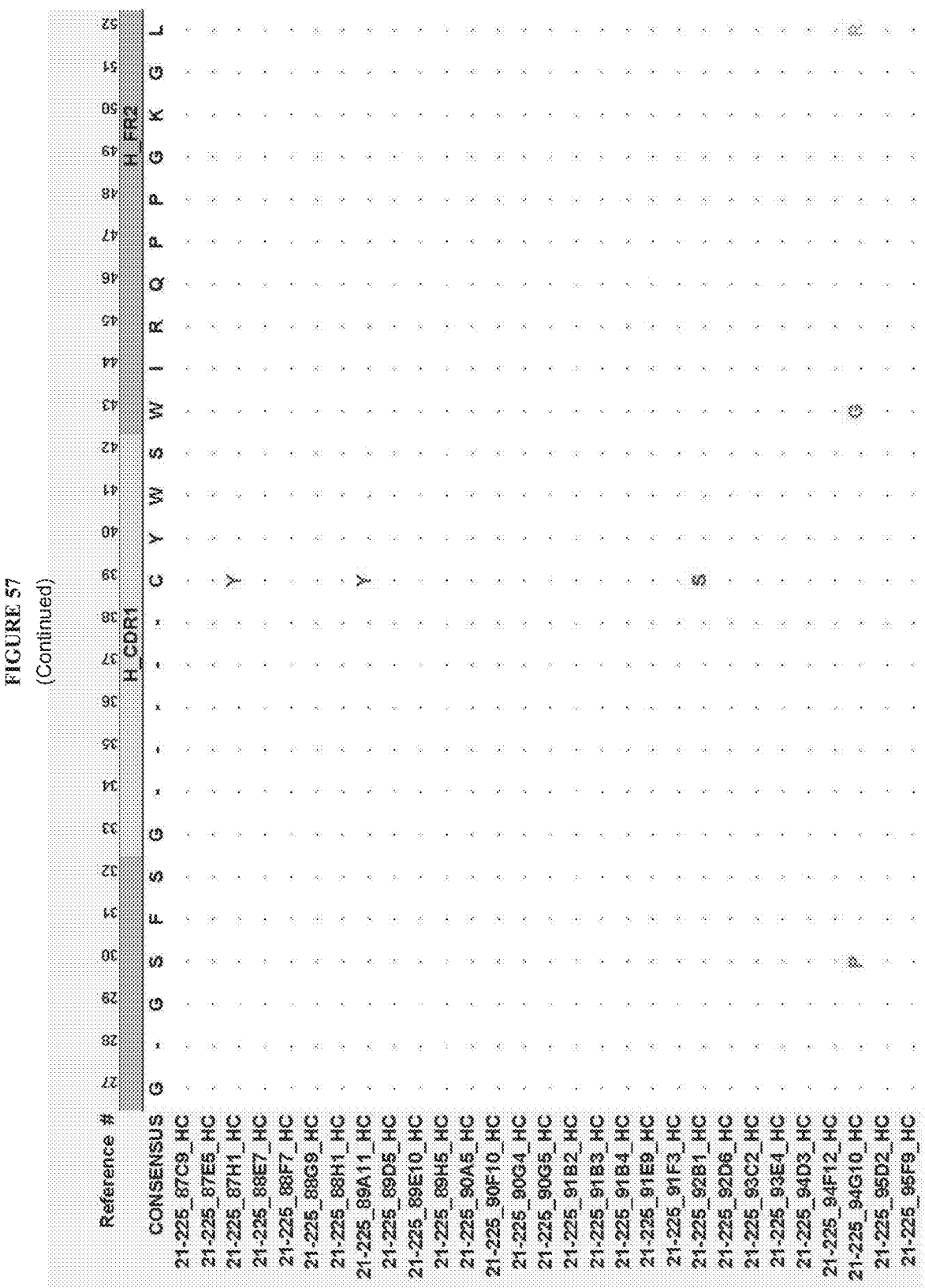
Figure 57:
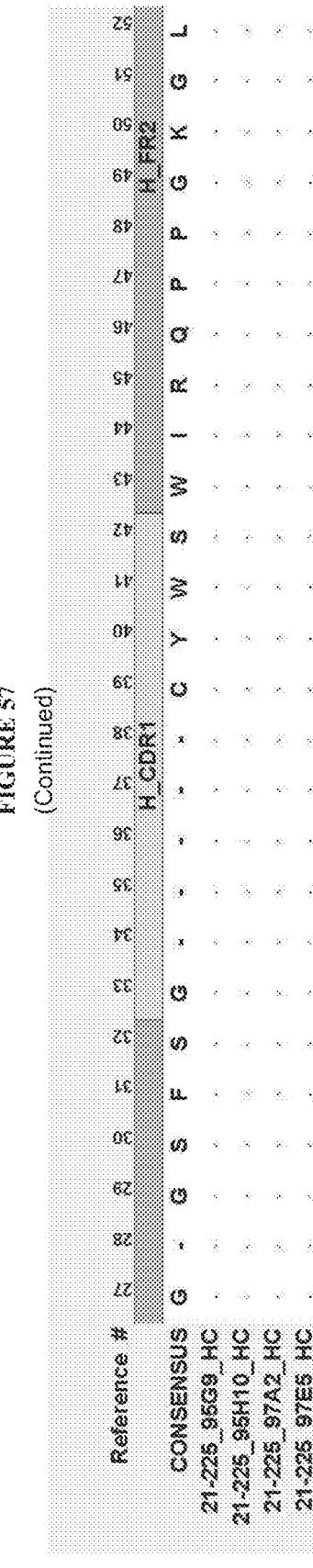
Figure 57:
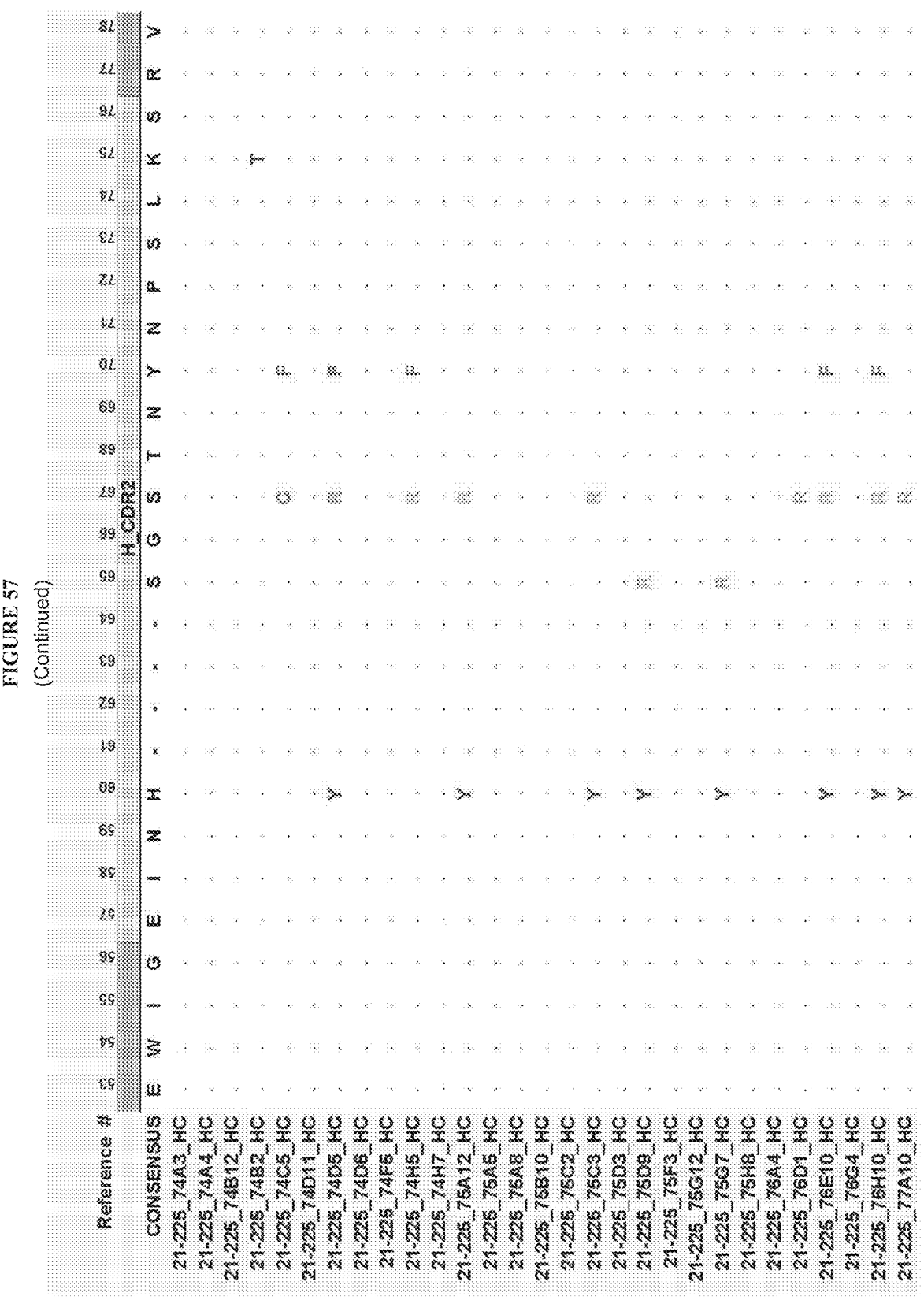
Figure 57:
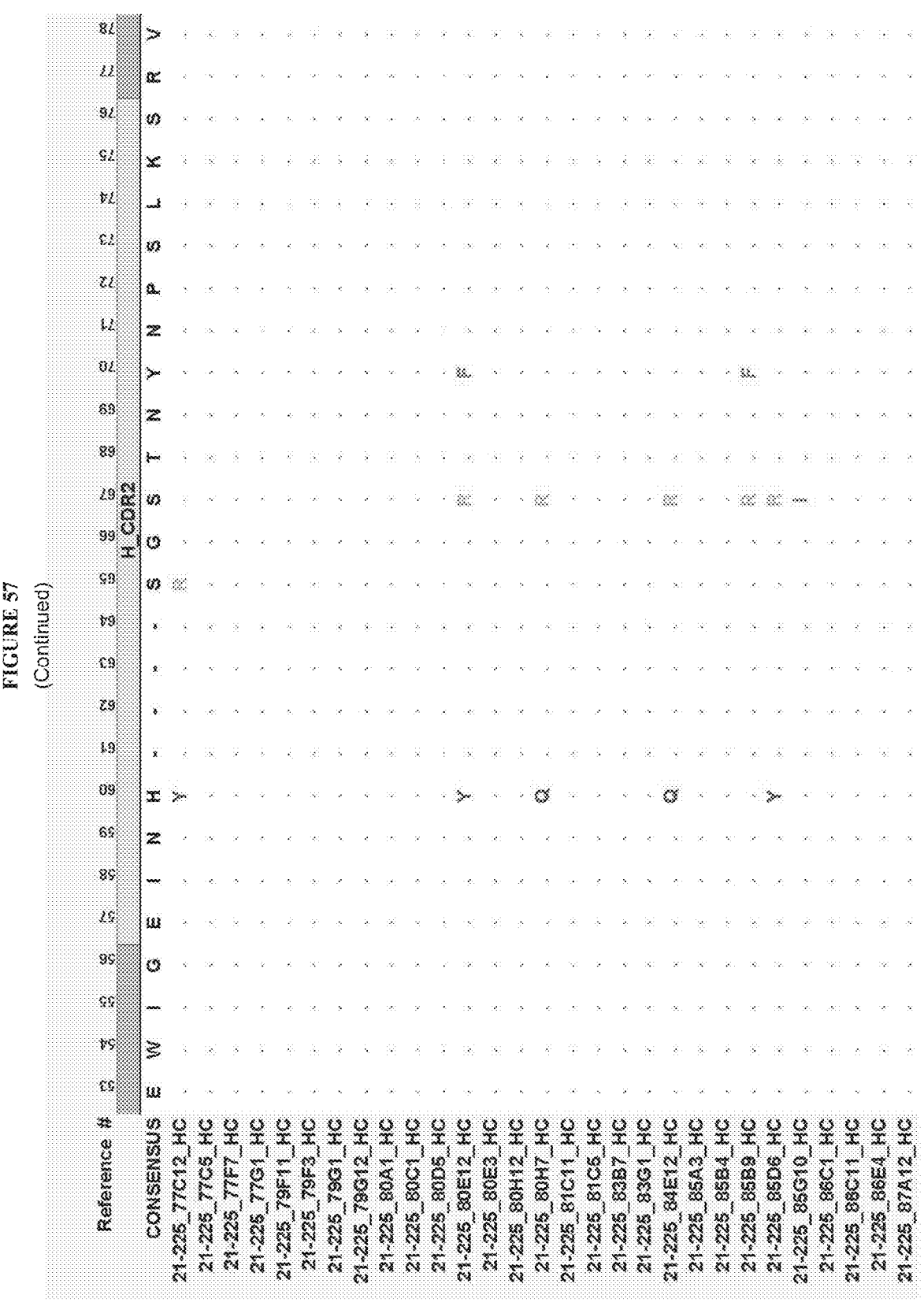
Figure 57:
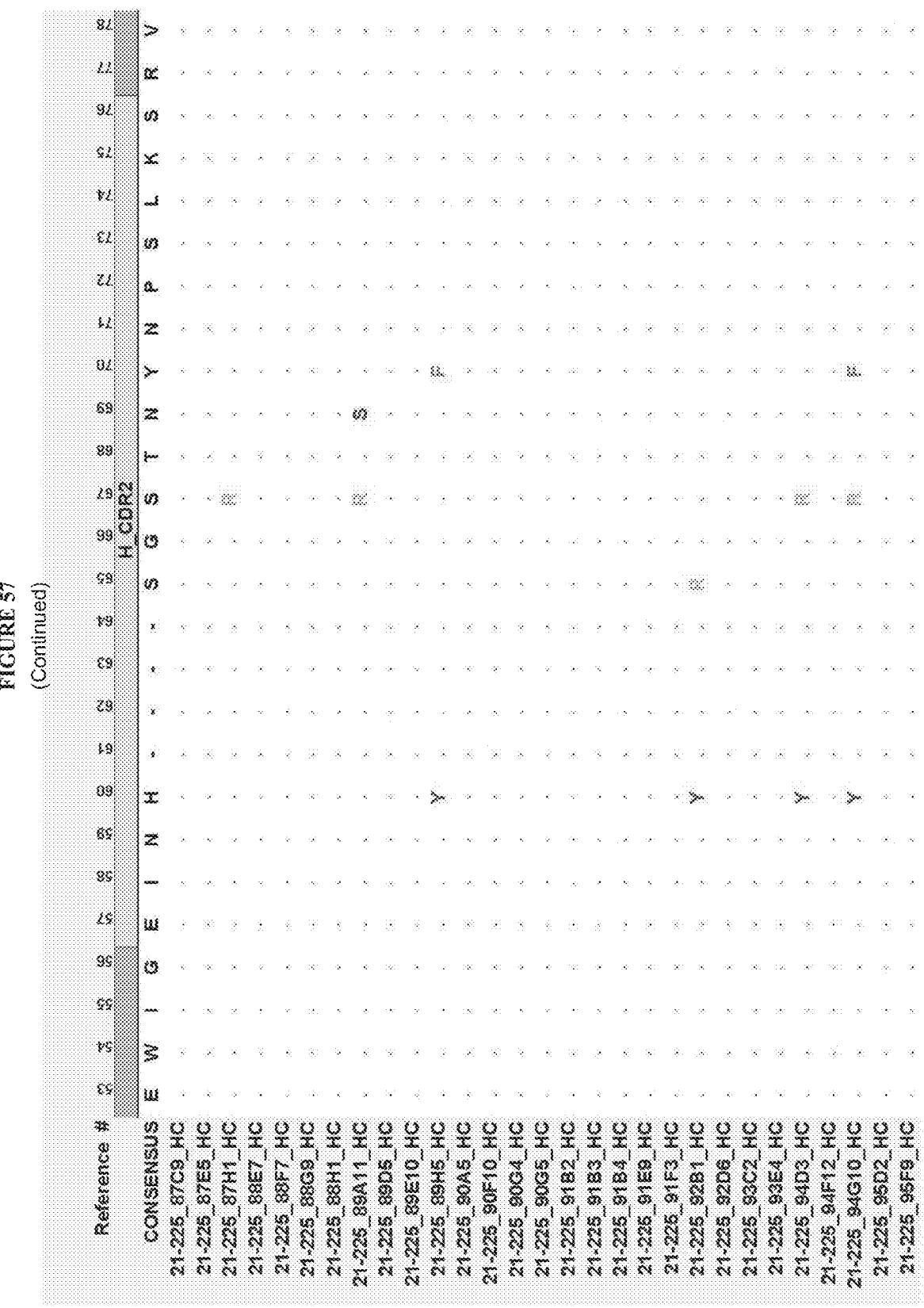
Figure 57:
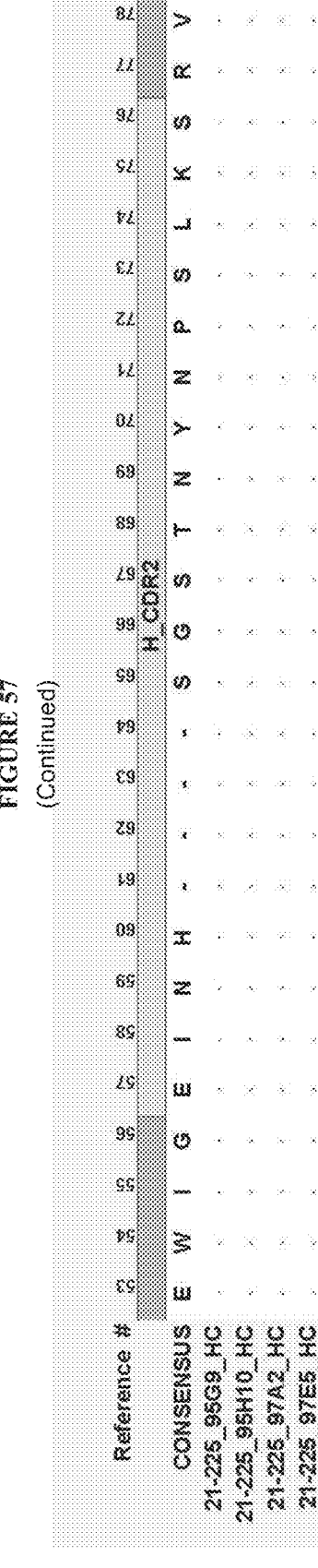
Figure 57:
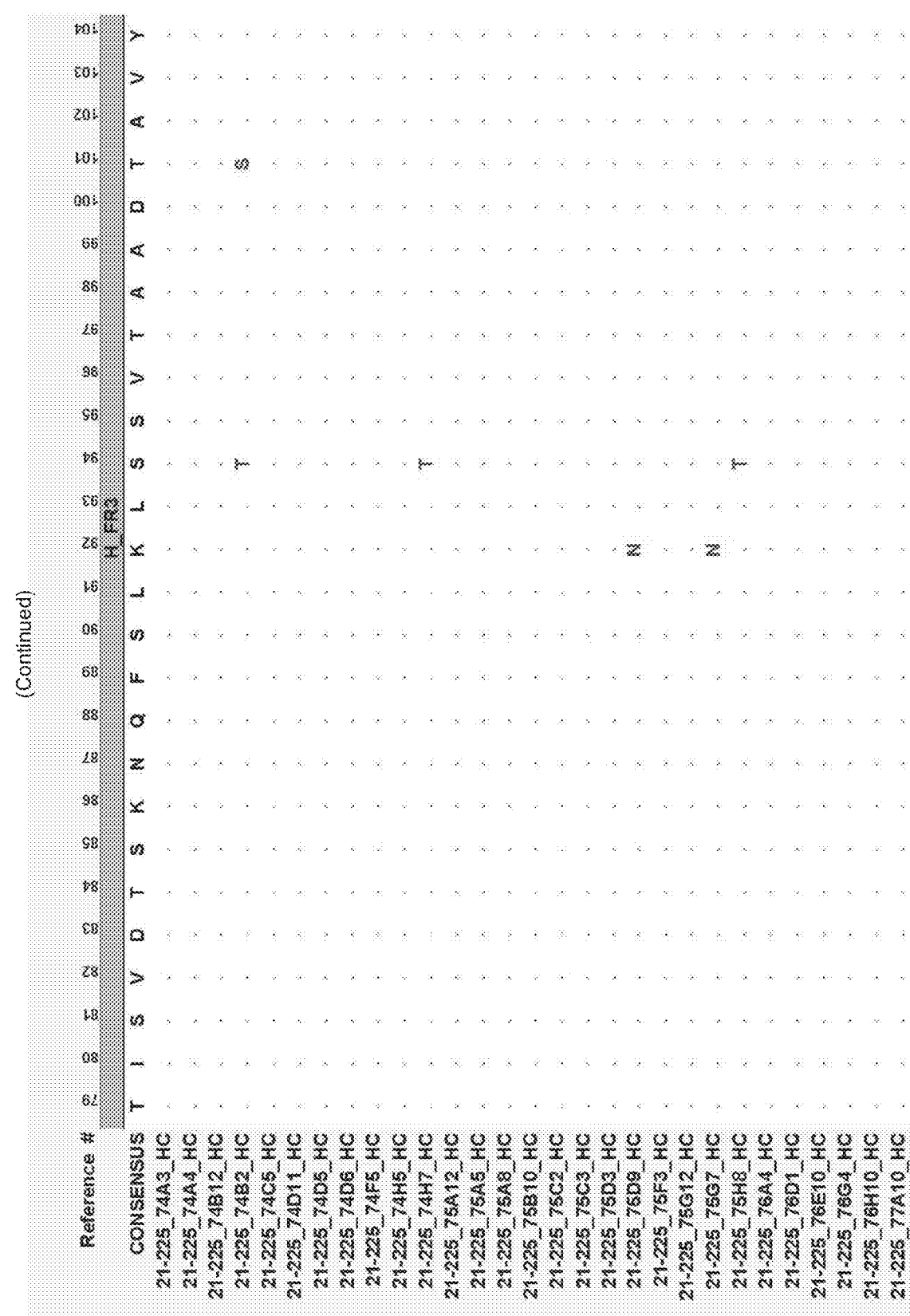
Figure 57:
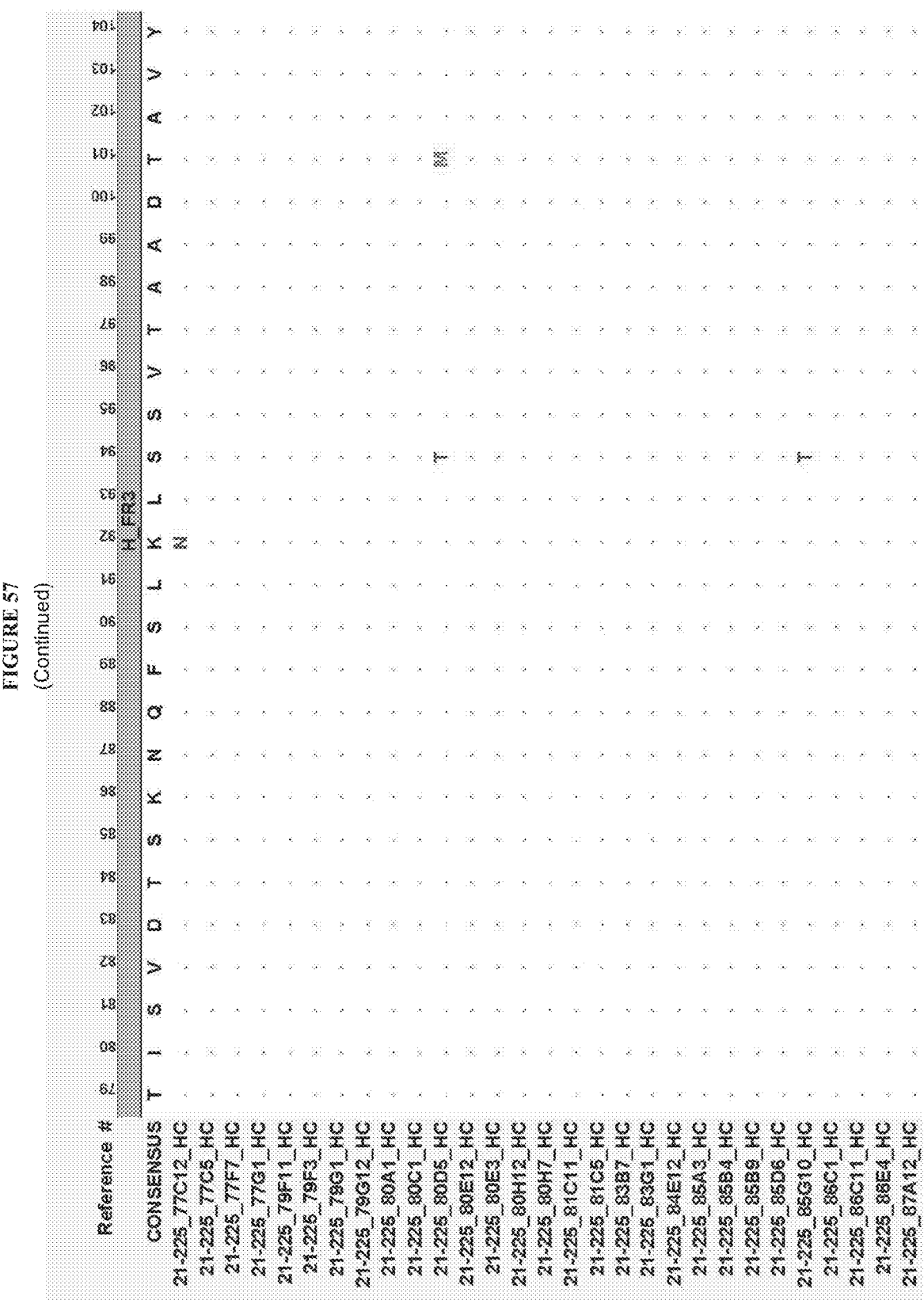
Figure 57:
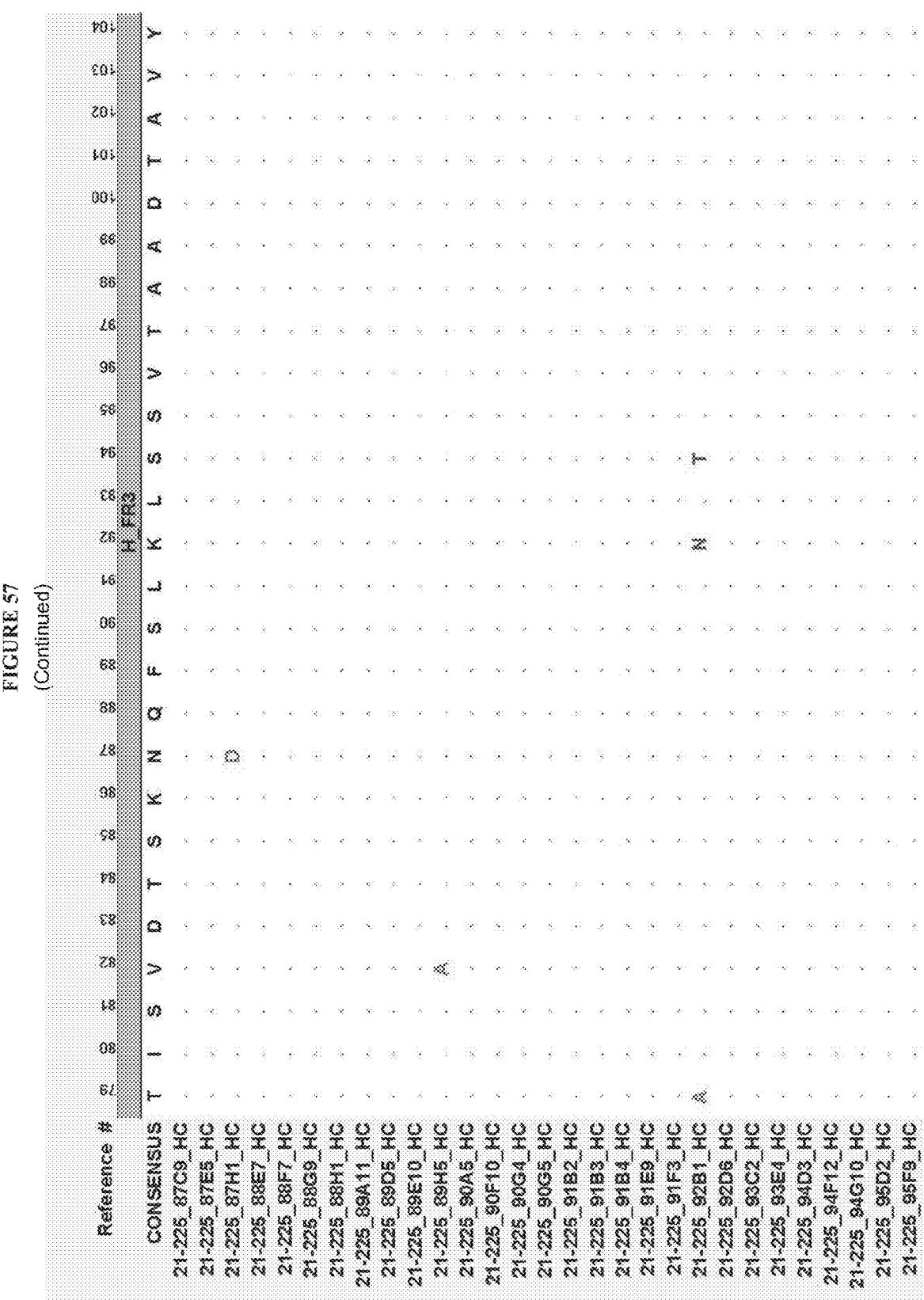
Figure 57:
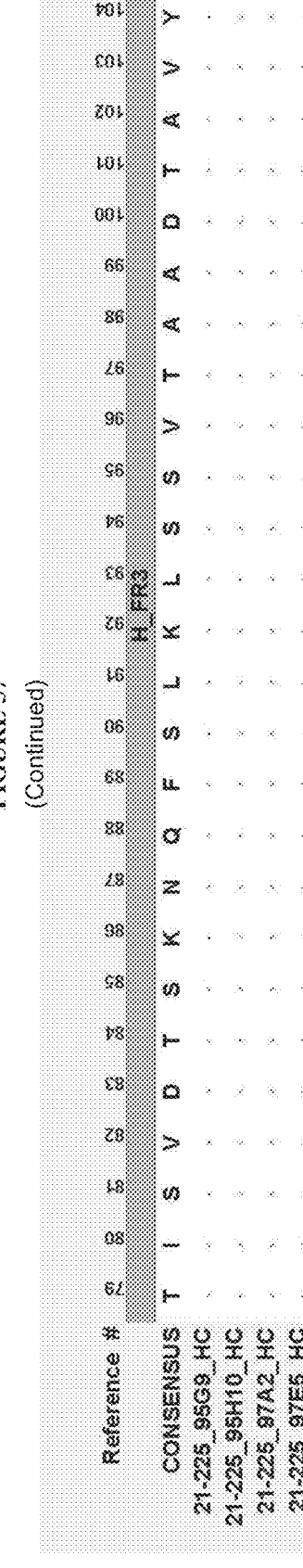
Figure 57:
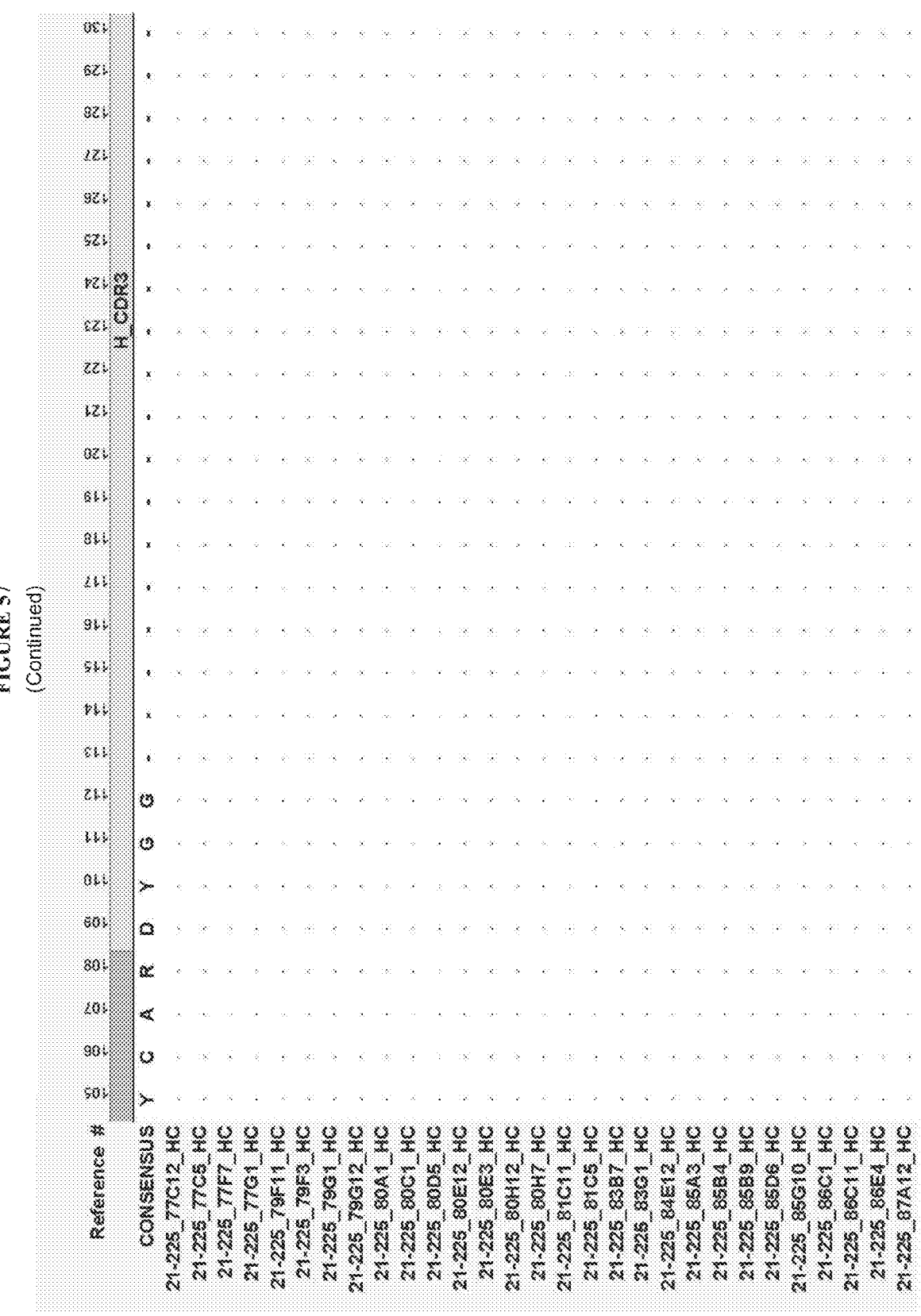
Figure 57:
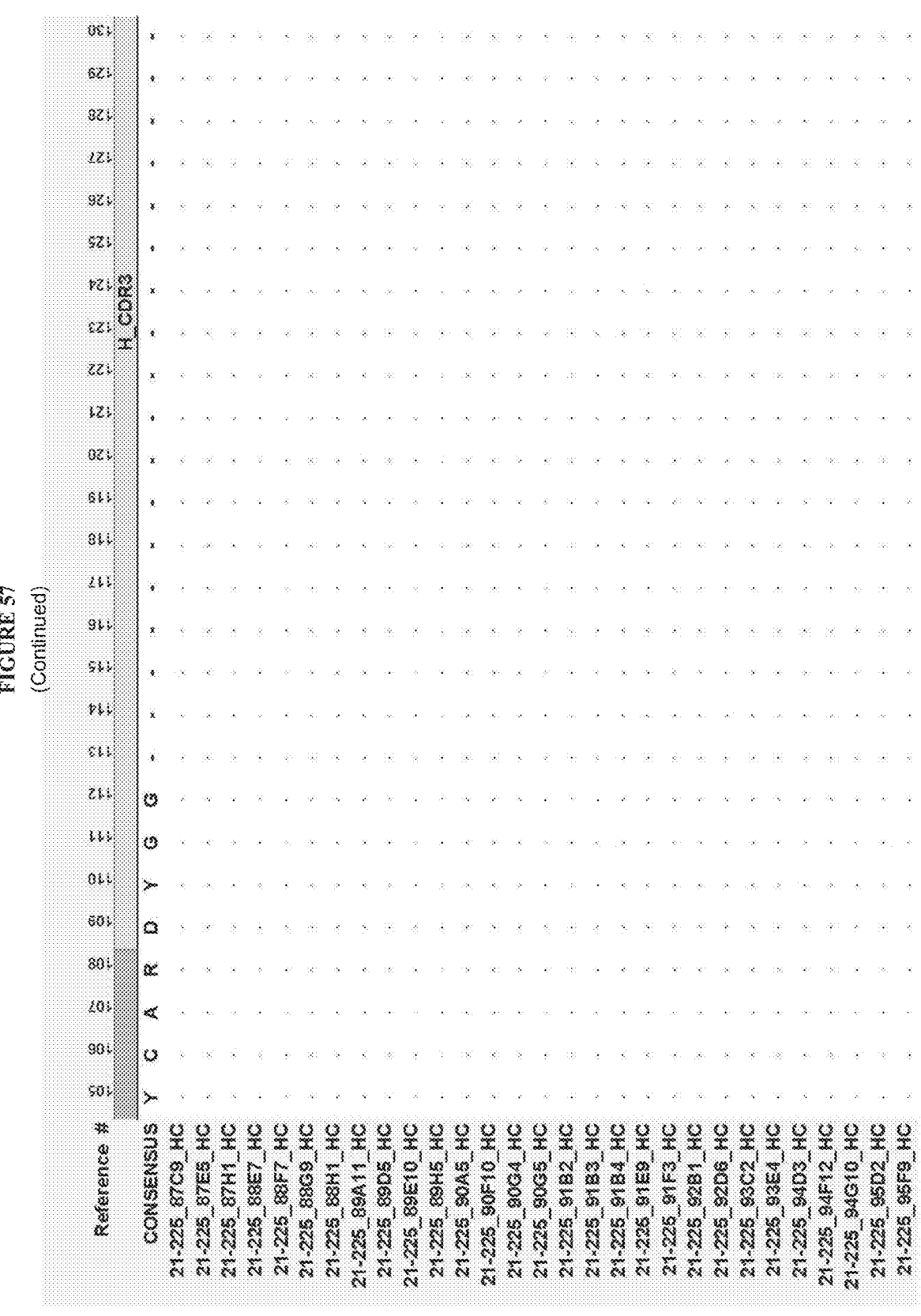
Figure 57:
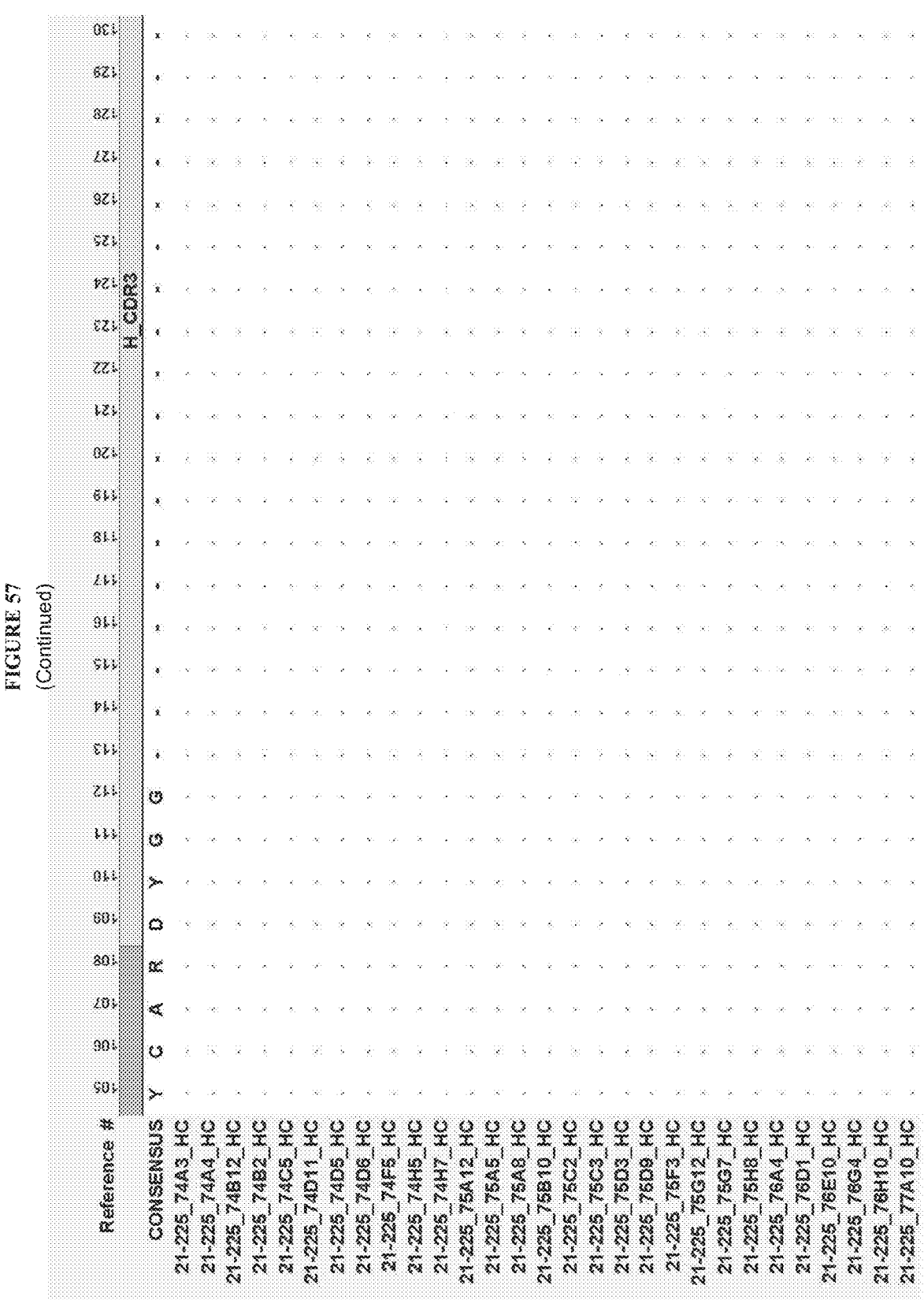
Figure 57:
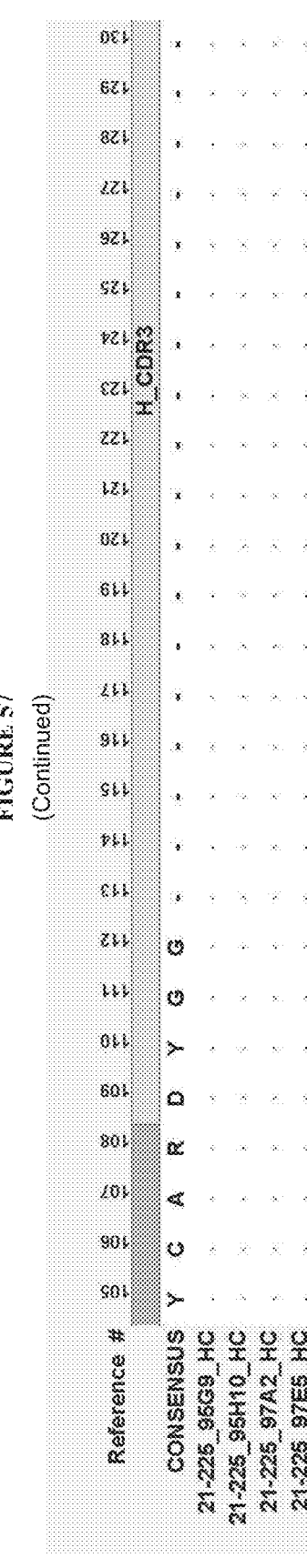
Figure 57:
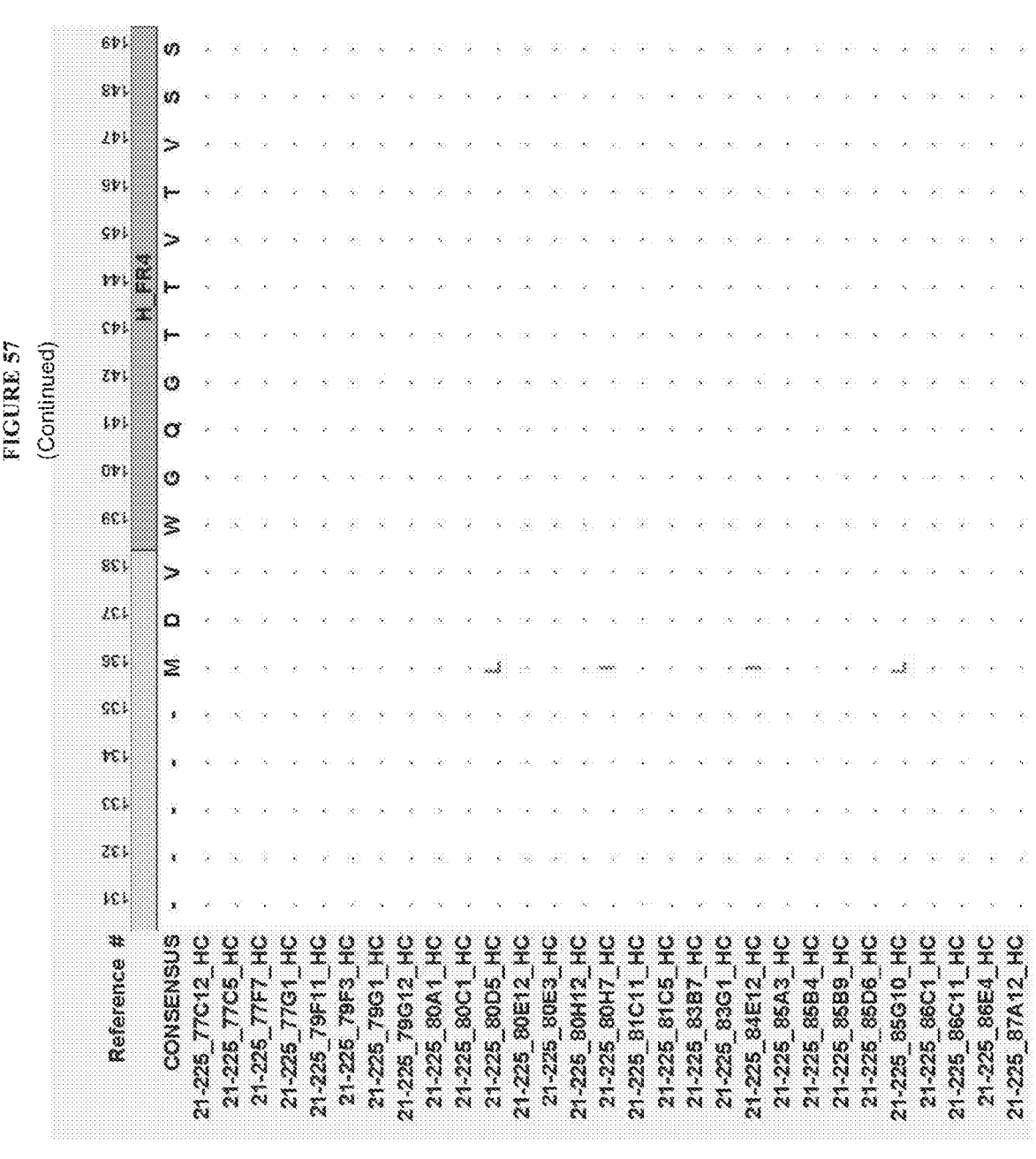
Figure 57:
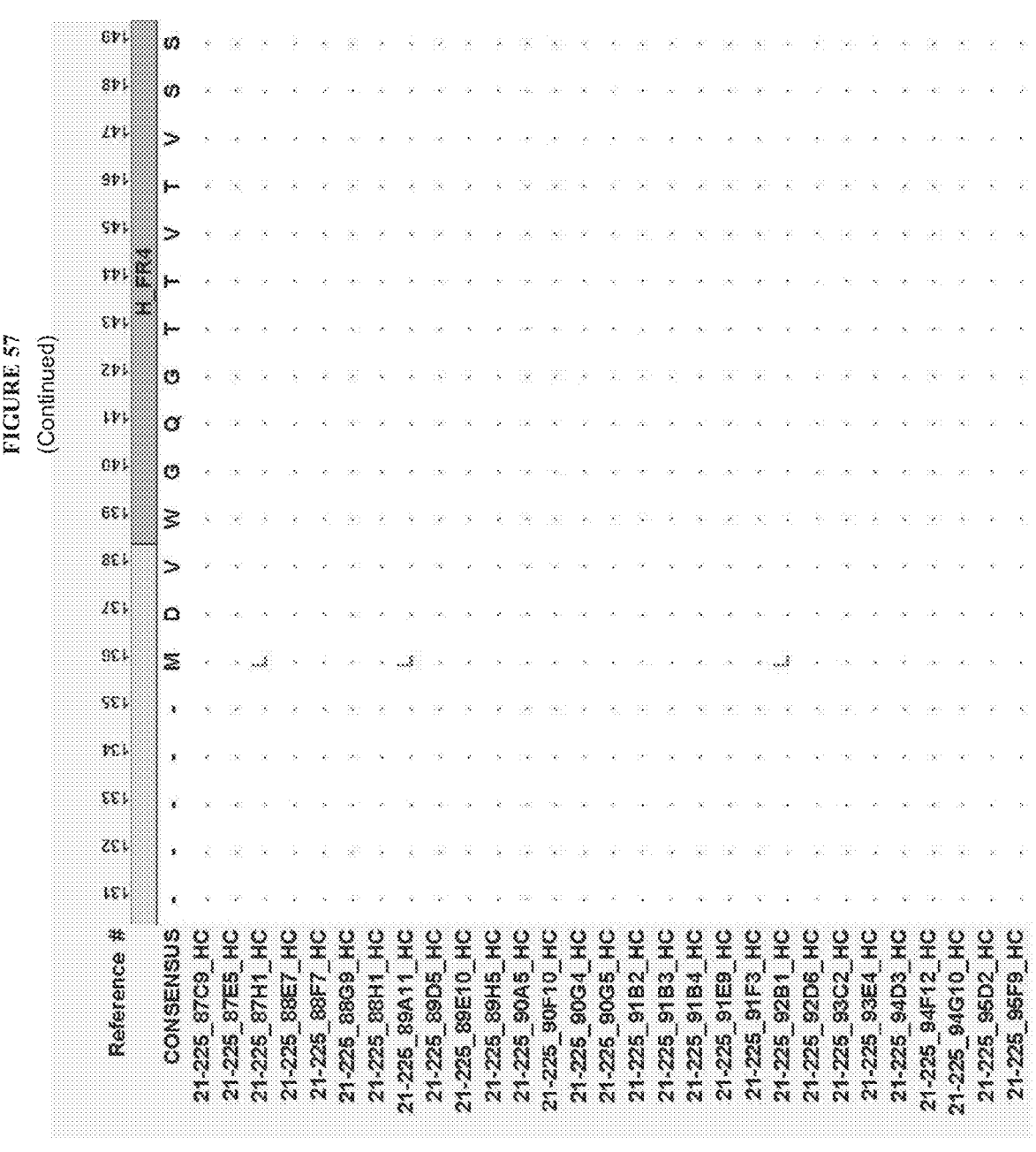
Figure 57:
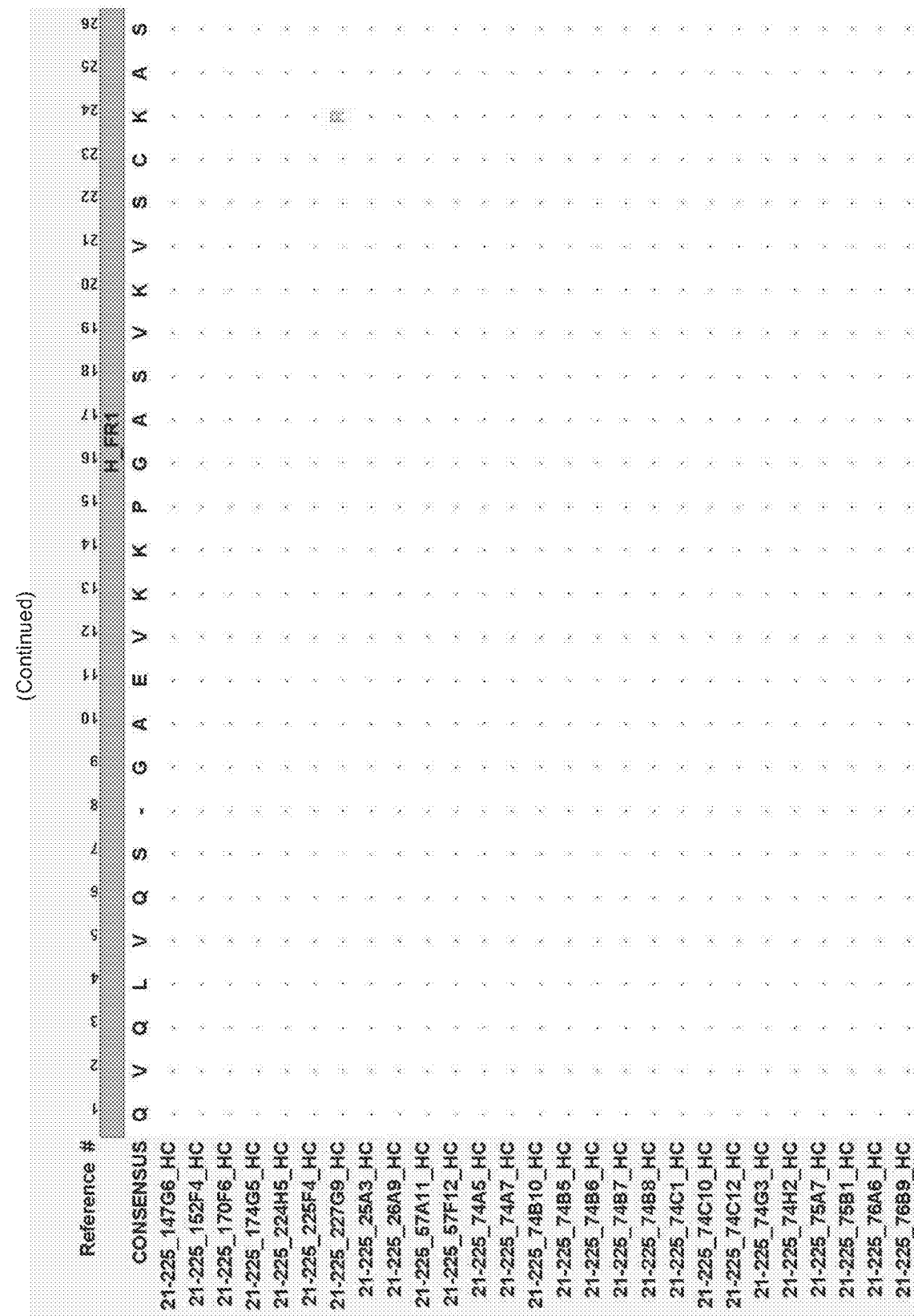
Figure 57:
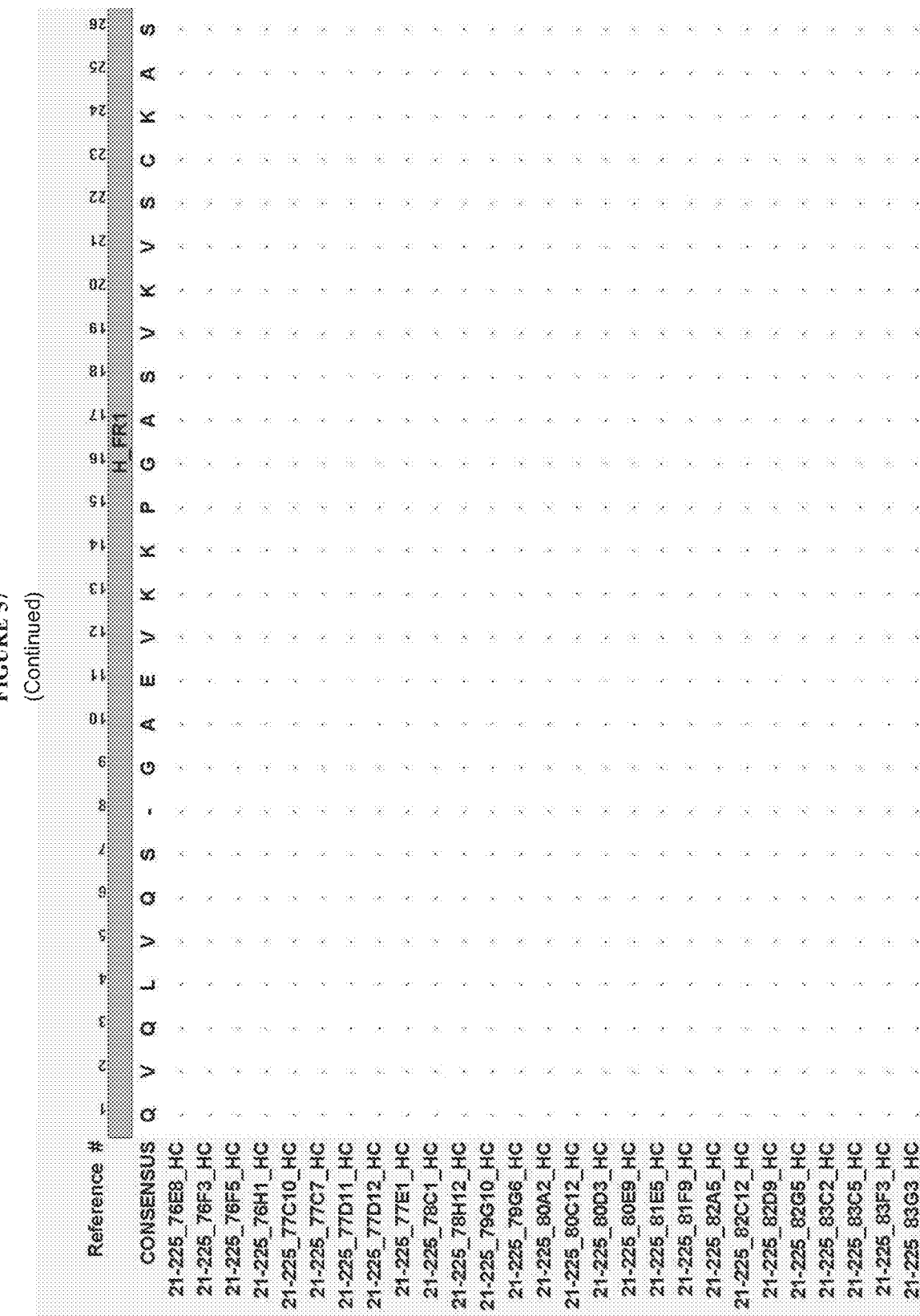
Figure 57:
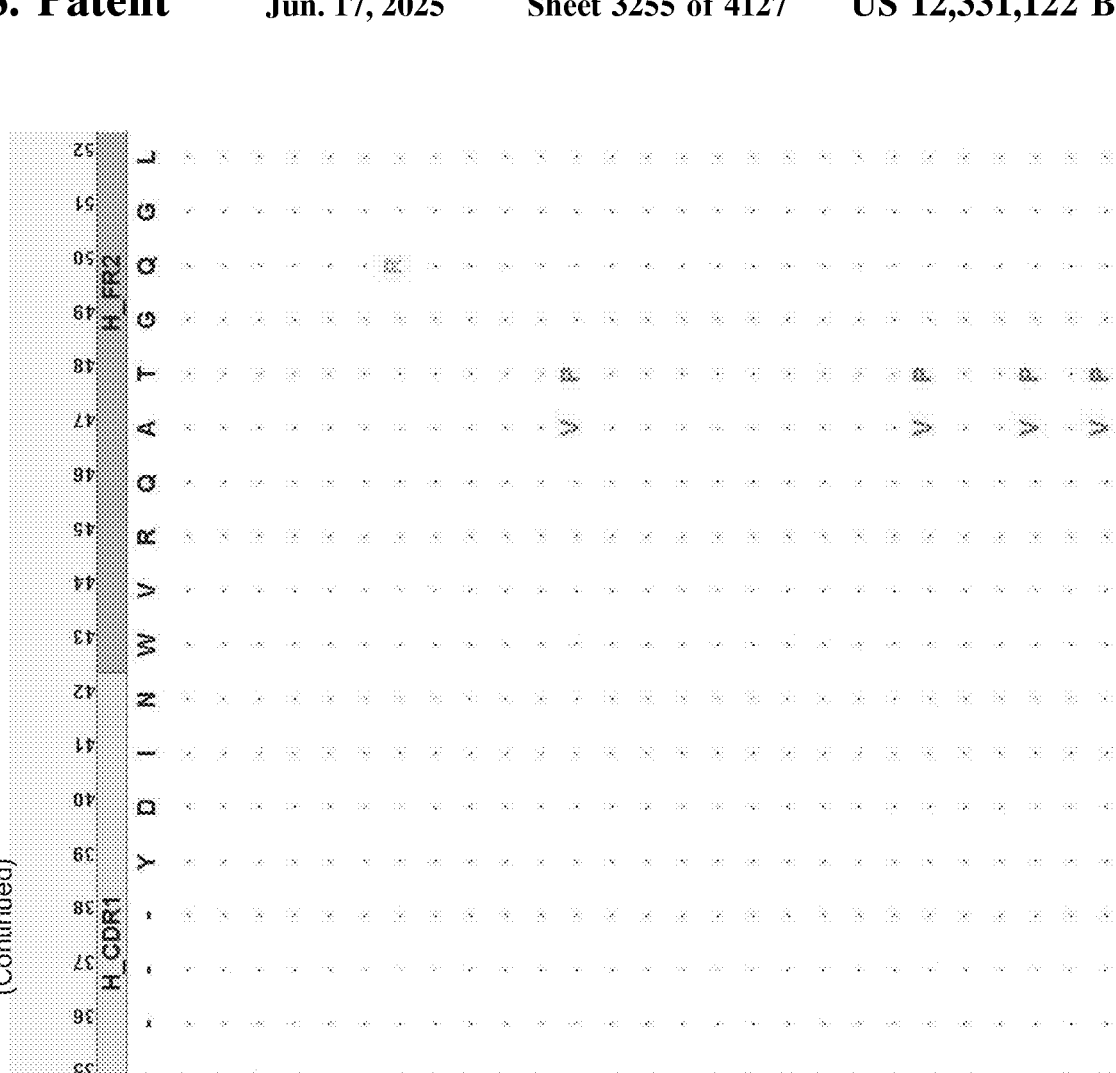
Figure 57:
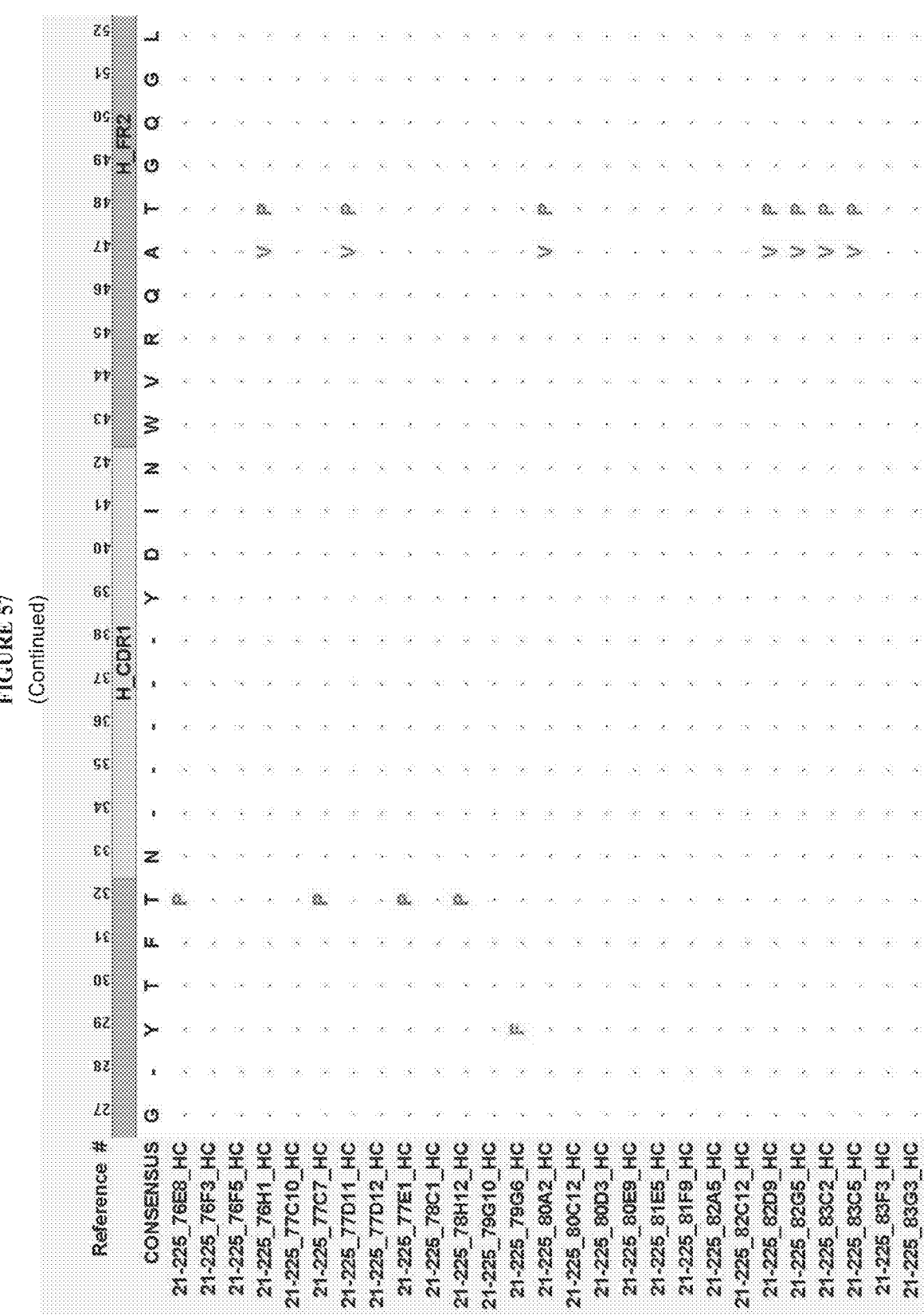
Figure 57:
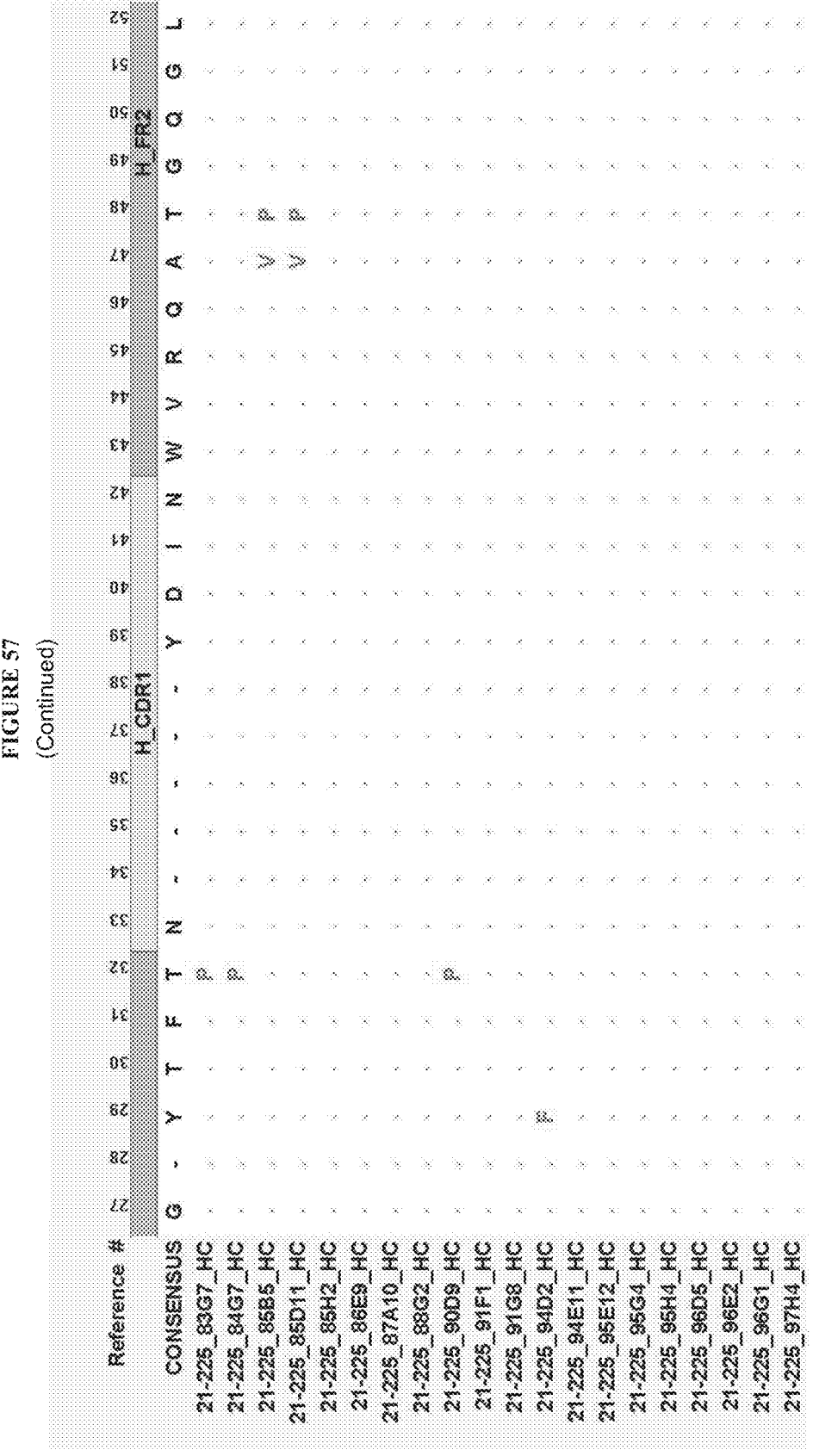
Figure 57:
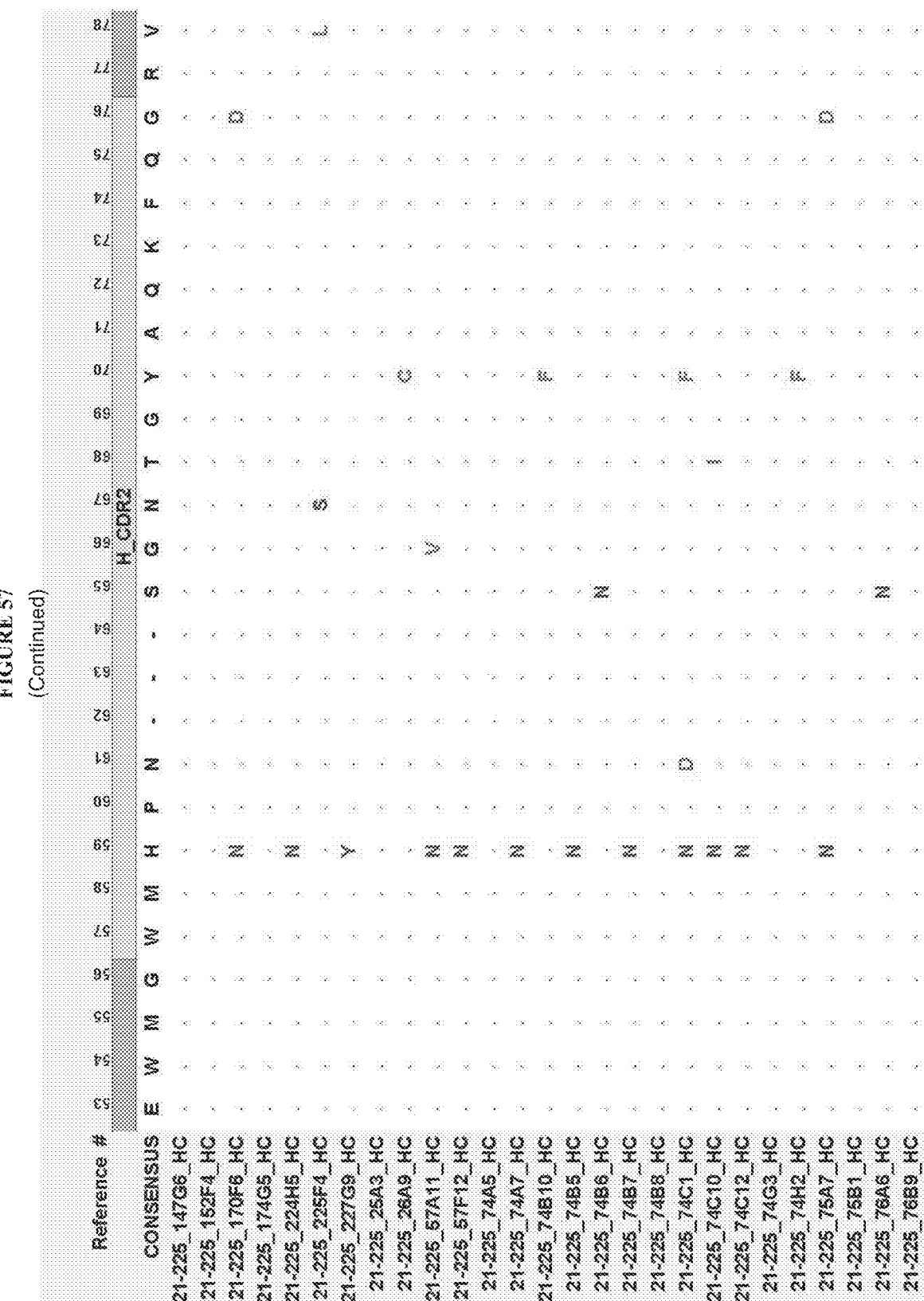
Figure 57:
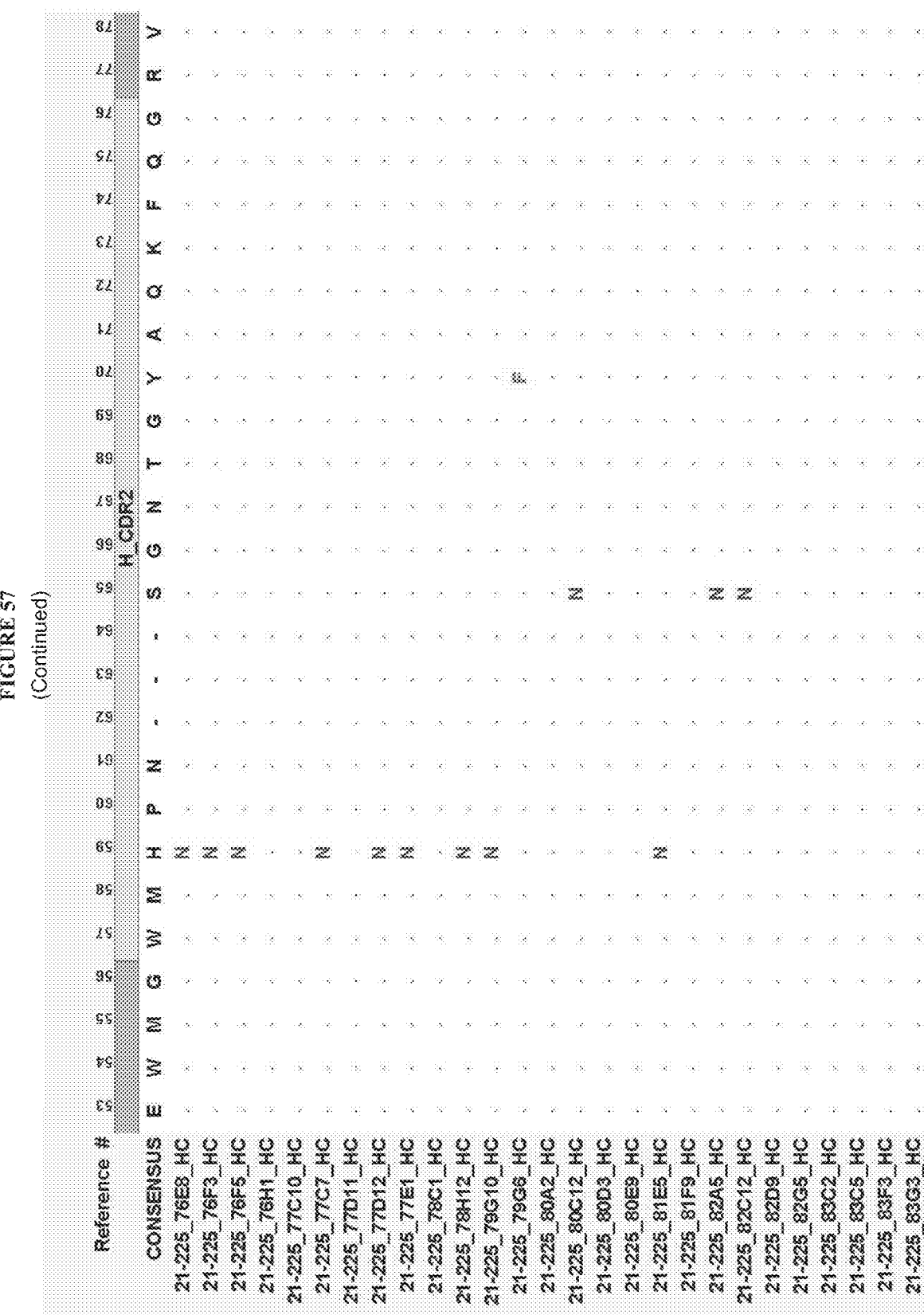
Figure 57:
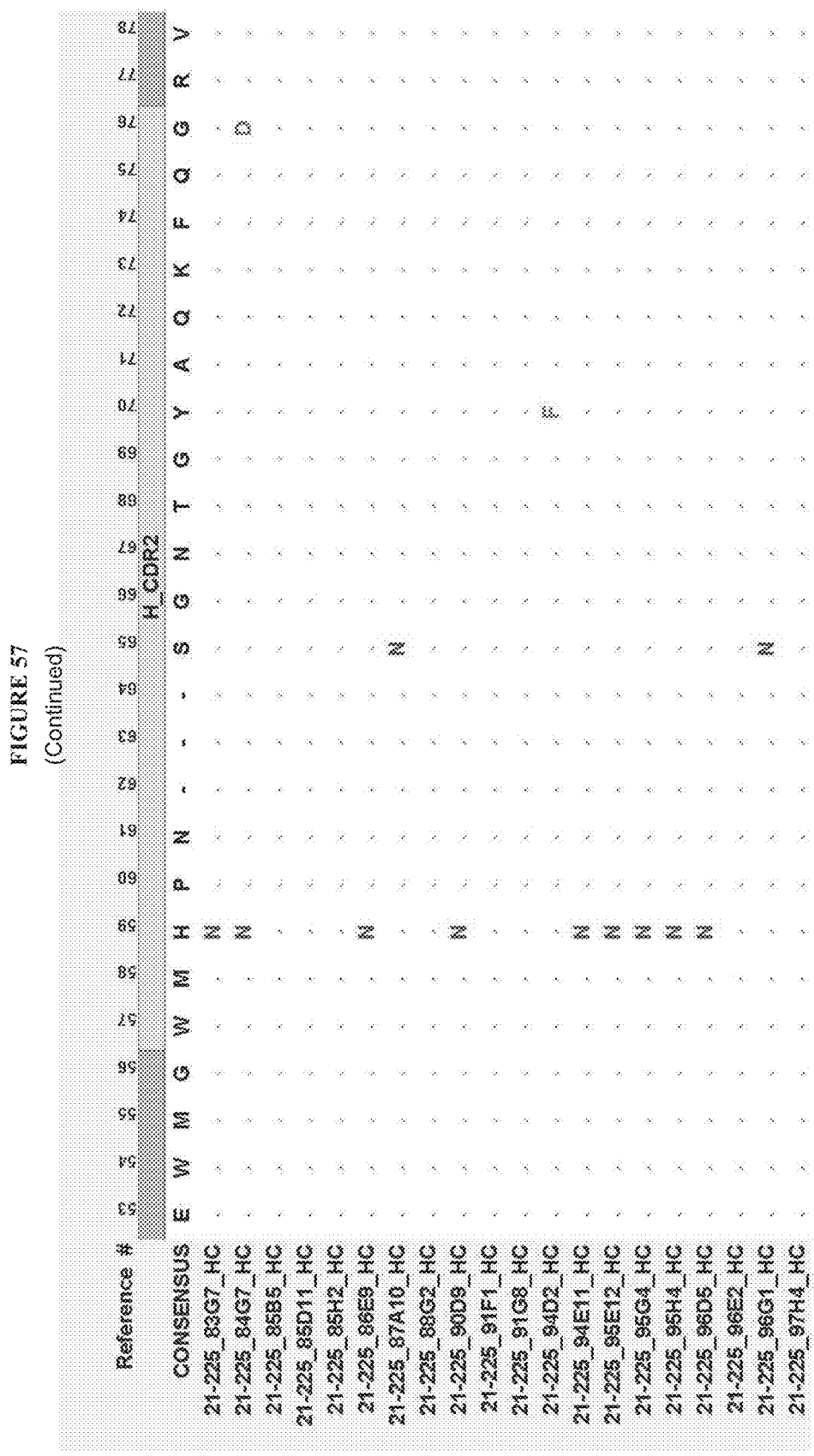
Figure 57:
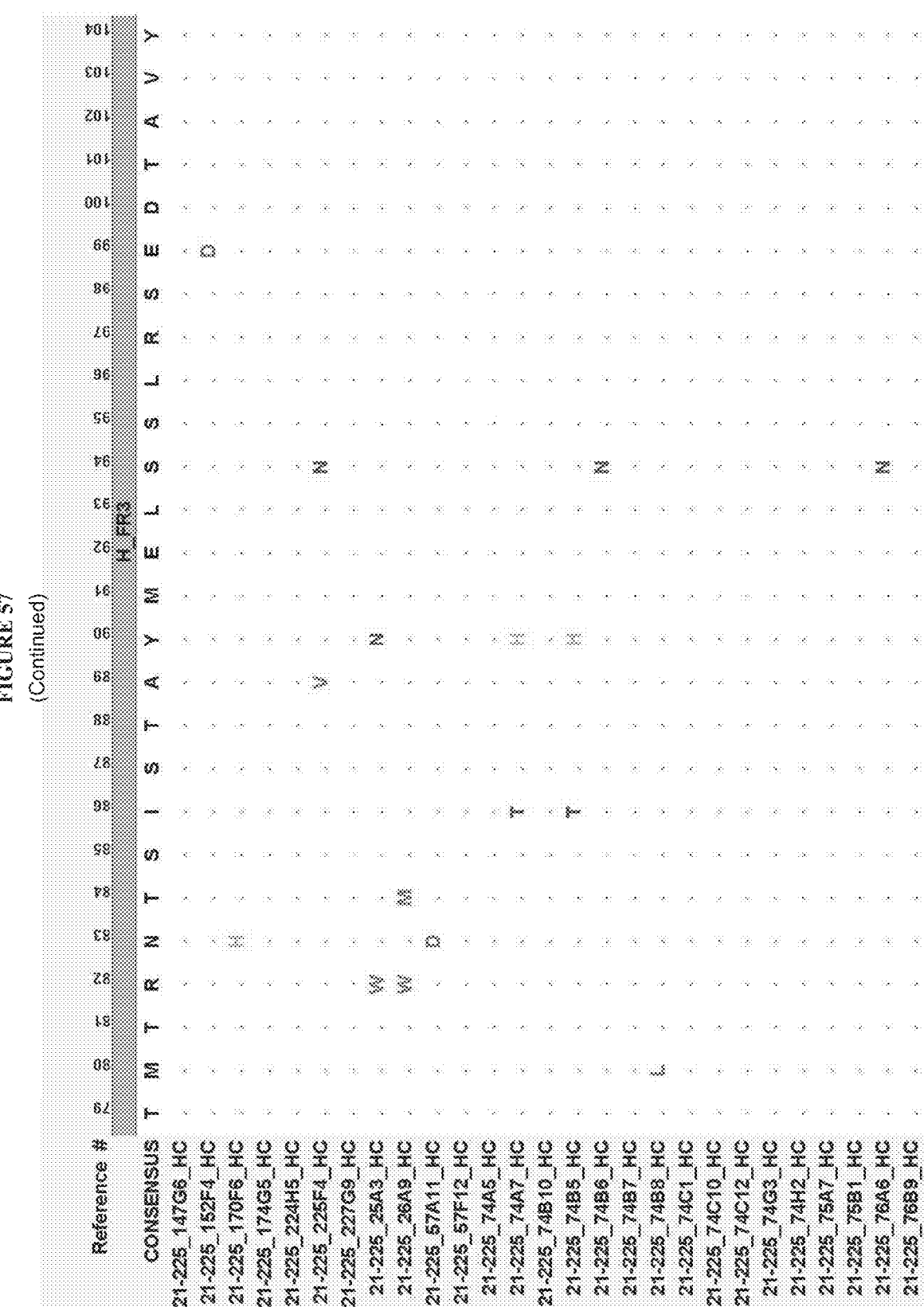
Figure 57:
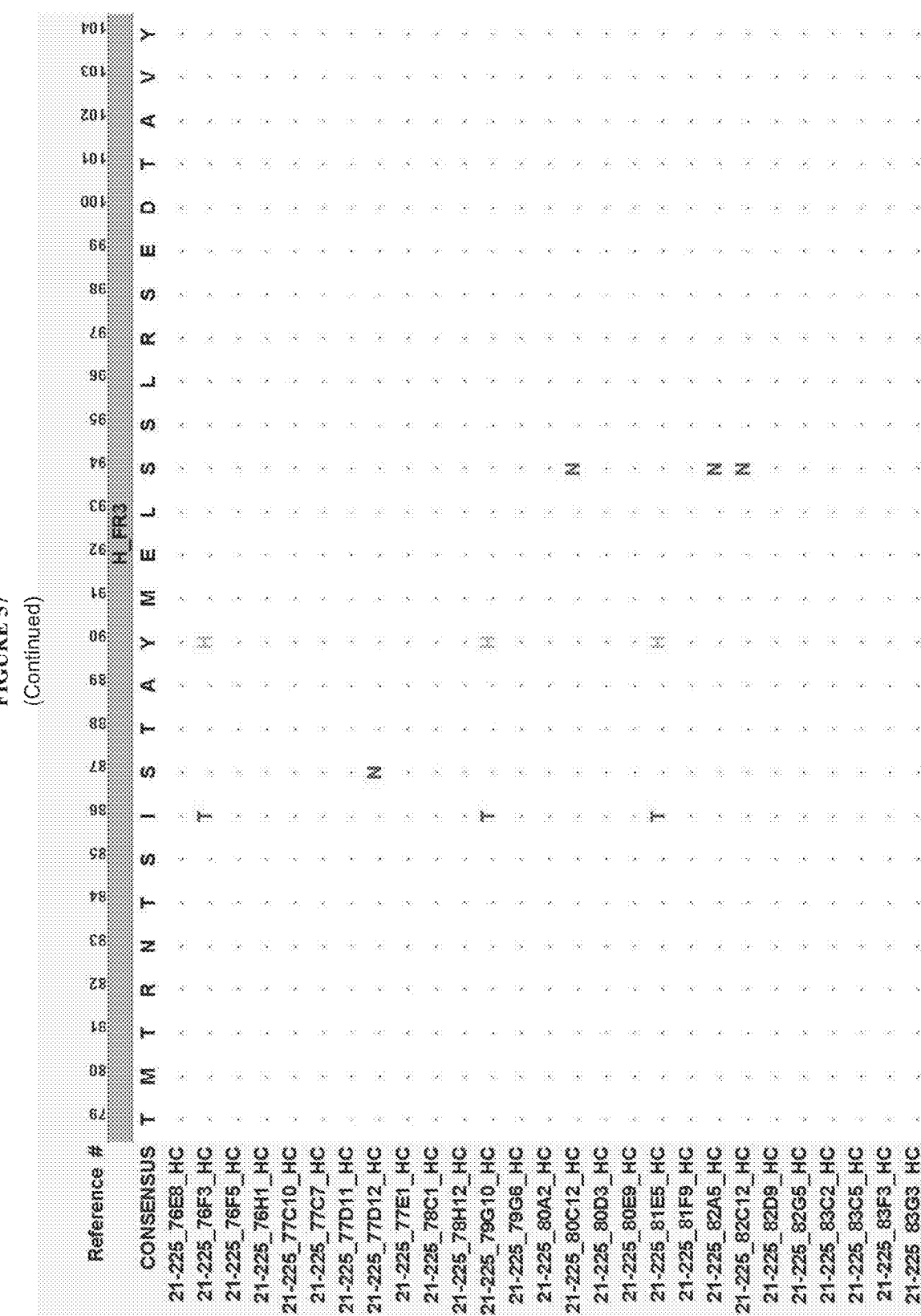
Figure 57:
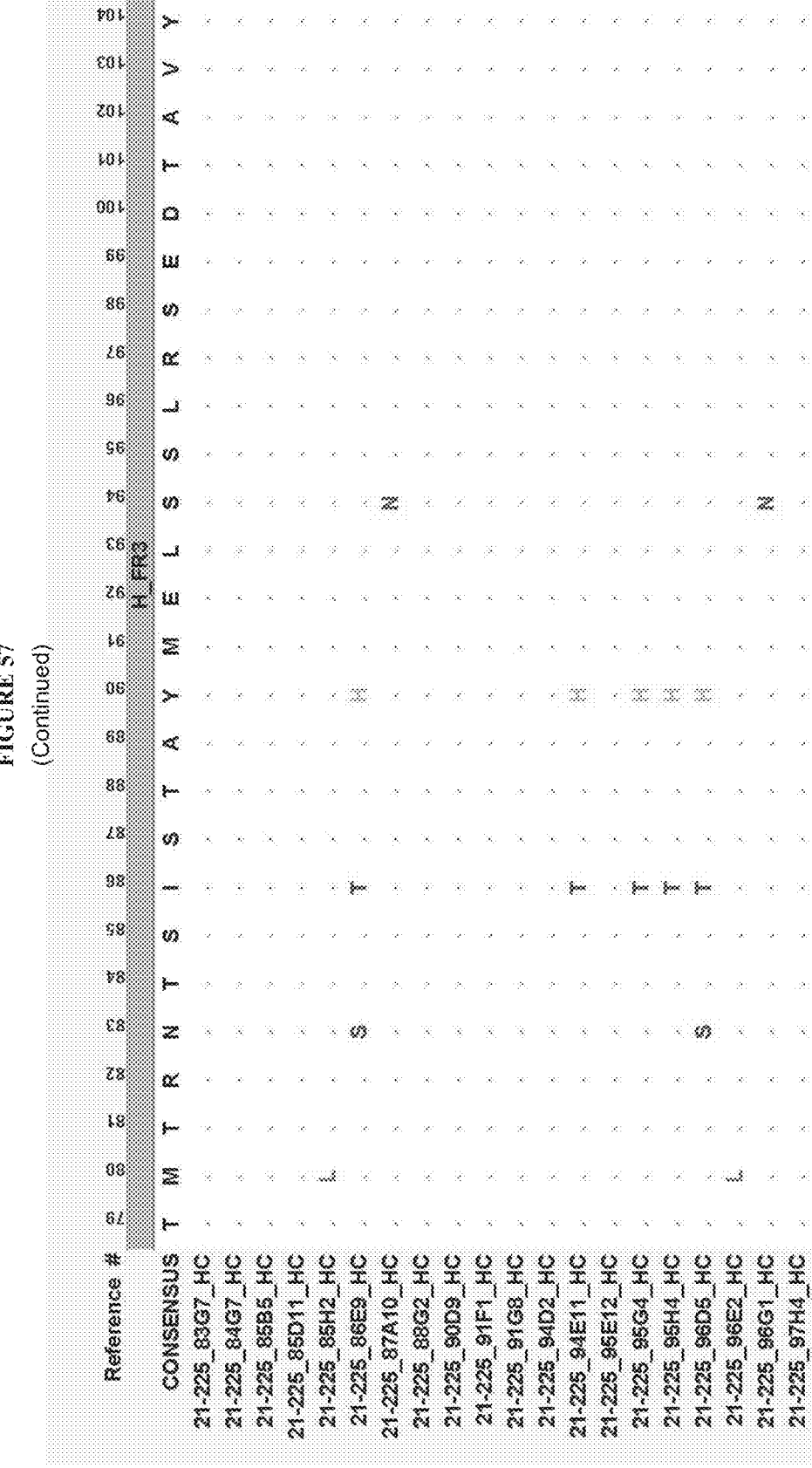
Figure 57:
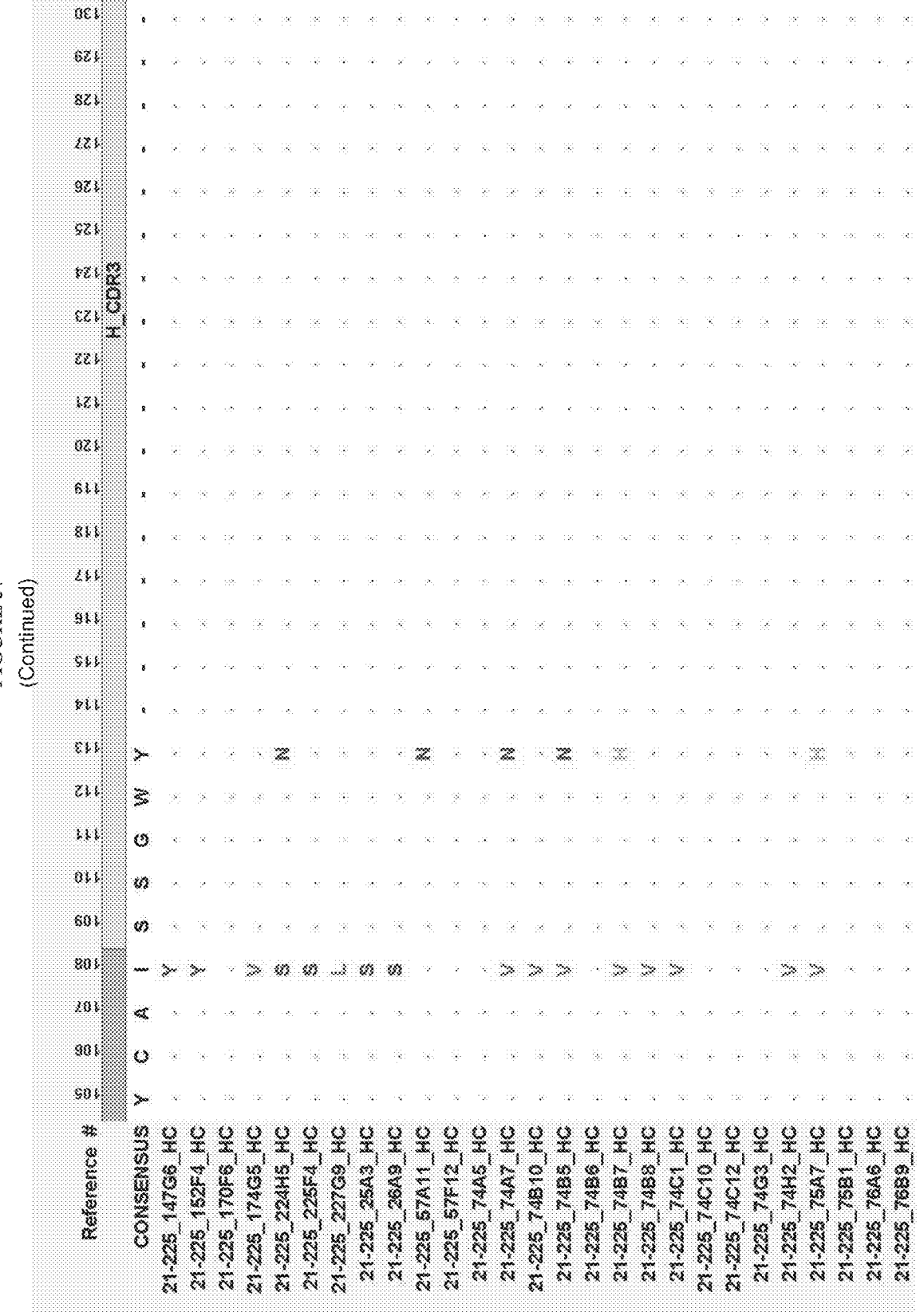
Figure 57:
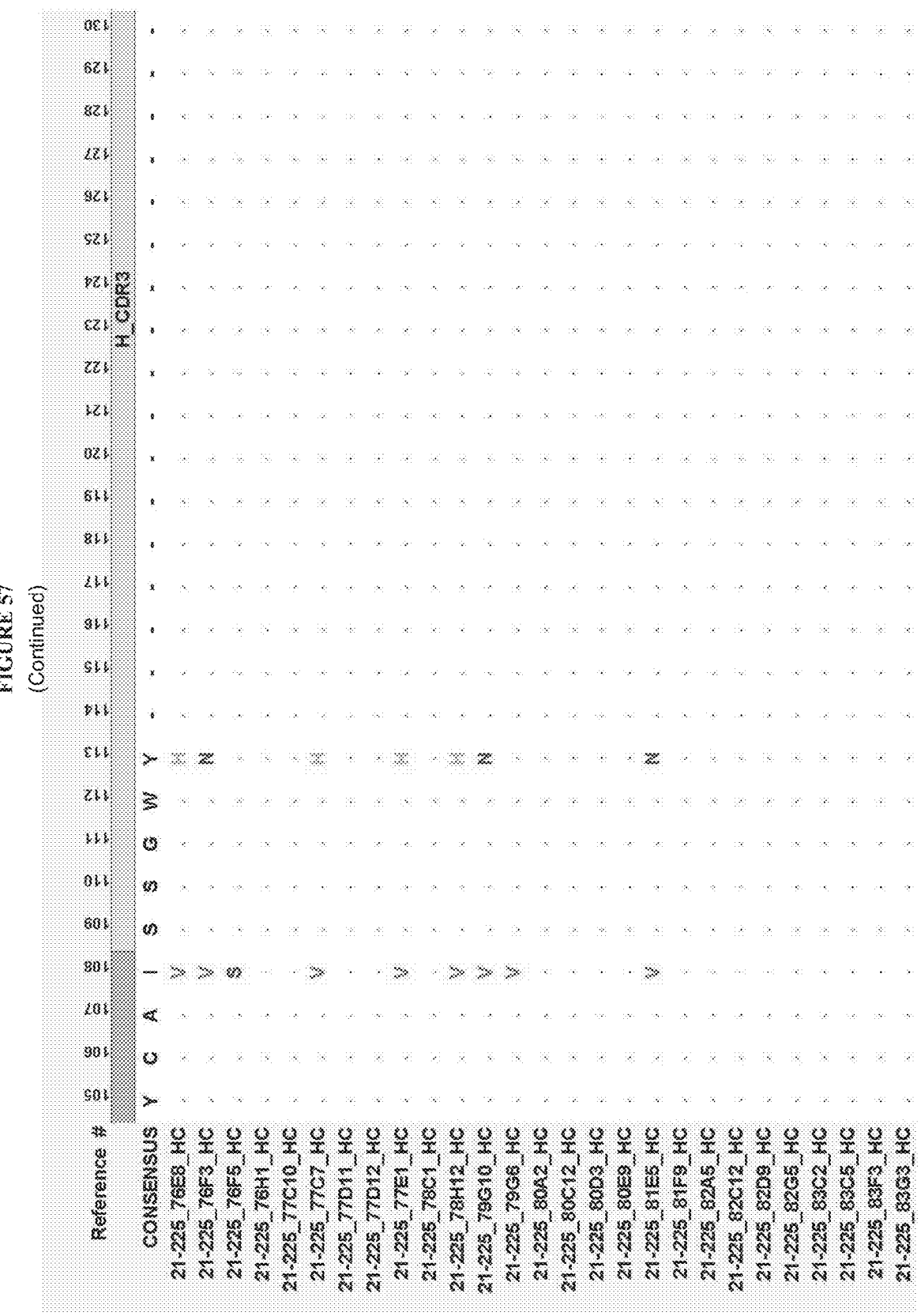
Figure 57:
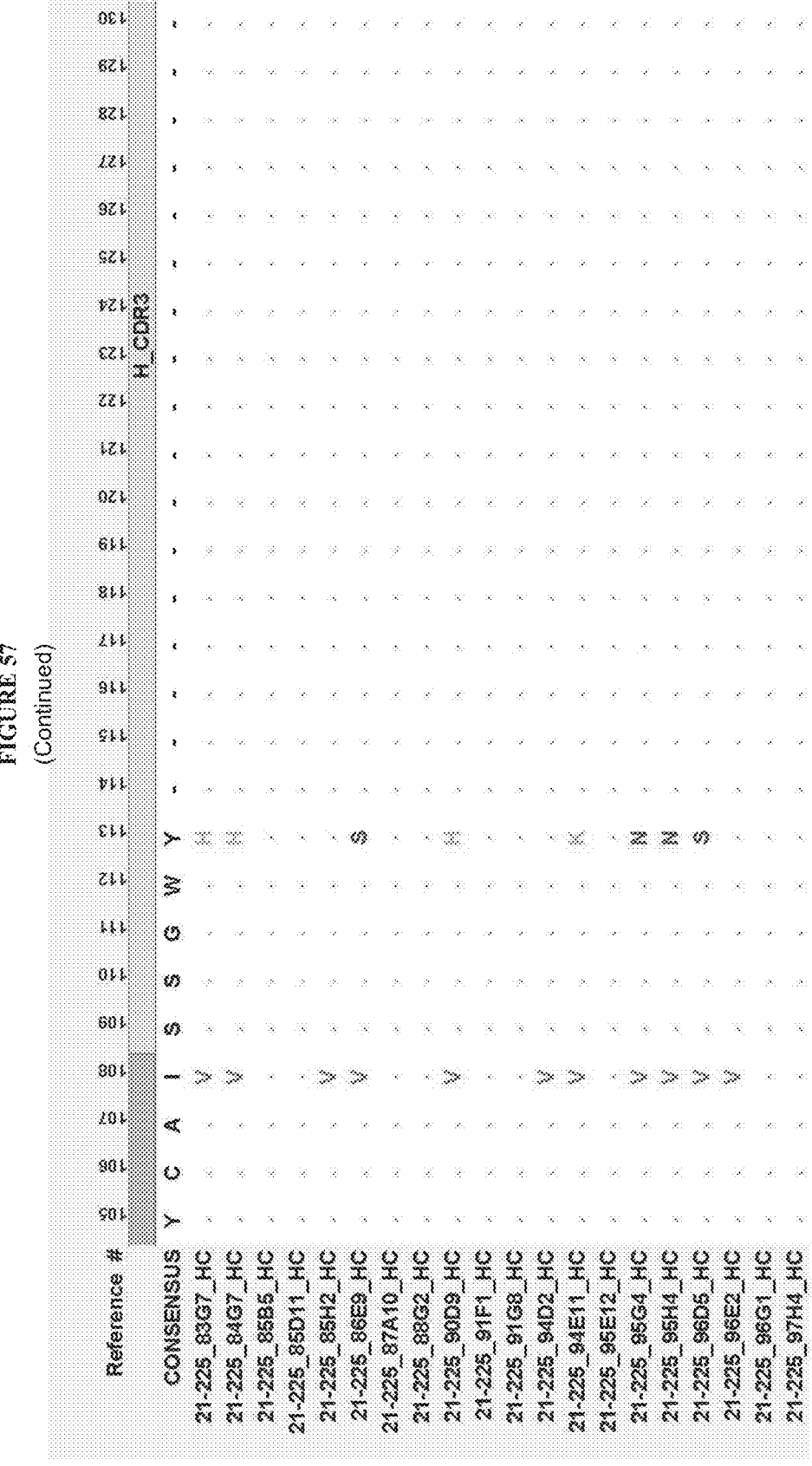
Figure 57:
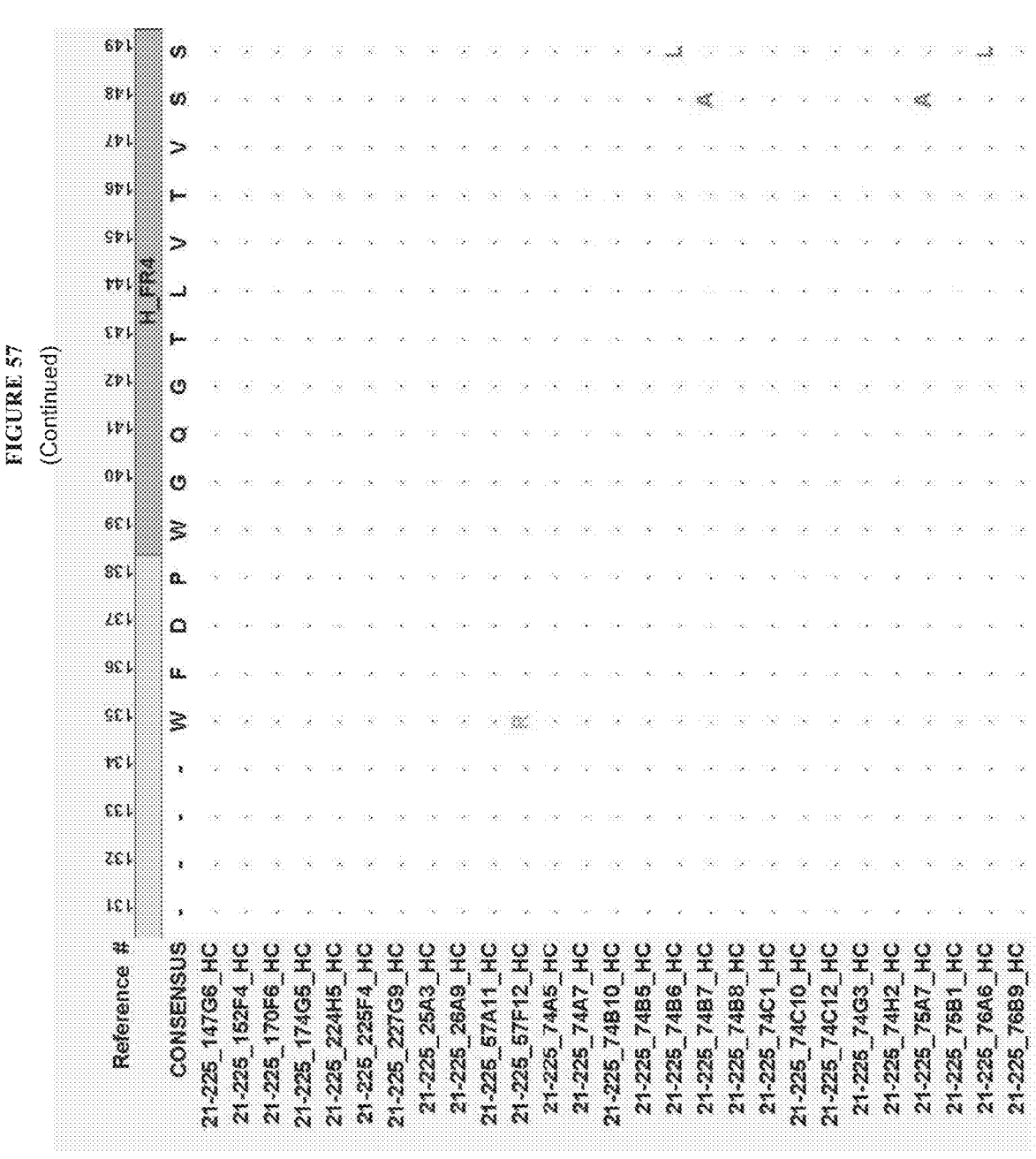
Figure 57:
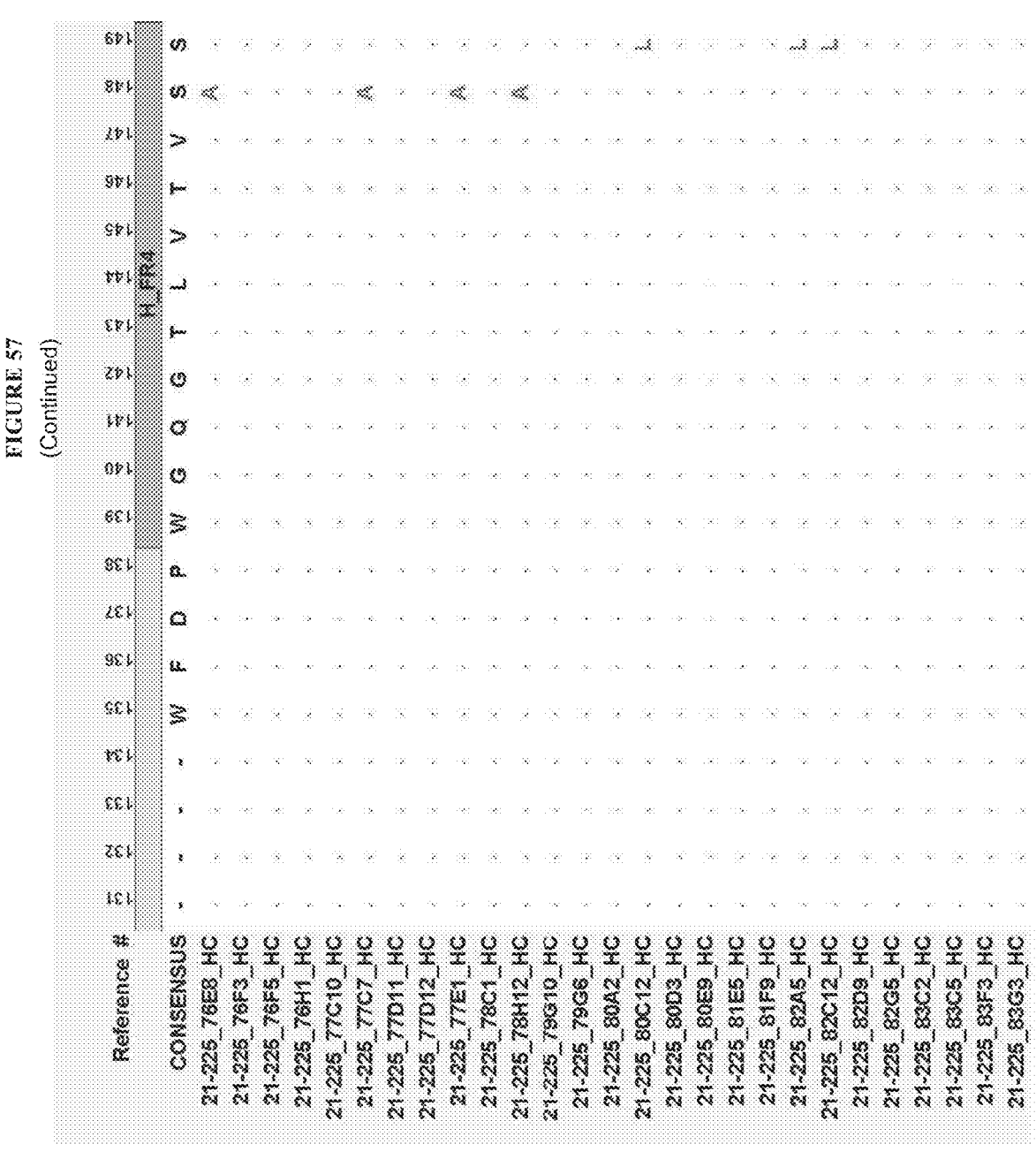
Figure 57:
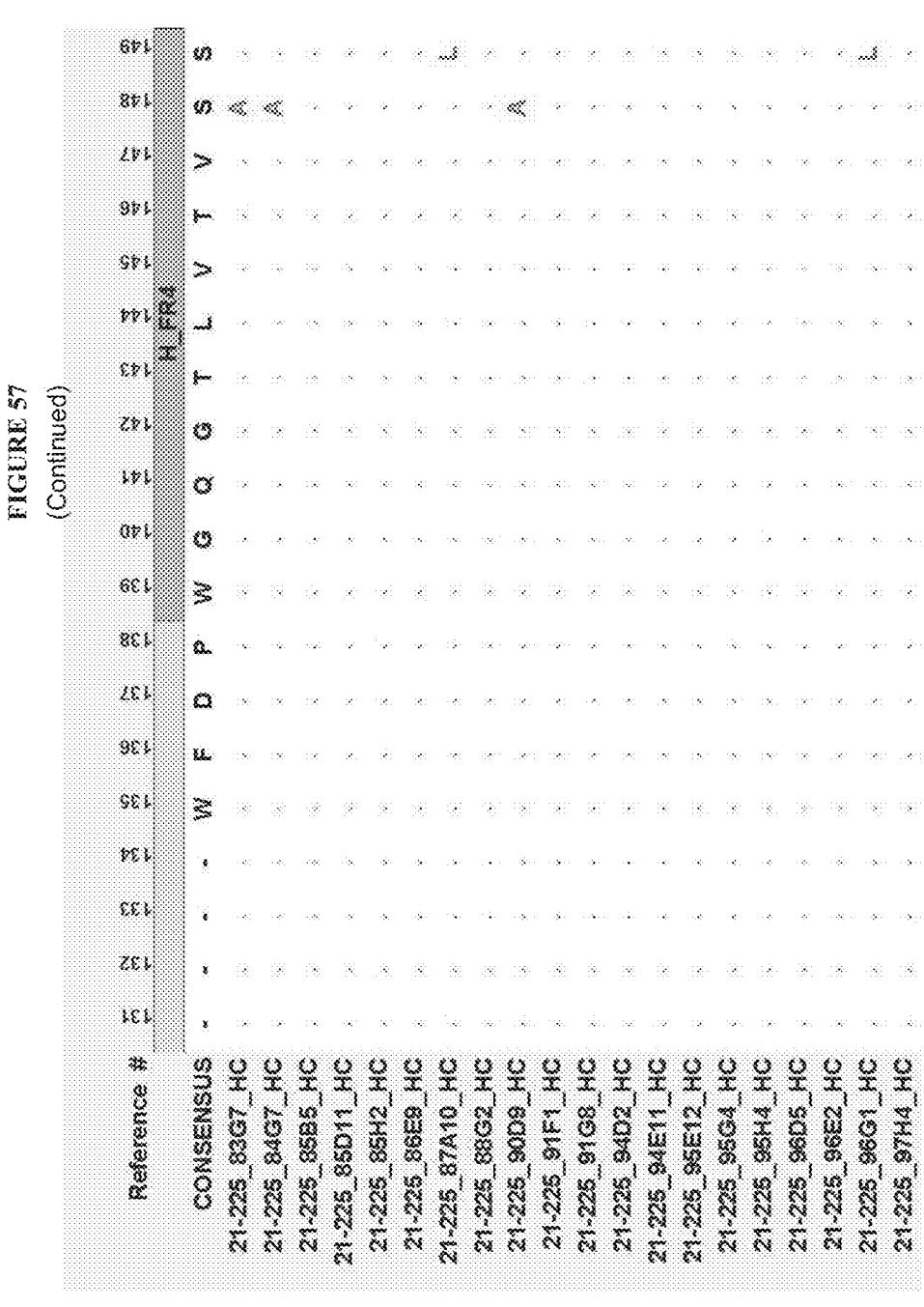
Figure 57:
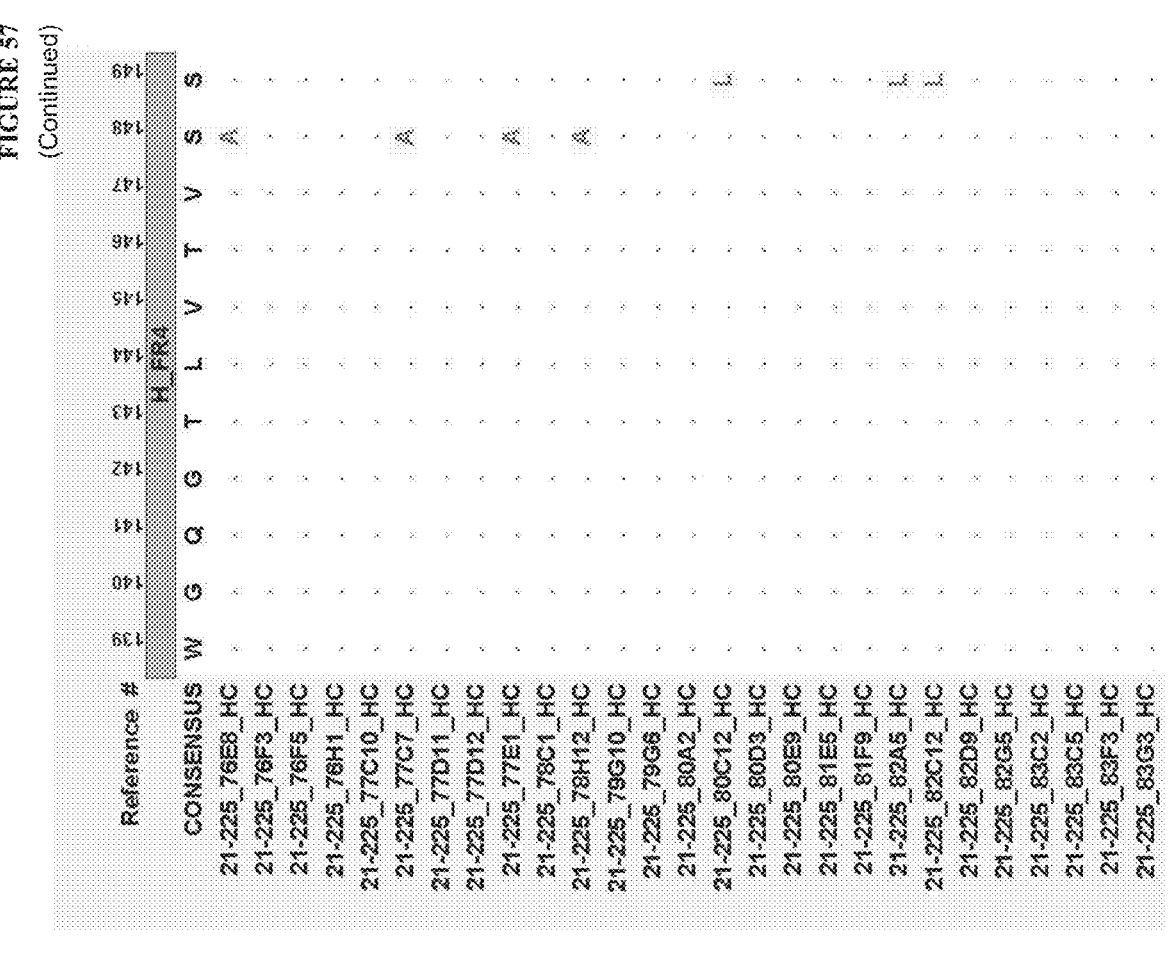
Figure 57:
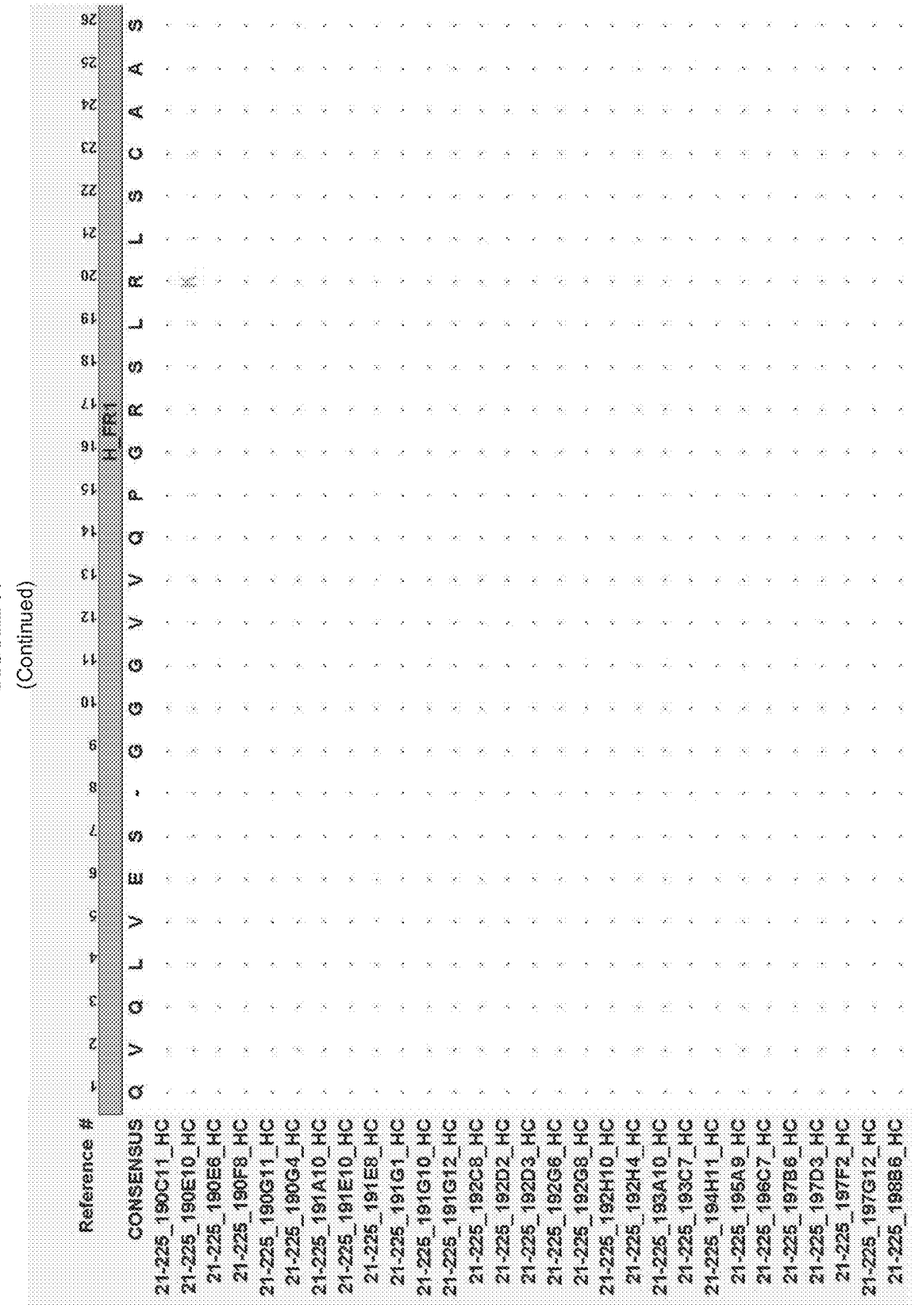
Figure 57:
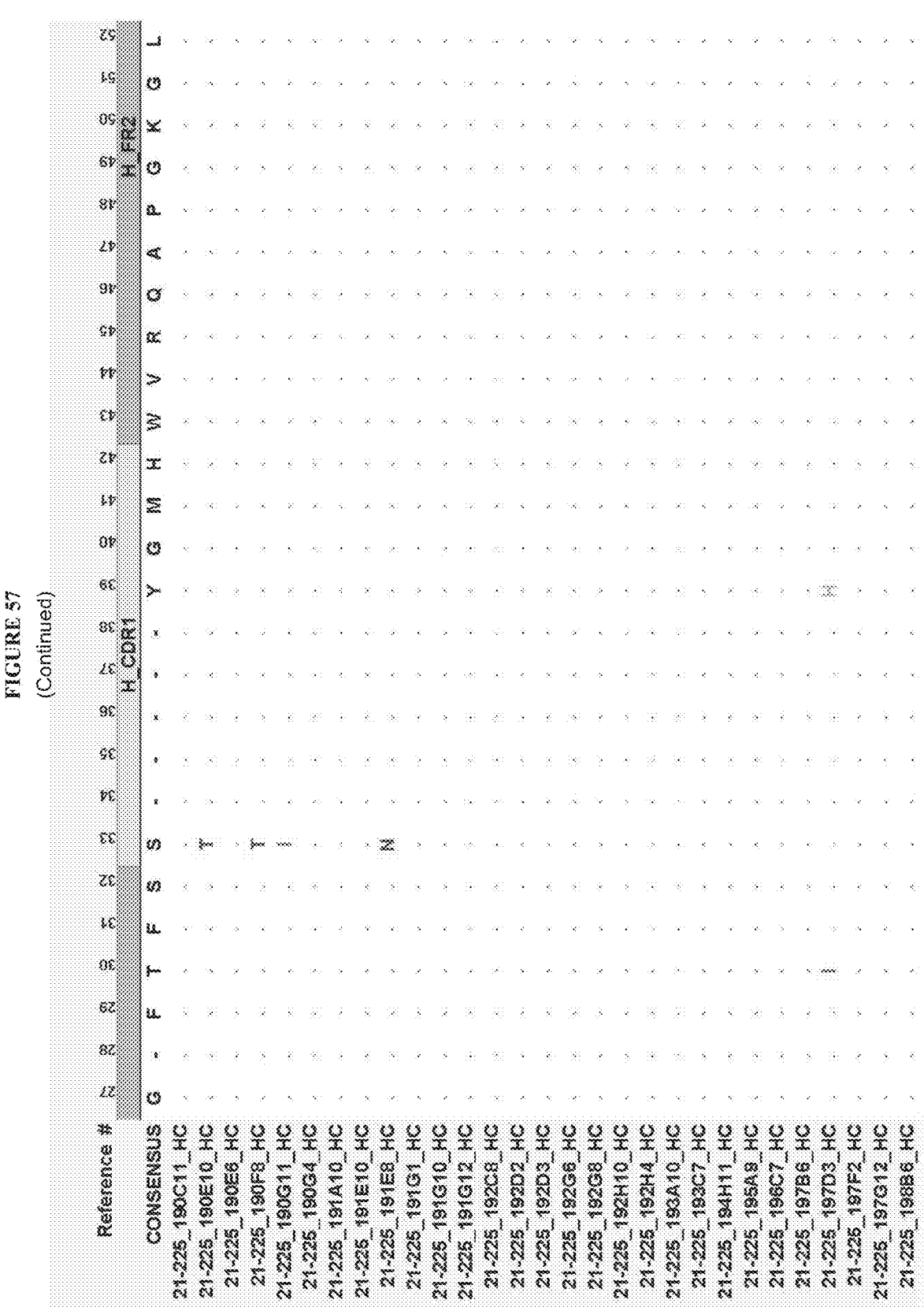
Figure 57:
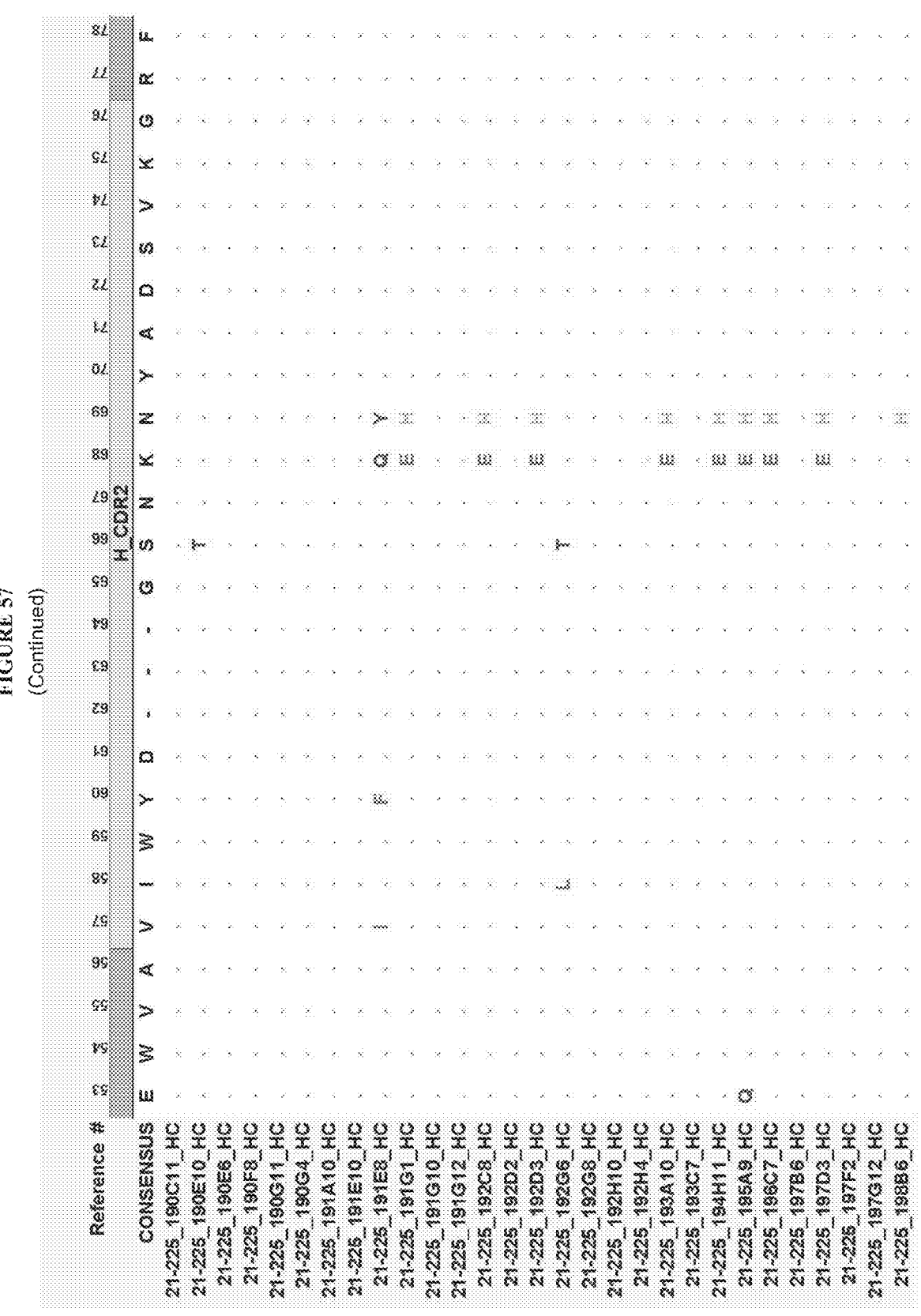
Figure 57:
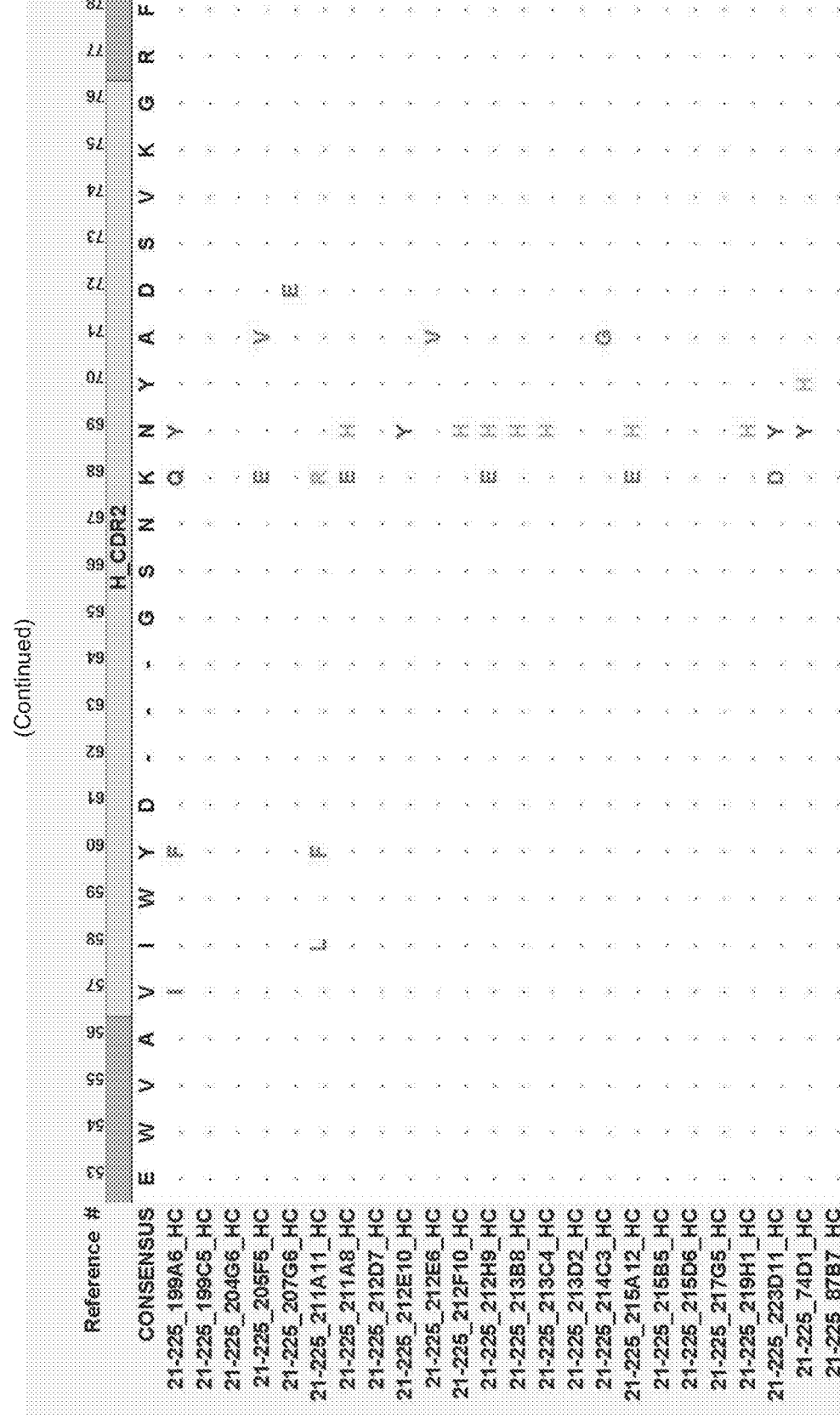
Figure 57:
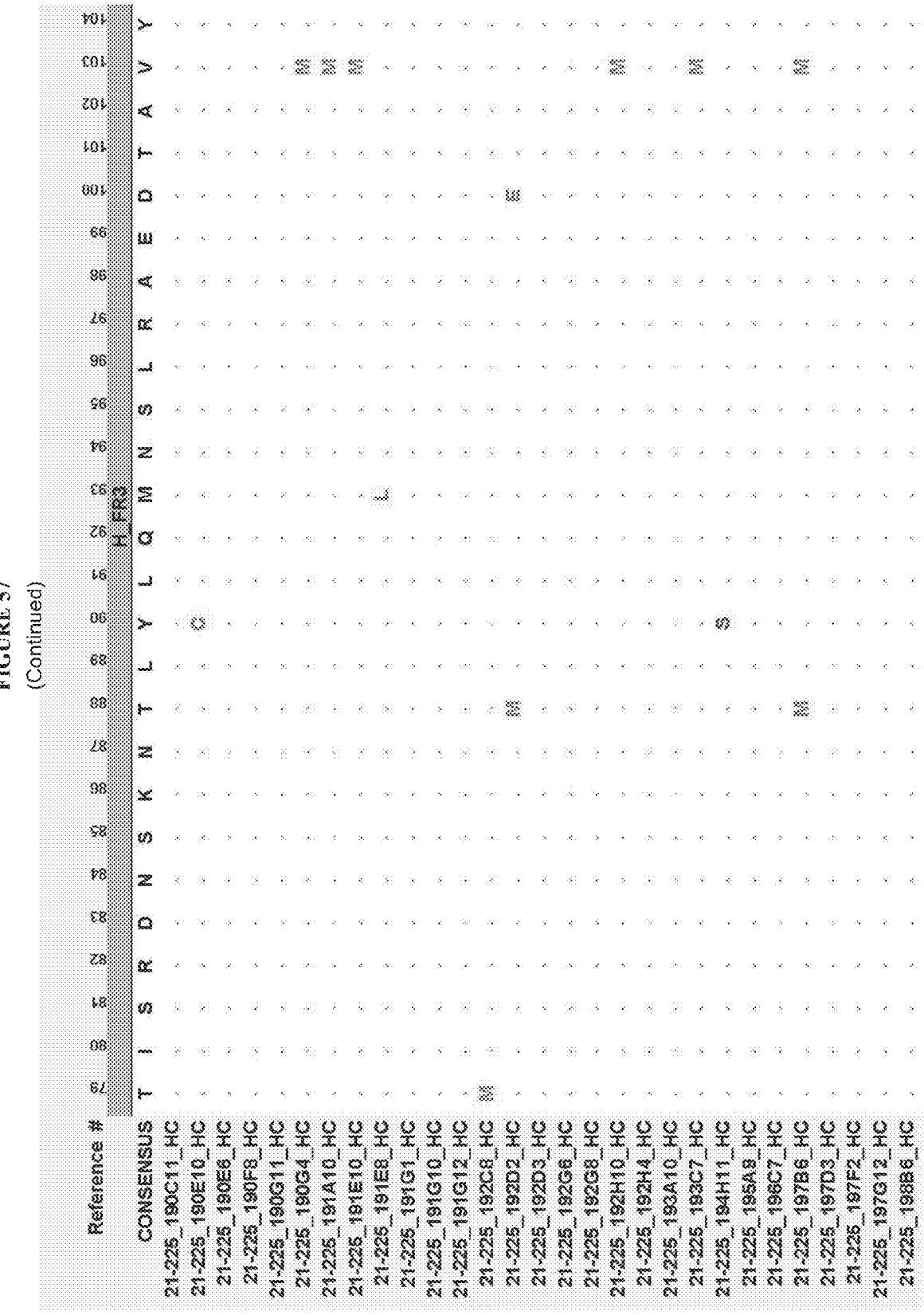
Figure 57:
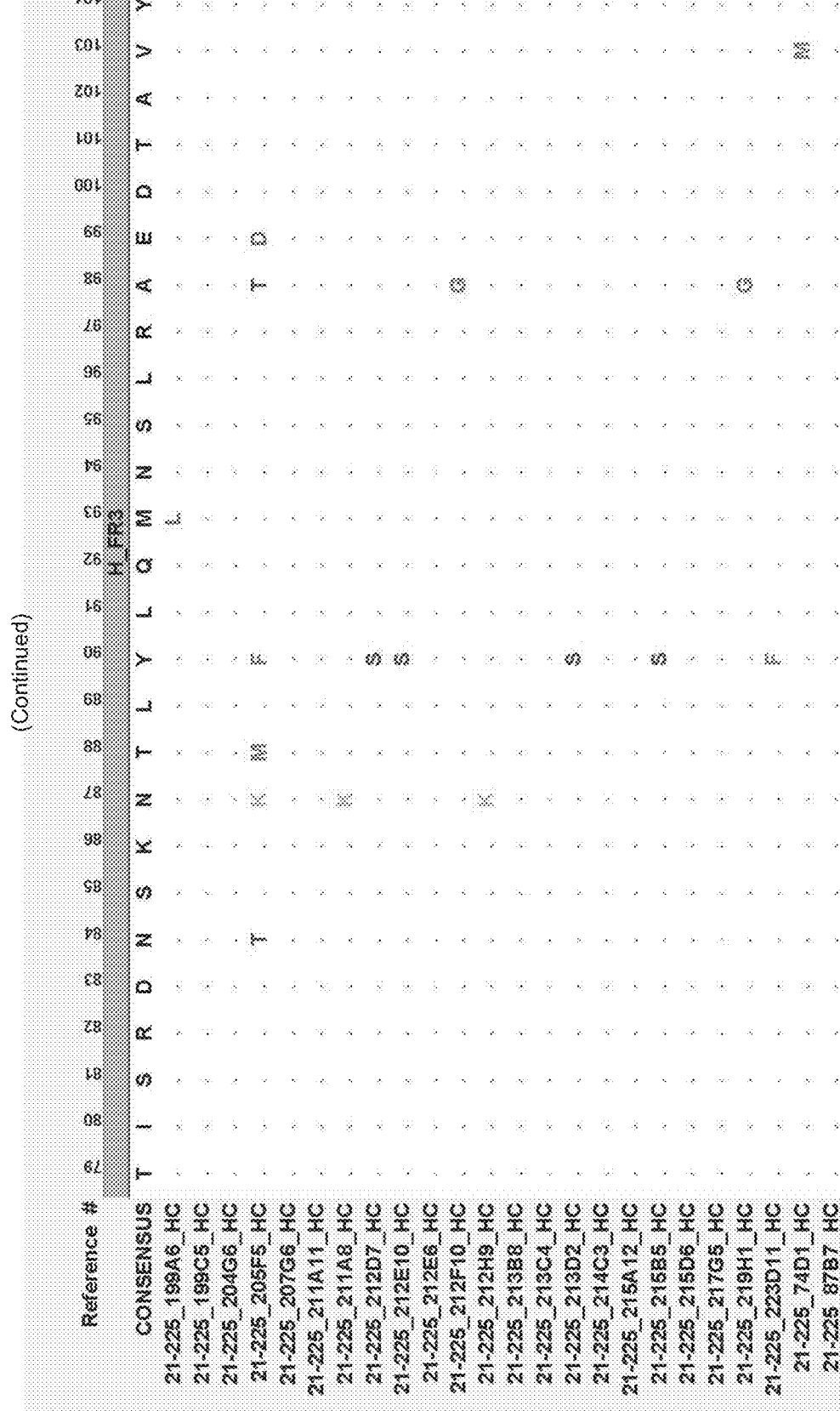
Figure 57:
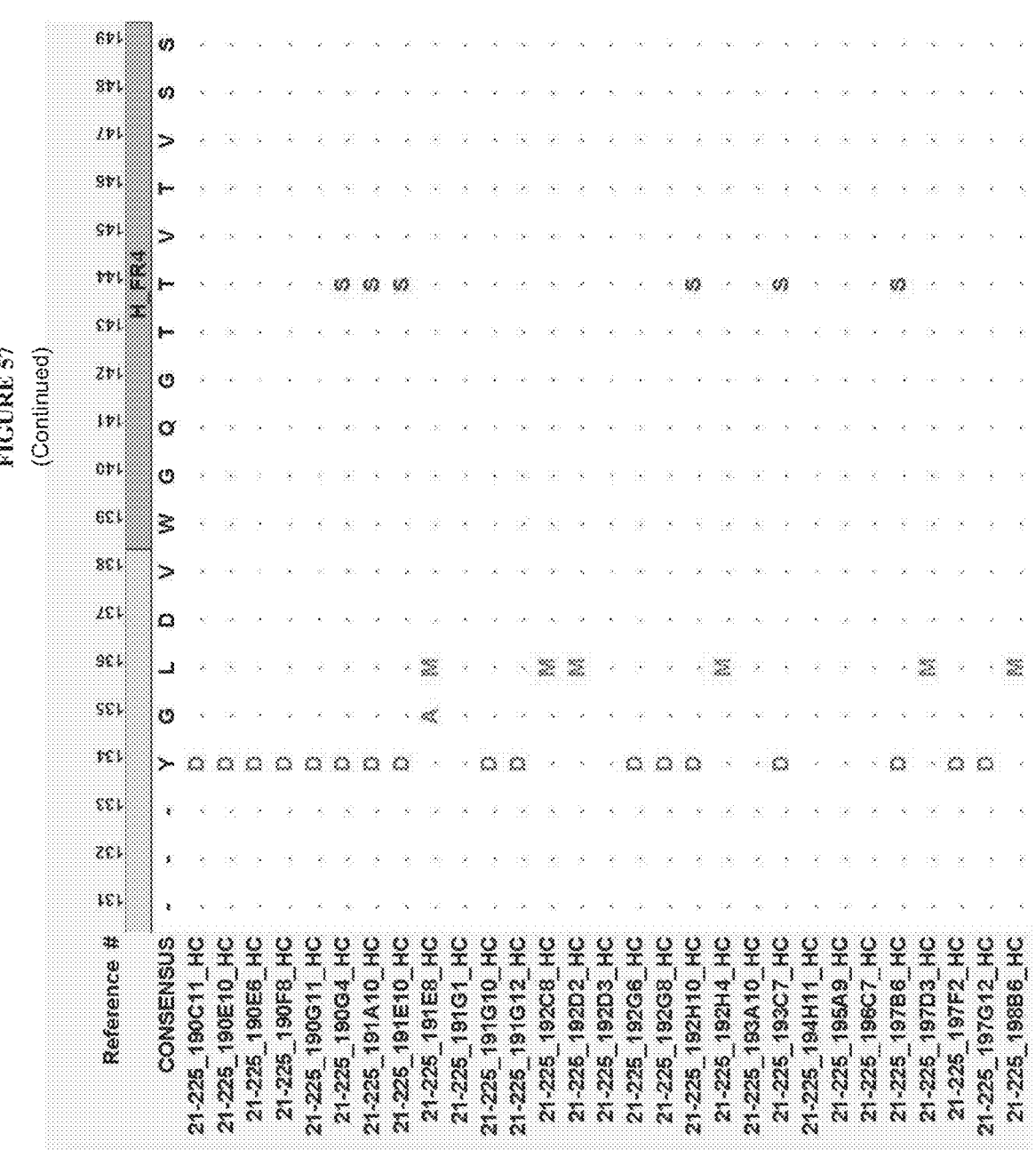
Figure 57:
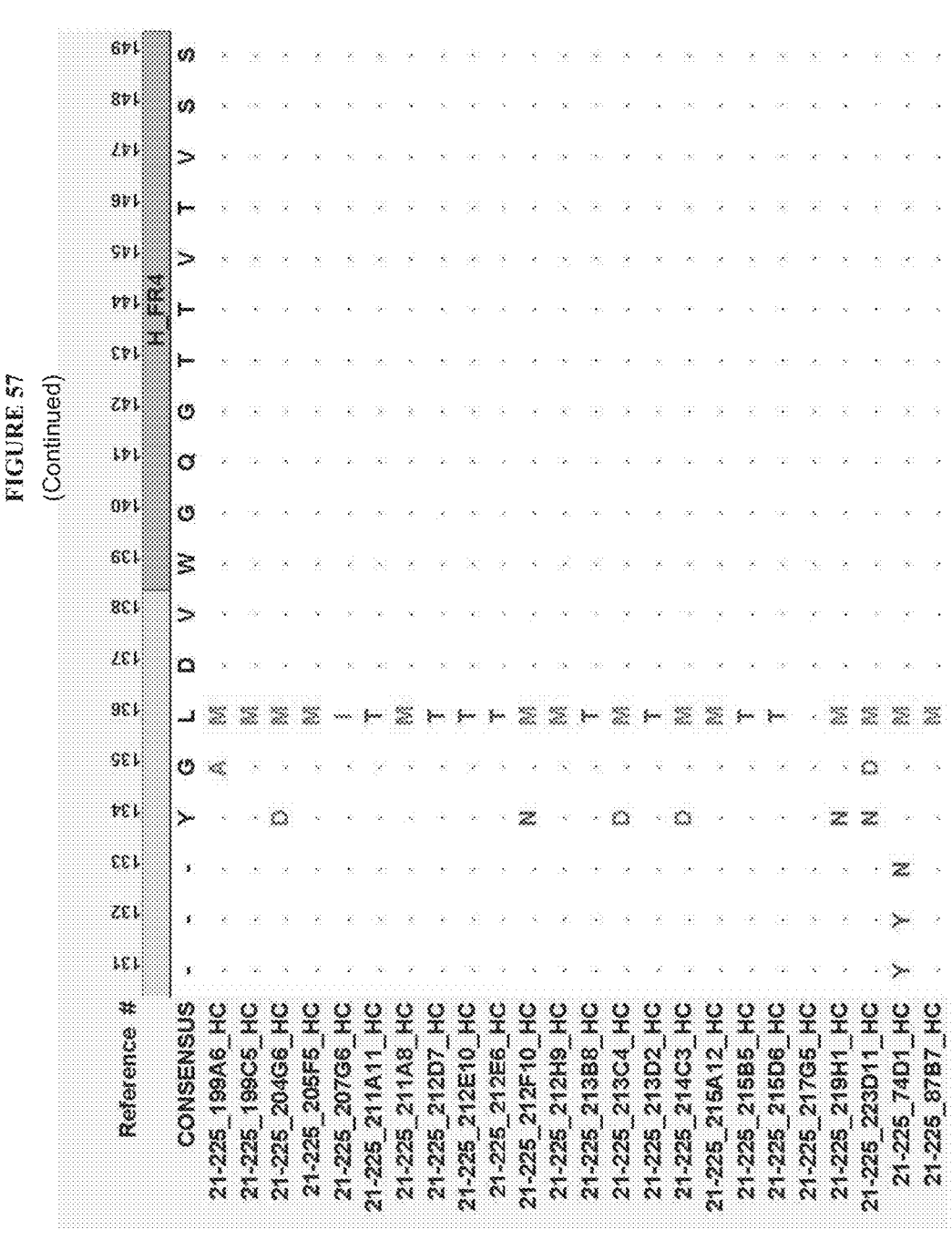
Figure 57:
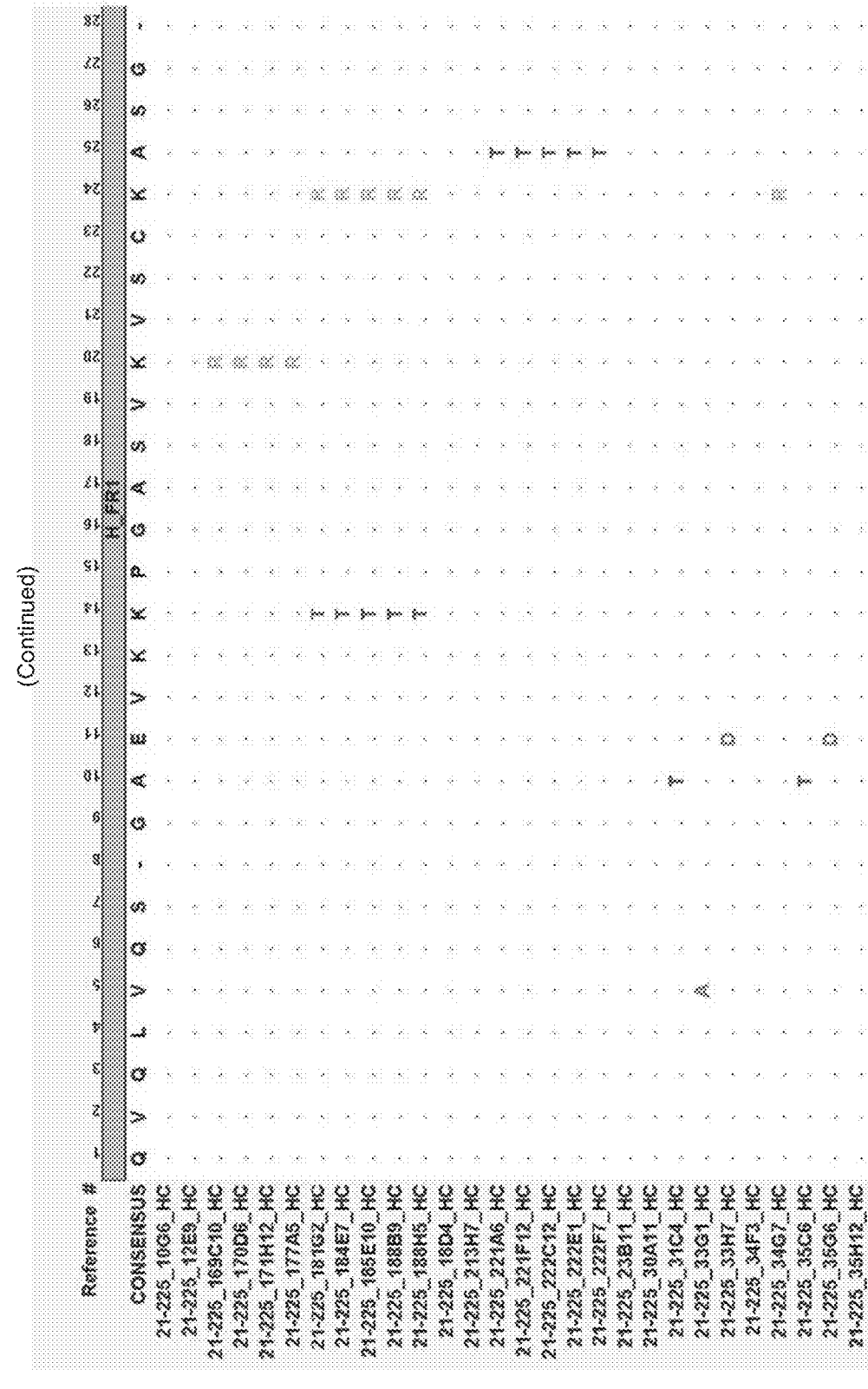
Figure 57:
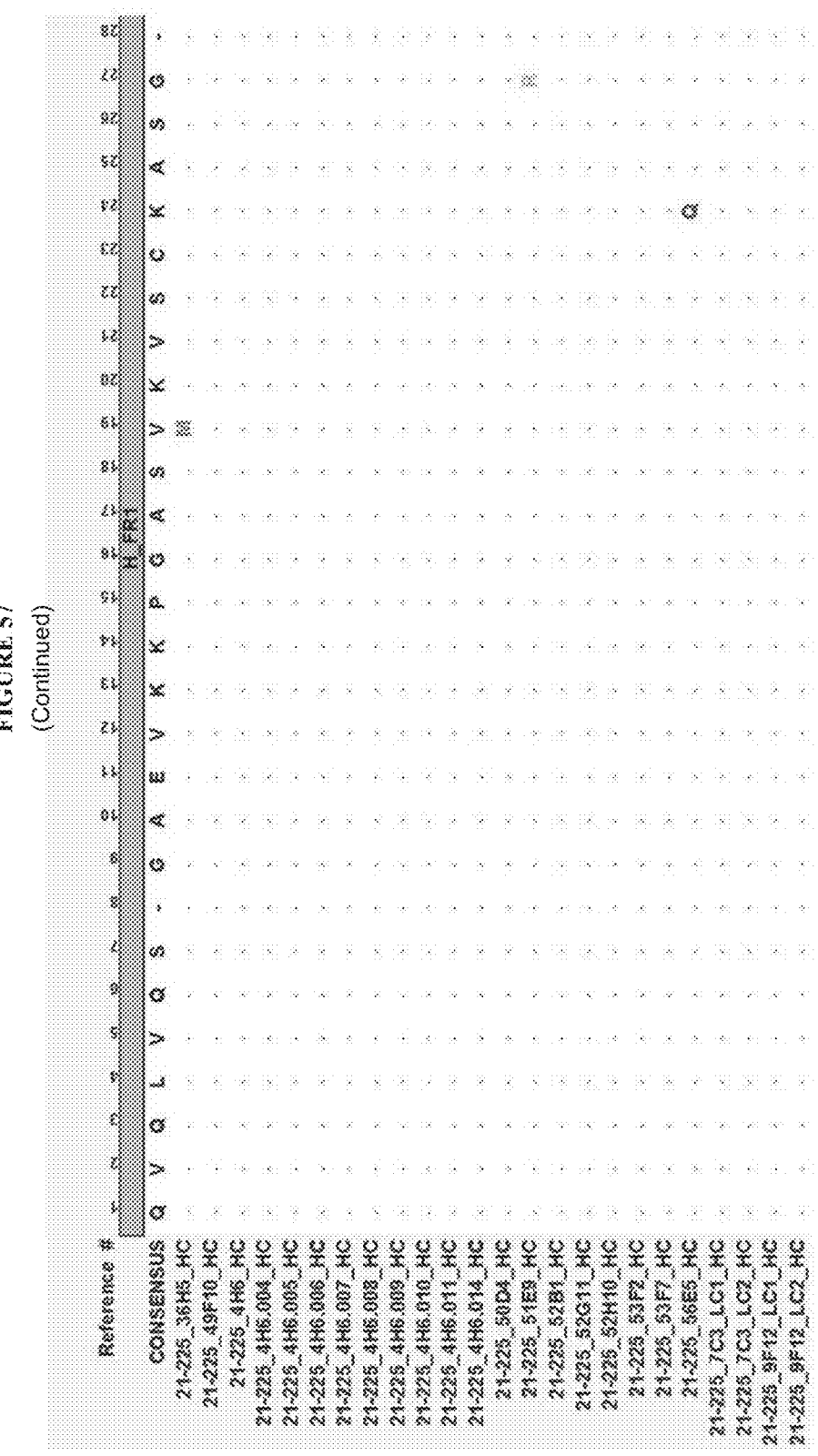
Figure 57:
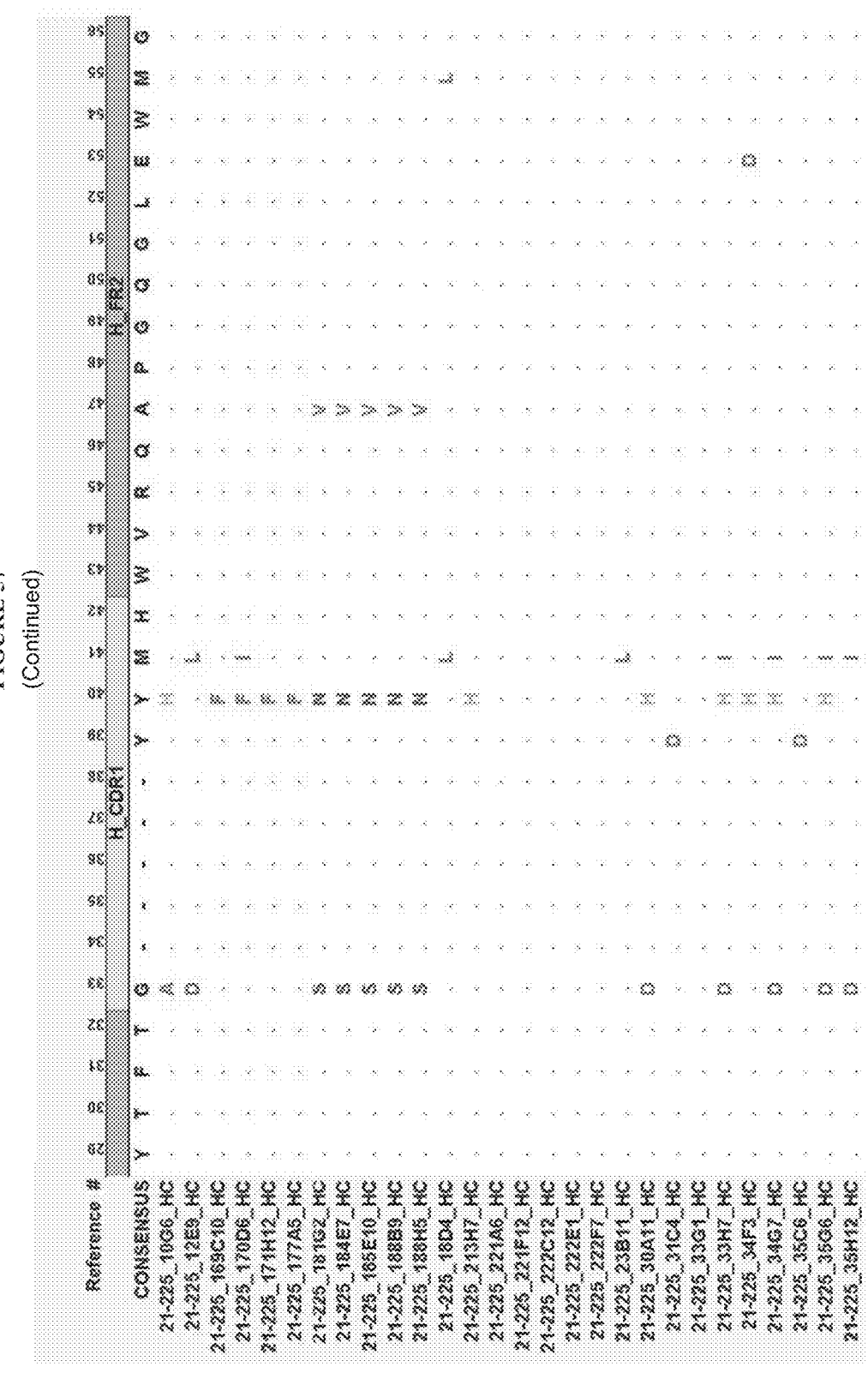
Figure 57:
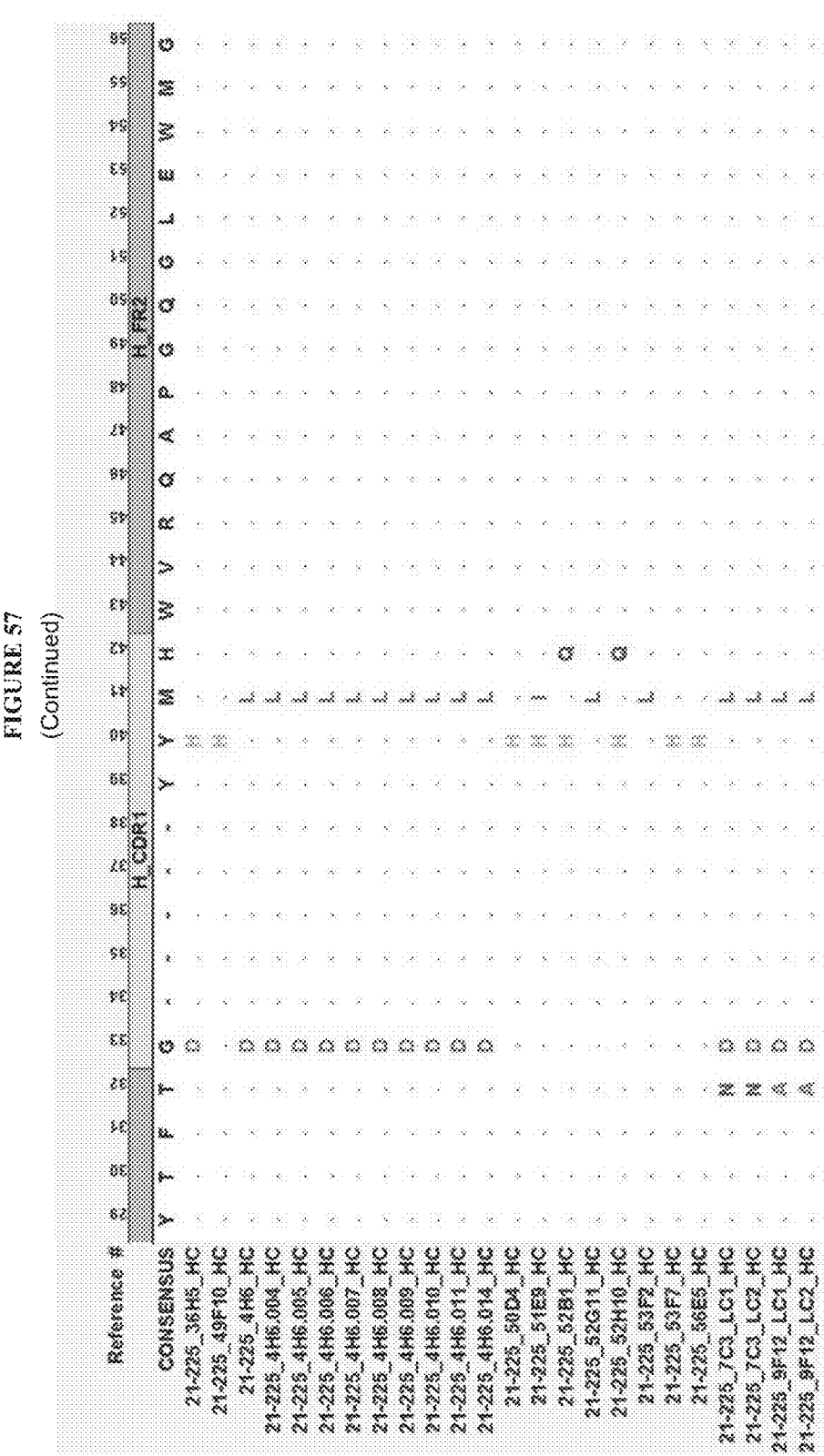
Figure 57:
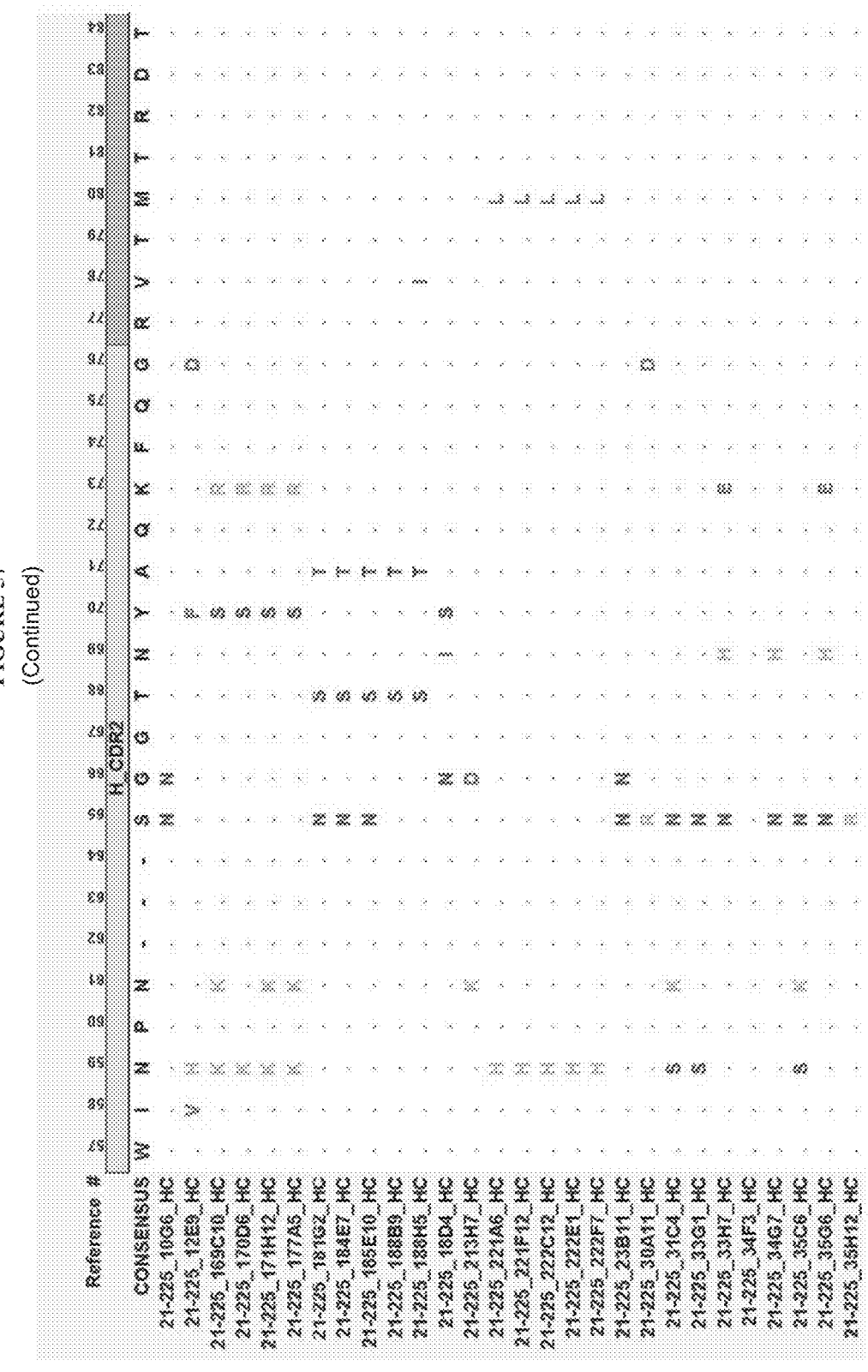
Figure 57:
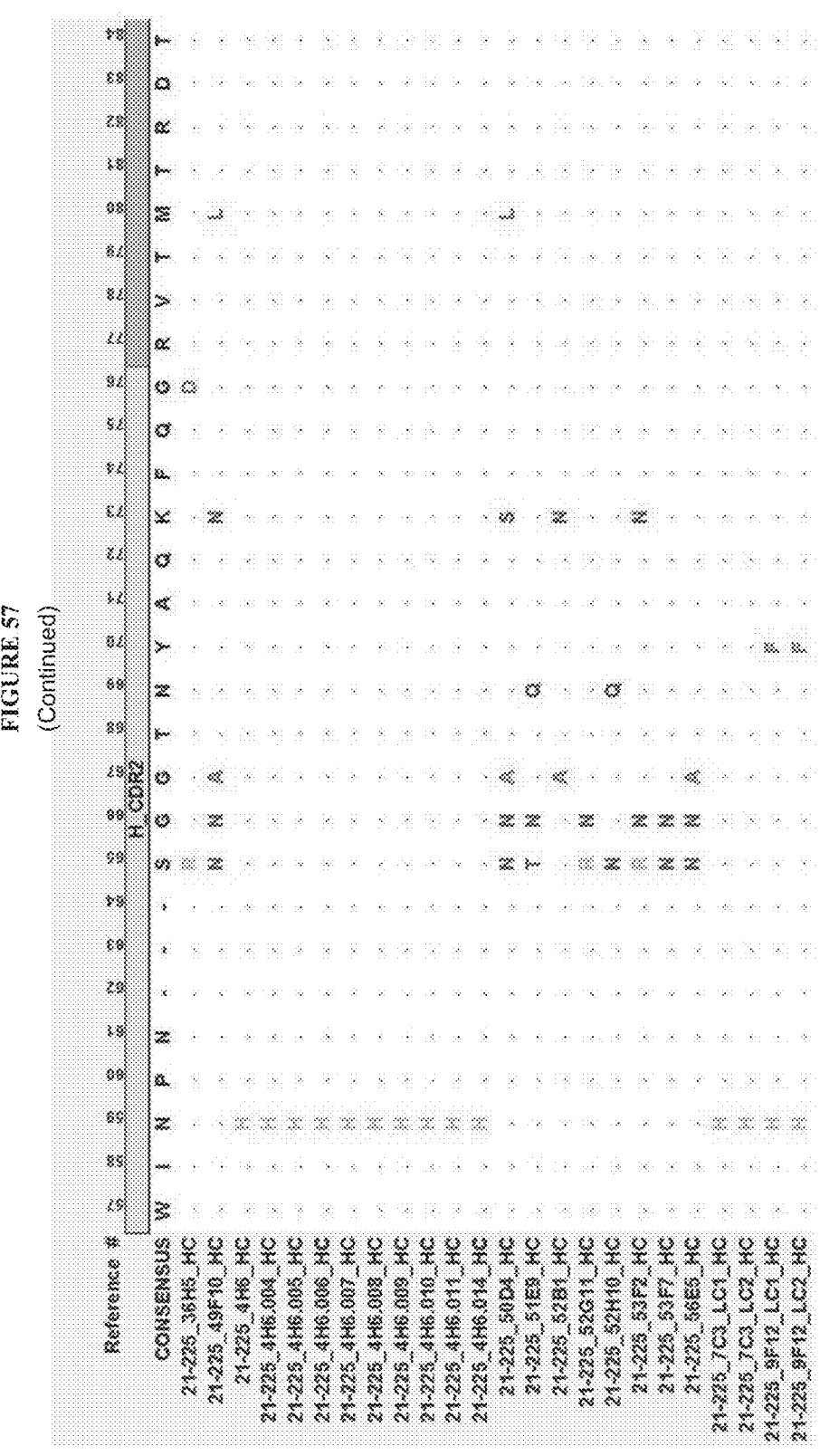
Figure 57:
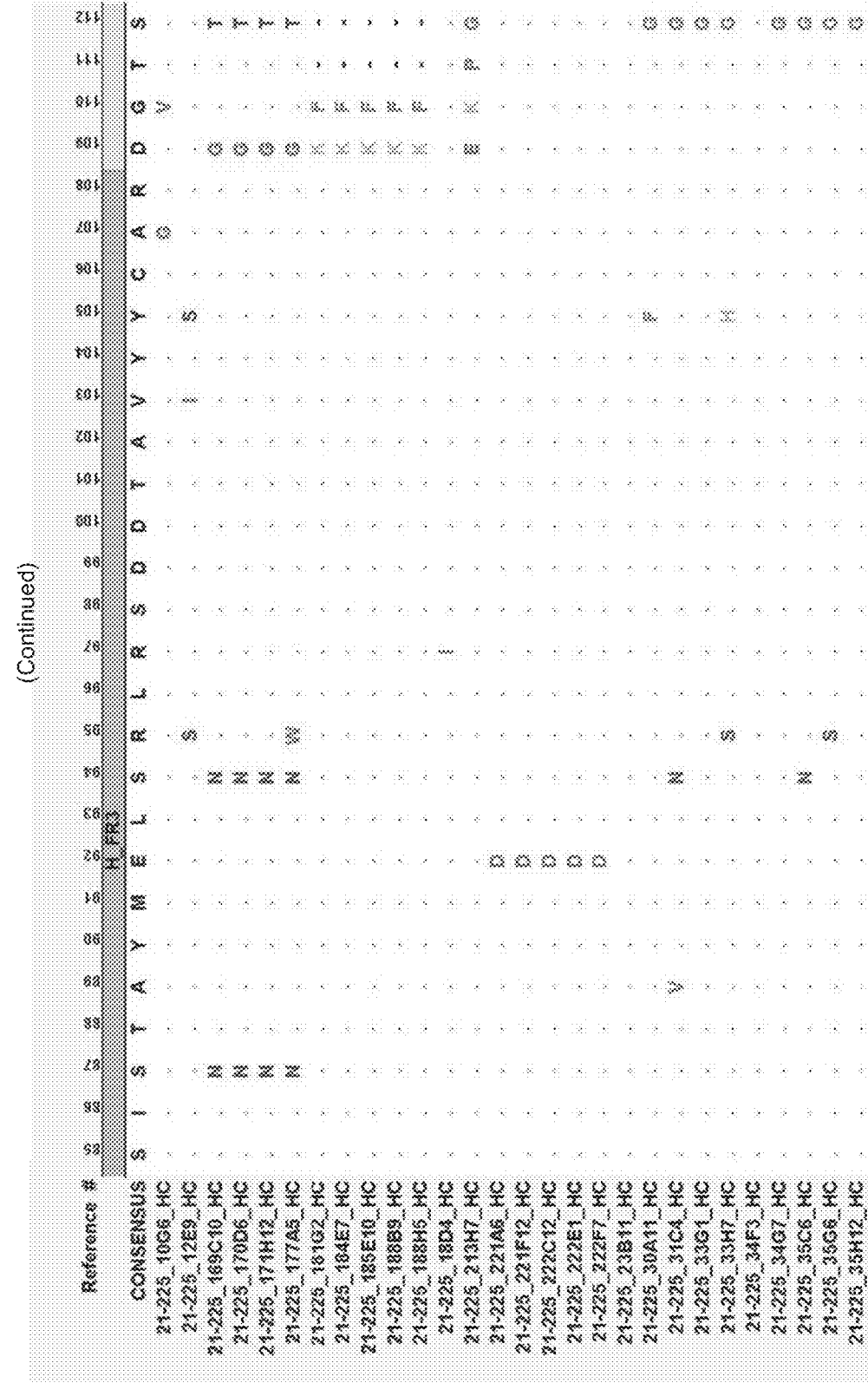
Figure 57:
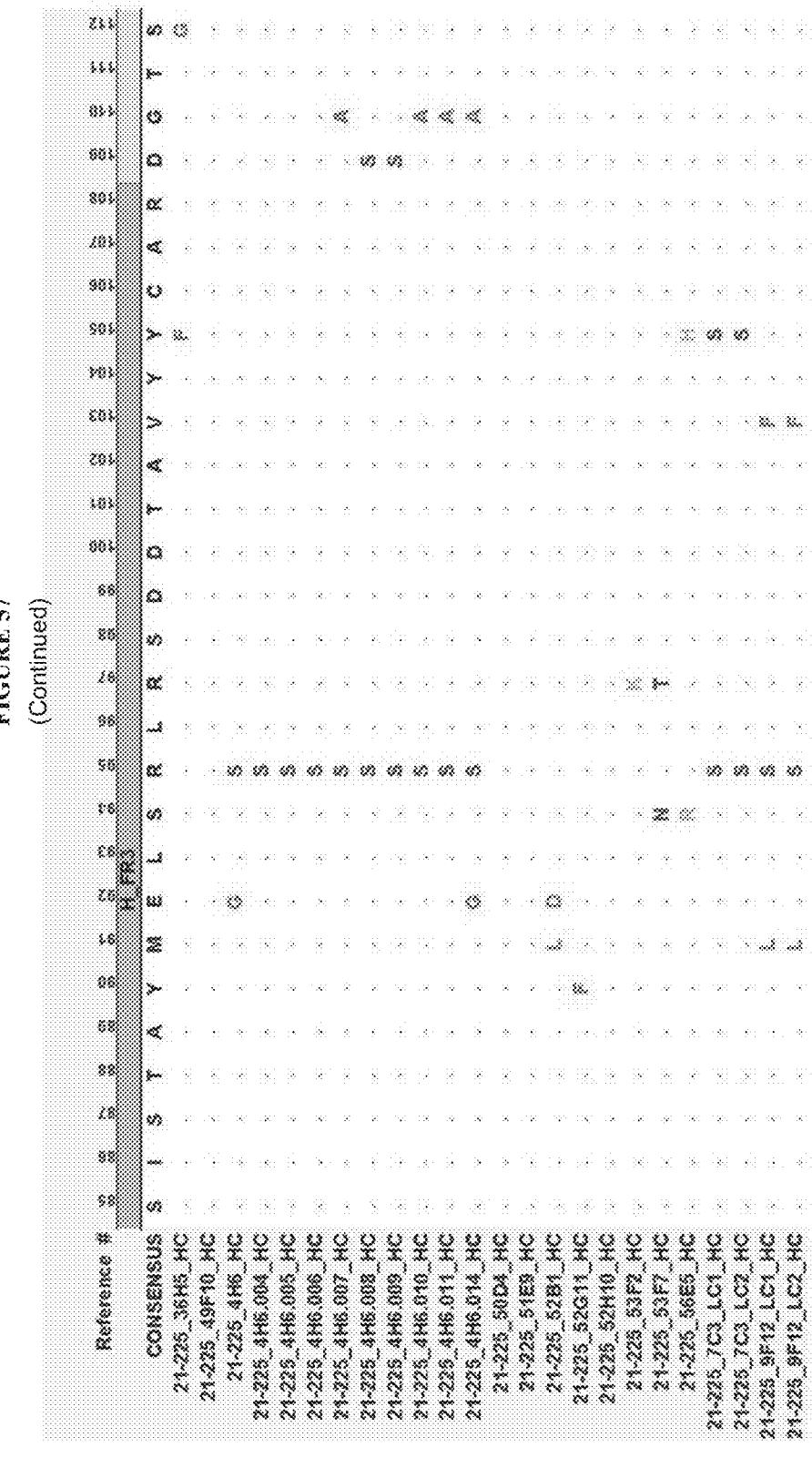
Figure 57:
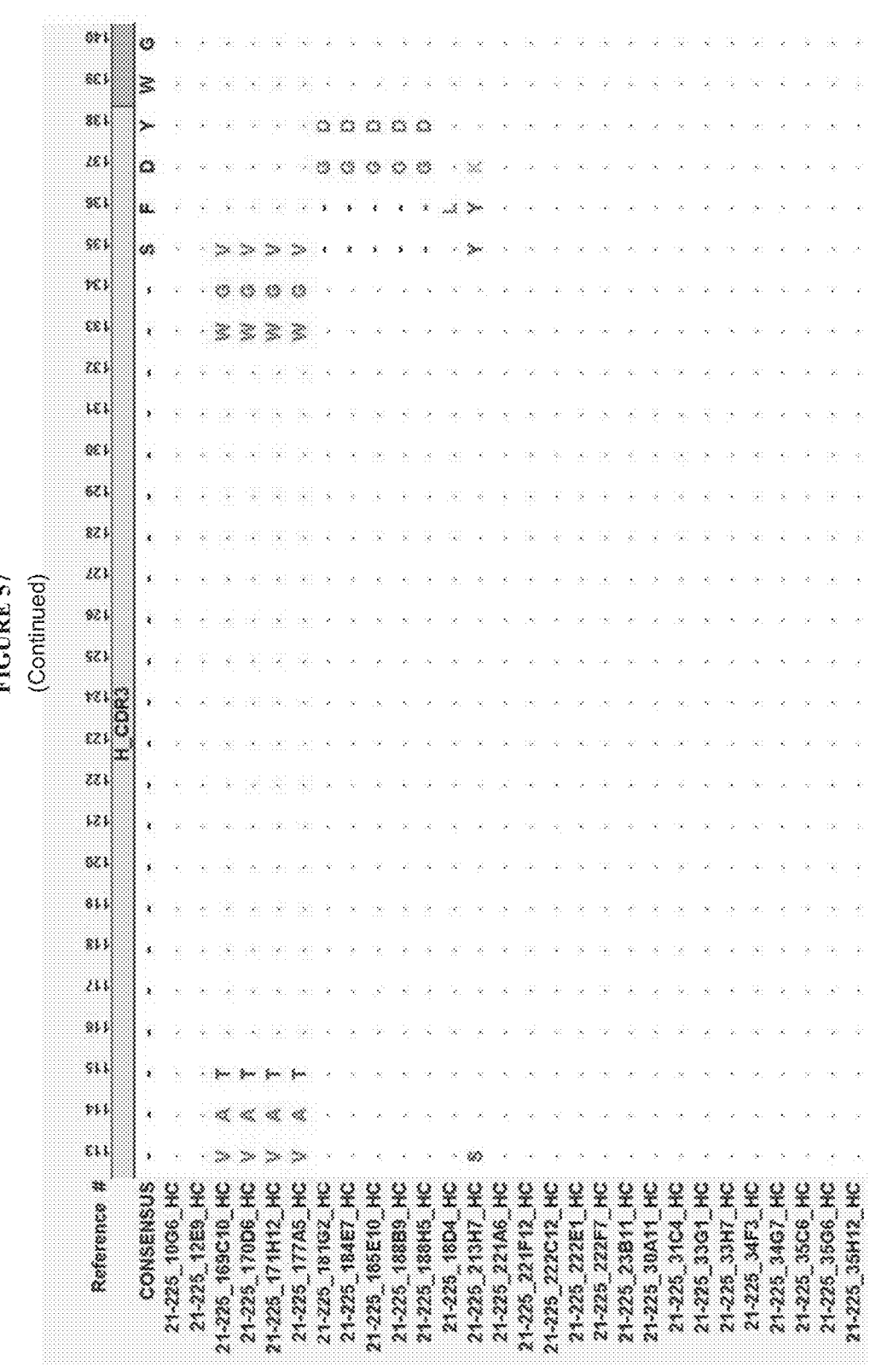
Figure 57:
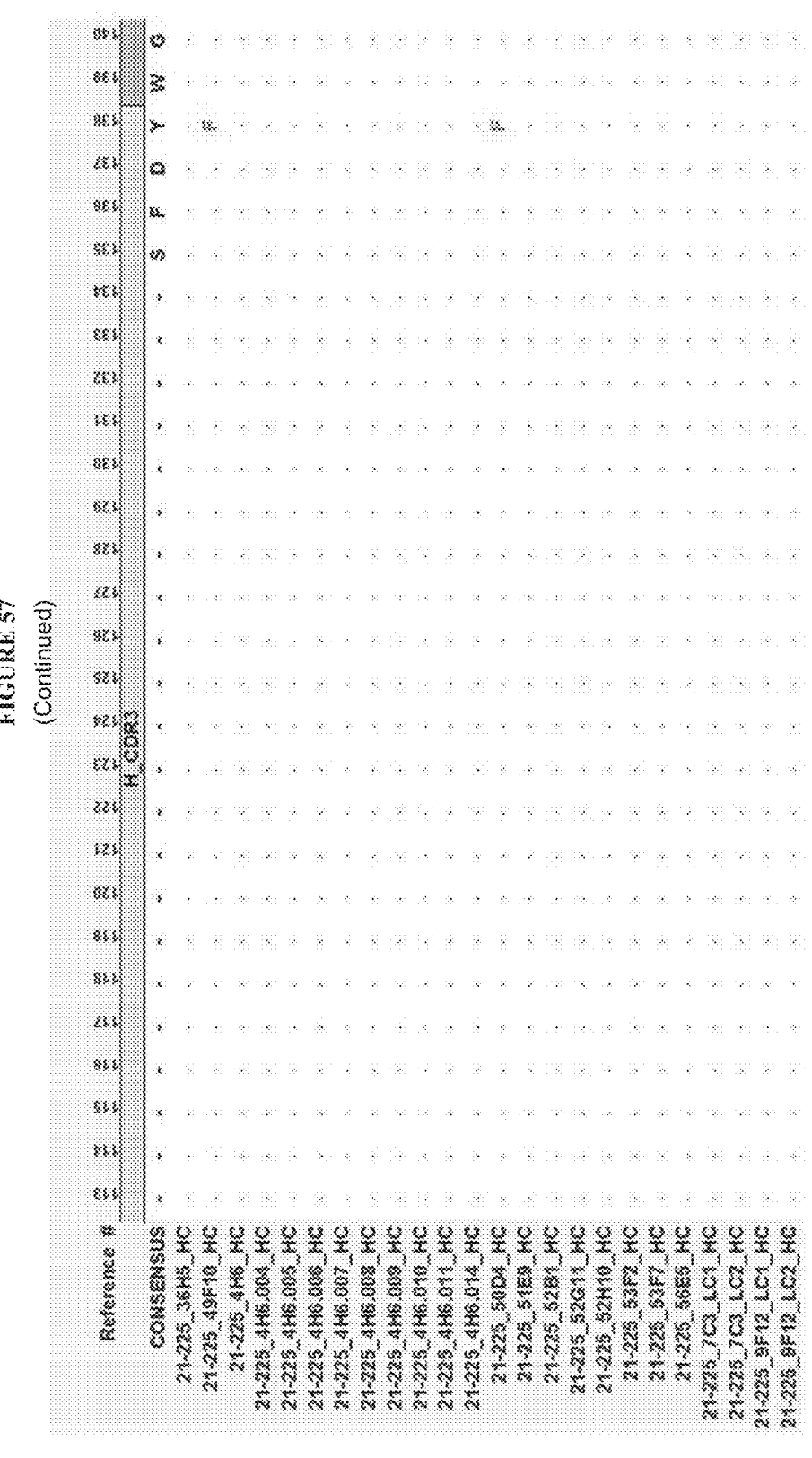
Figure 57:
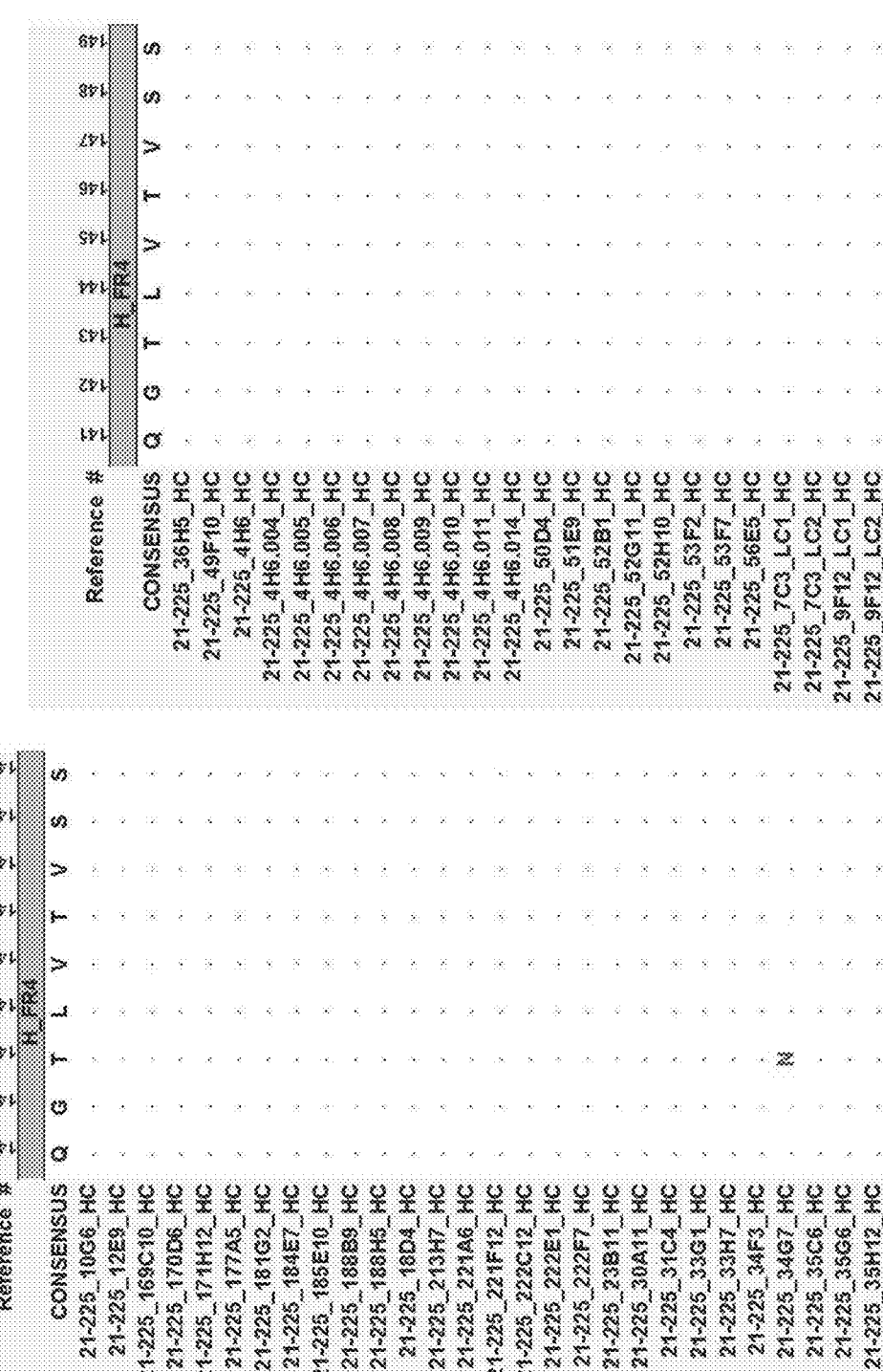
Figure 57:
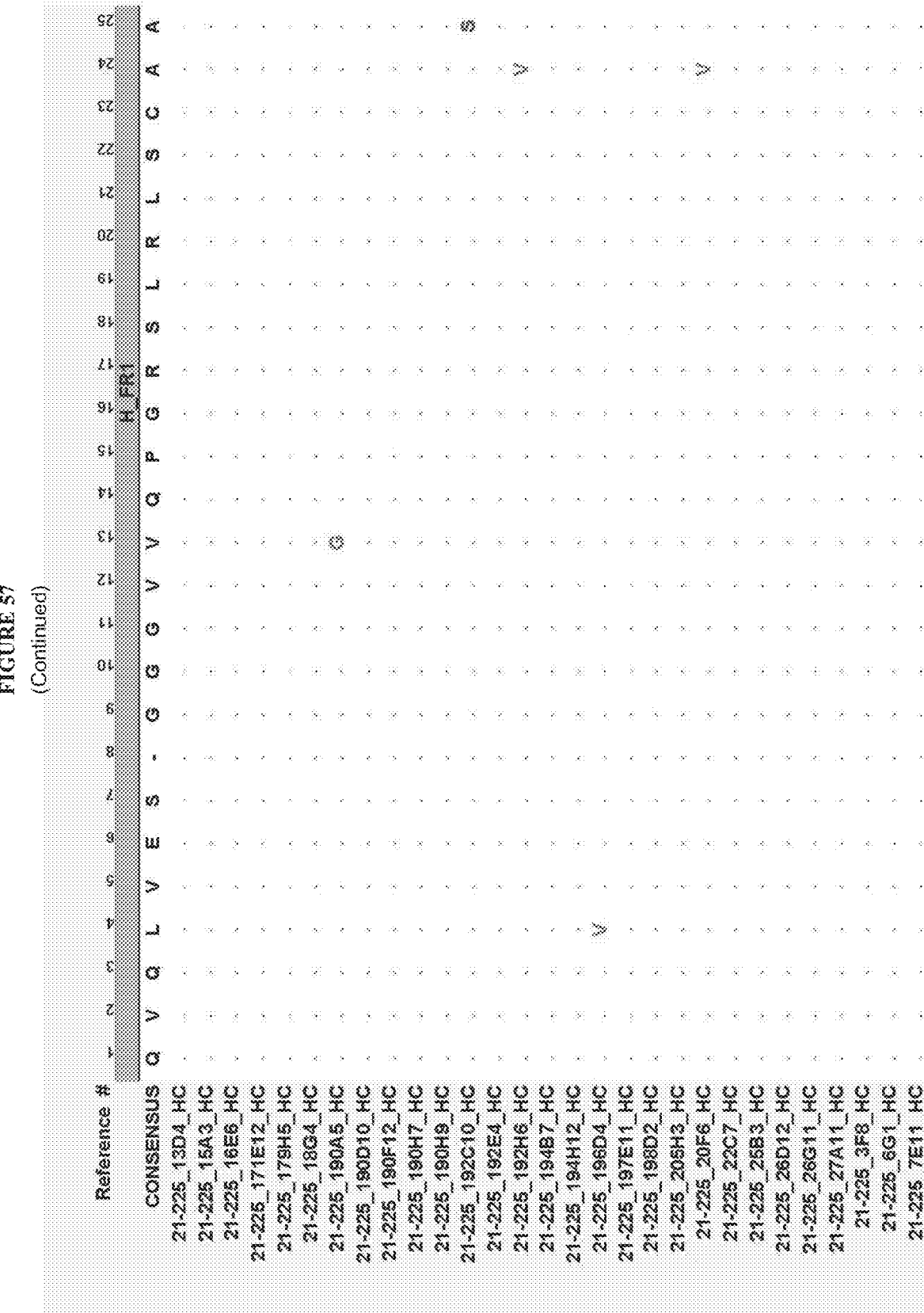
Figure 57:
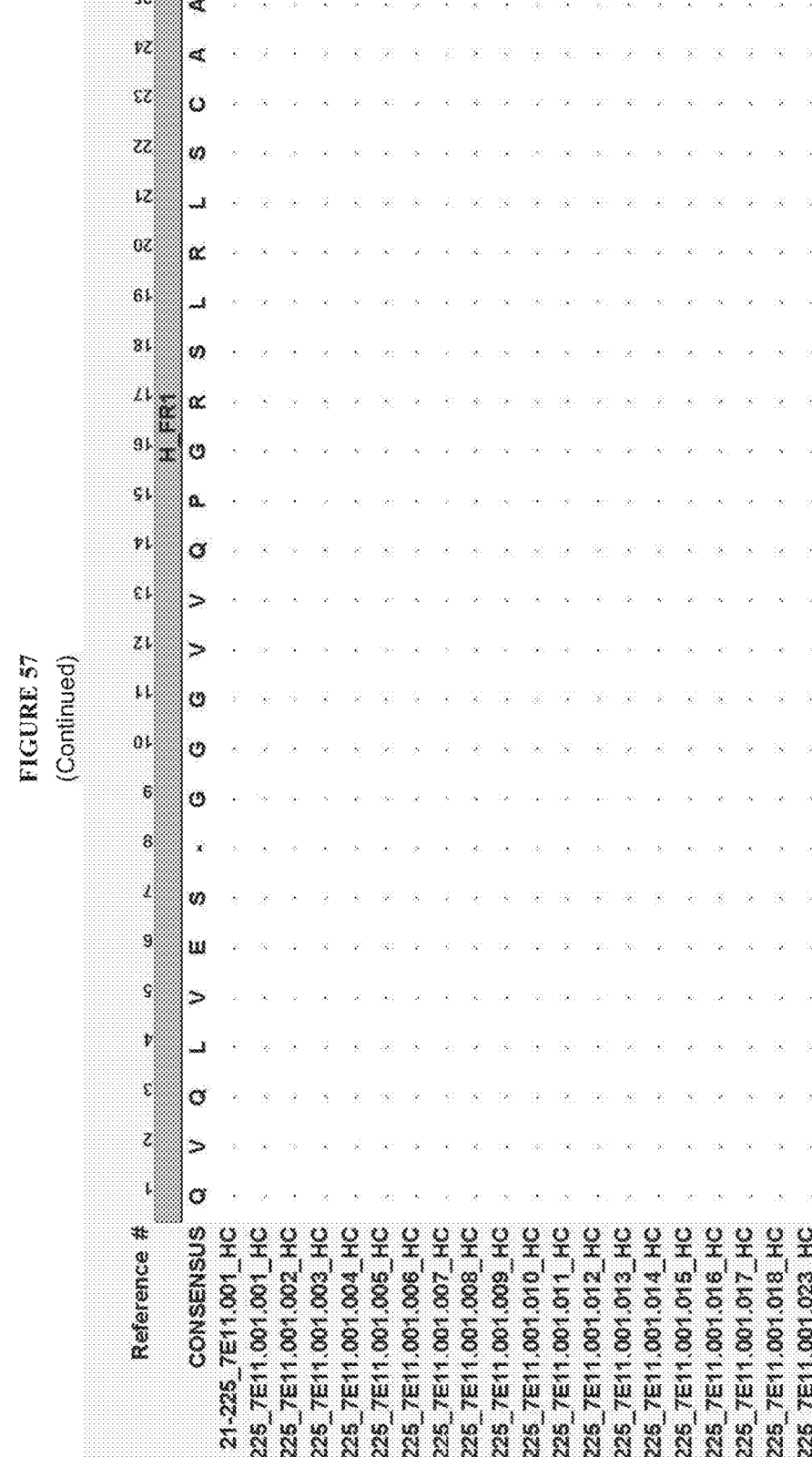
Figure 57:
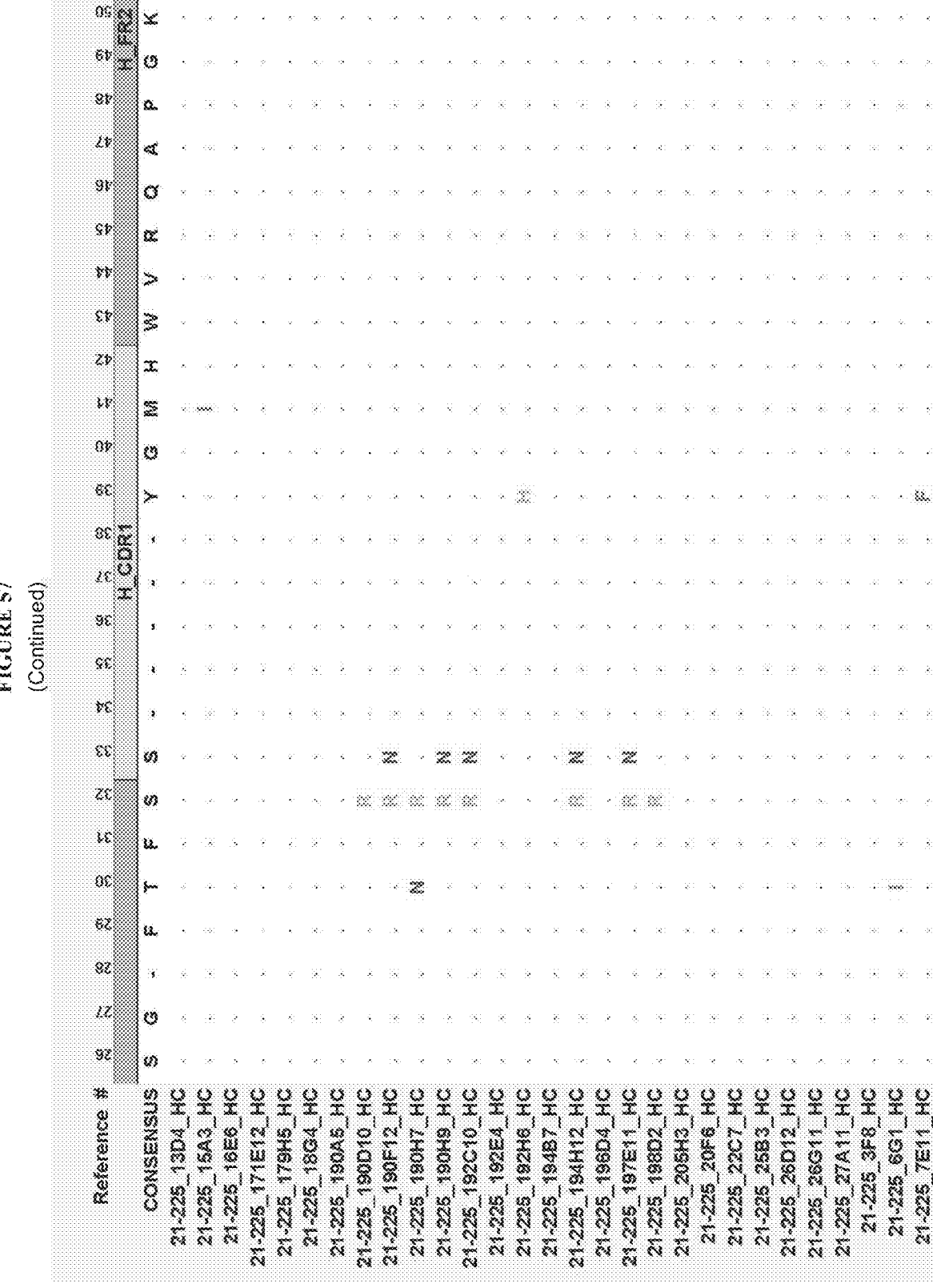
Figure 57:
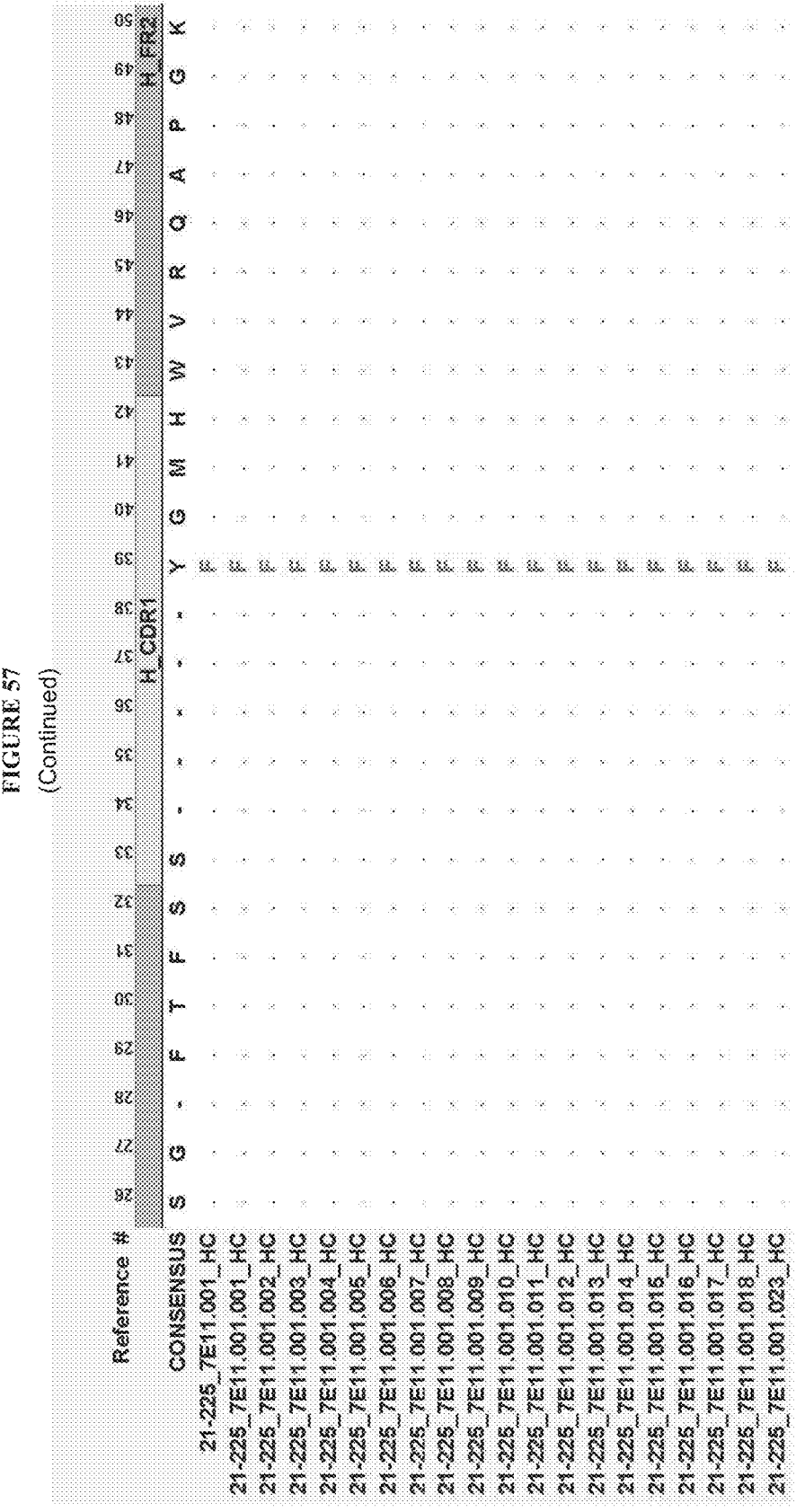
Figure 57:
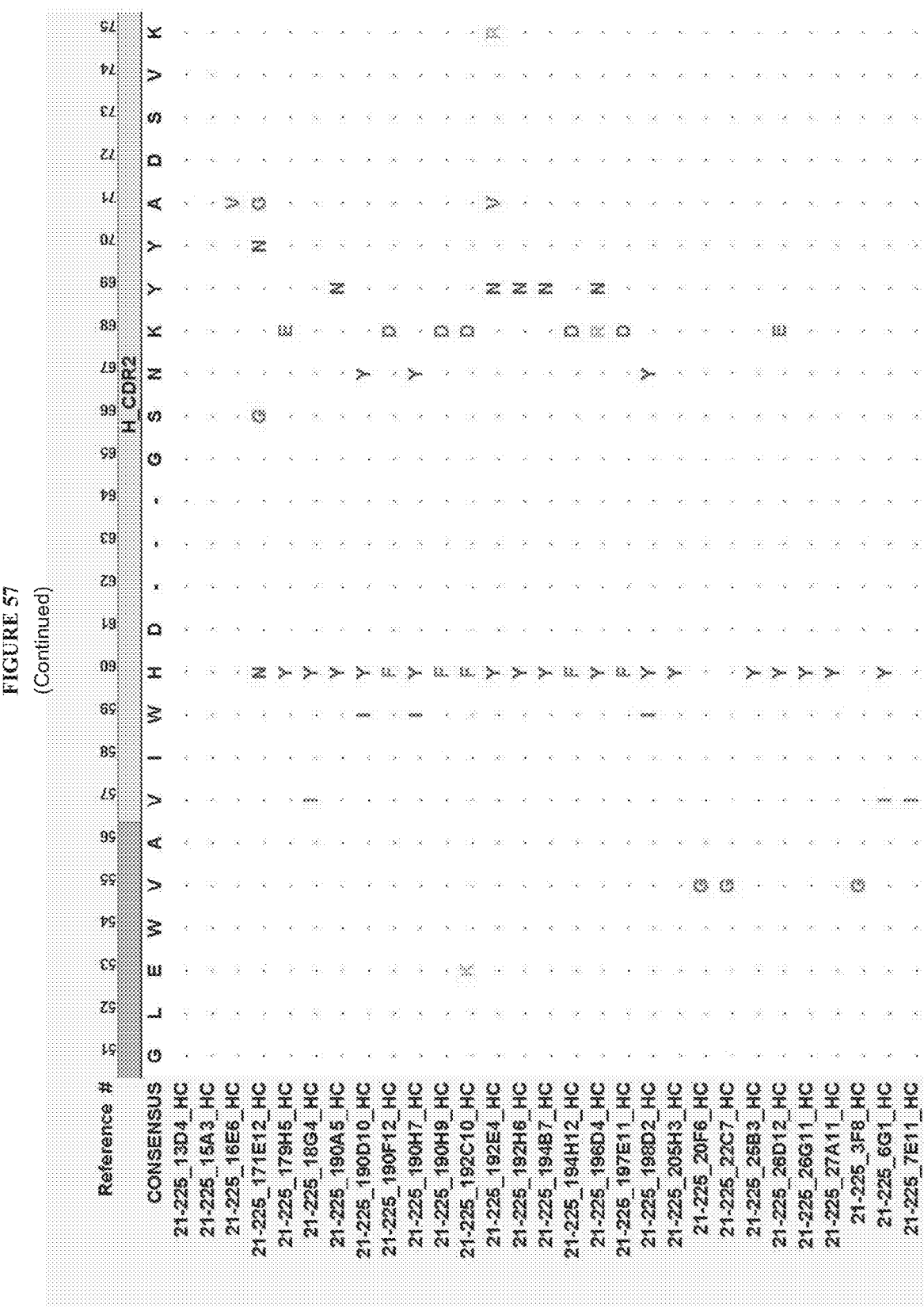
Figure 57:
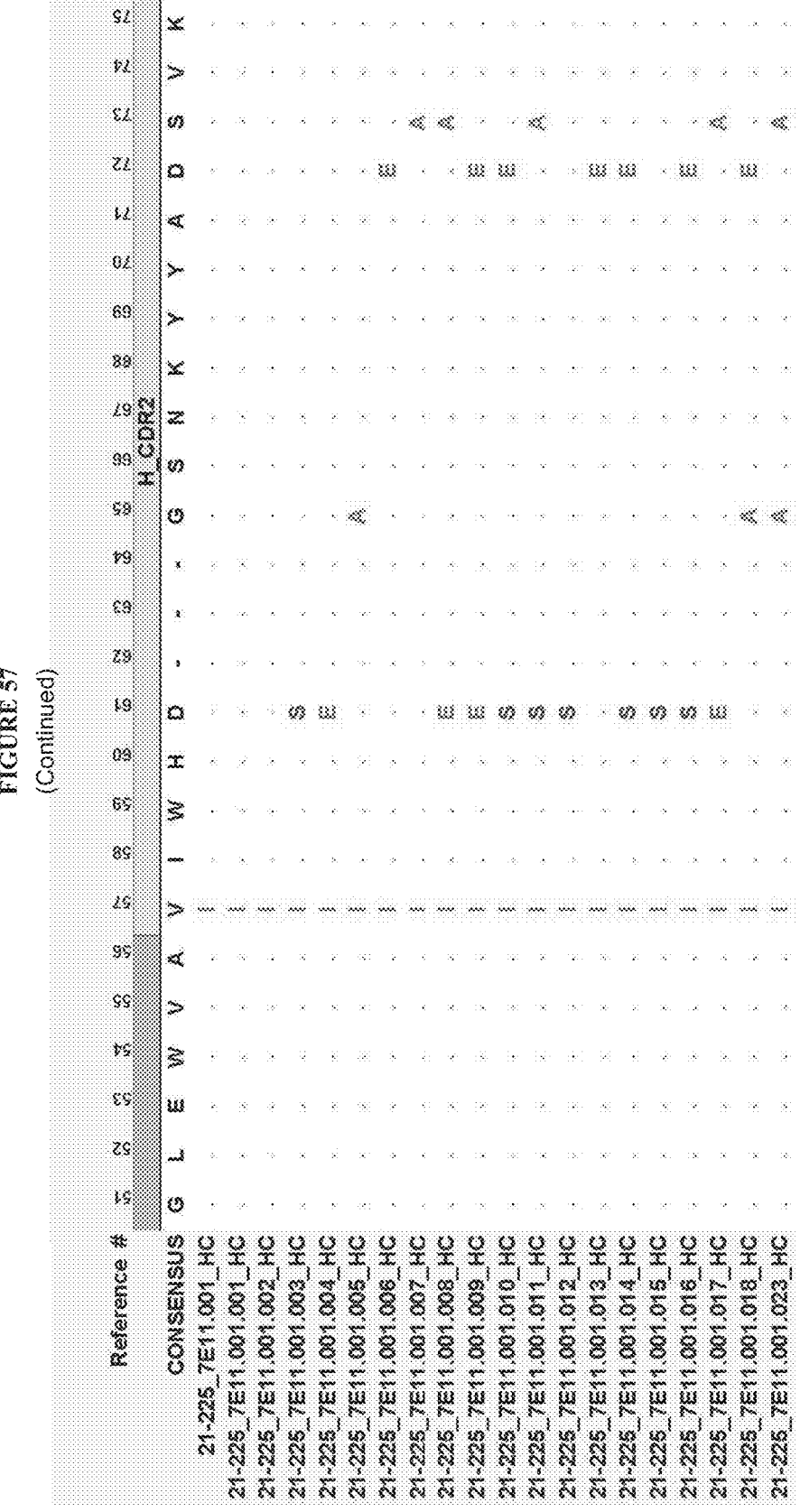
Figure 57:
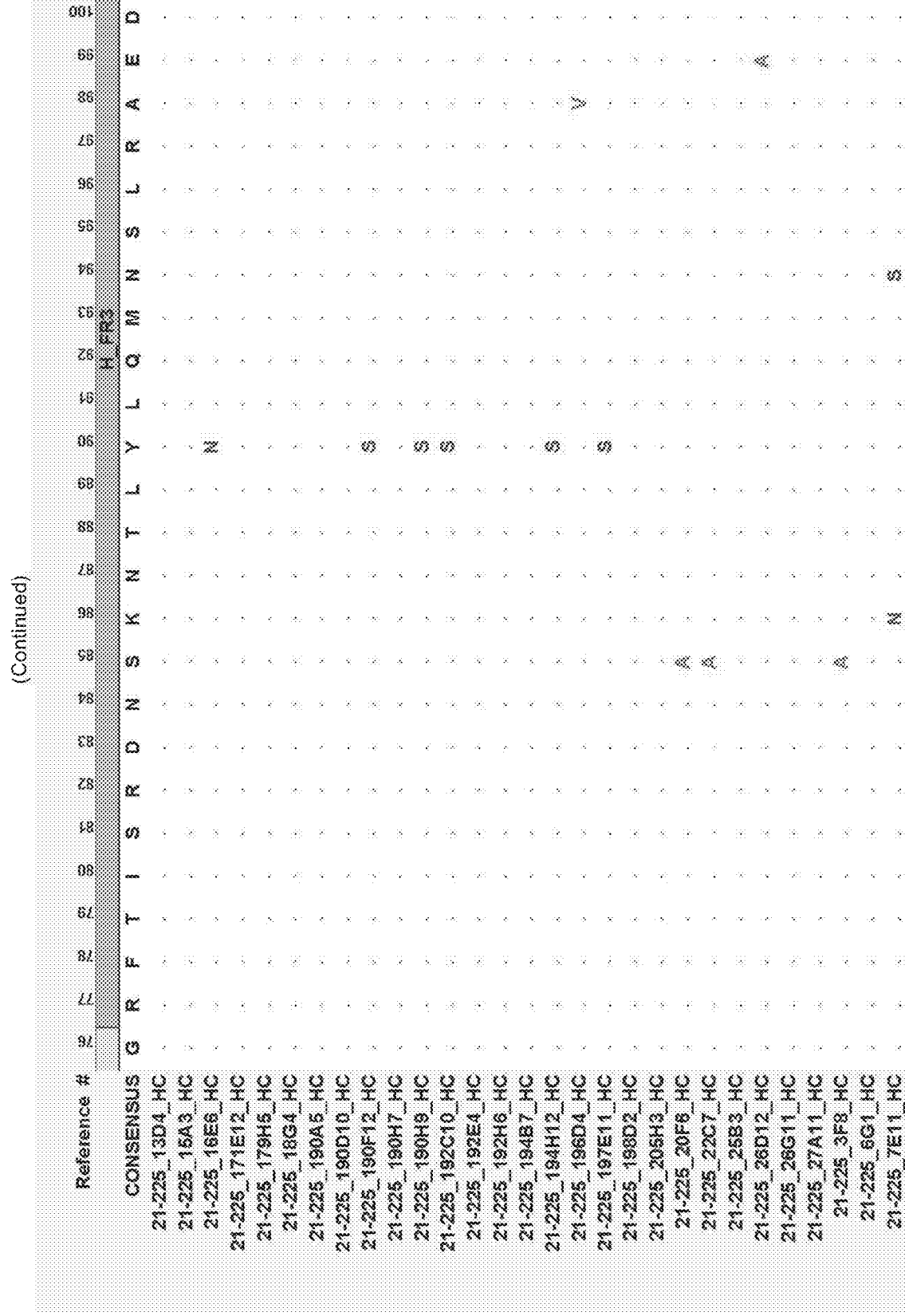
Figure 57:
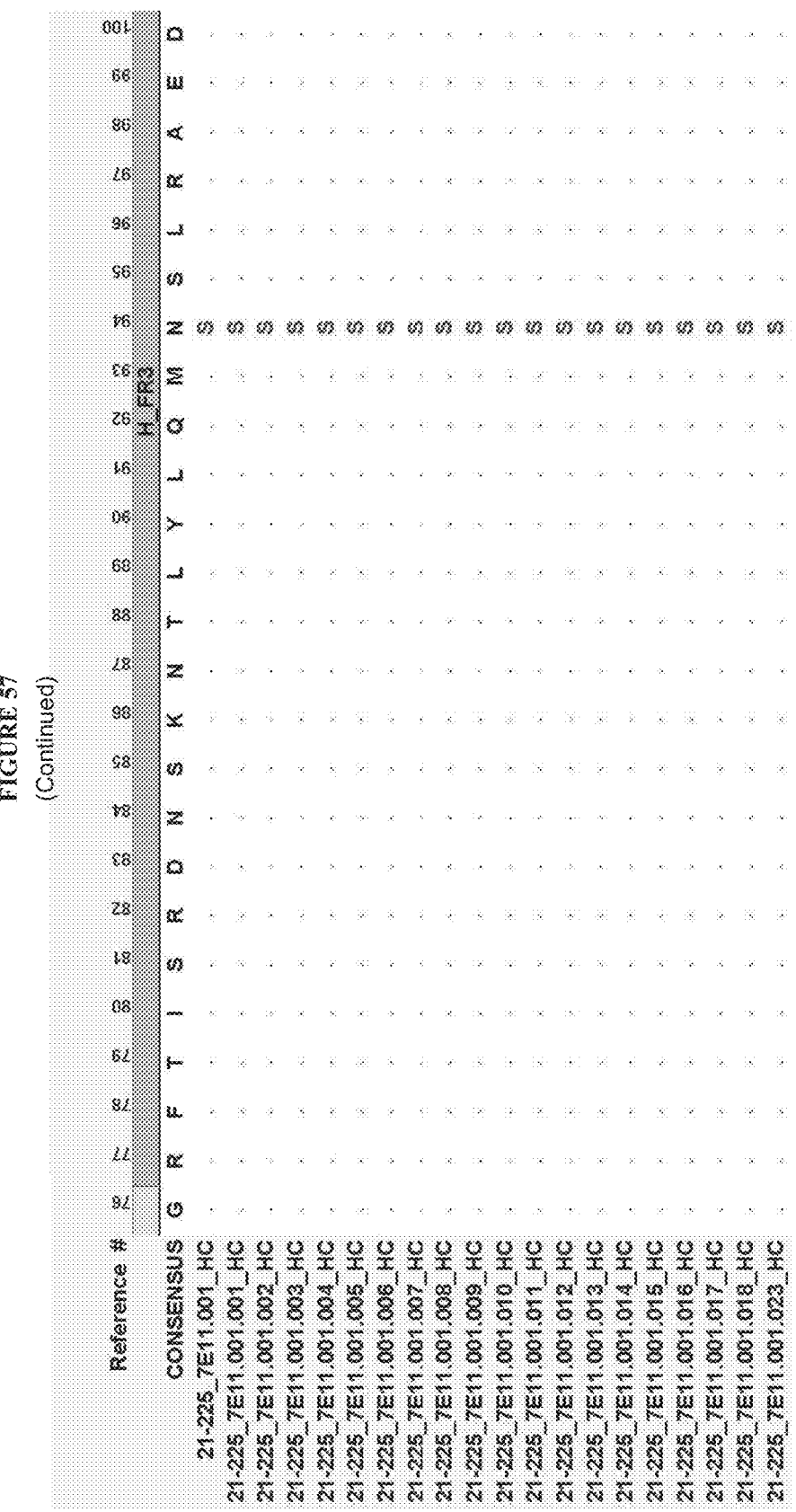
Figure 57:
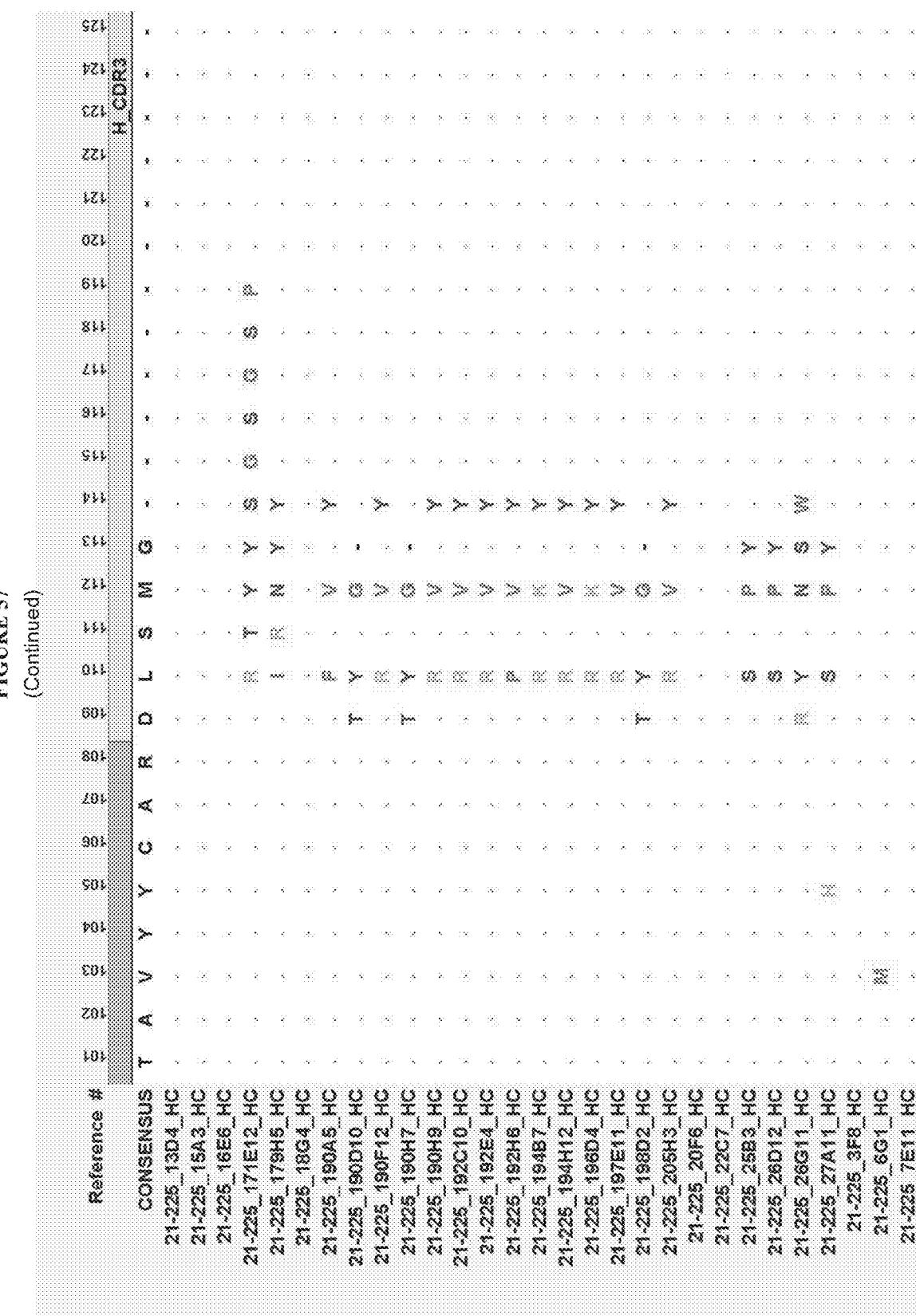
Figure 57:
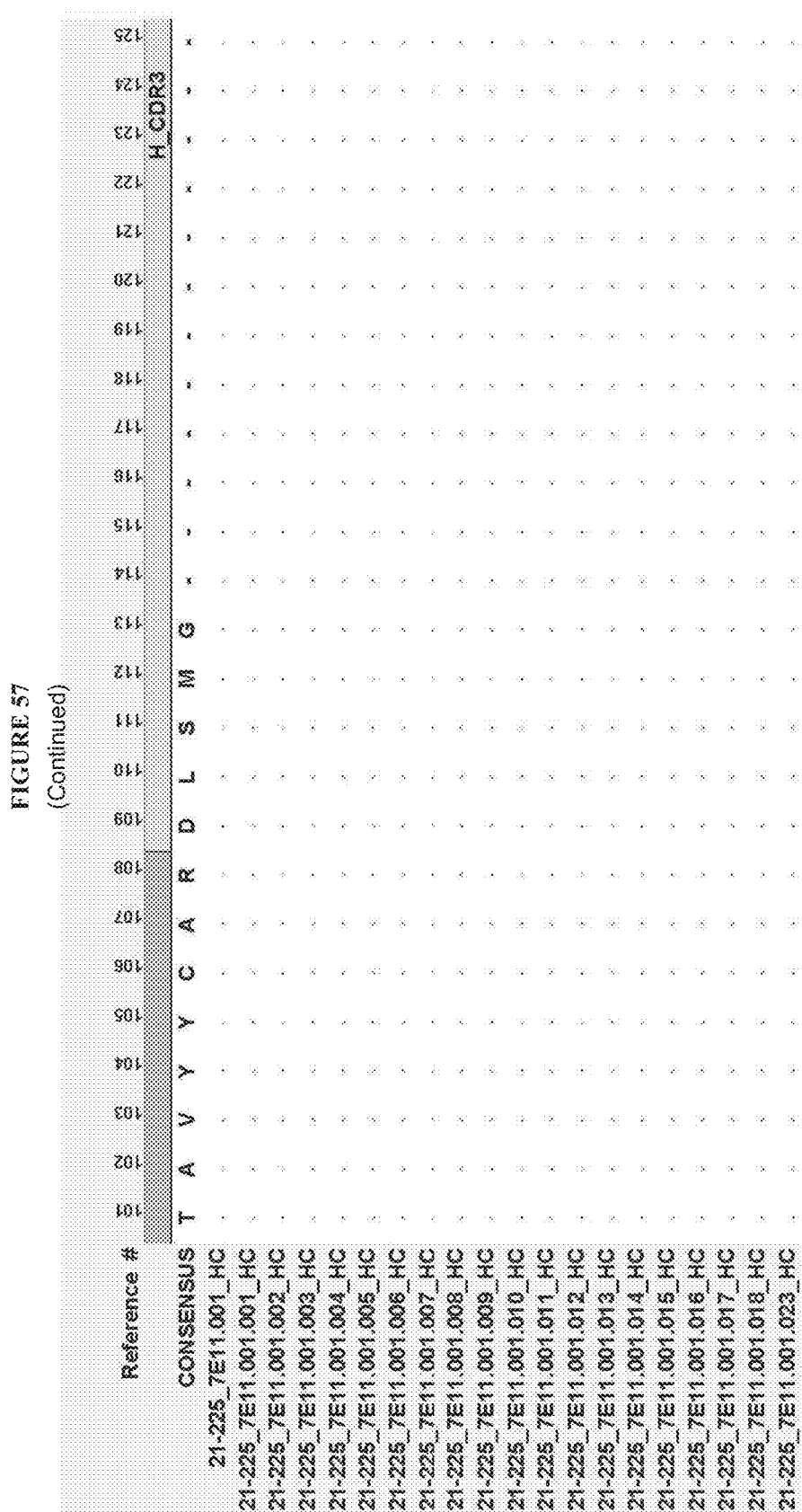
Figure 57:
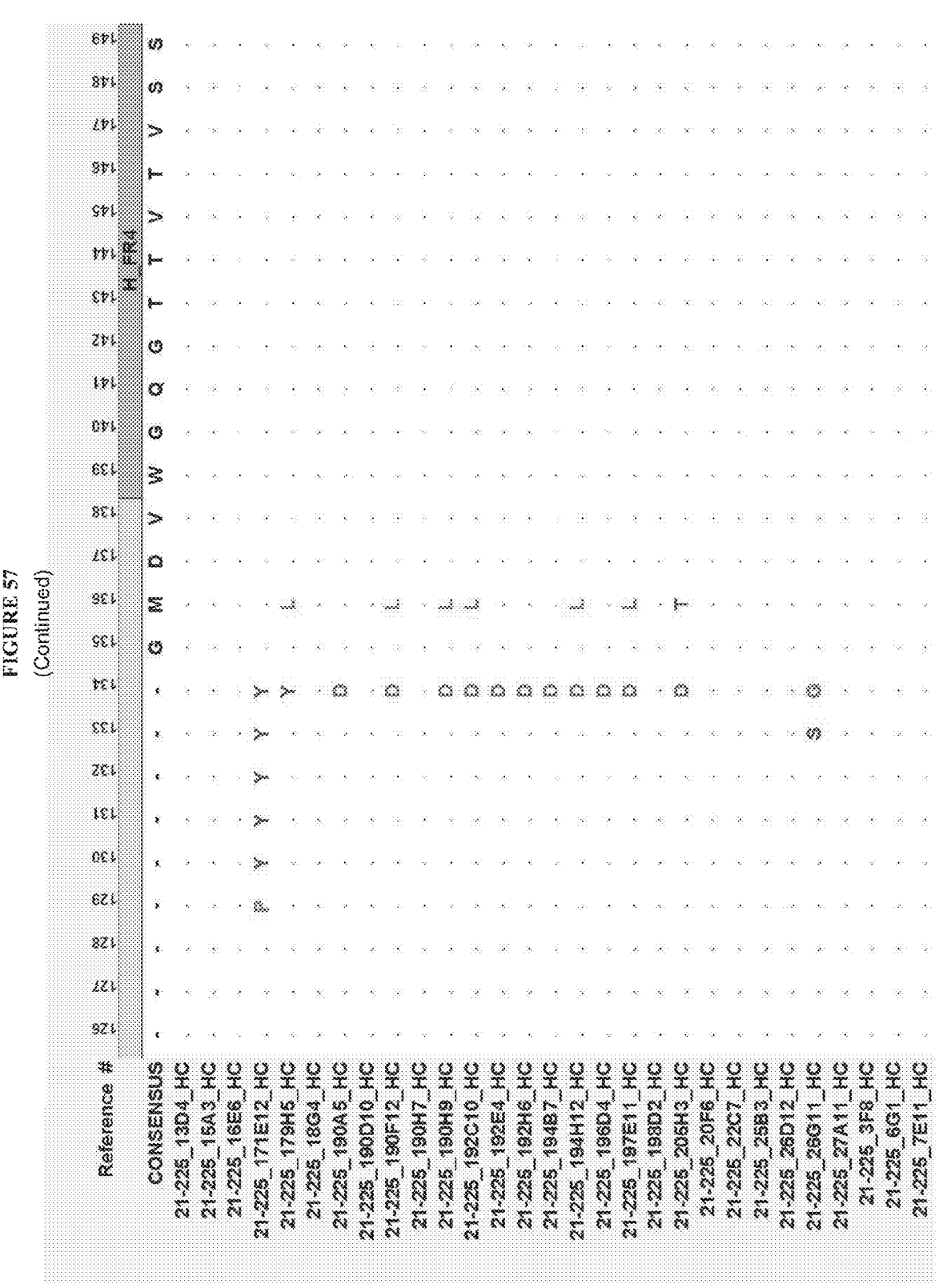
Figure 57:
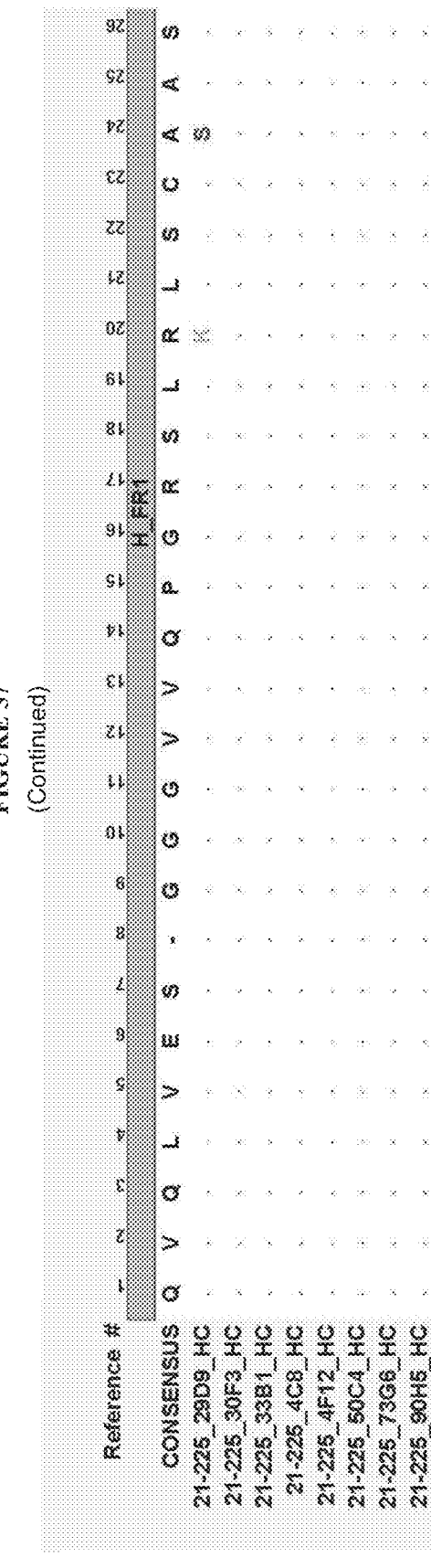
Figure 57:
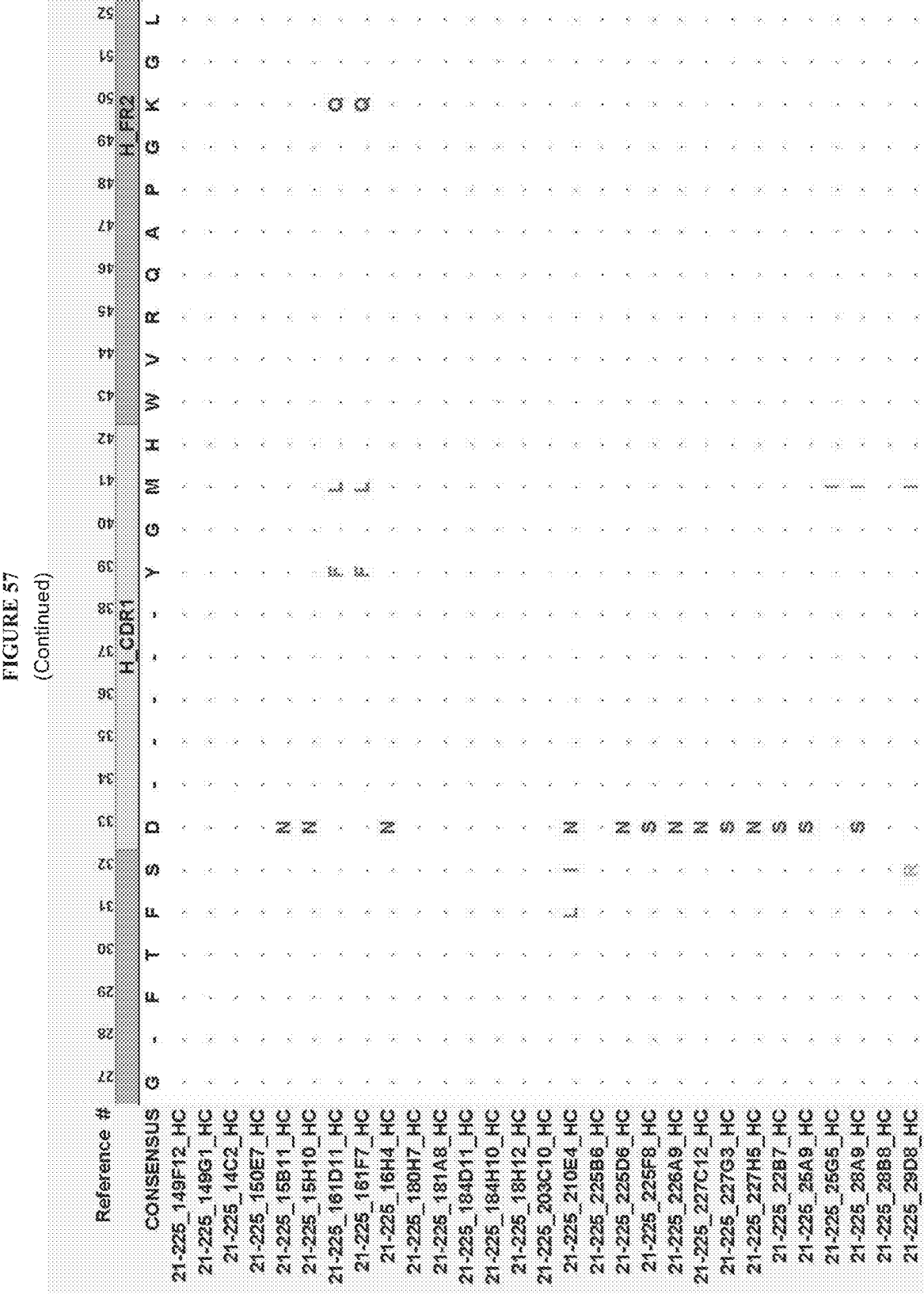
Figure 57:
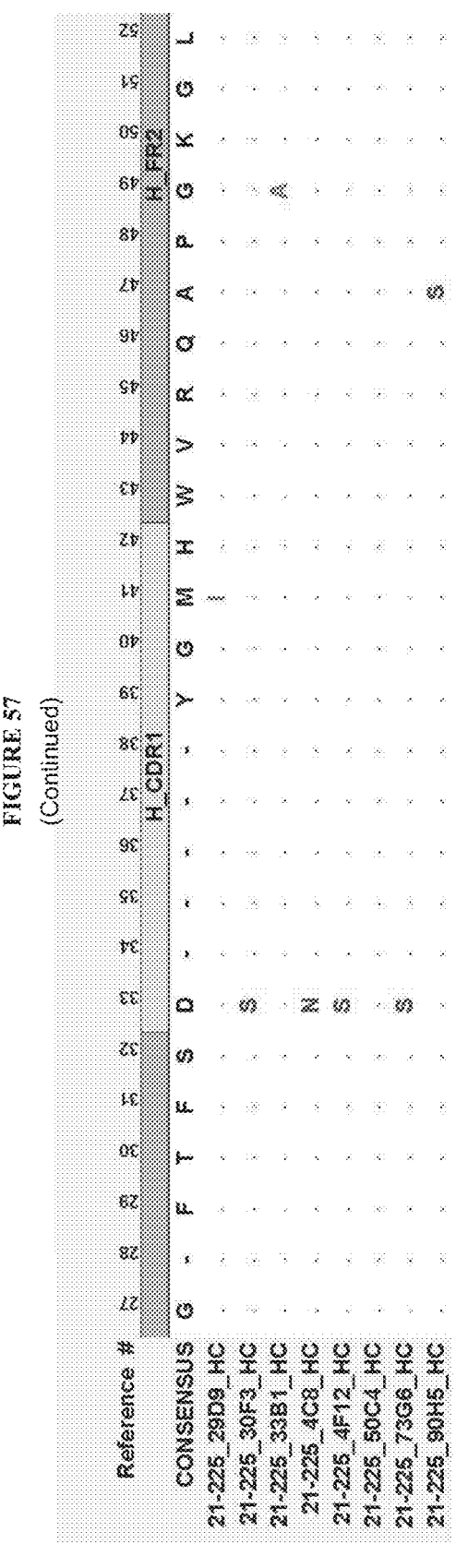
Figure 57:
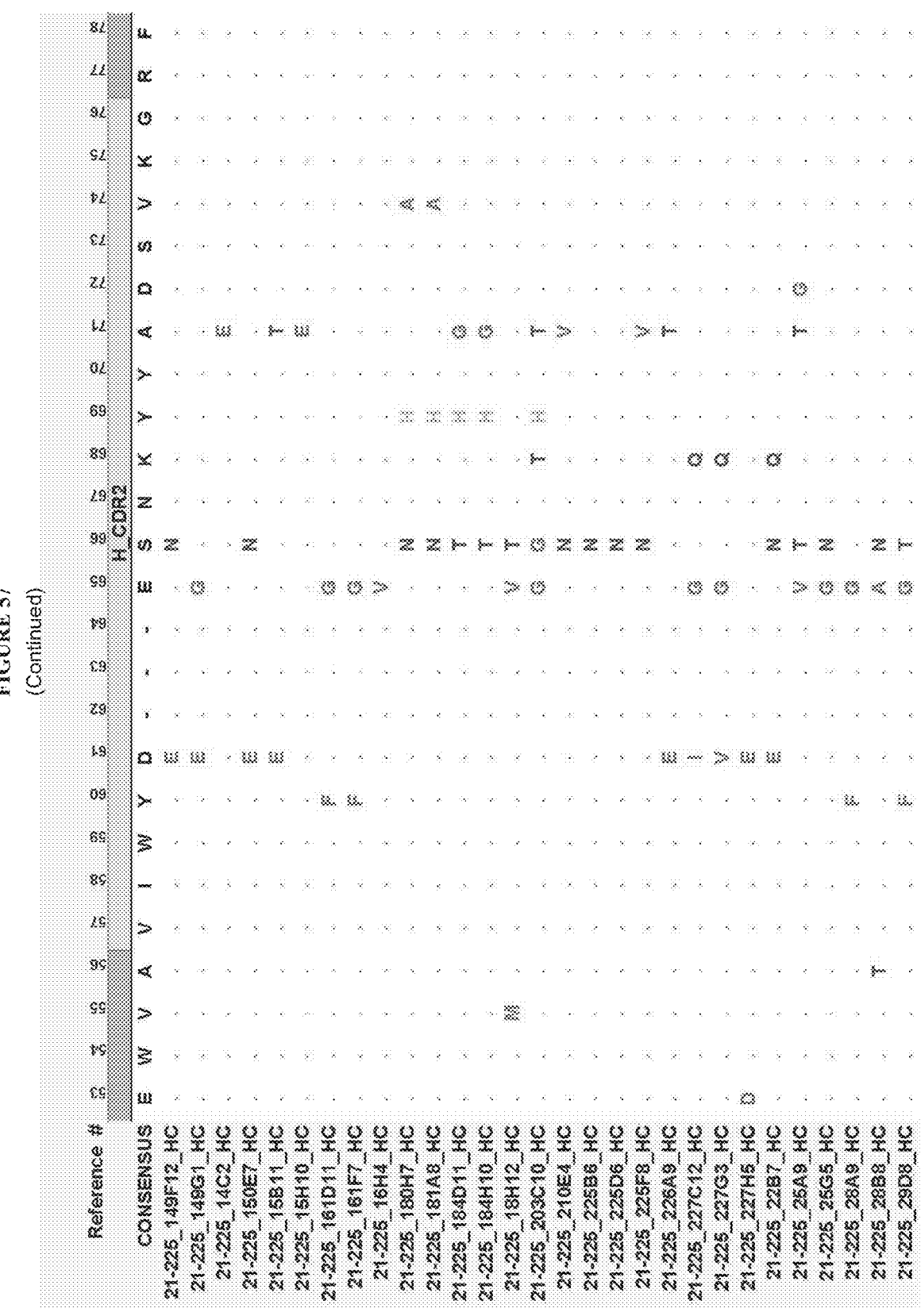
Figure 57:
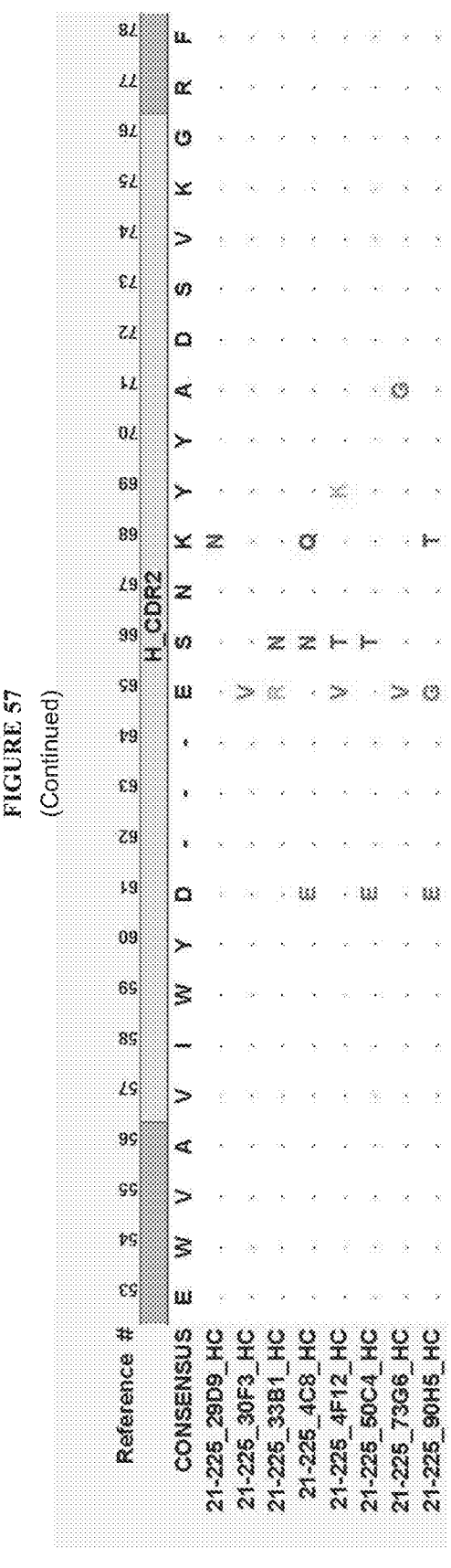
Figure 57:
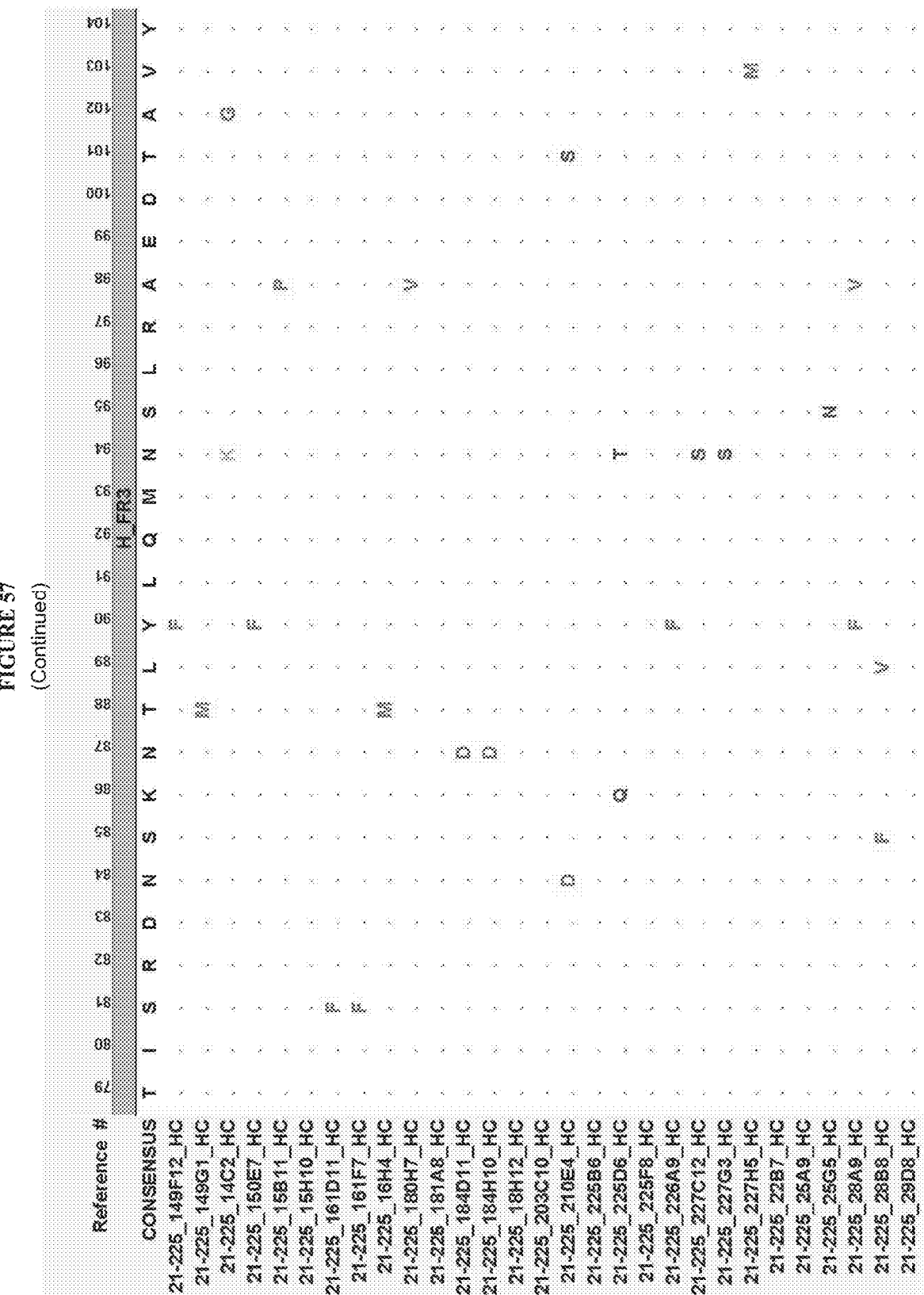
Figure 57:
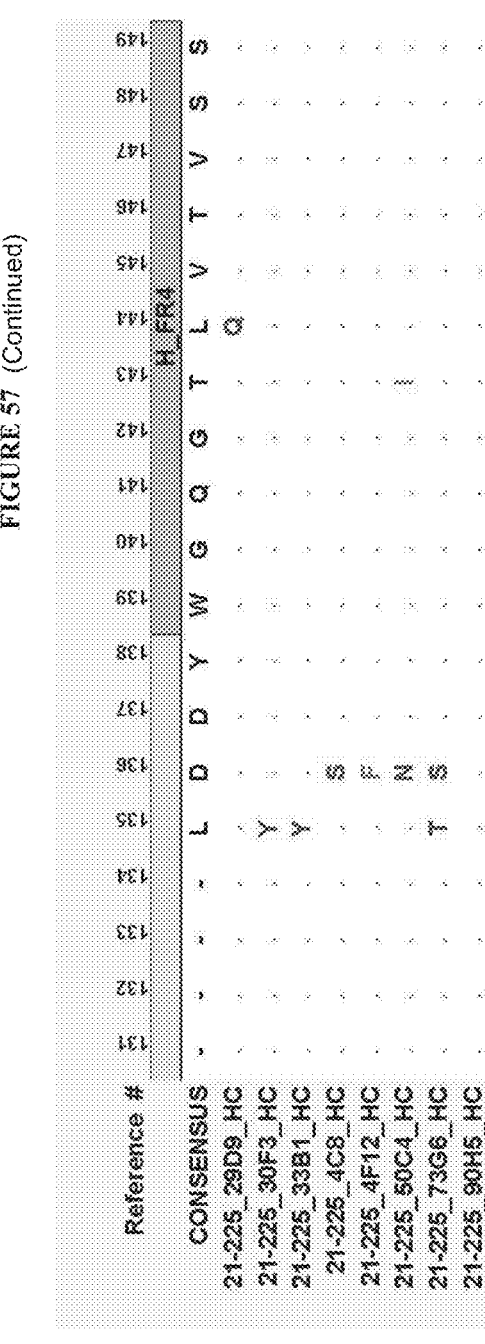
Figure 57:
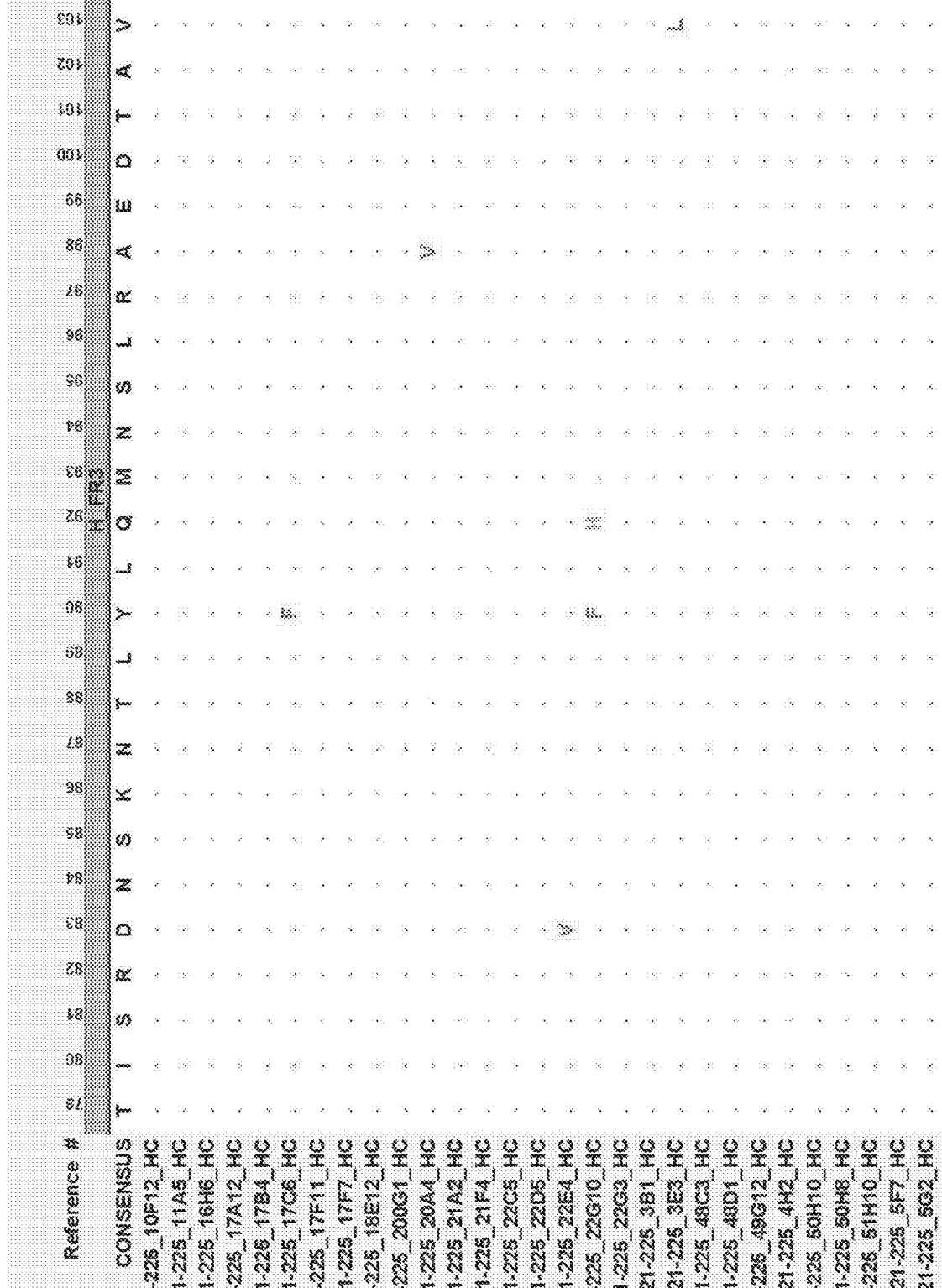
Figure 57:
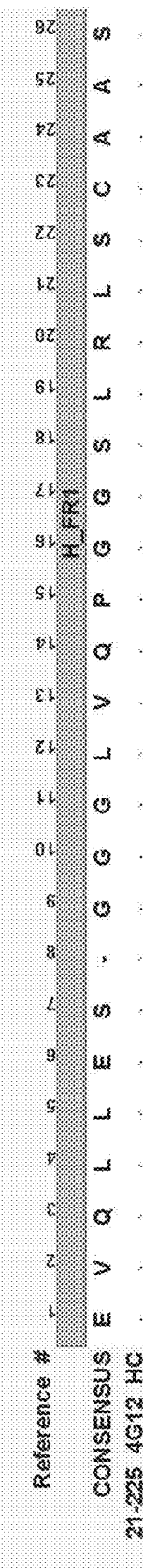
Figure 57:
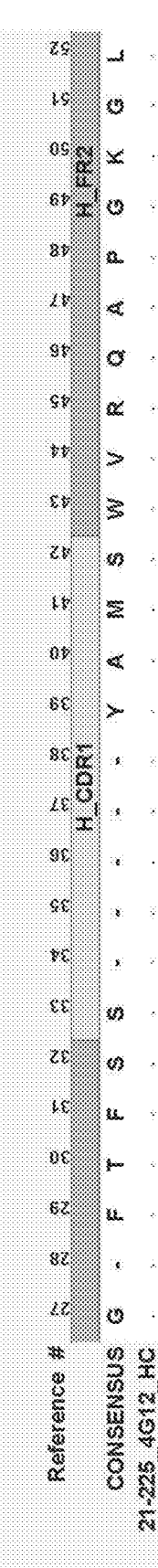
Figure 57:
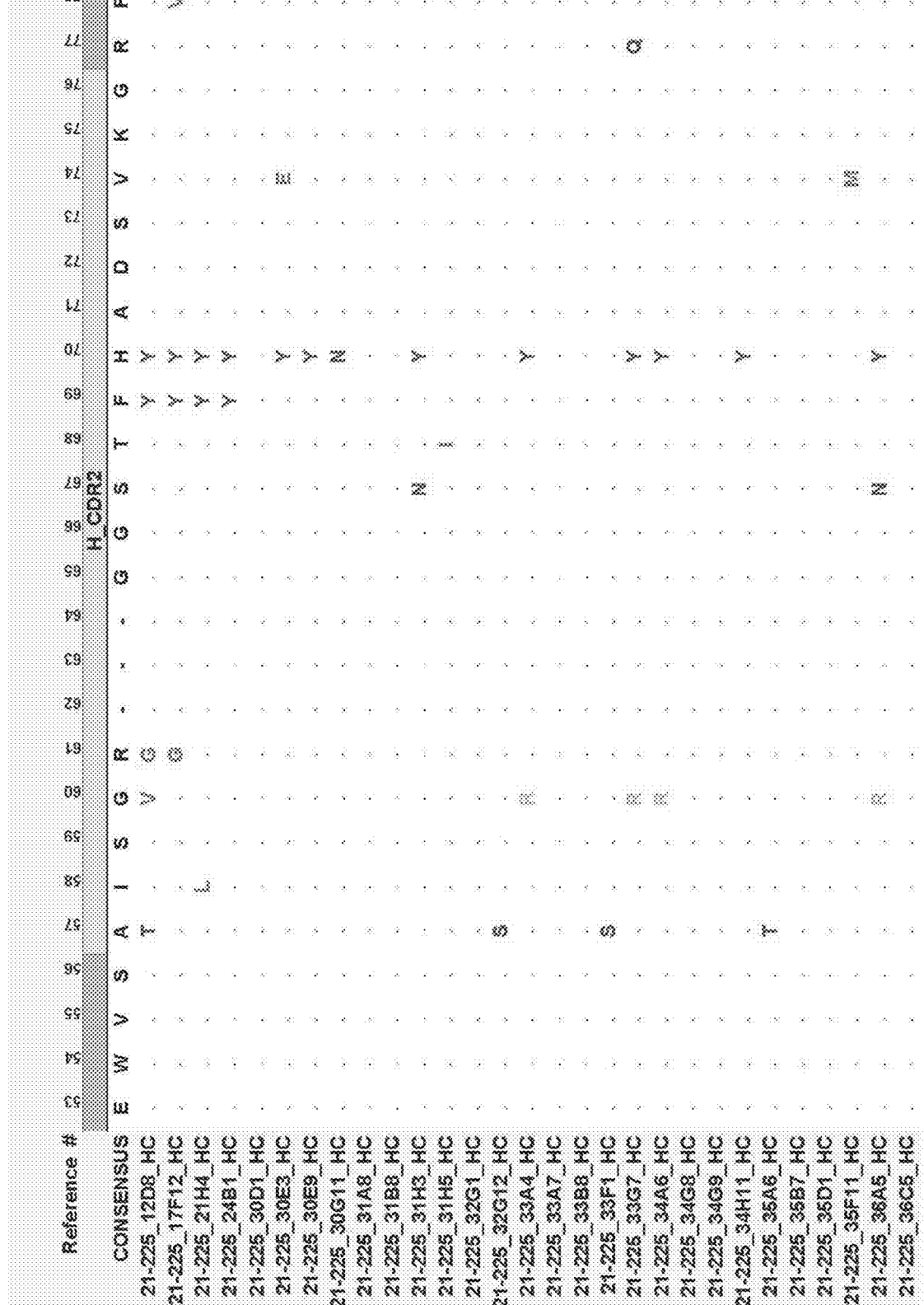
Figure 57:
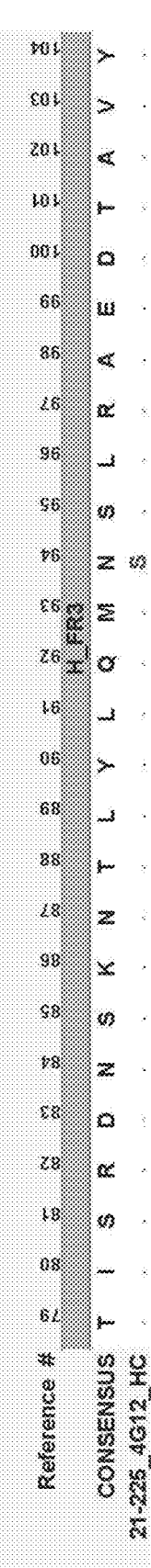
Figure 57:
Figure 57:
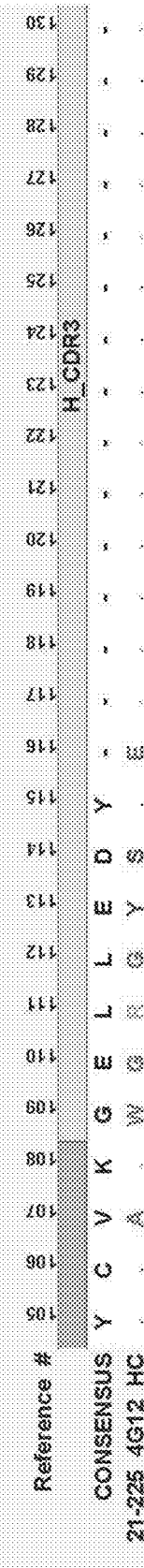
Figure 57:
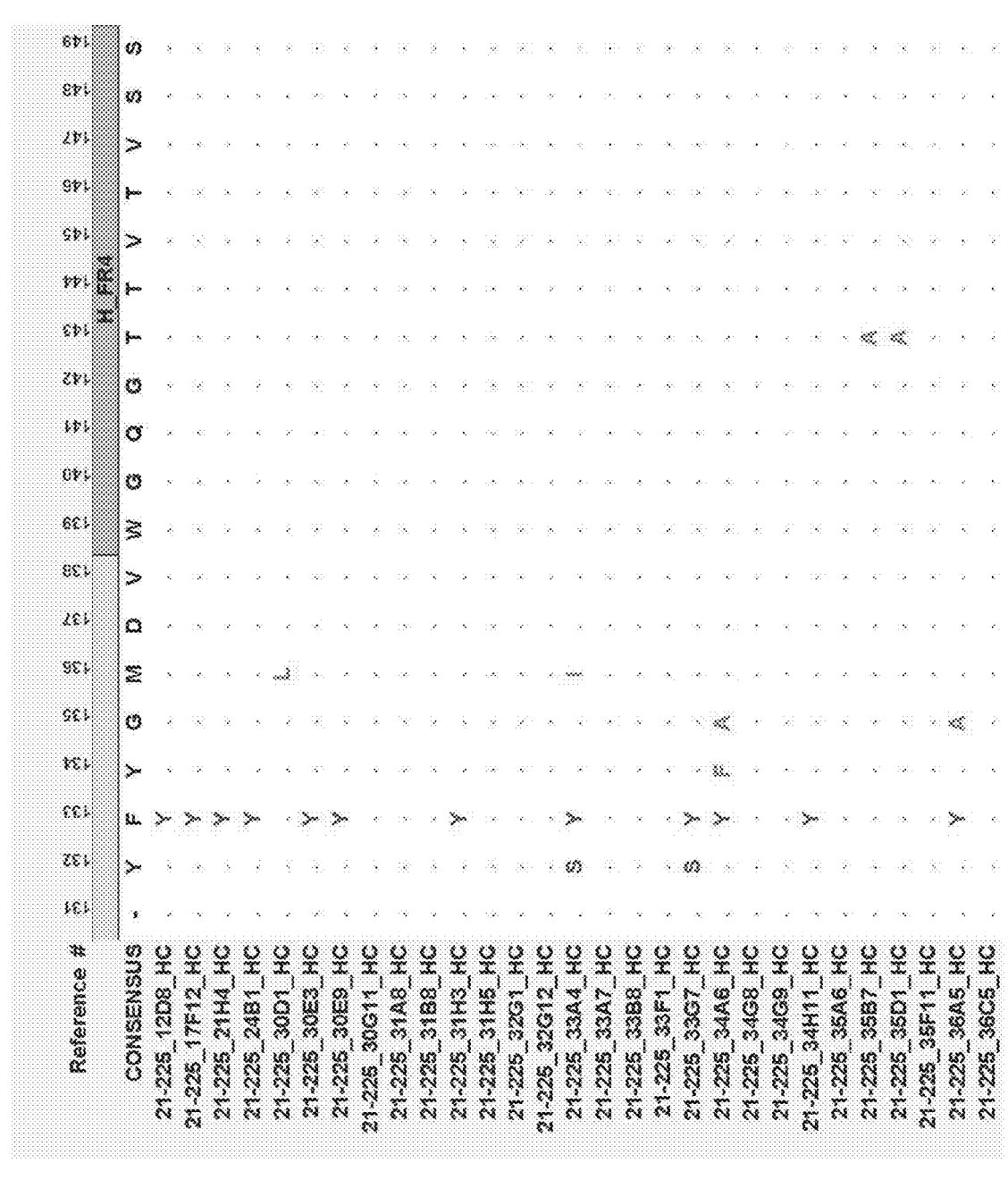
Figure 57:
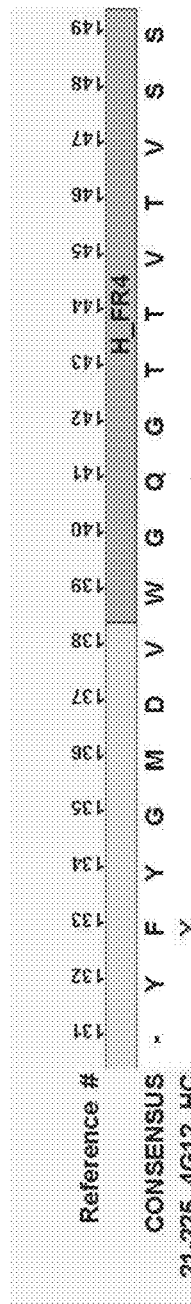
Figure 57:
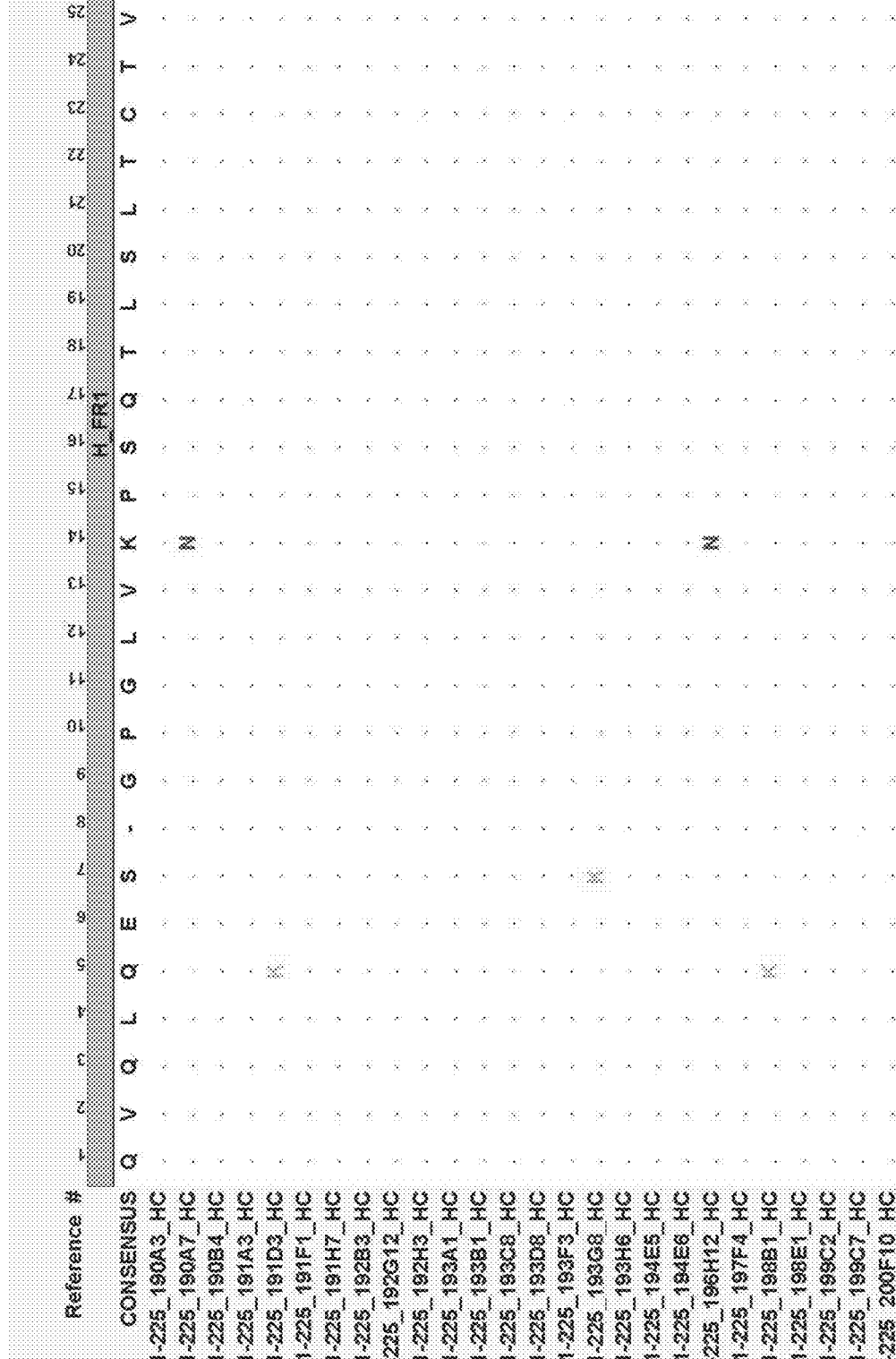
Figure 57:
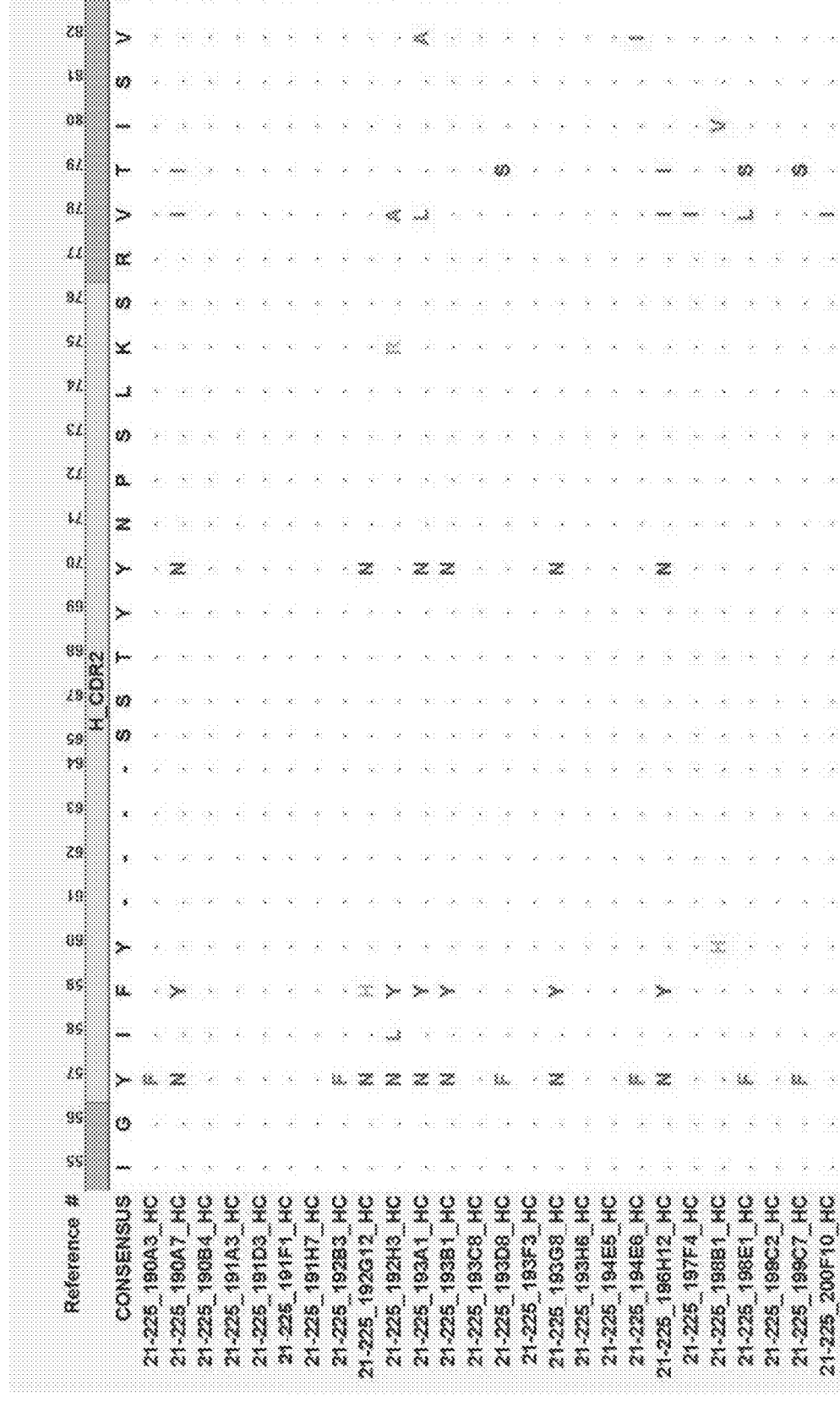
Figure 57:
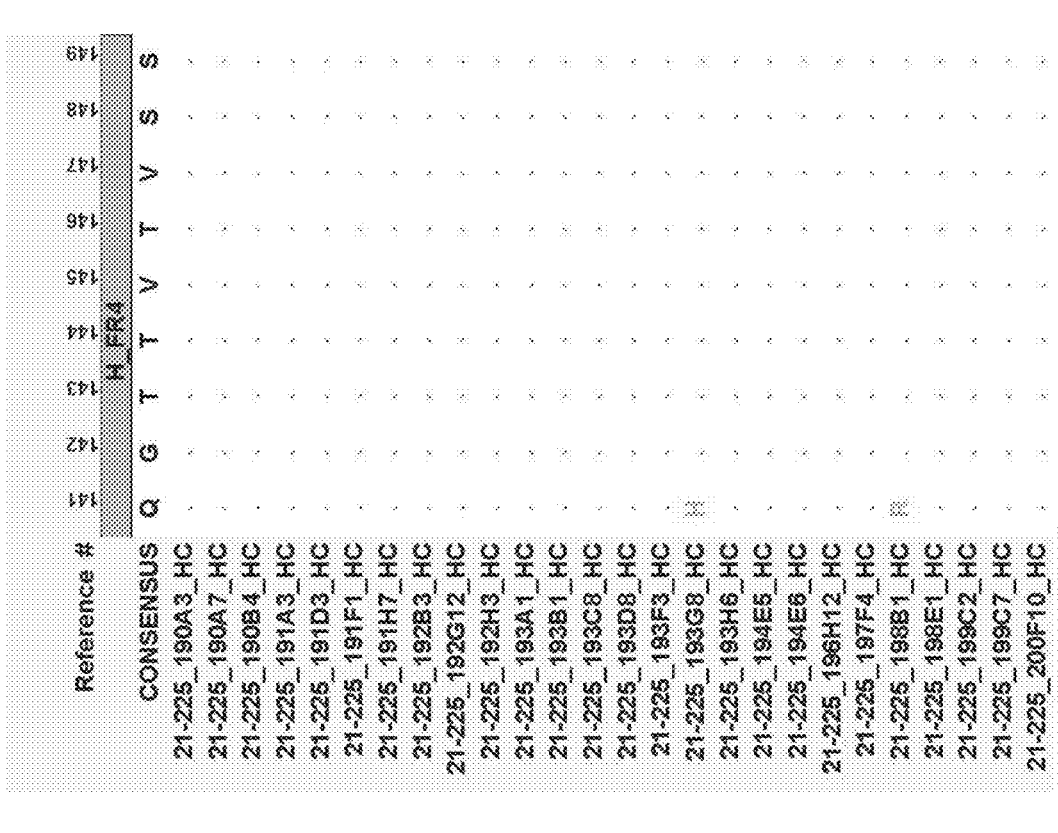
Figure 57:
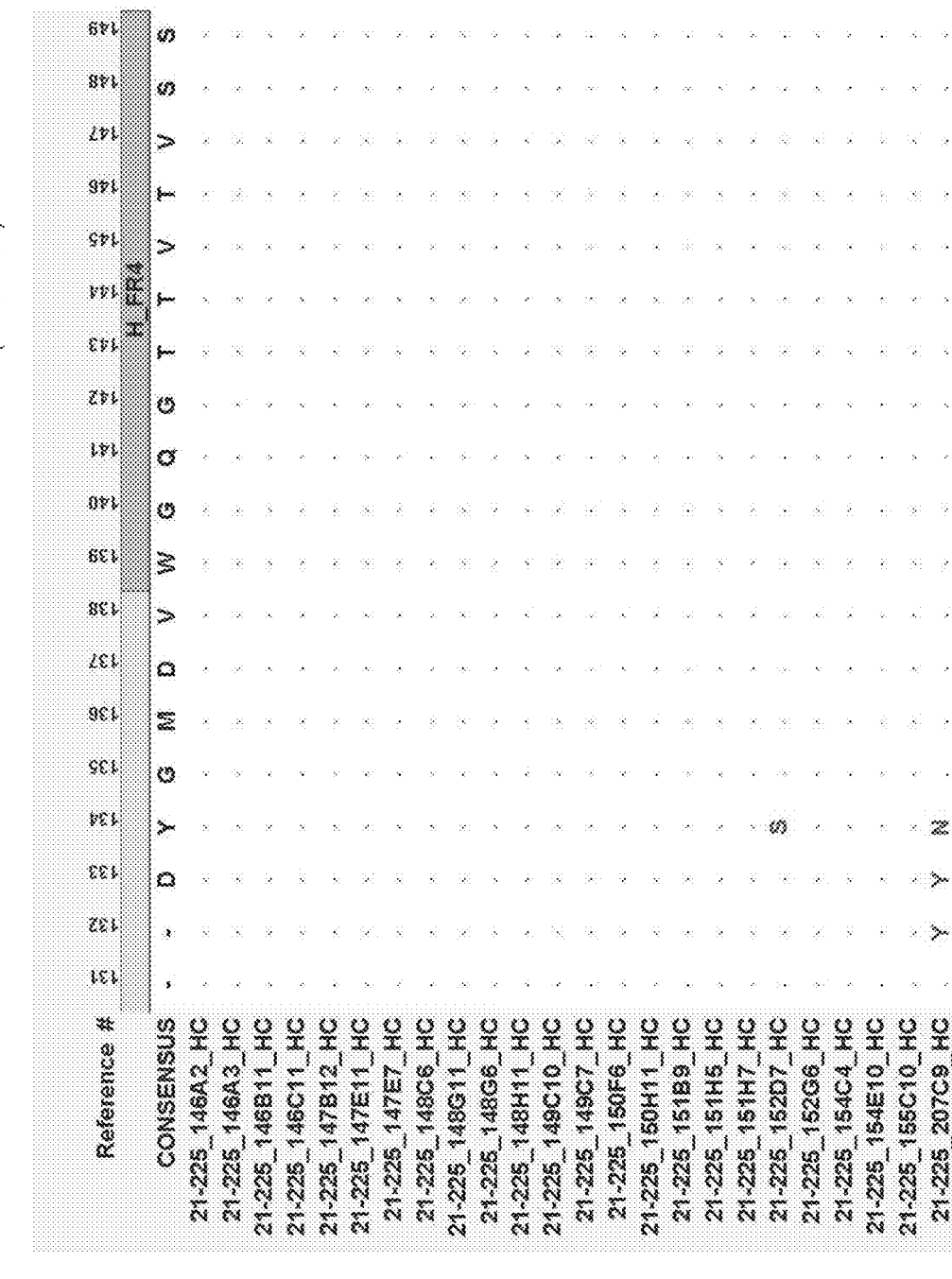
Figure 57:
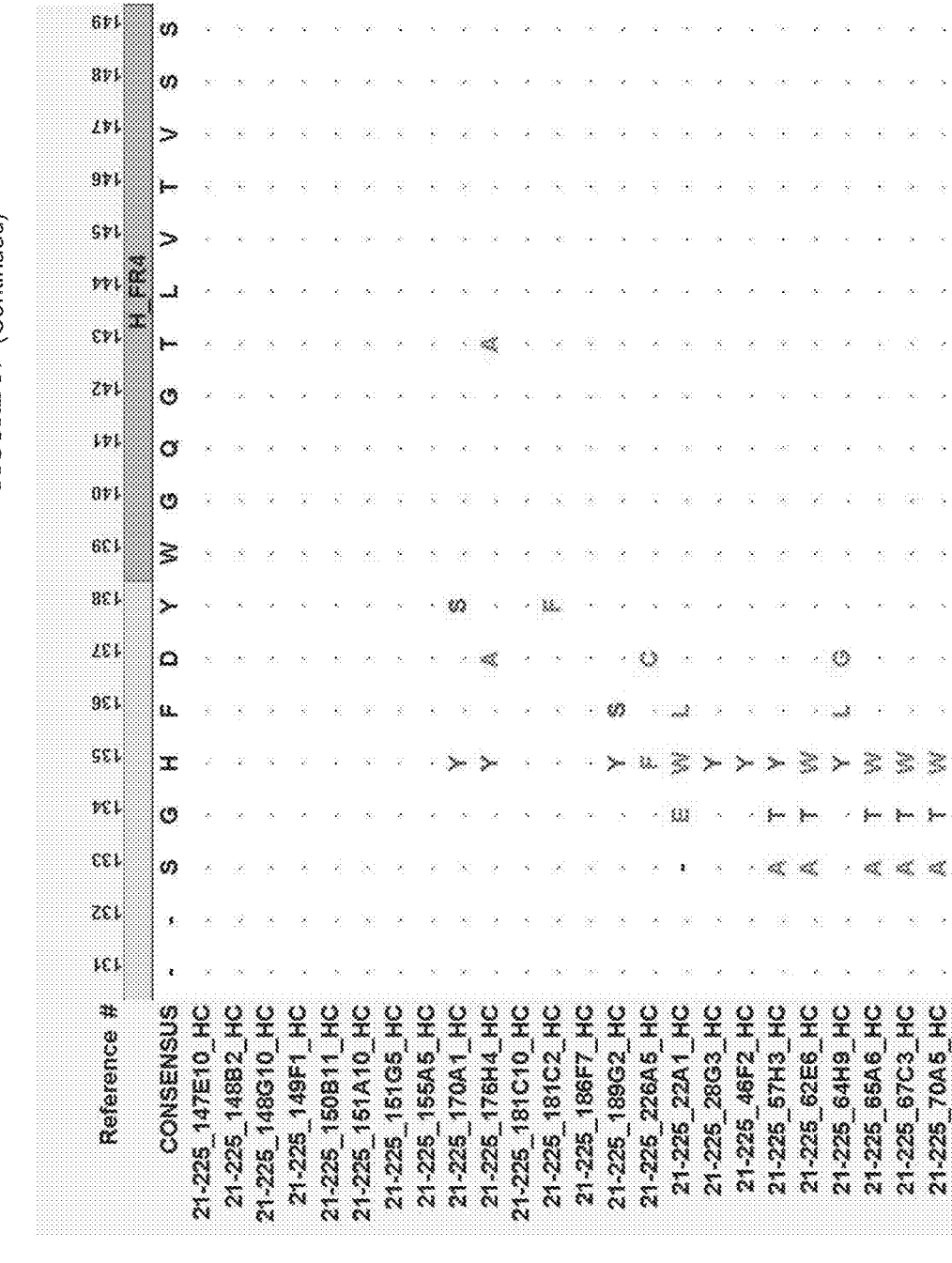
Figure 57:
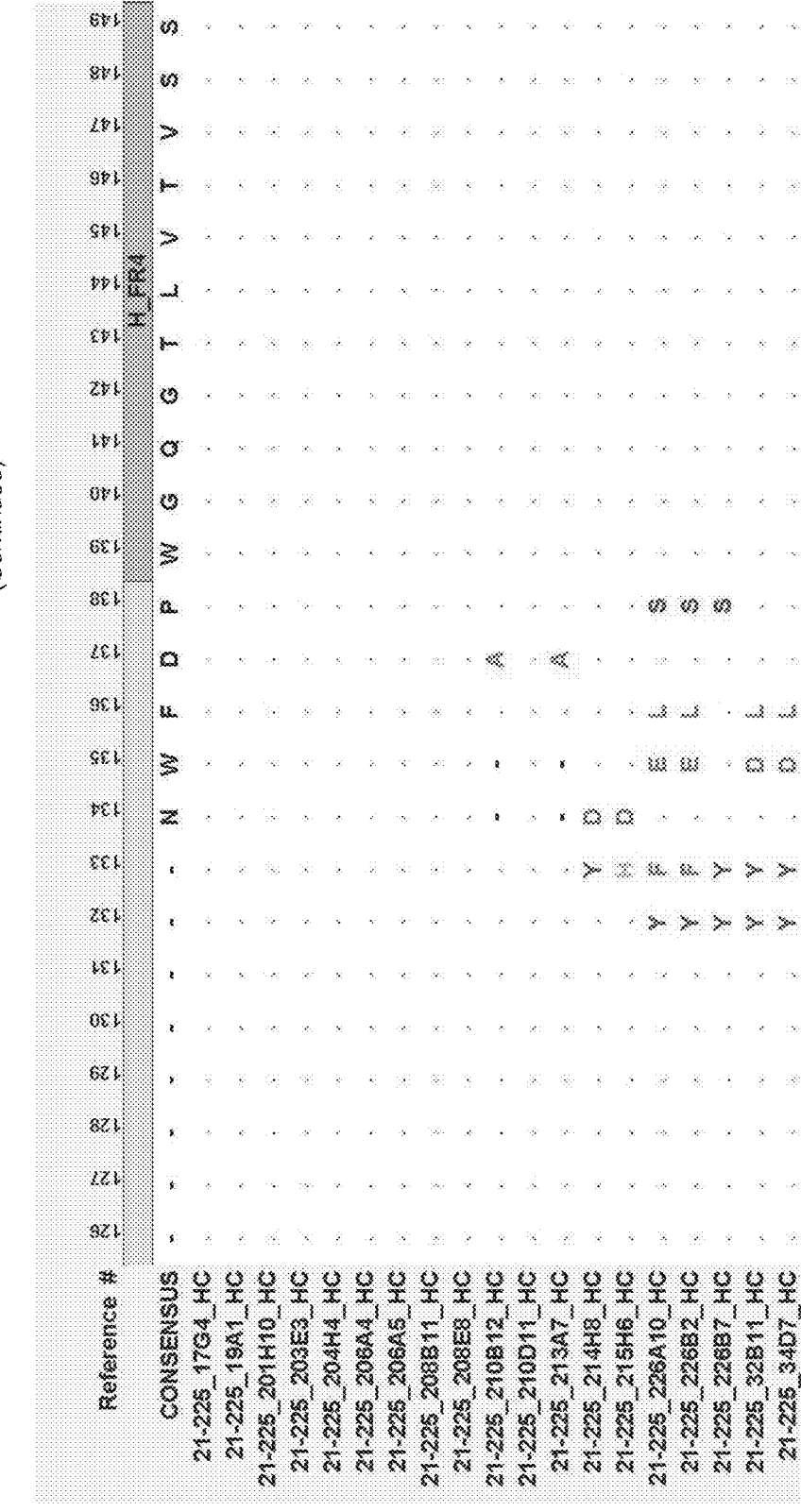
Figure 57:
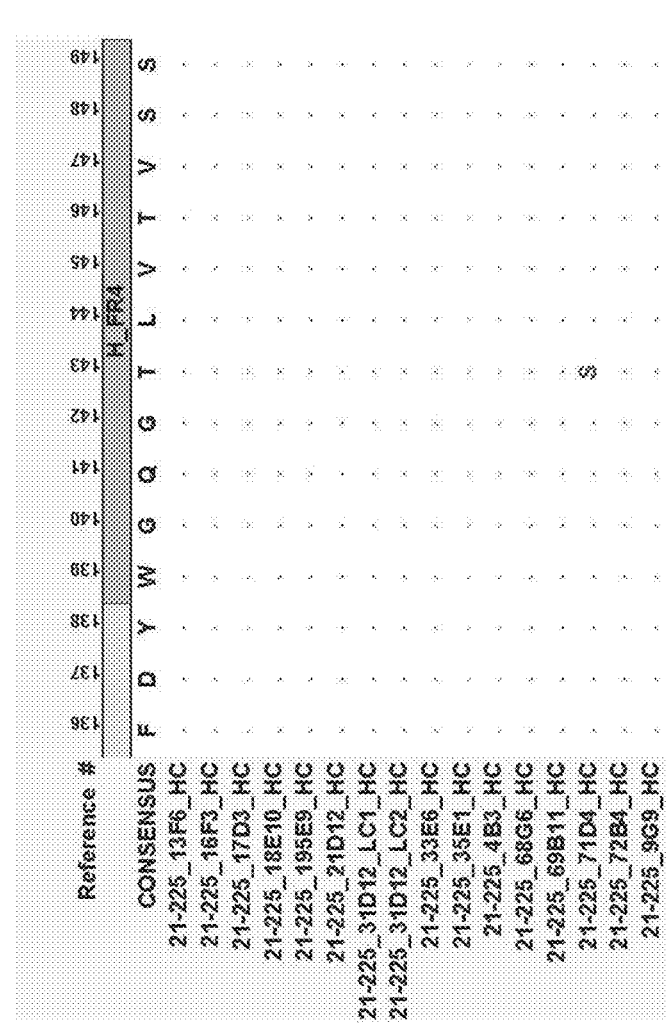
Figure 57:
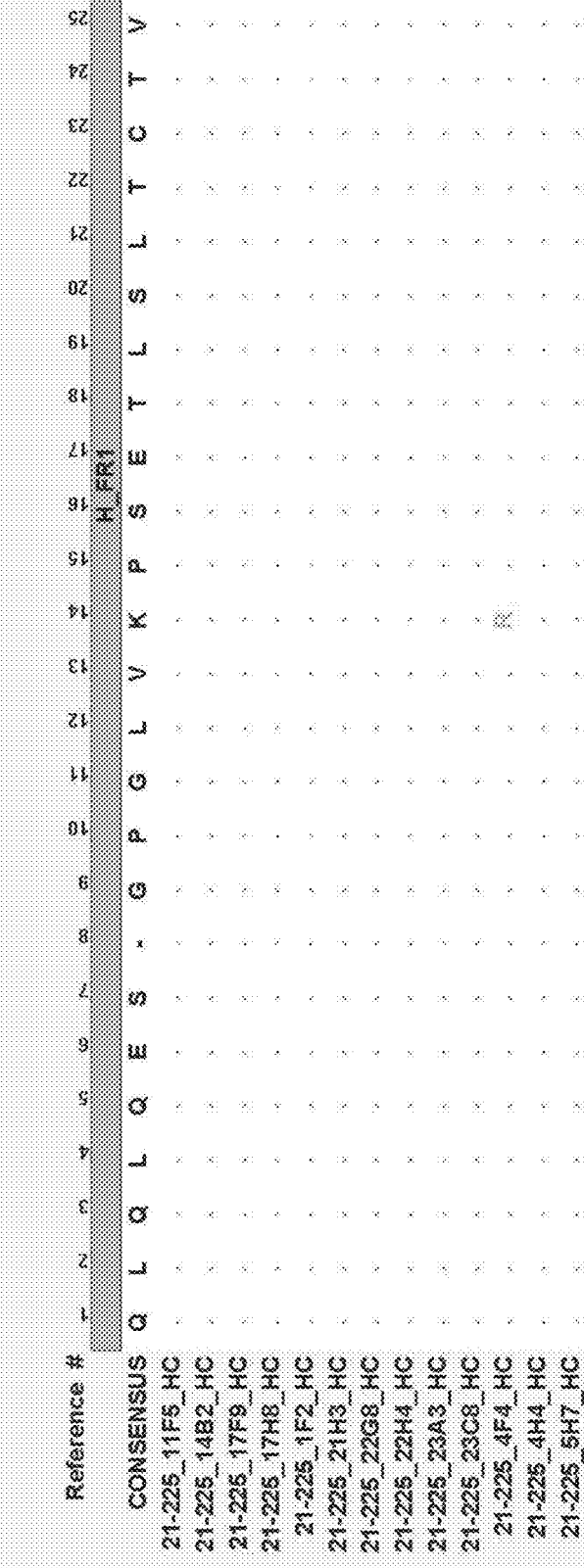
Figure 57:
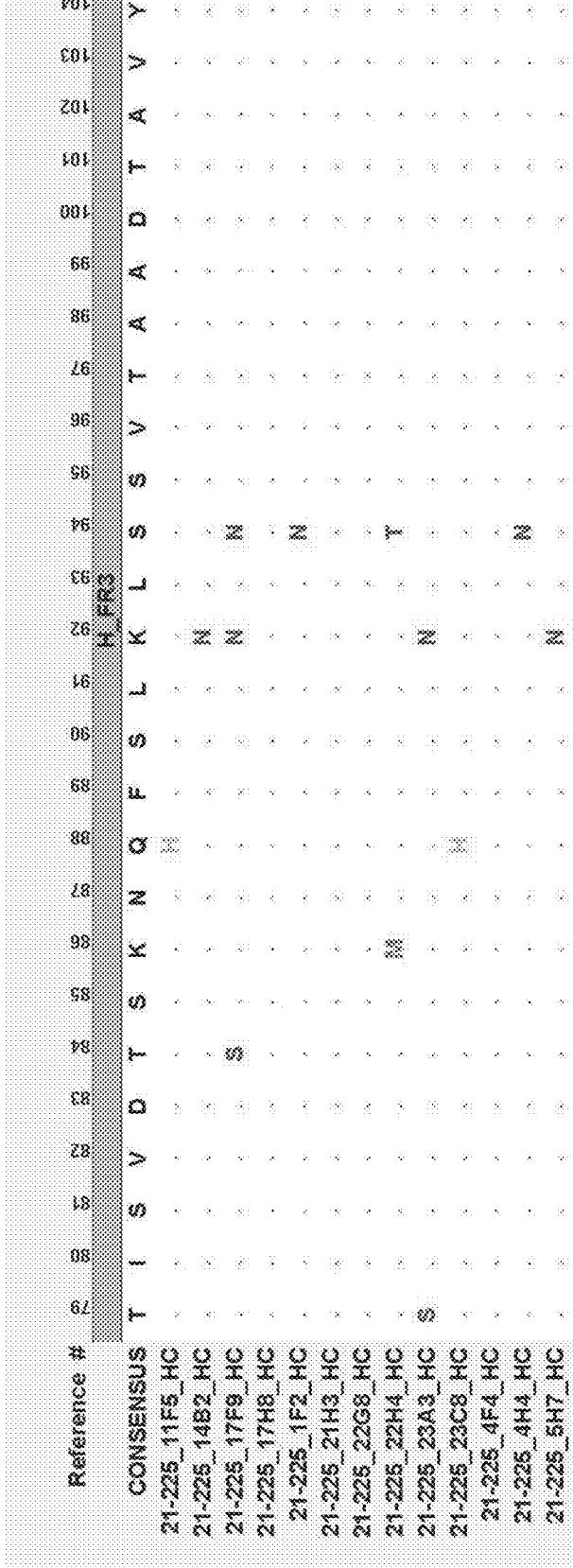
Figure 57:
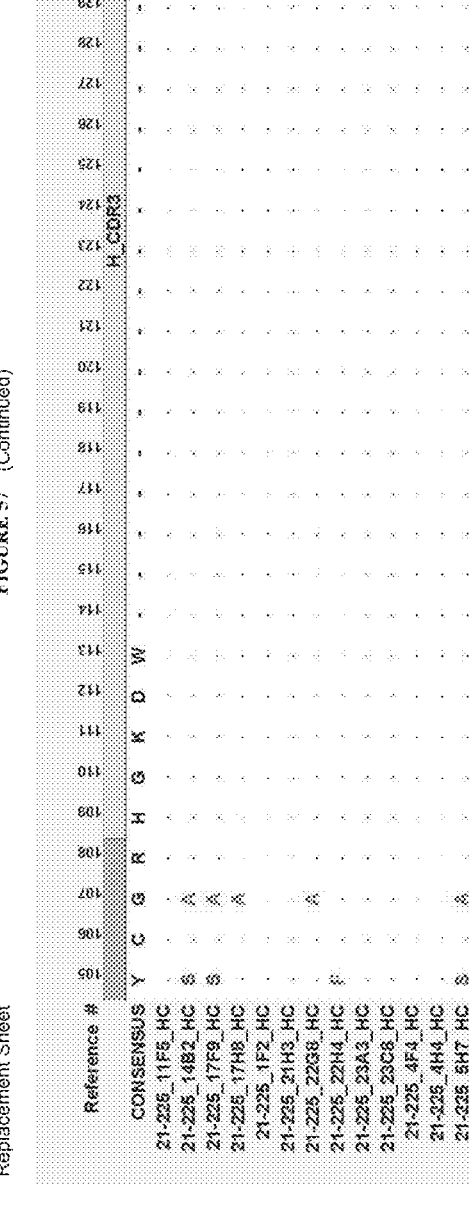
Figure 57:
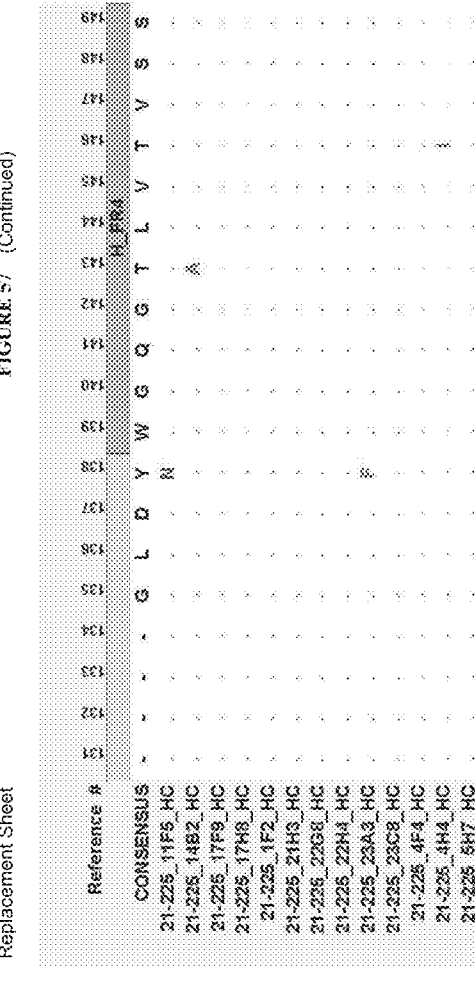
Figure 57:
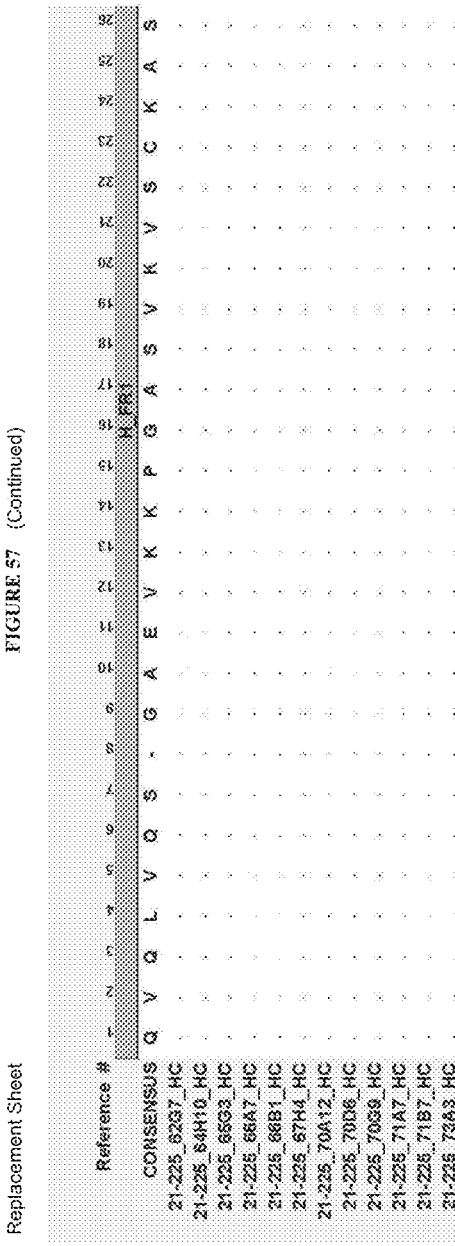
Figure 57:
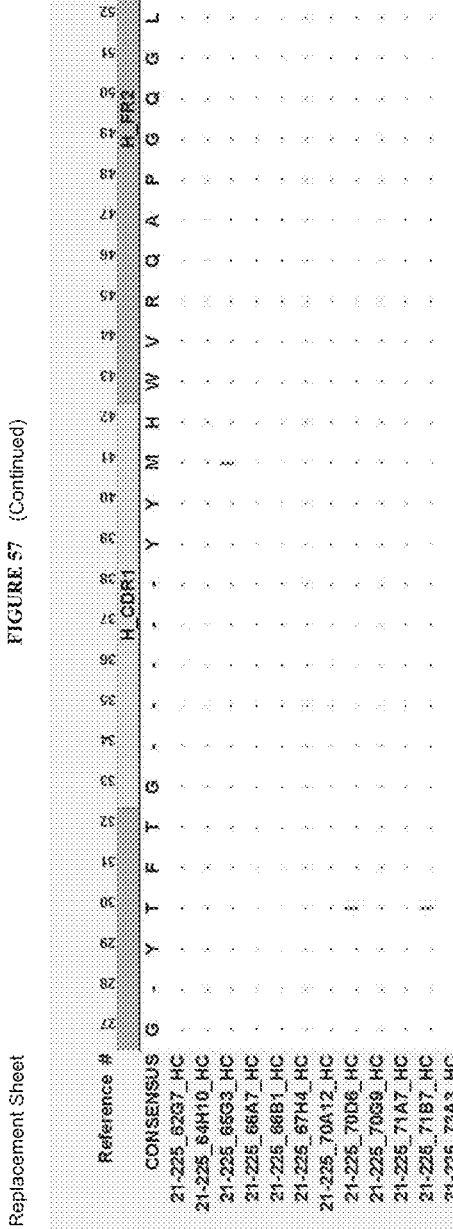
Figure 57:
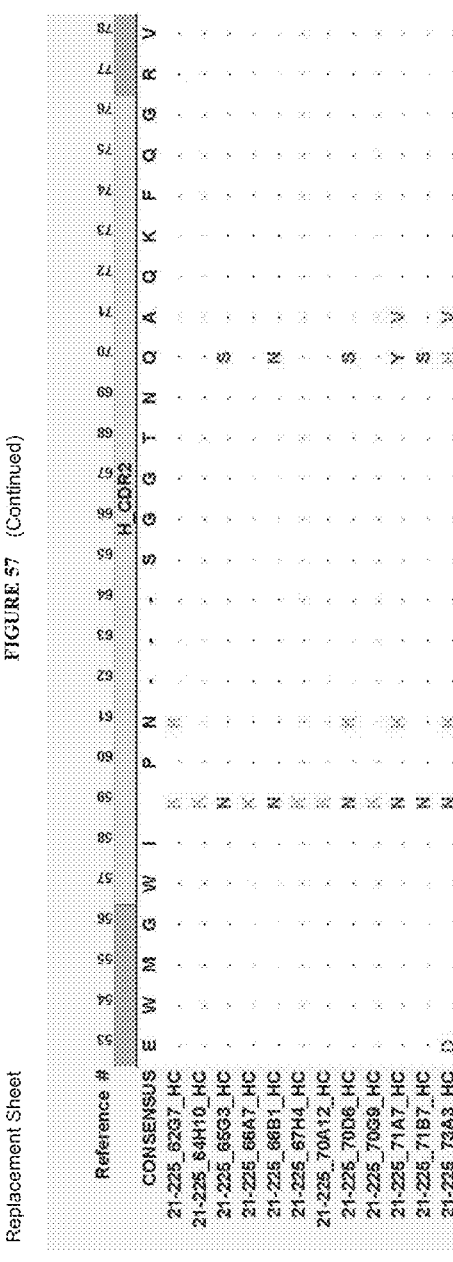
Figure 57:
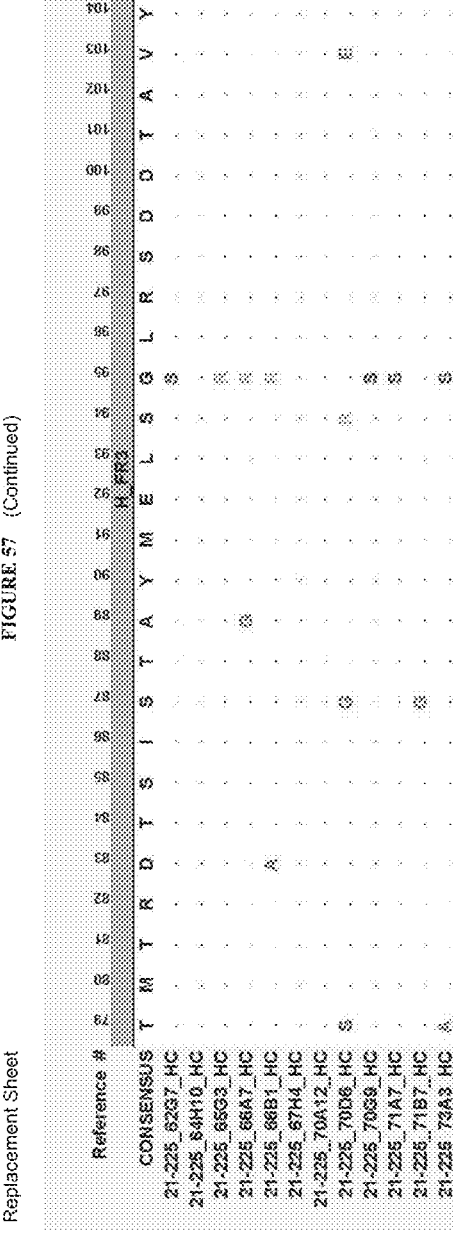
Figure 57:
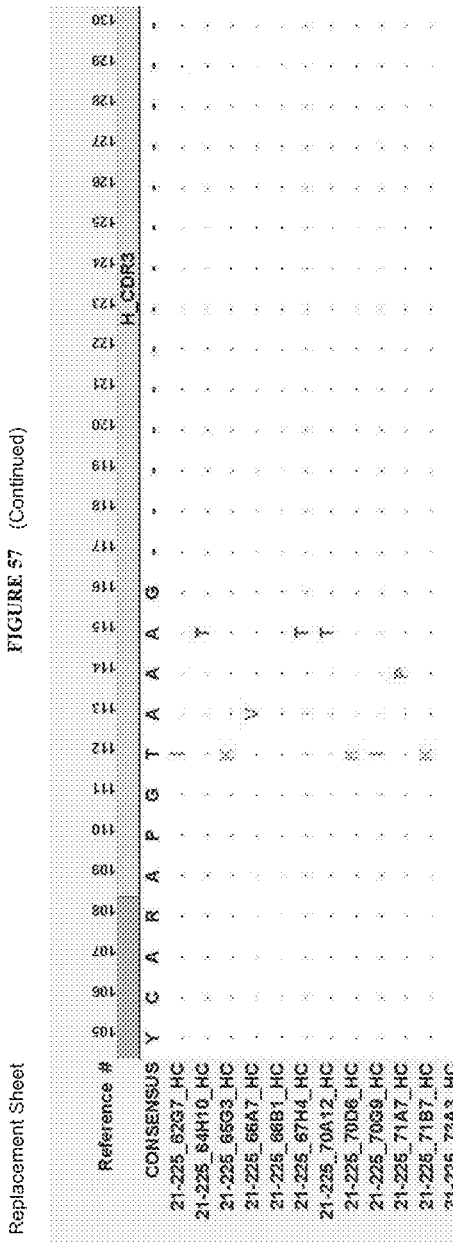
Figure 57:
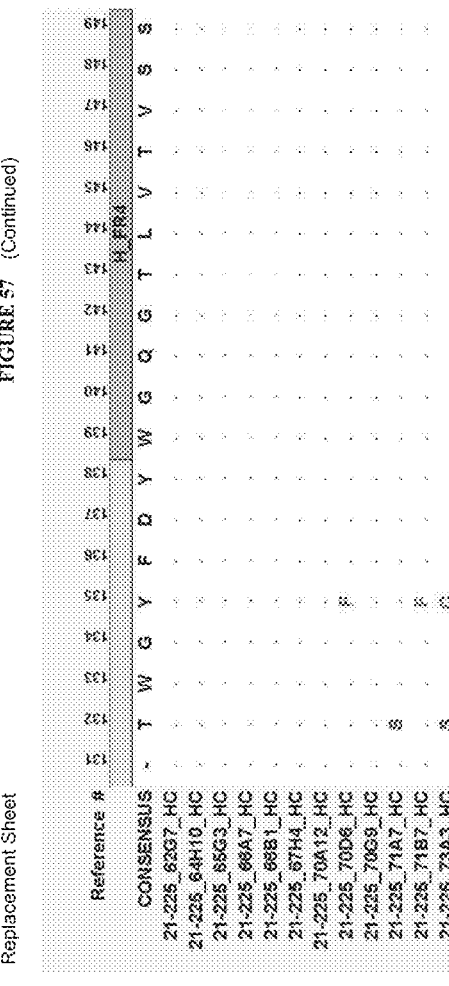
Figure 57:
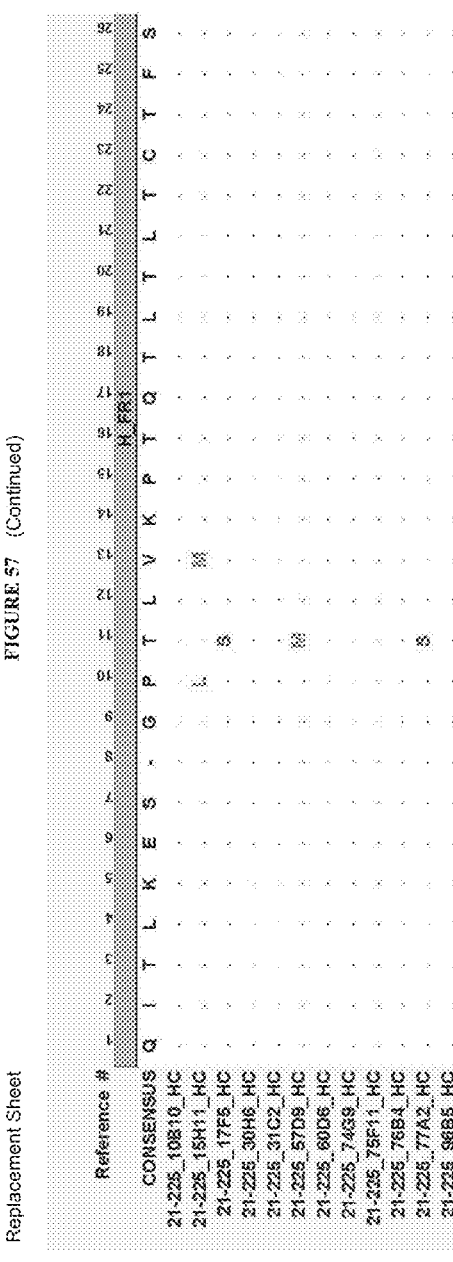
Figure 57:
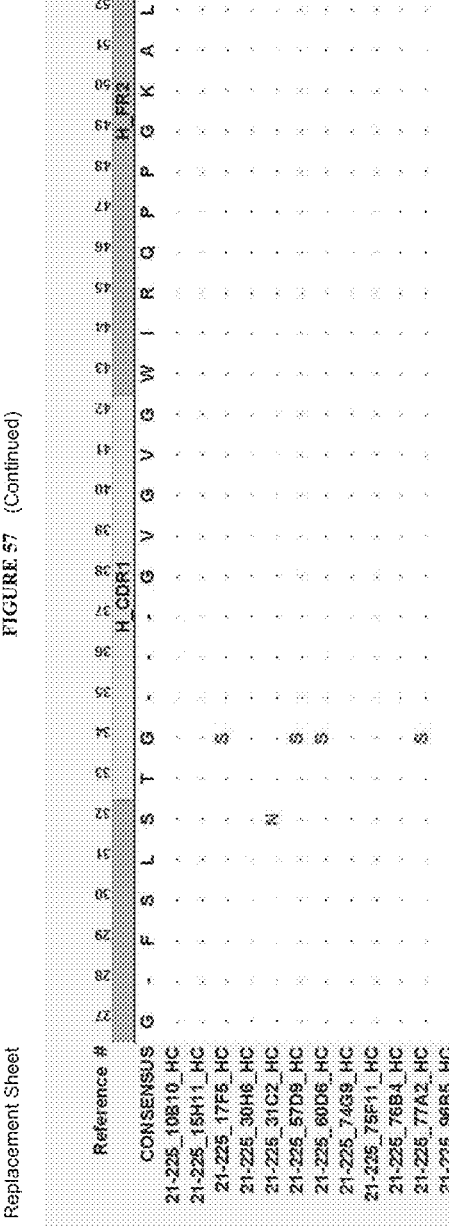
Figure 57:
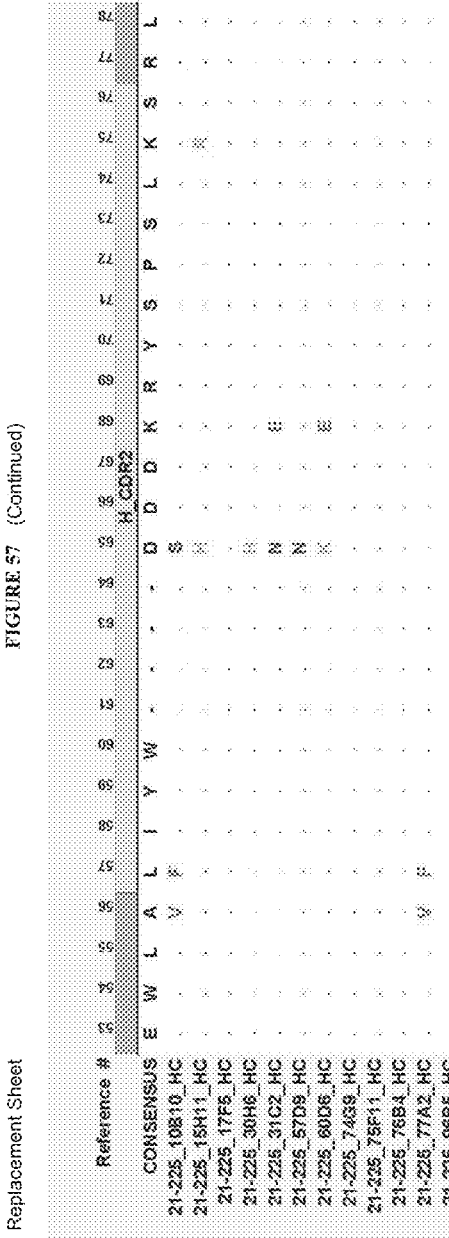
Figure 57:
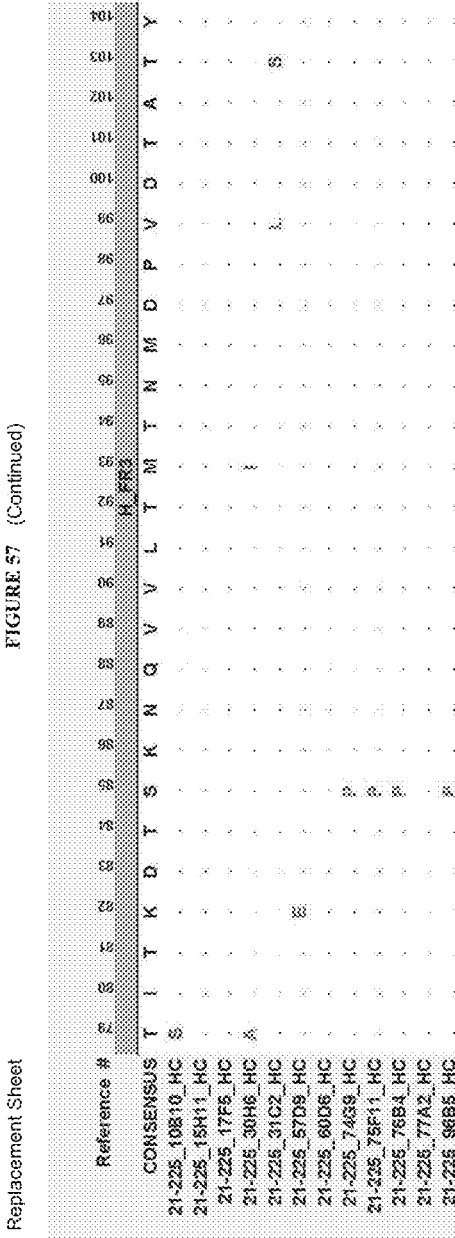
Figure 57:
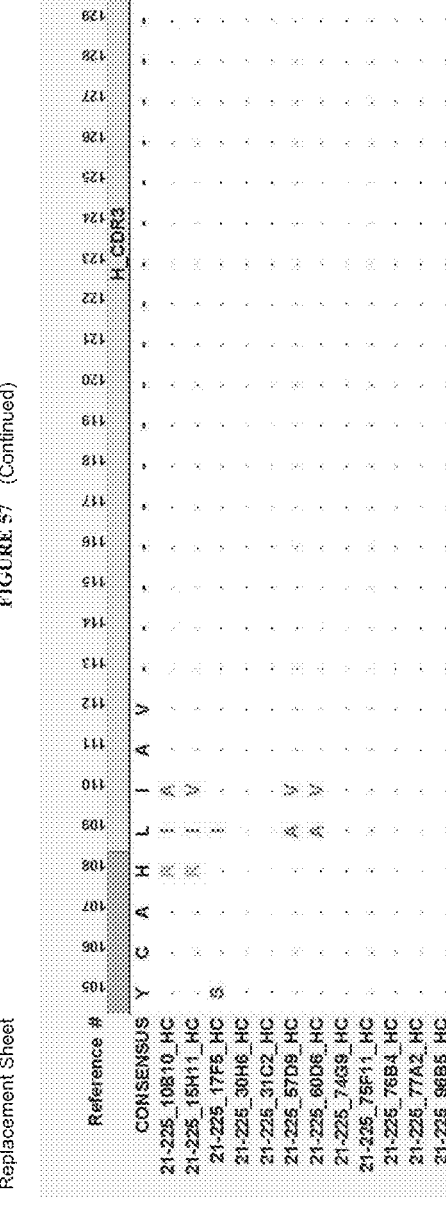
Figure 57:
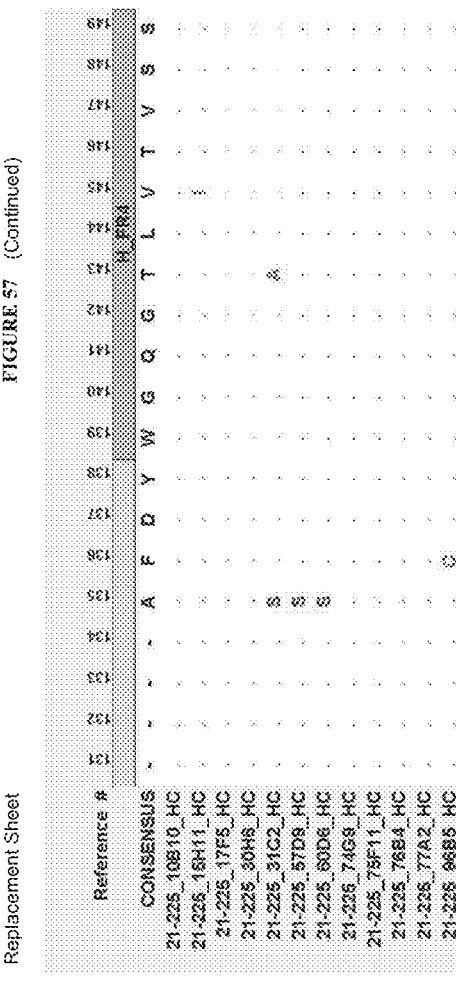
Figure 57:
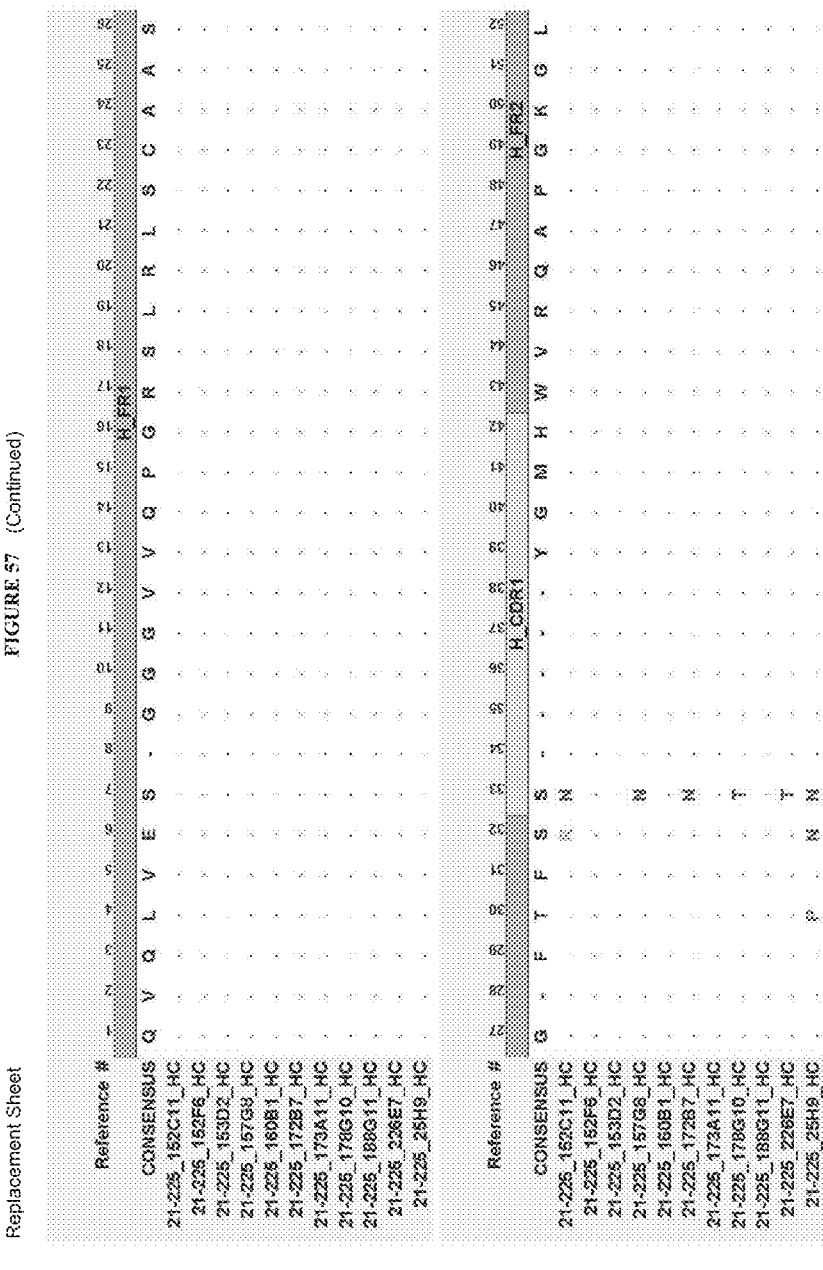
Figure 57:
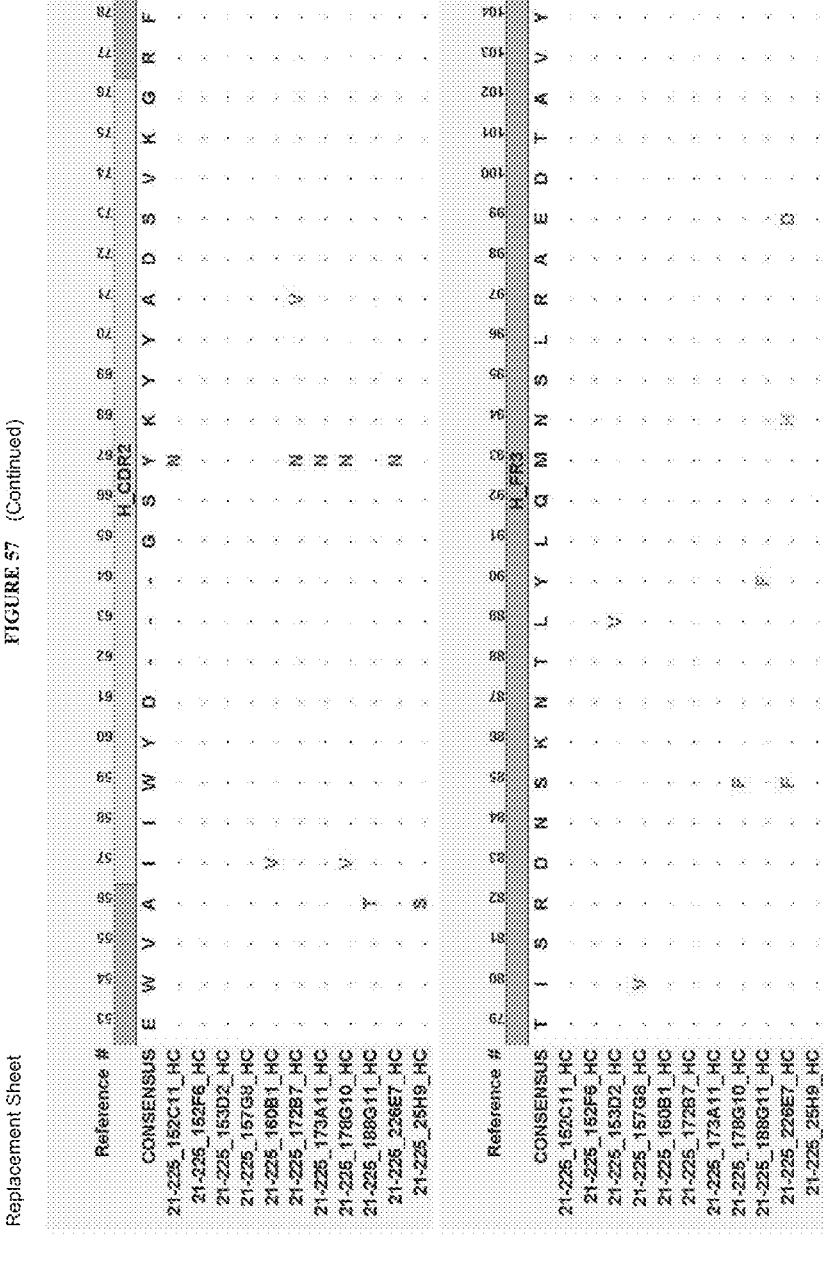
Figure 57:
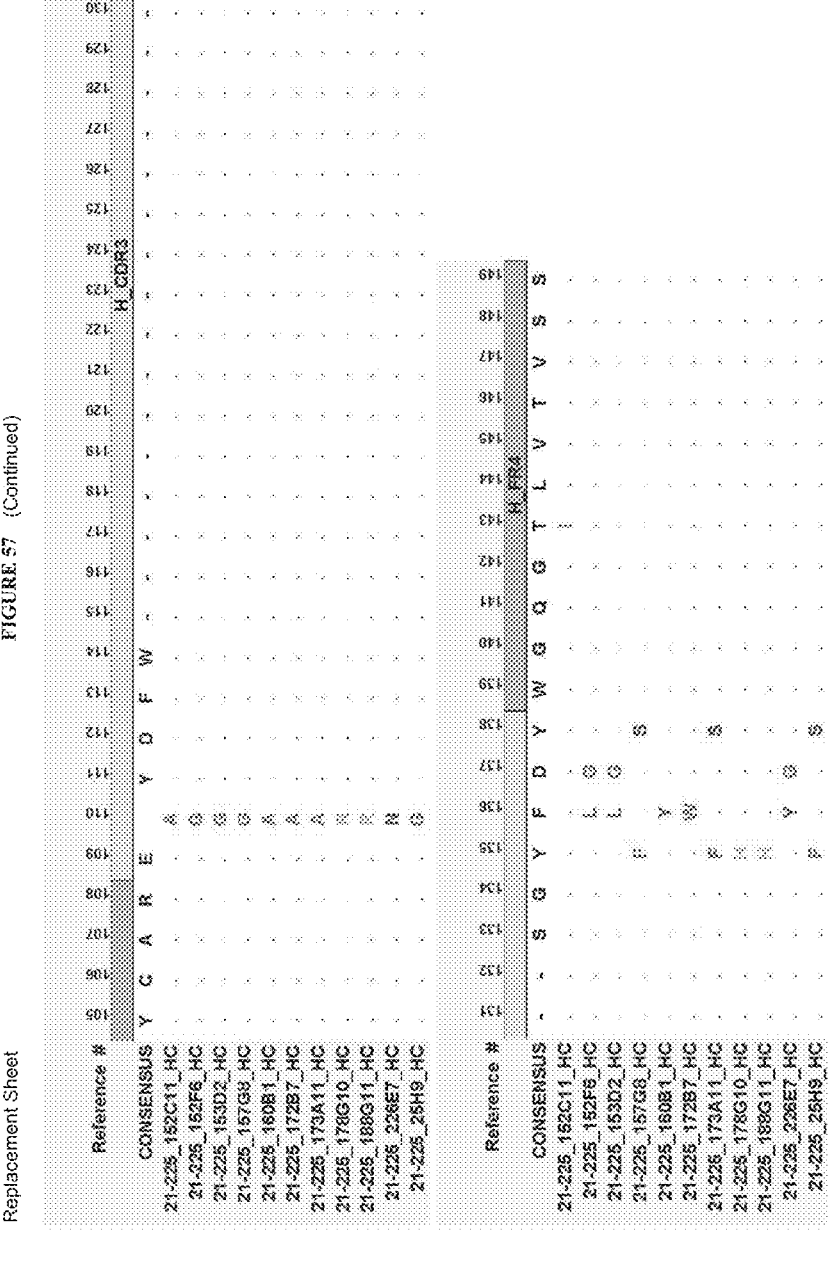
Figure 57:
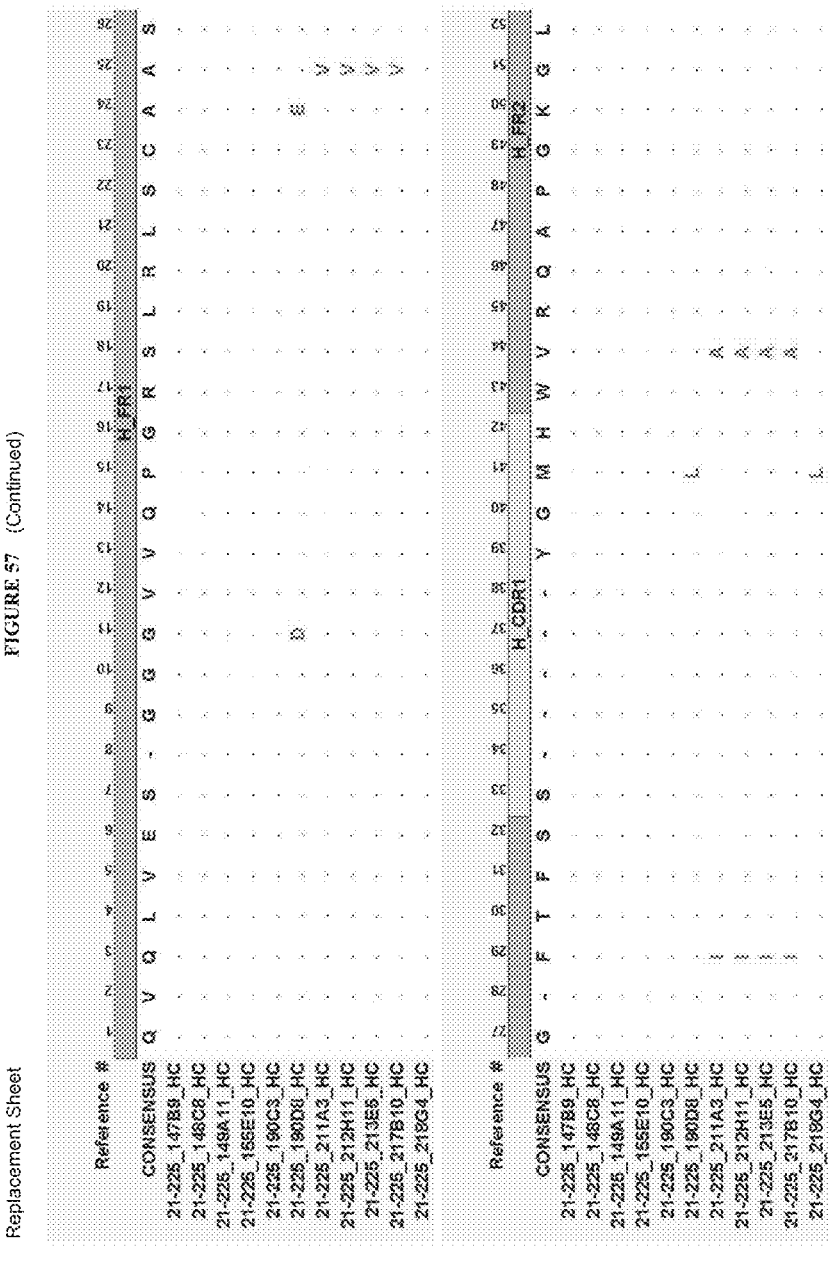
Figure 57:
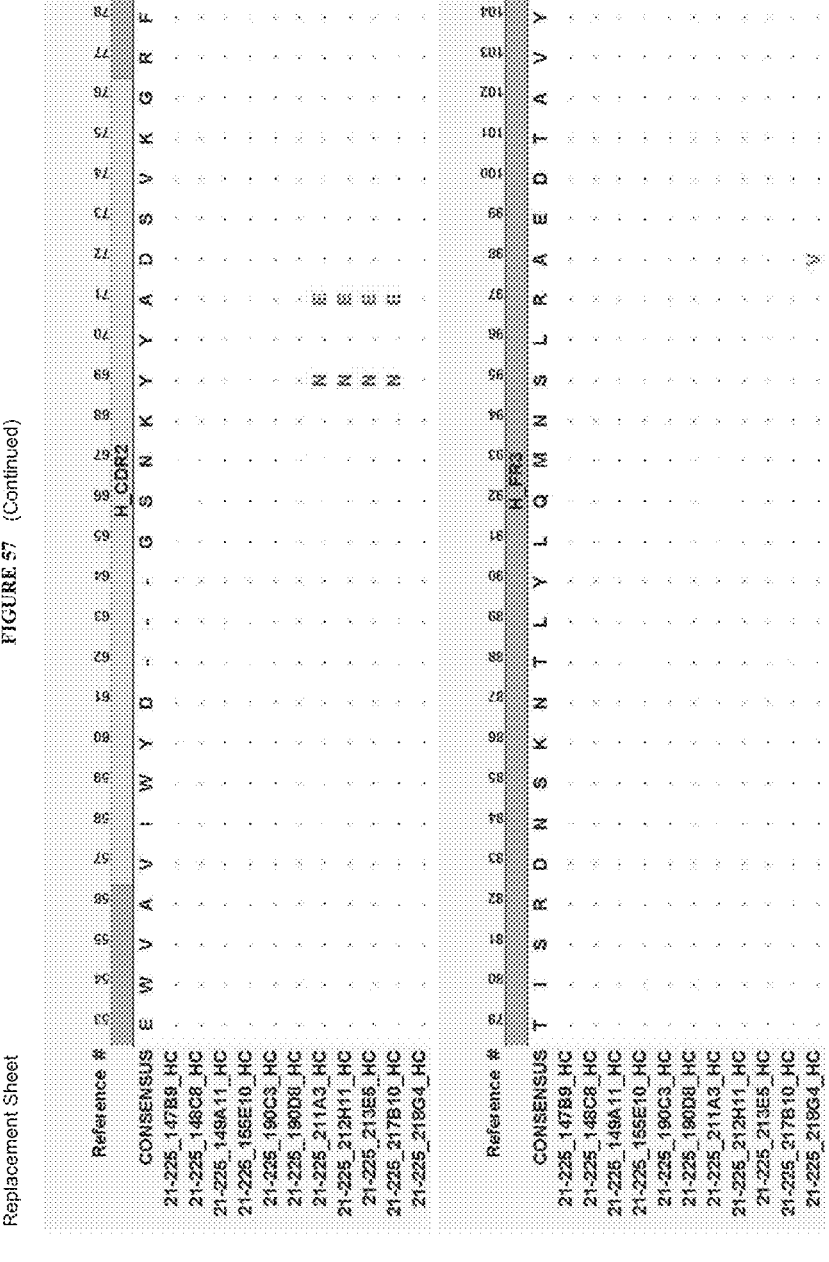
Figure 57:
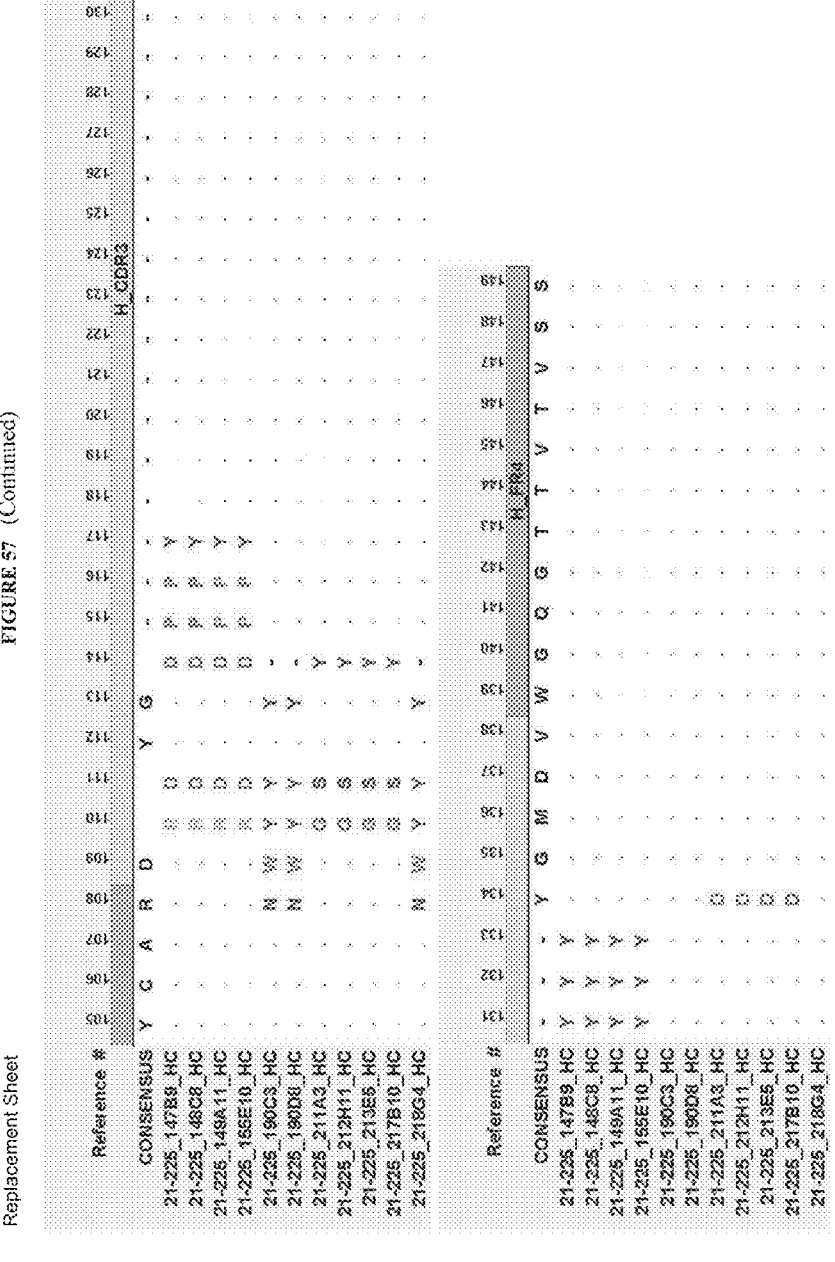
Figure 57:
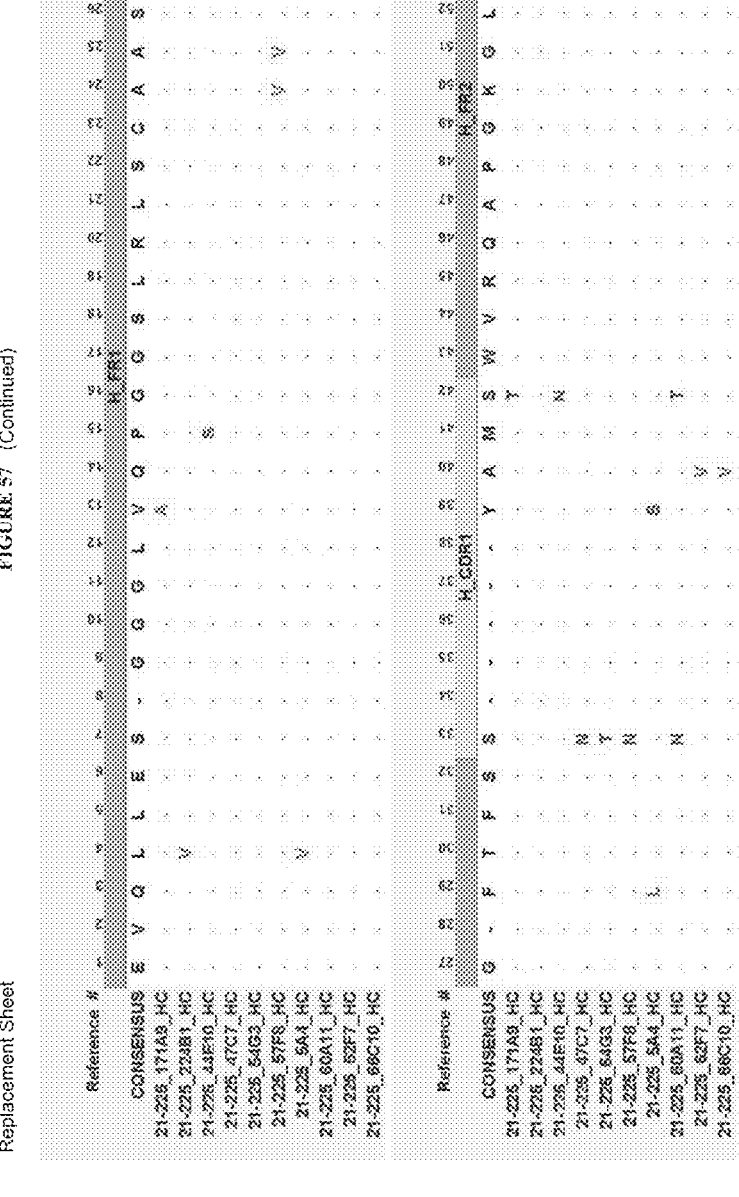
Figure 57:
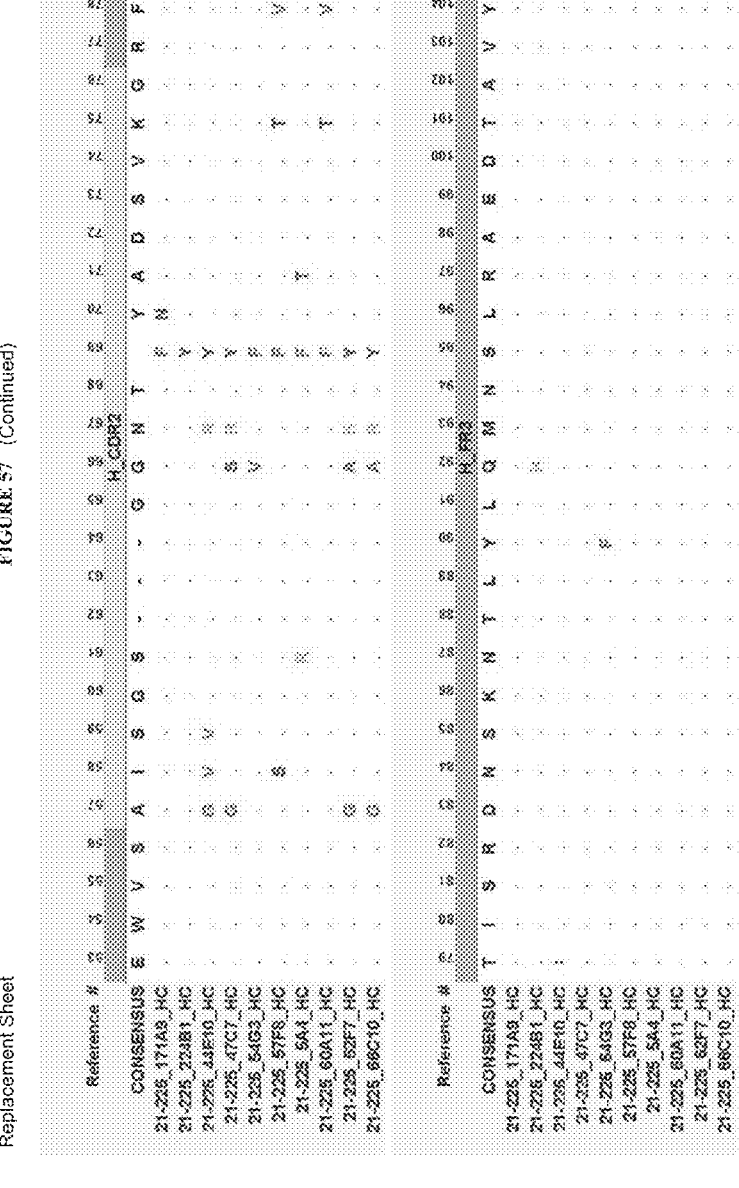
Figure 57:
Figure 57:
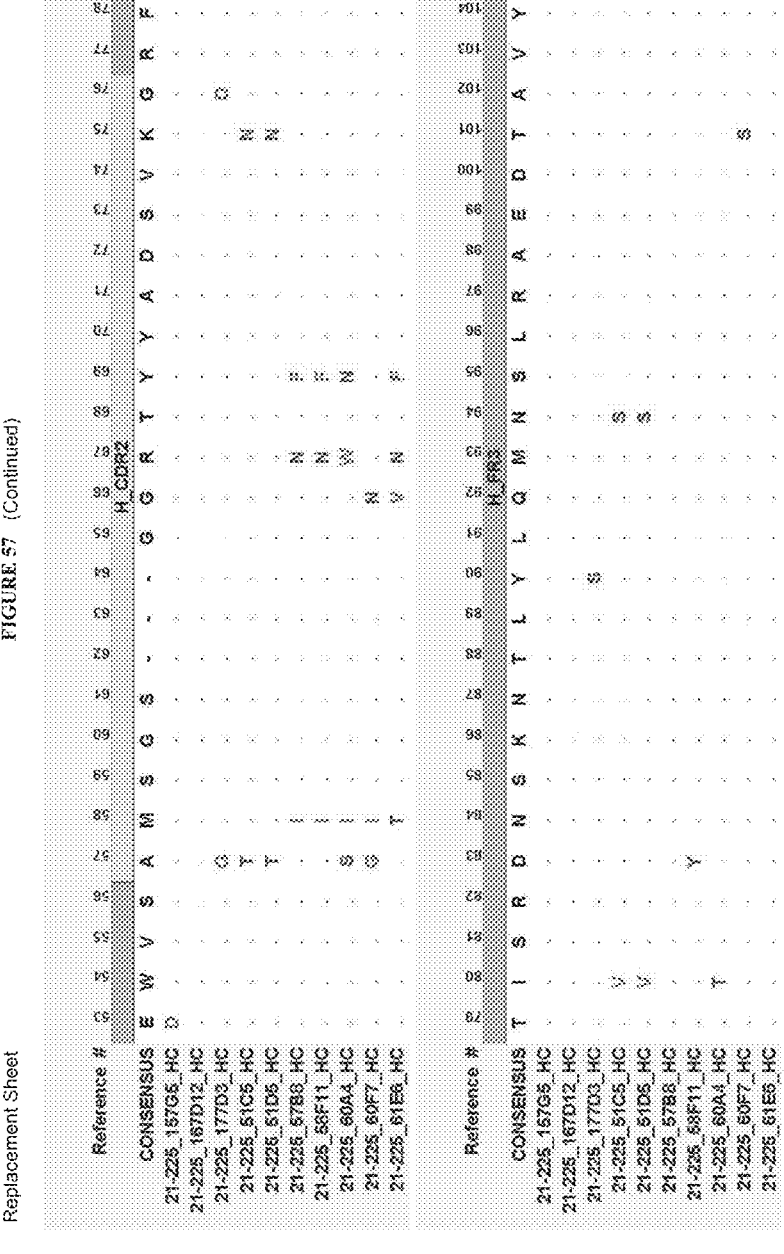
Figure 57:
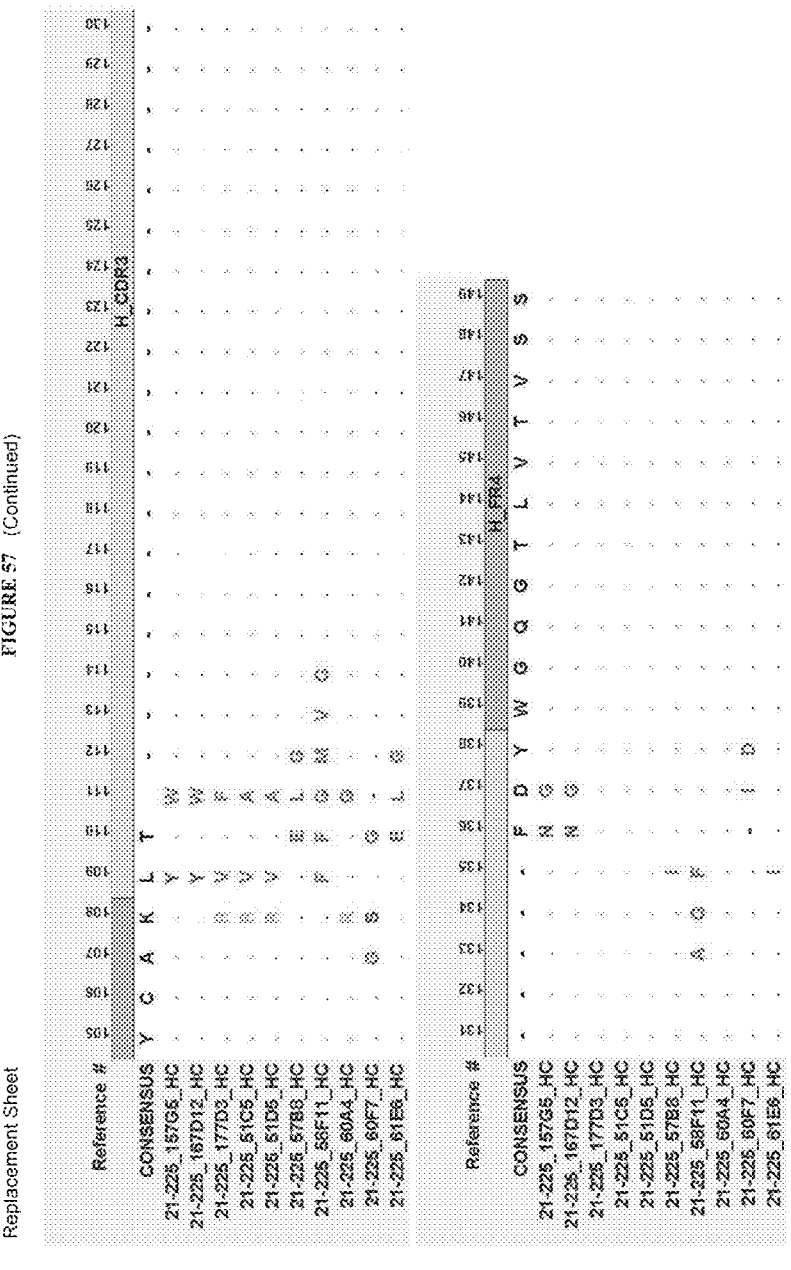
Figure 57:
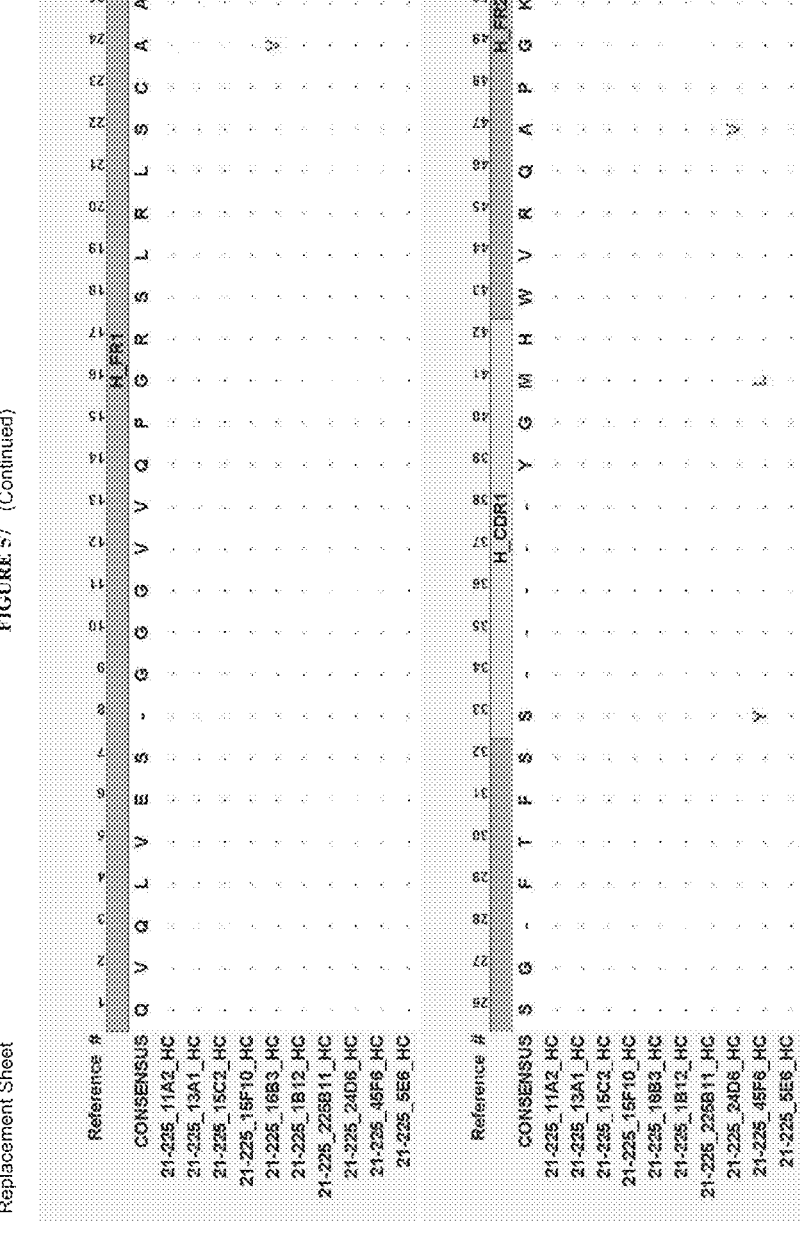
Figure 57:
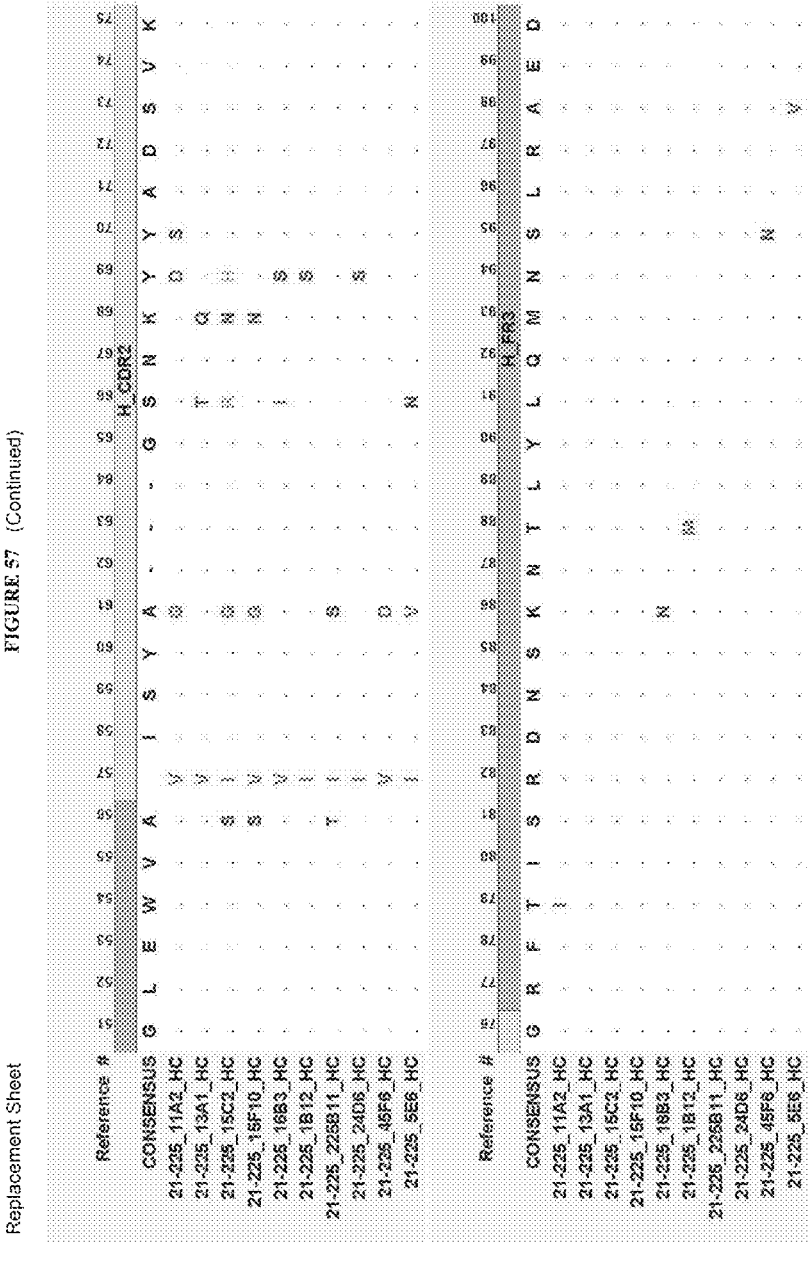
Figure 57:
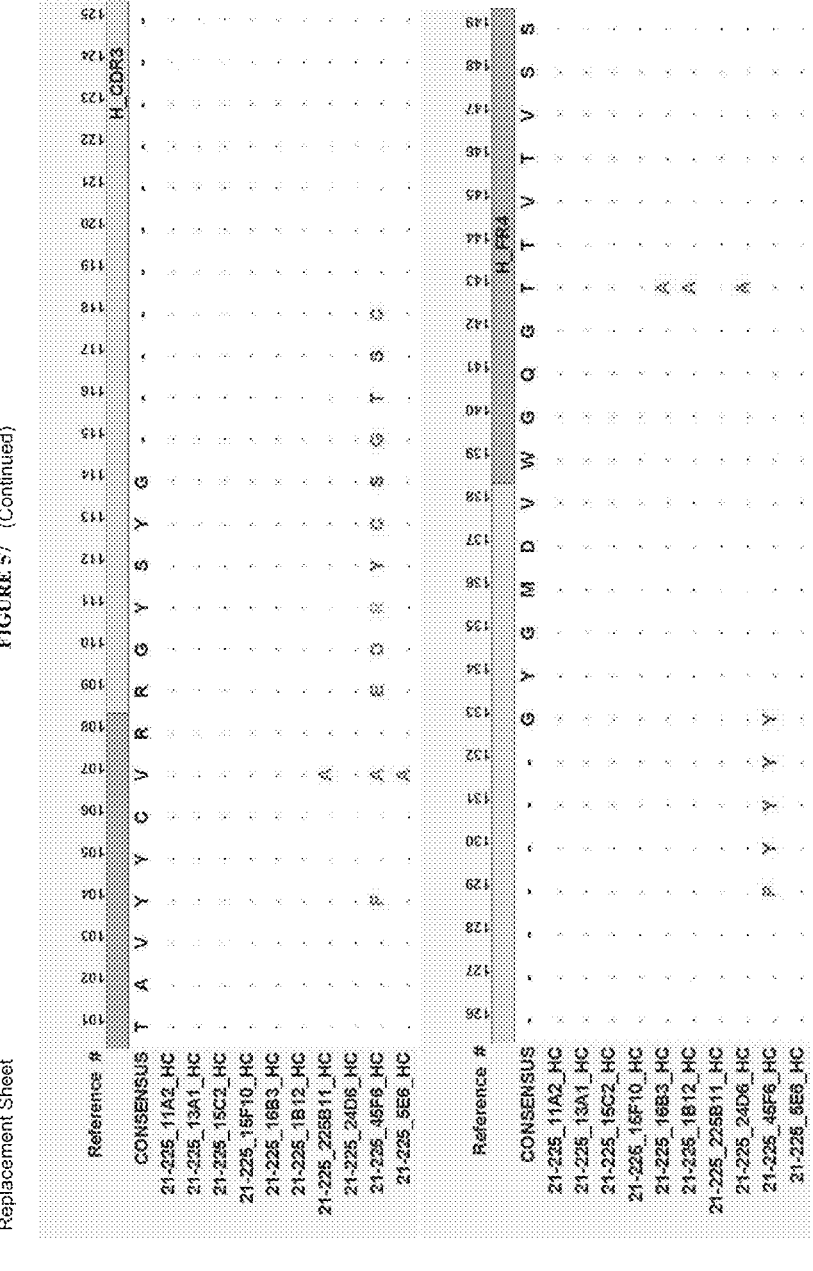
Figure 57:
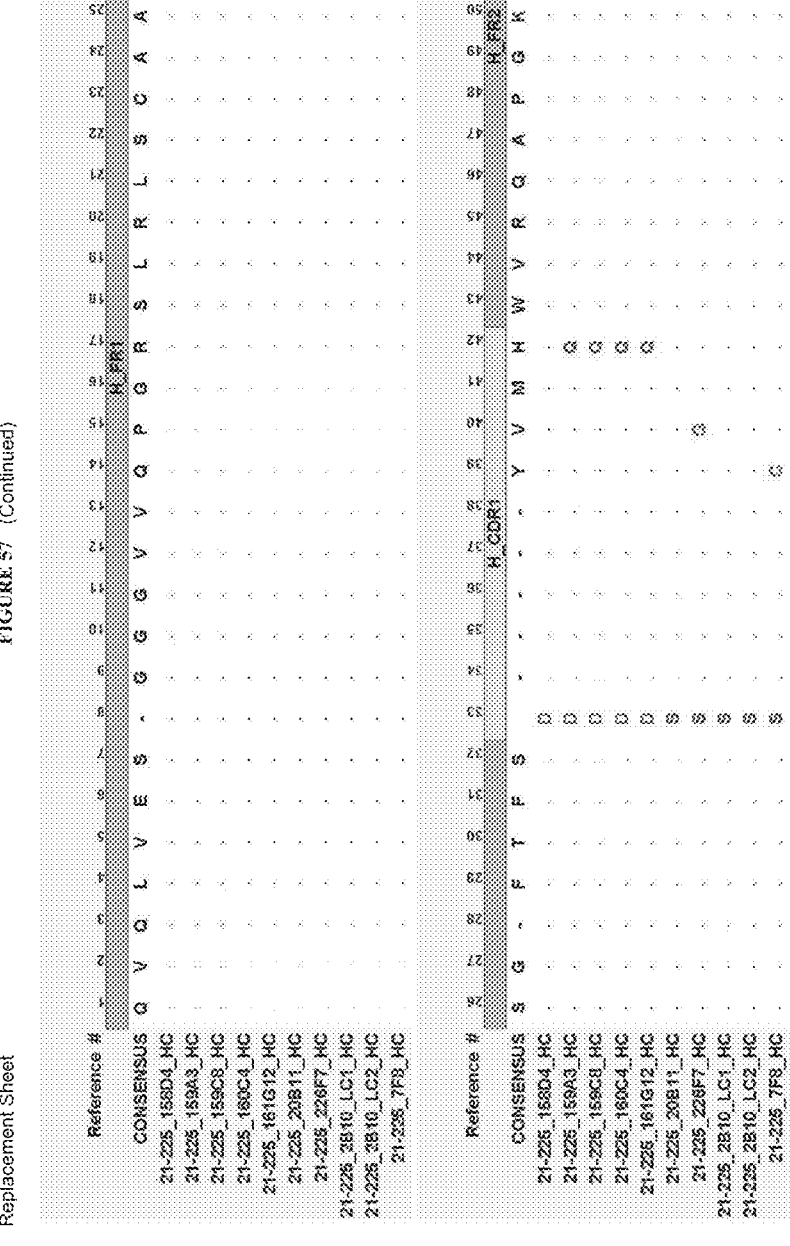
Figure 57:
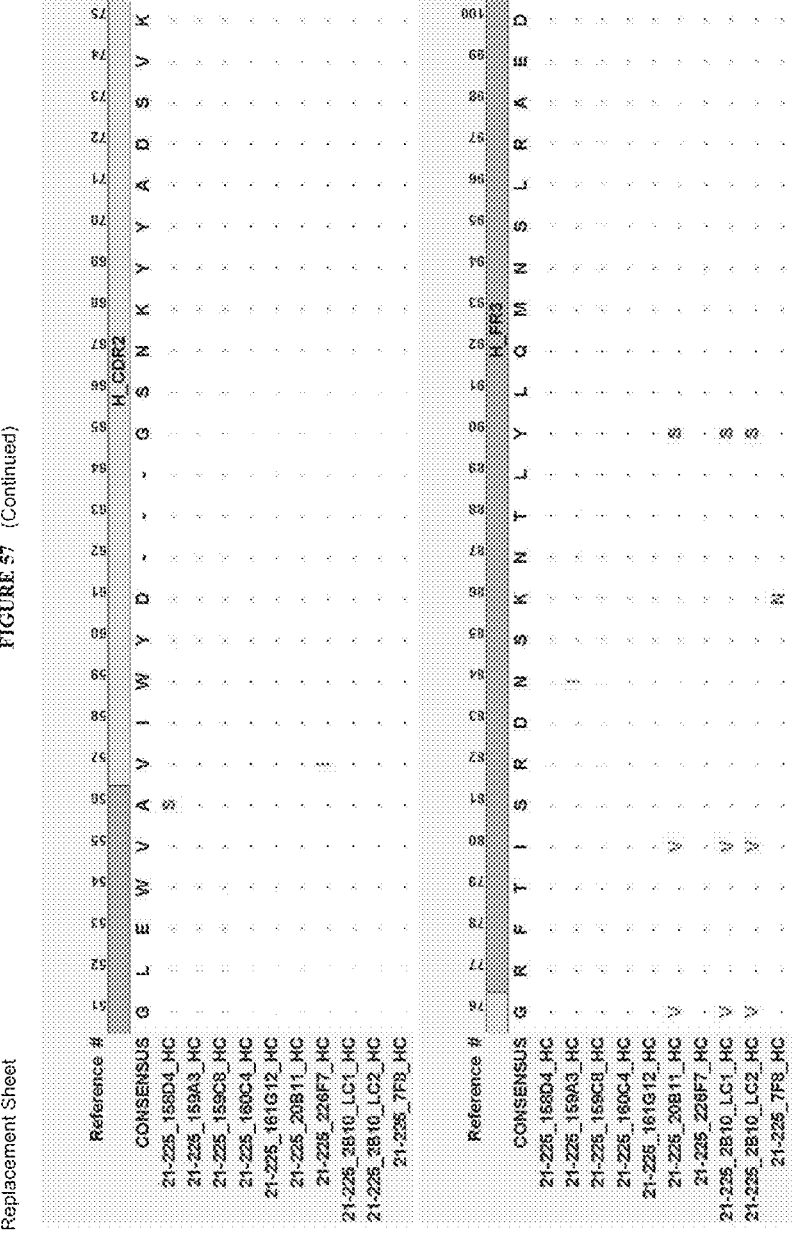
Figure 57:
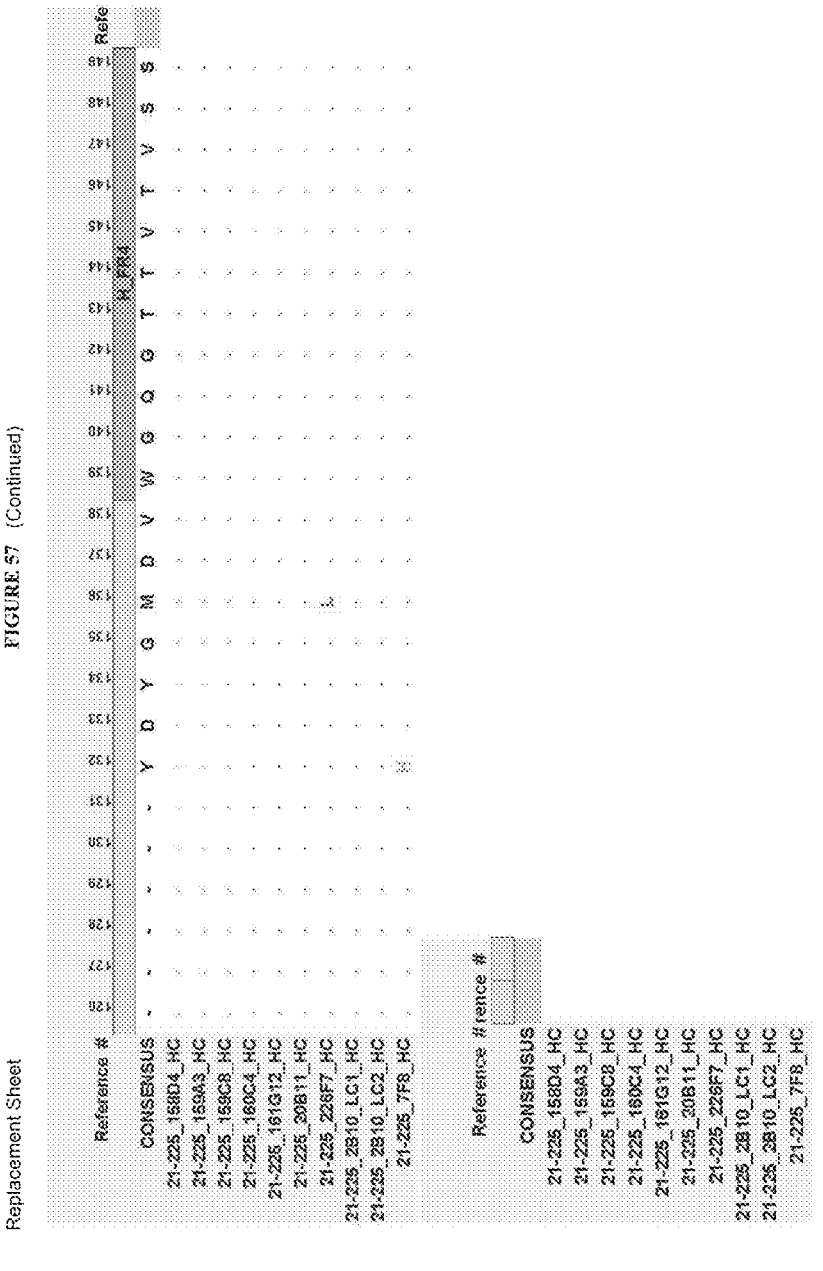
Figure 57:
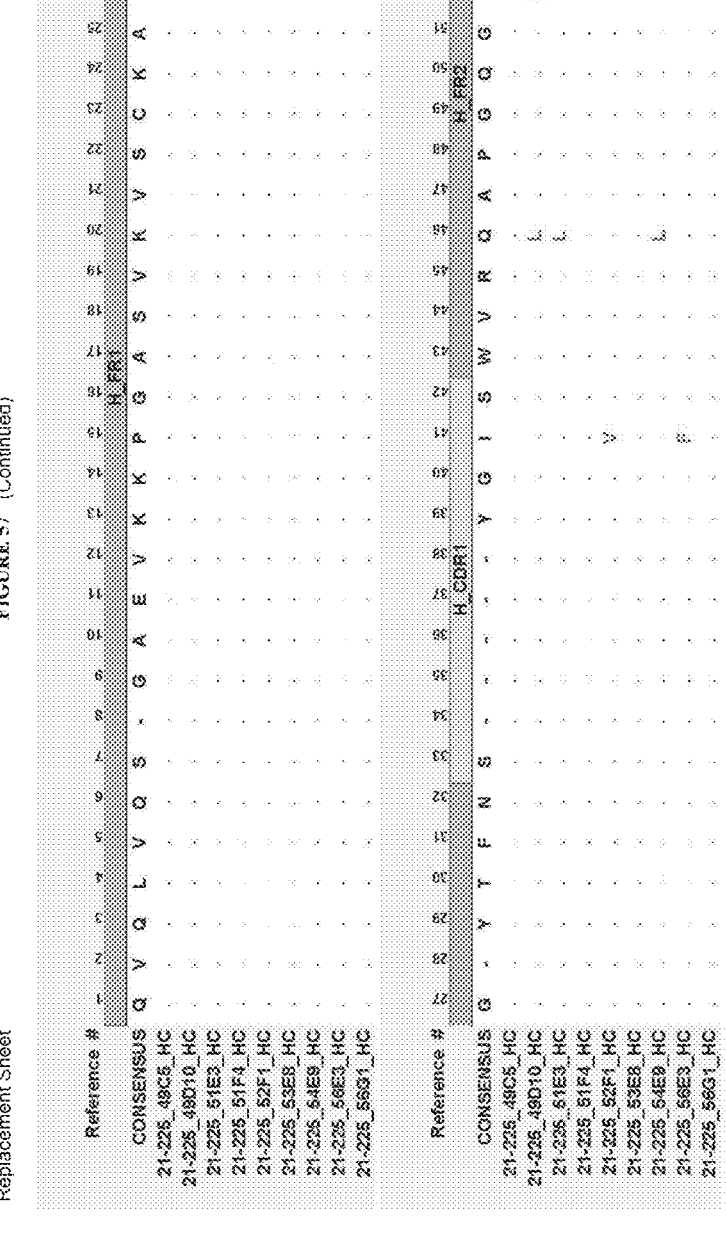
Figure 57:
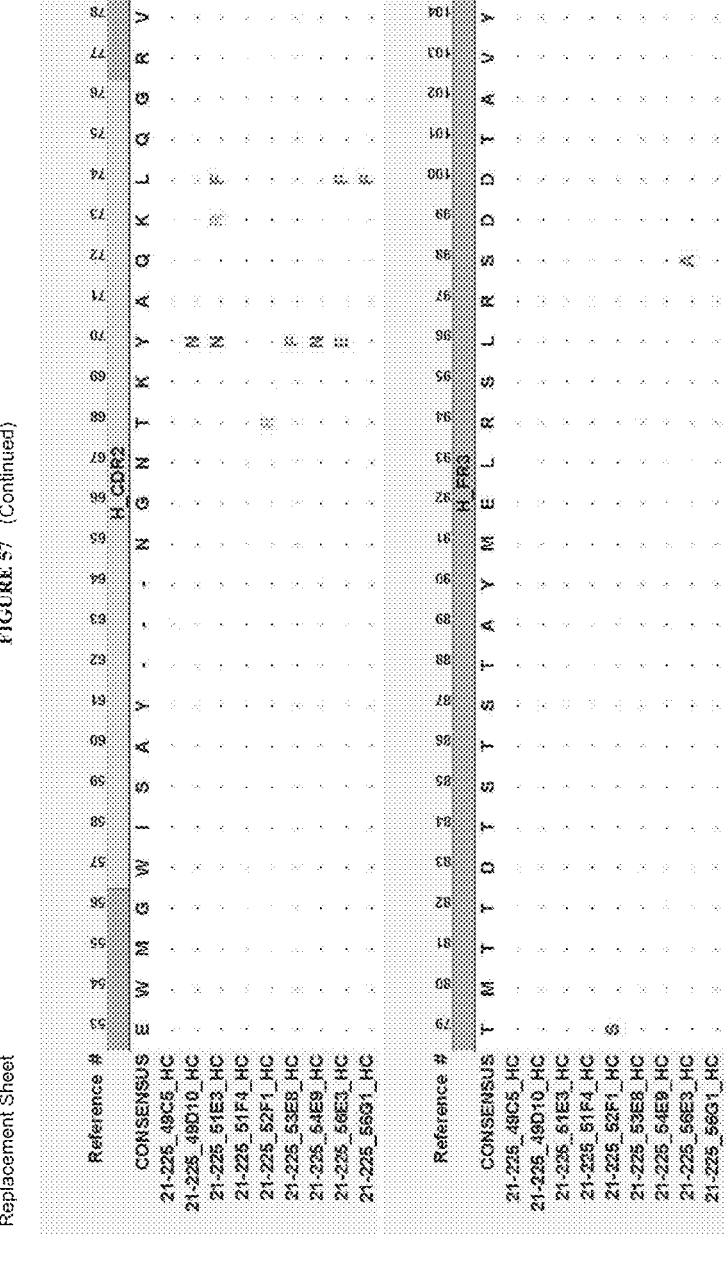
Figure 57:
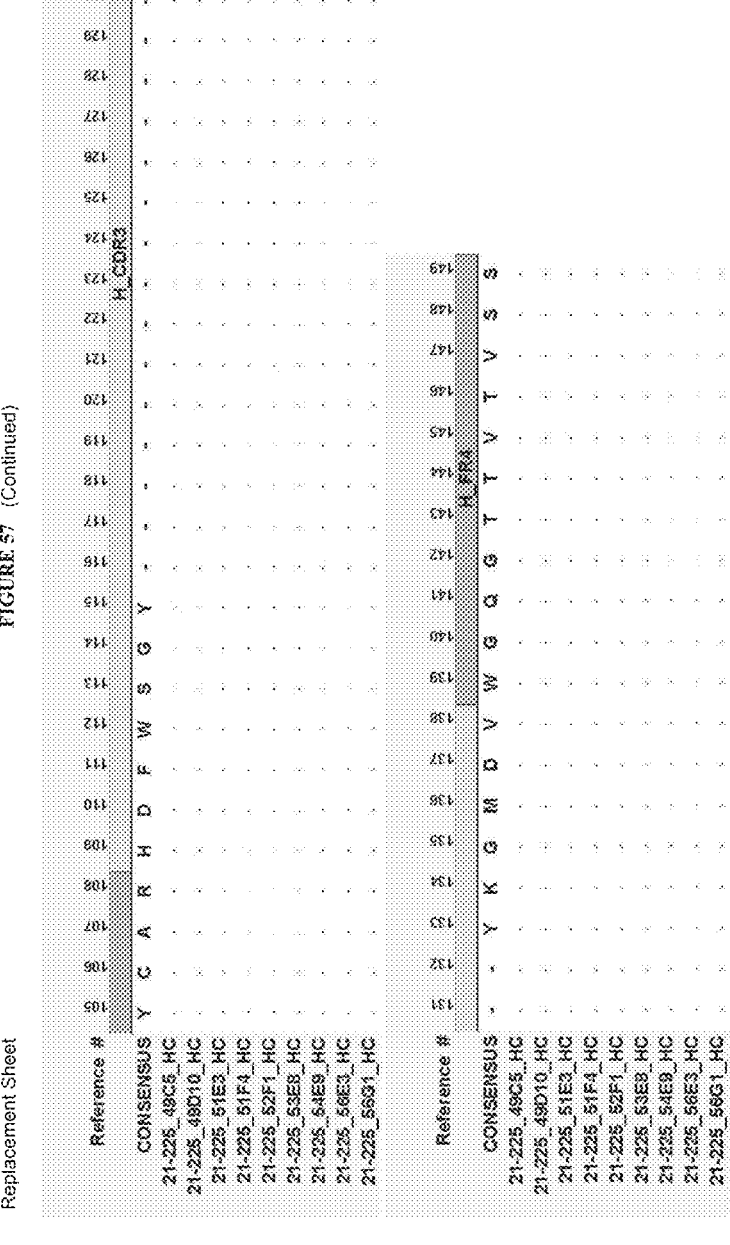
Figure 57:
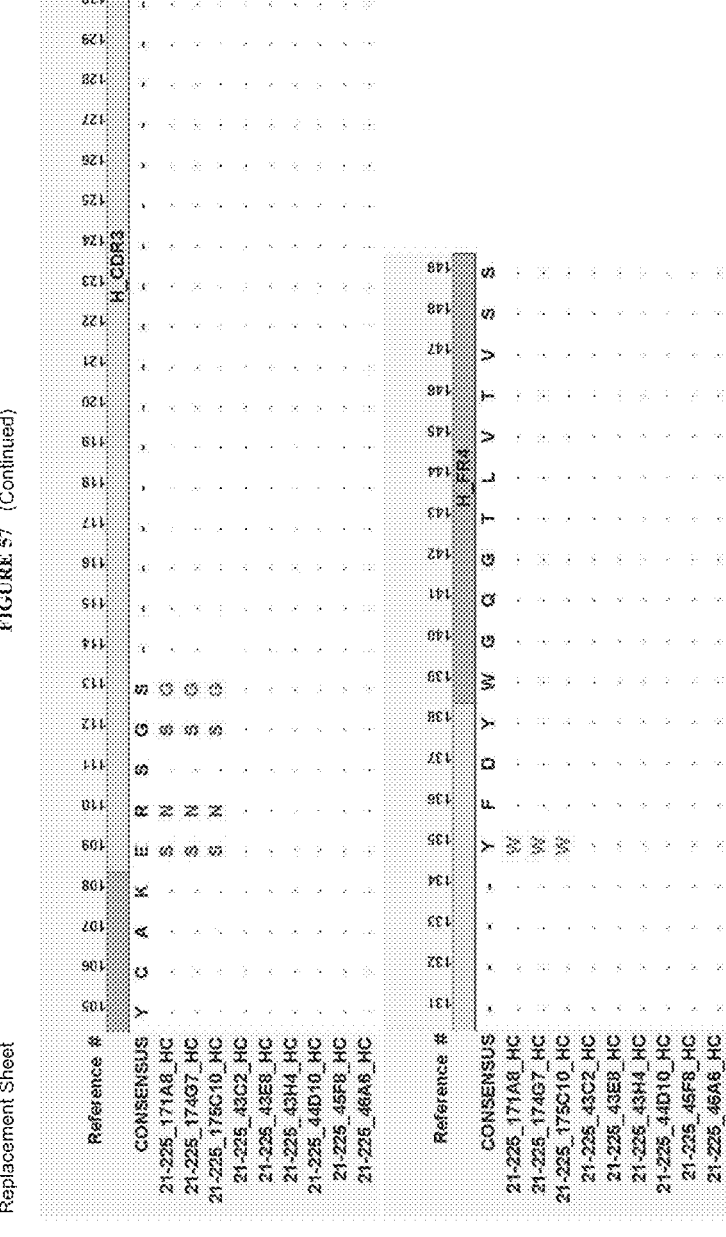
Figure 57:
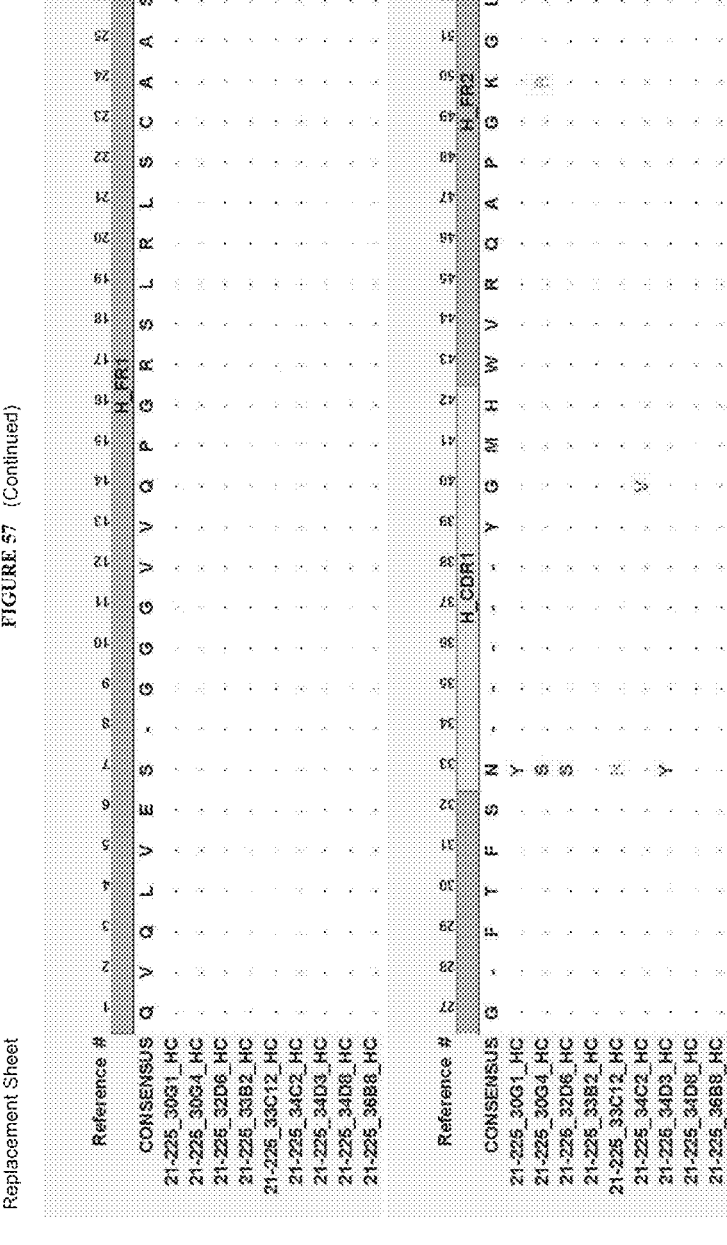
Figure 57:
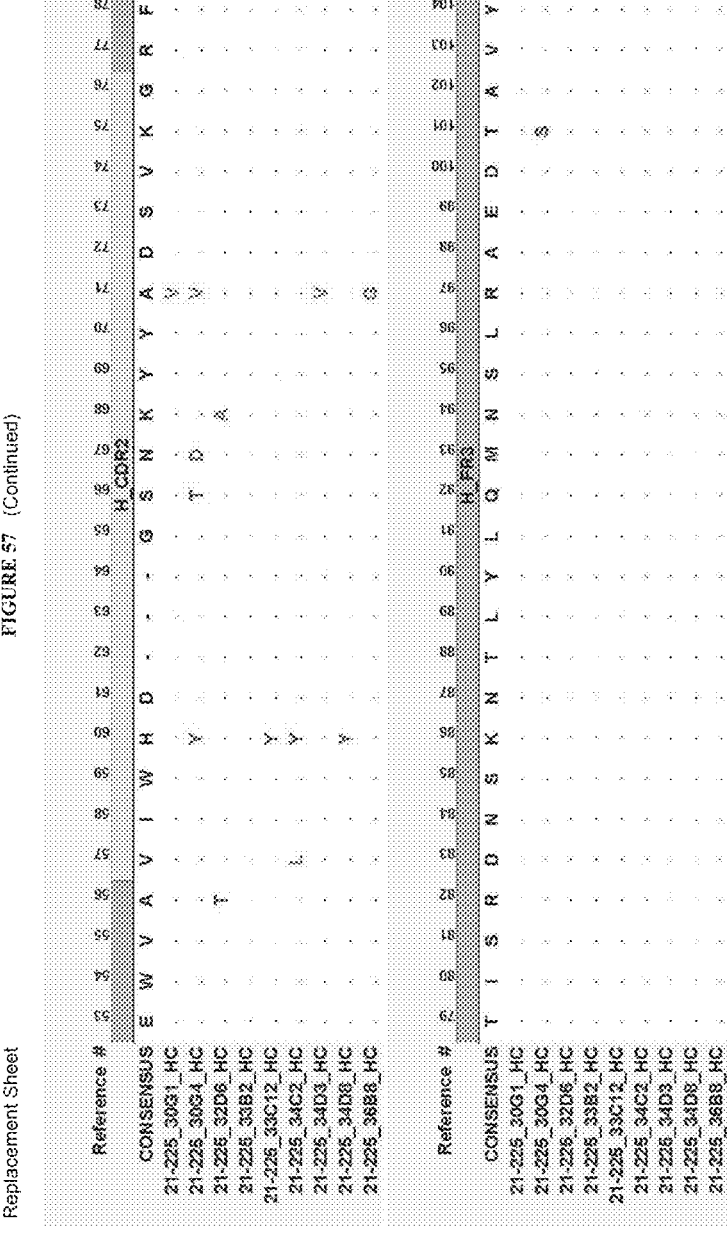
Figure 57:
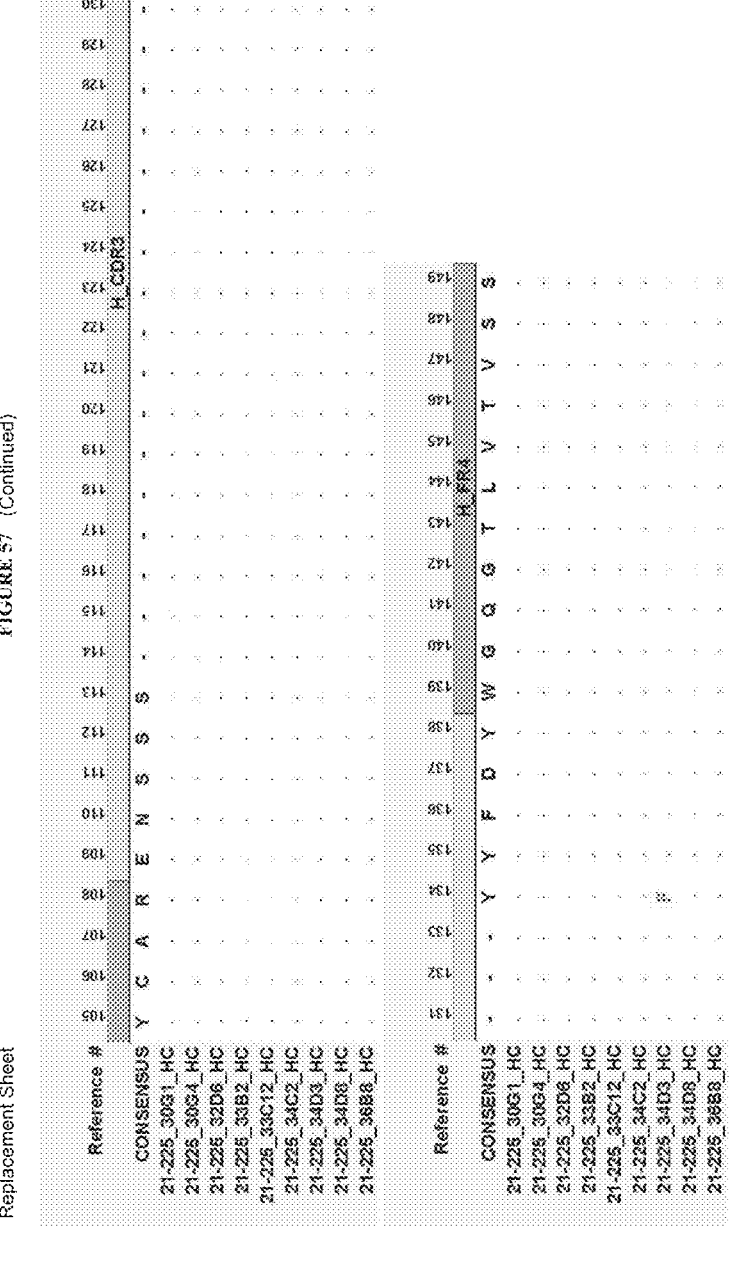
Figure 57:
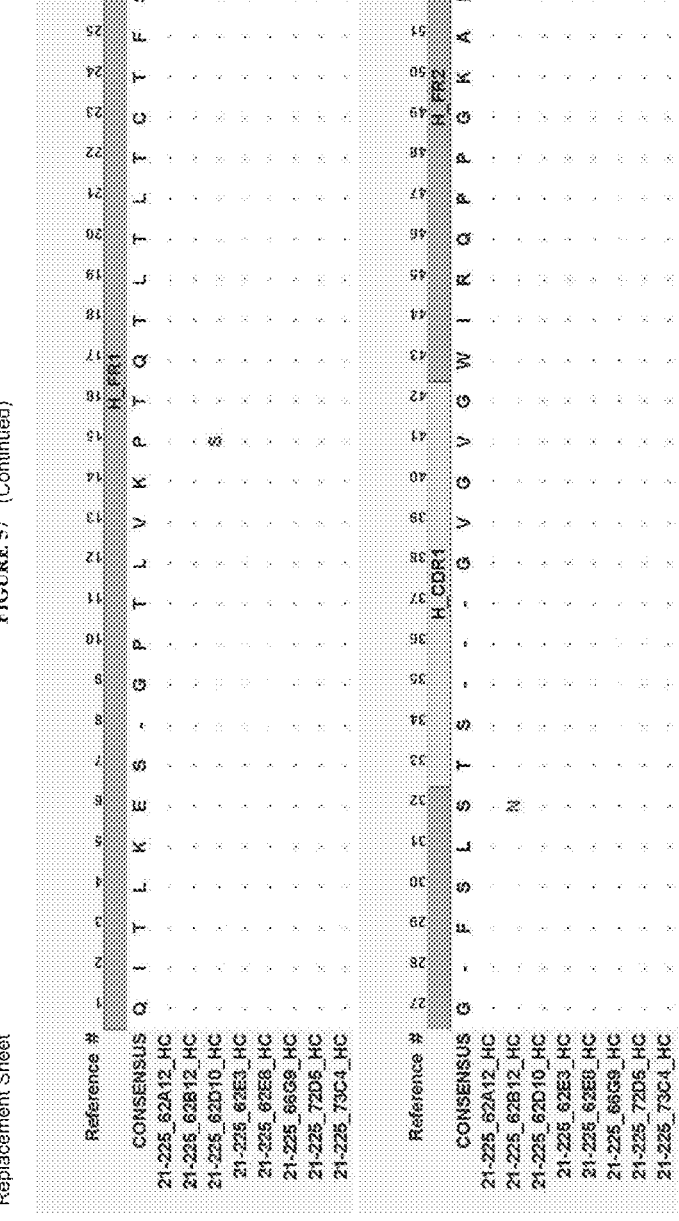
Figure 57:
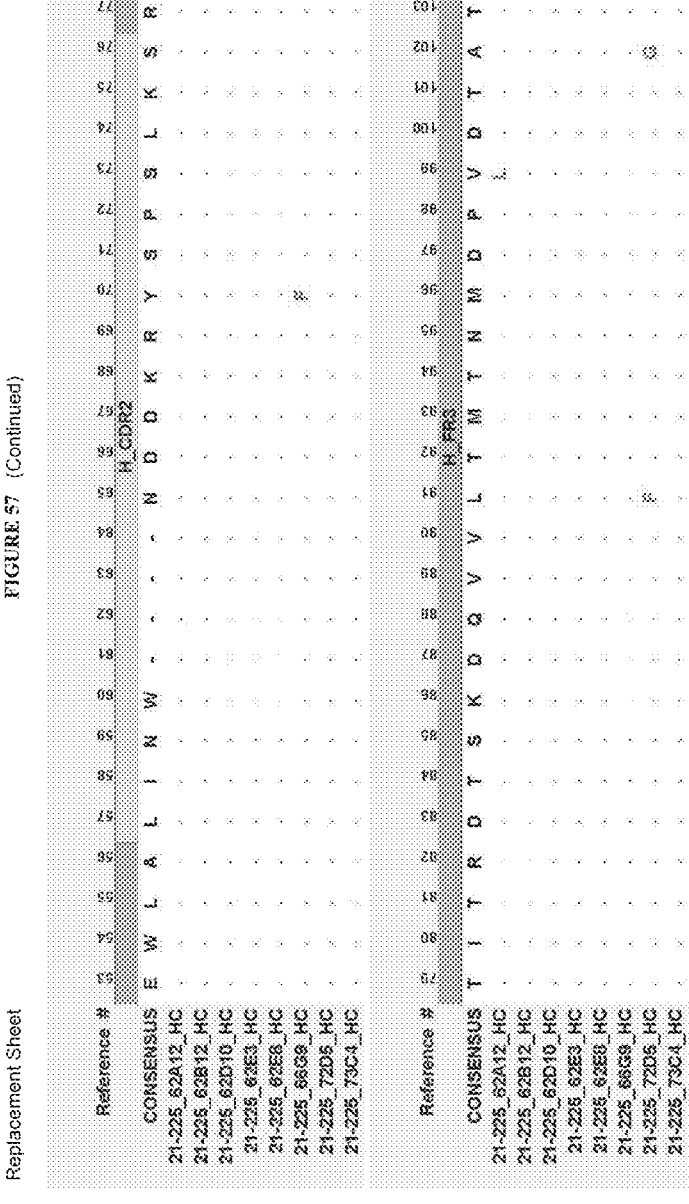
Figure 57:
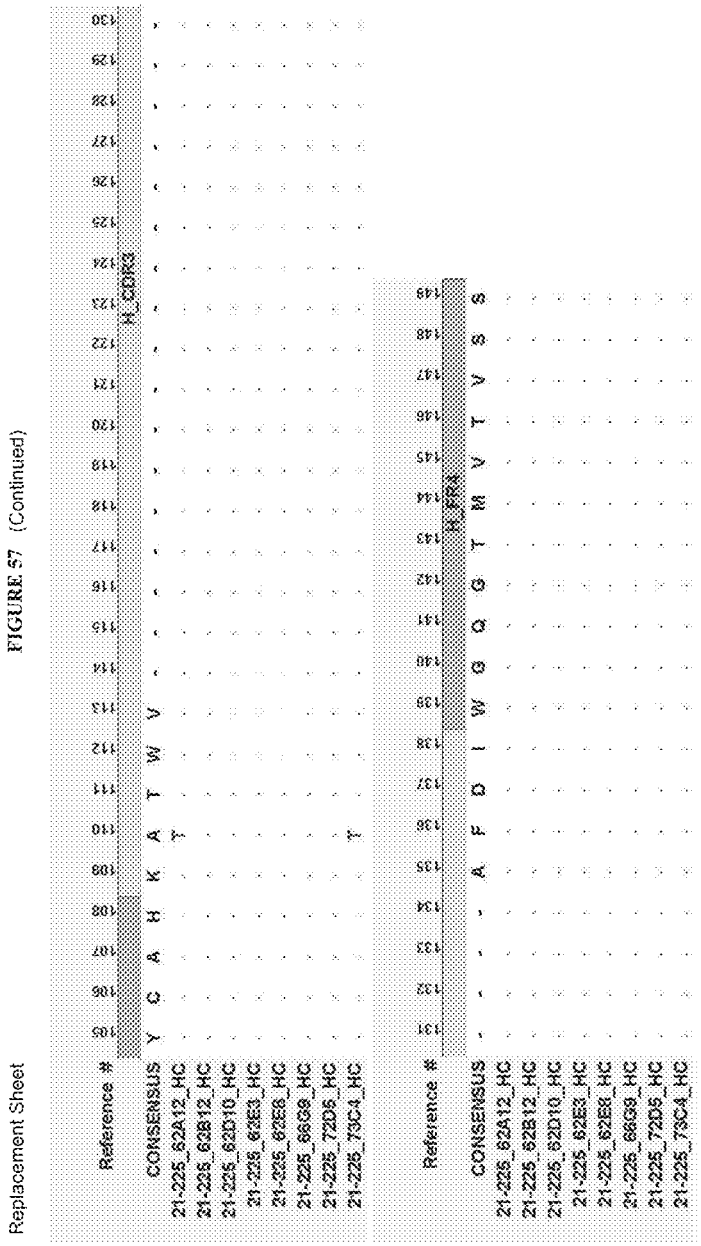
Figure 57:
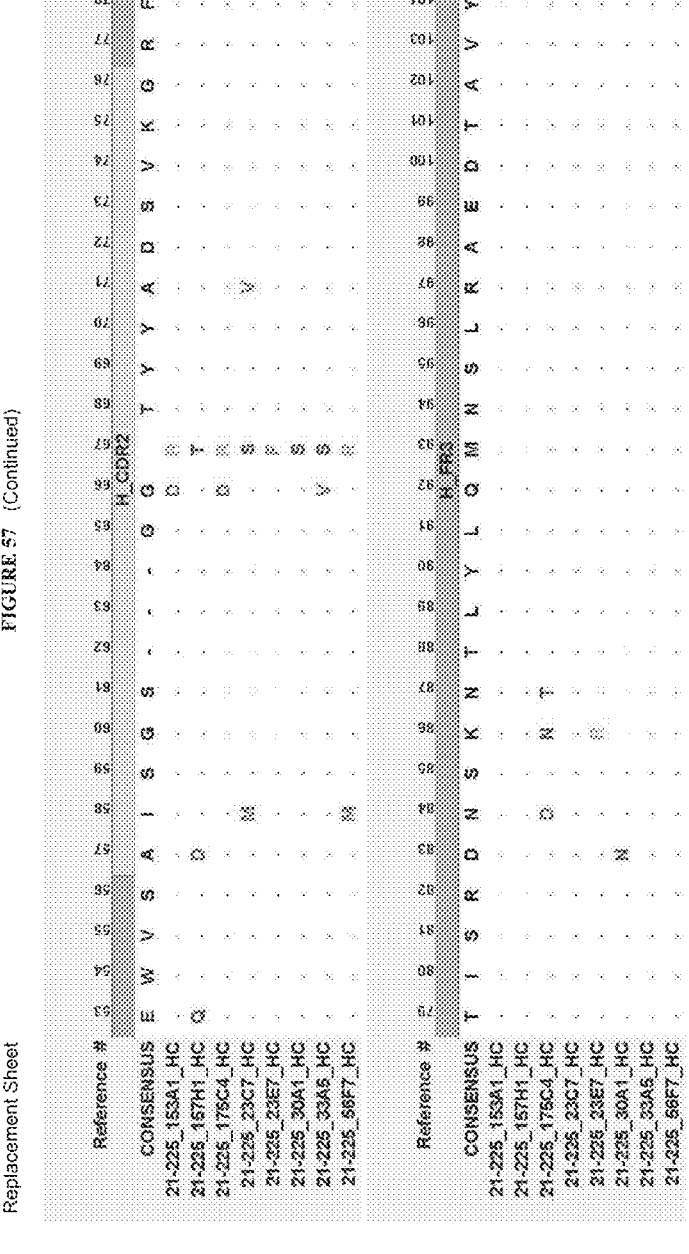
Figure 57:
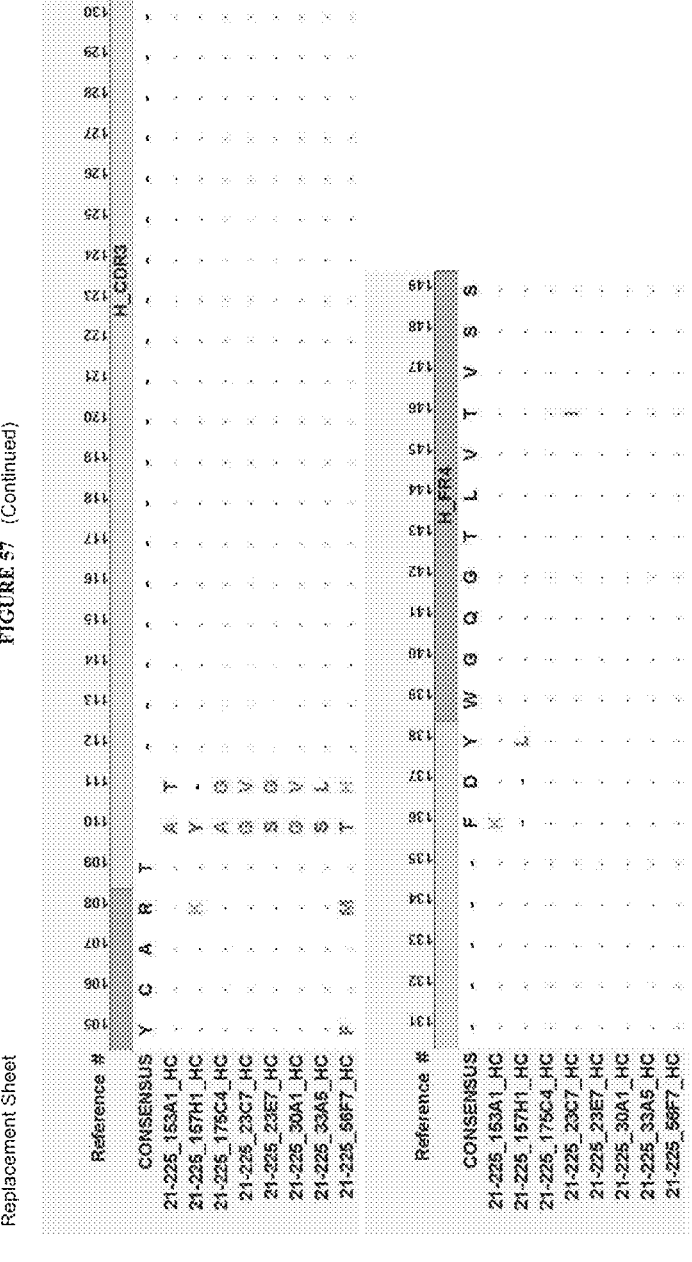
Figure 57:
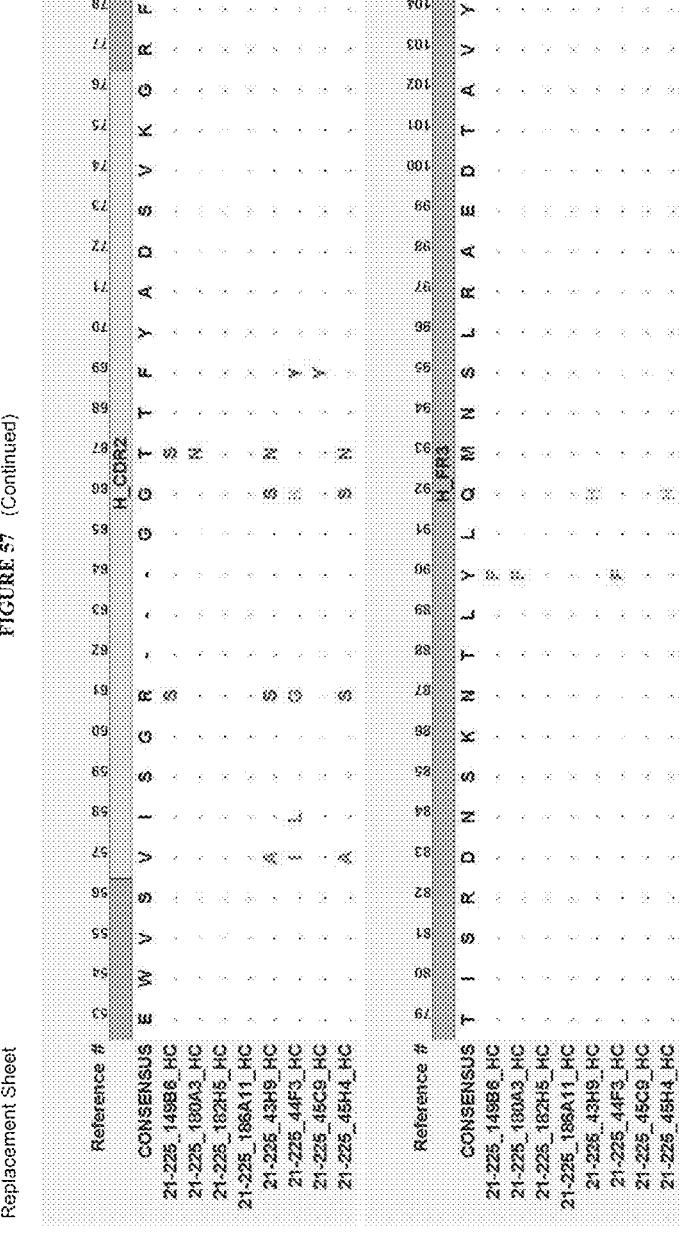
Figure 57:
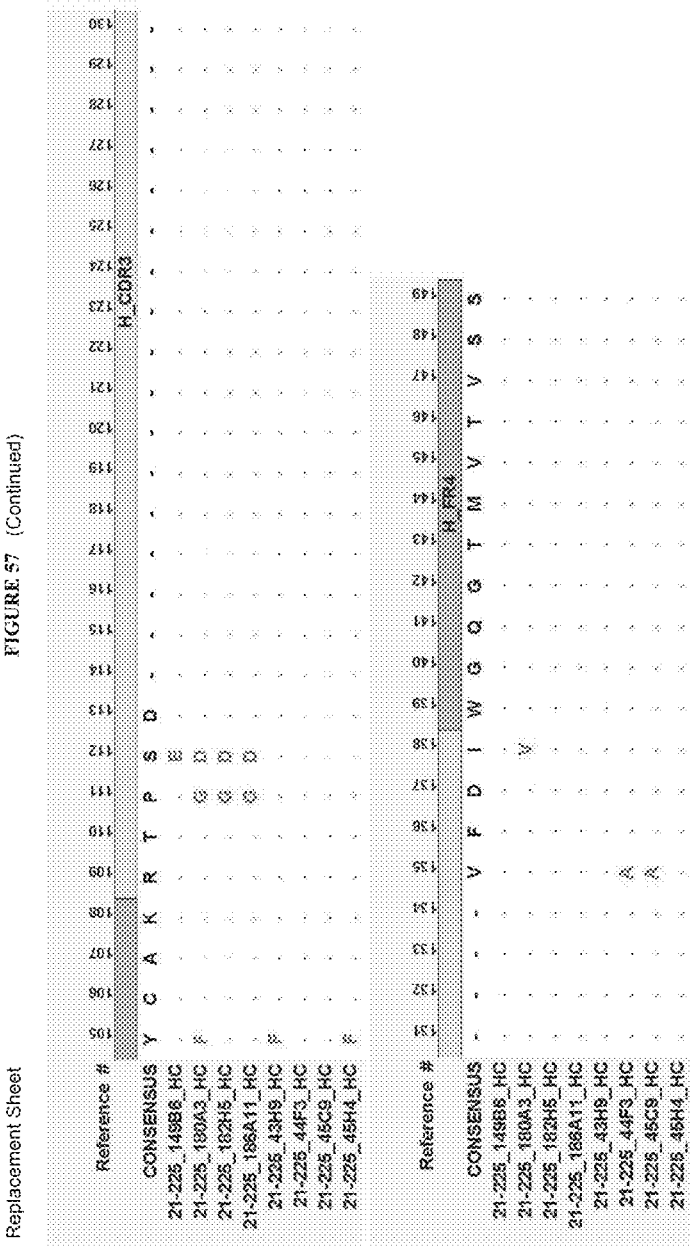
Figure 57:
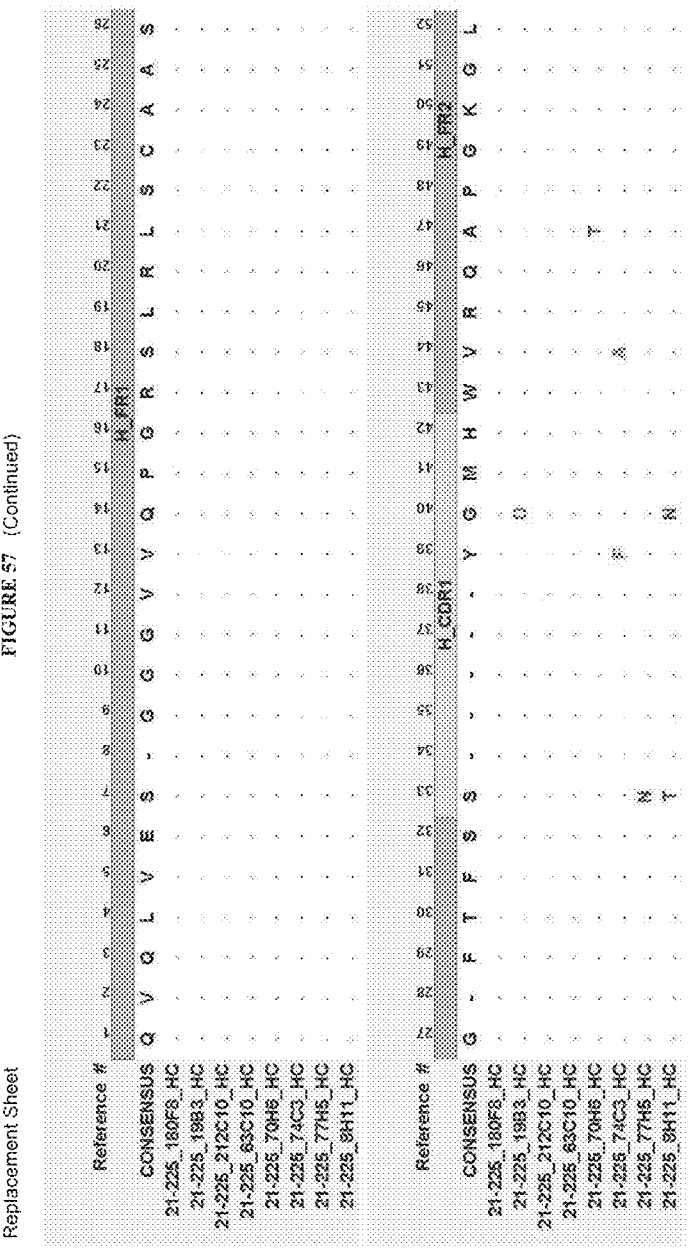
Figure 57:
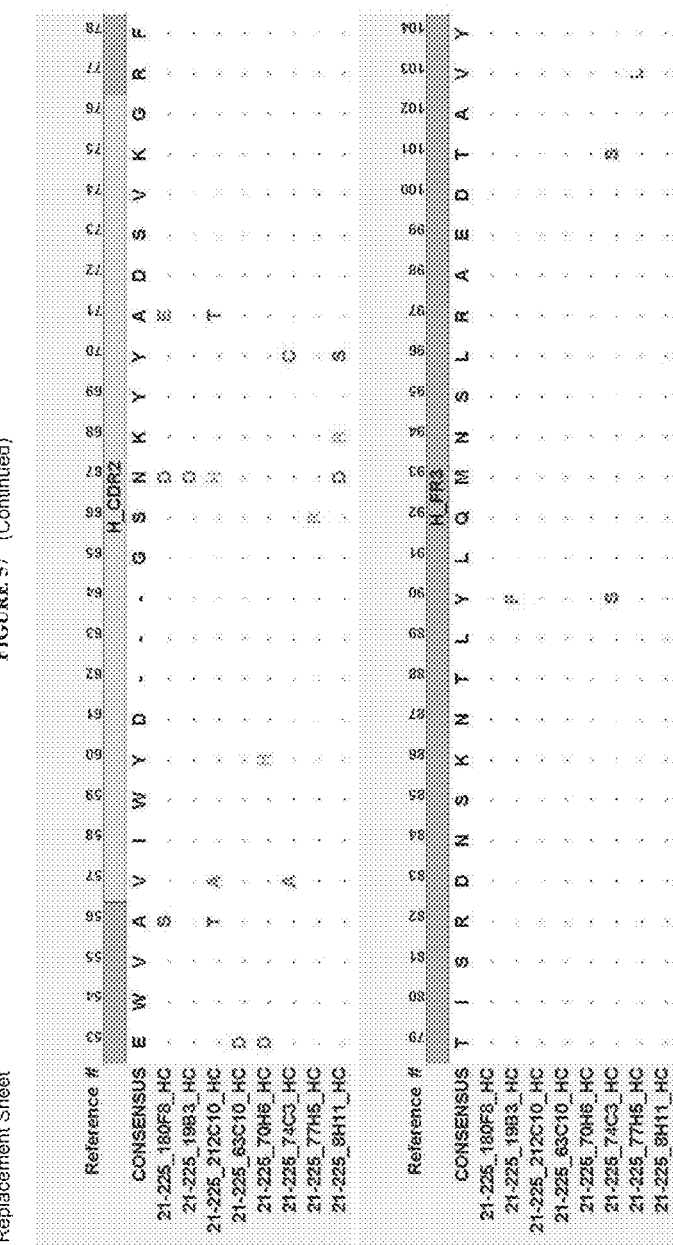
Figure 57:
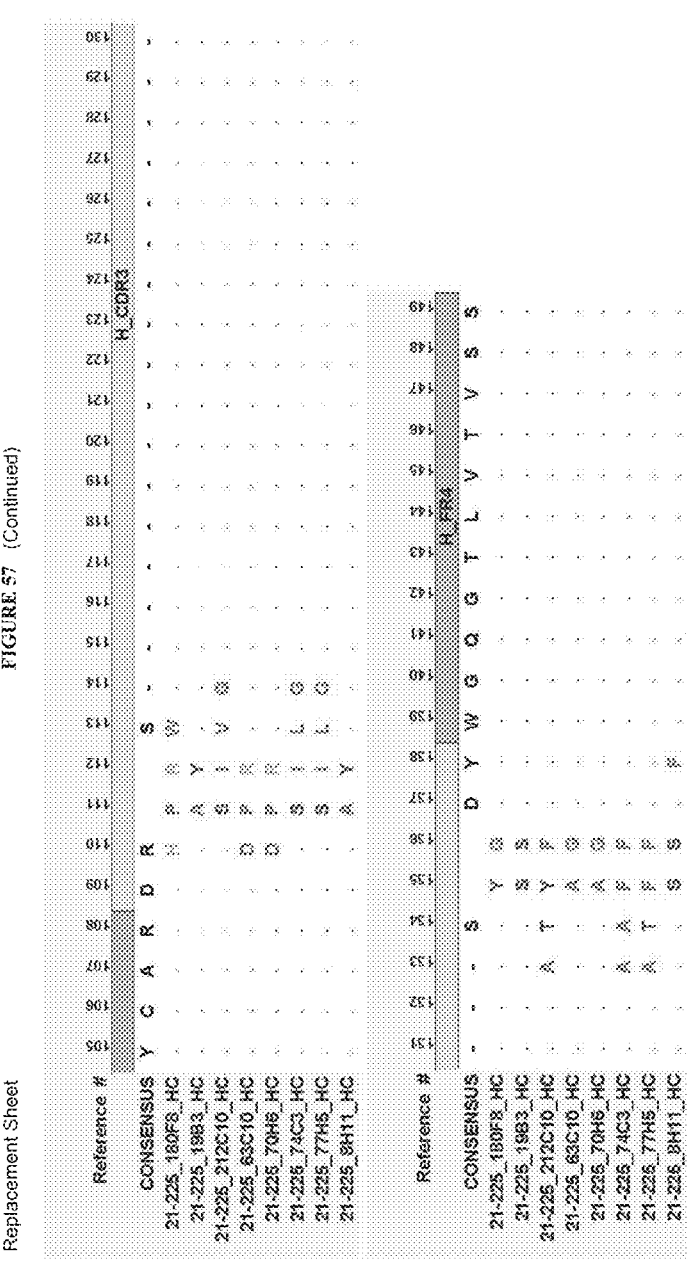
Figure 57:
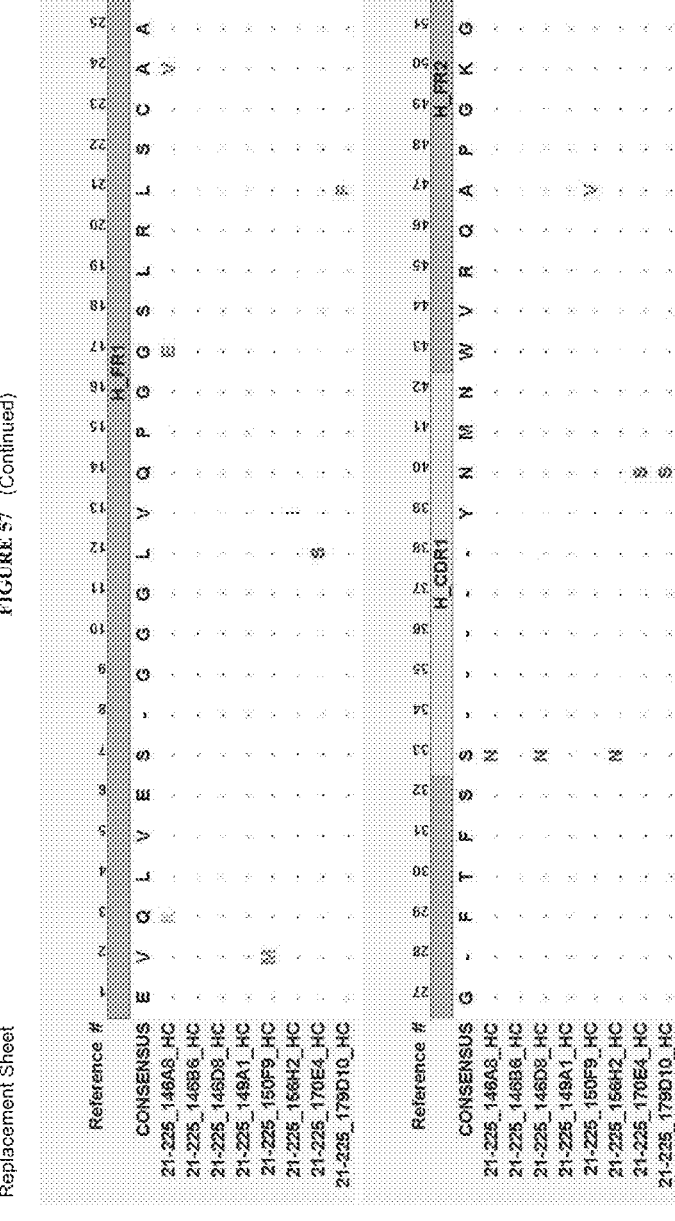
Figure 57:
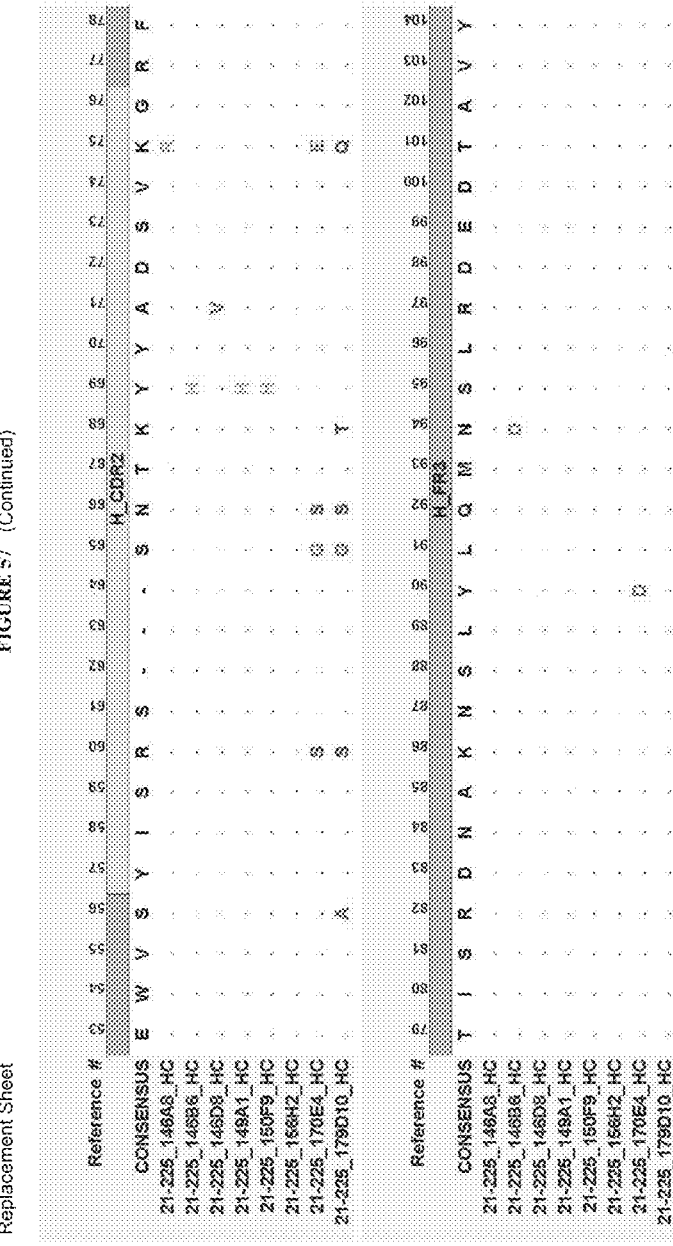
Figure 57:
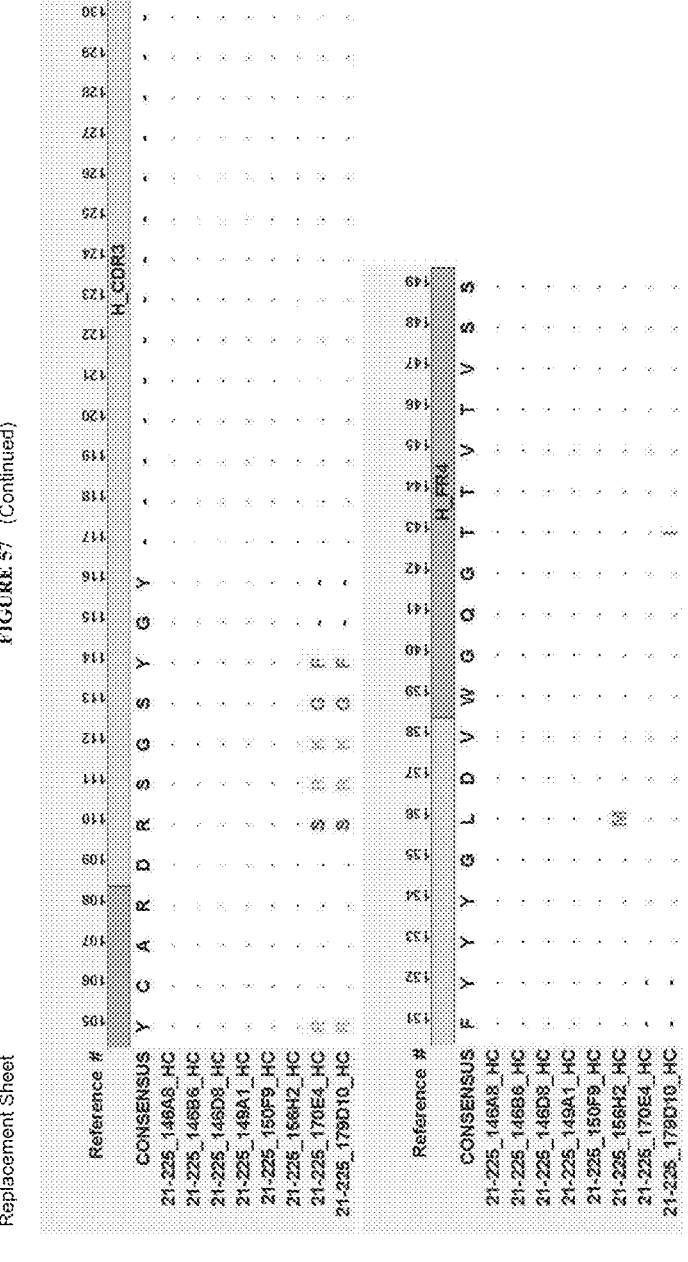
Figure 57:
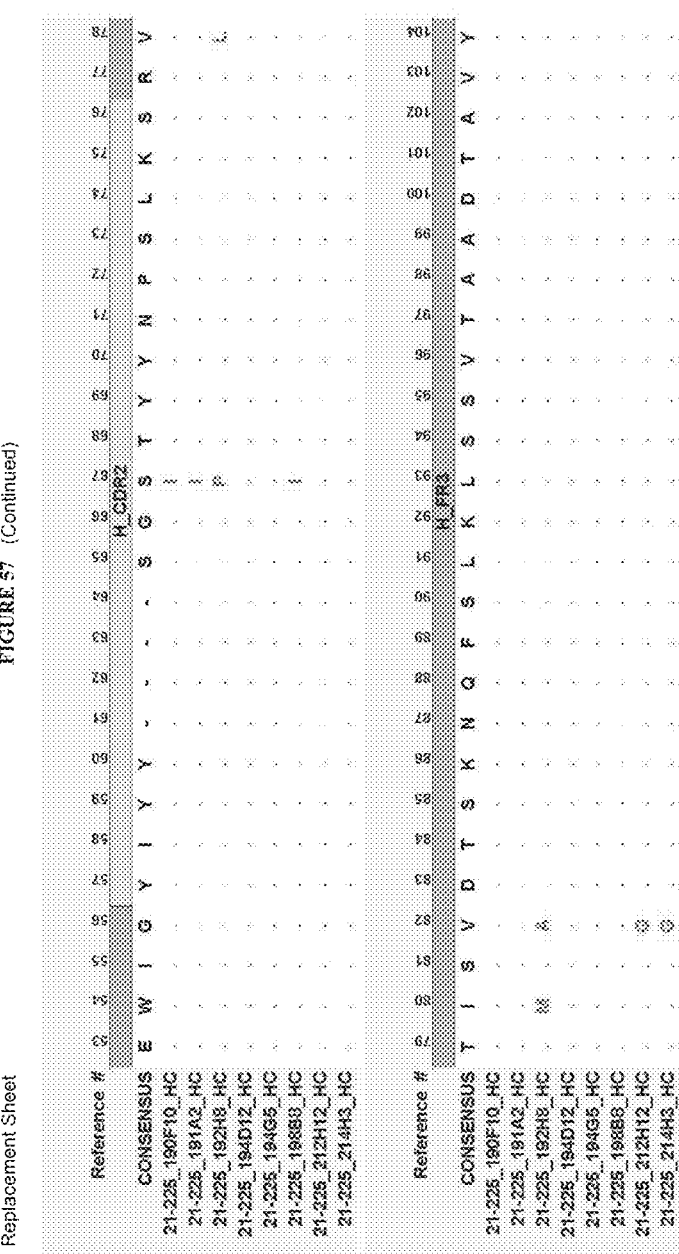
Figure 57:
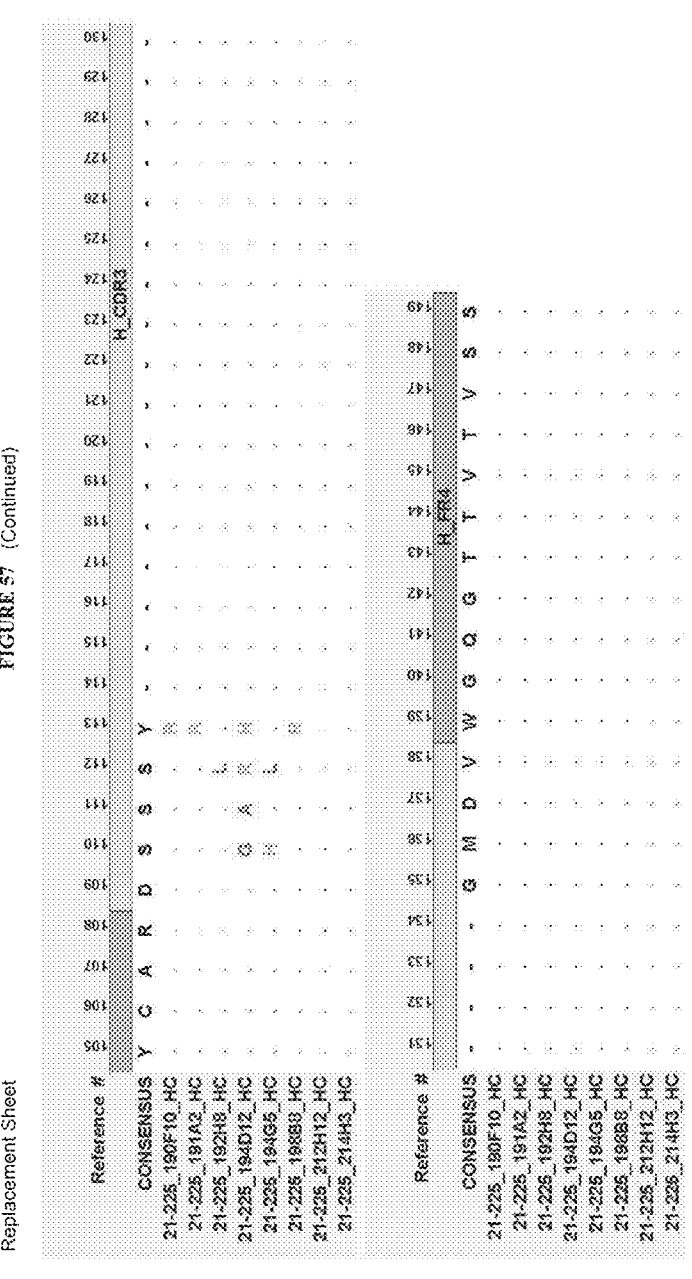
Figure 57:
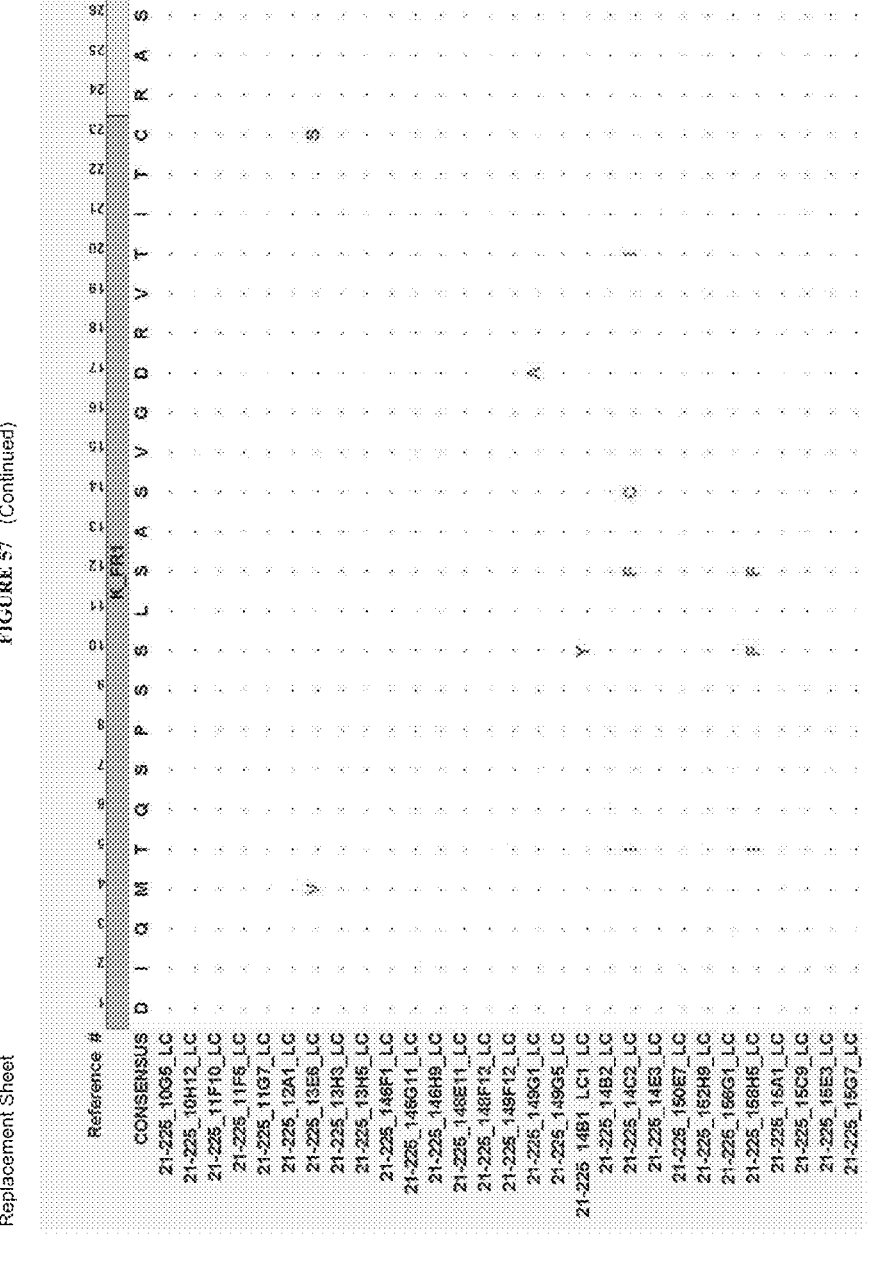
Figure 57:
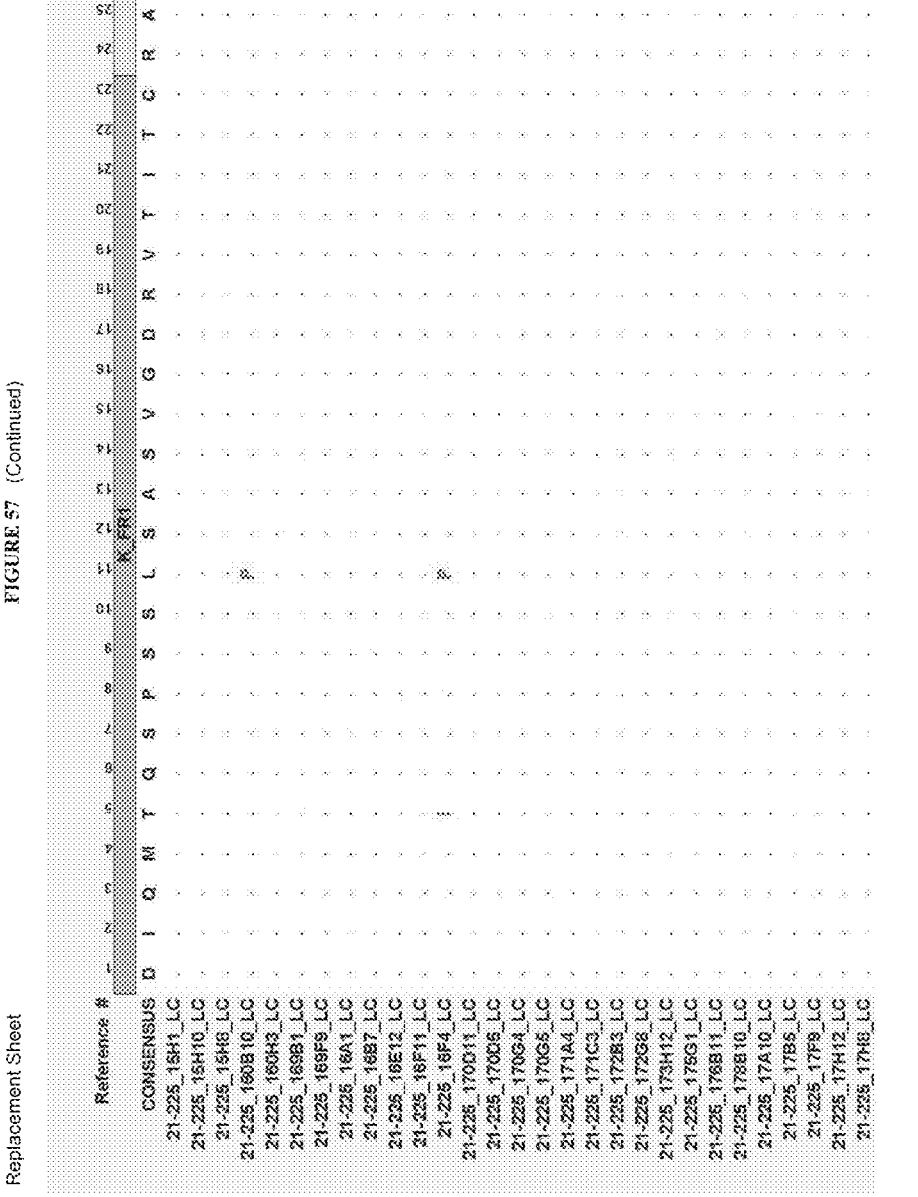
Figure 57:
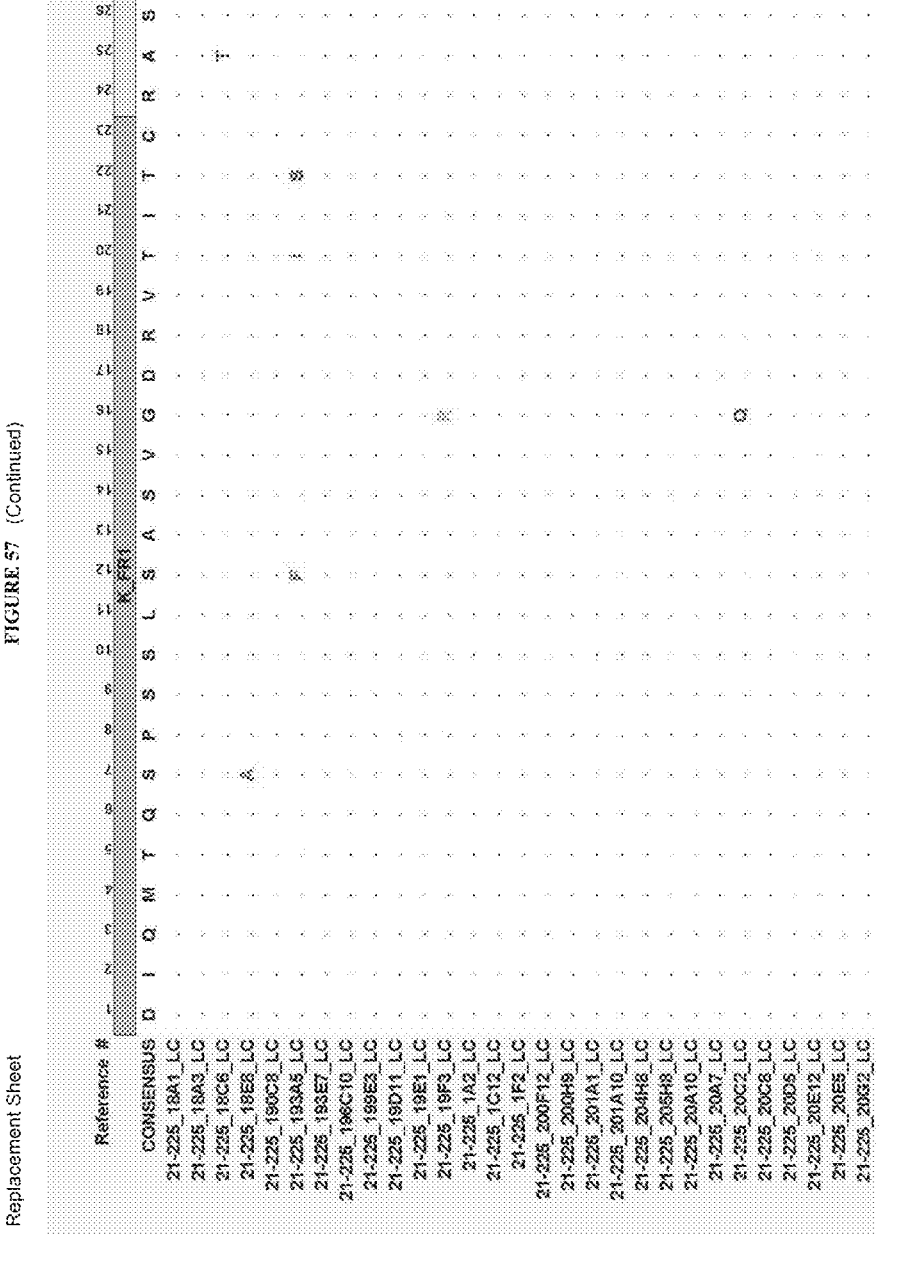
Figure 57:
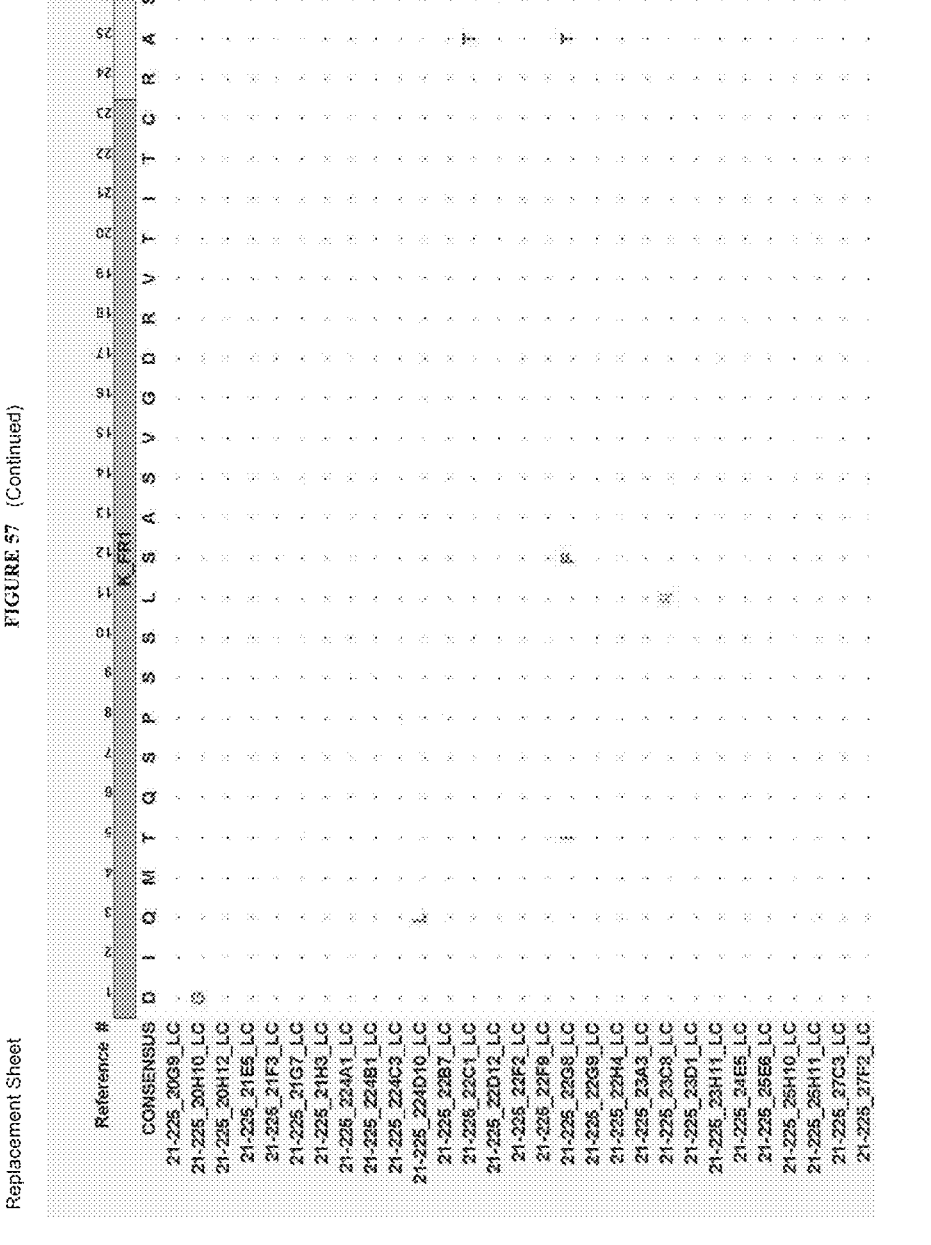
Figure 57:
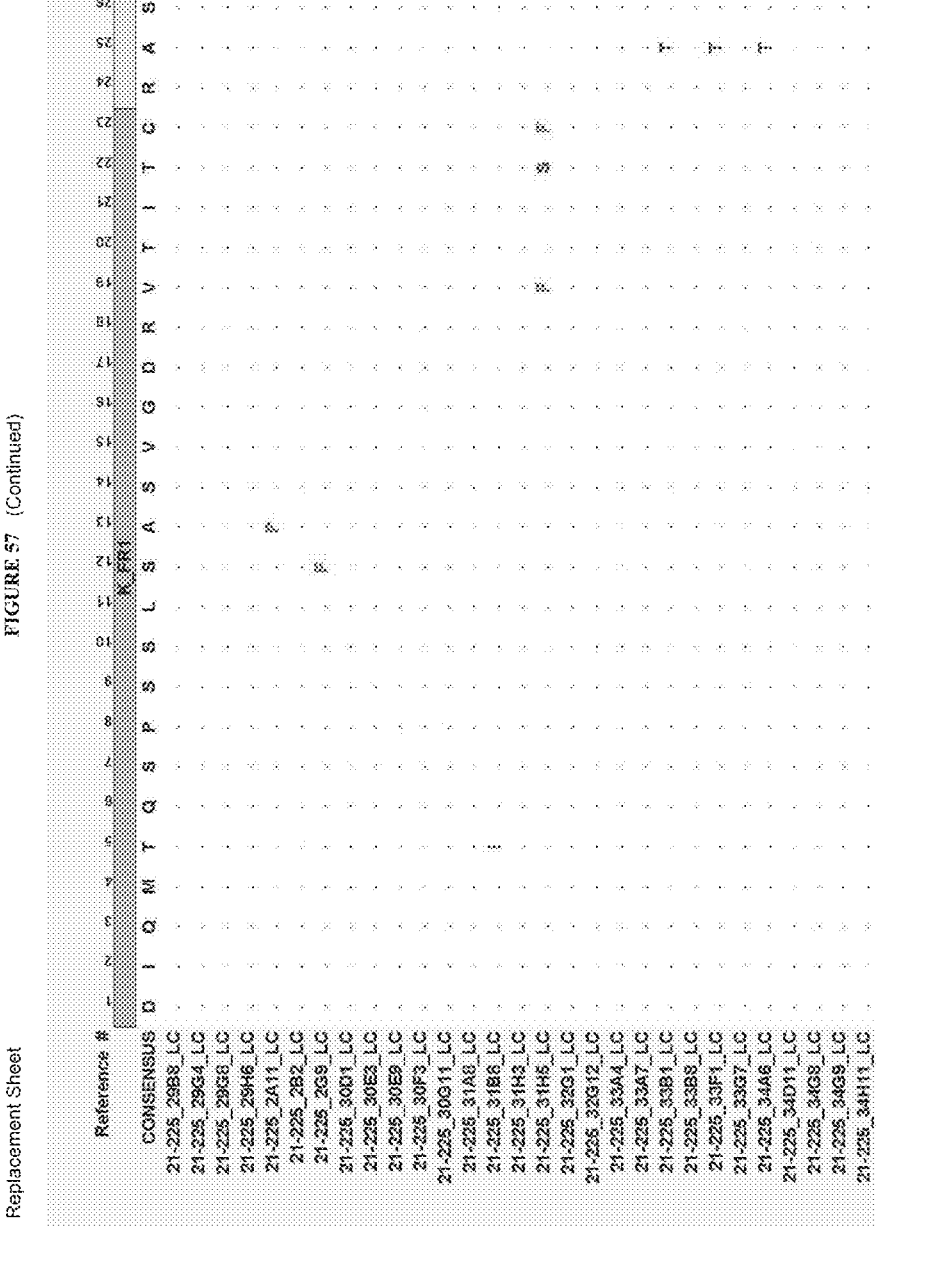
Figure 57:
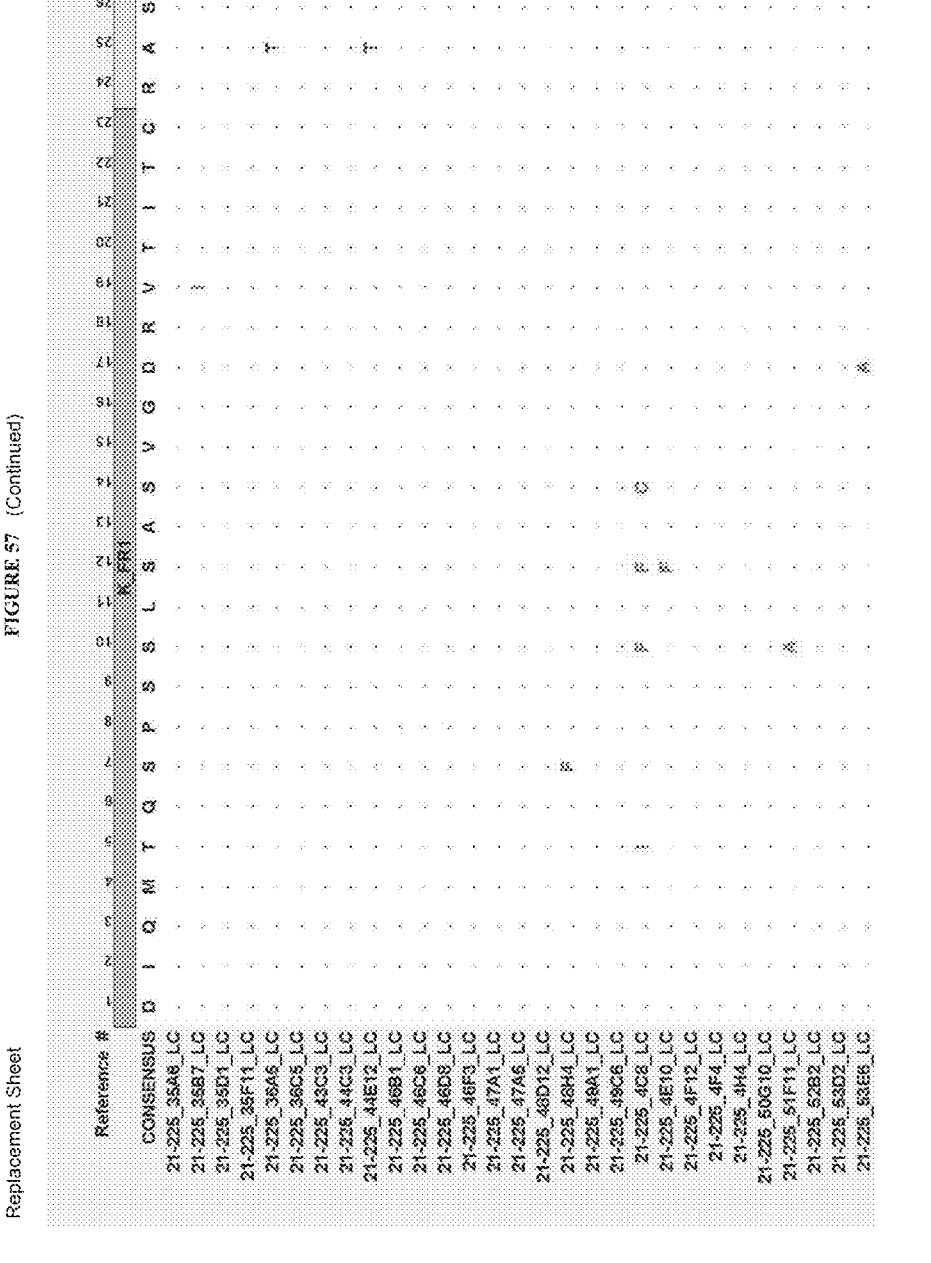
Figure 57:
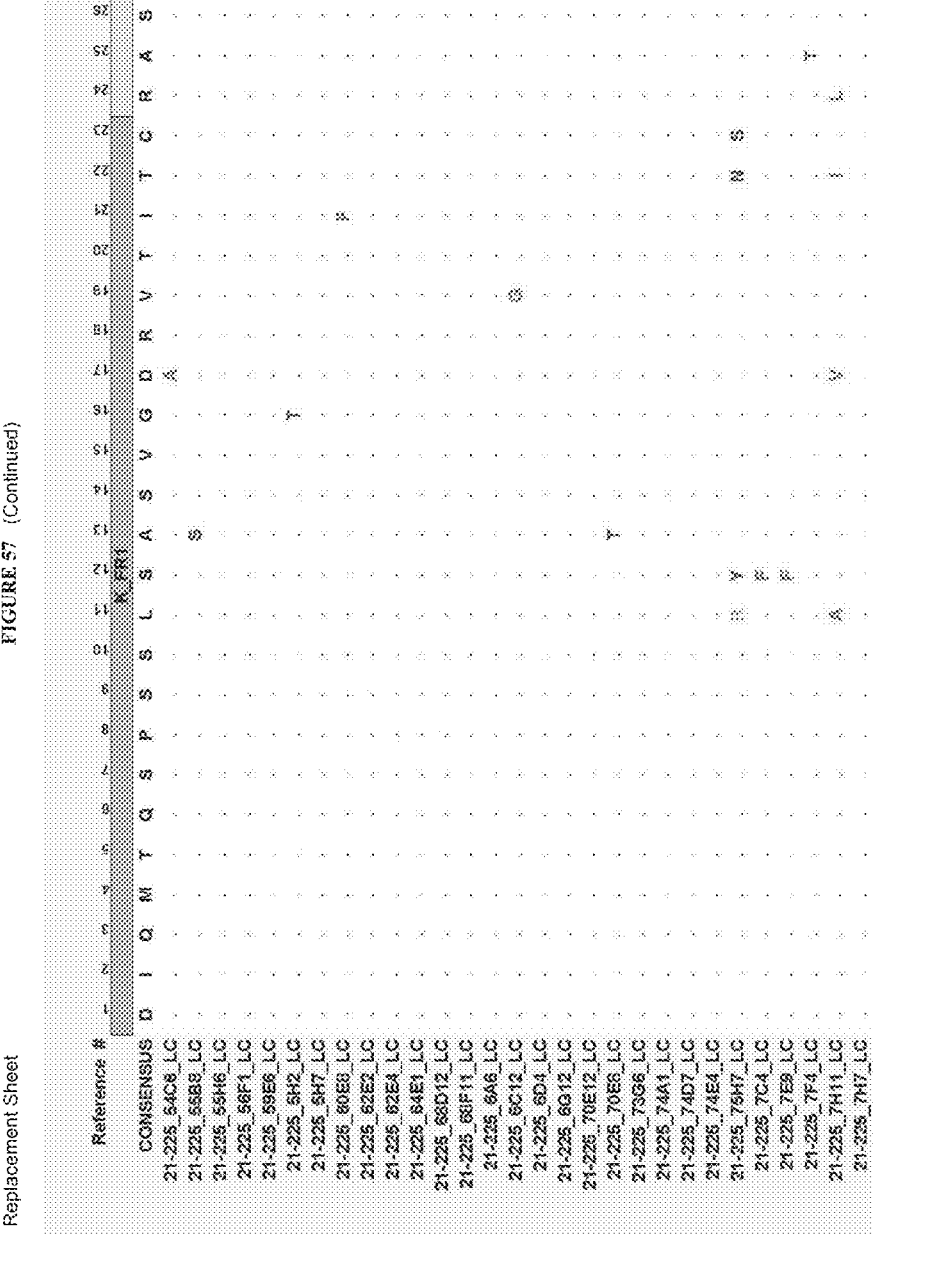
Figure 57:
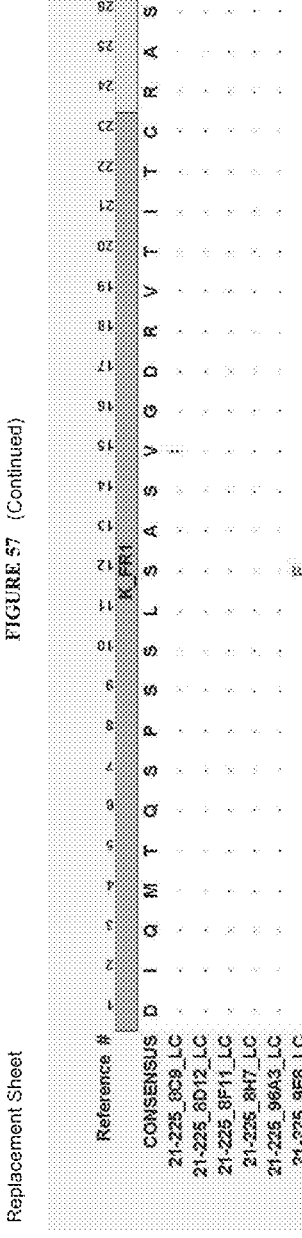
Figure 57:
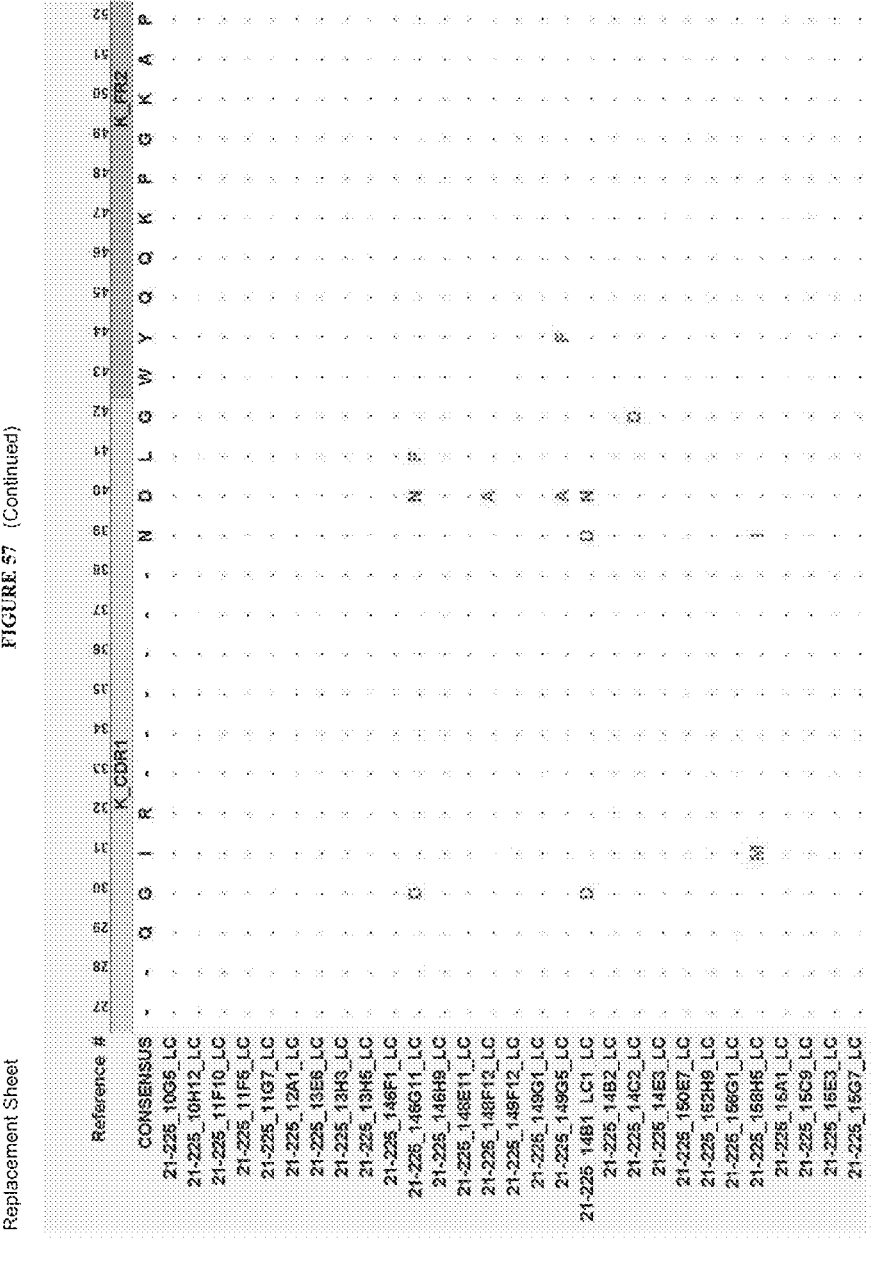
Figure 57:
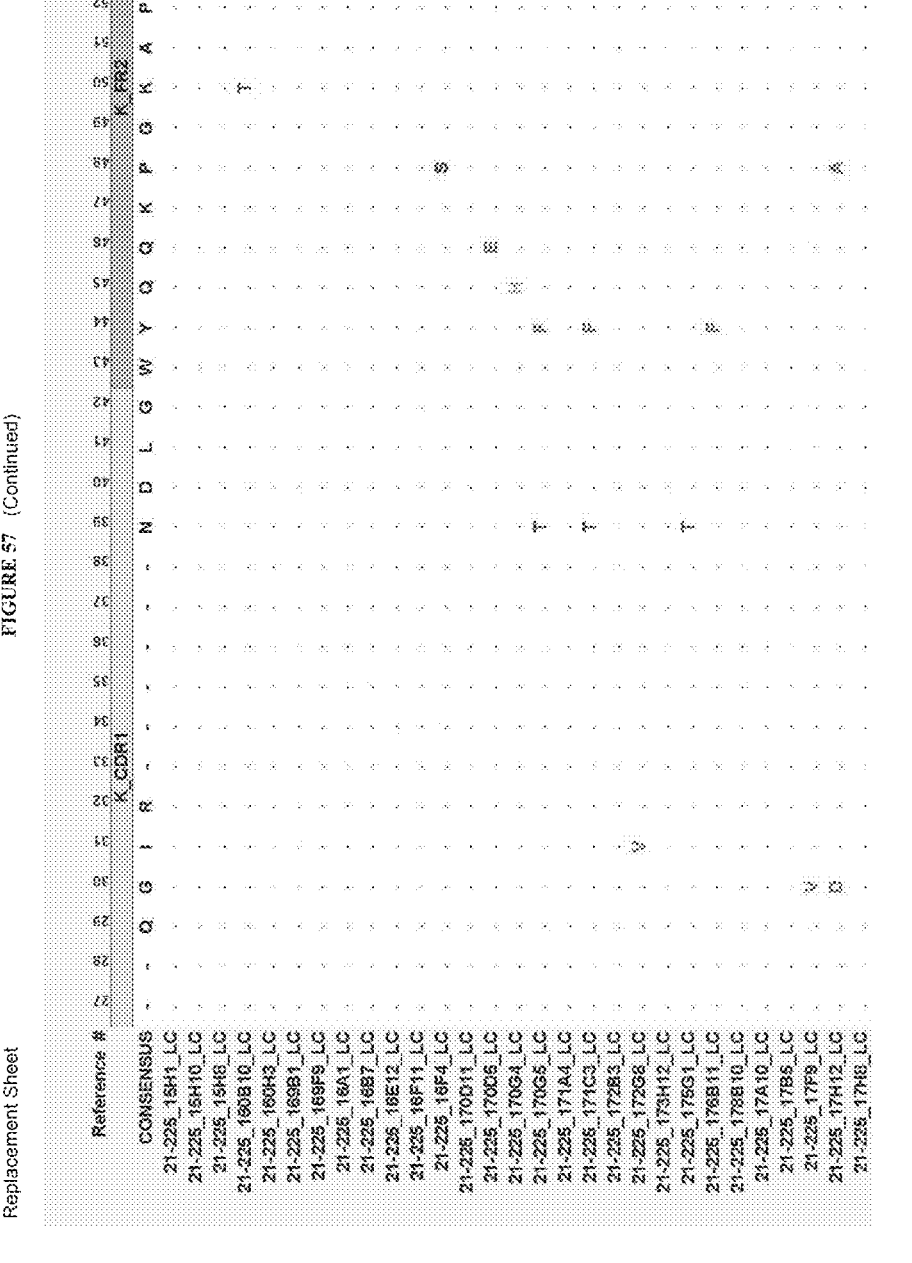
Figure 57:
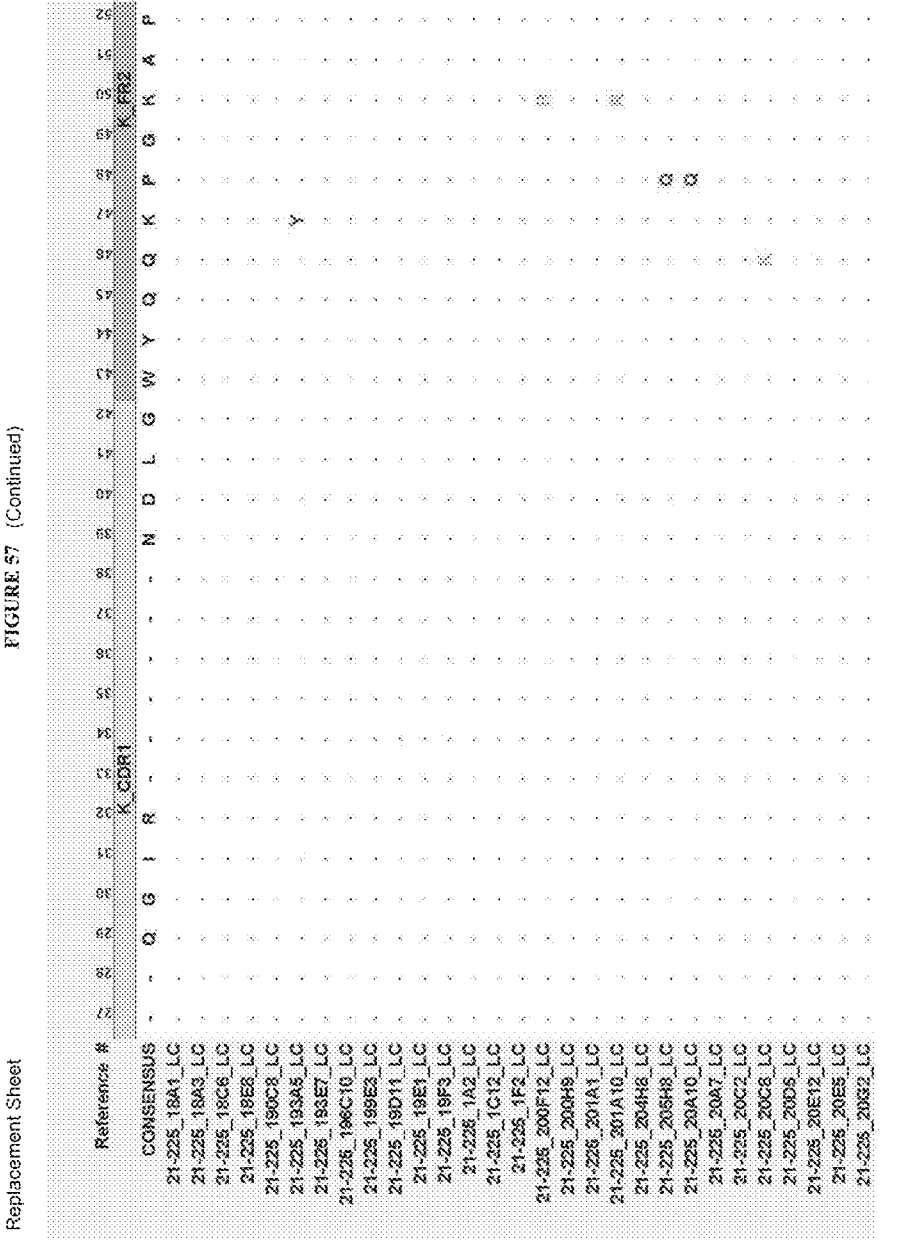
Figure 57:
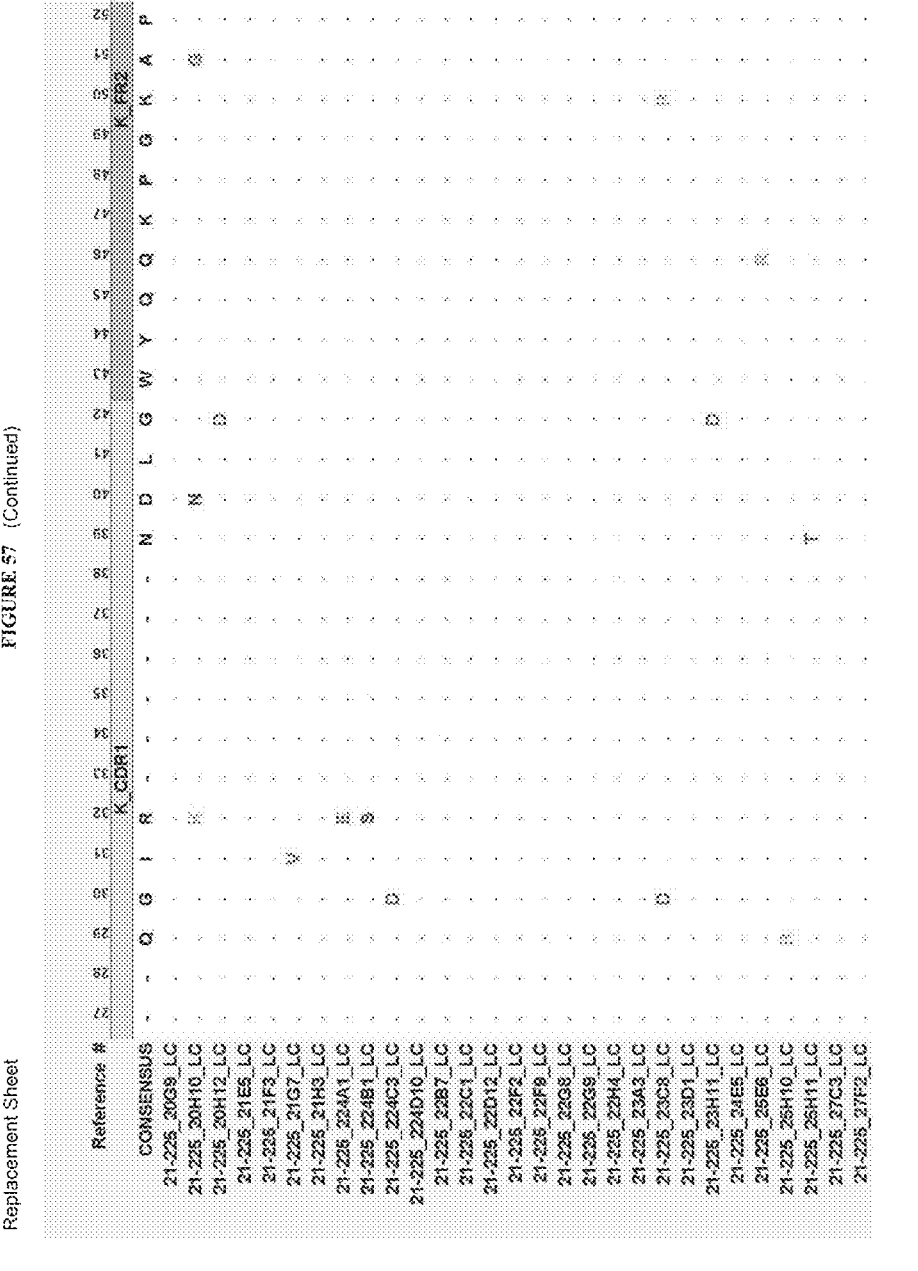
Figure 57:
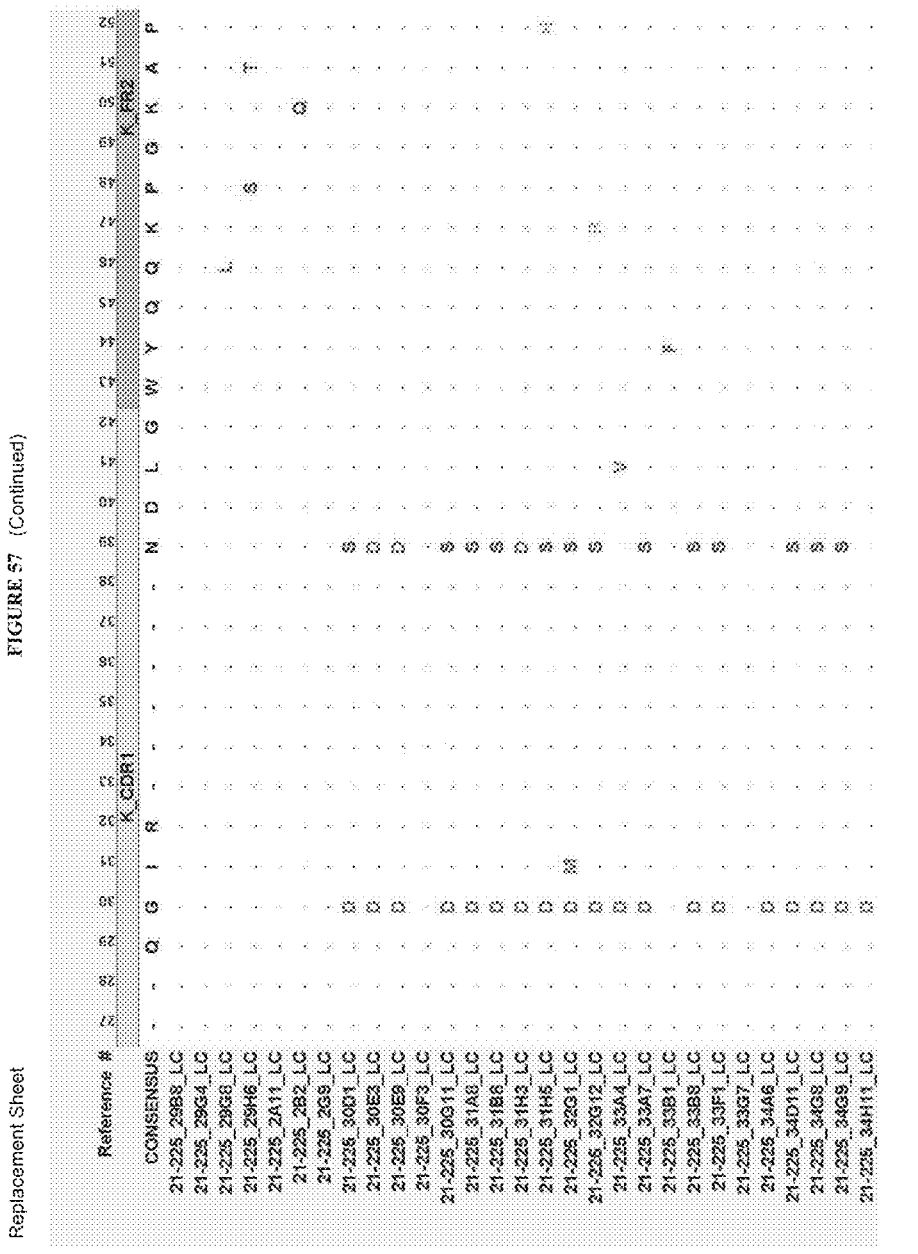
Figure 57:
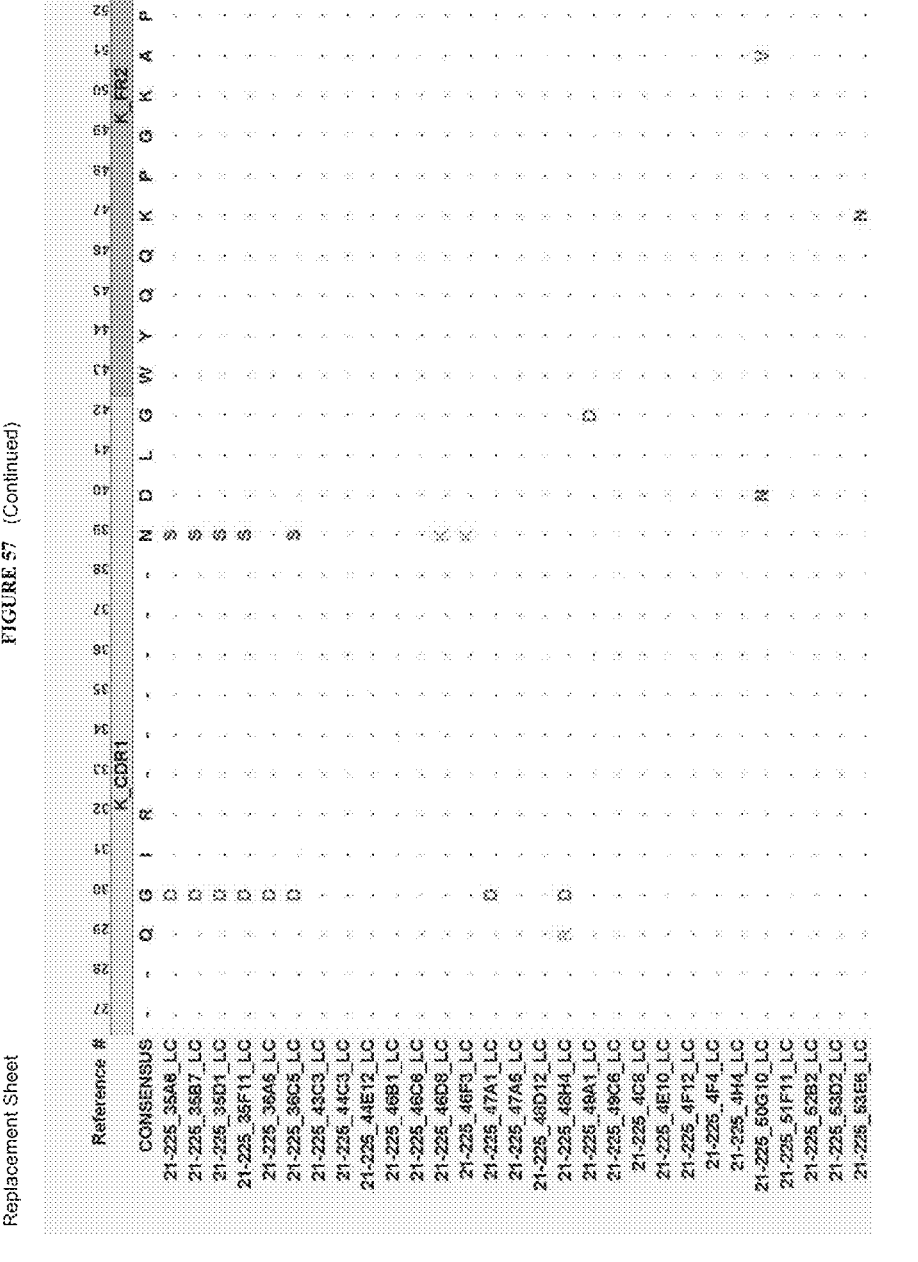
Figure 57:
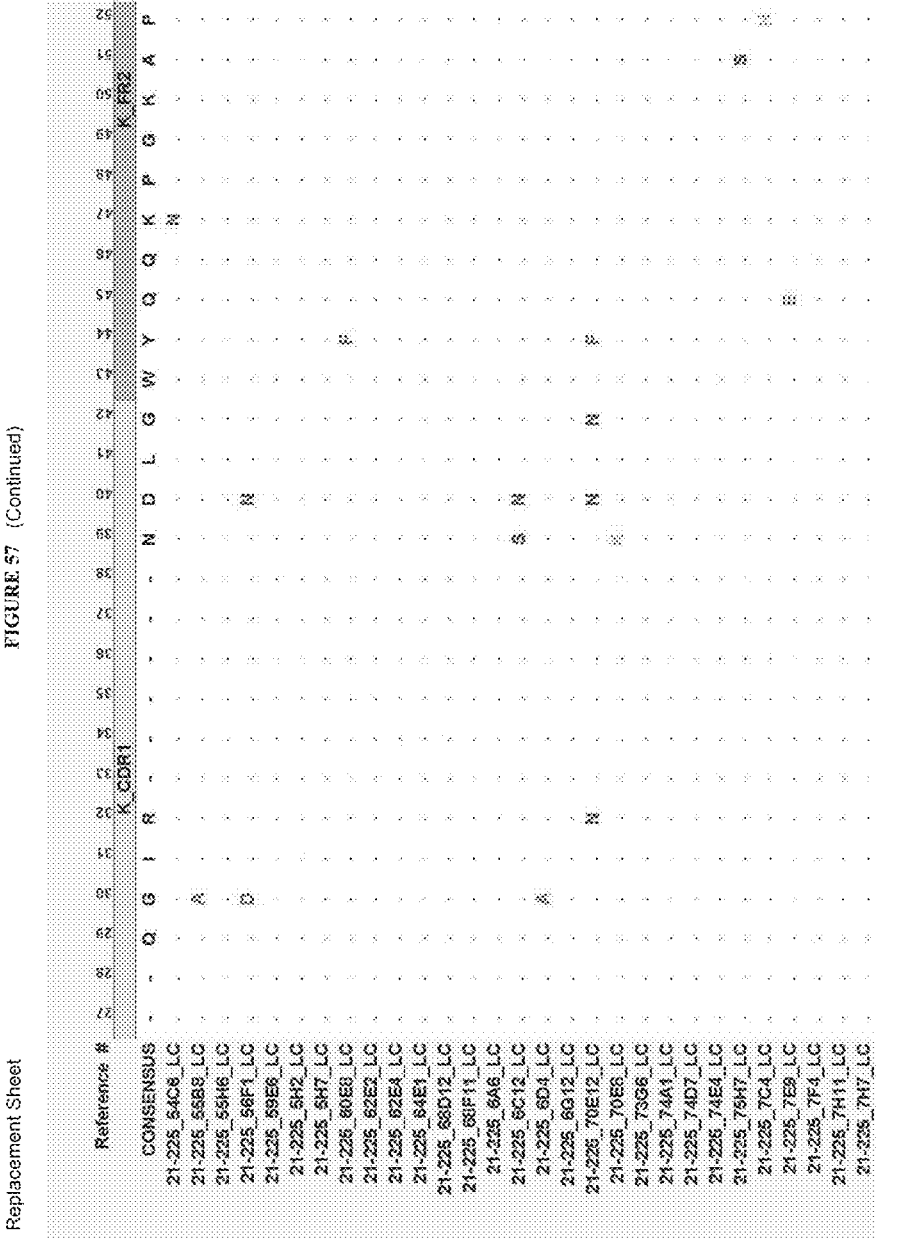
Figure 57:
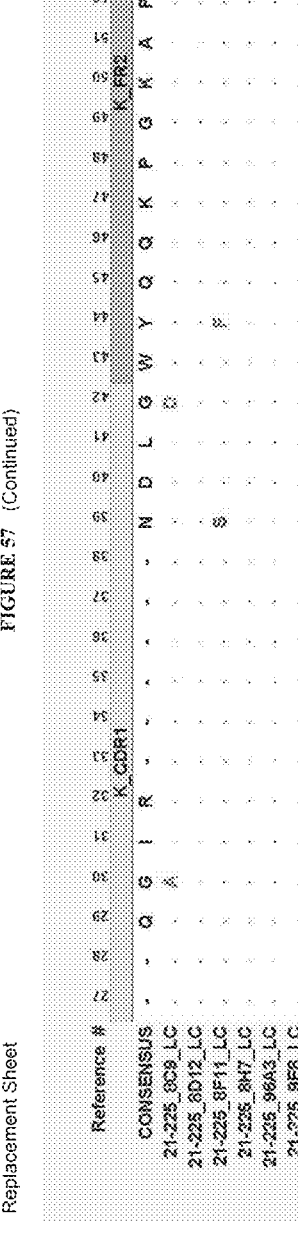
Figure 57:
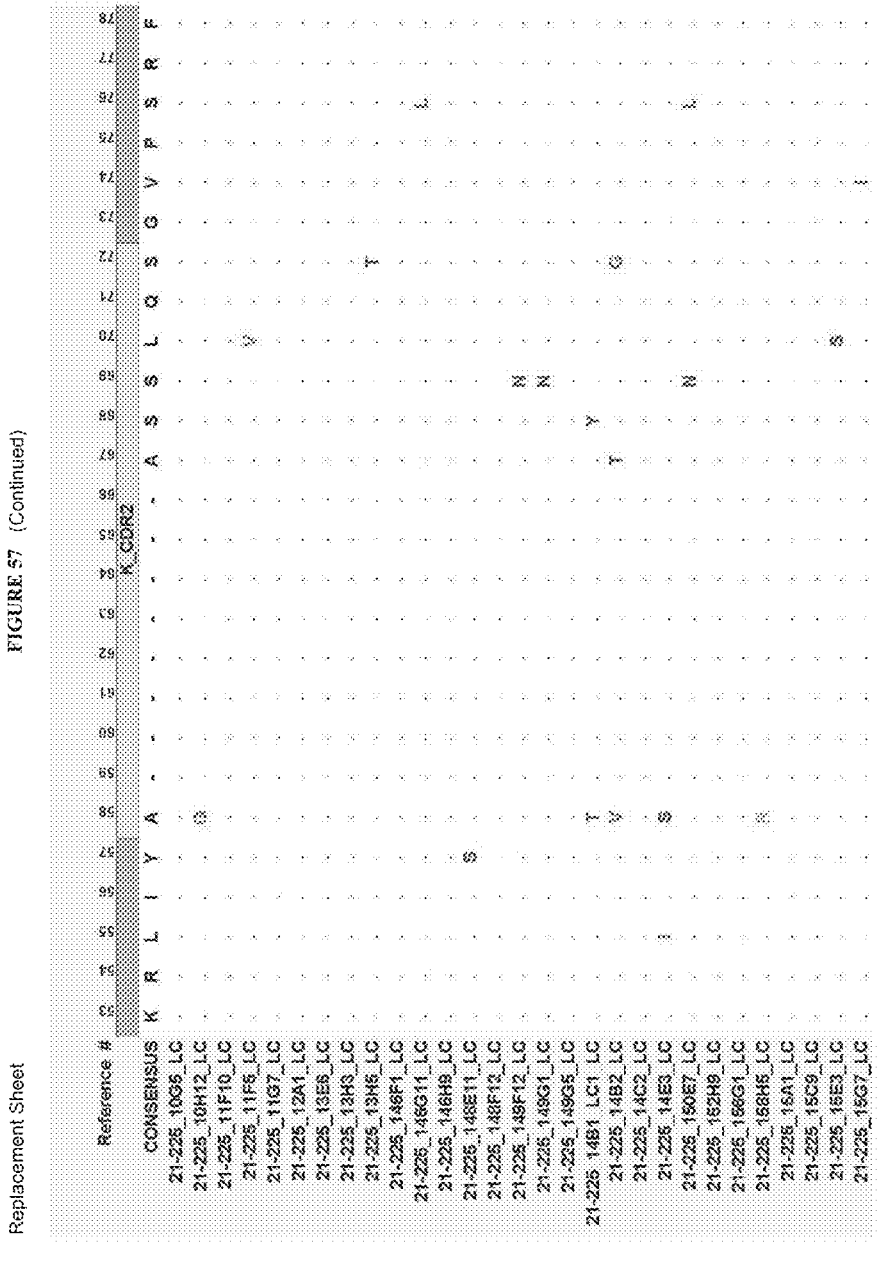
Figure 57:
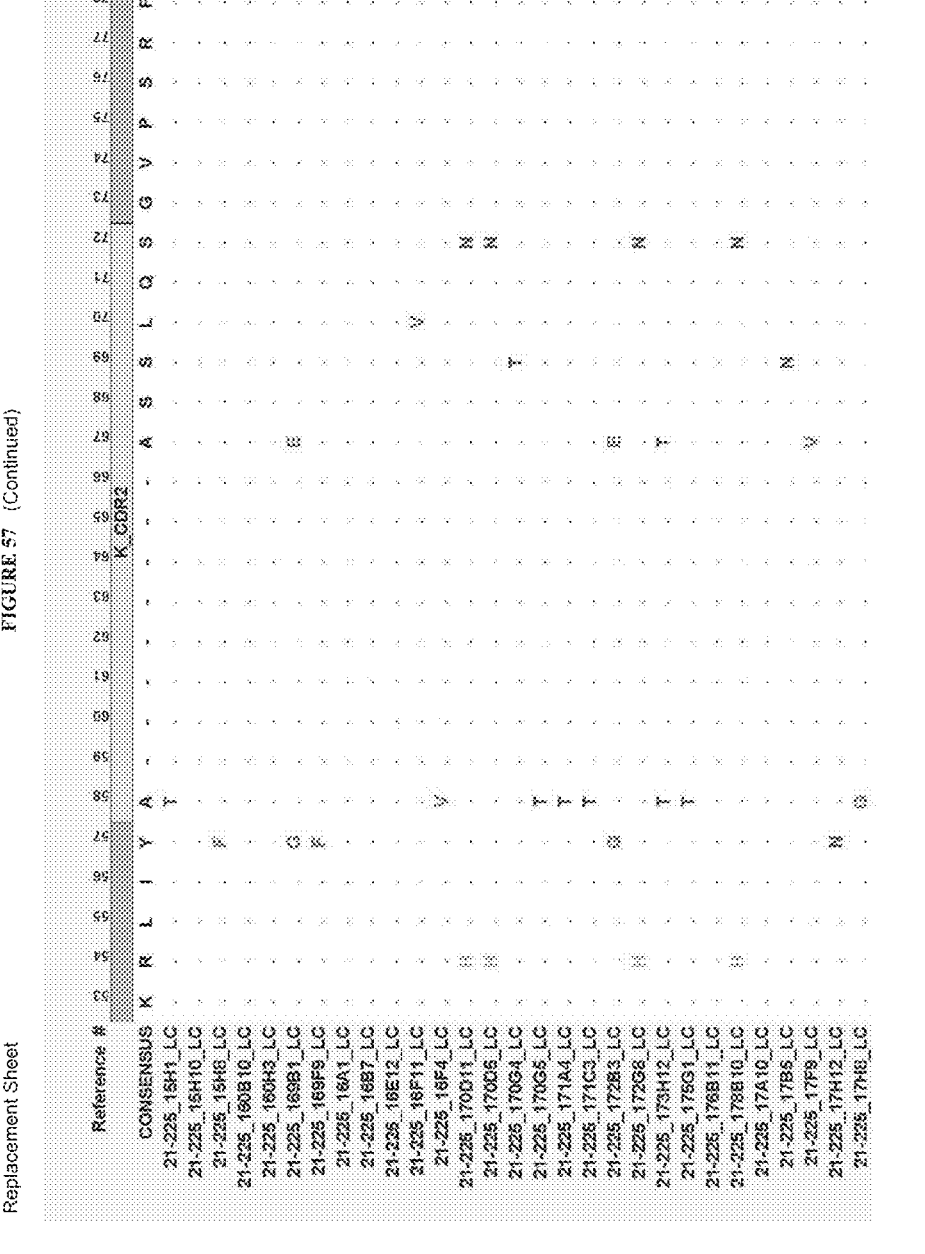
Figure 57:
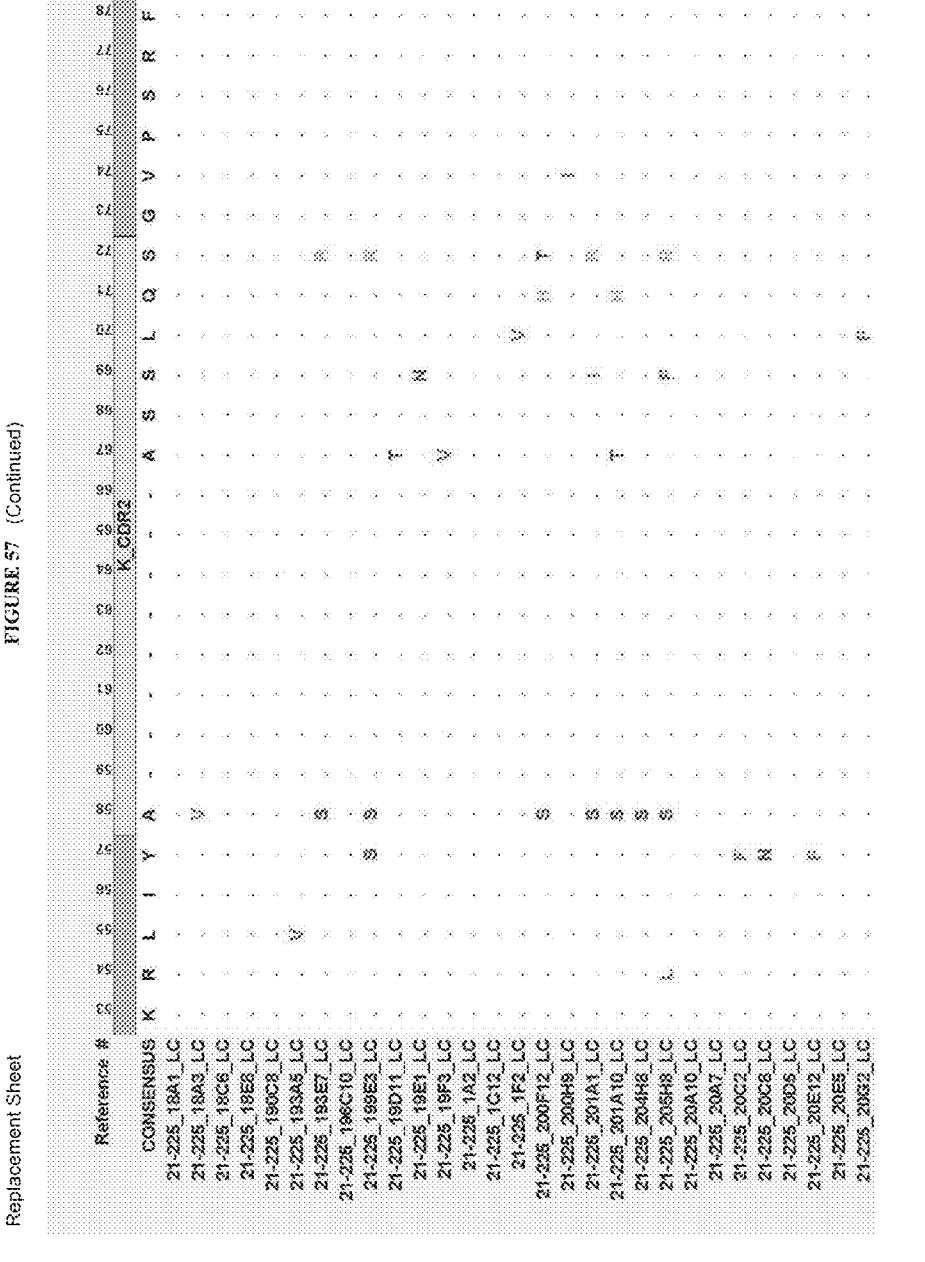
Figure 57:
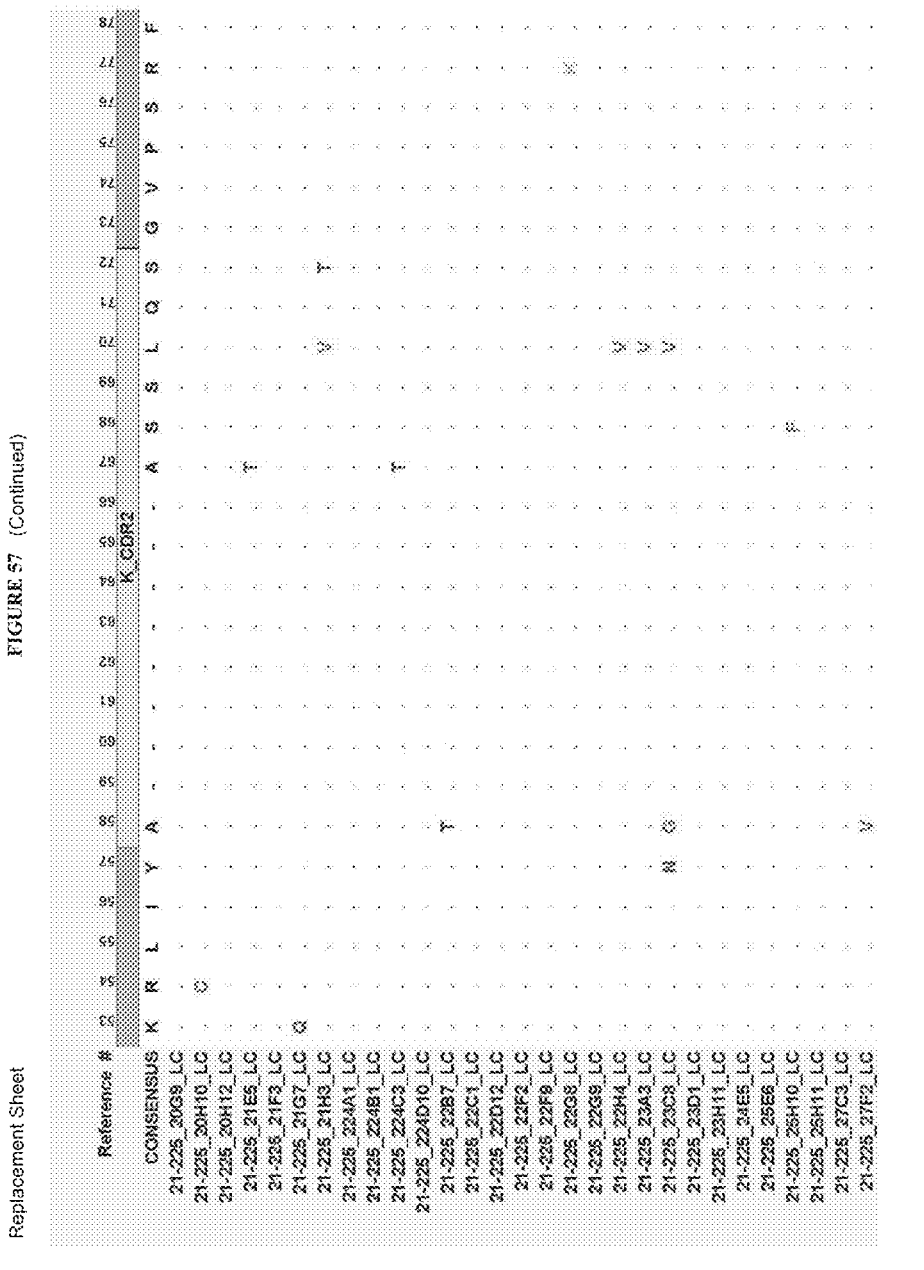
Figure 57:
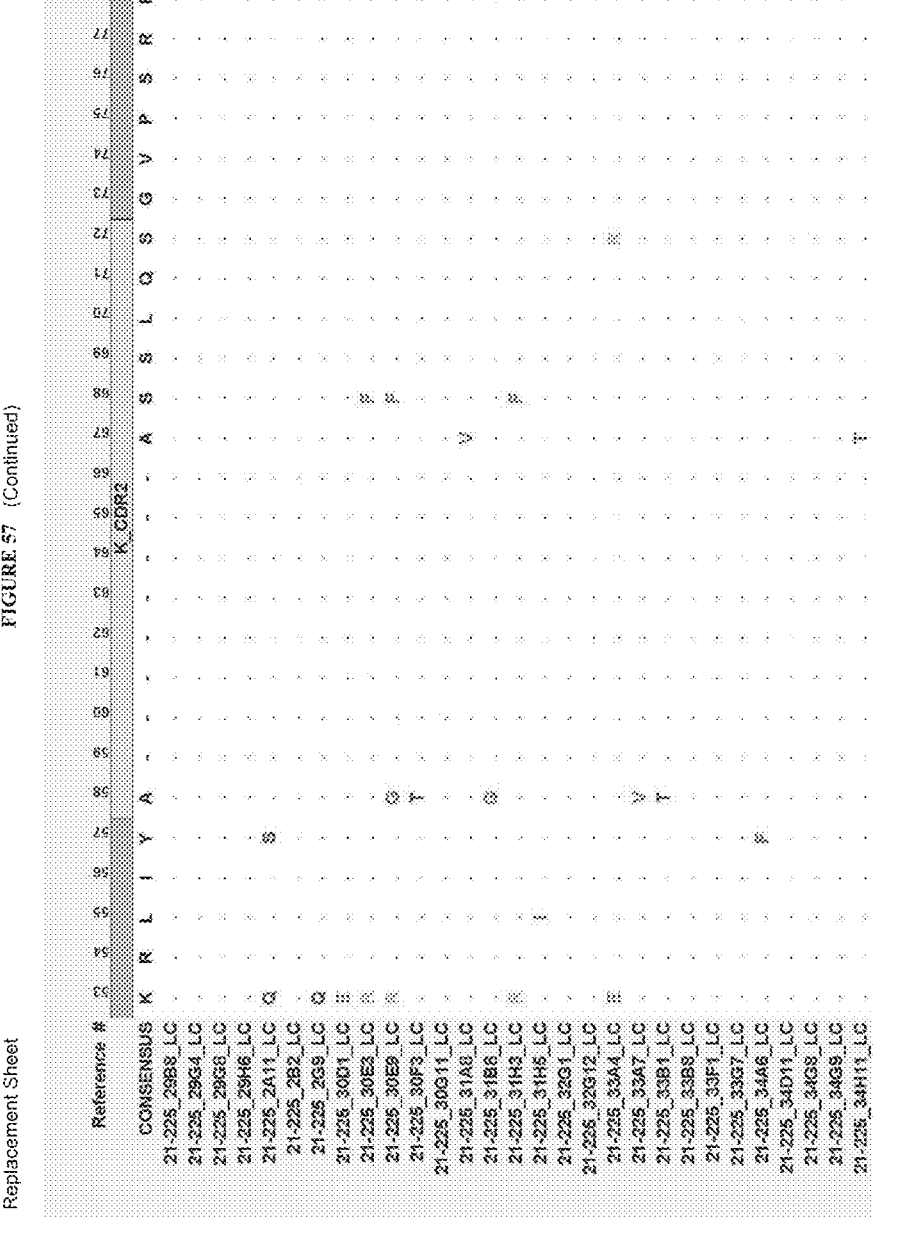
Figure 57:
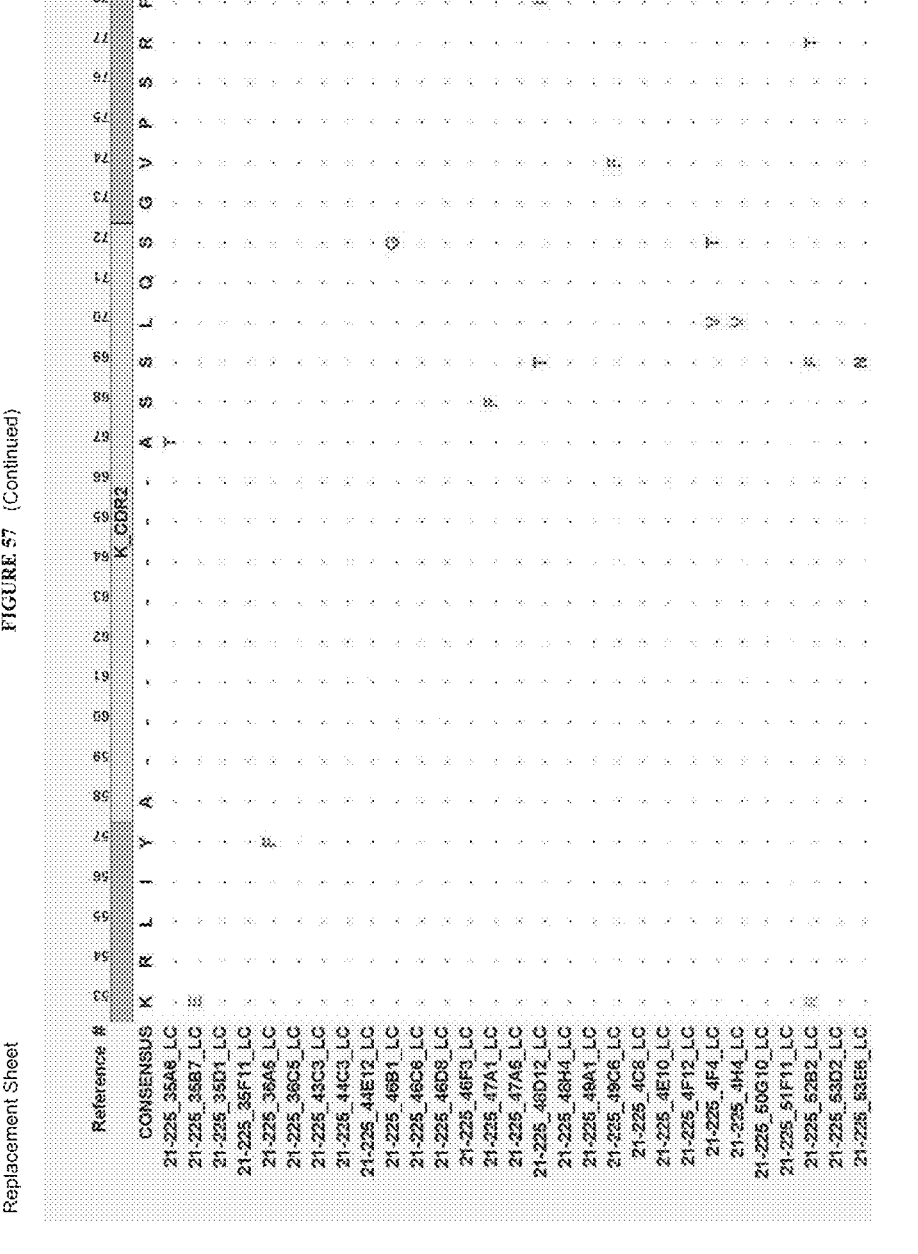
Figure 57:
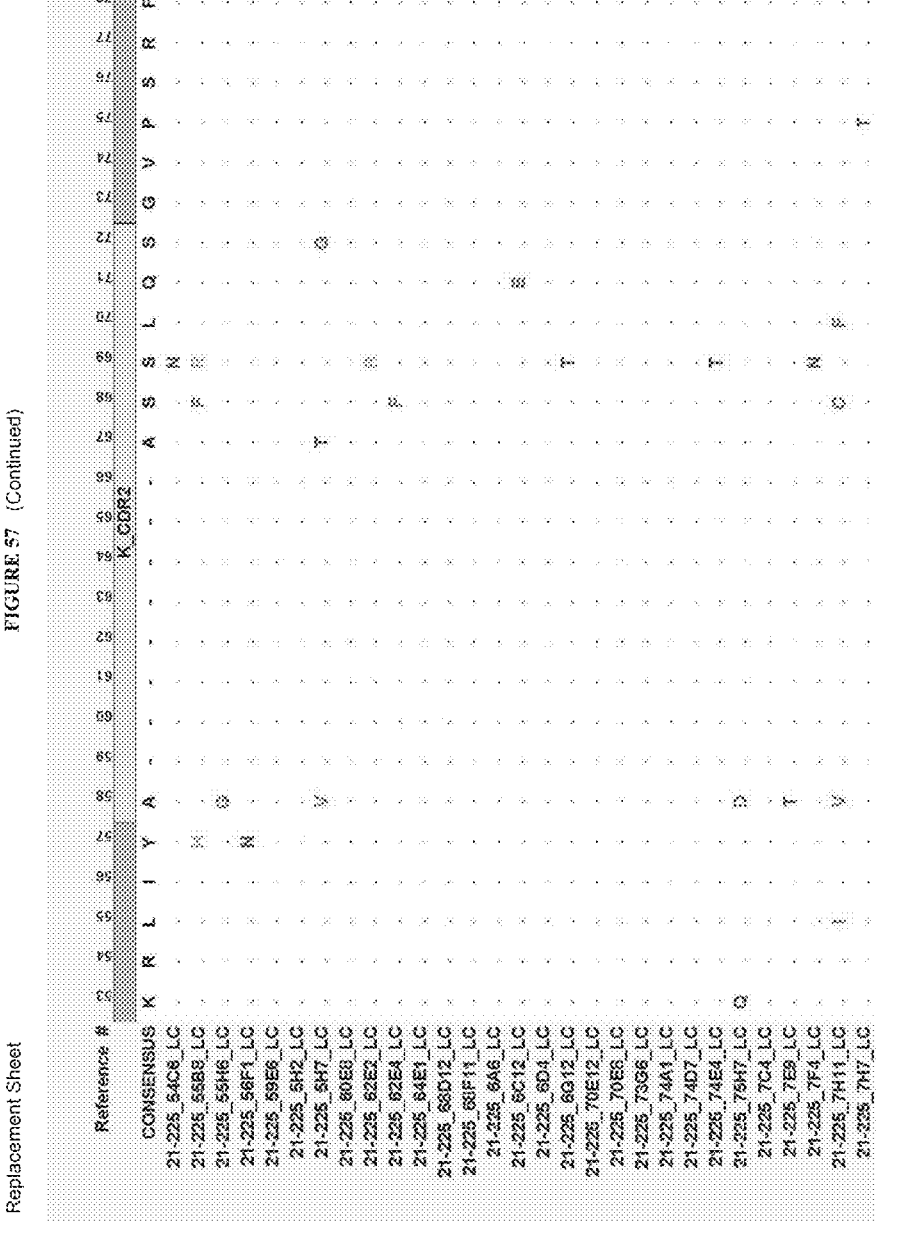
Figure 57:
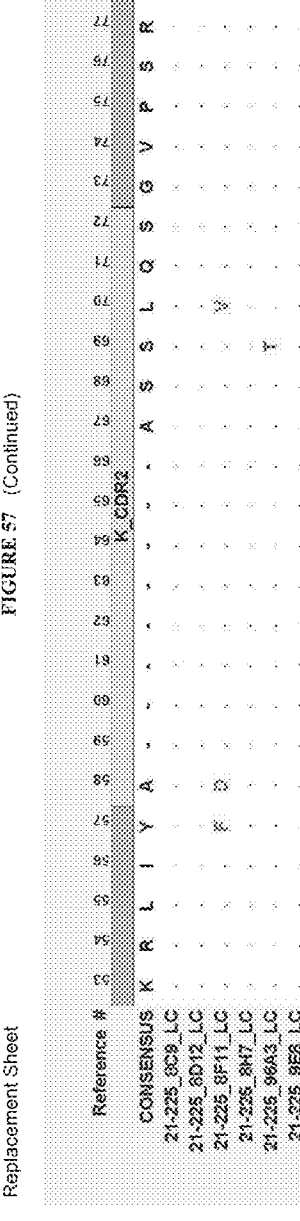
Figure 57:
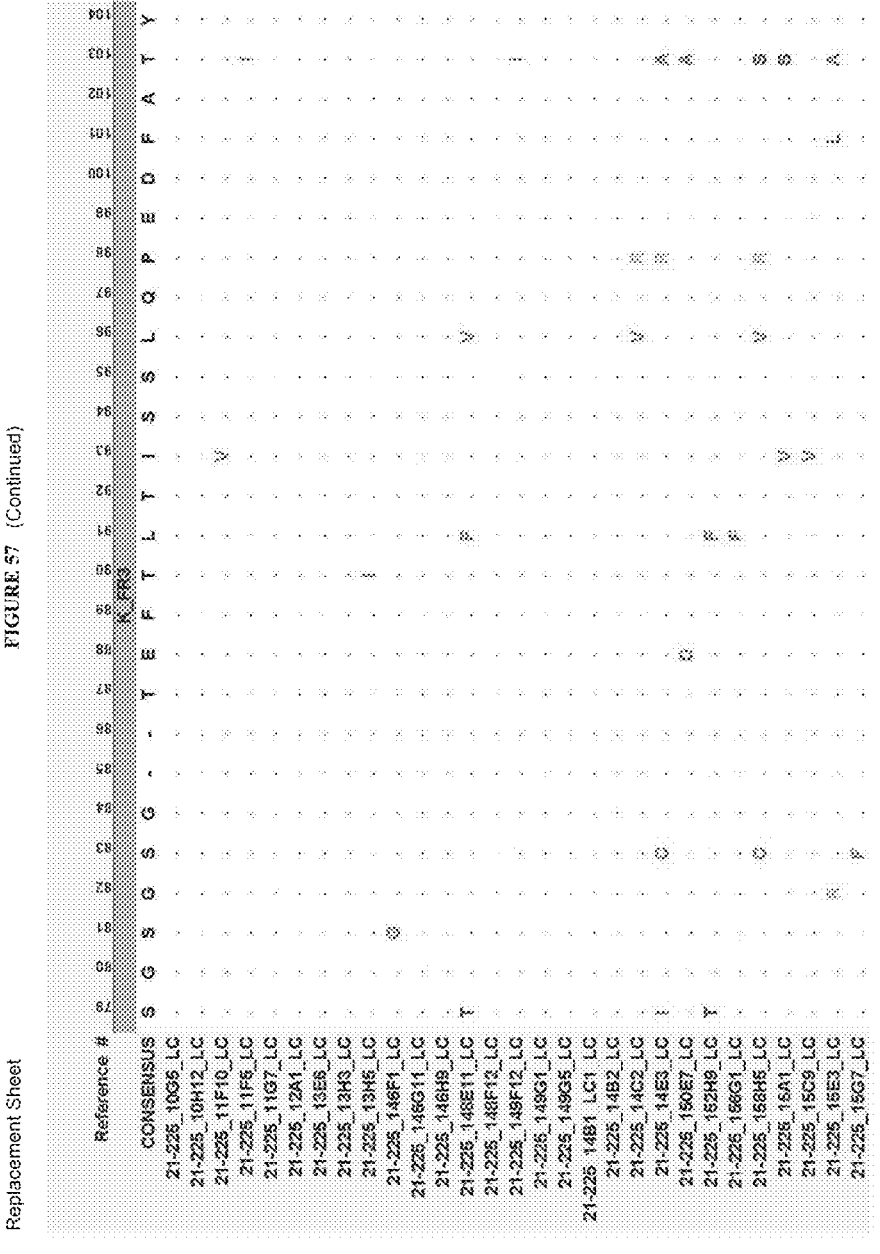
Figure 57:
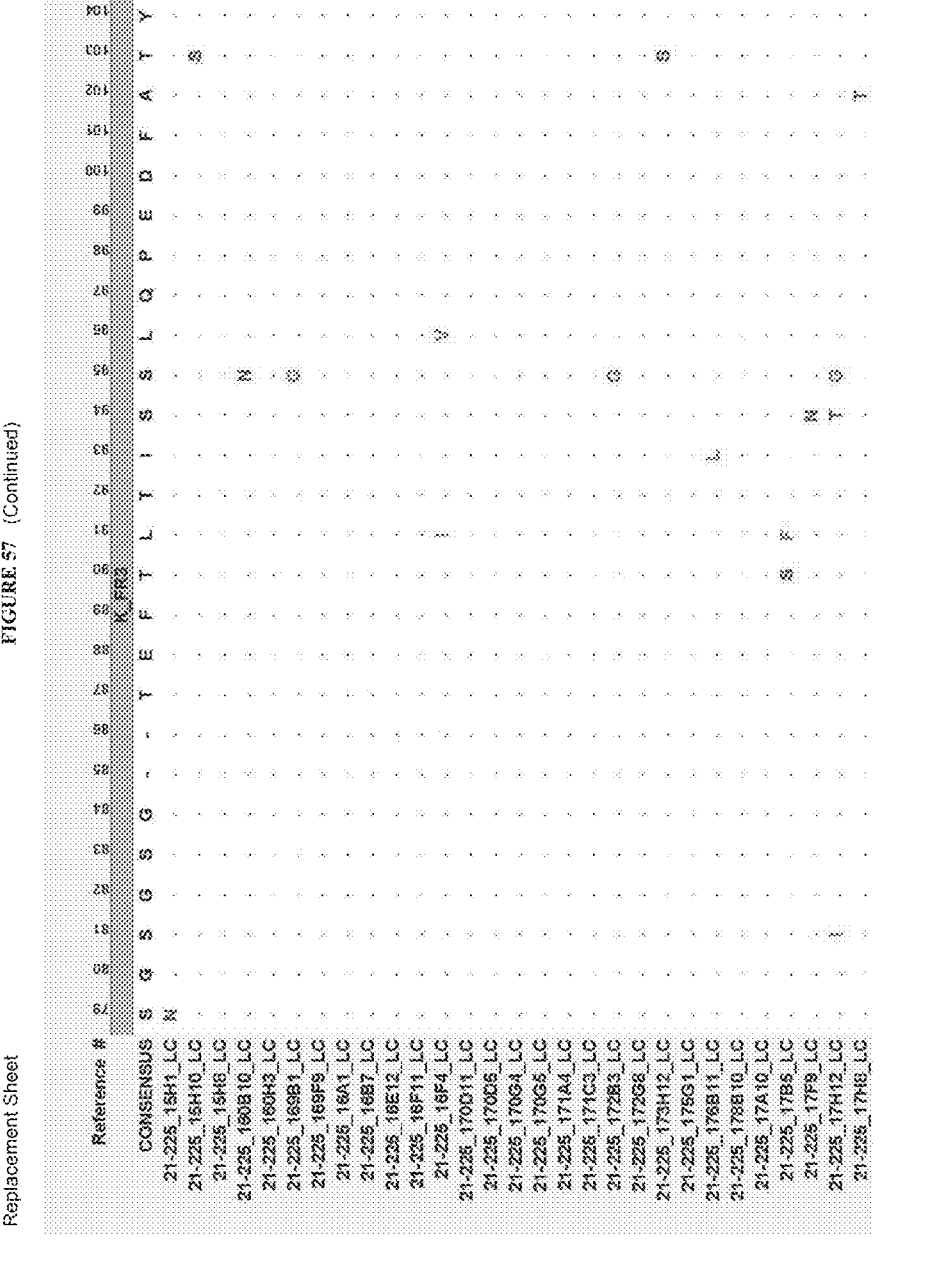
Figure 57:
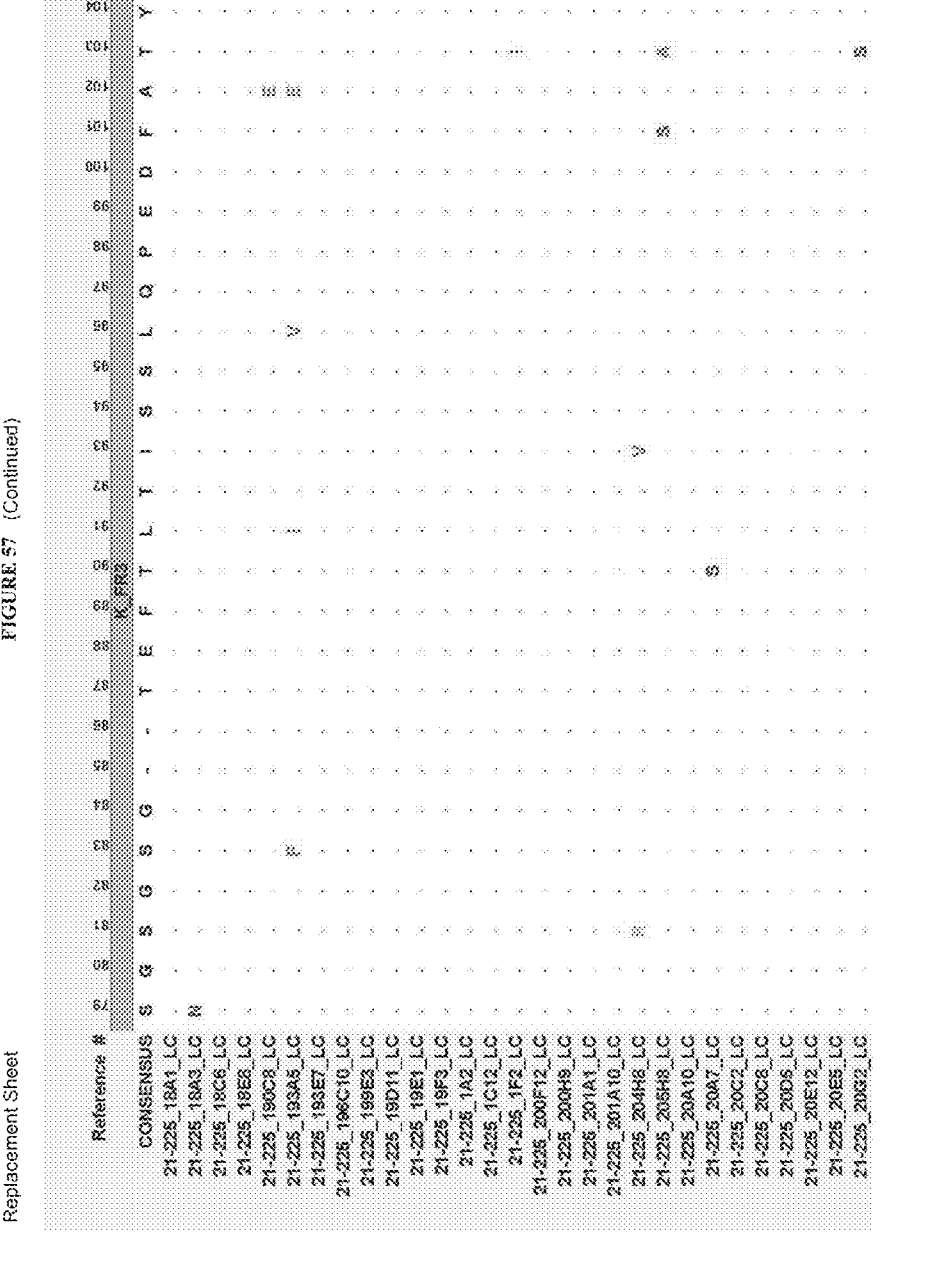
Figure 57:
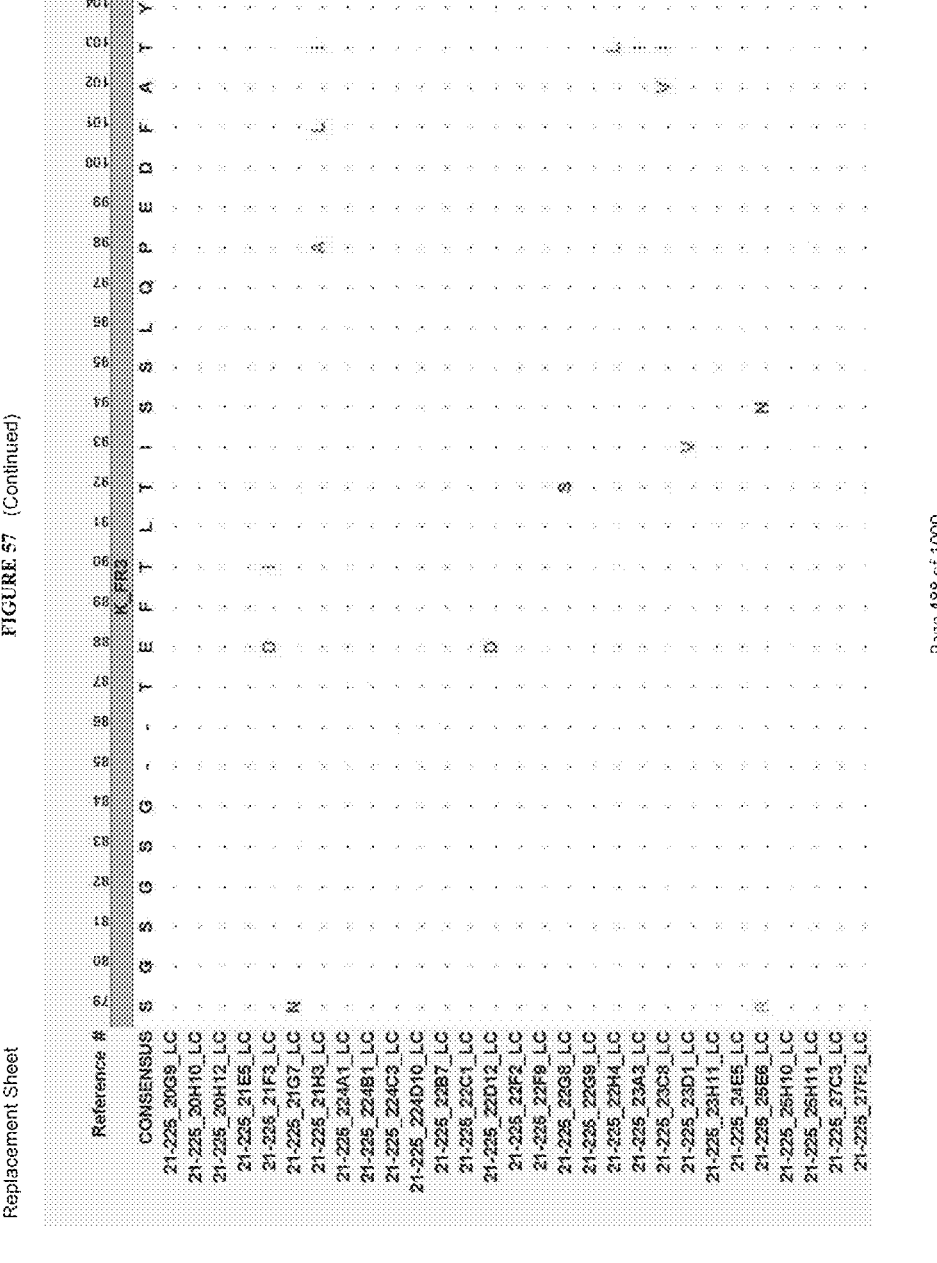
Figure 57:
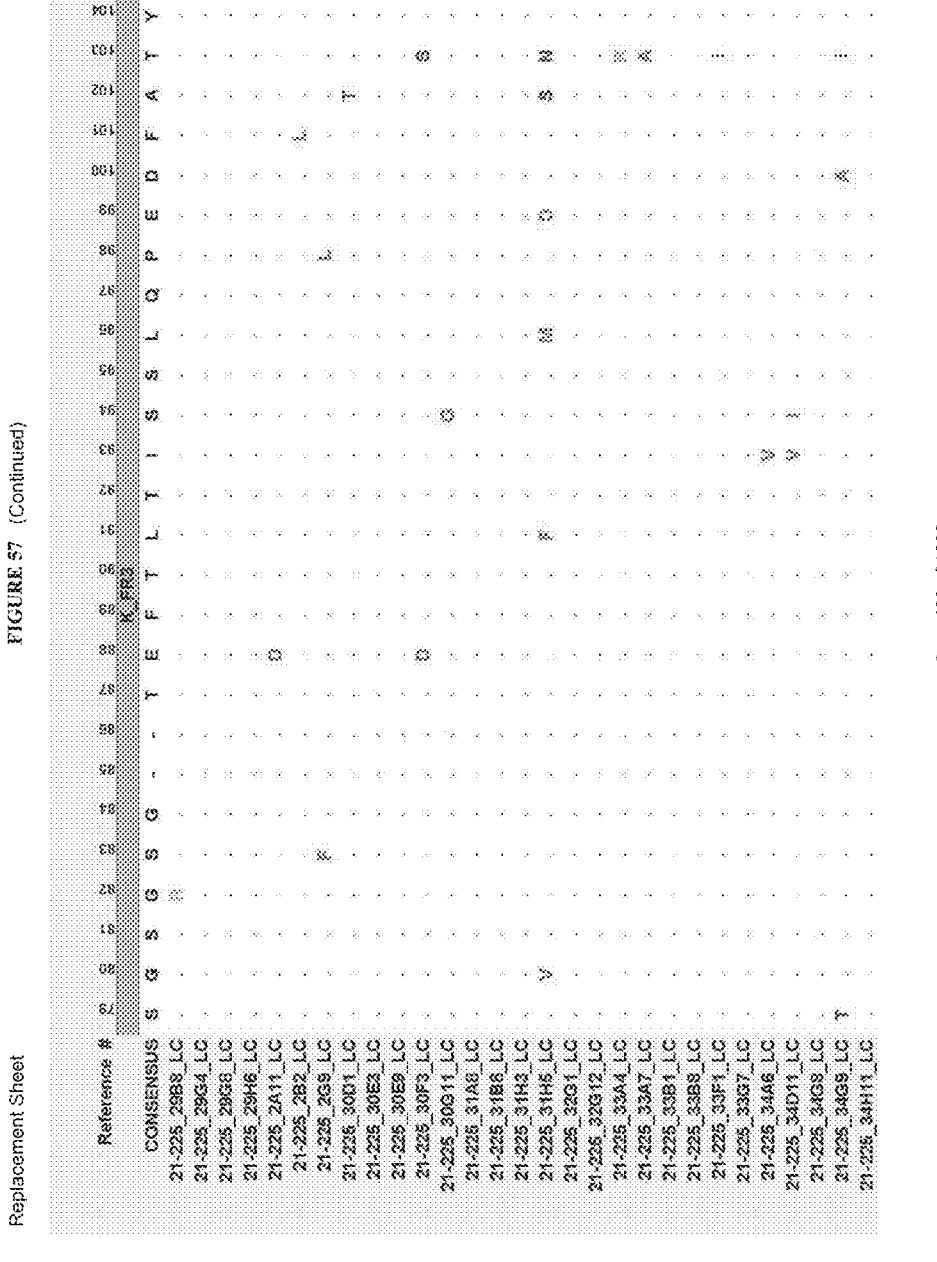
Figure 57:
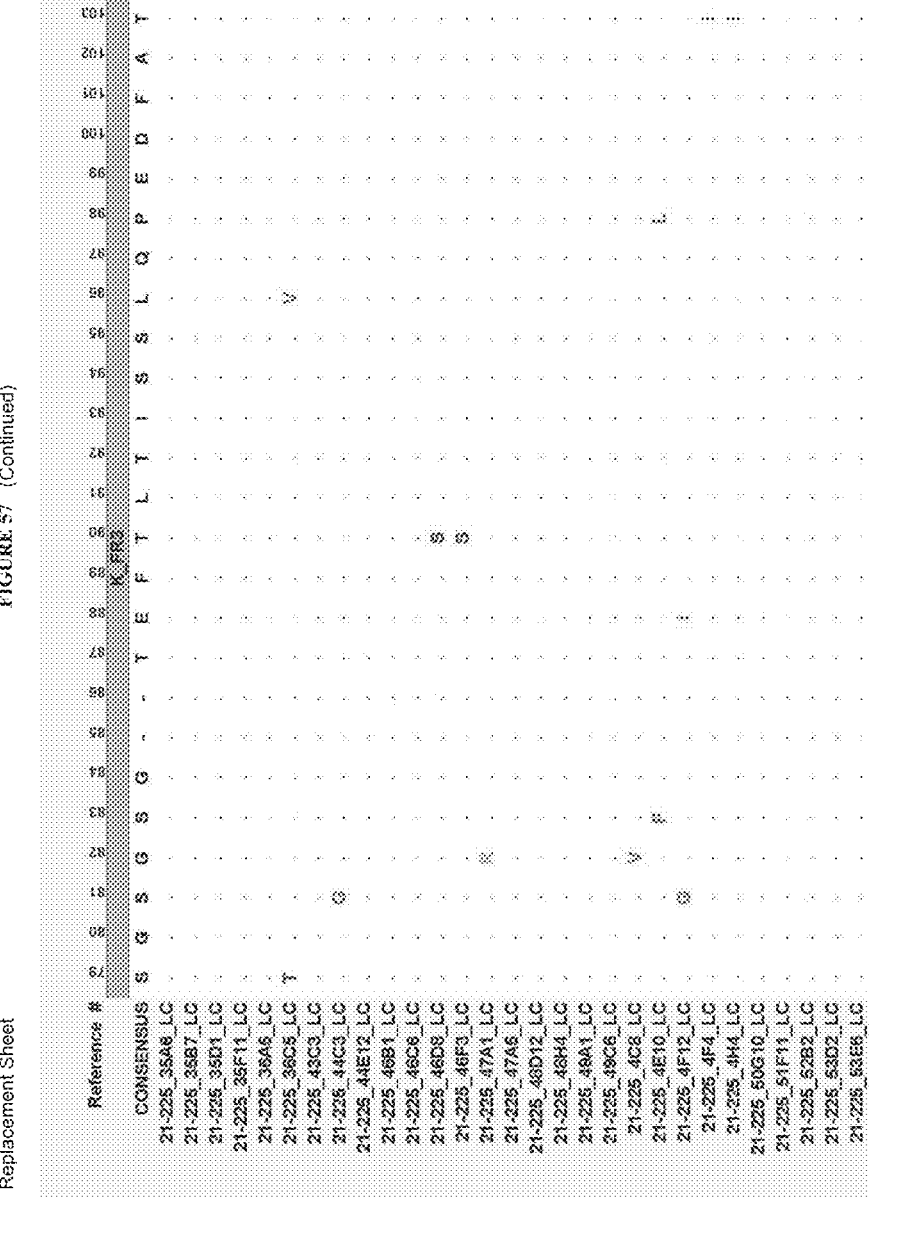
Figure 57:
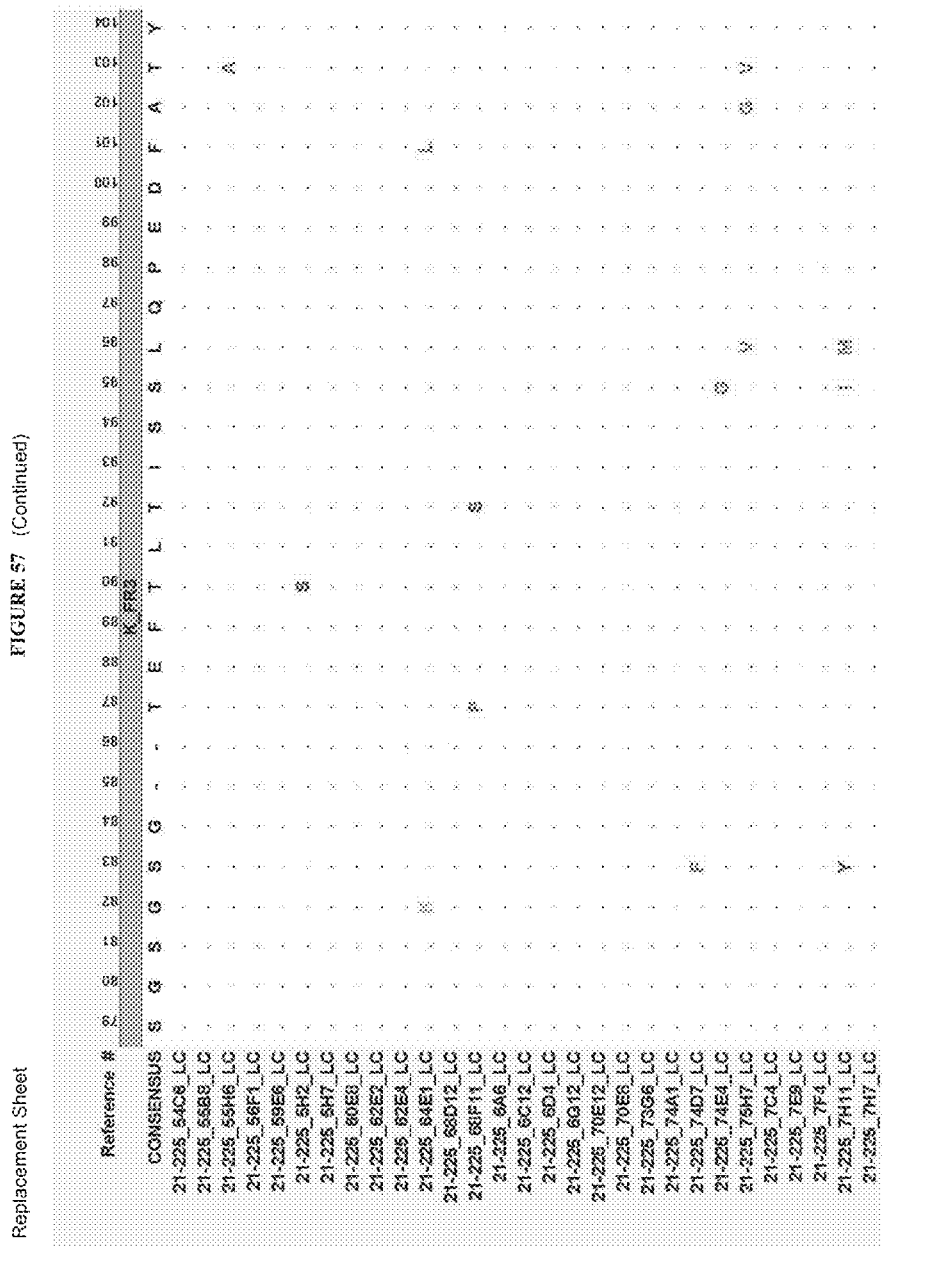
Figure 57:
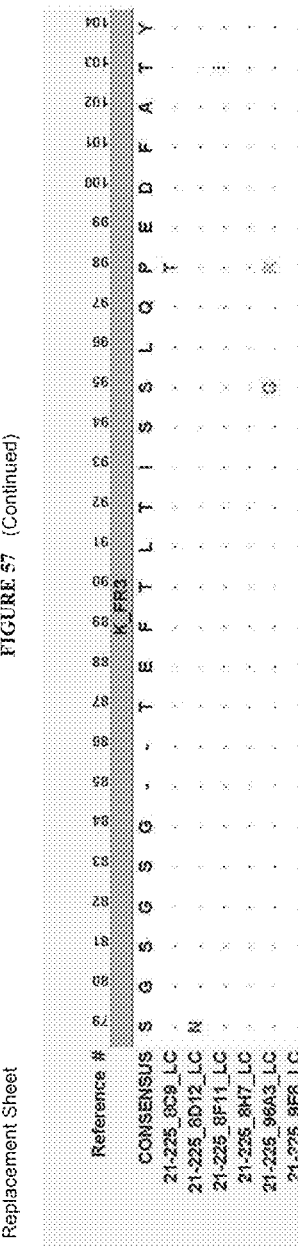
Figure 57:
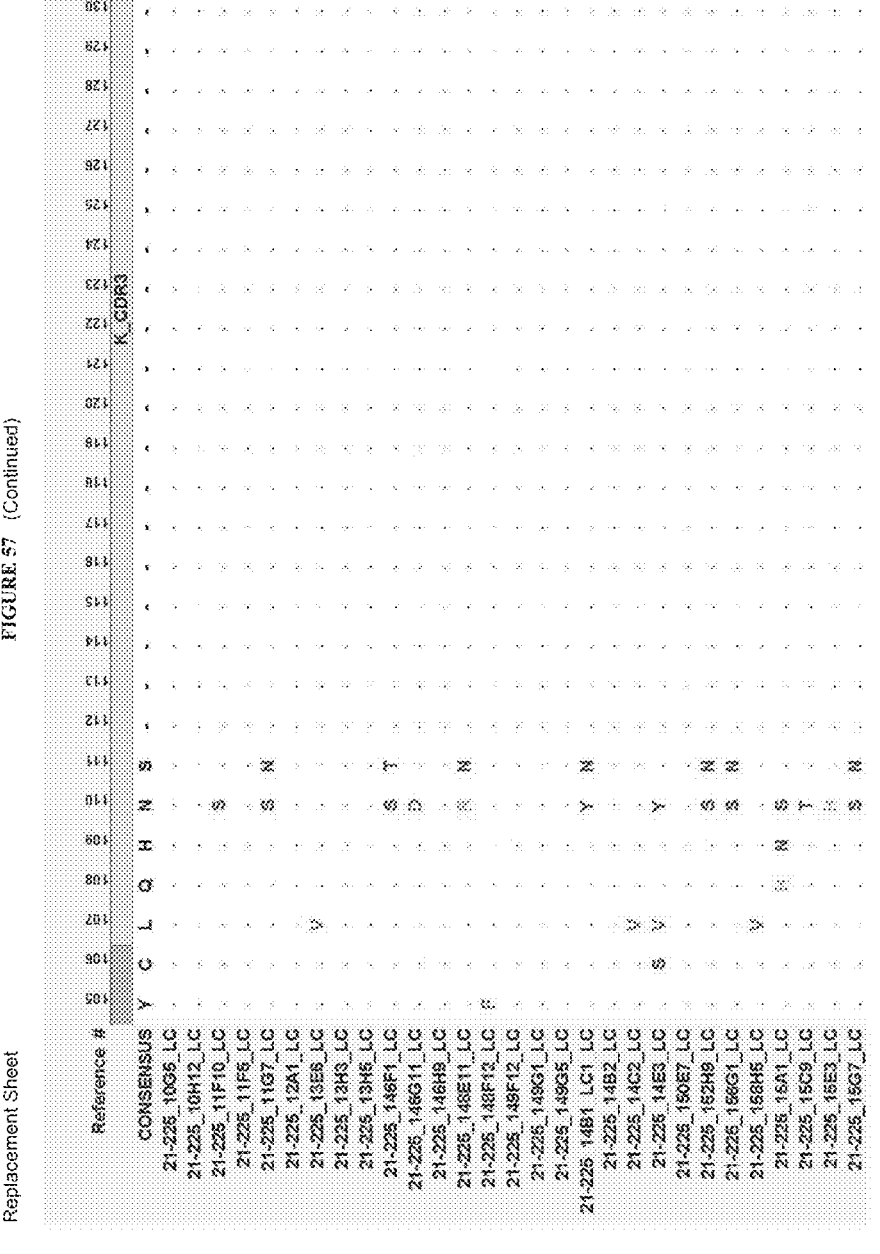
Figure 57:
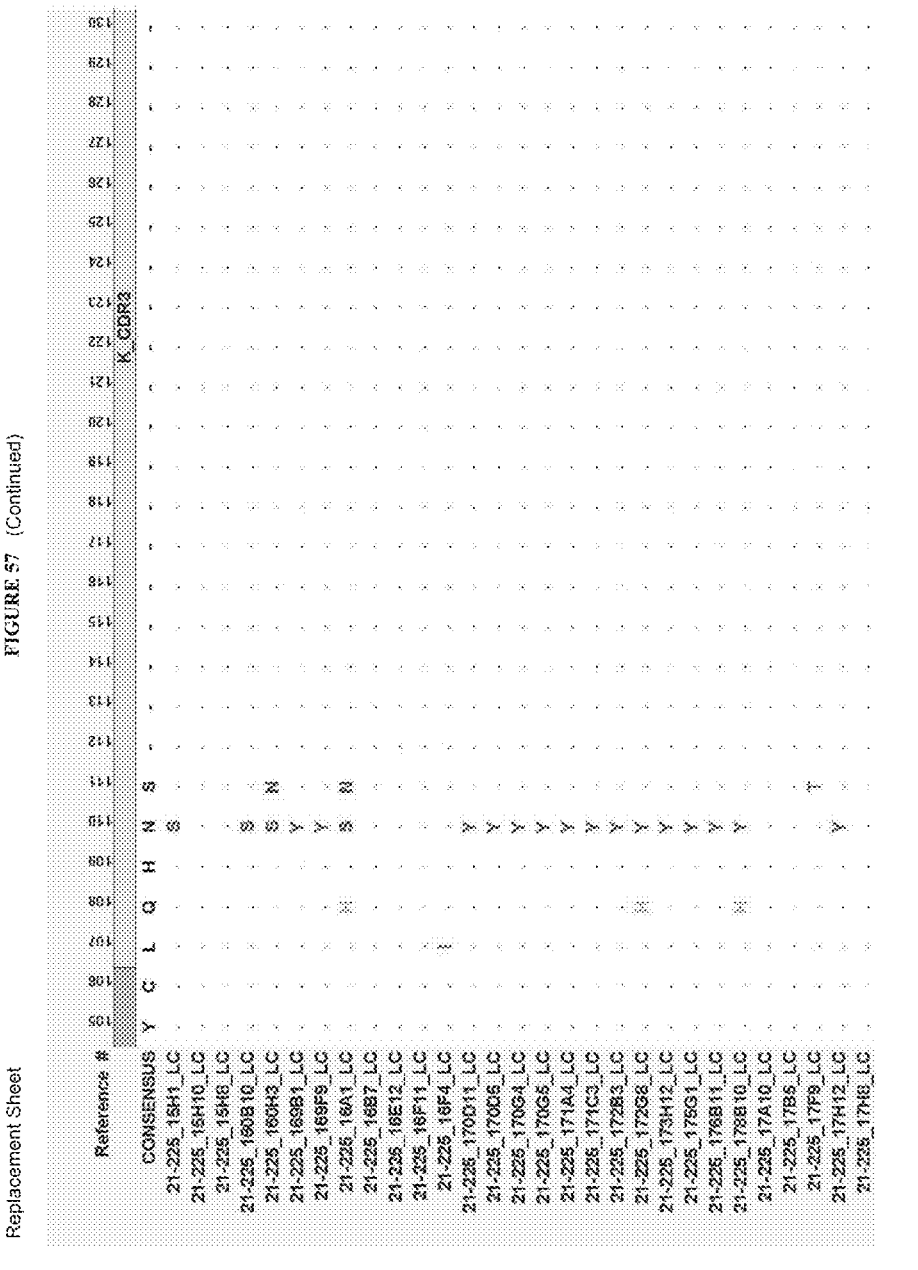
Figure 57:
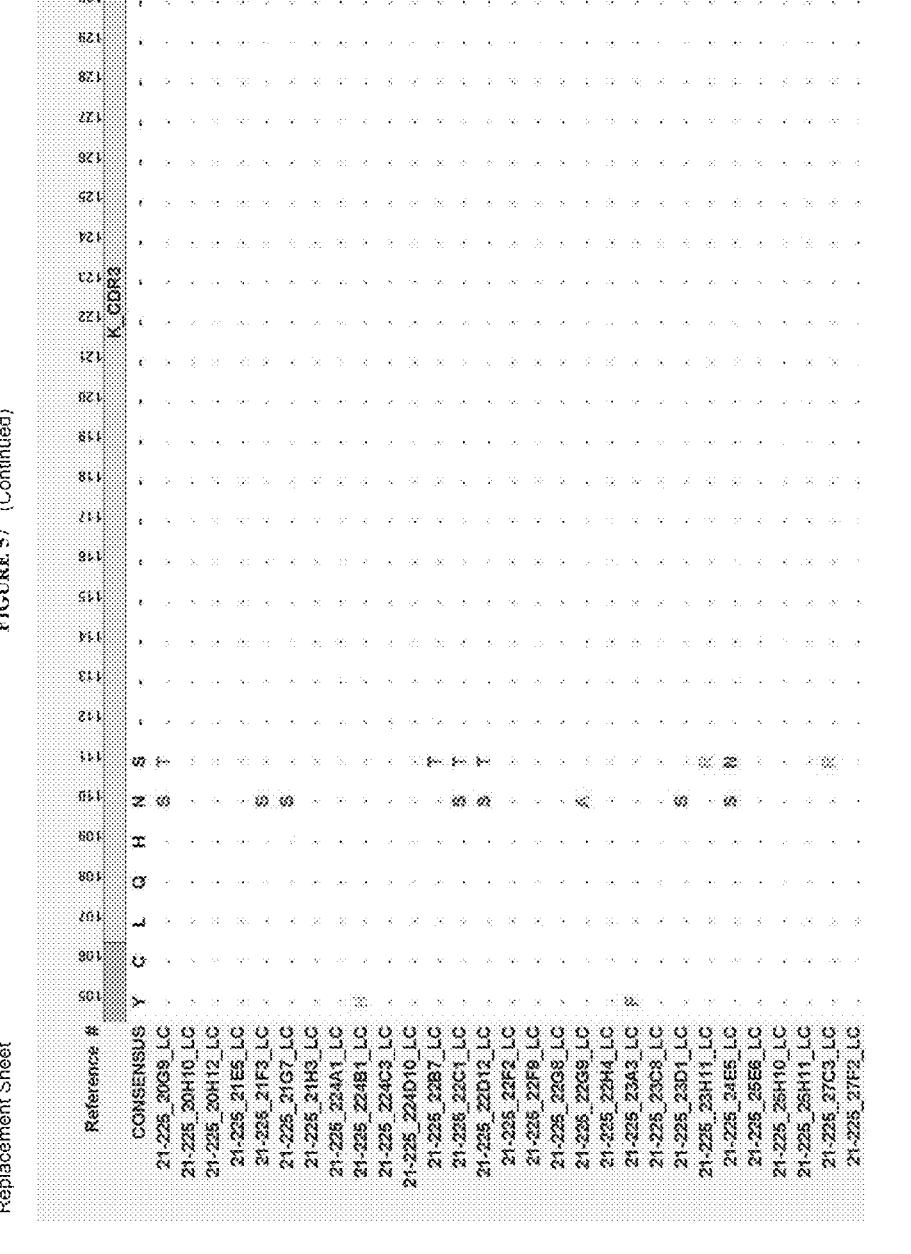
Figure 57:
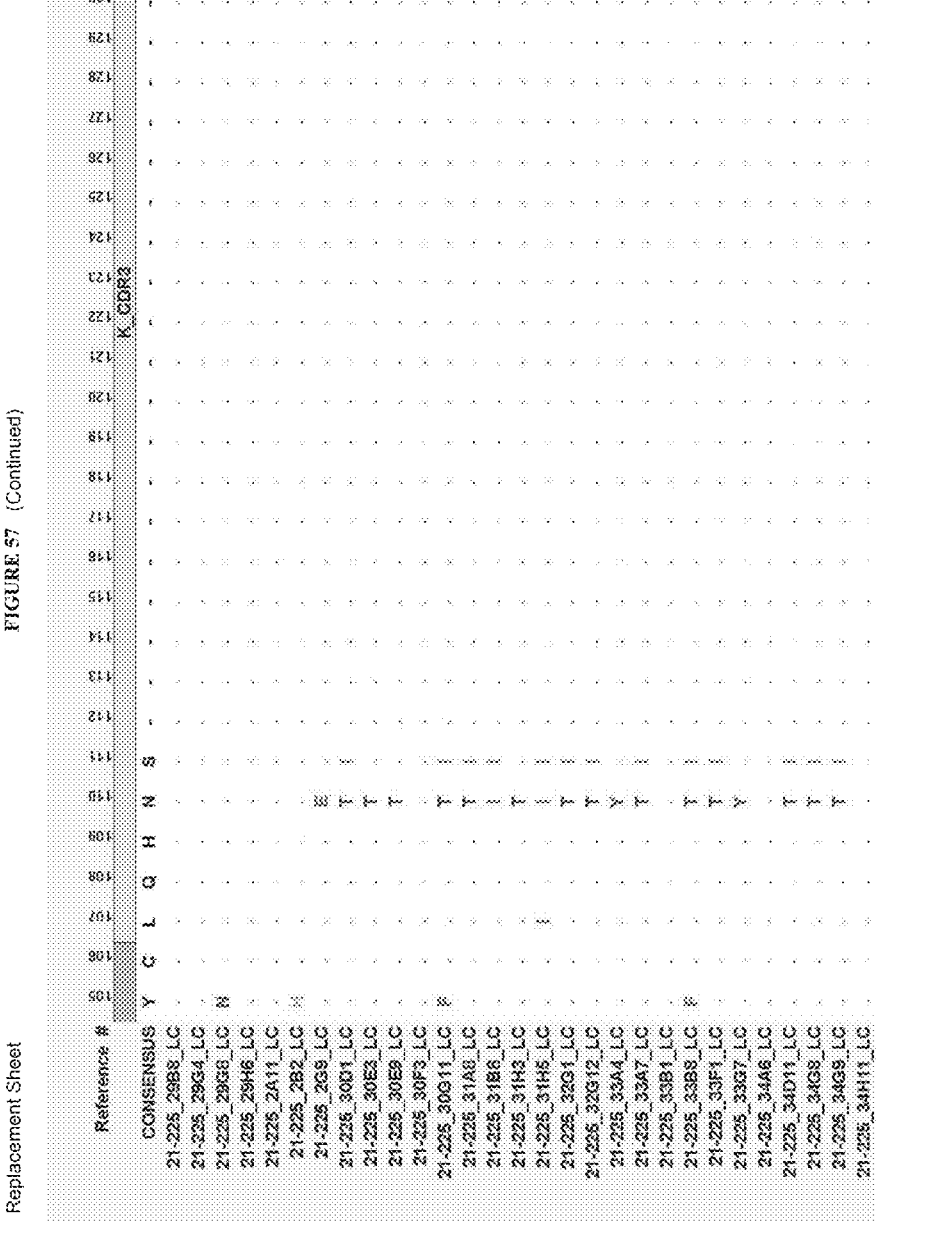
Figure 57:
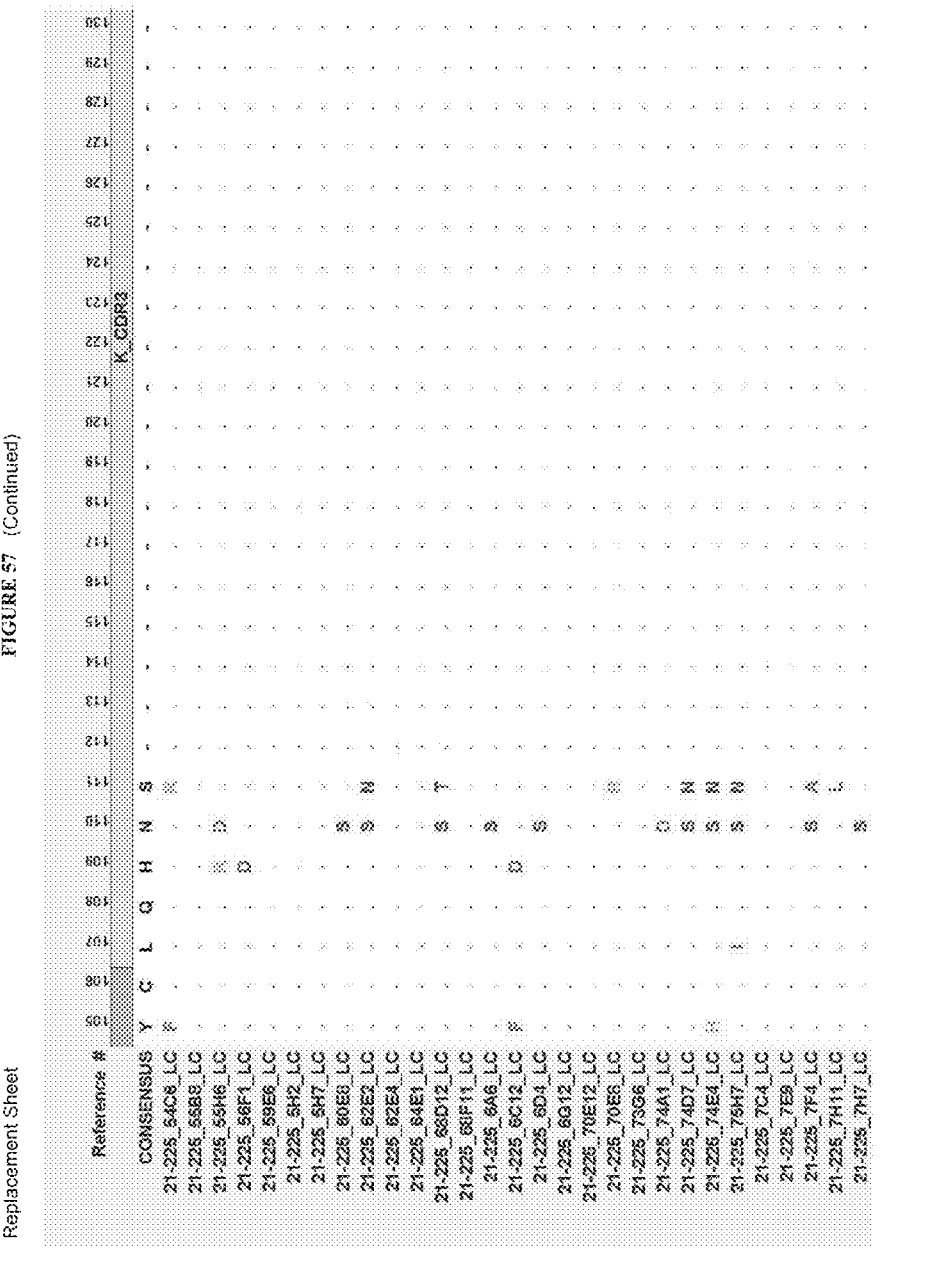
Figure 57:
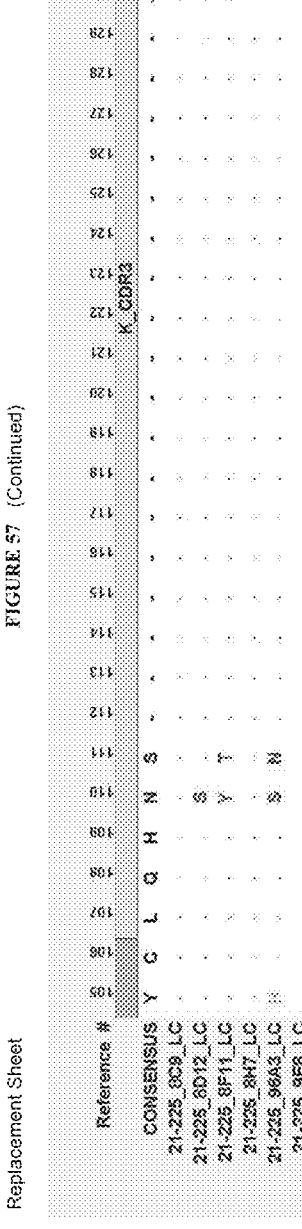
Figure 57:
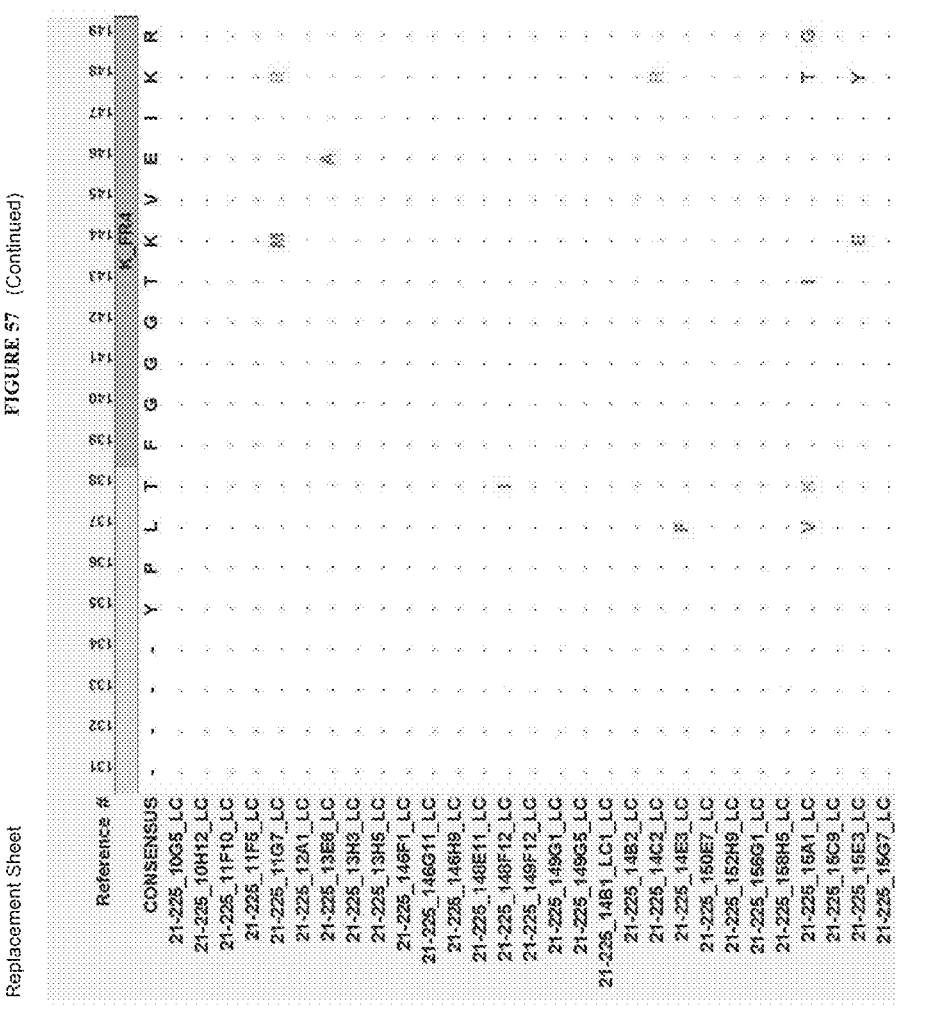
Figure 57:
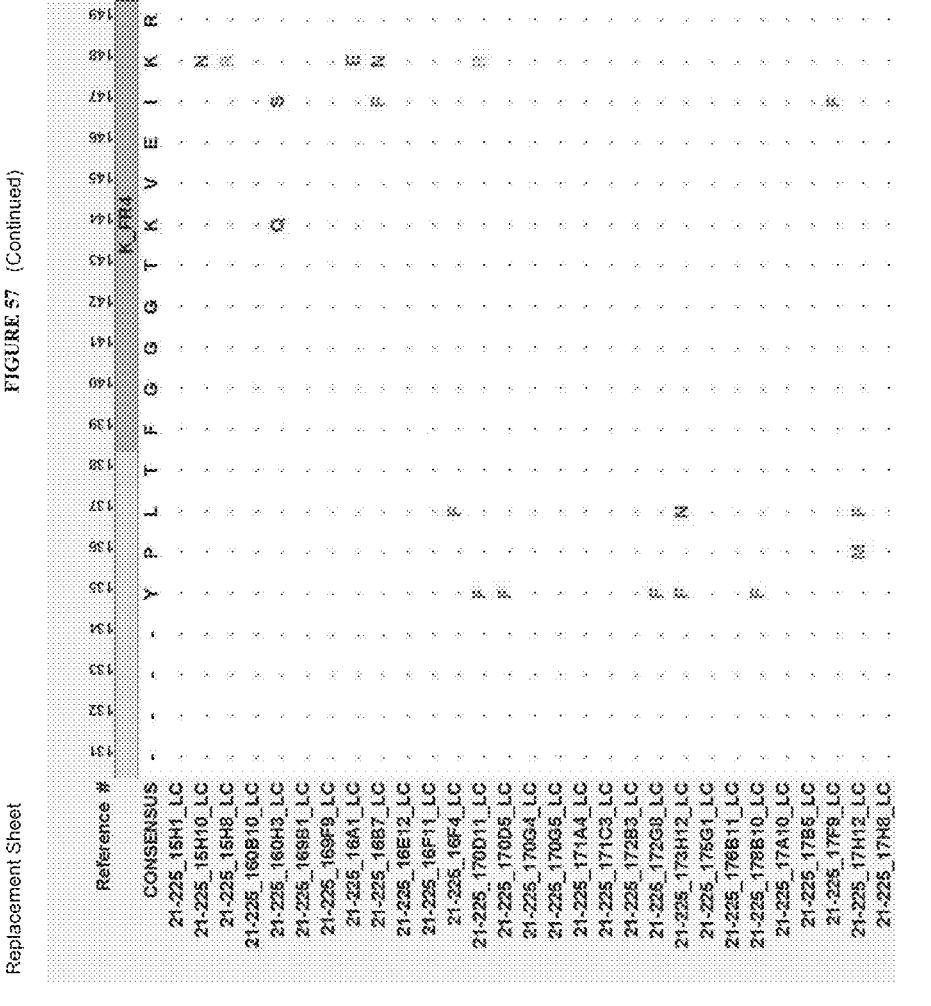
Figure 57:
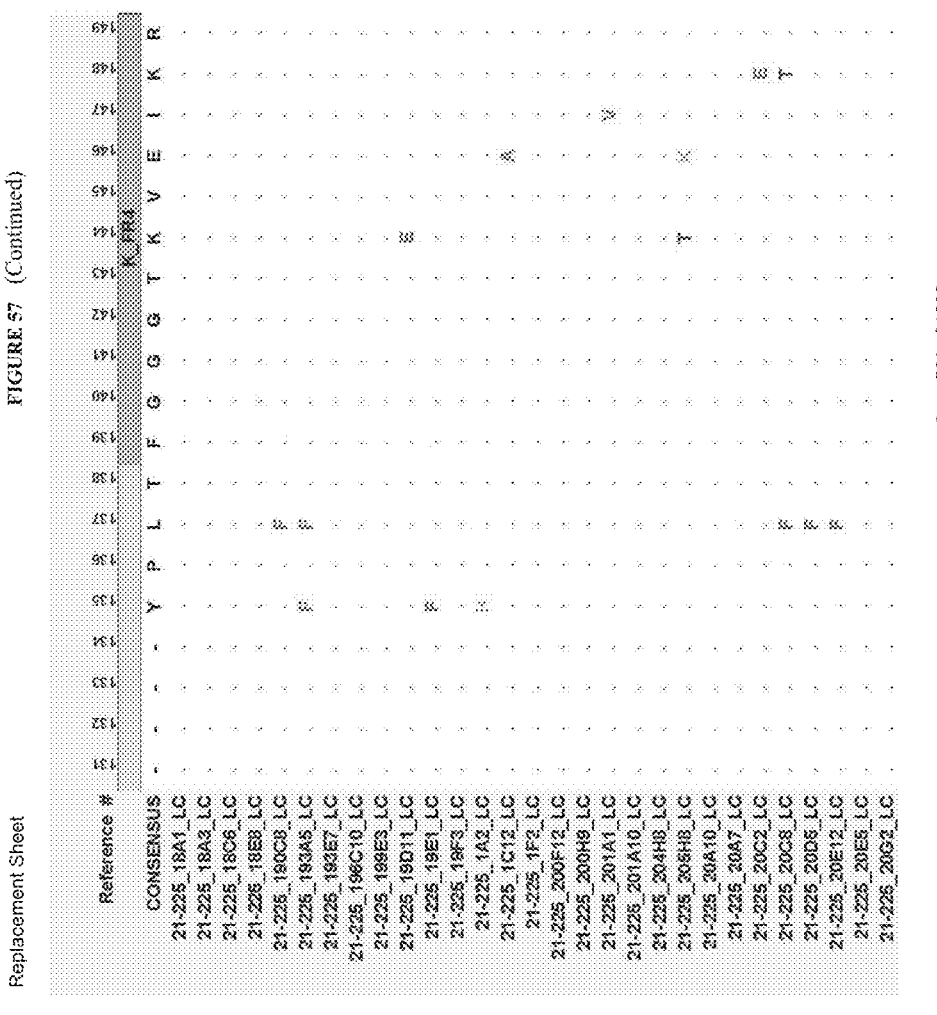
Figure 57:
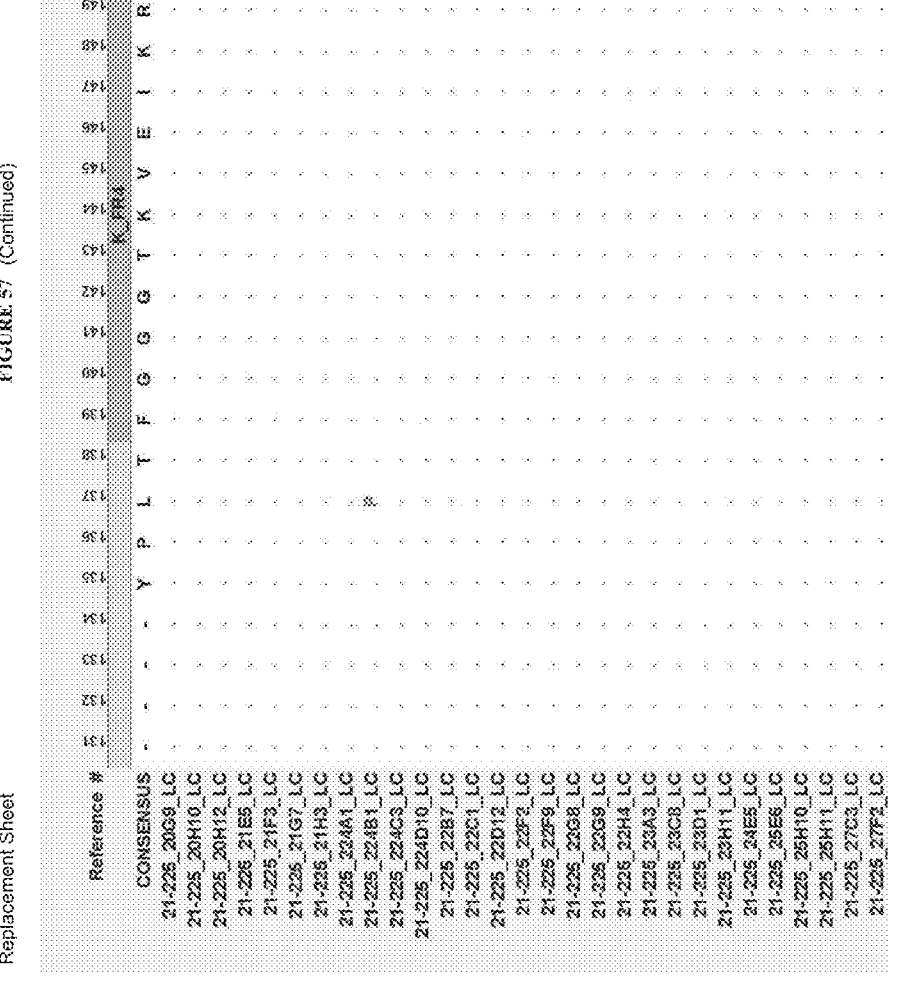
Figure 57:
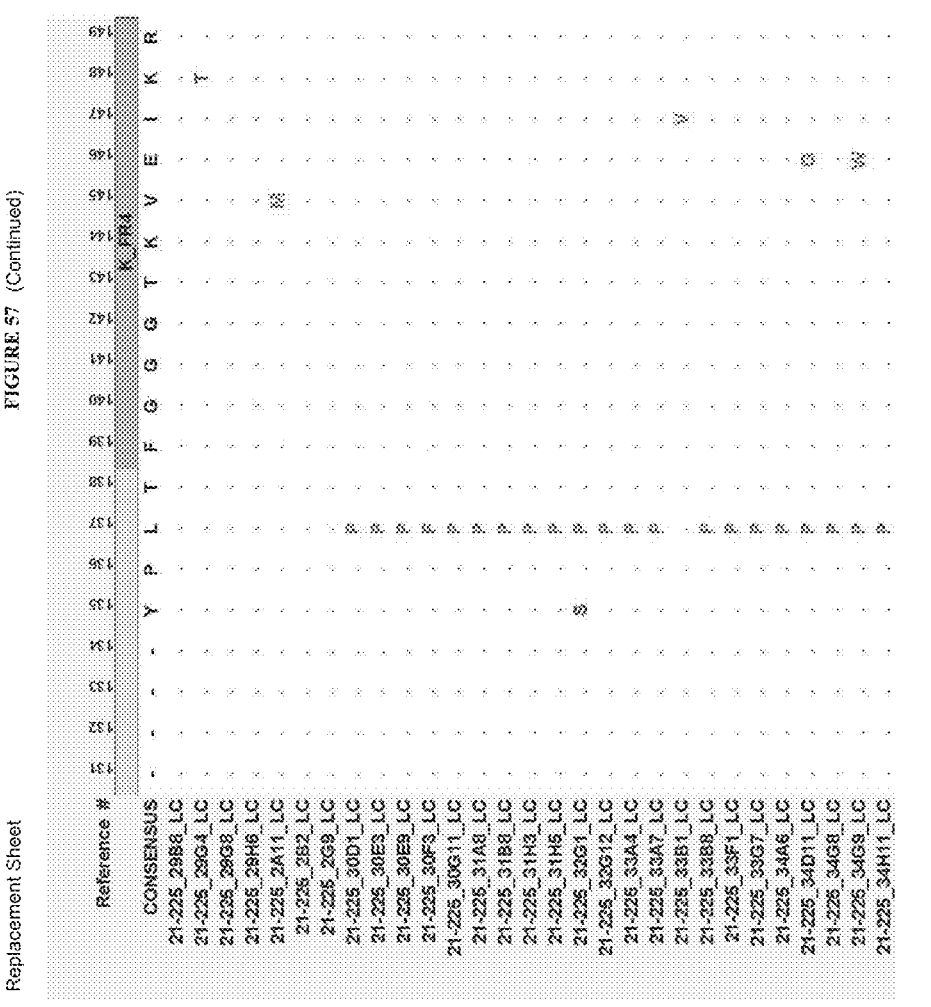
Figure 57:
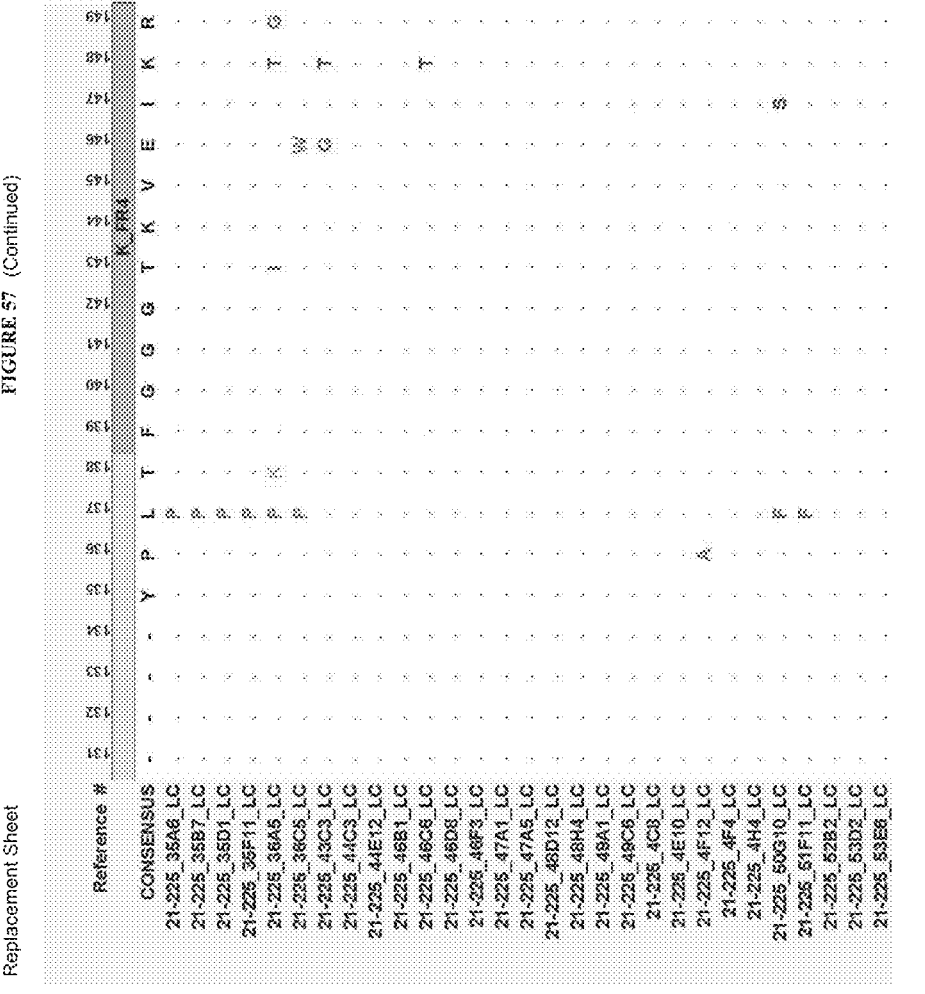
Figure 57:
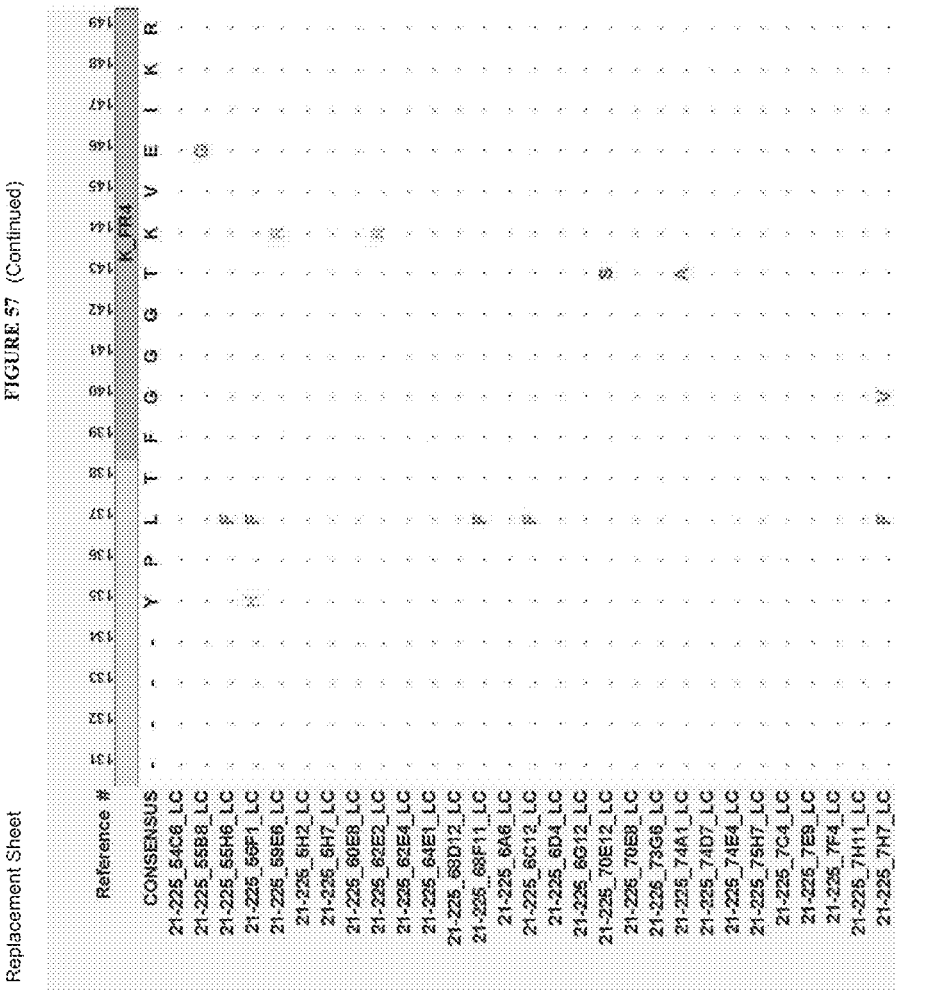
Figure 57:
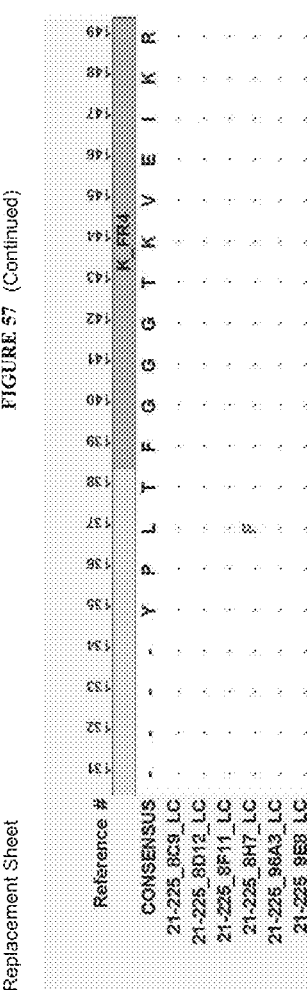
Figure 57:
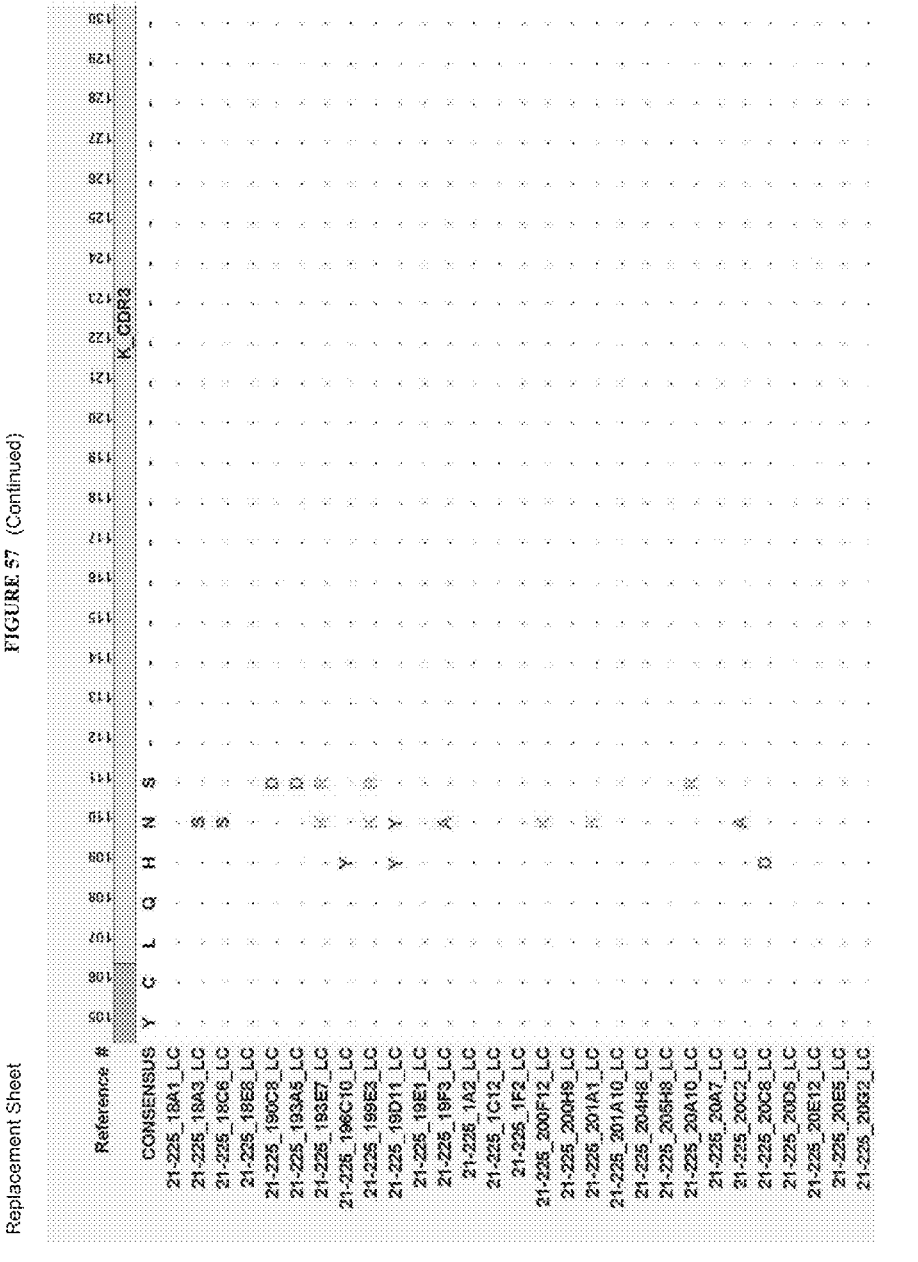
Figure 57:
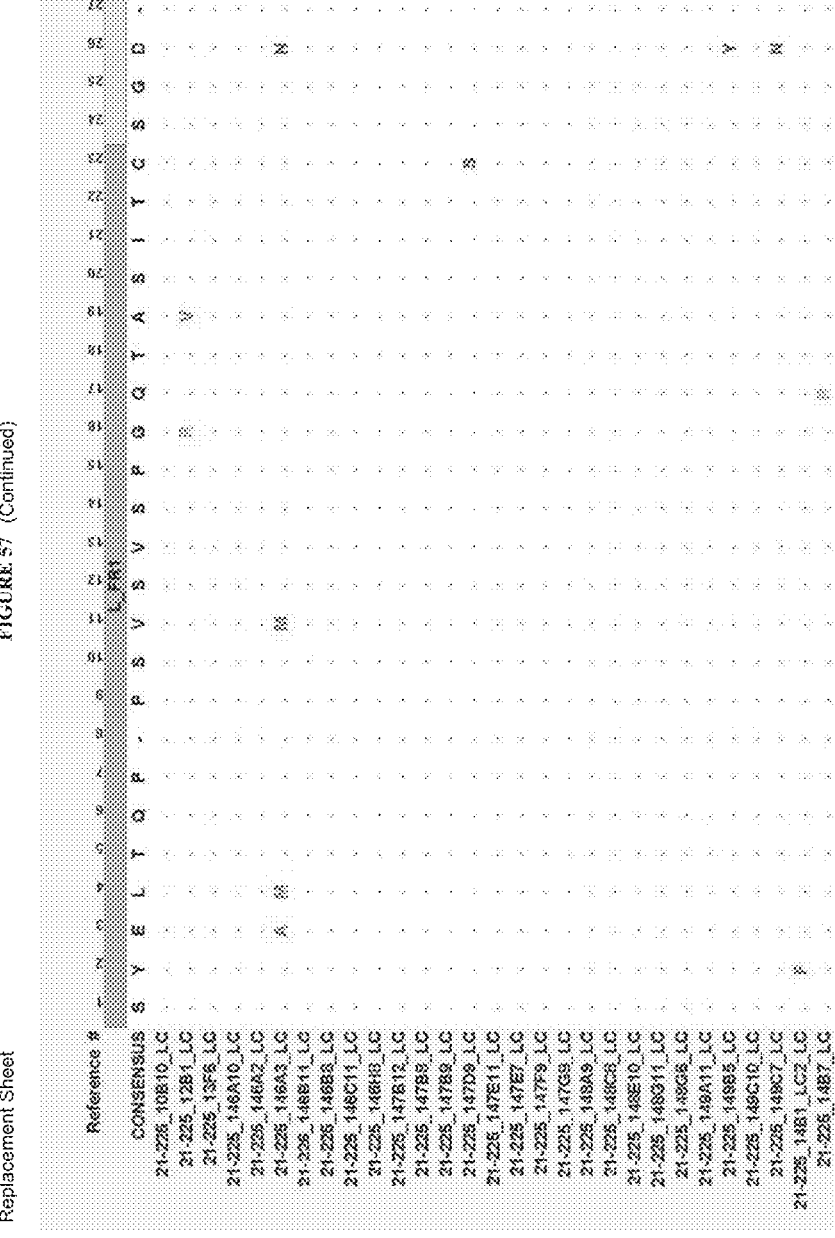
Figure 57:
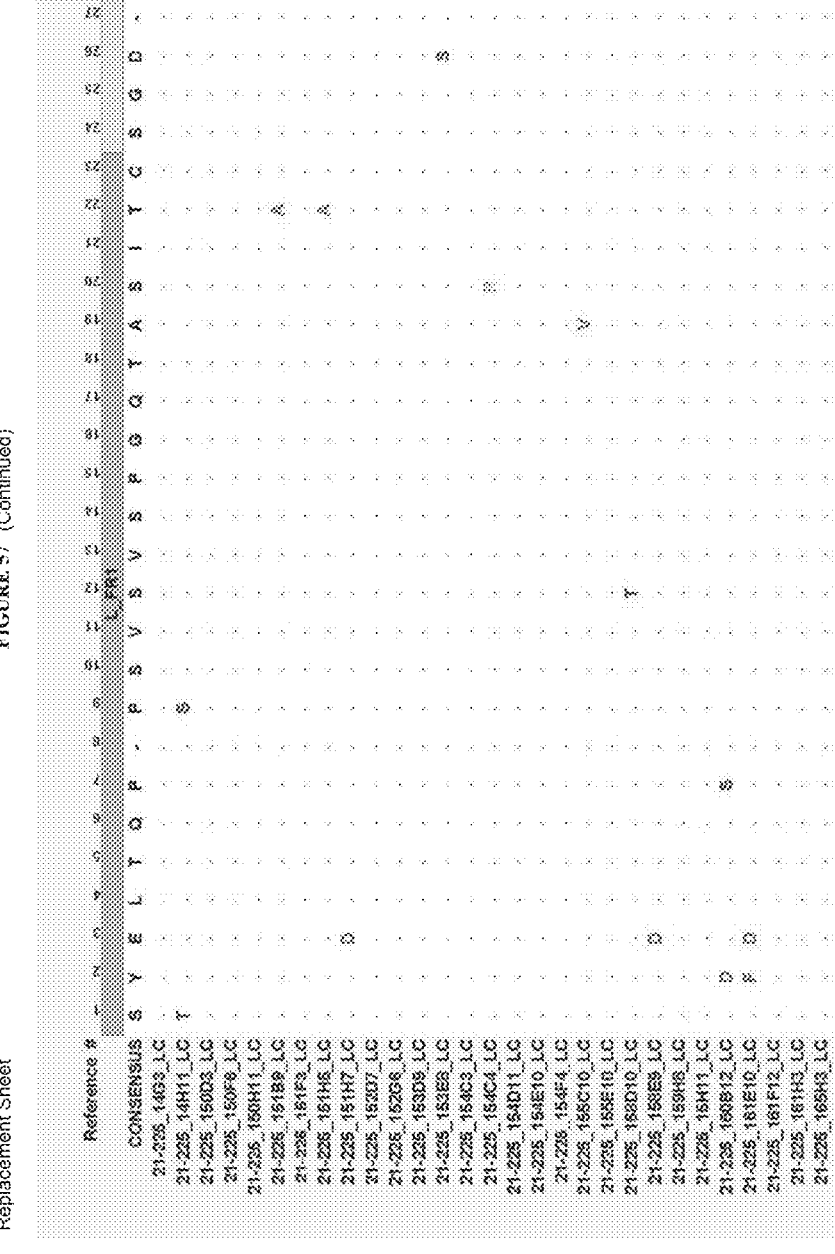
Figure 57:
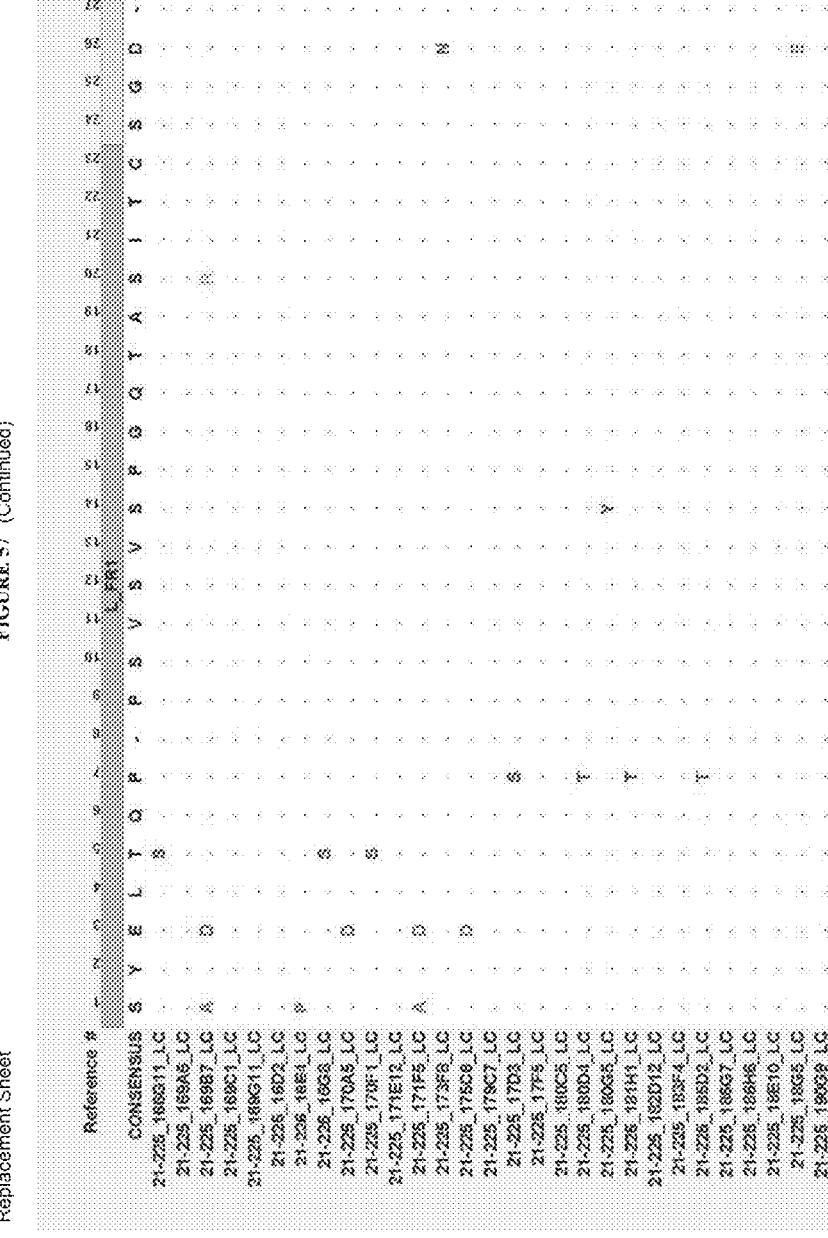
Figure 57:
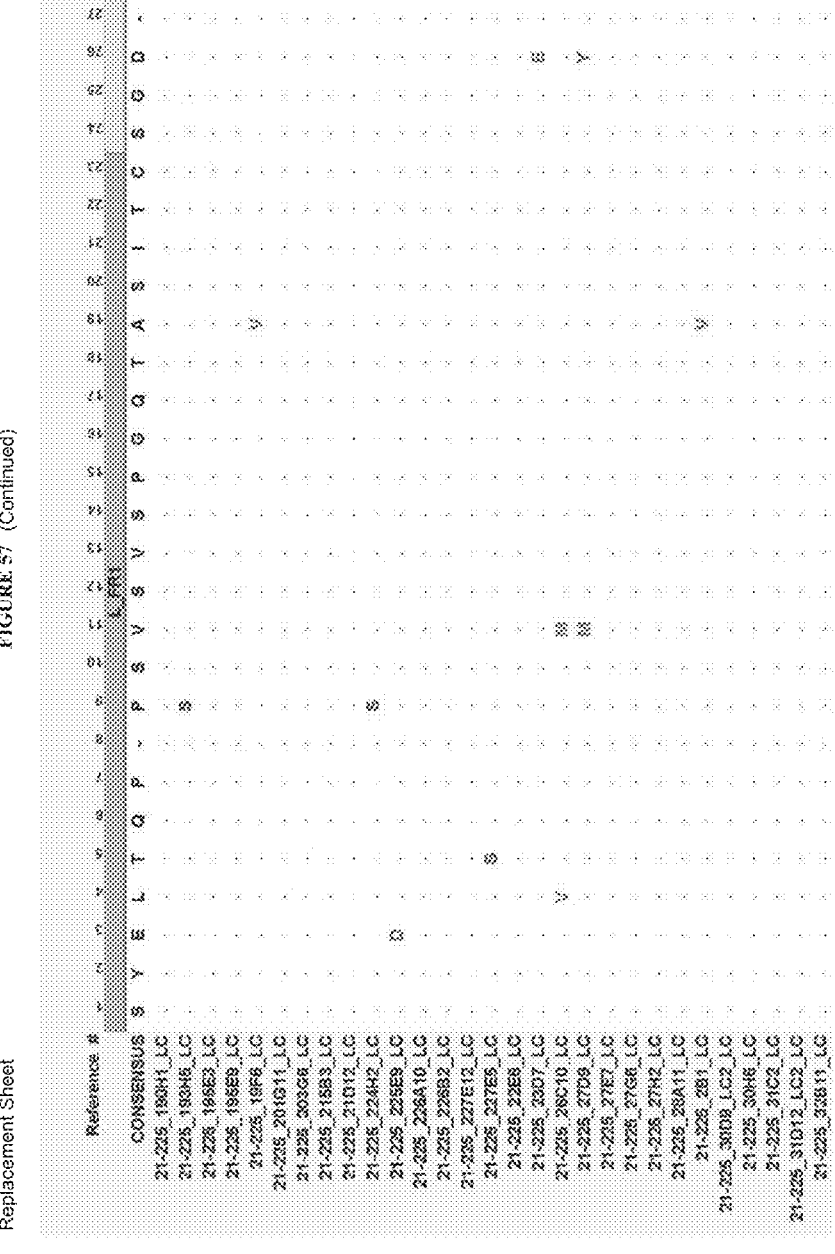
Figure 57:
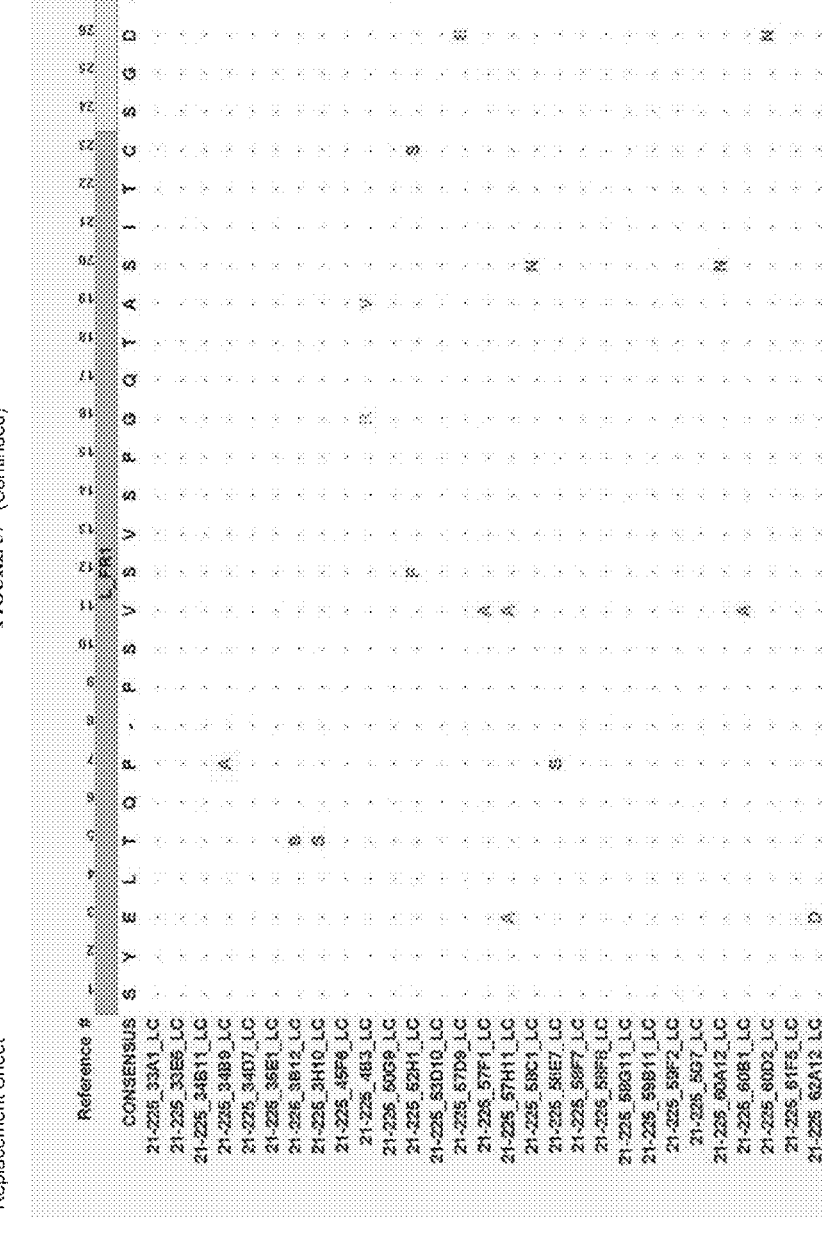
Figure 57:
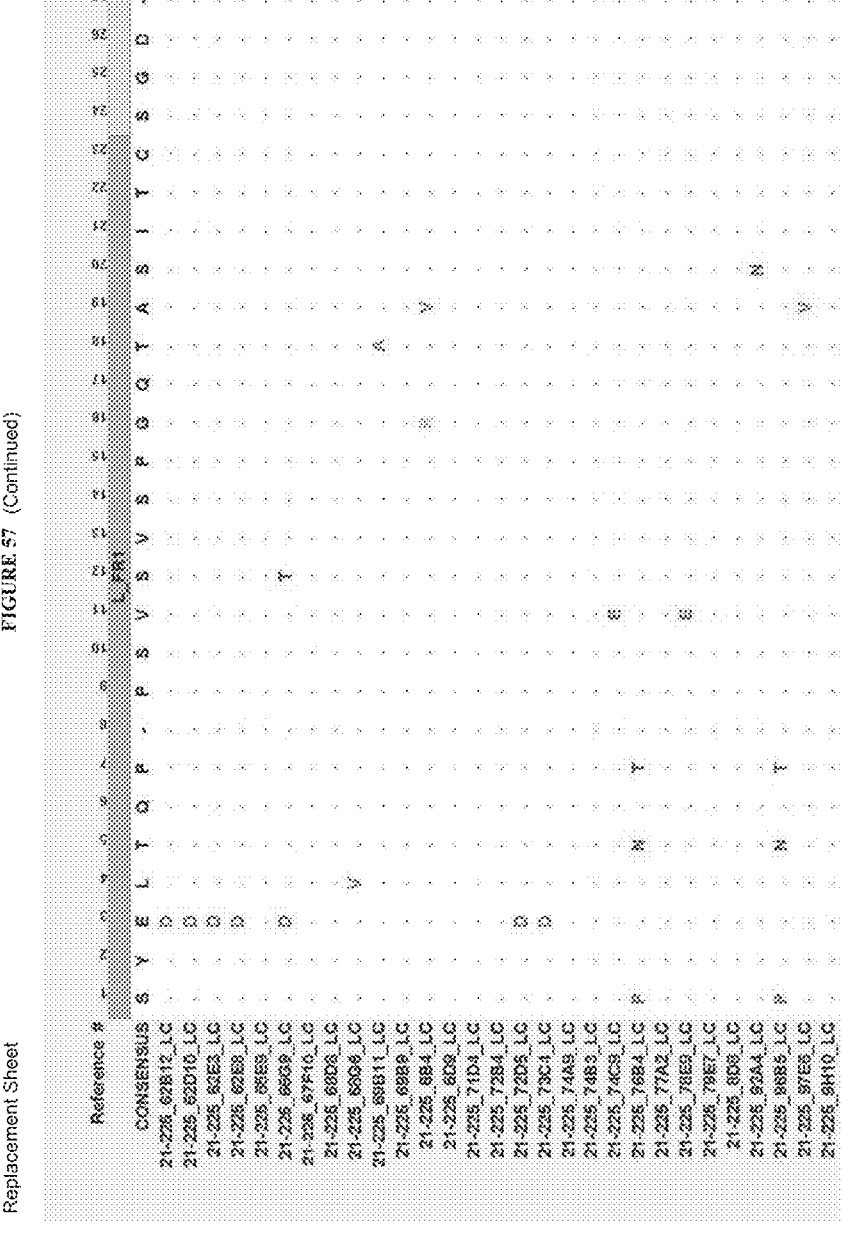
Figure 57:
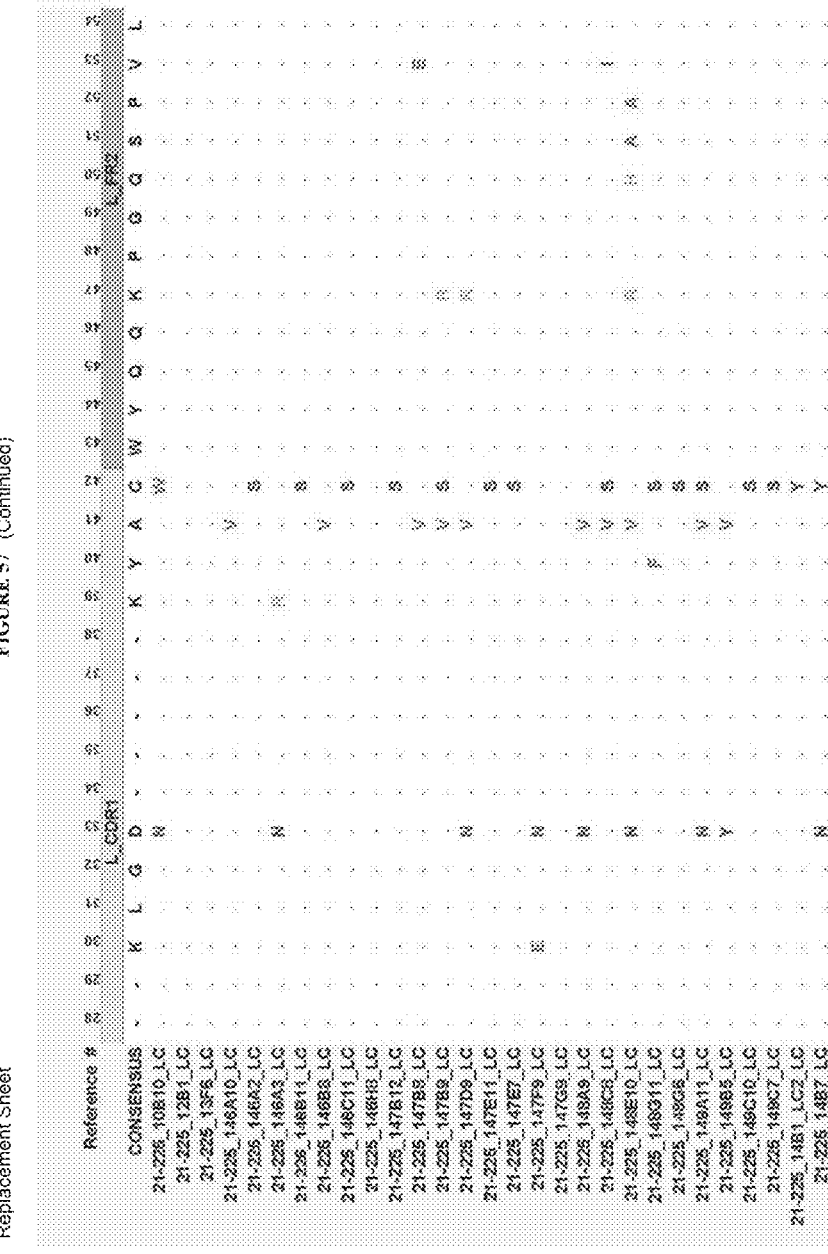
Figure 57:
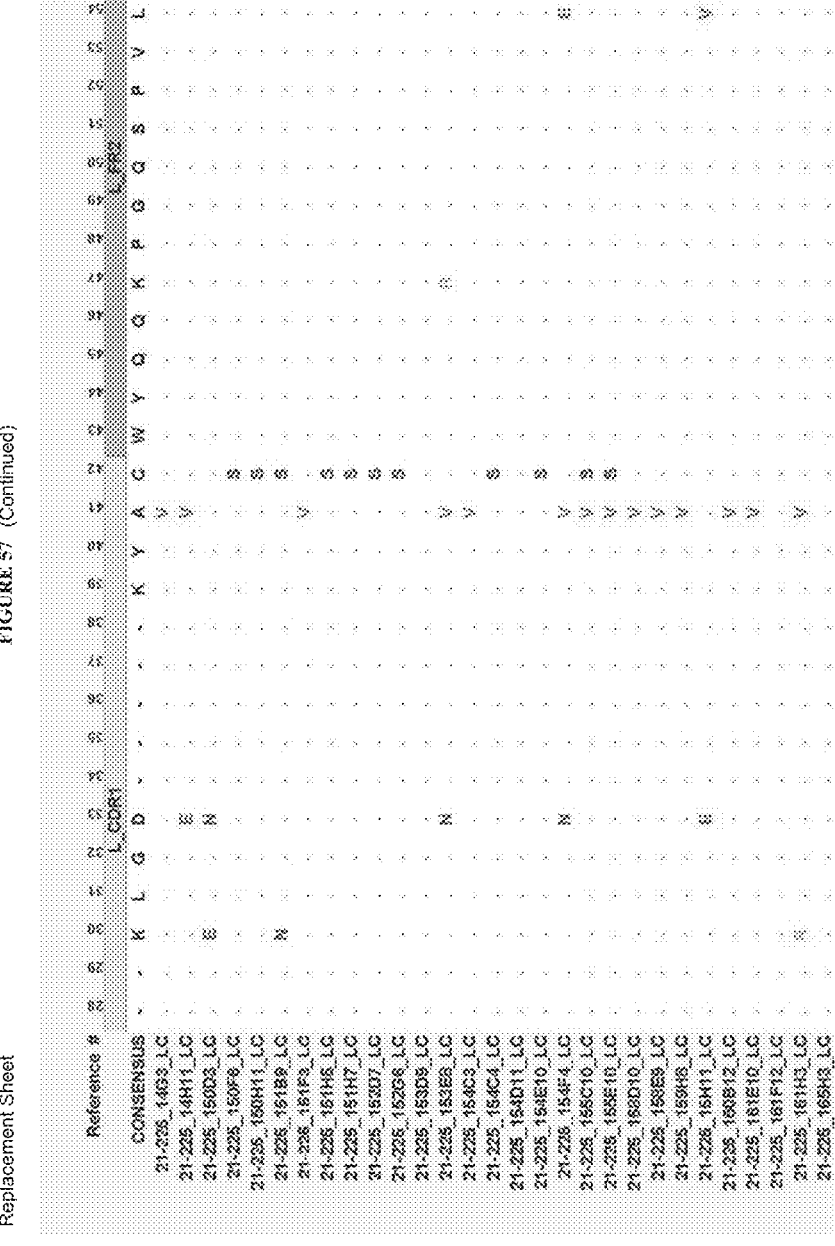
Figure 57:
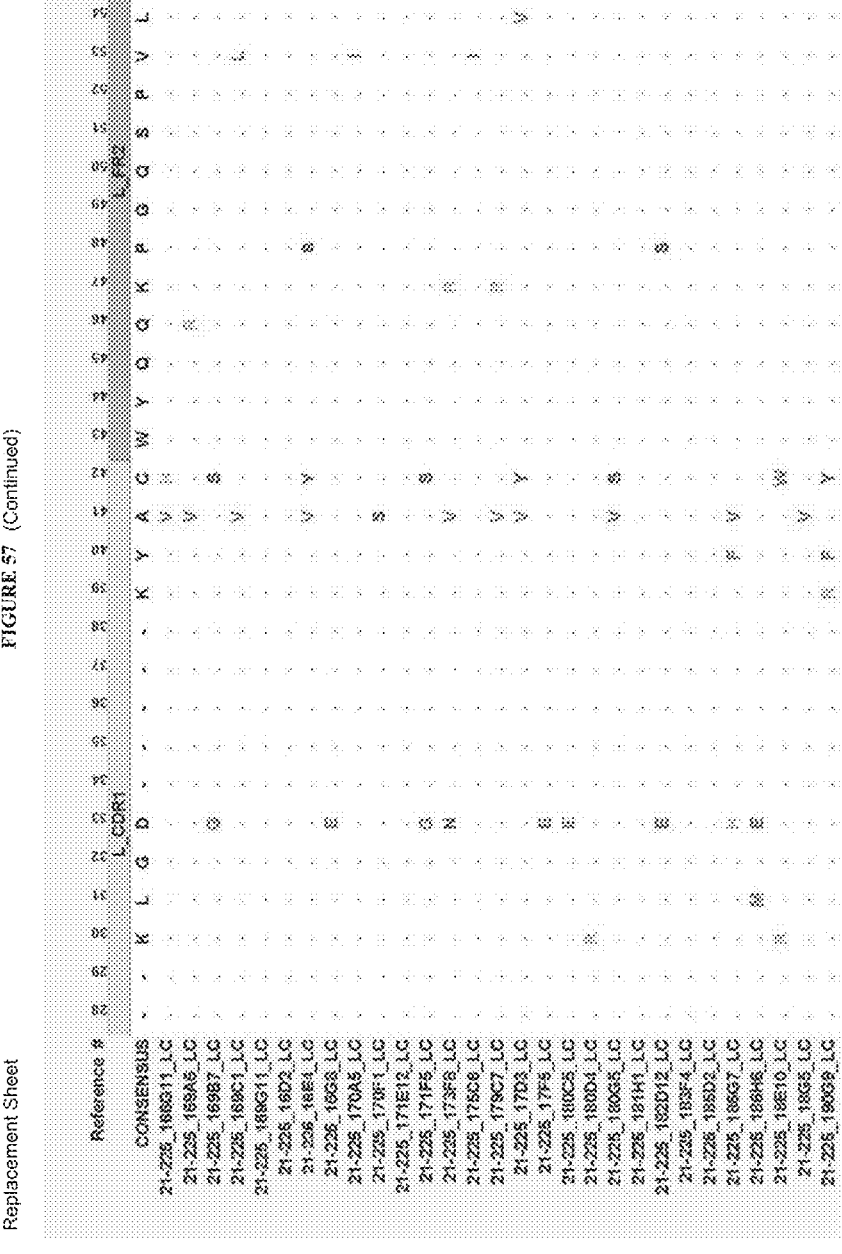
Figure 57:
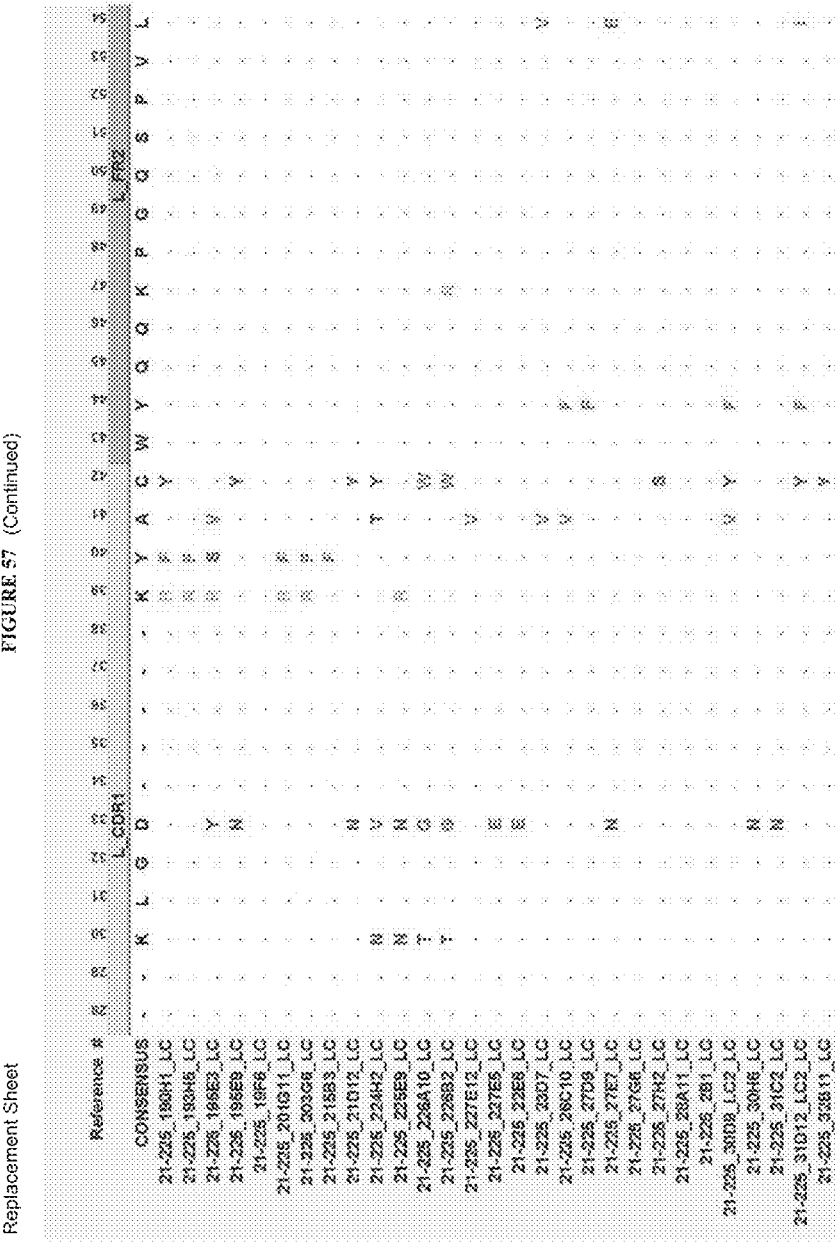
Figure 57:
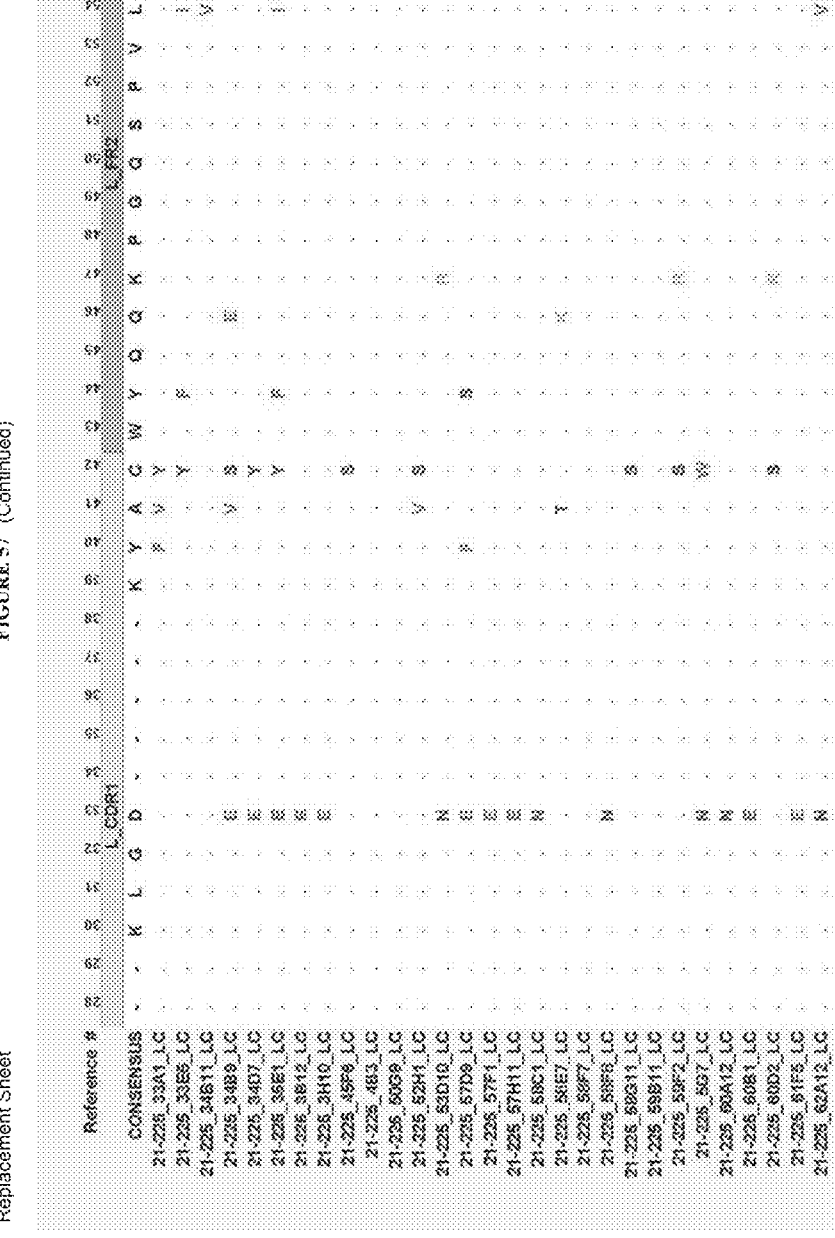
Figure 57:
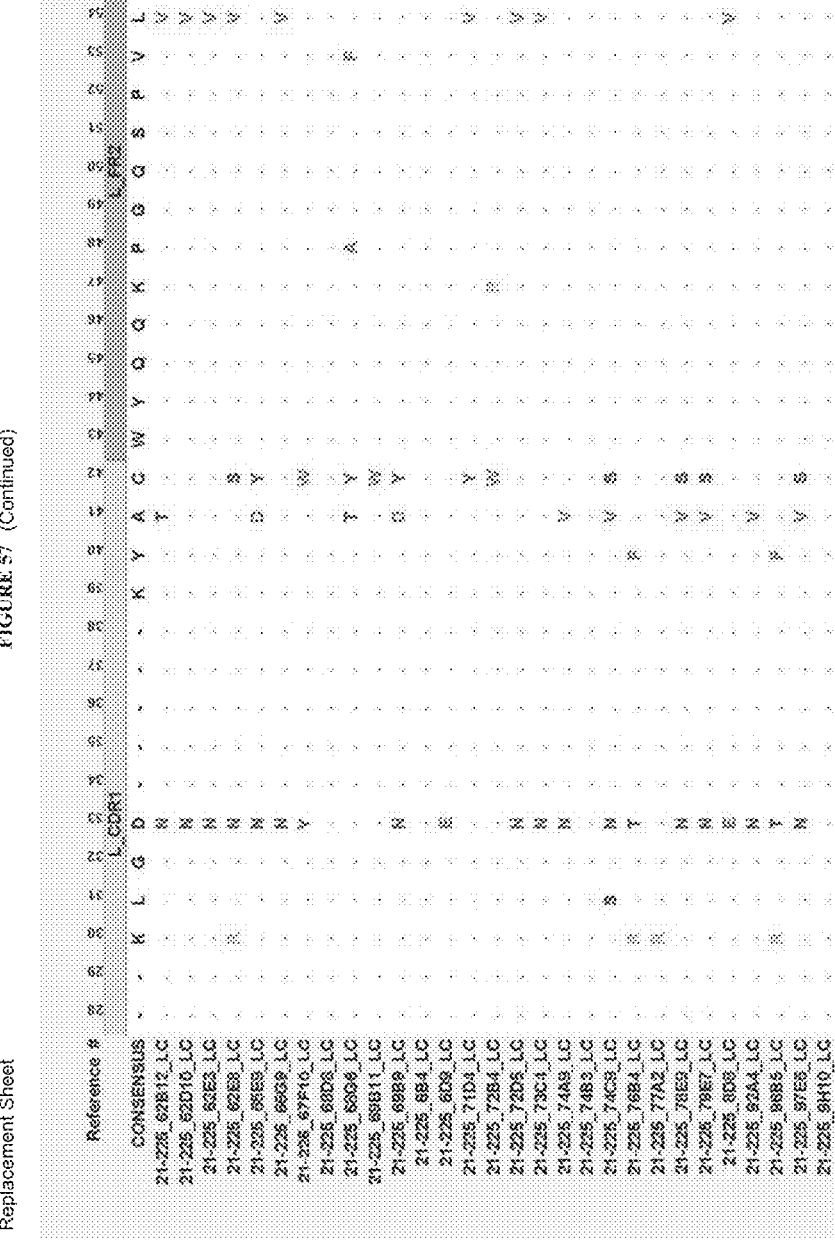
Figure 57:
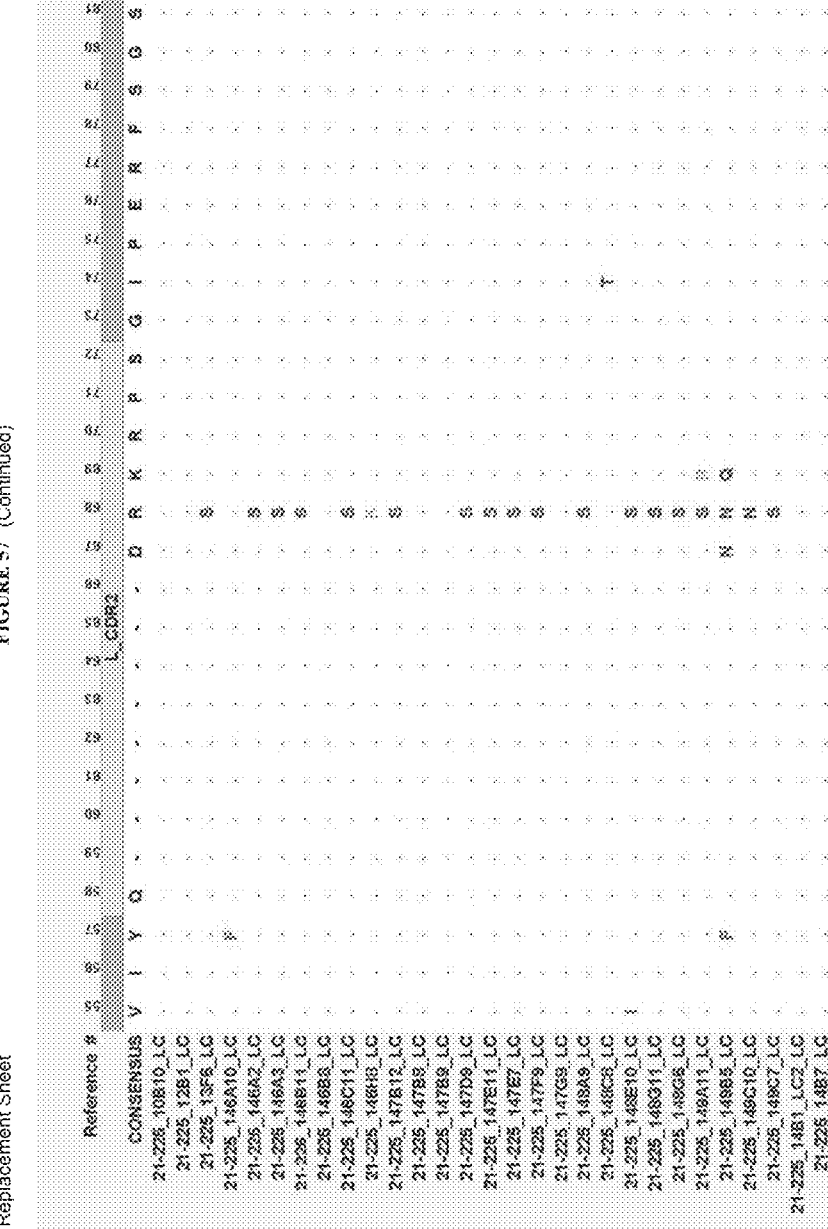
Figure 57:
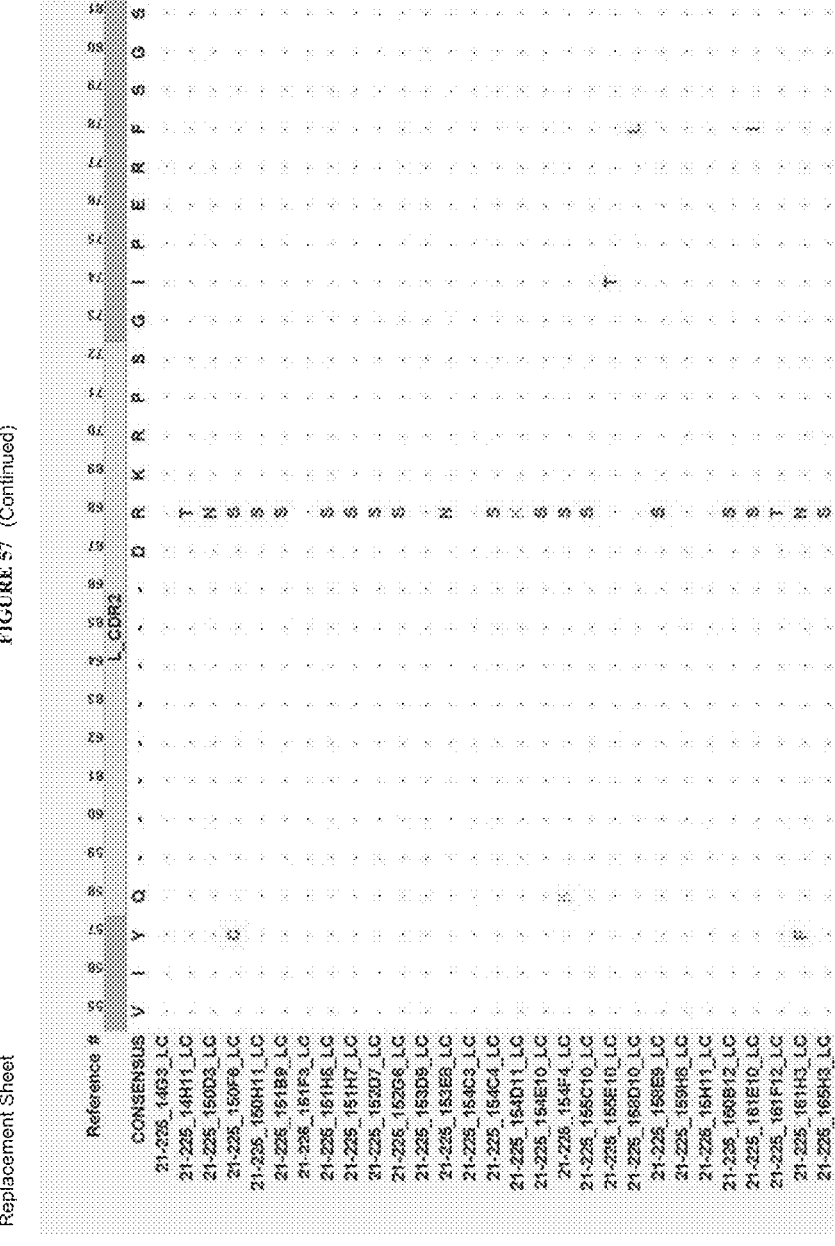
Figure 57:
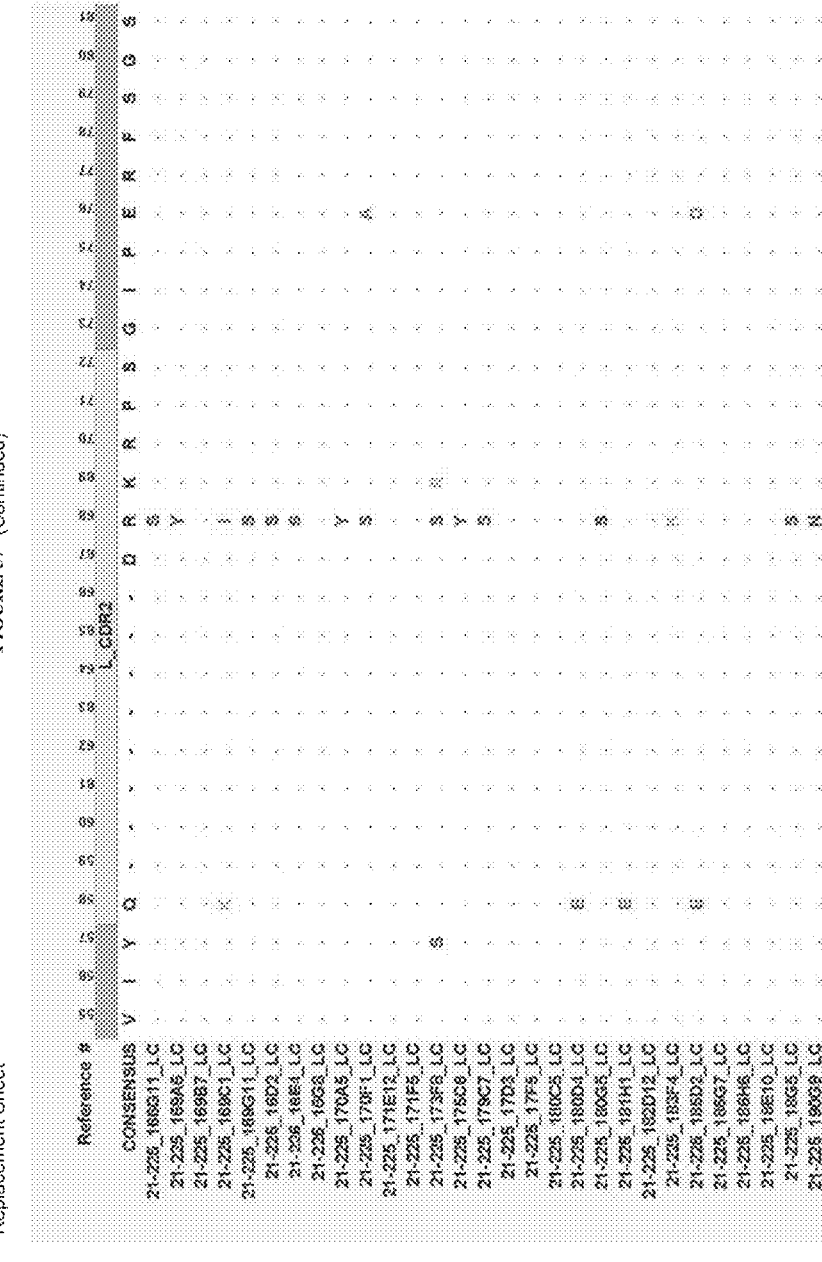
Figure 57:
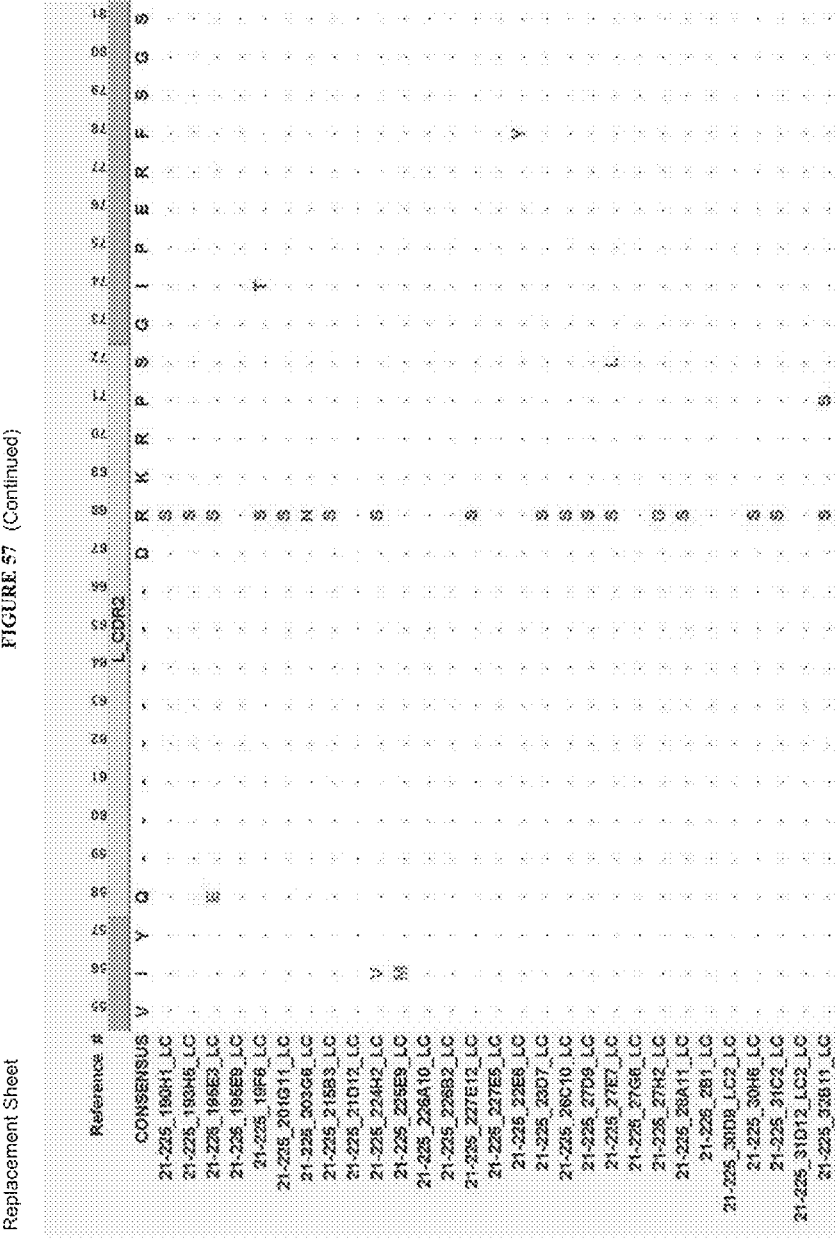
Figure 57:
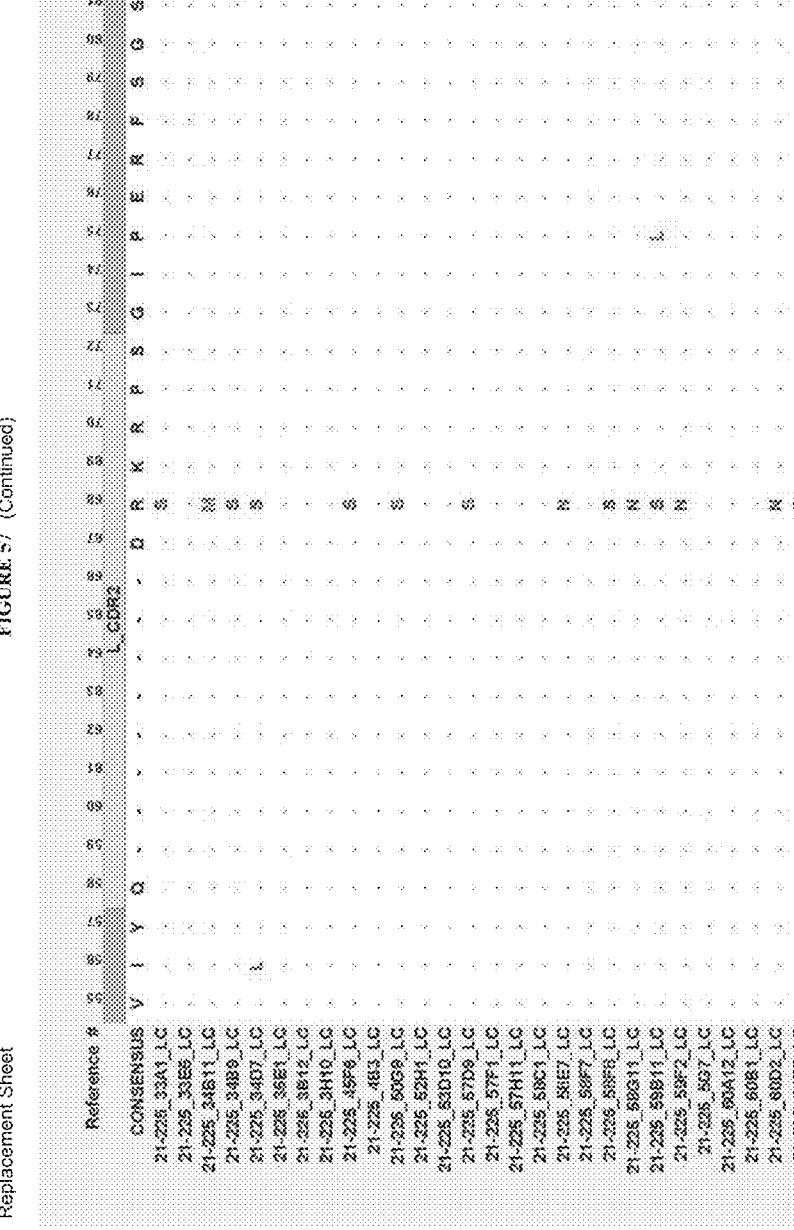
Figure 57:
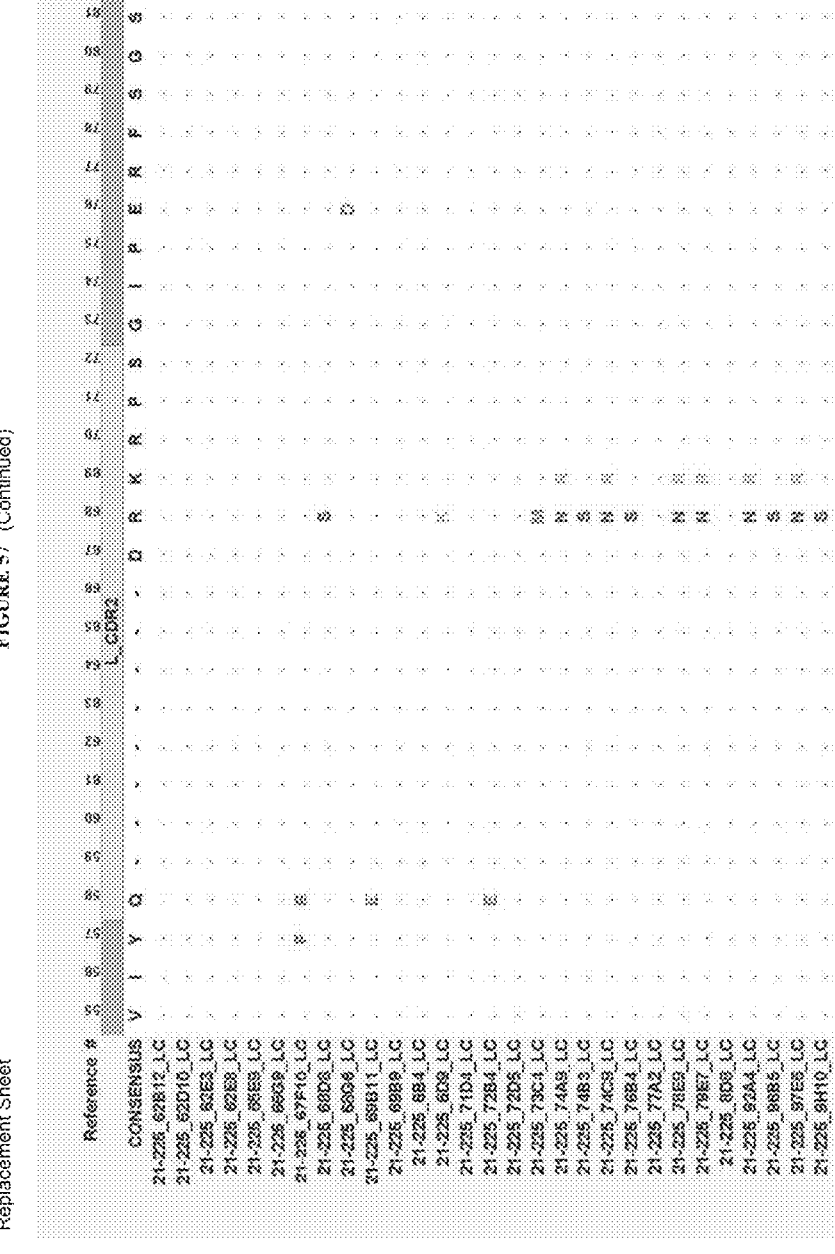
Figure 57:
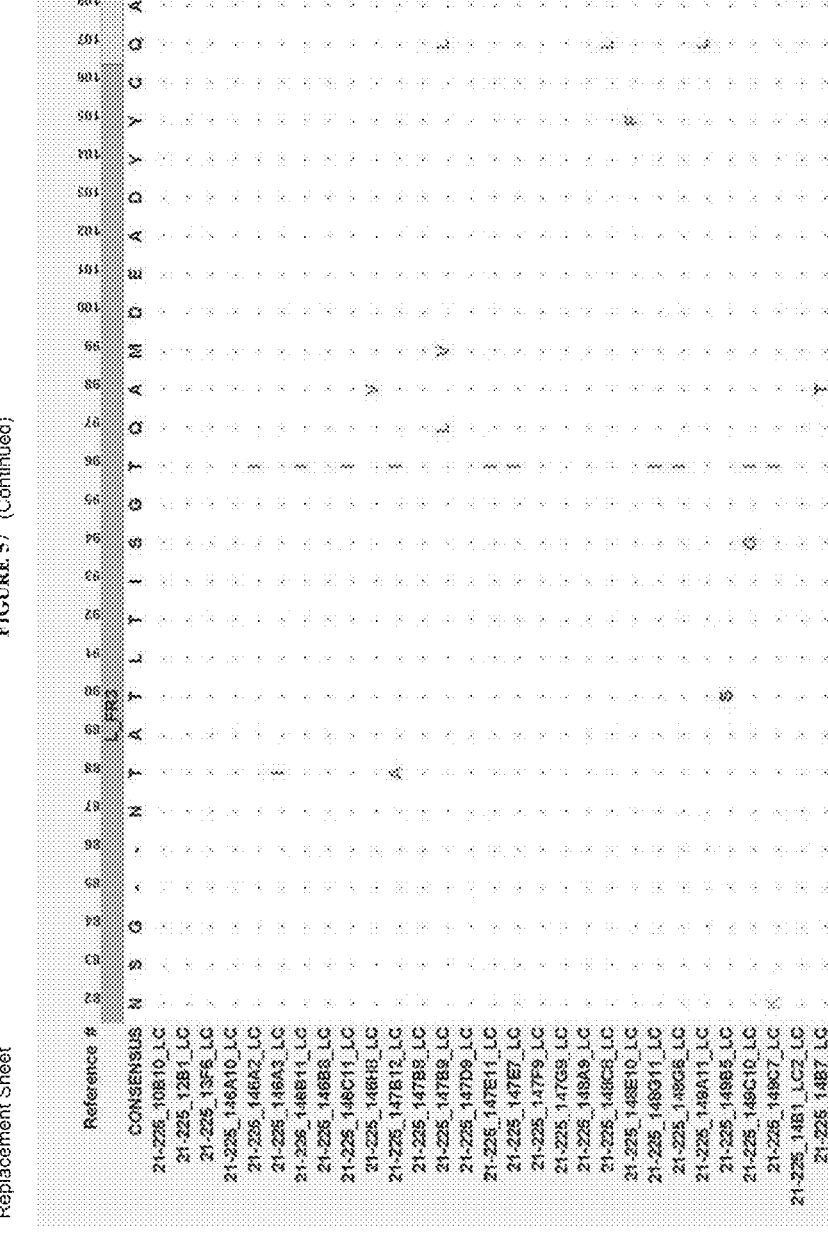
Figure 57:
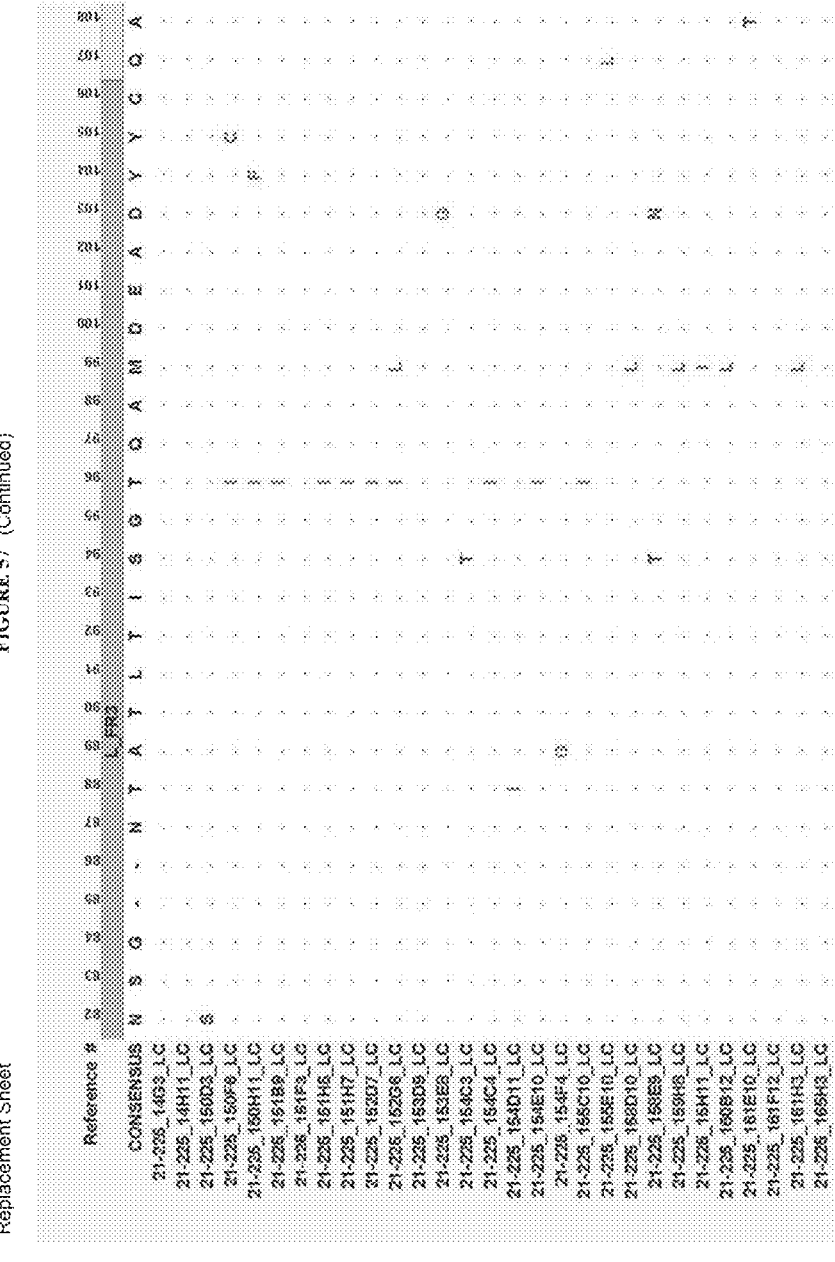
Figure 57:
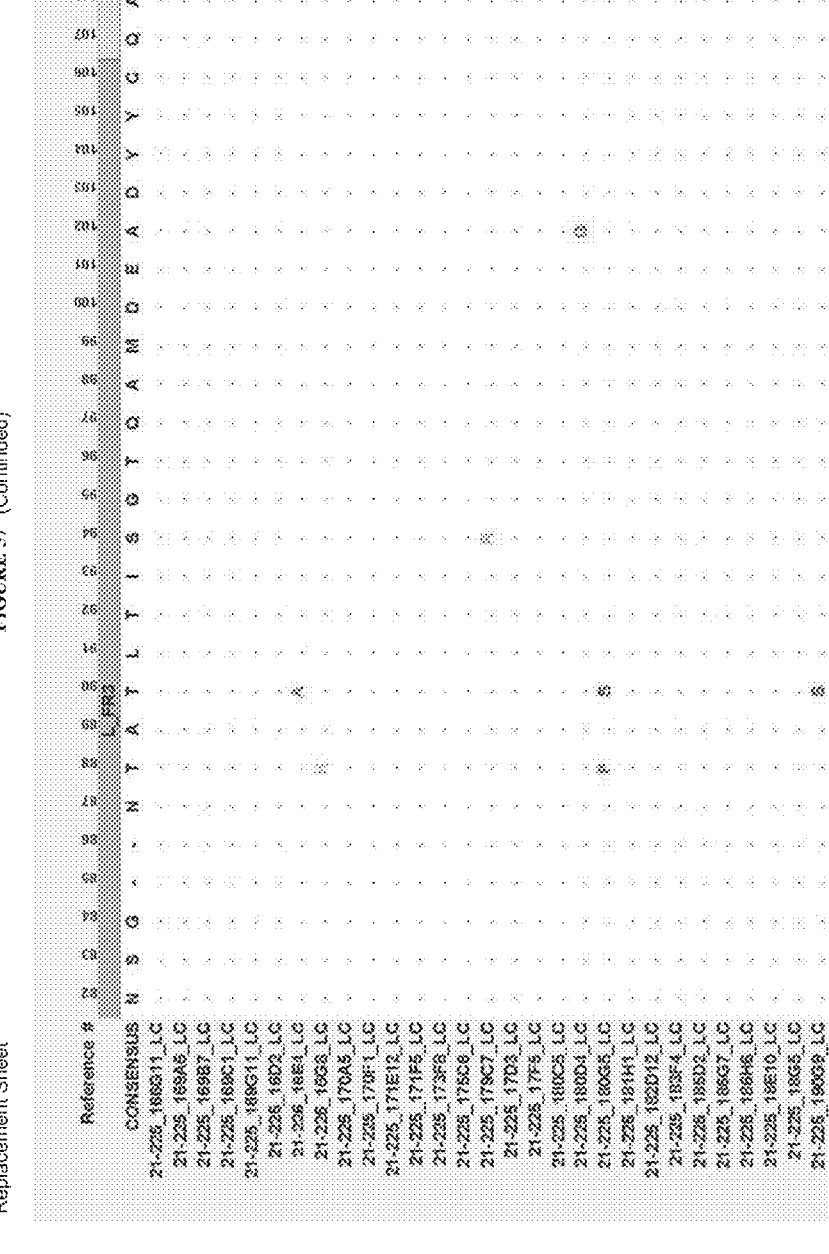
Figure 57:
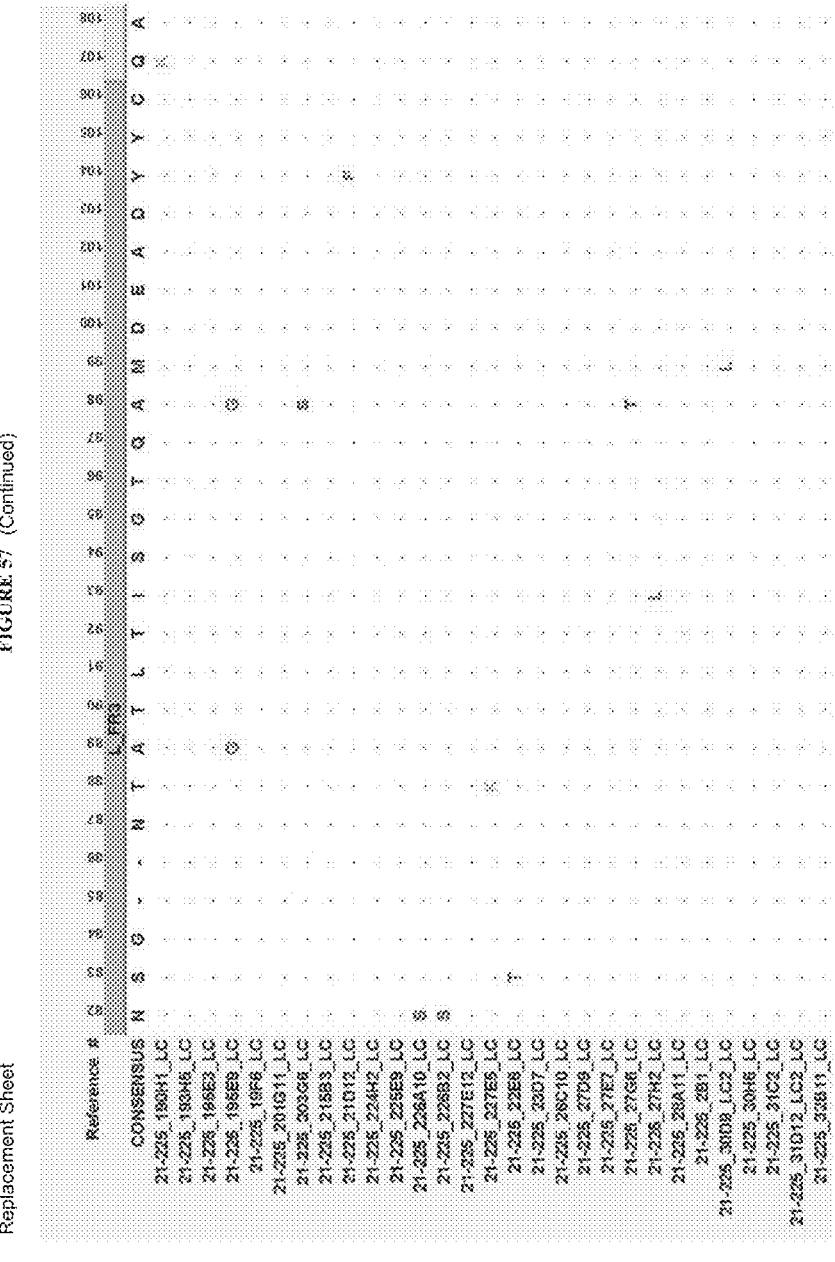
Figure 57:
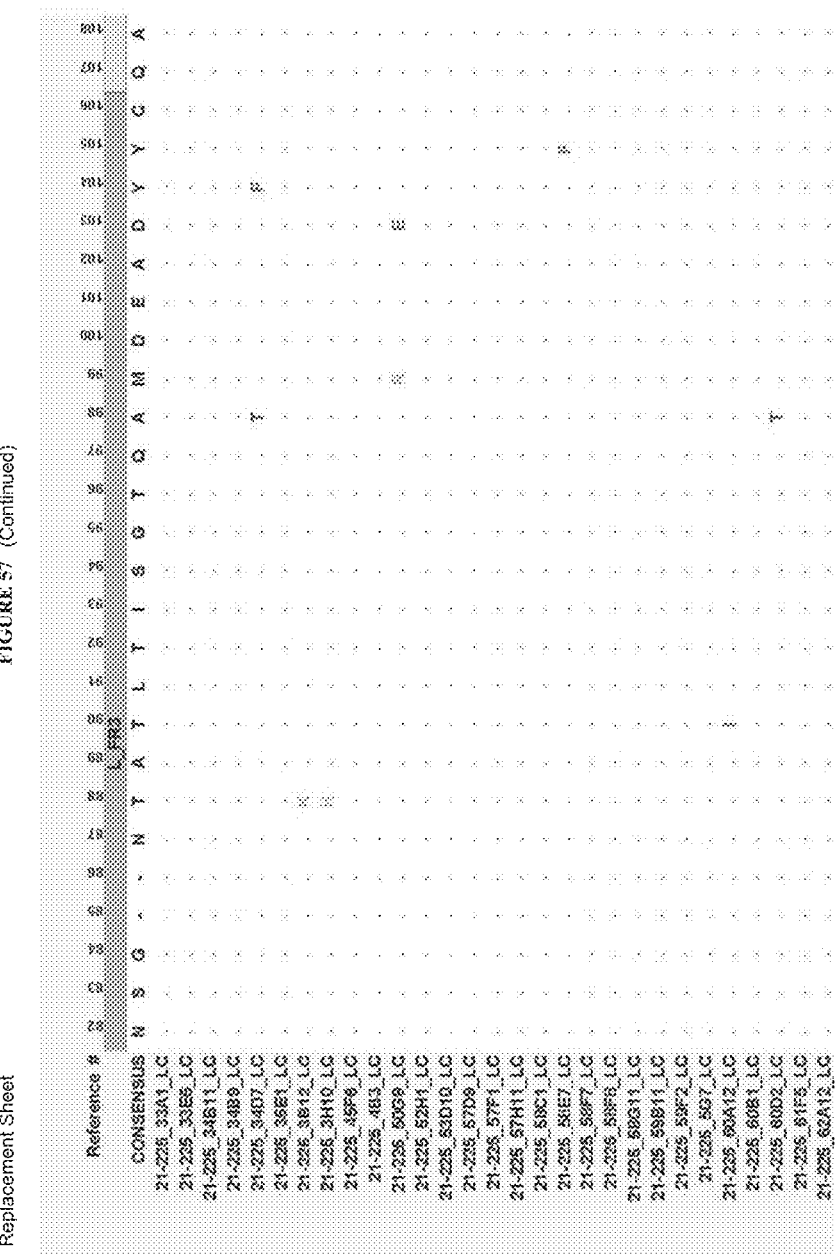
Figure 57:
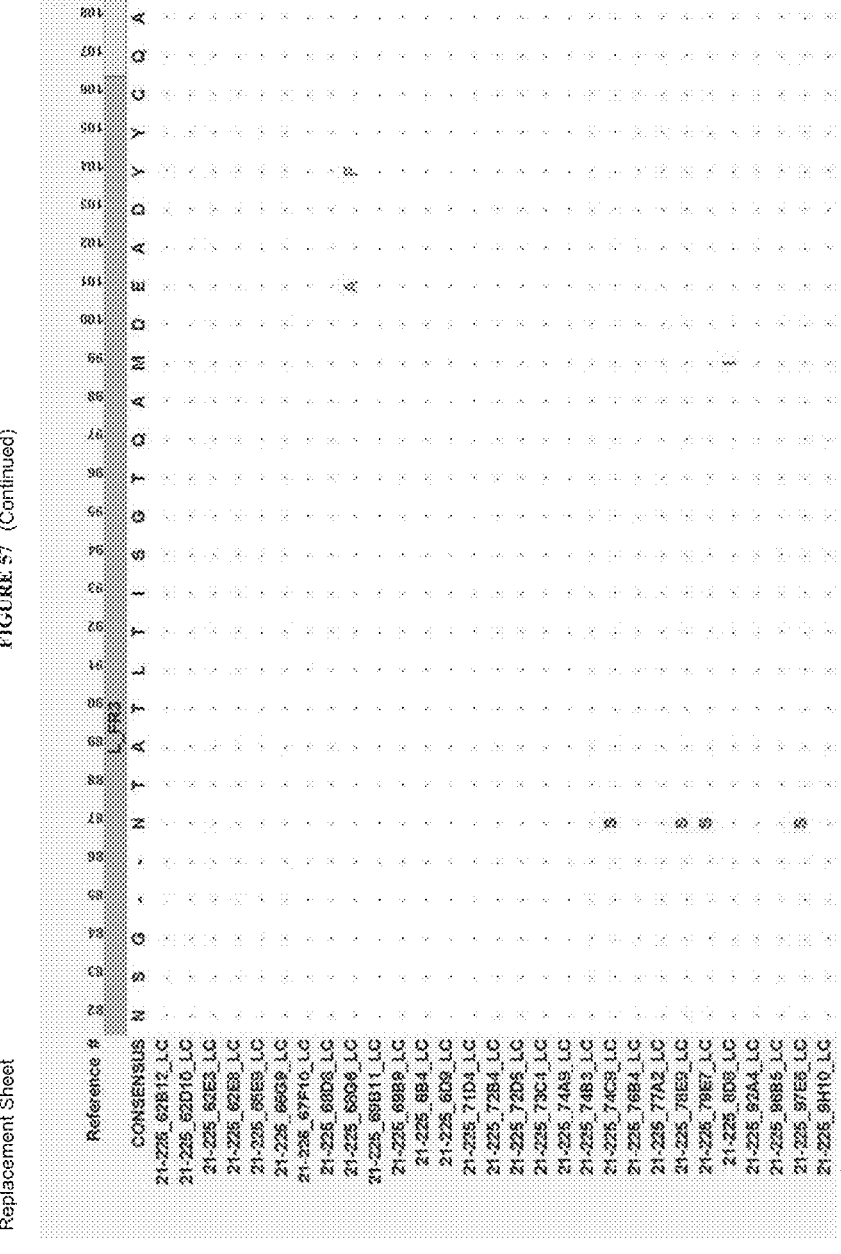
Figure 57:
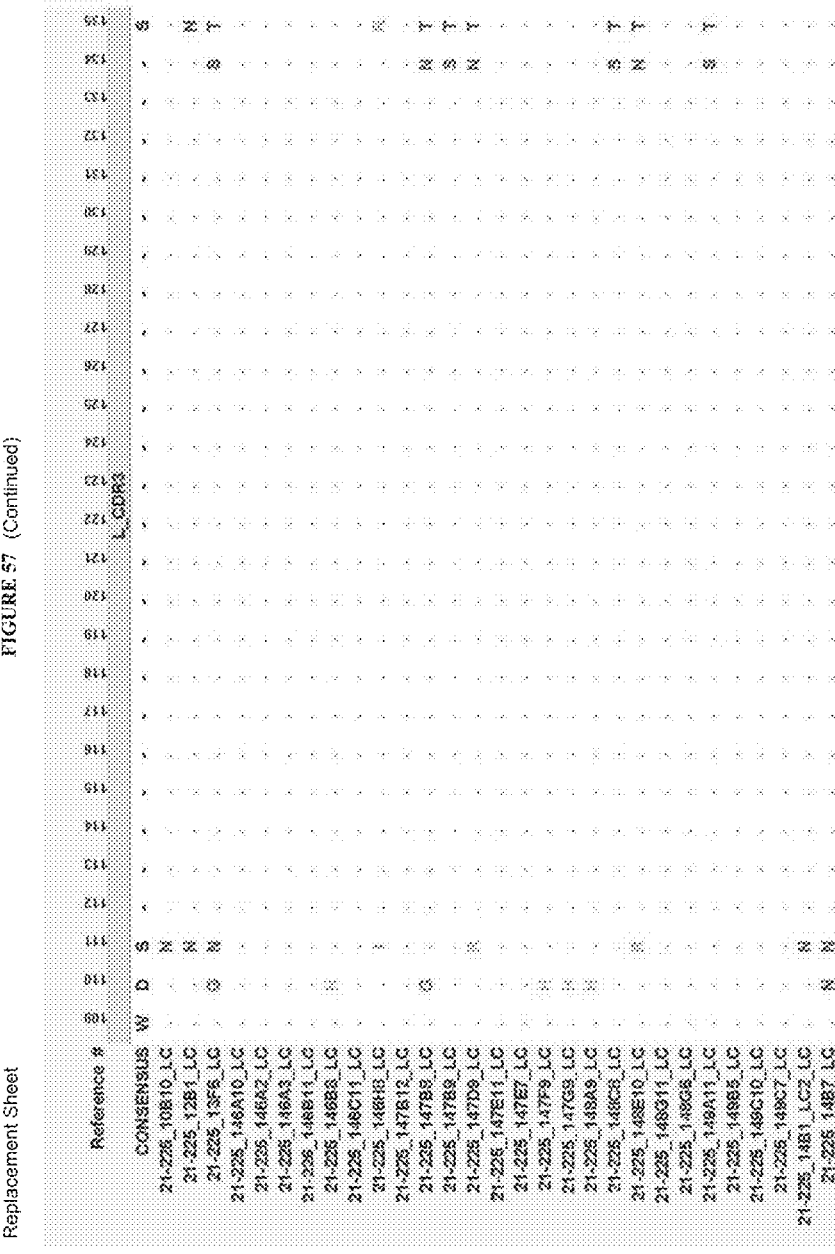
Figure 57:
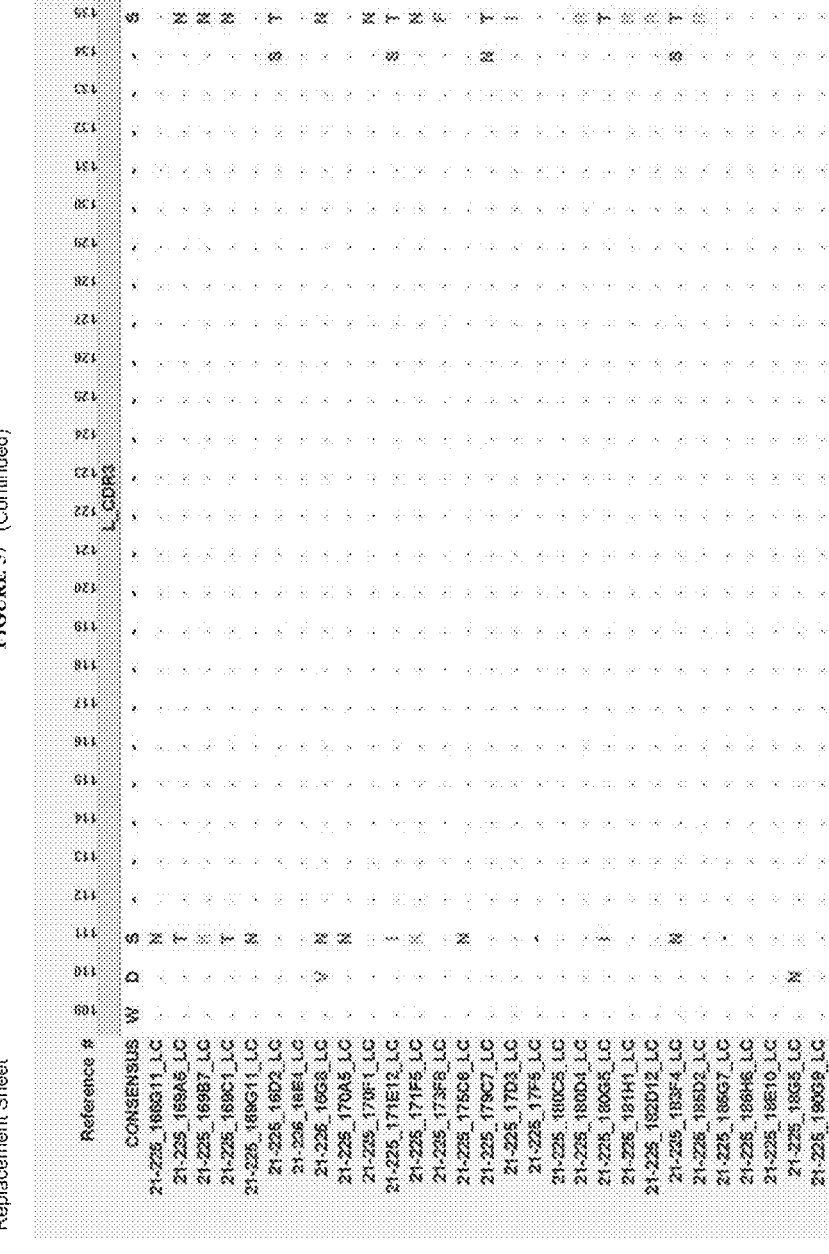
Figure 57:
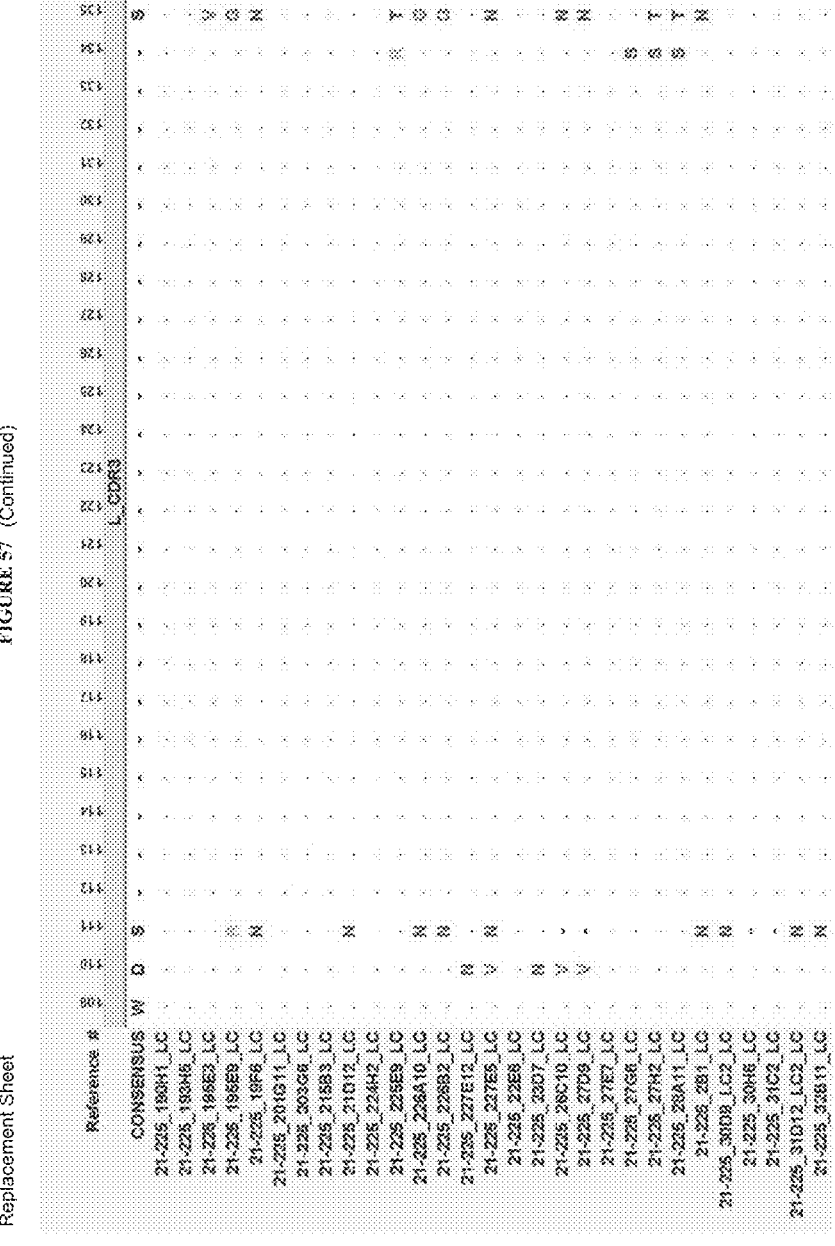
Figure 57:
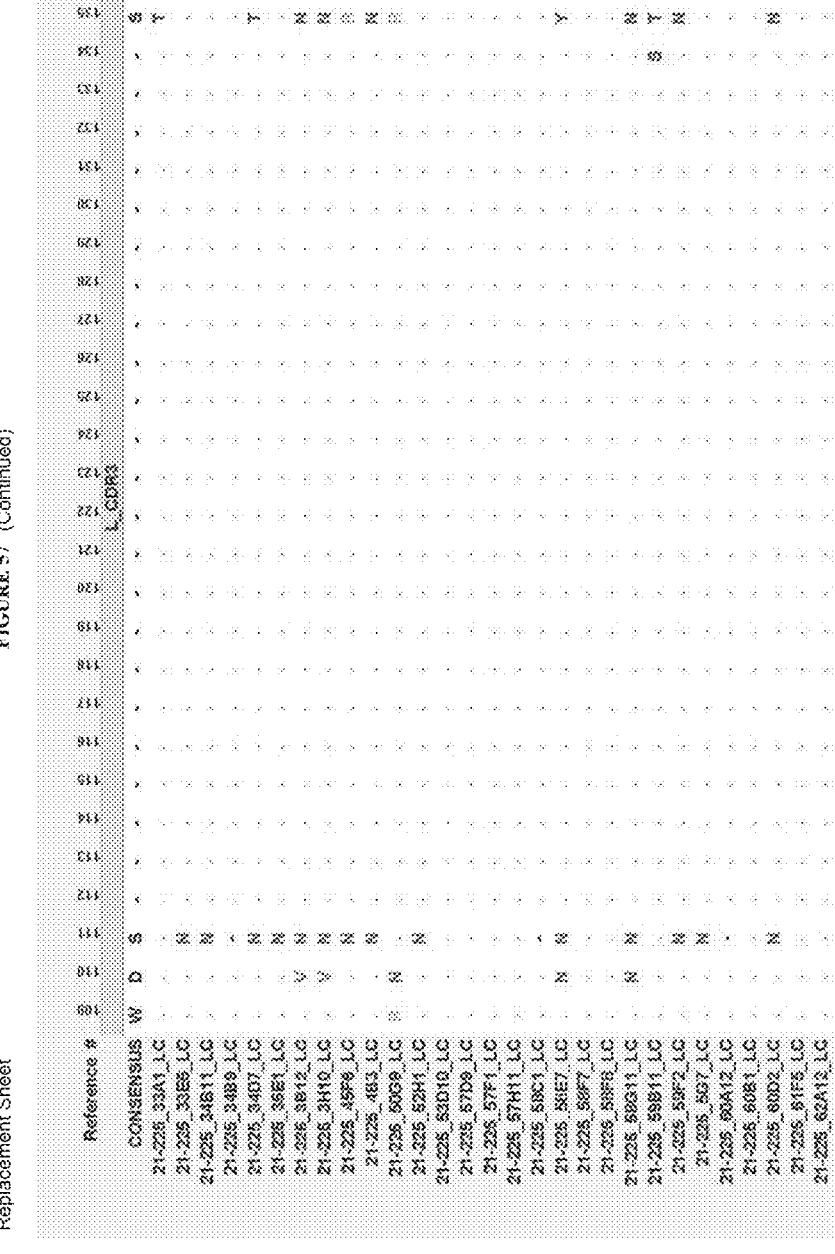
Figure 57:
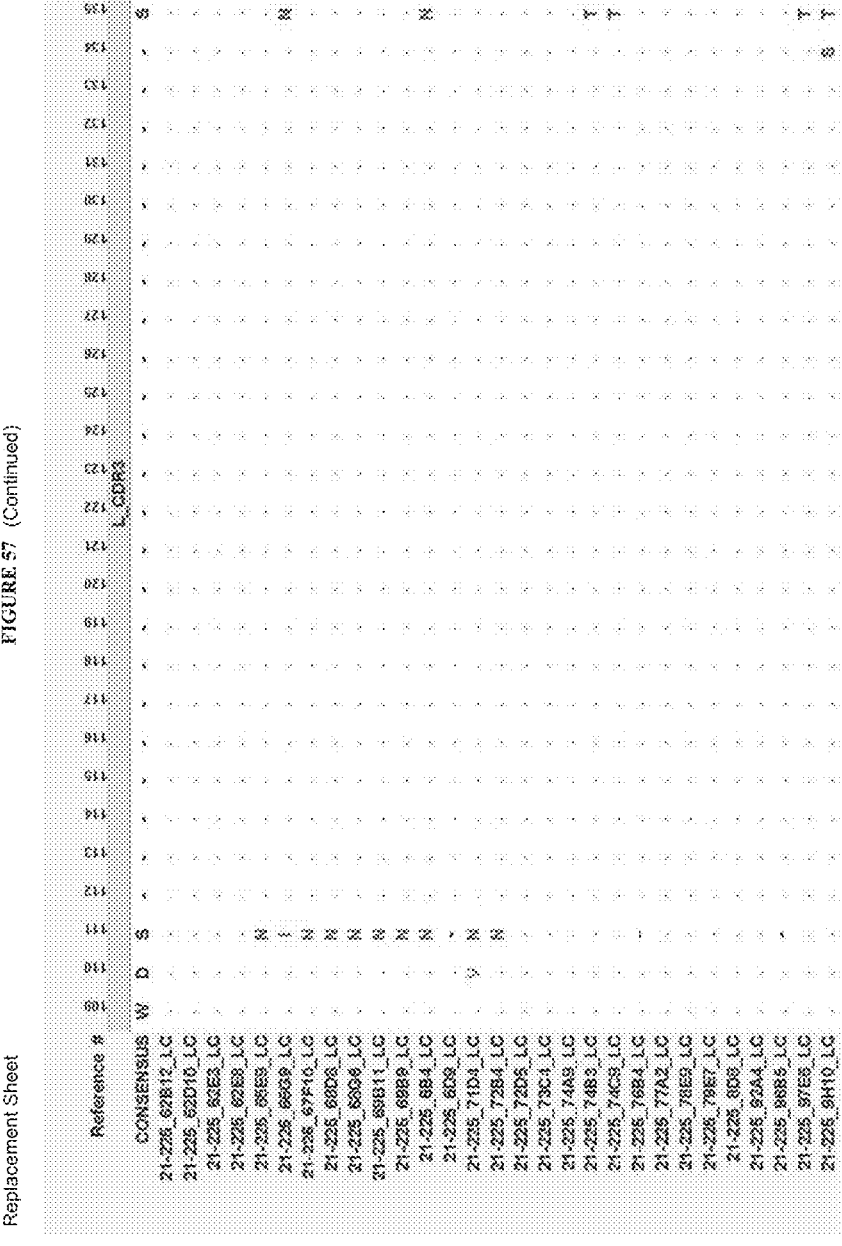
Figure 57:
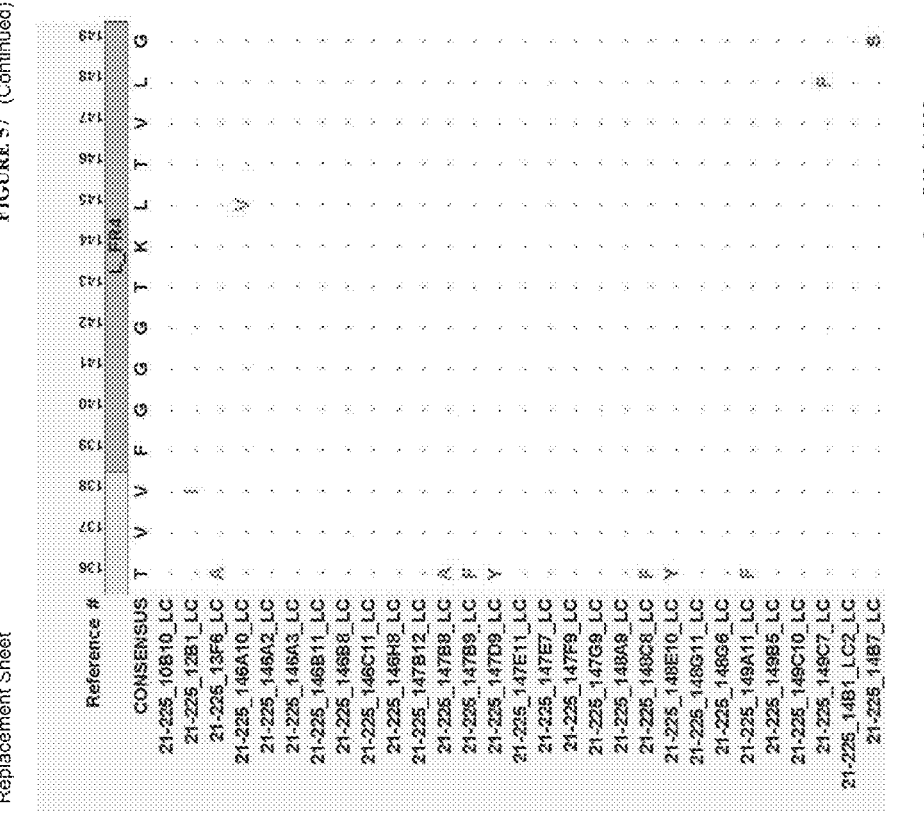
Figure 57:
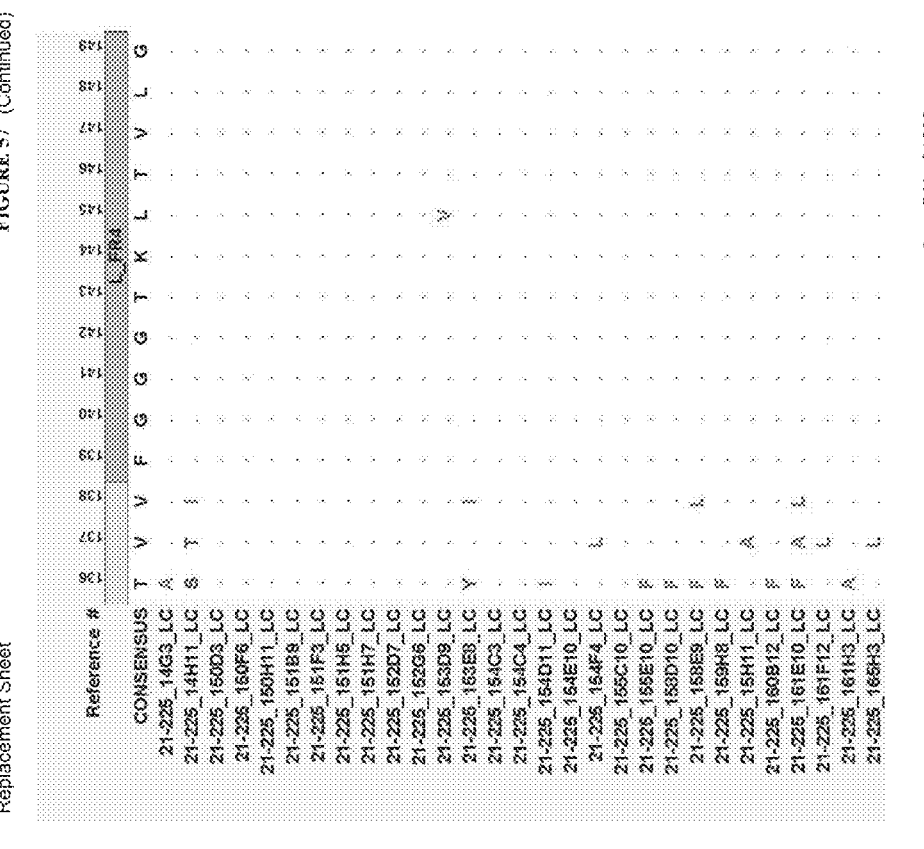
Figure 57:
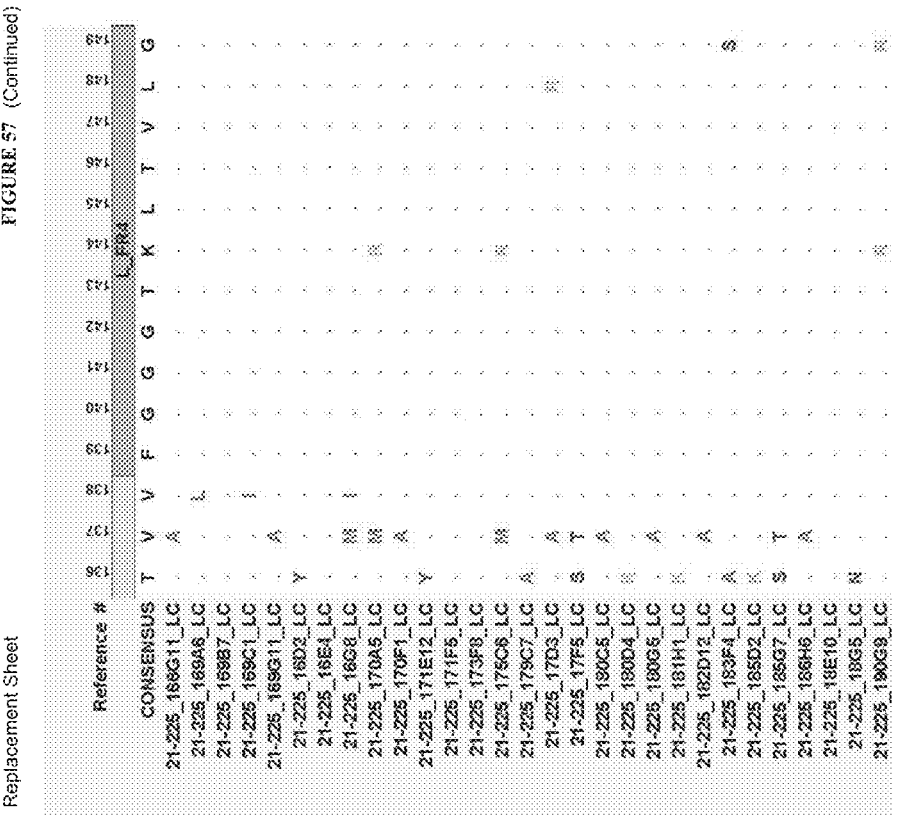
Figure 57:
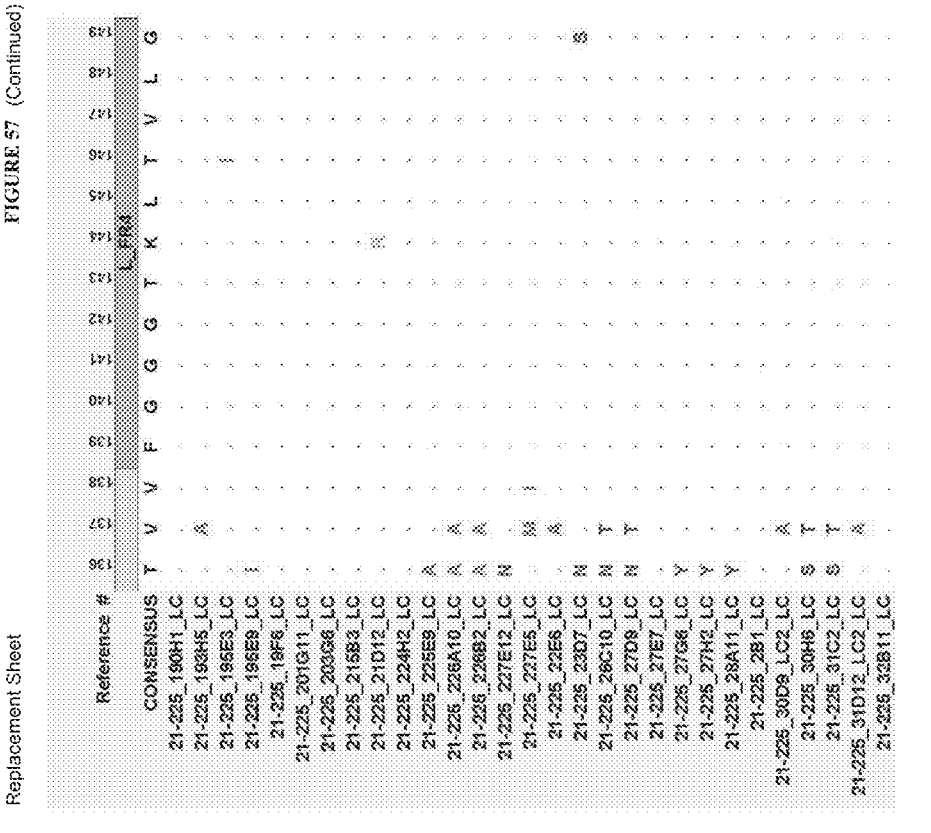
Figure 57:
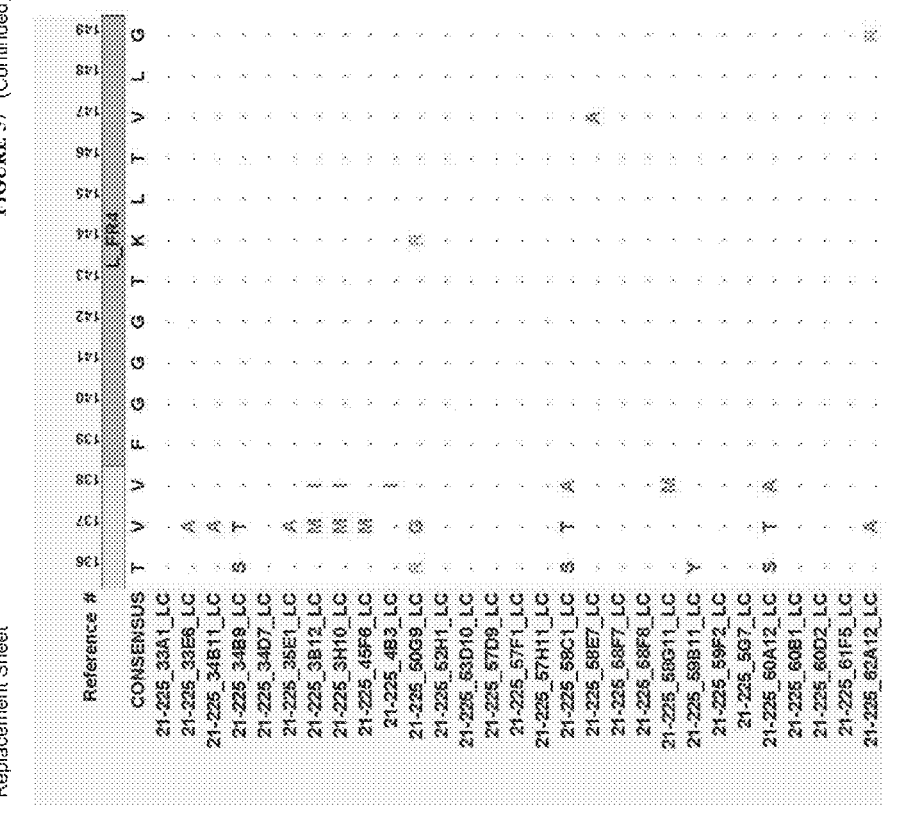
Figure 57:
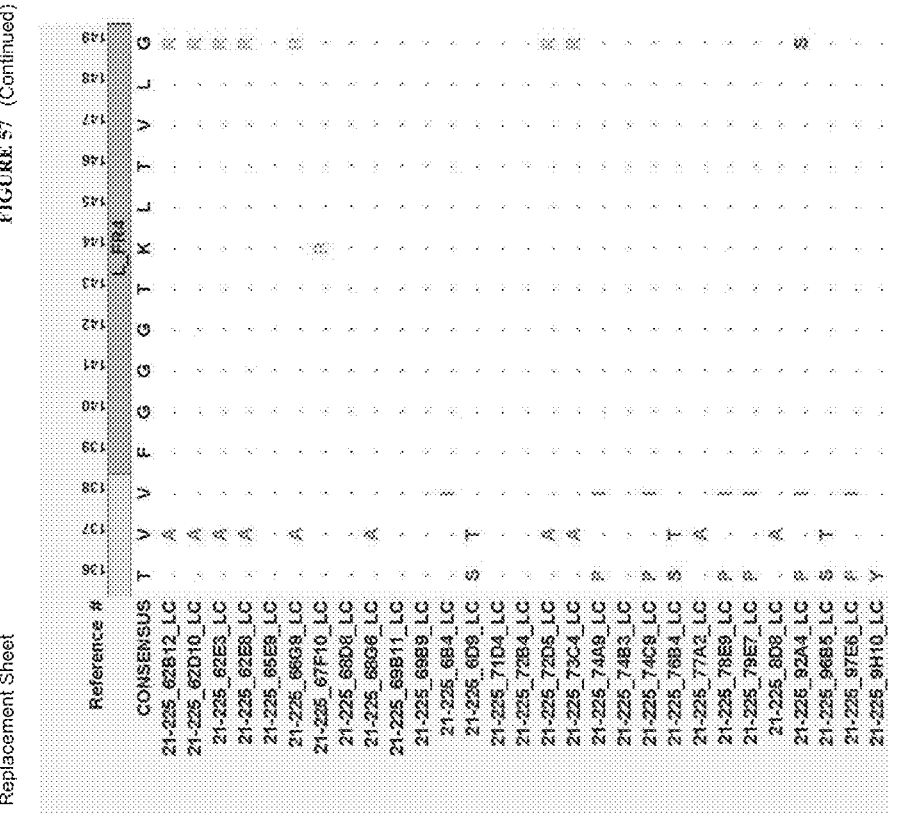
Figure 57:
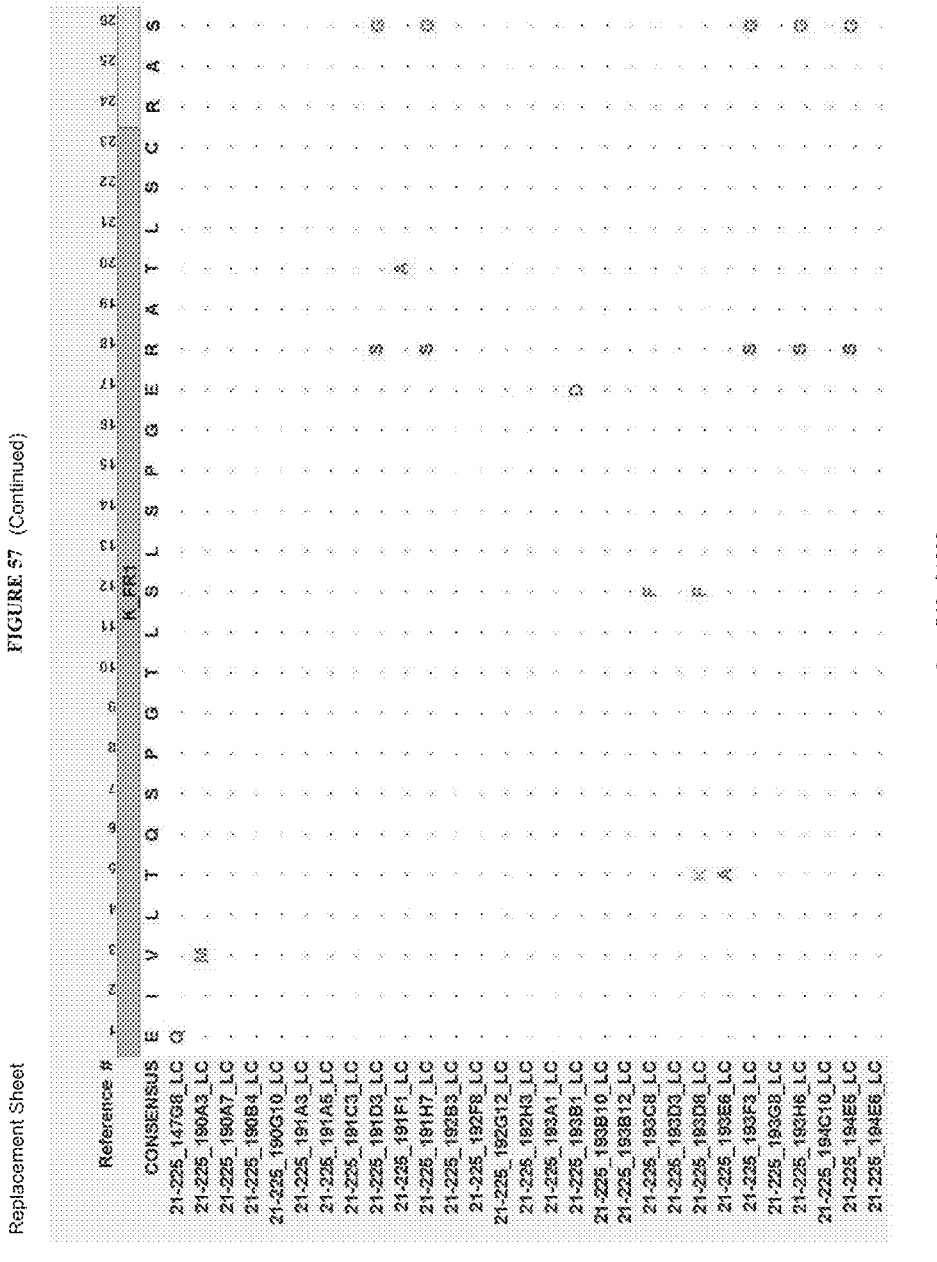
Figure 57:
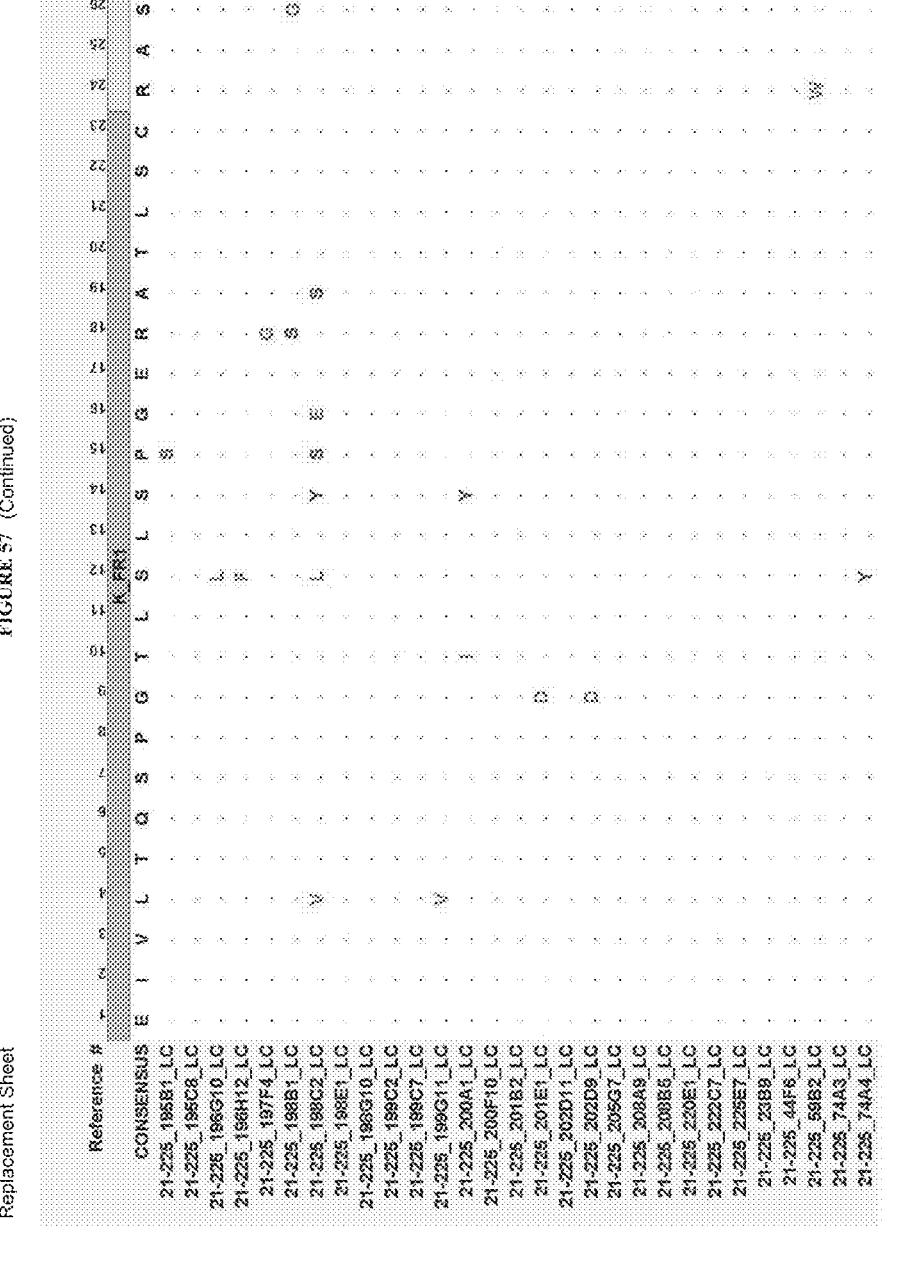
Figure 57:
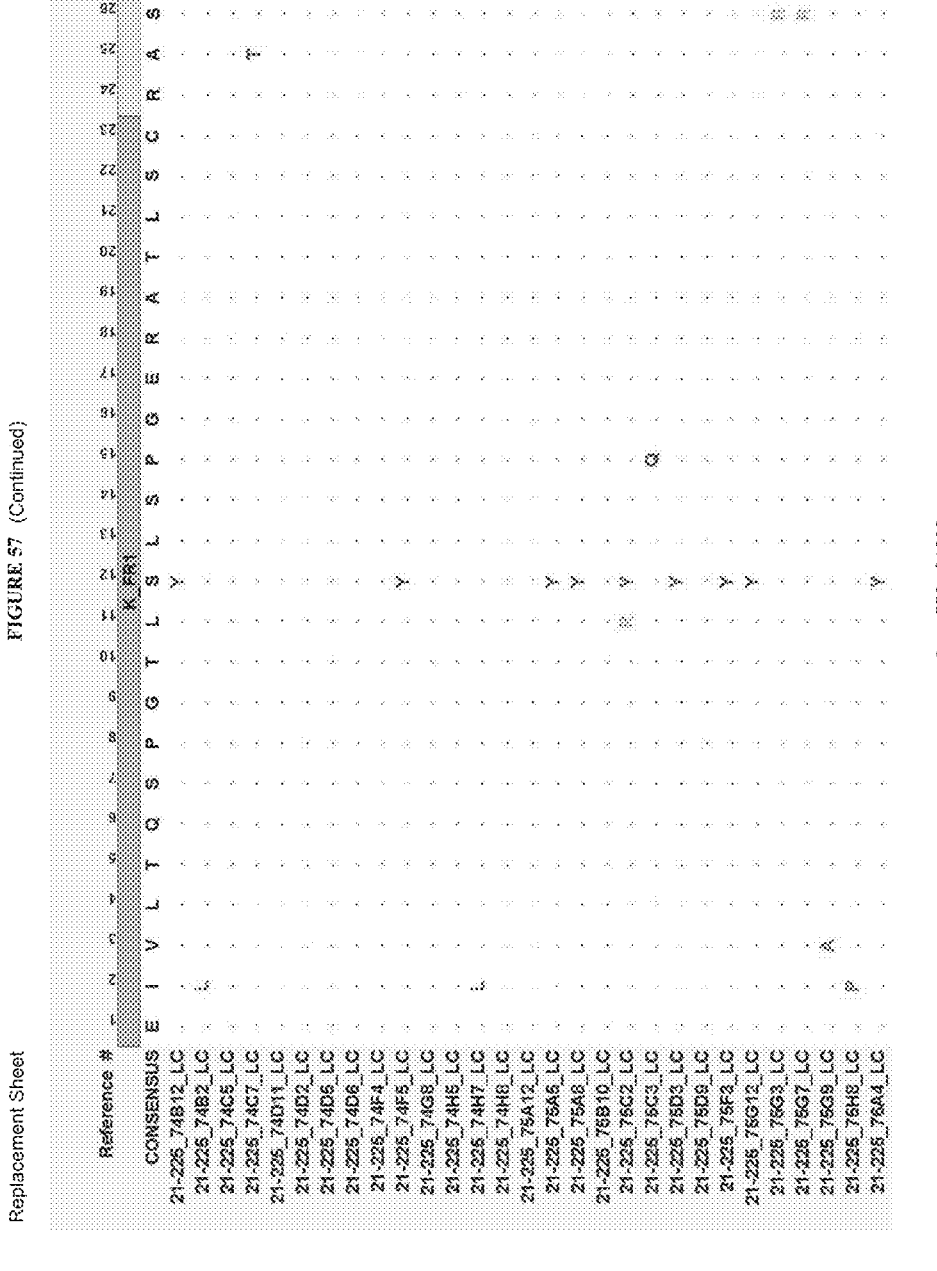
Figure 57:
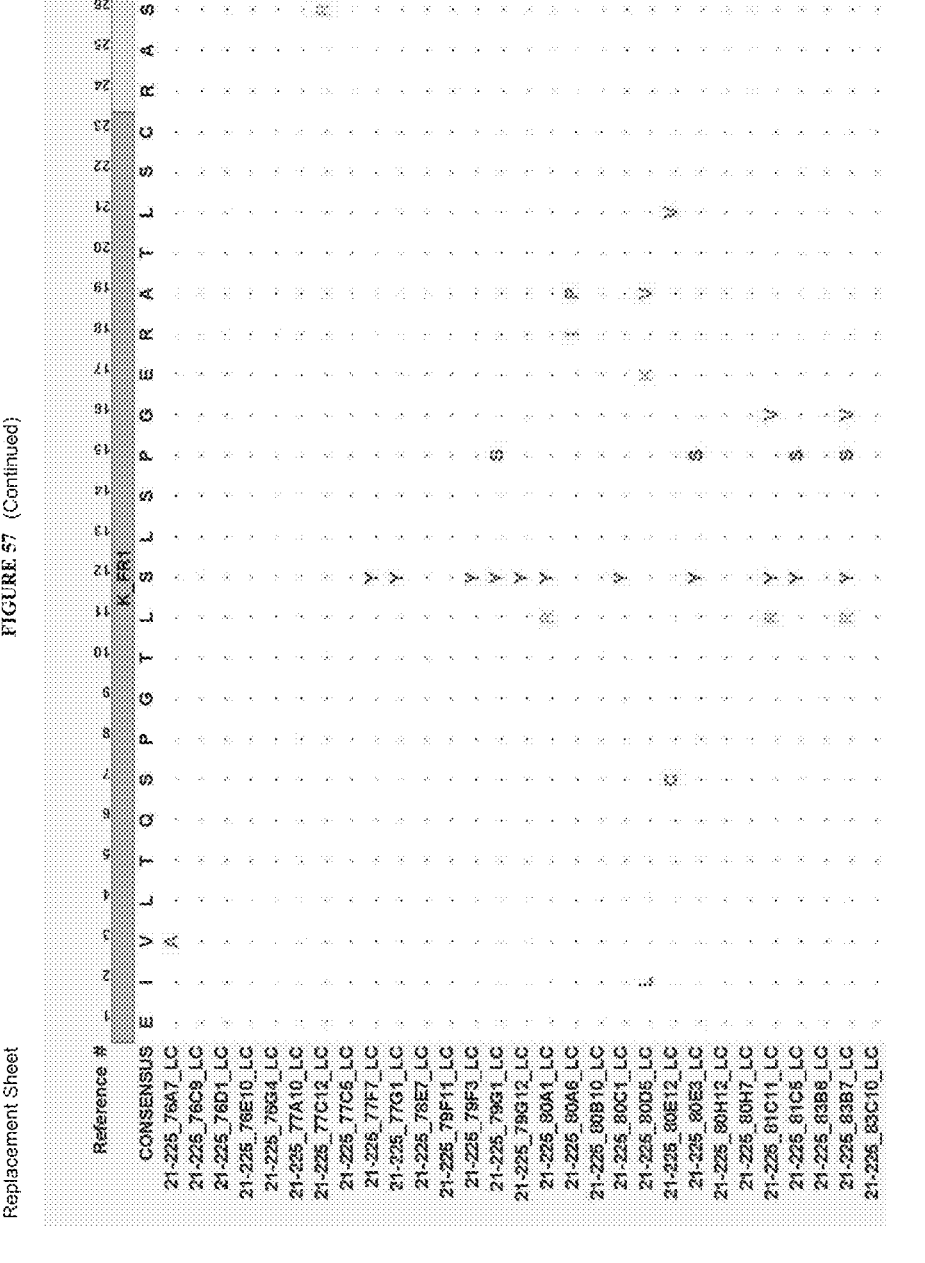
Figure 57:
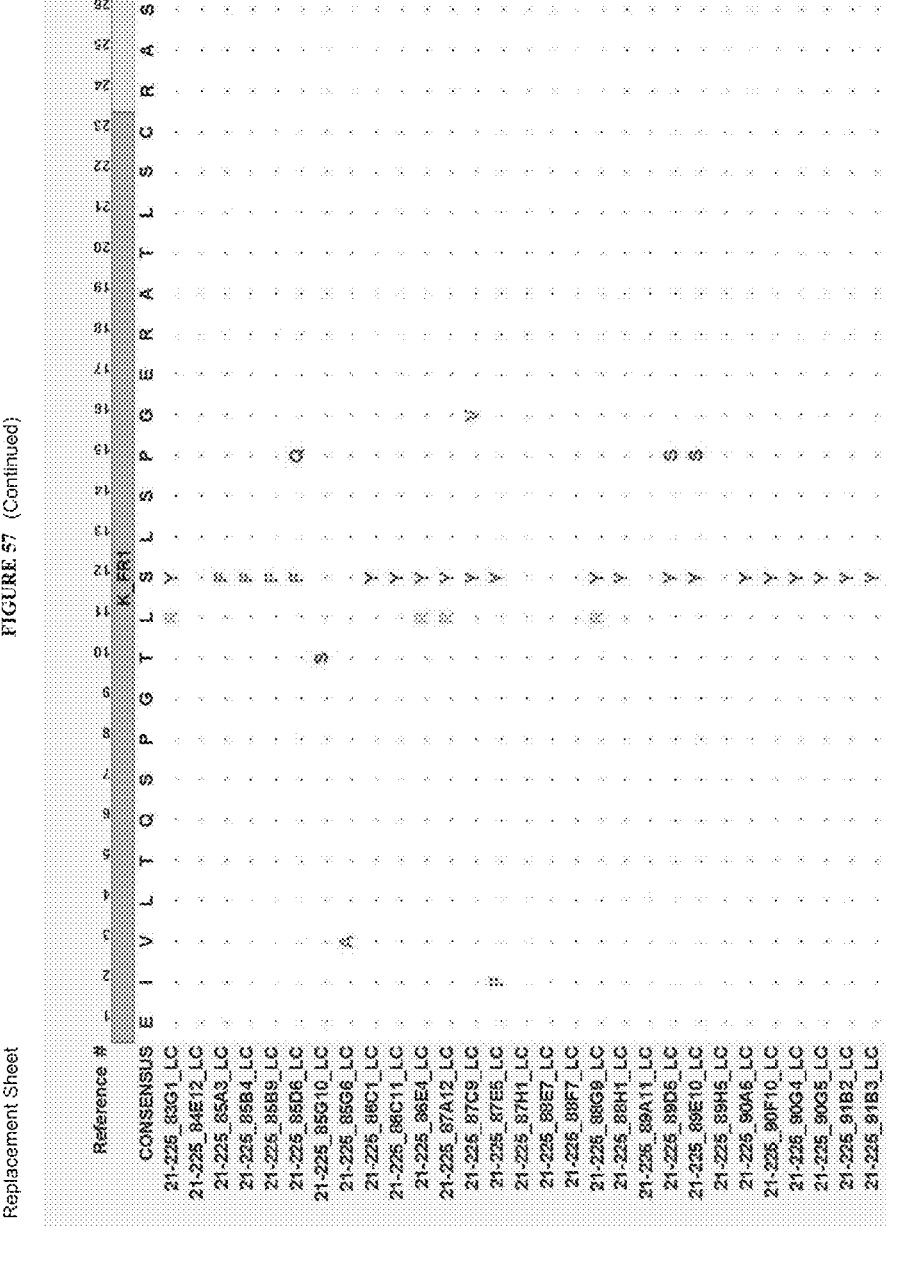
Figure 57:
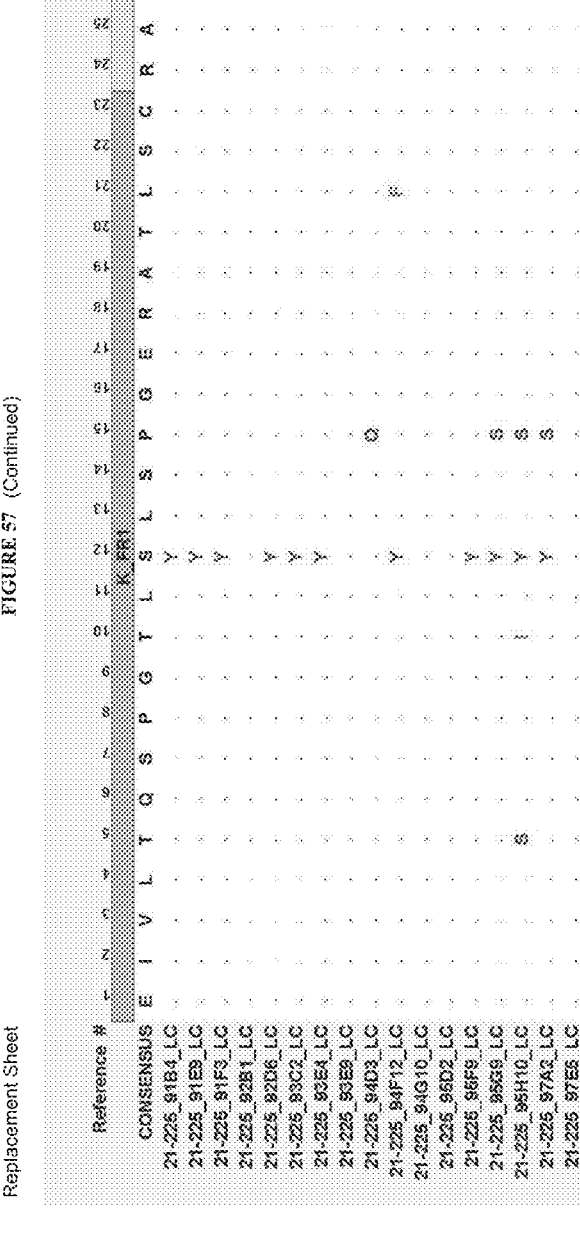
Figure 57:
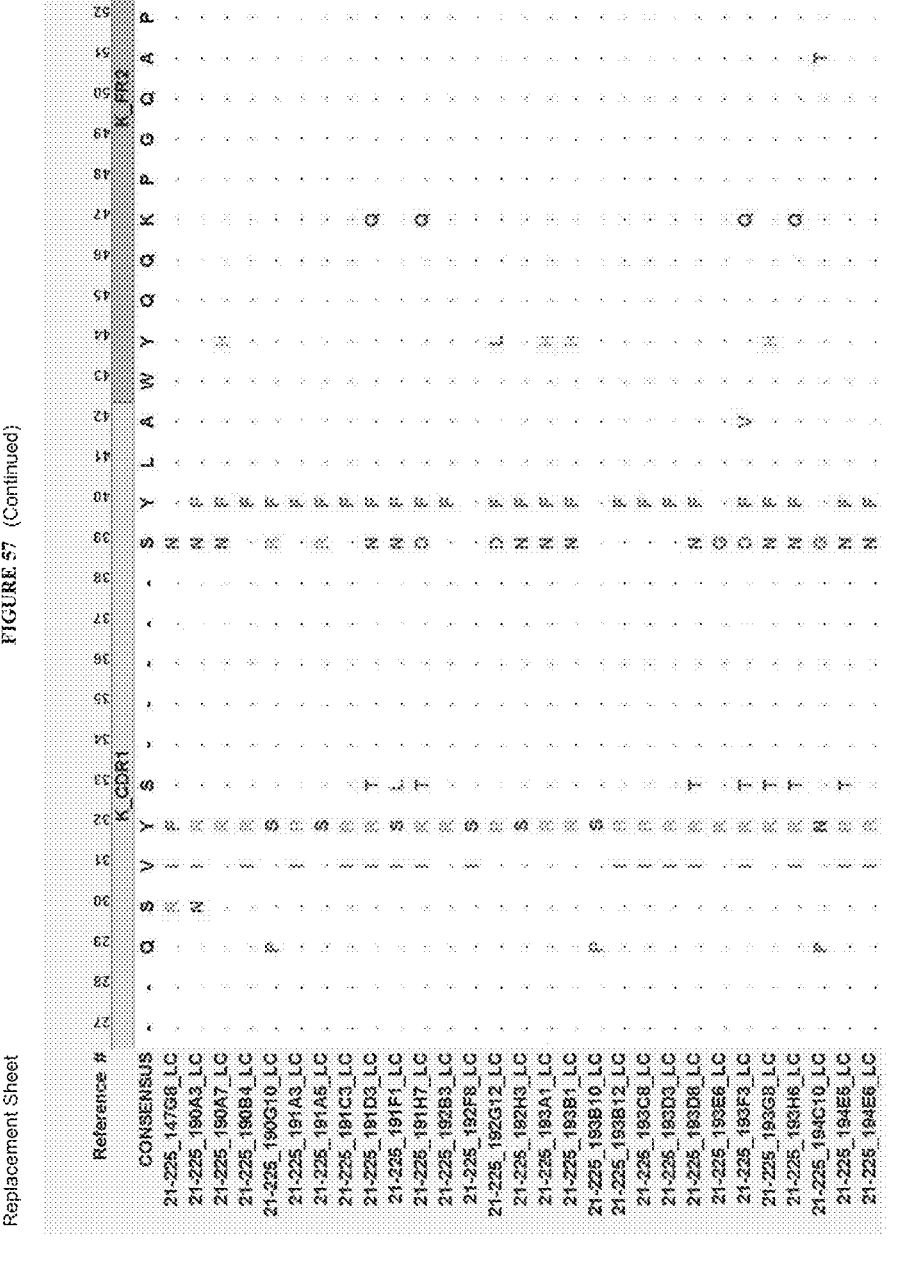
Figure 57:
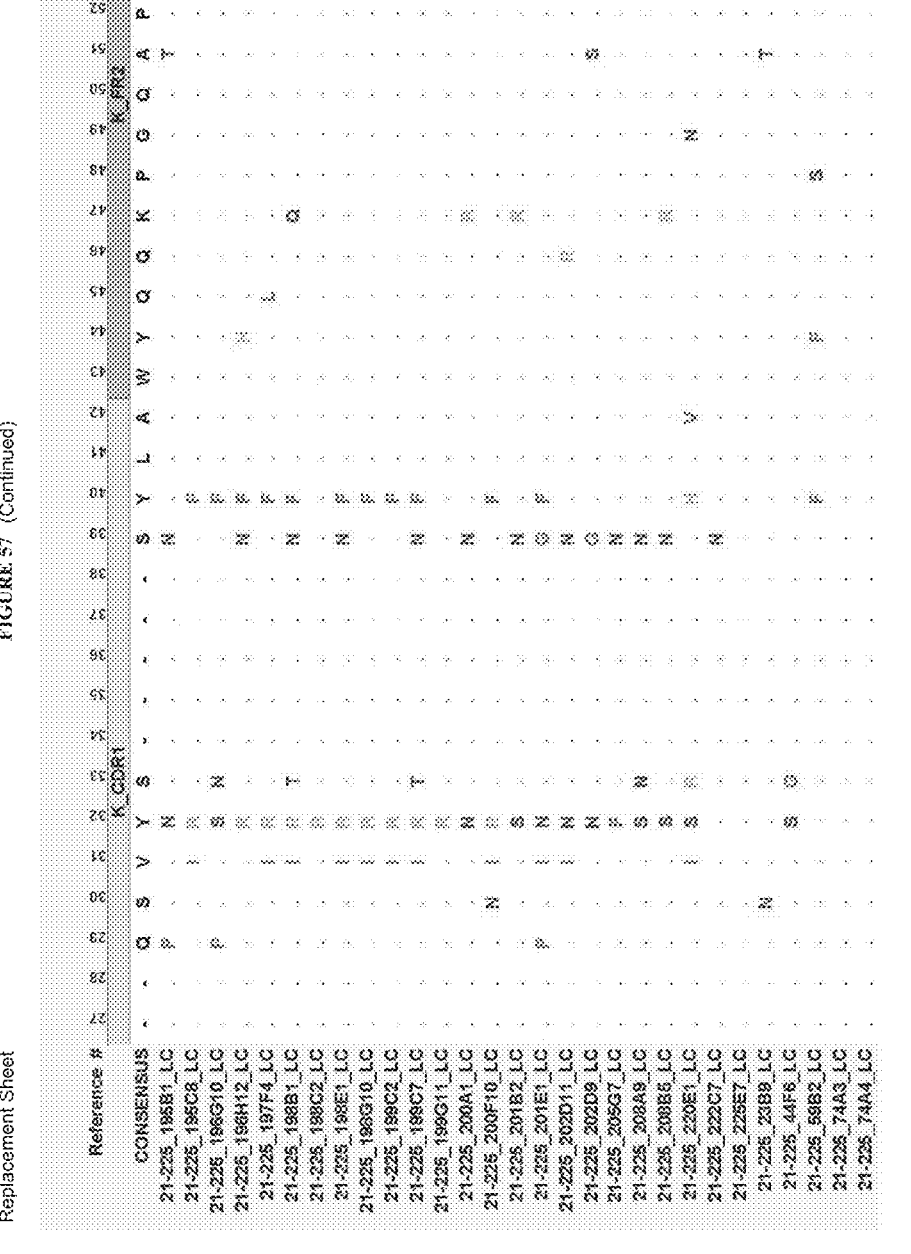
Figure 57:
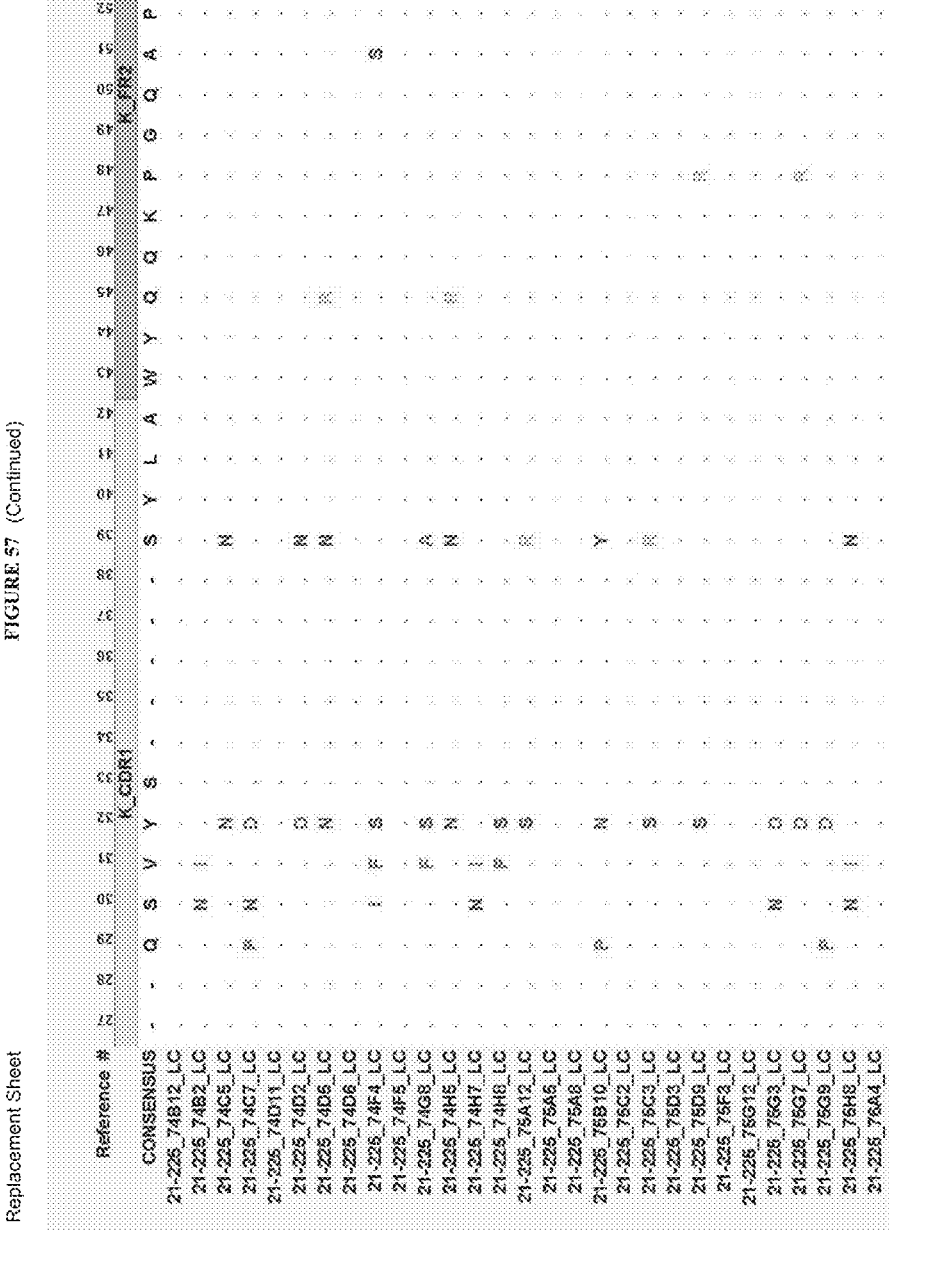
Figure 57:
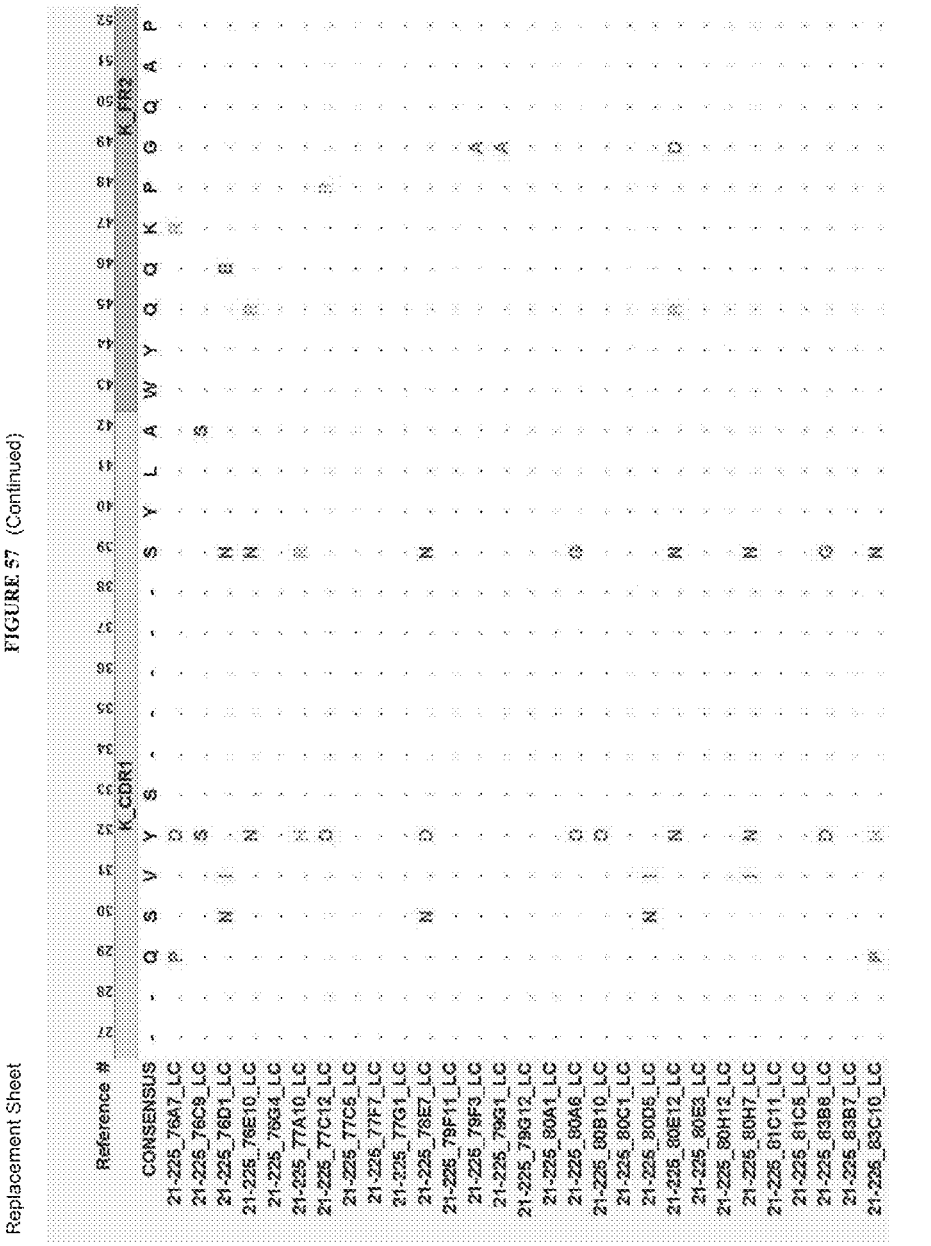
Figure 57:
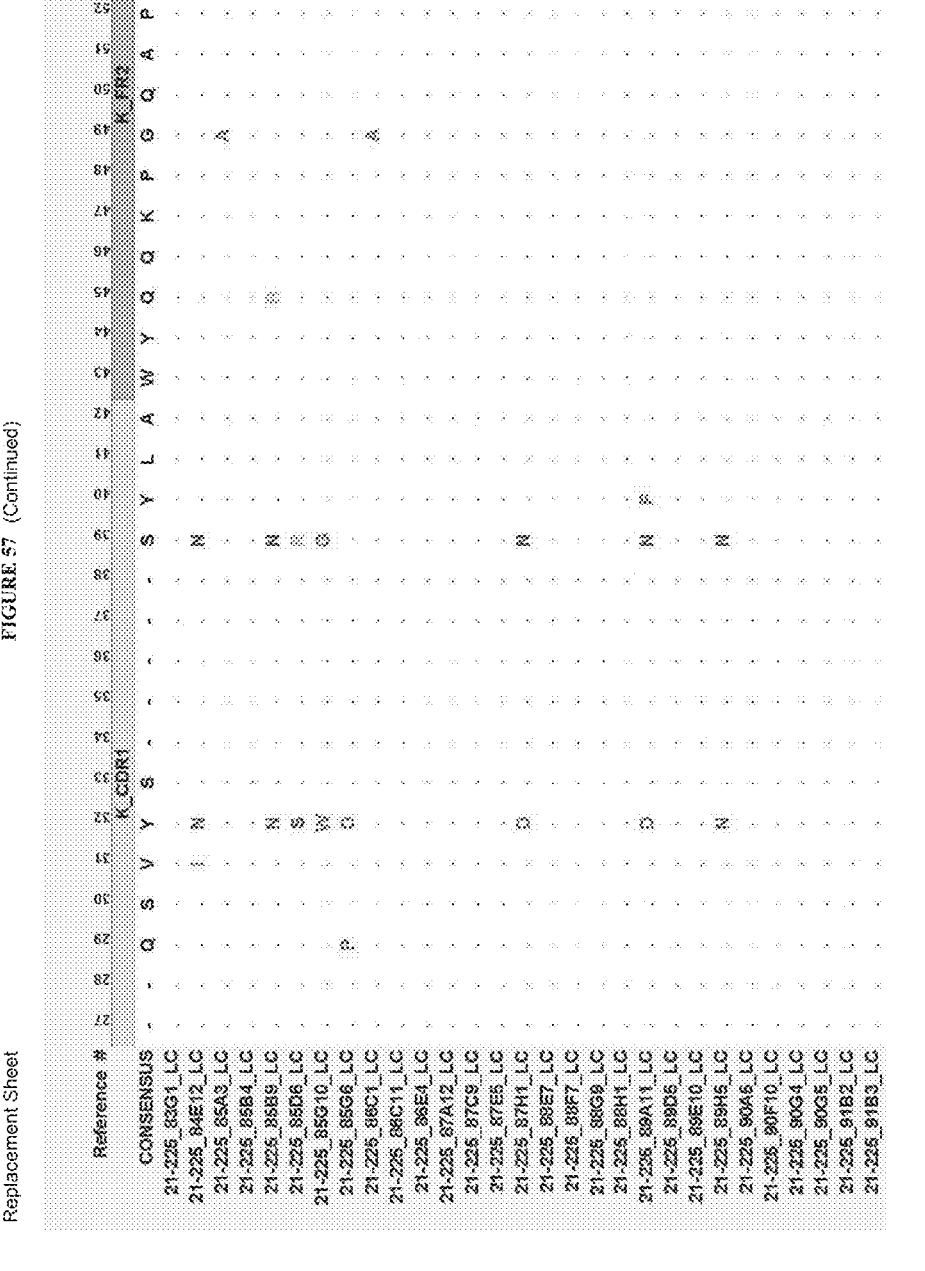
Figure 57:
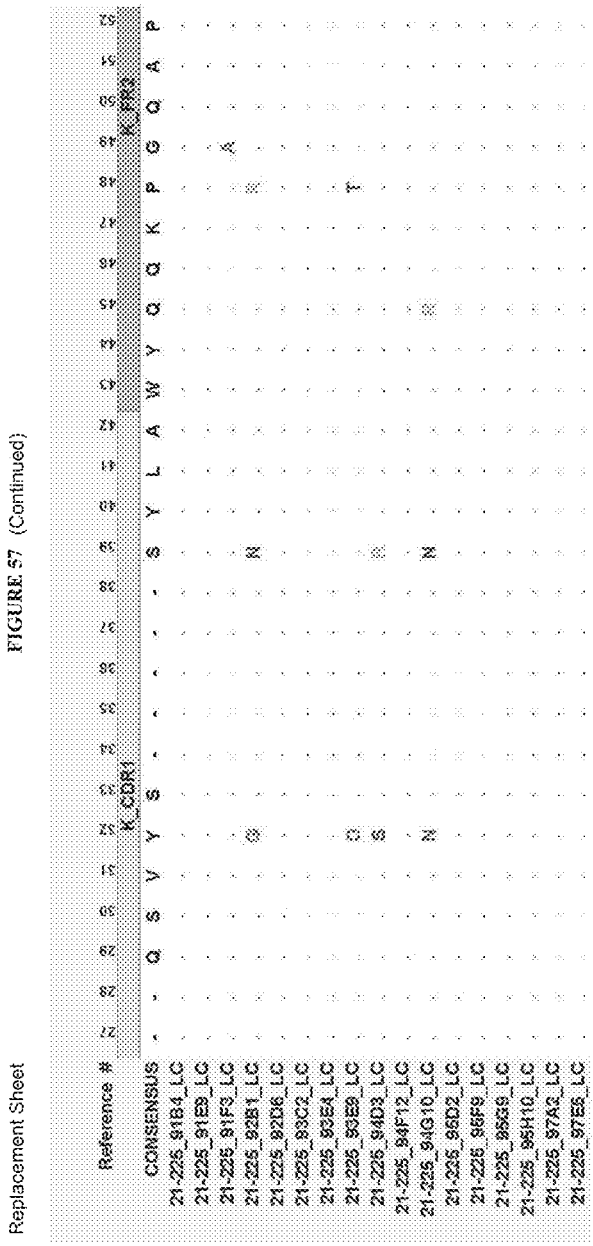
Figure 57:
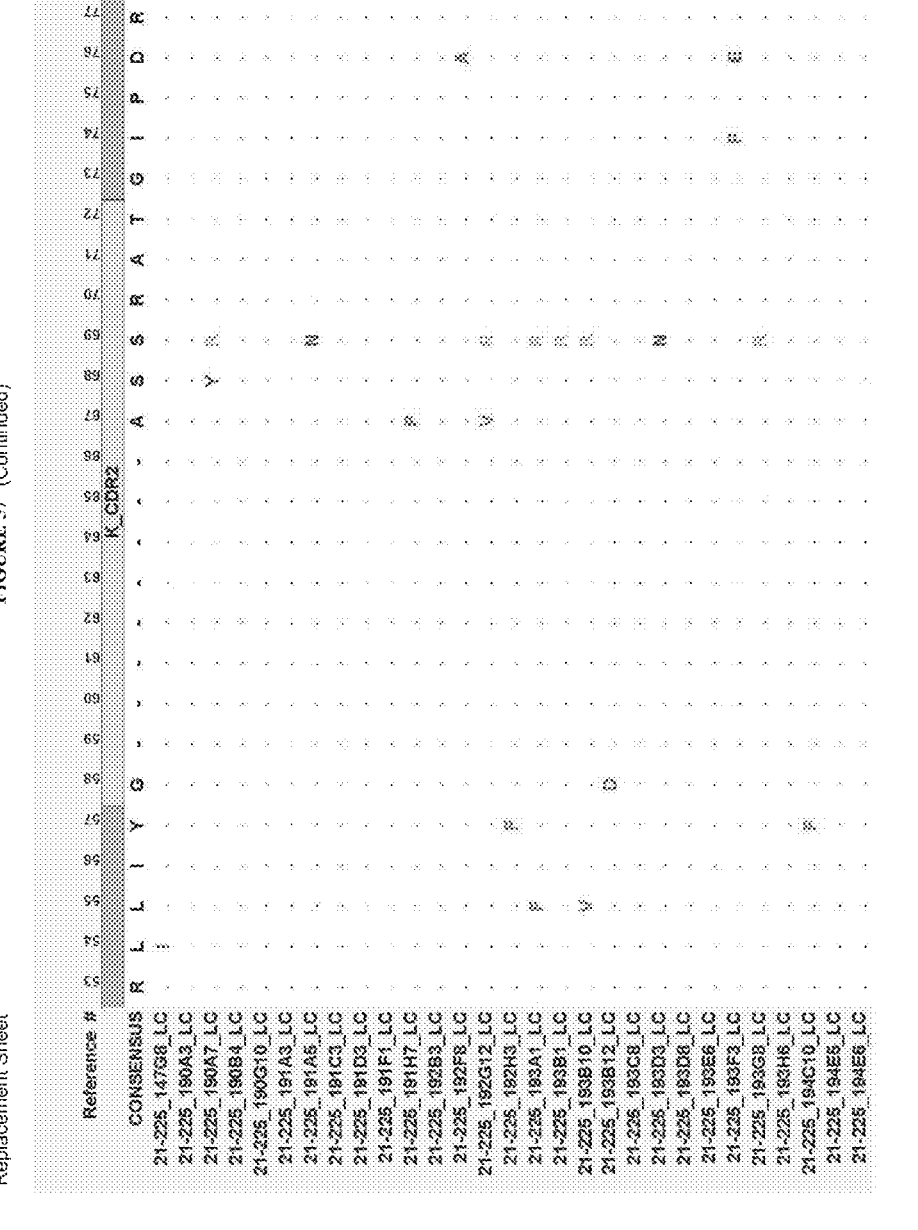
Figure 57:
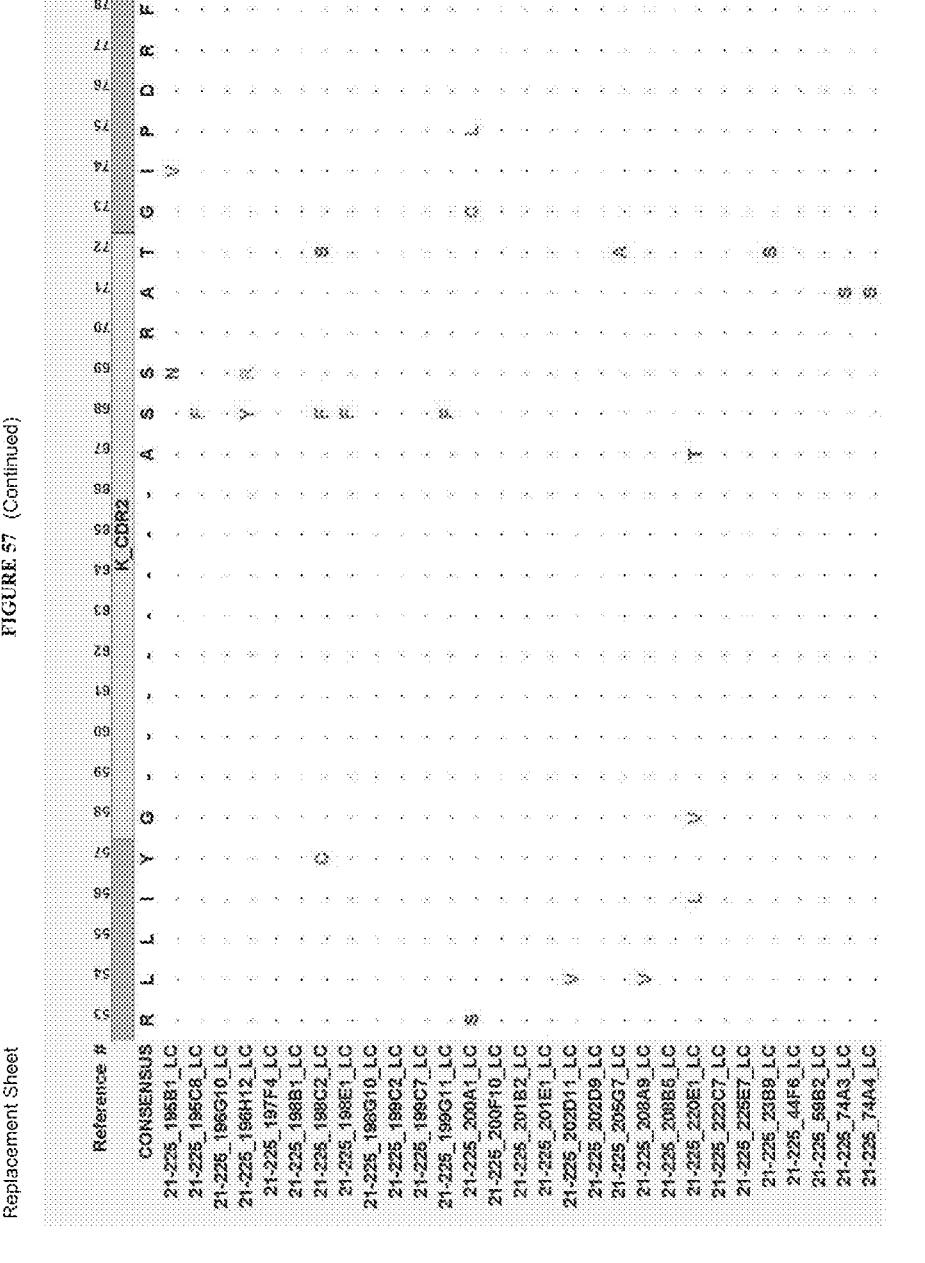
Figure 57:
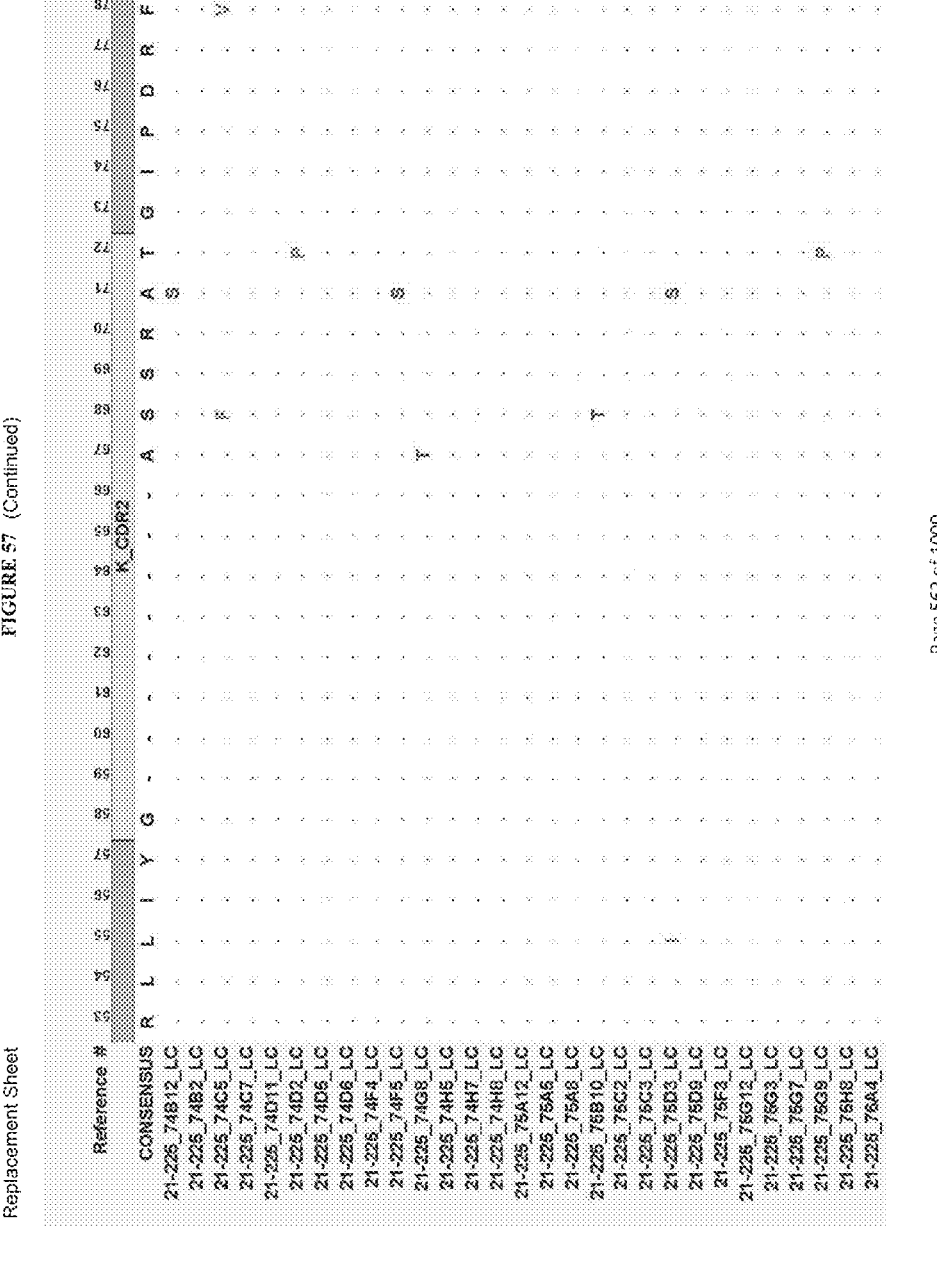
Figure 57:
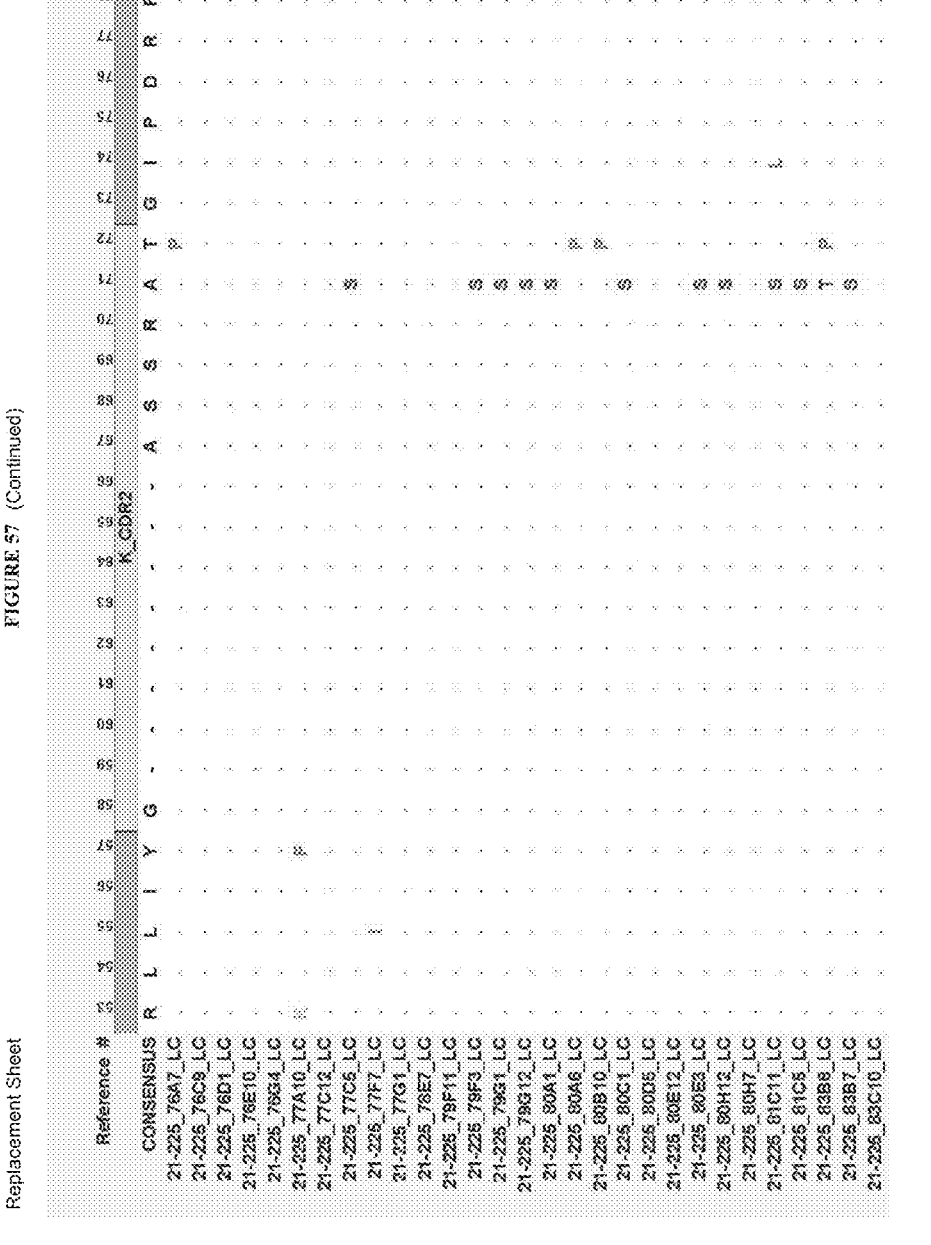
Figure 57:
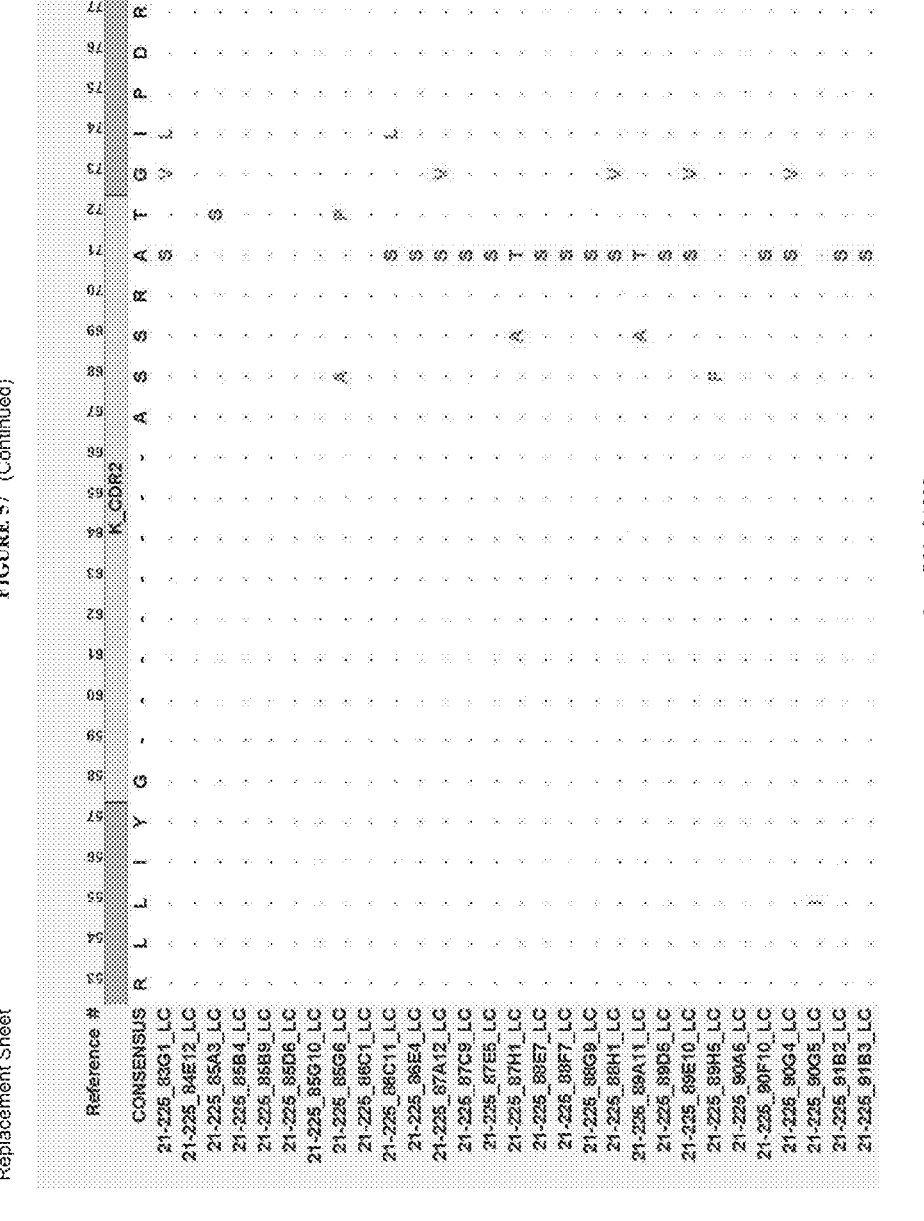
Figure 57:
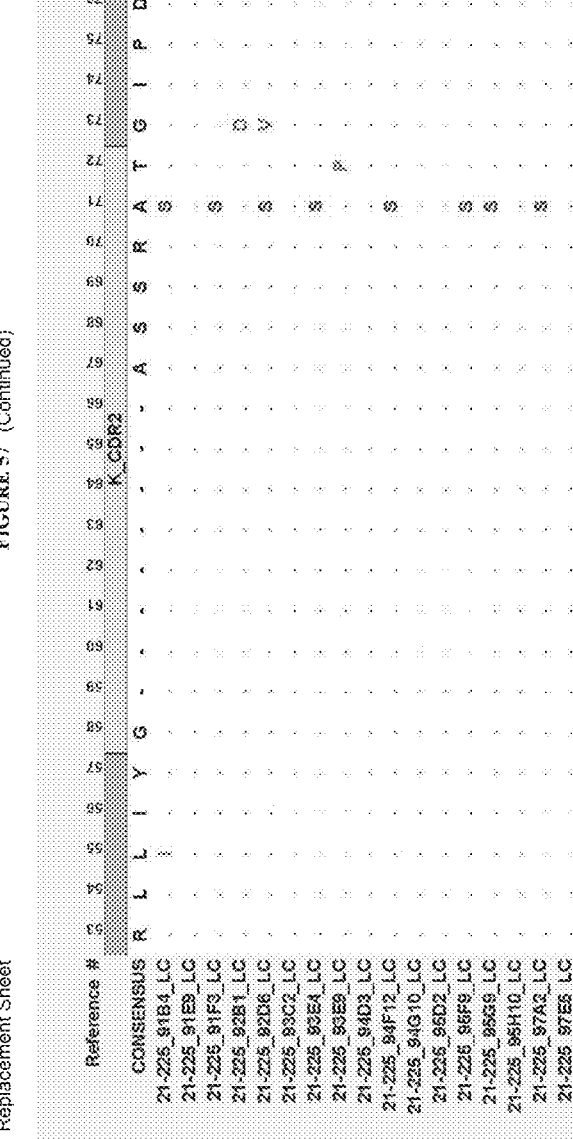
Figure 57:
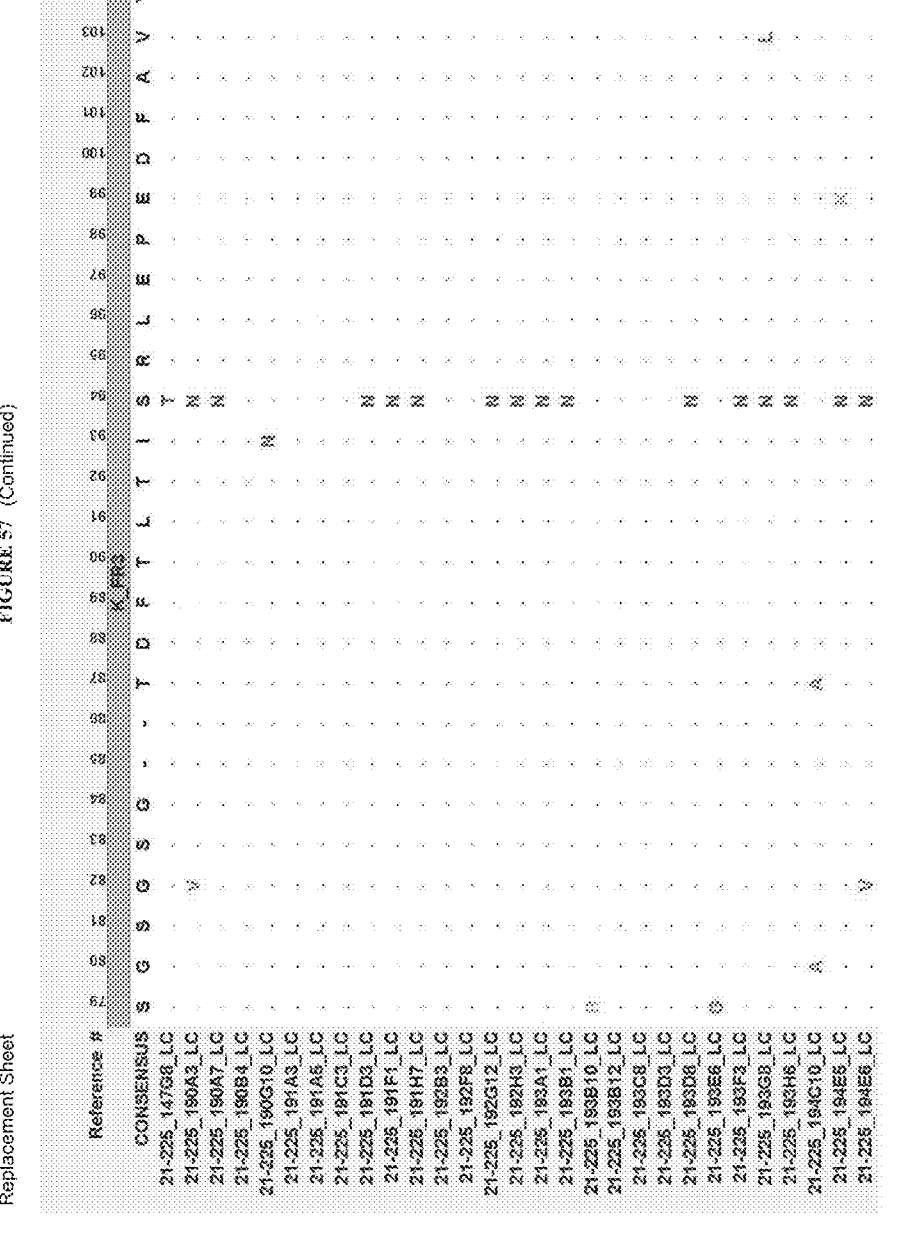
Figure 57:
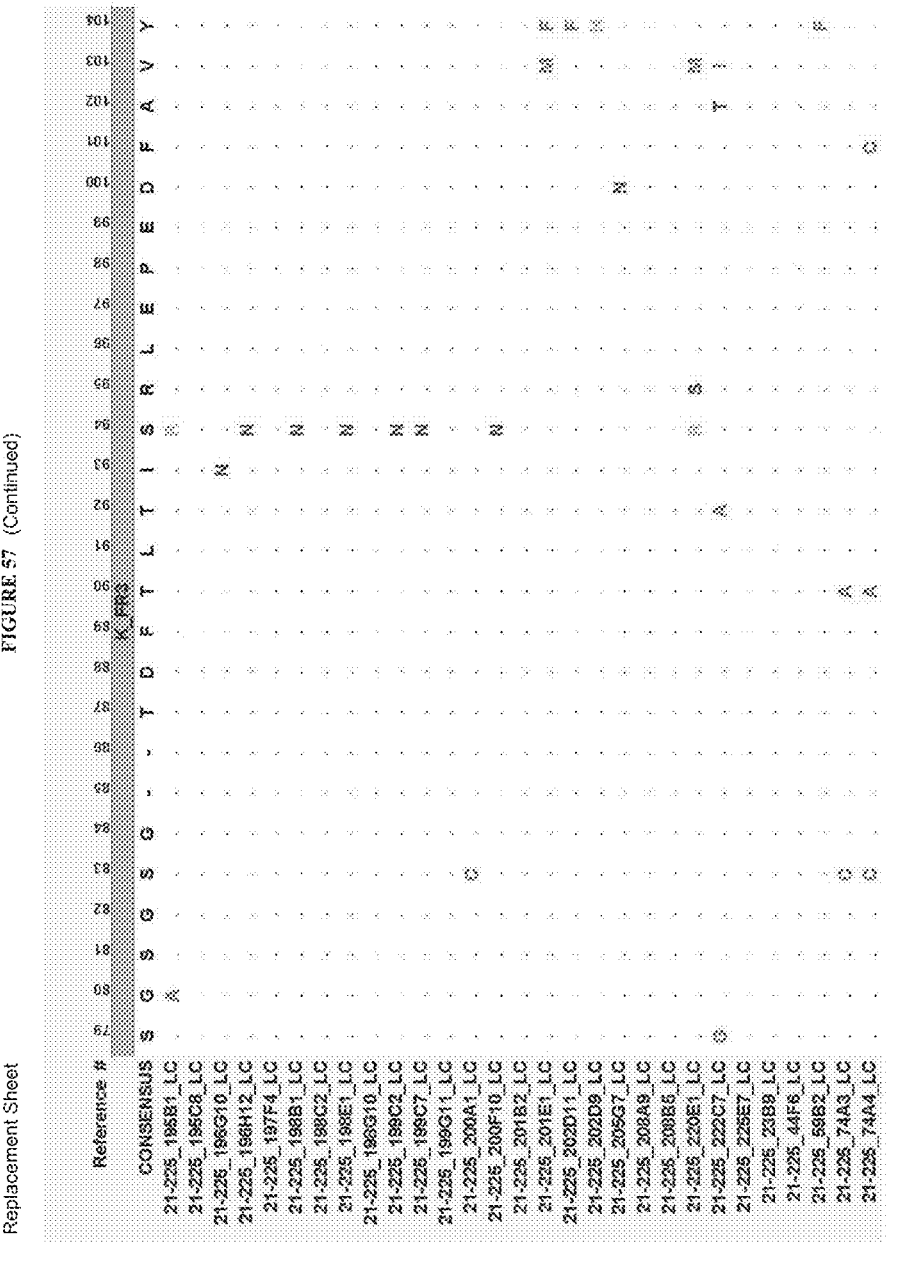
Figure 57:
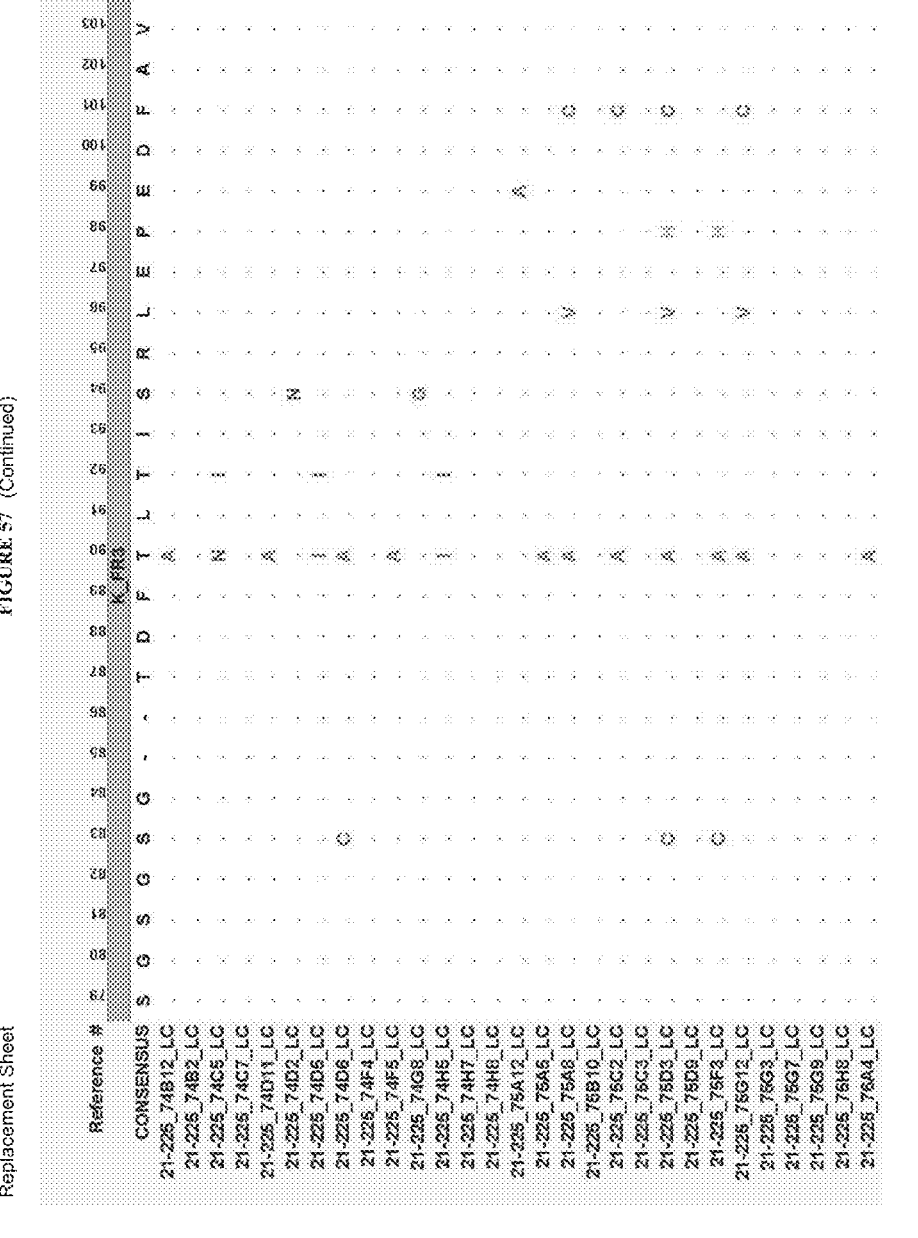
Figure 57:
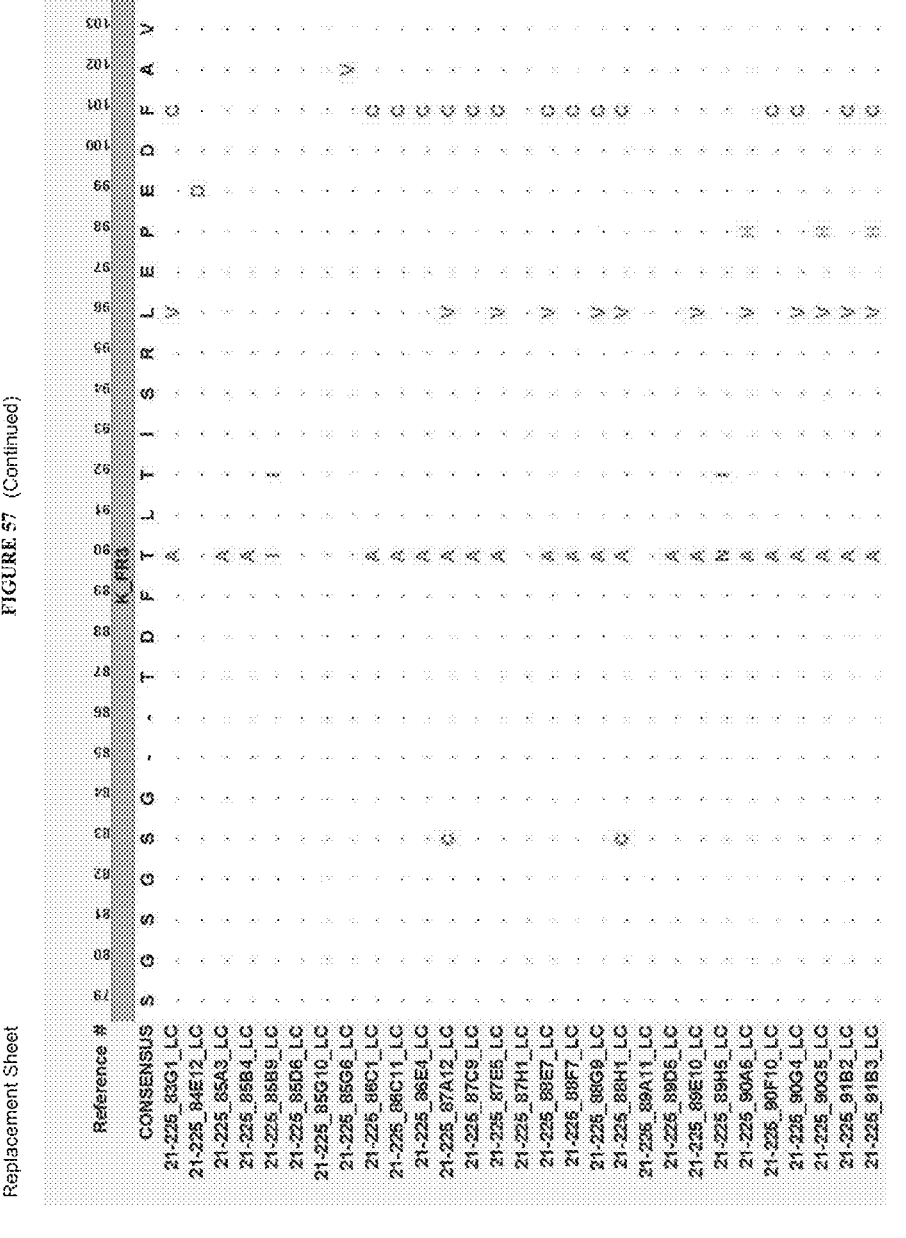
Figure 57:
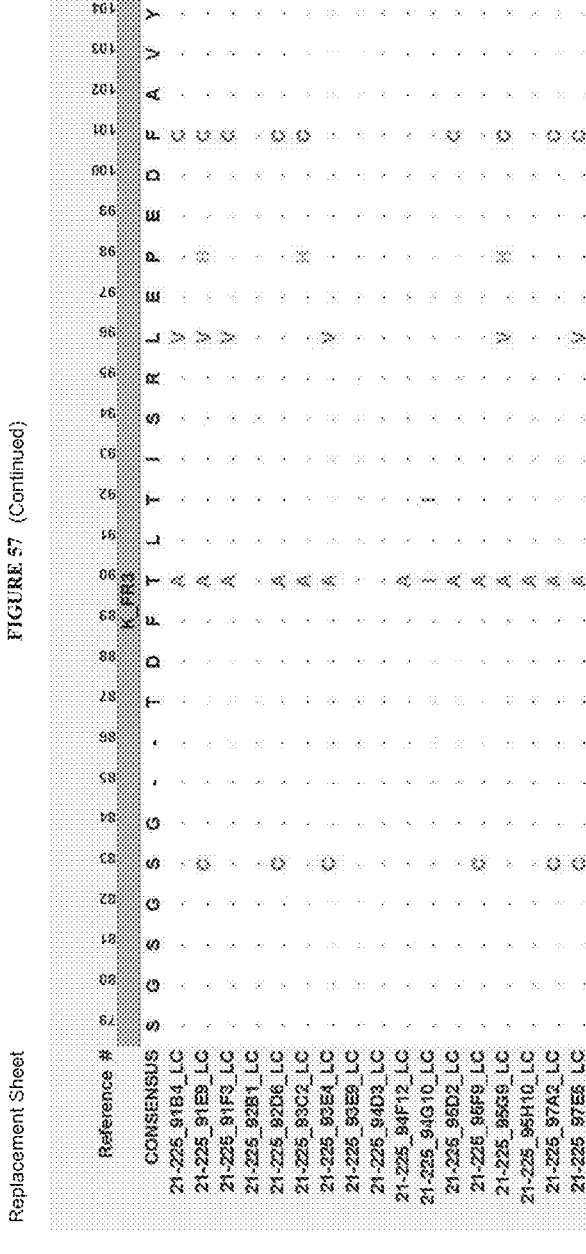
Figure 57:
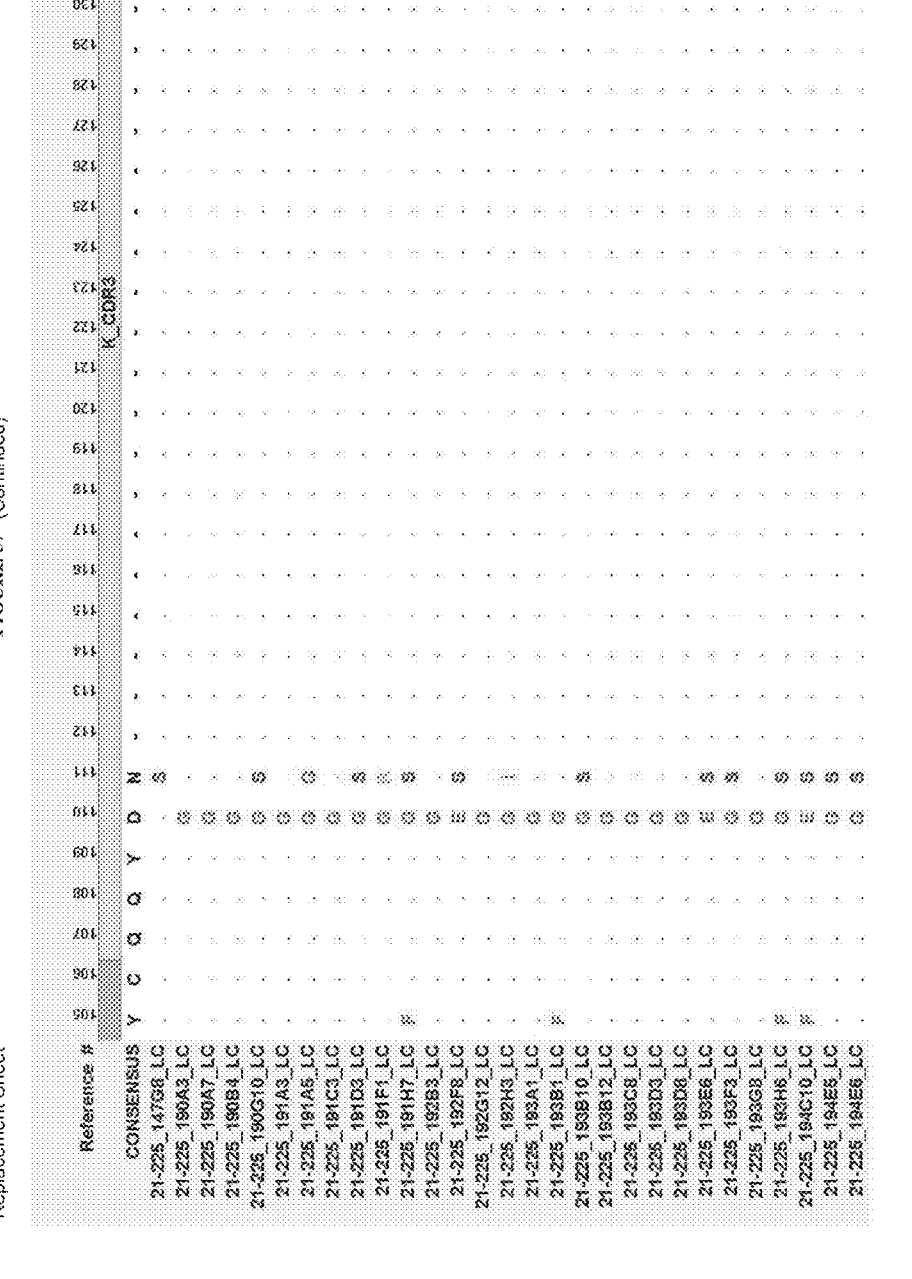
Figure 57:
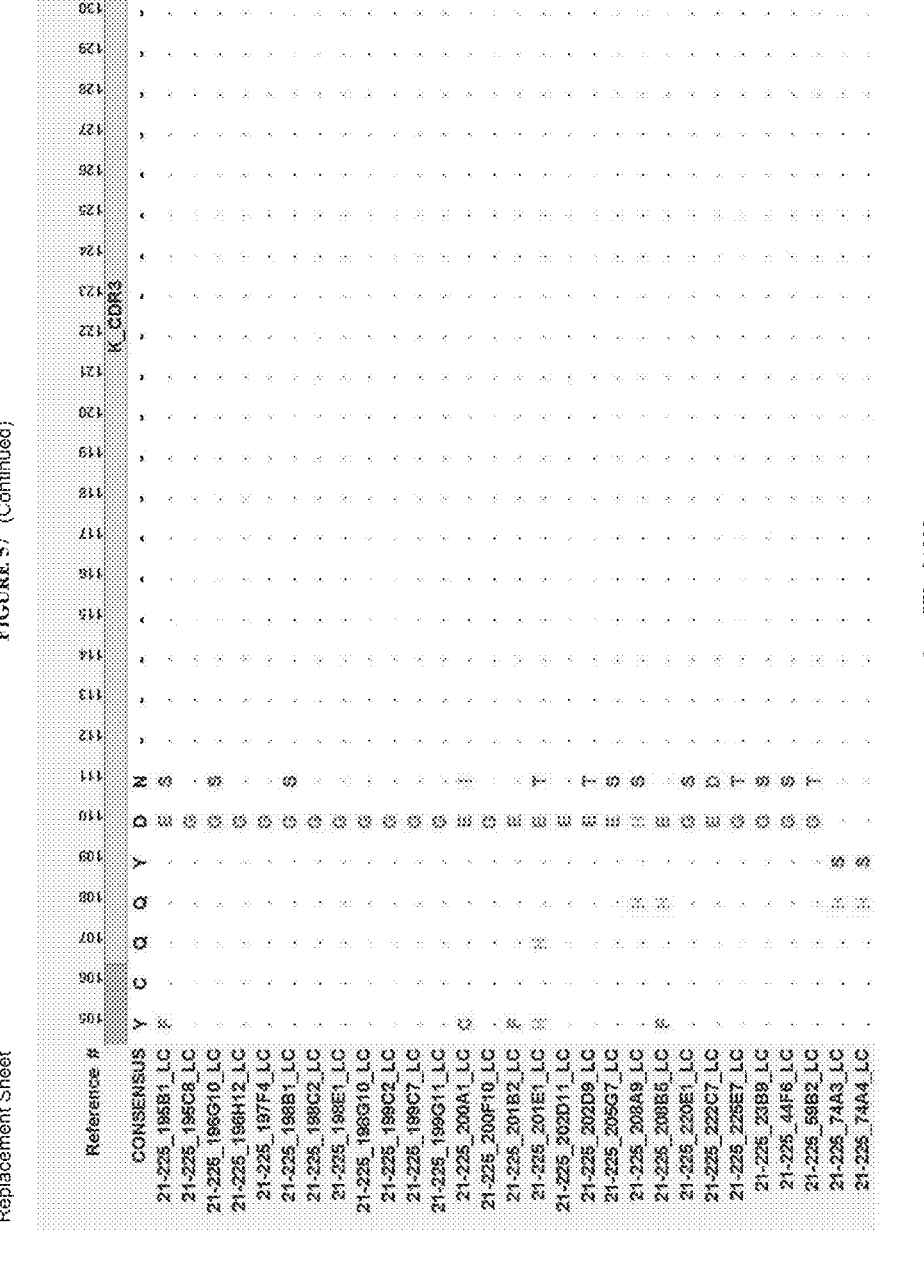
Figure 57:
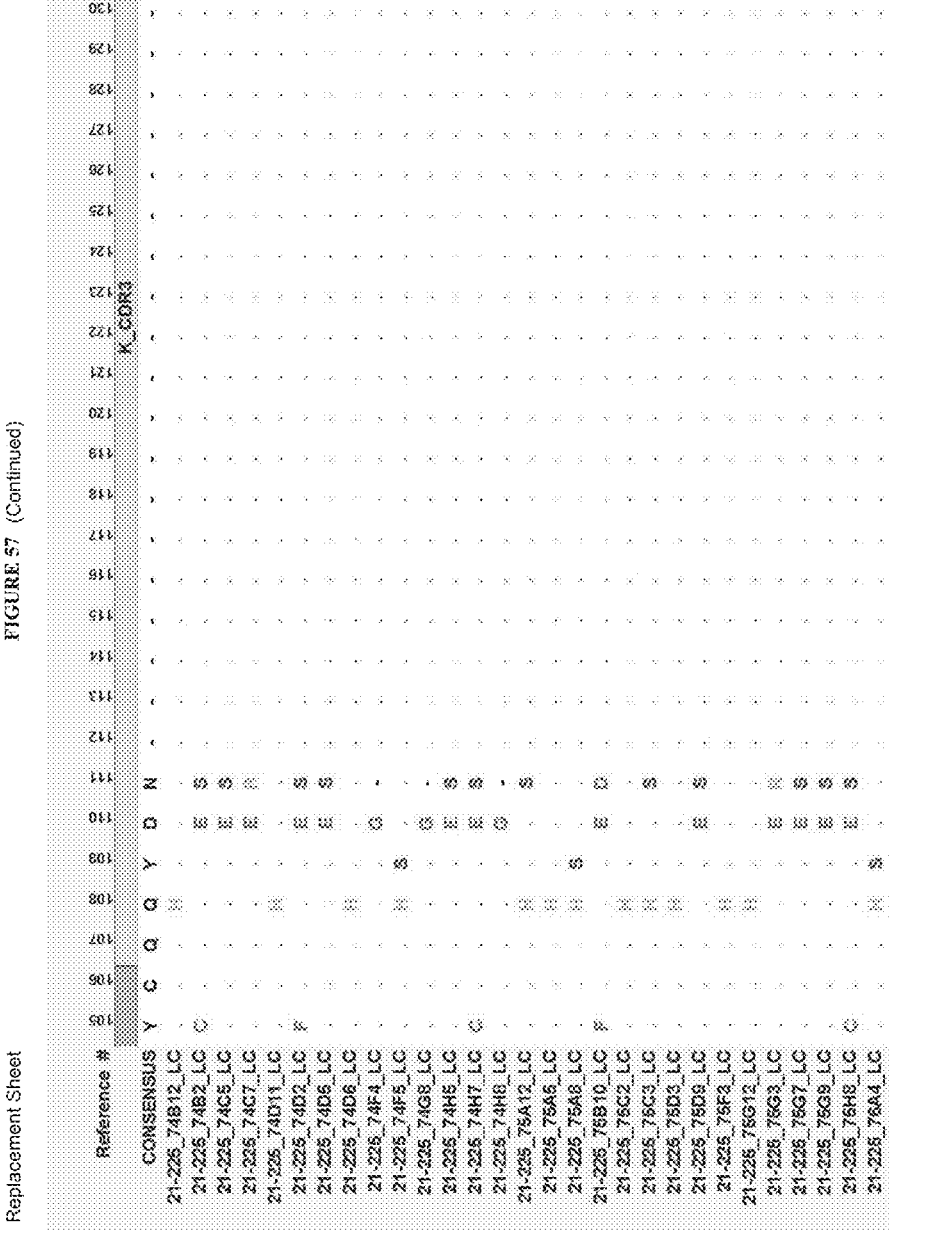
Figure 57:
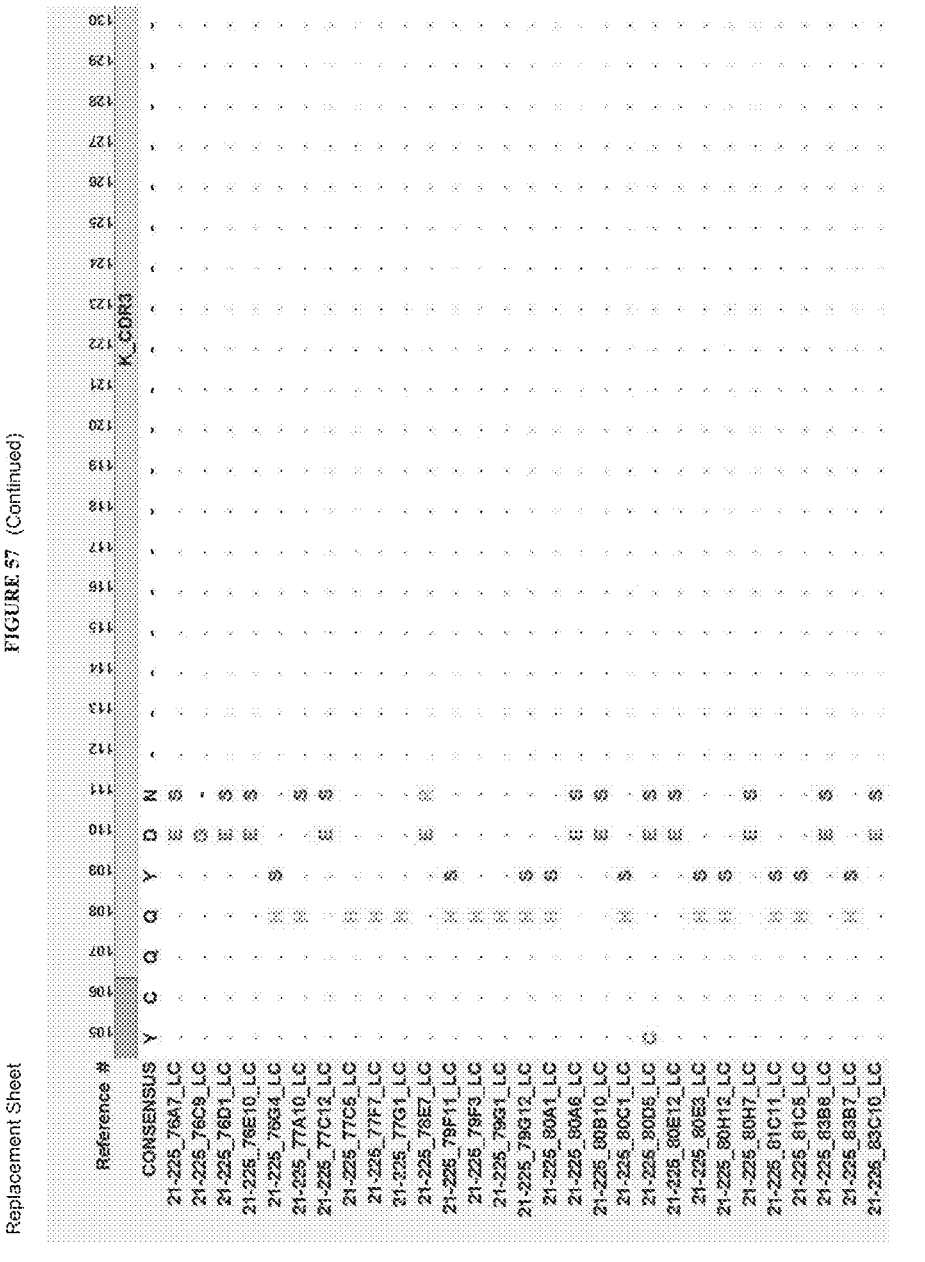
Figure 57:
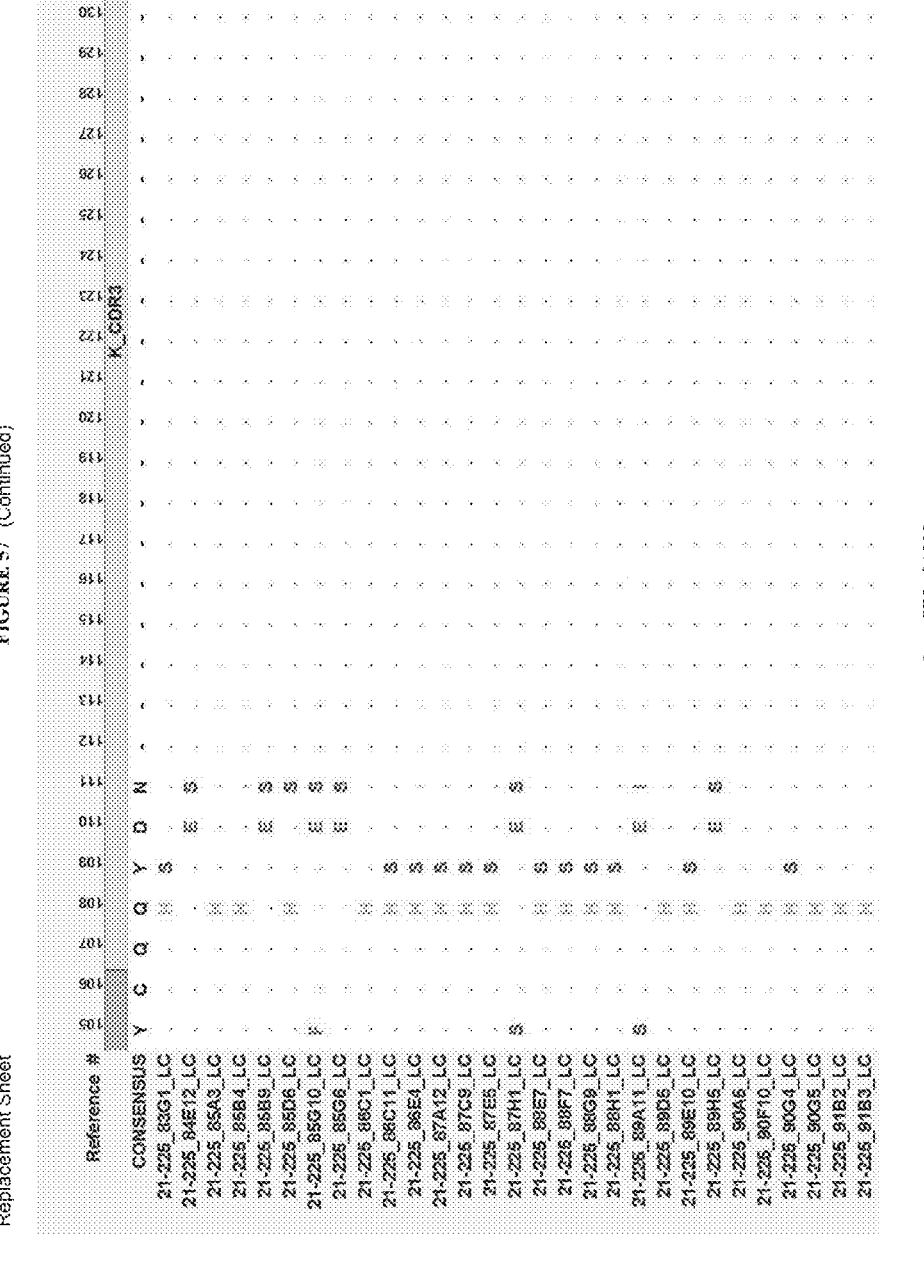
Figure 57:
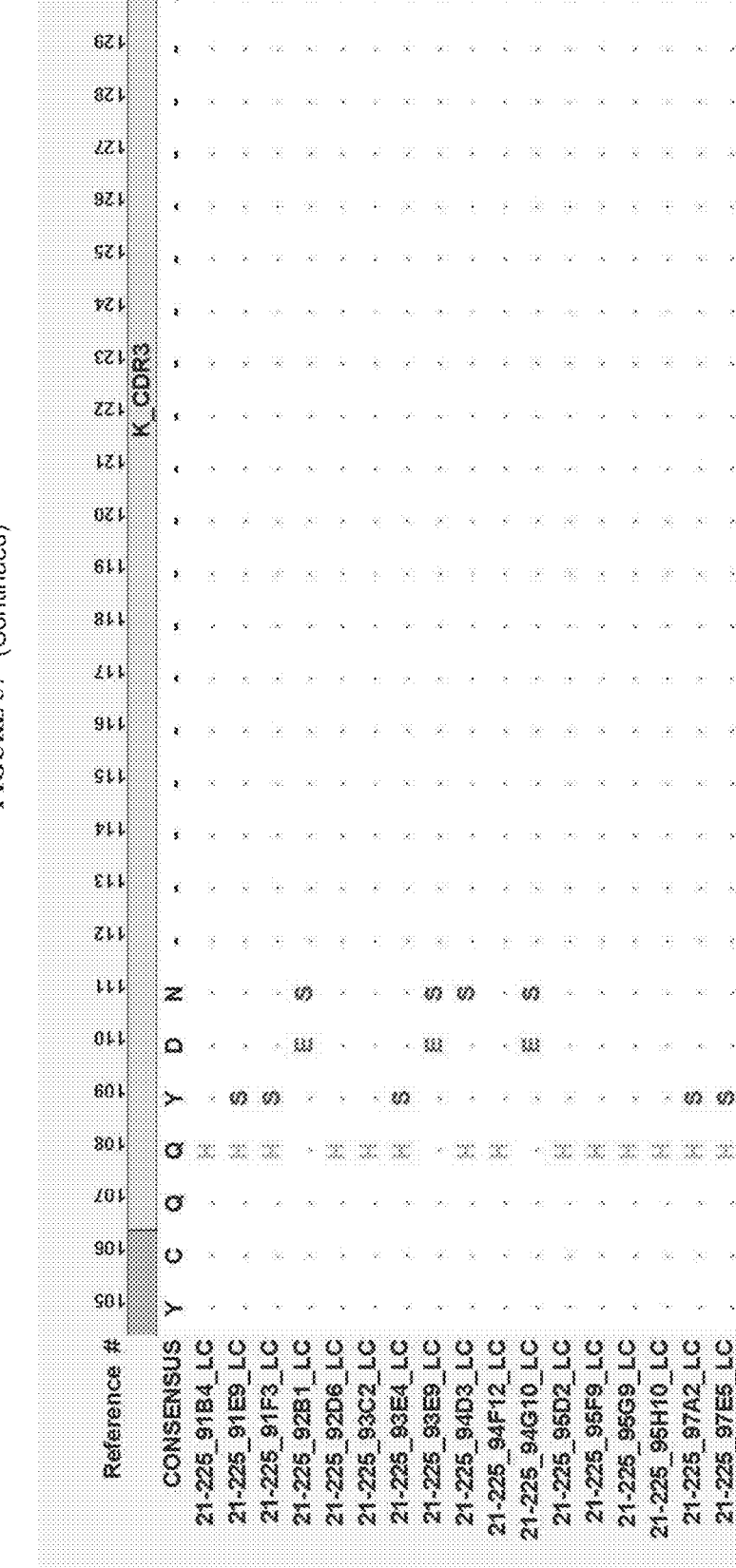
Figure 57:
Figure 57:
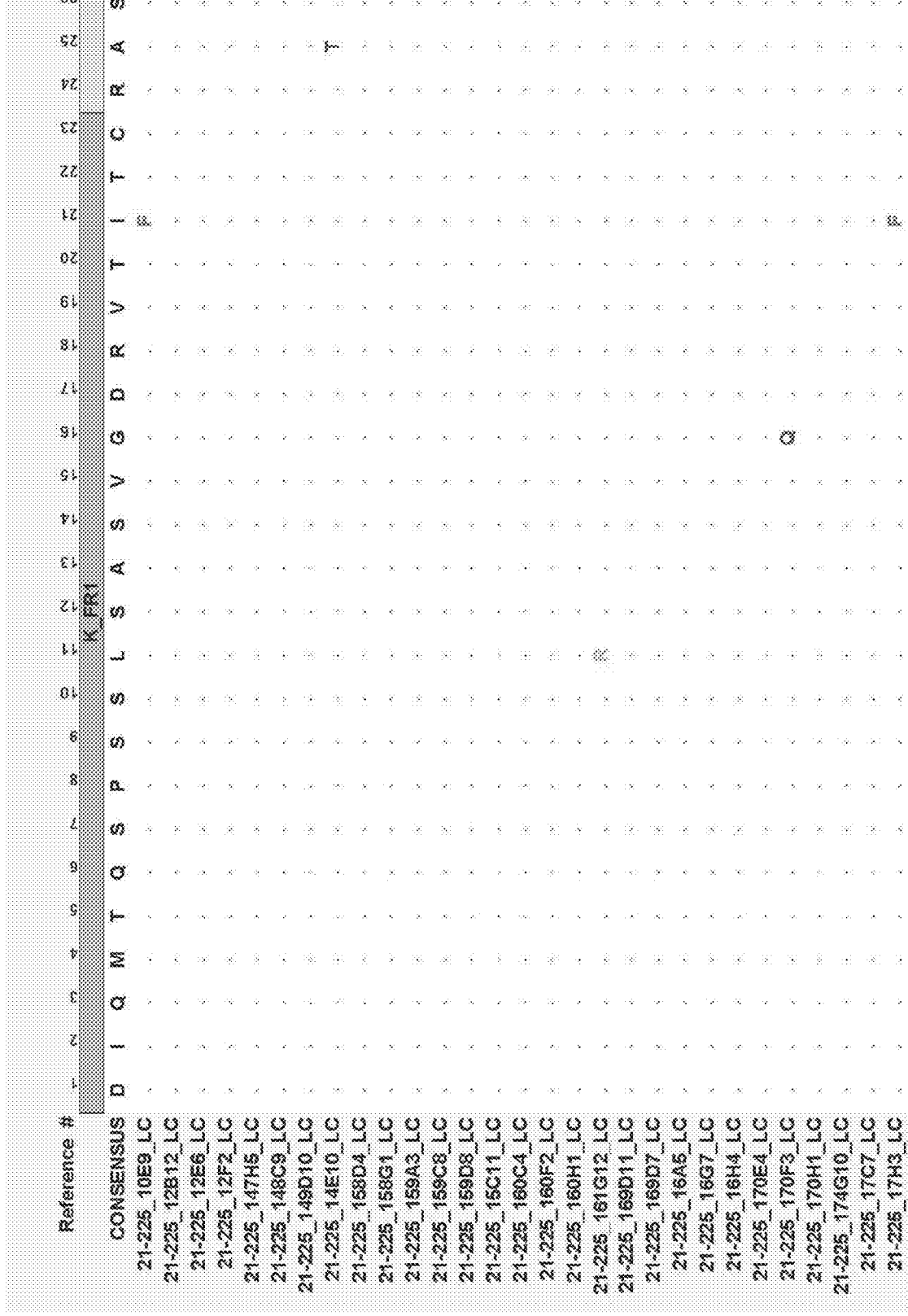
Figure 57:
Figure 57:
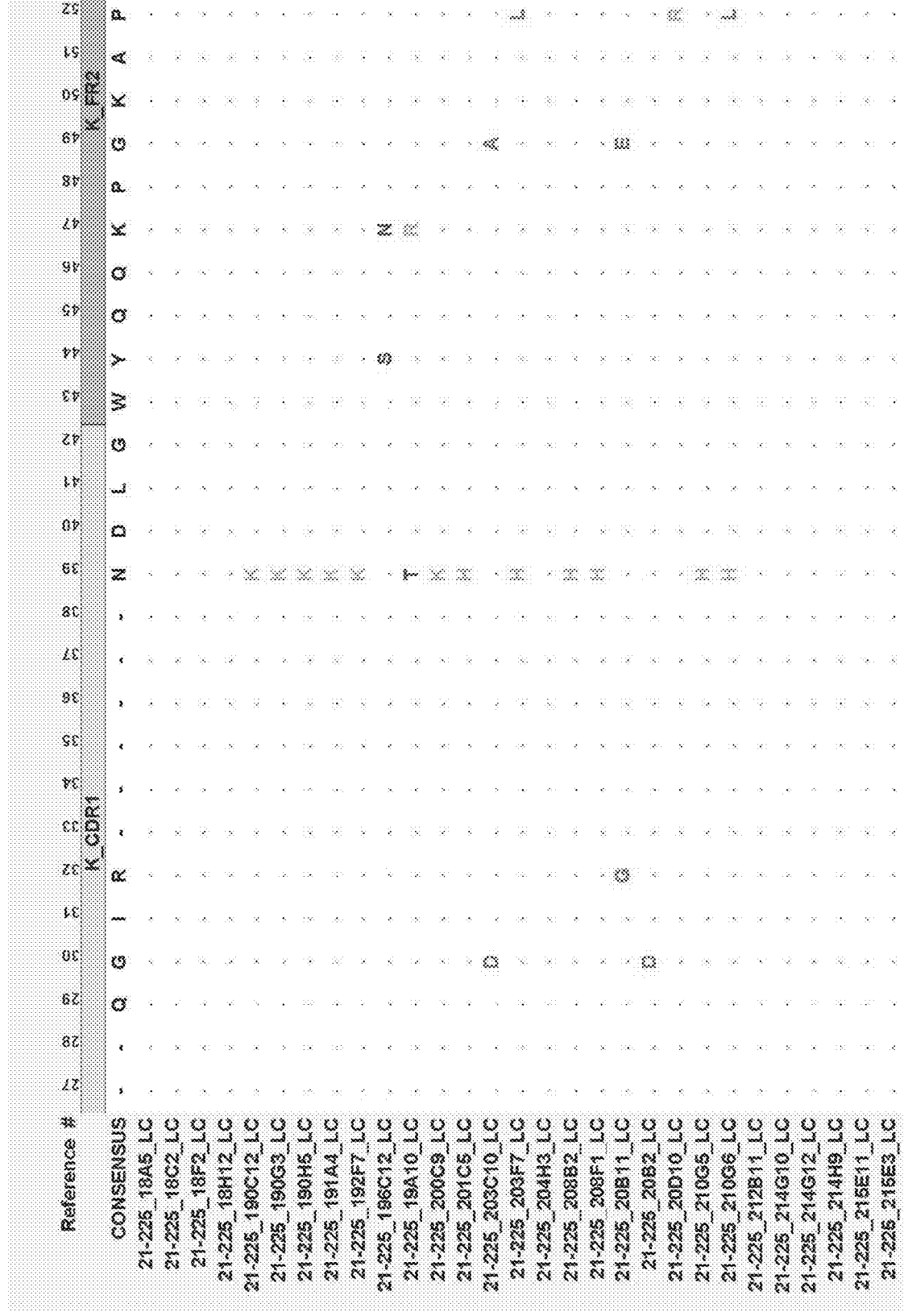
Figure 57:
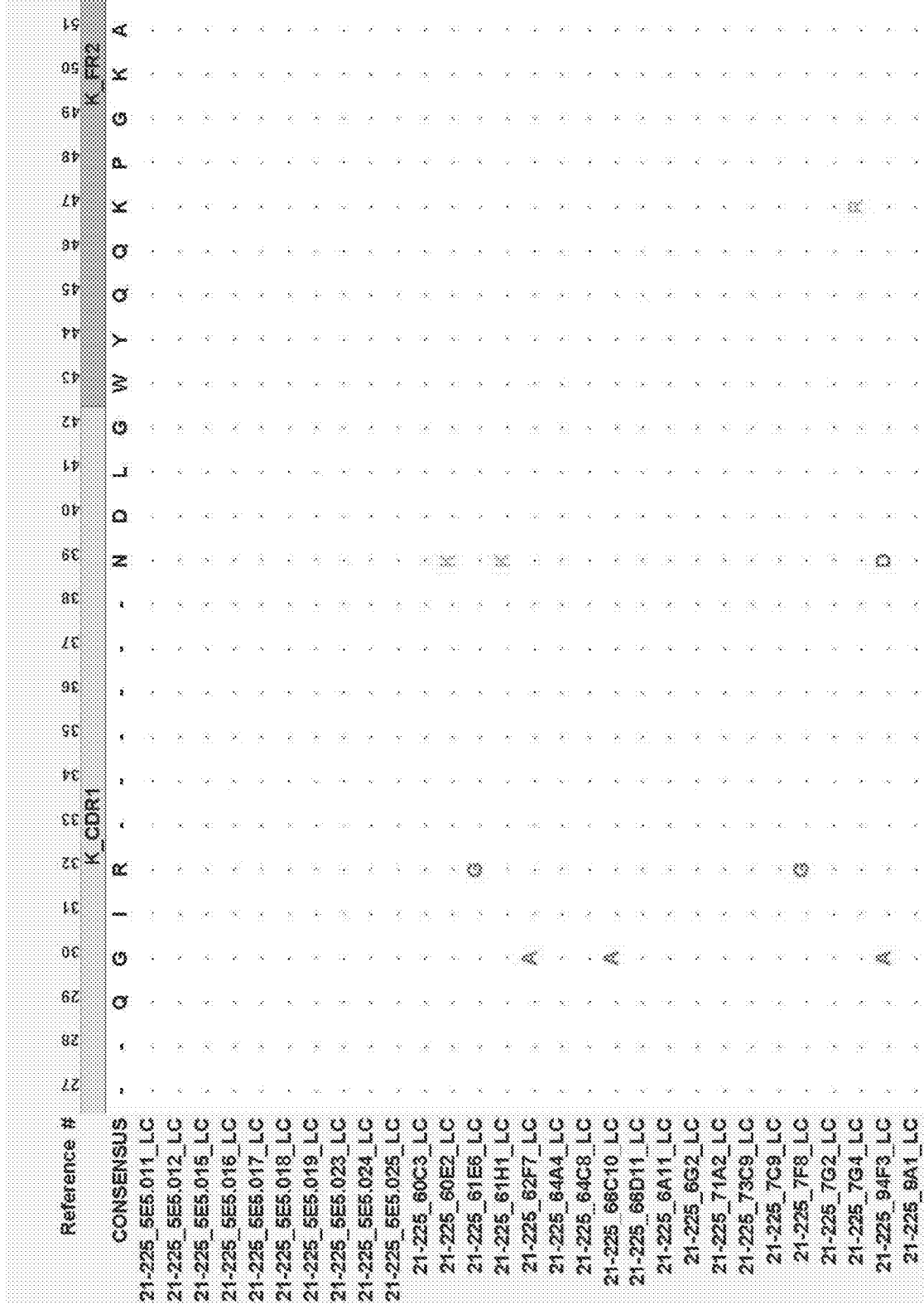
Figure 57:
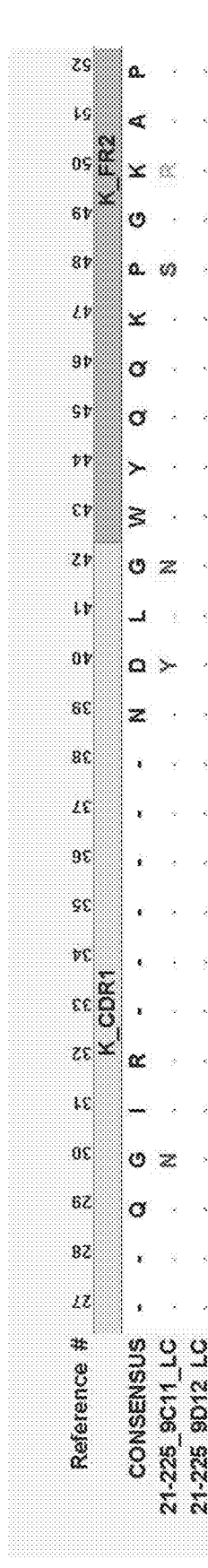
Figure 57:
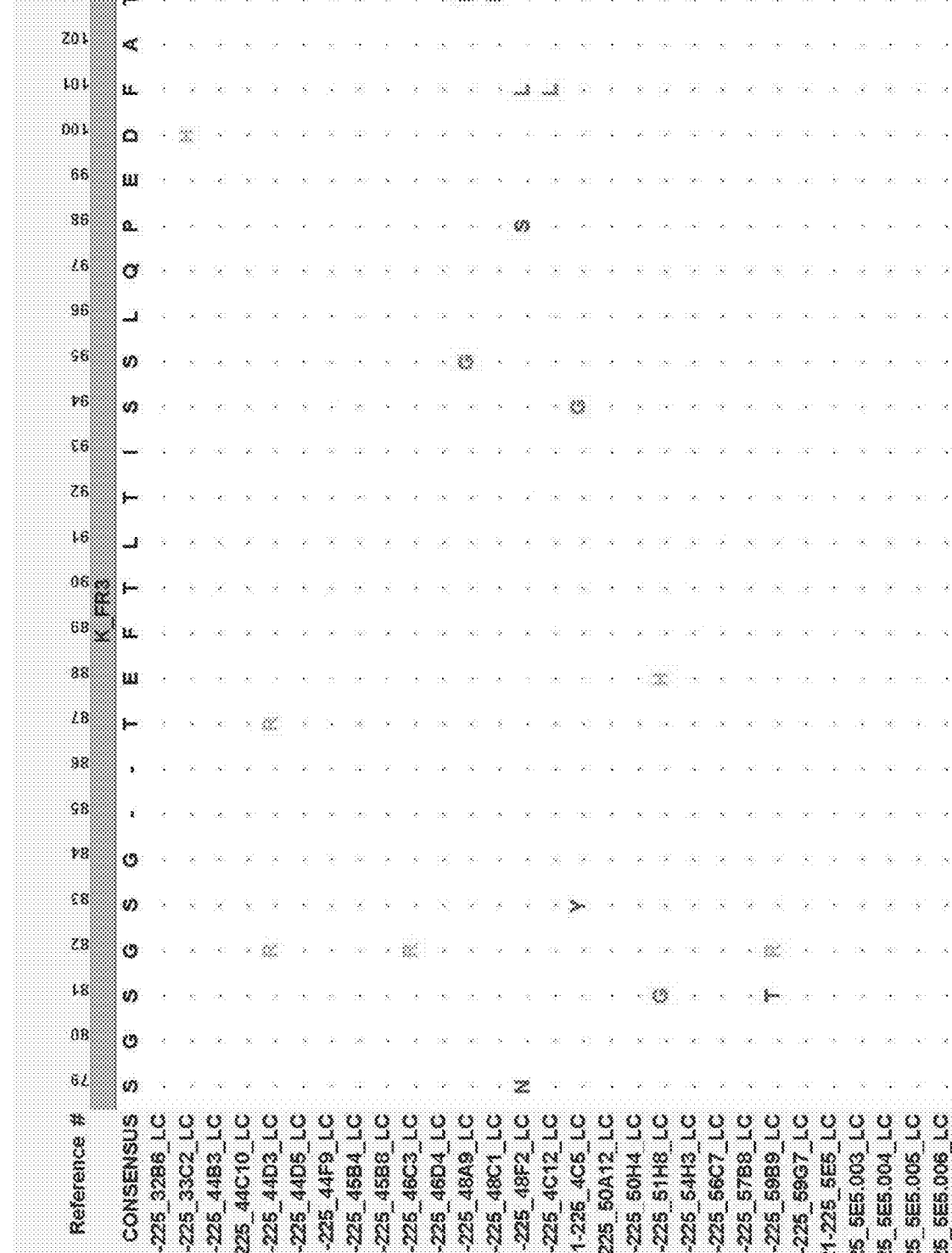
Figure 57:
Figure 57:
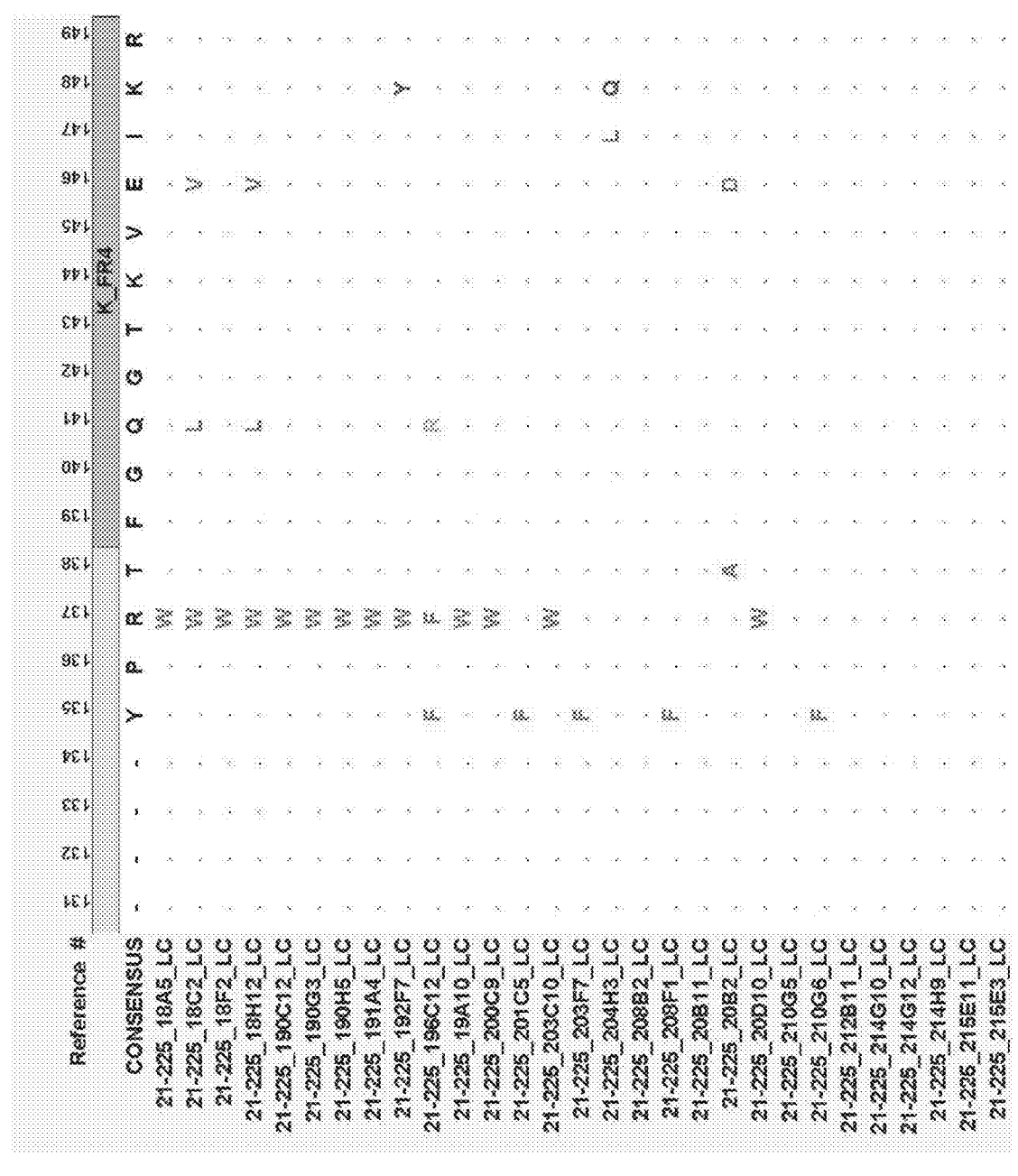
Figure 57:
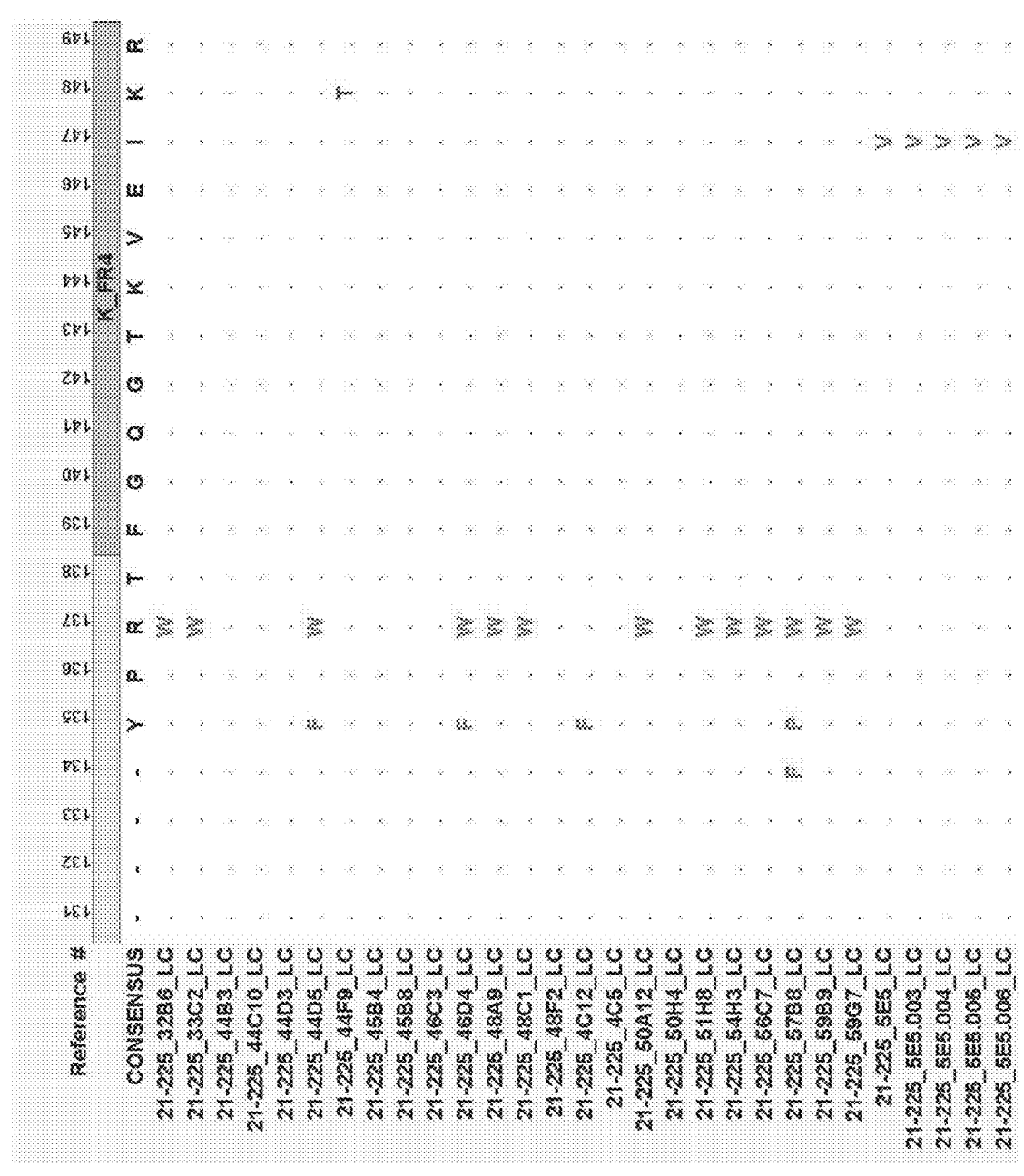
Figure 57:
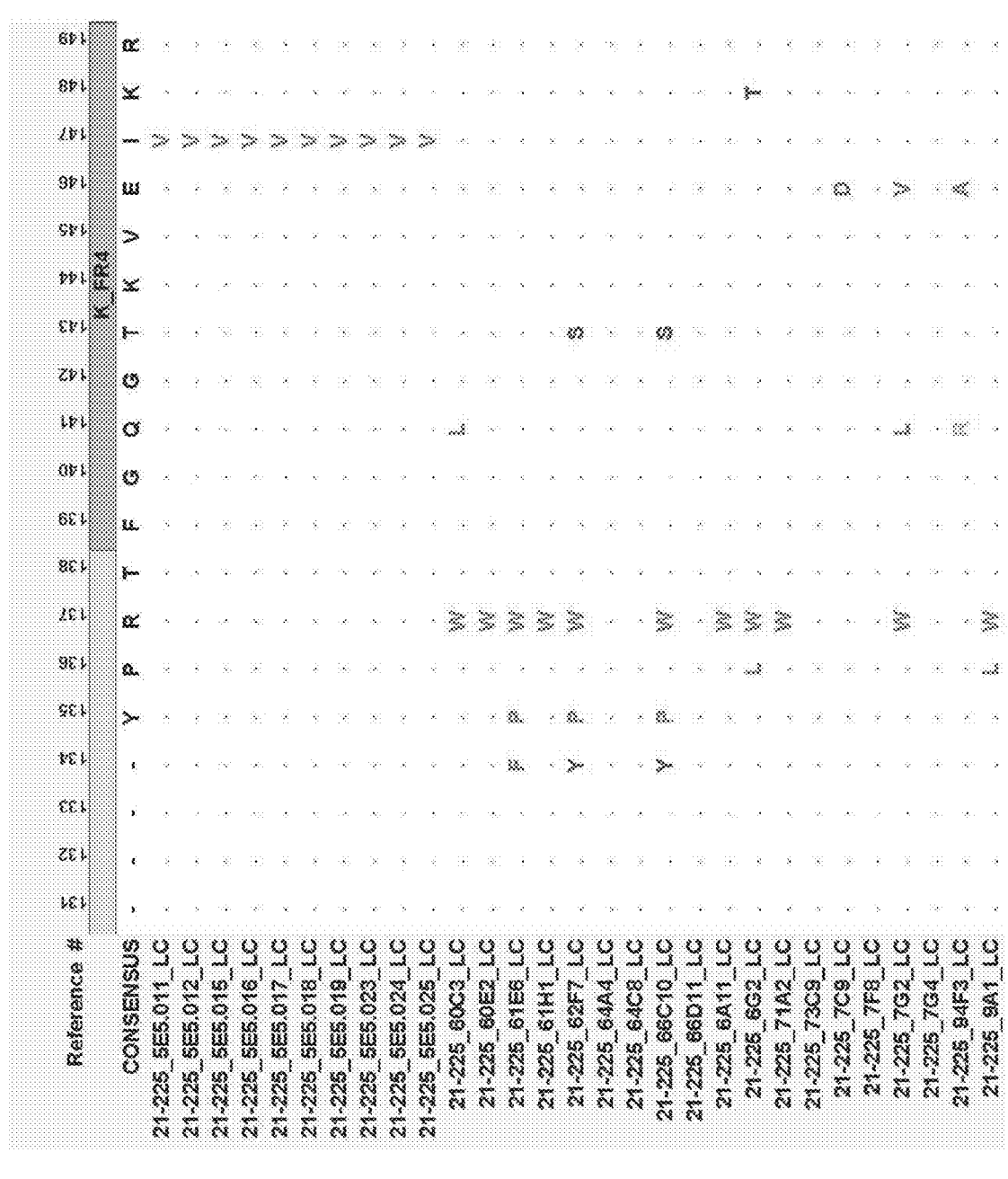
Figure 57:
Figure 57:
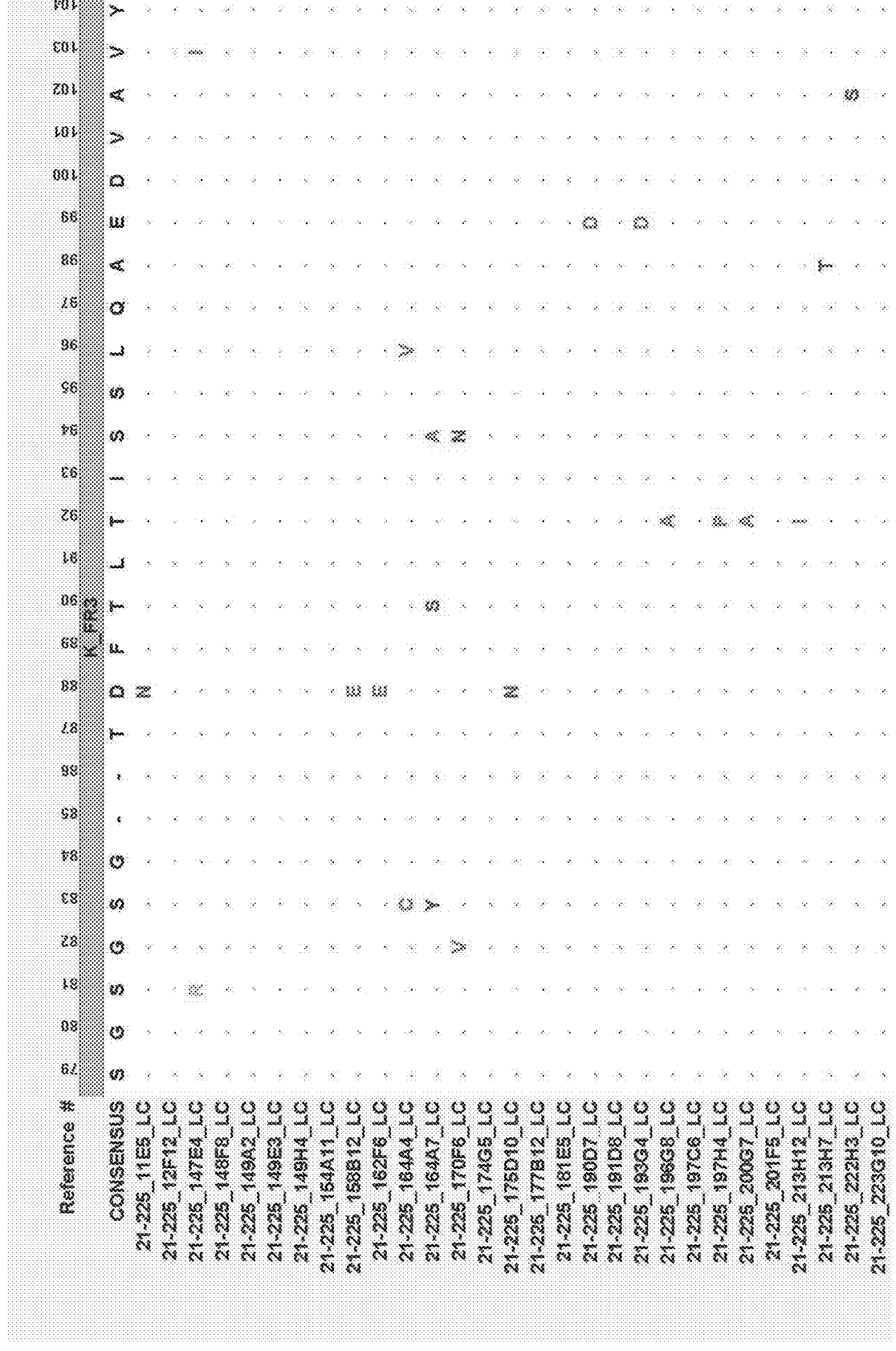
Figure 57:
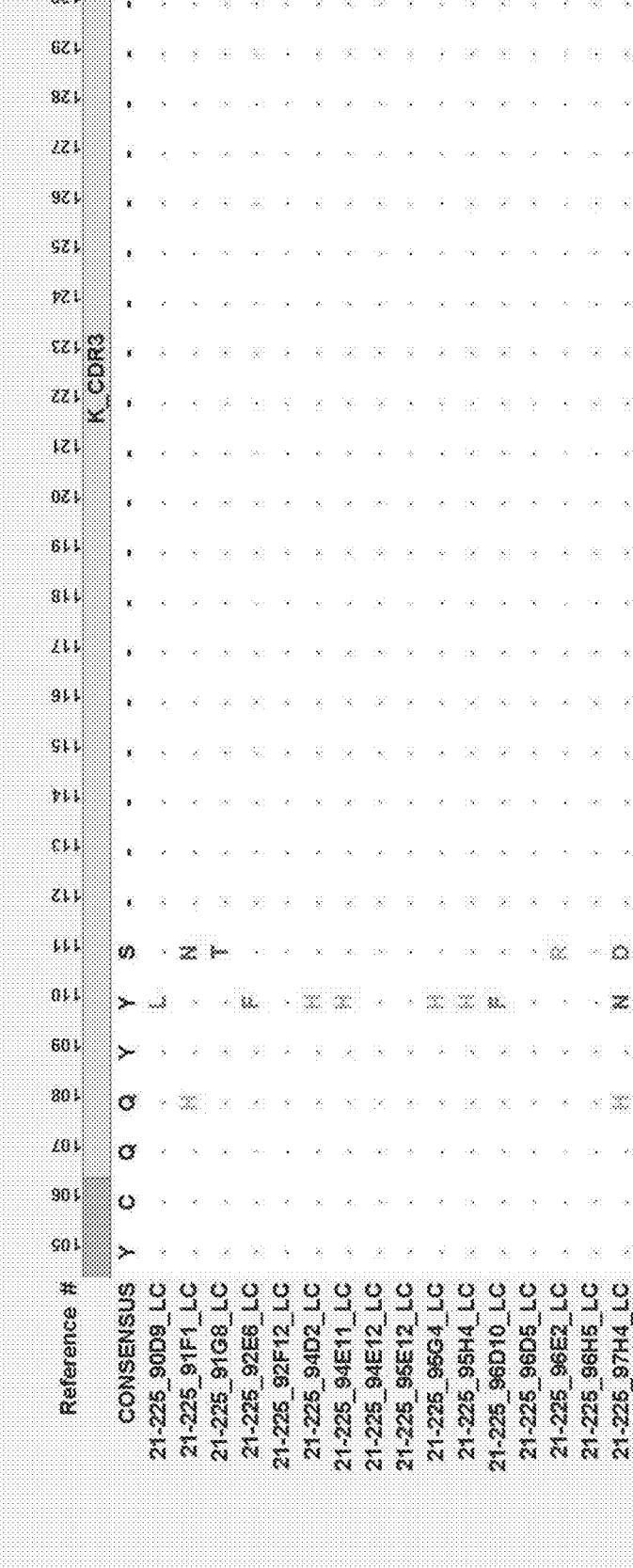
Figure 57:
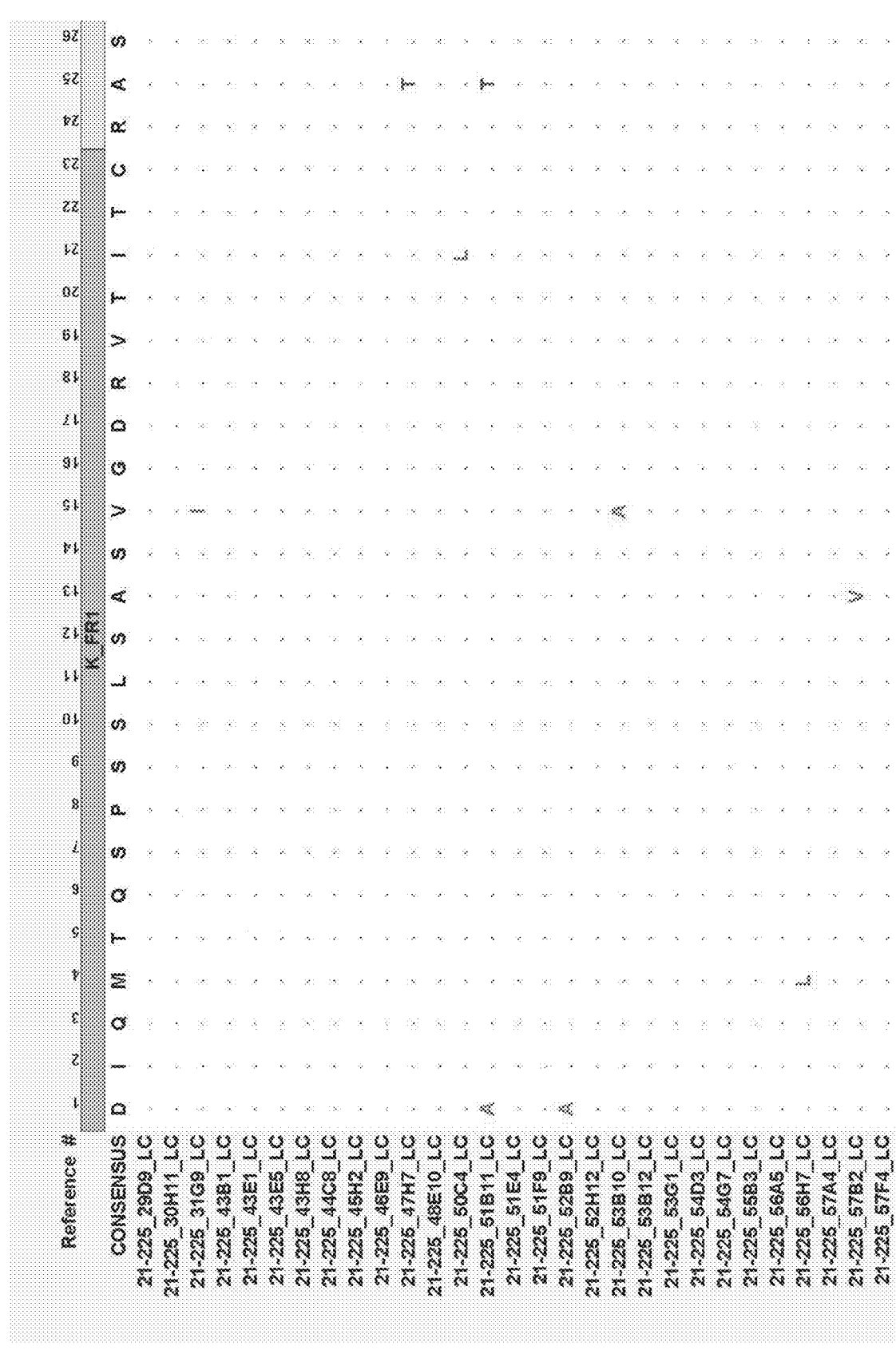
Figure 57:
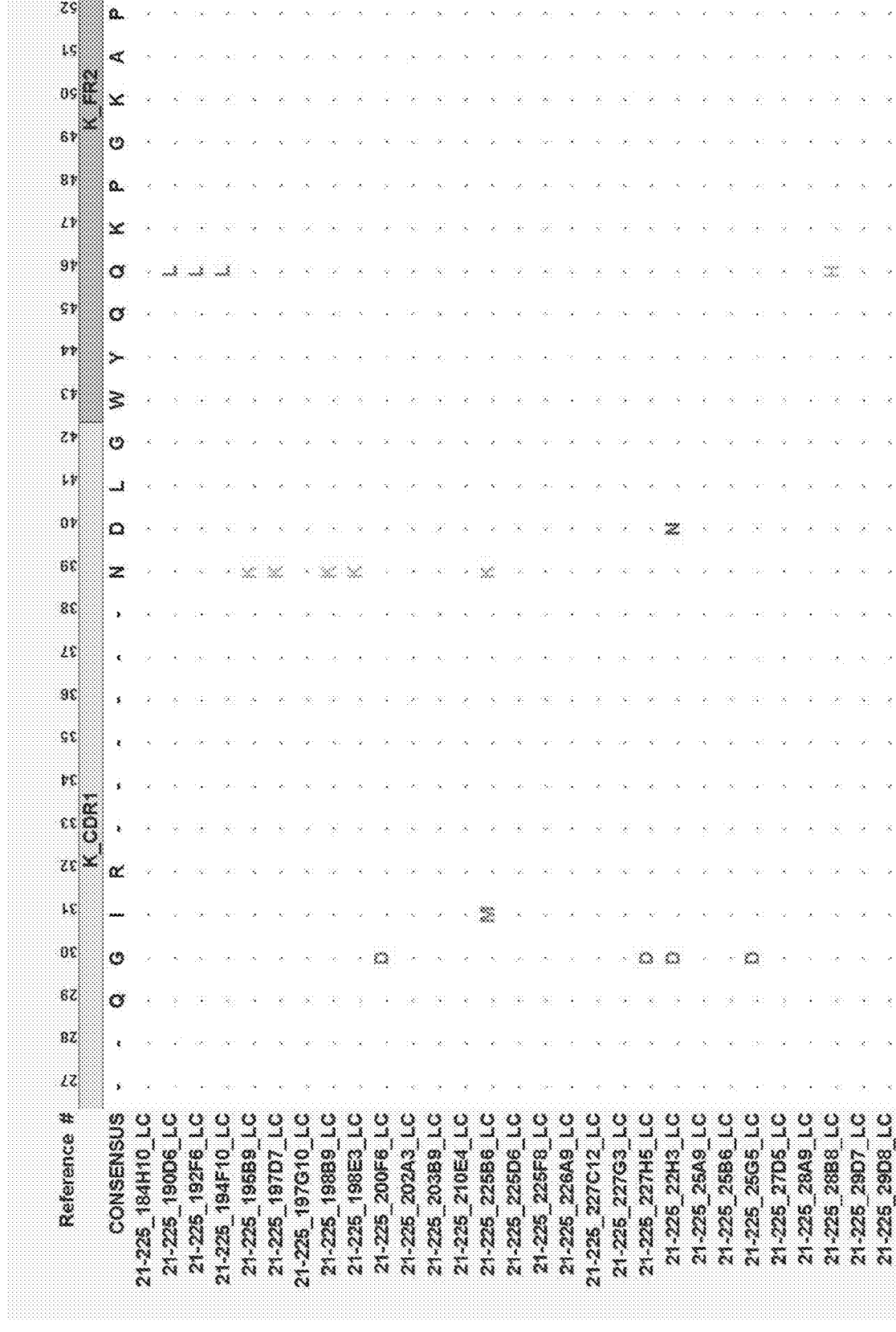
Figure 57:
Figure 57:
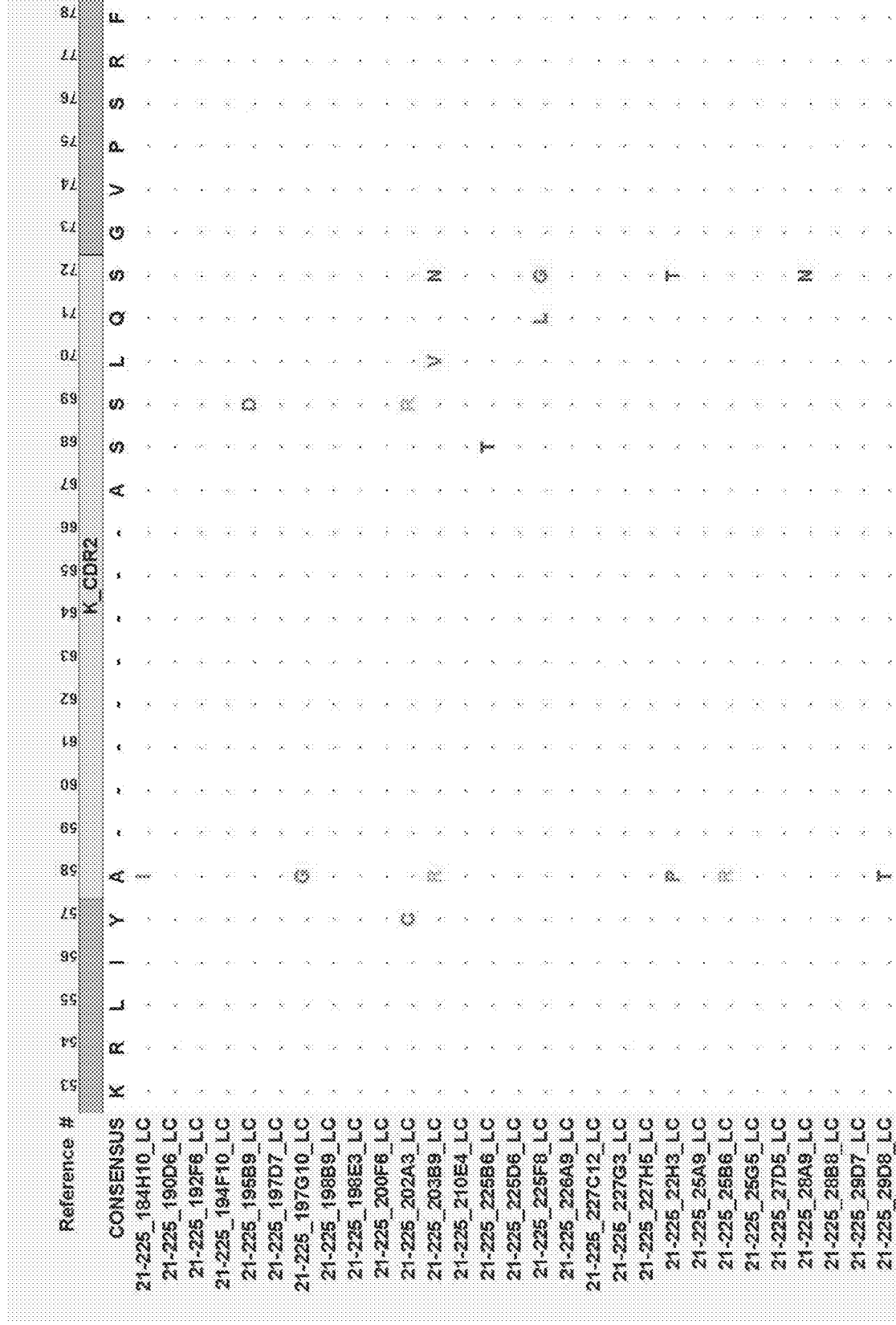
Figure 57:
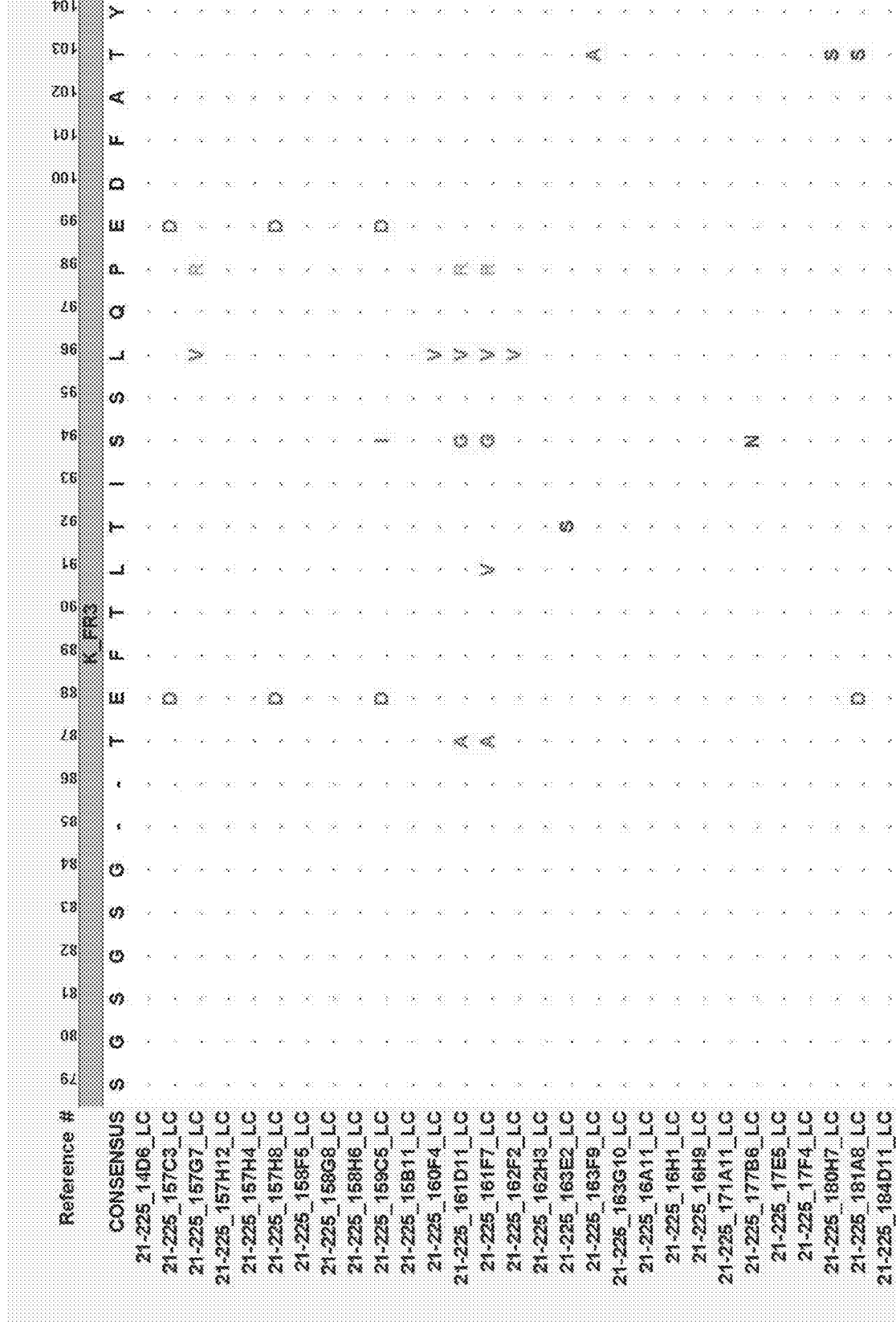
Figure 57:
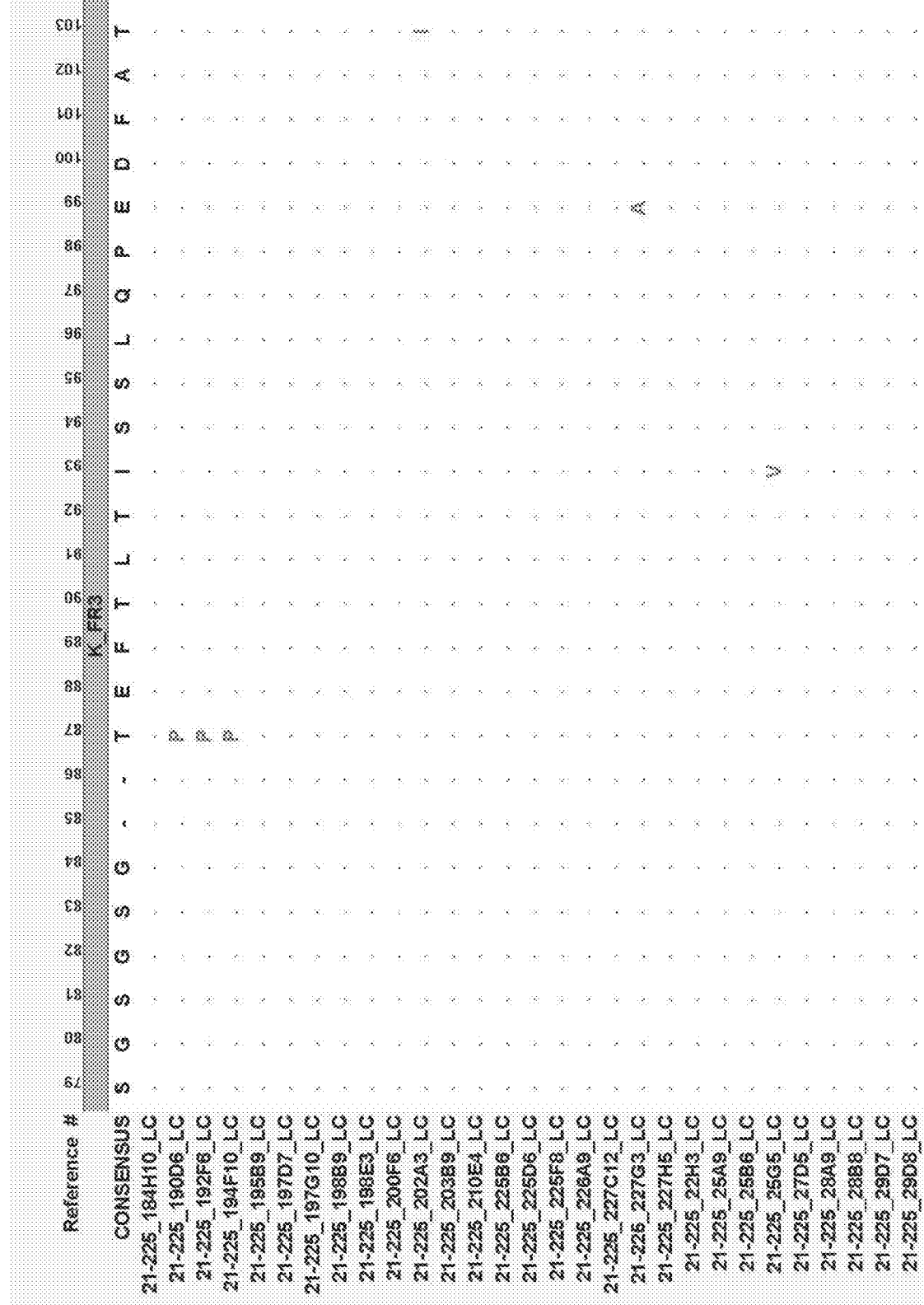
Figure 57:
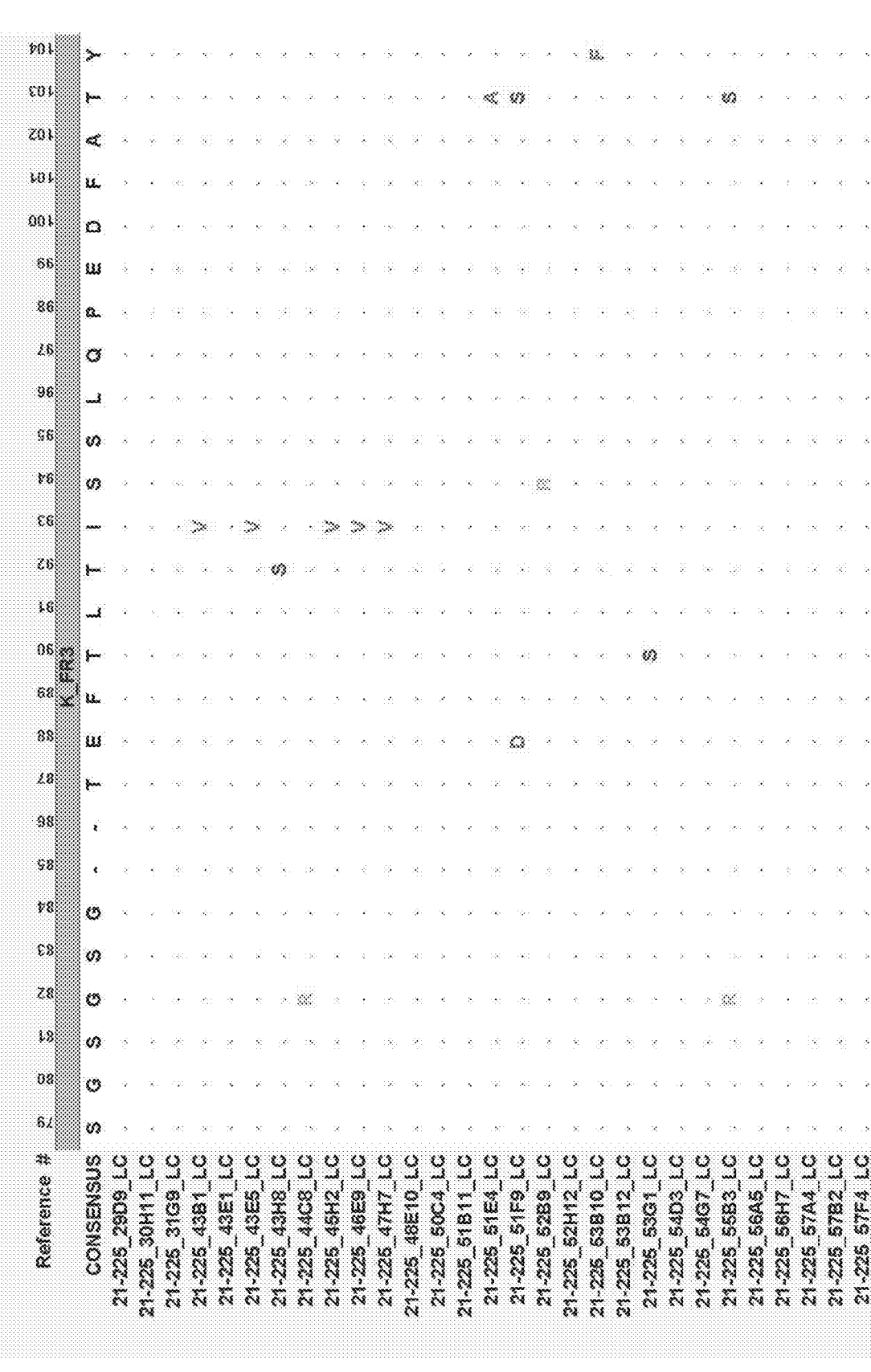
Figure 57:
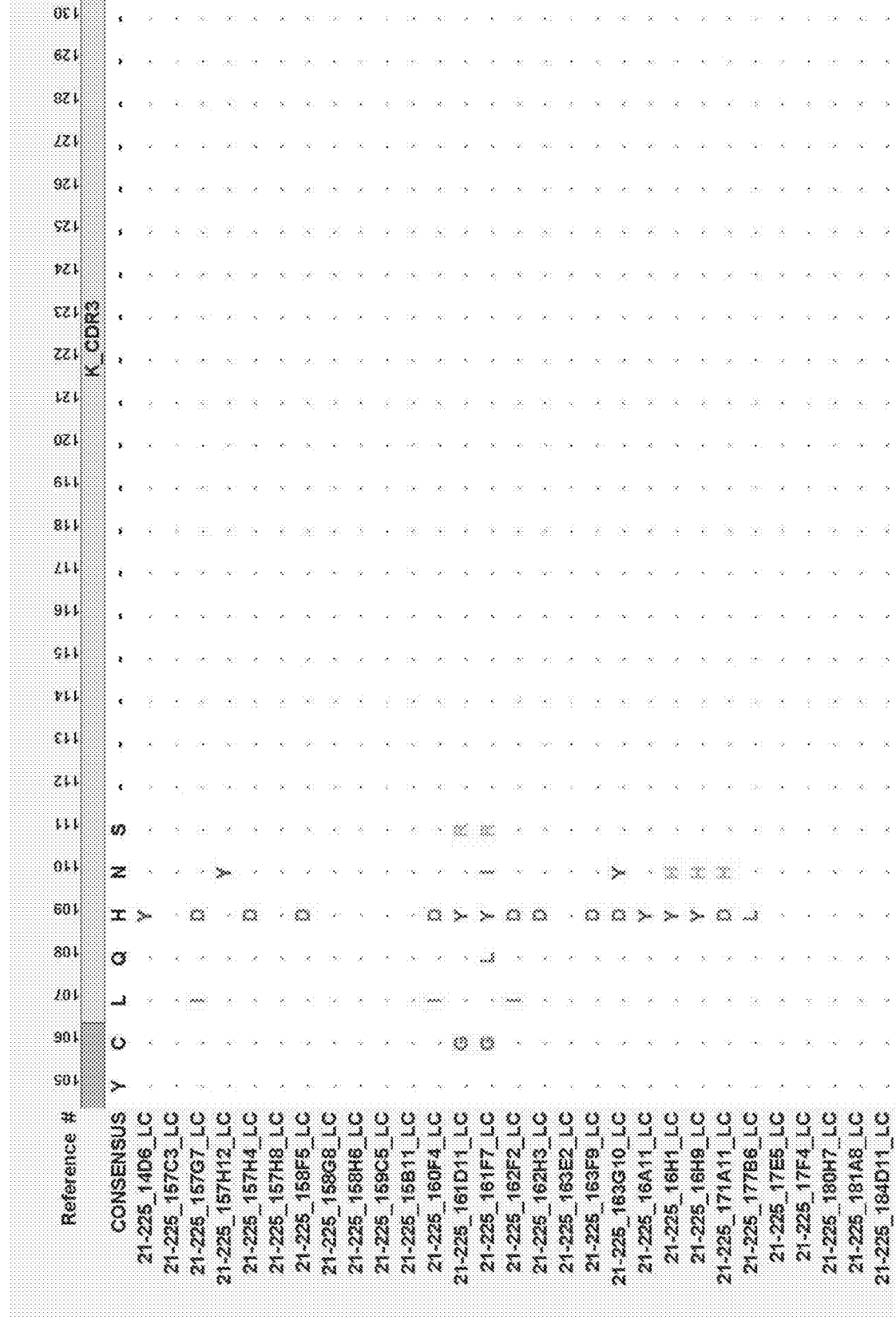
Figure 57:
Figure 57:
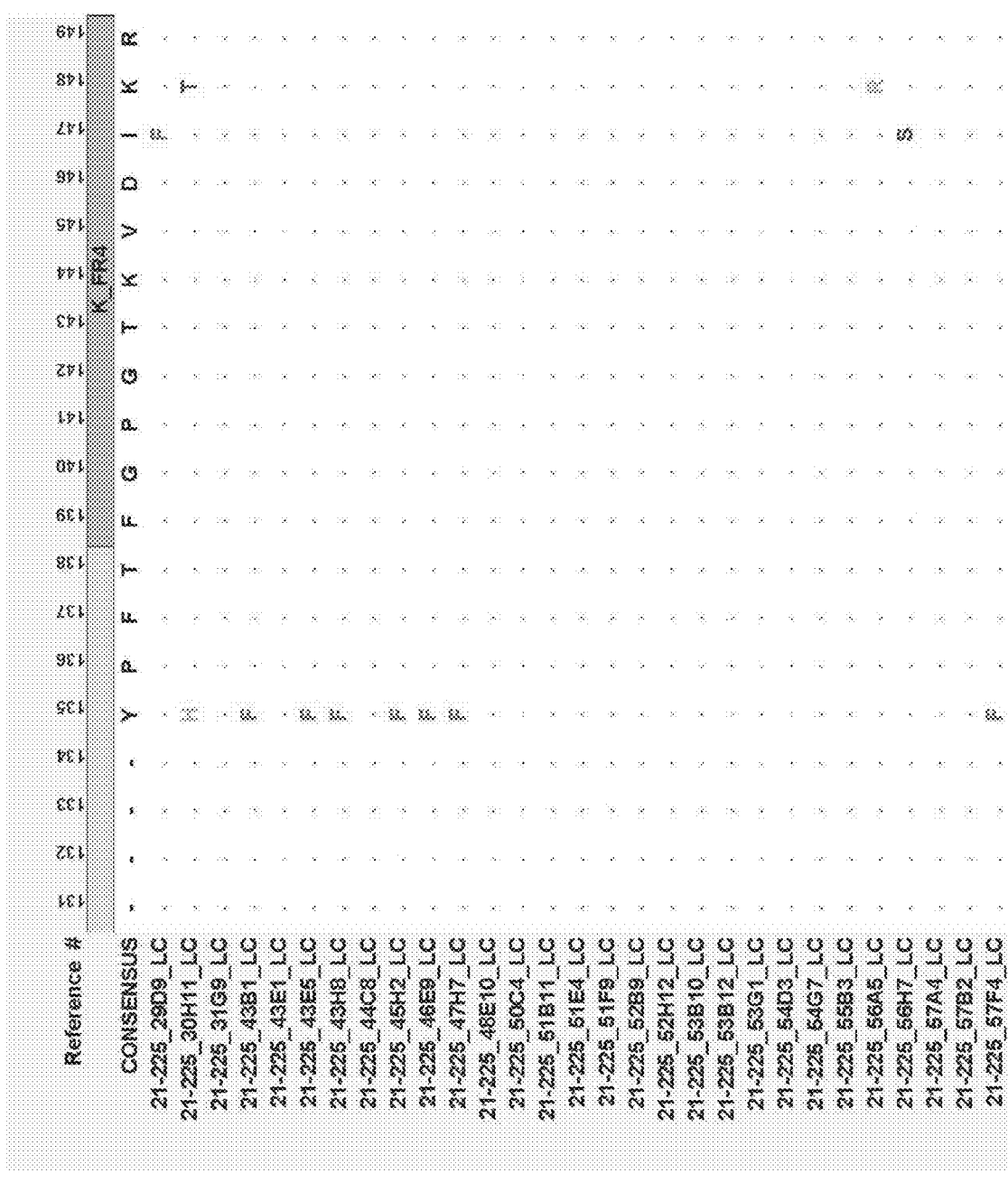
Figure 57:
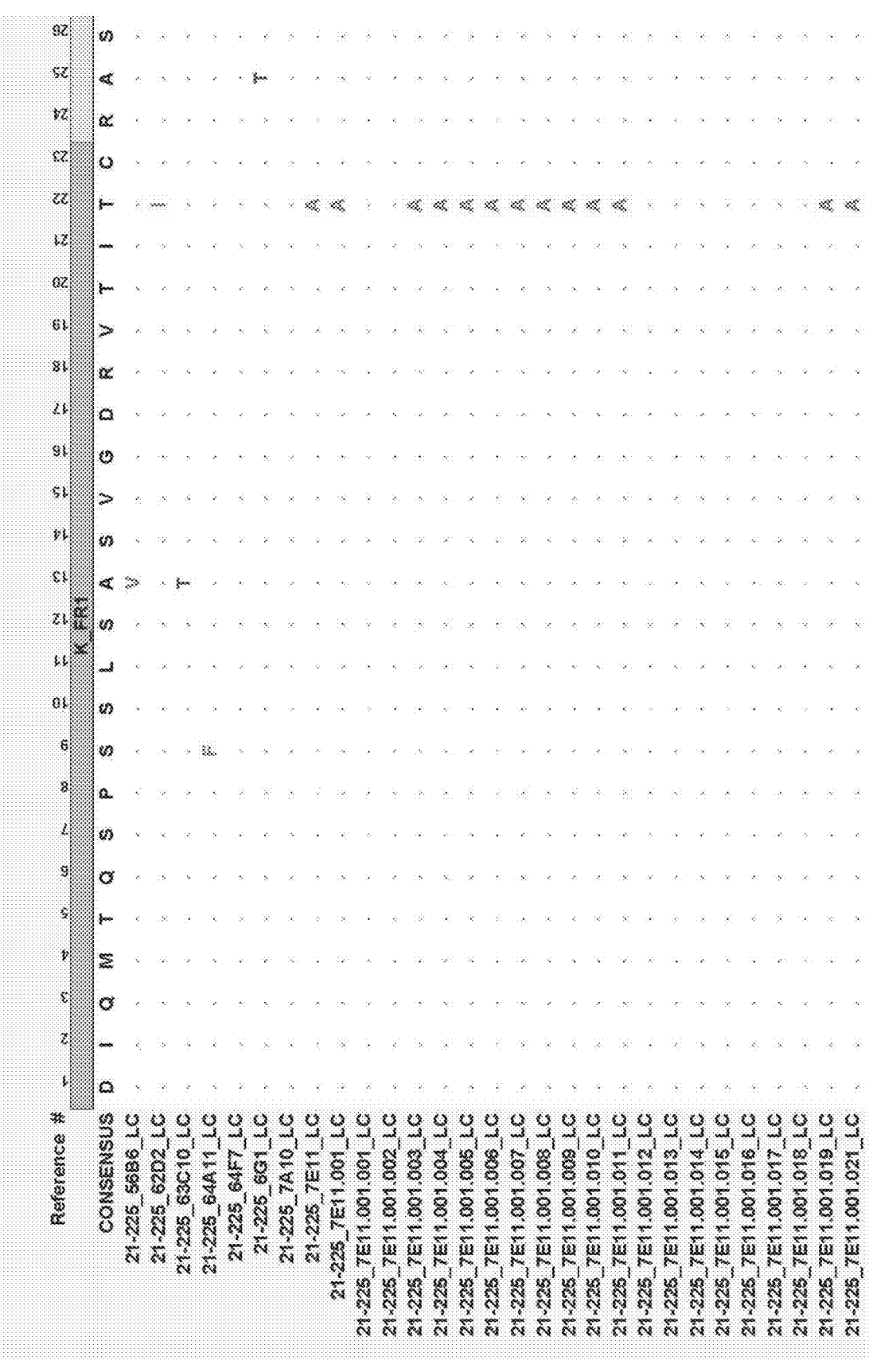
Figure 57:
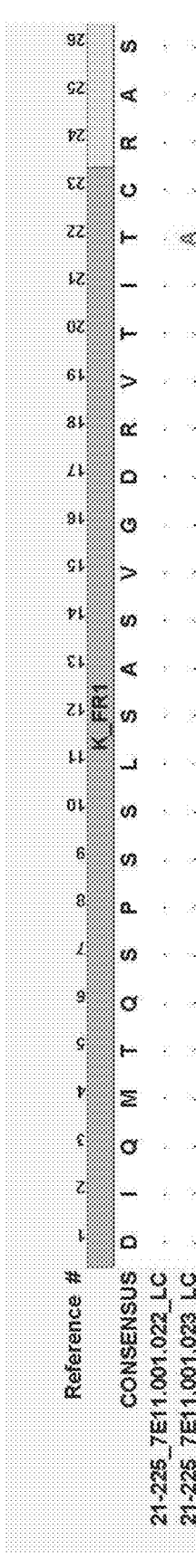
Figure 57:
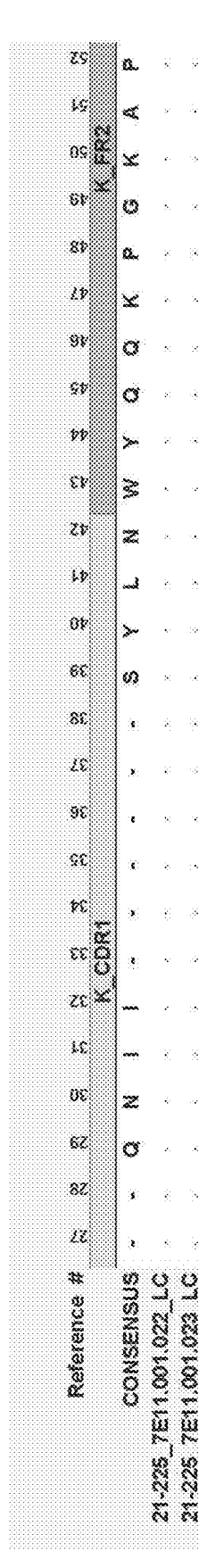
Figure 57:
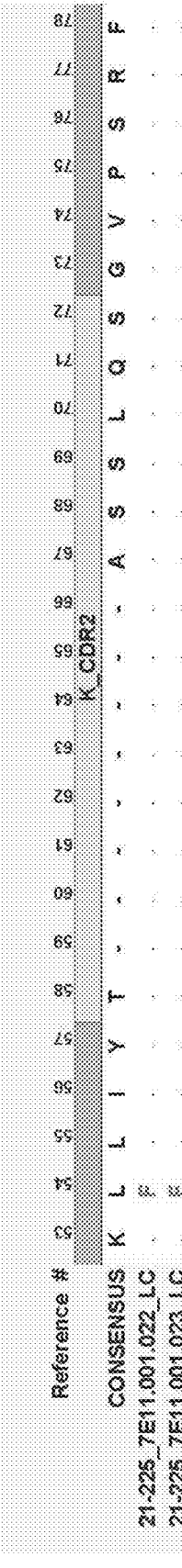
Figure 57:
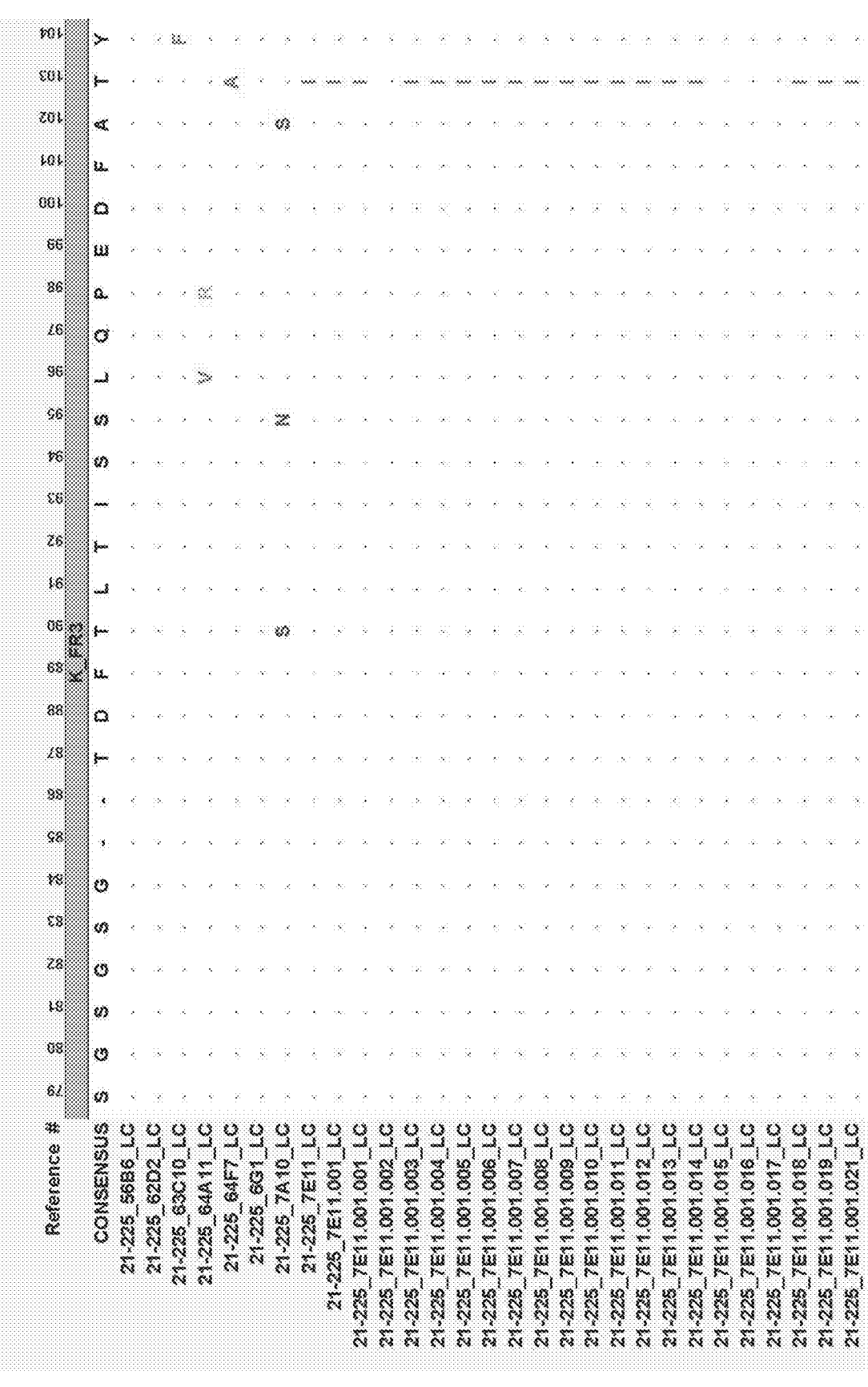
Figure 57:
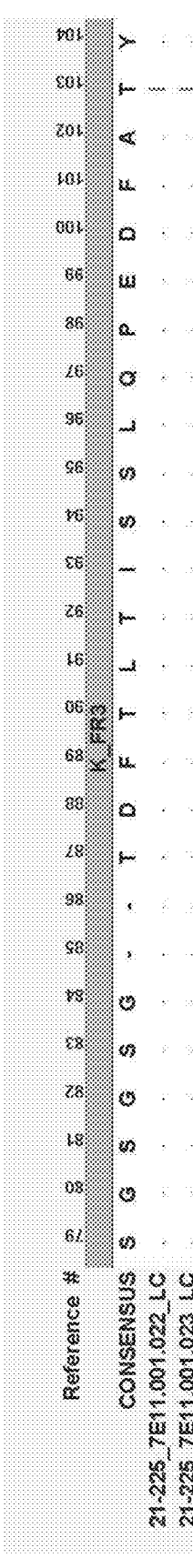
Figure 57:
Figure 57:
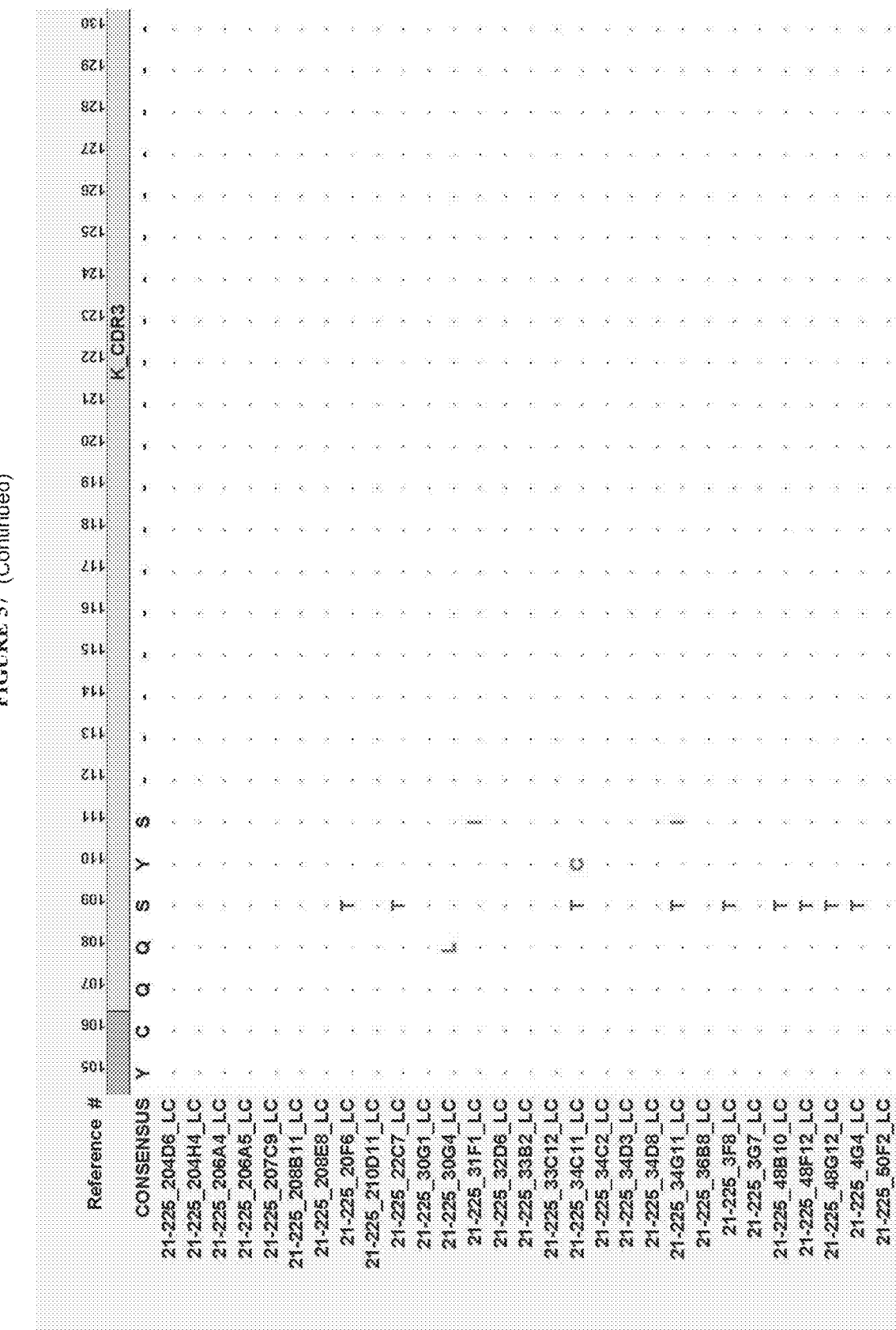
Figure 57:
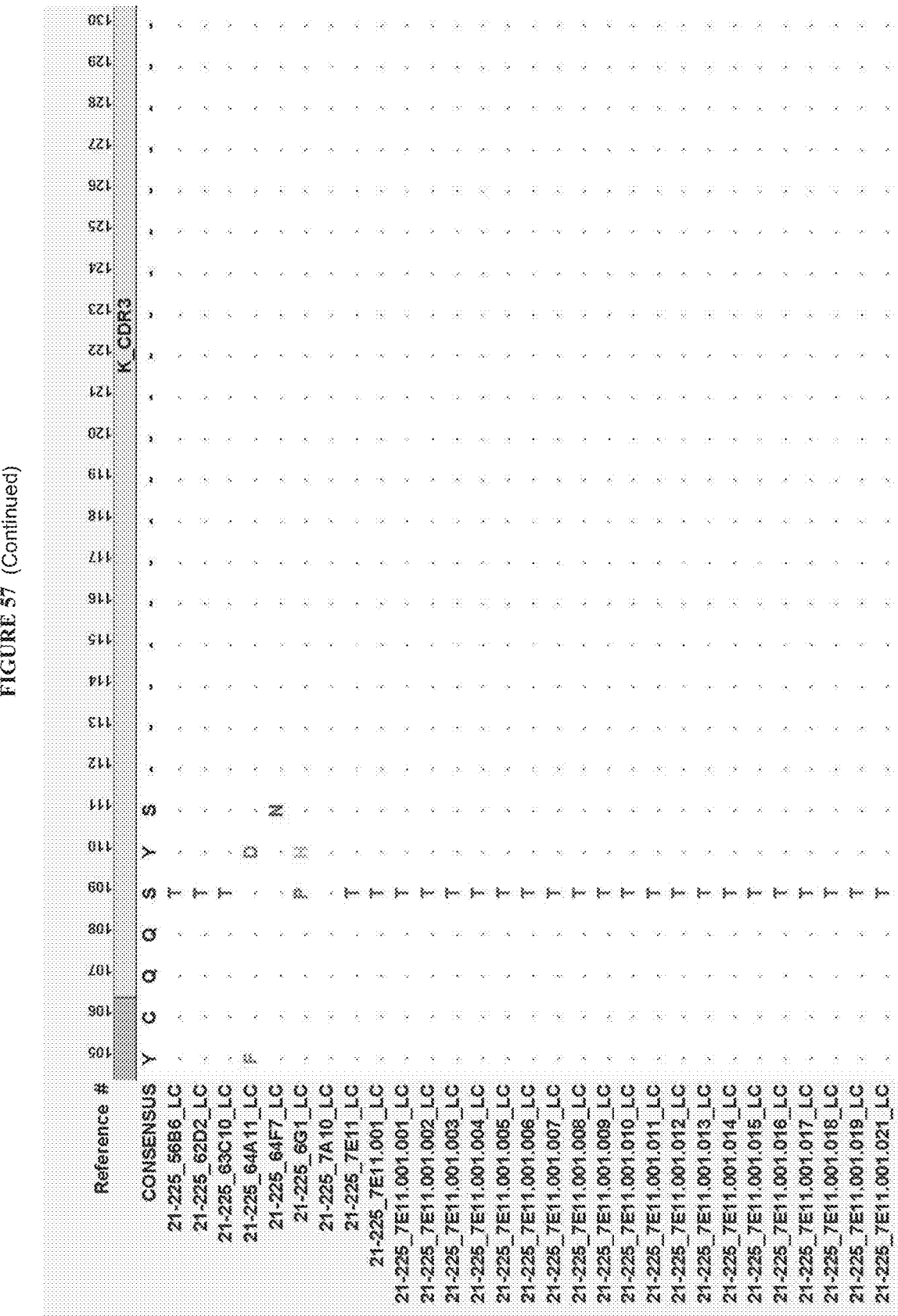
Figure 57:
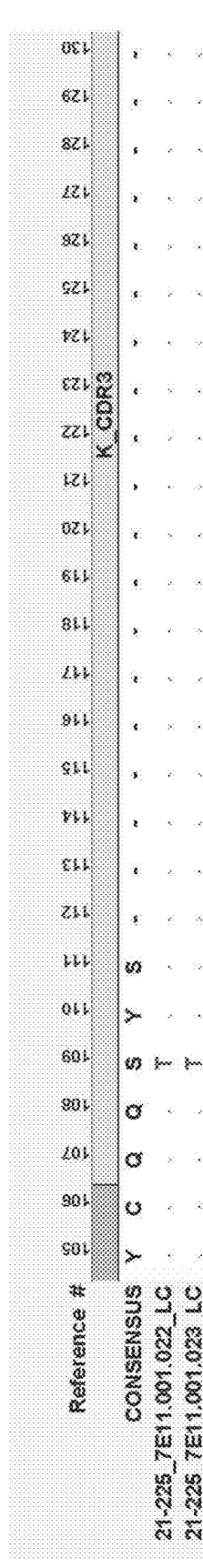
Figure 57:
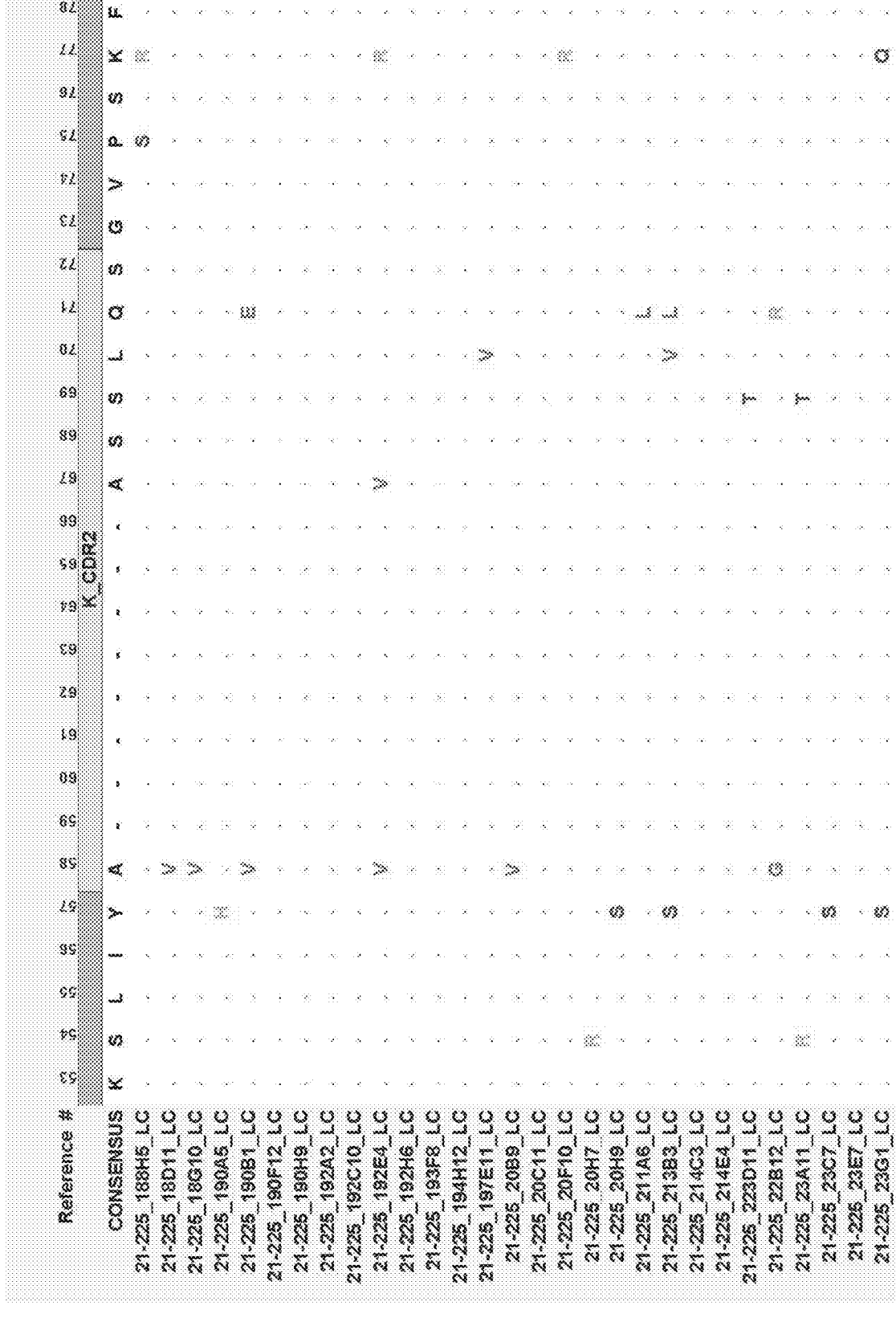
Figure 57:
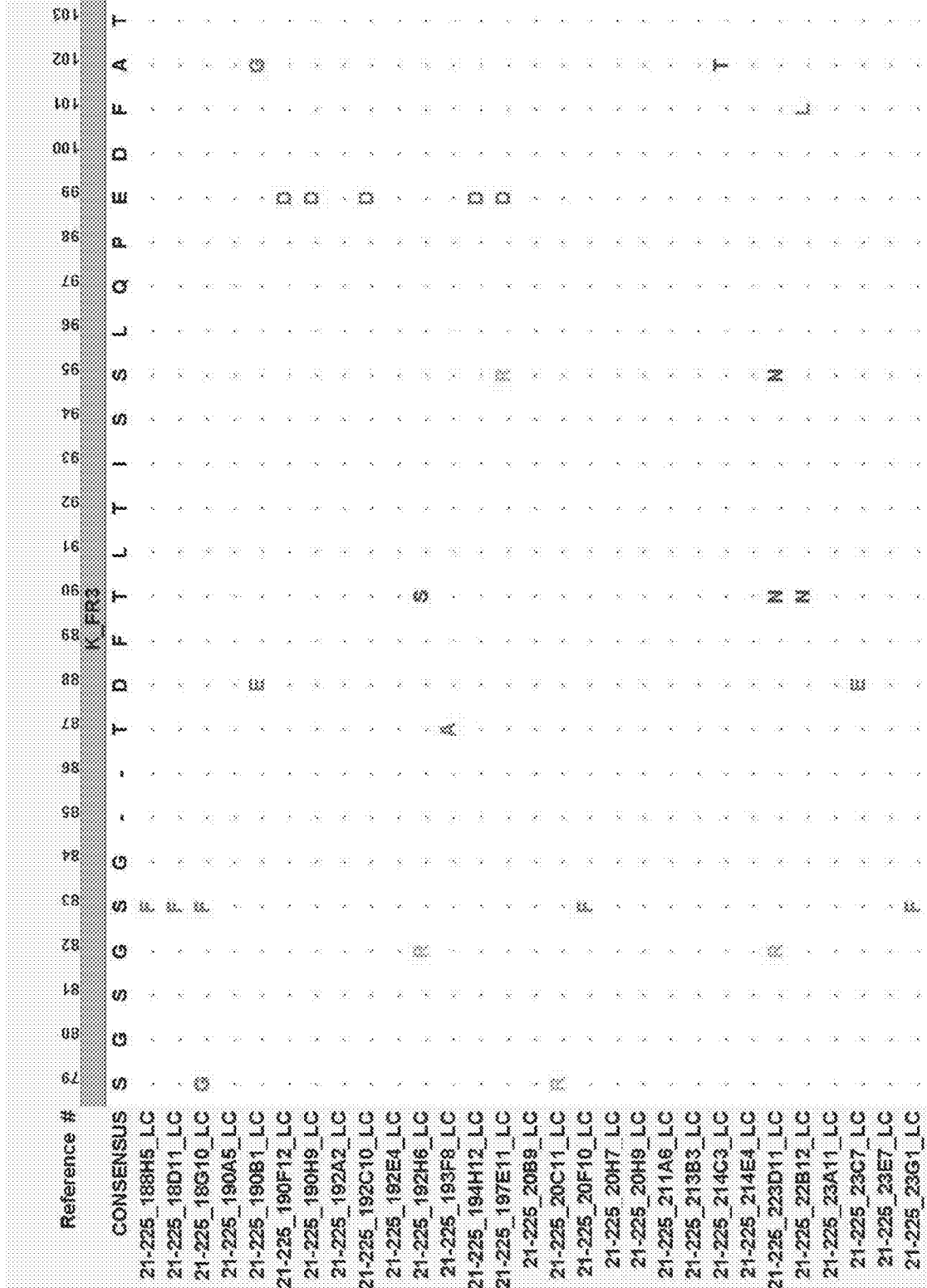
Figure 57:
Figure 57:
Figure 57:
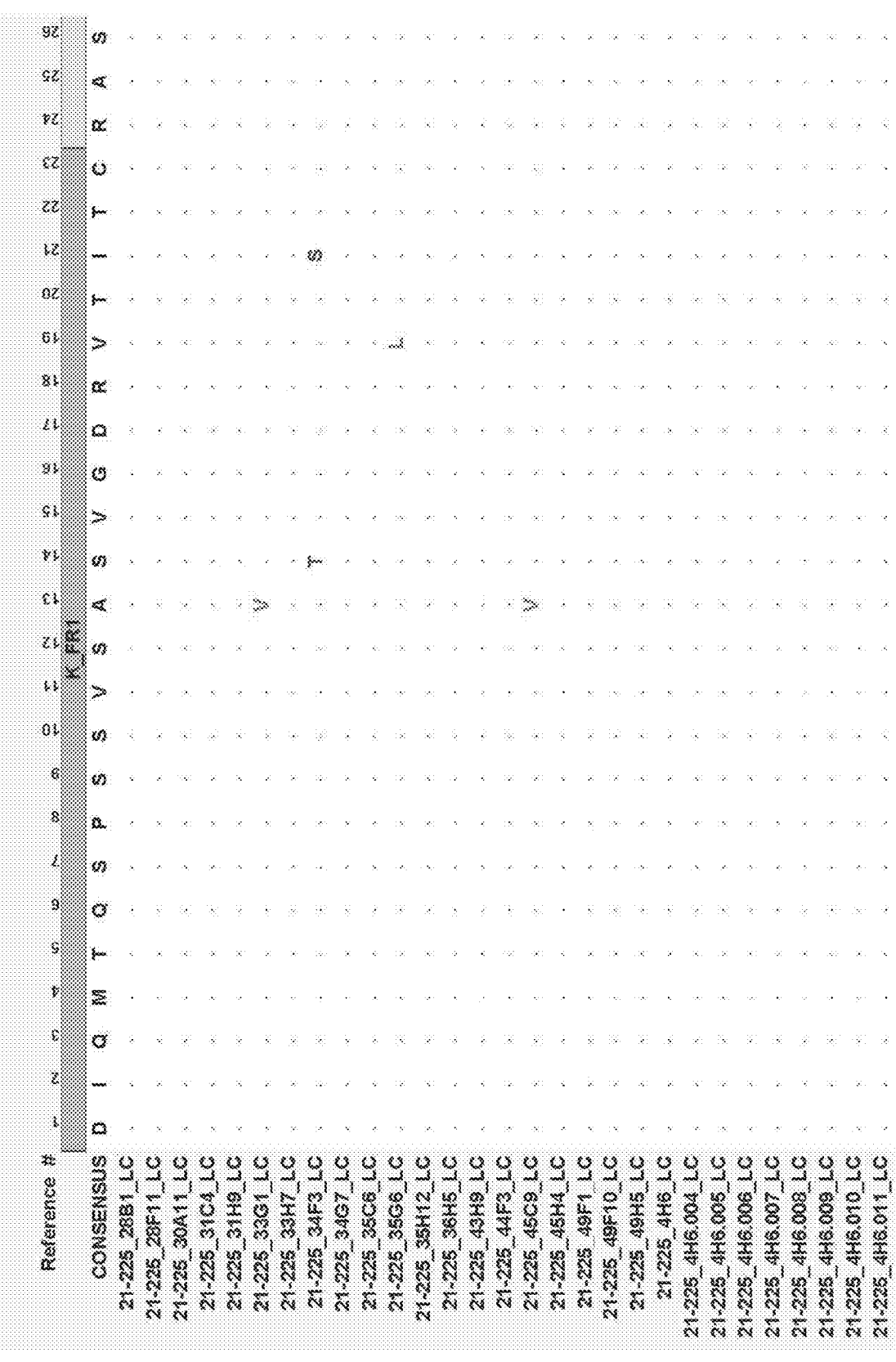
Figure 57:
Figure 57:
Figure 57:
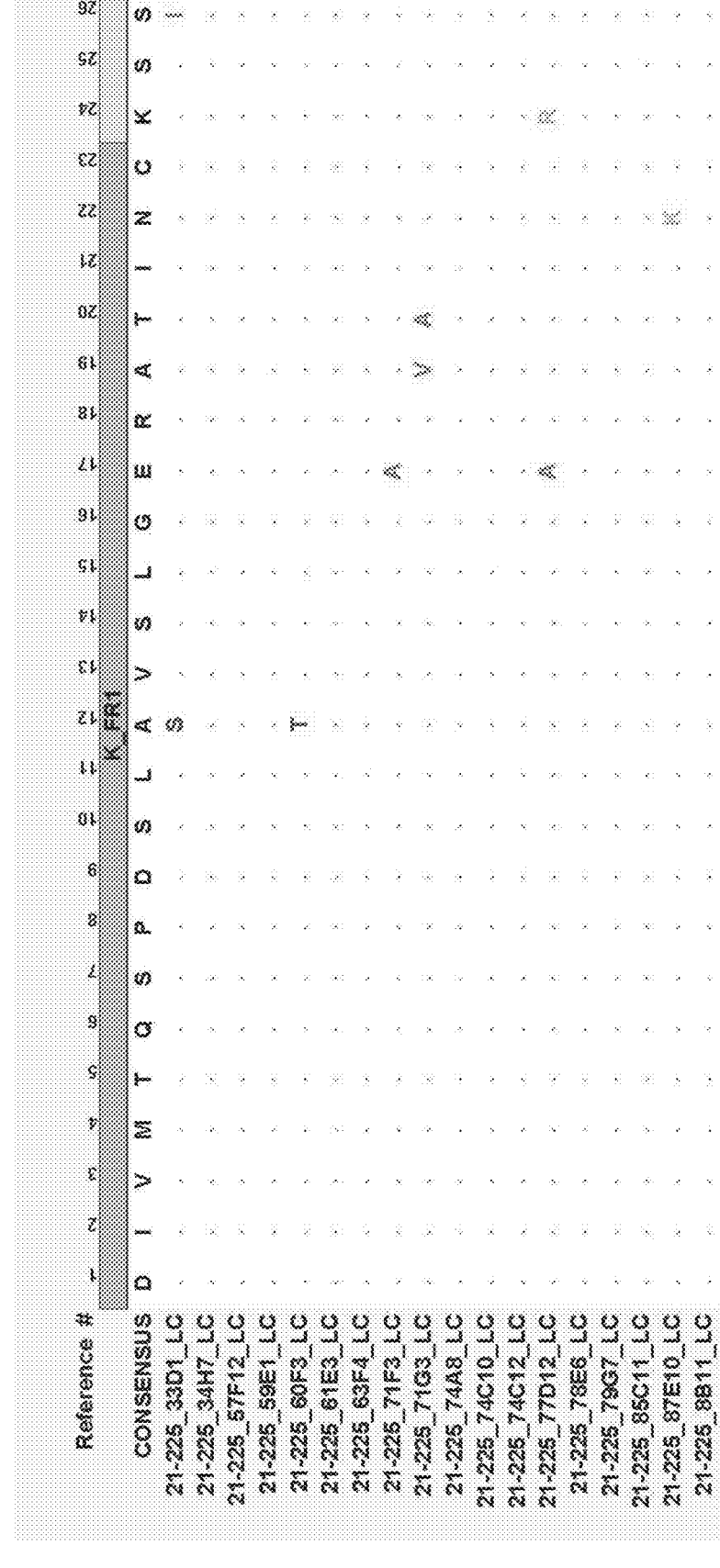
Figure 57:
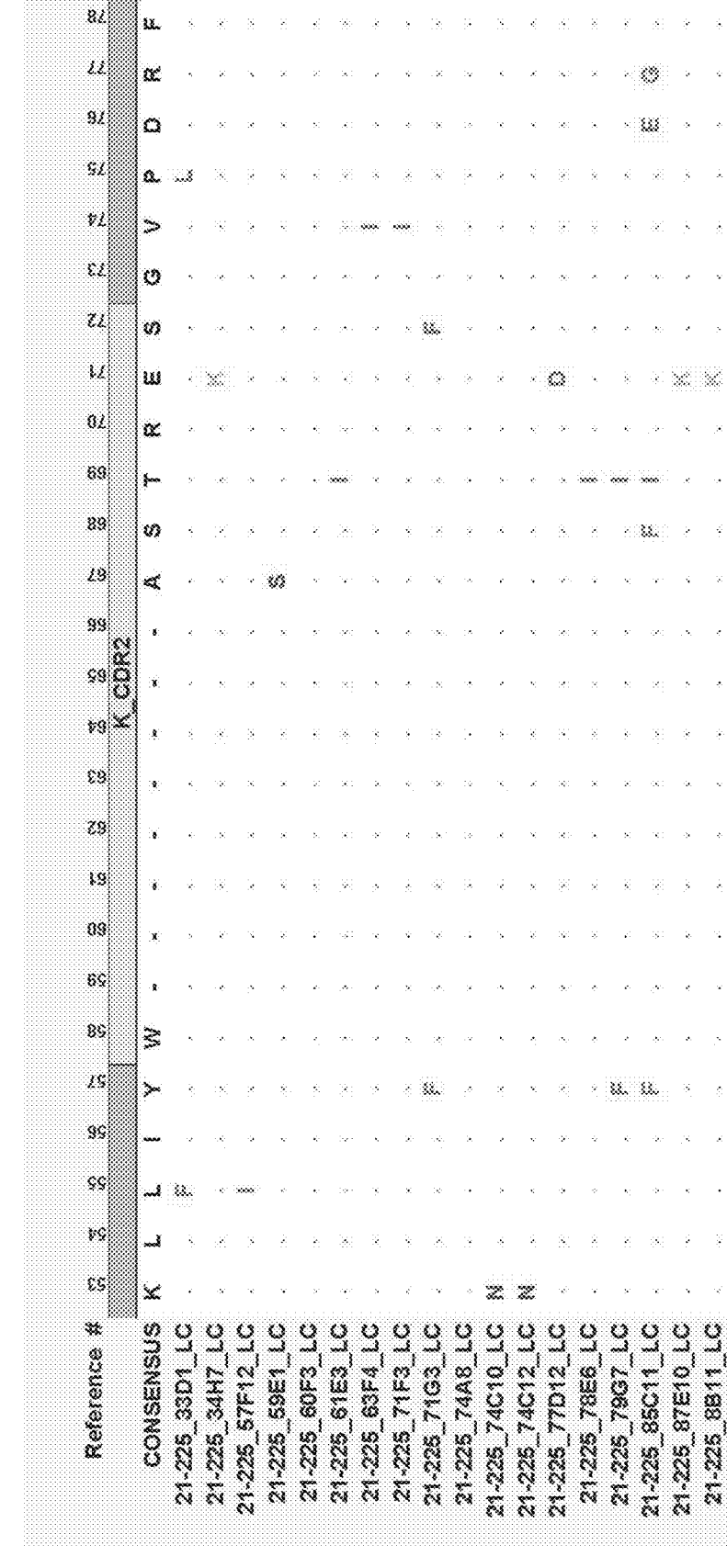
Figure 57:
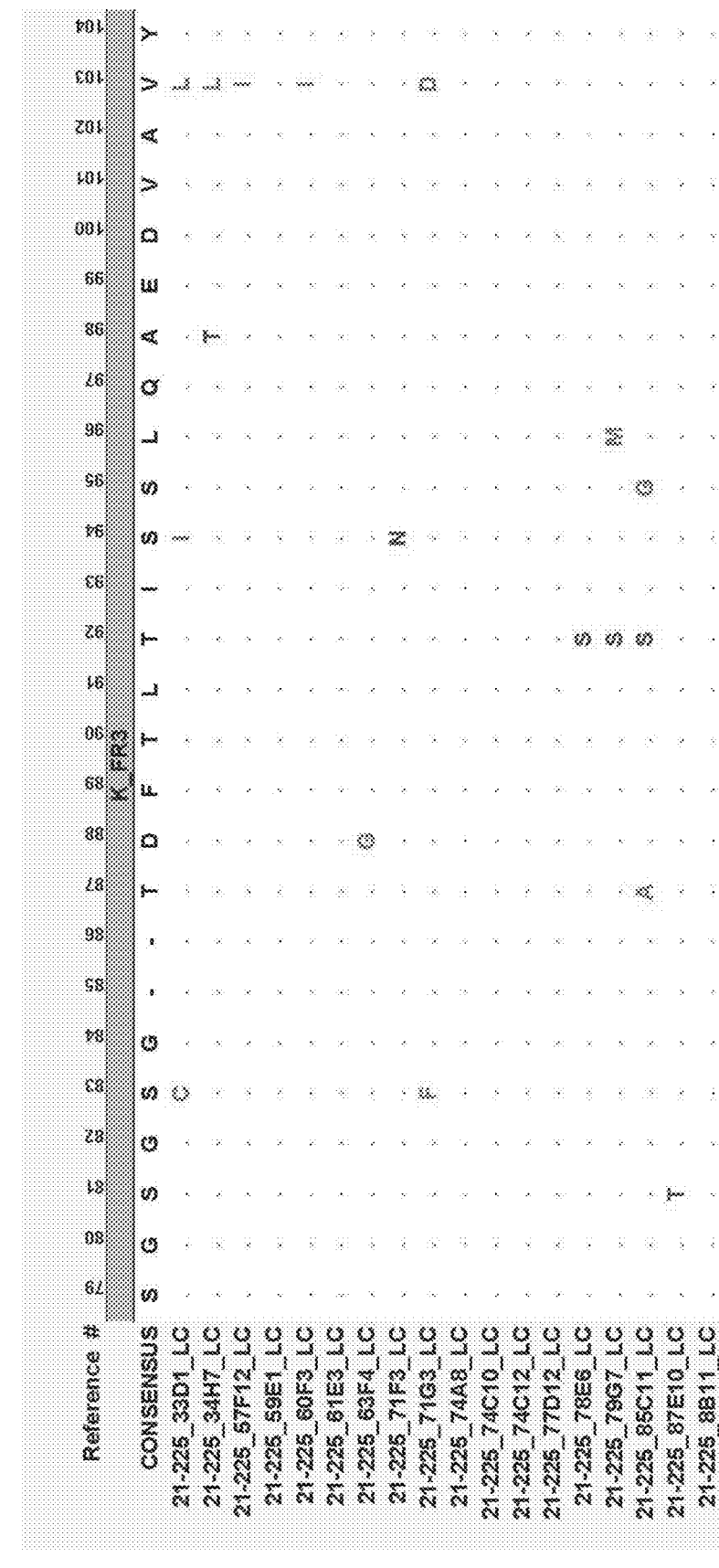
Figure 57:
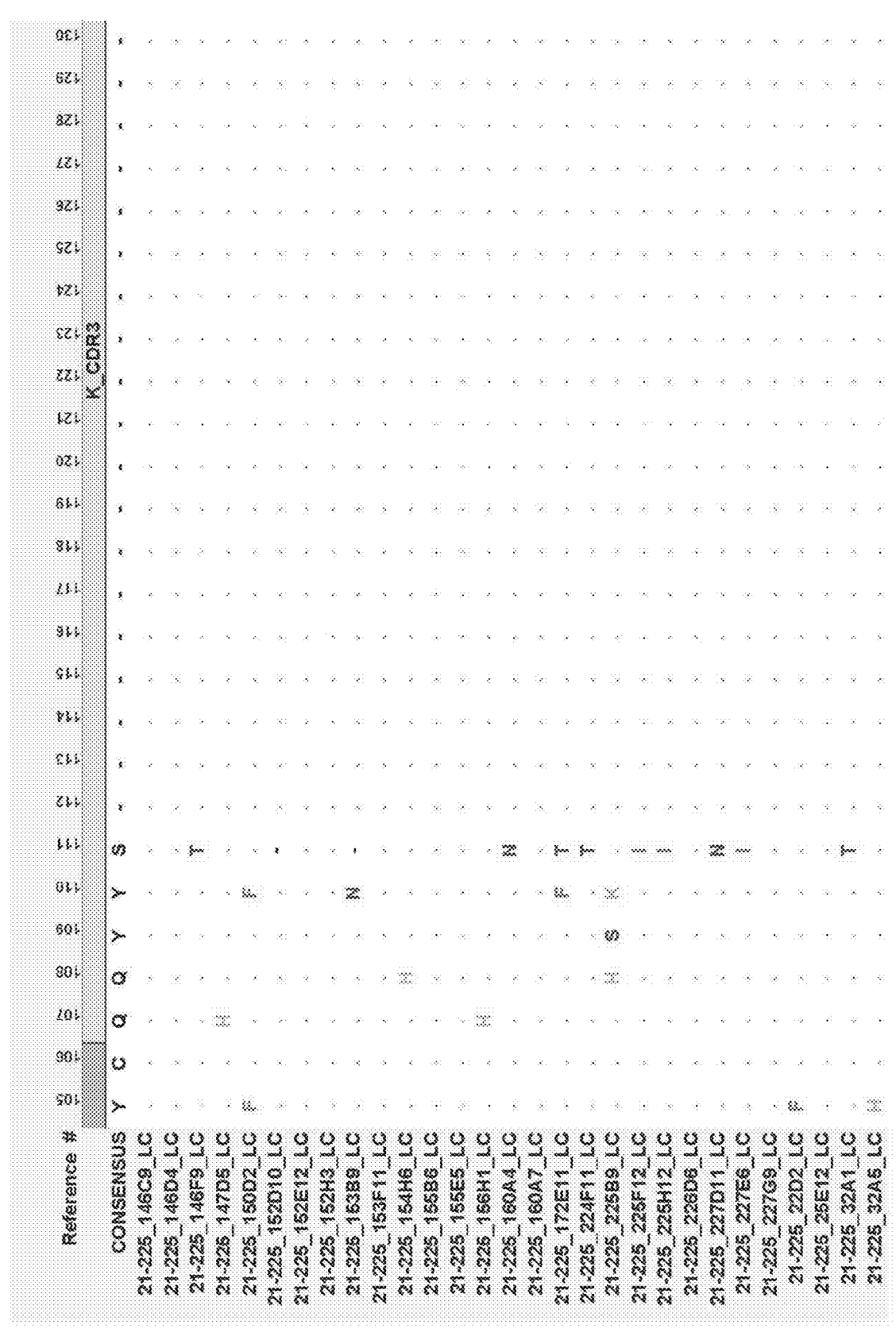
Figure 57:
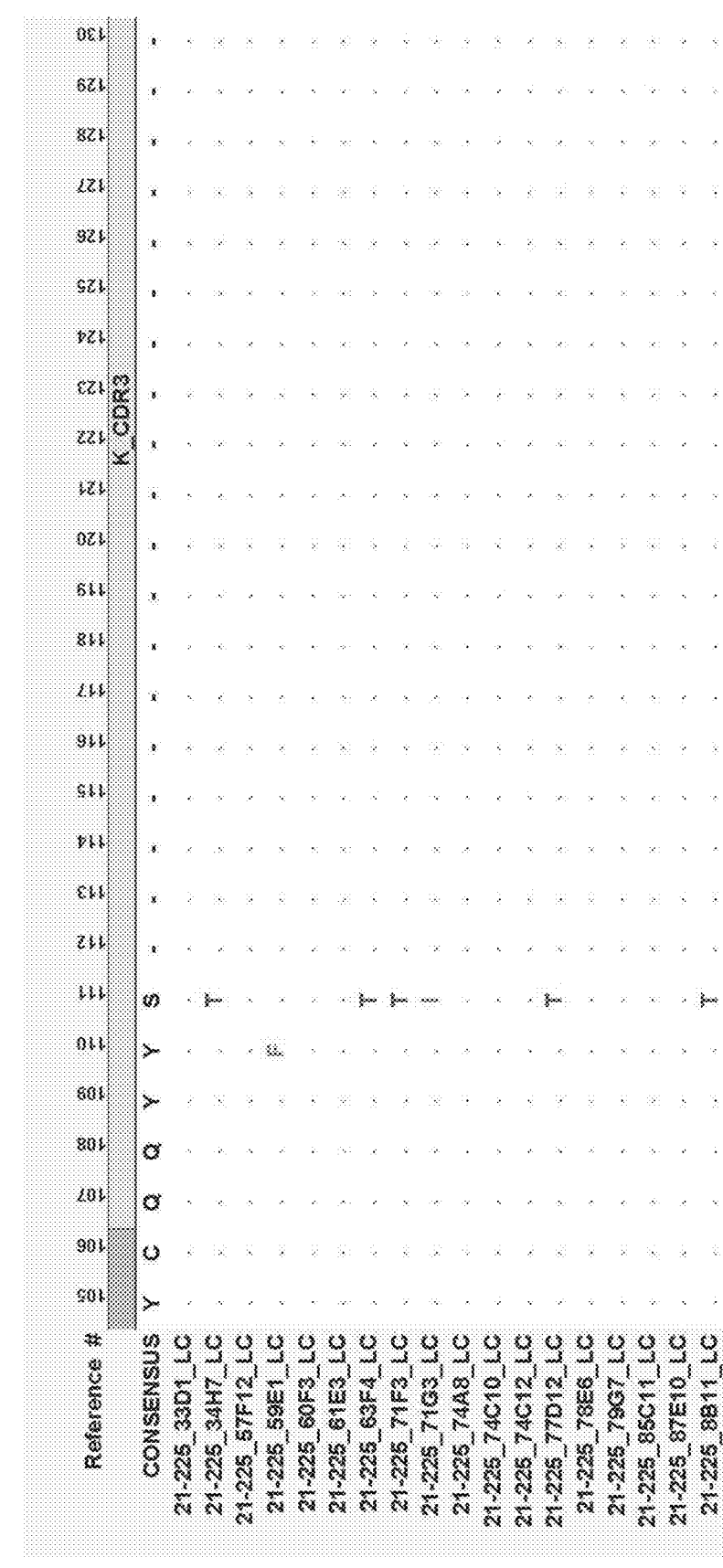
Figure 57:
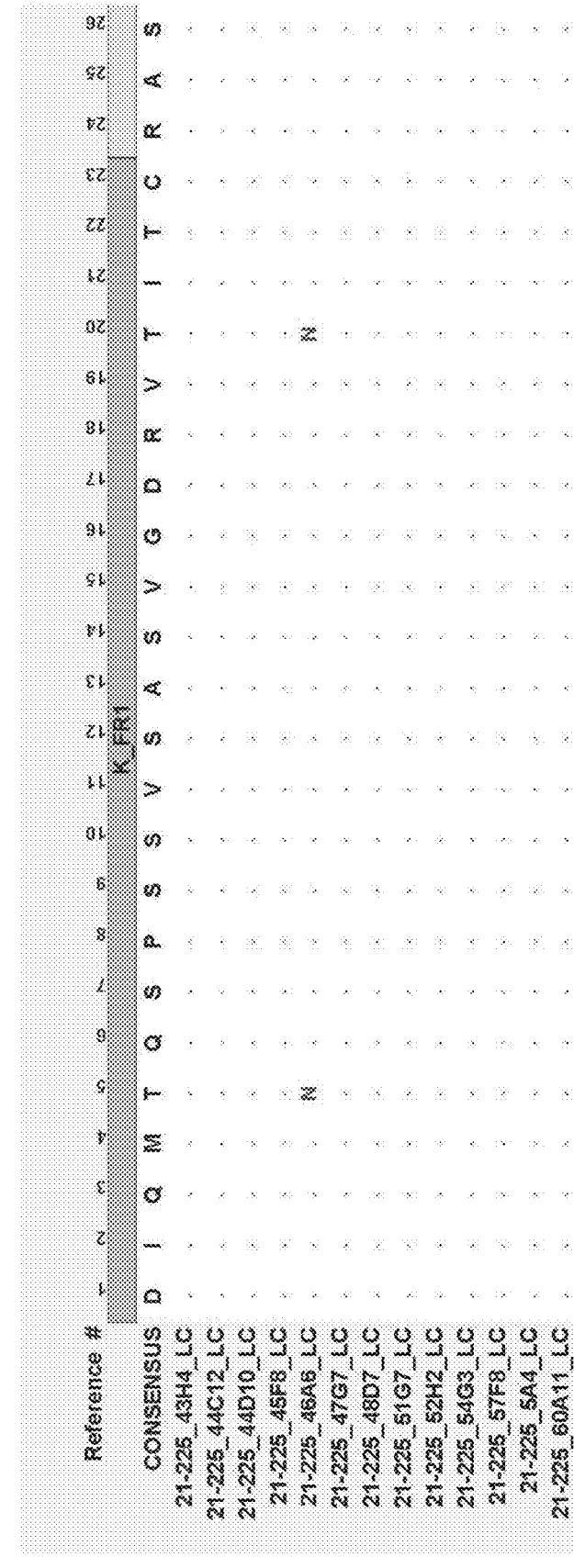
Figure 57:
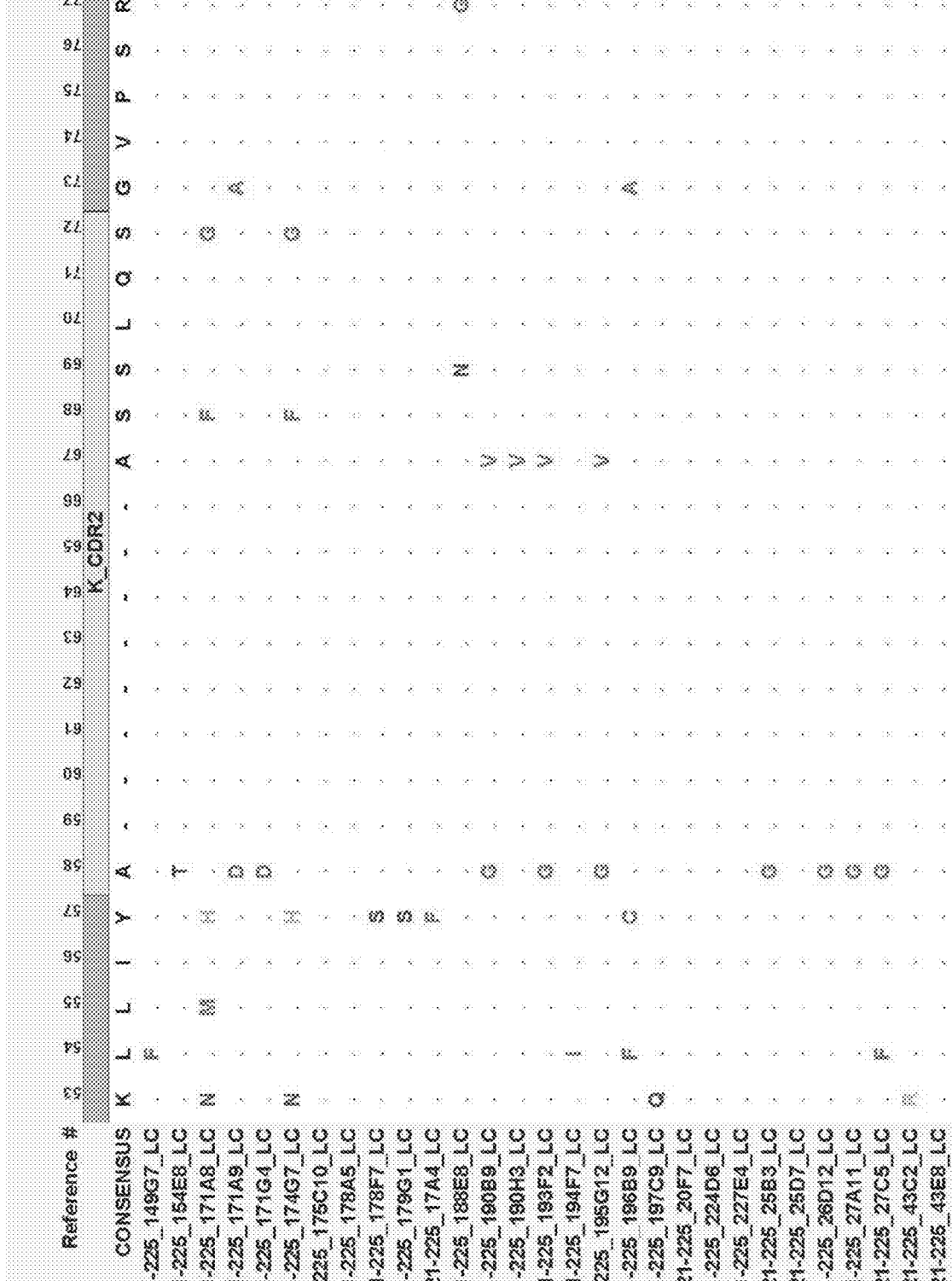
Figure 57:
Figure 57:
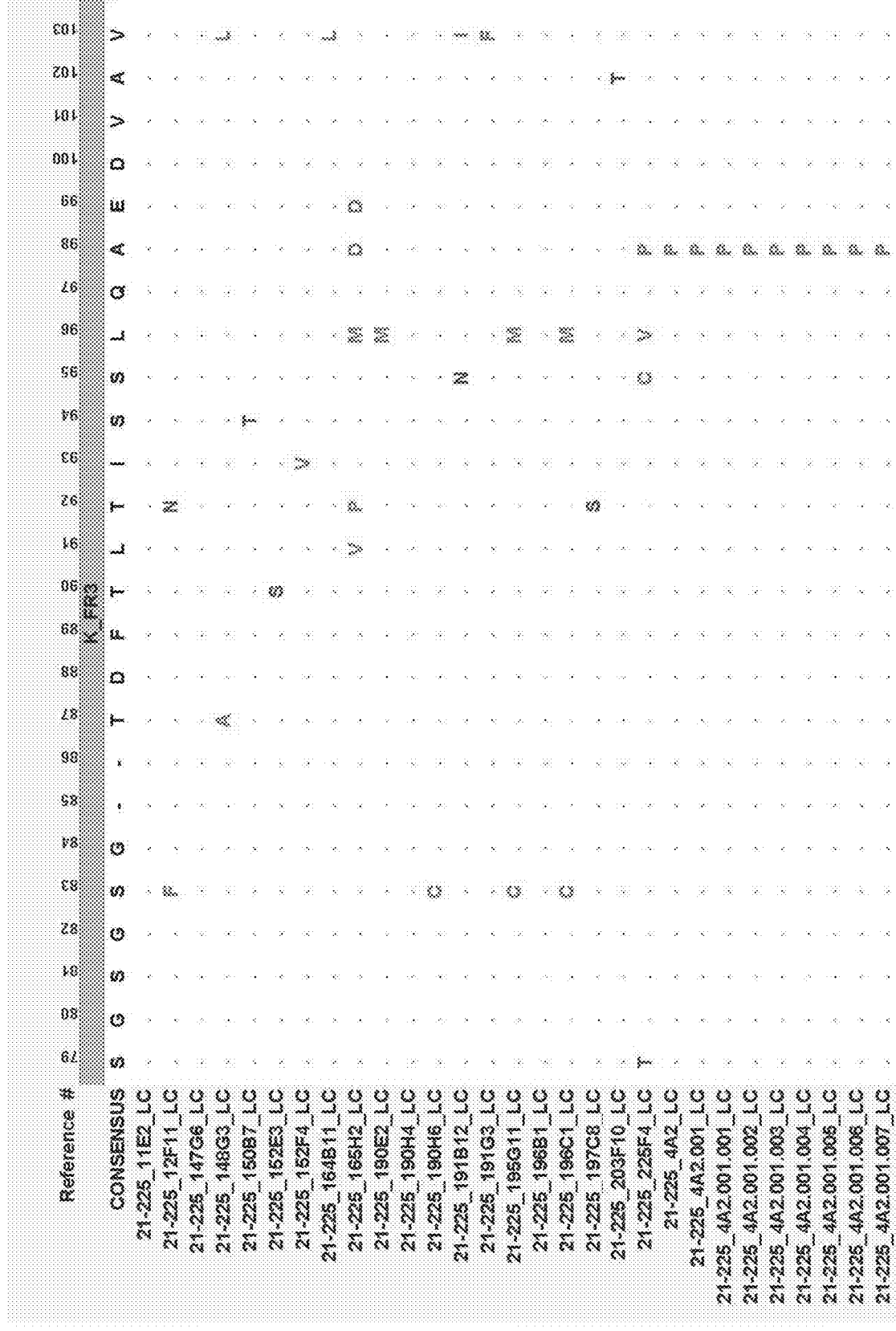
Figure 57:
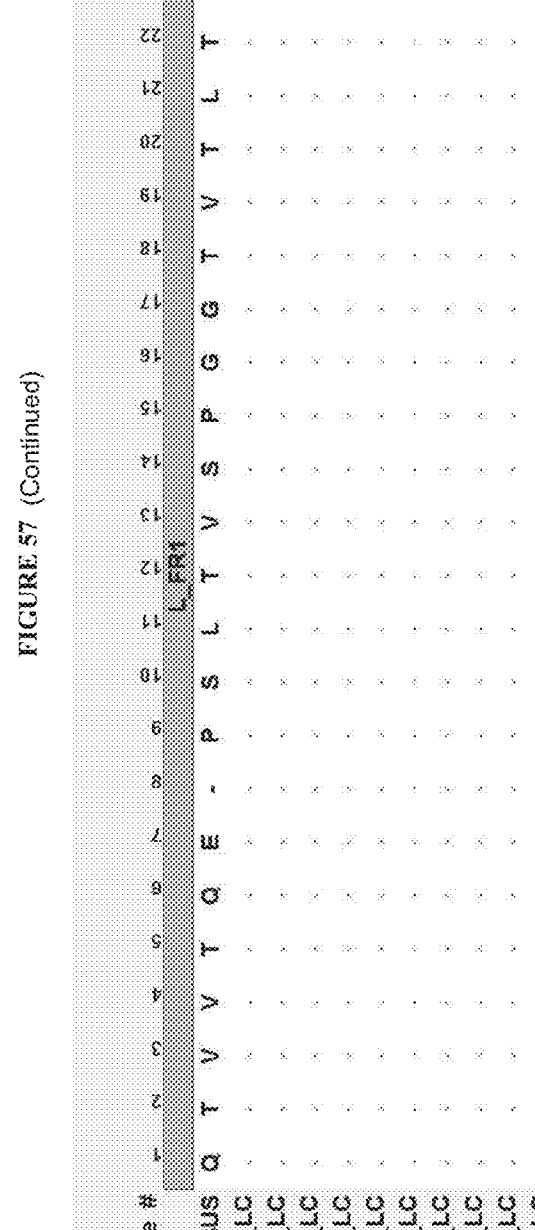
Figure 57:
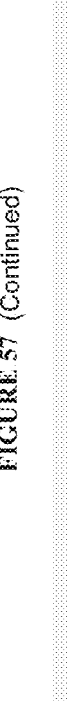
Figure 57:
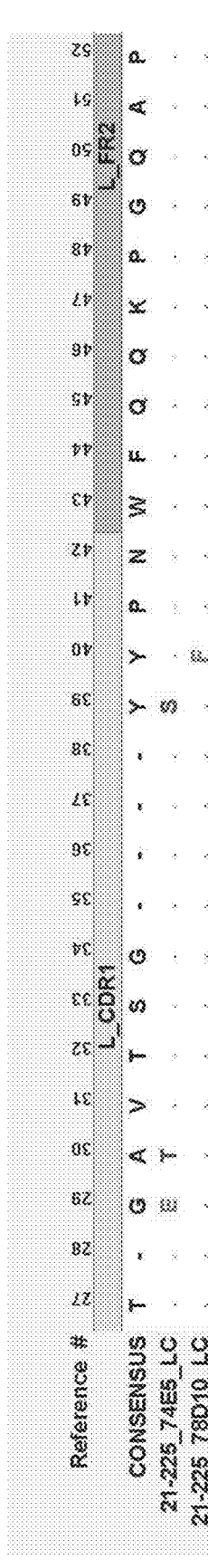
Figure 57:
Figure 57:
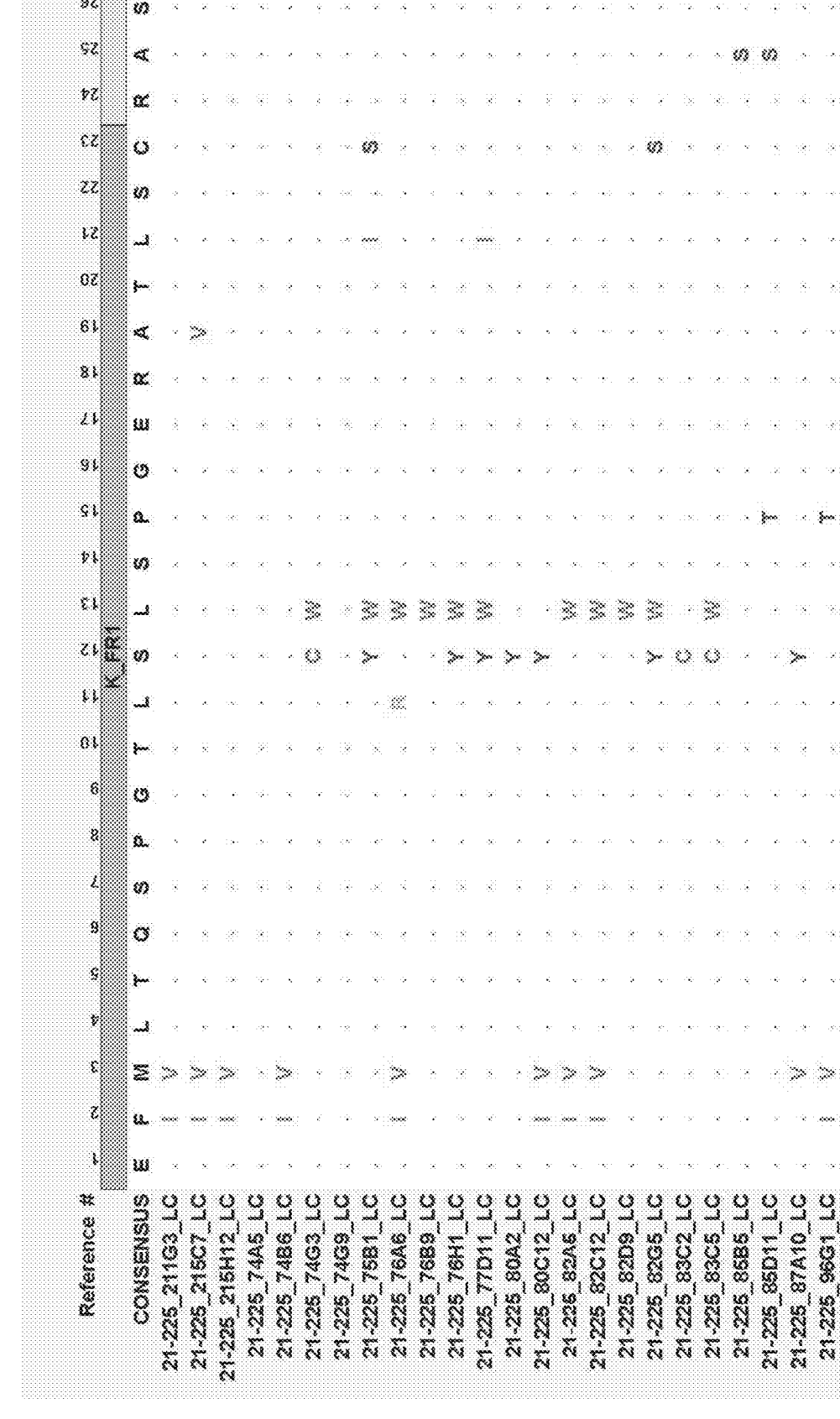
Figure 57:
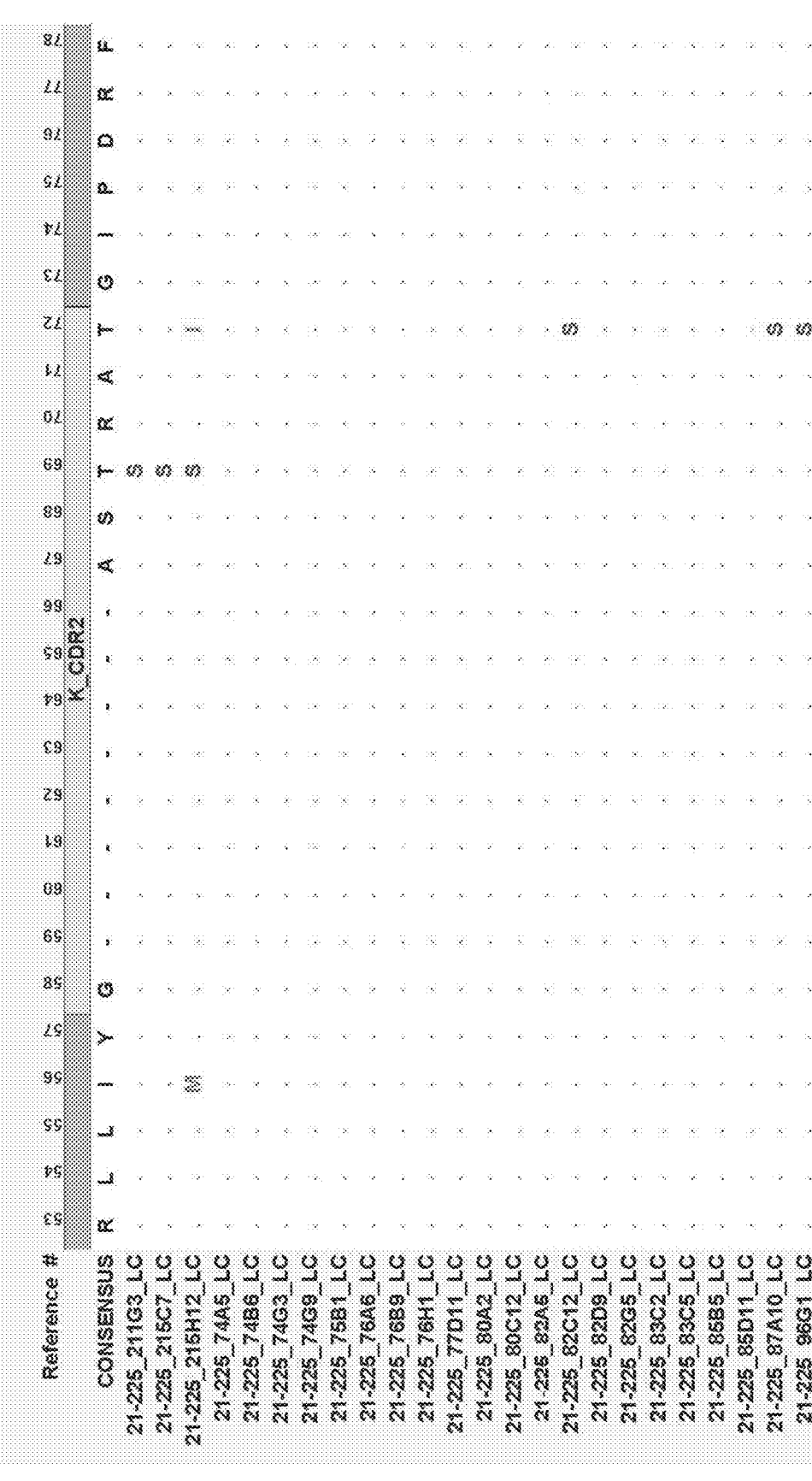
Figure 57:
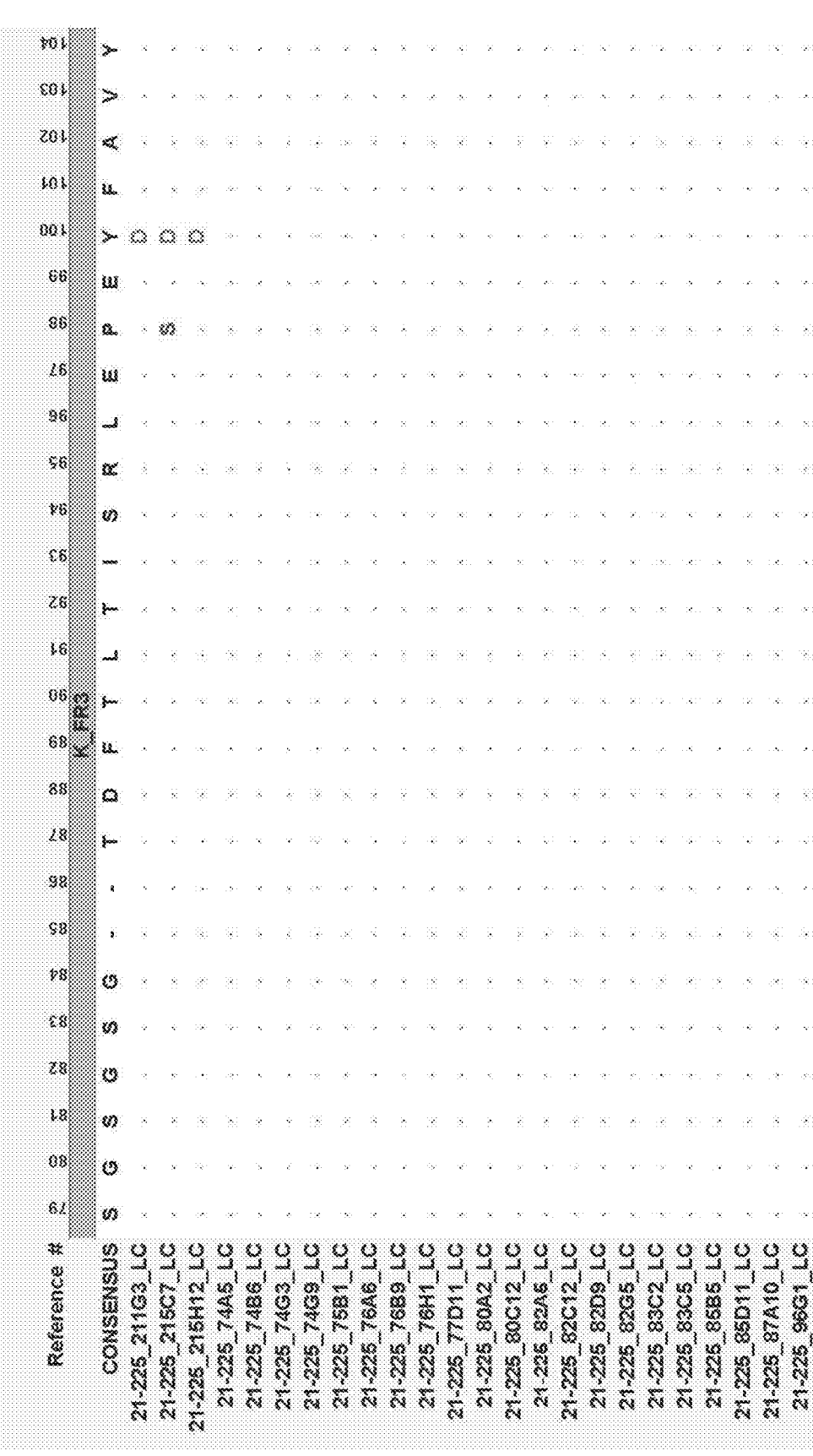
Figure 57:
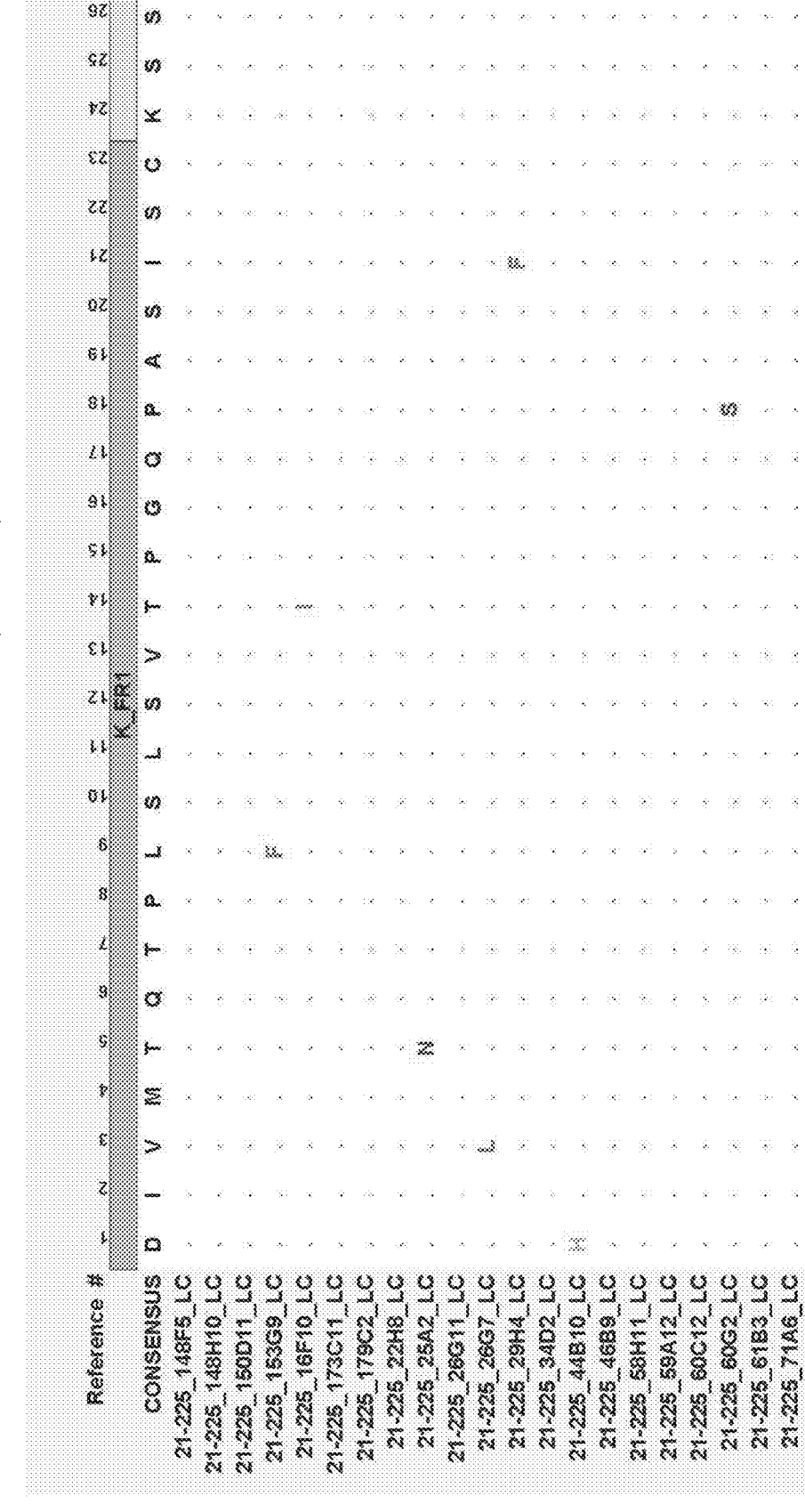
Figure 57:
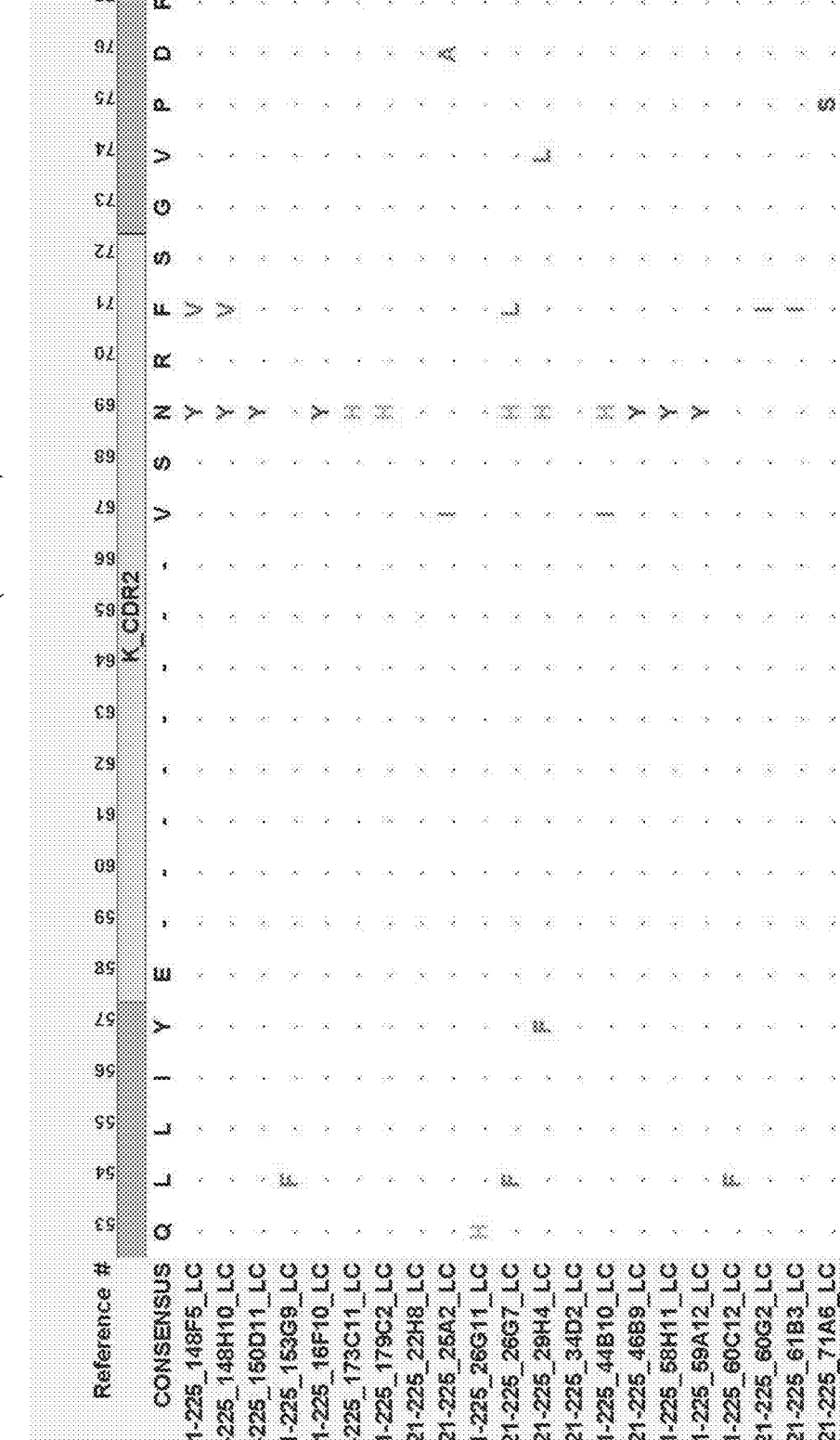
Figure 57:
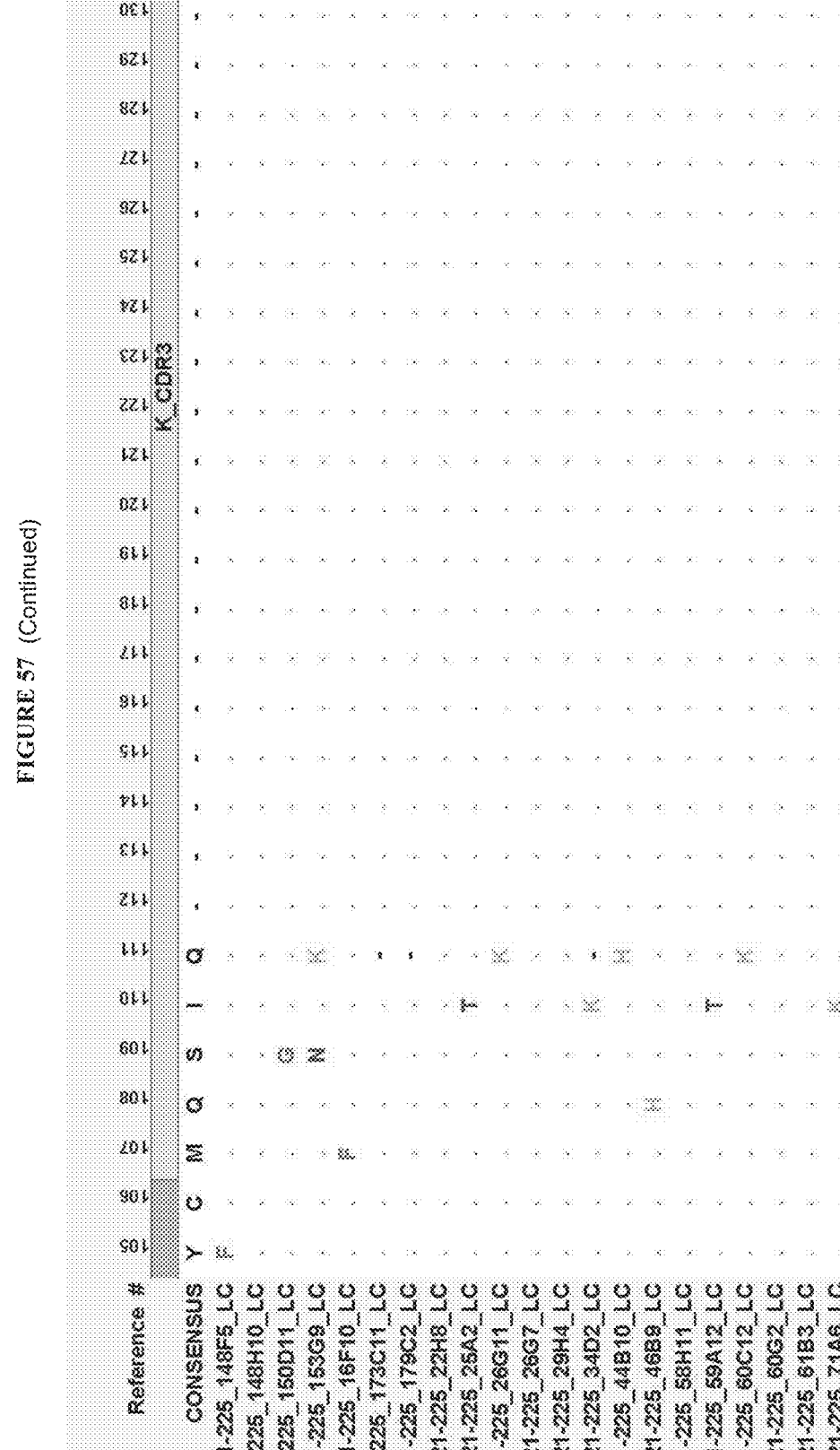
Figure 57:
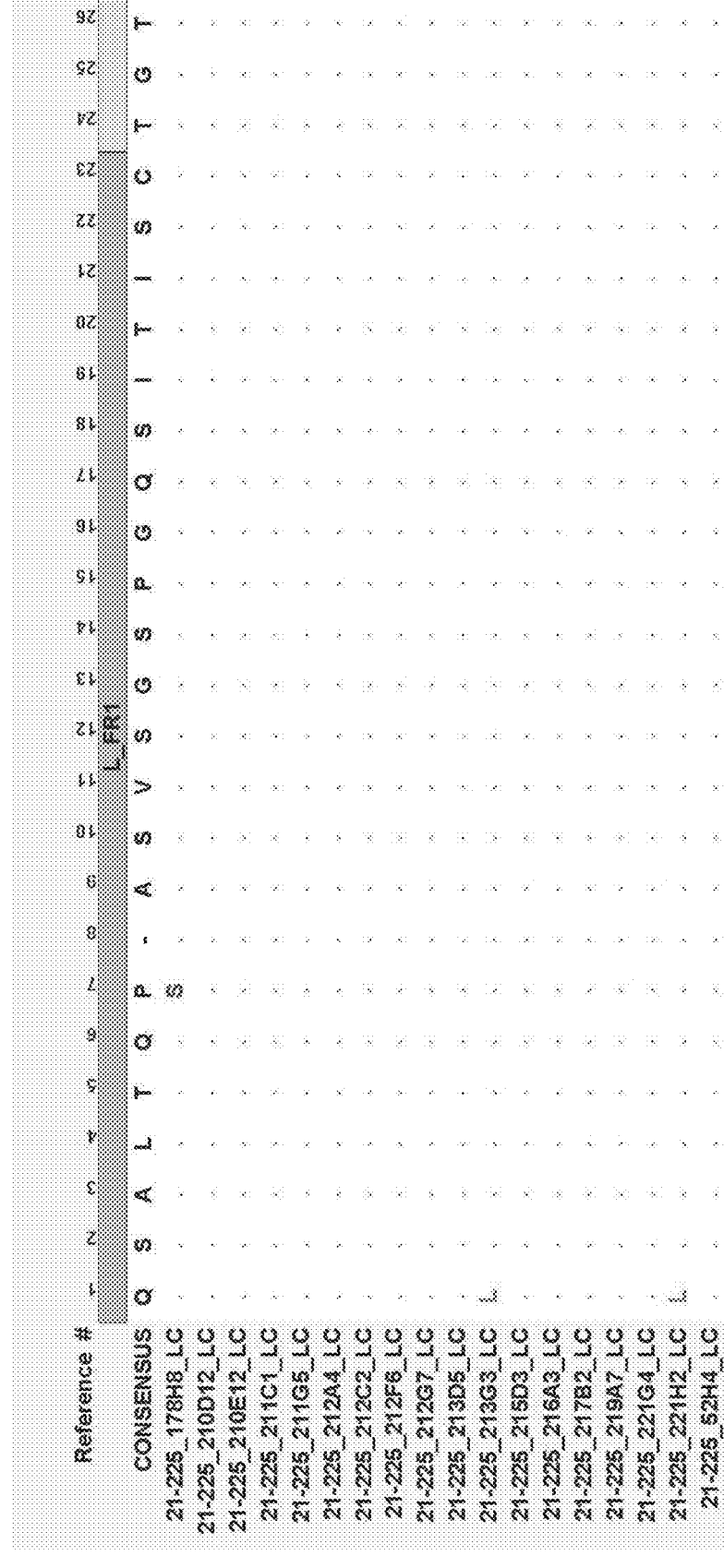
Figure 57:
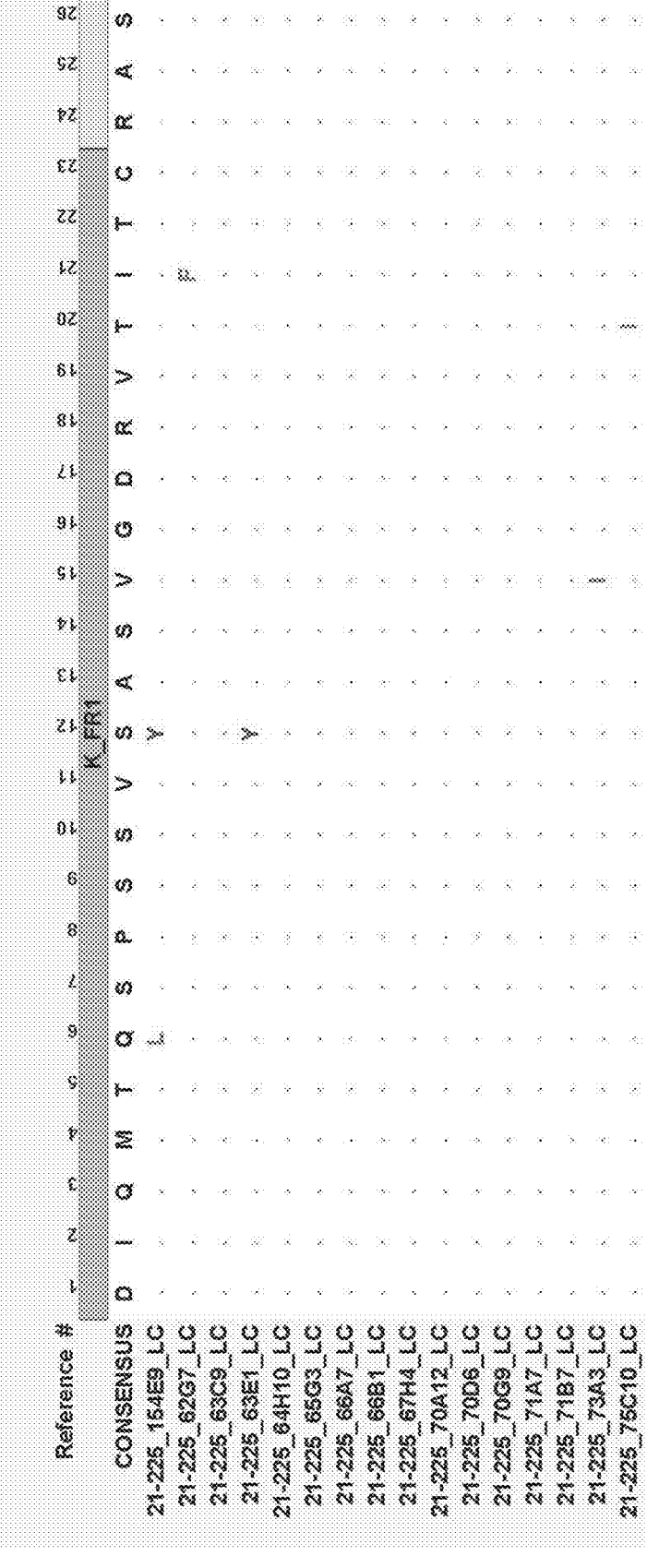
Figure 57:
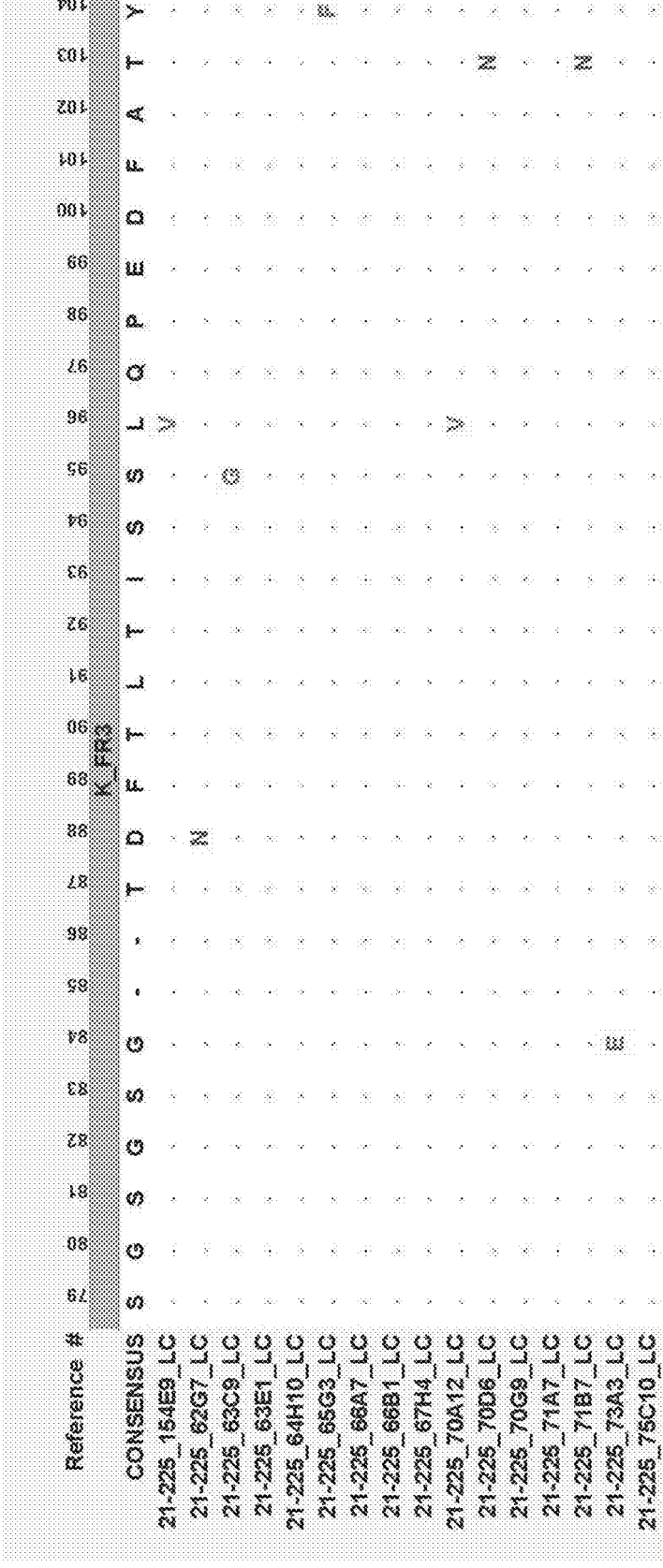
Figure 57:
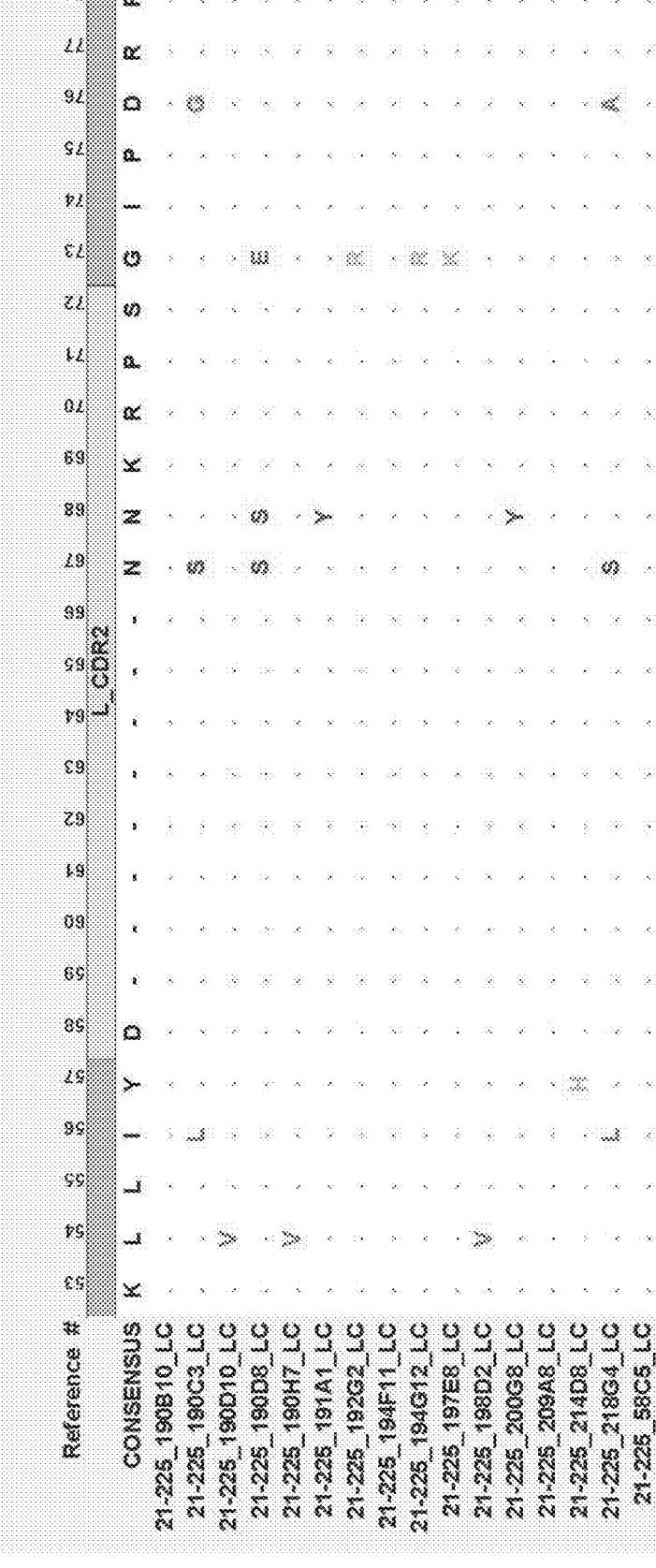
Figure 57:
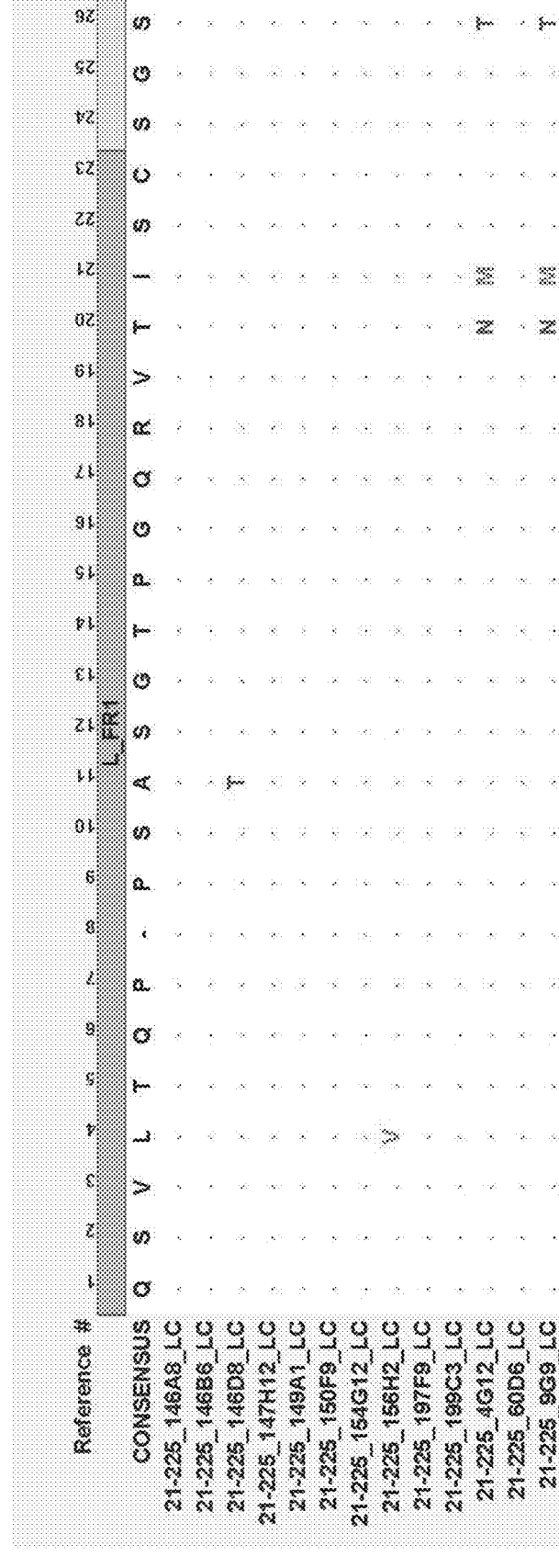
Figure 57:
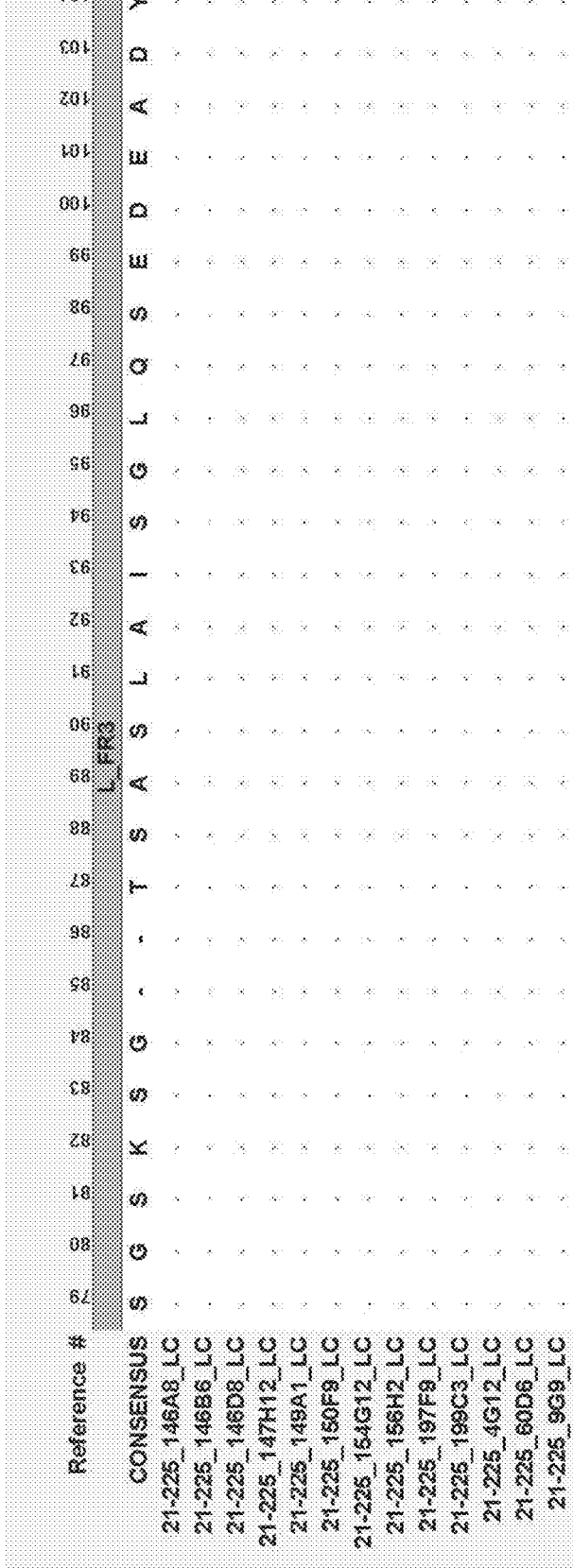
Figure 57:
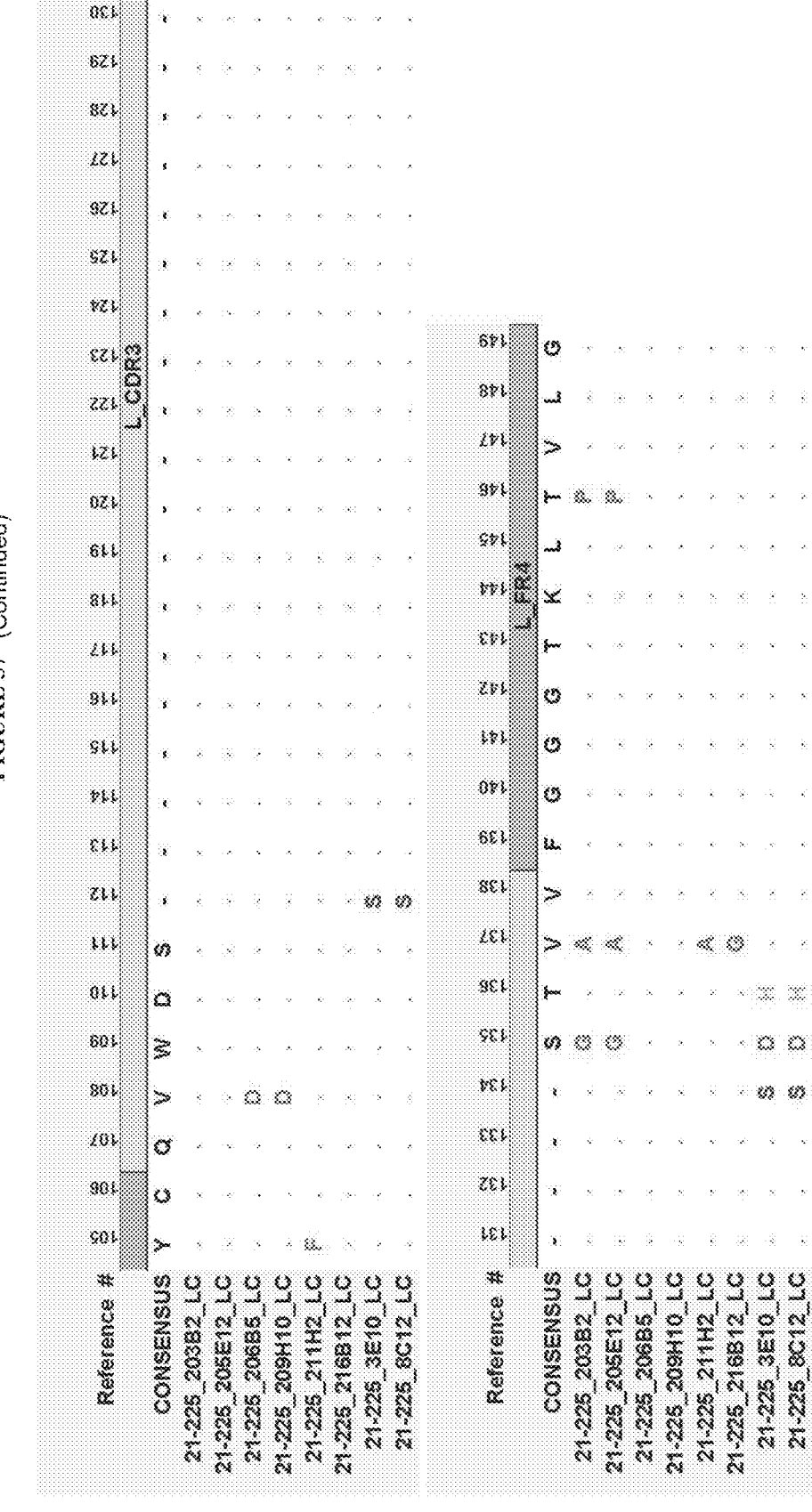

In some embodiments, an isolated antigen binding protein is provided, wherein the antigen binding protein specifically binds human ASGR-1 and comprises a heavy chain variable domain having at least 90% identity to any of the VH domain amino acid sequences set forth in Tables 19A, as depicted in FIG. 55 or in Tables 21-34 as depicted in FIG. 56 or in Tables 49-95 as depicted in FIG. 56. In some aspects, the invention provides an isolated antigen binding protein, wherein the antigen binding protein specifically binds human ASGR-1 and comprises a light chain variable domain having at least 90% identity to any of the VL domain amino acid sequences set forth in Table 20A, as depicted in FIG. 55, or in Tables 35-48, as depicted in FIG. 56 or in Tables 96-134 as depicted in FIG. 57. In some embodiments, the antigen binding protein comprises a heavy chain variable domain having at least 90% identity to any of the VH domain amino acid sequences set forth in Tables 19A as depicted in FIG. 55, or in Tables 21-34 as depicted in FIG. 56 or in Tables 49-95 as depicted in FIG. 57, and a light chain variable domain having at least 90% identity to any of the VL domain amino acid sequences set forth in Table 20A as depicted in FIG. 55 or in Tables 35-48 as depicted in FIG. 56 or in Tables 96-134 as depicted in FIG. 57. In some embodiments, the antigen binding protein comprises a heavy chain variable domain having any of the VH domain amino acid sequences set forth in Tables 19A as depicted in FIG. 55, or in Tables 21-34 as depicted in FIG. 56 or in Tables 49-95 as depicted in FIG. 57, and a light chain variable domain having any of the VL domain amino acid sequences set forth in Table 20A as depicted in FIG. 55 or in Tables 35-48 as depicted in FIG. 56 or in Tables 96-134 as depicted in FIG. 57.

In some embodiments, an antigen binding protein that specifically binds to human ASGR-1 at an epitope that is bound by any of the antigen binding proteins disclosed herein is provided. In some embodiments, the invention provides an isolated antigen binding protein that specifically binds to human ASGR-1 at an epitope that is bound by at least one of the antigen binding proteins set forth in Tables 2-7. In some embodiments, the invention provides an isolated antigen binding protein that specifically binds to human ASGR-1 at an epitope that is bound by at least one of the antigen binding proteins set forth in Table A. In some embodiments, the invention provides an isolated antigen binding protein that specifically binds to human ASGR-1 at an epitope that is bound by at least one of the antigen binding proteins set forth in Table B. In some embodiments, the invention provides an isolated antigen binding protein that specifically binds to human ASGR-1 at an epitope that is bound by at least one of the antigen binding proteins set forth in Table C. In some embodiments, the invention provides an isolated antigen binding protein that specifically binds to human ASGR-1 at an epitope that is bound by at least one of the antigen binding proteins set forth in Table 6.

In some embodiments, the invention provides an isolated antigen binding protein that competes for binding to human ASGR-1 with any of the antigen binding proteins disclosed herein. In some embodiments, the invention provides an isolated antigen binding protein that competes for binding with any of the antigen binding proteins set forth in Tables 2-7. In some embodiments, the invention provides an isolated antigen binding protein that competes for binding with any of the antigen binding proteins set forth in Table A. In some embodiments, the invention provides an isolated antigen binding protein that competes for binding with any of the antigen binding proteins set forth in Table B. In still some embodiments, the invention provides an isolated antigen binding protein that competes for binding with any of the antigen binding proteins set forth in Table C. In yet another embodiment, the invention provides an isolated antigen binding protein that competes for binding with any of the antigen binding proteins set forth in Table 6.

In some embodiments, an isolated antigen binding protein that binds to human ASGR-1 within the carbohydrate recognition domain ("CRD") (also known as the carbohydrate binding domain or "CBD") and inhibits human ASGR-1 binding to ligand is provided. In some embodiments, the antigen binding protein binds to human ASGR-1 within residues 148-291, or 149-291, or 150-291, or 151-291, or 152-291, or 153-291, or 154-291, or 155-291 of SEQ ID NO:5. In some embodiments, the invention comprises an isolated antigen binding protein that binds to human ASGR-1 CBD within Helix α-1. In some embodiments, the invention comprises an isolated antigen binding protein that binds to human ASGR-1 within residues 174-186 of SEQ ID NO:5. In some embodiments, the invention comprises an isolated antigen binding protein that binds to human ASGR-1 CBD within Helix α-2. In some embodiments, the invention comprises an isolated antigen binding protein that binds to human ASGR-1 CBD within residues 194-206 of SEQ ID NO:5. In some embodiments, the invention comprises an isolated antigen binding protein that binds to human ASGR-1 within residues 237-273 or residues 240-267 of SEQ ID NO:5. In some embodiments, the antigen binding protein binds to ASGR-1 having an amino acid sequence that is at least 90% identical to SEQ ID NO:5. In some embodiments, the antigen binding protein is an antibody.

In some embodiments, an isolated antigen binding protein or an antibody that binds to human ASGR-1 and inhibits human ASGR-1 function is provided. In some embodiments, the isolated antigen binding protein or an antibody binds to human ASGR-1 and inhibits human ASGR-1 from binding to a ligand. In some embodiments, the antigen binding protein or antibody or a paratope in an antibody binds to human ASGR-1 at an epitope comprising at least one of the following amino acid residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, R274 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, or Y273 (SEQ ID NO:5). In some embodiments, the antigen binding protein or antibody or paratope in an antibody binds to human ASGR-1 at an epitope comprising at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or paratope in an antibody binds to human ASGR-1 at an epitope comprising at least one of the following residues: D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments when the antigen binding protein or antibody or paratope in an antibody binds to human ASGR-1 at an epitope comprising at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or paratope in an antibody binds to human ASGR-1 at an epitope comprising at least one of the following residues: H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, N157, R170, S171, G172, Q202, H203, H204, I205, G206, P207, V208, N209, T210, D260, R271, P272, Y273, or R274 (SEQ ID NO:5). In some embodiments, the antigen binding protein or antibody or a paratope in an antibody binds to human ASGR-1 at an epitope comprising at least one of the following amino acid residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5). In some embodiments, the antigen binding protein or antibody or a paratope in an antibody binds to human ASGR-1 at an epitope comprising at least one of the following amino acid residues: H161, E162, W195, E196, Q198, K199, F200, Q202, H203, H204, G232, F233, K234, N235, W236, R237, P238, D261, G262, or R263 (SEQ ID NO:5). In some embodiments, the antigen binding protein or antibody or a paratope in an antibody binds to human ASGR1 at an epitope comprising at least one of the following amino acid residues: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5). In some embodiments, the antigen binding protein or antibody or a paratope in an antibody binds to human ASGR-1 at an epitope comprising at least one of the following amino acid residues: W167, S171, G172, K173, A174, A176, D177, N180, Y181, R183, L184, E185, D186, Q270, P272, or W275 (SEQ ID NO:5). In some embodiments, the antigen binding protein or antibody or a paratope in an antibody binds to human ASGR-1 at an epitope comprising at least one of the following amino acid residues: R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, or W264 (SEQ ID NO:5). In some embodiments, the antigen binding protein or antibody or a paratope in an antibody binds to human ASGR-1 at an epitope comprising at least one of the following amino acid residues: R170, W195, E196, K199, Q202, H203, H204, I205, G206, P207, V208, F233, K234, N235, W236, P238, D260, D261, G262, R263, or R274 (SEQ ID NO:5). In some embodiments, the antigen binding protein or antibody or a paratope in an antibody binds to human ASGR-1 at an epitope comprising at least one of the following amino acid residues: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5). In some embodiments, the antigen binding protein or antibody or a paratope in an antibody binds to human ASGR-1 at an epitope comprising at least one of the following amino acid residues: H161, S194, W195, E196, Q198, K199, F200, Q202, H203, F233, K234, N235, W236, R237, P238, or R263 (SEQ ID NO:5). In some embodiments, the antigen binding protein or antibody or a paratope in an antibody binds to human ASGR-1 at an epitope comprising at least one of the following amino acid residues: H161, E162, T193, S194, W195, E196, K199, Q202, T231, G232, F233, K234, N235, P238, D261, R263, R163, V192, E197, Q198, H203, P207, D228, E230, W236, R237, D260, G262, or W264 (SEQ ID NO:5). In some embodiments, the antigen binding protein or antibody or a paratope in an antibody binds to human ASGR-1 at an epitope comprising at least one of the following amino acid residues: H161, E162, T193, S194, W195, E196, K199, Q202, T231, G232, F233, K234, N235, P238, D261, or R263 (SEQ ID NO:5). In some embodiments, the antigen binding protein or antibody or a paratope in an antibody binds to human ASGR-1 at an epitope comprising at least one of the following amino acid residues: T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, or W264 (SEQ ID NO:5). In some embodiments, the antigen binding protein or antibody or a paratope in an antibody binds to human ASGR-1 at an epitope comprising at least one of the following amino acid residues: T193, S194, W195, E196, P220, W221, G226, T227, D228, Y229, E230, T231, G232, F233, K234, N235, W236, R237, P238, E239, or G252 (SEQ ID NO:5). In some embodiments, the antigen binding protein or antibody or a paratope in an antibody binds to human ASGR-1 at an epitope comprising at least one of the following amino acid residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, or C269 (SEQ ID NO:5). In some embodiments, the antigen binding protein or antibody or a paratope in an antibody binds to human ASGR-1 at an epitope comprising at least one of the following amino acid residues: D216, Q217, N218, G219, P220, W221, Y229, E230, K234, W236, E239, Q240, P241, D242, D243, W244, Y245, G246, L249, G250, G251, G252, D254, or Q270 (SEQ ID NO:5). In some embodiments, the antigen binding protein or antibody or a paratope in an antibody binds to human ASGR-1 at an epitope comprising at least one of the following amino acid residues: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W195, N209, N235, R237, P238, E239, Q240, D242, H257, T259, D260, D261, R263, N265, D267, R271, or Y273 (SEQ ID NO:5). In some embodiments, the antigen binding protein or antibody or a paratope in an antibody binds to human ASGR-1 at an epitope comprising at least one of the following amino acid residues: N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments, the antigen binding protein or antibody or a paratope in an antibody binds to human ASGR-1 at an epitope comprising at least one of the following amino acid residues: N157, R170, S171, G172, Q202, H203, H204, I205, G206, P207, V208, N209, T210, D260, R271, P272, Y273, or R274 (SEQ ID NO:5). In some embodiments, the antigen binding protein or antibody or a paratope in an antibody binds to human ASGR-1 at an epitope comprising at least one of the following amino acid residues: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5). In some embodiments, the antigen binding protein or antibody or a paratope in an antibody binds to human ASGR-1 at an epitope comprising at least one of the following amino acid residues: R170, S171, G172, A174, H204, I205, G206, P207, V208, N209, H257, D260, N265, D267, Q270, R271, P272, Y273, or R274 (SEQ ID NO:5). In some embodiments, the antigen binding protein or antibody or a paratope in an antibody binds to human ASGR-1 at an epitope comprising at least one of the following amino acid residues: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments, the antigen binding protein or antibody or a paratope in an antibody binds to human ASGR-1 at an epitope comprising at least one of the following amino acid residues: R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5).

In some embodiments, an isolated antigen binding protein or an antibody or a paratope in an antibody that specifically binds to human ASGR-1 and inhibits human ASGR-1 function is provided. In some embodiments, the isolated antigen binding protein or an antibody or a paratope in an antibody specifically binds to human ASGR-1 and inhibits human ASGR-1 from binding to a ligand. In some embodiments, the antigen binding protein or antibody or a paratope in an antibody specifically binds to human ASGR-1 within residues 148-291 of SEQ ID NO:5. In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5).

In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, Y273, P238, E239, P241, D243, Y245, G246, H247, G252, C255, F258, D260, R263, W264, V268, R271, D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, Y273, D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, R170, S171, G172, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, N209, R237, P238, E239, P241, D243, Y245, G246, H247, G252, C255, H257, T259, D260, V268, R271, Y273, R237, Q240, D242, W244, E253, N265, D266, D267, N209, P238, E239, P241, D243, Y245, G246, H247, G252, C255, H257, T259, V268, R271, Y273, N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: Q240, D242, W244, E253, N265, D266, D267, R237, Q240, D242, W244, E253, N265, D266, D267, N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: Q240, D242, W244, E253, N265, D266, or D267 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R237, Q240, D242, W244, E253, N265, D266, D267, N209, P238, E239, P241, D243, Y245, G246, H247, G252, C255, H257, T259, V268, R271, or Y273 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R237, Q240, D242, W244, E253, N265, D266, or D267 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: N209, R237, Q240, D242, W244, E253, H257, T259, N265, D266, D267, Y273, P238, E239, P241, D243, Y245, G246, H247, G252, C255, F258, D260, R263, W264, V268, or R271 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: N209, R237, Q240, D242, W244, E253, H257, T259, N265, D266, D267, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, or C269 (SEQ ID NO:5). In some embodiments when the antigen binding protein or antibody is bound to human ASGR-1, the antigen binding protein or antibody or a paratope in an antibody is positioned 5 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, or Q270 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: W195, N209, N235, R237, P238, E239, Q240, D242, H257, T259, D260, D261, R263, N265, D267, R271, Y273, Q198, Q202, P207, V208, F233, W236, D243, E253, F258, G262, W264, or D266 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W195, N209, N235, R237, P238, E239, Q240, D242, H257, T259, D260, D261, R263, N265, D267, R271, or Y273 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R170, S171, G172, A174, H204, I205, G206, P207, V208, N209, H257, D260, N265, D267, Q270, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: R170, S171, G172, K173, A174, D177, P207, V208, N209, R237, Q240, W244, G246, H247, G248, L249, E253, H257, T259, D260, N265, D267, Q270, R271, P272, Y273, or R274 (SEQ ID NO:5). In some embodiments when the antigen binding protein or antibody or a paratope in an antibody is positioned 8 angstroms or less from at least one of the following residues: D216, Q217, N218, G219, P220, W221, Y229, E230, K234, W236, E239, Q240, P241, D242, D243, W244, Y245, G246, L249, G250, G251, G252, D254, Q270, H215, K222, T231, G232, R237, P238, H247, G248, E253, C255, D266, V268, C269, W195, N209, N235, R237, P238, E239, Q240, D242, H257, T259, D260, D261, R263, N265, D267, R271, Y273, Q198, Q202, P207, V208, F233, W236, D243, E253, F258, G262, W264, D266, H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, R170, S171, G172, A174, H204, I205, G206, P207, V208, N209, H257, D260, N265, D267, Q270, R271, P272, Y273, R274, W167, F168, S169, K173, W175, D177, Y181, Q202, H203, T210, W211, R237, F258, T259, D261, D266, V268, C269, W275, R170, S171, G172, K173, A174, D177, P207, V208, N209, R237, Q240, W244, G246, H247, G248, L249, E253, H257, T259, D260, N265, D267, Q270, R271, P272, Y273, R274, S169, W175, A176, A178, T210, W211, W236, P238, E239, D242, Y245, G250, G251, F258, D261, G262, R263, W264, D266, V268, C269, W275, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues of human ASGR-1 (SEQ ID NO:5): D216, Q217, N218, G219, P220, W221, Y229, E230, K234, W236, E239, Q240, P241, D242, D243, W244, Y245, G246, L249, G250, G251, G252, D254, Q270, W195, N209, N235, R237, P238, E239, Q240, D242, H257, T259, D260, D261, R263, N265, D267, R271, Y273, H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, R170, S171, G172, A174, H204, I205, G206, P207, V208, N209, H257, D260, N265, D267, Q270, R271, P272, Y273, R274, R170, S171, G172, K173, A174, D177, P207, V208, N209, R237, Q240, W244, G246, H247, G248, L249, E253, H257, T259, D260, N265, D267, Q270, R271, P272, Y273, R274, N157, R170, S171, G172, Q202, H203, H204, I205, G206, P207, V208, N209, T210, D260, R271, P272, Y273, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, W264, W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, T279, R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, W264, H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, W264, H161, E162, T193, S194, W195, E196, K199, Q202, T231, G232, F233, K234, N235, P238, D261, R263, R163, V192, E197, Q198, H203, P207, D228, E230, W236, R237, D260, G262, or W264, T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, W264, N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270, or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, E162, W195, E196, Q198, K199, F200, Q202, H203, H204, G232, F233, K234, N235, W236, R237, P238, D261, G262, R263, W167, S171, G172, K173, A174, A176, D177, N180, Y181, R183, L184, E185, D186, Q270, P272, W275, R170, W195, E196, K199, Q202, H203, H204, I205, G206, P207, V208, F233, K234, N235, W236, P238, D260, D261, G262, R263, R274, H161, S194, W195, E196, Q198, K199, F200, Q202, H203, F233, K234, N235, W236, R237, P238, R263, H161, E162, T193, S194, W195, E196, K199, Q202, T231, G232, F233, K234, N235, P238, D261, R263, T193, S194, W195, E196, P220, W221, G226, T227, D228, Y229, E230, T231, G232, F233, K234, N235, W236, R237, P238, E239, G252, N157, R170, S171, G172, Q202, H203, H204, I205, G206, P207, V208, N209, T210, D260, R271, P272, Y273, R274, V156, W158, V159, H161, W167, F168, S169, K173, (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, W195, E196, Q198, K199, F200, Q202, H203, H204, G232, F233, K234, N235, W236, R237, P238, D261, G262, R263, V159, E160, R163, T193, S194, E197, V201, I205, G206, P207, Y229, E230, T231, E239, F258, T259, D260, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues of human ASGR-1 (SEQ ID NO:5): H161, E162, W195, E196, Q198, K199, F200, Q202, H203, H204, G232, F233, K234, N235, W236, R237, P238, D261, G262, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: W167, S171, G172, K173, A174, A176, D177, N180, Y181, R183, L184, E185, D186, Q270, P272, W275, P155, N157, W158, F168, S169, R170, W175, A178, D179, C182, A187, W211, C269, R271, Y273, R274, C277, or T279 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: W167, S171, G172, K173, A174, A176, D177, N180, Y181, R183, L184, E185, D186, Q270, P272, or W275 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: R170, W195, E196, K199, Q202, H203, H204, I205, G206, P207, V208, F233, K234, N235, W236, P238, D260, D261, G262, R263, R274, N157, V159, F168, S169, S171, S194, Q198, F200, V201, T210, R237, E239, Q240, F258, T259, or W264 (SEQ ID NO:5). In some embodiments when the antigen binding protein or a paratope in an antibody is bound to human ASGR-1, the antigen binding protein or a paratope in an antibody is positioned 5 angstroms or less from at least one of the following residues: R170, W195, E196, K199, Q202, H203, H204, I205, G206, P207, V208, F233, K234, N235, W236, P238, D260, D261, G262, R263, or R274 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, S194, W195, E196, Q198, K199, F200, Q202, H203, F233, K234, N235, W236, R237, P238, R263, E160, E162, V192, T193, E197, V201, H204, Y229, E230, T231, G232, E239, Q240, P241, D261, G262, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, S194, W195, E196, Q198, K199, F200, Q202, H203, F233, K234, N235, W236, R237, P238, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: H161, E162, T193, S194, W195, E196, K199, Q202, T231, G232, F233, K234, N235, P238, D261, R263, R163, V192, E197, Q198, H203, P207, D228, E230, W236, R237, D260, G262, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: H161, E162, T193, S194, W195, E196, K199, Q202, T231, G232, F233, K234, N235, P238, D261, or R263 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: T193, S194, W195, E196, P220, W221, G226, T227, D228, Y229, E230, T231, G232, F233, K234, N235, W236, R237, P238, E239, G252, H161, E162, V191, V192, E197, Q198, D216, G219, K222, W223, D225, R263, or W264 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: T193, S194, W195, E196, P220, W221, G226, T227, D228, Y229, E230, T231, G232, F233, K234, N235, W236, R237, P238, E239, or G252 (SEQ ID NO:5). In some embodiments when the antigen binding protein or antibody or a paratope in an antibody is bound to human ASGR-1, the antigen binding protein or antibody or a paratope in an antibody is positioned 8 angstroms or less from at least one of the following residues: N157, R170, S171, G172, Q202, H203, H204, I205, G206, P207, V208, N209, T210, D260, R271, P272, Y273, R274, V156, W158, V159, H161, W167, F168, S169, K173, K199, F200, V201, W211, R237, H257, F258, T259, D261, D267, V268, Q270 or W275 (SEQ ID NO:5). In some embodiments when the antigen binding protein or antibody or a paratope in an antibody is bound to human ASGR-1, the antigen binding protein or antibody or a paratope in an antibody is positioned 5 angstroms or less from at least one of the following residues: N157, R170, S171, G172, Q202, H203, H204, I205, G206, P207, V208, N209, T210, D260, R271, P272, Y273 or R274 (SEQ ID NO:5).

In some embodiments, an isolated antigen binding protein or antibody that specifically binds to human ASGR-1 and inhibits human ASGR-1 function is provided. In some embodiments, the isolated antigen binding protein or antibody that specifically binds to human ASGR-1 inhibits binding of human ASGR-1 binding to a ligand. In some embodiments, the antigen binding protein or antibody specifically binds to human ASGR-1 at a location that overlaps with a location where a ligand binds to human ASGR-1. In some embodiments, the location where a ligand binds to ASGR-1 includes at least one amino acid residue selected from the group consisting of: N209, R237, Q240, D242, W244, E253, H257, T259, N265, D266, D267, Y273, P238, E239, P241, D243, Y245, G246, H247, G252, C255, F258, D260, R263, W264, V268, or R271 (SEQ ID NO:5). In some embodiments, an isolated antigen binding protein or an antibody specifically binds to human ASGR-1 at a location that overlaps with a location that a ligand binds to ASGR-1. In some embodiments, the location that a ligand binds to human ASGR-1 includes at least one amino acid residue selected from the group consisting of: N209, R237, Q240, D242, W244, E253, H257, T259, N265, D266, D267, and Y273 (SEQ ID NO:5).

In some embodiments, an isolated antigen binding protein that binds to human ASGR-1 and inhibits human ASGR, ASGR-1 and/or ASGR-2 function is provided, wherein the antigen binding protein does not bind to a variant ASGR-1 protein, and wherein said variant ASGR-1 protein comprises a single mutation of a residue selected the group consisting of: R170, S171, G172, R183, L184, W195, E196, K199, H203, H204, P207, V208, N209, H215, D216, P220, D225, D228, R237, P238, E239, P241, D242, D243, Y245, G246, H247, G248, L249, G251, E253, T259, D260, R263, N265, Q270, R271, P272, R274, and E280 as shown in SEQ ID NO:5. In some embodiments, an isolated antigen binding protein or an antibody is contemplated. An antigen binding protein "does not bind" to a variant ASGR-1 protein when the measured reduction in antibody binding signal to a variant ASGR-1 protein (compared to that determined for binding to wild type ASGR-1) is statistically significant as measured by any number of methods known to one skilled in the art, such as the method described in Example 7E below. In some embodiments, the variant ASGR-1 protein comprises a single mutation of a residue at a position selected from the group consisting of: W195, E196, K199, H203, H204, P207, P220, G251, and R263 as shown in SEQ ID NO:5. In some embodiments, the single mutation is selected from the group consisting of H203, H204, P220, and G251. In some embodiments, the single mutation is selected from the group consisting of W195, E196 and K199. In some embodiments, the single mutation is selected from the group consisting of W195, E196 and H204. In some embodiments, the single mutation is selected from the group consisting W195, K199, and R263. In some embodiments, the single mutation is selected from the group consisting of W195 and E196. In some embodiments, the single mutation is selected from the group consisting of W195 and K199. In some embodiments, the single mutation is selected from the group consisting of W195 or P207. In some embodiments, the single mutation is selected from the group consisting of W195 and R263. In some embodiments, the single mutation is selected from the group consisting of H203 and H204. In some embodiments, the single mutation is selected from the group consisting of K199 and R263. In some embodiments, the single mutation is a mutation of residue W195. In some embodiments, the variant ASGR-1 protein comprises a single mutation of a residue selected the group consisting of: R170, S171, R183, L184, H215, P220, P238, G246, H247, G248, G251, and N265 as shown in SEQ ID NO:5. In some embodiments, the single mutation is selected from the group consisting of R183, L184, H215, P220, G246, G248, G251, and N265. In some embodiments, the single mutation is selected from the group consisting of L184, P220, P238, H247, and G251. In some embodiments, the single mutation is selected from the group consisting of R170, S171, and L184. In some embodiments, the single mutation is a mutation of residue R183. In some embodiments, the single mutation is a mutation of residue L184. In some embodiments, the variant ASGR-1 protein comprises a single mutation of a residue at a position selected from the group consisting of: P241, D242, D243, Y245, G251, E253 and D260 as shown in SEQ ID NO:5. In some embodiments, the single mutation is selected from the group consisting of P241, D243, Y245, G251, E253 and D260. In some embodiments, the single mutation is selected from the group consisting of P241, D243, and E253. In some embodiments, the single mutation is a mutation of residue D260. In some embodiments, the variant ASGR-1 protein comprises a single mutation of a residue at a position selected from the group consisting or comprising: R170, R237, E239, P241, T259, D260, R263, and N265 as shown in SEQ ID NO:5. In some embodiments, the single mutation is selected from the group consisting of R237, D260 and R263. In some embodiments, the single mutation is selected from the group consisting of R237, T259, D260 and R263. In some embodiments, the single mutation is selected from the group consisting of R170, R237, P241, T259, D260, R263 and N265. In some embodiments, the single mutation is selected from the group consisting of R237, E239, P241, T259, D260, R263 and N265. In some embodiments, the variant ASGR-1 protein comprises a single mutation of a residue at a position selected from the group consisting or comprising: R170, S171, G172, E196, H204, P207, V208, N209, H215, D216, D225, D228, P238, P241, D242, D243, H247, G248, L249, G251, D260, R263, N265, Q270, R271, P272, R274 and E280 as shown in SEQ ID NO:5. In some embodiments, the single mutation is selected from the group consisting of R170, S171, G172, E196, H204, P207, V208, N209, H215, D216, D225, D228, P238, P241, D242, D243, H247, G248, L249, G251, D260, R263, N265, Q270, R271, P272, R274 and E280 as shown in SEQ ID NO:5. In some embodiments, the single mutation is selected from the group consisting of R170, S171, G172, E196, H204, P207, H215, D216, D225, D228, D243, G248, L249, G251, D260, Q270, R271, P272, R274 and E280. In some embodiments, the single mutation is selected from the group consisting of G172, V208, R271, P272 and R274. In some embodiments, the single mutation is selected from the group consisting of G172, R271 and R274. In some embodiments, the single mutation is selected from the group consisting of G172, N209, and R271. In some embodiments, the single mutation is selected from the group consisting of R170, G172, V208, R271 and P272. In some embodiments, the single mutation is selected from the group consisting of G172, V208, P238, R271, P272 and R274. In some embodiments, the single mutation is selected from the group consisting of G172, P238, R271, P272 and R274. In some embodiments, the variant ASGR-1 protein comprises a single mutation of a residue at a position selected from the group consisting or comprising: G172, P238, R271 and R274 as shown in SEQ ID NO:5. In some embodiments, the variant ASGR-1 protein comprises a single mutation of a residue at a position selected from the group consisting or comprising: R170, G172, V208 and R274 as shown in SEQ ID NO:5. In some embodiments, the variant ASGR-1 protein comprises a single mutation of a residue at a position selected from the group consisting or comprising: R170, R183, H215 and Q270 as shown in SEQ ID NO:5. In some embodiments, the variant ASGR-1 protein comprises a single mutation of a residue at a position selected from the group consisting or comprising: P241, T259, and N265 as shown in SEQ ID NO:5. In some embodiments, the variant ASGR-1 protein comprises a single mutation of a residue at a position selected from the group consisting or comprising: P207 and R263 as shown in SEQ ID NO:5. In some embodiments, the variant ASGR-1 protein comprises a single mutation of a residue at a position selected from the group consisting or comprising: G172, P241, D242, H247, L249, N265, R271 and P272 as shown in SEQ ID NO:5. In some embodiments, the antigen binding protein or antibody does not bind to two or more variant ASGR-1 proteins, wherein the variant ASGR-1 proteins comprise the single mutations of the group individually.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein including an antibody "specifically binds" to an antigen, such as ASGR, ASGR-1 or ASGR-2, if it binds to the antigen with a tight binding affinity as determined by a equilibrium dissociation constant ($K_D$, or corresponding $K_D$, as defined below) value of $10^{-7}$ M or less. An antigen binding protein that specifically binds to human ASGR, ASGR-1 or ASGR-2 may be able to bind to ASGR, ASGR-1 or ASGR-2 from other species as well with the same or different affinities.

Affinity can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or Octet® analysis (ForteBio)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

Further embodiments of the invention provide antigen binding molecules (e.g., antibodies) that specifically bind ASGR, ASGR-1 and/or ASGR-2 with an equilibrium dissociation constant or $K_D$ ($k_{off}/k_{on}$) of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M, or of less than $5 \times 10^{-13}$ M (lower values indicating tighter binding affinity). Yet further embodiments of the invention are antigen binding molecules that specifically bind ASGR, ASGR-1 and/or ASGR-2 with an equilibrium dissociation constant or $K_D$ ($k_{off}/k_{on}$) of less than about $10^{-7}$ M, or of less than about $10^{-8}$ M, or of less than about $10^{-9}$ M, or of less than about $10^{-10}$ M, or of less than about $10^{-11}$ M, or of less than about $10^{-12}$ M, or of less than about $10^{-13}$ M, or of less than about $5 \times 10^{-13}$ M.

In still another embodiment, an antigen binding protein of the invention (e.g., an antibody) that specifically bind ASGR, ASGR-1 and/or ASGR-2 has an equilibrium dissociation constant or $K_D$ ($k_{off}/k_{on}$) of between about $10^{-7}$ M and about $10^{-8}$ M, between about $10^{-8}$ M and about $10^{-9}$ M, between about $10^{-9}$ M and about $10^{-10}$ M, between about $10^{-10}$ M and about $10^{-11}$ M, between about $10^{-11}$ M and about $10^{-12}$ M, between about $10^{-12}$ M and about $10^{-13}$ M. In still another embodiment, an antibody of the invention that specifically bind ASGR, ASGR-1 and/or ASGR-2 has an equilibrium dissociation constant or $K_D$ ($k_{off}/k_{on}$) of between $10^{-7}$ M and $10^{-8}$ M, between $10^{-8}$ M and $10^{-9}$ M, between $10^{-9}$ M and $10^{-10}$ M, between $10^{-10}$ M and $10^{-11}$ M, between $10^{-11}$ M and $10^{-12}$ M, between $10^{-12}$ M and $10^{-13}$ M.

It will be appreciated that an antigen binding protein of the present invention (e.g., an antibody or fragments thereof) may have at least one amino acid substitution, providing that the antigen binding protein retains the same or better desired binding specificity (e.g., binding to human ASGR, human ASGR-1, and/or human ASGR-2) (See Example 14). Therefore, modifications to the antigen binding protein structures are encompassed within the scope of the invention. In one embodiment, the antigen binding protein (e.g., but not limited to, an antibody) comprises sequences that each independently differ by 5, 4, 3, 2, 1, or 0 single amino acid additions, substitutions, and/or deletions from a CDR sequence of those set forth in Table 2 herein. As used herein, a CDR sequence that differs by no more than a total of, for example, four amino acid additions, substitutions and/or deletions from a CDR sequence shown in Table 2 below refers to a sequence with 4, 3, 2, 1 or 0 single amino acid additions, substitutions, and/or deletions compared with the sequences shown in Table 2. These may include amino acid substitutions, which may be conservative or non-conservative that do not destroy the desired binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position. In some embodiments, the one or more substitutions to one or more of the antibody sequences can be as follows for each noted section in the noted antibody: 1) VH1|1-08/D6|6-19|RF1/JH4, 25A4 H CDR2 sequence—WMYPN - - - SGNTGYAQKFQG, where N at 11 can be S or Q and T at 12 can be A or V, such that the sequence can be Trp Met Tyr Pro Asn Ser Gly X1 X2 Gly Tyr Ala Gln Lys Phe Gln Gly (SEQ ID NO: 50259) wherein X1=N or S or Q or a conservative substitution thereof, X2=T or A or V or a conservative substitution thereof. 2) VH1|1-08/D6|6-19|RF1/JH4, 4A2 H CDR2 sequence—WMHPN - - - SGNTGYAQKFQG, where N at 11 can be S or Q, and T at 12 can be A or E, such that the sequence can be Trp Met His Pro Asn Ser Gly X1 X2 Gly Tyr Ala Gln Lys Phe Gln Gly (SEQ ID NO: 50260) wherein X1=N or S or Q or a conservative substitution thereof, X2=T or A or E or a conservative substitution thereof. 3) VK4|B3/JK3, 4A2 L CDR3 sequence—QQYYN - - - TPVT, where N at 5 can be Q, and T at 29 can be A, such that the sequence can be Gln Gln Tyr Tyr X1 X2 Pro Val Thr (SEQ ID NO: 50261) wherein X1=N or Q or a conservative substitution thereof, X2=T or A or a conservative substitution thereof. 4) VH1|1-02/D1|1-1|RF1/JH4, 4H6 H CDR3 sequence—DGTS - - - SFDY, where D at 1 can be S, G at 2 can be A, such that the sequence can be X1 X2 Thr Ser Ser Phe Asp Tyr (SEQ ID NO: 50262) wherein X1=D or S or a conservative substitution thereof, X2=or A or a conservative substitution thereof. 5) VH3|3-33/D4|4-11|RF2/JH6 and VH3|3-07/D4|4-11|RF2/JH6, 7E11 H CDR2 sequence—IIWHD - - - GSNKYYADSVKG, where D at 5 can be S or E, G at 9 can be A, D at 16 can be E, and S at 17 can be A, such that the sequence can be Ile Ile Trp His X1 X2 Ser Asn Lys Tyr Tyr Ala X3 X4 Val Lys Gly (SEQ ID NO: 50263) wherein X1=D or S or E or a conservative substitution thereof, X2=G or A or a conservative substitution thereof, X3=D or E or a conservative substitution thereof, X4=S or A or a conservative substitution thereof. 6) VH3|3-33/D6|6-

6|RF1/JH6 and VH3|3-07/D6|6-6|RF1/JH6, 5E5 H CDR2 sequence VIWYD - - - GSNKYYADSVKG, where G at 9 can be A, D at 16 can be E or G, and S at 17 can be A, such that the sequence can be Val Ile Trp Tyr Asp X1 Ser Asn Lys Tyr Tyr Ala X2 X3 Val Lys Gly (SEQ ID NO: 50264) wherein X1=G or A or a conservative substitution thereof X2=D or E or G or a conservative substitution thereof X3=S or A or a conservative substitution thereof. 7) VH3|3-33/D6|6-6|RF1/JH6 and VH3|3-07/D6|6-6|RF1/JH6, 5E5 H CDR3 sequence EVYSSGW - - - YDYGMDV, where W at 7 can be F, such that the sequence can be Glu Val Tyr Ser Ser Gly X1 Tyr Asp Tyr Gly Met Asp Val (SEQ ID NO: 50265) wherein X1=W or F or a conservative substitution thereof.

In some embodiments, any one or more of the above CDR sequences can be combined with any one or more of the CDR sequences provided herein (e.g., Table 2 in FIG. 49, and Tables 19A-C and Tables 20A-C in FIG. 55). In some embodiments, any one or more of the above CDR sequences can be combined with any one or more CDR sequences provided herein for the designated antibody to provide an antibody of 6 CDRs (LCDR1, LCDR2, LCDR3, HCDR1, HCDR2, and HCDR3). For example, any one or more of the above CDRs can be used as one of the CDRs for the antibodies provided in Table 2 in FIG. 49 and/or Tables 19A, 19B, 19C, 20A, 20B and/or 20C in FIG. 55. In some embodiments, the variant positions provided in the above consensus sequences can be further combined as optional variations with the variations of sequence provided in Table 2 in FIG. 49, and Tables 19A-C and Tables 20A-C in FIG. 55, such that any demonstrated combination of sequences in one consensus sequence (e.g., for an antibody, such as 4A2 H CDR2 above) can be combined with all permissible options outlined for the relevant antibody in Table 2 in FIG. 49, and Tables 19A-C and Tables 20A-C in FIG. 55 (e.g., the corresponding 4A2 H CDR2), which can further be combined with any of the other 4A2 sequences in Table 2 in FIG. 49, and Tables 19A-C and Tables 20A-C in FIG. 55 (e.g., HCDR1, HCDR3, LCDR1, LCDR2, and LCDR3). Of course, 4A2 L CDR3 noted above can similarly be combined, and/or combined with the immediate combination as well. Thus, such sequences are not disclosed herein as needing to be alternative sequences, but are contemplated as additional options for the noted sequences. In some embodiments, variants of such sequences are also contemplated. Such variants can retain or have superior desired activity. Examples of such aspects are provided in Example 14 and tables 6 and 7. In some embodiments, any one or more of the FR regions in tables 6 and 7 can be combined with any one or more of the CDR sequences provided herein. In some embodiments, any one or more of the FR regions provided in Table 6 or 7 can be combined with the corresponding CDR set for the corresponding antibody (as a set of 6 CDRs). Thus, variants of antibody 4A2 are provided that include 6 CDRs (HCDR1, HCDR2, HCDR3, LCDR1, LCDR2, and LCDR3) and 8 FRs HFR1, HFR2, HFR3, HFR4, LFR1, LFR2, LFR3, and LFR4), any particular sequence of which can be from any of the designated sequences for antibody 4A2 provided herein (the present paragraph, Tables 2, 6 and/or 7, tables 19A, 19B, and 19C, 20A, 20B and 20C, etc).

Non-conservative substitutions may involve the exchange of a member of one class of amino acids or amino acid mimetics for a member from another class with different physical properties (e.g. size, polarity, hydrophobicity, charge). In certain embodiments, such substituted residues may be introduced into regions of a human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the antigen binding protein as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides as has been describe above. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

In some embodiments, one skilled in the art may identify residues that may be changed that result in enhanced properties as desired. For example, an amino acid substitution (conservative or non-conservative) may result in enhanced binding affinity to human ASGR, human ASGR-1, and/or human ASGR-2, or enhanced binding affinity to other species of ASGR, ASGR-1, and/or ASGR-2.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's or protein's structure. See Holm et al., Nucl. Acid. Res., 27(1):244-247 (1999). Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of the antigen binding protein include glycosylation variants wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to the target of interest, or to increase or decrease the affinity of the antibodies to the target of interest described herein.

According to certain embodiments, desired amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

Antigen Binding Protein Sequences

The amino acid sequences of the light chain CDRs of exemplary antigen binding proteins (antibodies) and the heavy chain CDRs of exemplary antigen binding proteins (antibodies) are shown in Tables 2-7, in addition to the exemplary antigen binding proteins described above as consensus light chain CDRs and/or consensus heavy chain CDRs (see Tables 19 B and C and Tables 20 B and C in FIG. 55). Also shown are polynucleotide sequences which encode the amino acid sequences of the CDRs (Table 2). Tables 3-7 and Tables A, B and C further provide the amino acid sequences of the VH and VL of exemplary antigen binding proteins (e.g., antibodies), in addition to the exemplary antigen binding proteins described above as consensus variable light chain sequences and/or consensus variable heavy chain sequences (see Table 19A and Table 20A in FIG. 55, as well as the Tables in FIGS. 56 and 57). Table 3 further provides the polynucleotide (DNA) sequences encoding the amino acid sequences of the variable light and variable heavy domains for exemplary antibodies.

Particular embodiments of antigen binding proteins of the present invention comprise one or more amino acid sequences that are identical to the amino acid sequences of one or more of the CDRs and/or FRs (framework regions) illustrated herein in Tables 2-7, and Tables A-C below. In one embodiment, the antigen binding protein comprises a light chain CDR1 sequence illustrated herein in Table 2 in FIG. 49 and Table C below. In another embodiment, the antigen binding protein comprises a light chain CDR2 sequence illustrated herein in Table 2 in FIG. 49 and Table C below. In another embodiment, the antigen binding protein comprises a light chain CDR3 sequence illustrated in herein in Table 2 in FIG. 49 and Table C below. In another embodiment, the antigen binding protein comprises a heavy chain CDR1 sequence illustrated in herein in Table 2 in FIG. 49 and Table C below. In another embodiment, the antigen binding protein comprises a heavy chain CDR2 sequence illustrated herein in Table 2 in FIG. 49 and Table C below. In another embodiment, the antigen binding protein comprises a heavy chain CDR3 sequence illustrated herein in Table 2 in FIG. 49 and Table C below. In another embodiment, the antigen binding protein comprises a light chain FR1 sequence illustrated herein in Tables 3-7 in FIGS. 50-54, respectively. In another embodiment, the antigen binding protein comprises a light chain FR2 sequence illustrated herein in Tables 3-7 in FIGS. 50-54, respectively. In another embodiment, the antigen binding protein comprises a light chain FR3 sequence illustrated herein in Tables 3-7 in FIGS. 50-54, respectively. In another embodiment, the antigen binding protein comprises a light chain FR4 sequence illustrated herein in Table 3-7 in FIGS. 50-54, respectively. In another embodiment, the antigen binding protein comprises a heavy chain FR1 sequence illustrated herein in Table 3-7 in FIGS. 50-54, respectively. In another embodiment, the antigen binding protein comprises a heavy chain FR2 sequence illustrated herein in Table 3-7 in FIGS. 50-54, respectively. In another embodiment, the antigen binding protein comprises a heavy chain FR3 sequence illustrated herein in Table 3-7 in FIGS. 50-54, respectively. In another embodiment, the antigen binding protein comprises a heavy chain FR4 sequence illustrated herein in Table 3-7 in FIGS. 50-54, respectively.

In another embodiment, at least one of the antigen binding protein's CDR3 sequences differs by no more than 6, 5, 4, 3, 2, 1 or 0 single amino acid addition, substitution, and/or deletion from a CDR3 sequence from the sequences as shown in Table 2 in FIG. 49 or Table C below. In another embodiment, the antigen binding protein's light chain CDR3 sequence differs by no more than 6, 5, 4, 3, 2, 1 or 0 single amino acid addition, substitution, and/or deletion from a light chain CDR3 sequence from the sequences as shown in Table 2 in FIG. 49 or Table C below and the antigen binding protein's heavy chain CDR3 sequence differs by no more than 6, 5, 4, 3, 2, 1 or 0 single amino acid addition, substitution, and/or deletion from a heavy chain CDR3 sequence from the sequences as shown in Table 2 in FIG. 49 or Table C below. In another embodiment, the antigen binding protein further comprises 1, 2, 3, 4, or 5 CDR sequences that each independently differs by 6, 5, 4, 3, 2, 1, or 0 single amino acid additions, substitutions, and/or deletions from a CDR sequence of the sequences shown in Table 2 in FIG. 49 or Table C below. In another embodiment, the antigen binding protein comprises the CDRs of the light chain variable region and the CDRs of the heavy chain variable region set forth in Table 2 in FIG. 49 or Table C below. In a further embodiment, the antigen binding protein comprises the CDRs of any one of the antibodies in Table 2 in FIG. 49 or Table C below. In one embodiment, the antigen binding protein is a human antibody. In another embodiment, the antigen binding protein is a humanized antibody. In certain embodiments, the VH CDRs and the VL CDRs are paired in a manner indicated in Tables 2-7 in FIGS. 49-54, respectively.

In one embodiment, the antigen binding protein (e.g., an antibody) comprises a light chain variable domain comprising a sequence of amino acids that differs from the sequence of a light chain variable domain listed in Table 3-7 in FIGS. 50-54, respectively at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the antigen binding protein (e.g., an antibody) comprises a heavy chain variable domain comprising a sequence of amino acids that differs from the sequence of a heavy chain variable domain listed in Table 3-7 in FIGS. 50-54, respectively at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In certain embodiments, the antigen binding protein comprises a light chain variable domain and a heavy chain variable domain that are paired in a manner indicated in Tables 3-7 in FIGS. 50-54, respectively. In certain embodiments, the antigen binding protein comprises a light chain variable domain and a heavy chain variable domain that are paired in a manner indicated in Tables A-C below.

In a particular embodiment, the antigen binding protein (e.g., antibody) binds to human ASGR-1 and comprises a heavy chain variable domain containing one or more VH CDR1 (HCDR1), VH CDR2 (HCDR2) and/or VH CDR3 (HCDR3), wherein the VH CDR1 (HCDR1) has an amino acid sequence identical to, or comprising not more than 3 amino acid additions/insertions, deletions or substitutions as compared to, the amino acid sequences selected from the group consisting of SEQ ID NO:5136, SEQ ID NO:50001, SEQ ID NO:50012 and SEQ ID NO:50468; the VH CDR2 (HCDR2) has an amino acid sequence identical to, or comprising not more than 3 amino acid additions/insertions, deletions or substitutions as compared to, the amino acid sequences selected from the group consisting of SEQ ID NO:13148, SEQ ID NO:50002, SEQ ID NO:50014, and SEQ ID NO:50260; and the VH CDR3 (HCDR3) has an amino acid sequence identical to, or comprising not more than 3 amino acid additions/insertions, deletions or substitutions as compared to, the amino acid sequences selected from the group consisting of SEQ ID NO:21160, SEQ ID NO:50003, and SEQ ID NO:50470.

In a particular embodiment, the antigen binding protein (e.g., antibody) binds to human ASGR-1 and comprises a light chain variable domain containing one or more VL CDR1 (LCDR1), VL CDR2 (LCDR2) and/or VL CDR3 (LCDR3), wherein the VL CDR1 (LCDR1) has an amino acid sequence identical to, or comprising not more than 3 amino acid additions/insertions, deletions or substitutions as compared to, the amino acid sequences selected from the group consisting of SEQ ID NO:1130, SEQ ID NO:50133, SEQ ID NO:50156 and SEQ ID NO:50162; the VL CDR2 (LCDR2) has an amino acid sequence identical to, or comprising not more than 3 amino acid additions/insertions, deletions or substitutions as compared to, the amino acid sequences selected from the group consisting of SEQ ID NO:9142, SEQ ID NO:50157, SEQ ID NO:50163, SEQ ID NO:50229, SEQ ID NO:50619, SEQ ID NO:50643 and SEQ ID NO:50649; and the VL CDR3 (LCDR3) has an amino acid sequence identical to, or comprising not more than 3 amino acid additions/insertions, deletions or substitutions as compared to, the amino acid sequences selected from the group consisting of SEQ ID NO:17154, SEQ ID NO:50134, SEQ ID NO:50164, and SEQ ID NO:50261.

In a particular embodiment, the antigen binding protein (e.g., antibody) binds to human ASGR-1 and comprises A) a heavy chain variable domain containing one or more VH CDR1 (HCDR1), VH CDR2 (HCDR2) and/or VH CDR3 (HCDR3), wherein the VH CDR1 (HCDR1) has an amino acid sequence identical to, or comprising not more than 3 amino acid additions/insertions, deletions or substitutions as compared to, the amino acid sequences selected from the group consisting of SEQ ID NO:5136, SEQ ID NO:50001, SEQ ID NO:50012 and SEQ ID NO:50468; the VH CDR2 (HCDR2) has an amino acid sequence identical to, or comprising not more than 3 amino acid additions/insertions, deletions or substitutions as compared to, the amino acid sequences selected from the group consisting of SEQ ID NO:13148, SEQ ID NO:50002, SEQ ID NO:50014, and SEQ ID NO:50260; and the VH CDR3 (HCDR3) has an amino acid sequence identical to, or comprising not more than 3 amino acid additions/insertions, deletions or substitutions as compared to, the amino acid sequences selected from the group consisting of SEQ ID NO:21160, SEQ ID NO:50003, and SEQ ID NO:50470; and B) a light chain variable domain containing one or more VL CDR1 (LCDR1), VL CDR2 (LCDR2) and/or VL CDR3 (LCDR3), wherein the VL CDR1 (LCDR1) has an amino acid sequence identical to, or comprising not more than 3 amino acid additions/insertions, deletions or substitutions as compared to, the amino acid sequences selected from the group consisting of SEQ ID NO:1130, SEQ ID NO:50133, SEQ ID NO:50156 and SEQ ID NO:50162; the VL CDR2 (LCDR2) has an amino acid sequence identical to, or comprising not more than 3 amino acid additions/insertions, deletions or substitutions as compared to, the amino acid sequences selected from the group consisting of SEQ ID NO:9142, SEQ ID NO:50157, SEQ ID NO:50163, SEQ ID NO:50229, SEQ ID NO:50619, SEQ ID NO:50643 and SEQ ID NO:50649; and the VL CDR3 (LCDR3) has an amino acid sequence identical to, or comprising not more than 3 amino acid additions/insertions, deletions or substitutions as compared to, the amino acid sequences selected from the group consisting of SEQ ID NO:17154, SEQ ID NO:50134, SEQ ID NO:50164, and SEQ ID NO:50261. In one embodiment, the antigen binding protein (e.g., antibody) comprises A) a heavy chain variable domain containing a VH CDR1 (HCDR1), a VH CDR2 (HCDR2) and a VH CDR3 (HCDR3), wherein the VH CDR1 (HCDR1) has an amino acid sequence identical to, or comprising not more than 3 amino acid additions/insertions, deletions or substitutions as compared to, the amino acid sequences selected from the group consisting of SEQ ID NO:5136, SEQ ID NO:50001, SEQ ID NO:50012 and SEQ ID NO:50468; the VH CDR2 (HCDR2) has an amino acid sequence identical to, or comprising not more than 3 amino acid additions/insertions, deletions or substitutions as compared to, the amino acid sequences selected from the group consisting of SEQ ID NO:13148, SEQ ID NO:50002, SEQ ID NO:50014, and SEQ ID NO:50260; and the VH CDR3 (HCDR3) has an amino acid sequence identical to, or comprising not more than 3 amino acid additions/insertions, deletions or substitutions as compared to, the amino acid sequences selected from the group consisting of SEQ ID NO:21160, SEQ ID NO:50003, and SEQ ID NO:50470; and B) a light chain variable domain containing a VL CDR1 (LCDR1), a VL CDR2 (LCDR2) and a VL CDR3 (LCDR3), wherein the VL CDR1 (LCDR1) has an amino acid sequence identical to, or comprising not more than 3 amino acid additions/insertions, deletions or substitutions as compared to, the amino acid sequences selected from the group consisting of SEQ ID NO:1130, SEQ ID NO:50133, SEQ ID NO:50156 and SEQ ID NO:50162; the VL CDR2 (LCDR2) has an amino acid sequence identical to, or comprising not more than 3 amino acid additions/insertions, deletions or substitutions as compared to, the amino acid sequences selected from the group consisting of SEQ ID NO:9142, SEQ ID NO:50157, SEQ ID NO:50163, SEQ ID NO:50229, SEQ ID NO:50619, SEQ ID NO:50643 and SEQ ID NO:50649; and the VL CDR3 (LCDR3) has an amino acid sequence identical to, or comprising not more than 3 amino acid additions/insertions, deletions or substitutions as compared to, the amino acid sequences selected from the group consisting of SEQ ID NO:17154, SEQ ID NO:50134, SEQ ID NO:50164, and SEQ ID NO:50261. In one embodiment, the antigen binding protein comprises A) a heavy chain variable domain containing a VH CDR1 (HCDR1), a VH CDR2 (HCDR2) and a VH CDR3 (HCDR3), wherein the VH CDR1 (HCDR1) amino acid sequence is selected from the group consisting of SEQ ID NO:5136, SEQ ID NO:50001, SEQ ID NO:50012 and SEQ ID NO:50468; the VH CDR2 (HCDR2) amino acid sequence is selected from the group consisting of SEQ ID NO:13148, SEQ ID NO:50002, SEQ ID NO:50014, and SEQ ID NO:50260; and the VH CDR3 (HCDR3) amino acid sequence is selected from the group consisting of SEQ ID NO:21160, SEQ ID NO:50003, and SEQ ID NO:50470; and B) a light chain variable domain containing a VL CDR1 (LCDR1), a VL CDR2 (LCDR2) and a VL CDR3 (LCDR3), wherein the VL CDR1 (LCDR1) amino acid sequence is selected from the group consisting of SEQ ID NO:1130, SEQ ID NO:50133, SEQ ID NO:50156 and SEQ ID NO:50162; the VL CDR2 (LCDR2) amino acid sequence is selected from the group consisting of SEQ ID NO:9142, SEQ ID NO:50157, SEQ ID NO:50163, SEQ ID NO:50229, SEQ ID NO:50619, SEQ ID NO:50643 and SEQ ID NO:50649; and the VL CDR3 (LCDR3) amino acid sequence is selected from the group consisting of SEQ ID NO:17154, SEQ ID NO:50134, SEQ ID NO:50164, and SEQ ID NO:50261. In one embodiment, the antigen binding protein comprises a heavy chain variable domain and a light chain variable domain containing a VH CDR1 having the amino acid sequence set forth in SEQ ID NO:5136; a VH CDR2 having the amino acid sequence set forth in SEQ ID NO:13148; a VH CDR3 having the amino acid sequence set forth in SEQ ID NO:21160; a VL CDR1 having the amino acid sequence set forth in SEQ ID NO:1130; a VL CDR2 having the amino acid sequence set forth in SEQ ID NO:9142; and a VL CDR3 having the amino acid sequence set forth in SEQ ID NO:17154.

In a particular embodiment, the antigen binding protein (e.g., antibody) comprises a) a light chain variable domain having no more than ten or no more than five amino acid additions/insertions, deletions or substitutions from the amino acid sequence set forth in SEQ ID NO:25164 or SEQ ID NO:50326; b) a heavy chain variable domain having no more than ten or no more than five amino acid additions/insertions, deletions or substitutions from the amino acid sequence set forth in SEQ ID NO:29170 or SEQ ID NO:50266; or c) the light chain variable domain of a) and the heavy chain variable domain of b). In one embodiment, the antigen binding protein comprises a light chain variable domain having the amino acid sequence set forth in SEQ ID NO:25164 or SEQ ID NO:50326; and a heavy chain variable domain having the amino acid sequence set forth in SEQ ID NO:29170 or SEQ ID NO:50266. In one embodiment, the antigen binding protein comprises a light chain variable domain having the amino acid sequence set forth in SEQ ID NO:50326; and a heavy chain variable domain having the amino acid sequence set forth in SEQ ID NO:50266. In one embodiment, the antigen binding protein comprises a light chain variable domain having the amino acid sequence set forth in SEQ ID NO:25164; and a heavy chain variable domain having the amino acid sequence set forth in SEQ ID NO:29170.

While specific embodiments relating to the antigen binding protein identified as 4A2 are set forth above with particularity, the embodiments of the present invention are not intended to be limited in scope to this individual embodiment. The embodiments directed to 4A2 are intended merely as single illustrations of individual embodiments. It is fully anticipated that the embodiments of the present invention include antigen binding proteins comprising heavy chain variable domains containing one or more VH CDR1 (HCDR1), VH CDR2 (HCDR2) and/or VH CDR3 (HCDR3) and/or light chain variable domains containing one or more VL CDR1 (LCDR1), VL CDR2 (LCDR2) and/or VL CDR3 (LCDR3) as set forth in Tables 2-7 in FIGS. 49-57, respectively, as well as Tables 19A-C and Tables 20A-C in FIG. 55, Tables 21-134 in FIGS. 56 and 57, and Tables A, B and C.

TABLE A

Exemplary Heavy and Light Chain Variable Regions

| Ab name | SEQ ID NOs: VH/VL | Ab name | SEQ ID NOs: VH/VL | Ab name | SEQ ID NOs: VH/VL | Ab name | SEQ ID NOs: VH/VL |
|---|---|---|---|---|---|---|---|
| 10G6 | 29184/25178 | 59F2 | 31512/27506 | 147E9 | 30172/26166 | 191G10 | 30846/26840 |
| 11E2 | 29040/25034 | 5E5 | 29016/25010 | 184E7 | 30660/26654 | 191G12 | 30730/26724 |
| 11F5 | 29054/25048 | 60D2 | 31518/27512 | 194A4 | 30820/26814 | 192C10 | 30764/26758 |

TABLE A-continued

Exemplary Heavy and Light Chain Variable Regions

| | | | | | | | |
|---|---|---|---|---|---|---|---|
| 12E9 | 29186/25180 | 60E8 | 29494/25488 | 208A2 | 28136/24130 | 192C8 | 30756/26750 |
| 12F11 | 29178/25172 | 63A10 | 31536/27530 | 210G10 | 31054/27048 | 192E4 | 30744/26738 |
| 12F12 | 29188/25182 | 63G7 | 31534/27528 | 4B1 | 28878/24872 | 192G6 | 30752/26746 |
| 13F6 | 28772/24766 | 64B12 | 29624/25618 | 60E12 | 29502/25496 | 192G8 | 30760/26754 |
| 148E10 | 28132/24126 | 65F10 | 28134/24128 | 61A1 | 29504/25498 | 192H10 | 30768/26762 |
| 154F4 | 31392/27386 | 68G6 | 28224/24218 | 62H10 | 31332/27326 | 193C7 | 30794/26788 |
| 159H8 | 31416/27410 | 6A6 | 28806/24800 | 63H8 | 29604/25598 | 194B7 | 30828/26822 |
| 160B12 | 31418/27412 | 6D4 | 28816/24810 | 72G9 | 32080/28074 | 194C1 | 30816/26810 |
| 175D10 | 30538/26532 | 6D9 | 29154/25148 | 8D8 | 29168/25162 | 196C7 | 30870/26864 |
| 177D2 | 31858/27852 | 6G6 | 29198/25192 | 12D2 | 29036/25030 | 197B6 | 30894/26888 |
| 25A4 | 28522/24516 | 70D1 | 29670/25664 | 148H10 | 30196/26190 | 197E11 | 30906/26900 |
| 25D12 | 28510/24504 | 7A10 | 29194/25188 | 173C11 | 30520/26514 | 197F2 | 30886/26880 |
| 26C4 | 28580/24574 | 7E11 | 28914/24908 | 179C2 | 30570/26564 | 197G3 | 30888/26882 |
| 27E7 | 28744/24738 | 7F4 | 28814/24808 | 47C1 | 29286/25280 | 198G3 | 30620/26614 |
| 28H2 | 29190/25184 | 7F8 | 28948/24942 | 49C1 | 29320/25314 | 213B3 | 31092/27086 |
| 29E2 | 29192/25186 | 7G4 | 28966/24960 | 60C12 | 29500/25494 | 219H1 | 31156/27150 |
| 29E6 | 28550/24544 | 8D12 | 29050/25044 | 60G2 | 29482/25476 | 74C8 | 29768/25762 |
| 29H8 | 28798/24792 | 9F12LC1 | 28216/24210 | 65D5 | 29632/25626 | 74G6 | 29894/25888 |
| 32D6 | 29196/25190 | 9F12LC2 | 28217/24211 | 66H11 | 28130/24124 | 75G3 | 29714/25708 |
| 3G7 | 28840/24834 | 9G9 | 28790/24784 | 71A6 | 28128/24122 | 89A11 | 30028/26022 |
| 45B4 | 29252/25246 | 65E9 | 31538/27532 | 73G1 | 31556/27550 | 74B2 | 29736/25730 |
| 49F10 | 29334/25328 | 72B4 | 31552/27546 | 49C5 | 32086/28080 | 74H7 | 29966/25960 |
| 4A2 | 29170/25164 | 7H7 | 28944/24938 | 49D10 | 32088/28082 | 85F7 | 29766/25760 |
| 4B3 | 28750/24744 | 9C11 | 28856/24850 | 51E3 | 30958/26952 | 198B9 | 30918/26912 |
| 4H6 | 28936/24930 | 12B12 | 28978/24972 | 51F4 | 31476/27470 | 199A7 | 30932/26926 |
| 50D4 | 29362/25356 | 147D10 | 30174/26168 | 53E8 | 32090/28084 | 218G4 | 31786/27780 |
| 50G9 | 32088/28076 | 149D11 | 30226/26220 | 54E9 | 31488/27482 | 146A8 | 31332/27326 |
| 51E9 | 29366/25360 | 149F8 | 30222/26216 | 56E3 | 31492/27486 | 146B6 | 31334/27328 |
| 52G11 | 28138/24132 | 151B9 | 31372/27366 | 56G1 | 31490/27484 | 149A1 | 31344/27338 |
| 52H1 | 31482/27476 | 175F4 | 31456/27450 | 190C11 | 30602/26596 | 172B12 | 31452/27446 |
| 53F2 | 28140/24134 | 22G5 | 28368/24362 | 190E6 | 30642/26636 | 172C3 | 31450/27444 |
| 53F7 | 29412/25406 | 48B12 | 31820/27814 | 190F12 | 30618/26612 | 193E7 | 30796/26790 |
| 55B1 | 29430/25424 | 52H2 | 29380/25374 | 190F8 | 30712/26706 | 199E3 | 30926/26920 |
| 56E5 | 29466/25460 | 6G7 | 28880/24874 | 190G11 | 30608/26602 | 226F9 | 31264/27258 |
| 65C12 | 32078/28072 | 7G2 | 28942/24936 | 190H9 | 30716/26710 | 227C1 | 31280/27274 |

| Ab name | SEQ ID NOs: VH/VL | Ab name | SEQ ID NOs: VH/VL | Ab name | SEQ ID NOs: VH/VL |
|---|---|---|---|---|---|
| 176H4 | 30542/26536 | 72F5 | 29700/25694 | 48D7 | 29306/25300 |
| 194C10 | 30832/26826 | 191A10 | 30724/26718 | 52D10 | 29388/25382 |
| 191E10 | 30726/26720 | 191G1 | 30628/26622 | 59E6 | 29590/25584 |
| 196F4 | 30868/26862 | 227F2 | 31282/27276 | 64E2 | 31836/27830 |
| 198D2 | 31604/27598 | 31D12LC1 | 29176/25170 | 57A7 | 29554/25548 |
| 202A3 | 30972/26966 | 31D12LC2 | 29174/25168 | 58G11 | 31510/27504 |
| 204G6 | 31004/26998 | 7C3LC1 | 28212/24206 | 64G12 | 29626/25620 |
| 224G1 | 31196/27190 | 7C3LC2 | 28214/24208 | | |

TABLE B

| Ab name | SEQ ID NOs: VH/VL | Ab name | SEQ ID NOs: VH/VL | Ab name | SEQ ID NOs: VH/VL | Ab name | SEQ ID NOs: VH/VL |
|---|---|---|---|---|---|---|---|
| 175D10 | 30538/26532 | 184E7 | 30660/26654 | 192E4 | 30744/26738 | 74B2 | 29736/25730 |
| 25A4 | 28522/24516 | 194A4 | 30820/26814 | 192G6 | 30752/26746 | 74H7 | 29966/25960 |
| 26C4 | 28580/24574 | 208A2 | 28136/24130 | 192G8 | 30760/26754 | 85F7 | 29766/25760 |
| 29H8 | 28798/24792 | 210G10 | 31054/27048 | 192H10 | 30768/26762 | 218G4 | 31786/27780 |
| 49F10 | 29334/25328 | 4B1 | 28878/24872 | 193C7 | 30794/26788 | 172B12 | 31452/27446 |
| 4A2 | 29170/25164 | 72G9 | 32080/28074 | 194B7 | 30828/26822 | 172C3 | 31450/27444 |
| 4H6 | 28936/24930 | 190C11 | 30602/26596 | 194C1 | 30816/26810 | 193E7 | 30796/26790 |
| 50D4 | 29362/25356 | 190E6 | 30642/26636 | 196C7 | 30870/26864 | 199E3 | 30926/26920 |
| 51E9 | 29366/25360 | 190F12 | 30618/26612 | 197B6 | 30894/26888 | 191E10 | 30726/26720 |
| 52H1 | 31482/27476 | 190F8 | 30712/26706 | 197E11 | 30906/26900 | 196F4 | 30868/26862 |
| 55B1 | 29430/25424 | 190G11 | 30608/26602 | 197F2 | 30886/26880 | 198D2 | 31604/27598 |
| 56E5 | 29466/25460 | 190H9 | 30716/26710 | 197G3 | 30888/26882 | 202A3 | 30972/26966 |
| 64B12 | 29624/25618 | 191A10 | 30724/26718 | 198G3 | 30620/26614 | 204G6 | 31004/26998 |
| 6G6 | 29198/25192 | 191G1 | 30628/26622 | 213B3 | 31092/27086 | 10G6 | 29184/25178 |
| 7F4 | 28814/24808 | 191G10 | 30846/26840 | 219H1 | 31156/27150 | 160B12 | 31418/27412 |
| 7G4 | 28966/24960 | 191G12 | 30730/26724 | 74C8 | 29768/25762 | 177D2 | 31858/27852 |
| 149F8 | 30222/26216 | 192C10 | 30764/26758 | 74G6 | 29894/25888 | 53F7 | 29412/25406 |
| 48B12 | 31820/27814 | 192C8 | 30756/26750 | 75G3 | 29714/25708 | 63A10 | 31536/24530 |
| 7E11 | 28914/24908 | 198B9 | 30918/26912 | 146B6 | 31334/27328 | 22G5 | 28368/24362 |
| 6G7 | 28880/24874 | 199A7 | 30932/26926 | 176H4 | 30542/26536 | 5E5 | 29016/25010 |

TABLE B-continued

| Ab name | SEQ ID NOs: VH/VL | Ab name | SEQ ID NOs: VH/VL | Ab name | SEQ ID NOs: VH/VL | Ab name | SEQ ID NOs: VH/VL |
|---|---|---|---|---|---|---|---|
| 147E9 | 30172/26166 | 146A8 | 31332/27326 | 149A1 | 31344/27338 | 194C10 | 30832/26826 |
| 54E9 | 31488/27482 | 12D2 | 29036/25030 | | | | |

TABLE C

Exemplary Heavy and Light Chain Variable Regions and Heavy and Light Chain CDR1/2/3

| Ab name | VH SEQ ID NOs: | VL SEQ ID NOs: | HCDR1 SEQ ID NOs: | HCDR2 SEQ ID NOs: | HCDR3 SEQ ID NOs: | LCDR1 SEQ ID NOs: | LCDR2 SEQ ID NOs: | LCDR3 SEQ ID NOs: |
|---|---|---|---|---|---|---|---|---|
| 25A4 | 28522 or 50266 | 24516 or 50316 | 4488, 50468, 50001 or 50013 | 12500, 50002, 50014 or 50259 | 20512, 50003 or 50470 | 480, 50133 or 50162 | 8492, 50157, 50229, 50619, 50643 or 50649 | 16504, 50134, 50164 or 50620 |
| 26C4 | 28580 or 50266 | 24574 or 50316 | 4546, 50001, 50013 or 50468 | 12588 or 50002 | 20570, 50003 or 50470 | 538, 50133 or 50156 | 8550, 50157, 50163, 50229, 50619, 50643 or 50649 | 16562, 50134, 50164 or 50620 |
| 29H8 | 28798 or 50266 | 24792 or 50316 | 4764, 50001, 50013 or 50468 | 12776 or 50002 | 20788 or 50003 or 50470 | 756 or 50133 | 8768, 50157, 50163 50229, 50619, 50643 or 50649 | 16780 or 50134 |
| 4A2 | 29170 or 50266 | 25164 or 50326 | 5136, 50001, 50013, or 50468 | 13148, 50002, 50014 or 50260 | 21160, 50003 or 50470 | 1130, 50133, 50156 or 50162 | 9142, 50157, 50163 50229, 50619, 50643 or 50649 | 17154, 50134, 50164 or 50261 |
| 4H6 | 28936 or 50272 | 24930 or 50321 | 4902 or 50019 | 12914 or 50020 | 20926 or 50021 or 50262 | 894, 50147 or 50159 | 8096, 50148 or 50160 | 16918 or 50149 |
| 56E5 | 29466 or 50272 | 25460 or 50321 | 5432, 50019 or 50058 | 13444 or 50020 | 21456 or 50021 | 1426 or 50147 | 9438, 50123, 50131, 50136, 50139, 50142, 50145, 50148, 50154, 50160, 50181, 50184, 50199, 50202, 50213 or 50248 | 17450 or 50149 |
| 7F4 | 28814 or 50284 | 24808 or 50312 | 4780, 50046 or 50075 | 12792 or 50047 | 20804 or 50048 | 772, 50122, 50130, 50135 or 50198 | 8784, 50123, 50131, 50136, 50139, 50142, 50145, 50148, 50154, 50160, 50181, 50199 or 50213 | 16796 or 50124 |
| 7G4 | 28966 or 50267 | 24960 or 50315 | 4932, 50004, 50037 or 50107 | 12944, 50005, 50008, 50017, | 20956 or 50006 | 924, 50122, 50130, 50135, | 8936, 50123, 50131, 50136, | 16948 |

TABLE C-continued

Exemplary Heavy and Light Chain Variable Regions and Heavy and Light Chain CDR1/2/3

| Ab name | VH SEQ ID NOs: | VL SEQ ID NOs: | HCDR1 SEQ ID NOs: | HCDR2 SEQ ID NOs: | HCDR3 SEQ ID NOs: | LCDR1 SEQ ID NOs: | LCDR2 SEQ ID NOs: | LCDR3 SEQ ID NOs: |
|---|---|---|---|---|---|---|---|---|
| | | | | 50023, 50026, 50038, 50053, 50067, 50073, 50085, 50088, 50100, 50108, 50238 or 50254 | | 50198, or 50247 | 50139, 50142, 50145, 50148, 50154, 50160, 50181, 50184, 50199, 50202, 50213 or 50248 | |
| 48B12 | 31820 or 50267 | 27814 | 7784, 50034, 50055, 50093, 50113 or 50116 | 15796, 50032, 50035, 50056, 50070, 50091, 50105 or 50117 | 23808 | 3780 | 11792 or 50126 | 19804 |
| 184E7 | 30660 or 50272 | 26654 or 50320 | 6626, 50019 or 50237 | 14638 or 50020 | 22650 | 2620, 50138, 50144, 50147, 50183 or 50212 | 10632, 50123, 50131, 50136, 50139, 50142, 50145, 50148, 50154, 50160, 50181, 50184, 50199, 50202, 50213 or 50248 | 18644 or 50146 |
| 194A4 | 30820 | 26814 or 50342 | 6786 | 14798, 50020, 50050, 50059 or 50079 | 22810 | 2780 or 50206 | 10792, 50128 or 50207 | 18804 or 50208 |
| 4B1 | 28878 | 24872 or 50323 | 4844 | 12856 | 20868 | 836, 50141 or 50153 | 8848, 50123, 50131, 50136, 50139, 50142, 50145, 50148, 50154, 50160, 50181, 50184, 50199, 50202, 50213 or 50248 | 16860, 50143 or 50203 |
| 190F8 | 30712 or 50271 | 26706 or 50318 | 6678, 50007, 50016, 50037, 50066, 50072 50084, 50237 or 50253 | 14690, 50017, 50023, 50038 or 50088 | 22702 or 50018 | 2672, 50138 or 50144 | 10684 or 50139 | 18696, 50140, or 50146 |
| 191G1 | 30628 or 50271 | 26622 or 50318 | 6594, 50004, 50007, 50016, 50022, 50025, 50037, 50066, | 14606, 50008 or 50017 | 22618 or 50018 | 2588, 50138, 50144, 50147, 50183, or 50212 | 10600, 50123, 50131, 50136, 50139, 50142, 50145, 50148, | 18612 or 50140 |

TABLE C-continued

Exemplary Heavy and Light Chain Variable Regions and Heavy and Light Chain CDR1/2/3

| Ab name | VH SEQ ID NOs: | VL SEQ ID NOs: | HCDR1 SEQ ID NOs: | HCDR2 SEQ ID NOs: | HCDR3 SEQ ID NOs: | LCDR1 SEQ ID NOs: | LCDR2 SEQ ID NOs: | LCDR3 SEQ ID NOs: |
|---|---|---|---|---|---|---|---|---|
| | | | 50072, 50084, 50087, 50096, 50099, 50107, 50237 or 50252 | | | | 50154, 50160, 50181, 50184, 50199, 50202, 50213 or 50214 | |
| 191G10 | 30846 or 50271 | 26840 or 50318 | 6812, 50004, 50007, 50016, 50022, 50025, 50037, 50066, 50072, 50084, 50087, 50096, 50099, 50107, 50237 or 50253 | 14824, 50017, 50023, 50038, or 50088 | 22836 or 50018 | 2806, 50138 or 50144 | 10818 or 50139 | 18830 or 50140 |
| 194C1 | 30816 | 26810 | 6782, 50004, 50007, 50016, 50022, 50025, 50037, 50066, 50072, 50084, 50087, 50096, 50099, 50107, 50237 or 50253 | 14794, 50008, or 50017 | 22806 | 2776, 50138, 50144, 50147, 50183 or 50212 | 10788, 50123, 50131, 50136, 50139, 50142, 50145, 50148, 50154, 50160, 50181, 50184, 50199, 50202, 50213 or 50248 | 18800 or 50140 |
| 197G3 | 30888 or 50273 | 26882 or 50320 | 6854, 50016 or 50022 | 14866, 50017, 50023, 50038, or 50088 | 22878 or 50024 | 2848, 50138 or 50144 | 10860, 50123, 50131, 50136, 50139, 50142, 50145, 50148, 50154, 50160, 50181, 50184, 50199, 50202, 50213 or 50248 | 18872 or 50140 |
| 198G3 | 30620 or 50271 | 26614 or 50318 | 6586, 50007, 50016, 50037, 50066, 50072, 50084, 50237 or 50253 | 14598, 50017, or 50038 | 22610 or 50018 | 2580 or 50138 | 10592 or 50139 | 18604 or 50140 |
| 75G3 | 29714 or 50283 | 25708 or 50314 | 5680, 50010 or 50233 | 13692 | 21704 or 50235 | 1674 or 50127 | 9686 or 50128 | 17698 or 50129 |
| 218G4 | 31786 or 50298 | 27780 or 50335 | 7750, 50004, 50025, 50037, 50087, 50096 or | 15762, 50005, 50008, 50017, 50023, 50026, | 23774 | 3746 or 50189 | 11758 or 50190 | 19770 or 50191 |

TABLE C-continued

Exemplary Heavy and Light Chain Variable Regions and Heavy and Light Chain CDR1/2/3

| Ab name | VH SEQ ID NOs: | VL SEQ ID NOs: | HCDR1 SEQ ID NOs: | HCDR2 SEQ ID NOs: | HCDR3 SEQ ID NOs: | LCDR1 SEQ ID NOs: | LCDR2 SEQ ID NOs: | LCDR3 SEQ ID NOs: |
|---|---|---|---|---|---|---|---|---|
| | | | 50253 | 50038, 50053, 50067, 50073, 50085, 50088, 50100, 50108, 50238 or 50254 | | | | |
| 193E7 | 30796 | 26790 or 50312 | 6762 | 14774, 50011, or 50234 | 22786 | 2756, 50122, 50130, 50135, 50198, or 50247 | 10768, 50123 or 50142 | 18780 or 50124 |
| 198D2 | 31604 or 50273 | 27598 or 50335 | 7568, 50004, 50007, 50016, 50022, 50025, 50037, 50066, 50072, 50084, 50087, 50096, 50099, 50107, 50237 or 50253 | 15580 or 50023 | 23592 | 3564 or 50189 | 11576 or 50190 | 19588 or 50191 |
| 202A3 | 30972 | 26966 or 50317 | 6938 | 14950 | 22962 | 2932, 50122, 50130, 50135, 50198, or 50247 | 10944, 50123, 50131, 50136, 50139, 50142, 50148, or 50213 | 18956 or 50137 |
| 7E11 | 28914 or 50273 | 24908 or 50319 | 4880, 50004, 50007, 50022, 50025 or 50037 | 12892 or 50263 or 50023 | 20904 or 50024 | 872 or 50141 or 50153 | 8884, 50123, 50131, 50136, 50139, 50142, 50145, 50148, 50154, 50160, 50181, 50199 or 50213 | 16896, or 50143 |
| 22G5 | 28368 | 24362 or 50323 | 4334, 50031, 50034, 50055, 50093, 50113 or 50116 | 12346 or 50032 | 20358 or 50033 | 326, 50141, 50153, 50180 or 50201 | 8338, 50123, 50131, 50136, 50139, 50142, 50148, 50154 or 50160 | 16350 |
| 5E5 | 29016 or 50267 | 25010 or 50315 | 4982 50004, 50037 or 50107 | 12994, 50005, 50008, 50017, 50023, 50026, 50038, 50053, 50067, 50073, 50085, 50088, | 21006, 50006 or 50265 | 974 50122, 50130, 50135, 50198, or 50247 | 8986, 50123, 50131, 50136, 50139, 50142, 50145, 50148, 50154, 50160, 50181, 50184, | 16998 or 50132 |

TABLE C-continued

Exemplary Heavy and Light Chain Variable Regions and Heavy and Light Chain CDR1/2/3

| Ab name | VH SEQ ID NOs: | VL SEQ ID NOs: | HCDR1 SEQ ID NOs: | HCDR2 SEQ ID NOs: | HCDR3 SEQ ID NOs: | LCDR1 SEQ ID NOs: | LCDR2 SEQ ID NOs: | LCDR3 SEQ ID NOs: |
|---|---|---|---|---|---|---|---|---|
| | | | | 50100, 50108, 50238, 50254 or 50264, | | | 50199, 50202, 50213 or 50248 | |
| 54E9 | 31488 or 50303 | 27482 or 50338 | 7452 or 50102 | 15464 or 50103 | 23476 or 50227 | 3448 or 50195 | 11460 or 50196 | 19472 or 50197 |
| 6G7 | 28880 | 24874 or 50334 | 4846, 50004, 50007, 50016, 50022, 50025, 50037, 50066, 50072, 50084, 50087, 50096, 50099, 50107, 50237 or 50253 | 12858 | 20870 or 50098 | 838 or 50186 | 8850 or 50187 | 16862 or 50188 |
| 176H4 | 30542 or 50282 | 26536 or 50322 | 6508, 50004, 50007, 50016, 50022, 50025, 50037, 50066, 50072, 50084, 50087, 50096, 50099, 50107, 50237 or 50253 | 14520, 50023, 50053, 50085 or 50254 | 22532, or 50255 | 2502, 50150, or 50174 | 10514, 50151, 50175 or 50205 | 18526 or 50152 |
| 194C10 | 30832 | 26826 or 50314 | 6798 or 50233 | 14810, 50011 or 50234 | 22822 | 2792 or 50146 | 10804 or 50128 | 18816 or 50129 |

In the exemplary embodiments described above, the antigen binding proteins maintain desired binding to the various desired species of ASGR, ASGR-1 and/or ASGR-2.

In another embodiment, the light-chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a light chain variable domain listed above.

In another embodiment, the light chain variable domain comprises a sequence of amino acids that is encoded by a nucleotide sequence that is at least 70%, 75%, 80%, 85%, 90%, 91%, 92%, 93%, 94%, 95%, 96%, 97%, 98%, 99% or 100% identical to the polynucleotide sequence listed above. In another embodiment, the light chain variable domain comprises a sequence of amino acids that is encoded by a polynucleotide that hybridizes under moderately stringent conditions to the complement of a polynucleotide that encodes a light chain variable domain selected from the sequences listed above. In another embodiment, the light chain variable domain comprises a sequence of amino acids that is encoded by a polynucleotide that hybridizes under stringent conditions to the complement of a polynucleotide that encodes a light chain variable domain selected from the group consisting of the sequences listed above.

In another embodiment, the heavy chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a heavy chain variable domain selected from the sequences listed above. In another embodiment, the heavy chain variable domain comprises a sequence of amino acids that is encoded by a nucleotide sequence that is at least 70%, 75%, 80%, 85%, 90%, 91%, 92%, 93%, 94%, 95%, 96%, 97%, 98%, 99% or 100% identical to a nucleotide sequence that encodes a heavy chain variable domain selected from the sequences listed above. In another embodiment, the heavy chain variable domain comprises a sequence of amino acids that is encoded by a polynucleotide that hybridizes under moderately stringent conditions to the complement of a polynucleotide that encodes a heavy chain variable domain selected from the sequences listed above. In another embodiment, the heavy chain variable domain comprises a sequence of amino acids that is encoded by a polynucleotide that hybridizes under stringent conditions to the complement of a polynucleotide that encodes a heavy chain variable domain selected from the sequences listed above.

In the exemplary embodiments described above, the antigen binding proteins maintain desired binding to the various desired species of ASGR, ASGR-1 and/or ASGR-2.

Antigen binding proteins of the invention (e.g., antibodies) can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In one embodiment, an antigen binding protein of the invention further comprises the constant light chain kappa or lambda domains or a fragment of these. Exemplary sequences of the light chain constant regions and polynucleotides encoding them are provided in Table 15 below, and are generally well known in the art. In another embodiment, an antigen binding protein of the invention further comprises a heavy chain constant domain, or a fragment thereof, such as the IgG1 or IgG2 heavy chain constant region provided in Table 15.

The antigen binding proteins (for example, antibodies) of the present invention include those having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407, (incorporated by reference herein) to alleviate a tendency to form intra-H chain disulfide bonds that can lead to heterogeneity in the IgG4 antibodies.

Generation of Antibodies

Antibodies of the invention may be prepared by techniques that are well known to those skilled in the art. For example, by immunizing an animal (e.g., a mouse or rat or rabbit) and then by immortalizing spleen cells harvested from the animal after completion of the immunization schedule. The spleen cells can be immortalized using any technique known in the art, e.g., by fusing them with myeloma cells to produce hybridomas. See, for example, Antibodies; Harlow and Lane, Cold Spring Harbor Laboratory Press, 1$^{st}$ Edition, e.g. from 1988, or 2$^{nd}$ Edition, e.g. from 2014).

In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139.

In one embodiment, the chimeric antibody is a CDR grafted antibody. Techniques for humanizing antibodies are discussed in, e.g., U.S. Pat. Nos. 5,869,619; 5,225,539; 5,821, 337; 5,859,205; 6,881,557, Padlan et al., 1995, FASEB J. 9:133-39, Tamura et al., 2000, J. Immunol. 164:1432-41, Zhang, W., et al., Molecular Immunology. 42(12):1445-1451, 2005; Hwang W. et al., Methods. 36(1):35-42, 2005; Dall'Acqua W F, et al., Methods 36(1):43-60, 2005; and Clark, M., Immunology Today. 21(8):397-402, 2000.

An antibody of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue.

Antibodies produced in the animal incorporate human immunoglobulin polypeptide chains encoded by the human genetic material introduced into the animal. In one embodiment, a non-human animal, such as a transgenic mouse, is immunized with a suitable immunogen.

Examples of techniques for production and use of transgenic animals for the production of human or partially human antibodies are described in U.S. Pat. Nos. 5,814,318, 5,569,825, and 5,545,806, Davis et al., Production of human antibodies from transgenic mice in Lo, ed. Antibody Engineering: Methods and Protocols, Humana Press, NJ: 191-200 (2003), Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B-cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455 58; Jakobovits et al., 1995 Ann. N. Y. Acad. Sci. 764:525 35. In addition, protocols involving the XenoMouse® (Abgenix, now Amgen, Inc.) are described, for example in U.S. Pub. No. 2005/0118643 and WO 05/694879, WO 98/24838, WO 00/76310, and U.S. Pat. No. 7,064,244.

Lymphoid cells from the immunized transgenic mice are fused with myeloma cells for example to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in such fusions include Sp-20, P3-X63/Ag8, P3-X63-Ag8.653, NS1/1.Ag41, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. One selection media is HAT (hypoxanthine, aminopterin, thymidine). After a sufficient time, usually about one to two weeks, colonies of cells are observed. Single colonies are isolated, and antibodies produced by the cells may be tested for binding activity to, for example, human ASGR-1, using any one of a variety of immunoassays known in the art and described herein. The hybridomas are cloned (e.g., by limited dilution cloning or by soft agar plaque isolation) and positive clones that produce an antibody specific to, for example, human ASGR-1, are selected and cultured. The monoclonal antibodies from the hybridoma cultures may be isolated from the supernatants of hybridoma cultures. Thus the present invention provides hybridomas that comprise polynucleotides encoding the antigen binding proteins of the invention in the chromosomes of the cell. These hybridomas can be cultured according to methods described herein and known in the art.

Another method for generating human antibodies of the invention includes immortalizing human peripheral blood cells by EBV transformation. See, e.g., U.S. Pat. No. 4,464,456. Such an immortalized B-cell line (or lymphoblastoid cell line) producing a monoclonal antibody that specifically binds to, for example, human ASGR-1, can be identified by immunodetection methods as provided herein, for example, an ELISA, and then isolated by standard cloning techniques. The stability of the lymphoblastoid cell line producing an antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B-cells with antigen, followed by fusion of primed B-cells with a heterohybrid fusion partner. See, e.g., Boerner et al., 1991 J. Immunol. 147:86-95.

In certain embodiments, a B-cell that is producing a desired antibody is selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing a desired antibody. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains antigen. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZap™(L) vectors (Stratagene, La Jolla, California). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli.*

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, California), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., Science 242:423-426, 1988).

In certain embodiments, the antigen binding proteins of the invention are obtained from transgenic animals (e.g., mice) that produce "heavy chain only" antibodies or "HCAbs." HCAbs are analogous to naturally occurring camel and llama single-chain VHH antibodies.

See, for example, U.S. Pat. Nos. 8,507,748 and 8,502,014, and U.S. Patent Application Publication Nos. US2009/0285805A1, US2009/0169548A1, US2009/0307787A1, US2011/0314563A1, US2012/0151610A1, WO2008/122886A2, and WO2009/013620A2.

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

In certain embodiments, antibodies are generated by first identifying antibodies that bind to cells expressing, for example, human ASGR, human ASGR-1 and/or human ASGR-2, and/or compete for binding with the antibodies described in this application.

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

Molecular evolution of the complementarity determining regions (CDRs) in the center of the antibody binding site also has been used to isolate antibodies with increased affinity, for example, those as described by Schier et al., 1996, J. Mol. Biol. 263:551. Accordingly, such techniques are useful in preparing antibodies of the invention.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (for example, monkey such as cynomologus or rhesus monkey or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antibodies also may be prepared by any of a number of other conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kenneth et al. (eds.), Plenum Press, New York (1980); and Antibodies: A Laboratory Manual, Harlow and Land (eds.), Cold Spring Harbor Laboratory Press, Cold Spring Harbor, NY, (1988).

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of *E. coli.* (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and additional PCR techniques (Crameri, et al., Nature, 391, 288-291, 1998). All of these methods of affinity maturation are discussed by Vaughan et al. (Nature Biotechnology, 16, 535-539, 1998).

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

Antigen binding fragments derived from an antibody can also be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')2. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light heavy chain fragments (Fd), further cleaving of fragments, or other enzymatic, chemical, or genetic techniques may also be used, so long as the fragments bind to the antigen that is recognized by the intact antibody.

Another exemplary form of an antigen binding protein is a peptide comprising one or more complementarity determining regions (CDRs) of an antibody. CDRs can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)). The antibody fragment further may comprise at least one variable region domain of an antibody described herein. Thus, for example, the V region domain may be monomeric and be a $V_H$ or $V_L$ domain, which is capable of independently binding a desired target (e.g., human ASGR-1) with an affinity at least equal to $10^{-7}$ M or less as described herein.

The variable region may be any naturally occurring variable domain or an engineered version thereof. By engineered version is meant a variable region that has been created using recombinant DNA engineering techniques. Such engineered versions include those created, for example, from a specific antibody variable region by insertions, deletions, or changes in or to the amino acid sequences of the specific antibody. One of ordinary skill in the art can use any known methods for identifying amino acid residues appropriate for engineering, such as the amino acid residues depicted with shading in Tables 21-48 of FIG. 56. Additional examples include engineered variable regions containing at least one CDR and optionally one or more framework amino acids from a first antibody and the remainder of the variable region domain from a second antibody. Engineered versions of antibody variable domains may be generated by any number of techniques with which those having ordinary skill in the art will be familiar, including but not limited to the methods outlined in Example 14 below.

The variable region may be covalently attached at a C-terminal amino acid to at least one other antibody domain or a fragment thereof. Thus, for example, a VH that is present in the variable region may be linked to an immunoglobulin CH1 domain. Similarly a $V_L$ domain may be linked to a $C_K$ domain. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Derivatives and Variants

The nucleotide sequences of the antigen binding proteins of the present invention, encoding the corresponding amino acid sequences of the antibodies of the present invention, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of the antigen binding proteins that have a desired property, for example, increased affinity, avidity, or specificity for a desired target, increased activity or stability in vivo or in vitro, or reduced in vivo side-effects as compared to the underivatized antibody.

Other derivatives of the antigen binding proteins within the scope of this invention include covalent or aggregative conjugates of the antigen binding proteins, with other proteins or polypeptides, such as by expression of recombinant fusion proteins comprising heterologous polypeptides fused to the N-terminus or C-terminus of a polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, MO).

In another embodiment, the antigen binding proteins within the scope of this invention include antibody conjugates where antibody is conjugated to a non-proteinaceous chemical (drug) to form an antibody drug conjugate (ADC). Generally the ADC comprises an antibody conjugated to a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and may be used in embodiments of the present invention. (See US20090028856; US2009/0274713; US2007/0031402; WO2005/084390; WO2009/099728; U.S. Pat. Nos. 5,208,020; 5,416,064; 5,475,092; 5,585,499; 6,436,931; 6,372,738; and 6,340,701, all incorporated herein by reference).

In another embodiment, oligomers that contain one or more antigen binding proteins may be employed in certain embodiments of the present invention. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing an antigen binding fragment of an anti-ASGR, ASGR-1, and/or ASGR-2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In some embodiments, the variable portion of the heavy and/or light chains of a desired antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising a desired antibody fragment or derivative fused to a leucine zipper peptide are expressed in suitable host cells, and the soluble oligomeric antibody fragments or derivatives that form are recovered from the culture supernatant.

In another embodiment, the antigen binding proteins (e.g., antibodies) can be conjugated to a suitable vehicle to enhance the half-life thereof. Suitable vehicles include, but are not limited to, Fc, albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose. In certain embodiments, antibodies of the invention may be chemically bonded with polymers, lipids, or other moieties.

Nucleic Acids Encoding Antigen Binding Proteins

In another embodiment, the present invention provides isolated nucleic acid molecules that encode the antigen binding proteins of the present invention. In addition, provided are vectors comprising the nucleic acids, cell comprising the nucleic acids, and methods of making the antigen binding proteins of the invention. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, antisense nucleic acids for inhibiting expression of a polynucleotide, and complementary sequences of the foregoing. The nucleic acids can be any length as appropriate for the desired use or function, and can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with antigen. The nucleic acid may be isolated by conventional procedures such as polymerase chain reaction (PCR).

Nucleic acid sequences encoding the variable regions of the heavy and light chain variable regions are included herein. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for of the antibodies of the present invention, or a desired fragment, variant, or derivative thereof, is mutated such that it encodes an amino acid sequence comprising one or more deletions or substitutions of amino acid residues that are shown herein for the light chains of the antibodies of the present invention or the heavy chains of the antibodies of the present invention to be residues where two or more sequences differ. In another embodiment, the mutagenesis inserts an amino acid adjacent to one or more amino acid residues shown herein for the light chains of the antibodies of the present invention or the heavy chains of the antibodies of the present invention to be residues where two or more sequences differ. Alternatively, one or more mutations can be introduced into a nucleic acid that selectively change the biological activity of a polypeptide that it encodes.

In another embodiment, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionein promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another embodiment, the present invention provides host cells into which a recombinant expression vector of the invention has been introduced. A host cell can be any prokaryotic cell or eukaryotic cell. Prokaryotic host cells include gram negative or gram positive organisms, for example E. coli or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, Cytotechnology 28:31) or CHO strain DXB-11, which is deficient in DHFR (see Urlaub et al., 1980, Proc. Natl. Acad. Sci. USA 77:4216-20). Additional CHO cell lines include CHO-K1 (ATCC #CCL-61), EM9 (ATCC #CRL-1861), and UV20 (ATCC #CRL-1862). Additional host cells include the COS-7 line of monkey kidney cells (ATCC CRL 1651) (see Gluzman et al., 1981, Cell 23:175), L cells, C127 cells, 3T3 cells (ATCC CCL 163), AM-1/D cells (described in U.S. Pat. No. 6,210,924), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, New York, 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Additional selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide recovered by conventional protein purification procedures. Polypeptides contemplated for use herein include substantially homogeneous recombinant mammalian antibody polypeptides substantially free of contaminating endogenous materials.

Cells containing the nucleic acid encoding the antigen binding proteins of the present invention also include hybridomas. The production and culturing of hybridomas are discussed in the antibody section above.

In some embodiments, a vector comprising a nucleic acid molecule as described herein is provided. In some embodiments, the invention comprises a host cell comprising a nucleic acid molecule as described herein.

In some embodiments, a nucleic acid molecule encoding the antigen binding protein as described herein is provided.

In some embodiments, a pharmaceutical composition comprising at least one antigen binding protein described herein is provided.

Antigen Binding Protein Production

The antigen binding proteins of the invention can be produced by any method known in the art for the synthesis of proteins (e.g., antibodies), in particular, by chemical synthesis or preferably, by recombinant expression techniques.

Recombinant expression of the antigen binding proteins requires construction of an expression vector containing a polynucleotide that encodes the the antigen binding proteins. Once a polynucleotide encoding the antigen binding proteins molecule has been obtained, the vector for the production of the antigen binding proteins may be produced by recombinant DNA technology. An expression vector is constructed containing the antigen binding proteins coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antigen binding proteins of the invention. In one embodiment of the invention, vectors encoding both the heavy and light chains of an antibody may be co-expressed in the host cell for expression of the entire immunoglobulin molecule, as detailed below.

A variety of host-expression vector systems may be utilized to express the antigen binding proteins of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" (DNA Cloning, Vol. 3. Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, for example, the first vector encoding an antibody heavy chain derived polypeptide and the second vector encoding an antibody light chain derived polypeptide. The two vectors may contain identical selectable markers which enable equal expression of heavy and light chain polypeptides. Alternatively, a single vector may be used which encodes, and is capable of expressing, for example, both antibody heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In some embodiments, the present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474,981; Gillies et al., Proc. Natl. Acad. Sci. 89:1428-1432 (1992); Fell et al., J. Immunol. 146:2446-2452 (1991).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Antibody Effector Function

In some embodiments, the present invention provides antigen binding proteins (e.g., antibodies) with altered effector function (e.g., decreasing or increasing effector function). Nonlimiting examples of methods for increasing effector function can be found in U.S. Pat. Nos. 5,624,821, 6,602,684, 7,029,872, U.S. Patent Application Publication Nos. 2006/0067930A1, 2005/0272128A1, 2005/0079605A1, 2005/0123546A1, 2004/0072290A1, 2006/0257399A1, 2004/0261148A1, 2007/0092521, 2006/0040325A1, and 2006/0039904A1, and International Patent Application Publication Nos. WO 04/029207, WO03011878, WO05044859, WO 06071856, and WO 06071280.

Methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for Fc gamma RIIB as compared with the binding affinity for FC gamma RIIA; see, also, PCT Publication Nos. WO 99/58572 to Armour et al., WO 99/51642 to Idusogie et al., and U.S. Pat. No. 6,395,272 to Deo et al.). Methods of modifying the Fc region to decrease binding affinity to Fc gamma RIIB are also known in the art (e.g., U.S. Patent Publication No. 20010036459 and PCT Publication No. WO 01/79299, both to Ravetch et al.). Modified antibodies having variant Fc regions with enhanced binding affinity for Fc gamma RIIIA and/or Fc gamma RIIA as compared with a wildtype Fc region have also been described (e.g., PCT Publication Nos. WO 2004/063351, to Stavenhagen et al., the disclosure of which is incorporated herein in its entirety).

Antibody effector function may also be modified through the generation of antibodies with altered glycosylation patterns. Such altered glycosylation patterns have been demonstrated to increase or decrease the ADCC ability of antibodies, as desired. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation.

Half-Life Alteration

In some embodiments, the present invention provides for antigen binding proteins (e.g., antibodies) which have an extended half-life in vivo. In particular, the present invention provides antigen binding proteins which have a half-life in a mammal (for example, but not limited to, a human), of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antigen binding proteins (for example, monoclonal antibodies) or antibody fragments (for example, Fab fragments) in vivo, for example, inert polymer molecules such as high molecular weight polyethyleneglycol (PEG) can be attached to the antibodies (including antibody fragments thereof) with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antigen binding proteins. Unreacted PEG can be separated from antigen binding proteins-PEG conjugates by size-exclusion or by ion-exchange chromatography. PEG-derivatized antigen binding proteins can be tested for binding activity as well as for in vivo efficacy using methods known to those of skill in the art, for example, by immunoassays described herein.

In certain embodiments, antibodies having an increased half-life in vivo can also be generated by introducing one or more amino acid modifications (i.e., substitutions, insertions or deletions) into an IgG constant domain, or FcRn binding fragment thereof (e.g., Fc or hinge Fc domain fragment). See, e.g., International Publication No. WO 98/23289; International Publication No. WO 97/34631; and U.S. Pat. No. 6,277,375, each of which is incorporated herein by reference in its entirety.

Conjugates

In some embodiments, covalent modifications of the antigen binding proteins of the invention are included within the scope of this invention. They may be made by chemical synthesis or by enzymatic or chemical cleavage of the antigen binding proteins, if applicable. Other types of covalent modifications of the antigen binding proteins are introduced into the molecule by reacting targeted amino acid residues of the antibody with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, alpha-bromo-beta-(5-imidazolyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues and/or e-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the epsilon-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively. Tyrosyl residues are iodinated using $I^{125}$ or $I^{131}$ to prepare labeled proteins for use in radioimmunoassay.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Interfering RNA

In some embodiments, the present invention provides polynucleotide compositions that target ASGR-1 and/or ASGR-2 and are useful for methods for treatment, therapy, and prophylaxis in disease related to ASGR, ASGR-1 and/or ASGR-2 expression, where reduction or inhibition of the expression or function of a selected target polynucleotide sequence is desired. Examples of polynucleotides that can be used to target ASGR-1 and/or ASGR-2 sequences and reduce ASGR-1 and/or ASGR-2 expression include, but are not limited to, antisense oligonucleotides, and RNA interference (RNAi) agents, including short or small interfering RNA (siRNA), short hairpin RNA (shRNA), and microRNA (miRNA). See, for example, U.S. Pat. Nos. 6,506,559; 8,394,628; 7,056,704; 7,078,196; 6,107,094; 5,898,031; 6,573,099; and European Patent No. 1,144,623. See also, for example, U.S. patent application publication nos. 2015/0259689; 2015/0197746; 2011/0092565; U.S. Pat. Nos. 8,877,917; 8,507,455; and 7,579,451.

In certain embodiments, a composition for inhibiting the function or expression of a target polynucleotide sequence (e.g. ASGR-1 mRNA sequence, ASGR-2 mRNA sequence) in a mammalian cell, according to this invention, comprises an agent that provides to a mammalian cell an at least partially double-stranded RNA molecule (e.g., an interfering RNA molecule). A double-stranded RNA molecule may include chemical modifications to ribonucleotides, including modifications to the ribose sugar, base, or backbone components of the ribonucleotides, such as those described herein or known in the art. Any such modifications, as used in a double-stranded RNA molecule (e.g. siRNA, shRNA, or the like), are encompassed by the term "double-stranded RNA" for the purposes of this disclosure. Thus, in general, the term "RNA" may also include RNA-DNA hybrids and polynucleotides comprising one or more modified nucleotides (e.g. nucleotides with modifications at the 2' position of the ribose ring), except where specified otherwise, e.g., where a 2'-OH group of ribose is required for a particular linkage.

In some embodiments at least 10% of a partially double-stranded RNA molecule is double-stranded. Alternatively, the double stranded portion of these RNA molecules can be at least 30% of the length of the molecule. In another embodiment, the double stranded portion of these molecules can be at least 50% of the the length of the molecule. In still another embodiment, the double stranded portion of these molecules can be at least 70% of the length of the molecule. In another embodiment, the double stranded portion of these molecules can be at least 90% of the length of the molecule. In another embodiment, the molecule can be double stranded over its entire length. Alternatively, the double-stranded portion of these molecules can occur at either or both termini, or in some middle portion of the molecule, if the molecule is linear. Similarly, the double-stranded portion can be in any location if the molecule is circular. In certain embodiments of the present invention, the double-stranded portion of the RNA molecule becomes double-stranded only when the molecule is in the mammalian cell. In still other embodiment of this invention, the partially double-stranded molecule is an RNA/DNA hybrid, for example, a single strand containing RNA and DNA, prepared in vitro; or a duplex of two such single strands or portions thereof. In yet another embodiment, the RNA molecule, made in vivo or in vitro, is a duplex comprised of an RNA single strand and a DNA single strand. In some embodiments, the partially double-stranded RNA molecule comprises a polynucleotide sequence that is substantially homologous to the target polynucleotide sequence in order to effectively reduce or inhibit the function or expression thereof. The necessary homology may be suitably defined by use of a computer algorithm. As known in the art and discussed herein, "homology" or "identity" means the degree of sequence relatedness between two polypeptide or two polynucleotide sequences as determined by the identity of the match between two lengths of such sequences. Both identity and homology can be readily calculated by methods in the prior art [See also, e.g., COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991)]. While there exist a number of methods to measure identity and homology between two polynucleotide sequences, the terms "identity", "similarity" and homology are well known to skilled artisans [H. Carillo and D. Lipton, SIAM J. Applied Math., 48:1073 (1988)]. Methods commonly employed to determine identity or homology between two sequences include, but are not limited to, those disclosed in Guide to Huge Computers, Martin J. Bishop, ed., Academic Press, San Diego, 1994, and H. Carillo and D. Lipton, SIAM J. Applied Math., 48:1073 (1988). Preferred methods to determine identity or homology are designed to give the largest match between the two sequences tested. Methods to determine identity and similarity are codified in computer programs. Preferred computer program to determine identity and homology between two sequences include, but are not limited to, the algorithm BESTFIT from the GCG program package [J. Devereux et al., Nucl. Acids Res., 12(1):387 (1984)], the related MACVECTOR program (Oxford), and the FASTA (Pearson) programs. For instance, searches for sequence similarities in databases between significant naturally occurring mammalian polynucleotide sequences and target polynucleotide sequences enable the design of suitable RNA molecules desired for use in the invention. The algorithm and/or the degree of homology necessary for any particular RNA molecule may be selected by one of skill in the art, depending on the identity of the target, and/or the closeness of homology of the target sequence to any naturally occurring mammalian sequence, which is desired to be left functioning normally after use of the methods of this invention.

In some embodiments, a polynucleotide composition for reducing the expression or function of ASGR-1 and/or ASGR-2 sequences is an RNAi agent comprising a double-stranded RNA molecule which comprises two antiparallel strands of contiguous nucleotides that are sufficiently complementary to each other to hybridize to form a duplex region. "Hybridize" or "hybridization" refers to the pairing of complementary polynucleotides, typically via hydrogen bonding (e.g. Watson-Crick, Hoogsteen or reversed Hoogsteen hydrogen bonding) between complementary bases in the two polynucleotides. The strand comprising a region having a sequence that is substantially complementary to a target sequence (e.g. target mRNA) is referred to as the "antisense strand." The "sense strand" refers to the strand that includes a region that is substantially complementary to a region of the antisense strand. In some embodiments, the sense strand may comprise a region that has a sequence that is substantially identical to the target sequence.

As used herein, a first sequence is "complementary" to a second sequence if a polynucleotide comprising the first sequence can hybridize to a polynucleotide comprising the second sequence to form a duplex region under certain conditions, such as physiological conditions. Other such conditions can include moderate or stringent hybridization conditions, which are known to those of skill in the art. A first sequence is considered to be fully complementary (100% complementary) to a second sequence if a polynucleotide comprising the first sequence base pairs with a polynucleotide comprising the second sequence over the entire length of one or both nucleotide sequences without any mismatches. A sequence is "substantially complementary" to a target sequence if the sequence is at least about 80%, 85%, 90%, 95%, 96%, 97%, 98%, 99% or 100% complementary to a target sequence. Percent complementarity can be calculated by dividing the number of bases in a first sequence that are complementary to bases at corresponding positions in a second or target sequence by the total length of the first sequence. A sequence may also be said to be substantially complementary to another sequence if there are no more than 5, 4, 3, or 2 mismatches over a 30 base pair duplex region when the two sequences are hybridized. Generally, if any nucleotide overhangs, as defined herein, are present, the sequence of such overhangs is not considered in determining the degree of complementarity between two sequences. By way of example, a sense strand of 21 nucleotides in length and an antisense strand of 21 nucleotides in length that hybridize to form a 19 base pair duplex region with a 2 nucleotide overhang at the 3' end of each strand would be considered to be fully complementary as the term is used herein.

In some embodiments, a region of the antisense strand comprises a sequence that is fully complementary to a region of the target RNA sequence (e.g. ASGR-1 and/or ASGR-2 mRNA). In such embodiments, the sense strand may comprise a sequence that is fully complementary to the sequence of the antisense strand. In other such embodiments, the sense strand may comprise a sequence that is substantially complementary to the sequence of the antisense strand, e.g. having 1, 2, 3, 4, or 5 mismatches in the duplex region formed by the sense and antisense strands. In certain embodiments, it is preferred that any mismatches occur within the terminal regions (e.g. within 6, 5, 4, 3, or 2 nucleotides of the 5' and/or 3' ends of the strands). In one embodiment, any mismatches in the duplex region formed from the sense and antisense strands occur within 6, 5, 4, 3, or 2 nucleotides of the 5' end of the antisense strand.

In certain embodiments, the sense strand and antisense strand of the double-stranded RNA may be two separate molecules that hybridize to form a duplex region, but are otherwise unconnected. Such double-stranded RNA molecules formed from two separate strands are referred to as "small interfering RNAs" or "short interfering RNAs" (siRNAs).

In other embodiments, the sense strand and the antisense strand that hybridize to form a duplex region may be part of a single RNA molecule, i.e. the sense and antisense strands are part of a self-complementary region of a single RNA molecule. In such cases, a single RNA molecule comprises a duplex region (also referred to as a stem region) and a loop region. The 3' end of the sense strand is connected to the 5' end of the antisense strand by a contiguous sequence of unpaired nucleotides, which will form the loop region. The loop region is typically of a sufficient length to allow the RNA molecule to fold back on itself such that the antisense strand can base pair with the sense strand to form the duplex or stem region. The loop region can comprise from about 3 to about 25, from about 5 to about 15, or from about 8 to about 12 unpaired nucleotides. Such RNA molecules with at least partially self-complementary regions are referred to as "short hairpin RNAs" (shRNAs). The length of a single, at least partially self-complementary RNA molecule can be from about 35 nucleotides to about 100 nucleotides, from about 45 nucleotides to about 85 nucleotides, or from about 50 to about 60 nucleotides and comprise a duplex region and loop region each having the lengths recited herein.

In some embodiments, the double-stranded RNA molecule comprises a sense strand and an antisense strand, wherein the antisense strand comprises a region having a sequence that is substantially or fully complementary to an ASGR-1 messenger RNA (mRNA) sequence and/or ASGR-2 mRNA sequence. As used herein, an "ASGR-1 mRNA sequence" or "ASGR-2 mRNA sequence" refers to any messenger RNA sequence, including splice variants, encoding an ASGR-1 protein or ASGR-2 protein, including ASGR-1 or ASGR-2 protein variants or isoforms from any species (e.g. mouse, rat, non-human primate, human).

The sense strand of the double-stranded RNA molecule typically comprises a sequence that is sufficiently complementary to the sequence of the antisense strand such that the two strands hybridize under physiological conditions to form a duplex region. A "duplex region" refers to the region in two complementary or substantially complementary polynucleotides that form base pairs with one another, either by Watson-Crick base pairing or other hydrogen bonding interaction, to create a duplex between the two polynucleotides. The duplex region of the RNA molecule should be of sufficient length to allow the RNA molecule to enter the RNA interference pathway, e.g. by engaging the Dicer enzyme and/or the RISC complex. For instance, in some embodiments, the duplex region is about 15 to about 30 base pairs in length. Other lengths for the duplex region within this range are also suitable, such as about 15 to about 28 base pairs, about 15 to about 26 base pairs, about 15 to about 24 base pairs, about 15 to about 22 base pairs, about 17 to about 28 base pairs, about 17 to about 26 base pairs, about 17 to about 24 base pairs, about 17 to about 23 base pairs, about 17 to about 21 base pairs, about 19 to about 25 base pairs, about 19 to about 23 base pairs, or about 19 to about 21 base pairs. In one embodiment, the duplex region is about 17 to about 24 base pairs in length. In another embodiment, the duplex region is about 19 to about 21 base pairs in length.

For embodiments in which the sense strand and antisense strand are two separate molecules (e.g. RNAi agent is a siRNA), the sense strand and antisense strand need not be the same length as the length of the duplex region. For instance, one or both strands may be longer than the duplex region and have one or more unpaired nucleotides or mismatches flanking the duplex region. Thus, in some embodiments, the double-stranded RNA molecule comprises at least one nucleotide overhang. As used herein, a "nucleotide overhang" refers to the unpaired nucleotide or nucleotides that extend beyond the duplex region at the terminal ends of the strands. Nucleotide overhangs are typically created when the 3' end of one strand extends beyond the 5' end of the other strand or when the 5' end of one strand extends beyond the 3' end of the other strand. The length of a nucleotide overhang is generally between 1 and 6 nucleotides, 1 and 5 nucleotides, 1 and 4 nucleotides, 1 and 3 nucleotides, 2 and 6 nucleotides, 2 and 5 nucleotides, or 2 and 4 nucleotides. In some embodiments, the nucleotide overhang comprises 1, 2, 3, 4, 5, or 6 nucleotides. In one particular embodiment, the nucleotide overhang comprises 1 to 4 nucleotides. In certain embodiments, the nucleotide overhang comprises 2 nucleotides. The nucleotides in the overhang can be ribonucleotides, deoxyribonucleotides, or modified nucleotides as described herein.

The nucleotide overhang can be at the 5' end or 3' end of one or both strands. For example, in one embodiment, the double-stranded RNA molecule comprises a nucleotide overhang at the 5' end and the 3' end of the antisense strand. In another embodiment, the double-stranded RNA molecule comprises a nucleotide overhang at the 5' end and the 3' end of the sense strand. In some embodiments, the double-stranded RNA molecule comprises a nucleotide overhang at the 5' end of the sense strand and the 5' end of the antisense strand. In other embodiments, the double-stranded RNA molecule comprises a nucleotide overhang at the 3' end of the sense strand and the 3' end of the antisense strand.

The double-stranded RNA molecules may comprise a single nucleotide overhang at one end of the molecule and a blunt end at the other. A "blunt end" means that the sense strand and antisense strand are fully base-paired at the end of the molecule and there are no unpaired nucleotides that extend beyond the duplex region. In some embodiments, the double-stranded RNA molecule comprises a nucleotide overhang at the 3' end of the sense strand and a blunt end at the 5' end of the sense strand and 3' end of the antisense strand. In other embodiments, the double-stranded RNA molecule comprises a nucleotide overhang at the 3' end of the antisense strand and a blunt end at the 5' end of the antisense strand and the 3' end of the sense strand. In certain embodiments, the double-stranded RNA molecule comprises a blunt end at both ends of the double-stranded RNA molecule. In such embodiments, the sense strand and antisense strand have the same length and the duplex region is the same length as the sense and antisense strands (i.e. the molecule is double-stranded over its entire length).

The sense strand and antisense strand can each independently be about 15 to about 30 nucleotides in length, about 18 to about 28 nucleotides in length, about 19 to about 27 nucleotides in length, about 19 to about 25 nucleotides in length, about 19 to about 23 nucleotides in length, about 21 to about 25 nucleotides in length, or about 21 to about 23 nucleotides in length. In certain embodiments, the sense strand and antisense strand are each about 18, about 19, about 20, about 21, about 22, about 23, about 24, or about 25 nucleotides in length. In some embodiments, the sense strand and antisense strand have the same length but form a duplex region that is shorter than the strands such that the double-stranded RNA molecule has two nucleotide overhangs. For instance, in one embodiment, the double-stranded RNA molecule comprises (i) a sense strand and an antisense strand that are each 21 nucleotides in length, (ii) a duplex region that is 19 base pairs in length, and (iii) nucleotide overhangs of 2 unpaired nucleotides at both the 3' end of the sense strand and the 3' end of the antisense strand. In another embodiment, the double-stranded RNA molecule comprises (i) a sense strand and an antisense strand that are each 23 nucleotides in length, (ii) a duplex region that is 21 base pairs in length, and (iii) nucleotide overhangs of 2 unpaired nucleotides at both the 3' end of the sense strand and the 3' end of the antisense strand. In other embodiments, the sense strand and antisense strand have the same length and form a duplex region over their entire length such that there are no nucleotide overhangs on either end of the double-stranded molecule. In one such embodiment, the double-stranded RNA molecule is blunt ended and comprises (i) a sense strand and an antisense strand, each of which is 21 nucleotides in length, and (ii) a duplex region that is 21 base pairs in length. In another such embodiment, the double-stranded RNA molecule is blunt ended and comprises (i) a sense strand and an antisense strand, each of which is 23 nucleotides in length, and (ii) a duplex region that is 23 base pairs in length.

In other embodiments, the sense strand or the antisense strand is longer than the other strand and the two strands form a duplex region having a length equal to that of the shorter strand such that the double-stranded RNA molecule comprises at least one nucleotide overhang. For example, in one embodiment, the double-stranded RNA molecule comprises (i) a sense strand that is 19 nucleotides in length, (ii) an antisense strand that is 21 nucleotides in length, (iii) a duplex region of 19 base pairs in length, and (iv) a single nucleotide overhang of 2 unpaired nucleotides at the 3' end of the antisense strand. In another embodiment, the double-stranded RNA molecule comprises (i) a sense strand that is 21 nucleotides in length, (ii) an antisense strand that is 23 nucleotides in length, (iii) a duplex region of 21 base pairs in length, and (iv) a single nucleotide overhang of 2 unpaired nucleotides at the 3' end of the antisense strand.

Off-target toxicity is a constant concern in the development of pharmaceutical products. With interfering RNA agents, the potential exists for homology with certain endogenous polynucleotide sequences that could lead to unintended toxic effects in the patient receiving the interfering RNA. Accordingly, in some embodiments, the RNA molecule comprises a polynucleotide sequence that is also substantially non-homologous to any naturally occurring, normally functioning, and essential mammalian polynucleotide sequence, so that the RNA molecule does not adversely affect the function of any essential naturally occurring mammalian polynucleotide sequence, when used in the methods of this invention. Such naturally occurring functional mammalian polynucleotide sequences include mammalian sequences that encode desired proteins, as well as mammalian sequences that are non-coding, but that provide for essential regulatory sequences in a healthy mammal. Preferably, the RNA molecule useful in the methods of the invention must be sufficiently distinct in sequence from any mammalian polynucleotide sequence expressed in the target cells (e.g. liver cells) for which the function is intended to be undisturbed after any of the methods of this invention are performed. As described for determining the homology to the target sequence above, one of skill in the art may resort to the above-identified computer algorithms to define the essential lack of homology between the RNA molecule polynucleotide sequence and the normal mammalian sequences expressed in the target cells. For example, in a specific embodiment, the homology between the sequence of an RNAi agent and the selected normal sequence expressed in the target cells is less than the homologies of the formulae described above. In some embodiments, there is almost no homology at all between the sequence of an RNAi agent and any normal mammalian sequence.

The double-stranded RNA molecules used in the methods of the invention may comprise one or more modified nucleotides. A "modified nucleotide" refers to a nucleotide that has one or more chemical modifications to the nucleoside, nucleobase, pentose ring, or phosphate group. The double-stranded RNA molecules may comprise combinations of modified nucleotides, ribonucleotides, and deoxyribonucleotides. Incorporation of modified nucleotides into one or both strands of double-stranded RNA molecules can improve the in vivo stability of the RNA molecules, e.g., by reducing the molecules' susceptibility to nucleases and other degradation processes. The potency of double-stranded RNA molecules for reducing expression of the target gene can also be enhanced by incorporation of modified nucleotides.

In certain embodiments, the modified nucleotides have a modification of the ribose sugar. These sugar modifications can include modifications at the 2' and/or 5' position of the pentose ring. A 2'-modified nucleotide refers to a nucleotide having a pentose ring with a substituent at the 2' position other than H or OH. Such 2'-modifications include, but are not limited to, 2'-O-alkyl (e.g. O—$C_1$-$C_{10}$ or O—$C_1$-$C_{10}$ substituted alkyl), 2'-O-allyl (O—$CH_2CH$=$CH_2$), 2'-C-allyl, 2'-fluoro, 2'-O-methyl ($OCH_3$), 2'-O-methoxyethyl (O—$(CH_2)_2OCH_3$), 2'-$OCF_3$, 2'-O$(CH_2)_2SCH_3$, 2'-O-aminoalkyl, 2'-amino (e.g. $NH_2$), 2'-O-ethylamine, and 2'-azido. Modifications at the 5' position of the pentose ring include, but are not limited to, 5'-methyl (R or S); 5'-vinyl, and 5'-methoxy.

The double-stranded RNA molecules employed in the methods of the invention may also comprise one or more modified internucleotide linkages. As used herein, the term "modified internucleotide linkage" refers to an internucleotide linkage other than the natural 3' to 5' phosphodiester linkage. In some embodiments, the modified internucleotide linkage is a phosphorous-containing internucleotide linkage, such as a phosphotriester, aminoalkylphosphotriester, an alkylphosphonate (e.g. methylphosphonate, 3'-alkylene phosphonate), a phosphinate, a phosphoramidate (e.g. 3'-amino phosphoramidate and aminoalkylphosphoramidate), a phosphorothioate (P=S), a chiral phosphorothioate, a phosphorodithioate, a thionophosphoramidate, a thionoalkylphosphonate, a thionoalkylphosphotriester, and a boranophosphate. In one embodiment, a modified internucleotide linkage is a 2' to 5' phosphodiester linkage. In other embodiments, the modified internucleotide linkage is a non-phosphorous-containing internucleotide linkage and thus can be referred to as a modified internucleoside linkage. Such non-phosphorous-containing linkages include, but are not limited to, morpholino linkages (formed in part from the sugar portion of a nucleoside); siloxane linkages (—O—Si$(H)_2$—O—); sulfide, sulfoxide and sulfone linkages; formacetyl and thioformacetyl linkages; alkene containing backbones; sulfamate backbones; methylenemethylimino (—$CH_2$—$N(CH_3)$—O—$CH_2$—) and methylenehydrazino linkages; sulfonate and sulfonamide linkages; amide linkages; and others having mixed N, O, S and $CH_2$ component parts. In one embodiment, the modified internucleoside linkage is a peptide-based linkage (e.g. aminoethylglycine) to create a peptide nucleic acid or PNA, such as those described in U.S. Pat. Nos. 5,539,082; 5,714,331; and 5,719,262. Other suitable modified internucleotide and internucleoside linkages that may be employed in the double-stranded RNA molecules are described in U.S. Pat. Nos. 6,693,187, and 9,181,551, U.S. Patent Publication No. 2016/0122761, and Deleavey and Damha, Chemistry and Biology, Vol. 19: 937-954, 2012, all of which are hereby incorporated by reference in their entireties.

Interfering RNA Delivery

The interfering RNA compounds can be administered by any method suitable for administration of nucleic acid agents, such as a DNA vaccine or gene therapy vectors. These methods include gene guns, bio injectors, and skin patches as well as needle-free methods such as the microparticle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for example, Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The interfering RNA molecule may be conjugated to one or more carbohydrate moieties to optimize one or more properties of the interfering RNA molecule. In many cases, the carbohydrate moiety will be attached to a modified subunit of the interfering RNA molecule or at the 5' or 3' end of one of strands of the interfering RNA molecule. E.g., the ribose sugar of one or more ribonucleotide subunits of an interfering RNA molecule can be replaced with another moiety, e.g., a non-carbohydrate (preferably cyclic) carrier to which is attached a carbohydrate moiety. A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carbohydrate moiety may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In some embodiments the interfering RNA molecule of the invention is conjugated to a carbohydrate moiety via a carrier, wherein the carrier can be cyclic group or acyclic group; in specific embodiments, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

Targeting the Interfering RNA

Given that ASGR, ASGR-1 and/or ASGR-2 is expressed on the surface of liver cells (e.g. hepatocytes), in certain embodiments, it is desirable to deliver the interfering RNA molecules to those liver cells so that the interfering effect can be exerted specifically within liver cells. Accordingly, in certain embodiments, the interfering RNA molecules are specifically targeted to liver cells using various methodologies known in the art and described herein. For example, in certain embodiments, antigen binding proteins (e.g. antibodies) or other targeting moieties disclosed herein below can be used to specifically target the interfering RNA molecules to the hepatocytes using various different receptors expressed on the surface of hepatocytes. In certain embodiments, the interfering RNA molecules are targeted to liver cells using the surface expressed ASGR, ASGR-1 and/or ASGR-2. In these embodiments, it is envisioned that this can result in a self-regulating system that reduces the amount of RNAi agent delivered to the liver cells as expression of ASGR, ASGR-1, and/or ASGR-2 is reduced due to the effect of the targeted interfering RNA.

A wide variety of targeting moieties can be coupled to the oligonucleotides of the present invention. In some embodiments, the targeting moieties are coupled, e.g., covalently, either directly or indirectly via an intervening tether.

In some embodiments, a targeting moiety alters the distribution, targeting or lifetime of the molecule into which it is incorporated. In preferred embodiments a targeting moiety provides an enhanced affinity for a selected target, e.g., molecule, cell or cell type, compartment, receptor e.g., a cellular or organ compartment, tissue, organ or region of the body, as, e.g., compared to a species absent such a targeting moiety. Targeting moieties providing enhanced affinity for a selected target are also termed targeting moieties.

Some targeting moieties can have endosomolytic properties. The endosomolytic targeting moieties promote the lysis of the endosome and/or transport of the composition of the invention, or its components, from the endosome to the cytoplasm of the cell. The endosomolytic targeting moiety may be a polyanionic peptide or peptidomimetic which shows pH-dependent membrane activity and fusogenicity. In one embodiment, the endosomolytic targeting moiety assumes its active conformation at endosomal pH. The "active" conformation is that conformation in which the endosomolytic targeting moiety promotes lysis of the endosome and/or transport of the composition of the invention, or its components, from the endosome to the cytoplasm of the cell. Exemplary endosomolytic targeting moieties include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched.

In certain embodiments, targeting moieties can improve transport, hybridization, and specificity properties and may also improve nuclease resistance of the resultant natural or modified oligoribonucleotide, or a polymeric molecule comprising any combination of monomers described herein and/or natural or modified ribonucleotides.

In some embodiments, targeting moieties in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Targeting moieties can include a naturally occurring substance, such as a protein (e.g., human serum albumin (I), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The targeting moiety may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly (L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Targeting moieties can also include other targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of targeting moieties include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g, cholesterol, cholic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Targeting moieties can be proteins, e.g., glycoproteins, or peptides, e.g., molecules having a specific affinity for a co-moiety, or antigen binding proteins, such as antibodies; e.g., an antibody, that binds to a specified cell type such as a liver hepatocyte. Targeting moieties may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The targeting moiety can be, for example, a lipopolysaccharide.

The targeting moiety can be a substance, e.g, a drug, which can increase the uptake of the interfering RNA molecule into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, jasplakinolide, latrunculin A, phalloidin, swinholide A, indanocine, or myoseverin.

The targeting moiety can increase the uptake of the interfering RNA molecule into the cell by activating an inflammatory response, for example. Exemplary targeting moieties that would have such an effect include tumor necrosis factor alpha (TNFalpha), interleukin-1 beta, or gamma interferon.

In one embodiment, the targeting moiety is a lipid or lipid-based molecule. Such a lipid or lipid-based molecule preferably binds a serum protein, e.g., human serum albumin (I). A serum protein binding targeting moiety, in certain embodiments, allows for distribution of the conjugate to a target tissue, e.g., a non-kidney target tissue of the body. For example, the target tissue can be the liver, including hepatocytes or parenchymal cells of the liver. Other molecules that can bind serum proteins can also be used as targeting moieties. For example, naproxen or aspirin can be used. A lipid or lipid-based targeting moiety can (a) increase resistance to degradation of the conjugate, (b) increase targeting or transport into a target cell or cell membrane, and/or (c) can be used to adjust binding to a serum protein.

A lipid based targeting moiety can be used to modulate, e.g., control the binding of the conjugate to a target tissue. For example, a lipid or lipid-based targeting moiety that binds to a serum protein more strongly will be less likely to be targeted to the kidney and therefore less likely to be cleared from the body. A lipid or lipid-based targeting moiety that binds to a serum protein less strongly can be used to target the conjugate to the kidney, if so desired.

In one embodiment, the lipid based targeting moiety binds human serum albumin. In a specific embodiment, it binds human serum albumin with a sufficient affinity such that the conjugate will be preferably distributed to a non-kidney tissue. In certain embodiments, it is preferred that the affinity not be so strong that the human serum albumin targeting moiety binding cannot be reversed.

In another preferred embodiment, the lipid based targeting moiety binds human serum albumin weakly or not at all, such that the conjugate will be preferably distributed to the kidney. Other moieties that target to kidney cells can also be used in place of or in addition to the lipid-based targeting moiety.

In another embodiment, the targeting moiety is for example a vitamin, e.g., a vitamin, which is taken up by a target cell, e.g., a proliferating cell. Exemplary vitamins include vitamin A, E, and K. Other exemplary vitamins include B vitamins, e.g., folic acid, B12, riboflavin, biotin, pyridoxal or other vitamins or nutrients taken up by cells. Also included are low density lipoprotein (LDL) and high-density lipoprotein (HDL).

In another embodiment, the targeting moiety is a cell-permeation agent, preferably a helical cell-permeation agent. In some embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The targeting moiety can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). In some embodiments, the peptide or peptidomimetic tethered to an interfering RNA molecule via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide can facilitate targeting of an interfering RNA molecule to cells of a variety of other tissues, including the lung, kidney, spleen, or liver (Aoki et al., Cancer Gene Therapy 8:783-787, 2001). The RGD peptide can be linear or cyclic, and can be modified, e.g., glycosylated or methylated to facilitate targeting to specific tissues. For example, a glycosylated RGD peptide can deliver an interfering RNA molecule to a cell expressing αVβ$_3$ (Haubner et al., Jour. Nucl. Med., 42:326-336, 2001). Peptides that target markers enriched in proliferating cells can be used. E.g., RGD containing peptides and peptidomimetics can target cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Cecropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, pardaxins, buforin, CPF, bombinin-like peptide (BLP), cathelicidins, ceratotoxins, S. clava peptides, hagfish intestinal antimicrobial peptides (HFIAPs), magainins, brevinins-2, dermaseptins, melittins, pleurocidin, H.sub.2A peptides, Xenopus peptides, esculentin-1, and caerins.

Peptide and peptidomimetic targeting moieties include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting moiety can be any moiety that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting moieties also include integrin receptor moieties, chemokine receptor moieties, transferrin, biotin, serotonin receptor moieties, PSMA, endothelin, GCPII, somatostatin, LDL and HDL moieties. The targeting moieties can also be based on nucleic acid, e.g., an aptamer. The aptamer can be unmodified or have any combination of modifications disclosed herein.

Other exemplary endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

Pharmacokinetic ("PK") modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as targeting moieties (e.g. as PK modulating moieties). In addition, aptamers that bind serum components (e.g. serum proteins) are also amenable to the present invention as PK modulating moieties.

When two or more targeting moieties are present, the targeting moieties can all have same properties, all have different properties or some targeting moieties have the same properties while others have different properties. For example, a targeting moiety can have targeting properties, have endosomolytic activity and/or have PK modulating properties. In certain embodiments, all the have different properties.

In some embodiments, a targeting moiety can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

It is envisioned that any suitable targeting moiety in the field of RNA interference may be used, although the targeting moiety is typically a carbohydrate e.g. monosaccharide (such as GalNAc), disaccharide, trisaccharide, tetrasaccharide, polysaccharide. Linkers that conjugate the targeting moiety to the nucleic acid include those discussed herein. For example, the targeting moiety can be one or more GalNAc derivatives attached through a bivalent or trivalent branched linker.

In certain embodiments, cleavable linking groups are utilized. A cleavable linking group is one which is sufficiently stable outside the cell, but which upon entry into a target cell is cleaved to release the two parts the linker is holding together. In one embodiment, the cleavable linking group is cleaved at least 10 times or more, and in some embodiments, at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the moiety inside the cell, or into the desired compartment of the cell.

A linker can include a cleavable linking group that is cleavable by a particular enzyme. The type of cleavable linking group incorporated into a linker can depend on the cell to be targeted. For example, liver targeting moieties can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In some embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, redox cleavable linking groups are utilized. Redox cleavable linking groups are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular interfering RNA molecule and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a specific embodiment, candidate compounds are cleaved by at most 10% in the blood. In some embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In yet some embodiments, phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(Ork)-O—, —O—P(S)(Ork)-O—, —O—P(S)(SRk)-O—, —S—P(O) (Ork)-O—, —O—P(O) (Ork)-S—, —S—P(O)(Ork)-S—, —O—P(S)(Ork)-S—, —S—P(S)(Ork)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Specific embodiments include —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. Another specific embodiment is —O—P(O)(OH)—O—. These candidates can be evaluated using methods analogous to those described above.

In some embodiments, acid cleavable linking groups, which are linking groups that are cleaved under acidic conditions, are envisioned. In some embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O) O, or —OC(O). A specific embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

In some embodiments, ester-based cleavable linking groups, which are cleaved by enzymes such as esterases and amidases in cells, are envisioned. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In yet further embodiments, peptide-based cleavable linking groups, which are cleaved by enzymes such as peptidases and proteases in cells, are envisioned. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O) NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums.

Synthesis of Interfering RNA

The interfering RNA molecules that can be employed in the methods of the present invention can readily be made using techniques known in the art, for example, using conventional RNA solid phase synthesis. See, for example, U.S. Pat. No. 8,877,917. The polynucleotides of the double-stranded RNA molecules can be assembled on a suitable nucleic acid synthesizer utilizing standard nucleotide or nucleoside precursors (e.g. phosphoramidites). Automated nucleic acid synthesizers are sold commercially by several vendors, including DNA/RNA synthesizers from Applied Biosystems (Foster City, CA), MerMade synthesizers from BioAutomation (Irving, TX, and OligoPilot synthesizers from GE Healthcare Life Sciences (Pittsburgh, PA).

The 2' silyl protecting group can be used in conjunction with acid labile dimethoxytrityl (DMT) at the 5' position of ribonucleosides to synthesize oligonucleotides via phosphoramidite chemistry. Final deprotection conditions are known not to significantly degrade RNA products. All syntheses can be conducted in any automated or manual synthesizer on large, medium, or small scale. The syntheses may also be carried out in multiple well plates or glass slides.

The 2'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydro-fluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is orthogonal to a 5'-O-dimethoxytrityl protecting group, e.g., one stable to treatment with acid. Silyl protecting groups meet this criterion and can be readily removed in a final fluoride deprotection step that can result in minimal RNA degradation.

Tetrazole catalysts can be used in the standard phosphoramidite coupling reaction. Preferred catalysts include e.g., tetrazole, S-ethyl-tetrazole, p-nitrophenyltetrazole.

See also, for example, Trufert et al., Tetrahedron, 52:3005, 1996; and Manoharan, "Oligonucleotide Conjugates in Antisense Technology," in Antisense Drug Technology, ed. S. T. Crooke, Marcel Dekker, Inc., 2001. The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Methods of Treatment

In further embodiments of the present invention, a method of treating a human subject, comprising administering a therapeutic dosage of the antigen binding proteins or antibodies or interfering RNA (e.g., siRNA or shRNA) of the present invention is provided. In one embodiment, the antigen binding proteins are monoclonal antibodies. In one embodiment, the antigen binding proteins are human antibodies. In another embodiment, the antigen binding proteins or antibodies are humanized antibodies. In another embodiment, interfering RNA (e.g., siRNA or shRNA) is administered. As used herein the term "subject" refers to a mammal, including humans, and can be used interchangeably with the term "patient".

Given the results of the Icelandic study presented in the examples below, there need not be any particular further manipulation downstream in a host receiving a therapy involving administering the ASGR inhibitor (e.g., antigen binding proteins or antibodies or RNAi) to the host. That is, in some embodiments, the antibody (or RNAi) need simply be one or more of the antibodies (or RNAi) described herein, which binds to (and inhibits) ASGR (such as ASGR1), and be administered in an amount, and at a frequency sufficient to reduce the risk of cardiovascular disease, myocardial infarction, or other disorders provided herein. In some embodiments, the antibody (or RNAi) is administered in an amount sufficient to result in a lowering of non-HDL cholesterol. In some embodiments, the antibody (or RNAi) is administered in an amount sufficient to result in lowering LDL cholesterol. While not intended to be limiting unless expressed otherwise, below is a description of various embodiments through which ASGR can have an impact on various disorders, and thus, how the various antibodies (or RNAi) provided herein (which can inhibit (e.g., reduce) ASGR function) can have an impact on the various disorders provided herein.

In some embodiments, the ASGR inhibitor (e.g., antigen binding proteins or antibodies or RNAi) operates through ASGR's role in platelet clearance. Inhibiting (e.g., reducing) the receptor results in a reduction in clearance of old platelets. Such older platelets do not coagulate as well as new platelets and as a result, the blood is thinner. As a result, plaques can lessen and there can be a positive impact (e.g., stroke is lessened) for the subject.

In some embodiments, the ASGR inhibitor (e.g., antigen binding proteins or antibodies or RNAi) binds to ASGR to alter inflammation. For example, reducing the ASGR-1 receptor results in a modification of the immune response. Normally, there can be an increase in proinflammatory cytokines. These proinflammatory cytokines are circulating in the native state (one where the ASGR1 receptor is not reduced). However, ALP (alkaline phosphatase) can have an anti-inflammatory role thereby reducing inflammation and coagulopathy systemically. In some embodiments, the mechanism of action involves reducing ASGR1 which increases ALP and therefore reduces inflammation.

In some embodiments, and without intending to be limited by theory (unless expressed otherwise), the ASGR inhibitor (e.g., antigen binding proteins or antibodies or RNAi) can reduce an activity due to ASGR interacting with one or more other molecules, either directly or indirectly. For example, various embodiments for various proteins are provided herein in Examples 18 and 19. As noted above, this selection of proteins can also be useful for determining the effectiveness of the ASGR inhibitor (e.g., antigen binding proteins or antibodies or RNAi) (and/or the amount of the antibody and/or identification of a subject who can respond to the therapy (or RNAi)) by monitoring one or more of these proteins as a Cardiovascular Disease marker. Thus, these markers are useful as markers and, without intending to be limited by theory, in some embodiments, one or more of the proteins disclosed below is the protein through which (directly or indirectly) ASGR1 modulation achieves its benefit for one or more of the disorders provided herein, including cardiovascular disease.

In addition to the marker proteins described in Examples 18 and 19 herein (which also allow for various mechanisms of action and monitoring the effectiveness of various ASGR inhibitors (e.g., antigen binding proteins or antibodies or RNAi) and dosage regimes), the following proteins of interest are those that interact with ASGR, and ASGR-1 in particular, directly by binding to them. Thus, these are additional interactions that can be inhibited (e.g., reduced) for various embodiments provided herein, by various ASGR inhibitors (e.g., antigen binding proteins or antibodies or RNAi). While not intending to be limited by theory (unless explicitly stated otherwise), ASGR-1's binding to one or more of the following proteins can be inhibited (e.g., reduced) by using an ASGR-1 inhibitor (e.g., antigen binding protein or antibody or RNAi) provided herein that inhibits (e.g., reduces) the noted binding. While in some embodiments, the protein interactions are contemplated as resulting mechanisms of action that occur downstream from when ASGR levels are effectively reduced by an ASGR inhibitor (e.g., antigen binding protein or antibody binding or via RNAi), the following list is a list of proteins that directly bind to ASGR1, and thus whose direct binding to ASGR-1 can be inhibited (e.g., reduced) by one or more of the antigen binding proteins or antibodies provided herein (or RNAi). In some embodiments, the ASGR-1 inhibitor (e.g., antigen binding protein or antibody or RNAi) inhibits (e.g., reduces) ASGR-1's binding to one or more of: Alpha-2-HS-glycoprotein (aka Fetuin A) (see Tozawa et al, J Biol Chem (2001) 276:12624-12628); Asialoglycoprotein receptor 1 (see Stockert et al (1977) Science 197:667-668), Orosomucoid (aka alpha-1-acid glycoprotein) (see Tozawa et al, J Biol Chem (2001) 276:12624-12628), Alkaline phosphatase, (see Hardonk M J, Scholtens H B. Histochemistry. 1980; 69(3):289-97 and Scholtens H B, Meijer D K, Hardonk M J. Liver. 1982 March; 2(1):14-21), LDL and chylomicrons (Windler et al Biochem J (1991) 276:79-87), Fibronectin (see Rotundo et al Hepatology (1998) 28:475-485), and IgA (see Stockert et al PNAS (1982) 79:6229-6231). In some embodiments, the ASGR inhibitor (e.g., antigen binding protein or antibody or RNAi) antibody binds to ASGR and inhibits (e.g., reduces) ASGR's interaction with a molecule that has a terminal Gal or GalNAc, including, but not limited to protein ligands, synthetic polysaccharides, solid substrates, etc. In some embodiments, the ASGR inhibitor (e.g., antigen binding proteins or antibodies or RNAi) inhibits (e.g., reduces) ASGR1's ability to bind to an asialylated molecule. In some embodiments, the invention provides a method of treating or preventing a cardiovascular disease comprising administering to a patient in need thereof a therapeutically effective dose of an ASGR inhibitor as described herein. In some embodiments, the cardiovascular disease is coronary artery disease or myocardial infarction. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the relative risk reduction of a cardiovascular event is at least about 5%, at least about 10%, at least about 15%, at least about 20%, at least about 25%, at least about 30%, at least about 35%, at least about 40%, at least about 45%, at least about 50%, at least about 55%, at least about 60% in the patient. Some non-limiting examples of cardiovascular disease include atherosclerotic diseases, such as, for example, coronary heart disease, coronary artery disease, peripheral arterial disease, stroke (ischaemic and hemorrhagic), angina pectoris, cerebrovascular disease, acute coronary syndrome, and myocardial infarction. In some embodiments, the ASGR, ASGR-1 and/or ASGR-2 inhibitors of the present invention are useful in reducing the risk of: nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries. In some embodiments, the ASGR, ASGR-1 and/or ASGR-2 inhibitors of the present invention and methods can be used to reduce the risk of recurrent cardiovascular events.

In some embodiments, the invention provides a method of decreasing the risk of acquiring coronary artery disease or having an MI comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the relative risk reduction of coronary artery disease or MI is at least about 5%, at least about 10%, at least about 15%, at least about 20%, at least about 25%, at least about 30%, at least about 35%, at least about 40%, at least about 45%, at least about 50%, at least about 55%, at least about 60% in the patient.

In some embodiments, the invention provides a method of reducing blood LDL cholesterol levels in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the blood LDL cholesterol level in the patient is reduced by at least about 15%, as compared to a predose level of blood LDL cholesterol in the patient. In some embodiments of this aspect of the invention, the blood LDL cholesterol level of said patient is lowered by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as compared to a predose level of blood LDL cholesterol in the patient.

In some embodiments, the invention provides a method of reducing non-HDL cholesterol levels in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the non-HDL cholesterol level in the patient is reduced by at least about 5%, as compared to a predose level of non-HDL cholesterol in the patient. In some embodiments of this aspect of the invention, the non-HDL cholesterol level of said patient is lowered by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% as compared to a predose level of non-HDL cholesterol in the patient.

In some embodiments, the invention provides a method of increasing ALP levels in a patient comprising administering to a patient in need thereof a therapeutically effective dose of of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the ALP level in the patient is increased by at least about 30%, as compared to a predose level of ALP in the patient. In some embodiments of this aspect of the invention, the ALP level of said patient is increased by at least about at least about 35%, at least about 40%, at least about 45%, at least about 50%, at least about 55%, at least about 60%, at least about 65%, at least about 70%, at least about 75%, at least about 80%, at least about 85%, or at least about 90% as compared to a predose ALP level in the patient. In some embodiments, ALP levels are increased at least about, 1.5×, 2×, 2.5×, 3×, 3.5×, 4×, 4.5×, and 5× over pretreatment.

In some embodiments, the invention provides a method of antagonizing ASGR, ASGR-1 and/or ASGR-2 in a patient comprising administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein.

In some embodiments, a method of treating or preventing a cardiovascular disease is provided and comprises administering to a patient in need thereof a therapeutically effective dose of an ASGR inhibitor as described herein. In some embodiments, the ASGR inhibitor is an inhibitor of ASGR-1. In some embodiments, the ASGR inhibitor is an inhibitor of ASGR-2. In some embodiments, the ASGR inhibitor is an inhibitor of ASGR-1 and ASGR-2. In some embodiments, the ASGR, ASGR-1 and/or ASGR-2 inhibitor is one or more of the antigen binding proteins described herein. In some embodiments, the ASGR, ASGR-1 and/or ASGR-2 inhibitor is an interfering RNA (e.g., siRNA or shRNA) as described herein. In some embodiments, the relative risk reduction of a cardiovascular event is at least about 5%, at least about 10%, at least about 15%, at least about 20%, at least about 25%, at least about 30%, at least about 35%, at least about 40%, at least about 45%, at least about 50%, at least about 55%, at least about 60% in the patient.

The term "treatment" encompasses alleviation of at least one symptom or other embodiment of a disorder, or reduction of disease severity, and the like. An antigen binding protein, in particular a human antibody according to the present invention, need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antigen binding protein or interfering RNA in an amount and for a time sufficient to induce a sustained improvement over baseline of an indicator that reflects the severity of the particular disorder.

The term "prevention" encompasses prevention of at least one symptom or other embodiment of a disorder, and the like. A prophylactically administered treatment incorporating an antigen binding protein, in particular a human antibody according to the present invention, need not be completely effective in preventing the onset of a condition in order to constitute a viable prophylactic agent. Simply reducing the likelihood that the disease will occur or worsen in a subject, is sufficient.

The term "non-HDL cholesterol" encompasses all cholesterol-containing proatherogenic lipoproteins, including LDL cholesterol, very-low-density lipoprotein, intermediate-density lipoprotein, lipoprotein(a), and chylomicron. Non-HDL cholesterol levels are calculated by subtracting HDL cholesterol levels from total cholesterol levels.

As is understood in the pertinent field, pharmaceutical compositions comprising the antigen binding proteins and/or interfering RNA are administered to a subject in a manner appropriate to the indication and the composition. In one embodiment, pharmaceutical compositions comprise the human antibodies of the present invention. In another embodiment, pharmaceutical compositions comprise interfering RNA. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Delivery by inhalation includes, for example, nasal or oral inhalation, use of a nebulizer, inhalation of the antigen binding protein in aerosol form, and the like. Other alternatives include oral preparations including pills, syrups, or lozenges.

Advantageously, the antigen binding proteins or interfering RNA are administered in the form of a composition comprising one or more additional components such as a physiologically acceptable carrier, excipient or diluent. Optionally, the composition additionally comprises one or more physiologically active agents. In various particular embodiments, the composition comprises one, two, three, four, five, or six physiologically active agents in addition to one or more antigen binding proteins (e.g, human antibodies) or interfering RNA.

Kits for use by medical practitioners are provided including one or more antigen binding proteins or interfering RNA and a label or other instructions for use in treating any of the conditions discussed herein. In one embodiment, the kit includes a sterile preparation of one or more human antibodies, or one or more interfering RNA which may be in the form of a composition as disclosed herein, and may be in one or more vials.

Dosages and the frequency of administration may vary according to such factors as the route of administration, the particular antigen binding proteins or interfering RNA employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An antigen binding protein, e.g., monoclonal antibodies, or interfering RNA may be administered, for example, once or more than once, e.g., at regular intervals over a period of time. In particular embodiments, an antigen binding protein or interfering RNA is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein or interfering RNA is administered until the patient manifests a medically relevant degree of improvement over baseline for the chosen indicator or indicators.

One example of therapeutic regimens provided herein comprise subcutaneous injection of an antigen binding protein or interfering RNA once a week, or once every two weeks, or once every month, once every other month, once every three months, once every six months or longer, at an appropriate dosage, to treat a condition in which it is desired to target cells expressing ASGR, ASGR-1 and/or ASGR-2. Weekly or monthly administration of antigen binding protein could be continued until a desired result is achieved, e.g., the subject's symptoms subside. Treatment may resume as needed, or, alternatively, maintenance doses may be administered.

In some embodiments, one or more of the markers in Tables 18.1, 18.2, 19.3, and 19.4 can be used to determine whether or not the amount of ASGR inhibitor (e.g., antigen binding protein and/or antibody and/or RNAi) administered is sufficient for its intended therapeutic application. In some embodiments, when one or more of the alterations in protein level, for the proteins outlined in one or more of Tables 18.1, 18.2, 19.3, and 19.4 changes in response to administering the antigen binding protein, antibody and/or RNAi, the antigen binding protein, antibody and/or RNAi is having an effect in the host. In some embodiments, the amount is sufficient when it alters the level of non-HDL cholesterol to a desired amount or reduces it by a desired amount. In some embodiments, the markers used can be one or more of those in one or more of Tiers 1, 2, 3, 4, and 5 of Table 19.4. In some embodiments, the markers used can be one or more of those in one or more of Tiers 1 and 5 of Table 19.4.

Combination Therapies

Particular embodiments of methods and compositions of the invention involve the use of at least one antigen binding protein and/or interfering RNA and one or more other therapeutics useful for treating or preventing cardiovascular disease, for example. In one embodiment, antigen binding proteins and/or interfering RNA are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient. In certain embodiments, an antigen binding protein or interfering RNA is administered prior to the administration of at least one other therapeutic agent. In certain embodiments, an antigen binding protein or interfering RNA is administered concurrent with the administration of at least one other therapeutic agent. In certain embodiments, an antigen binding protein or interfering RNA is administered subsequent to the administration of at least one other therapeutic agent.

In one embodiment, the at least one antigen binding protein or antibody and/or the interfering RNA is administered to a subject in combination with an anti-PCSK9 antibody (e.g., Repatha®, Praluent®, bococizumab). In another embodiment, the at least one antigen binding protein or antibody and/or the interfering RNA is administered to a subject in combination with at least one other cholesterol-lowering (serum and/or total body cholesterol) agent. In some embodiments, the agents that increase the expression of LDLR, have been observed to increase serum HDL levels, lower LDL levels or lower triglyceride levels. Exemplary agents include, but are not limited to, statins (e.g., atorvastatin, cerivastatin, fluvastatin, lovastatin, mevastatin, pitavastatin, pravastatin, rosuvastatin, simvastatin), Nicotinic acid (Niacin) (NIACOR, NIASPAN (slow release niacin), SLO-NIACIN (slow release niacin)), Fibric acid (LOPID (Gemfibrozil), TRICOR (fenofibrate), Bile acid sequestrants (QUESTRAN (cholestyramine), colesevelam (WELCHOL), COLESTID (colestipol)), Cholesterol absorption inhibitors (ZETIA (ezetimibe)), combining nicotinic acid with statin (ADVICOR (LOVASTATIN and NIASPAN), combining a statin with an absorption inhibitor (VYTORIN (ZOCOR and ZETIA) and/or lipid modifying agents. In some embodiments, the at least one antigen binding protein and/or interfering RNA is combined with PPAR gamma agonists, PPAR alpha/gamma agonists, squalene synthase inhibitors, CETP inhibitors, anti-hypertensives, anti-diabetic agents (such as sulphonyl ureas, insulin, GLP-1 analogs, DDPIV inhibitors), ApoB modulators, MTP inhibitors and/or arteriosclerosis obliterans treatments. In some embodiments, the at least one antigen binding protein and/or interfering RNA is combined with an agent that increases the level of LDLR protein in a subject, such as statins, certain cytokines like oncostatin M, estrogen, and/or certain herbal ingredients such as berberine. In some embodiments, the at least one antigen binding protein and/or interfering RNA is combined with an agent that increases serum cholesterol levels in a subject (such as certain antipsychotic agents, certain HIV protease inhibitors, dietary factors such as high fructose, sucrose, cholesterol or certain fatty acids and certain nuclear receptor agonists and antagonists for RXR, RAR, LXR, FXR). The combination of the two can allow for the undesirable side-effects of other agents to be mitigated by the antigen binding protein or interfering RNA.

Diagnostic Uses

In one embodiment, antigen binding proteins of the invention are useful for detecting the presence of ASGR, ASGR-1 and/or ASGR-2 in a biological sample. The term "detecting" as used herein encompasses quantitative or qualitative detection. In certain embodiments, a biological sample comprises a cell or tissue. In certain embodiments, such tissues include tissues that express ASGR, ASGR-1 and/or ASGR-2 at higher levels relative to other tissues.

In one embodiment, the invention provides a method of detecting the presence of ASGR, ASGR-1 and/or ASGR-2 in a biological sample. In certain embodiments, the method comprises contacting the biological sample with an antigen binding protein of the invention under conditions permissive for binding of an antigen binding protein to ASGR, ASGR-1 and/or ASGR-2, and detecting whether a complex is formed between the antigen binding protein and ASGR, ASGR-1 and/or ASGR-2.

In one embodiment, the invention provides a method of diagnosing a disorder associated with increased or decreased expression of ASGR, ASGR-1 and/or ASGR-2. In certain embodiments, the method comprises contacting a test cell with an antigen binding protein; determining the level of expression (either quantitatively or qualitatively) of ASGR, ASGR-1 and/or ASGR-2 by the test cell by detecting binding of the antigen binding protein to ASGR, ASGR-1 and/or ASGR-2; and comparing the level of expression of ASGR, ASGR-1 and/or ASGR-2 by the test cell with the level of expression of ASGR, ASGR-1 and/or ASGR-2 by a control cell (e.g., a normal cell of the same tissue origin as the test cell or a cell that expresses ASGR, ASGR-1 and/or ASGR-2 at levels comparable to such a normal cell), wherein a higher or lower level of expression of ASGR, ASGR-1 and/or ASGR-2 by the test cell as compared to the control cell indicates the presence of a disorder associated with increased or decreased expression of ASGR, ASGR-1 and/or ASGR-2. In certain embodiments, the test cell is obtained from an individual suspected of having a disorder associated with increased or decreased expression of ASGR, ASGR-1 and/or ASGR-2.

In certain embodiments, a method of diagnosis or detection, such as those described above, comprises detecting binding of an antigen binding protein of the invention to ASGR, ASGR-1 and/or ASGR-2 expressed on the surface of a cell or in a membrane preparation obtained from a cell expressing ASGR, ASGR-1 and/or ASGR-2 on its surface. In certain embodiments, the method comprises contacting a cell with an antigen binding protein under conditions permissive for binding of an antigen binding protein of the invention to ASGR, ASGR-1 and/or ASGR-2, and detecting whether a complex is formed between the antigen binding protein of the invention and ASGR, ASGR-1 and/or ASGR-2 on the cell surface. An exemplary assay for detecting binding of an antigen binding protein of the invention to ASGR, ASGR-1 and/or ASGR-2 expressed on the surface of a cell is a "FACS" assay.

Certain other methods can be used to detect binding of antigen binding protein of the invention to ASGR, ASGR-1 and/or ASGR-2. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, antigen binding proteins of the invention are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, antigen binding proteins of the invention are immobilized on an insoluble matrix. Immobilization entails separating the antigen binding protein of the invention from any ASGR, ASGR-1 and/or ASGR-2 that remains free in solution. This conventionally is accomplished by either insolubilizing the antigen binding protein of the invention before the assay procedure, as by adsorption to a water-insoluble matrix or surface (see, e.g., Bennich et al., U.S. Pat. No. 3,720,760), or by covalent coupling (for example, using glutaraldehyde cross-linking), or by insolubilizing the antigen binding protein of the invention after formation of a complex between the antigen binding protein of the invention and ASGR, ASGR-1 and/or ASGR-2, e.g., by immunoprecipitation.

The invention having been described, the following examples are offered by way of illustration, and not limitation.

Numerous sequences have been provided herein. Where there is a discrepancy in the sequences, the sequences in the tables presented within the figures control, unless there is an indication otherwise. If there is any unintended difference between the same consensus sequences, the consensus sequences as provided in the figures (from the tables within the figures) will control (unless indicated otherwise). For any further descrepancies (rather than just alternative sequences) the sequences within Tables 1-7 will control, unless designated otherwise. The figures contain multiple sequences, sequence alignments and sequence components of various nucleic and amino acid sequences. The present specification references this information in terms of the designated tables and/or the designated figures. Either reference (via figure or table) can be used and either designation (figure or table) will indicate the alternative designation as well, where appropriate. Thus, FIG. 48 designates Table 1, FIG. 49 designates Table 2, FIG. 50 designates Table 3, FIG. 51 designates Table 4, FIG. 52 designates Table 5, FIG. 53 designates Table 6, FIG. 54 designates Table 7, FIG. 55 designates Tables 19A, 19B, 19C, 20A, 20B, and 20C, FIG. 56 designates Tables 21-48, and FIG. 57 designates Tables 49-134, and vice versa. As such, any discussion herein in regard to the above figures or tables is interchangeable with respect to the "table" or "figure" nomenclature.

EXAMPLES

Example 1—Identification of Rare Sequence Variants that Disrupt ASGR-1 Function and Lower Non-HDL Cholesterol and Protect Against Coronary Artery Disease The level of circulating non-high density lipoprotein (non-HDL) cholesterol is heritable and strongly correlated with the risk of coronary artery disease (CAD) and myocardial infraction (MI). Whole-genome sequencing offers the potential to search for rare sequence variants that have large effects on serum lipid levels and hence the risk of cardiovascular disease, such as CAD and MI.
Methods
Study Participants:
Details of the population sample sets from Iceland, Denmark and The Netherlands, used to measure the various lipids traits (non-HDL cholesterol, HDL cholesterol, LDL cholesterol and triglycerides), alkaline phosphatase (ALP), ferritin, and vitamin B12, are outlined in Table 1.2. The dataset for ferritin is not shown. The coronary artery disease case-control sample sets that were a part of the study are outlined in Table 1.1.
Icelandic Study Population Study participants were enrolled as part of various genetics programs at deCODE. Blood lipid levels (total cholesterol, non-high density lipoprotein cholesterol (non-HDL-C), low density lipoprotein cholesterol (LDL-C), high density lipoprotein cholesterol (HDL-C) and triglycerides), alkaline phosphatase and vitamin B12 levels were obtained from three of the largest laboratories in Iceland: 1) Landspítali—The National University Hospital of Iceland (LUH), Reykjavík (measurements performed between the years 1993 and 2012, hospitalized and ambulatory patients), 2) The Laboratory in Mjódd (RAM), Reykjavík (measurements performed between 2004 and 2012, ambulatory patients) and 3) Akureyri Hospital, The Regional Hospital in North Iceland, Akureyri (performed between 2004 and 2010, hospitalized and ambulatory patients). Information on the participants is outlined in Table 1.2. Lipid levels were adjusted for sex, year of birth and age at measurement, lipid lowering medication and measurement site, using the average of multiple measurements for an individual, and then normalized to a standard normal distribution using quantile normalization. To obtain effect estimates in mmol/L the estimates from the regression analysis were multiplied by the estimated standard deviation of lipid level in the population. Given their approximately log-normal distribution, triglyceride levels were log-transformed before adjustment and the corresponding effect estimates are presented as percentage change instead of units of mmol/L. The total number of individuals with non-HDL cholesterol, LDL cholesterol, HDL cholesterol and triglycerides in Iceland is shown in the Table 1.3 below. For each lipid, the number of chip-typed and directly imputed individuals and those with familial imputations is also shown.

TABLE 1.3

Lipid levels of Icelandic Study Participants

| | Non-HDL-C | LDL-C | HDL-C | Triglycerides |
|---|---|---|---|---|
| Total number | 119,146 | 53,841 | 119,514 | 80,111 |
| Direct imputation | 69,277 | 51,029 | 69,414 | 59,678 |
| Familial imputation | 49,869 | 2,812 | 50,100 | 20,433 |

The total number of Icelandic individuals with lipid values used in the study and the breakdown into those that were chip-typed and directly imputed (Direct imputation) and those that were first and second degree relatives of chip-typed individuals and had their genotypes inferred based on genealogy (Familial imputation).

Non-HDL cholesterol was obtained by subtracting HDL cholesterol from total cholesterol and measures the amount of cholesterol carried within all atherogenic lipoprotein particles (VLDL, IDL, LDL, chylomicrons and Lp(a)). The LDL cholesterol was calculated using the Friedewald equation (for triglyceride levels <4.00 mmol/L) (Friedewald, W. T., Levy, R. I. & Fredrickson, D. S. Estimation of the concentration of low-density lipoprotein cholesterol in plasma, without use of the preparative ultracentrifuge. Clin. Chem. 18, 499-502 (1972)). Total cholesterol and HDL-cholesterol values are a mixture of fasting and non-fasting values, whereas triglycerides are fasting values exclusively.

Coronary artery disease (CAD) was defined as a) individuals in the MONICA registry who suffered myocardial infarction (MI) before the age of 75 in Iceland between 1981 and 2002 and satisfied the MONICA criteria (Gudbjartsson, et al., Large-scale whole-genome sequencing of the Icelandic population. Nature genetics 2015), b) subjects with CAD discharge diagnoses (ICD 9 codes 410.*, 411.*, 412.*, 414.* or ICD 10 codes I20.0, I21.*, I22.*, I23.*, I24.*, I25.*) from LUH, c) subjects diagnosed with significant angiographic CAD (see defined below) identified from a nationwide clinical registry of coronary angiography and percutaneous coronary interventions at LUH between the years 1987 and 2012, d) subjects undergoing coronary artery bypass grafting (CABG) procedures at LUH between the years 2002 and 2011 or e) cause of death or contributing cause of death listed as MI or CAD (ICD 9 or 10 codes) on death registries between the years 1996 and 2009. Coronary angiograms in the nationwide registry were evaluated by an interventional cardiologist. Patients were considered to have significant angiographic CAD if one or more of the three major epicardial coronary vessels or the left main coronary artery was found to have at least 50% stenosis by visual estimation.

Non-Icelandic Study Populations

Characteristics of the non-Icelandic sample sets are outlined in Table 1.1 and Table 1.2. All the studies outlined in Tables 1.1 and 1.2 were approved by appropriate bioethics and/or data protection authorities. For samples from the Nijmegen Biomedical Study, Netherlands, the lipid values (namely, total cholesterol, HDL-cholesterol and triglycerides) were all non-fasting values. For samples from the Danish Inter99 and Addition studies, the lipid values were all fasting values. All participating subjects donating biological samples signed informed consents. Personal identities of the phenotypes and biological samples were encrypted by a third party system provided by the Icelandic Data Protection Authority.

Data Generation and Analysis

Whole-Genome Sequencing, SNP Calling, and Imputation

The Icelandic samples were genotyped using Illumina microarrays (Samani N J et al., Genomewide association analysis of coronary artery disease. The New England journal of medicine 2007; 357:443-53). The whole-genomes of 2,636 Icelanders were sequenced using the standard TruSeq methodology (Illumina) to a mean depth of at least 10× (median 20×) (Samani N J et al., Genomewide association analysis of coronary artery disease. The New England journal of medicine 2007; 357:443-53). For improved sequencing coverage of the GC-rich intron 4 in ASGR-1 gene, the whole-genome sequence data generated for 738 Icelanders was analyzed using TruSeq PCR-free method from Illumina (mean depth of 30×). The del12 variant in intron 4 of ASGR-1 was detected in this dataset.

Single-Track Assay SNP and Microsatellite Genotyping:

We performed single SNP genotyping of rs186021206, using the Centaurus (Nanogen) platform (Gretarsdottir S, et al., Genome-wide association study identifies a sequence variant within the DAB2IP gene conferring susceptibility to abdominal aortic aneurysm. Nature genetics 2010; 42:692). The del12 variant was genotyped using a PCR based method with the following primers: forward primer (NED labelled) 5'-TTCATCTTTCTTCCCACATTGC-3' (SEQ ID NO: 32600), reverse primer 5'-GGGCCTGAGAGA-GACGTTCA-3' (SEQ ID NO: 32601). An internal size standard was added to the resulting PCR products and the fragments were separated and detected on an Applied Biosystems model 3730 sequencer, using in-house Allele Caller software.

Statistical Analyses:

Associations between imputed genotypes and serum lipids (non-HDL cholesterol, HDL cholesterol, LDL cholesterol and triglycerides), ALP, ferritin and vitamin B12 levels in the Icelandic dataset were tested using a generalized linear regression, assuming an additive genetic model (Samani N J et al., Genomewide association analysis of coronary artery disease. The New England journal of medicine 2007; 357:443-53; and Olsen M H, et al., N-terminal pro-brain natriuretic peptide, but not high sensitivity C-reactive protein, improves cardiovascular risk prediction in the general population. European heart journal 2007; 28:1374-81). For the Icelandic dataset, logistic regression was used to test for association between the del12 variant and coronary artery disease and myocardial infarction, treating the disease status as the response and the number of copies of del12 an individual carries as the explanatory variable. Coronary artery disease case-control association analysis for the non-Icelandic sample sets was done using the NEMO software (Jorgensen A B, et al., Loss-of-function mutations in APOC3 and risk of ischemic vascular disease. The New England journal of medicine 2014; 371:32-41) assuming a multiplicative risk model. Results for the Icelandic and the non-Icelandic sample sets were combined using a Mantel-Haenszel fixed effects model. To estimate the effect of the del12 variant on myocardial infarction-free survival, Kaplan-Meier curves were estimated for survival to first myocardial infarction in heterozygous carriers and non-carriers (Hoogendoorn E H, et al., Thyroid function and prevalence of anti-thyroperoxidase antibodies in a population with borderline sufficient iodine intake: influences of age and sex. Clinical chemistry 2006; 52:104-11) by dividing the corresponding chi-square statistic by 1.36 for non-HDL cholesterol, 1.57 for HDL cholesterol, 1.40 for triglycerides, 1.53 for ALP, 1.30 for vitamin B 12, 1.71 for coronary artery disease and 1.48 for myocardial infarction.

To obtain a reliable imputation of the del12 variant, 3,799 Icelandic individuals were genotyped for the del12 variant and those genotypes were used as a training set for imputation of the del12 variant into the rest of the Icelandic population. The imputation information for del12 was 0.99.

The Icelandic samples were genotyped using Illumina microarrays as described above (Gudbartssoon, D F, et al., Large Scale whole-genome sequencing of the Icelandic population. Nature Genetics 2015). The whole-genomes of 2,636 Icelanders were sequenced using Illumina standard TruSeq methodology to a mean depth of at least 10× (median 20×) (Di Angelantonio E, et al., Major lipids, apolipoproteins, and risk of vascular disease. Jama 2009; 302:1993-2000). A total of 35.5 million autosomal SNPs and INDEL's were identified using the Genome Analysis Toolkit version 2.3.9. Information about haplotype sharing was used to improve variant genotyping, taking advantage of the fact that all sequenced individuals had also been chip-typed and long-range-phased. Variants were annotated using Ensembl release 72 and Variant Effect Predictor (VEP) version 2.8. Of the 35.5 million sequence variants found, 25.3 million variants passed the quality threshold and were imputed into 104,220 Icelanders who had been genotyped using Illumina chips. Additionally, using the Icelandic genealogy, genotype probabilities were calculated for 294,212 untyped individuals who are first and second degree relatives of the chip-typed individuals born after 1880 (Gudbartssoon, D F, et al., Large Scale whole-genome sequencing of the Icelandic population. Nature Genetics 2015). The informativeness of genotype imputation (imputation information) was estimated by the ratio of the variance of imputed expected allele counts and the variance of the actual allele counts:

$$\frac{Var(E(\theta \mid chip\ data))}{Var(\theta)},$$

where $\theta$ is the allele count. $Var(E(\theta|chip\ data))$ was estimated by the observed variance of the imputed expected counts and $Var(\theta)$ was estimated by $p(1-p)$, where p is the allele frequency.

For improved sequencing coverage of the GC-rich intron 4 in ASGR-1 gene, whole-genome sequence ("WGS") data generated for 738 Icelanders was analyzed using TruSeq PCR-free method from Illumina (mean depth of 30×). This PCR-free method gave much better coverage of GC-rich regions including the ASGR-1 intron 4. The del12 variant in intron 4 of ASGR-1 was detected in five individuals in this dataset.

To provide improved coverage of the associated region (1 Mb centered on ASGR-1), a new dataset was analyzed that included an additional 5,817 WGS individuals (on top of the 2,636 WGS Icelanders). These additional individuals were sequenced with either Illumina TrueSeq PCR free or TrueSeq Nano methods. These Illumina TrueSeq methods give enhanced sequence coverage as compared to the standard Illumina TrueSeq method (median sequencing depth 32×). The identified sequence variants were imputed into 150,656 Icelandic chipped-typed individuals, and with the use of genealogy information, into primary and secondary relatives of chip-typed individuals that were untyped. In this expanded dataset, we identified another rare (0.027%), novel variant, W158X. The W158X variant is a four bp INDEL in exon 7 of ASGR-1 (NM_001671.4:c.469_472dupAACT) that causes frameshift and introduction of premature stop codon at amino acid 158 out of the 291 amino acid full length protein (NP_001662.1:p.Trp158X). A total of 345 individuals were Sanger-sequenced based on the imputation predicted carriers and non-carriers of c.469_472dupAACT. In this dataset, 79 c.469_472dupAACT carriers and 270 non-carriers were identified. This genotype data was then used to re-impute the variant into the Icelandic dataset. For non-HDL cholesterol, a larger sample set (n=136,261) was used in the association analysis outlined in Tables 1.4A and 1.4B.

Associations between imputed genotypes and serum lipids (non-HDL cholesterol, HDL cholesterol, LDL cholesterol and triglycerides), ALP and vitamin B12 levels in the Icelandic dataset were tested using a generalized linear regression, assuming an additive genetic model (Gudbjartsson D F, et al., Large-scale whole-genome sequencing of the Icelandic population. Nature genetics 2015; and Steinthorsdottir V, et al., Identification of low-frequency and rare sequence variants associated with elevated or reduced risk of type 2 diabetes. Nature genetics 2014; 46:294-8). All measurements were adjusted for age, sex and measurement site, and average was taken over the available measurements after adjustment and inverse normal transformation. The lipid measurements were further adjusted for statin use. Removing individual known to take lipid lowering drugs in the Icelandic dataset did not alter the association with non-HDL cholesterol. The effect, in standardized units, changed from −0.29 (95% CI −0.38, −0.20; P=4.0×10$^{-11}$) to −0.30 (−0.39, −0.21; P=6.7×10$^{-11}$). This amounted to excluding 16,295 individuals, out of 119,146 individuals with non-HDL cholesterol information.

The lipid, ALP and vitamin B12 measurements from the Danish Inter99 study, ADDITION Denmark screening cohort, and the Nijmegen biomedical study, were adjusted and transformed in the same way and tested for association with allele count of del12 and rs186021206 using the linear regression implemented in the R software package. Results from the different populations were combined using the inverse variance fixed-effects method with METAL (Willer C J, et al., METAL: fast and efficient meta-analysis of genomewide association scans. Bioinformatics 2010; 26:2190-1). Effect estimates from the regression analysis are expressed in units of standard deviation (SD). To obtain effect estimates in mg/dL for non-HDL cholesterol, LDL cholesterol and HDL cholesterol, the estimates from the regression analysis were multiplied by the estimated SD of the population distributions. Triglyceride, ALP and vitamin B12 levels were log-transformed before adjustment as their distributions are approximately log-normal, and the corresponding effect estimates are presented as percentage change.

For the Icelandic dataset, logistic regression was used to test for association between the del12 variant and coronary artery disease and myocardial infarction, treating the disease status as the response and the number of copies of the deletion an individual carries as the explanatory variable. Other available individual characteristics that correlate with disease status were also included in the model as nuisance variables (Gudbjartsson D F, et al., Large-scale whole-genome sequencing of the Icelandic population. Nature genetics 2015). Coronary artery disease case-control association analysis for the non-Icelandic sample sets was done using the NEMO software (Gretarsdottir S, et al., The gene encoding phosphodiesterase 4D confers risk of ischemic stroke. Nature genetics 2003; 35:131-8) assuming a multiplicative risk model. Results for the Icelandic and the non-Icelandic sample sets were combined using a Mantel-Haenszel fixed-effects model. Heterogeneity in the effect estimate was tested assuming that the estimated odds ratios for different groups follows a log-normal distribution using a likelihood ratio test with degrees of freedom equal to the number of groups compared minus one.

To estimate the effect of the del12 variant on myocardial infarction free survival, we estimated the Kaplan-Meier curves for survival to first myocardial infarction in heterozygous carriers and non-carriers stratified by sex and tested the difference in survival between carriers and non-carriers using the Cox proportional model. The analysis was performed using the survival library in the R software package. The survival analysis was based on 87,718 chip genotyped Icelanders and 44,655 Icelandic first and second degree relatives of chip typed individuals after restricting our analysis to those who lived to be at least 40 years old. Death was treated as a censoring event.

Functional Characterization of the del12 Variant in ASGR-1 cDNA Preparation, Amplification, Sanger Sequencing and Next Generation Sequencing:

RNA was isolated from blood samples from carriers and non-carriers of del12. Following cDNA generation, the region between exon 3 and 5 in ASGR-1 was PCR amplified and the identified PCR products (two for del12 carriers and one for non-carriers) were Sanger sequenced using standard methodology to determine the sequence difference between the identified cDNA products. To quantify the ratio between the two amplified cDNA PCR products, they were sequenced using Illumina MiSeq instrument coupled with the MiSeq v2 reagent kit.

Western Blot Analysis:

The wild type ASGR-1 cDNA and ASGR-1 cDNA with the 22 bp deletion were transiently overexpressed in HeLa cells to determine if ASGR-1 transcripts with the 22 bp deletion generated stable truncated ASGR-1 protein as evaluated by western blot analysis.

RNA was isolated from blood samples using a Qiagen RNA maxi kit. Concentration and quality of the RNA was determined using an Agilent 2100 Bioanalyzer (Agilent Technologies), all samples had RIN values over 7. Following cDNA generation, the region between exon 3 and 5 in ASGR-1 was PCR amplified using the Advantage® 2 Polymerase kit (Clontech) with the forward primer, CACTCAGGTCCTTCTGCTGTTTC (SEQ ID NO: 32602) and the reverse primer, 5'-ACCTCGCCTCCTCCTGCT-3' (SEQ ID NO: 32603). The resulting products were resolved on agarose gel and the identified PCR products (two for del12 carriers and one for non-carriers) were Sanger sequenced using standard methodology to determine the sequence difference between the identified cDNA products. To quantitate the ratio between the two amplified cDNA PCR products, they were sequenced using Illumina MiSeq instrument coupled with the MiSeq v2 reagent kit.

Transient Overexpression of Wild Type and Mutated ASGR-1 Harbouring the 22 bp Deletion at the End of Exon 4 in HeLa Cells.

Generation and Cloning of Wild Type and Mutated ASGR-1 cDNA:

cDNA of ASGR-1 was obtained by PCR on human liver marathon ready cDNA (BD biosciences Clontech). The primers used were Forward 5'GCCAGCCCTATCATGAC-CAA'3 (SEQ ID NO: 32604) and Reverse 5'GCAGGTCGAGGCATTGAAGA'3 (SEQ ID NO: 32605). The resulting cDNA contained all exons including the start and stop codons of ASGR-1. PCR product was run on 1.6% Agarose gel and a band of the correct size was excised out and purified using QIAquick gel extraction kit (QIAGEN 28704) following the manufacturer's protocol. For cloning of ASGR-1 cDNA into pcDNA3.1/V5-His TOPO vector (Invitrogen K4800-01), 2 µl of the gel extraction product was used and the manufacturer's protocol was followed resulting in pcDNA3.1_ASGR-1_WT. Transformed TOP10 chemically competent cells (Invitrogen C4040-10) were plated on LB plates containing 50 µg/ml ampicillin. Colonies were expanded in 3 ml LB medium containing 50 µg/ml ampicillin. Plasmids were purified using QIAGEN plasmid mini kit (QIAGEN 12125) following the manufacturer's protocol. The plasmid sequence was confirmed by Sanger sequencing using the following sequencing primers: T7: 5'TAATACGACTCAC-TATAGGG'3 (SEQ ID NO: 32606), BGH: 5'TAGAAGGCACAGTCGAGG'3 (SEQ ID NO: 32607) and ASGR-1: 5'GAGGCAATGTGGGAAGAAAGATG'3 (SEQ ID NO: 32608)

Introduction of 22 bp Deletion in ASGR-1:

In order to generate a cDNA representative of the del12 carrier mRNA, targeted mutagenesis was performed. The Q5 Site-directed mutagenesis kit (New England BioLabs E0554S) and the pcDNA3.1_ASGR-1_WT plasmid was used as a template. In short, a PCR reaction was performed using the following primers 5'GAGGCAATGTGG-GAAGAAAGATGAAGTCG'3 (SEQ ID NO: 32609) and 5'CTGGGCCTCCGTGCTCGC'3 (SEQ ID NO: 32610), resulting in a double-stranded DNA fragment representing the entire pcDNA3.1_ASGR-1_WT plasmid lacking the 22 bp at the end of exon 4. Following the manufacturers recommendation, 1 uL of the PCR reaction was used in the KLD reaction (New England BioLabs E0554S) wherein the PCR fragment is phosphorylated, re-circularized and the non-mutated template plasmid is removed. Mutated plasmids were transformed into NEB 5-alpha Competent cells (New England BioLabs C2987H) and plated on LB plates containing 50 µg/ml ampicillin. Colonies were expanded in 3 ml LB medium containing 50 µg/ml ampicillin. Plasmids were purified using QIAGEN plasmid mini kit (QIAGEN 12125) following the manufacturer's protocol. ASGR-1_22bp_del sequence was confirmed by Sanger sequencing.

Expression of ASGR-1 in Cultured Cells:

Two days prior to transfection, 100,000 HeLa cells (Public Health England 93021013) were seeded into each well of a 6-well plate in 3 mL of DMEM medium (11995-065, ThermoFisher) supplemented with 10% fetal calf serum (ThermoFisher 10500-064) and 50 units/mL penicillin and 50 ug/mL streptomycin (ThermoFisher 15070-063). Cells were incubated at 37° C. and 5% $CO_2$ in a humidified incubator.

The day before transfection, media was replaced with the without antibiotics. On the day of transfection, for each transfected well, 2.5 ug of plasmids containing ASGR-1_WT or ASGR-1_del22 cDNA were diluted in 125 uL Opti-Mem medium (ThermoFisher 31985-047) and 5 uL of P3000 reagent (ThermoFisher L3000-008). Next, 3.75 uL Lipofectamine 3000 (ThermoFisher L3000-008) were mixed with 125 uL of Opti-Mem. Subsequently, the diluted plasmid solution was mixed with the Lipofectamine 3000 solution at a 1:1 ratio and incubated at room temperature for 5 minutes before the addition of 250 uL of the combined solution to each transfected well.

24 hours post transfection, the spent media was replaced with fresh without antibiotics. Selected wells were supplemented with 10 uM MG132 (TOCRIS 1748) for 4.5 hours prior to harvesting of cells. 48 hours post transfection cells were harvested for analysis by washing wells 2× with PBS (ThermoFisher 14190-250) followed by an 8 minute incubation with 1 mL of 0.5 mM EDTA in PBS (ThermoFisher 15575-020). Next, the EDTA solution was aspirated and cells dislodged by pipetting of 2 mL of fresh media. 3×6-wells were pooled for each experimental condition and cells were spun down at 300× g for 5 minutes. The equivalent of 2×6-wells were lysed in 200 uL of RIPA buffer for Western blot analysis. The remainder of cells were split in two and lysed in 300 uL RLT buffer (Qiagen 74106) or 900 uL Tissue and Cell lysis solution (Epicentre MTC096H) and snap frozen on dry ice for RNA and DNA extraction respectively. Three different transient expression experiments were done and all gave the same results.

Quantitative PCR Analysis:

RNA was isolated from cells using the RNeasy Mini Kit (Qiagen 74106) according to manufacturer's recommendations, and concentration and quality was determined with Nanodrop 1000 spectrophotometer (Thermo Scientific). cDNA was synthesized using the High capacity cDNA reverse transcriptase kit (ThermoFisher). DNA was isolated from cells using the MasterPure DNA Purification Kit (Epicentre MCD85201) according to manufacturer's recommendation.

Analysis of gene expression and transfection efficiency was performed on total cDNA and DNA respectively, with real-time PCR on an ABI Prism 7900HT Sequence Detection System (ThermoFisher) using forward (AGACCTTCAGCATCTGGACAATG (SEQ ID NO: 32611)) and reverse (CGAGGTCCGGAGCAGAGA (SEQ ID NO: 32612)) primers and fluorescent labelled probe spanning exon junction 2-3 of the ASGR-1 gene (6FAM-CAGAAAAGGGCCACCTC-MGB (SEQ ID NO: 32613) (ThermoFisher). Human betaActin assay (ThermoFisher 4326315E) was run in parallel to verify normalization of input cDNA and DNA.

Western Blot Analysis:

Cells corresponding to two wells of a 6 well plate were lysed using 200 µl of RIPA buffer with 1:100 Halt protease and phosphatase inhibitor cocktail (Thermo Scientific 78442). Lysates were kept on ice for 10 min with agitation followed by sonication for 20 sec (Branson 2510) and additional agitation on ice for 10 min. Lysates were spun down at 4° C. for 15 min at 14,000× g. Total protein amount of lysates was estimated using the Pierce BCA protein assay kit (Thermo Scientific 23227). Samples were prepared using Novex Bolt LDS sample buffer (4×) (Life technologies B0007) and Novex Bolt sample reducing agent (10×) (Life technologies B0009) and run on Novex Nupage 4-12% Bis-Tris gel (Life technologies NP0335BOX). Total protein amount per lane was 24 μg and PageRuler (Thermo scientific 26616) was used to estimate protein size. The gel was run at a constant of 200V for 50 min. Proteins were transferred to a nitrocellulose membrane (Life technologies IB23002) using iBlot2 (Life technologies). Membranes were allowed to dry and were then hydrated with MQ water before blotting. Membranes were blocked for 1 hour at room temperature using Odyssey blocking buffer PBS (Li-Cor 927-40000). Primary antibodies used were α-ASGR-1 (Sigma-Aldrich HPA011954) 1:500 (recognizes amino acid 1-41) and α-beta-actin (Abcam ab6276) 1:5000 incubated in blocking buffer with the addition of 0.1% Tween for 3 hours at room temperature. Secondary antibodies used were α-Rabbit 680RD (Li-Cor 926-68073) and α-Mouse 800CW (Li-Cor 926-32212) both 1:20,000 in PBST+0.01% SDS for 1 hour at room temperature. After washing the membrane it was allowed to dry and then scanned using the Odyssey infrared imaging system (Li-Cor Biosciences).

Other Diseases and Traits in deCODE Database:

The deCODE Genetics phenotype database contains medical information on diseases and traits obtained through collaboration with specialists in each field. This includes information on cardiovascular diseases (e.g., myocardial infarction, coronary arterial disease, peripheral arterial disease, atrial fibrillation, sick sinus syndrome and stroke), metabolic disorders (e.g., obesity, diabetes, and metabolic syndrome), psychiatric disorders (e.g., schizophrenia, bipolar disorder, anxiety and depression), addictions (e.g., nicotine, alcohol), inflammatory diseases (e.g., rheumatoid arthritis, lupus, and asthma), musculoskeletal disorders (e.g., osteoarthritis, osteoporosis), eye diseases (e.g., glaucoma), kidney diseases (e.g., kidney stones, kidney failure) and 29 types of cancer. Anthropometric measures have also been collected through several of these projects. Routinely measured traits from patient workups (e.g., sodium, potassium, bicarbonate, calcium, phosphate, creatinine, blood cell counts, hemoglobin, hematocrit, immunoglobulins, iron, vitamins, lipids, liver function tests and more) were obtained from the Landspitali University Hospital, Reykjavik, and the Icelandic Medical Center Laboratory in Mjodd (Laeknasetrid), Reykjavik. The number of independent and uncorrelated secondary traits tested for association with del12 amounts to 400.

Results

Association of Sequence Variants with Non-HDL Cholesterol Levels

Sequence variants were first identified through whole-genome sequencing ("WSG") of 2,636 Icelanders to a median depth of 20×. These variants were imputed (assisted by long-range phased haplotypes) into the genomes of 104,220 Icelanders who had been genotyped using Illumina single nucleotide polymorphism (SNP) arrays. In addition, Icelandic genealogical information was used to calculate genotype probabilities for 294,212 close relatives to those genotyped. Using these data we screened for novel rare variants that associated with non-HDL cholesterol levels (n=119,146). A set of seven correlated (pairwise $r^2$>0.7) rare non-coding SNPs on chromosome 17p13.1 associated with non-HDL cholesterol level. The seven variants span 80 kb, including the asialoglycoprotein receptor 1 and 2 (ASGR-1 and ASGR-2) genes. The strongest association was represented by rs186021206 (minor allele frequency (MAF) =0.43%) located downstream of ASGR-1 that associates with 8.9±1.5 mg/dl lowering of non-HDL cholesterol ($P=1.4\times10^{-9}$) (Table 1.4B).

The associated region was well covered by the whole-genome sequencing except for intron 4 of ASGR-1. This intron is 79 base pairs (bp) long and very GC rich. To explore this region further 738 individuals were whole genome sequenced with PCR-free sequencing (Illumina), that gave enhanced coverage of the intron and led to the identification of a 12 bp deletion within the intron; NM_001671.4:c.284-36_283+33delCTGGGGCTGGGG here after referred to as del12. Following direct genotyping of del12 and imputation into the Icelandic dataset, we observed that del12 (MAF=0.41%) is highly correlated with rs186021206 ($r2=0.86$) and the six other correlated SNPs and associates even more strongly with lowering of non-HDL cholesterol levels (decrease of 10.2±1.5 mg/dl, P=2.5× 10-10) (Table 1.9A). Del12 also increases HDL cholesterol and decreases triglyceride (TG) levels, albeit to a much lesser degree than for non-HDL cholesterol (Tables 1.4A and 1.9B). None of the seven SNPs maintained a significant association with non-HDL cholesterol after adjusting for del12 indicating that del12 is sufficient to explain the non-HDL association.

To validate the del12 association with non-HDL cholesterol levels, del12 in samples from The Netherlands (Nijmegen Biomedical Study 18) and Denmark (Danish Inter9919 and Danish Addition study20) were genotyped. Del12 associated with non-HDL cholesterol in each sample set with similar effect size as in Iceland (Table 1.2, Tables 1.4A and 1.4B and Table 1.9B). When all three datasets were combined with the Icelandic discovery data, it was established that del12 lowers non-HDL cholesterol by 11.6±1.5 mg/dl ($P=1.0\times10^{-16}$) (Table 1.9B).

To identify additional additional loss of function variants in ASGR-1, an extended dataset was screened based on sequence variants identified through whole-genome sequencing ("WSG") of an additional group of 5,817 WGS Icelanders on top of the 2,636 described above. In this dataset, a rare four bp insertion mutation was identified; namely, MAF=0.027%; NM_001671.4: c.469_472dupAACT. As mentioned throughout, this frameshift mutation introduces a premature stop codon at amino acid 158 out of the 291 amino acid full length protein (NP_001662.1:p.W158X). Potential carriers and non-carriers were directly genotyped using Sanger sequencing. Those genotypes were then used to re-impute p.W158X into 150, 656 Icelandic chipped typed individuals and their first and second degree relatives. In this dataset, c.469_472dupAACT associates significantly with a decrease in non-HDL cholesterol (-21.6 mg/dL, 95% CI-34.2 to -9.6) and an increase in ALP (45.3% increase, 95% CI 20.4 to 68.2, $P=7.9\times10^{-6}$) (Table 1.8). The direction of the effects of c.469_472dupAACT and the effect sizes are similar to that of del12 (Table 1.8). Given that a single test was performed, these results provide a significant replication of the ASGR-1 loss of function effect on non-HDL and ALP. Furthermore, since W158X is not correlated with del12 (i.e. there was no overlap between individuals carrying W158X and del12), the W158X variant provides yet further proof that the loss of function in the ASGR-1 gene is responsible for the observed changes in non-HDL, Triglycerides, Alkaline Phosphatase, Ferritin and Vitamin B12 levels. For coronary artery disease, the odds ratio for W158X (c.469_472dupAACT) was 0.65 (95% CI 0.26 to 1.40; P=0.24). As mentioned above, the W158X (c.469_472dupAACT) variant is independent of del12 and none of the 79 carriers found in Iceland carried del12. The variant also appears to be specific to the Icelandic population as it is not detected in large population databases such as (Exome Aggregation Consortium (ExAC), Exome Variant Server (EVS), Genomes of the Netherlands (GoNL) and dbSNP.

Figure 4:
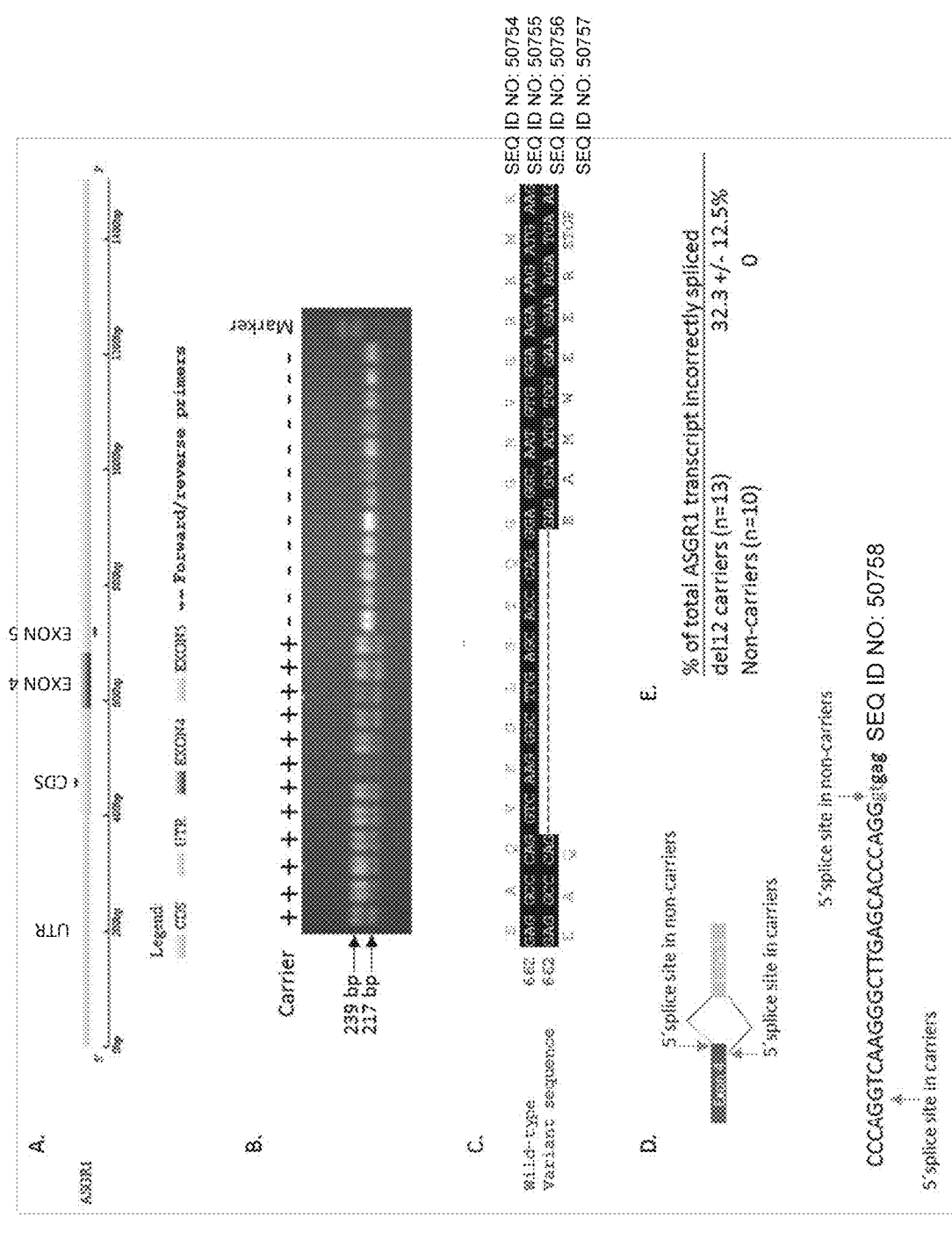
FIG. 4. The del12 variant is associated with a splicing error and frameshift in ASGR-1. (A) Overview of the structure of the ASGR-1 mRNA. Exons 4 and 5 are highlighted (the del12 variant lies within intron 4 between exons 4 and 5 in the unspliced RNA) along with the positions of the PCR primers (red arrows) used to amplify the cDNA. (B) Agarose gel showing the PCR products generated by amplifying cDNA generated from RNA isolated from the blood of del12 carriers and non-carriers. Arrows indicate both the size of the expected PCR product (239 bp) along with the size of the truncated band (217 bp) observed only in del12 heterozygote carriers. (C) Shown is the sequence difference between the full-length (239 bp) and variant (217 bp) cDNA fragments based on Sanger sequencing. The variant sequence in del12 carriers lacks 22 bp at the end of exon 4 compared to the wild-type sequence that results in frameshift and introduction of a stop codon. (D) Diagrammatic representation of the splicing defect observed in del12 carriers. The sequence around the exon 4-intron 4 boundary (exon 4 sequence in capital letters and intron 4 sequence in small letters) is shown along with the 5' splice site in non-carriers and the cryptic 5' splice site activated in del12 carriers. (E) Quantification of the full-length (239 bp) and variant (217 bp) cDNA fragments from heterozygote del12 carriers and non-carriers by direct digital counting of sequencing reads generated following sequencing of the amplified cDNA product from carriers and non-carriers of del12 using the Illumina TruSeq method. The percentage of incorrectly spliced ASGR-1 transcript is shown. Note that the incorrectly spliced form was completely undetectable in non-carriers.

DEL12 within Intron 4 of ASGR-1 Causes a Splicing Error Resulting in a Frameshift Since del12 is located in intron 4 of ASGR-1, we examined its effect on splicing between exons 4 and 5. The region between exon 3 and 5 in cDNA generated from blood samples from 12 non-carriers and 12 heterozygous carriers of del12 was PCR amplified (FIG. 4). The PCR products were resolved by gel electrophoresis demonstrating a band of 239 bp in non-carrier. In del12 carriers, however, a smaller 217 bp band was noted in addition to the expected 239 bp PCR product (FIG. 4B). Upon Sanger sequencing of the cDNA products we identified in the 217 bp cDNA fragment a 22 bp deletion at the end of exon 4 (FIG. 4C). The deletion of these 22 bp from the ASGR-1 transcript appears to be driven by a pseudo 5'-splice site in exon 4 (FIG. 4D). It causes a frameshift in carriers such that, if translated, the resulting protein would lack both the oligomerization and carbohydrate recognition domains. To quantify this splicing defect we used the Illumina TruSeq method for direct digital counting of sequencing reads that were generated by sequencing the two cDNA products found in del12 carriers. On average, 32±13% of the total ASGR-1 transcripts were accounted for by the incorrectly spliced isoform (FIG. 4E). This form could not be detected in non-carriers (FIG. 4E). Together, these data identify ASGR-1 as the target gene for the non-HDL association at this locus and are consistent with the associated mutation, del12, disrupting the function of the ASGR-1 protein. ASGR-1 is the major subunit of the hepatic asialoglycoprotein receptor (ASGR) known to recognize and mediate the endocytosis and degradation of a wide variety of desialylated glycoproteins that contain terminal galactose (Gal) or N-acetylgalactosamine (Gal-NAc) residues on their N-linked carbohydrate chains (Morell A G, Gregoriadis G, Scheinberg I H, Hickman J, Ashwell G. The role of sialic acid in determining the survival of glycoproteins in the circulation. The Journal of biological chemistry 1971; 246: 1461-7; Van Den Hamer C J, Morell A G, Scheinberg I H, Hickman J, Ashwell G. Physical and chemical studies on ceruloplasmin. IX. The role of galactosyl residues in the clearance of ceruloplasmin from the circulation. The Journal of biological chemistry 1970; 245:4397-402; Ashwell G, Harford J. Carbohydrate-specific receptors of the liver. Annual review of biochemistry 1982; 51:531-54; Weigel P H. Galactosyl and N-acetylgalactosaminyl homeostasis: a function for mammalian asialoglycoprotein receptors. BioEssays: news and reviews in molecular, cellular and developmental biology 1994; 16:519-24).

The DEL12 Variant in ASGR-1 and Risk of Coronary Artery Disease

Given the effect of del12 on non-HDL cholesterol levels, its impact on risk of CAD in 33,090 cases and 236,254 controls from Iceland and 8,558 cases and 11,120 controls from the USA, the UK, New Zealand and Denmark was assessed. It was found that carriers of del12 have a lower risk of CAD than non-carriers (odds ratio 0.66; 95% confidence interval [CI] 0.55 to 0.79; P=6.3×10-6) (FIG. 5A). There was no evidence of heterogeneity across the eight study populations (Phet=0.96). Del12 also decreases risk of MI in Iceland (hazard ratio 0.64; 95% CI, 0.64 to 0.80; P=8.5× 10-5) (FIG. 5B). In addition, del12 carriers have a 1.5 years longer lifespan than non-carriers (95% CI, 0.2 to 2.8 years; P=0.020).

Figure 6:
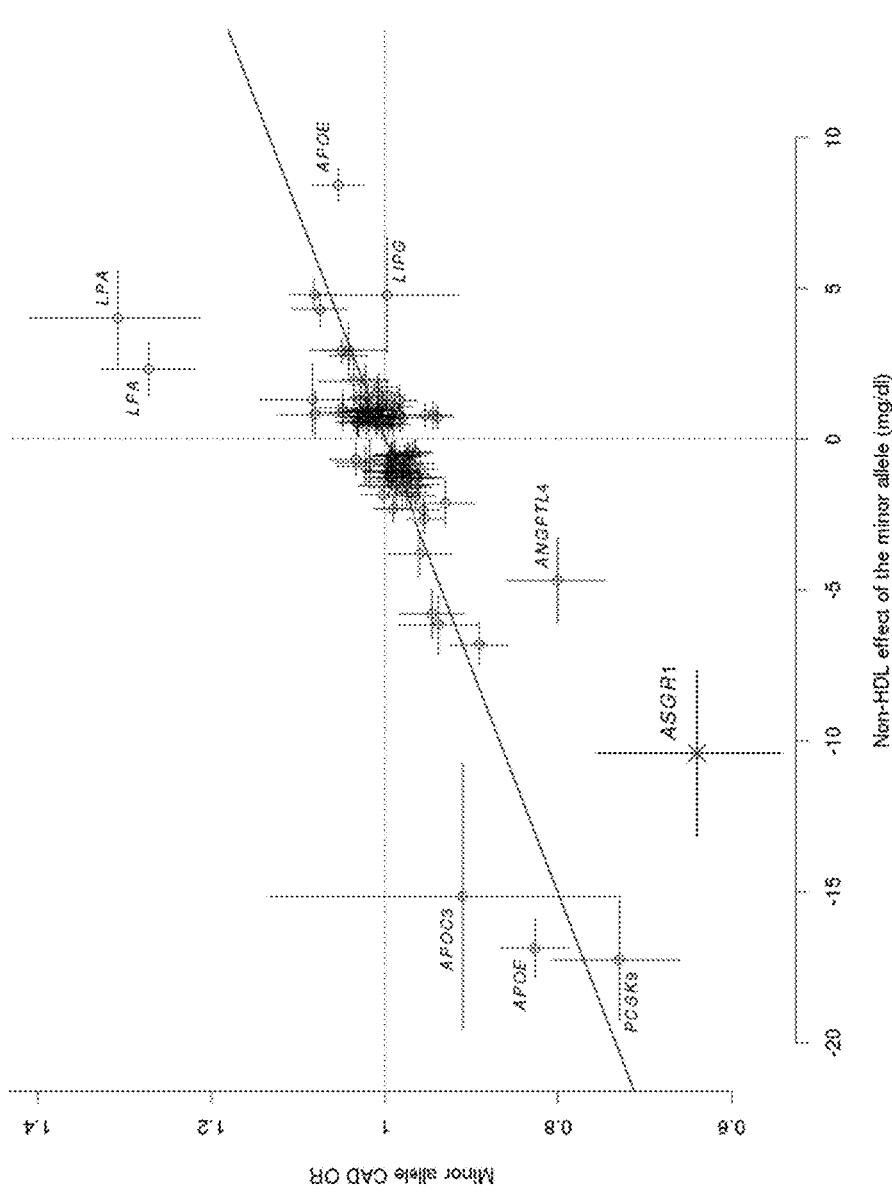
FIG. 6. Comparison of relationship between CAD and non-HDL cholesterol levels between previously identified sequence variants and del12 in ASGR-1. Based on the Icelandic population, the estimated odds ratio (OR) of the minor allele for coronary artery disease (CAD, 41,648 cases and 247,374 controls) as a function of the estimated effect of the minor allele on non-HDL cholesterol levels (N=119, 146). A full list of the sequence variants included is provided in Table 1.7. The error bars represent 95% confidence intervals. The del12 variant in ASGR-1 is shown. The line indicates the best linear regression fit through the origin.

There is a strong positive correlation between the effect of sequence variants on non-HDL cholesterol levels and risk of CAD (Haddad L, Day I N, Hunt S, Williams R R, Humphries S E, Hopkins P N. Evidence for a third genetic locus causing familial hypercholesterolemia. A non-LDLR, non-APOB kindred. Journal of lipid research 1999; 40:1113-22; Timms K M, Wagner S, Samuels M E, et al. A mutation in PCSK9 causing autosomal-dominant hypercholesterolemia in a Utah pedigree. Human genetics 2004; 114:349-53; Varret M, Rabes J P, Saint-Jore B, et al. A third major locus for autosomal dominant hypercholesterolemia maps to 1p34.1-p32. American journal of human genetics 1999; 64:1378-87; Hunt S C, Hopkins P N, Bulka K, et al. Genetic localization to chromosome 1p32 of the third locus for familial hypercholesterolemia in a Utah kindred. Arterioscler Thromb Vasc Biol 2000; 20:1089-93; Do R, Willer C J, Schmidt E M, et al. Common variants associated with plasma triglycerides and risk for coronary artery disease. Nature genetics 2013; 45:1345-52) (FIG. 6, Table 1.5). However, several published variants, deviate from the overall trend. For example, LPA and ANGPTL4 variants have a substantially greater effect on CAD than their non-HDL effects would predict while the effect of the APOE variants is weaker than predicted by the non-HDL effect. Del12 in ASGR-1 is another example of a variant whose effect on CAD is stronger than predicted by the effect non-HDL cholesterol effect (FIG. 6, Table 1.5).

Association of DEL12 with Serum Levels of ALP and Vitamin B12

To determine the overall effect of del12 in ASGR-1, its effect on a variety of human diseases and other traits in the Icelandic dataset was screened. A highly significant association of del12 with higher levels of circulating alkaline phosphatase (ALP) (33.6±2.8 U/L increase, P=3.6×10-63) and vitamin B12 (58.4±8.3 pmol/L increase, P=3.1×10-12) was observed (Tables 8A and 8B and Table 18). An increase in ALP levels may reflect liver disease, however, there was no increase in del 12 carriers in serum gamma glutamyl transferase (GGT), bilirubin, alanine aminotransferase or other measures of liver function that commonly parallel changes in ALP in liver disease (Table 1.6).

The del12 association with higher levels of ALP and vitamin B12 in individuals from the Danish Inter99 study with comparable effect sizes (P=9.9×10-69 for ALP and P=9.9×10-14 for vitamin B12) was replicated (Table 1.10).

A common variant upstream of ASGR-1 (rs314253; MAF=35.1%) has been reported to associate modestly with both LDL cholesterol and ALP levels (Chambers J C, Zhang W, Sehmi J, et al. Genome-wide association study identifies loci influencing concentrations of liver enzymes in plasma. Nature genetics 2011; 43:1131-8; Willer C J, Schmidt E M, Sengupta S, et al. Discovery and refinement of loci associated with lipid levels. Nature genetics 2013; 45:1274-83). This common variant association is replicated in the data of the present invention (strongest association for both ALP and non-HDL with the correlated rs56093546; MAF=21.6%) and that its associations with ALP and non-HDL are independent of the rare signal represented by del12 (r2<0.001, Table 1.5) as demonstrated. As for del12, this common variant has opposite effects on ALP and non-HDL; the allele that increases ALP decreases non-HDL (see Chambers; Willer) (Table 1.7).

TABLE 1.1

| Study | Design | Definition of CAD and MI cases | Ascertainment of controls | Reference |
| --- | --- | --- | --- | --- |
| Iceland | Case/control | CAD and MI cases were defined by: a) discharge diagnoses (ICD 9 codes 410.*, 411.*, 412.*, 414.* or ICD 10 codes I20.0, I21.*, I22.*. I23.*, I24.*, I25.*) from LUH, b) significant angiographic CAD (≥50% stenosis of the major coronary vessels), c) undergone coronary revascularisation (CABG) d) MI or CAD (ICD 9 or 10 codes) listed in death registries, or e) MI before the age of 75 from MONICA registry | Study participants from various deCODE genetics programs without known CVD. | Helgadottir A, Thorleifsson G, Manolescu A, et al. A common variant on chromosome 9p21 affects the risk of myocardial infarction. Science (New York, NY) 2007; 316: 1491-3. |
| UK 1-Leicester MI Study | Case/control | Cases included MI patients admitted to the coronary care units of the Leicester Royal Infirmary, Leicester and the Royal Hallamshire Hospital, Sheffield and satisfied the WHO criteria for acute MI. | Controls included adult visitors of individuals with non-cardiovascular disease from each hospital or individuals from three primary care practices located in the same geographical area. Individuals who reported a history of CAD were excluded. | Helgadottir A, Manolescu A, Thorleifsson G, et al. The gene encoding 5-lipoxygenase activating protein confers risk of myocardial infarction and stroke. Nature genetics 2004; 36: 233-9. |
| UK2-BHF Family Heart Study | Case/control | The British Heart Foundation Family Heart Study (BHF-FHS) CAD cases were index cases from families of European ancestry with a strong familial history of defined CAD recruited from throughout the United Kingdom. CAD was defined as a validated history of myocardial infarction or coronary revascularisation (PTCA or CABG) before the 66th birthday. | Controls were blood donors recruited by the United Kingdom Blood Service (UKBS) as part of the Wellcome Trust Case Control Consortium Study. | Genome-wide association study of 14,000 cases of seven common diseases and 3,000 shared contorls. Nature 2007; 447: 661-78, and Samani NJ, Erdmann J, Hall AS, et al. Genomewide association analysis of coronary artery disease. The New England journal of medicine 2007; 357: 443-53. |
| Emory (Atlanta, Georgia, USA) | Case/control | Cases were identified from subjects undergoing cardiac catheterization at the Emory University Hospital. CAD cases included those that had at least one significant stenosis (≥50%) in any of the major coronary arteries on angiography, or those without significant stenosis but had history of MI, CABG, or PCI. | Controls included individuals undergoing cardiac catheterization with no or minimal CAD (<20% stenosis) and had no prior history of MI or CAD. Additional controls were recruited from the Grady Memorial Hospitals and Clinical Registry in Neurology (CRIN) and included individuals with non-vascular neurological diseases (mainly Parkinson's and Alxheimer's diseases), their spouses, unrelated friends and community volunteers; excluding those with a known history of CAD. | Helgadottir A, et al. (2007) |

TABLE 1.1-continued

| Study | Design | Definition of CAD and MI cases | Ascertainment of controls | Reference |
| --- | --- | --- | --- | --- |
| Duke (Durham, North Carolina USA) | Case/control | Participants were enrolled at Duke University Medical Center through the cardiac catheterization laboratories. MI cases included those with self-reported history of MI (corroborated by review of medical records), or those who suffered an MI during the study follow-up period. | Controls included those with no history of MI prior or subsequent to the index cardiac catheterization and no PCI or CABG ejection fraction on left ventriculogram greater than 40% and stenosis less than 50% on coronary angiography. | Helgadottir A, et al. (2007) |
| Upenn (Philadelphia, Pennsylvania, USA) | Case/control | The study participants were enrolled at the University of Pennsylvania Medical Center and included subjects undergoing cardiac catheterization. CAD cases included those that had at least one significant stenosis (≥50%) in any of the major coronary arteries on angiography, or those without significant stenosis but had history of MI, CABG, or PCI. | Controls included individuals without significant luminal stenosis on coronary angiography (luminal stenosis less than 50%). | Helgadottir A, et al. (2007) |
| New Zeland | Case/control | a) Significant angiographic CAD (≥50% stenosis of the major coronary vessels), b) CABG-procedures c)MI or CAD (ICD 9 or 10 codes) in a clinical registry. | Study participants without known CAD and ultrasound screened for carotid artery disease and abdominal aortic aneurysm, with ankle brachial index to exclude peripheral artery disease. | Gretarsdottir S, Baas AF, Thorleifsson G, et al. Genome-wide association study identifies a sequence variant within the DAB2IP gene conferring susceptibility to abdominal aortic aneurysm. nature genetics 2010; 42: 69 2-7. |
| Denmark 1 (Gentofte cadlab) | Case/control | Cases were identified from subject investigated by coronary artery angiography because of suspected ischemic heart disease, valvular heart disease or cardiomyopaty. CAD cases included those that had at least one significant stenosis (≥50%) in any of the major coronary arteries on angiography | Individual in Monica10 and Inter99 studies without CAD diagnosis based on information from the Danish National Patient Registry and the Danish Register of Causes of Death. | |
| Denmark 2 (Monica10) | Case/control | Monica10 is a population based study. Paricipants were recruited from the Danish Central Personal Register as random samples of the population in the southern part of the former Copenhagen County. Cardiovascular events were defined as first ever non-fatal or fatal CVD (ICD-8: 390-448/ ICD-10: 100-I79). Assesment of the cardiovascular endpoints was based on data from the Danish National Patient Register of Causes of Death. | Individual in Monica10 and Inter99 studies without CAD diagnosis based on information from the Danish National Patient Registry and the Danish Register of Causes of Death. | Olsen MH, Hansen TW, Christensen MK, et al. N-terminal pro-brain natriuretic peptide, but not high sensitivity C-reactive protein, improves cardiovascular risk prediction in the general population. European heart journal 2007; 28: 13 74-81. |
| Denmark 3 (Inter99) | Case/control | The Inter99 study is a population-based randomized controlled trial (CT00289237, ClinicalTrials.gov) investigating the effects of lifestyle intervention on cardiovascular disease. Cardiovascular events were defined as first ever non-fatal or fatal CVD (ICD-8: 390-448/ | Individual in Monica10 and Inter99 studies without CAD diagnosis based on information from the Danish National Patient Registry and the Danish Register of Causes of Death. | 14. Jorg ensen AB, Frikke-Schmidt R, Nordestgaard BG, Tybjaerg-Hansen A. Loss-of-function mutations in APOC3 and risk of ischemic vascular disease. The New England journal of medicine 2014; 371: 3 2-41. |

TABLE 1.1-continued

| Study | Design | Definition of CAD and MI cases | Ascertainment of controls | Reference |
|---|---|---|---|---|
| | | ICD-10: 100-I79). Assesment of the cardiovascular endpoints was based on data from the Danish National Patient Registry and the Danish Register of Causes of Death. | | |
| Sweden | Case/Control | Ischemic stroke patients from the clinic at Karolinska University Hospital, Stockholm. The ischemic stroke diagnosis was based on clinical findings and brain imaging (CT or MRI). | Population-based controls, either healthy blood donors or healthy volunteers recruited at the Karolinska Hospital | Gretardottir et al (2008) Traylor et al (2012) |
| South Germany | Case/Control | Ischemic stroke patients recruited at the stroke unit of the Department of Neurology, Klinikum Grosshadern, University of Munich. Diagnoses were based on clinical findings and imaging evidence (either CT or MRI), and were clinically confirmed by neurologists. | Gender and age matched individuals without history of cardiovascular disease selected from KORA S4 Study | Traylor et al (2008) Gschwendt ner et al (2009) Wichmann et al (2005) |
| West Germany | Case/Control | Ischemic stroke patients recruited through hospitals participating in the regional Westphalian Stroke Register. Diagnoses were based on clinical findings and imaging evidence (either CT or MRI), and were clinically confirmed by neurologists. | Population controls with a self-reported history of stroke from the population based Dortmund Health Study | Traylor et al (2008) Berger et al (2007) |
| United Kingdom | Case/Control | Ischemic stroke patients recruited through a cerebrovascular service clinic. All cases were phenotyped by one experienced stroke neurologist with review of original brain imaging with CT or MRI. | Community controls, age and gender matched and free of symptomatic cerebrovascular disease were recruited from the same geographic area as the patients. | Traylor et al (2008) Gschwendt ner et al (2009) |

TABLE 1.2

Characteristics of Participants in the Discovery and Replication Studies of the association of del12 Variant with Plasma Lipid, Alkaline Phosphatase, and Vitamin B12 levels

| Trait[a] | Iceland | Nijmegen Biomedical study (Netherlands)[c] | Inter99 Study (Denmark)[d] | Addition Study (Denmark)[e] |
|---|---|---|---|---|
| Ancestry | Caucasian | Caucasian | Caucasian | Caucasian |
| N[b] | 194,958 | 5,645 | 7,633 | 9,689 |
| Mean age (SD), yrs | 58.2 (40.6-75.8) | 55.8 (38.0-73.6) | 48.5 (36.1-55.5) | 59.9 (53.1-66.7) |
| Gender, % female | 53.4% | 53.6% | 49.9% | 46.4% |
| Non-HDL cholesterol (SD), mg/dL | 154.7 (109.1-200.3) | 170.7 (129.4-212.0) | 161.6 (117.5-205.7) | 164.7 (124.0-205.4) |
| LDL cholesterol (SD), mg/dL | 133.0 (91.6-174.4) | 138.6 (102.2-175.0) | 137.2 (99.7-174.7) | 139.3 (101.9-176.1) |
| HDL cholesterol (SD), mg/dL | 54.7 (37.7-71.7) | 52.6 (39.2-66.0) | 54.2 (38.4-70.0) | 60.0 (43.6-76.4) |
| Total Cholesterol (SD), mg/dL | 208.0 (162.6-253.4) | 223.4 (180.9-265.9) | 215.8 (173.6-258.0) | 224.7 (183.9-265.5) |
| Triglycerides (SD), mg/dL | 133.6 (67.6-190.5) | 155.8 (94.5-256.8) | 105.8 (60.8-183.9) | 117.4 (73.5-187.3) |
| Alkaline phosphatase (SD), IU/l | 87.1 (53.5-141.7) | na | 41.3 (30.7-55.6) | na |
| Vitamin B12 (SD), pmol/l | 398 (256-618) | na | 398 (286-554) | na |

[a]The average values (where available) for each of the traits listed is shown (±one SD).
[b]Number of individuals with measurements for at least one of the traits.
[c]Wetzels et al (2007)[5],
[d]Jörgensen et al (2003)[6],
[e]Lauritzen et al (2000)[7].

TABLE 1.4A

Association of del12 with Non-HDL Cholesterol, LDL Cholesterol, HDL Cholesterol, Triglyceride, ALP and Vitamin B12 in Iceland, Denmark and The Netherlands

| Study population (n) | | del12 freq. (%) | Effect (95% CI)[a] | P value | population mean value[e] (±1SD) |
|---|---|---|---|---|---|
| | Non-HDL cholesterol | | mg/dL | | mg/dL |
| Discovery | Iceland (119,146) | 0.41 | −13.6 (−17.7, −9.4) | $2.5 \times 10^{-10}$ | 154.7 (109.1-200.3) |
| Replication | Denmark A[b] (6,182) | 0.22 | −21.3 (−36.8, −5.9) | 0.0069 | 161.6 (117.5-205.7) |
| Replication | Denmark B[c] (9,656) | 0.32 | −22.2 (−32.8, −11.7) | $3.8 \times 10^{-5}$ | 164.7 (124.0-205.4) |
| Replication | The Netherlands[d] (5,537) | 0.50 | −17.0 (−28.3, −5.7) | 0.0032 | 170.7 (129.4-212.0) |
| | Combined | | −15.3 (−18.9, −11.7) | $1.0 \times 10^{-16}$ | |
| | LDL cholesterol | | mg/dL | | |
| Discovery | Iceland (53,841) | 0.41 | −9.5 (−14.0, −5.1) | $2.8 \times 10^{-5}$ | 133.0 (91.6-174.4 |
| Replication | Denmark A (6,098) | 0.22 | −22.1 (−35.5, −8.7) | 0.0012 | 137.2 (99.7-174.7) |
| Replication | Denmark B (8,080) | 0.32 | −19.0 (−29.2, −8.8) | 0.00026 | 139.3 (101.9-176.1) |
| Replication | The Netherlands (5,523) | 0.50 | −16.0 (−26.1, −6.0) | 0.0018 | 138.6 (102.2-175.0) |
| | Combined | | −12.5 (−16.2, −8.8) | $3.9 \times 10^{-11}$ | |
| | HDL cholesterol | | mg/dL | | mg/dL |
| Discovery | Iceland (119,514) | 0.41 | 2.4 (0.7, 4.1) | 0.0058 | 54.7 (37.7-71.7) |
| Replication | Denmark A (6,182) | 0.22 | 4.6 (−0.8, 9.9) | 0.096 | 54.2 (38.4-70.0) |
| Replication | Denmark B (9,656) | 0.32 | 2.4 (−1.8, 6.7) | 0.26 | 60.0 (43.6-76.4) |
| Replication | The Netherlands (5,537) | 0.50 | 2.4 (−1.3, 6.0) | 0.20 | 52.6 (39.2-66.0) |
| | Combined | | 2.5 (1.1, 4.0) | 0.00039 | |
| | Triglyceride | | % change | | mg/dL |
| Discovery | Iceland (80,011) | 0.41 | −6.1 (−10.8, −1.5) | 0.012 | 133.6 (67.6-190.5) |
| Replication | Denmark A (6,182) | 0.22 | −6.0 (−25.2, 11.4) | 0.53 | 105.8 (60.8-183.9) |
| Replication | Denmark B (8,163) | 0.32 | −8.9 (−21.0, 2.3) | 0.15 | 117.4 (73.5-187.3) |
| Replication | The Netherlands (5,537) | 0.50 | −4.4 (−17.9, 8.2) | 0.52 | 155.8 (94.5-256.8) |
| | Combined | | −6.3 (−10.3, −2.3) | 0.0032 | |
| | ALP | | % change | | U/L |
| Discovery | Iceland (126,060) | 0.41 | 50.1 (42.9, 57.2) | $3.6 \times 10^{-63}$ | 87.1 (53.5-141.7) |
| Replication | Denmark A[c] (5,829) | 0.22 | 29.1 (14.8, 42.5) | $3.1 \times 10^{-6}$ | 41.3 (30.7-55.6) |
| | Combined | | 46.5 (40.1, 52.7) | $5.6 \times 10^{-69}$ | |
| | Vitamin B12 | | % change | | pmol/L |
| Discovery | Iceland (97,910) | 0.41 | 16.6 (11.5, 21.5) | $3.1 \times 10^{-12}$ | 398 (256-618) |
| Replication | Denmark A[c] (5,826) | 0.22 | 18.6 (3.9, 32.4) | 0.0053 | 398 (286-554) |
| | Combined | | 16.8 (12.0, 21.5) | $8.3 \times 10^{-14}$ | |

[a]Effect estimates and 95% confidence intervals (95% CI) in mg/dL for the non-HDL cholesterol and HDL cholesterol and as percentage change for triglyceride, ALP and vitamin B12.
[b]The Danish Inter99 study (JørgeFnsen et al. 2003).
[c]The Danish Addition study (van den Donk et al. 2011).
[d]The Nijmegen Biomedical Study (Hoogendoorn et al. 2006).
[e]For triglyceride, ALP and vitamin B12, the population mean and the SD are calculated for log-transformed values and transformed back to original units. To convert the values for non-HDL and HDL cholesterol to millimoles per liter, multiply by 0.02586. To convert triglyceride to mmol/L, multiply by 0.01129.

TABLE 1.4B

Association of del12 and rs186021206 with Cholesterols, Triglyceride, Alkaline Phosphatase and Vitamin B12 Measurements in Iceland, Denmark and the Netherlands.

| | rs186021206 | | | | del12 | | |
|---|---|---|---|---|---|---|---|
| Trait/Cohort (n)[a] | Effect[b] | Effect (95% CI)[c] | P | $P_{adj}$[d] | Effect[b] | Effect (95% CI)[c] | P |
| Non-HDL cholesterol | SD | mg/dL | | | | mg/dL | |
| Iceland (119,146) | −0.28 | −12.9 (−17.1, −8.7) | $1.4 \times 10^{-9}$ | 0.39 | −0.30 | −13.6 (−17.7, −9.4) | $2.5 \times 10^{-10}$ |
| Denmark A (6,182) | −0.38 | −16.7 (−27.9, −5.4) | 0.0038 | 0.64 | −0.48 | −21.3 (−36.8, −5.9) | 0.0069 |
| Denmark B (9,656) | −0.32 | −13.1 (−21.0, −5.3) | 0.0011 | 0.74 | −0.55 | −22.2 (−32.8, −11.7) | $3.8 \times 10^{-5}$ |

TABLE 1.4B-continued

Association of del12 and rs186021206 with Cholesterols, Triglyceride, Alkaline Phosphatase and Vitamin B12 Measurements in Iceland, Denmark and the Netherlands.

| | | | | | | | | |
|---|---|---|---|---|---|---|---|---|
| The Netherlands (5,537) | −0.23 | −9.7 (−19.9, 0.5) | 0.062 | 0.19 | −0.41 | −17.0 (−28.3, −5.7) | 0.0032 |
| Combined | −0.29 | −12.9 (−16.3, −9.6) | $2.0 \times 10^{-14}$ | 0.24 | −0.34 | −15.3 (−18.9, −11.7) | $1.0 \times 10^{-16}$ |
| LDL cholesterol | | mg/dL | | | | mg/dL | | |
| Iceland (53,841) | −0.22 | −9.2 (−13.6, −4.7) | $5.5 \times 10^{-5}$ | 0.78 | −0.23 | −9.5 (−14.0, −5.1) | $2.8 \times 10^{-5}$ |
| Denmark A (6,098) | −0.43 | −16.1 (−25.8, −6.3) | 0.0012 | 0.56 | −0.59 | −22.1 (−35.5, −8.7) | 0.0012 |
| Denmark B (8,080) | −0.34 | −12.5 (−20.3, −4.7) | 0.0016 | 0.86 | −0.51 | −19.0 (−29.2, −8.8) | 0.00026 |
| The Netherlands (5,523) | −0.36 | −13.2 (−22.3, −4.2) | 0.0041 | 0.81 | −0.44 | −16.0 (−26.1, −6.0) | 0.0018 |
| Combined | −0.28 | −11.1 (−14.5, −7.8) | $1.0 \times 10^{-10}$ | 0.70 | −0.31 | −12.5 (−16.2, −8.8) | $3.9 \times 10^{-11}$ |
| Total cholesterol | | mg/dL | | | | mg/dL | | |
| Iceland (125,381) | −0.22 | −9.9 (−14.0, −5.7) | $3.1 \times 10^{-6}$ | 0.78 | −0.23 | −10.5 (−14.7, −6.4) | $6.5 \times 10^{-7}$ |
| Denmark A (6,182) | −0.32 | −13.5 (−24.2, −2.8) | 0.014 | 0.54 | −0.33 | −14.0 (−28.7, 0.8) | 0.063 |
| Denmark B (9,656) | −0.30 | −12.0 (−19.9, −4.2) | 0.0027 | 0.97 | −0.47 | −19.2 (−29.8, −8.6) | 0.00040 |
| The Netherlands (5,537) | −0.21 | −9.0 (−19.5, 1.5) | 0.0927 | 0.48 | −0.33 | −14.1 (−25.7, −2.5) | 0.018 |
| Combined | −0.24 | −10.5 (−13.8, −7.2) | $5.1 \times 10^{-10}$ | 0.68 | −0.27 | −12.0 (−15.6, −8.5) | $5.6 \times 10^{-11}$ |
| HDL cholesterol | | mg/dL | | | | mg/dL | | |
| Iceland (119,514) | 0.13 | 2.2 (0.5, 3.9) | 0.011 | 0.0055 | 0.14 | 2.4 (0.7, 4.1) | 0.0058 |
| Denmark A (6,182) | 0.15 | 2.4 (−1.5, 6.4) | 0.22 | 0.84 | 0.29 | 4.6 (−0.8, 9.9) | 0.096 |
| Denmark B (9,656) | 0.03 | 0.4 (−2.7, 3.6) | 0.79 | 0.32 | 0.15 | 2.4 (−1.8, 6.7) | 0.26 |
| The Netherlands (5,537) | 0.02 | 0.2 (−3.1, 3.5) | 0.9 | 0.043 | 0.18 | 2.4 (−1.3, 6.0) | 0.20 |
| Combined | 0.10 | 1.6 (0.4, 2.9) | 0.01 | 0.001 | 0.15 | 2.5 (1.1, 4.0) | 0.00039 |
| Triglyceride | | % change | | | | % change | | |
| Iceland (80,011) | −0.11 | −5.4 (−10.1, −0.8) | 0.027 | 0.13 | −0.12 | −6.1 (−10.8, −1.5) | 0.012 |
| Denmark A (6,182) | −0.26 | −13.4 (−26.1, −1.6) | 0.046 | 0.11 | −0.11 | −6.0 (−25.2, 11.4) | 0.53 |
| Denmark B (8,163) | −0.03 | −1.3 (−11.2, 8.0) | 0.79 | 0.099 | −0.2 | −8.9 (−21.0, 2.3) | 0.15 |
| The Netherlands (5,537) | 0.13 | 6.5 (−7.0, 19.1) | 0.32 | 0.0057 | −0.09 | −4.4 (−17.9, 8.2) | 0.52 |
| Combined | −0.09 | −4.2 (−7.9, −0.6) | 0.028 | 0.0066 | −0.13 | −6.3 (−10.3, −2.3) | 0.003 |
| ALP | | % change | | | | % change | | |
| Iceland (126,060) | 0.82 | 48.9 (41.8, 55.8) | $1.2 \times 10^{-61}$ | 0.10 | 0.84 | 50.1 (42.9, 57.2) | $3.6 \times 10^{-63}$ |
| Denmark A (6,035) | 0.70 | 23.0 (13.2, 32.4) | $2.2 \times 10^{-7}$ | 0.092 | 0.86 | 29.1 (14.8, 42.5) | $3.1 \times 10^{-6}$ |
| Combined | 0.80 | 41.5 (35.9, 47.0) | $1.9 \times 10^{-67}$ | 0.026 | 0.84 | 46.5 (40.1, 52.7) | $5.6 \times 10^{-69}$ |
| Vitamin B12 | | % change | | | | % change | | |
| Iceland (97,910) | 0.33 | 15.8 (10.8, 20.7) | $2.0 \times 10^{-11}$ | 0.15 | 0.35 | 16.6 (11.5, 21.5) | $3.1 \times 10^{-12}$ |
| Denmark A (6,032) | 0.49 | 17.6 (7.2, 27.7) | 0.00027 | 0.011 | 0.52 | 18.6 (3.9, 32.4) | 0.0053 |
| Combined | 0.35 | 16.1 (11.6, 20.6) | $4.3 \times 10^{-14}$ | 0.84 | 0.36 | 16.8 (12.0, 21.5) | $8.3 \times 10^{-14}$ |

[a]Number of individuals with trait value and genotypes.
[b]Effect estimates from the regression in units of standard deviations (SD) of the distributions of the adjusted values.
[c]Effect estimates and 95% confidence intervals (95% CI) in mg/dL for the cholesterol, and as percentage change for triglyceride, ALP and vitamin B12.
[d]P-values adjusted for the effect of del12. "The Netherlands", The Nijmegen Biomedical Study[15]; "Denmark A", The Danish Inter99 study[6]; "Denmark B", The Danish Addition study[16].

TABLE 1.5

The association of published lipid variants with non-HDL cholesterol levels and coronary artery disease in Iceland.

| Build 36 position | | | | Non-HDL (mg/dL) | | Coronary artery disease | | |
| --- | --- | --- | --- | --- | --- | --- | --- | --- |
| Chr | Position (hg18) | MAF | Info | Effect | SE | OR | 95% CI | |
| 1 | 25,641,524 | 0.47184 | 0.996 | 0.7 | 0.2 | 0.99 | 0.97 | 1.02 |
| 1 | 55,278,235 | 0.01173 | 0.986 | −17.2 | 1.0 | 0.73 | 0.66 | 0.81 |
| 1 | 62,725,961 | 0.21814 | 0.996 | 1.6 | 0.3 | 1.01 | 0.98 | 1.03 |
| 1 | 62,906,518 | 0.33844 | 0.998 | −2.3 | 0.2 | 0.99 | 0.97 | 1.01 |
| 1 | 92,766,395 | 0.19052 | 0.999 | 0.8 | 0.3 | 0.99 | 0.97 | 1.02 |
| 1 | 109,620,053 | 0.20789 | 0.999 | 4.8 | 0.3 | 1.08 | 1.06 | 1.11 |
| 1 | 110,000,250 | 0.41287 | 0.995 | 1.0 | 0.2 | 1.01 | 0.99 | 1.03 |
| 1 | 149,225,460 | 0.15162 | 0.997 | −0.7 | 0.3 | 1.03 | 1.00 | 1.06 |
| 1 | 154,967,275 | 0.28892 | 0.998 | −0.5 | 0.2 | 0.99 | 0.97 | 1.02 |
| 1 | 219,036,651 | 0.28689 | 0.994 | 0.9 | 0.2 | 1.01 | 0.98 | 1.03 |
| 1 | 228,362,314 | 0.39128 | 0.999 | −1.1 | 0.2 | 0.99 | 0.97 | 1.01 |
| 1 | 232,915,962 | 0.4424 | 0.999 | 1.2 | 0.2 | 1.00 | 0.98 | 1.03 |
| 2 | 21,087,477 | 0.04518 | 0.999 | −6.1 | 0.5 | 0.94 | 0.89 | 0.99 |
| 2 | 21,117,405 | 0.3491 | 0.997 | 2.9 | 0.2 | 1.05 | 1.03 | 1.07 |
| 2 | 21,139,562 | 0.1408 | 0.999 | 4.3 | 0.3 | 1.08 | 1.04 | 1.11 |
| 2 | 27,584,444 | 0.34466 | 0.998 | −1.8 | 0.2 | 1.00 | 0.98 | 1.03 |
| 2 | 27,584,716 | 0.20151 | 0.995 | −1.4 | 0.3 | 1.00 | 0.97 | 1.02 |
| 2 | 43,927,385 | 0.27892 | 0.999 | −2.6 | 0.2 | 0.95 | 0.93 | 0.98 |
| 2 | 43,953,086 | 0.19027 | 0.997 | −1.5 | 0.3 | 0.96 | 0.94 | 0.99 |
| 2 | 63,003,061 | 0.32014 | 0.997 | 0.9 | 0.2 | 1.02 | 1.00 | 1.05 |
| 2 | 118,293,189 | 0.07895 | 0.998 | −0.8 | 0.4 | 1.02 | 0.98 | 1.06 |
| 2 | 121,025,958 | 0.41077 | 0.994 | 0.6 | 0.2 | 1.03 | 1.01 | 1.06 |
| 2 | 169,538,401 | 0.37685 | 0.999 | −0.5 | 0.2 | 0.99 | 0.97 | 1.01 |
| 2 | 216,012,629 | 0.32322 | 0.998 | 0.8 | 0.2 | 0.95 | 0.93 | 0.97 |
| 3 | 12,271,469 | 0.3667 | 0.998 | −1.2 | 0.2 | 0.99 | 0.97 | 1.02 |
| 3 | 32,508,014 | 0.07924 | 0.997 | −1.6 | 0.4 | 0.98 | 0.94 | 1.02 |
| 3 | 133,691,893 | 0.11977 | 0.998 | −1.1 | 0.3 | 0.99 | 0.96 | 1.03 |
| 3 | 172,209,912 | 0.07646 | 0.999 | 0.8 | 0.4 | 1.08 | 1.04 | 1.12 |
| 4 | 3,442,937 | 0.40281 | 0.991 | 0.7 | 0.2 | 1.03 | 1.00 | 1.05 |
| 4 | 25,672,088 | 0.14802 | 0.993 | 0.9 | 0.3 | 1.04 | 1.01 | 1.07 |
| 4 | 88,249,285 | 0.40279 | 0.999 | 0.7 | 0.2 | 1.00 | 0.98 | 1.02 |
| 4 | 100,233,828 | 0.42298 | 0.998 | 0.5 | 0.2 | 1.01 | 0.99 | 1.03 |
| 5 | 74,661,243 | 0.35407 | 0.999 | 2.8 | 0.2 | 1.04 | 1.02 | 1.06 |
| 5 | 122,883,315 | 0.47211 | 0.995 | 0.5 | 0.2 | 1.00 | 0.98 | 1.02 |
| 5 | 156,322,875 | 0.35741 | 0.998 | 1.7 | 0.2 | 1.01 | 0.99 | 1.03 |
| 6 | 16,217,142 | 0.46163 | 0.995 | −0.8 | 0.2 | 0.99 | 0.97 | 1.01 |
| 6 | 26,201,120 | 0.06713 | 1.000 | −1.5 | 0.4 | 0.99 | 0.95 | 1.03 |
| 6 | 31,373,469 | 0.29084 | 0.993 | 0.8 | 0.2 | 1.02 | 1.00 | 1.04 |
| 6 | 43,865,874 | 0.47286 | 0.993 | 0.9 | 0.2 | 1.02 | 1.00 | 1.04 |
| 6 | 100,706,818 | 0.19956 | 0.998 | −1.0 | 0.3 | 1.00 | 0.97 | 1.02 |
| 6 | 116,444,196 | 0.40848 | 0.998 | −0.6 | 0.2 | 0.98 | 0.96 | 1.00 |
| 6 | 127,494,332 | 0.47183 | 0.999 | 0.9 | 0.2 | 1.01 | 0.99 | 1.03 |
| 6 | 139,873,450 | 0.42692 | 0.999 | −0.7 | 0.2 | 0.98 | 0.96 | 1.00 |
| 6 | 160,881,127 | 0.01773 | 1.000 | 4.0 | 0.8 | 1.31 | 1.21 | 1.41 |
| 6 | 160,930,108 | 0.06104 | 0.984 | 2.3 | 0.4 | 1.27 | 1.22 | 1.33 |
| 7 | 21,573,877 | 0.22512 | 0.992 | 1.5 | 0.3 | 1.00 | 0.98 | 1.02 |
| 7 | 25,958,351 | 0.14423 | 0.993 | 0.9 | 0.3 | 1.05 | 1.02 | 1.08 |
| 7 | 44,548,856 | 0.2013 | 0.990 | 2.0 | 0.3 | 1.02 | 1.00 | 1.05 |
| 7 | 44,567,220 | 0.42549 | 0.998 | −1.2 | 0.2 | 0.97 | 0.95 | 0.99 |
| 7 | 72,620,810 | 0.11552 | 0.998 | −0.9 | 0.3 | 1.02 | 0.99 | 1.06 |
| 7 | 72,697,942 | 0.46468 | 0.997 | 0.5 | 0.2 | 0.99 | 0.97 | 1.01 |
| 7 | 130,095,474 | 0.44163 | 0.998 | −0.5 | 0.2 | 0.96 | 0.94 | 0.98 |
| 8 | 9,221,641 | 0.07554 | 0.997 | 1.9 | 0.4 | 1.04 | 1.00 | 1.08 |
| 8 | 18,316,718 | 0.18705 | 0.996 | −1.3 | 0.3 | 0.96 | 0.94 | 0.99 |
| 8 | 19,888,502 | 0.08181 | 0.996 | −2.1 | 0.4 | 0.93 | 0.89 | 0.97 |
| 8 | 19,910,123 | 0.45471 | 0.996 | −1.0 | 0.2 | 0.96 | 0.94 | 0.98 |
| 8 | 55,584,167 | 0.24432 | 1.000 | 1.0 | 0.2 | 1.02 | 0.99 | 1.04 |
| 8 | 59,548,473 | 0.31037 | 0.998 | −1.4 | 0.2 | 0.99 | 0.97 | 1.01 |
| 8 | 116,733,072 | 0.26318 | 0.999 | −1.1 | 0.2 | 1.00 | 0.97 | 1.02 |
| 8 | 126,543,488 | 0.22755 | 0.997 | −1.9 | 0.3 | 0.96 | 0.94 | 0.99 |
| 8 | 126,551,803 | 0.49199 | 0.999 | −2.3 | 0.2 | 0.95 | 0.93 | 0.97 |
| 8 | 145,094,645 | 0.385 | 0.990 | 0.7 | 0.2 | 0.98 | 0.96 | 1.00 |
| 9 | 2,630,759 | 0.09898 | 0.998 | −1.3 | 0.4 | 0.97 | 0.94 | 1.01 |
| 9 | 16,894,846 | 0.31865 | 0.998 | −0.5 | 0.2 | 0.97 | 0.95 | 0.99 |
| 9 | 106,704,122 | 0.25781 | 0.999 | −1.1 | 0.2 | 0.97 | 0.95 | 0.99 |
| 9 | 106,724,051 | 0.28833 | 0.997 | −0.6 | 0.2 | 0.99 | 0.97 | 1.02 |
| 9 | 135,122,694 | 0.38646 | 0.997 | −0.9 | 0.2 | 0.99 | 0.97 | 1.01 |
| 9 | 135,143,989 | 0.15248 | 0.995 | 1.0 | 0.3 | 1.05 | 1.02 | 1.08 |
| 10 | 94,829,632 | 0.42892 | 0.993 | −0.6 | 0.2 | 0.99 | 0.97 | 1.01 |
| 11 | 18,612,847 | 0.30731 | 0.998 | 0.8 | 0.2 | 1.02 | 1.00 | 1.04 |
| 11 | 61,305,450 | 0.27208 | 0.991 | 0.8 | 0.2 | 1.01 | 0.99 | 1.04 |
| 11 | 61,354,548 | 0.38782 | 0.998 | −1.1 | 0.2 | 1.00 | 0.98 | 1.02 |
| 11 | 116,144,314 | 0.06787 | 0.999 | −5.8 | 0.4 | 0.94 | 0.91 | 0.98 |

TABLE 1.5-continued

The association of published lipid variants with non-HDL cholesterol levels and coronary artery disease in Iceland.

| Build 36 position | | | | Non-HDL (mg/dL) | | Coronary artery disease | | |
|---|---|---|---|---|---|---|---|---|
| Chr | Position (hg18) | MAF | Info | Effect | SE | OR | 95% CI | |
| 11 | 116,159,645 | 0.46743 | 0.999 | −0.5 | 0.2 | 0.97 | 0.95 | 0.99 |
| 11 | 116,206,564 | 0.00228 | 0.979 | −15.1 | 2.3 | 0.91 | 0.73 | 1.14 |
| 11 | 122,039,714 | 0.40275 | 0.996 | 0.6 | 0.2 | 1.01 | 0.99 | 1.03 |
| 11 | 125,749,162 | 0.10572 | 0.999 | 0.7 | 0.3 | 1.02 | 0.99 | 1.06 |
| 12 | 110,492,139 | 0.38236 | 0.999 | 0.8 | 0.2 | 0.94 | 0.92 | 0.96 |
| 12 | 110,794,963 | 0.2284 | 0.999 | 0.8 | 0.3 | 0.94 | 0.92 | 0.97 |
| 12 | 119,901,033 | 0.30901 | 0.994 | 0.9 | 0.2 | 1.03 | 1.01 | 1.05 |
| 13 | 31,851,388 | 0.44766 | 0.999 | −0.7 | 0.2 | 0.99 | 0.97 | 1.01 |
| 14 | 23,953,727 | 0.49889 | 0.995 | 0.8 | 0.2 | 0.98 | 0.96 | 1.01 |
| 15 | 56,518,445 | 0.19278 | 0.999 | −0.6 | 0.3 | 0.99 | 0.97 | 1.02 |
| 16 | 55,542,640 | 0.38939 | 0.991 | −1.8 | 0.2 | 0.97 | 0.95 | 0.99 |
| 16 | 55,572,592 | 0.06047 | 0.997 | 2.9 | 0.5 | 1.04 | 1.00 | 1.09 |
| 16 | 66,485,543 | 0.10432 | 1.000 | −0.8 | 0.3 | 0.97 | 0.94 | 1.01 |
| 16 | 70,665,594 | 0.14755 | 0.997 | 1.3 | 0.3 | 1.03 | 1.00 | 1.06 |
| 17 | 7,032,374 | 0.35058 | 0.996 | −1.0 | 0.2 | 0.98 | 0.96 | 1.00 |
| 17 | 8,101,874 | 0.49481 | 0.998 | −0.4 | 0.2 | 0.96 | 0.94 | 0.98 |
| 17 | 39,281,652 | 0.03364 | 0.989 | 1.3 | 0.6 | 1.08 | 1.02 | 1.15 |
| 17 | 42,746,803 | 0.28266 | 0.998 | 0.6 | 0.2 | 1.02 | 1.00 | 1.04 |
| 17 | 64,394,061 | 0.32561 | 0.995 | 0.5 | 0.2 | 1.03 | 1.01 | 1.05 |
| 18 | 45,363,953 | 0.01171 | 0.999 | 4.8 | 1.0 | 1.00 | 0.91 | 1.09 |
| 19 | 8,335,323 | 0.02392 | 0.965 | −4.7 | 0.7 | 0.80 | 0.74 | 0.86 |
| 19 | 11,063,306 | 0.0888 | 0.995 | −6.8 | 0.4 | 0.89 | 0.86 | 0.92 |
| 19 | 11,088,602 | 0.45236 | 0.997 | 1.4 | 0.2 | 1.02 | 1.00 | 1.04 |
| 19 | 19,268,718 | 0.07838 | 0.997 | −3.8 | 0.4 | 0.96 | 0.92 | 1.00 |
| 19 | 50,103,781 | 0.16819 | 0.980 | 8.4 | 0.3 | 1.05 | 1.02 | 1.08 |
| 19 | 50,103,919 | 0.05236 | 0.968 | −16.9 | 0.5 | 0.83 | 0.79 | 0.87 |
| 19 | 53,898,229 | 0.39118 | 0.997 | 1.1 | 0.2 | 1.00 | 0.98 | 1.03 |
| 19 | 57,016,028 | 0.27115 | 0.999 | 0.6 | 0.2 | 1.03 | 1.01 | 1.06 |
| 19 | 59,489,660 | 0.21613 | 0.990 | −0.6 | 0.3 | 0.99 | 0.96 | 1.02 |
| 20 | 12,910,718 | 0.45731 | 0.998 | 0.4 | 0.2 | 1.00 | 0.98 | 1.03 |
| 20 | 17,793,921 | 0.15541 | 0.991 | 0.8 | 0.3 | 0.98 | 0.95 | 1.01 |
| 20 | 38,613,850 | 0.34358 | 0.997 | −1.1 | 0.2 | 0.98 | 0.96 | 1.00 |
| 20 | 39,157,752 | 0.45945 | 0.997 | 1.1 | 0.2 | 0.99 | 0.97 | 1.01 |
| 20 | 42,475,778 | 0.04599 | 0.993 | −1.3 | 0.5 | 0.98 | 0.93 | 1.03 |
| 20 | 44,018,827 | 0.21978 | 0.998 | 1.3 | 0.3 | 0.98 | 0.96 | 1.01 |

Shown are the build 36 positions (hg18), minor allele frequency (MAF), imputation information, the non-HDL effect in mg/dL and the standard error of the estimate (SE), and the OR for coronary artery disease and 95% CI for the minor allele.

TABLE 1.6

Association of del12 with various measures of liver function in Iceland

| Phenotype | $n^a$ | Effect$^b$ | Effect (95% CI)$^c$ | P | Mean (±1SD)$^d$ |
|---|---|---|---|---|---|
| | | | % change | | |
| Alanine Transaminase | 144,402 | 0.087 | 5.8 (−0.4, 12.2) | 0.065 | 28.7 (15.0-54.8) units/L |
| Alkaline Phosphatase | 126,060 | 0.840 | 50.1 (42.9, 57.2) | $3.6 \times 10^{-63}$ | 87.1 (53.5-141.7) units/L |
| Aspartate Transaminase | 144,931 | 0.072 | 4.1 (−2.9, 11.4) | 0.095 | 28.1 (14.2-55.6) units/L |
| Bilirubin | 94,805 | 0.054 | 3.7 (−2.6, 10.4) | 0.25 | 9.1 (4.6-18.0) μm/L |
| Gamma Glutamyl Transpeptidase | 138,844 | 0.113 | 10.3 (1.7, 19.2) | 0.015 | 30.9 (13.1-72.9 ) units/L |
| | | | g/L | | |
| Albumin | 78,555 | −0.109 | −0.72 (−1.37, 0.06) | 0.033 | 39.5 (33.0-46.0) g/L |

$^a$Number of individuals used in the association analysis for each of the traits.
$^b$Effect estimate, in units of standard deviation, from regression of adjusted trait values on the expected genotype count of del12.
$^c$Effect estimates and 95% CI in original units. For traits with log-normal distribution the effects are presented as percentage change with 95% CI.
$^d$Mean trait values, ± one SD, in the Icelandic population. For traits with log-normal distribution the mean and SD is calculated for log-transformed trait values and transformed back to original units.

TABLE 1.7

Common Variants at the ASGR-1 Locus Associated with Non-HDL Cholesterol and Alkaline Phosphatase in Iceland

|  | rs314253 | rs56093546 | del12 |
|---|---|---|---|
| Chromosome position | 17:7032374 | 17:7004539 | 17:7020979 |
| MAF (%) | 35.06 | 21.63 | 0.43 |
| Effect[a] on non-HDL cholesterol (P value) | −0.03 ($5.9 \times 10^{-6}$) | −0.04 ($2.0 \times 10^{-6}$) | −0.30 ($2.5 \times 10^{-10}$) |
| Adjusted for rs314253 (P) | — | 0.022 | $7.9 \times 10^{-11}$ |
| Adjusted for rs56093546 (P) | 0.0068 | — | $7.2 \times 10^{-11}$ |
| Adjusted for del12 (P) | $6.4 \times 10^{-7}$ | $1.7 \times 10^{-6}$ | — |
| Effect[a] on ALP (P value) | 0.050 ($3.9 \times 10^{-21}$) | 0.068 ($7.4 \times 10^{-28}$) | 0.82 ($3.6 \times 10^{-63}$) |
| Adjusted for rs314253 (P) | — | $5.7 \times 10^{-12}$ | $4.1 \times 10^{-66}$ |
| Adjusted for rs56093546 (P) | 0.000042 | — | $2.0 \times 10^{-66}$ |
| Adjusted for del12 (P) | $4.2 \times 10^{-24}$ | $4.0 \times 10^{-31}$ | — |
| $r^2$, D' (relative to rs314253) | — | 0.29, 0.76 | 0.001, 0.60 |
| $r^2$, D' (relative to rs56093546) | 0.29, 0.76 | — | 0.001, 1.00 |

[a]Effect estimates from the regression in units of standard deviations of the distributions of the adjusted values.
The association of rs314253 with LDL cholesterol was reported in Willer et al 2013 and with ALP in Chambers et al., 2011.

TABLE 1.8

Association of p.w158X and del12 with Cholesterols, Triglyceride, Alkaline Phosphatase, Vitamin B12 and CAD in an extended Icelandic dataset

| Trait/(n)[a] | p.W158X | | | del12 | | |
|---|---|---|---|---|---|---|
|  | Effect[b] | Effect (95% CI)[c] | P | Effect[b] | Effect (95% CI)[c] | P |
| Non-HDL cholesterol | SD | mg/dL |  | SD | mg/dL |  |
| (136,261) | −0.45 | −21.6 (−34.2, −9.6) | 0.00057 | −0.29 | −13.3 (−17.2, −9.3) | $4.0 \times 10^{-11}$ |
| LDL cholesterol |  | mg/dL |  |  | mg/dL |  |
| (53,932) | −0.38 | −15.9 (−32.7, 0.9) | 0.064 | −0.23 | −9.7 (−14.1, −5.1) | $2.8 \times 10^{-5}$ |
| Total cholesterol |  | mg/dL |  |  | mg/dL |  |
| (131,879) | −0.30 | −13.5 (−29.3, 2.2) | 0.091 | −0.23 | −10.4 (−14.2, −6.5) | $1.4 \times 10^{-7}$ |
| HDL cholesterol |  | mg/dL |  |  | mg/dL |  |
| (124,437) | 0.14 | 2.4 (−3.9, 8.7) | 0.45 | 0.15 | 2.5 (1.0, 4.0) | 0.0016 |
| Triglyceride |  | % change |  |  | % change |  |
| (82,569) | −0.17 | −8.4 (−25.5, 7.2) | 0.33 | −0.12 | −6.0 (−10.4, −1.8) | 0.0075 |
| ALP |  | % change |  |  | % change |  |
| (131,966) | 0.77 | 45.3 (20.4, 68.2) | $7.9 \times 10^{-6}$ | 0.80 | 47.7 (2.2, 87.1) | $5.6 \times 10^{-76}$ |
| Vitamin B12 |  | % change |  |  | % change |  |
| (102,624) | 0.26 | 15.6 (−4.3, 34.0) | 0.084 | 0.33 | 17.5 (3.1, 30.9) | $5.6 \times 10^{-16}$ |
| CAD |  | OR | P |  | OR | P |
| (35,134/275,567) |  | 0.61 (0.26, 1.40) | 0.24 |  | 0.66 (0.54, 0.81) | $4.5 \times 10^{-5}$ |

[a]Number of individuals with trait value and genotypes.
[b]Effect estimates from the regression in units of standard deviations (SD) of the distributions of the adjusted values.
[c]Effect estimates and 95% confidence intervals (95% CI) in mg/dL for the cholesterols, and as percentage change for triglyceride, ALP and vitamin B12.
[d]P-values adjusted for the effect of del12. This analysis was done on an updated Icelandic dataset that includes 8,453 WGS individuals and imputation into 150,656 Icelandic individuals. For none-HDL cholesterol association analysis an updated sample set was used that contained 136,261 Icelanders.

TABLE 1.9A

Correlation and conditional analysis for del12 and the seven other SNPs that show the strongest association at 17p13.1 with non-HDL cholesterol in Iceland

| Variant | Pos | EA | OA | EA. freq (%) | $r^{2\,d}$ | non-HDL Effect$^c$ | P | $P_{adjdel12}{}^a$ | $P_{adjSNP}{}^b$ |
|---|---|---|---|---|---|---|---|---|---|
| chr17: 6930020:S | 6930020 | T | C | 0.39 | 0.85 | −0.243 | $5.2 \times 10^{-7}$ | 0.10 | 2.8E−05 |
| rs188743906 | 6931736 | T | C | 0.39 | 0.85 | −0.243 | $5.2 \times 10^{-7}$ | 0.18 | 2.9E−05 |
| rs150983647 | 6942021 | T | C | 0.44 | 0.76 | −0.232 | $5.3 \times 10^{-7}$ | 0.39 | 7.6E−05 |
| chr17: 6944653:S | 6944653 | A | G | 0.39 | 0.85 | −0.242 | $5.9 \times 10^{-7}$ | 0.10 | 2.3E−05 |
| rs146261845 | 6952978 | T | C | 0.40 | 0.75 | −0.259 | $1.1 \times 10^{-7}$ | 0.88 | 0.00053 |
| chr17: 6961021:S | 6961021 | C | T | 0.39 | 0.85 | −0.250 | $2.2 \times 10^{-7}$ | 0.18 | 0.00010 |
| rs186021206 | 7010136 | A | G | 0.43 | 0.86 | −0.283 | $1.4 \times 10^{-9}$ | 0.39 | 0.067 |
| del12 | 7020979 | del12 | — | 0.41 | | −0.297 | $2.5 \times 10^{-10}$ | — | — |

$^a$P-value for correlation between the SNP and the trait, tested conditional on the association of the trait with del12.
$^b$P-value for the correlation between the trait and del12, tested conditional on the association of the trait with the SNP.
$^c$Effect estimated in units of standardized trait values.
$^d$Correlation $r^2$ between del12 and sequencing genotypes of the SNPs in 2,128 Icelandic individuals. Shown are the build 36 positions (hg18).

TABLE 1.9B

Association of del12 with Non-HDL Cholesterol, HDL Cholesterol and Triglyceride Measurements, in Iceland, Denmark and the Netherlands

| | Study population (n) | Change$^a$ ± SE | P value | Mean value$^b$ in non-carriers (SD) |
|---|---|---|---|---|
| | Non-HDL cholesterol | mg/dl | | mg/dl |
| Discovery | Iceland (119,146) | −10.4 ± 1.5 | $2.5 \times 10^{-10}$ | 156.8 (38.2) |
| Replication | The Netherlands$^c$ (5,156) | −15.4 ± 5.4 | 0.0032 | 170.7 (41.3) |
| Replication | Denmark A$^d$ (5,968) | −17.4 ± 8.1 | 0.0069 | 158.3 (42.9) |
| Replication | Denmark B$^e$ (8,822) | −21.6 ± 5.4 | $3.8 \times 10^{-5}$ | 164.5 (40.5) |
| | Combined | −11.6 ± 1.5 | $1.0 \times 10^{-16}$ | |
| | HDL cholesterol | mg/dl | | mg/dl |
| Discovery | Iceland (119,514) | 0 ± 0.4 | 0.0058 | 55.2 (15.8) |
| Replication | The Netherlands (5,537) | 2.7 ± 1.5 | 0.20 | 52.2 (13.1) |
| Replication | Denmark A (6,182) | 1.2 ± 2.7 | 0.096 | 55.2 (15.4) |
| Replication | Denmark B (9,656) | 1.5 ± 1.2 | 0.26 | 59.9 (16.2) |
| | Combined | 0 ± 0.4 | 0.00039 | |
| | Triglyceride - mg/dl | mg/dl | | mg/dl |
| Discovery | Iceland (80,011) | −1.2 ± 1.5 | 0.012 | 130.9 (75.2) |
| Replication | The Netherlands (5,537) | −0.4 ± 5.8 | 0.52 | 176.9 (121.2) |
| Replication | Denmark A (6,182) | 8.1 ± 6.9 | 0.53 | 116.8 (84.0) |
| Replication | Denmark B (8,163) | −3.5 ± 2.3 | 0.15 | 131.8 (118.5) |
| | Combined | −1.5 ± 1.2 | 0.0030 | |

$^a$Effect size, ± standard error, represents the difference in mean values between heterozygote carriers and non-carriers of the variants after adjusting for age, sex and, for Iceland, site and statin use.
$^b$Calculated based on unadjusted values.
$^c$The Nijmegen Biomedical Study (Wetzels et al. 2007).
$^d$The Danish Inter99 study (Jørgensen et al. 2003).
$^e$The Danish Addition study (Lauritzen et al. 2000). To convert the values for non-HDL cholesterol to millimoles per liter, multiply by 0.02586.

TABLE 1.10

Association of del12 with Alkaline Phosphatase and Vitamin B12 Serum Measurements in Iceland and Denmark

| | Study population (n) ALP | Change$^{3a}$ ± SE U/L | P value | Mean value$^b$ in non-carriers (SD) U/L |
|---|---|---|---|---|
| Discovery | Iceland (126,060) | +33.6 ± 2.8 | $3.6 \times 10^{-63}$ | 92.8 (64.0) |
| Replication | Denmark A (5,829) | +15.8 ± 2.6 | $1.7 \times 10^{-6}$ | 42.9 (13.5) |
| | Combined | +24.1 ± 1.9 | $9.9 \times 10^{-69}$ | |

TABLE 1.10-continued

Association of del12 with Alkaline Phosphatase and Vitamin B12 Serum Measurements in Iceland and Denmark

| | Vitamin B12 | pmol/L | | pmol/L |
|---|---|---|---|---|
| Discovery | Iceland (97,910) | +58.4 ± 8.3 | $3.1 \times 10^{-12}$ | 439.0 (171.0) |
| Replication | Denmark A (5,826) | +75.9 ± 29.2 | 0.0069 | 420.0 (146.0) |
| | Combined | +59.7 ± 7.9 | $9.9 \times 10^{-14}$ | |

[a]Effect size, ± standard error, represents the difference in mean values between heterozygote carriers and non-carriers of the variants after adjusting for age, sex and, for Iceland, site and statin use.
[b]Calculated based on unadjusted values.
[c]The Nijmegen Biomedical Study (Wetzels et al. 2007).
[d]The Danish Inter99 study (Jørgensen et al. 2003).
[e]The Danish Addition study (Lauritzen et al. 2000). To convert the values for non-HDL cholesterol to millimoles per liter, multiply by 0.02586

Example 2—ALP Data from ASGR-1 Knockout Mice

Figure 7:
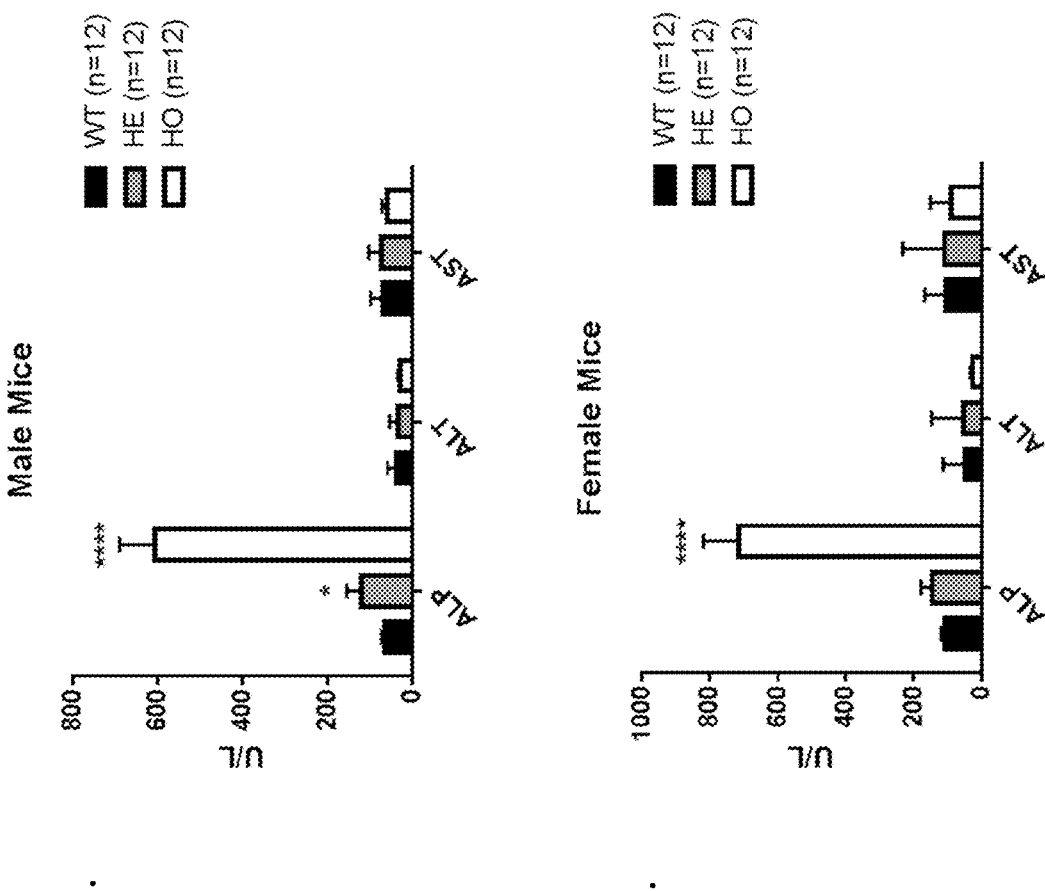
FIG. 7. Analysis of serum ALP, ALT, and AST from ASGR-1 knockout mice is provided. Panel A is data from the male mice studied and Panel B is data from the female mice.
Figure 17:
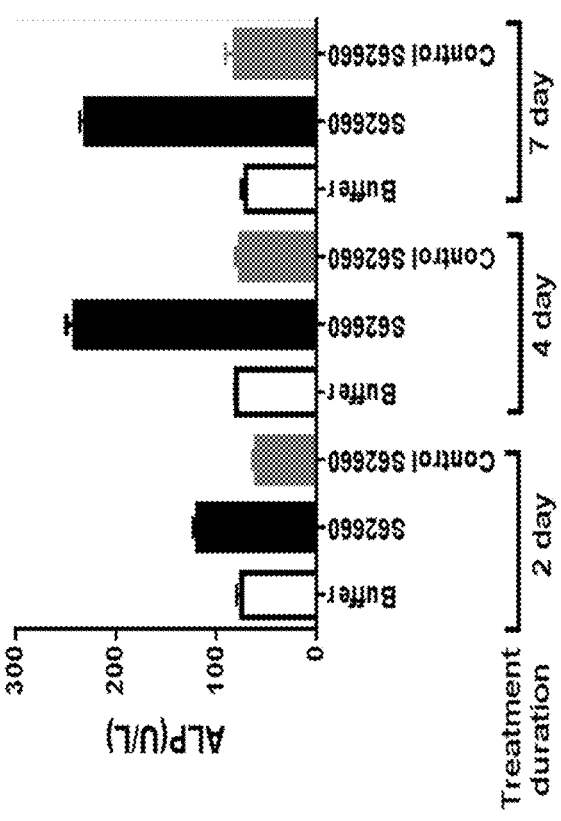
FIG. 17. RNAi in vivo data in C57BL/6J mice using various ASGR-2 constructs over the course of 7 days with one injection at day 0. The figure is a graphical representation of the relative increase in serum ALP activity.
Figure 20:
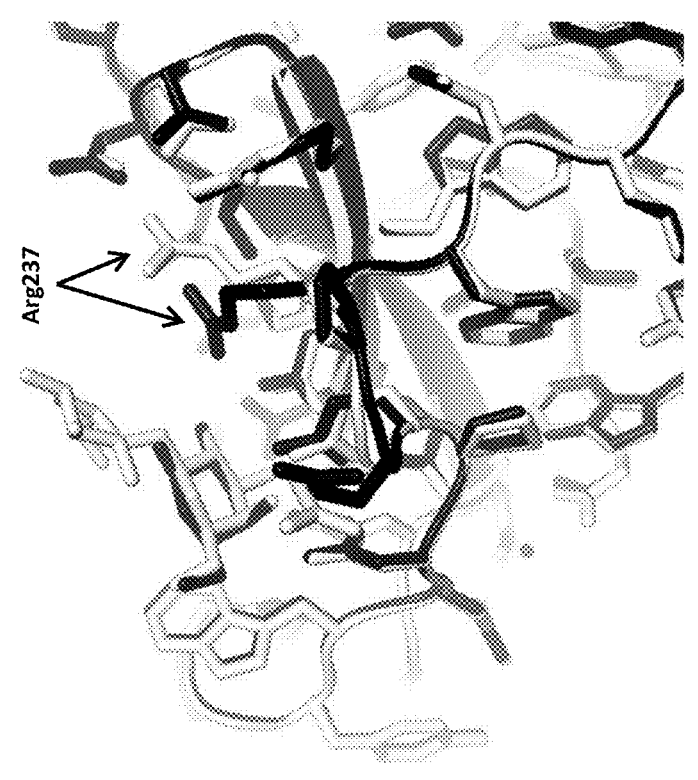
FIG. 20. A computer representation of the crystal structure of an enlarged view of the conformational difference of R237 between the ASGR-1/lactose (white) complex and ASGR-1/galactose (black) complex.

ASGR-1 KO mice (strain B6.129S4-ASGR-1$^{tm1Sau}$/SaubJxmJ) were obtained from Jackson Labs and maintained on a chow diet. Serum was collected from male and female animals after a 4 hr fast and tested in an Olympus AU640 Clinical Chemistry Analyzer. Compared to wild-type mice, serum ALP is elevated in ASGR-1 knockout mice (*, p<0.05; ****, p<0.0001, one-way ANOVA with Dunnett test). Levels of alanine transaminase (ALT) and aspartate transaminase (AST) were not significantly different between the groups. These data are summarized in FIG. 7 herein. WT=wild-type; HE=heterozygous; HO=homozygous.

Example 3—RNAi

Material and Methods siRNA Constructs

TABLE 3.1

| Vendor | Vendor catalog# | Primary Gene Target | Target Sequence | SEQ ID NO: | matched control | SEQ ID NO: |
|---|---|---|---|---|---|---|
| Fisher/Ambion | S1662 | hASGR-1 | ACUUCACAGC GAGCACGGA | 32614 | ACUUCACACGC AGCACGGA | 32632 |
| GE/Dharmacon | D-011215-01 | hASGR-2 | GCCAAGGACU UUCAAGAUA | 32615 | GCCAAGGAGAA UCAAGAUA | 32633 |
| GE/Dharmacon | D-011215-03 | hASGR-2 | UGACGGAGGU CCAGGCAAU | 32616 | UGACGGAGCAG CAGGCAAU | 32634 |
| GE/Dharmacon | D-011215-04 | hASGR-2 | AGUGAUGGCU CUUGGAAAU | 32617 | AGUGAUGGGAG UUGGAAAU | 32635 |
| Fisher/Ambion | S1665 | hASGR-2 | GACUAUAGGC ACAACUACA | 32618 | GACUAUAGCGU CAACUACA | 32636 |
| Fisher/Ambion | 194296 | hASGR-2 | CUGUGUGACUG GGUCCCAA | 32619 | CUGUGUGAGAC GGUCCCAA | 32637 |
| Fisher/Ambion | S194297 | hASGR-2 | CACCUCUGGCU AACCCAUA | 32620 | CACCUCUGCGAA ACCCAUA | 32638 |
| GE/Dharmacon | D-042958-01 | mASGR-1 | GAGACAGGCUU CCAGAAUU | 32621 | GAGACAGGGAA CCAGAAUU | 32639 |
| GE/Dharmacon | D-042958-04 | mASGR-1 | UGAAGUUAGUG GAGUCGAA | 32622 | UGAAGUUACAC GAGUCGAA | 32640 |
| Fisher/Ambion | S62656 | mASGR-1 | AGAUCACUCCA GUUUGCUA | 32623 | AGAUCACUGGU GUUUGCUA | 32641 |
| Qiagen | S102735796 | mASGR-1 | CCAUCAUGACA AAGGAUUA | 32624 | CCAUCAUGUGU AAGGAUUA | 32642 |
| GE/Dharmacon | D-061966-01 | mASGR-2 | GGAUGGAACU GAUUAUAGA | 32625 | GGAUGGAAGAC AUUAUAGA | 32643 |
| GE/Dharmacon | D-061966-02 | mASGR-2 | GGAAUUGGGCC UUCACUCA | 32626 | GGAAUUGGCGG UUCACUCA | 32644 |
| GE/Dharmacon | D-061966-03 | mASGR-2 | GACGGAACAUC ACCCACUA | 32627 | GACGGAACUAG ACCCACUA | 32645 |

TABLE 3.1-continued

| Vendor | Vendor catalog# | Primary Gene Target | Target Sequence | SEQ ID NO: | matched control | SEQ ID NO: |
|---|---|---|---|---|---|---|
| GE/Dharmacon | D-061966-04 | mASGR-2 | GGAUAGGUCUUACCGACAG | 32628 | GGAUAGGUGAAACCGACAG | 32646 |
| GE/Dharmacon | S62659 | mASGR-2 | GCAGGAUCCUAGGAUAGAA | 32629 | GCAGGAUCGAUGGAUAGAA | 32647 |
| Fisher/Ambion | S62660 | mASGR-2 | ACAUUGCUCUUUCACCUGA | 32630 | ACAUUGCUGAAUCACCUGA | 32648 |
| Fisher/Ambion | S62661 | mASGR-2 | GAAGAGUUUCGGACCCUGA | 32631 | GAAGAGUUAGCGACCCUGA | 32649 |

Expression Analysis

RNA was isolated from the HepG2, CHOs stable cell lines, or liver tissues treated with scrambled siRNA, matched control siRNA or siRNAs against hASGR-1, hASGR-2, mASGR-1 or mASGR-2 using the Qiacube and standard Qiagen RNA isolation protocol. The RNA was DNase treated using the RQ1 DNase kit (Promega). Quantitative PCR was performed according to the manufacturer's protocol on the Quantstudio 7 using the indicated primer probe set (hASGR-1: Hs01005019_m1; hASGR-2: Hs00910102_m1; mASGR-1: Mm01245581_m1, mASGR-2:Mm00431863_m1) from Applied Biosystems. 50 ng RNA/well was used and normalized with 18S internal control.

siRNA Transfection

Cells were transfected with 10 nM indicated scrambled siRNA, matched control siRNA or siRNAs against hASGR-1, hASGR-2, mASGR-1 or mASGR-2 siRNA for 3-4 days, using Lipofectamine RNAIMAX (Thermo Scientific) following manufacturer's RNAi reverse transfection protocol. Transfection was done in 96 well Screenstar microplates (Greiner bio-one) for internalization assay as well as in 96 well clear tissue culture plates (Corning) for QPCR and Western blotting.

Western Blotting

Cells were lysed in RIPA buffer containing inhibitors 3-4 days after siRNA transfection. Cell lysates were passed through a 21 gauge syringe five times and then centrifuged at 13000 rpm at 4° C. for 15 mins. Supernatants were collected and protein concentrations were determined. If needed, 30 ug of protein was deglycosylated using the deglycosylation kit (Genzyme). 10 ug-30 ug of total protein was loaded in each well. The gel was transferred onto a nitrocellulose membrane and the membrane was blocked with 5% blocking buffer for 1 hr at RT. Membrane was then probed with anti-mASGR-1 (1:1000, R &D), hASGR-1 (1:1000, ProteinTech), hASGR-2 (1:1000, Abcam), anti-flag (1:5000, Sigma), anti-his (1:1000, Cell signaling) and mouse anti β-actin (1:5000, Thermo Fisher or Cell signaling) o/n at 4° C. The membrane was further probed with anti-mouse and anti-rat secondary antibodies to detection the indicated bands.

Ligand Internalization Assay

CHO stable cell lines were treated with scrambled siRNA, matched control siRNA or siRNAs against hASGR-1, hASGR-2, mASGR-1 or mASGR-2 siRNA for 3-4 days and plated in 96-well plate. Biotin-GalNAc-PAA was incubated and streptavidin-Alexa488 was further added to cells. Draq5 was used to counterstain cells (for both cytoplasm and nuclei). Cells were scanned with Operetta Image System and data analyzed by Columbus.

Animal Study

All animal housing conditions and research protocols were approved by the Amgen Institutional Animal Care and Use Committee (IACUC). Mice were housed in a specified-pathogen free, AAALAC, Intl-accredited facility in ventilated microisolators. Procedures and housing rooms are positively pressured and regulated on a 12:12 dark:light cycle. All animals received reverse-osmosis purified water ad libitum via an automatic watering system. 10-12 week old C57BL/6J animals (The Jackson Laboratory) were singly housed and were fed standard chow (2020× Teklad global soy protein-free extruded rodent diet; Harlan).

siRNAs modified for in vivo studies were formulated with Invivofectamine 3.0 (Thermo Scientific) following the manufacturer's protocol. In brief, siRNAs were pre-mixed with complex buffer (provided by manufacturer) and Invivofectamine 3.0, and then incubated at 50° C. for 30 minute and further diluted by PBS before injection.

Mice were i.v. injected with buffer, indicated siRNA and matched control siRNA at 1-2 mg/kg body weight in 0.25 ml buffer at indicated time. Liver total RNA from harvested animals was processed for qPCR analysis.

Data from these studies is provided in FIGS. 8-17 herein.

Example 4—Y272C Mutant Data

Stable pools of Chinese hamster ovary (CHO) cells expressing C-terminal FLAG epitope-tagged murine wild-type or Y272C ASGR-1 were generated by established methods using puromycin selection. Cell surface expression of ASGR-1 was confirmed by FACS using anti-FLAG antibody both during selection process and at the time of the experiment. Ligand binding was assessed by FACS using β-GalNAc-PAA-biotin (Glycotech Corporation) and streptavidin-phycoerythrin (PE). Briefly, ligand was added to 100 ul cells (1×106 cells) in Dulbecco's Modified Eagle Medium (DMEM) without phenol red plus 2% bovine serum albumin (BSA) and incubated on ice for 60 minutes. Cells were then washed 3× with DMEM without phenol red plus 2% BSA. Streptavidin-PE was then added at 1 μg/ml for 20 minutes on ice followed by 3 more washes in DMEM without phenol red plus 2% BSA, at which point the cells were resuspended in 0.5 ml DMEM without phenol red plus 2% BSA and 5 ul of 0.1 mM SyTOx Blue viability dye and analyzed on a BD LSR II (BD Biosciences). Data are presented as Median Fluorescence Intensity as shown in Table 4.1, below.

TABLE 4.1

ASGR-1 Y272C has reduced ligand binding
compared to wild-type ASGR-1

|  | β-GalNAc-PAA-biotin, ug/ml | | | Anti-FLAG antibody |
| --- | --- | --- | --- | --- |
|  | 0 | 0.1 | 0.3 |  |
| Parental | 5.23 | 5.52 | 5.57 | 7.3 |
| WT | 4.87 | 763.51 | 1394.86 | 3959.65 |
| Y272C | 5.28 | 5.47 | 6.10 | 973.38 |

Example 5—Generation of Antibodies

Molecular Cloning of ASGR-1 and ASGR-2 Sequences

For production of recombinant ASGR-1 and ASGR-2 vectors, cDNA sequences were synthesized, obtained from a commercial source or compiled from RNA sequencing data (Amgen). Human, mouse and rat ASGR cDNA clones were from obtained commercially (OriGene Technologies, Inc.). All other ASGR cDNAs were synthesized (Integrated DNA Technologies, Inc.). GenBank accession numbers are as follows: human ASGR-1 (NM_001671.4), human ASGR-2 (NM_080913.3), mouse ASGR-1 (BC022106.1), mouse ASGR-2 (BC011197.1), rat ASGR-1 (NM_012503), rat ASGR-2 (NM_017189), pig ASGR-1 (NM_001244458), pig ASGR-2 (XM_005669199), dog ASGR-1 (XM_546579), dog ASGR-2 (XM_003434599), cynomolgus monkey ASGR-1 (XP_005582755). Since the NCBI entry for cynomologus ASGR-2 was a partial amino acid sequence (NCBI protein accession #EHH57653), the complete nucleotide sequence was compiled through the analysis of the cyno genome (genome build Macaca_fascicularis_5.0; GenBank accession number GCA_000364345.1; Washington University) and RNA sequencing data (Amgen) from cyno liver, heart and skin tissue. For transient or stable mammalian expression, cDNAs were cloned into pTT5 (National Research Council of Canada), pSLX235a (SureTech) or pJiF1 (Boyce Lab, Massachusetts General Hospital, U.S. Pat. No. 7,192,933). For individual recombinant protein production in mammalian cells, most sequences were tagged at their C-termini with a 6×His purification tag. For complexes of huASGR-1 and huASGR-2, huASGR-2 was expressed without the 6×His tag. For recombinant expression in E. coli, sequences were cloned into pET21a (Novagen, EMD Millipore). The amino acid sequences of the resultant ASGR proteins are shown in Table 1.

Expression and Purification of Recombinant Proteins

Generation of Stable CHO-S Cell Pools for Recombinant Protein Expression

CHO-S (Invitrogen, Carlsbad, California) cells were transfected with the pSLX235a vector encoding ASGR-1 or ASGR-2 using Lipofectamine LTX according to the manufacturer's recommendations (ThermoFisher Scientific). Stable pools were selected using 10 ug/ml puromycin (single selections) or 10 ug/ml puromycin and 400 ug/ml hygromycin (double selections) and by culturing the cells in fresh media every 2 days. Stable pools were then used for recombinant protein production.

Recombinant Protein Production and Purification from CHO-S Cell Stable Pools

Cells from the selected stable pools were expanded in growth medium. When sufficient cell numbers had been obtained, cultures were seeded in 2 L conical flasks in a volume of 1 L of growth medium at a viable cell density of $8 \times 10^5$ cells/ml. Cells were then cultured in suspension at 37° C., in 5% $CO_2$ for three days, after which the temperature was dropped to 31° C. for the final 7 days of production. Centrifugation was used to pellet the cells, and the resulting supernatant was filtered to generate conditioned medium.

Individual recombinant proteins were purified via the 6×His tag using Ni-Excel resin (GE Healthcare). Briefly, 1.4 L of conditioned medium was loaded onto 3×5 ml Ni-Excel Hi-trap columns and then washed with 10 column volumes of wash buffer (25 mM HEPES, pH 7.6, 250 mM NaCl, 1 mM $CaCl_2$, 50 mM imidazole). Protein was eluted from the columns with 7 column volumes of elution buffer (25 mM HEPES, pH 7.6, 250 mM NaCl, 1 mM $CaCl_2$, 400 mM imidazole). The eluted fractions were loaded onto a HiLoad Superdex 200 column via 2×10 ml injections and eluted with 25 mM HEPES, pH 7.6; 150 mM NaCl, 1 mM $CaCl_2$. The final fractions were collected based on their expected molecular weight. The identity of the proteins in each eluted peak was confirmed by LC-TOF-MS after deglycosylation (with N-glycanase, O-glycanase and sialidase) and reduction. ASGR-1/ASGR-2 complexes were purified by pre-incubating the ASGR-1-6×His Tag conditioned medium with ASGR-2-no 6×His Tag conditioned medium. These conditions permitted association of both proteins giving a complex that could be purified via the standard two-step Ni-Excel/SEC method.

Recombinant Protein Production and Purification from E. coli

E. coli codon optimized sequences were cloned into the pET21a expression plasmid. Plasmids were transformed into E. coli strain BL21(DE3) Star (ThermoFisher Scientific Inc.) and individual clones were selected using carbenicillin. For expression, cells were grown in 1 L TB growth medium (supplemented with carbenicillin) in a 4 L flask at 37° C. with shaking. When an optical density of 2 was achieved, protein expression was induced by the addition of 1 mM IPTG (final concentration). After 4 hours of induction at 37° C., the cell paste was harvested by centrifugation (recovering between 7 and 14 g cell paste/L culture). Protein localization into the insoluble fraction was confirmed by SDS-PAGE.

Inclusion bodies were recovered from the cell paste and solubilized in 6M guanidinium containing 10 mM DTT. Successful protein refolding was established by screening a matrix of 32 conditions that included a variety of buffers, pHs, denaturants, stabilizing agents and reducing agents. The refolding procedure was initiated by rapidly diluting the dissolved inclusion bodies at a ratio of 1:15 into the appropriate refold buffer, maintaining approximately 1 mg of protein per condition. The samples were then incubated at 4° C. for 60 hours. The resulting batches were analysed by SDS-PAGE and Ion Exchange chromatography to identify the optimal refolding conditions. For the ASGR-1 CBD (148-291), the final refold conditions were: pH 9.5, 2.5M urea, 20% glycerol, 4 mM cysteine and 4 mM cystamine.

Generation of Anti-ASGR Immune Responses

Mouse Strains

Fully human antibodies to human ASGR were generated by immunizing XENOMOUSE® transgenic mice (U.S. Pat. Nos. 6,114,598; 6,162,963; 6,833,268; 7,049,426; 7,064,244, which are incorporated herein by references in their entirety; Green et al., 1994, Nature Genetics 7:13-21; Mendez et al., 1997, Nature Genetics 15:146-156; Green and Jakobovitis, 1998, J. Ex. Med, 188:483-495; Kellerman and Green, Current Opinion in Biotechnology 13, 593-597, 2002). Animals from the XMG2-K, XMG2-KL, XMG4-K and XMG4-KL XENOMOUSE® strains were used for all immunizations.

Mouse anti-human ASGR antibodies were generated by immunizing BALB/c, C57BL/6 and CD-1 mice (Charles River Laboratories, San Diego, California) as well as B6.129S4-ASGR-1$^{tm1Sau}$/SaubJxmJ (ASGR-1 KO mice) and C57BL6×129 F1 mice (Jackson Laboratory, Sacramento, CA).

Fully human, heavy chain only antibodies (HCAbs) were generated by immunizing the VH4 and 8V3 strains of transgenic Harbour mice (Janssens et al. 2006, PNAS 103: 15130-15135; Harbour Biologics, Rotterdam, Netherlands). Rat anti-mouse ASGR antibodies were generated using Brown Norway Rats (Charles River Laboratories, San Diego, California).

Immunizations

Multiple immunogens and routes of immunization were used to generate anti-human ASGR immune responses. For genetic immunizations, mice were immunized 12-14 times over 6-8 weeks using the Helios Gene Gun system according to the manufacturer's instructions (BioRad, Hercules, California). Briefly, expression vectors encoding wild type human or mouse ASGR-1 (or both huASGR-1+huASGR-2, muASGR-1+muASGR-2) were coated onto gold beads (BioRad, Hercules, California) and delivered to the epidermis of a shaved mouse or rat abdomen. For cell-based immunizations, mice and rats were immunized with CHO-s cells (Invitrogen, Carlsbad, California) or 293-6E cells (National Resource Council of Canada) transiently transfected with expression vectors encoding human or mouse ASGR-1 (or both huASGR-1+huASGR-2, muASGR-1+muASGR-2). Animals were immunized with cells mixed with Alum prepared from aluminum potassium sulfate (EMD Chemicals Inc., Gibbstown, NJ) and CpG-ODN (Eurofins MWG Operon LLC, Huntsville, AL) 10 times over 6 weeks using a protocol that alternated between sub-cutaneous and intra-peritoneal injections. The initial boost was comprised of 4×10⁶ cells while subsequent boosts contained 2×10⁶ cells. For soluble protein immunizations, mice were immunized with a variety of human ASGR recombinant proteins representing the complete extracellular domain (ECD), the carbohydrate binding domain (CBD) or the complex of ASGR-1 and ASGR-2 ECDs (Table 5.1). Animals were immunized with recombinant protein (or recombinant protein conjugated to KLH using standard methods) mixed with Alum and CpG-ODN, Complete Freund's Adjuvant (Sigma), or MPL+ Adjuvant (Sigma) 10 times over 4-6 weeks using sub-cutaneous injections. The initial boost was comprised of 10 µg while subsequent boosts contained 5-10 µg. Human ASGR-1-specific serum titers were monitored by live-cell FACS analysis on an Accuri flow cytometer (BD Biosciences). Animals with the highest antigen-specific serum titers were sacrificed and used for hybridoma generation (Kohler and Milstein, 1975).

TABLE 5.1

Soluble, Recombinant Protein Antigens Used for Immunizations

| Recombinant Protein Immunogen | Source |
| --- | --- |
| huASGR-1 (Cat#: C428) ECD-KLH conjugate | Novoprotein |
| huASGR-1 (64-291) ECD-KLH conjugate | Amgen |
| huASGR-1 (64-291) ECD | Amgen |
| huASGR-1 (154-291) CBD | Amgen |
| huASGR-1(64-291)/huASGR-2 (61-287) ECD Complex | Amgen |
| huASGR-1(64-291)/huASGR-2 (61-287) ECD Complex-KLH conjugate | Amgen |
| muASGR-1 (63-284) | Amgen |

Preparation of Monoclonal Antibodies
Hybridoma Generation

Animals exhibiting suitable serum titers were identified and lymphocytes were obtained from spleen and/or draining lymphnodes. Pooled lymphocytes (from each immunization cohort) were dissociated from lymphoid tissue by grinding in a suitable medium (for example, Dulbecco's Modified Eagle Medium (DMEM); Invitrogen, Carlsbad, CA). B cells were selected and/or expanded using standard methods, and fused with a suitable fusion partner using techniques that were known in the art.

Antigen Enrichment of Hybridoma Pools

Fused hybridoma pools from each immune tissue harvest were used as a source of material for FACS-based enrichments using a variety of probes. To enrich for hybridomas expressing antibodies specific to native (full length, on-cell) human, cyno, mouse, rat, dog, or pig ASGR-1 (and native human ASGR-2) membranes were prepared from 293T cells transiently expressing the relevant ASGR cDNA construct. 24 hours after transfection using 293-fectin (ThermoFisher Scientific Inc.), cells were biotinylated with E-Z link NHS-LC-LC-Biotin according to the manufacturer's recommendation (ThermoFisher Scientific Inc.). After biotinylation, cells were homogenized with a needle and syringe to form membrane fragments and referred to as "membrane preps". The biotinylated membrane preps were then used to detect hybridomas expressing surface antibodies specific to the target of interest via standard biotin-streptavidin chemistry. To enrich for hybridomas capable of binding to the recombinant ASGR-1 ECD or CBD, soluble, 6×His-tagged ASGR-1 proteins were used (Amgen).

To enrich hybridoma pools for the antigen of interest, they were first incubated with the appropriate membrane prep or soluble probe. For soluble forms of ASGR-1, the recombinant protein probes were added to the hybridomas and allowed to bind. Excess probe was then washed away and the antigen-specific hybridomas were identified by simultaneous detection of surface IgG (with an Alexa 488 conjugated secondary antibody (Jackson ImmunoResearch) (Gt anti-mouse Fc for wild type mouse hybridomas and Gt anti-human Fc for transgenic mouse hybridomas)) and the soluble ASGR-1 probe via its 6×His tag (using an Amgen-derived anti-6×His monoclonal antibody conjugated to Alexa 647 via an Alexa 647 labeling kit (ThermoFisher Scientific Inc). Hybridomas expressing surface IgG and binding antigen were detected by FACS analysis on an Accuri flow cytometer. Dual positive events were sorted as single cells into 384-well plates on a FACS Aria cell sorter (BD Biosciences). For native forms of ASGR-1, biotinylated membrane preps were prepared as described from 293T cells transiently expressing the appropriate antigen. After washing away unbound probe, dual positive hybridomas expressing cell surface IgG and binding antigen were detected using an Alexa 488 conjugated secondary antibody (to detect IgG) and streptavidin conjugated to Alexa 647 (Jackson ImmunoResearch) to detect antigen. These events were sorted as single cells into 384-well plates on a FACS Aria cell sorter. After several days of culture, the hybridoma supernatants containing monoclonal antibodies were collected and used in the screening assays described in the examples below.

Example 6: Identification of ASGR-1 Specific Antibodies

The following Table 6.1 summarizes the approximate numbers of antibodies assayed:

TABLE 6.1

Summary of the identification and selection of huASGR-1 binding, ligand blocking antibodies.

| ASGR-1 Screen | Number of Antibodies |
| --- | --- |
| huASGR-1 Binders | 15731 |
| huASGR-1-Ligand Blockers (>60%) | 5306 |
| Sequences Unique huASGR-1-Ligand Blockers | 2603 (disclosed in Table 3) |
| huASGR-1-Ligand Blockers (>50%) | 172 (disclosed in Table 3) |

Example 6-A: Initial Selection of ASGR-1 Specific Binding Antibodies

Hybridoma supernatants (monoclonal antibodies) were screened for binding to human ASGR-1 transiently expressed on Human Embryonic Kidney (HEK) 293 cells using the Cell Insight™ High Content Imaging Platform (ThermoFisher Scientific). Human ASGR-1 was transiently expressed on host HEK 293 cells by transfection using human ASGR-1 DNA, Gibco™ Opti-MEM® media and 293Fectin™ reagents following the protocol set out by the manufacturer. Transfected HEK 293 cells expressing the human ASGR-1, hybridoma supernatant or control samples, Alexa Fluor® 488 IgG Fc fragment-specific detection antibody and Hoechst 33342 stain were mixed and incubated for 3 hours at room temperature. Samples were then washed and analyzed on the CellInsight™ system. Supernatants were counter-screened against HEK 293 cells transfected with empty parental vector (referred to as mock). Analysis was done using irrelevant IgG antibody supernatant sample signal; hybridoma supernatant samples showing two times or greater signal over irrelevant IgG antibody sample were considered to be exhibiting ASGR-1-specific binding profiles and selected for further characterization. See Table 6.1.

Example 6-B: Identification of ASGR-1 Receptor-Ligand Blocking Antibodies

ASGR-1-binding hybridoma supernatants were tested for their ability to block ASGR-1 from binding ligand. Competitive binding assays were performed on the antigen specific hybridoma supernatant samples using FACS on either HEK 293 cells transiently expressing human ASGR-1 or CHO-S cells stably expressing Human ASGR-1 as follows. HEK 293 cells or CHO-S cells expressing human ASGR-1 were mixed with the antibody sample (hybridoma supernatants specific for ASGR-1) and incubated for 1 hour at 4° C., and then washed twice. Cells with bound sample were then incubated with precomplexed β-GalNAc-PAA-Biotin (GlycoTech, Gaithersburg, Maryland)/Alexa Fluor® 647-Streptavidin for 45 minutes at 4° C. The concentration of β-GalNAc-PAA-Biotin was used at the binding EC50 concentration on the specific cell line. The concentration of Alexa Fluor® 647 Streptavidin was used at a 2:1 molar ratio to β-GalNAc-PAA-Biotin. The 7-AAD cell viability stain was then added and the cells incubated for a further 15 minutes at 4° C., washed twice and resuspended in FACS buffer. Where tolerated by cell viability, FACS buffer supplemented with 1 mM Calcium Chloride was used in all steps. Samples were analyzed using a BD Accuri™ Flow Cytometer and an Intellicyt HyperCyt Autosampler. Analysis was done using irrelevant (non-ASGR-1 specific) IgG antibody supernatant control signal on both mock transfected HEK 293 cells and Human ASGR-1 transfected HEK 293 cells to determine maximum and minimum β-GalNAc-PAA-Biotin binding signal. Using these maximum and minimum binding signals, the % β-GalNAc-PAA-Biotin binding inhibition was determined. ASGR-1 antibodies having the ability to reduce ligand binding ≥60% were identified (Table 6.1), and sequenced using methods available to those skilled in the art. The sequences of unique ASGR-1-specific, ligand blocking antibodies are displayed in Table 2-7 herein.

The unique ASGR-1-specific, ligand blocking antibodies were then tested for their ability to block the GalNAc ligand under more stringent conditions using a single, known antibody concentration (5 ug/ml). The receptor-ligand blocking assays were performed using 293T cells transiently expressing ASGR-1 or CHOs cells that had been stably transfected with ASGR-1. ASGR-1 antibodies having the ability to reduce ligand binding ≥50% were identified. See Table 6.1.

Example 7: Antibody Characterization Assays

A. ASGR-1 Species Cross Reactivity, ASGR-2 Selectivity Assays and Hepatoma (HEPG2) Binding Assays Human ASGR-1-specific, ligand competing antibody samples were tested for binding to ASGR-1 from other species (cynomolgous monkey ASGR-1, mouse ASGR-1, rat ASGR-1, dog ASGR-1, and pig ASGR-1) as well as to human ASGR-2 in FACS binding assays at normalized antibody concentrations. For cell-based assays, HEK 293 cells expressing the appropriate antigen of interest were mixed with antibody sample or controls, incubated for 1 hour at 4° C., and then washed twice. Cells with bound antibody were then incubated with Alexa Fluor® 647 IgG Fc fragment-specific detection antibody and 7-AAD viability stain for 15 minutes at 4° C., washed once and resuspended in FACS buffer. Samples were analyzed using a BD Accuri™ Flow Cytometer and an Intellicyt HyperCyt Autosampler. As a negative control, supernatants and controls were also screened against HEK 293 cells transfected with empty parental vector. Analysis was done using irrelevant (non-ASGR-1 specific) IgG antibody supernatant sample signal; hybridoma supernatant samples showing at least two times the signal over irrelevant IgG antibody sample were considered to be exhibiting ASGR-1-species specific binding profiles. For membrane-prep binding assays, ASGR-1 species specific membrane preps were used to coat LumAvidin® microspheres (beads) and tested for binding to selected hybridoma supernatants or controls. Briefly, ASGR-1 species specific membrane preps were incubated with streptavidin-coated LumAvidin® beads for 45 minutes in the dark at room temperature and washed twice. Beads were resuspended in FACS buffer containing StabilGuard®. Antigen-bound beads were then incubated with normalized antibody sample for 1 hour in the dark at room temperature, washed twice, incubated with Alexa Fluor® 488 IgG Fc fragment-specific detection antibody for 15 minutes in the dark at room temperature, washed once and finally resuspended in FACS buffer. Samples were analyzed using an Intellicyt iQue™ Screener Platform. FACS buffer supplemented with 1 mM Calcium Chloride was used in all steps. As a negative control, supernatants and controls were also screened against a non-ASGR-1 antigen membrane prep coated on the LumAvidin® beads. Analysis was done using irrelevant (non-ASGR-1 specific) IgG antibody supernatant sample signal; hybridoma supernatant samples showing at least two times the signal over irrelevant IgG antibody sample were considered to be exhibiting specific binding profiles. See Table 7.1.

Human ASGR-1-specific, ligand competing hybridoma supernatant samples were screened for binding to the human hepatocellular carcinoma cell line HepG2 (ATCC HB-8065) at normalized antibody concentrations. For FACS binding assays, HepG2 cells were mixed with normalized antibody samples or controls, incubated for 1 hour at 4° C., and washed twice. Cells with bound antibody were then incubated with Alexa Fluor® 647 IgG Fc fragment-specific detection antibody and 7-AAD viability stain for 15 minutes at 4° C., washed once and resuspended in FACS buffer. Samples were analyzed using a BD Accuri™ Flow Cytometer and an Intellicyt HyperCyt Autosampler. For high content imaging binding assays, HepG2 cells were mixed with normalized antibody samples or controls, incubated for 1 hour at room temperature and washed twice. Cells with bound antibody were then incubated with Alexa Fluor® 488 IgG Fc fragment-specific detection antibody and Hoechst 33342 stain for 30 minutes at room temperature, washed twice and analyzed on the CellInsight™ system. Where tolerated by cell viability, FACS buffer supplemented with 1 mM Calcium Chloride was used in all steps. Analysis was done using irrelevant (non-ASGR-1 specific) IgG antibody supernatant sample signal; hybridoma supernatant samples showing two times or greater signal over irrelevant IgG antibody sample were considered to be exhibiting HepG2 ASGR-1 specific binding profiles. See Table 7.1.

TABLE 7.1

Summary of the binding specificities of the selected human ASGR-1 binding antibodies.

| mAb | Human ASGR-1 | Cyno ASGR-1 | Mouse ASGR-1 | Rat ASGR-1 | Dog ASGR-1 | Pig ASGR-1 | HEPG2 Cells | Human ASGR-2 |
|---|---|---|---|---|---|---|---|---|
| 25A4 | Y | Y | N | Y | N | Y | Y | N |
| 26C4 | Y | Y | N | Y | N | Y | Y | N |
| 29H8 | Y | Y | N | Y | N | Y | Y | N |
| 4A2 | Y | Y | N | Y | N | Y | Y | N |
| 4H6 | Y | Y | Y | Y | N | Y | Y | N |
| 56E5 | Y | Y | N | N | N | Y | Y | N |
| 7F4 | Y | Y | N | no data | Y | Y | Y | Y |
| 7G4 | Y | Y | N | N | N | Y | Y | N |
| 48B12 | Y | Y | N | N | N | Y | Y | N |
| 184E7 | Y | Y | Y | Y | Y | Y | Y | N |
| 194A4 | Y | Y | N | Y | Y | Y | Y | N |
| 4B1 | Y | Y | Y | Y | Y | Y | Y | N |
| 72G9 | Y | Y | Y | Y | Y | Y | Y | N |
| 190F8 | Y | Y | N | N | Y | Y | Y | N |
| 191G1 | Y | Y | N | N | Y | Y | Y | N |
| 191G10 | Y | Y | N | N | Y | Y | Y | N |
| 194C1 | Y | Y | N | N | Y | Y | Y | N |
| 197G3 | Y | Y | N | N | Y | Y | Y | N |
| 198G3 | Y | Y | N | N | Y | Y | Y | N |
| 75G3 | Y | Y | N | N | Y | Y | Y | N |
| 218G4 | Y | Y | N | N | Y | Y | Y | N |
| 193E7 | Y | Y | N | N | Y | N | Y | N |
| 198D2 | Y | Y | N | Y | N | Y | Y | N |
| 202A3 | Y | Y | N | N | Y | Y | Y | N |
| 7E11 | Y | Y | N | N | N | Y | Y | N |
| 22G5 | Y | Y | N | N | N | N | Y | N |
| 5E5 | Y | Y | N | Y | N | N | Y | N |
| 54E9 | Y | Y | N | N | Y | N | Y | N |
| 6G7 | Y | Y | N | Y | N | N | Y | Y |
| 176H4 | Y | Y | N | N | Y | Y | Y | N |
| 194C10 | Y | Y | N | N | Y | Y | Y | N |
| 12D2 | Y | Y | Y | Y | Y | Y | Y | N |

B. Relative Binding Affinities for ASGR-Specific mAbs

To assess antibody and antigen interaction strength (relative binding affinity), ASGR-1 specific, ligand competing antibody hybridoma supernatants were tested in a limiting antigen binding assay. Titrated amounts of recombinant, soluble ASGR-1 biotinylated protein was incubated with streptavidin-coated LumAvidin Beads® for 45 minutes in the dark at room temperature and washed twice. Beads were resuspended in FACS buffer containing StabilGuard® and 0.05% Sodium Azide. Antigen-bound beads were then incubated with normalized hybridoma supernatant sample or controls for 18 hours in the dark at room temperature, washed twice, incubated with Alexa Fluor® 488 IgG fragment-specific detection antibody for 15 minutes in the dark at room temperature, washed once and finally resuspended in FACS buffer. Samples were analyzed using an Intellicyt iQue™ Screener Platform. FACS buffer supplemented with 1 mM Calcium Chloride was used in all steps. Analysis was done using irrelevant (non-ASGR-1 specific) IgG antibody supernatant sample signal; hybridoma supernatant samples showing at least two times or greater signal over irrelevant IgG antibody sample were considered to be exhibiting ASGR-1 specific binding profiles. In this assay method, the antibody binding signal correlates with antibody affinity. Antibody binding data for a representative antigen coating concentration that fell in the linear range of the instrument signal detection is shown in Table 7.2. The degree of antibody binding to the target (ASGR-1) correlates with the measured fluorescent intensity and thus allows a relative comparison of affinities across the panel.

TABLE 7.2

Limited Antigen Binding Assay to Assess Relative Affinities of selected mAbs

| mAb | Soluble ASGR-1 2.5 ng/mL (FACS Geomean) | mAb | Soluble ASGR-1 2.5 ng/mL (FACS Geomean) | mAb | Soluble ASGR-1 2.5 ng/mL (FACS Geomean) | mAb | Soluble ASGR-1 2.5 ng/mL (FACS Geomean) |
|---|---|---|---|---|---|---|---|
| 25A4 | 17952 | 48B12 | 26989 | 194C1 | 16937 | 7E11 | 4662 |
| 26C4 | 12007 | 184E7 | 40198 | 197G3 | 17708 | 22G5 | 1078 |
| 29H8 | 12179 | 194A4 | 38934 | 198G3 | 25969 | 5E5 | 3278 |
| 4A2 | 16604 | 4B1 | 10060 | 75G3 | 35840 | 54E9 | 6487 |
| 4H6 | 2990 | 72G9 | 34014 | 218G4 | 15105 | 6G7 | 2290 |
| 56E5 | 22648 | 190F8 | 13899 | 193E7 | 18315 | 176H4 | 29444 |
| 7F4 | 4910 | 191G1 | 9546 | 198D2 | 1872 | 194C10 | 21854 |
| 7G4 | 6795 | 191G10 | 24154 | 202A3 | 2152 | 12D2 | 105 |

C. pH and Calcium Sensitivity

This Example characterizes ASGR-1 antibodies based on the effect of pH and/or calcium on their ability to bind the target. For this example, a label-free, kinetic antibody-ASGR-1 binding assay was employed to assess the sensitivity of the antibodies to changes in pH and calcium. Briefly, the ASGR-1-specific, ligand-competing antibodies were first immobilized and then allowed to bind recombinant, soluble huASGR-1 under physiological conditions (ie. pH 7.4, 1 mM CaCl2). The amount of binding was determined and set to 100%. In order to determine if the antibody-ASGR-1 interaction was sensitive to changes in pH or Ca, the assay buffer was then changed to conditions lacking calcium, a reduced pH (pH 5.6) or both lacking calcium and reduced pH (pH 5.6), and dissociation of ASGR-1 from the mAbs monitored. The amount of ASGR-1 remaining bound under each condition was assessed and expressed as a percent of the starting signal. If a >10% difference in ASGR-1 binding signal was calculated (when compared to that measured under physiological conditions), a particular antibody was classified as being sensitive to that condition. Using this method, the selected antibodies were classified into 5 categories:

1. affected by the removal of calcium
2. unaffected by the removal of calcium or drop in pH
3. affected when both calcium is removed and pH is dropped
4. affected by calcium removal, pH drop and both combined
5. affected by the drop in pH The relative dissociation of ASGR-1 from antibodies was measured using a label-free assay on an OctetHTX instrument (ForteBio). Antibody samples were captured on anti-HuFc kinetic biosensors (ForteBio cat #18-5064) at 5 ug/mL in assay buffer (10 mM Tris, 0.1% Triton, 150 mM NaCl, 1 mg/mL BSA, 1 mM CaCl2, pH 7.4) for three minutes. A one minute baseline stabilization step was performed in assay buffer. Soluble ASGR-1 (Amgen) at 6 ug/ml in assay buffer was added and association to the antibodies was monitored for two minutes. Subsequent dissociation of ASGR-1 from the antibodies was performed by incubating the ASGR-1-mAb complexes for 10 minutes under each of the following conditions:

| | |
|---|---|
| pH 7.4 + calcium | 10 mM Tris, 0.1% Triton, 150 mM NaCl, 1 mg/mL BSA, pH 7.4, 1 mM CaCl2 |
| pH 7.4 − calcium | 10 mM Tris, 0.1% Triton, 150 mM NaCl, 1 mg/mL BSA, pH 7.4 |
| pH 5.6 + calcium | 10 mM Tris, 0.1% Triton, 150 mM NaCl, 1 mg/mL BSA, pH 5.6, 1 mM CaCl2 |
| pH 5.6 − calcium | 10 mM Tris, 0.1% Triton, 150 mM NaCl, 1 mg/mL BSA, pH 5.6 |

The binding signal at the end of the 2 minute association phase for each dissociation experiment was set to 100% and used to represent the maximal level of ASGR-1 binding. After 1 minute of dissociation, the percentage of ASGR-1 remaining bound was calculated. The lower the percent remaining at a given time point indicates increased levels of dissociation in response to the test conditions (ie. different pH and/or calcium concentrations). The change in the percentage of ASGR-1 remaining bound in response to each test condition relative to the percent remaining in the control conditions (ie. pH 7.4+calcium) was determined. Cut-offs for an antibody to be categorized as being sensitive to a particular condition were set to >10% (ie. if >10% of the ASGR-1 dissociates from the antibody under a particular test condition compared to control condition, it was deemed sensitive to that condition). The analysis was done using the 1 minute dissociation time point (except for mAb 149A1 which was binned based on the 4 minute dissociation time point). Using this analysis, the ASGR-1-binding, receptor-ligand blocking antibodies were separated into groups according to their dissociation profiles in response to pH and calcium (Table 7.3). Antibodies belonging to each category were observed.

TABLE 7.3 pH and Calcium Sensitivity of ASGR-1-mAb Interactions
pH and Calcium Sensitivity Determination
(% Change Compared to pH 7.4 + Calcium)

| mAb | pH 7.4 minus Calcium | pH 5.6 plus Calcium | pH 5.6 minus Calcium | Calcium sensitive | pH sensitive | pH and calcium sensitive | pH bin |
|---|---|---|---|---|---|---|---|
| 10G6 | 7% | 4% | 15% | N | N | Y | 3 |
| 148E10 | 7% | 19% | 33% | N | Y | Y | 5 |
| 154F4 | 10% | 41% | 67% | N | Y | Y | 5 |
| 159H8 | 6% | 10% | 26% | N | Y | Y | 5 |
| 160B12 | 6% | 8% | 22% | N | N | Y | 3 |
| 175D10 | 4% | −3% | 2% | N | N | N | 2 |
| 177D2 | 3% | 2% | 10% | N | N | Y | 3 |
| 25A4 | 2% | −3% | −1% | N | N | N | 2 |
| 26C4 | 3% | 2% | 2% | N | N | N | 2 |
| 27E7 | 20% | 35% | 46% | Y | Y | Y | 4 |
| 29E2 | 5% | 25% | 38% | N | Y | Y | 5 |
| 29H8 | 2% | −2% | 2% | N | N | N | 2 |
| 31D12 | 10% | 27% | 34% | Y | Y | Y | 4 |
| 32D6 | 26% | 33% | 55% | Y | Y | Y | 4 |
| 45B4 | 4% | 10% | 23% | N | Y | Y | 5 |
| 49F10 | 4% | −2% | 8% | N | N | N | 2 |
| 4A2 | 1% | −3% | 1% | N | N | N | 2 |
| 4B3 | 12% | 33% | 45% | Y | Y | Y | 4 |
| 4H6 | 5% | −1% | 2% | N | N | N | 2 |
| 50D4 | 6% | 0% | 9% | N | N | N | 2 |
| 50G9 | 37% | 62% | 44% | Y | Y | Y | 4 |
| 51E9 | 3% | −5% | 2% | N | N | N | 2 |
| 52G11 | 15% | 1% | 13% | Y | N | Y | 1 |
| 52H1 | 5% | −1% | 10% | N | N | N | 2 |
| 53F2 | 15% | 1% | 13% | Y | N | Y | 1 |
| 53F7 | 9% | 3% | 13% | N | N | Y | 3 |
| 55B1 | 5% | −2% | 4% | N | N | N | 2 |
| 56E5 | 1% | −6% | −1% | N | N | N | 2 |
| 57A7 | 13% | 13% | 29% | Y | Y | Y | 4 |
| 58G11 | 38% | 12% | 51% | Y | Y | Y | 4 |
| 59F2 | 48% | 52% | 74% | Y | Y | Y | 4 |
| 5E5 | 7% | 18% | 42% | N | Y | Y | 5 |
| 60D2 | 20% | 42% | 49% | Y | Y | Y | 4 |
| 60E8 | 3% | 11% | 18% | N | Y | Y | 5 |
| 63A10 | 8% | 3% | 47% | N | N | Y | 3 |
| 63G7 | 20% | 15% | 59% | Y | Y | Y | 4 |
| 64B12 | 6% | 6% | 7% | N | N | N | 2 |
| 65F10 | 25% | 18% | 37% | Y | Y | Y | 4 |
| 68G6 | 22% | 39% | 47% | Y | Y | Y | 4 |
| 6D9 | 14% | 25% | 42% | Y | Y | Y | 4 |
| 6G6 | 1% | −3% | 0% | N | N | N | 2 |
| 70D1 | 17% | 12% | 29% | Y | Y | Y | 4 |
| 7E11 | 9% | 5% | 14% | N | N | Y | 3 |
| 7F4 | 4% | 6% | 9% | N | N | N | 2 |
| 7G4 | 2% | 1% | 7% | N | N | N | 2 |
| 9G9 | 25% | 38% | 55% | Y | Y | Y | 4 |
| 65E9 | 22% | 30% | 35% | Y | Y | Y | 4 |
| 72B4 | 32% | 26% | 43% | Y | Y | Y | 4 |
| 147D10 | 13% | 4% | 11% | Y | N | Y | 1 |
| 149D11 | 11% | 3% | 11% | Y | N | Y | 1 |
| 149F8 | 1% | −8% | −1% | N | N | N | 2 |
| 22G5 | 40% | 35% | No Data | Y | Y | No Data | 4* |
| 48B12 | 4% | −6% | 0% | N | N | N | 2 |
| 52H2 | 26% | 11% | 32% | Y | Y | Y | 4 |
| 6G7 | 8% | 4% | 16% | N | N | Y | 3 |
| 64G12 | 24% | 10% | 24% | Y | N | Y | 1 |
| 72F5 | 64% | 20% | 30% | Y | Y | Y | 4 |
| 147E9 | 5% | −4% | 20% | N | N | Y | 3 |
| 184E7 | 1% | −9% | −3% | N | N | N | 2 |
| 194A4 | −1% | −7% | −3% | N | N | N | 2 |
| 208A2 | −4% | −10% | −5% | N | N | N | 2 |
| 210G10 | −3% | −10% | −5% | N | N | N | 2 |
| 4B1 | 6% | −5% | −2% | N | N | N | 2 |
| 62H10 | 13% | −2% | 14% | Y | N | Y | 1 |
| 72G9 | 1% | −7% | −1% | N | N | N | 2 |
| 148H10 | 45% | 10% | 47% | Y | N | Y | 1 |
| 173C11 | 17% | 0% | 29% | Y | N | Y | 1 |
| 179C2 | 25% | 0% | 45% | Y | N | Y | 1 |
| 47C1 | 13% | −1% | 10% | Y | N | Y | 1 |
| 49C1 | 72% | 23% | 64% | Y | Y | Y | 4 |
| 60C12 | 14% | −3% | 12% | Y | N | Y | 1 |
| 60G2 | 36% | 7% | 31% | Y | N | Y | 1 |

TABLE 7.3-continued pH and Calcium Sensitivity of ASGR-1-mAb Interactions
pH and Calcium Sensitivity Determination
(% Change Compared to pH 7.4 + Calcium)

| mAb | pH 7.4 minus Calcium | pH 5.6 plus Calcium | pH 5.6 minus Calcium | Calcium sensitive | pH sensitive | pH and calcium sensitive | pH bin |
|---|---|---|---|---|---|---|---|
| 65D5 | 34% | 7% | 61% | Y | N | Y | 1 |
| 66H11 | 81% | 36% | 52% | Y | Y | Y | 4 |
| 73G1 | 100% | 33% | 62% | Y | Y | Y | 4 |
| 51E3 | 65% | 16% | 42% | Y | Y | Y | 4 |
| 53E8 | 68% | 20% | 64% | Y | Y | Y | 4 |
| 54E9 | 79% | 24% | 75% | Y | Y | Y | 4 |
| 56E3 | 75% | 21% | 16% | Y | Y | Y | 4 |
| 190C11 | −1% | −6% | −6% | N | N | N | 2 |
| 190E6 | −1% | −12% | −6% | N | N | N | 2 |
| 190F12 | −1% | −6% | −6% | N | N | N | 2 |
| 190F8 | −1% | −5% | −5% | N | N | N | 2 |
| 190G11 | −2% | −8% | −5% | N | N | N | 2 |
| 190H9 | −1% | −6% | −7% | N | N | N | 2 |
| 191A10 | 0% | −5% | −5% | N | N | N | 2 |
| 191G1 | −10% | −15% | −11% | N | N | N | 2 |
| 191G10 | 0% | −5% | −5% | N | N | N | 2 |
| 191G12 | −2% | −5% | −6% | N | N | N | 2 |
| 192C10 | −1% | −6% | −6% | N | N | N | 2 |
| 192C8 | −9% | −14% | −14% | N | N | N | 2 |
| 192E4 | −2% | −9% | −8% | N | N | N | 2 |
| 192G6 | −1% | −6% | −6% | N | N | N | 2 |
| 192G8 | −1% | −5% | −6% | N | N | N | 2 |
| 192H10 | 0% | −5% | −4% | N | N | N | 2 |
| 193C7 | −1% | −8% | −8% | N | N | N | 2 |
| 194B7 | 1% | −4% | −4% | N | N | N | 2 |
| 194C1 | −7% | −12% | −8% | N | N | N | 2 |
| 196C7 | −8% | −12% | −12% | N | N | N | 2 |
| 197B6 | −1% | −8% | −7% | N | N | N | 2 |
| 197E11 | −1% | −5% | −4% | N | N | N | 2 |
| 197F2 | 0% | −6% | −6% | N | N | N | 2 |
| 197G3 | 2% | −3% | −3% | N | N | N | 2 |
| 198G3 | −1% | −4% | −4% | N | N | N | 2 |
| 213B3 | −1% | −7% | −3% | N | N | N | 2 |
| 219H1 | 2% | −3% | 1% | N | N | N | 2 |
| 74C8 | 1% | −7% | −3% | N | N | N | 2 |
| 74G6 | 1% | −9% | −4% | N | N | N | 2 |
| 75G3 | −1% | −1% | 2% | N | N | N | 2 |
| 74B2 | 8% | −9% | −5% | N | N | N | 2 |
| 74H7 | 1% | −2% | 1% | N | N | N | 2 |
| 85F7 | 2% | −2% | 2% | N | N | N | 2 |
| 198B9 | 3% | 2% | 11% | N | N | Y | 3 |
| 199A7 | 1% | 1% | 10% | N | N | Y | 3 |
| 218G4 | 1% | −4% | 0% | N | N | N | 2 |
| 146A8 | 2% | −9% | 25% | N | N | Y | 3 |
| 146B6 | 2% | −5% | 13% | N | N | Y | 3 |
| 149A1 | 2% | −7% | 9% | N | N | Y | 3* |
| 172B12 | −14% | −27% | −13% | N | N | N | 2 |
| 172C3 | −9% | −26% | 0% | N | N | N | 2 |
| 193E7 | −9% | −9% | −4% | N | N | N | 2 |
| 199E3 | −5% | −4% | −4% | N | N | N | 2 |
| 226F9 | 100% | 51% | 77% | Y | Y | Y | 4 |
| 227C1 | 100% | 54% | 73% | Y | Y | Y | 4 |
| 227F2 | 80% | 50% | 100% | Y | Y | Y | 4 |
| 65C12 | 13% | 0% | 23% | Y | N | Y | 1 |
| 176H4 | 2% | −4% | 26% | N | N | Y | 3 |
| 194C10 | 2% | 10% | 16% | N | Y | Y | 5 |
| 191E10 | −1% | −9% | −9% | N | N | N | 2 |
| 196F4 | −8% | −5% | −6% | N | N | N | 2 |
| 198D2 | −8% | −30% | −28% | N | N | N | 2 |
| 202A3 | −21% | −22% | −23% | N | N | N | 2 |
| 204G6 | −5% | −11% | −10% | N | N | N | 2 |
| 224G1 | 77% | 41% | 65% | Y | Y | Y | 4 |
| 52D10 | 21% | 3% | 45% | Y | N | Y | 1 |
| 64E2 | 48% | 29% | 49% | Y | Y | Y | 4 |

*No actual data; bin predicted on the totality of information regarding the antibody.

D. Relative Epitope Binning/Profiling

A common way to characterize epitopes is through competition experiments. Antibodies that compete with each other can be thought of as binding the same or overlapping site on the target. This example describes a method of determining competition for binding to hASGR-1 and the results of the method when applied to a number of antibodies described herein.

Binning experiments can be conducted in a number of ways, and the method employed may have an effect on the assay results. Common to these methods is that ASGR-1 is typically bound by one reference antibody and probed by another. If the reference antibody prevents the binding of the probe antibody then the antibodies are said to be in the same bin. The order in which the antibodies are employed is important. If antibody A is employed as the reference antibody and blocks the binding of antibody B the converse is not always true: antibody B used as the reference antibody will not necessarily block antibody A. There are a number of factors in play here: the binding of an antibody can cause conformational changes in the target which prevent the binding of the second antibody, or epitopes which overlap but do not completely occlude each other may allow for the second antibody to still have enough high-affinity interactions with the target to allow binding. In general, if competition is observed in either order the antibodies are said to bin together, and if both antibodies can block each other then it is likely that the epitopes overlap more completely.

For this example, a modified antibody-antibody competition assay was used to determine the relative epitope binning profiles of the ASGR-1 specific, ligand blocking antibodies in a high throughput manner. Briefly, individual antibodies were tested for their ability to compete for binding with a panel of reference antibodies chosen based on their different binding characteristics (eg. species cross reactivity, HEPG2 binding, etc.) and primary sequences. The pattern of competition/binding of each test antibody with the reference antibody panel was then determined and compared to those produced from the other test antibodies. The degree of correlation between the individual test antibody competition/binding profiles was then compared. Antibodies that showed similar competition/binding profiles were binned (grouped) together (eg. Binning Profile A, B, etc.).

Biotinylated recombinant soluble human ASGR-1 protein was coupled to streptavidin coated, uniquely barcoded LumAvidin Beads® (LumAvidin Microspheres, Cat #:L101-LXXX-01; Luminex Corp., Austin, Texas, U.S.A.) for 45 minutes in the dark at room temperature and washed twice. The reference antibody hybridoma supernatant samples were incubated with the antigen-coated beads for 1 hour in the dark at room temperature and washed three times. Beads were resuspended in FACS buffer containing StabilGuard®. The antigen-coated, reference antibody-bound beads were pooled and then divided into individual sample wells containing a normalized (2.5 ug/ml) test antibody (hybridoma supernatant) sample (or negative control), incubated for 1 hour in the dark at room temperature and washed twice. The samples were then incubated with Alexa Fluor® 488 IgG fragment-specific detection antibody for 15 minutes in the dark at room temperature, washed once and resuspended in FACS buffer. FACS buffer supplemented with 1 mM Calcium Chloride was used in all steps. Samples were analyzed using an Intellicyt iQue™ Screener Platform.

To determine the antibody competition/binding profiles of the individual test antibodies, the reference-only antibody binding signal was subtracted from the reference plus test antibody signal for each competition/binding reaction (ie. across the entire reference antibody set). An individual antibody binding profile was defined as the collection of net binding values for each competition/binding reaction. The degree of similarity between individual profiles was then assessed by calculating the coefficient of determination between each of the test antibody profiles. Test antibodies showing high degrees of similarity ($R^2 \geq 0.8$) to each other were then grouped into common binning profiles. Separate binning profiles were only defined if there were two or more samples with a high degree of correlation. If individual unique antibody binning profiles were observed (ie. they displayed a low degree of similarity to other test antibody binding profiles), the bin was classified as unknown. Using this method, the ASGR-1-binding, receptor-ligand blocking antibodies were sub-divided into 14 unique binning profiles (A, B, C, D, E, L, M, N, O, P, Q, R, T and unknown) (Table 7.4). Antibodies that displayed a unique binning profile (as defined above) but shared a relatively high degree of similarity to another profile ($R^2=0.6-0.8$) were categorized as a sub-bin (ie. A.1, A.2, etc.) of that profile.

TABLE 7.4

Relative Epitope Binning/Profiling of ASGR-1 Specific Receptor-Ligand Blocking mAbs

| mAb | Epitope BIN | mAb | Epitope BIN | mAb | Epitope BIN | mAb | Epitope BIN |
|---|---|---|---|---|---|---|---|
| 10G6 | A | 52H1 | A | 9C11 | A.3 | 60G2 | E |
| 11E2 | A | 53F2 | A | 12B12 | B | 65D5 | E |
| 11F5 | A | 53F7 | A | 147D10 | B | 66H11 | E |
| 12E9 | A | 55B1 | A | 149D11 | B | 71A6 | E |
| 12F11 | A | 56E5 | A | 149F8 | B | 73G1 | E |
| 12F12 | A | 57A7 | A | 151B9 | B | 49C5 | E.1 |
| 13F6 | A | 58G11 | A | 175F4 | B | 49D10 | E.1 |
| 148E10 | A | 59F2 | A | 22G5 | B | 51E3 | E.1 |
| 154F4 | A | 5E5 | A | 48B12 | B | 51F4 | E.1 |
| 159H8 | A | 60D2 | A | 52H2 | B | 53E8 | E.1 |
| 160B12 | A | 60E8 | A | 6G7 | B | 54E9 | E.1 |
| 175D10 | A | 63A10 | A | 7G2 | B | 56E3 | E.1 |
| 177D2 | A | 63G7 | A | 64G12 | B.1 | 56G1 | E.1 |
| 25A4 | A | 64B12 | A | 72F5 | B.1 | 190C11 | L |
| 25D12 | A | 65F10 | A | 147E9 | C | 190E6 | L |
| 26C4 | A | 68G6 | A | 184E7 | C | 190F12 | L |
| 27E7 | A | 6A6 | A | 194A4 | C | 190F8 | L |
| 28H2 | A | 6D4 | A | 208A2 | C | 190G11 | L |
| 29E2 | A | 6D9 | A | 210G10 | C | 190H9 | L |
| 29E6 | A | 6G6 | A | 4B1 | C | 191A10 | L |
| 29H8 | A | 70D1 | A | 60E12 | C | 191G1 | L |
| 31D12 | A | 7A10 | A | 61A1 | C | 191G10 | L |
| 32D6 | A | 7C3 | A | 62H10 | C | 191G12 | L |
| 3G7 | A | 7E11 | A | 63H8 | C | 192C10 | L |
| 45B4 | A | 7F4 | A | 72G9 | C | 192C8 | L |
| 49F10 | A | 7F8 | A | 8D8 | D.1 | 192E4 | L |
| 4A2 | A | 7G4 | A | 12D2 | E | 192G6 | L |
| 4B3 | A | 8D12 | A | 148H10 | E | 192G8 | L |
| 4H6 | A | 9F12 | A | 173C11 | E | 192H10 | L |
| 50D4 | A | 9G9 | A | 179C2 | E | 193C7 | L |
| 50G9 | A | 65E9 | A.1 | 47C1 | E | 194B7 | L |
| 51E9 | A | 72B4 | A.1 | 49C1 | E | 194C1 | L |
| 52G11 | A | 7H7 | A.2 | 60C12 | E | 196C7 | L |
| 197B6 | L | 197F2 | L | 198G3 | L | 219H1 | L |
| 197E11 | L | 197G3 | L | 213B3 | L | 74C8 | L |
| 74G6 | L | 74H7 | M.1 | 218G4 | O | 172B12 | Q |
| 75G3 | M | 85F7 | M.1 | 146A8 | P | 172C3 | Q |
| 89A11 | M | 198B9 | N | 146B6 | P | 193E7 | Q |
| 74B2 | M.1 | 199A7 | N | 149A1 | P | 199E3 | Q |
| 226F9 | Q | 227F2 | Q | 176H4 | R | | |
| 227C1 | Q | 65C12 | Q | 194C10 | T | | |

E. Epitope Mapping—Arginine/Glutamic Acid Mutational Profiling

This Example characterizes ASGR-1 antibodies based on the effect of mutagenesis of ASGR-1 on their ability to bind the target. Previous data indicated that the ASGR-1 CBD is primarily responsible for antibody binding for the panel of antibodies. As such, only the ASGR-1 CBD was considered structurally in the context of the full length ASGR-1 in the design of mutation sites.

Arginine/Glutamic acid mutational mapping was used to characterize epitopes bound by human ASGR-1-specific, ligand blocking antibodies. Briefly, 144 individual point mutations were made across the CBD domain of human ASGR-1 protein (SEQ ID NO:5) starting at position 148. Ninety-one constructs, representing surface residues (modelled using the ASGR-1 crystal structure in the PyMOL Molecular Graphics System (Version 1.8; Schrödinger, LLC.)) and therefore potentially accessible for antibody binding, were selected for these assays. Mutant hASGR-1 variants were constructed such that non-arginine residues were changed to arginine and where wild type arginine residues were mutated to glutamic acid. Each mutant hASGR-1 sequence was then cloned into a mammalian expression vector and used to transiently transfect CHOs cells. The ability of human ASGR-1-specific, ligand competing antibodies to bind to the mutant hASGR-1 proteins was assessed by FACS as described above.

Antibodies were tested for binding to the individual mutant and wild type ASGR-1 constructs using normalized antibody concentrations (5 ug/ml). CHO-S cells transiently expressing the appropriate mutated or non-mutated antigen of interest were mixed with antibody sample or controls, incubated for 1 hour at 4° C., and then washed twice. Cells with bound antibody were then incubated with Alexa Fluor® 647 IgG Fc fragment-specific detection antibody and 7-AAD viability stain for 15 minutes at 4° C., washed once and resuspended in FACS buffer. Samples were analyzed using a BD Accuri™ Flow Cytometer and an Intellicyt HyperCyt Autosampler. As a negative control, supernatants and controls were also screened against CHO-S cells transfected with empty parental vector (referred to as mock). In order to exclude mutants that were poorly expressed or produced mis-folded antigen, only constructs that yielded a binding data average of at least 25% or greater compared to the average binding observed on wildtype hASGR-1 was used for further analysis. Because mutant hASGR-1 expression levels varied relative to each other, sample binding data for each construct was normalized for expression by dividing the binding data from an antibody not affected by the mutations (e.g., 65C12) by the binding values of each test antibody on a given mutant construct. Also, because the antibody binding affinities varied amongst the samples, the expression corrected data (above) was further normalized by comparing test antibody binding on each mutant construct to wild type hASGR-1. Identification of specific mutations that affected test antibody binding was performed by an interquartile range (IQR) analysis to determine statistical outliers. A mutation was identified as a "hit" if the calculated values were ≥3× the IQR (above the $3^{rd}$ quartile/upper fence) for a given mutant construct. Although IQR analysis was used here to determine significance and identify hits, one skilled in the art will recognize that a number of methods could be employed in order to normalize the data (eg. using epitope-tagged constructs or other ASGR-1-binding antibodies directed against non-CBD epitopes). Any statistically significant reduction in antibody binding signal to a mutant construct (compared to that determined for binding to wild type ASGR-1) determined by these methods could be used for hit identification.

For illustrative purposes, Table 7.5 shows the IQR analysis with a single mutant construct (i.e., H203).

TABLE 7.5

IQR analysis (representative data for construct H203)

| mAb | FACS Binding Geomean | | Expression Normalization to mAb 65C12 | | Antibody Binding Normalization to wt ASGR1 Binding | | >Q3 + 3xIQR Gating | |
|---|---|---|---|---|---|---|---|---|
| | wt ASGR1 | H203 | wt ASGR1 | H203 | wt ASGR1 | H203 | wt ASGR1 | H203 |
| 4A2 | 41104 | 18946 | 1.3644 | 1.3597 | 1.0000 | 0.9966 | 1.0000 | 0.9966 |
| 7E11 | 45453 | 14714 | 1.2338 | 1.7509 | 1.0000 | 1.4191 | 1.0000 | 1.4191 |
| 56E5 | 42617 | 20345 | 1.3159 | 1.2662 | 1.0000 | 0.9622 | 1.0000 | 0.9622 |
| 7G4 | 48526 | 18542 | 1.1557 | 1.3893 | 1.0000 | 1.2022 | 1.0000 | 1.2022 |
| 53F7 | 43474 | 18081 | 1.2900 | 1.4248 | 1.0000 | 1.1045 | 1.0000 | 1.1045 |
| 10G6 | 43059 | 18213 | 1.3024 | 1.4145 | 1.0000 | 1.0860 | 1.0000 | 1.0860 |
| 26C4 | 45991 | 13484 | 1.2194 | 1.9105 | 1.0000 | 1.5668 | 1.0000 | 1.5668 |
| 6G6 | 47628 | 20505 | 1.1775 | 1.2564 | 1.0000 | 1.0670 | 1.0000 | 1.0670 |
| 29H8 | 40927 | 13217 | 1.3702 | 1.9491 | 1.0000 | 1.4225 | 1.0000 | 1.4225 |
| 25A4 | 55579 | 20036 | 1.0090 | 1.2858 | 1.0000 | 1.2743 | 1.0000 | 1.2743 |
| 32D6 | 36128 | 13465 | 1.5522 | 1.9132 | 1.0000 | 1.2325 | 1.0000 | 1.2325 |
| 198D2 | 16882 | 7138 | 3.3219 | 3.6090 | 1.0000 | 1.0864 | 1.0000 | 1.0864 |
| 4B3 | 35561 | 1696 | 1.5770 | 15.1900 | 1.0000 | 9.6323 | 1.0000 | _9.6323_ |
| 50G9 | 37326 | 1506 | 1.5024 | 17.1095 | 1.0000 | 11.3879 | 1.0000 | _11.3879_ |
| 60D2 | 29631 | 1368 | 1.8926 | 18.8256 | 1.0000 | 9.9467 | 1.0000 | _9.9467_ |
| 59F2 | 27915 | 1346 | 2.0089 | 19.1372 | 1.0000 | 9.5260 | 1.0000 | _9.5260_ |
| 60E8 | 38653 | 1518 | 1.4509 | 16.9692 | 1.0000 | 11.6960 | 1.0000 | _11.6960_ |
| 65E9 | 29613 | 1471 | 1.8938 | 17.5097 | 1.0000 | 9.2460 | 1.0000 | _9.2460_ |
| 5E5 | 40651 | 12616 | 1.3796 | 2.0420 | 1.0000 | 1.4802 | 1.0000 | 1.4802 |
| 29E2 | 25781 | 15058 | 2.1752 | 1.7108 | 1.0000 | 0.7865 | 1.0000 | 0.7865 |
| 45B4 | 30350 | 14012 | 1.8478 | 1.8385 | 1.0000 | 0.9950 | 1.0000 | 0.9950 |
| 6G7 | 38643 | 15089 | 1.4512 | 1.7073 | 1.0000 | 1.1764 | 1.0000 | 1.1764 |
| 72F5 | 27993 | 10499 | 2.0034 | 2.4537 | 1.0000 | 1.2248 | 1.0000 | 1.2248 |
| 22G5 | 45048 | 15060 | 1.2449 | 1.7105 | 1.0000 | 1.3740 | 1.0000 | 1.3740 |
| 48B12 | 52493 | 20467 | 1.0683 | 1.2587 | 1.0000 | 1.1782 | 1.0000 | 1.1782 |
| 151B9 | 23527 | 9738 | 2.3837 | 2.6454 | 1.0000 | 1.1098 | 1.0000 | 1.1098 |
| 52H2 | 47957 | 18609 | 1.1694 | 1.3843 | 1.0000 | 1.1838 | 1.0000 | 1.1838 |
| 149D11 | 23601 | 8866 | 2.3761 | 2.9055 | 1.0000 | 1.2228 | 1.0000 | 1.2228 |
| 175F4 | 33619 | 14804 | 1.6681 | 1.7401 | 1.0000 | 1.0432 | 1.0000 | 1.0432 |
| 147E9 | 40166 | 21513 | 1.3962 | 1.1975 | 1.0000 | 0.8577 | 1.0000 | 0.8577 |
| 61A1 | 39965 | 20142 | 1.4032 | 1.2790 | 1.0000 | 0.9115 | 1.0000 | 0.9115 |
| 184E7 | 42704 | 18354 | 1.3132 | 1.4036 | 1.0000 | 1.0688 | 1.0000 | 1.0688 |

TABLE 7.5-continued

IQR analysis (representative data for construct H203)

| mAb | FACS Binding Geomean | | Expression Normalization to mAb 65C12 | | Antibody Binding Normalization to wt ASGR1 Binding | | >Q3 + 3xIQR Gating | |
|---|---|---|---|---|---|---|---|---|
| | wt ASGR1 | H203 | wt ASGR1 | H203 | wt ASGR1 | H203 | wt ASGR1 | H203 |
| 72G9 | 36507 | 18778 | 1.5361 | 1.3719 | 1.0000 | 0.8931 | 1.0000 | 0.8931 |
| 194A4 | 16291 | 12149 | 3.4424 | 2.1204 | 1.0000 | 0.6160 | 1.0000 | 0.6160 |
| 60C12 | 31286 | 19812 | 1.7925 | 1.3003 | 1.0000 | 0.7254 | 1.0000 | 0.7254 |
| 173C11 | 28526 | 13861 | 1.9659 | 1.8586 | 1.0000 | 0.9454 | 1.0000 | 0.9454 |
| 56E3 | 33876 | 20425 | 1.6555 | 1.2613 | 1.0000 | 0.7619 | 1.0000 | 0.7619 |
| 54E9 | 38589 | 15344 | 1.4533 | 1.6789 | 1.0000 | 1.1552 | 1.0000 | 1.1552 |
| 65D5 | 41007 | 20291 | 1.3676 | 1.2696 | 1.0000 | 0.9283 | 1.0000 | 0.9283 |
| 190F8 | 36503 | 15073 | 1.5363 | 1.7091 | 1.0000 | 1.1125 | 1.0000 | 1.1125 |
| 198G3 | 21467 | 13143 | 2.6124 | 1.9600 | 1.0000 | 0.7503 | 1.0000 | 0.7503 |
| 191G10 | 33829 | 17045 | 1.6578 | 1.5114 | 1.0000 | 0.9117 | 1.0000 | 0.9117 |
| 202A3 | 24848 | 12497 | 2.2570 | 2.0614 | 1.0000 | 0.9134 | 1.0000 | 0.9134 |
| 194C1 | 20860 | 11044 | 2.6884 | 2.3325 | 1.0000 | 0.8676 | 1.0000 | 0.8676 |
| 176H4 | 33506 | 10237 | 1.6737 | 2.5166 | 1.0000 | 1.5036 | 1.0000 | 1.5036 |
| 197G3 | 13308 | 3503 | 4.2141 | 7.3547 | 1.0000 | 1.7453 | 1.0000 | 1.7453 |
| 191G1 | 25298 | 10876 | 2.2168 | 2.3687 | 1.0000 | 1.0685 | 1.0000 | 1.0685 |
| 213B3 | 15070 | 12846 | 3.7212 | 2.0054 | 1.0000 | 0.5389 | 1.0000 | 0.5389 |
| 218G4 | 12212 | 7933 | 4.5923 | 3.2472 | 1.0000 | 0.7071 | 1.0000 | 0.7071 |
| 75G3 | 37223 | 14472 | 1.5066 | 1.7801 | 1.0000 | 1.1815 | 1.0000 | 1.1815 |
| 194C10 | 28138 | 13217 | 1.9930 | 1.9491 | 1.0000 | 0.9780 | 1.0000 | 0.9780 |
| 85F7 | 32968 | 16509 | 1.7010 | 1.5605 | 1.0000 | 0.9174 | 1.0000 | 0.9174 |
| 199A7 | 17005 | 9455 | 3.2978 | 2.7247 | 1.0000 | 0.8262 | 1.0000 | 0.8262 |
| 146B6 | 24138 | 14412 | 2.3233 | 1.7875 | 1.0000 | 0.7694 | 1.0000 | 0.7694 |
| 193E7 | 35508 | 13783 | 1.5794 | 1.8691 | 1.0000 | 1.1835 | 1.0000 | 1.1835 |
| 65C12 | 56080 | 25761 | 1.0000 | 1.0000 | 1.0000 | 1.0000 | 1.0000 | 1.0000 |

The bolded, underlined, and italicized values for antibodies 4B3, 50G9, 60D2, 59F2, 60E8, and 65E9 in Table 7.5 represent the statistically significant hits (i.e., >3× the IQR) whose binding was affected by mutations H203.

A summary of the hASGR-1 residues important for binding of the representative antibodies is shown in (FIG. 60, labeled as Table 7.6 in the figure). In addition, this analysis revealed that the mutation of some ASGR-1 residues had more dramatic effects on a given antibody binding than others. This likely reflects the relative contribution or importance that these residues have in mediating interactions with specific test antibodies. The degree by which each mutation impacted the ability of a test antibody to bind was determined by calculating the magnitude of an individual binding data point above the upper gate determined by each IQR analysis. The relative impact of each mutation on the binding of a given test antibody was then ranked using this method and displayed as a heatmap in FIG. 60. Dark grey shading indicates the data point deviated dramatically from the upper gate (ie. a large effect on antibody binding), while light grey/white shading indicates the data point was very close to the cut offs (ie. 3× the IQR) (FIG. 60). When aligned with the relative epitope profiling bin assignments (Example 7D above), this analysis reveals a set of core ASGR-1 amino acid positions that, when mutated, disrupt test antibody binding. As such, these positions are likely part of the ASGR-1 epitopes bound by the selected antibodies. These amino acid residues either directly contact or are involved in the interaction with the antibody, or are in close enough proximity that, when mutated, interfere with antibody binding. Amino acid positions identified as statistically significant hits, but barely made the cut offs, and map to surface ASGR-1 locations distinct from the main epitope bins (FIG. 47) may represent residues that, when mutated, disrupt the conformation of ASGR-1 such that an antibody that binds to a distinct epitope is affected (ie. an indirect effect). mAb 197G3 is an example of an antibody displaying a range of binding sensitivities in this assay, yet the most important residues (R274 and R271) can be identified by rank ordering them as described.

In order to compare the mutational hit patterns of the individual test antibodies with each other, the coefficient of determination between the test antibodies was determined. The expression and antibody binding normalized data set was used to generate binding profiles for each test antibody across the mutant panel. The resulting profiles for each individual test antibody were then compared for their degree of similarity to all of the other test antibodies. The coefficient of determination ($R^2$) for each combination was determined and converted into a heat map in order to visualize the resulting patterns (FIG. 46). For simplicity, a representative antibody from each unique mutational profile (Reference Antibody) is shown in FIG. 46. This analysis revealed 7 predominant hit patterns or mutational clusters. Test antibodies affected by the 7 predominant mutational clusters correspond to those from competition/binding binning profiles A, B, C, E and L (3 distinct hit/mutational clusters of bin A antibodies and 1 distinct hit/mutational cluster of bin B, bin C, bin E and bin L antibodies). The remaining antibodies, categorized as displaying separate binning profiles (compared to bins A, B, C, E and L), are affected by distinct mutations in ASGR-1, but also include residues that partially overlap with test antibodies belonging to the predominant bins.

This data indicates the selected antibodies bind to epitopes that partially overlap with the 7 predominant epitope regions. The residues important for the binding of antibodies belonging to the 7 predominant epitope regions were then mapped onto a computer representation of the surface of the ASGR-1 structure using the PyMOL Molecular Graphics System (Version 1.8; Schrödinger, LLC.) (FIG. 47). A residue on the surface of ASGR-1 was considered part of the same epitope region if at least one antibody from a distinct binning profile (ie. A, B, C, E and L) was identified as being sensitive to mutation. For example, the predominant epitope region for antibodies belonging to binning profile C includes hASGR-1 residues P241, D242, D243, Y245, G251 and E253 (SEQ ID NO:5). The binding of antibody 147E9 is affected by mutation of all of these residues, while antibody 184E7 is only disrupted by mutation of P241, D243 and E253. Thus, the predominant epitope region of ASGR-1 bound by antibodies belonging to binning profile C is defined as including one or more of (but not limited to) P241, D242, D243, Y245, G251 and E253 (SEQ ID NO:5). Also, note that the antibody 194A4 was classified as belonging to Bin C as determined in Example 7D, however, the results of this arginine/glutamic acid mutational profiling (as well as the results from crystal structure analysis of the ASGR-1 CBD/194A4 complex described in Example 10H) suggests that the relative epitope profiling may have been inaccurate.

Antibodies belonging to binning profile A were further sub-divided into 3 distinct mutational clusters. These clusters mapped to ASGR-1 surface positions that overlap with, or are in extremely close physical proximity to, each other consistent with a common binning profile. Antibodies that displayed binning profiles distinct from the 5 major bins (i.e., A, B, C, E and L) also showed distinct patterns of mutations that affected their binding (FIG. 46). Some binning profiles (R, O, M, M.1 and T) share significant overlap with antibodies from binning profile L, and can be considered sub-bins of this profile. Taken together, this data indicates that antibodies capable of blocking ASGR-1-ligand interactions bind to 5 major epitope regions. In addition, blocking antibodies were identified that bind to partially overlapping epitopes of these major regions.

Example 8: ASGR Internalization Assay

To determine whether the antibodies bind and also prevent internalization of ASGR-1 into cells expressing ASGR-1, an in vitro internalization assay is performed of various antibody samples.

Human ASGR-1 Internalization Cellular Imaging Assay Protocol

Reagents:

- U2OS (Human Osteosarcoma) cell line
- McCoy's 5A Medium: Gibco, #16600-082
- MEM NEAA (100×): Gibco, #11140-050
- Penicillin-Streptomycin (10,000 U/ml, 100×) Gibco, #15140-122
- L-Glutamine (100×): Gibco, #25030-081
- Fetal Bovine Serum: Gibco, #16000-044
- DPBS (without Ca and Mg): Gibco, #14190-136
- DPBS (with Ca and Mg): Gibco, #14040-133
- Cell Dissociation Buffer: Gibco, #13151-014
- 1 Liter Filter: Corning, #430517
- Hepes Buffer (1M): Gibco, #15630-080
- BacMam Virus—huASGR-1: GS: SNAP26f
- β-GalNAc-PAA-Biotin: GlycoTech, #01-011
- SNAP-Surface Alexa Fluor 546: New England Biolabs, #S9132S
- Streptavidin-Alexa Fluor 633: Life Technologies, #S21375
- Hoechst 33342: Invitrogen, #H3570
- Pitstop2: abcam Biochemical, #ab120687
- Pitstop2—negative control: abcam Biochemical, #ab120688
- Paraformaldehyde (8% Aqueous Solution): Electron Microscopy Sciences, #157-8-100
- Imaging plate—96 well Optical Bottom: Thermo Scientific Nunc, #165305
- Operetta High Content Imager: Perkin Elmer U2OS Complete Growth Medium:

- McCoy's 5A with 10% FBS, 1×MEM NEAA, 1×L-Glutamine, and 1× Penicillin-Streptomycin
- Medium was filtered before use on cells
- U2OS cell plating and culturing:
- U2OS cells were grown to 75-85% confluence in T175 before plating into a 96 well plate.

1. The U2OS culture medium was aspirated off the cells in the T175 flask
2. Cells were washed with 10 mls of DPBS and aspirated off
3. 3 mls of Cell Dissociation Buffer was added to the cells and incubated for 5 minutes inside a cell incubator (37° C., 5% CO2) to detach the cells from the T175 flask.
4. The detached cells were diluted with 7 mls of the growth medium
5. 1 ml of cells were used to count the number of cells available to plate
6. GalNAc-biotin (100 nM) and -streptavidin-Alexa633 (100 nM) were pre-mixed in assay buffer and incubated for 10 minutes at room temperature.
7. The cells were mixed together with the BacMam virus for 1-2 minutes and then plated on the 96 well imaging plate at a volume of 100 ul/well.
8. After the 15 minutes incubation, both GalNAc-biotin-streptavidin-Alexa633 and SNAP-Surface Alexa Fluor 546 were directly added (10 ul) to the medium containing Pitstop2 inhibitors for 30 minutes inside the incubator.

Treatment of Cells (16-20 Hours Incubation)

1. The next day, the medium on the 96 well plate was dumped out and washed once with DPBS.
2. McCoy's 5A Medium plus 10 mM of Hepes buffer (assay buffer) was added to the cells (100 ul) for 1 hour inside the incubator.
3. After the 1 hour incubation, the medium was dumped out and washed once with DPBS containing Ca and Mg.
4. Pitstop2 and Pitstop2 negative control were prepared in assay buffer at 20 uM.
5. Volume of 100 ul per well of the inhibitors were added to the U2OS cells for 15 minutes inside the incubator.
6. GalNAc-biotin (100 nM) and strepavidin-Alexa633 (100 nM) were pre-mixed in assay buffer and incubated for 10 minutes at room temperature.
7. SNAP-Surface Alexa Fluor 546 (2.5 uM) was prepared in assay buffer.
8. After the 15 minutes incubation, both GalNAc-biotin-streptavidin-Alexa633 and SNAPSurface Alexa Fluor 546 were directly added (10 ul) to the medium containing Pitstop2 inhibitors for 30 minutes inside the incubator.
9. After the 30 minutes incubation, medium was dumped out and the cells were washed once with DPBS.
10. The cells were fixed by adding 50 ul of 4% Paraformaldehyde (8% paraformaldehyde was diluted with DPBS) containing Hoechst dye (1:5000 dilution) to the cells for 10 minutes at room temperature.
11. After 10 minutes incubation, the cells were washed twice with DPBS and 100 ul of DPBS was added to each well.

12. The plate was imaged on the Operetta instrument with three channels measuring the different fluorescence dyes.
1) Hoechst was measured using filters in the range of excitation: 360-400 nm and emission: 410-480 nm
2) GalNAc-biotin-streptavidin-Alexa633 was measured using filters in the range of excitation: 600-630 nm and emission: 640-680 nm
3) SNAP-Surface Alexa Fluor 546 was measured using filters in the range of excitation: 520-550 nm and emission: 560-630
13. Harmony 3.5 software (Perkin Elmer) was used to identify and quantify internalized spots for fluorescence dyes added in the assay.

This internalization assay can be performed to assay the antigen binding proteins of the invention to determine how much they reduce or inhibit internalization of ASGR, ASGR-1, and/or ASGR-2.

Example 9: Additional Ligand Blocking Assays

Preparation of Desialylated Protein Ligands (Asialofetuin And Orosomucoid)
A. Asialofetuin Bovine fetuin (AHSG) was obtained commercially (Sigma) and purified using a CaptoQ Impres (GE Healthcare Life Sciences) matrix. Briefly, the material was loaded in 25 mM TRIS pH 7.9 at up to 17 mg/ml resin, resolved in 20 mM BisTRIS (pH 6.5) with a gradient of sodium chloride. The main peak was gradient pooled (~0.15M NaCl final) and resolved on a SuperDex200 SEC (GE Healthcare Life Sciences) in Hepes-buffered saline (pH 7.9). The purified AHSG was then concentrated and incubated with Innolink Biotin 354S (EMD Millipore) according to the manufacturer's instructions. The biotinylated protein was then desalted by gel filtration and concentrated once again.

The purified, biotinylated protein was subsequently desialylated by incubation with C. perfringens neuraminidase (Sigma; 1 unit/10 mg protein for 12 hours at 37° C. in 50 mM sodium phosphate, 9 mM HEPES, 0.12M NaCl, pH 6). The resulting material was harvested and digested for an additional 3 hours with A. ureafaciens neuraminidase (QAbio; 0.5 units/10 mg protein at 37° C.). The digested sample was diluted 3 fold with 20 mM HEPES containing 0.15M NaCl (pH 7.5) (HBS) to neutral pH and applied to a monomeric Avidin agarose (Pierce) HR16/10 column, run at 60 cm/hour. The loaded column was held for 15 minutes then washed with four column volumes of HBS. The biotinylated, desialylated protein was finally eluted with three column volumes of HBS containing 2 mM Biotin plus an additional two column volumes of 0.1M Glycine-HCl (pH 2.8), which was immediately neutralized during collection with 50 mM TRIS Base). Protein-containing fractions from both types of elutions were identified, pooled, concentrated, dialyzed extensively against 10 mM HEPES, 0.14M NaCl (pH 7.5), re-concentrated and finally filtered sterilized. The purified lots were then analyzed by SDS-PAGE and mass spectrometry prior to use in the described assays.
B. Orosomucoid Bovine orosomucoid (AGP) was obtained commercially (Sigma) and purified over SuperDex200 resin equilibrated in HBS (pH7.9) by size exclusion chromatography. The front of the main AGP peak was combined from 3 individual runs to generate hyperglycosylated AGP, with the remainder of the main peaks (from the 3 combined runs) to generate hypoglycosylated AGP. For biotinylation, the purified AGP was concentrated to 5 mg/ml and incubated with Innolink Biotin 354S as described. The biotinylated protein was then desalted by gel filtration and concentrated.

After biotinylation, the protein was desialylated by incubating it for 18 hours at 37° C. with one unit of C. perfringens neuraminidase (Sigma) per 10 mg protein in 50 mM sodium phosphate, 9 mM HEPES, 0.12M NaCl (pH 6). The resulting material was harvested and digested for an additional 6 hours at 37° C. with 0.5 units A. ureafaciens neuraminidase (QAbio) per 10 mg protein. The sample was diluted 3 fold with HBS to achieve a neutral pH and applied to a monomeric Avidin agarose (Pierce) HR16/10 column, run at 60 cm/hour. The loaded column was held for 15 minutes and then washed with four column volumes of HBS. The biotinylated, desialylated protein was subsequently eluted with three column volumes of HBS containing 2 mM Biotin, plus two column volumes 0.1M Glycine-HCl (pH 2.8), which was immediately neutralized during collection with 50 mM TRIS Base. Protein-containing fractions from both types of elutions were identified, pooled, concentrated, dialyzed extensively against 10 mM HEPES, 0.14M NaCl (pH 7.5), re-concentrated and finally filtered sterilized. The purified lots were then analyzed by SDS-PAGE and mass spectrometry prior to use in the described assays.

These ligands can be used in additional ligand binding assays to determine antigen binding protein inhibition of ligand binding to ASGR, ASGR-1 and/or ASGR-2.

Example 10: Crystal Structure Analysis of Interaction Between Ligands and ASGR-1 and Antibodies and ASGR-1

A. Crystal Structures of ASGR-1 Carbohydrate Binding Domain with Ligand Bound
Introduction The crystal structure of ligand free ASGR-1 CBD (carbohydrate binding domain) has been previously described (1). Protein expression of ASGR-1 CBD (SEQ ID NO:5), purification and crystallization was performed similar to the published method, however the structures described here differ from the published crystal structure. Analysis of these structures shows extra N- and C-terminal amino acids compared to the published structure, how various ligands interact with the ASGR-1 carbohydrate binding domain, and possible selectivity determinants between ASGR-1/ASGR-2 for various saccharides.
Results
Lactose Binds in the Carbohydrate Binding Pocket of ASGR-1

Protein crystals of the ASGR-1/Lactose complex were grown and the crystal structure was determined at 2.05 Å. Although a method similar to that of the published structure was followed, clear electron density is present for the lactose disaccharide in the carbohydrate binding pocket. See FIGS. 18A and 18B. In this structure, the galactose ring of the lactose disaccharide sits on top of the calcium ion at the carbohydrate binding domain and forms the majority of the contacts with the ASGR-1 protein. Hydrogen bonds are formed between lactose and ASGR-1 amino acids Q240, D242, E253, and N265. Additionally, van der Waals interactions are formed with at least W244 (SEQ ID NO:5). See FIG. 18C.

Analysis of the crystal structure identifies specific amino acids involved in the interaction between ASGR-1 and lactose. Interacting with at least these amino acids by an alternate molecule can completely or partially affect the interaction between ASGR-1 and lactose.

ASGR-1/Lactose Analysis (Distances Below were Calculated with PyMOL):

Amino acids with at least one non-hydrogen atom 4.5 Å or less to the bound lactose molecule were identified and include: Q240, D242, W244, E253, N265, D266, D267 (SEQ ID NO:5).

Amino acids with at least one non-hydrogen atom 5 Å or less to the bound lactose molecule were identified and include: Q240, D242, W244, E253, N265, D266, D267 (SEQ ID NO:5).

Amino acids with at least one non-hydrogen atom 5-8 Å from the bound lactose molecule were identified and include: N209, R237, P238, E239, P241, D243, Y245, G246, H247, G252, C255, H257, T259, D260, V268, R271, Y273 (SEQ ID NO:5).

Galactose Binds in the Carbohydrate Binding Pocket of ASGR-1 Similar to Lactose

Protein crystals of the ASGR-1/Galactose complex were grown and the crystal structure was determined at 2.4 Å. Although a method similar to that of the published structure was followed, clear electron density is present for the galactose saccharide in the carbohydrate binding domain. See FIGS. 19A and 19B.

In this structure, galactose sits on top of the calcium ion at the carbohydrate binding site and forms contacts with the ASGR-1 protein. Hydrogen bonds are formed between galactose and ASGR-1 amino acids Q240, D242, E253, and N265 (SEQ ID NO:5). Additionally, van der Waals interactions are formed with at least W244. See FIG. 19C.

Analysis of the crystal structure identifies specific amino acids involved in the interaction between ASGR-1 and galactose. Interacting with at least these amino acids by an alternate molecule may completely or partially affect the interaction between ASGR-1 and galactose. Distances below were calculated with PyMOL.

ASGR-1/Galactose Analysis (Distances Below were Calculated with PyMOL):

Amino acids with at least one non-hydrogen atom 4.5 Å or less to the bound galactose molecule were identified and include: R237, Q240, D242, W244, E253, N265, D266, D267 (SEQ ID NO:5). Amino acids with at least one non-hydrogen atom 5 Å or less to the bound lactose molecule were identified and include: R237, Q240, D242, W244, E253, N265, D266, D267 (SEQ ID NO:5).

Amino acids with at least one non-hydrogen atom 5-8 Å from the bound lactose molecule were identified and include: N209, P238, E239, P241, D243, Y245, G246, H247, G252, C255, H257, T259, V268, R271, Y273 (SEQ ID NO:5).

When comparing the ASGR-1/Lactose and ASGR-1/Galactose structures, the galactose rings of each saccharide superimpose very well. One difference in the proteins in the two structures is the conformation of R237, an amino acid in close proximity to the carbohydrate binding site. In the superimposition shown in FIG. 20, the ASGR-1/Lactose structure is shown in white and the ASGR-1/Galactose structure is shown in black.

N-acetyl-D-galactosamine (GalNAc) binds in the Carbohydrate Binding Pocket of ASGR-1 Similar to Galactose, but Forms Additional Interactions Protein crystals of the ASGR-1/GalNAc complex were grown and the crystal structure was determined at 2.2 Å. Although a method similar to that of the published structure was followed, clear electron density is present for the GalNAc saccharide in the carbohydrate binding pocket. See FIG. 21A and FIG. 21B.

In this structure, GalNAc sits on top of the calcium ion at the carbohydrate binding site and forms contacts with the ASGR-1 protein. Hydrogen bonds are formed between GalNAc and ASGR-1 amino acids Q240, D242, E253, and N265. Additionally, van der Waals interactions are formed with at least W244. In this structure, R237 is in a similar conformation as observed in the galactose complex. However, in this case hydrogen bonds are formed between R237 and the acetyl of GalNAc. These additional interactions with R237 help explain both the observed tighter binding of GalNAc (than galactose) to ASGR-1, and the tighter binding to GalNAc to ASGR-1 (than ASGR-2, in which this amino acid is Ala rather than Arg). See FIG. 21C.

ASGR-1/GalNAc Analysis (Distances were Calculated with PyMOL):

Analysis of the crystal structure identifies specific amino acids involved in the interaction between ASGR-1 and GalNAc. Interacting with at least one of these amino acids by an alternate molecule may completely or partially inhibit the interaction between ASGR-1 and GalNAc.

Amino acids with at least one atom 4.5 Å or less to the bound GalNAc molecule were identified and include: N209, R237, Q240, D242, W244, E253, H257, T259, N265, D266, D267, Y273 (SEQ ID NO:5). Amino acids with at least one non-hydrogen atom 5 Å or less to the bound lactose molecule were identified and include: N209, R237, Q240, D242, W244, E253, H257, T259, N265, D266, D267, Y273 (SEQ ID NO:5).

Amino acids with at least one non-hydrogen atom 5-8 Å from the bound lactose molecule were identified and include: P238, E239, P241, D243, Y245, G246, H247, G252, C255, F258, D260, R263, W264, V268, R271 (SEQ ID NO:5).

The coordinates for the ASGR-1 CBD/GalNAc crystal structure complex are presented in Table 10.1.

Methods

ASGR-1 Expression and Purification

For all crystallography experiments in Example 12, Human ASGR-1 CBD protein (SEQ ID NO:5) was expressed in E. coli and refolded and purified.

ASGR-1 Crystallization

Purified human ASGR-1 CBD (148-291) protein was concentrated to 8-12 mg/ml. ASGR-1/carbohydrate complex crystals grow in 0.1 M sodium cacodylate pH 6.8, 0.08 M ammonium sulfate, 21-23% PEG 8000 in the presence of 20 mM ligand (lactose, galactose or GalNAc).

Data Collection and Structure Determination

Datasets for ASGR-1 CBD complexes were collected on a Rigaku FR-E X-ray source (ASGR-1/Lactose and ASGR-1/Galactose) or at Berkeley Advanced Light Source beamline 5.0.2 (ASGR-1/GalNAc). All datasets were processed with iMosflm(2) and scaled with AIMLESS(3) from the CCP4 program suite(4).

ASGR-1/Lactose crystals grow in the C2 space group with unit cell dimensions a=113.5, b=32.3, c=40.4 Å, β=92.3° with one complex molecule per asymmetric unit, and diffract to 2.05 Å resolution. The ASGR-1 structure was solved by molecular replacement with the program PHASER(5) using the published ASGR-1 structure(1) as the starting search model. The structure was improved with multiple rounds of model building with Coot(6) and refinement with PHENIX(7). The refined structure has R=18.9 and $R_{free}$=24.4.

ASGR-1/Galactose crystals grow in the C2 space group with unit cell dimensions a=113.1, b=32.7, c=40.7 Å, β=91.6° with one complex molecule per asymmetric unit, and diffract to 2.4 Å resolution. The ASGR-1/Lactose structure was used as the starting molecule for molecular replacement, and model building and refinement were performed as described for the ASGR-1/Lactose complex to R=15.8 and $R_{free}$=22.9.

ASGR-1/GalNAc crystals grow in the C2 space group with unit cell dimensions a=112.7, b=32.3, c=40.5 Å, β=91.7° with one complex molecule per asymmetric unit, and diffract to 2.2 Å resolution. The ASGR-1/Lactose structure was used as the starting molecule for molecular replacement, and model building and refinement were performed as described for the ASGR-1/Lactose complex to R=16.5 and $R_{free}$=23.0.

Structure analysis and distance calculations were performed with the program PyMOL(8).

REFERENCES

1. Meier, M., Bider, M. D., Malashkevich, V. N., Spiess, M., and Burkhard, P. (2000) Crystal structure of the carbohydrate recognition domain of the H1 subunit of the asialoglycoprotein receptor. Journal of molecular biology 300, 857-865
2. Battye, T. G., Kontogiannis, L., Johnson, O., Powell, H. R., and Leslie, A. G. (2011) iMOSFLM: a new graphical interface for diffraction-image processing with MOSFLM. Acta crystallographica 67, 271-281
3. Evans, P. (2006) Scaling and assessment of data quality. Acta crystallographica 62, 72-82
4. CCP4. (1994) The CCP4 suite: programs for protein crystallography. Acta crystallographica 50, 760-763
5. McCoy, A. J., Grosse-Kunstleve, R. W., Adams, P. D., Winn, M. D., Storoni, L. C., and Read, R. J. (2007) Phaser crystallographic software. Journal of applied crystallography 40, 658-674
6. Emsley, P., Lohkamp, B., Scott, W. G., and Cowtan, K. (2010) Features and development of Coot. Acta crystallographica 66, 486-501
7. Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffner, R., Read, R. J., Richardson, D. C., Richardson, J. S., Terwilliger, T. C., and Zwart, P. H. (2010) PHENIX: a comprehensive Python-based system for macromolecular structure solution. Acta crystallographica 66, 213-221
8. DeLano, W. L. (2002) The PyMOL Molecular Graphics System. Palo Alto B. Crystal Structure of ASGR-1 Carbohydrate Binding Domain (CBD) with 5E5

The present example presents the crystal structure of the ASGR-1 CBD bound to the Fab fragment of 5E5, determined to 1.95 Å resolution (the conditions for which are described in the below). This structure, depicted in FIGS. 22A&B, shows that when 5E5 binds to/interacts with ASGR-1, a conformational rearrangement of the carbohydrate binding loop occurs, impairing the carbohydrate binding loop from binding to/interacting with ligand (i.e., carbohydrates). This demonstrates that the 5E5 Fab indirectly inhibits the ASGR-1 CBD/Ligand binding.

The depicted structure also allows one to identify specific core ASGR amino acid residues for the interaction interface of 5E5 with ASGR-1. This was defined as residues that are within 5 Å of the 5E5 protein. The core residues are as follows: H161, E162, W195, E196, Q198, K199, F200, Q202, H203, H204, G232, F233, K234, N235, W236, R237, P238, D261, G262, R263 (SEQ ID NO:5).

The structures were also used to identify boundary ASGR-1 amino acid residues for the interaction interface with 5E5. These residues were ASGR-1 residues that were from 5-8 Å of the 5E5 protein. The boundary residues are as follows: V159, E160, R163, T193, S194, E197, V201, I205, G206, P207, Y229, E230, T231, E239, F258, T259, D260, W264 (SEQ ID NO:5).

Specific core 5E5 amino acid residues of the interaction interface with ASGR-1 were defined as 5E5 residues that are within 5 Å of the ASGR-1 protein. The core 5E5 Heavy Chain residues include: S30, N31, W52, Y53, D54, S56, N57, Y59, Y101, S102, S103, G104, W105, Y106, D107; and the core 5E5 Light Chain residues include: 5E5 Light Chain: Q27, R30, D32, H91, Y92, S93, Y94.

Boundary 5E5 amino acid residues of the interaction interface with ASGR-1 were defined as 5E5 residues that are 5-8 Å from the ASGR-1 protein. The boundary 5E5 Heavy Chain residues include: Y32, V33, V50, G55, K58, N74, E99, V100, Y108; and the boundary 5E5 Light Chain residues include: I2, G28, I29, L33, Q90, P95, R96.

Methods

Expression and Purification of Protein Samples

The 5E5 Fab fragment was generated by cleaving the 5E5 mAb with caspase 3. Post caspase cleavage, the Fab was isolated by purification on a MonoS ion exchange column. Ni Sepharose Excel subtraction was then performed to ensure the Fc domain was removed from the sample.

5E5 mAb Heavy Chain (SEQ ID NO: 32695):
QVQLVESGGGVVQPGRSLRLSCAASGFTFSNYVMHWVRQAPGKGLEWVA

VIWYDGSNKYYADSVKGRFTISRDNSKNTLYLQMNSLRAEDTAVYYCTR

EVYSSGWYDYGMDVWGQGTTVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCGSDEVDGGDKTHTCPPCPA

PELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSV

MHEALHNHYTQKSLSLSPGHHHHHH

5E5 mAb Light Chain (SEQ ID NO: 32696):
DIQMTQSPSSLSASVGDRVTITCRASQGIRNDLGWYQQKPGKAPKRLIY

AASSLQSGVPSRFSGSGSGTEFTLTISSLQPEDFATYYCLQHYSYPRTF

GQGTKVEVKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

5E5 Fab Heavy Chain (Post Cleavage) (SEQ ID NO: 32697):
QVQLVESGGGVVQPGRSLRLSCAASGFTFSNYVMHWVRQAPGKGLEWVA

VIWYDGSNKYYADSVKGRFTISRDNSKNTLYLQMNSLRAEDTAVYYCTR

EVYSSGWYDYGMDVWGQGTTVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCGSDEVD

5E5 Fab Light Chain (Post Cleavage) (SEQ ID NO: 32698):

```
-continued
DIQMTQSPSSLSASVGDRVTITCRASQGIRNDLGWYQQKPGKAPKRLIY

AASSLQSGVPSRFSGSGSGTEFTLTISSLQPEDFATYYCLQHYSYPRTF

GQGTKVEVKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Complex Formation and Crystallization

The ASGR-1 CBD/5E5 Fab complex was made by mixing a molar excess of ASGR-1 CBD with 5E5 Fab. The complex was separated from excess ASGR-1 by purification on a size exclusion chromatography column. The ASGR-1 CBD/5E5 Fab complex was concentrated to 10 mg/ml and crystallizes in 0.1 M Tris pH 8.5, 12% PEG 4000.

Data Collection and Structure Determination

The dataset for the ASGR-1 CBD/5E5 Fab complex crystal was collected on beamline 5.0.2 at the Berkeley synchrotron and processed with Mosflm[1]/Aimless[2].

ASGR-1 CBD/5E5 Fab complex crystals grow in the P21 space group with unit cell dimensions a=62.93, b=41.75, c=118.89 Å and β=97.16 with one complex molecule per asymmetric unit, and diffract to 1.95 Å resolution. The ASGR-1 CBD/5E5 Fab complex structure was solved by molecular replacement with the program Molrep[2]. The structure was improved with multiple rounds of model building with Coot[3] and refinement with Phenix[4], to a final R=25.9/$R_{free}$=30.5. While the electron density for the ASGR-1 CBD and 5E5 Fab variable domain (along with the corresponding interface) is quite good, the electron density for the 5E5 constant domain is poor (most likely due to poor packing within the crystal lattice). This likely explains the higher R/$R_{free}$ observed from this structure refinement.

Core interaction interface amino acids were determined as being all amino acid residues with at least one non-hydrogen atom less than or equal to 5 Å from the partner protein. 5 Å was chosen as the core region cutoff distance to allow for atoms within a van der Waals radius plus a possible water-mediated hydrogen bond. Boundary interaction interface amino acids were determined as all amino acid residues with at least one non-hydrogen atom less than or equal to 8 Å from the partner protein but not included in the core interaction list. Less than or equal to 8 Å was chosen as the boundary region cutoff distance to allow for the length of an extended arginine amino acid. Amino acids that met these distance criteria were calculated with the program PyMOL[5].

REFERENCES

1. Battye, T. G., Kontogiannis, L., Johnson, O., Powell, H. R. & Leslie, A. G. iMOSFLM: a new graphical interface for diffraction-image processing with MOSFLM. *Acta Crystallogr D Biol Crystallogr* 67, 271-81 (2011).
2. CCP4. The CCP4 suite: programs for protein crystallography. *Acta Crystallogr D Biol Crystallogr* 50, 760-3 (1994).
3. Emsley, P., Lohkamp, B., Scott, W. G. & Cowtan, K. Features and development of Coot. *Acta Crystallogr D Biol Crystallogr* 66, 486-501 (2010).
4. Adams, P. D. et al. PHENIX: a comprehensive Python-based system for macromolecular structure solution. *Acta Crystallogr D Biol Crystallogr* 66, 213-21 (2010).
5. DeLano, W. L. The PyMOL Molecular Graphics System. (Palo Alto, 2002).

C. Crystal Structure of ASGR-1 Carbohydrate Binding Domain (CBD) with 22G5

Figure 23:
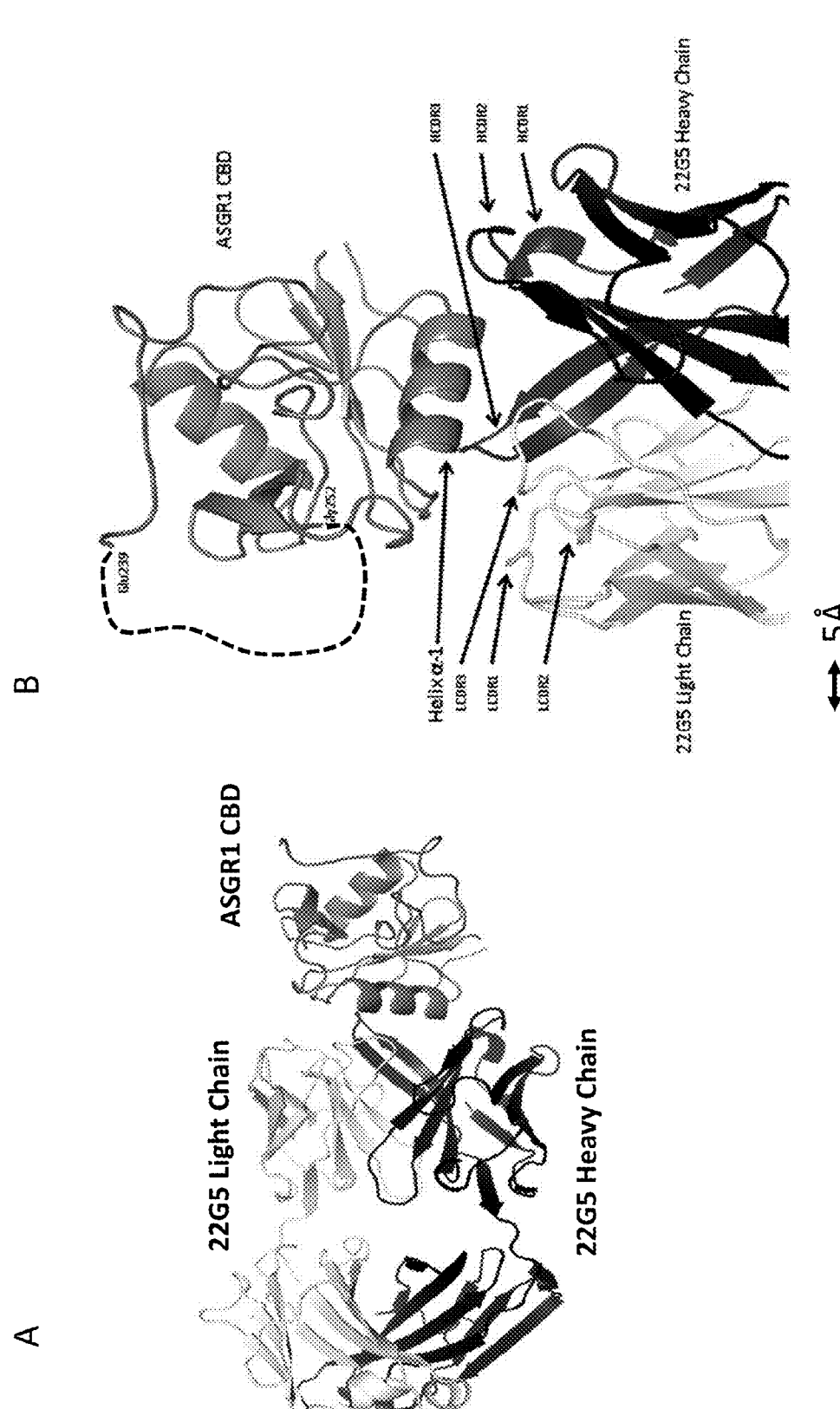
FIG. 23. Panel A shows a depiction of the structure of the ASGR-1 CB and the 22G5 Fab. Panel B is an enlarged view of the ASGR-1 CBD and 22G5 Fab that represents a disordered carbohydrate binding loop with a dashed line and highlights the indirect inhibition of ASGR-1 CBD and the ligand (GalNAc) binding. Panel B also incorporates a double-headed arrow which represents a 5 angstrom distance from tip to tip.

The present example presents the crystal structure of the ASGR-1 CBD bound to the Fab fragment of 22G5, determined to 2.1 Å resolution (the conditions of which are described above in B). This structure, depicted in FIGS. 23A&B, shows that when 22G5 binds to/interacts with ASGR-1, a conformational rearrangement of the carbohydrate binding loop occurs, impairing the carbohydrate binding loop from binding to/interacting with ligand (i.e., carbohydrates). This demonstrates that the 22G5 Fab indirectly inhibits the ASGR-1 CBD/Ligand binding.

The depicted structure also allows one to identify specific core ASGR amino acid residues for the interaction interface of 22G5 with ASGR-1. This was defined as residues that are within 5 Å of the 22G5 protein. The core residues are as follows: W167, S171, G172, K173, A174, A176, D177, N180, Y181, R183, L184, E185, D186, Q270, P272, W275 (SEQ ID NO:5).

The structures were also used to identify boundary ASGR-1 amino acid residues for the interaction interface with 22G5. These residues were ASGR-1 residues that were from 5-8 Å of the 22G5 protein. The boundary residues are as follows: P155, N157, W158, F168, S169, R170, W175, A178, D179, C182, A187, W211, C269, R271, Y273, R274, C277, T279 (SEQ ID NO:5).

Specific core 22G5 amino acid residues of the interaction interface with ASGR-1 were defined as 22G5 residues that are within 5 Å of the ASGR-1 protein. The core 22G5 Heavy Chain residues include: A33, V50, I51, S52, R53, S54, G55, G56, Y57, Y59, R99, A101, A103, G104, E106; and the core 22G5 Light Chain residues include: 22G5 Light Chain: Y32, S91, Y92, R93, Thr94, Pro95, F97.

Boundary 22G5 amino acid residues of the interaction interface with ASGR-1 were defined as 22G5 residues that are 5-8 Å from the ASGR-1 protein. The boundary 22G5 Heavy Chain residues include: S30, S31, Y32, M34, N35, W47, S49, T58, R72, N74, L100, V102, S105; and the boundary 22G5 Light Chain residues include: I2, Q27, N28, NAG100, I29, S30, S31, Q90, L96.

Methods:

The same methods were followed as described above in Example 10B except for the following changes:

The 22G5 Fab fragment was generated by cleaving the 22G5-IgG4 mAb with papain;

The ASGR-1 CBD/22G5 Fab complex was concentrated to 8 mg/ml and crystallized in 0.1 Bis-Tris pH 6.5, 0.2 sodium malonate, 20% PEG 3350;

The dataset was processed with XDS/Aimless;

ASGR-1 CBD/22G5 Fab complex crystals grow in the P212121 space group with unit cell dimensions a=46.04, b=80.34, c=169.14 Å with one complex molecule per asymmetric unit, and diffract to 2.1 Å resolution; and The structure was improved with multiple rounds of model building with Coot3 and refinement with Phenix4, to a final R=17.8/$R_{free}$=22.5.

D. Crystal Structure of ASGR-1 Carbohydrate Binding Domain (CBD) with 4A2

Figure 25:
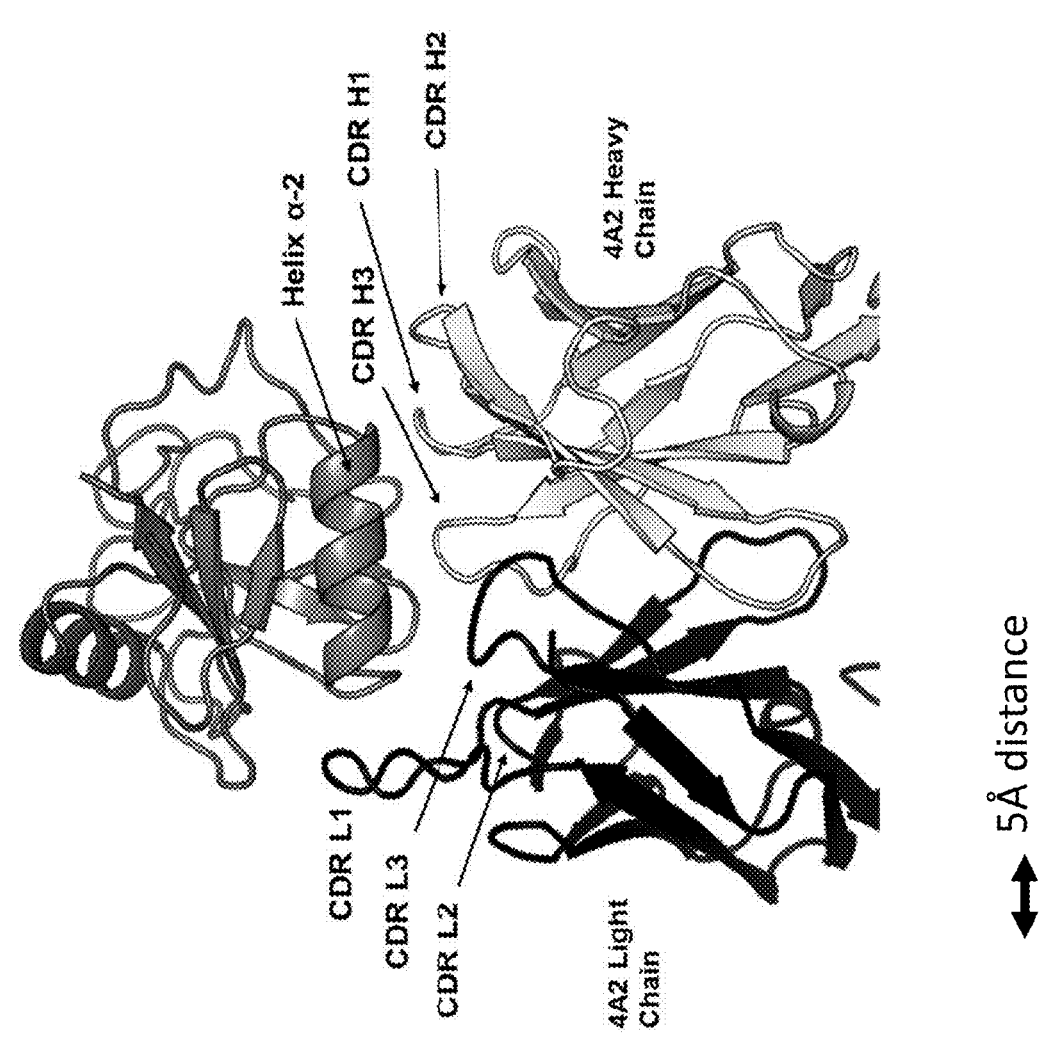
FIG. 25. An enlarged view of the structure of the ASGR-1 CBD and the 4A2 Fab that shows the CDRs of the 4A2 Fab that interact with ASGR-1 CBD Helix alpha-2 and highlights the indirect inhibition of ASGR-1 CBD and the ligand (GalNAc) binding. The figure incorporates a double-headed arrow which represents a 5 angstrom distance from tip to tip.
Figure 26:
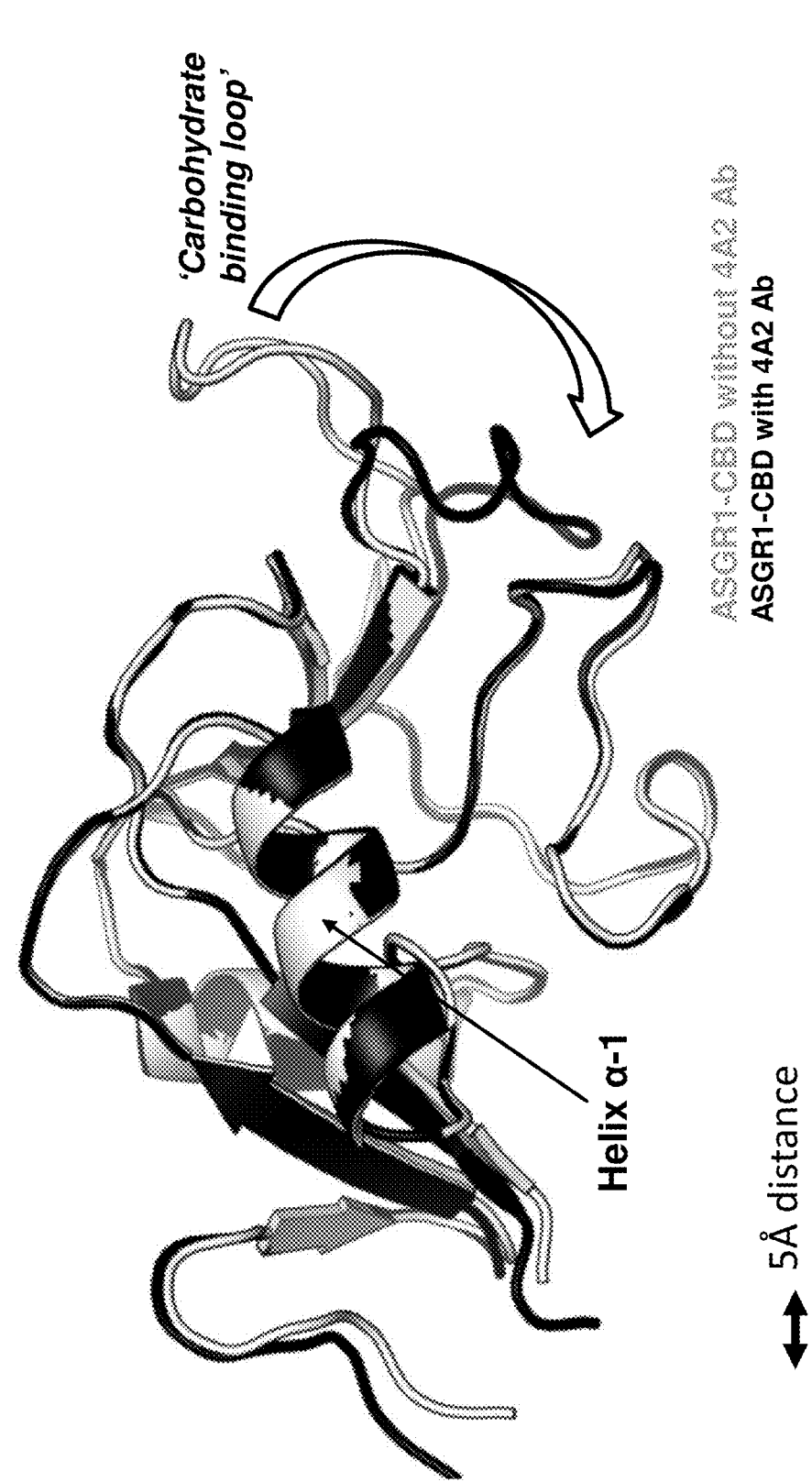
FIG. 26. An enlarged view of the structure of the ASGR-1 CBD and the carbohydrate binding loop with and without and the 4A2 Fab that includes a double-headed arrow which represents a 5 angstrom distance from tip to tip.
Figure 27:
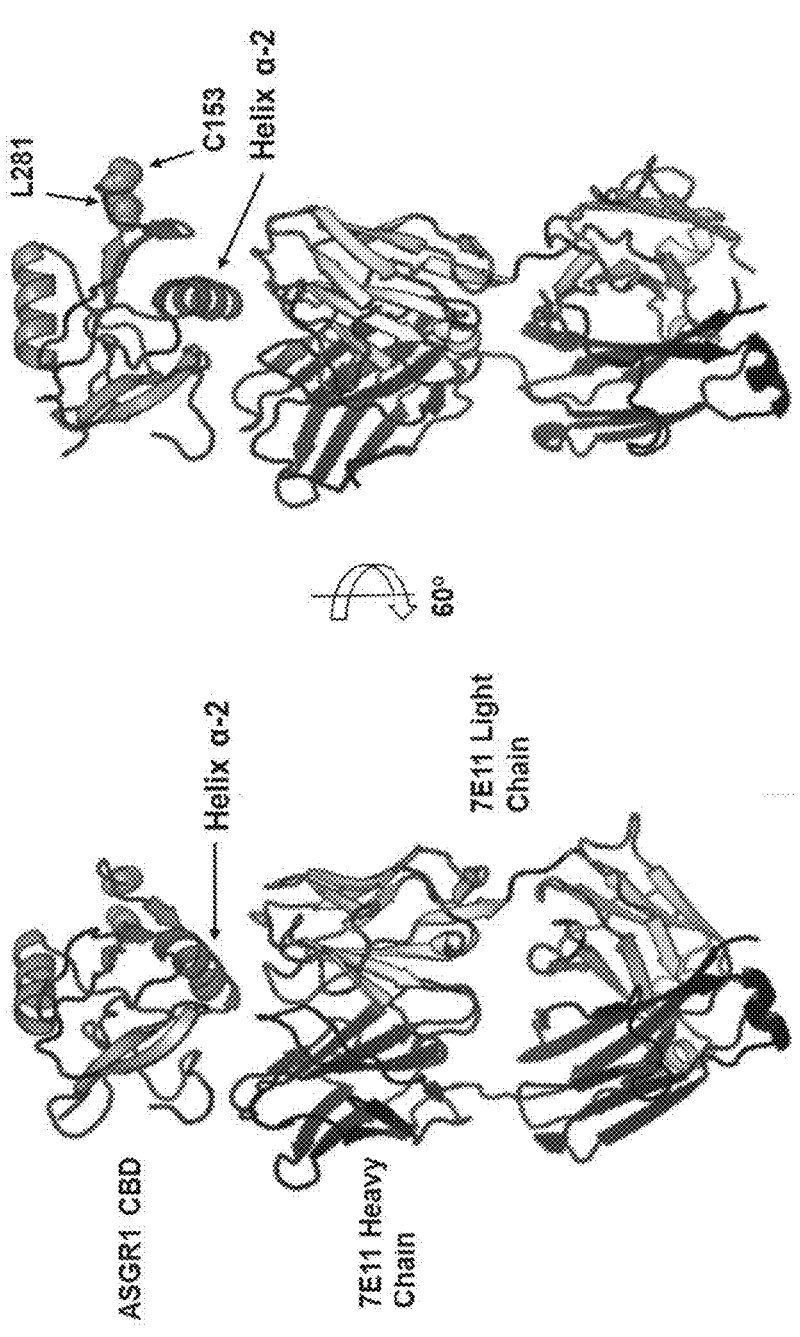
FIG. 27. A depiction of the structure of ASGR-1 CBD and the 7E11 Fab.
Figure 28:
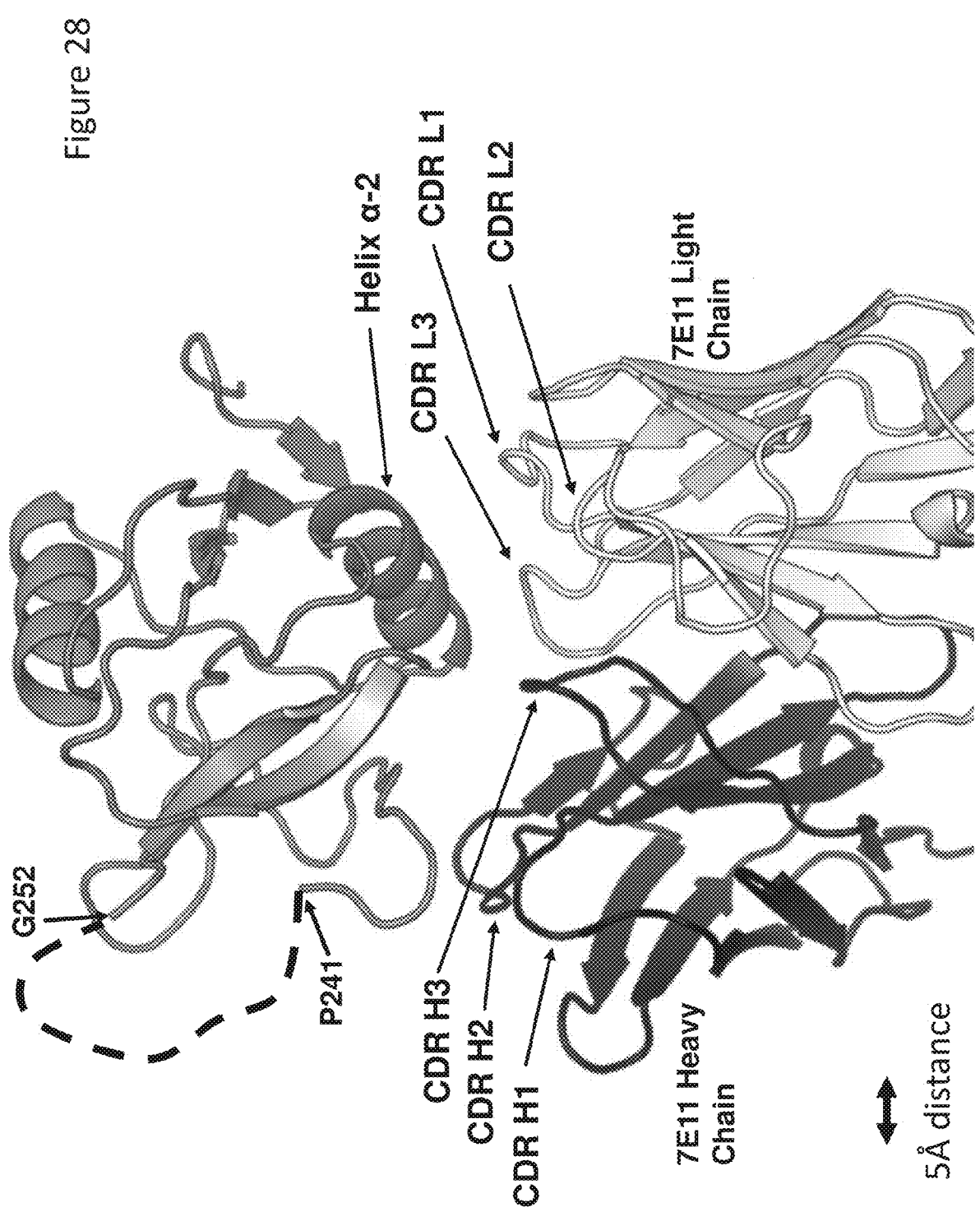
FIG. 28. An enlarged view of the structure of the ASGR-1 CBD and the 7E11 Fab. The figure represents a disordered carbohydrate binding loop with a dashed line and highlights the indirect inhibition of ASGR-1 CBD and the ligand (GalNAc) binding. The figure incorporates a double-headed arrow which represents a 5 angstrom distance from tip to tip.

The present example presents the crystal structure of the ASGR-1 CBD bound to the Fab fragment of 4A2, determined to 2.15 Å resolution (the conditions of which are described above in section B of this Example). This structure, depicted in FIGS. 24, 25 and 26, shows that when 4A2 binds to/interacts with ASGR-1, a conformational rearrangement of the carbohydrate binding loop occurs, impairing the carbohydrate binding loop from binding to/interacting with ligand (i.e., carbohydrates). This demonstrates that the 4A2 Fab indirectly inhibits the ASGR-1 CBD/Ligand binding.

The depicted structure also allows one to identify specific core ASGR amino acid residues for the interaction interface of 4A2 with ASGR-1. This was defined as residues that are within 5 Å of the 4A2 protein. The core residues are as follows: R170, W195, E196, K199, Q202, H203, H204, I205, G206, P207, V208, F233, K234, N235, W236, P238, D260, D261, G262, R263, R274 (SEQ ID NO:5).

The structures were also used to identify boundary ASGR-1 amino acid residues for the interaction interface with 4A2. These residues were ASGR-1 residues that were from 5-8 Å of the 4A2 protein. The boundary residues are as follows: N157, V159, F168, S169, S171, S194, Q198, F200, V201, T210, R237, E239, Q240, F258, T259, W264 (SEQ ID NO:5).

Specific core 4A2 amino acid residues of the interaction interface with ASGR-1 were defined as 4A2 residues that are within 5 Å of the ASGR-1 protein. The core 4A2 Heavy Chain residues include: T28, F29, T30, N31, Y32, D33, W50, H52, S55, N57, S99, S100, G101, W102, Y103; and the core 4A2 Light Chain residues include: 4A2 Light Chain: H31, S33, N34, N36, Y38, W56, Y97, Y98.

Boundary 4A2 amino acid residues of the interaction interface with ASGR-1 were defined as 4A2 residues that are 5-8 Å from the ASGR-1 protein. The boundary 4A2 Heavy Chain residues include: Y27, I34, N35, W47, M51, P53, N54, G56, T58, G59, Y104, D106; and the boundary 4A2 Light Chain residues include: I29, S32, N35, N37, Y55, T59, Q96, N99, T100.

The coordinates for the ASGR-1 CBD/4A2 crystal structure complex are presented in Table 10.2.

Methods:
The same methods were followed as described above in part B of this Example except for the following chang -continued 7E11 mAb Light Chain (SEQ ID NO: 32653):
DIQMTQSPSSLSASVGDRVTIACRASQNIISYLNWYQQKPGKAPKFLIY

TASSLQSGVPSRFSGSGSGTDFTLTISSLQPEDFAIYYCQQTYSTPLTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

7E11 Fab Heavy Chain (Post-Cleavage) (SEQ ID NO: 32654):
QVQLVESGGGVVQPGRSLRLSCAASGFTFSSFGMHWVRQAPGKGLEWVA

IIWHDGSNKYYADSVKGRFTISRDNSNNTLYLQMSSLRAEDTAVYYCAR

DLSMGGMDVWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCGSDEVD

7E11 Fab Light Chain (Post-Cleavage) (SEQ ID NO: 32655):
DIQMTQSPSSLSASVGDRVTIACRASQNIISYLNWYQQKPGKAPKFLIY

TASSLQSGVPSRFSGSGSGTDFTLTISSLQPEDFAIYYCQQTYSTPLTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

1. The ASGR-1 CBD/7E11 Fab complex was concentrated to 20 mg/ml and crystallized in 0.2 M Potassium Phosphate monobasic and 20% PEG3350;
2. The ASGR-1 CBD/7E11 Fab complex crystals grow in the P6222 space group with unit cell dimensions a=105.75, b=105.75, c=193.75 Å and γ=120.0° with one complex molecule per asymmetric unit, and diffract to 2.0 Å resolution;
3. The dataset was processed with XDS/CCP4;
4. The ASGR-1 CBD/7E11 Fab complex structure was solved by molecular replacement with the program Phaser; and
5. The structure was improved with multiple rounds of model building with Coot³ and refinement with Phenix⁴, to a final R=21.4/$R_{free}$=26.9.

E. Crystal Structure of ASGR-1 Carbohydrate Binding Domain (CBD) with 4H6

Figure 29:
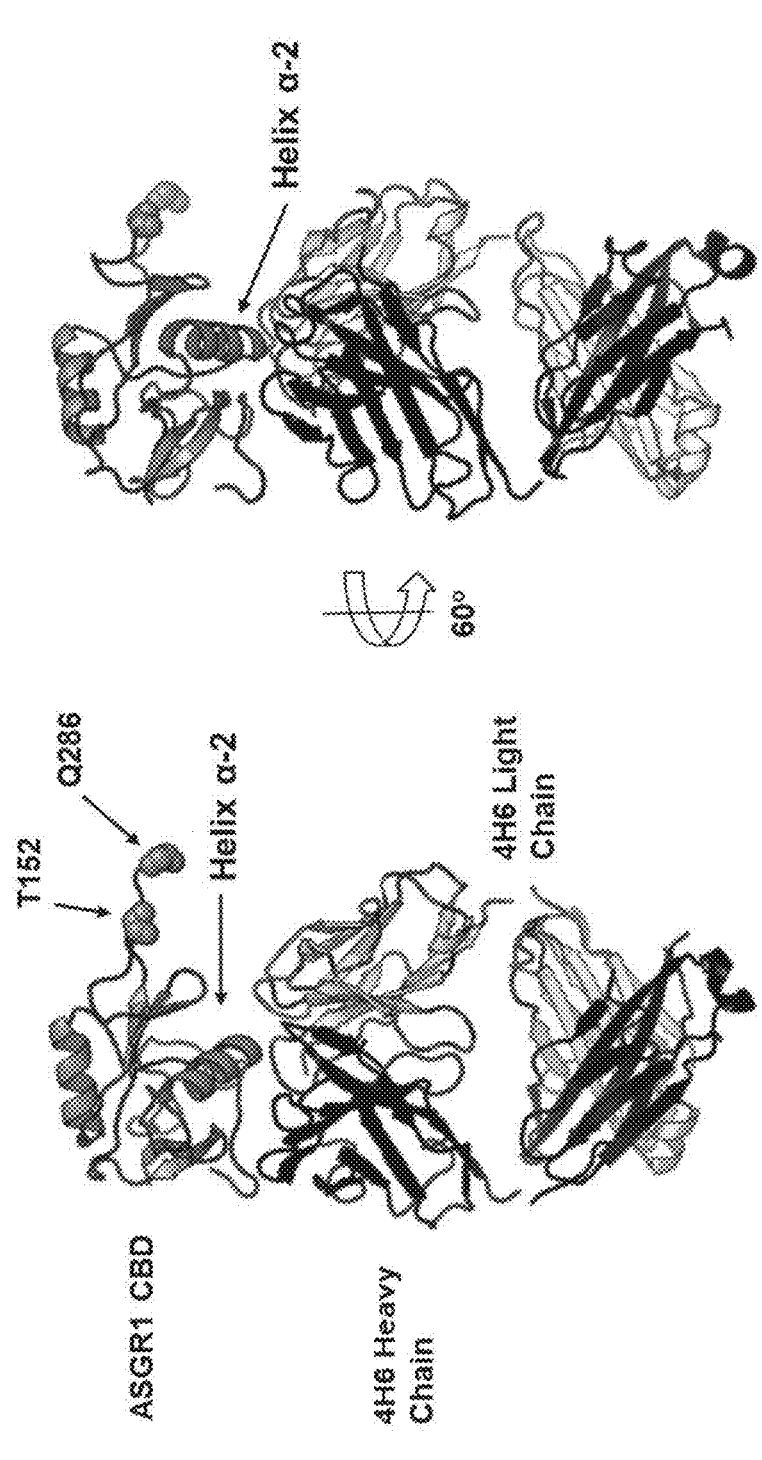
FIG. 29. A depiction of the structure of the ASGR-1 CBD and the 4H6 Fab.
Figure 30:
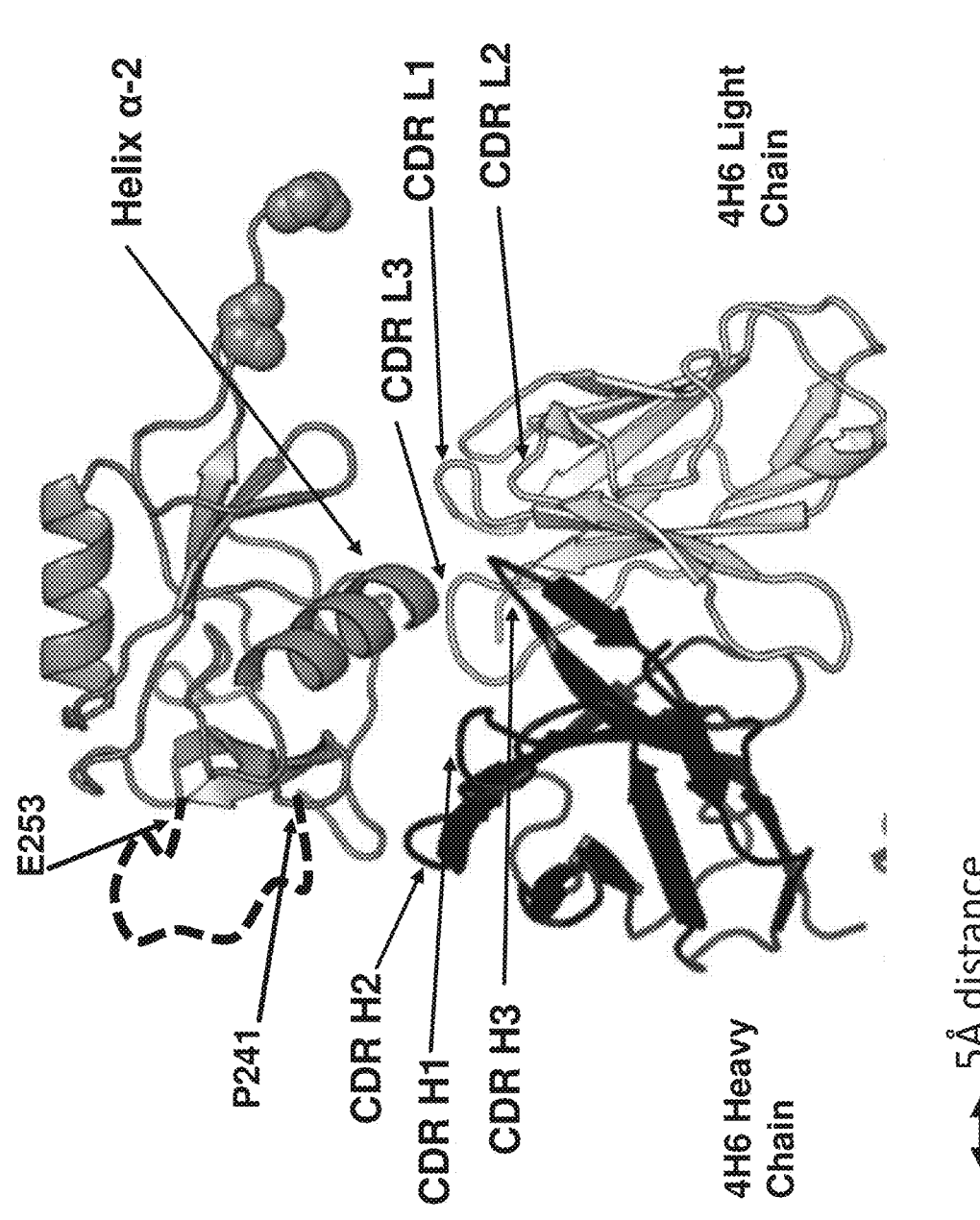
FIG. 30. An enlarged view of structure of the ASGR-1 CBD and the 4H6 Fab. The figure represents a disordered carbohydrate binding loop with a dashed line and highlights the indirect inhibition of ASGR-1 CBD and the ligand (GalNAc) binding. The figure incorporates a double-headed arrow which represents a 5 angstrom distance from tip to tip.

The present example presents the crystal structure of the ASGR-1 CBD bound to the Fab fragment of 4H6, determined to 2.6 Å resolution (the conditions of which are described above in section B of this Example). This structure, depicted in FIGS. 29 and 30, shows that when 4H6 binds to/interacts with ASGR-1, a conformational rearrangement of the carbohydrate binding loop occurs, impairing the carbohydrate binding loop from binding to/interacting with ligand (i.e., carbohydrates). This demonstrates that the 4H6 Fab indirectly inhibits the ASGR-1 CBD/Ligand binding.

The depicted structure also allows one to identify specific core ASGR amino acid residues for the interaction interface of 4H6 with ASGR-1. This was defined as residues that are within 5 Å of the 4H6 protein. The core residues are as follows: H161, E162, T193, S194, W195, E196, K199, Q202, T231, G232, F233, K234, N235, P238, D261, R263 (SEQ ID NO:5).

The structures were also used to identify boundary ASGR-1 amino acid residues for the interaction interface with 4H6. These residues were ASGR-1 residues that were from 5-8 Å of the 4H6 protein. The boundary residues are as follows: R163, V192, E197, Q198, H203, P207, D228, E230, W236, R237, D260, G262, W264 (SEQ ID NO:5).

Specific core 4H6 amino acid residues of the interaction interface with ASGR-1 were defined as 4H6 residues that are within 5 Å of the ASGR-1 protein. The core 4H6 Heavy Chain residues include: Y33, H35, W50, H52, S55, G57, T58, N59, D99, G100, T101, S102; and the core 4H6 Light Chain residues include: Q27, W32, A91, N92, S93, F94, F96.

Boundary 4H6 amino acid residues of the interaction interface with ASGR-1 were defined as 4H6 residues that are 5-8 Å from the ASGR-1 protein. The boundary 4H6 Heavy Chain residues include: D31, Y32, L34, W47, I51, N54, G56, Y60, Q65, S103, F104; and the boundary 4H6 Light Chain residues include: D1, I2, G28, I29, S30, R31, Y49, G50, Q89, Q90, P95.

Methods:

The same methods were followed as described above in part B of this example except for the following changes:

1. The 4H6 Fab fragment was generated by cleaving the 4H6 mAb with caspase 3.

4H6 mAb Heavy Chain (SEQ ID NO: 32656):
QVQLVQSGAEVKKPGASVKVSCKASGYTFTDYYLHWVRQAPGQGLEWMG

WIHPNSGGTNYAQKFQGRVTMTRDTSISTAYMGLSSLRSDDTAVYYCAR

DGTSSFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCGSDEVDGGDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALH

NHYTQKSLSLSPGHHHHHH

4H6 mAb Light Chain (SEQ ID NO: 32657):
DIQMTQSPSSVSASVGDRVTITCRASQGISRWLAWYQQKPGKAPKLLIY

GASSLQSGVPSRFSGSGSGTDFTLTISSLQPEDFAIYYCQQANSFPFTF

GPGTKVDIKGTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

4H6 Fab Heavy Chain (Post-Cleavage) (SEQ ID NO: 32658):
QVQLVQSGAEVKKPGASVKVSCKASGYTFTDYYLHWVRQAPGQGLEWMG

WIHPNSGGTNYAQKFQGRVTMTRDTSISTAYMGLSSLRSDDTAVYYCAR

DGTSSFDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCGSDEVD

4H6 Fab Light Chain (Post-Cleavage) (SEQ ID NO: 32659):
DIQMTQSPSSVSASVGDRVTITCRASQGISRWLAWYQQKPGKAPKLLIY

GASSLQSGVPSRFSGSGSGTDFTLTISSLQPEDFAIYYCQQANSFPFTF

GPGTKVDIKGTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

2. The ASGR-1 CBD/4H6 Fab complex was concentrated to 20 mg/ml and crystallized in 0.2M Sodium fluoride, 0.1 M Bis Tris propane pH 8.5, 20% PEG3350;

3. The dataset was collected on beamline ID22 at the APS synchrotron and processed with HKL2000/CCP4;

4. The ASGR-1 CBD/4H6 Fab complex crystals grow in the P12₁1 space group with unit cell dimensions a=57.20, b=43.58, c=131.65 Å and β=90.7° with one complex molecule per asymmetric unit, and diffract to 2.6 Å resolution;

5. The ASGR-1 CBD/4H6 Fab complex structure was solved by molecular replacement with the program Phaser; and 6. The structure was improved with multiple rounds of model building with Coot[3] and refinement with Phenix[4], to a final R=17.9/R$_{free}$=22.5.

F. Crystal Structure of ASGR-1 Carbohydrate Binding Domain (CBD) with 72G9

Figure 31:
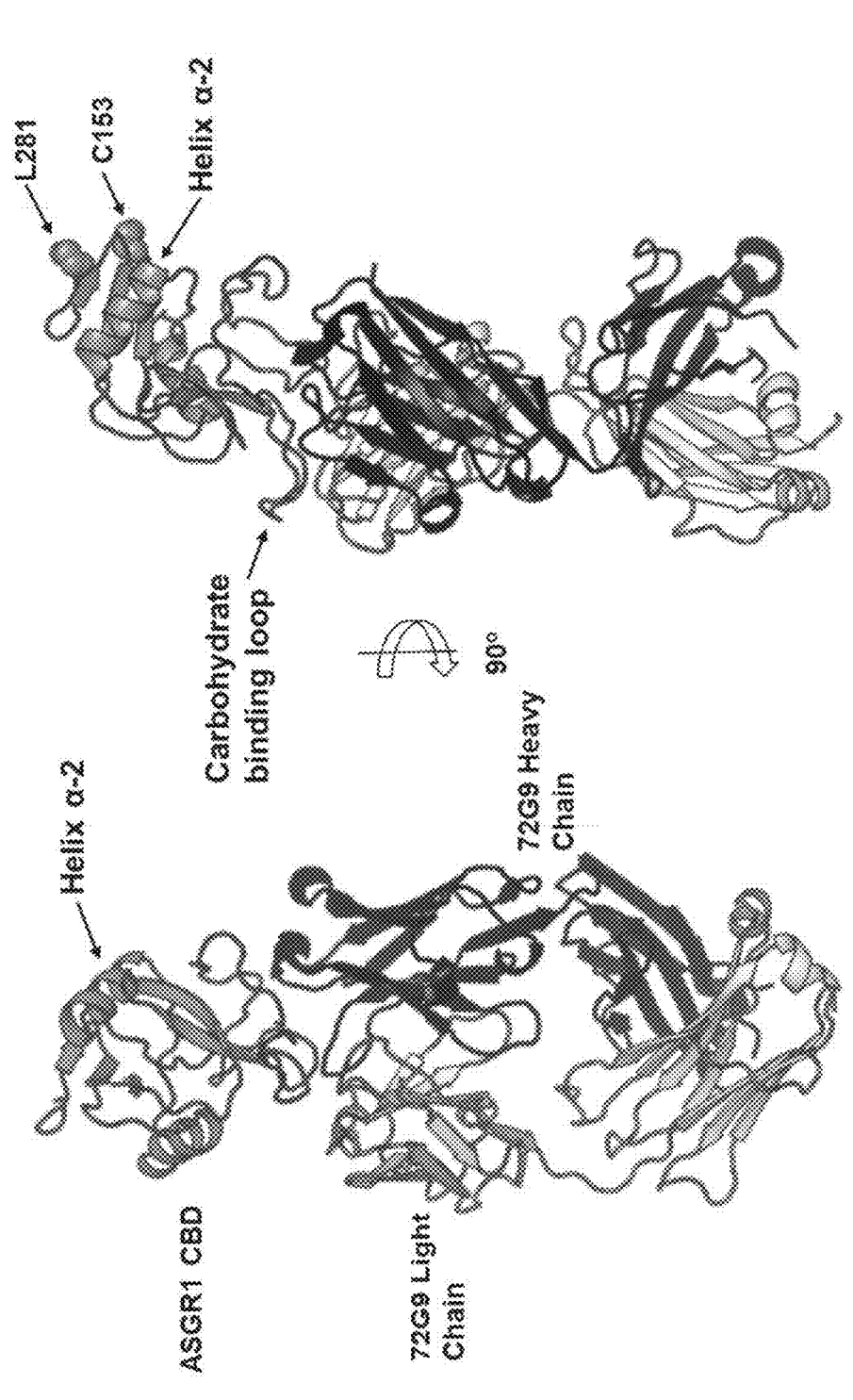
FIG. 31. A depiction of the structure of the ASGR-1 CBD and the 72G9 Fab.
Figure 32:
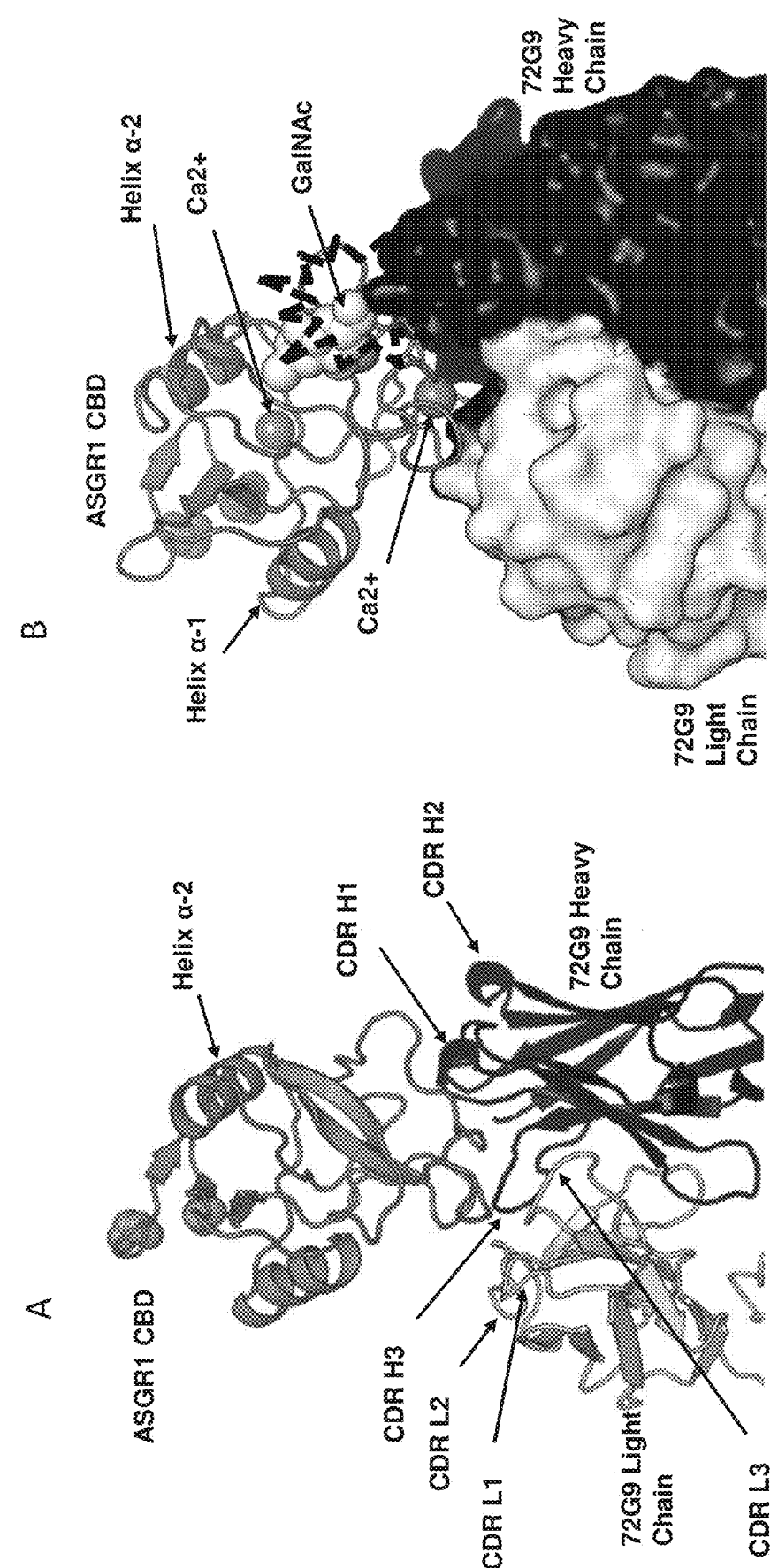
FIG. 32. Panel A is an enlarged view of the structure of ASGR-1 CBD and the 72G9 Fab; and Panel B is a depiction of the structure of ASGR-1 CBD and the 72G9 Fab that also overlays the structure of ASGR-1 CBD and the ligand and highlights the direct inhibition of ASGR-1 CBD and the ligand (GalNAc) binding.

The present example presents the crystal structure of the ASGR-1 CBD bound to the Fab fragment of 72G9, determined to 2.55 Å resolution (the conditions of which are described above in section B of this Example). This structure, depicted in FIGS. 31 and 32A and 32B, shows that when 72G9 binds to/interacts with ASGR-1, the CDR H2 loop of the Fab fragment appears to directly block the ligand (i.e., carbohydrate) binding/interacting to ASGR-1 CBD. This demonstrates that the 72G9 Fab directly inhibits the ASGR-1 CBD/Ligand binding.

The depicted structure also allows one to identify specific core ASGR amino acid residues for the interaction interface of 72G9 with ASGR-1. This was defined as residues that are within 5 Å of the 72G9 protein. The core residues are as follows: D216, Q217, N218, G219, P220, W221, Y229, E230, K234, W236, E239, Q240, P241, D242, D243, W244, Y245, G246, L249, G250, G251, G252, D254, Q270 ((SEQ ID NO:5).

The structures were also used to identify boundary ASGR-1 amino acid residues for the interaction interface with 72G9. These residues were ASGR-1 residues that were from 5-8 Å of the 72G9 protein. The boundary residues are as follows: H215, K222, T231, G232, R237, P238, H247, G248, E253, C255, D266, V268, C269 (SEQ ID NO:5).

Specific core 72G9 amino acid residues of the interaction interface with ASGR-1 were defined as 72G9 residues that are within 5 Å of the ASGR-1 protein. The core 72G9 Heavy Chain residues include: G26, F27, T28, S30, S31, Y32, S33, S52, G53, S54, S56, Y57, Y59, R98, G100, S101, R102; and the core 72G9 Light Chain residues include: Y32, Y49, T50, Q55, S91, H92, S93, F94, F96.

Boundary 72G9 amino acid residues of the interaction interface with ASGR-1 were defined as 72G9 residues that are 5-8 Å from the ASGR-1 protein. The boundary 72G9 Heavy Chain residues include: V2, F29, N35, S50, T51, S55, I58, R72, G99, G103, F104, D105; and the boundary 72G9 Light Chain residues include: S28, I29, T30, N33, L46, S53, L54, S56, Q89, Q90, P95.

Methods:

The same methods were followed as described above in part B of this example except for the following changes:

1. The 72G9 Fab fragment was generated by cleaving the 72G9 mAb with caspase 3.

72G9 mAb Heavy Chain (SEQ ID NO: 32660):
EVQLVESGGGLVKPGGSLRLSCAASGFTFSSYSMNWVRQAPGKGLEWVS

SISGSSSYIYYADSVKGRFTISRDNAKNSLYLQMNSLRAEDTAVYFCAR

GGSRGFDPWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCGSDEVDGGDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALH

NHYTQKSLSLSPGHHHHHH

72G9 mAb Light Chain (SEQ ID NO: 32661):
DIQMTQSPSSLSASVGDRVTITCRASQSITSYLNWYQQKPGKAPKLLIY

TASSLQSGVPSRFSGSGSGTDFTLTISSLQPEDFATYYCQQSHSFPFTF

GPGTKVDIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

72G9 Fab Heavy Chain (Post-Cleavage) (SEQ ID NO: 32662):
EVQLVESGGGLVKPGGSLRLSCAASGFTFSSYSMNWVRQAPGKGLEWVS

SISGSSSYIYYADSVKGRFTISRDNAKNSLYLQMNSLRAEDTAVYFCAR

GGSRGFDPWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCGSDEVD

72G9 Fab Light Chain (Post-Cleavage) (SEQ ID NO: 32663):
DIQMTQSPSSLSASVGDRVTITCRASQSITSYLNWYQQKPGKAPKLLIY

TASSLQSGVPSRFSGSGSGTDFTLTISSLQPEDFATYYCQQSHSFPFTF

GPGTKVDIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

2. The 72G9 Fab/ASGR-1 CBD complex was concentrated to 0.2 M Magnesium Sulfate heptahydrate, 20% PEG3350;

3. The ASGR-1 CBD/72G9 Fab complex crystals grew in the P21 space group with unit cell dimensions a=100.98, b=64.95, c=100.68 Å and β=96.43° with one complex molecule per asymmetric unit, and diffract to 2.55 Å resolution;

4. The dataset was processed with XDS/CCP4;

5. The ASGR-1 CBD/72G9 Fab complex structure was solved by molecular replacement with the program Phaser; and 6. The structure was improved with multiple rounds of model building with Coot[3] and refinement with Phenix[4], to a final R=20.4/R$_{free}$=23.4.

G. Crystal Structure of ASGR-1 Carbohydrate Binding Domain (CBD) with 194A4

Figure 33:
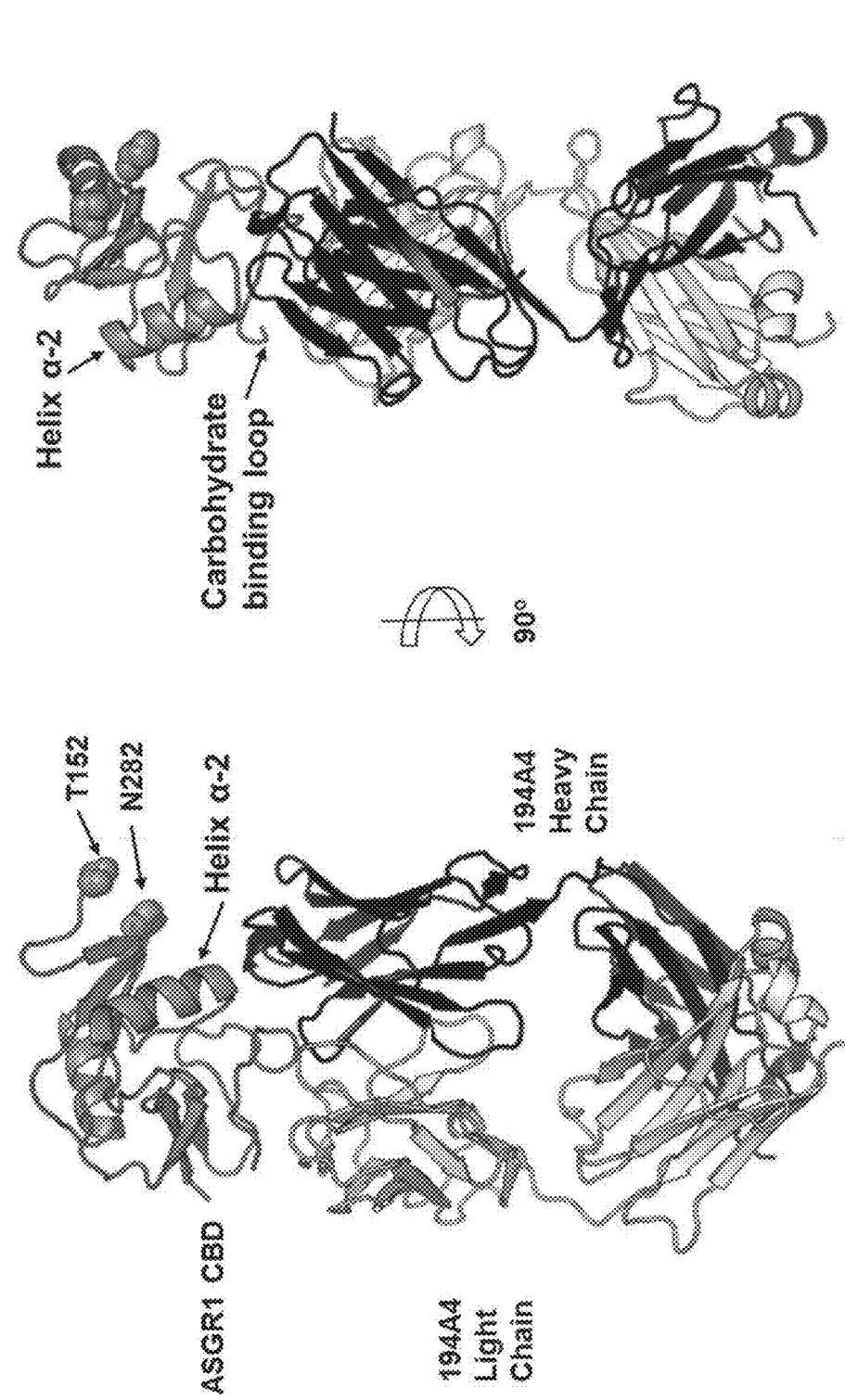
FIG. 33. A depiction of the structure of the ASGR-1 CBD and the 194A4 Fab.
Figure 34:
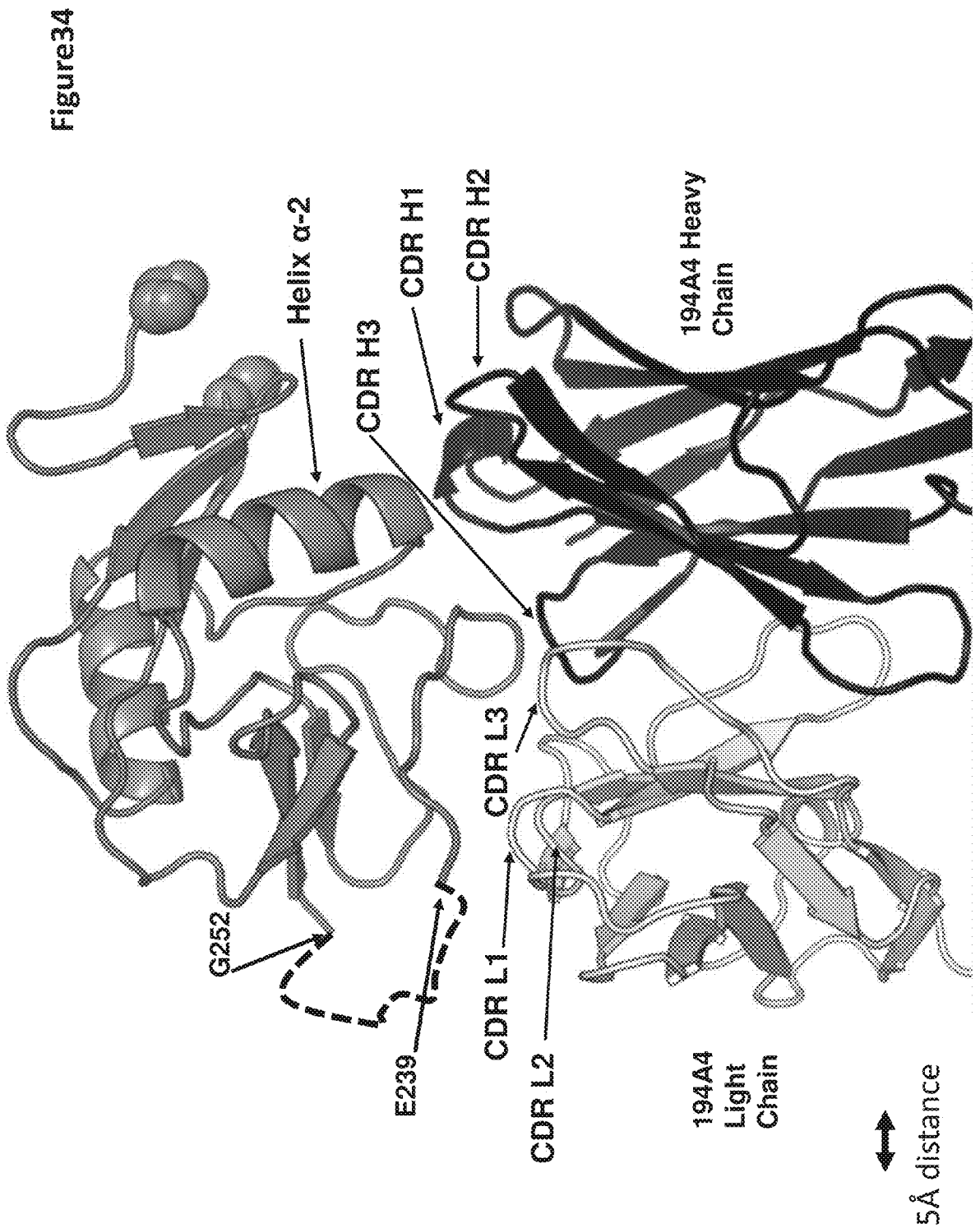
FIG. 34. An enlarged view of the structure of the ASGR-1 CBD and the 194A4 Fab. The figure represents a disordered carbohydrate binding loop with a dashed line and highlights the indirect inhibition of ASGR-1 CBD and the ligand (GalNAc) binding. The figure incorporates a double-headed arrow which represents a 5 angstrom distance from tip to tip.

The present example presents the crystal structure of the ASGR-1 CBD bound to the Fab fragment of 194A4, determined to 2.6 Å resolution (the conditions of which are described above in section B of this Example). This structure, depicted in FIGS. 33 and 34, shows that when 194A4 binds to/interacts with ASGR-1, a conformational rearrangement of the carbohydrate binding loop occurs, impairing the carbohydrate binding loop from binding to/interacting with ligand (i.e., carbohydrates). This demonstrates that the 194A4 Fab indirectly inhibits the ASGR-1 CBD/Ligand binding.

The depicted structure also allows one to identify specific core ASGR amino acid residues for the interaction interface of 194A4 with ASGR-1. This was defined as residues that are within 5 Å of the 194A4 protein. The core residues are as follows: T193, S194, W195, E196, P220, W221, G226, T227, D228, Y229, E230, T231, G232, F233, K234, N235, W236, R237, P238, E239, G252 (SEQ ID NO:5).

The structures were also used to identify boundary ASGR-1 amino acid residues for the interaction interface with 194A4. These residues were ASGR-1 residues that were from 5-8 Å of the 194A4 protein. The boundary residues are as follows: H161, E162, V191, V192, E197, Q198, D216, G219, K222, W223, D225, R263, W264 (SEQ ID NO:5).

Specific core 194A4 amino acid residues of the interaction interface with ASGR-1 were defined as 194A4 residues that are within 5 Å of the ASGR-1 protein. The core 194A4 Heavy Chain residues include: V31, Y32, Y33, W50, N52, S55, G57, R98, G99, Y100, D101, I102, T204; and the core 194A4 Light Chain residues include: V29, S30, I32, Y33, L47, Y50, R55, A56, T57, Y94.

Boundary 194A4 amino acid residues of the interaction interface with ASGR-1 were defined as 194A4 residues that are 5-8 Å from the ASGR-1 protein. The boundary 194A4 Heavy Chain residues include: V2, Y27, T30, L34, N35, P53, N54, G56, T58, N59, A97, L103, G105; and the boundary 194A4 Light Chain residues include: G28, N31, L48, I49, G51, N54, G58, I59, S68, G69, D93, S95.

Methods:
The same methods were followed as described above in part B of this example except for the following changes:
1. The 194A4 Fab fragment was generated by cleaving the 194A4 mAb with caspase 3.

```
194A4 mAb Heavy Chain (SEQ ID NO: 32664):
QVQLVQSGTEVKKPGASLKVSCKASGYTFTVYYLNWVRQAPGQGLEWMG

WINPNSGGTNYAQKFQGRVTMTRDTSISTAYMELSRLRSDDTAVYYCAR

GYDILTGWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCGSDEVDGGDKTHTCPPCPAPELLGGP

SVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHN

HYTQKSLSLSPGHHHHHH

194A4 mAb Light Chain (SEQ ID NO: 32665):
EIVLTQSPGTLSLSPGERATLSCRASRGVSNIYLAWYQQKPGQAPRLLI

YGASNRATGIPDRFSGSGSGTDFTLTISRLEPEDFAVYYCQHNDYSMFT

FGPGTKVDIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

194A4 Fab Heavy Chain (Post-Cleavage) (SEQ ID NO: 32666):
QVQLVQSGTEVKKPGASLKVSCKASGYTFTVYYLNWVRQAPGQGLEWMG

WINPNSGGTNYAQKFQGRVTMTRDTSISTAYMELSRLRSDDTAVYYCAR

GYDILTGWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCGSDEVD

194A4 Fab Light Chain (Post-Cleavage) (SEQ ID NO: 32667):
EIVLTQSPGTLSLSPGERATLSCRASRGVSNIYLAWYQQKPGQAPRLLI

YGASNRATGIPDRFSGSGSGTDFTLTISRLEPEDFAVYYCQHNDYSMFT

FGPGTKVDIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC
```

2. The 194A4 Fab/ASGR-1 CBD complex was concentrated to 13.1 mg/mL and crystallized with 0.2 M Sodium chloride, 0.1M MES pH6.0, 20% PEG2000 MME;
3. The dataset was processed with XDS/CCP4;
4. The 194A4 Fab/ASGR-1 CBD complex crystals grow in the $P2_12_12_1$ space group with unit cell dimensions a=52.23, b=66.40, c=177.75 Å with one complex molecule per asymmetric unit, and diffract to 2.6 Å resolution;
5. The ASGR-1 CBD/194A4 Fab complex structure was solved by molecular replacement with the program Phaser; and
6. The structure was improved with multiple rounds of model building with Coot[3] and refinement with Phenix[4], to a final R=20.1/$R_{free}$=24.6.

H. Crystal Structure of ASGR-1 Carbohydrate Binding Domain (CBD) with 54E9

Figure 36:
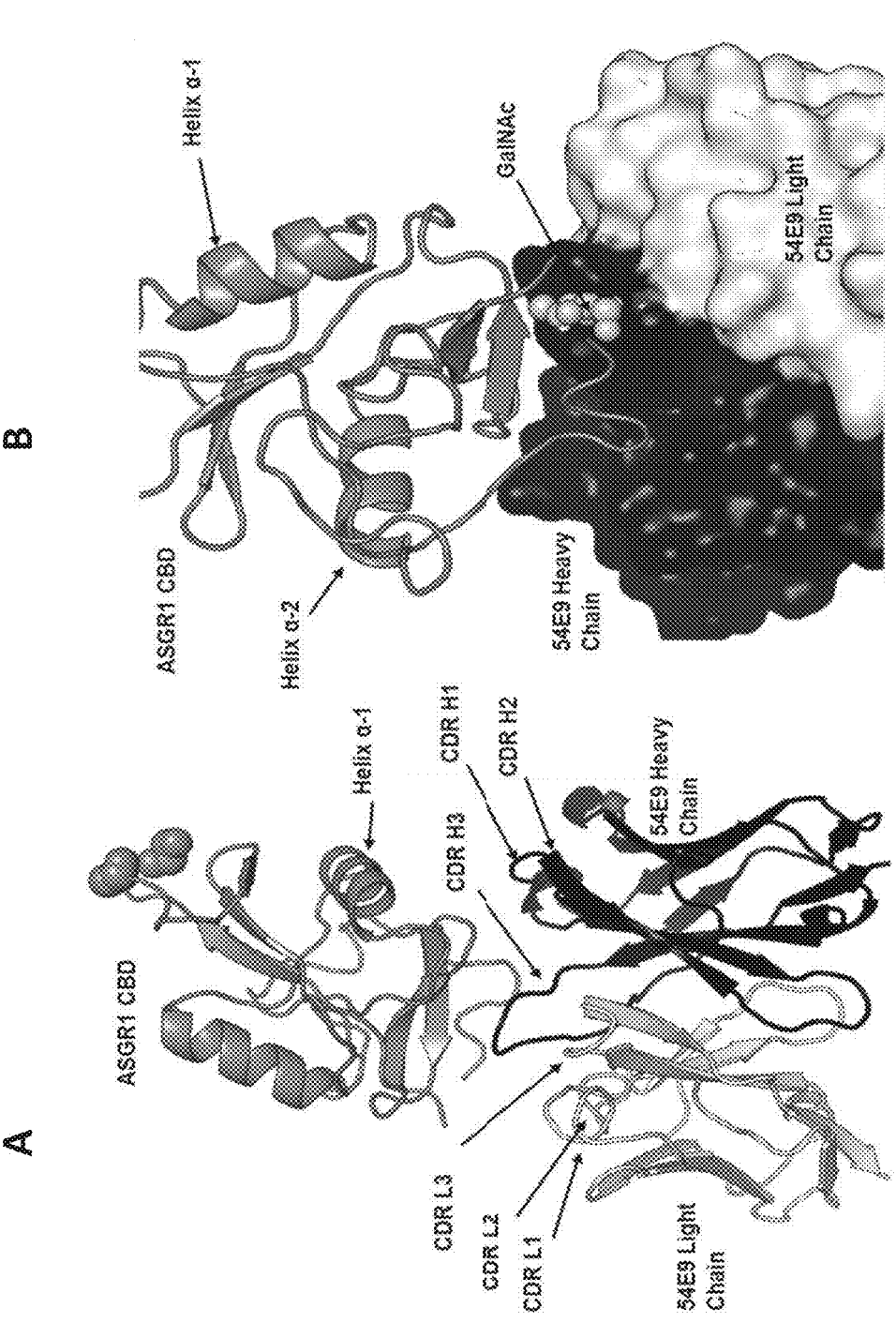
FIG. 36. Panel A is an enlarged view of the structure of the ASGR-1 CBD and the 54E9 Fab; and Panel B is a depiction of the structure of the ASGR-1 CBD and the 54E9 Fab that also overlays the structure of ASGR-1 CBD and the ligand and highlights the direct inhibition of ASGR-1 CBD and the ligand (GalNAc) binding.

The present example presents the crystal structure of the ASGR-1 CBD bound to the Fab fragment of 54E9, determined to 2.6 Å resolution (the conditions of which are described above in section B of this Example). This structure, depicted in FIG. 35 and FIG. 36A and FIG. 36B, shows that when 54E9 binds to/interacts with ASGR-1, the CDR H3 loop of the Fab fragment appears to directly block the ligand (i.e., carbohydrate) from binding/interacting to ASGR-1 CBD. This demonstrates that the 54E9 Fab directly inhibits the ASGR-1 CBD/Ligand binding.

The depicted structure also allows one to identify specific core ASGR amino acid residues for the interaction interface of 54E9 with ASGR-1. This was defined as residues that are within 5 Å of the 54E9 protein. The core residues are as follows: W195, N209, N235, R237, P238, E239, Q240, D242, H257, T259, D260, D261, R263, N265, D267, R271, Y273 (SEQ ID NO:5).

The structures were also used to identify boundary ASGR-1 amino acid residues for the interaction interface with 54E9. These residues were ASGR-1 residues that were from 5-8 Å of the 54E9 protein. The boundary residues are as follows: Q198, Q202, P207, V208, F233, W236, D243, E253, F258, G262, W264, D266 (SEQ ID NO:5).

Specific core 54E9 amino acid residues of the interaction interface with ASGR-1 were defined as 54E9 residues that are within 5 Å of the ASGR-1 protein. The core 54E9 Heavy Chain residues include: N30, S31, Y32, S52, Y54, N55, K59, R98, D100, F101, W102, S103, G104, Y105, K107, D110; and the core 54E9 Light Chain residues include: none.

Boundary 54E9 amino acid residues of the interaction interface with ASGR-1 were defined as 54E9 residues that are 5-8 Å from the ASGR-1 protein. The boundary 54E9

Heavy Chain residues include: V2, Y27, T28, F29, G33, W50, A53, G56, N57, H99, Y106, G108; and the boundary 54E9 Light Chain residues include: N31, Y50, V51, Q54.

Methods:

The same methods were followed as described above in part B of this example except for the following changes:
1. The 54E9 Fab fragment was generated by cleaving the 54E9 mAb with caspase 3.

54E9 mAb Heavy Chain (SEQ ID NO: 32668):
QVQLVQSGAEVKKPGASVKVSCKASGYTFNSYGISWVRLAPGQGLEWMG

WISAYNGNTKNAQKLQGRVTMTTDTSTSTAYMELRSLRSDDTAVYYCAR

HDFWSGYYKGMDVWGQGTTVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSDEVDGGDKTHTCPPCPAP

ELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVM

HEALHNHYTQKSLSLSPGHHHHHH

54E9 mAb Light Chain (SEQ ID NO: 32669):
QSVLTQPPSASGTPGQRVTISCSGSNSNIGNNIVTWYQQLPGTAPKLLI

YVNDQRPSGVPDRFSGSKSGTSASLAISGLQSEDEADYYCAAWDDSLNG

WVFGGGTTLTVLGQPKAAPSVTLFPPSSEELQANKATLVCLISDFYPGA

VTVAWKADSSPVKAGVETTTPSKQSNNKYAASSYLSLTPEQWKSHRSYS

CQVTHEGSTVEKTVAPTECS

54E9 Fab Heavy Chain (Post-Cleavage) (SEQ ID NO: 32670):
QVQLVQSGAEVKKPGASVKVSCKASGYTFNSYGISWVRLAPGQGLEWMG

WISAYNGNTKNAQKLQGRVTMTTDTSTSTAYMELRSLRSDDTAVYYCAR

HDFWSGYYKGMDVWGQGTTVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSDEVD

54E9 Fab Light Chain (Post-Cleavage) (SEQ ID NO: 32671):
QSVLTQPPSASGTPGQRVTISCSGSNSNIGNNIVTWYQQLPGTAPKLLI

YVNDQRPSGVPDRFSGSKSGTSASLAISGLQSEDEADYYCAAWDDSLNG

WVFGGGTTLTVLGQPKAAPSVTLFPPSSEELQANKATLVCLISDFYPGA

VTVAWKADSSPVKAGVETTTPSKQSNNKYAASSYLSLTPEQWKSHRSYS

CQVTHEGSTVEKTVAPTECS

1. The 54E9 Fab/ASGR-1 CBD complex was concentrated to 14.8 mg/mL and crystallized with 0.2 M Magnesium Chloride hexahydrate, 20% PEG3350;
2. The dataset was processed with XDS/CCP4;
3. The 54E9 Fab/ASGR-1 CBD complex crystals grow in the I2 space group with unit cell dimensions a=64.66, b=41.65, c=224.59 Å and β=97.60° with one complex molecule per asymmetric unit, and diffract to 2.6 Å resolution;
4. The 54E9 Fab/ASGR-1 CBD complex structure was solved by molecular replacement with the program Phaser; and
5. The structure was improved with multiple rounds of model building with Coot[3] and refinement with Phenix[4], to a final R=19.1/$R_{free}$=25.9.

I. Crystal Structure of ASGR-1 Carbohydrate Binding Domain (CBD) with 218G4

Figure 38:
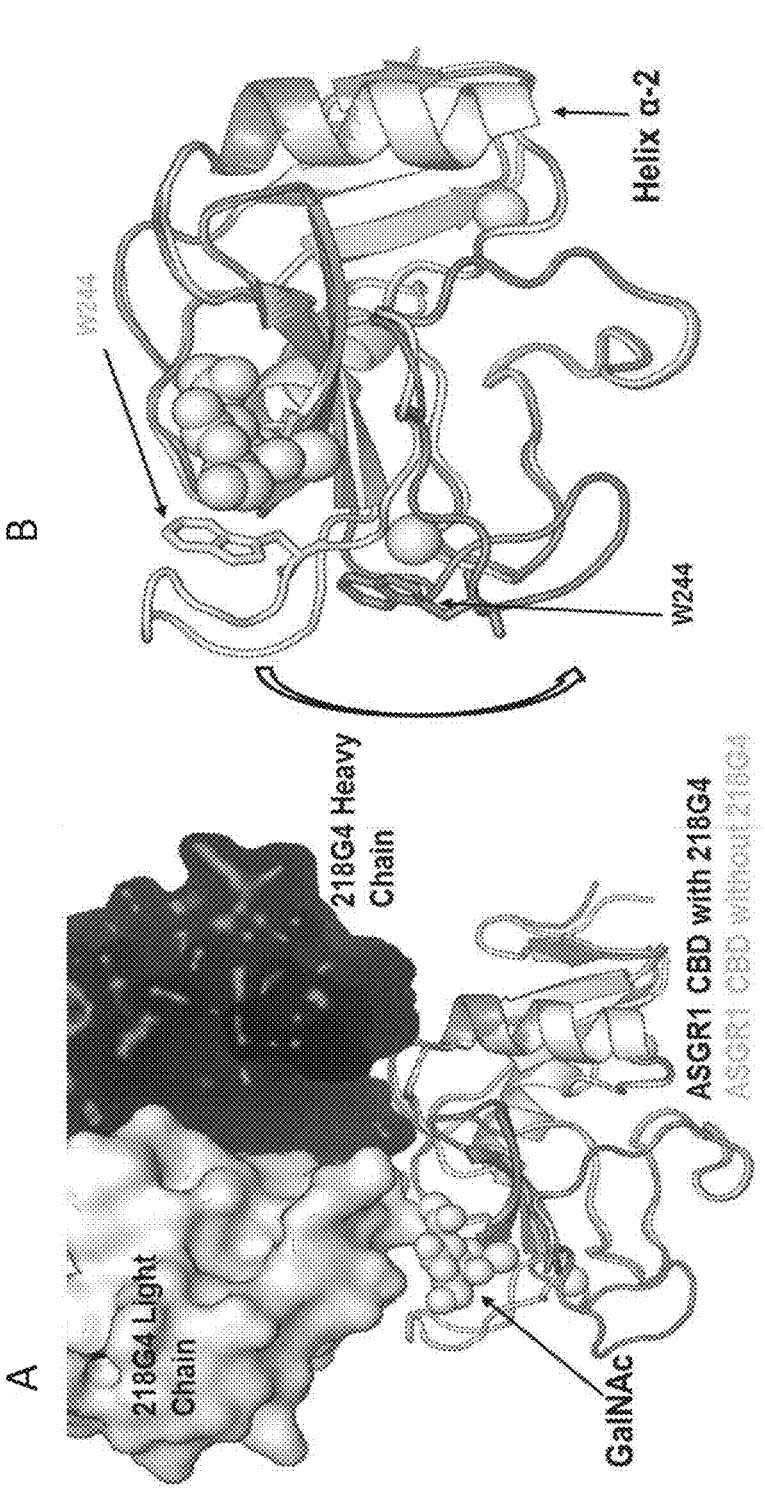
FIG. 38. Panels A and B are enlarged views of the structure of ASGR-1 CBD and the 218G4 Fab that also overlays the structure of ASGR-1 CBD and the ligand. These figures highlight the direct inhibition of ASGR-1 CBD and the ligand (GalNAc) binding when the 218G4 Fab is present.

The present example presents the crystal structure of the ASGR-1 CBD bound to the Fab fragment of 218G4, determined to 2.4 Å resolution (the conditions of which are described above in section B of this Example). This structure, depicted in FIGS. 37 and 38, shows that when 218G4 binds to/interacts with ASGR-1, it impairs its ability to bind to ligand (e.g., carbohydrate). This demonstrates that the 218G4 Fab directly inhibits the ASGR-1 CBD/Ligand binding.

The depicted structure also allows one to identify specific core ASGR amino acid residues for the interaction interface of 218G4 with ASGR-1. This was defined as residues that are within 5 Å of the 218G4 protein. The core residues are as follows: R170, S171, G172, A174, H204, I205, G206, P207, V208, N209, H257, D260, N265, D267, Q270, R271, P272, Y273, R274 (SEQ ID NO:5).

The structures were also used to identify boundary ASGR-1 amino acid residues for the interaction interface with 218G4. These residues were ASGR-1 residues that were from 5-8 Å of the 218G4 protein. The boundary residues are as follows: W167, F168, S169, K173, W175, D177, Y181, Q202, H203, T210, W211, R237, F258, T259, D261, D266, V268, C269, W275 (SEQ ID NO:5).

Specific core 218G4 amino acid residues of the interaction interface with ASGR-1 were defined as 218G4 residues that are within 5 Å of the ASGR-1 protein. The core 218G4 Heavy Chain residues include: Q1, V2, F27, S30, S31, Y32, Y53, D54, W99, Y100, Y101, Y102; and the core 218G4 Light Chain residues include: Y33, Y50, D51, N53, K54, S57.

Boundary 218G4 amino acid residues of the interaction interface with ASGR-1 were defined as 218G4 residues that are 5-8 Å from the ASGR-1 protein. The boundary 218G4 Heavy Chain residues include: G26, T28, F29, G33, W52, G55, R72, N74, N98, Y103, Y104, D107, V108; and the boundary 218G4 Light Chain residues include: V34, S52, R55, P56, G58, G65.

The coordinates for the ASGR-1 CBD/GalNAc crystal structure complex are presented in Table 10.3.

Methods:

The same methods were followed as described above in part B of this example except for the following changes:
1. The 218G4 Fab fragment was generated by cleaving the 218G4 mAb with caspase 3.

218G4 mAb Heavy Chain (SEQ ID NO: 32672):
QVQLVESGGGVVQPGRSLRLSCAASGFTFSSYGLHWVRQAPGKGLEWVA

VIWYDGSNKYYADSVKGRFTISRDNSKNTLYLQMNSLRVEDTAVYYCAN

WYYYYYGMDVWGQGTTVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCGSDEVDGGDKTHTCPPCPAPELL

GGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWE

-continued

SNGQPENNYKTTPPVLDSDGSFFLYSKLTVDKSRWQQGNVFSCSVMHEA

LHNHYTQKSLSLSPGHHHHHH

218G4 mAb Light Chain (SEQ ID NO: 32673):
QSVLTQPPSVSAAPGQKVTISCSGSSSNIGNNYVSWYQQLPGTAPKLLL

YDSNKRPSGIPARFSGSKSGTSATLGITGLQTGDEADYYCGTWDSSLNT

VVFGGGTKLTVLSQPKAAPSVTLFPPSSEELQANKATLVCLISDFYPGA

VTVAWKADSSPVKAGVETTTPSKQSNNKYAASSYLSLTPEQWKSHRSYS

CQVTHEGSTVEKTVAPTECS

218G4 Fab Heavy Chain (Post-Cleavage)(SEQ ID NO: 32674):
QVQLVESGGGVVQPGRSLRLSCAASGFTFSSYGLHWVRQAPGKGLEWVA

VIWYDGSNKYYADSVKGRFTISRDNSKNTLYLQMNSLRVEDTAVYYCAN

WYYYYYGMDVWGQGTTVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCGSDEVD

218G4 Fab Light Chain (Post-Cleavage):
Same sequence as 218G4 mAb Light chain

1. The 218G4 Fab/ASGR-1 CBD complex was concentrated to 16.4 mg/mL and crystallized with 0.1M Tris pH8 and 1.6M Lithium Sulfate;
2. The dataset was collected from a single crystal on beamline ID22 at the Argonne National Laboratory and processed with XDS/CCP4;
3. The 218G4 Fab/ASGR-1 CBD complex crystals grow in the C222 space group with unit cell dimensions a=137.24, b=245.26, c=118.91 Å with two complex molecules per asymmetric unit and diffract to 2.6 Å resolution;
4. The 218G4 Fab/ASGR-1 CBD complex structure was solved by molecular replacement with the program Phaser; and
5. The structure was improved with multiple rounds of model building with Coot[3] and refinement with Phenix[4], to a final Rfactor=18.4/$R_{free}$=21.6.

J. Crystal Structure of ASGR-1 Carbohydrate Binding Domain (CBD) with 176H4

Figure 39:
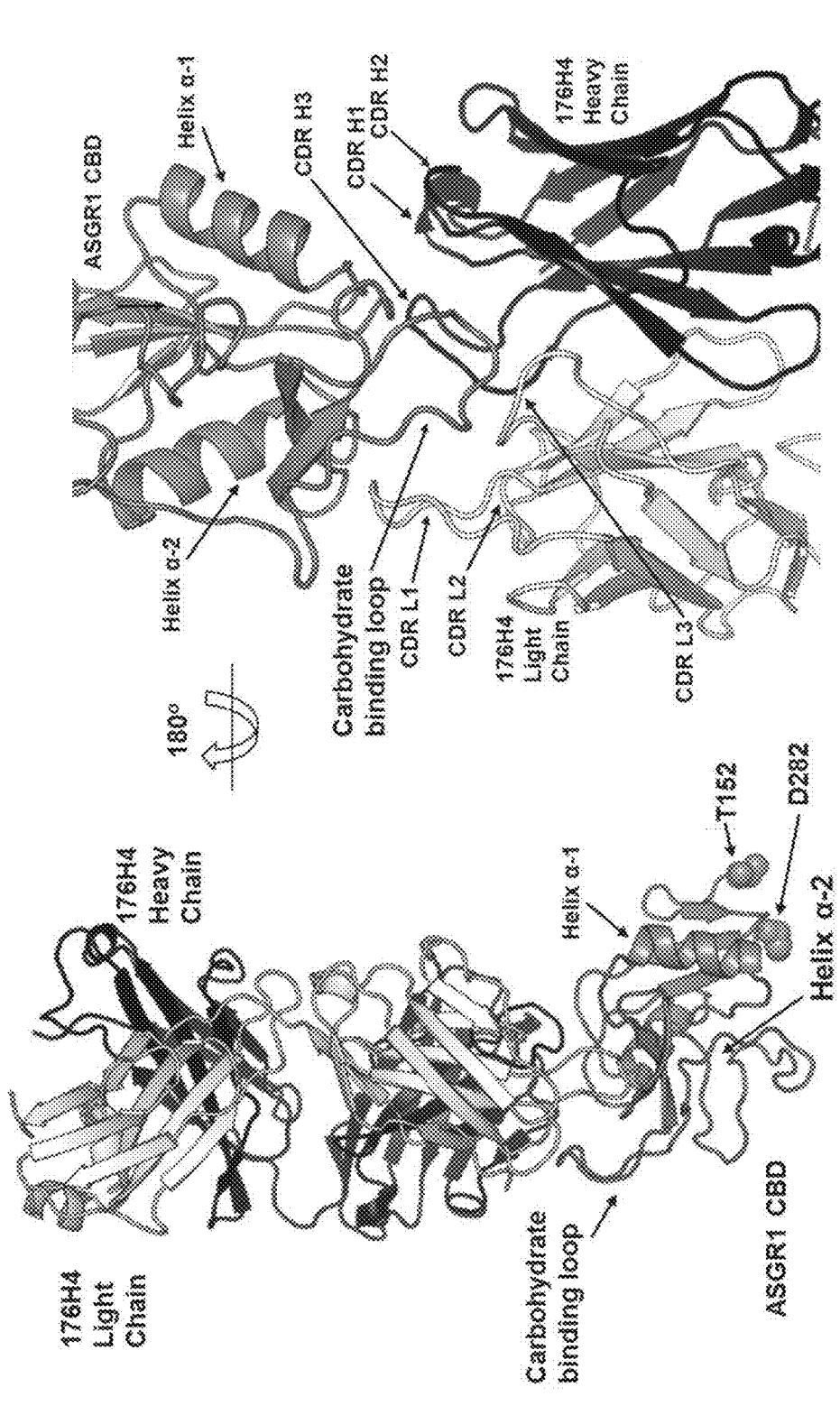
FIG. 39. A depiction of the structure of the ASGR-1 CBD and the 176H4 Fab.
Figure 40:
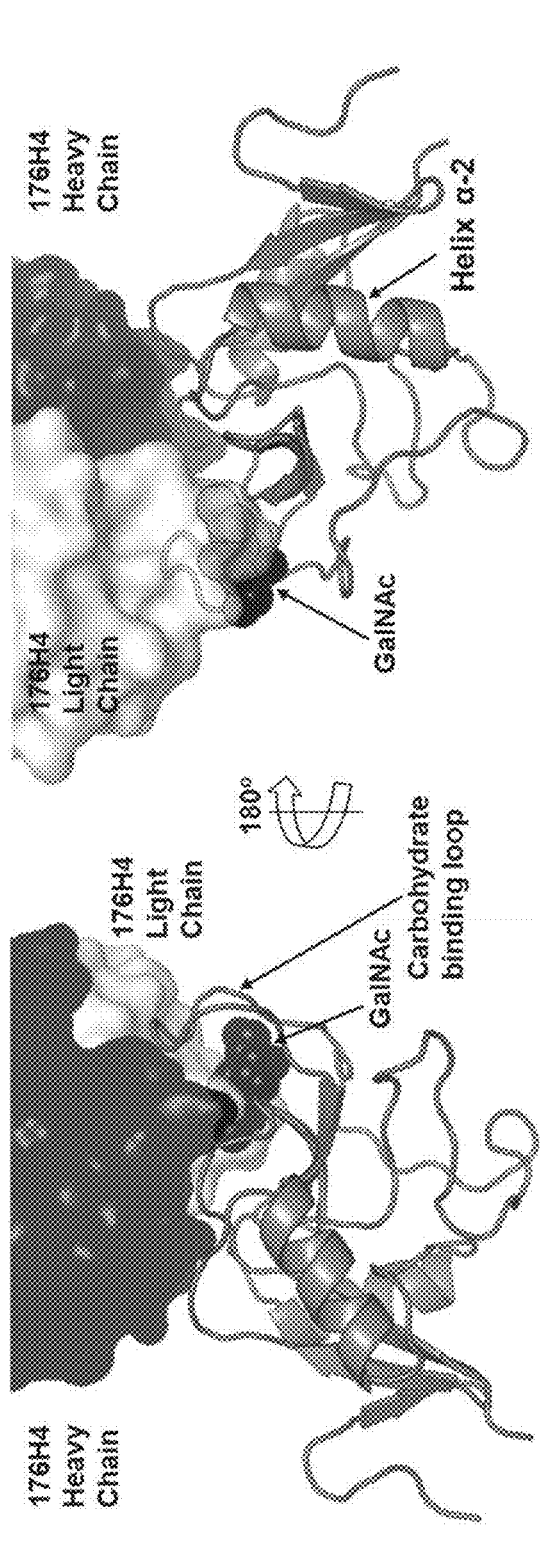
FIG. 40. An enlarged view of the structure of the ASGR-1 CBD and the 176H4 Fab that also overlays the structure of ASGR-1 CBD and the ligand. This figure highlight the direct inhibition of ASGR-1 CBD and the ligand (GalNAc) binding when the 176H4 Fab is present.

The present example presents the crystal structure of the ASGR-1 CBD bound to the Fab fragment of 176H5, determined to 2.3 Å resolution (the conditions of which are described above in section B of this Example). This structure, depicted in FIGS. 39 and 40, show that when 176H4 binds to/interacts with ASGR-1, it appears to block ligand (e.g., carbohydrate) binding by ASGR-1 CBD, with the paratope of the 176H4 antibody located directly on top of the carbohydrate binding pocket. This demonstrates that the 174H4 Fab directly inhibits the ASGR-1 CBD/Ligand binding.

The depicted structure also allows one to identify specific core ASGR amino acid residues for the interaction interface of 176H4 with ASGR-1. This was defined as residues that are within 5 Å of the 176H4 protein. The core residues are as follows: R170, S171, G172, K173, A174, D177, P207, V208, N209, R237, Q240, W244, G246, H247, G248, L249, E253, H257, T259, D260, N265, D267, Q270, R271, P272, Y273, R274 (SEQ ID NO:5).

The structures were also used to identify boundary ASGR-1 amino acid residues for the interaction interface with 176H4. These residues were ASGR-1 residues that were from 5-8 Å of the 176H4 protein. The boundary residues are as follows: S169, W175, A176, A178, T210, W211, W236, P238, E239, D242, Y245, G250, G251, F258, D261, G262, R263, W264, D266, V268, C269, W275 (SEQ ID NO:5).

Specific core 176H4 amino acid residues of the interaction interface with ASGR-1 were defined as 176H4 residues that are within 5 Å of the ASGR-1 protein. The core 176H4 Heavy Chain residues include: S31, W52, Y53, D54, Y57, Y59, D102, F103, W104; and the core 176H4 Light Chain residues include: H31, G32, D33, G34, K35, Y37, I97, Q98, I99.

Boundary 176H4 amino acid residues of the interaction interface with ASGR-1 were defined as 176H4 residues that are 5-8 Å from the ASGR-1 protein. The boundary 176H4 Heavy Chain residues include: T28, S30, Y32, G33, W47, I50, I51, S56, K58, Y60, K65, D99, H101, S105, G106; and the boundary 176H4 Light Chain residues include: I2, Q27, S28, L29, L30, T36, E55, Q95, S96, P100, W101.

Methods:

The same methods were followed as described above in part B of this example except for the following changes:

1. The 176H4 Fab fragment was generated by cleaving the 176H4 mAb with caspase 3.

176H4 mAb Heavy Chain (SEQ ID NO: 32675):
QVQLVESGGGVVQPGRSLRLSCAASGFTFSSYGMHWVRQAPGKGLEWVA

IIWYDGSYKYYADSVKGRFTISRDNSKNTLYLQMSSLRAEDTAVYYCAR

DAHDFWSGYFAYWGQGALVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCGSDEVDGGDKTHTCPPCPAPE

LLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMH

EALHNHYTQKSLSLSPGHHHHHH

176H4 mAb Light Chain (SEQ ID NO: 32676):
DIVMTQTPLSLSVTPGQPASISCKSSQSLLHGDGKTYLYWYLQKPGQPP

QLLIYEVSNRFSGVPDRFSGSGSGTDFTLKISRVEAEDVGIYYCMQSIQ

IPWTFGQGTRVEIKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC

176H4 Fab Heavy Chain (Post-Cleavage)(SEQ ID NO: 32677):
QVQLVESGGGVVQPGRSLRLSCAASGFTFSSYGMHWVRQAPGKGLEWVA

IIWYDGSYKYYADSVKGRFTISRDNSKNTLYLQMSSLRAEDTAVYYCAR

DAHDFWSGYFAYWGQGALVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCGSDEVD

176H4 Fab Light Chain (Post-Cleavage):
Same sequence as 176H4 mAb Light chain

1. The 176H4 Fab/ASGR-1 CBD complex was concentrated to 14.9 mg/mL and crystallized 1 with 0.2 M Sodium Nitrate, 20% PEG3350;

2. The dataset was collected from a single crystal on beamline ID22 at the Argonne National Laboratory and processed with XDS/CCP4;
3. The 176H4 Fab/ASGR-1 CBD complex crystals grow in the I121 space group with unit cell dimensions a=68.31, b=126.31, c=134.13 Å and β=101.6° with two complex molecules per asymmetric unit, and diffract to 2.3 Å resolution;
4. The 176H4 Fab/ASGR-1 CBD complex structure was solved by molecular replacement with the program Phaser; and
5. The structure was improved with multiple rounds of model building with Coot[3] and refinement with Phenix[4], to a final final $R_{factor}$=17.9/$R_{free}$=23.3.

K. Crystal Structure of ASGR-1 Carbohydrate Binding Domain (CBD) with 194C10

Figure 41:
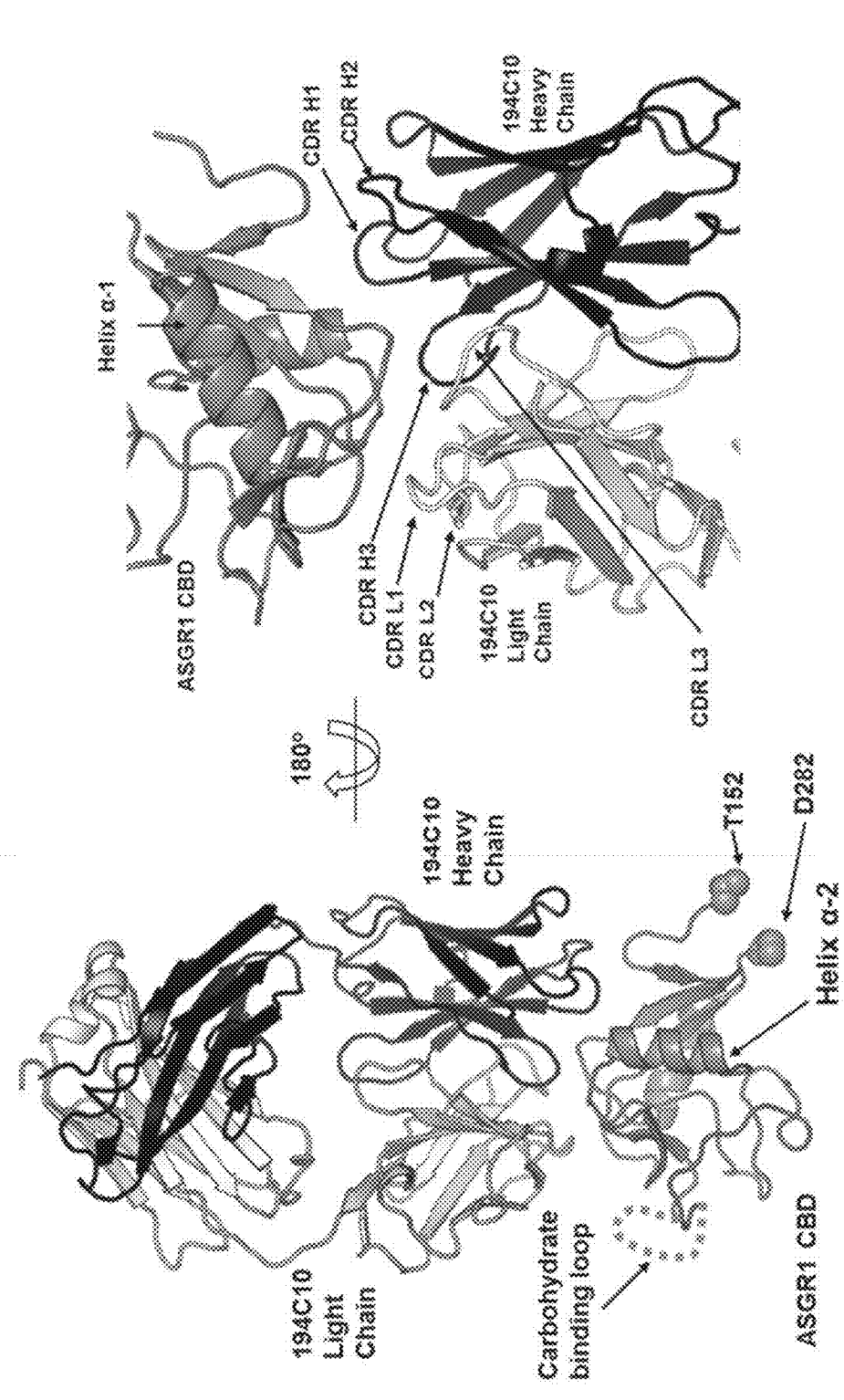
FIG. 41. A depiction of the structure of the ASGR-1 CBD and the 194C10 Fab. This figure depicts represents a disordered carbohydrate binding loop with a dashed line and highlights possible indirect inhibition of ASGR-1 CBD and the ligand (GalNAc) binding.
Figure 42:
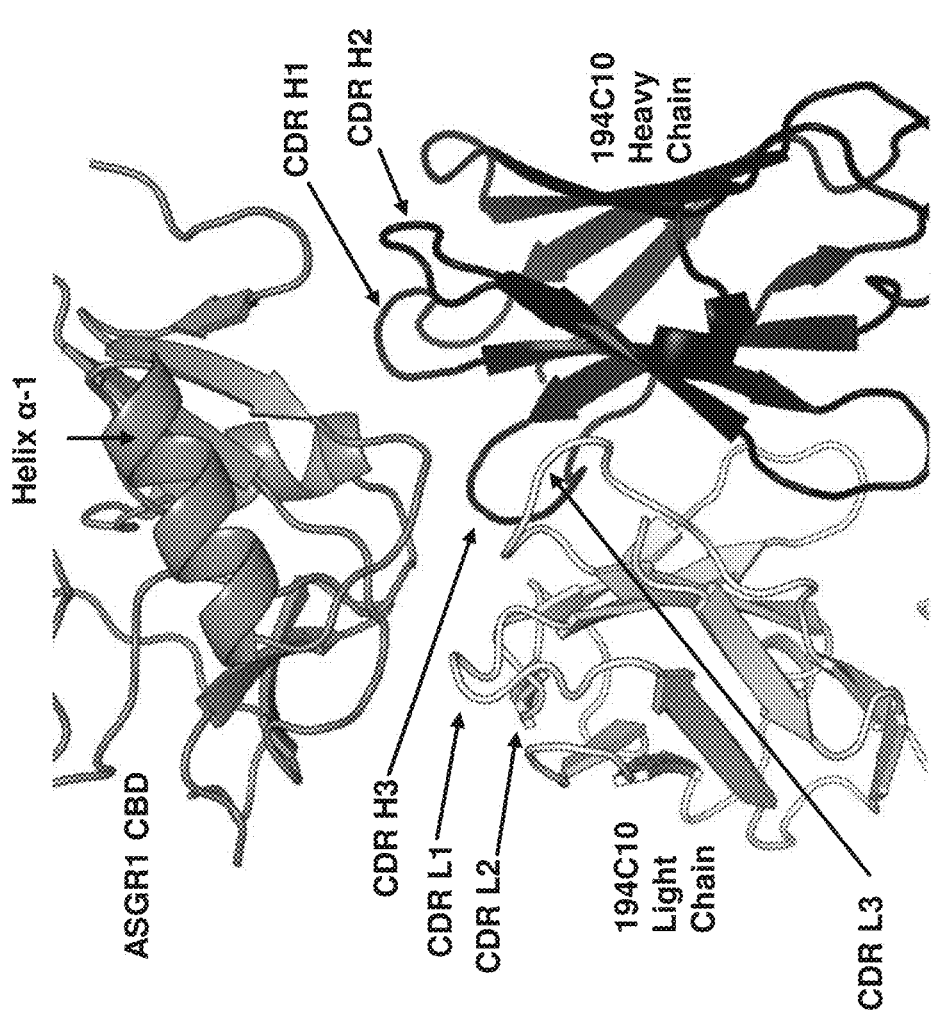
FIG. 42. An enlarged view of the structure of the ASGR-1 CBD and the 194C10 Fab. This figure shows the CDRs of the 194C10 that interact with the ASGR-1 CBD and highlights that there may be direct inhibition of the ASGR-1 CBD and the ligand (GalNAc) binding.

The present example presents the crystal structure of the ASGR-1 CBD bound to the Fab fragment of 194C10, determined to 2.6 Å resolution (the conditions of which are described above in section B of this Example). This structure, depicted in FIGS. 41 and 42, shows that when 194C10 binds to/interacts with ASGR-1, it likely induces a conformational rearrangement of the carbohydrate binding loop, impairing ASGR-1 CBD from binding to ligand (e.g., carbohydrate), as well as possibly blocking the ligand (e.g., carbohydrate) binding by ASGR-1 CBD, with the paratope of the 194C10 Fab. These data indicate that the 174H4 Fab may directly and/or indirectly inhibit the ASGR-1 CBD/Ligand binding.

The depicted structure also allows one to identify specific core ASGR amino acid residues for the interaction interface of 194C10 with ASGR-1. This was defined as residues that are within 5 Å of the 194C10 protein. The core residues are as follows: N157, R170, S171, G172, Q202, H203, H204, I205, G206, P207, V208, N209, T210, D260, R271, P272, Y273, R274 (SEQ ID NO:5).

The structures were also used to identify boundary ASGR-1 amino acid residues for the interaction interface with 194C10. These residues were ASGR-1 residues that were from 5-8 Å of the 194C10 protein. The boundary residues are as follows: V156, W158, V159, H161, W167, F168, S169, K173, K199, F200, V201, W211, R237, H257, F258, T259, D261, D267, V268, Q270, W275 (SEQ ID NO:5).

Specific core 194C10 amino acid residues of the interaction interface with ASGR-1 were defined as 194C10 residues that are within 5 Å of the ASGR-1 protein. The core 194C10 Heavy Chain residues include: R30, Y31, Y33, E50, S54, S56, N58, D98, Y99, G100; and the core 194C10 Light Chain residues include: N30, S31, Y33, F50, S54, S68, Y92, E93, W97.

Boundary 194C10 amino acid residues of the interaction interface with ASGR-1 were defined as 194C10 residues that are 5-8 Å from the ASGR-1 protein. The boundary 194C10 Heavy Chain residues include: S28, Y32, W34, S35, W47, G49, I51, S52, H53, G55, T57, R97, A101, F102, D103; and the boundary 194C10 Light Chain residues include: S28, V29, G32, L47, G51, A52, S53, R55, A56, G69, Q90, Q91, S94, S95.

The coordinates for the ASGR-1 CBD/GalNAc crystal structure complex are presented in Table 10.4.

Methods:
The same methods were followed as described above in part B of this example except for the following changes:
1. 194C10 Fab fragment was generated by cleaving the 194C10 mAb with caspase 3.

194C10 mAb Heavy Chain (SEQ ID NO: 32678):
QVQLQQWGAGLLKPSETLSLTCAVSGGSFRYYYWSWIRQPPGKGLEWFG

EINHAGSTNYNPSLKSRVTISIDTSKNQFSLKLRSVTAADTAVYYCARD

YGAFDIWGQGTMVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCG

194C10 mAb Light Chain (SEQ ID NO: 32679):
EIVLTQSPGTLSLSPGERATLSCRASPSVNSGYLAWYQQKPGQTPRLLI

FGASSRATGIPDRFSASGSGADFTLTISRLEPEDFAVYFCQQYESSPWT

FGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC*

194C10 Fab Heavy Chain (Post-Cleavage)(SEQ ID NO: 32680):
QVQLQQWGAGLLKPSETLSLTCAVSGGSFRYYYWSWIRQPPGKGLEWFG

EINHAGSTNYNPSLKSRVTISIDTSKNQFSLKLRSVTAADTAVYYCARD

YGAFDIWGQGTMVTVSSASTKGPSVFPLAPSSKSTSGGTAALGCLVKDY

FPEPVTVSWNSGALTSGVHTFPAVLQSSGLYSLSSVVTVPSSSLGTQTY

ICNVNHKPSNTKVDKKVEPKSCGSDEVD

194C10 Fab Light Chain (Post-Cleavage):
Same sequence as 194C10 mAb Light chain

1. The 194C10 Fab/ASGR-1 CBD complex was concentrated to 13.6 mg/mL and crystallized with 0.2 M Ammonium Sulfate, 0.1 M Tris pH 7.5, 20% PEG5000MME;
2. The dataset was collected from a single crystal on beamline ID22 at the Argonne National Laboratory and processed with XDS/CCP4;
3. The 194C10 Fab/ASGR-1 CBD complex crystals grow in the P12$_1$1 space group with unit cell dimensions a=65.62, b=130.44, c=85.93 Å and β=111.6° with two complex molecules per asymmetric unit, and diffract to 2.6 Å resolution;
4. The 194C10 Fab/ASGR-1 CBD complex structure was solved by molecular replacement with the program Phaser; and
5. The structure was improved with multiple rounds of model building with Coot[3] and refinement with Phenix[4], to a final $R_{factor}$=17.1/$R_{free}$=22.8.

L. Interaction Between GalNAc, ASGR-1 and Certain Antibodies

The structure of the 72G9/ASGR-1 complex (Item G above) was overlaid on the ASGR-1/ligand (GalNac) structure (Item A above) and the result of this combination is depicted in FIG. 31B. The structure of the 54E9/ASGR-1 complex (Item I above) was also overlaid on the ASGR-1/ligand (GalNac) structure (Item A above) and the result of this combination is depicted in FIG. 35B. The structure of the 218G4/ASGR-1 complex (Item J above) was overlaid on the ASGR-1/ligand (GalNac) structure (Item A above) and the result of this combination is depicted in FIG. 38. The structure of the 176H4/ASGR-1 complex (Item K above) was overlaid on the ASGR-1/ligand (GalNac) structure (Item A above) and the result of this combination is depicted in FIG. 40. These figures demonstrate areas on ASGR-1 which can be usefully targeted to inhibit ASGR-1 interaction with a ligand, e.g., GalNac. These figures show that 72G9, 54E9, 218G4 and 176H4 directly interact with a subset of amino acid residues that are specifically involved in binding to the ligand (e.g., GalNAc).

As noted above, analysis of the crystal structures identified specific amino acids involved in the interaction between ASGR-1 and the partner proteins (the core and boundary regions of the interface on the ASGR-1 surface) and the spatial requirements of these partner proteins to interact with ASGR-1. The structures suggest ways to inhibit the interaction between ASGR-1 and a ligand, GalNAc. First, as noted above, binding an agent to ASGR-1 where it shares residues in common with the binding site of a ligand such as GalNAc would inhibit the interaction between ASGR-1 and the ligand. Second, an agent that binds outside of the residues in common can sterically interfere with the ligand that are either N- or C-terminal to the ligand to prevent the interaction between ASGR-1 and a ligand.

In some embodiments, the residues that are involved in both ligand binding and are close to the areas where the above noted antigen binding proteins bind are especially useful for manipulating ASGR-1 binding to ligand. For example, amino acid residues from interfaces in common in both the core region and boundary region for the different binding partners are listed in Table 10.5 below.

TABLE 10.5

| Parameters | Amino acid position(s) |
|---|---|
| 72G9/GalNAc both under 5 Å | Q240, D242, W244 |
| 72G9 under 5 Å/GalNAc 5-8 Å | E239, P241, D243, Y245, G246, G252 |
| 72G9 at 5-8 Å/GalNAc under 5 Å | R237, E253 |
| 72G9/GalNAc both at 5-8 Å | P238, H247, C255, V268 |
| 54E9/GalNAc both under 5 Å | N209, R237, Q240, D242, H257, T259, N265, D267, Y273 |
| 54E9 under 5 Å/GalNAc 5-8 Å | P238, E239, D260, R263, R271 |
| 54E9 at 5-8 Å/GalNAc under 5 Å | E253, D266 |
| 54E9/GalNAc both at 5-8 Å | D243, F258, W264 |
| 218G4/GalNAc both under 5 Å | N209, H257, N265, D267, Y273 |
| 218G4 under 5 Å/GalNAc 5-8 Å | D260, R271 |
| 218G4 at 5-8 Å/GalNAc under 5 Å | R237, T259, D266 |
| 218G4/GalNAc both at 5-8 Å | F258, V268 |
| 176H4/GalNAc both under 5 Å | N209, R237, Q240, W244, E253, H257, T259, N265, D267, Y273 |
| 176H4 under 5 Å/GalNAc 5-8 Å | G246, H247, D260, R271 |
| 176H4 at 5-8 Å/GalNAc under 5 Å | D266 |
| 176H4/GalNAc both at 5-8 Å | P238, E239, Y245, F258, R263, W264, V268 |

As will be appreciated by one of skill in the art, in some embodiments, the antigen binding proteins bind to and/or block at least one of the above noted residues.

Antigen binding proteins and molecules that interact with the relevant areas or residues of the structure of ASGR-1 (including those areas or residues within 15, 15-8, 8, 8-5, 5, or fewer angstroms from where ligands, such as GalNAc, or the antibodies, interact with ASGR-1) depicted in the figures (e.g., FIGS. 19-42) and/or their corresponding positions on the structures from the coordinates are also contemplated.

Example 11: Determination of the Binding Affinity of ASGR-1 Specific Antibodies To quantitate the binding affinity of specific antibodies for ASGR-1 (either purified from hybridoma supernatants or made recombinantly), association and dissociation rates can be measured using a ForteBio Octet instrument. The antibodies were covalently coupled to AR2G tips to load levels close to 2 nm and then bound to the soluble human ASGR-1 carbohydrate binding domain (CBD; amino acid residues 154-281; N-terminal 6×His tag) in a 3-fold serial dilution series starting typically at 30 nM with either 3-point or 6-point dilution series. Experimental kinetic results were globally fit to a 1:1 binding model in order to determine the association and dissociation rate constants as well as the equilibrium dissociation constant. Association and dissociation times were chosen to ensure that curvature was present during association curves and measured dissociation levels dropped at least 5% from starting levels. All Octet buffers contained 10 mM Tris (pH7.5), 150 mM NaCl, 1 mM $CaCl_2$, 0.10 mg/ml BSA and 0.13% Triton X-100. Octet assays were run at 27° C. Because this assay only measures binding to the ASGR-1 CBD, antibodies that recognize epitopes partially or entirely outside the CBD and/or recognize ASGR-1 in the context of a native ASGR complex, for example, as could occur on cell membranes, may not score as positive in this assay. Data provided for representative antibodies in TABLE 11.1.

TABLE 11.1

| Ab name | Octet binding $K_D$ (nM) |
|---|---|
| 4H6 | 4.8 |
| 4B1 | >30 |
| 4A2 | 0.06 |
| 5E5 | 7.6 |
| 6G7 | 2.0 |
| 7G4 | 0.9 |
| 7F4 | 1.2 |
| 7E11 | 1.6 |
| 12D2 | >30 |
| 22G5 | 1.4 |
| 25A4 | 0.03 |
| 26C4 | 0.4 |
| 29H8 | 1.0 |
| 48B12 | 0.3 |
| 54E9 | >30 |
| 56E5 | 0.5 |
| 72G9 | 0.5 |
| 75G3 | 1.0 |
| 176H4 | 0.8 |
| 184E7 | 0.3 |
| 190F8 | 0.6 |
| 191G1 | 2.4 |
| 191G10 | 0.5 |
| 193E7 | 3.5 |
| 194A4 | 0.7 |
| 194C1 | 1.3 |
| 194C10 | 4 |
| 197G3 | 0.8 |
| 198D2 | >30 |
| 198G3 | 0.04 |
| 202A3 | >30 |
| 218G4 | 2.6 |
| 4A2.001 | 0.06 |
| 4A2.001.003 | 0.04 |
| 4A2.001.004 | 0.03 |
| 4A2.001.005 | 0.02 |
| 4A2.001.010 | 0.04 |
| 4A2.001.012 | 0.04 |
| 25A4.001 | 0.06 |
| 25A4.001.021 | 0.04 |
| 4H6.009 | 0.28 |
| 7E11.001 | 0.71 |
| 7E11.001.005 | 0.42 |
| 7E11.001.007 | 0.62 |
| 5E5.016 | 1.46 |
| 5E5.019 | 1.80 |
| 5E5.005 | 2.00 |

Example 12: CHO-S:huASGR-1 Cell Binding Assay

CHO-S stable high-expressing cell line were developed for both human ASGR-1 as well as mouse ASGR-1. A typical 384 well plate multiplex flow cytometry-based cell binding method is described as followed: Parental CHO-S cells and CHO-S:huASGR-1 cells were respectively labeled using a CellTrace CFSE Cell Proliferation Kit (ThermoFisher Catalog #C34554) and CellTrace Violet Cell Proliferation Kit (ThermoFisher Catalog #C34557) CHO-S: muASGR-1 were not labeled. 20 ul of cells at 4° C. were added to duplicate wells of the 384 well plate. The cells were equally mixed from all three cell lines (30K cells/well). Then 20 ul of the ASGR-1 antibodies (either purified from hybridoma supernatants or made recombinantly) were added in an 11-point dose response using a 1:2 fold serial dilution starting at 100 nM. The cells and antibodies were incubated for 30 min at 4° C. and then spun down and washed twice with FACS buffer containing 1 mM CaCl2. 30 ul of anti-huIgG-APC secondary antibodies were then added at a 1:1000 dilution) for 30 min at 4° C. and then washed once with the same buffer. 60 ul of PI (1:1000) was added and then the cells were read by a core flow cytometry facility. The cells were gated first for live cells, then for single cells and finally for the cell dyes to separate the mixed cells into the three different cell populations. Histograms of signal vs count representing the binding profile of each antibody at each antibody concentration were automatically analyzed for the median of the binding signal and then a binding graph was made with log 10 antibody concentration in nM on the X axis with standard deviation of the median signals from the duplicate wells on the Y-axis. The binding curves were fit with a standard four parameter sigmoidal binding curve and EC50's reported for all graphs with full curves. Data provided for representative antibodies in TABLE 12.1.

TABLE 12.1

| Ab name | Cell binding EC50 (nM) |
| --- | --- |
| 4H6 | 1.70 |
| 4B1 | 4.1 |
| 4A2 | 0.82 |
| 4A2.001 | 1.8 |
| 5E5 | 3.80 |
| 6G7 | 0.6 |
| 7G4 | 0.69 |
| 7F4 | 5.40 |
| 7E11 | 1.40 |
| 7E11.001 | 3.2 |
| 12D2 | 3.2 |
| 22G5 | 7.2 |
| 25A4 | 1.6 |
| 25A4.001 | 1.2 |
| 26C4 | 11 |
| 29H8 | 1.9 |
| 48B12 | 38 |
| 54E9 | 5 |
| 56E5 | 1.1 |
| 72G9 | 0.41 |
| 75G3 | 1 |
| 176H4 | 1 |
| 184E7 | 1 |
| 190F8 | 9 |
| 191G1 | 0.16 |
| 191G10 | 0.31 |
| 193E7 | 0.13 |
| 194A4 | 25 |
| 194C1 | 0.11 |
| 194C10 | 0.56 |
| 197G3 | 0.25 |
| 198D2 | 0.14 |
| 198G3 | 0.21 |
| 202A3 | 0.8 |
| 218G4 | 2.2 |

Figure 43:
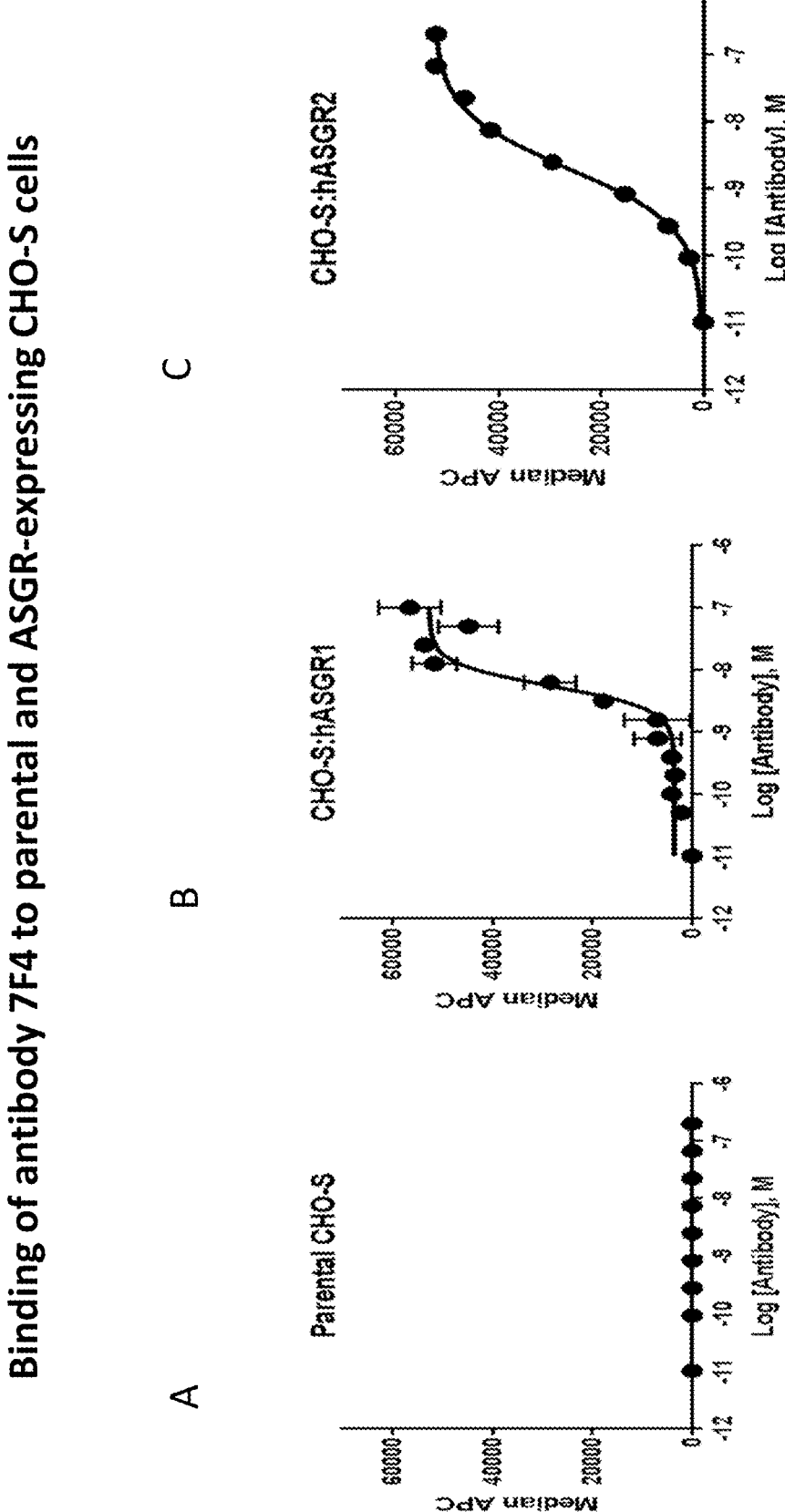
FIG. 43. Panels A-C are graphical representations showing antibody binding results from human ASGR-1 and human ASGR-2 expressing cells.

For human ASGR-2, CHO-S stable cells expressing C-terminal His-tagged human ASGR-2 were resuspended in cold flow buffer (10 mM Tris, pH 7.5, 137 mM NaCl, 1 mM CaCl2 and 2% fetal bovine serum) and 1.5×10e6 cells per well were added to a 96-well, v-bottom plate in a volume of 80 ul. 80 ul of antibody at 400 nM was then added to each well. After incubation on ice for 30 min, the cells were centrifuged at 1400 rpm for 3 min and then washed twice in cold flow buffer. The cells were then resuspended in 120 ul of anti-human IgG-APC (diluted 1:1000 in flow buffer) and incubated on ice for 30 minutes, centrifuged and washed twice as before, and resuspended in 200 ul cold flow buffer, and then analyzed on a BD-LSR II flow cytometer. Data provided for antibody 7F4 in FIG. 43.

Example 13: CHO-S:huASGR-1 Ligand Blocking Assay

All ASGR-1 antibodies that bound either human or mouse ASGR-1 stable CHO-S cells were then tested for ligand blocking using both a protein ligand and a synthetic sugar ligand. The method in brief is as follows: first, 20 ul of either CHO-Shuman or mouse ASGR-1 cells were added to wells of a 384 well plate (30 k cells/well) followed by spin and discarding the supernatant. Second, 10 ul of the antibodies (either purified from hybridoma supernatants or made recombinantly) were added in duplicate to the cells in a dilution series (200 nM top concentration, 1:2 serial dilution, 11 point curve) and were incubated for 30 min at 4° C. Third, 10 ul of the minimally biotinylated ligands were added at 2× their binding EC05, so that the wells contained a final 20 ul volume with Ab starting at 100 nM and the ligand at their EC50. After 30 min incubation at 4□C, the plate was spun and washed twice with FACS buffer+1 mM CaCl2 followed by the detection streptavidin-AF647 at 1:1000 dilution. After 30 min at 4° C., the cells were spun and washed once and then 60 ul PI added at 1:1000 dilution and the plates delivered to a core flow cytometry facility. The plates were read and processed similarly to the cell binding method except the signal now represents an inhibition curve and typically decreases a function of increasing antibody concentration. IC50 nM potency and % Inhibition were reported. The desialylated, biotinylated asialofetuin (see Example 9A) and biotinylated GalNAc-PAA (Fisher #NC9024754) were used as ligands with measured binding EC50s of 10.7 and 5.4 nM. Differences in the ability of antibodies to block these two ligands could occur as a result of differences in, for example, avidity stemming from differences in the number and/or orientation of the ASGR binding terminal sugar residues of each ligand, steric hindrance between antibody and each ligand, and/or changes in the conformation of ASGR induced by antibody binding that selectively alters the binding of each ligand. Data provided for representative antibodies in TABLE 13.1.

TABLE 13.1

| | Ligand Blocking | | | |
| --- | --- | --- | --- | --- |
| | bn-GalNAc-PAA | | bn-asialofetuin | |
| Ab name | IC50 (nM) | % Inhibition | IC50 (nM) | % Inhibition |
| 4H6 | 8.1 | 20% | 12 | 85% |
| 4B1 | 42 | 36% | 64 | 75% |
| 4A2 | 54 | 70% | 11 | 99% |
| 4A2.001 | 28 | 75 | 12 | 99 |
| 5E5 | >200 | 0% | 16 | 95% |

TABLE 13.1-continued

| | Ligand Blocking | | | |
| | bn-GalNAc-PAA | | bn-asialofetuin | |
| Ab name | IC50 (nM) | % Inhibition | IC50 (nM) | % Inhibition |
|---|---|---|---|---|
| 6G7 | >200 | 0% | 11 | 99% |
| 7G4 | 20 | −30% | 14 | 96% |
| 7F4 | 0.24 | 30% | 2.6 | 99% |
| 7E11 | 40 | 37% | 13 | 99% |
| 7E11.001 | >100 | 50 | 13 | 99 |
| 12D2 | 2.1 | 10% | 10 | 20% |
| 22G5 | 11 | 93% | 3.4 | 99% |
| 25A4 | 40 | 77% | 11 | 99% |
| 25A4.001 | 31 | 68 | 8.1 | 99 |
| 26C4 | 36 | 83% | 6.6 | 99% |
| 29H8 | 17 | 99% | 7 | 99% |
| 48B12 | 86 | 94% | 19 | 99% |
| 54E9 | 100 | 19% | 50 | 75% |
| 56E5 | 45 | 99% | 23 | 99% |
| 72G9 | 24 | 20% | 53 | 20% |
| 75G3 | 115 | 99% | 29 | 99% |
| 176H4 | 73 | 79% | 59 | 99% |
| 184E7 | 10 | 99% | 23 | 99% |
| 190F8 | 44 | 83% | 34 | 98% |
| 191G1 | 62 | 78% | 24 | 99% |
| 191G10 | 56 | 99% | 27 | 99% |
| 193E7 | 33 | 60% | 30 | 99% |
| 194A4 | 48 | 60% | 57 | 99% |
| 194C1 | 72 | 89% | 34 | 99% |
| 194C10 | 87 | 99% | 30 | 99% |
| 197G3 | 15 | 74% | 29 | 90% |
| 198D2 | 55 | 99% | 22 | 99% |
| 198G3 | 5 | 81% | 26 | 99% |
| 202A3 | 32 | 96% | 16 | 98% |
| 218G4 | 71 | 99% | 28 | 99% |

Example 14: ASGR-1 Specific Antibody Optimization (Chemical Degradation Site Engineering)

Variable domain sequence motifs having a high risk of sidechain degradation were engineered out of ASGR-1 specific antibodies. See for example, ASGR-1 specific antibody sequences in Tables 6 and 7.

Certain high risk motifs included: (1) CDR 'NG' and 'NT' sequences prone to asparagine deamidation, (2) CDR 'DG,' 'DH', 'DS,' and 'DT' sequences prone to aspartic acid isomerization, (3) and CDR3 tryptophans prone to oxidation. Bioinformatics and structural analyses were used to identify substitutions likely to retain binding affinity to the ASGR-1 CBD. Typically, substitution identities were derived from germline sequences or from sequence-related ASGR-1 CBD-binding mAbs. These substitutions were then modeled into a homology model of the unbound mAb using the software MOE (CCG)[1] to predict structural fitness. For cases in which the bioinformatics or structural analyses did not provide a clear substitution identity, residue types chemically similar to the parent residue were identified.

Variable domain sequence motifs violating multiple sequence alignment-based pair-wise residue covariance trends[2] were also engineered out of ASGR-1 specific antibodies. Substitution identities for covariance violators were identified using a hybrid bioinformatics/structural approach similar to that used to remediate degradation sites.

1. *Molecular Operating Environment* (*MOE*), 2013.08; Chemical Computing Group, Inc., 1010 Sherbooke St. West, Suit #910, Montreal, QC, Canada, H3A 2R7, 2016.
2. Kannan, G. *Method of Correlated Mutational Analysis to Improve Therapeutic Antibodies*. US Patent Application PCT/US2012/028596 filed Mar. 9, 2012.

Example 15: Epitope Mapping Using Peptide Arrays

Custom peptide microarrays were obtained commercially (PEPperPRINT GmbH). For epitope mapping using linear arrays, the antigen (ASGR-1) was translated into 291 different overlapping 15 amino acid (aa) peptides printed in duplicate (582 peptide spots per array copy). For epitope mapping using cyclized arrays, the antigen (ASGR-1) was translated into 888 different overlapping 7 aa, 10 aa and 13 aa peptides printed in duplicate (1,776 peptide spots per array copy). Peptide cyclization was accomplished using N- to C-terminal thioether formation with and without an additional scaffold for varying conformational restriction. Each PEPperCHIP® Peptide array is framed by Flag (DYKDDDDKAS) and HA (YPYDVPDYAG) control peptides. Assay buffer was PBS-T (PBS, pH 7.4, 0.05% Tween 20), blocking buffer was Rockland Blocking Buffer (Rockland Immunochemicals), staining buffer was assay buffer+10% Rockland Blocking buffer. Secondary antibody was goat anti-human IRDye680LT (Li-Cor). Control antibodies were anti-FLAG M2 DyLight800, anti-HA DyLight680. Arrays were scanned on Li-Cor Odyssey with an offset of 0.65 mm, 21 um resolution.

Array staining and detection was per manufacturer's instructions. Briefly, arrays were pre-stained with secondary antibodies for 30 minutes, washed and scanned to detect background binding. Arrays were then stained with commercially available primary antibodies overnight, followed by washing and 30 minute incubation with labeled secondary antibodies. Arrays were scanned to detect binding of anti-ASGR-1 antibodies. Finally, arrays were stained with control antibodies for 45 minutes prior to washing and scanning to detect control peptides.

Antigen binding proteins with desired binding properties can be identified using this assay.

Example 16: In Vivo Studies

RNAi constructs that reduce expression of ASGR-1 and/or ASGR-2 and/or antigen binding proteins, such as monoclonal antibodies, that inhibit ligand binding to ASGR, ASGR-1, and/or ASGR-2 in vitro can be administered in vivo to a relevant animal model and levels and/or activity of endogenous blood proteins like alkaline phosphatase measured. In addition, the clearance of exogenously administered ASGR ligands (for example asialoglycoproteins, certain non-asialylated proteins, synthetic ligands, etc.) can be inhibited by pre-treatment with RNAi or a co- or pre-administered antibody.

Additionally, physiologic effects of the antigen binding proteins or RNAi can be evaluated in relevant animal models of cardiovascular disease using readouts including blood pressure, primary and secondary hemostasis, heart function and morphology, endothelial function, LDL cholesterol levels, non-HDL cholesterol levels, inflammation, and atherosclerosis.

Example 17: Effect of ASGR-1 Antibody 4A2 on Serum LDL Cholesterol and Alkaline Phosphatase in Normal and Obese Cynomolgus Monkeys The purpose of the study was to evaluate the LDL cholesterol (LDL-C)-lowering activity of anti-ASGR inhibitors. In general, cynomolgus monkeys do not have high levels of total cholesterol, HDL-C or LDL-C. Therefore, both normal and dyslipidemic models were utilized in this example. In the dyslipidemic model, monkeys were selected if their LDL levels were at least 100 mg/dL (normal is 40-60 mg/dL), and if there body mass index was over 41 kg/m$^2$ (normal is below 35 kg/m$^2$). Animals that met these criteria on standard diet were classified as spontaneously obese dyslipidemic. Other animals were fed a high-fat diet (HFD; 4.15 kcal/gm, 32% fat) prior to inclusion in the study and were classified as HFD obese dyslipidemic.

Naive male spontaneous obese dyslipidemic and HFD obese dyslipidemic cynomolgus monkeys were given a single subcutaneous injection of anti-ASGR-1 antibody 4A2.001 (IgG1z-SEFL2) (10 mg/kg in 10 mM sodium acetate, 9% sucrose, 0.01% polysorbate-80, pH 5.2). Naïve male and female normal cynomolgus monkeys were given a single intravenous injection of anti-ASGR-1 antibody 4A2.001 (IgG1z-SEFL2) (100 mg/kg in 10 mM sodium acetate, 9% sucrose, 0.01% polysorbate-80, pH 5.2). Blood was collected from overnight fasted animals to monitor LDL-C and alkaline phosphatase (ALP) levels post-antibody injection. Blood was collected 70, 118, 190 and 268 hours post-injection (dyslipidemic models) and at 0.05, 0.25, 0.5, 1, 4, 8, 24, 48, 72, 168, 240, 336, 504, 672, 840, 1008, and 1176 hours post-injection (normal). LDL-C decrease (%) and ALP increase (%) were the main endpoints of the study and were measured on Roche C311 and C501 chemistry analyzers. Baseline levels of LDL-C and ALP were established from blood collected 7 days prior to antibody administration.

Figure 44:
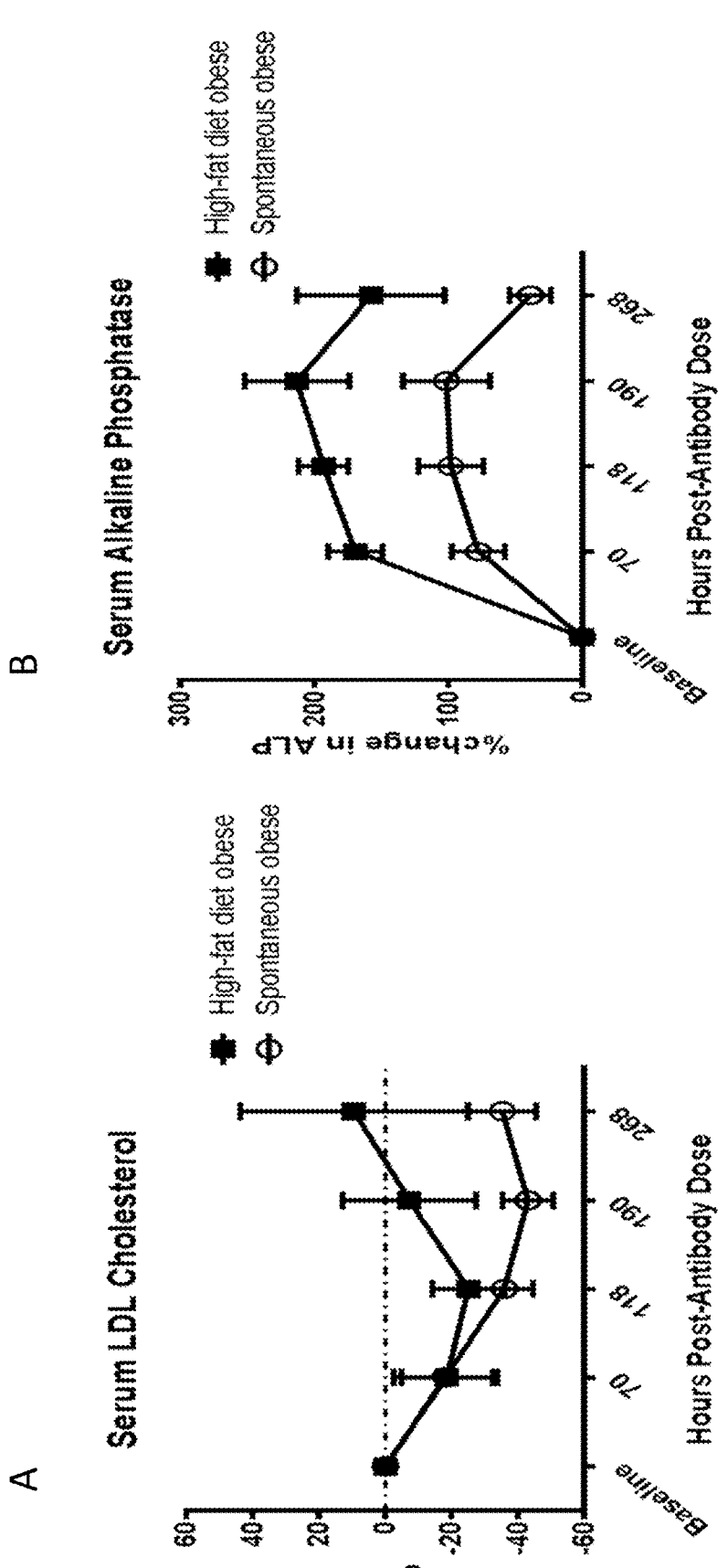
FIG. 44. Panel A is a graphical representation of the effect of ASGR-1 antibody, 4A2, on serum LDL cholesterol levels in obese cynomolgus monkeys. Panel B is a graphical representation of the effect of ASGR-1 antibody, 4A2, on serum alkaline phosphatase levels in obese cynomolgus monkeys. Data is expressed in the % change from baseline.
Figure 45:
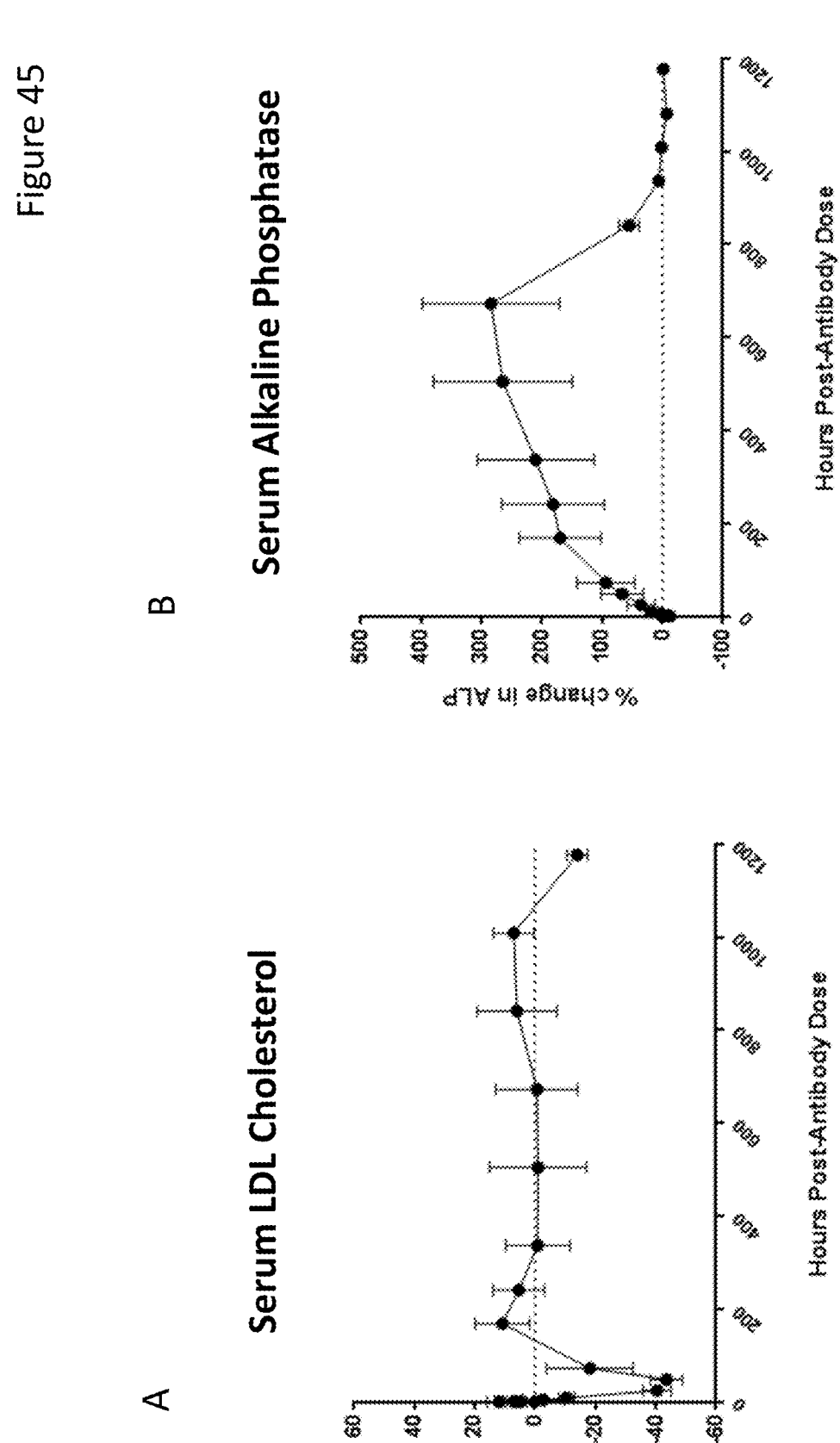
FIG. 45. Panel A is a graphical representation of the effect of ASGR-1 antibody, 4A2, on serum LDL cholesterol levels in normal cynomolgus monkeys. Panel B is a graphical representation of the effect of ASGR-1 antibody, 4A2, on serum alkaline phosphatase levels in normal cynomolgus monkeys. Data is expressed in the % change from baseline.
Figure 46:
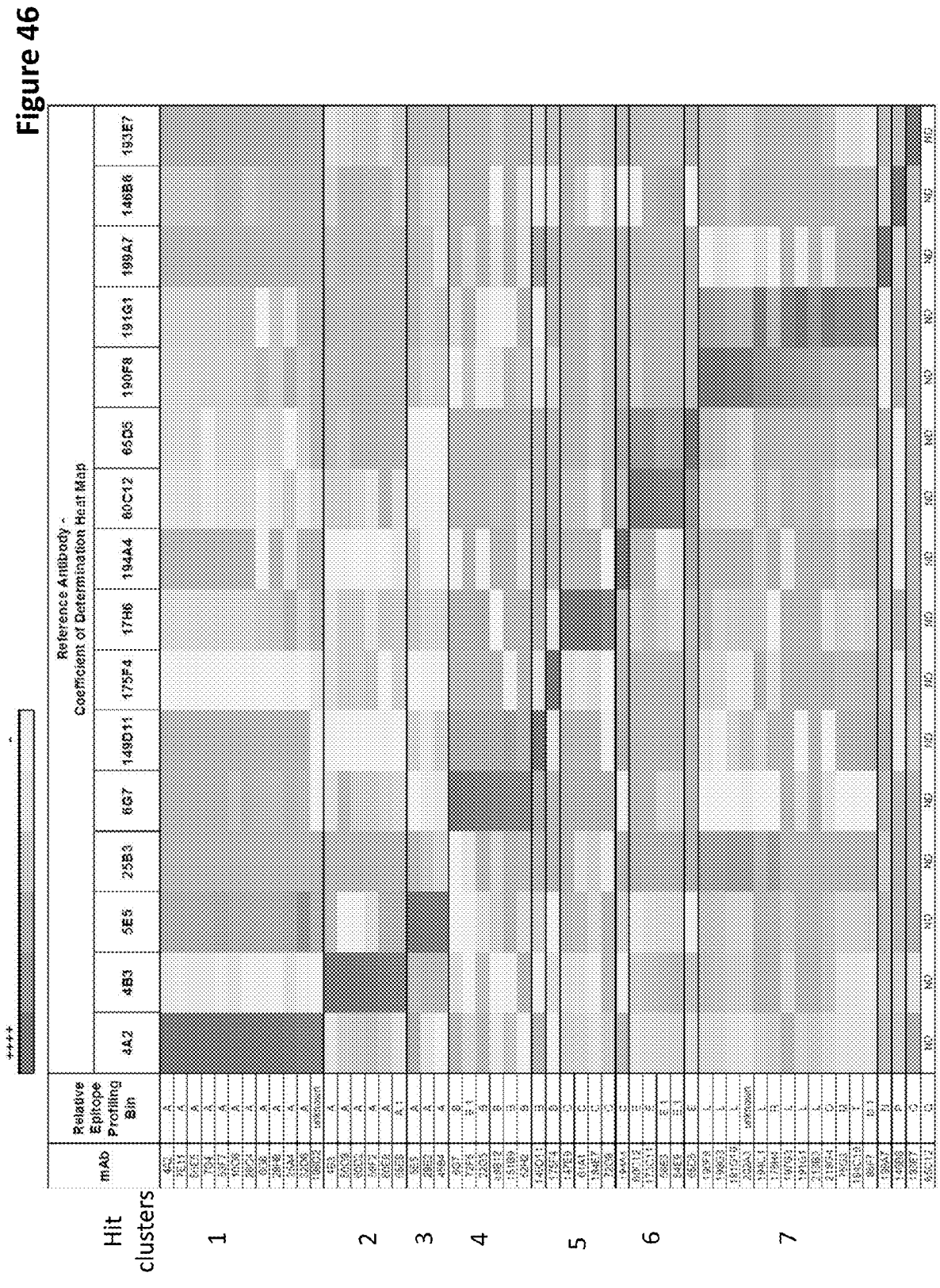
FIG. 46. A coefficient of determination heat map representing the coefficient of determination profiles of test ASGR-1 ligand blocking antibody-reference antibody combinations from an Arginine/Glutamic Acid scanning mutagenesis (Example 7E). Dark shading represents highly similar data, while light shading represents highly dissimilar data. The relative epitope profiling (antibody competition/binding) bin assignments are also indicated.
Figure 47:
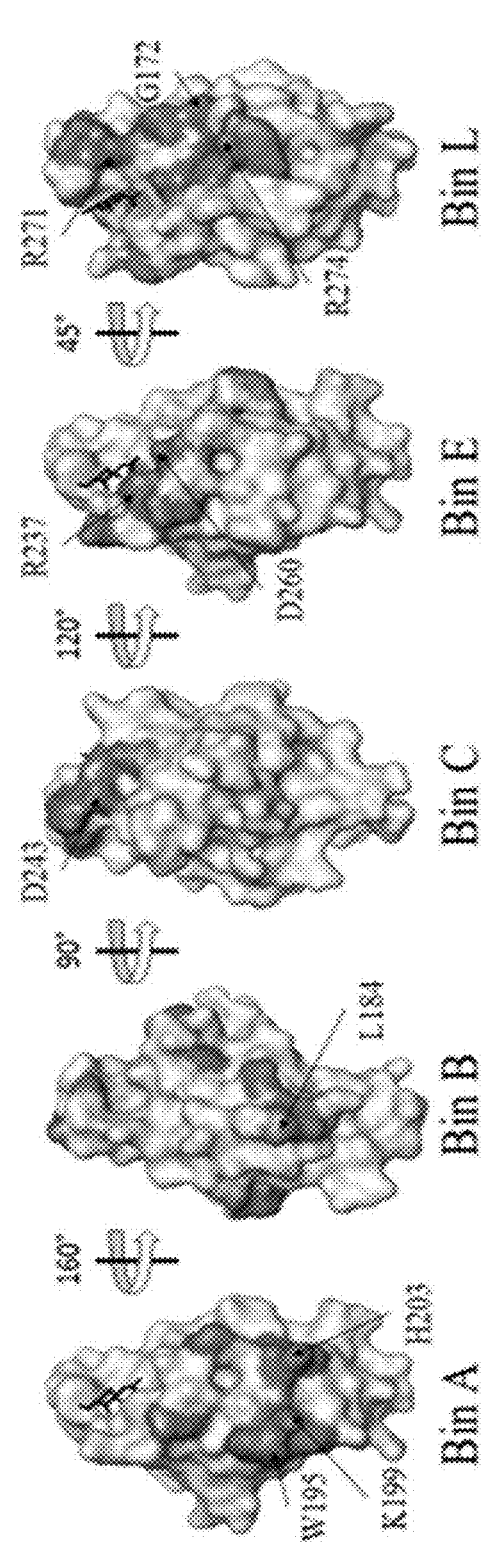
FIG. 47. A computer representation showing alternative views of the ASGR-1 CBD protein and the surface locations of amino acid residues identified as being important for antibody binding via Arginine/Glutamic Acid scanning mutagenesis (Example 7E). The relative epitope profiling (antibody competition/binding) bin assignments are also indicated. Ligand (GalNAc) is shown as a stick representation (black). The ASGR-1 CBD is shown as a surface representation (light grey). The positions of amino acids identified by Arg/Glu mutational scanning are indicated (dark grey surface). The relative positions of key amino acids in each bin are shown for reference only.

Dyslipidemic Model:
  Species: *Macaca fascicularis*
  Weight Range: >7.0 kg
  BMI Range: >41 kg/m$^2$
  Age range: 12-17 years
  Time on HFD: 6 months
  Source: KBI monkey colony
  Number and Sex: 3 male spontaneous obese monkeys and 3 male HFD induced obese monkeys (BMI>41, LDL>80 mg/dL)). Animals were selected from a larger pool based on similar baseline LDL and ALP levels Normal Model:
  Species: *Macaca fascicularis*
  Weight Range: 2.6-4.2 kg
  Age range: 2.5-4 years
  Number and Sex: 2 male and 1 female fed normal laboratory diet Data for this study is provided in FIG. 44 (dyslipidemic model) and FIG. 45 (normal model).

Example 18: Proteomic Profiling of Serum Samples from Human ASGR1 Carriers and Controls Introduction As described above in Example 1, ASGR1 loss-of-function (LOF) was found to be associated with a beneficial phenotype (protected from coronary artery disease, lower LDL cholesterol and longer life span) in human[1]. To understand the mechanism of action underlying this association and find potential biomarkers, proteomic measurement of human serum samples were performed and compared to changes in circulating protein levels between the ASGR1 LOF variant carriers and controls.

Materials and Methods

Sample Collection and Proteomic Profiling

A total of 333 human serum samples were acquired from the deCODE Icelandic population study, including 100 ASGR1 del12 heterozygous carriers (cases group) and 233 non-carriers (controls group). The Case/Control Groups are well matched by sex, age and collection time/freezer storage time. 150 ul serum samples were shipped to SomaLogic Inc, where 1310 proteins were measured by the SOMAscan Assay 1.3 k. The 1310 proteins were SOMAmer® Reagents Generated to Human Proteins, the complete list of tested proteins are summarized in the SOMAscan Assay 1.3K Content, Rev 1 (Effective: Sep. 21, 2015) which is incorpored by reference herein in its entirety.

The SOMAscan assay measured serum protein concentration using a Slow Off-rate Modified DNA Aptamer (SOMAmer)-based capture array[2]. Each of the 1310 proteins is bond by its respective fluorescently labeled SOMAmer in the assay and their concentrations are reflected by the respective SOMAmer's relative fluorescence units (RFU).

Data Analysis

2 Samples were removed due to low volume that did not meet Somascan requirements and 13 samples were removed because they had been treated with EDTA. The RFU data of each measured protein was log transformed, then centered and scaled to calculate standardized RFU values for this protein. Principle components (PCs) were derived from 1310 standardized RFU values by principle components analysis. An outlier removal based on Hotellings T2 distribution of PC1 and PC2 was applied and excluded another 8 samples from further analysis.

After QC, the remaining 93 ASGR1 Del12 heterozygous Carriers (cases group) and 217 samples without the Del12 allele (controls group) and their standardized RFU values of each protein were analyzed by a linear model adjusting for Age, Sex, FreezerTime and the first 10 PCs, $$Yi = \beta 0 + \beta 1 Gi + \beta 2 AGEi + \beta 3 SEXi + \beta 4 FTi + \beta 5 PC1i + \ldots + \beta 15 PC10i + \varepsilon i$$

where is the standardized RFU value for the i$^{th}$ sample for a particular protein, Gi is the Del12 genotype the i$^{th}$ sample and β1 capture the estimates of the mean difference between human samples with Del12 and without Del12. Since 1310 tests were performed for the proteins on Somascan platform, we calculated the significant threshold by Bonferroni method ($0.05/1310 = 3.82 \times 10^{-5}$) assuming these are independent tests. However, the Bonferroni correction is likely too stringent because proteins are often correlated with each other therefore these tests are not independent. Thus a realistic threshold of significance ($5.19 \times 10^{-5}$) was obtained by performing 100,000 permutations using the method by Sham and Purcell 2014[3].

Results and Discussion

Using the permutation threshold, 41 Proteins were identified to have significant serum levels between human ASGR1 del12 carriers and non-carriers ($P < 5.19 \times 10^{-5}$). Of those, 26 show significant increase in the carriers (Table 18.1) and 15 decrease significantly in the carriers (Table 18.2). These changes are likely to mediate the beneficial effects resulting from ASGR1 loss of function seen in the del12 carriers. The levels of these proteins in blood can serve as biomarkers for ASGR1 loss of function and be used to assess ASGR1-targeted therapy during drug development.

TABLE 18.1

Proteins with significant increase in serum of ASGR1 del12 carriers.

| p value | Estimate (SD) | Gene | Full Name |
|---|---|---|---|
| 3.71E−54 | 1.34 | TNFSF8 | Tumor necrosis factor ligand superfamily member 8 |
| 1.33E−52 | 1.45 | CD163 | Scavenger receptor cysteine-rich type 1 protein M130 |
| 2.07E−25 | 1.09 | CSF1R | Macrophage colony-stimulating factor 1 receptor |
| 1.44E−24 | 1.16 | LYVE1 | Lymphatic vessel endothelial hyaluronic acid receptor 1 |
| 1.03E−22 | 0.65 | IL6ST | Interleukin-6 receptor subunit beta |
| 4.56E−15 | 0.67 | IL18BP | Interleukin-18-binding protein |
| 1.16E−12 | 0.74 | CD300C | CMRF35-like molecule 6 |
| 2.47E−12 | 0.59 | TYRO3 | Tyrosine-protein kinase receptor TYRO3 |
| 8.85E−12 | 0.80 | LRP8 | Low-density lipoprotein receptor-related protein 8 |
| 1.76E−09 | 0.66 | IL1RL1 | Interleukin-1 receptor-like 1 |
| 2.62E−09 | 0.61 | ISLR2 | Immunoglobulin superfamily containing leucine-rich repeat protein 2 |
| 4.01E−09 | 0.55 | SIGLEC7 | Sialic acid-binding Ig-like lectin 7 |
| 4.47E−09 | 0.48 | NRXN3 | Neurexin-3-beta |
| 1.03E−07 | 0.58 | PLAU | Urokinase-type plasminogen activator |
| 2.96E−07 | 0.37 | CD55 | Complement decay-accelerating factor |
| 8.27E−07 | 0.53 | CD48 | CD48 antigen |
| 1.22E−06 | 0.31 | TNFRSF21 | Tumor necrosis factor receptor superfamily member 21 |
| 1.62E−06 | 0.36 | MRC2 | C-type mannose receptor 2 |
| 3.82E−06 | 0.57 | KLK13 | Kallikrein-13 |
| 4.95E−06 | 0.33 | IGF1R | Insulin-like growth factor 1 receptor |
| 1.46E−05 | 0.45 | ANGPT2 | Angiopoietin-2 |
| 2.02E−05 | 0.39 | CNTN4 | Contactin-4 |
| 2.57E−05 | 0.47 | FCGR3B | Low affinity immunoglobulin gamma Fc region receptor III-B |
| 2.93E−05 | 0.38 | C1S | Complement C1s subcomponent |
| 3.92E−05 | 0.40 | LY9 | T-lymphocyte surface antigen Ly-9 |
| 4.48E−05 | 0.46 | CD200R1 | Cell surface glycoprotein CD200 receptor 1 |

TABLE 18.2

Proteins with significant decrease in serum of ASGR1 del12 carriers.

| p value | Estimate (SD) | Gene | Target Full Name |
|---|---|---|---|
| 1.08E−09 | −0.52 | CD93 | Complement component C1q receptor |
| 6.32E−09 | −0.50 | IDS | Iduronate 2-sulfatase |
| 1.56E−07 | −0.34 | RGMB | RGM domain family member B |
| 2.91E−07 | −0.44 | TGFBI | Transforming growth factor-beta-induced protein ig-h3 |
| 5.56E−07 | −0.48 | LUM | Lumican |
| 6.67E−07 | −0.46 | MMP2 | 72 kDa type IV collagenase |
| 1.36E−06 | −0.38 | FLRT2 | Leucine-rich repeat transmembrane protein FLRT2 |
| 2.18E−06 | −0.48 | AHSG | Alpha-2-HS-glycoprotein |
| 2.44E−06 | −0.37 | CSH1 CSH2 | Chorionic somatomammotropin hormone |
| 3.16E−06 | −0.54 | ESM1 | Endothelial cell-specific molecule 1 |
| 1.36E−05 | −0.52 | AFM | Afamin |
| 1.67E−05 | −0.48 | TNFRSF17 | Tumor necrosis factor receptor superfamily member 17 |
| 2.68E−05 | −0.46 | OMD | Osteomodulin |
| 4.69E−05 | −0.23 | GDI2 | Rab GDP dissociation inhibitor beta |
| 5.09E−05 | −0.45 | SPOCK2 | Testican-2 |

REFERENCES

1 See also, Nioi, P. et al. Variant ASGR1 Associated with a Reduced Risk of Coronary Artery Disease. *The New England journal of medicine* 374, 2131-2141, doi: 10.1056/NEJMoa1508419 (2016).

2 Gold, L. et al. Aptamer-based multiplexed proteomic technology for biomarker discovery. *PLoS One* 5, e15004, doi:10.1371/journal.pone.0015004 (2010).

3 Sham, P. C. & Purcell, S. M. Statistical power and significance testing in large-scale genetic studies. *Nature reviews. Genetics* 15, 335-346, doi:10.1038/nrg3706 (2014).

Example 19: Proteomic Profiling of Serum Samples from ASGR1 Cyno PK-PD Study

Introduction

As described above in Example 1, ASGR1 loss-of-function (LOF) was found to be associated with a beneficial phenotype (protected from coronary artery disease, lower LDL cholesterol and longer life span) in human[1]. Certain ASGR-1 antigen binding proteins disclosed herein were found to mimic the LOF effects, and can be useful in the treatment of coronary artery disease. In brief, cynomolgus monkeys were treated with certain ASGR-1 specific, ligand blocking antibodies in order to study the PK-PD profile of these antibodies. Moreover, a dose-dependent elevation of alkaline phosphatase (ALP) levels was observed in the Ab-treated cynos, which resembles the ALP elevation seen in human ASGR1 LOF carriers. In addition to ALP, proteomic profiling in human serum identified 41 proteins that potentially underlie the beneficial effects caused by ASGR1 LOF as described above in Example 18. To compare effects of anti-ASGR1 antibody treatment with the human ASGR1 LOF and identify comparable signatures in cynomolgus monkey, proteomic measurement of the serum samples from this study was conducted. The list of proteins with altered levels in the antibody-treated animals is compared to the ones identified in human LOF carriers.

Materials and Methods

Sample Selection and Proteomic Profiling 6 animal groups with 3 animals in each group were selected for proteomic profiling. The 6 groups include 5 antibody-treated groups (mAb1/25A4, mAb2/4A2, mAb3/7E11, mAb4/5E5 and mAb8/4H6) and a vehicle control group (mAb6). The animals were dosed once at 100 mg/kg. Serum samples from time points 0, 168, 336, 504, 672 and 1176 hours were collected for each animal (Table 19.1 & 19.2). The only exception is group mAb8/4H6, where time point 1008 hour is used instead of 1176 hour. 120 ul serum samples were shipped to SomaLogic Inc, where 1310 proteins (see table 18.0) were measured by the SOMAscan Assay 1.3k.

The SOMAscan assay measures serum protein concentration using a Slow Off-rate Modified DNA Aptamer (SOMAmer)-based capture array. Each of the 1310 proteins is bond by its respective fluorescently labeled SOMAmer in the assay and their concentrations are reflected by the respective SOMAmer's relative fluorescence units (RFU).

TABLE 19.1

Serum sample selection

| Animal group | Animal Number | Time points | | | | | |
|---|---|---|---|---|---|---|---|
| | | D 0 0 hr | D 8 168 hr | D 15 336 hr | D 22 504 hr | D 29 672 hr | D 50 1176 hr |
| 25A4 | 701, 702, 703 | ✓ | ✓ | ✓ | ✓ | ✓ | ✓ |
| 4A2 | 704, 705, 706 | ✓ | ✓ | ✓ | ✓ | ✓ | ✓ |
| 7E11 | 707, 708, 711 | ✓ | ✓ | ✓ | ✓ | ✓ | ✓ |
| 5E5 | 709, 710, 712 | ✓ | ✓ | ✓ | ✓ | ✓ | ✓ |
| SEFL2-control | 716, 717, 718 | ✓ | ✓ | ✓ | ✓ | ✓ | ✓ |
| 4H6 | 204, 205, 206 | ✓ | ✓ | ✓ | ✓ | ✓ | ✓* |

*4H6 was collected at D 43 (1008 hr).

TABLE 19.2

List of all sample groups by treatment and time points.

| Sample group | Treatment (e.g., drug, vehicle, etc.) | Time point | # of Samples in Group | Subject ID |
|---|---|---|---|---|
| 25A4_D0 | mAb1 | 0 Hr | 3 | 701, 702, 703 |
| 25A4_D8 | mAb1 | 168 Hr | 3 | 701, 702, 703 |
| 25A4_D15 | mAb1 | 336 Hr | 3 | 701, 702, 703 |
| 25A4_D22 | mAb1 | 504 Hr | 3 | 701, 702, 703 |
| 25A4_D29 | mAb1 | 672 Hr | 3 | 701, 702, 703 |
| 25A4_D50 | mAb1 | 1176 Hr | 3 | 701, 702, 703 |
| 4A2_D0 | mAb2 | 0 Hr | 3 | 704, 705, 706 |
| 4A2_D8 | mAb2 | 168 Hr | 3 | 704, 705, 706 |
| 4A2_D15 | mAb2 | 336 Hr | 3 | 704, 705, 706 |

TABLE 19.2-continued

List of all sample groups by treatment and time points.

| Sample group | Treatment (e.g., drug, vehicle, etc.) | Time point | # of Samples in Group | Subject ID |
|---|---|---|---|---|
| 4A2_D22 | mAb2 | 504 Hr | 3 | 704, 705, 706 |
| 4A2_D29 | mAb2 | 672 Hr | 3 | 704, 705, 706 |
| 4A2_D50 | mAb2 | 1176 Hr | 3 | 704, 705, 706 |
| 7E11_D0 | mAb3 | 0 Hr | 3 | 707, 708, 711 |
| 7E11_D8 | mAb3 | 168 Hr | 3 | 707, 708, 711 |
| 7E11_D15 | mAb3 | 336 Hr | 3 | 707, 708, 711 |
| 7E11_D22 | mAb3 | 504 Hr | 3 | 707, 708, 711 |
| 7E11_D29 | mAb3 | 672 Hr | 3 | 707, 708, 711 |
| 7E11_D50 | mAb3 | 1176 Hr | 3 | 707, 708, 711 |
| 5E5_D0 | mAb4 | 0 Hr | 3 | 709, 710, 712 |
| 5E5_D8 | mAb4 | 168 Hr | 3 | 709, 710, 712 |
| 5E5_D15 | mAb4 | 336 Hr | 3 | 709, 710, 712 |
| 5E5_D22 | mAb4 | 504 Hr | 3 | 709, 710, 712 |
| 5E5_D29 | mAb4 | 672 Hr | 3 | 709, 710, 712 |
| 5E5_D50 | mAb4 | 1176 Hr | 3 | 709, 710, 712 |
| CTL_D0 | mAb6 | 0 Hr | 3 | 716, 717, 718 |
| CTL_D8 | mAb6 | 168 Hr | 3 | 716, 717, 718 |
| CTL_D15 | mAb6 | 336 Hr | 3 | 716, 717, 718 |
| CTL_D22 | mAb6 | 504 Hr | 3 | 716, 717, 718 |
| CTL_D29 | mAb6 | 672 Hr | 3 | 716, 717, 718 |
| CTL_D50 | mAb6 | 1176 Hr | 3 | 716, 717, 718 |
| 4H6_D0 | mAb8 | 0 Hr | 3 | 204, 205, 206 |
| 4H6_D8 | mAb8 | 168 Hr | 3 | 204, 205, 206 |
| 4H6_D15 | mAb8 | 336 Hr | 3 | 204, 205, 206 |
| 4H6_D22 | mAb8 | 504 Hr | 3 | 204, 205, 206 |
| 4H6_D29 | mAb8 | 672 Hr | 3 | 204, 205, 206 |
| 4H6_D43 | mAb8 | 1008 Hr | 3 | 204, 205, 206 |

Data Analysis

Figure 58:
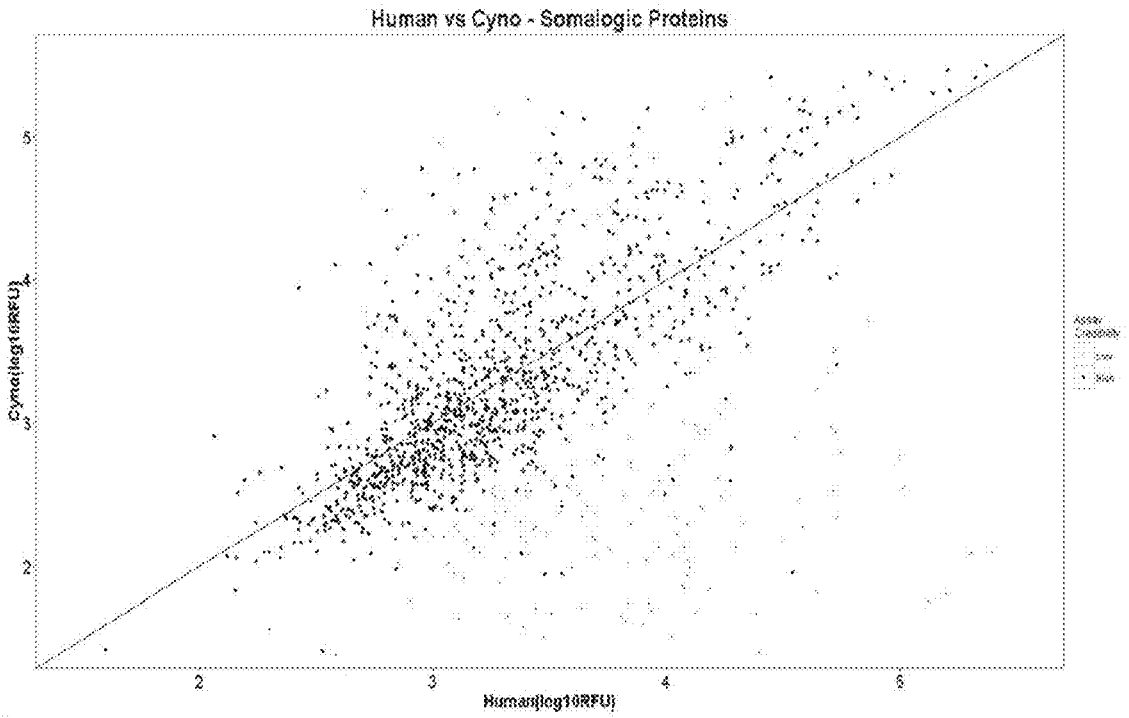
FIG. 58. A graph depicting the credibility of protein measurements in cynomolgus monkey. Log 10 RFU of mean protein levels in the two species are plotted and the ones with low credibility (light dots) and high credibility (darker dots) are marked.
Figure 59:
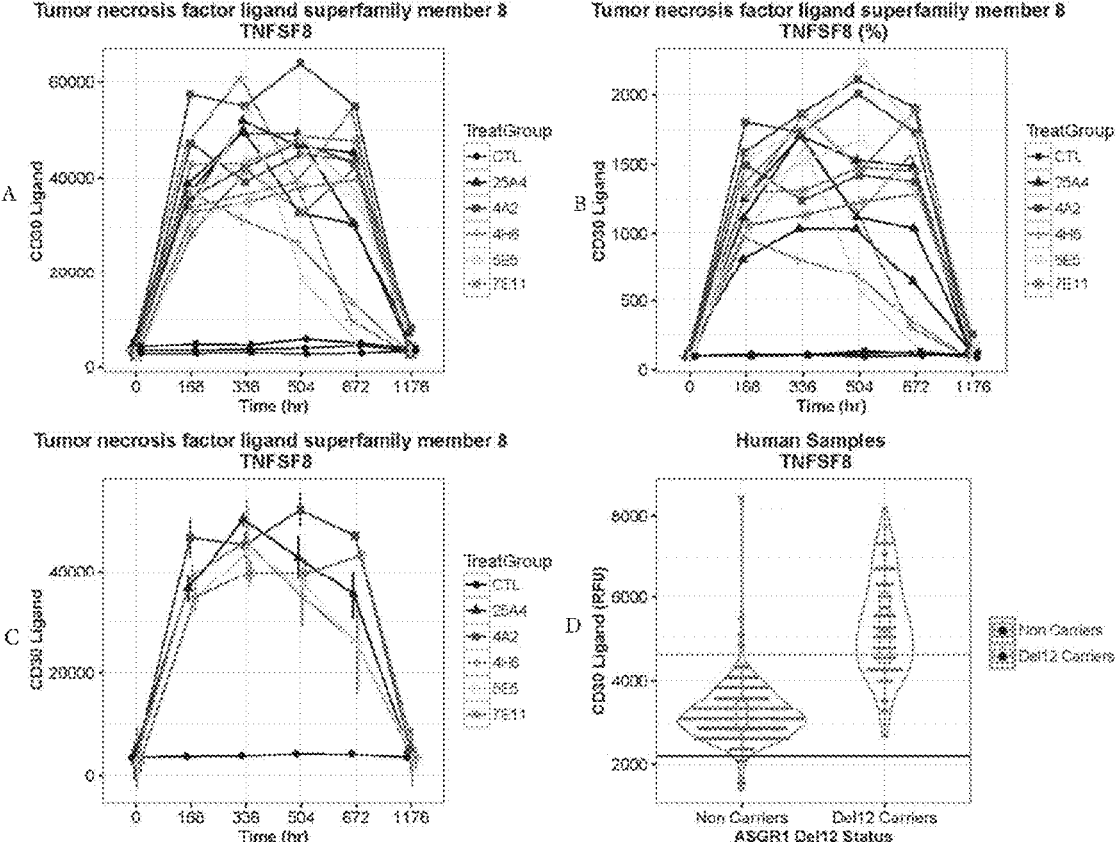
FIG. 59. Serum protein analysis of cynomolgus monkey treated with anti-ASGR-1 antibodies. Panel A is a graph depicting TNFSF8 protein levels in individual animals of different treatment group across the time points. Panel B is a graph depicting normalized TNFSF8 protein levels (percent of time point 0) in individual animals of different treatment groups across the time points. Panel C is a graph depicting TNFSF8 protein levels in each treatment group (n=3, error bar represents the SEM), and Panel D is a graph depicting the distribution of TNFSF8 protein levels in human ASGR1 del12 carriers and non-carriers.

As the SOMAscan assay was developed for humans, some proteins in cynomolgus monkey may not be recognized by the SOMAmer reagents. As a result, SOMAscan measurements of these proteins would have low credibility and may not reflect the true protein levels. A simple criterion was defined to determine the credibility of the measurements, assuming the serum levels of a given protein are in relatively close range in human and cynomolgus monkey. The mean and range of each protein level in human are calculated based on the 217 human control samples from the human proteomic study described in Example 18. The mean and range of each protein level in cynomolgus monkey are calculated based on a total of 48 samples including measurements of all time points for the SEFL-2 control group and the pre-treatment (D0) and washout period (D50) measurements of all the other groups. A protein measurement would be assigned low credibility if (1) its range in cynomolgus monkey is not overlapping with human; and (2)

there is a 5 fold difference between the mean level of this protein in human and cynomolgus monkey. A total of 162 proteins were determined as low-credibility by these criteria and were excluded (FIG. 58, which depicts a summary of the credibility of protein measurements in cynomolgus monkey). In FIG. 58, log 10 RFU of mean protein levels in the two species are plotted and the ones with low credibility (light shading) and high credibility (black) are marked.

One sample in the 4H6 group was removed due to low volume that did not meet the requirements for the SOMAscan assay. No outliers were found in the principle components analysis. A linear mixed model adjusting for potential confounding factors was used to test whether the ASGR1 antibody treatment changes each protein level differently from the control group over time points, $$Y_{ti} = \beta_0 + \beta_1 \text{TREATGROUP}_i + \beta_2 \text{TIME}_{ti} + \beta_3 (\text{TREATGROUP}_i)(\text{TIME}_{ti}) + \beta_4 \text{COV}_{ti} + \ldots + \beta_{m+4} \text{COV}_{ti} + b_{0i} + \varepsilon_{ti}$$

which is determined by the p-value for $\beta_3$ (i.e., treatment by time interaction; mean difference in slopes between treatment conditions). The random effect $b_{0i}$ captures individual animal heterogeneity. The TREATGROUP is coded as (25A4=4A2=7E11=5E5=4H6=1; SELF-2=0) and TIME is coded as (D8=D15=D22=D29=1; D0=D50=0) to test for the ASGR1 antibodies effect after treatment comparing to pre-treatment and washout period. Since multiple tests were performed for the proteins on SOMAscan platform, a Bonferroni corrected significant threshold ($5 \times 10^{-5}$) was used.

Results and Discussion 33 proteins were identified to have significant serum level changes after ASGR1 antibody treatment (Table 19.3; $P < 5 \times 10^{-5}$). Interestingly, all the 33 proteins show increased levels (1.36~10.18 fold) after ASGR1 antibody treatment.

TABLE 19.3

Proteins with significant changes after ASGR1 antibody treatment in Cynomolgus monkey.

| P-value | Estimated Fold Change | Gene | Full Name |
|---|---|---|---|
| 1.87E−13 | 10.18 | TNFSF8 | Tumor necrosis factor ligand superfamily member 8 |
| 1.01E−06 | 8.56 | ASGR1 | Asialoglycoprotein receptor 1 |
| 1.35E−10 | 3.93 | ADGRE2 | Adhesion G protein-coupled receptor E2 |
| 2.74E−11 | 2.86 | CD86 | T-lymphocyte activation antigen CD86 |
| 1.46E−11 | 2.81 | TNFRSF21 | Tumor necrosis factor receptor superfamily member 21 |
| 7.48E−10 | 2.57 | L1CAM | Neural cell adhesion molecule L1 |
| 6.09E−12 | 2.42 | PLXNC1 | Plexin-C1 |
| 1.22E−07 | 2.11 | MRC2 | C-type mannose receptor 2 |
| 1.18E−06 | 2.10 | AMIGO2 | Amphoterin-induced protein 2 |
| 2.28E−11 | 2.02 | ANGPT2 | Angiopoietin-2 |
| 6.68E−09 | 1.99 | INSR | Insulin receptor |
| 1.02E−10 | 1.93 | IL17RA | Interleukin-17 receptor A |
| 7.12E−12 | 1.90 | NRXN3 | Neurexin-3-beta |
| 5.95E−06 | 1.85 | GPNMB | Transmembrane glycoprotein NMB |
| 2.03E−06 | 1.74 | IGF1R | Insulin-like growth factor 1 receptor |
| 3.91E−09 | 1.73 | PLAUR | Urokinase plasminogen activator surface receptor |
| 3.58E−09 | 1.69 | FGFR1 | Fibroblast growth factor receptor 1 |
| 1.26E−06 | 1.60 | LRP8 | Low-density lipoprotein receptor-related protein 8 |
| 3.87E−09 | 1.55 | LYPD3 | Ly6/PLAUR domain-containing protein 3 |
| 3.17E−06 | 1.55 | GRN | Granulins |
| 4.27E−05 | 1.54 | CNTN4 | Contactin-4 |
| 4.59E−07 | 1.54 | KDR | Vascular endothelial growth factor receptor 2 |
| 4.99E−06 | 1.53 | IL12RB2 | Interleukin-12 receptor subunit beta-2 |
| 5.85E−06 | 1.52 | ROBO3 | Roundabout homolog 3 |
| 1.44E−06 | 1.50 | ALCAM | CD166 antigen |
| 3.83E−05 | 1.46 | TYRO3 | Tyrosine-protein kinase receptor TYRO3 |
| 3.09E−05 | 1.45 | CADM1 | Cell adhesion molecule 1 |
| 1.53E−08 | 1.44 | JAG1 | Protein jagged-1 |
| 2.58E−09 | 1.43 | ISLR2 | Immunoglobulin superfamily containing leucine-rich repeat protein 2 |
| 3.11E−05 | 1.39 | SET | Protein SET |
| 4.64E−05 | 1.38 | IL20RA | Interleukin-20 receptor subunit alpha |
| 2.15E−06 | 1.36 | KLRK1 | NKG2-D type II integral membrane protein |
| 2.39E−05 | 1.36 | GFRA2 | GDNF family receptor alpha-2 |

To compare results from this study with the human proteomic study, a list of proteins made by the 33 proteins in Table 19.3 and the top 41 proteins identified in human was compiled. This results in a list of 64 proteins total. The estimates of protein level change and p-value of the changes in the studies were compared (Table 19.4). Based on concordance of change in the cyno (in response to ASGR1 antibody treatment) and human (in response to ASGR1 LOF) studies, the proteins are classified into 5 tiers. Tier 1 includes 10 proteins that pass the stringent Bonferroni corrected significance level ($p < 5 \times 10^{-5}$) in both studies with the same direction of changes. The number of proteins supported by strong evidence in both studies are much higher than the number one would expect by chance ($p = 1.58 \times 10^{-8}$; Fisher's exact test). It indicates that ASGR1 Ab treatment can induce a serum protein levels change in cyno that is similar to the effect of del12 LOF variant in Human. Therefore, these proteins are the core biomarkers. For example, the strongest biomarker TNFSF8 had more than 10 fold increase after ASGR1 Antibody treatment (FIGS. 59A-59D, which depict the results of serum protein levels of TNFSF8 in cyno and human studies).

Tier 2 contains 12 proteins with strong evidence ($p < 5 \times 10^{-5}$) in the cyno study and suggestive evidence ($p < 0.05$) in human with the same direction of changes. Both Tier 1 and 2 proteins have increased levels in both studies. Tier 3 includes 11 proteins that are found significant only in the cyno study but not human. These proteins are likely to be biomarkers specific for the drug modality or for cynomolgus monkeys. For example, the soluble secreted form of ASGR1 increased more than 10 fold after antibody treatment but no significant difference was observed in human between the ASGR1 del12 carriers and non-carriers. Tier 4 contains 17 proteins with significant evidence ($p < 5 \times 10^{-5}$) in the human study but not supported by the cyno study. Majority of the proteins in Tier 4 has decrease levels in human del12 carriers. This observation may indicate a difference between antibody treatment and constitutive gene LOF. It could also possibly be due to species difference or simply caused by lower statistical power in the cyno study.

Lastly, there are 14 proteins with significant changes in human classified as Tier 5 because they were excluded in the cyno study due to the low credibility of their SOMAmer reagents.

In summary, the two studies show high degree of concordance between the antibody treatment in cynomolgus monkey and ASGR1 LOF in humans, with 10 proteins (Tier 1) showing very significant changes in the same direction in both studies. The ASGR-1 antibody treatment is working well as a way of mimicking the effects of ASGR1 LOF in humans and can be useful in the treatment of coronary artery disease.

TABLE 19.4

Five tiers of protein biomarkers and comparison of the estimates of protein level change and p-value between the two studies.

| Target Full Name | Gene | human | | Cyno | | Tier |
| --- | --- | --- | --- | --- | --- | --- |
| | | Estimate (SD) | P-value | Estimate log2FC | P-value | |
| Tumor necrosis factor ligand superfamily member 8 | TNFSF8 | 1.34 | 3.7E−54 | 3.35 | 1.87E−13 | 1 |
| Tumor necrosis factor receptor superfamily member 21 | TNFRSF21 | 0.31 | 1.2E−06 | 1.49 | 1.46E−11 | 1 |
| C-type mannose receptor 2 | MRC2 | 0.36 | 1.6E−06 | 1.08 | 1.22E−07 | 1 |
| Angiopoietin-2 | ANGPT2 | 0.45 | 1.5E−05 | 1.01 | 2.28E−11 | 1 |
| Neurexin-3-beta | NRXN3 | 0.48 | 4.5E−09 | 0.93 | 7.12E−12 | 1 |
| Insulin-like growth factor 1 receptor | IGF1R | 0.33 | 5.0E−06 | 0.80 | 2.03E−06 | 1 |
| Low-density lipoprotein receptor-related protein 8 | LRP8 | 0.80 | 8.9E−12 | 0.68 | 1.26E−06 | 1 |
| Contactin-4 | CNTN4 | 0.39 | 2.0E−05 | 0.63 | 4.27E−05 | 1 |
| Tyrosine-protein kinase receptor TYRO3 | TYRO3 | 0.59 | 2.5E−12 | 0.55 | 3.83E−05 | 1 |
| Immunoglobulin superfamily containing leucine-rich repeat protein 2 | ISLR2 | 0.61 | 2.6E−09 | 0.52 | 2.58E−09 | 1 |
| T-lymphocyte activation antigen CD86 | CD86 | 0.39 | 2.1E−03 | 1.52 | 2.74E−11 | 2 |
| Neural cell adhesion molecule L1 | L1CAM | 0.30 | 5.5E−03 | 1.36 | 7.48E−10 | 2 |
| Plexin-C1 | PLXNC1 | 0.40 | 1.0E−04 | 1.28 | 6.09E−12 | 2 |
| Amphoterin-induced protein 2 | AMIGO2 | 0.44 | 1.9E−04 | 1.07 | 1.18E−06 | 2 |
| Interleukin-17 receptor A | IL17RA | 0.29 | 0.03 | 0.95 | 1.02E−10 | 2 |
| Urokinase plasminogen activator surface receptor | PLAUR | 0.35 | 3.3E−04 | 0.79 | 3.91E−09 | 2 |
| Fibroblast growth factor receptor 1 | FGFR1 | 0.30 | 2.3E−03 | 0.75 | 3.58E−09 | 2 |
| Granulins | GRN | 0.27 | 5.7E−03 | 0.63 | 3.17E−06 | 2 |
| CD166 antigen | ALCAM | 0.20 | 9.1E−03 | 0.58 | 1.44E−06 | 2 |
| Protein jagged-1 | JAG1 | 0.17 | 0.01 | 0.53 | 1.53E−08 | 2 |
| Protein SET | SET | 0.28 | 2.1E−03 | 0.47 | 3.11E−05 | 2 |
| GDNF family receptor alpha-2 | GFRA2 | 0.39 | 9.2E−05 | 0.44 | 2.39E−05 | 2 |
| Asialoglycoprotein receptor 1 | ASGR1 | 0.00 | 0.99 | 3.10 | 1.01E−06 | 3 |
| Adhesion G protein-coupled receptor E2 | ADGRE2 | 0.04 | 0.70 | 1.97 | 1.35E−10 | 3 |
| Insulin receptor | INSR | 0.20 | 0.06 | 1.00 | 6.68E−09 | 3 |
| Transmembrane glycoprotein NMB | GPNMB | −0.22 | 0.01 | 0.89 | 5.95E−06 | 3 |
| Ly6/PLAUR domain-containing protein 3 | LYPD3 | −0.06 | 0.26 | 0.63 | 3.87E−09 | 3 |
| Vascular endothelial growth factor receptor 2 | KDR | 0.19 | 0.09 | 0.63 | 4.59E−07 | 3 |
| Interleukin-12 receptor subunit beta-2 | IL12RB2 | 0.11 | 0.38 | 0.61 | 4.99E−06 | 3 |
| Roundabout homolog 3 | ROBO3 | 0.08 | 0.55 | 0.61 | 5.85E−06 | 3 |
| Cell adhesion molecule 1 | CADM1 | −0.17 | 0.02 | 0.53 | 3.09E−05 | 3 |
| Interleukin-20 receptor subunit alpha | IL20RA | 0.05 | 0.69 | 0.47 | 4.64E−05 | 3 |
| NKG2-D type II integral membrane protein | KLRK1 | −0.14 | 0.25 | 0.44 | 2.15E−06 | 3 |
| Lymphatic vessel endothelial hyaluronic acid receptor 1 | LYVE1 | 1.16 | 1.44E−24 | 0.00 | 0.96 | 4 |
| CMRF35-like molecule 6 | CD300C | 0.74 | 1.16E−12 | 0.03 | 0.39 | 4 |
| Interleukin-1 receptor-like 1 | IL1RL1 | 0.66 | 1.76E−09 | 0.75 | 0.10 | 4 |
| Kallikrein-13 | KLK13 | 0.57 | 3.82E−06 | 0.08 | 0.42 | 4 |
| CD48 antigen | CD48 | 0.53 | 8.27E−07 | −0.06 | 0.81 | 4 |
| Rab GDP dissociation inhibitor beta | GDI2 | −0.23 | 4.69E−05 | −0.27 | 0.09 | 4 |
| Chorionic somatomammotropin hormone | CSH1 CSH2 | −0.37 | 2.44E−06 | 0.19 | 9.4E−03 | 4 |
| Leucine-rich repeat transmembrane protein FLRT2 | FLRT2 | −0.38 | 1.36E−06 | 0.30 | 0.03 | 4 |
| Transforming growth factor-beta-induced protein ig-h3 | TGFBI | −0.44 | 2.91E−07 | 0.13 | 0.46 | 4 |
| Testican-2 | SPOCK2 | −0.45 | 5.09E−05 | 0.10 | 0.96 | 4 |
| 72 kDa type IV collagenase | MMP2 | −0.46 | 6.67E−07 | 0.13 | 0.48 | 4 |
| Osteomodulin | OMD | −0.46 | 2.68E−05 | 0.12 | 0.78 | 4 |
| Alpha-2-HS-glycoprotein | AHSG | −0.48 | 2.18E−06 | 0.00 | 0.97 | 4 |
| Iduronate 2-sulfatase | IDS | −0.50 | 6.32E−09 | 0.05 | 0.33 | 4 |
| Complement component C1q receptor | CD93 | −0.52 | 1.08E−09 | 0.19 | 0.15 | 4 |

TABLE 19.4-continued

Five tiers of protein biomarkers and comparison of the estimates
of protein level change and p-value between the two studies.

| Target Full Name | Gene | human Estimate (SD) | human P-value | Cyno Estimate log2FC | Cyno P-value | Tier |
|---|---|---|---|---|---|---|
| Afamin | AFM | −0.52 | 1.36E−05 | 0.02 | 0.94 | 4 |
| Endothelial cell-specific molecule 1 | ESM1 | −0.54 | 3.16E−06 | 0.09 | 0.56 | 4 |
| Scavenger receptor cysteine-rich type 1 protein M130 | CD163 | 1.45 | 1.33E−52 | NA | NA | 5 |
| Macrophage colony-stimulating factor 1 receptor | CSF1R | 1.09 | 2.07E−25 | NA | NA | 5 |
| Interleukin-18-binding protein | IL18BP | 0.67 | 4.56E−15 | NA | NA | 5 |
| Interleukin-6 receptor subunit beta | IL6ST | 0.65 | 1.03E−22 | NA | NA | 5 |
| Urokinase-type plasminogen activator | PLAU | 0.58 | 1.03E−07 | NA | NA | 5 |
| Sialic acid-binding Ig-like lectin 7 | SIGLEC7 | 0.55 | 4.01E−09 | NA | NA | 5 |
| Low affinity immunoglobulin gamma Fc region receptor III-B | FCGR3B | 0.47 | 2.57E−05 | NA | NA | 5 |
| Cell surface glycoprotein CD200 receptor 1 | CD200R1 | 0.46 | 4.48E−05 | NA | NA | 5 |
| T-lymphocyte surface antigen Ly-9 | LY9 | 0.40 | 3.92E−05 | NA | NA | 5 |
| Complement C1s subcomponent | C1S | 0.38 | 2.93E−05 | NA | NA | 5 |
| Complement decay-accelerating factor | CD55 | 0.37 | 2.96E−07 | NA | NA | 5 |
| RGM domain family member B | RGMB | −0.34 | 1.56E−07 | NA | NA | 5 |
| Lumican | LUM | −0.48 | 5.56E−07 | NA | NA | 5 |
| Tumor necrosis factor receptor superfamily member 17 | TNFRSF17 | −0.48 | 1.67E−05 | NA | NA | 5 |

REFERENCES

1 See also, Nioi, P. et al. Variant ASGR1 Associated with a Reduced Risk of Coronary Artery Disease. *The New England journal of medicine* 374, 2131-2141, doi: 10.1056/NEJMoa1508419 (2016).
2 Gold, L. et al. Aptamer-based multiplexed proteomic technology for biomarker discovery. *PLoS One* 5, e15004, doi:10.1371/journal.pone.0015004 (2010).

Example 20: Method of Reducing a Risk of Cardiovascular Disease

A subject at risk of cardiovascular disease is identified. One or more antibodies as provided herein (see Example 7, as well as Tables A, B and C) and/or RNAi constructs that reduce expression of ASGR-1 and/or ASGR-2 (as outlined in Example 3), are administered to a subject at risk of cardiovascular disease. The antibody and/or RNAi construct reduces the level of expression of ASGR, ASGR-1 and/or ASGR-2. Subsequent rounds of antibodies and/or RNAi are administered to the subject. One or more of the markers in Example 19 (e.g., Tier 1) is monitored to make certain that an adequate amount of the antibody and/or RNAi construct is administered and is functioning as desired. The risk that the subject will experience cardio vascular disease is decreased.

Additionally, as a further option, physiologic effects of the antibody and/or RNAi can be evaluated in relevant animal models of cardiovascular disease using readouts including blood pressure, primary and secondary hemostasis, heart function and morphology, endothelial function, LDL cholesterol levels, non-HDL cholesterol levels, inflammation, and/or atherosclerosis.

Example 21: Method of Reducing a Risk of Myocardial Infarction or Coronary Artery Disease A subject at risk of a myocardial infarction or coronary artery disease is identified. One or more antibodies as provided herein (see Example 7, as well as Tables A, B and C) and/or RNAi constructs that reduce expression of ASGR-1 and/or ASGR-2 (as outlined in Example 3), are administered to a subject at risk of a myocardial infarction or coronary artery disease. The antibody and/or RNAi construct reduces the level of expression of ASGR, ASGR-1 and/or ASGR-2. Subsequent rounds of antibodies and/or RNAi are administered to the subject. One or more of the markers in Example 19 (e.g., Tier 1) is monitored to make certain that an adequate amount of the antibody and/or RNAi construct is administered and is functioning as desired. The risk that the subject will experience a myocardial infarction or coronary artery disease is decreased.

Additionally, as a further option, physiologic effects of the antibody and/or RNAi can be evaluated in relevant animal models of myocardial infarction or coronary artery disease using readouts including blood pressure, primary and secondary hemostasis, heart function and morphology, endothelial function, LDL cholesterol levels, non-HDL cholesterol levels, inflammation, and/or atherosclerosis.

Example 22: Method of Reducing LDL Cholesterol

A subject having a LDL cholesterol level to be lowered is identified. One or more antibodies as provided herein (see Example 7, as well as Tables A, B and C) and/or RNAi constructs that reduce expression of ASGR-1 and/or ASGR-2 (as outlined in Example 3), are administered to the subject. The antibody and/or RNAi construct reduces the level of expression of ASGR, ASGR-1 and/or ASGR-2. Subsequent rounds of antibodies and/or RNAi are administered to the subject. One or more of the markers in Example 19 (e.g., tier 1) is monitored to make certain that an adequate amount of the antibody and/or RNAi construct is administered and is functioning as desired. The level of LDL cholesterol in the subject is thereby reduced.

Example 23: Method of Reducing Non-HDL Cholesterol

A subject having a non-HDL cholesterol level to be lowered is identified. One or more antibodies as provided herein (see Example 7, as well as Tables A, B and C) and/or RNAi constructs that reduce expression of ASGR-1 and/or ASGR-2 (as outlined in Example 3), are administered to the subject. The antibody and/or RNAi construct reduces the level of expression of ASGR, ASGR-1 and/or ASGR-2. Subsequent rounds of antibodies and/or RNAi are administered to the subject. One or more of the markers in Example 19 (e.g., Tier 1) is monitored to make certain that an adequate amount of the antibody and/or RNAi construct is administered and is functioning as desired. The level of non-HDL cholesterol in the subject is thereby reduced.

Example 24: Method of Increasing ALP Levels

One or more antibodies as provided herein (see Example 7, as well as Tables A, B, and C) and/or RNAi constructs that reduce expression of ASGR-1 and/or ASGR-2 (as outlined in Example 3), are administered to the subject. The antibody and/or RNAi construct reduces the level of expression of ASGR, ASGR-1 and/or ASGR-2. Subsequent rounds of antibodies and/or RNAi are administered to the subject. One or more of the markers in Example 19 (e.g., Tier 1) is monitored to make certain that an adequate amount of the antibody and/or RNAi construct is administered and is functioning as desired. The level of ALP in the subject is thereby increased.

Example 25: Method of Monitoring the Effectiveness of an ASGR-1 Therapy

One or more antibodies as provided herein (see Example 7, as well as Tables A, B and C) and/or RNAi constructs that reduce expression of ASGR-1 and/or ASGR-2 (as outlined in Example 3), are administered to the subject. One or more of the markers in Example 19 is monitored to make certain that an adequate amount of the antibody and/or RNAi construct is administered and is functioning as desired. When the marker level changes in a similar manner to those changes noted in Example 19 (e.g., Tier 1), it is evidence that the amount of the one or more antibody and/or RNAi is effective. Additionally, as a further option, the effectiveness of this biochemical change can be observed by its physiologic effects from the antibody and/or RNAi, which can be evaluated using readouts including blood pressure, primary and secondary hemostasis, heart function and morphology, endothelial function, LDL cholesterol levels, non-HDL cholesterol levels, inflammation, and/or atherosclerosis.

Lengthy table referenced here

US12331122-20250617-T00001

Please refer to the end of the specification for access instructions.

Lengthy table referenced here

US12331122-20250617-T00002

Please refer to the end of the specification for access instructions.

Lengthy table referenced here

US12331122-20250617-T00003

Please refer to the end of the specification for access instructions.

Lengthy table referenced here

US12331122-20250617-T00004

Please refer to the end of the specification for access instructions.

Lengthy table referenced here

US12331122-20250617-T00005

Please refer to the end of the specification for access instructions.

Each reference cited herein is hereby incorporated by reference in its entirety for all that it teaches and for all purposes.

The present invention is not to be limited in scope by the specific embodiments described herein, which are intended as single illustrations of individual embodiments of the invention, and functionally equivalent methods and components are invention. Indeed, various modifications of the invention, in addition to those shown and described herein will become apparent to those skilled in the art from the foregoing description and accompanying drawings. Such modifications are intended to fall within the scope of the appended claims.

LENGTHY TABLES

The patent contains a lengthy table section. A copy of the table is available in electronic form from the USPTO web site (https://seqdata.uspto.gov/?pageRequest=docDetail&DocID=US12331122B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/?pageRequest=docDetail&DocID=US12331122B2). An electronic copy of the sequence listing will also be available from the USPTO upon request and payment of the fee set forth in 37 CFR 1.19(b)(3).

What is claimed is:

1. An isolated monoclonal antibody or antigen binding fragment thereof, wherein the isolated monoclonal antibody or antigen binding fragment thereof specifically binds to human asialoglycoprotein receptor 1 ("ASGR-1") and comprises a heavy chain variable domain comprising a VH CDR1, a VH CDR2 and a VH CDR3 and a light chain variable domain comprising a VL CDR1, a VL CDR2 and a VL CDR3, wherein:

(i) VH CDR1, VH CDR2, and VH CDR3 comprise the sequences of SEQ ID NOs: 4880, 12892, and 20904, respectively; and VL CDR1, VL CDR2 and VL CDR3 comprise the sequences of SEQ ID NOs: 872, 8884, and 16896, respectively;

(ii) VH CDR1, VH CDR2, and VH CDR3 comprise the sequences of SEQ ID NOs: 4700, 12712, and 20724, respectively; and VL CDR1, VL CDR2 and VL CDR3 comprise the sequences of SEQ ID NOs: 692, 8704, and 16716, respectively;

(iii) VH CDR1, VH CDR2, and VH CDR3 comprise the sequences of SEQ ID NOs: 5150, 13162, and 21174, respectively; and VL CDR1, VL CDR2 and VL CDR3 comprise the sequences of SEQ ID NOs: 1144, 9156, and 17168, respectively;

(iv) VH CDR1, VH CDR2, and VH CDR3 comprise the sequences of SEQ ID NOs: 7382, 15394, and 23406, respectively; and VL CDR1, VL CDR2 and VL CDR3 comprise the sequences of SEQ ID NOs: 3378, 11390, and 19402, respectively;

(v) VH CDR1, VH CDR2, and VH CDR3 comprise the sequences of SEQ ID NOs: 7822, 15834, and 23846, respectively; and VL CDR1, VL CDR2 and VL CDR3 comprise the sequences of SEQ ID NOs: 3818, 11830, and 19842, respectively;

(vi) VH CDR1, VH CDR2, and VH CDR3 comprise the sequences of SEQ ID NOs: 5378, 13390, and 21402, respectively; and VL CDR1, VL CDR2 and VL CDR3 comprise the sequences of SEQ ID NOs: 1372, 9384, and 17396, respectively;

(vii) VH CDR1, VH CDR2, and VH CDR3 comprise the sequences of SEQ ID NOs: 7500, 15512 and 23524, respectively; and VL CDR1, VL CDR2 and VL CDR3 comprise the sequences of SEQ ID NOs: 3496, 11508, and 19520, respectively;

(viii) VH CDR1, VH CDR2, and VH CDR3 comprise the sequences of SEQ ID NOs: 4846, 12858, and 20870, respectively; and VL CDR1, VL CDR2 and VL CDR3 comprise the sequences of SEQ ID NOs: 838, 8850, and 16862, respectively;

(ix) VH CDR1, VH CDR2, and VH CDR3 comprise the sequences of SEQ ID NOs: 6138, 14150, and 22162, respectively; and VL CDR1, VL CDR2 and VL CDR3 comprise the sequences of SEQ ID NOs: 2132, 10144, and 18156, respectively;

(x) VH CDR1, VH CDR2, and VH CDR3 comprise the sequences of SEQ ID NOs: 6884, 14896, and 22908, respectively; and VL CDR1, VL CDR2 and VL CDR3 comprise the sequences of SEQ ID NOs: 2878, 10890, and 18902, respectively;

(xi) VH CDR1, VH CDR2, and VH CDR3 comprise the sequences of SEQ ID NOs: 6898, 14910, and 22922, respectively; and VL CDR1, VL CDR2 and VL CDR3 comprise the sequences of SEQ ID NOs: 2892, 10904, and 18916, respectively;

(xii) VH CDR1, VH CDR2, and VH CDR3 comprise the sequences of SEQ ID NOs: 7296, 15308, and 23320, respectively; and VL CDR1, VL CDR2 and VL CDR3 comprise the sequences of SEQ ID NOs: 3292, 11304, and 19316, respectively;

(xiii) VH CDR1, VH CDR2, and VH CDR3 comprise the sequences of SEQ ID NOs: 7298, 15310, and 23322, respectively; and VL CDR1, VL CDR2 and VL CDR3 comprise the sequences of SEQ ID NOs: 3294, 11306, and 19318, respectively;

(xiv) VH CDR1, VH CDR2, and VH CDR3 comprise the sequences of SEQ ID NOs: 7308, 15320, and 23332, respectively; and VL CDR1, VL CDR2 and VL CDR3 comprise the sequences of SEQ ID NOs: 3304, 11316, and 19328, respectively; or (xv) VH CDR1, VH CDR2, and VH CDR3 comprise the sequences of SEQ ID NOs: 6508, 14520, and 22532, respectively; and VL CDR1, VL CDR2 and VL CDR3 comprise the sequences of SEQ ID NOs: 2502, 10514, and 18526, respectively.

2. The isolated monoclonal antibody or antigen binding fragment thereof of claim 1, comprising a heavy chain variable domain having at least 80% identity to any of the VH domain amino acid sequences set forth in SEQ ID NOs: 28734, 29184, 31418, 31858, 29412, 31536, 28914, 28880, 30172, 31332, 31334, 31344, 30542, 30918, and 30932.

3. The isolated monoclonal antibody or antigen binding fragment thereof of claim 1, comprising a heavy chain variable domain having at least 90% identity to any of the VH domain amino acid sequences set forth in SEQ ID NOs: 28734, 29184, 31418, 31858, 29412, 31536, 28914, 28880, 30172, 31332, 31334, 31344, 30542, 30918, and 30932.

4. The isolated monoclonal antibody or antigen binding fragment thereof of claim 1, comprising a light chain variable domain having at least 80% identity to any of the VL domain amino acid sequences set forth in SEQ ID NOs: 24728, 25178, 27412, 27852, 25406, 27530, 24908, 24874, 26166, 27326, 27328, 27338, 26536, 26912, and 26926.

5. The isolated monoclonal antibody or antigen binding fragment thereof of claim 1, comprising a light chain variable domain having at least 90% identity to any of the VL domain amino acid sequences set forth in SEQ ID NOs: 24728, 25178, 27412, 27852, 25406, 27530, 24908, 24874, 26166, 27326, 27328, 27338, 26536, 26912, and 26926.

6. The isolated monoclonal antibody or antigen binding fragment thereof of claim 1, wherein the heavy chain variable domain and the light chain variable domain are selected from one of the following paired VH and VL sequences, respectively:

SEQ ID NOs: 28734 and 24728;
SEQ ID NOs: 29184 and 25178;
SEQ ID NOs: 31418 and 27412;
SEQ ID NOs: 31858 and 27852;
SEQ ID NOs: 29412 and 25406;
SEQ ID NOs: 31536 and 27530;
SEQ ID NOs: 28914 and 24908;
SEQ ID NOs: 28880 and 24874;
SEQ ID NOs: 30172 and 26166;
SEQ ID NOs: 31332 and 27326;
SEQ ID NOs: 31334 and 27328;
SEQ ID NOs: 31344 and 27338;
SEQ ID NOs: 30542 and 26536;
SEQ ID NOs: 30918 and 26912; and
SEQ ID NOs: 30932 and 26926.

7. The isolated monoclonal antibody or antigen binding fragment thereof of claim 1 that is a humanized or a human monoclonal antibody or antigen binding fragment thereof.

8. An isolated neutralizing monoclonal antibody that binds to human asialoglycoprotein receptor 1 ("ASGR-1") comprising the amino acid sequence of SEQ ID NO:5 but has a statistically significant reduction in binding to a variant human ASGR-1, wherein the variant human ASGR-1 comprises a single mutation of a residue selected from the group consisting of: R170, S171, G172, R183, L184, W195, E196, K199, H203, H204, P207, V208, N209, H215, D216, P220, D225, D228, R237, P238, E239, P241, D242, D243, Y245, G246, H247, G248, L249, G251, E253, T259, D260, R263, N265, Q270, R271, P272, R274 and E280 as shown in SEQ ID NO:5.

9. The isolated neutralizing monoclonal antibody of claim 8, wherein the single mutation is selected from the group consisting of: W195, E196, K199, H203, H204, P207, P220, G251, and R263 as shown in SEQ ID NO:5.

10. The isolated monoclonal antibody of claim 8, wherein the single mutation comprises a substitution of a non-arginine residue with arginine, or a substitution of an arginine residue to glutamic acid.

11. The isolated monoclonal antibody of claim 9, wherein the single mutation comprises a substitution of a non-arginine residue with arginine, or a substitution of an arginine residue to glutamic acid.

12. An isolated humanized or human monoclonal antibody that binds to human asialoglycoprotein receptor 1 ("ASGR-1") comprising the amino acid sequence of SEQ ID NO: 5, wherein the binding of the monoclonal antibody to human ASGR-1 is reduced at a pH of 5.6 as compared to its binding at a pH of 7.4, and wherein the monoclonal antibody inhibits ASGR-1 ligand binding.

13. The isolated humanized or human monoclonal antibody of claim 12, wherein the binding of the monoclonal antibody to human ASGR-1 is reduced in the absence of calcium as compared to its binding in the presence of calcium.

14. A pharmaceutical composition comprising the isolated monoclonal antibody or antigen binding fragment thereof of claim 1, and a pharmaceutically acceptable excipient.

15. A pharmaceutical composition comprising the isolated monoclonal antibody of claim 8, and a pharmaceutically acceptable excipient.

16. A pharmaceutical composition comprising the isolated monoclonal antibody of claim 12, and a pharmaceutically acceptable excipient.

17. A pharmaceutical composition comprising the isolated monoclonal antibody of claim 13, and a pharmaceutically acceptable excipient.

* * * * *